US011685751B2

(12) United States Patent
Geum et al.

(10) Patent No.: US 11,685,751 B2
(45) Date of Patent: Jun. 27, 2023

(54) COMPOUND AND ORGANIC LIGHT-EMITTING ELEMENT COMPRISING SAME

(71) Applicant: LG CHEM, LTD., Seoul (KR)

(72) Inventors: Sujeong Geum, Daejeon (KR); Hye Min Cho, Daejeon (KR); Seonwoo Kim, Daejeon (KR); Wanpyo Hong, Daejeon (KR); Jaegoo Lee, Daejeon (KR); Hoon Jun Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 71 days.

(21) Appl. No.: 17/428,851

(22) PCT Filed: Nov. 27, 2020

(86) PCT No.: PCT/KR2020/017074
§ 371 (c)(1),
(2) Date: Aug. 5, 2021

(87) PCT Pub. No.: WO2021/107680
PCT Pub. Date: Jun. 3, 2021

(65) Prior Publication Data
US 2023/0061019 A1     Mar. 2, 2023

(30) Foreign Application Priority Data

Nov. 29, 2019 (KR) .................. 10-2019-0156840
May 20, 2020 (KR) .................. 10-2020-0060630

(51) Int. Cl.
*C07F 5/02* (2006.01)
*C09K 11/06* (2006.01)
(Continued)

(52) U.S. Cl.
CPC ............ *H01L 51/008* (2013.01); *C07F 5/027* (2013.01); *C09K 11/06* (2013.01);
(Continued)

(58) Field of Classification Search
CPC .............................. C07F 5/027; H01L 51/008
See application file for complete search history.

(56) References Cited

U.S. PATENT DOCUMENTS

2004/0251816 A1   12/2004   Leo et al.
2018/0301629 A1   10/2018   Hatakeyama et al.
(Continued)

FOREIGN PATENT DOCUMENTS

CN   106467553 A   3/2017
CN   110943176 A   3/2020
(Continued)

OTHER PUBLICATIONS

Computer-generated English-language translation of WO-2020218079-A1.*
(Continued)

*Primary Examiner* — Vu A Nguyen
(74) *Attorney, Agent, or Firm* — Dentons US LLP

(57) ABSTRACT

A compound of Chemical Formula 1, and an organic light emitting device including the same, the compound used as a material of an organic material layer of the organic light emitting device and providing high color purity and enhanced lifetime properties.

[Chemical Formula 1]

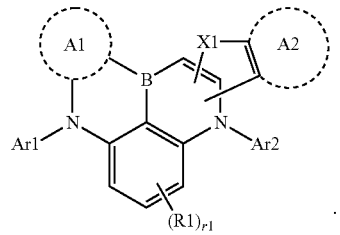

8 Claims, 12 Drawing Sheets

(51) Int. Cl.
*H01L 51/00* (2006.01)
*H01L 51/50* (2006.01)

(52) U.S. Cl.
CPC .. *C07B 2200/05* (2013.01); *C09K 2211/1018* (2013.01); *H01L 51/5016* (2013.01); *H01L 51/5028* (2013.01); *H01L 2251/5384* (2013.01)

(56) References Cited

U.S. PATENT DOCUMENTS

| | | |
|---|---|---|
| 2019/0058124 A1 | 2/2019 | Hatakeyama et al. |
| 2019/0165279 A1 | 5/2019 | Fujita |
| 2019/0207112 A1 | 7/2019 | Hatakeyama et al. |
| 2019/0280209 A1 | 9/2019 | Fujita |
| 2019/0341571 A1* | 11/2019 | Liaptsis ............. H01L 51/5024 |
| 2020/0024263 A1 | 1/2020 | Ito et al. |
| 2020/0058885 A1 | 2/2020 | Hong et al. |
| 2020/0098991 A1 | 3/2020 | Kim et al. |
| 2020/0144513 A1 | 5/2020 | Hatakeyama et al. |
| 2020/0144514 A1 | 5/2020 | Hatakeyama et al. |
| 2020/0144515 A1 | 5/2020 | Hatakeyama et al. |
| 2020/0172558 A1 | 6/2020 | Joo et al. |
| 2020/0176679 A1 | 6/2020 | Jeong et al. |
| 2020/0227639 A1 | 7/2020 | Yamatani |
| 2020/0403165 A1 | 12/2020 | Park et al. |
| 2021/0005825 A1 | 1/2021 | Tasaki et al. |
| 2021/0184121 A1 | 6/2021 | Suh et al. |
| 2022/0089617 A1 | 3/2022 | Kim et al. |
| 2022/0263027 A1 | 8/2022 | Kim et al. |
| 2022/0271226 A1 | 8/2022 | Heo et al. |

FOREIGN PATENT DOCUMENTS

| | | |
|---|---|---|
| CN | 111253421 A | 6/2020 |
| CN | 113227066 A | 8/2021 |
| CN | 113348171 A | 9/2021 |
| CN | 113366002 A | 9/2021 |
| CN | 113454092 A | 9/2021 |
| CN | 113454093 A | 9/2021 |
| CN | 113795497 A | 12/2021 |
| CN | 113812015 A | 12/2021 |
| CN | 113841262 A | 12/2021 |
| CN | 113906580 A | 1/2022 |
| CN | 113924665 A | 1/2022 |
| CN | 114026147 A | 2/2022 |
| EP | 3565018 A1 | 6/2019 |
| EP | 3792989 A1 | 3/2021 |
| EP | 3 907 228 A1 | 10/2021 |
| EP | 3915979 A1 | 12/2021 |
| EP | 3 960 744 A1 | 2/2022 |
| EP | 4001284 A1 | 5/2022 |
| JP | 2010215759 A | 9/2010 |
| KR | 10-2017-0127593 A | 11/2017 |
| KR | 10-2017-0130434 A | 11/2017 |
| KR | 10-1876763 B1 | 7/2018 |
| KR | 10-2018-0122298 A | 11/2018 |
| KR | 2018-0134850 A | 12/2018 |
| KR | 10-2019-0062177 A | 6/2019 |
| KR | 10-2019-0101900 A | 10/2019 |
| KR | 10-2019-0126791 A | 11/2019 |
| KR | 10-2019-0127529 A | 11/2019 |
| KR | 2020-0066208 A | 6/2020 |
| KR | 2020-0087906 A | 7/2020 |
| KR | 10-2020-0125583 A | 11/2020 |
| KR | 2020-0145674 A | 12/2020 |
| KR | 2021-0010389 A | 1/2021 |
| KR | 2021-0027179 A | 3/2021 |
| KR | 102430998 B1 | 8/2022 |
| WO | 03/012890 A2 | 2/2003 |
| WO | 2015/102118 A1 | 7/2015 |
| WO | 2017/188111 A1 | 11/2017 |
| WO | 2018/186374 A1 | 10/2018 |
| WO | 2020054676 A1 | 3/2020 |
| WO | WO-2020218079 A1 * | 10/2020 ............. H01L 51/50 |
| WO | 2020/231214 A1 | 11/2020 |
| WO | 2021010770 A1 | 1/2021 |

OTHER PUBLICATIONS

Kondo, et al.(2019). Narrowband Deep-Blue Organic Light-Emitting Diode Featuring an Organoboron-Based Emitter.Nature Photonics. vol. 13, pp. 678-682.

Santoro, et al.(2008).Effective Method for the Computation of Optical Spectra of Large Molecules at Finite Temperature Including the Duschinsky and Herzberg-Teller effect:The Qx . . . The Journal of Chemical Physics.vol.128, 224311.

STN Registry RN2377144-83-5, Oct. 15, 2019 (2 Pgs).

* cited by examiner

【FIG. 1】
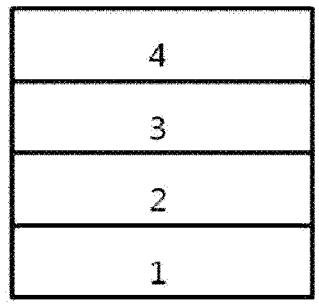
【FIG. 2】
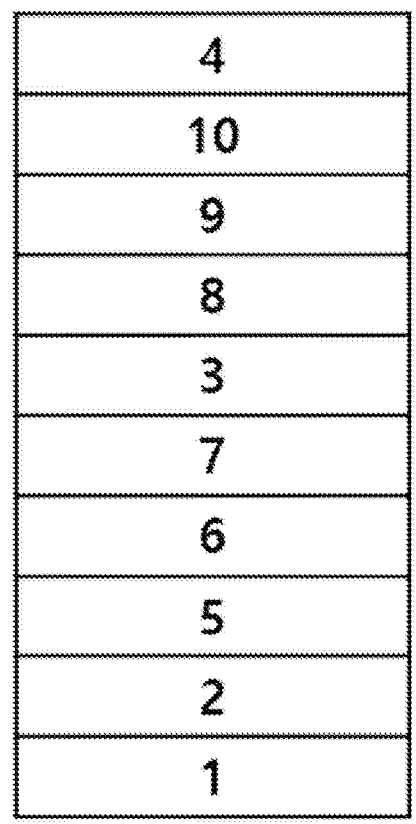

[FIG. 3]
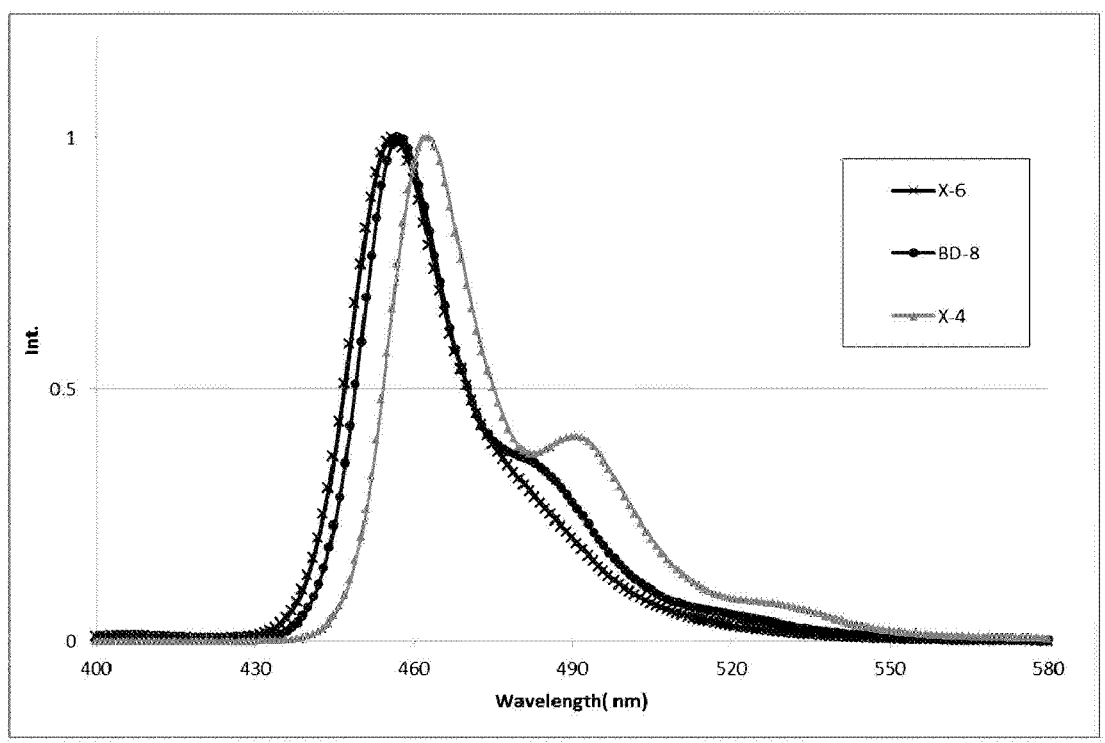

【FIG. 4】
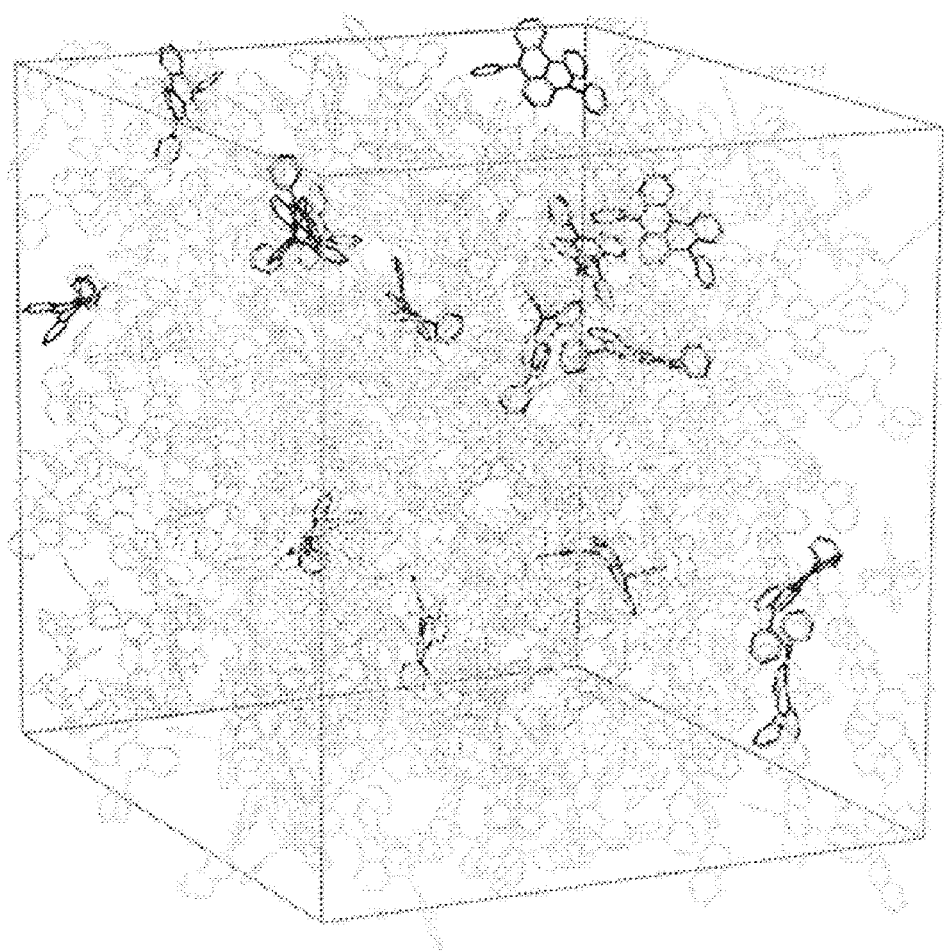

[FIG. 5]
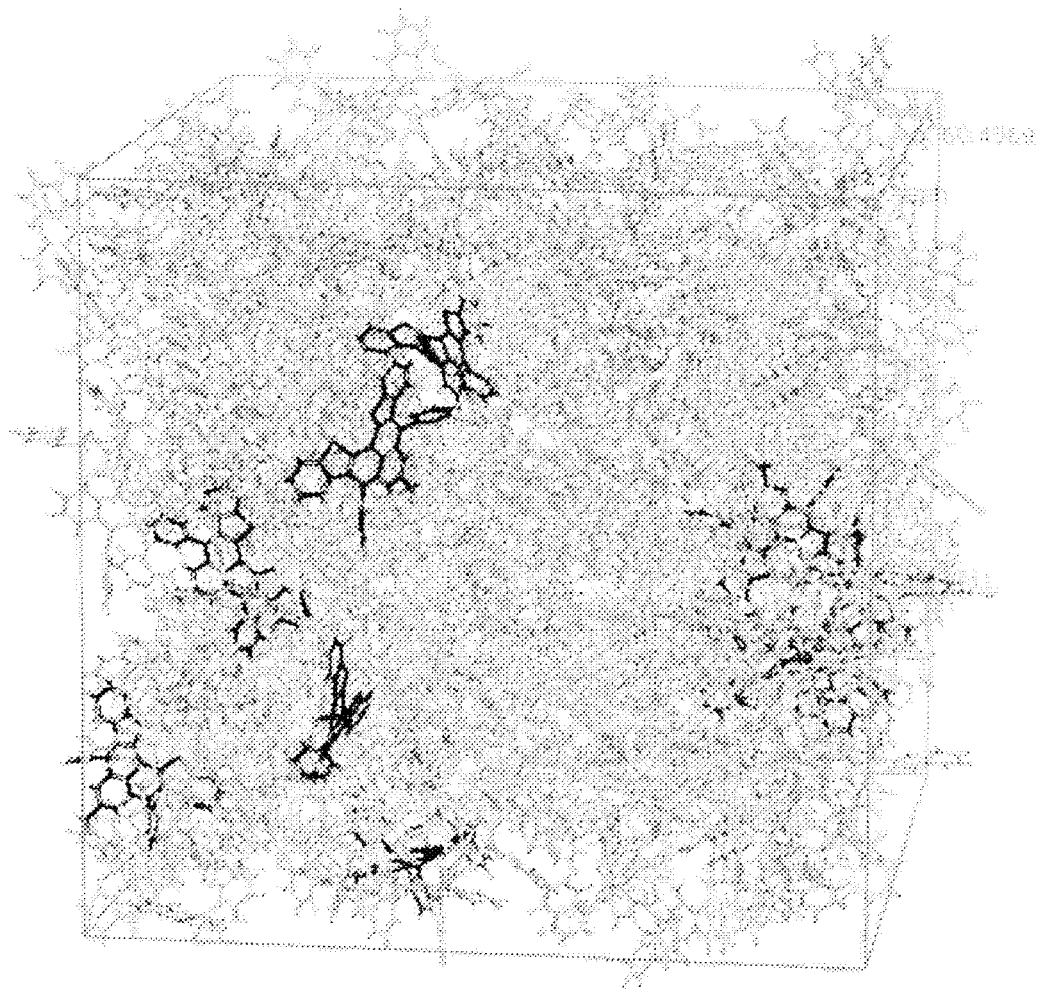

【FIG. 6】
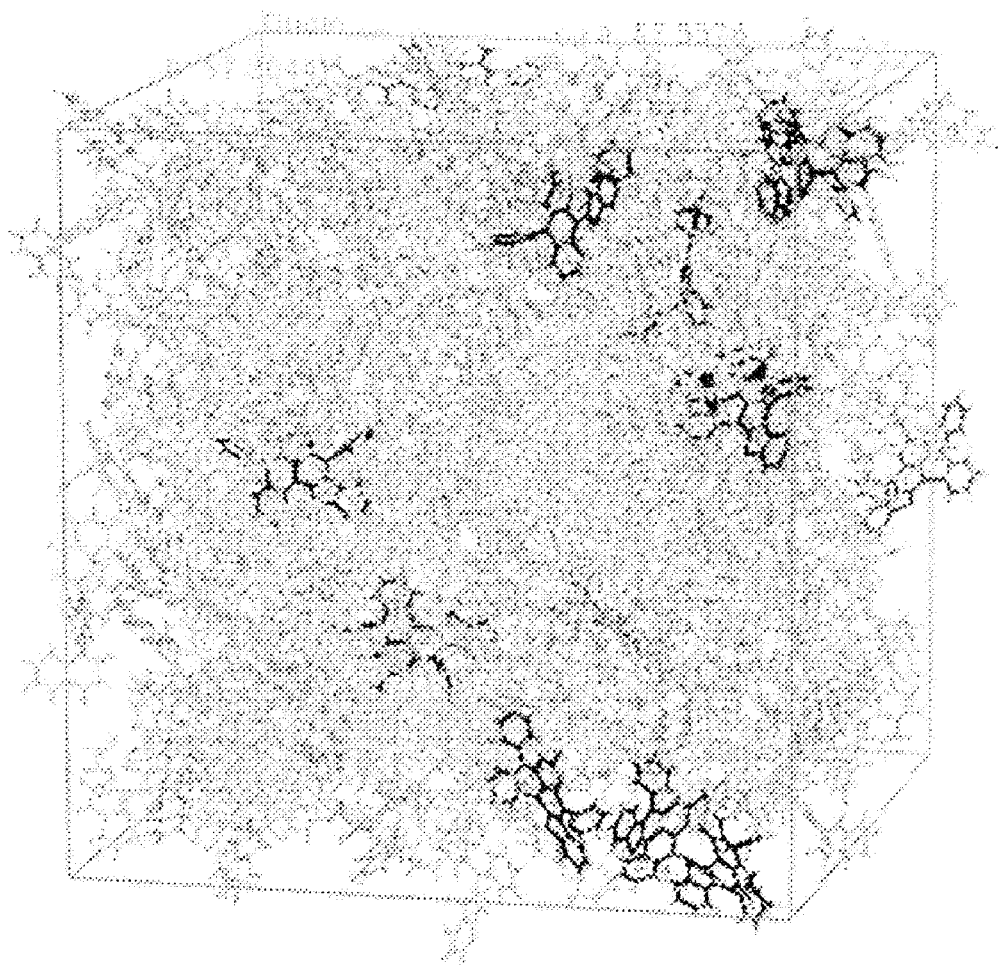

[FIG. 7]
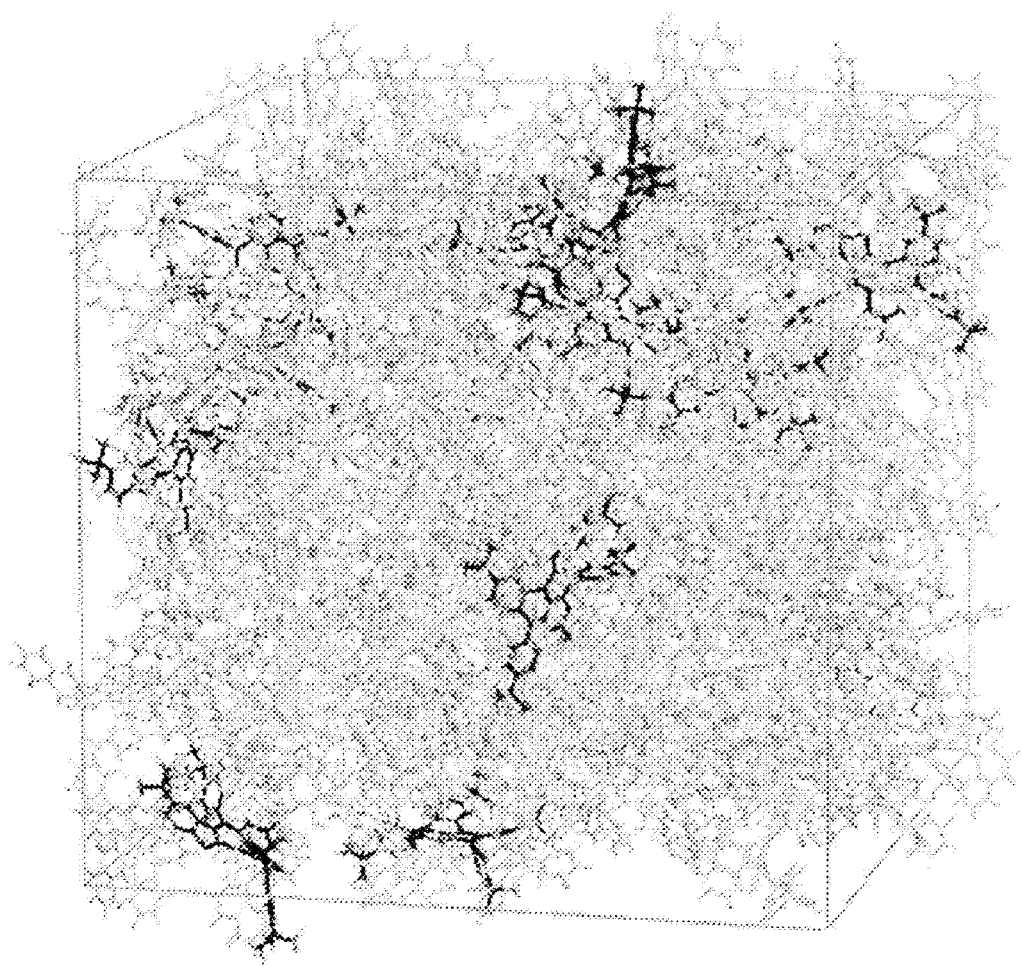

[FIG. 8]
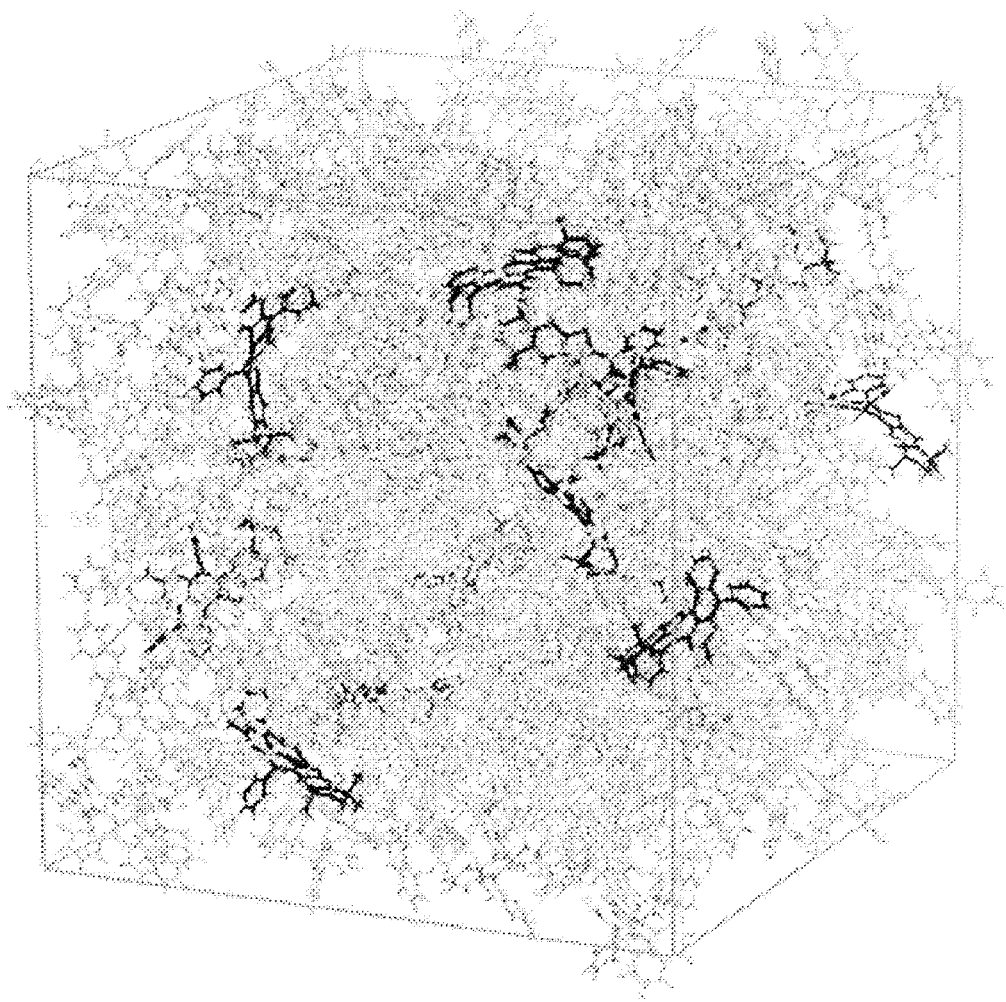

[FIG. 9]
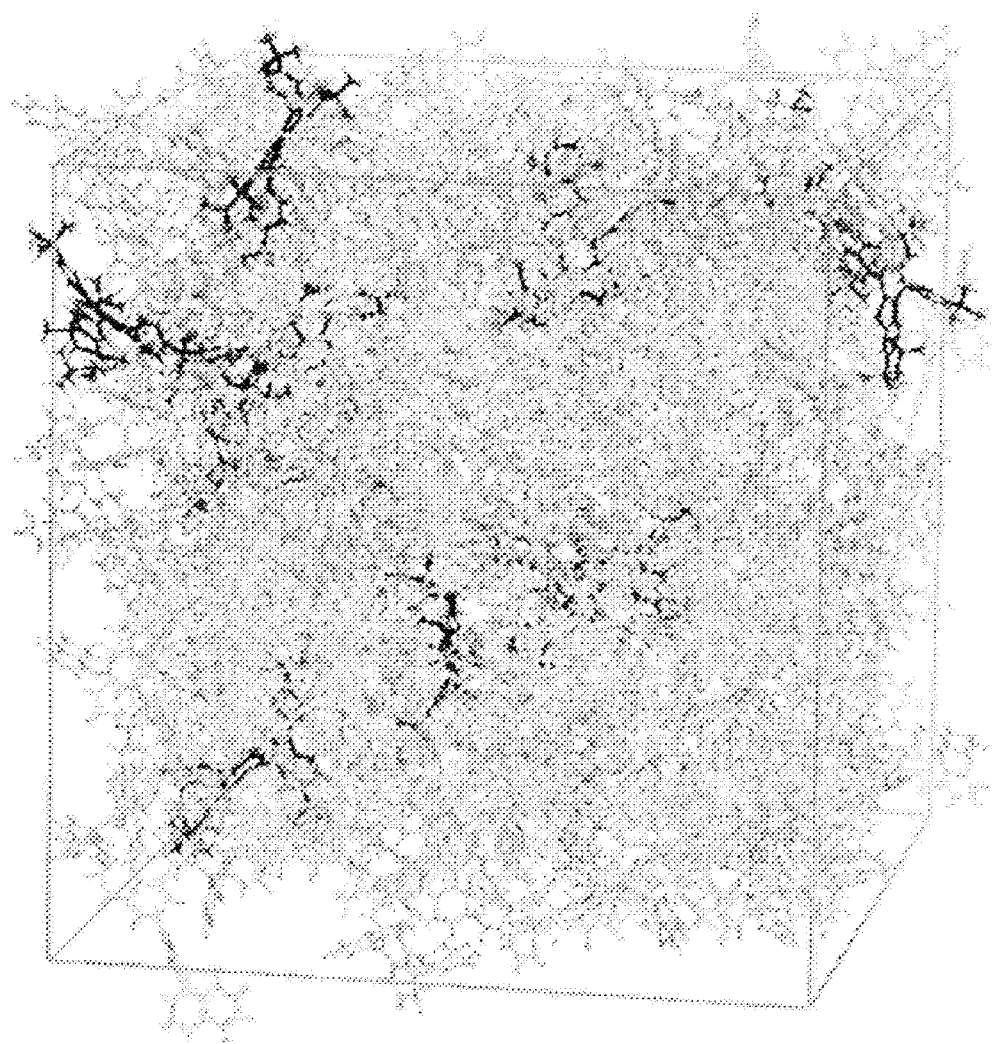

[FIG. 10]
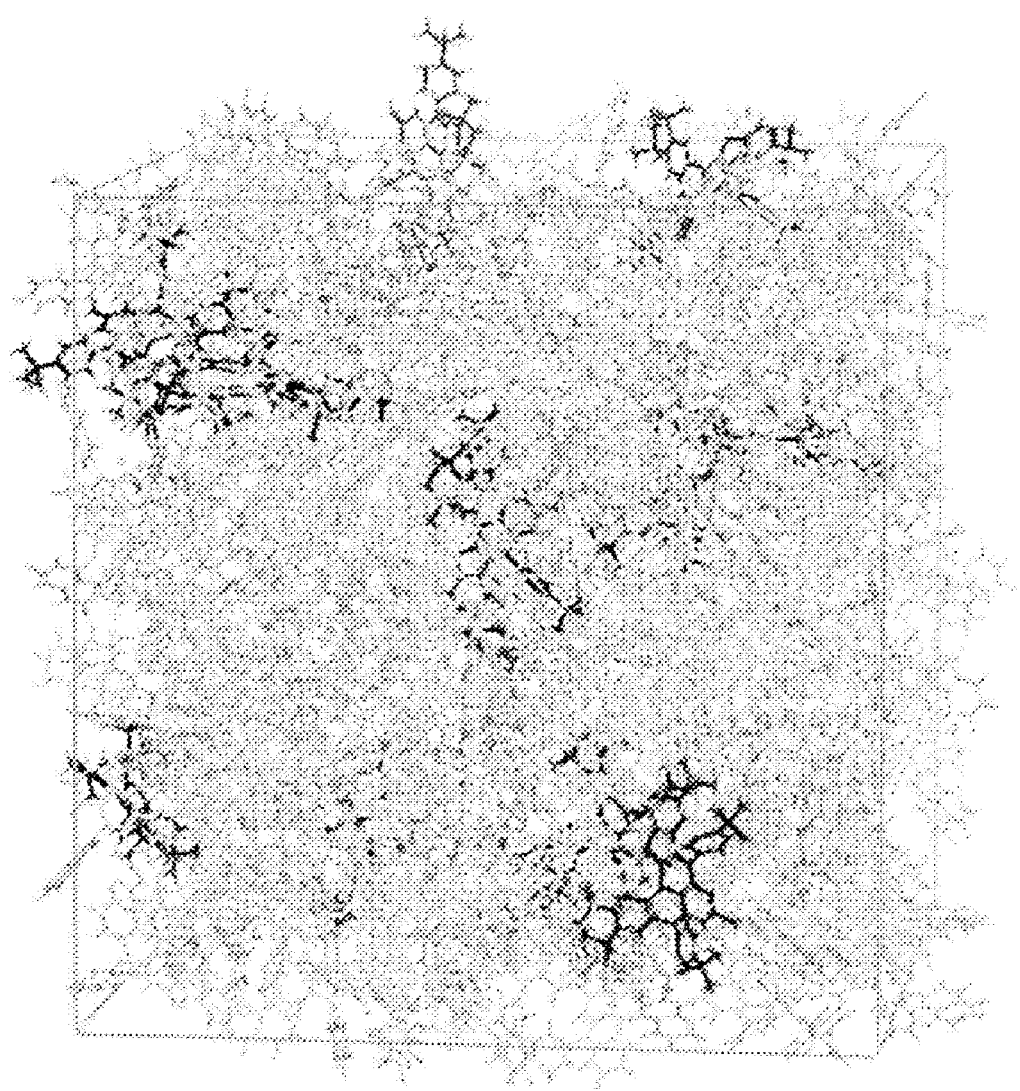

[FIG. 11]
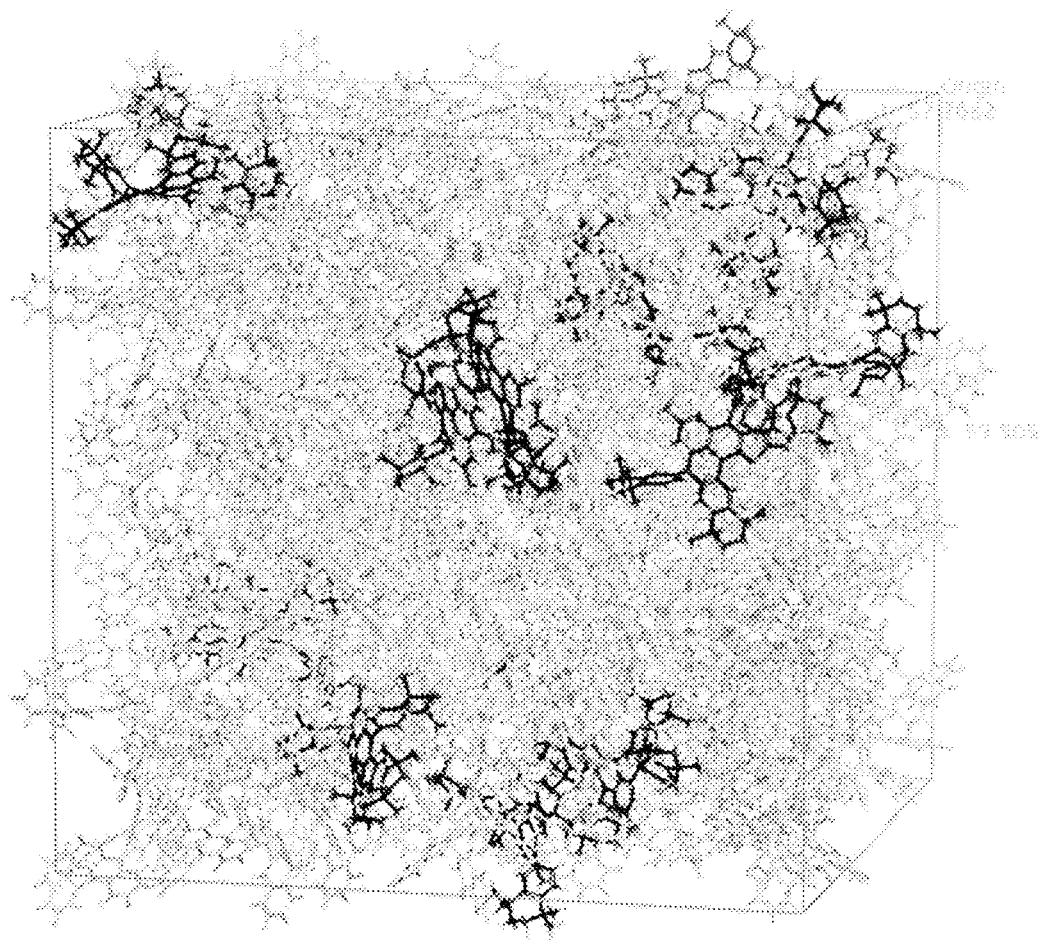

[FIG. 12]
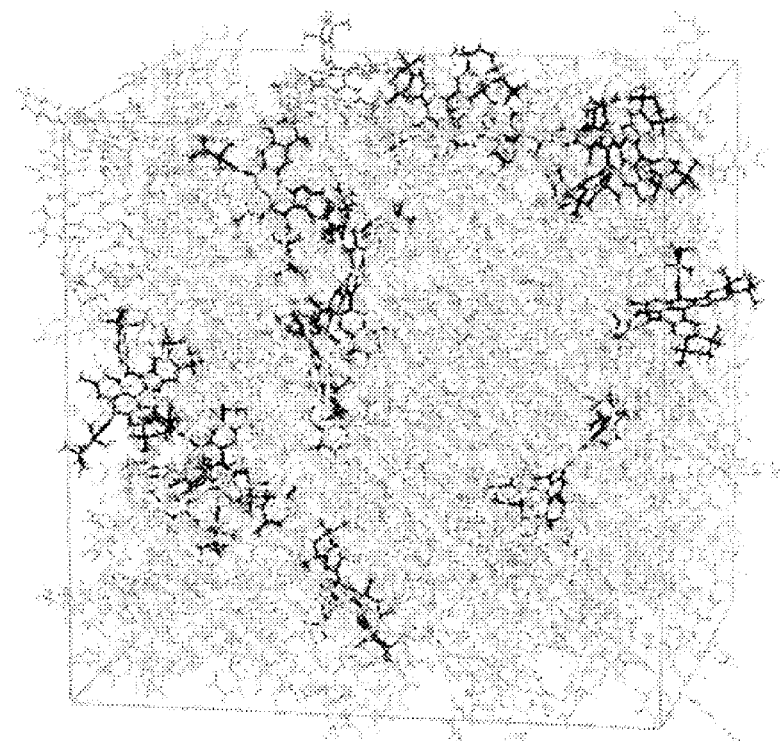
[FIG. 13]
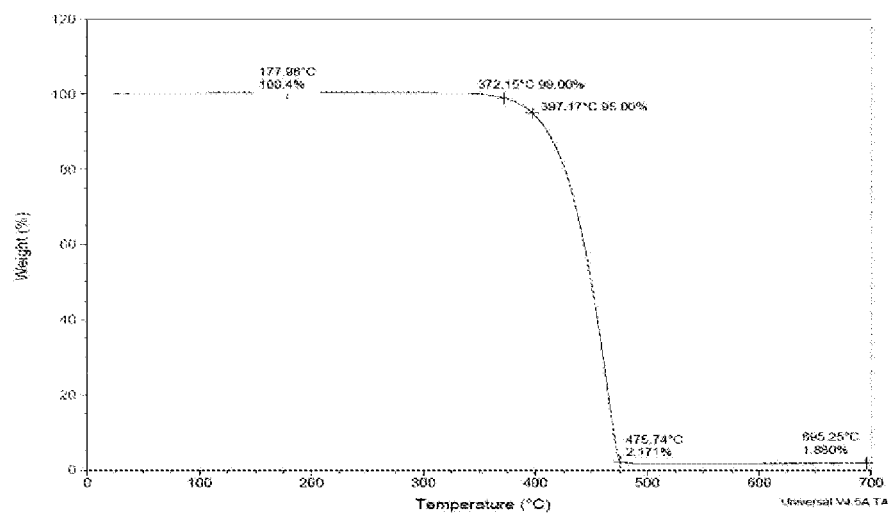

【FIG. 14】
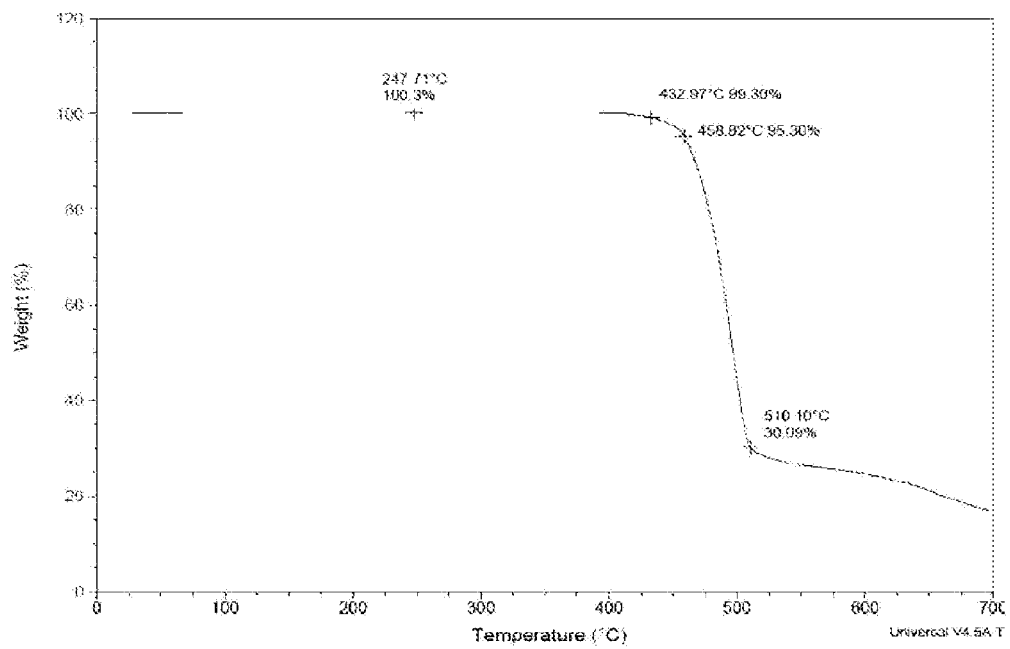
【FIG. 15】
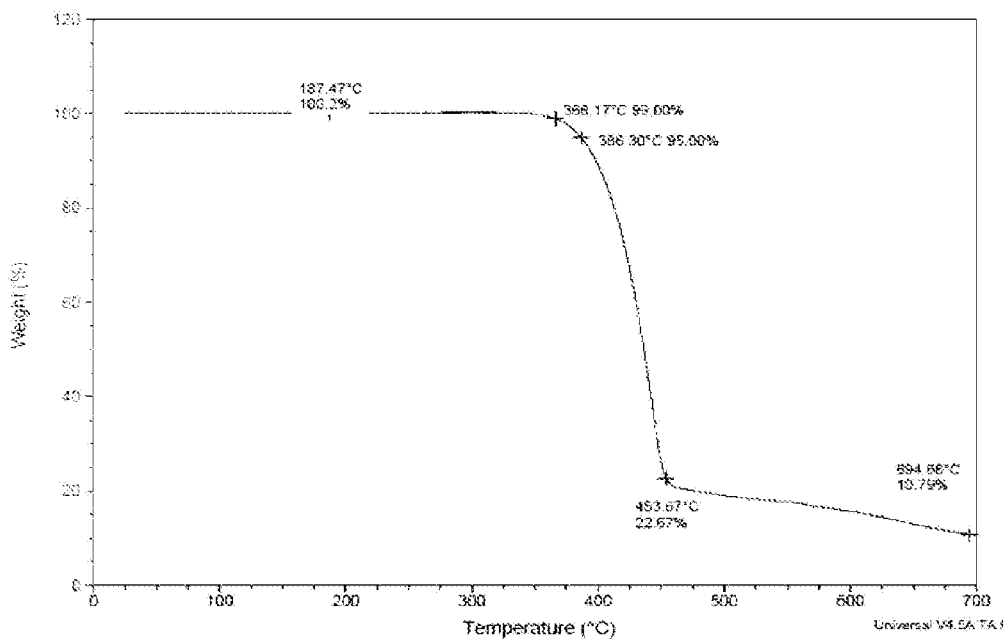

COMPOUND AND ORGANIC LIGHT-EMITTING ELEMENT COMPRISING SAME

CROSS-REFERENCE TO RELATED APPLICATIONS

This application is a National Phase entry pursuant to 35 U.S.C. § 371 of International Application No. PCT/KR2020/017074 filed on Nov. 27, 2020, and claims priority to and the benefits of Korean Patent Application No. 10-2019-0156840, filed on Nov. 29, 2019, and Korean Patent Application No. 10-2020-0060630, filed on May 20, 2020, the disclosures of which are incorporated herein by reference in their entireties.

FIELD OF DISCLOSURE

The present specification relates to a compound, and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required. In a blue organic light emitting device among these, high color purity and long lifetime properties are essential, however, there are lack of technologies to obtain these both due to instability caused by high energy of a blue material. Recently, a thermally active delayed fluorescent material having a core structure including boron has been newly developed and received attention for high efficiency and color purity, however, the material has a disadvantage of short lifetime due to high triplet energy and low inverse interphase transition rate. Accordingly, development of a blue organic light emitting body capable of obtaining both high color purity and long lifetime properties has been required.

SUMMARY

The present specification is directed to providing a compound, and an organic light emitting device including the same.

One embodiment of the present specification provides a compound represented by the following Chemical Formula 1.

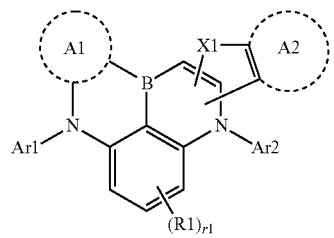

[Chemical Formula 1]

in Chemical Formula 1,

X1 is O or S,

A1 is a substituted or unsubstituted heteroring; a substituted or unsubstituted aromatic hydrocarbon ring; or a substituted or unsubstituted fused ring of aromatic hydrocarbon ring and aliphatic hydrocarbon ring, A2 is a substituted or unsubstituted aromatic hydrocarbon ring; a substituted or unsubstituted aliphatic hydrocarbon ring; or a substituted or unsubstituted fused ring of aromatic hydrocarbon ring and aliphatic hydrocarbon ring, Ar1 and Ar2 are the same as or different from each other, and each independently a substituted or unsubstituted cycloalkyl group; a substituted or unsubstituted aryl group; a substituted or unsubstituted heterocyclic group; or a substituted or unsubstituted fused ring group of aromatic hydrocarbon ring and aliphatic hydrocarbon ring, R1 is hydrogen; deuterium; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; a substituted or unsubstituted fused ring group of aromatic hydrocarbon ring and aliphatic hydrocarbon ring; or a substituted or unsubstituted heterocyclic group, r1 is an integer of 1 to 3, r1 is 2 or greater, the two or more R1s are the same as or different from each other, and Chemical Formula 1 includes at least one fused aliphatic hydrocarbon ring substituted with a substituted or unsubstituted alkyl group.

Another embodiment of the present specification provides an organic light emitting device including a first electrode; a second electrode provided opposite to the first electrode; and an organic material layer including one or more layers provided between the first electrode and the second electrode, wherein one or more layers of the organic material layer include the compound.

Advantageous Effects

A compound according to one embodiment of the present specification can be used as a material of an organic material layer of an organic light emitting device, and by using the same, high color purity and/or enhancement in lifetime properties of the organic light emitting device can be obtained.

DESCRIPTION OF DRAWINGS

FIG. 1 and FIG. 2 each illustrates an organic light emitting device according to an exemplary embodiment of the present specification.

FIG. 3 is a graph showing a result of photoluminescence analysis according to Experimental Example 2 of the present specification.

FIG. 4 to FIG. 12 are diagrams showing molecular models obtained through simulations of Experimental Example 1 of the present specification.

FIG. 13 is a graph showing a result of thermos gravimetric analysis of Example 46 of the present specification.

FIG. 14 is a graph showing a result of thermos gravimetric analysis of Comparative Example 16 of the present specification.

FIG. 15 is a graph showing a result of thermos gravimetric analysis of Comparative Example 17 of the present specification.

DESCRIPTION OF REFERENCE NUMERAL

1: Substrate
2: First Electrode
3: Light Emitting Layer
4: Second Electrode
5: Hole Injection Layer
6: Hole Transfer Layer
7: Electron Blocking Layer
8: First Electron Transfer Layer
9: Second Electron Transfer Layer
10: Electron Injection Layer

DETAILED DESCRIPTION

Hereinafter, the present specification will be described in more detail.

An organic light emitting device using an existing boron-based compound has more favorable efficiency compared to an organic light emitting device using a pyrene-based compound, but has a disadvantage of short lifetime. However, the compound represented by Chemical Formula 1 includes S or O, which lowers first triplet excitation energy of Chemical Formula 1, and thereby increases a difference between first singlet excitation energy and the first triplet excitation energy. Accordingly, triplet quenching is suppressed, and an organic light emitting device including the same has an increased device lifetime in a host-dopant system.

In addition, Chemical Formula 1 includes at least one fused aliphatic hydrocarbon ring substituted with a substituted or unsubstituted alkyl group, and has a left-right asymmetric structure, and therefore, a lifetime of an organic light emitting device including the same increases since Chemical Formula 1 is 1) thermally stable due to a lower sublimation temperature compared to an existing boron-based compound considering the molecular weight and has 2) high oxidation stability, and with the structural properties, efficiency of the organic light emitting device including the same increases by minimizing concentration quenching since 3) molecular planarity is minimized, and 4) molecular volume increases.

Throughout the specification of the present application, a term "combination thereof" included in a Markush-type expression means a mixture or a combination of one or more selected from the group consisting of constituents described in the Markush-type expression, and means including one or more selected from the group consisting of the constituents.

Examples of substituents in the present specification are described below, however, the substituents are not limited thereto.

In the present specification,

means a linking site.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted with one or more substituents selected from the group consisting of deuterium; a halogen group; a cyano group; an alkyl group; a cycloalkyl group; an alkoxy group; an aryloxy group; an alxylthioxy group; an arylthioxy group; an alkenyl group; a haloalkyl group; a haloalkoxy group; an arylalkyl group; a silyl group; a boron group; an amine group; an aryl group; a hydrocarbon ring group; and a heterocyclic group, or being substituted with a substituent, linking two or more substituents among the substituents illustrated above, or having no substituents.

In the present specification, linking two or more substituents refers to linking hydrogen of any one substituent to another substituent. For example, linking two substituents may include a phenyl group and a naphthyl group being linked to become a substituent of

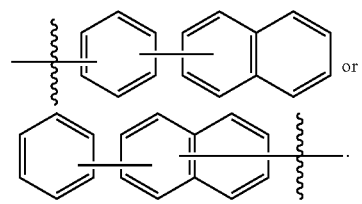

In addition, linking three substituents includes not only continuously linking (substituent 1)-(substituent 2)-(substituent 3), but also linking (substituent 2) and (substituent 3) to (substituent 1). For example, a phenyl group, a naphthyl group and an isopropyl group may be linked to become a substituent of

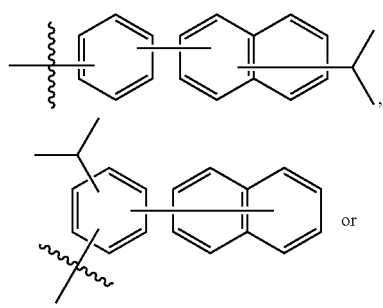

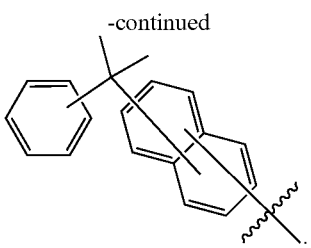

The same rule described above applies to cases of linking four or more substituents.

In the present specification, examples of the halogen group may include fluorine, chlorine, bromine or iodine.

In the present specification, the alkyl group may be linear or branched, and although not particularly limited thereto, the number of carbon atoms is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, an adamantyl group, a bicyclo[2.2.1]heptyl group, a bicyclo[2.2.1]octyl group, a norbornyl group and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, n-butoxy, isobutoxy, tert-ethoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the haloalkyl group means, in the definition of the alkyl group, hydrogen of the alkyl group being substituted with at least one halogen group.

In the present specification, the haloalkoxy group means, in the definition of the alkoxy group, hydrogen of the alkoxy group being substituted with at least one halogen group.

In the present specification, the aryl group is not particularly limited, but preferably has 6 to 30 carbon, atoms, and the aryl group may be monocyclic or polycyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthracene group, a phenanthrene group, a triphenylene group, a pyrene group, a phenalene group, a perylene group, a chrysene group, a fluorene group and the like, but are not limited thereto.

In the present specification, the fluorene group may be substituted, and adjacent groups may bond to each other to form a ring.

When the fluorene group is substituted,

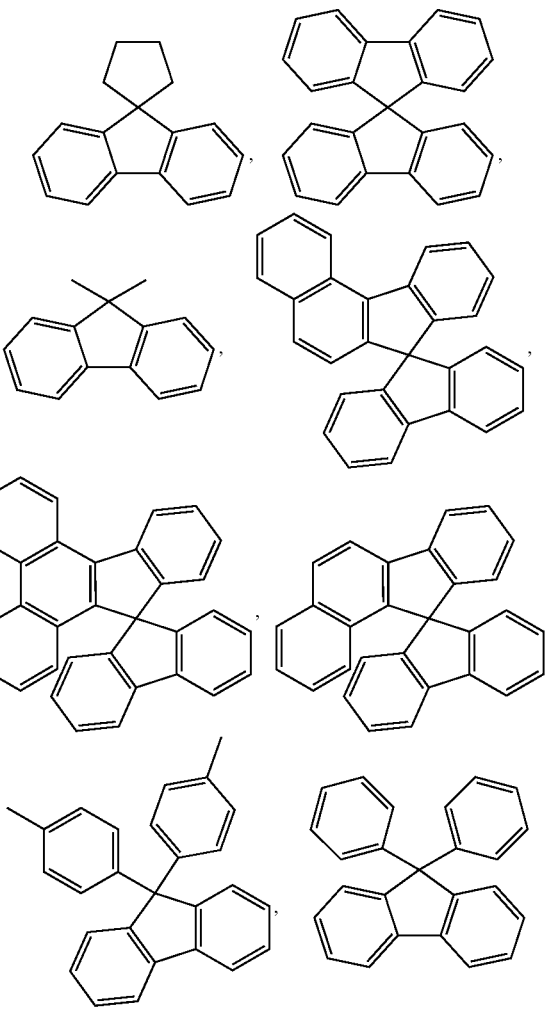

and the like may be included, however, the structure is not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the arylalkyl group means the alkyl group being substituted with an aryl group, and the examples of the aryl group and the alkyl group described above may be applied to the aryl group and the alkyl group of the arylalkyl group.

In the present specification, the aryloxy group means, in the definition of the alkoxy group, the alkyl group of the alkoxy group being substituted with an aryl group. Examples of the aryloxy group may include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, but are not limited thereto.

In the present specification, the alkyl group of the alkylthioxy group is the same as the examples of the alkyl group described above. Specific examples of the alkylthioxy group may include a methylthioxy group, an ethylthioxy group, a tert-butylthioxy group, a hexylthioxy group, an octylthioxy group and the like, but are not limited thereto.

In the present specification, the aryl group in the arylthioxy group is the same as the examples of the aryl group described above. Specific examples of the arylthioxy group may include a phenylthioxy group, a 2-methylphenylthioxy group, a 4-tert-butylphenylthioxy group and the like, but are not limited thereto.

In the present specification, the heterocyclic group is a group including one or more atoms that are not carbon, that is, heteroatoms, and specifically, the heteroatom may include one or more atoms selected from the group consisting of O, N, Se, S and the like, and includes an aromatic heterocyclic group or an aliphatic heterocyclic group. The aromatic heterocyclic group may be represented by a heteroaryl group. The number of carbon atoms of the heterocyclic group is not particularly limited, but is preferably from 2 to 30, and the heterocyclic group may be monocyclic or polycyclic. Examples of the heterocyclic group may include a thiophene group, a furan group, a pyrrole group, an imidazole group, a thiazole group, an oxazole group, an ozadiazole group, a pyridine group, a bipyridine group, a pyrimidine group, a triazine group, a triazole group, an acridine group, a pyridazine group, a pyrazine group, a quinoline group, a quinazoline group, a quinoxaline group, a phthalazine group, a pyridopyrimidine group, a pyridopyrazine group, a pyrazinopyrazine group, an isoquinoline group, an indole group, a carbazole group, a benzoxazole group, a benzimidazole group, a benzothiazole group, a benzocarbazole group, a benzothiophene group, a dibenzothiophene group, a benzofuran group, a phenanthridine group, a phenanthroline group, an isoxazole group, a thiadiazole group, a dibenzofuran group, dibenzosilole group, a phenoxanthine group, a phenoxazine group, a phenothiazine group, a decahydrobenzocarbazole group, a hexahydrocarbazole group, a dihydrobenzoazasiline group, a dihydroindenocarbazole group, a spirofluorenexanthene group, a spirofluorenethioxanthene group, a tetrahydronaphthothiophene group, a tetrahydronaphthofuran group, a tetrahydrobenzothiophene group, a tetrahydrobenzofuran group and the like, but are not limited thereto.

In the present specification, the silyl group may be an alkylsilyl group, an arylsilyl group, an alkylarylsilyl group, a heteroarylsilyl group or the like. As the alkyl group in the alkylsilyl group, the examples of the alkyl group described above may be applied, and as the aryl group in the arylsilyl group, the examples of the aryl group described above may be applied. As the alkyl group and the aryl group in the alkylarylsilyl group, the examples of the alkyl group and the aryl group may be applied, and as the heteroaryl group in the heteroarylsilyl group, the examples of the heterocyclic group may be applied.

In the present specification, the boron group may be $—BR_{100}R_{101}$. $R_{100}$ and $R_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heterocyclic group having 2 to 30 carbon atoms. Specific examples of the boron group may include a trimethylboron group, a triethylboron group, a t-butyldimethylboron group, a triphenylboron group, a phenylboron group and the like, but are not limited thereto.

In the present specification, the amine group may be selected from the group consisting of $—NH_2$, an alkyl amine group, an N-alkylarylamine group, an arylamine group, an N-arylheteroarylamine group, an N-alkylheteroarylamine group and a heteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group and the like, but are not limited thereto.

In the present specification, the N-alkylarylamine group means an amine group in which N of the amine group is substituted with an alkyl group and an aryl group. The alkyl group and the aryl group in the N-alkylarylamine group are the same as the examples of the alkyl group and the aryl group described above.

In the present specification, the N-arylheteroarylamine group means an amine group in which N of the amine group is substituted with an aryl group and a heteroaryl group. The aryl group and the heteroaryl group in the N-arylheteroarylamine group are the same as the examples of the aryl group and the heterocyclic group described above.

In the present specification, the N-alkylheteroarylamine group means an amine group in which N of the amine group is substituted with an alkyl group and a heteroaryl group. The alkyl group and the heteroaryl group in the N-alkylheteroarylamine group are the same as the examples of the alkyl group and the heterocyclic group described above.

In the present specification, examples of the alkyl amine group include a substituted or unsubstituted monoalkylamine group, or a substituted or unsubstituted dialkylamine group. The alkyl group in the alkylamine group may be a linear or branched alkyl group. The alkylamine group including two or more alkyl groups may include linear alkyl groups, branched alkyl groups, or both linear alkyl groups and branched alkyl groups. For example, the alkyl group in the alkylamine group may be selected from among the examples of the alkyl group described above.

In the present specification, examples of the heteroarylamine group include a substituted or unsubstituted monoheteroarylamine group, or a substituted or unsubstituted diheteroarylamine group. The heteroarylamine group including two or more heteroaryl groups may include monocyclic heteroaryl groups, polycyclic heteroaryl groups, or both monocyclic heteroaryl groups and polycyclic heteroaryl groups. For example, the heteroaryl group in the heteroarylamine group may be selected from among the examples of the heterocyclic group described above.

In the present specification, the hydrocarbon ring group may be an aromatic hydrocarbon ring group, an aliphatic hydrocarbon ring group, or a fused ring group of aromatic hydrocarbon ring and aliphatic hydrocarbon ring, and may be selected from among the examples of the cycloalkyl group, the aryl group, and combination thereof. Examples of the hydrocarbon ring group may include a phenyl group, a cyclohexyl group, an adamantyl group, a bicycle[2.2.1]heptyl group, a bicycle[2.2.1]octyl group, a tetrahydronaphthalene group, a tetrahydroanthracene group, a 1,2,3,4-tetrahydro-1,4-methanonaphthalene group, a 1,2,3,4-tetrahydro-1,4-ethanonaphthalene group and the like, but are not limited thereto.

In the present specification, the meaning of "adjacent" in the "adjacent groups bond to each other to form a ring" is the same as described above, and the "ring" means a substituted or unsubstituted hydrocarbon ring; or a substituted or unsubstituted heteroring.

In the present specification, the hydrocarbon ring may be an aromatic hydrocarbon ring, an aliphatic hydrocarbon ring, or a fused ring of aromatic hydrocarbon ring and aliphatic hydrocarbon ring, and may be selected from among the examples of the cycloalkyl group, the aryl group and combinations thereof except for those that are not monovalent. Examples of the hydrocarbon ring may include benzene, cyclohexane, adamantane, bicyclo[2.2.1]heptane, bicyclo[2.2.1]octane, tetrahydronaphthalene, tetrahydroanthracene, 1,2,3,4-tetrahydro-1,4-methanonaphthalene, 1,2,3,4-tetrahydro-1,4-ethanonaphthalene and the like, but are not limited thereto.

In the present specification, the heteroring includes one or more atoms that are not carbon, that is, heteroatoms, and specifically, the heteroatom may include one or more atoms selected from the group consisting of O, N, Se, S and the like. The heteroring may be monocyclic or polycyclic, may be aromatic, aliphatic, or a fused ring of aromatic and aliphatic, and the aromatic heteroring may be selected from among the examples of the heteroaryl group of the heterocyclic group except for those that are not monovalent.

In the present specification, the aliphatic heteroring means an aliphatic ring including one or more of heteroatoms. Examples of the aliphatic heteroring may include oxirane, tetrahydrofuran, 1,4-dioxane, pyrrolidine, piperidine, morpholine, oxepane, azokane, thiokane, tetrahydronaphthothiophene, tetrahydronaphthofuran, tetrahydrobenzothiophene, tetrahydrobenzofuran and the like, but are not limited thereto.

Unless defined otherwise in the present specification, all technological and scientific terms used in the present specification have the same meanings as terms commonly understood by those skilled in the art. Although methods and materials similar or equivalent to those described in the present specification may be used in carrying out or experimenting embodiments of the present disclosure, suitable methods and materials are described later. All publications, patent applications, patents and other reference documents mentioned in the present specification are incorporated by reference in the present specification as a whole, and when conflicting, the present specification including definitions has priority unless specific passage is mentioned. Furthermore, materials, methods and examples are for illustrative purposes only, and not to limit the present specification.

According to one embodiment of the present specification, X1 is O.

According to one embodiment of the present specification, X1 is S.

According to one embodiment of the present specification, the compound of Chemical Formula 1 is represented by the following Chemical Formula 2 or 3.

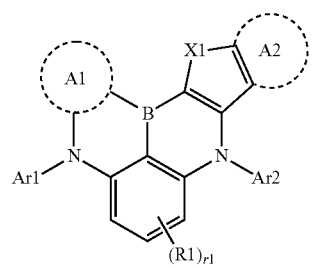

[Chemical Formula 2]

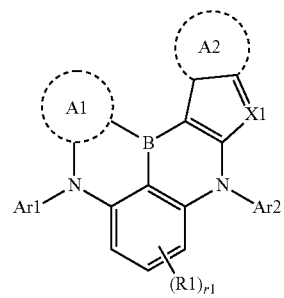

[Chemical Formula 3]

In Chemical Formulae 2 and 3,

A1, A2, X1, Ar1, Ar2, R1, and r1 have the same definitions as in Chemical formula 1.

According to one embodiment of the present specification, the compound of Chemical Formula 1 is represented by the following Chemical Formula 1-1 or 1-2.

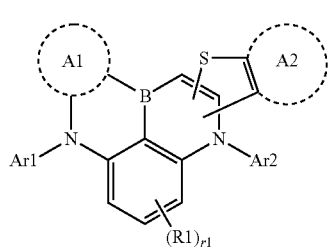

[Chemical Formula 1-1]

[Chemical Formula 1-2]

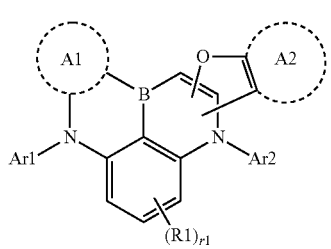

In Chemical Formulae 1-1 and 1-2,

A1, A2, Ar1, Ar2, R1 and r have the same definitions as in Chemical Formula 1.

According to one embodiment of the present specification, the compound of Chemical Formula 1 is represented by any one of the following Chemical Formulae 1-1-1, 1-1-2, 1-2-1 and 1-2-2.

[Chemical Formula 1-1-1]

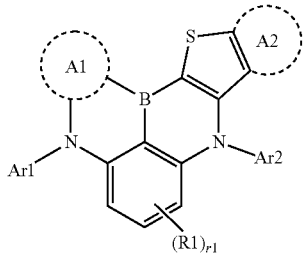

[Chemical Formula 1-1-2]

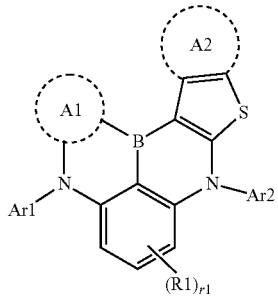

[Chemical Formula 1-2-1]

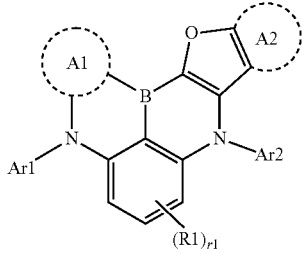

[Chemical Formula 1-2-2]

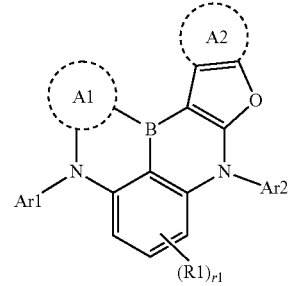

In Chemical Formulae 1-1-1, 1-1-2, 1-2-1 and 1-2-2,
A1, A2, Ar1, Ar2, R1 and r1 have the same definitions as in Chemical Formula 1.

According to one embodiment of the present specification, the compound of Chemical Formula 1 is represented by the following Chemical Formula 1-3 or 1-4.

[Chemical Formula 1-3]

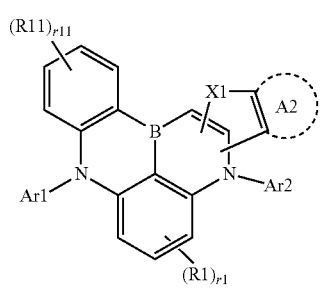

[Chemical Formula 1-4]

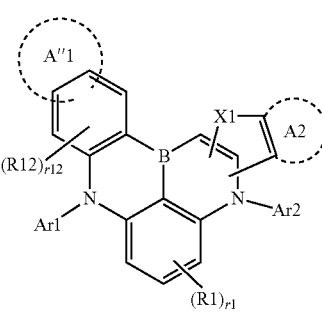

In Chemical Formulae 1-3 and 1-4,

X1, A2, Ar1, Ar2, R1 and r1 have the same definitions as in Chemical Formula 1,

A"1 is a substituted or unsubstituted aliphatic hydrocarbon ring,

R11 and R12 are the same as or different from each other, and each independently hydrogen; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; or a substituted or unsubstituted heterocyclic group, or adjacent groups bond to each other to form a ring.

r11 is an integer of 1 to 4, and when r11 is 2 or greater, the two or more R11s are the same as or different from each other, and r12 is 1 or 2, and when r12 is 2, the two R12s are the same as or different from each other.

According to one embodiment of the present specification, the compound of Chemical Formula 1 is represented by any one of the following Chemical Formulae 1-3-1, 1-3-2, 1-4-1 and 1-4-2.

[Chemical Formula 1-3-1]

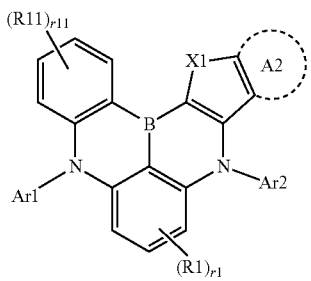

[Chemical Formula 1-3-2]

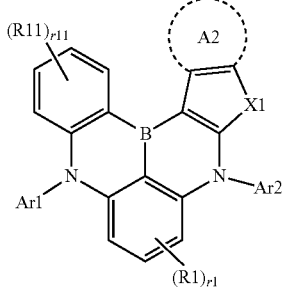

[Chemical Formula 1-4-1]

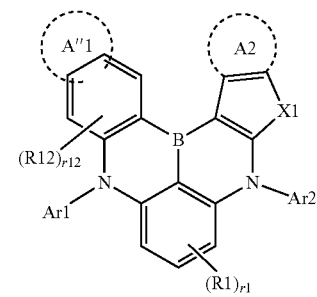

[Chemical Formula 1-4-2]

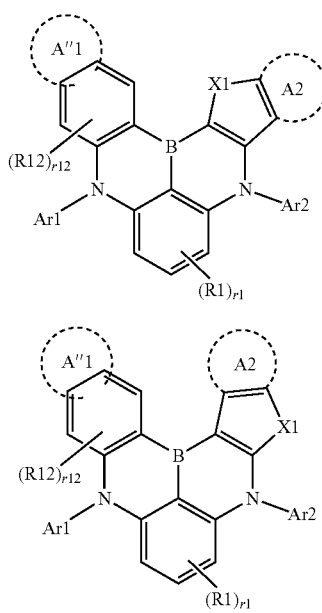

In Chemical Formulae 1-3-1, 1-3-2, 1-4-1 and 1-4-2,

X1, A2, Ar1, Ar2, R1 and r1 have the same definitions as in Chemical Formula 1,

A"1 is a substituted or unsubstituted aliphatic hydrocarbon ring,

R11 and R12 are the same as or different from each other, and each independently hydrogen; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; or a substituted or unsubstituted heterocyclic group, or adjacent groups bond to each other to form a ring, r11 is an integer of 1 to 4, and when r11 is 2 or greater, the two or more R11s are the sane as or different from each other, and r12 is 1 or 2, and when r12 is 2, the two R12s are the same as or different from each other.

According to one embodiment of the present specification, the compound of Chemical Formula 1-4 is represented by the following Chemical Formula 1-4-3 or 1-4-4.

[Chemical Formula 1-4-3]

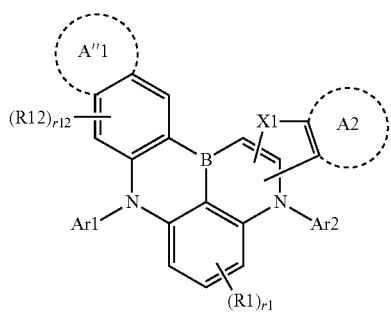

[Chemical Formula 1-4-4]

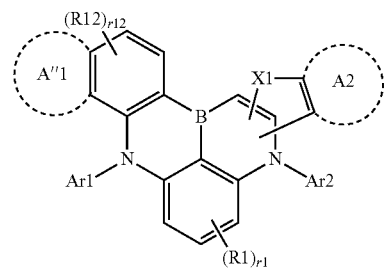

In Chemical Formulae 1-4-3 and 1-4-4,

X1, A2, Ar1, Ar2, R1 and r1 have the same definitions as in Chemical Formula 1,

A"1 is a substituted or unsubstituted aliphatic hydrocarbon ring,

R12 is hydrogen; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; or a substituted or unsubstituted heterocyclic group, and r12 is 1 or 2, and when r12 is 2, the two R12s are the same as or different from each other.

According to one embodiment of the present specification, the compound of Chemical Formula 1-4 is represented by any one of the following Chemical Formulae 1-4-5, 1-4-6, 1-4-7 and 1-4-8.

[Chemical Formula 1-4-5]

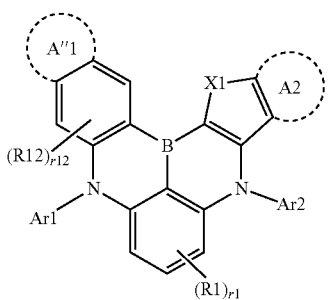

[Chemical Formula 1-4-6]

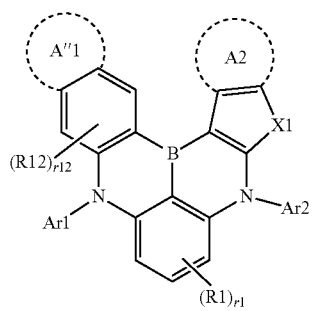

[Chemical Formula 1-4-7]

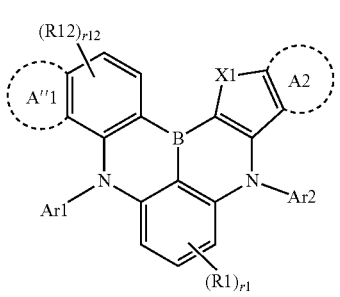

[Chemical Formula 1-4-8]

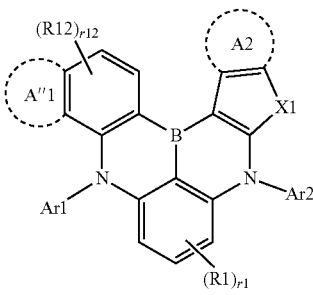

In Chemical Formulae 1-4-5, 1-4-6, 1-4-7 and 1-4-3,

X1, A2, Ar1, Ar2, R1 and r1 have the same definitions as in Chemical Formula 1,

A″1 is a substituted or unsubstituted aliphatic hydrocarbon ring,

R12 is hydrogen; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; or a substituted or unsubstituted heterocyclic group, and r12 is 1 or 2, and when r12 is 2, the two R12s are the same as or different from each other.

According to one embodiment of the present specification, Chemical Formula 1 includes one fused aliphatic hydrocarbon ring substituted with a substituted or unsubstituted alkyl group.

According to one embodiment of the present specification, Chemical Formula 1 includes two fused aliphatic hydrocarbon rings substituted with a substituted or unsubstituted alkyl group.

According to one embodiment of the present specification, Chemical Formula 1 includes three fused aliphatic hydrocarbon rings substituted with a substituted or unsubstituted alkyl group.

According to one embodiment of the present specification, Chemical Formula 1 includes four fused aliphatic hydrocarbon rings substituted with a substituted or unsubstituted alkyl group.

According to one embodiment of the present specification, Chemical Formula 1 includes at least one monocyclic or polycyclic fused aliphatic hydrocarbon ring having 3 to 30 carbon atoms substituted with a substituted or unsubstituted linear or branched alkyl group having 1 to 30 carbon atoms.

According to one embodiment of the present specification, Chemical Formula 1 includes at least one monocyclic or polycyclic fused aliphatic hydrocarbon ring having 3 to 20 carbon atom substituted with a substituted or unsubstituted linear or branched alkyl group having 1 to 20 carbon atoms.

According to one embodiment of the present specification, Chemical Formula 1 includes at least one monocyclic or polycyclic fused aliphatic hydrocarbon ring having 3 to 10 carbon atoms substituted with a substituted or unsubstituted linear or branched alkyl group having 1 to 10 carbon atoms.

According to one embodiment of the present specification, Chemical Formula 1 includes at least one monocyclic or polycyclic fused aliphatic hydrocarbon ring having 3 to 30 carbon atoms substituted with a linear or branched alkyl group having 1 to 30 carbon atoms unsubstituted or substituted with deuterium.

According to one embodiment of the present specification, Chemical Formula 1 includes at least one monocyclic or polycyclic fused aliphatic hydrocarbon ring having 3 to 20 carbon atoms substituted with a linear or branched alkyl group having 1 to 20 carbon atoms unsubstituted or substituted with deuterium.

According to one embodiment of the present specification, Chemical Formula 1 includes at least one monocyclic or polycyclic fused aliphatic hydrocarbon ring having 3 to 10 carbon atoms substituted with a linear or branched alkyl group having 1 to 10 carbon atoms unsubstituted or substituted with deuterium.

According to one embodiment of the present specification, Chemical Formula 1 includes at least one monocyclic or polycyclic aliphatic hydrocarbon ring having 3 to 10 carbon atoms substituted with a linear or branched alkyl group having 1 to 30 carbon atoms unsubstituted or substituted with deuterium.

According to one embodiment of the present specification, Chemical Formula 1 includes at least one monocyclic or polycyclic fused aliphatic hydrocarbon ring having 5 to 10 carbon atoms substituted with a linear or branched alkyl group having 1 to 10 carbon atoms unsubstituted or substituted with deuterium.

According to one embodiment of the present specification, Chemical Formula 1 includes at least one monocyclic or polycyclic fused aliphatic hydrocarbon ring having 6 to 10 carbon atoms substituted with a linear or branched alkyl group having 1 to 10 carbon atoms unsubstituted or substituted with deuterium.

According to one embodiment of the present specification, Chemical Formula 1 includes at least one monocyclic or polycyclic fused aliphatic hydrocarbon ring having 5 to 8 carbon atoms substituted with a linear or branched alkyl group having 1 to 10 carbon atoms unsubstituted or substituted with deuterium.

According to one embodiment of the present specification, Chemical Formula 1 includes at least one monocyclic or polycyclic fused aliphatic hydrocarbon ring having 6 to 8 carbon atoms substituted with a linear or branched alkyl group having 1 to 10 carbon atoms unsubstituted or substituted with deuterium.

According to one embodiment of the present specification, Chemical Formula 1 includes at least one monocyclic or polycyclic fused aliphatic hydrocarbon ring having 5 to 10 carbon atoms substituted with a linear or branched alkyl group having 1 to 5 carbon atoms unsubstituted or substituted with deuterium.

According to one embodiment of the present specification, Chemical Formula 1 includes at least one monocyclic or polycyclic fused aliphatic hydrocarbon ring having 6 to 10 carbon atoms substituted with a linear or branched alkyl group having 1 to 5 carbon atoms unsubstituted or substituted with deuterium.

According to one embodiment of the present specification, Chemical Formula 1 includes at least one monocyclic or polycyclic fused aliphatic hydrocarbon ring having 5 to 8 carbon atoms substituted with a linear or branched alkyl group having 1 to 5 carbon atoms unsubstituted or substituted with deuterium.

According to one embodiment of the present specification, Chemical Formula 1 includes at least one monocyclic or polycyclic fused aliphatic hydrocarbon ring having 6 to 8 carbon atoms substituted with a linear or branched alkyl group having 1 to 5 carbon atoms unsubstituted or substituted with deuterium.

According to one embodiment of the present specification, Chemical Formula 1 includes at least one monocyclic fused aliphatic hydrocarbon ring having 5 or 6 carbon atoms substituted with a linear or branched alkyl group having 1 to 30 carbon atoms unsubstituted or substituted with deuterium.

According to one embodiment of the present specification, Chemical Formula 1 includes at least one monocyclic fused aliphatic hydrocarbon ring having 5 or 6 carbon atoms substituted with a linear or branched alkyl group having 1 to 10 carbon atoms unsubstituted or substituted with deuterium.

According to one embodiment of the present specification, Chemical Formula 1 includes one or more selected from the group consisting of a fused cyclohexane ring substituted with one or more selected from the group consisting of a methyl group substituted with deuterium, a methyl group and deuterium; a fused bicycle[2.2.1]heptane ring substituted with a methyl group; and a fused bicyclo[2.2.1]octane ring substituted with a methyl group.

According to one embodiment of the present specification, Chemical Formula 1 includes one or more selected from the group consisting of a fused tetramethylcyclohexane ring; tetradeuteriumtetramethylcyclohexane; a fused tetratrideuteriummethylcyclohexane ring; a fused dimethylbicyclo[2.2.1]heptane ring; and a fused dimethylbicyclo[2.2.1]octane ring.

According to one embodiment of the present specification, Chemical Formula 1 includes at least one of a fused cyclohexane ring substituted with one or more selected from the group consisting of deuterium, a methyl group, and a methyl group substituted with deuterium; a fused bicyclo[2.2.1]heptane ring substituted with a methyl group; or a fused bicyclo[2.2.1]octane ring substituted with a methyl group.

According to one embodiment of the present specification, Chemical Formula 1 includes at least one of a fused tetramethylcyclohexane ring; tetradeuteriumtetramethylcyclohexane; a fused tetratrideuteriummethylcyclohexane ring; a fused bicyclo[2.2.1]heptane ring substituted with a methyl group; or a fused bicyclo[2.2.1]octane ring substituted with a methyl group.

According to one embodiment of: the present specification, Chemical Formula 1 includes at least one fused cyclohexane ring substituted with a methyl group.

According to one embodiment of the present specification, Chemical Formula 1 includes at least one fused cyclohexane ring substituted with a methyl group substituted with deuterium.

According to one embodiment of the present specification, Chemical Formula 1 includes at least one fused cyclohexane ring substituted with a methyl group and deuterium.

According to one embodiment of the present specification, Chemical Formula 1 includes at least one fused bicyclo[2.2.1]heptane ring substituted with a methyl group.

According to one embodiment of the present specification, Chemical Formula 1 includes at least one fused bicyclo[2.2.1]octane ring substituted with a methyl group.

According to one embodiment of the present specification, Chemical Formula 1 includes at least one tetramethylcyclohexane.

According to one embodiment of the present specification, Chemical Formula 1 includes at least one tetramethylcyclohexane substituted with deuterium.

According to one embodiment of the present specification, Chemical Formula 1 includes at least one tetradeuteriumtetramethylcyclohexane.

According to one embodiment of the present specification, Chemical Formula 1 includes at least one fused tetratrideuteriummethylcyclohexane ring.

According to one embodiment of the present specification, Chemical Formula 1 includes at least one fused tetratrideuteriummethylcyclohexane ring substituted with deuterium.

According to one embodiment of the present specification, Chemical Formula 1 includes at least one fused dimethylbicyclo[2.2.1]heptane ring.

According to one embodiment of the present specification, Chemical Formula 1 includes at least one fused dimethylbicyclo[2.2.1]octane ring.

According to one embodiment of the present specification, Chemical Formula 1 includes at least one of the following structures.

-continued

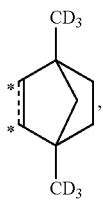 , 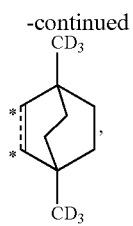 , 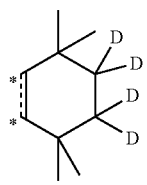

In the structures,

is a bonding site to adjacent ring atoms, and in the structure, hydrogen at a position substitutable with deuterium may be substituted with deuterium.

Two tert-butyl groups may bond to form the structures.

According to one embodiment of the present specification, the meaning of "including at least one fused aliphatic hydrocarbon ring substituted with a substituted or unsubstituted alkyl group" is an aliphatic hydrocarbon ring substituted with an alkyl group being fused to at least one of fusible positions of Chemical Formula 1.

According to one embodiment of the present specification, the fused aliphatic hydrocarbon ring substituted with an alkyl group is included in at least one of A1, A2, Ar1, Ar2 and R2 of Chemical Formula 1.

In the present specification, including at least one fused aliphatic hydrocarbon ring substituted with an alkyl group in Chemical Formula 1 will be described using examples as follows, however, the structure is not limited thereto.

For example, 1) case of including a fused aliphatic hydrocarbon ring substituted with an alkyl group in Ar1 of Chemical Formula 1

When Ar1 of Chemical Formula 1 is a phenyl group, and

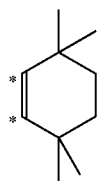

is included in Ar1 as the fused aliphatic hydrocarbon ring substituted with an alkyl group, Ar2 may be represented as a tetrahydronaphthalene group substituted with a methyl group, and may be represented by the following structure, however, the structure is not limited thereto.

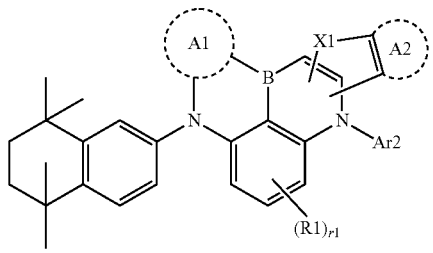

2) case of including a fused aliphatic hydrocarbon ring substituted with an alkyl group in A2 of Chemical Formula 1

When A2 of Chemical Formula 1 is benzene and includes

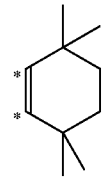

as the fused aliphatic hydrocarbon ring substituted with an alkyl group, A2 may be represented as tetrahydronaphthalene substituted with a methyl group, and may be represented by the following structure, however, Chemical Formula 1 is not limited to the following structure.

According to one embodiment of the present specification, A1 is a substituted or unsubstituted monocyclic or polycyclic heteroring having 2 to 30 carbon atoms; a substituted or unsubstituted monocyclic or polycyclic aromatic hydrocarbon ring having 6 to 30 carbon atoms; a substituted or unsubstituted monocyclic or polycyclic aliphatic hydrocarbon ring having 3 to 30 carbon atoms; or a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms, A2 is a substituted or unsubstituted monocyclic or polycyclic aromatic hydrocarbon ring having 6 to 30 carbon atoms; a substituted or unsubstituted monocyclic or polycyclic aliphatic hydrocarbon ring having 3 to 30 carbon atoms; or a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms, Ar1 and Ar2 are the same as or different from each other, and each independently a substituted or unsubstituted monocyclic or polycyclic aryl group having 6 to 30 carbon atoms; a substituted or unsubstituted monocyclic or polycyclic heterocyclic group having 2 to 30 carbon atoms; or a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms, and R1 is hydrogen; a substituted or unsubstituted linear or branched alkyl group having 1 to 30 carbon atoms; a substituted or unsubstituted monocyclic or polycyclic cycloalkyl group having 3 to 30 carbon atoms; a substituted or unsubstituted amine group; a substituted or unsubstituted monocyclic or polycyclic aryl group having 6 to 30 carbon atoms; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a monocyclic or polycyclic heterocyclic group having 2 to 30 carbon atoms.

According to one embodiment of the present specification, A1 is a substituted or unsubstituted monocyclic or polycyclic heterering having 2 to 30 carbon atoms; a substituted or unsubstituted monocyclic or polycyclic aromatic hydrocarbon ring having 6 to 30 carbon atoms; a substituted or unsubstituted monocyclic or polycyclic aliphatic hydrocarbon ring having 3 to 30 carbon atoms; or a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms.

According to one embodiment of the present specification, A1 is a substituted or unsubstituted monocyclic or polycyclic heterering having 2 to 20 carbon atoms; a substituted or unsubstituted monocyclic or polycyclic aromatic hydrocarbon ring having 6 to 20 carbon atoms; a substituted or unsubstituted monocyclic or polycyclic aliphatic hydrocarbon ring having 3 to 20 carbon atoms; or a substituted or unsubstituted fused ring of monocyclic or polycyclic aromatic hydrocarbon ring having 6 to 20 carbon atoms and monocyclic or polycyclic aliphatic hydrocarbon ring having 3 to 20 carbon atoms.

According to one embodiment of the present specification, A1 is substituted or unsubstituted tetrahydronaphthalene; substituted or unsubstituted naphthalene; substituted or unsubstituted 1,2,3,4-tetrahydro-1,4-methanonaphthalene; substituted or unsubstituted 1,2,3,4-tetrahydro-1,4-ethanonaphthalene; substituted or unsubstituted benzene; substituted or unsubstituted dibenzofuran; substituted or unsubstituted dibenzothiophene; substituted or unsubstituted fluorene; substituted or unsubstituted xanthene; or substituted or unsubstituted dibenzosilole.

In A1, the "substituted or unsubstituted" means being substituted with one or more substituents selected from the group consisting of deuterium; a linear or branched alkyl group having 1 to 30 carbon atoms unsubstituted or substituted with one or more selected from the group consisting of deuterium, and a monocyclic or polycyclic aryl group having 6 to 30 carbon atoms; a monocyclic or polycyclic aryl group having 6 to 30 carbon atoms unsubstituted or substituted with one or more selected from the group consisting of deuterium, a halogen group, a linear or branched alkyl group having 1 to 30 carbon atoms, and a monocyclic or polycyclic aryl group having 6 to 30 carbon atoms; a linear or branched alkylsilyl group having 1 to 30 carbon atoms; a monocyclic or polycyclic arylsilyl group having 6 to 30 carbon atoms; a monocyclic or polycyclic arylamine group having 6 to 30 carbon atoms unsubstituted or substituted with one or more selected from the group consisting of deuterium, a linear or branched alkyl group having 1 to 30 carbon atoms, and a linear or branched alkylsilyl group having 1 to 30 carbon atoms; an N-arylheteroarylamine group; an amine group including a fused ring group of monocyclic or polycyclic aromatic and aliphatic hydrocarbon ring having 6 to 30 carbon atoms unsubstituted or substituted with a linear or branched alkyl group having 1 to 30 carbon atoms; a monocyclic or polycyclic heterocyclic group having 2 to 30 carbon atoms unsubstituted or substituted with one or more selected from the group consisting of a linear or branched alkyl group having 1 to 30 carbon atoms, and a monocyclic or polycyclic aryl group having 6 to 30 carbon atoms; and combinations thereof, or being unsubstituted.

In A1, the "substituted or unsubstituted" means being substituted with one or more substituents selected from the group consisting of deuterium; a cumyl group unsubstituted or substituted with deuterium; a methyl group unsubstituted or substituted with deuterium; an isopropyl group; a tert-butyl group; a phenyl group unsubstituted or substituted with one or more selected from the group consisting of deuterium, F, a methyl group, a tert-butyl group and a phenyl group; a diphenylamine group unsubstituted or substituted with one or more selected from the group consisting of deuterium, a methyl group, a tert-butyl group and a trimethylsilyl group; a phenyltetrahydronaphthylamine group unsubstituted or substituted with one or more selected from the group consisting of a methyl group and a tert-butyl group; a phenylbiphenylamine group; a ditetrahydronaphthylamine group unsubstituted or substituted with a methyl group; a phenylfluorenylamine group unsubstituted or substituted with a methyl group; an N-phenyldibenzofuranamine group; a trimethylsilyl group; a triphenylsilyl group; a carbazole group; a hexahydrocarbazole group unsubstituted or substituted with one or more selected from the group consisting of a methyl group and a phenyl group; and combinations thereof, or being unsubstituted.

According to one embodiment of the present specification, A1 is tetrahydronaphthalene; naphthalene; 1,2,2,4-tetrahydro-1,4-methanonaphthalene; 1,2,3,4-tetrahydro-1,4-ethanonaphthalene; benzene; dibenzofuran; dibenzothiophene; fluorene; xanthene; or dibenzosilole, and the substituent may be substituted with one or more substituents selected from the group consisting of deuterium; a cumyl group; a cumyl group substituted with deuterium; a methyl group; an isopropyl group; a tert-butyl group; a phenyl group unsubstituted or substituted with one or more selected from the group consisting of deuterium, F, a methyl group, a tert-butyl group and a phenyl group; a diphenylamine group unsubstituted or substituted with one or more selected from the group consisting of deuterium, a methyl group, a tert-butyl group and a trimethylsilyl group; a phenyltetrahydronaphthylamine group unsubstituted or substituted with one or more selected from the group consisting of a methyl group and a tert-butyl group; a phenylbipbenylamine group; a ditetrahydronaphthylamine group unsubstituted or substituted with a methyl group; a phenylfluorenylamine group unsubstituted or substituted with a methyl group; an N-phenyldibenzofuranamine group; a trimethylsilyl group; a triphenylsilyl group; a carbazole group; a hexahydrocarbazole group unsubstituted or substituted with one or more selected from the group consisting of a methyl group and a phenyl group; and combinations thereof, or may be unsubstituted.

According to one embodiment of the present specification, A2 is a substituted or unsubstituted monocyclic or polycyclic aromatic hydrocarbon ring having 6 to 30 carbon atoms; a substituted or unsubstituted monocyclic or polycyclic aliphatic hydrocarbon ring having 3 to 30 carbon atoms; or a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms.

According to one embodiment of the present specification, A2 is a substituted or unsubstituted monocyclic or polycyclic aromatic hydrocarbon ring having 6 to 20 carbon atoms; a substituted or unsubstituted monocyclic or polycyclic aliphatic hydrocarbon ring having 3 to 20 carbon atoms; or a substituted or unsubstituted fused ring of monocyclic or polycyclic aromatic hydrocarbon ring having 6 to 20 carbon atoms and monocyclic or polycyclic aliphatic hydrocarbon ring having 3 to 20 carbon atoms.

According to one embodiment of the present specification, A2 is substituted or unsubstituted benzene; substituted or unsubstituted cyclohexane; substituted or unsubstituted tetrahydronaphthalene; substituted or unsubstituted 1,2,3,4-tetrahydro-1,4-methanonaphthalene; or substituted or unsubstituted 1,2,3,4-tetrahydro-1,4-ethanonaphthalene.

In A2, the "substituted or unsubstituted" means being substituted with one or more substituents selected from the group consisting of deuterium; a linear or branched alkyl group having 1 to 30 carbon atoms unsubstituted or substituted with one or more selected from the group consisting of deuterium, and a monocyclic or polycyclic aryl group having 6 to 30 carbon atoms; a monocyclic or polycyclic cycloalkyl group having 3 to 30 carbon atoms; a monocyclic or polycyclic aryl group having 6 to 30 carbon atoms unsubstituted or substituted with a linear or branched alkyl group having 1 to 30 carbon atoms; and combinations thereof, or being unsubstituted.

In A2, the "substituted or unsubstituted" means being substituted with one or more substituents selected from the group consisting of deuterium; a cumyl group unsubstituted or substituted with deuterium; a methyl group unsubstituted or substituted with deuterium; an isopropyl group; a tert-butyl group; an adamantyl group; a phenyl group unsubstituted or substituted with a methyl group or a tert-butyl group; and combinations thereof, or being unsubstituted.

According to one embodiment of the present specification, A2 is benzene; cyclohexane; tetrahydronaphthalene; 1,2,3,4-tetrahydro-1,4-methanonaphthalene; or 1,2,3,4-tetrahydro-1,4-ethanonaphthalene, and the substituent may be substituted with one or more substituents selected from the group consisting of deuterium; a cumyl group unsubstituted or substituted with deuterium; a methyl group unsubstituted or substituted with deuterium; an isopropyl group; a tert-butyl group; an adamantyl group; a phenyl group unsubstituted or substituted with a methyl group or a tert-butyl group; and combinations thereof, or my be unsubstituted.

According to one embodiment of the present specification, Ar1 and Ar2 are the same as or different from each other, and each independently a substituted or unsubstituted monocyclic or polycyclic aryl group having 6 to 30 carbon atoms; a substituted or unsubstituted monocyclic or polycyclic heterocyclic group having 2 to 30 carbon atoms; or a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms.

According to one embodiment of the present specification, Ar1 and Ar2 are the same as or different from each other, and each independently a substituted or unsubstituted phenyl group; a substituted or unsubstituted biphenyl group; a substituted or unsubstituted terphenyl group; a substituted or unsubstituted naphthyl group; a substituted or unsubstituted anthracene group; a substituted or unsubstituted phenanthrene group; a substituted or unsubstituted fluorene group; a substituted or unsubstituted dibenzofuran group; a substituted or unsubstituted dibenzothiophene group; a substituted or unsubstituted dibenzosilole group; a substituted or unsubstituted benzofluorene group; a substituted or unsubstituted naphthobenzofuran group; a substituted or unsubstituted naphthobenzothiophene group; a substituted or unsubstituted tetrahydronaphthobenzofuran group; or a substituted or unsubstituted tetrahydronaphthalene group.

In Ar1 and Ar2, the "substituted or unsubstituted" means being substituted with one or more substituents selected from the group consisting of deuterium; a halogen group; a cyano group; a linear or branched alkoxy group having 1 to 30 carbon atoms; a linear or branched alkyl group having 1 to 30 carbon atoms unsubstituted or substituted with one or more selected from the group consisting of deuterium, a halogen group, and a monocyclic or polycyclic aryl group having 6 to 30 carbon atoms; a monocyclic or polycyclic cycloalkyl group having 3 to 30 carbon atoms; a linear or branched alkylsilyl group having 1 to 30 carbon atoms; a monocyclic or polycyclic arylsilyl group having 6 to 30 carbon atoms; NRR' unsubstituted or substituted with a linear or branched alkyl group having 1 to 30 carbon atoms; a fused ring group of monocyclic or polycyclic aromatic hydrocarbon ring having 6 to 30 carbon atoms and monocyclic or polycyclic aliphatic hydrocarbon ring having 3 to 30 carbon atoms unsubstituted or substituted with a linear or branched alkyl group having 1 to 30 carbon atoms; a monocyclic or polycyclic aryl group having 6 to 30 carbon atoms unsubstituted or substituted with one or more selected from the group consisting of deuterium, a halogen group, a cyano group, a linear or branched haloalkyl group having 1 to 30 carbon atoms, a linear or branched alkylsilyl group having 1 to 30 carbon atoms, and a linear or branched alkyl group having 1 to 30 carbon atoms unsubstituted or substituted with deuterium; and combinations thereof, or being unsubstituted.

In Ar1 and Ar2, the "substituted or unsubstituted" means being substituted with one or more substituents selected from the group consisting of deuterium; F; a cyano group; a methoxy group; a trifluoromethyl group; a trideuteriummethyl group; a methyl group; an isopropyl group; a tert-butyl group; an n-butyl group; a cumyl group unsubstituted or substituted with deuterium; a cyclohexyl group; a trimethylsilyl group; a triphenylsilyl group; a phenyl group unsubstituted or substituted with one or more substituents selected from the group consisting of deuterium, F, a cyano group, a trifluoromethyl group, a trideuteriummethyl group, a trimethylsilyl group, a methyl group, an isopropyl group, a tert-butyl group and a phenyl group; a naphthyl group unsubstituted or substituted with deuterium; a biphenyl group; a phenanthrene group; an anthracene group; a tetrahydronaphthyl group unsubstituted or substituted with a methyl group; NRR'; and combinations thereof, or being unsubstituted, and R and R' are the same as or different from each other, and each independently a phenyl group unsubstituted or substituted with a methyl group or a tert-butyl group; a biphenyl group; or a tetrahydronaphthyl group unsubstituted or substituted with a methyl group.

According to one embodiment of the present specification, Ar1 and Ar2 are the same as or different from each other, and each independently a phenyl group; a biphenyl group; a terphenyl group; a naphthyl group; an anthracene group; a phenanthrene group; a fluorene group; a dibenzofuran group; a dibenzothiophene group; a dibenzosilole group; a benzofluorene group; a naphthobenzofuran group; a naphthobenzothiophene group; a tetrahydronaphthobenzofuran group; or a tetrahydronaphthalene group, the substituent may be substituted with one or more substituents selected from the group consisting of deuterium; F; a cyano group; a methoxy group; a trifluoromethyl group; a trideuteriummethyl group; a methyl group; an isopropyl group; a tert-butyl group; an n-butyl group; a cumyl group unsubstituted or substituted with deuterium; a cyclohexyl group; a trimethylsilyl group; a triphenylsilyl group; a phenyl group unsubstituted or substituted with one or more substituents selected from the group consisting of deuterium, F, a cyano group, a trifluoromethyl group, a trideuteriummethyl group, a trimethylsilyl group, a methyl group, an isopropyl group, a tert-butyl group and a phenyl group; a naphthyl group unsubstituted or substituted with deuterium; a biphenyl group; a phenanthrene group; an anthracene group; a tetrahydronaphthyl group unsubstituted or substituted with a methyl group; NRR'; and combinations thereof, or may be unsubstituted, and R and R' are the same as or different from each other, and each independently a phenyl group unsubstituted or substituted with a methyl group or a tert-butyl group; a biphenyl group; or a tetrahydronaphthyl group unsubstituted or substituted with a methyl group.

According to one embodiment of the present specification, R1 is hydrogen; a substituted or unsubstituted linear or branched alkyl group having 1 to 30 carbon atoms; a substituted or unsubstituted monocyclic or polycyclic cycloalkyl group having 3 to 30 carbon atoms; a substituted or unsubstituted amine group; a substituted or unsubstituted monocyclic or polycyclic aryl group having 6 to 30 carbon atoms; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a monocyclic or polycyclic heterocyclic group having 2 to 30 carbon atoms, and the amine group is represented by NR"R'".

According to one embodiment of the present specification, R1 is hydrogen; a substituted or unsubstituted methyl group; a substituted or unsubstituted ethyl group; a substituted or unsubstituted isopropyl group; a substituted or unsubstituted n-butyl group; a substituted or unsubstituted tert-butyl group; a substituted or unsubstituted cyclohexyl group; a substituted or unsubstituted adaxnantyl group; a substituted or unsubstituted hexahydrocarbazole group; a substituted or unsubstituted carbazole group; a substituted or unsubstituted fluorene group; a substituted or unsubstituted dihydroacridine group; a substituted or unsubstituted dihydrobenzoazasiline group; a substituted or unsubstituted phenoxazine group; a substituted or unsubstituted phenothiazine group; a substituted or unsubstituted phenyl group; a substituted or unsubstituted biphenyl group; a substituted or unsubstituted naphthyl group; a substituted or unsubstituted tetrahydronaphthyl group; a substituted or unsubstituted decahydrobenzocarbazole group; or substituted or unsubstituted NR"/R'", and R" and R'" are the same as or different from each other, and each independently a substituted or unsubstituted phenyl group; a substituted or unsubstituted biphenyl group; a substituted or unsubstituted dibenzofuran group; a substituted or unsubstituted naphthyl group; a substituted or unsubstituted dibenzothiophene group; a substituted or unsubstituted fluorene group; or a substituted or unsubstituted tetrahydronaphthyl group.

In R1, R" and R'", the "substituted or unsubstituted" means being substituted with one or more substituents selected from the group consisting of deuterium; a halogen group; a cyano group; a linear or branched alkyl group having 1 to 30 carbon atoms unsubstituted or substituted with deuterium, or a monocyclic or polycyclic aryl group having 6 to 30 carbon atoms; a linear or branched alkoxy group having 1 to 30 carbon atoms unsubstituted or substituted with a halogen group; a linear or branched alkylsilyl group having 1 to 30 carbon atoms; a monocyclic or polycyclic arylsilyl group having 6 to 30 carbon atoms; a monocyclic or polycyclic arylamine group having 6 to 30 carbon atoms; a monocyclic or polycyclic aryl group having 6 to 30 carbon atoms unsubstituted or substituted with deuterium; a monocyclic or polycyclic heterocyclic group having 2 to 30 carbon atoms unsubstituted or substituted with a linear or branched alkyl group having 1 to 30 carbon atoms; and combinations thereof, or being unsubstituted.

In R1, R" and R'", the "substituted or unsubstituted" means being substituted with one or more substituents selected from the group consisting of deuterium; F; a cyano group; a methoxy group; a trifluoromethyl group; a trideuteriummethyl group; a trifluoromethoxy group; a trimethylsilyl group; a terphenylsilyl group; a dimethyltert-butylsilyl group; a methyl group unsubstituted or substituted with deuterium; a cumyl group unsubstituted or substituted with deuterium; an isopropyl group; a tert-butyl group; a phenyl group unsubstituted or substituted with deuterium; a carbazole group unsubstituted or substituted with a tert-butyl group; and combinations thereof, or being unsubstituted.

According to one embodiment of the present specification, R1 is hydrogen; a methyl group; an ethyl group; an isopropyl group; an n-butyl group; a tert-butyl group; a cyclohexyl group; an adamantyl group; a hexahydrocarbazole group; a carbazole group; a fluorene group; a dihydroacridine group; a dihydrobenzoazasiline group; a phenozazine group; a phenothiazine group; a phenyl group; a biphenyl group; a naphthyl group; a tetrahydronaphthyl group; a decahydrobenzocarbazole group; or NR"R'", and R" and R'" are the same as or different from each other, and each independently a phenyl group; a biphenyl group; a dibenzofuran group; a naphthyl group; a dibenzothiophene group; a fluorene group; or a tetrahydronaphthyl group. The substituent may be substituted with one or more substituents selected from the group consisting of deuterium; F; a cyano group; a methoxy group; a trifluoromethyl group; a trideuteriummethyl group; a trifluoromethoxy group; a trimethylsilyl group; a terphenylsilyl group; a dimethyltert-butylsilyl group; a methyl group unsubstituted or substituted with deuterium; a cumyl group unsubstituted or substituted with deuterium; an isopropyl group; a tert-butyl group; a phenyl group unsubstituted or substituted with deuterium; a carbazole group unsubstituted or substituted with a tert-butyl group; and combinations thereof, or may be unsubstituted.

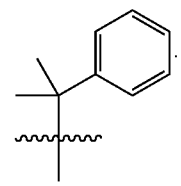 [SMILES: *C(C)(C)c1ccccc1]

According to one embodiment of the present specification, Chemical Formula 1 is any one selected from among the following compounds.

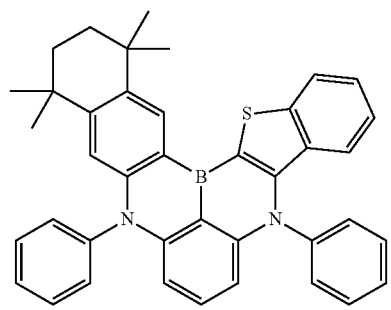

-continued
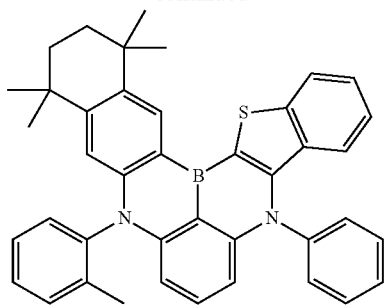
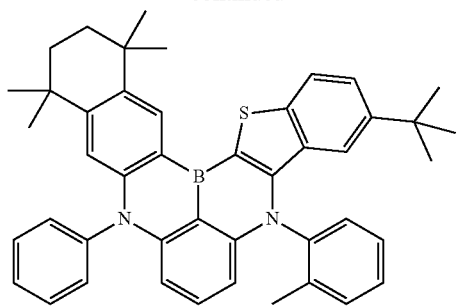
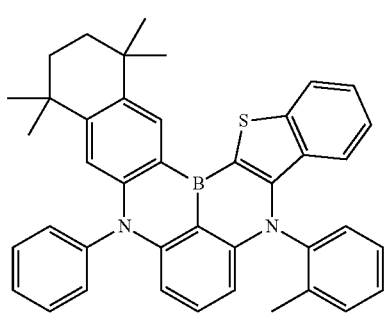
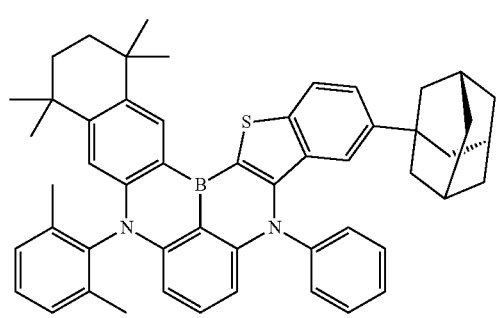
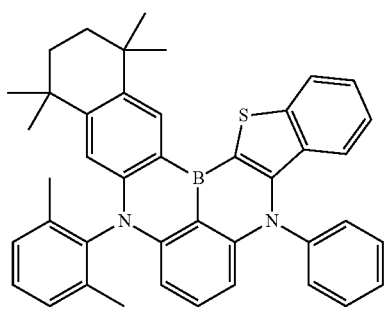
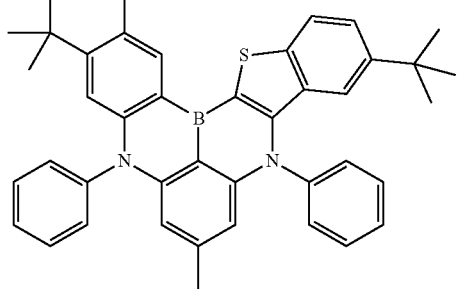
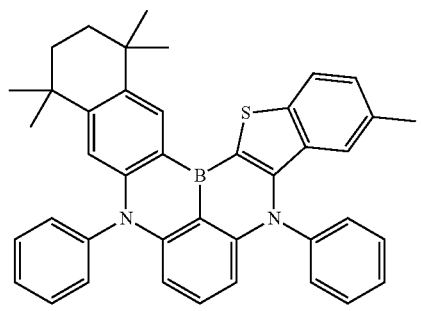
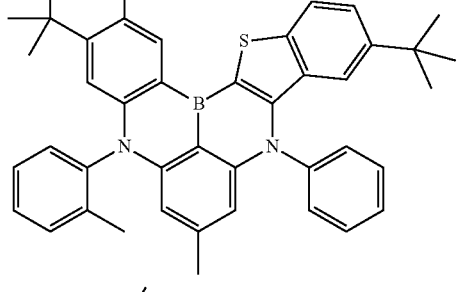
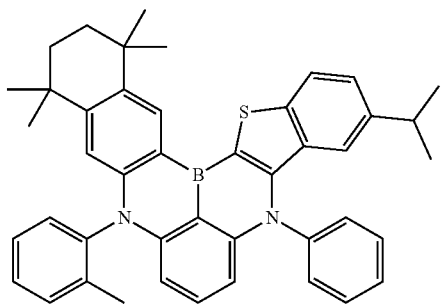

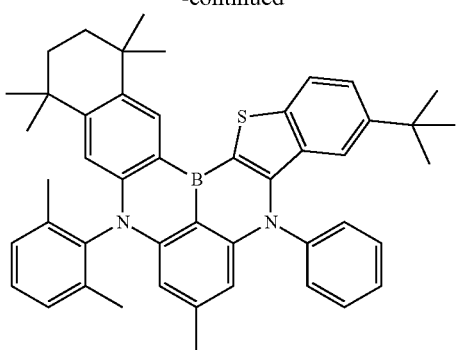
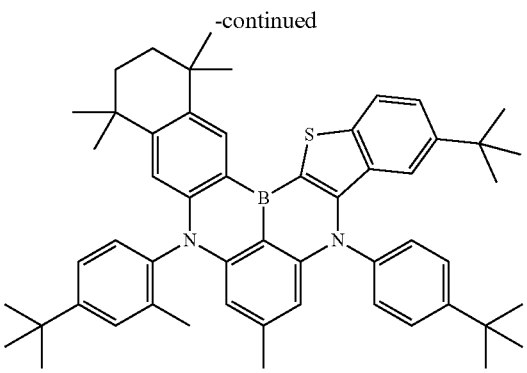
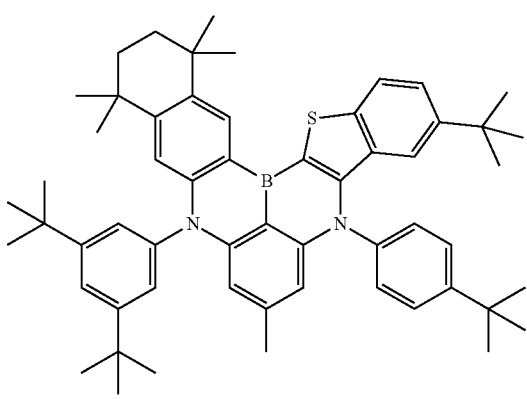
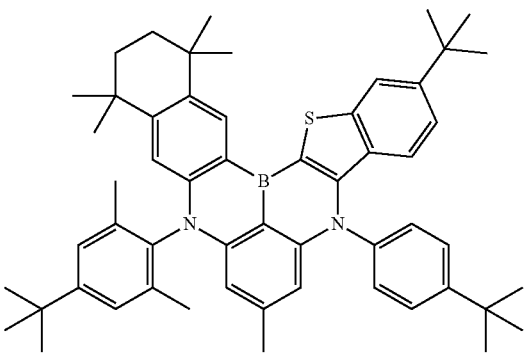
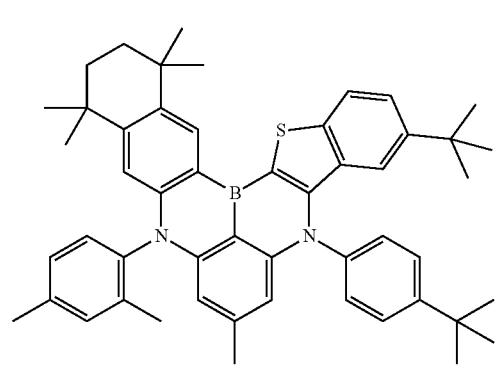
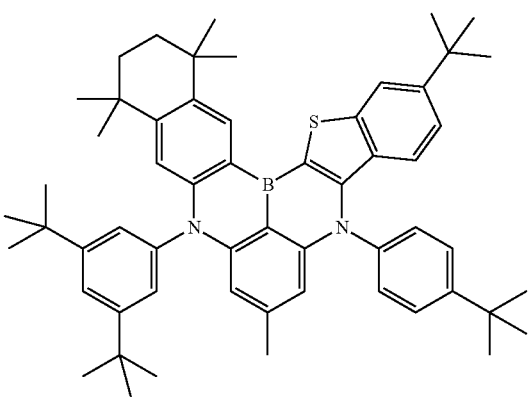

31
-continued
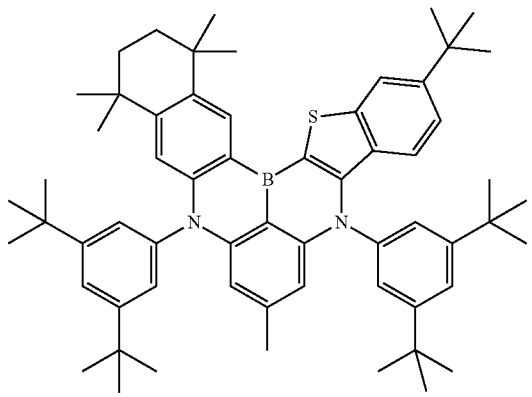
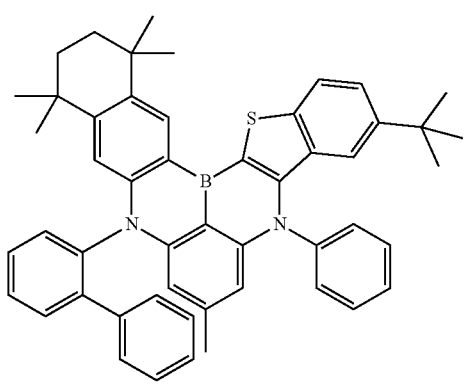
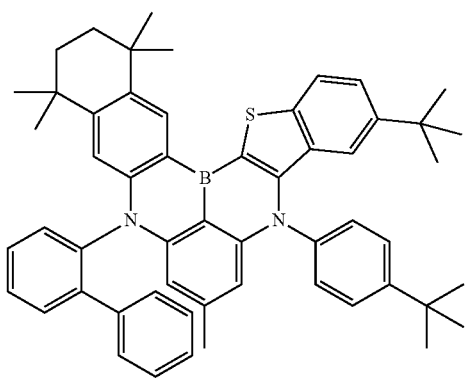
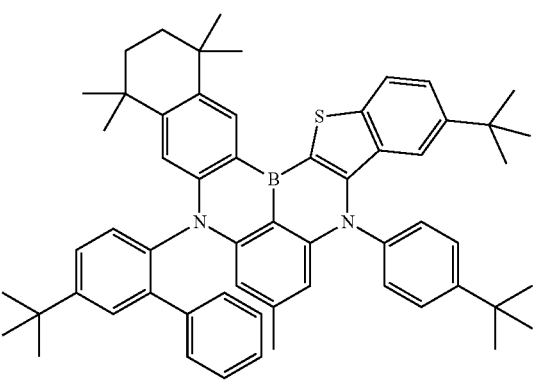
32
-continued
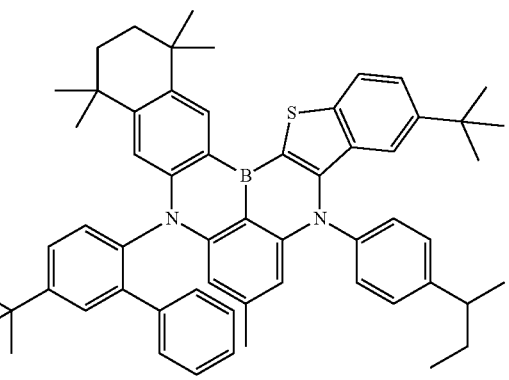
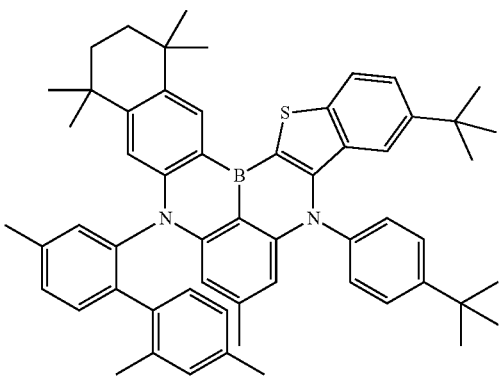
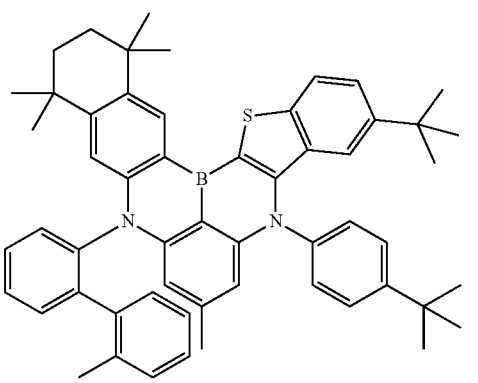
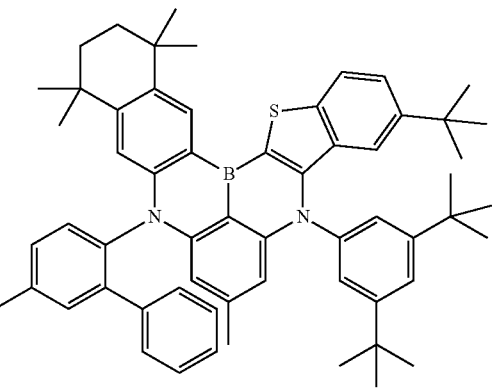

33
-continued
34
-continued
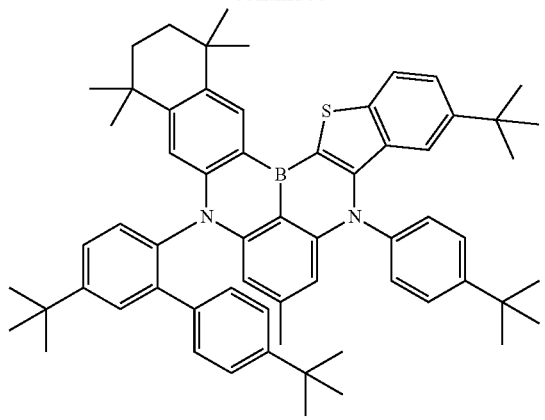
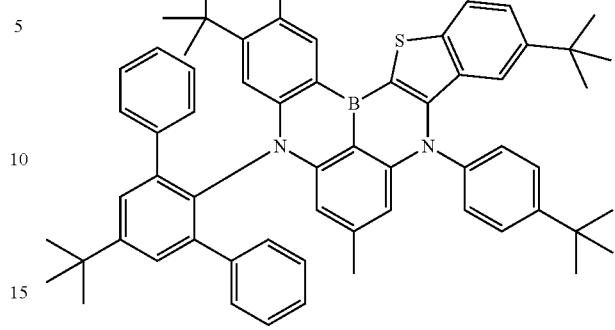
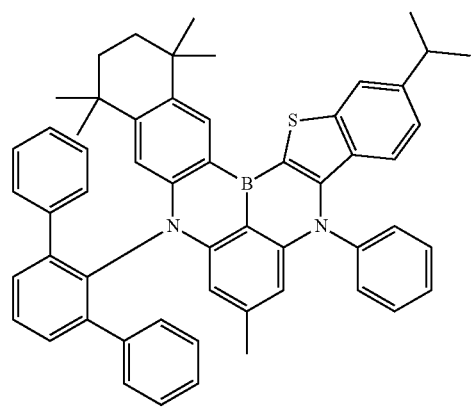
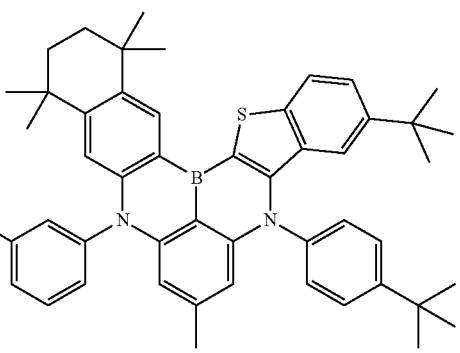
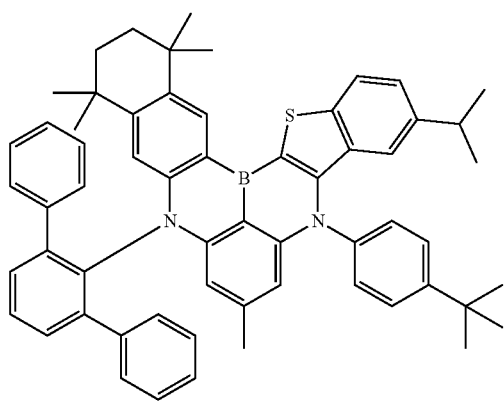
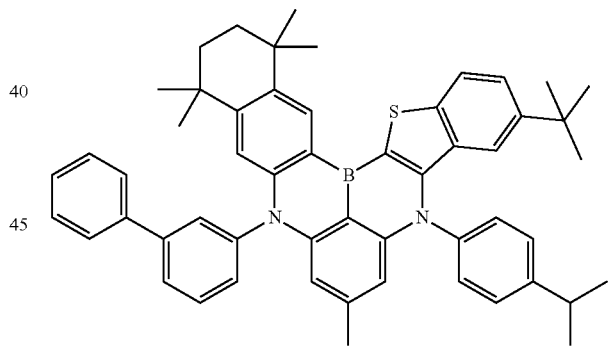
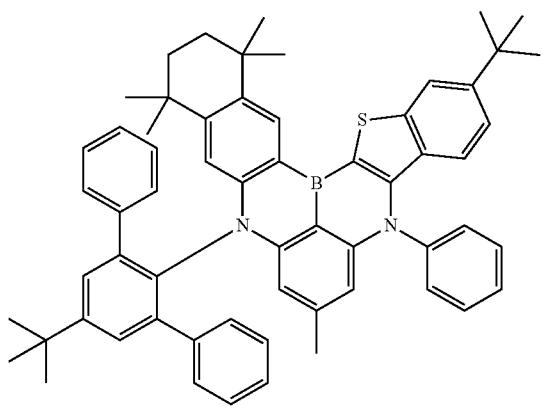
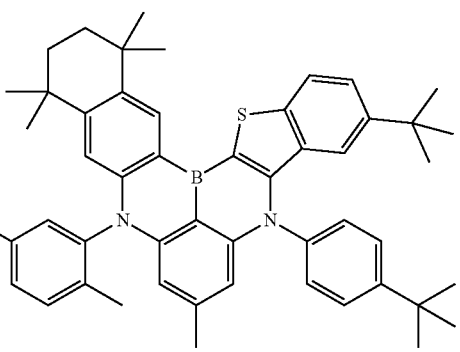

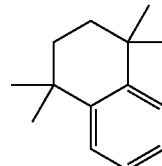
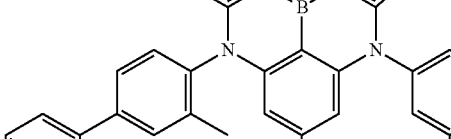

-continued
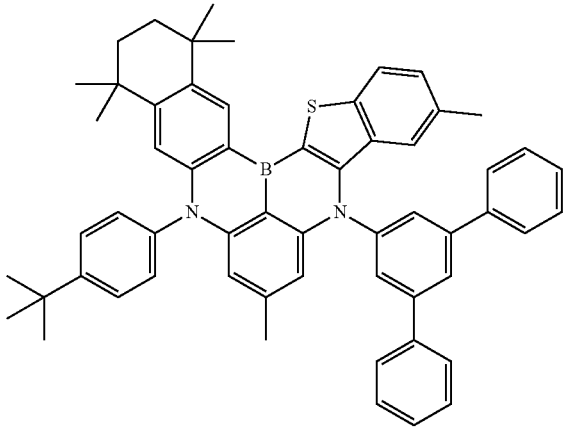
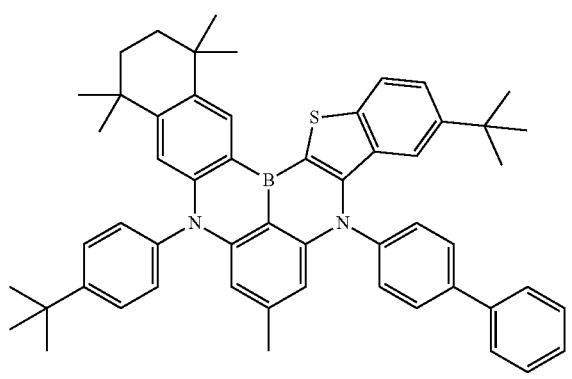
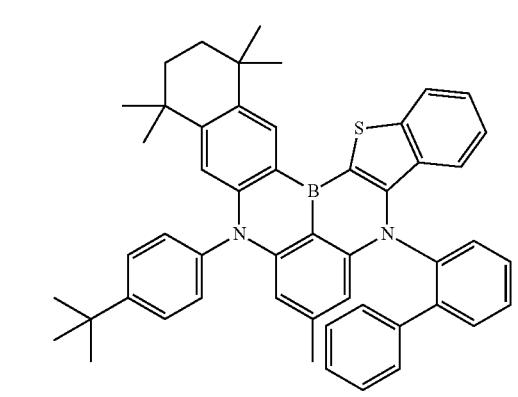
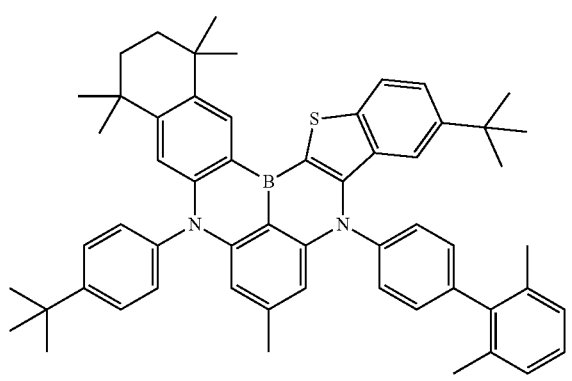
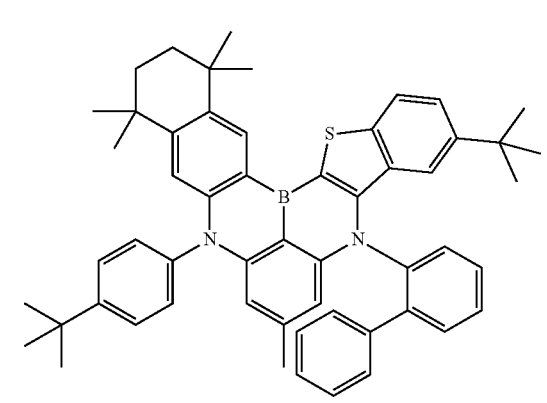
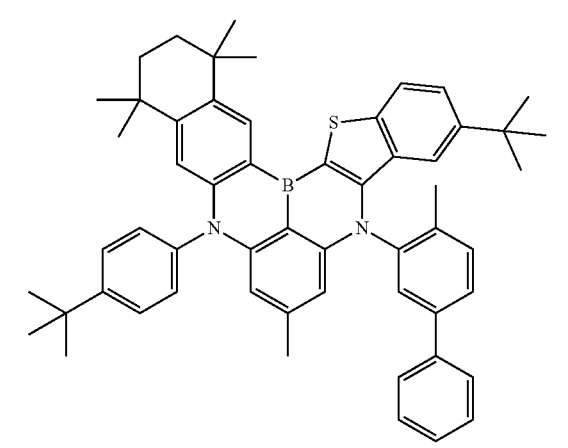
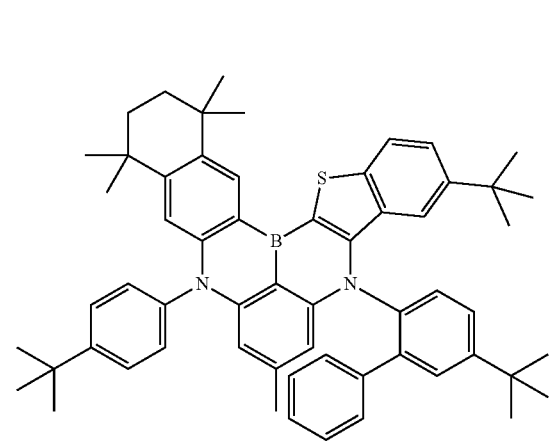

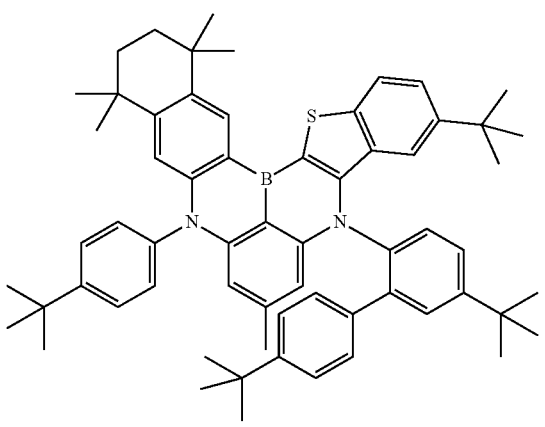
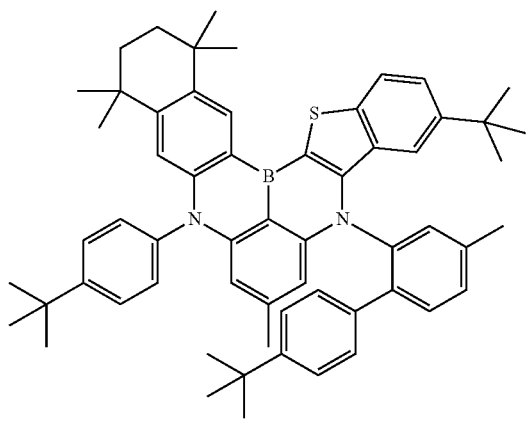
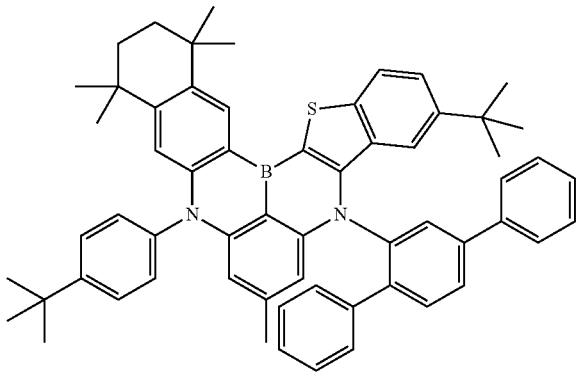

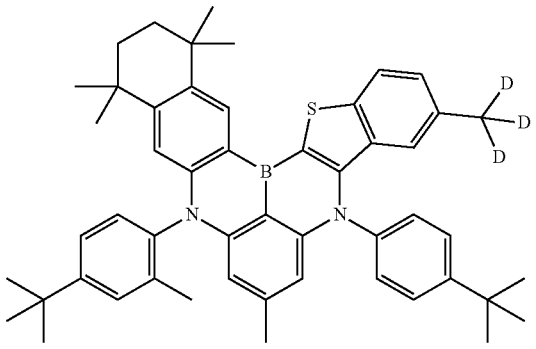
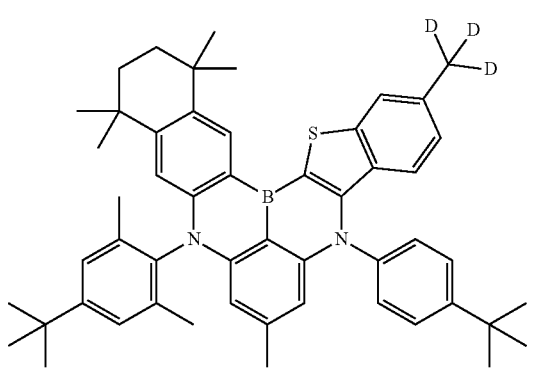
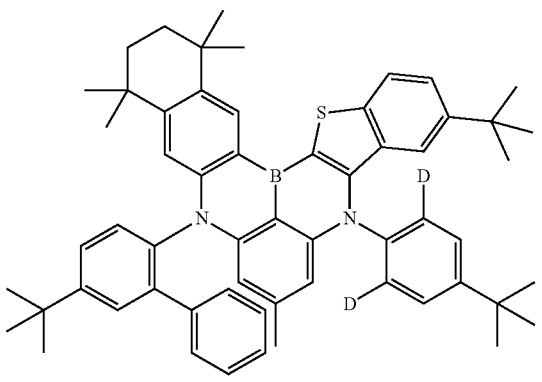
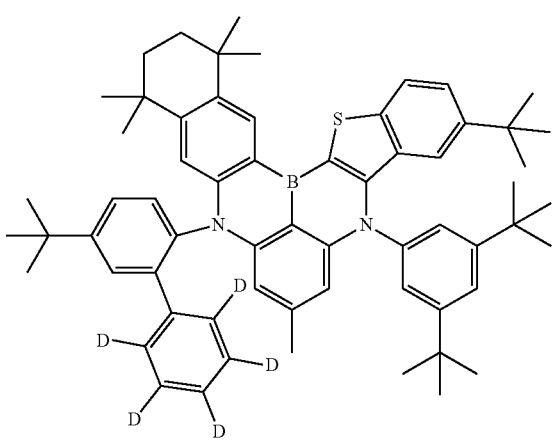
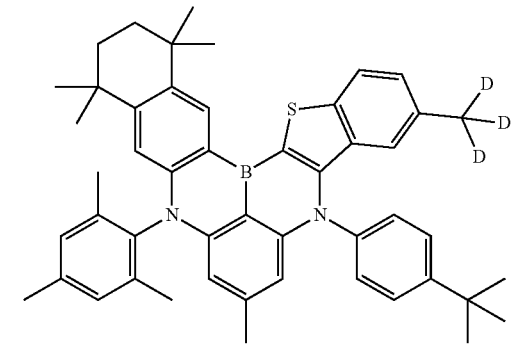
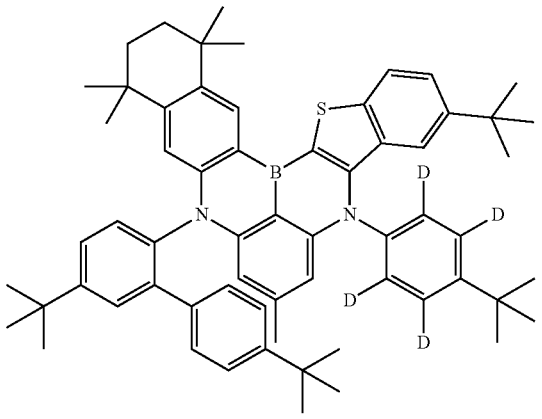

-continued
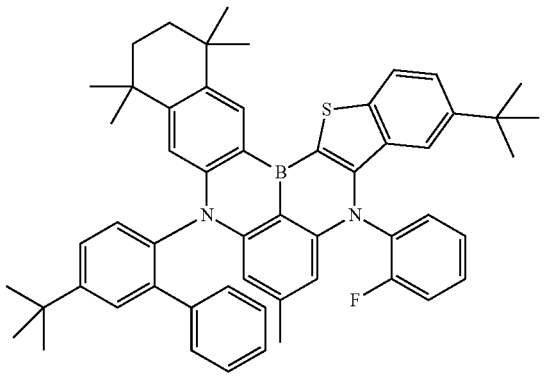
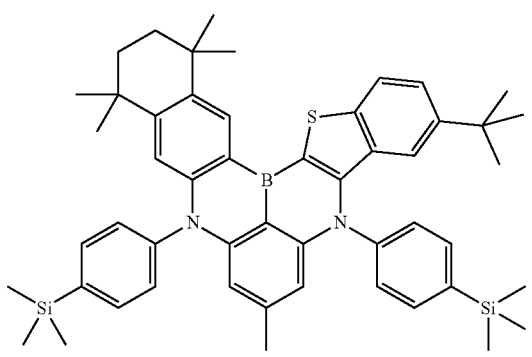
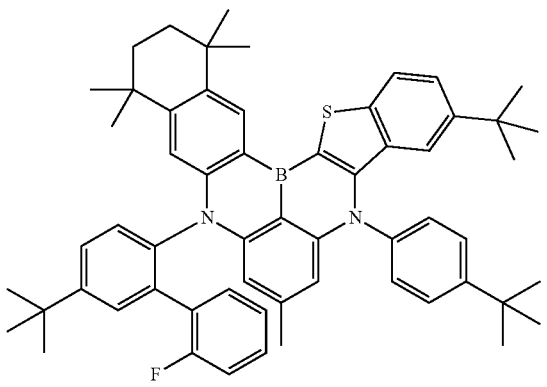
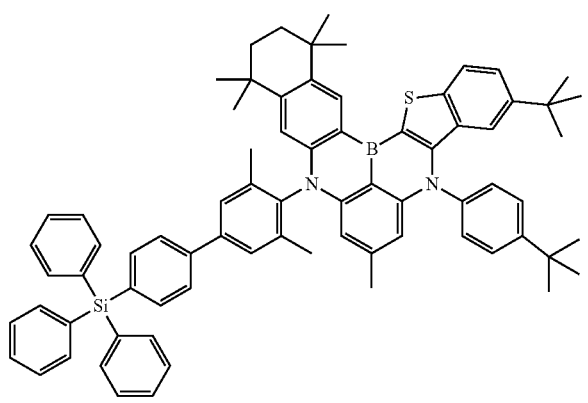
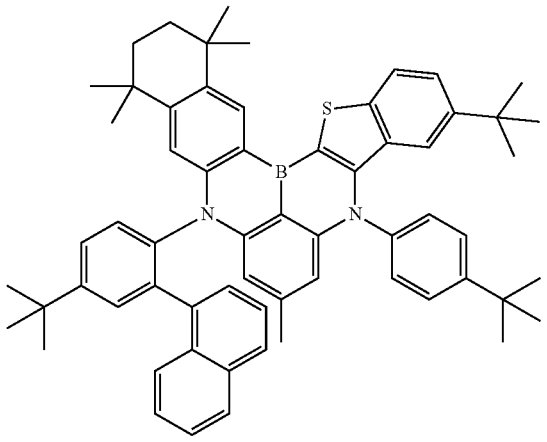
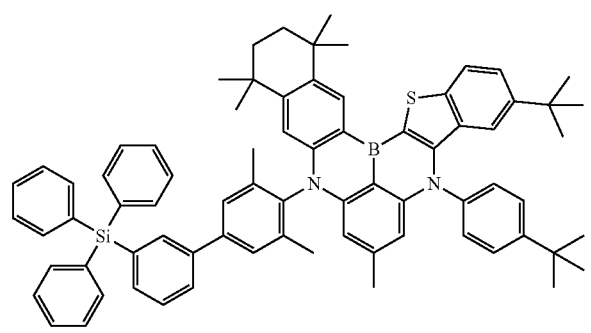
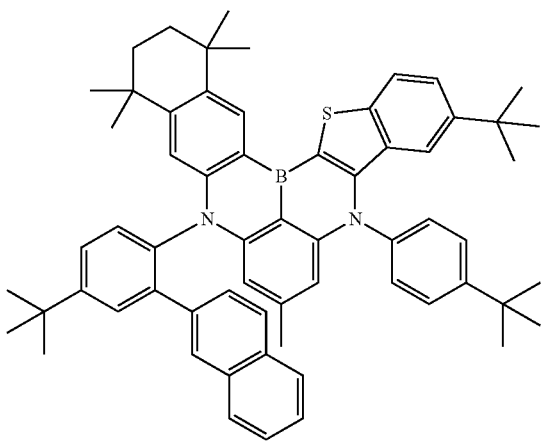

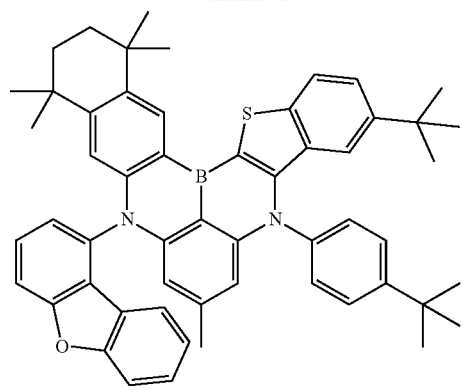
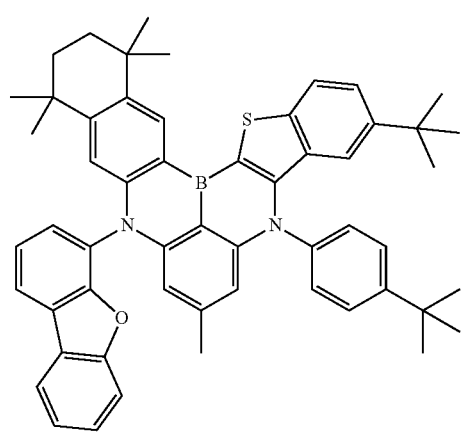
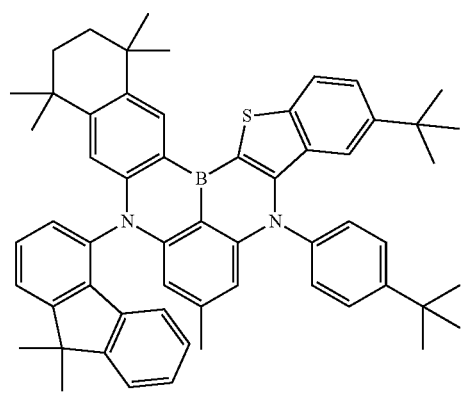
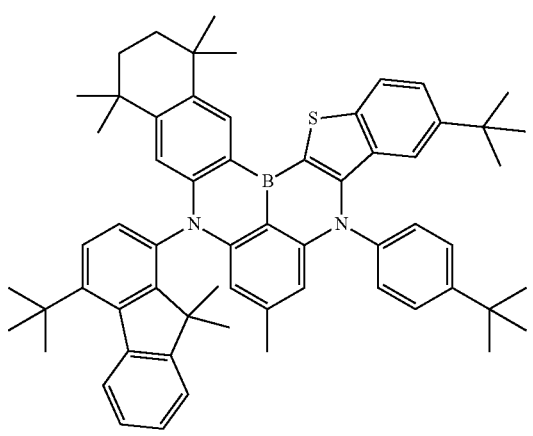

47
-continued
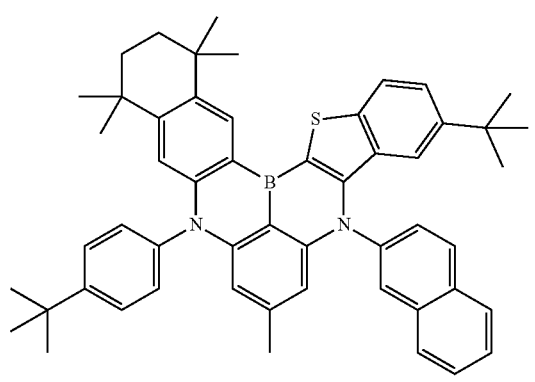
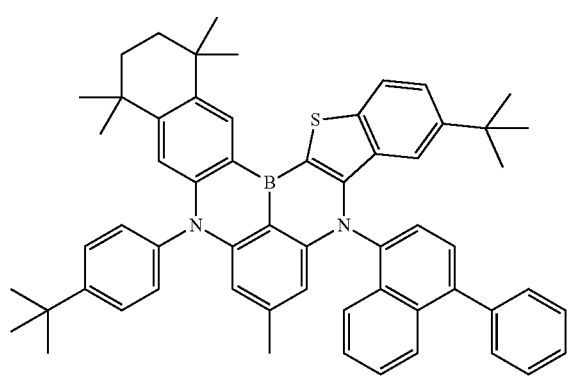
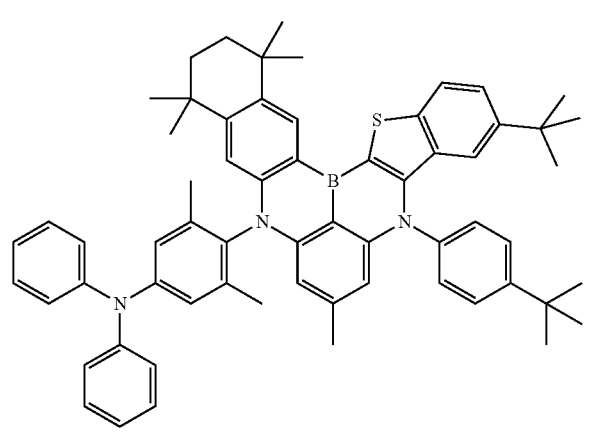
48
-continued
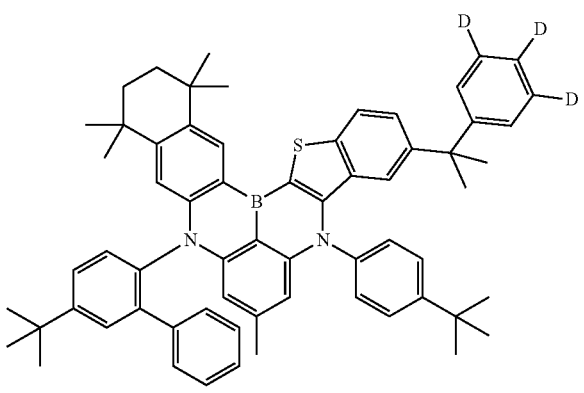
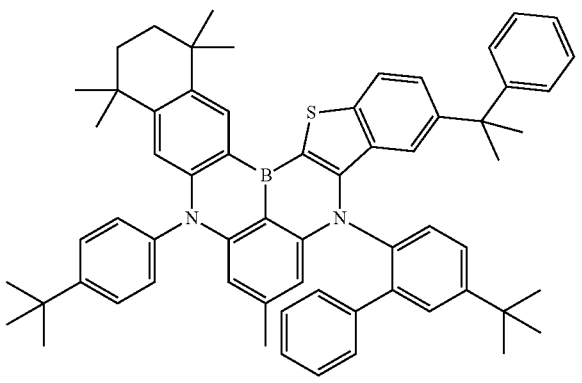
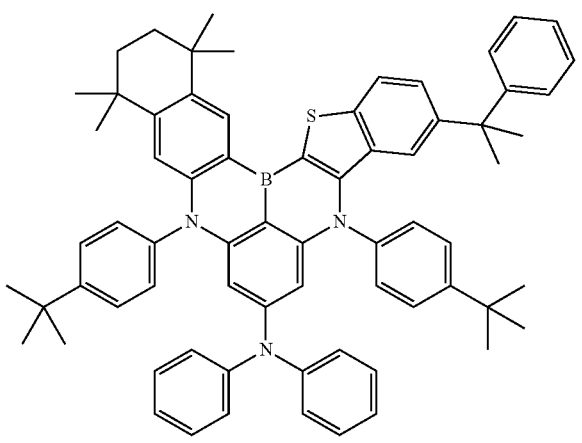

51
-continued
52
-continued
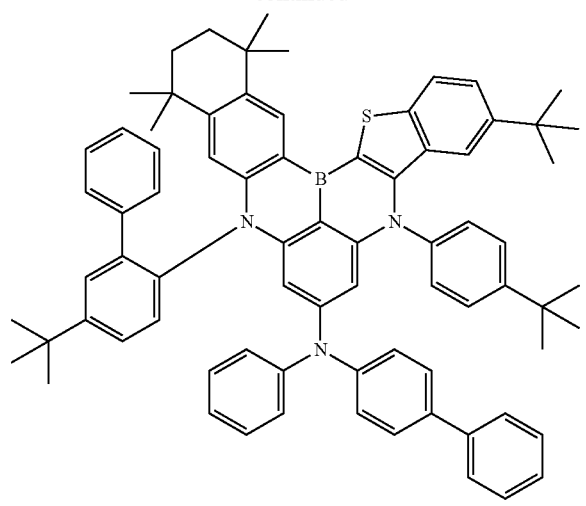
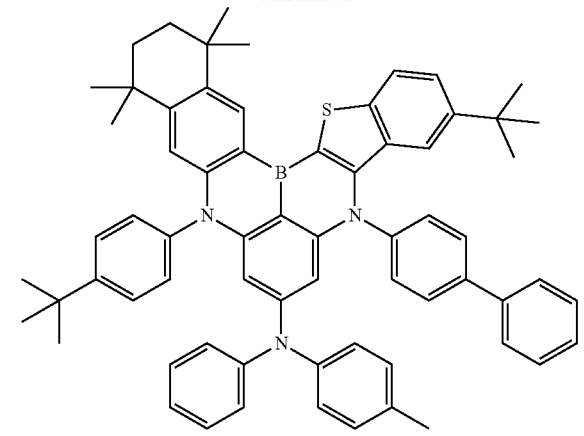
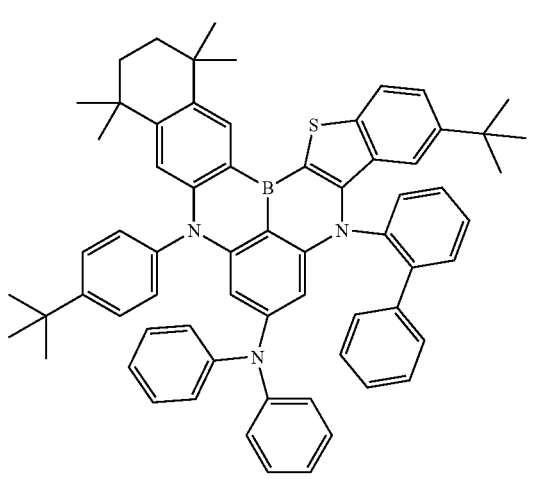
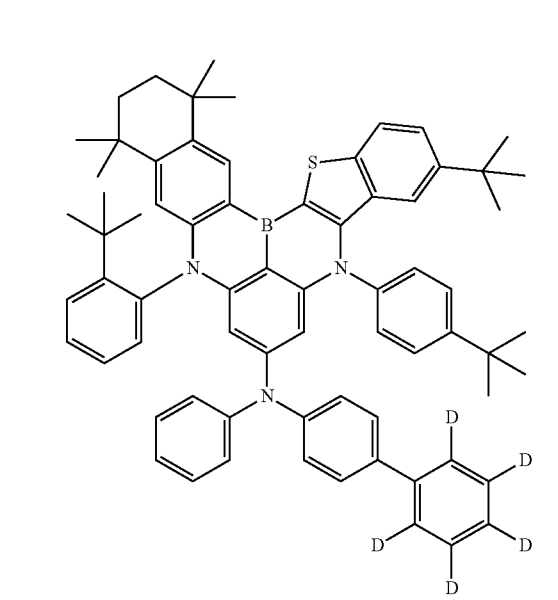

53
-continued
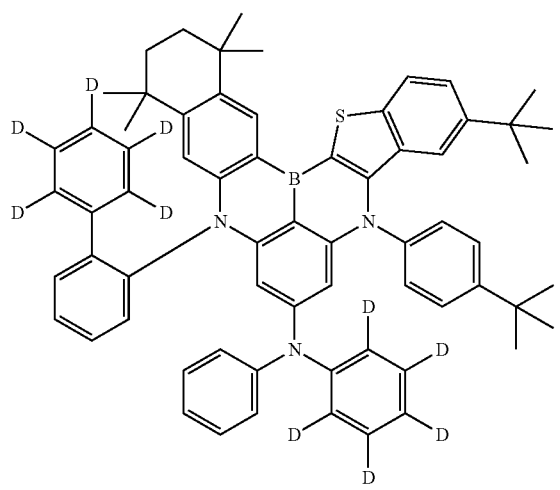
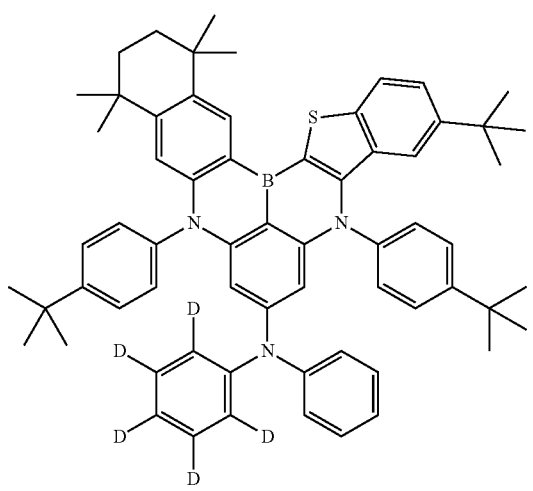
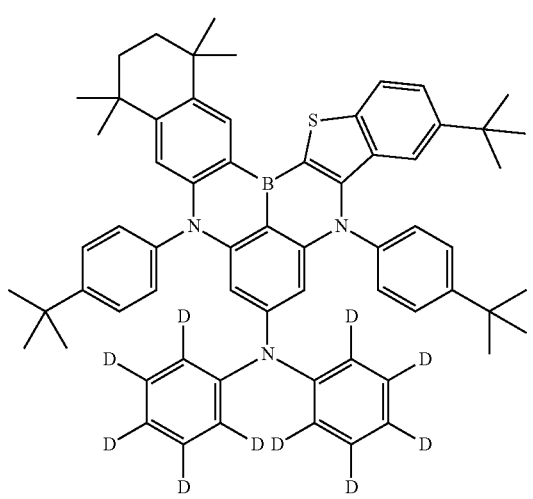
54
-continued
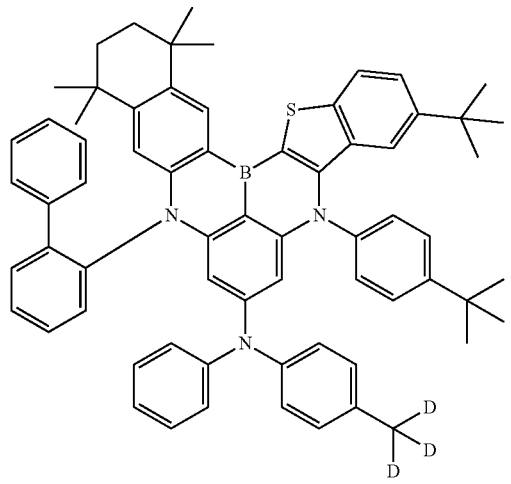
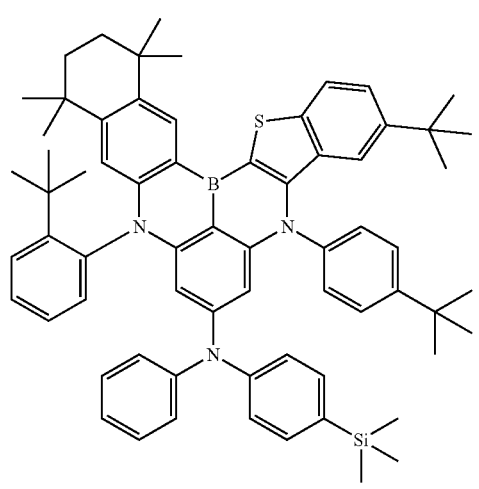
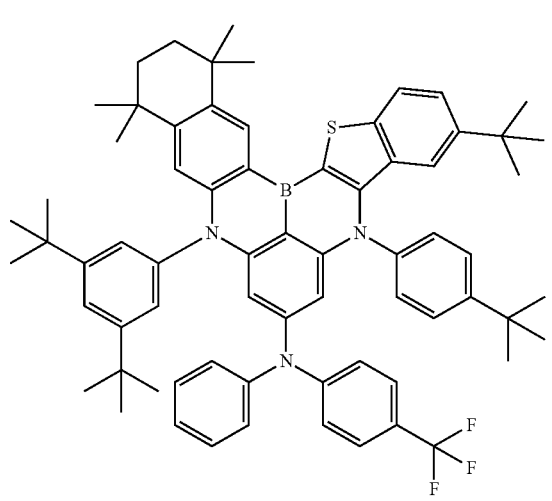

55
-continued
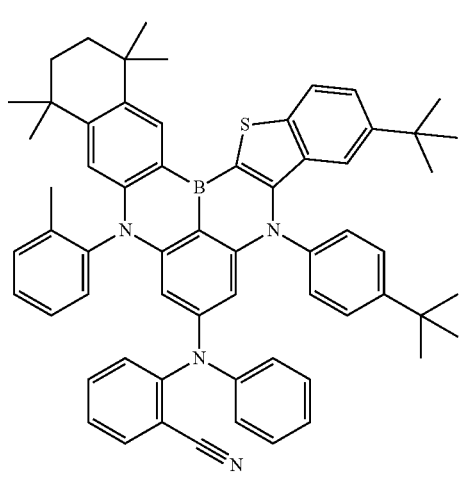
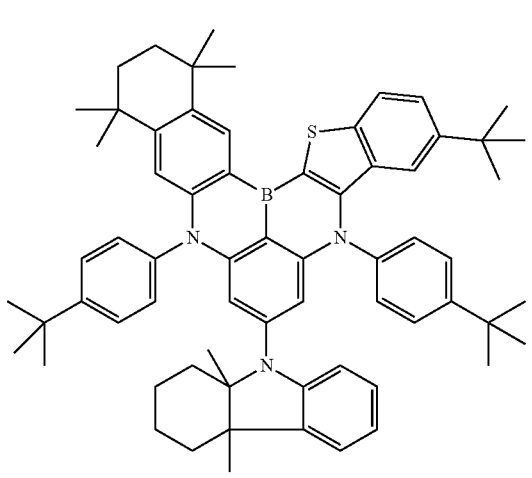
56
-continued
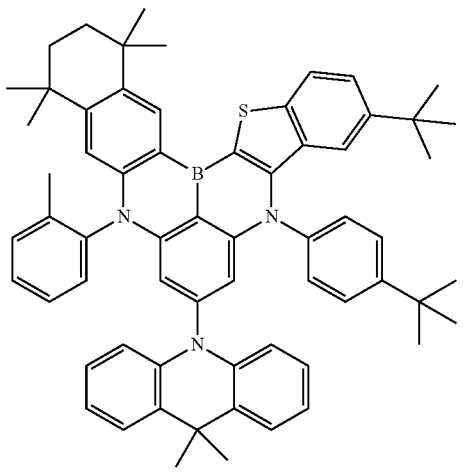

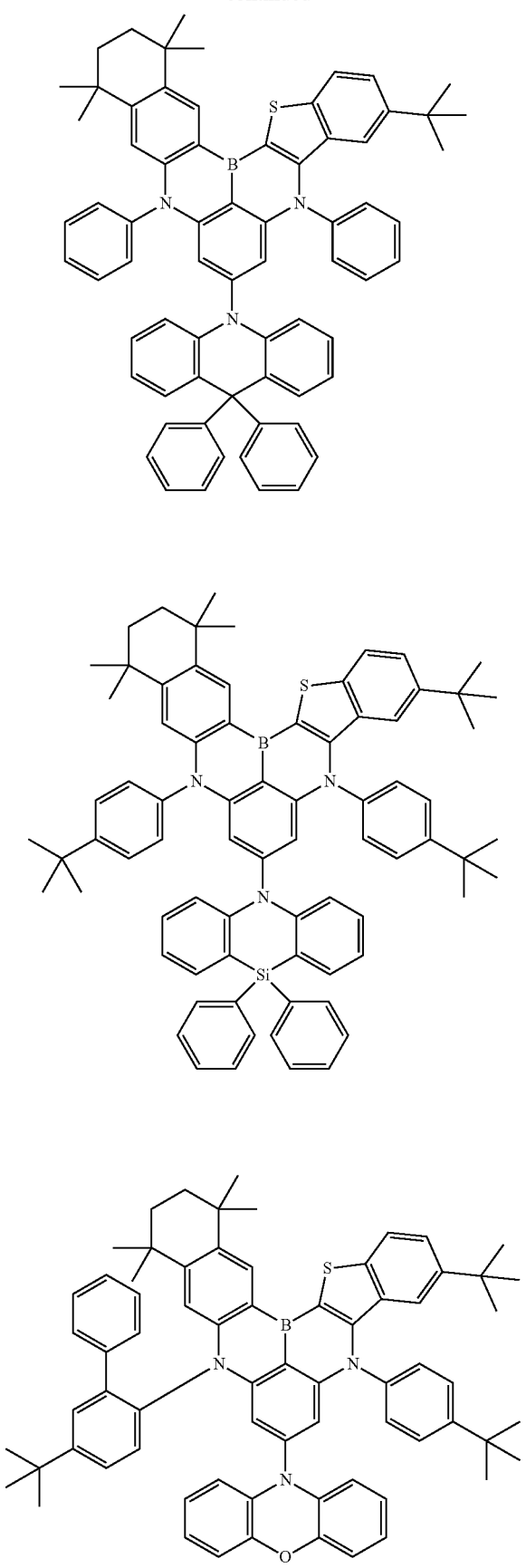

59
-continued
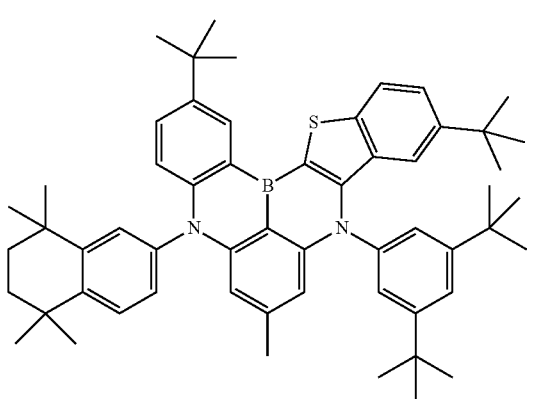
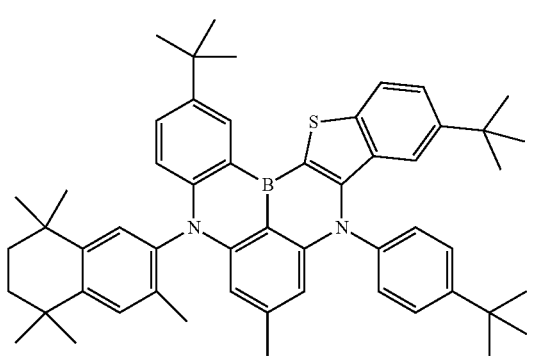
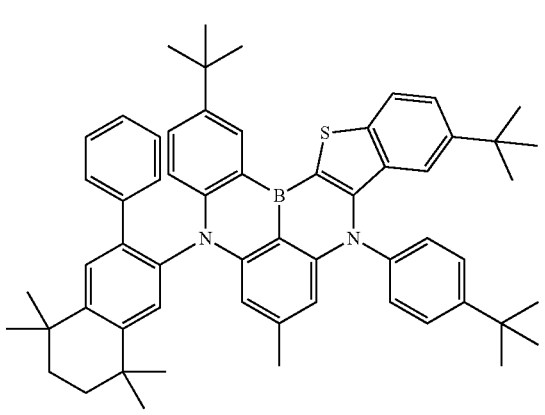
60
-continued
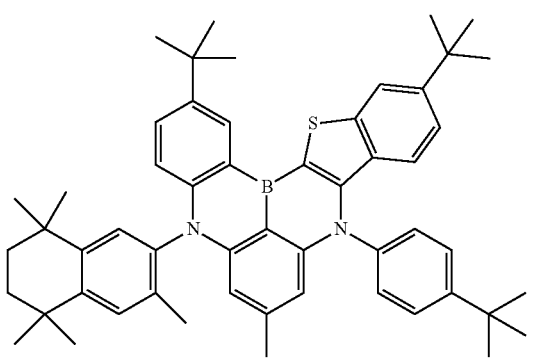
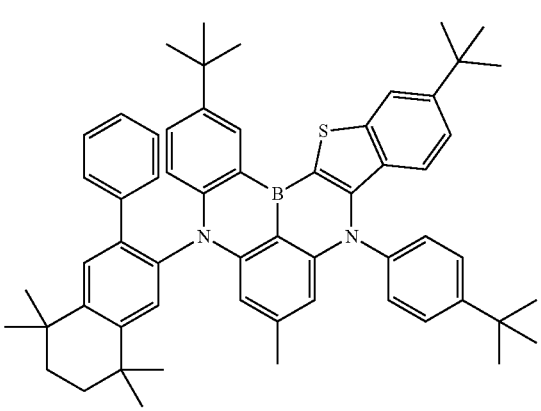

61
-continued
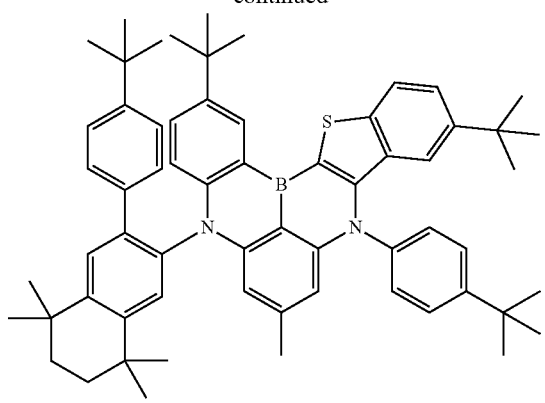
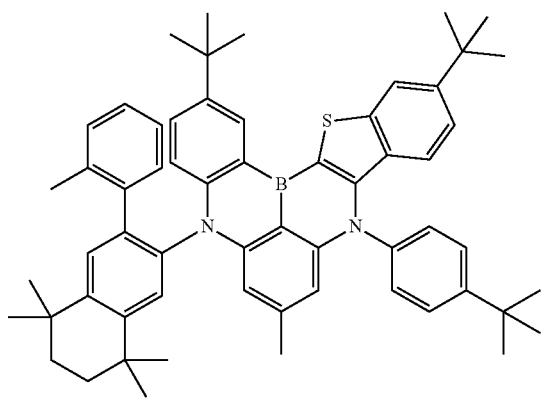
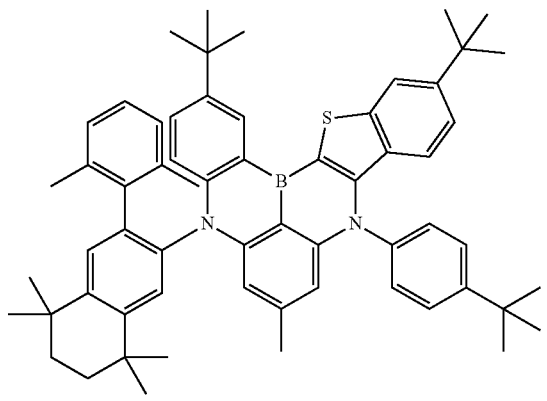
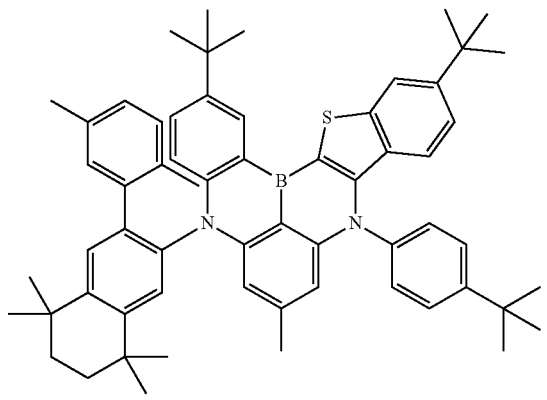
62
-continued
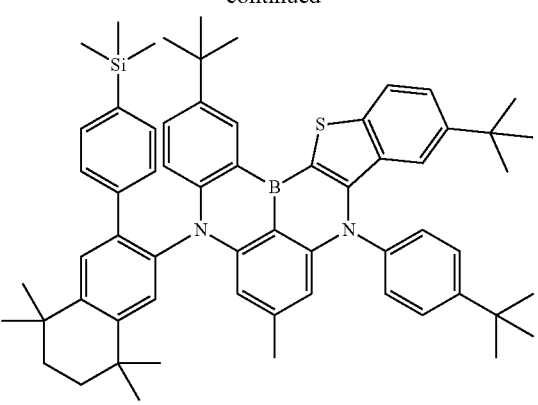
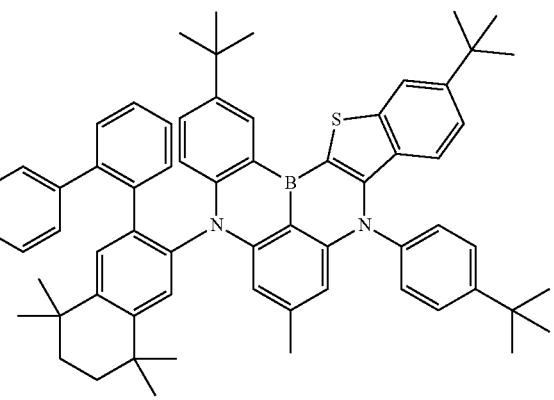
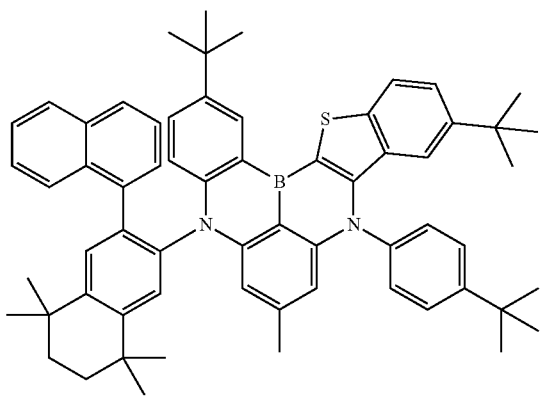
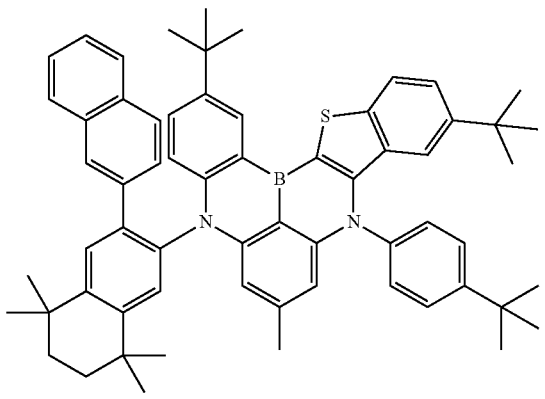

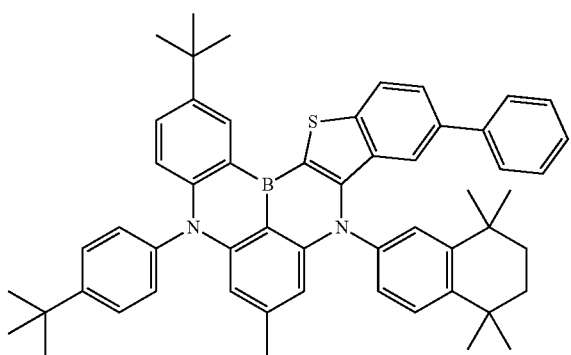
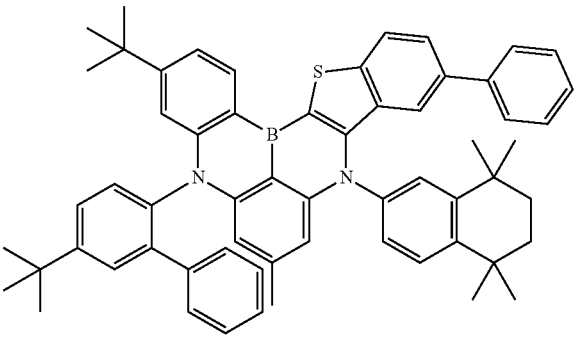
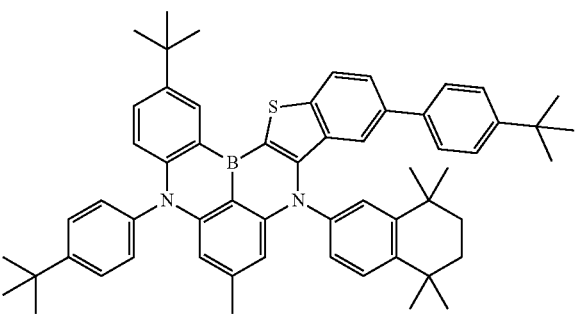
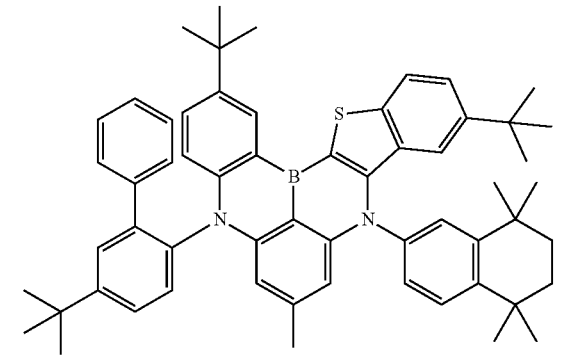
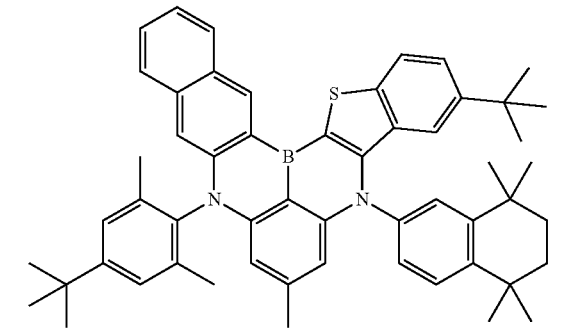
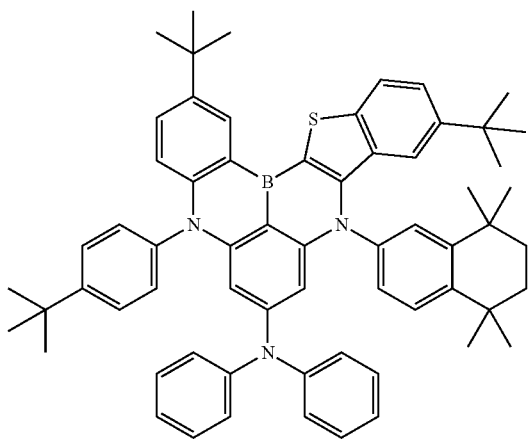
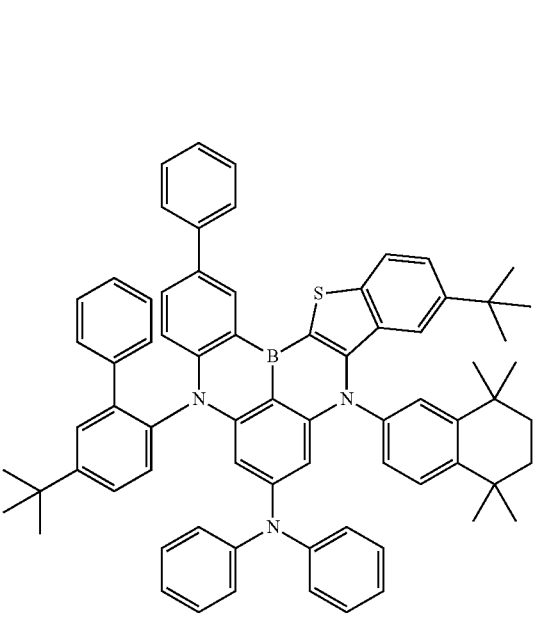

65
-continued
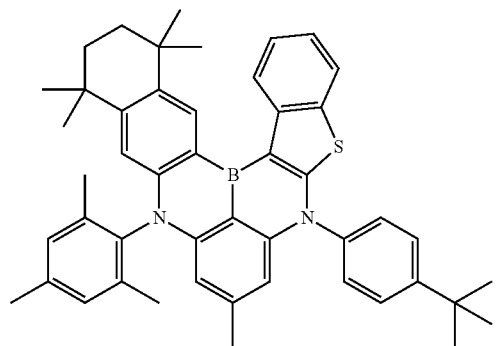
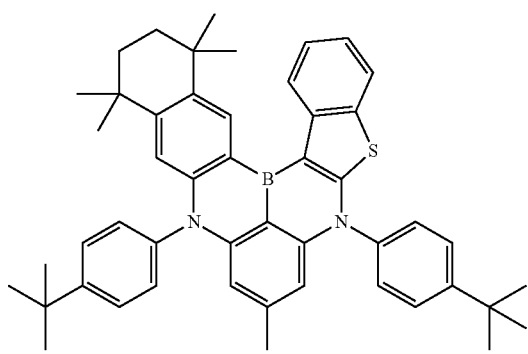
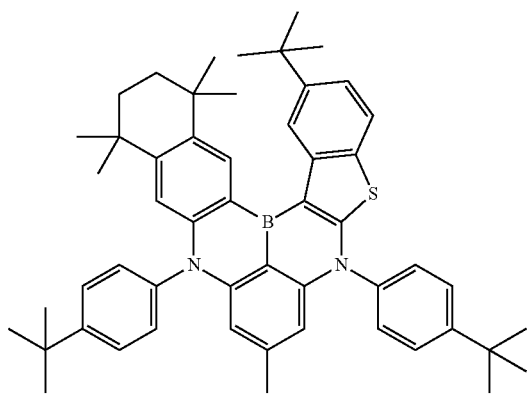
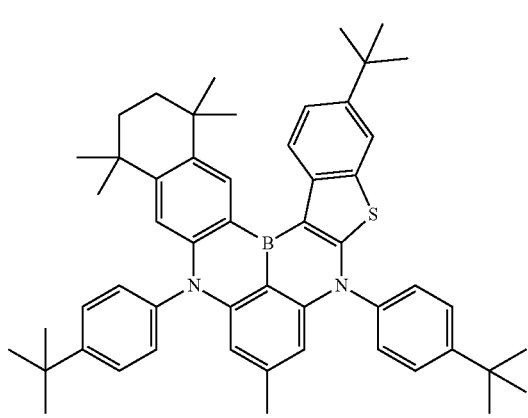
66
-continued
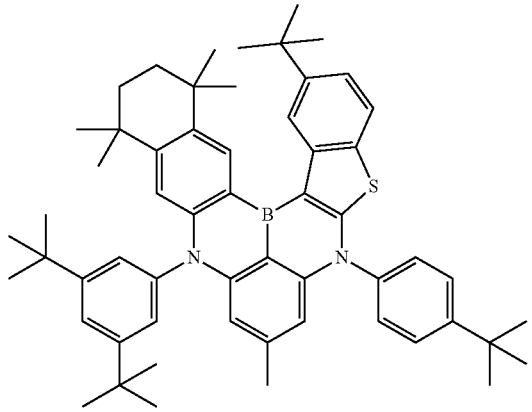
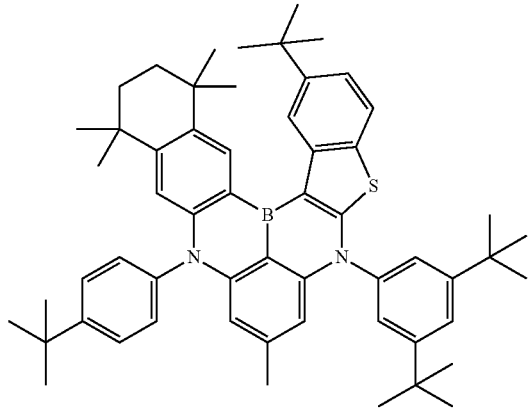
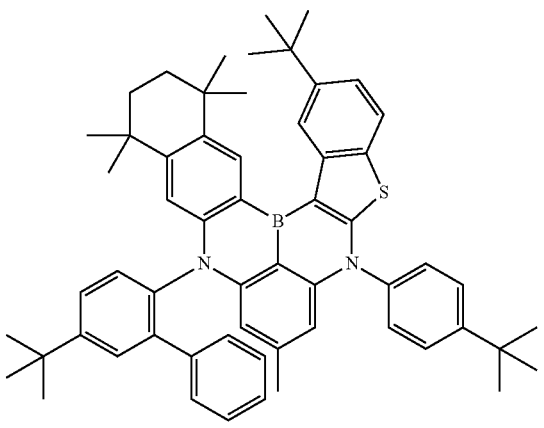
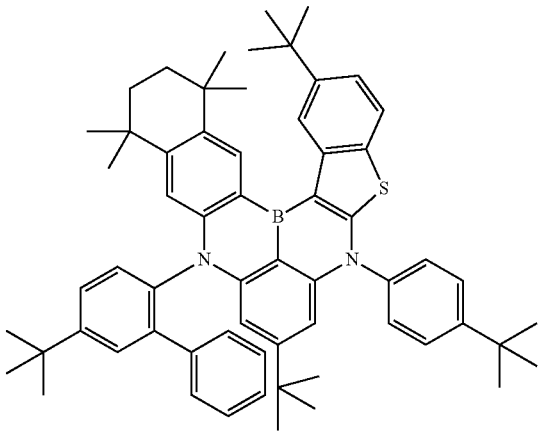

-continued
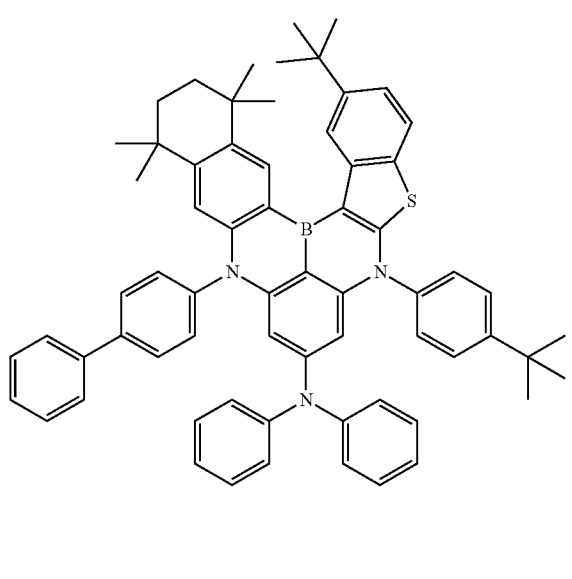
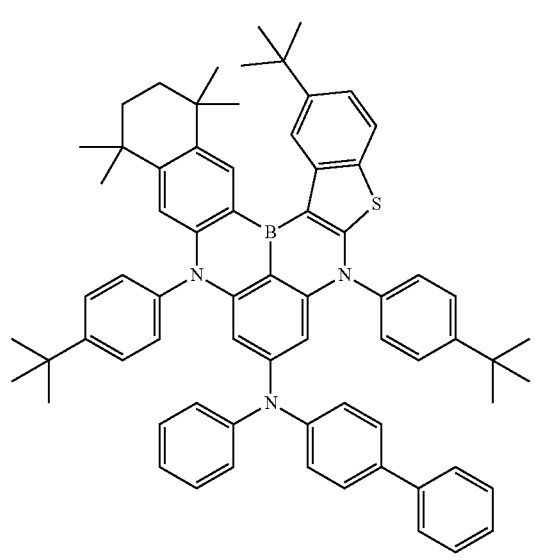
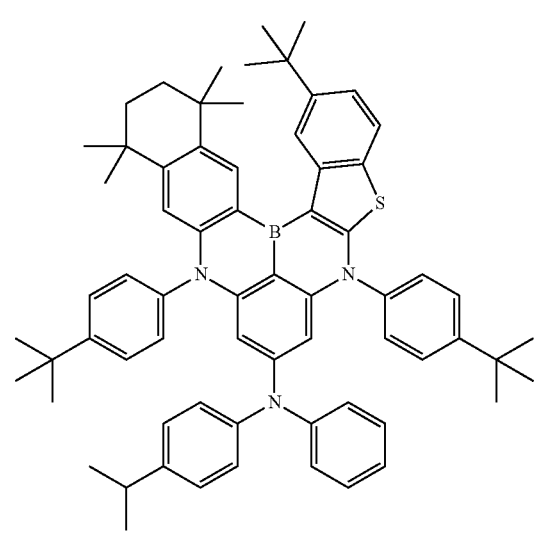
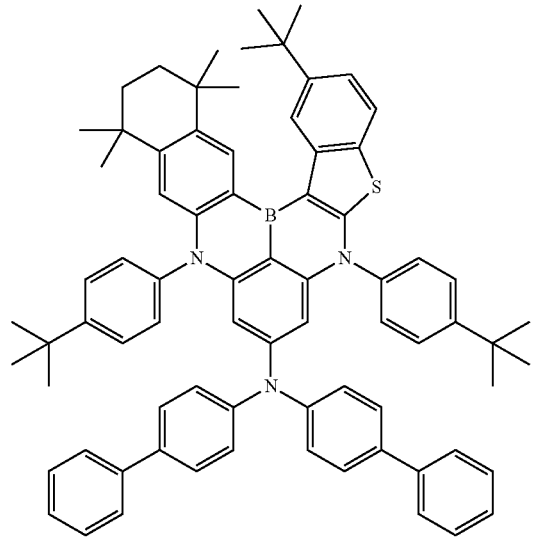

69
-continued
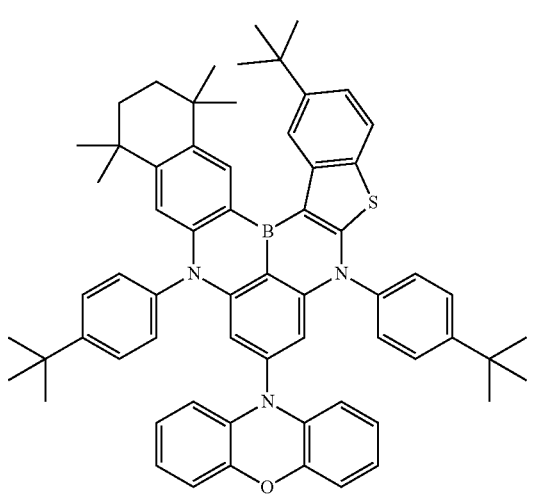
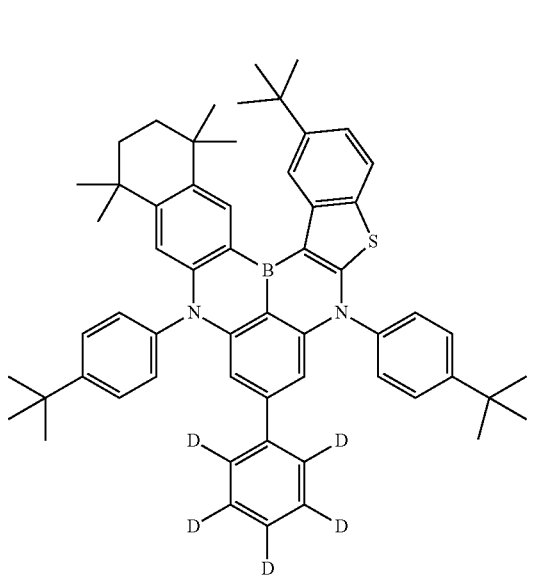
70
-continued

71
-continued
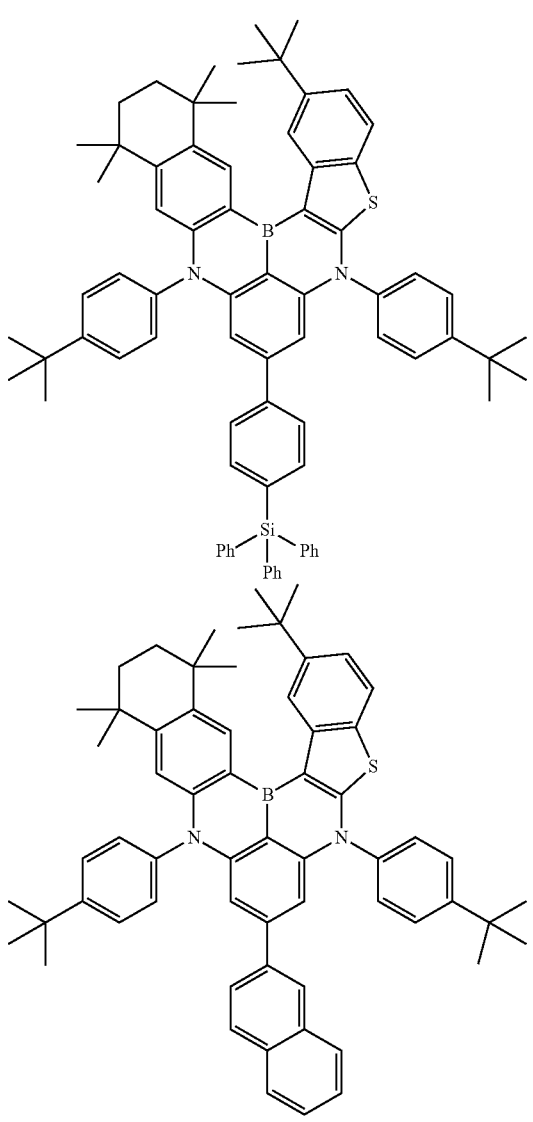
72
-continued
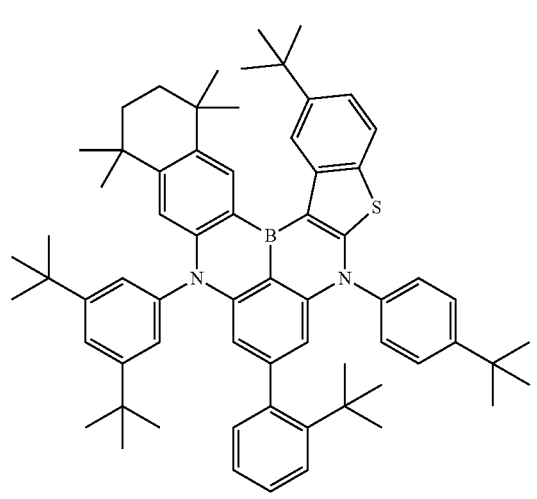

75
-continued
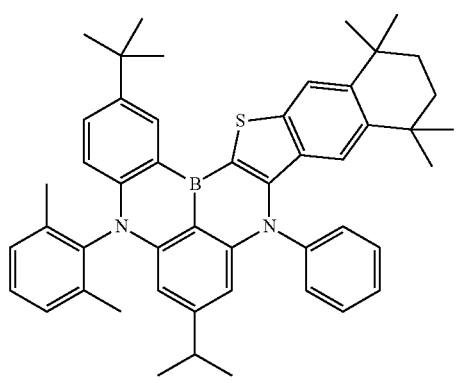
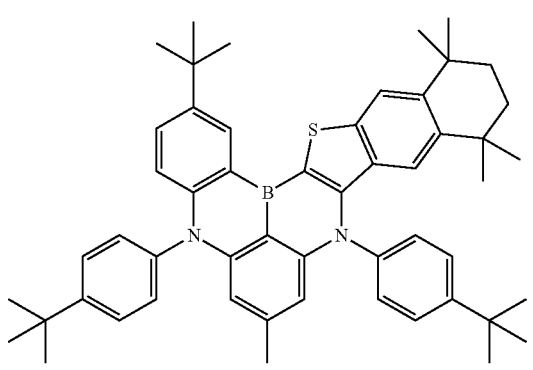
76
-continued
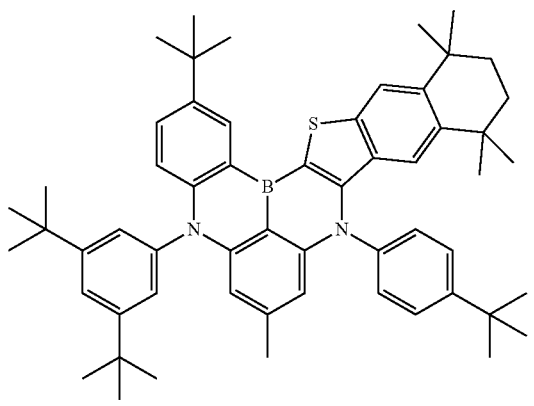
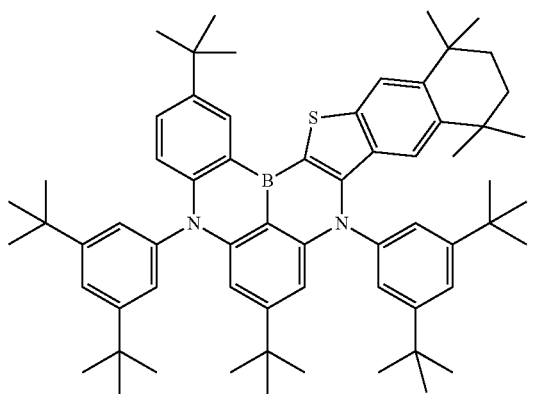
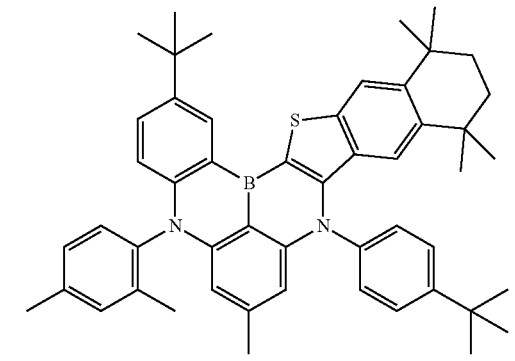
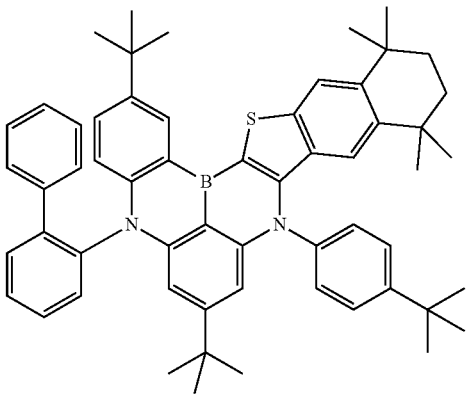

77
-continued
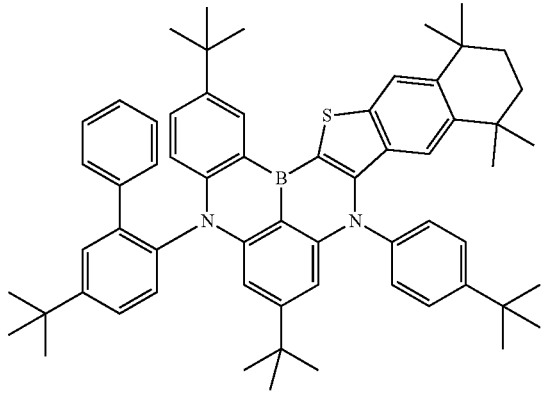
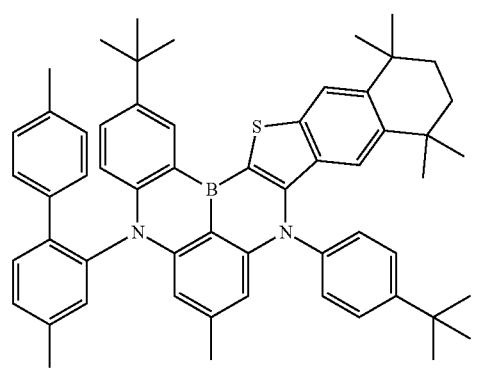
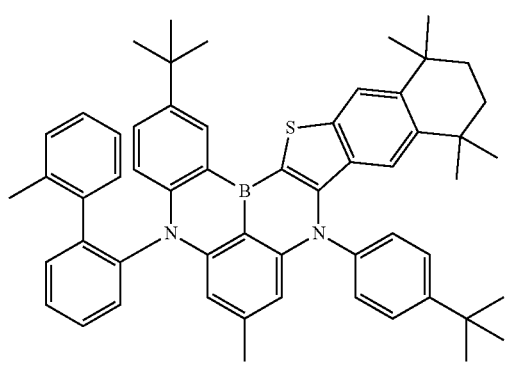
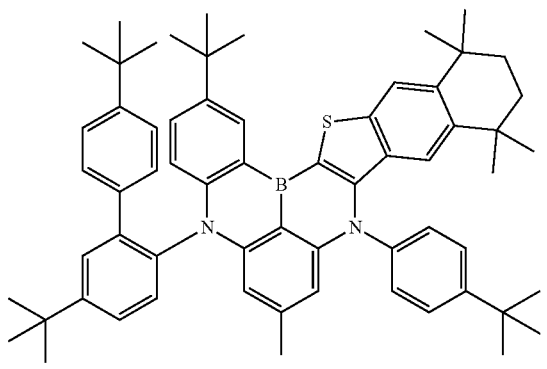
78
-continued
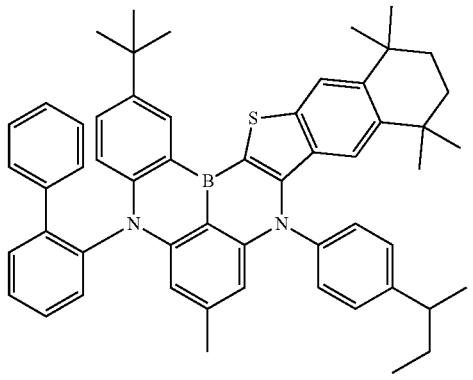
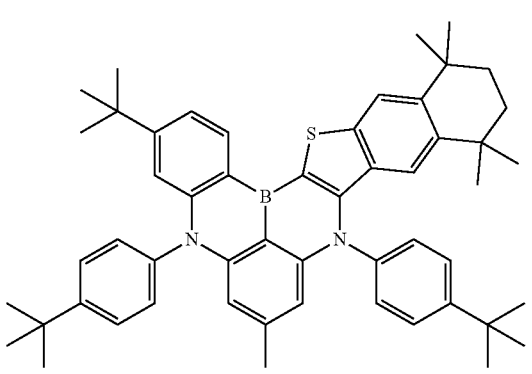
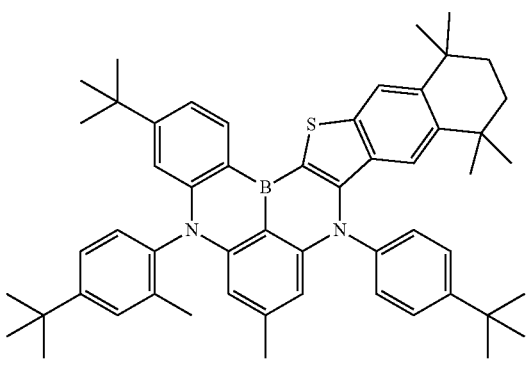
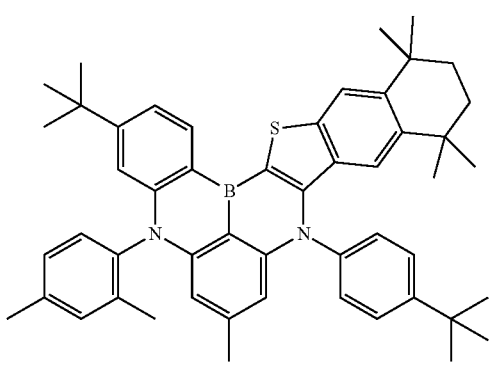

79
-continued
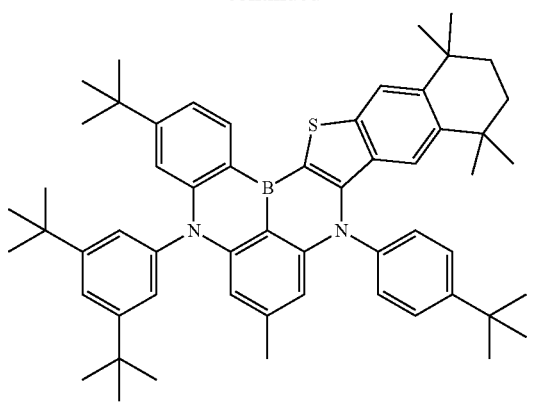
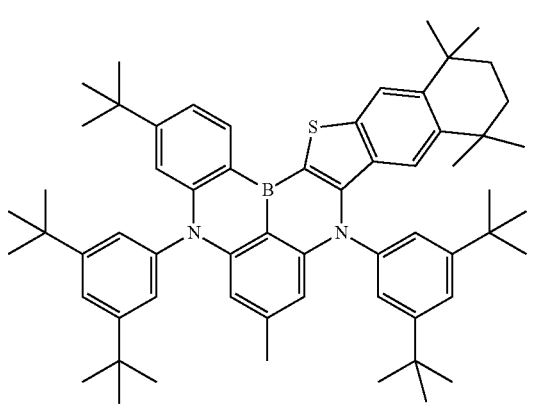
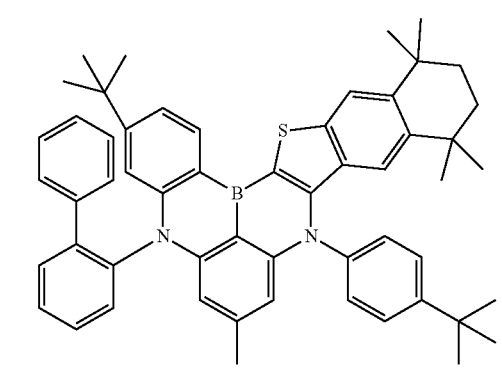
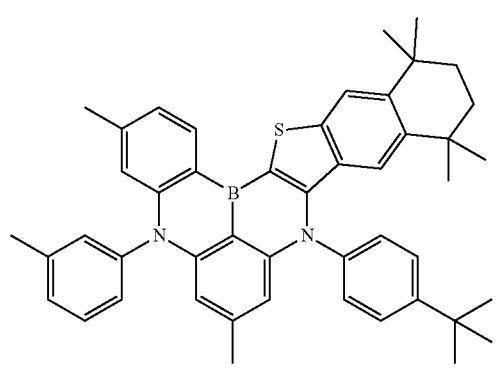
80
-continued
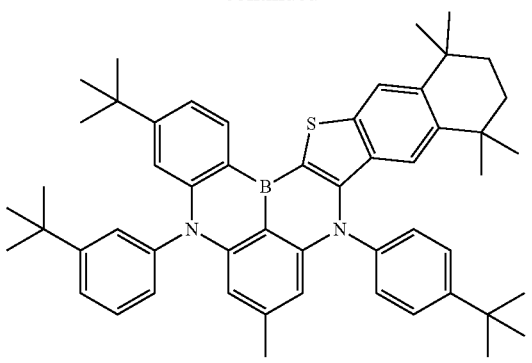
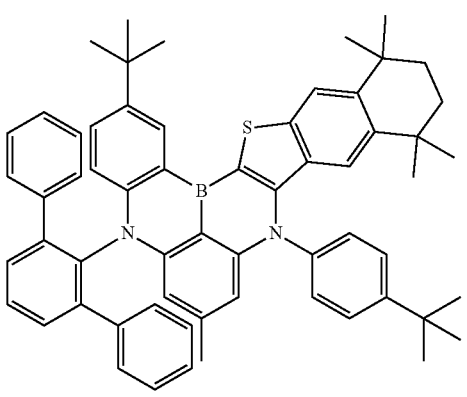
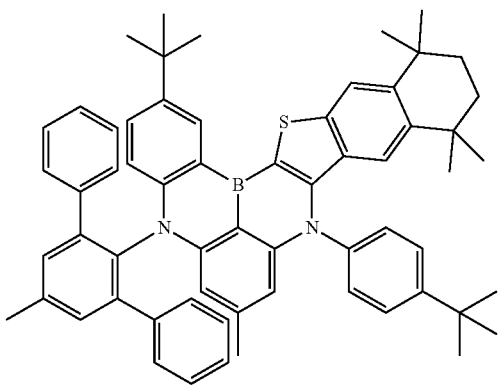
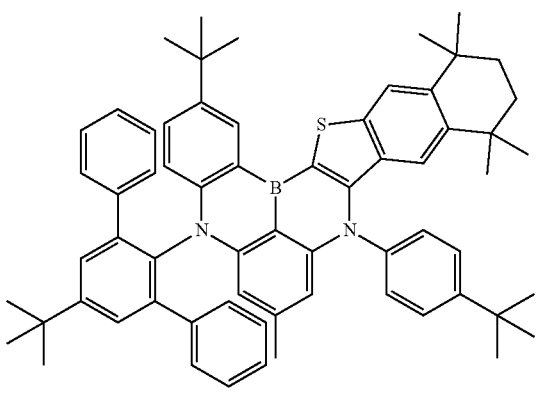

81
-continued
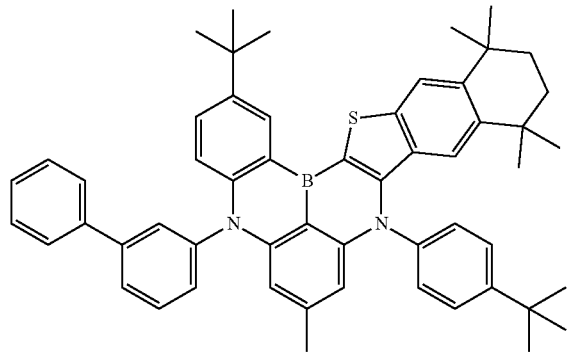
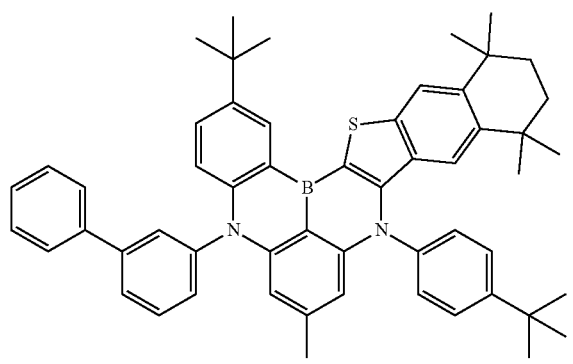
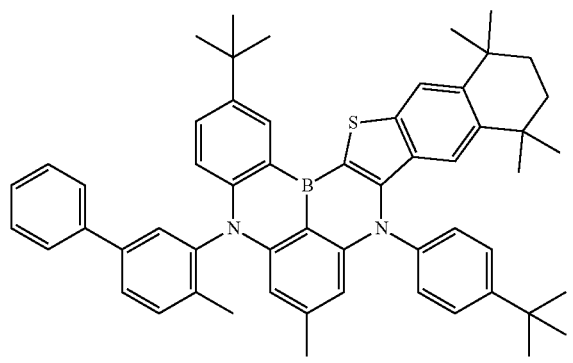
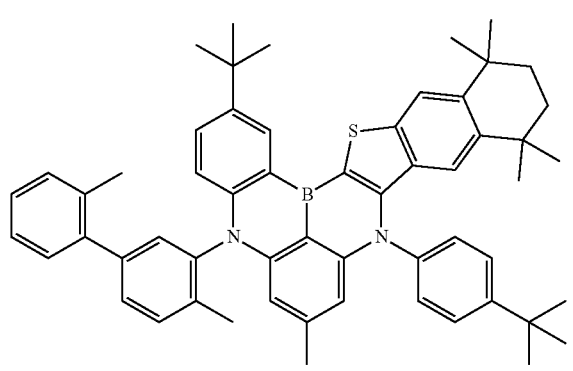
82
-continued
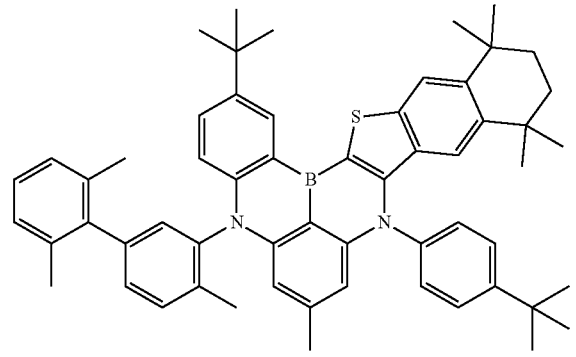
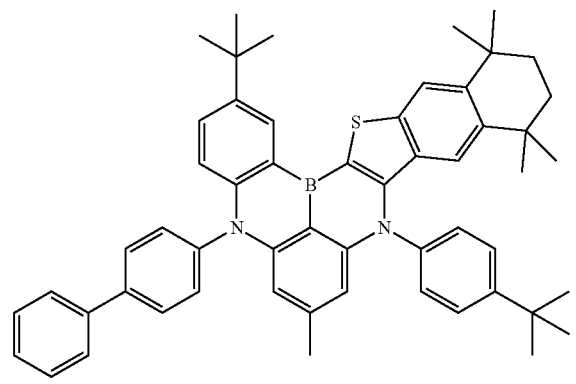
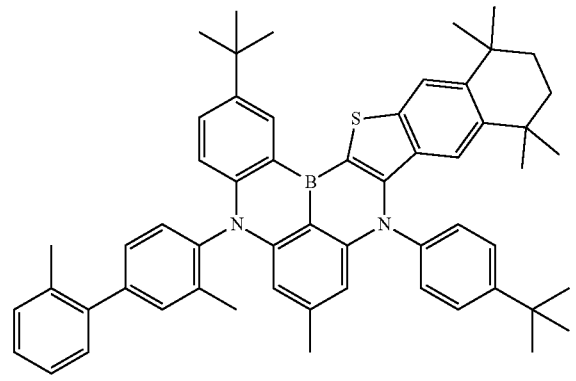

85
-continued
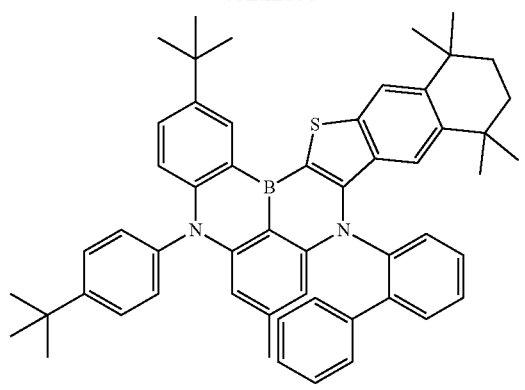
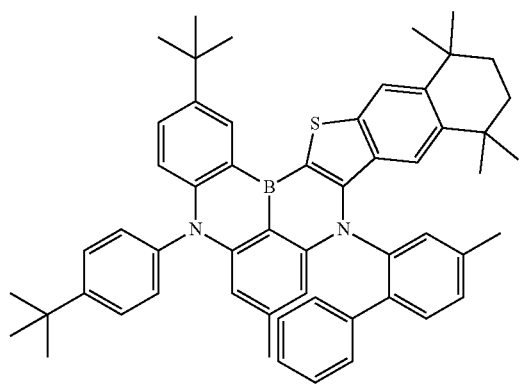
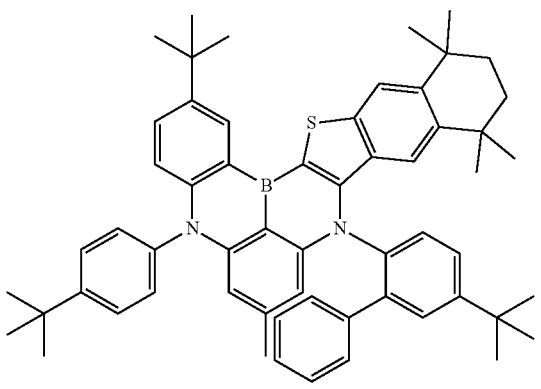
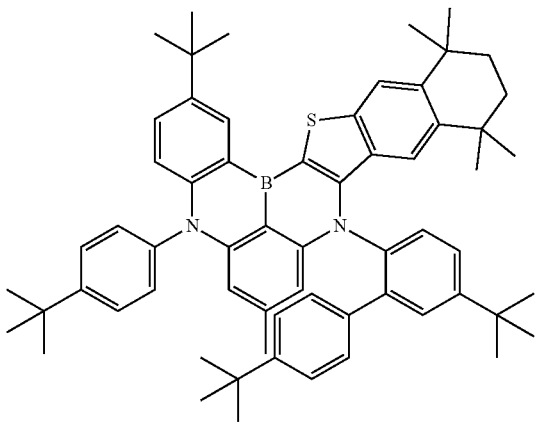
86
-continued
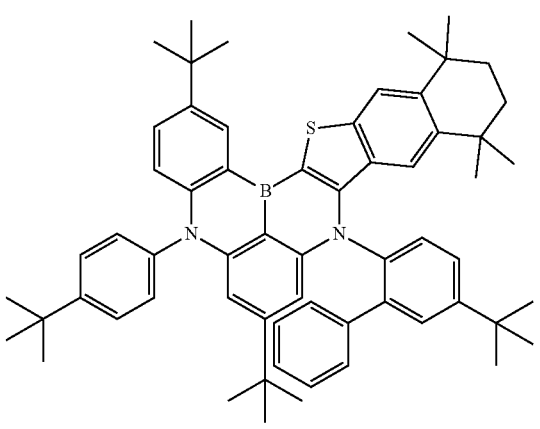
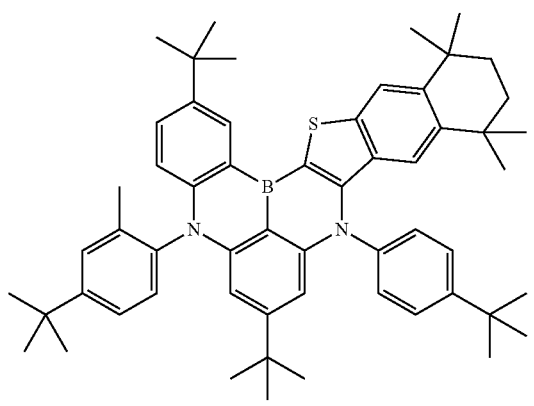
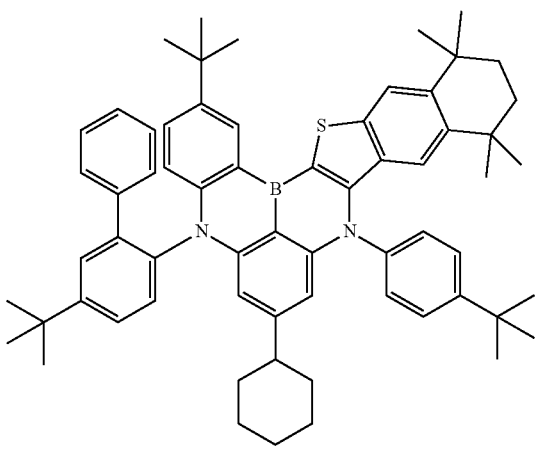

87
-continued
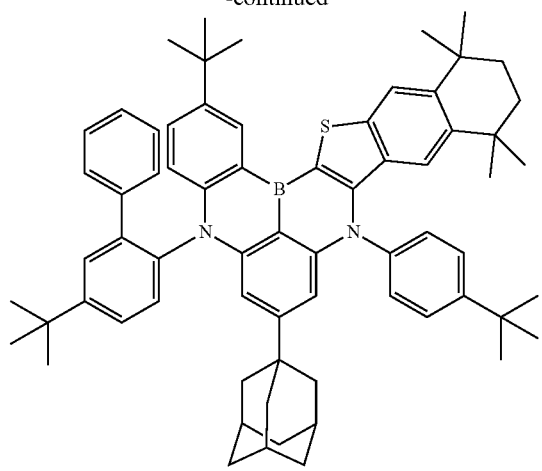
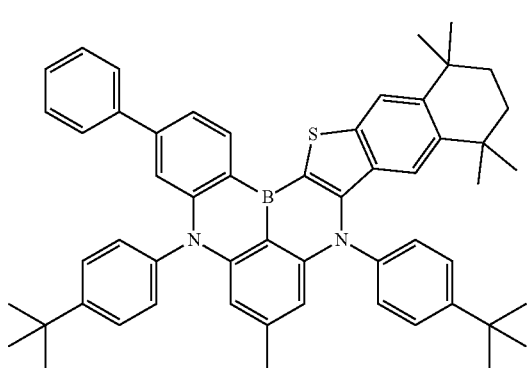
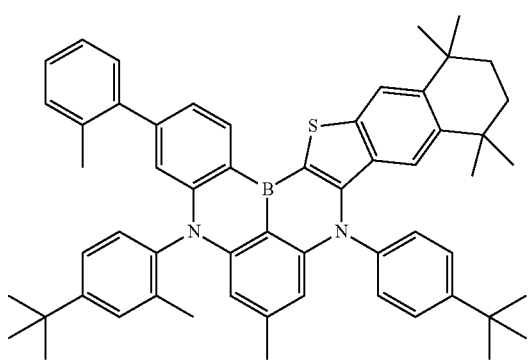
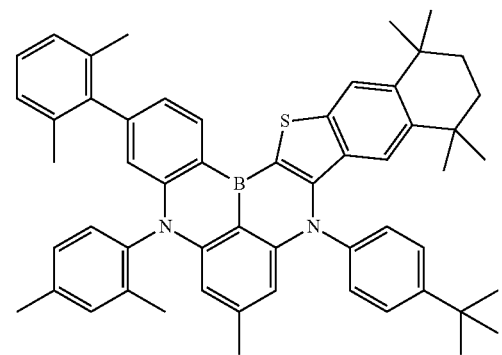
88
-continued
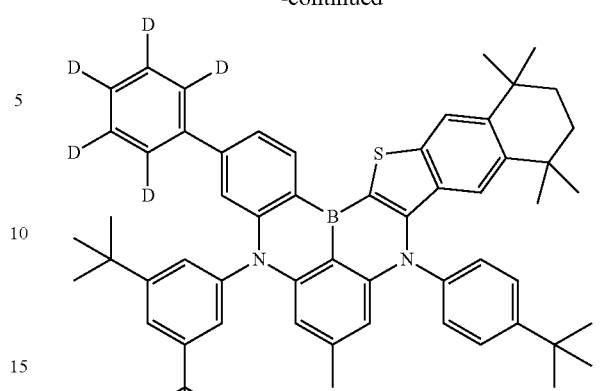
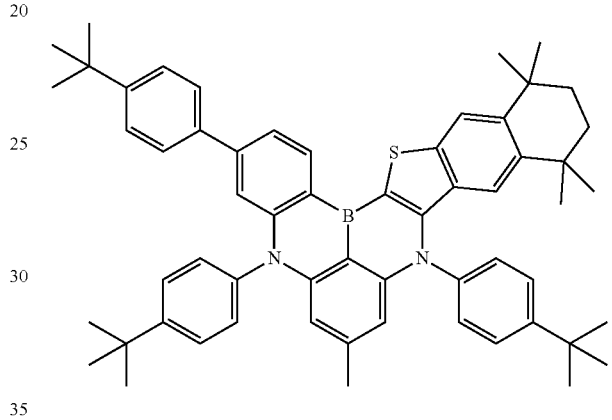
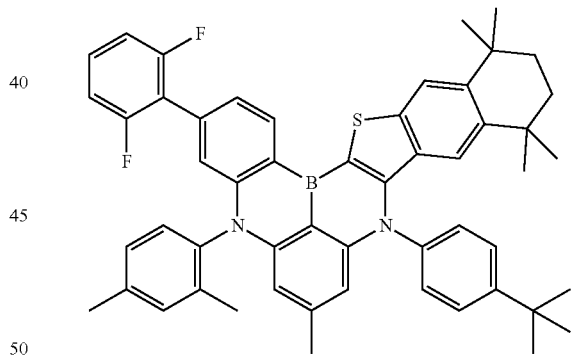
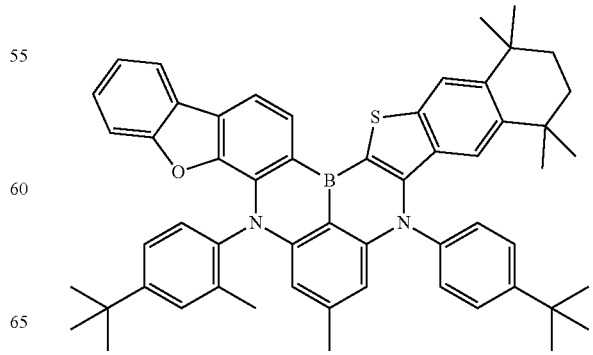

89
-continued
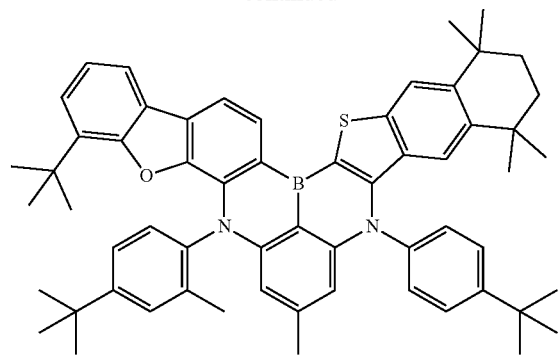
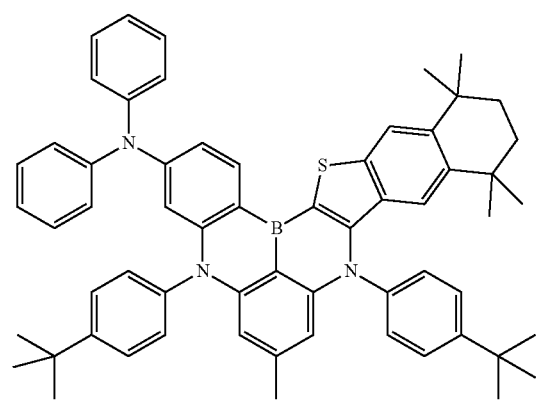
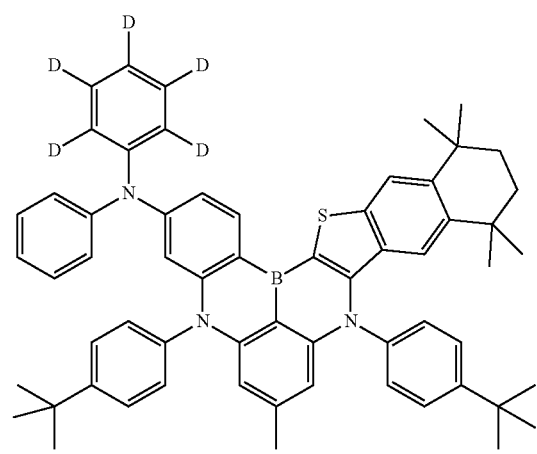
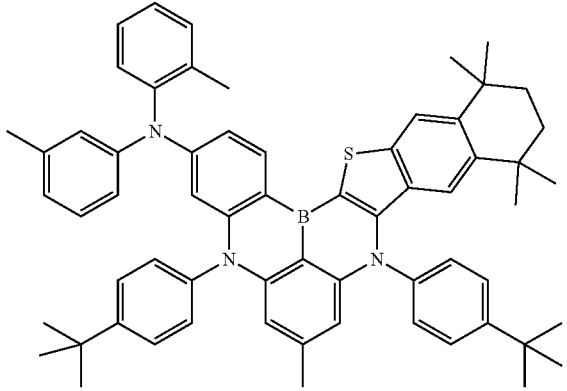
90
-continued
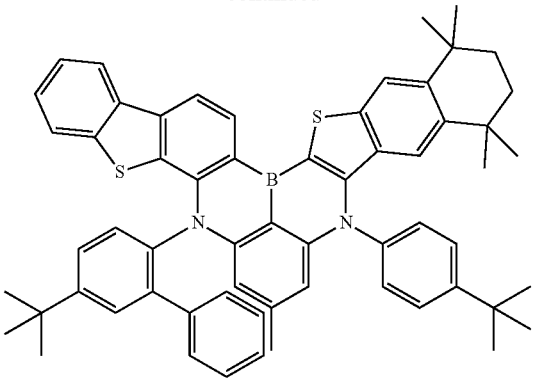
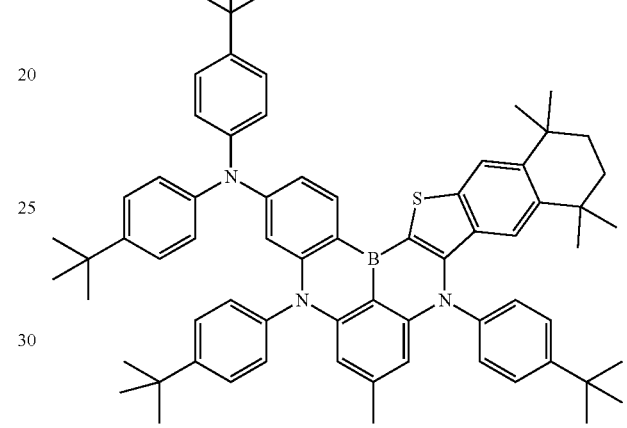
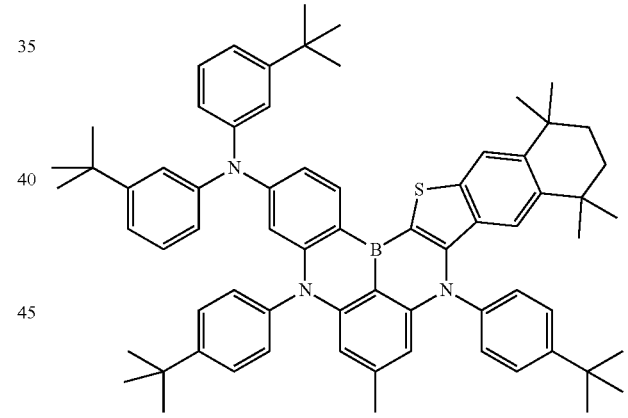
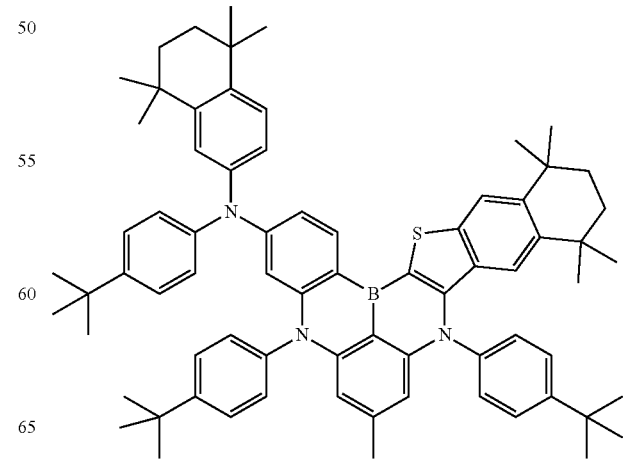

91
-continued
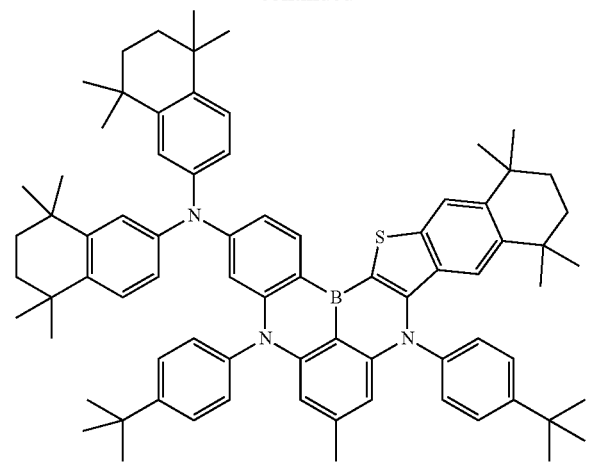
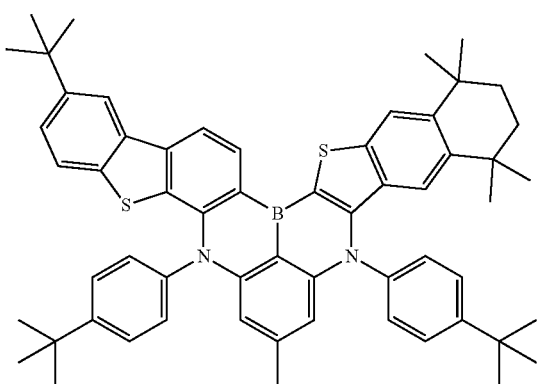
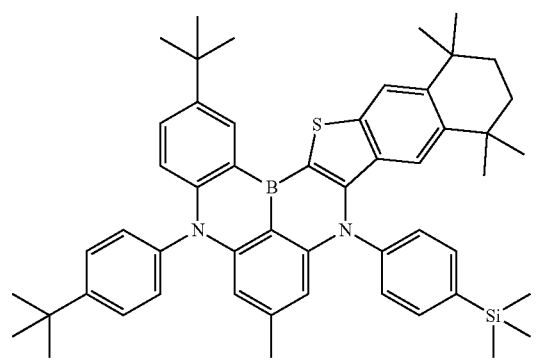
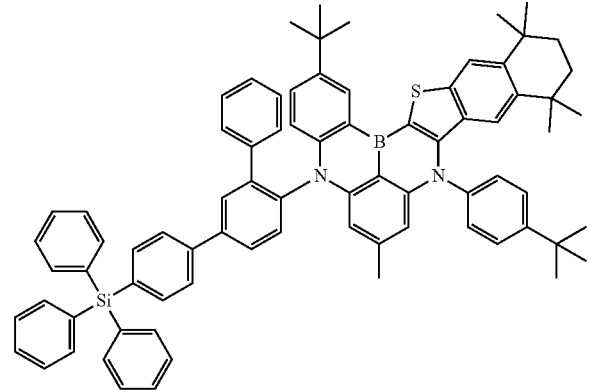
92
-continued
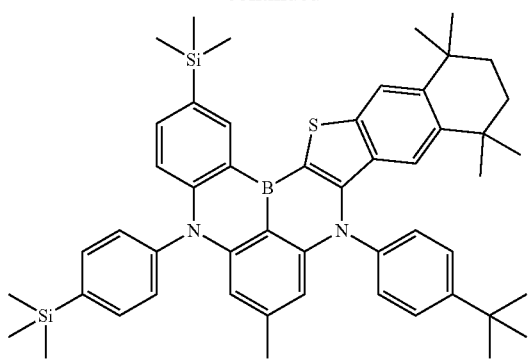
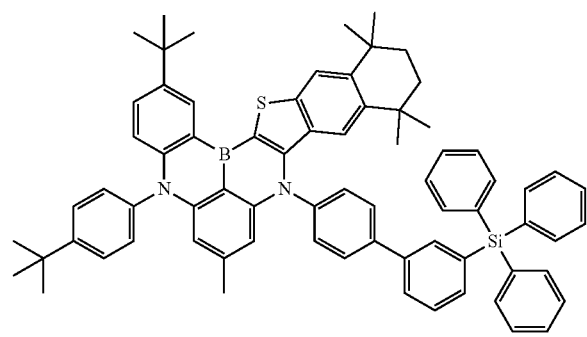
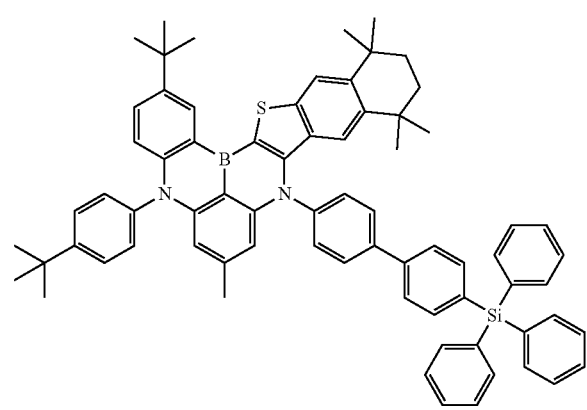
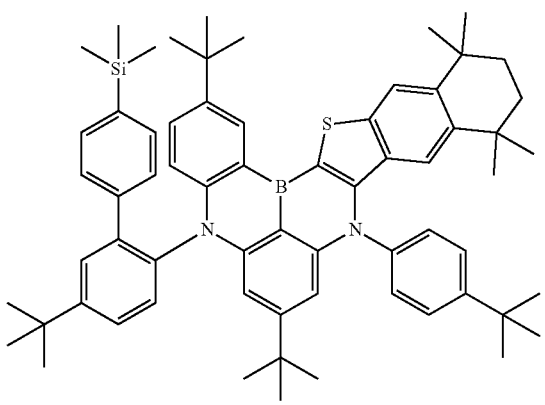

-continued
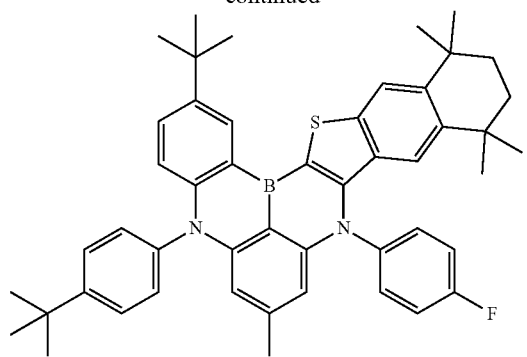
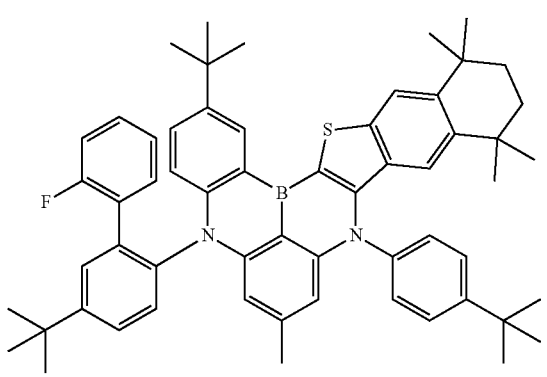
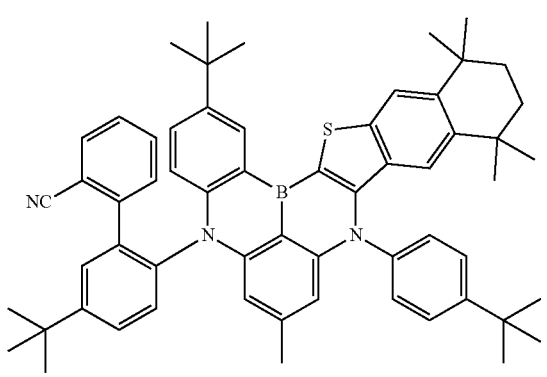
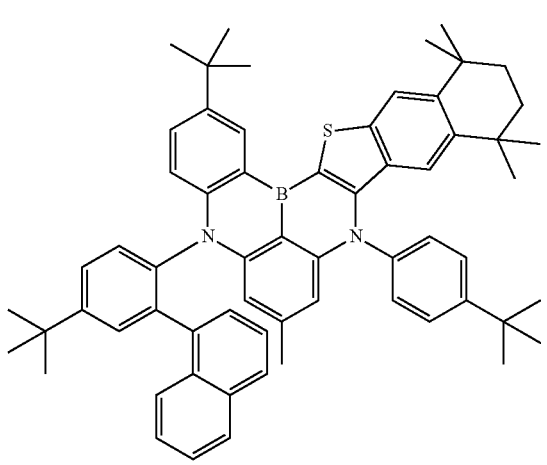
-continued
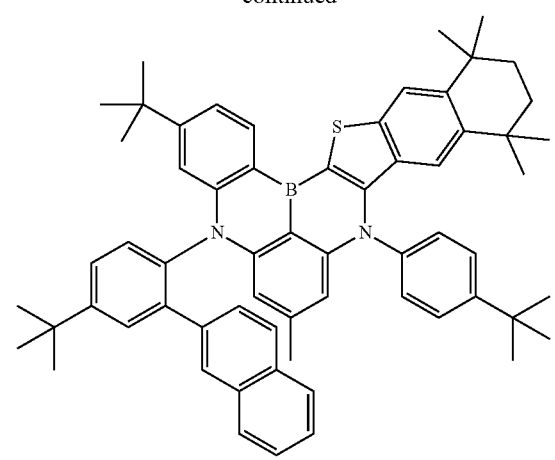
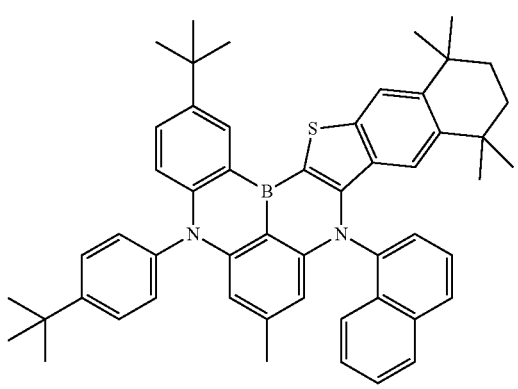
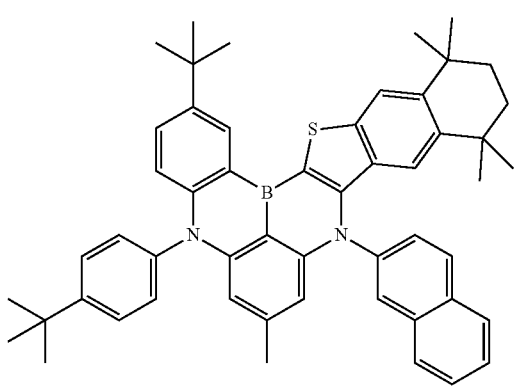
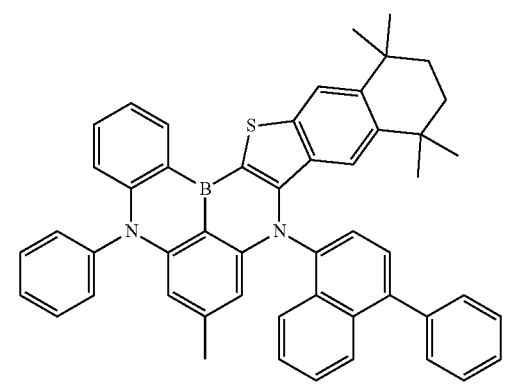

95
-continued
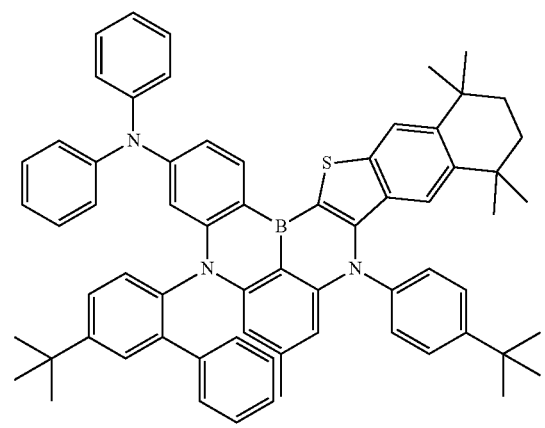
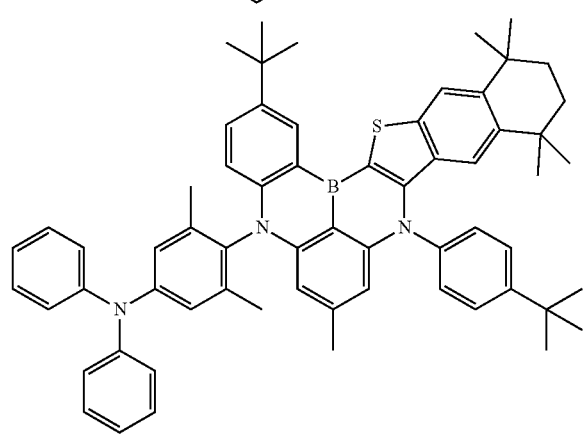
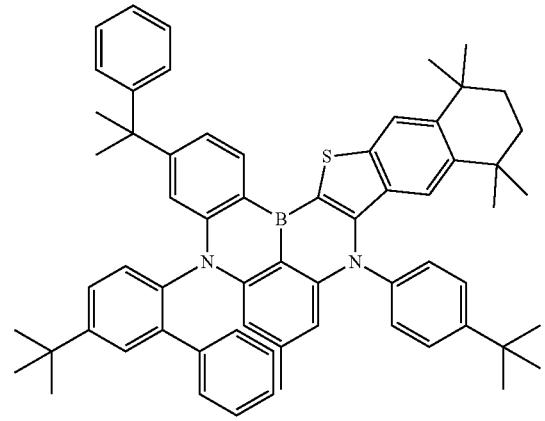
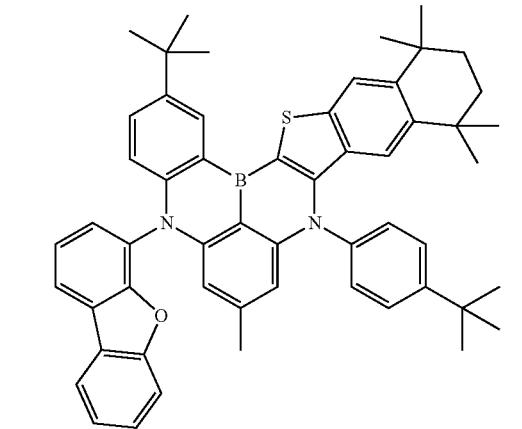
96
-continued
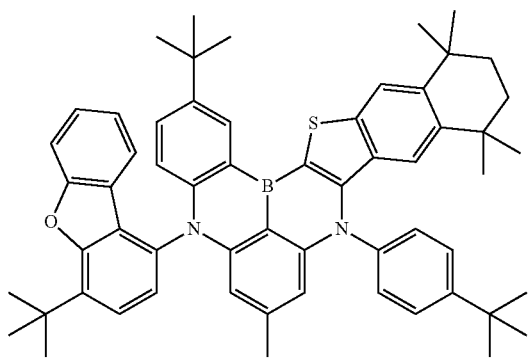
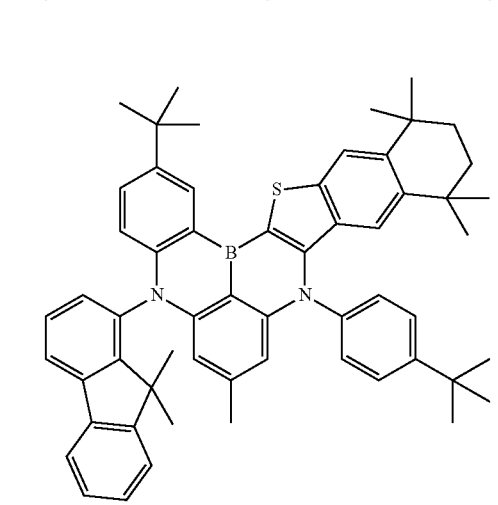
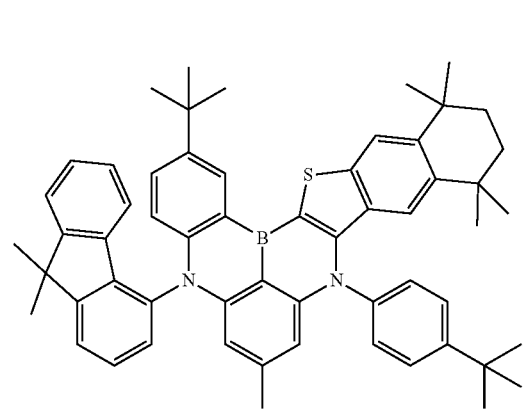
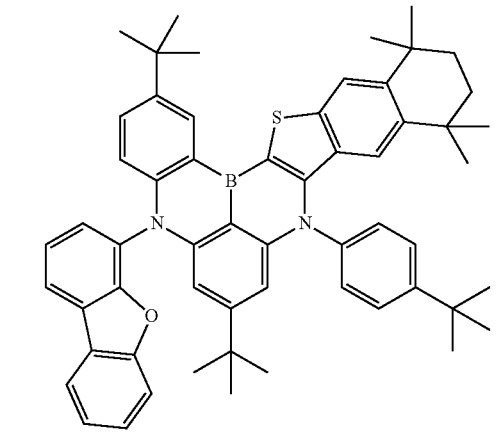

97
-continued
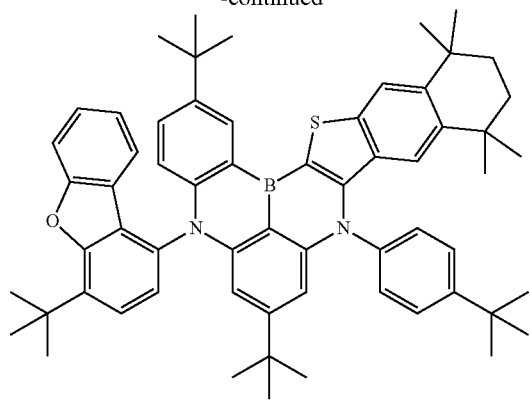
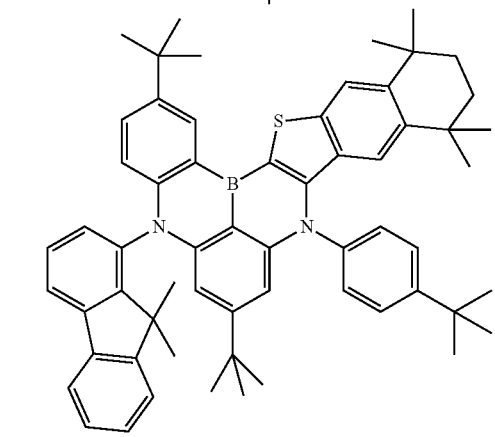
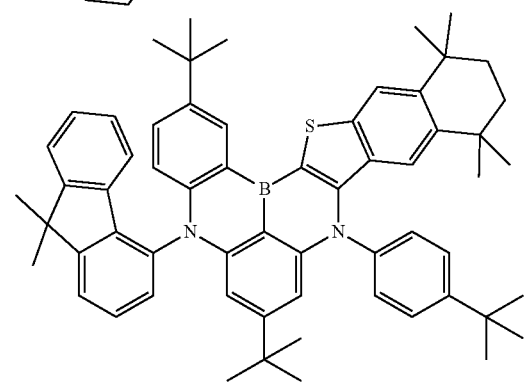
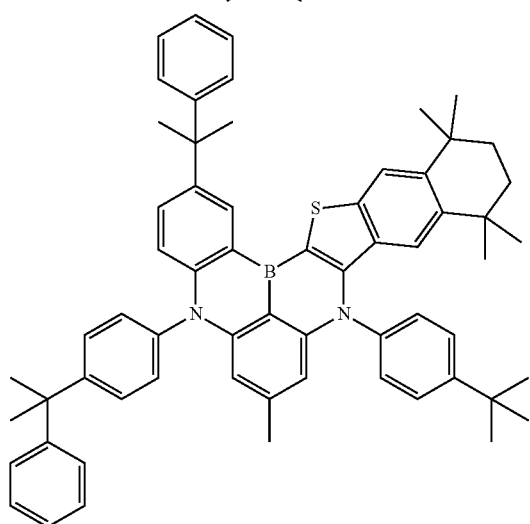
98
-continued
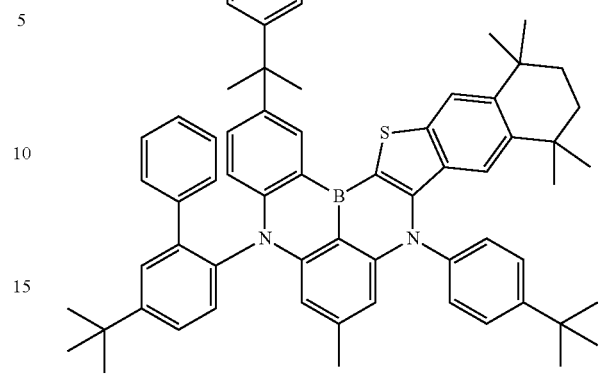
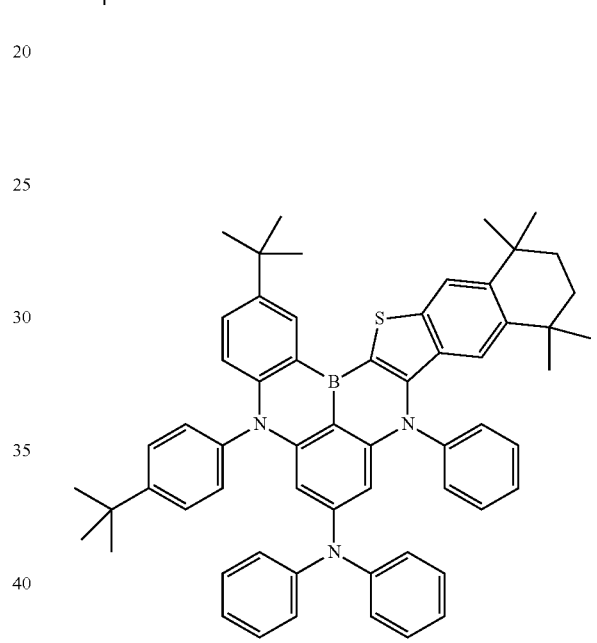
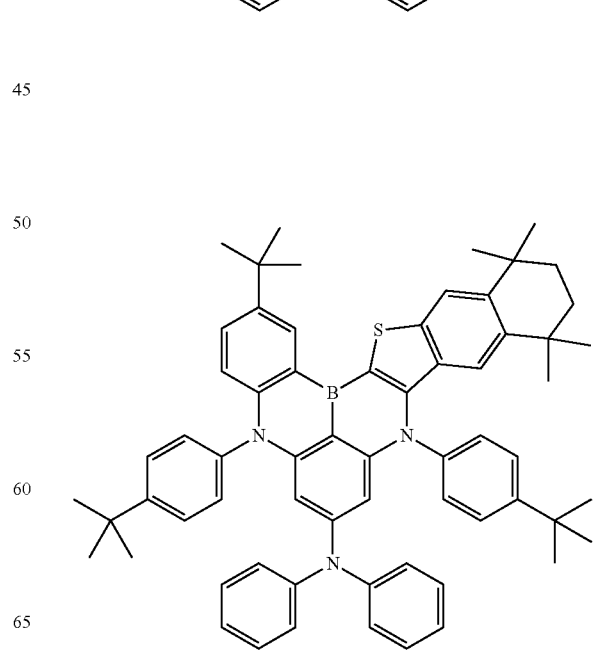

99
-continued
100
-continued
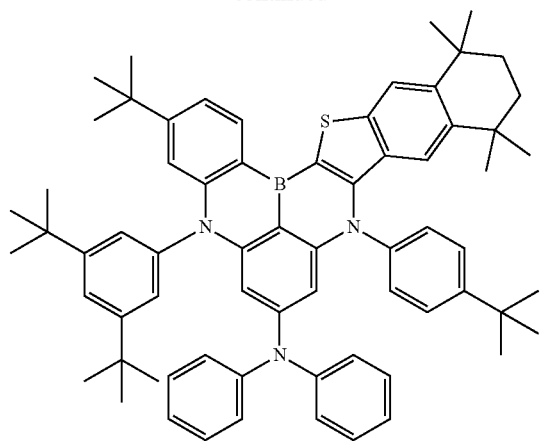
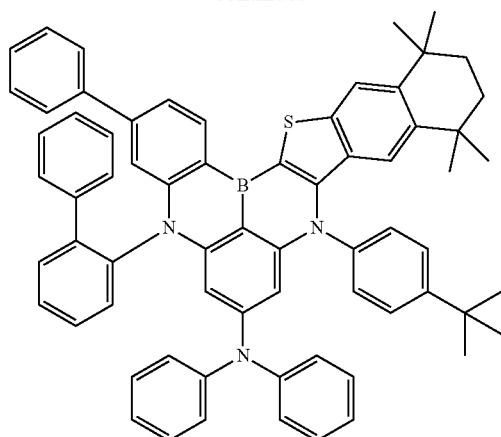
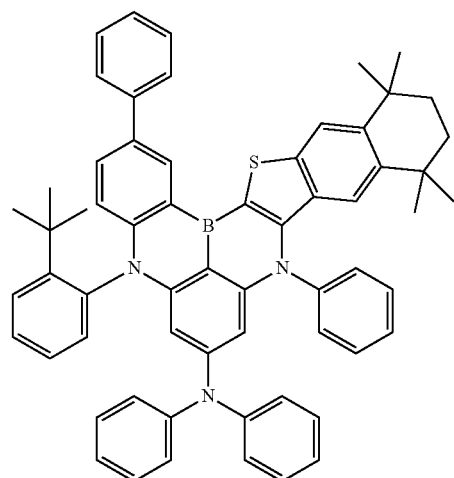
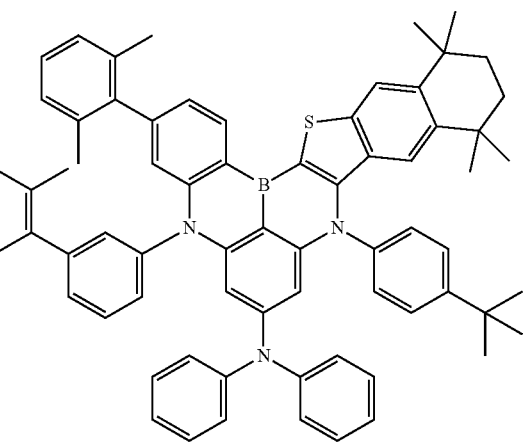
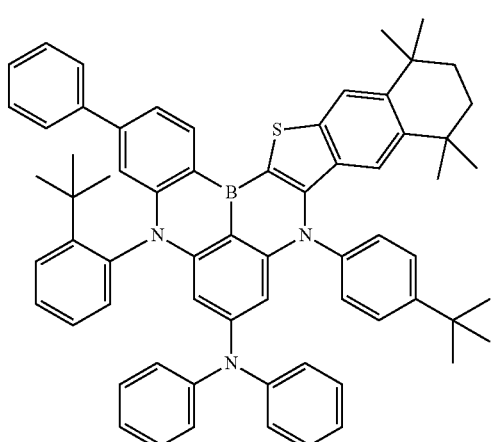

101
-continued
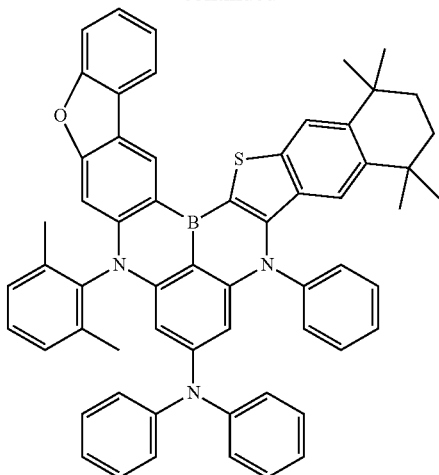
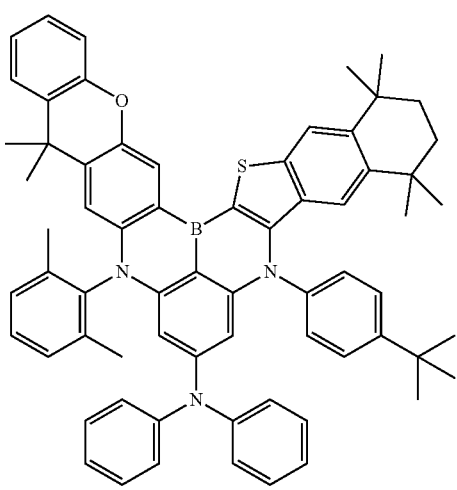
102
-continued
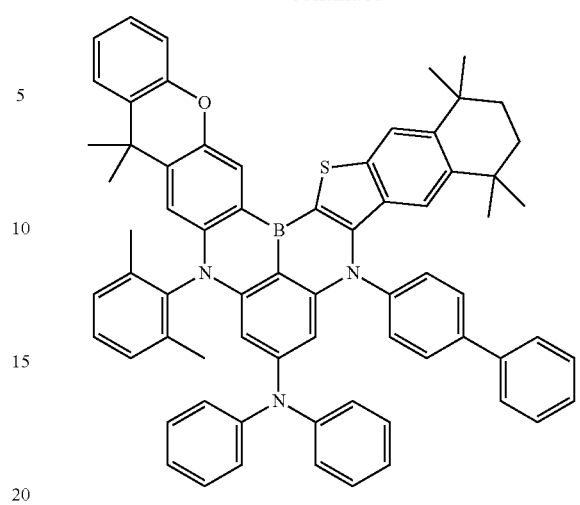
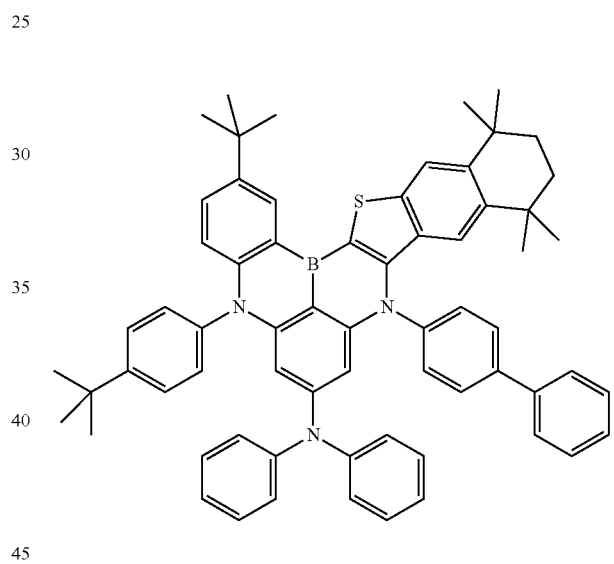
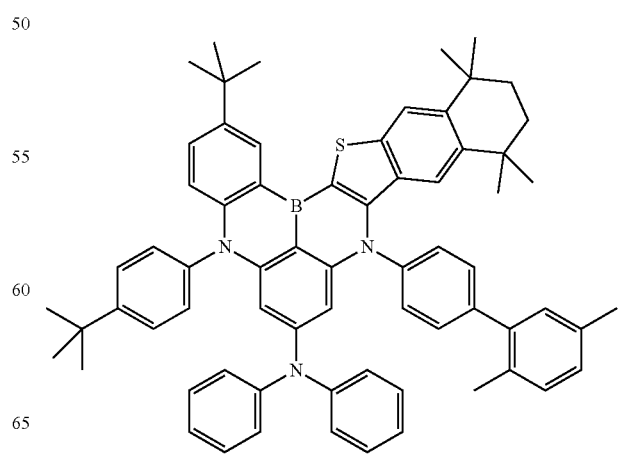

103
-continued
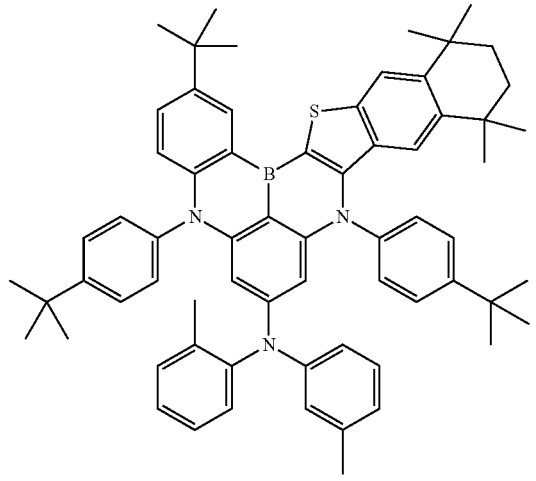
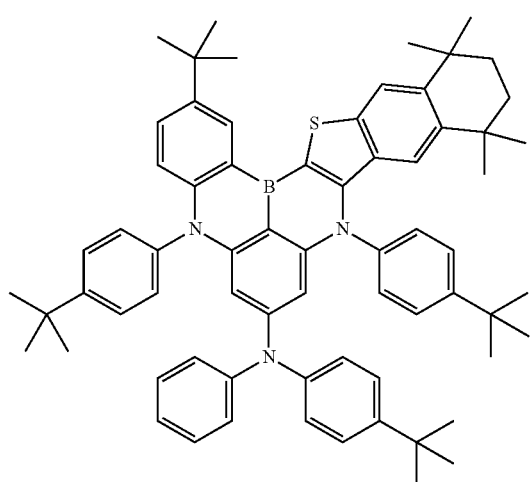
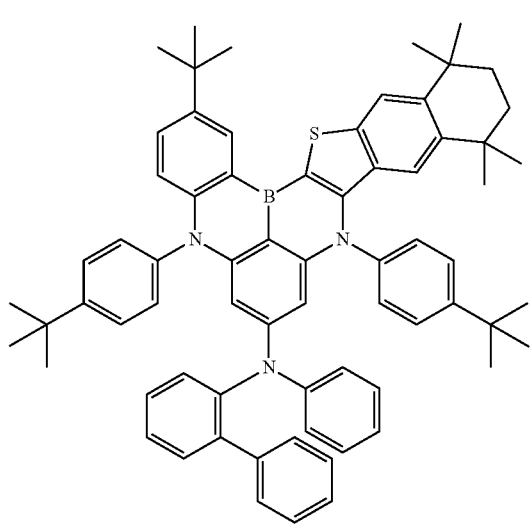
104
-continued
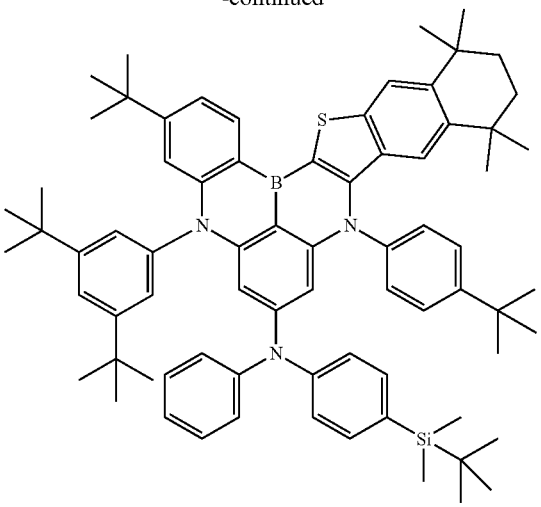
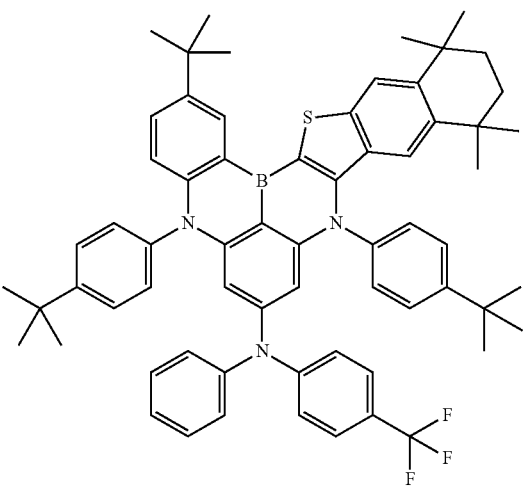
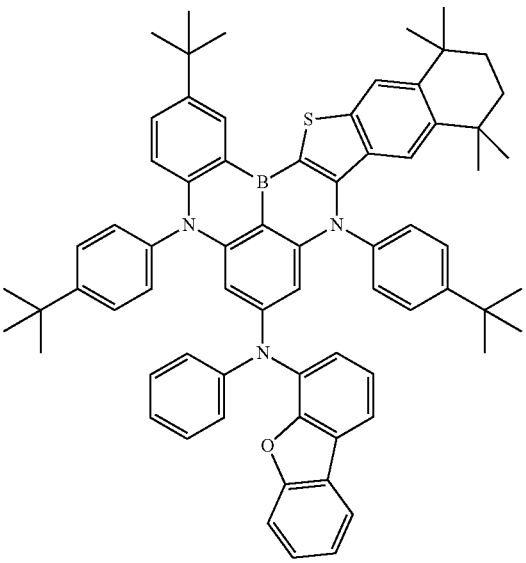

105
-continued
106
-continued
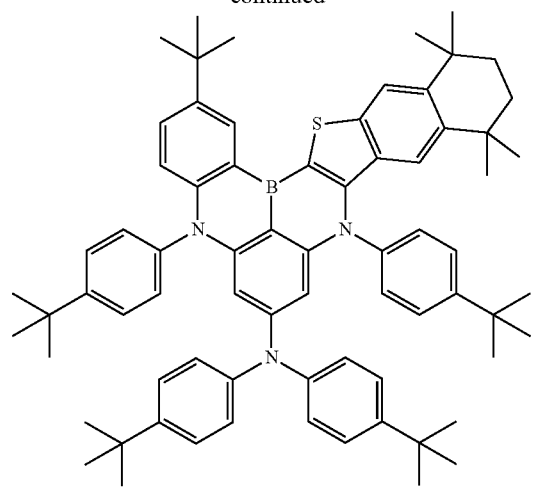
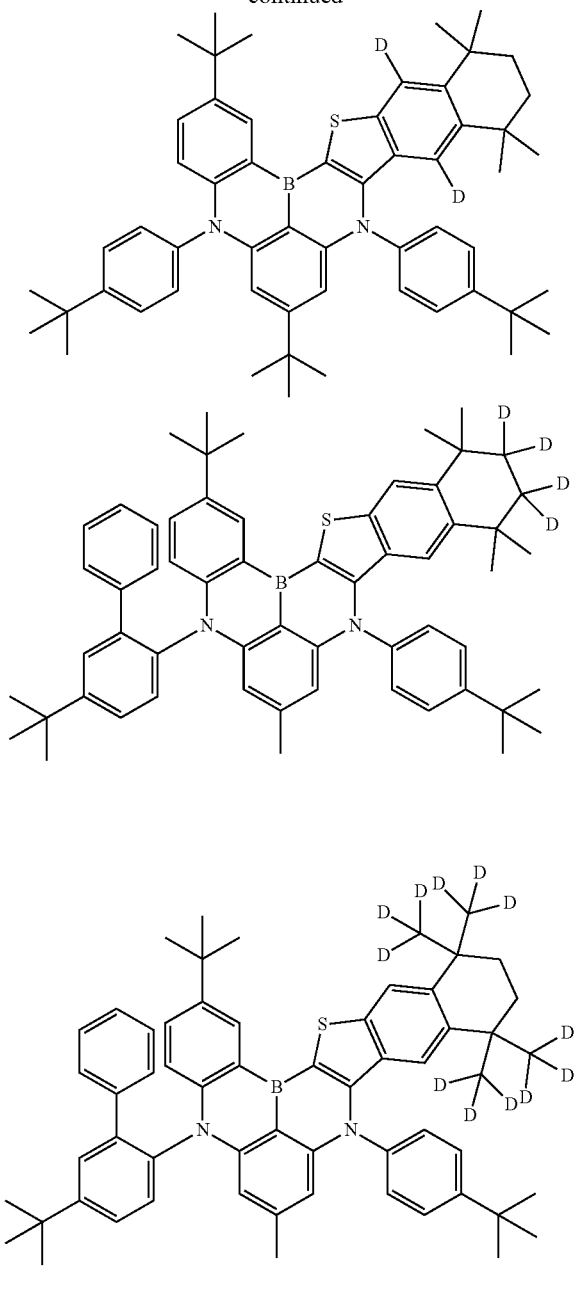
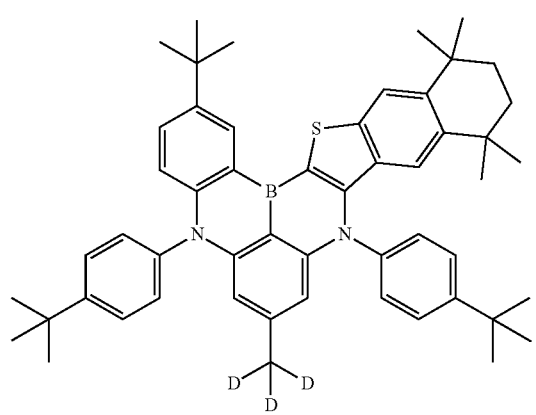
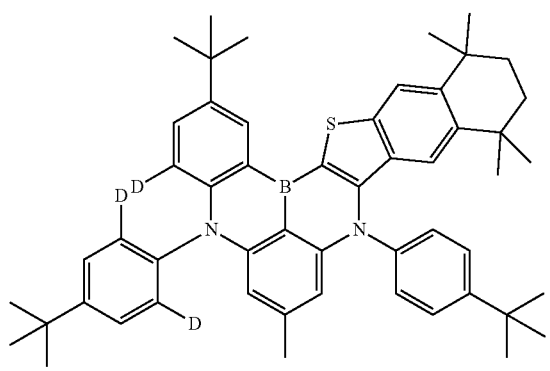

| 107 -continued | 108 -continued |
|---|---|
| 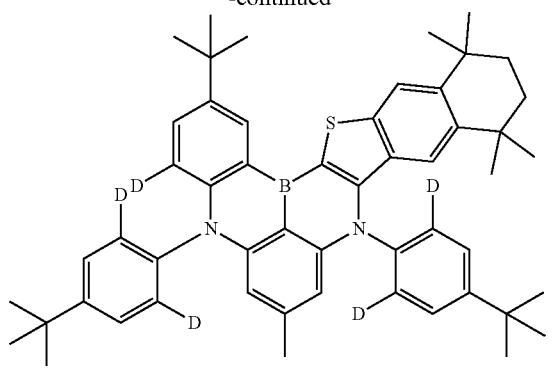 | 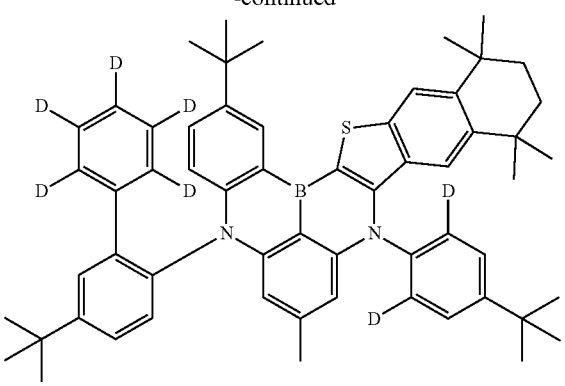 |
| 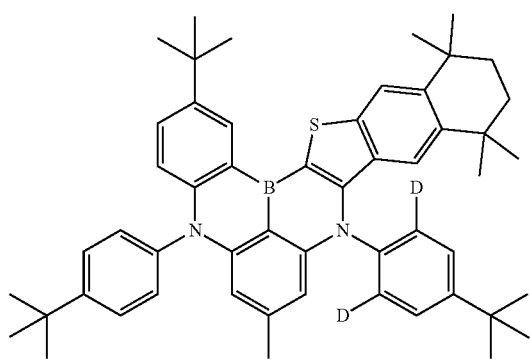 | 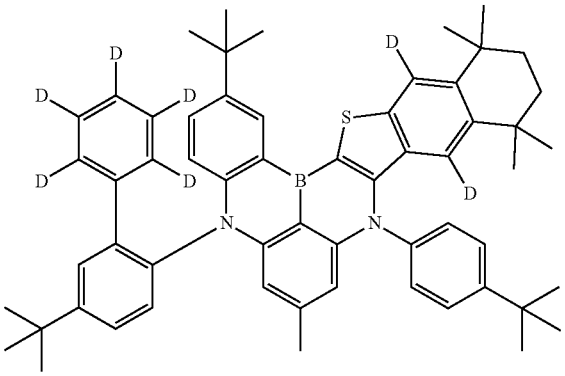 |
| 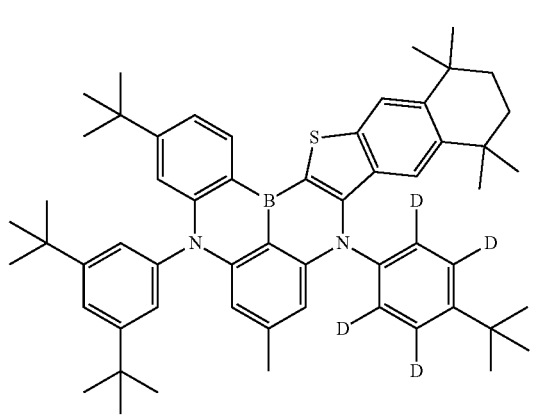 | 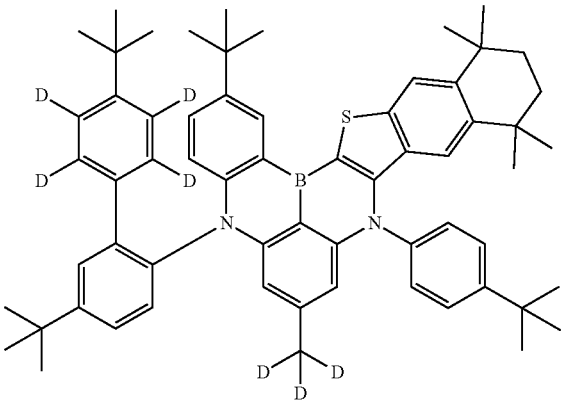 |
| 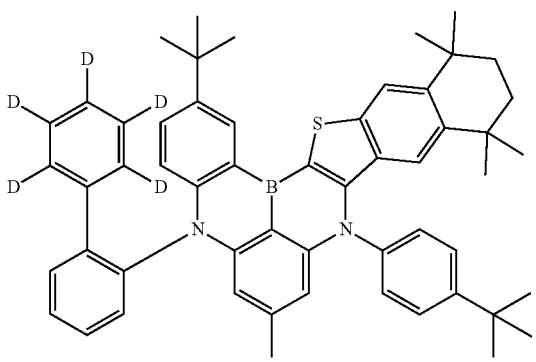 | 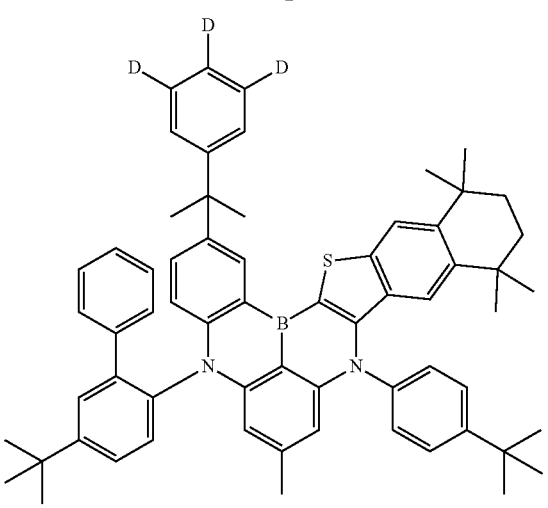 |

109
-continued
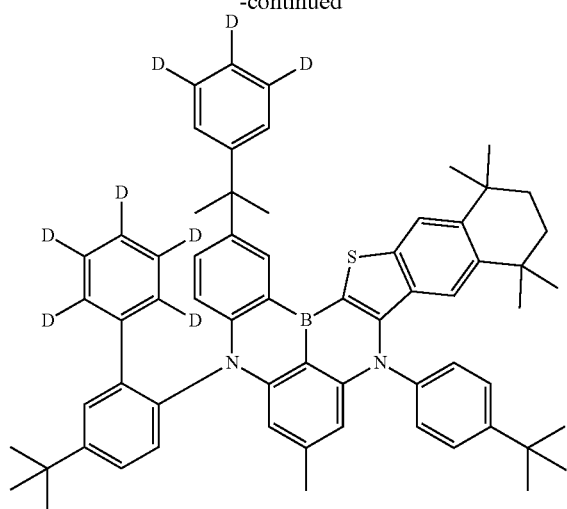
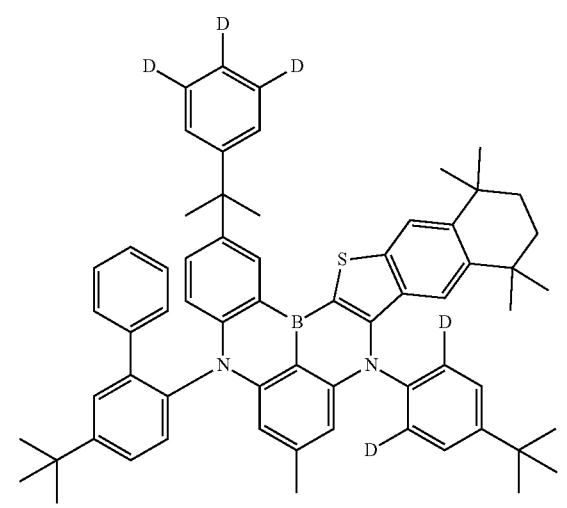
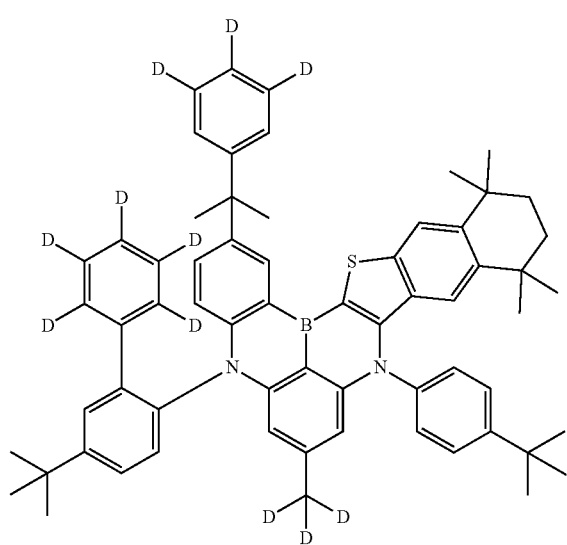
110
-continued
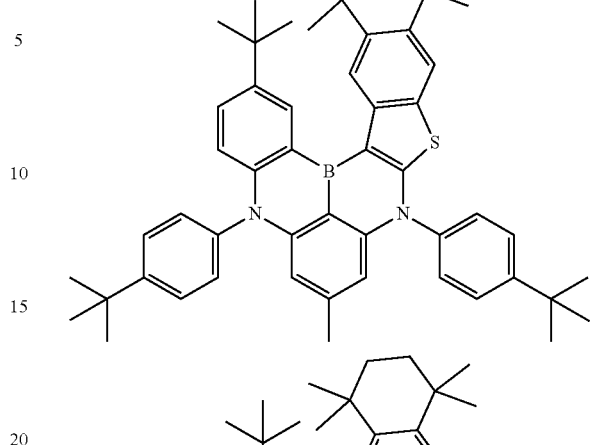
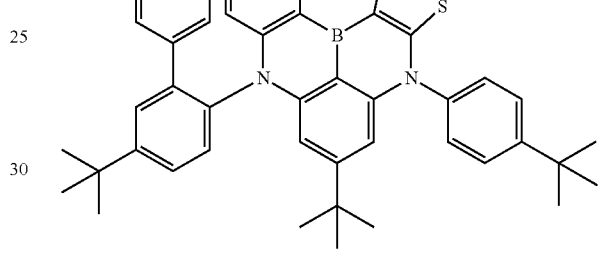
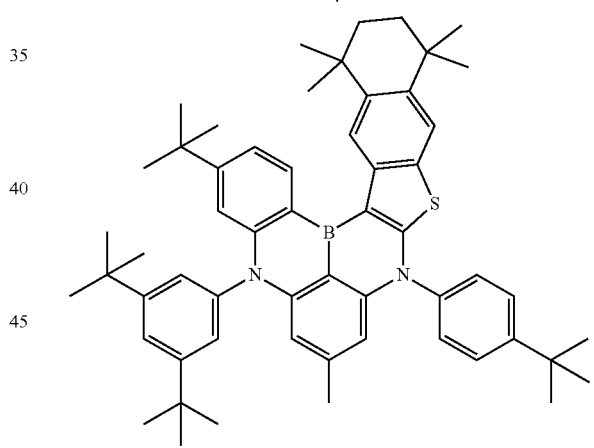
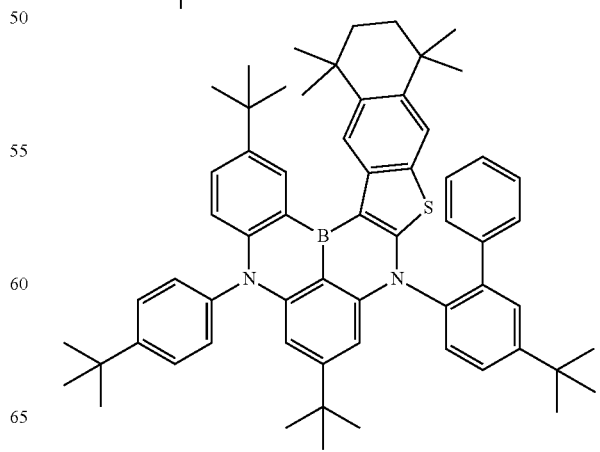

111
-continued
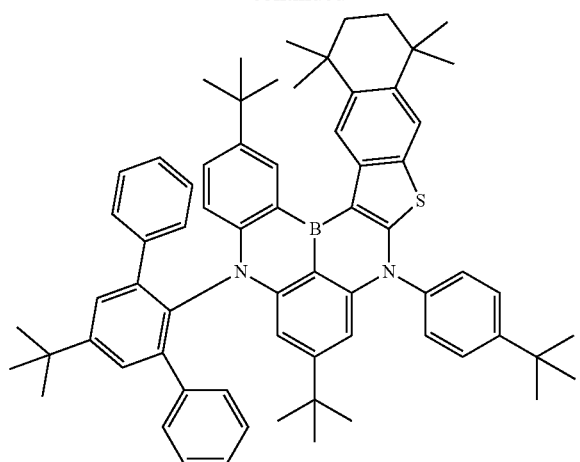
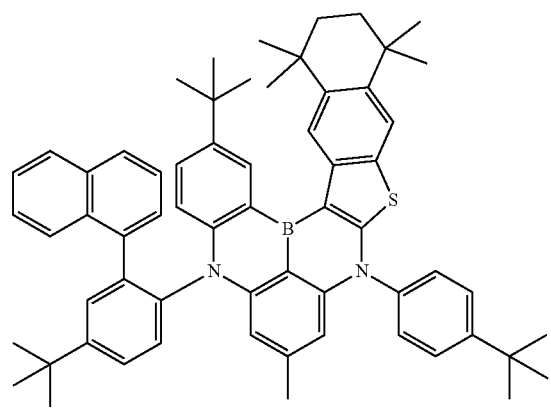
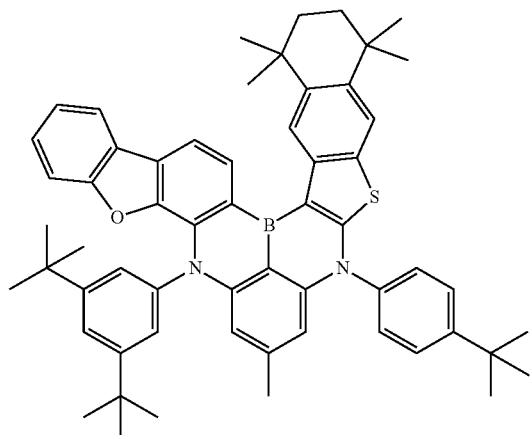
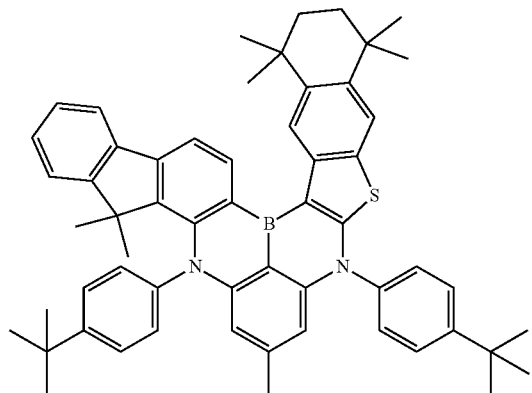
112
-continued
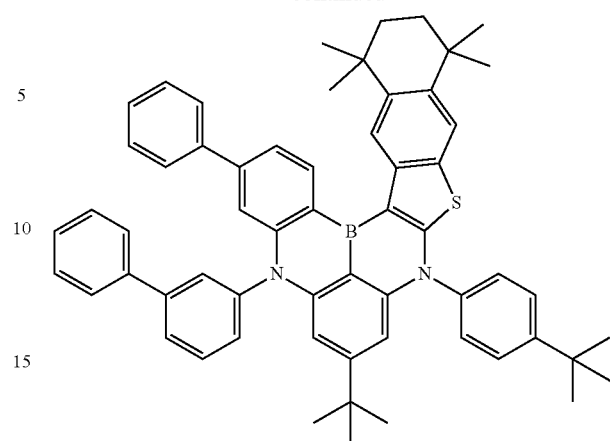
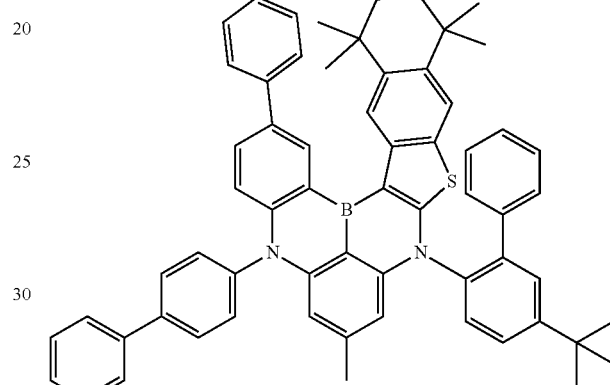
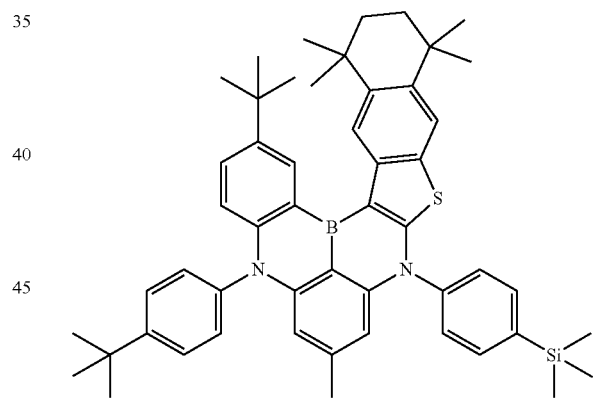
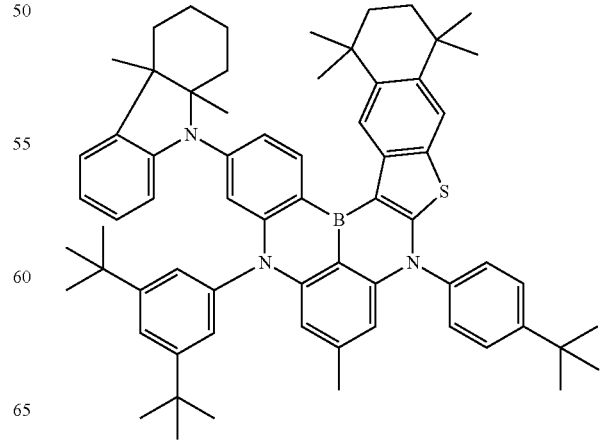

113
-continued
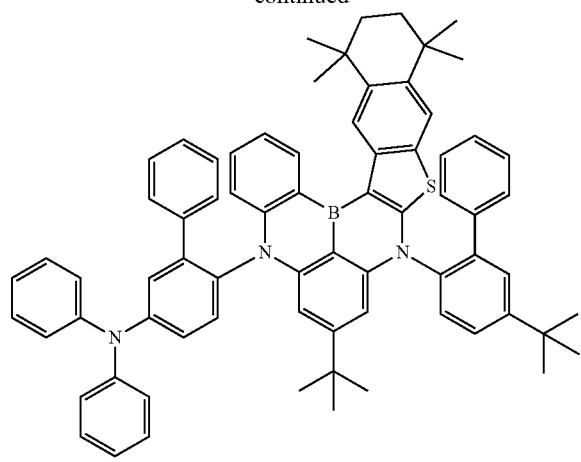
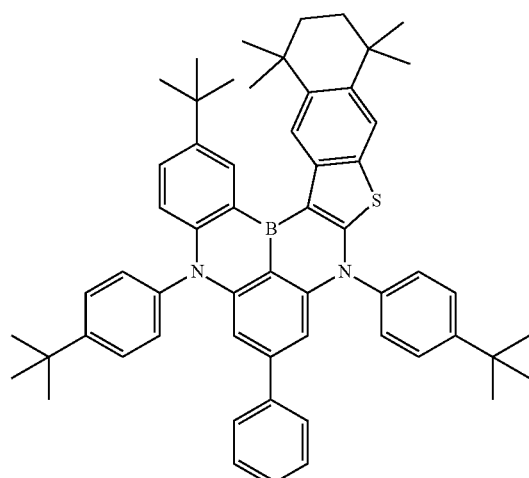
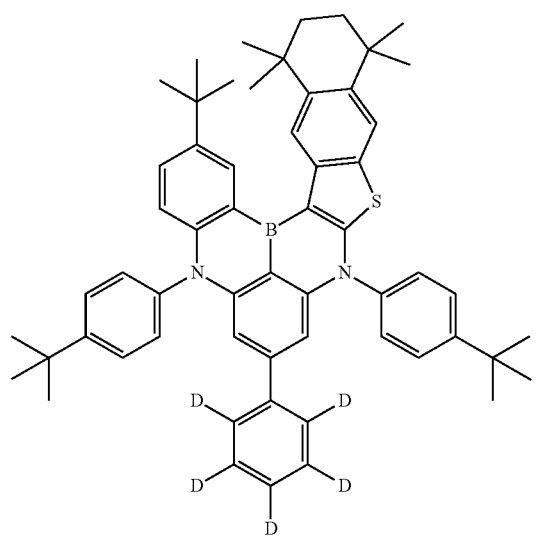
114
-continued
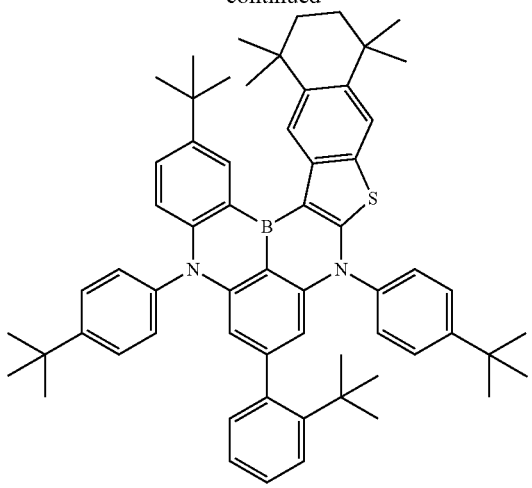
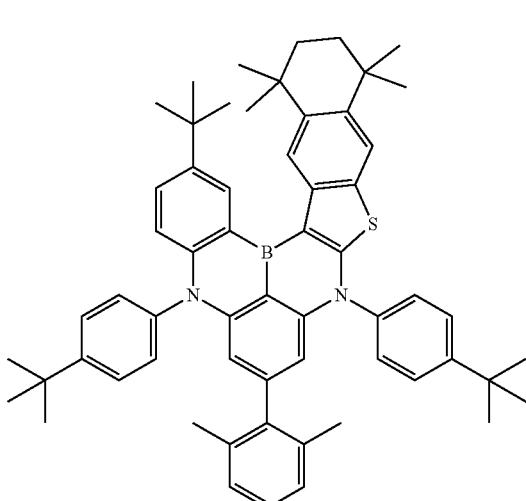
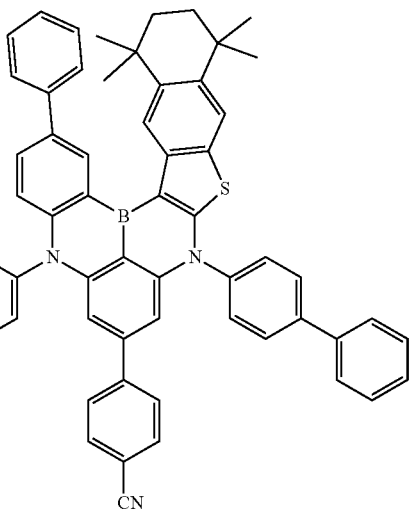

115 -continued
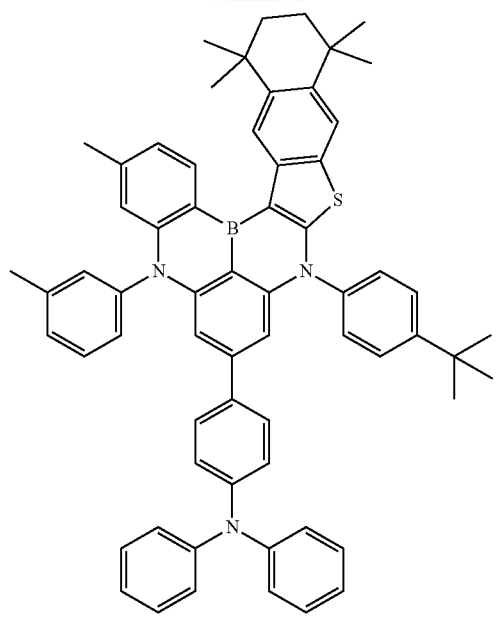
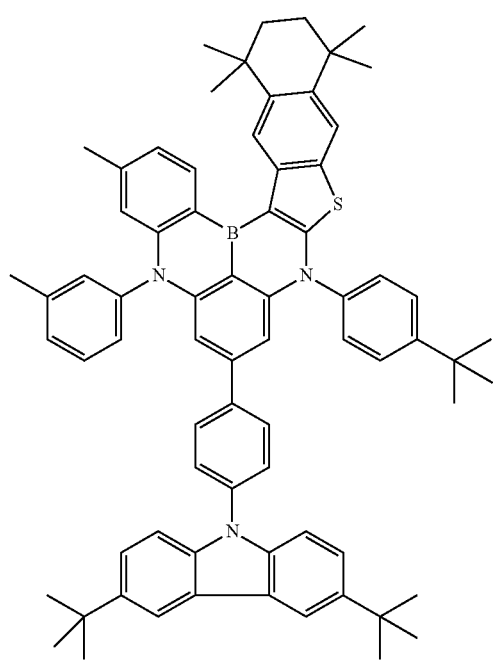
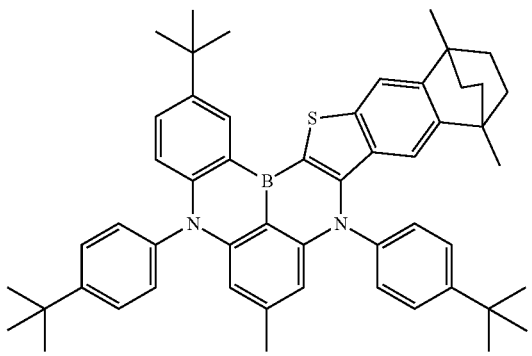
116 -continued
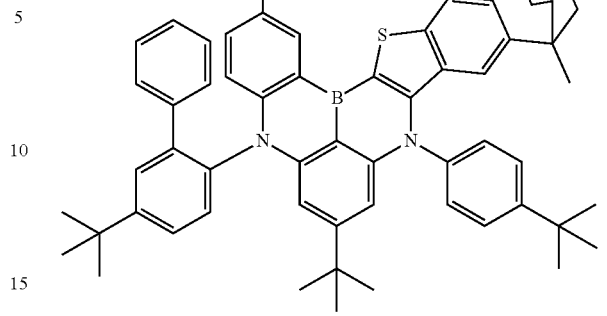
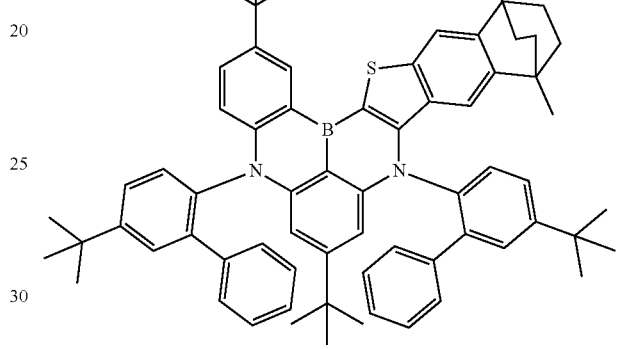
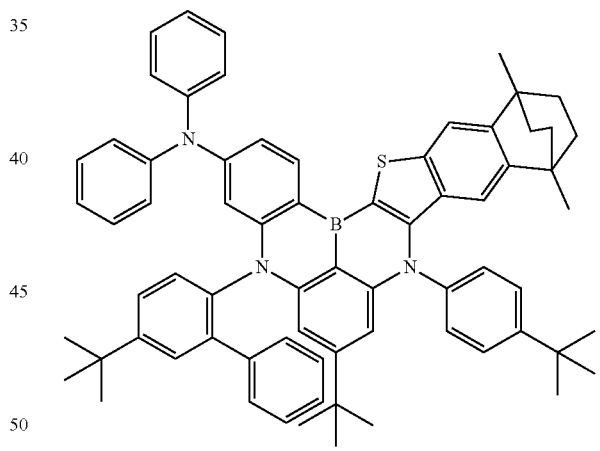
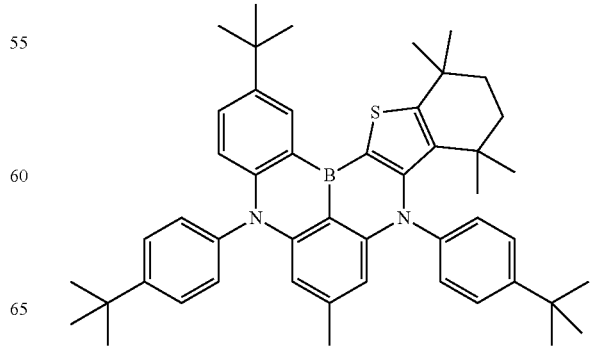

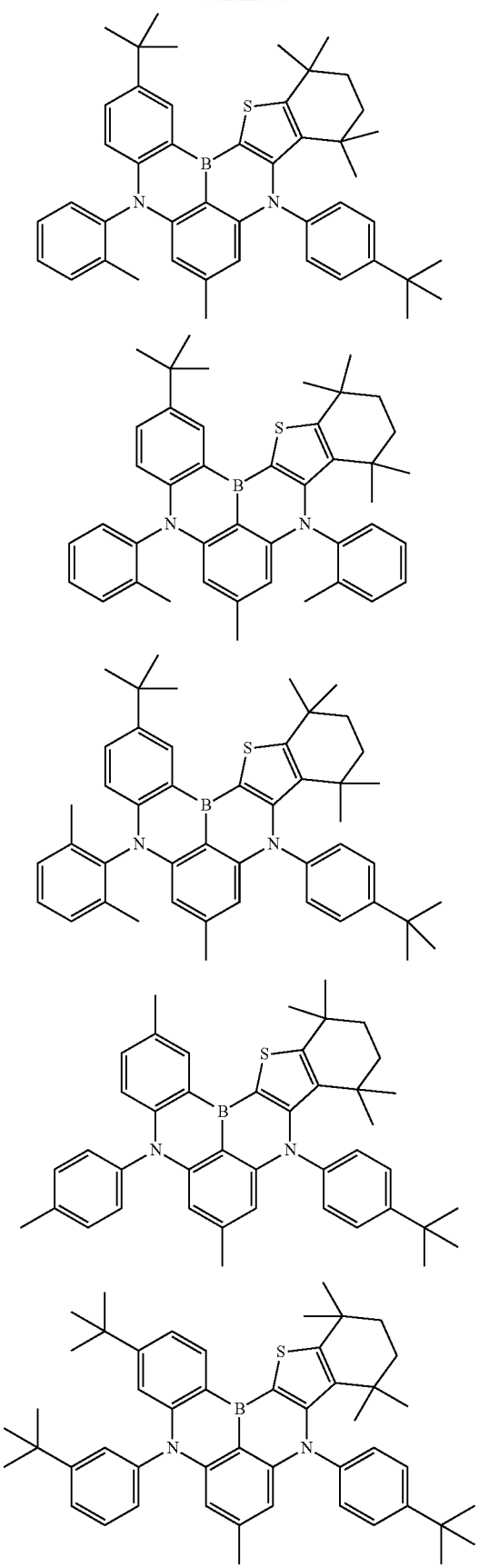
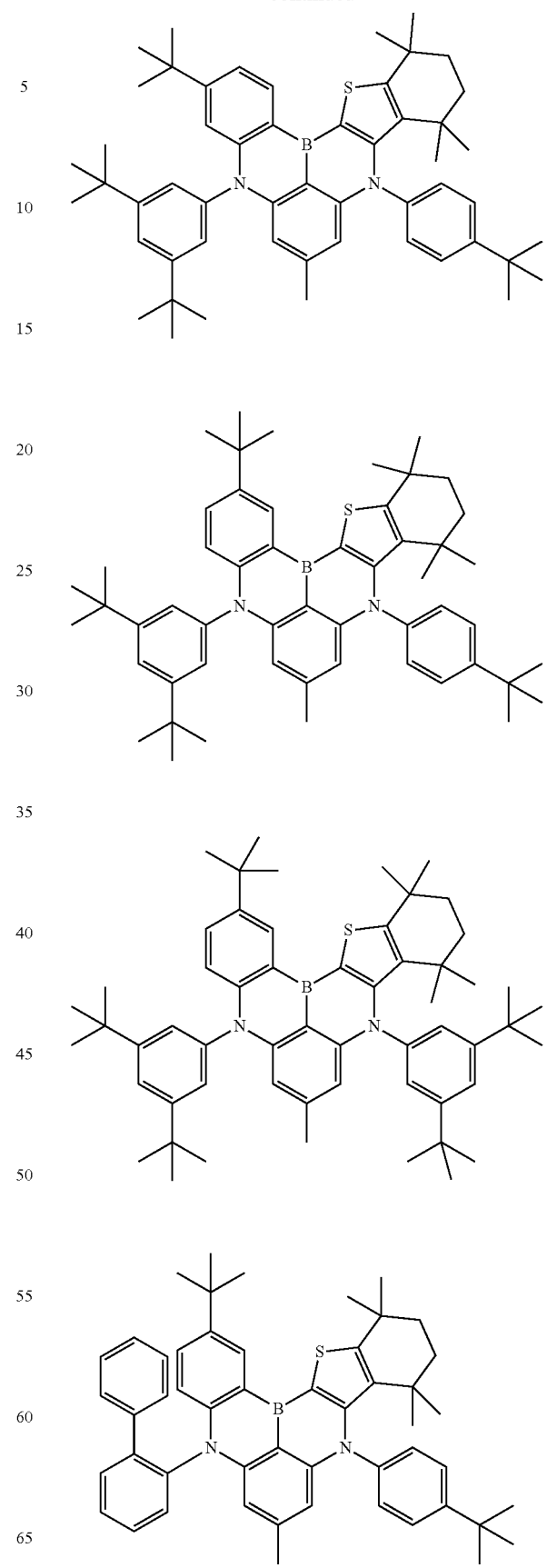

119
-continued
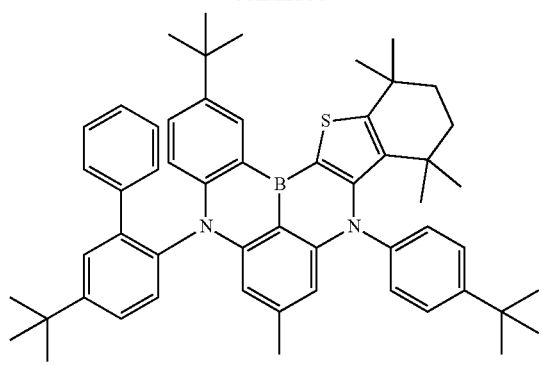
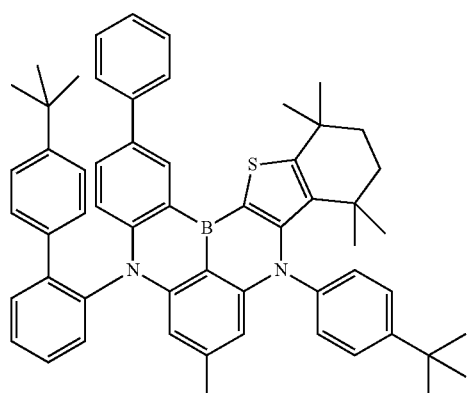
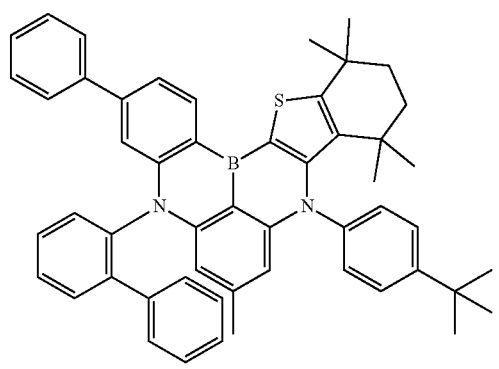
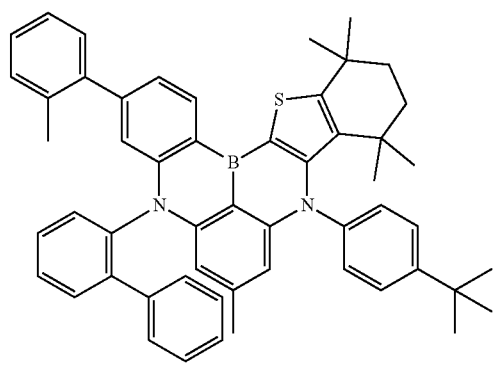
120
-continued
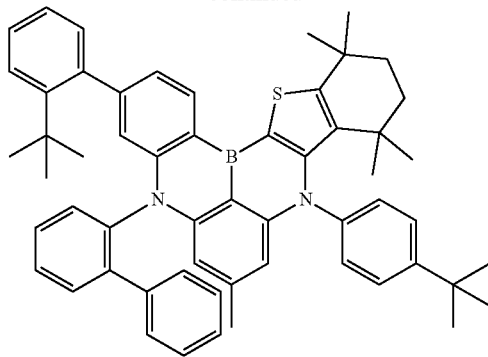
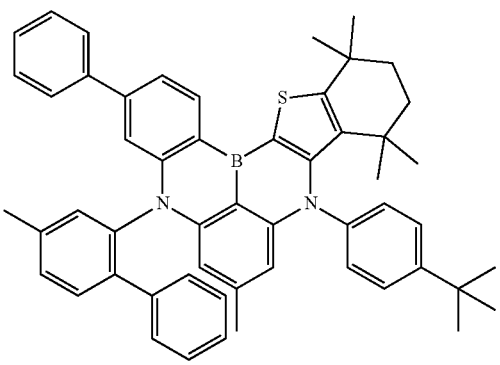
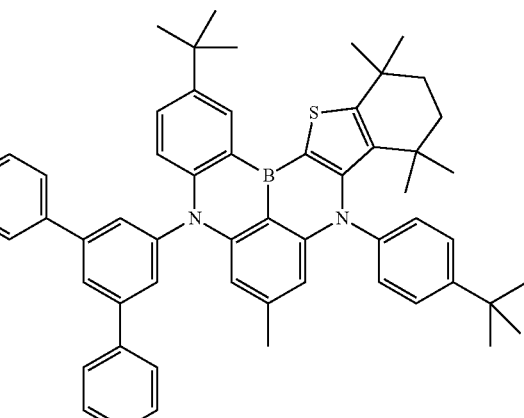
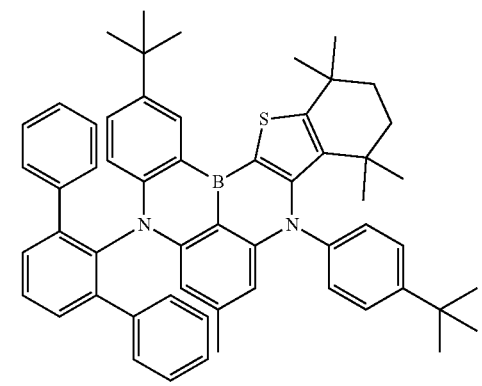

| 121 | 122 |
|---|---|
| -continued | -continued |
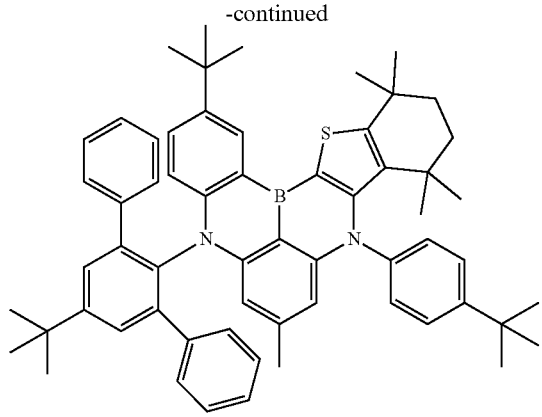
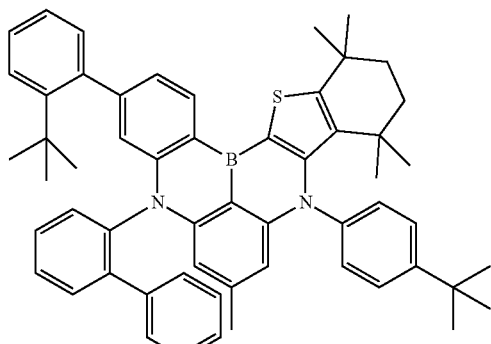
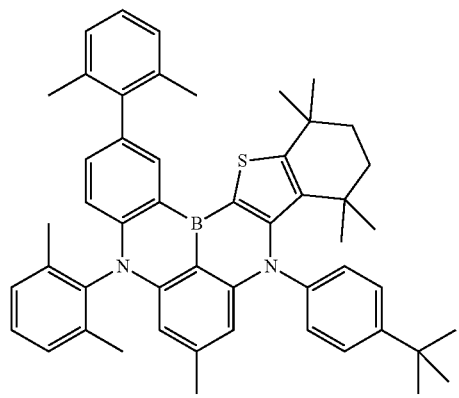
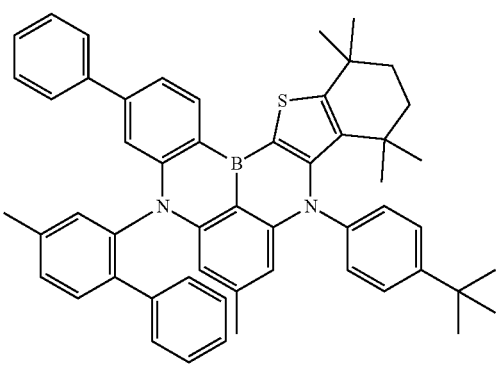
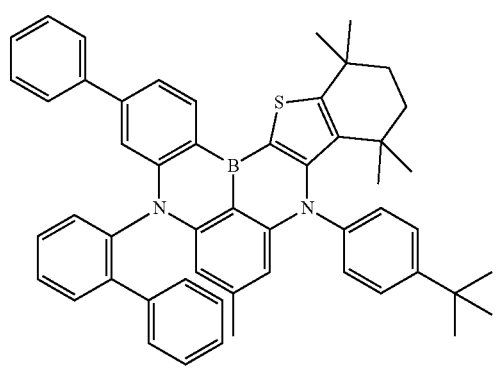
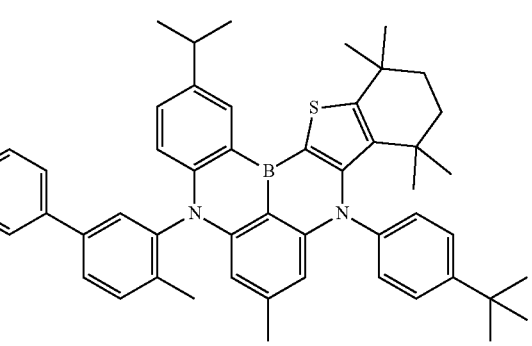
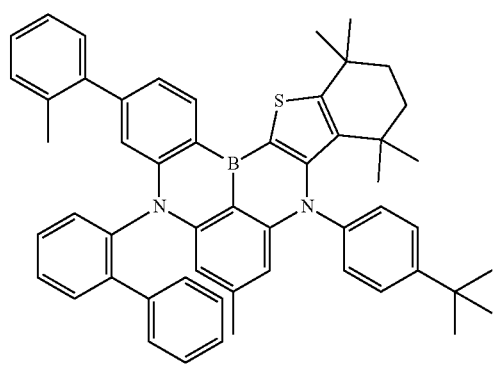
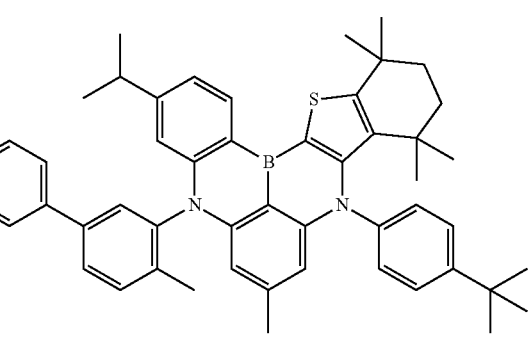

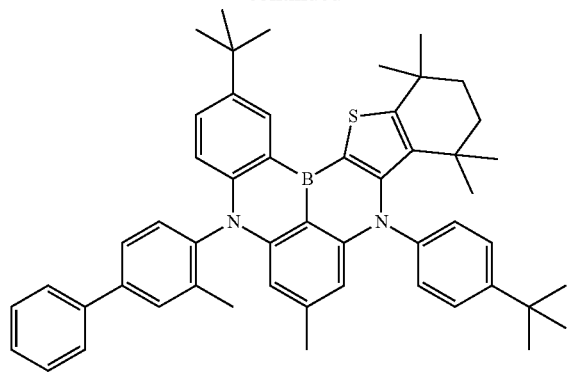
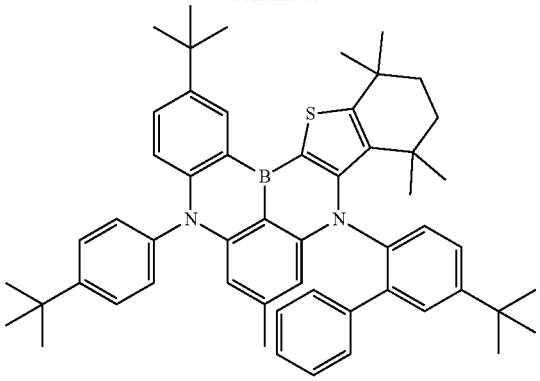
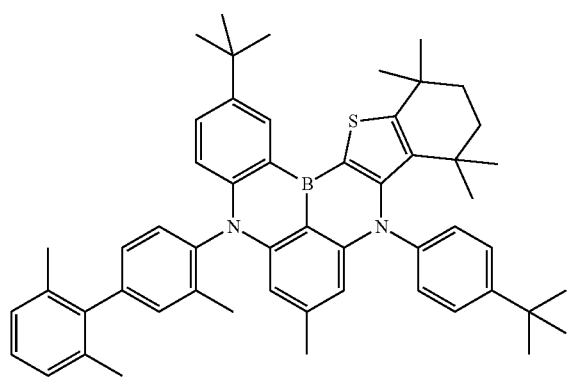
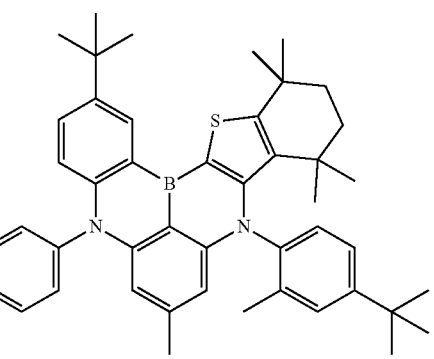
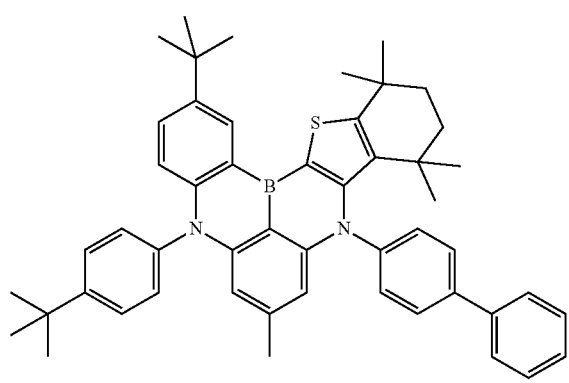
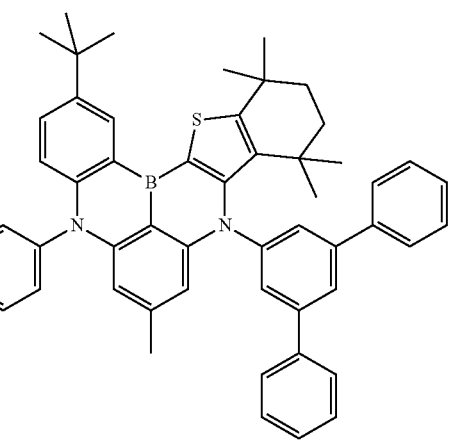
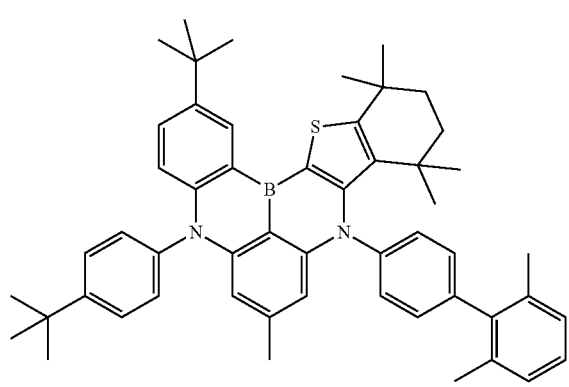
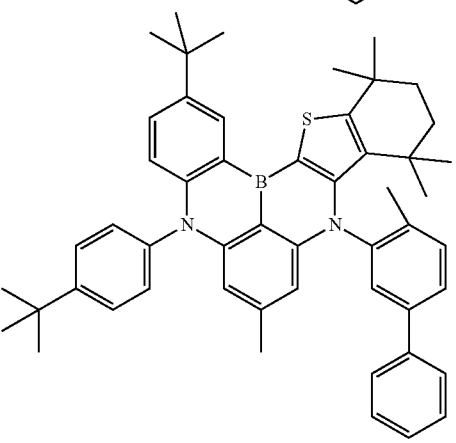

125
-continued
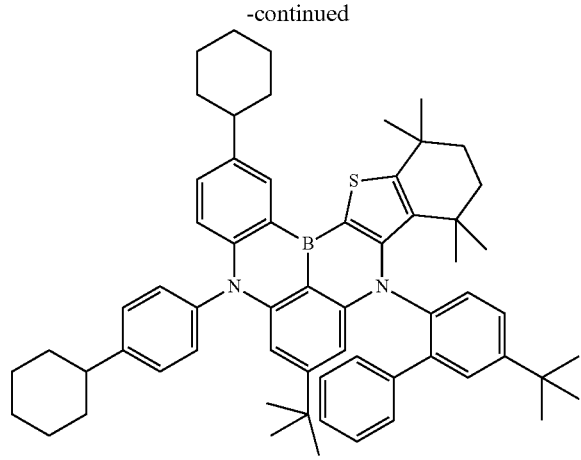
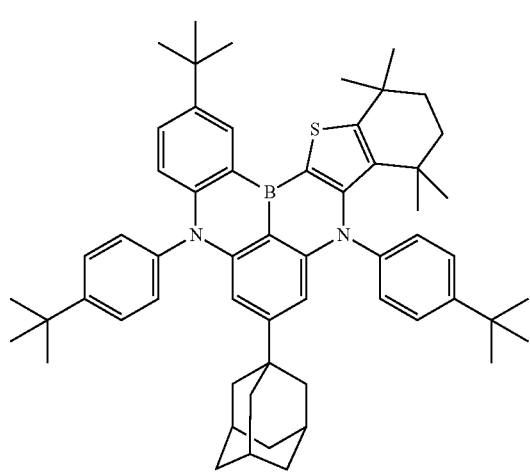
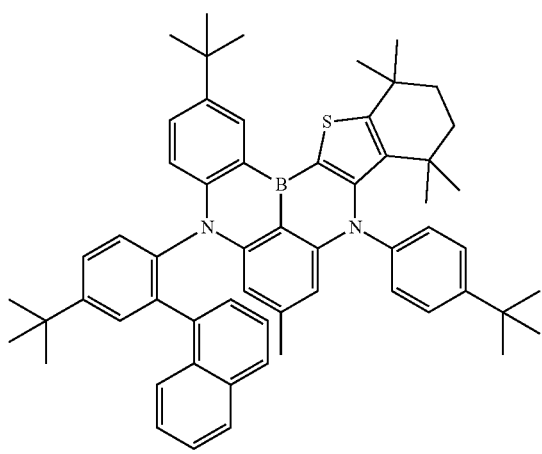
126
-continued
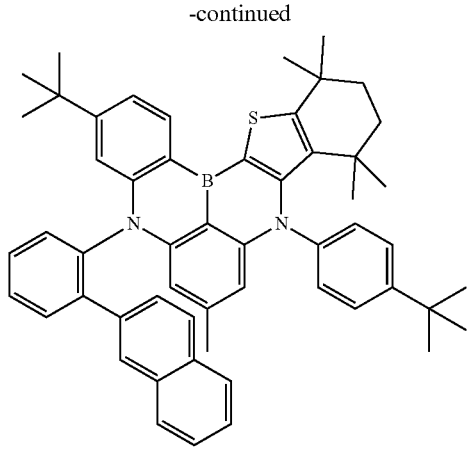
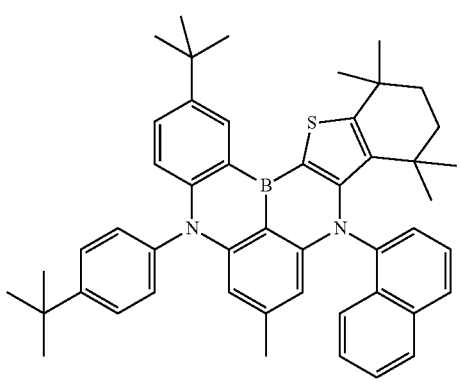
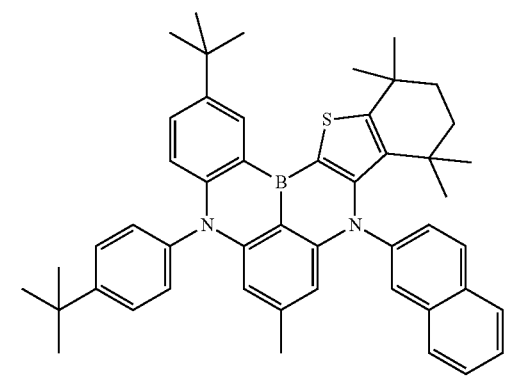
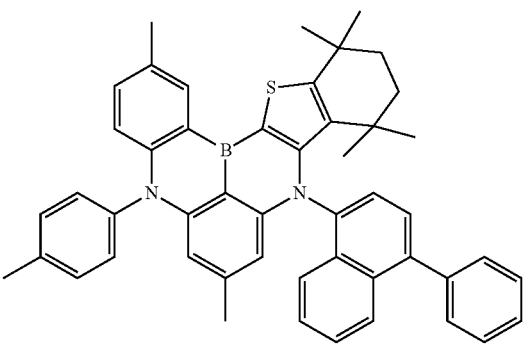

127
-continued
128
-continued
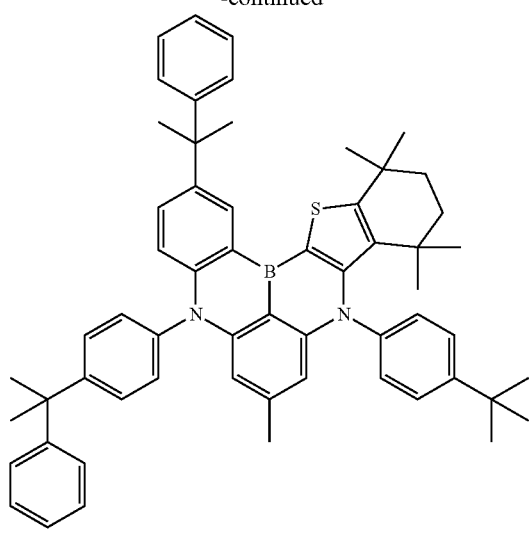
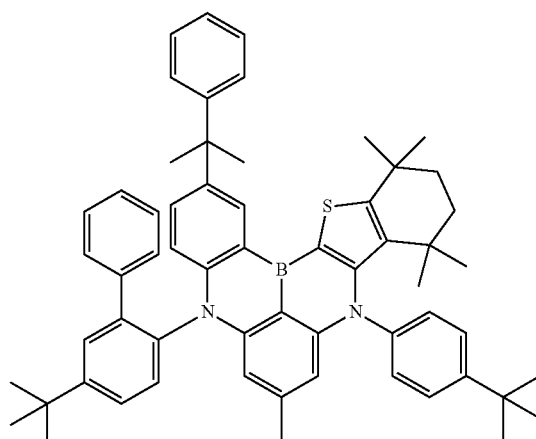
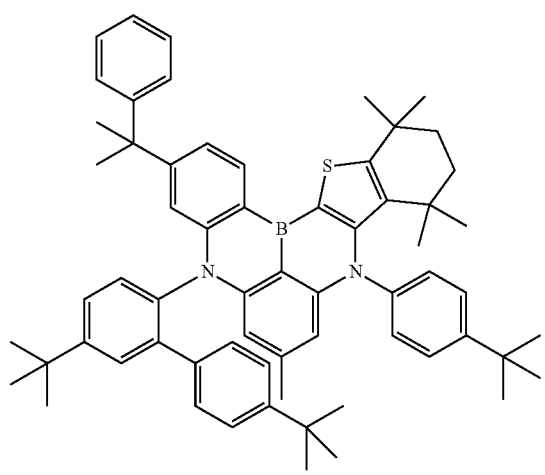
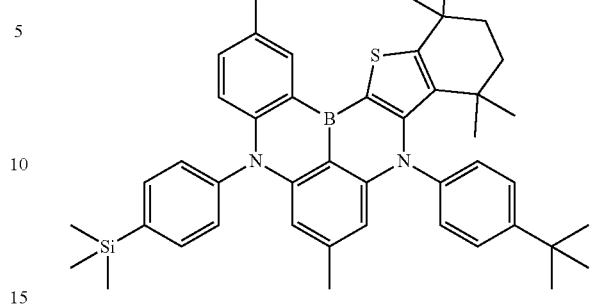
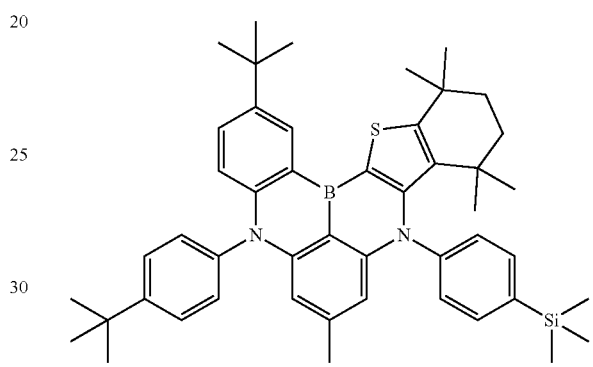
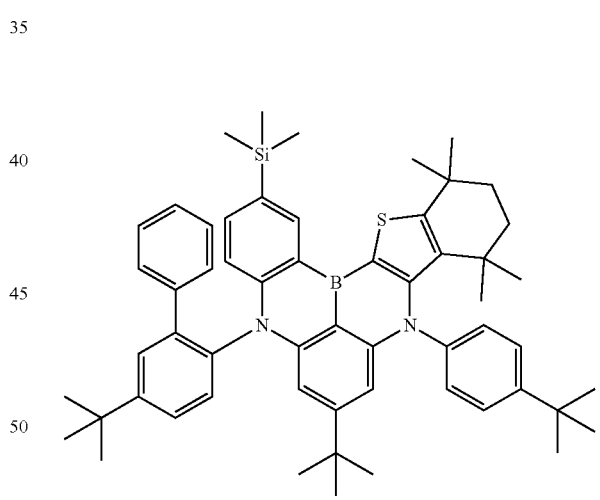
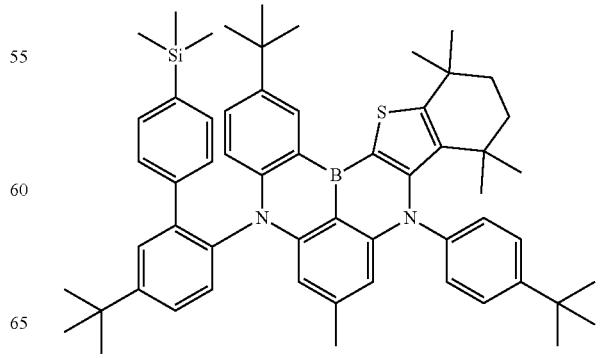

129
-continued
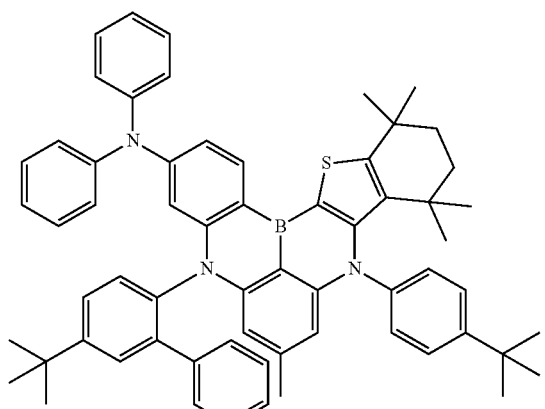
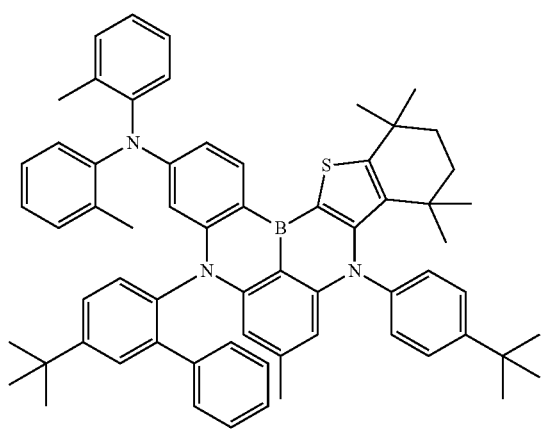
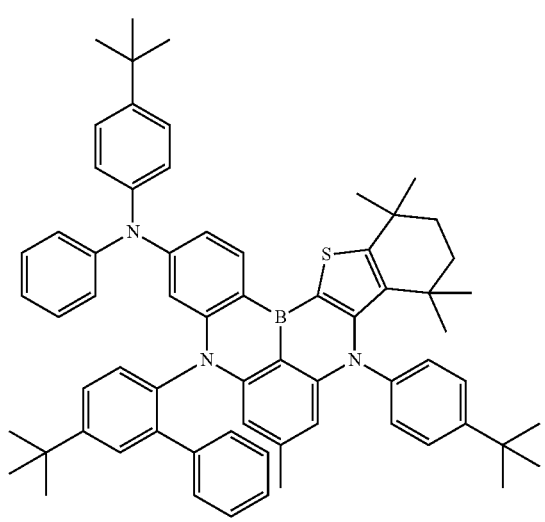
130
-continued
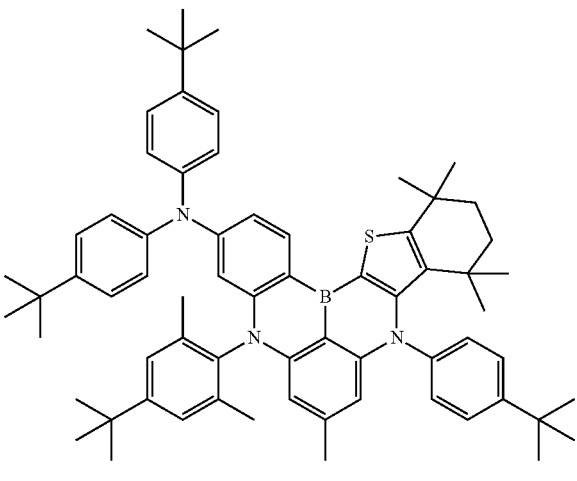
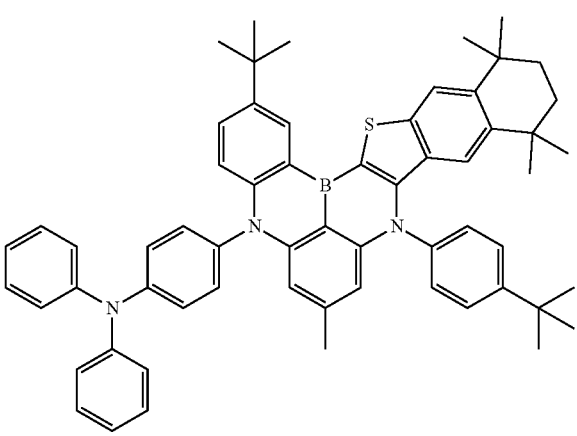
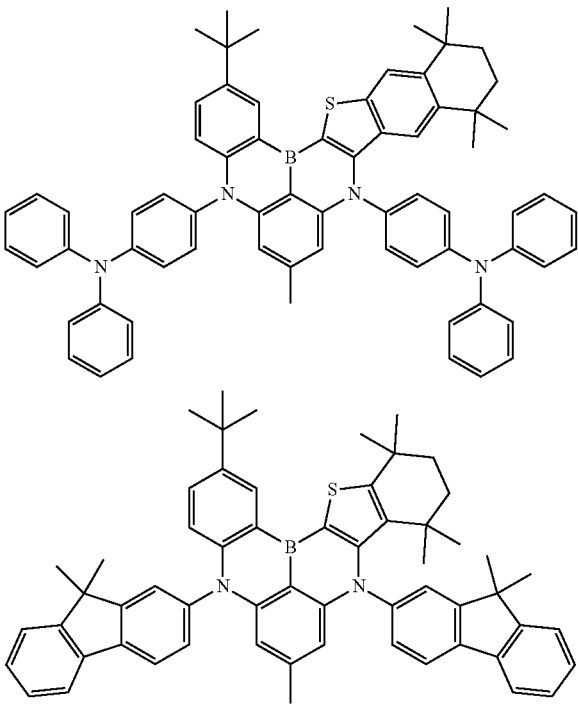

131
-continued
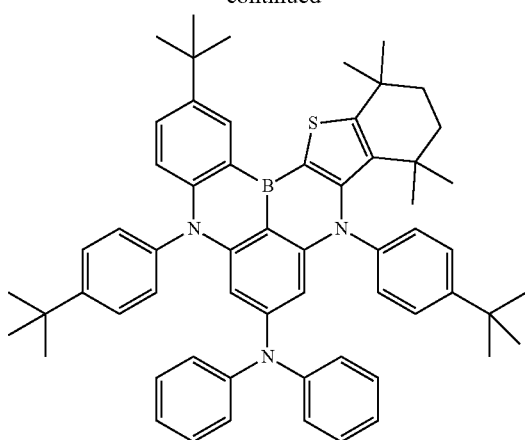
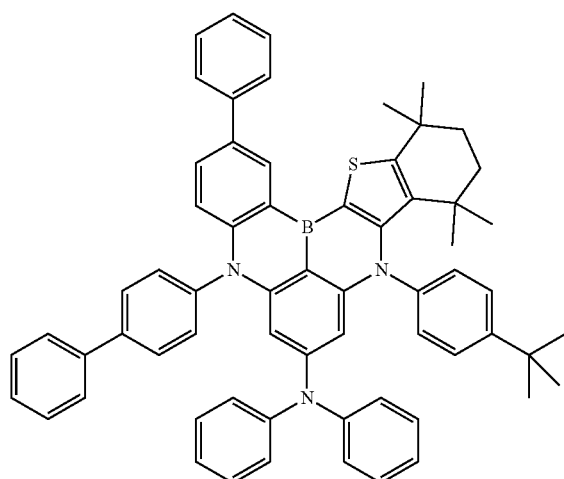
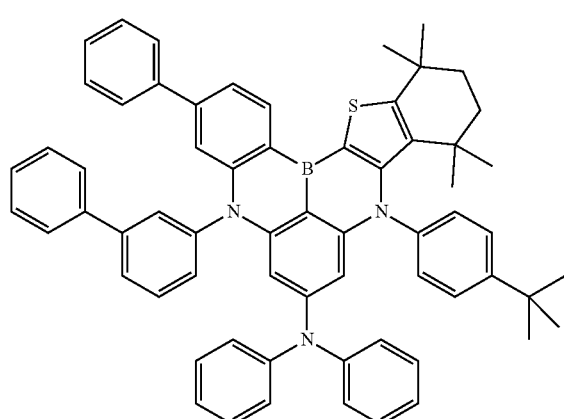
132
-continued
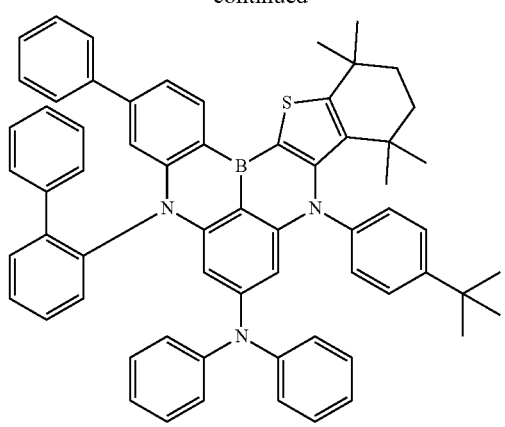
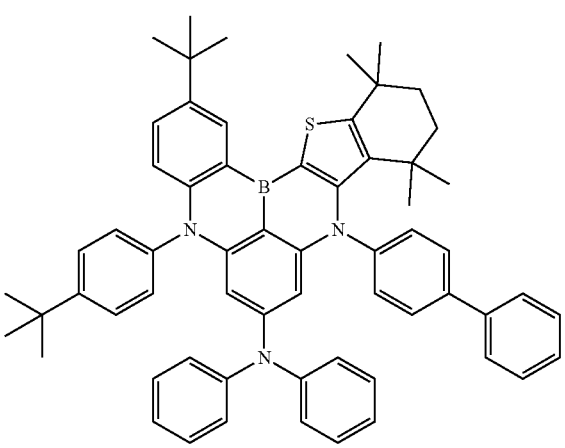
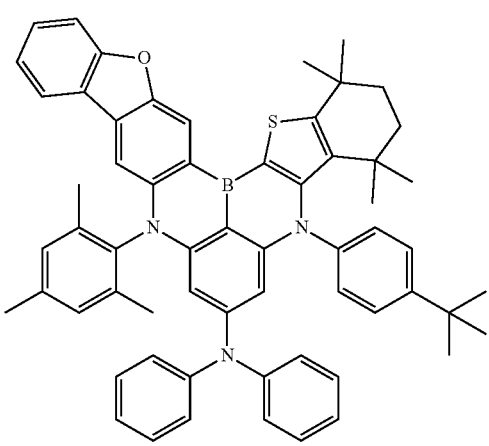

133
-continued
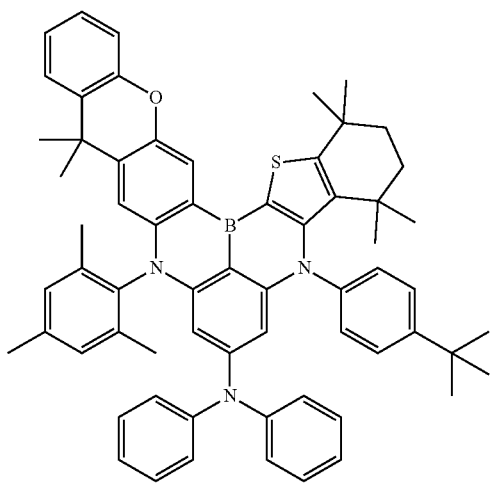
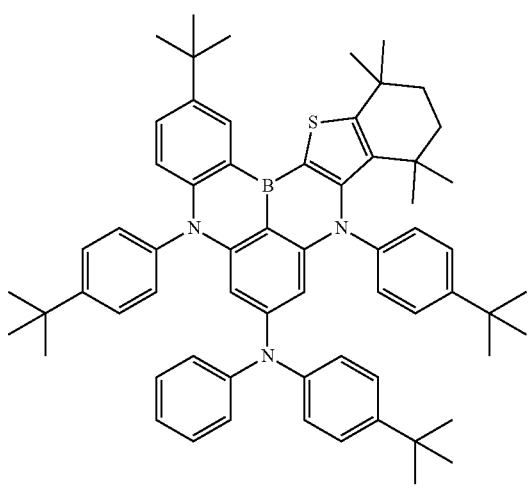
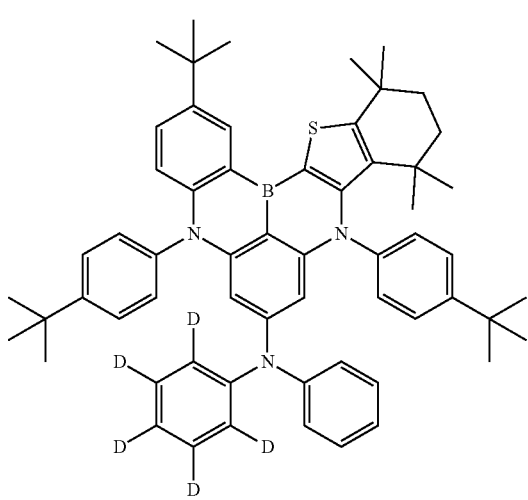
134
-continued
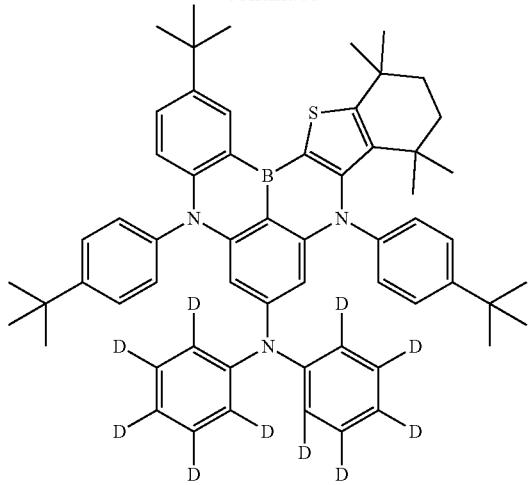
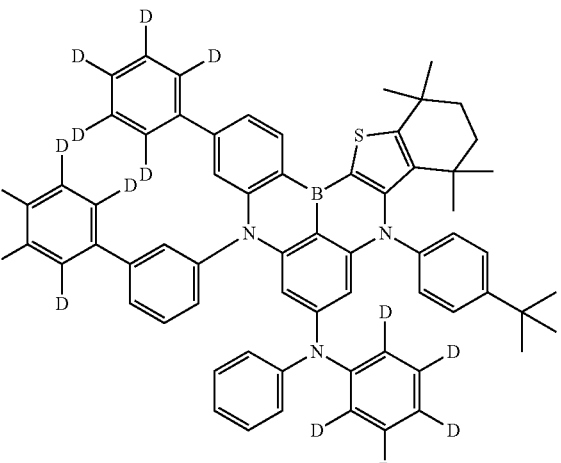
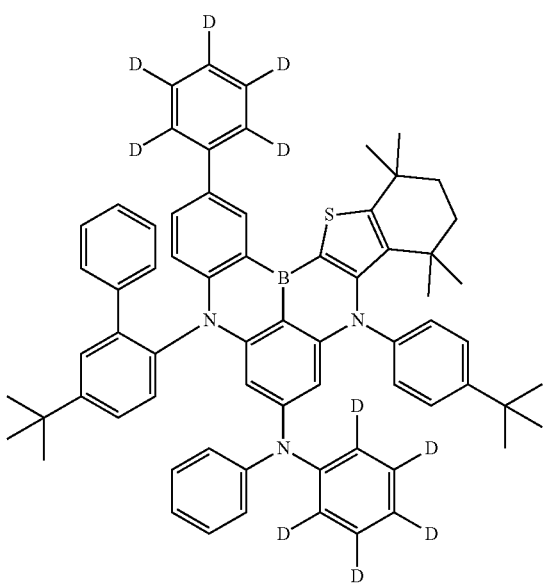

135
-continued

136
-continued

137
-continued
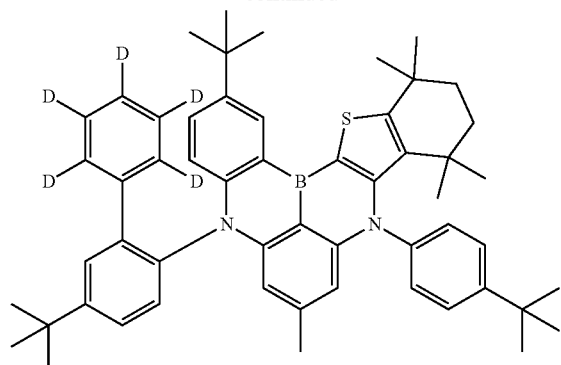
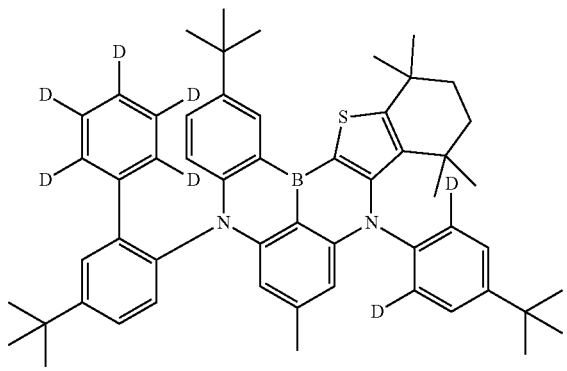
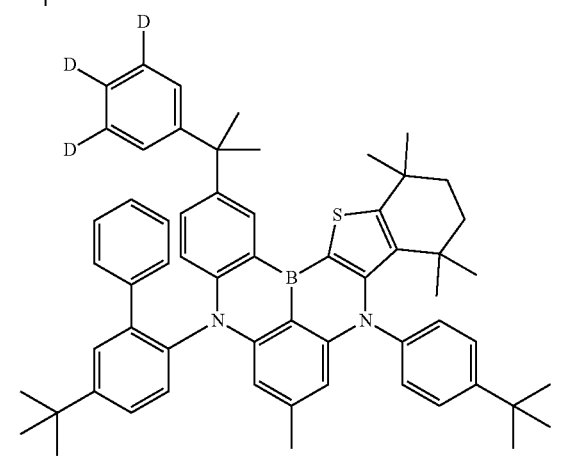
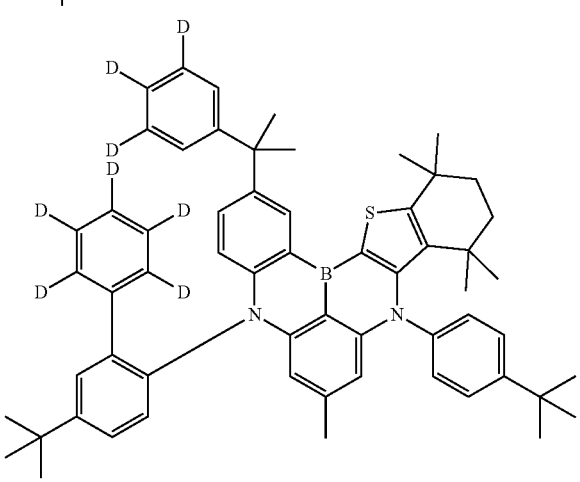
138
-continued
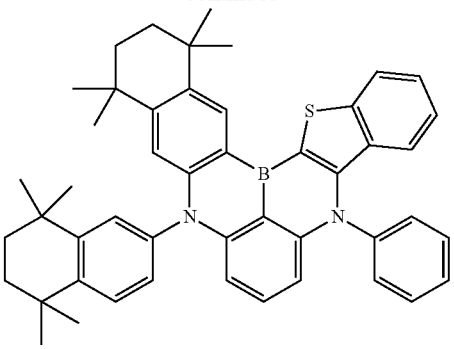
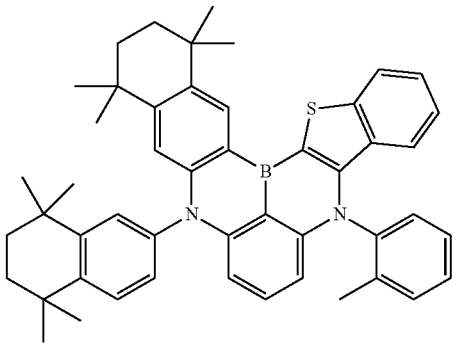
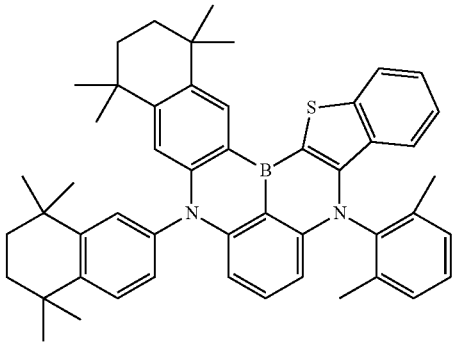
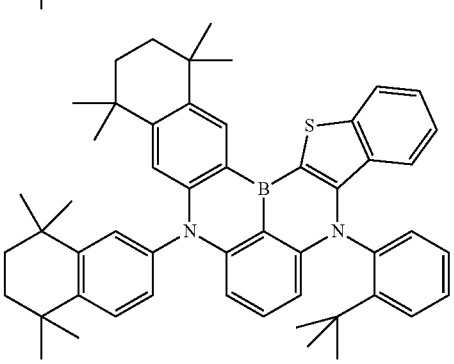
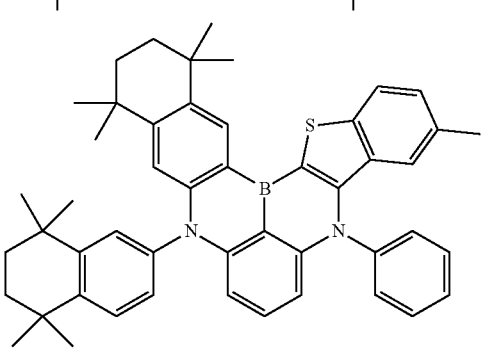

| 139 -continued | 140 -continued |
|---|---|
| 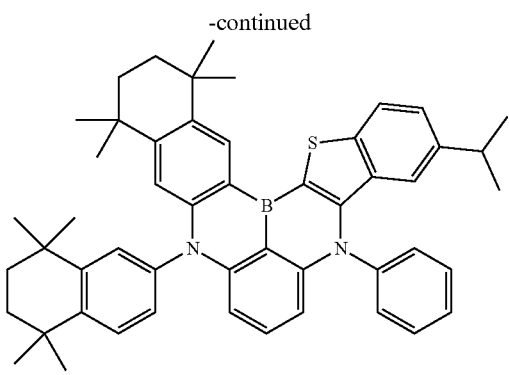 | 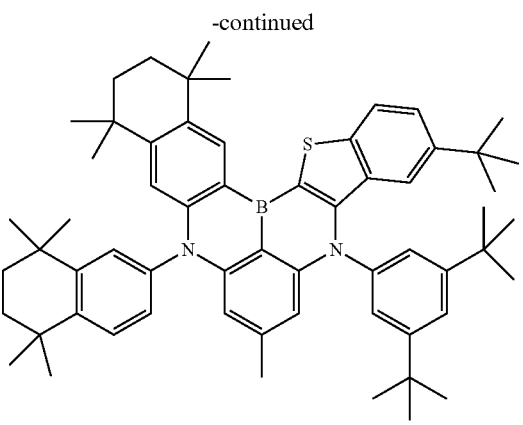 |
| 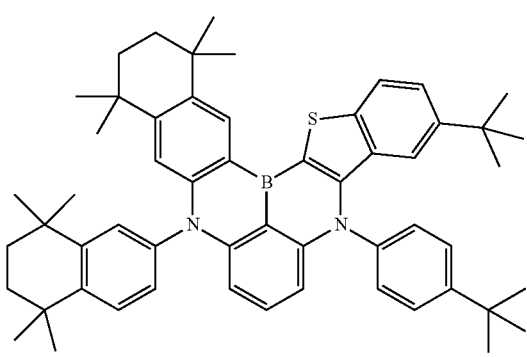 | 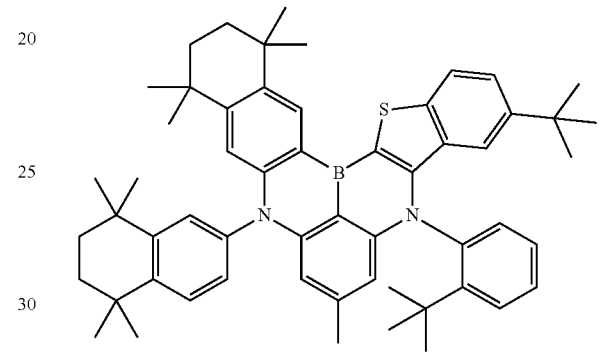 |
| 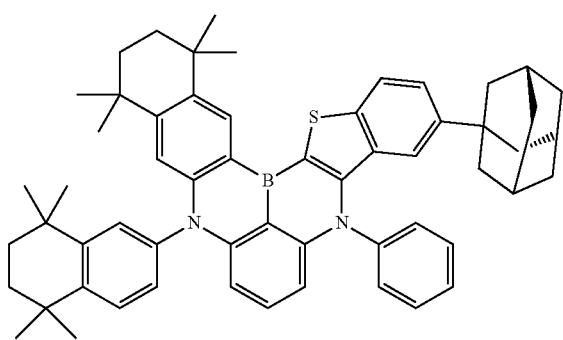 | 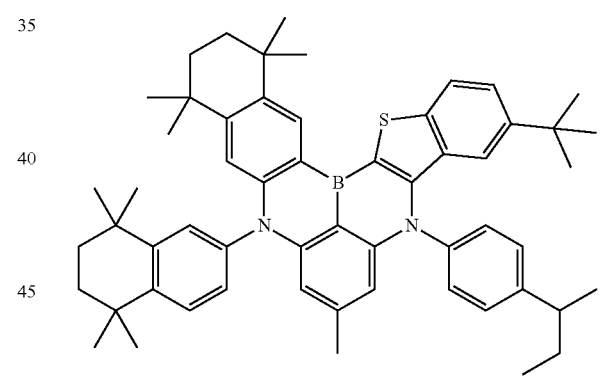 |
| 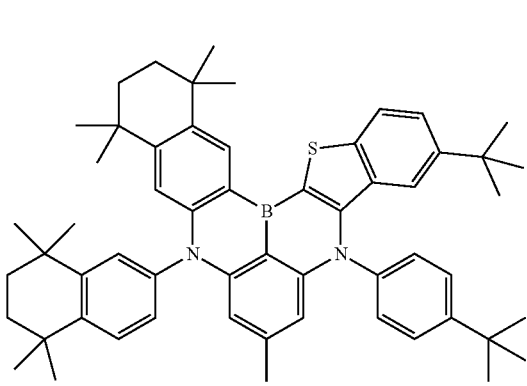 | 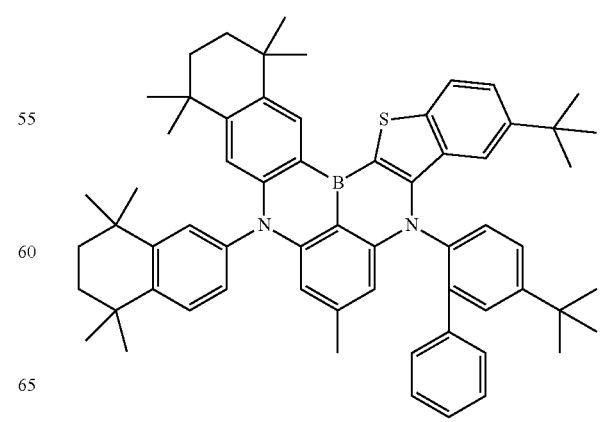 |

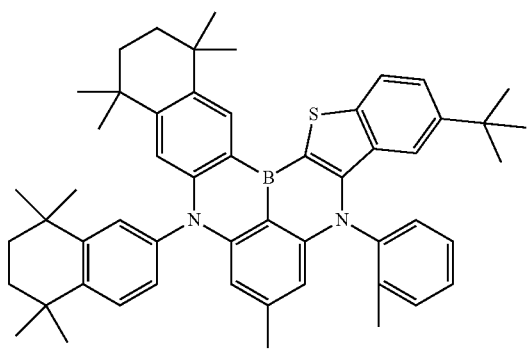
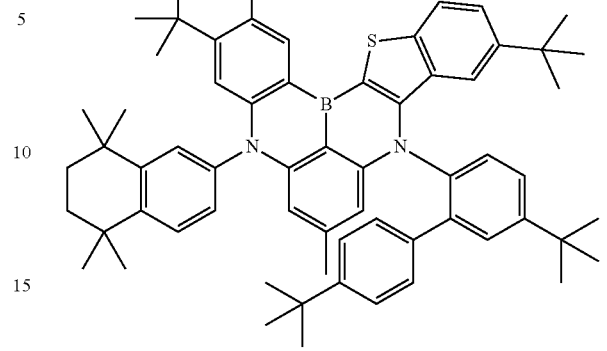
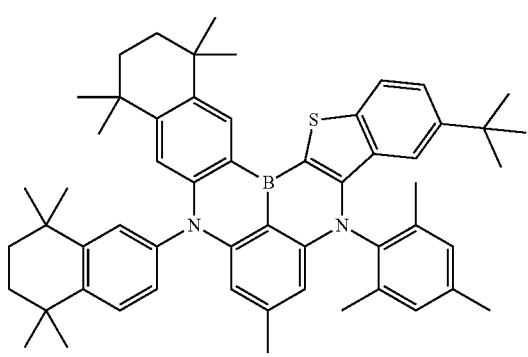
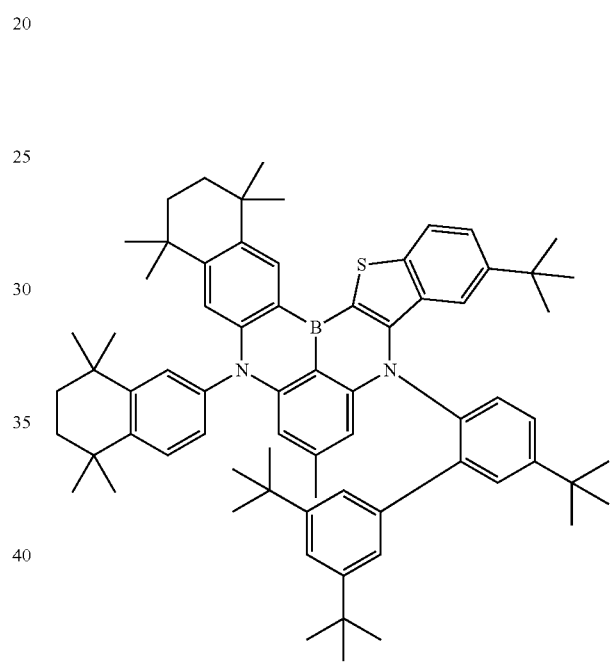
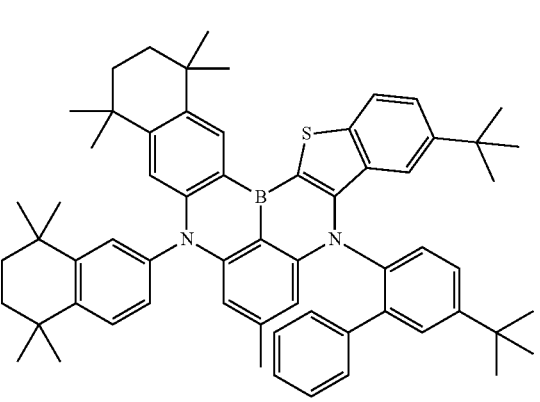
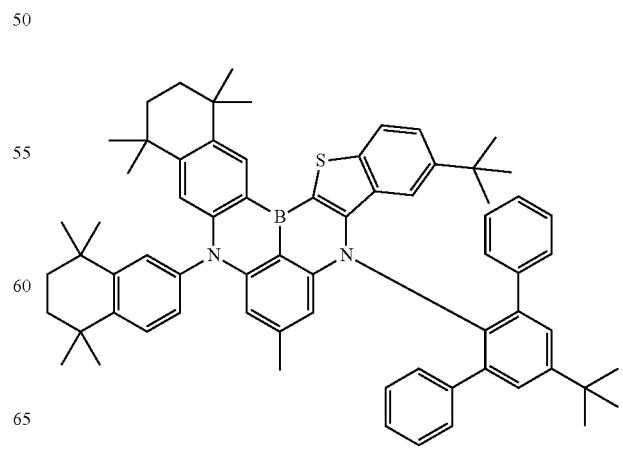

143
-continued
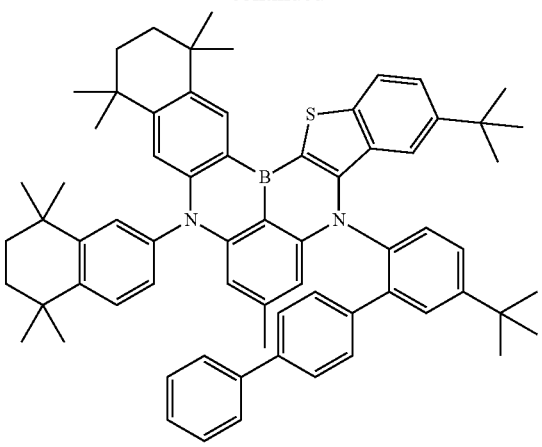
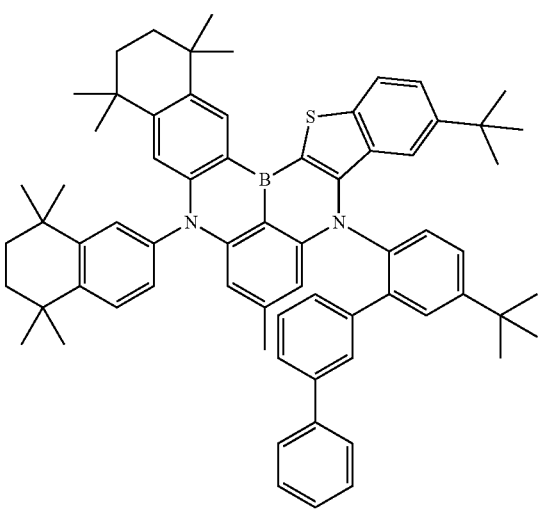
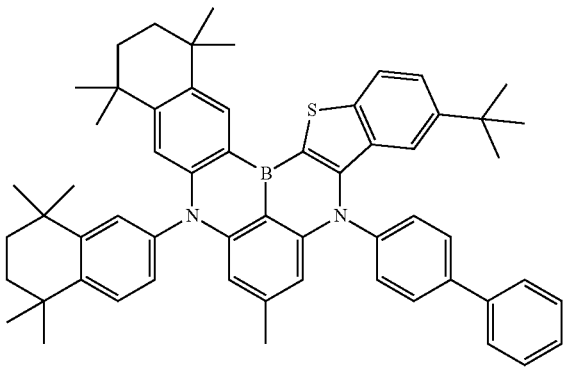
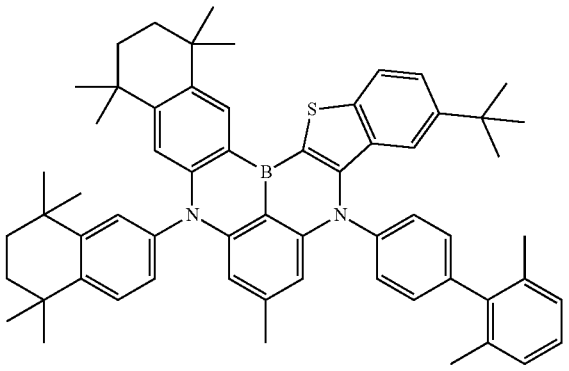
144
-continued
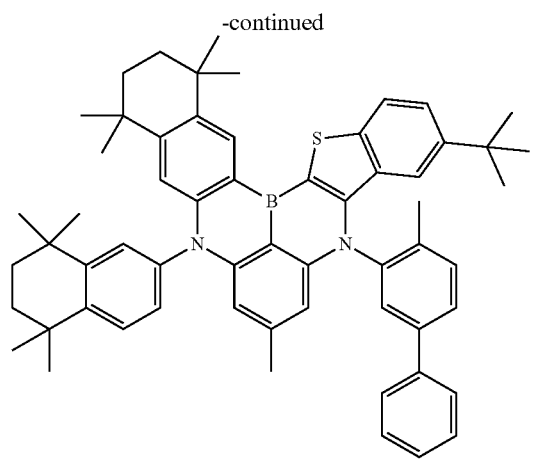
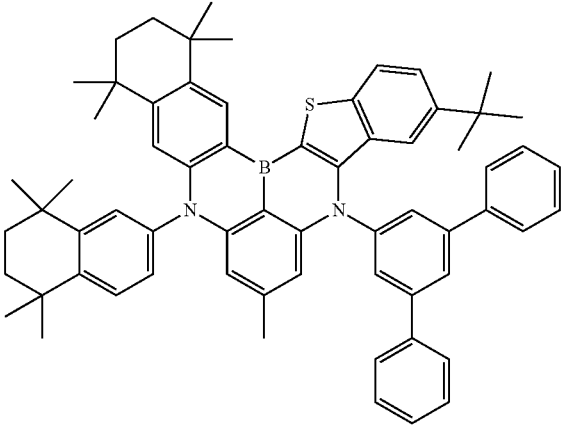
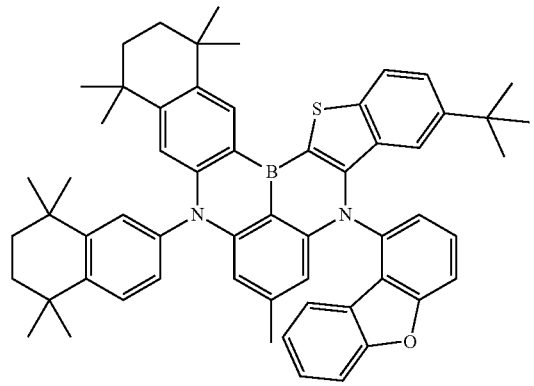
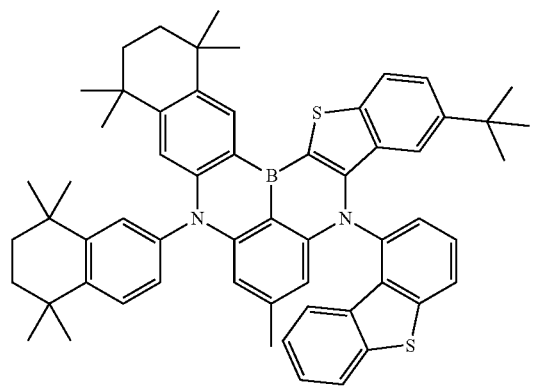

145
-continued
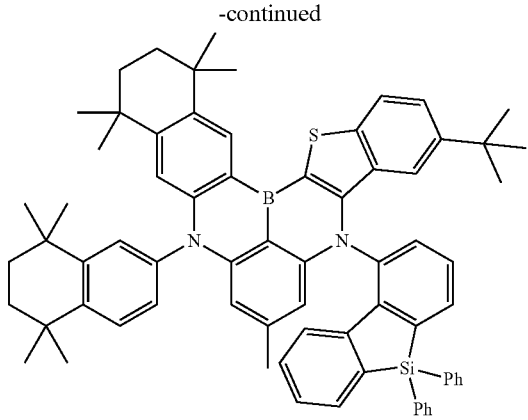
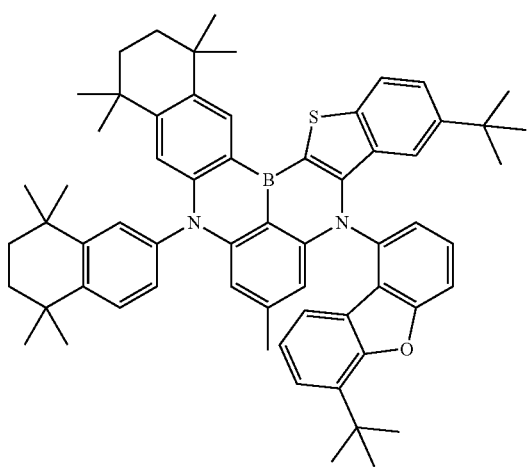
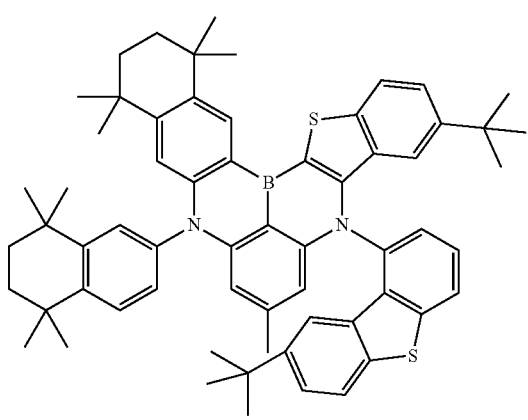
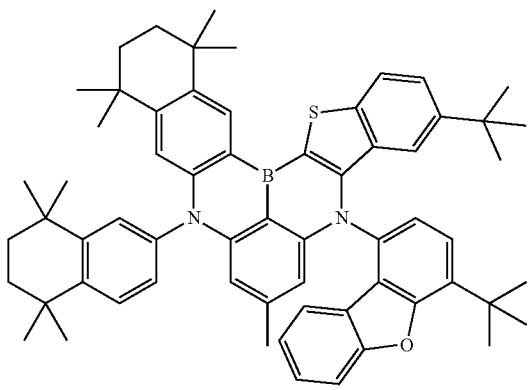
146
-continued
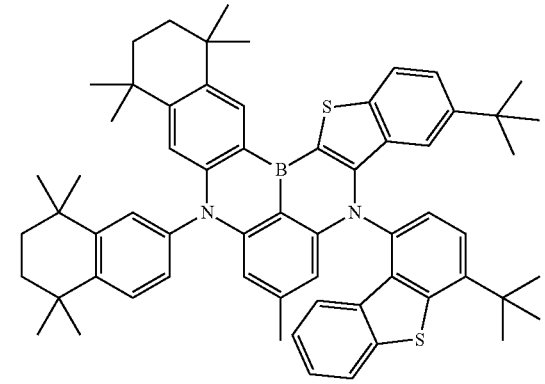
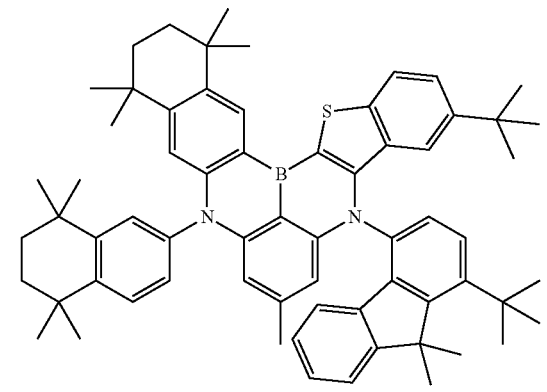
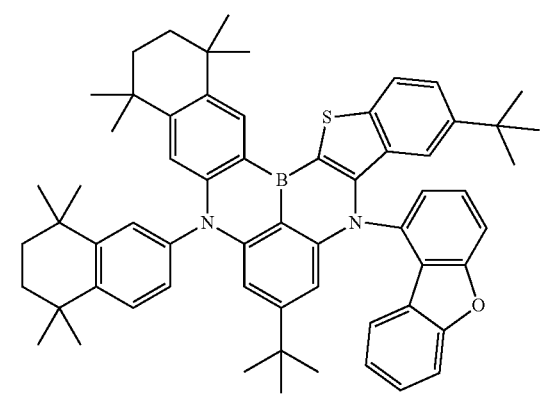
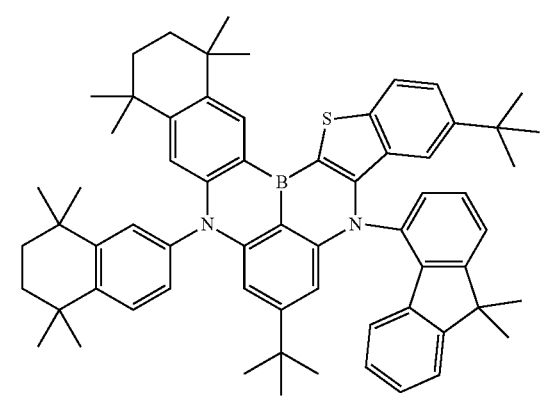

147
-continued
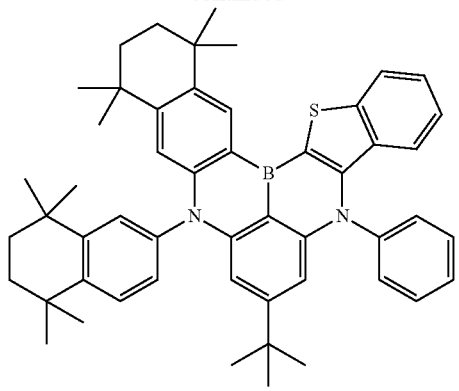
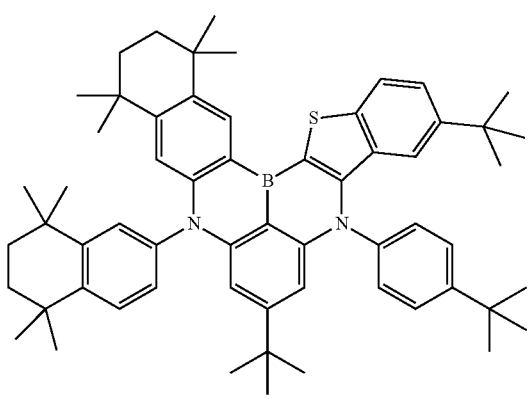
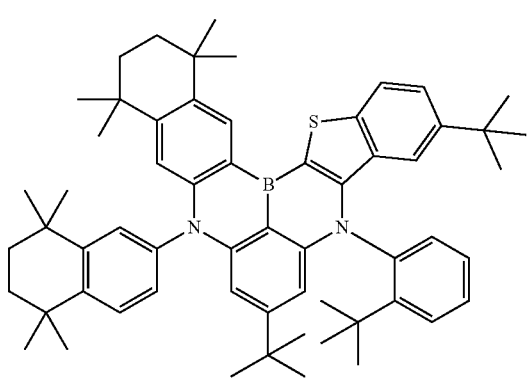
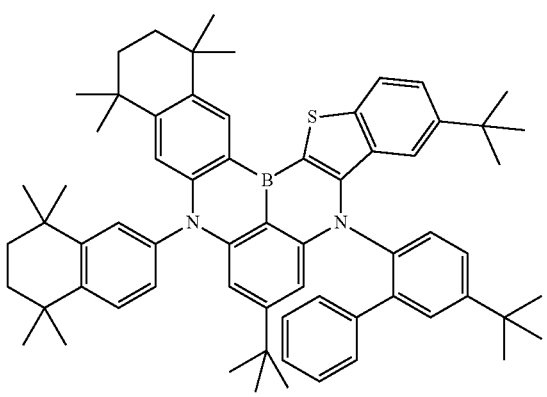
148
-continued
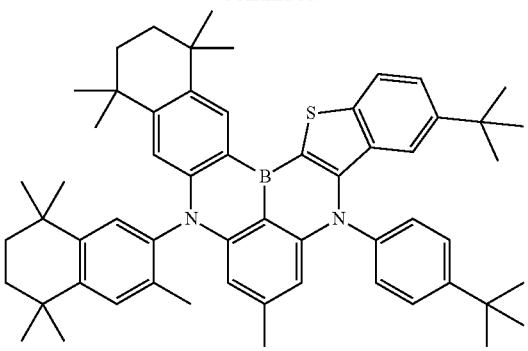
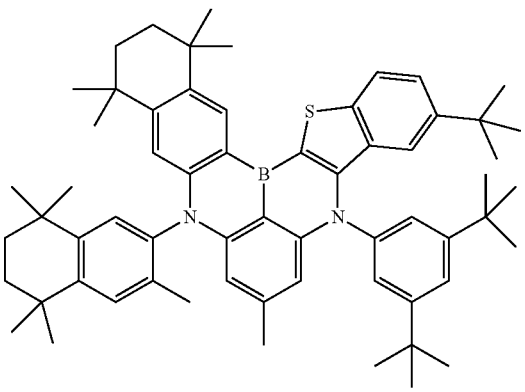
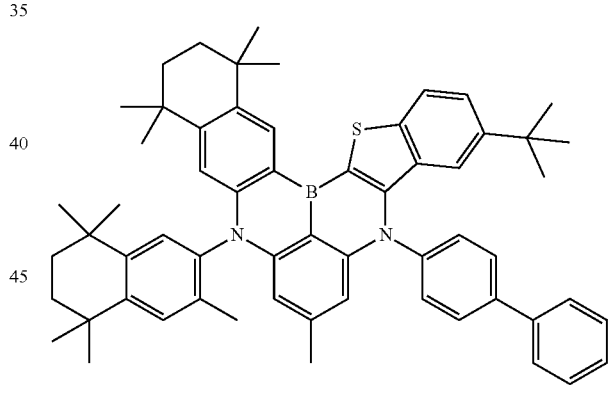
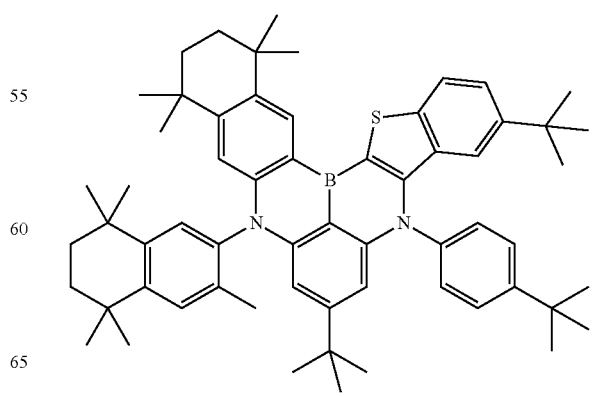

| 149 -continued | 150 -continued |
|---|---|
| 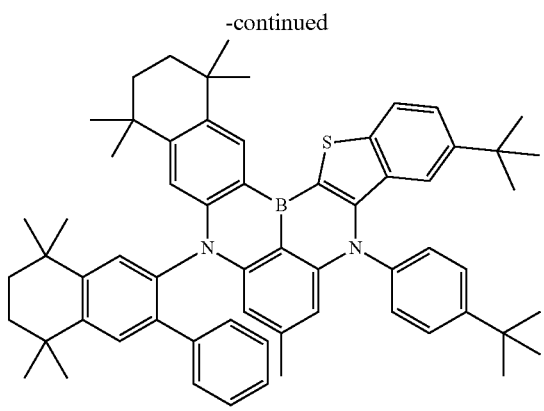 | 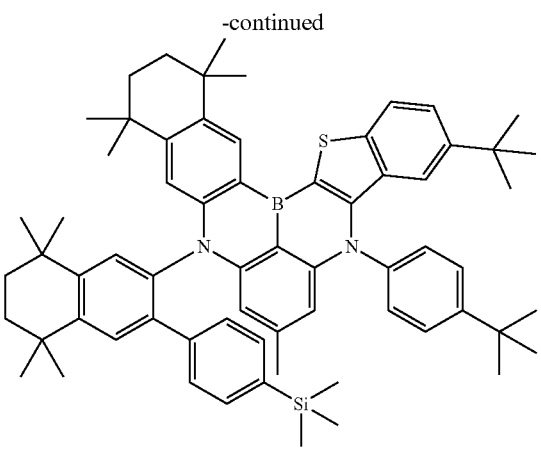 |
| 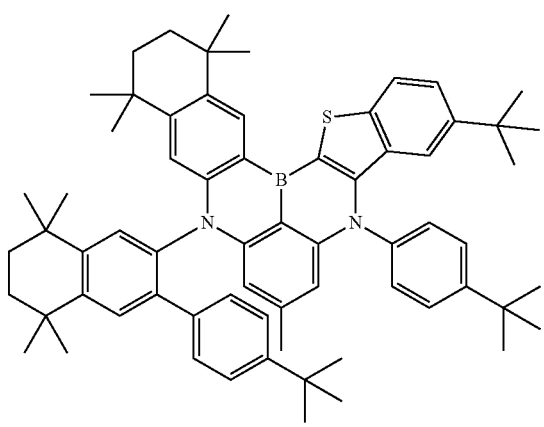 | 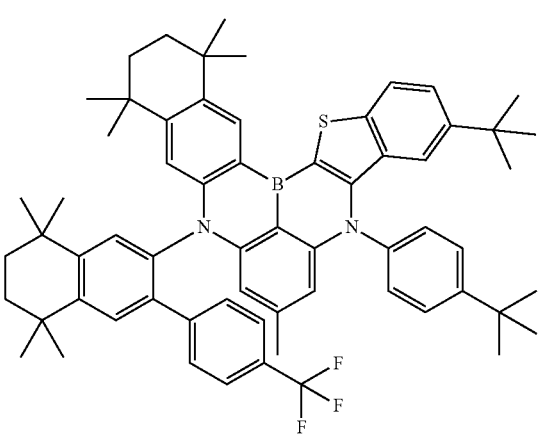 |
| 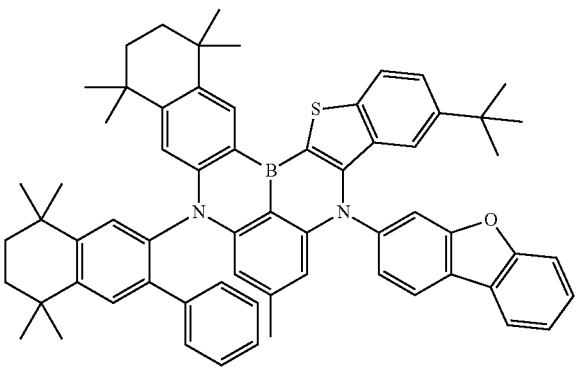 | 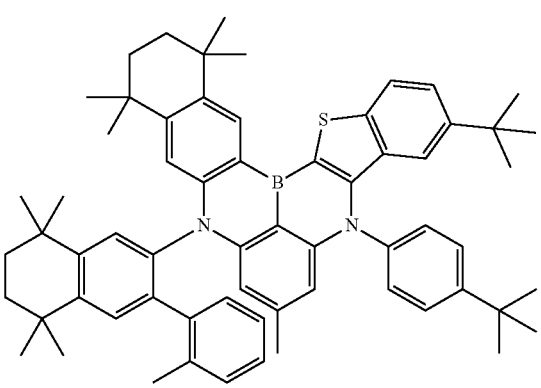 |
| 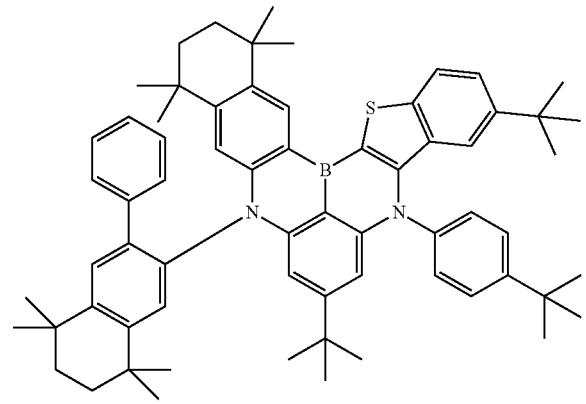 | 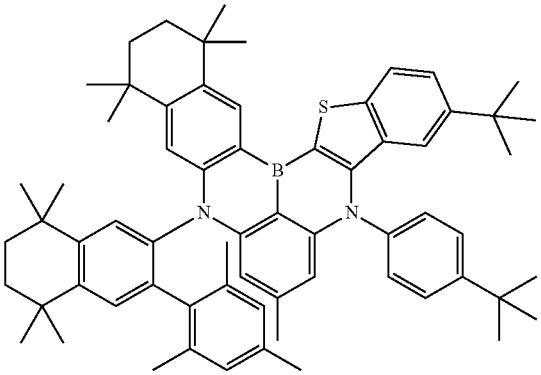 |

151
-continued
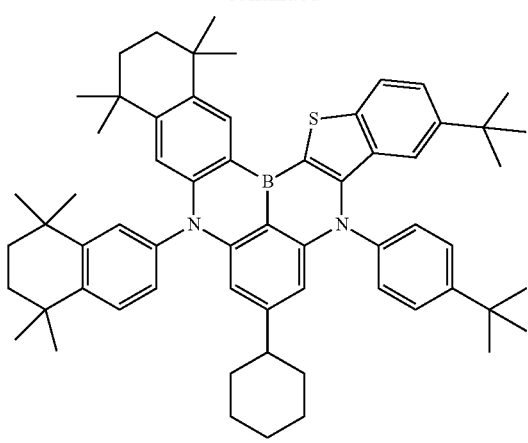
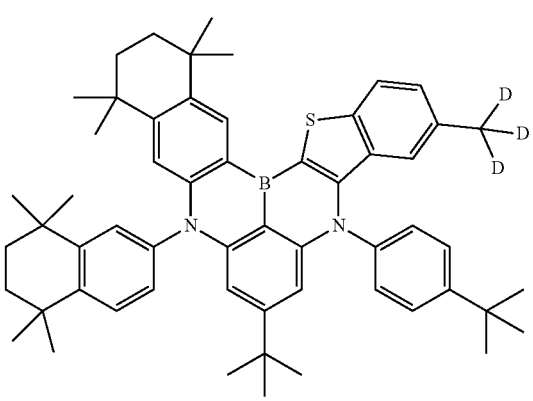
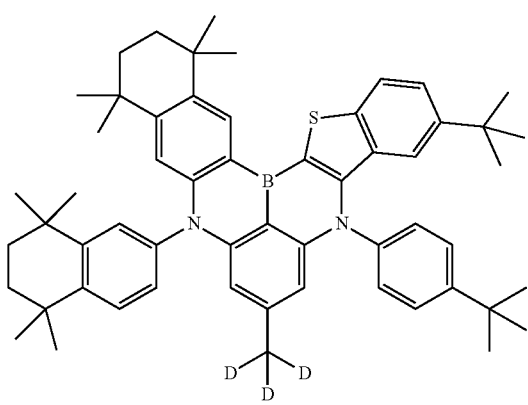
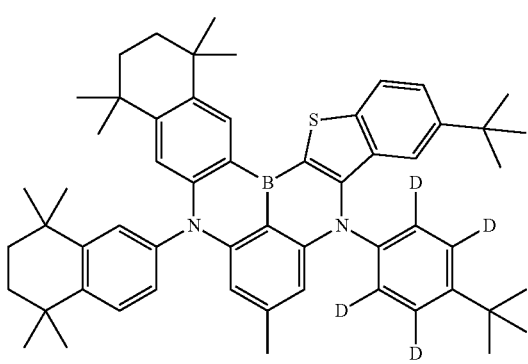
152
-continued
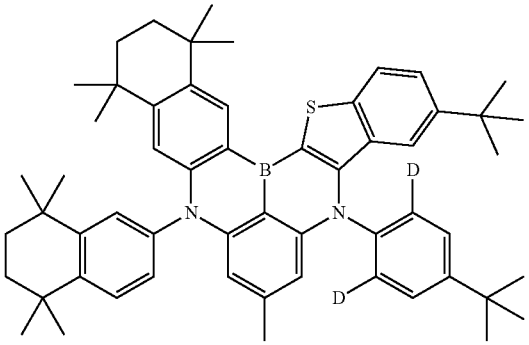
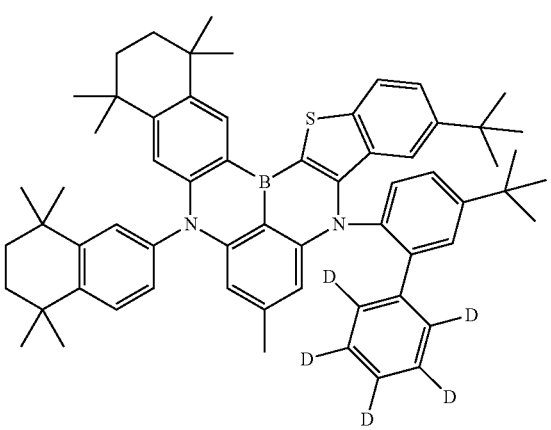
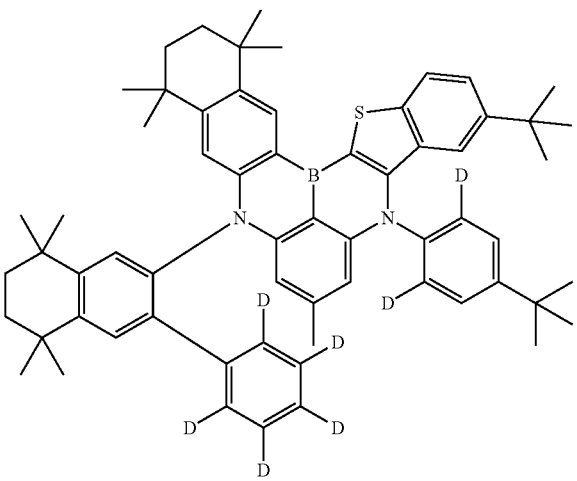
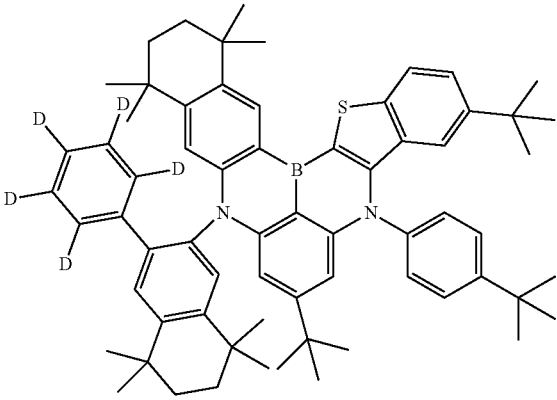

153
-continued
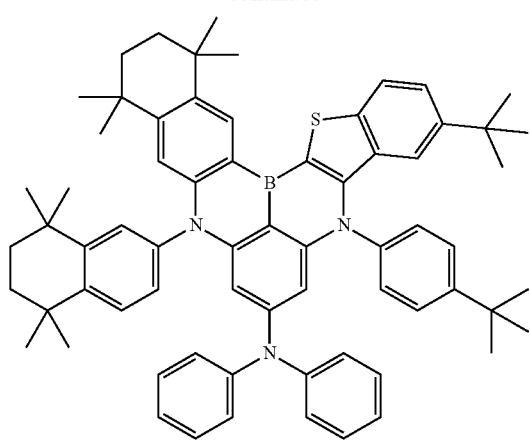
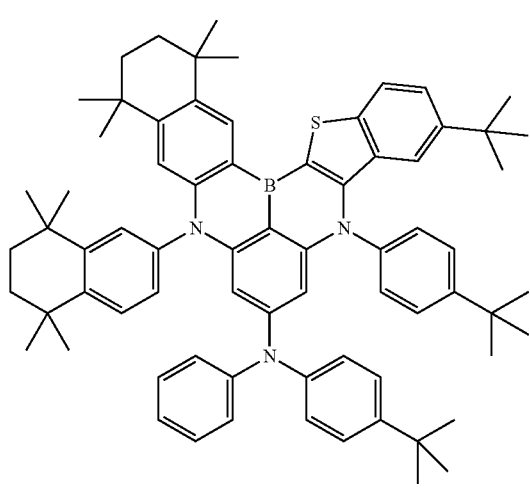
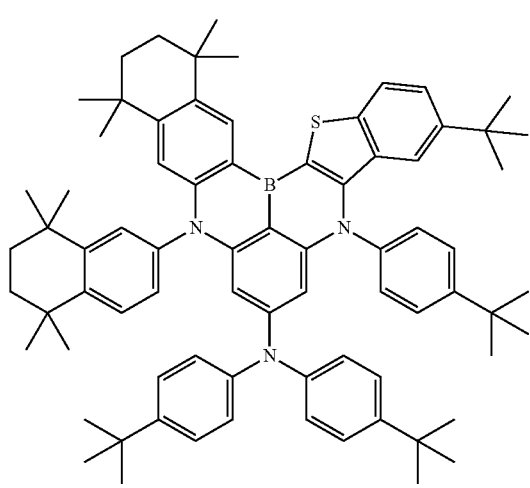
154
-continued
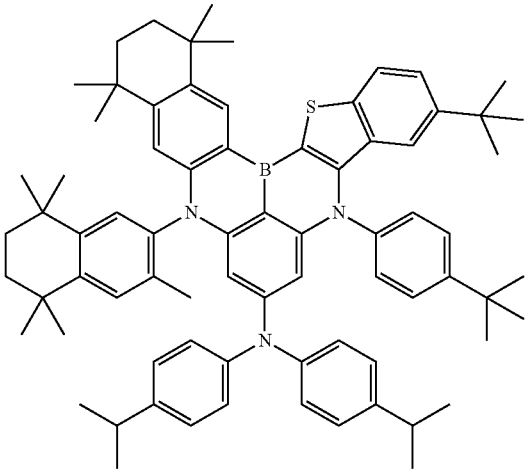
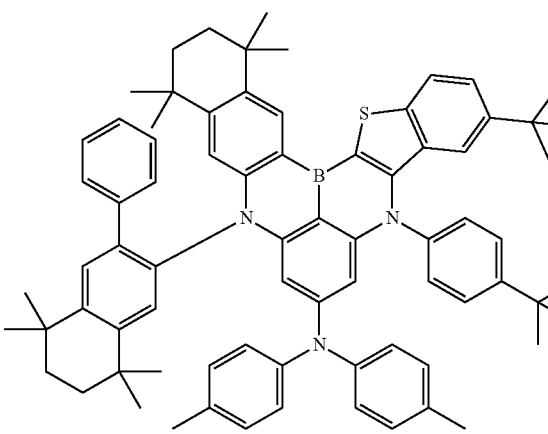
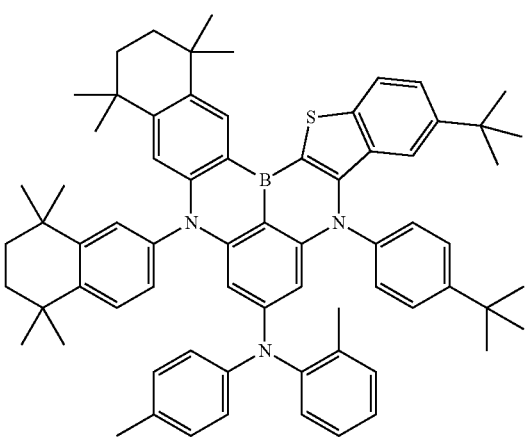

155
-continued

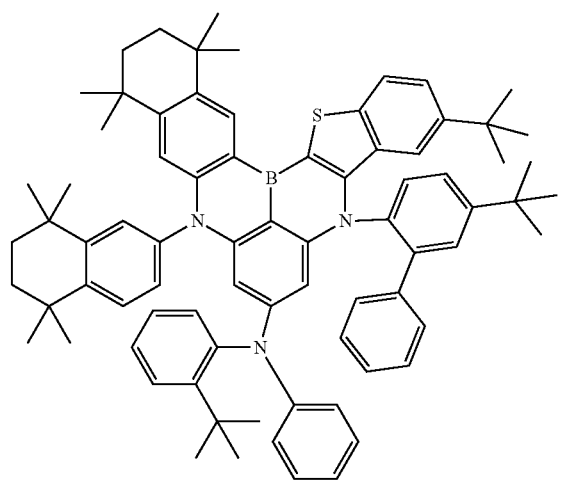
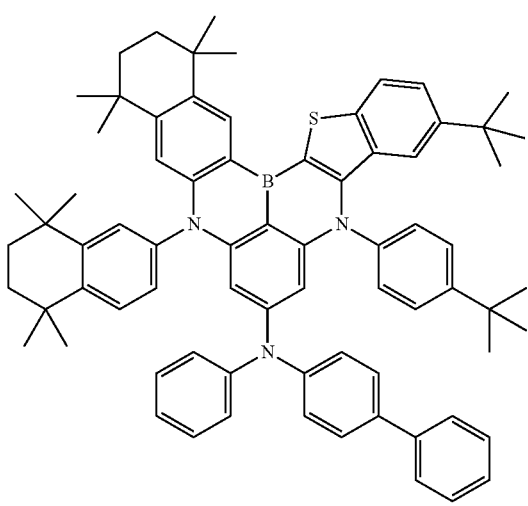
156
-continued
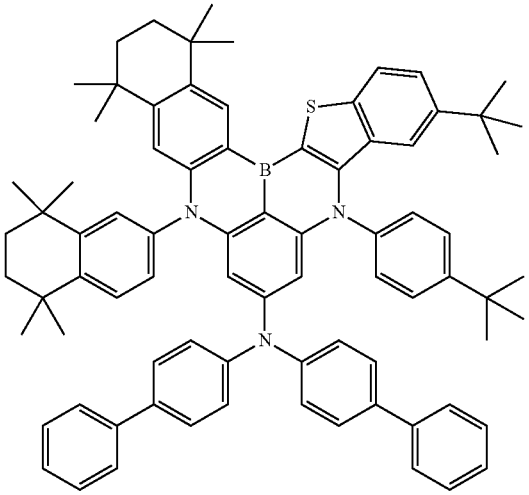
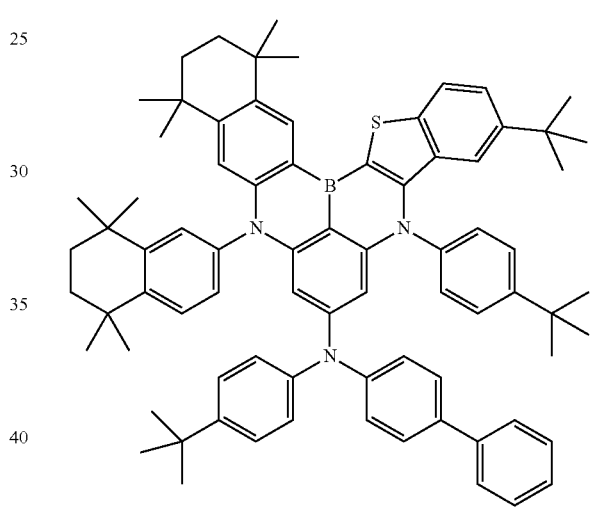
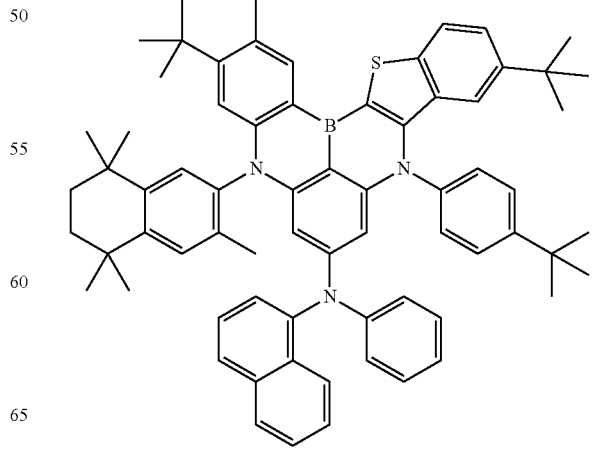

157
-continued
158
-continued
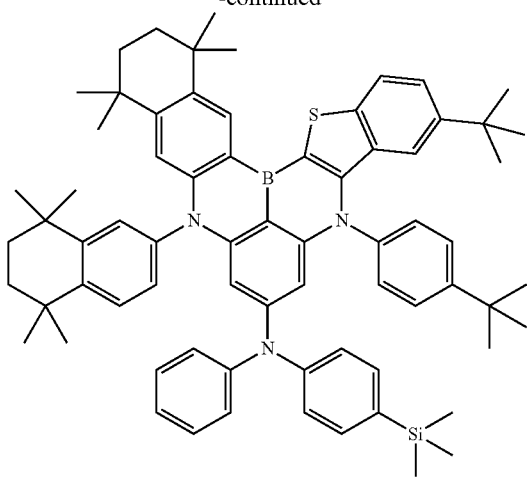
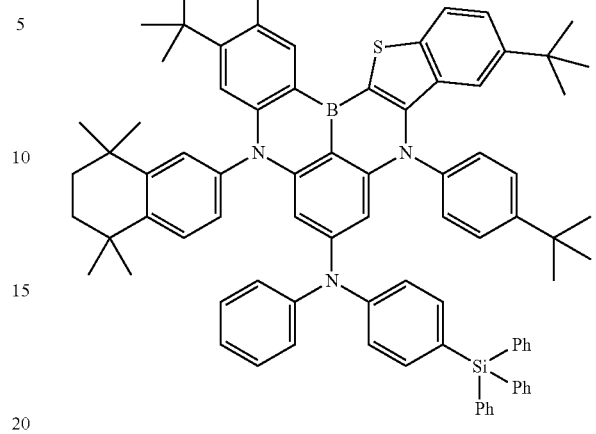
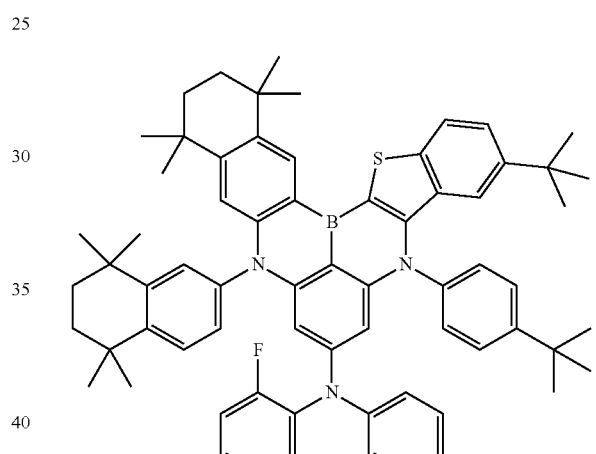
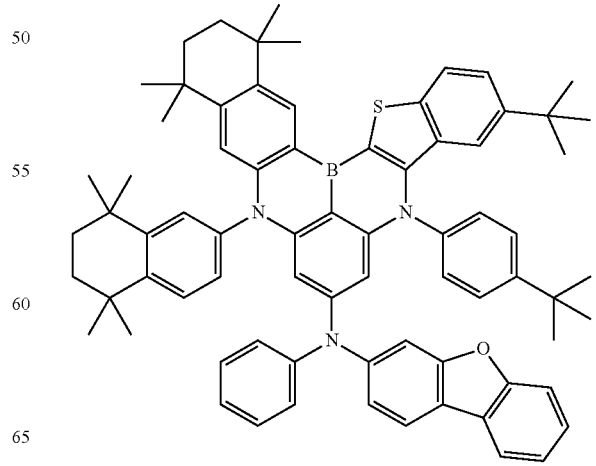

159
-continued
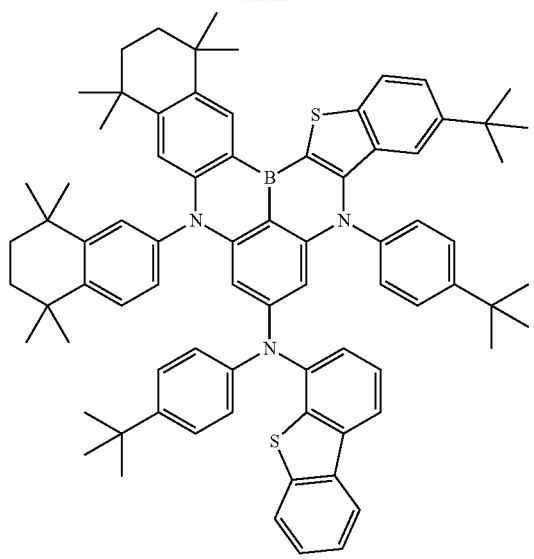
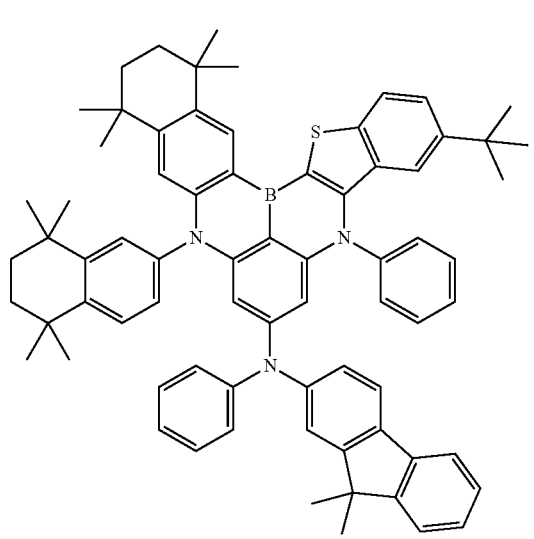
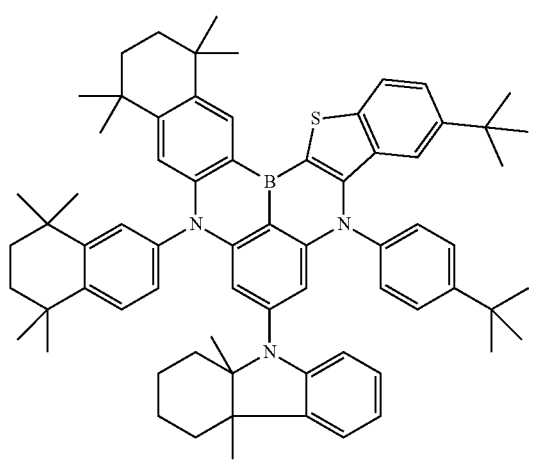
160
-continued
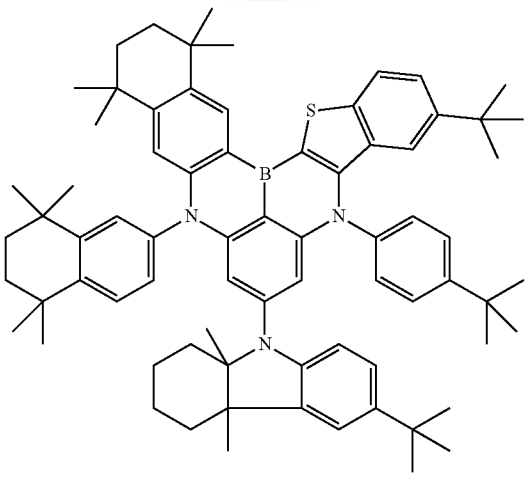
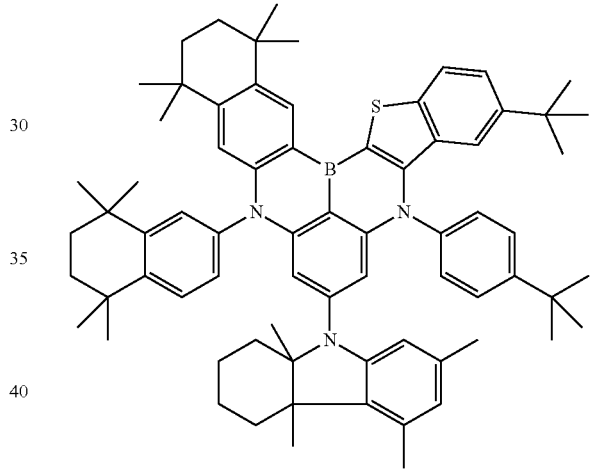
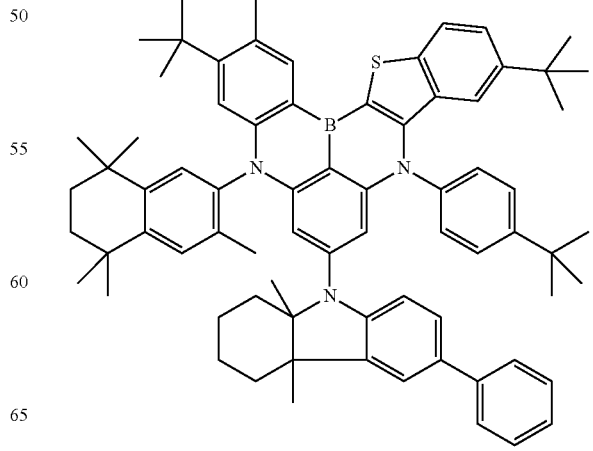

161
-continued
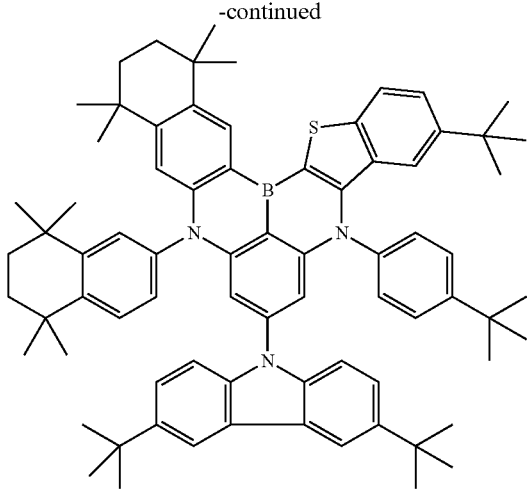
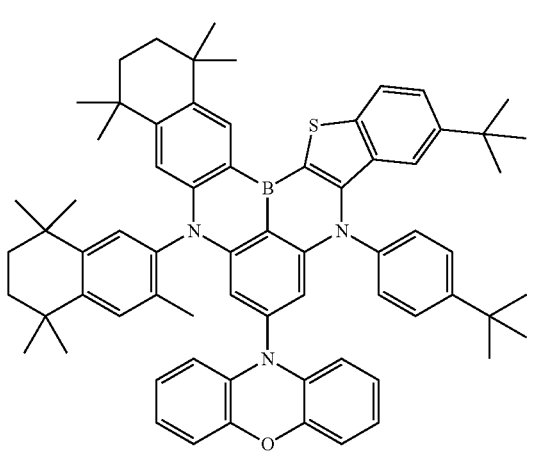
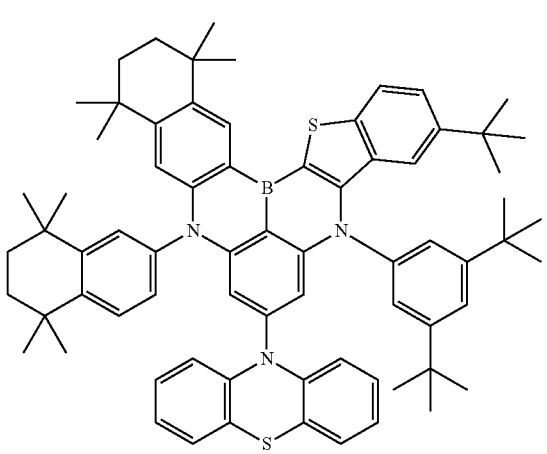
162
-continued
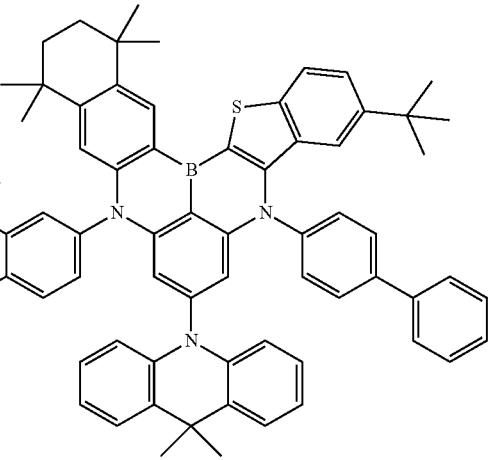
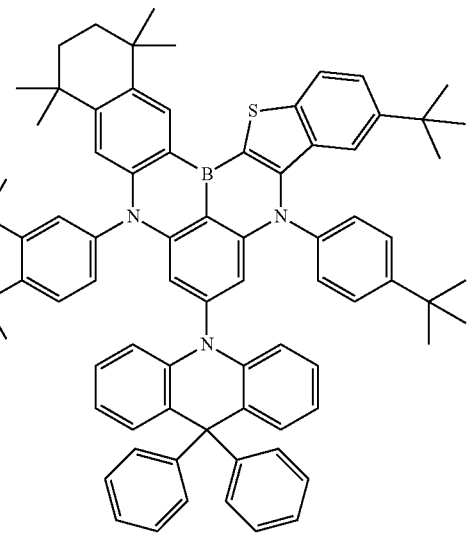
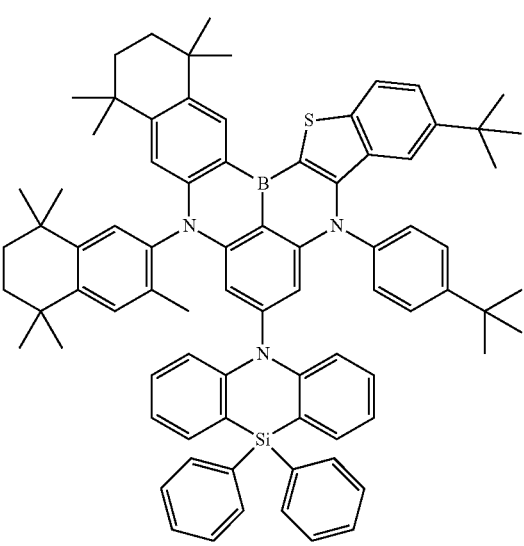

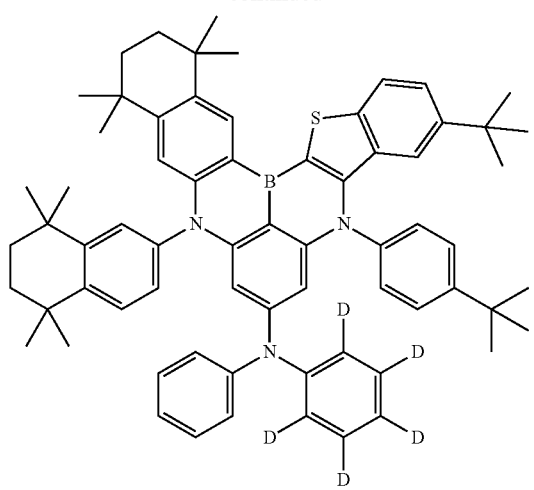
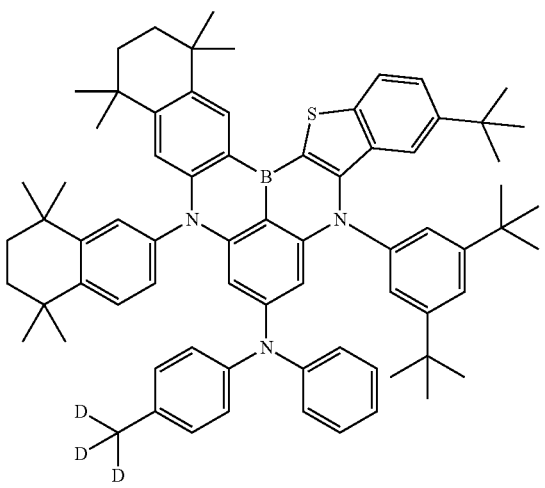
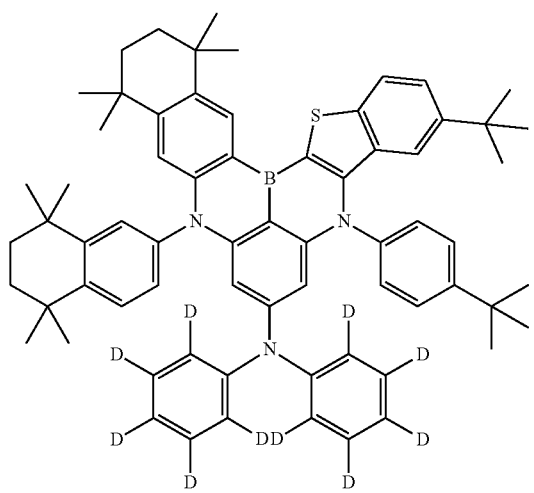
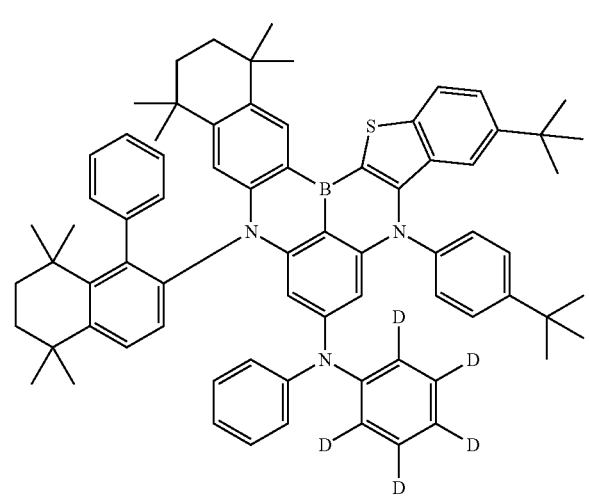
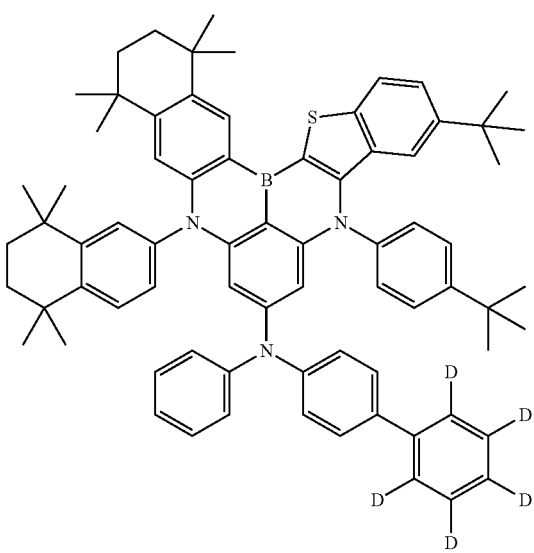

165
-continued
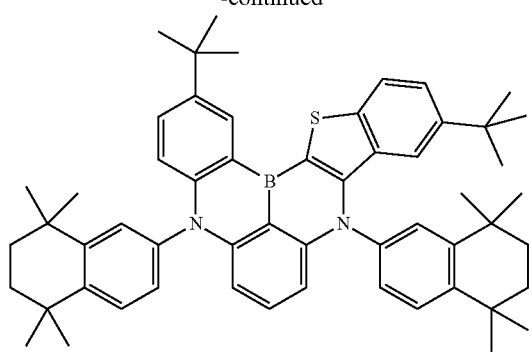
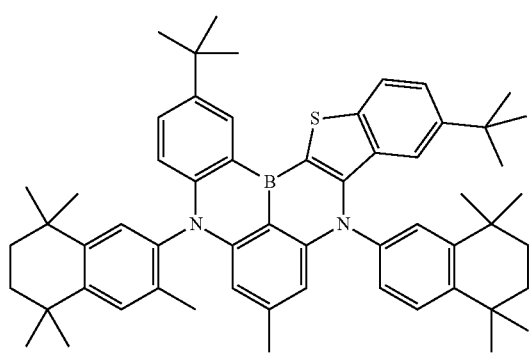
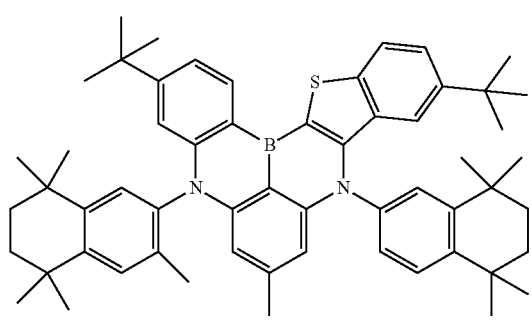
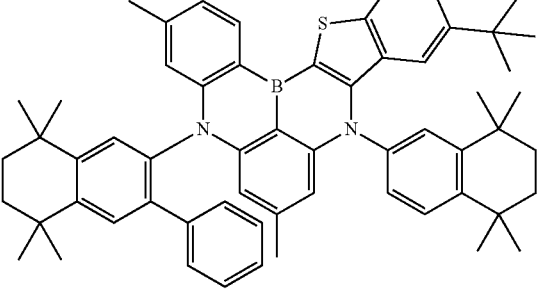
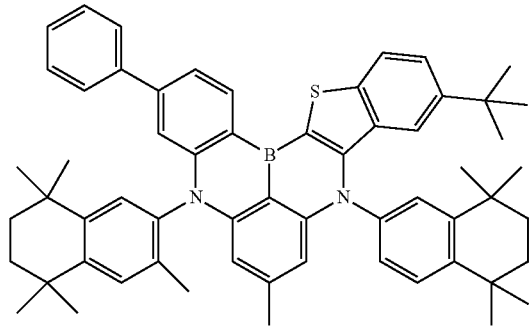
166
-continued
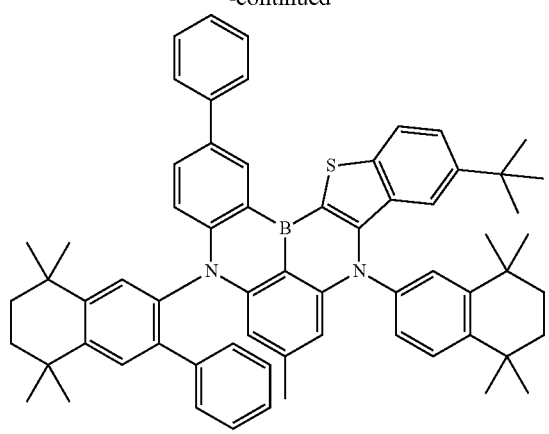
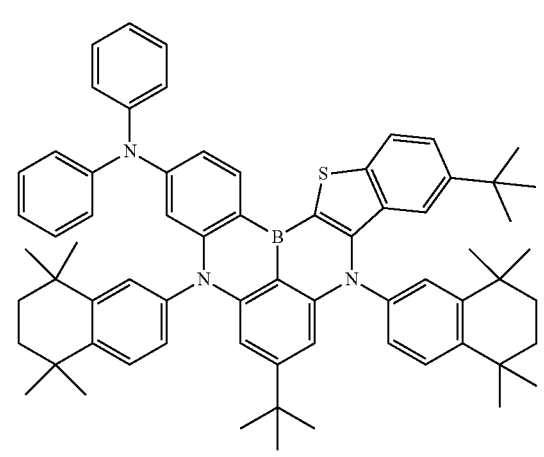
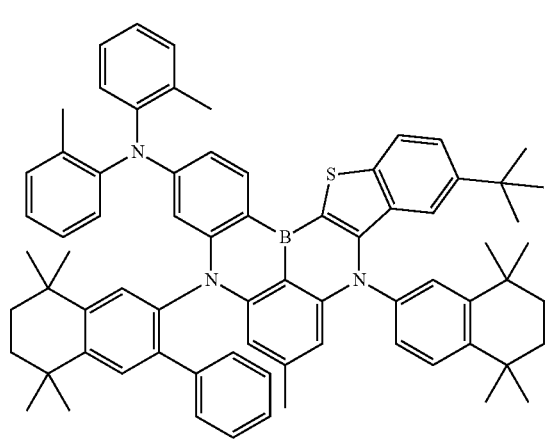
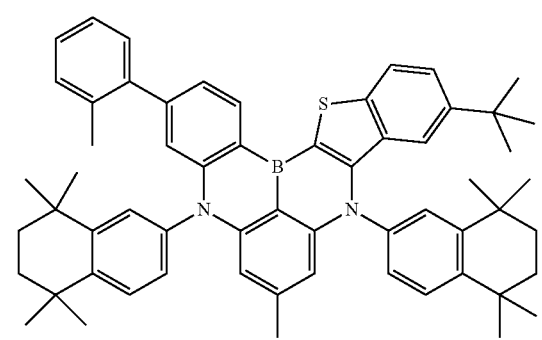

167
-continued
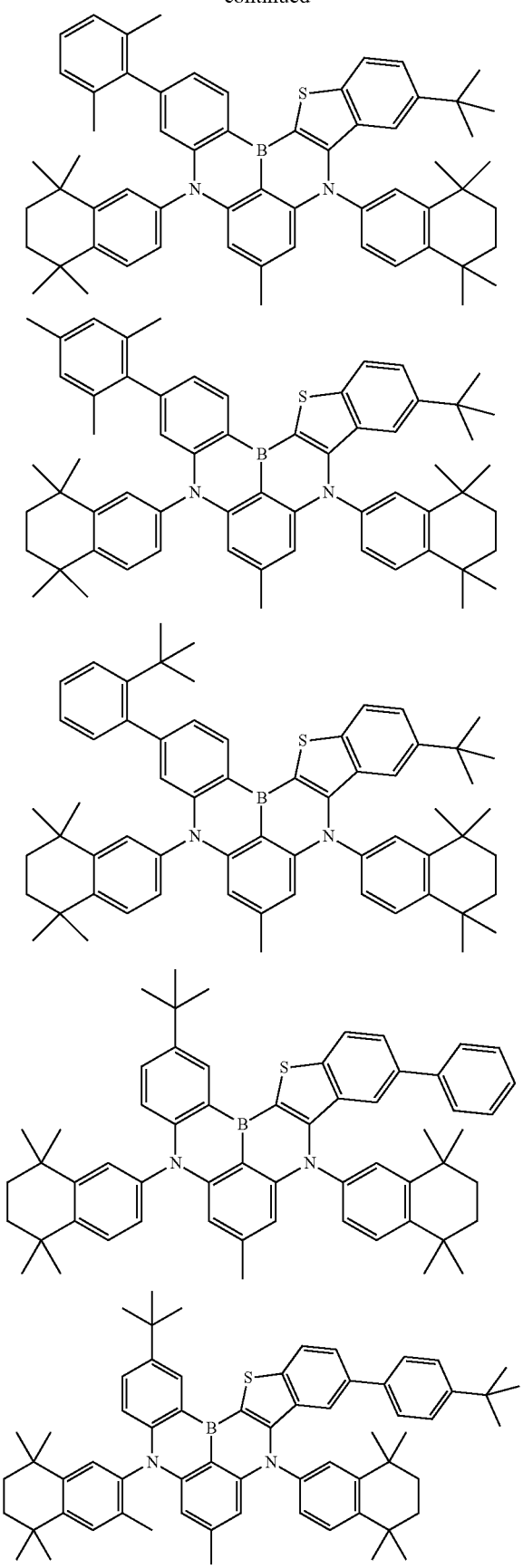
168
-continued
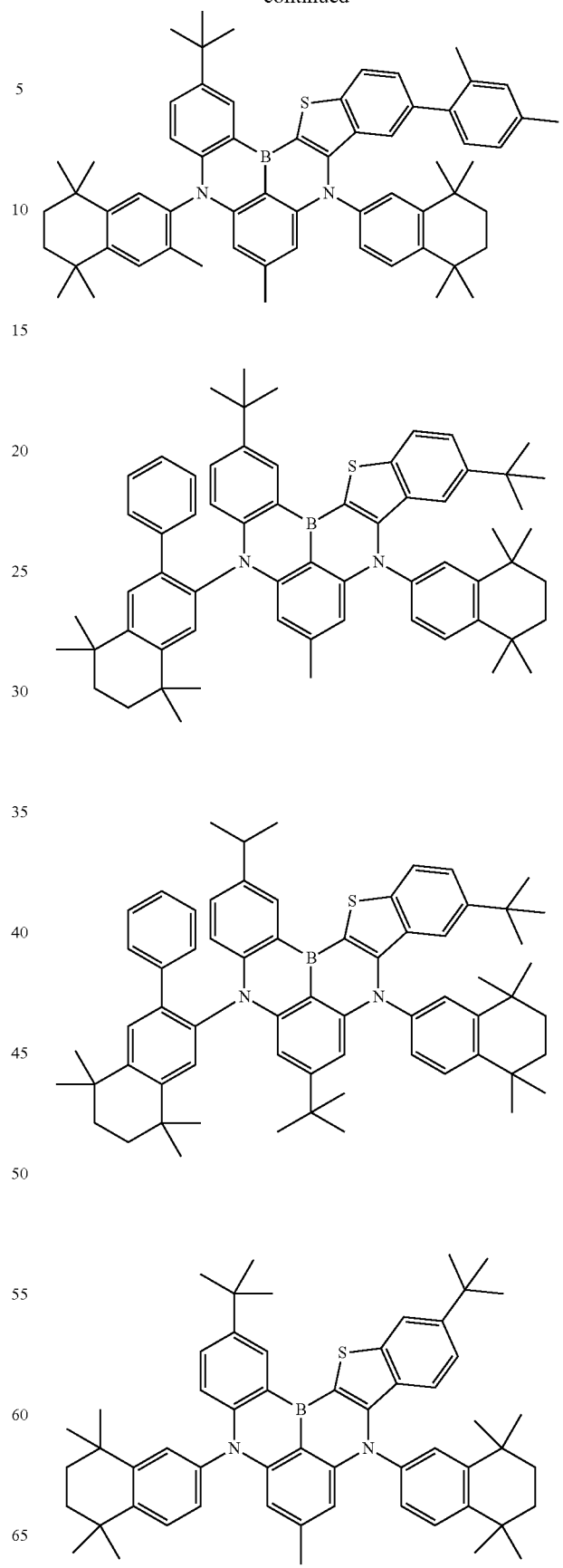

169
-continued
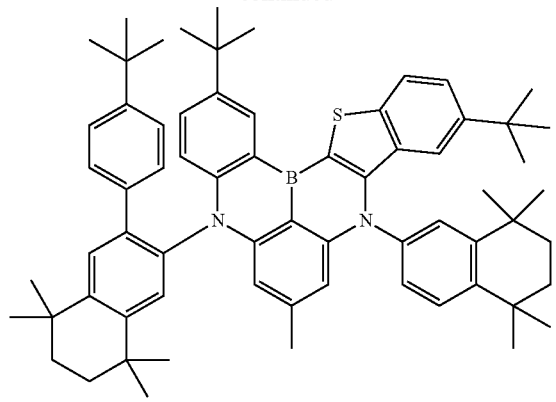
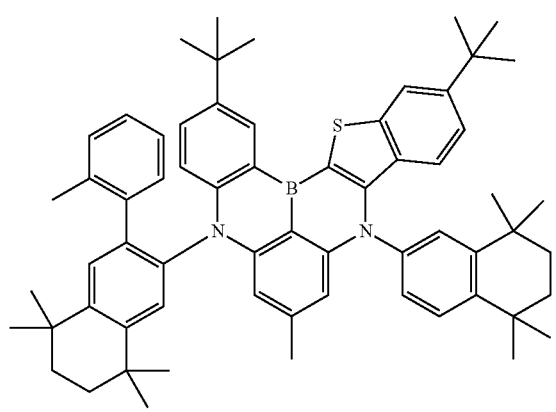
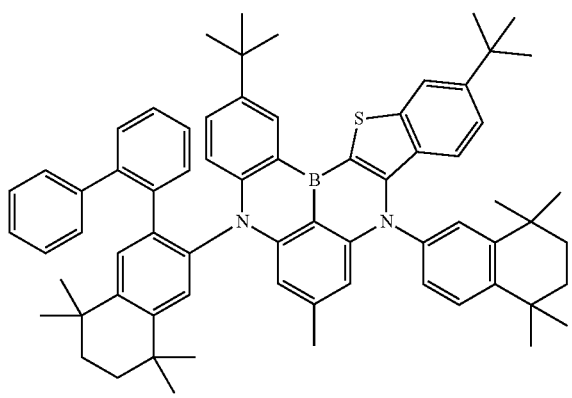
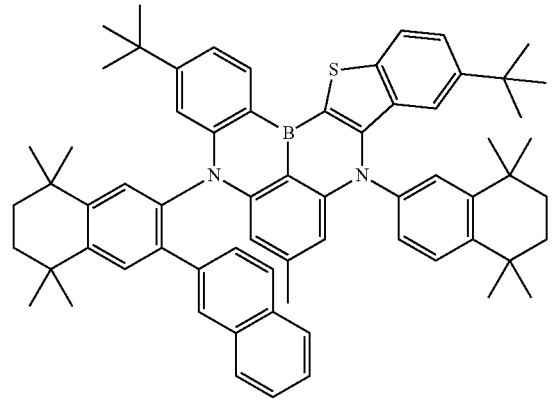
170
-continued
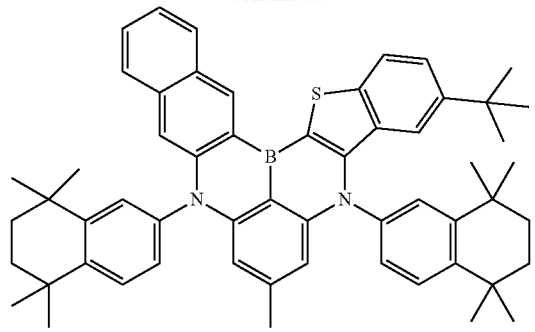
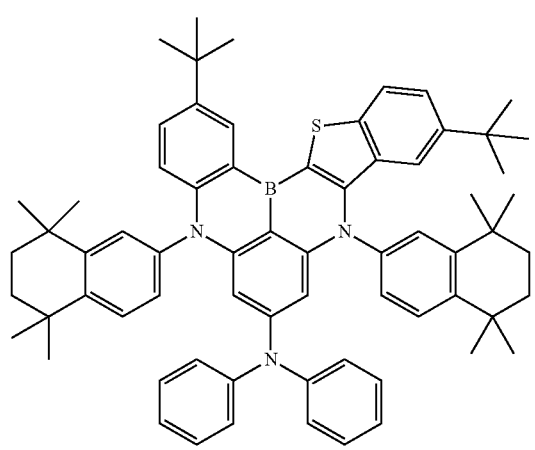

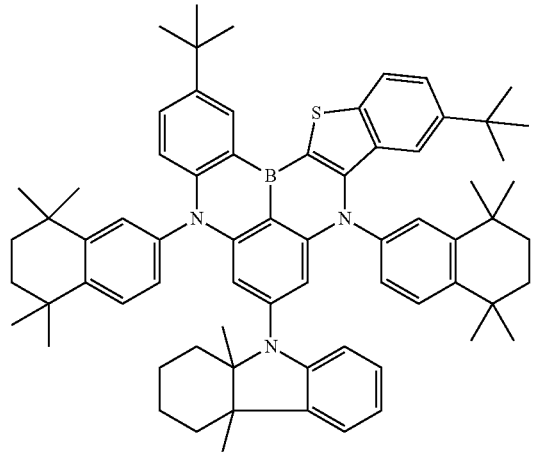

171
-continued
172
-continued
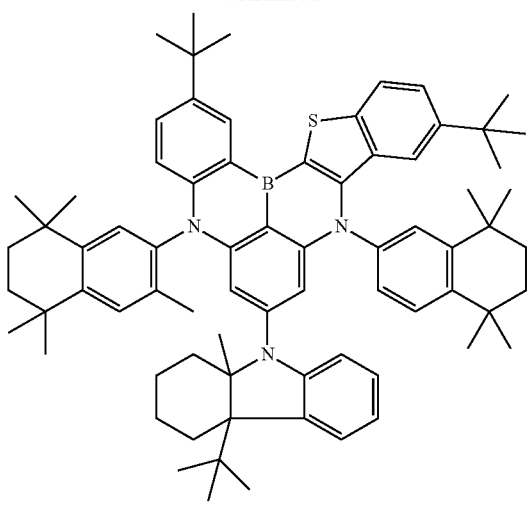
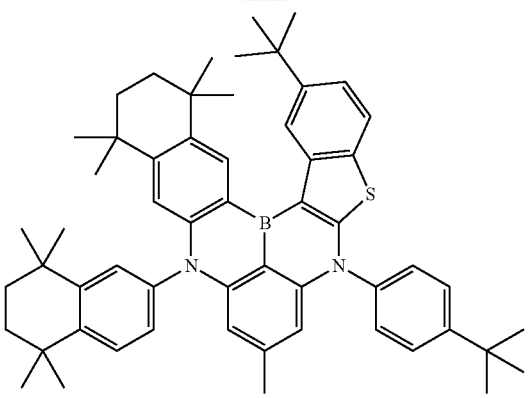
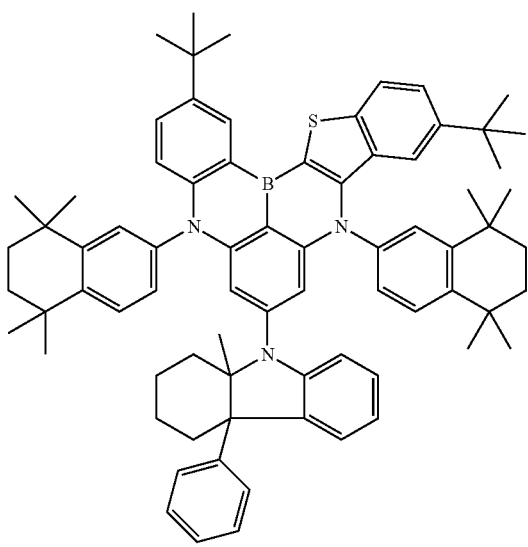
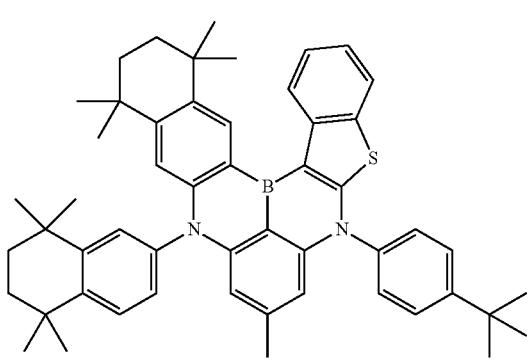
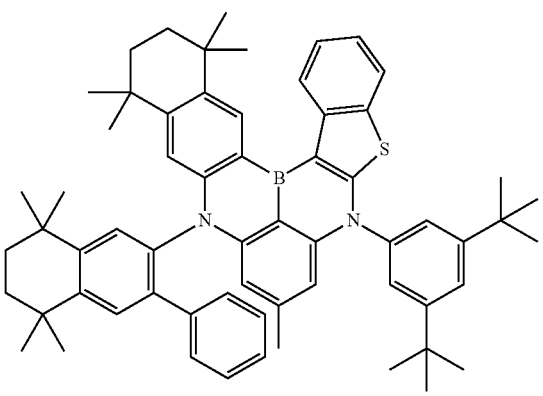

173
-continued
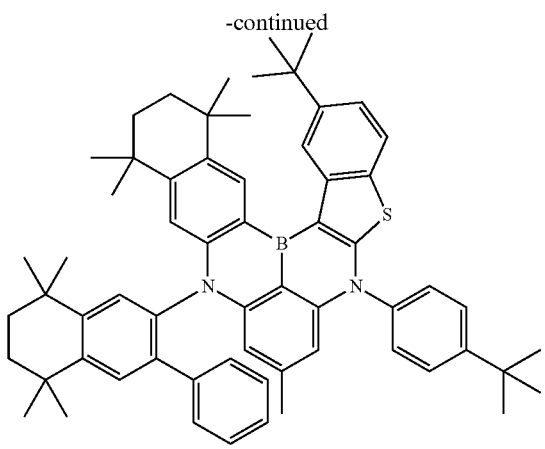
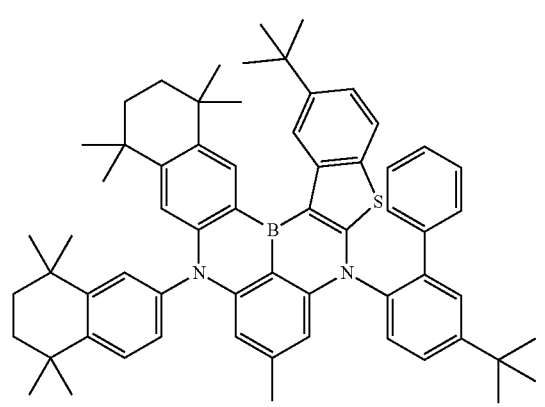
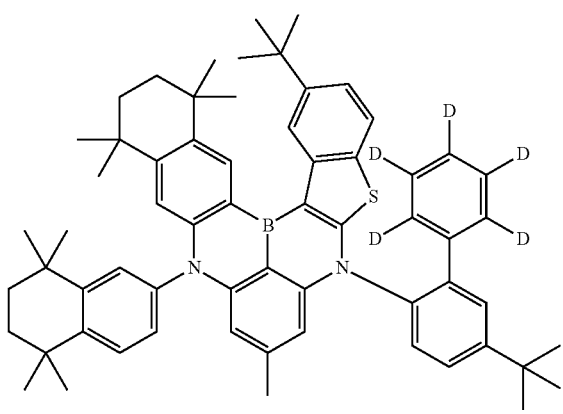
174
-continued
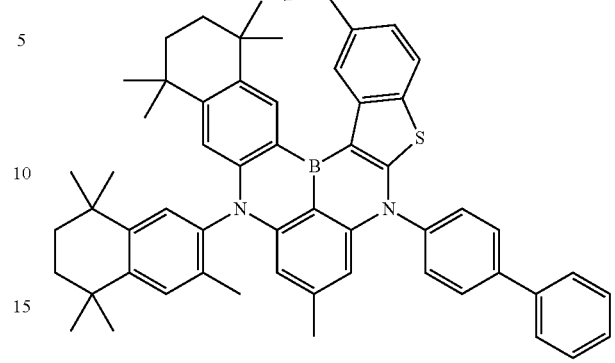
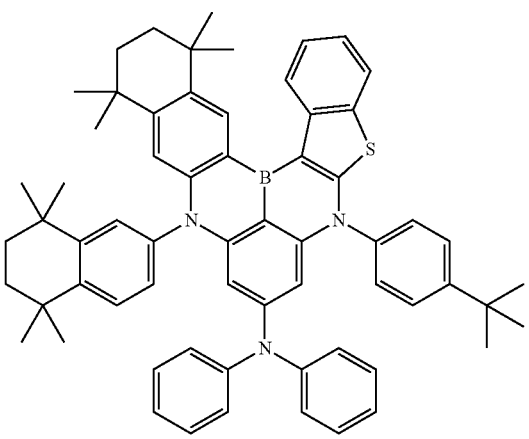
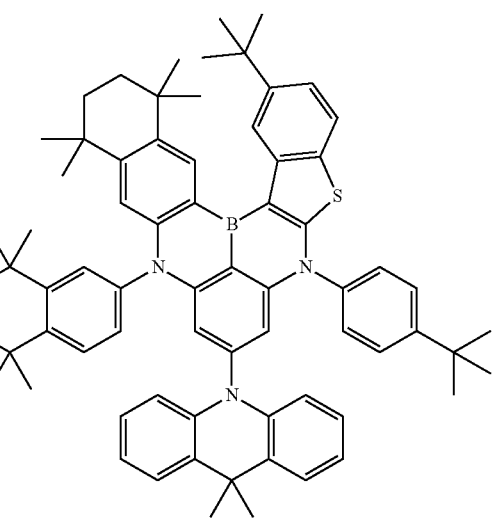

175
-continued
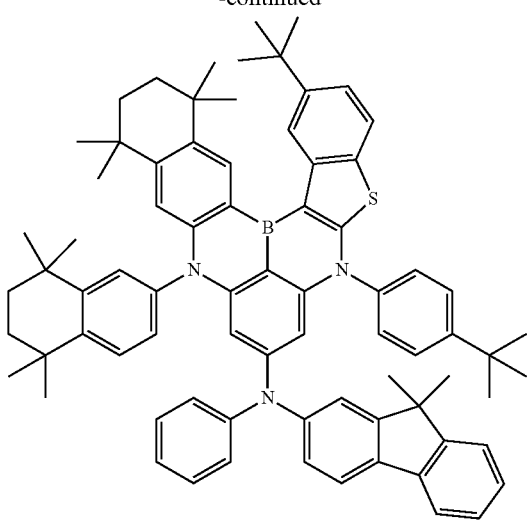
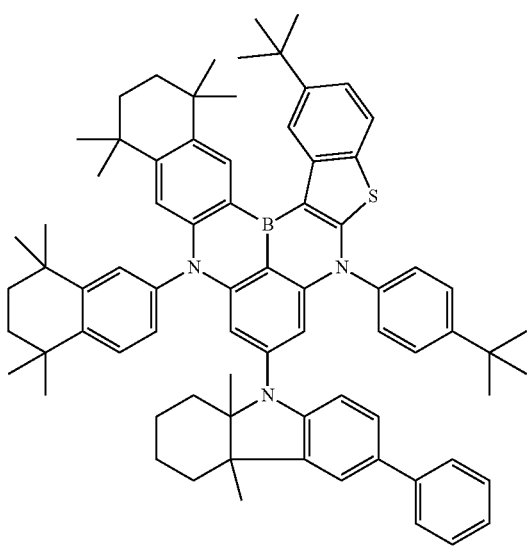
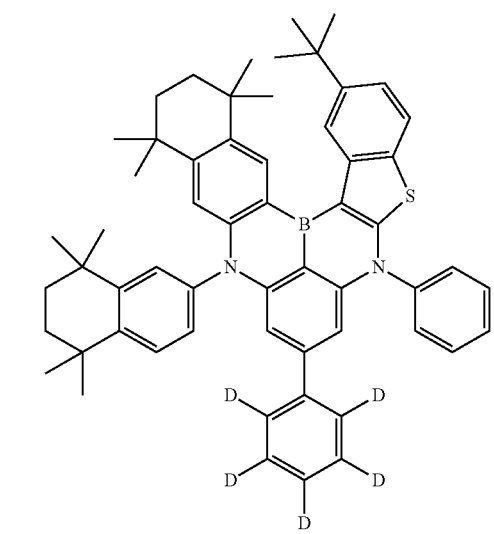
176
-continued
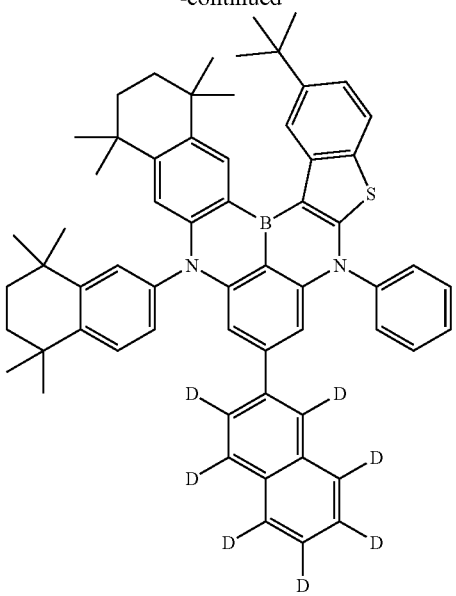
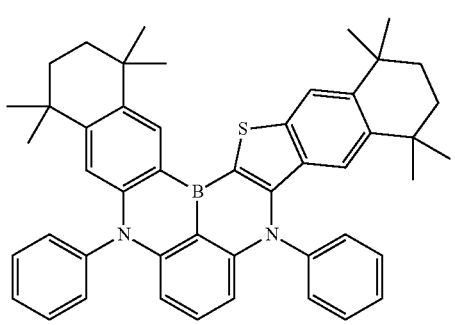
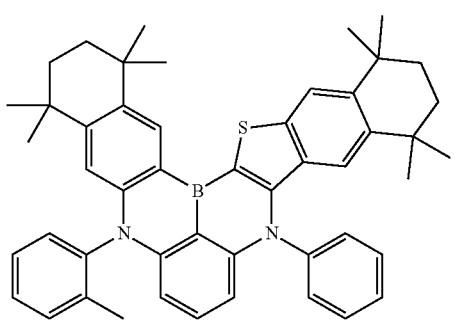
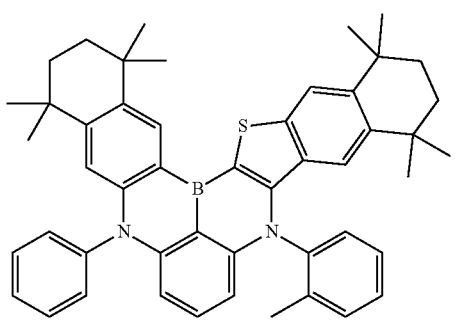

177
-continued
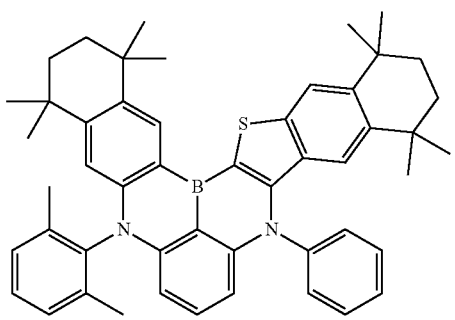
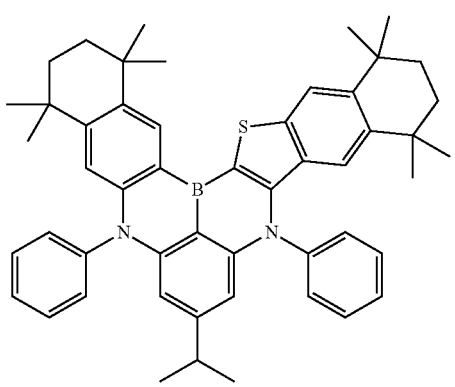
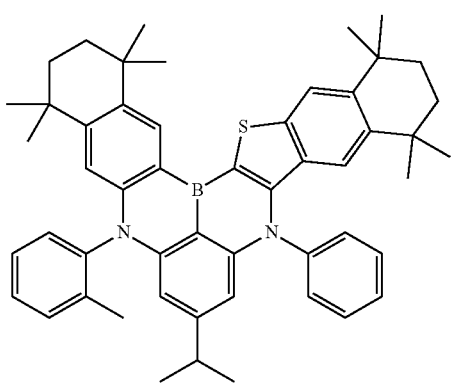
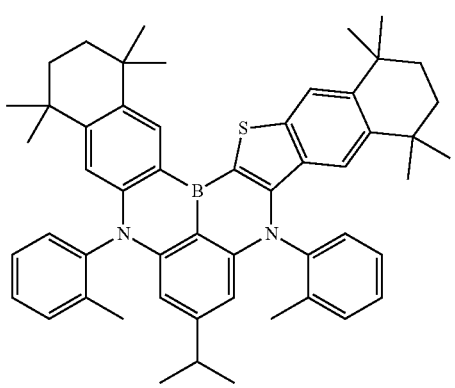
178
-continued
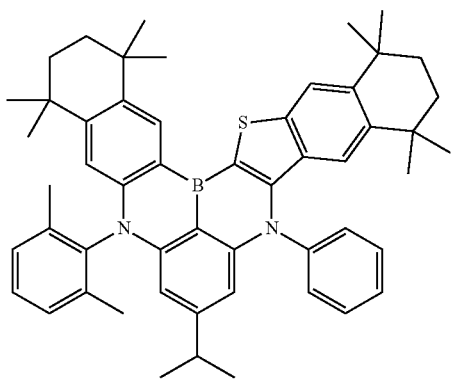
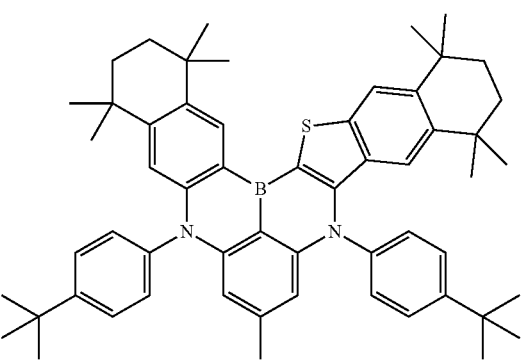
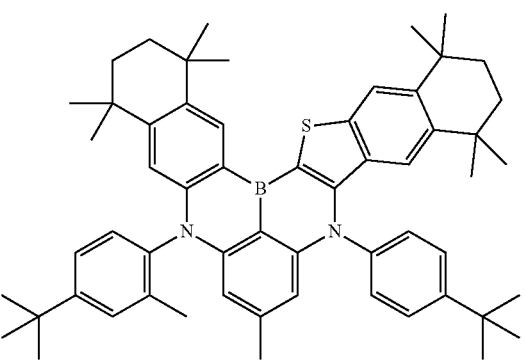
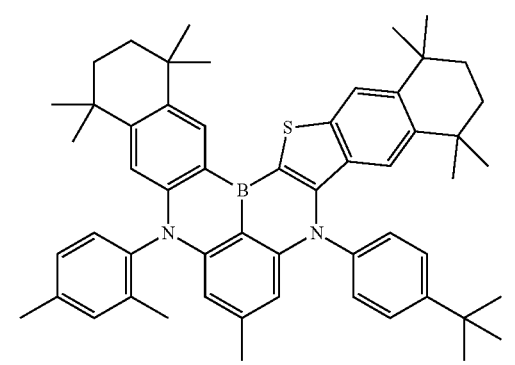

| 179 -continued | 180 -continued |
|---|---|
| 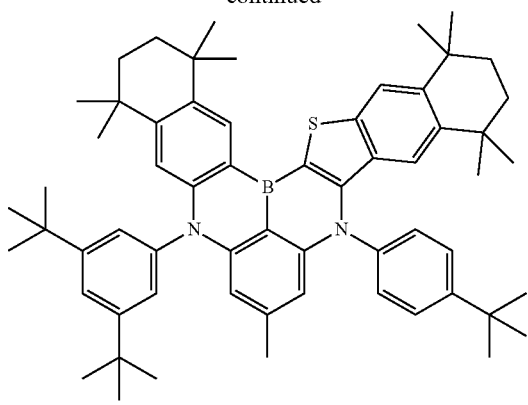 |  |
| 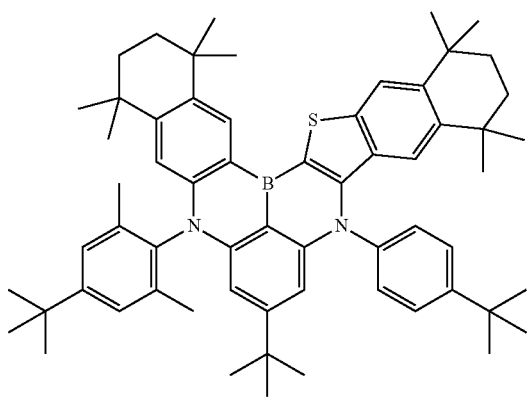 | 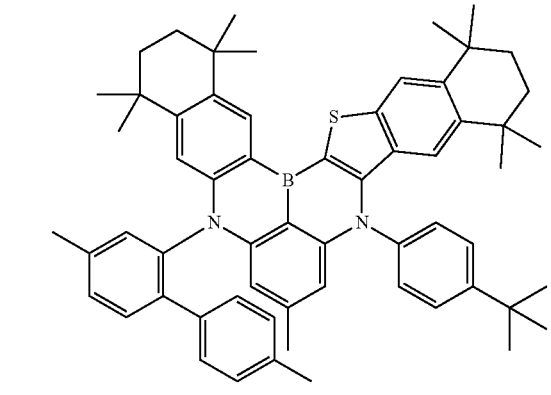 |
| 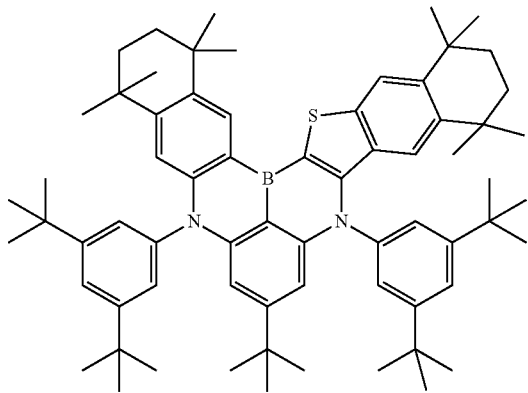 | 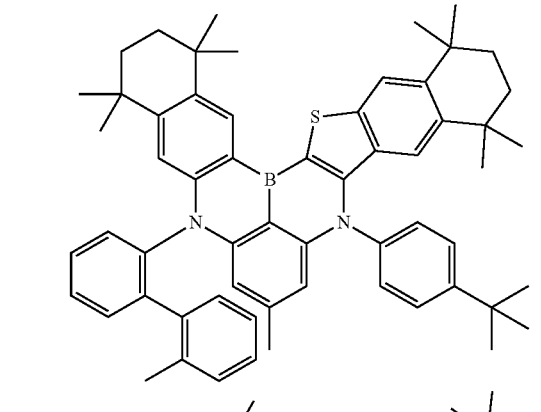 |
| 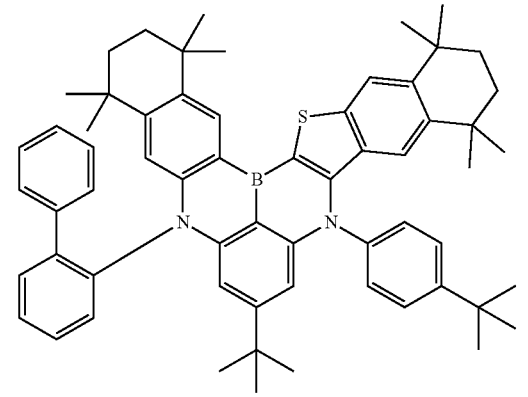 | 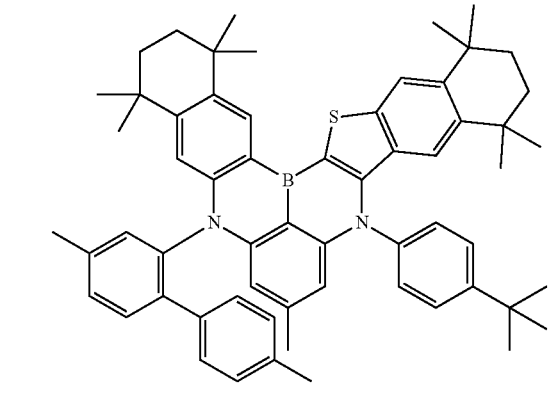 |

181
-continued
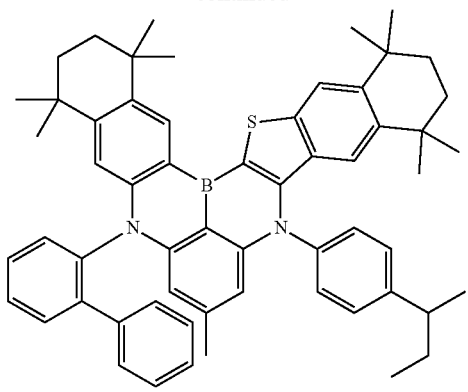
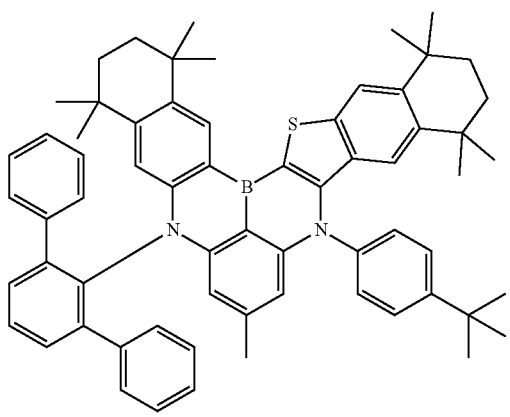
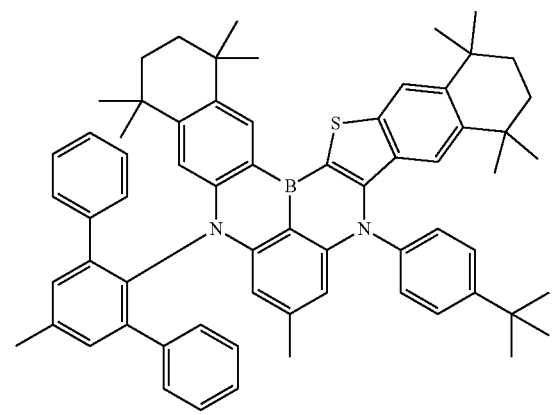
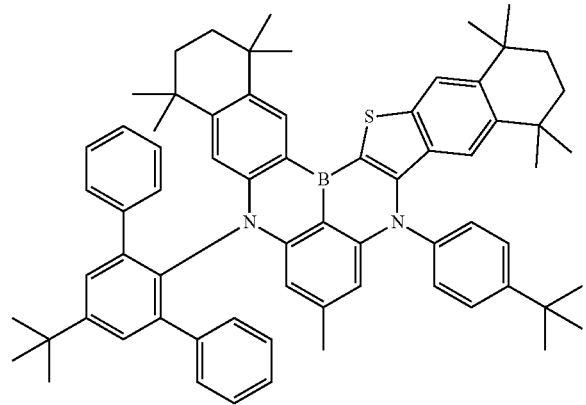
182
-continued
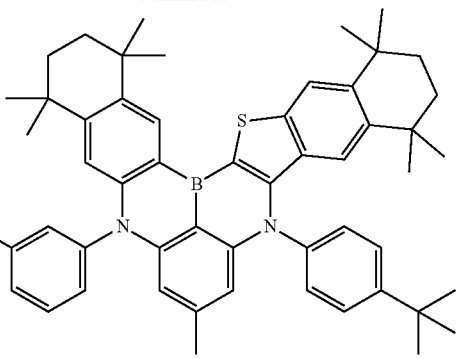
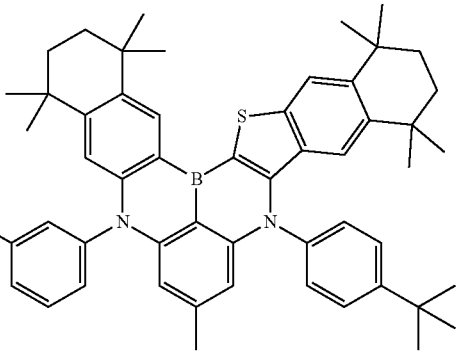
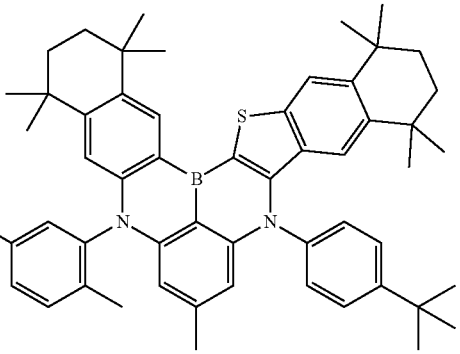
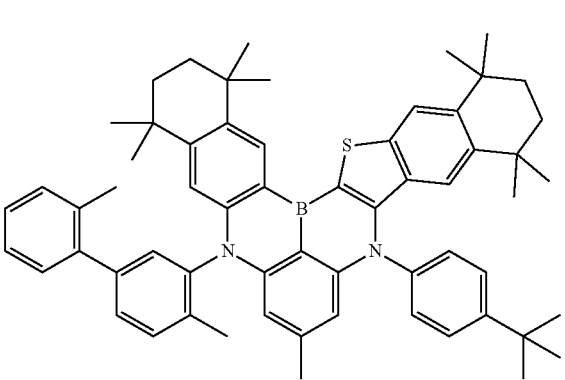

183
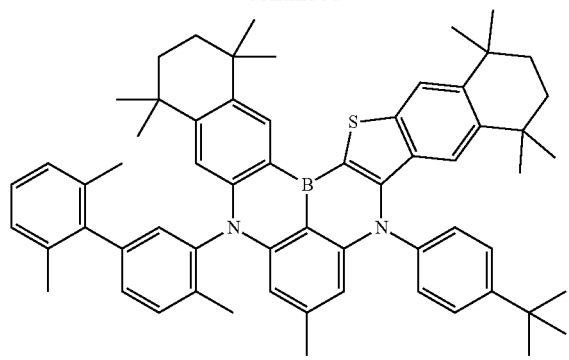
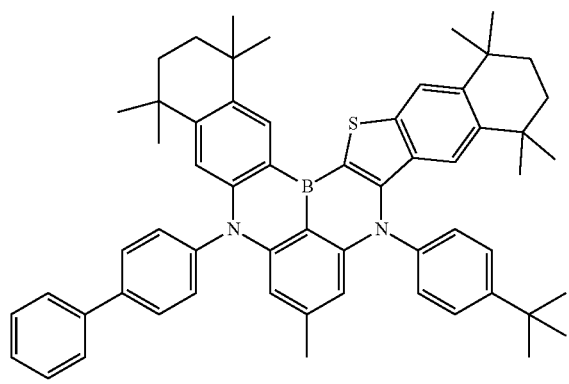
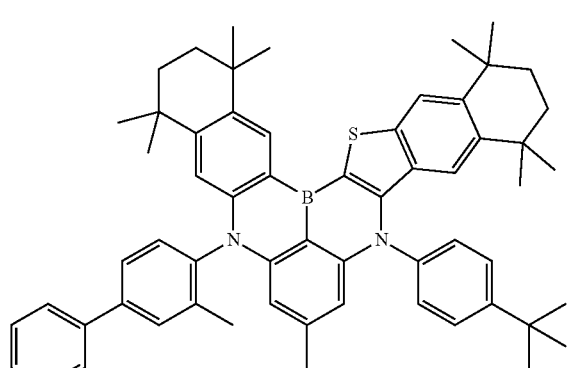
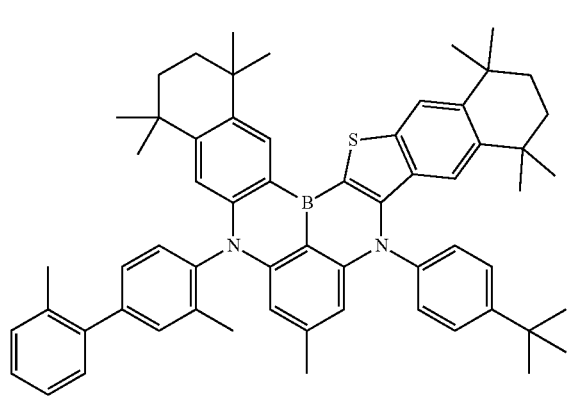
184
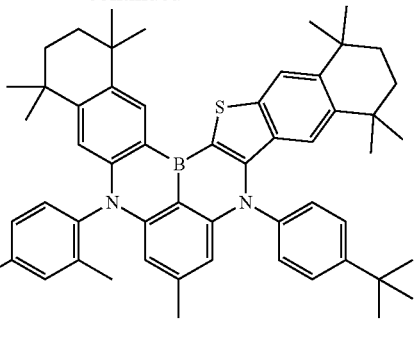
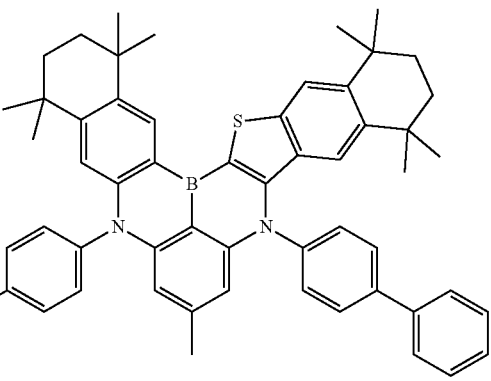
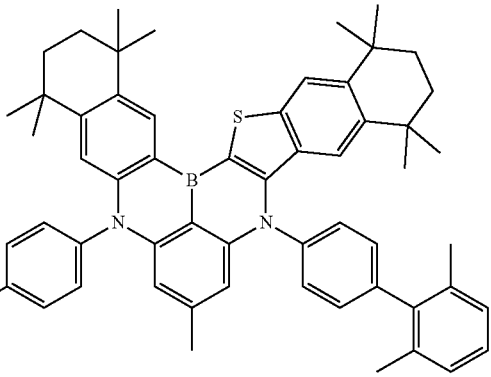
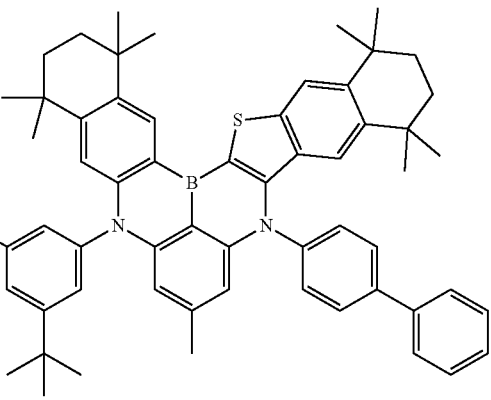

185
-continued
186
-continued
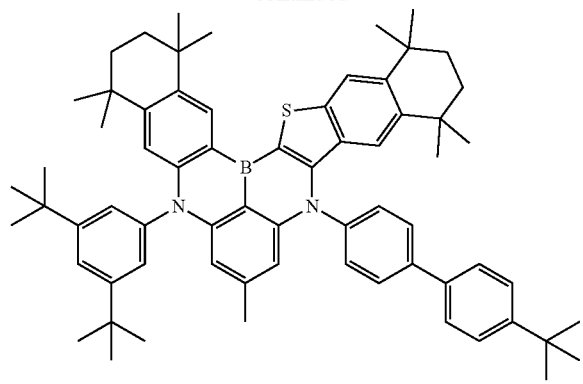
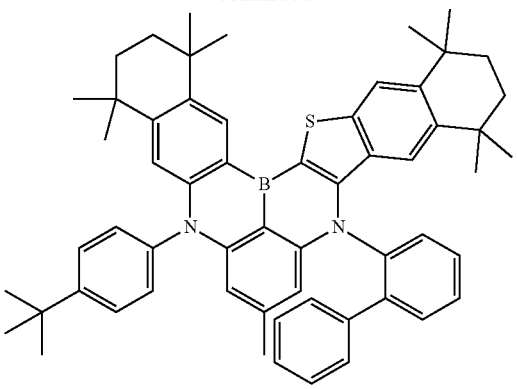

187
-continued
188
-continued
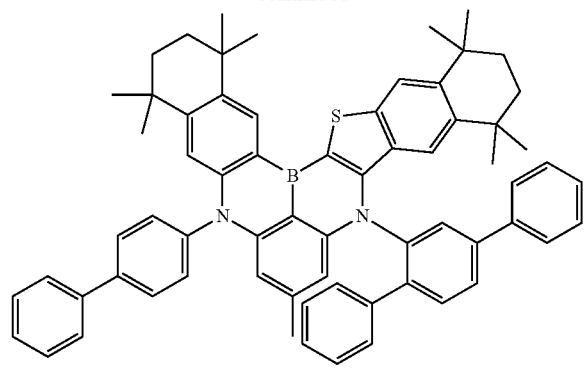
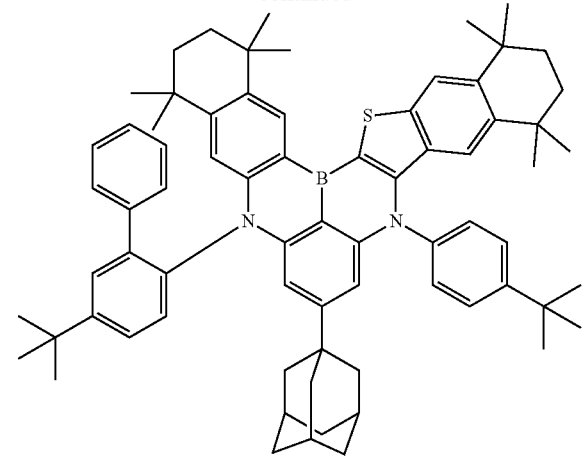
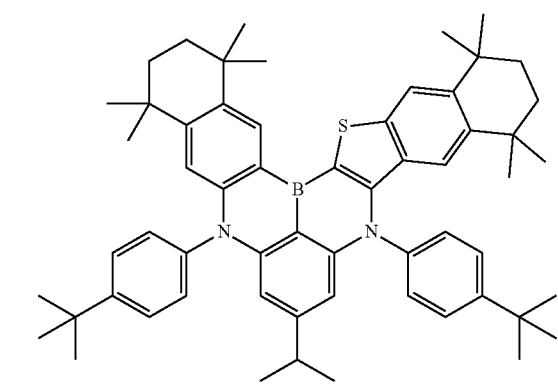
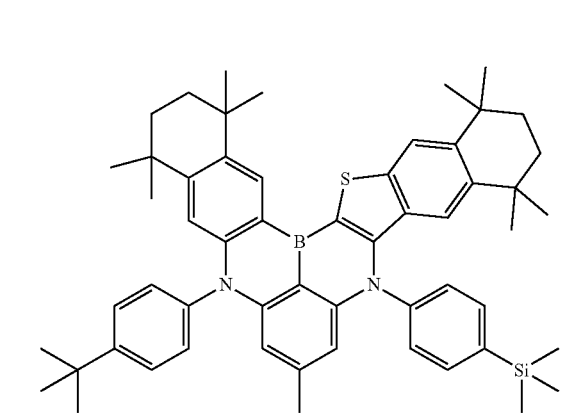
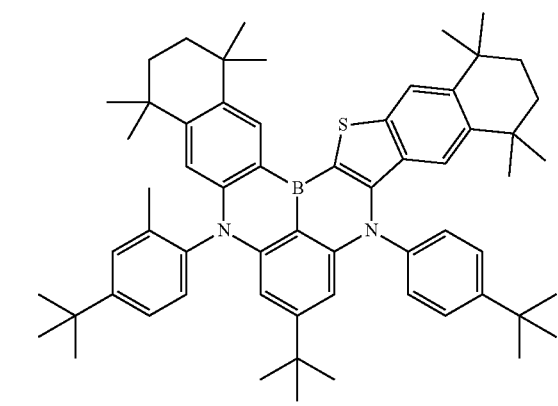
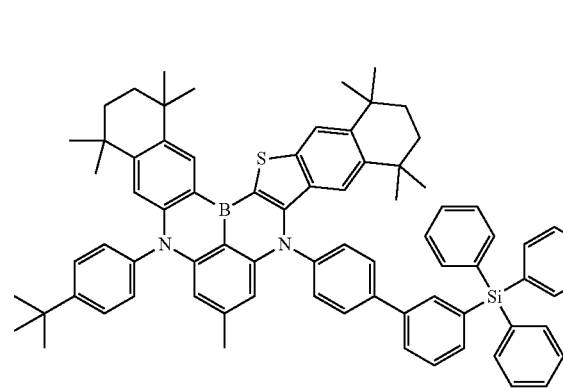
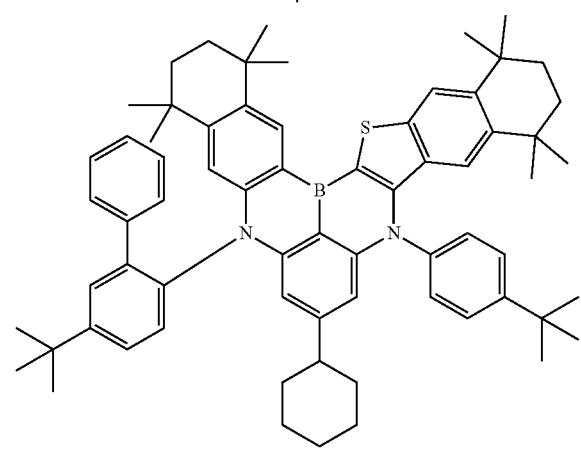
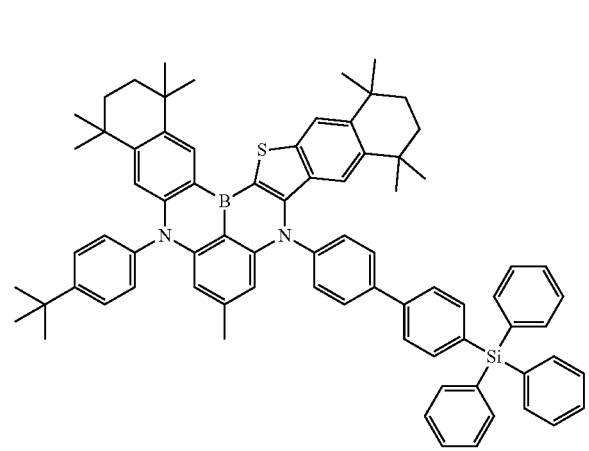

189
-continued
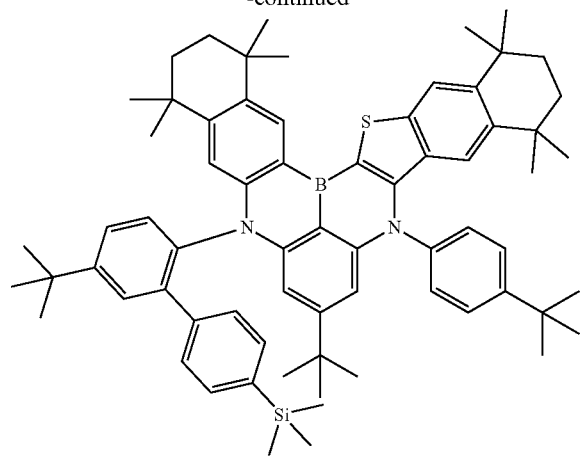
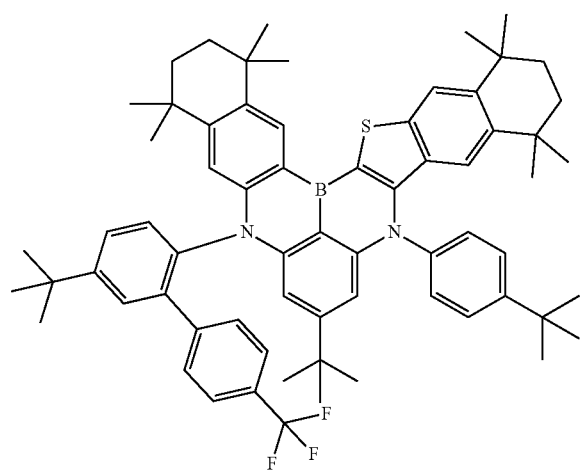
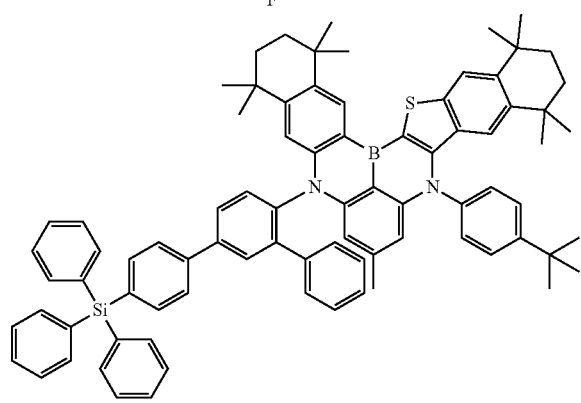
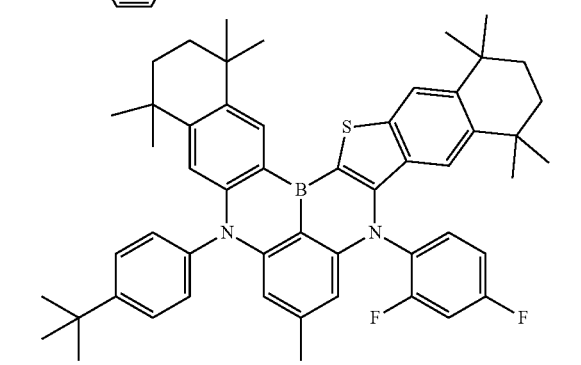
190
-continued
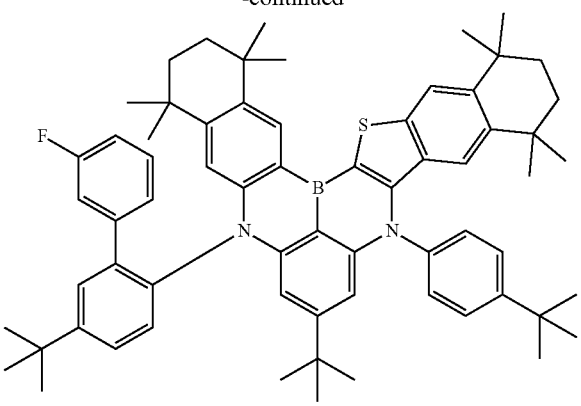
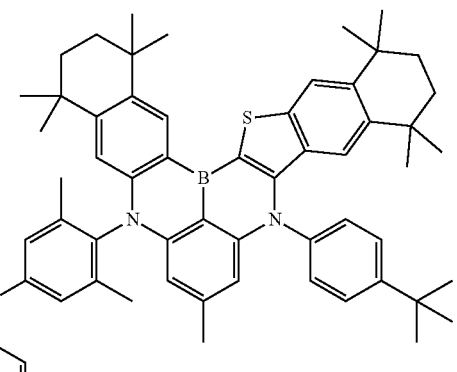
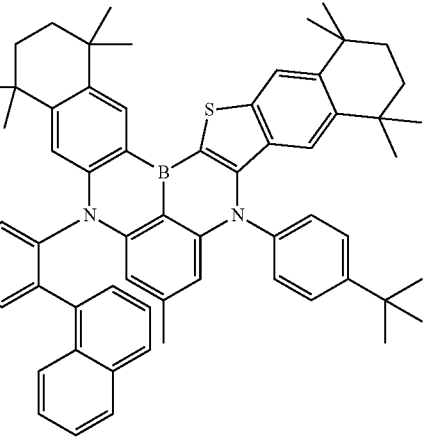
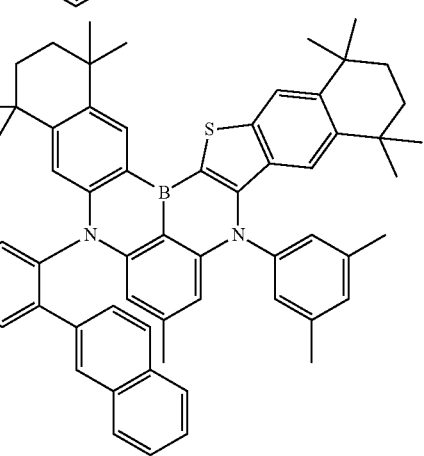

191
-continued
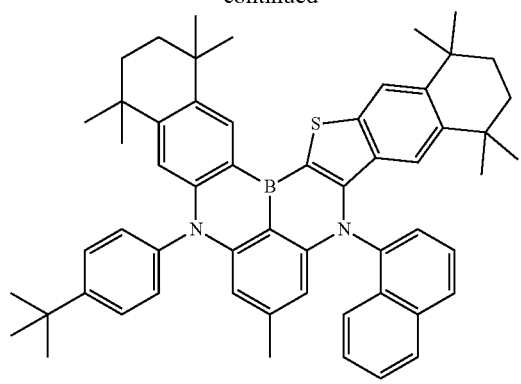
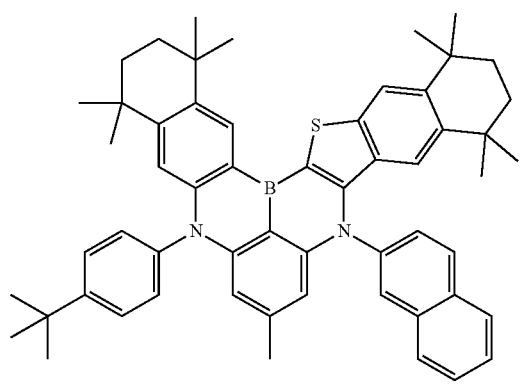
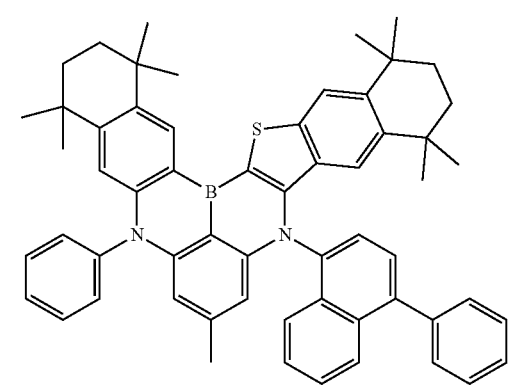
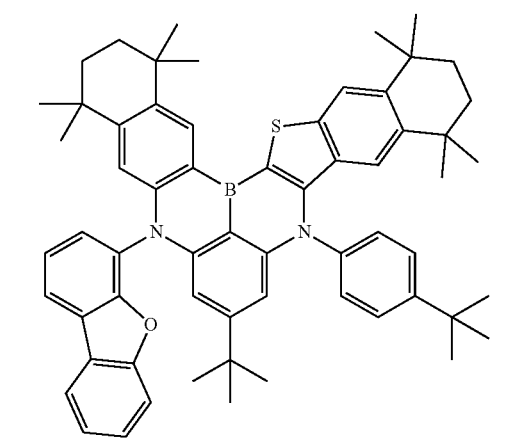
192
-continued
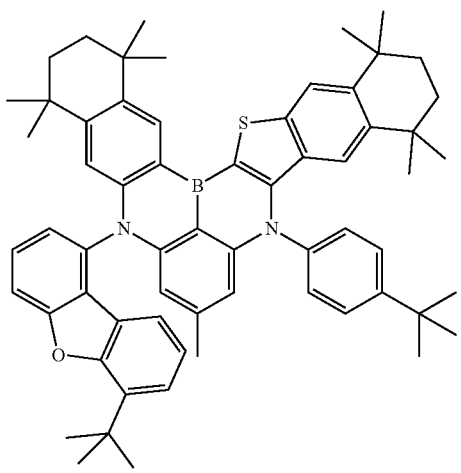
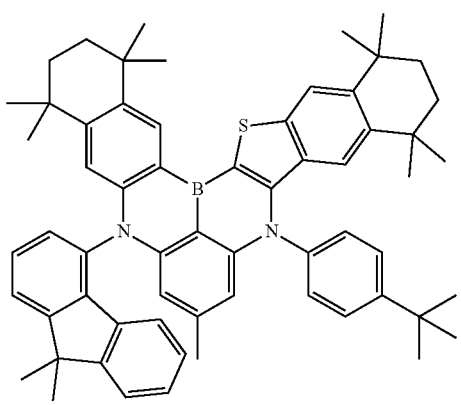
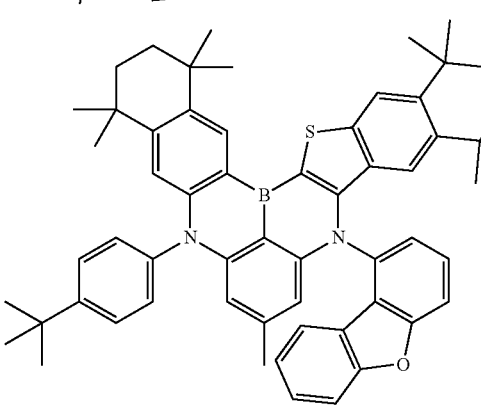
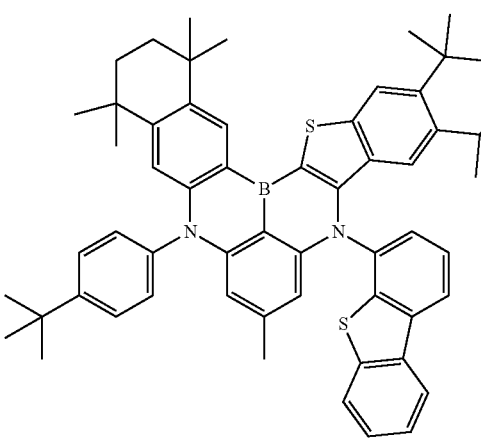

193
-continued
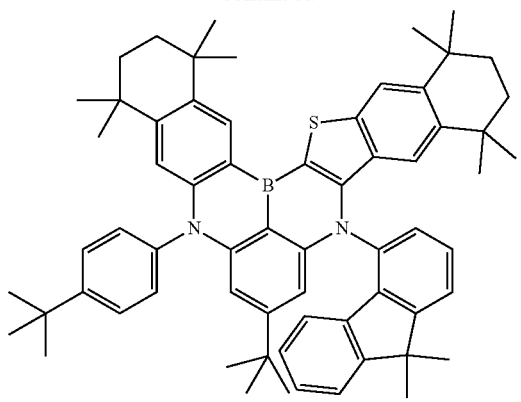
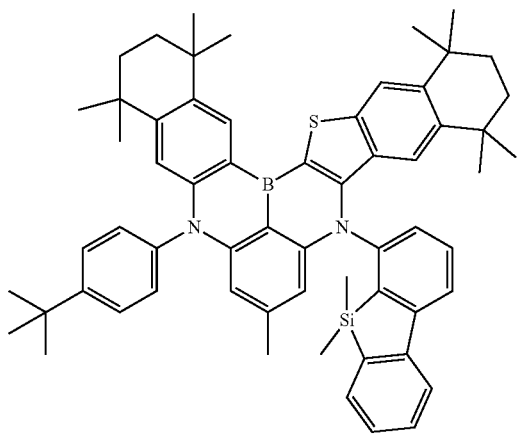
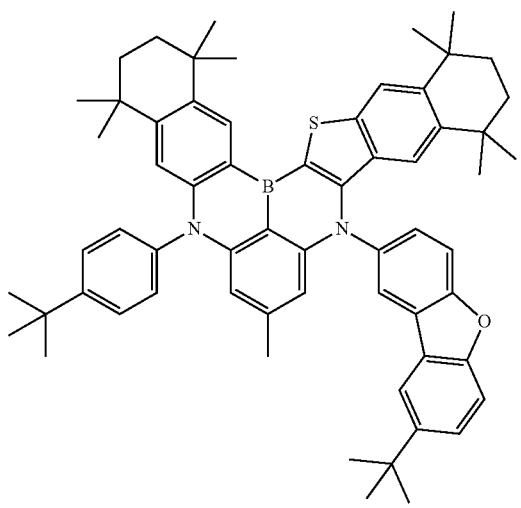
194
-continued
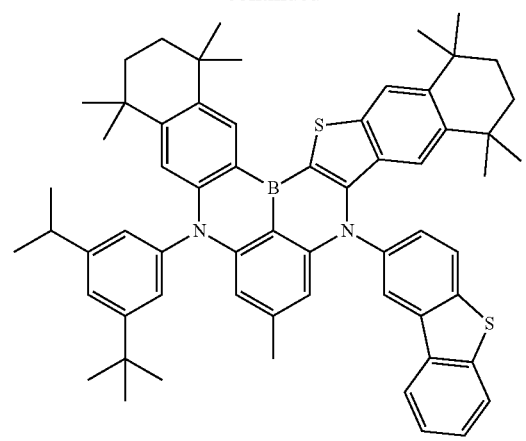
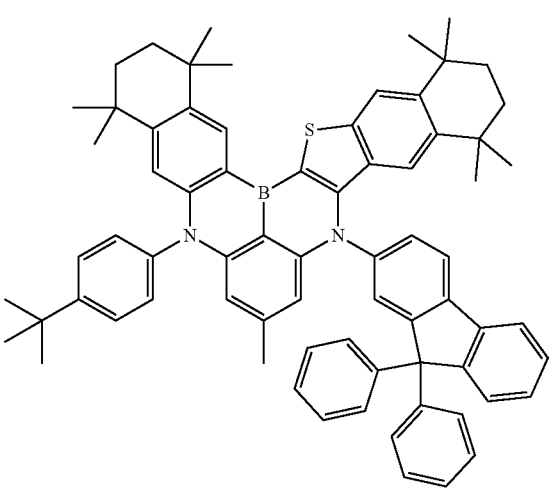
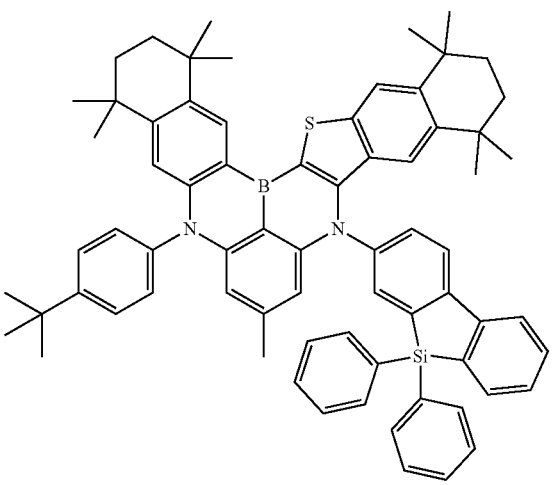

| 195 -continued | 196 -continued |
|---|---|
| 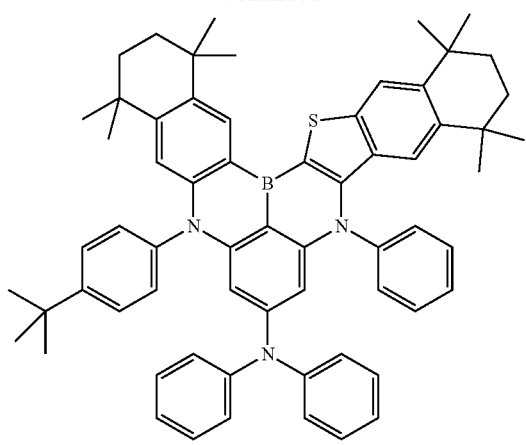 | 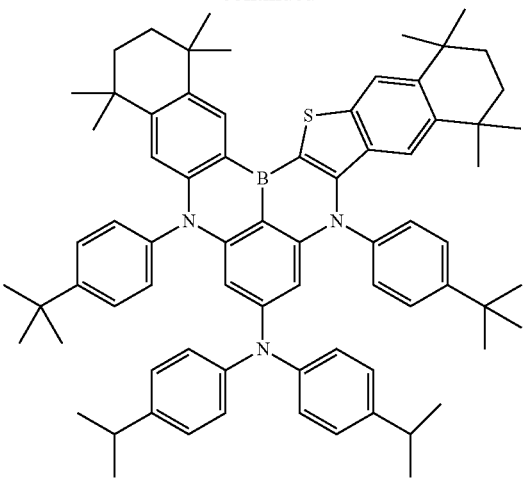 |
| 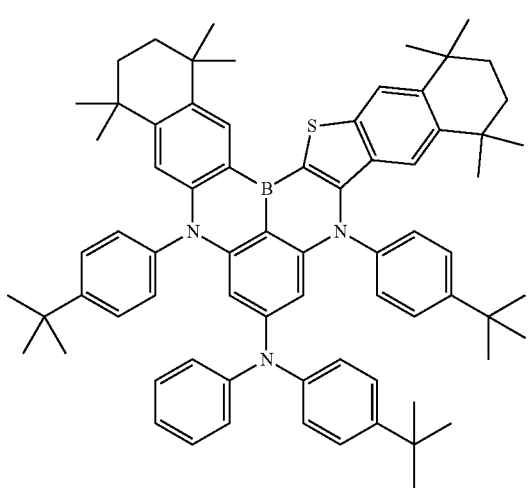 | 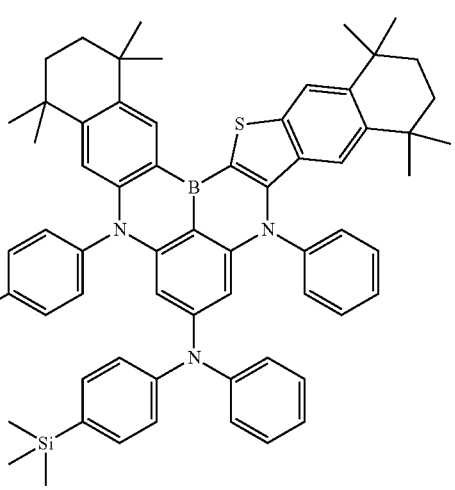 |
| 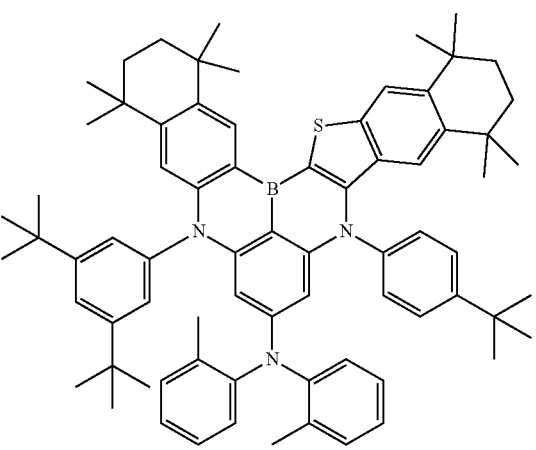 | 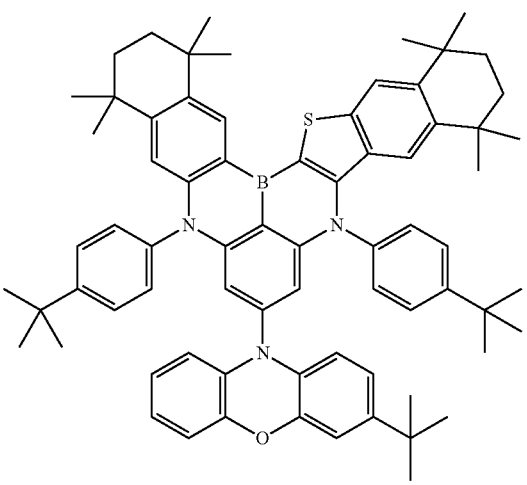 |

197
-continued
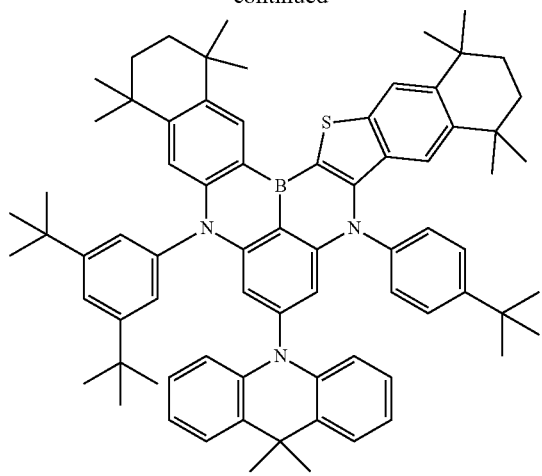
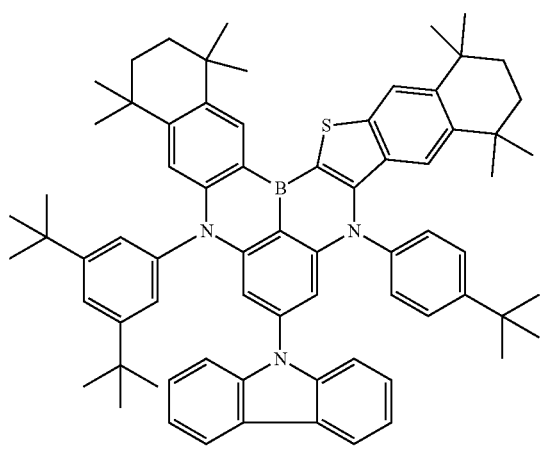
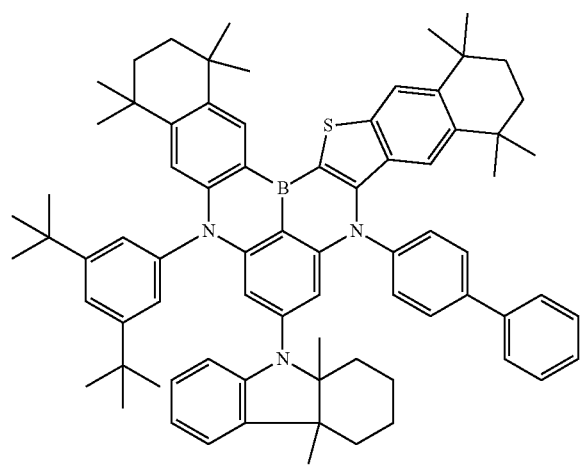
198
-continued
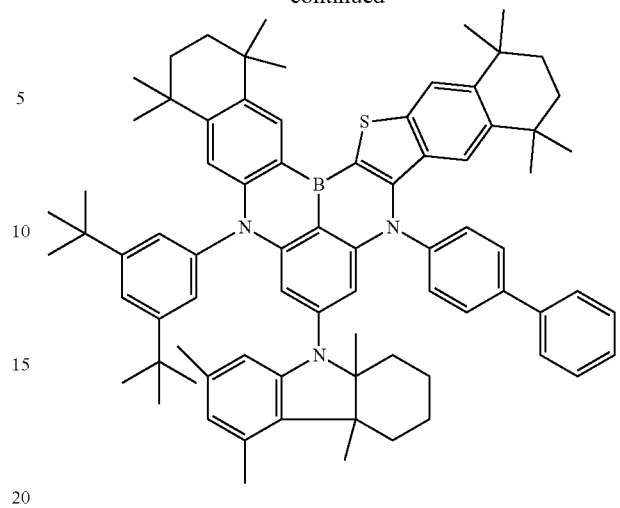
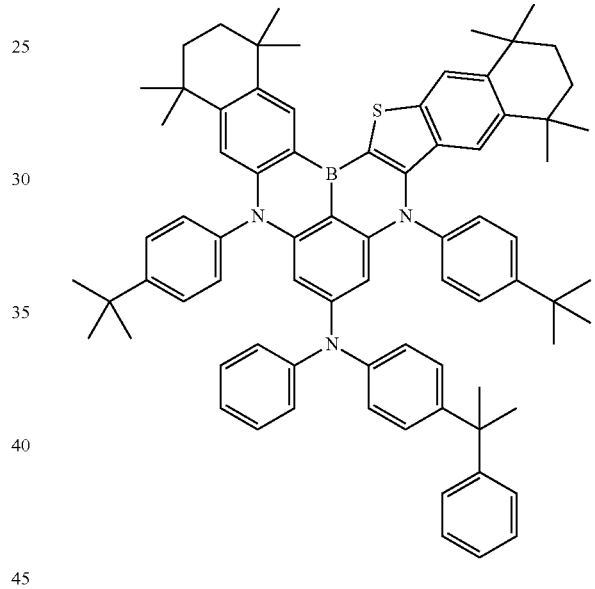
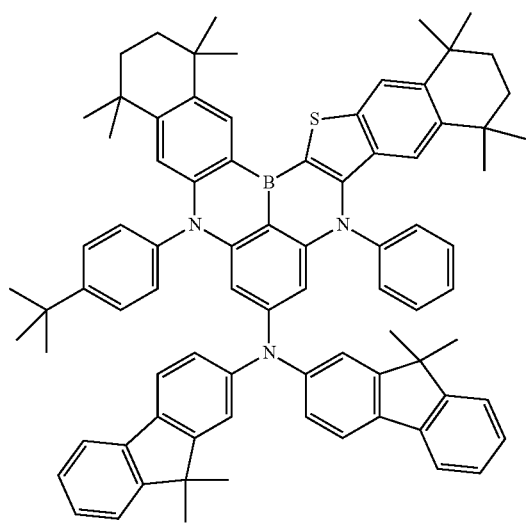

199
-continued
200
-continued
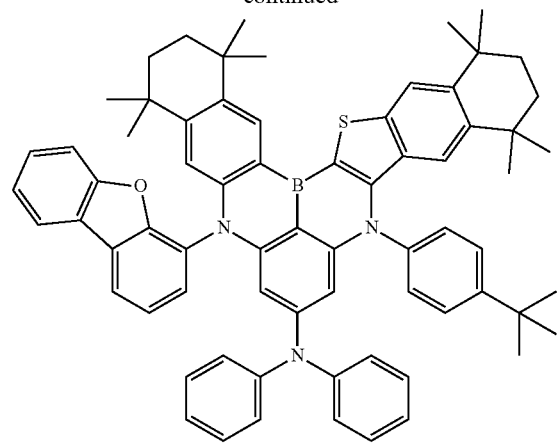

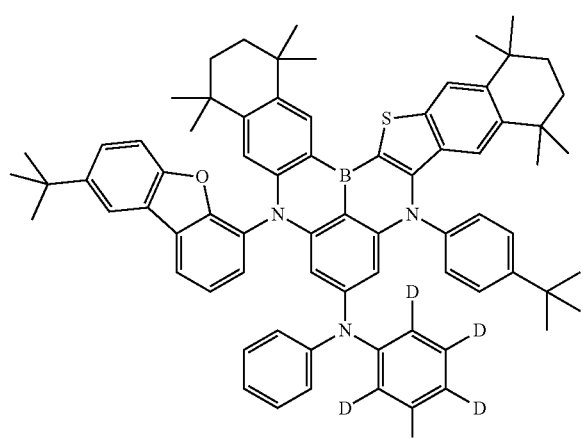
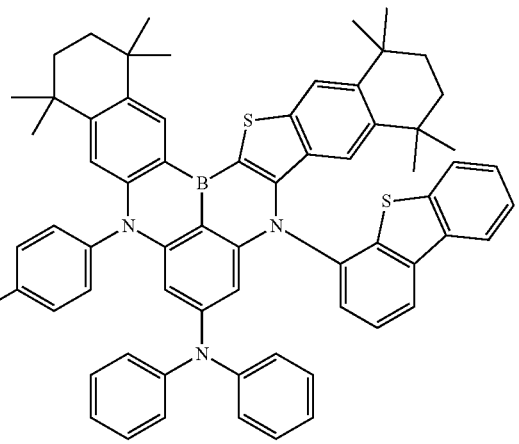
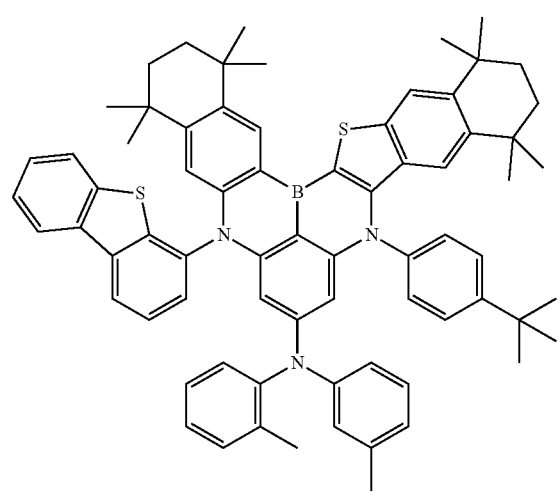
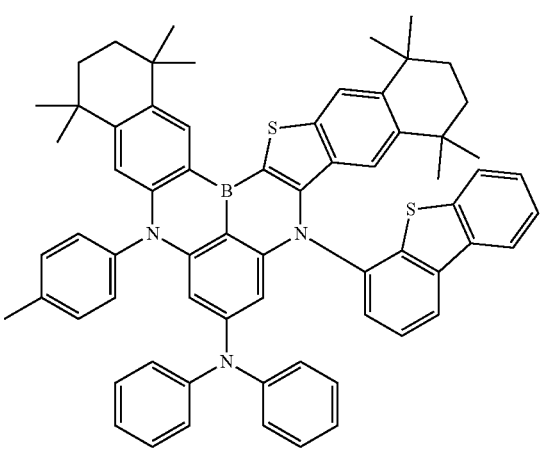

201
-continued
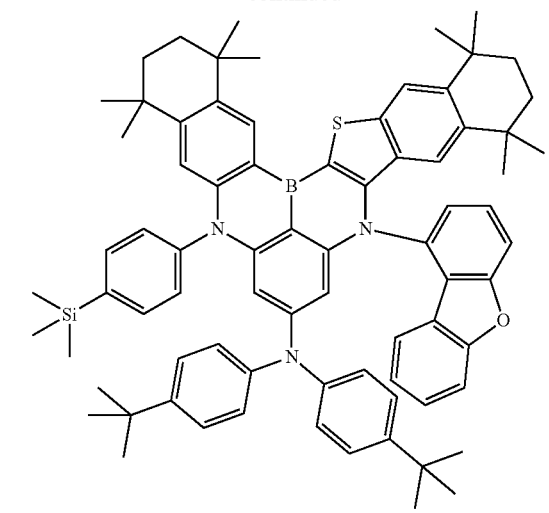
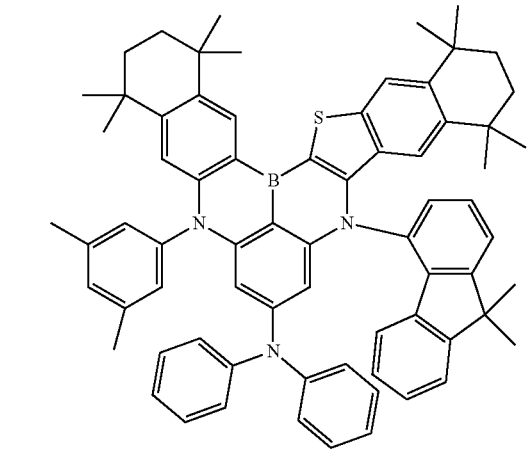
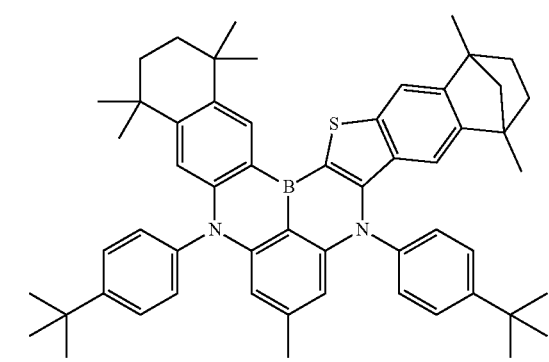
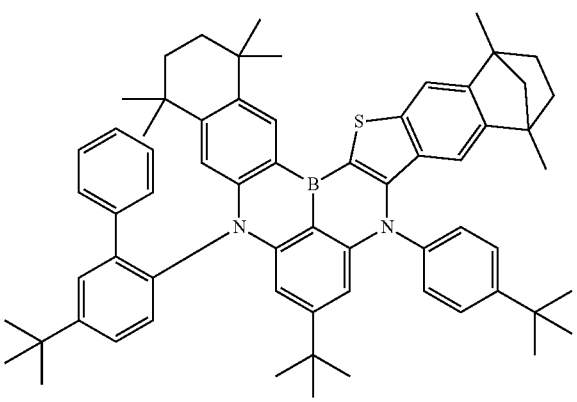
202
-continued
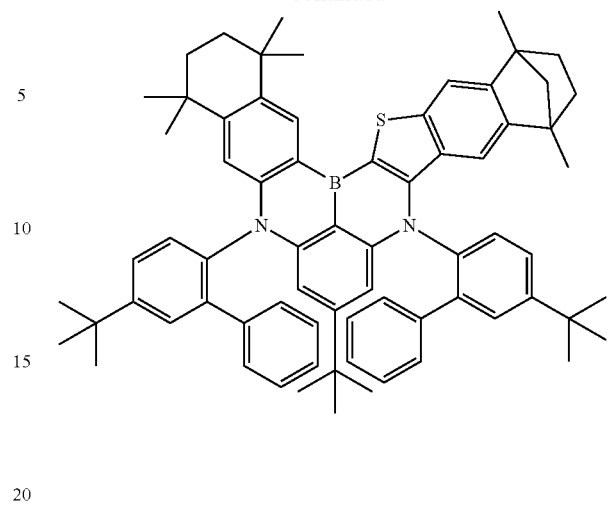
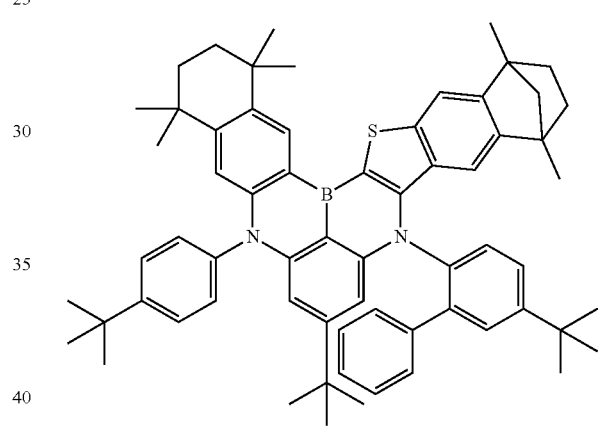
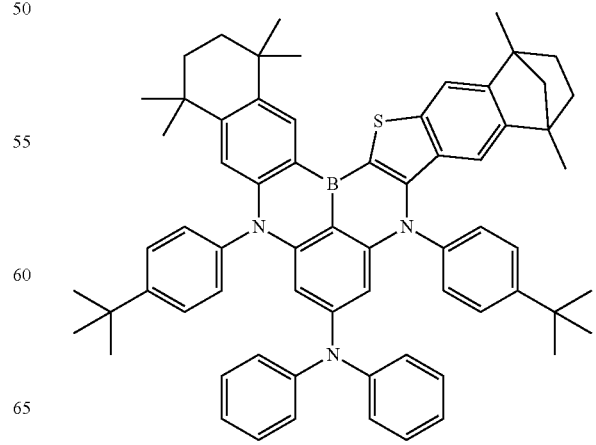

203
-continued
204
-continued
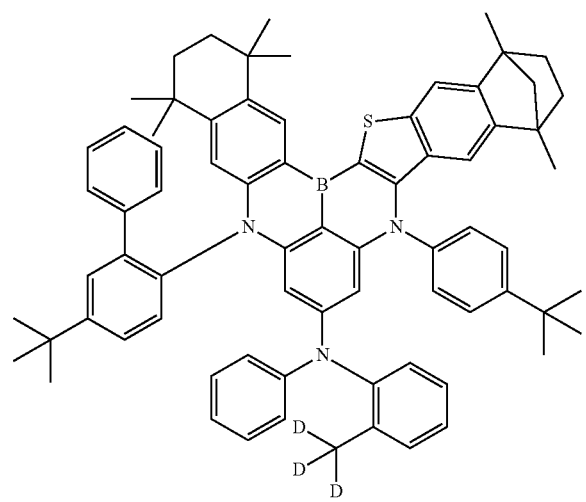
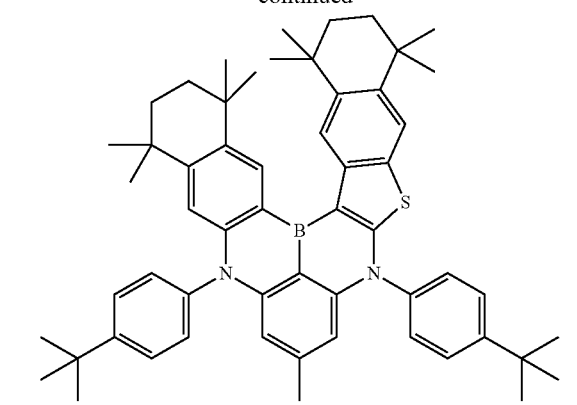
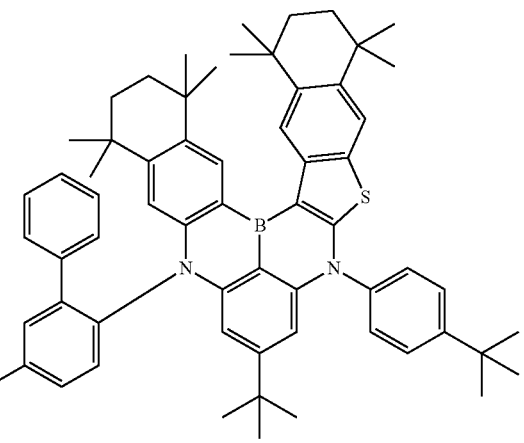
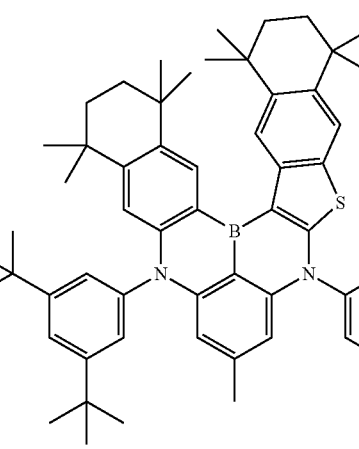
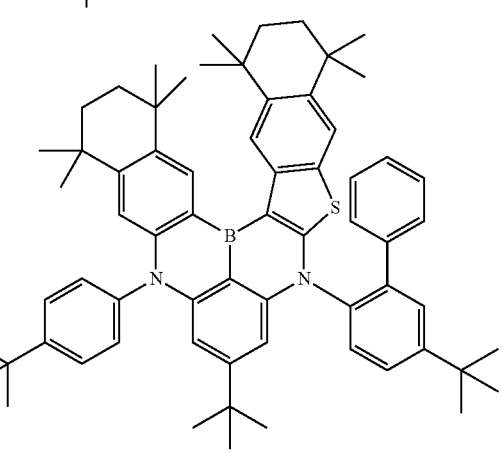

205
-continued
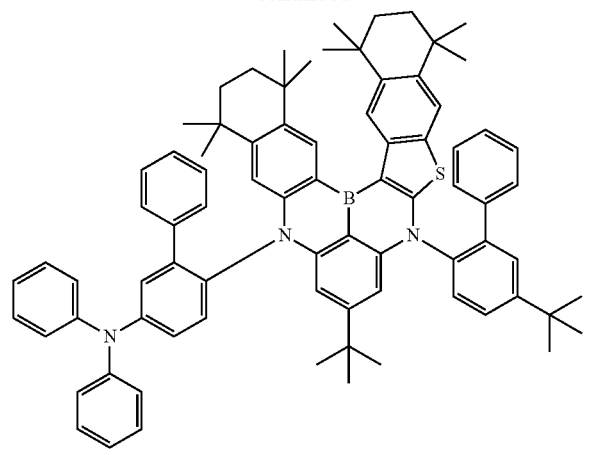
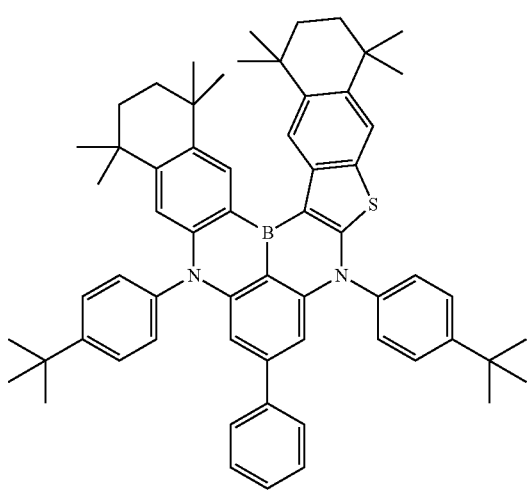
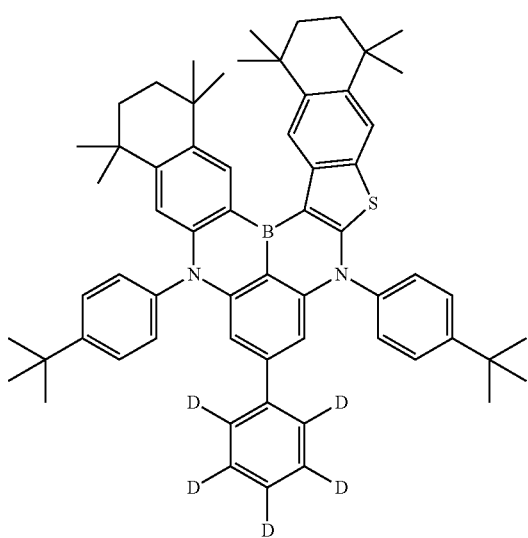
206
-continued
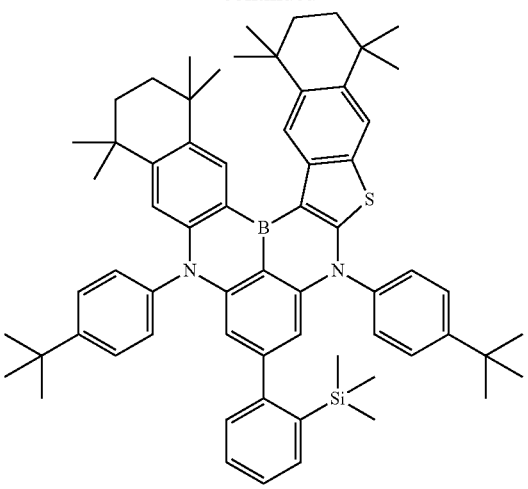
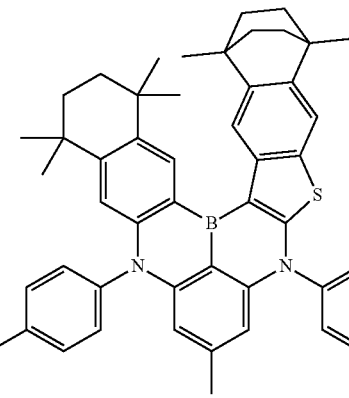
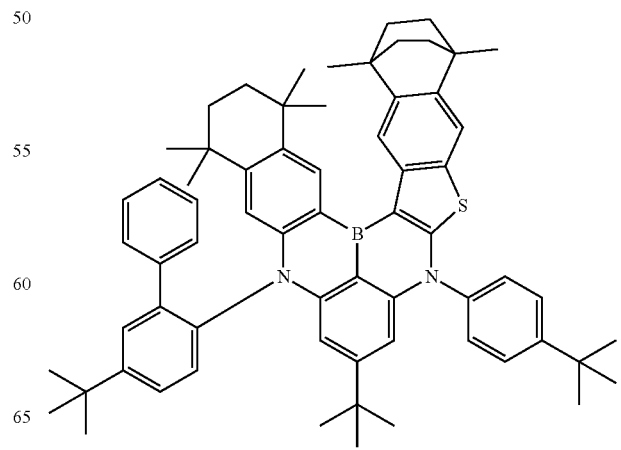

207
-continued
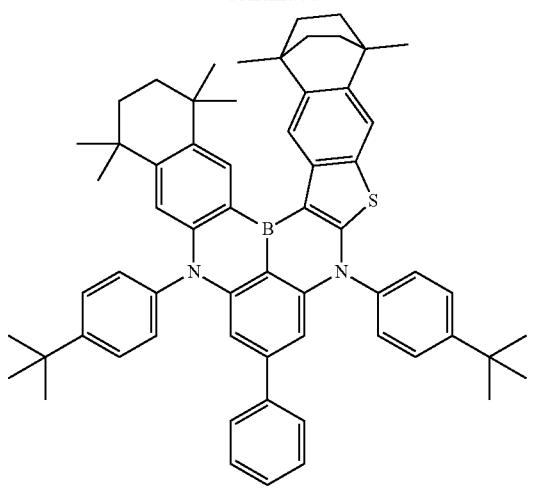
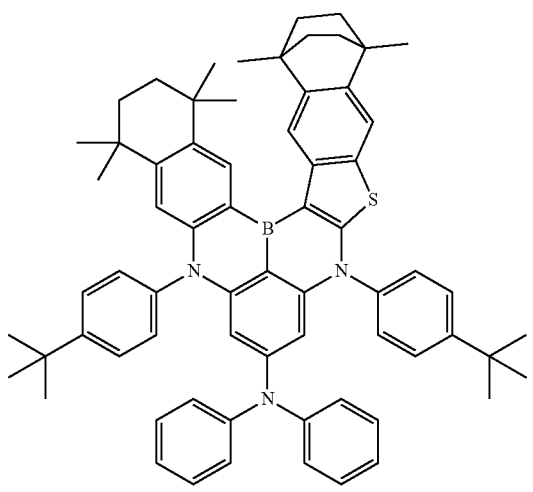
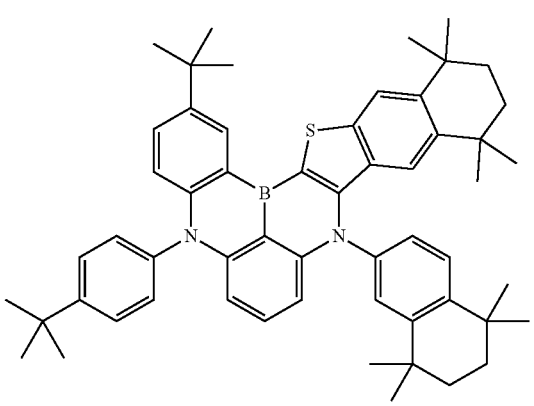
208
-continued
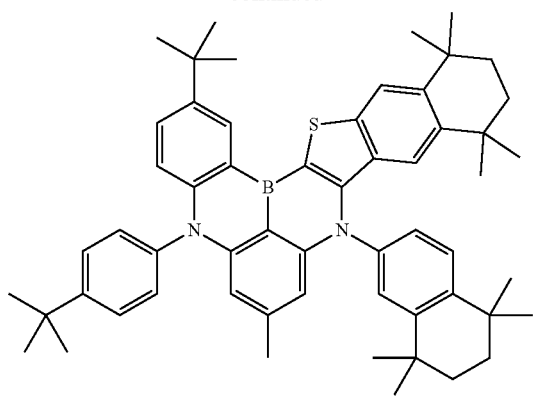
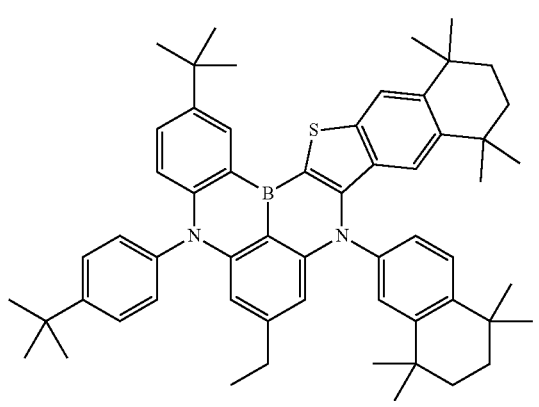
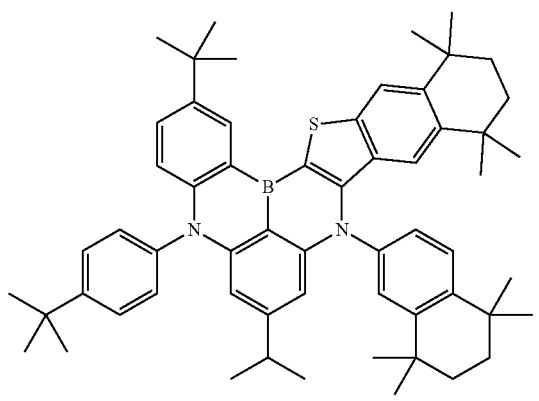
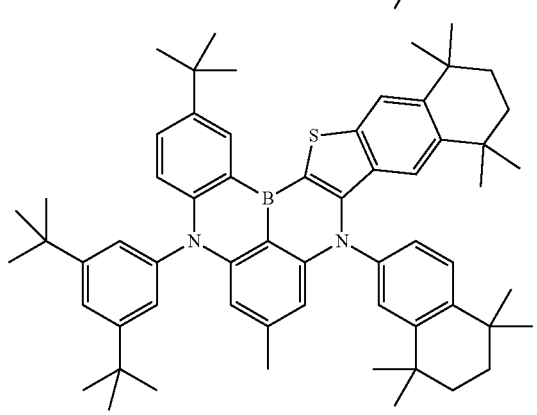

209
-continued
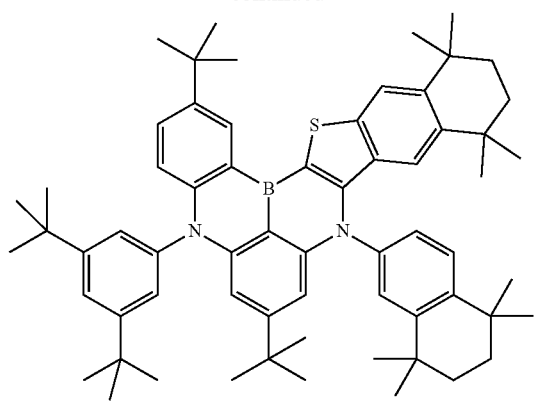
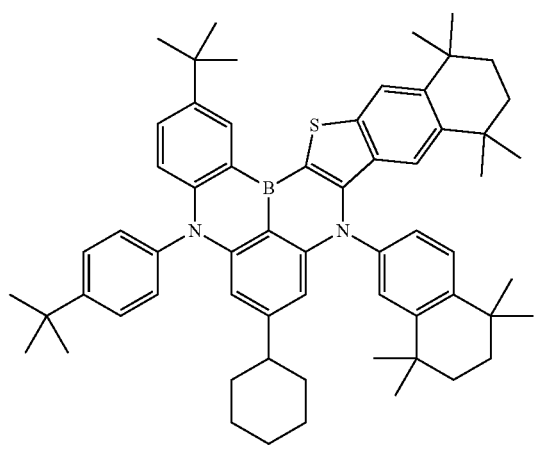
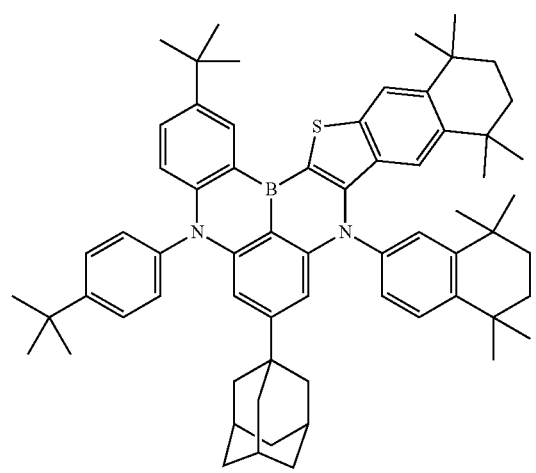
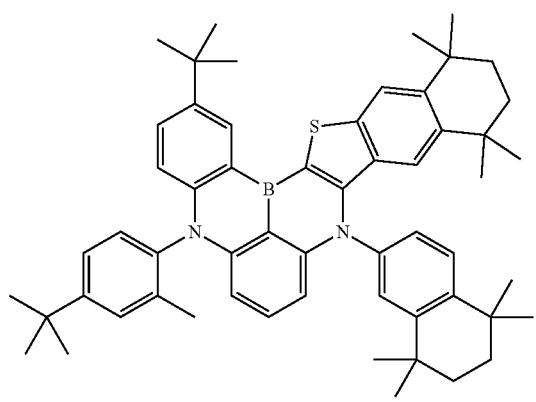
210
-continued
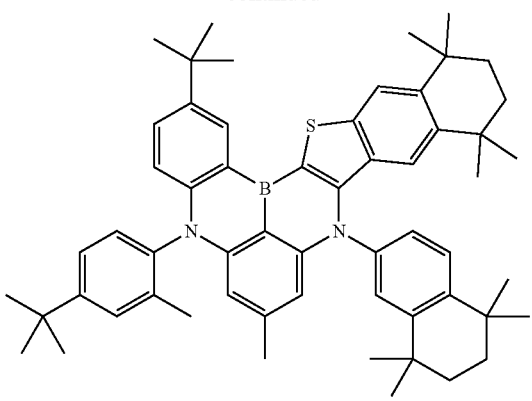
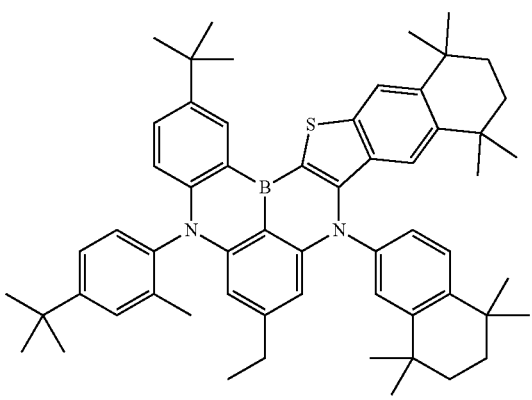
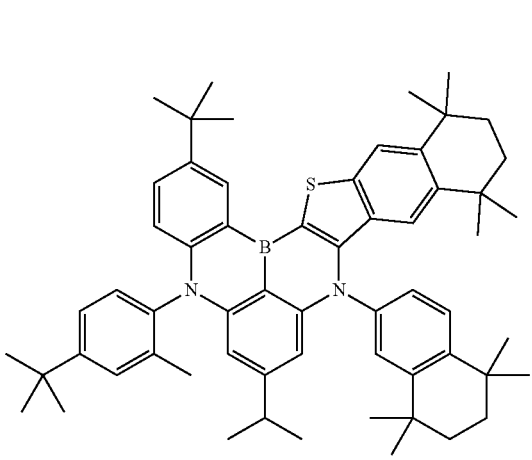
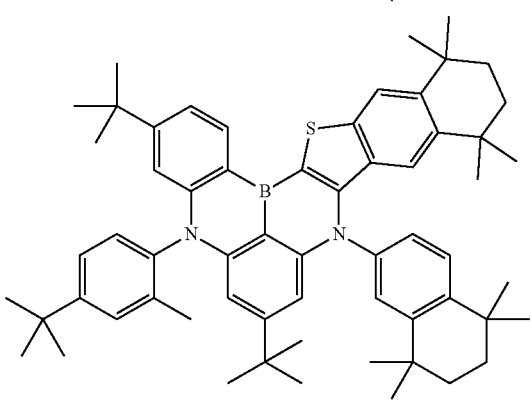

211
-continued
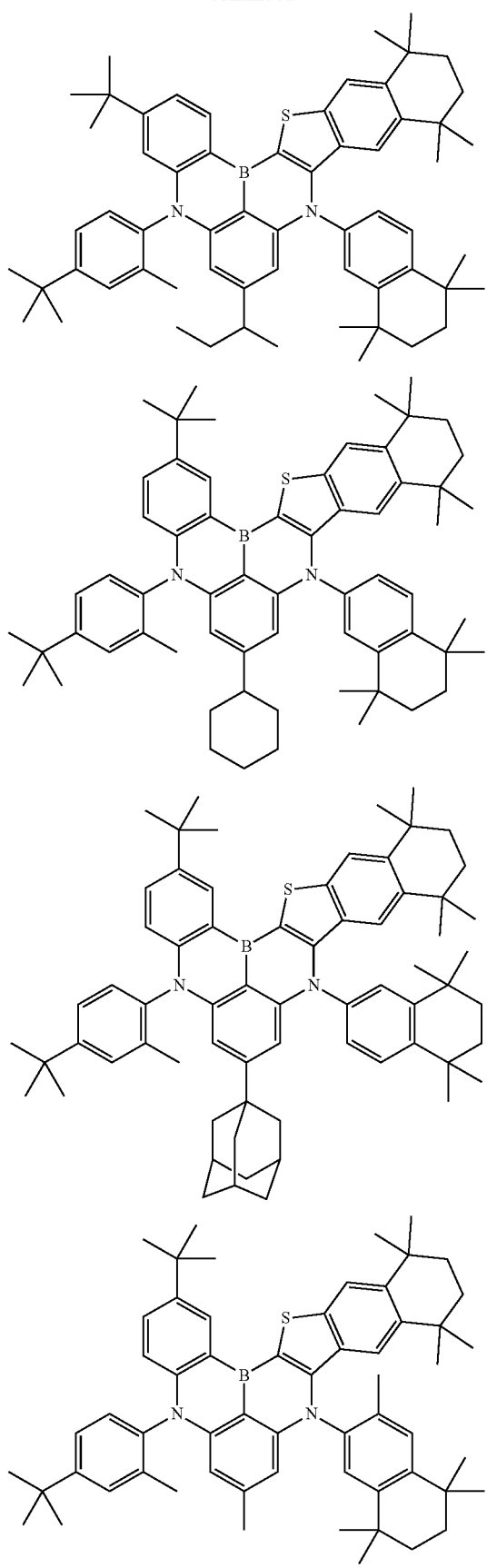
212
-continued
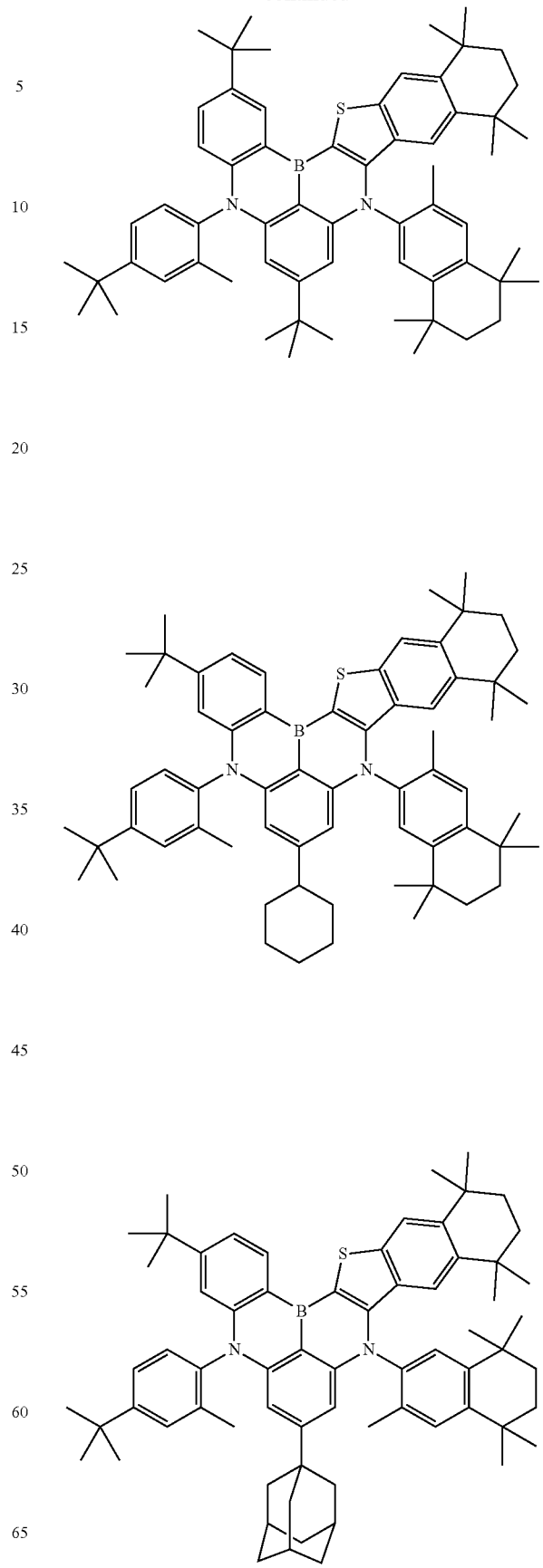

213
-continued
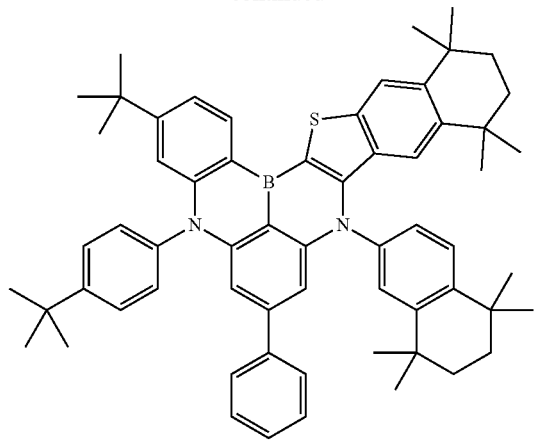
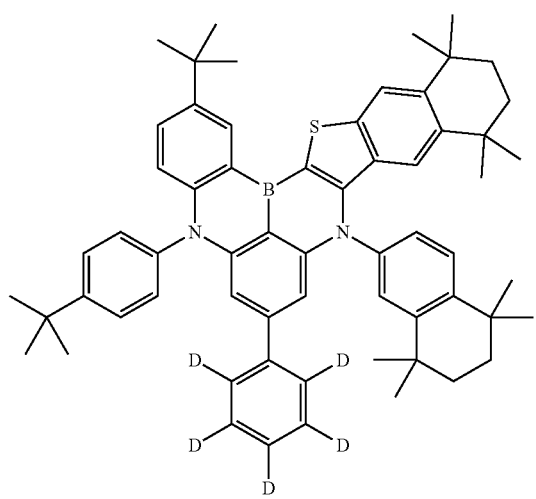
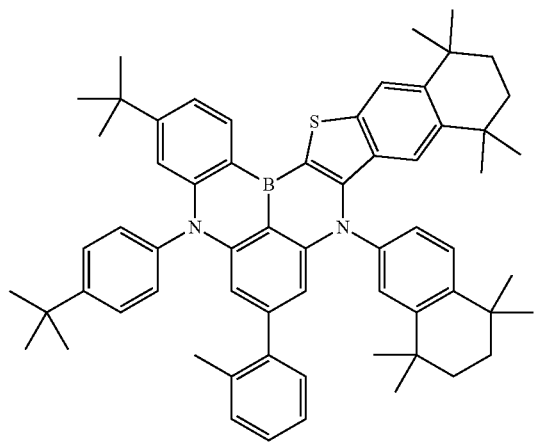
214
-continued
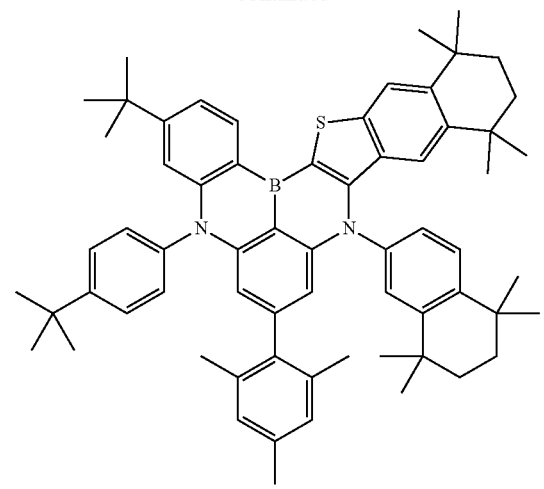
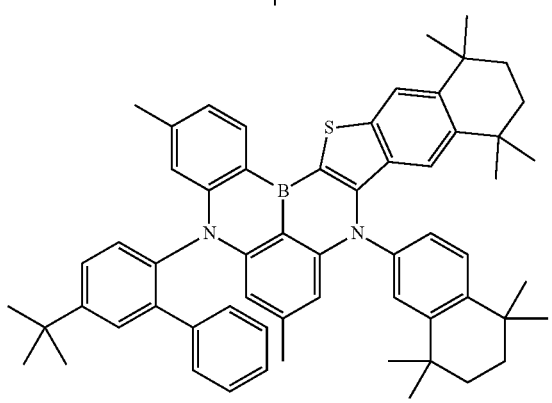
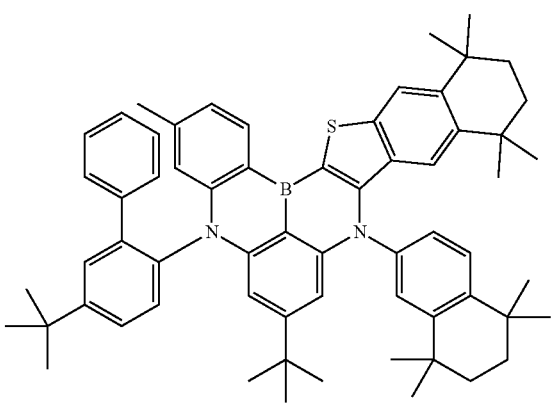
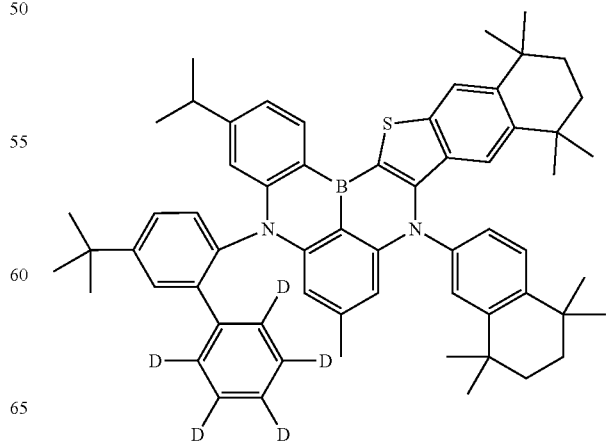

215
-continued
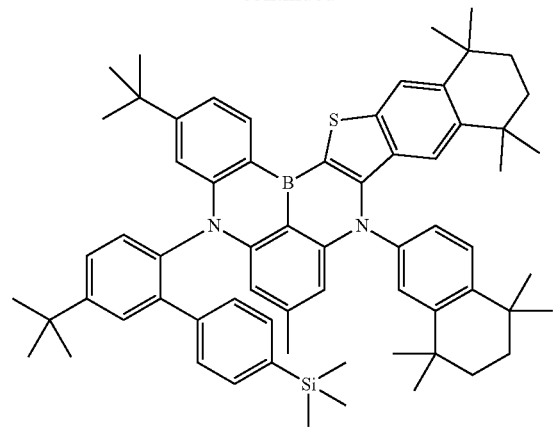
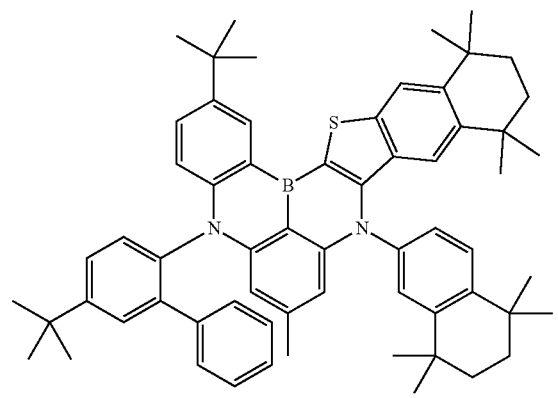
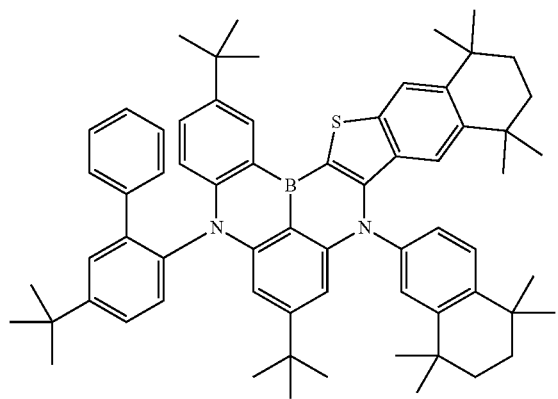
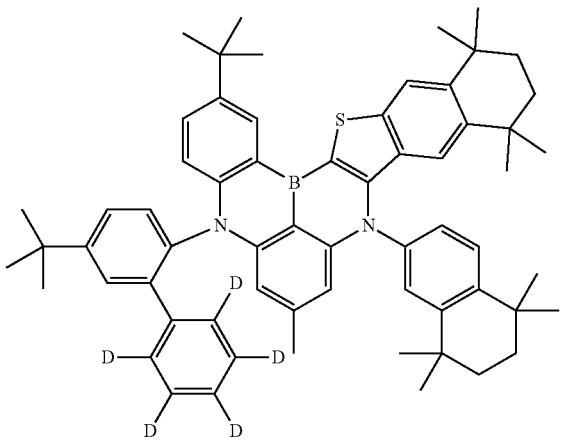
216
-continued
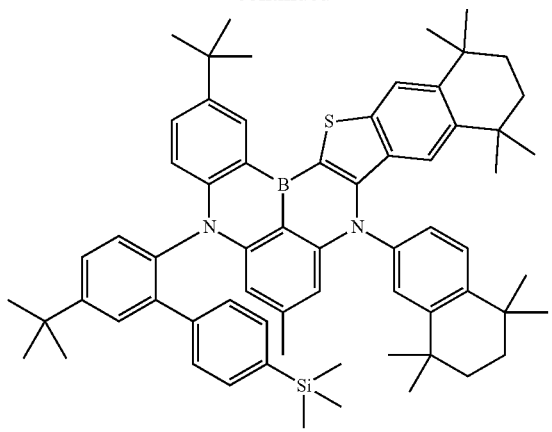
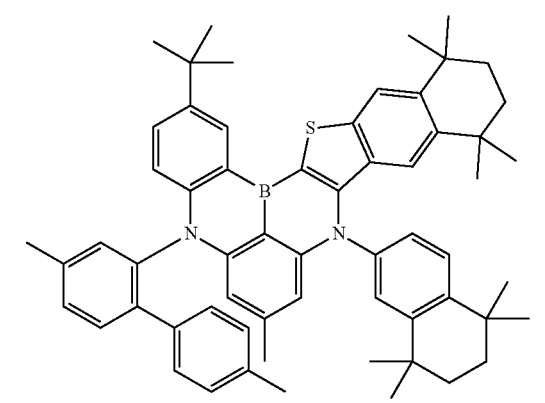
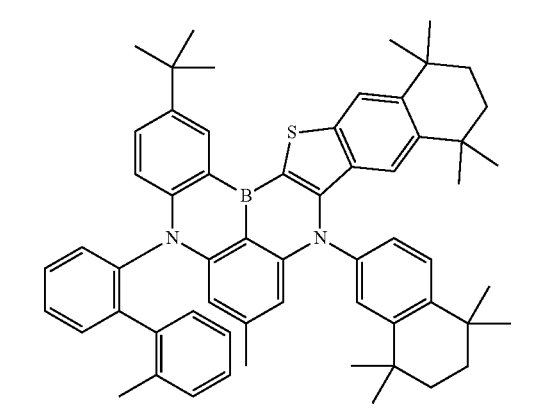
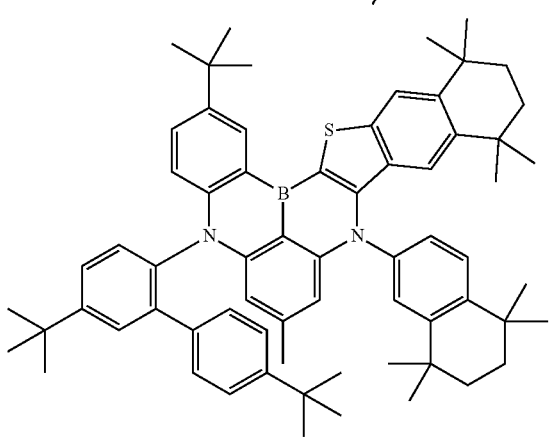

217
-continued
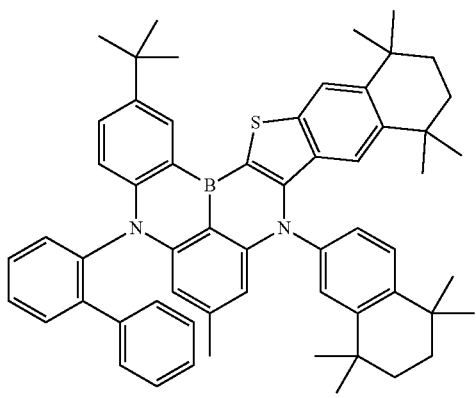
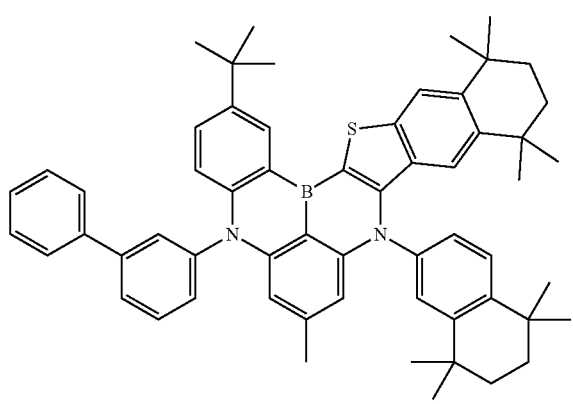
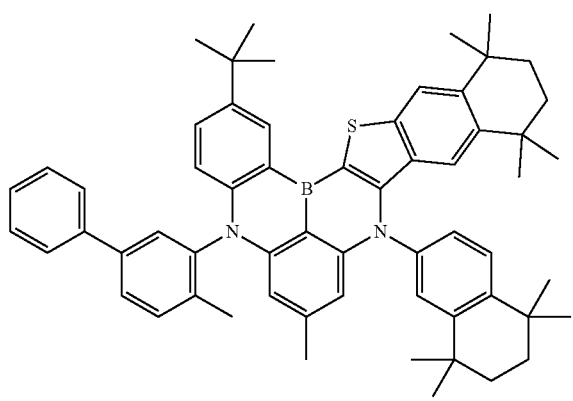
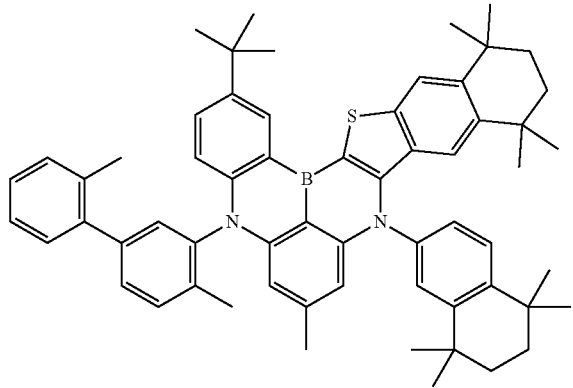
218
-continued
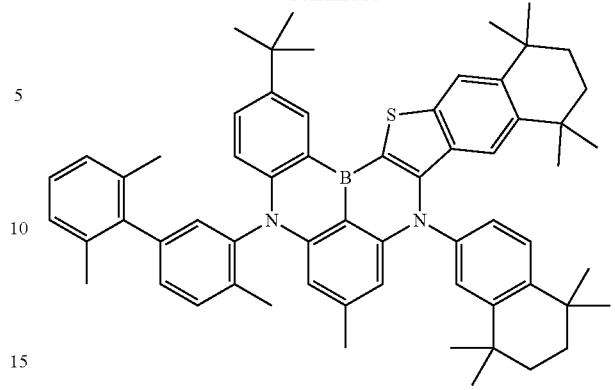
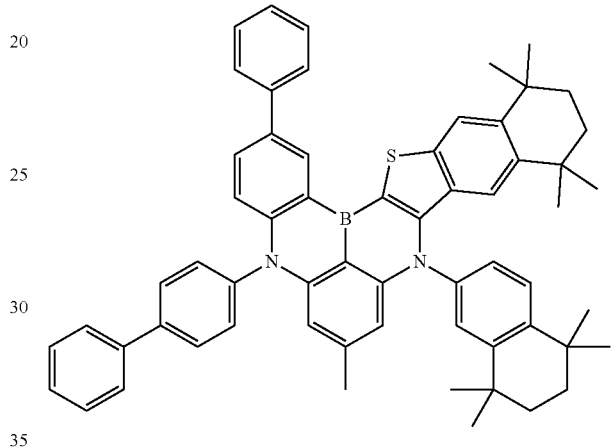
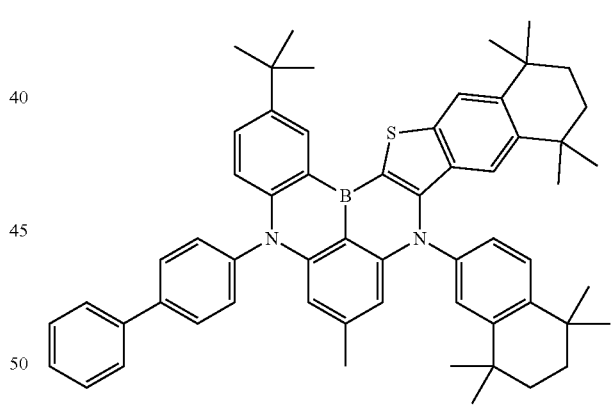
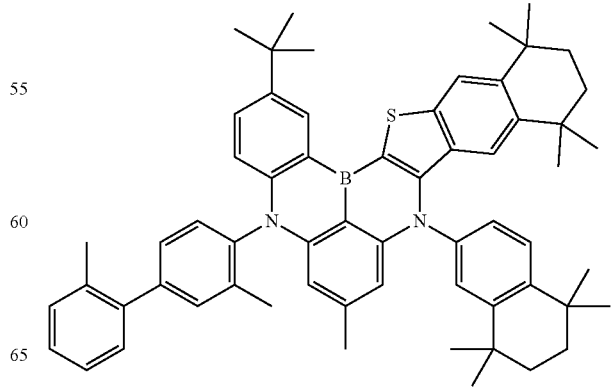

219
-continued
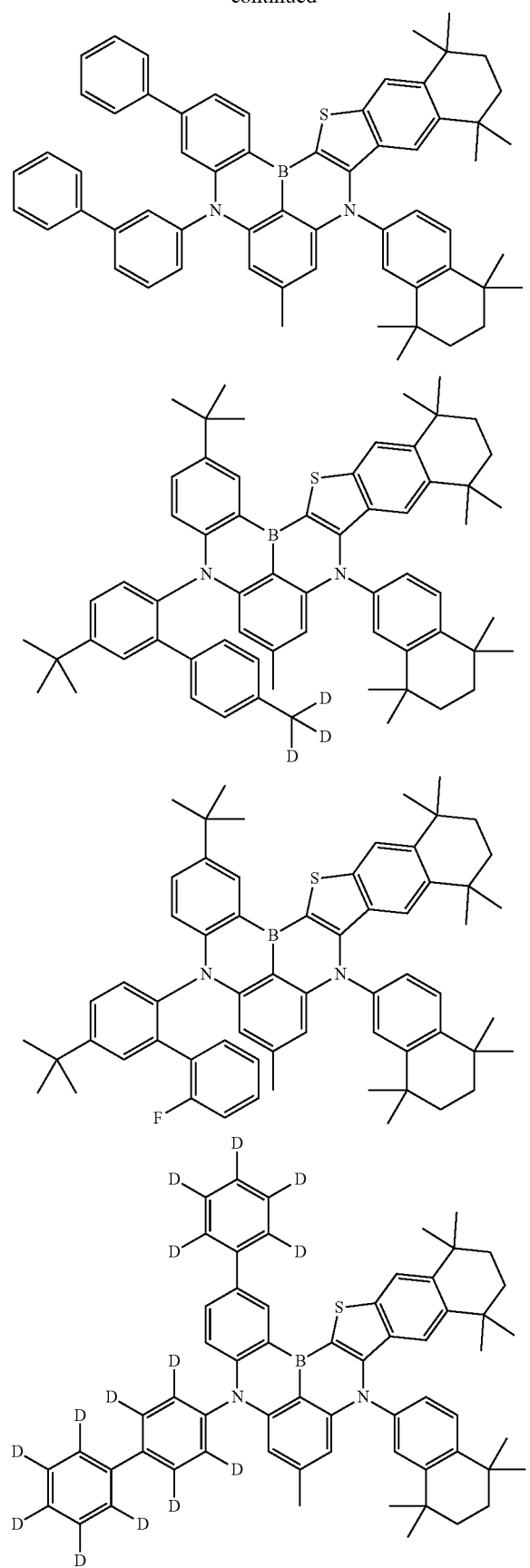
220
-continued
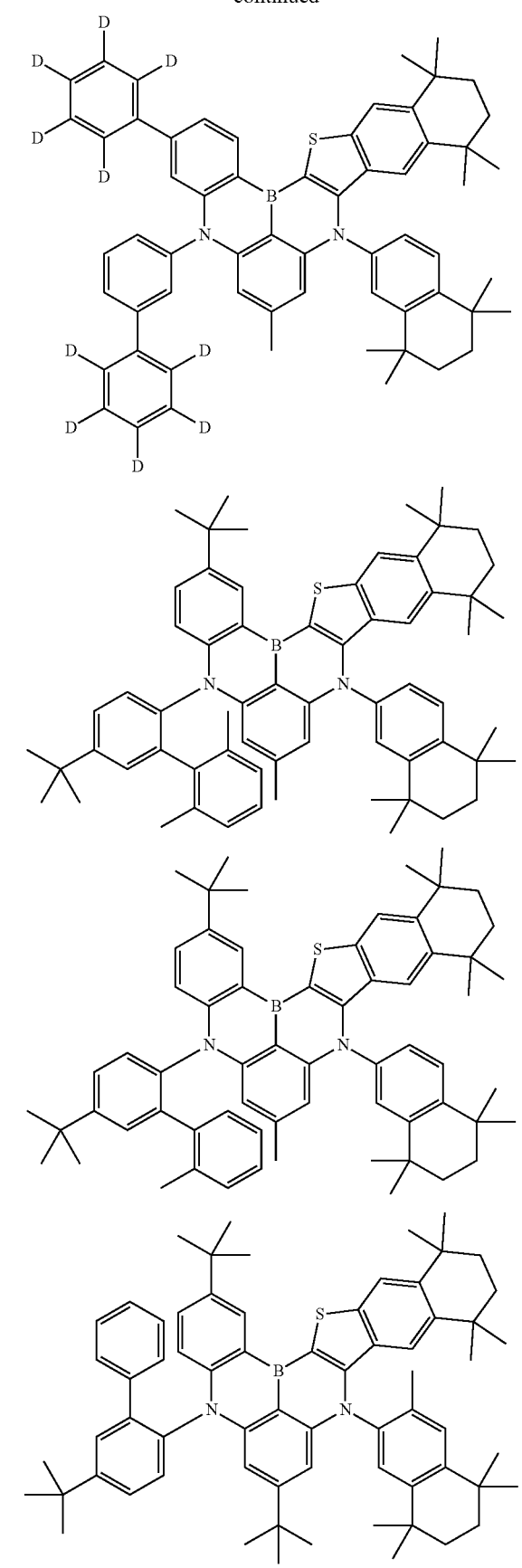

221
-continued
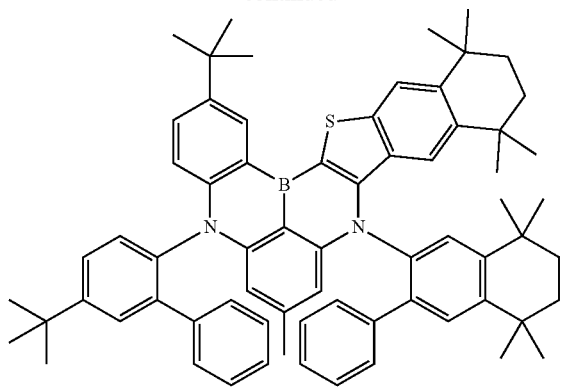
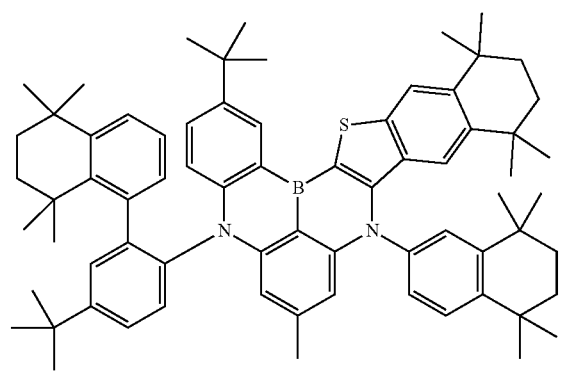
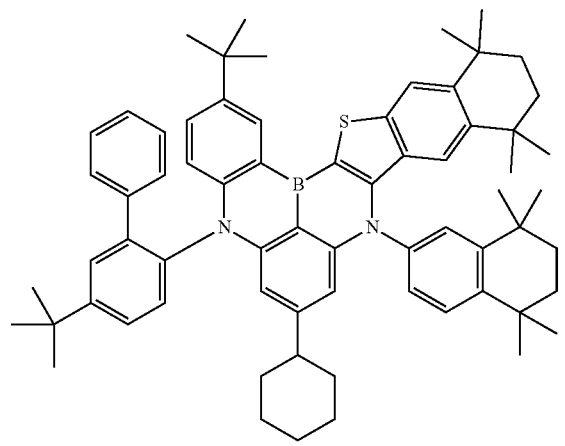
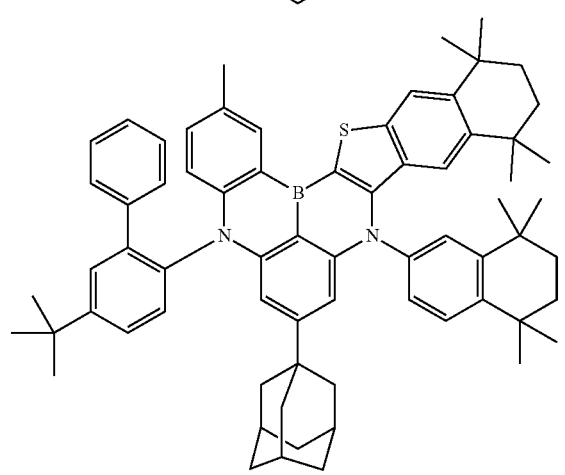
222
-continued
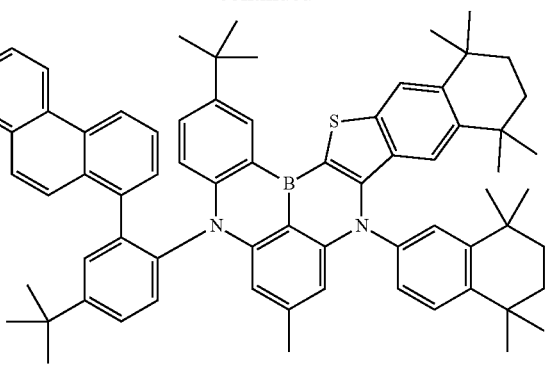
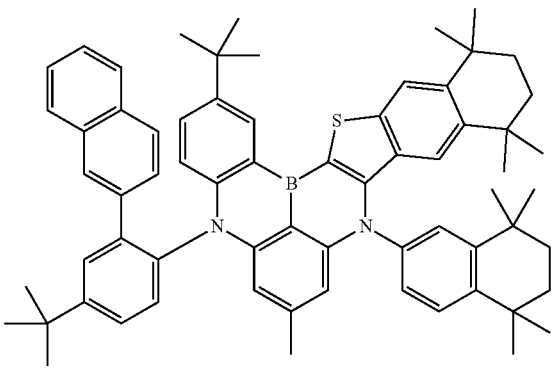
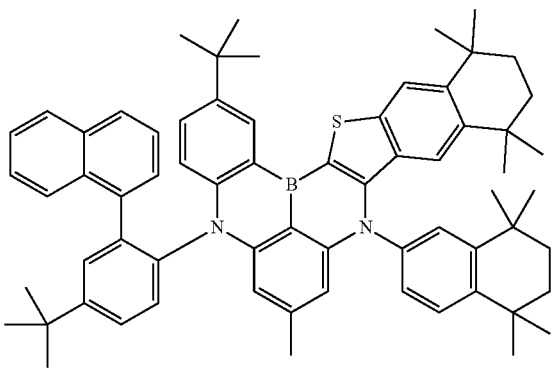
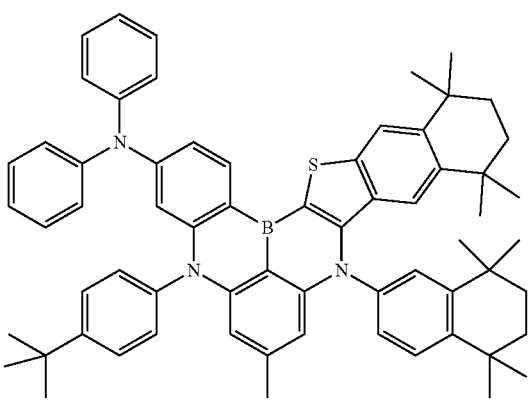

223
-continued
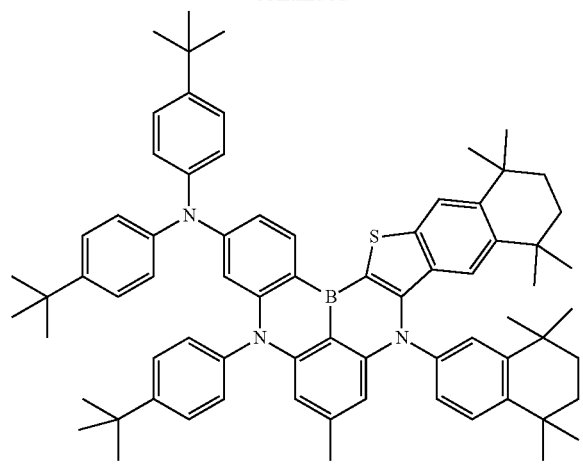
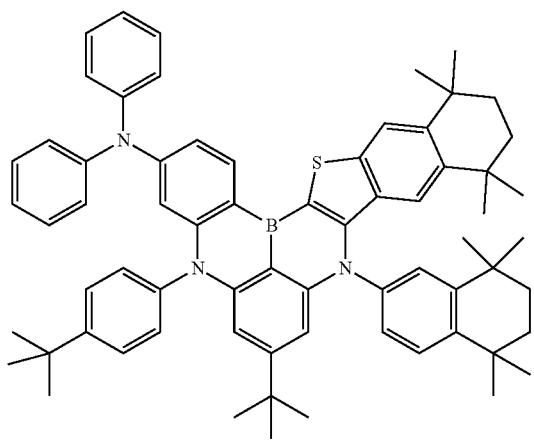
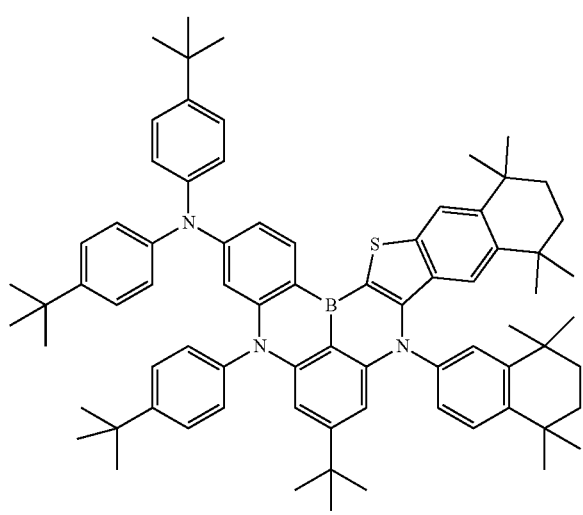
224
-continued
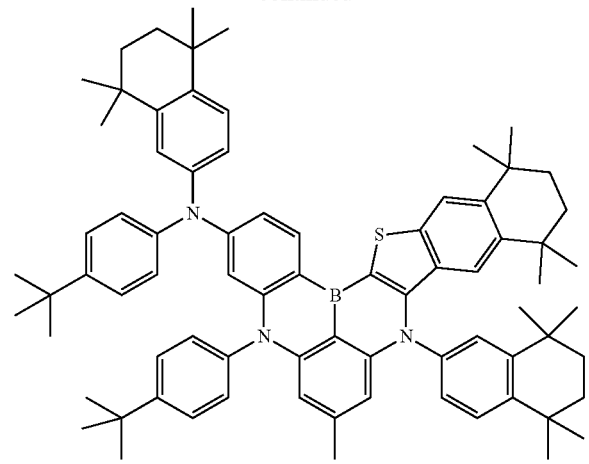
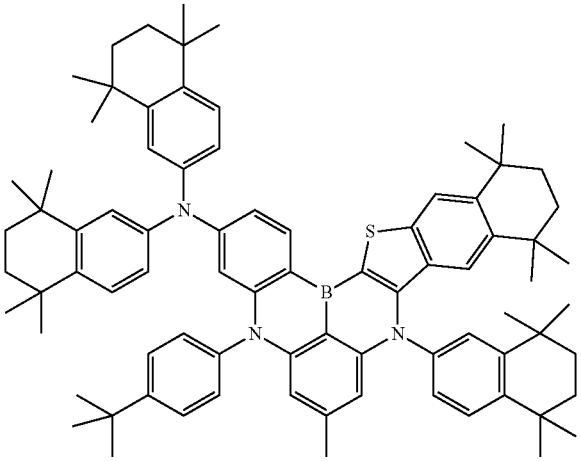
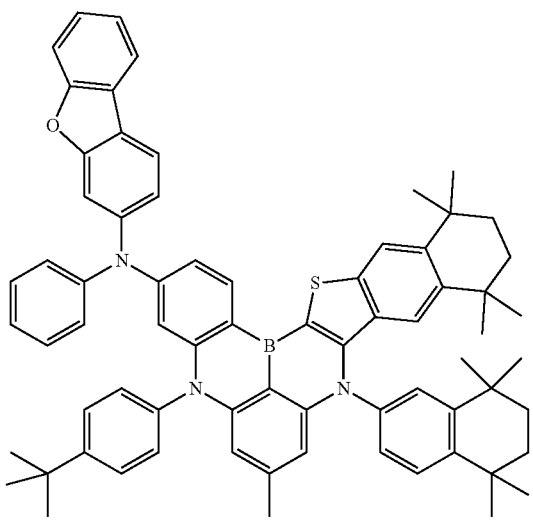

225
-continued
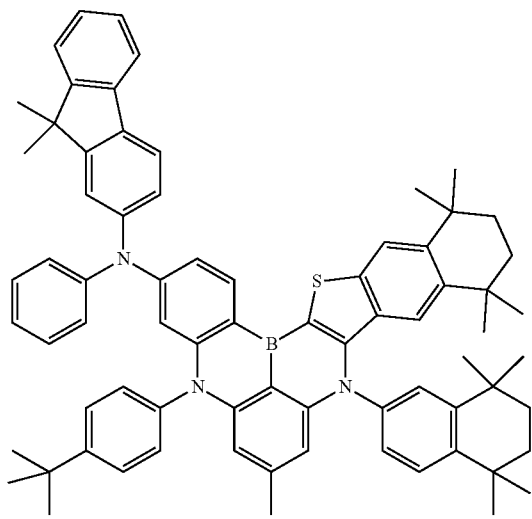
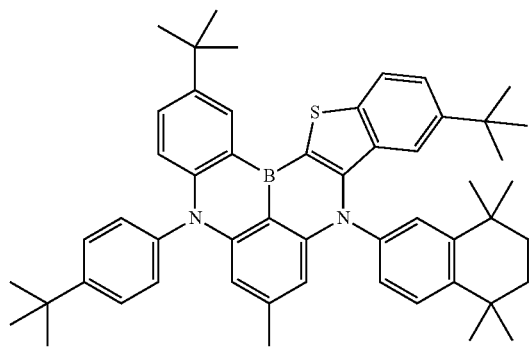
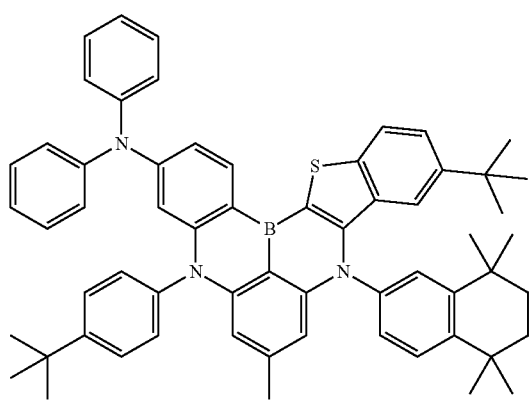
226
-continued
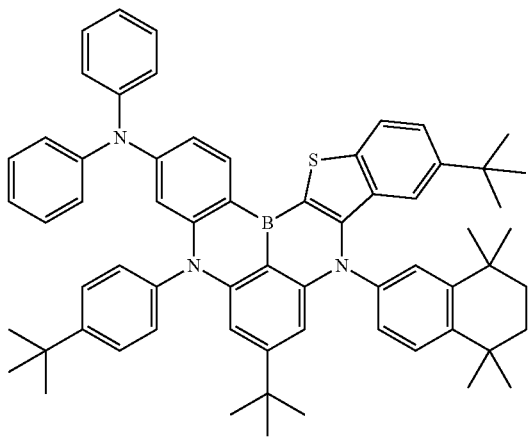
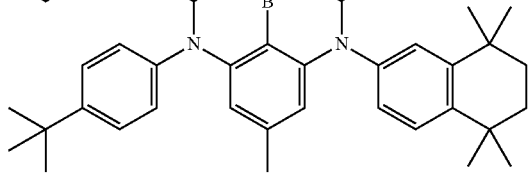
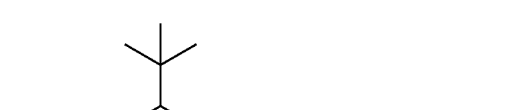

227
-continued
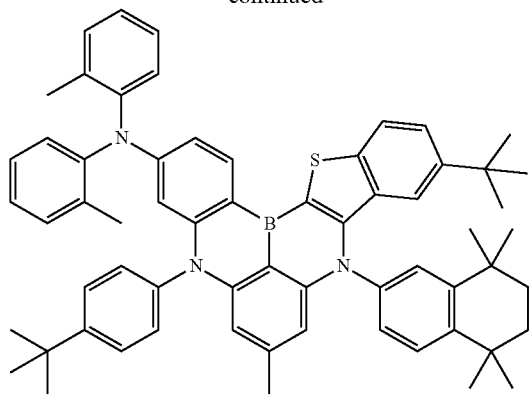
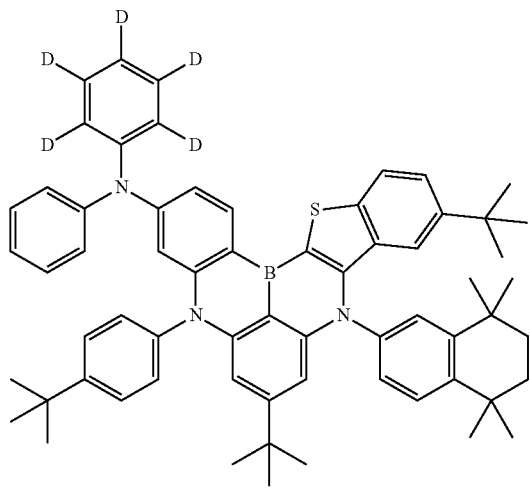
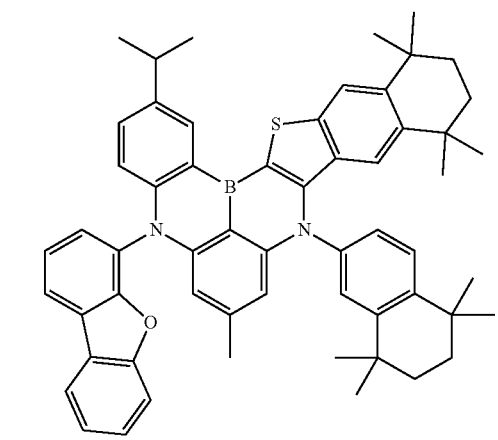
228
-continued
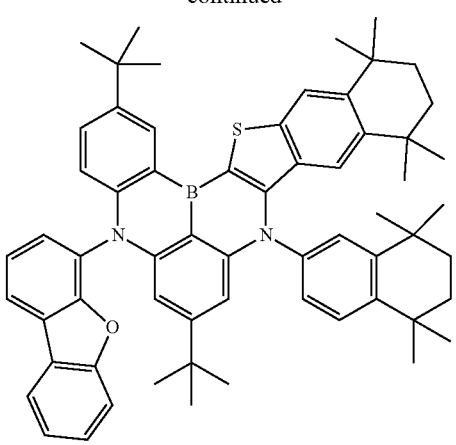
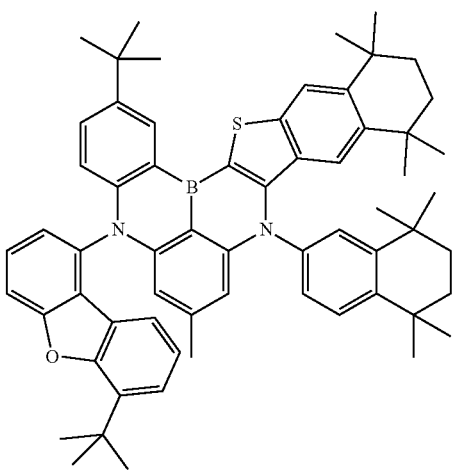
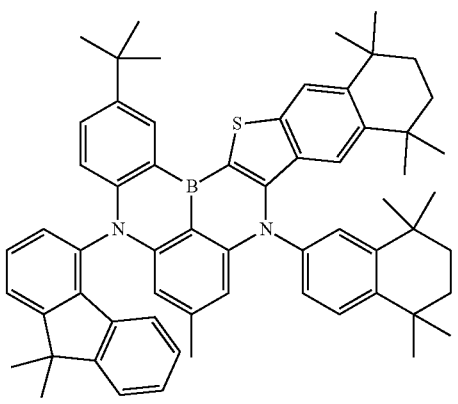
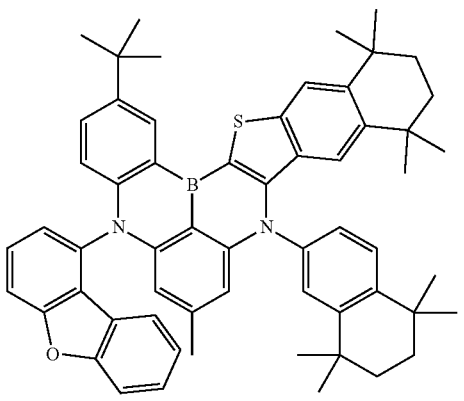

229
-continued
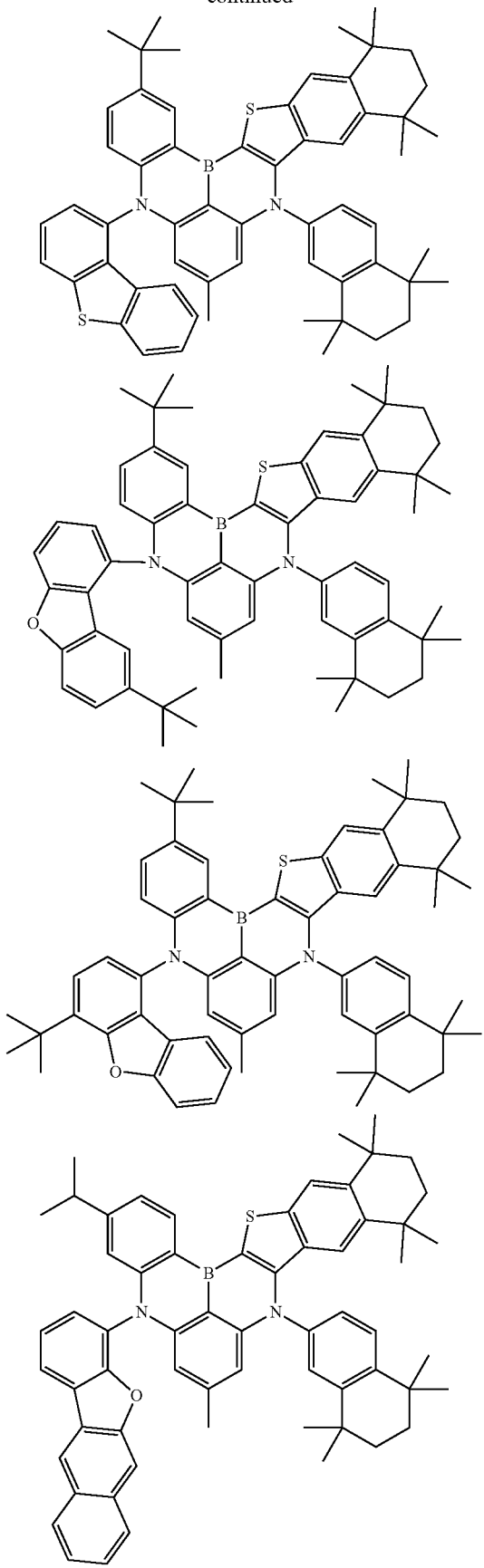
230
-continued
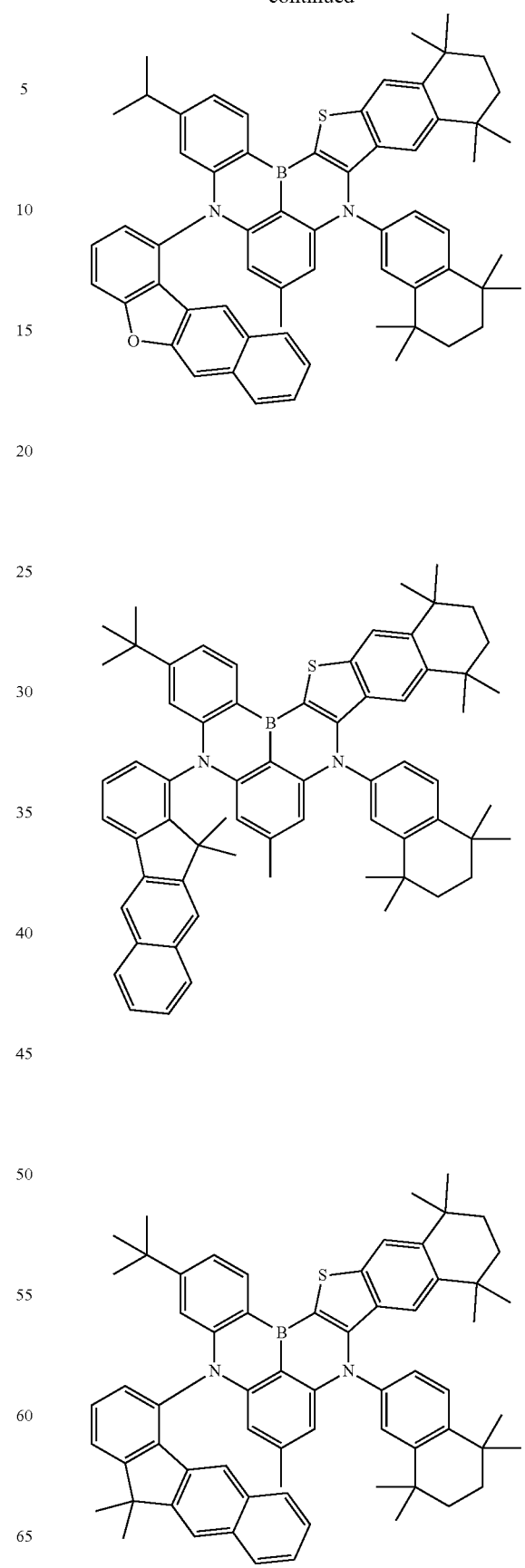

231
-continued
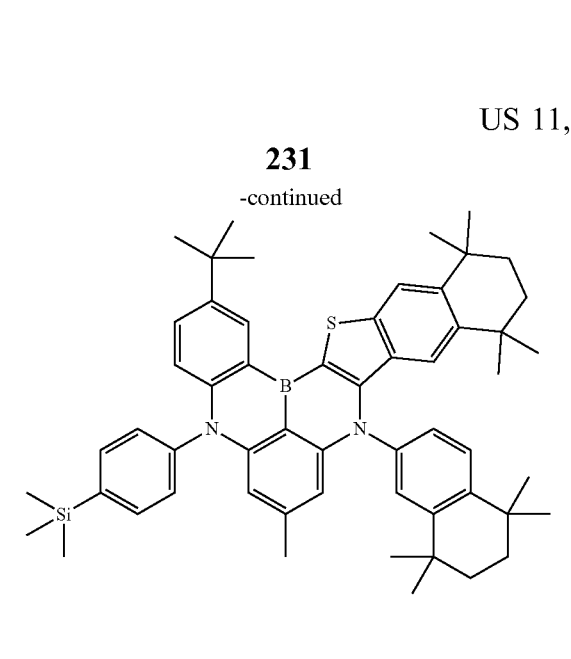
232
-continued
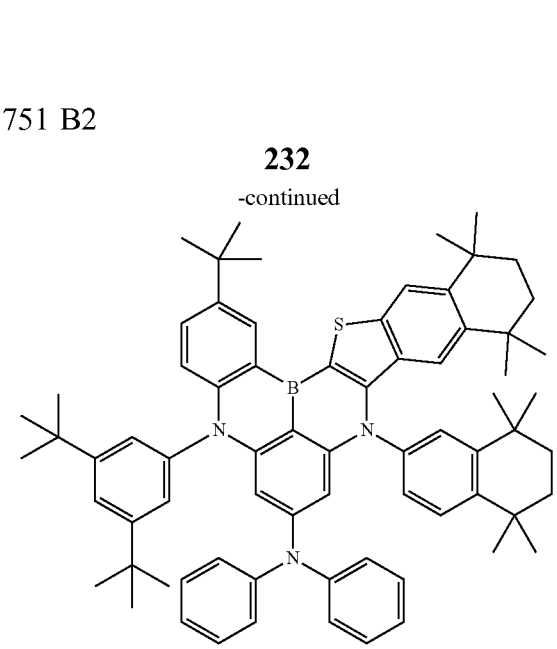

233
-continued
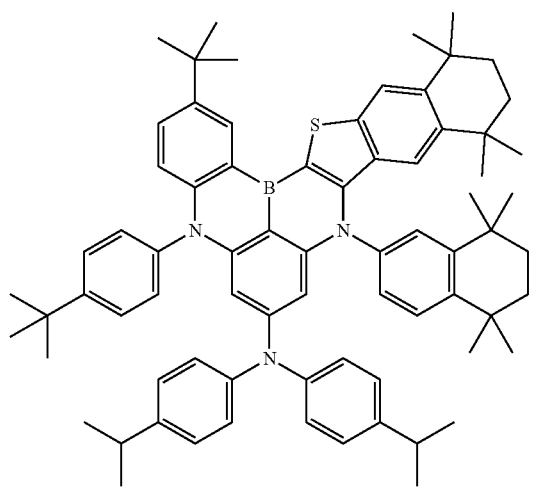
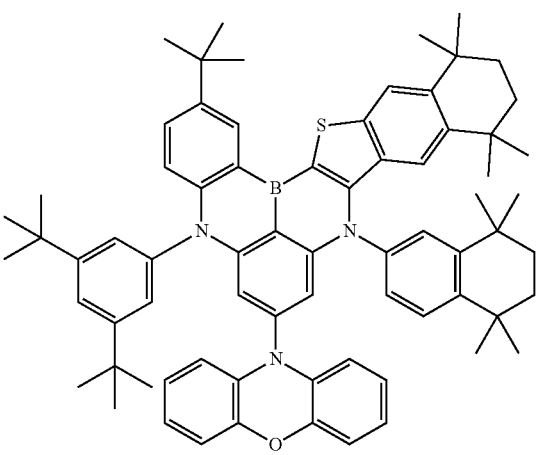
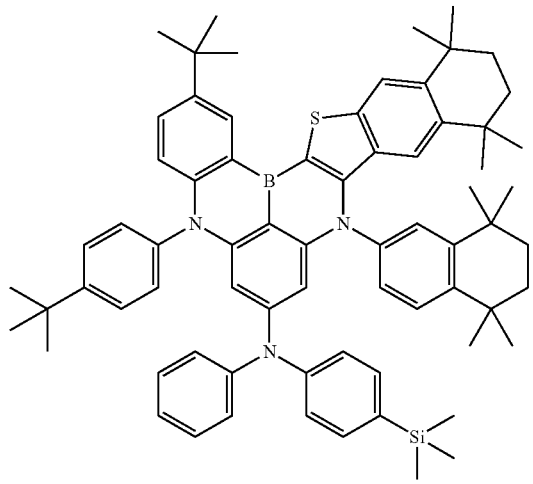
234
-continued
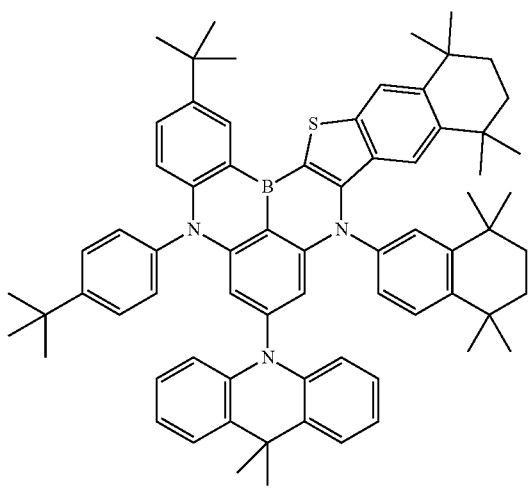
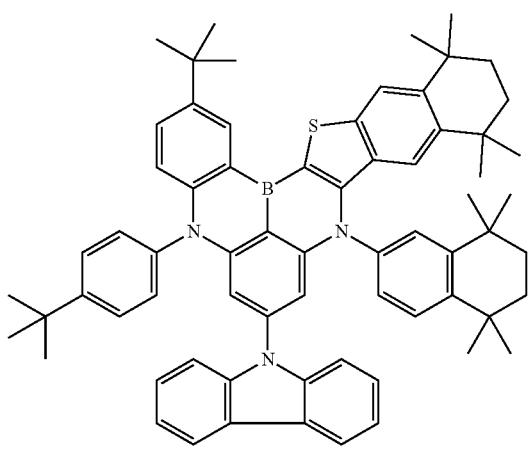
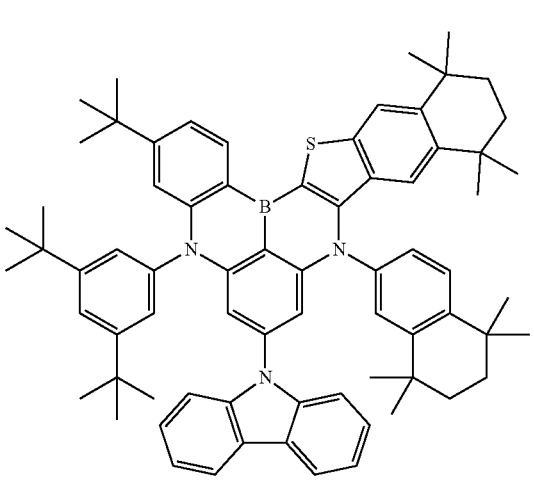

235
-continued
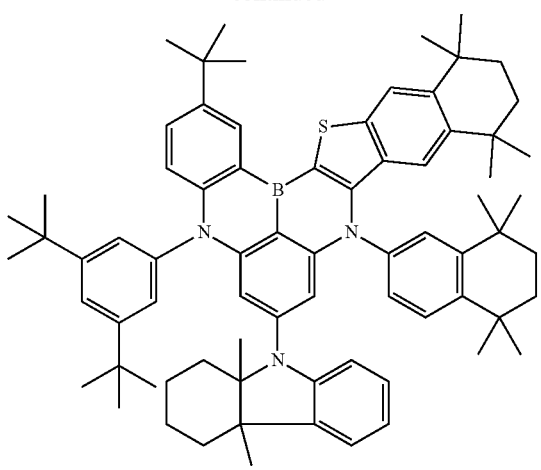
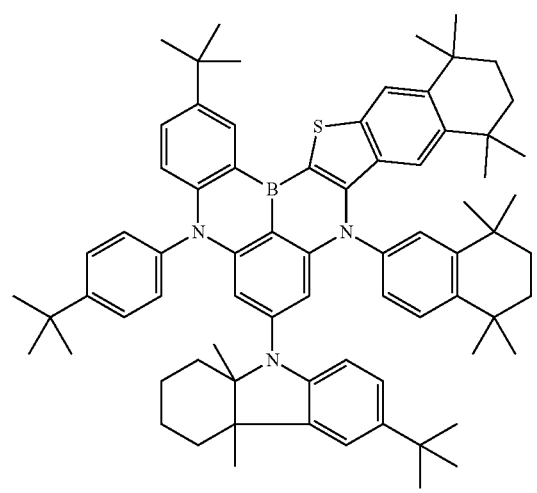
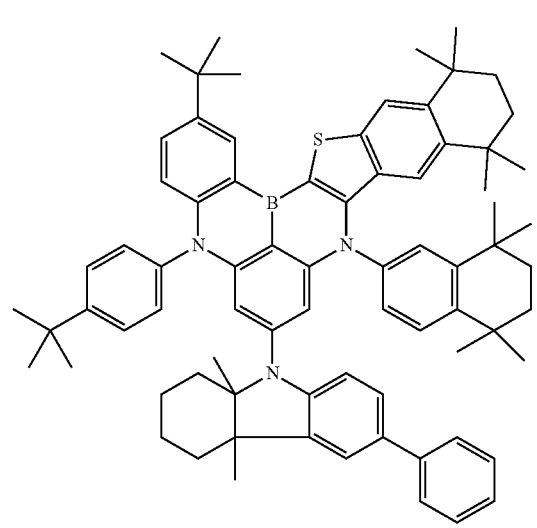
236
-continued
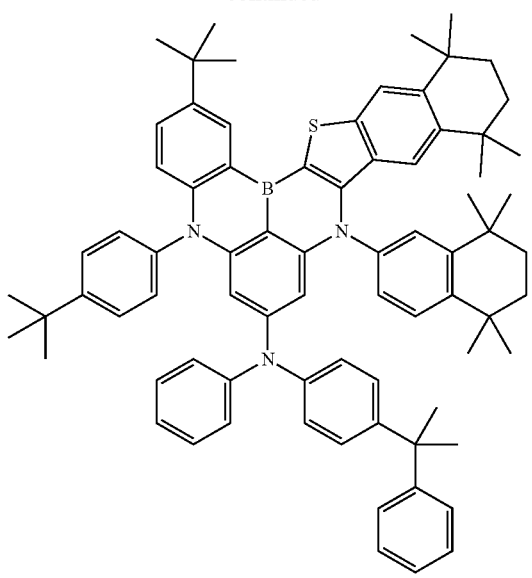
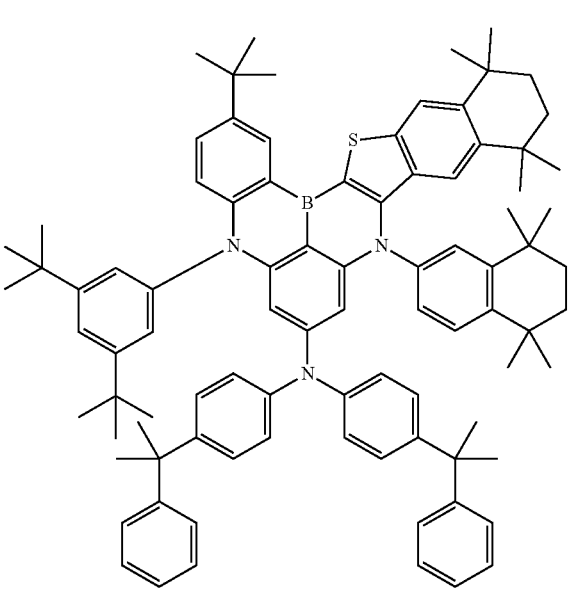
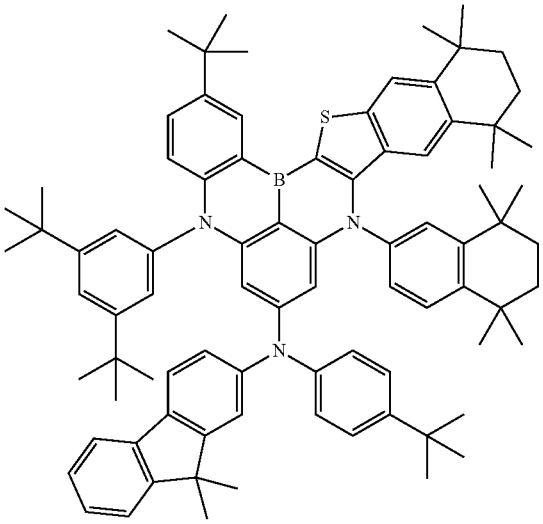

237
-continued
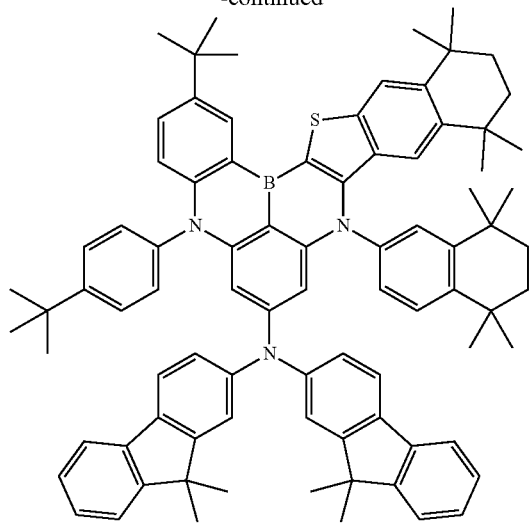
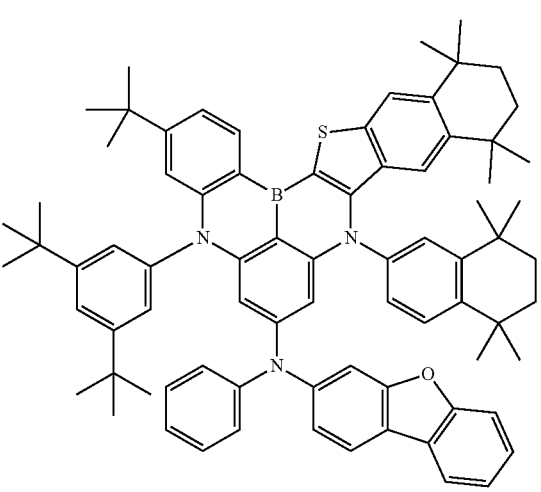
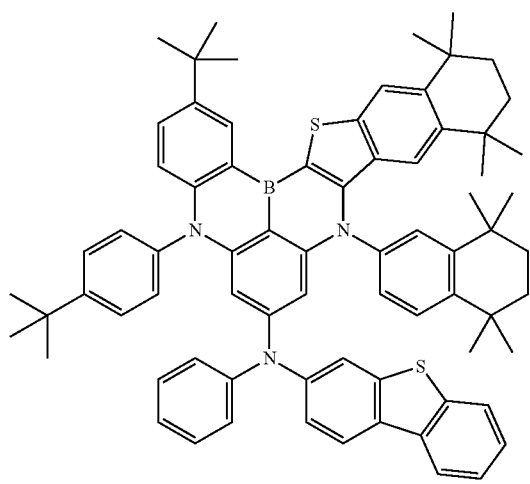
238
-continued
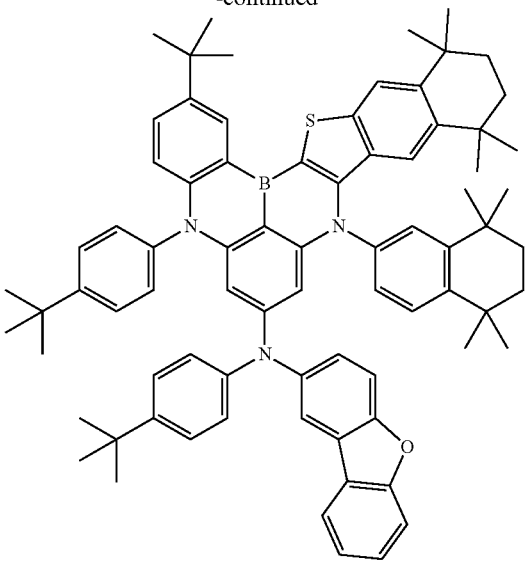
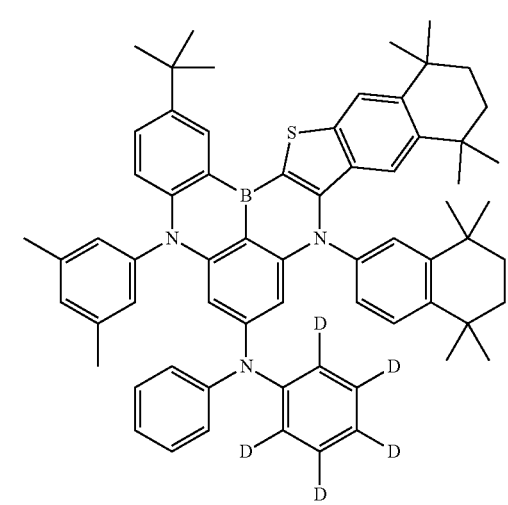
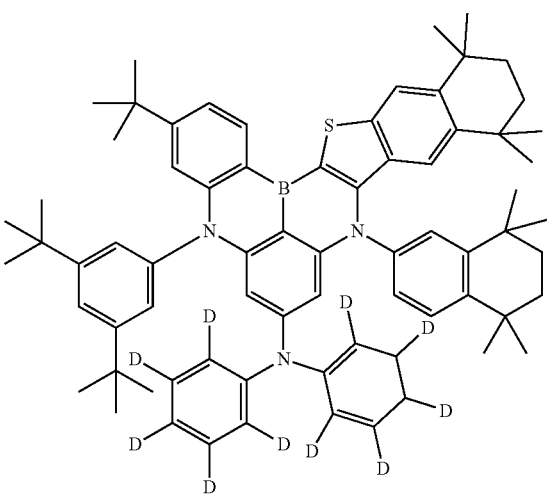

239
-continued
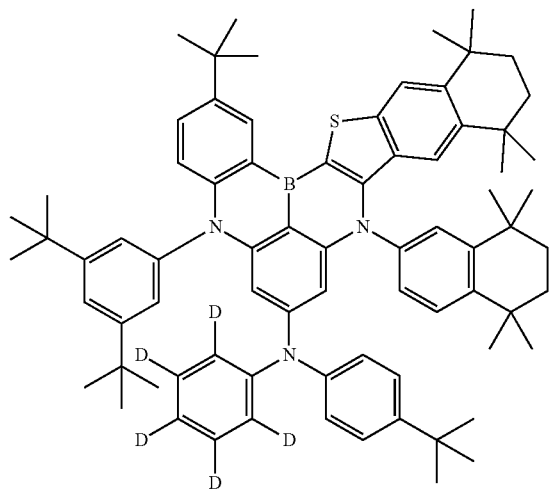
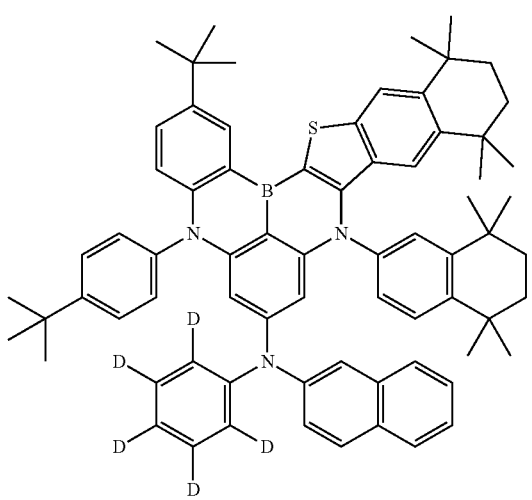
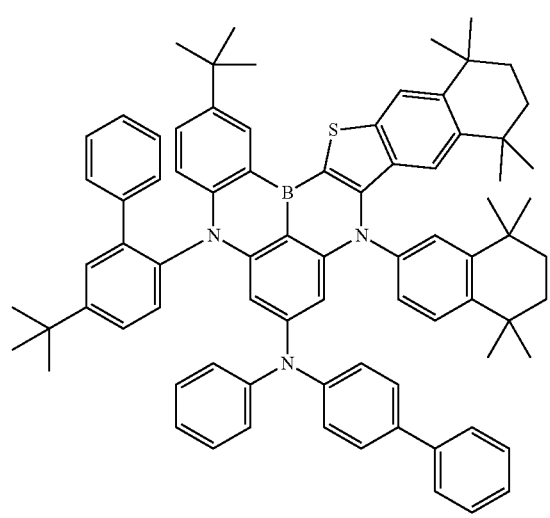
240
-continued
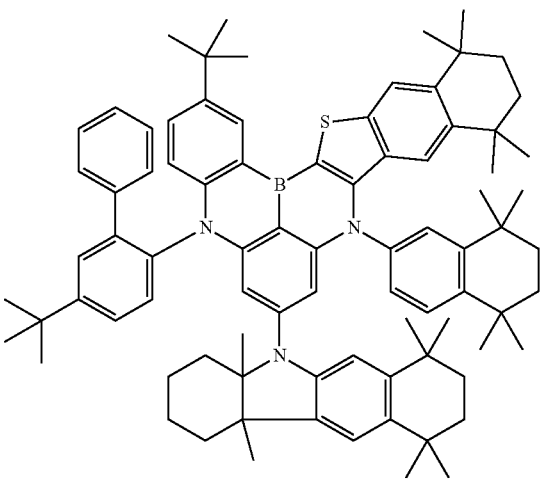
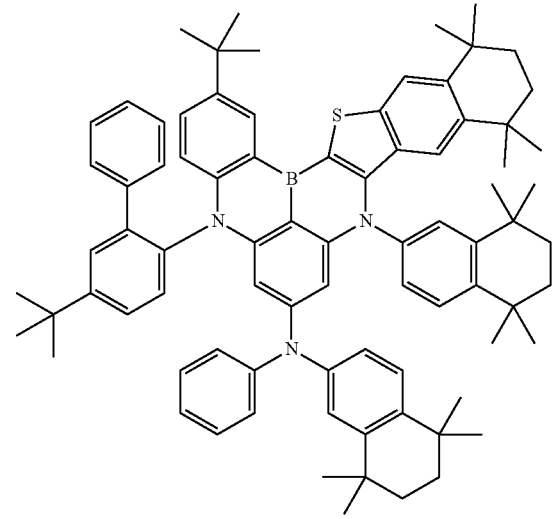
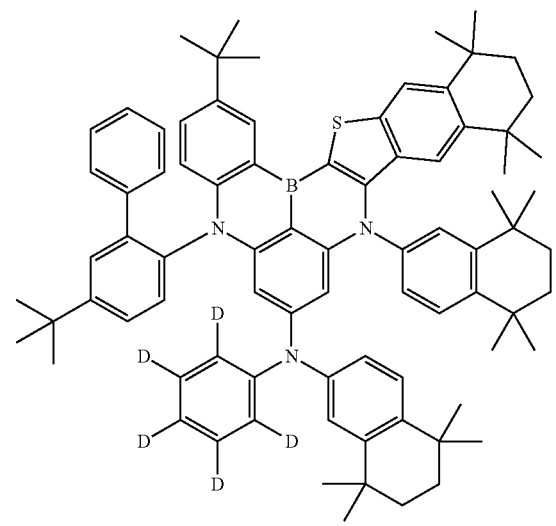

241
-continued
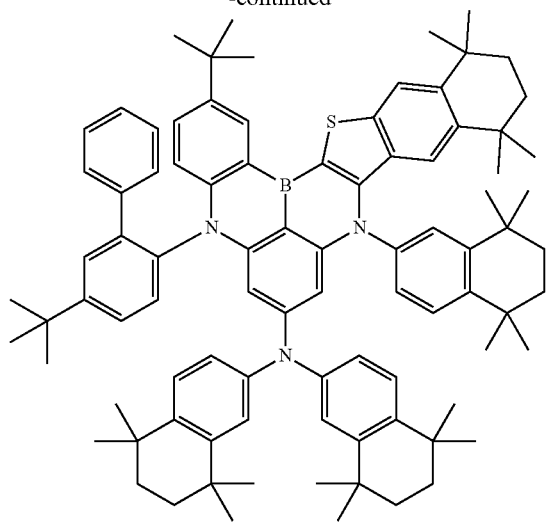
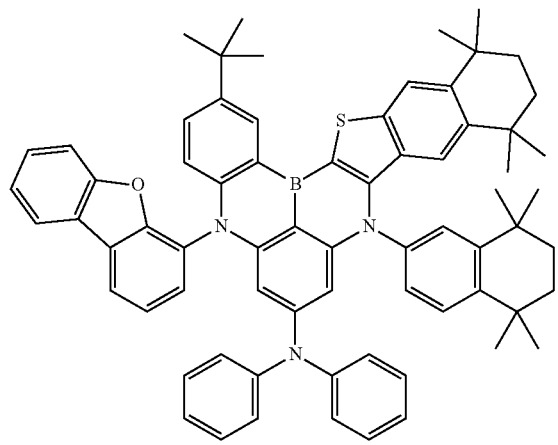
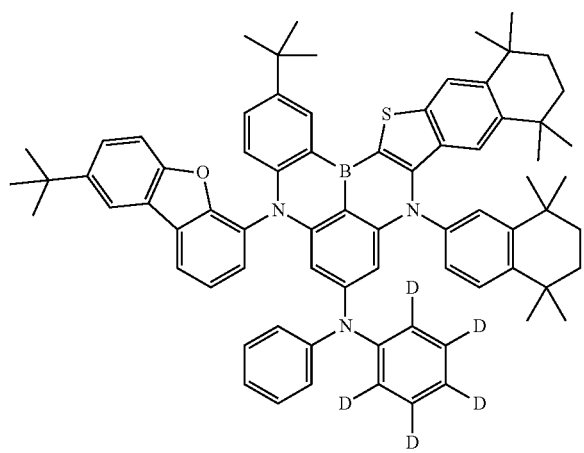
242
-continued
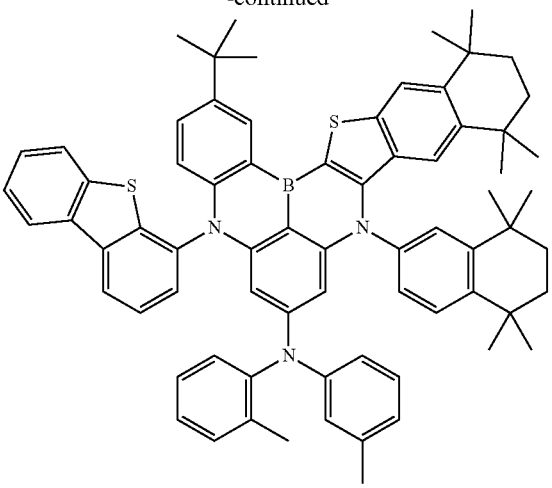
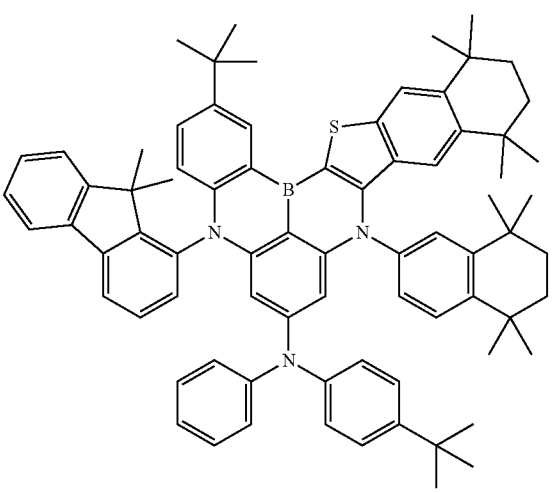
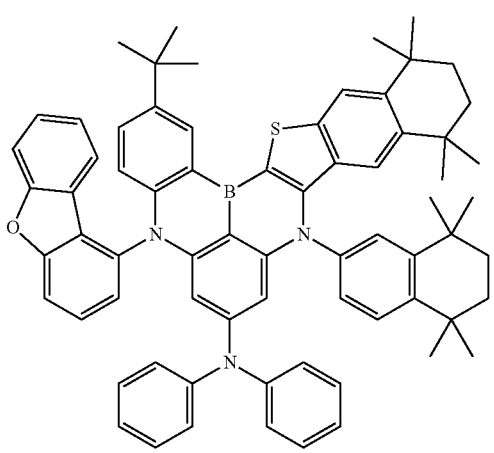

243
-continued
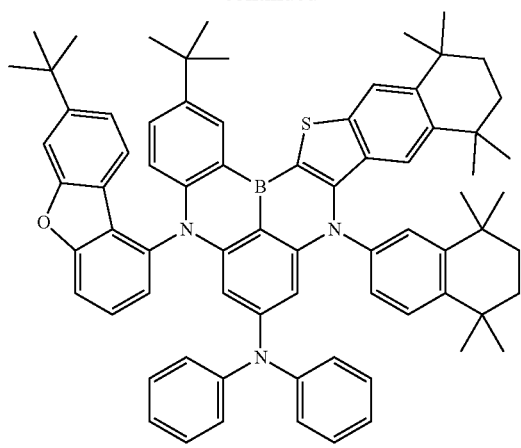
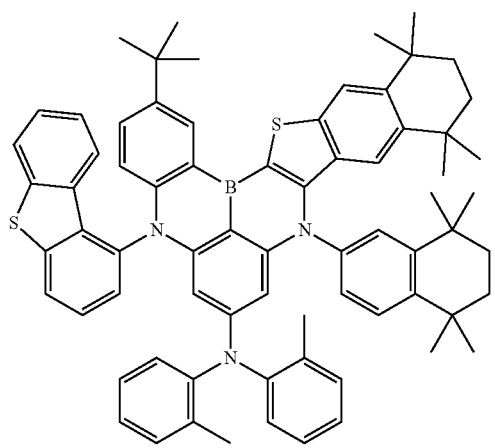
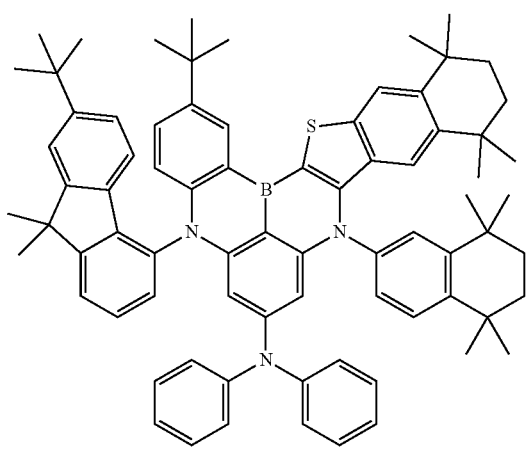
244
-continued
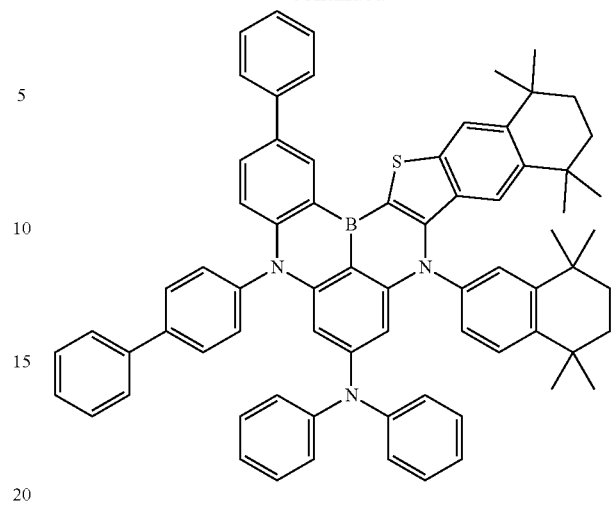
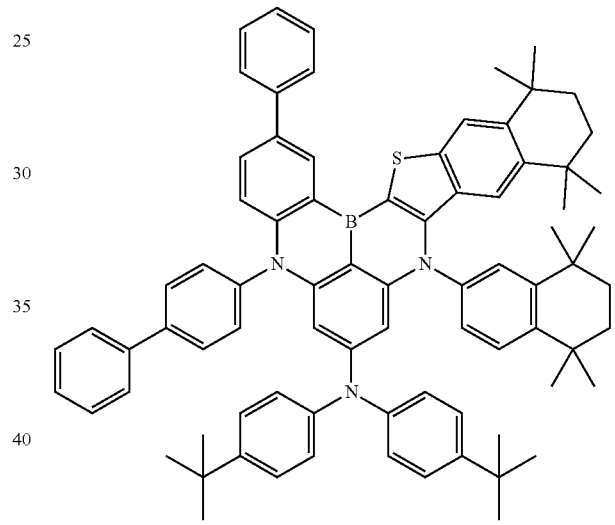
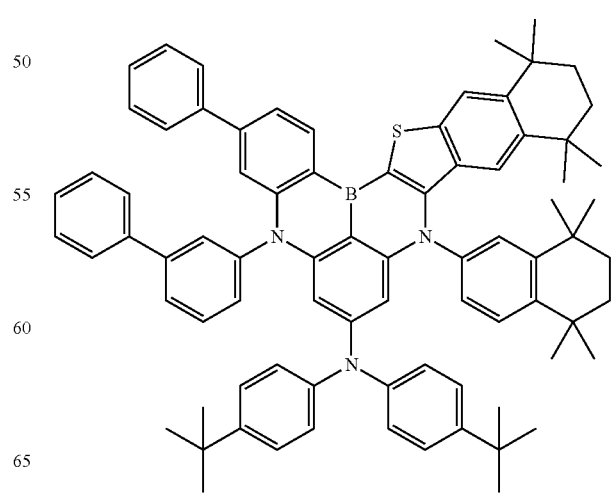

245
-continued
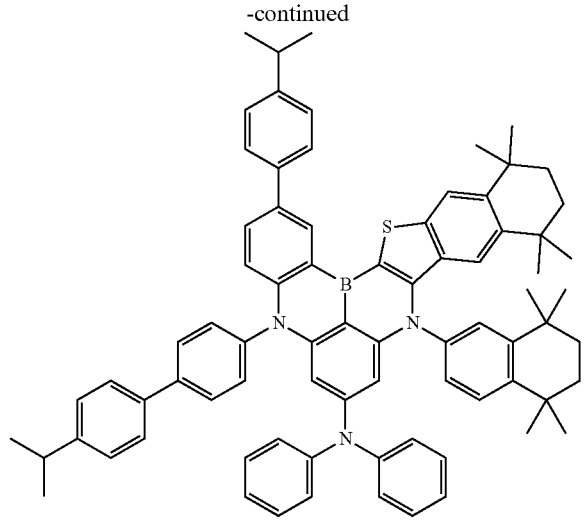
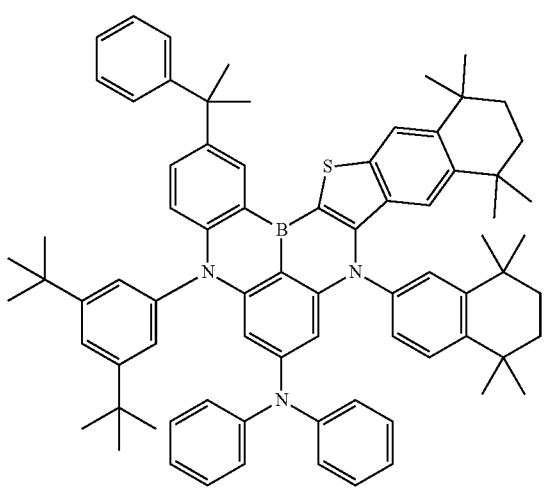
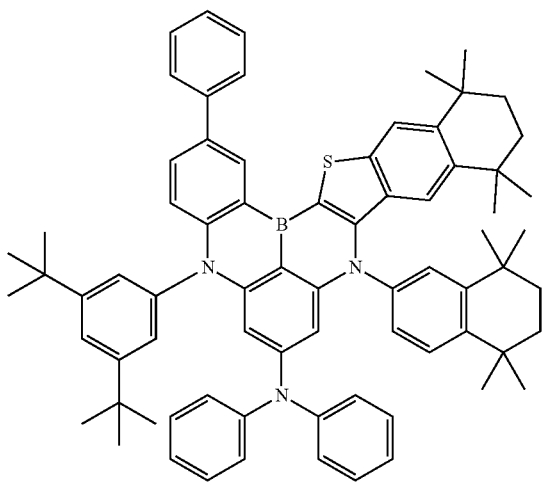
246
-continued
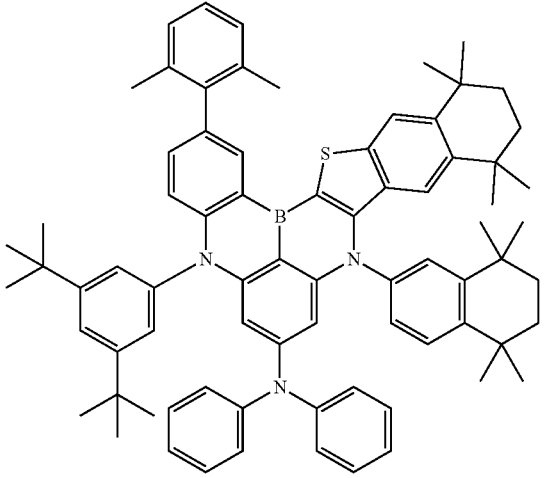
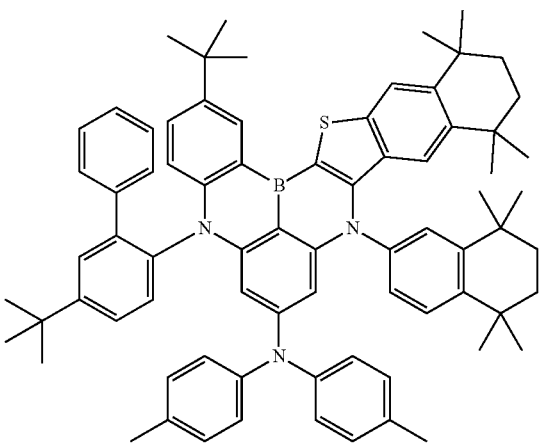
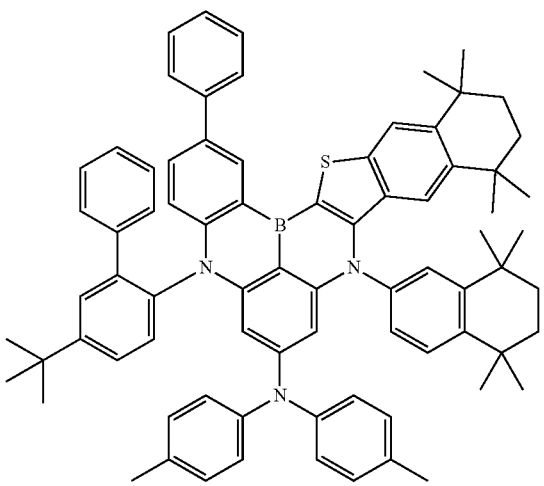

247
-continued
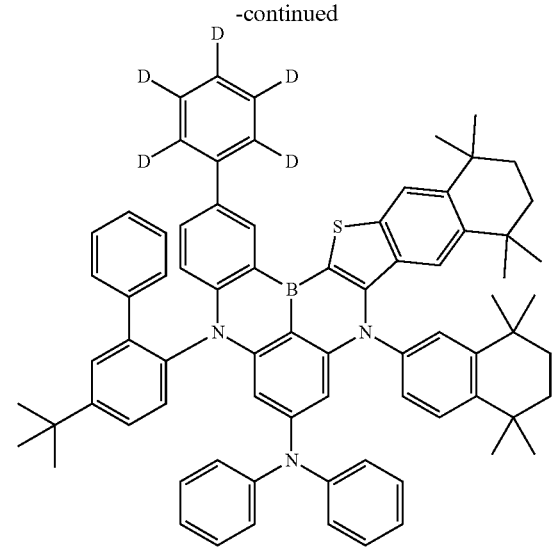
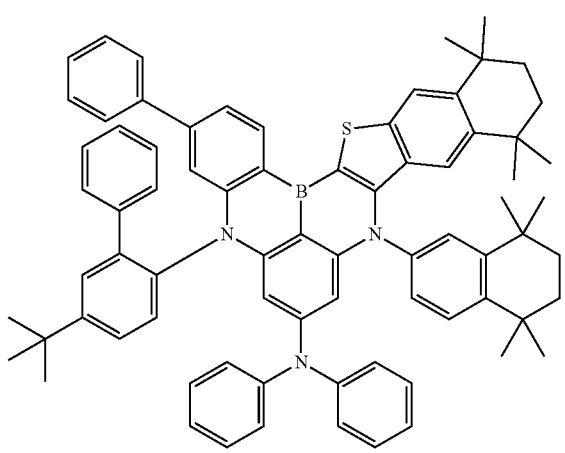
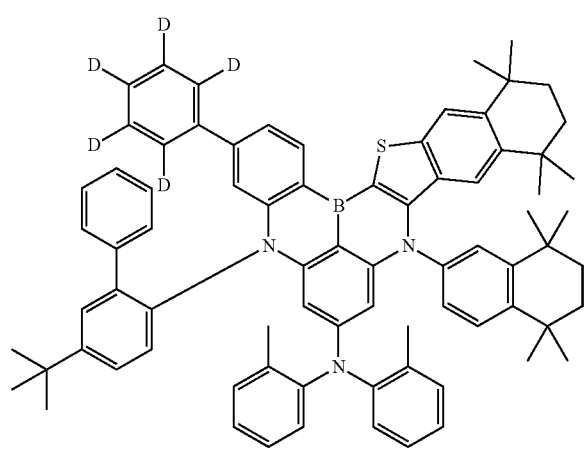
248
-continued
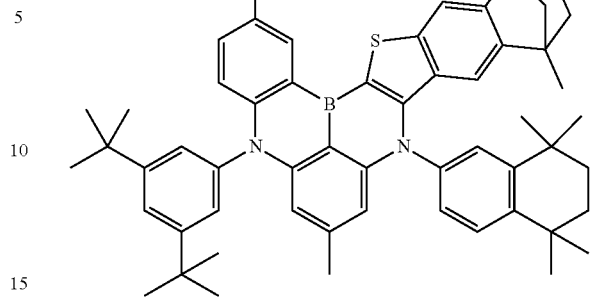
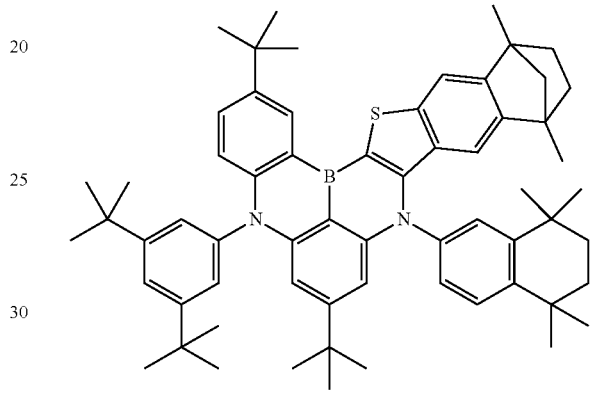
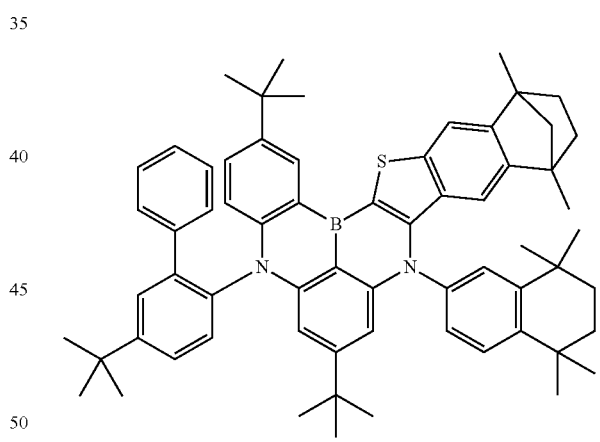
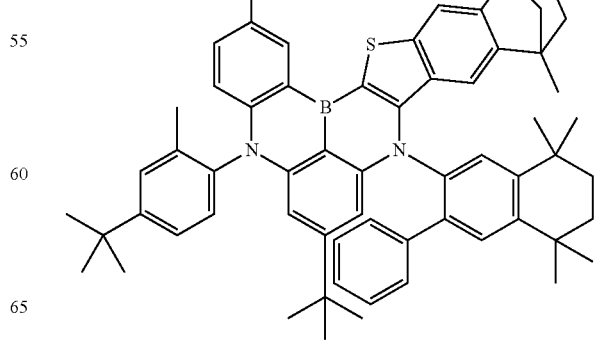

249
-continued
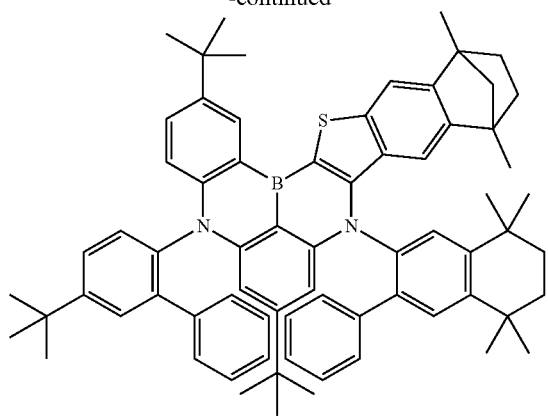
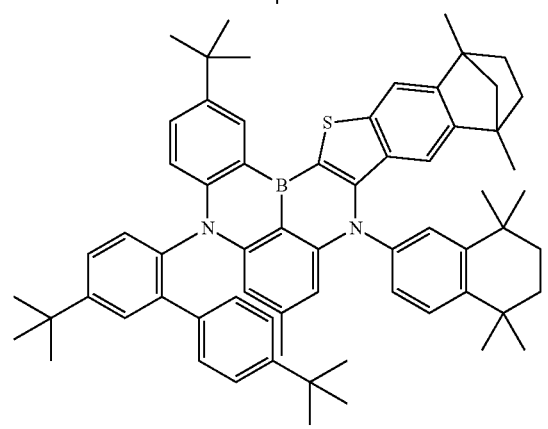
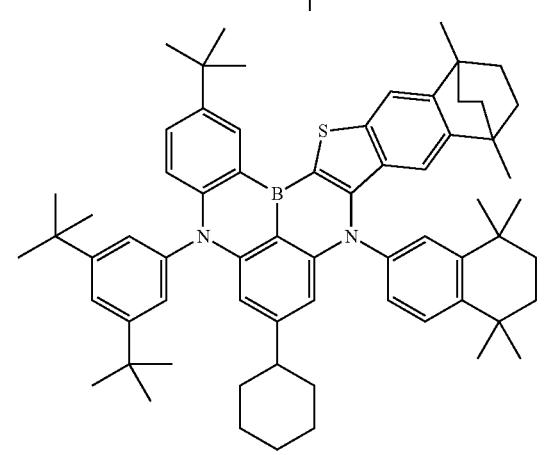
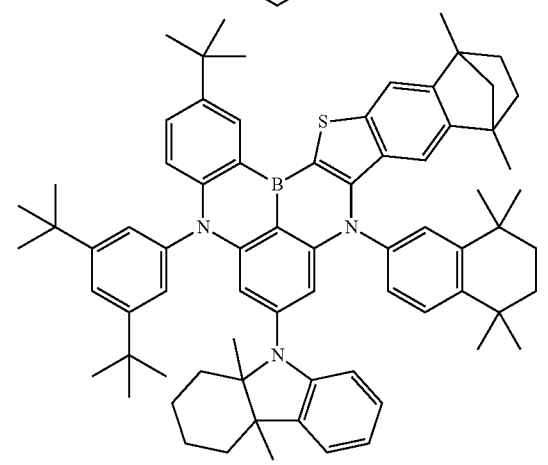
250
-continued
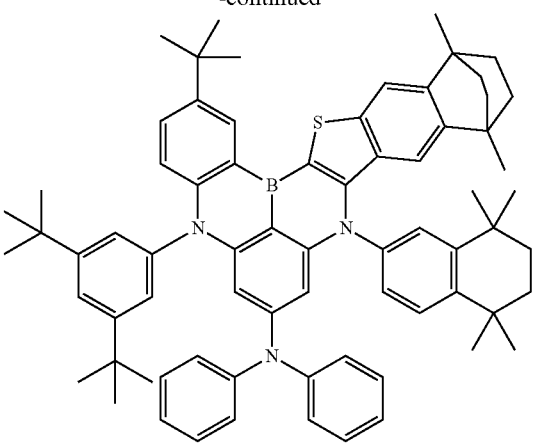
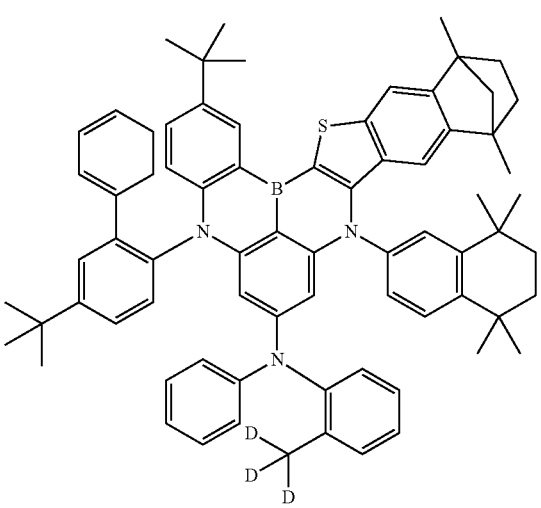
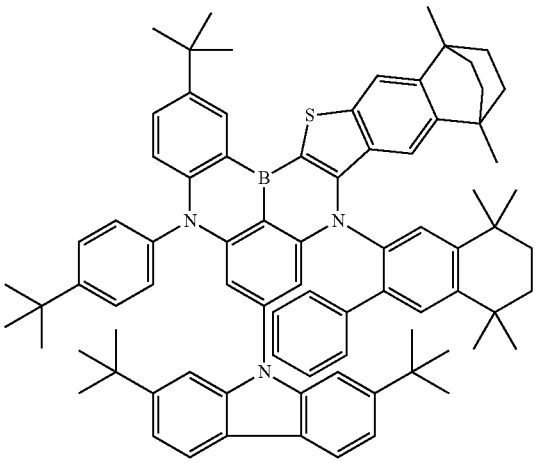

251
-continued
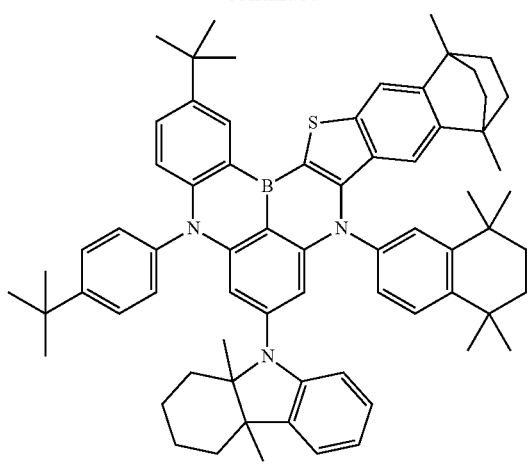
252
-continued
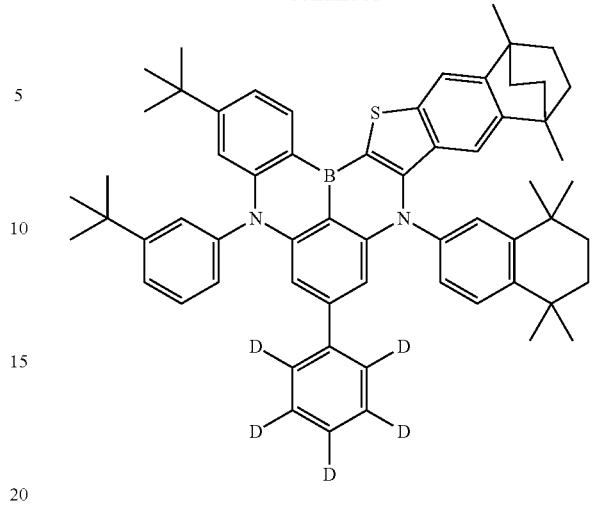
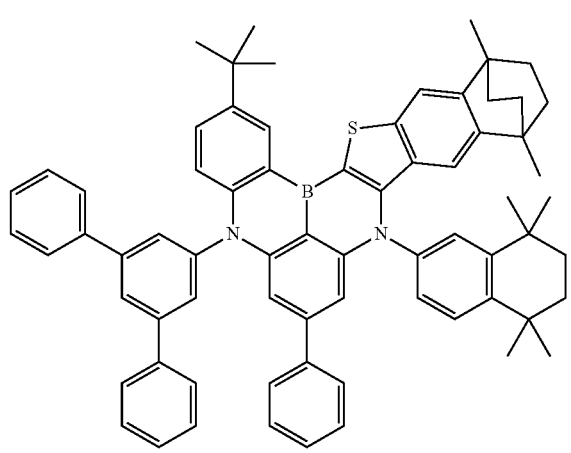
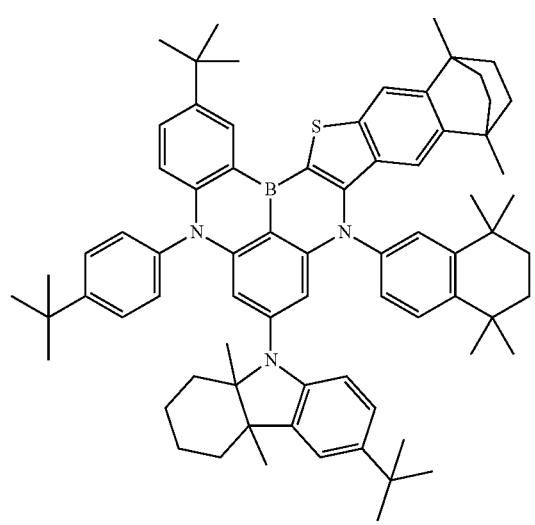
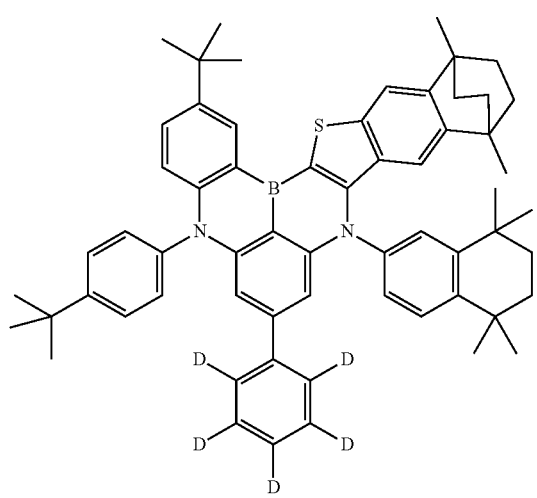
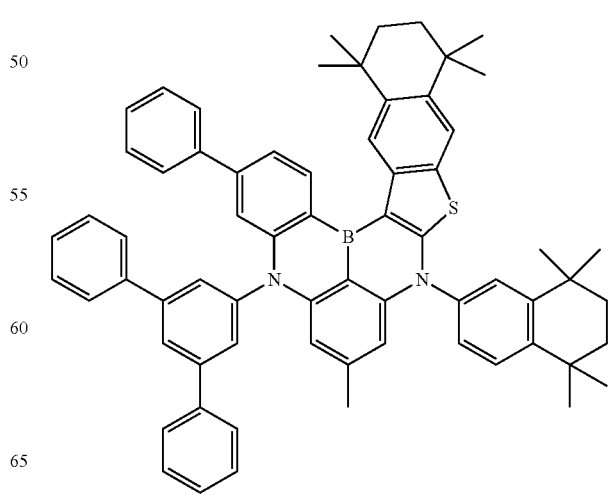

253
-continued
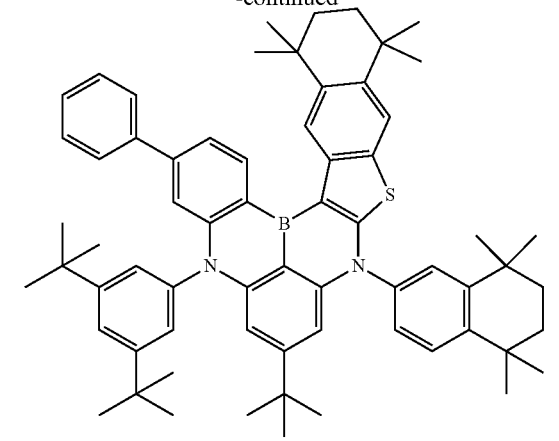
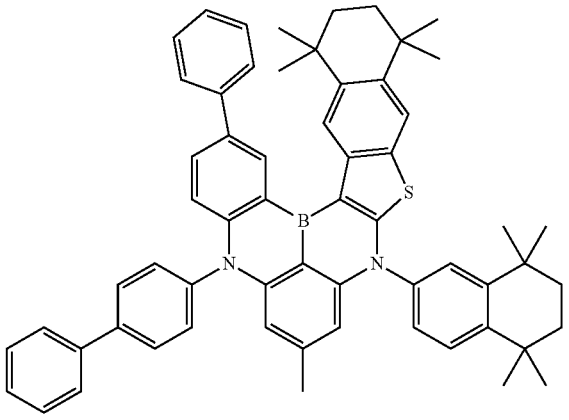
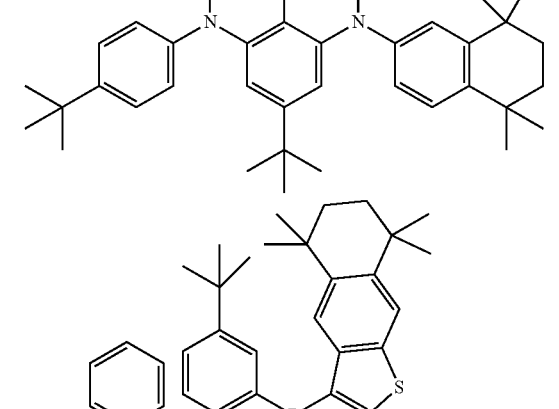
254
-continued
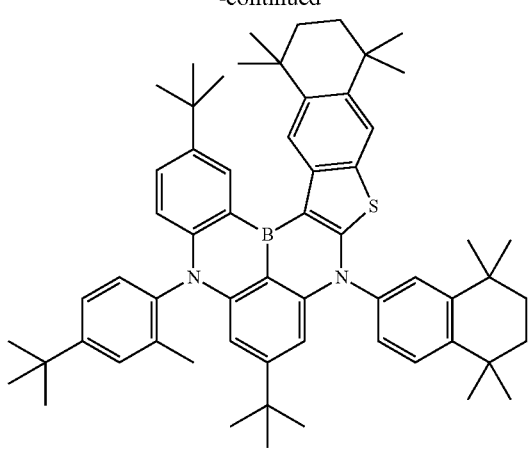
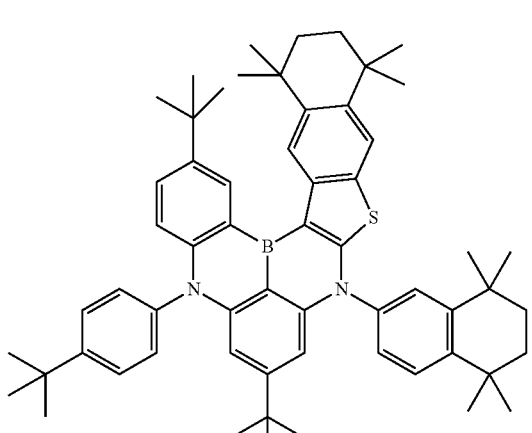
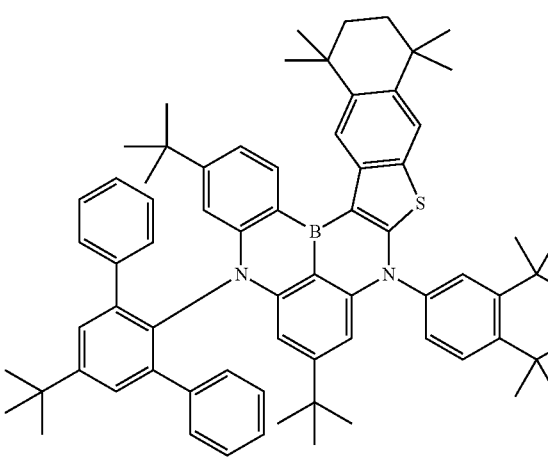

255
-continued
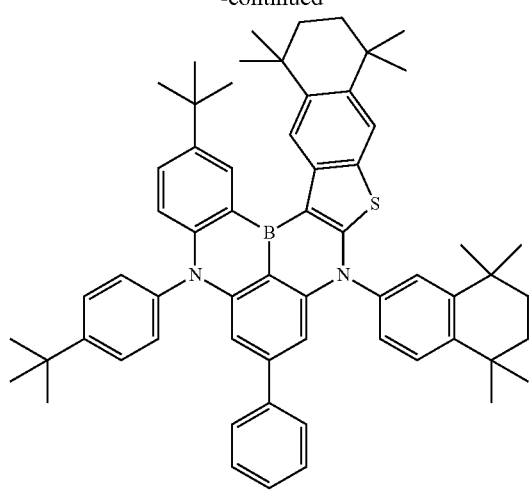
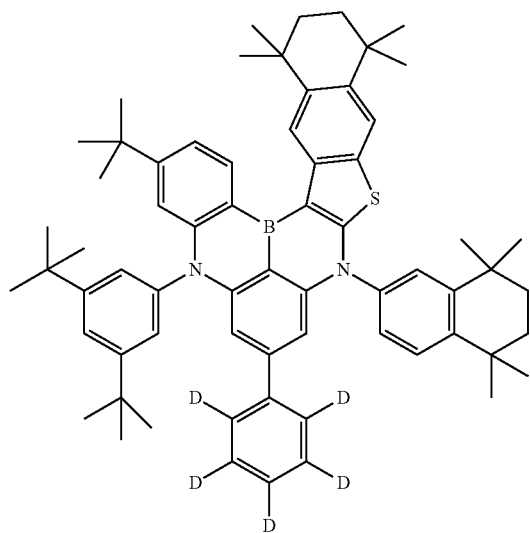
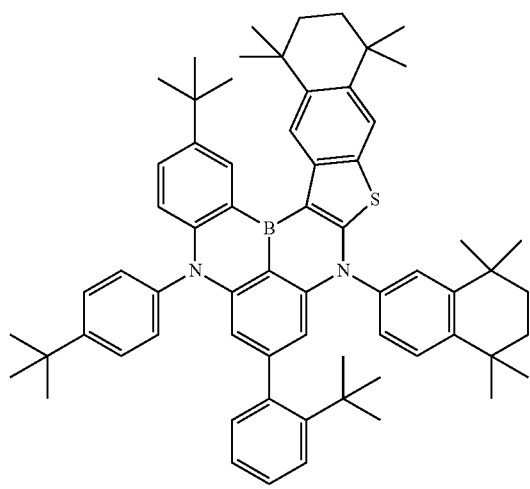
256
-continued
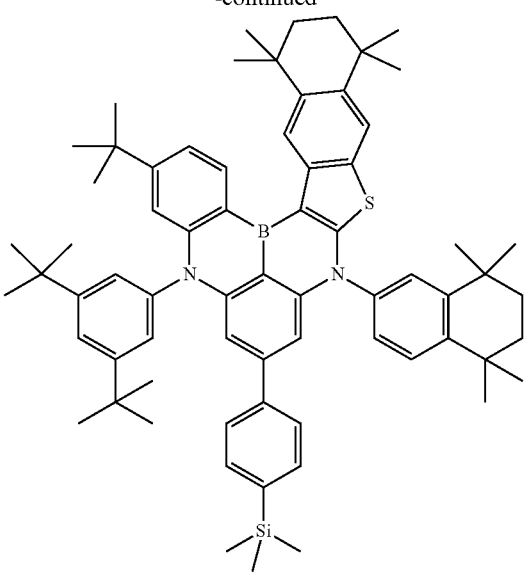
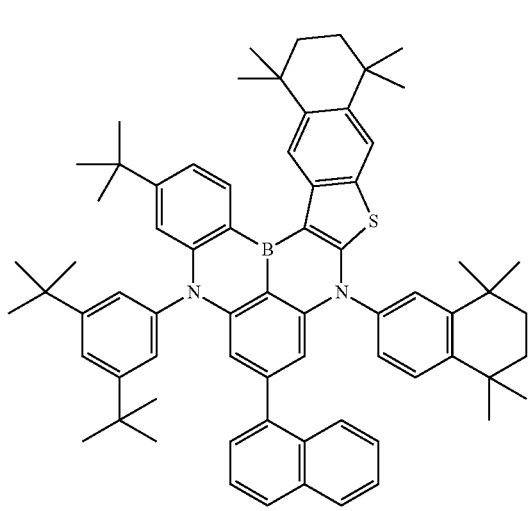
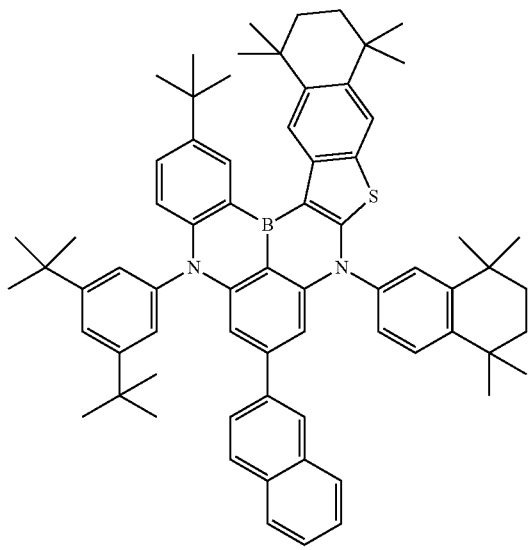

257
-continued
258
-continued

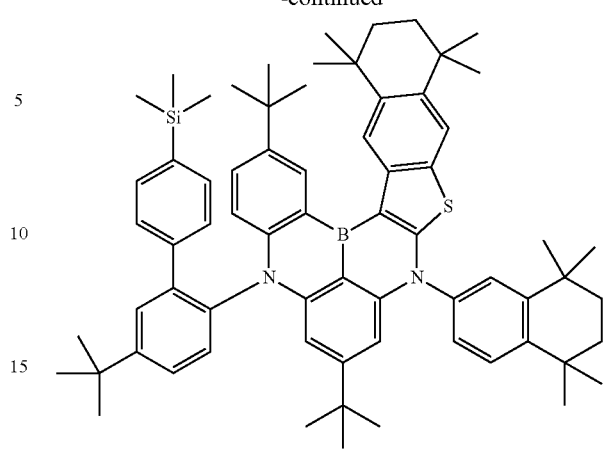
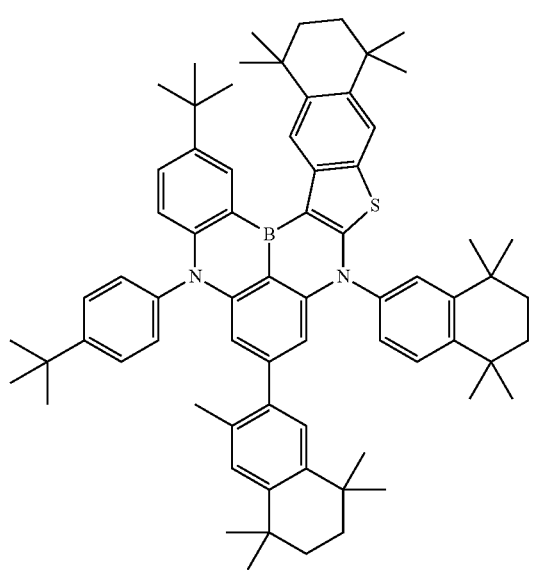
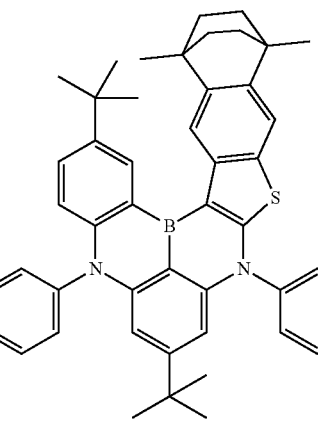
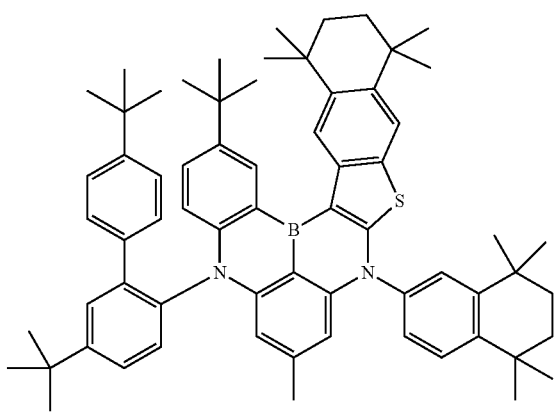
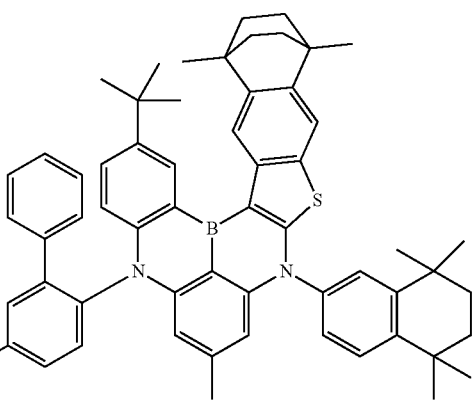

259
-continued
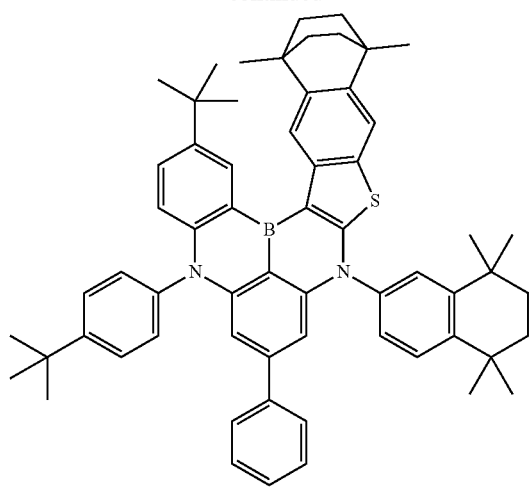
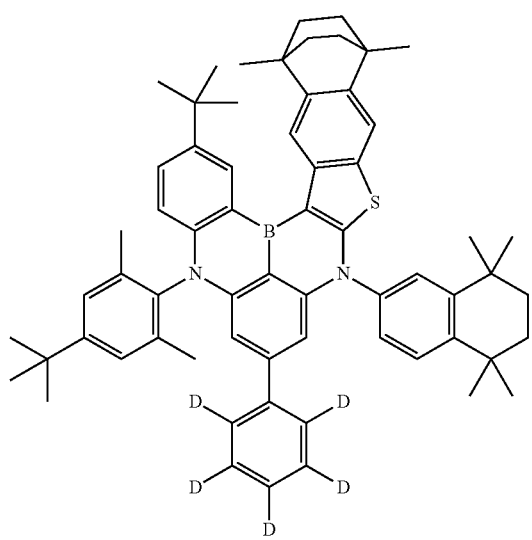
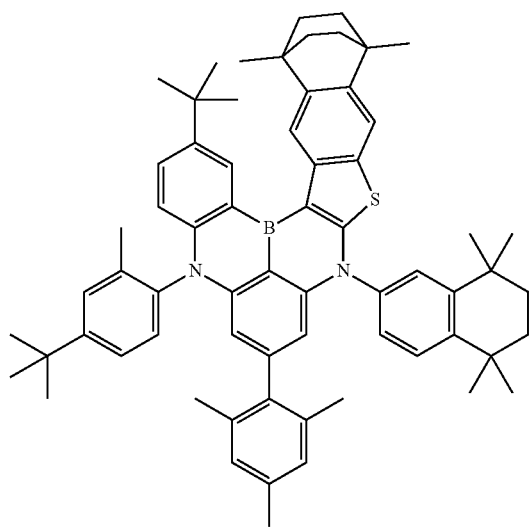
260
-continued
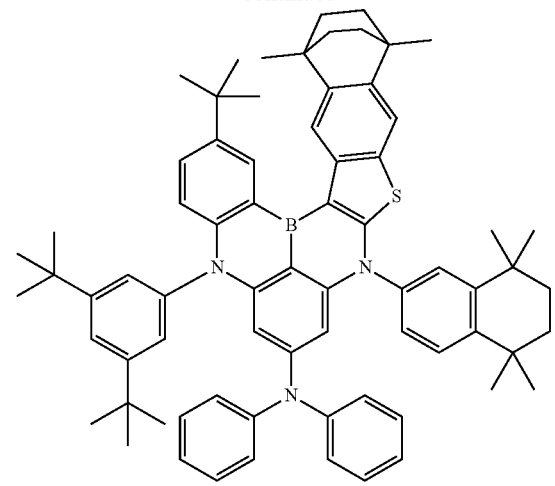
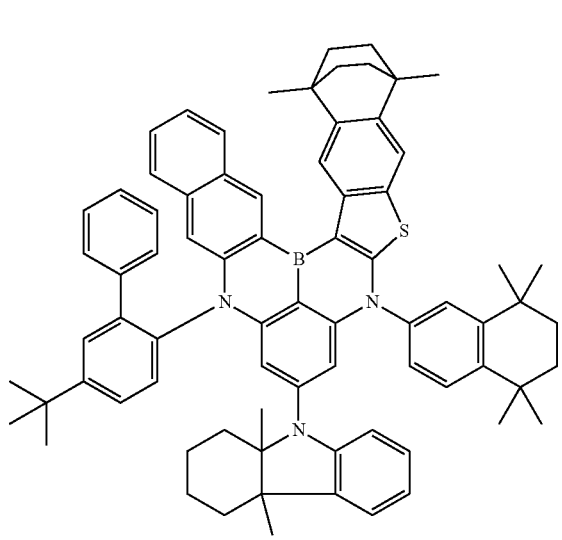

261
-continued
262
-continued
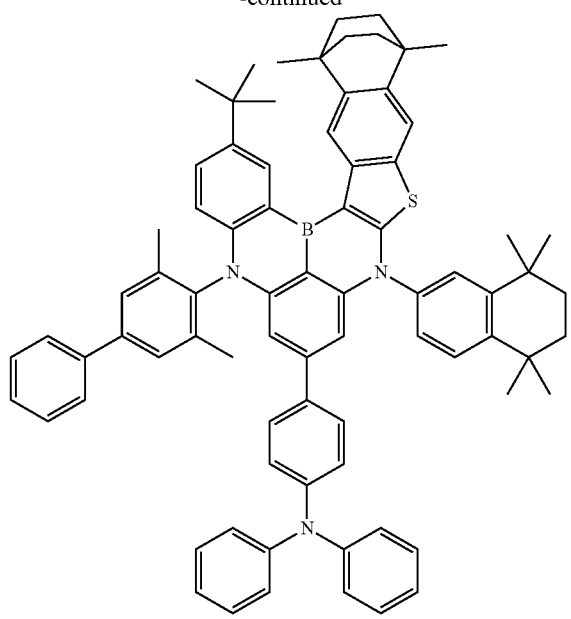
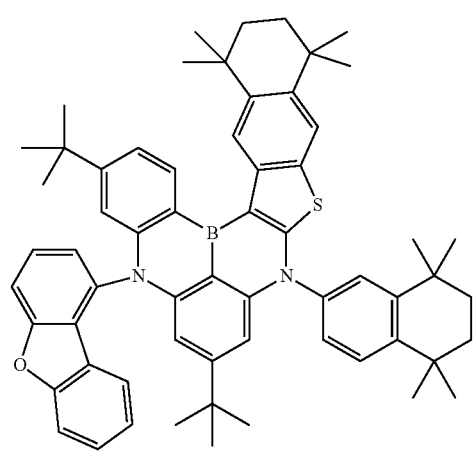
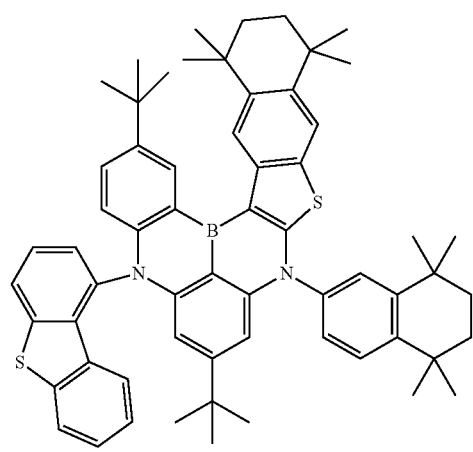
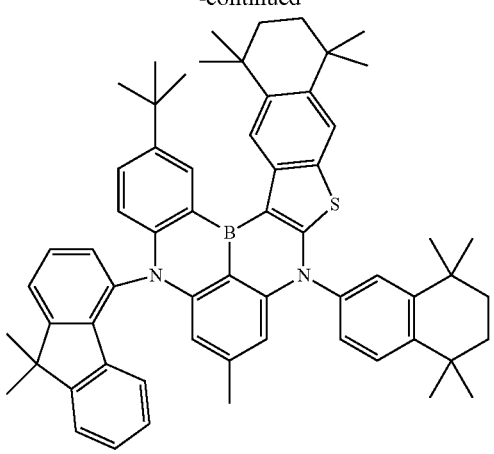
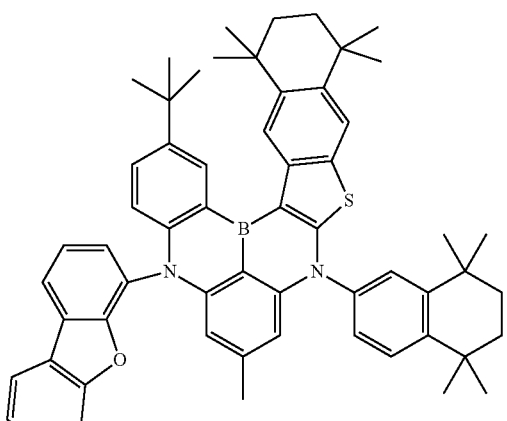
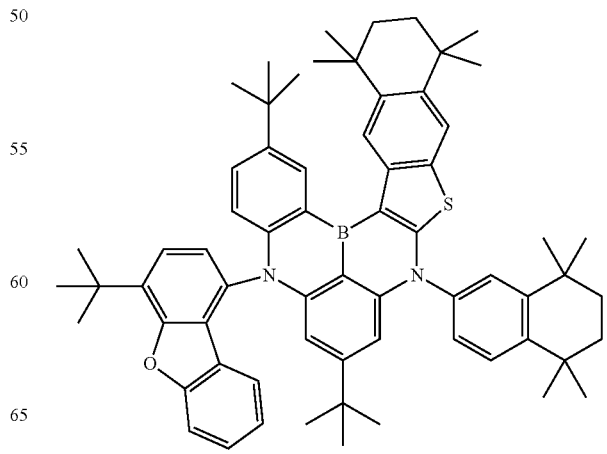

263
-continued
264
-continued
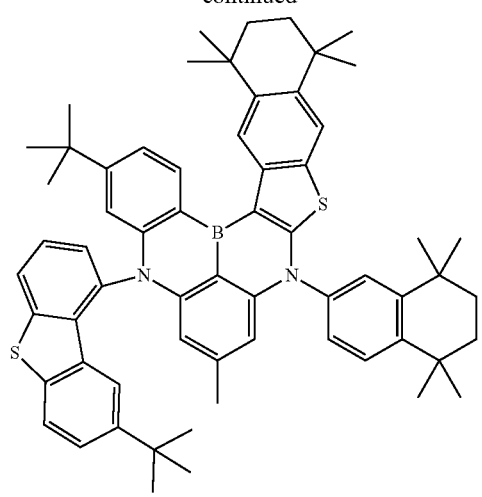
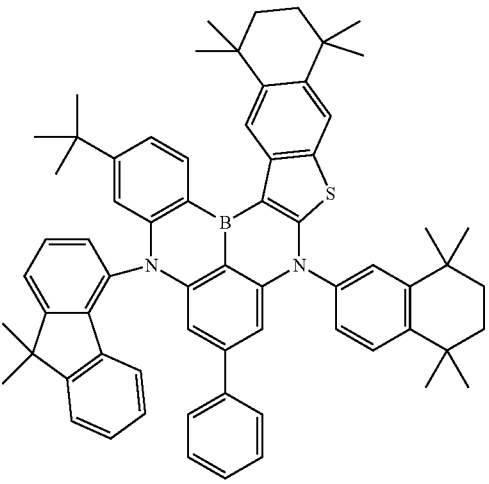
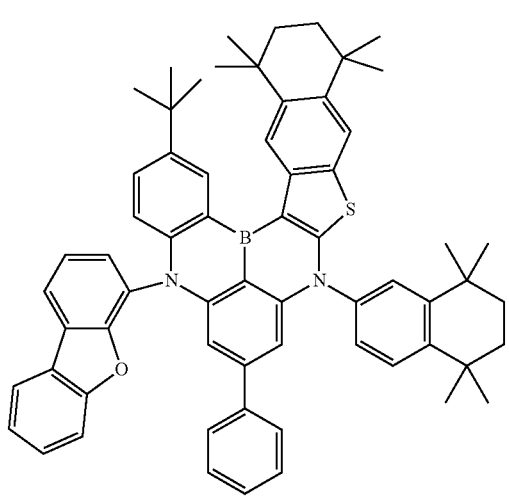
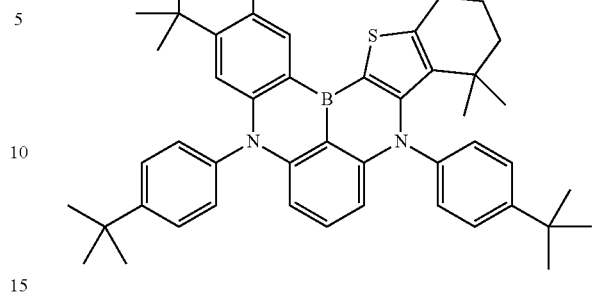
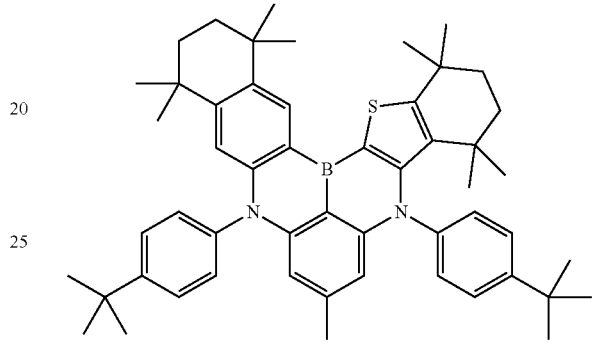
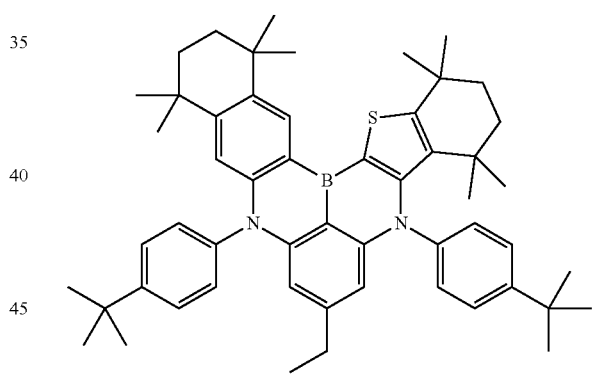
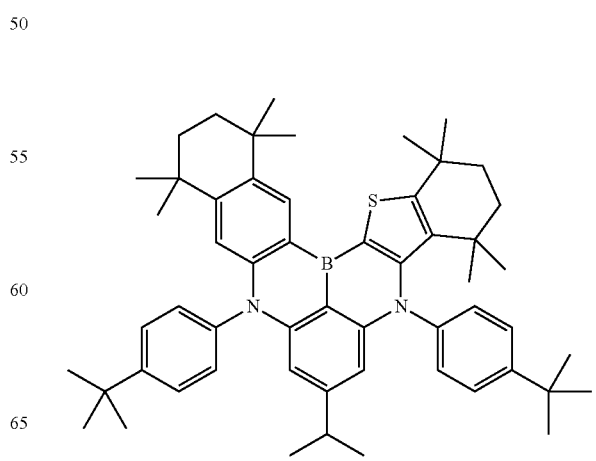

265
-continued
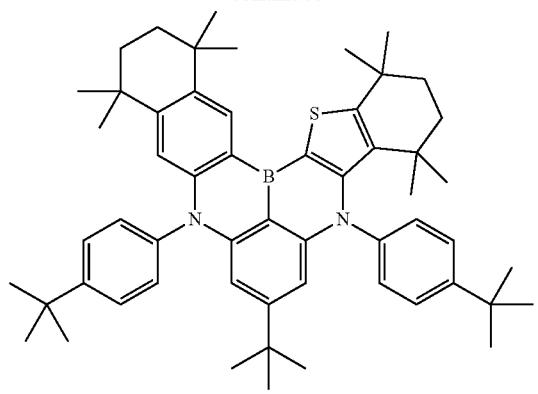
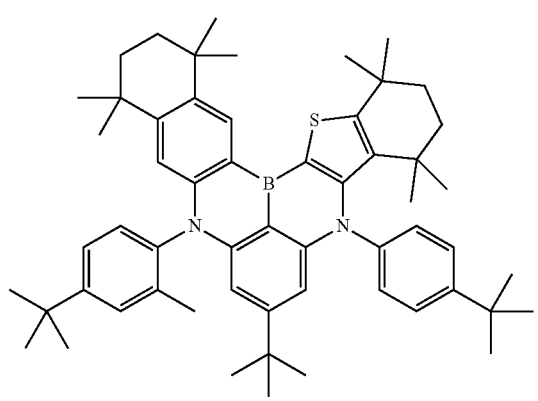
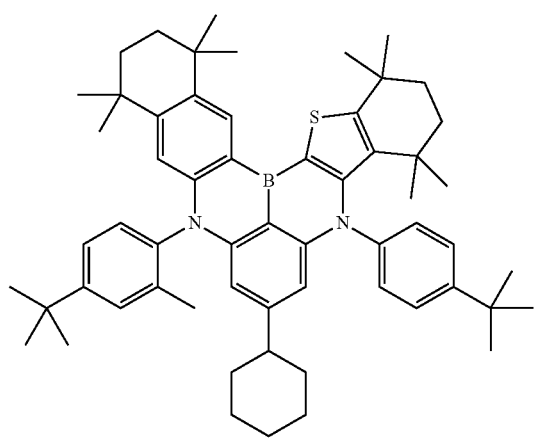
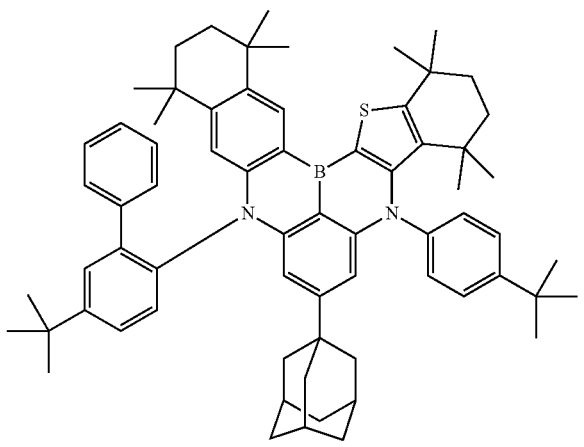
266
-continued
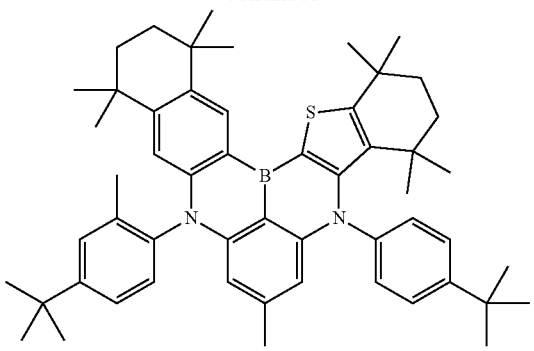
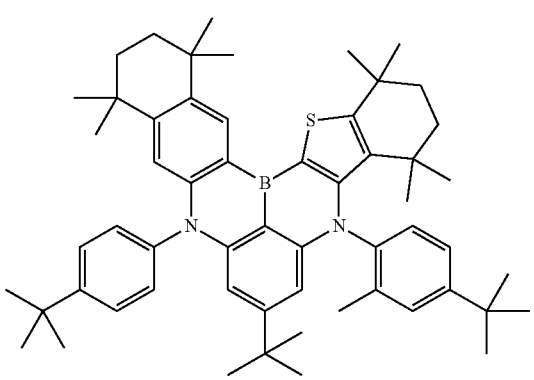
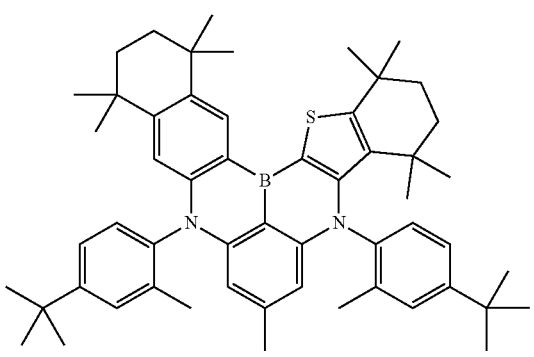
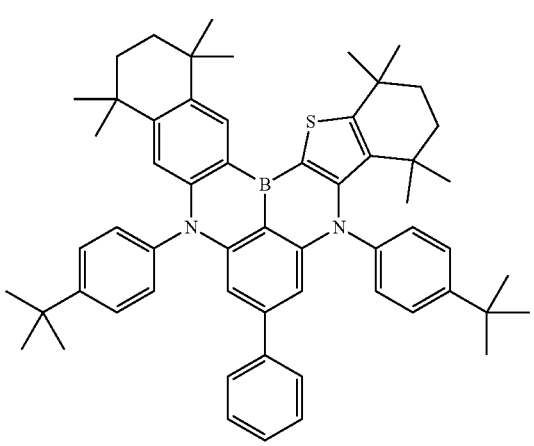

267
-continued
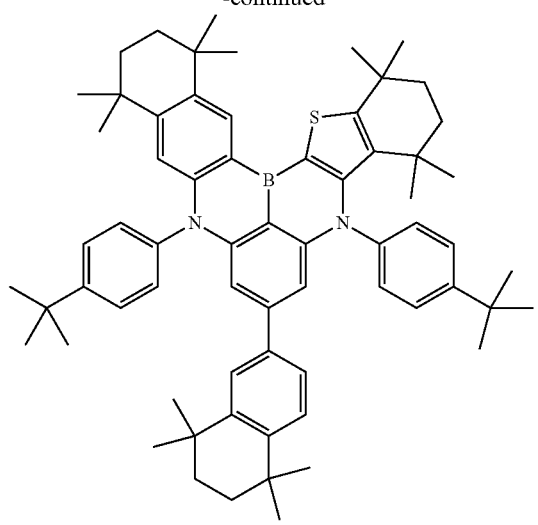
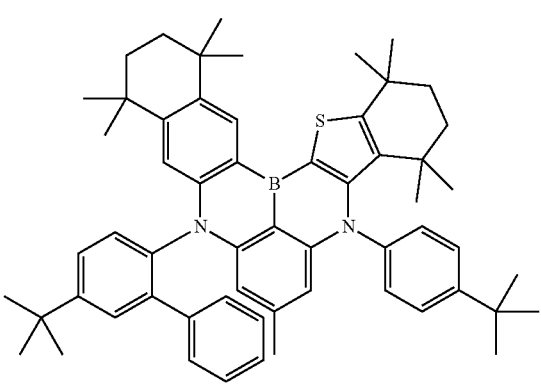
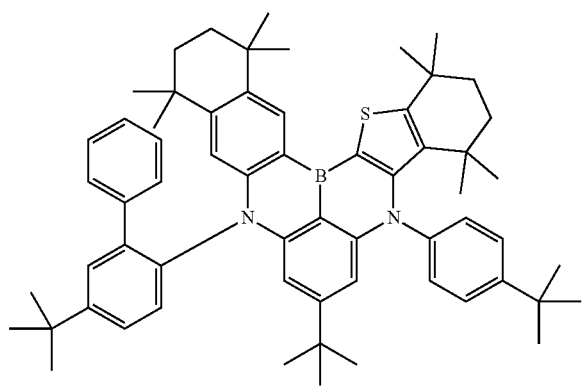
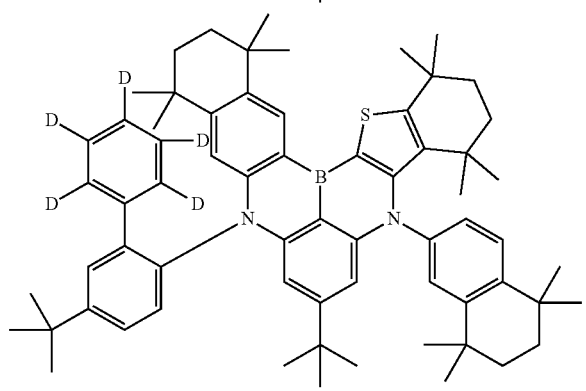
268
-continued
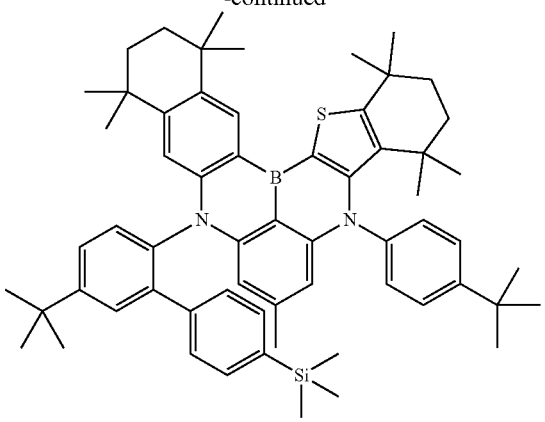
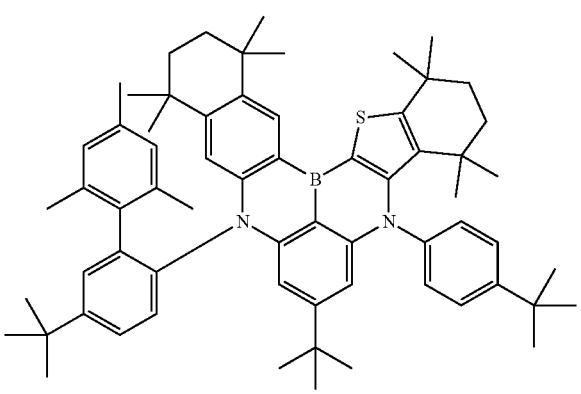
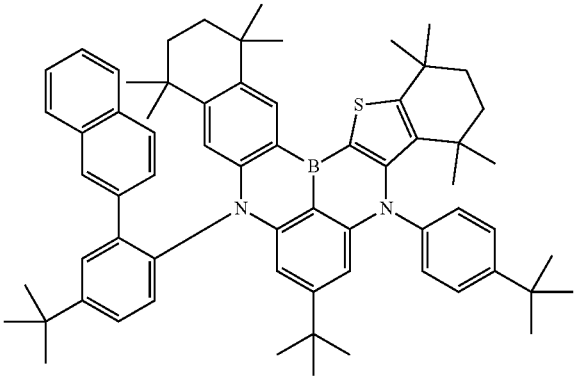
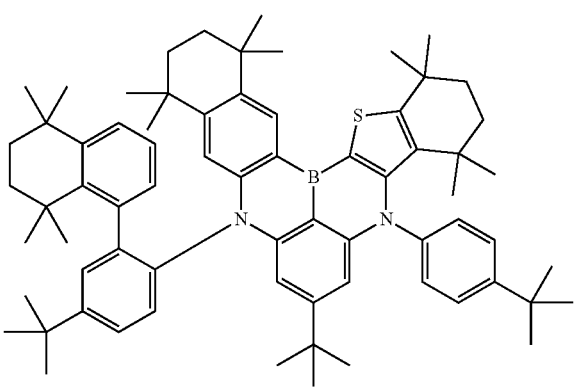

269
-continued
270
-continued
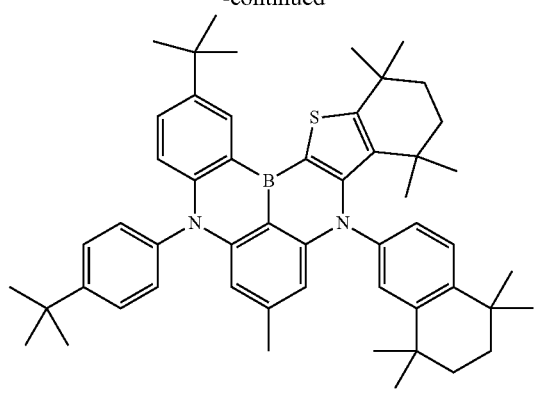
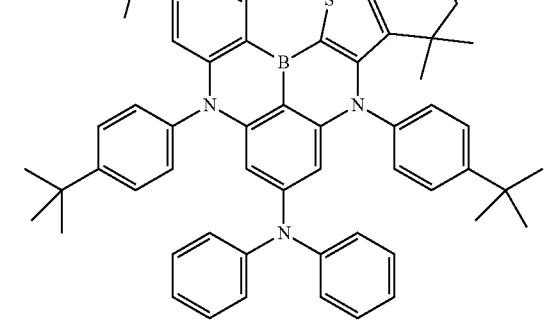
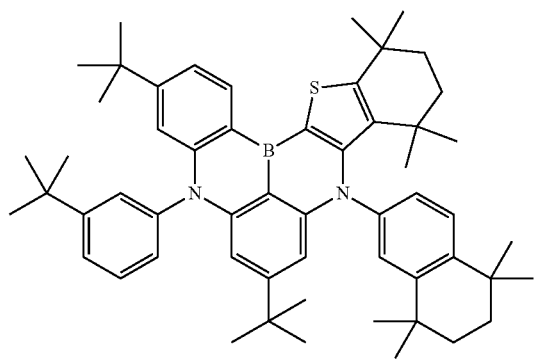
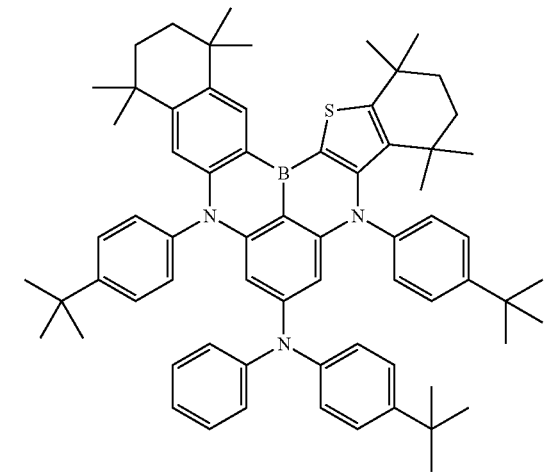
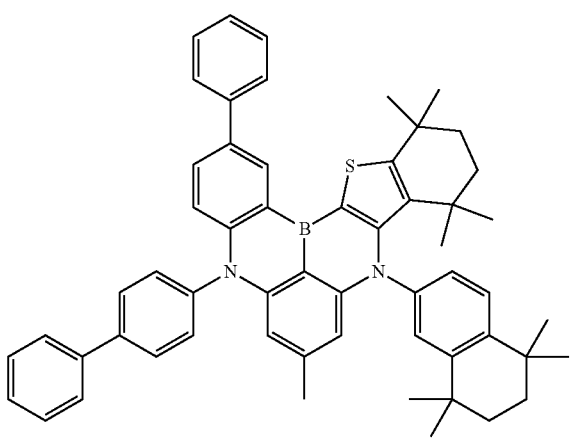
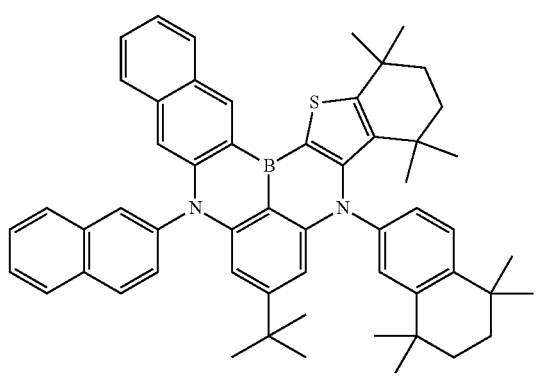
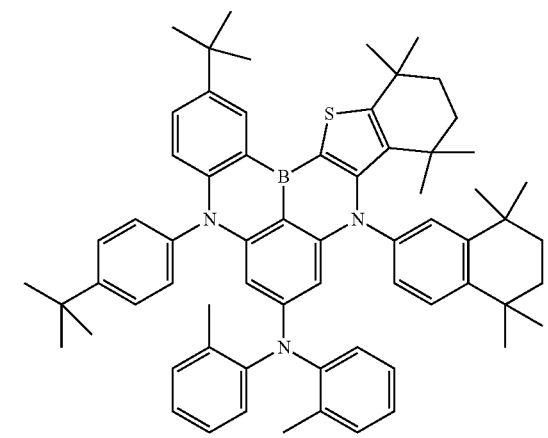

271
-continued
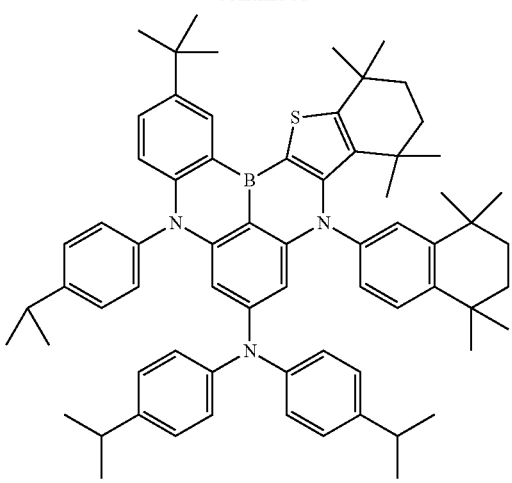
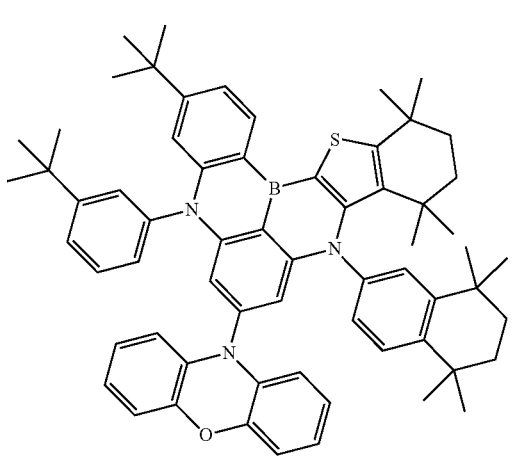
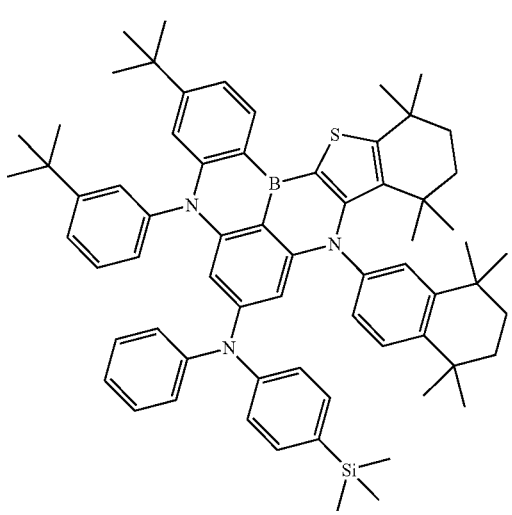
272
-continued
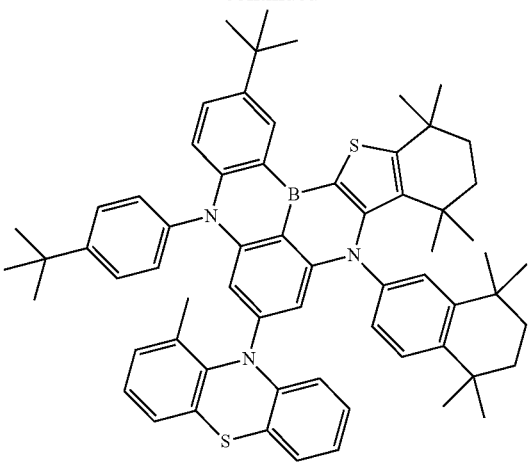
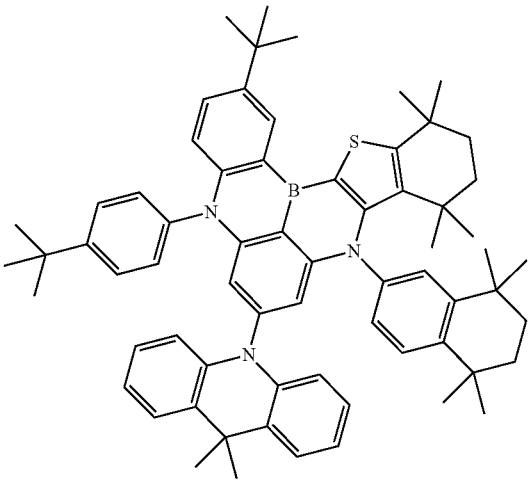
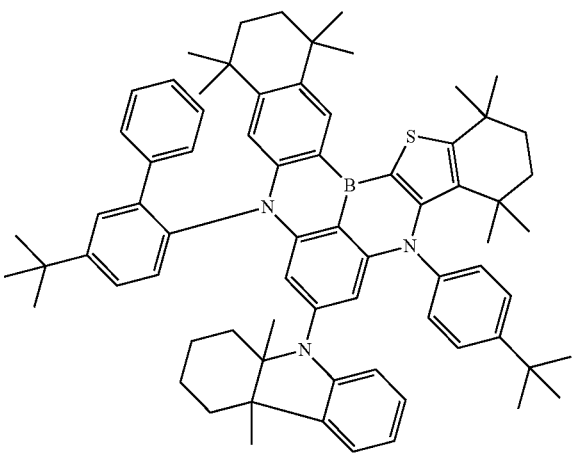

273
-continued
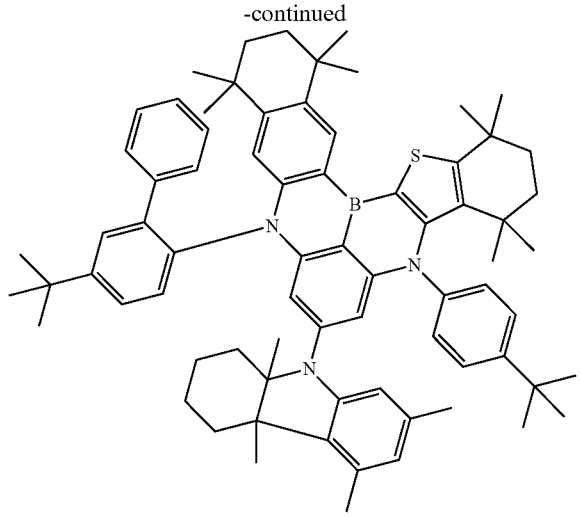
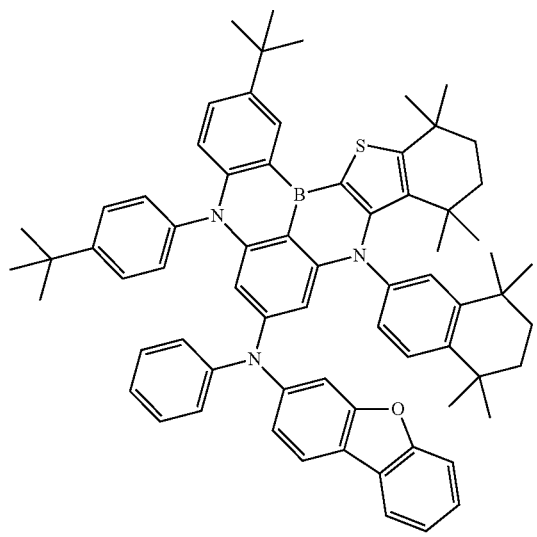
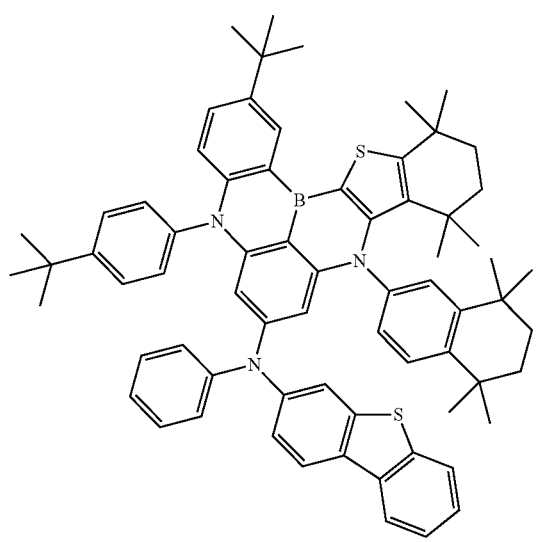
274
-continued
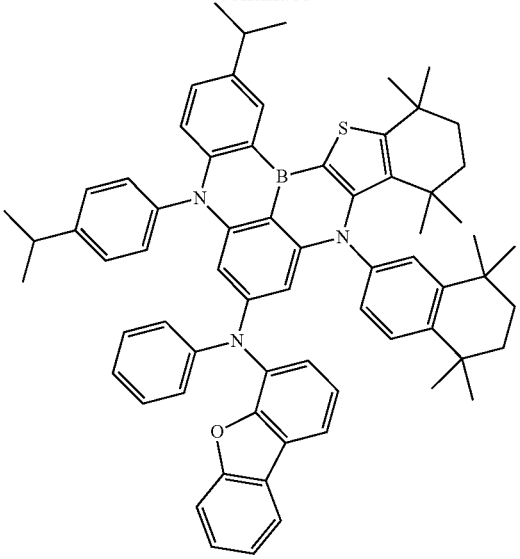
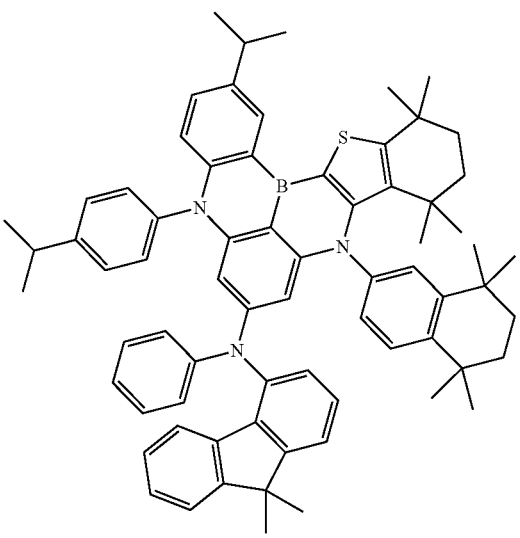
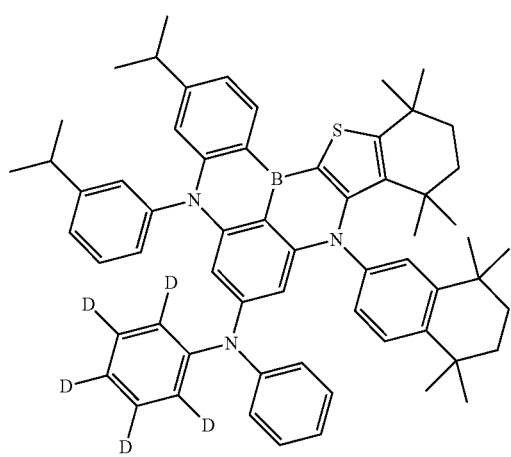

275
-continued
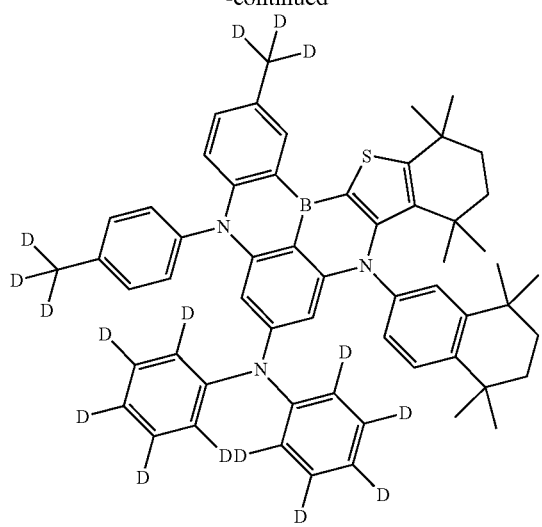
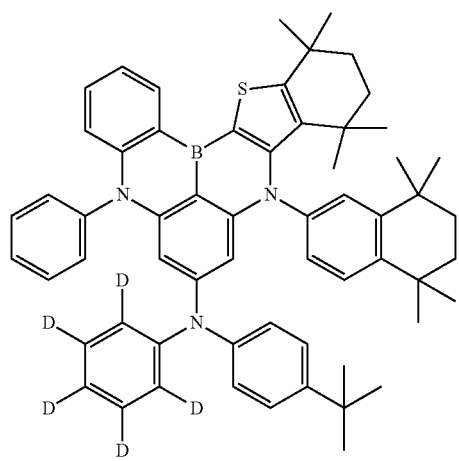
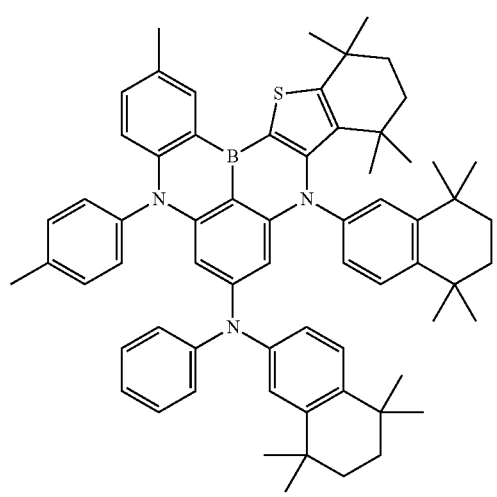
276
-continued
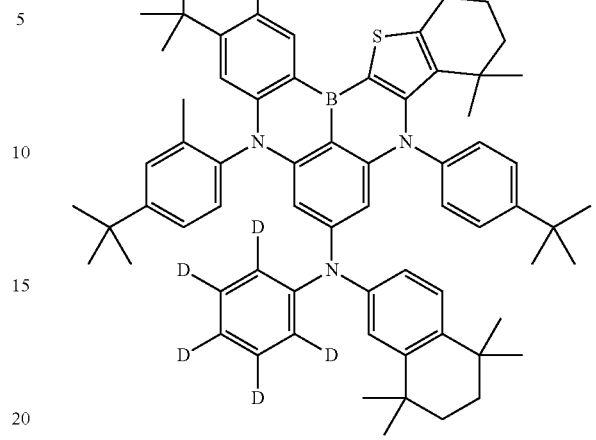
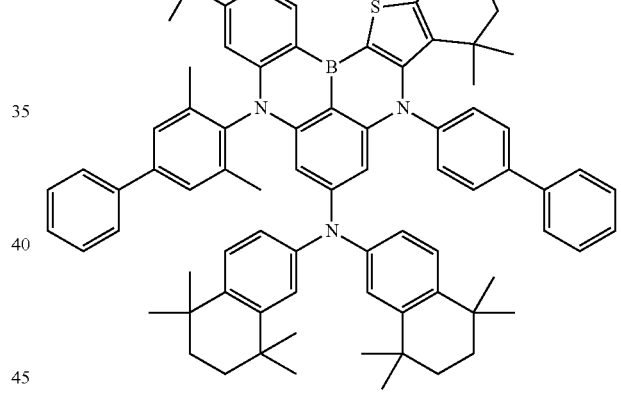
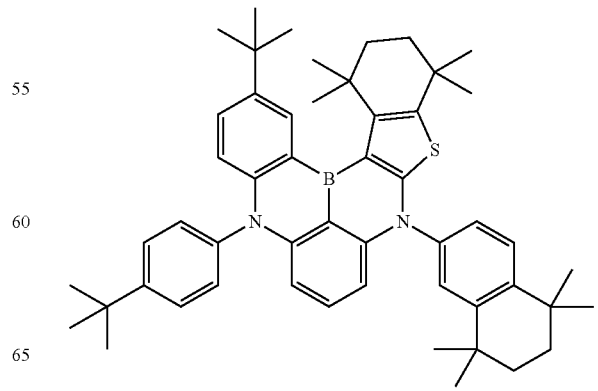

277
-continued
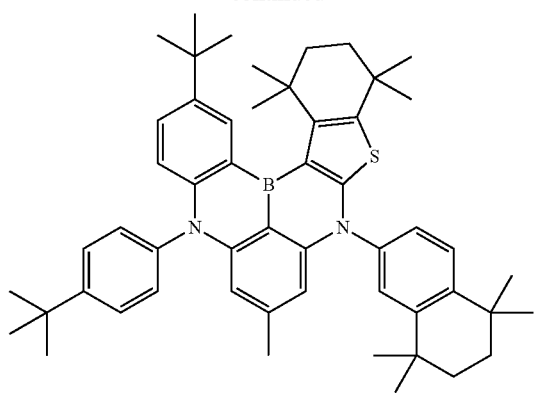
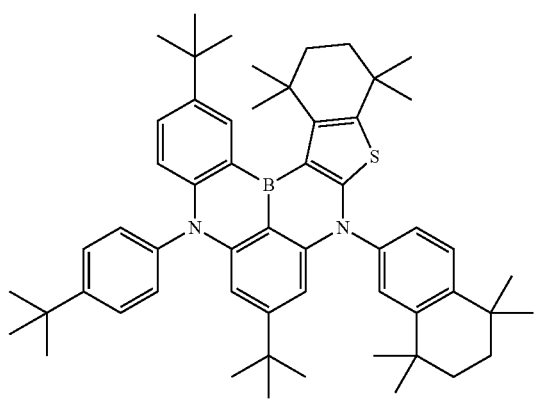
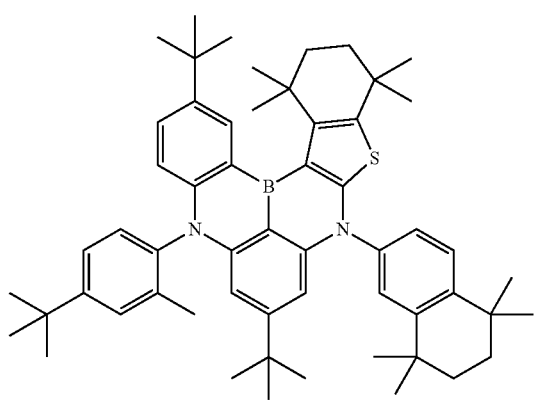
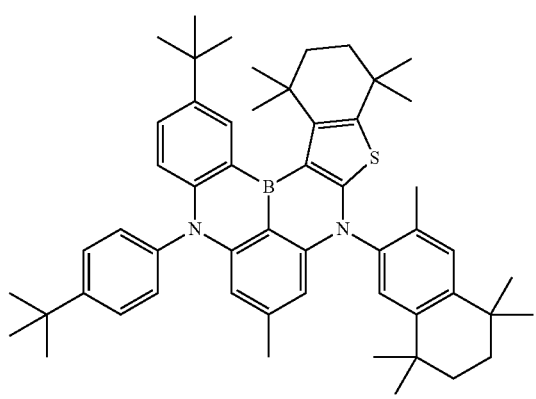
278
-continued
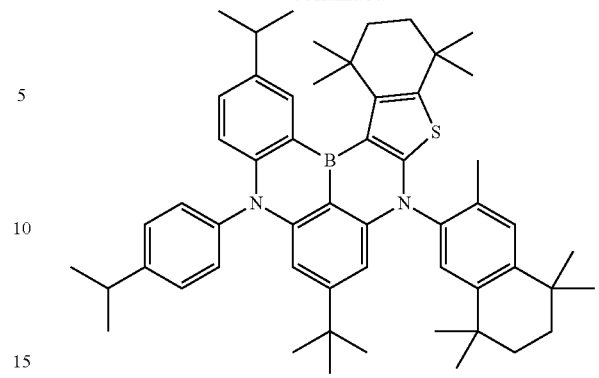
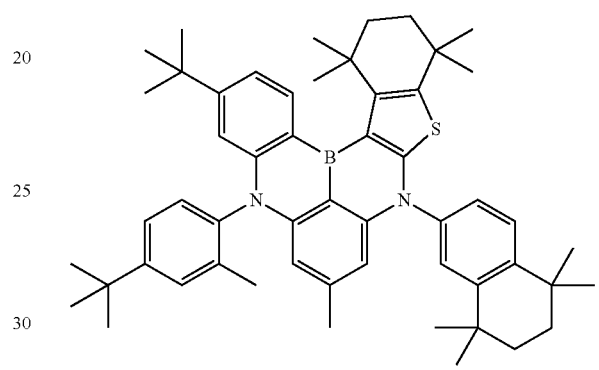
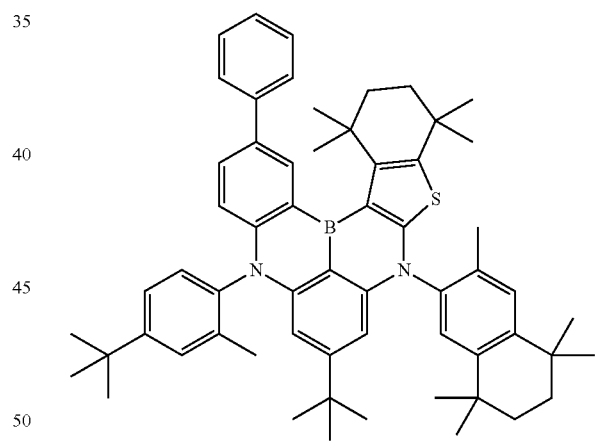
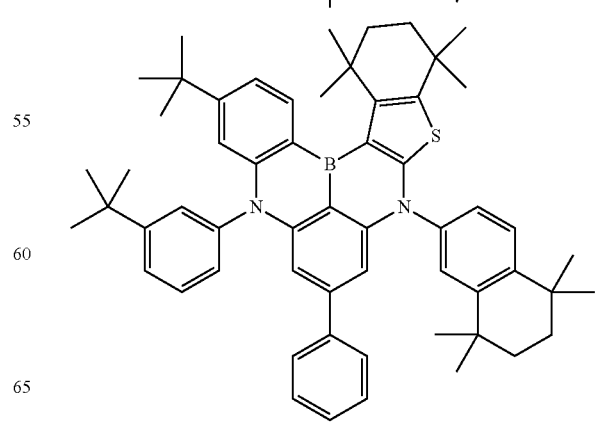

279
-continued
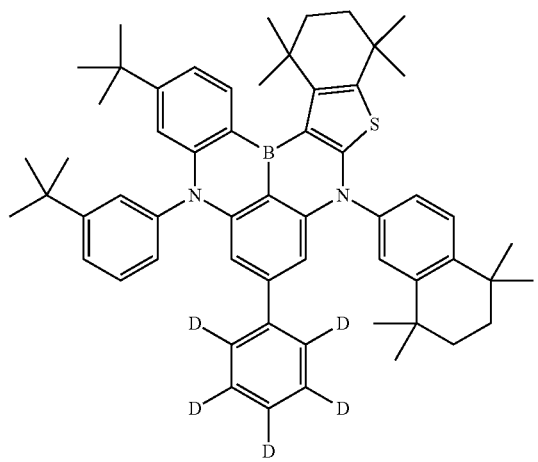
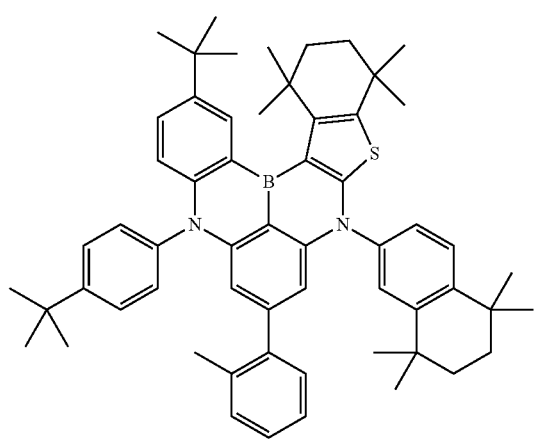
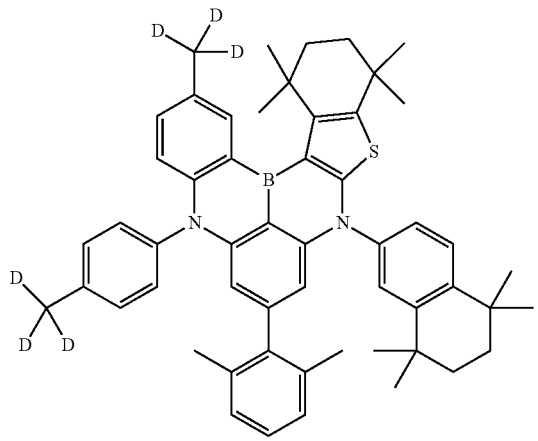
280
-continued
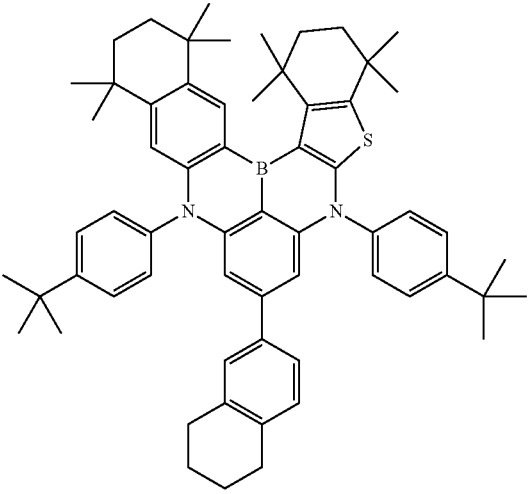
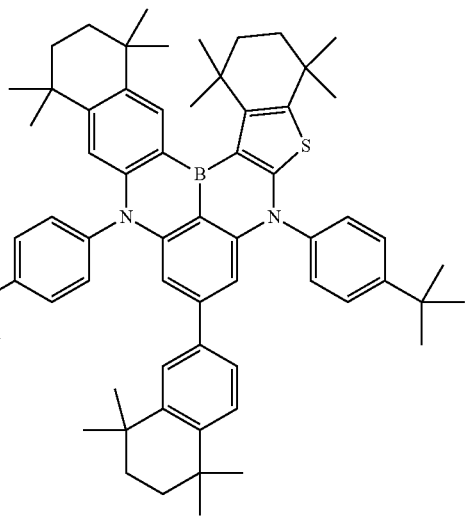
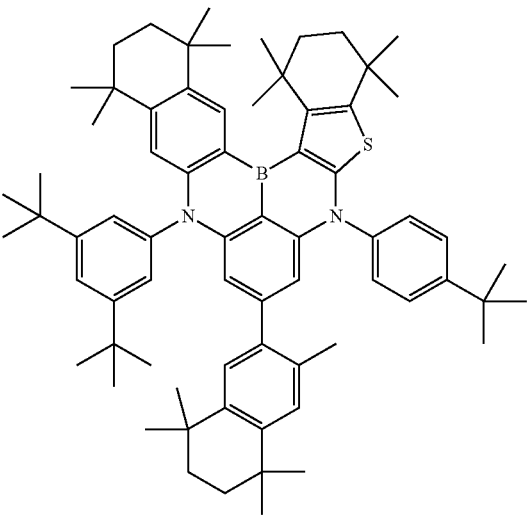

281
-continued
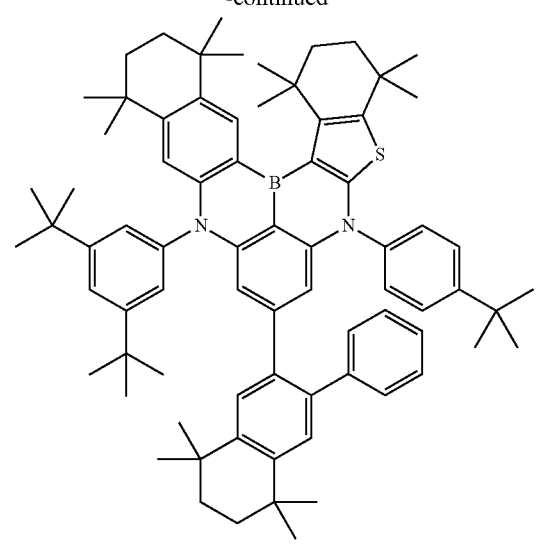
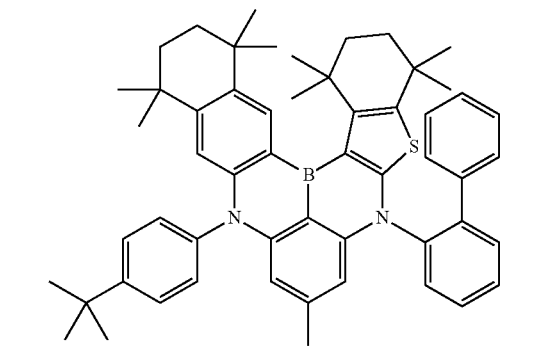
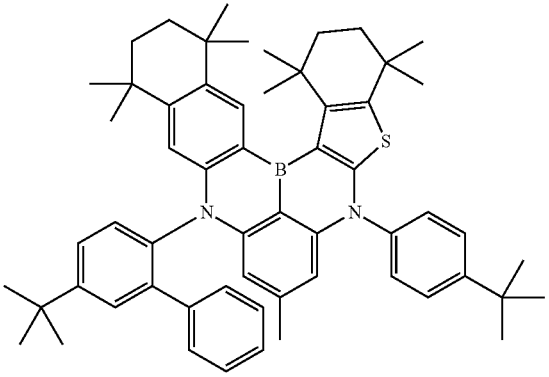
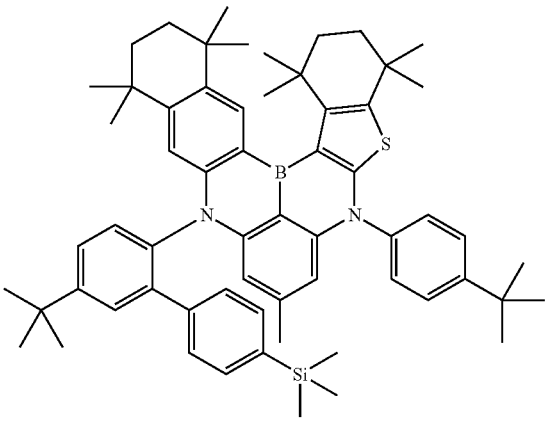
282
-continued
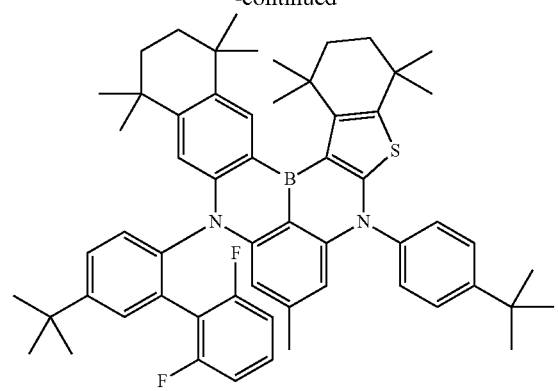
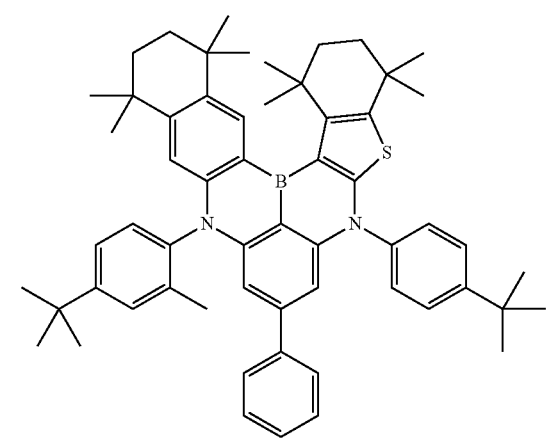
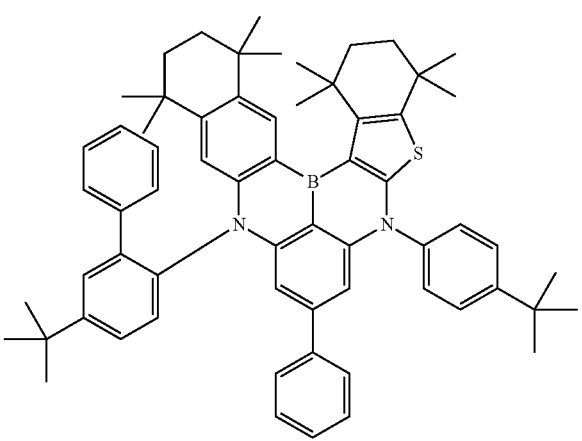
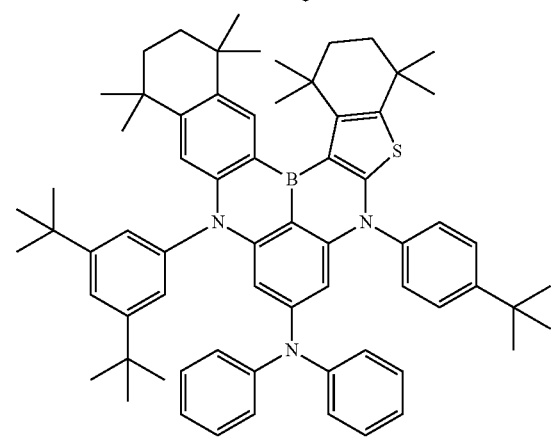

283
-continued
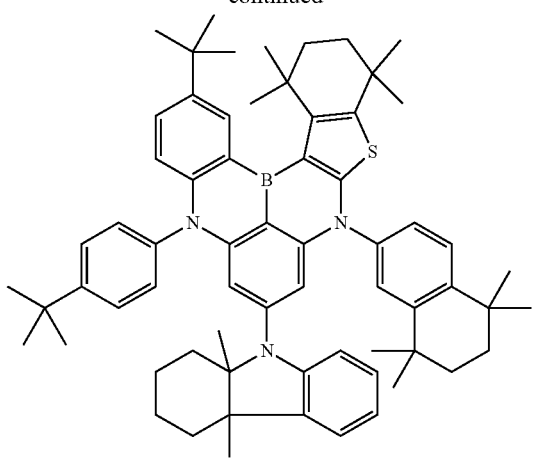
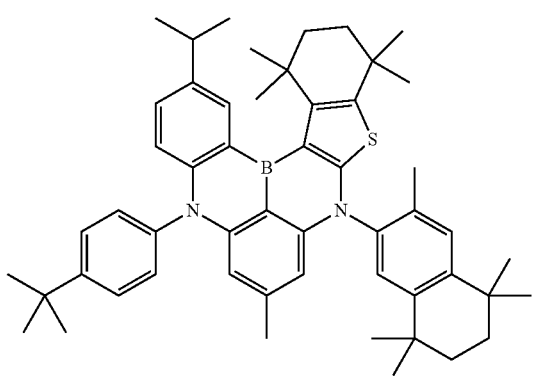
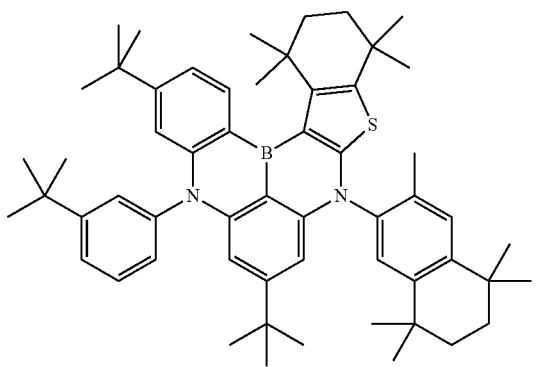
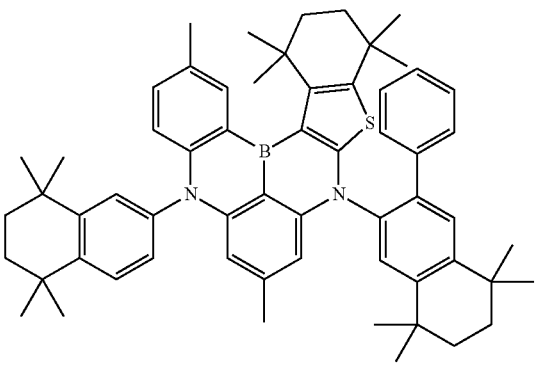
284
-continued
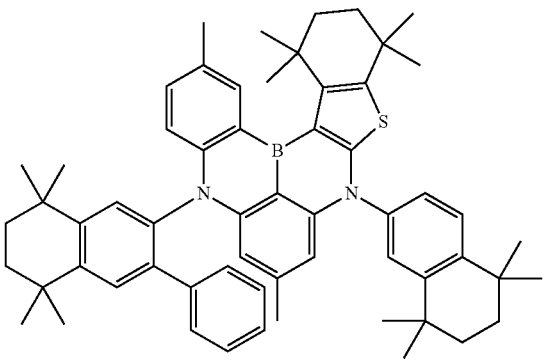
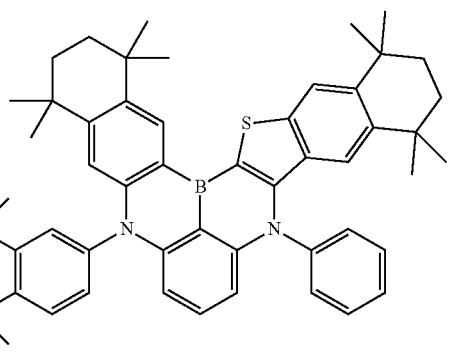
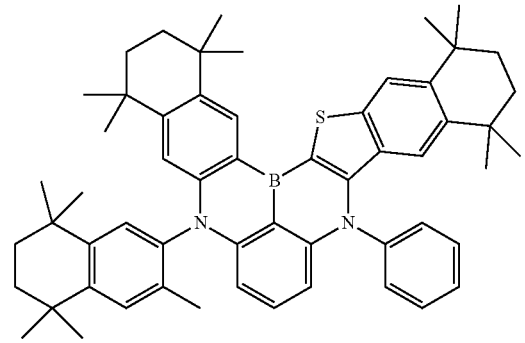
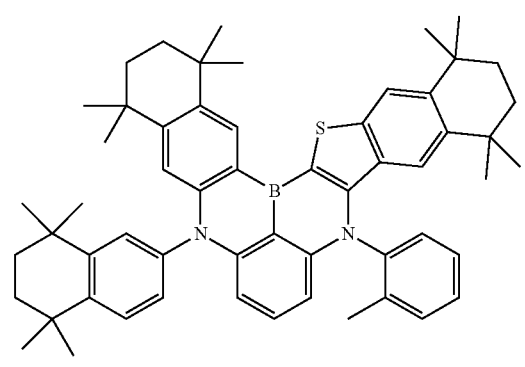

285
-continued
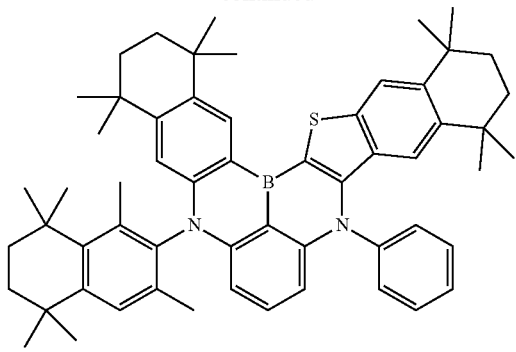
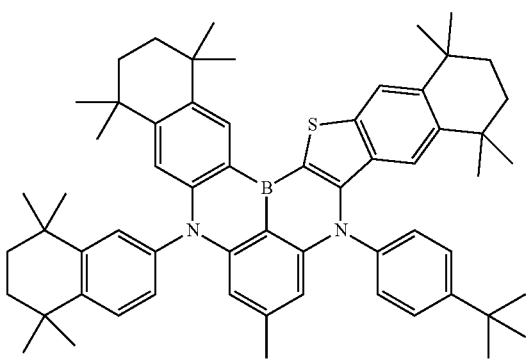
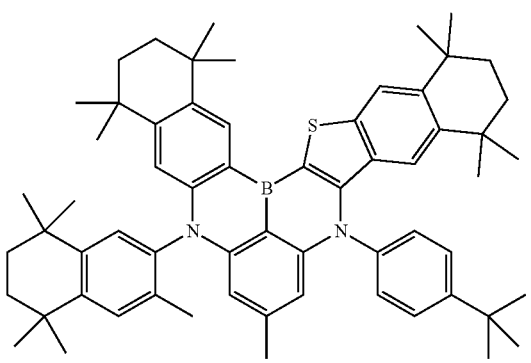
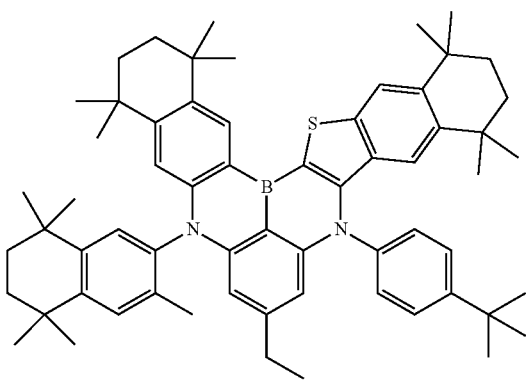
286
-continued
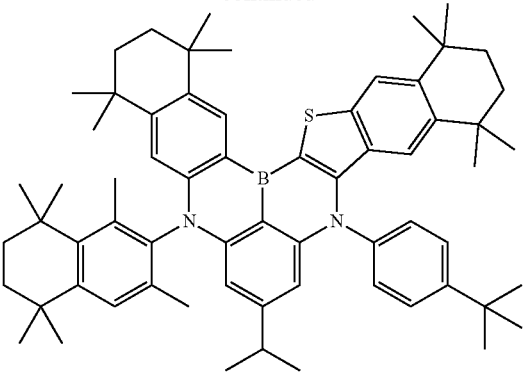
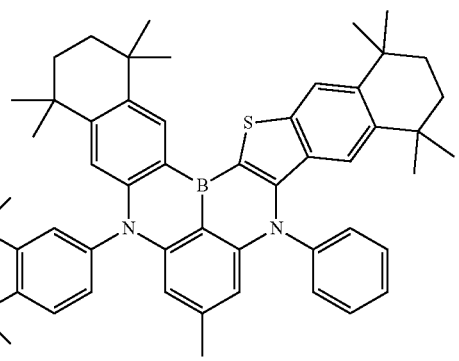
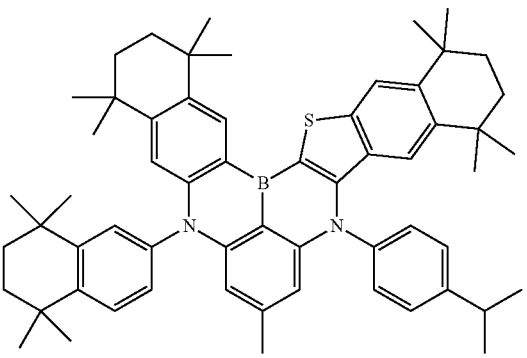
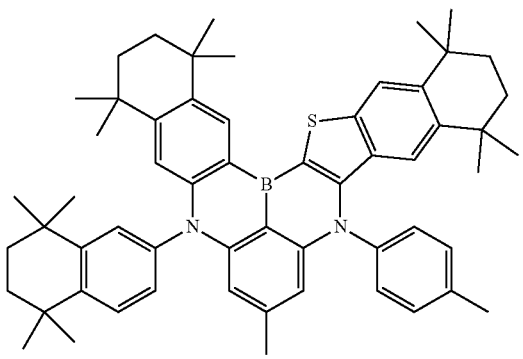

287
-continued
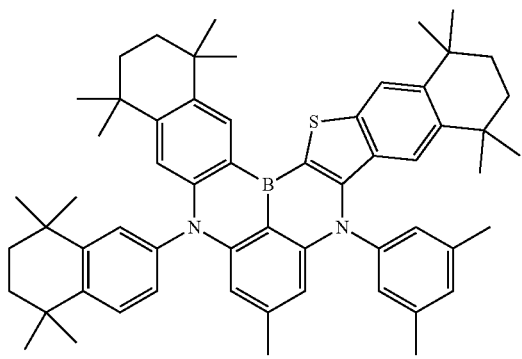
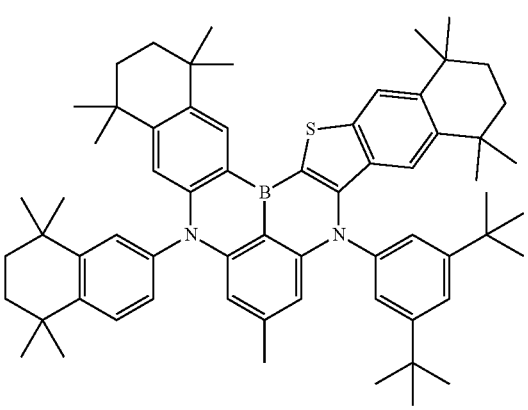
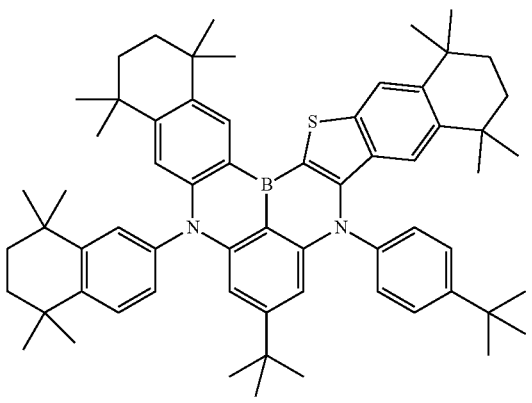
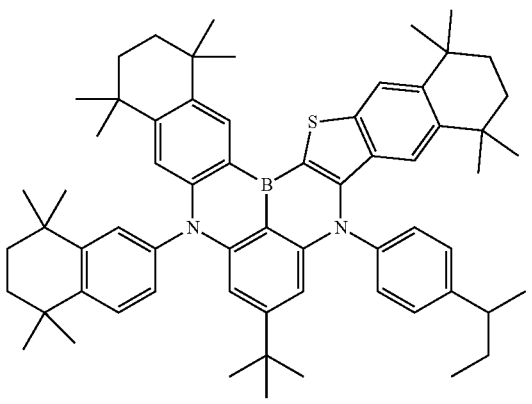
288
-continued
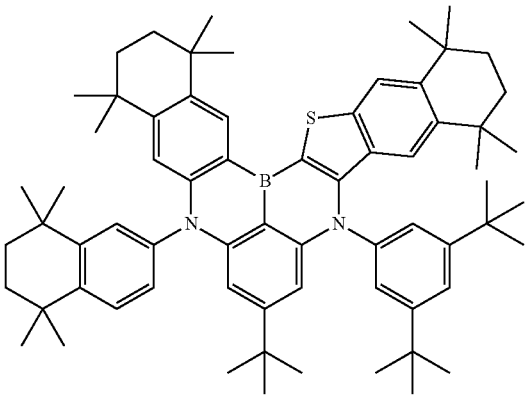
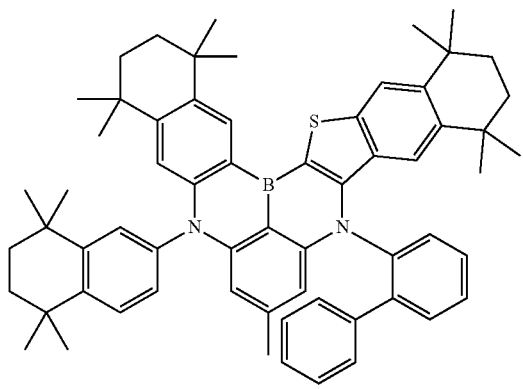
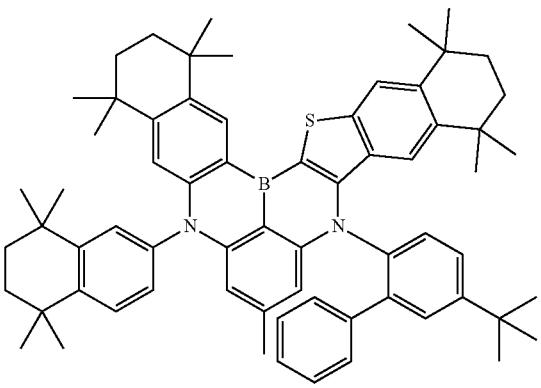
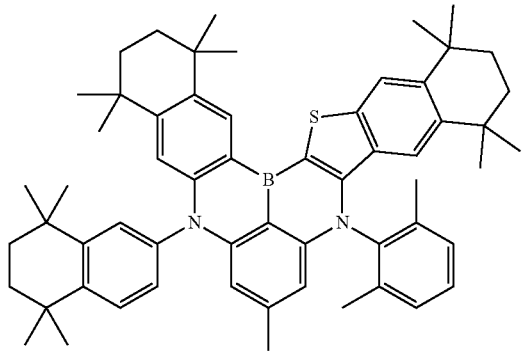

289
-continued
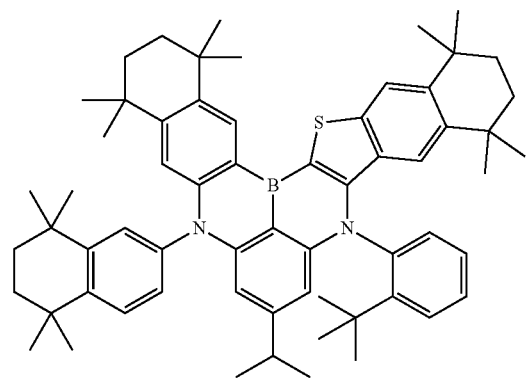
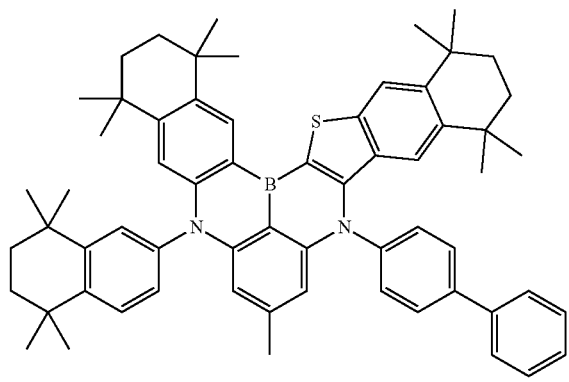
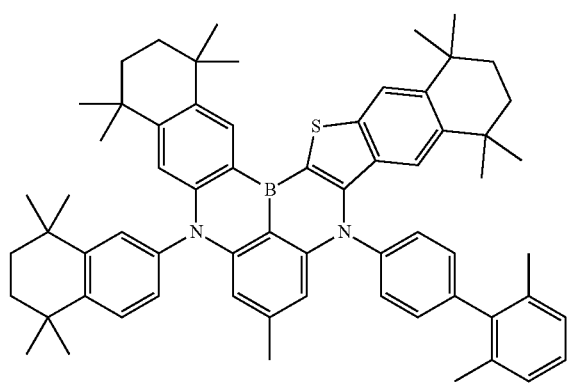
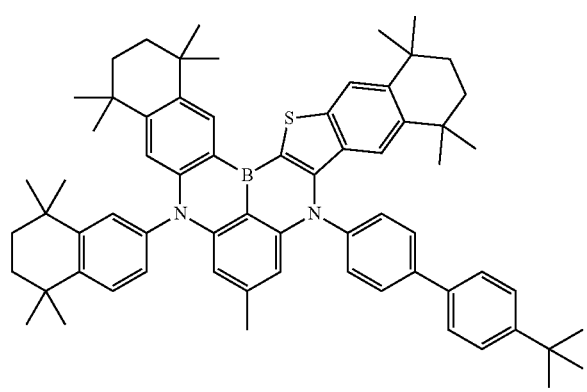
290
-continued
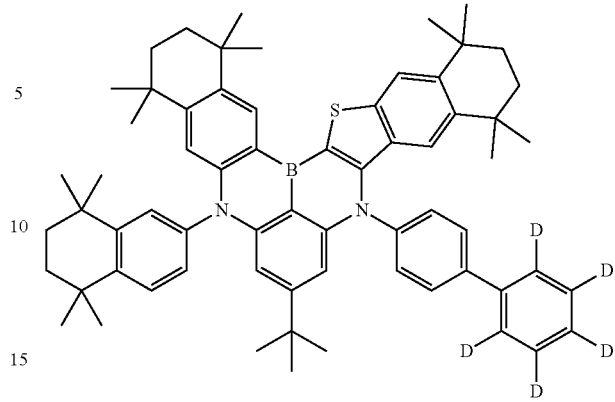
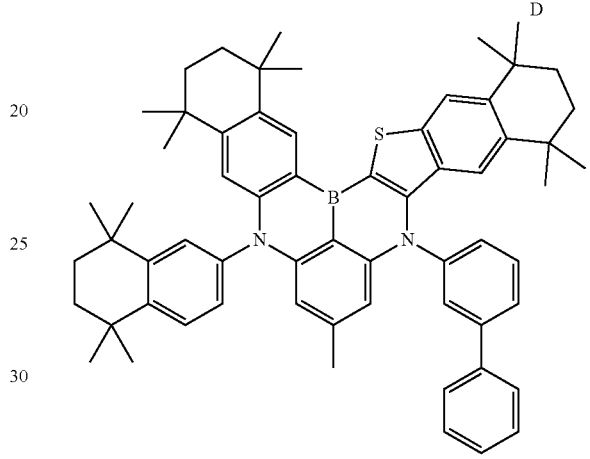
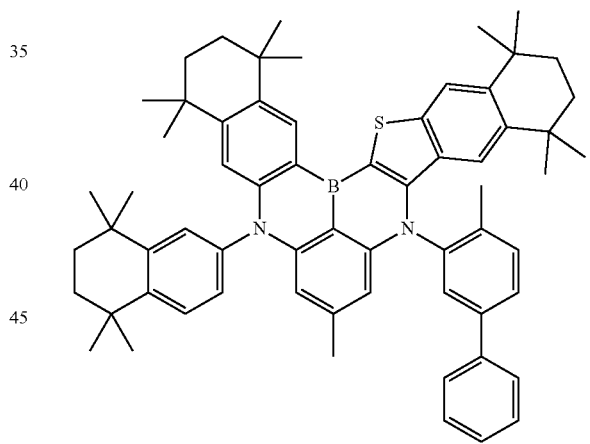
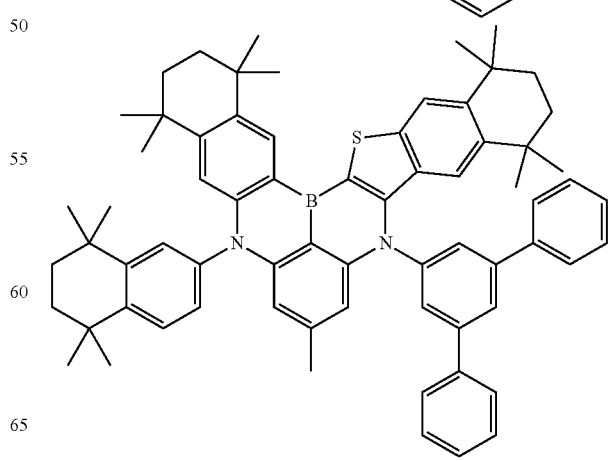

291
-continued
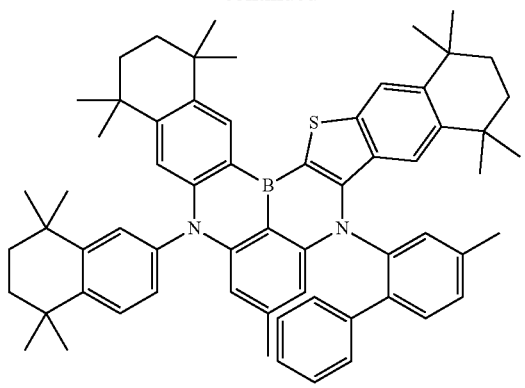
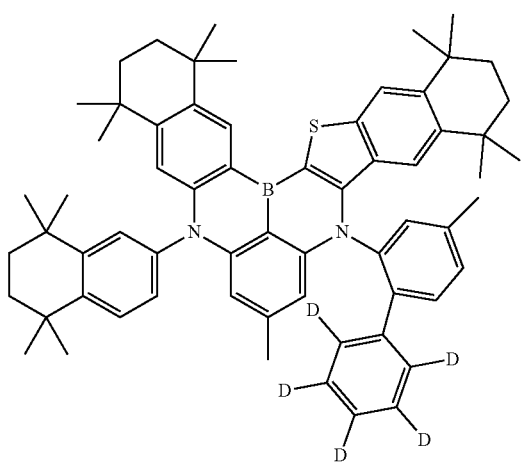
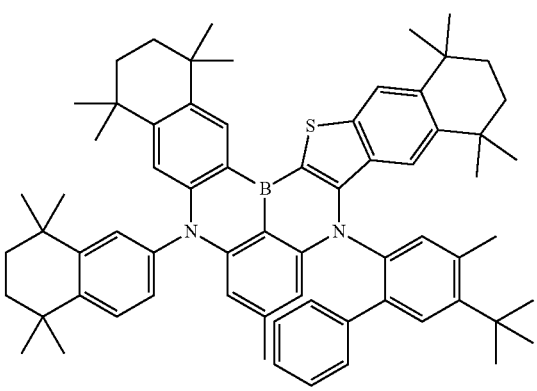
292
-continued
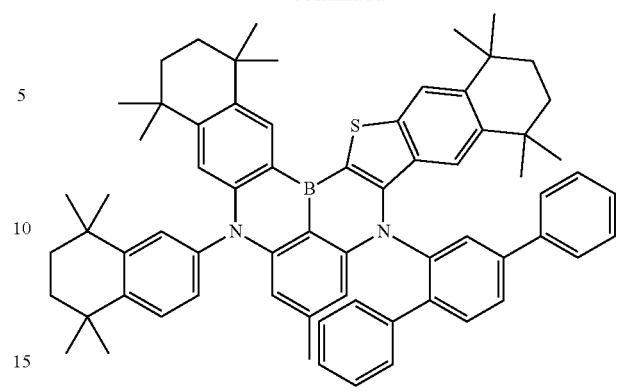
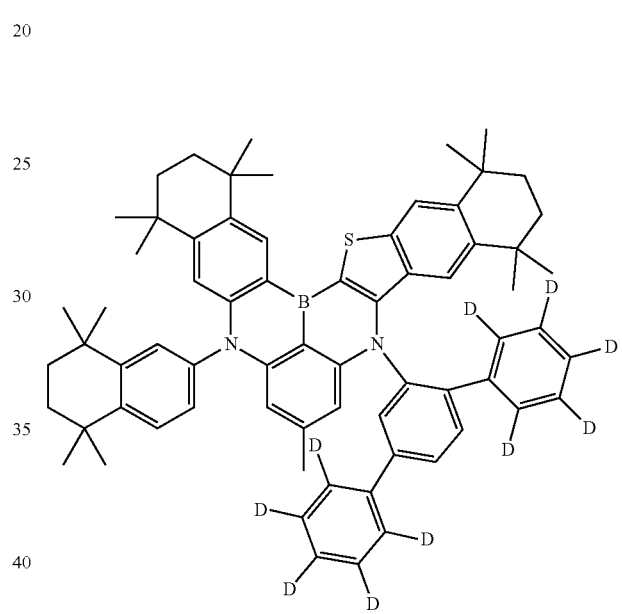
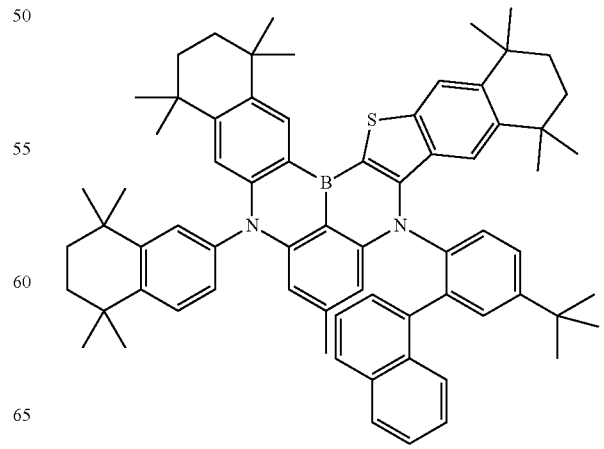

293
-continued
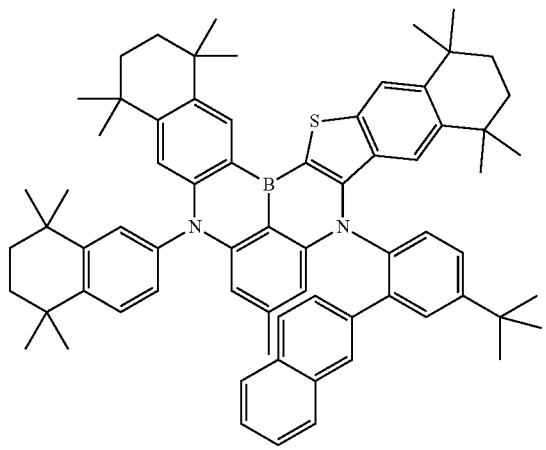
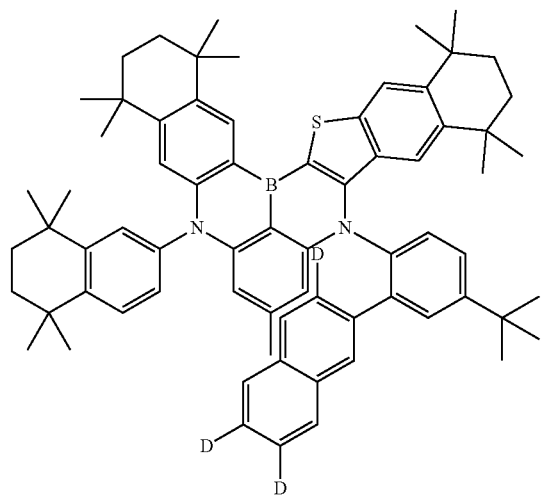
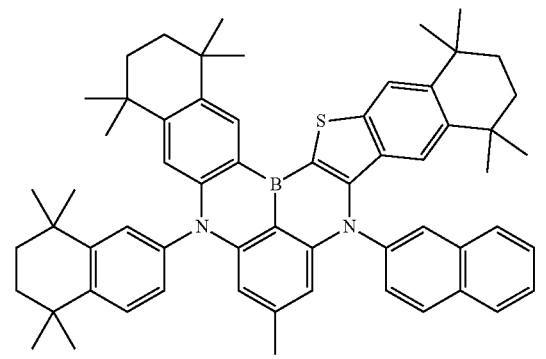
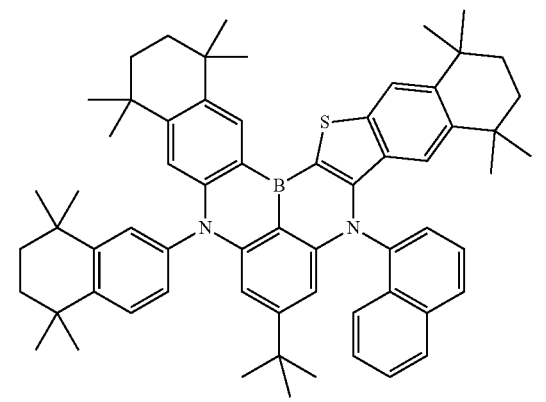
294
-continued
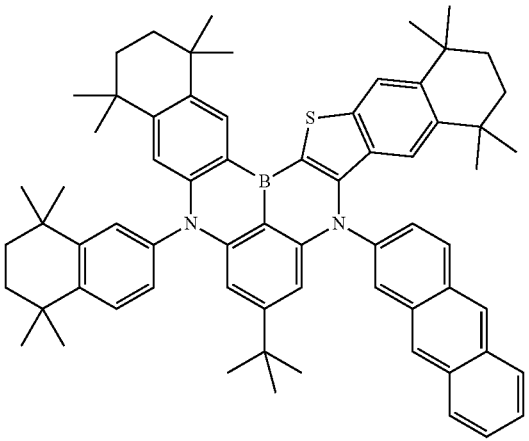
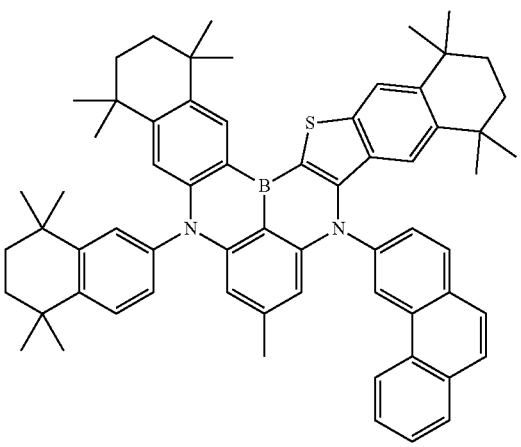
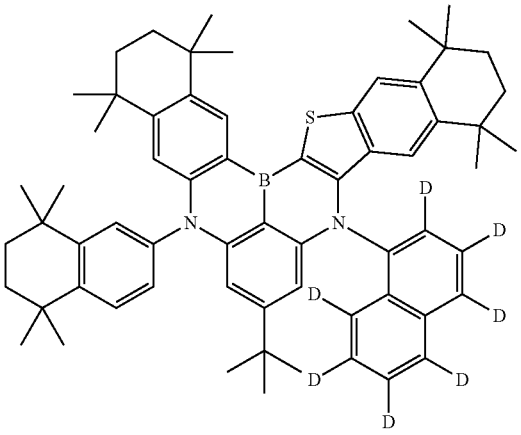
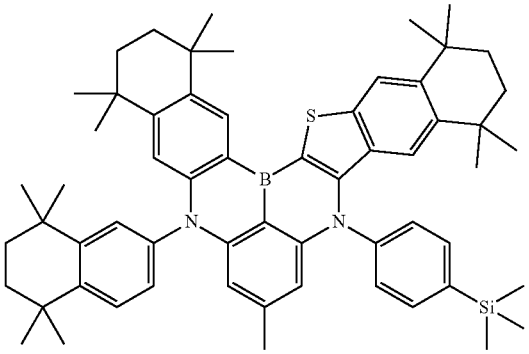

295
-continued
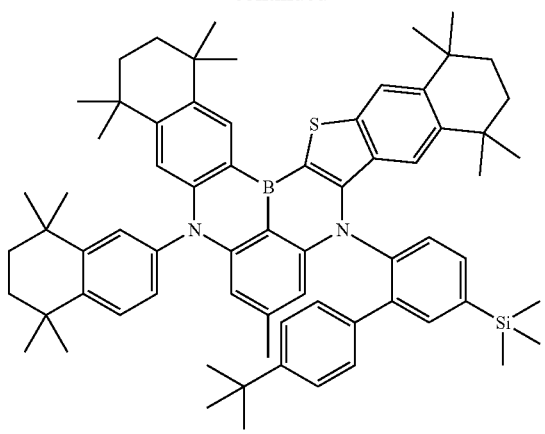
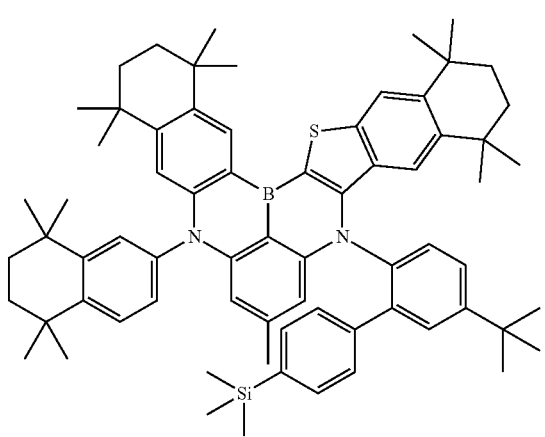
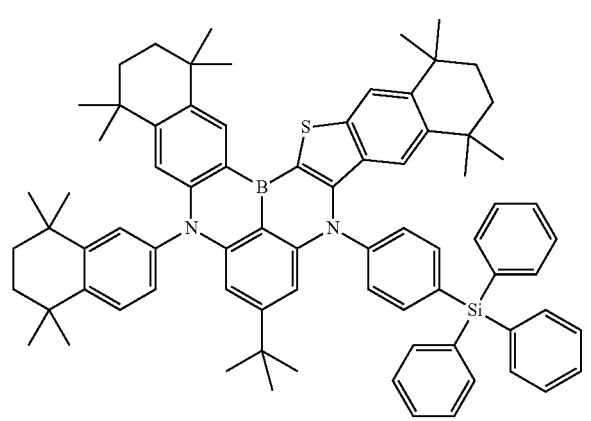
296
-continued
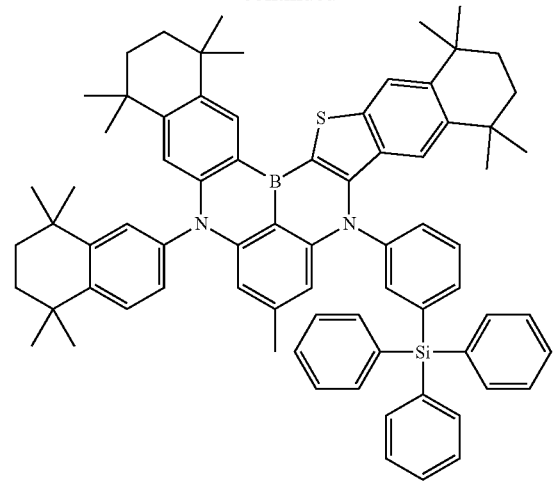
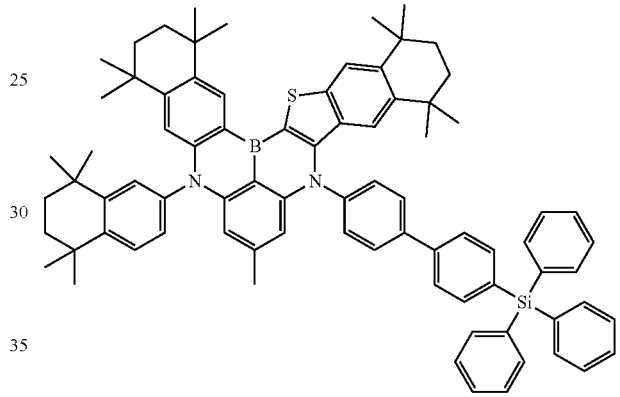
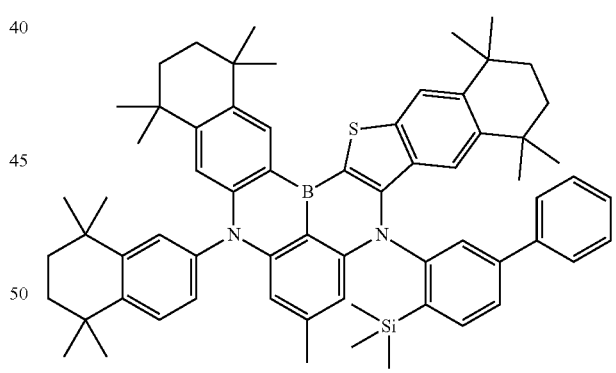
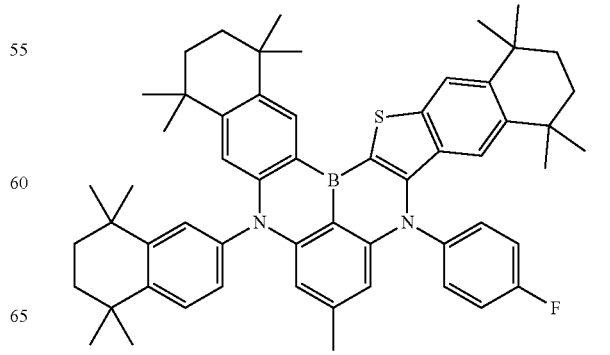

297
-continued
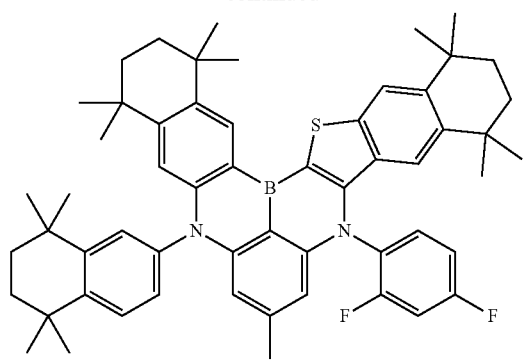
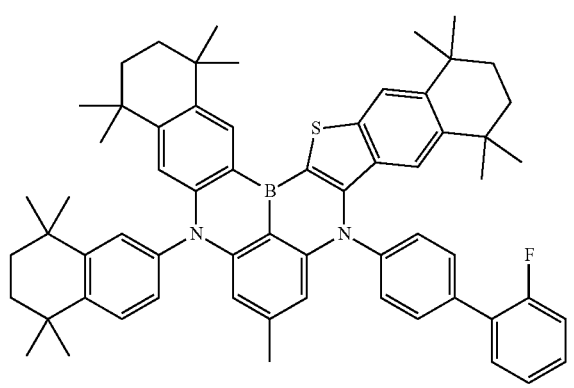
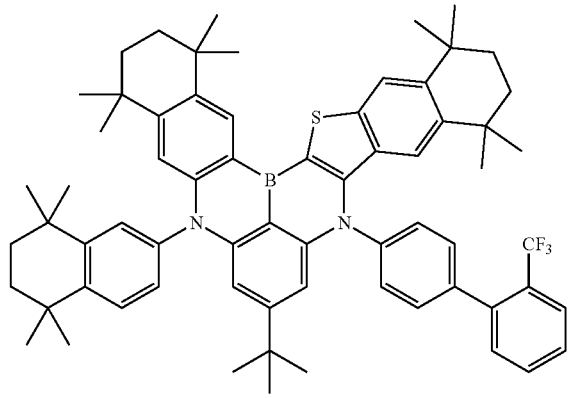
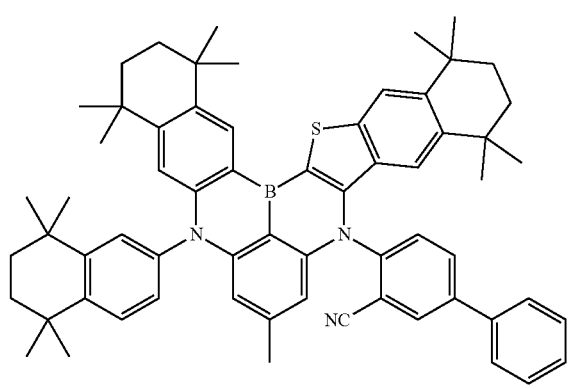
298
-continued
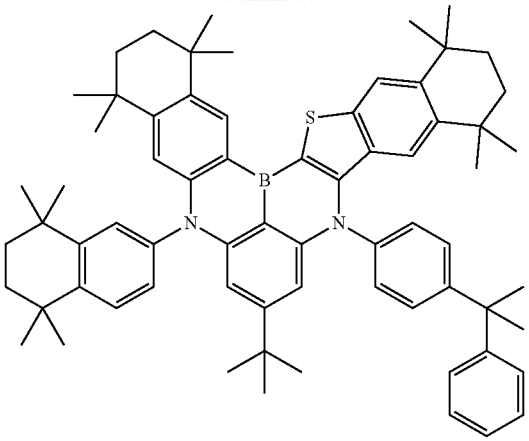
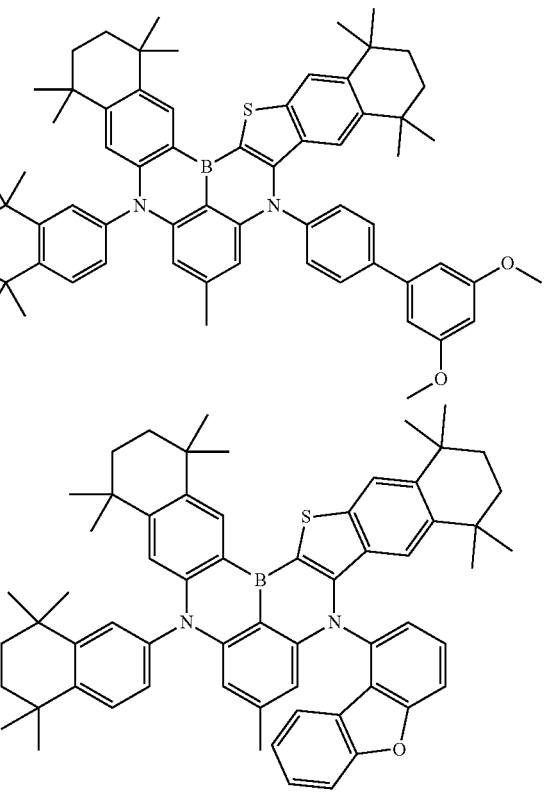
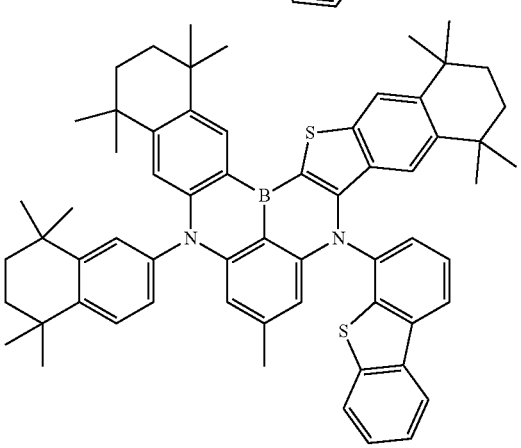

299 -continued
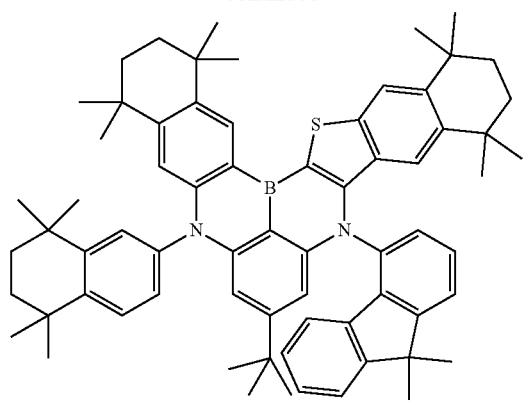
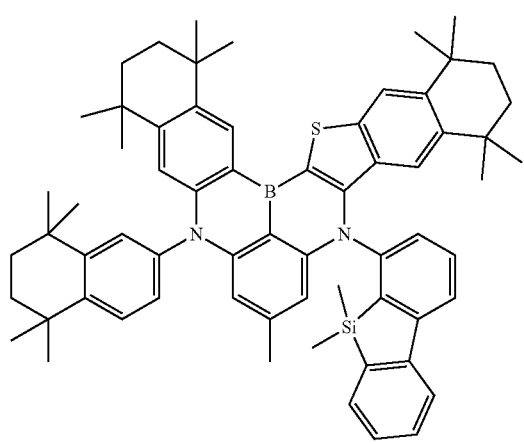
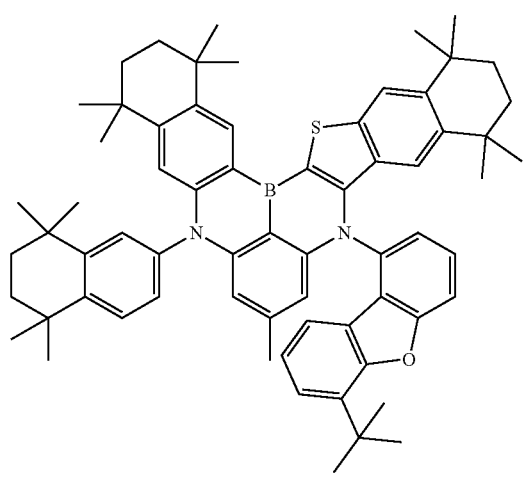
300 -continued
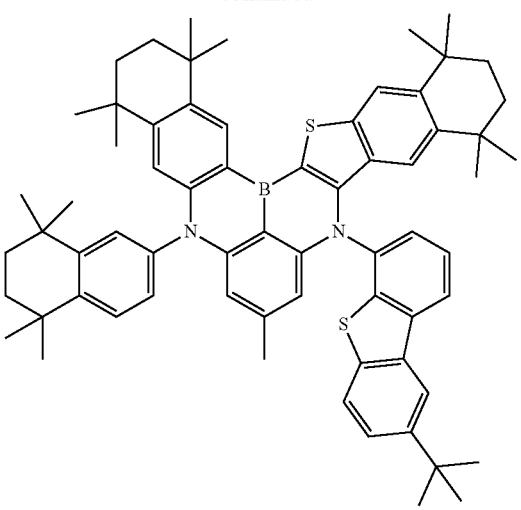
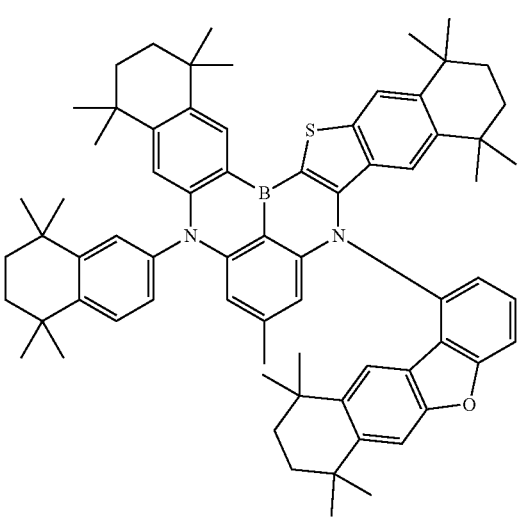
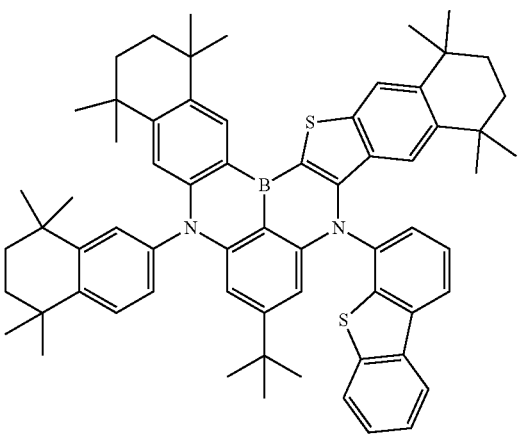

301
-continued
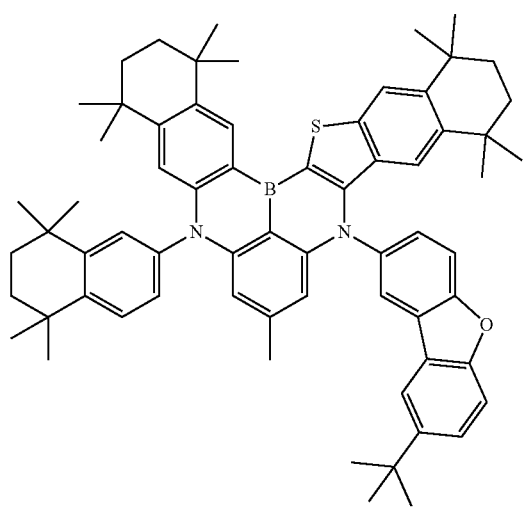
302
-continued
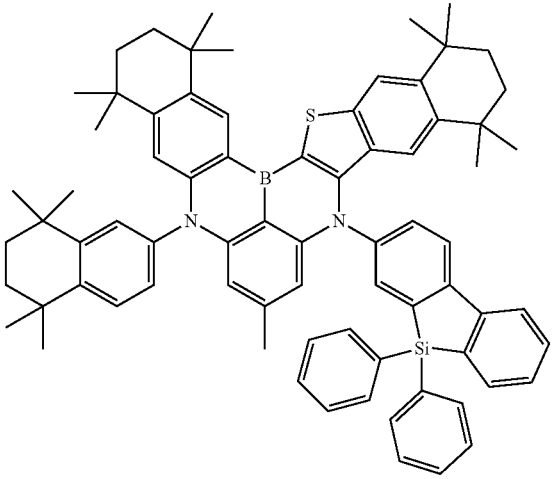
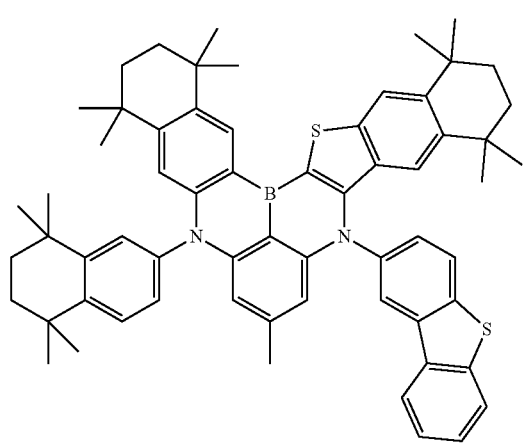
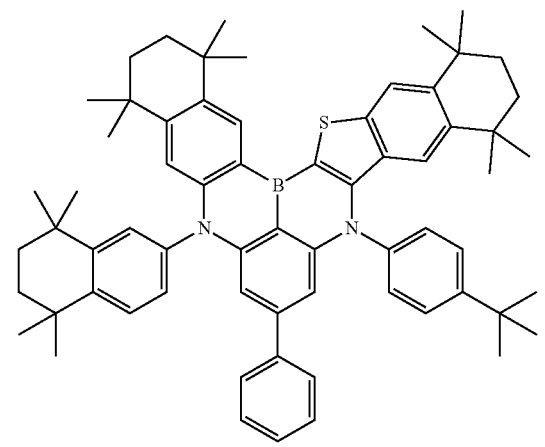
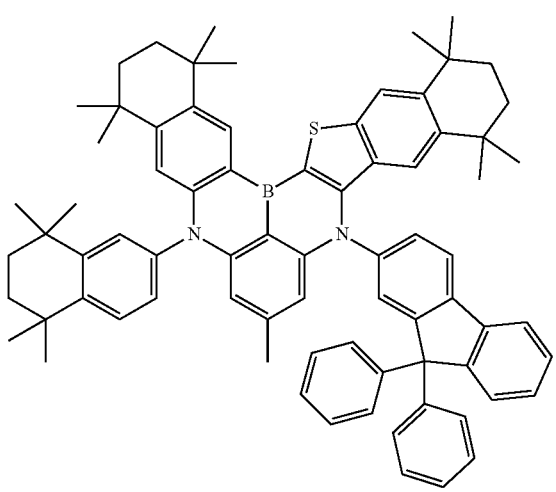
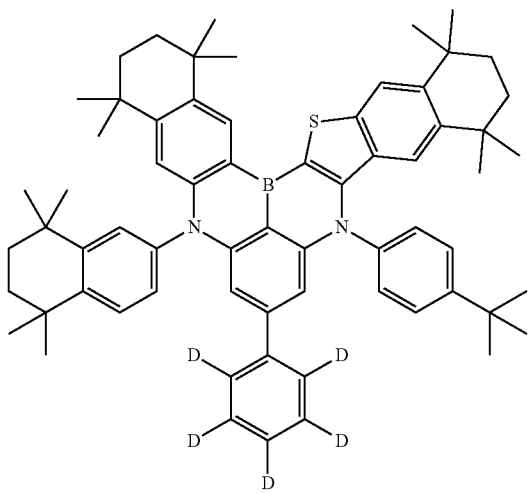

303
-continued
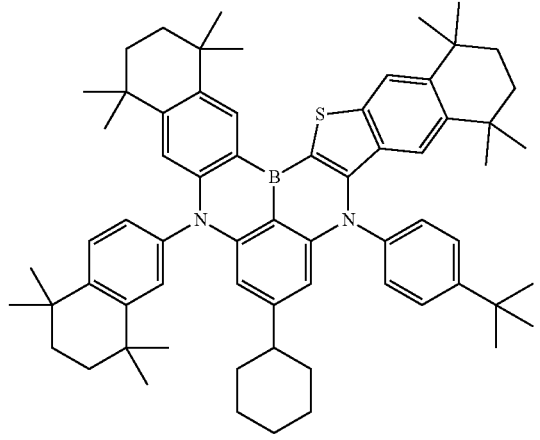
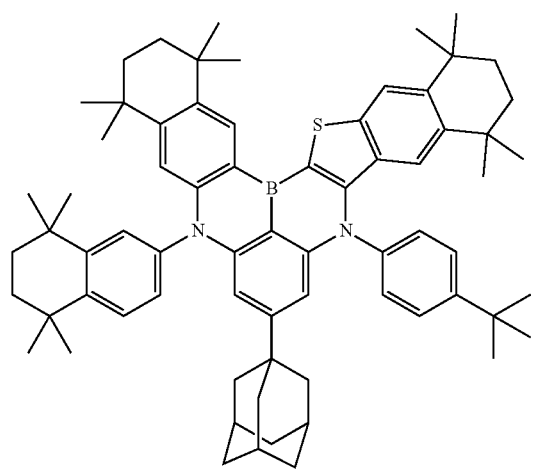
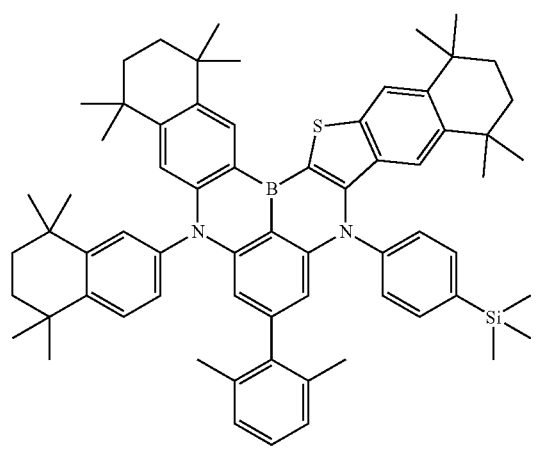
304
-continued
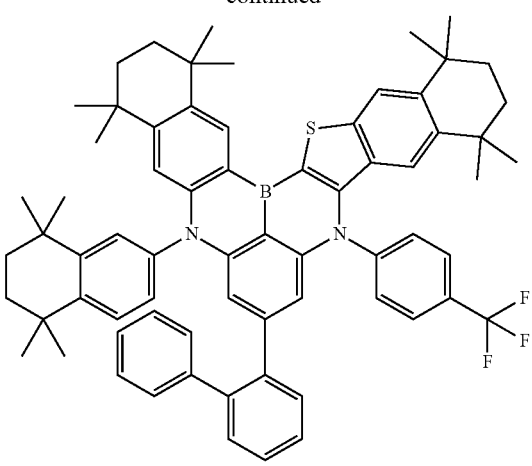
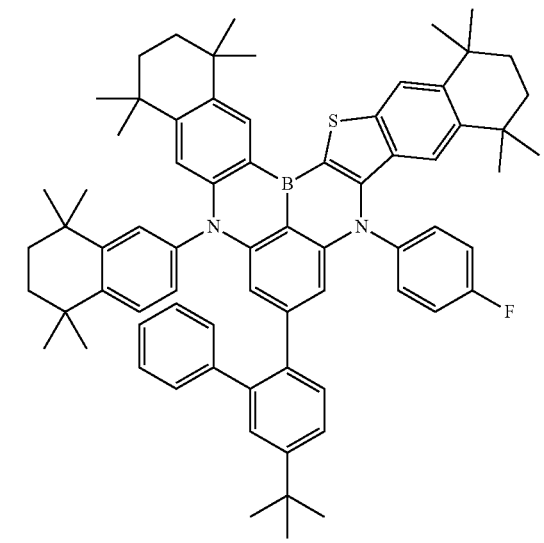
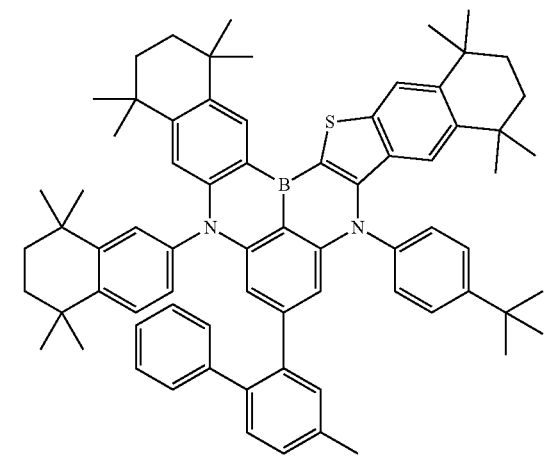

305
-continued
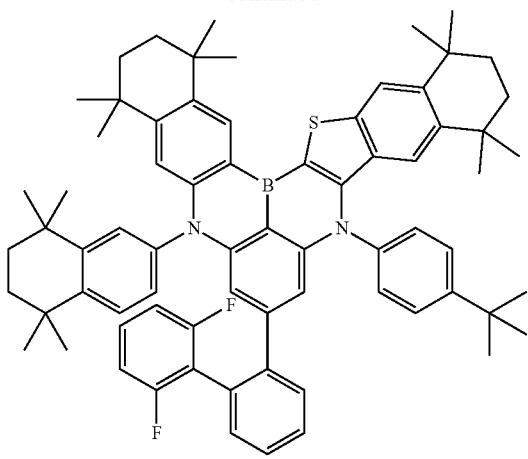
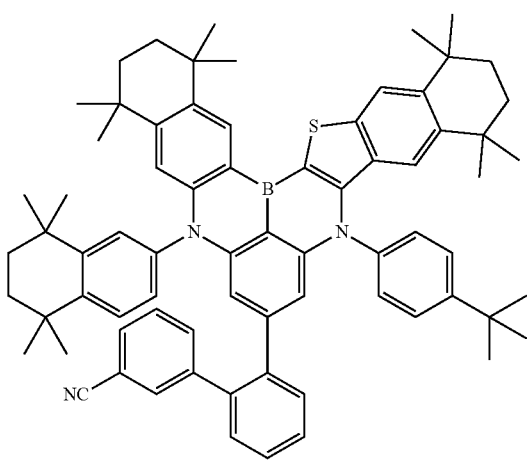
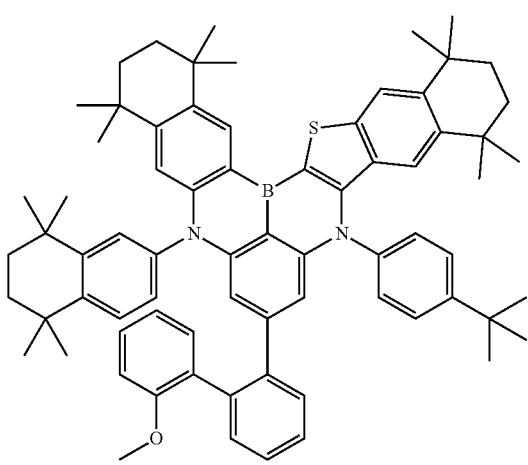
306
-continued
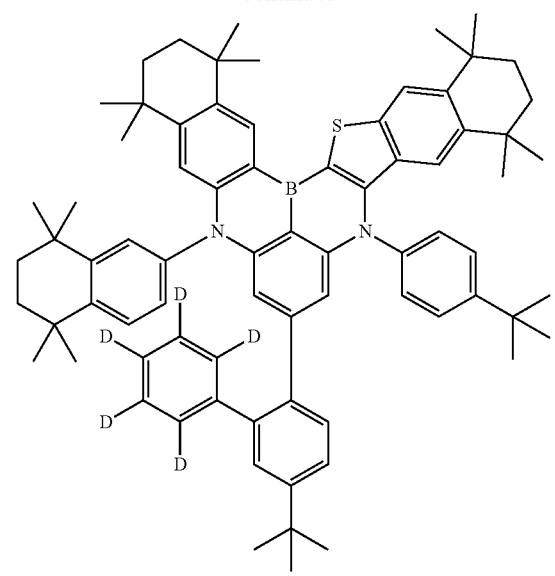
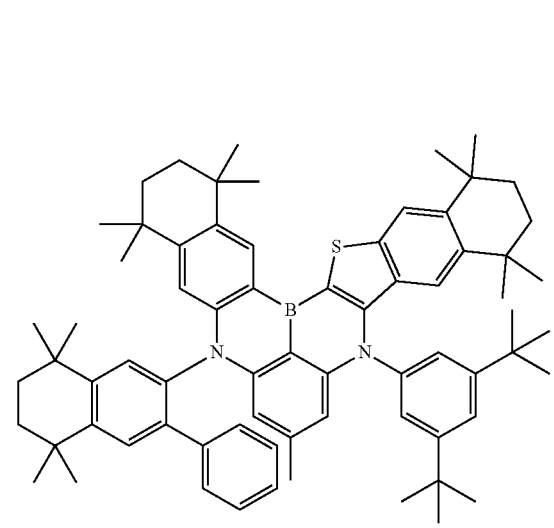
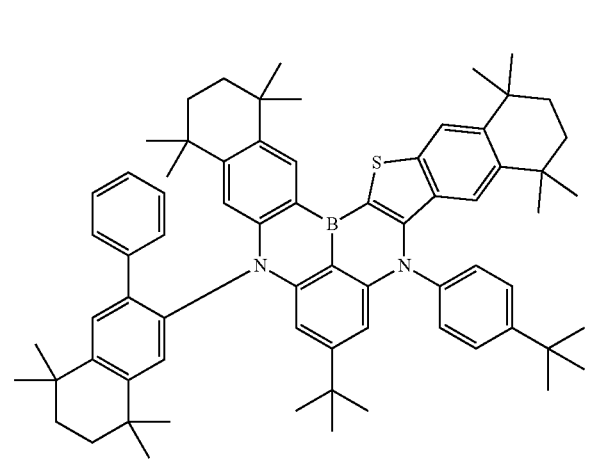

| 307 -continued | 308 -continued |
|---|---|
| 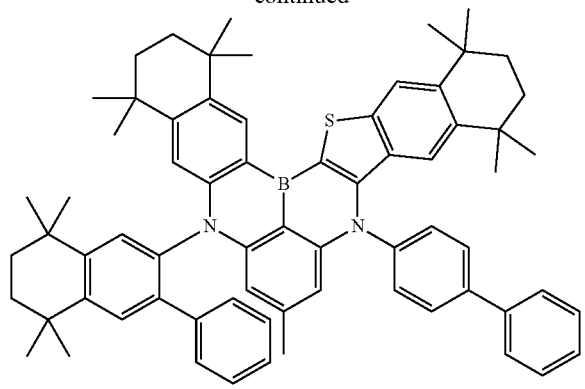 | 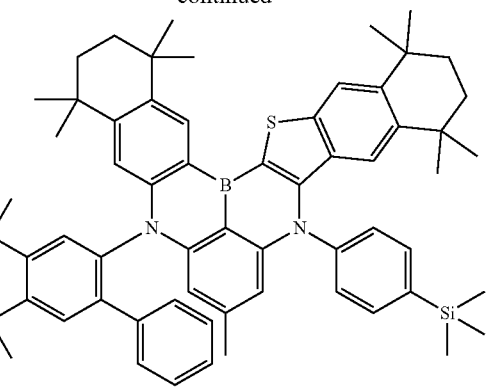 |
| 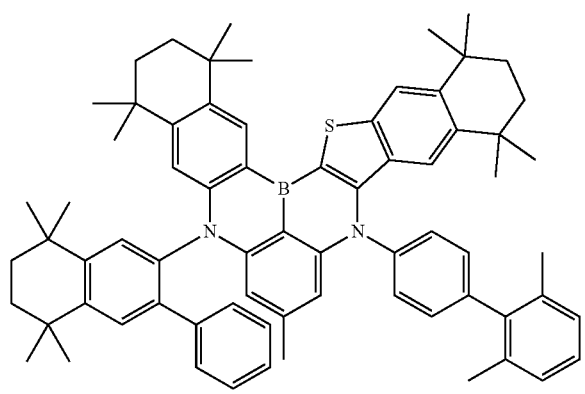 | 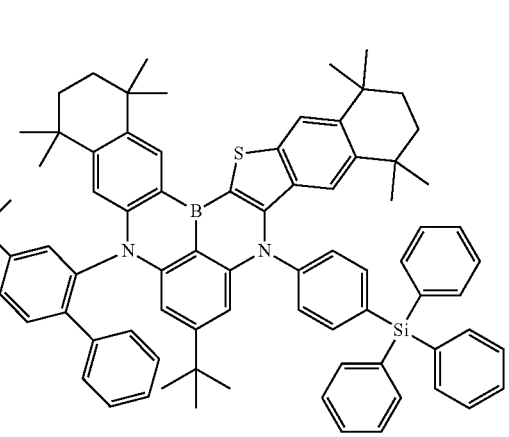 |
| 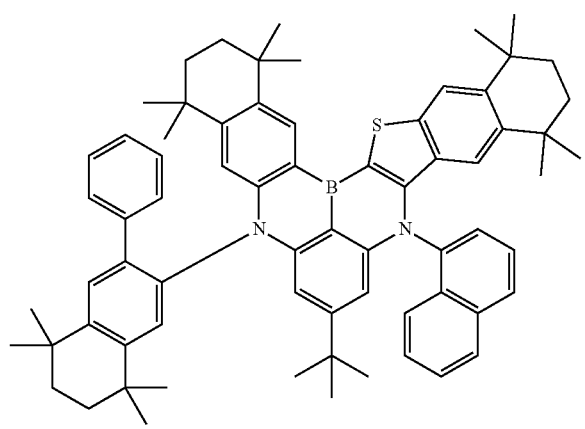 |  |
| 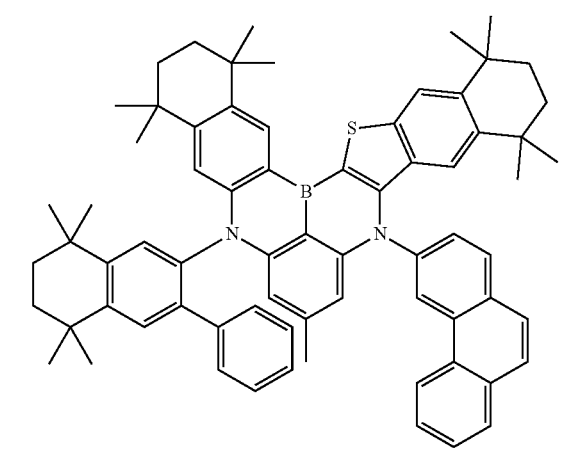 | 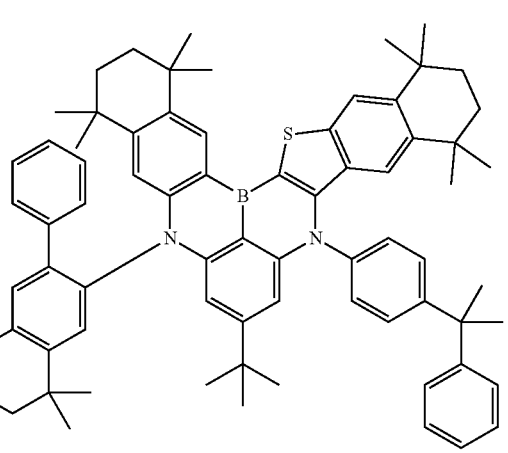 |

309
-continued
310
-continued
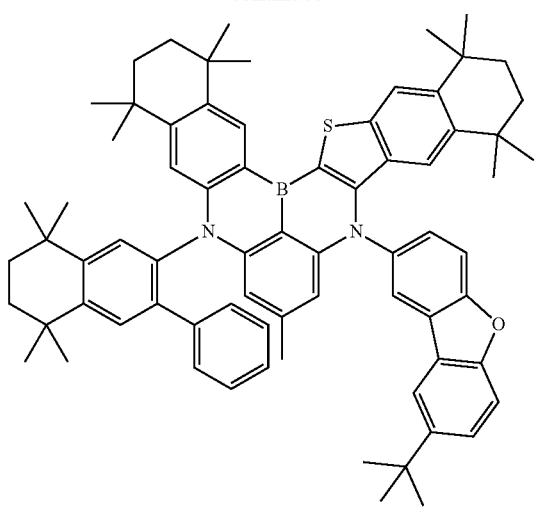
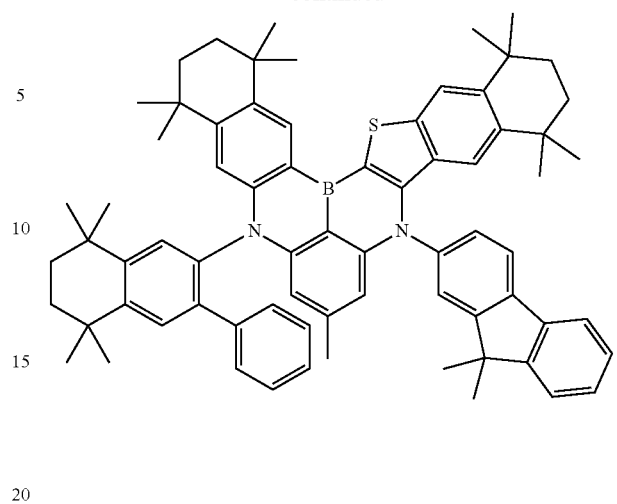
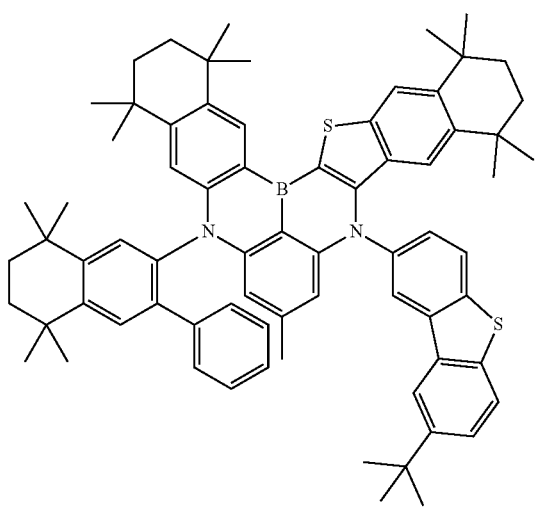
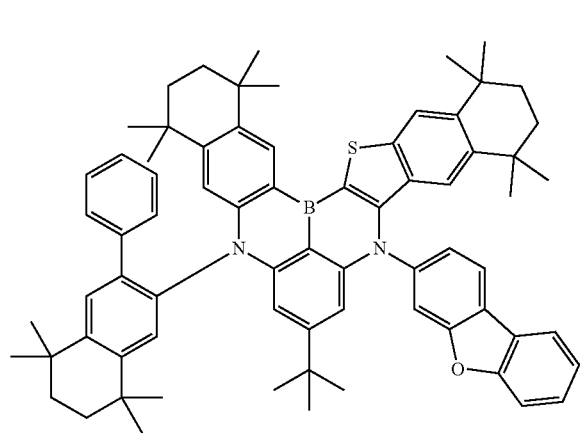
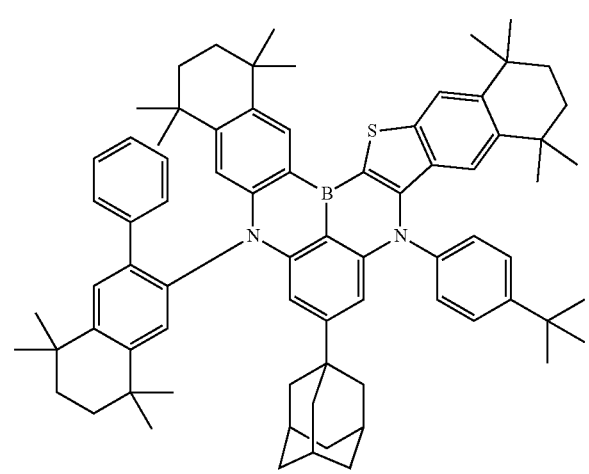

311
-continued
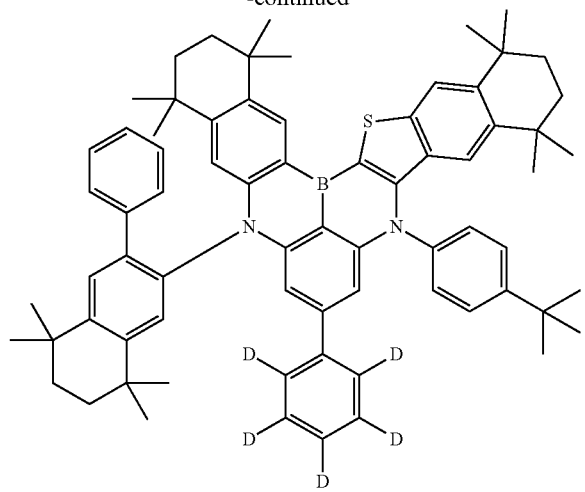
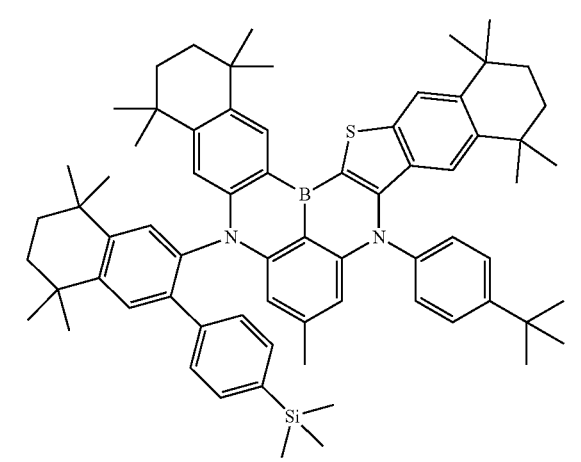
312
-continued
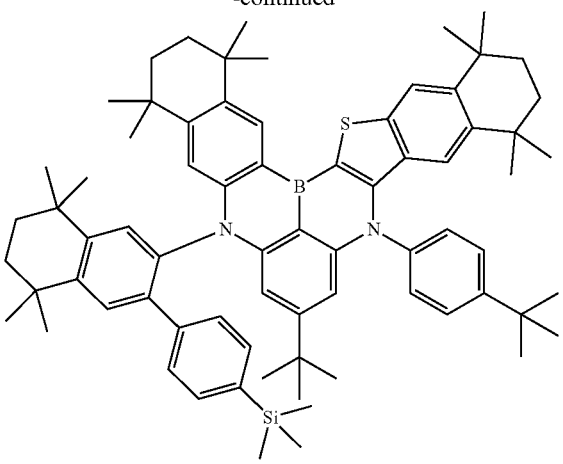
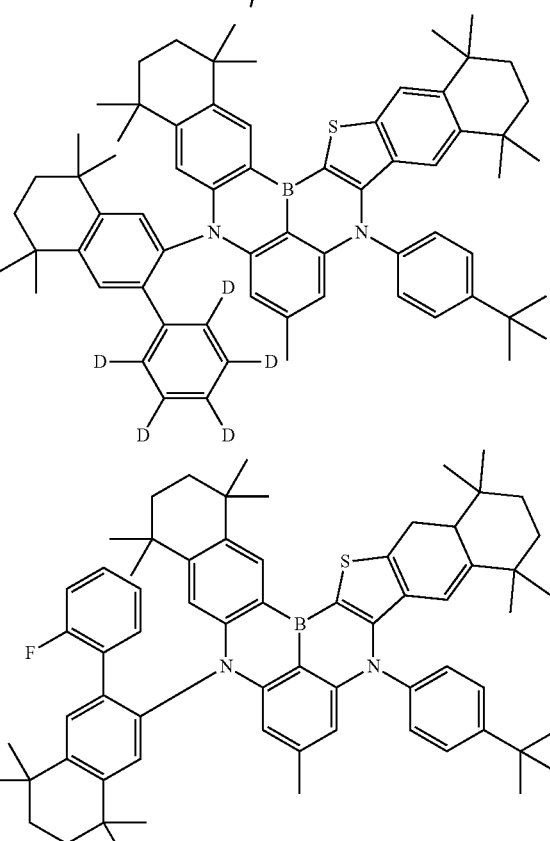
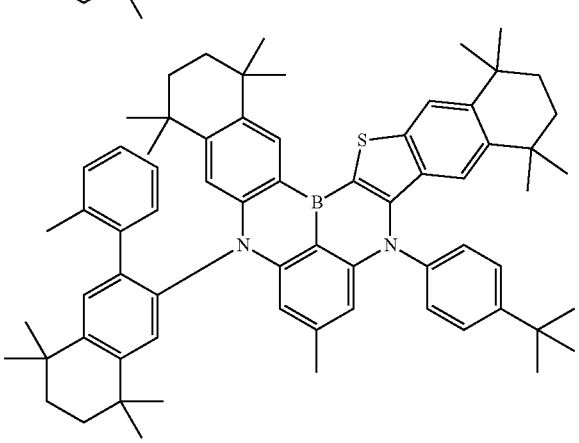

313
-continued
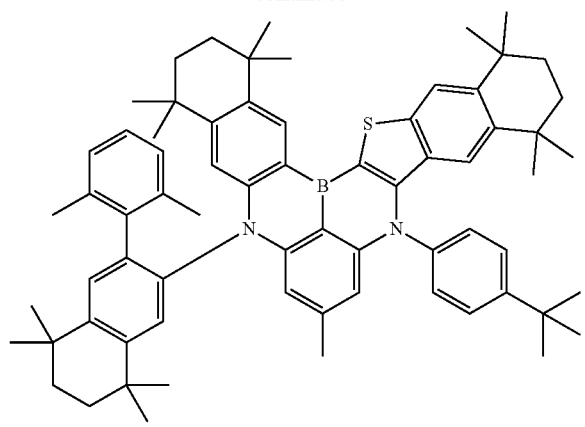
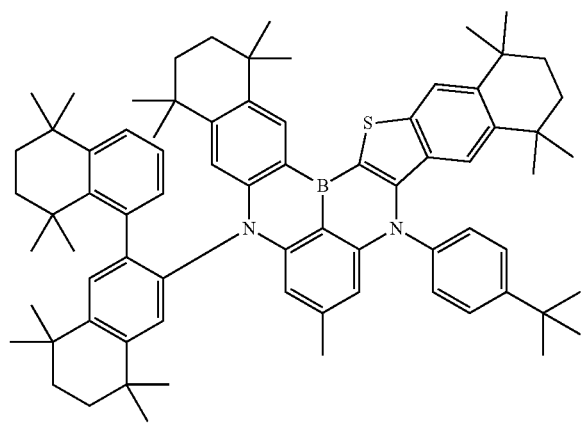
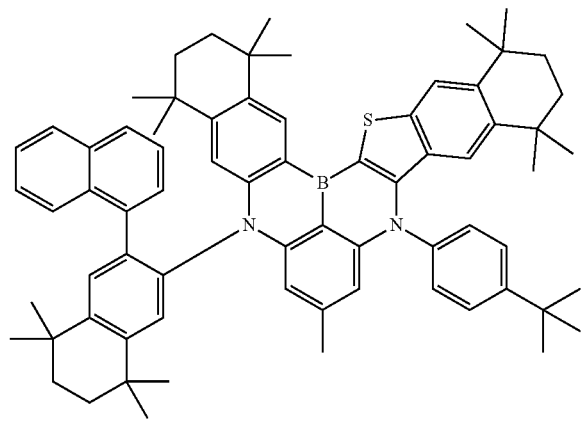
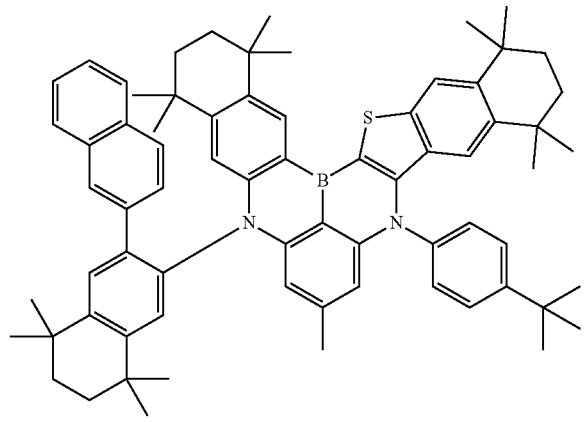
314
-continued
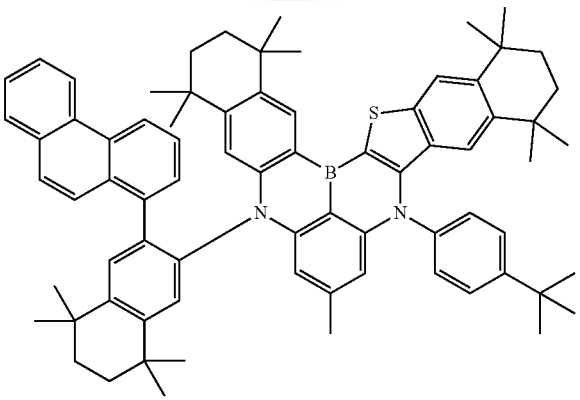
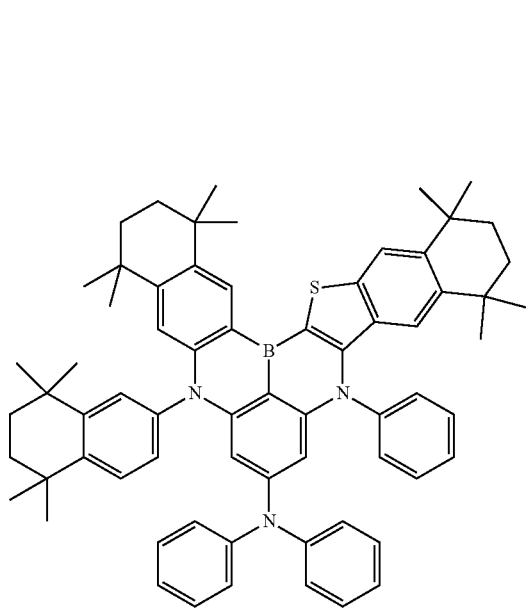
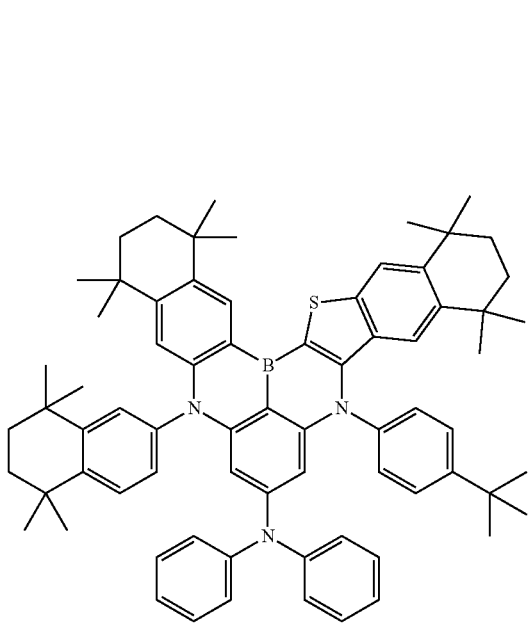

315
-continued
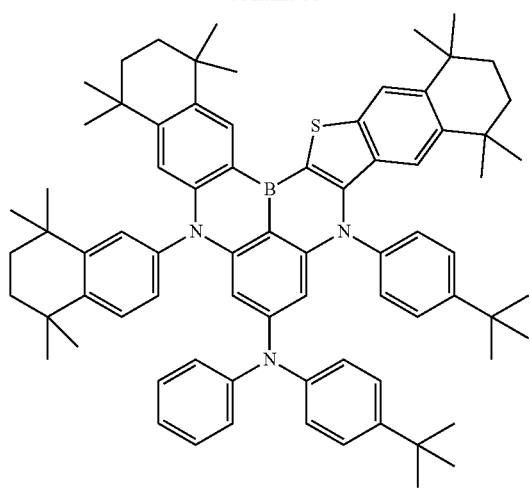
316
-continued
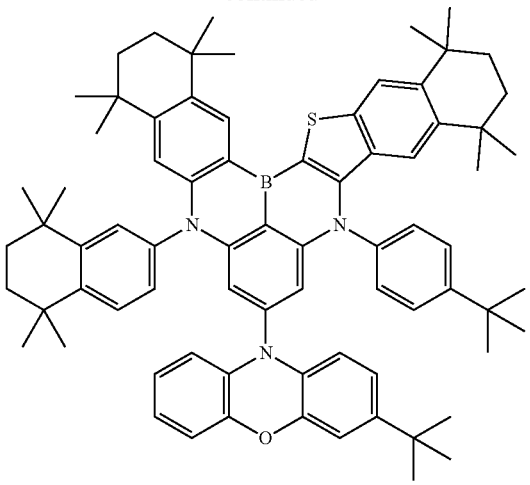
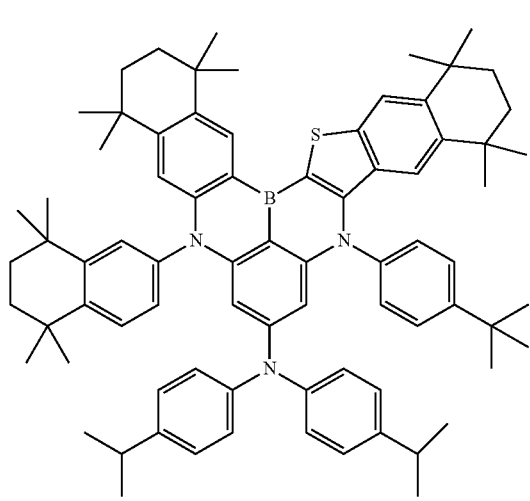
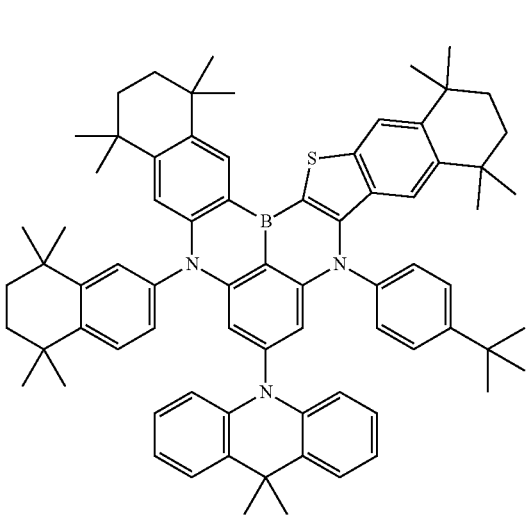
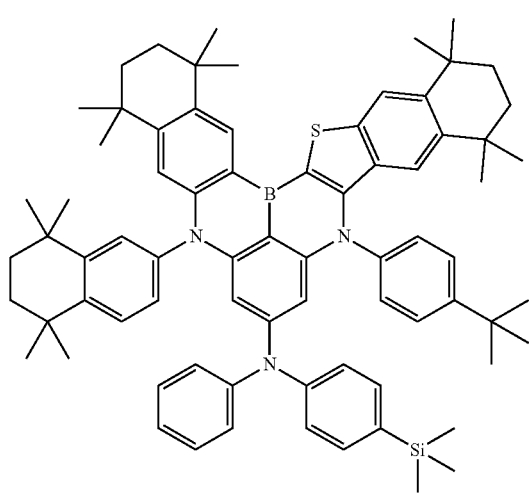
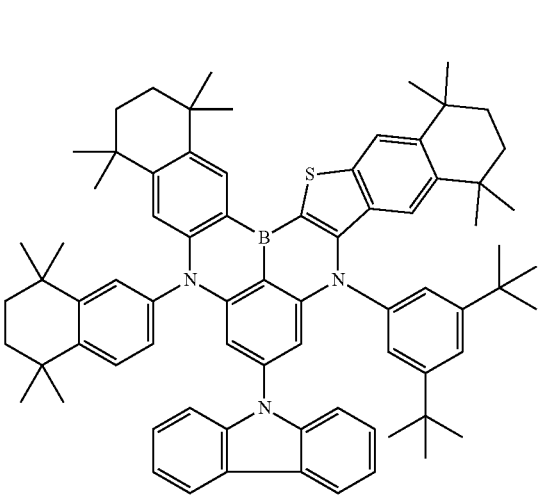

317
-continued
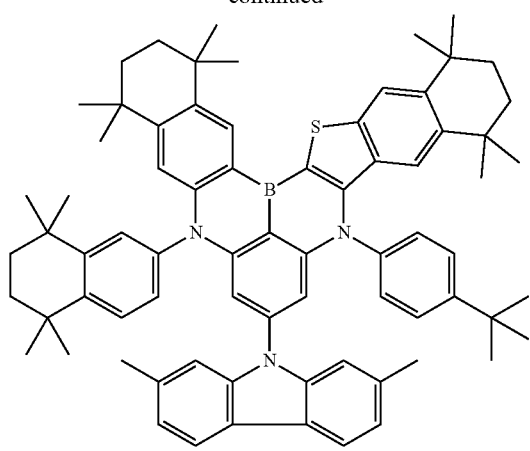
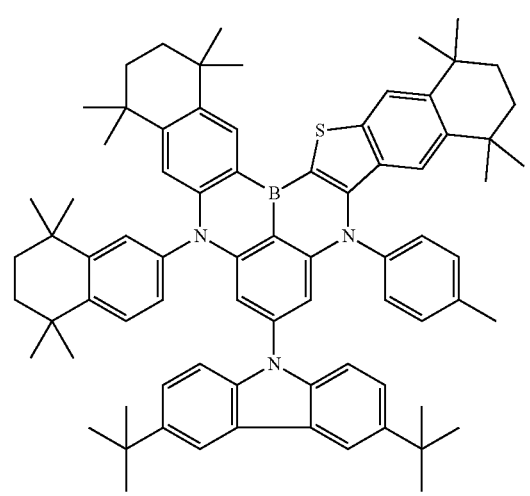
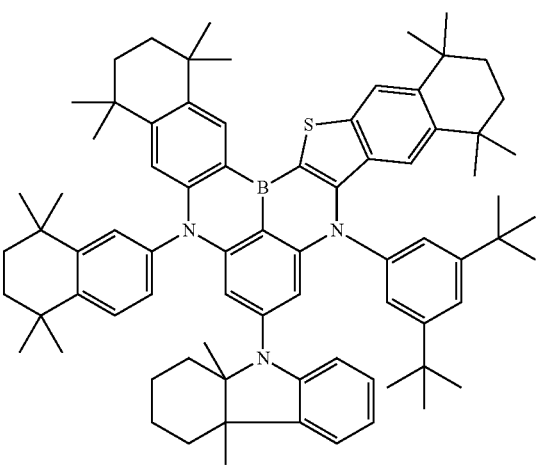
318
-continued
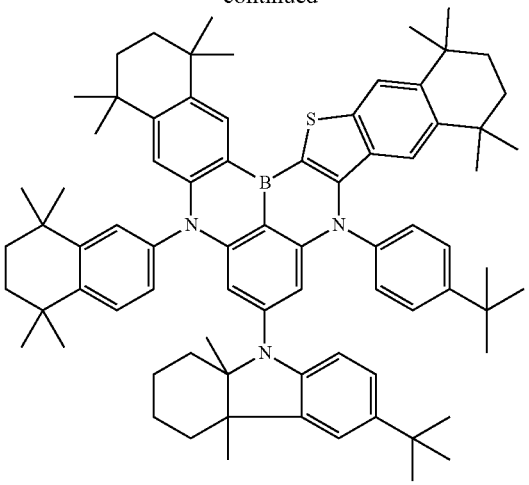
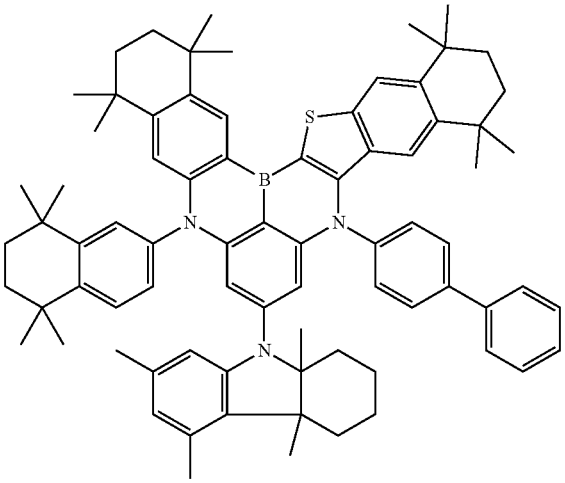
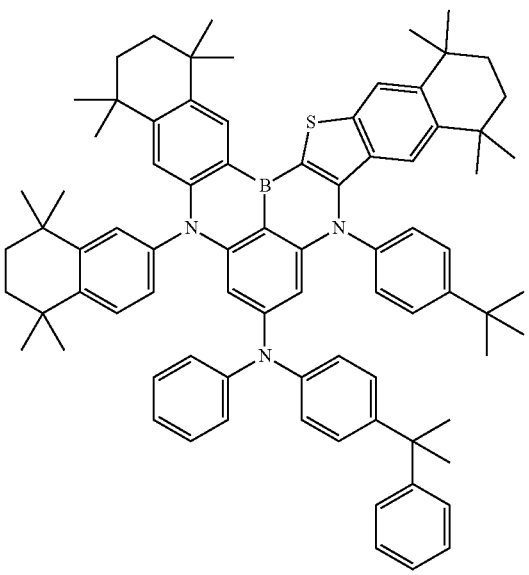

319
-continued
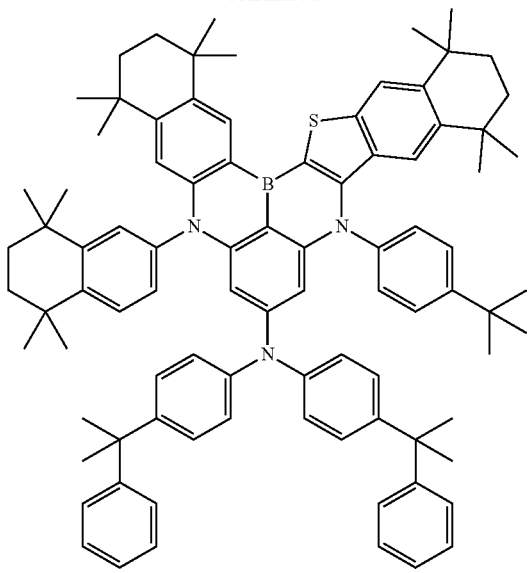
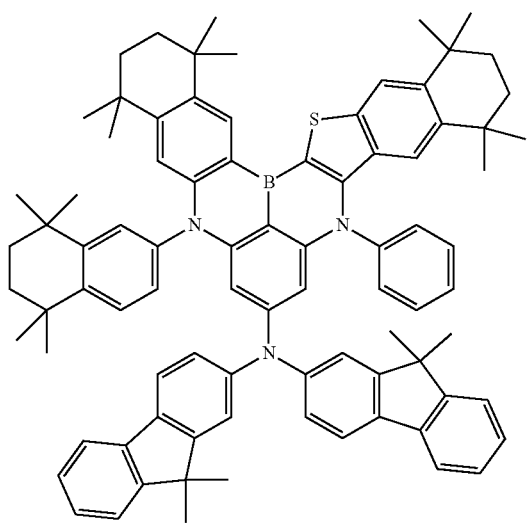
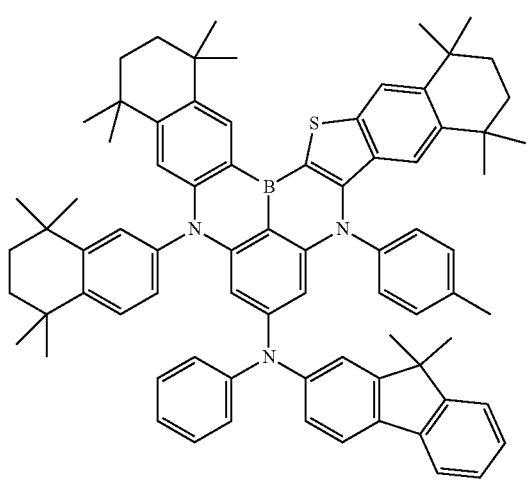
320
-continued
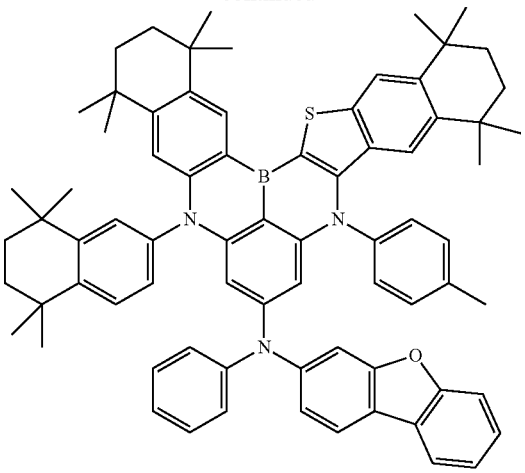
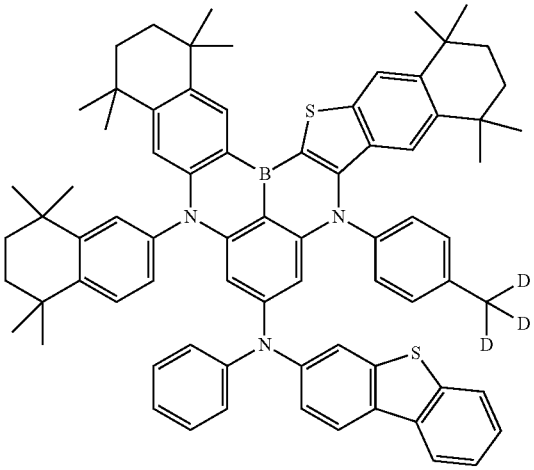
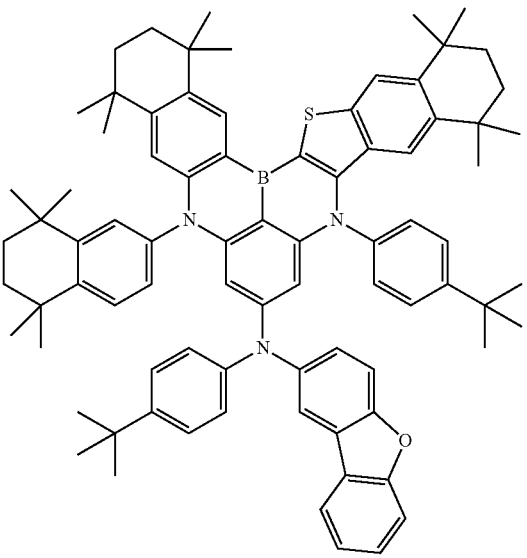

321
-continued
322
-continued
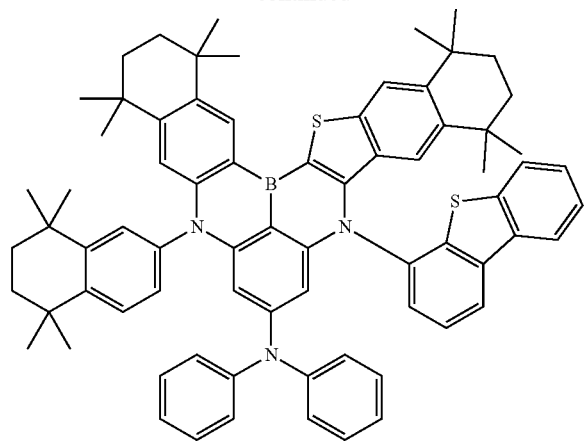
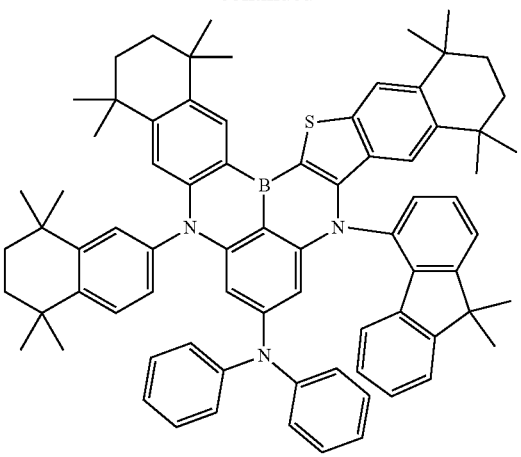
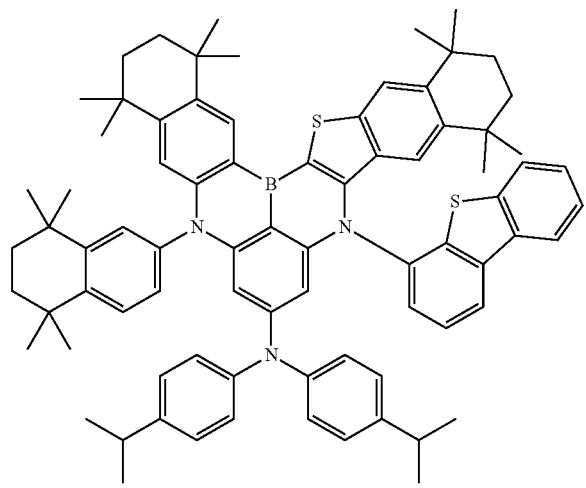
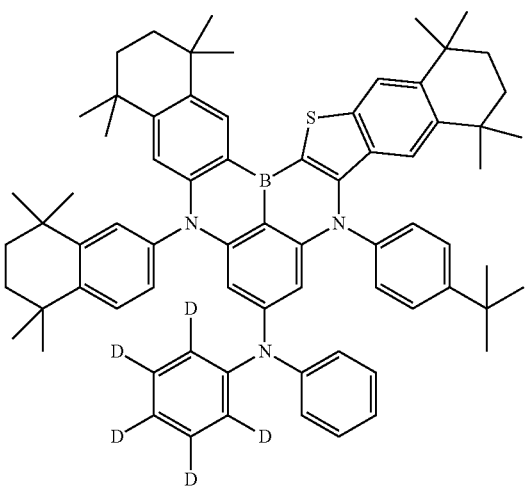
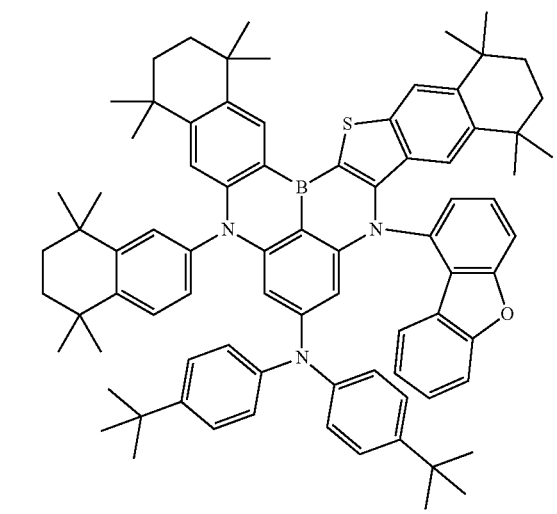
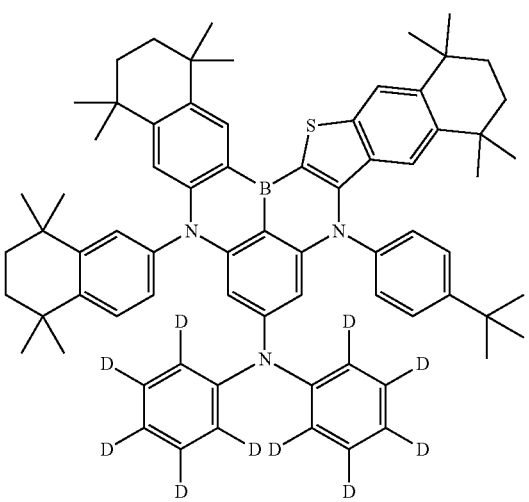

323
-continued
324
-continued
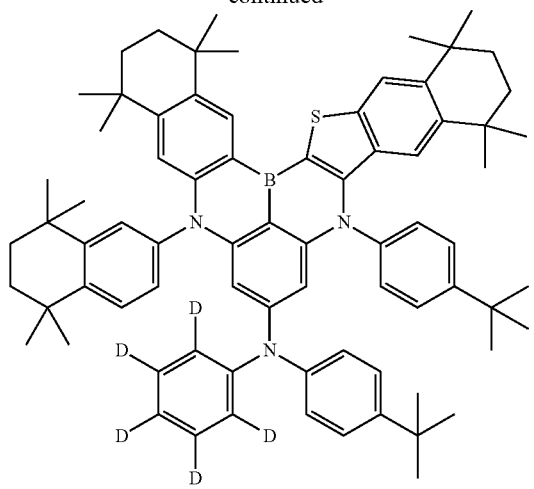
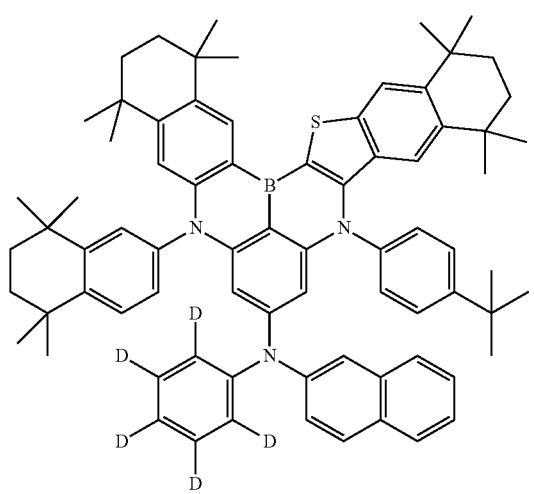
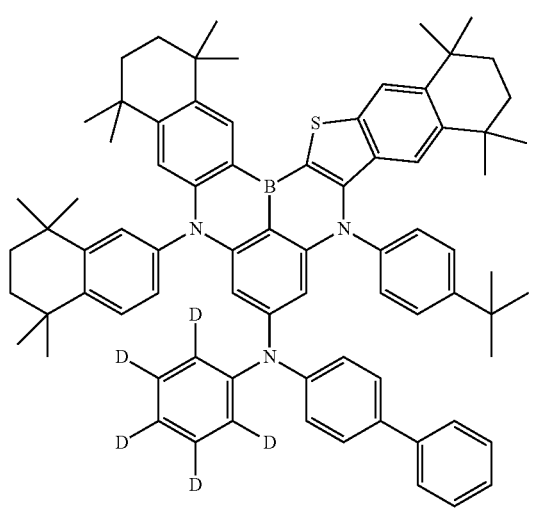
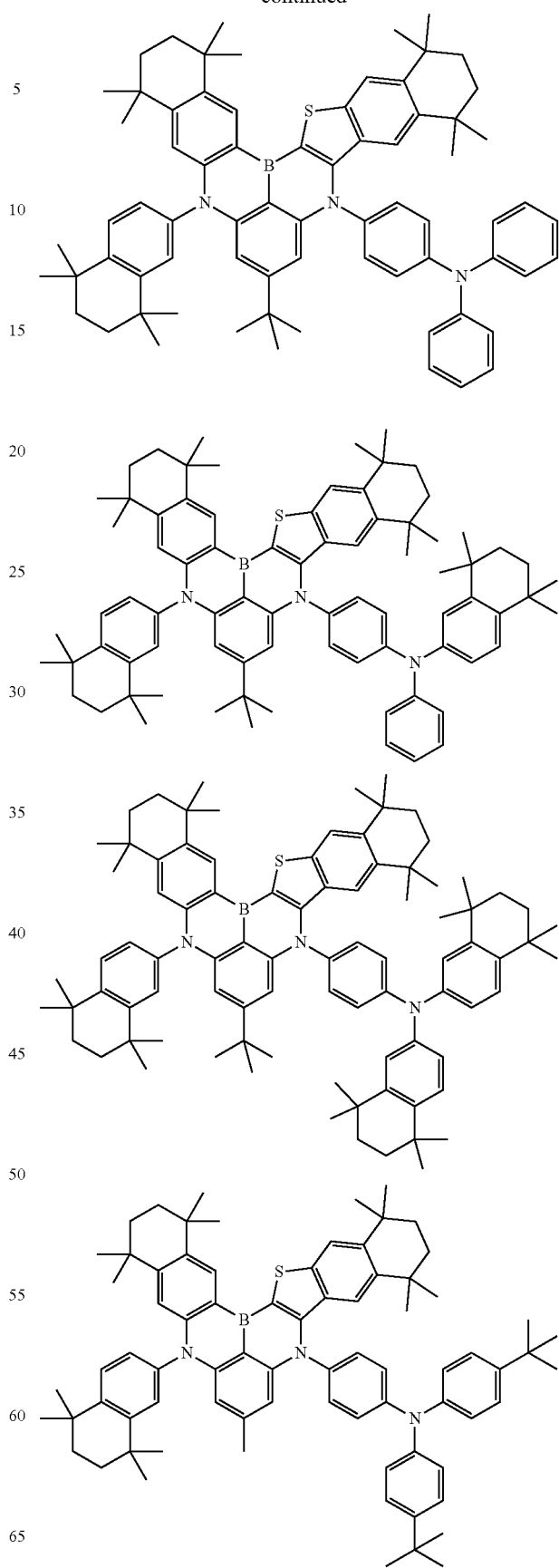

325
-continued
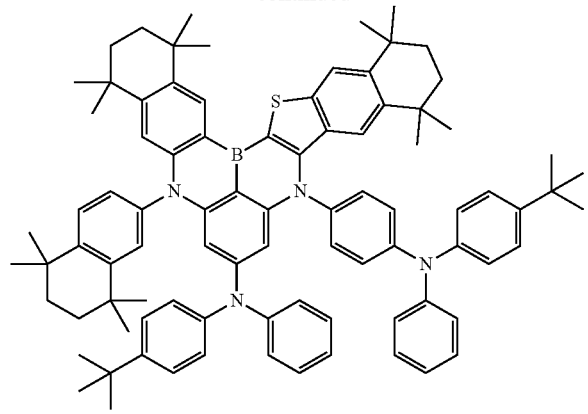
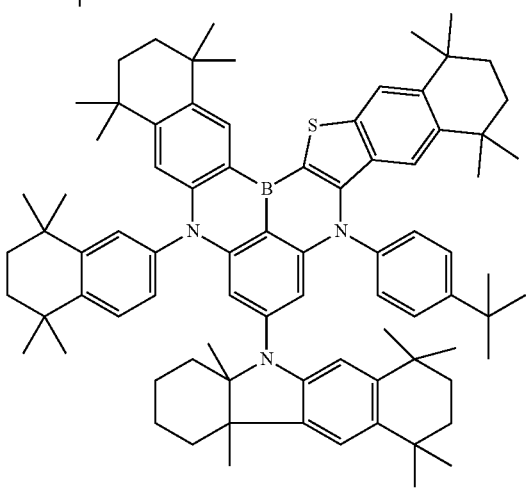
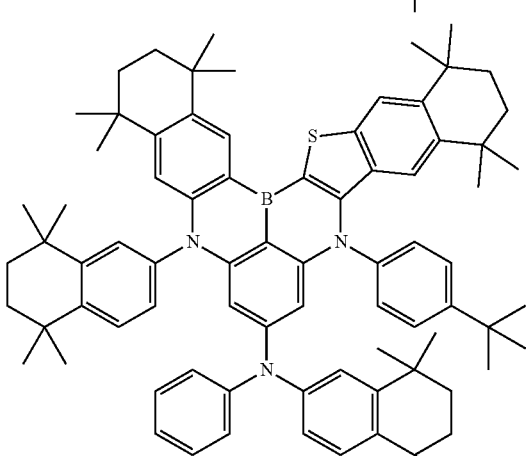
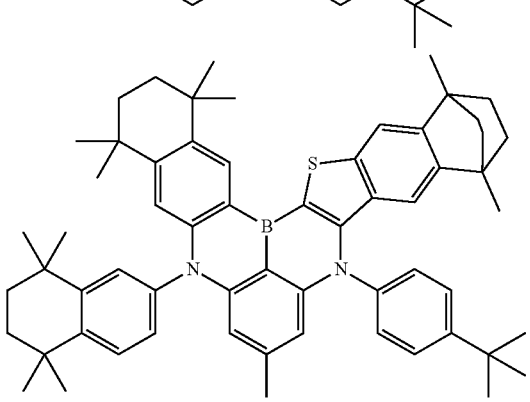
326
-continued
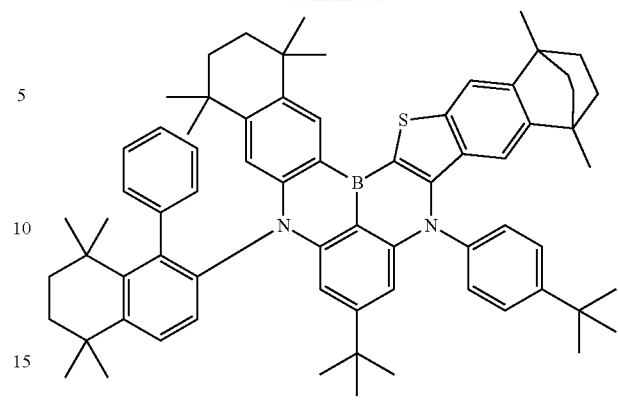
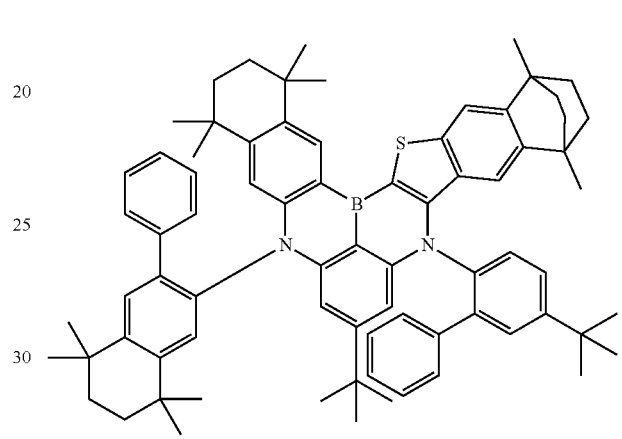
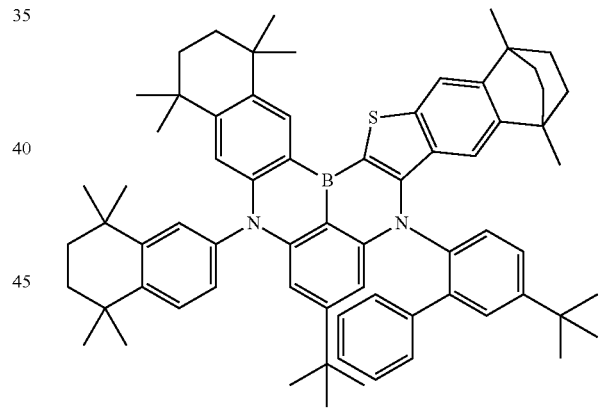
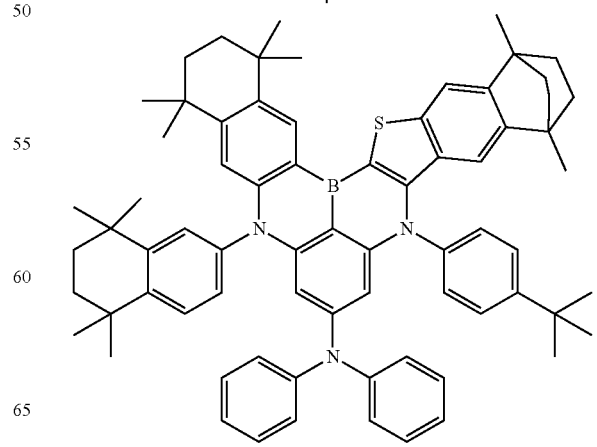

327
-continued
328
-continued
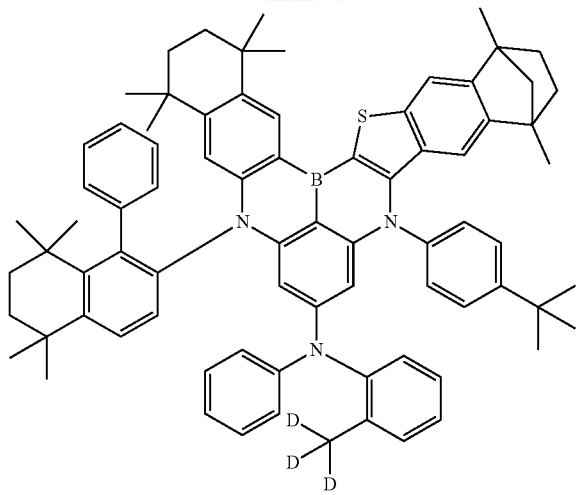
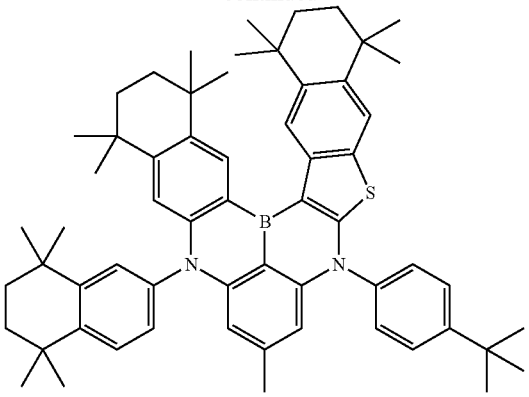
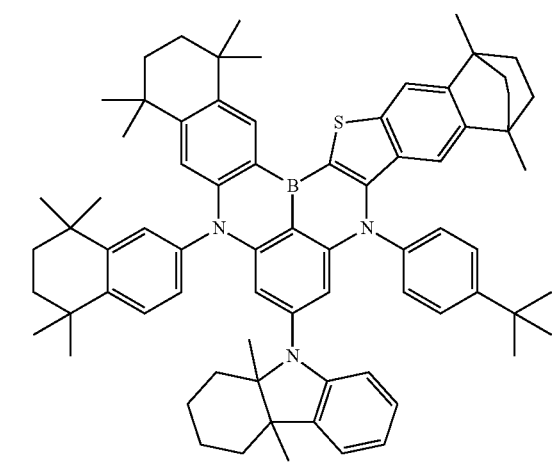
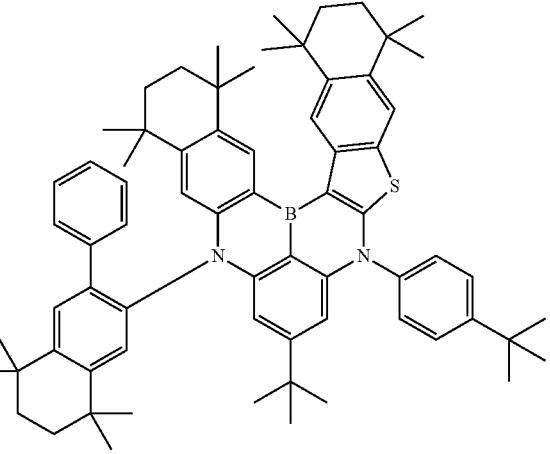
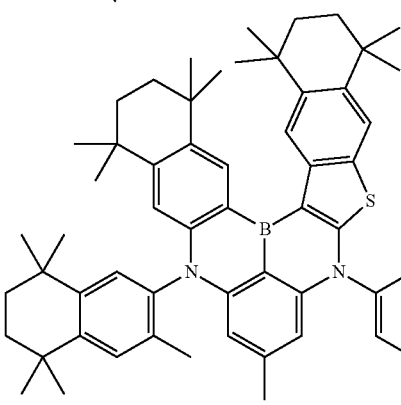
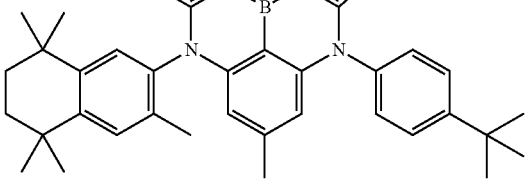
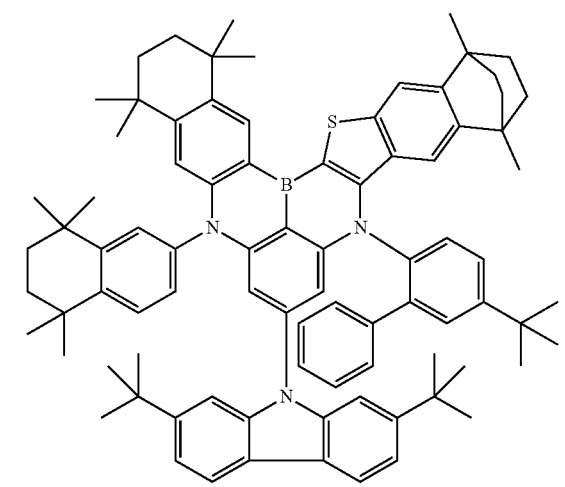
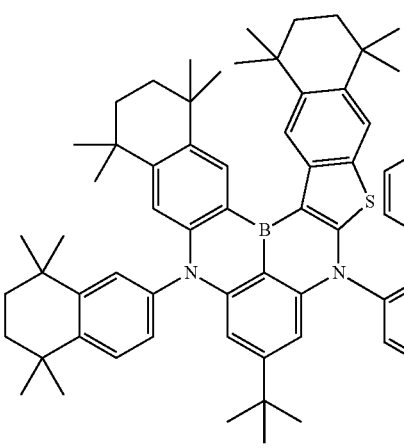

329
-continued
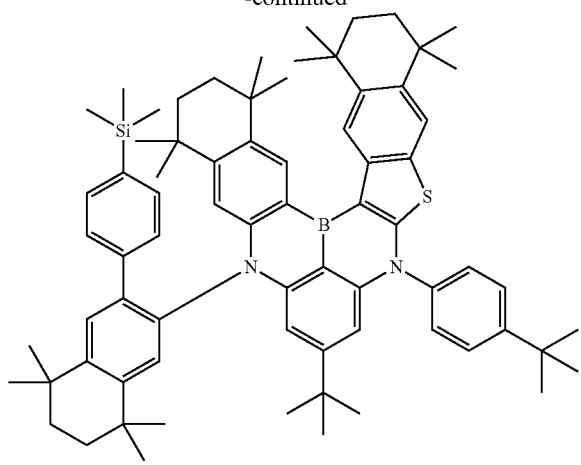
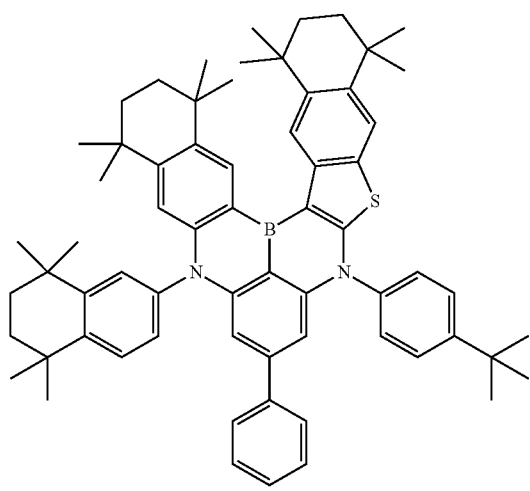
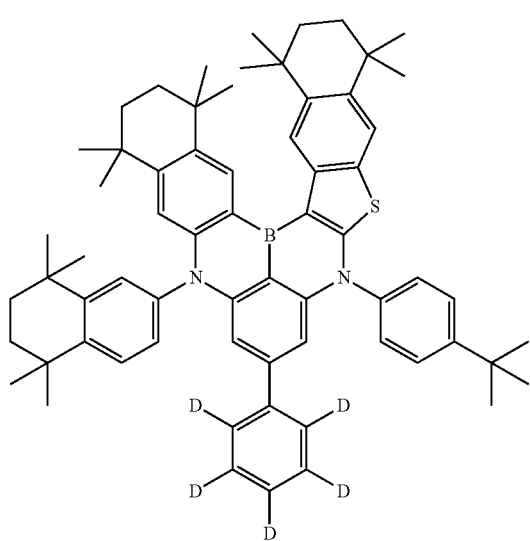
330
-continued
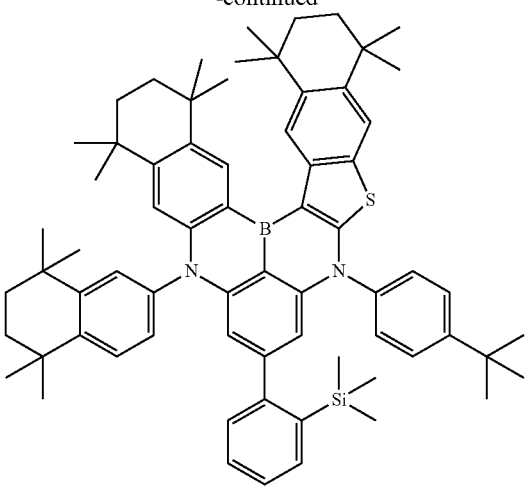
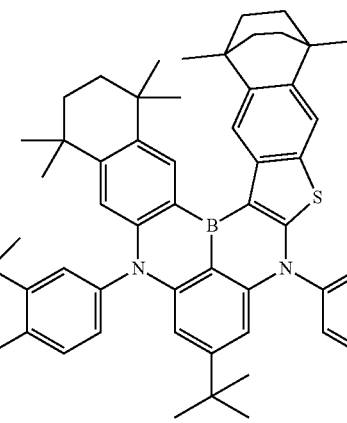
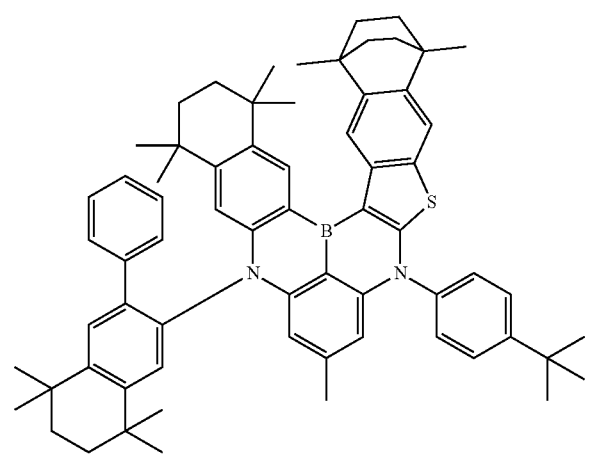

331
-continued
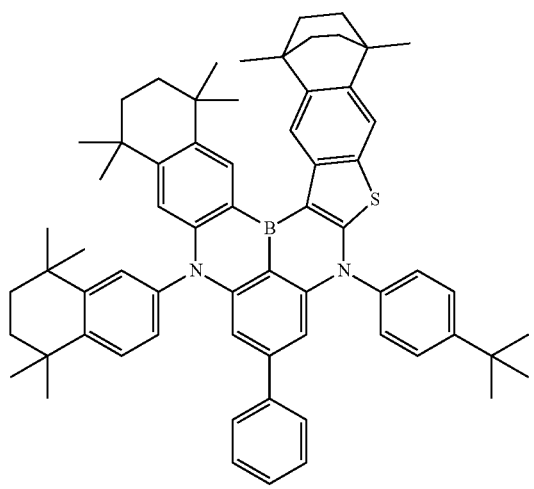
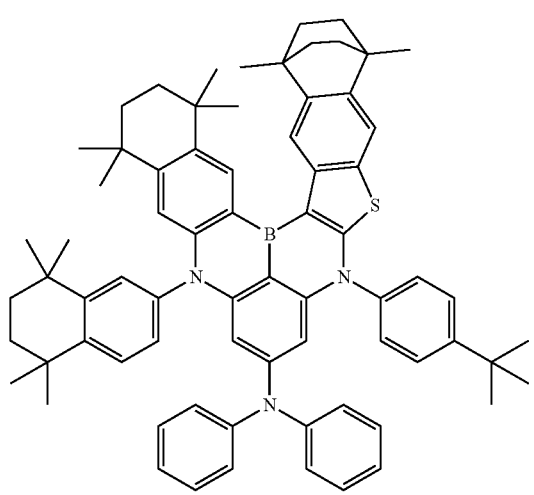
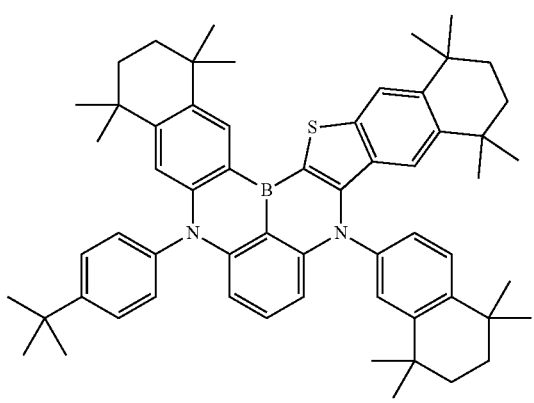
332
-continued
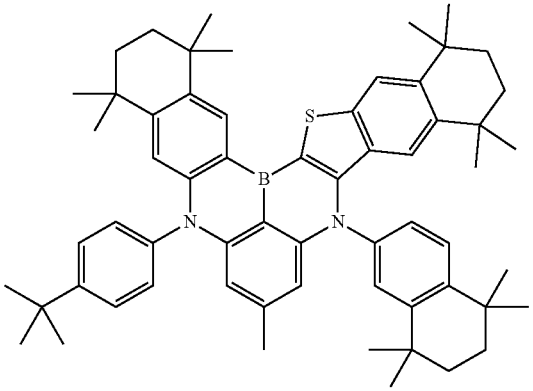
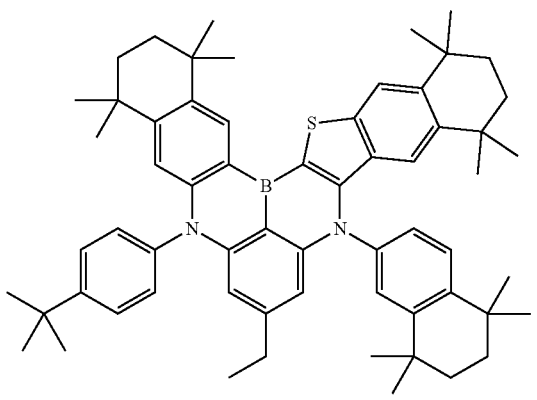
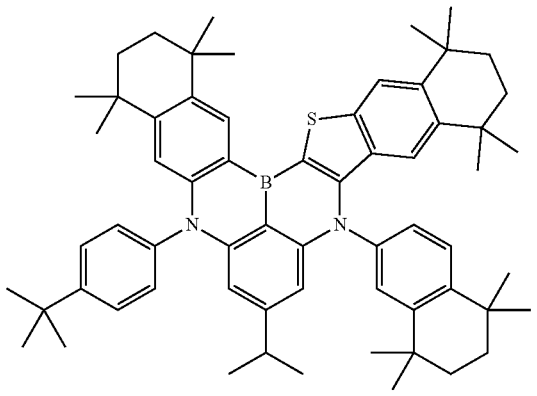
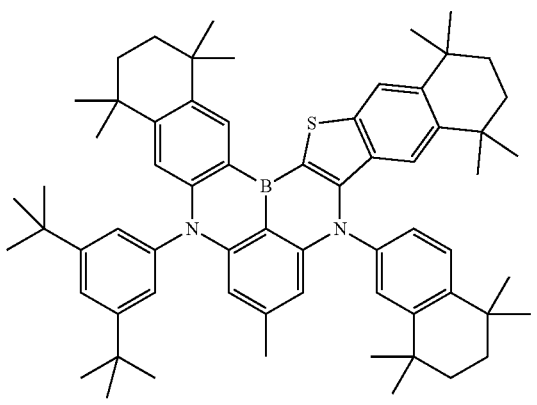

333
-continued
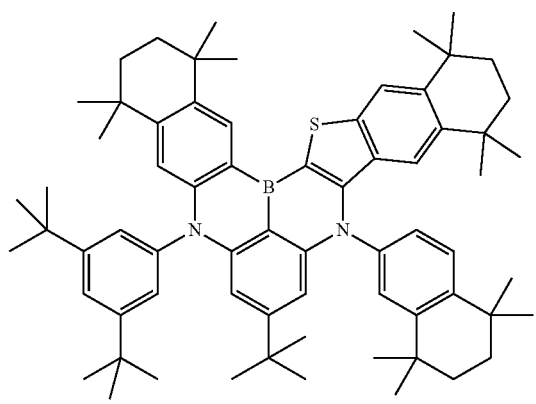
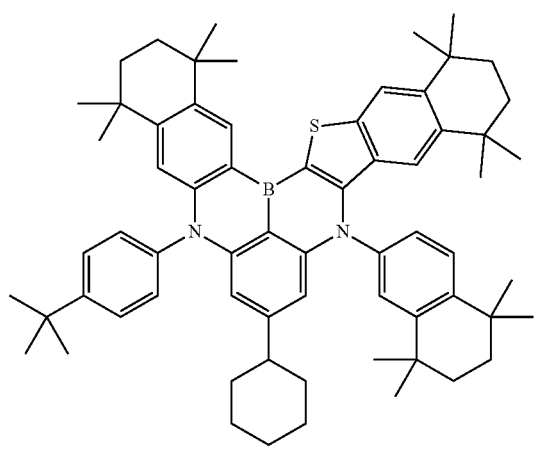
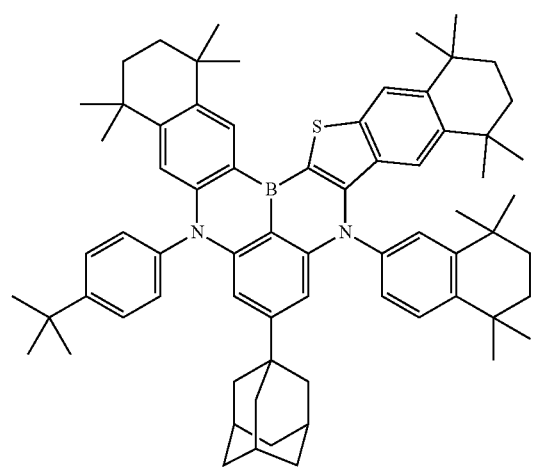
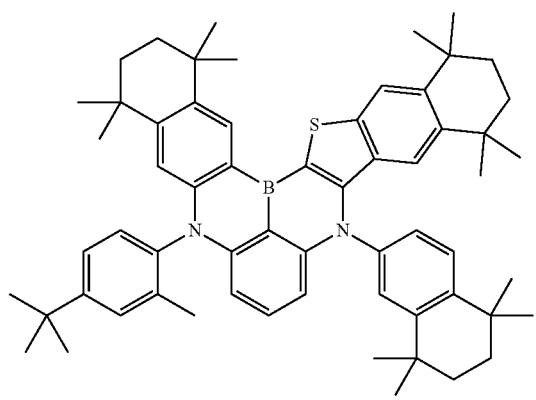
334
-continued
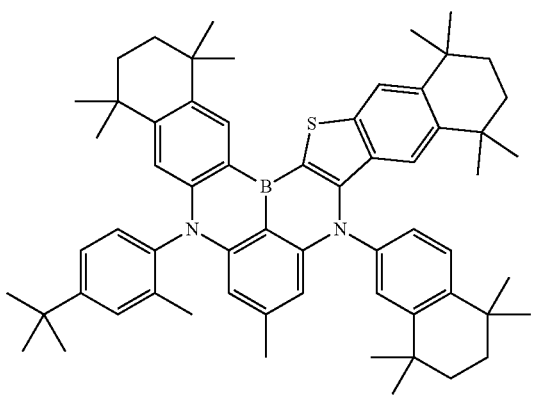
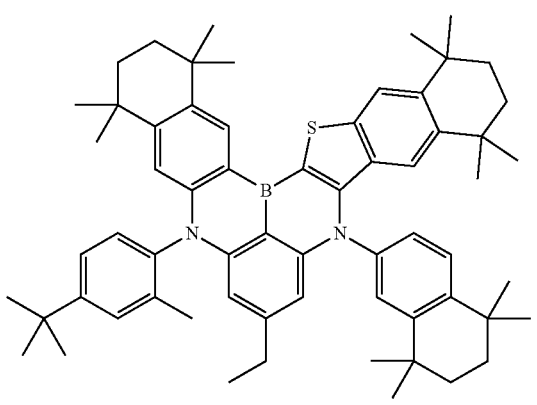
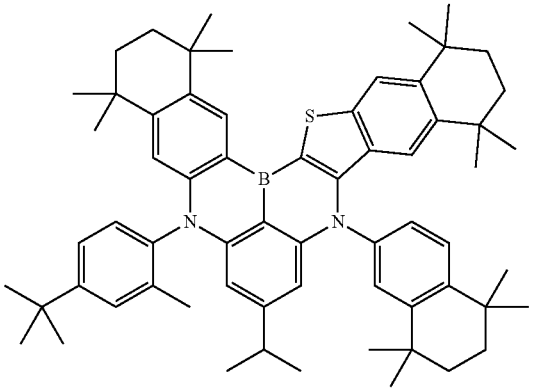
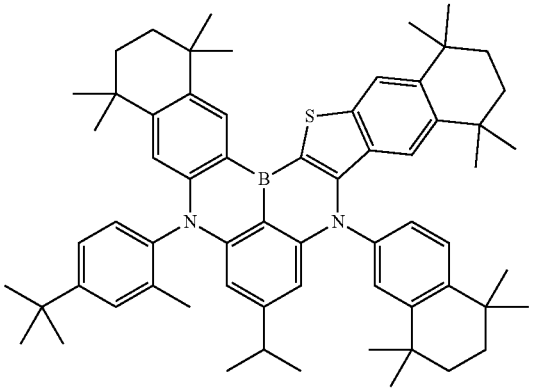

335
-continued
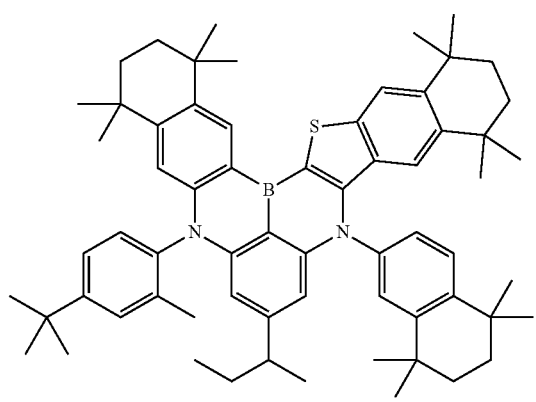
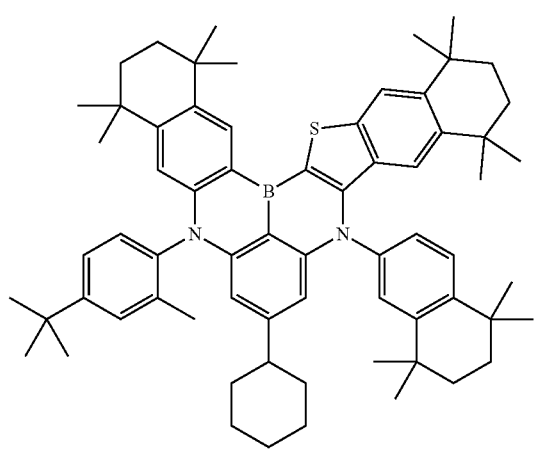
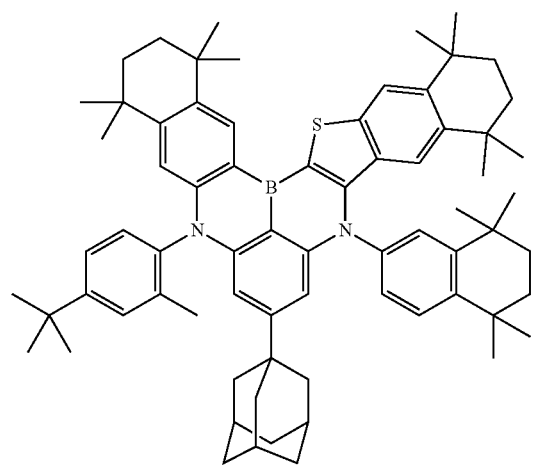
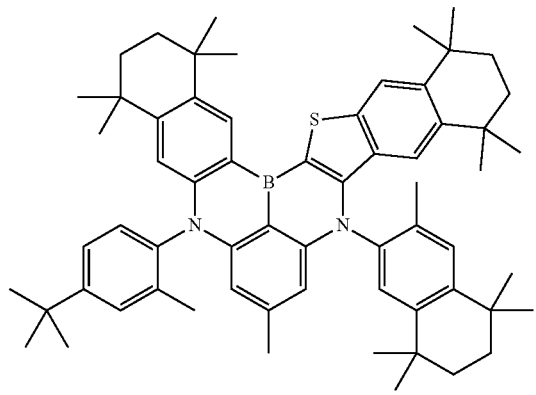
336
-continued
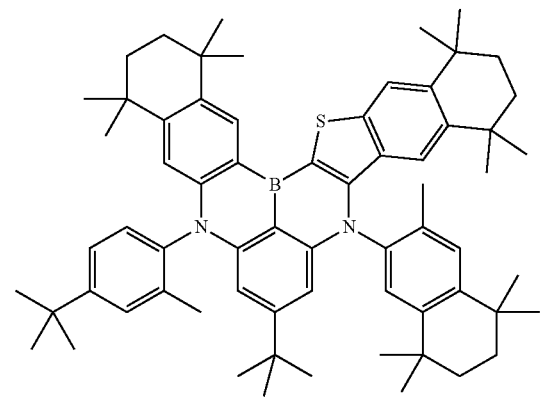
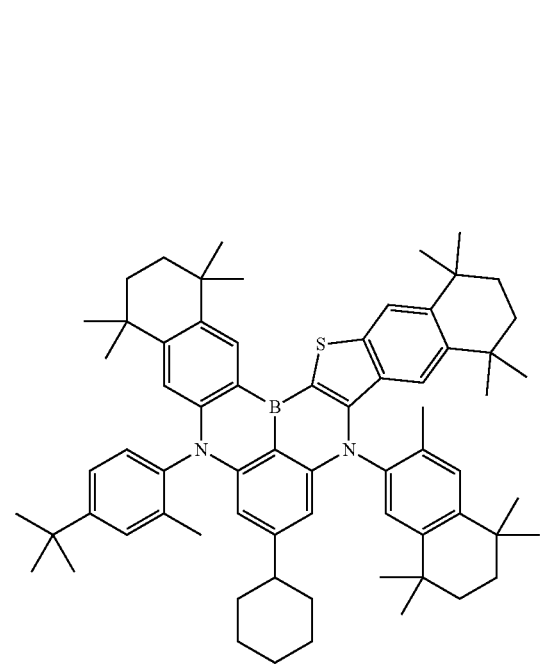
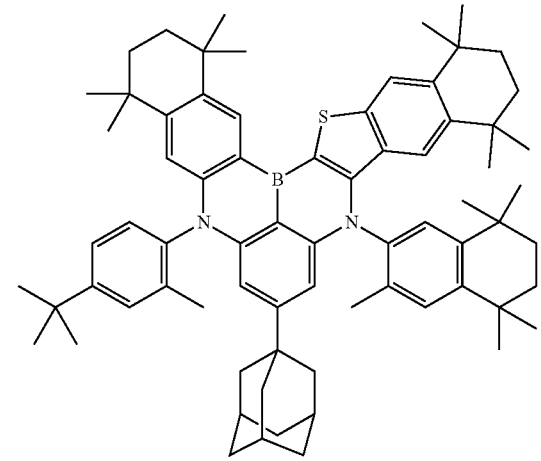

337
-continued
338
-continued
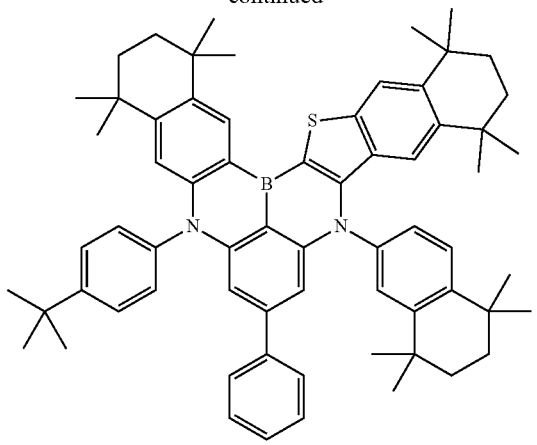
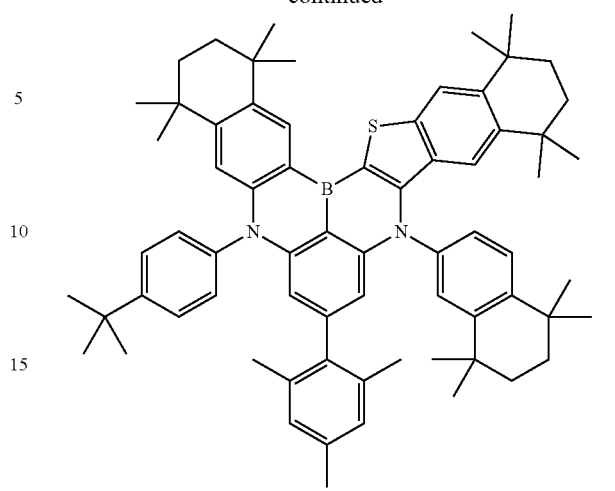
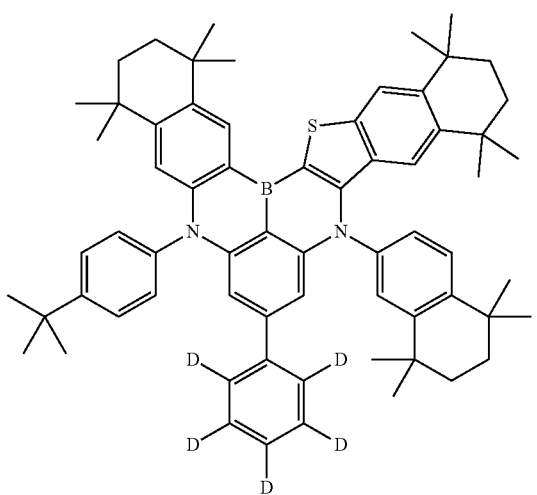
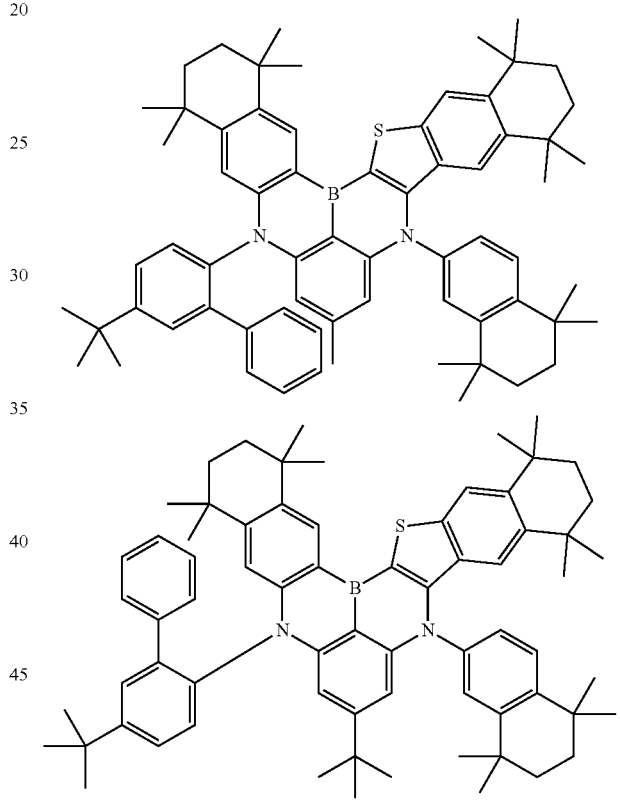
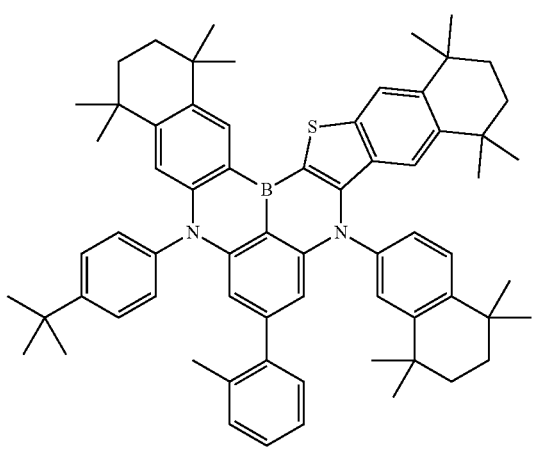
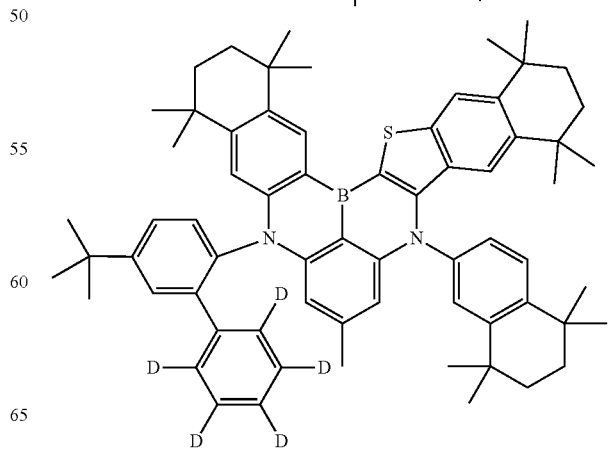

339
-continued
340
-continued
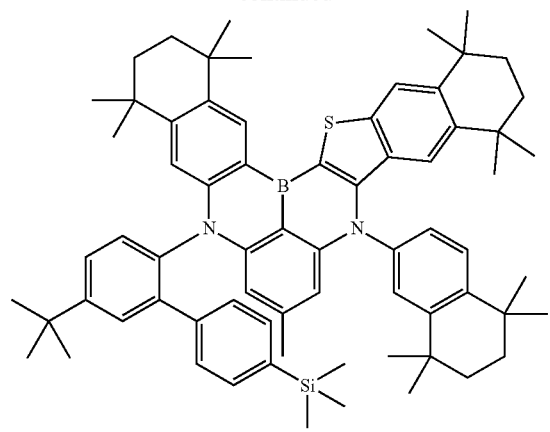
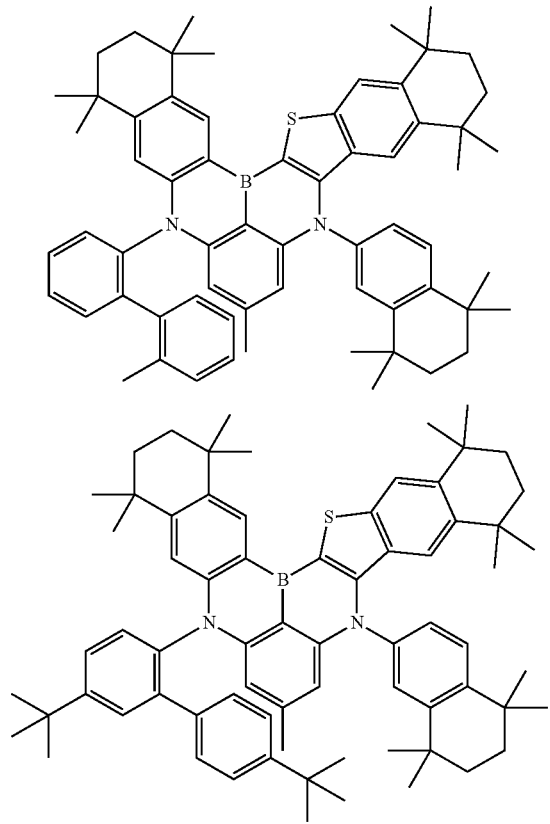
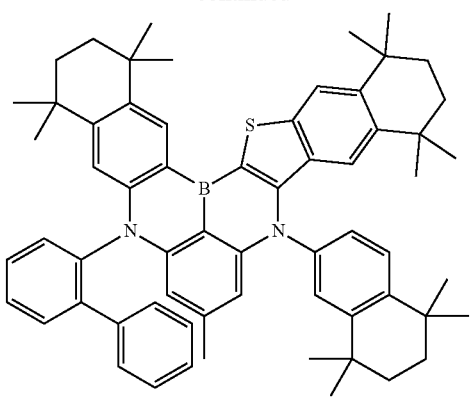
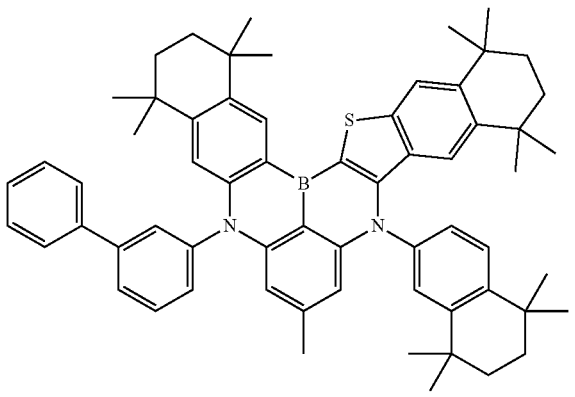
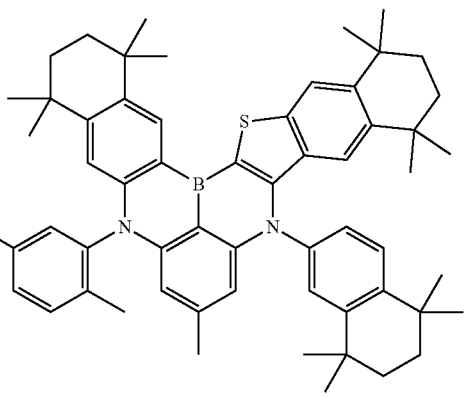

341
-continued
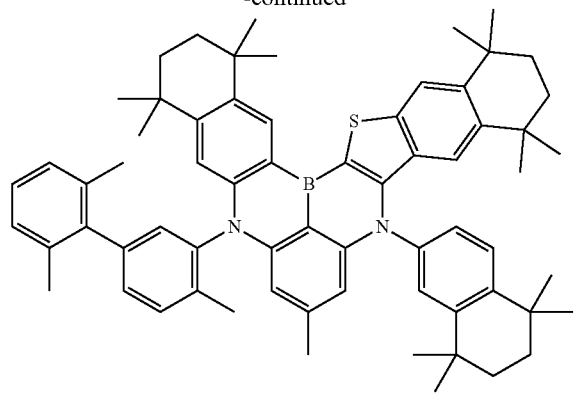
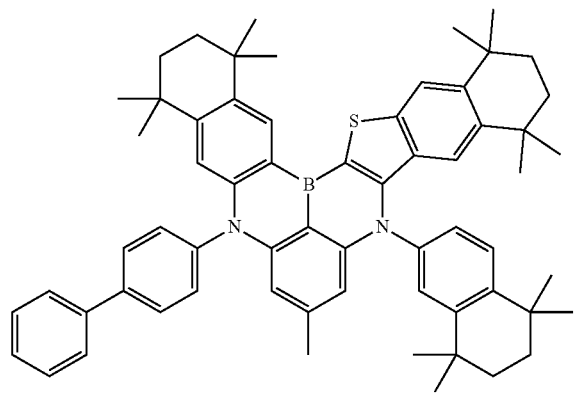
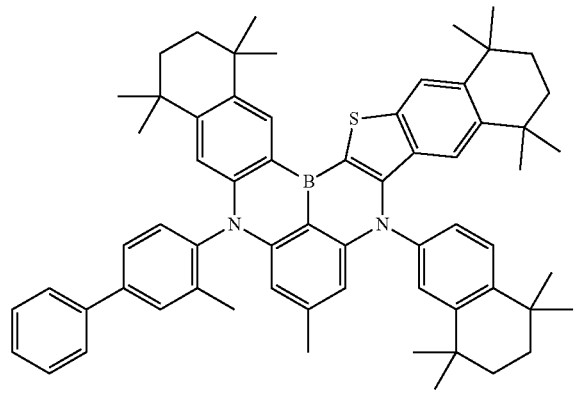
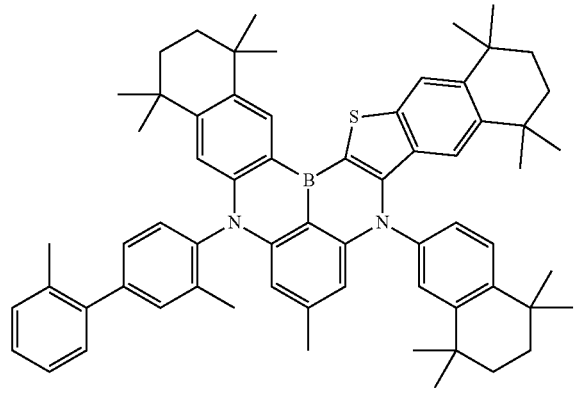
342
-continued
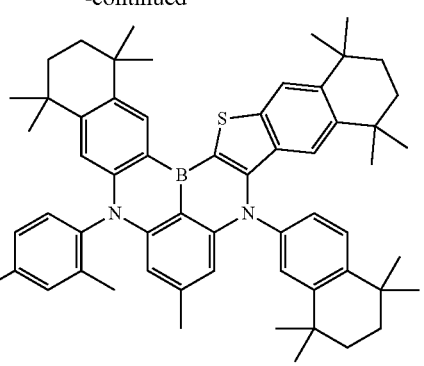
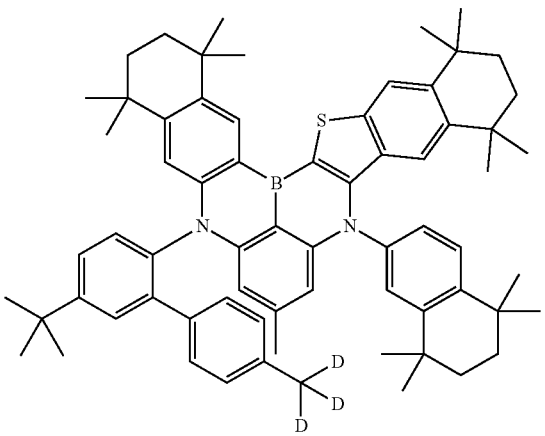
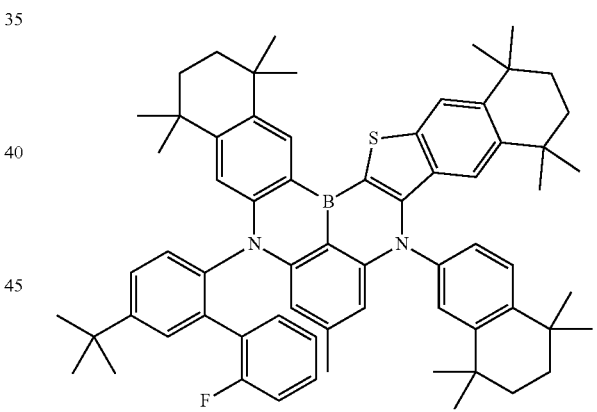
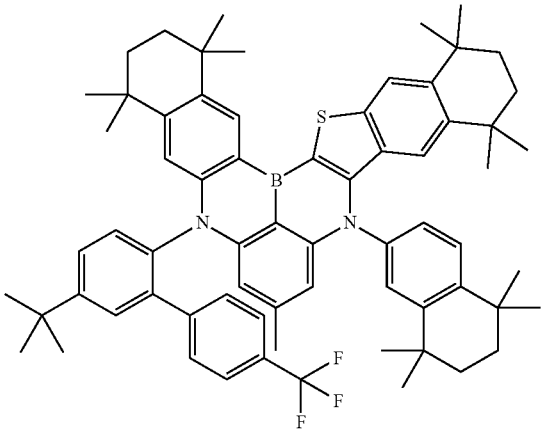

343
-continued
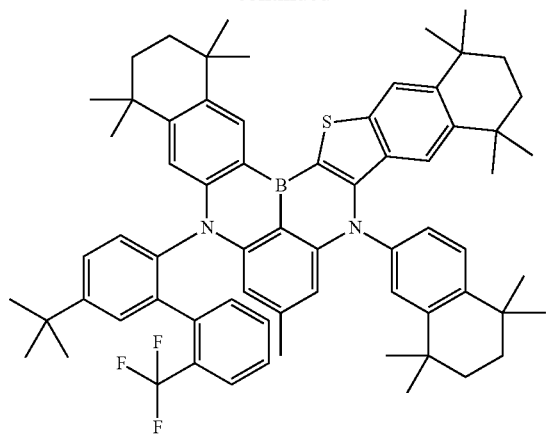
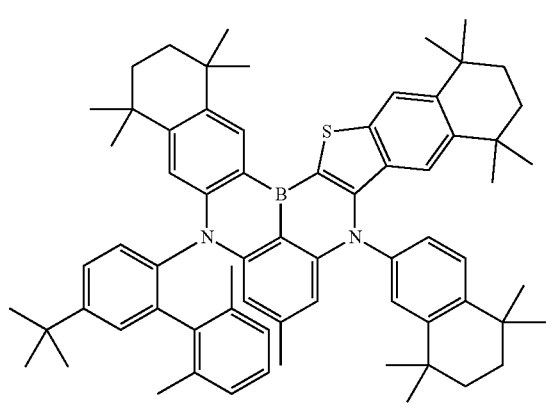
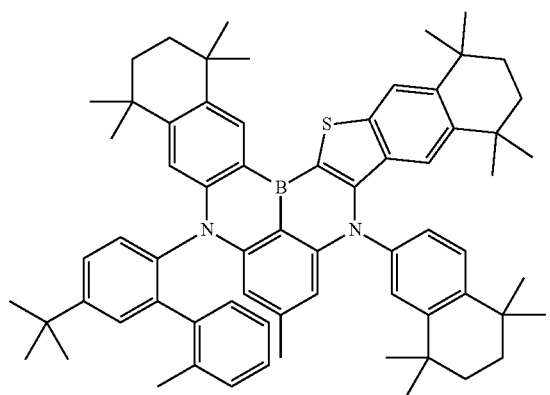
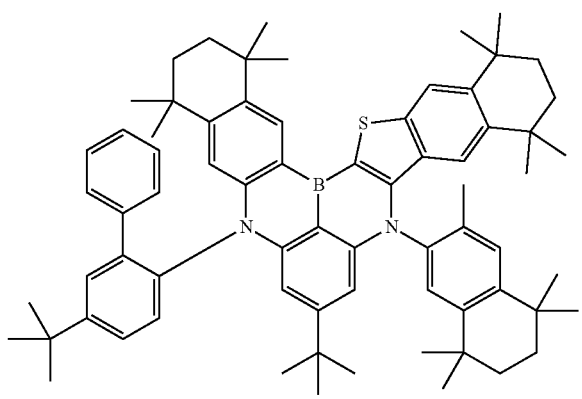
344
-continued
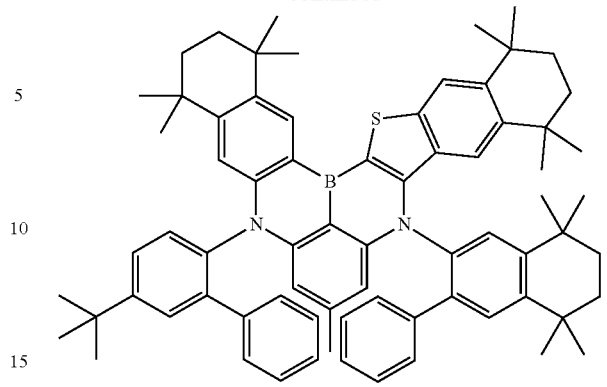
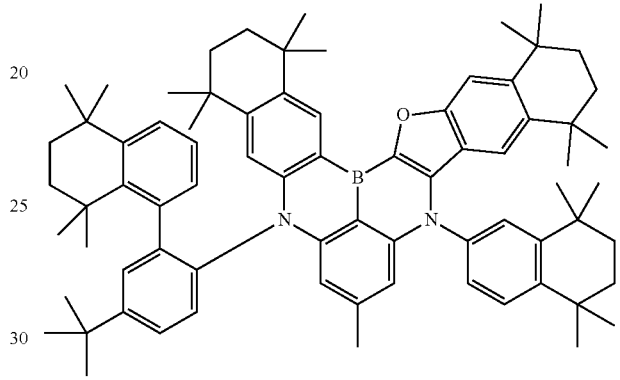
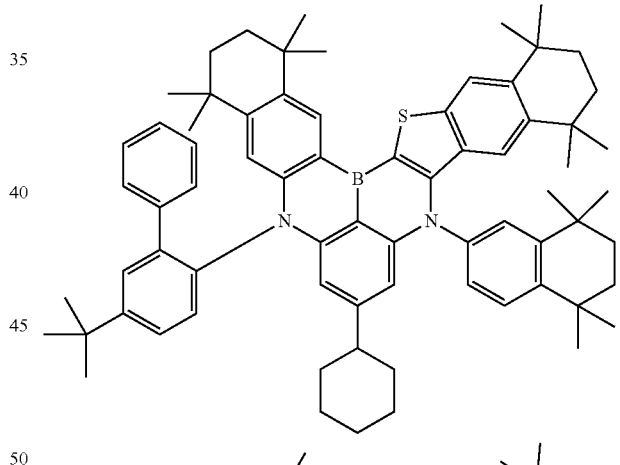
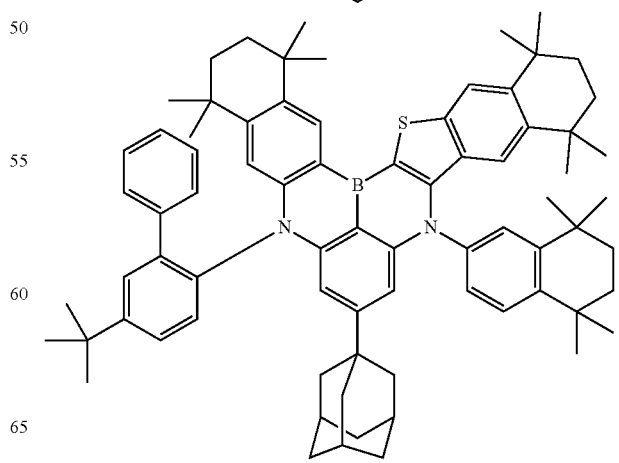

345
-continued
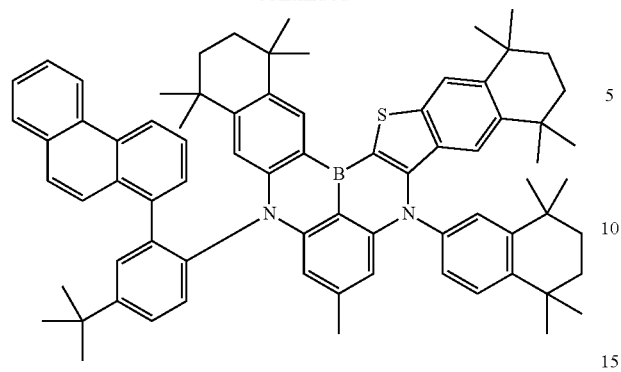
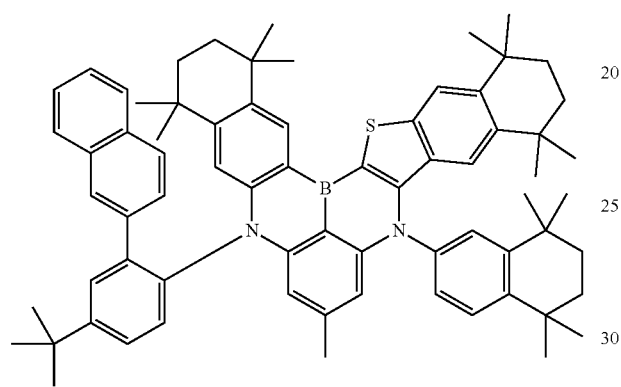
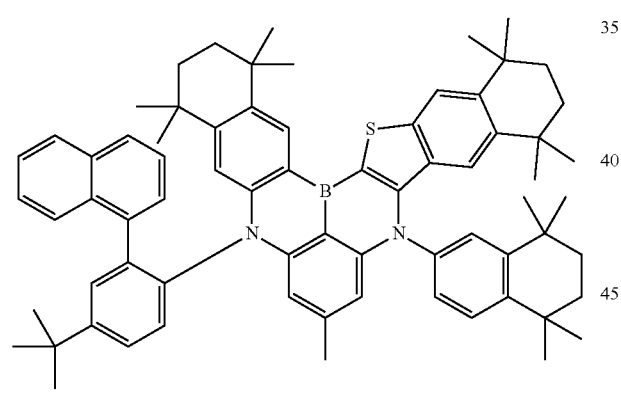
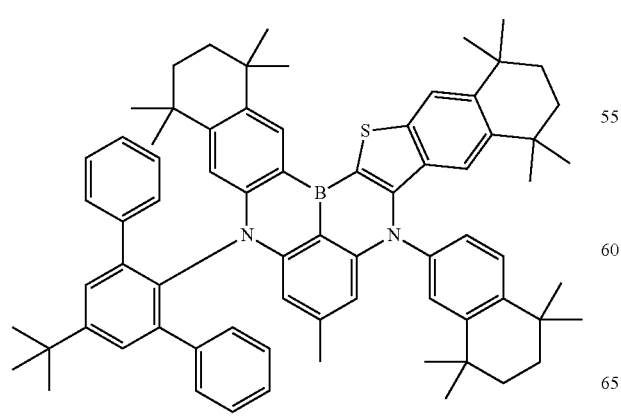
346
-continued
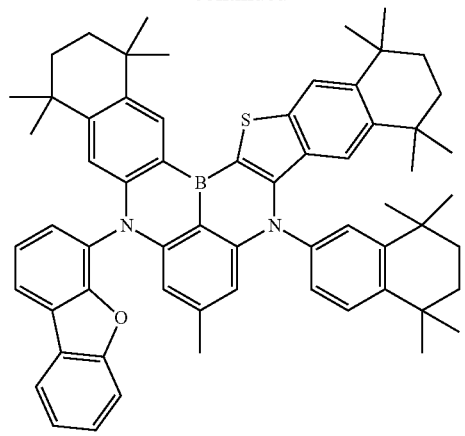
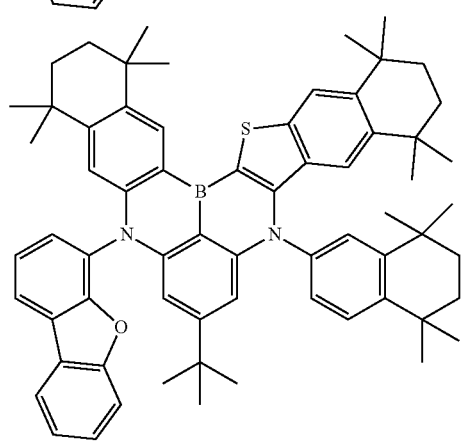
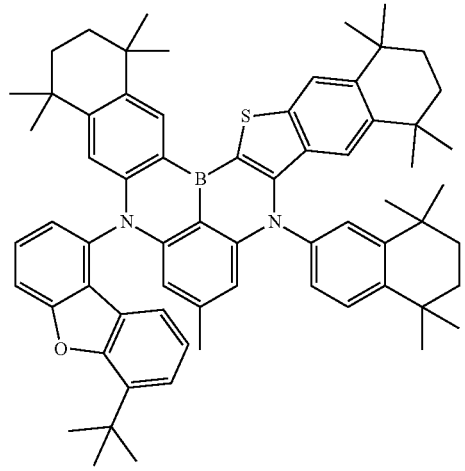
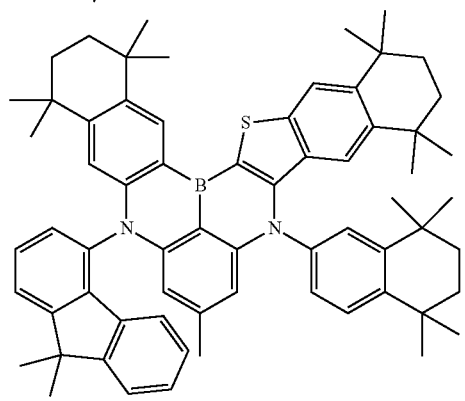

347
-continued
348
-continued
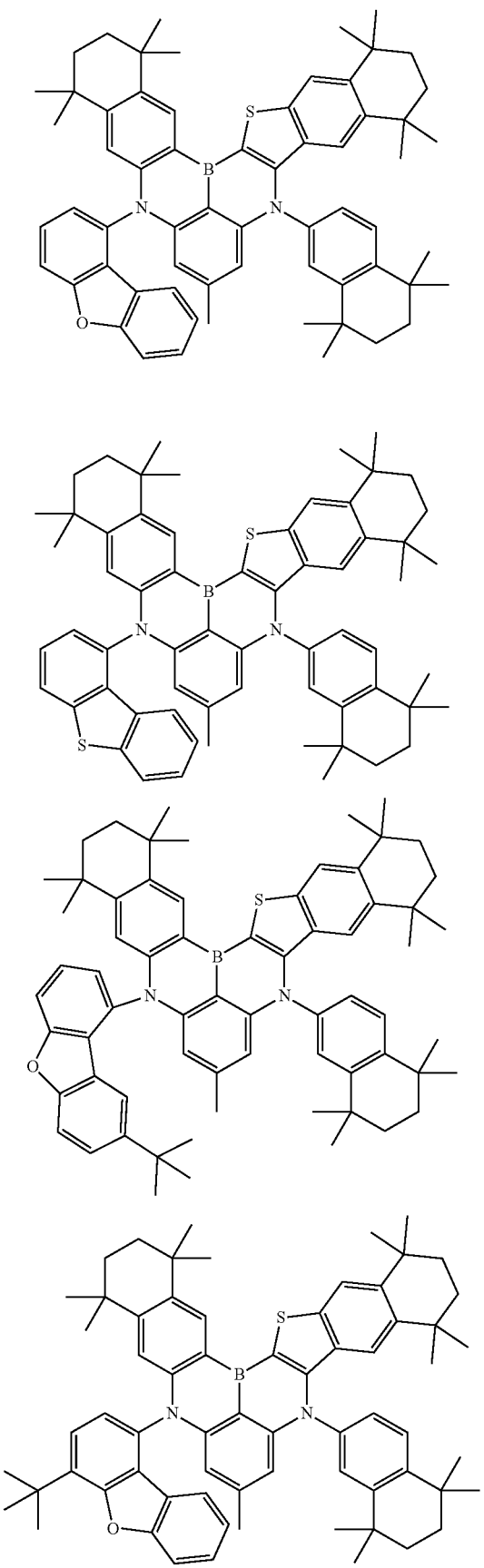
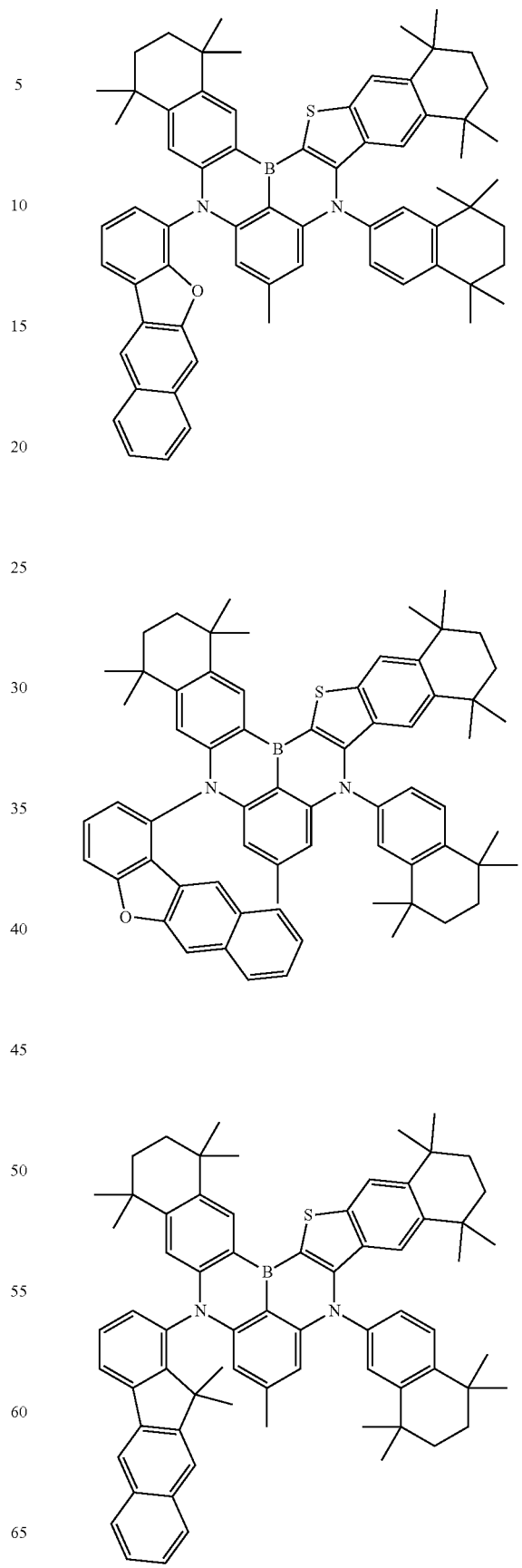

349
-continued
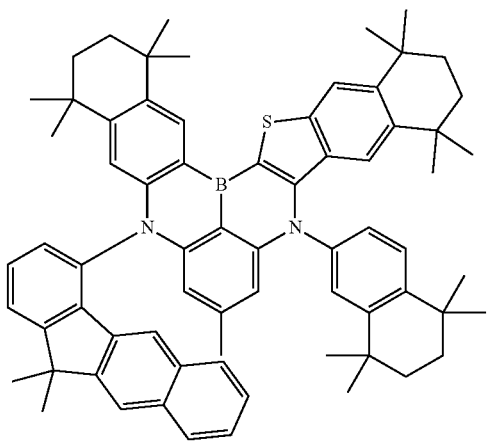
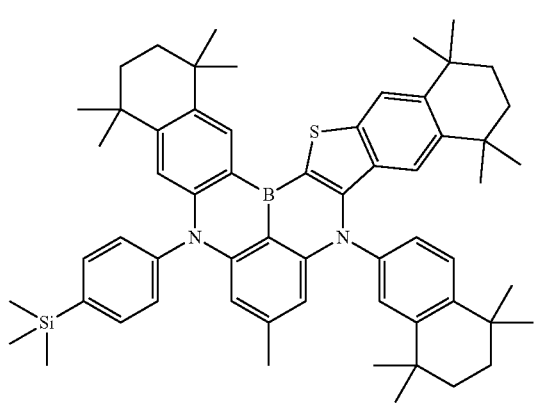
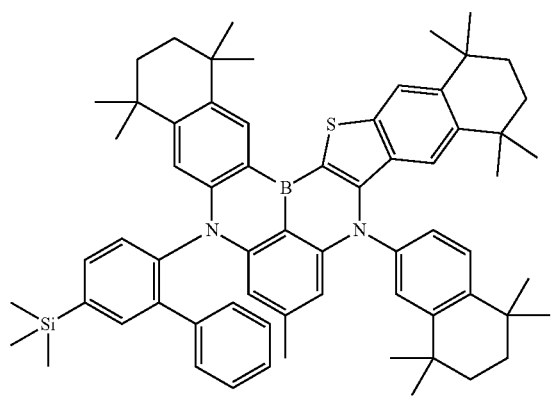
350
-continued
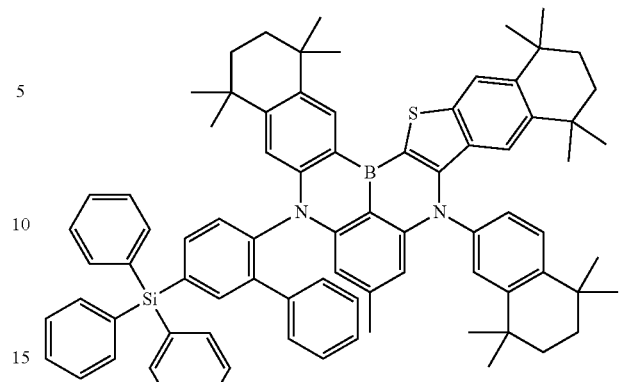
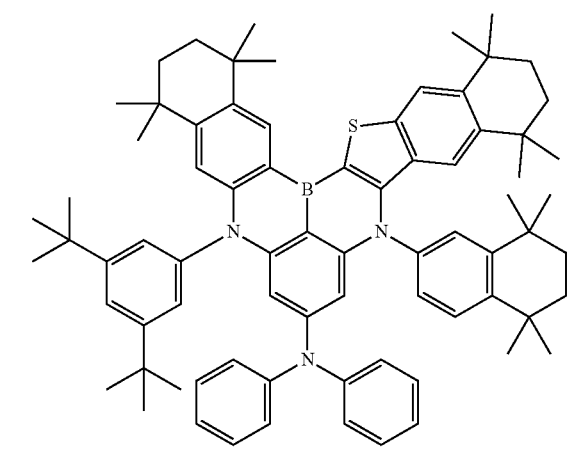
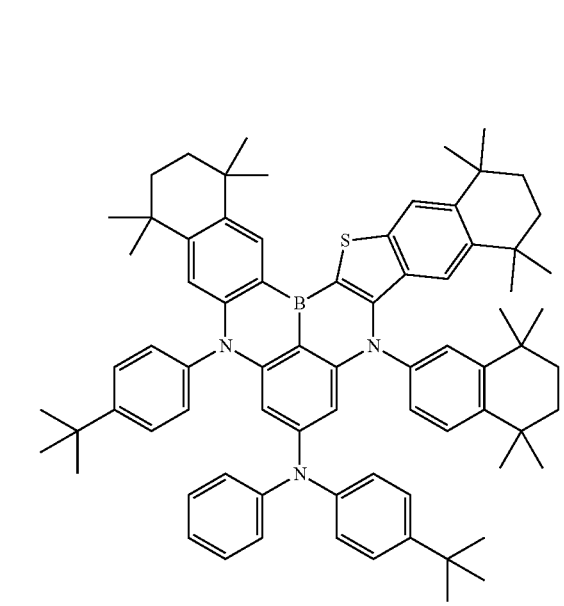

351
-continued
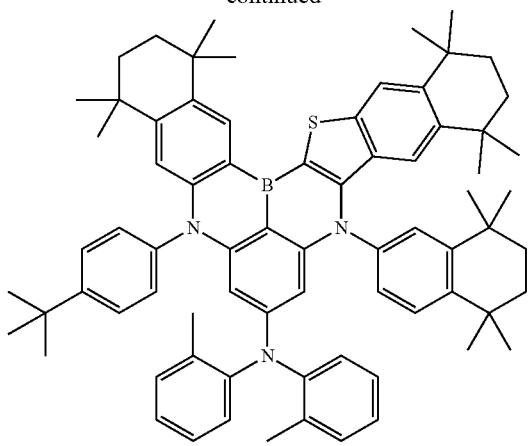
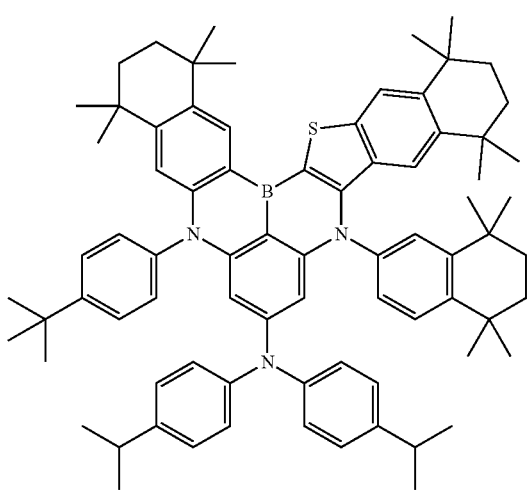
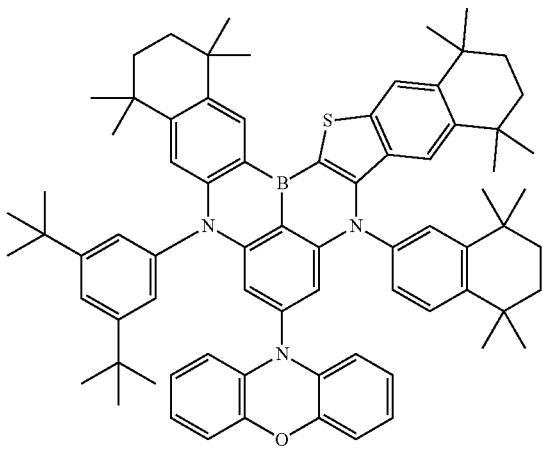
352
-continued
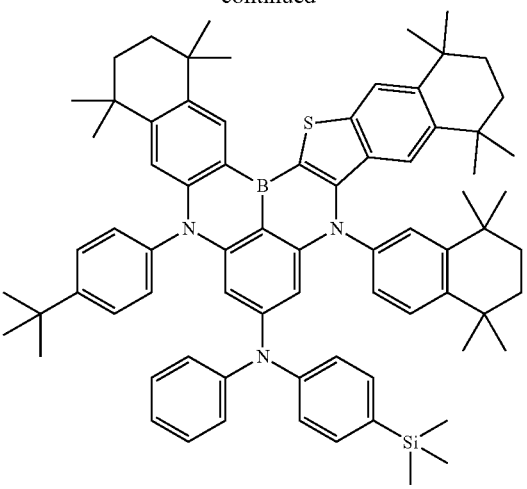
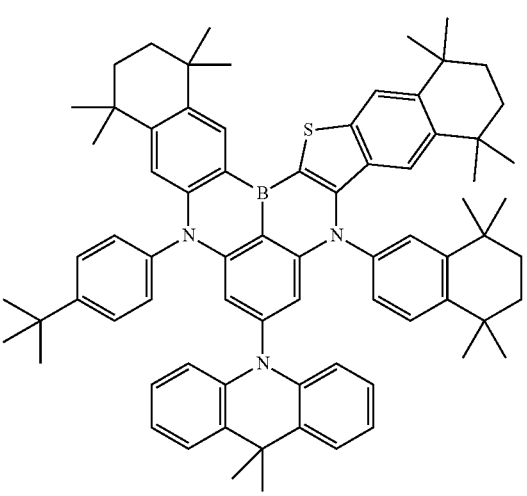
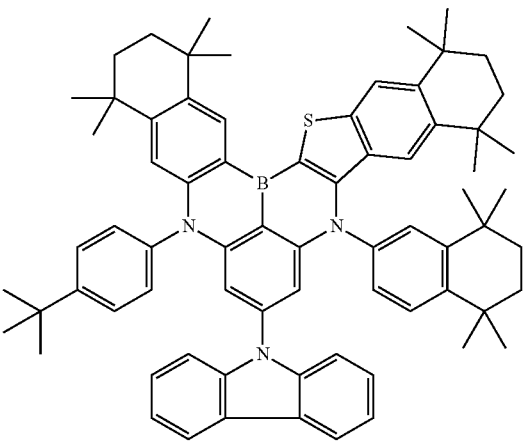

353
-continued
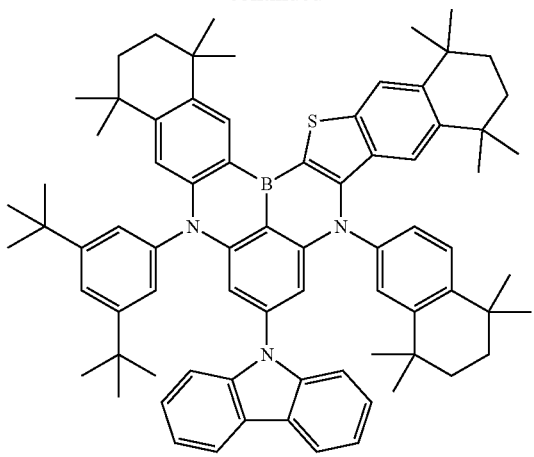
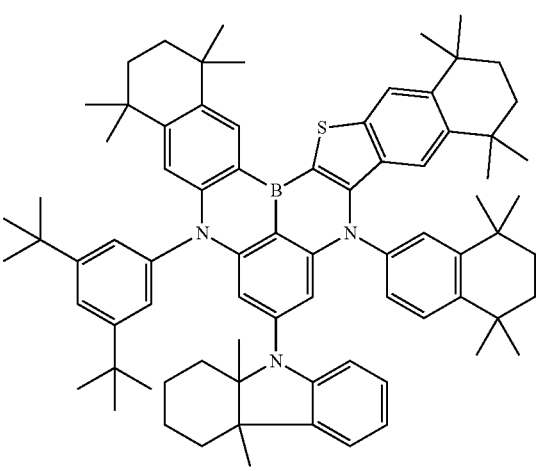
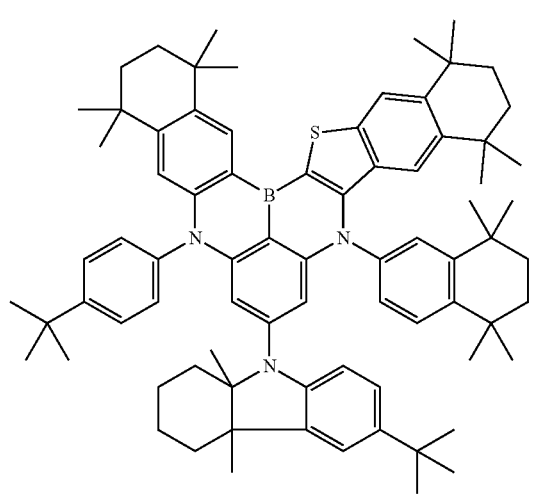
354
-continued
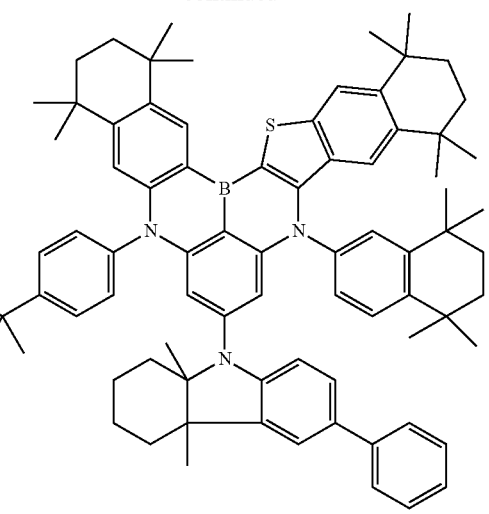
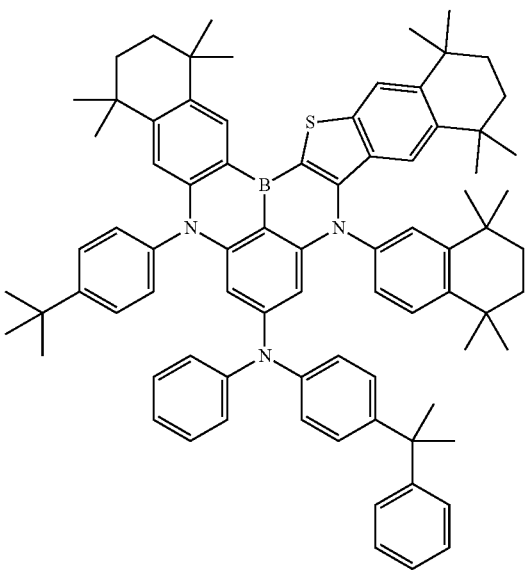
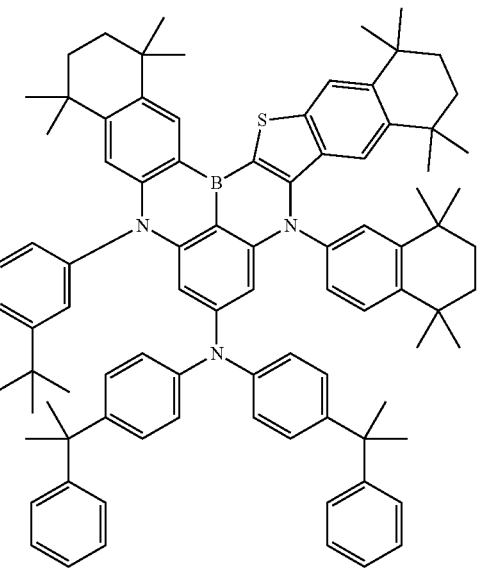

| 355 -continued | 356 -continued |
|---|---|
| 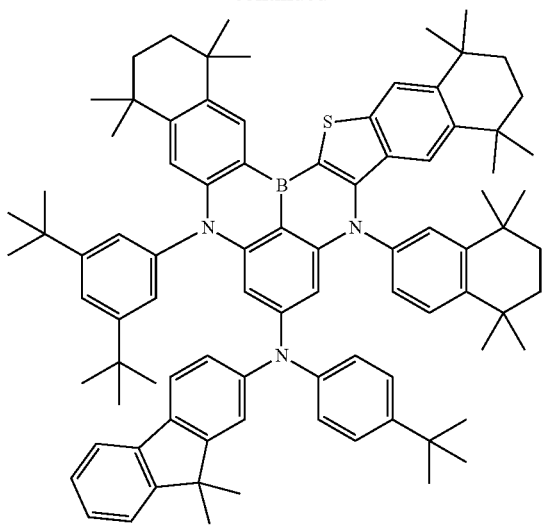 | 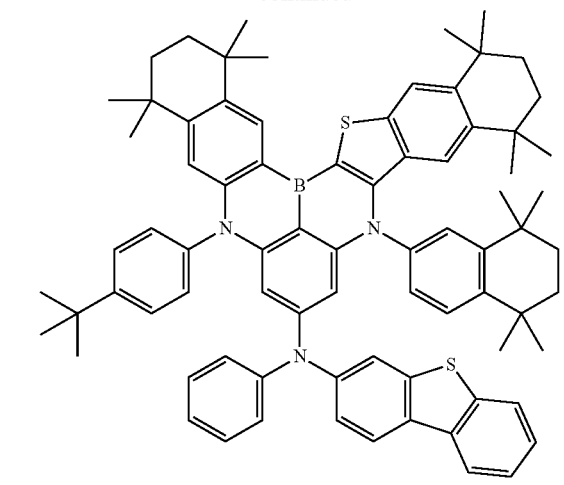 |
| 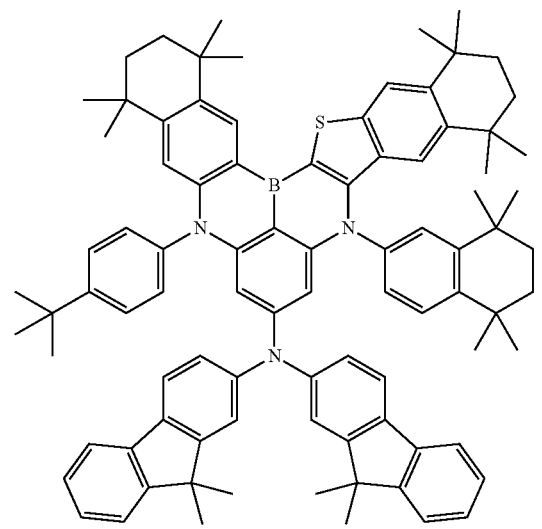 | 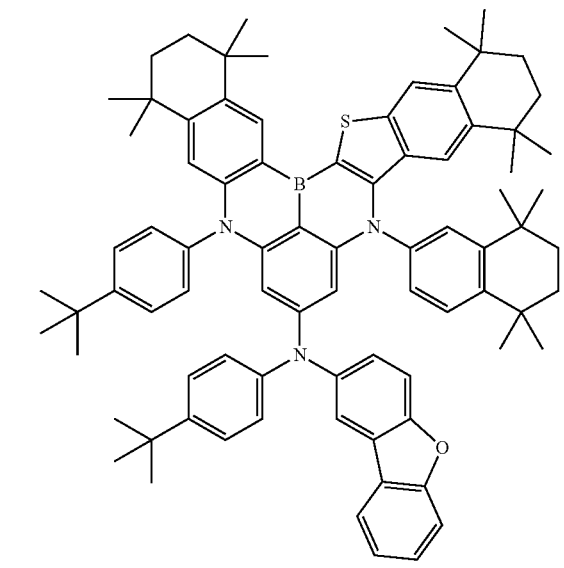 |
| 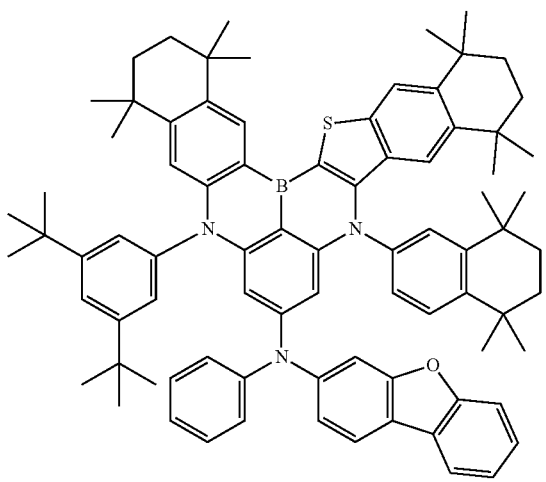 | 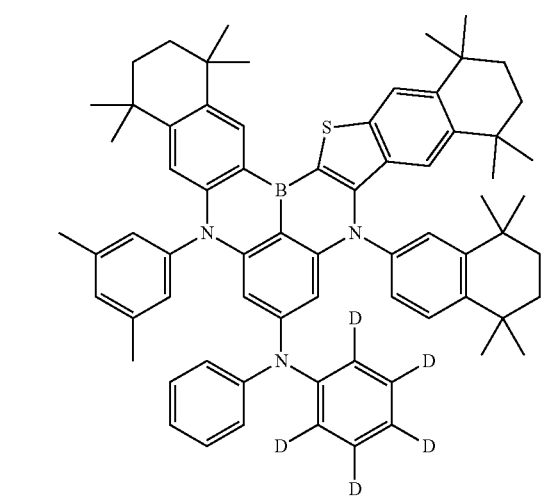 |

357
-continued
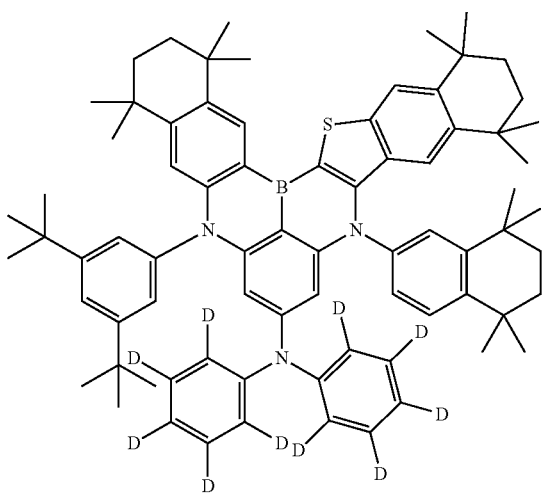
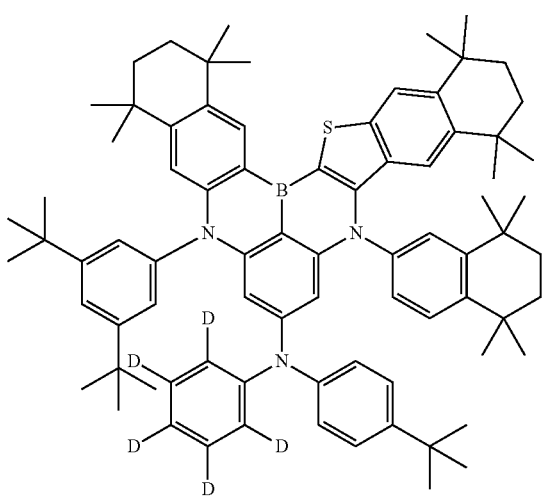
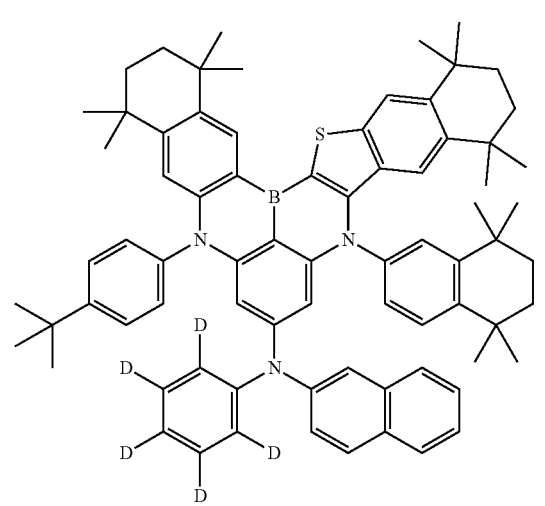
358
-continued
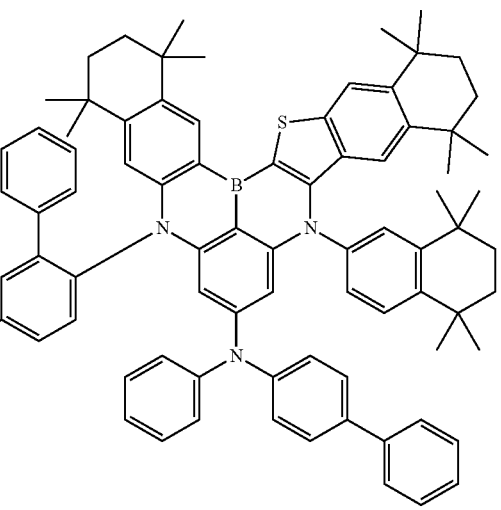
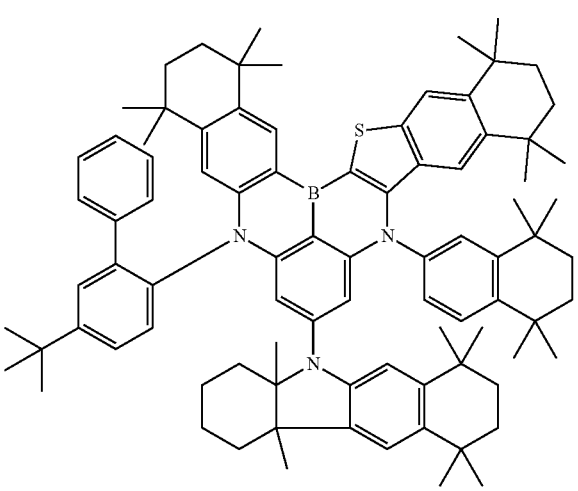
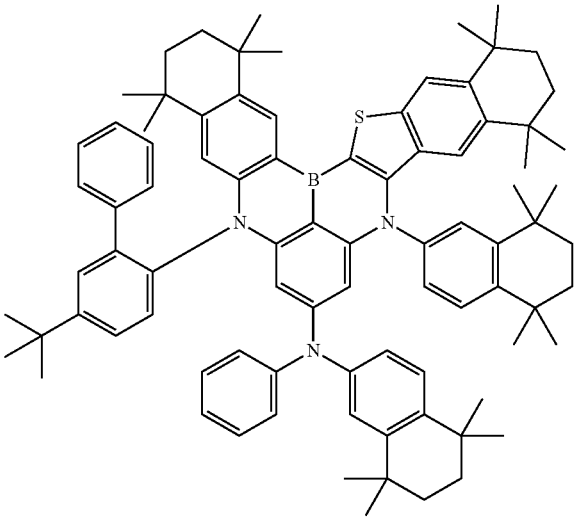

359
-continued
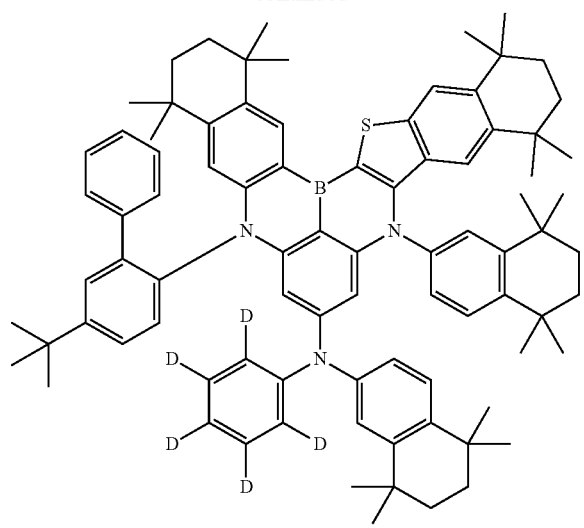
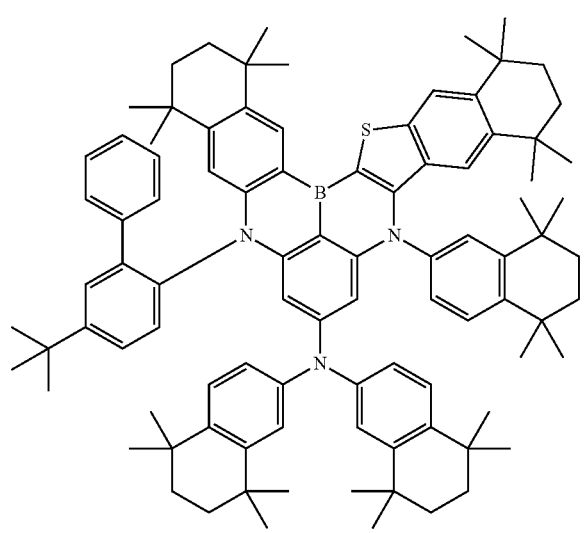
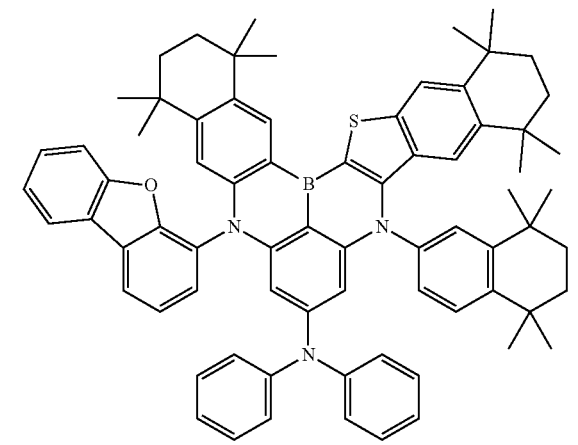
360
-continued
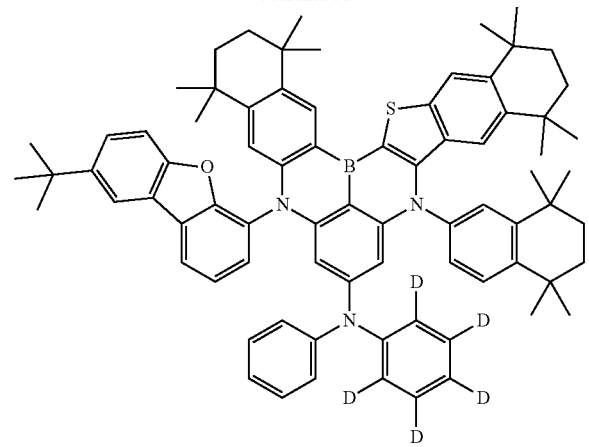
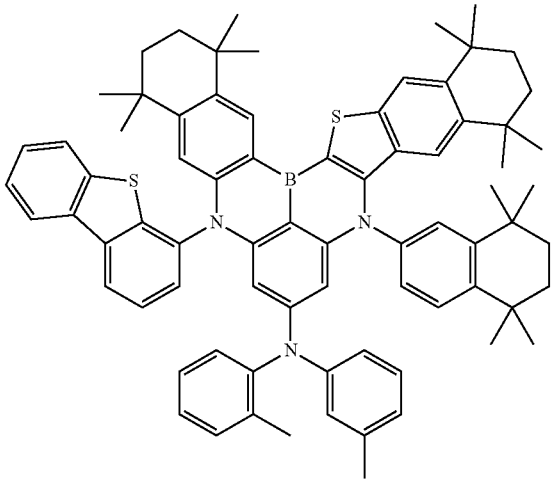
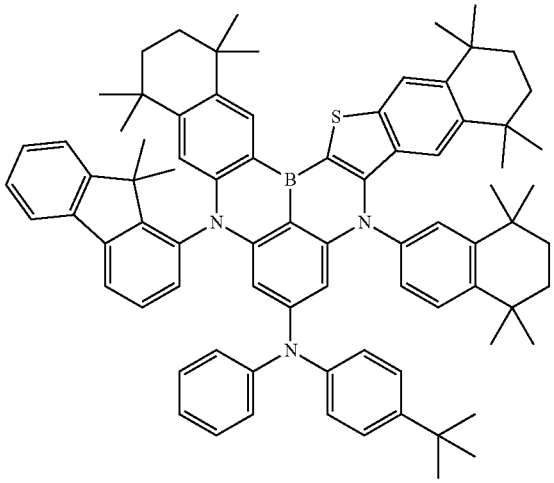

361
-continued
362
-continued
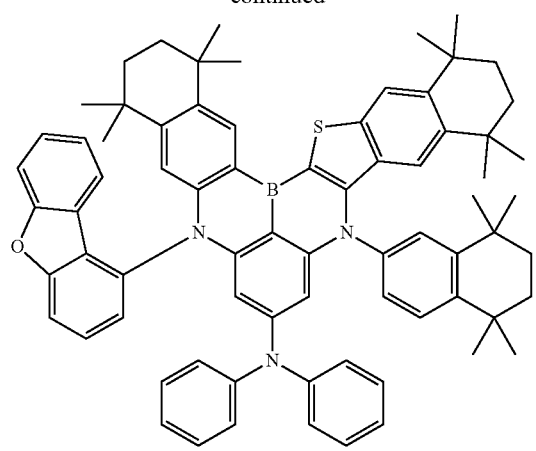
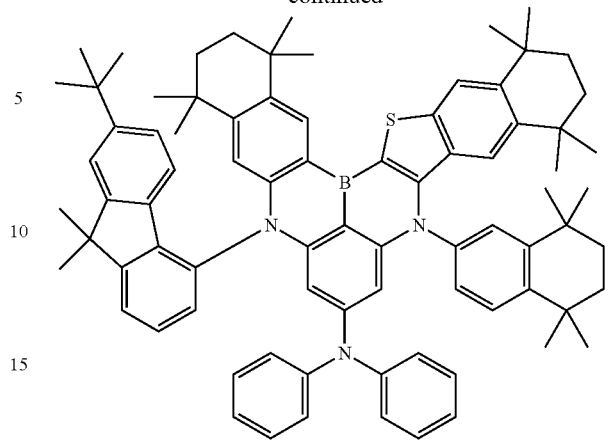
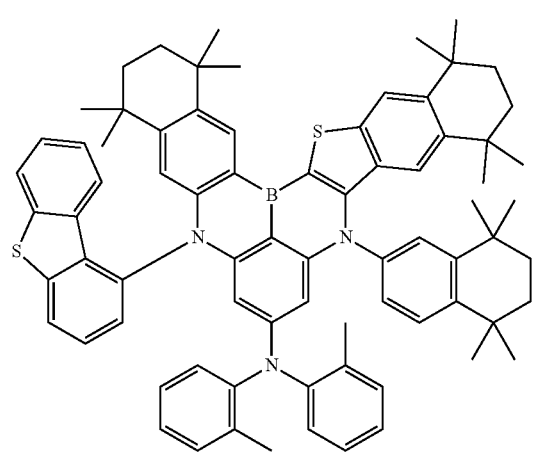
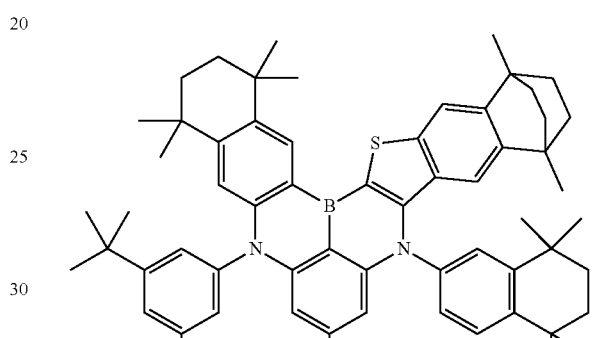
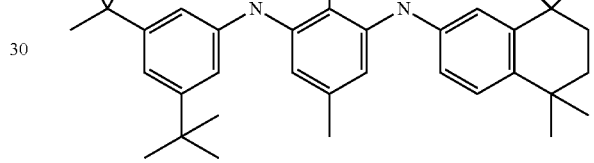
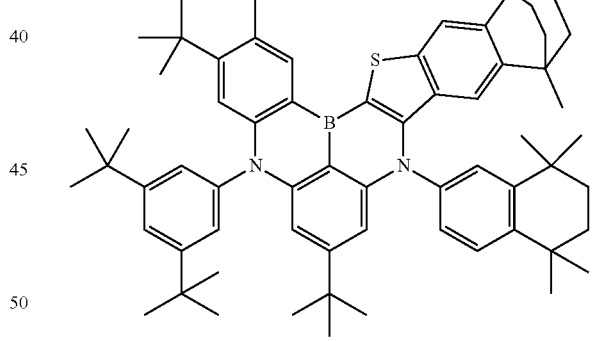
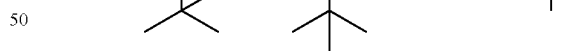
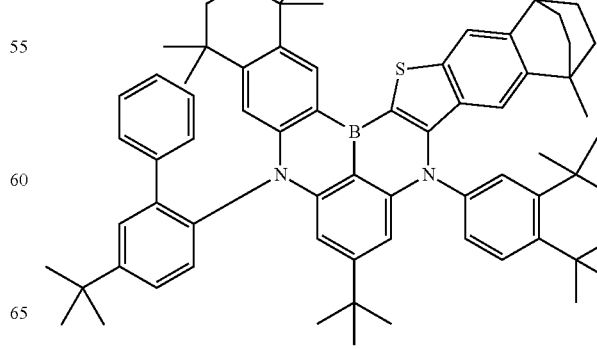

363
-continued
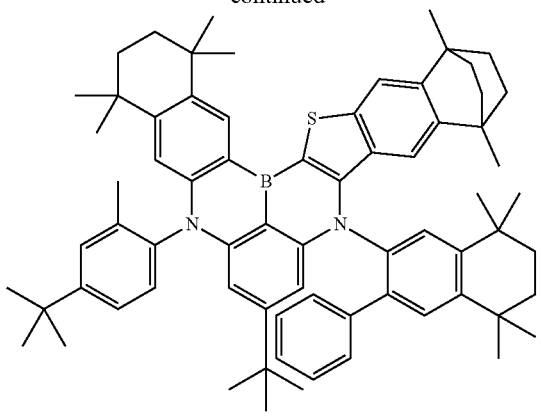
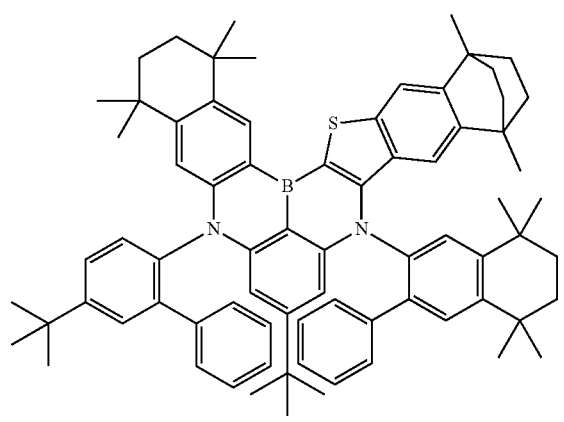
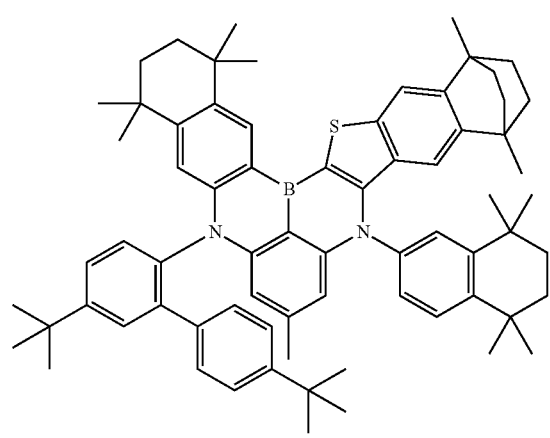
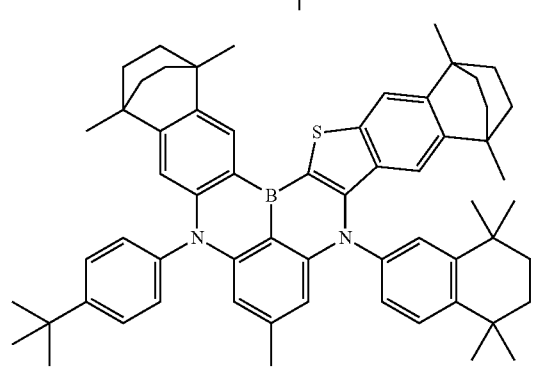
364
-continued
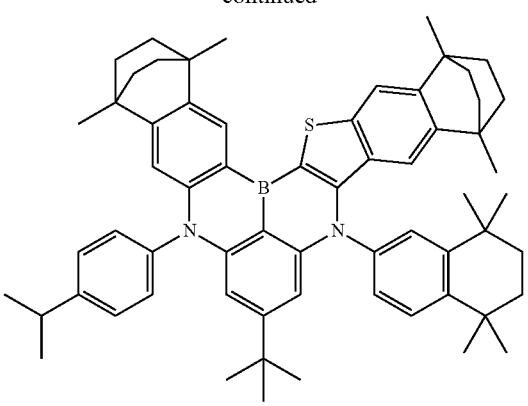
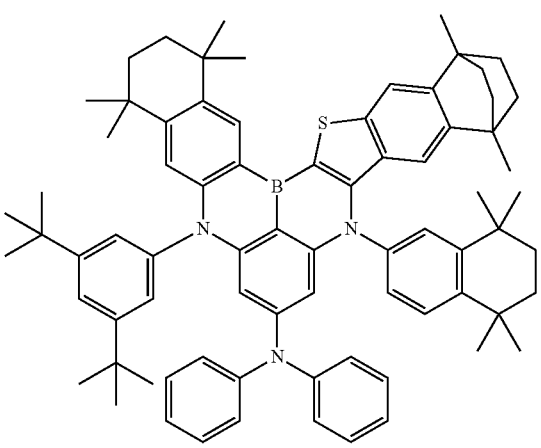
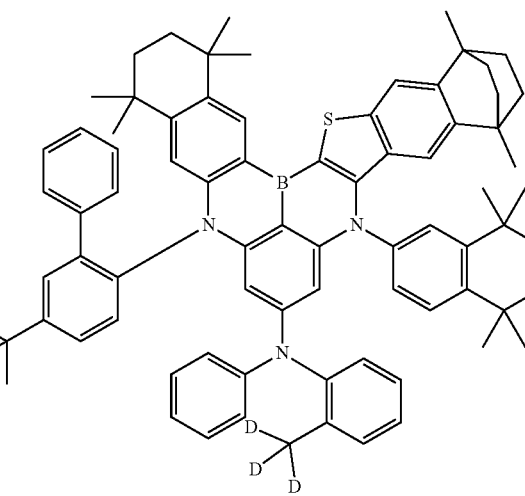

365
-continued
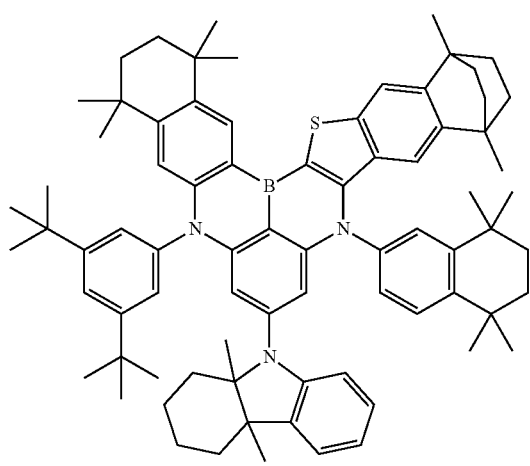
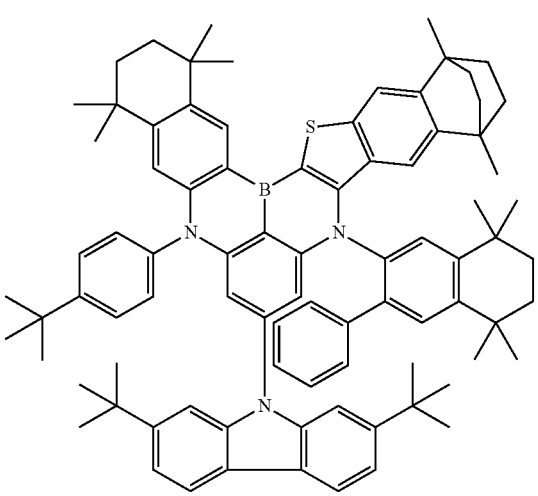
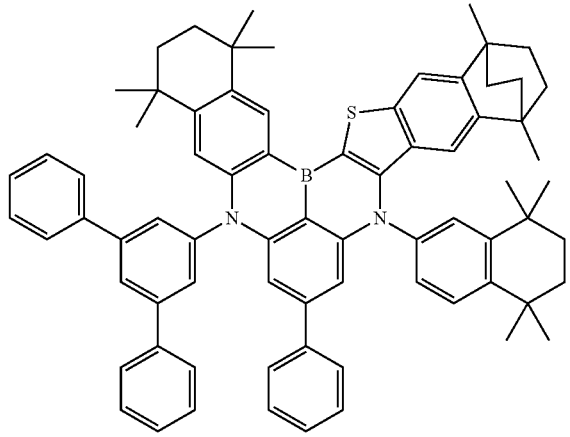
366
-continued
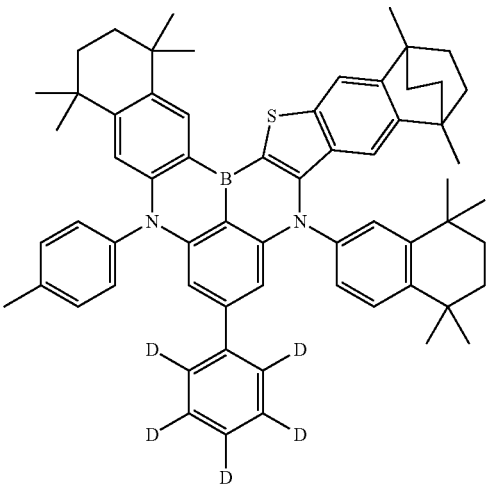
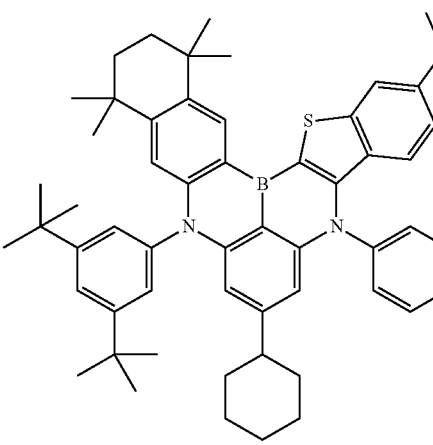
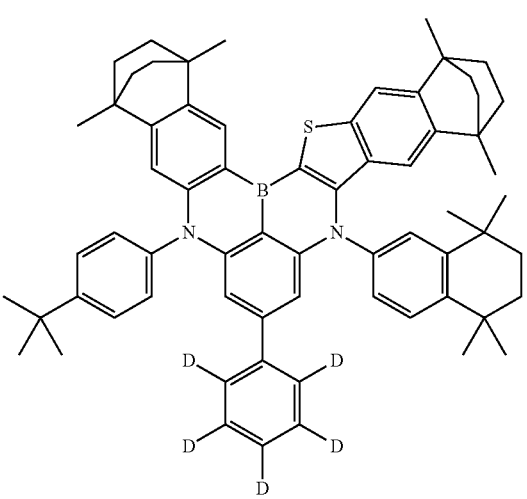

367
-continued
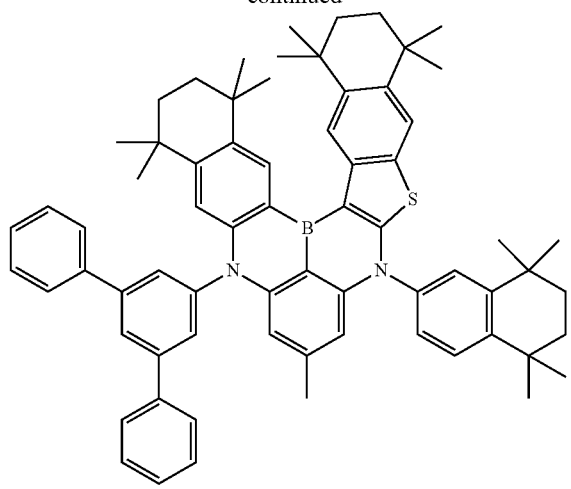
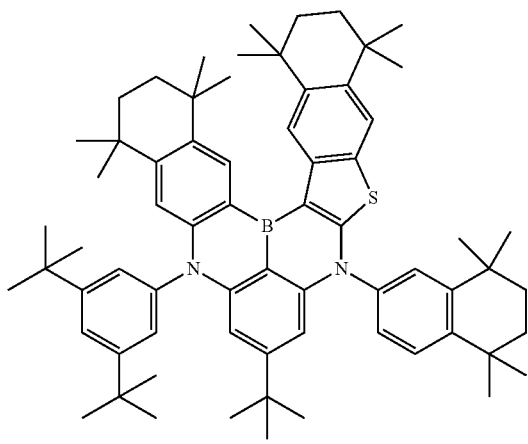
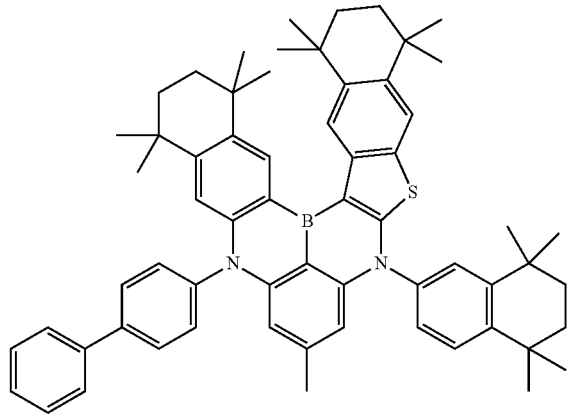
368
-continued
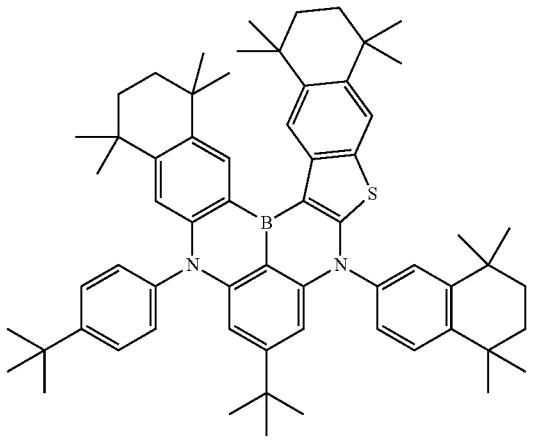
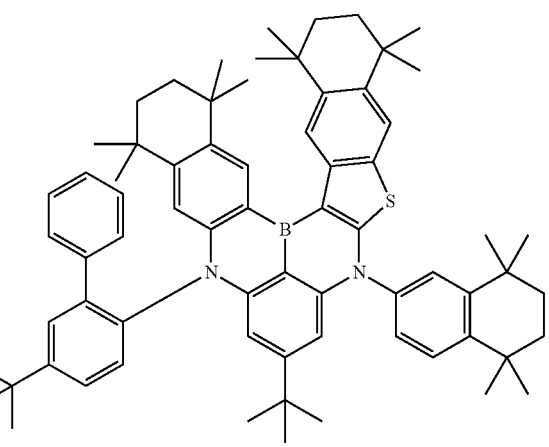
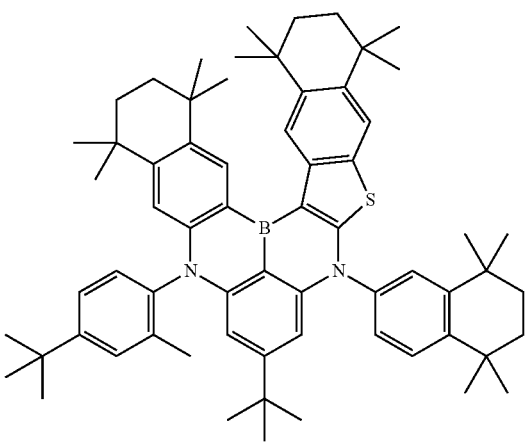

369
-continued
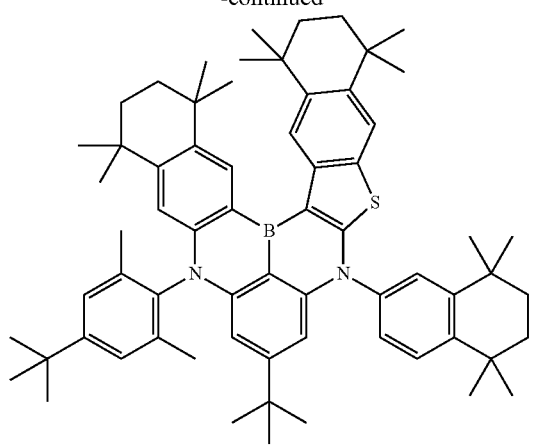
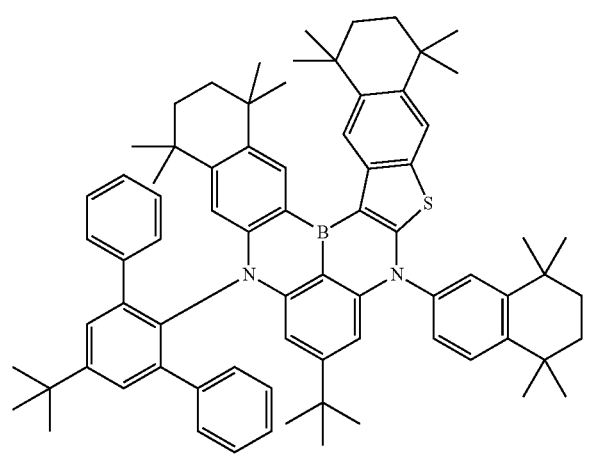
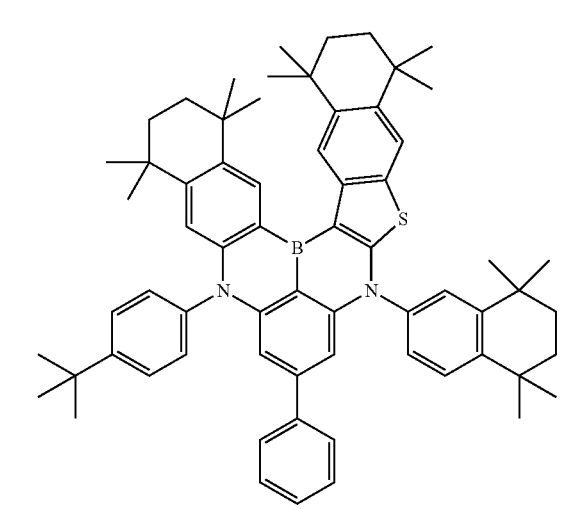
370
-continued
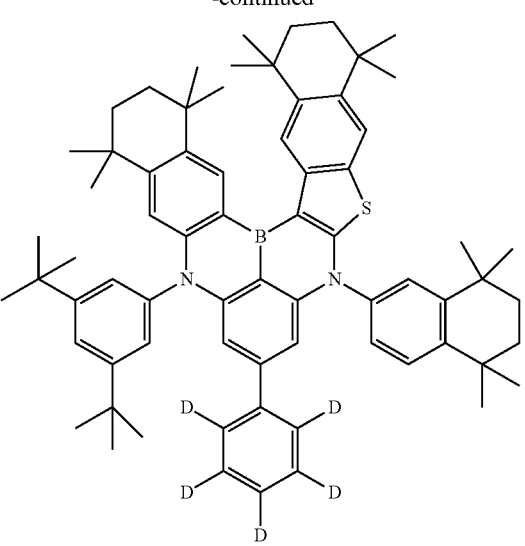
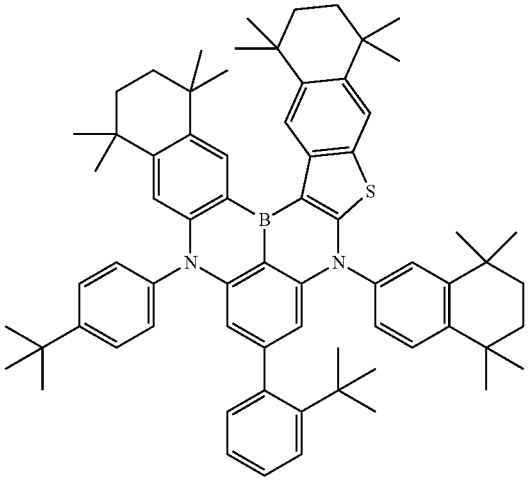
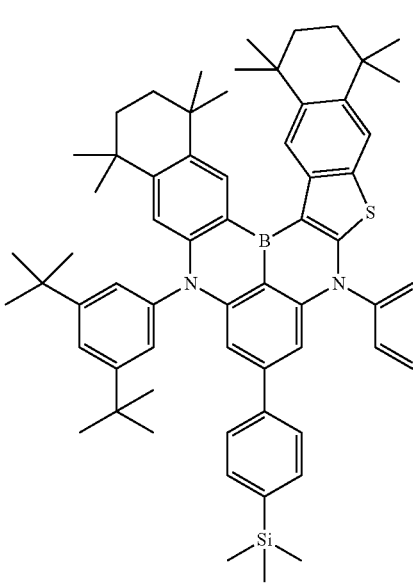

371
-continued
372
-continued
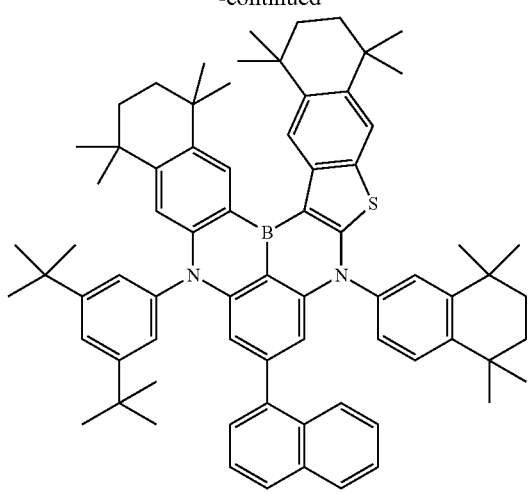
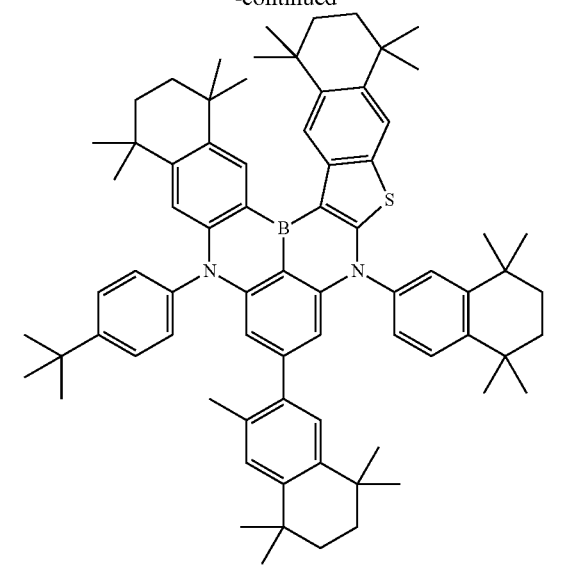
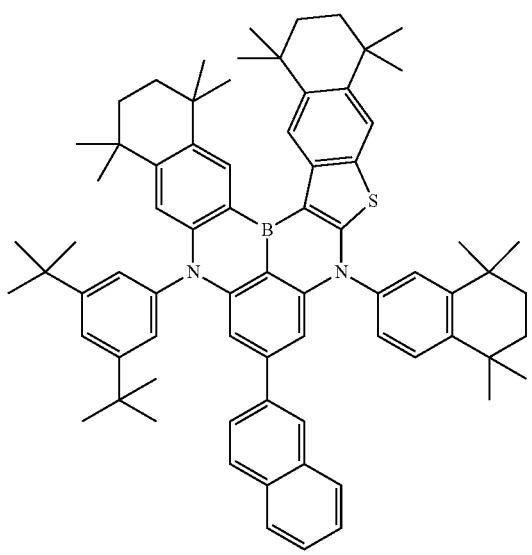
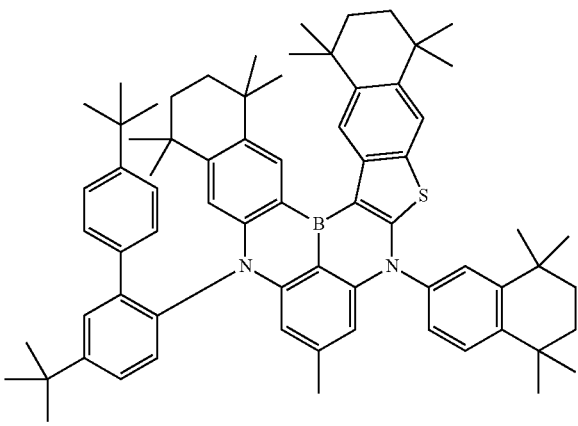
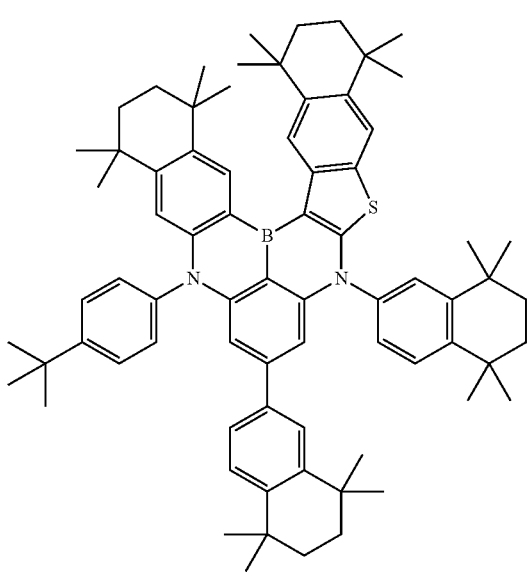
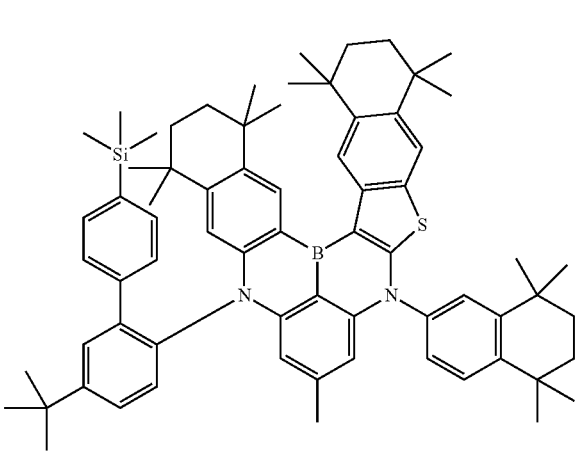

373
-continued
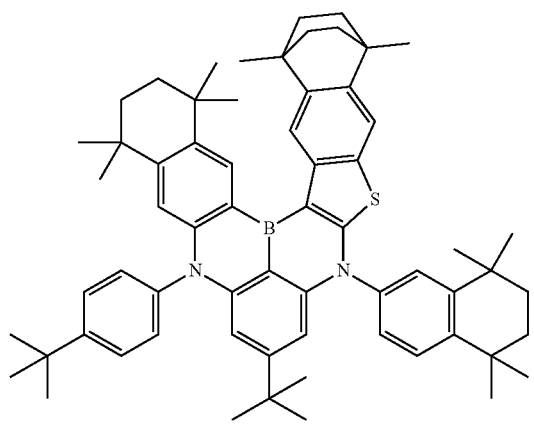
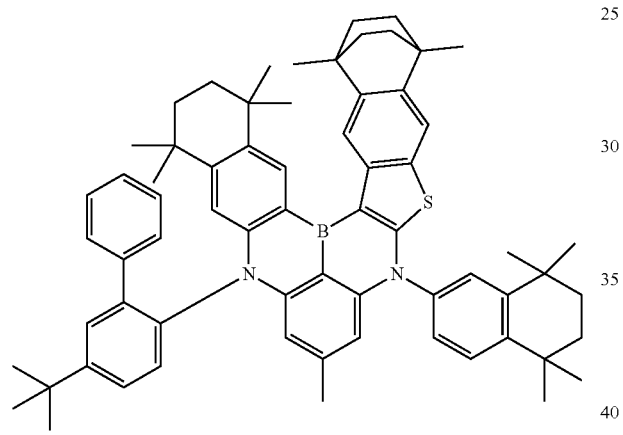
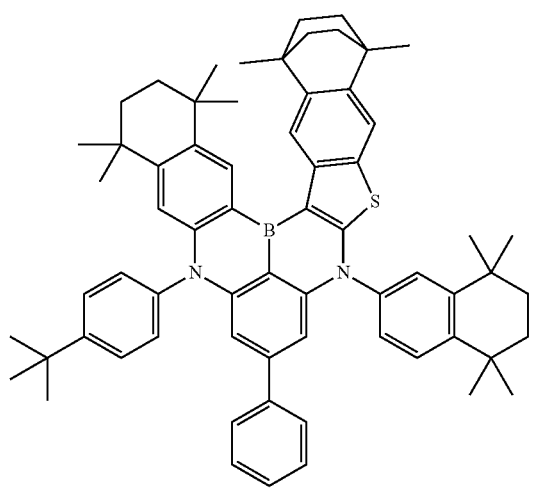
374
-continued
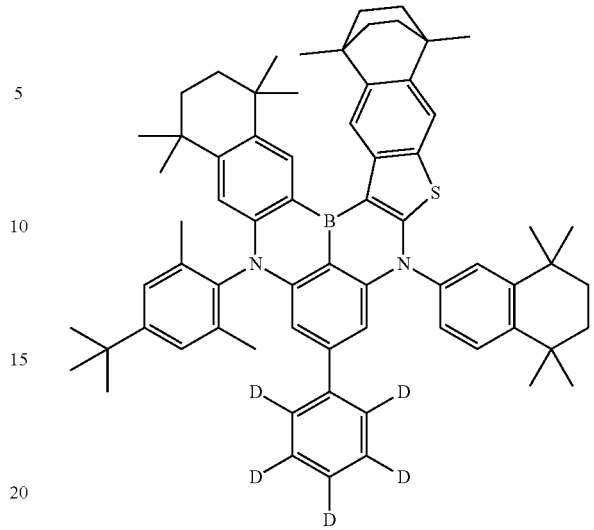
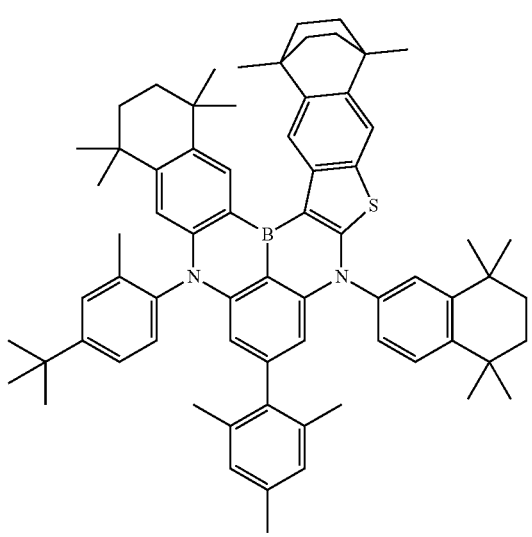
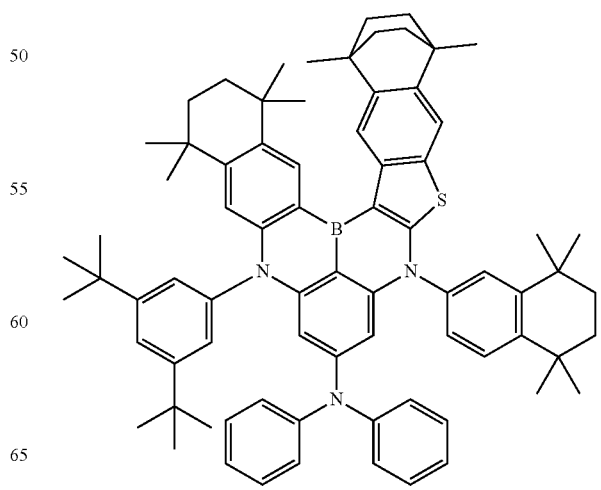

-continued
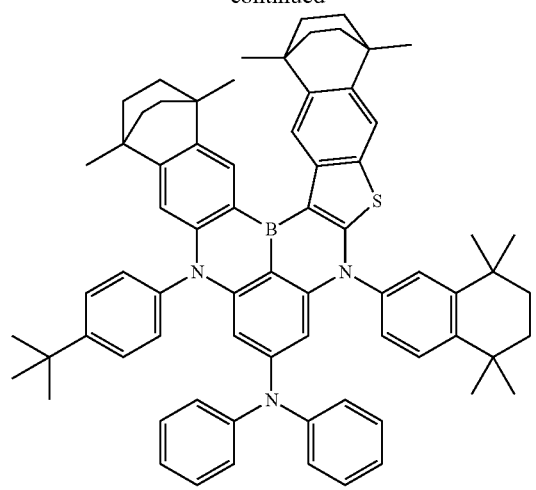
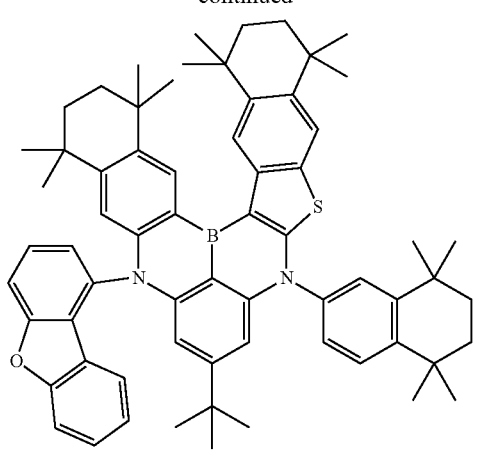
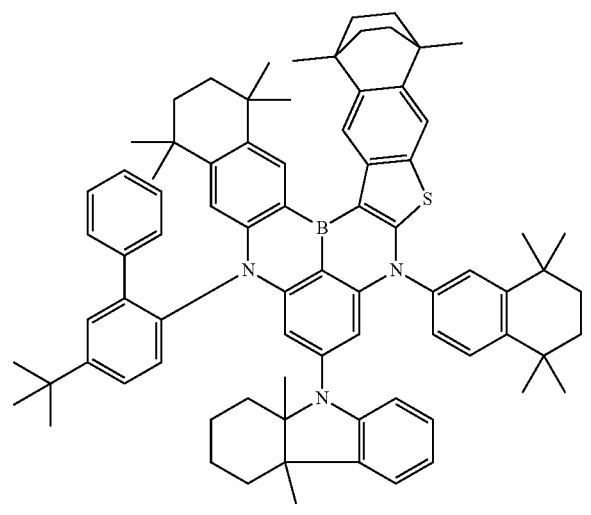
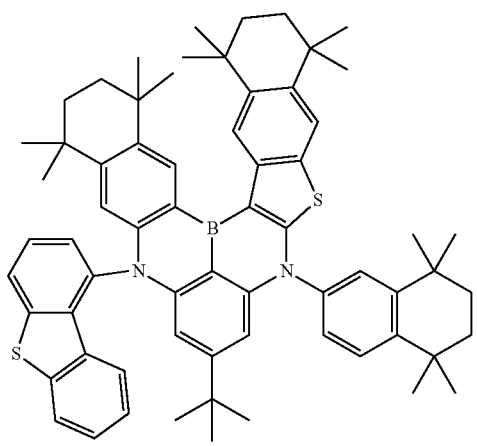
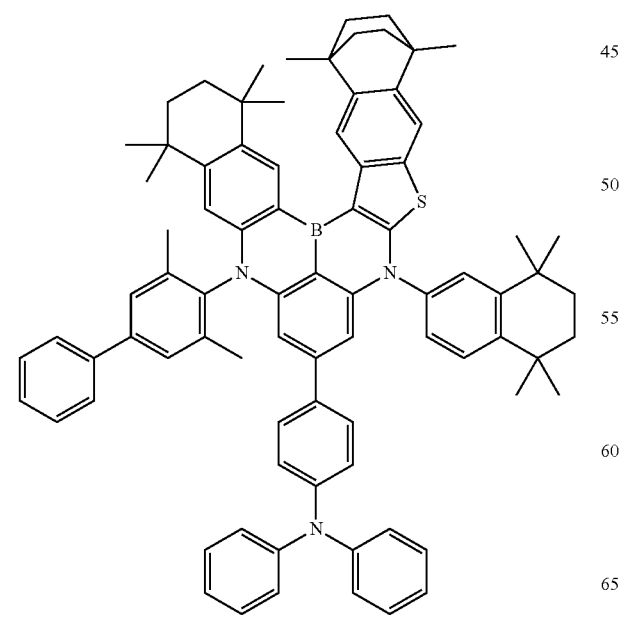
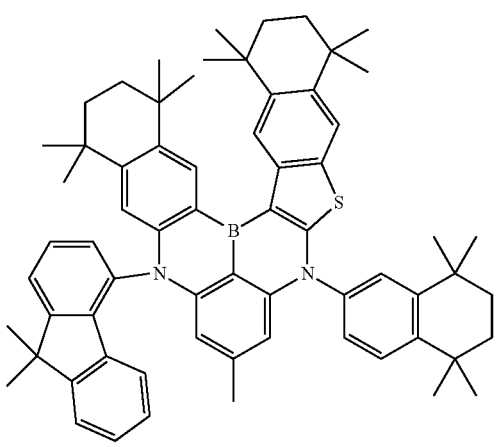

377
-continued
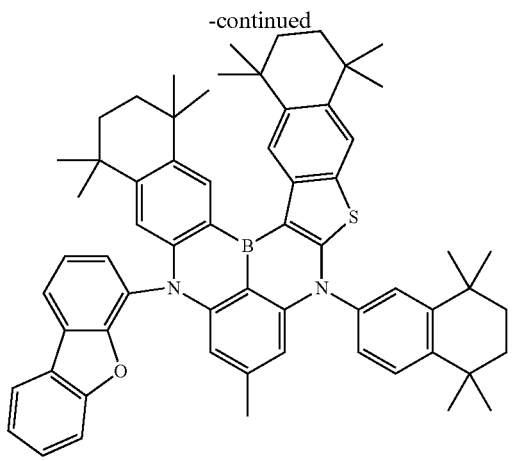
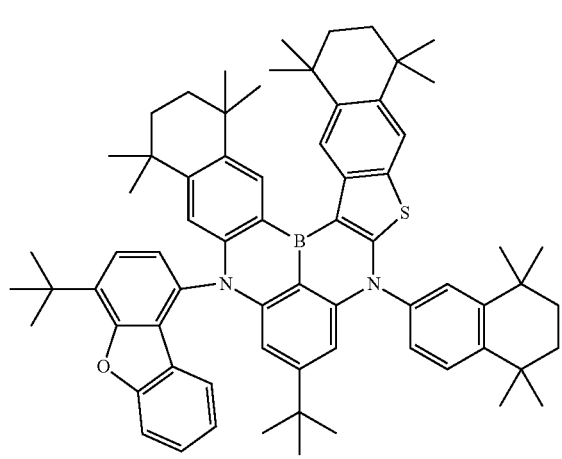
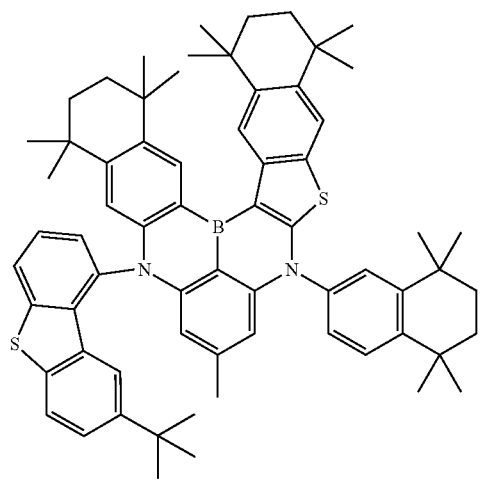
378
-continued
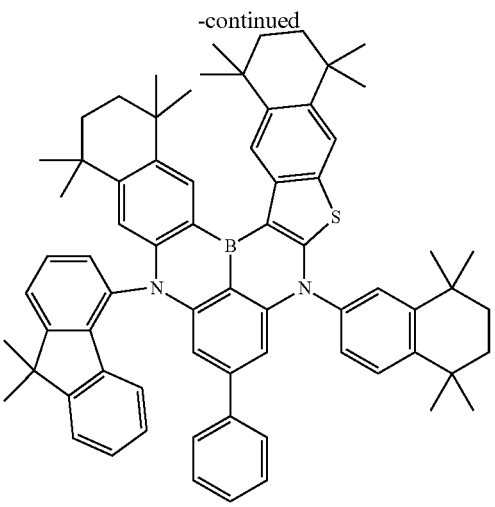
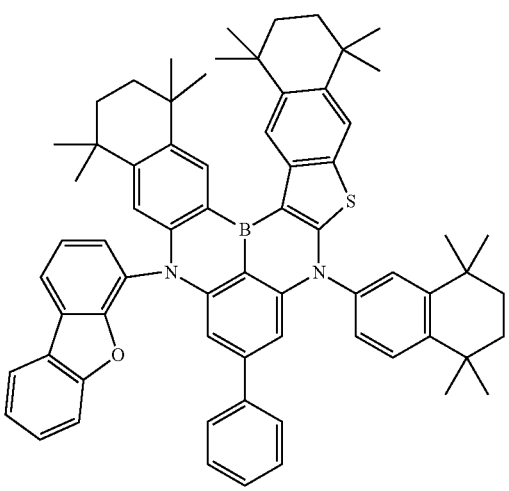
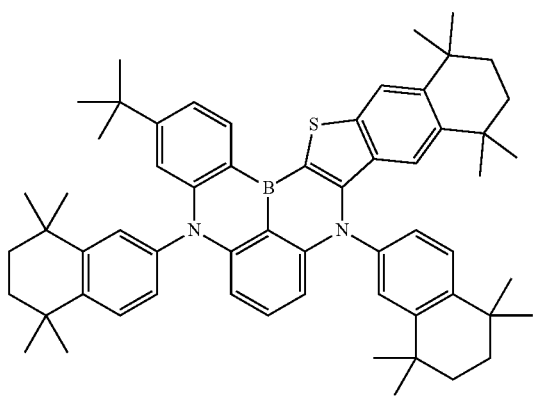

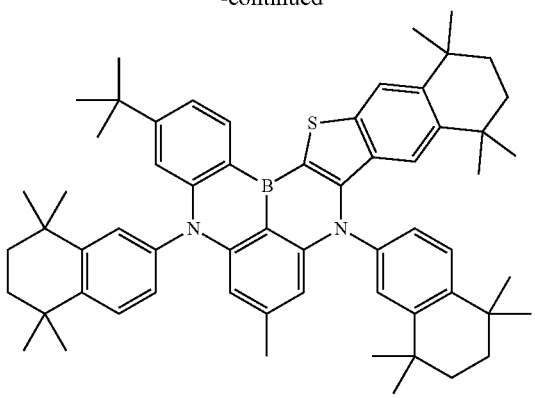
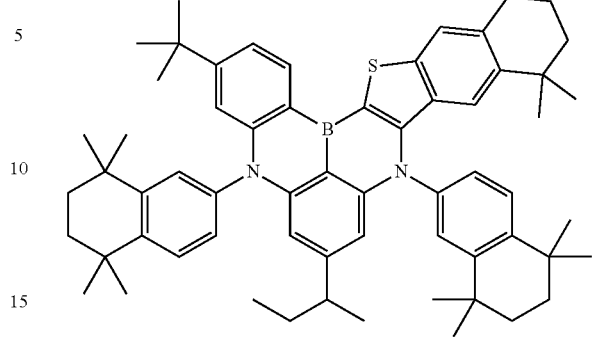
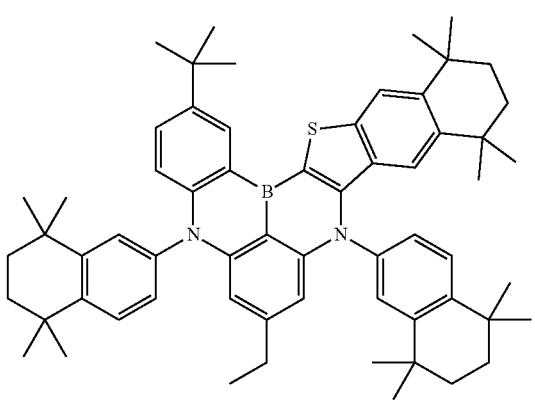
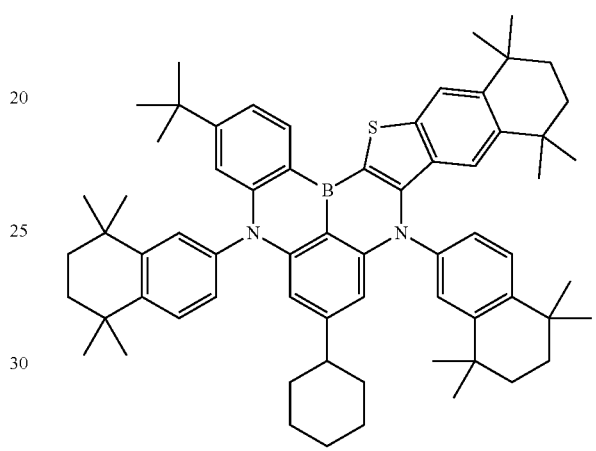
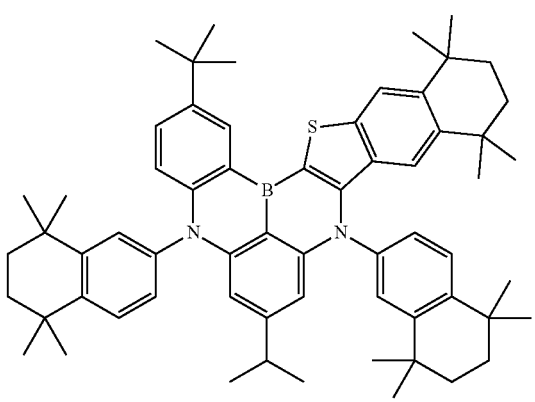
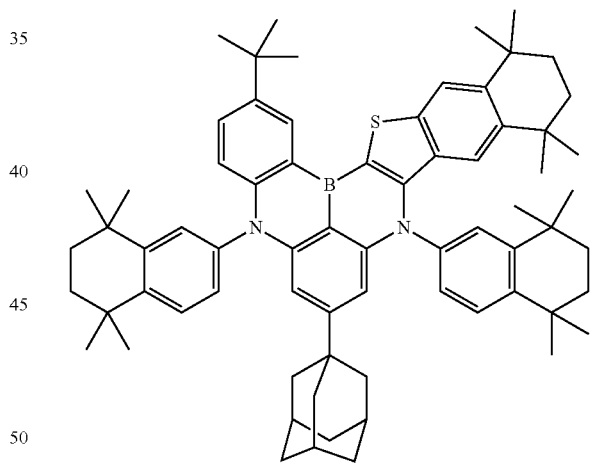
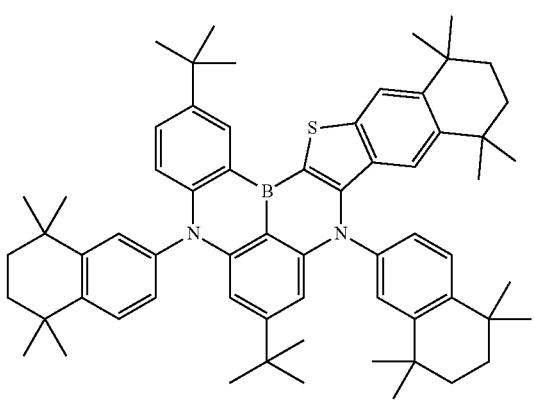
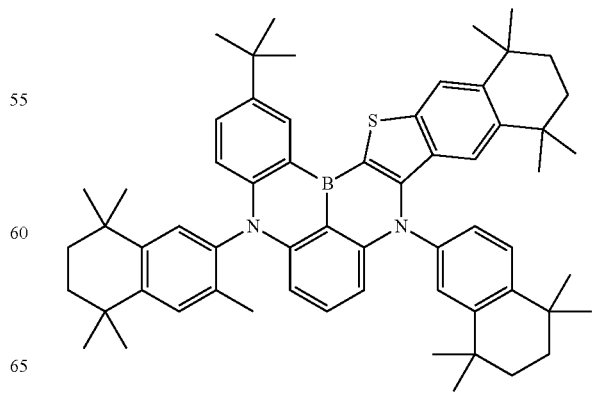

381
-continued
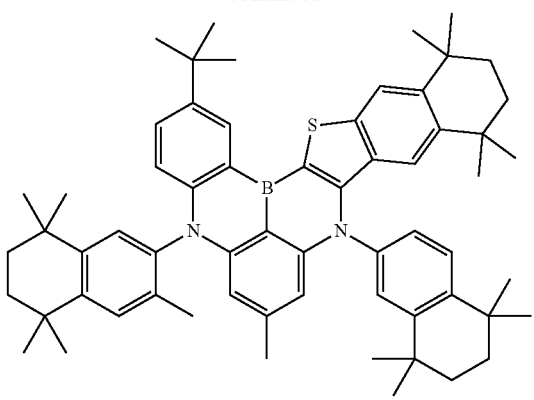
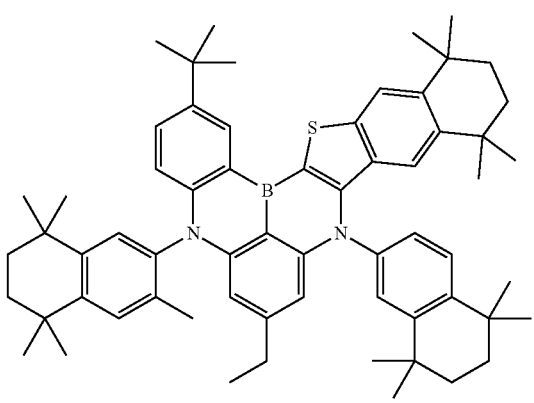
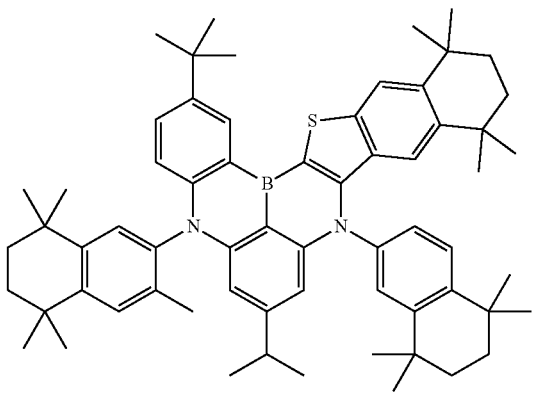
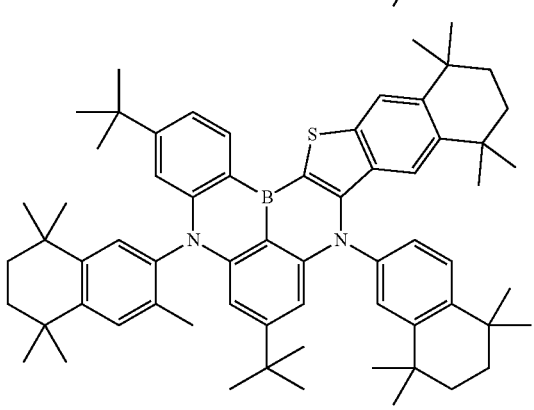
382
-continued
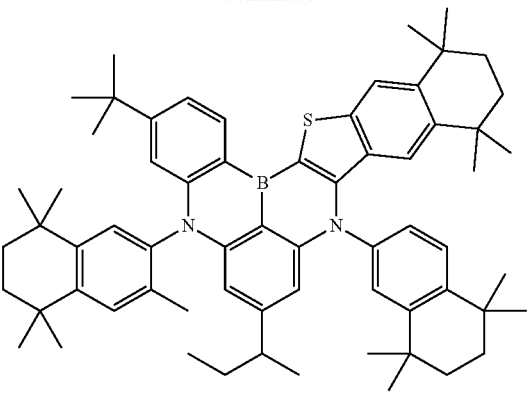
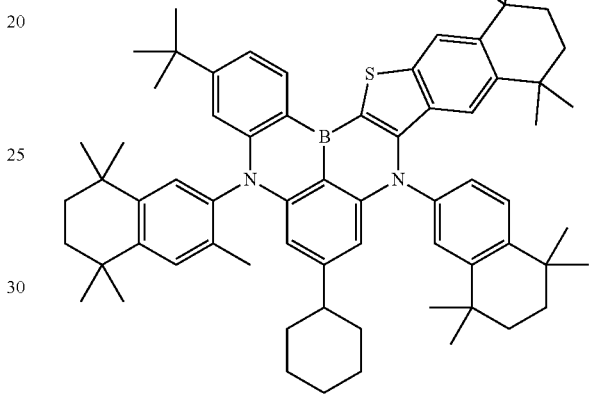
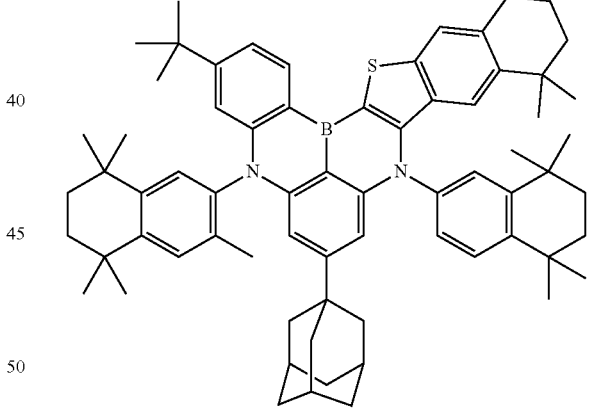
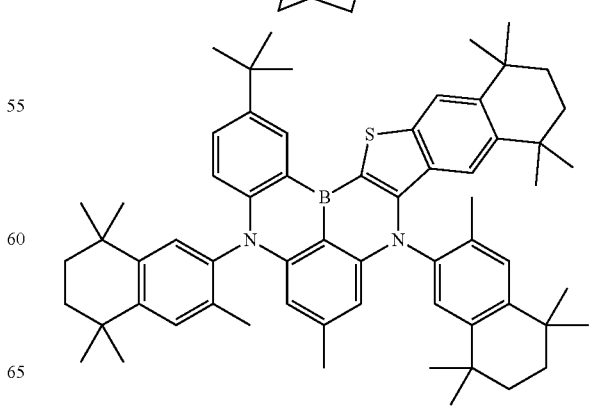

383
-continued
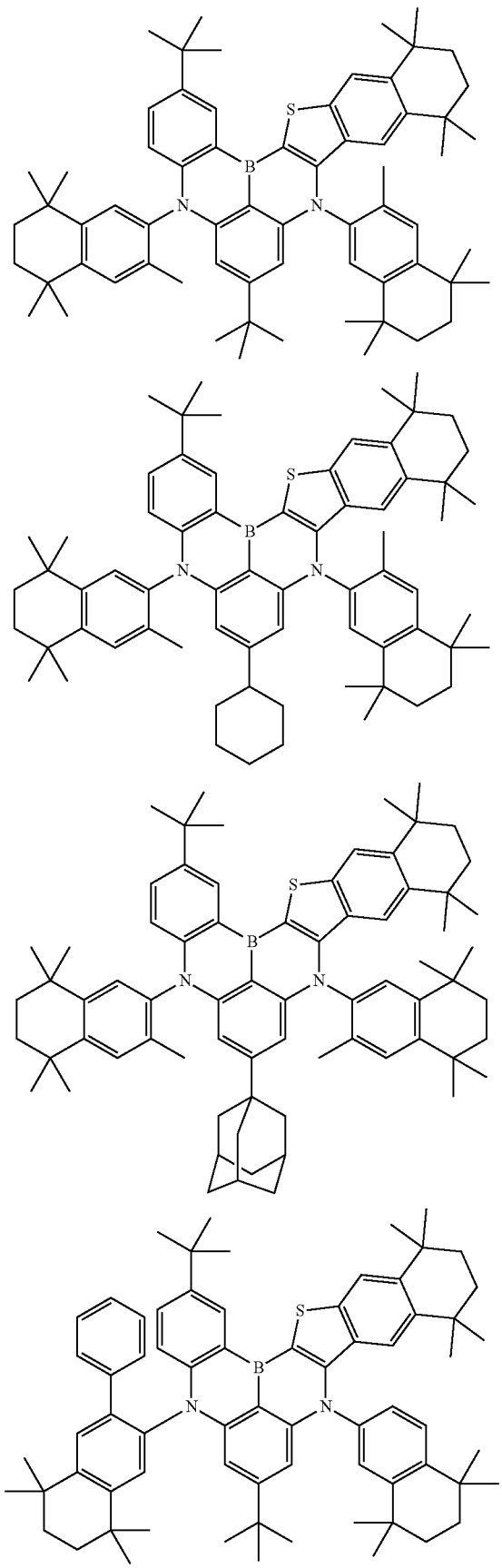
384
-continued
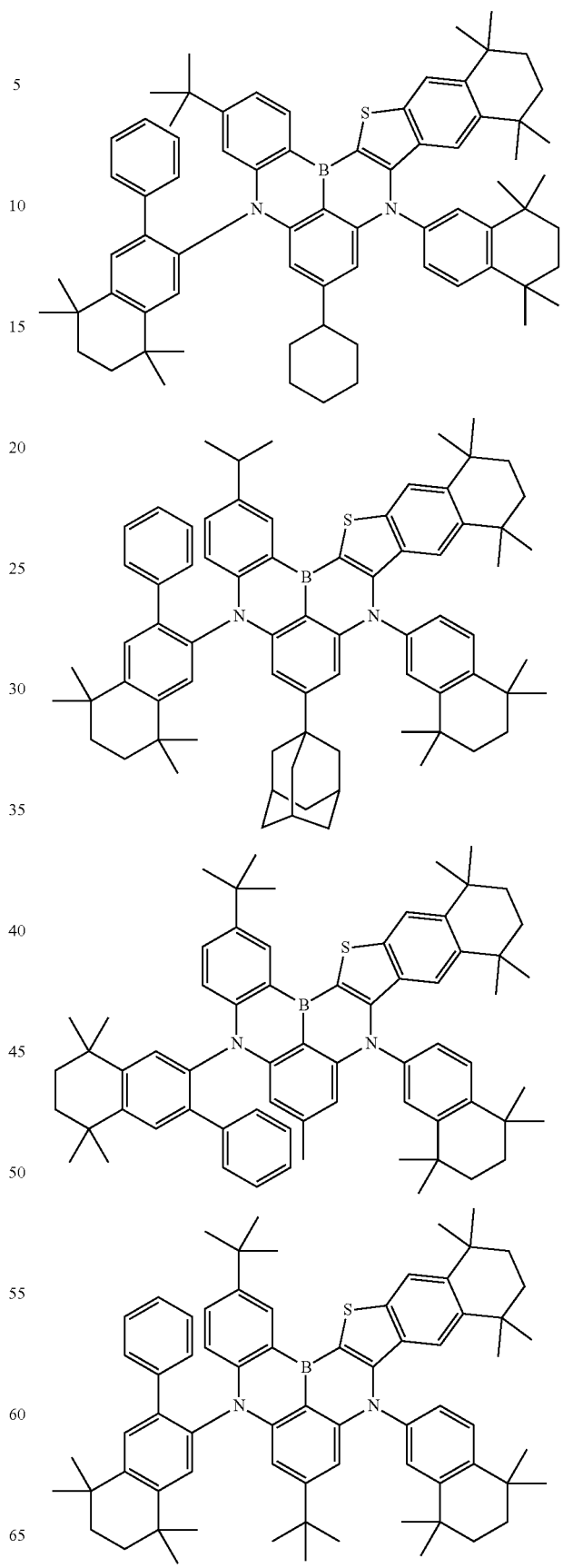

385
-continued
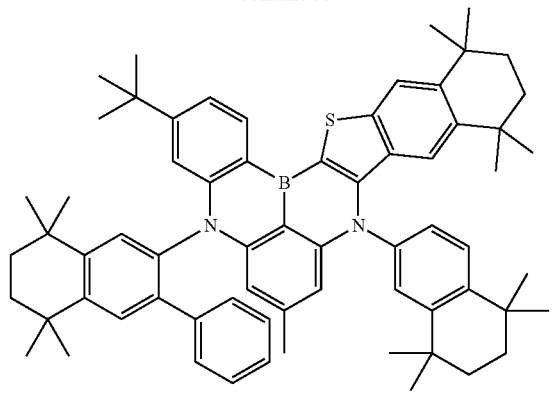
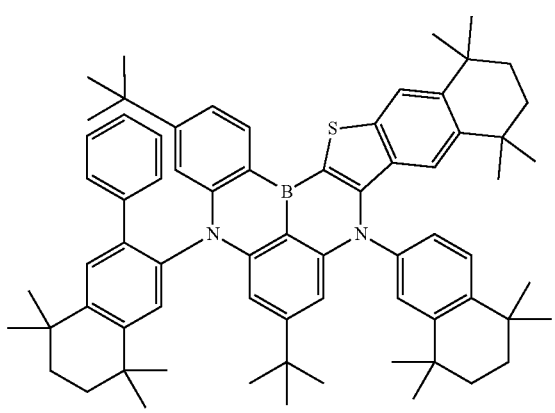
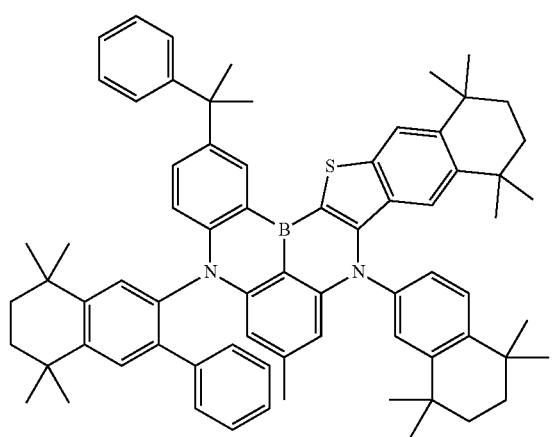
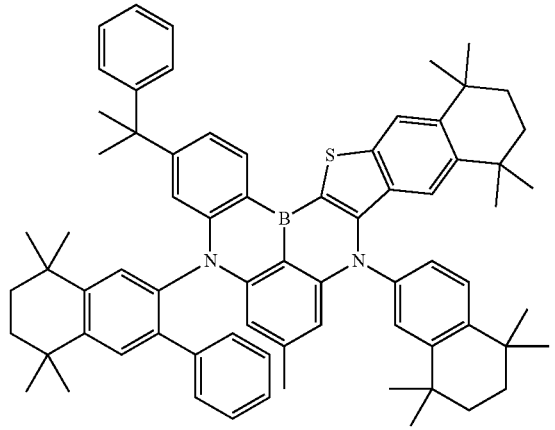
386
-continued
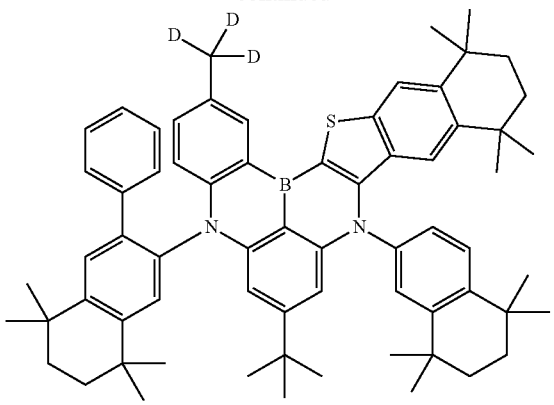
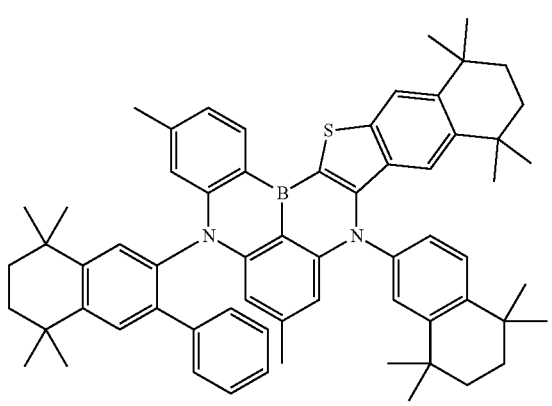
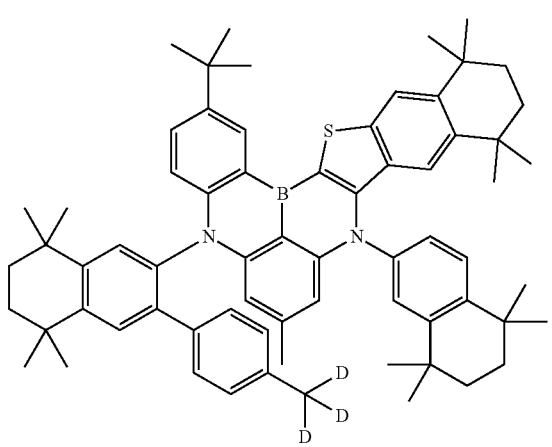
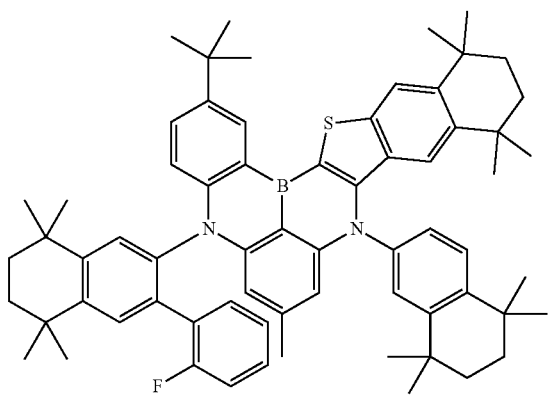

387
-continued
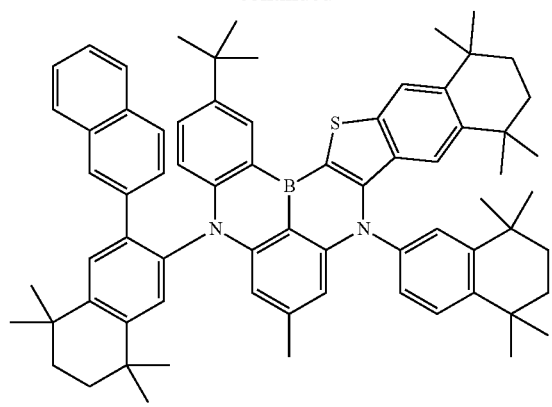
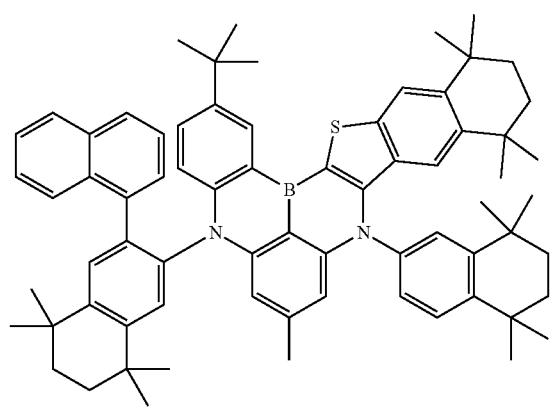
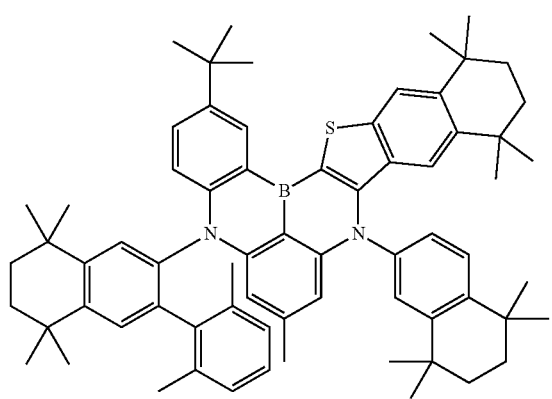
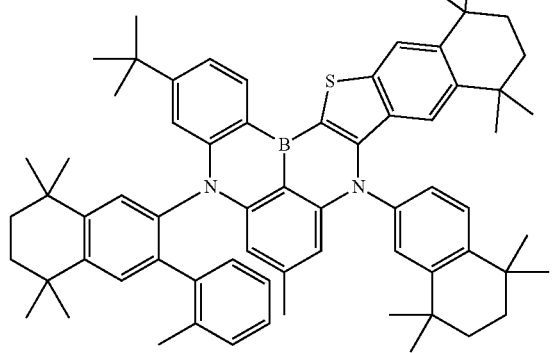
388
-continued
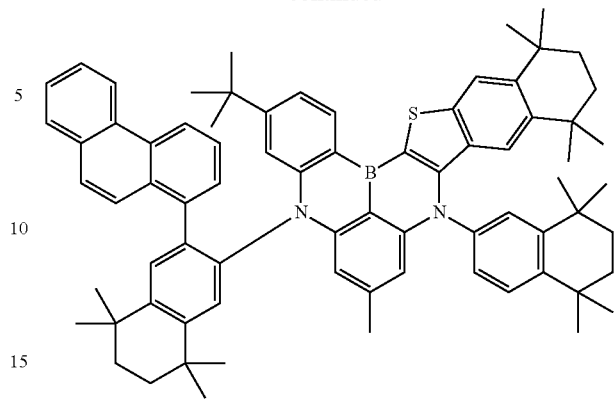
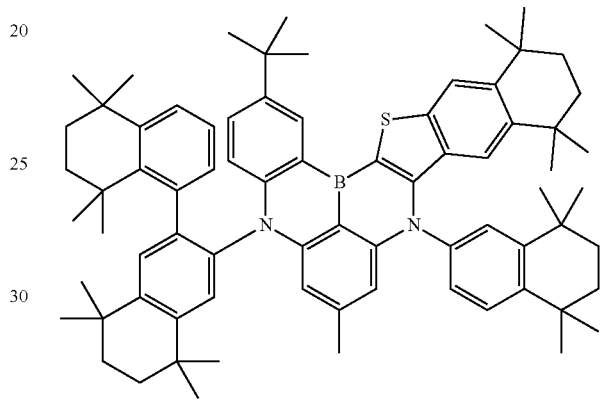
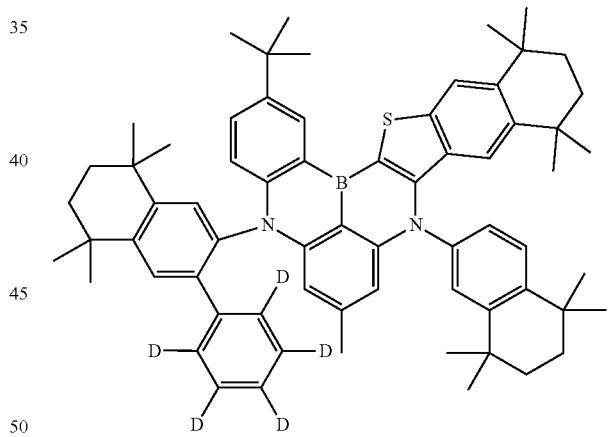
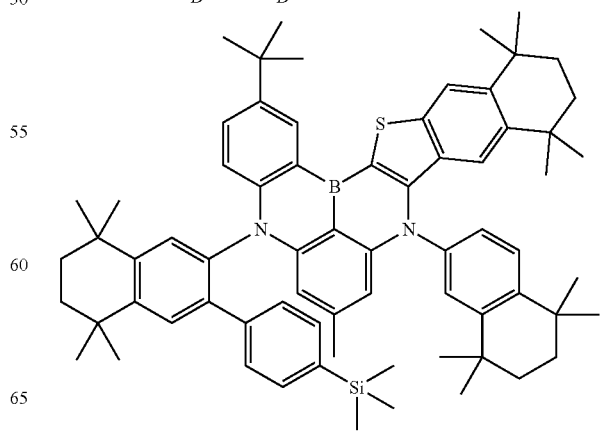

389
-continued
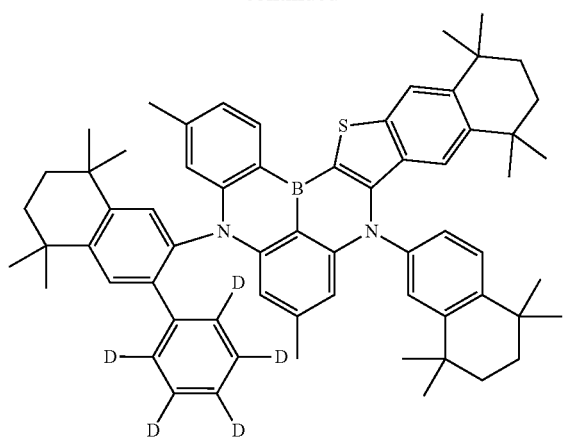
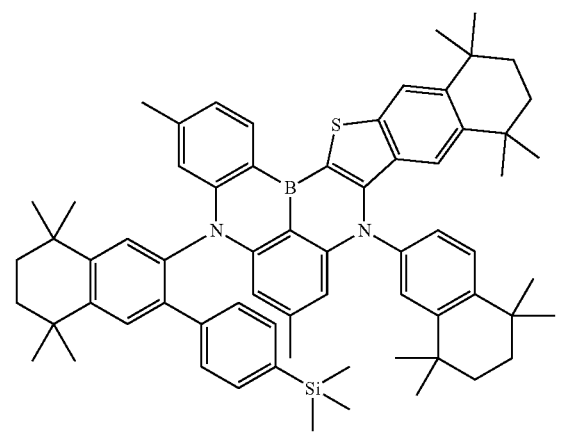
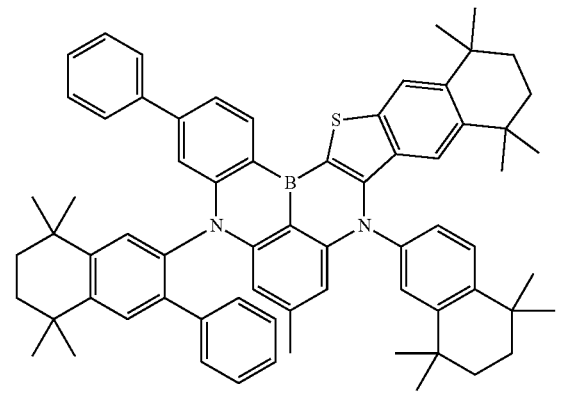
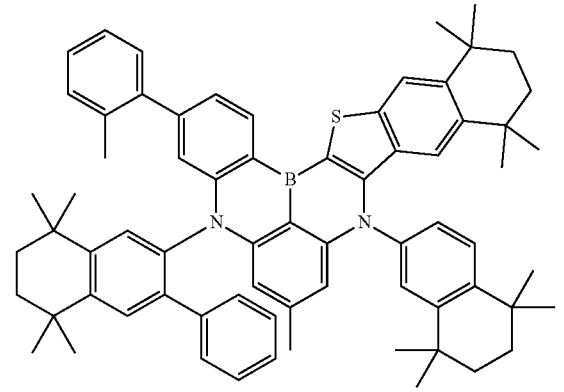
390
-continued
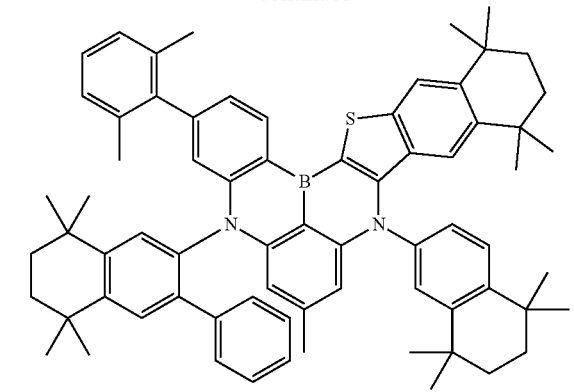
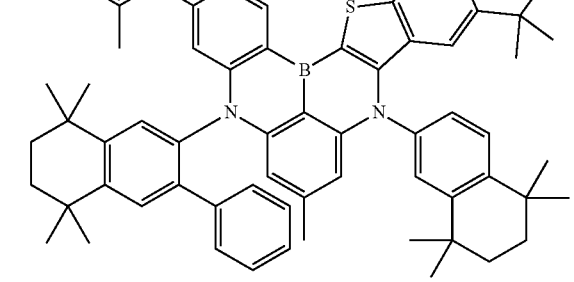
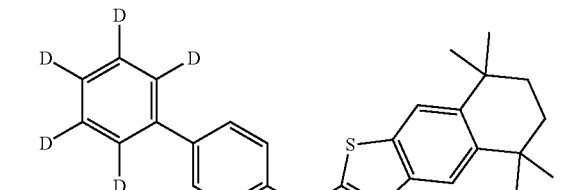
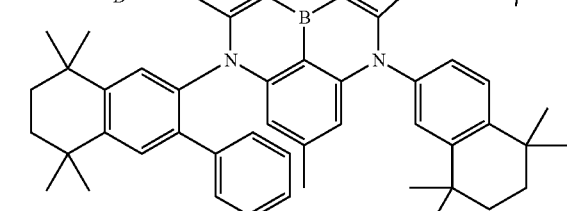
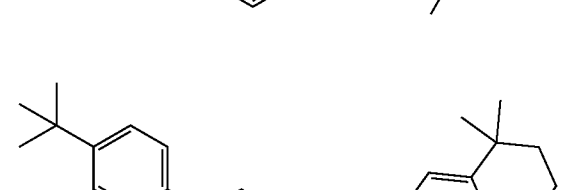
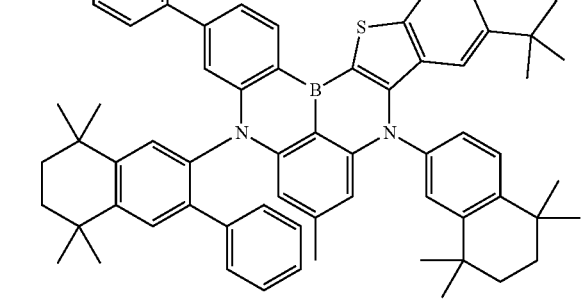

| 391 -continued | 392 -continued |
|---|---|
| 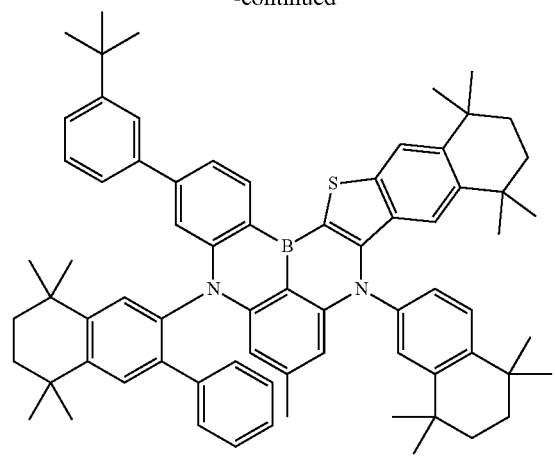 | 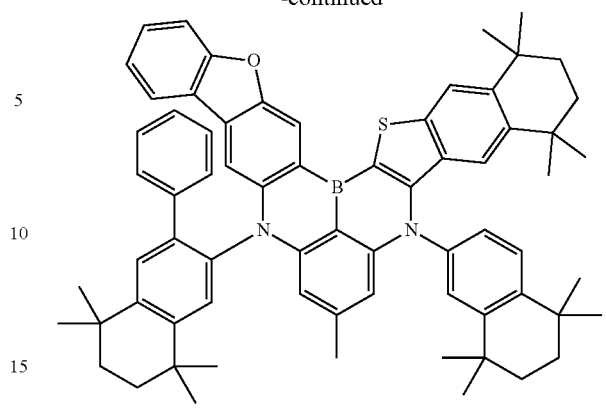 |
| 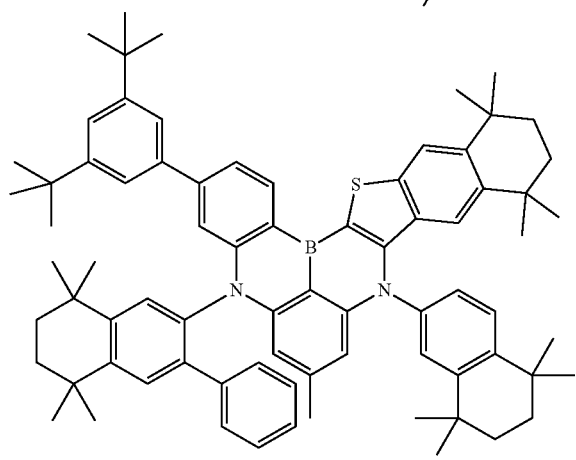 | 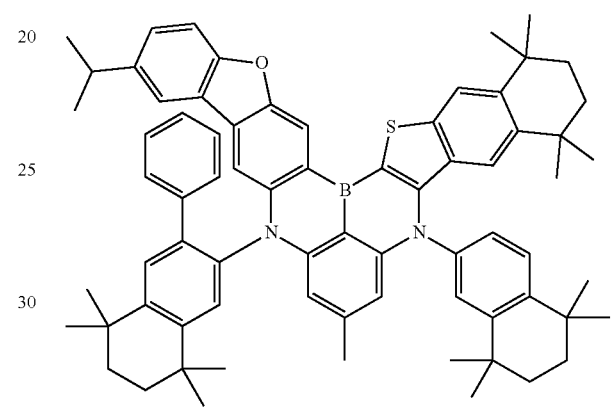 |
| 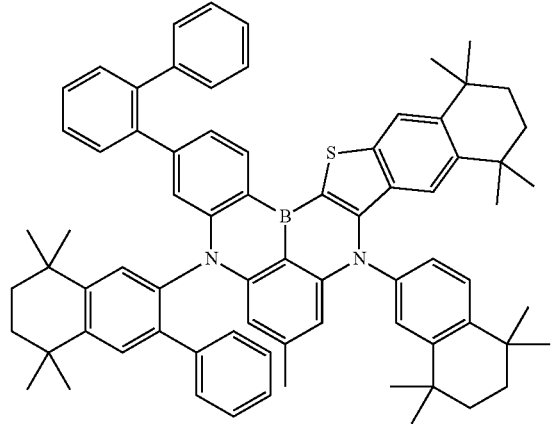 | 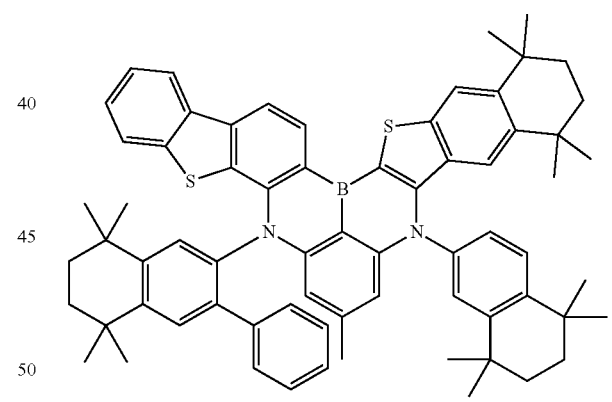 |
| 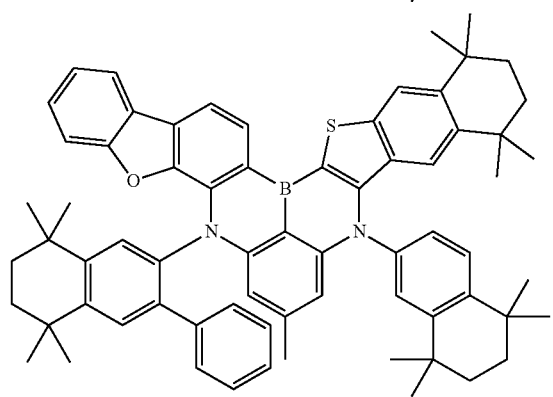 | 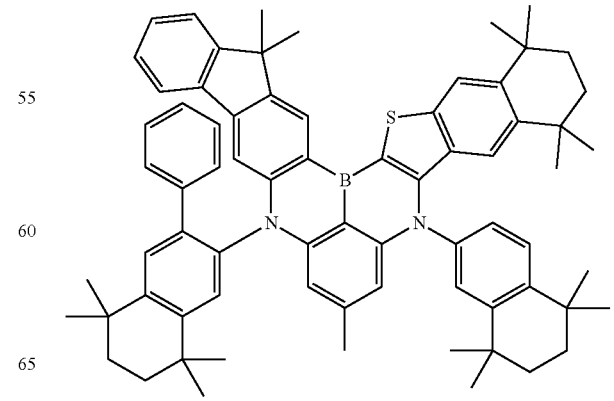 |

393
-continued
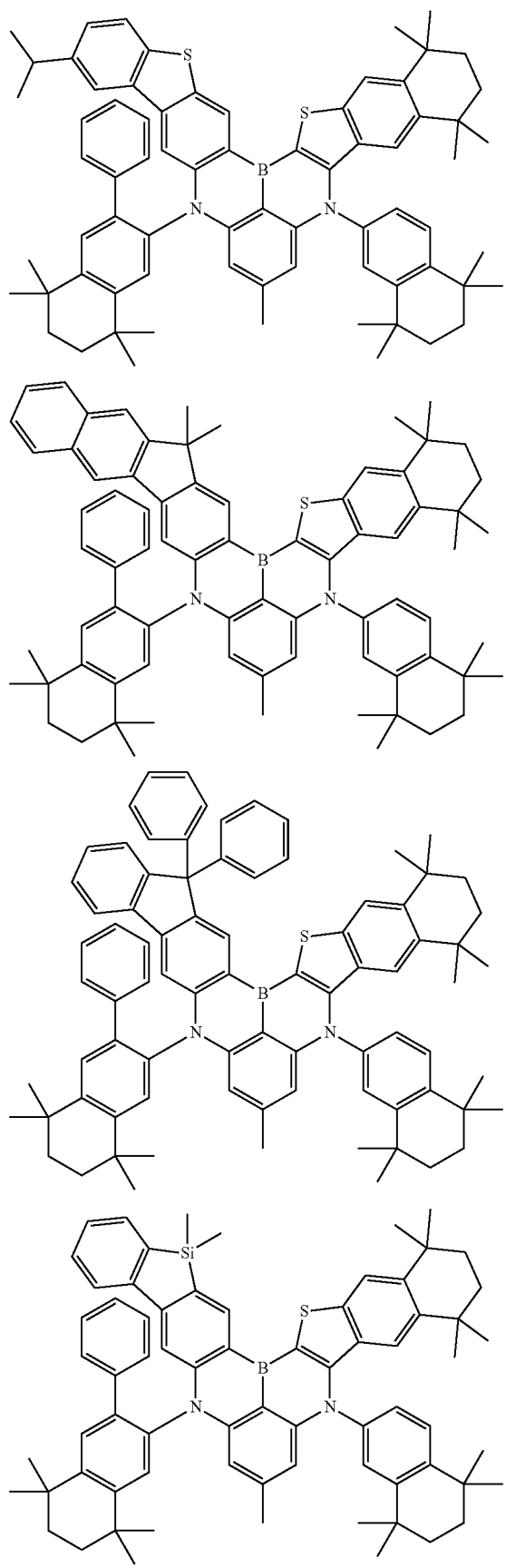
394
-continued
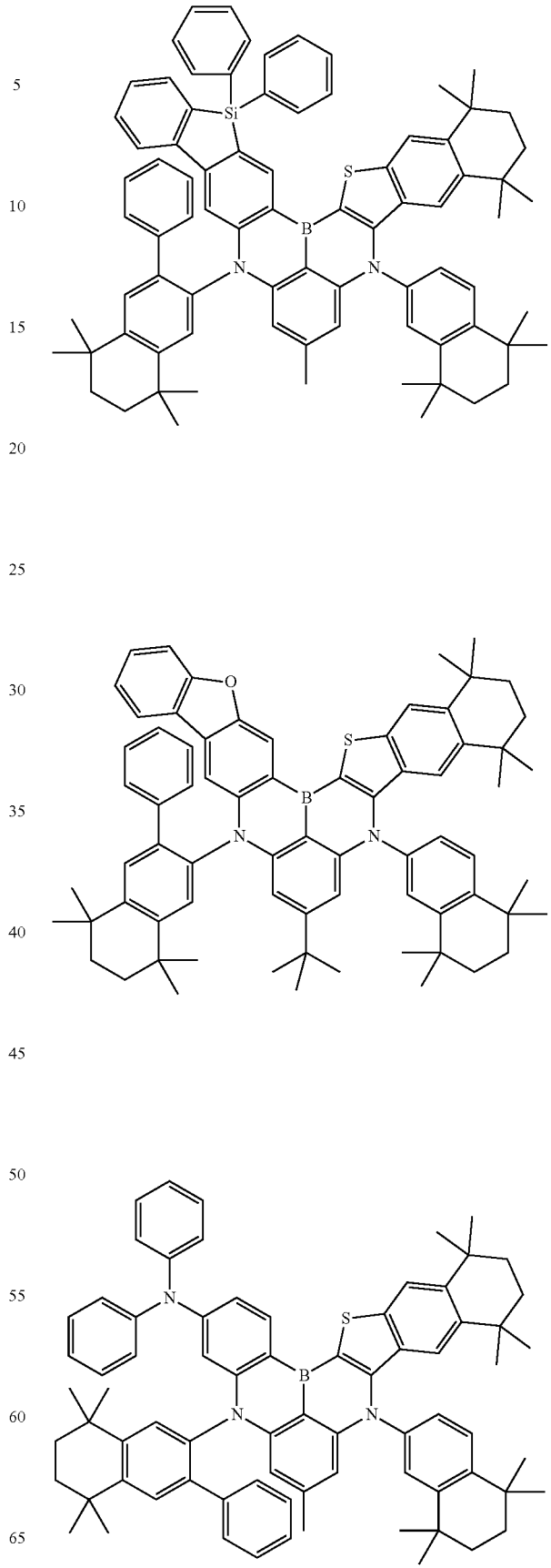

395
-continued
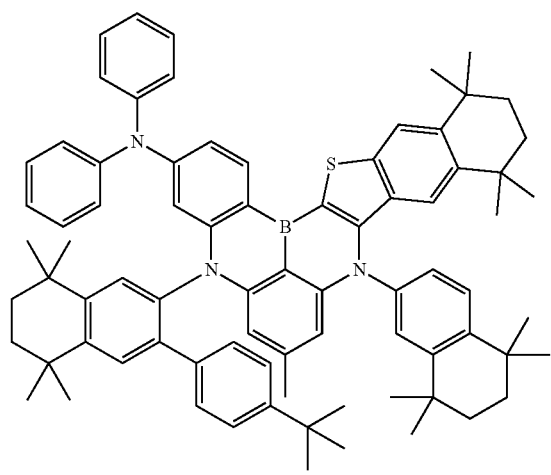
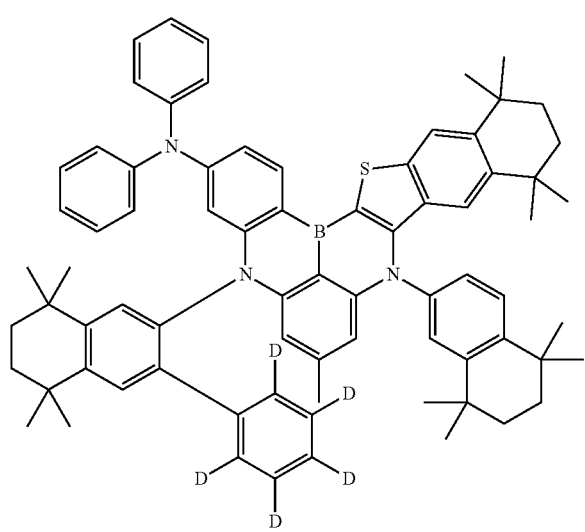
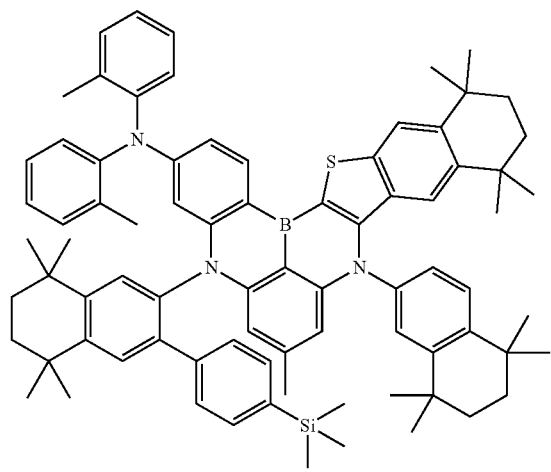
396
-continued
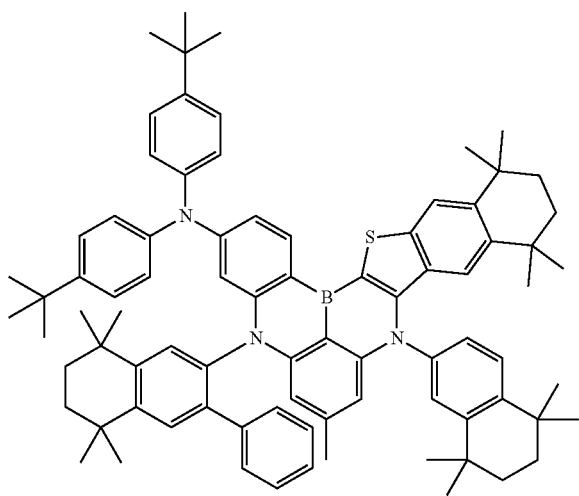
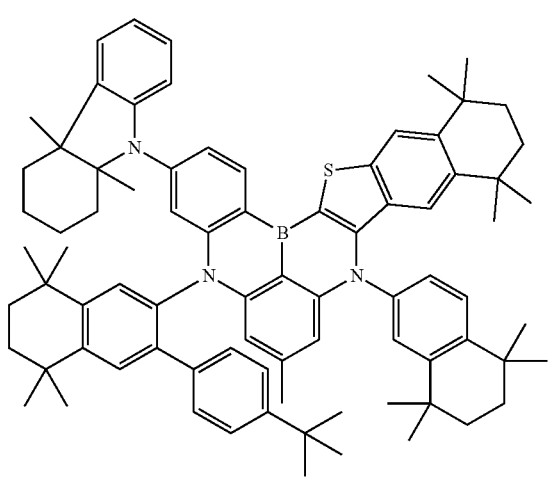
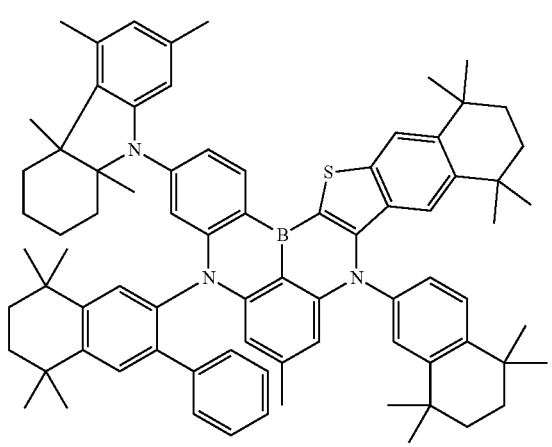

397
-continued
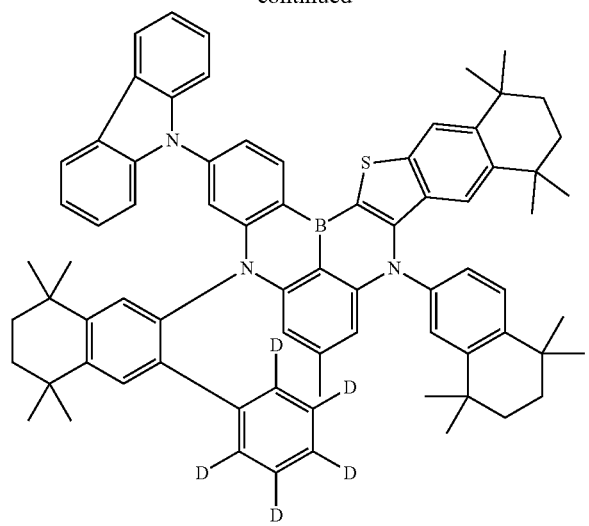
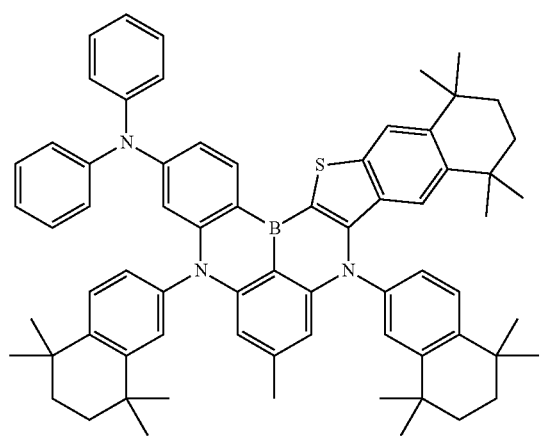
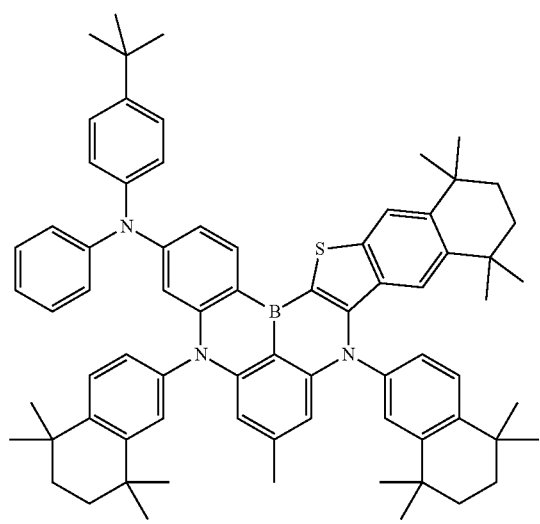
398
-continued
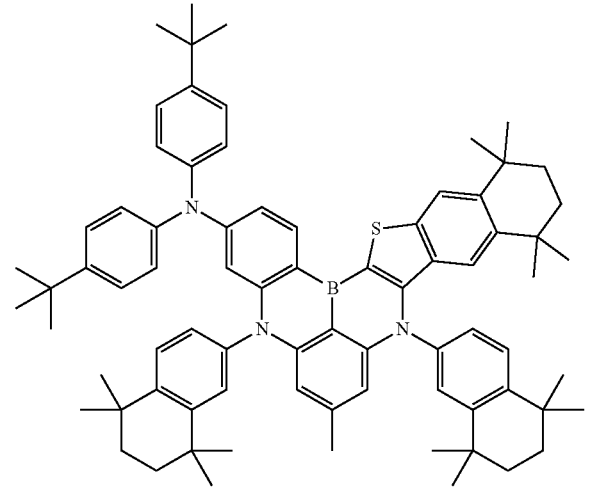
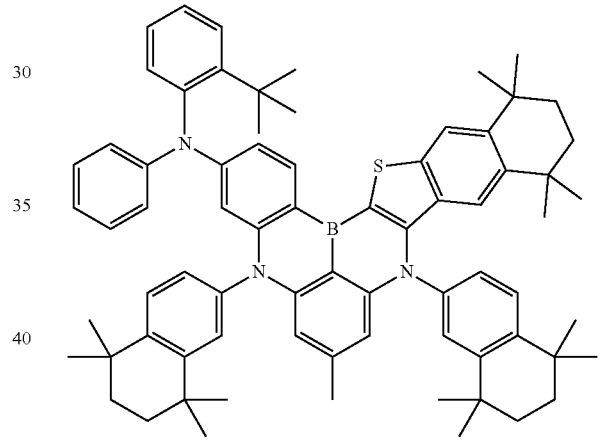
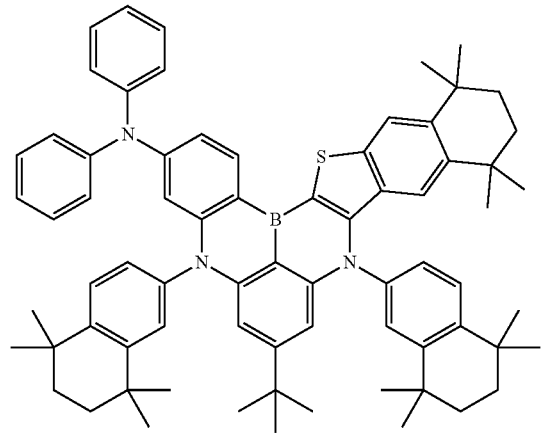

399
-continued
400
-continued
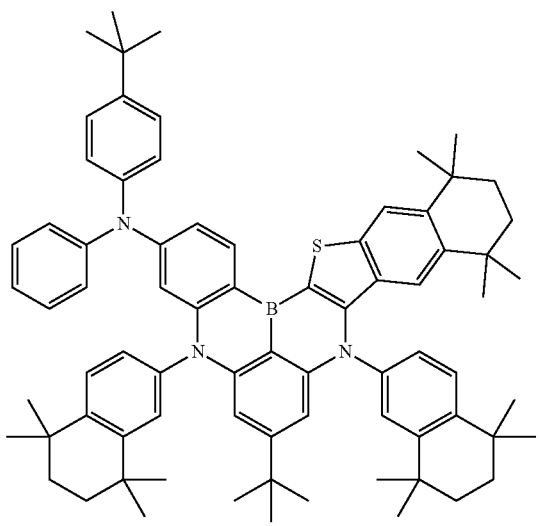

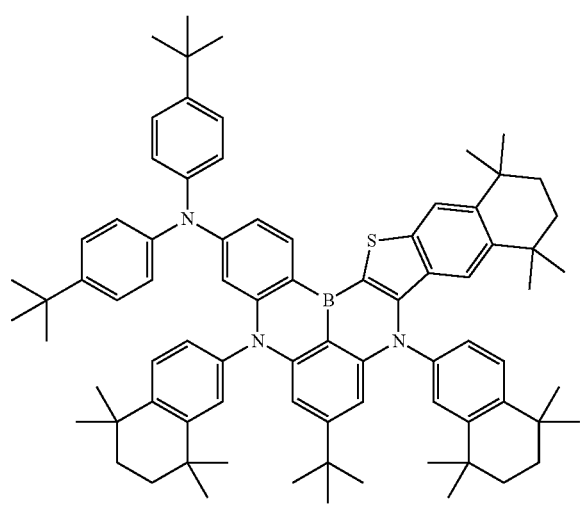
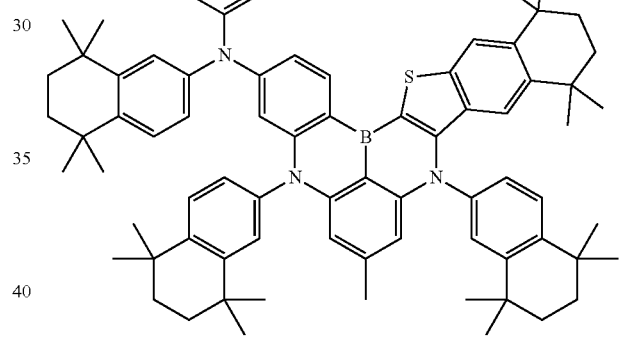
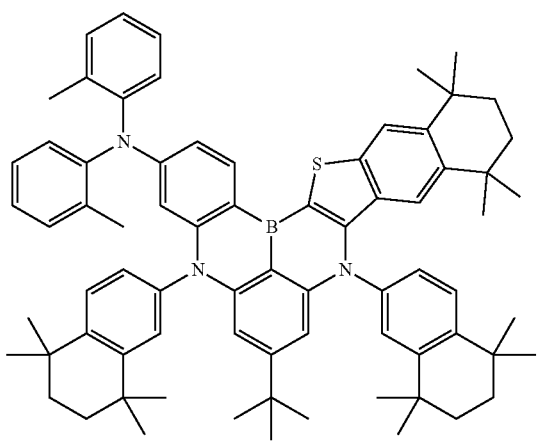
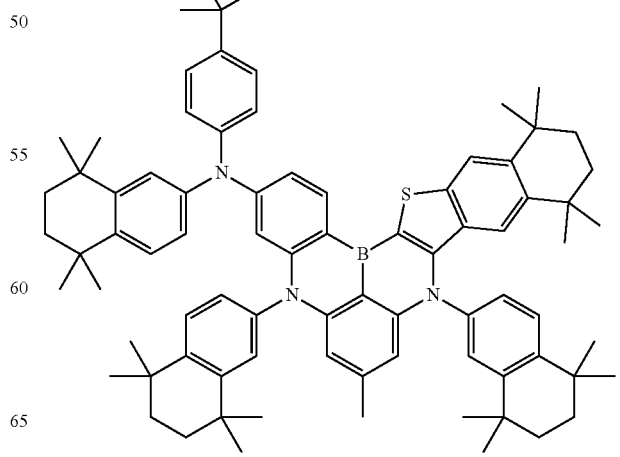

401
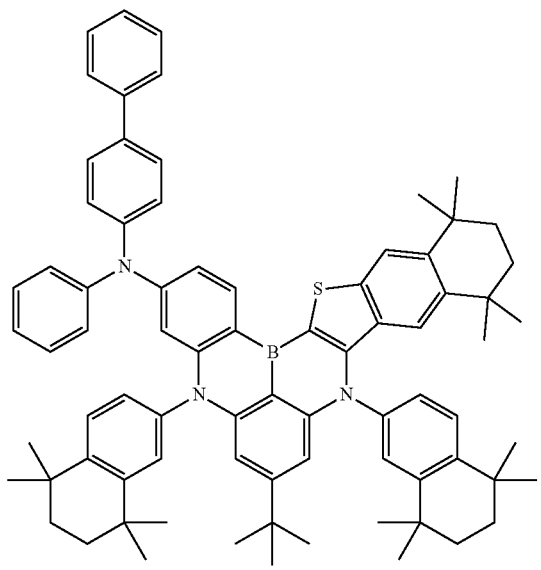
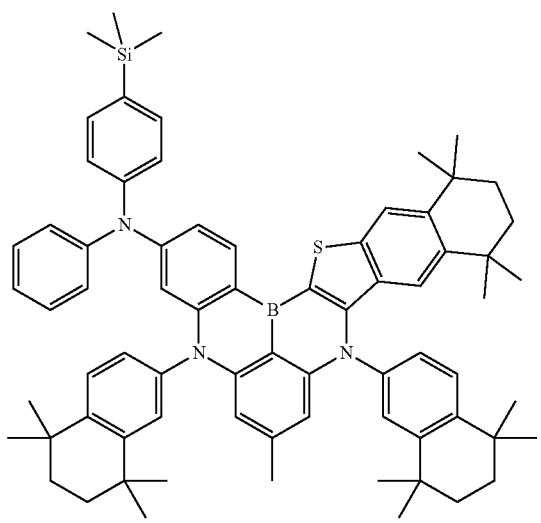
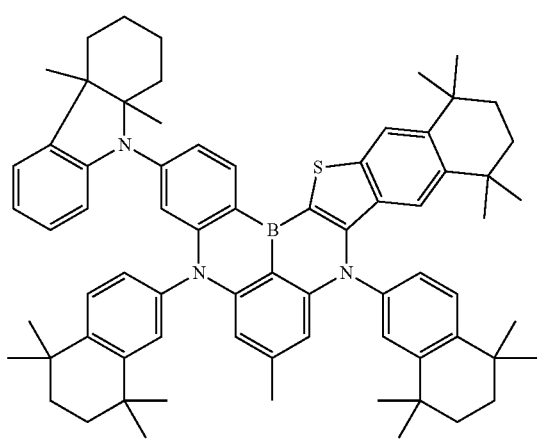
402
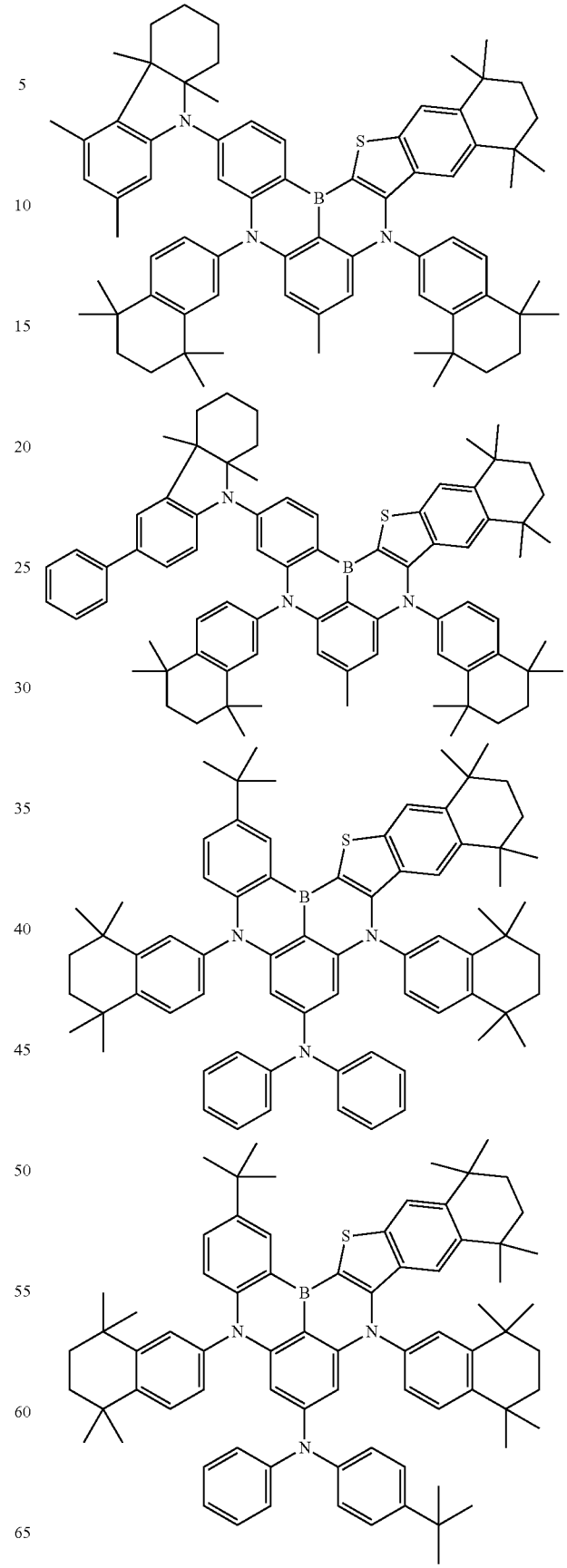

403
-continued
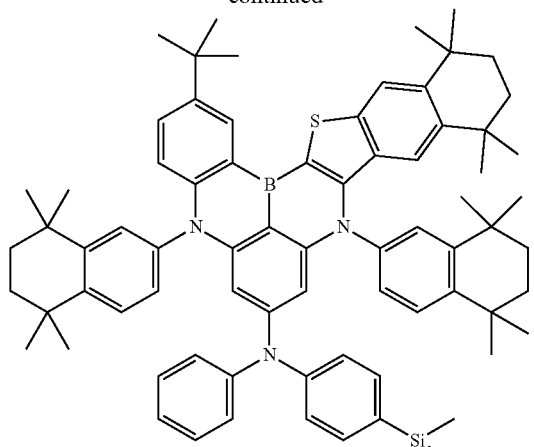
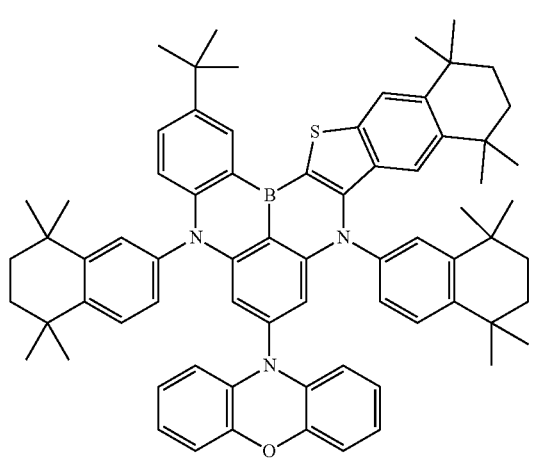
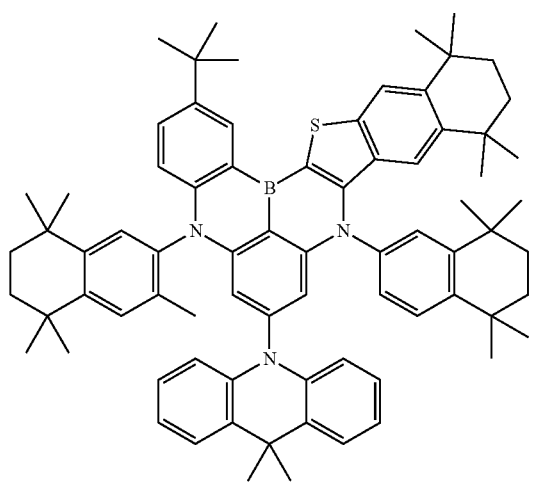
404
-continued
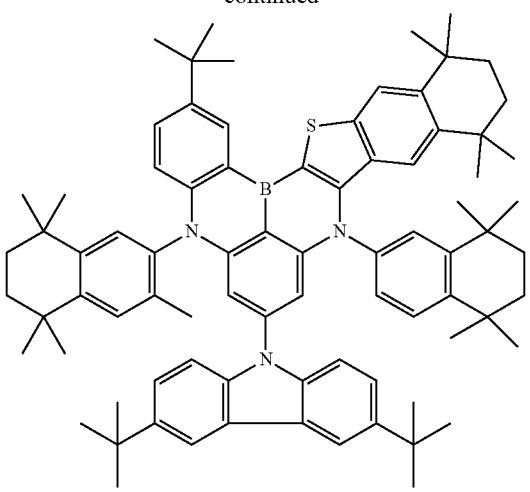
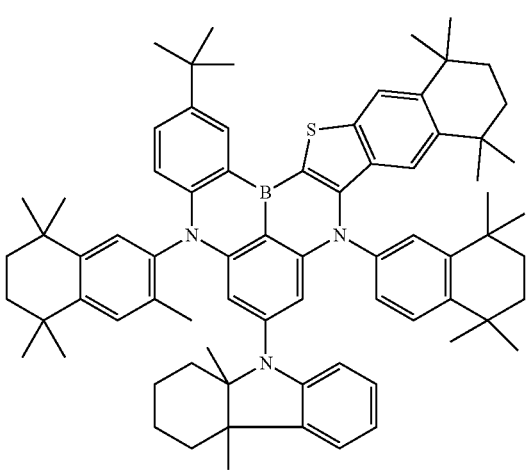
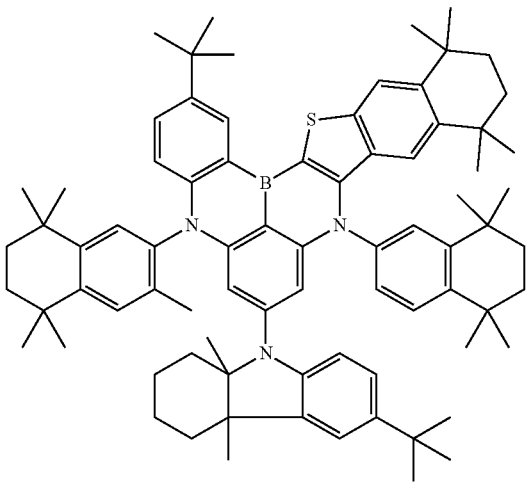

405
-continued
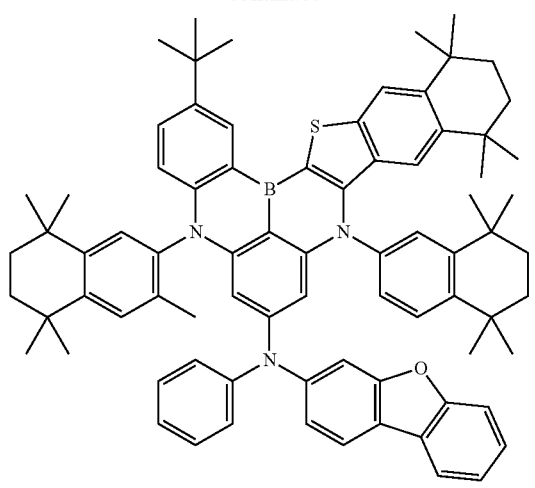
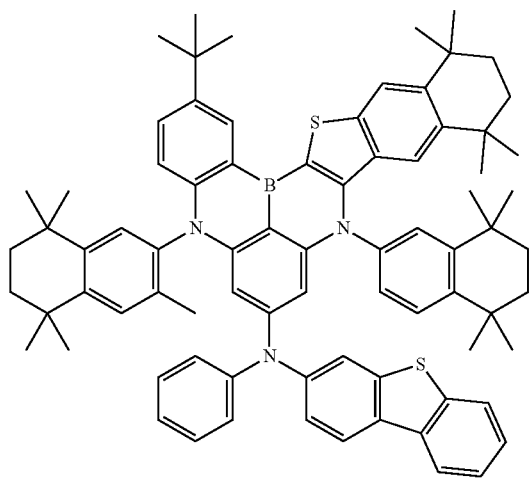
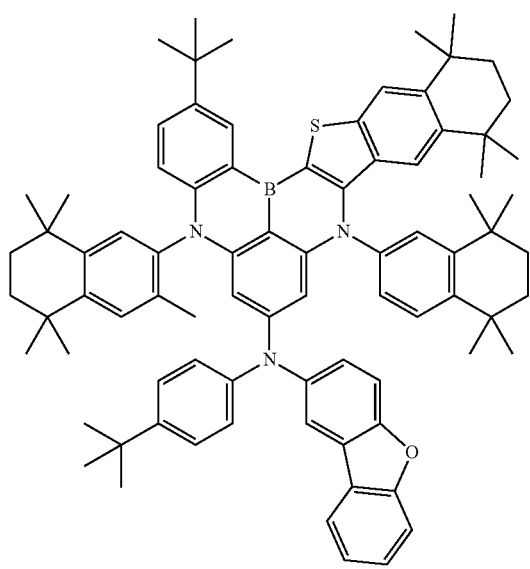
406
-continued
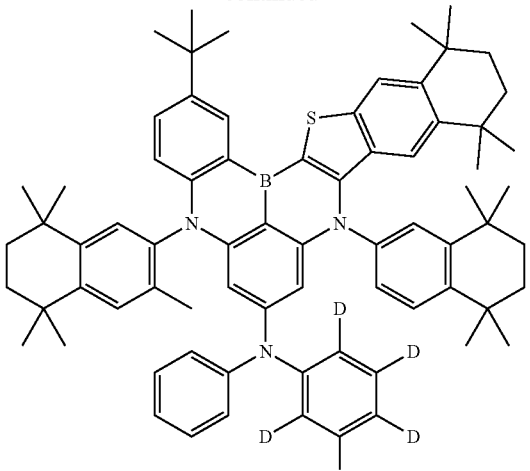
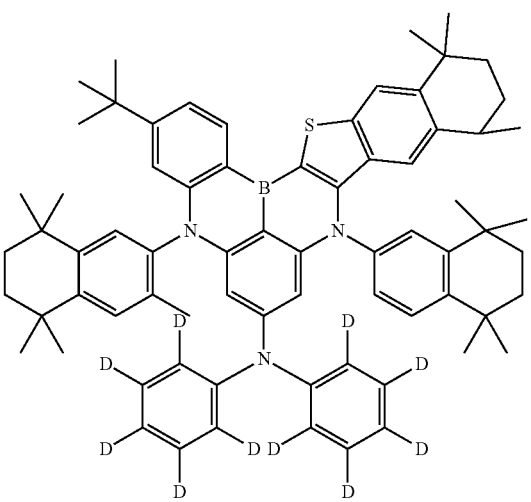
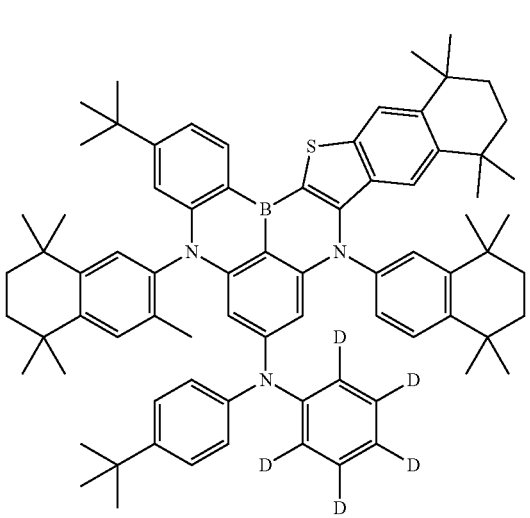

407
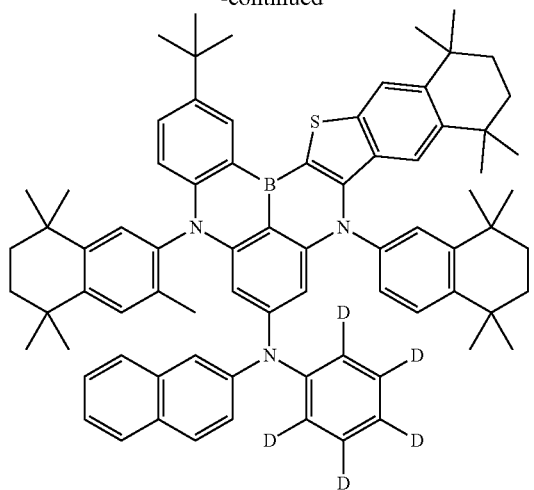
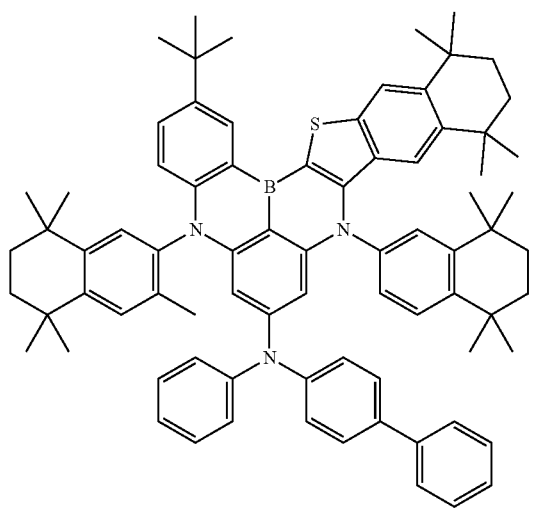
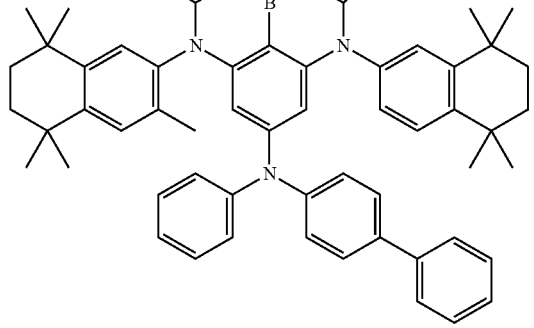
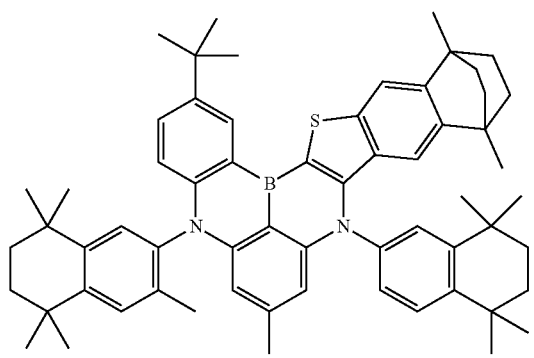
408
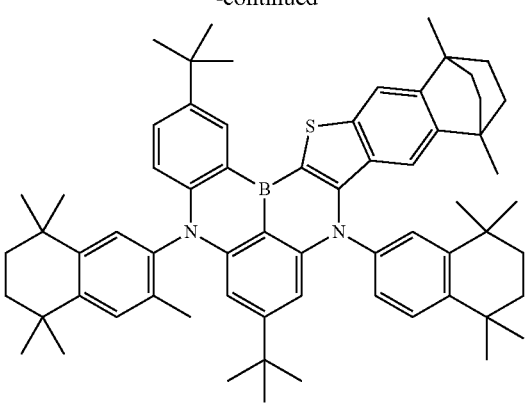
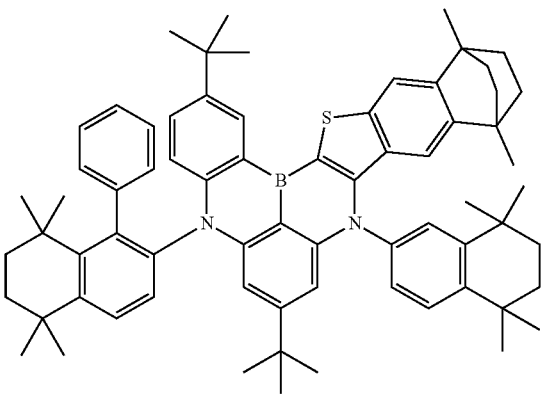
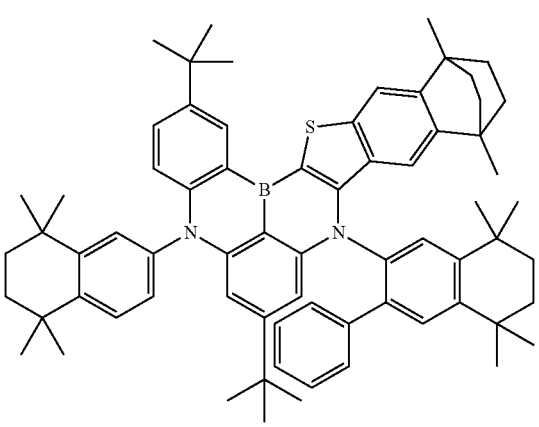
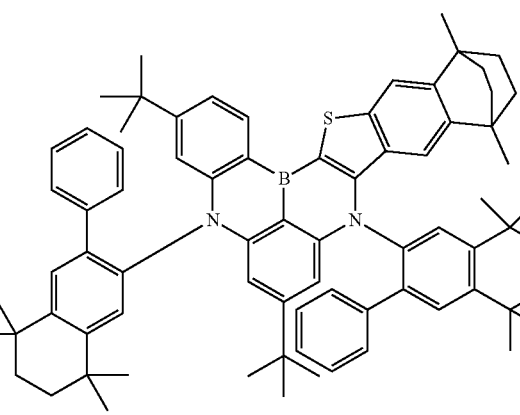

| 409 -continued | 410 -continued |
|---|---|
| 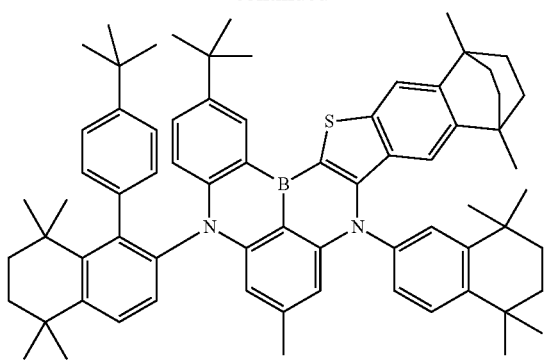 | 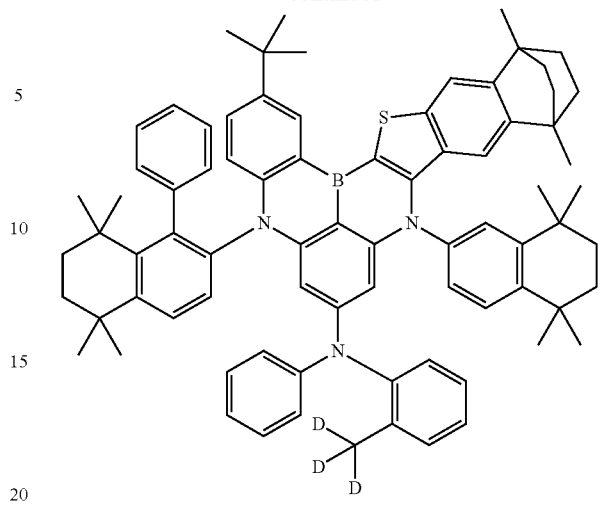 |
| 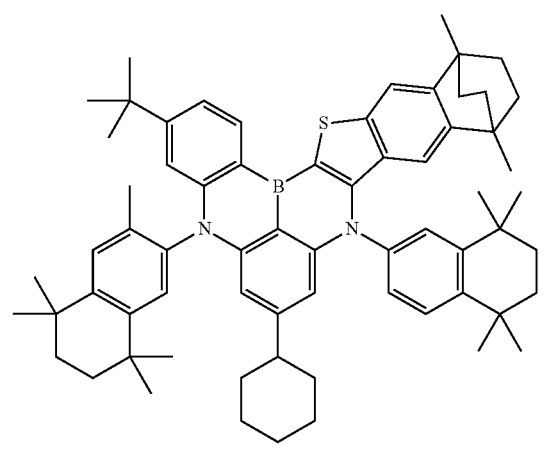 | |
| 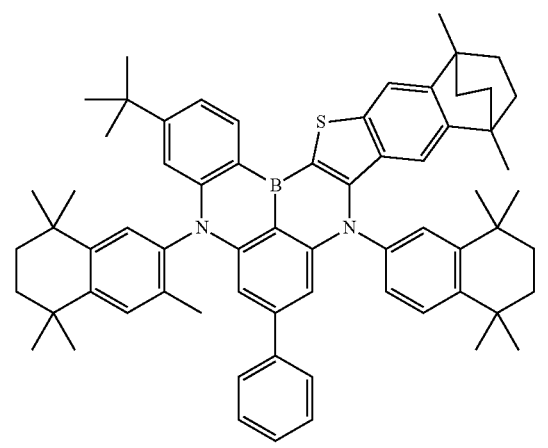 |  |
| 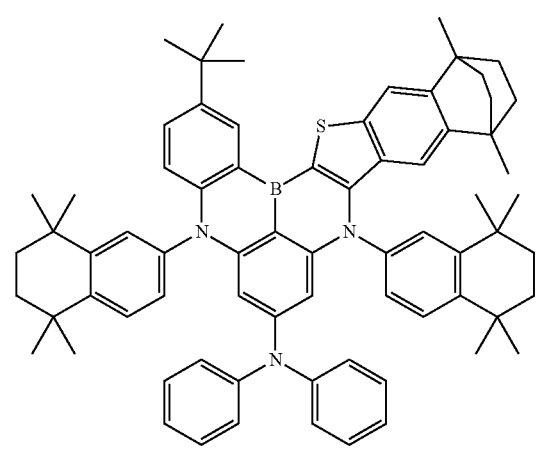 |  |

411
-continued
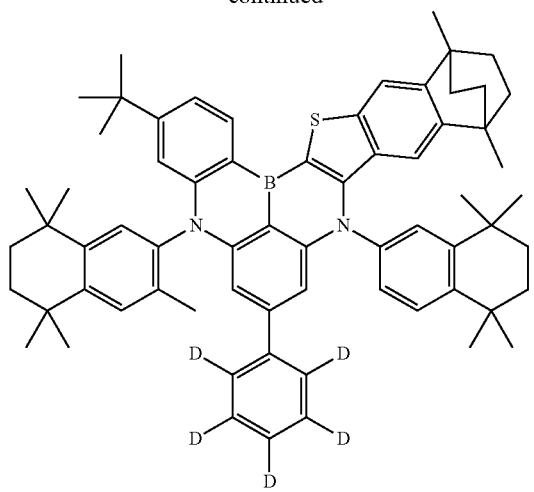
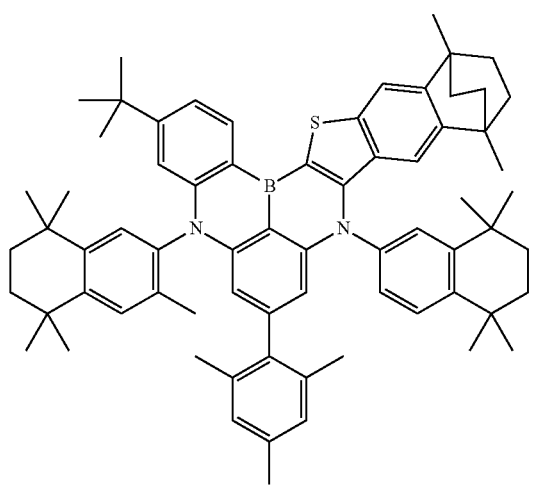
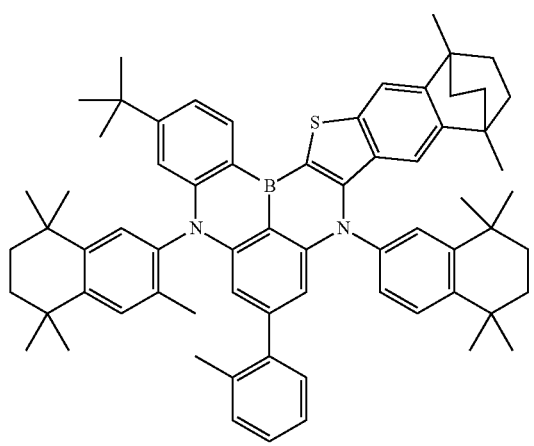
412
-continued
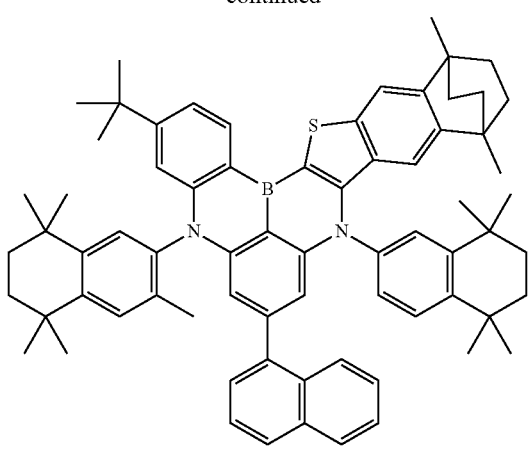
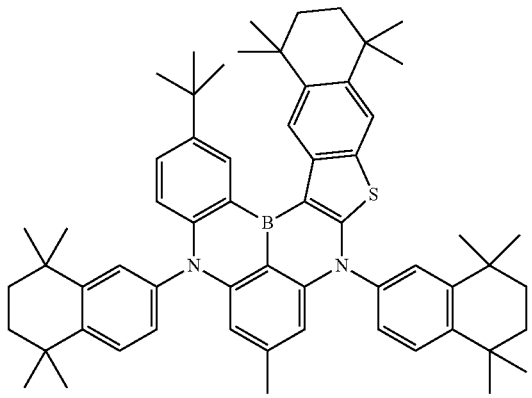
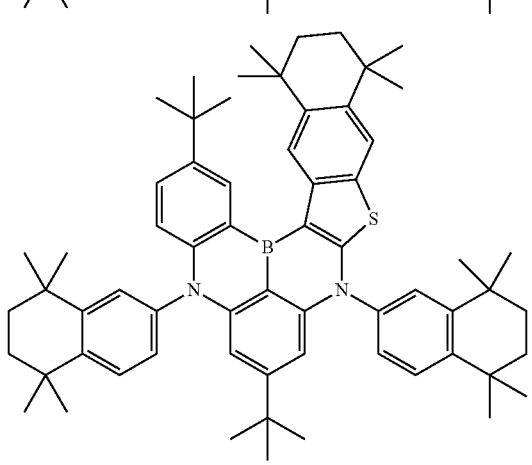
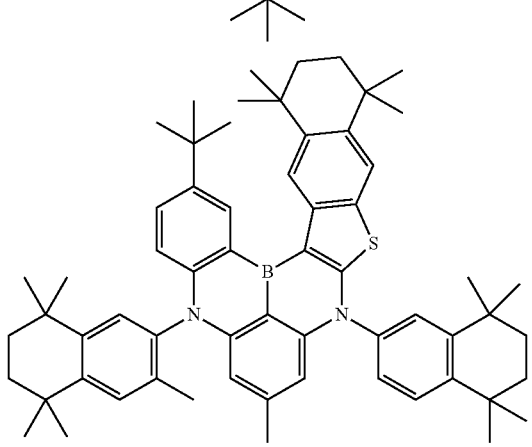

413
-continued
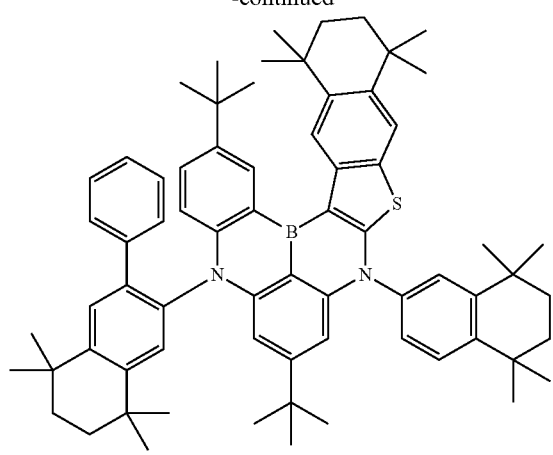
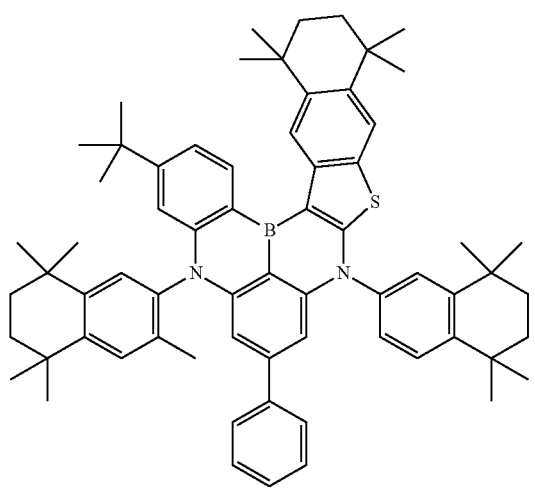
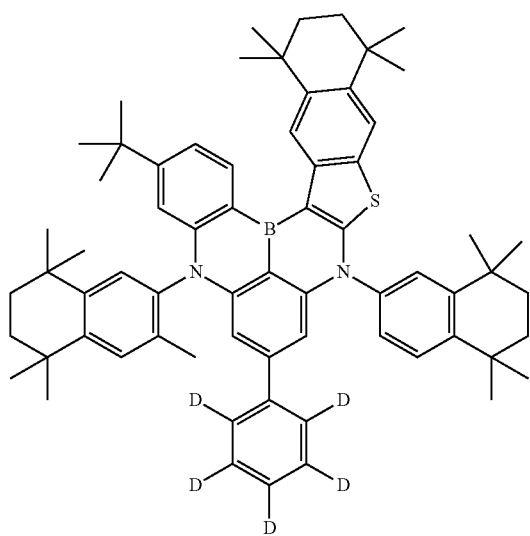
414
-continued
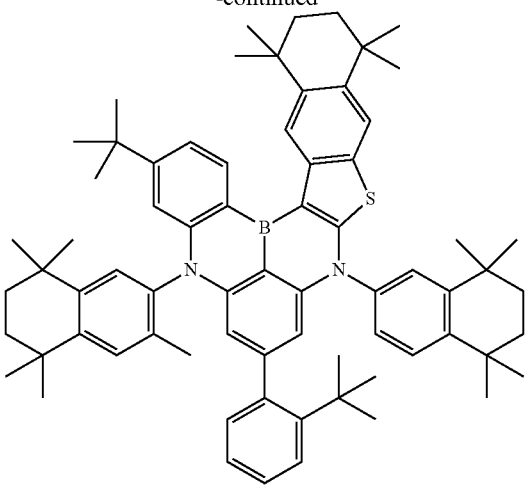
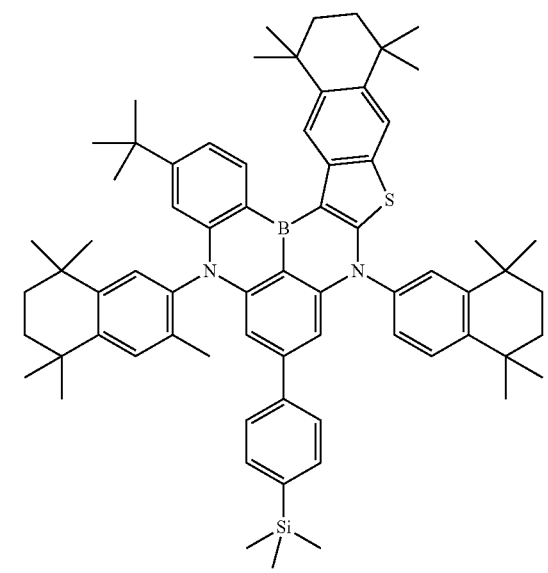
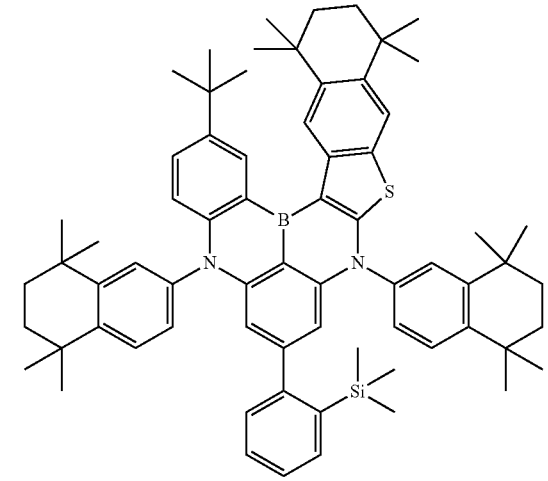

415
-continued
416
-continued
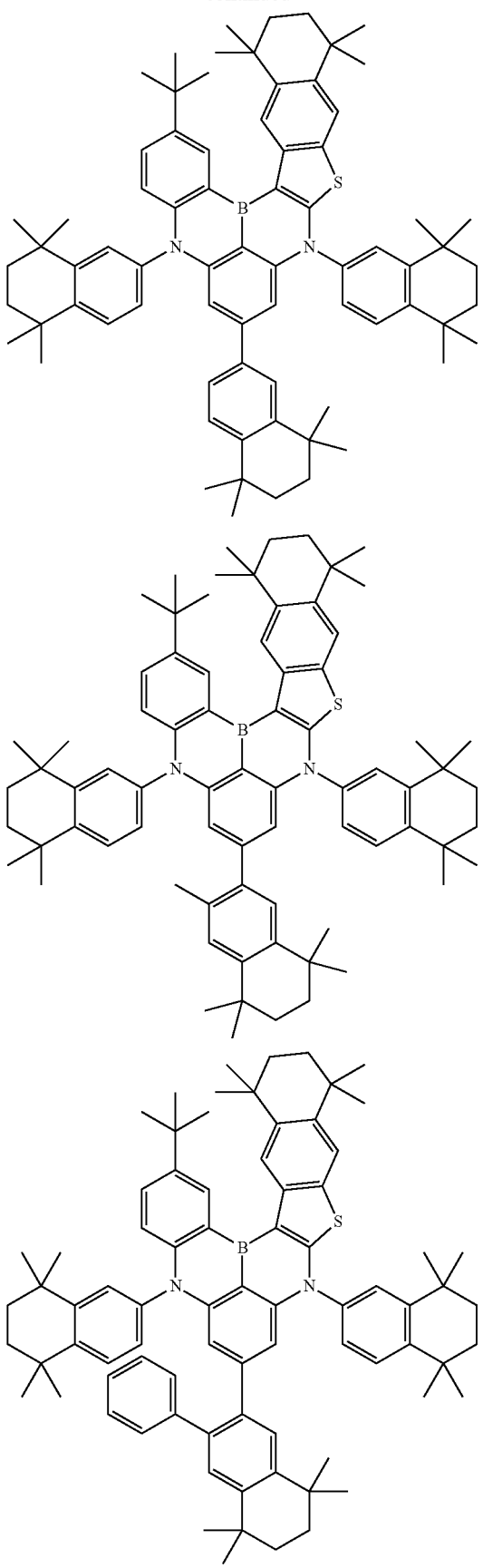

417
-continued
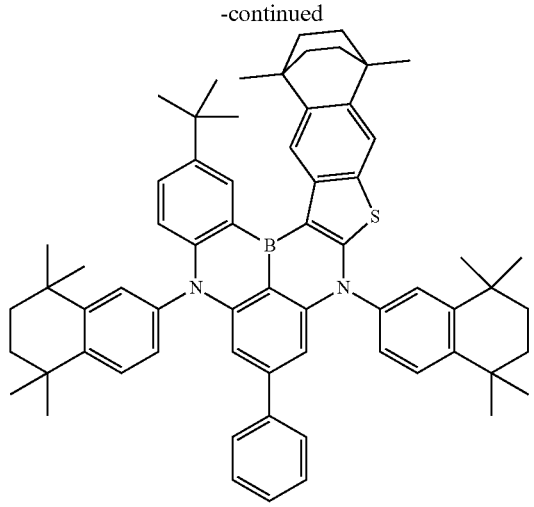
418
-continued
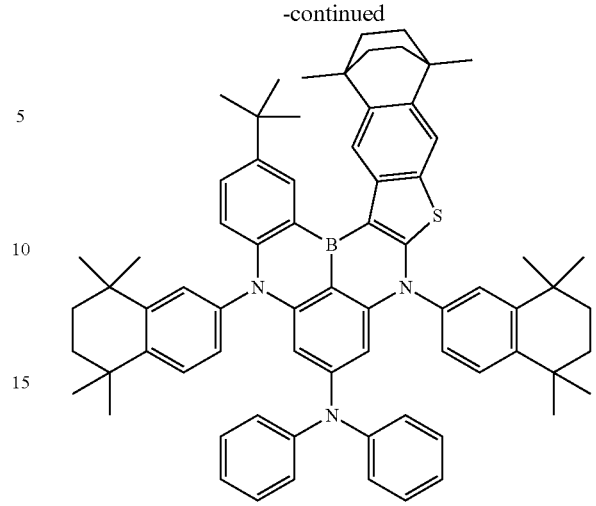
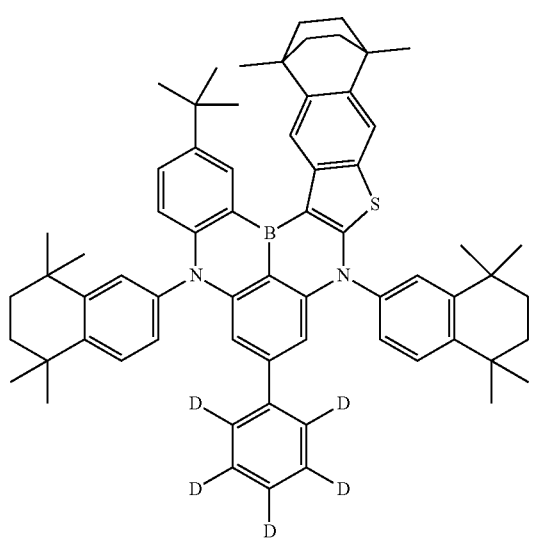
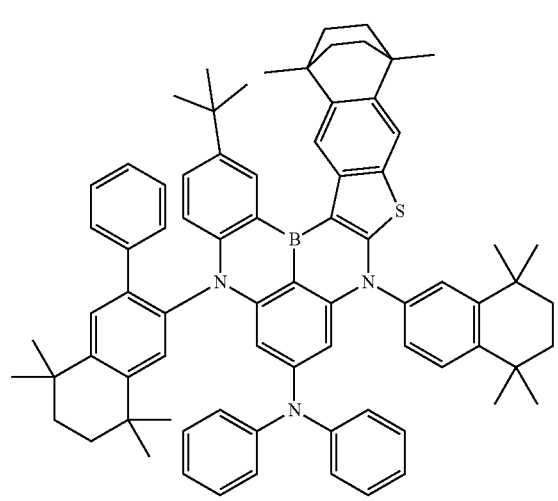
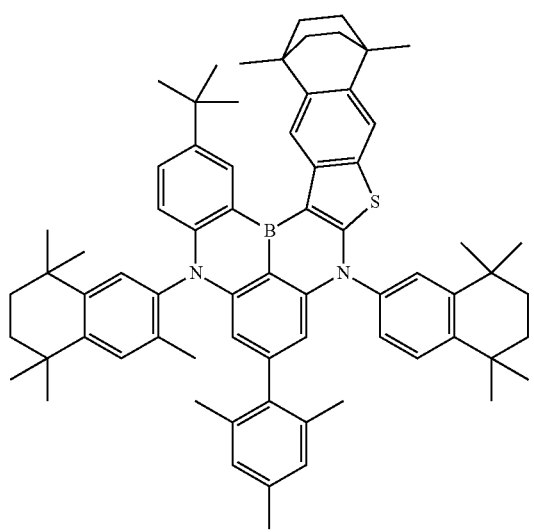
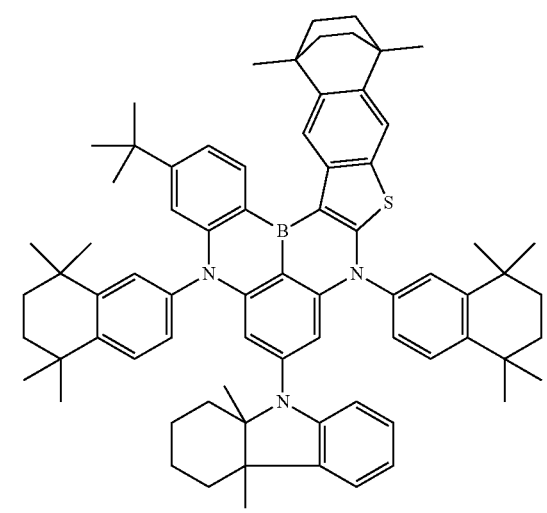

419
-continued
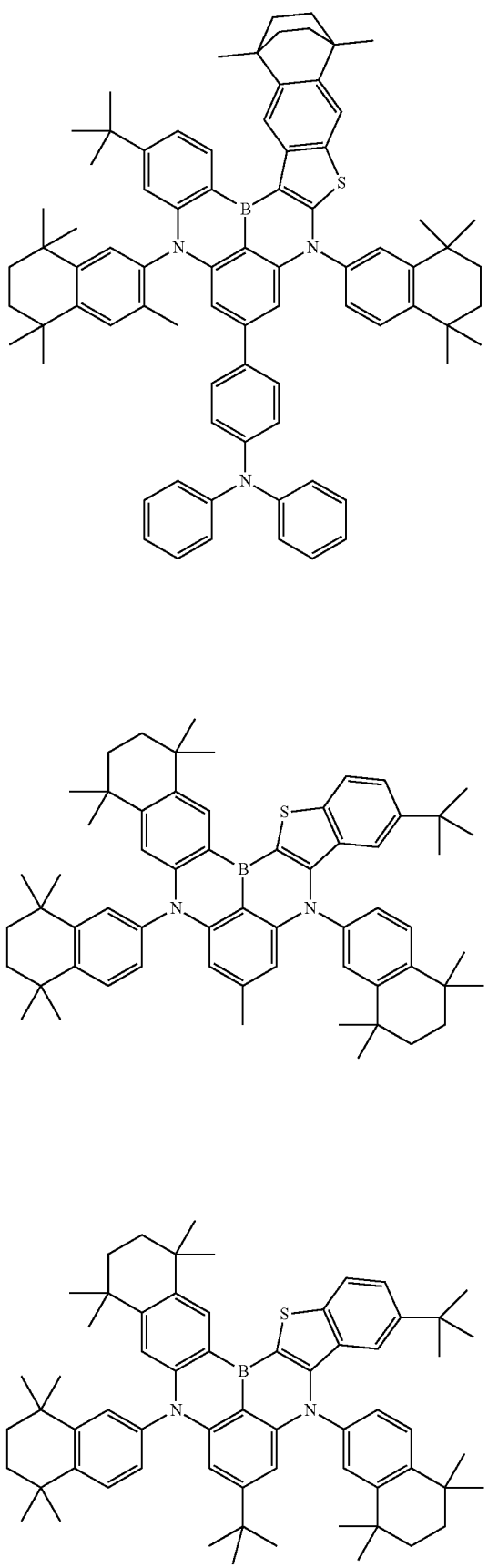
420
-continued
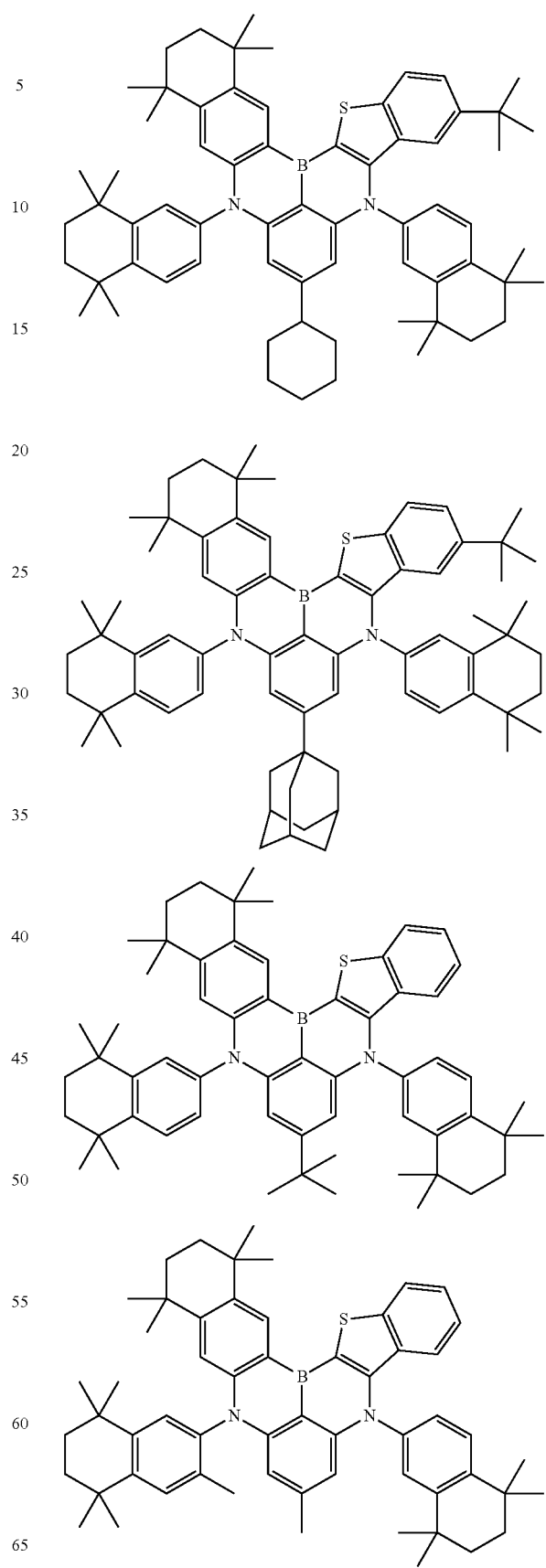

421
-continued
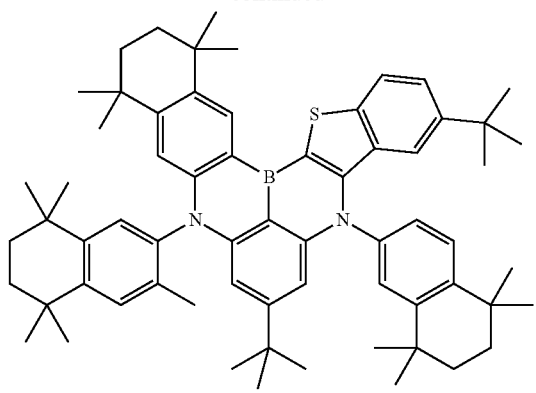
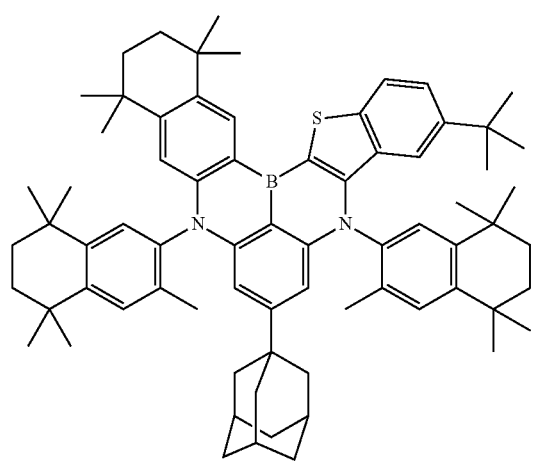
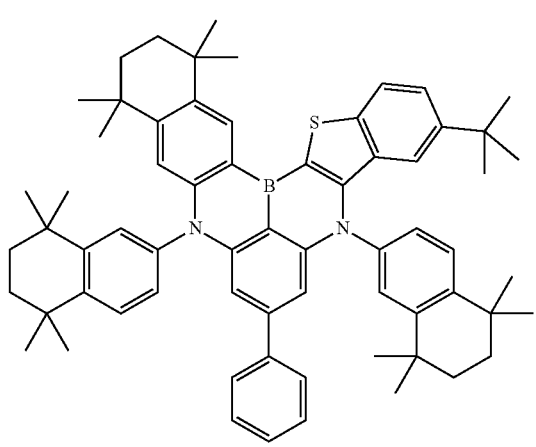
422
-continued
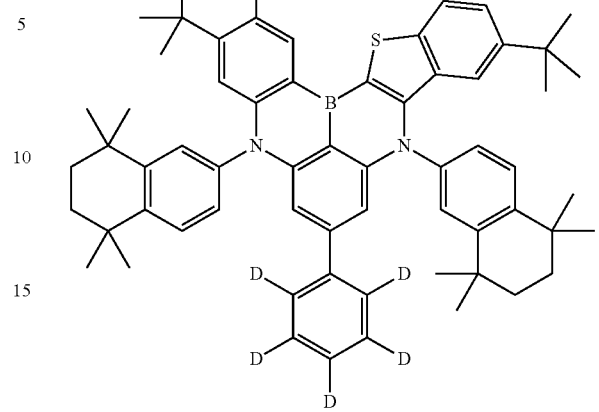
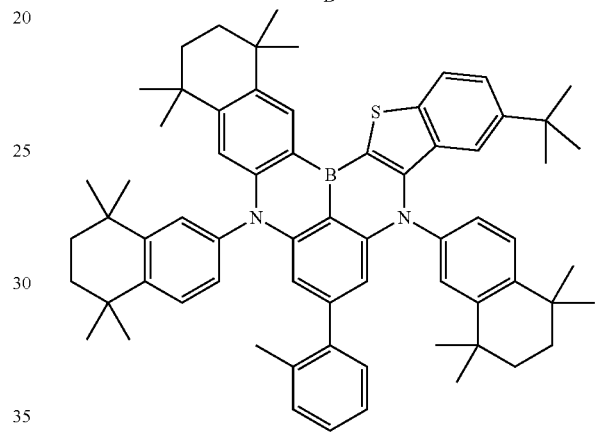
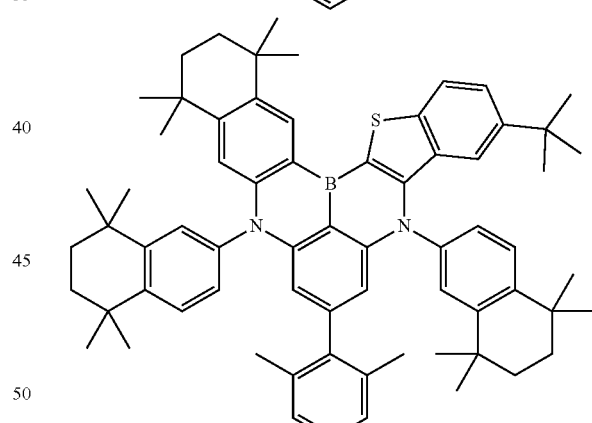
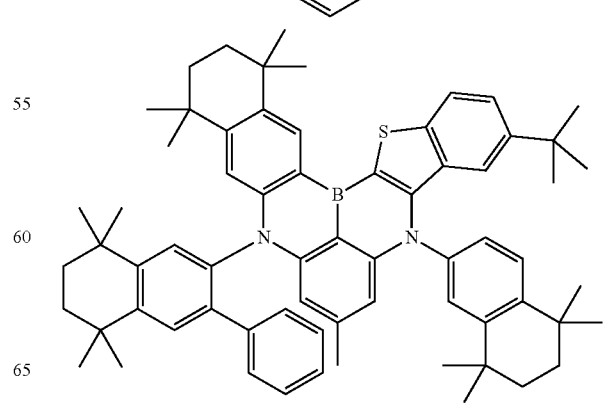

423
-continued
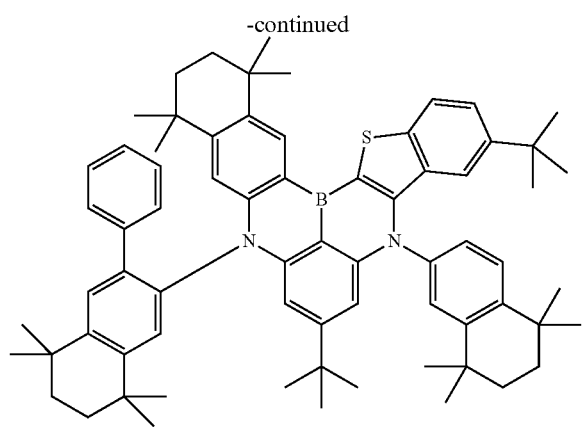
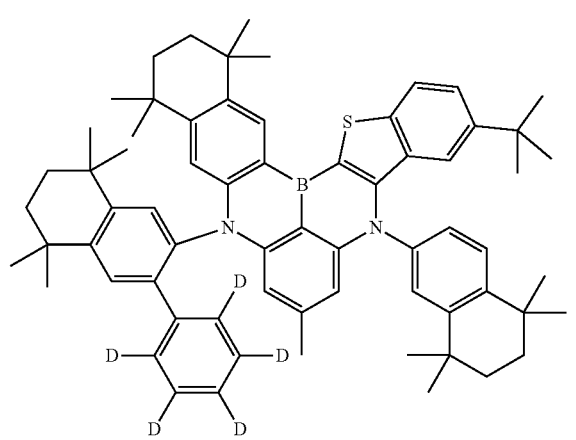
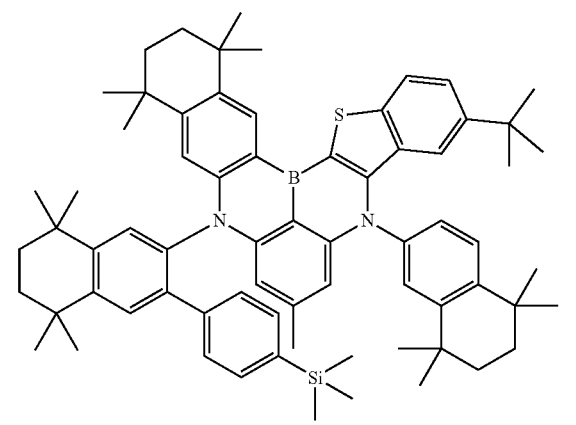
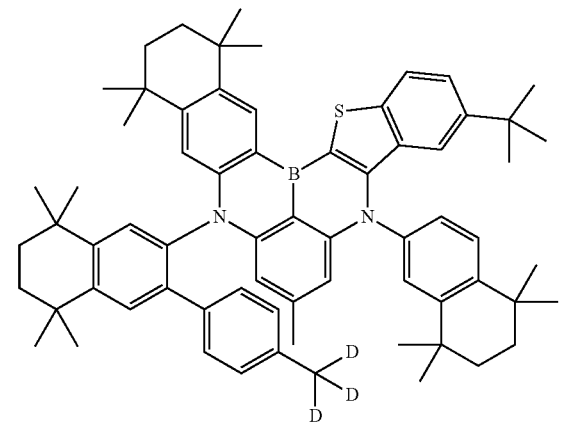
424
-continued
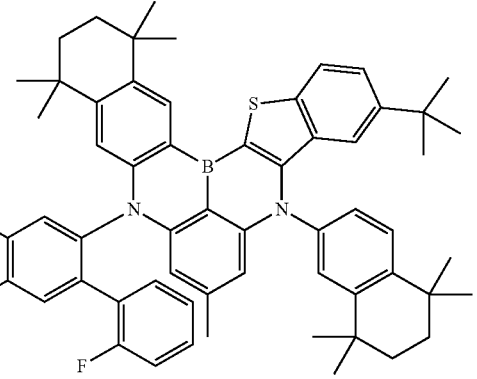
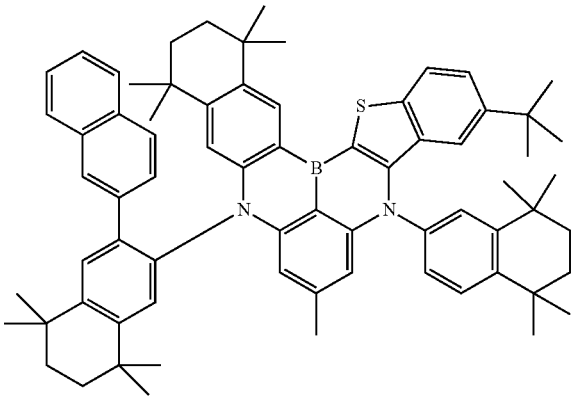
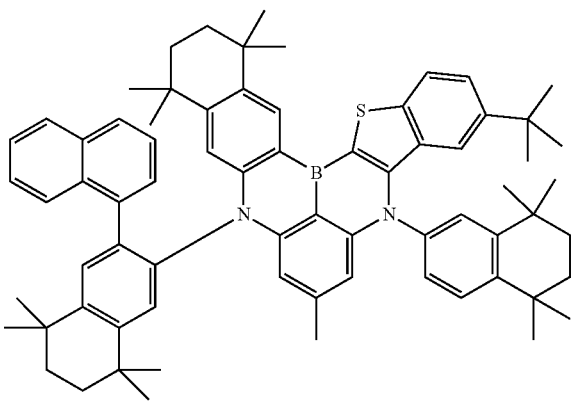
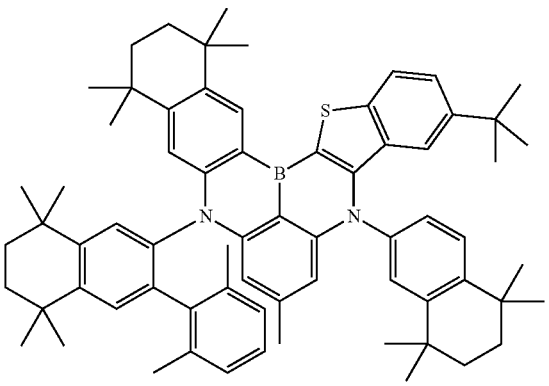

425
-continued
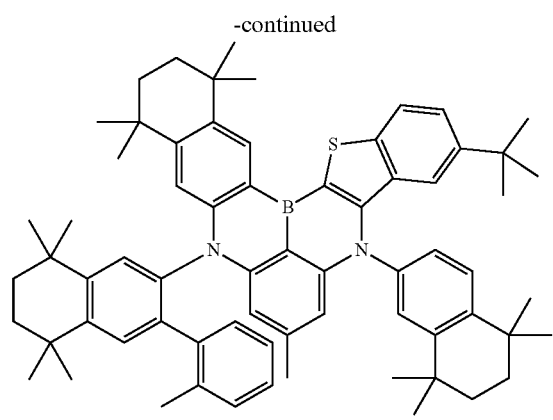
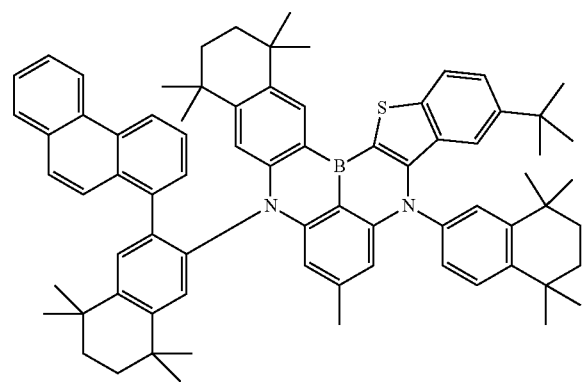
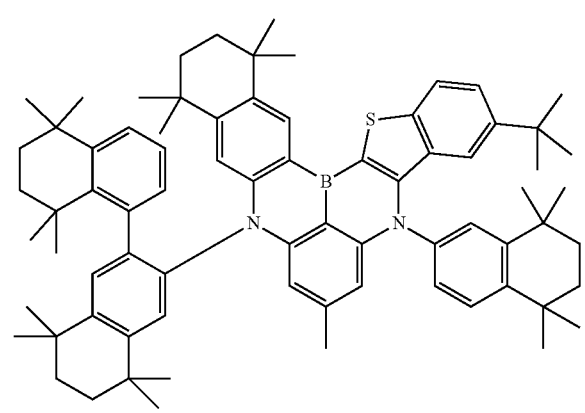
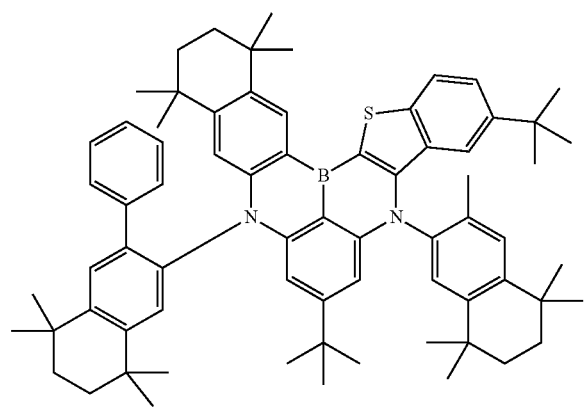
426
-continued
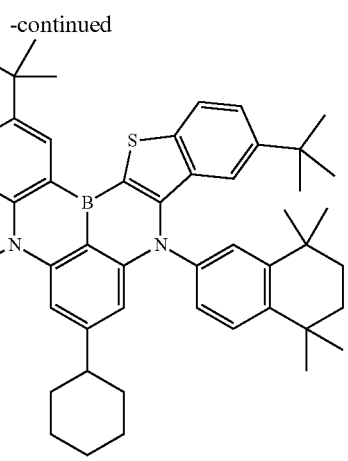
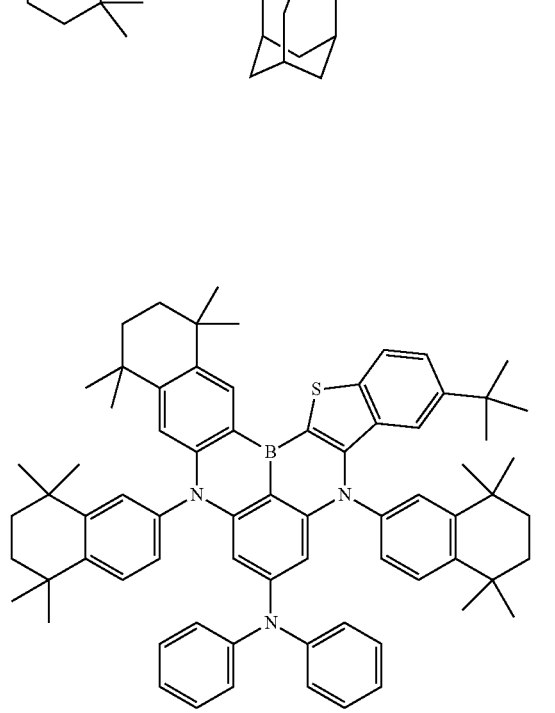

427
-continued
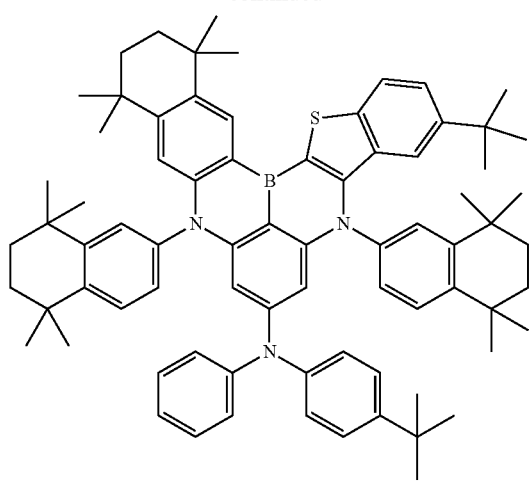
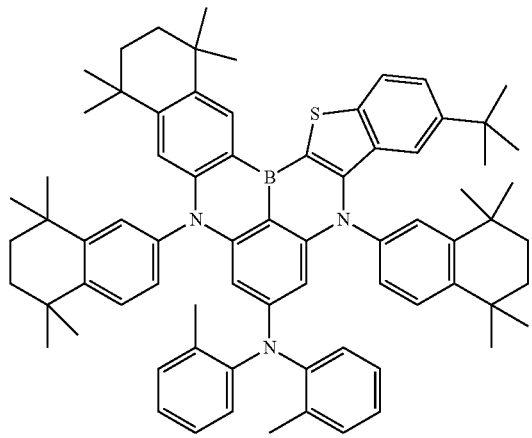
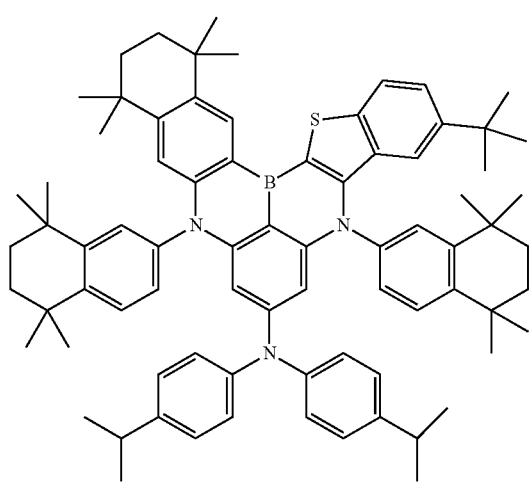
428
-continued
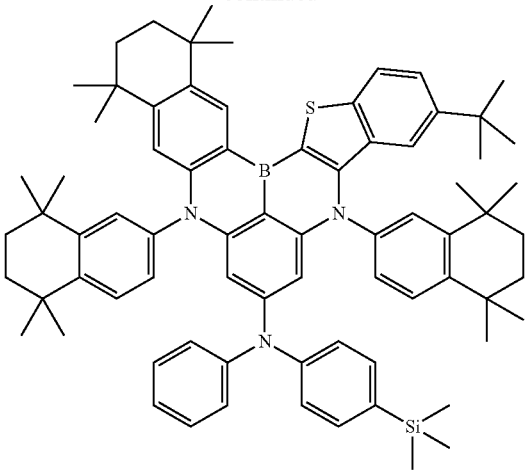
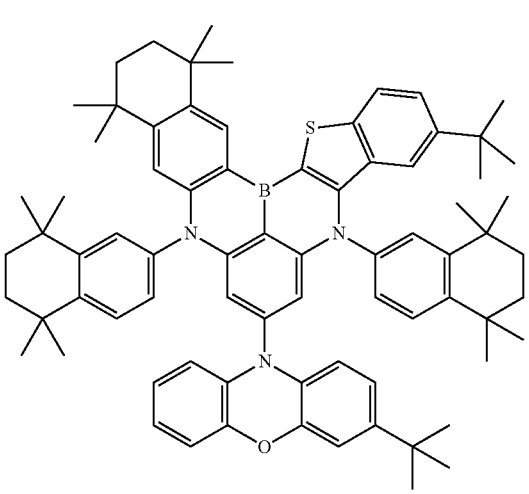
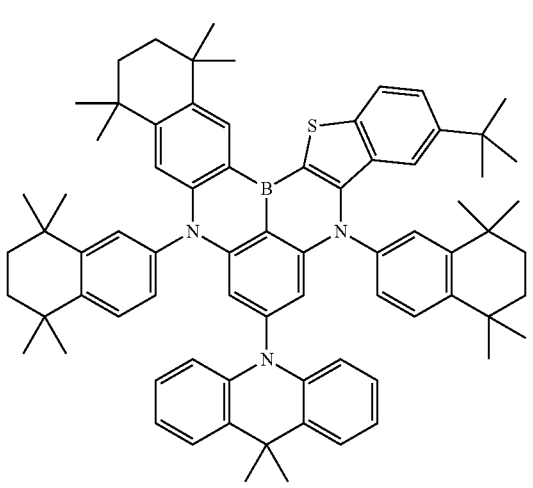

429
-continued
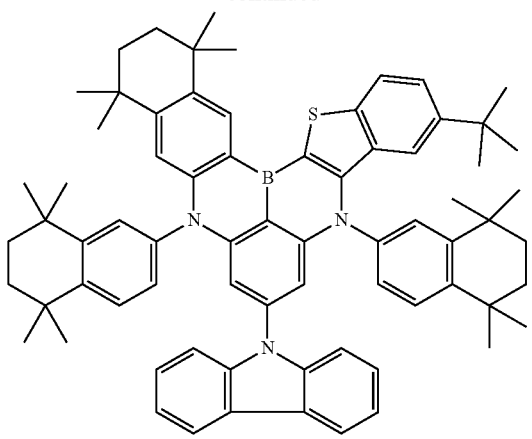
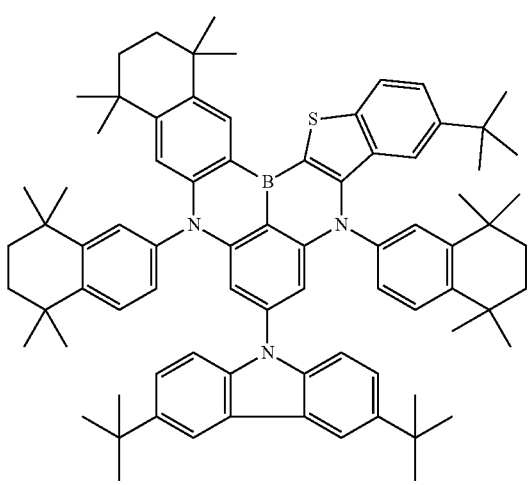
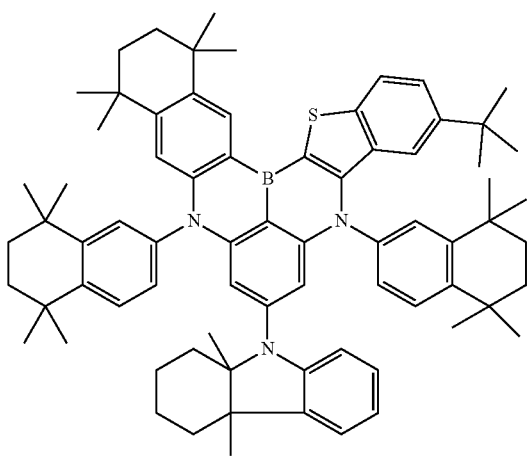
430
-continued
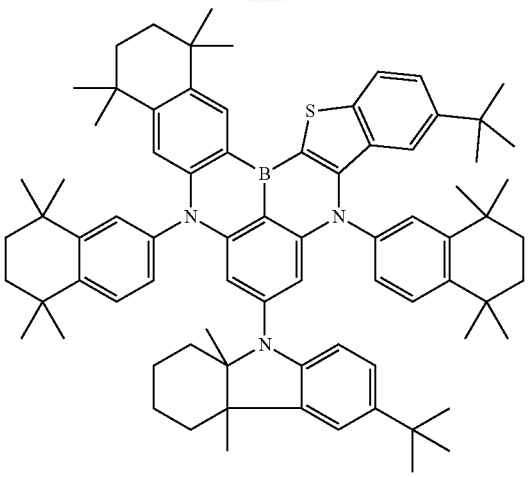
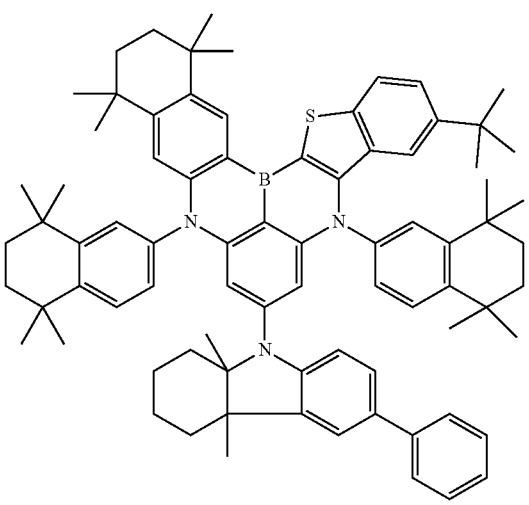
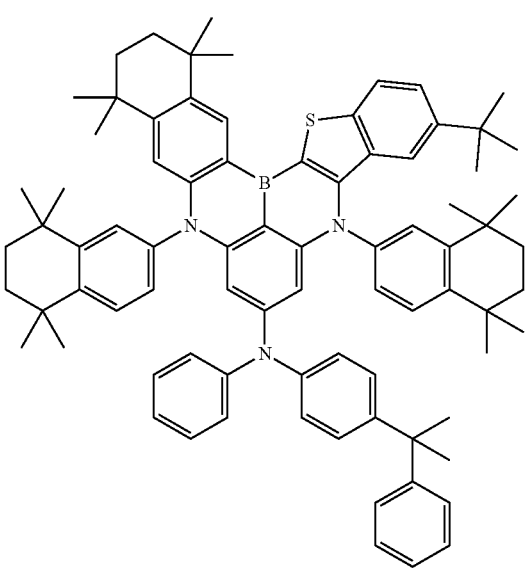

431
-continued
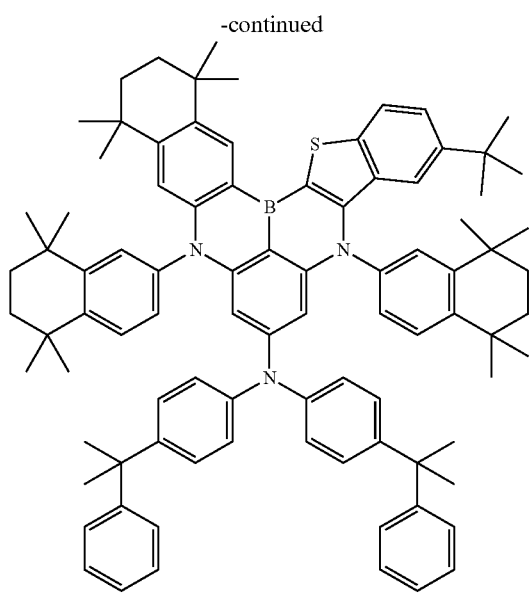
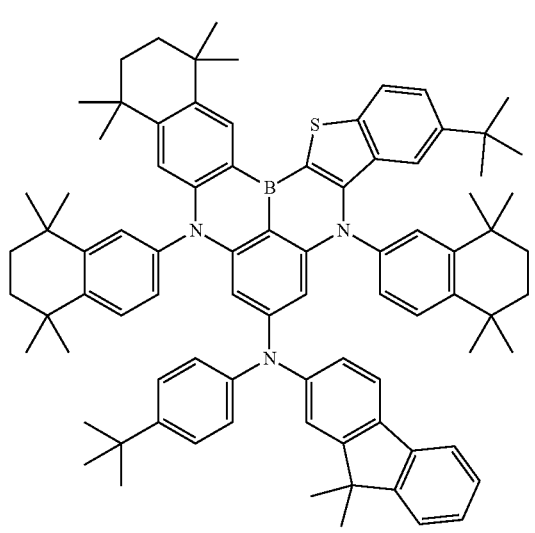
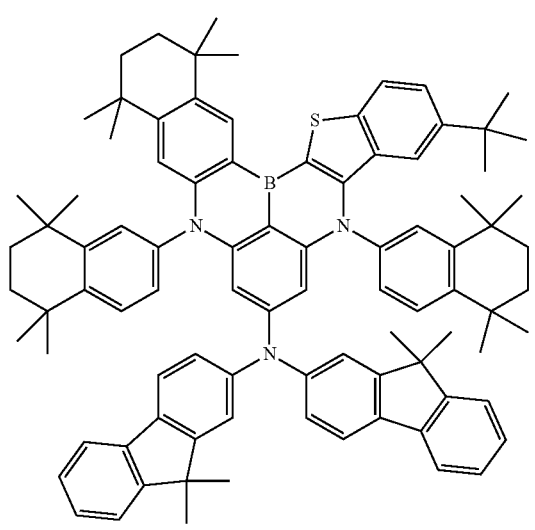
432
-continued
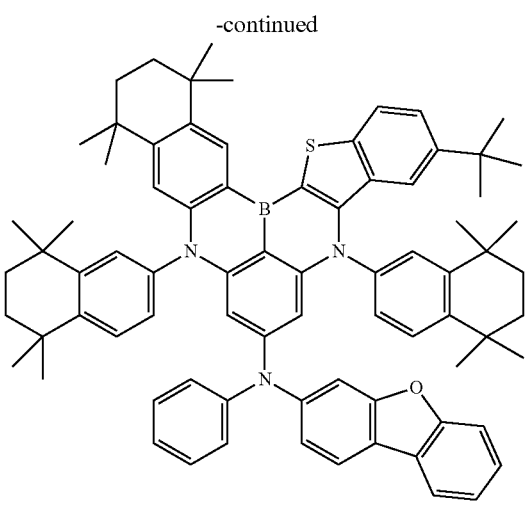
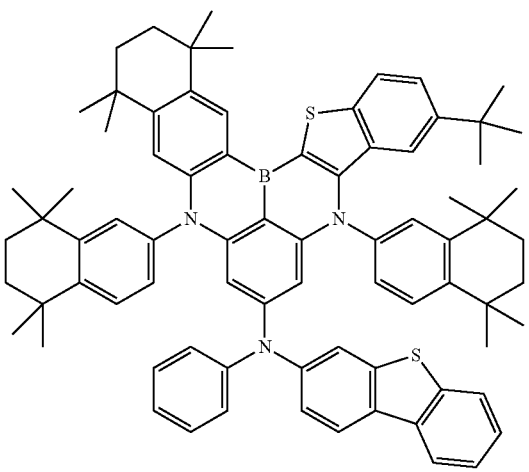
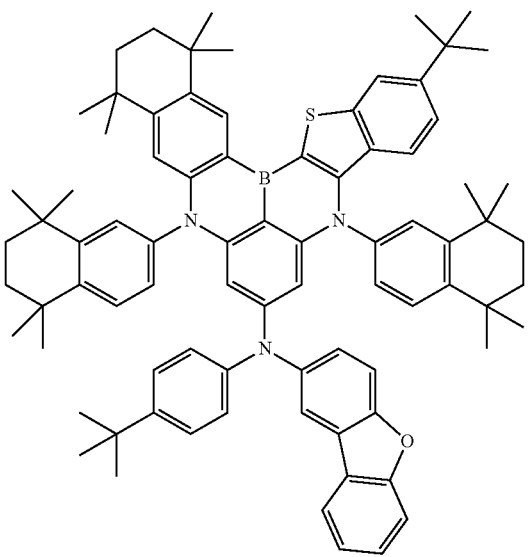

433
-continued
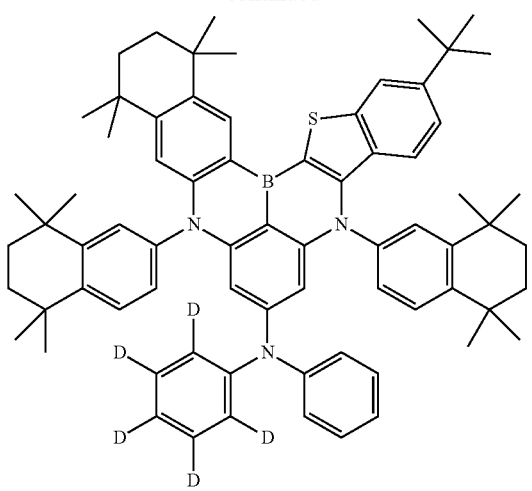
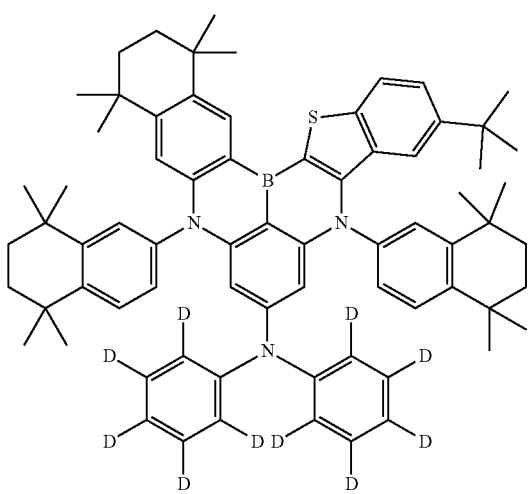
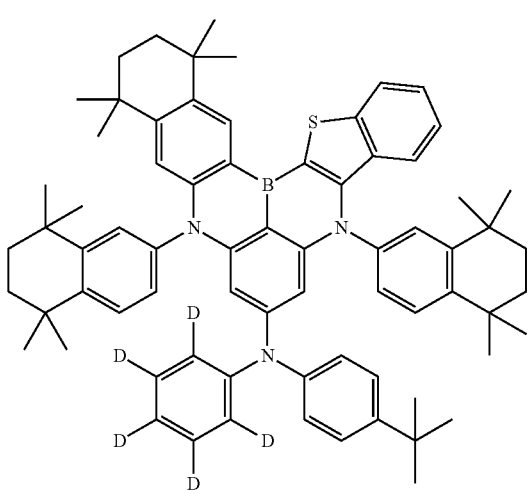
434
-continued
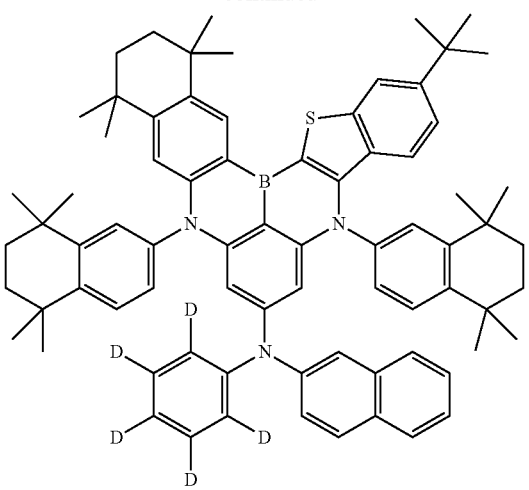
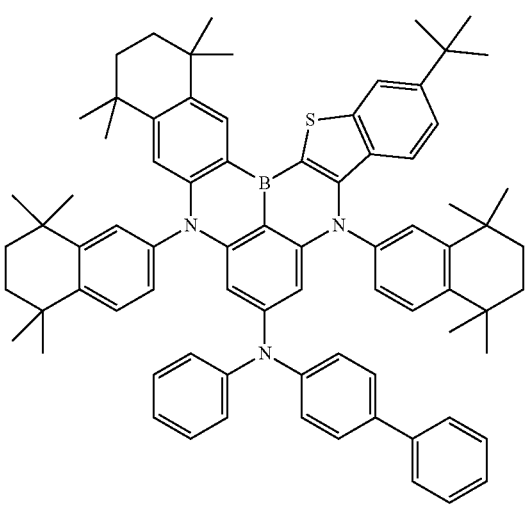
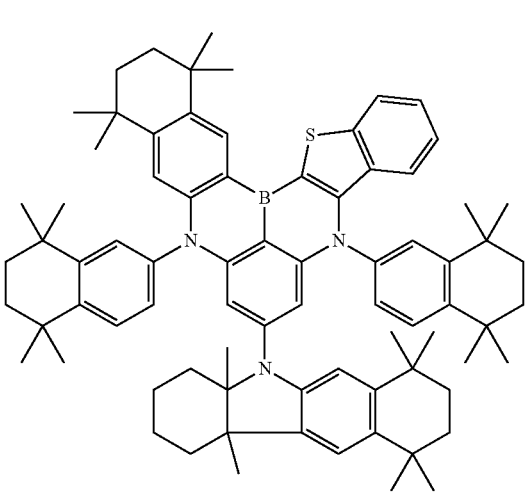

-continued
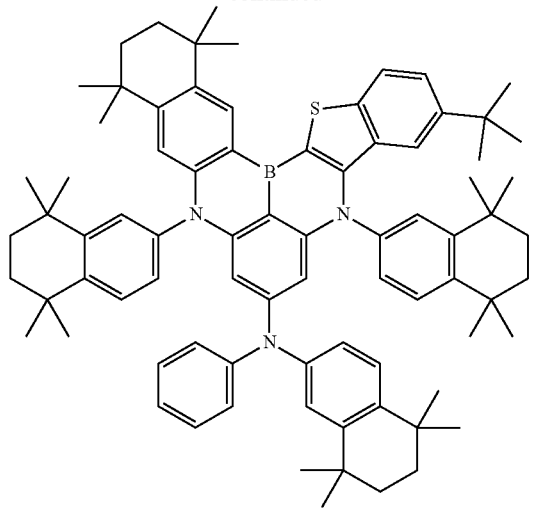
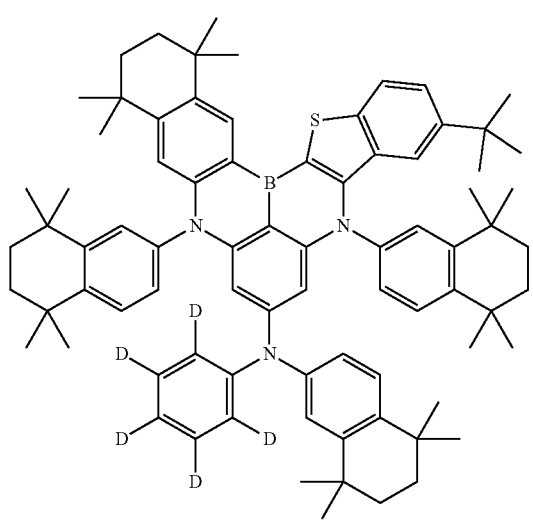
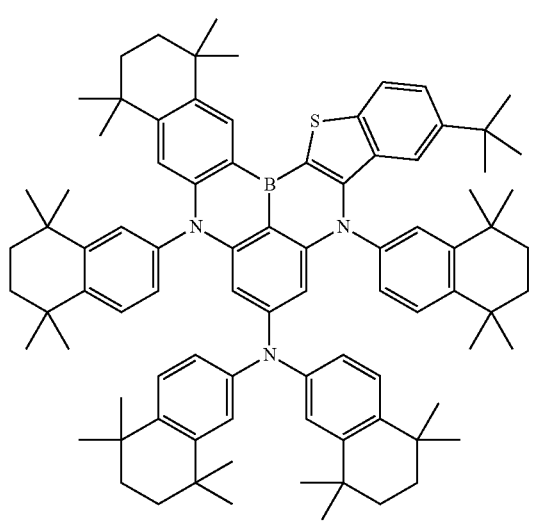
-continued

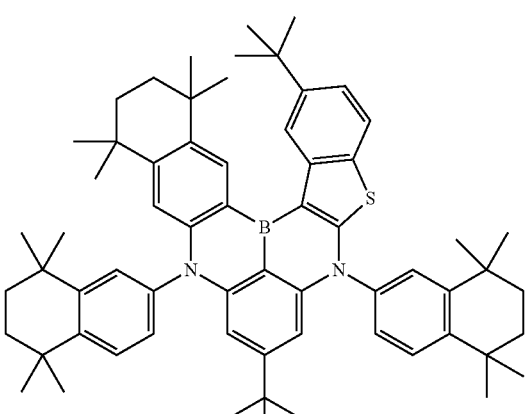
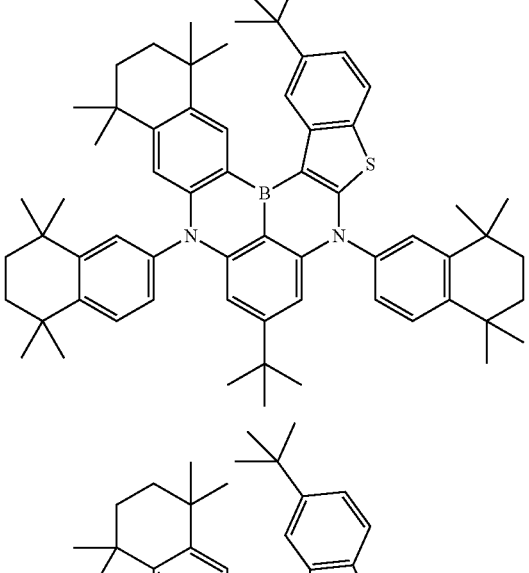
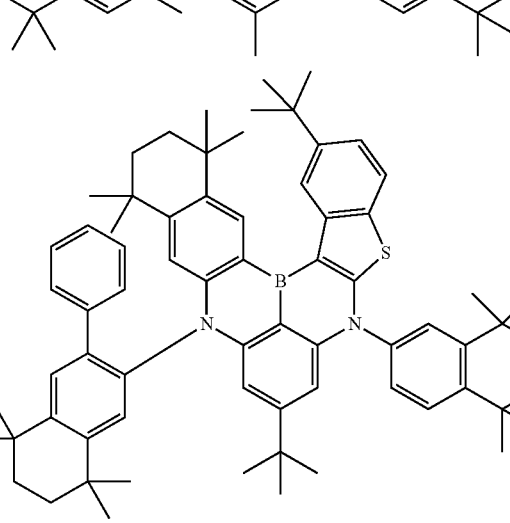

437
-continued
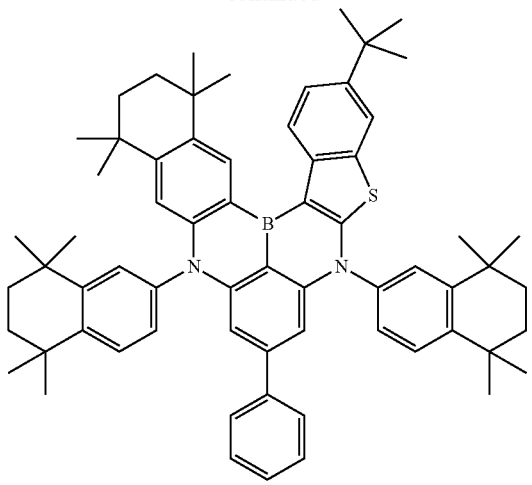
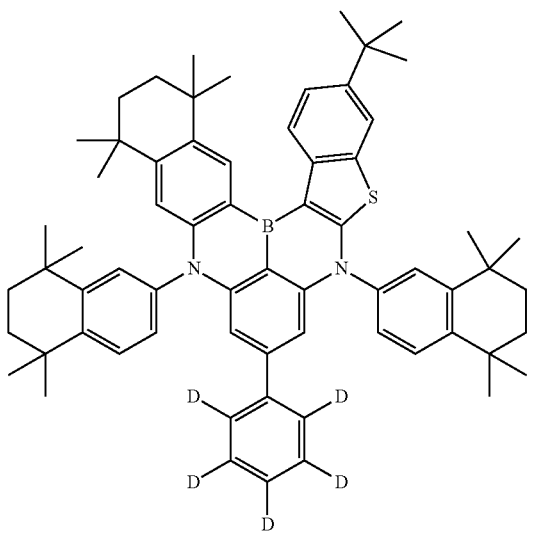
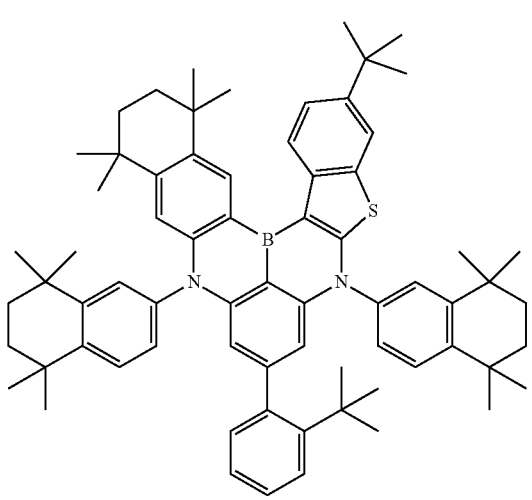
438
-continued
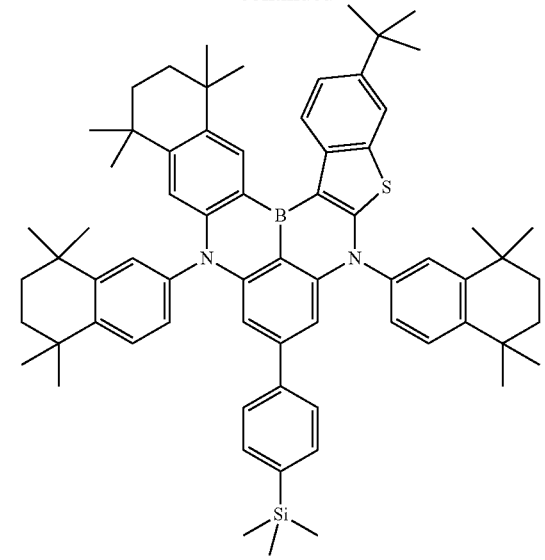
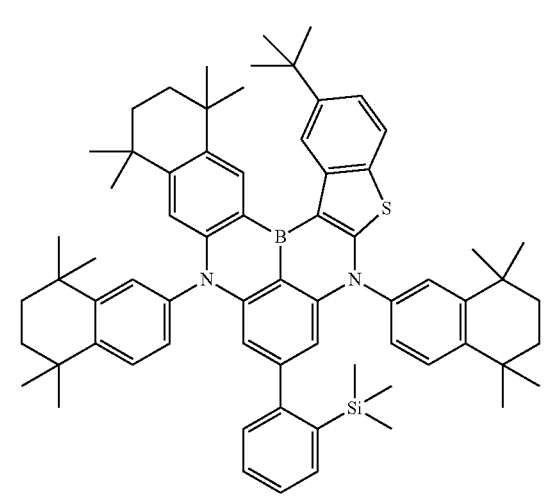
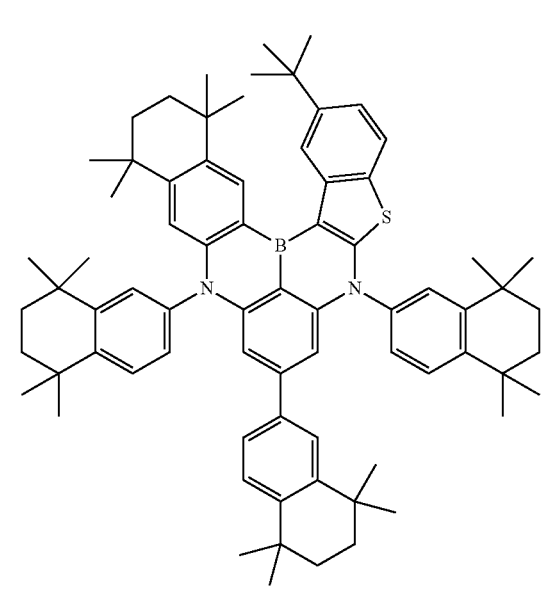

439
-continued
440
-continued
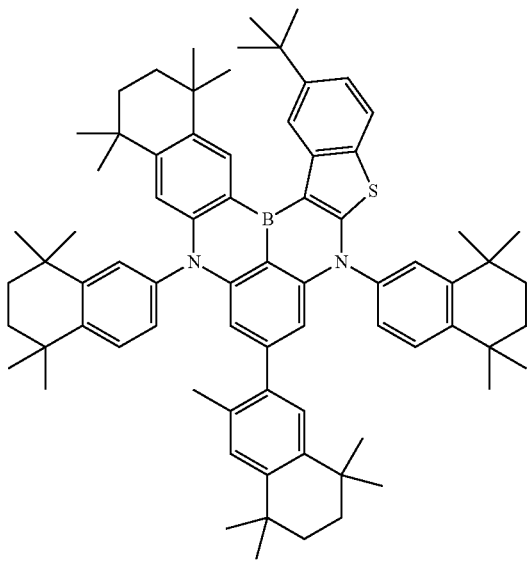
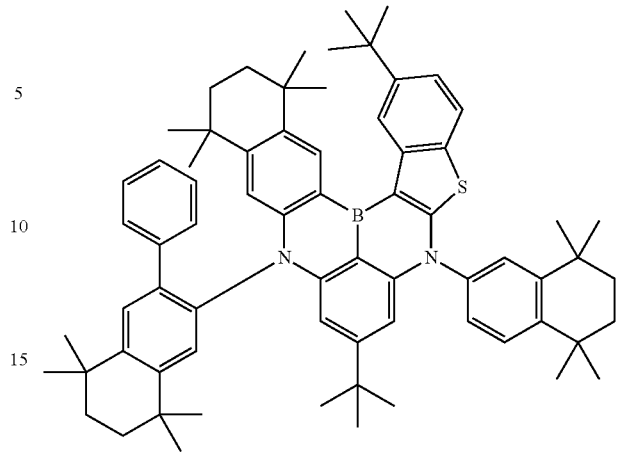
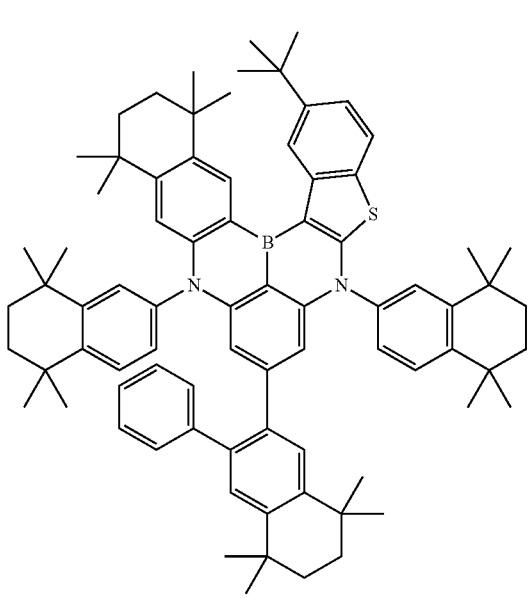
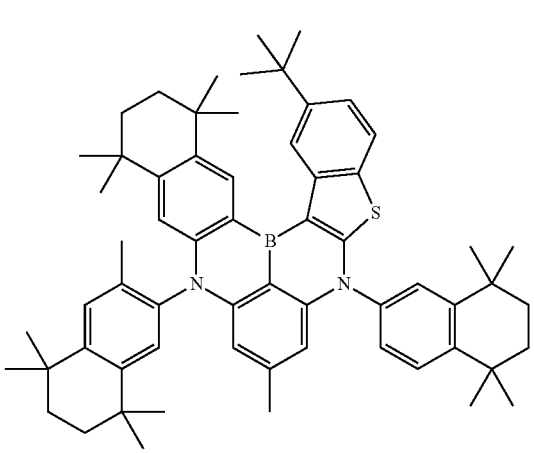
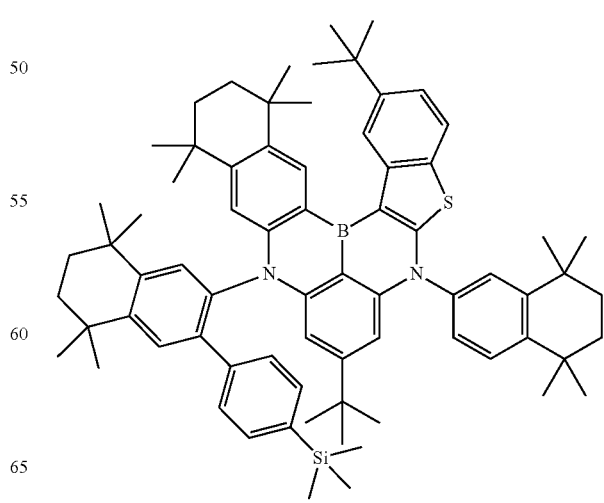

441
-continued
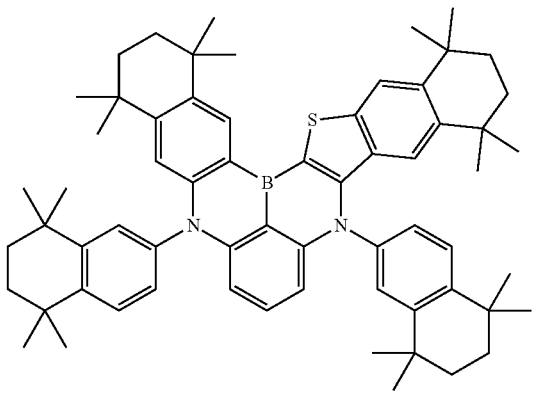
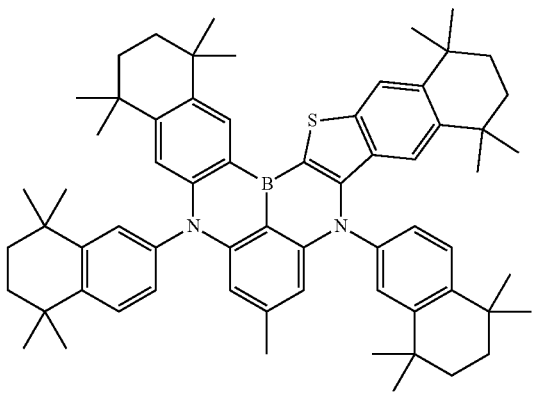
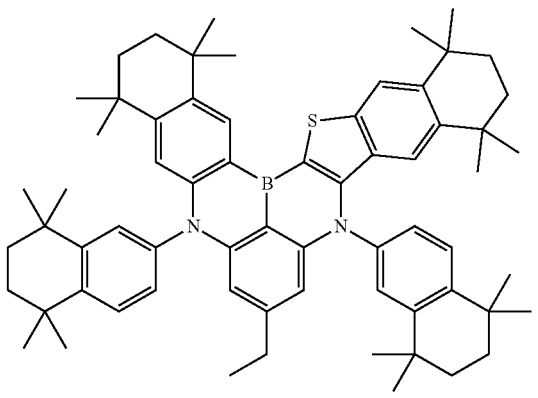
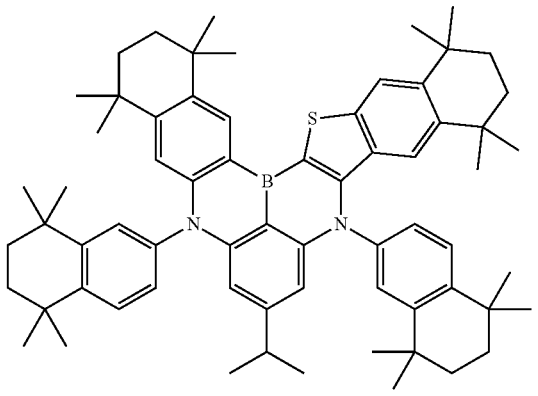
442
-continued
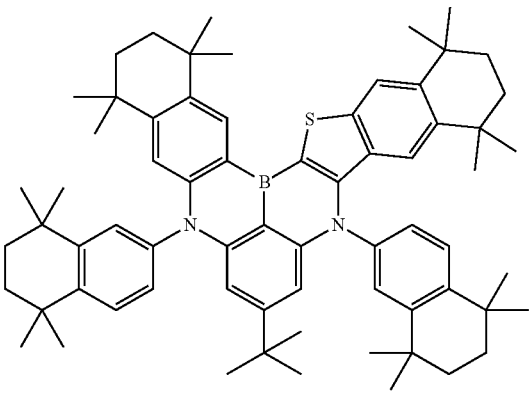
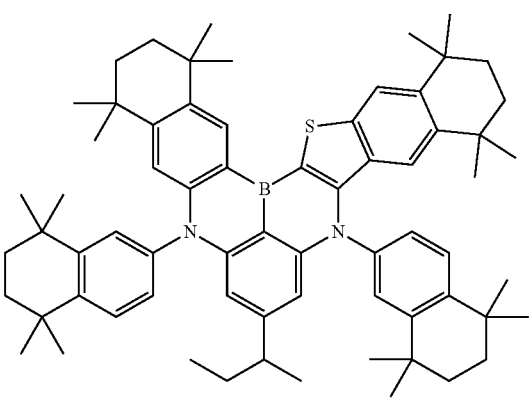
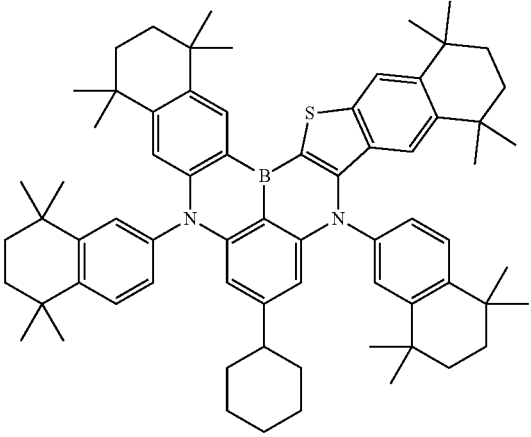
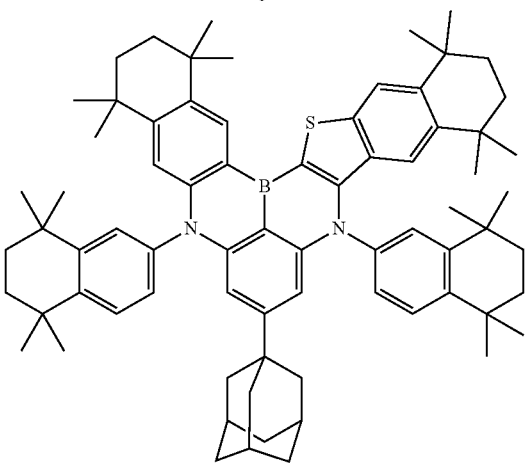

443
-continued

444
-continued

445
-continued
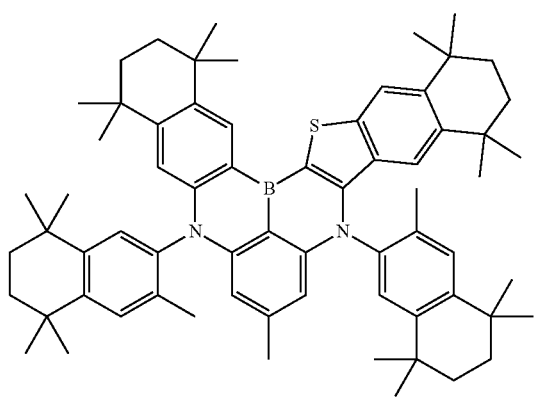
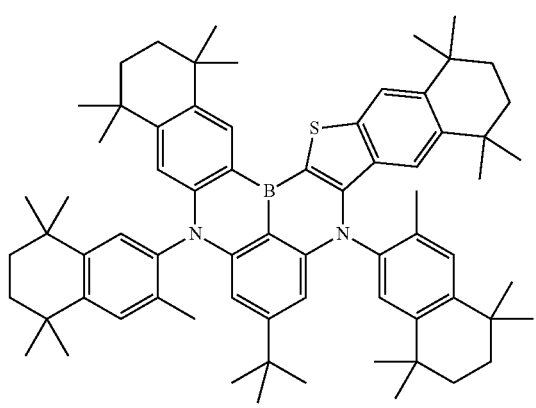
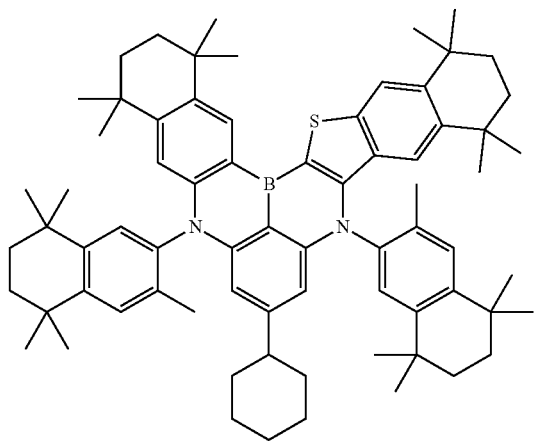
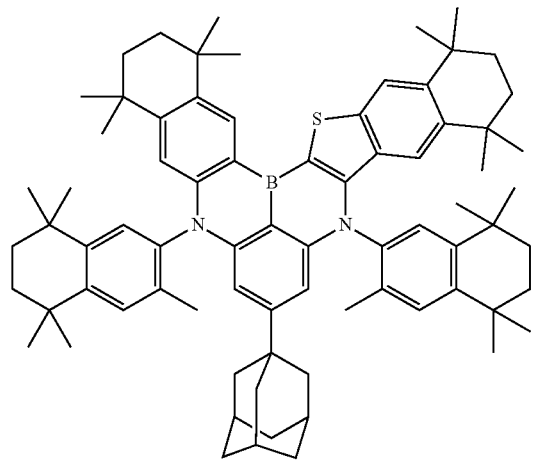
446
-continued
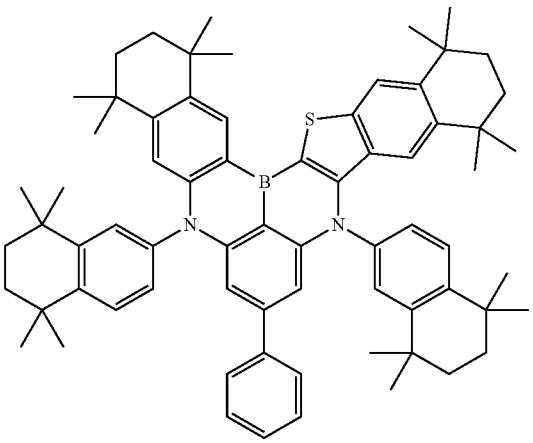
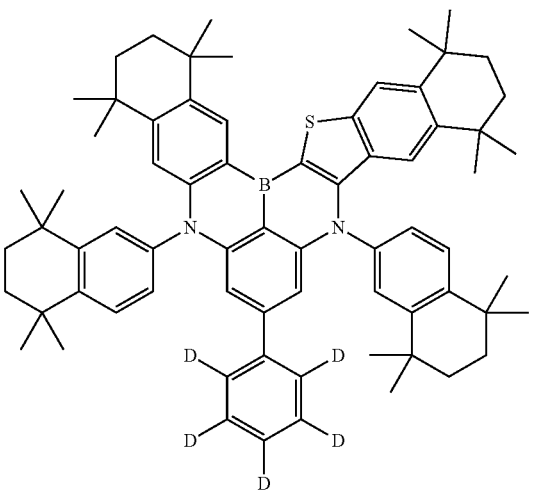
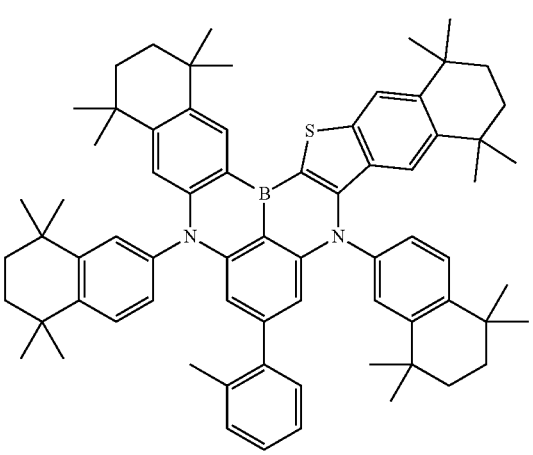

447
-continued
448
-continued
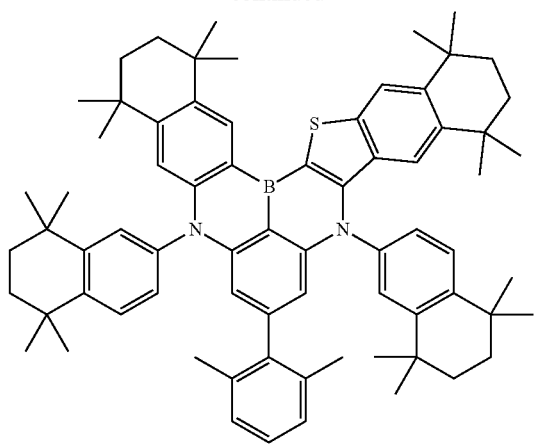
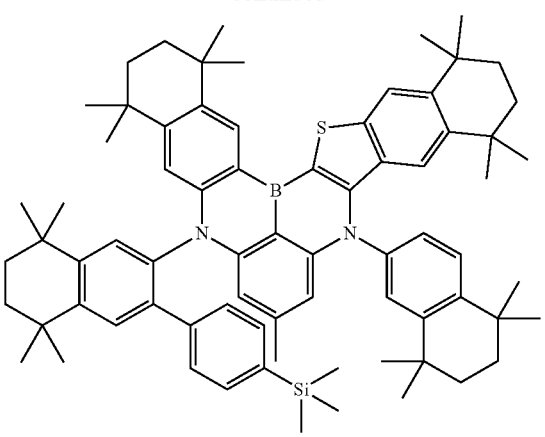

449
-continued
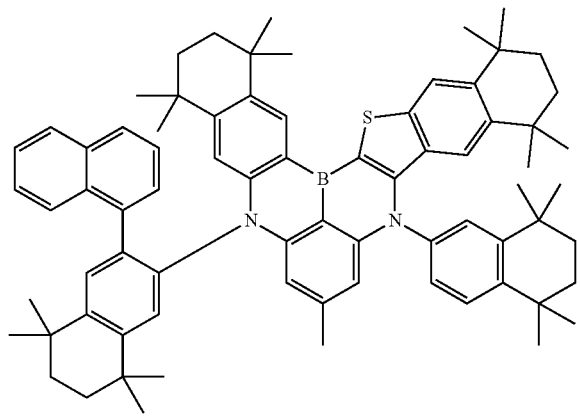
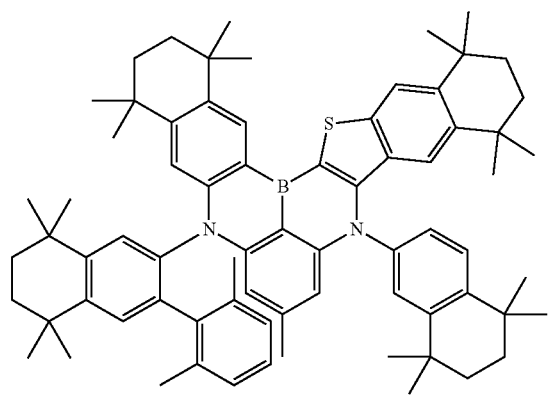
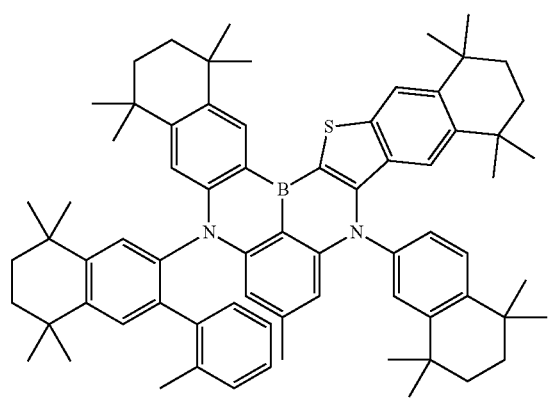
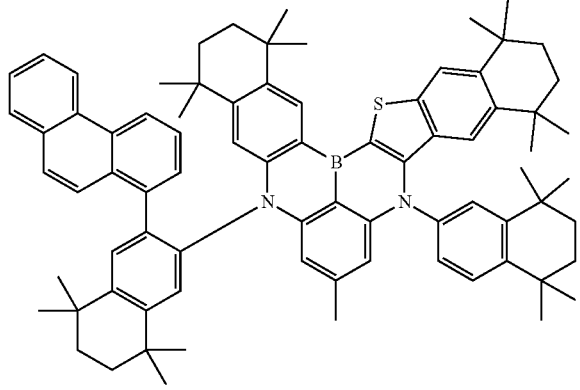
450
-continued
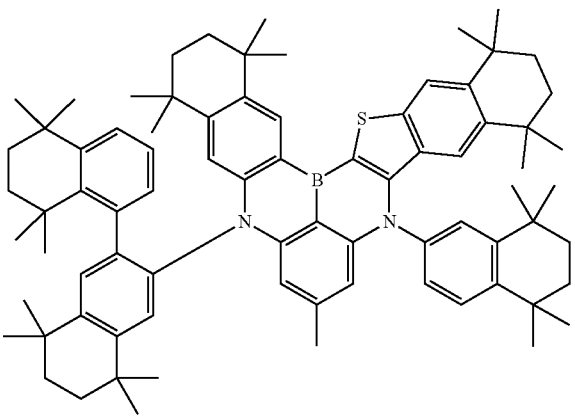
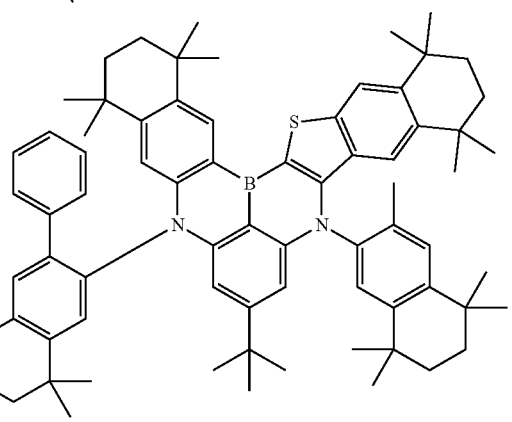
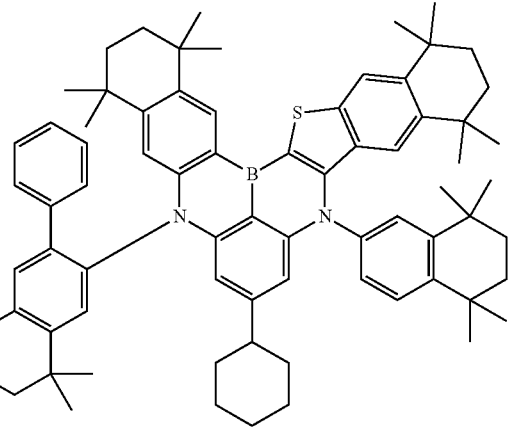
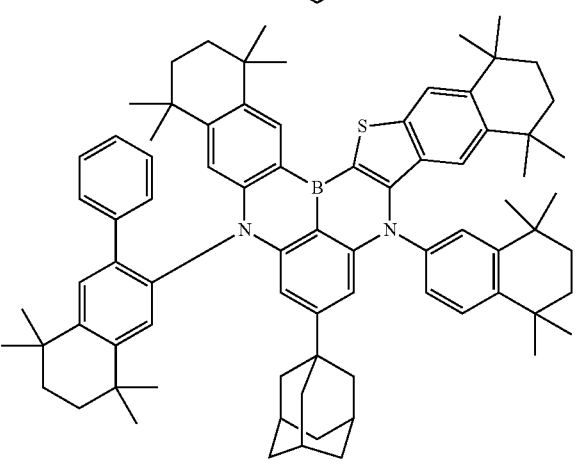

451
-continued
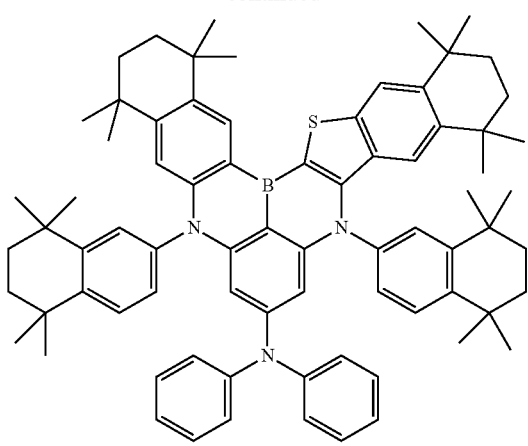
452
-continued
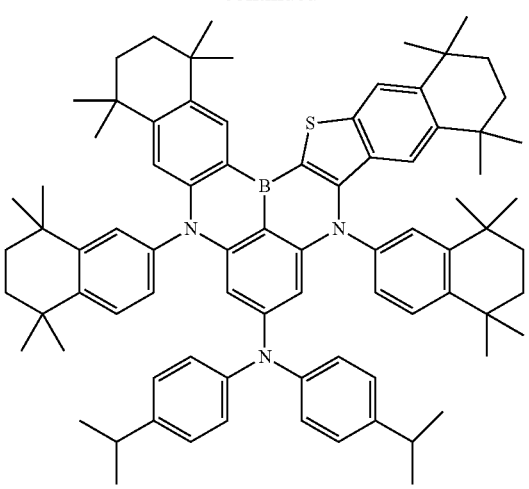
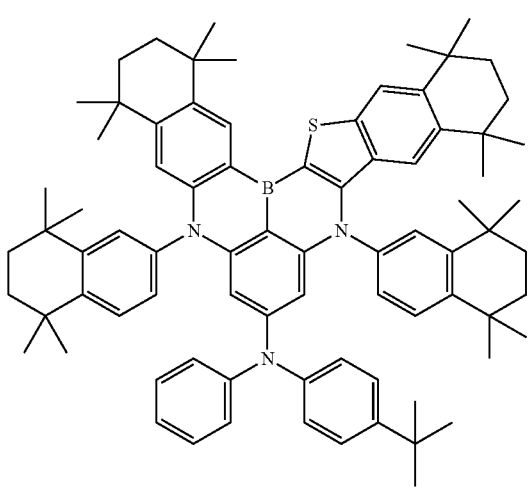
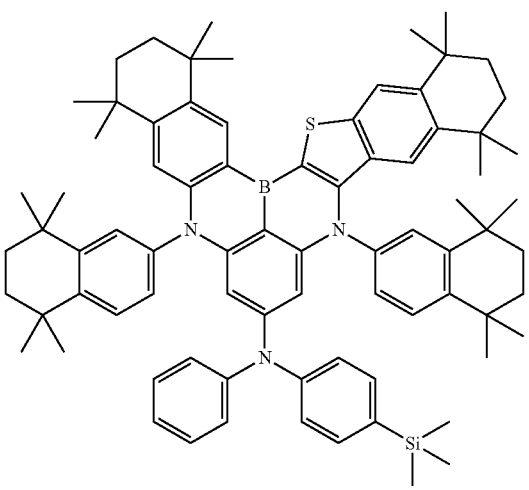
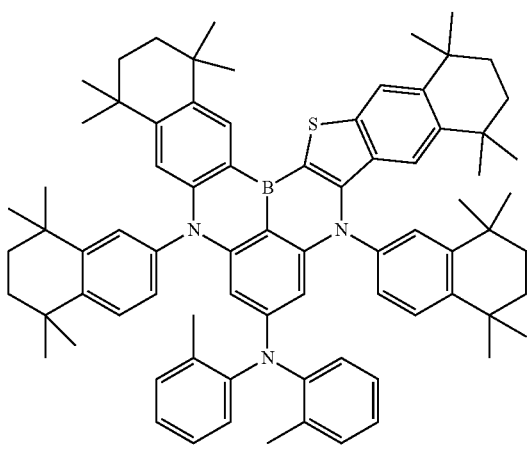
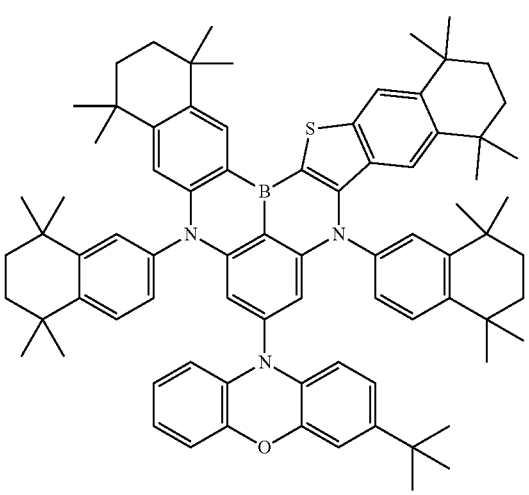

453
-continued
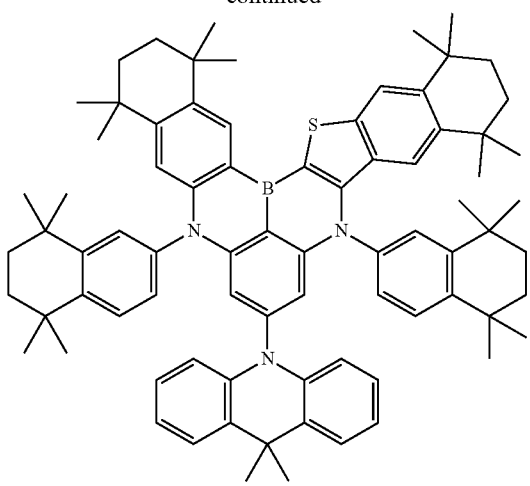
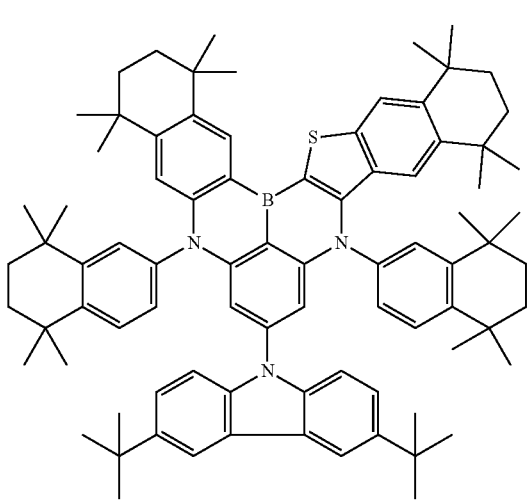
454
-continued
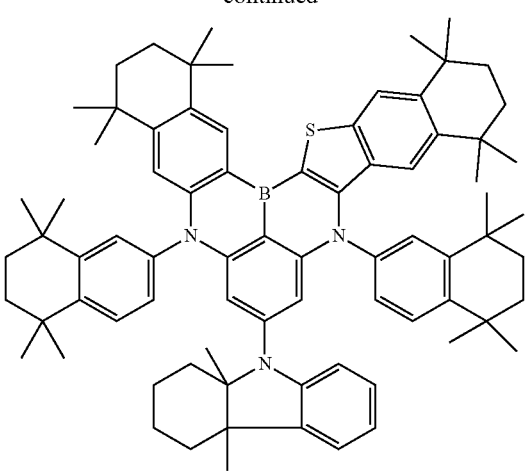
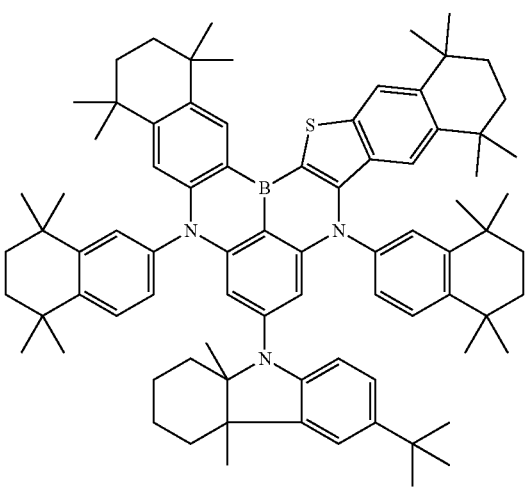
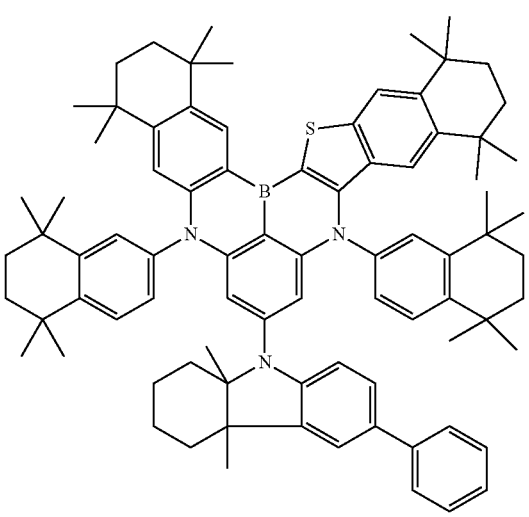

455
-continued
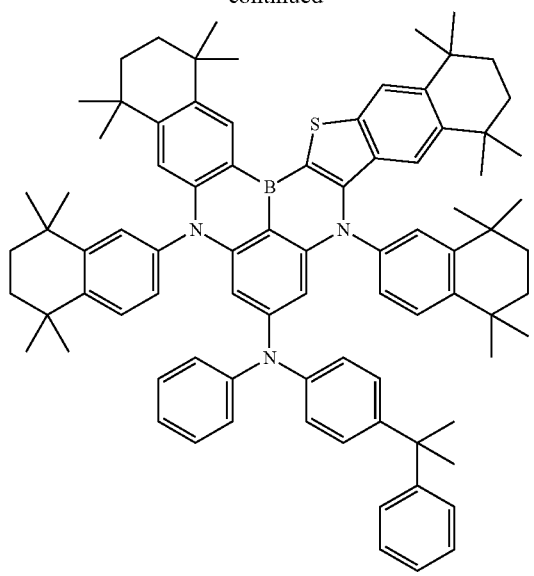
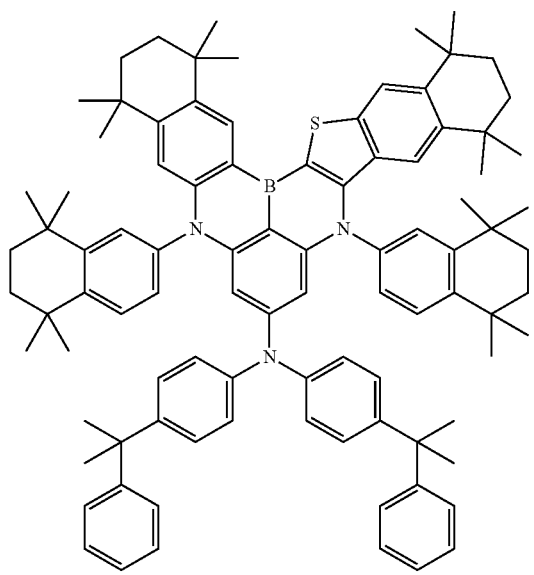
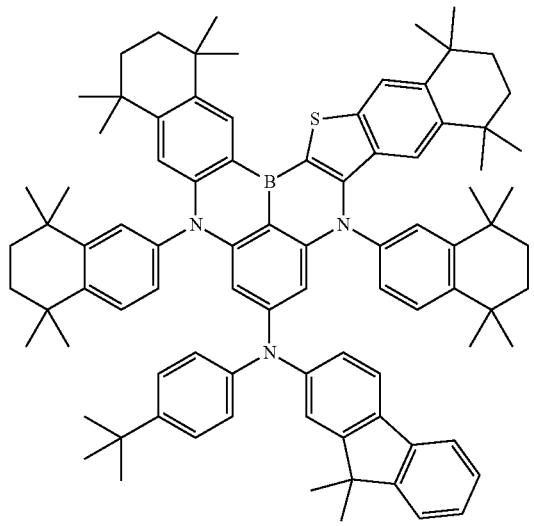
456
-continued
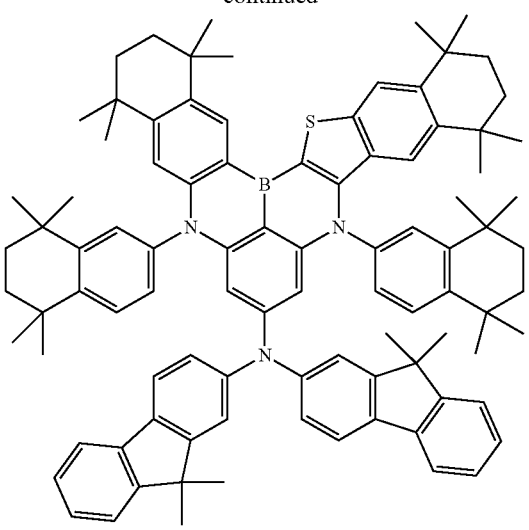
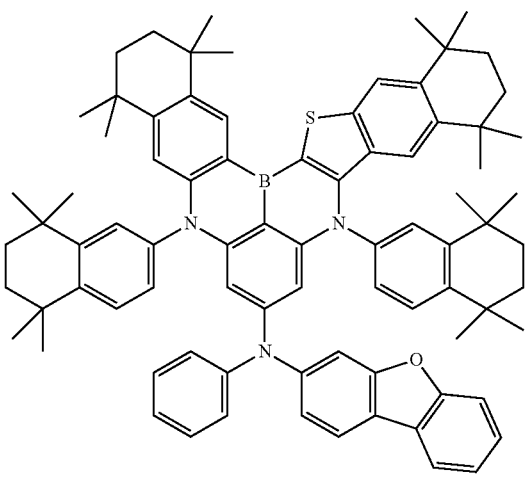
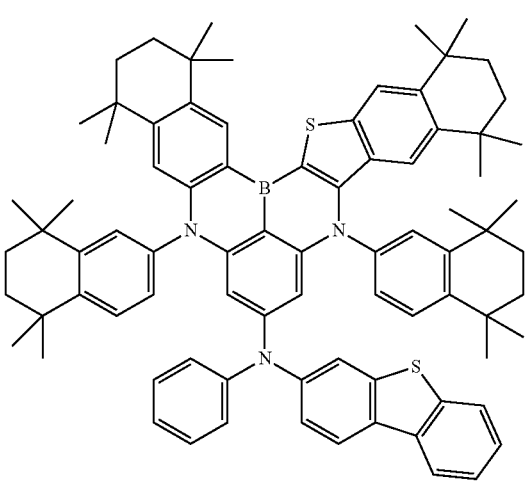

457
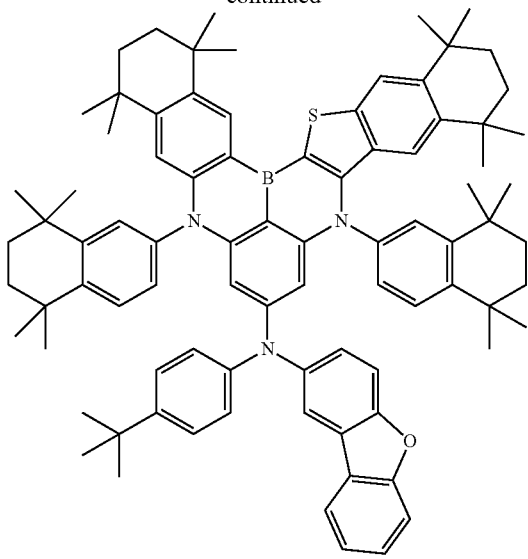
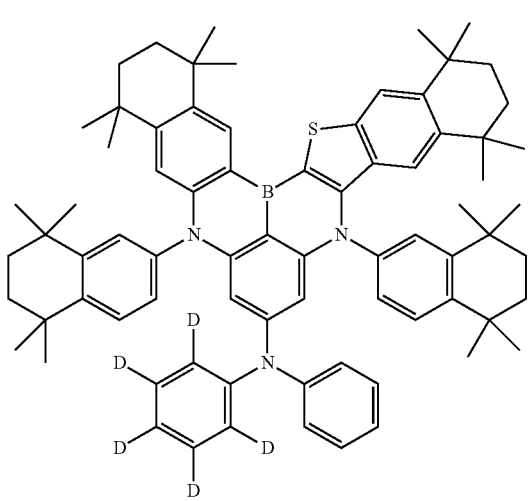
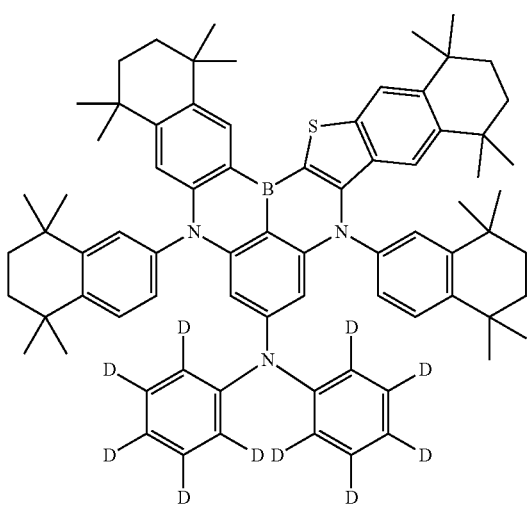
458
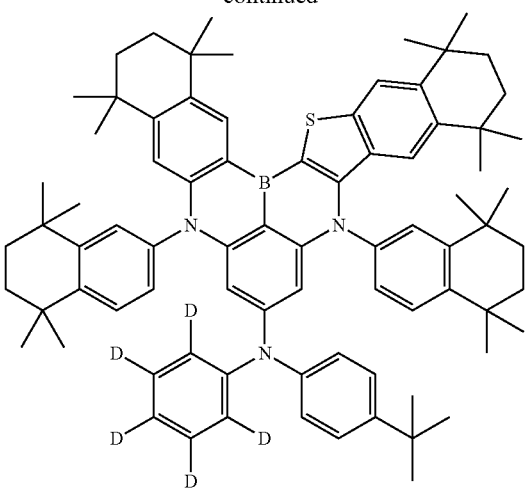
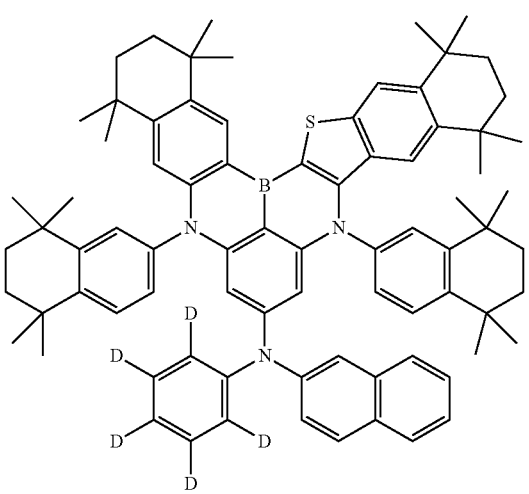
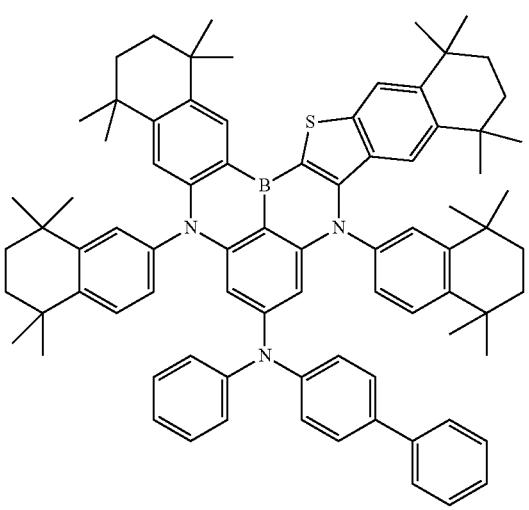

459
-continued
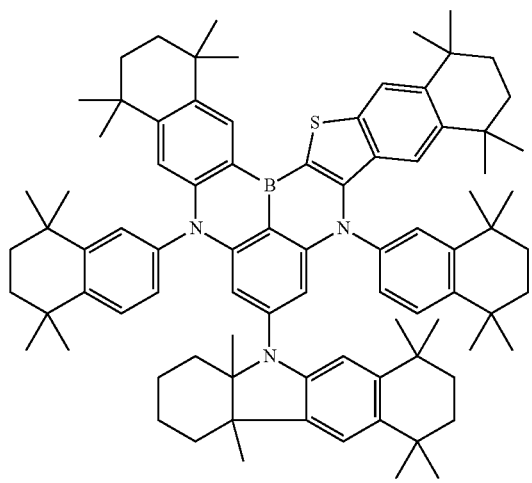
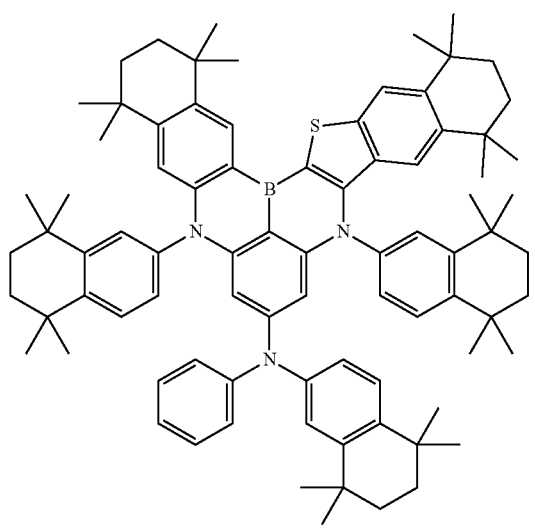
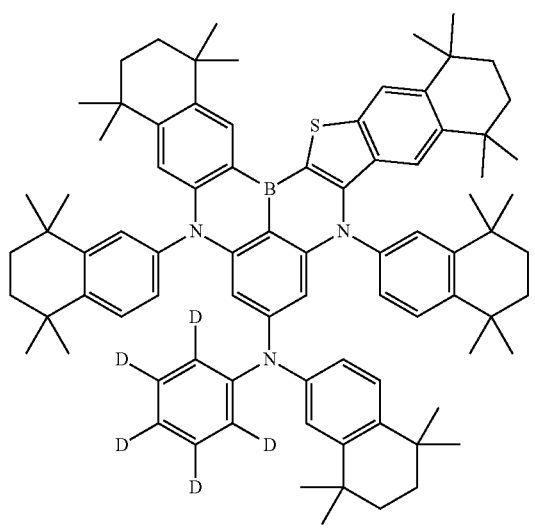
460
-continued
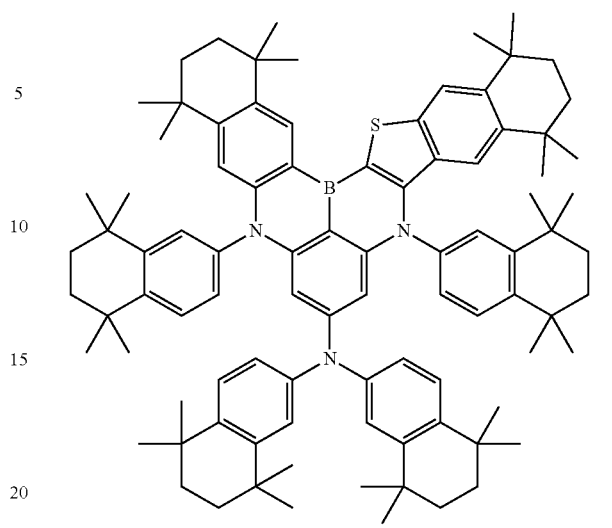
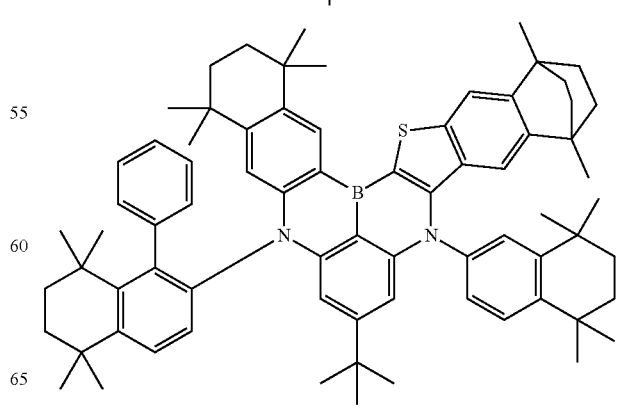

461
-continued
462
-continued
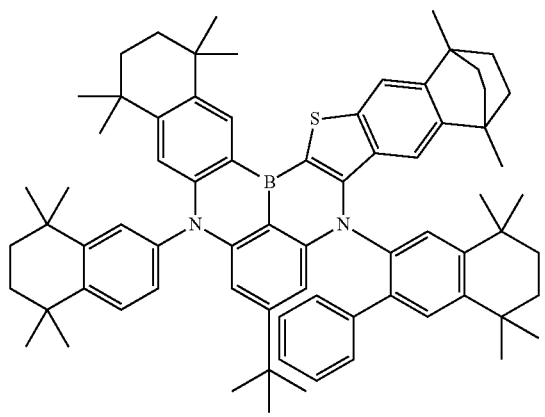
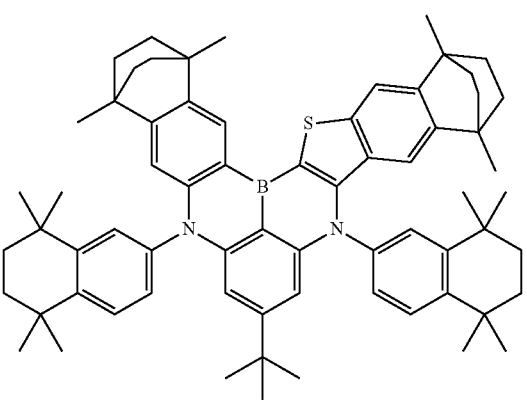

463
-continued
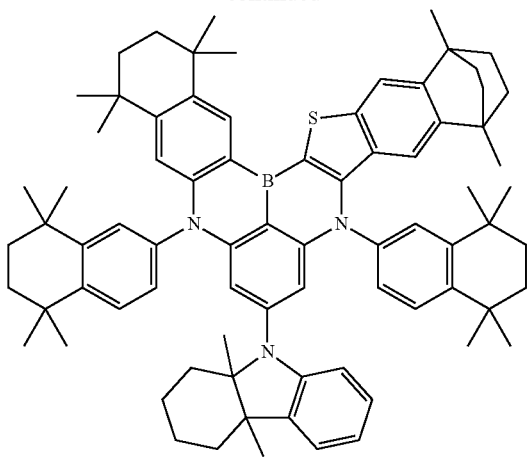
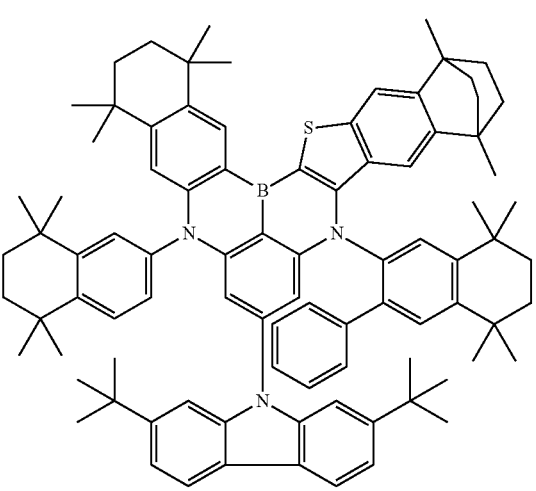
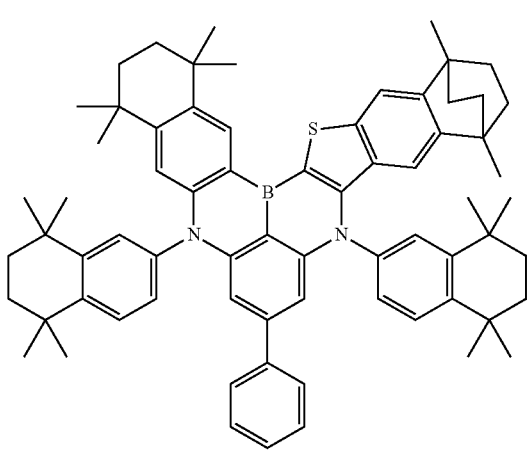
464
-continued
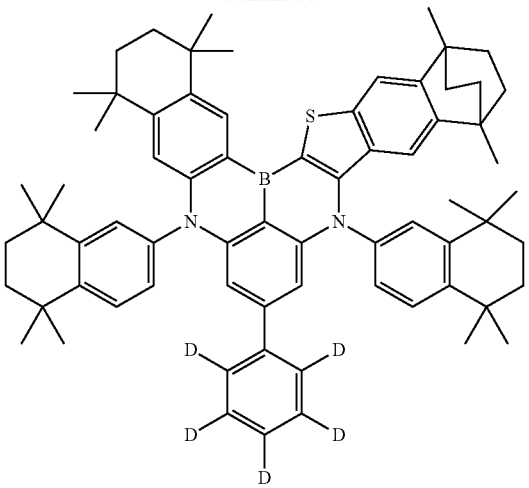
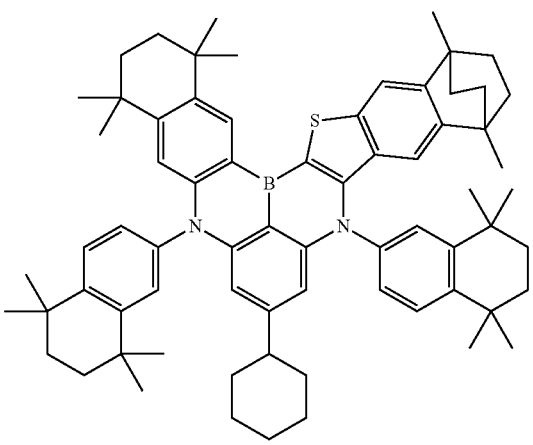
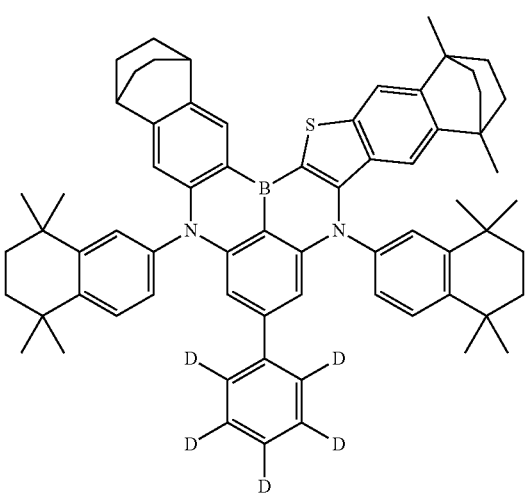

465
-continued
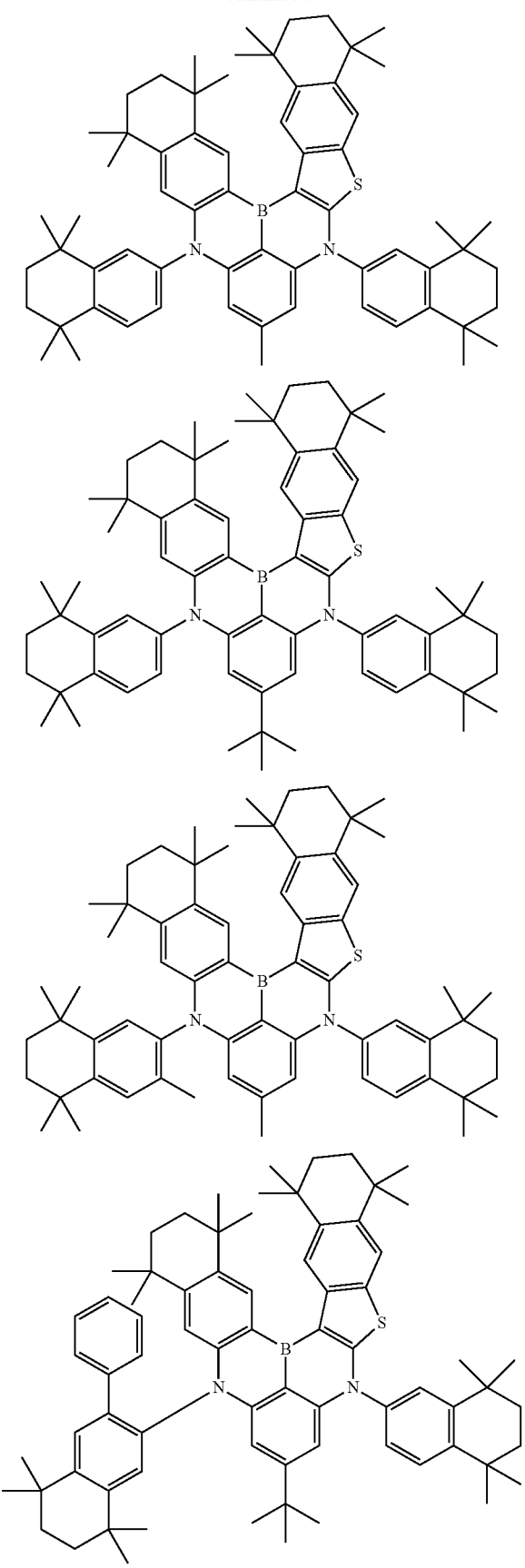
466
-continued
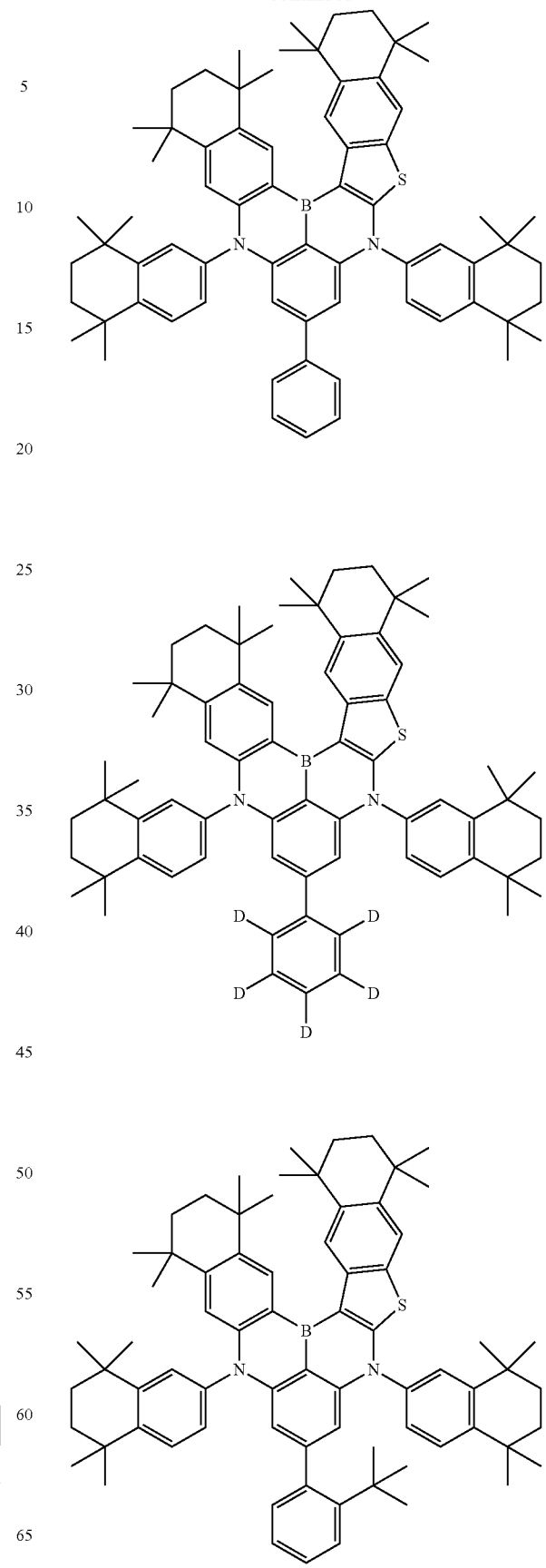

467
-continued
468
-continued
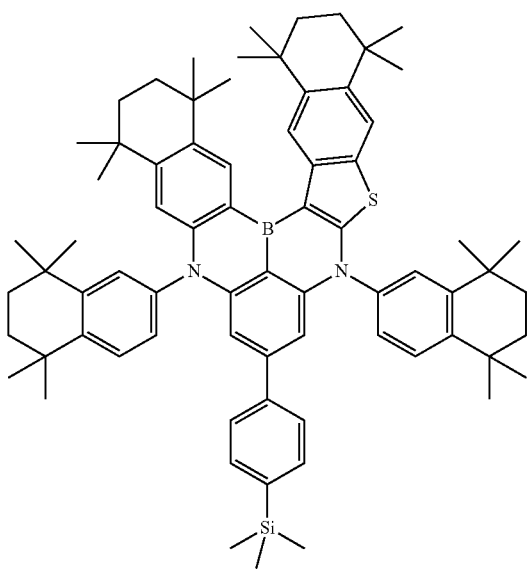
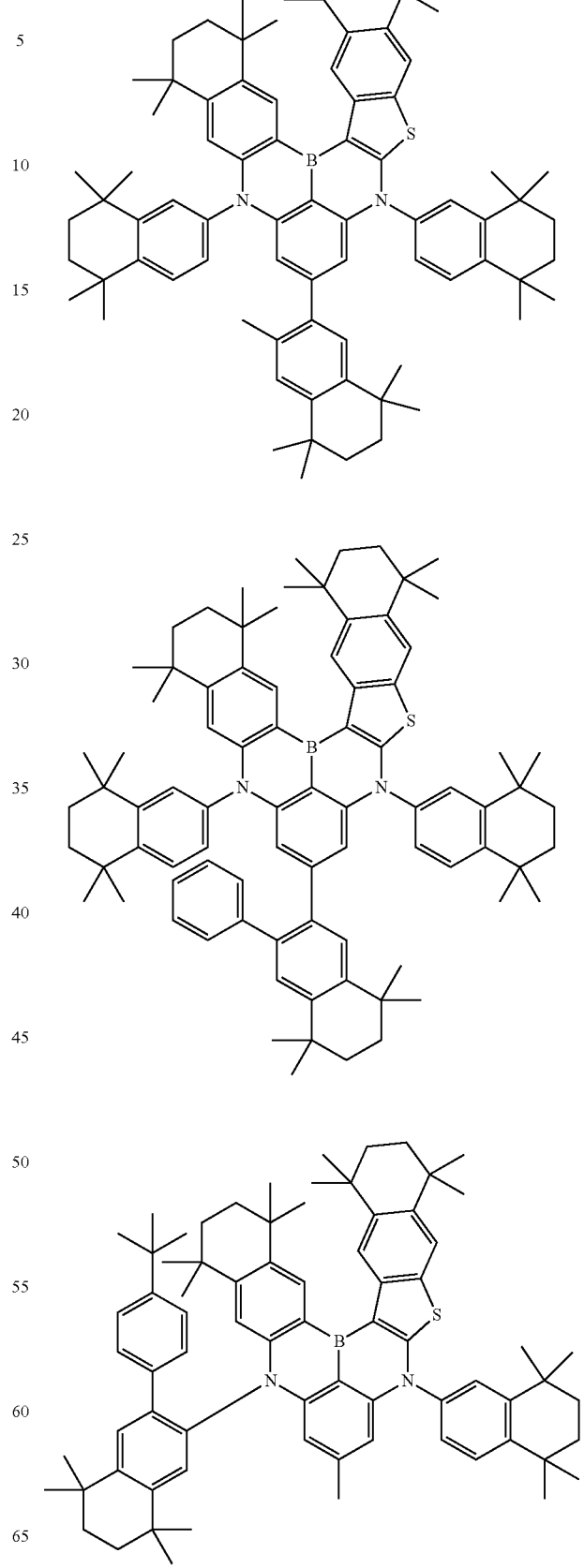

469
-continued
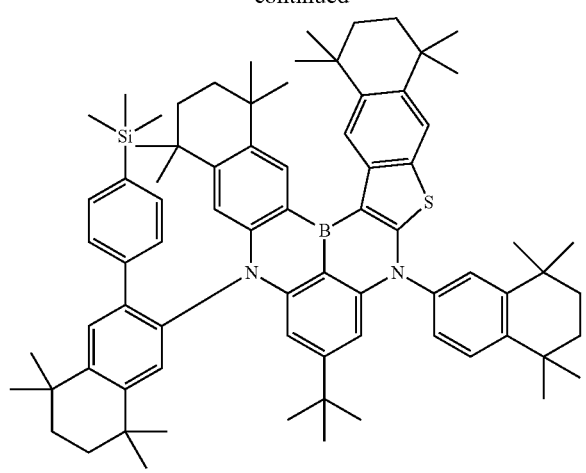
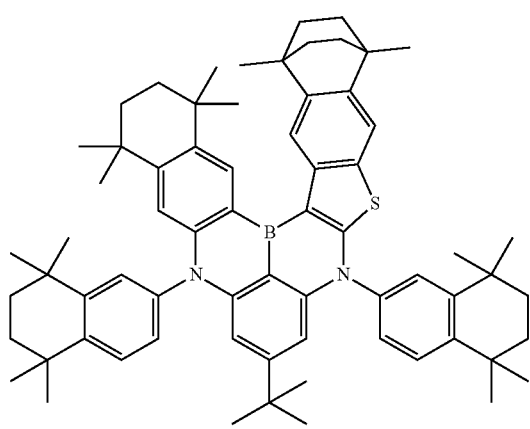
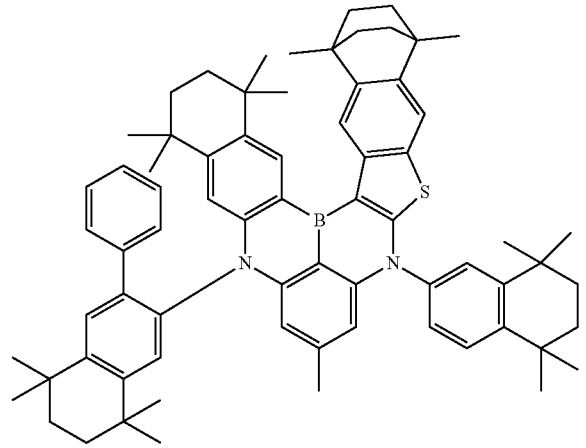
470
-continued
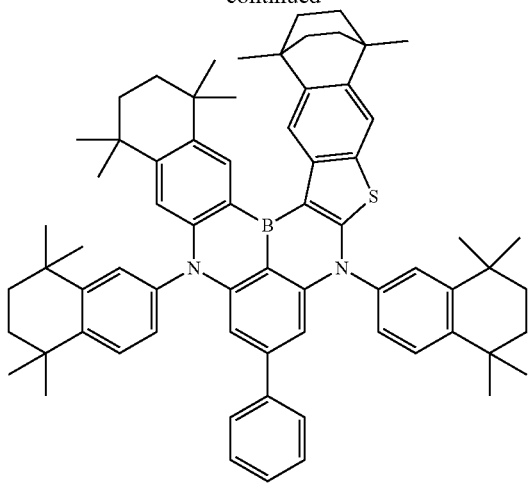
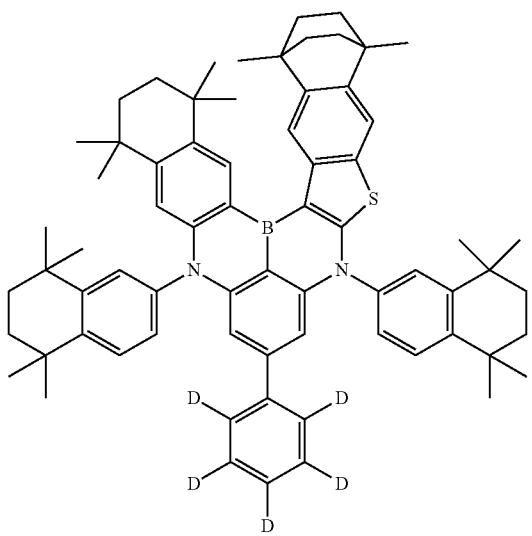
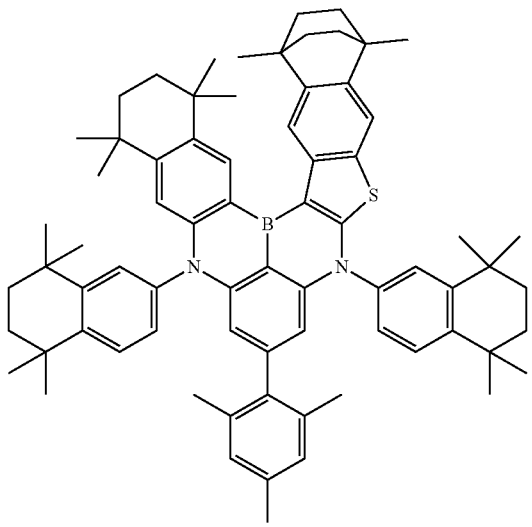

471
-continued
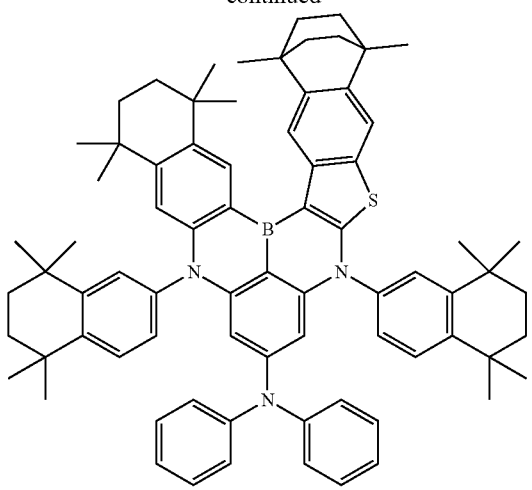
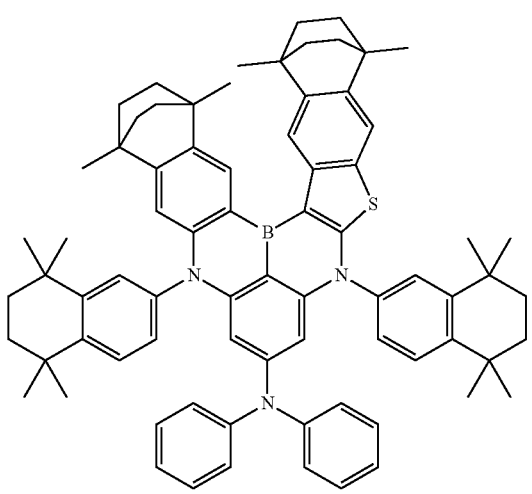
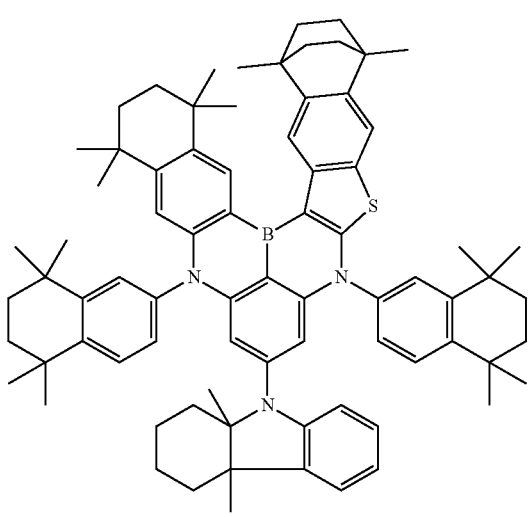
472
-continued
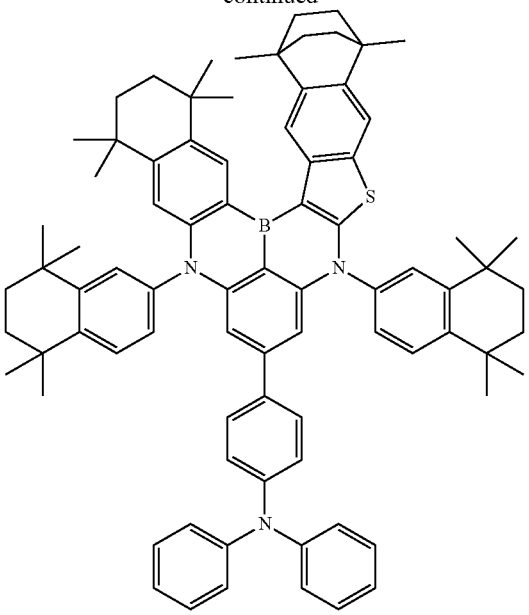
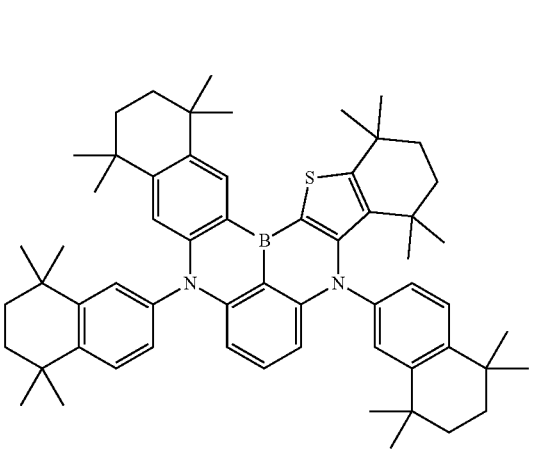
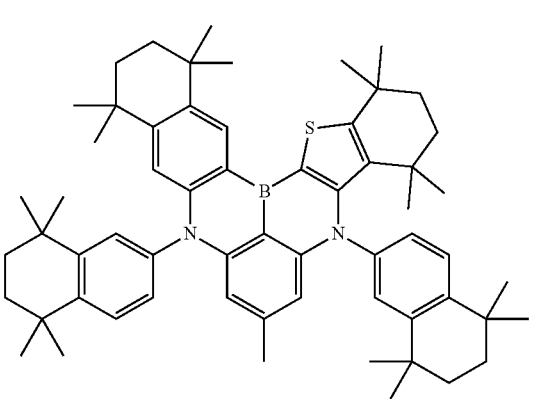

473
-continued
474
-continued
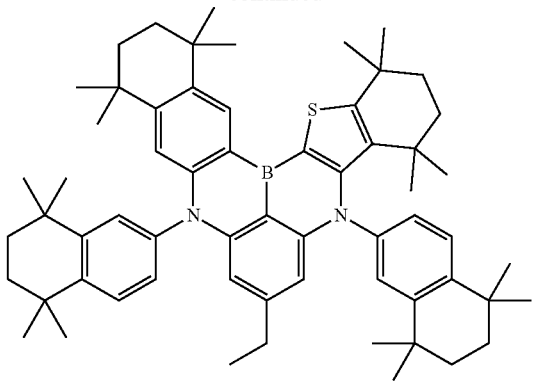
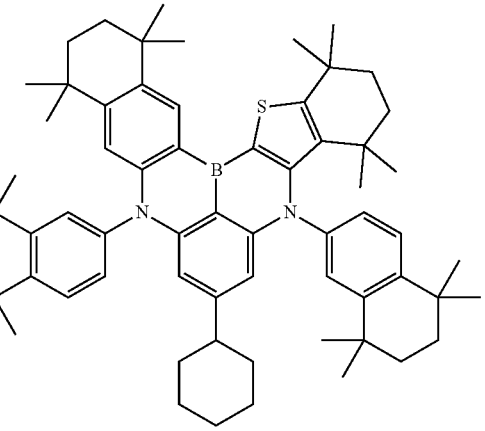
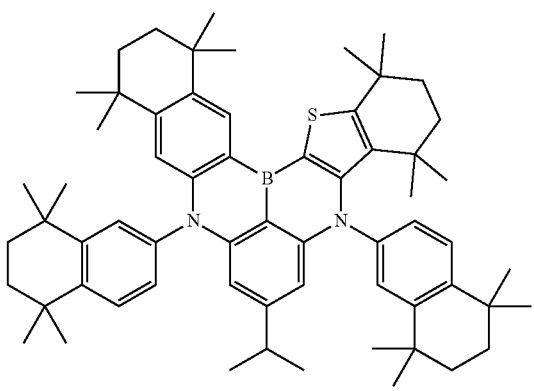
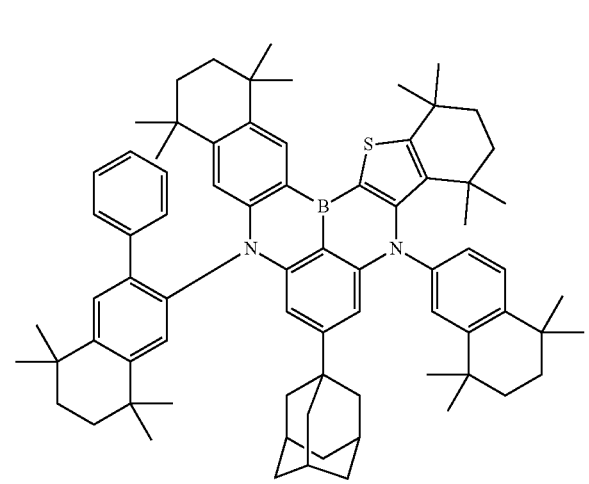
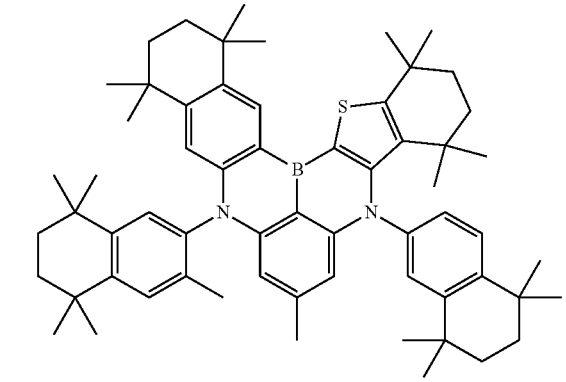
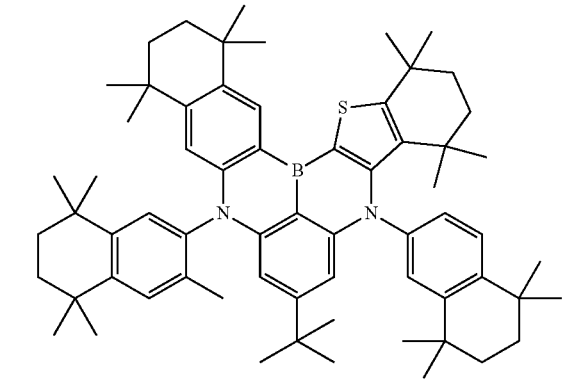

475
-continued
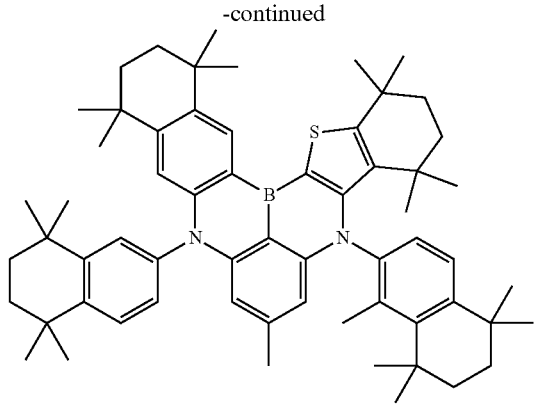
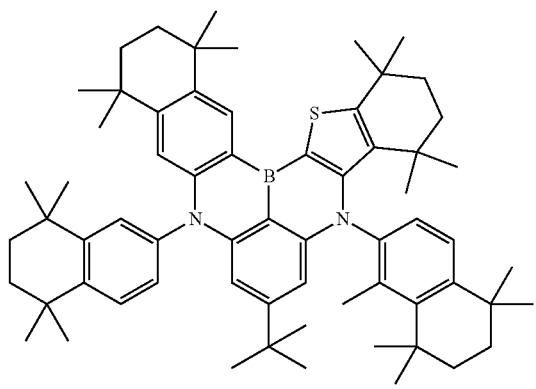
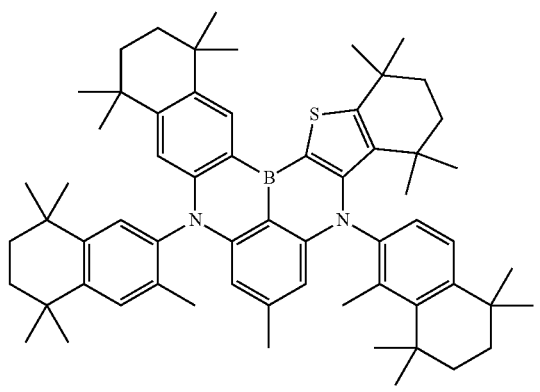
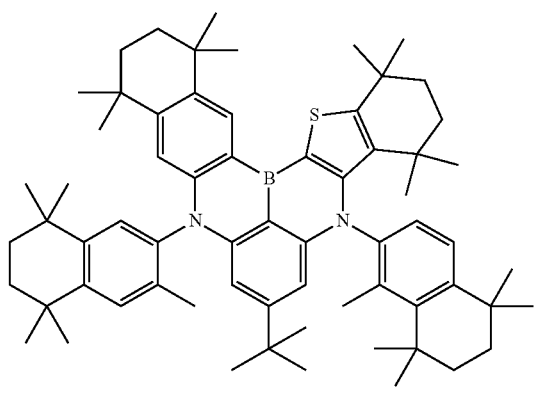
476
-continued
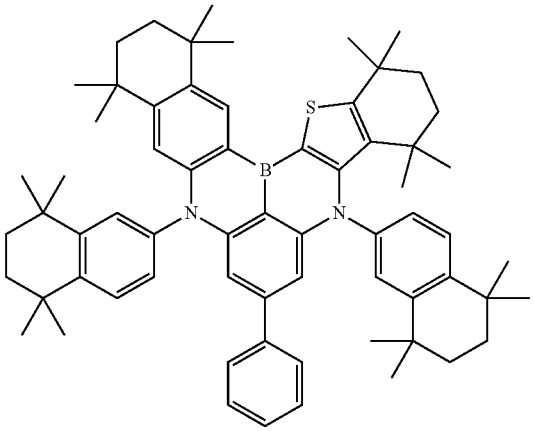
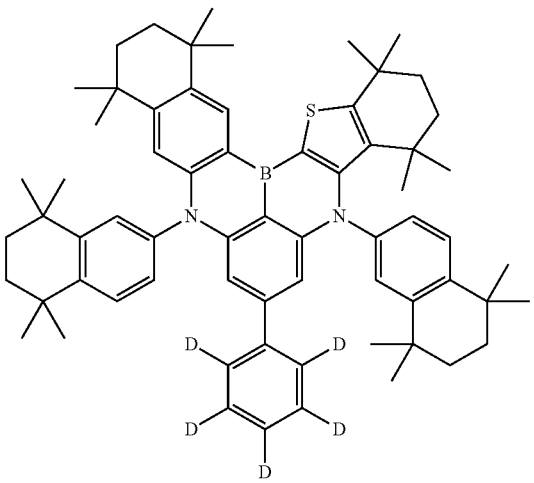
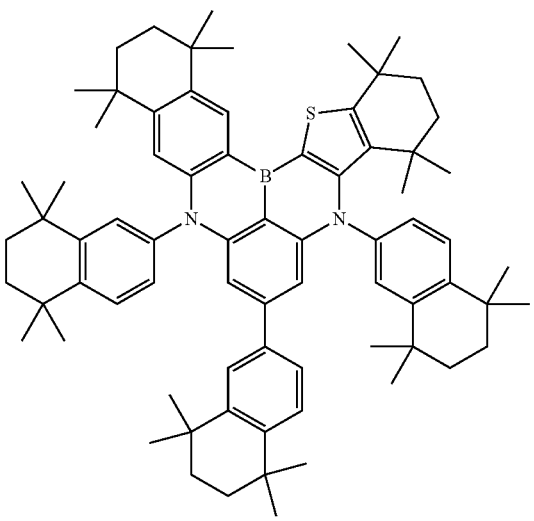

477
-continued
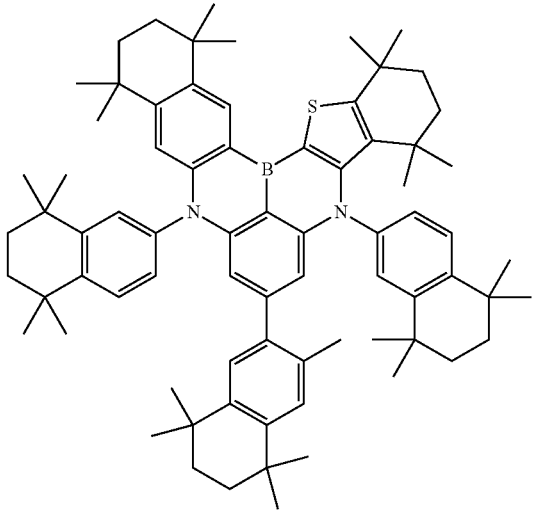
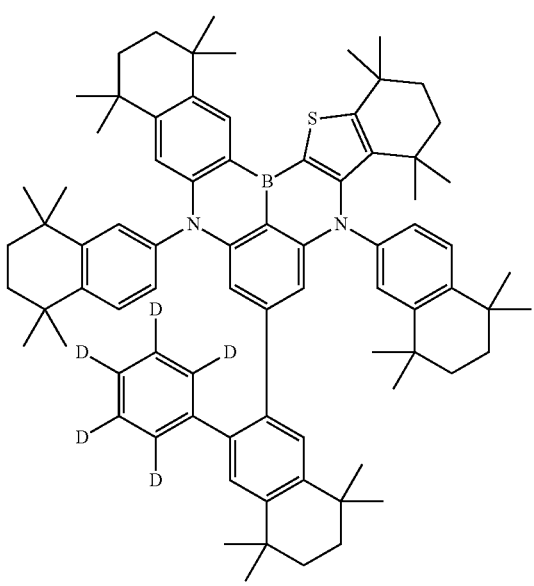
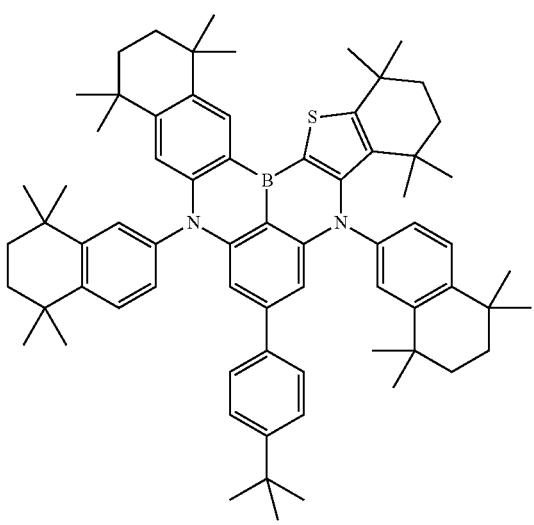
478
-continued
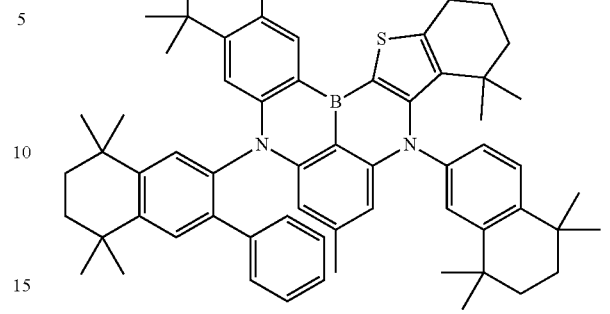
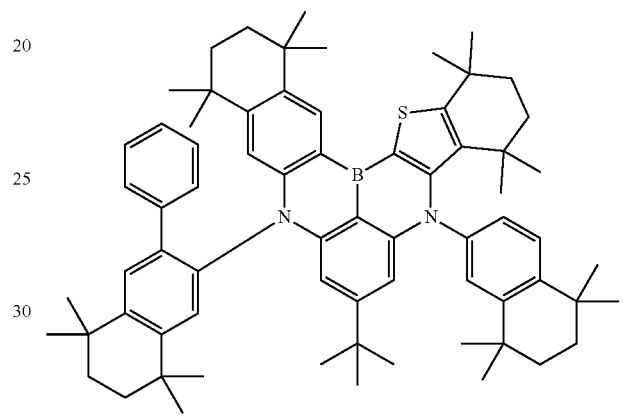
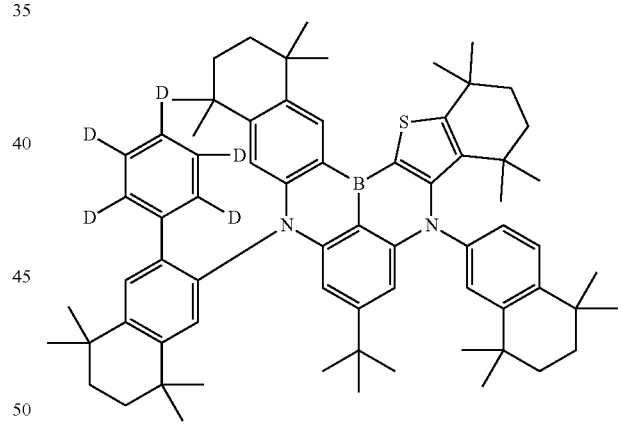
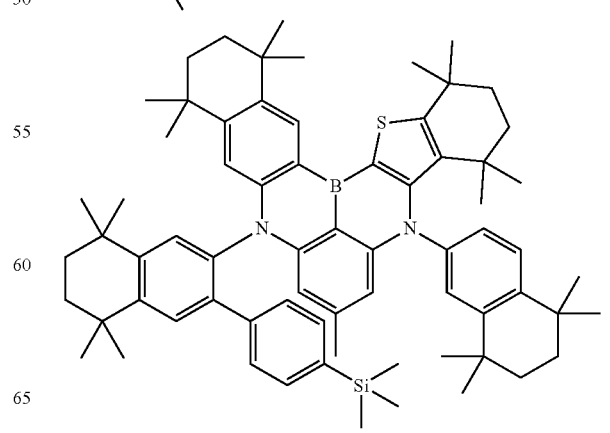

479
-continued
480
-continued
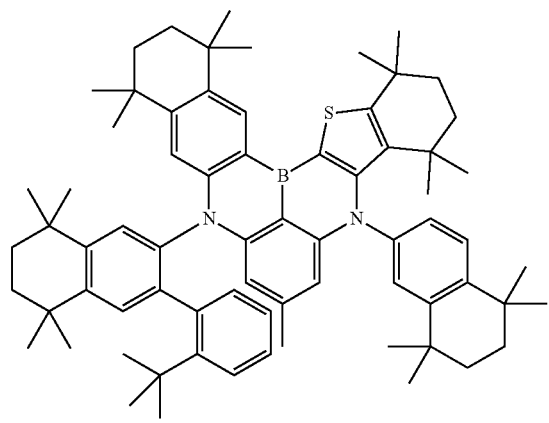
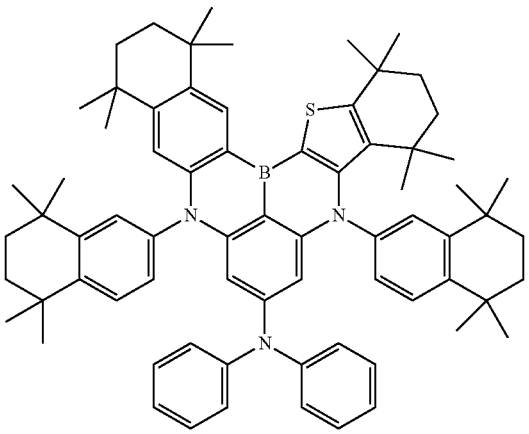
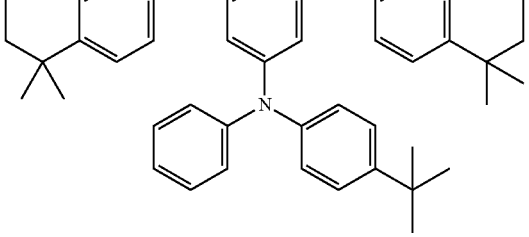
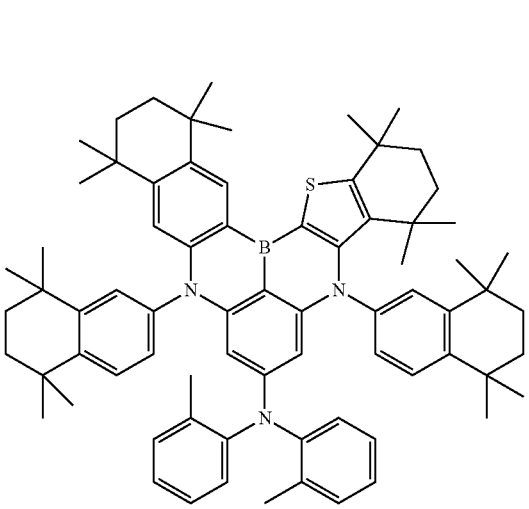

481
-continued
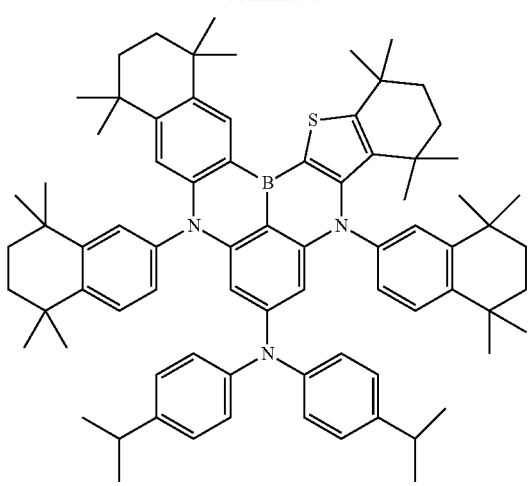
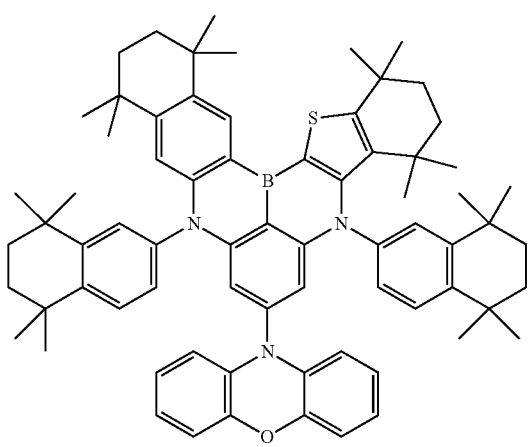
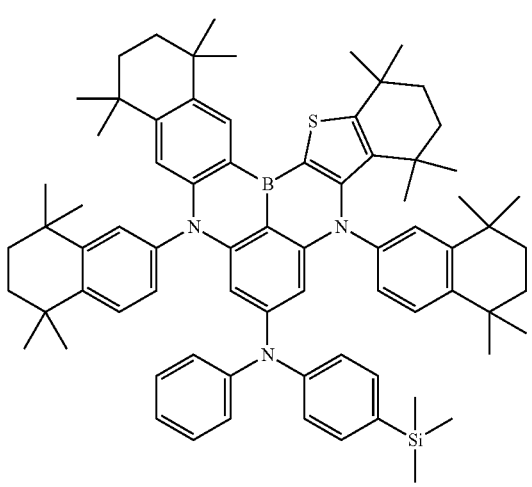
482
-continued
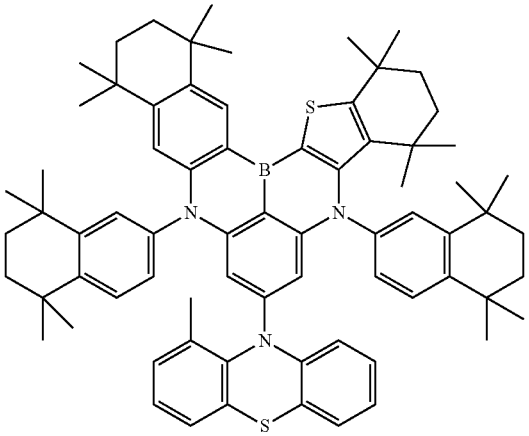
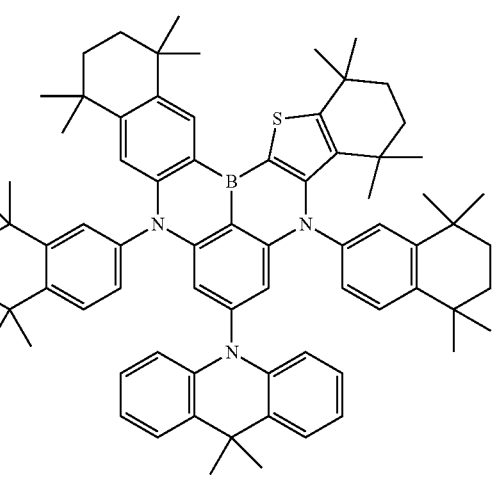
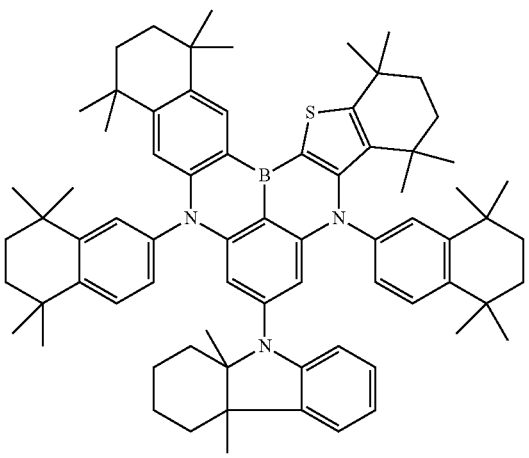

483
-continued
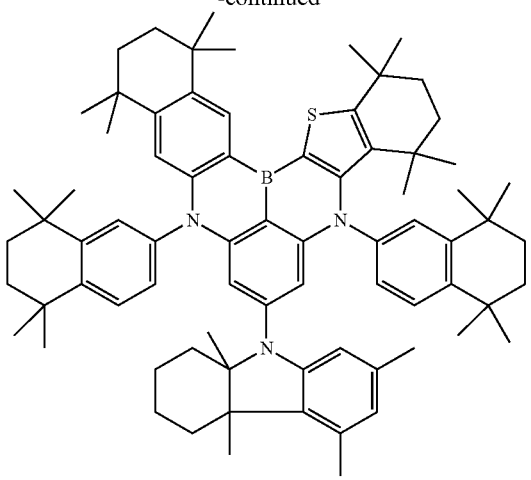
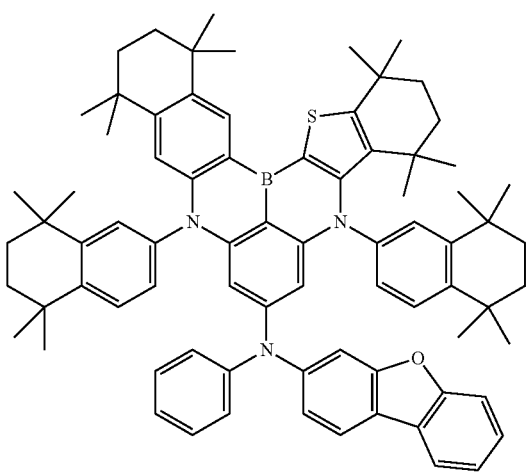
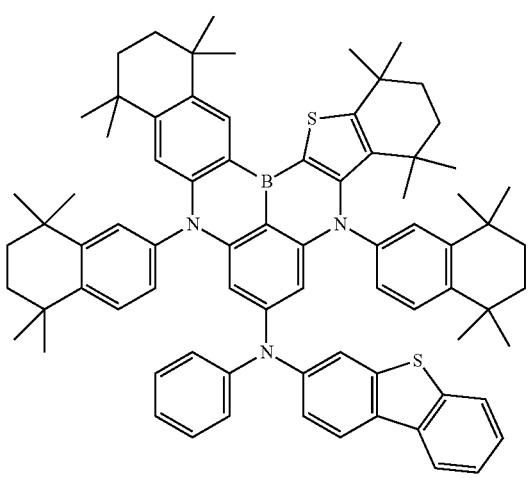
484
-continued
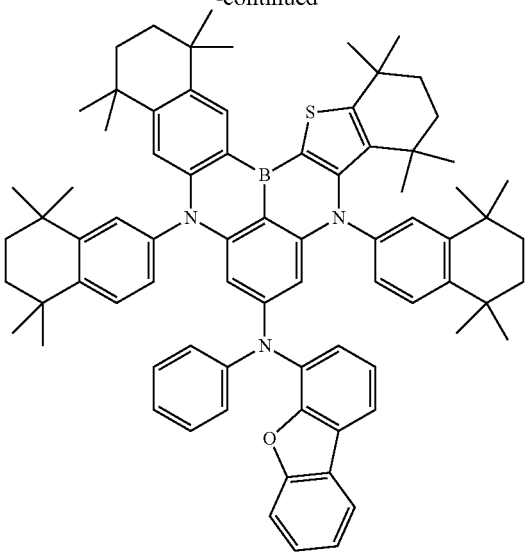
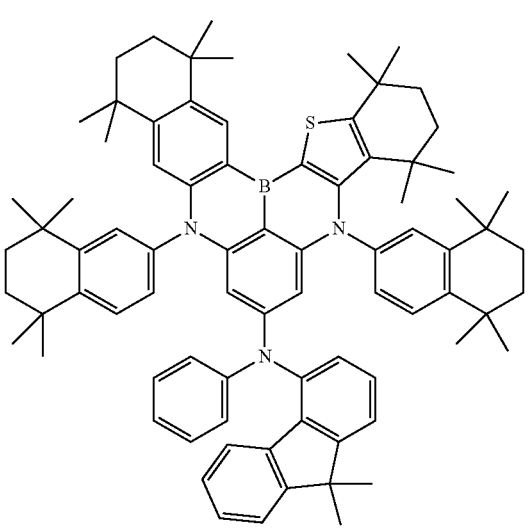
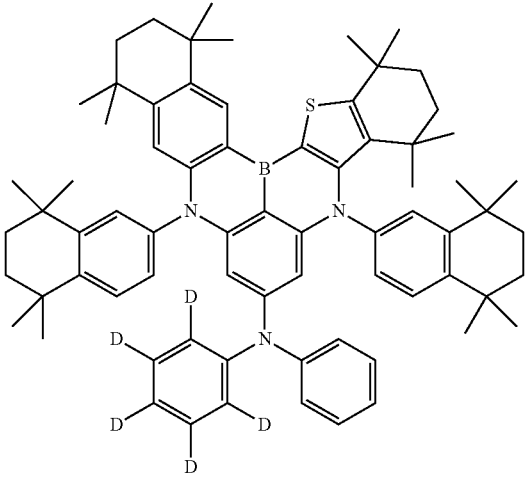

485
-continued
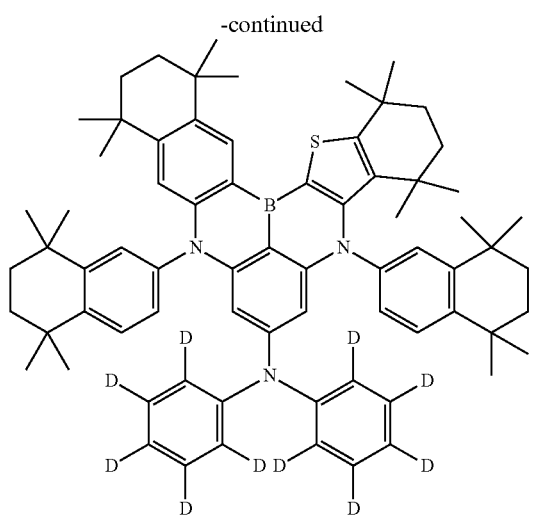
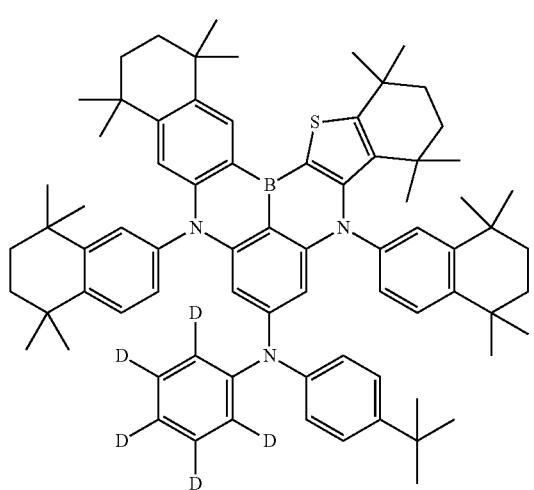
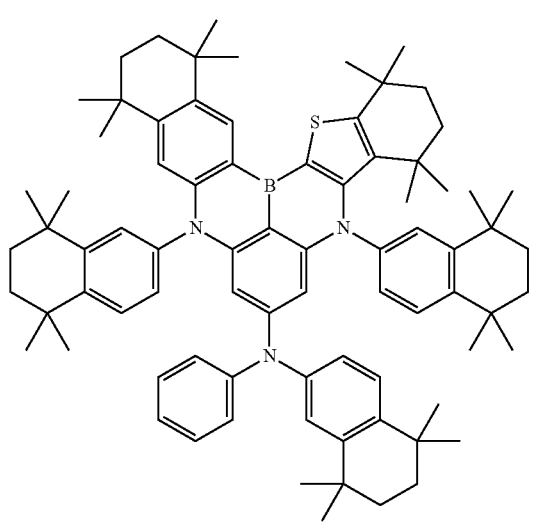
486
-continued
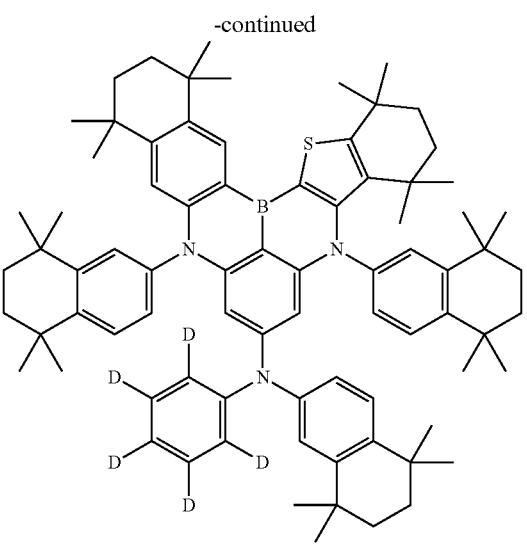
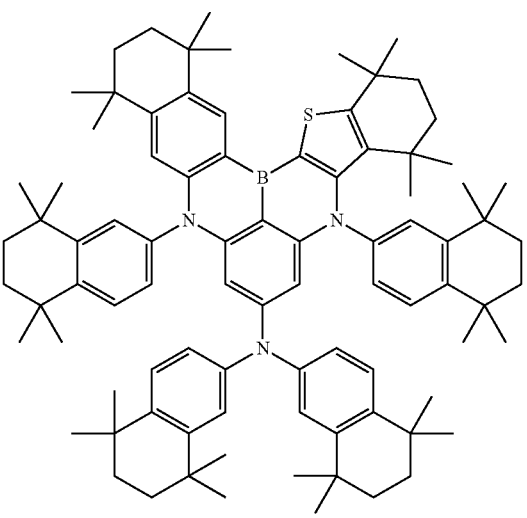
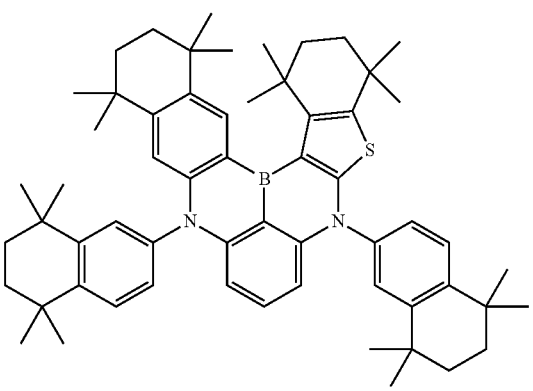

487
-continued
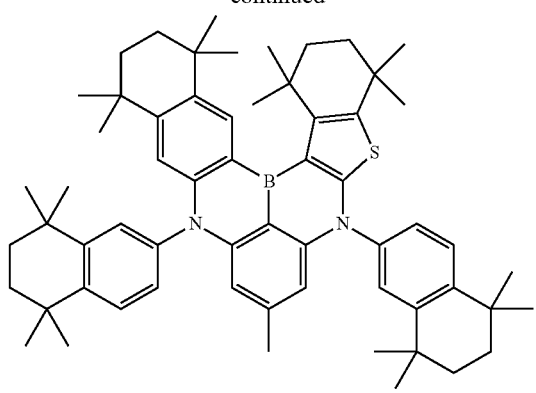
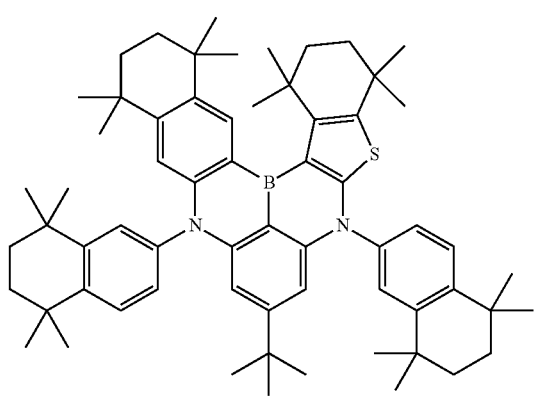
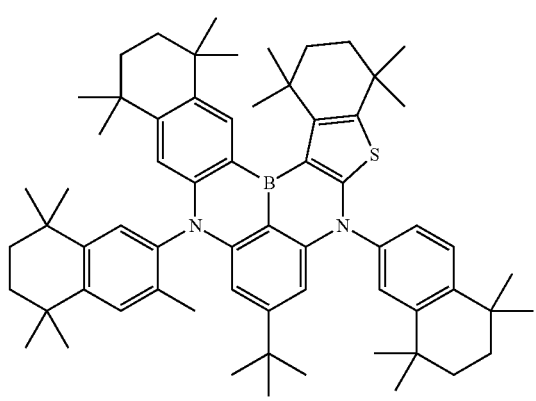
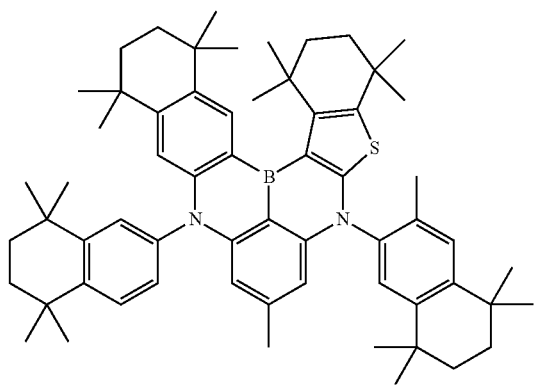
488
-continued
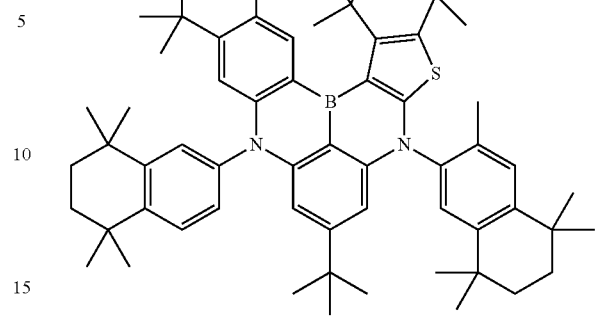
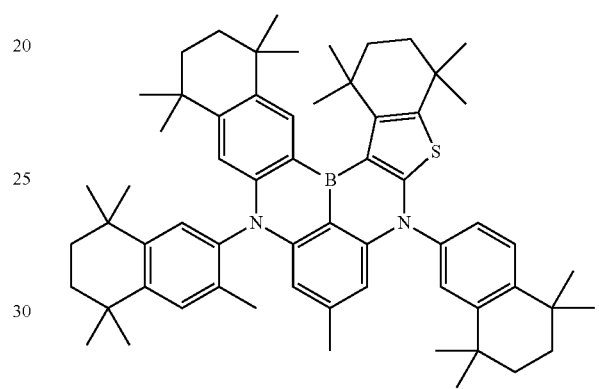
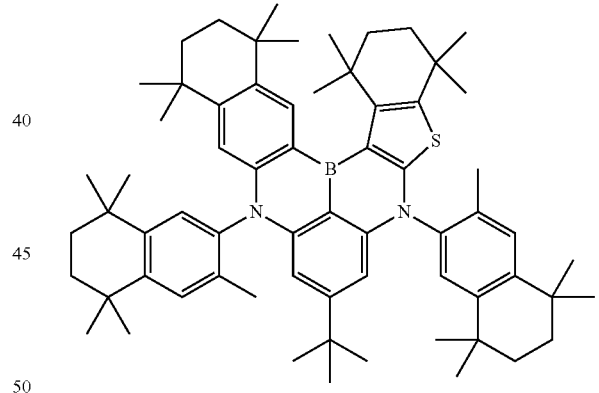
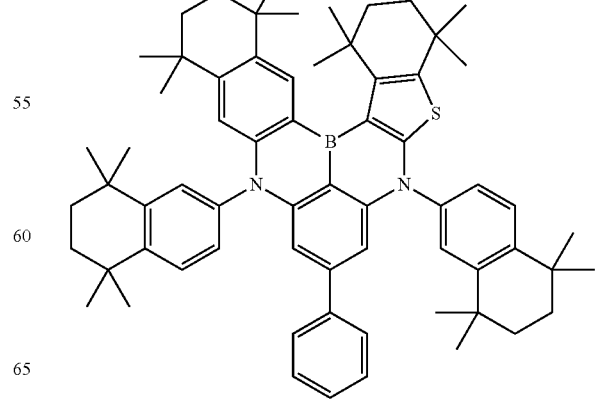

489
-continued
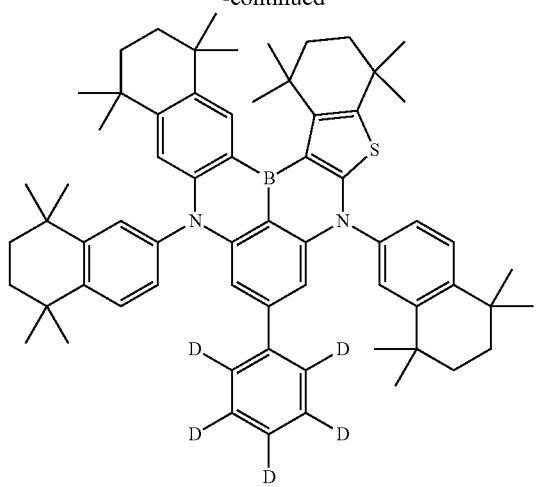
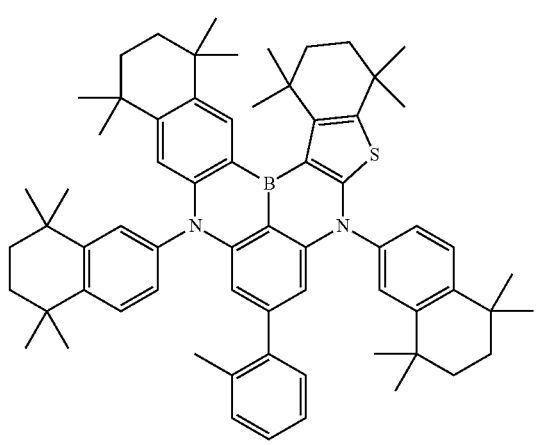
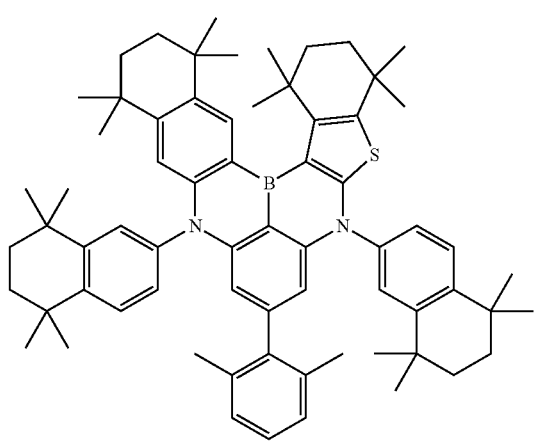
490
-continued
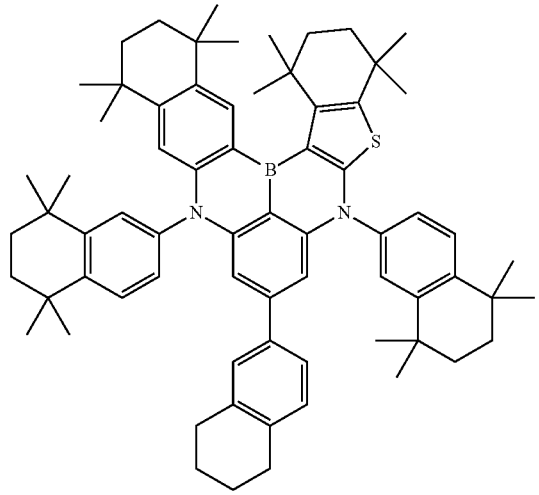
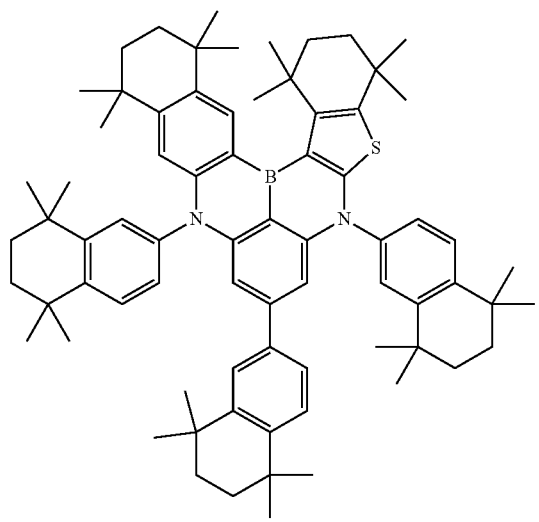
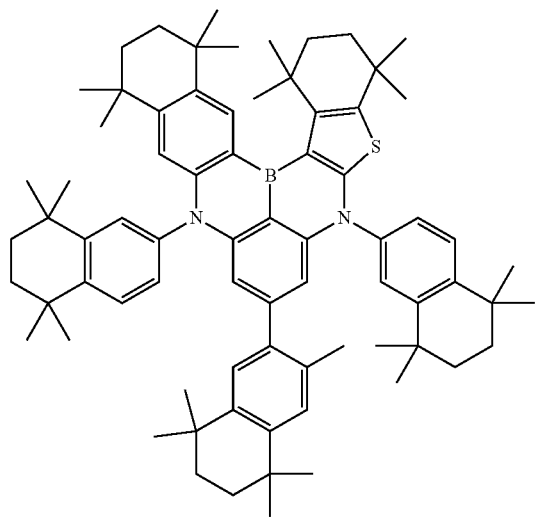

491
-continued
492
-continued
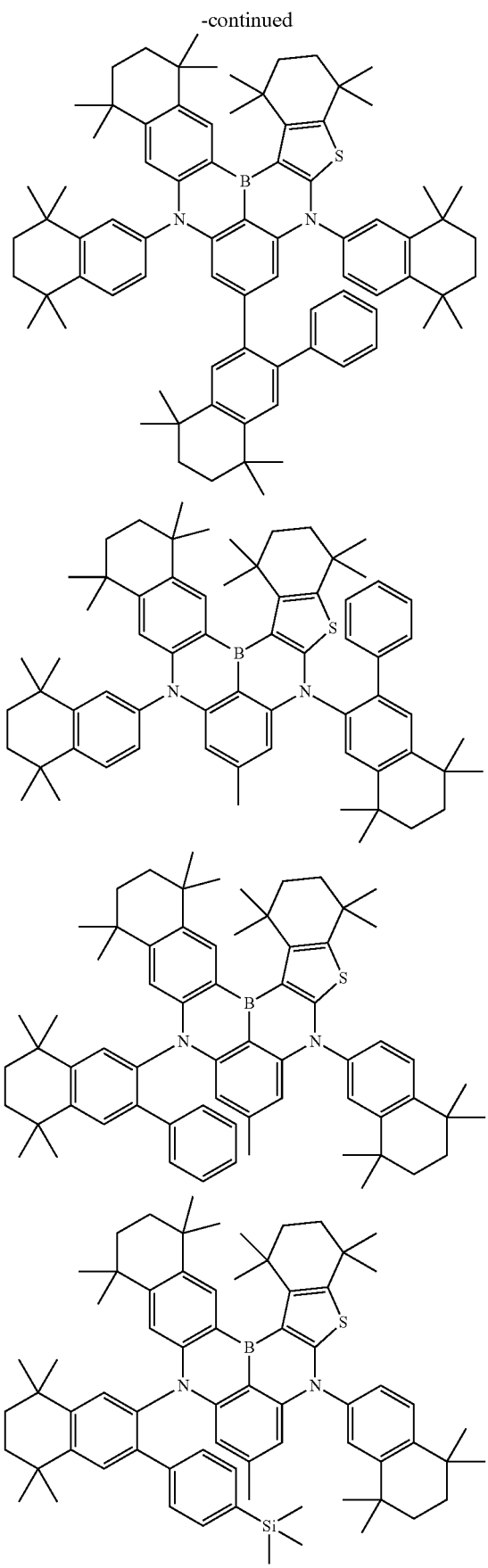
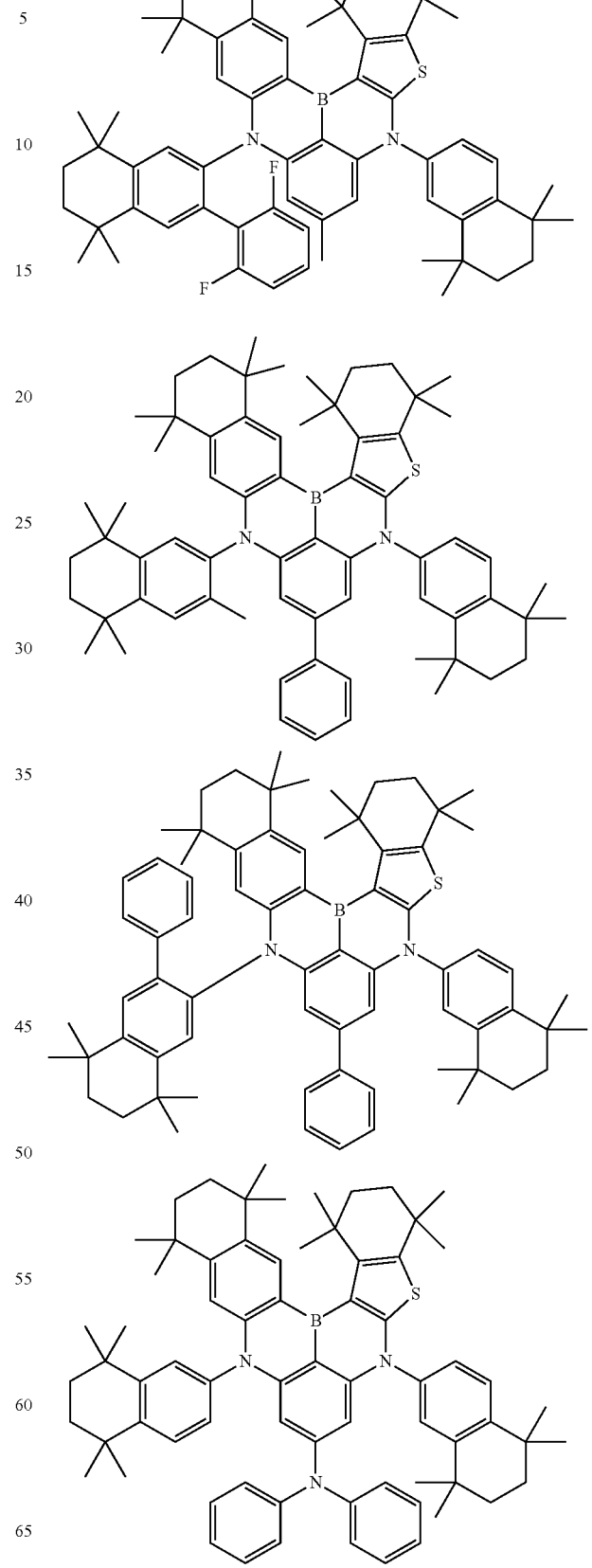

493
-continued
494
-continued
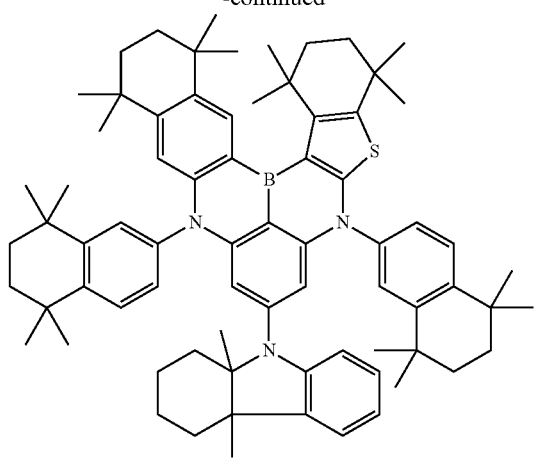
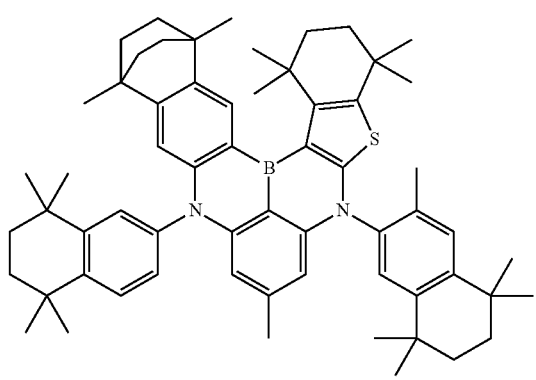
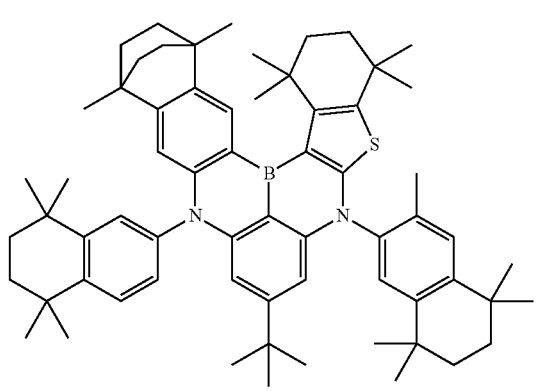
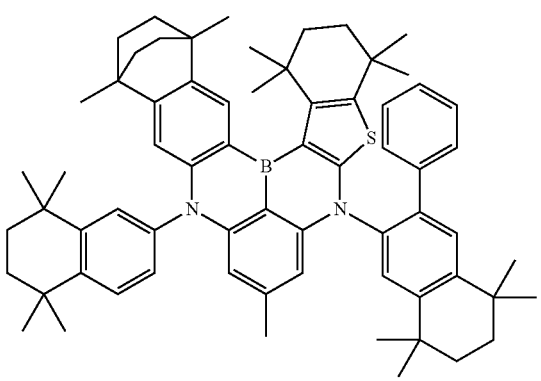
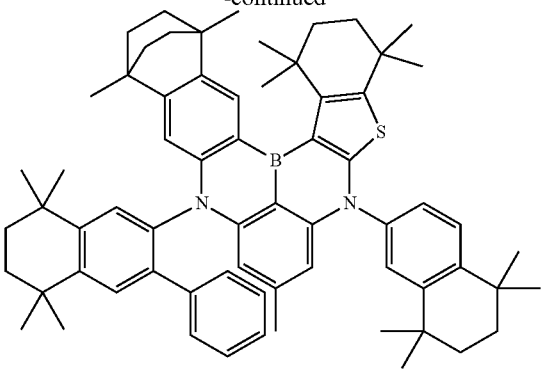
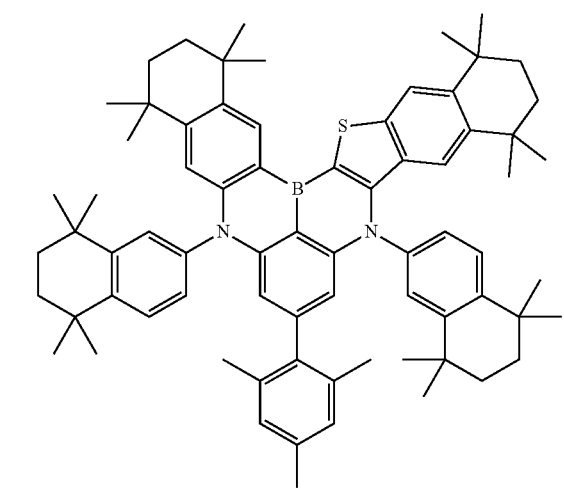
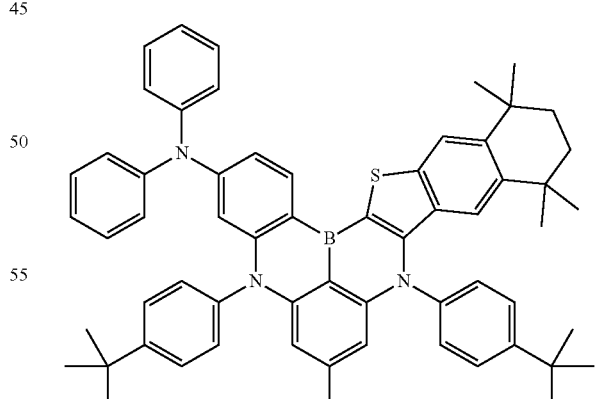

495
-continued
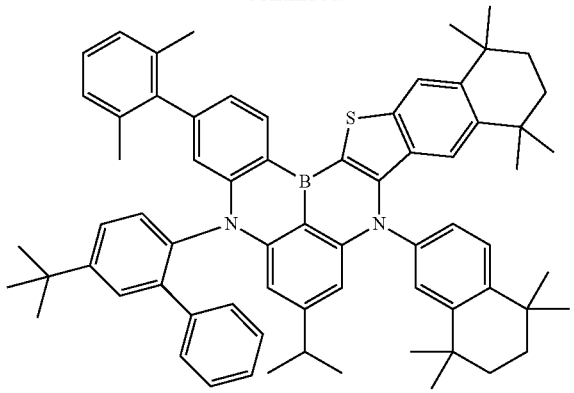
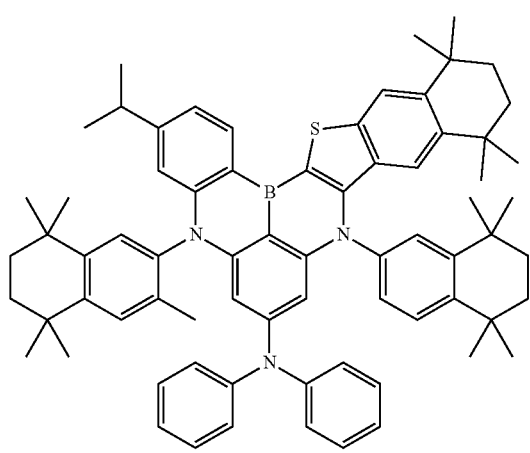
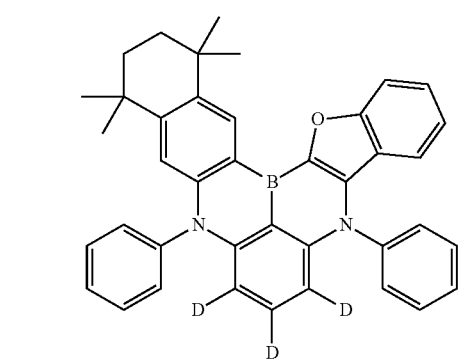
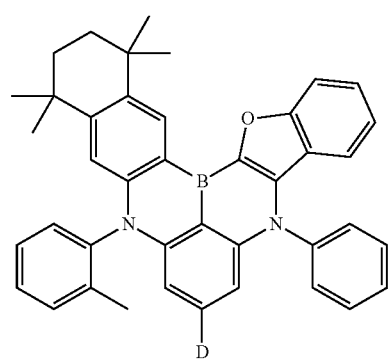
496
-continued
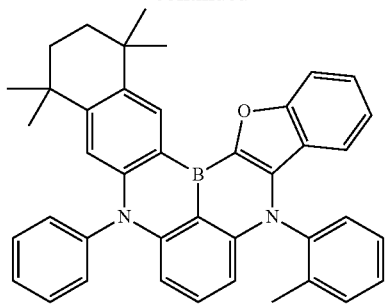
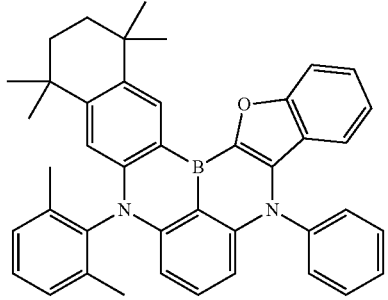
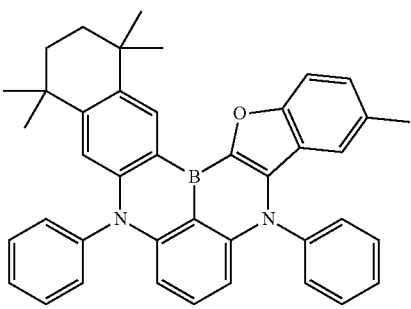
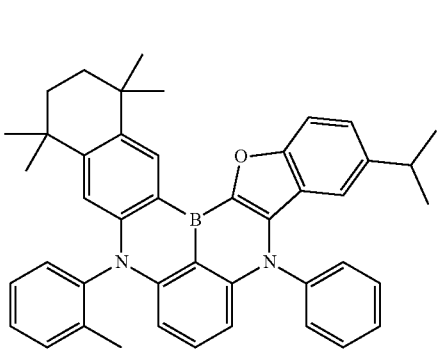
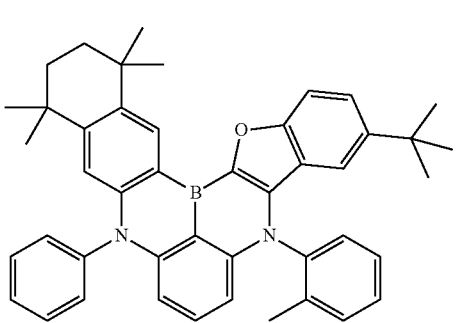

497
-continued
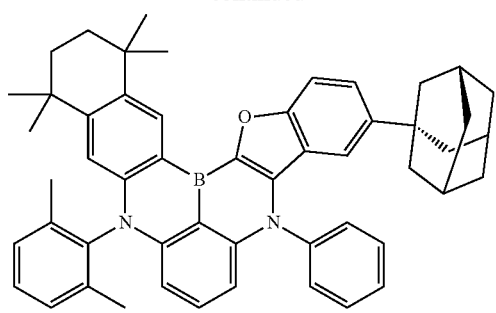
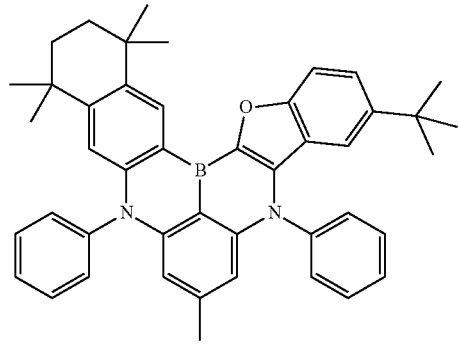
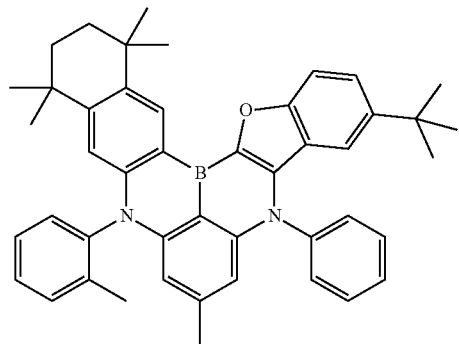
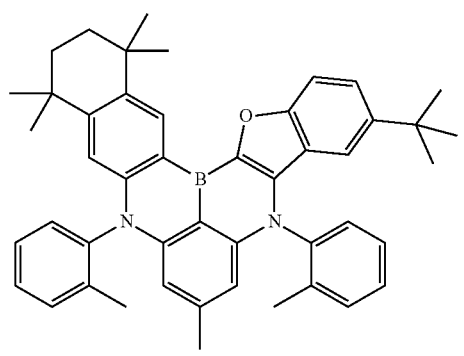
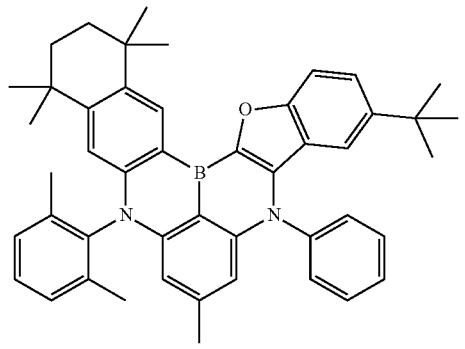
498
-continued
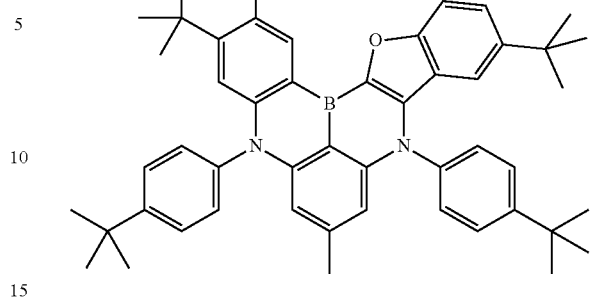
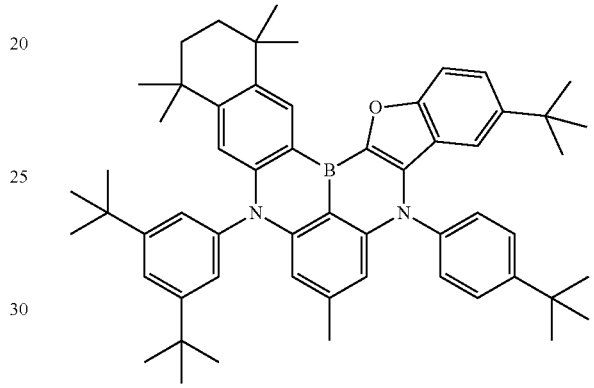
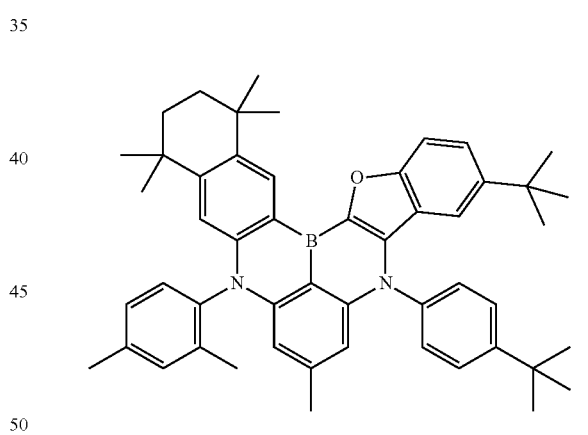

499 -continued
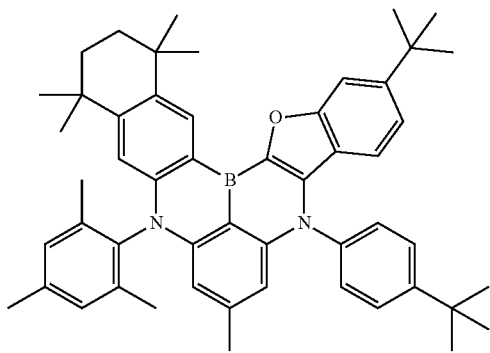
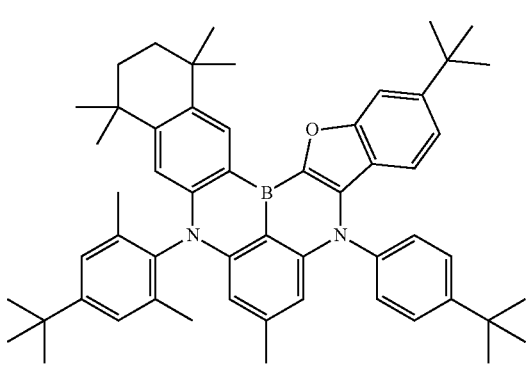
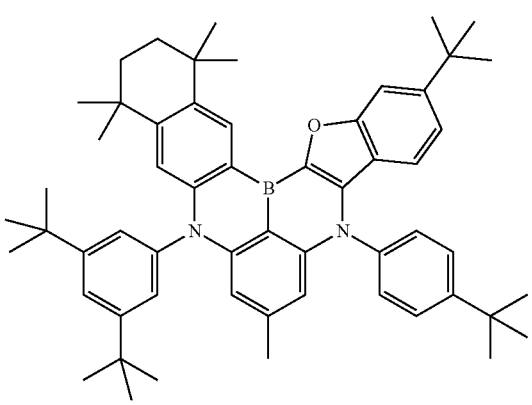
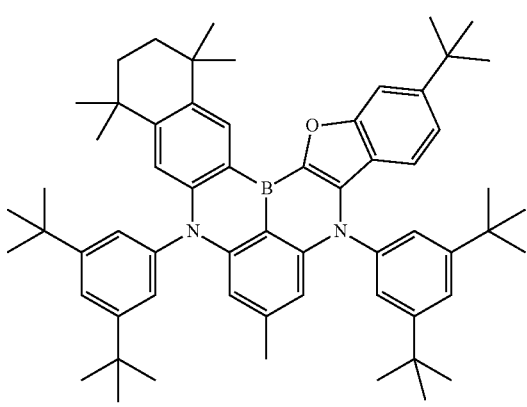
500 -continued
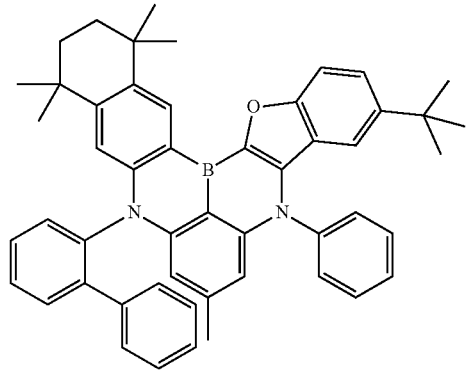
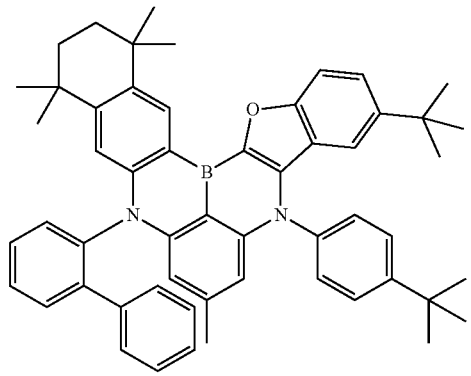
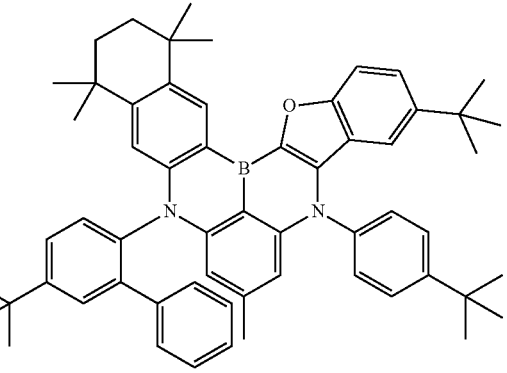
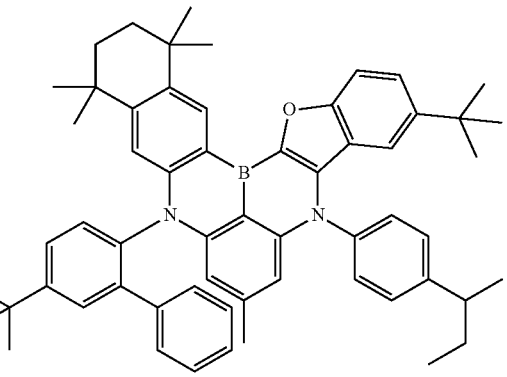

| 501 -continued | 502 -continued |
|---|---|
| 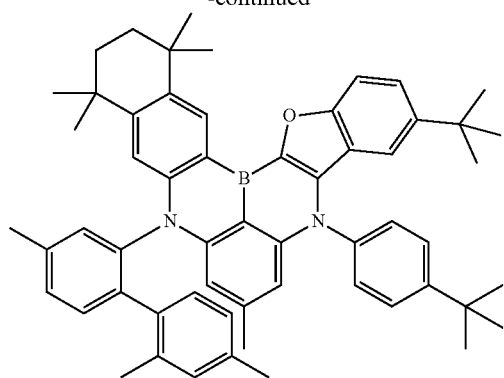 | 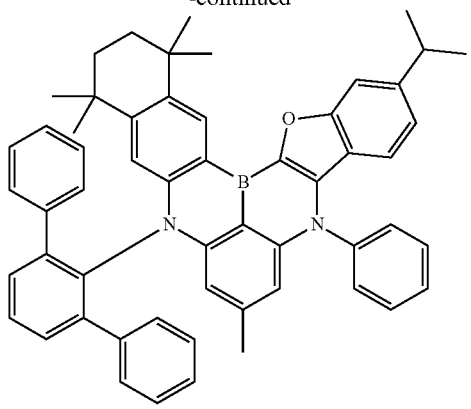 |
| 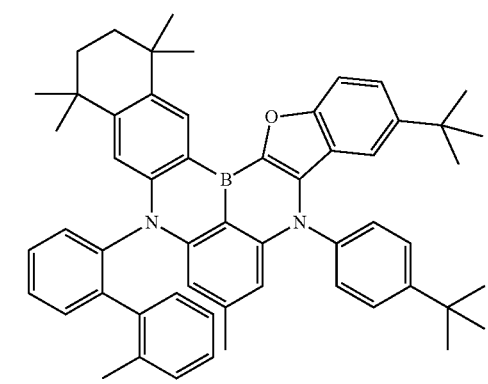 | 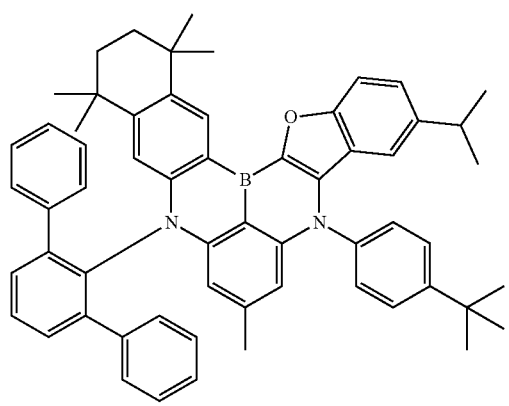 |
| 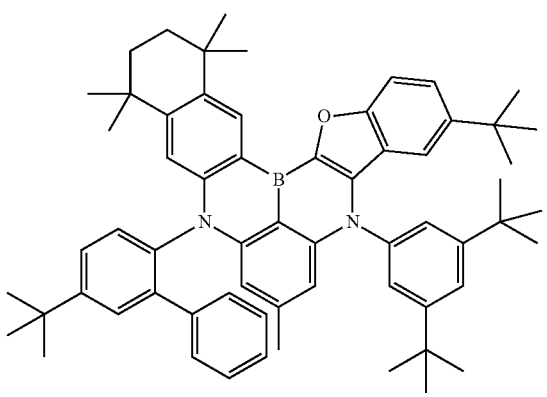 | 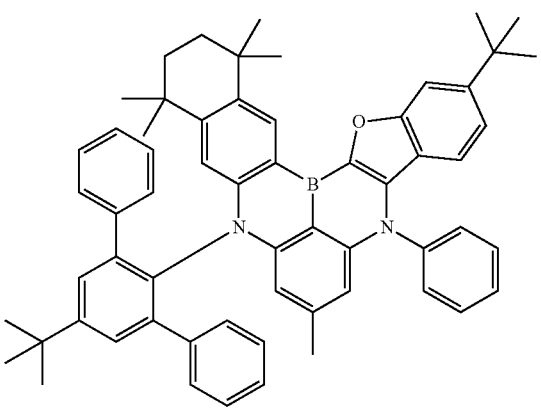 |
| 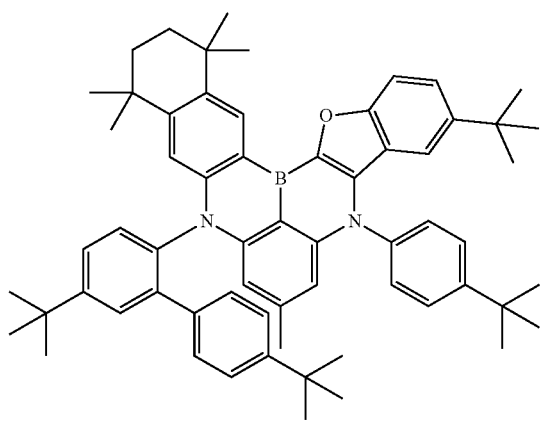 | 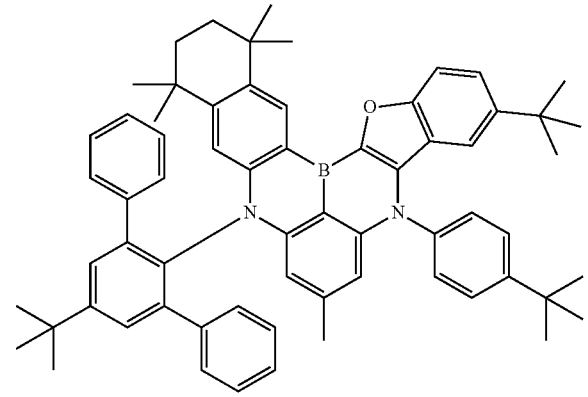 |

503
-continued
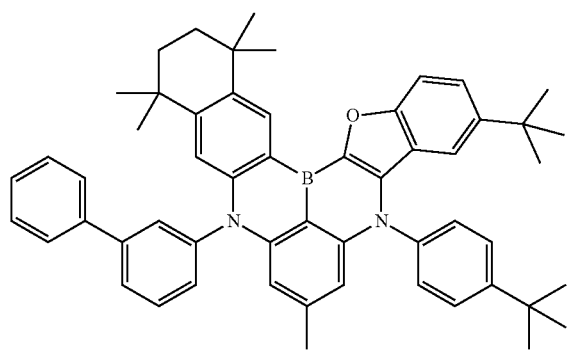
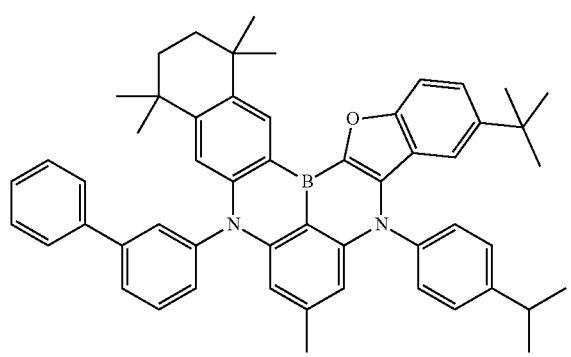
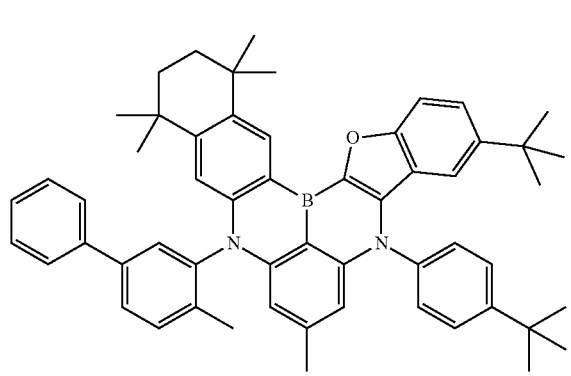
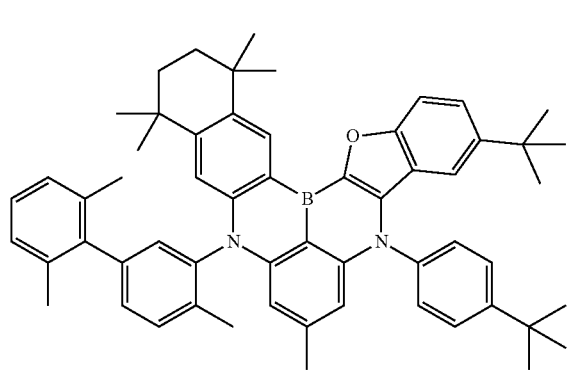
504
-continued
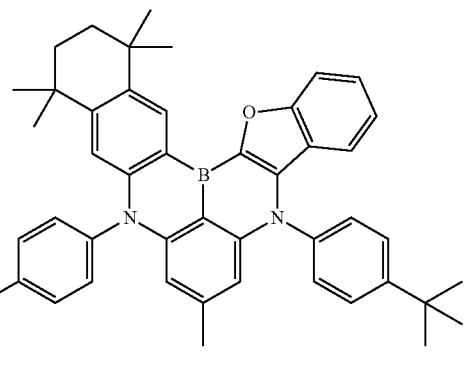
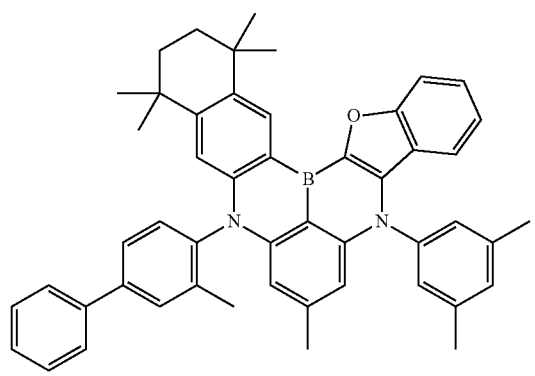
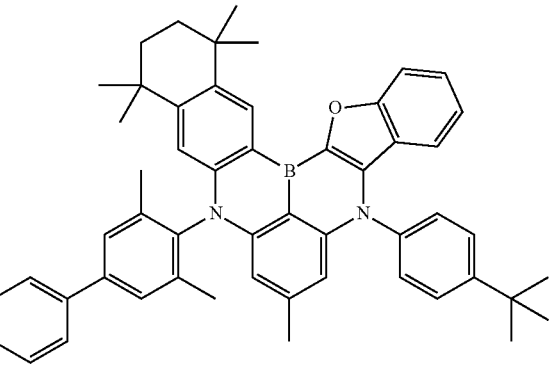
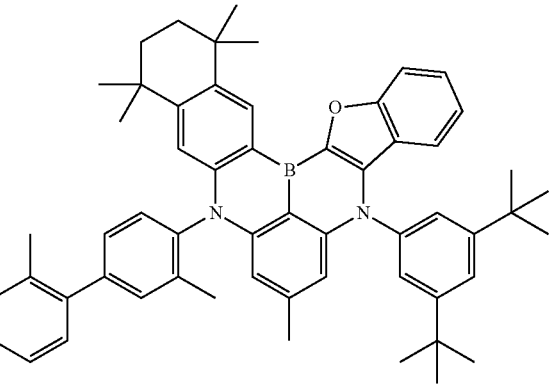

505
506

507
-continued
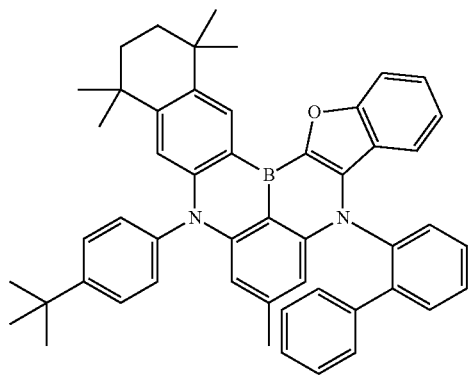
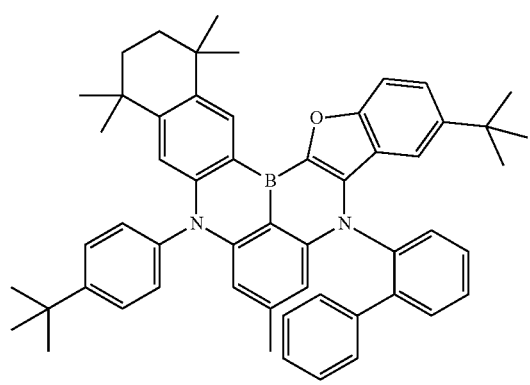
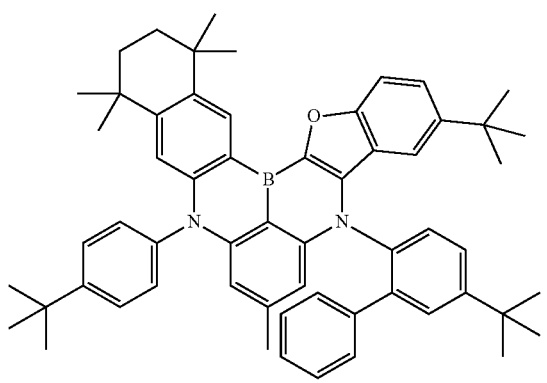
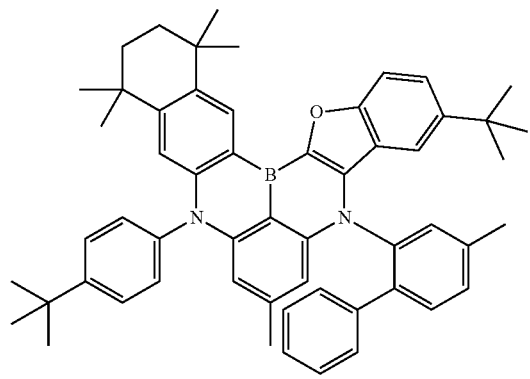
508
-continued
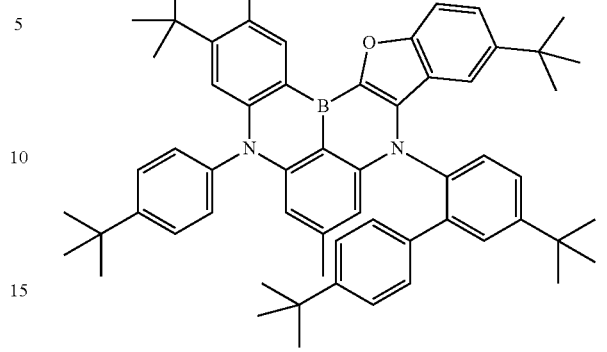
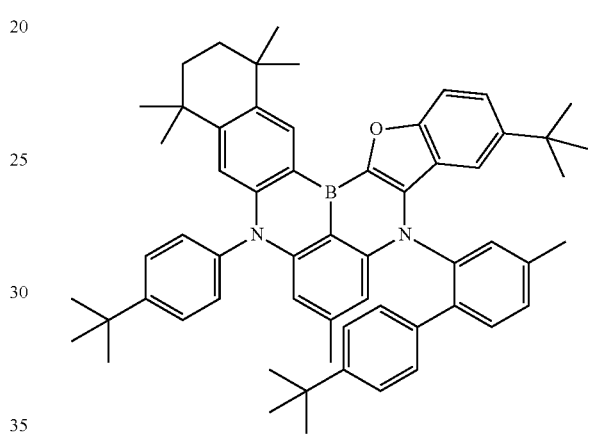
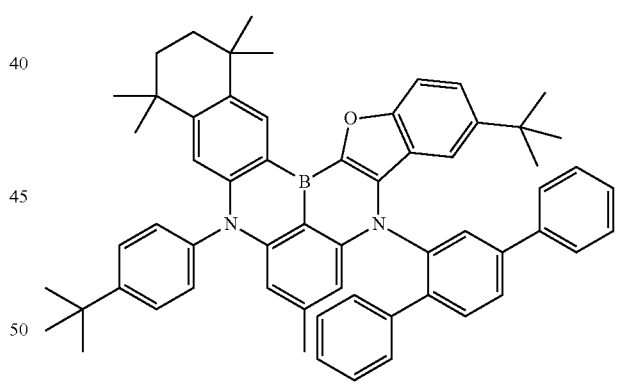
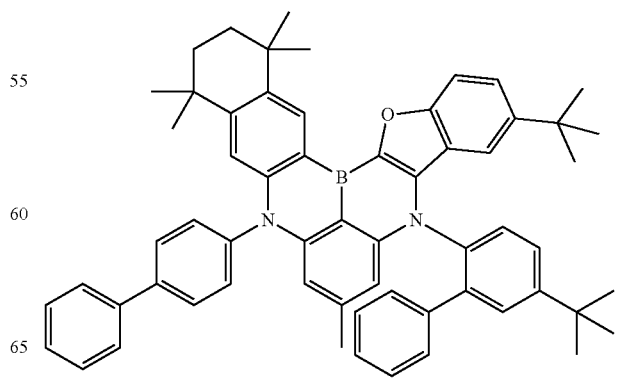

509
-continued
510
-continued
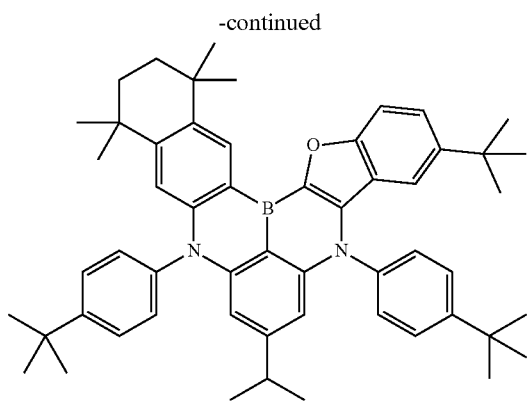
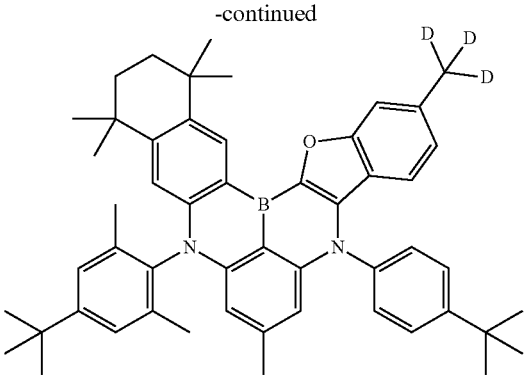
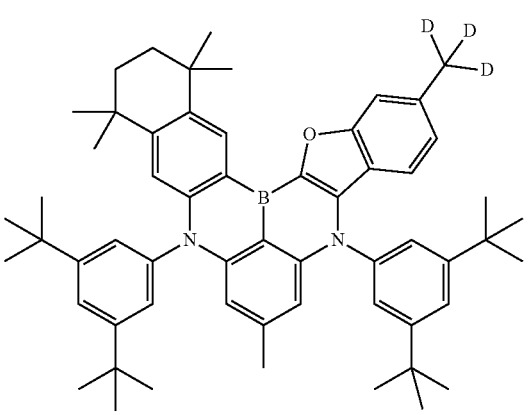
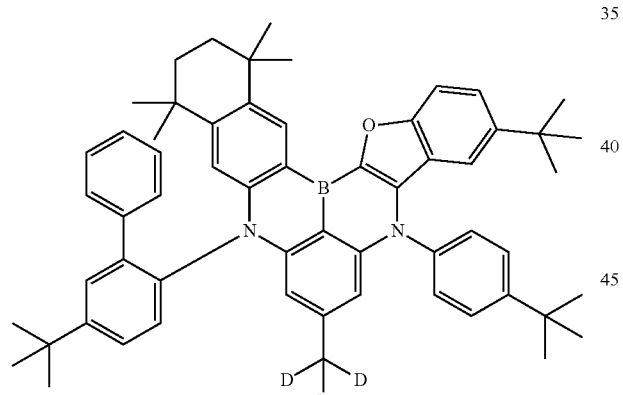
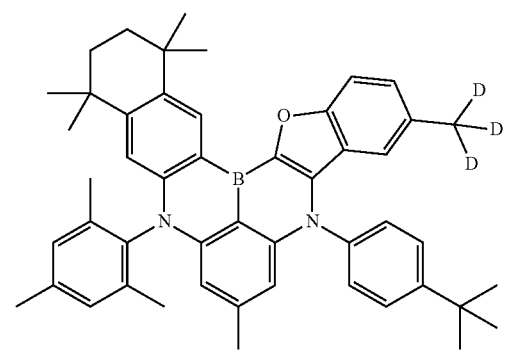
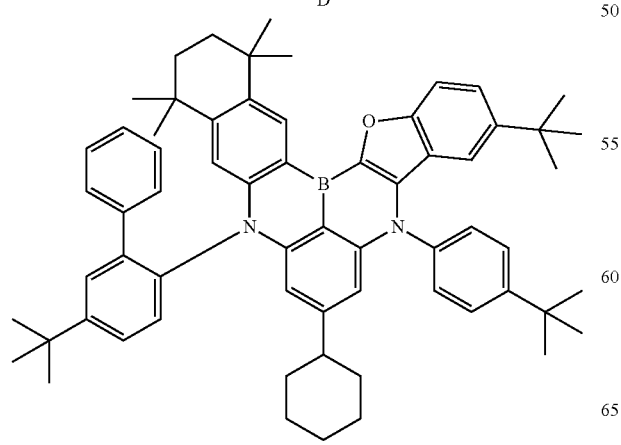
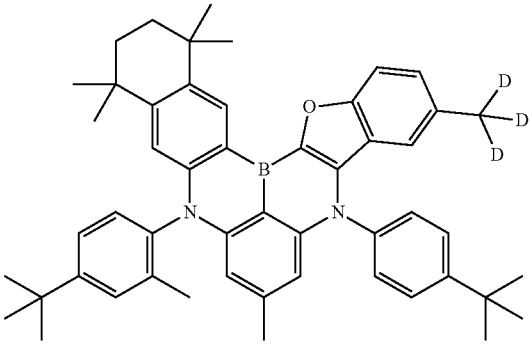

| 511 -continued | 512 -continued |
|---|---|
| 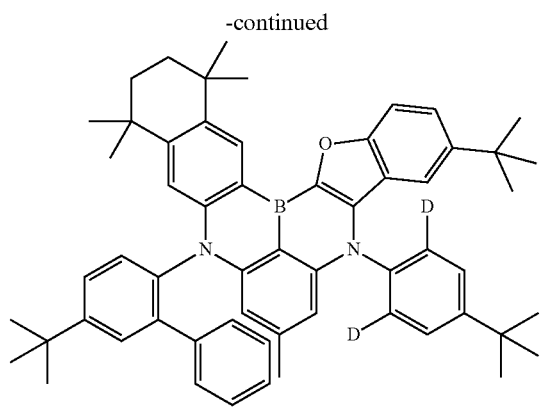 | 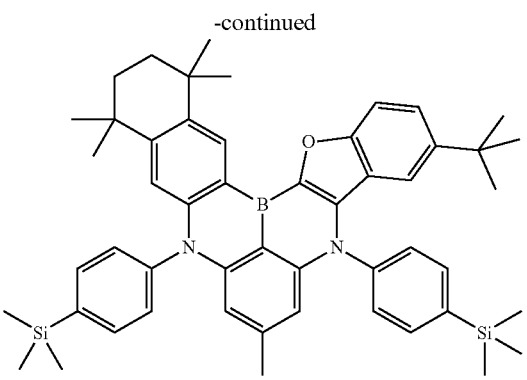 |
| 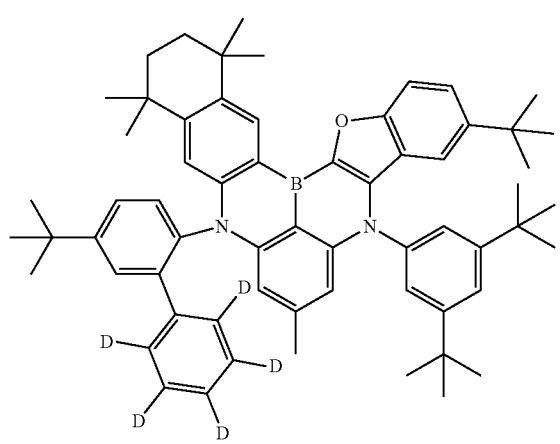 | 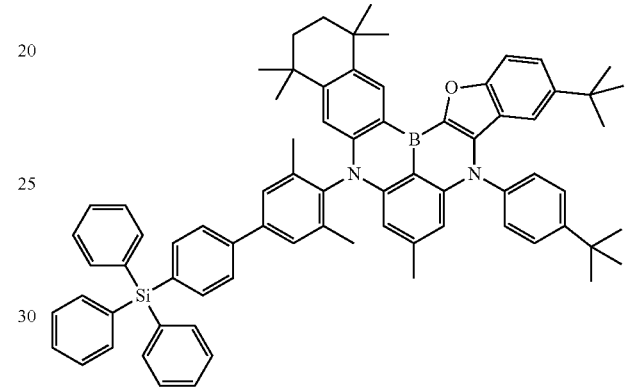 |
| 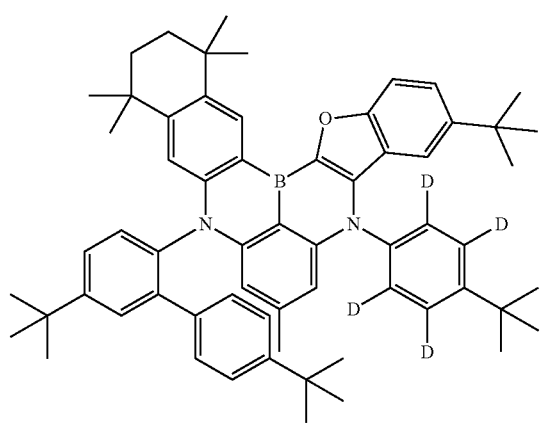 | 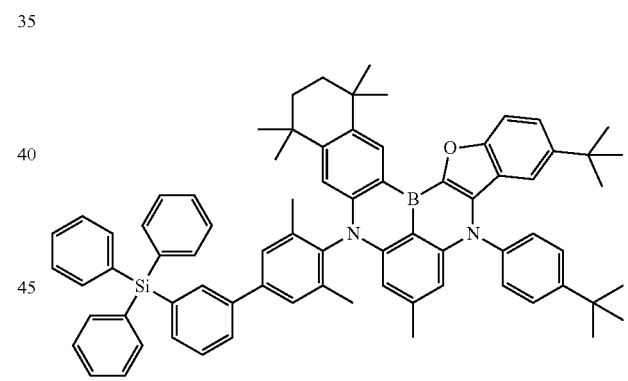 |
| 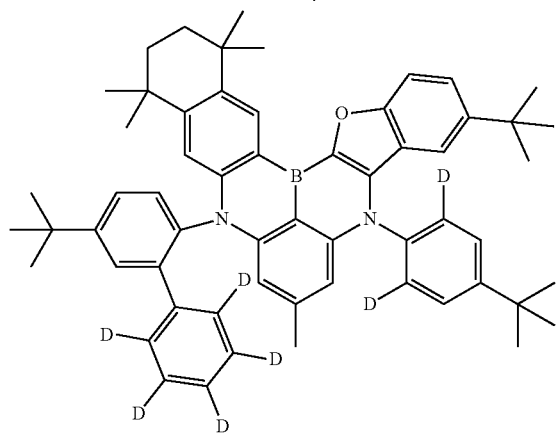 | 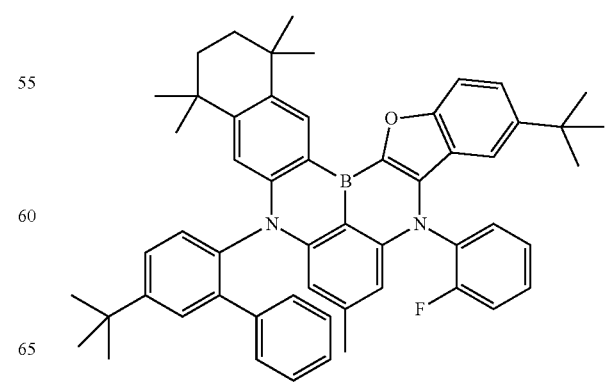 |

513
-continued
514
-continued
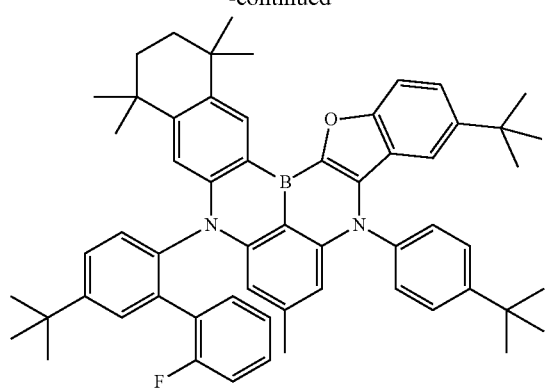
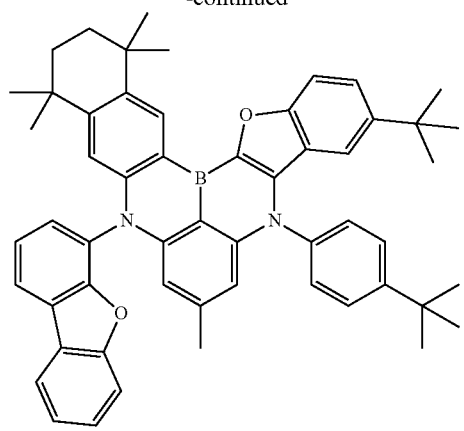
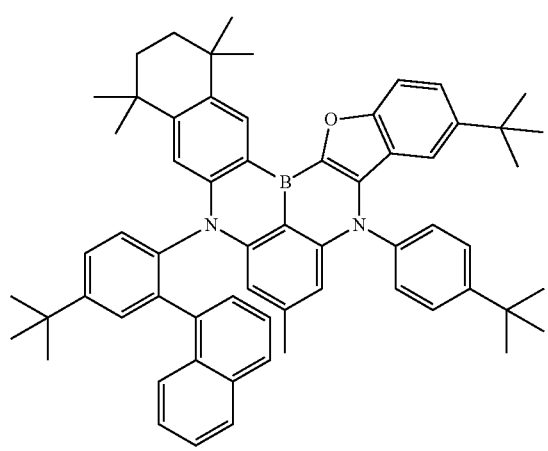
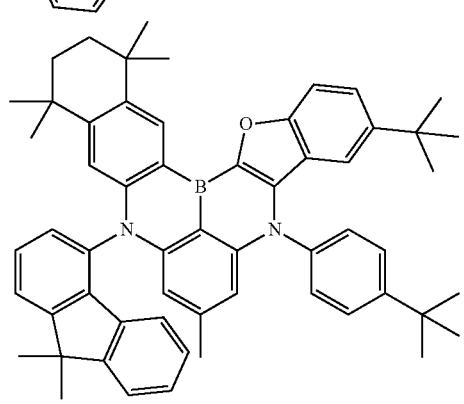
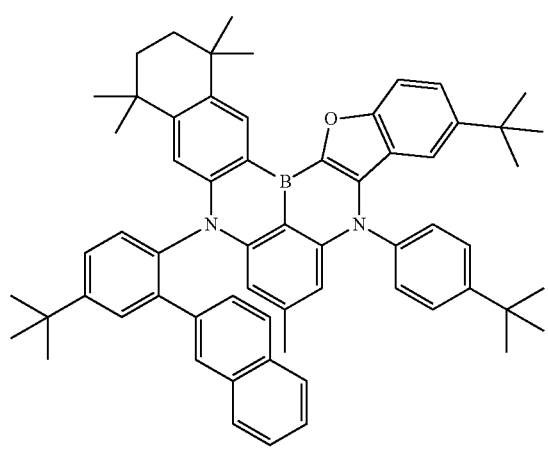
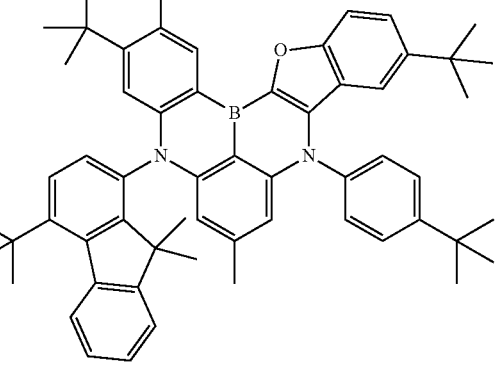
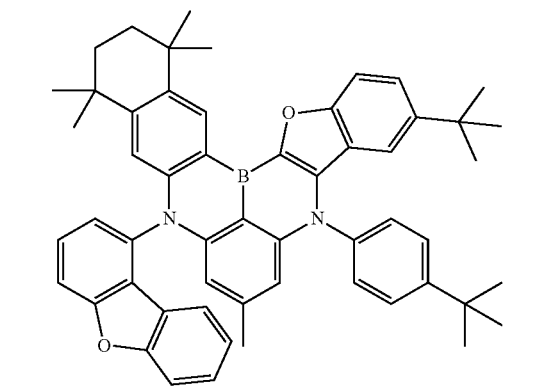

515
-continued
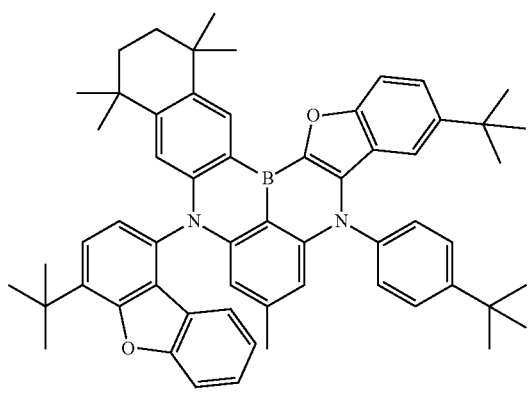
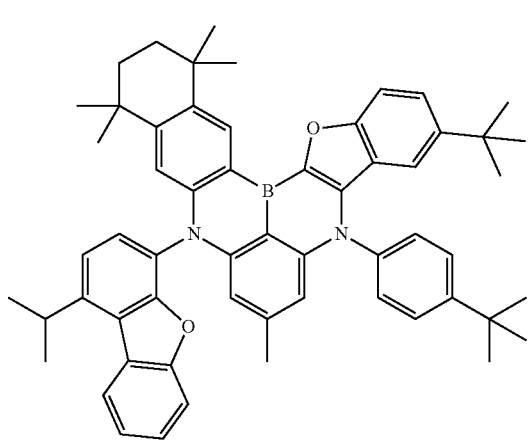
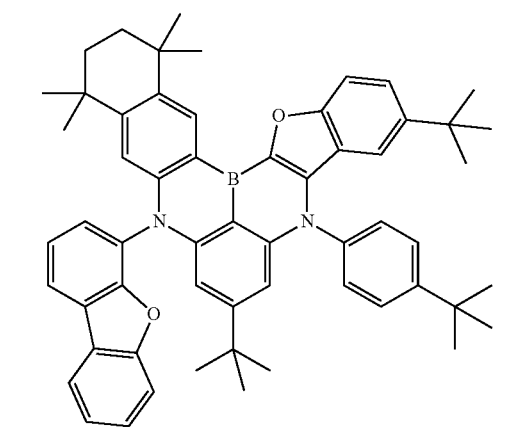
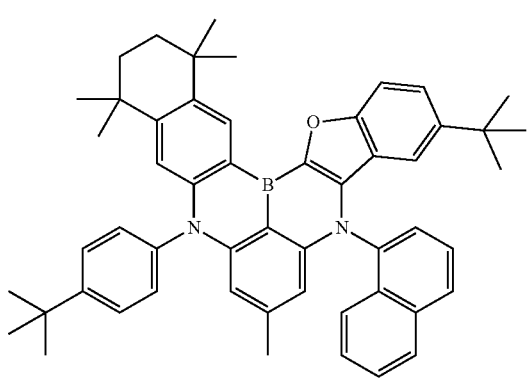
516
-continued
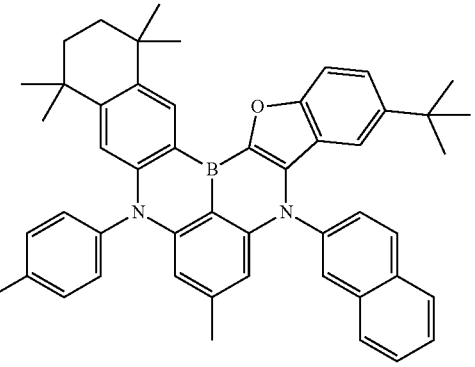
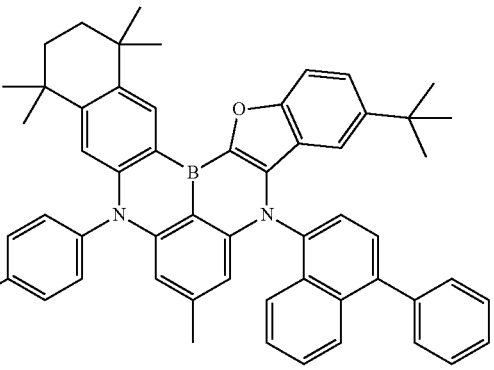
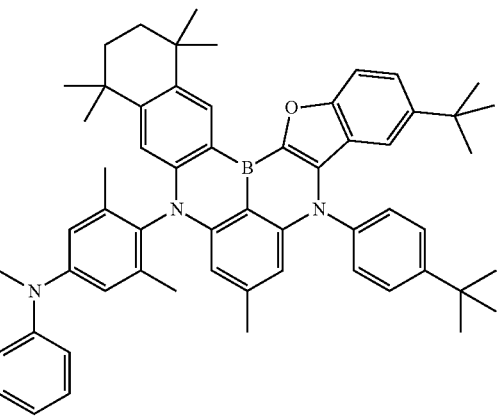
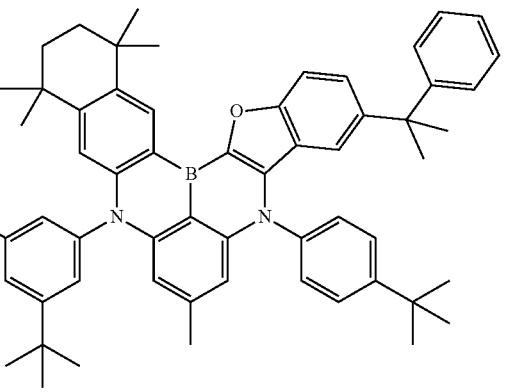

517
-continued
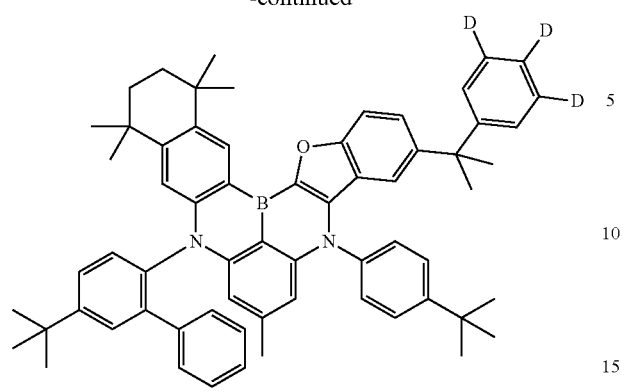
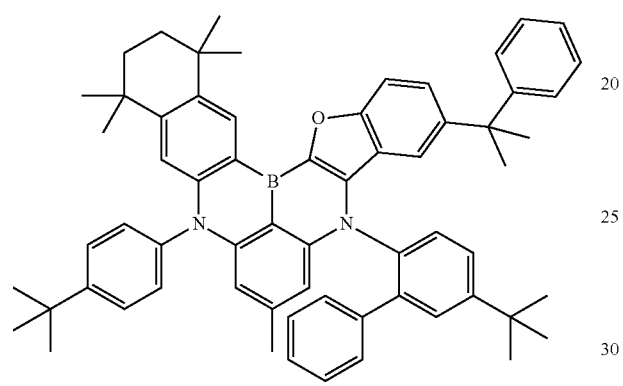
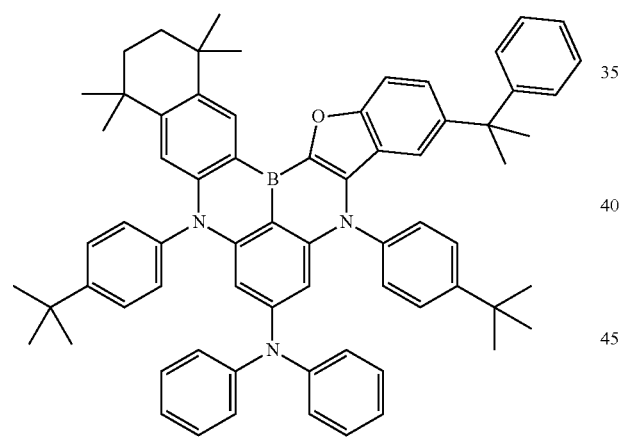
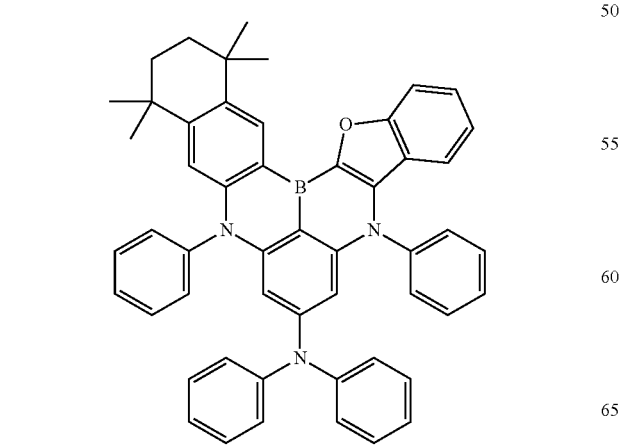
518
-continued
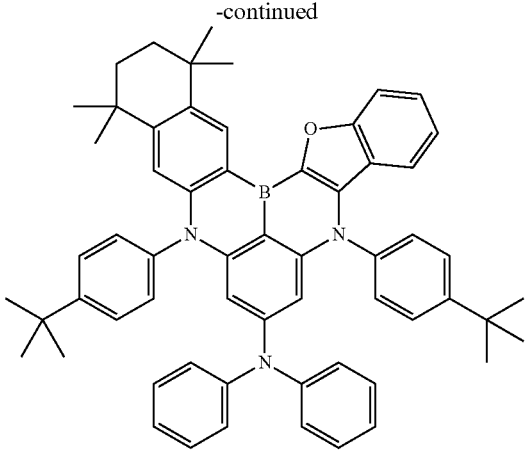
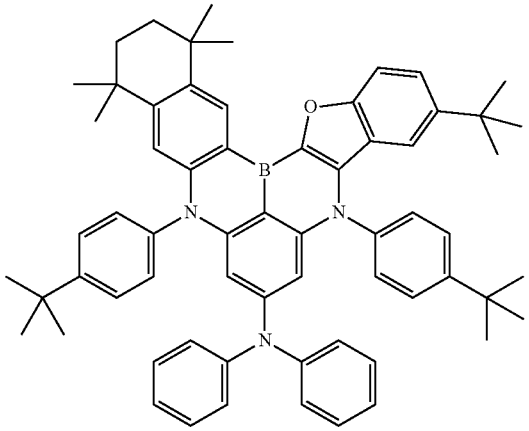
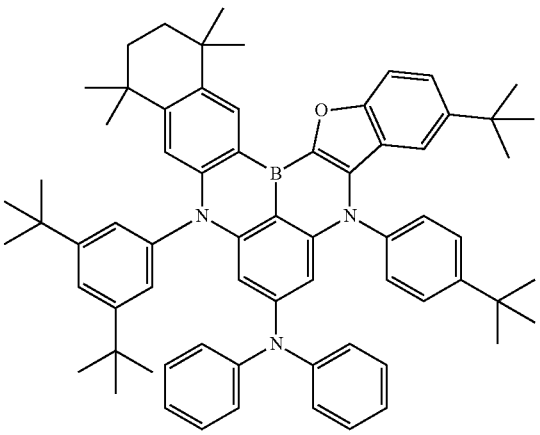
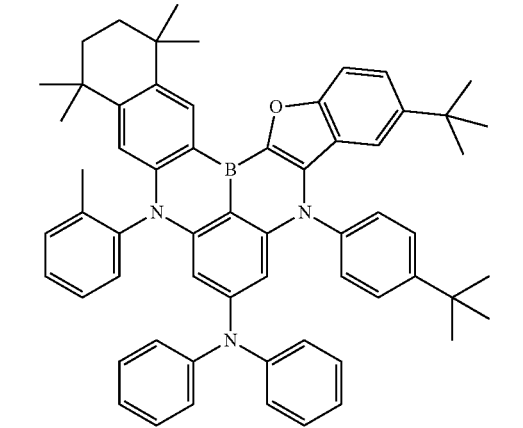

519
-continued
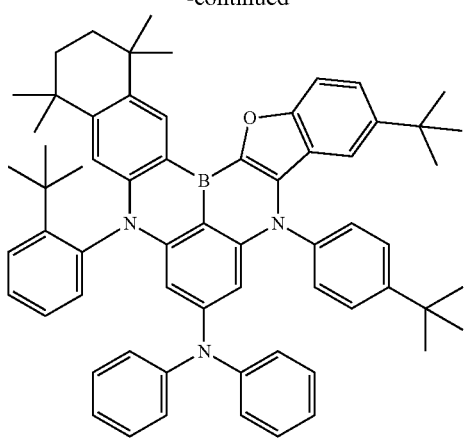
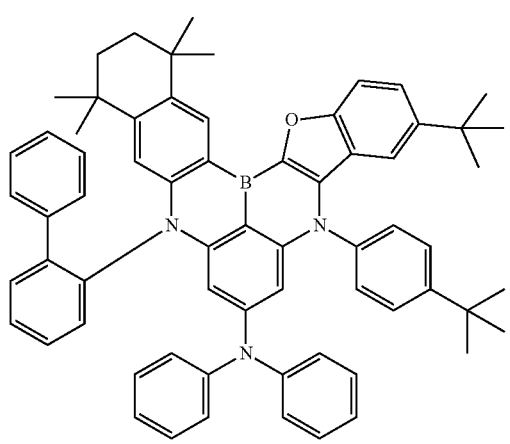
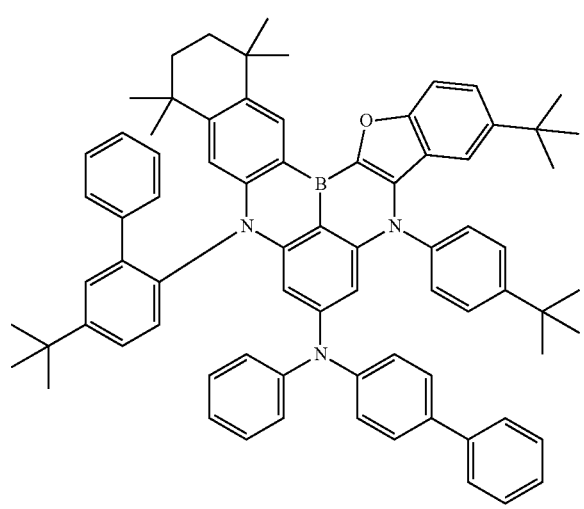
520
-continued
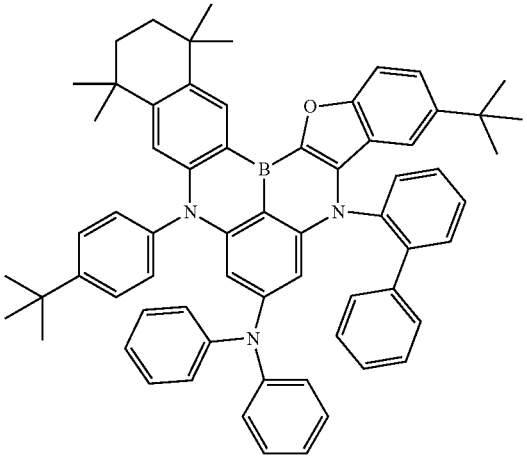
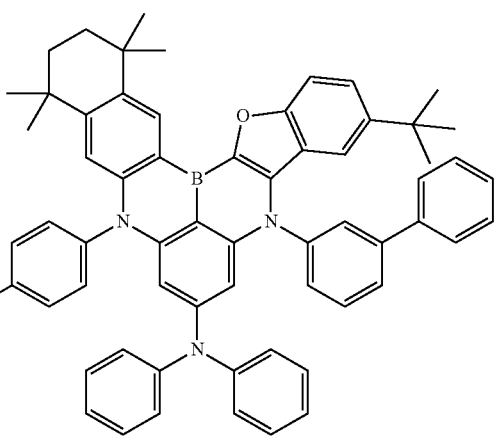
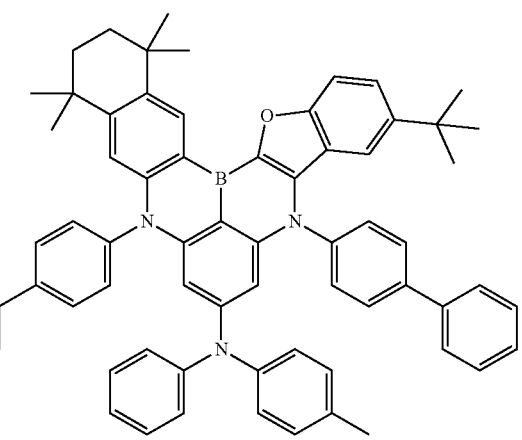

| 521 -continued | 522 -continued |
|---|---|
| 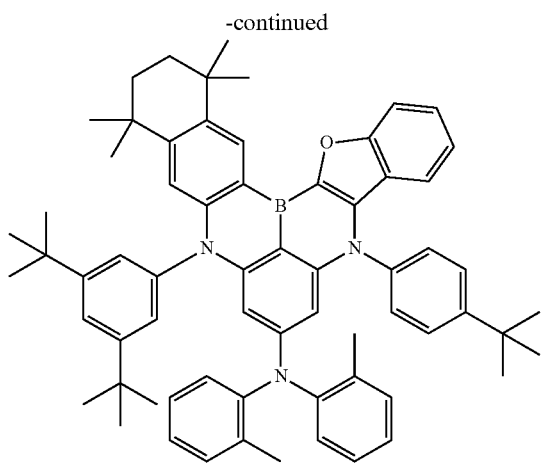 | 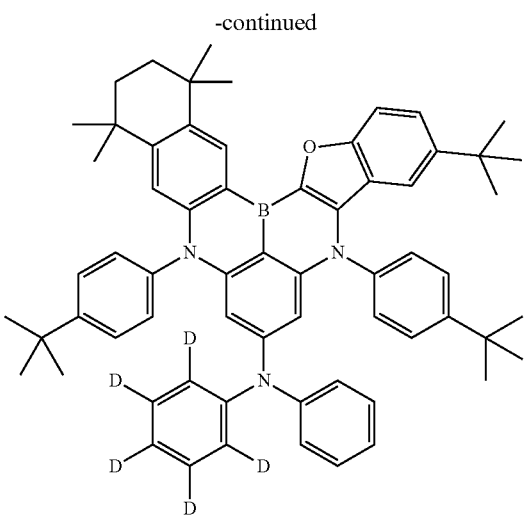 |
| 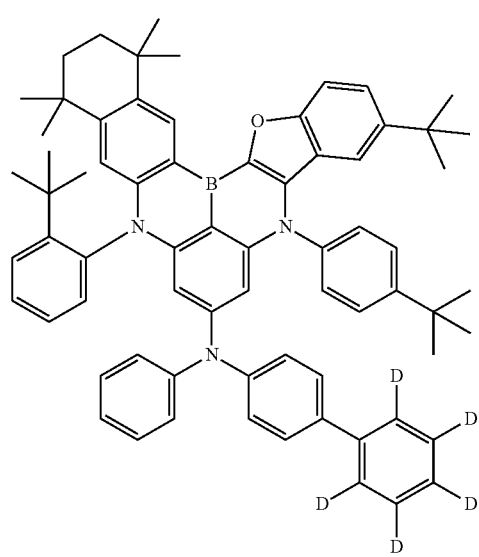 | 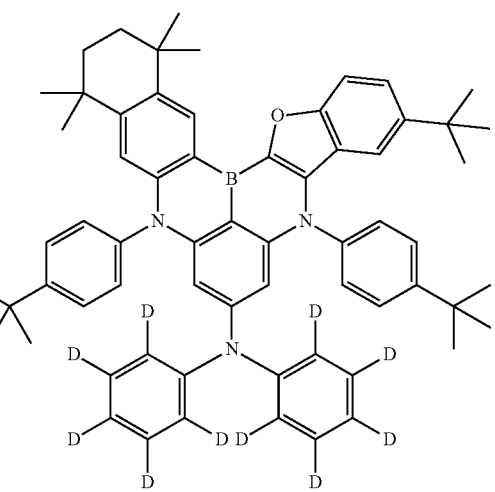 |
| 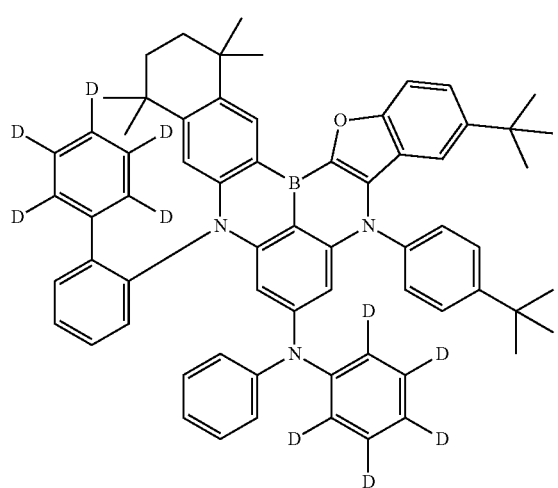 | 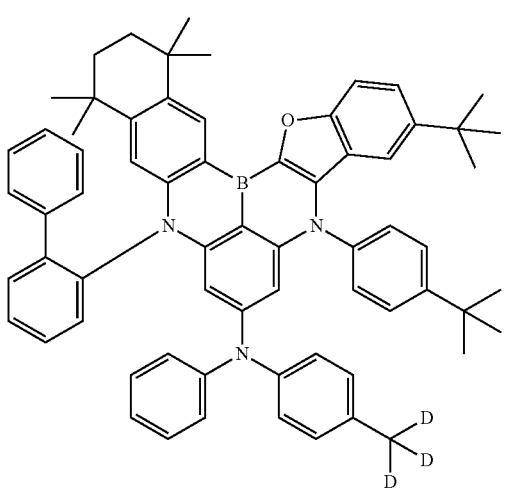 |

523
-continued
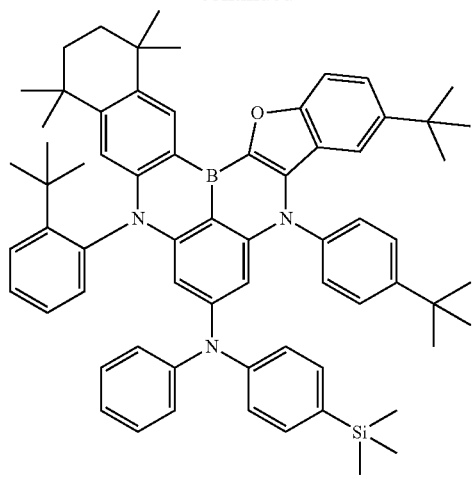
524
-continued
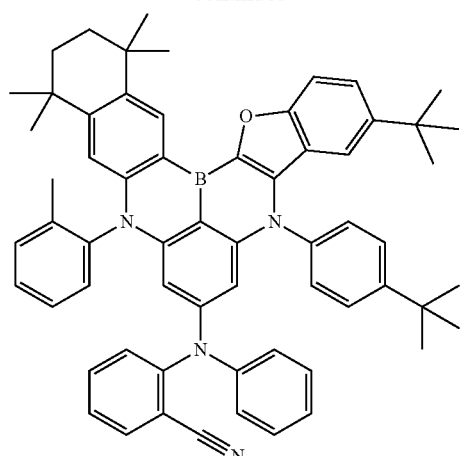
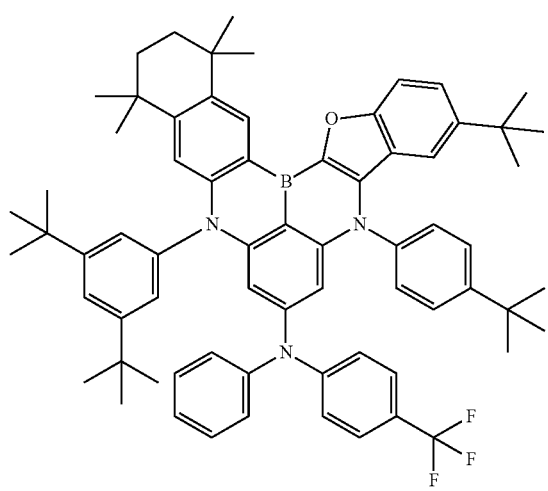
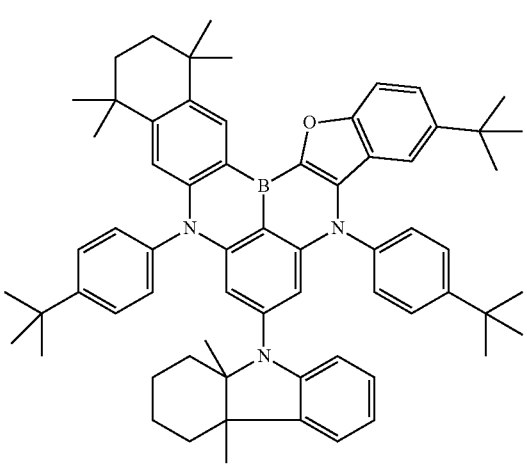
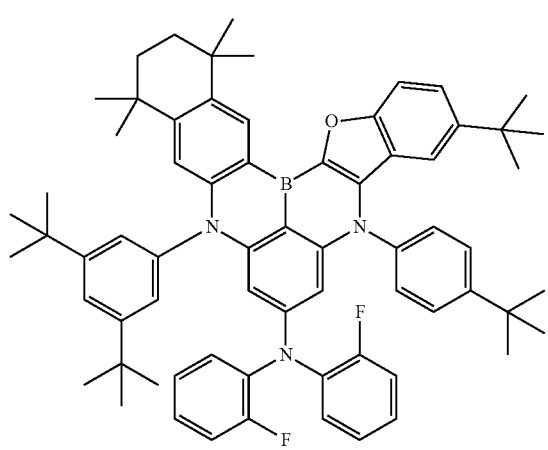
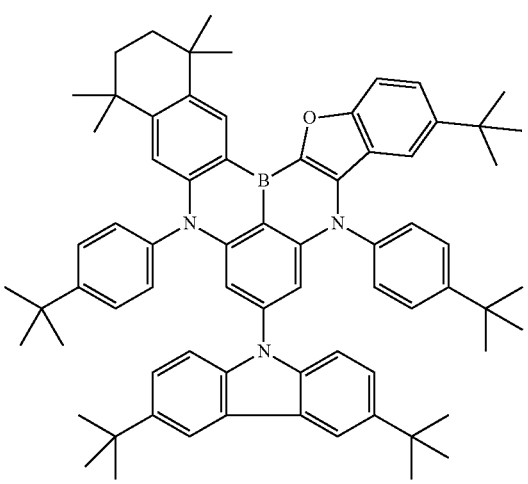

525
-continued
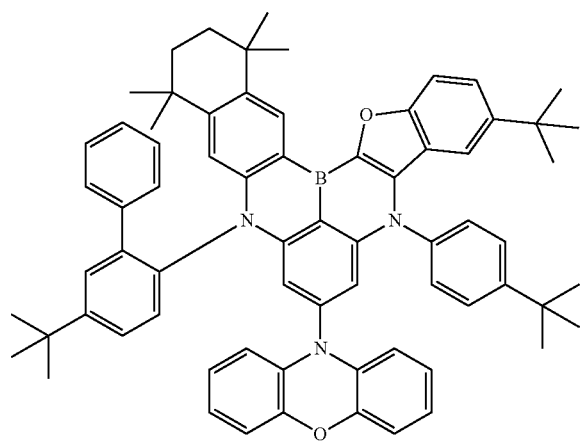
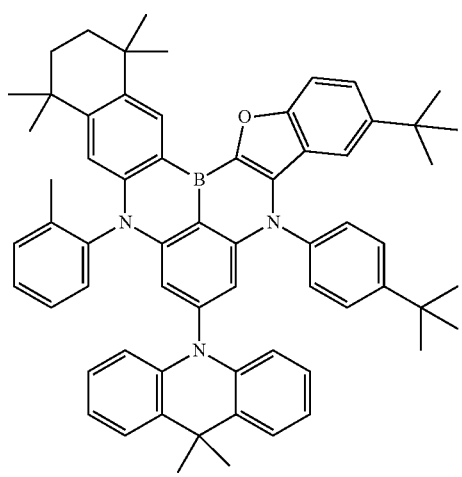
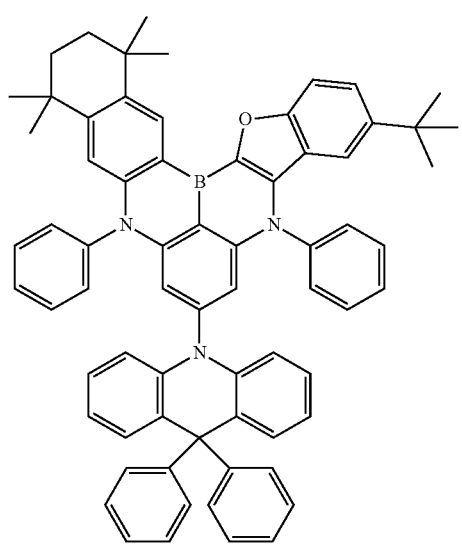
526
-continued
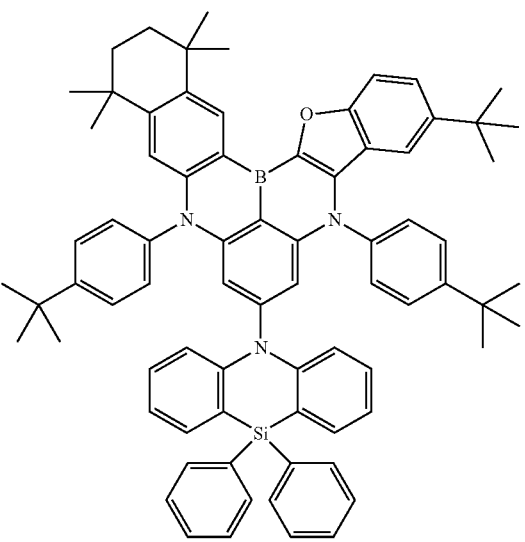
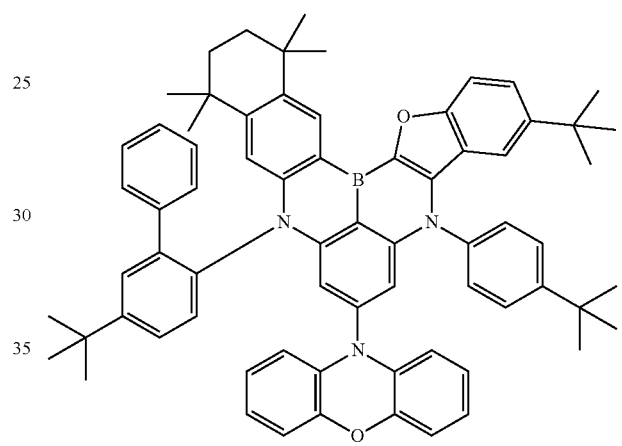
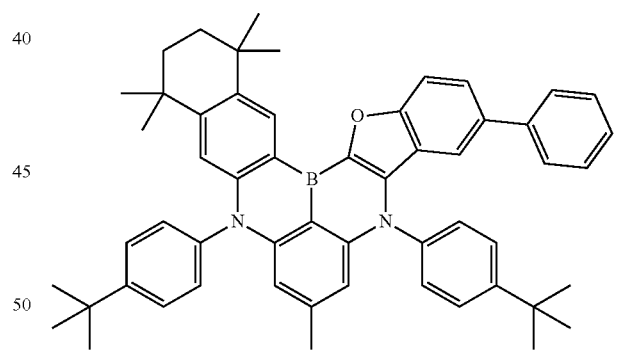
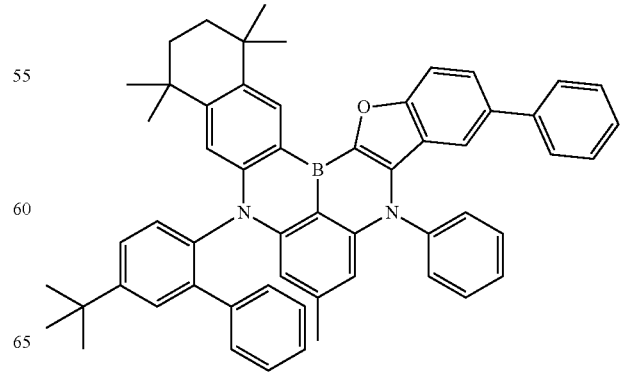

527
-continued
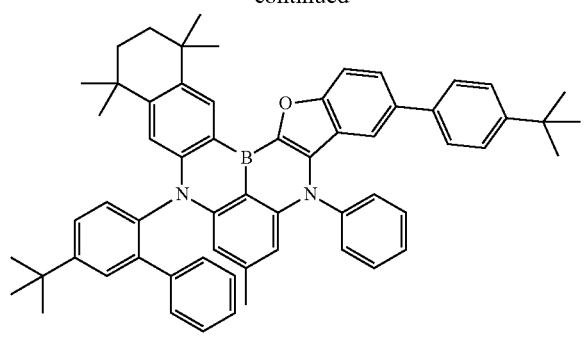
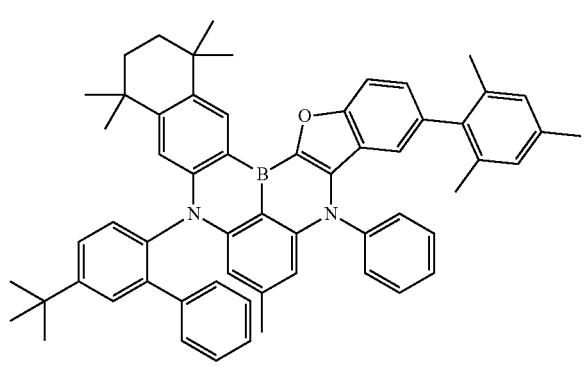
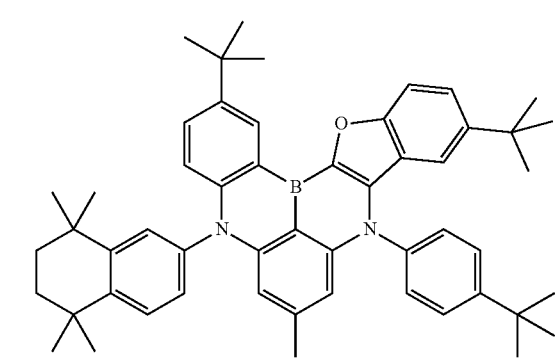
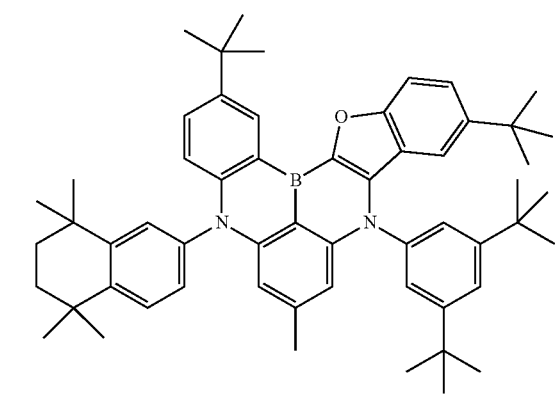
528
-continued
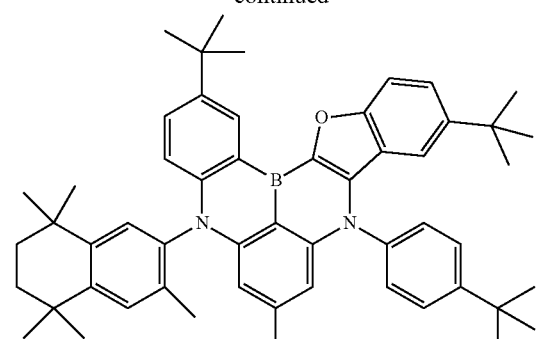
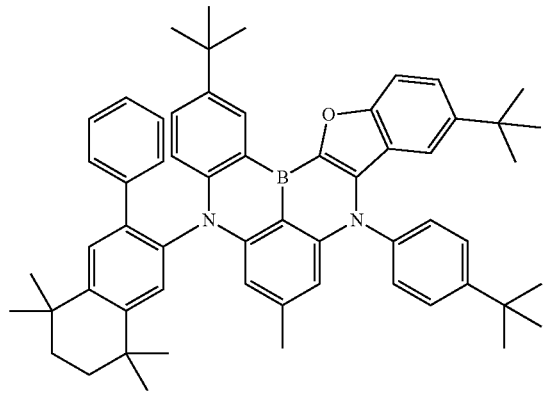
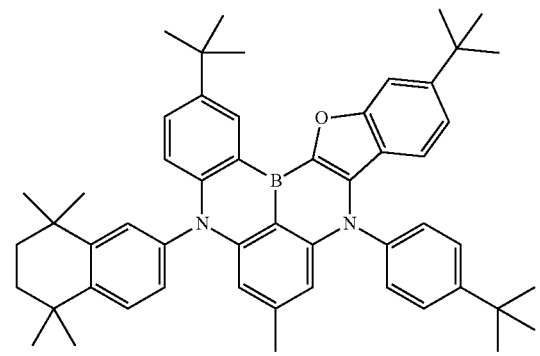
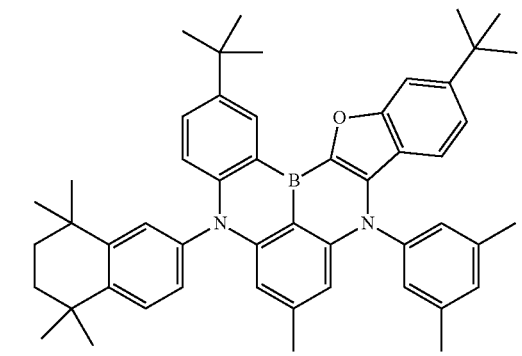

529
-continued
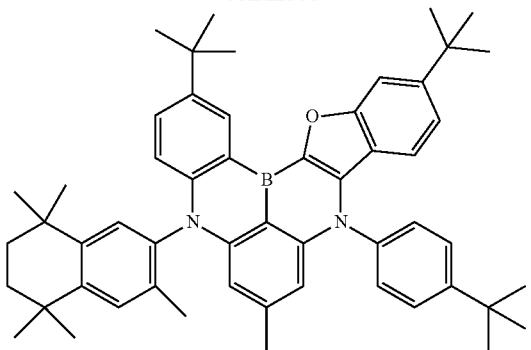
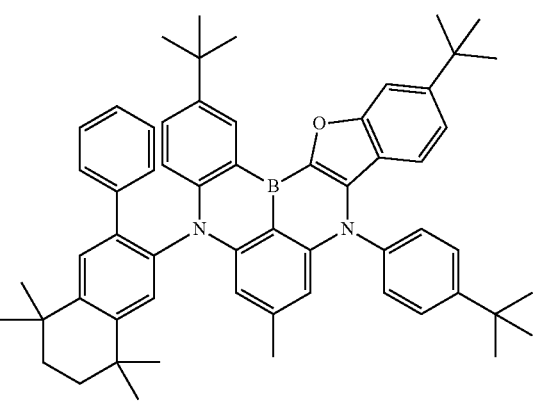
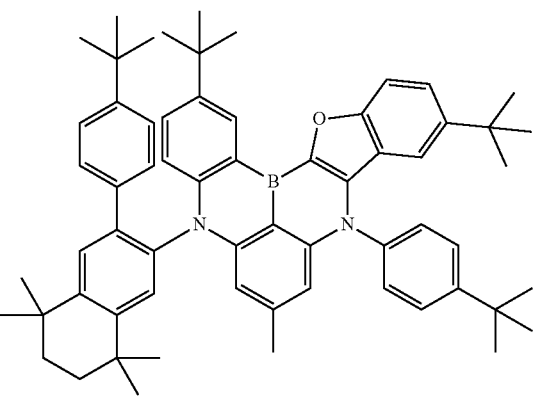
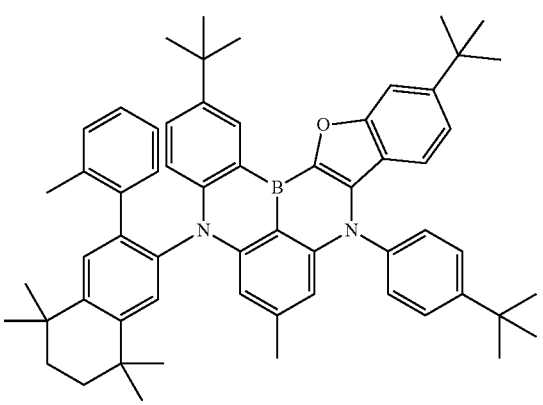
530
-continued
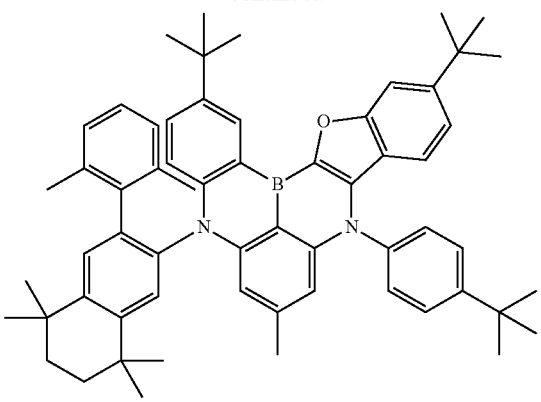
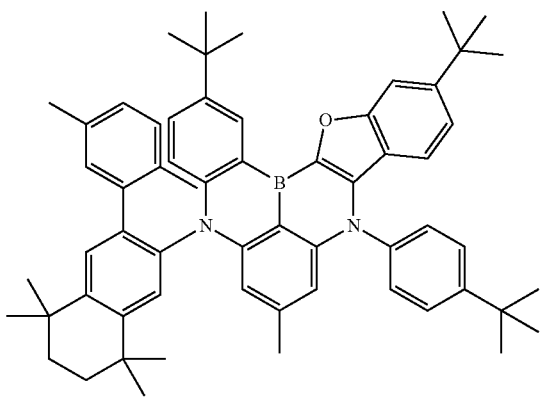
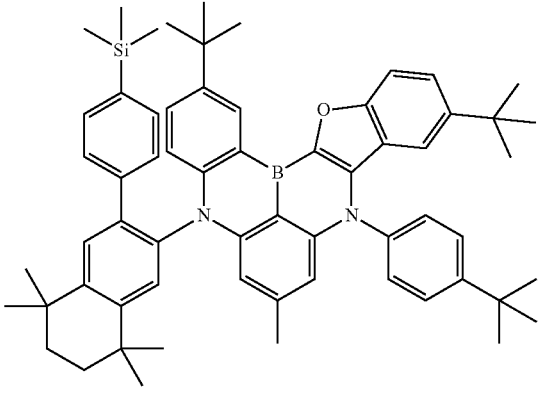
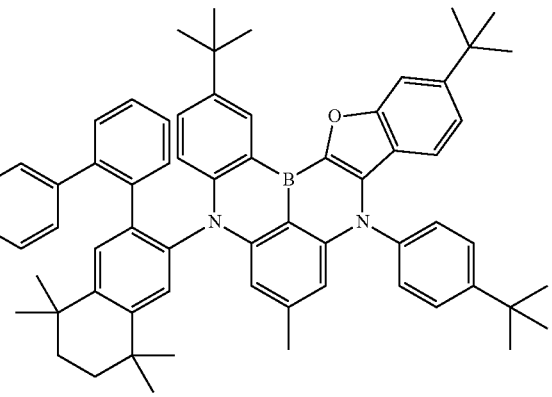

531
-continued
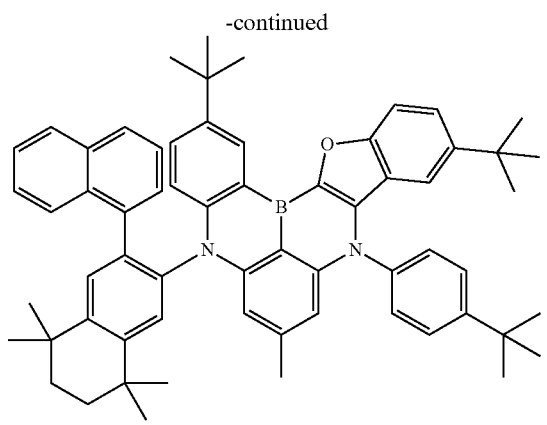
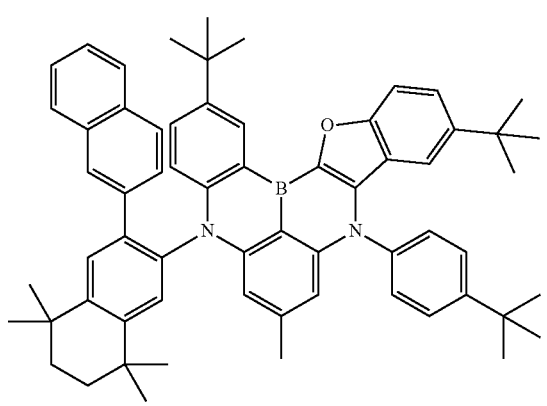
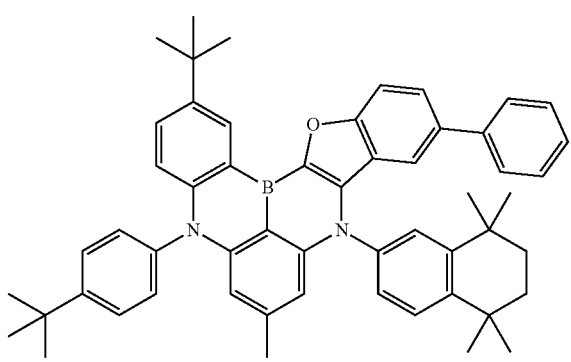
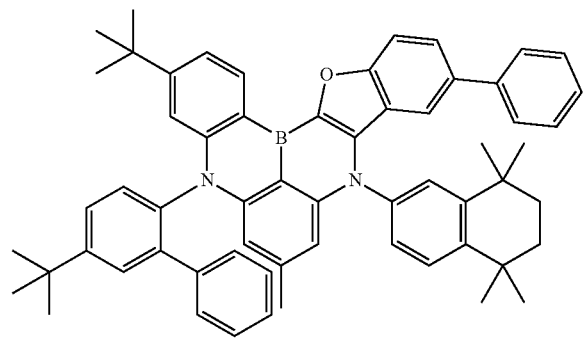
532
-continued
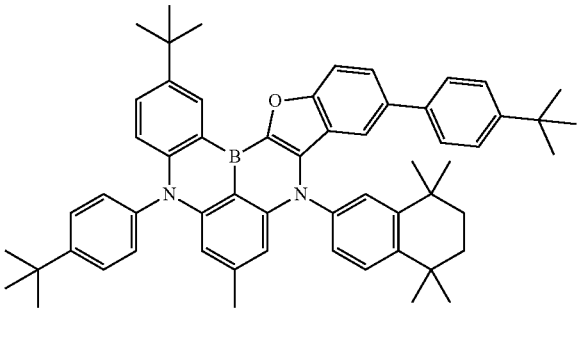
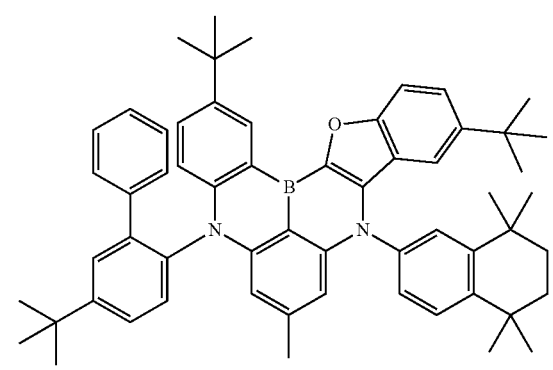
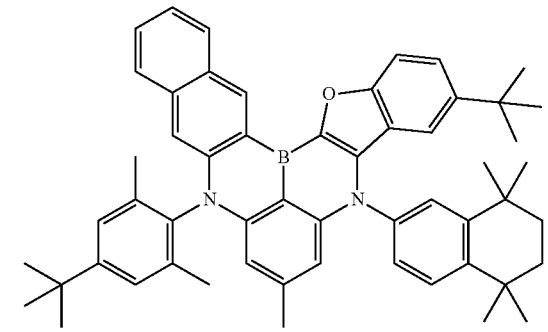
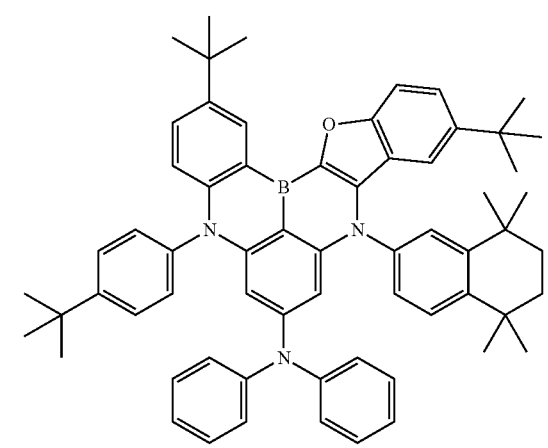

533
-continued
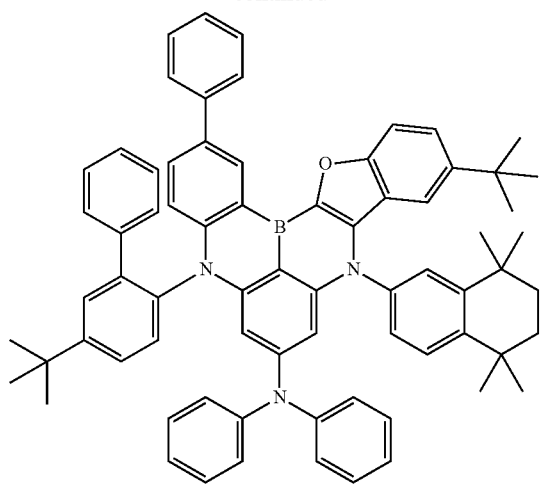
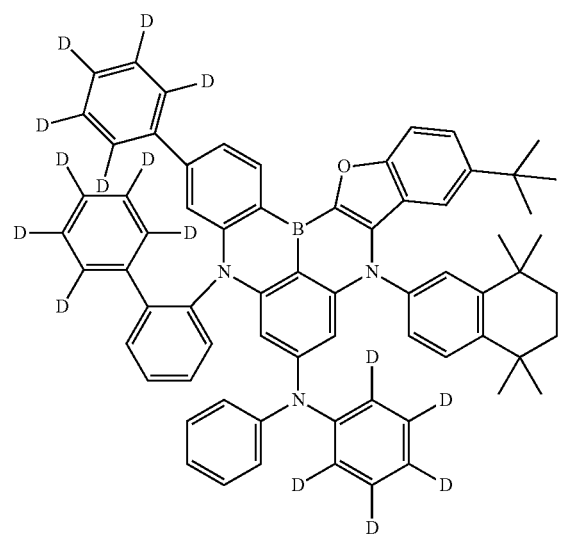
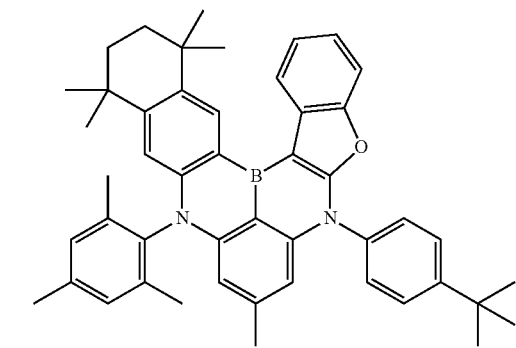
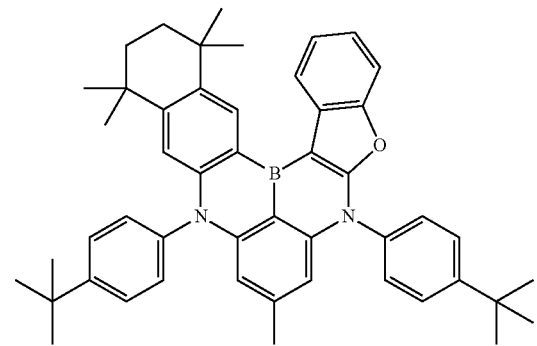
534
-continued
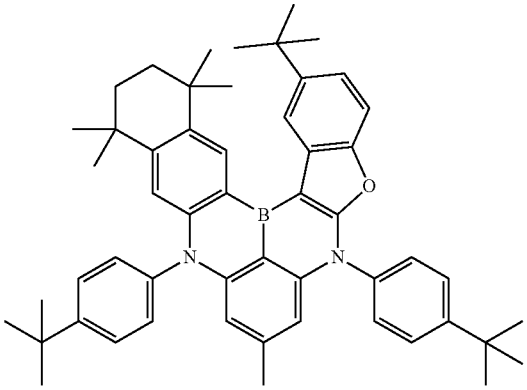
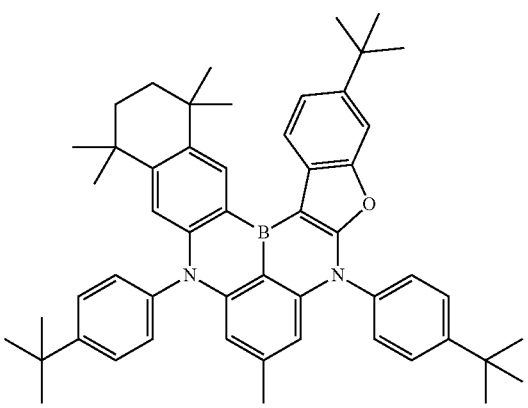
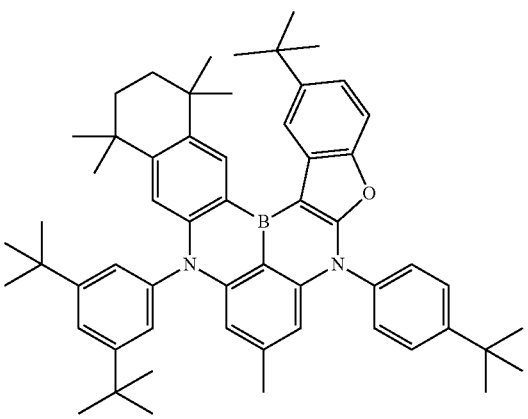
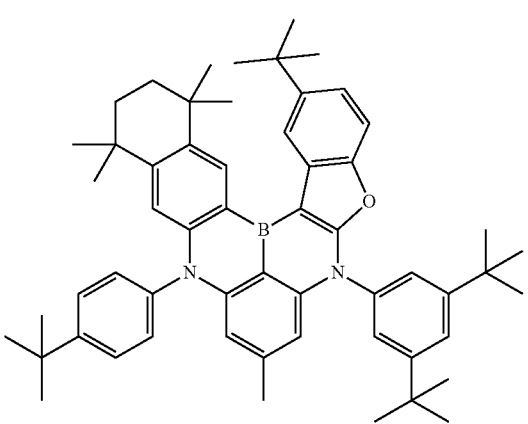

535
-continued
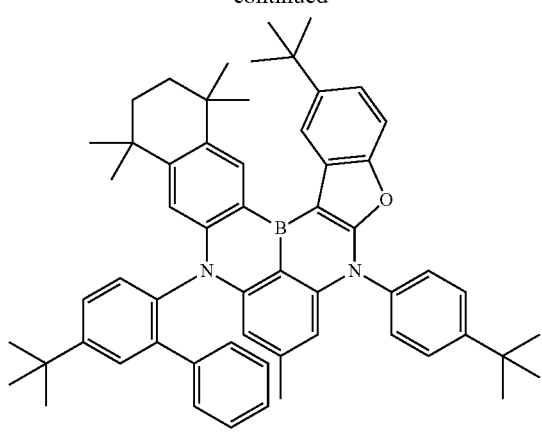
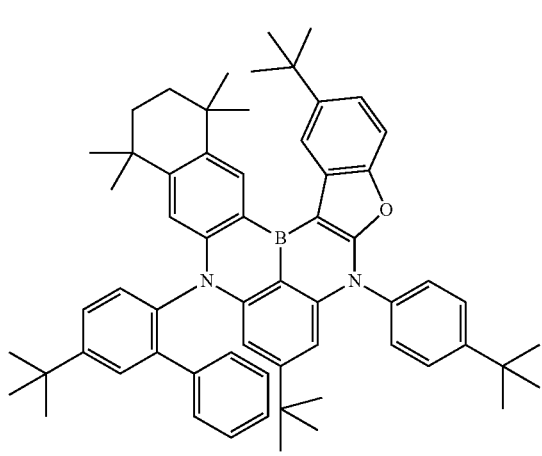
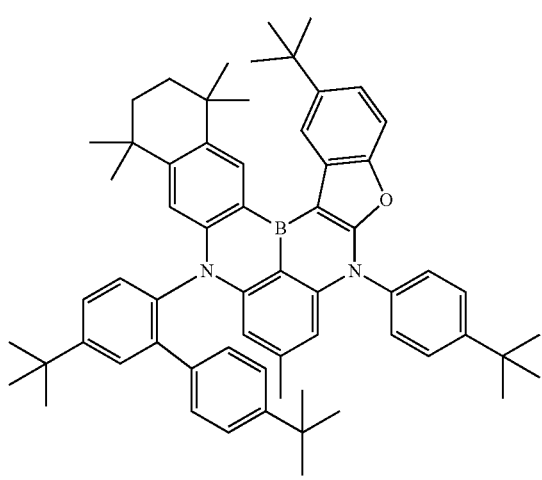
536
-continued
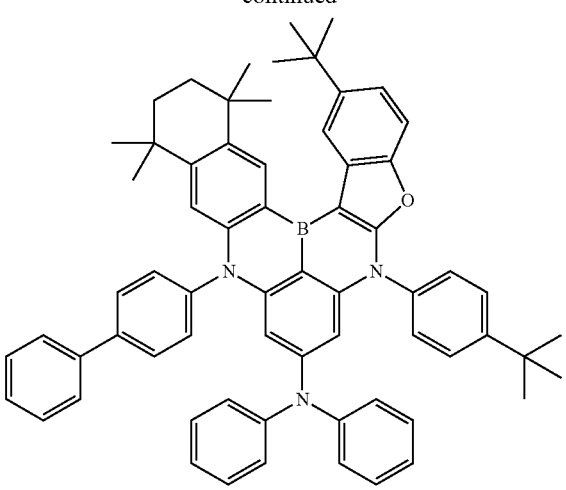
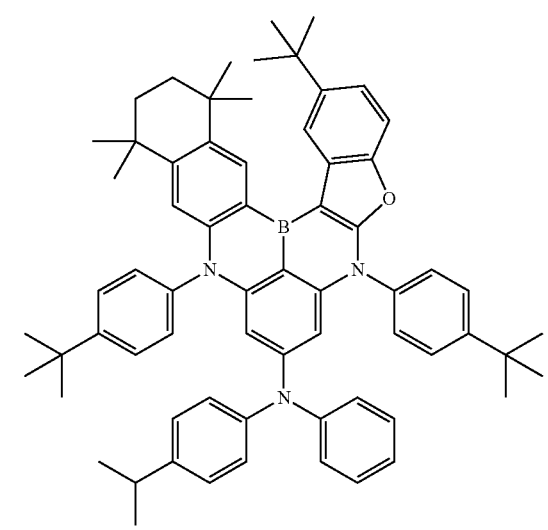
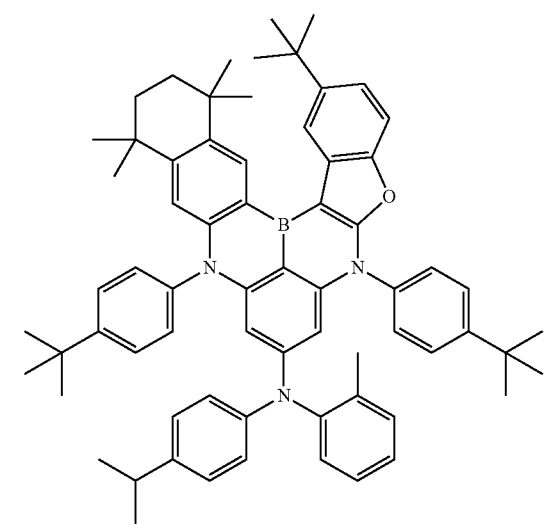

| 537 -continued | 538 -continued |
|---|---|
| 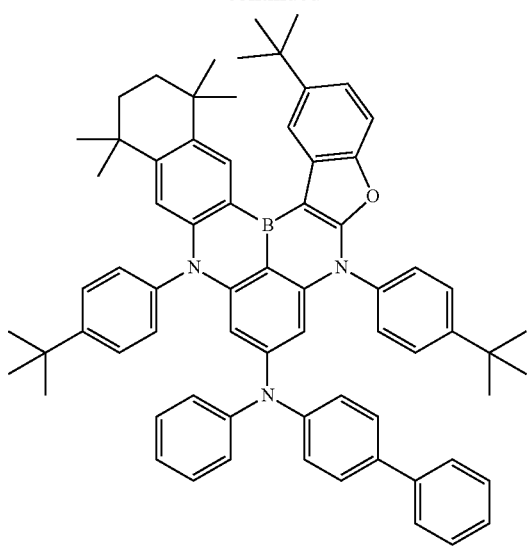 | 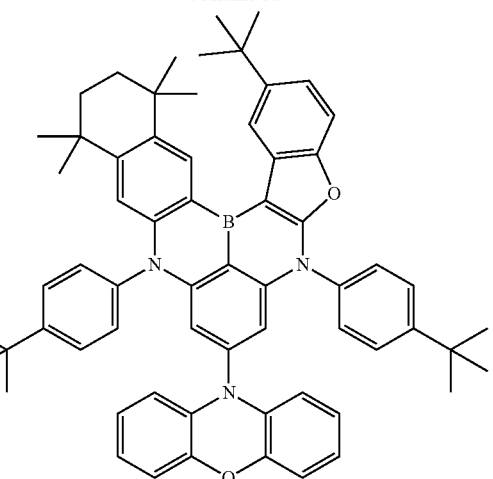 |
| 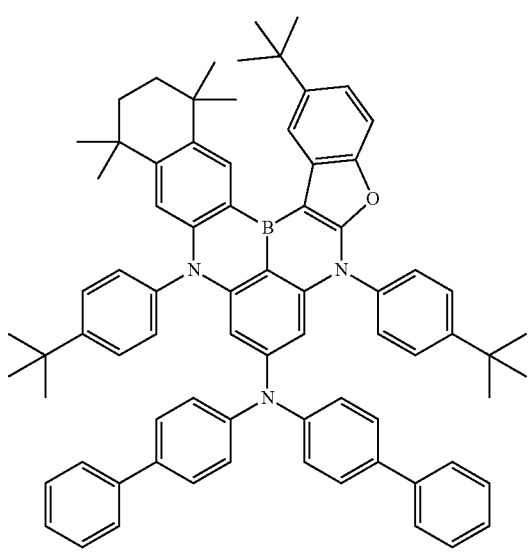 | 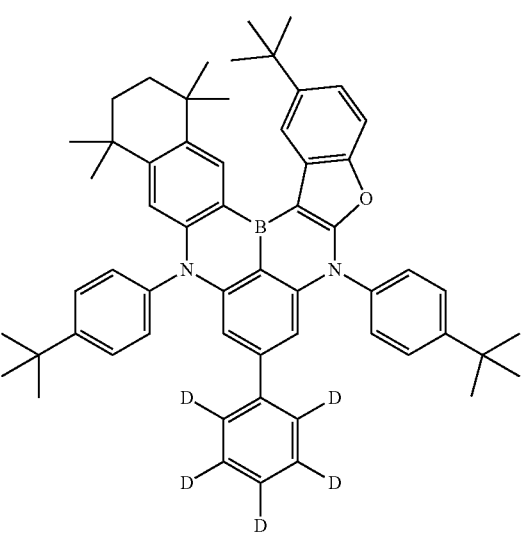 |
| 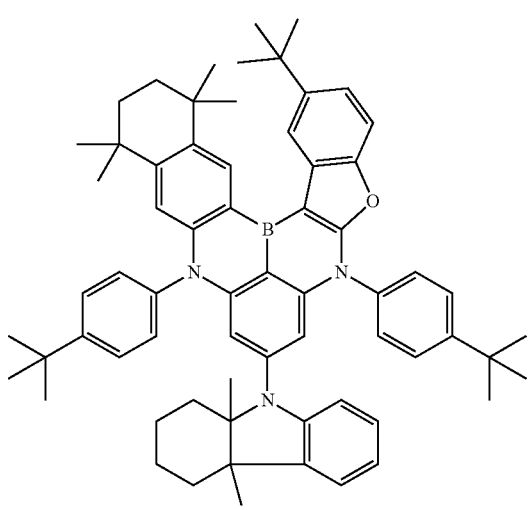 | 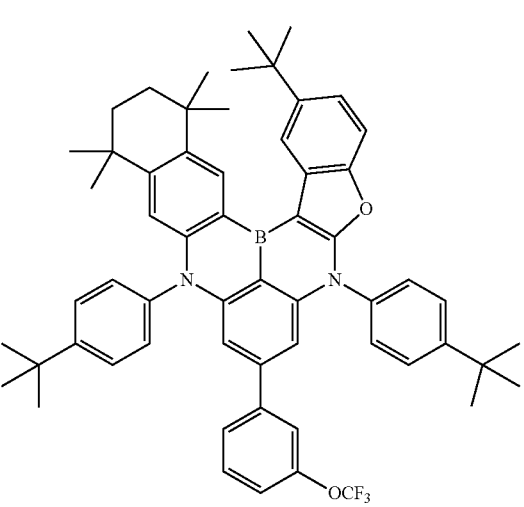 |

539
-continued
540
-continued
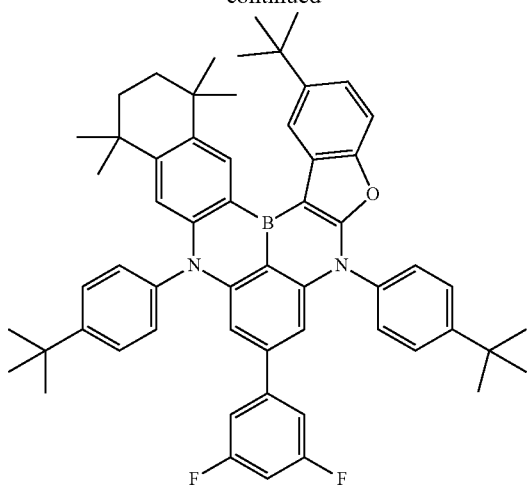
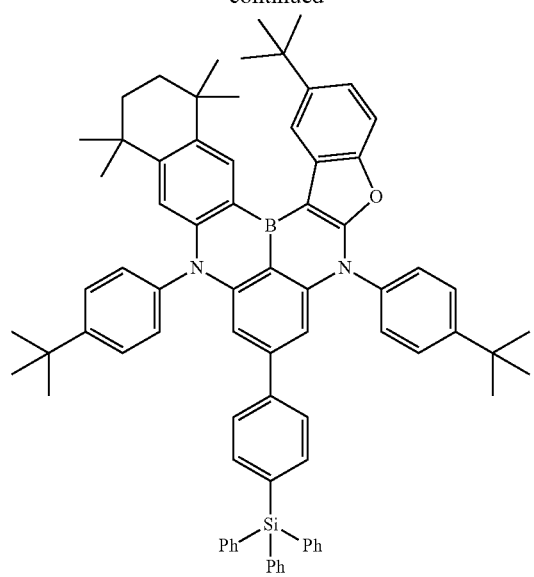
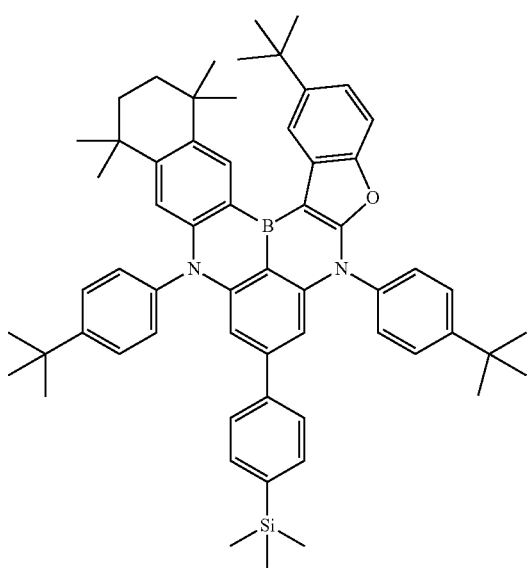
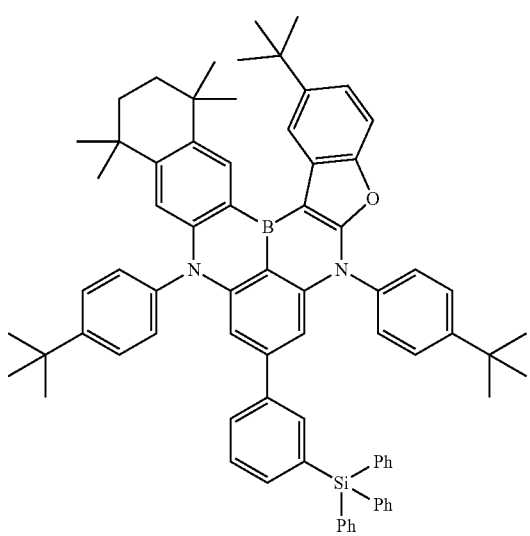

541
-continued
542
-continued
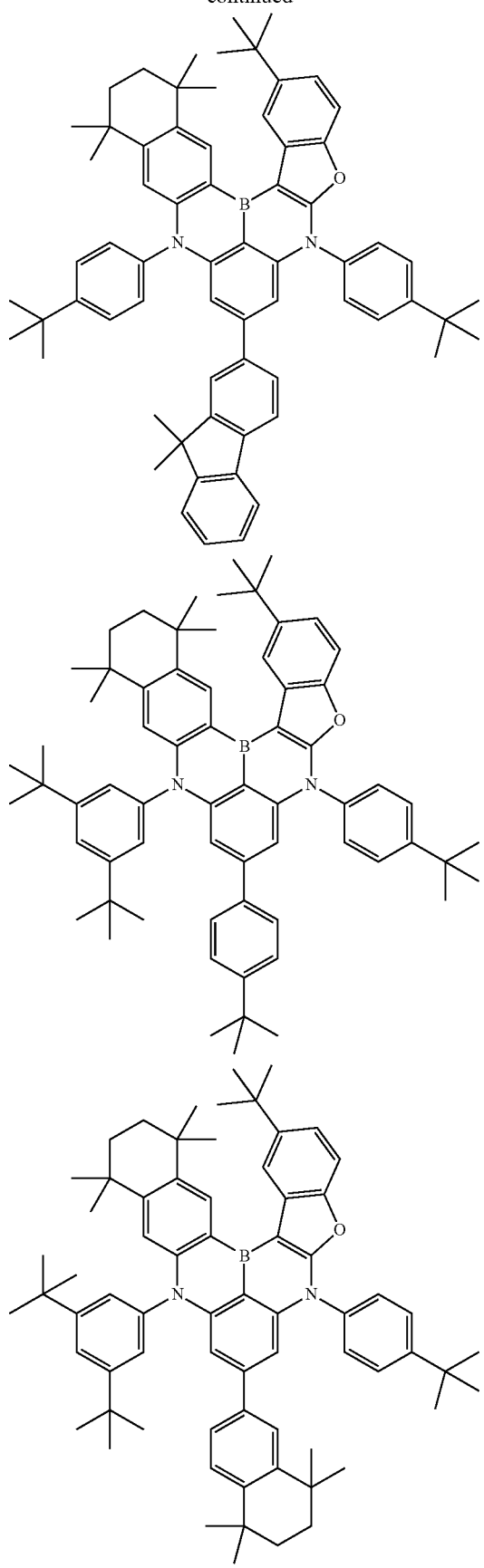
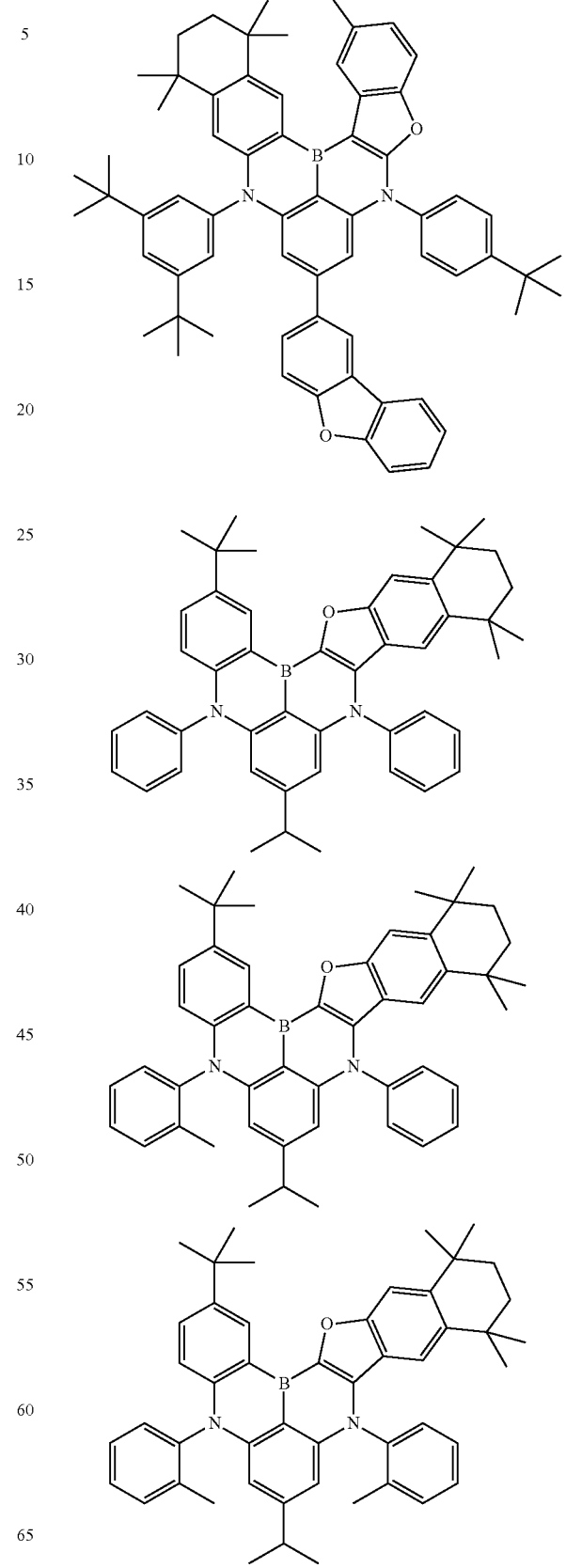

| 543 -continued | 544 -continued |
|---|---|
| 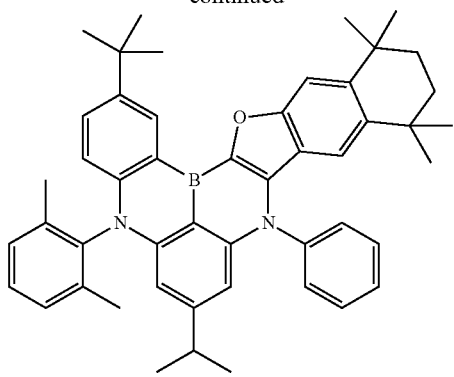 | 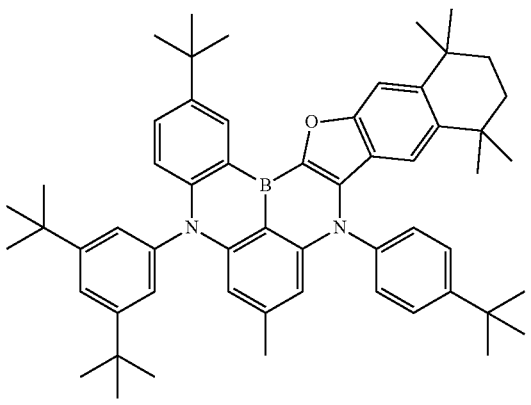 |
| 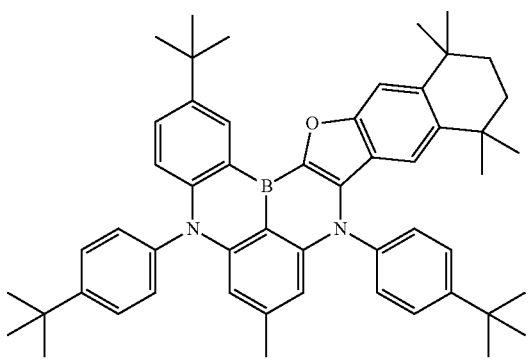 | 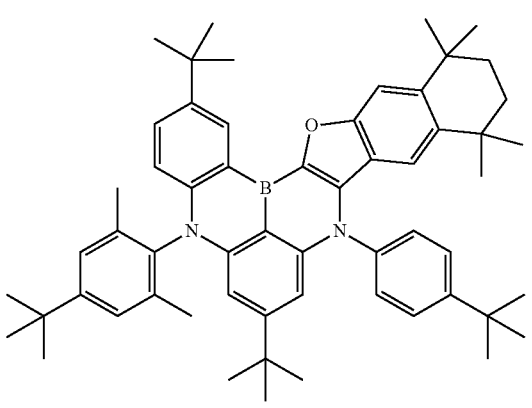 |
| 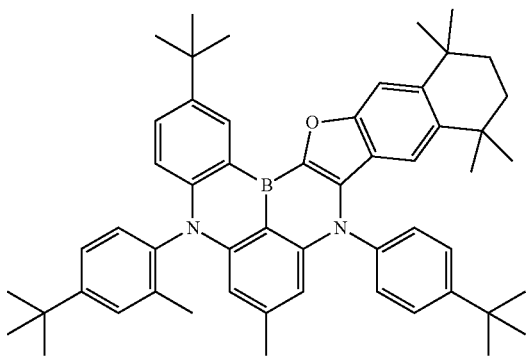 | 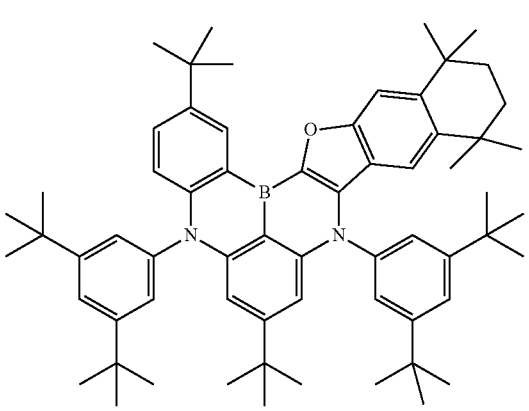 |
| 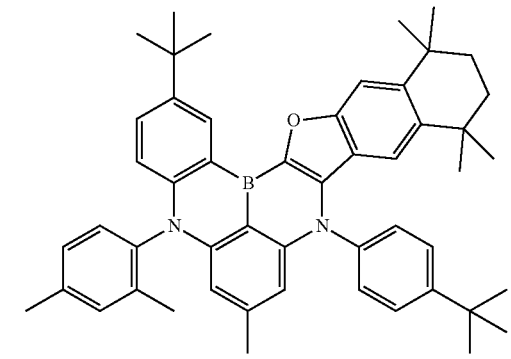 | 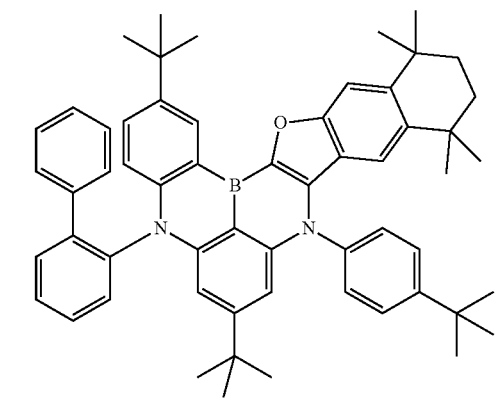 |

545
-continued
546
-continued
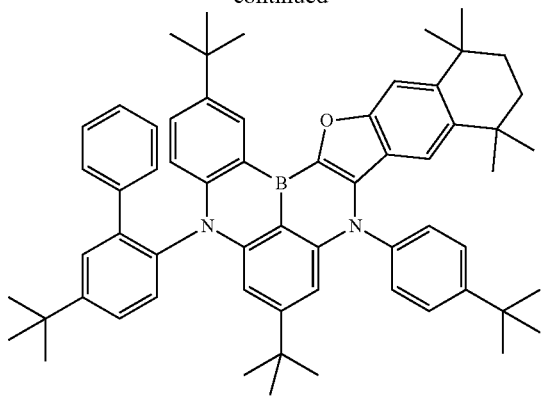
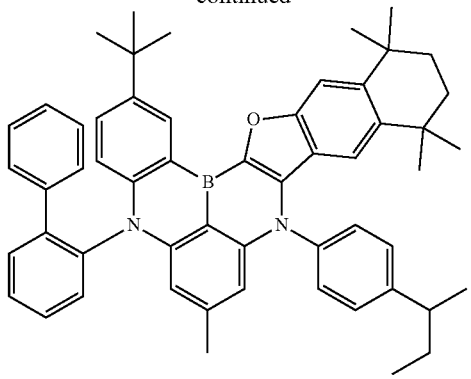
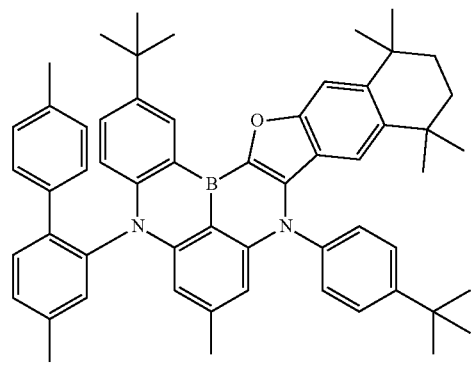
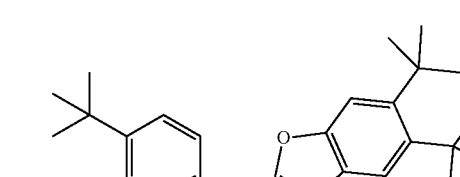
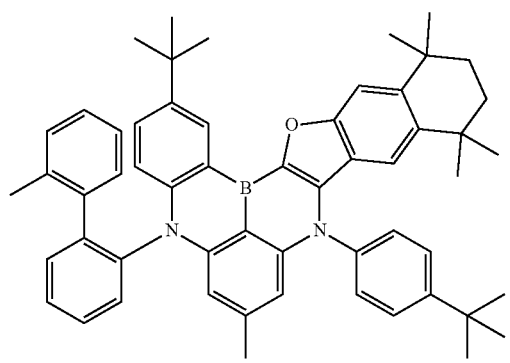
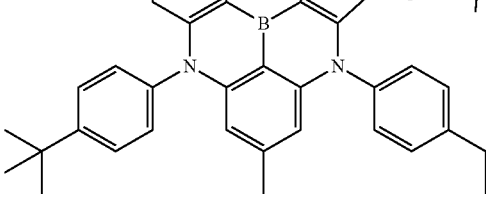
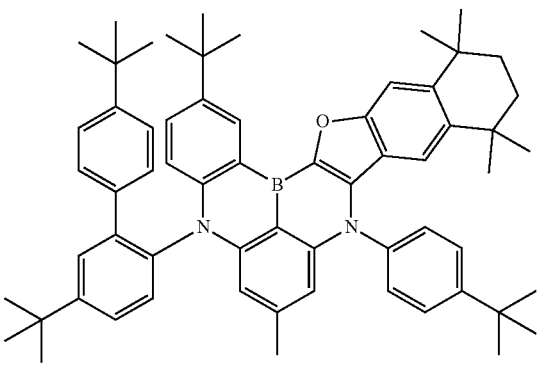
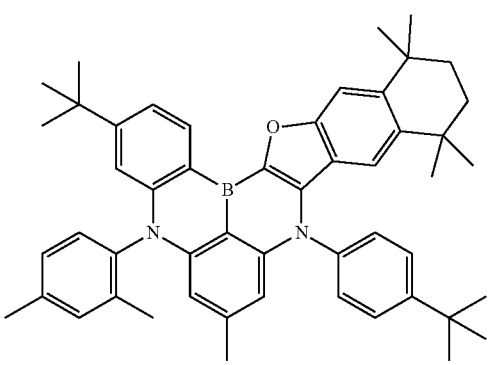

547
-continued
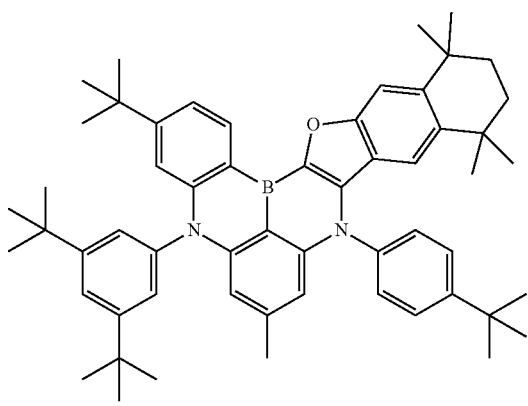
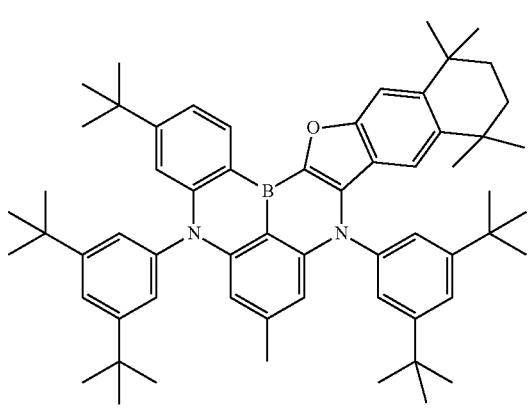
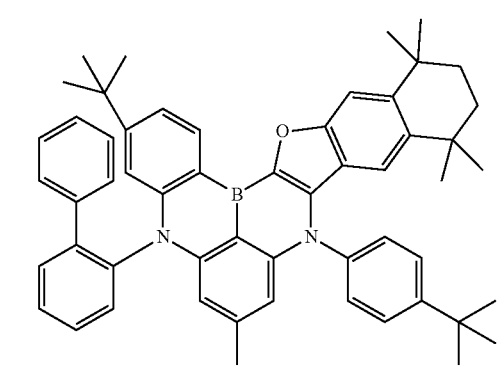
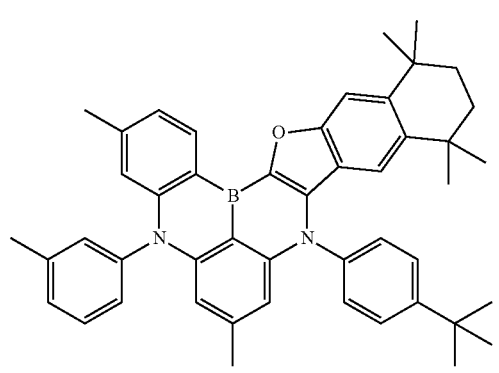
548
-continued
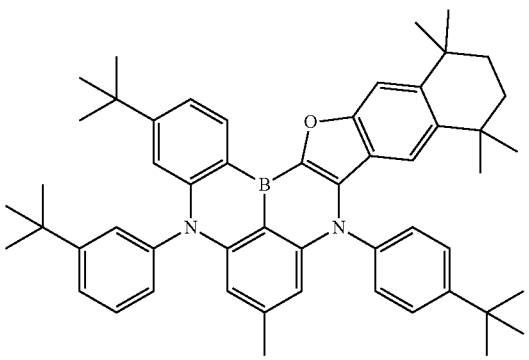
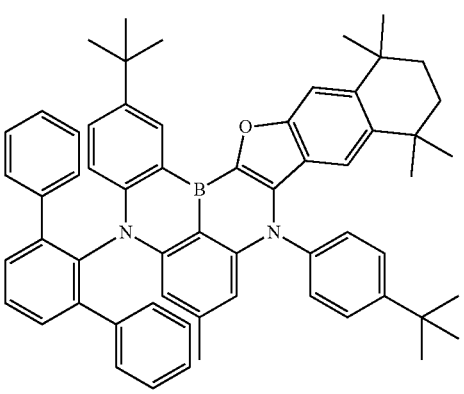
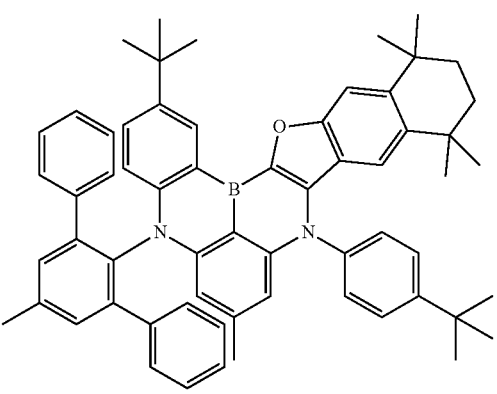
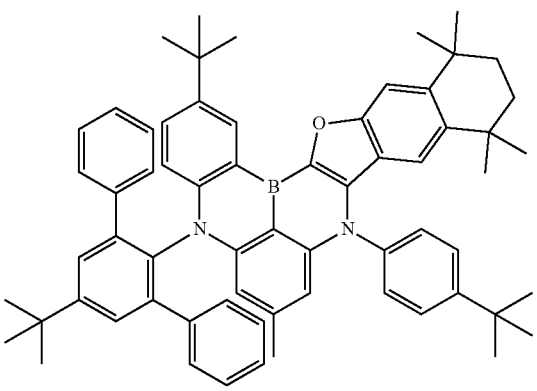

549
-continued
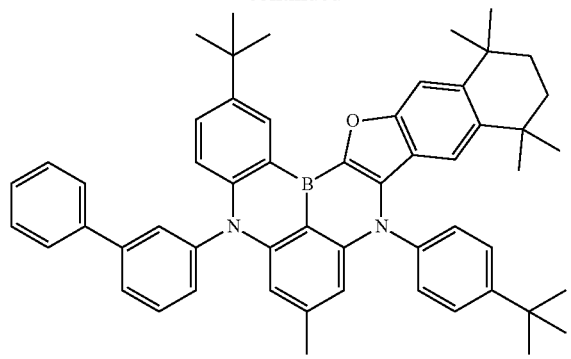
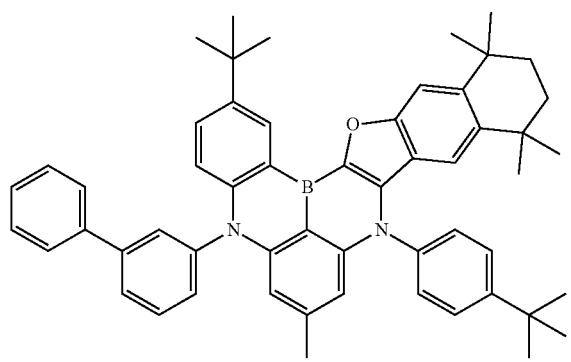
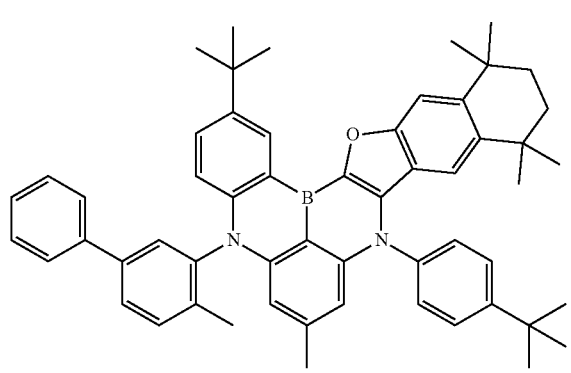
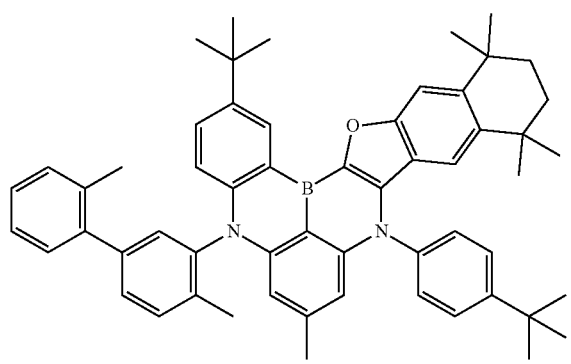
550
-continued
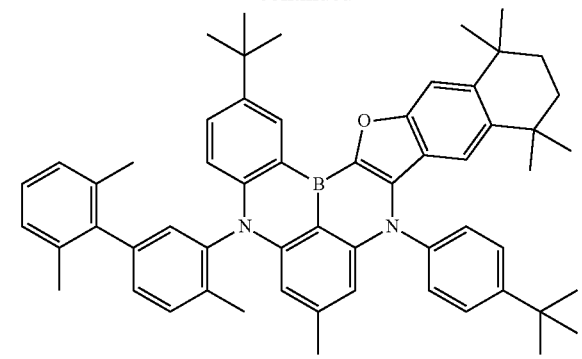
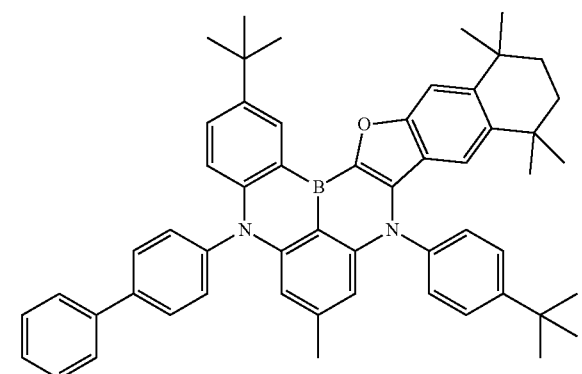
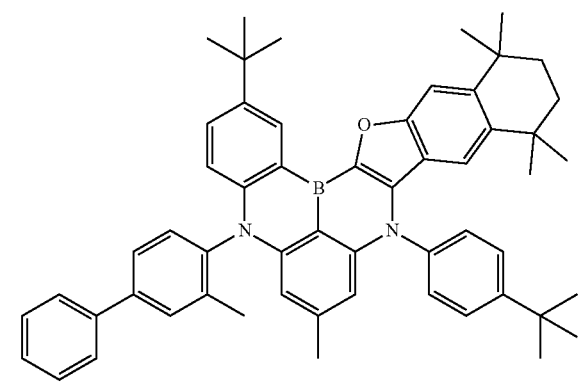
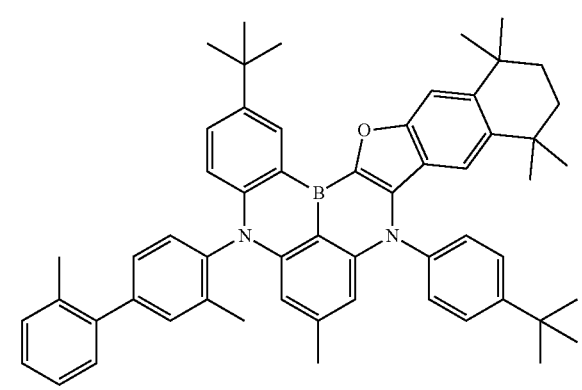

551
-continued
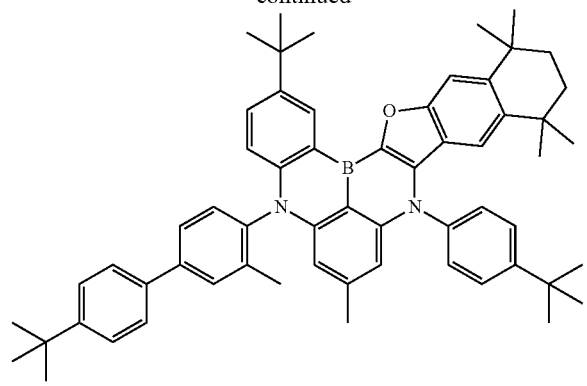
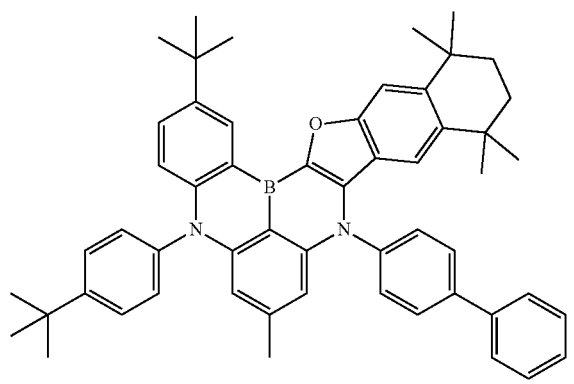
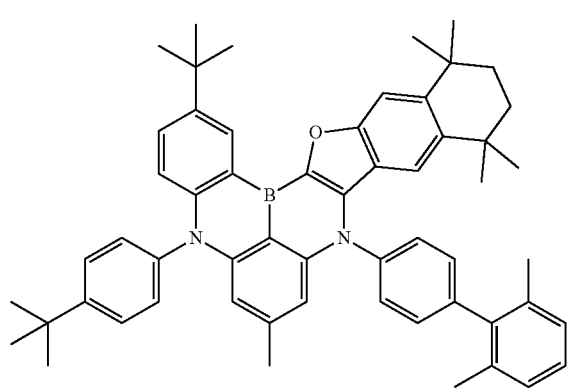
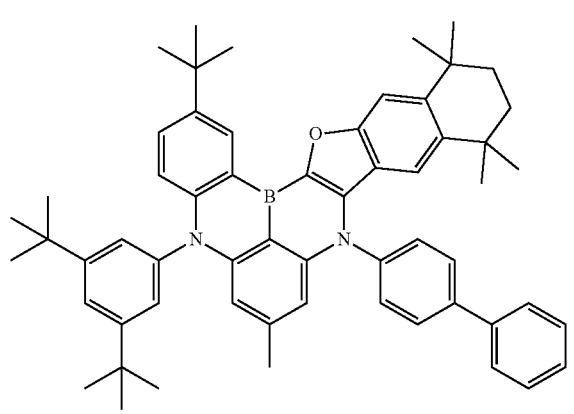
552
-continued
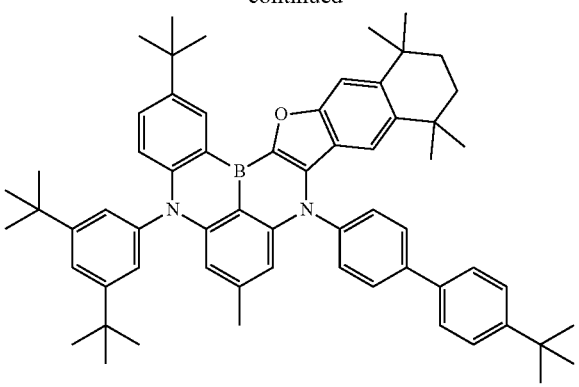
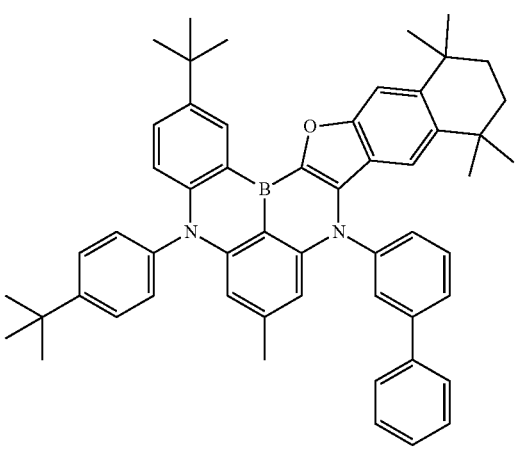
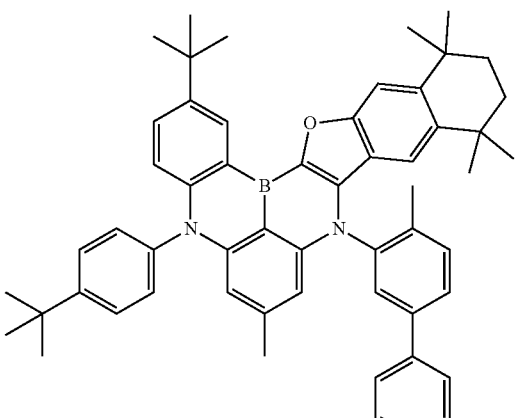
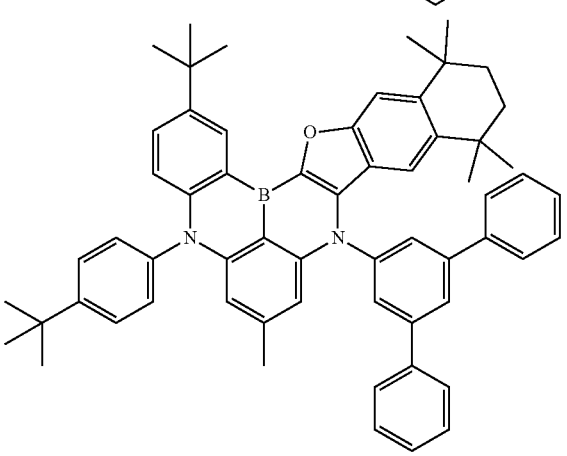

553
-continued
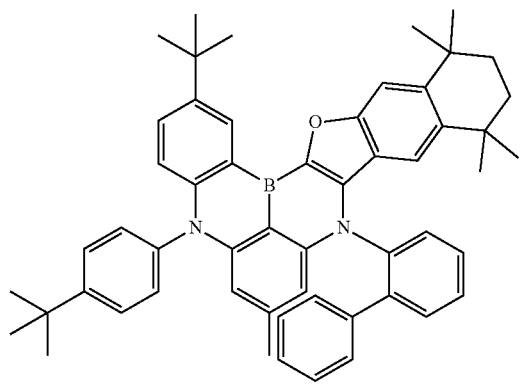
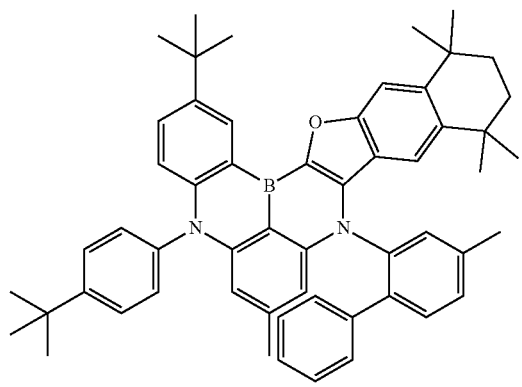
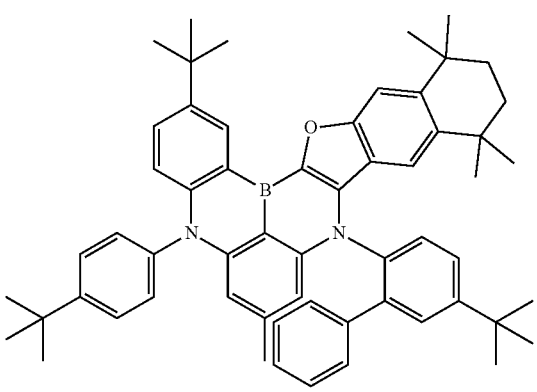
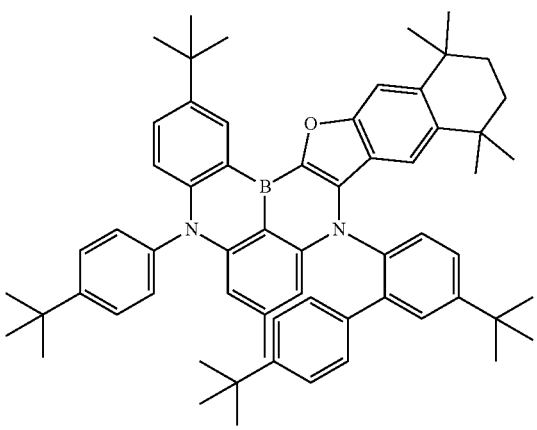
554
-continued
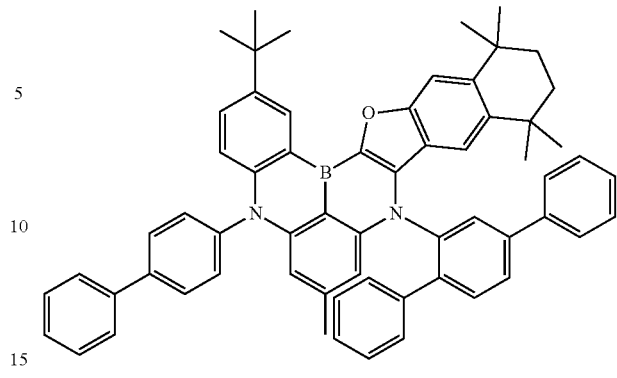
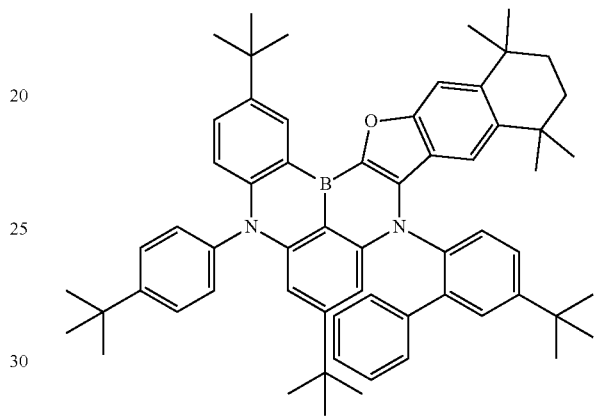
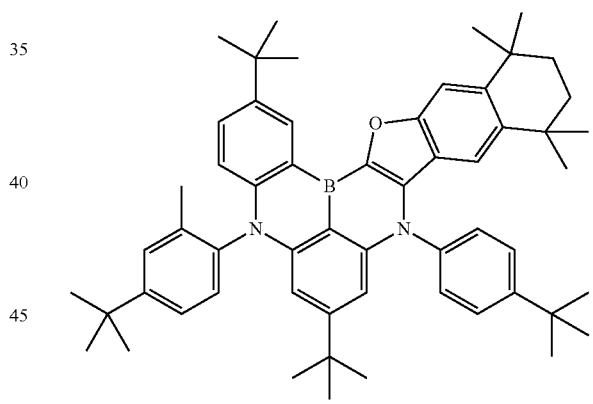
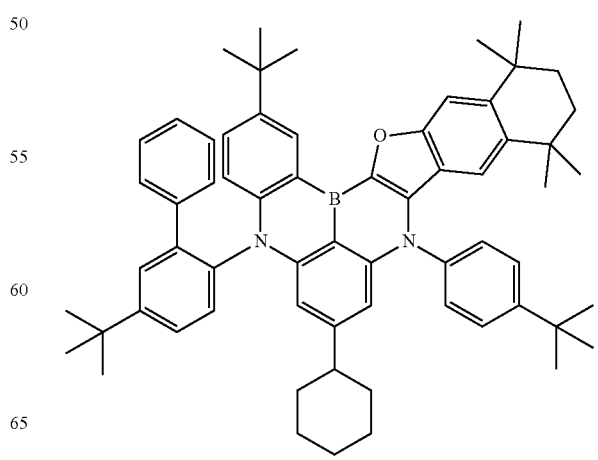

555
-continued
556
-continued
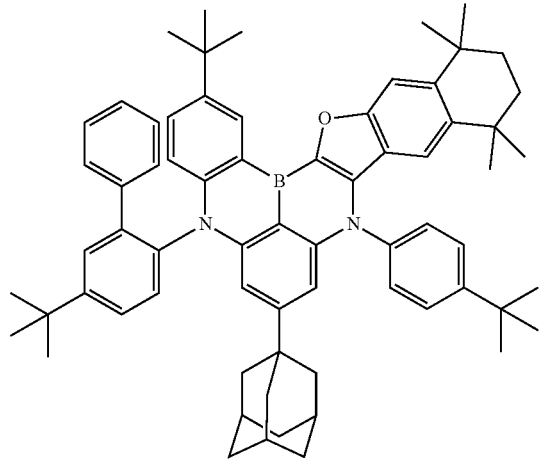
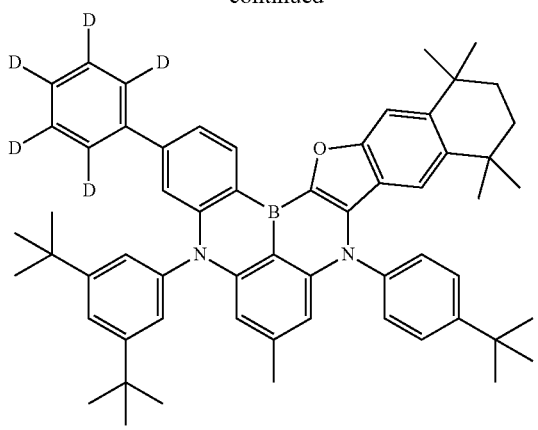
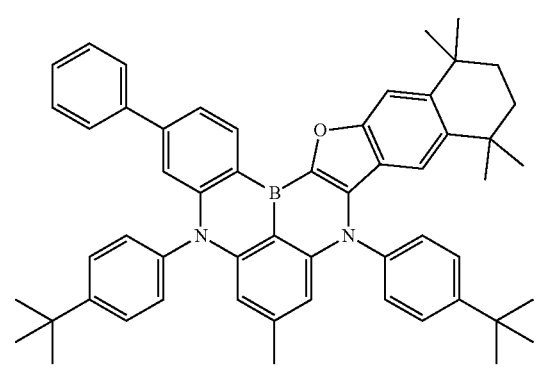
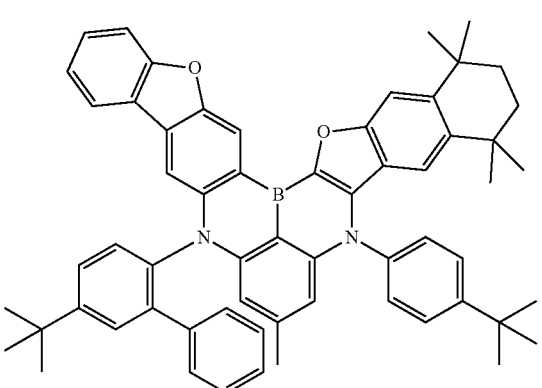
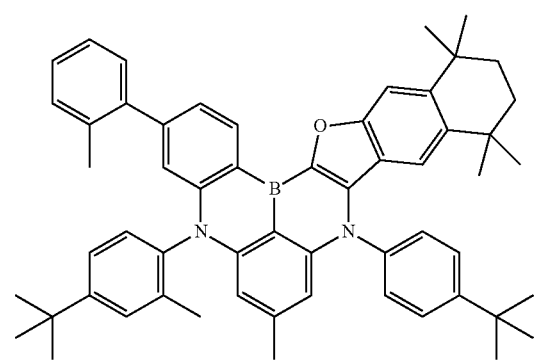
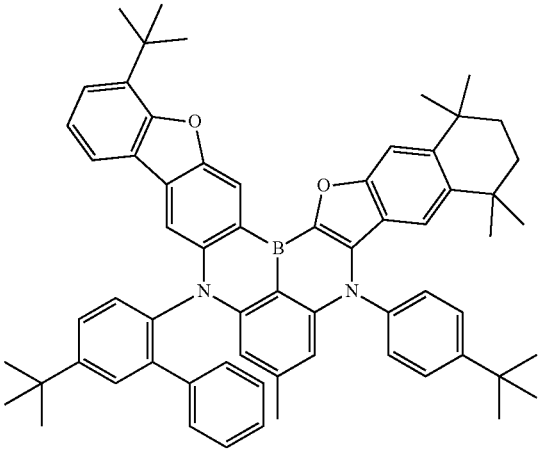
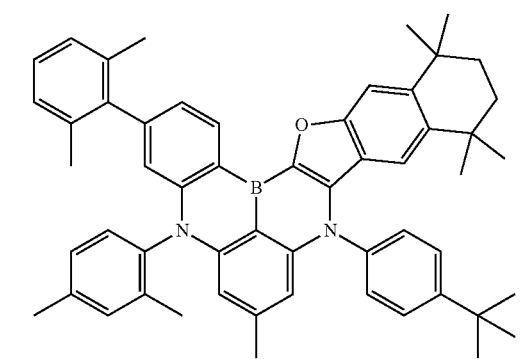
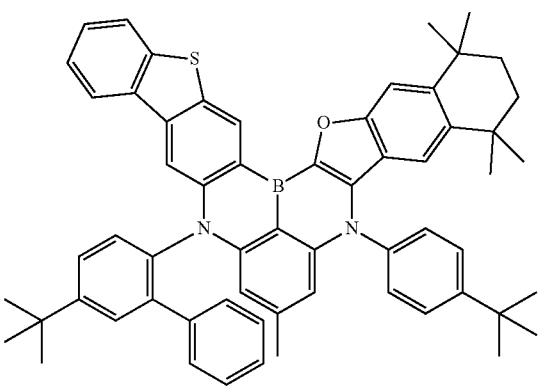

557
-continued
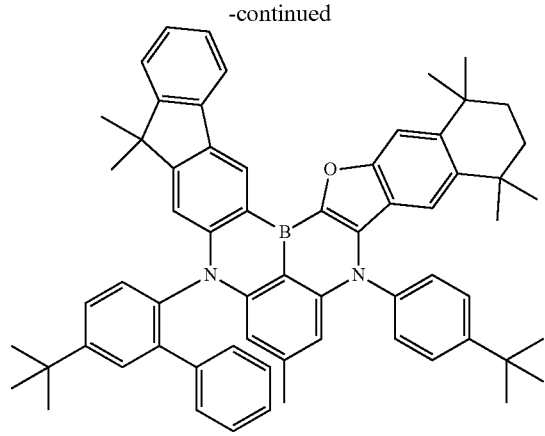
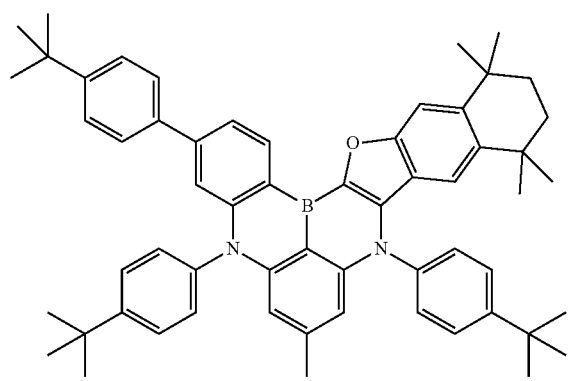
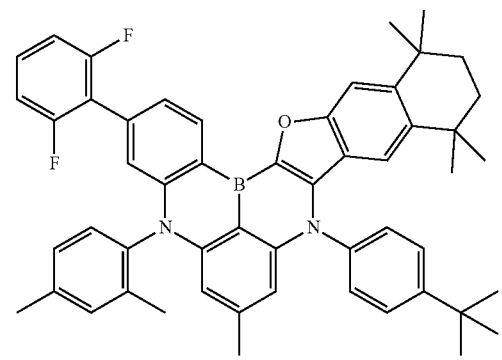
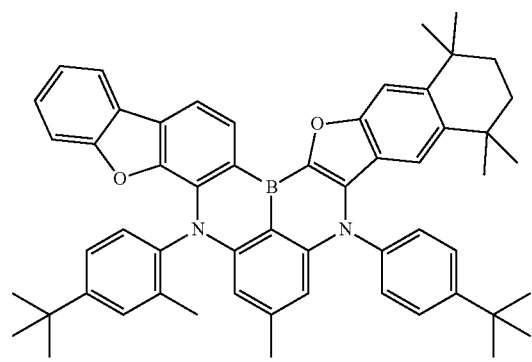
558
-continued
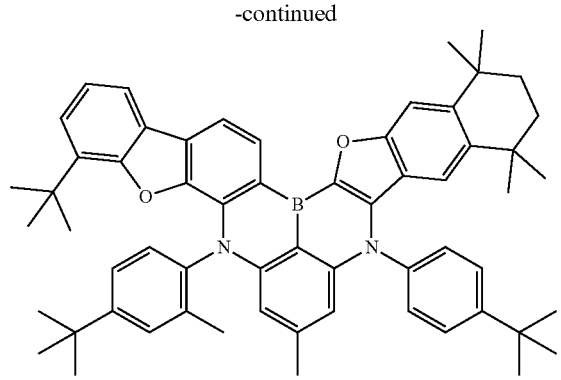
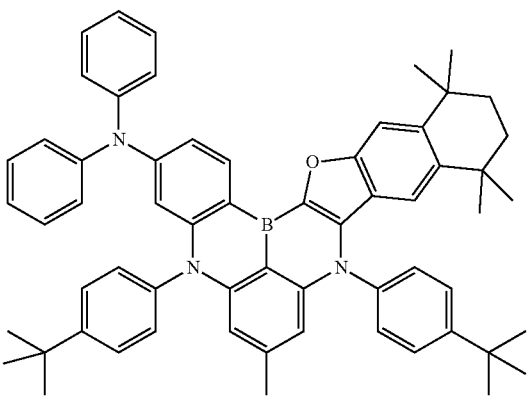
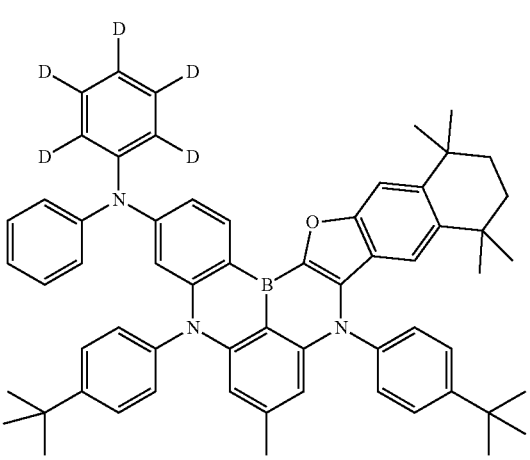
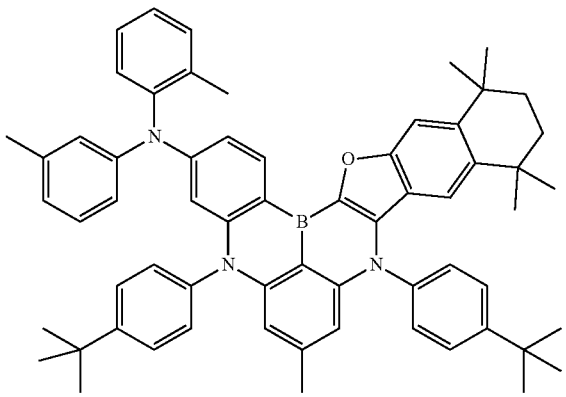

559
-continued
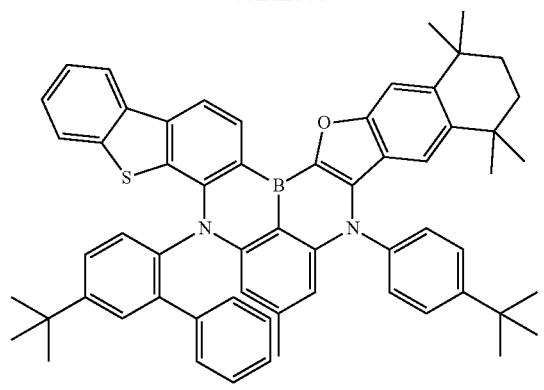
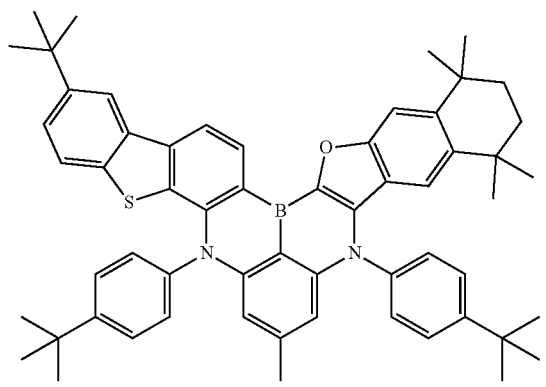
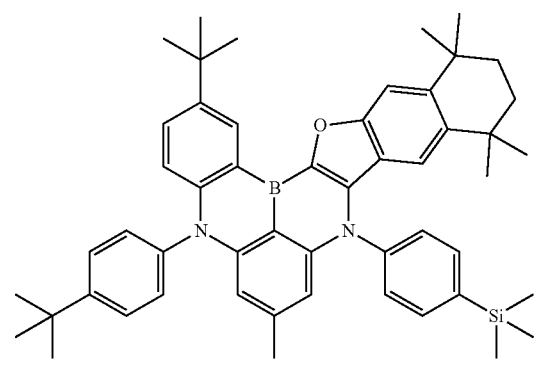
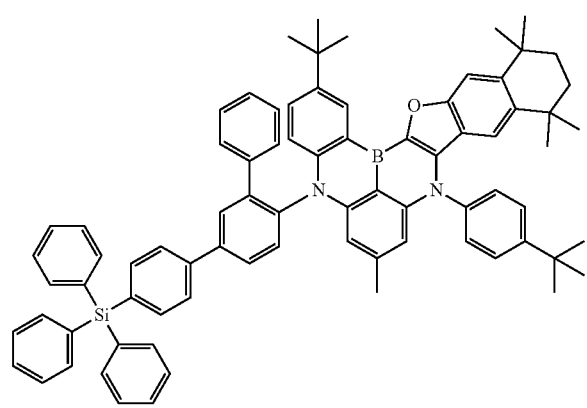
560
-continued
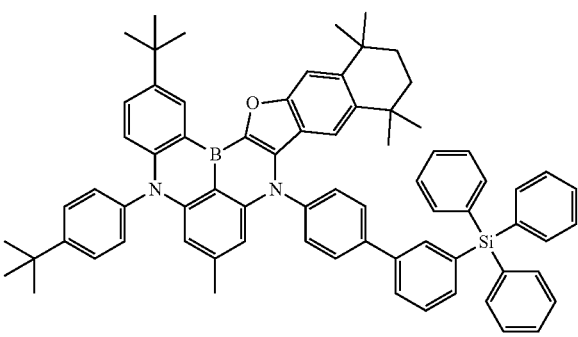
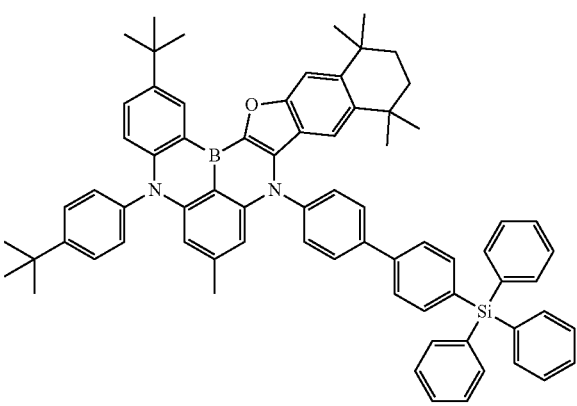
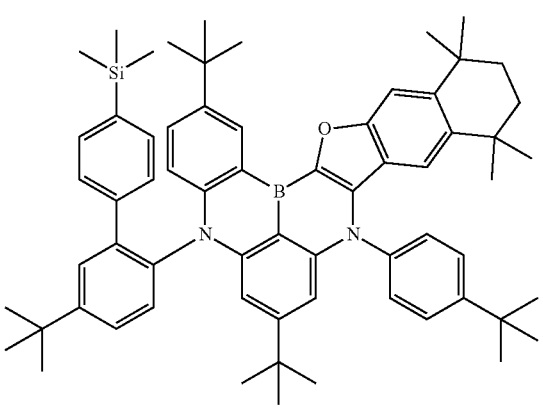

561
-continued
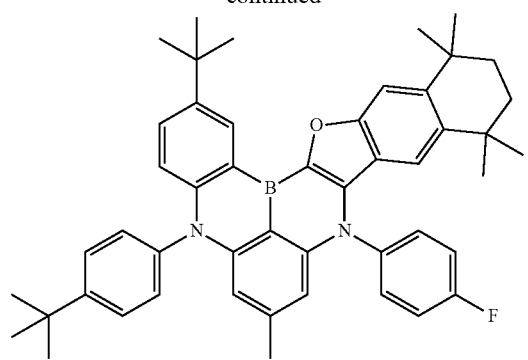
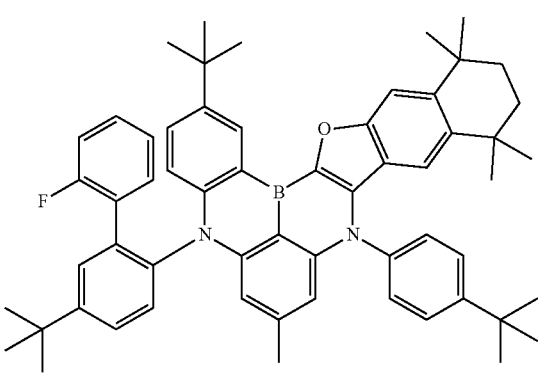
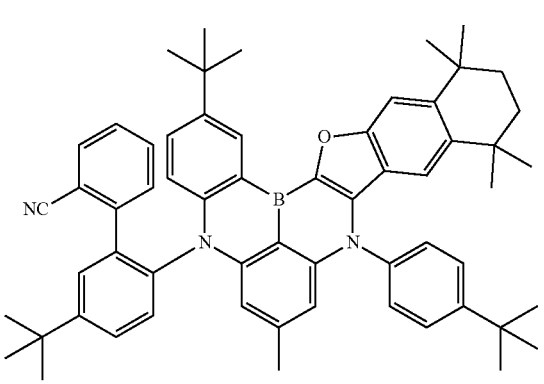
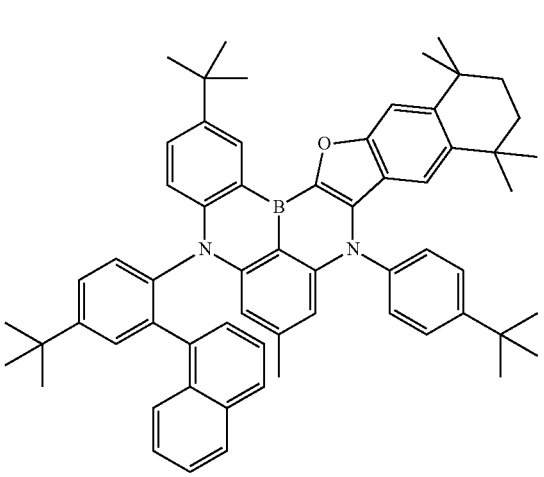
562
-continued
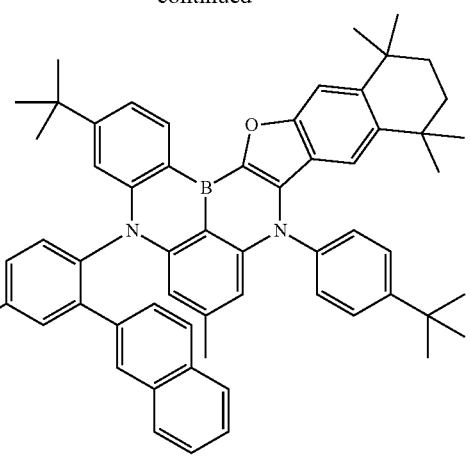
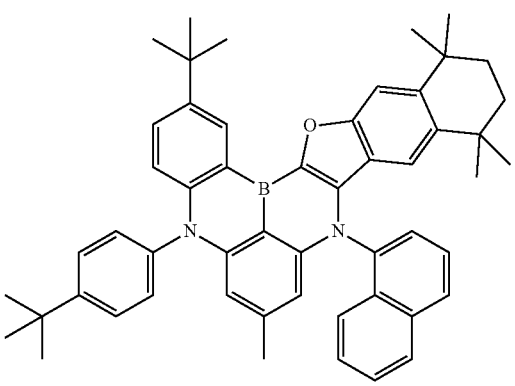
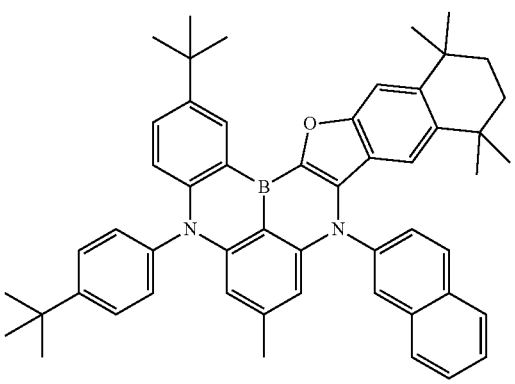
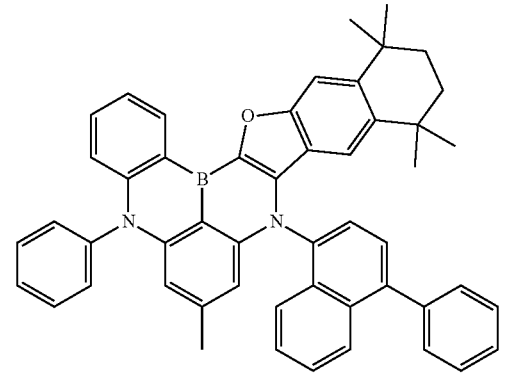

563
-continued
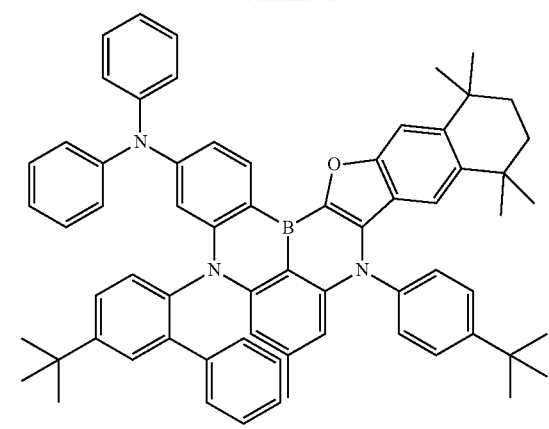
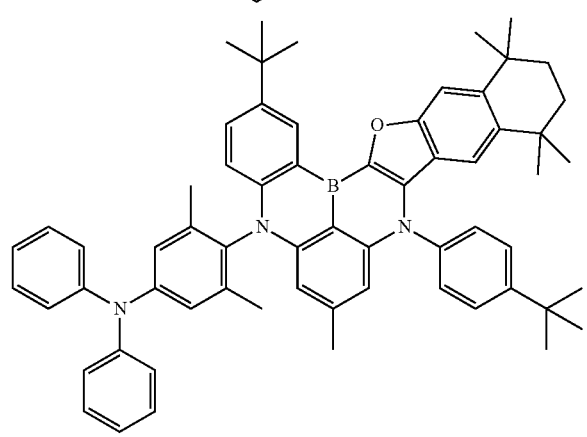
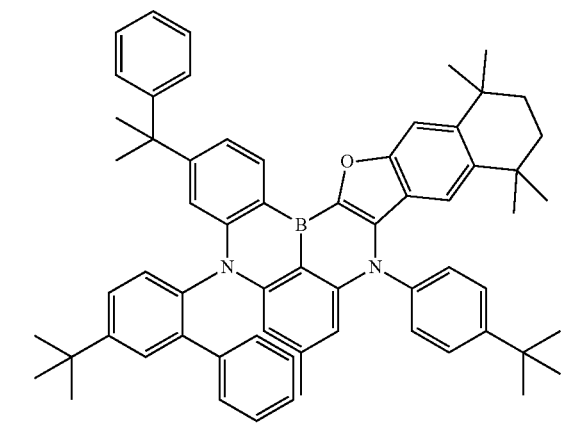
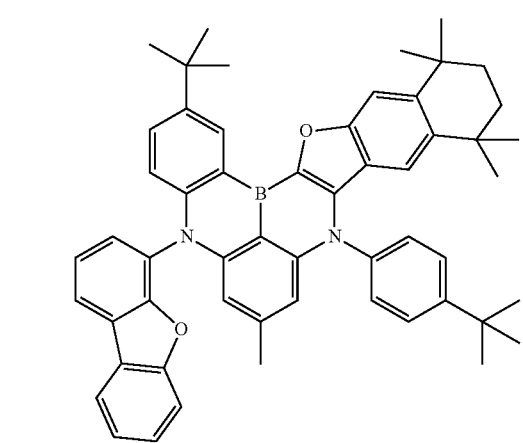
564
-continued
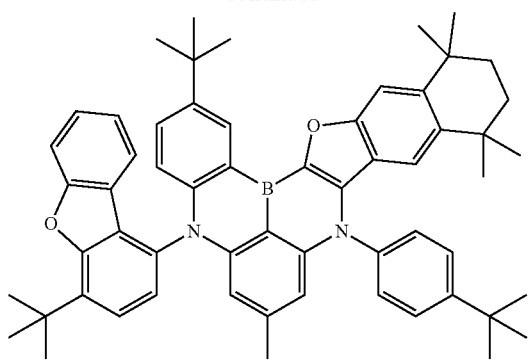
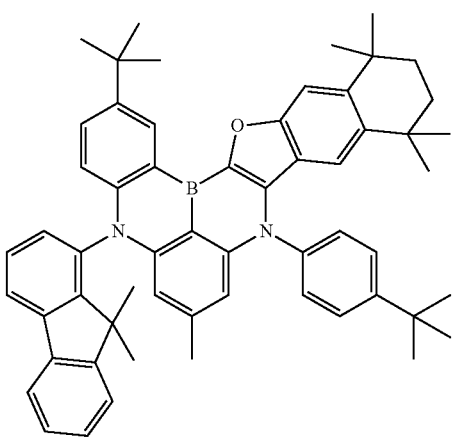
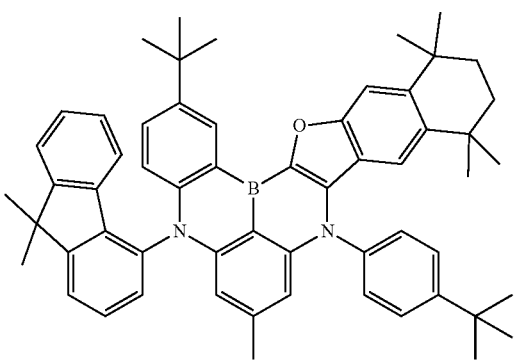
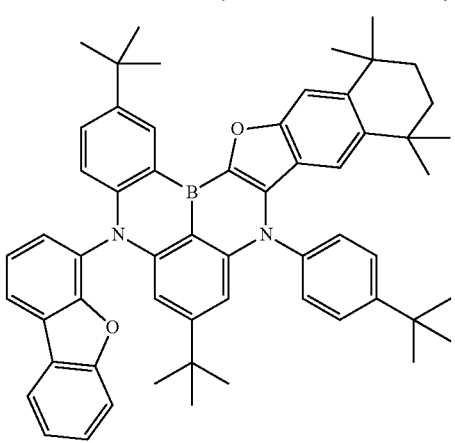

565
-continued
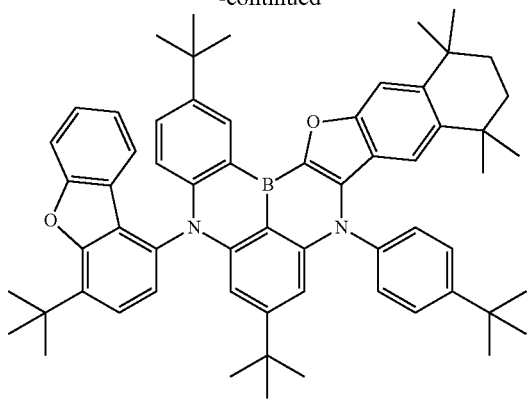
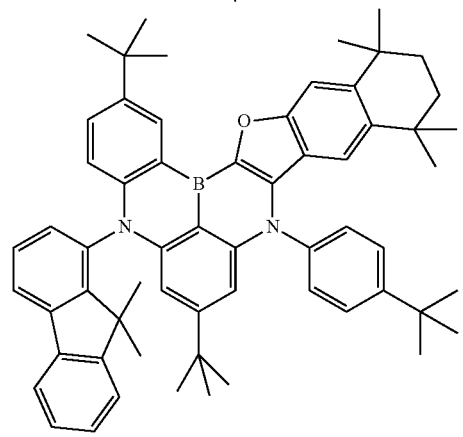
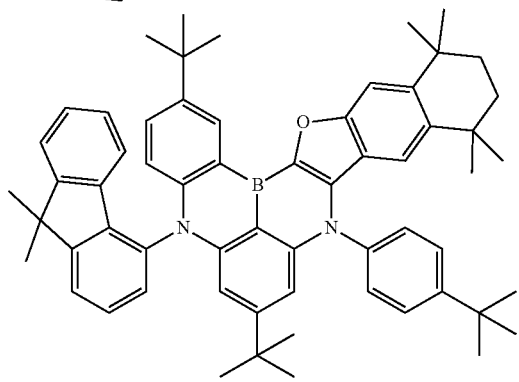
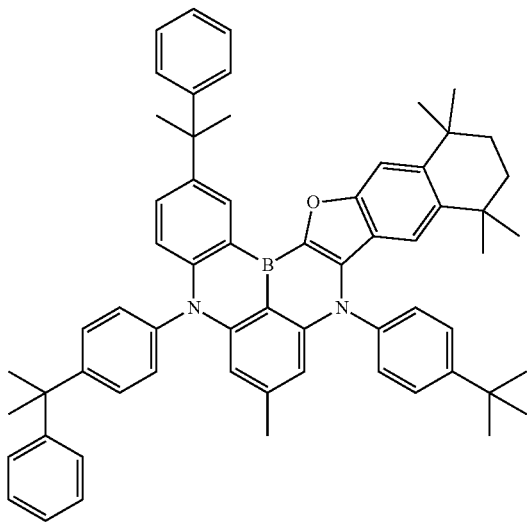
566
-continued
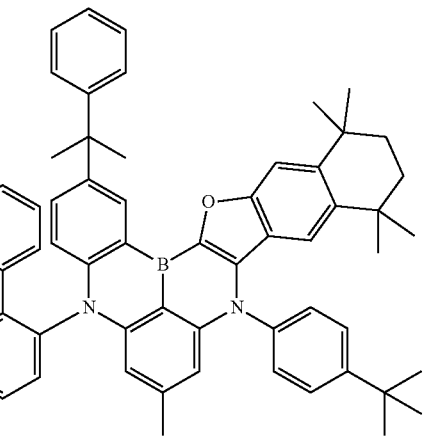
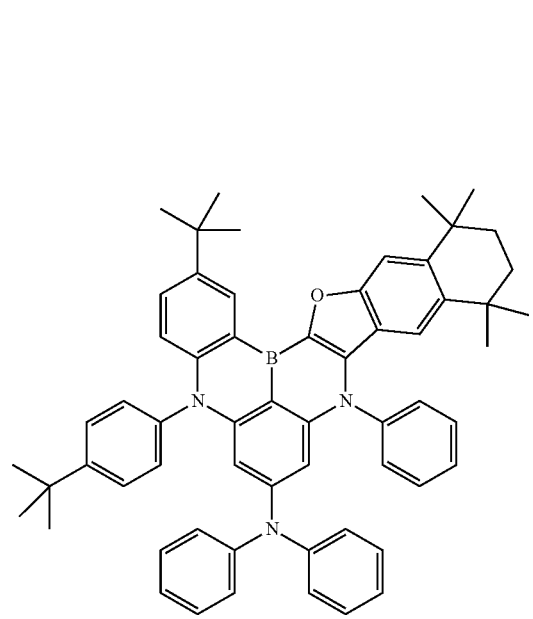
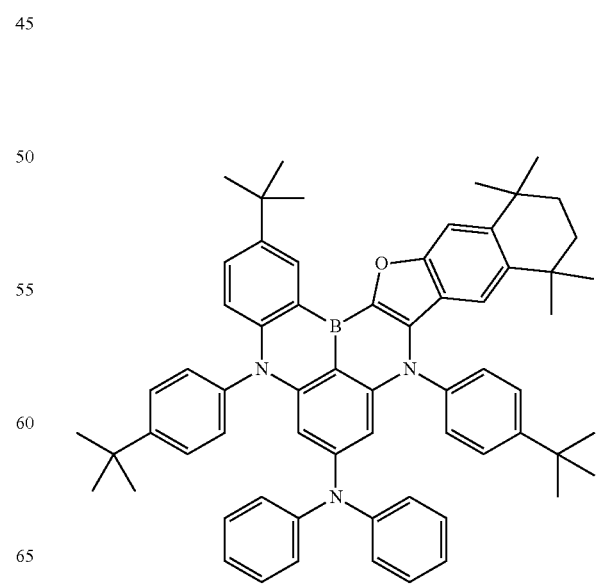

567
-continued
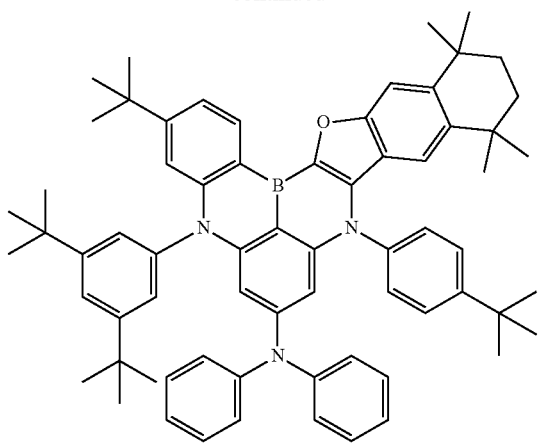
568
-continued
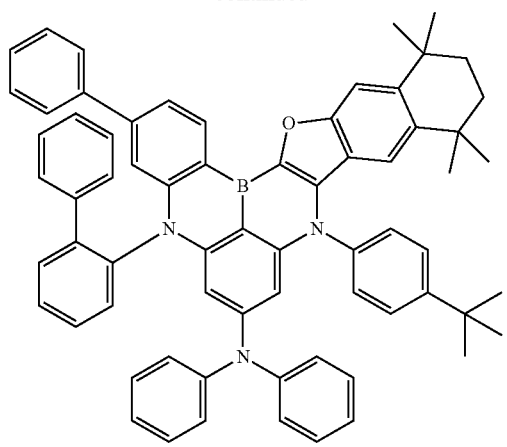
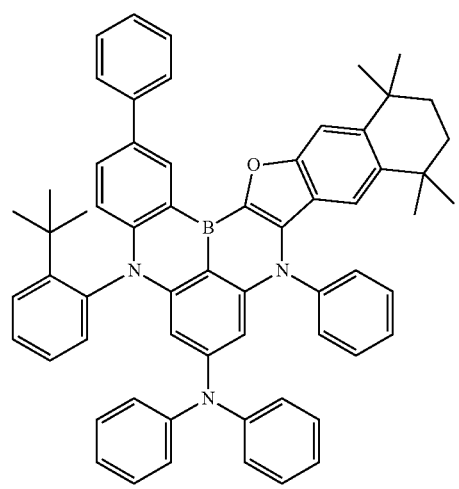
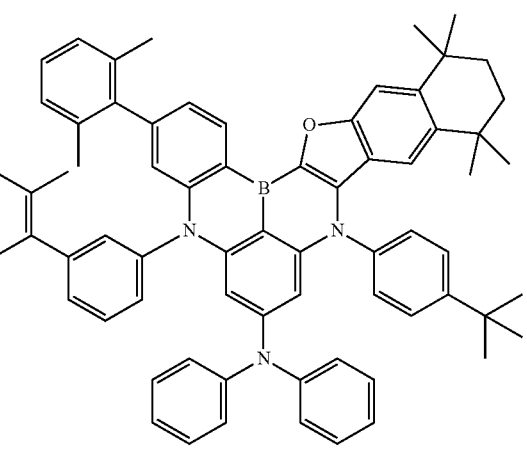
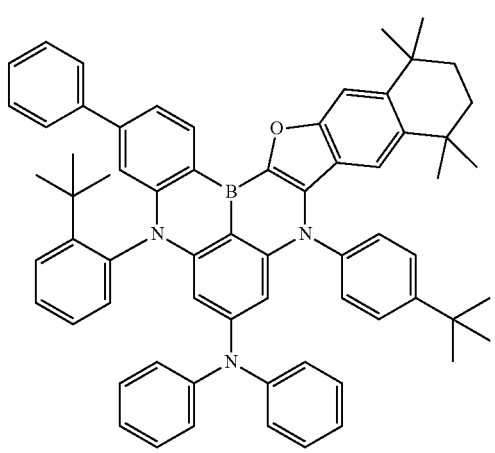
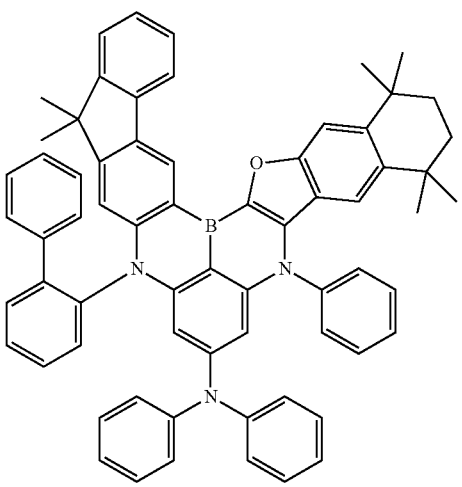

569
-continued
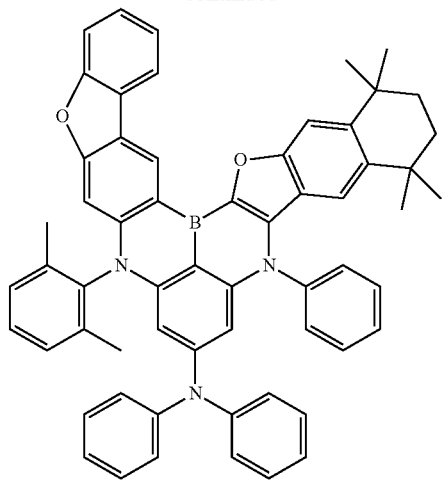
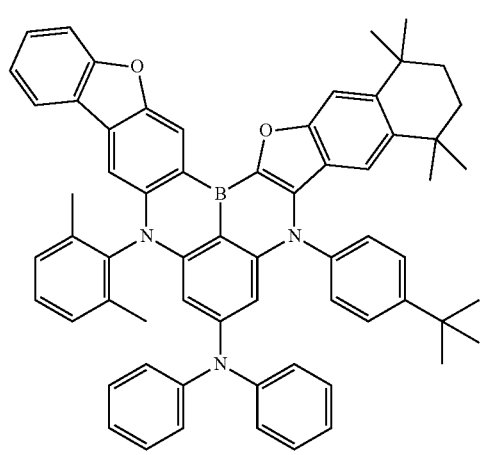
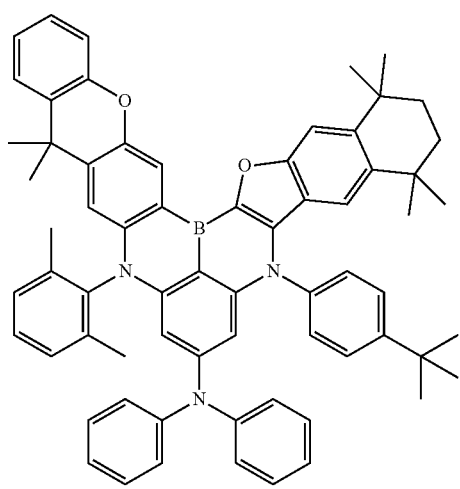
570
-continued
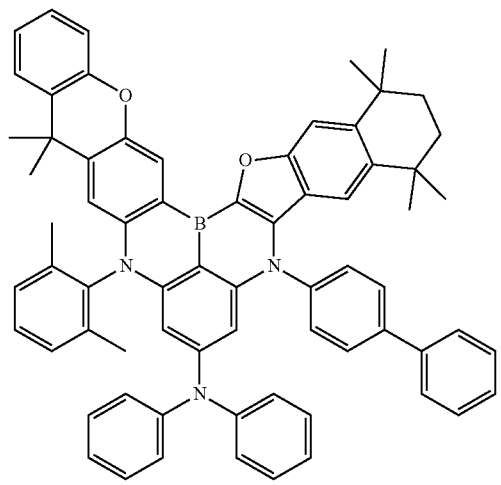
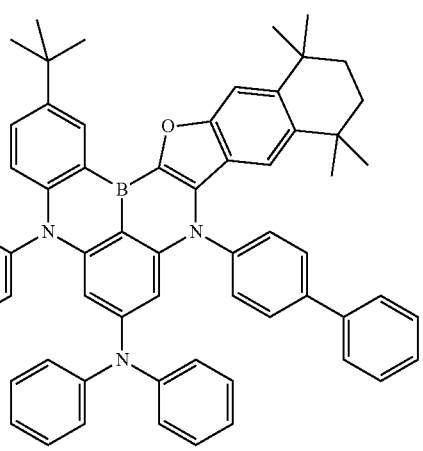
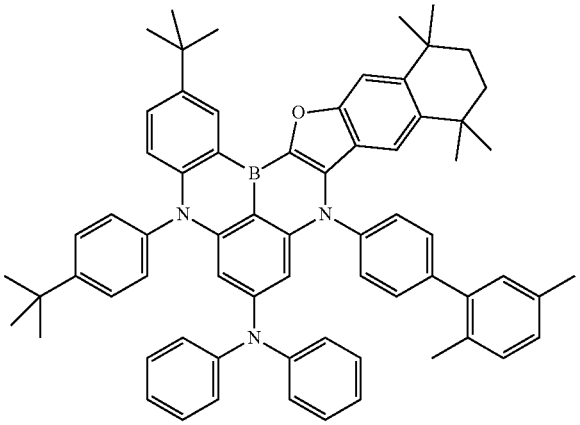

571
-continued
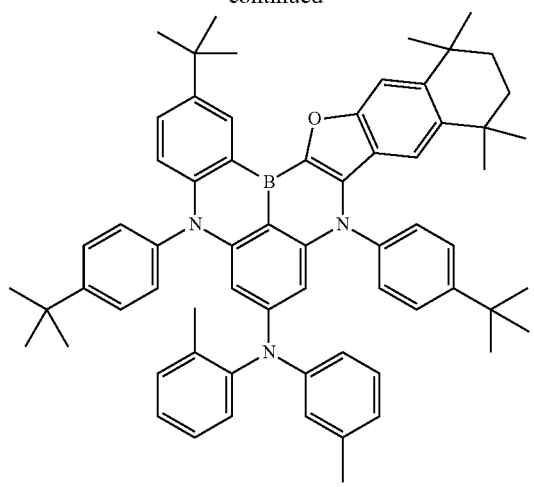
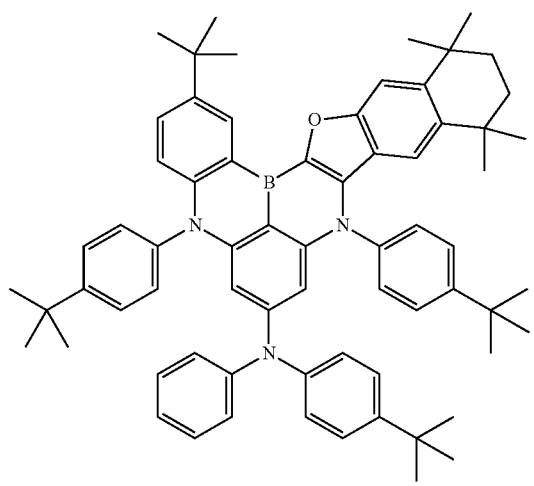
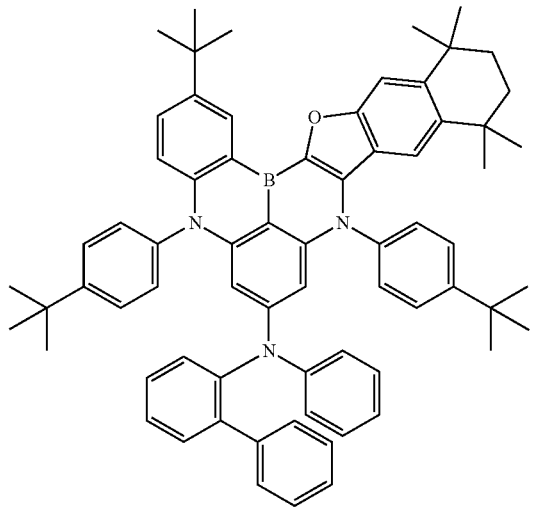
572
-continued
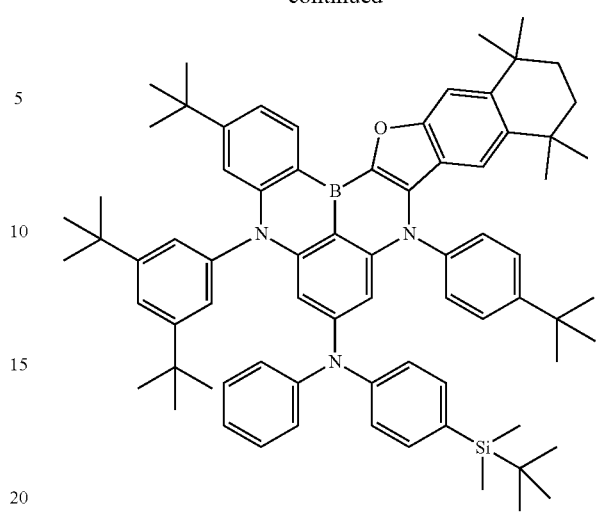
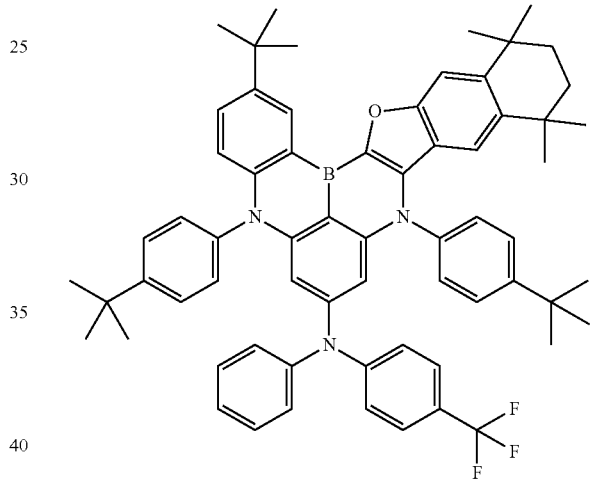
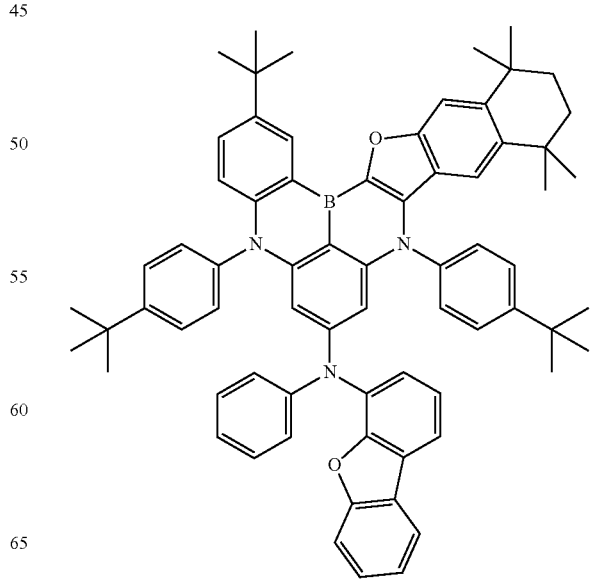

573
-continued
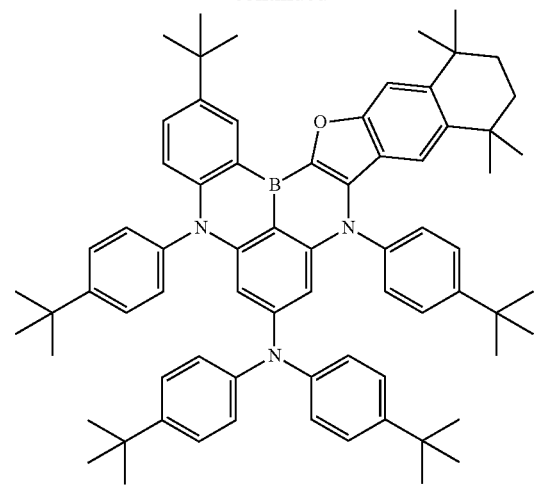
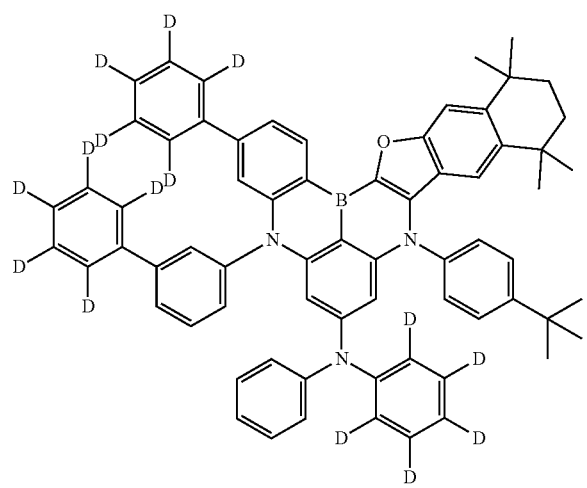
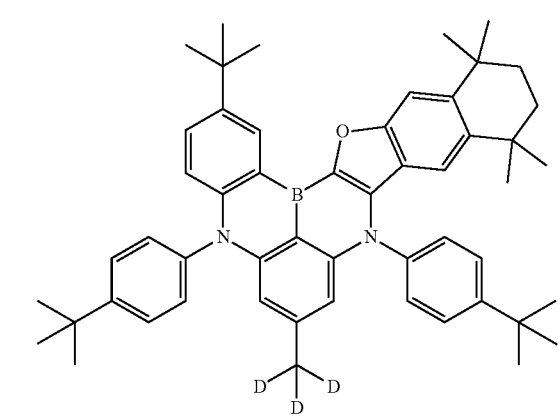
574
-continued
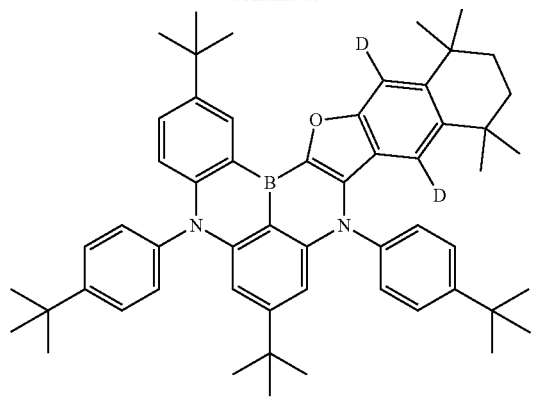
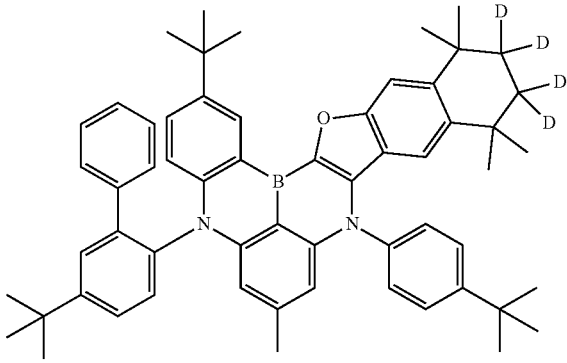
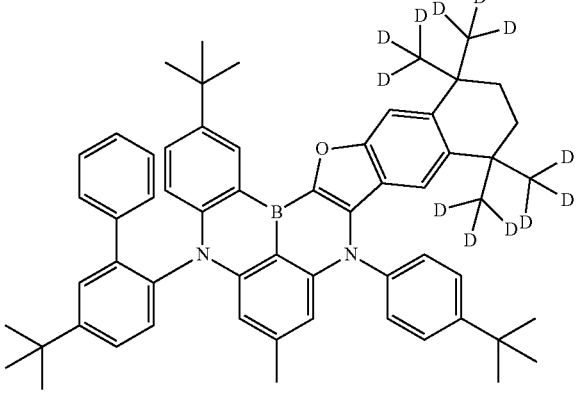
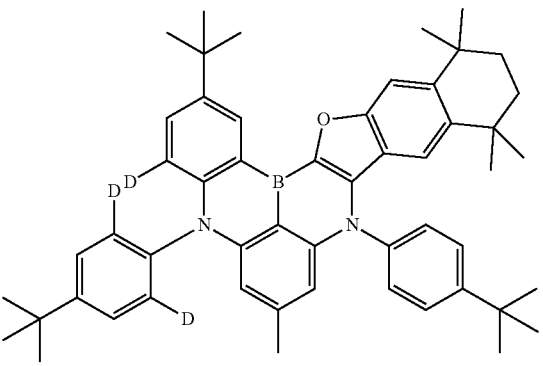

575
-continued
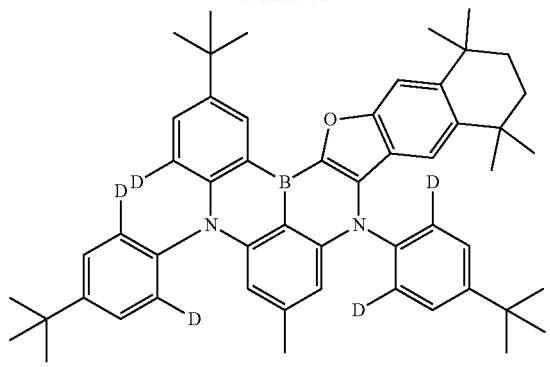
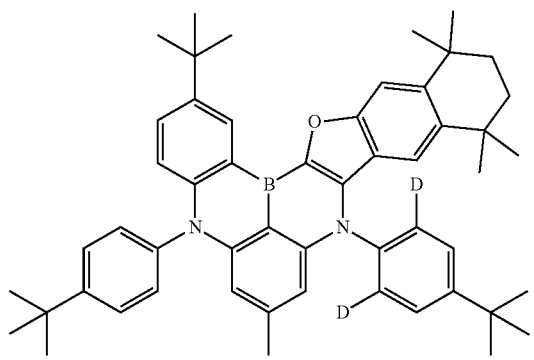
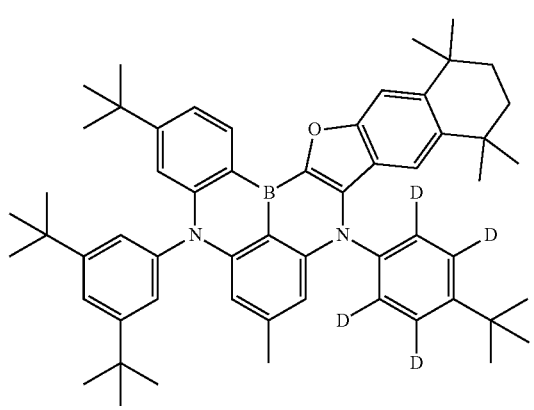
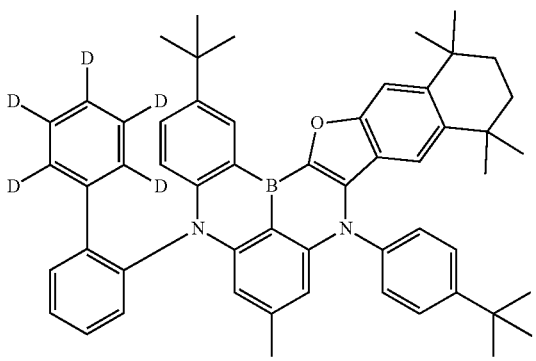
576
-continued
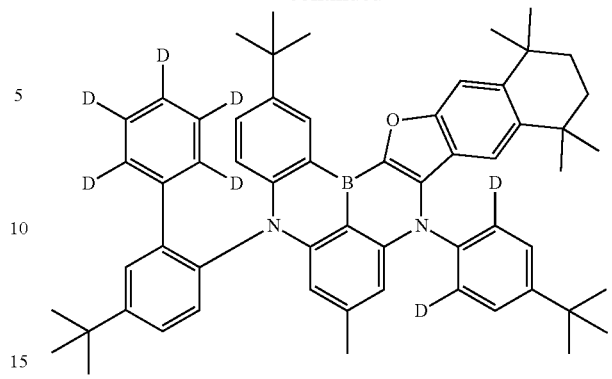
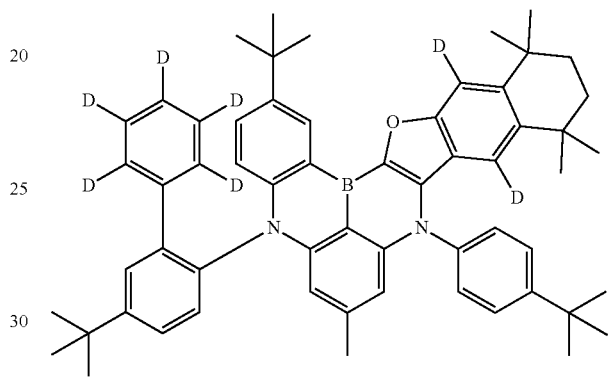
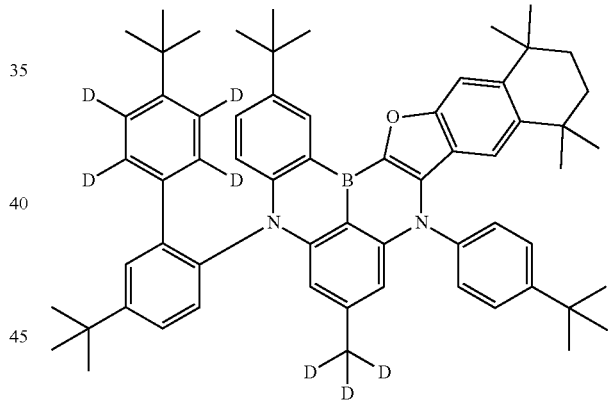
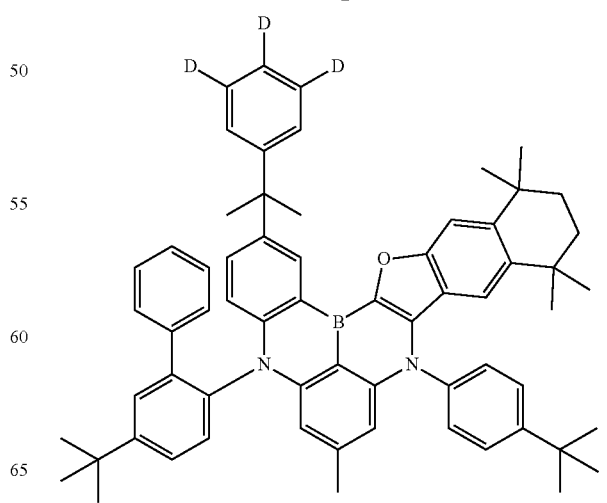

577
-continued
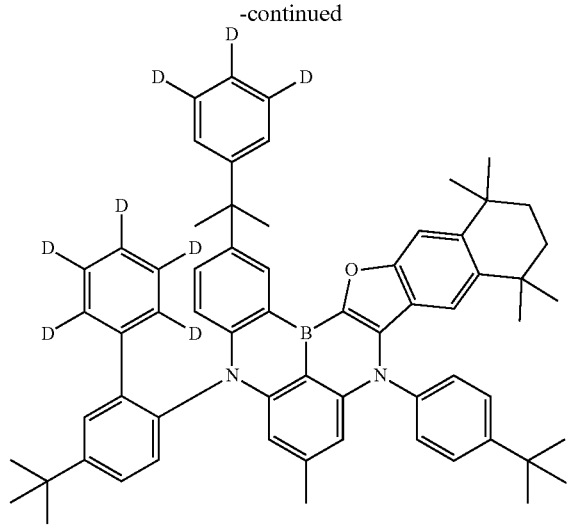
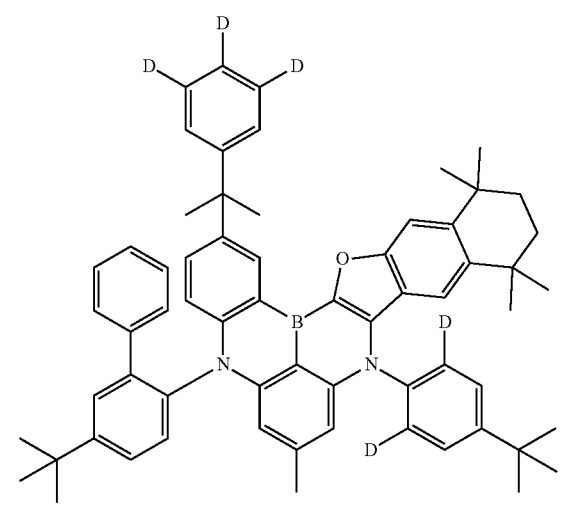
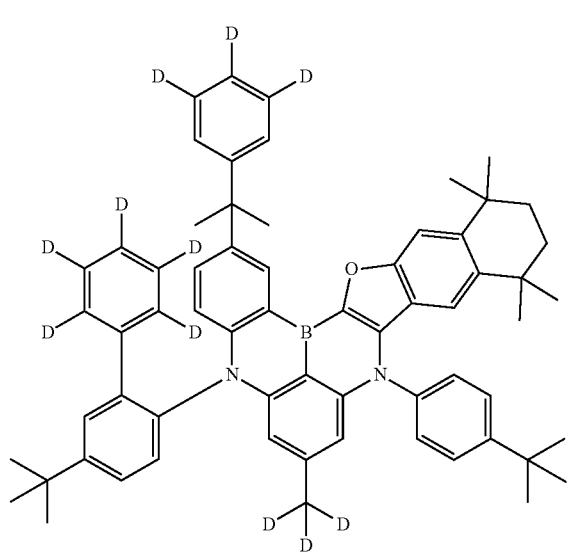
578
-continued
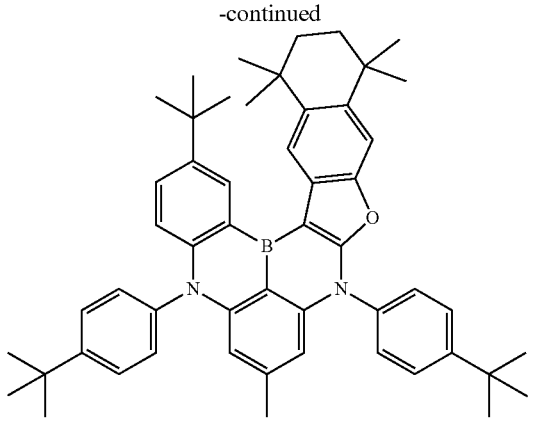
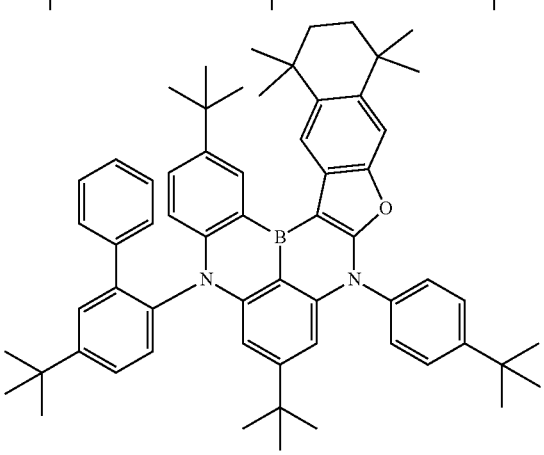
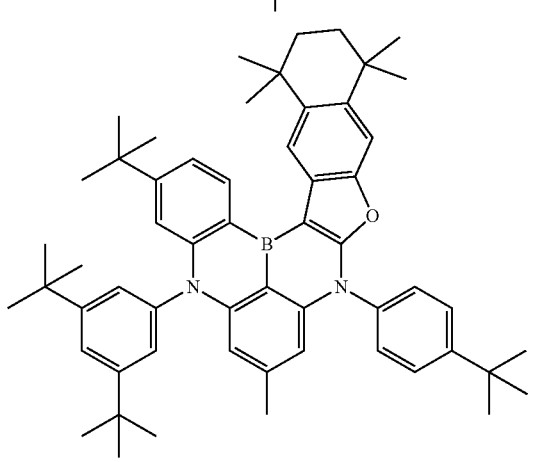
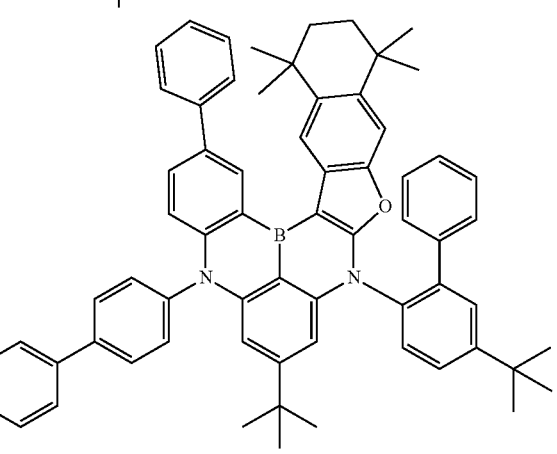

579
-continued
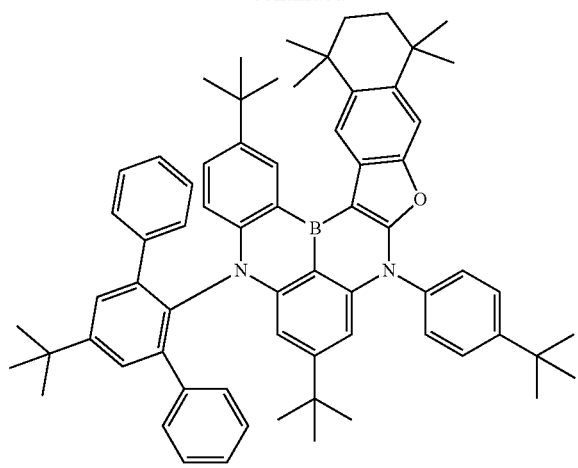
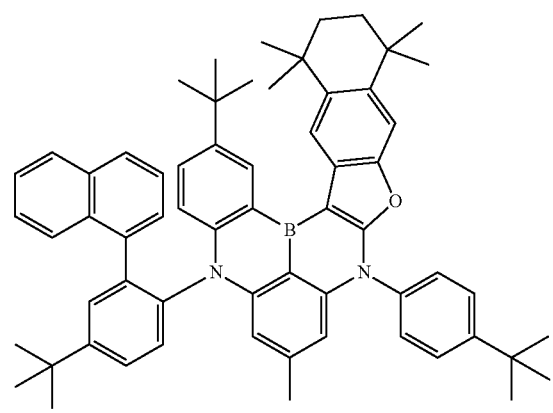
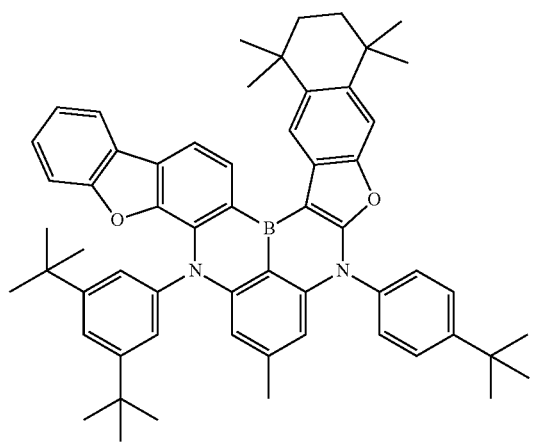
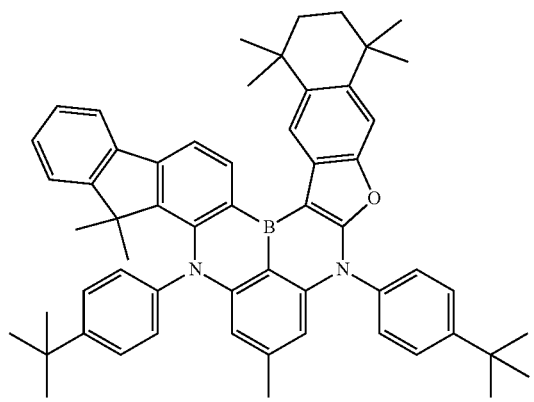
580
-continued
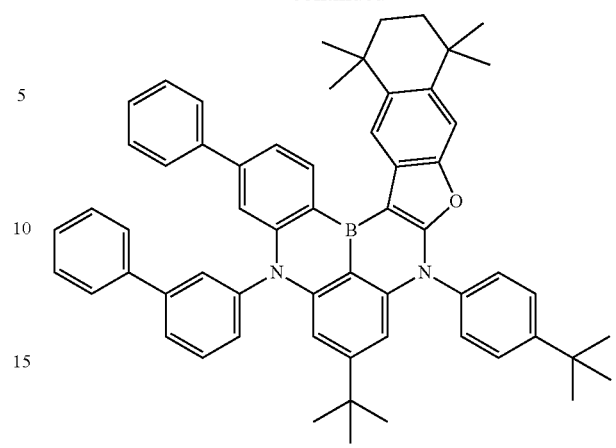
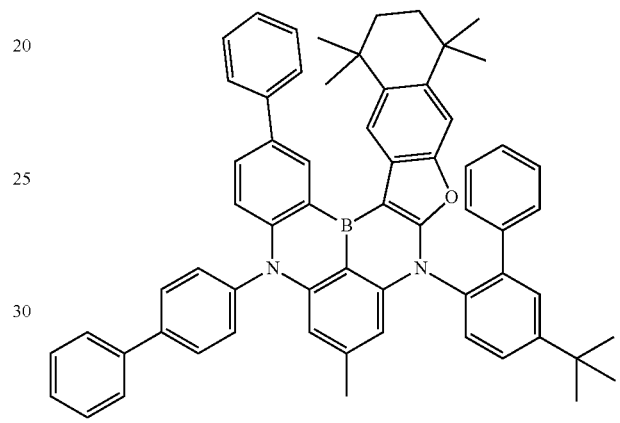
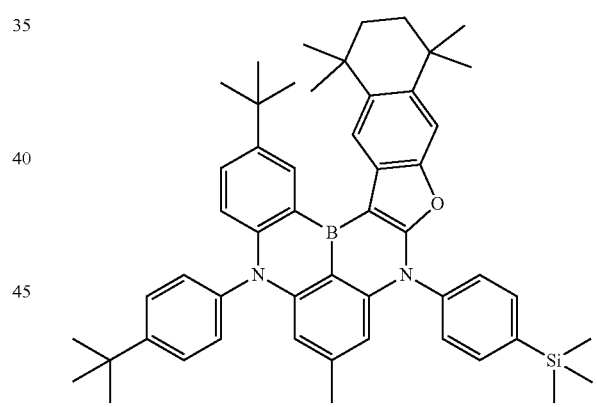
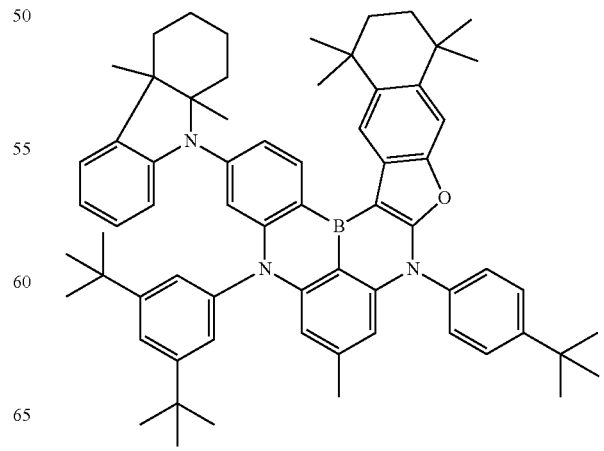

581
-continued
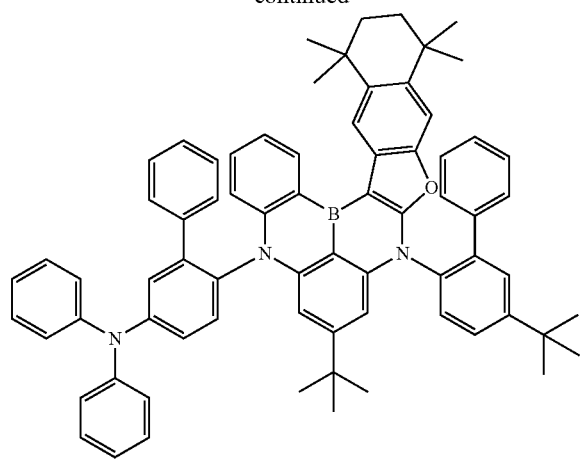
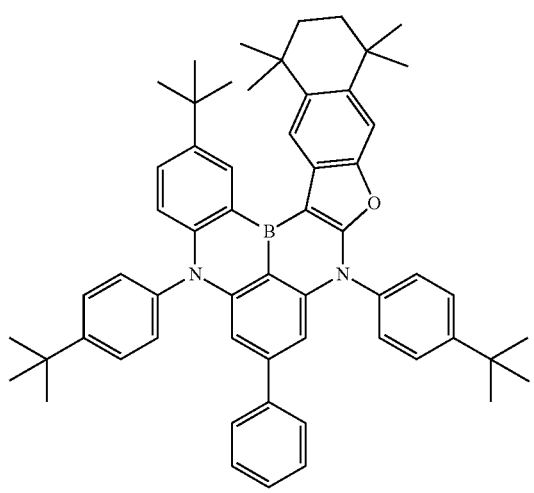
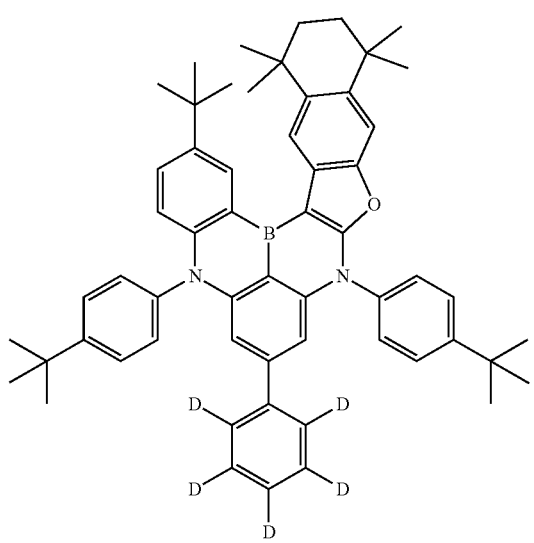
582
-continued
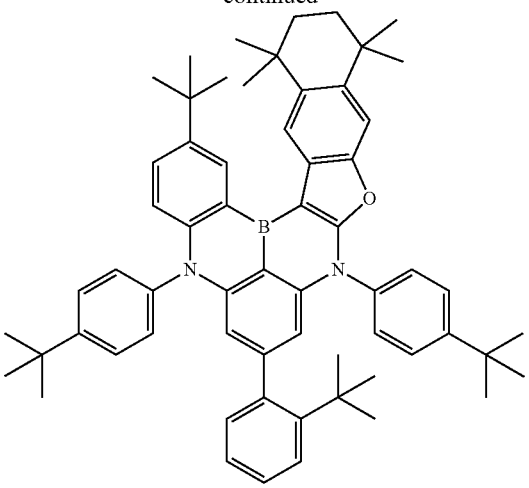
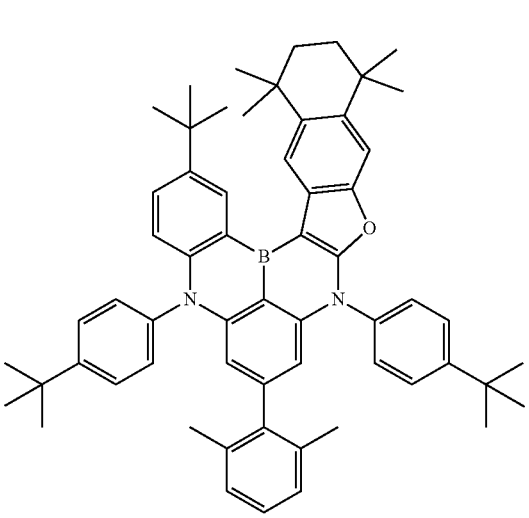
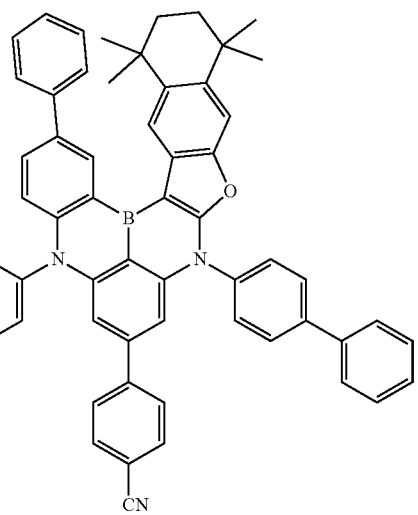

583
-continued
584
-continued
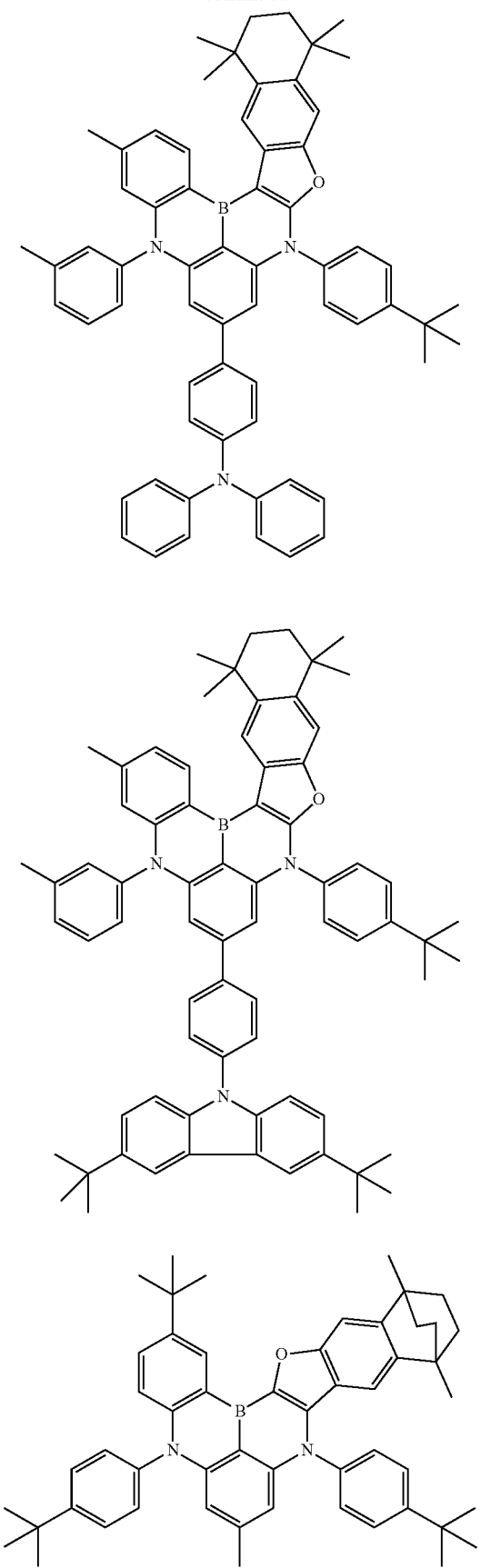
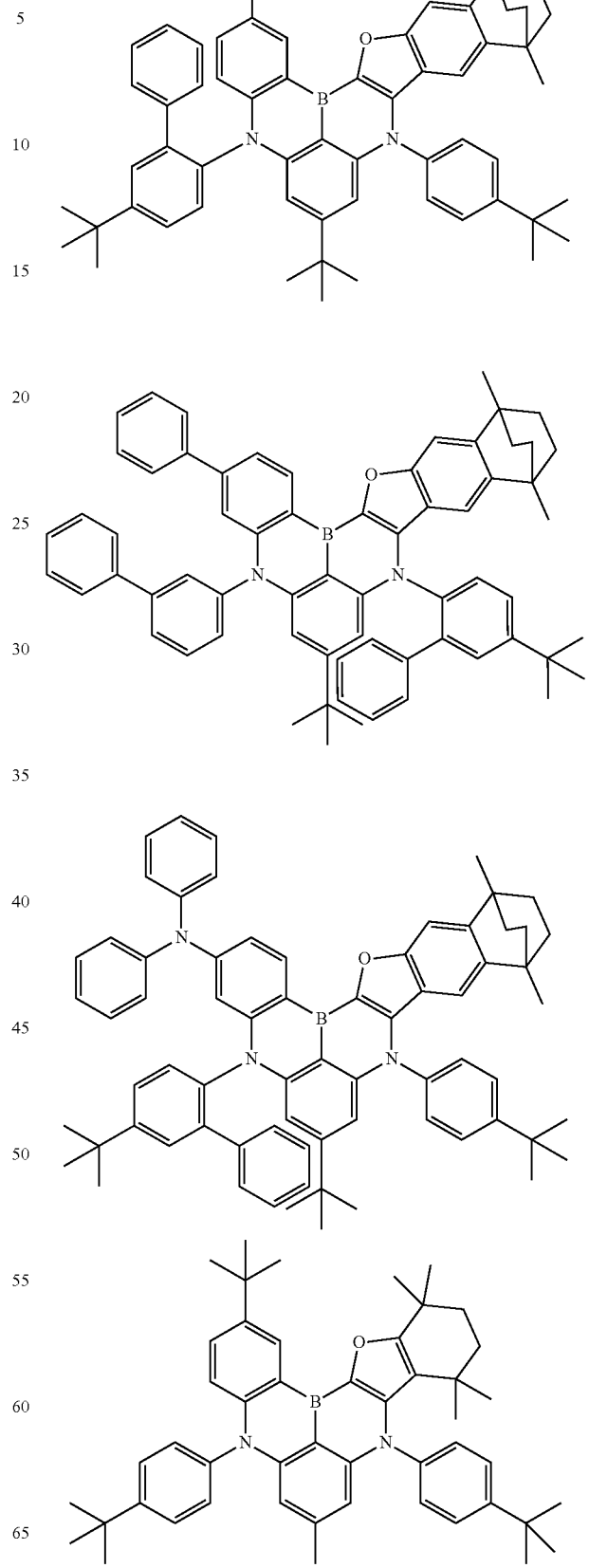

585
-continued
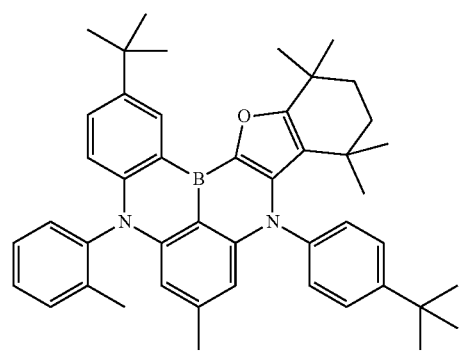
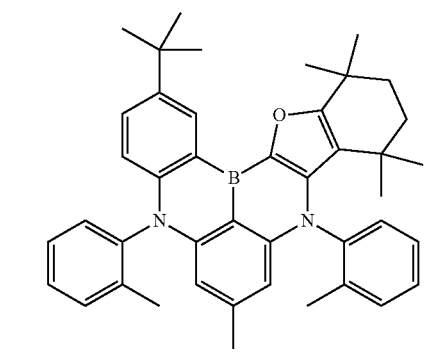
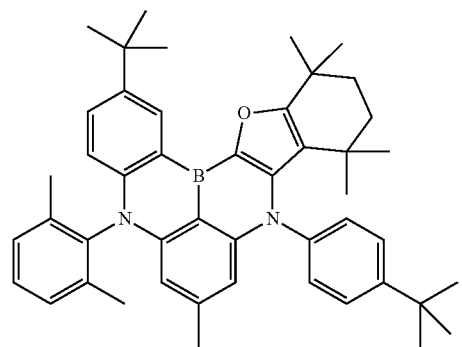
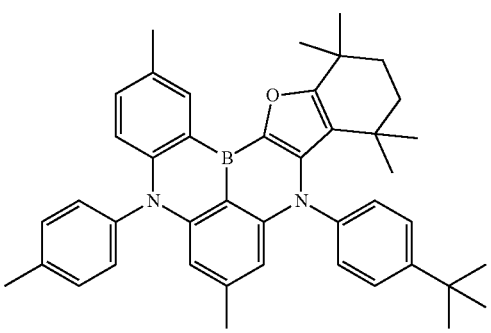
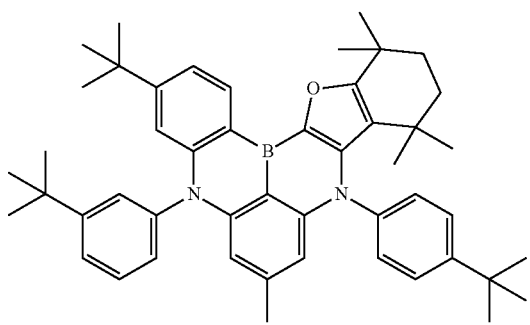
586
-continued
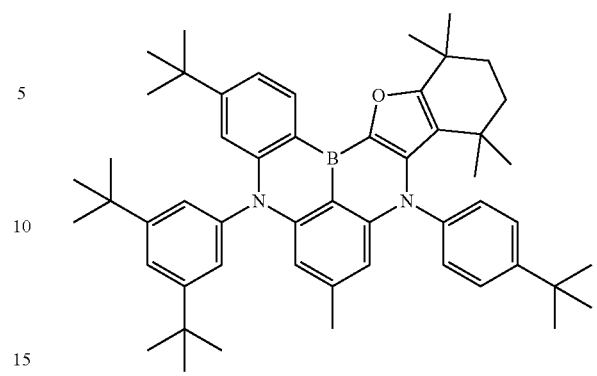
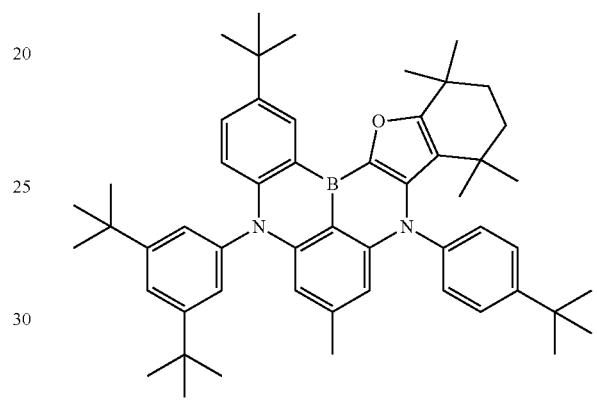
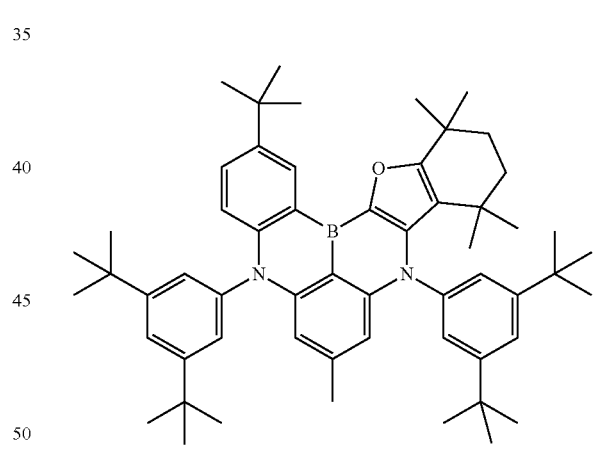
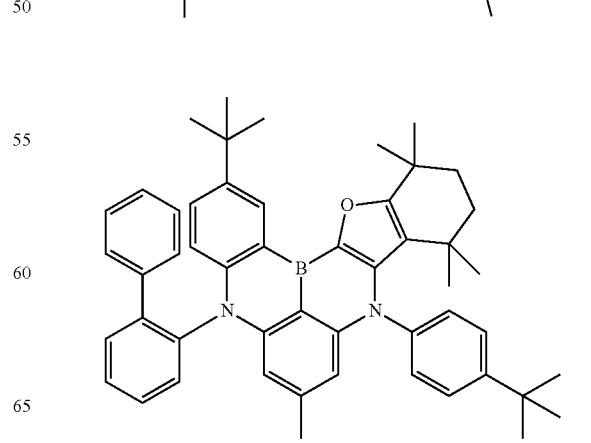

587
-continued
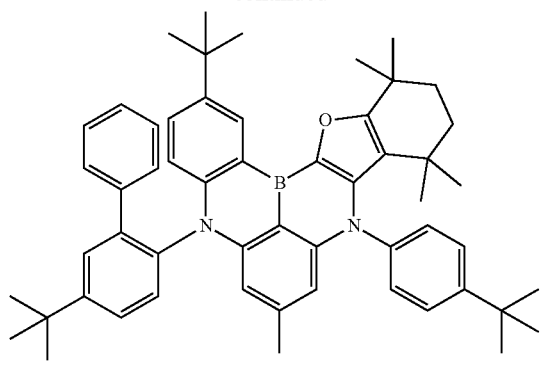
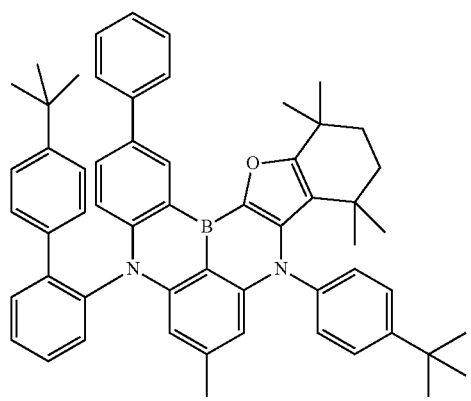
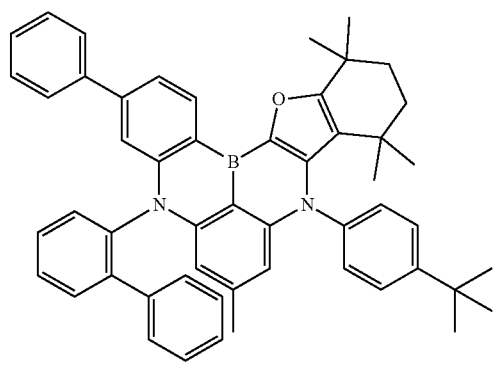
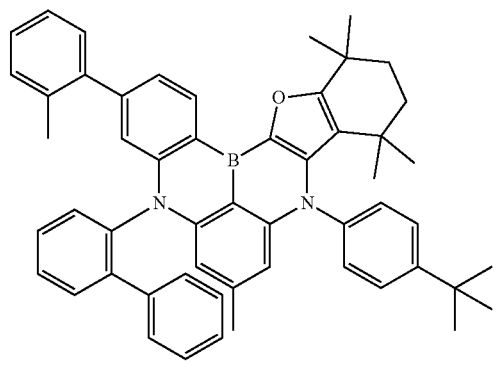
588
-continued
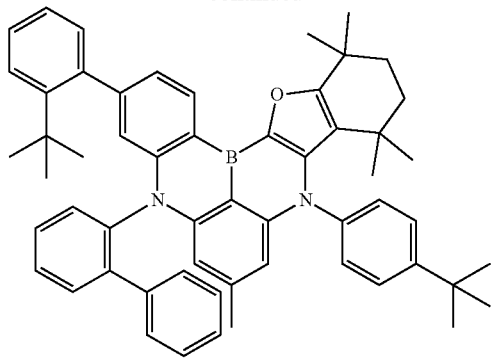
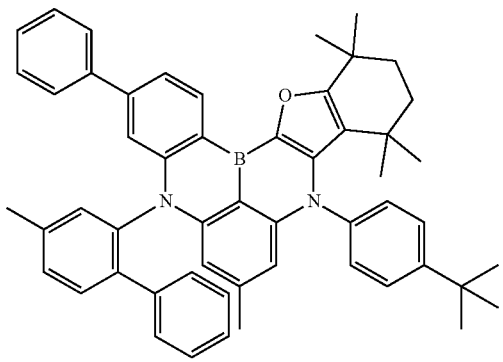
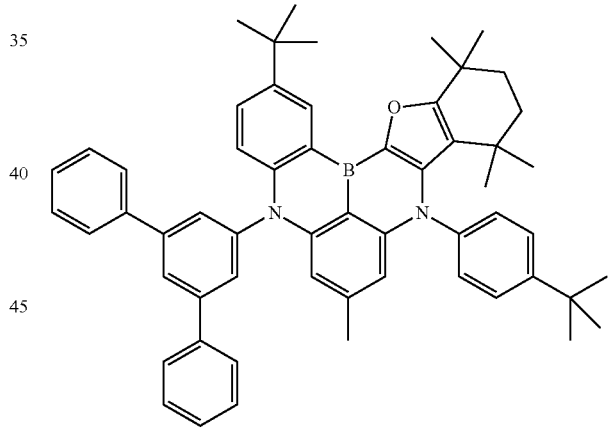
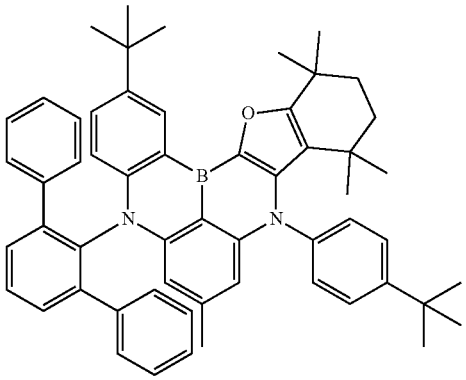

589
-continued
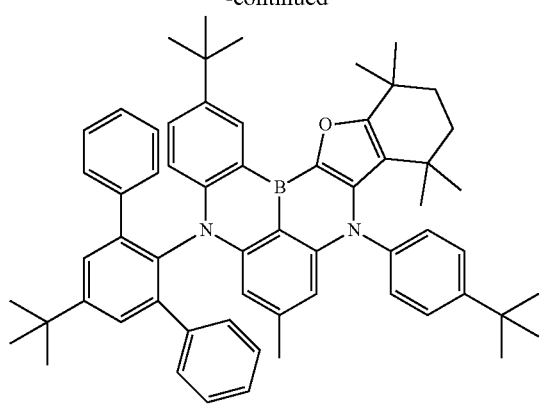
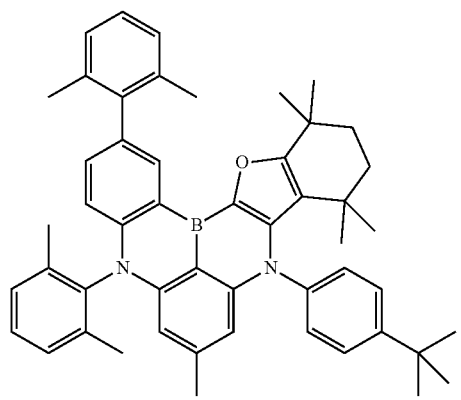
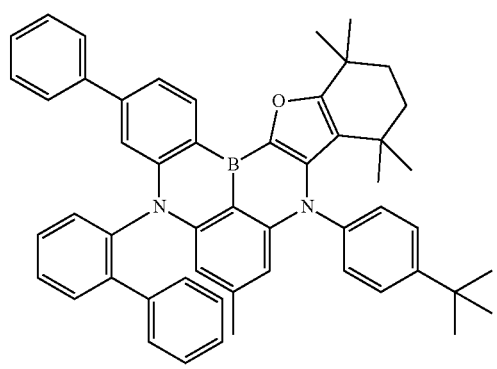
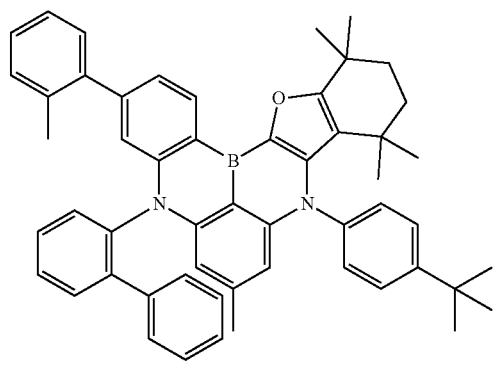
590
-continued
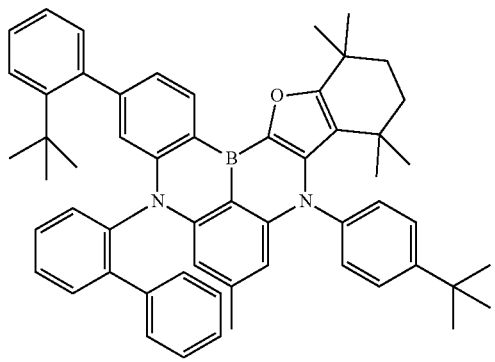
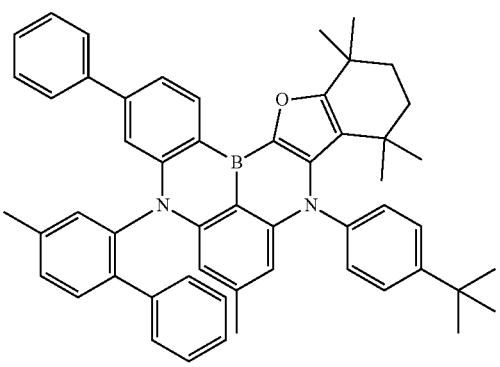
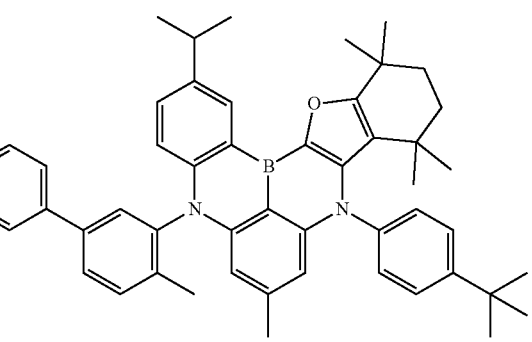
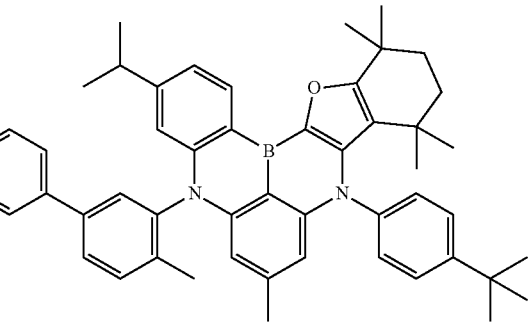

591
-continued
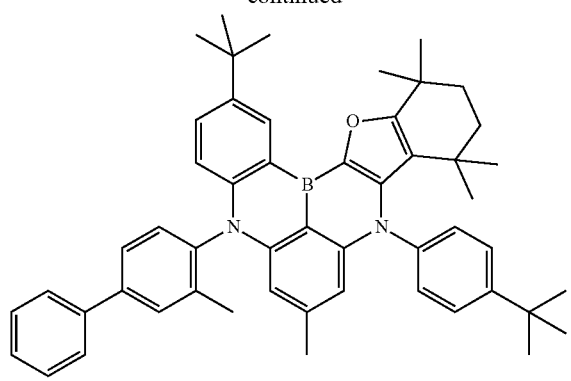
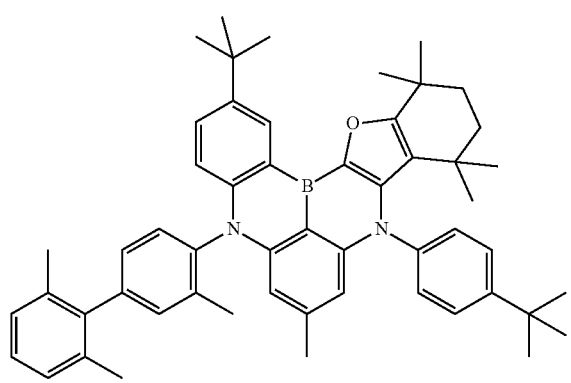
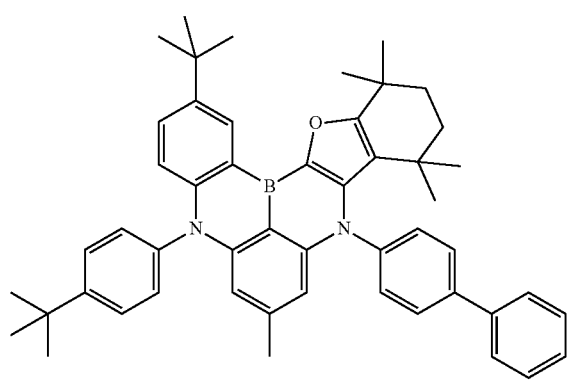
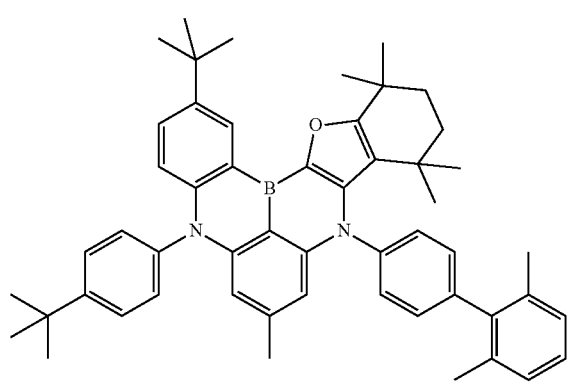
592
-continued
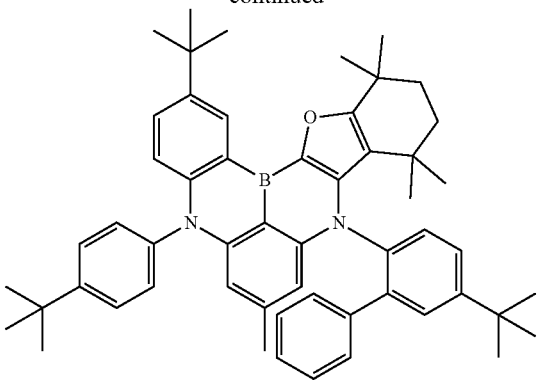
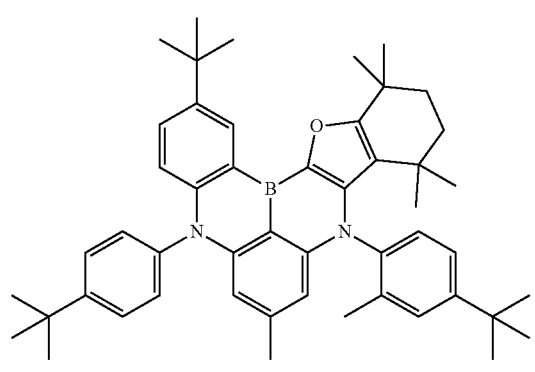
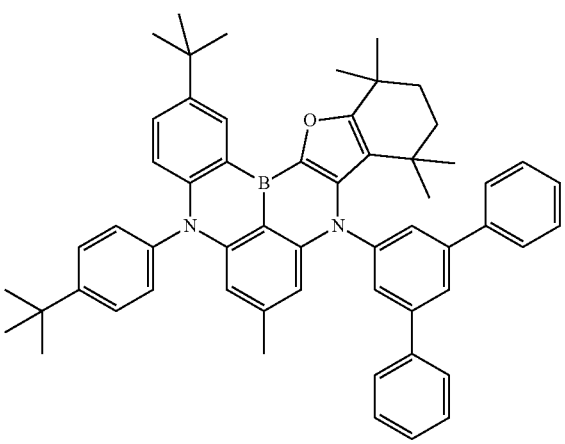
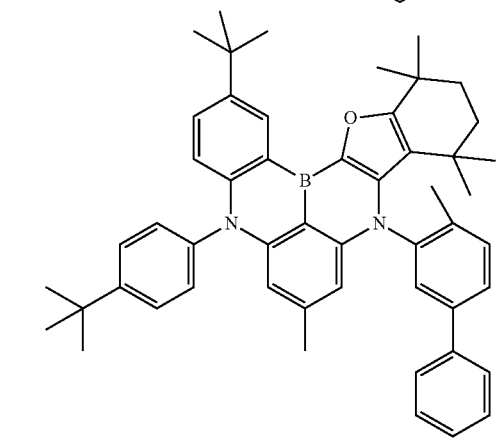

593
-continued
594
-continued
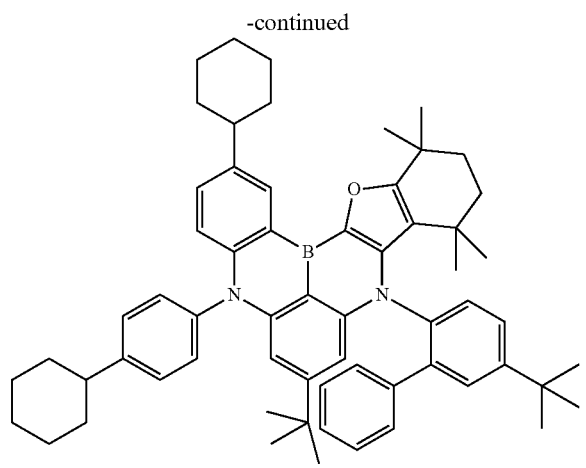
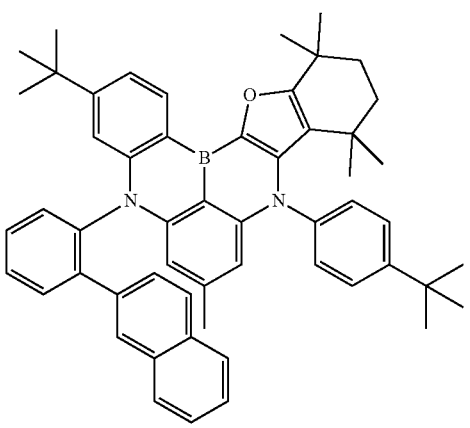
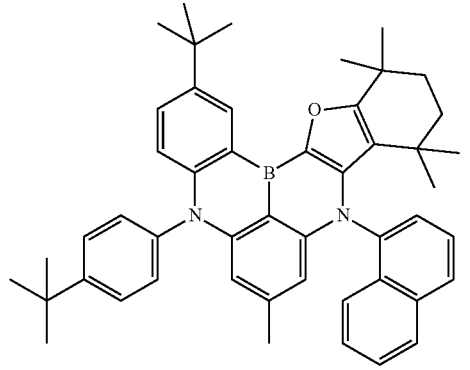
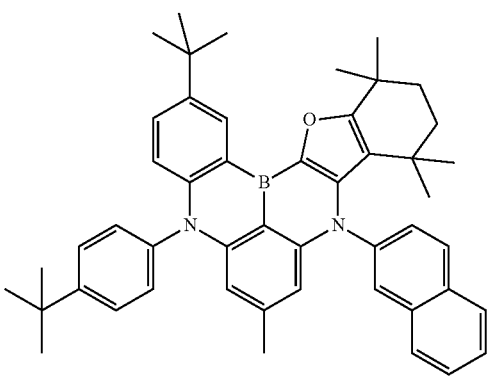
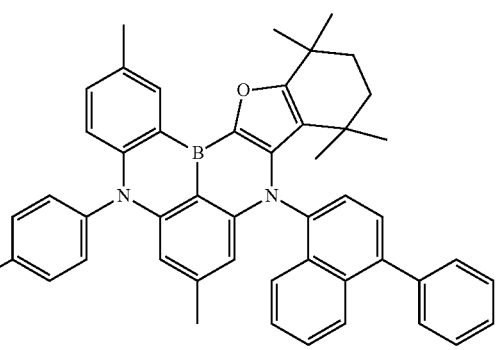

595
-continued
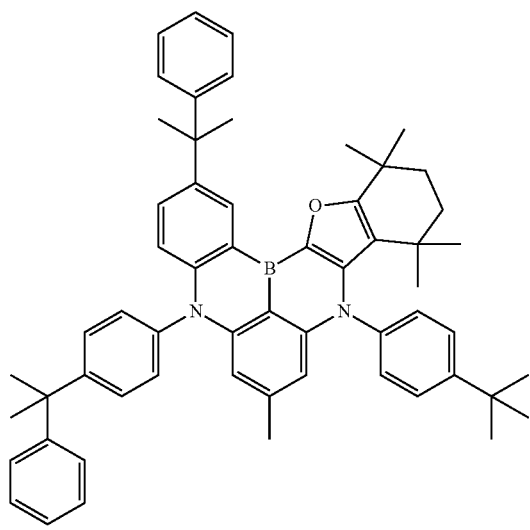
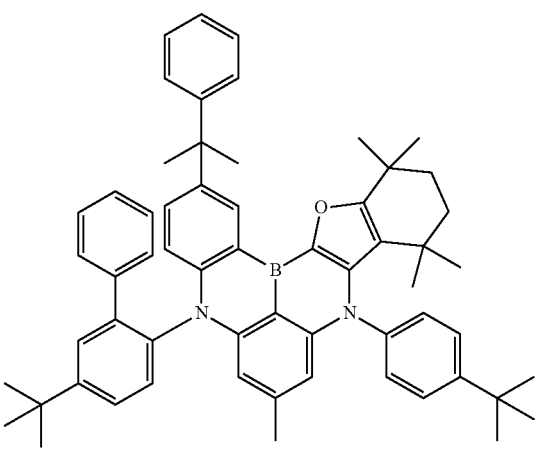
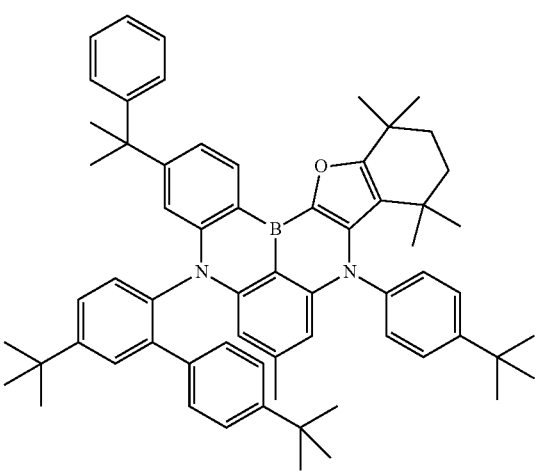
596
-continued
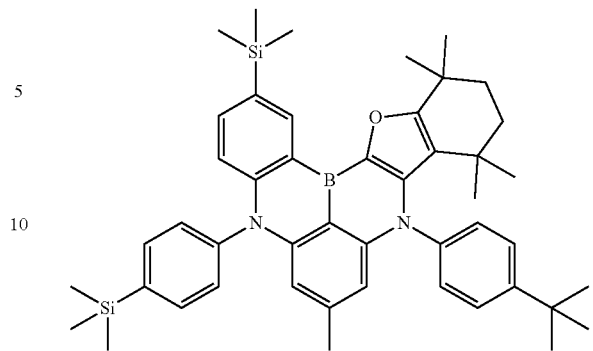
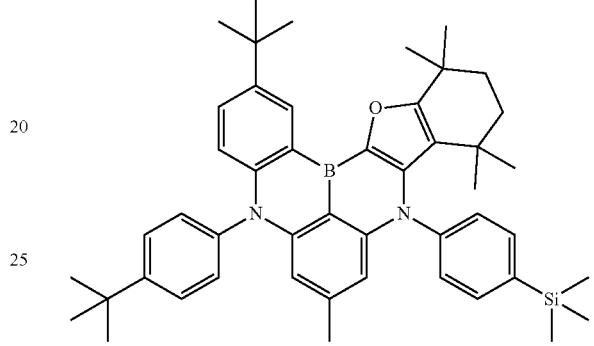
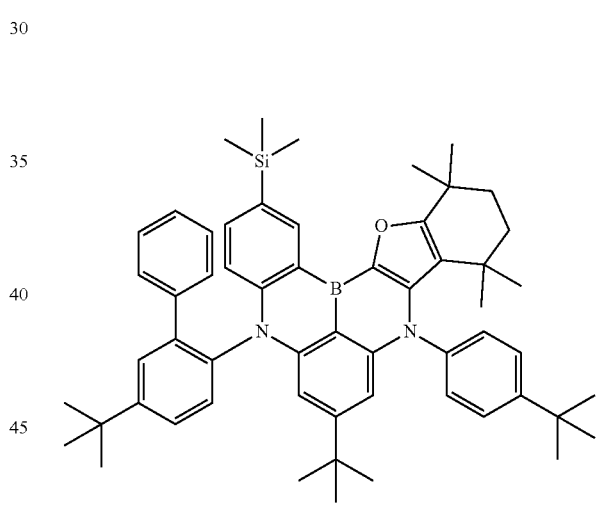

597
-continued
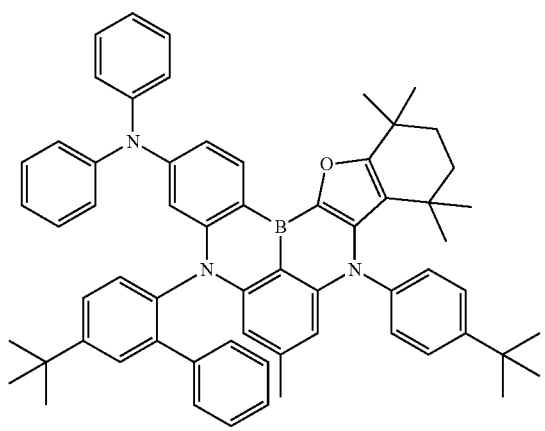
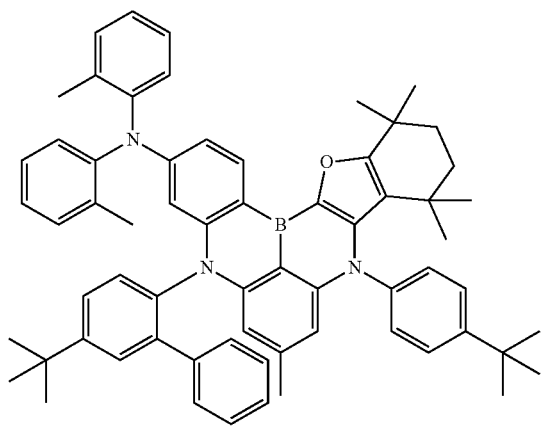
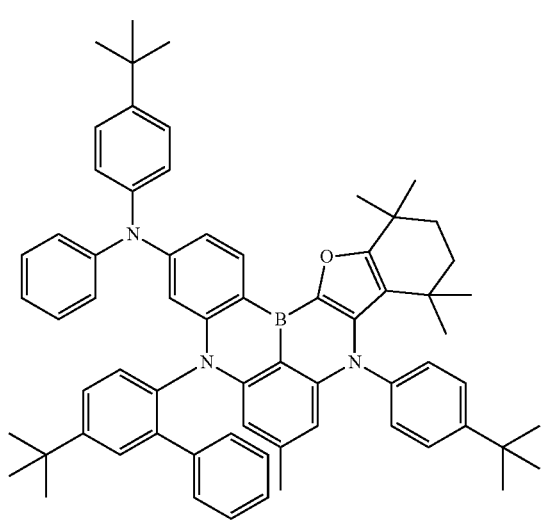
598
-continued
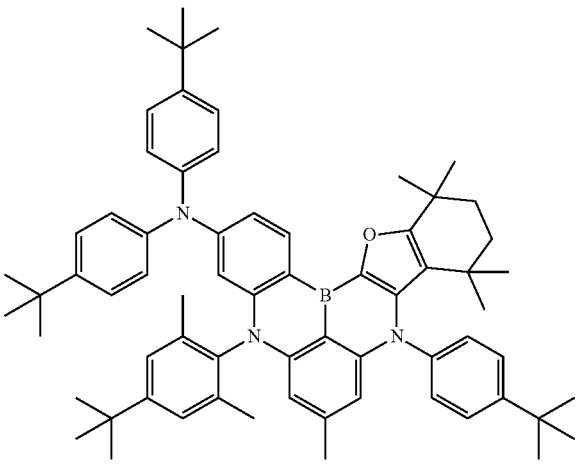
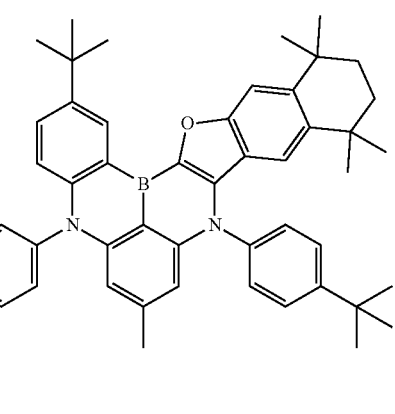
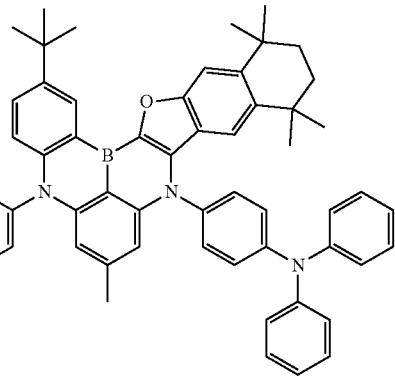
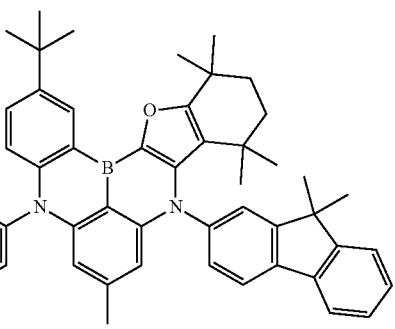

599
-continued
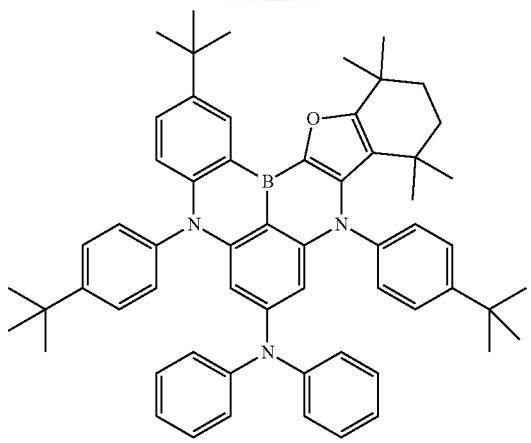
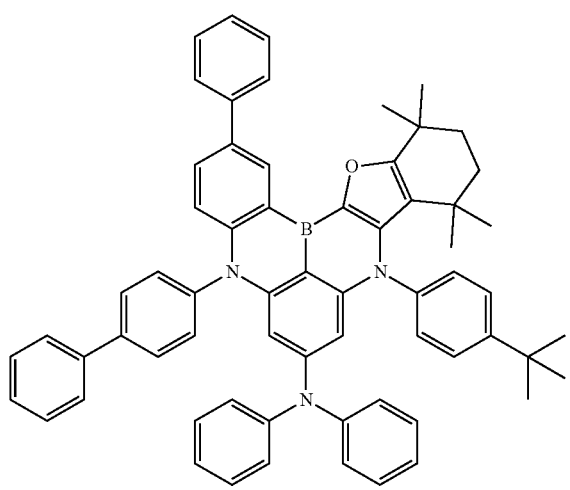
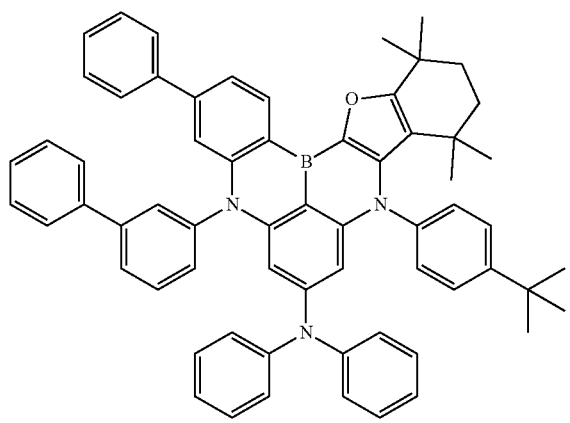
600
-continued
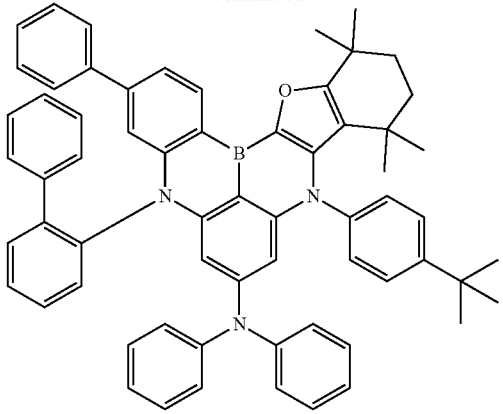
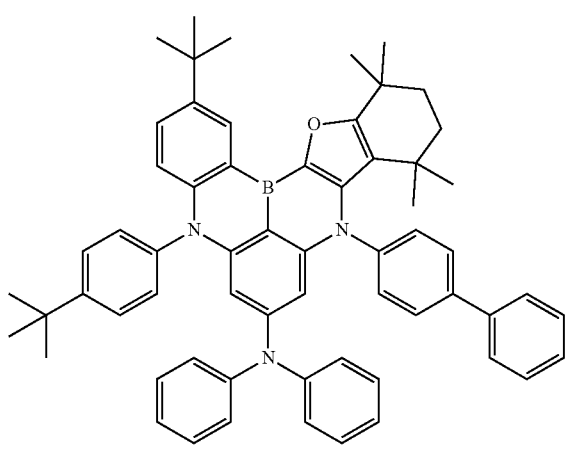
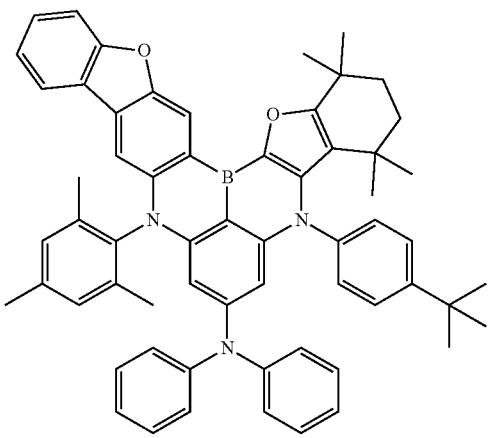

601
-continued
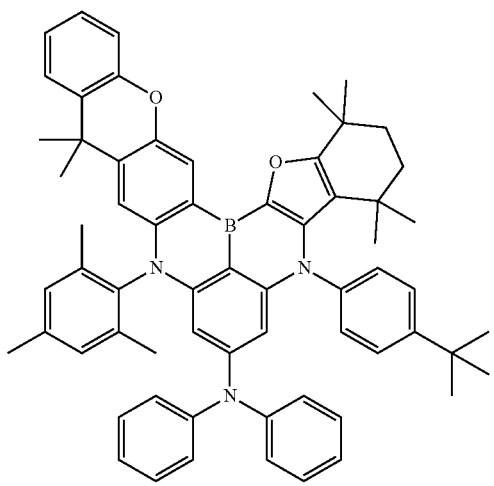
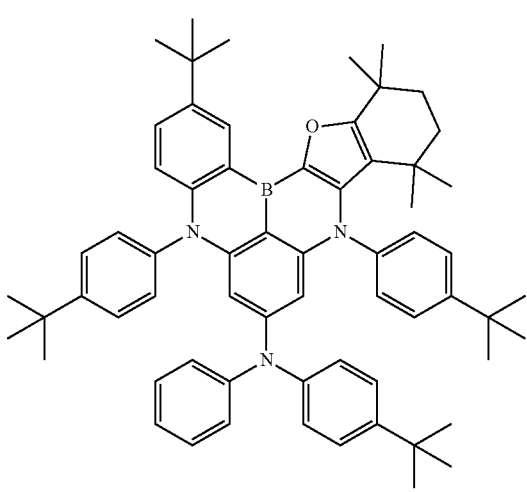
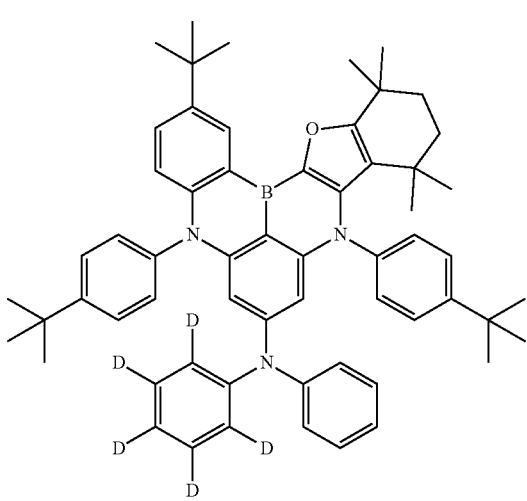
602
-continued
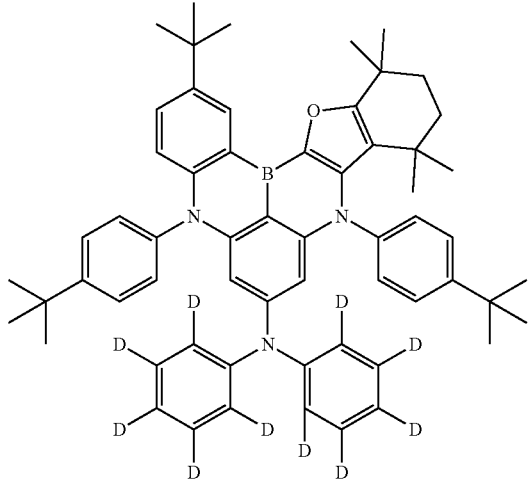
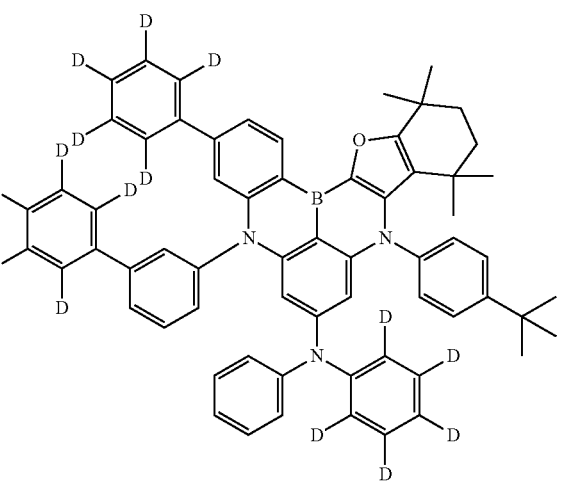
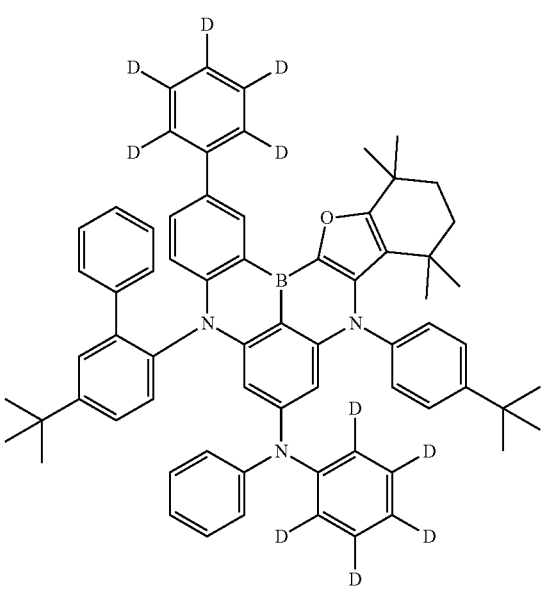

603 -continued

604 -continued

605
-continued

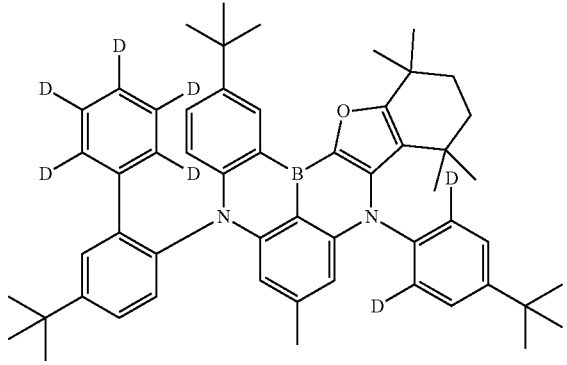
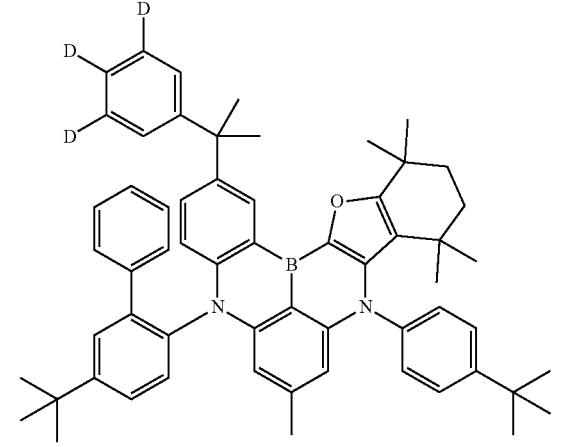
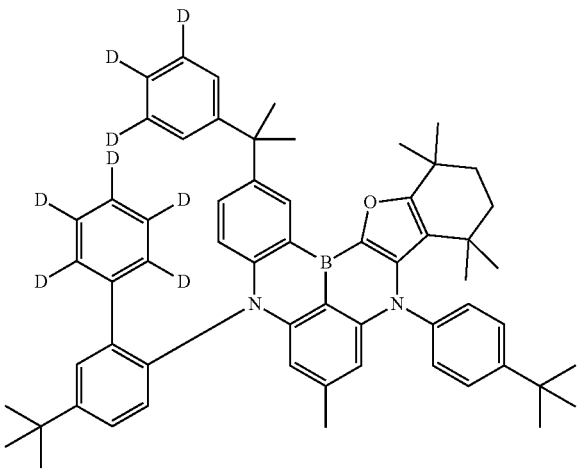
606
-continued
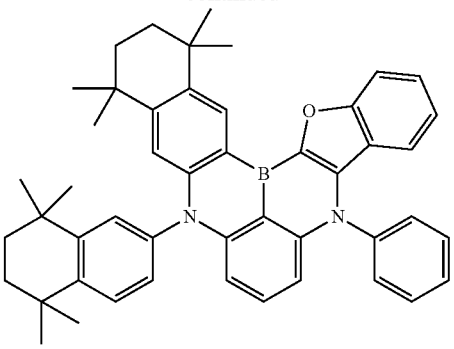
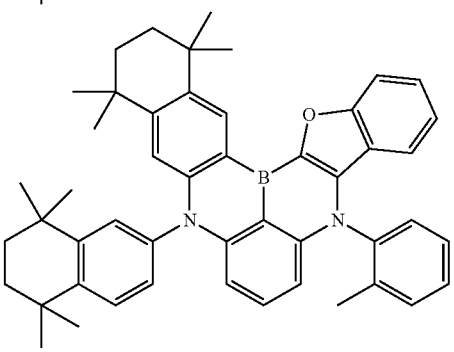
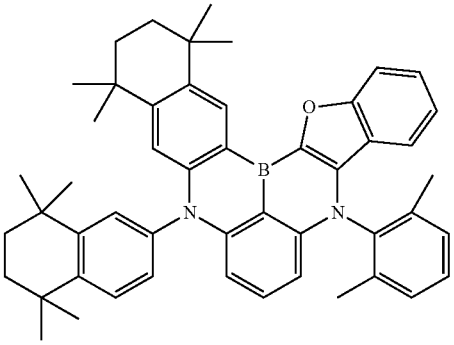
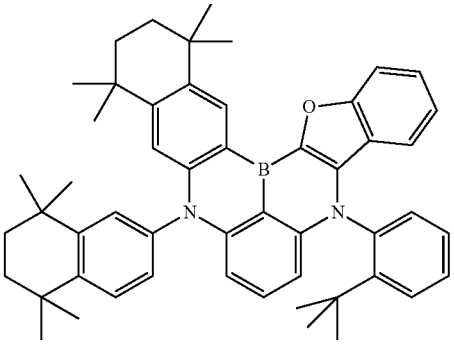
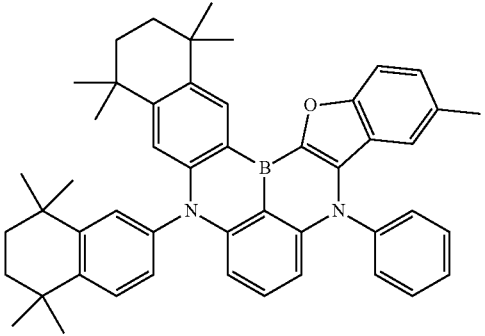

607
-continued
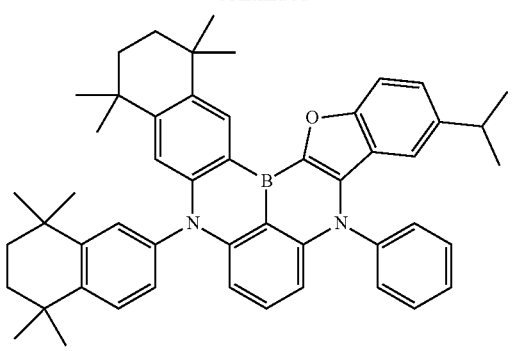
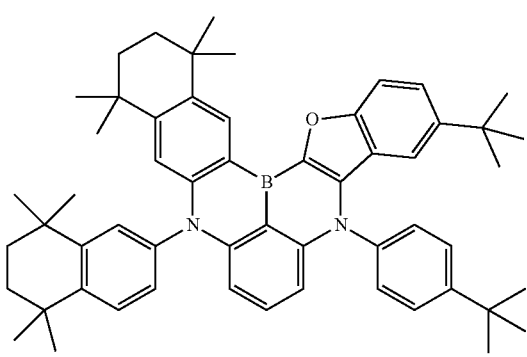
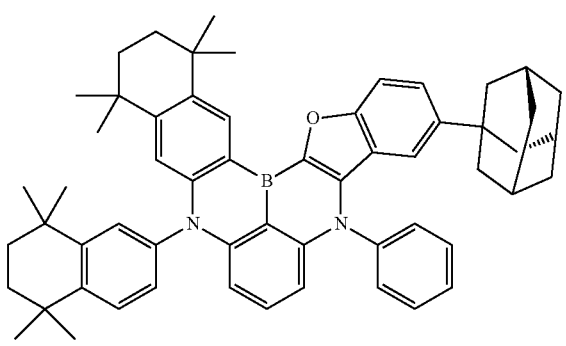
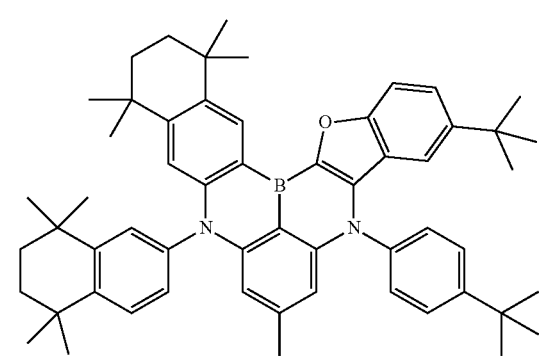
608
-continued
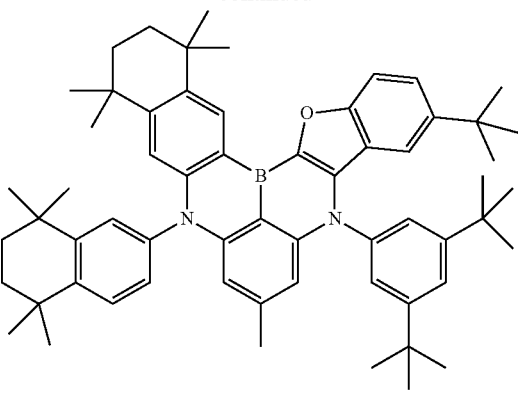
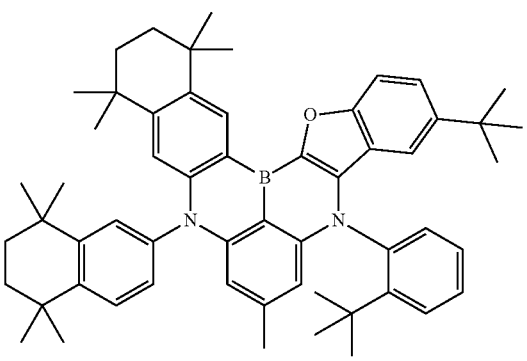
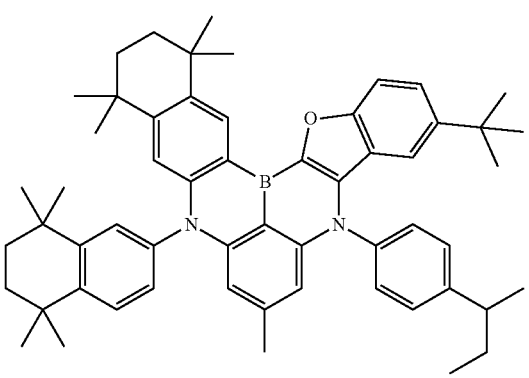
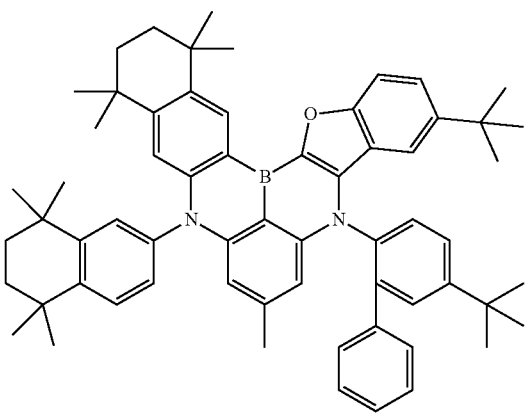

609
-continued
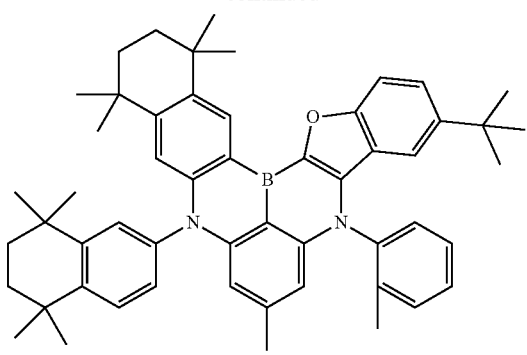
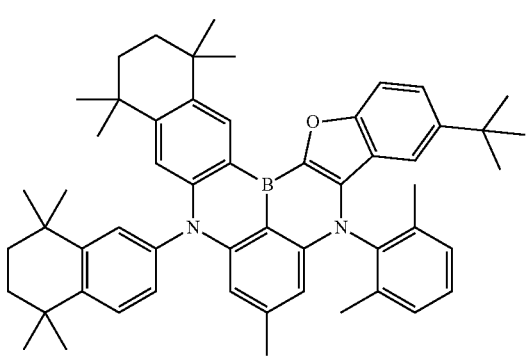
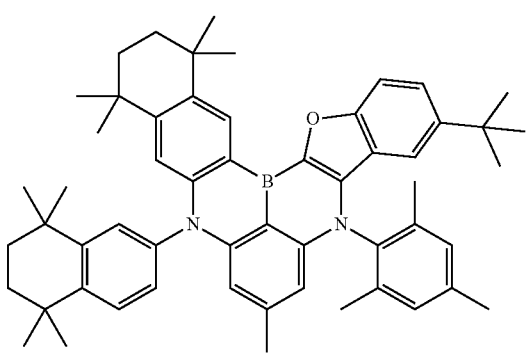
610
-continued
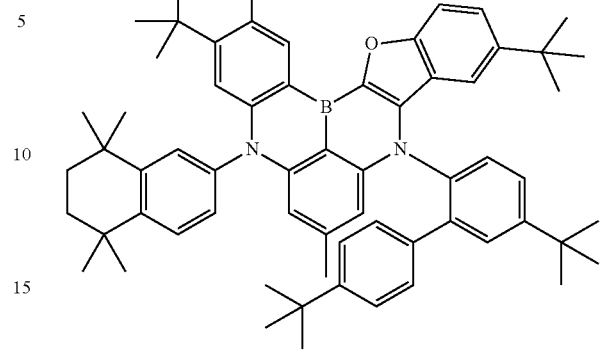
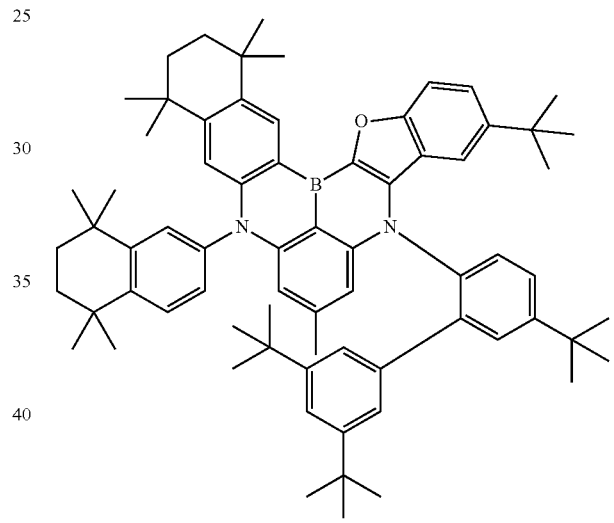
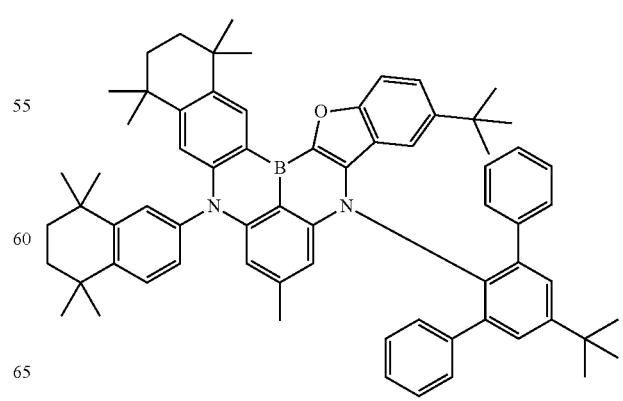

611
-continued
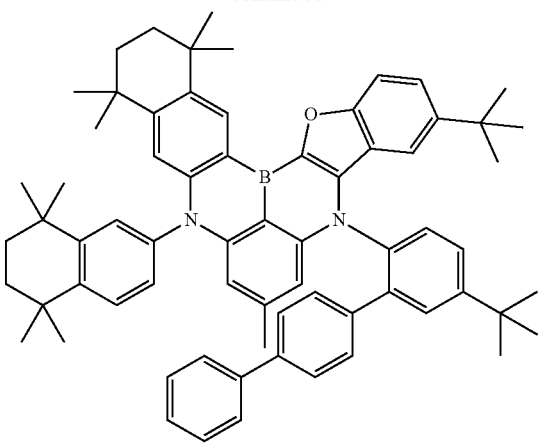
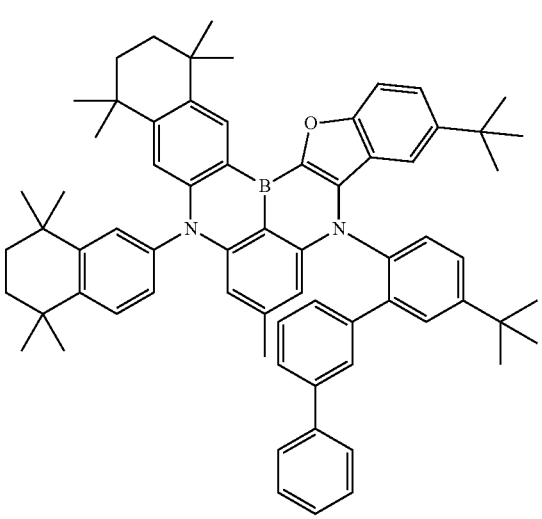
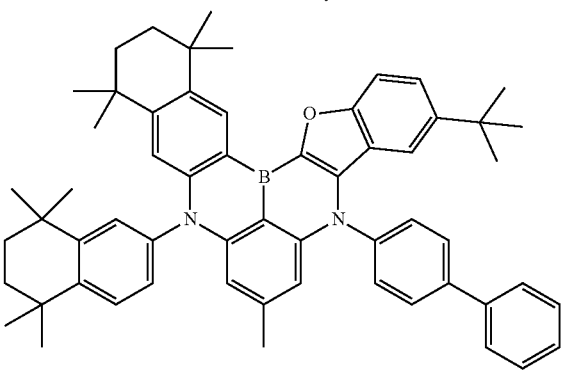
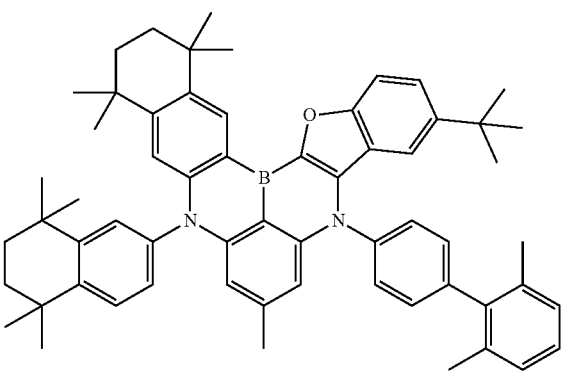
612
-continued
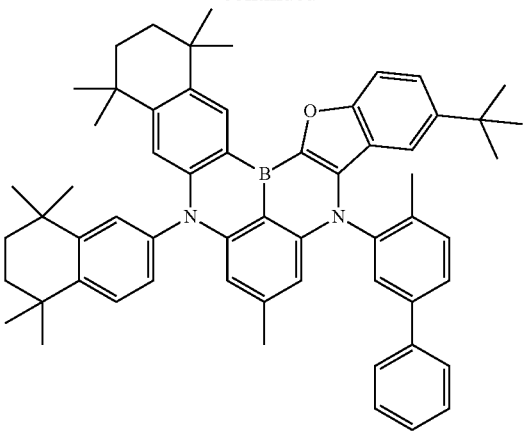
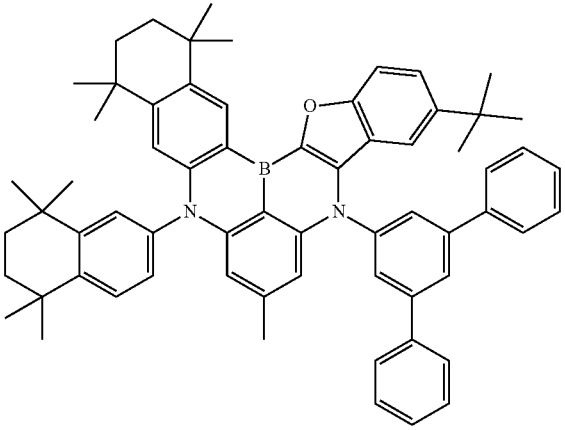
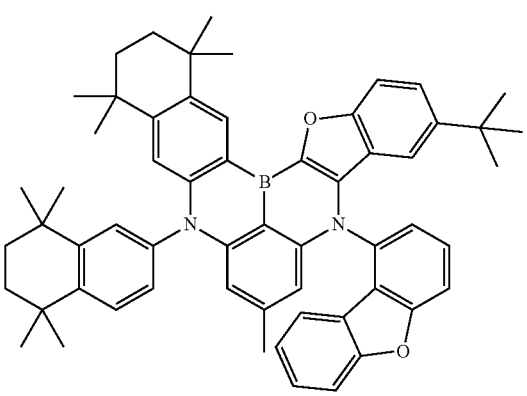
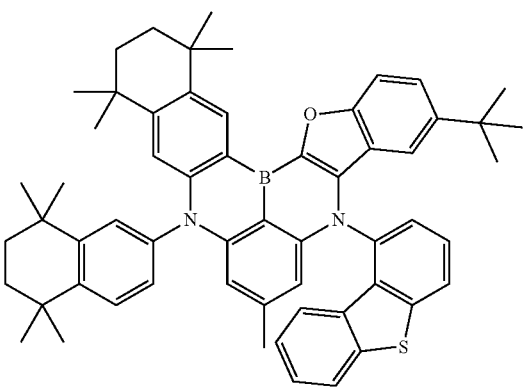

613
-continued
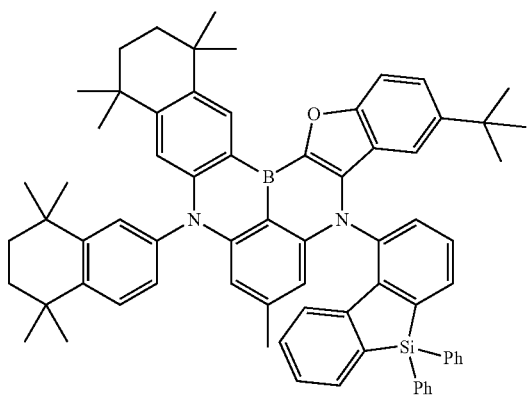
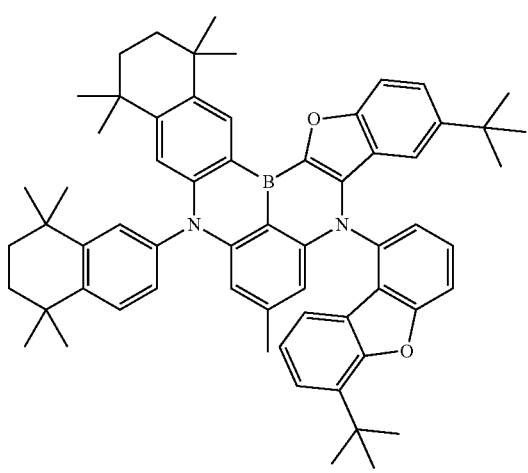
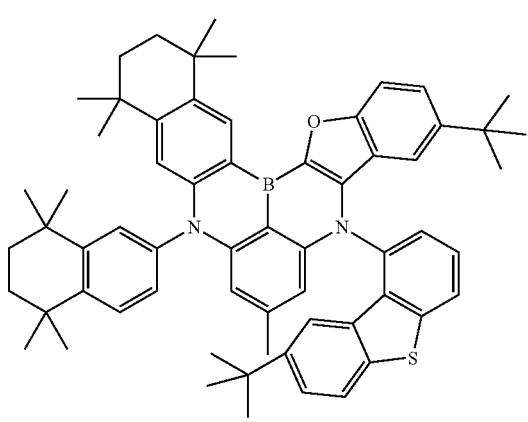
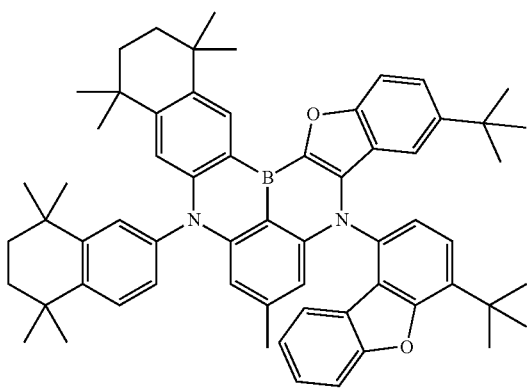
614
-continued
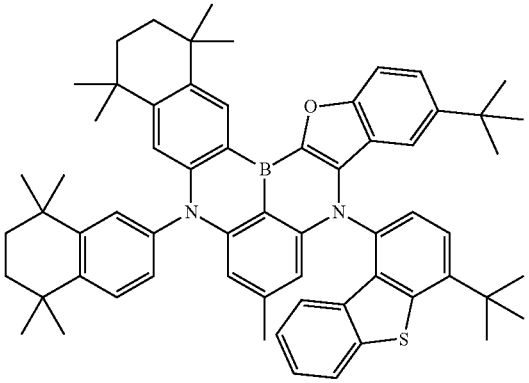
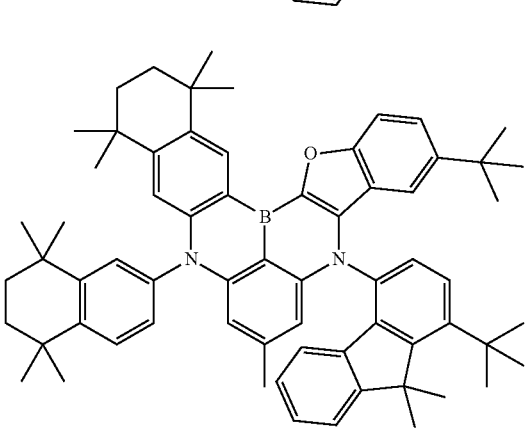
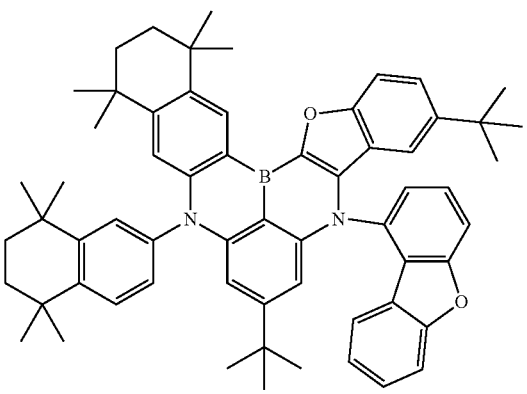
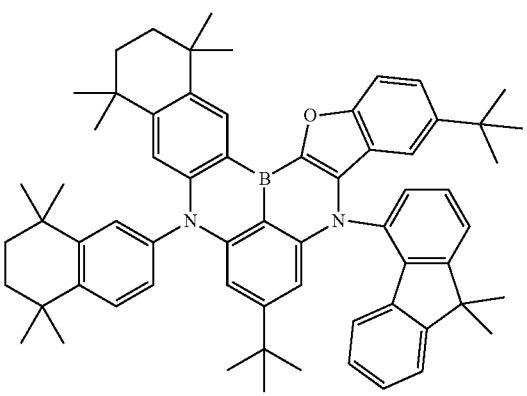

615
-continued
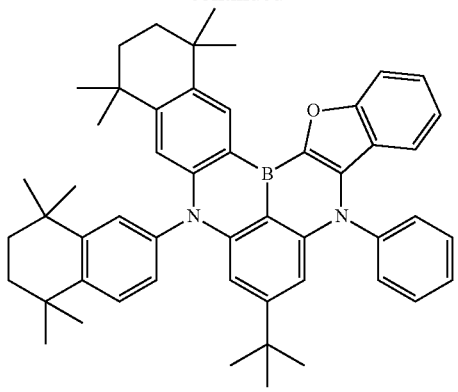
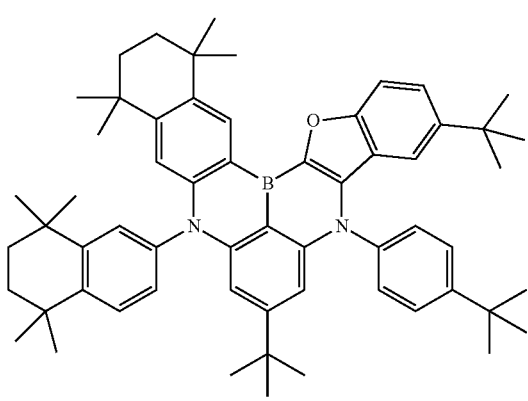
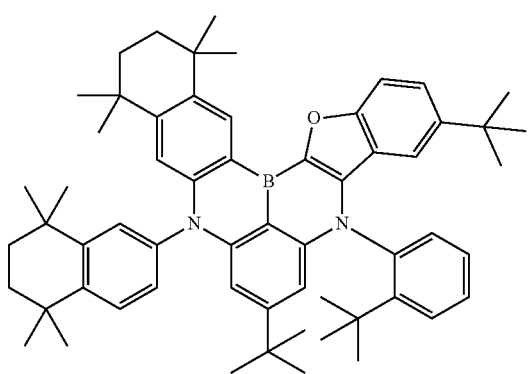
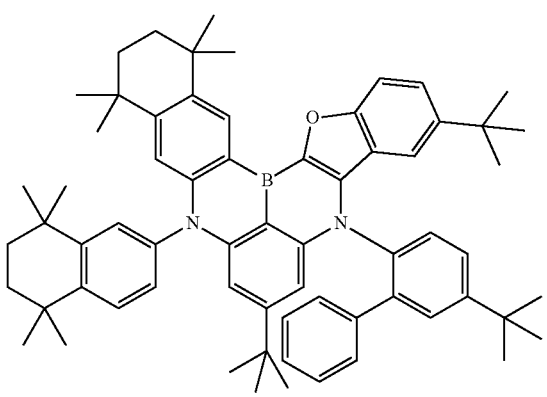
616
-continued

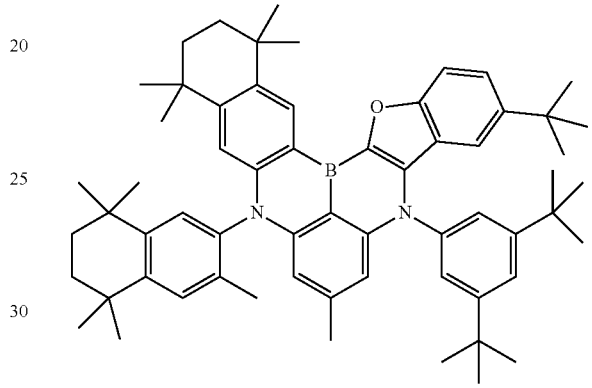
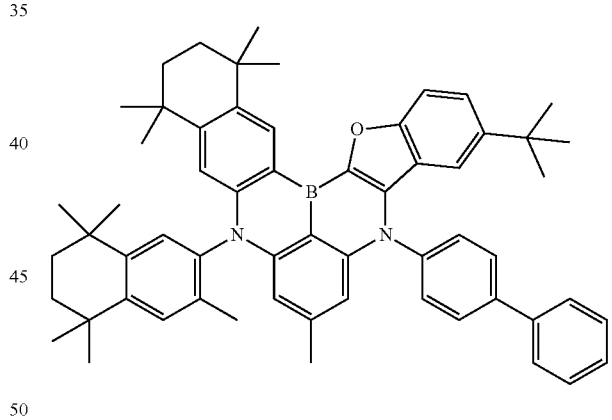
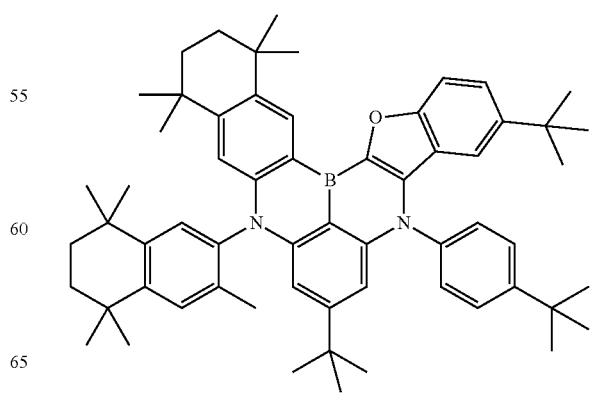

617
-continued
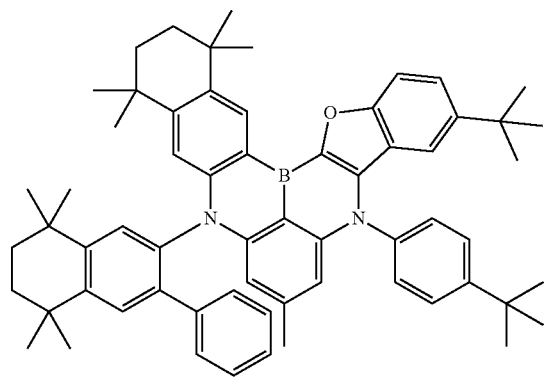
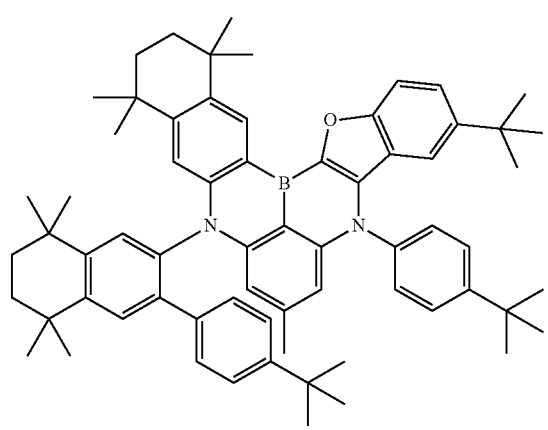
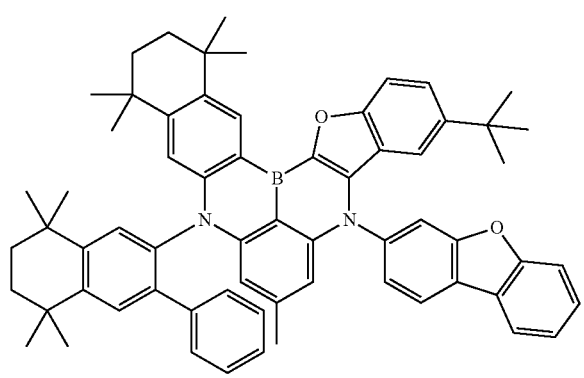
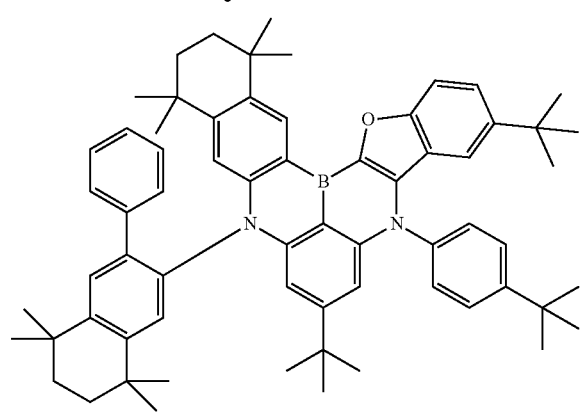
618
-continued
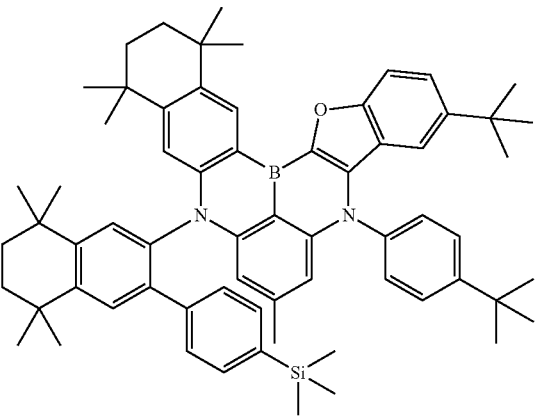
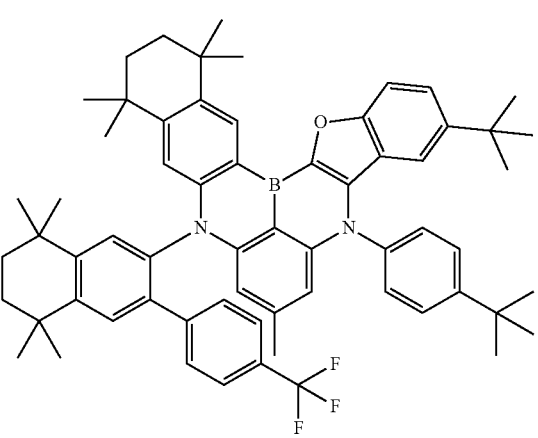
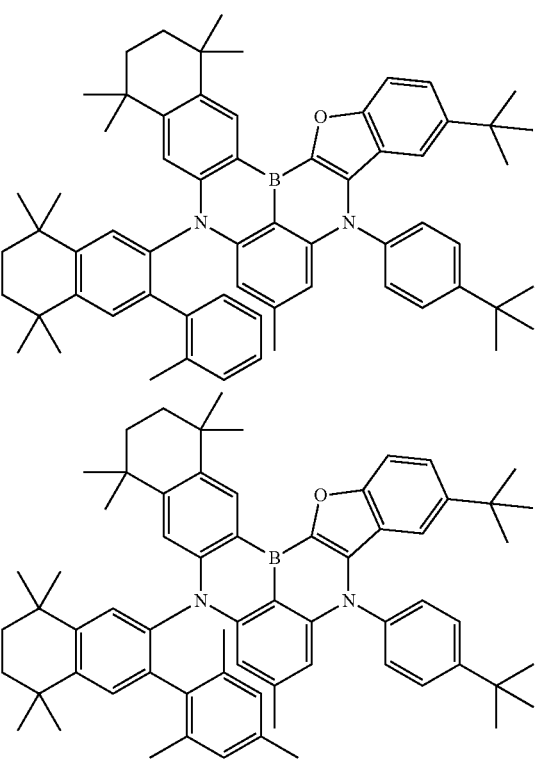

619
-continued
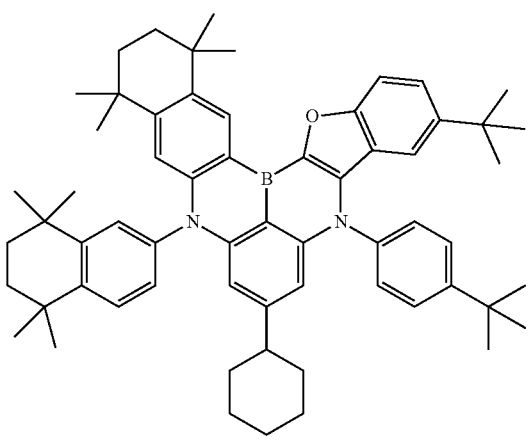
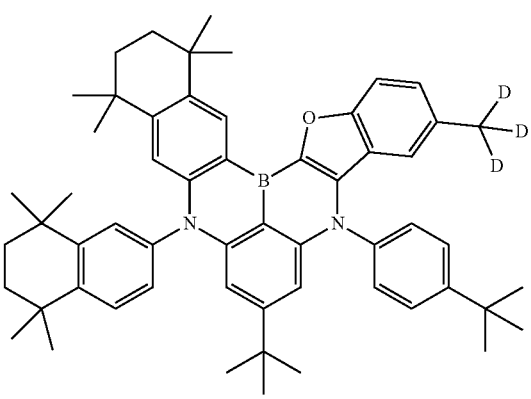
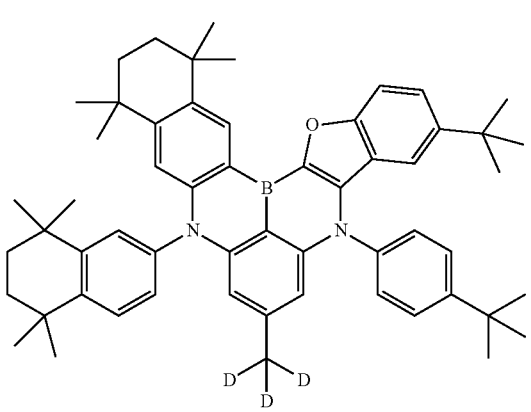
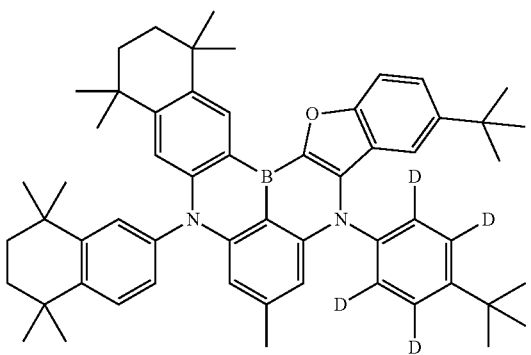
620
-continued
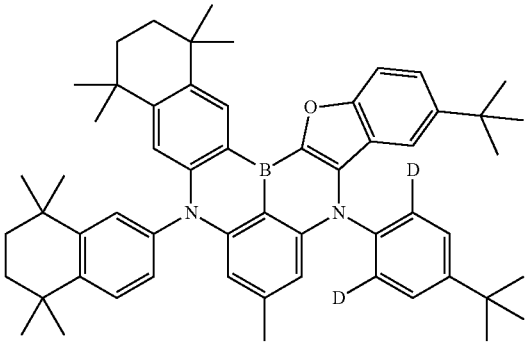
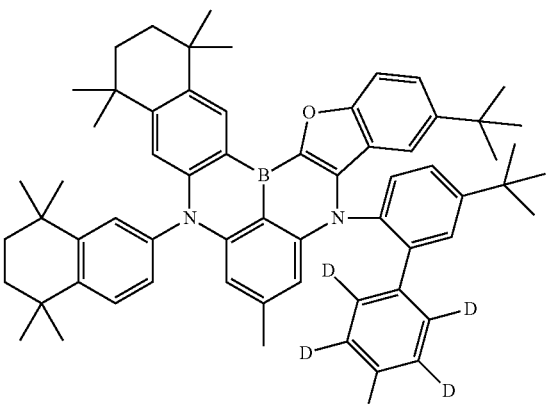
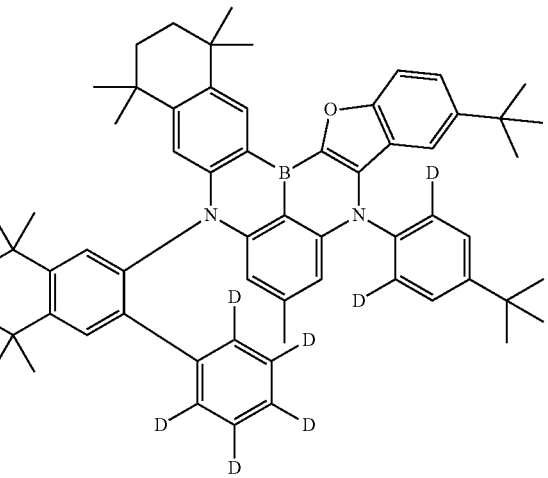
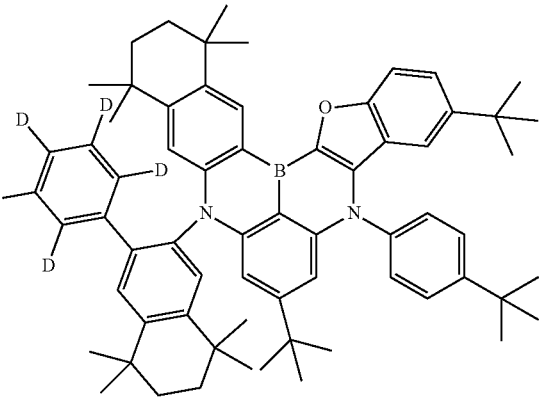

621
-continued
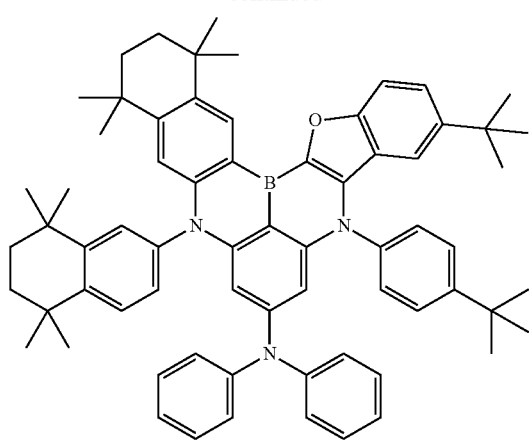
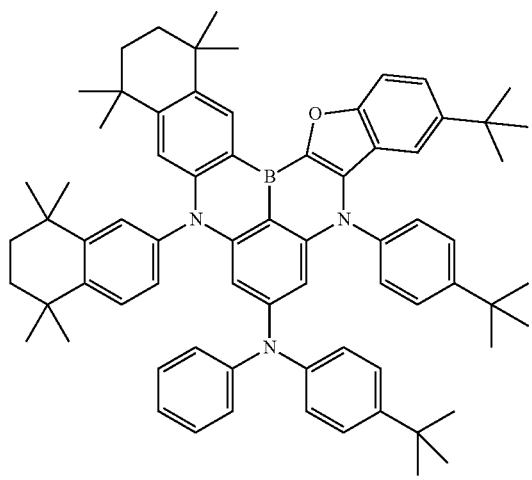
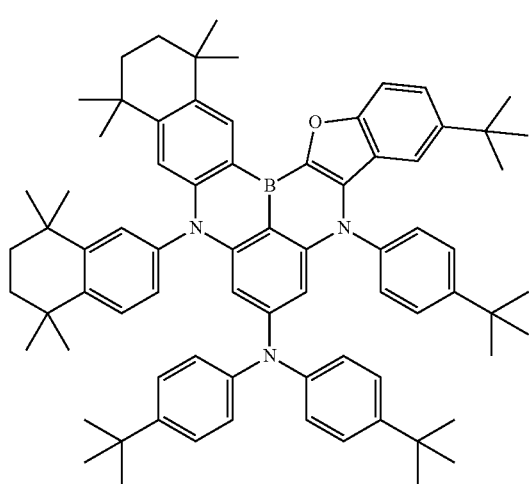
622
-continued
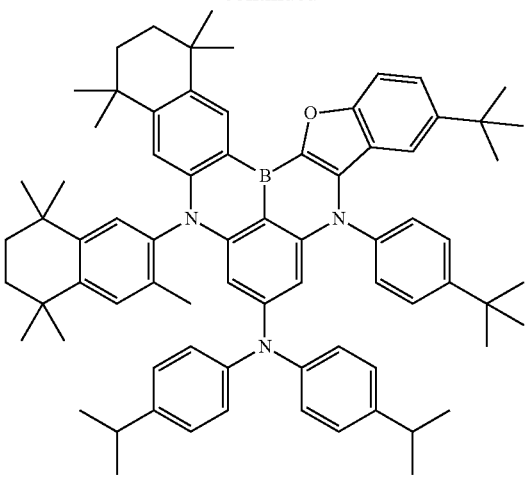
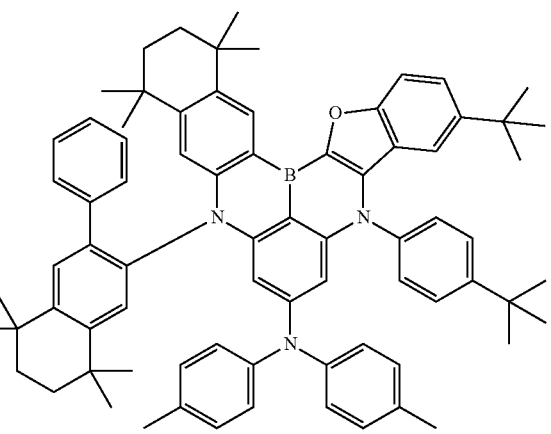
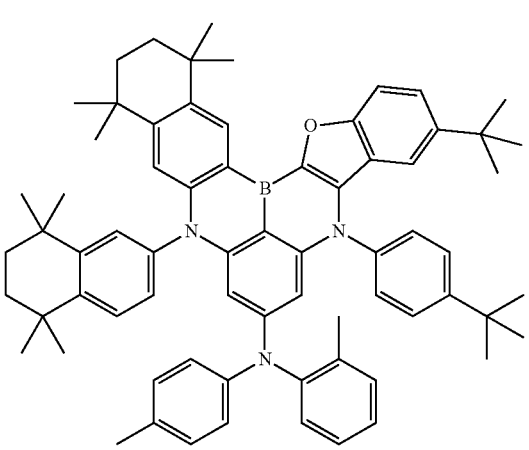

623
-continued
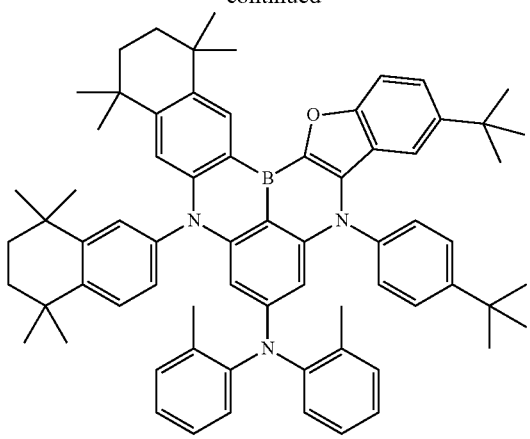
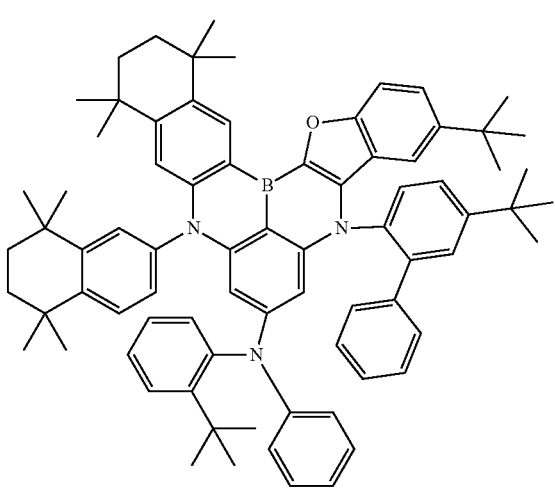
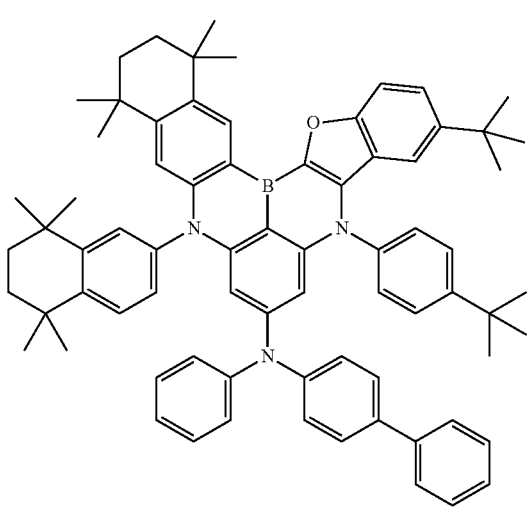
624
-continued
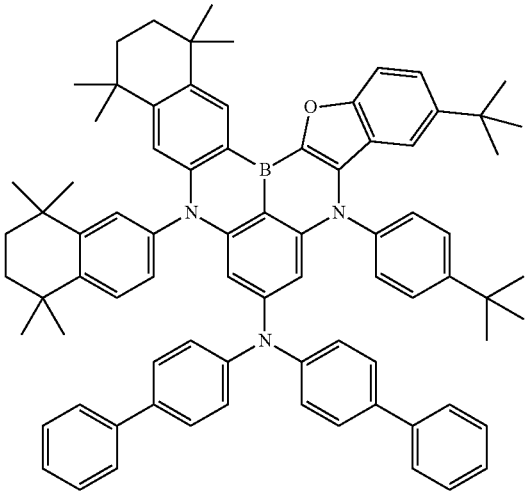
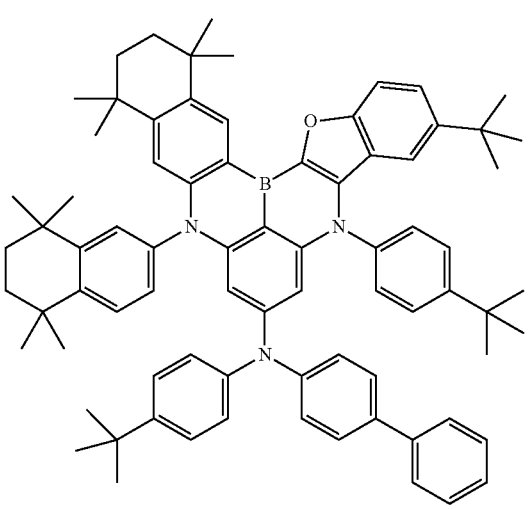
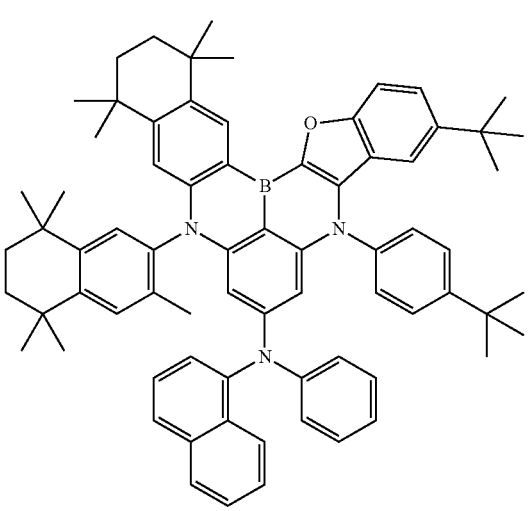

625
-continued
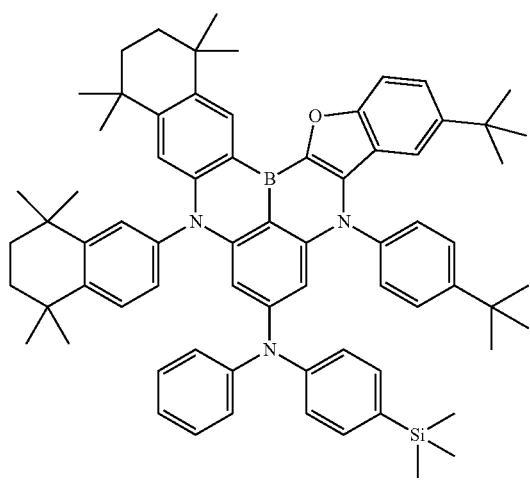
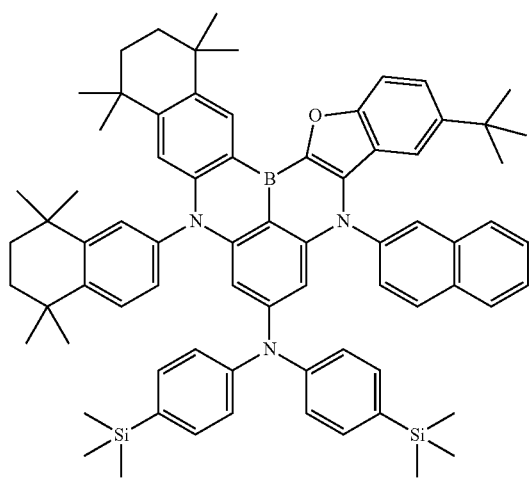
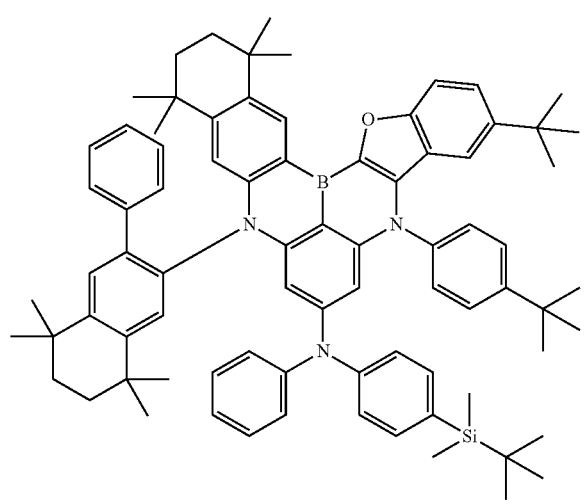
626
-continued
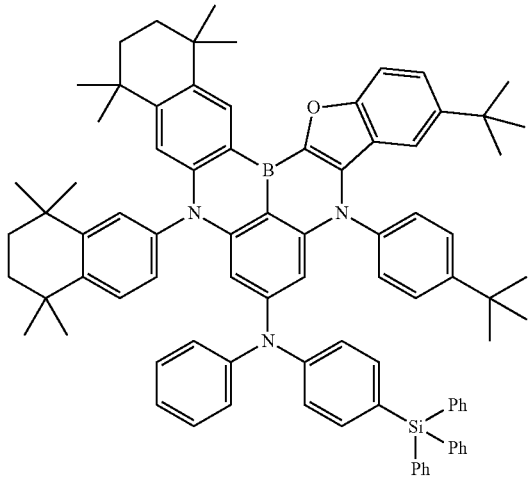
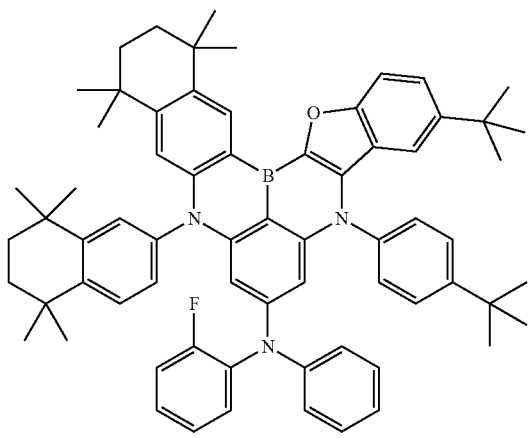
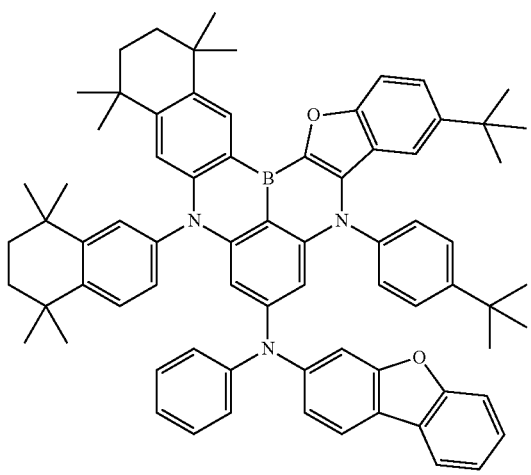

627
-continued
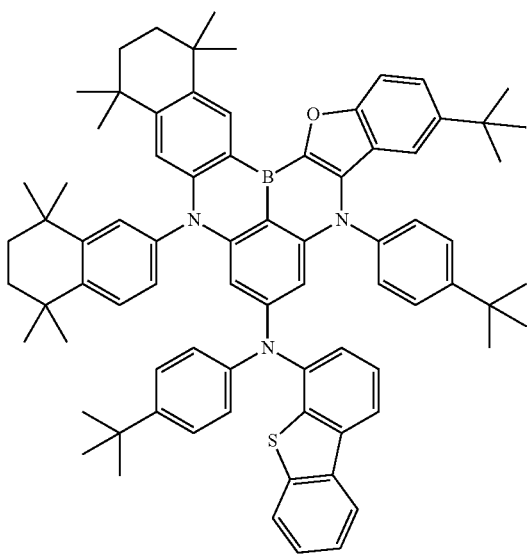
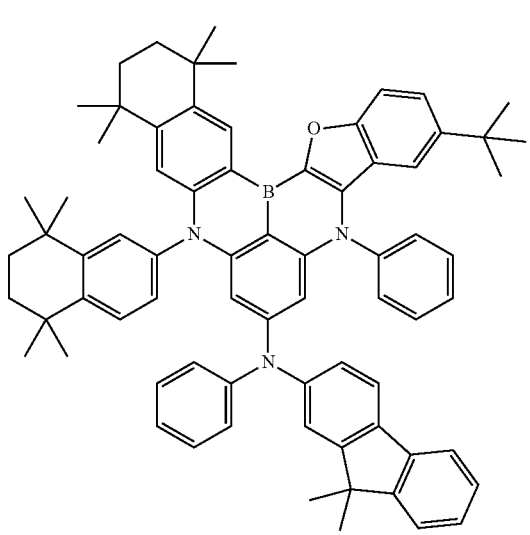
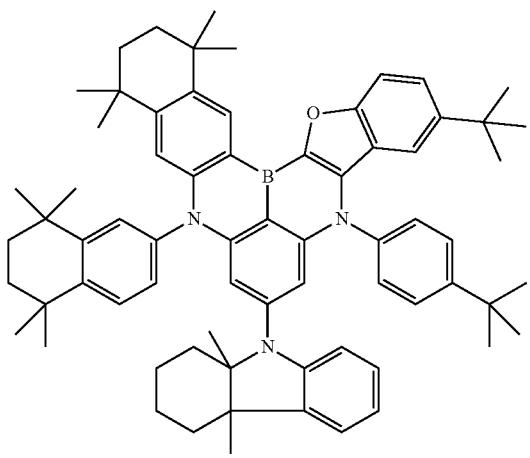
628
-continued
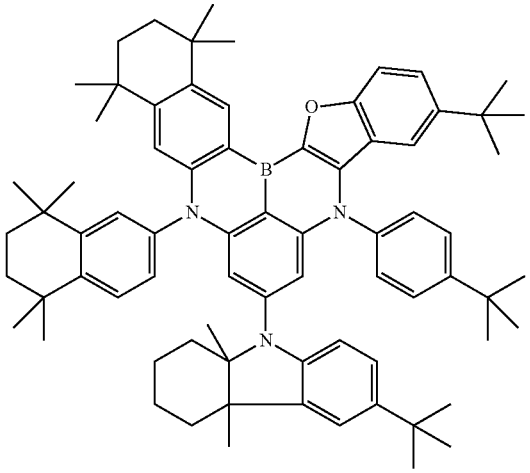
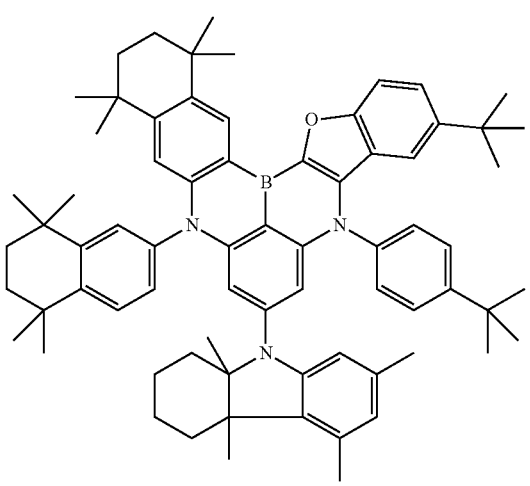
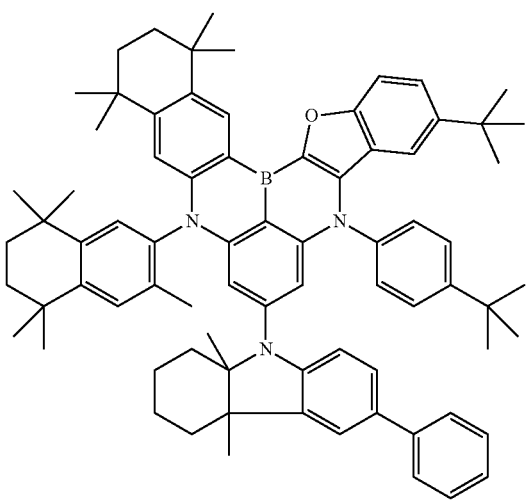

629 -continued
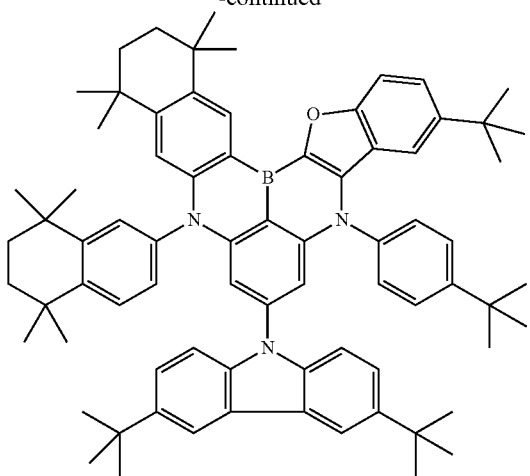
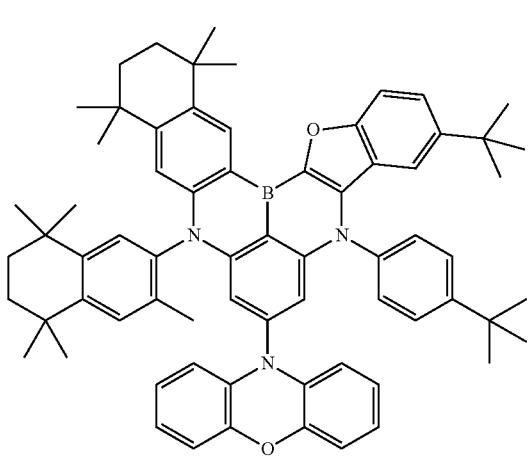
630 -continued
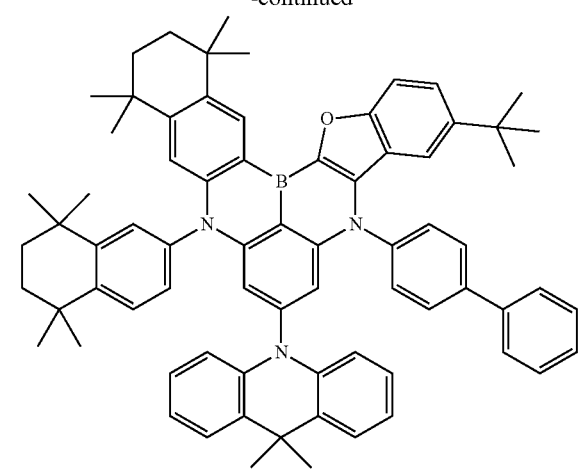
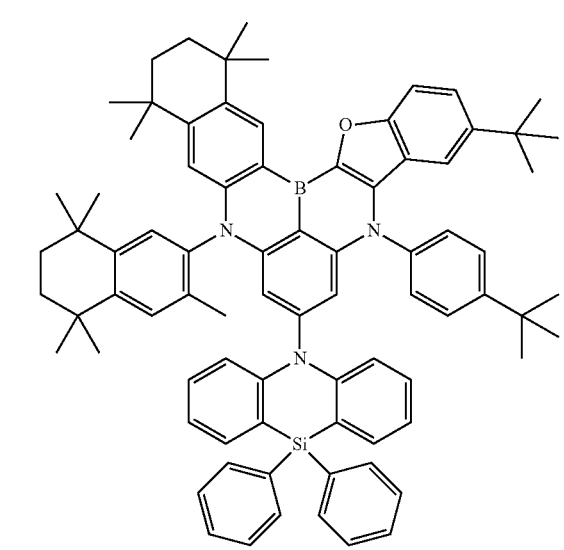

631
-continued
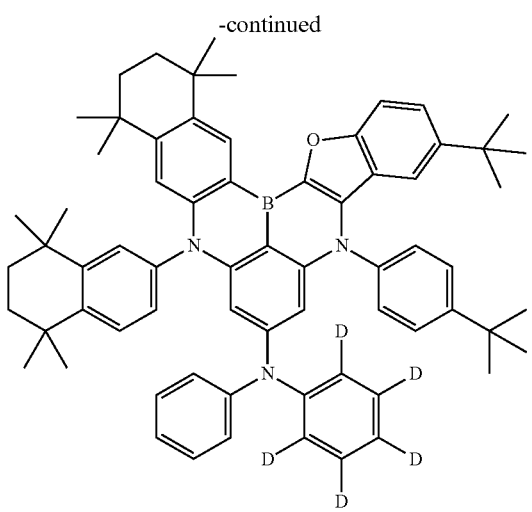
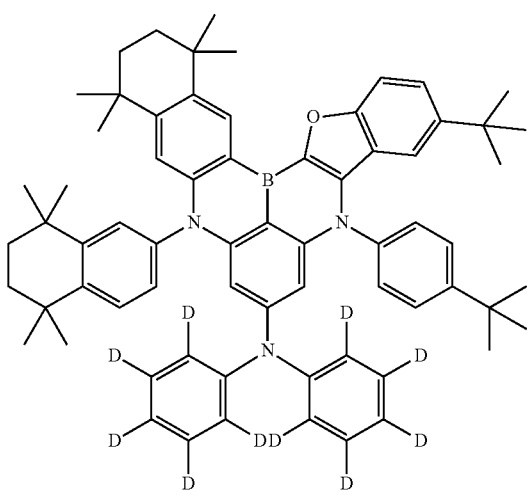
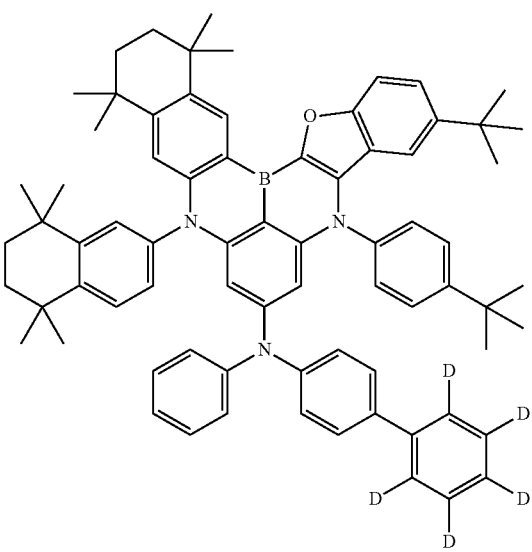
632
-continued
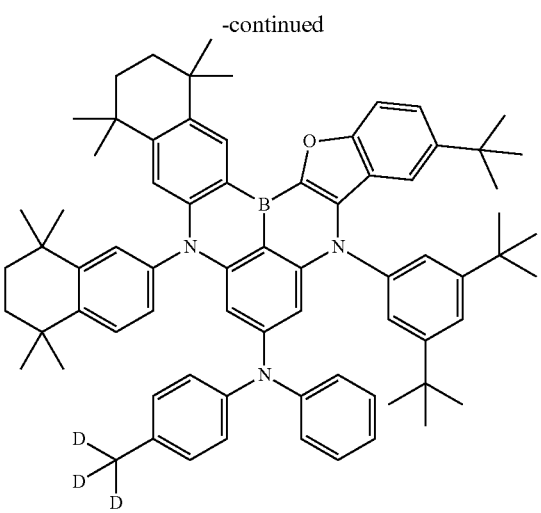
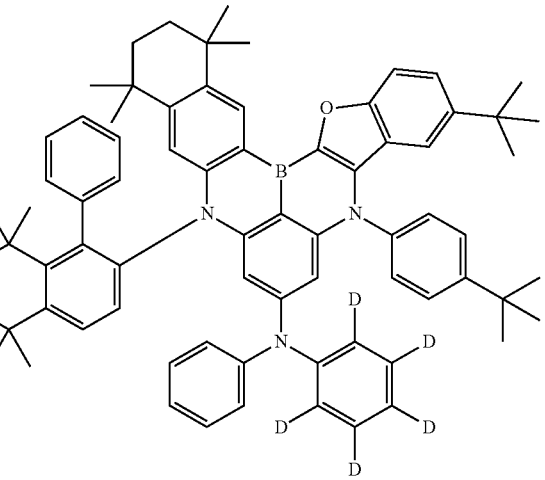
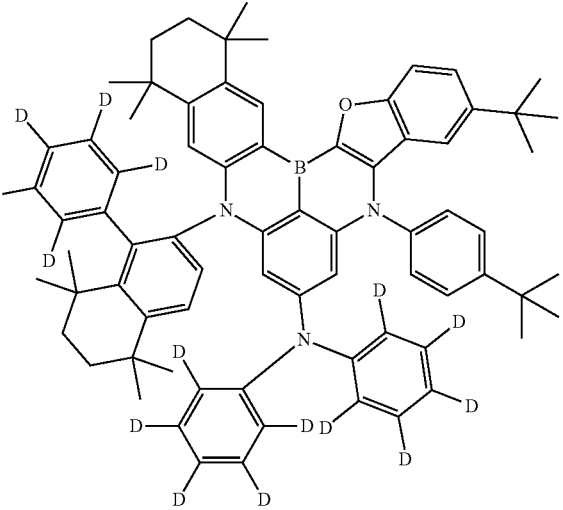

633
-continued
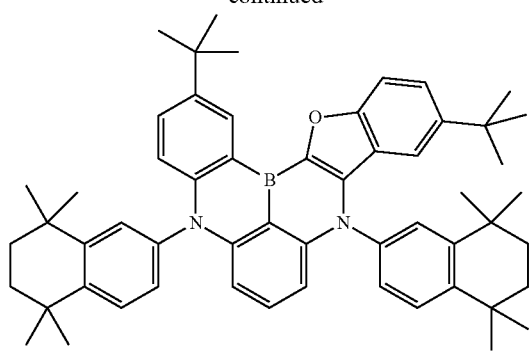
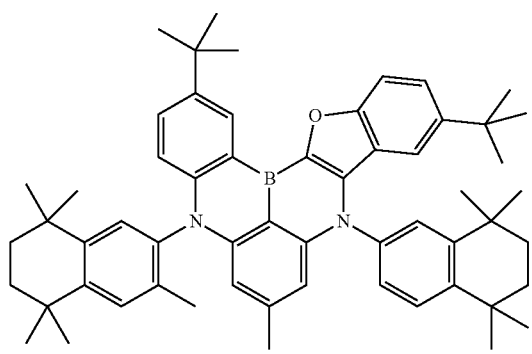
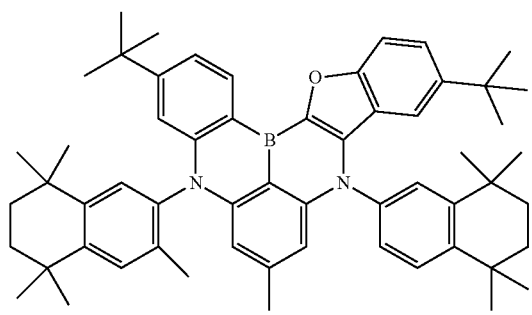
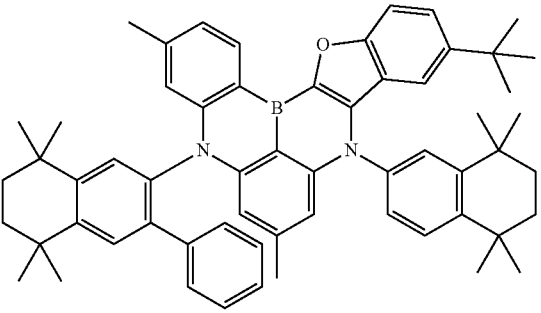
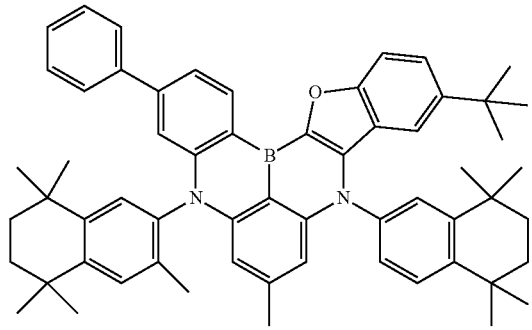
634
-continued
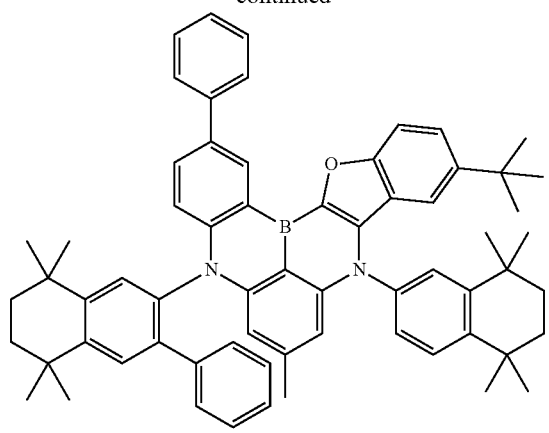
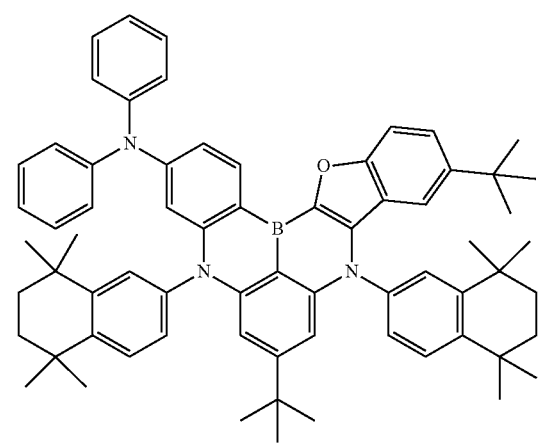
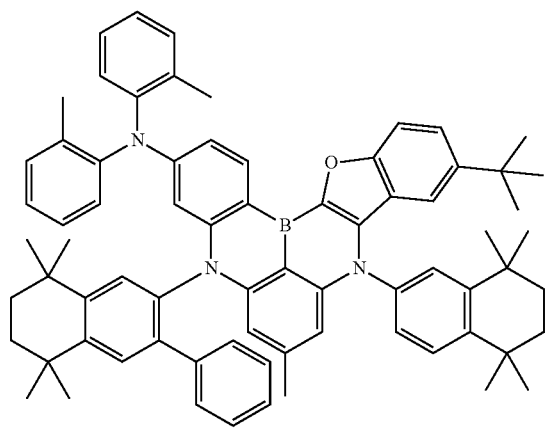
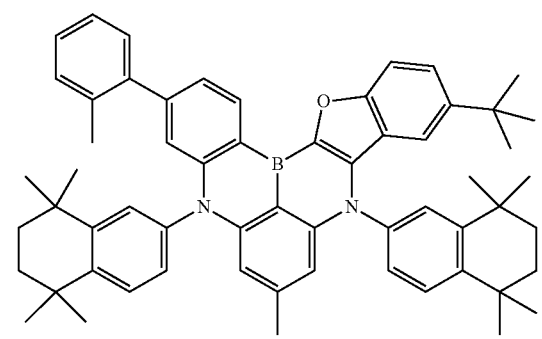

635
-continued
636
-continued
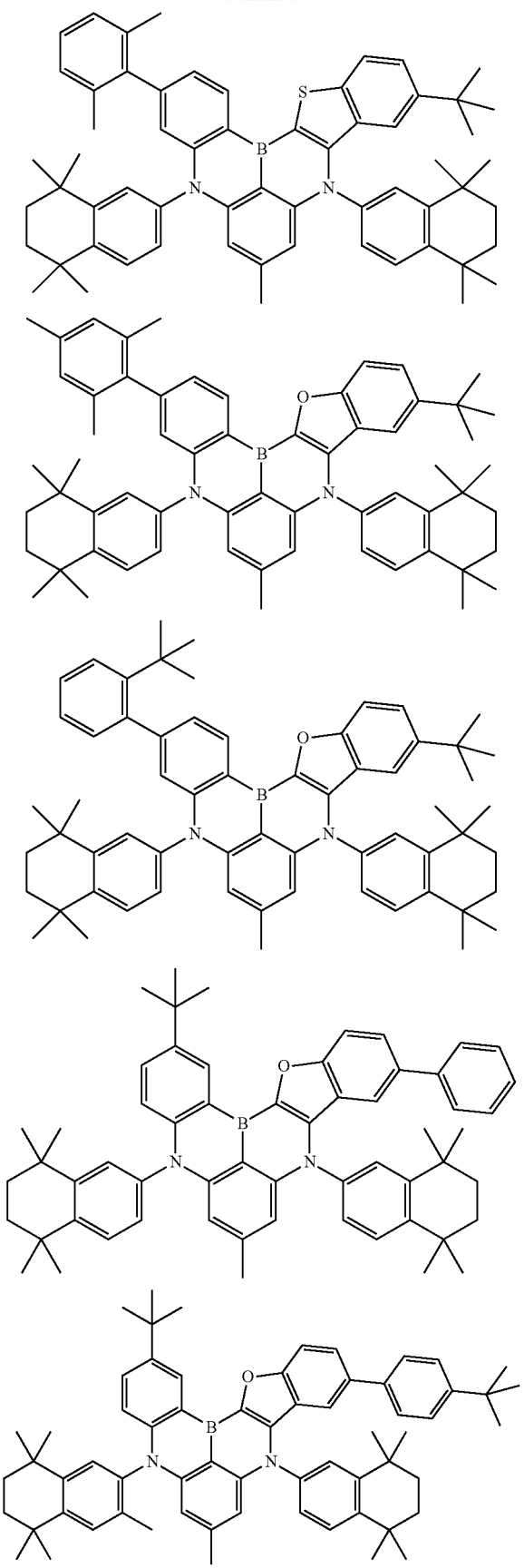
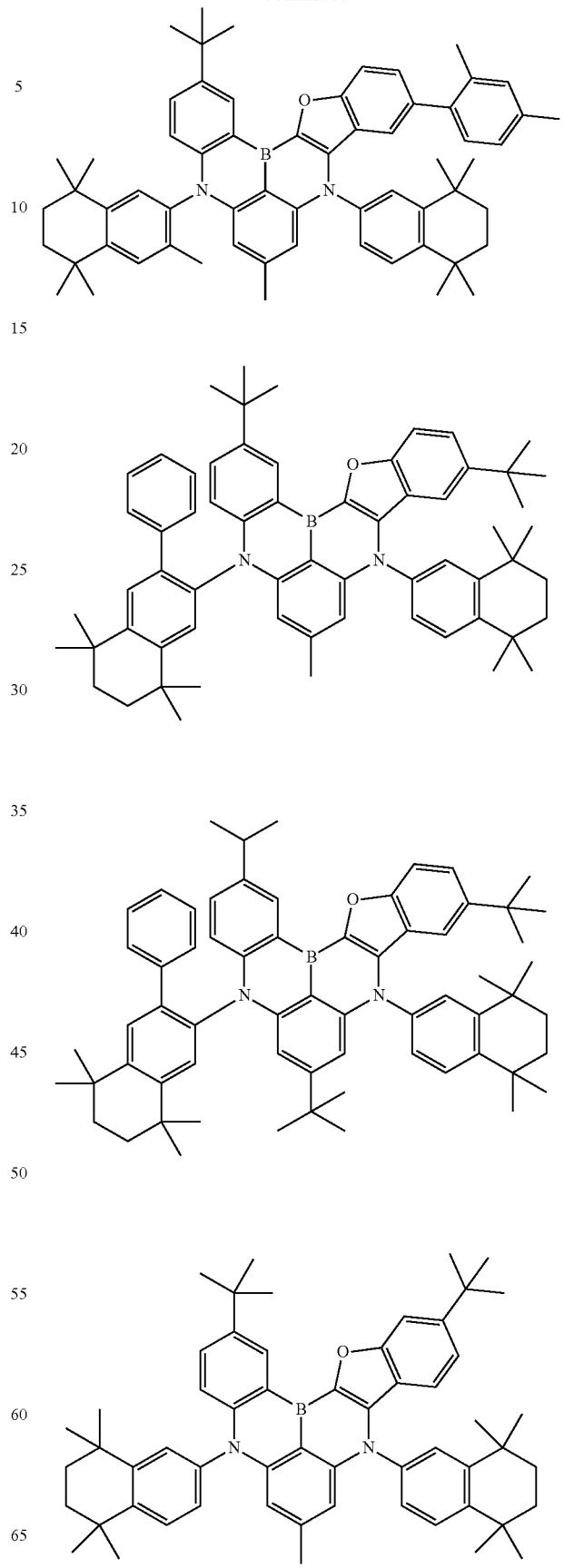

637
-continued
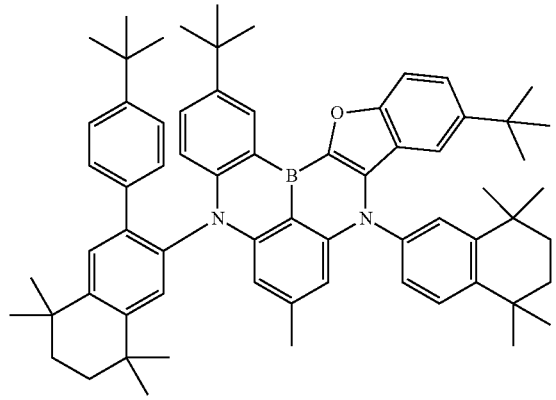
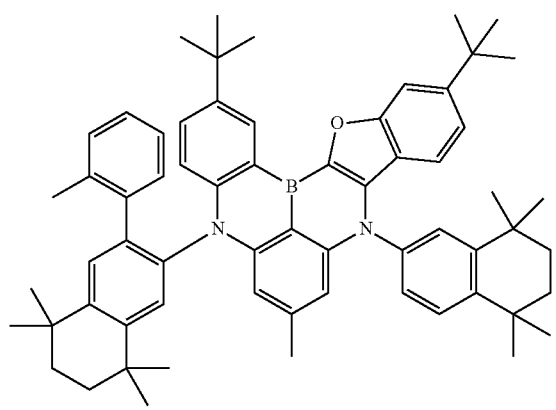
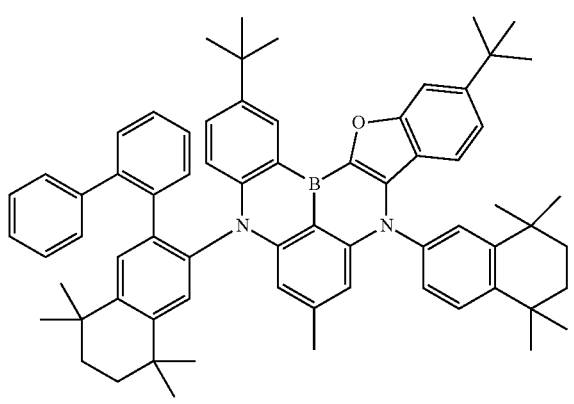
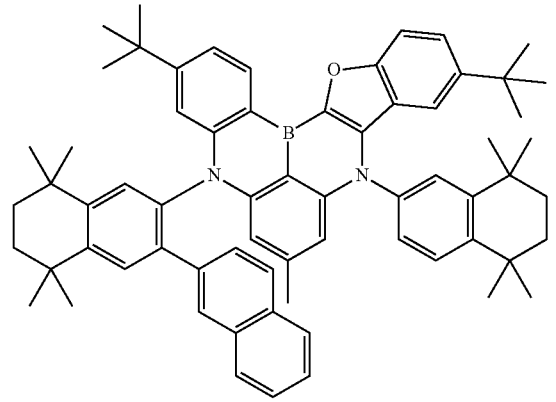
638
-continued
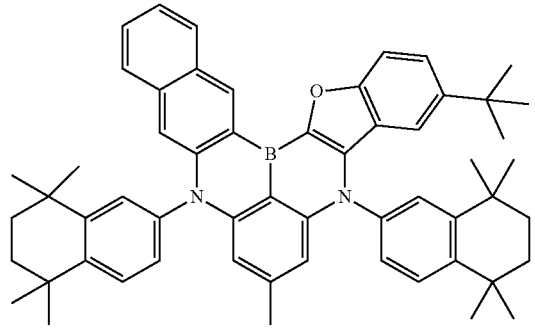
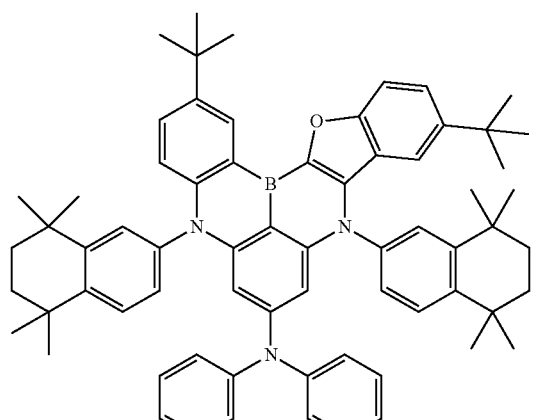
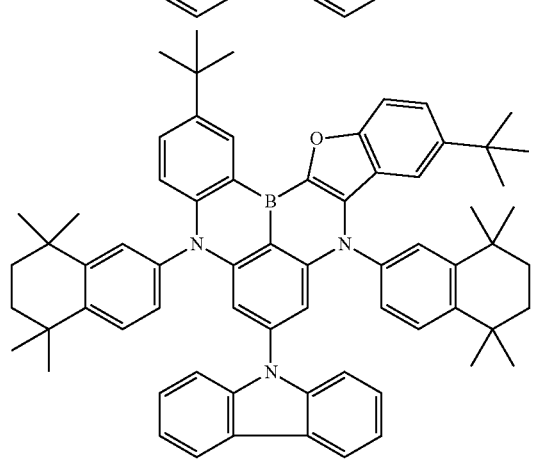
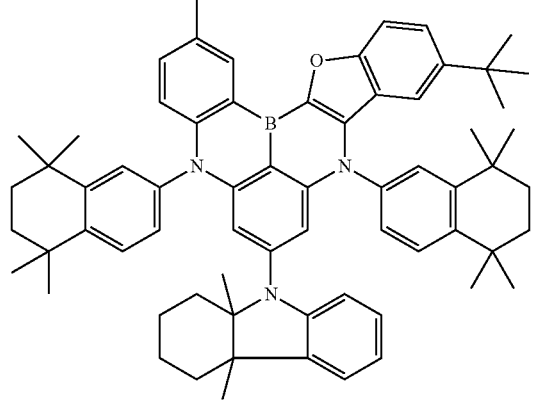

639
-continued
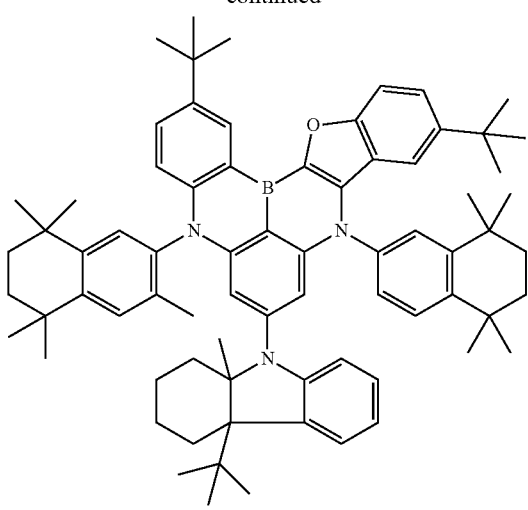
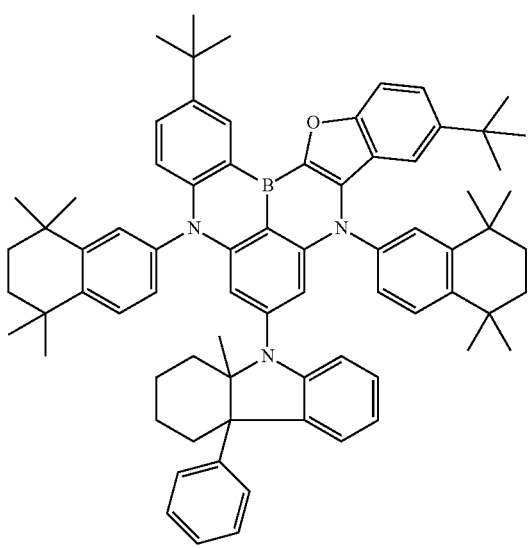
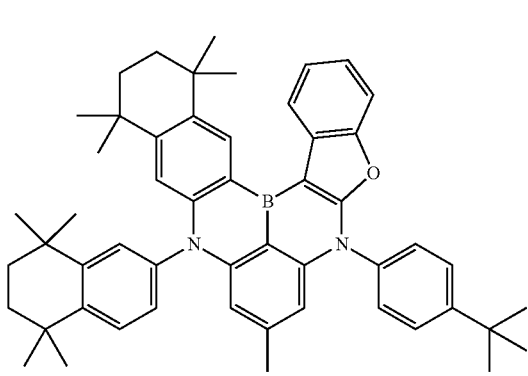
640
-continued
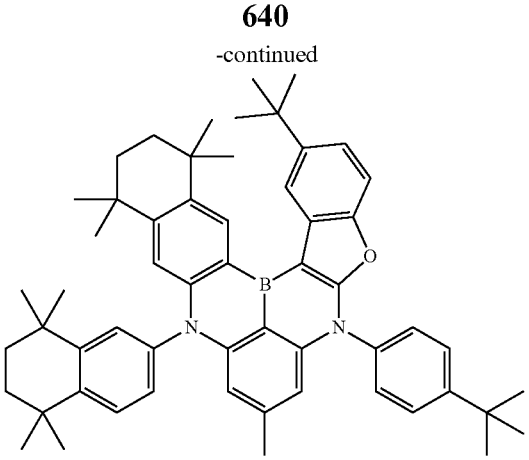
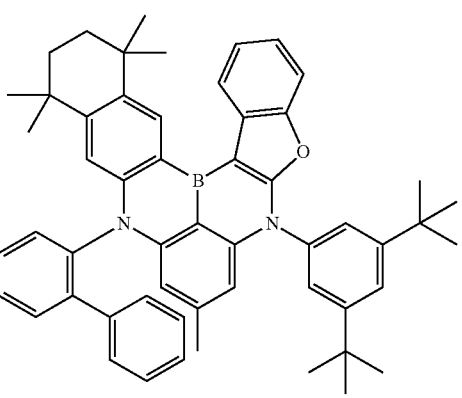

641
-continued
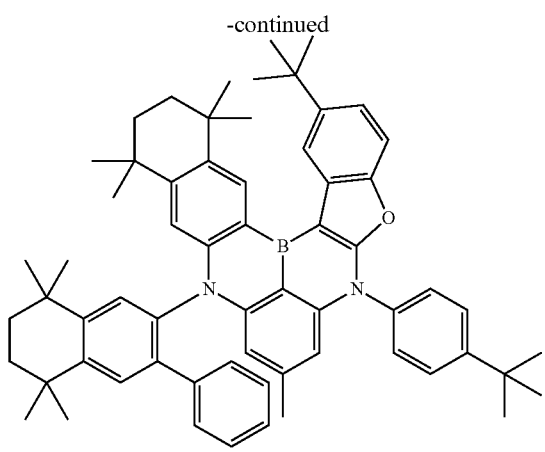
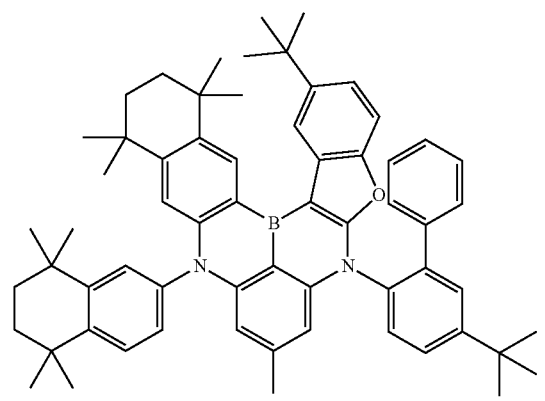
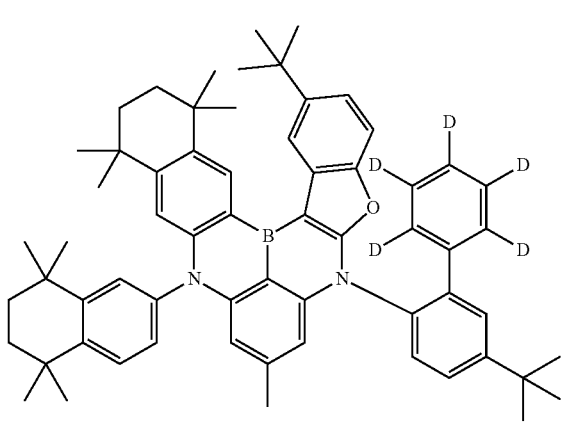
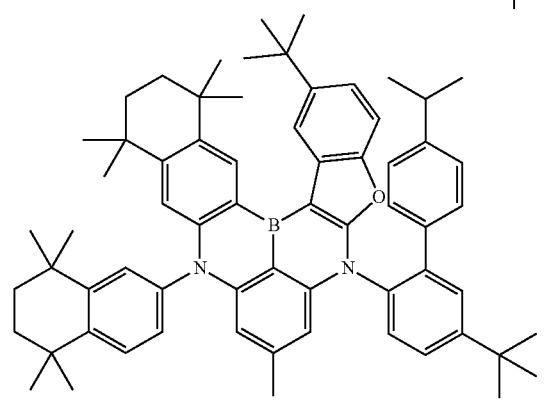
642
-continued
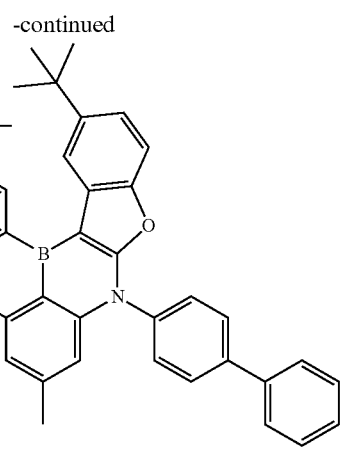
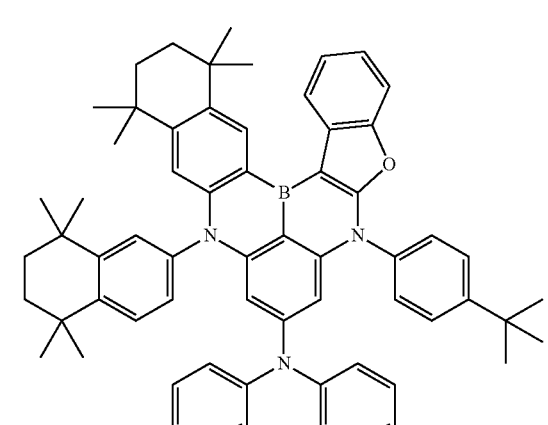
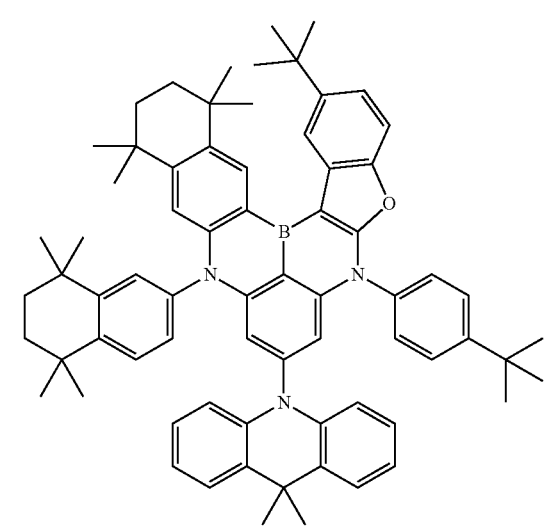

643
-continued
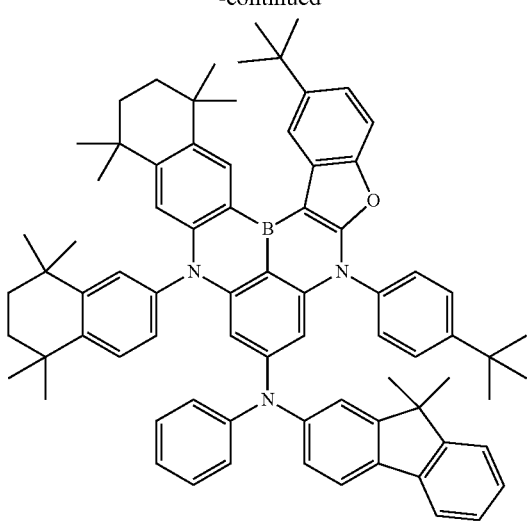
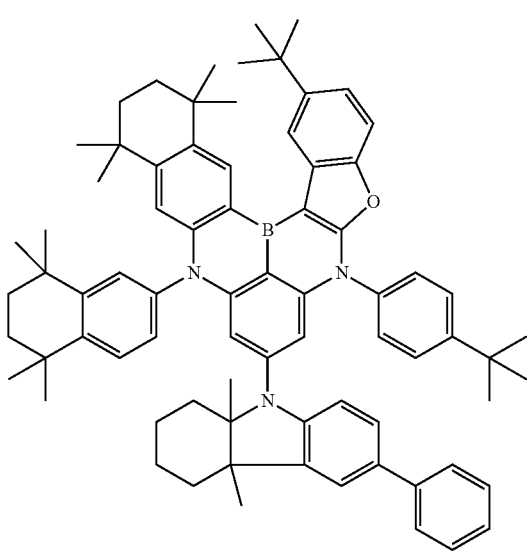
644
-continued
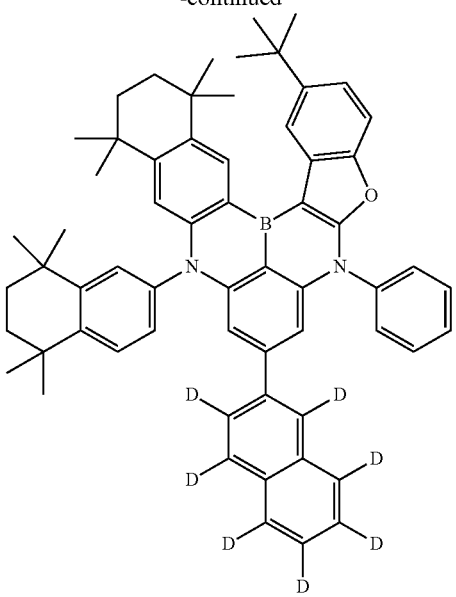
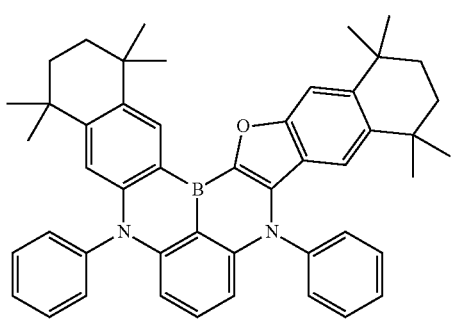
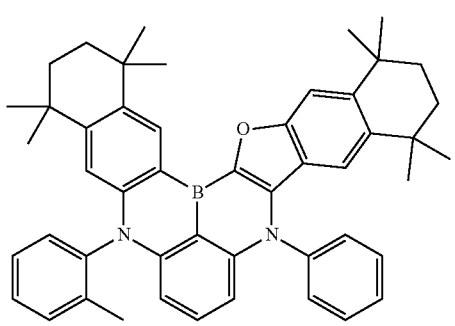
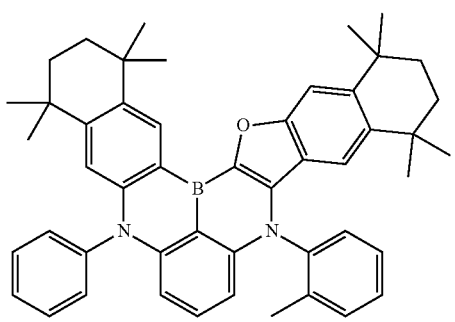

645
-continued
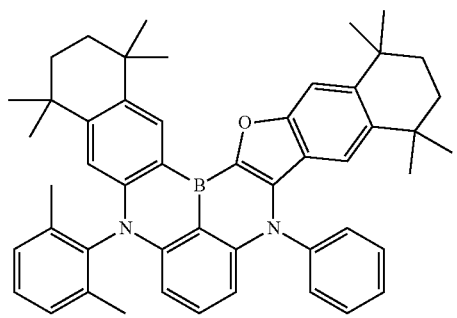
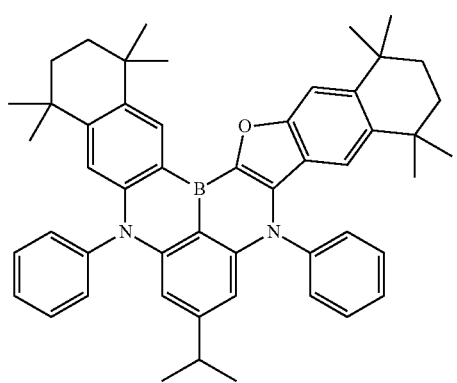
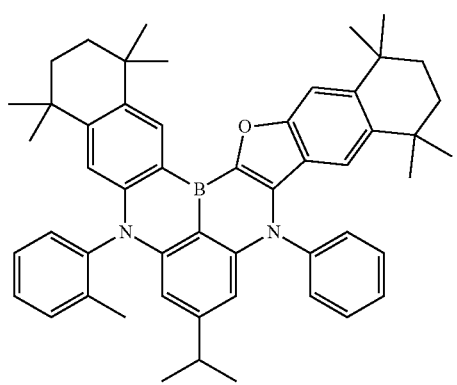
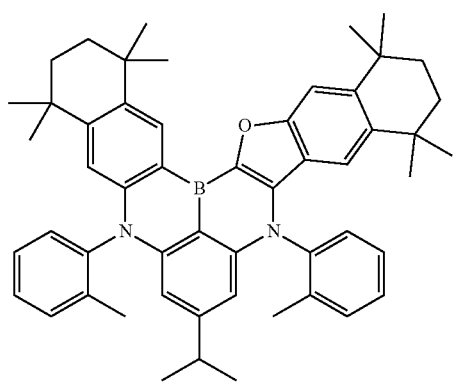
646
-continued
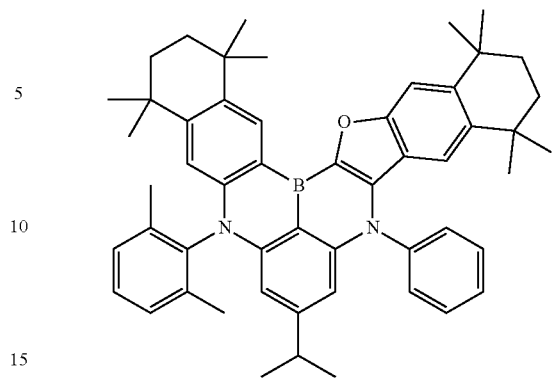
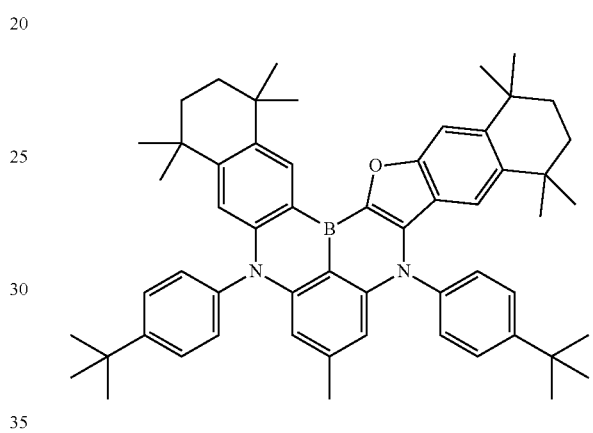
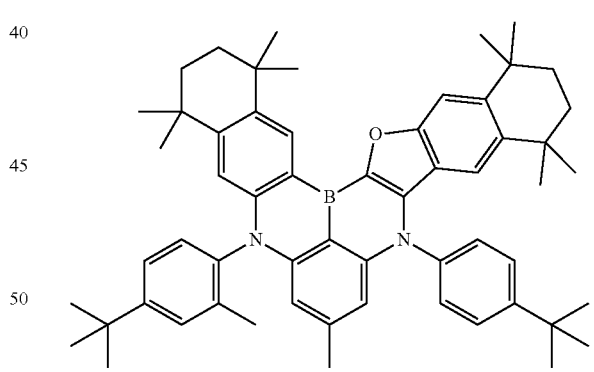
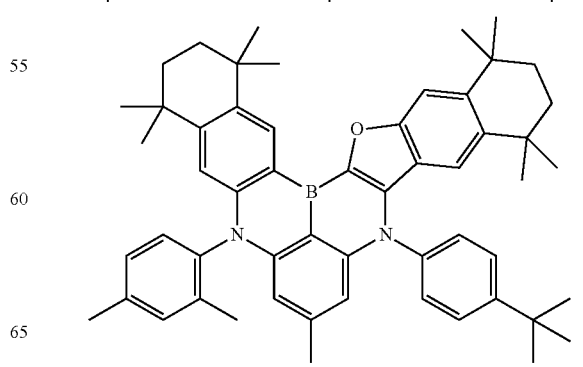

647
-continued
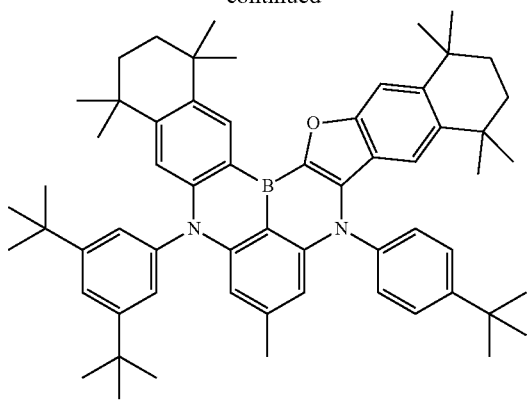
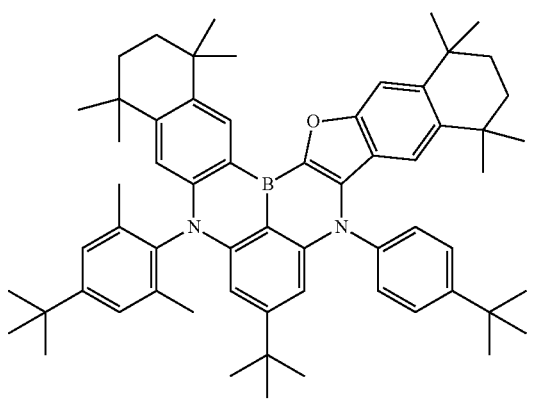
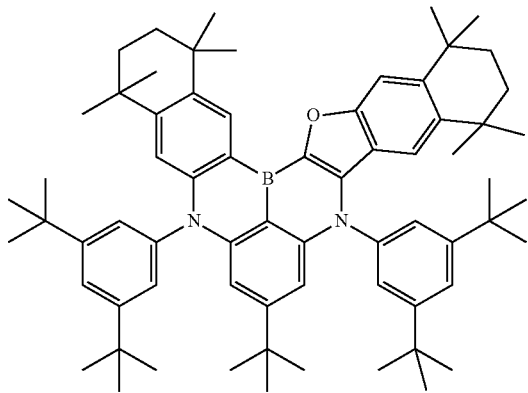
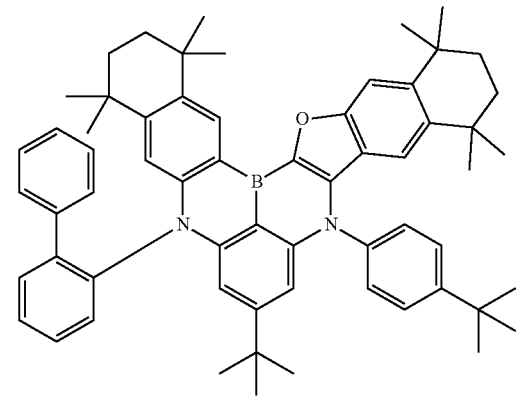
648
-continued
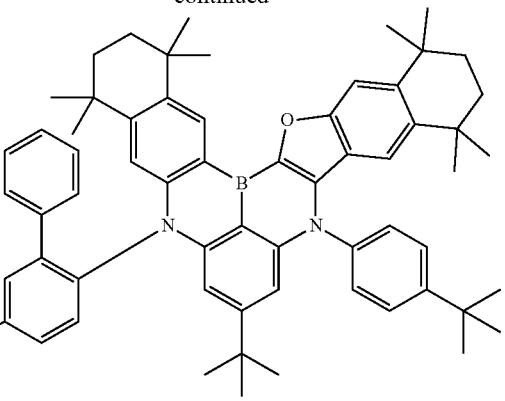
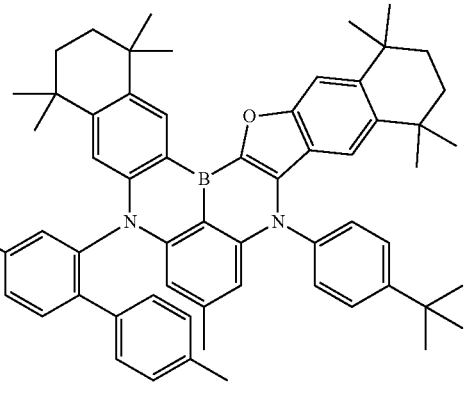
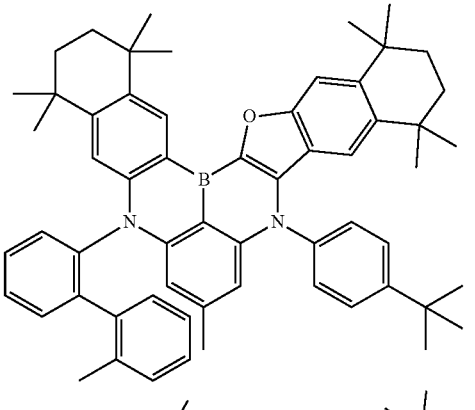
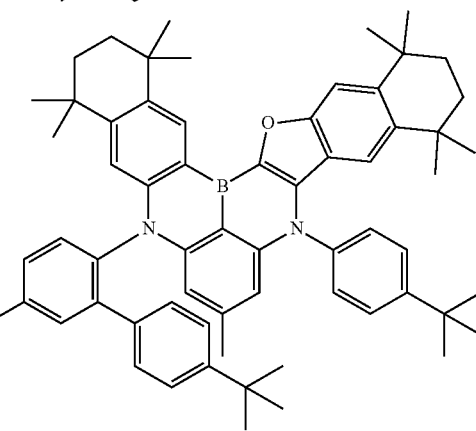

| 649 -continued | 650 -continued |
|---|---|
| 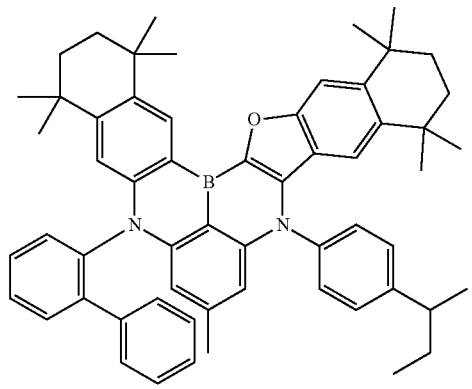 | 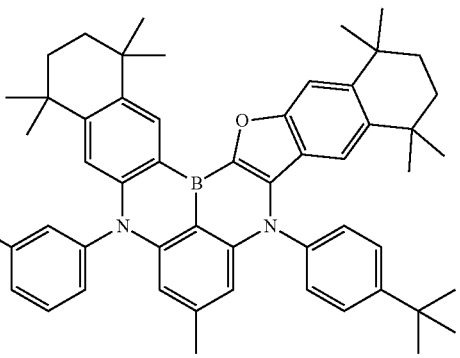 |
| 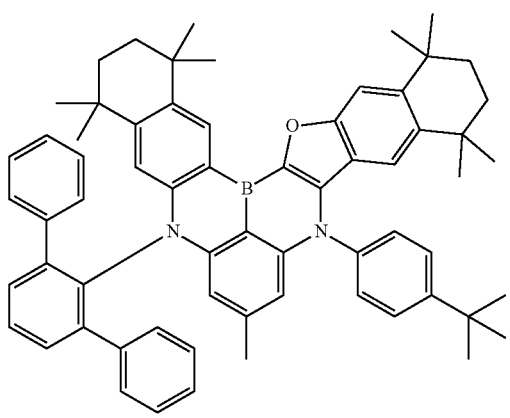 | 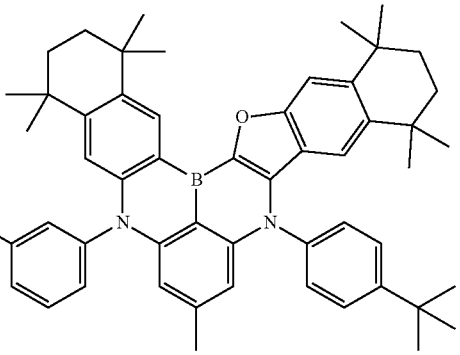 |
| 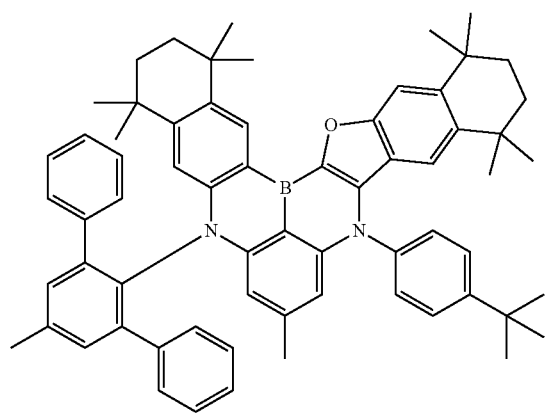 | 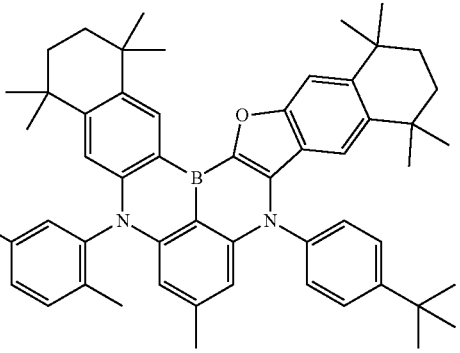 |
| 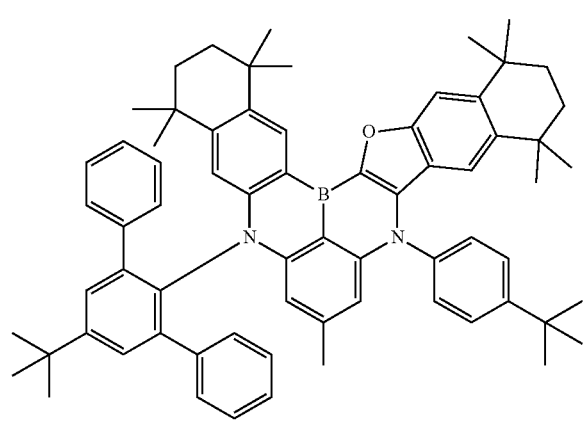 | 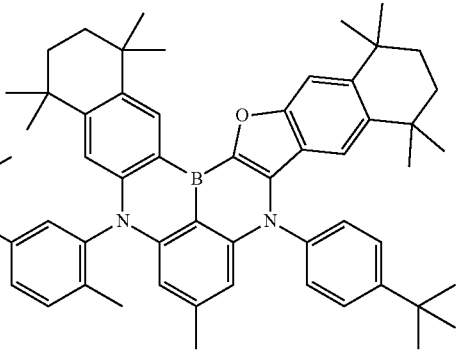 |

651
-continued
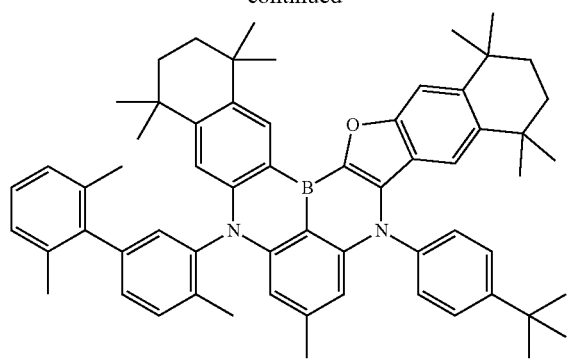
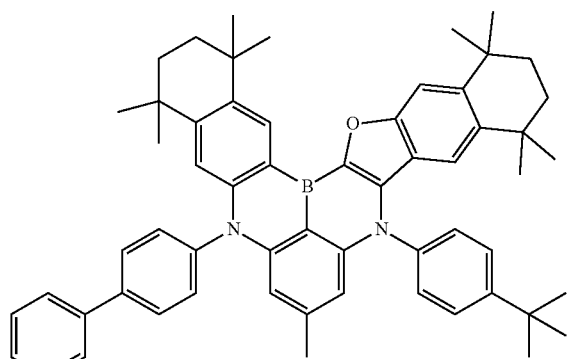

652
-continued
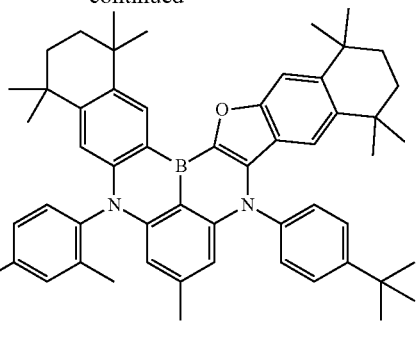
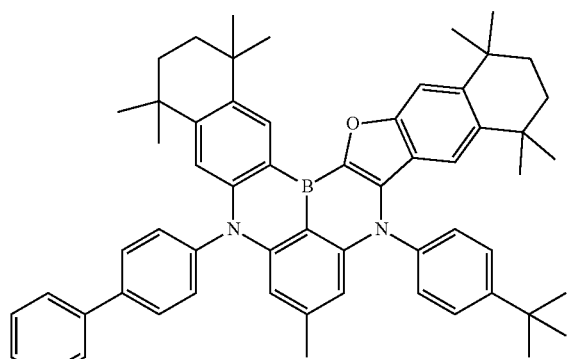
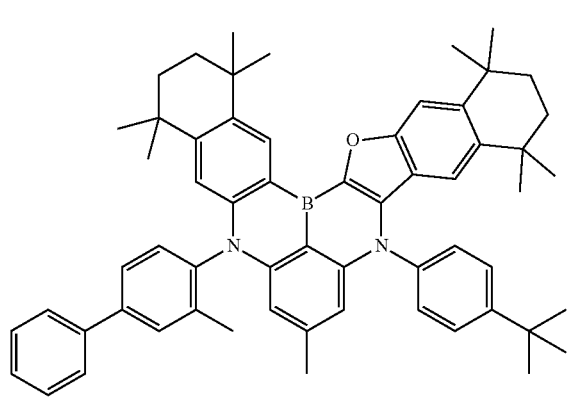

653
-continued
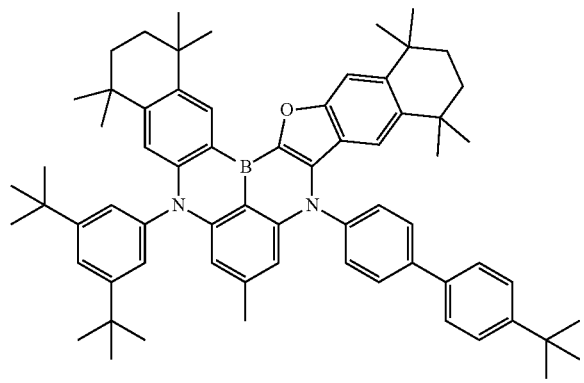
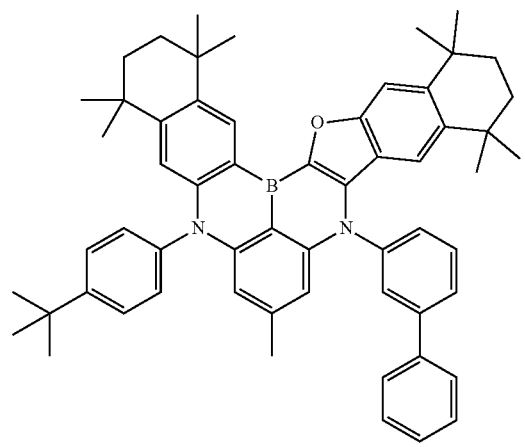
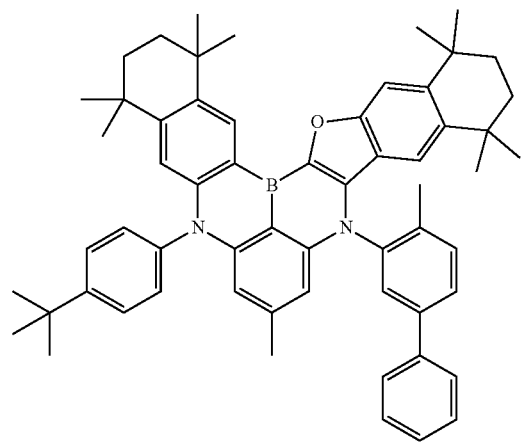
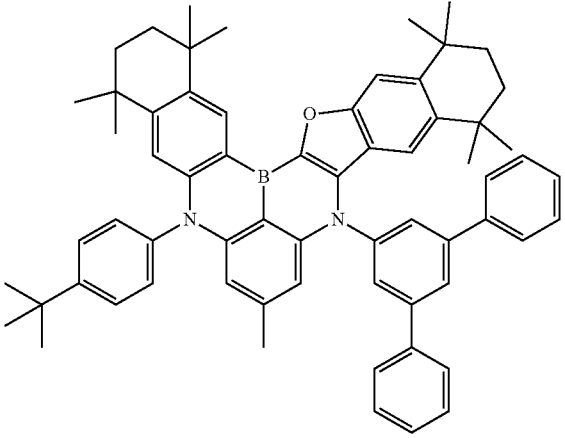
654
-continued
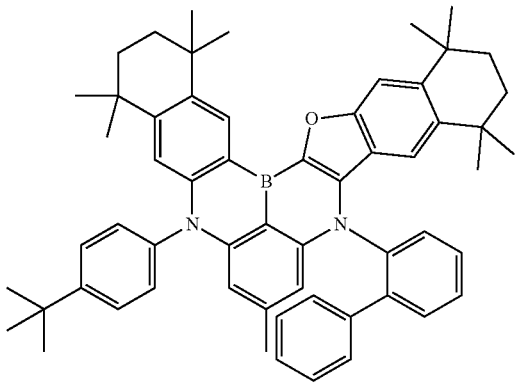
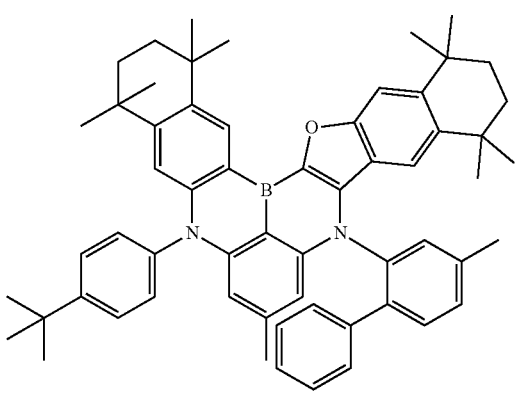
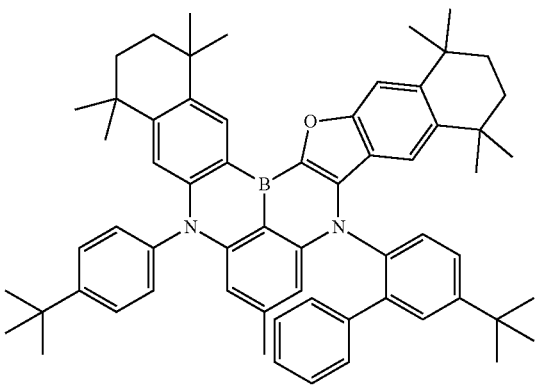
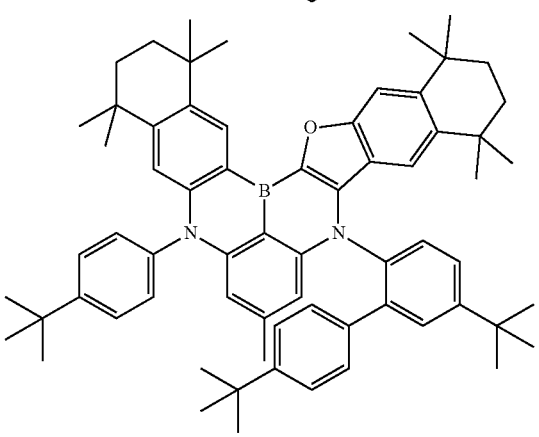

655
-continued
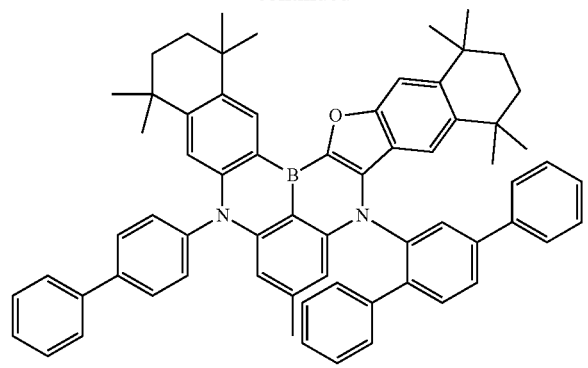
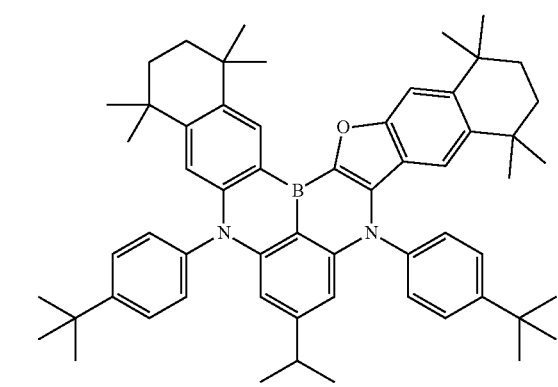
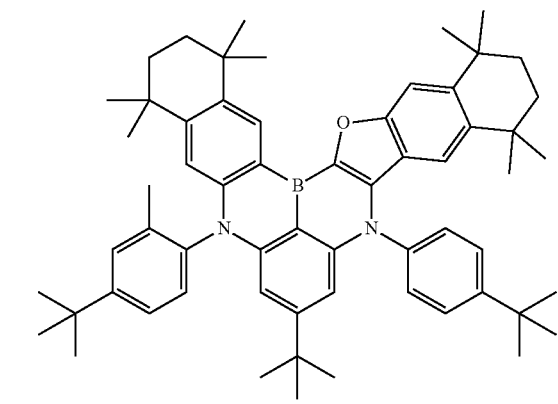
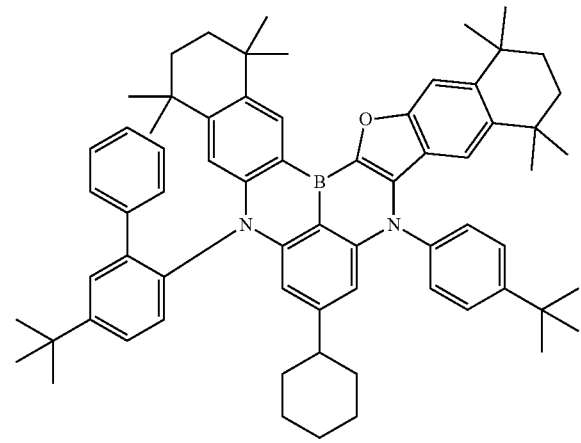
656
-continued
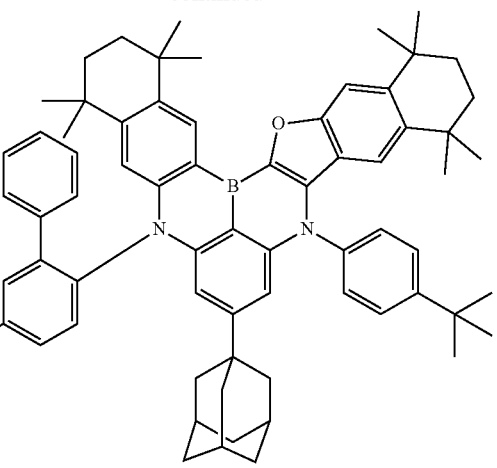
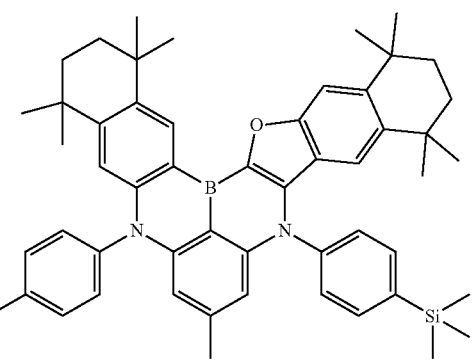

657
-continued
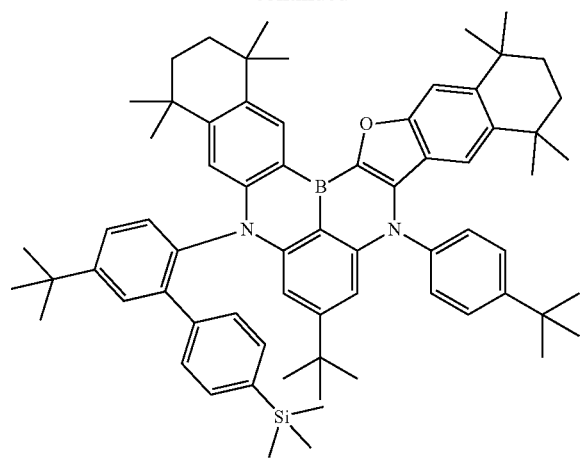
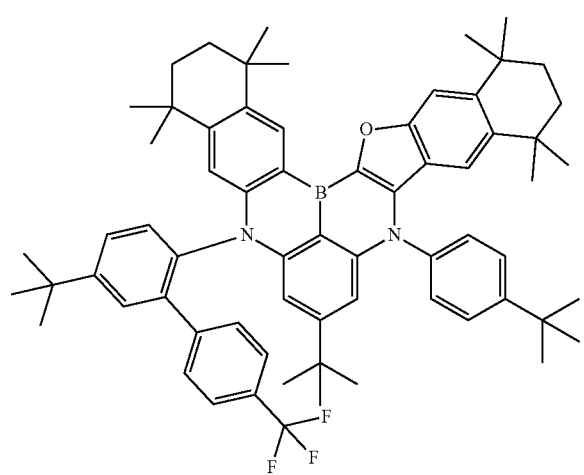
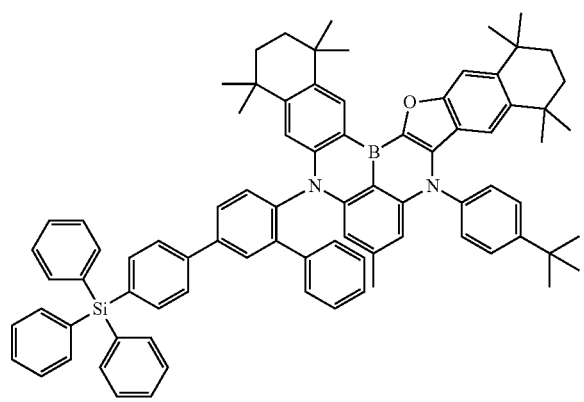
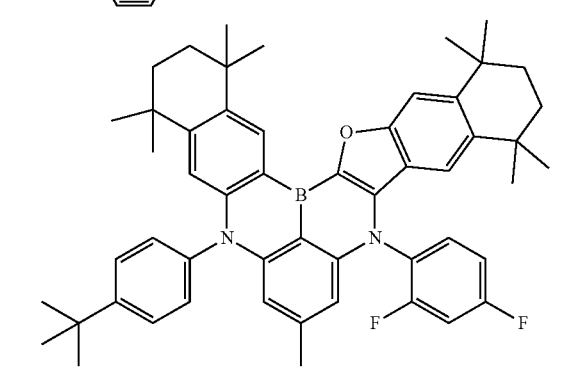
658
-continued
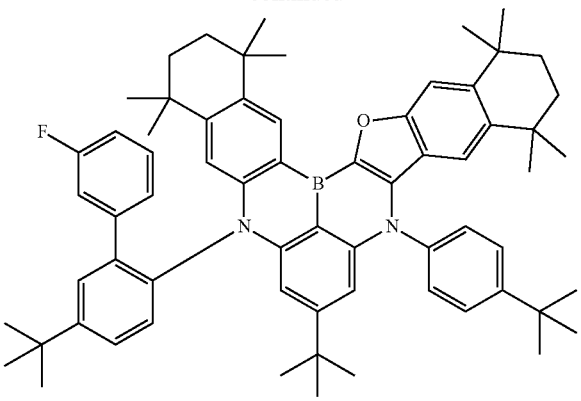
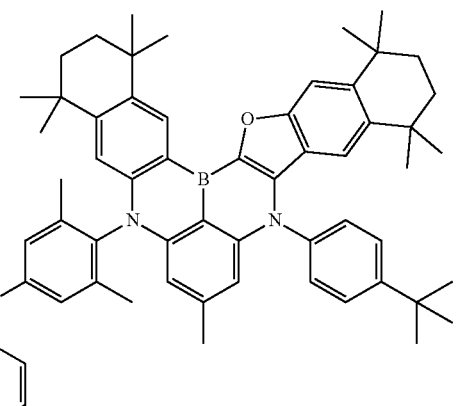
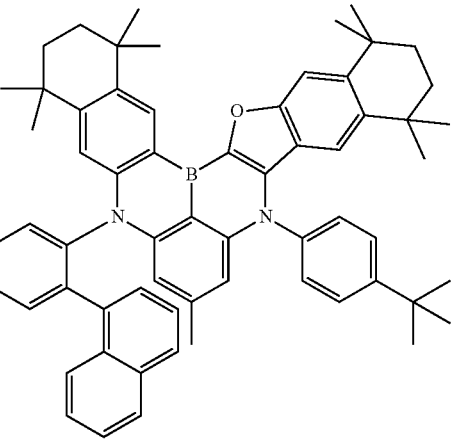
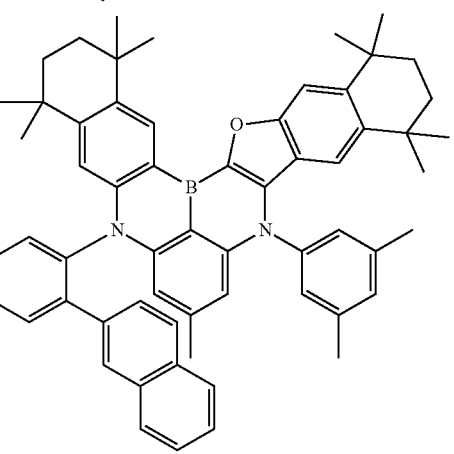

659
-continued
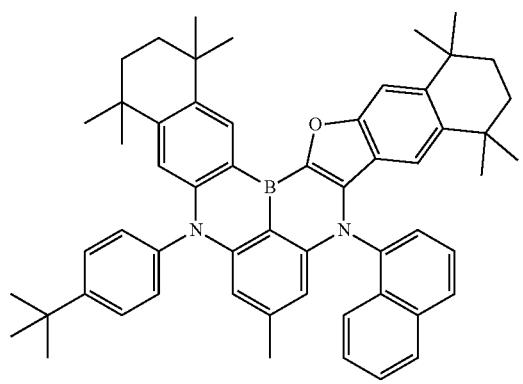
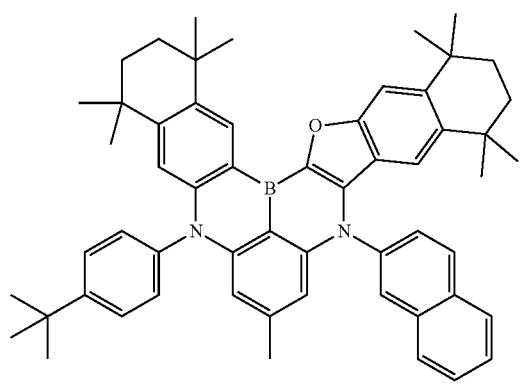
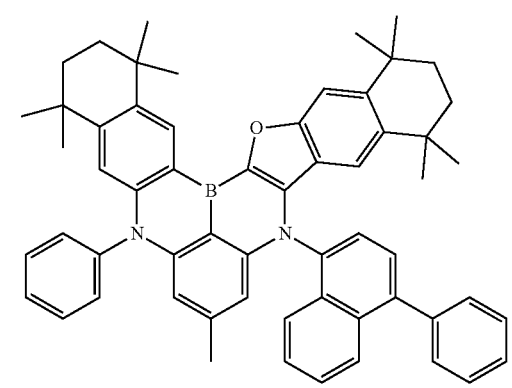
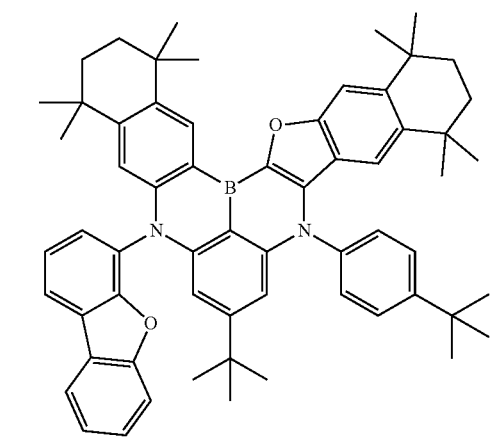
660
-continued
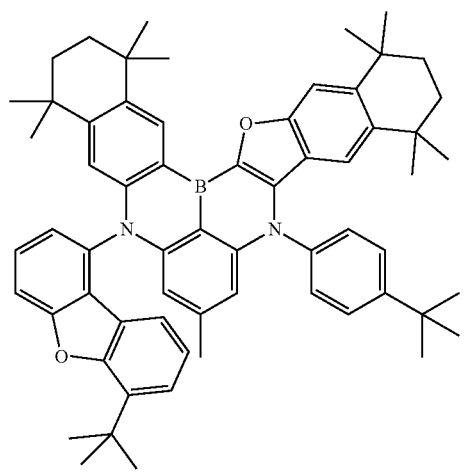
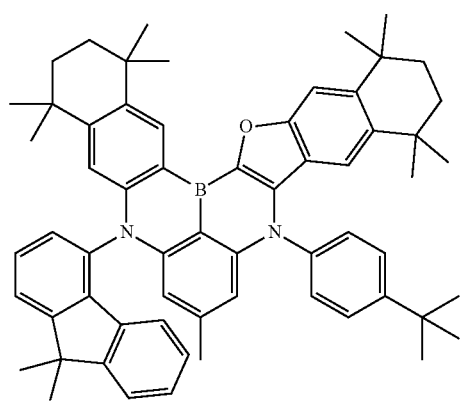
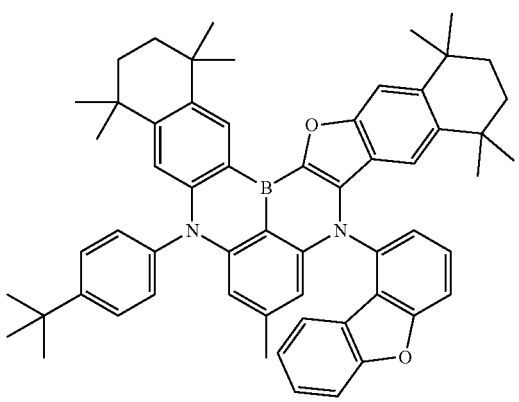
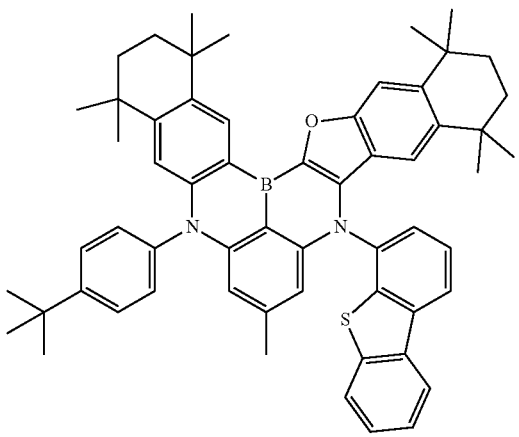

661
-continued
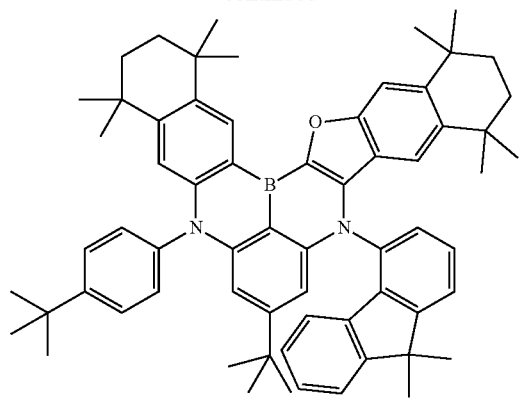
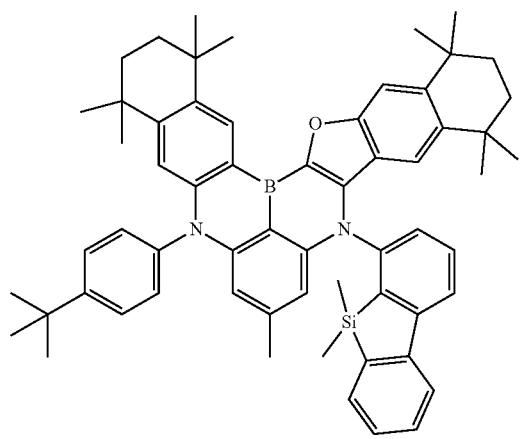
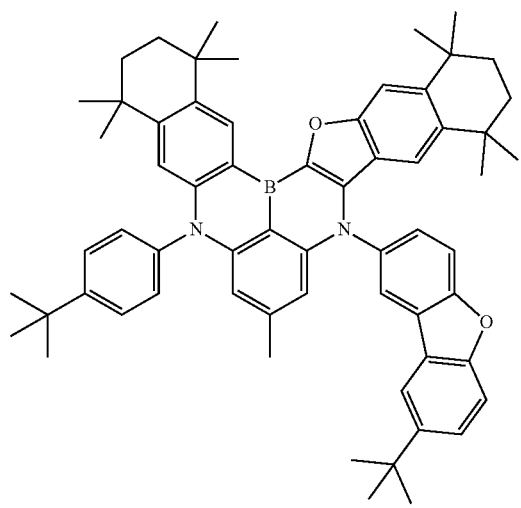
662
-continued
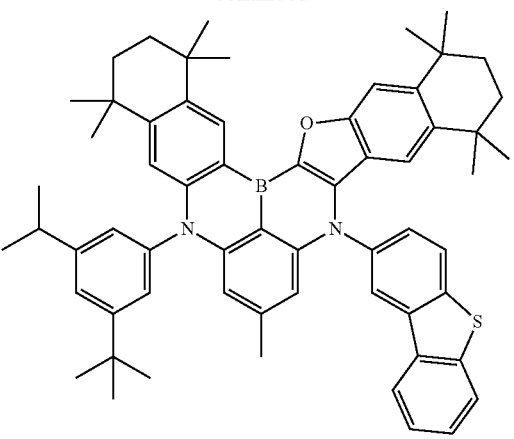
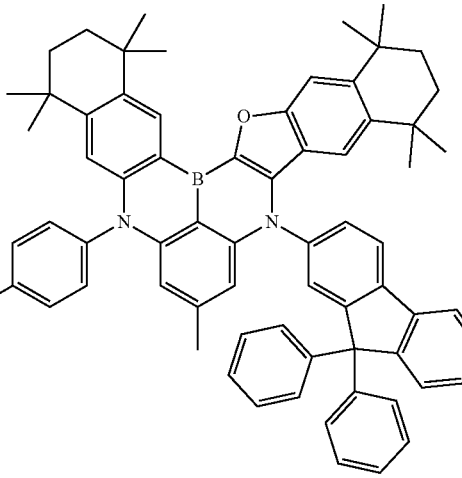
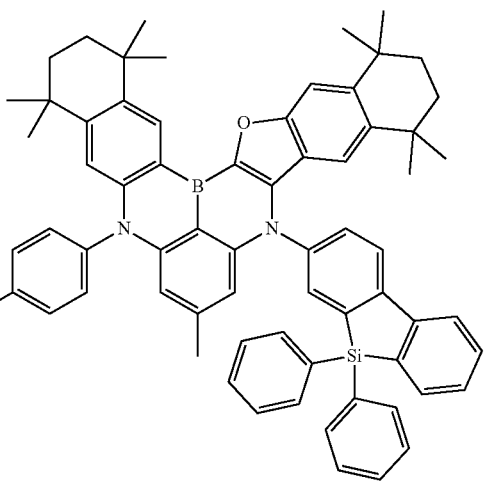

663
-continued
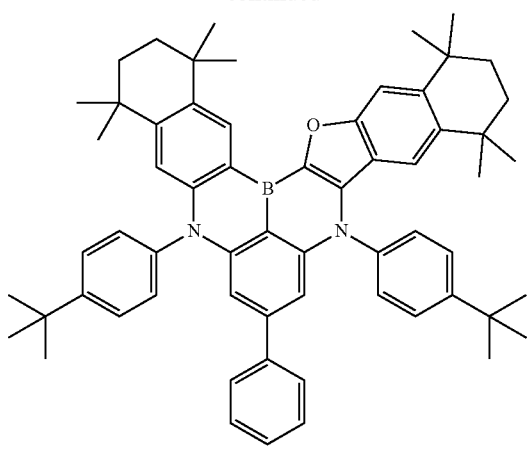
664
-continued
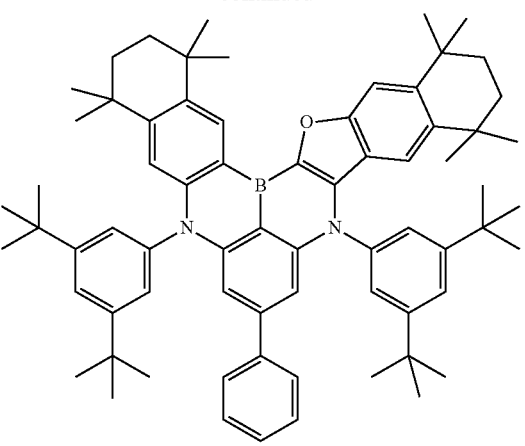
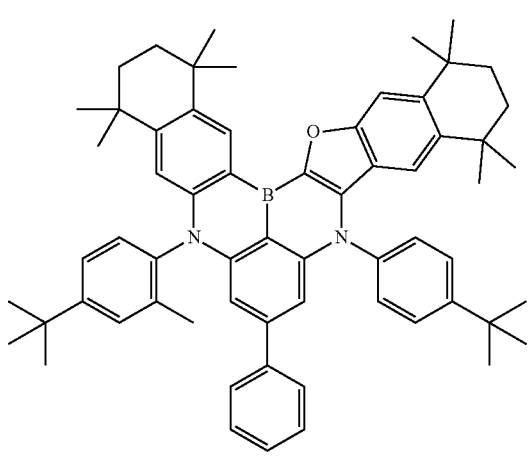
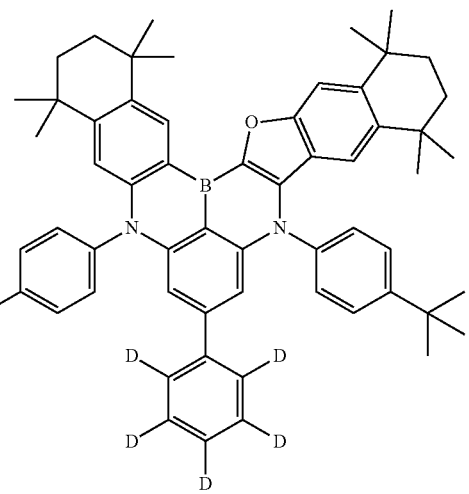
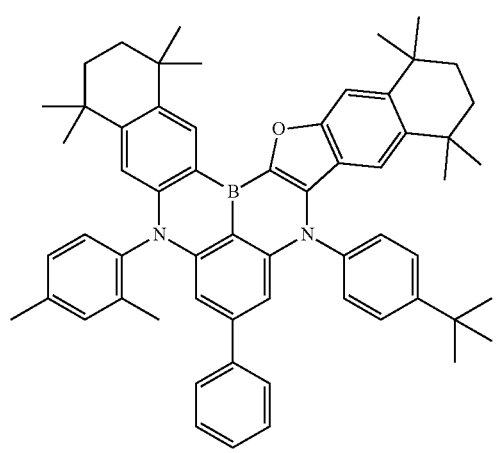
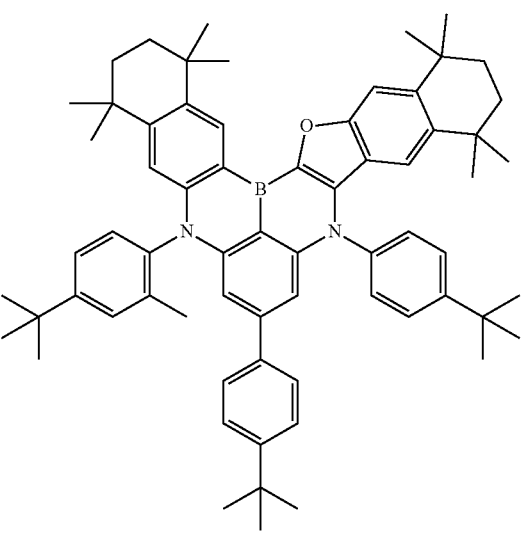

665
-continued
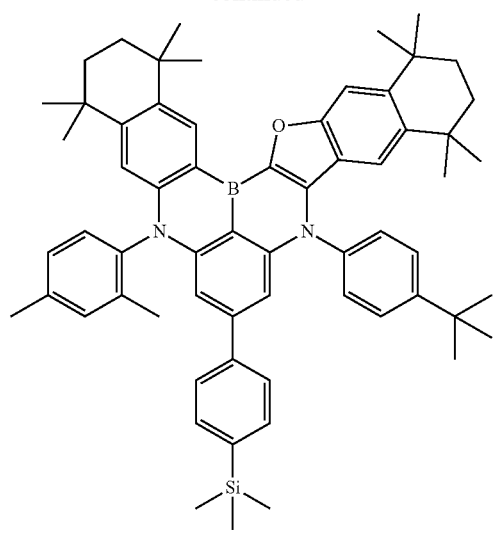
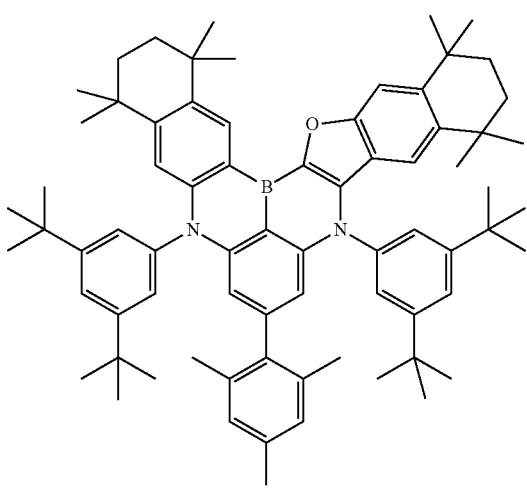
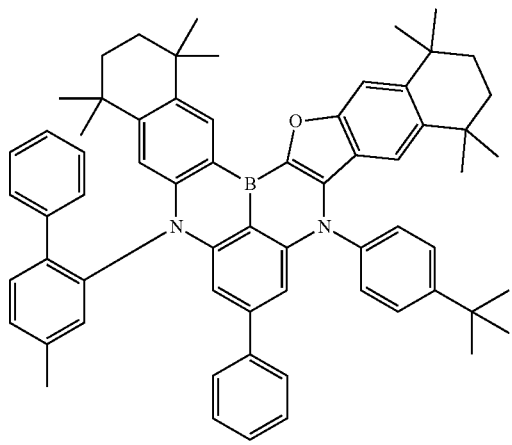
666
-continued
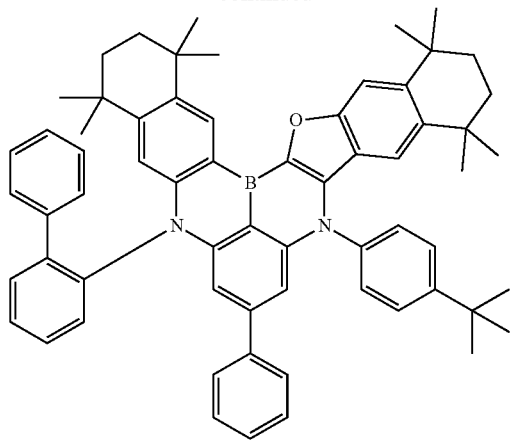
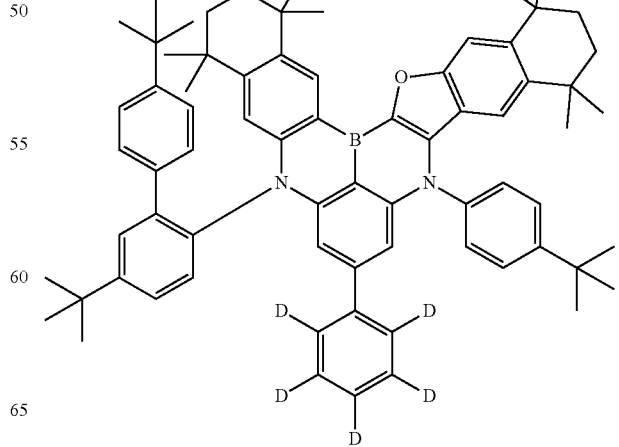

667
-continued
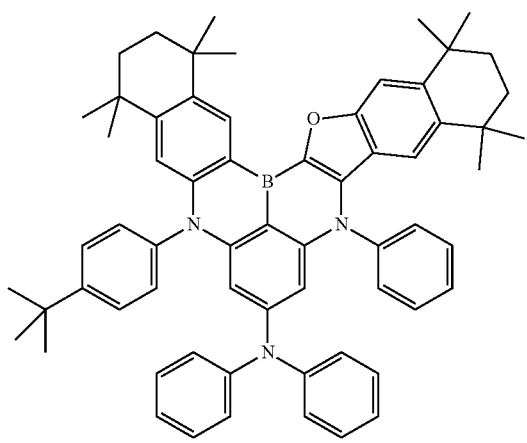
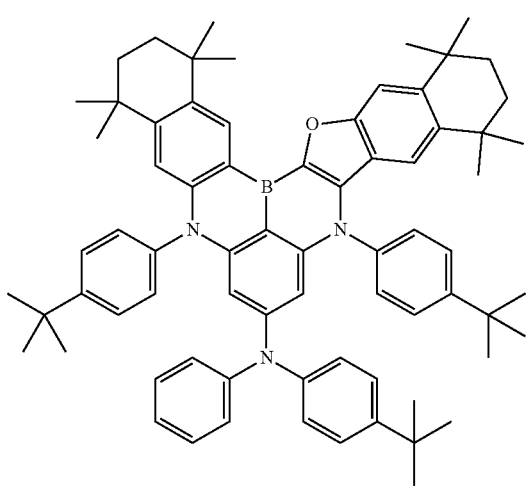
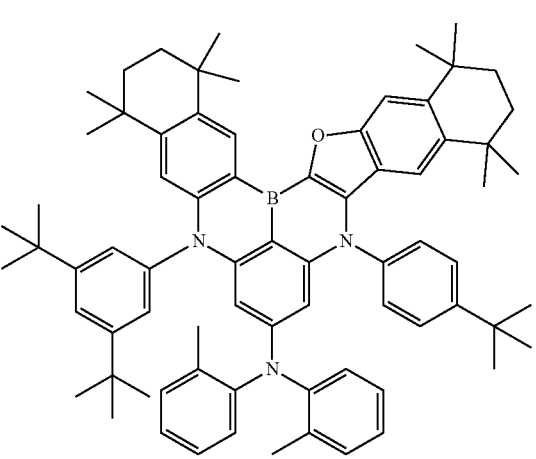
668
-continued
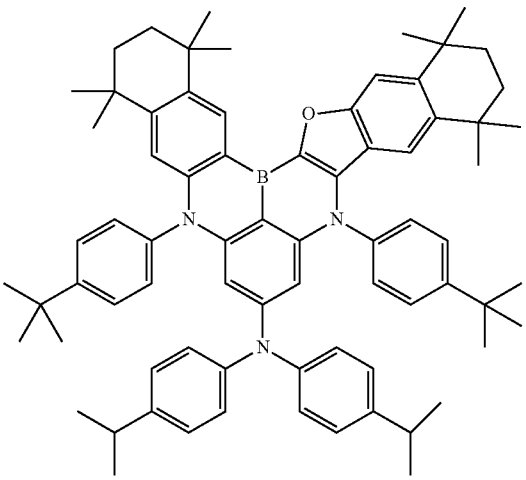
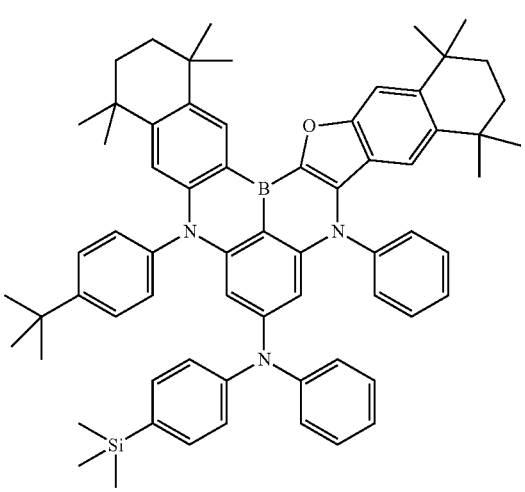
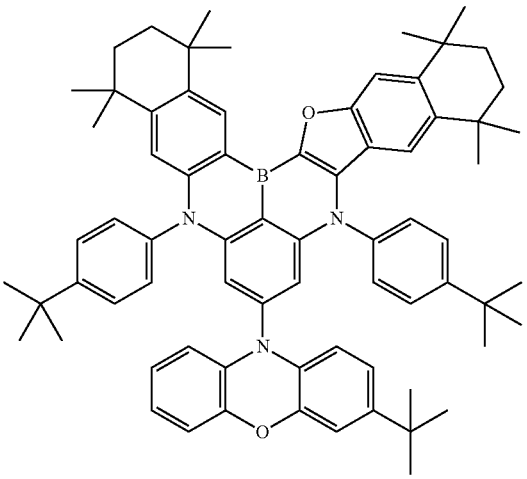

669
-continued
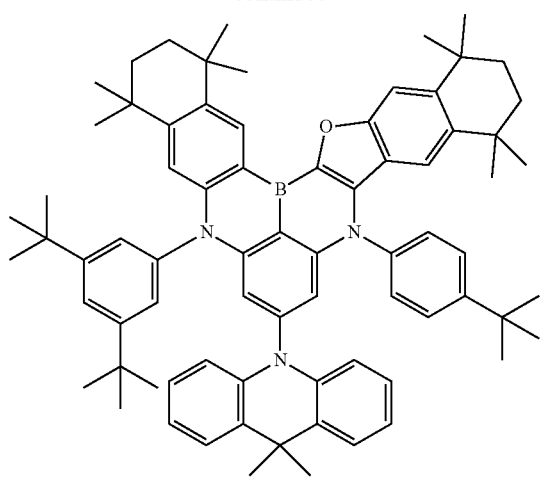
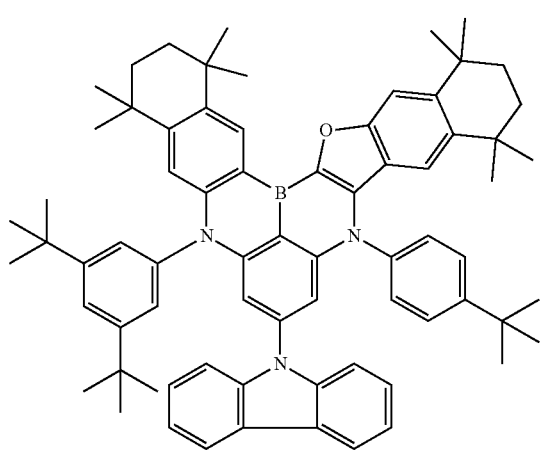
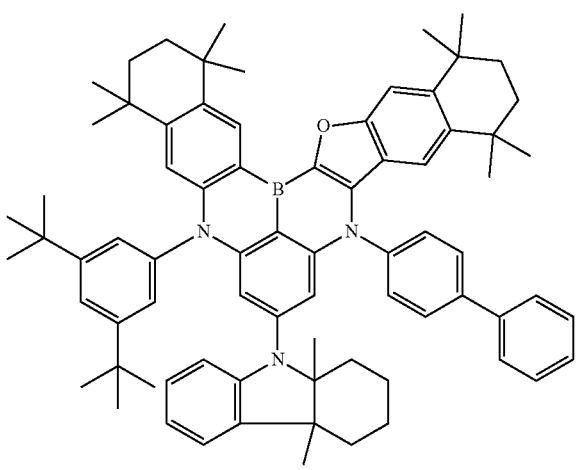
670
-continued
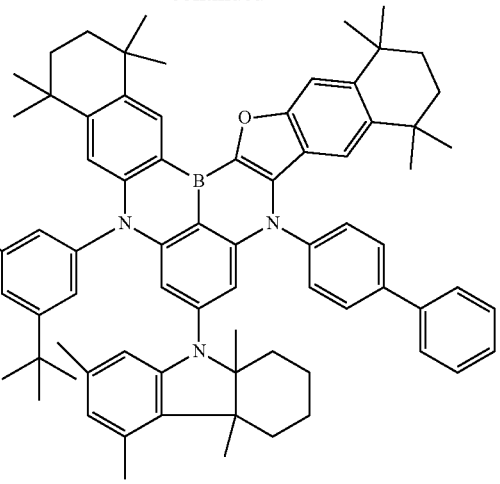
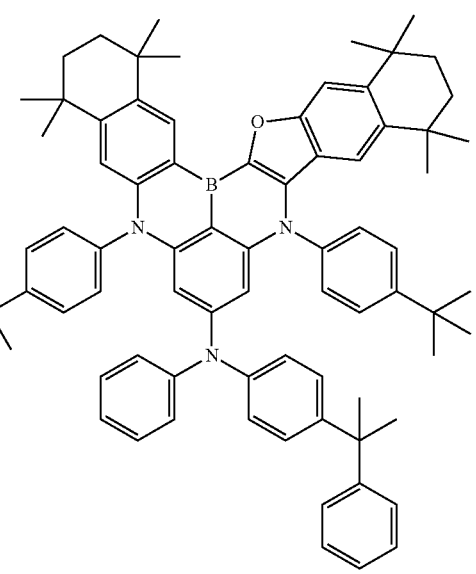
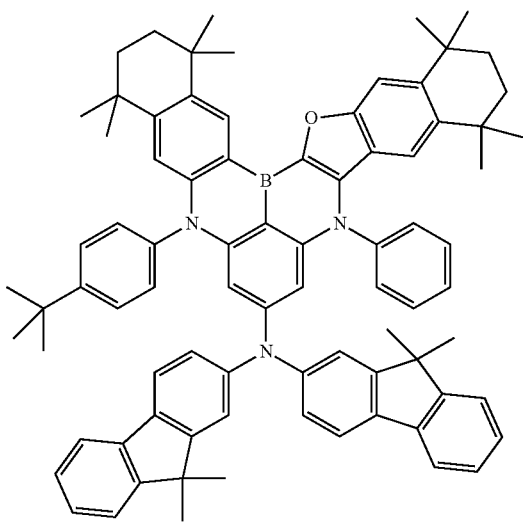

671
-continued
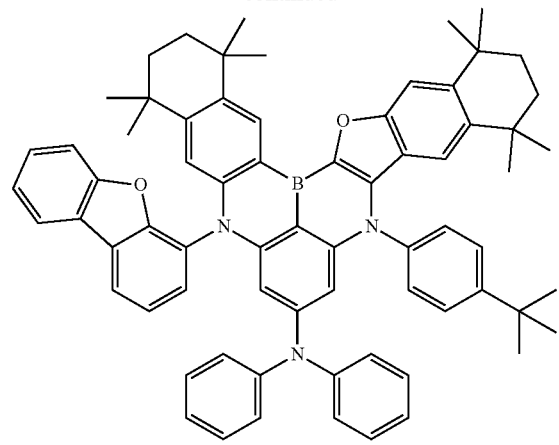
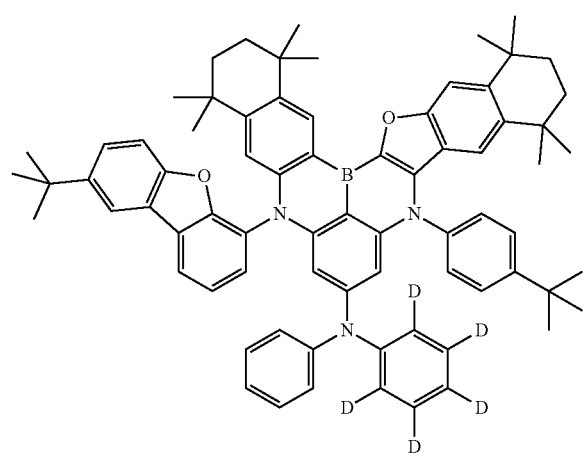
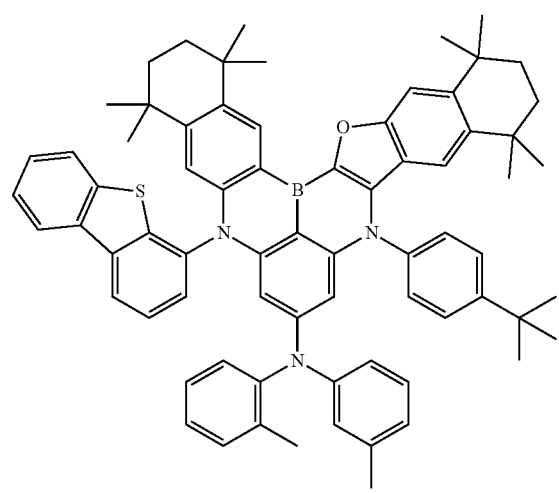
672
-continued
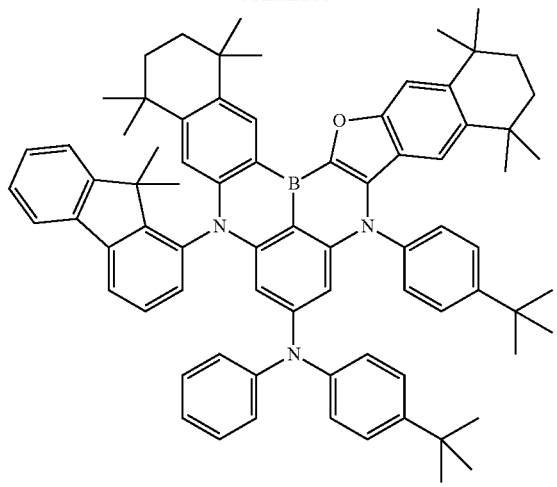
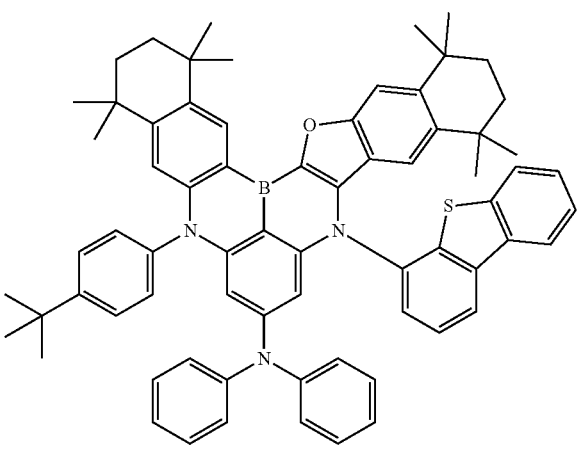
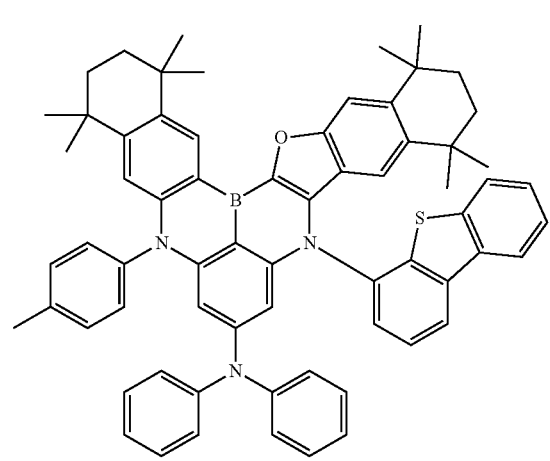

673
-continued
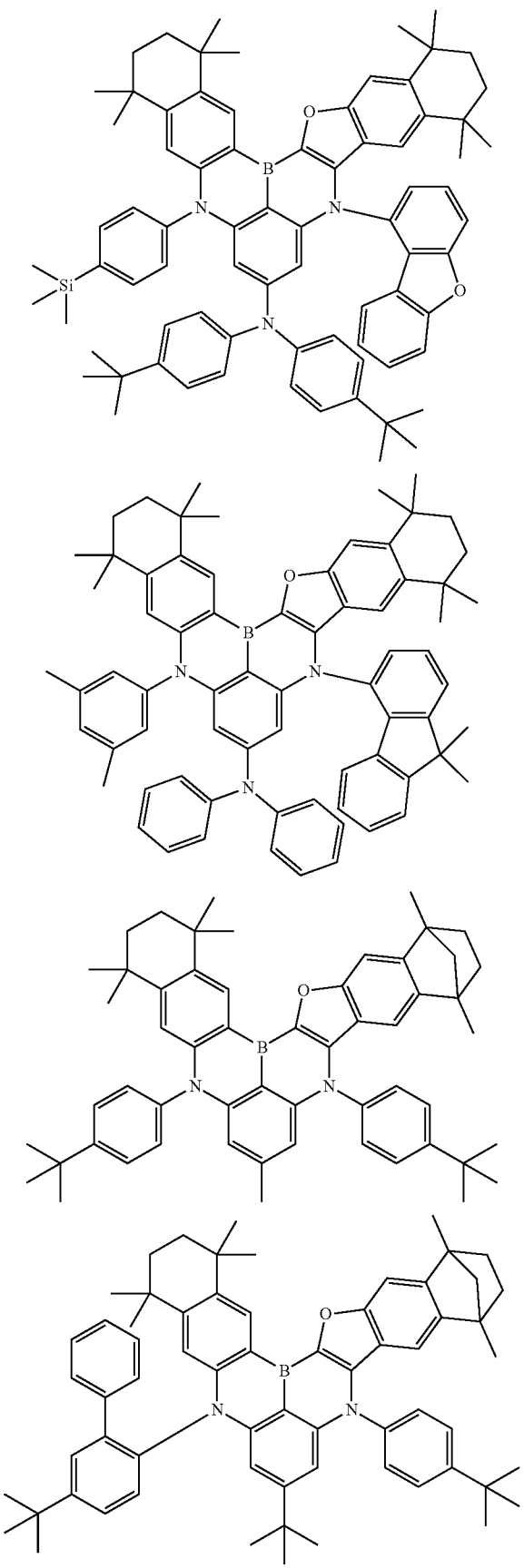
674
-continued
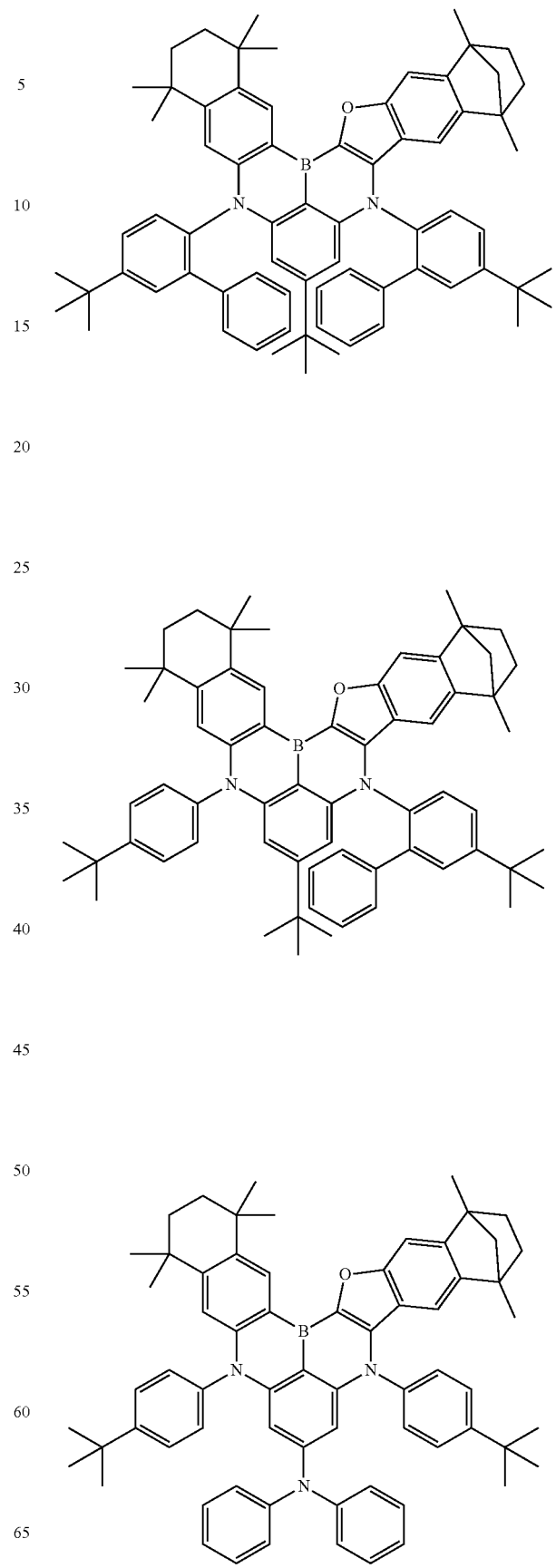

675
-continued
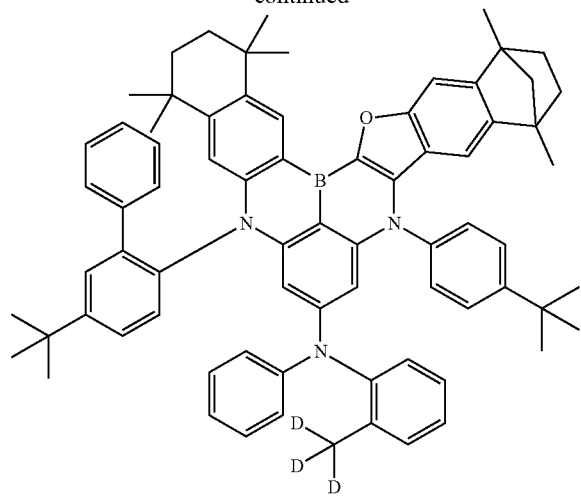
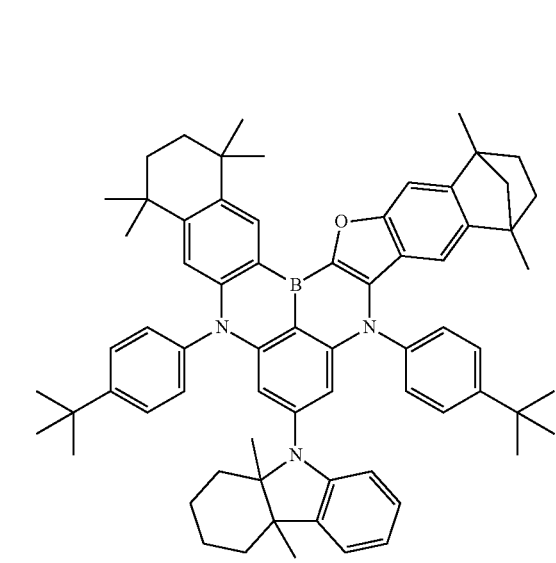
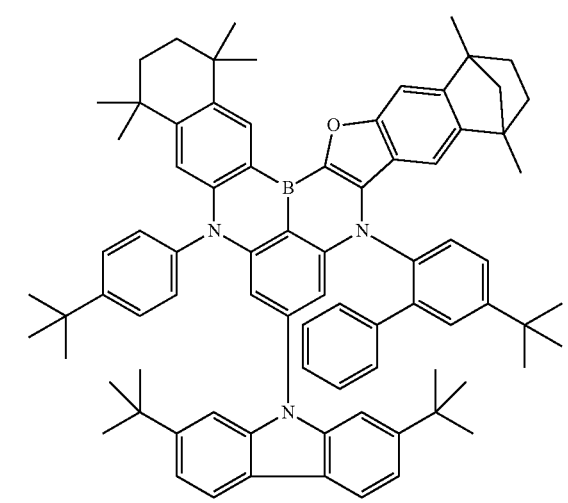
676
-continued
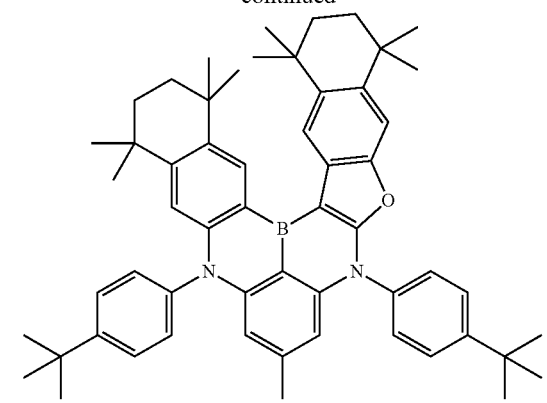
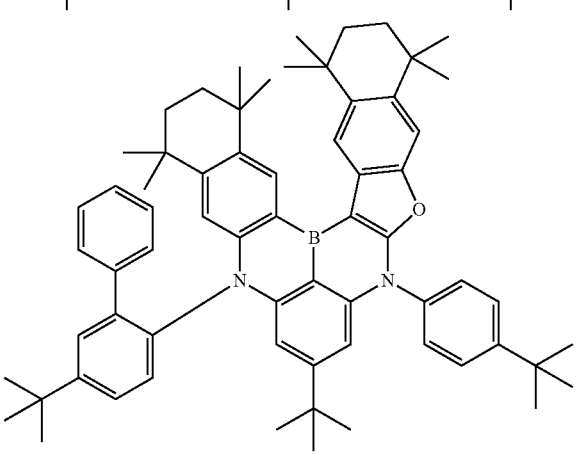
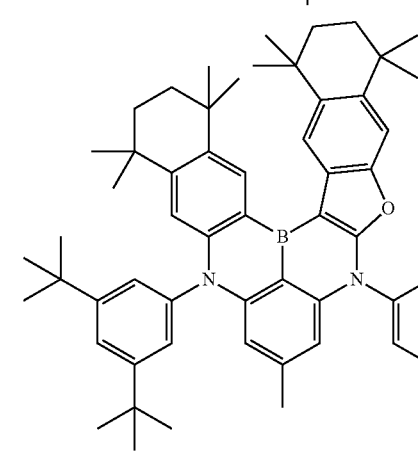
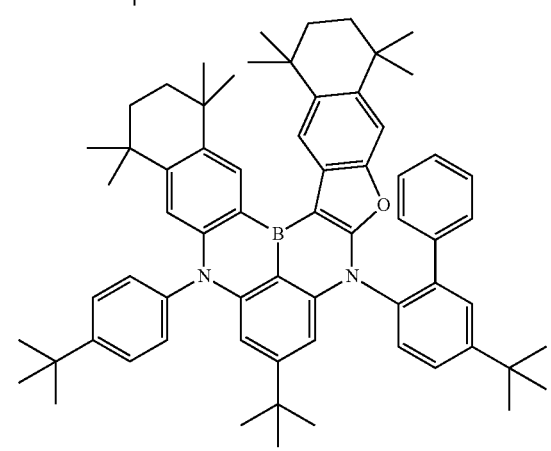

677
-continued
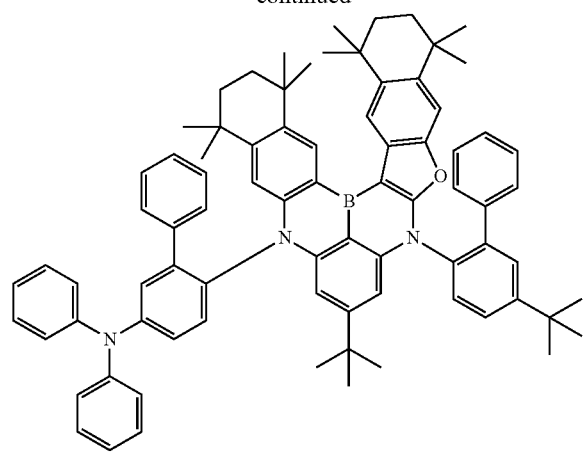
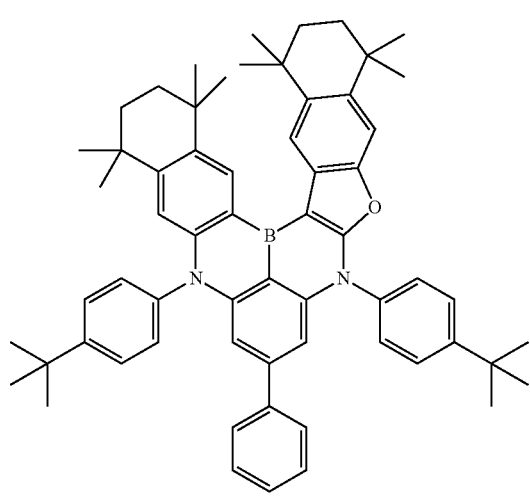
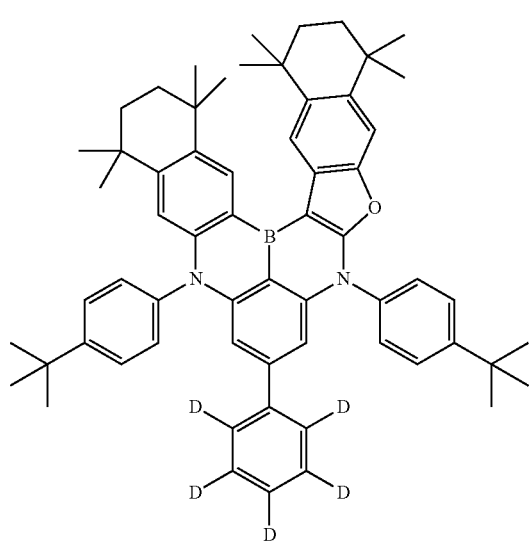
678
-continued
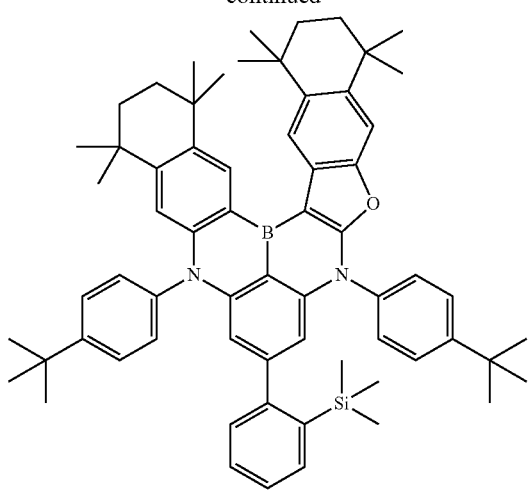
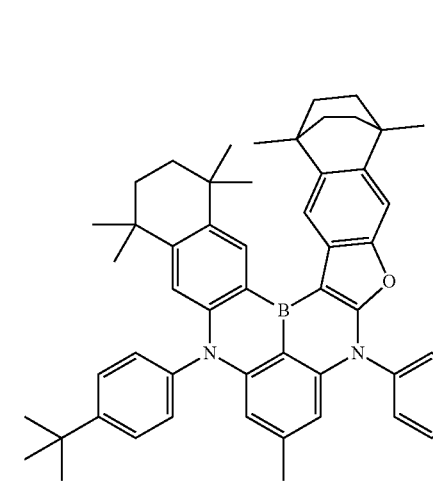
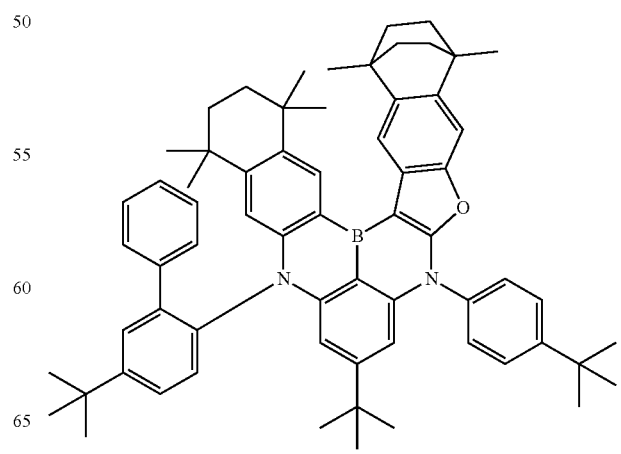

679
-continued
680
-continued
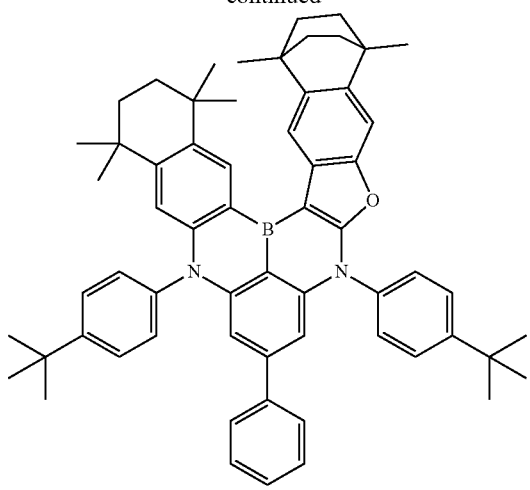
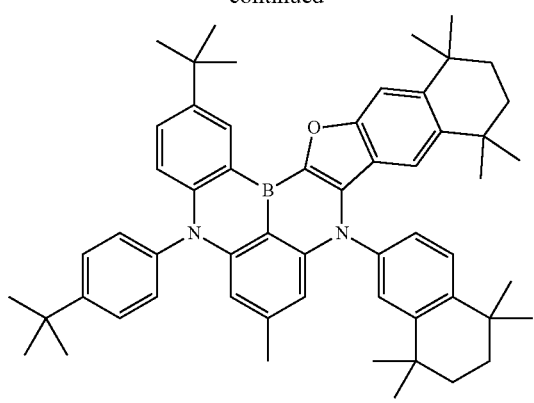
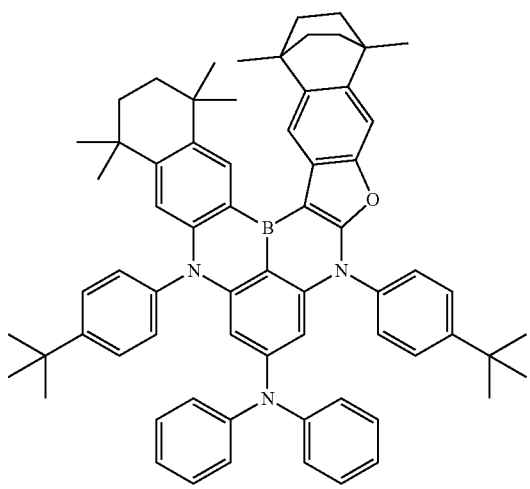
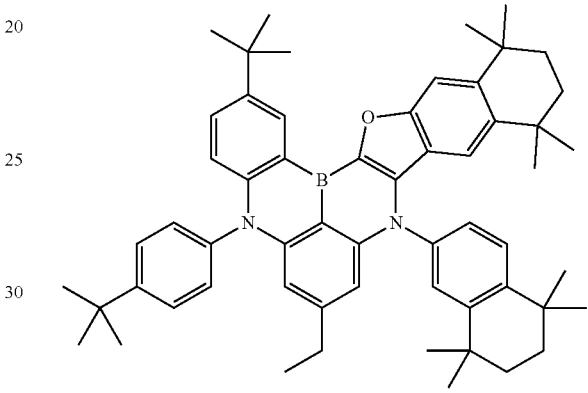
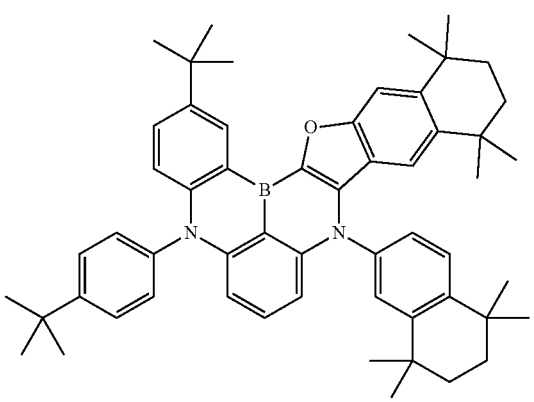
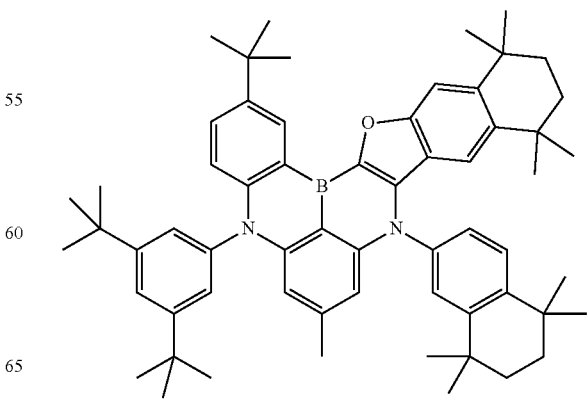

681
-continued
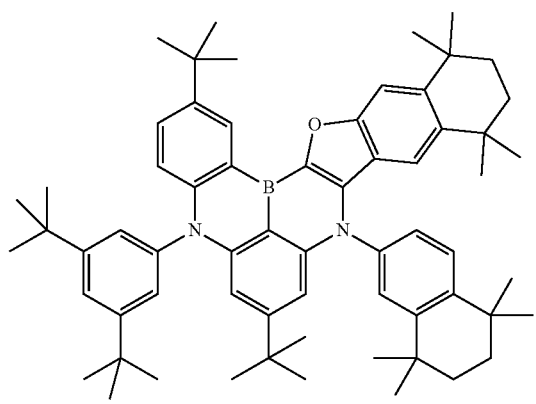
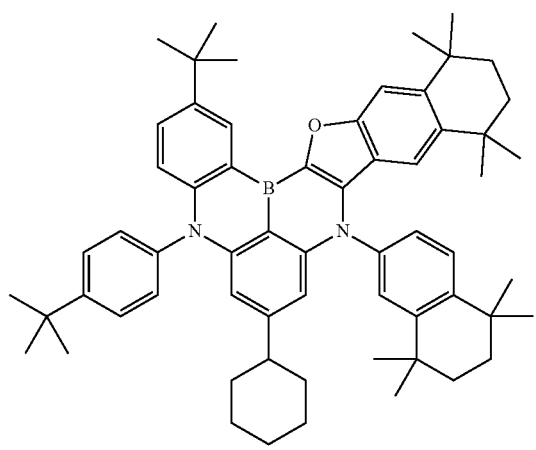
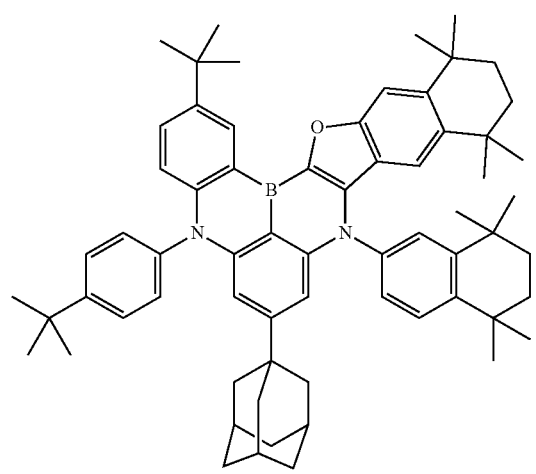
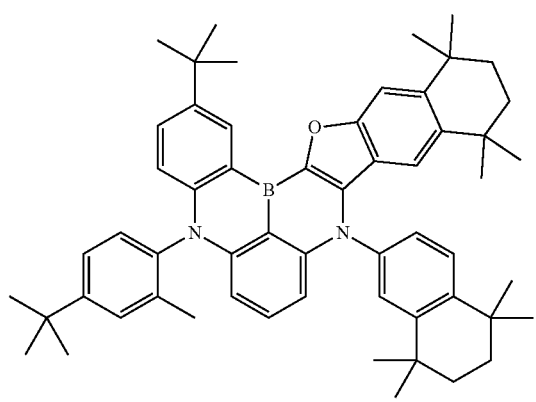
682
-continued
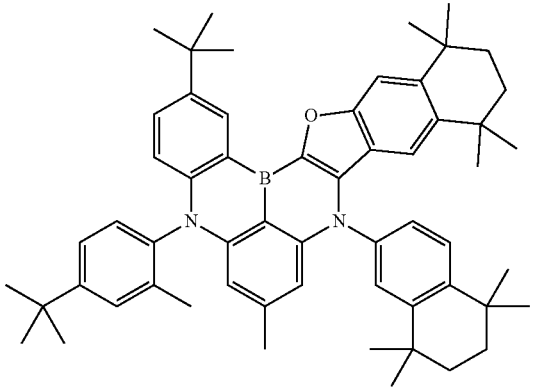
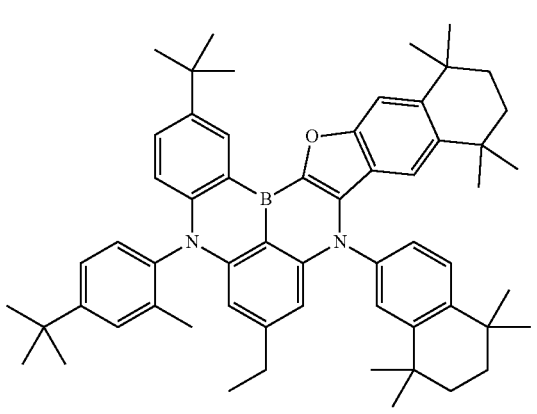
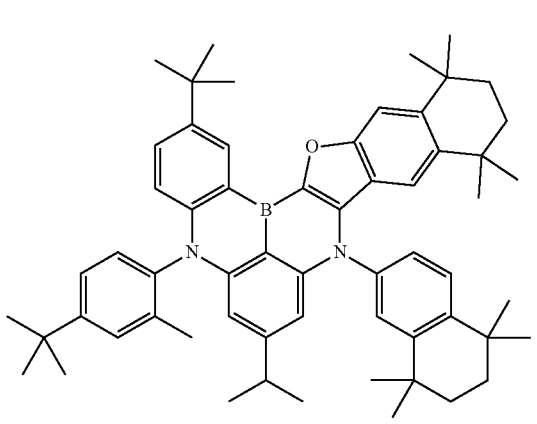
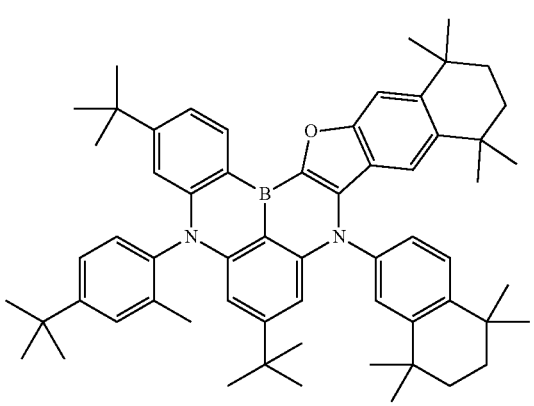

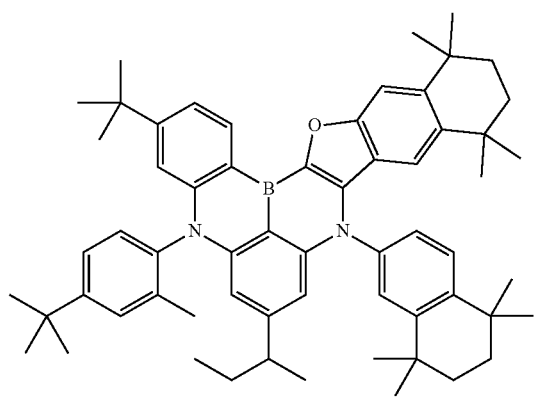
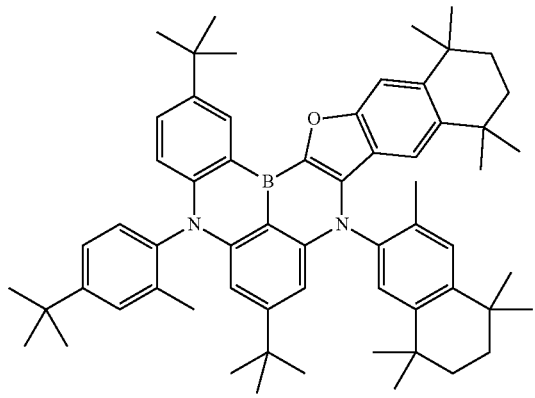
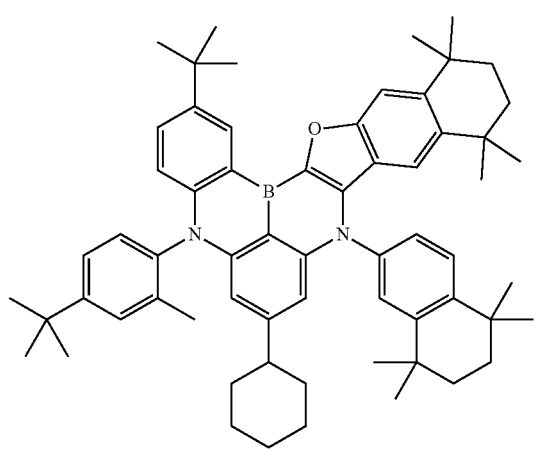
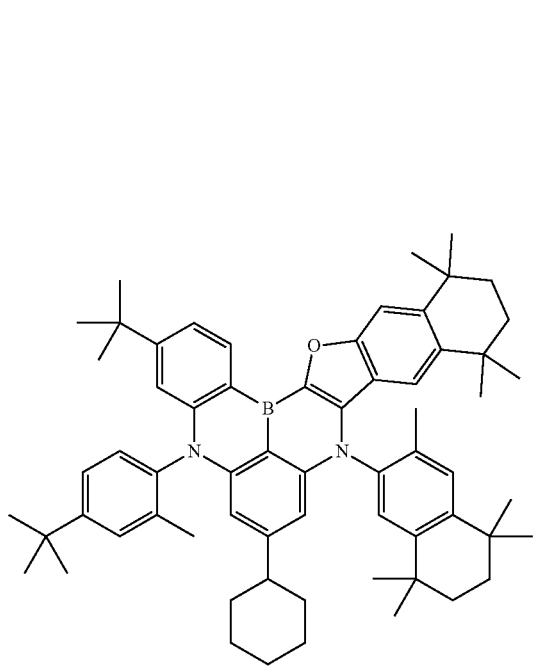
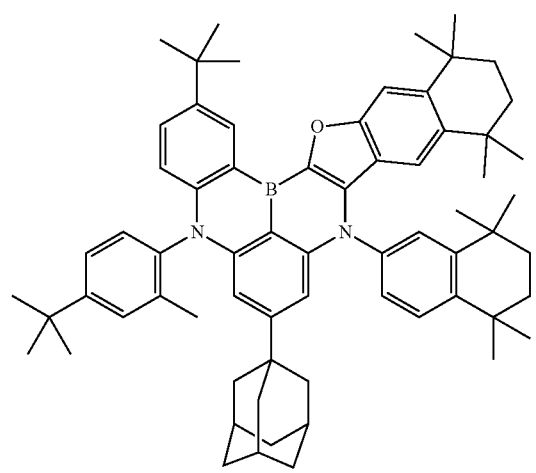
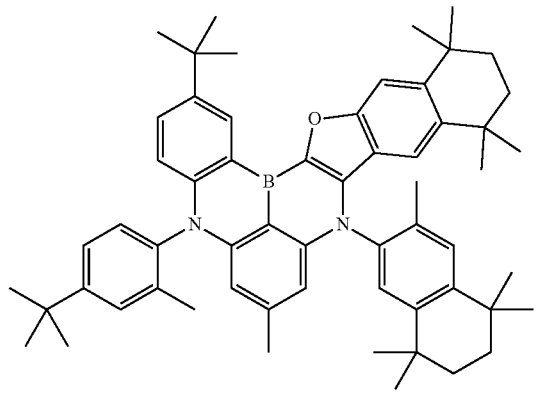
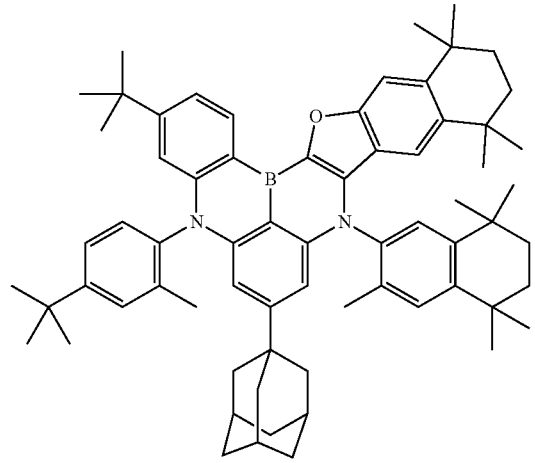

685
-continued
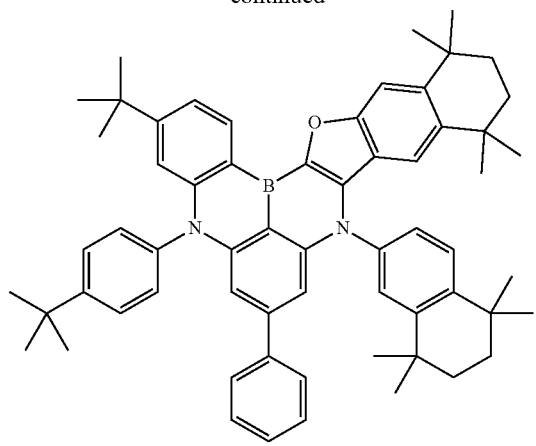
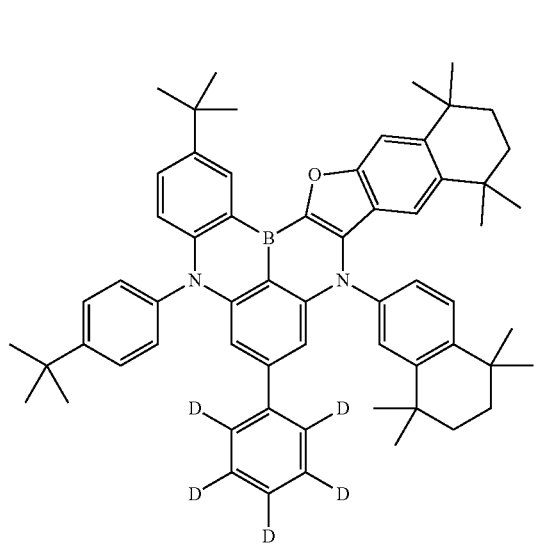
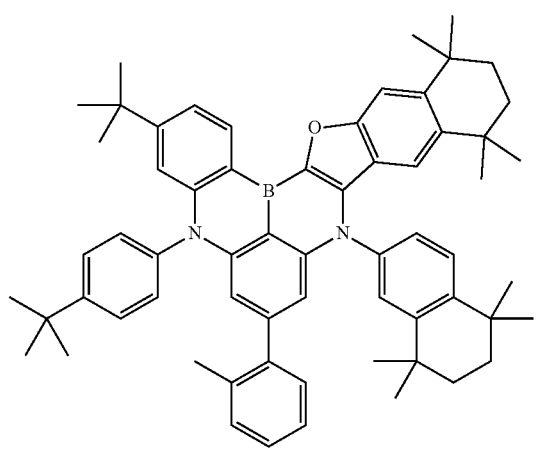
686
-continued
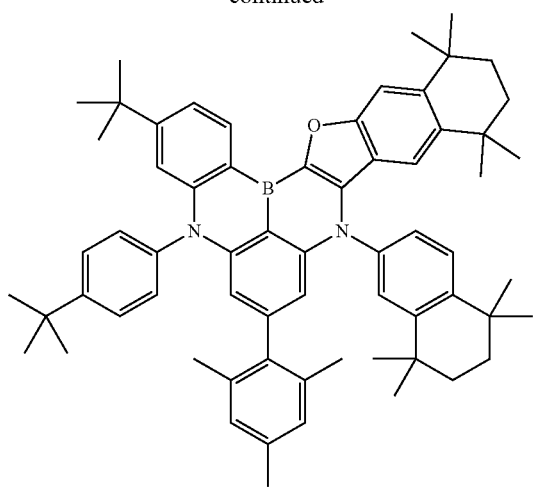
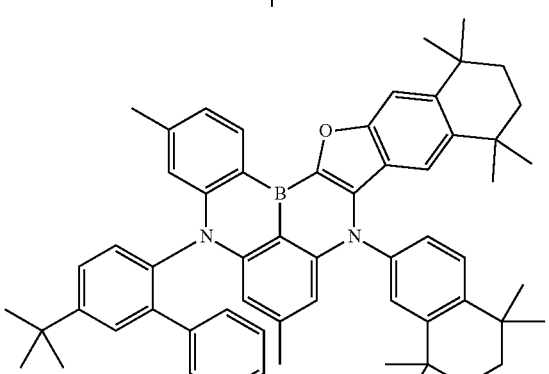
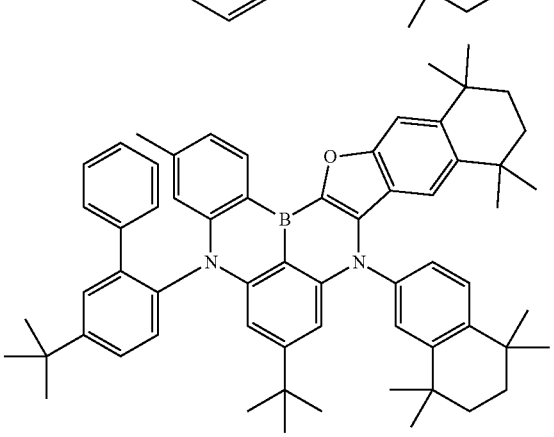
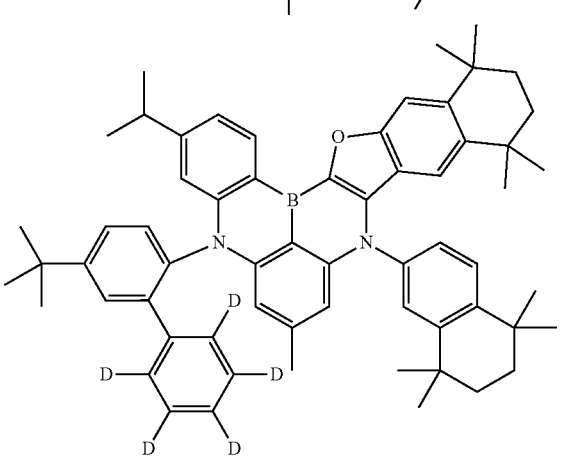

687
-continued
688
-continued
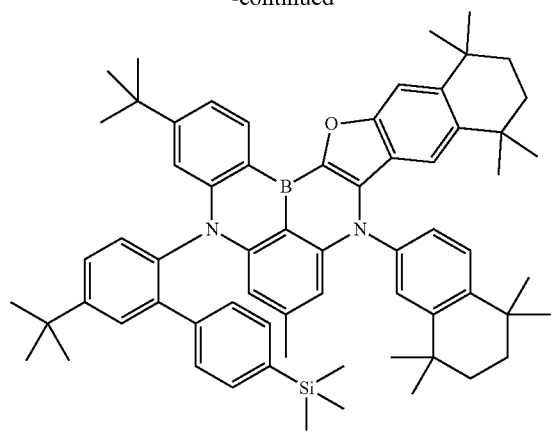
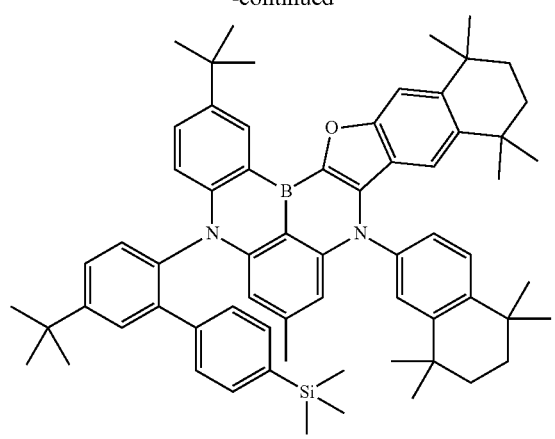
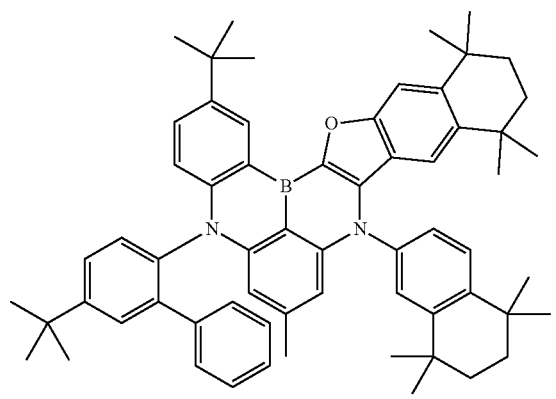
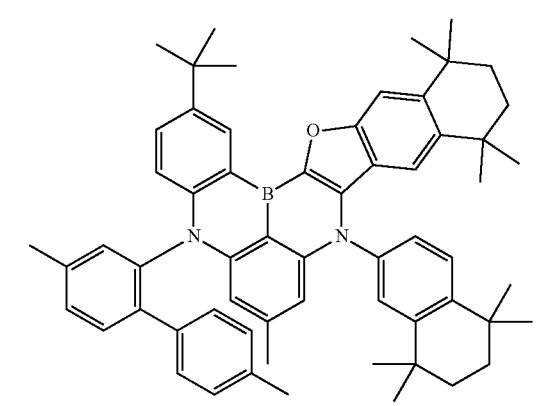
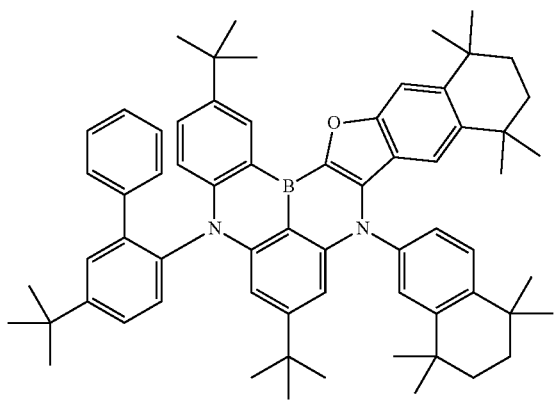
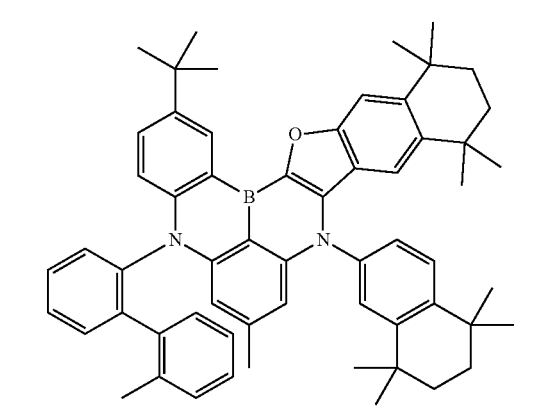
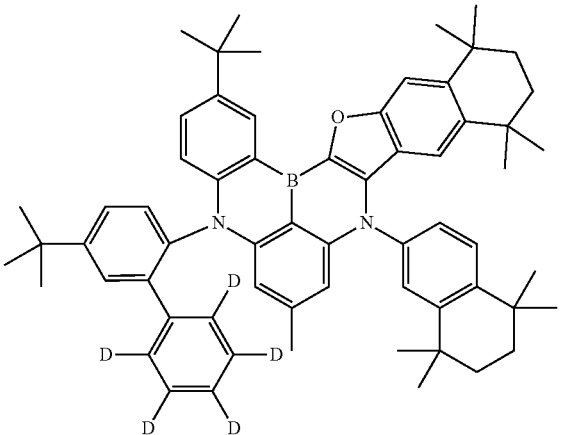
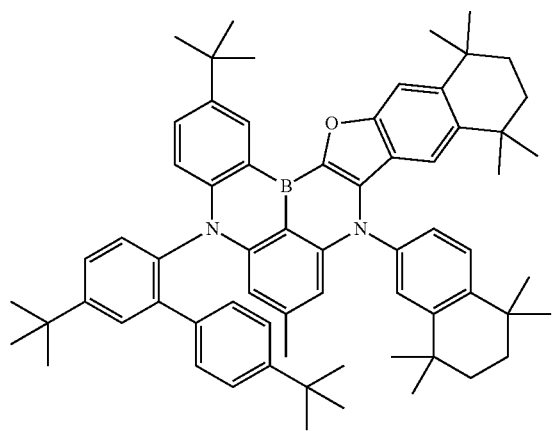

689
-continued
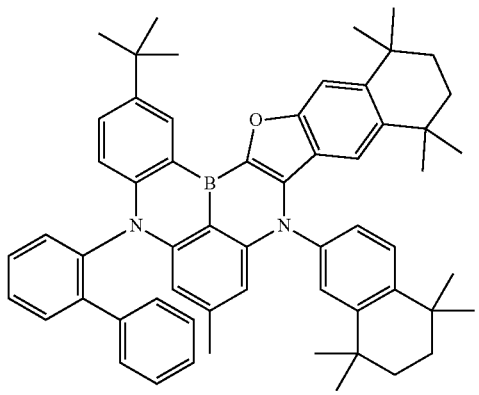
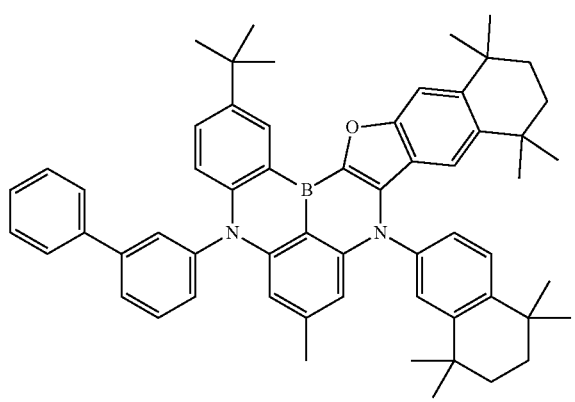
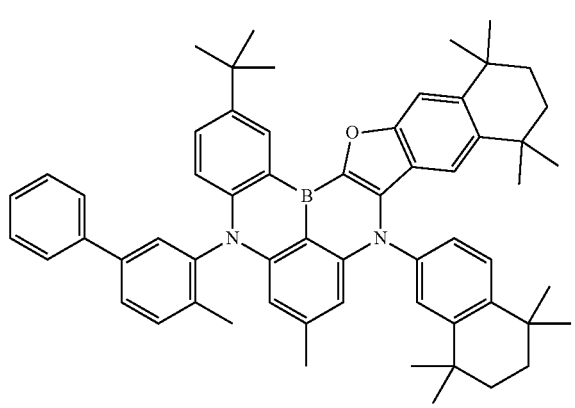
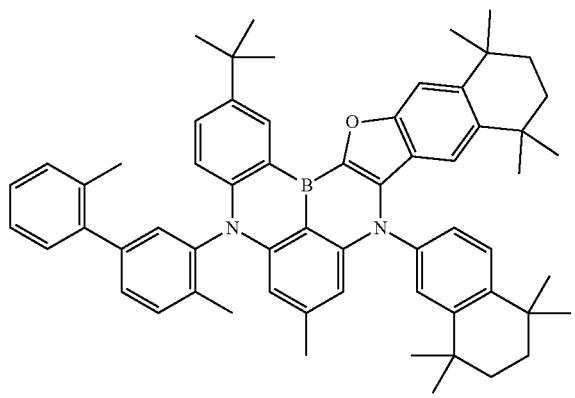
690
-continued
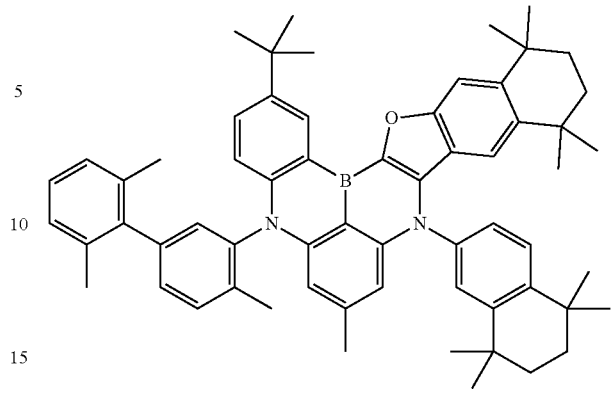
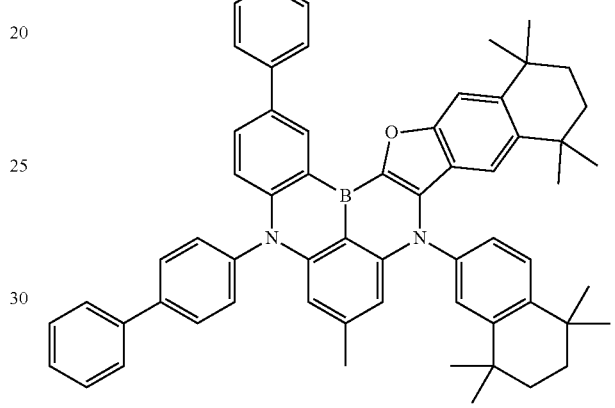
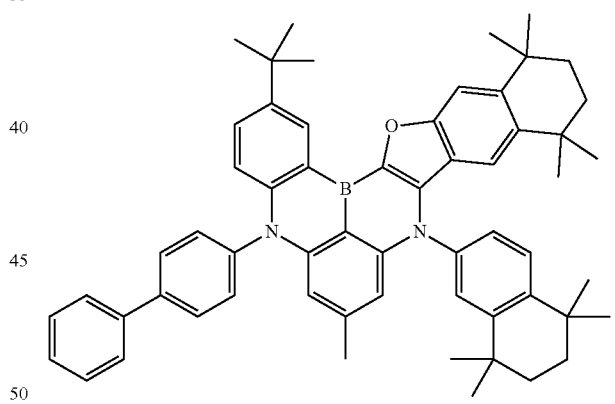
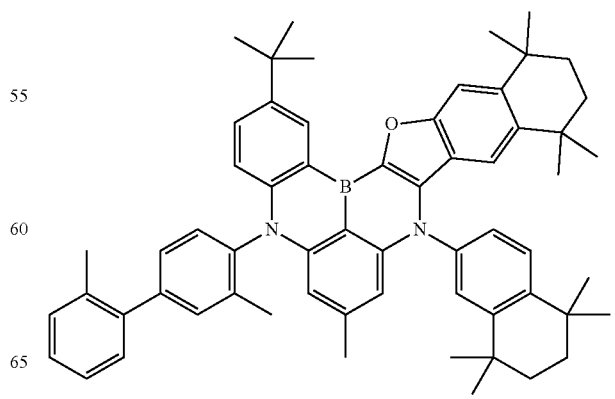

691
-continued
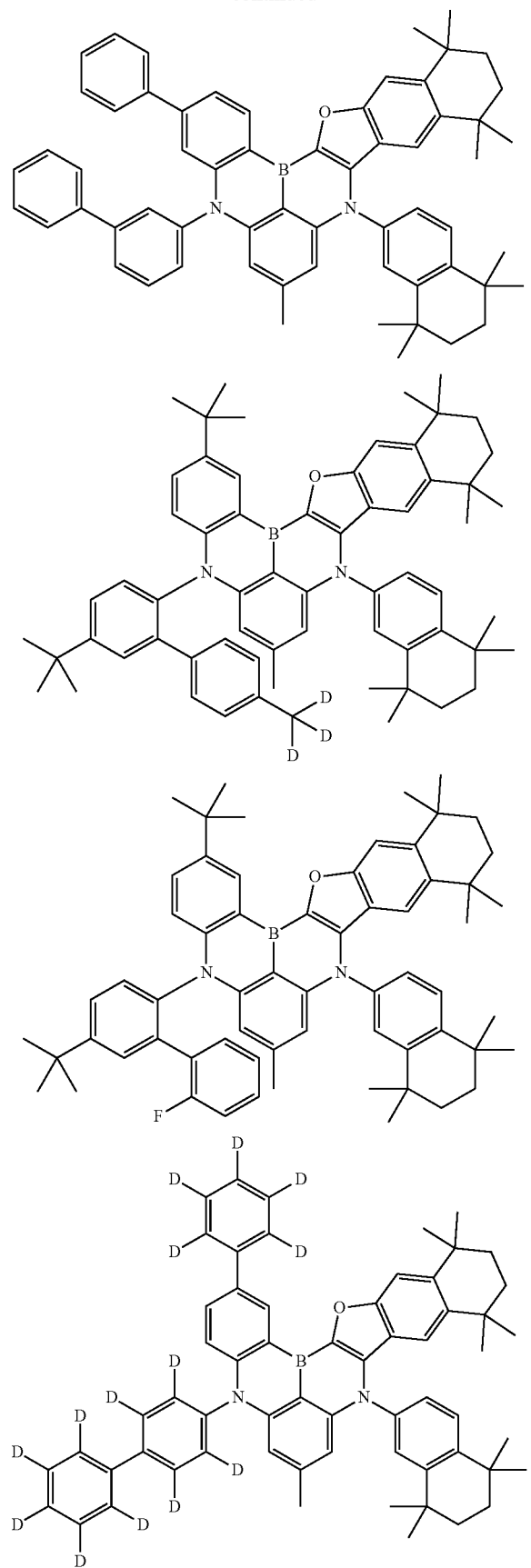
692
-continued
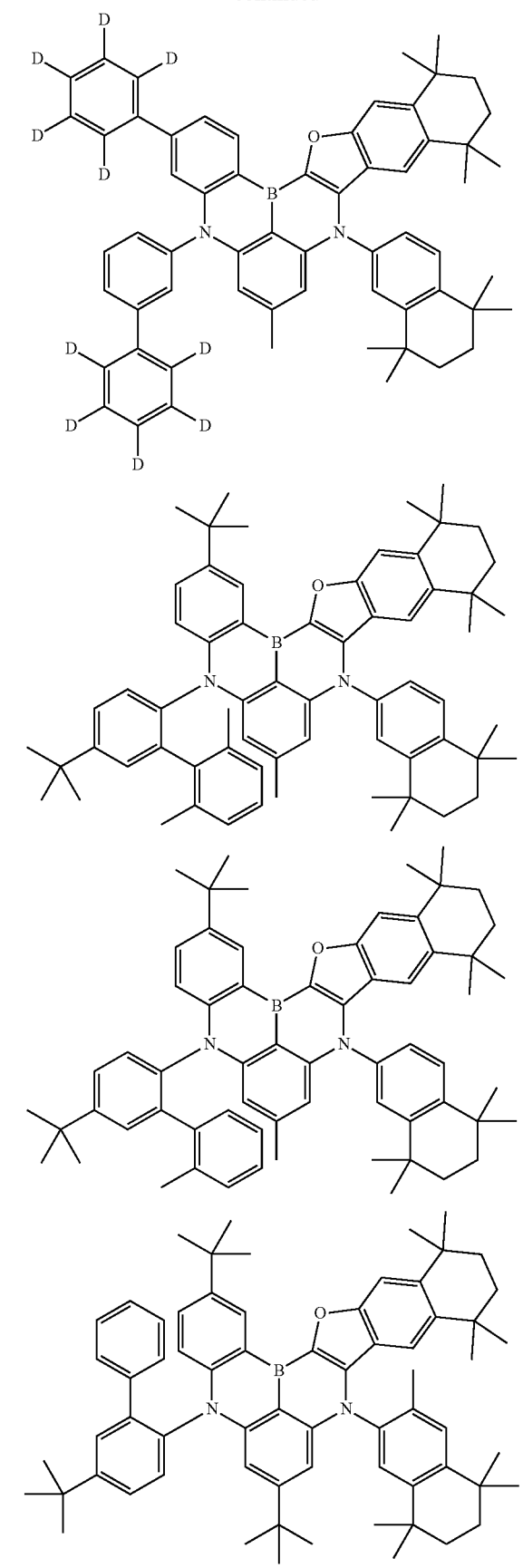

693
-continued
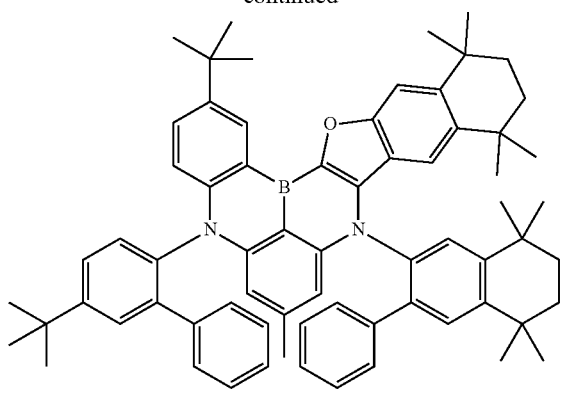
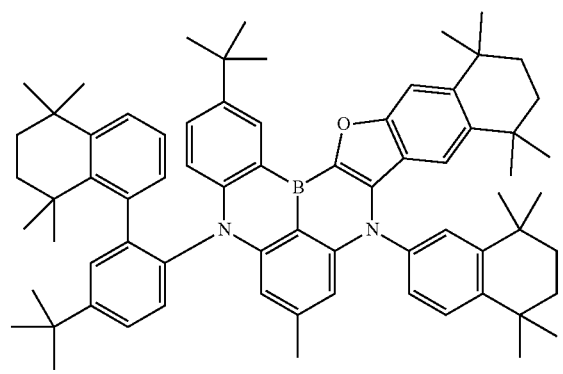
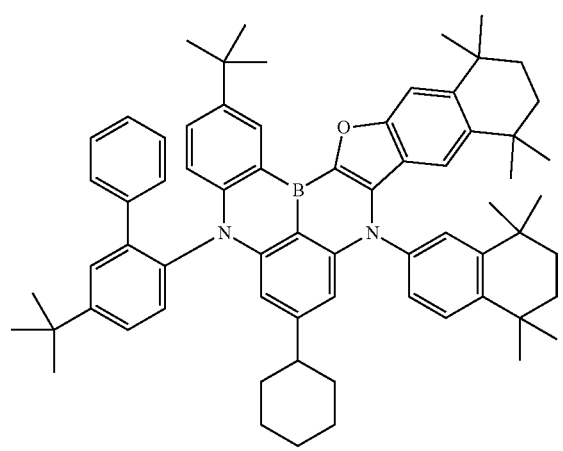
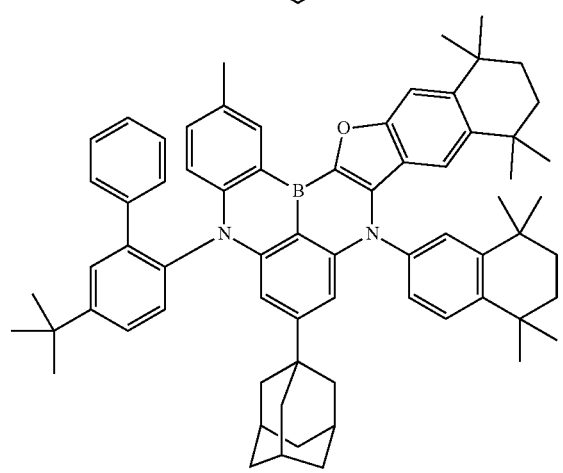
694
-continued
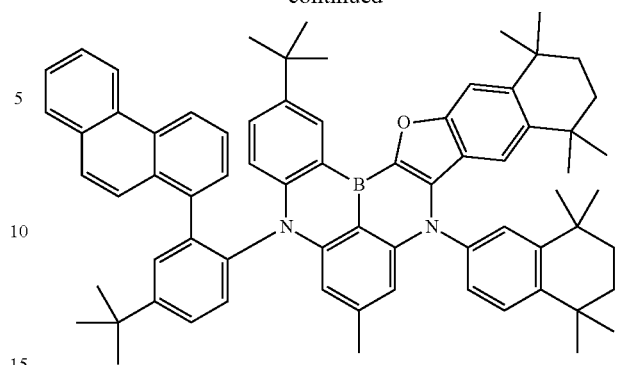
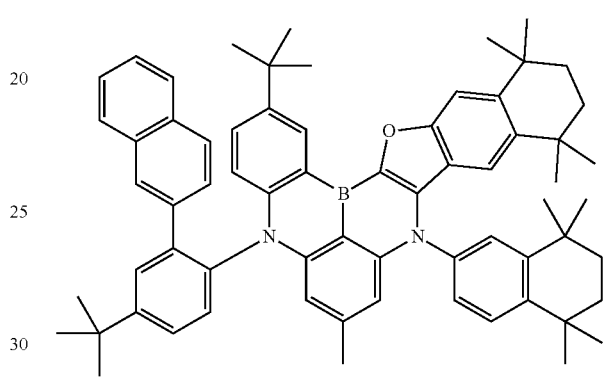
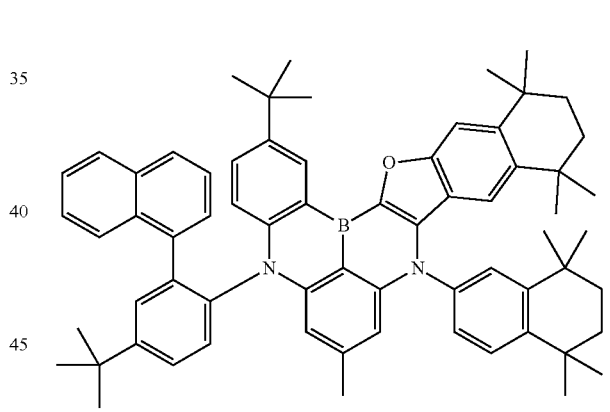
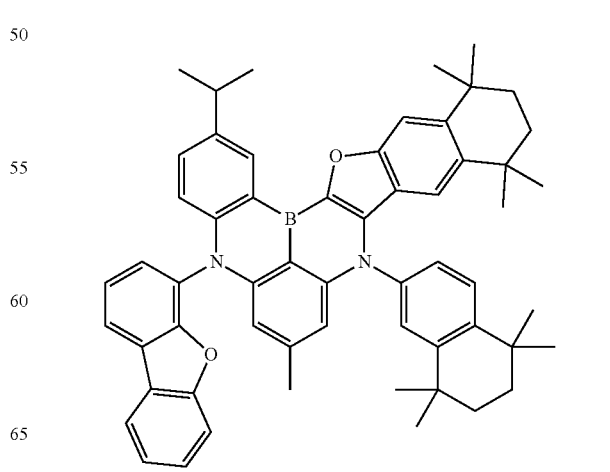

695
-continued
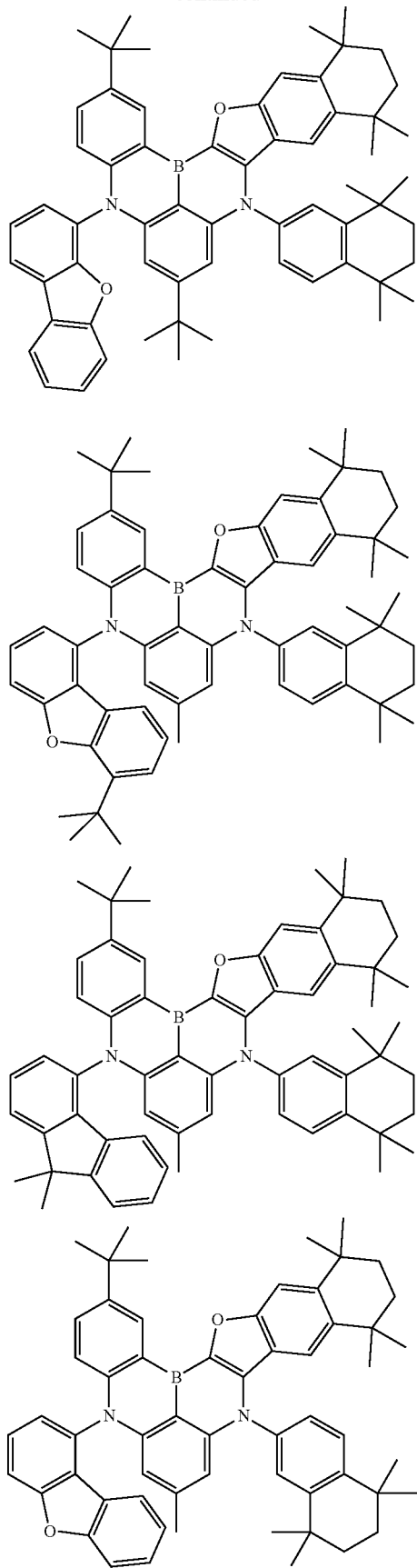
696
-continued
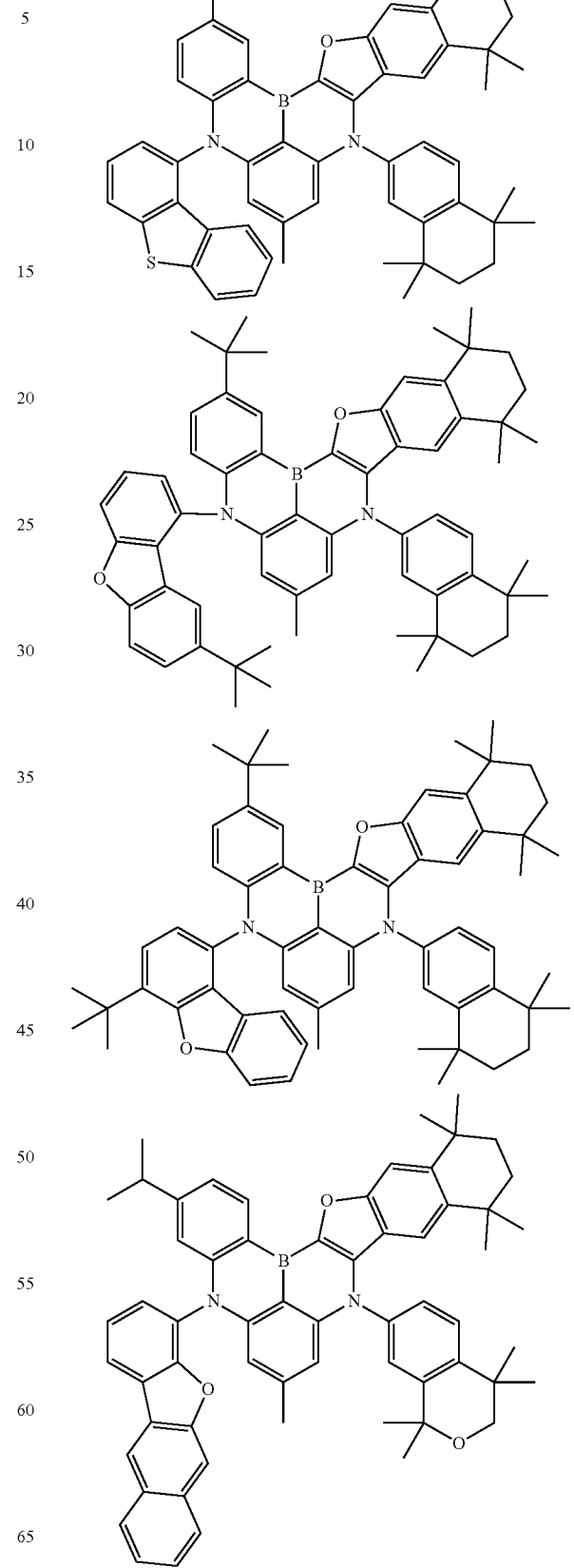

697
-continued
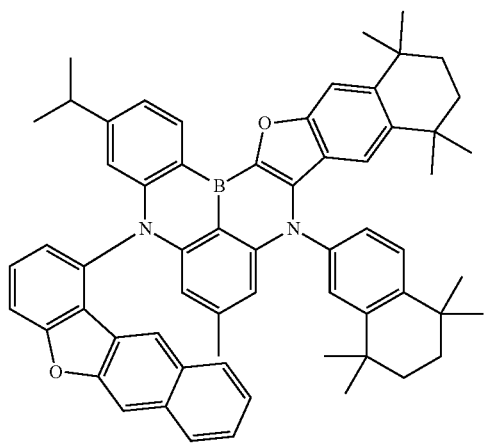
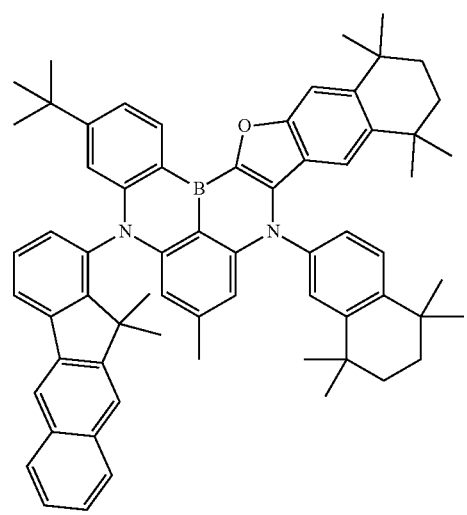
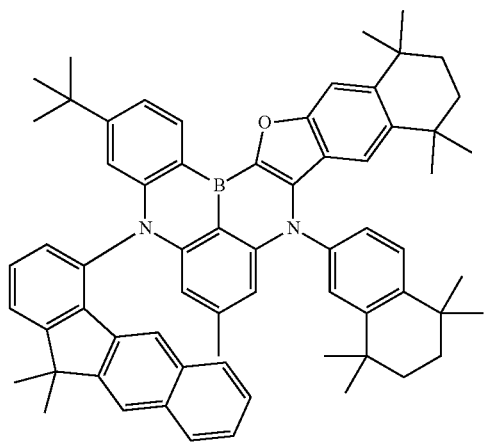
698
-continued
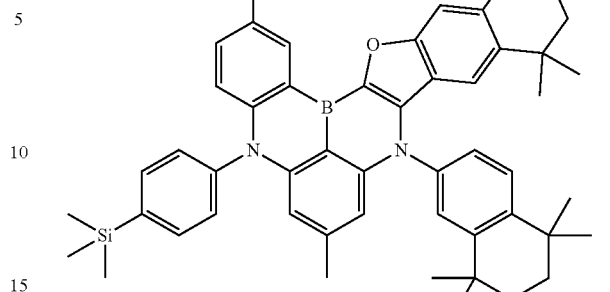
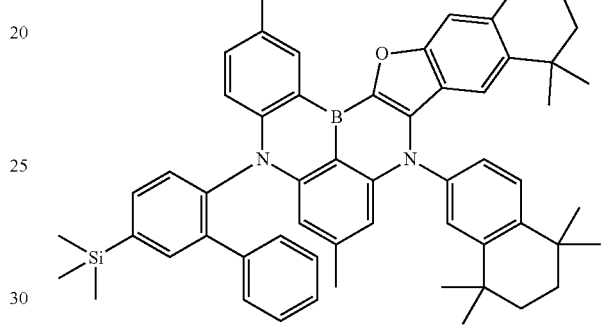
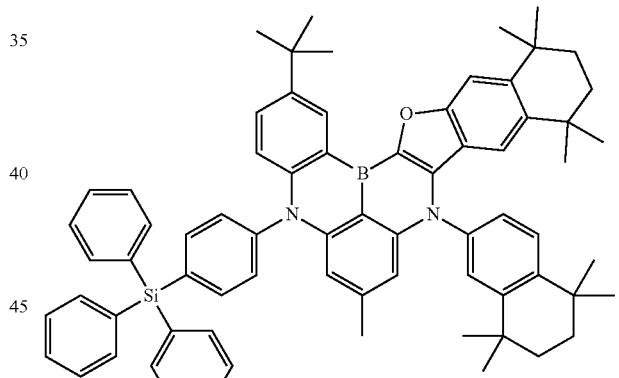
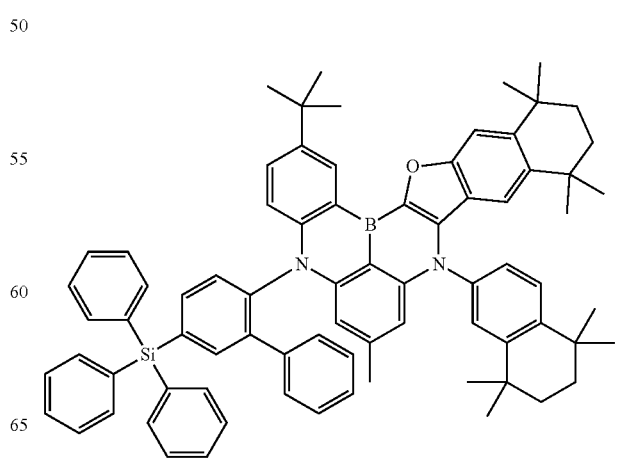

699
-continued
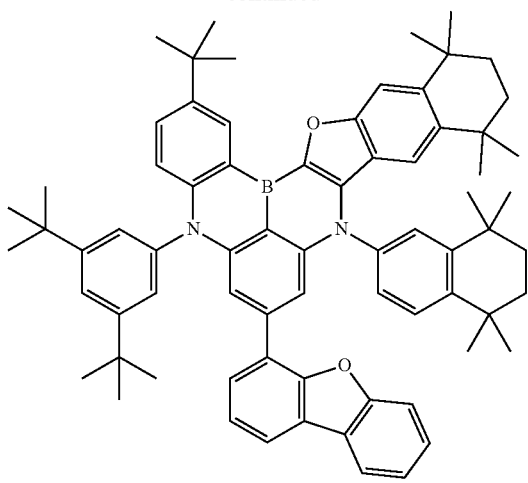
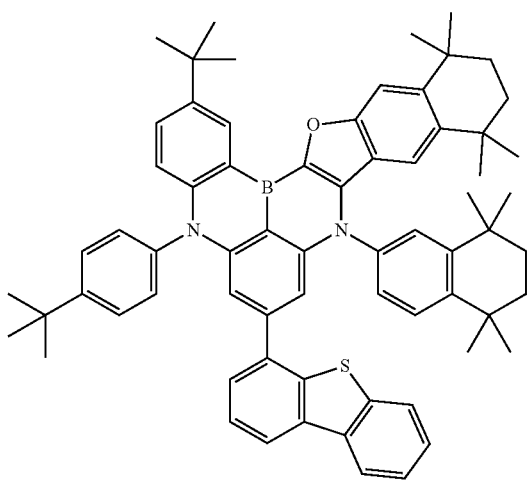
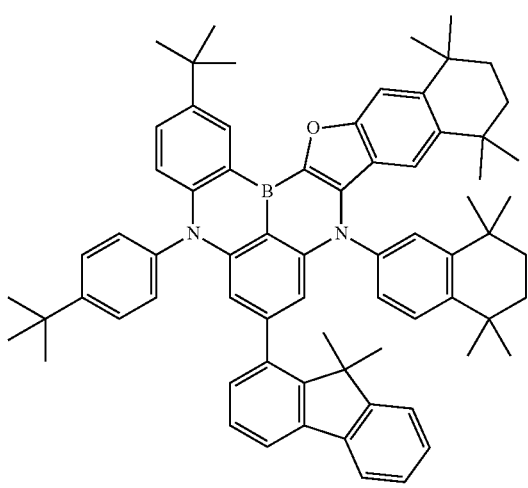
700
-continued
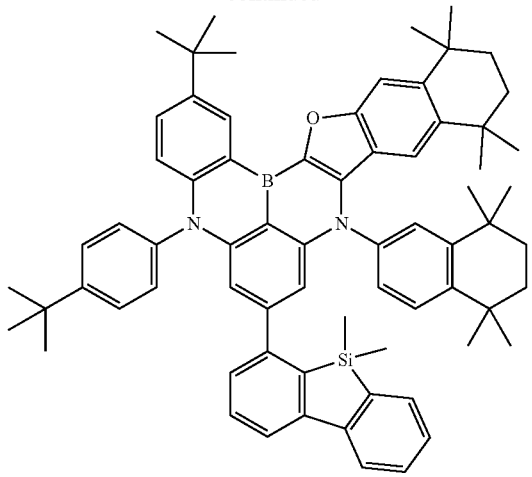
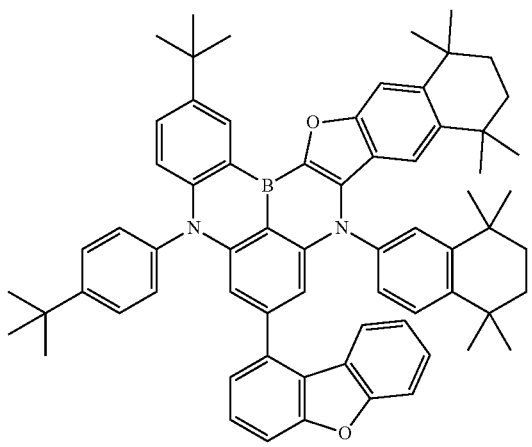
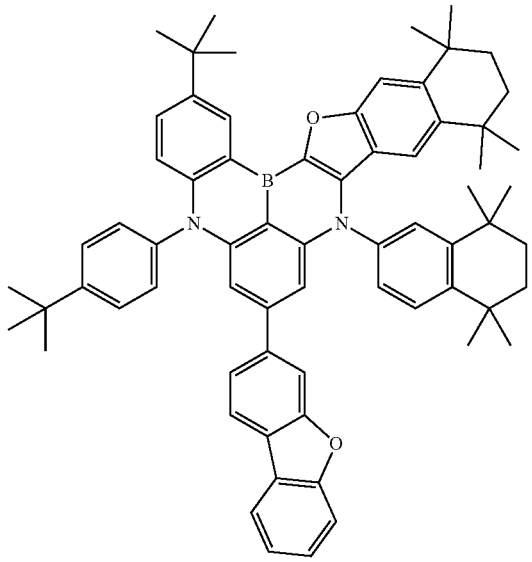

701
-continued
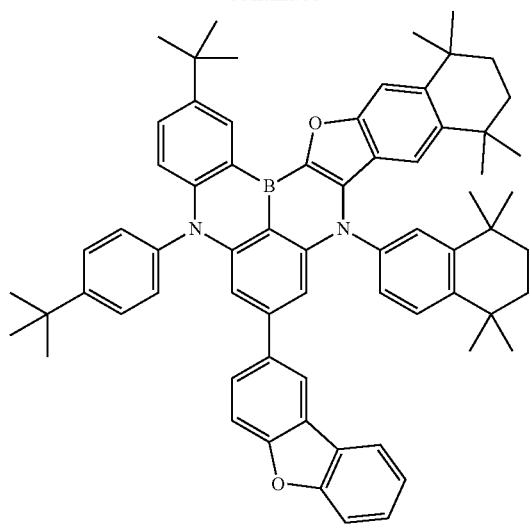
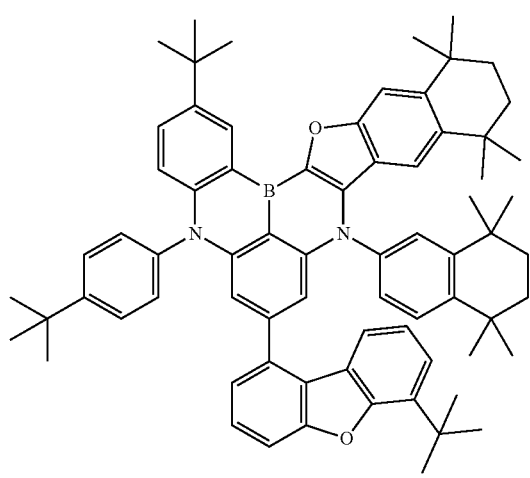
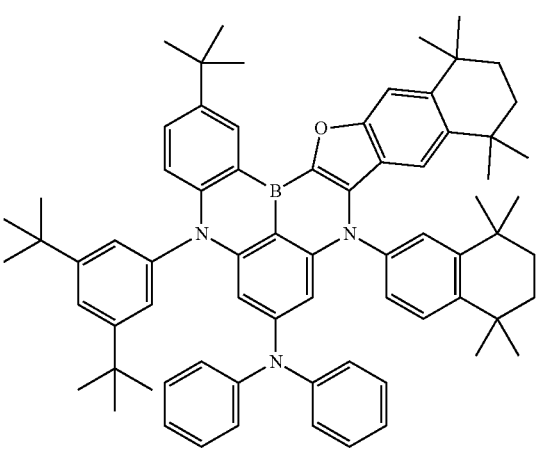
702
-continued
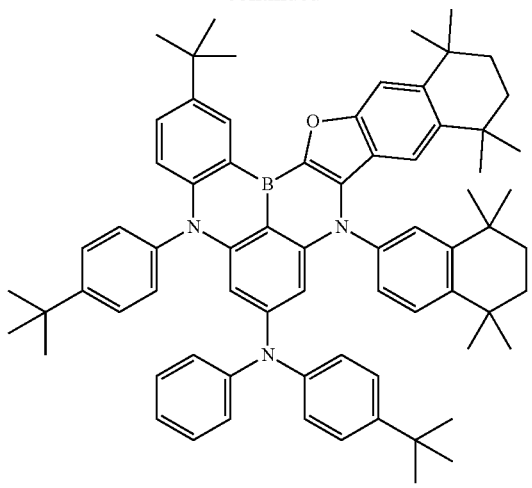
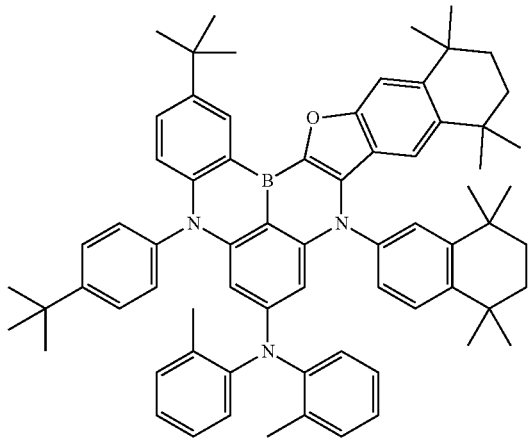
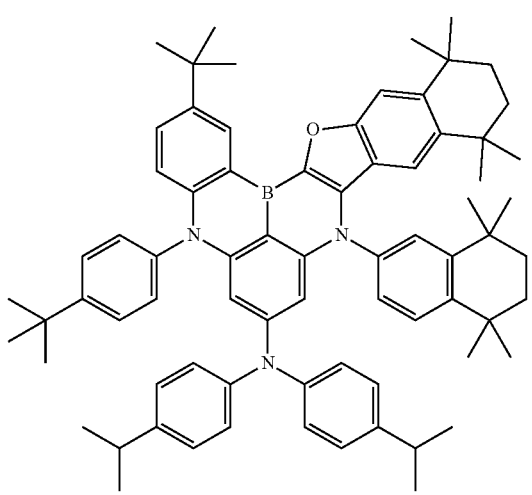

703
-continued
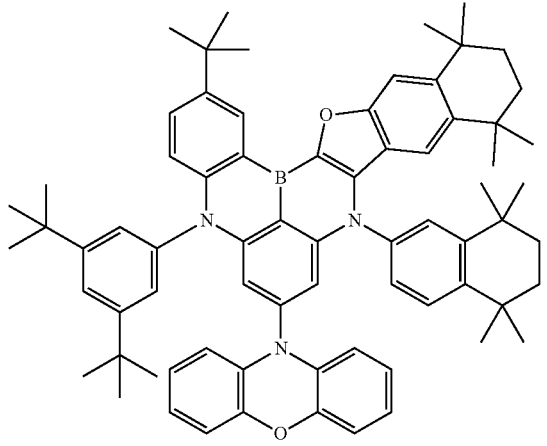
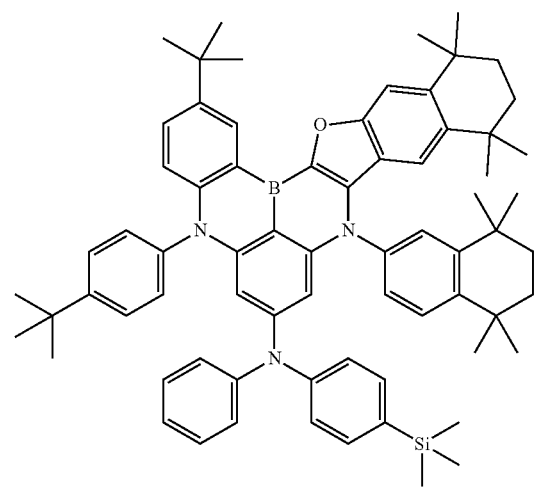
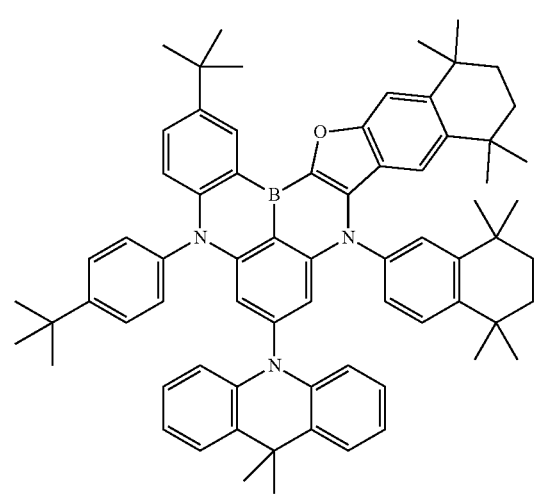
704
-continued
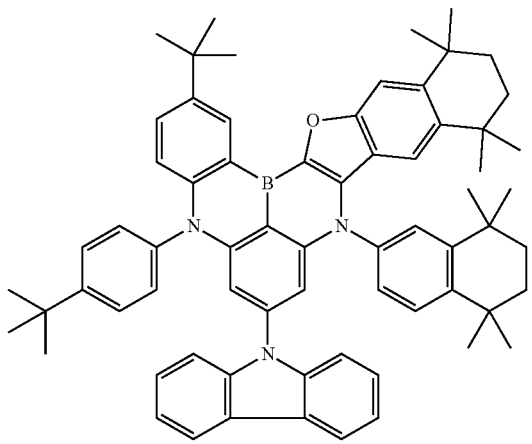
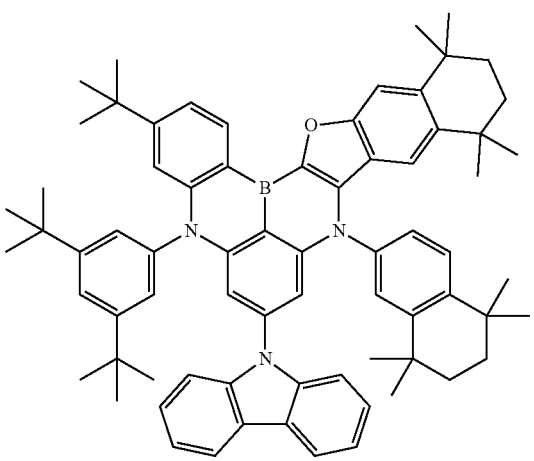
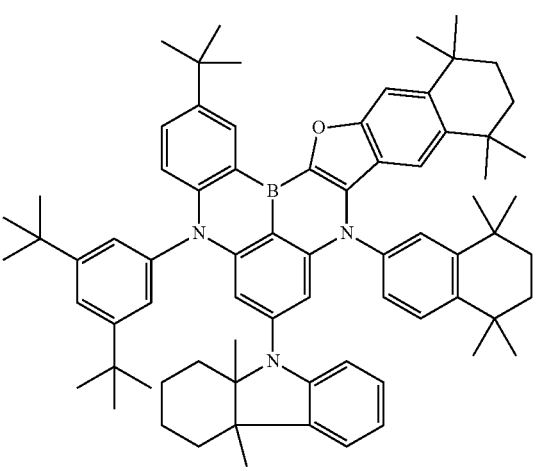

| 705 -continued | 706 -continued |
|---|---|
| 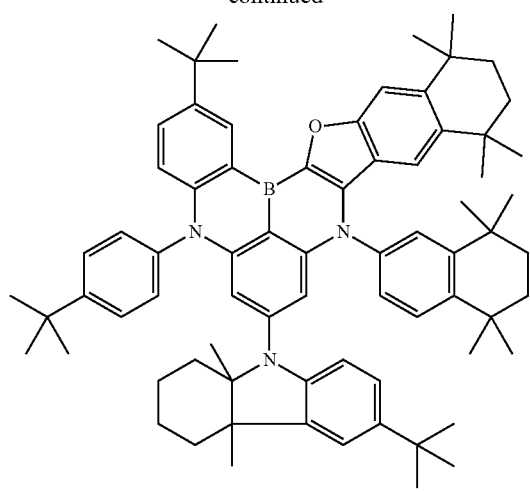 | 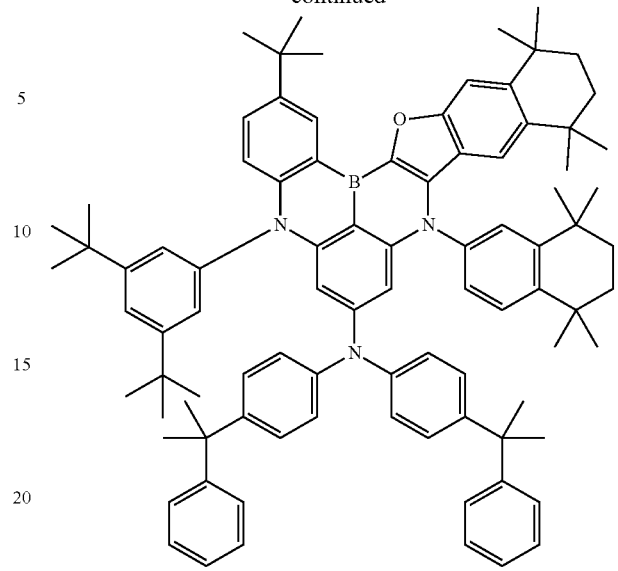 |
| 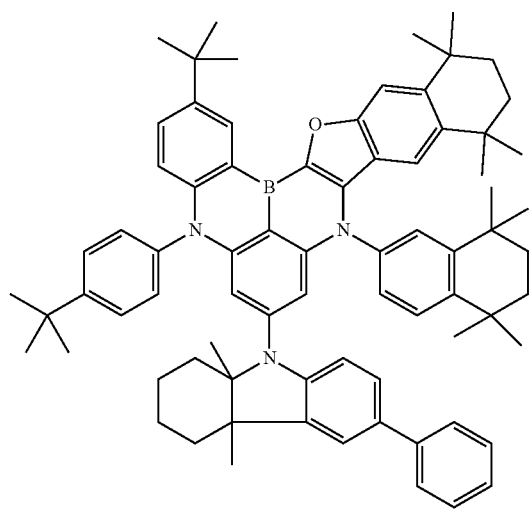 | 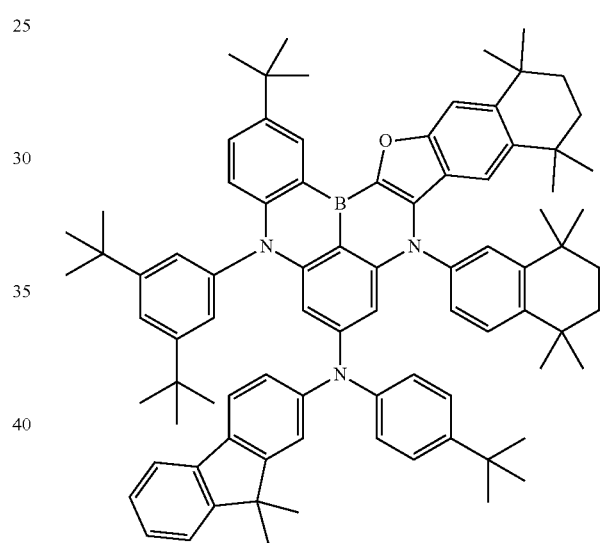 |
| 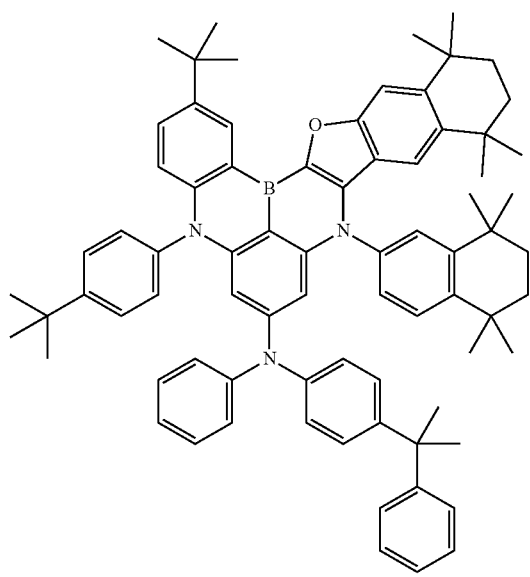 | 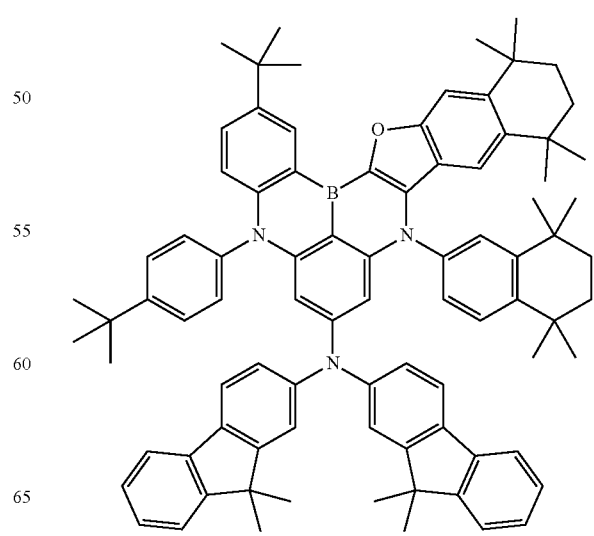 |

707
-continued
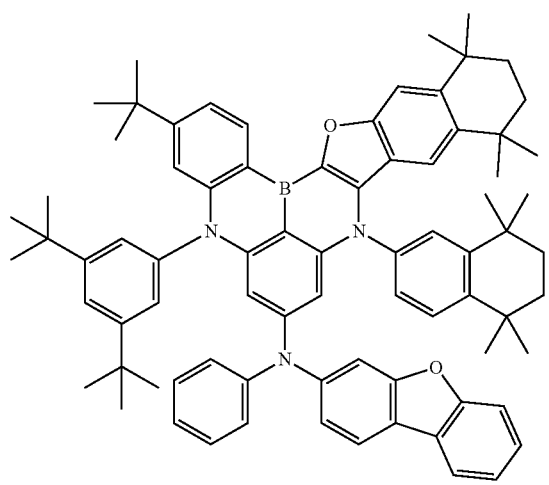
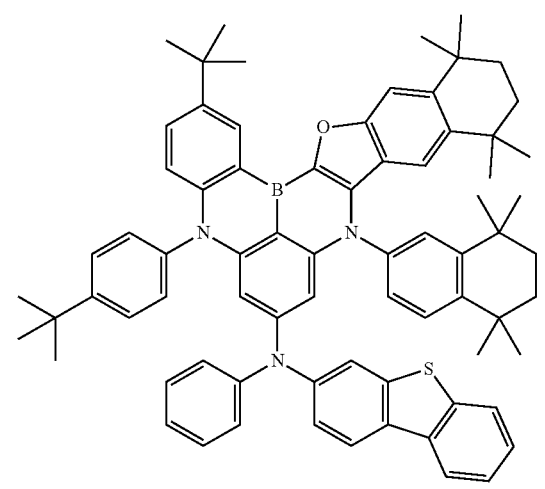
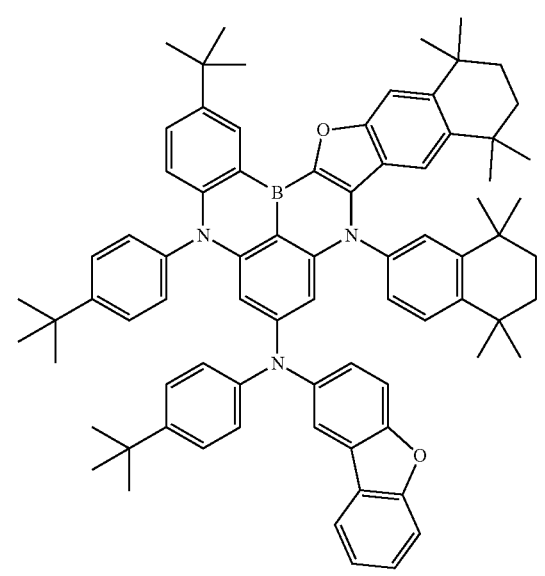
708
-continued
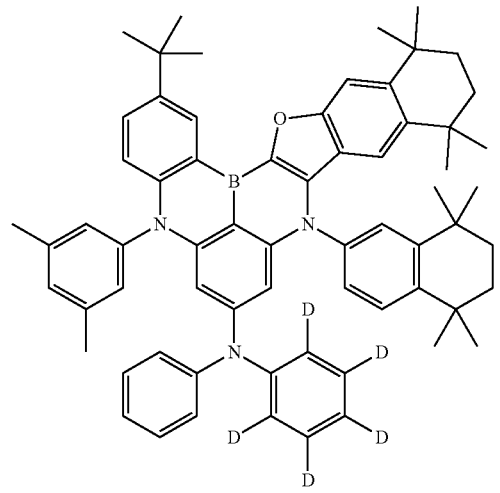
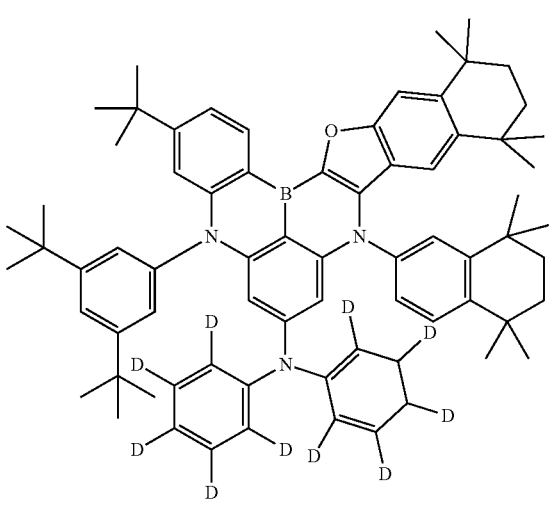

709
-continued
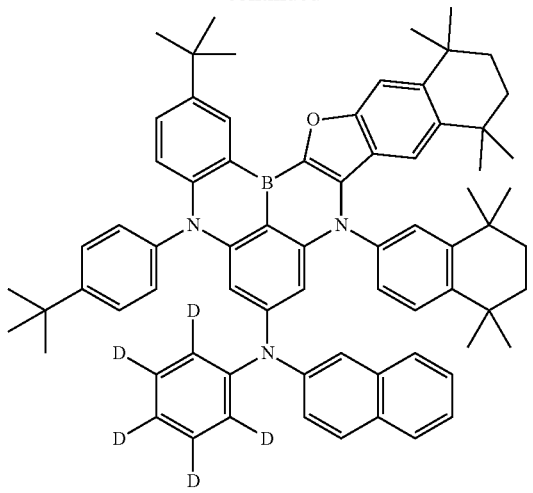
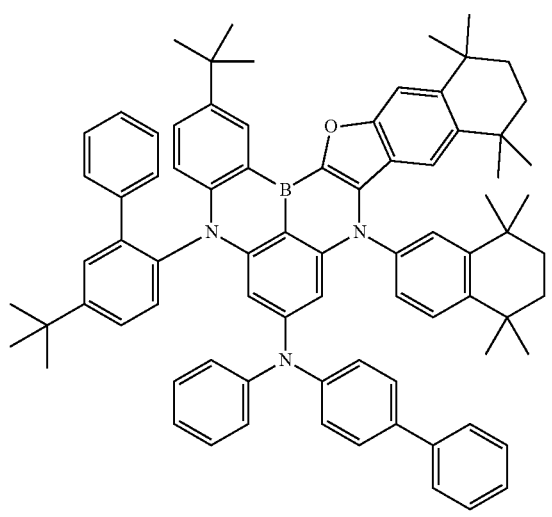
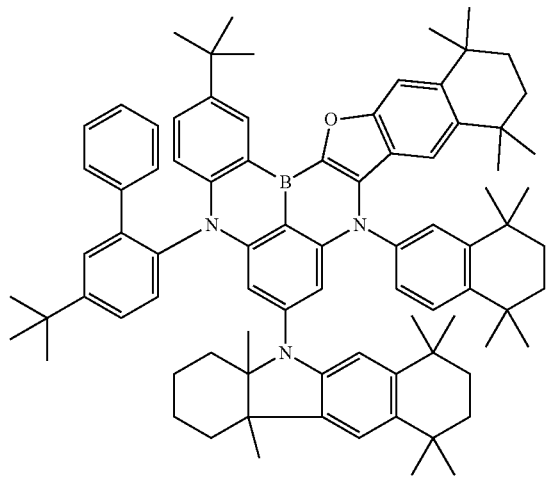
710
-continued
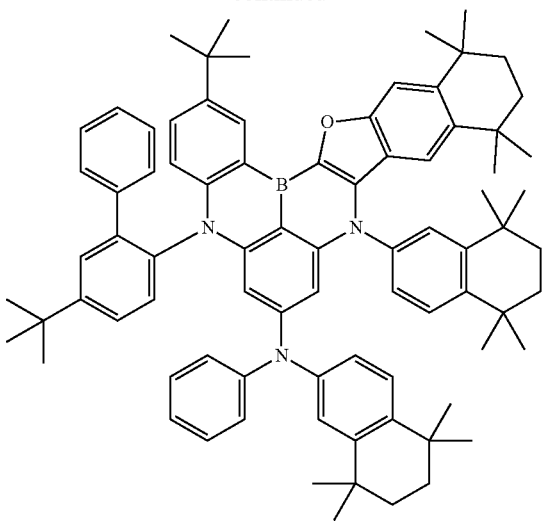
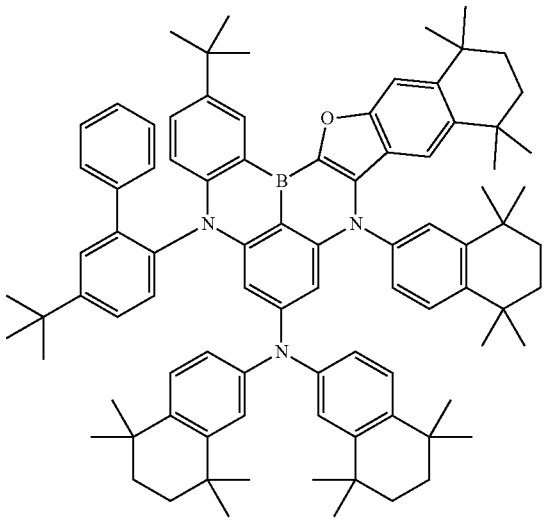

711
-continued
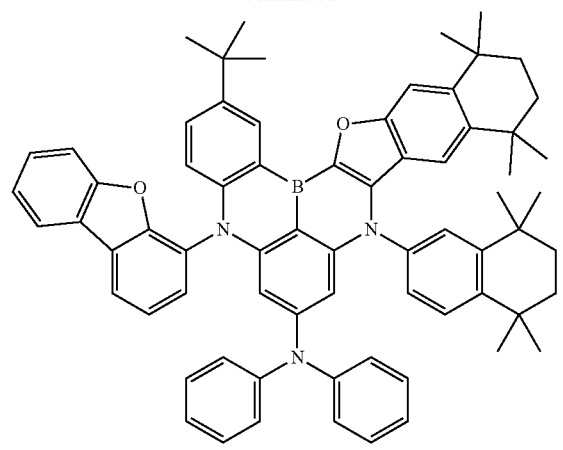
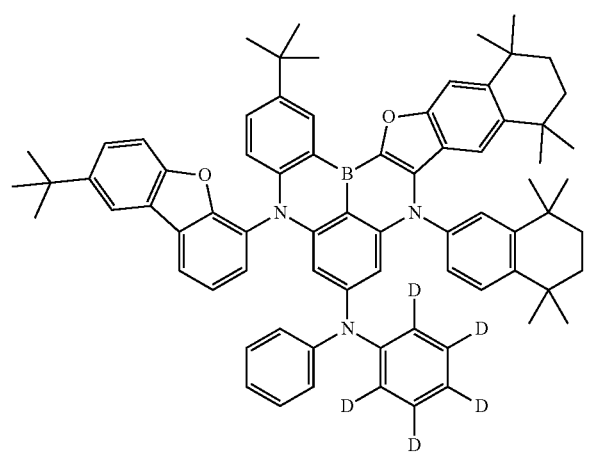
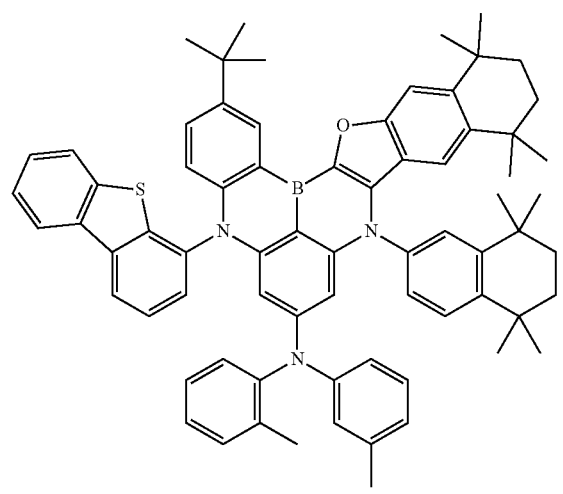
712
-continued
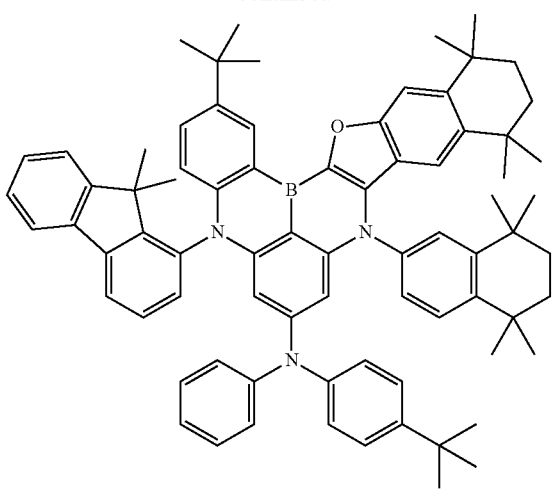
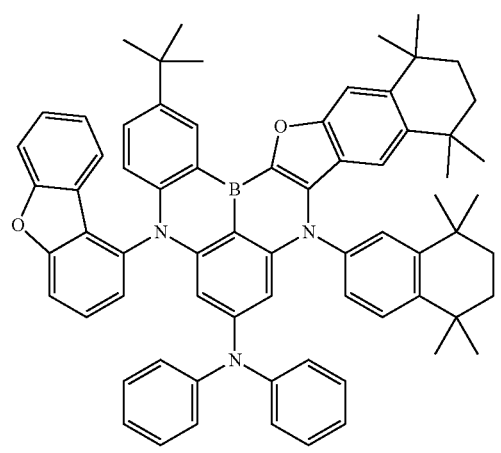
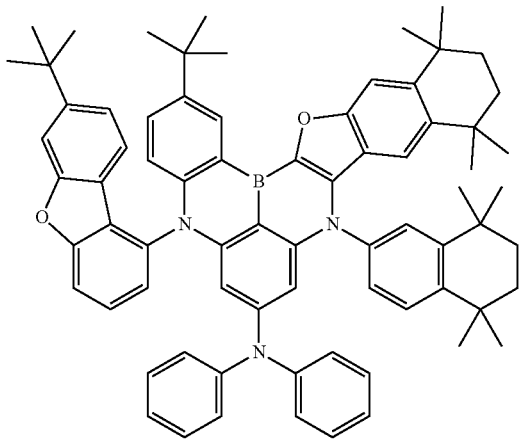

713
-continued
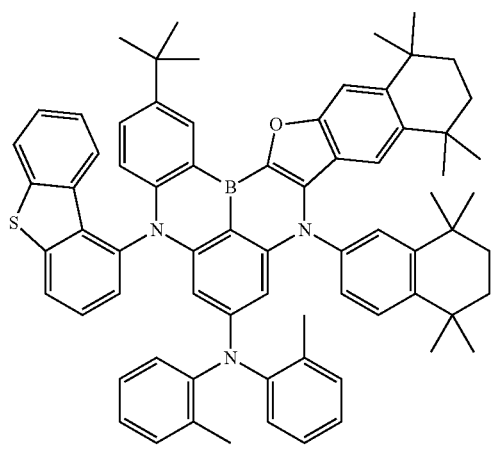
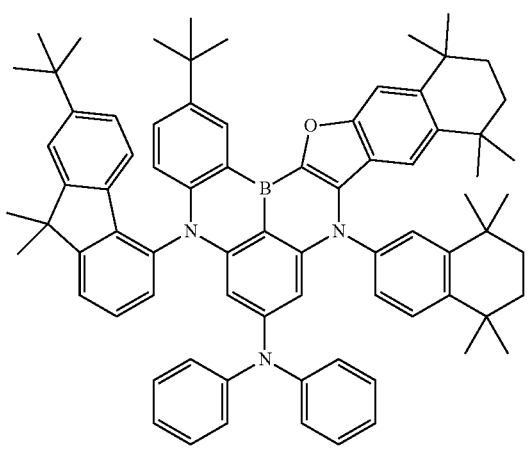
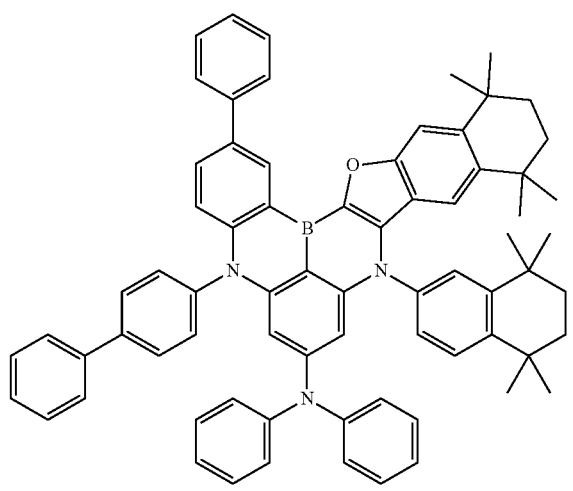
714
-continued

715
-continued
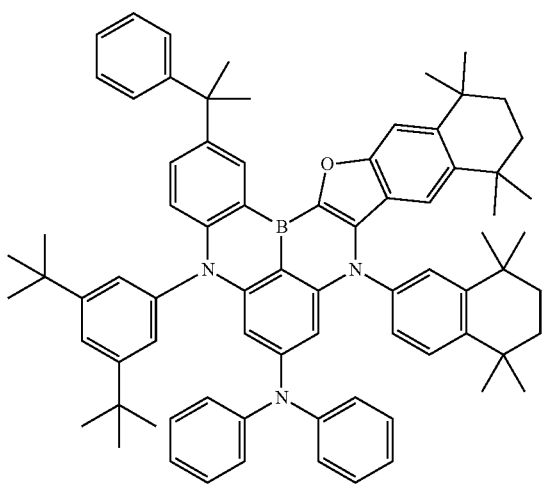
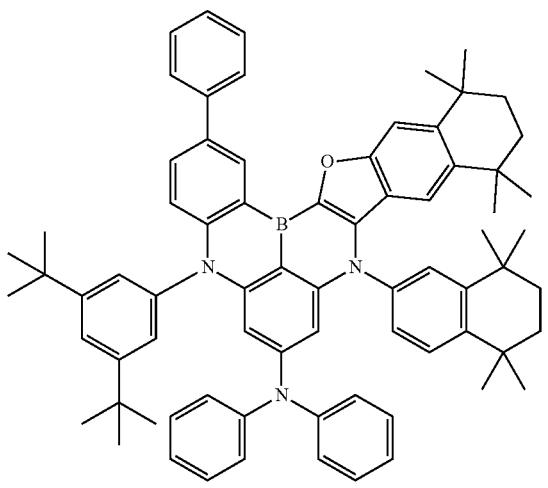
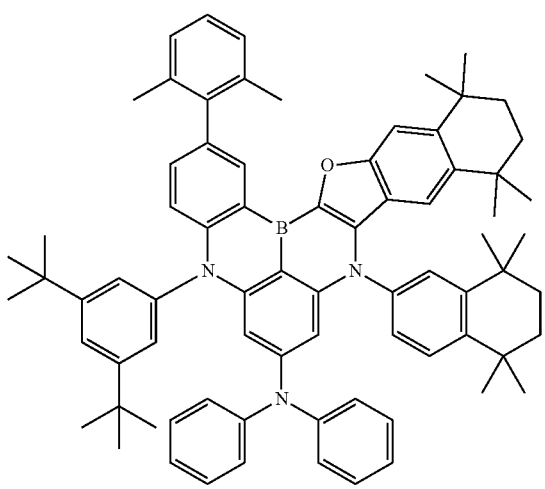
716
-continued
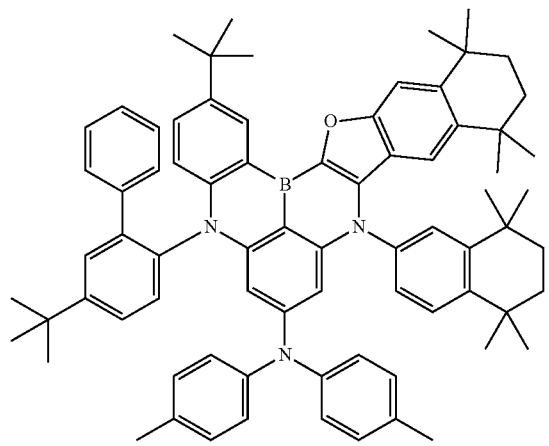

717
-continued
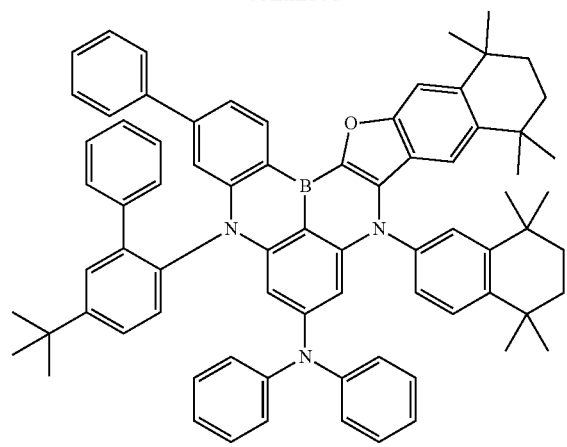
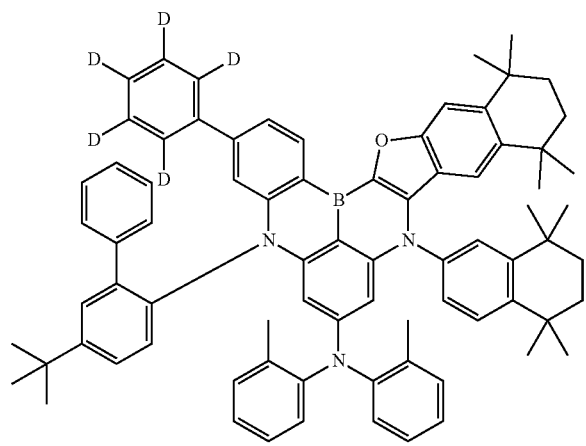
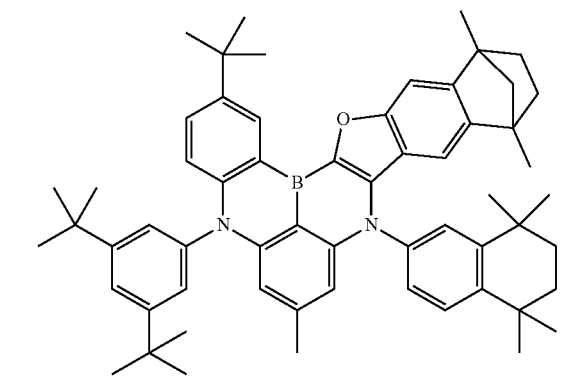
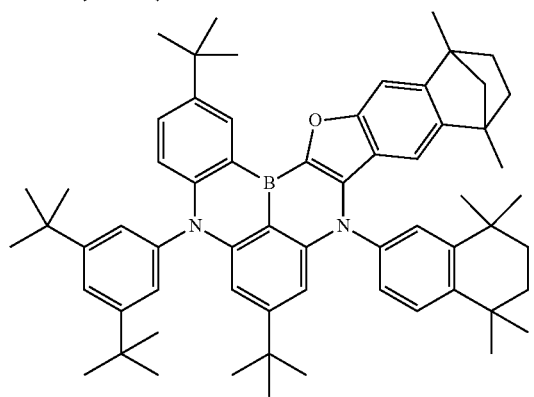
718
-continued
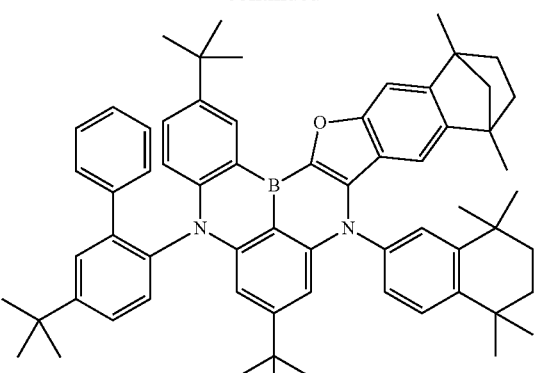
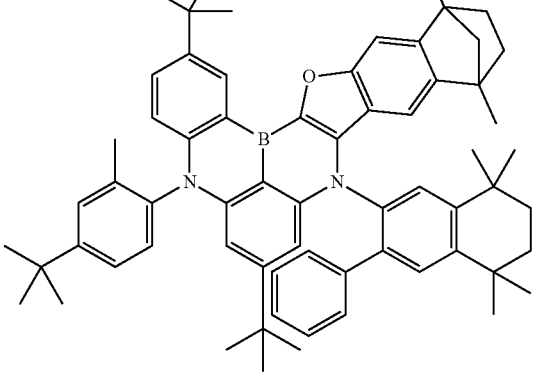
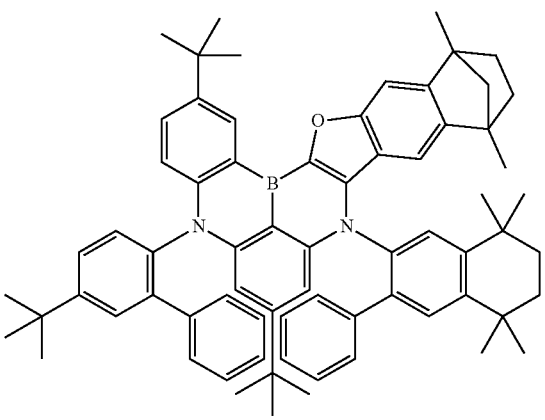
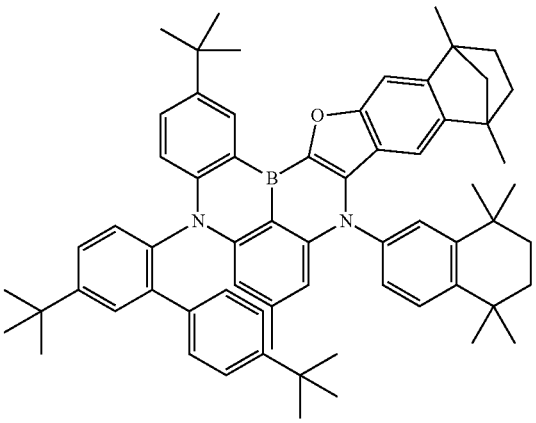

719
-continued
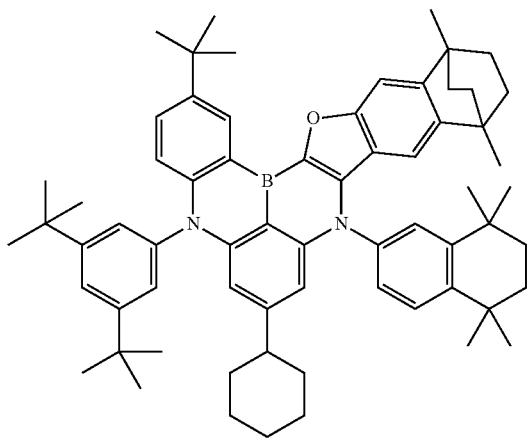
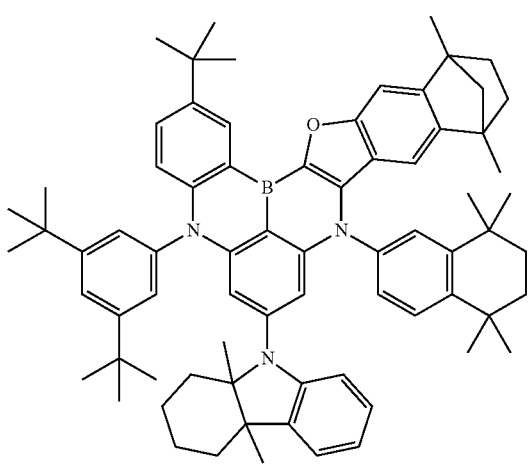
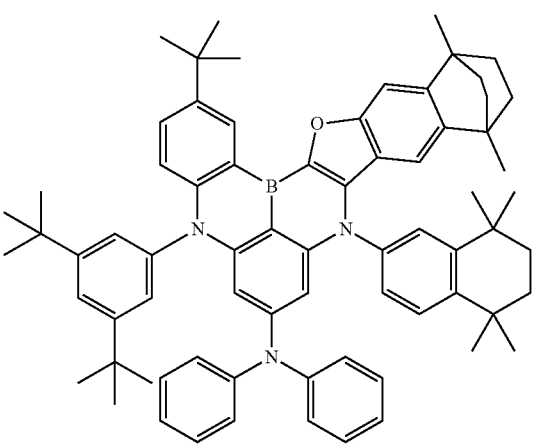
720
-continued
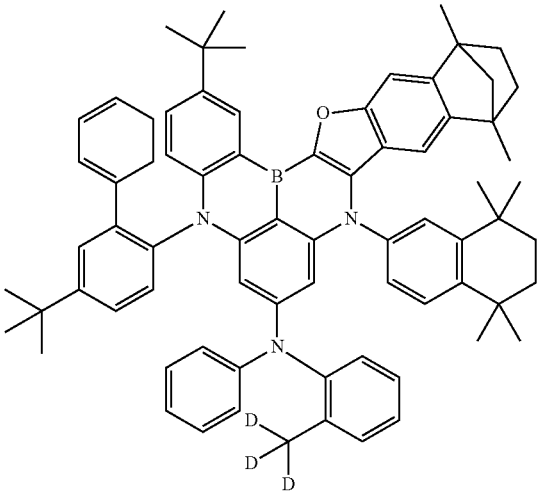
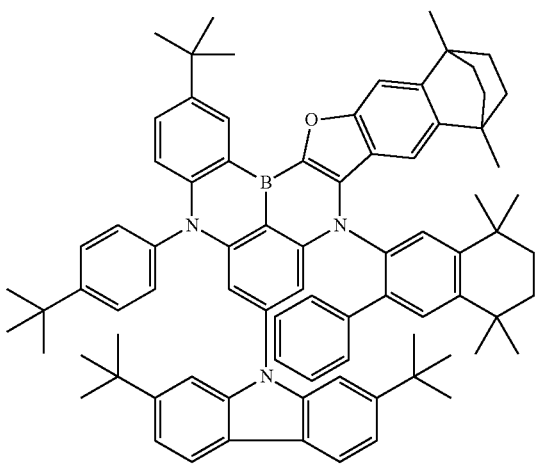
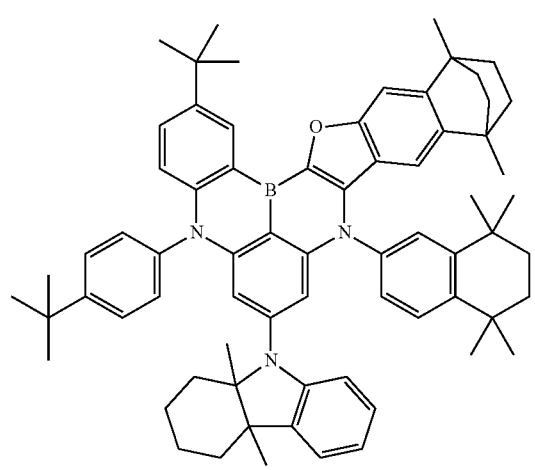

721
-continued
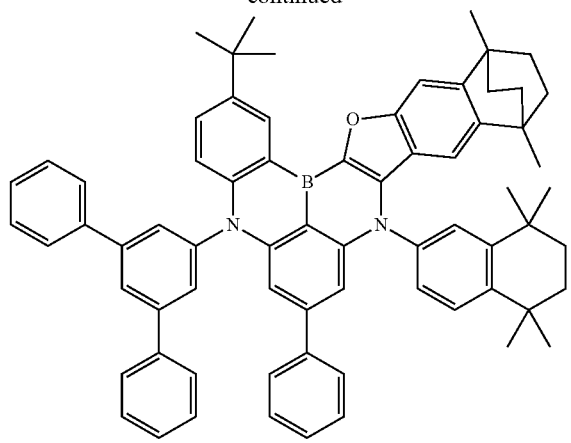
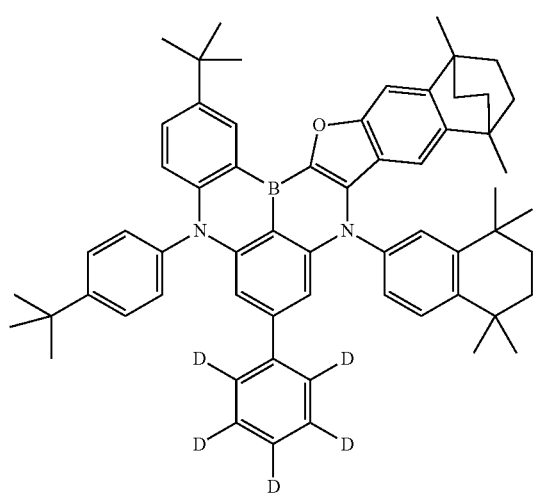
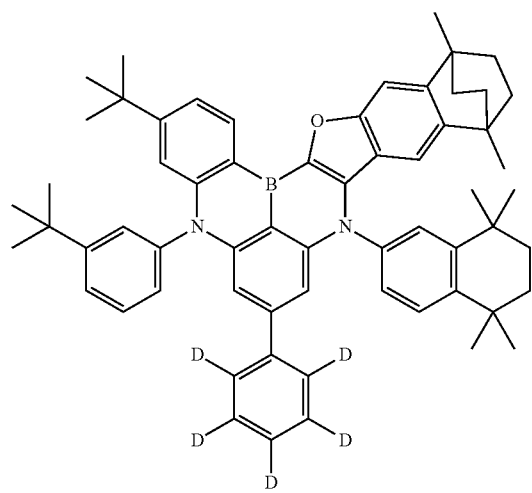
722
-continued
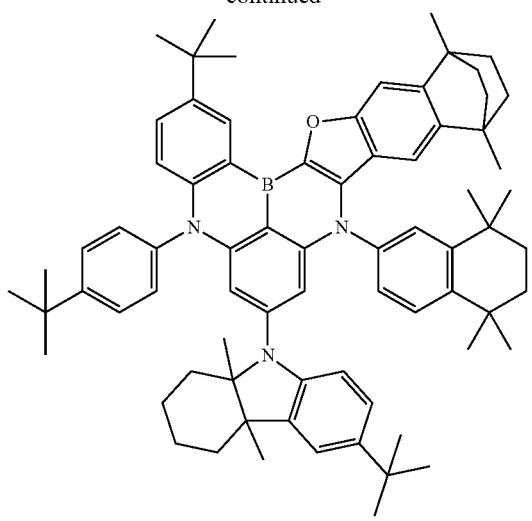
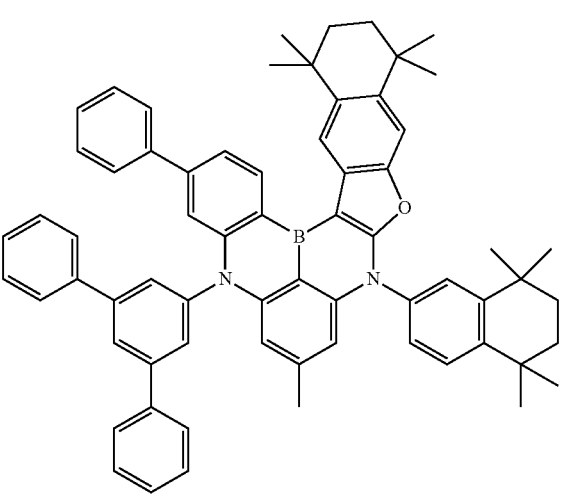
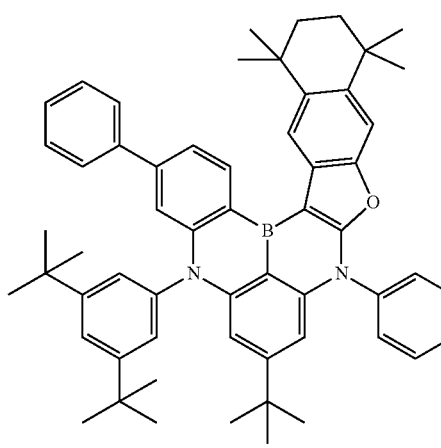

723 -continued
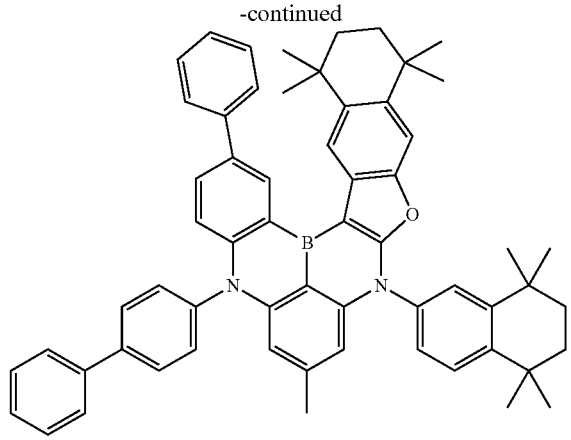
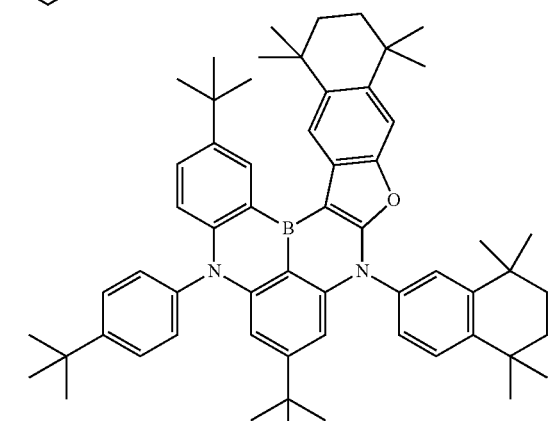
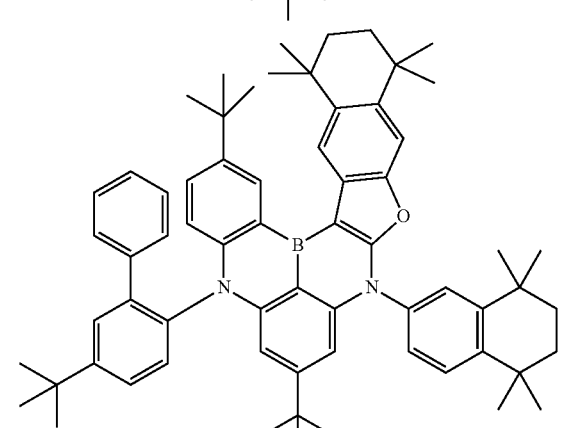
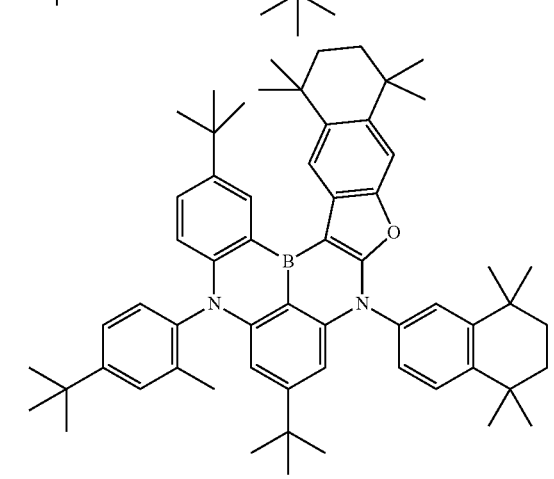
724 -continued
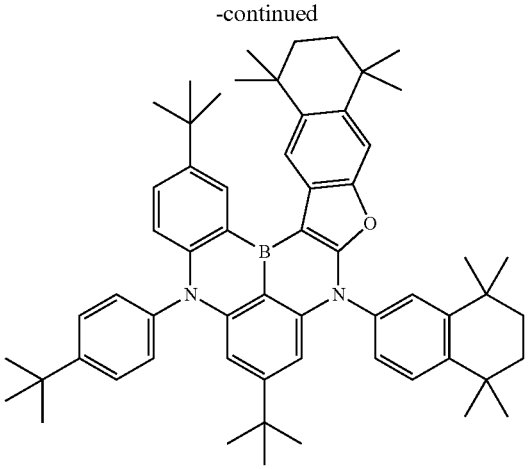
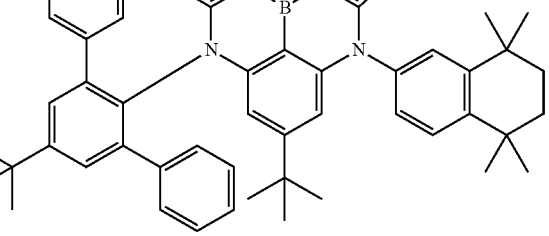
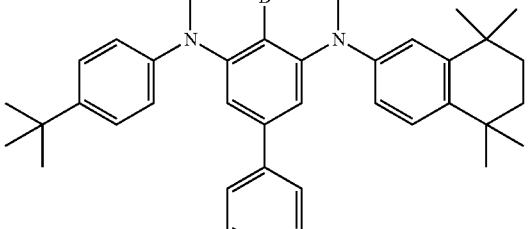

725
-continued
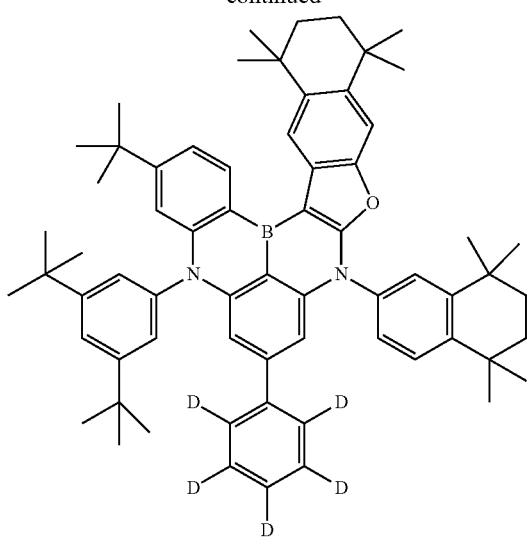
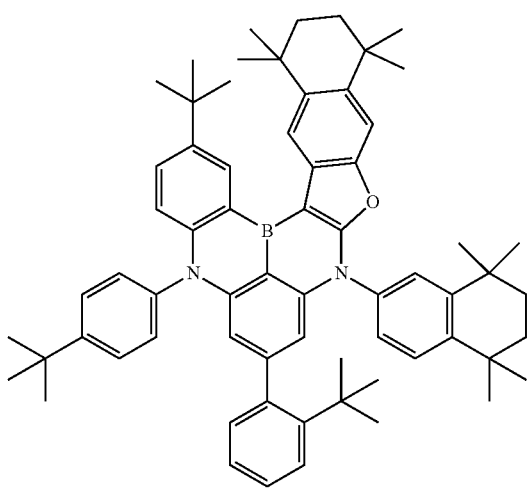
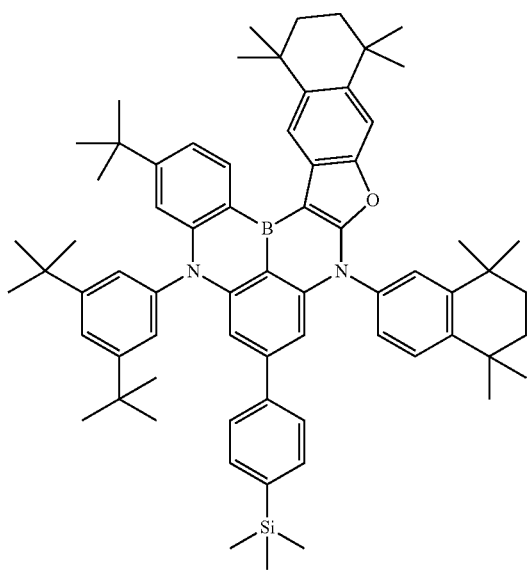
726
-continued
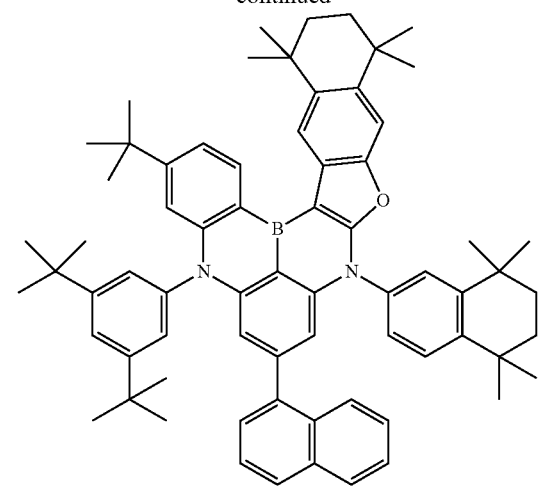
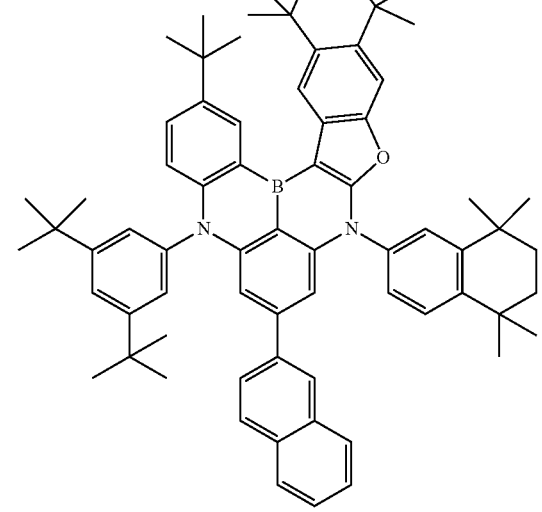
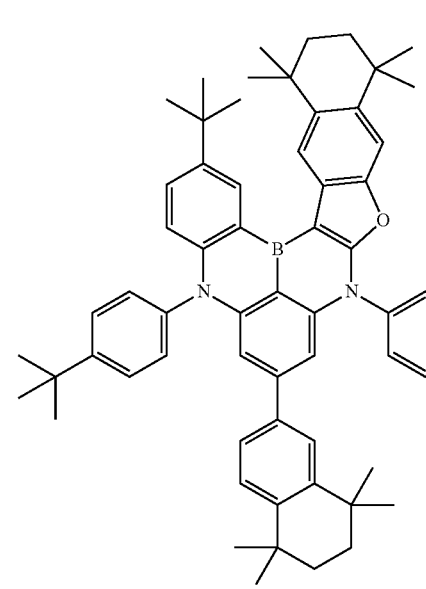

727
-continued
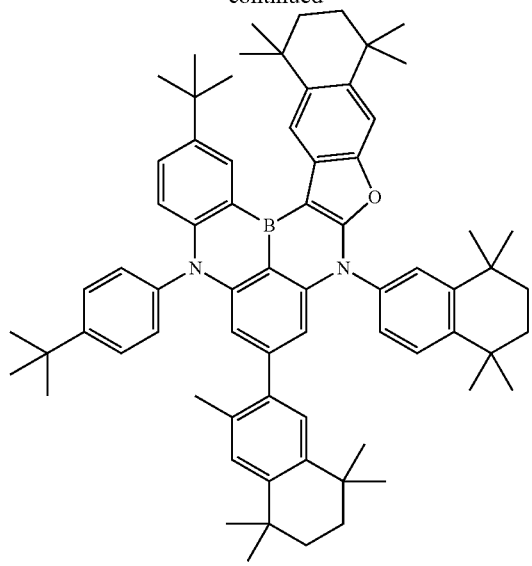
728
-continued
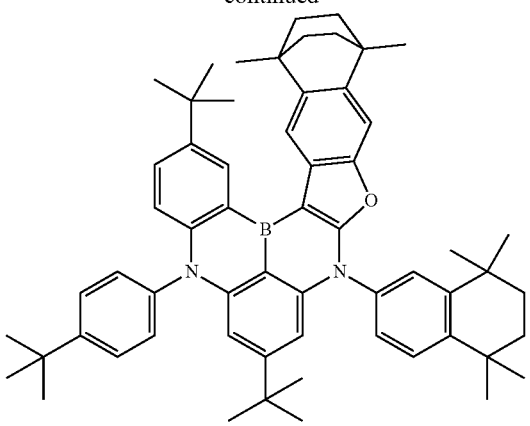
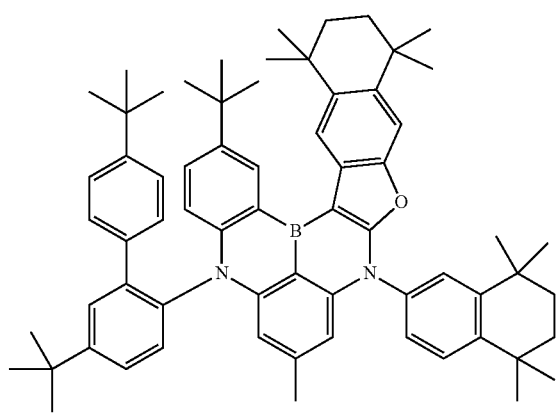
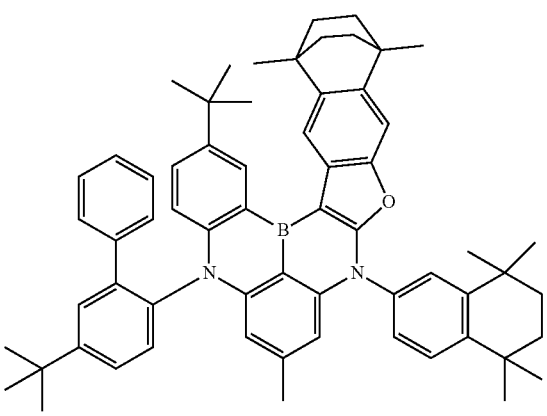
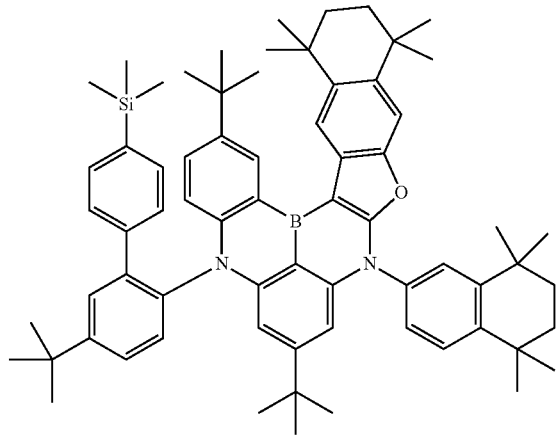

729
-continued
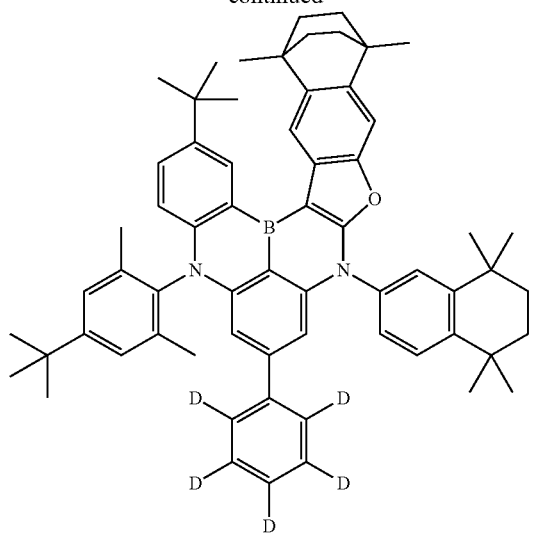
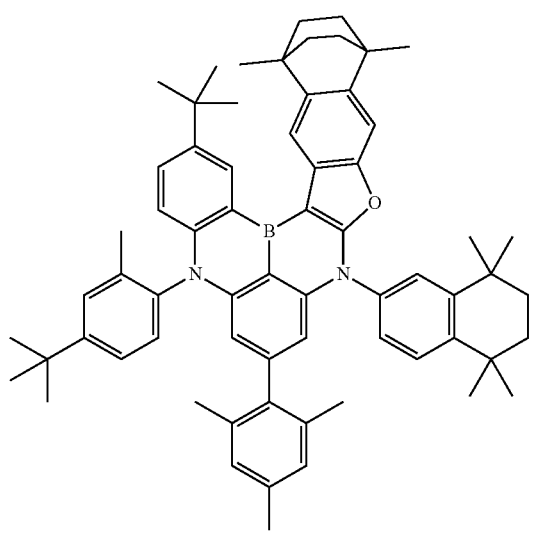
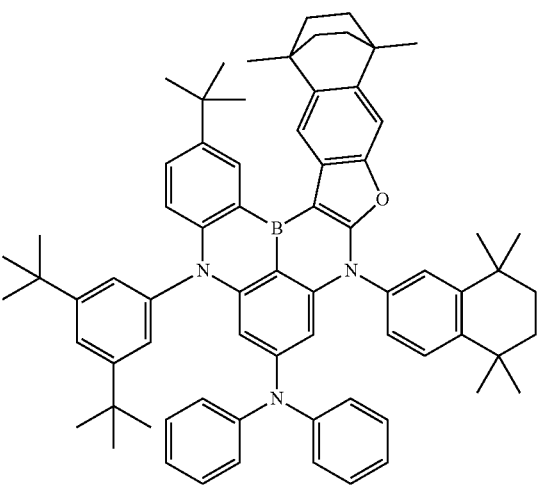
730
-continued
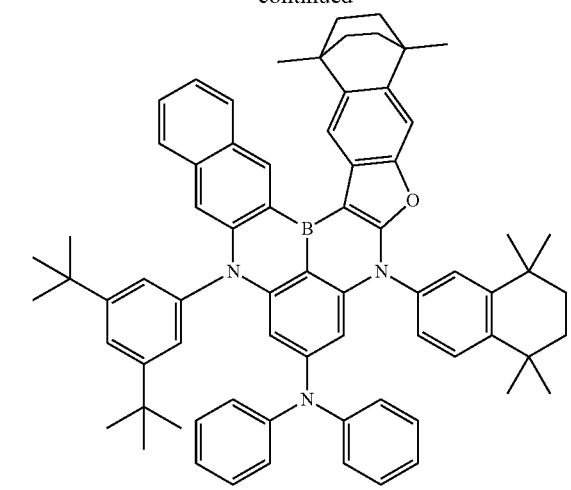
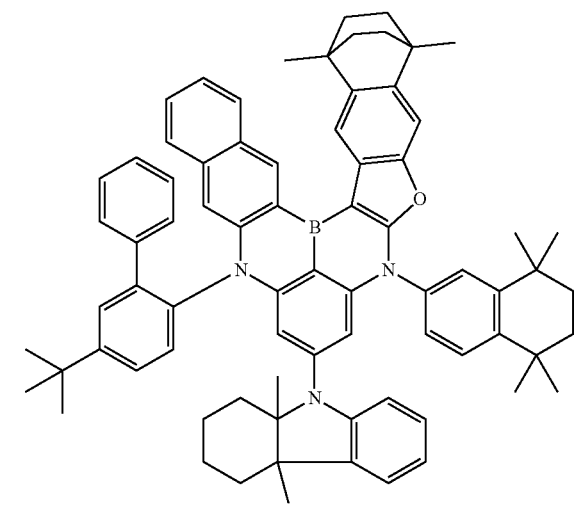
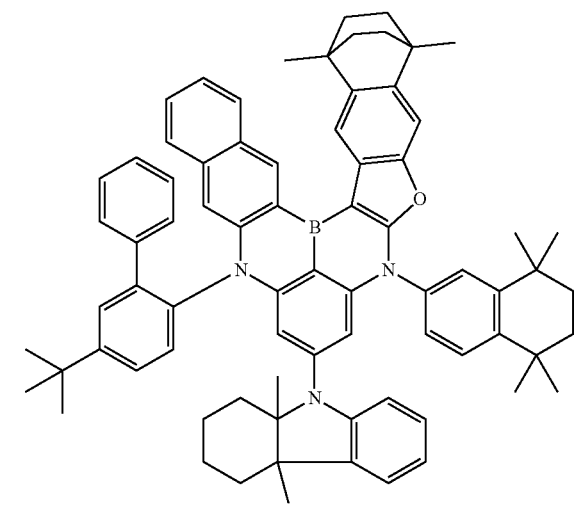

731
-continued
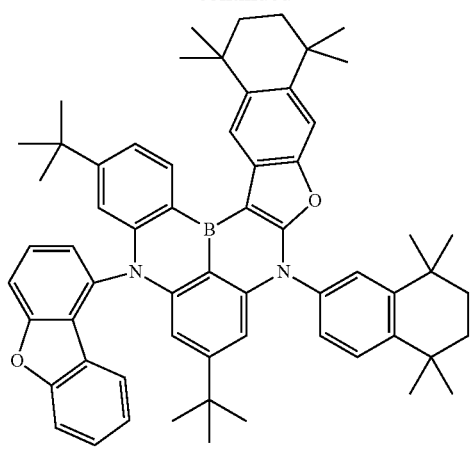
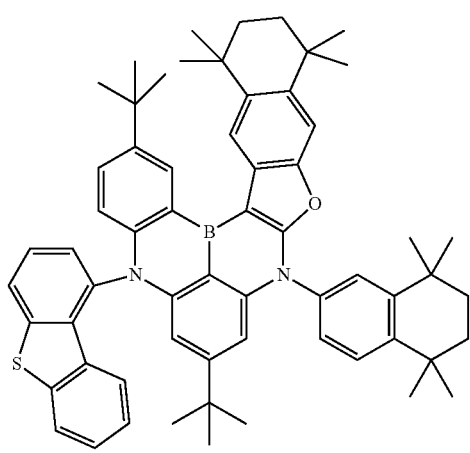
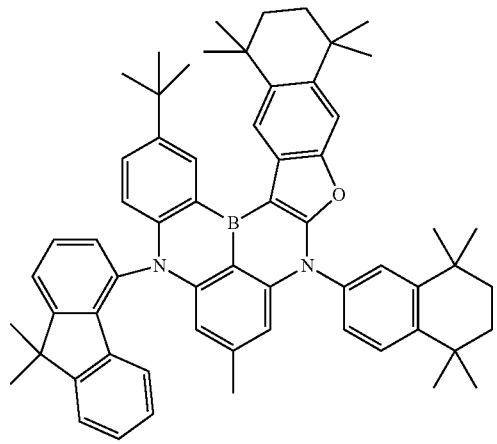
732
-continued
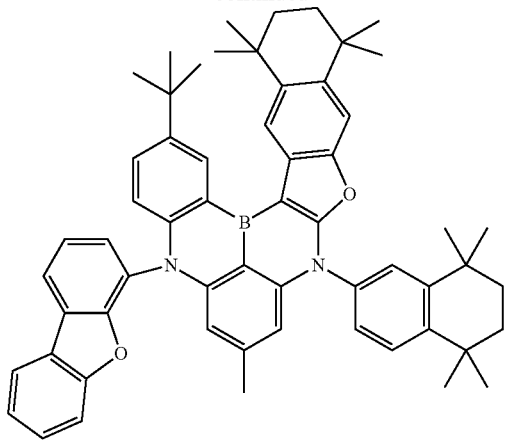
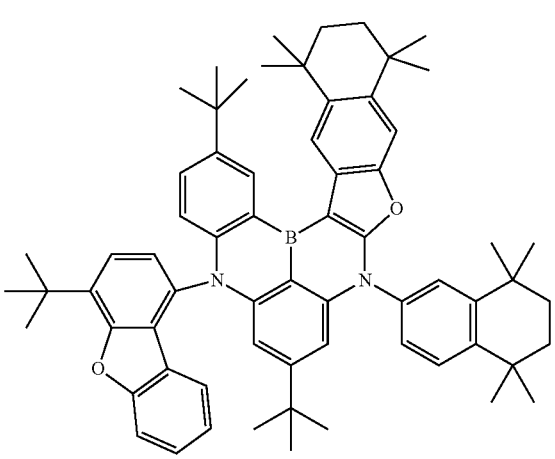
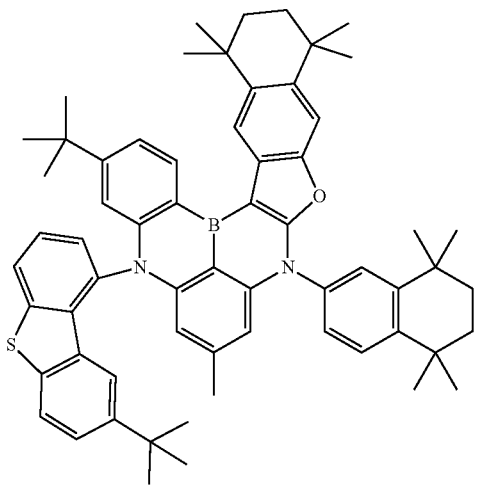

733
-continued
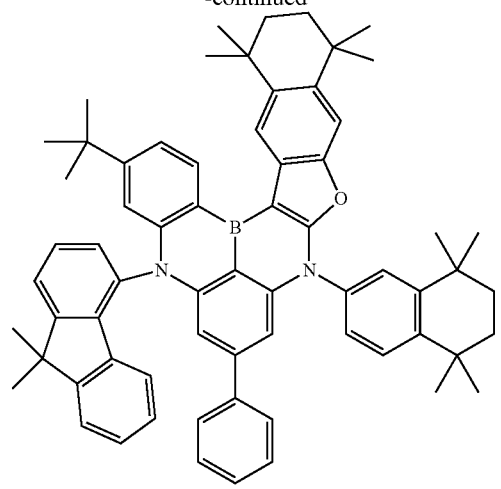
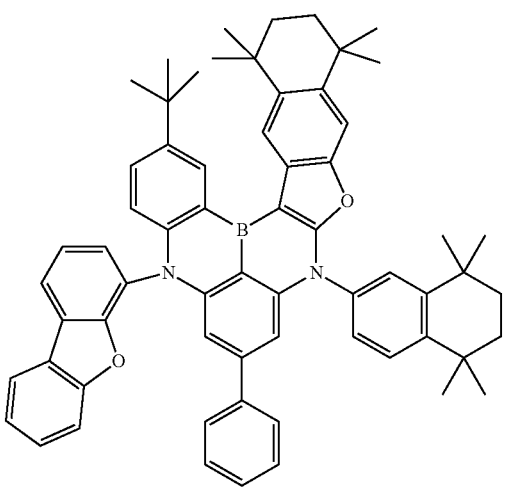
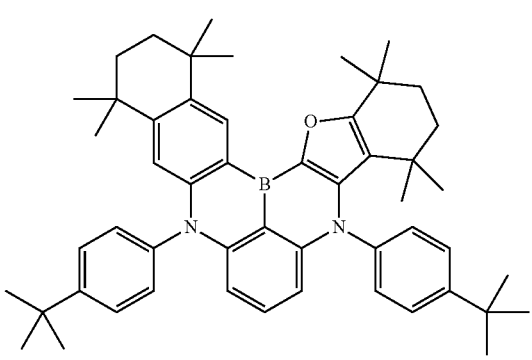
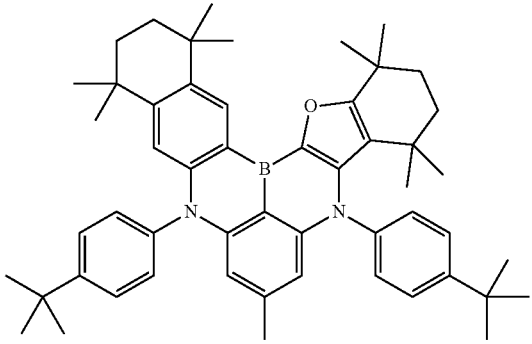
734
-continued
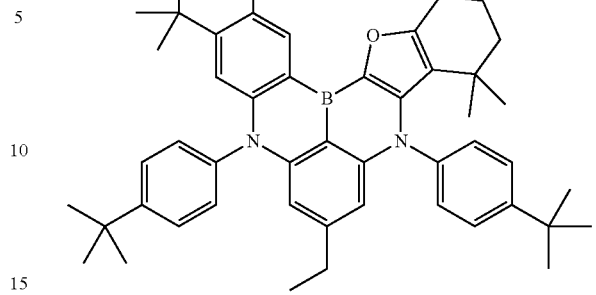
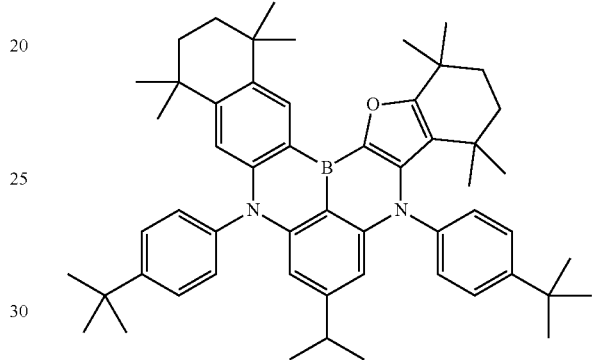
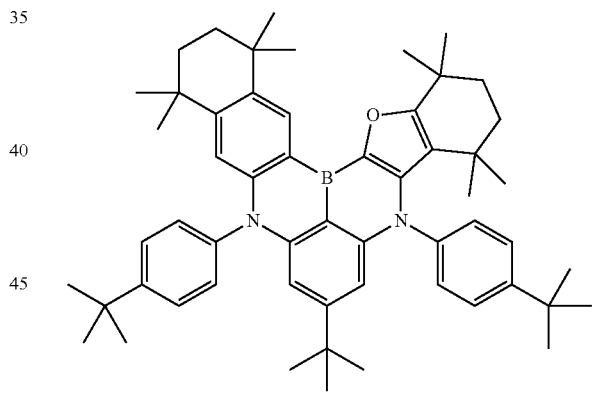
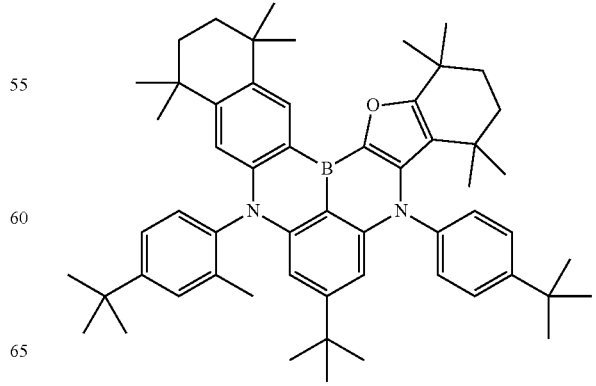

735
-continued
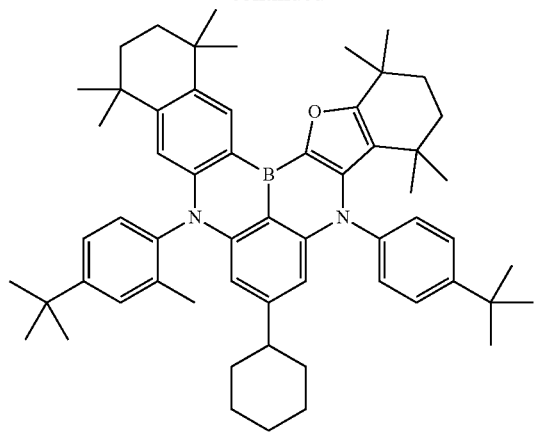
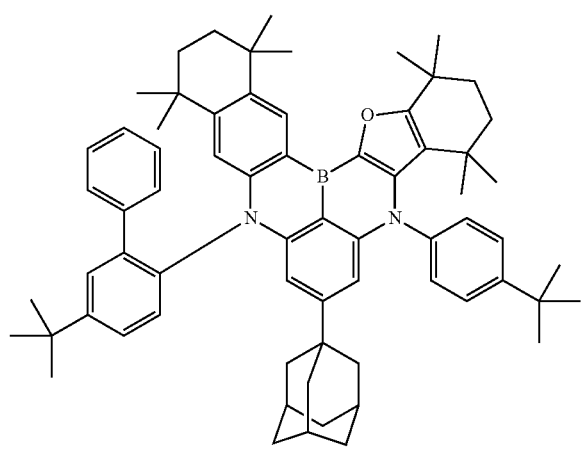
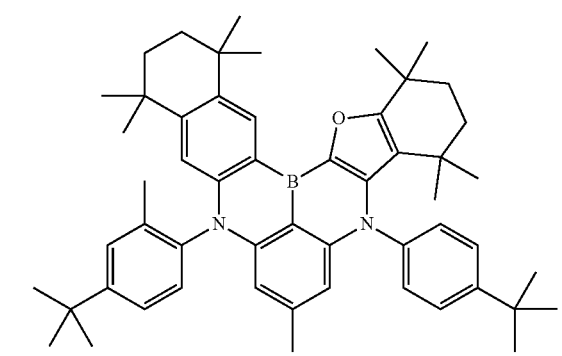
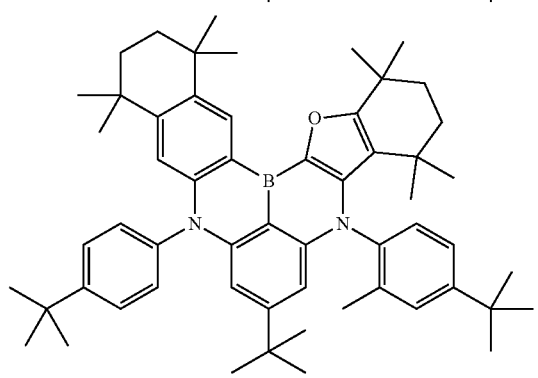
736
-continued
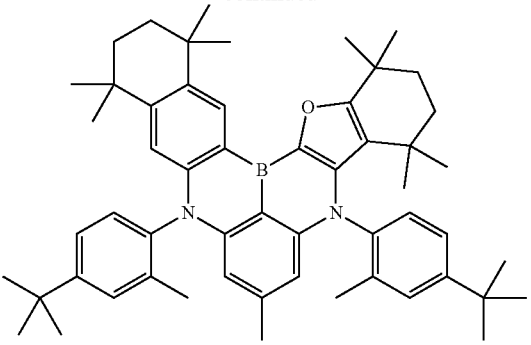
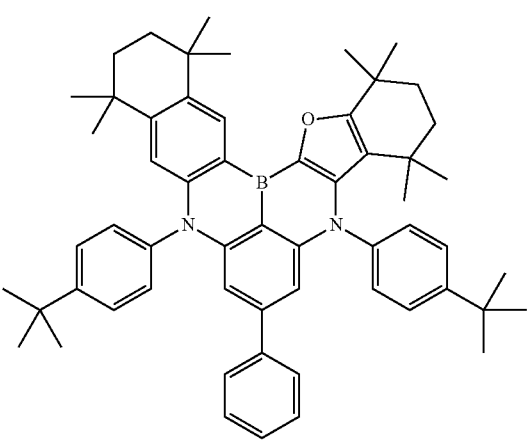
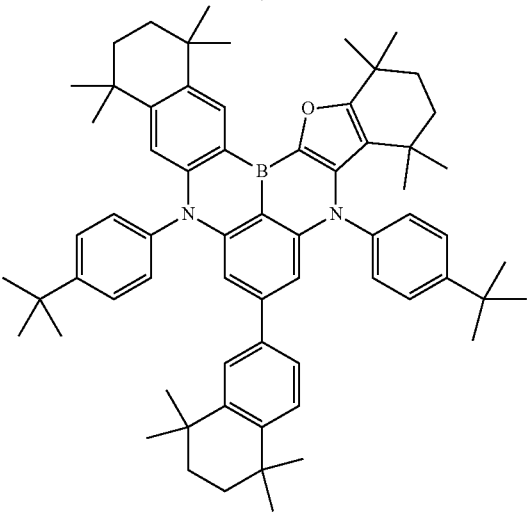
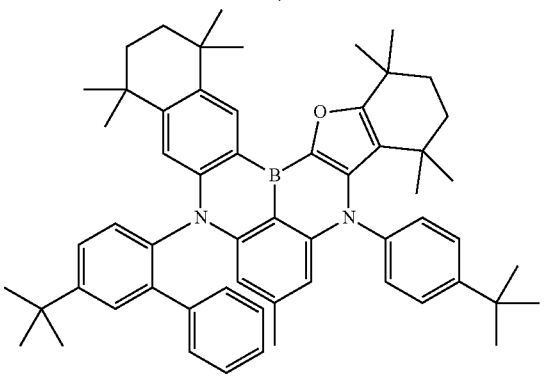

737
-continued
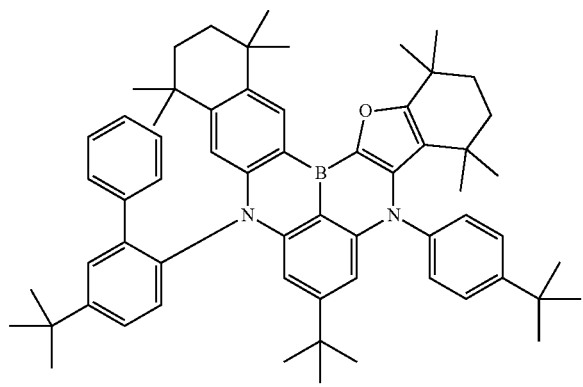
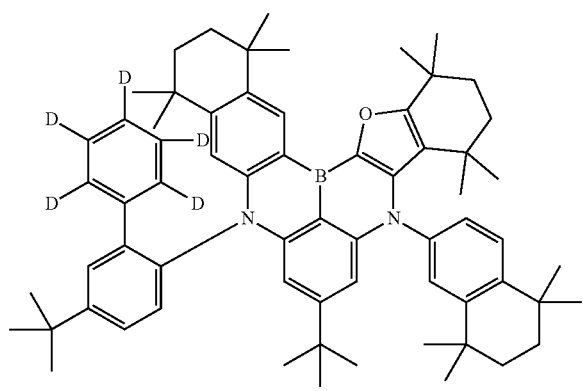
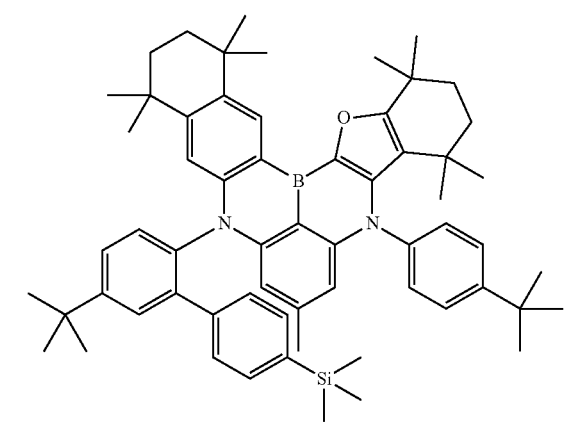
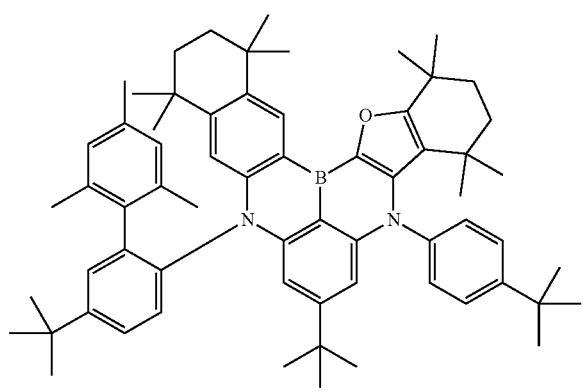
738
-continued
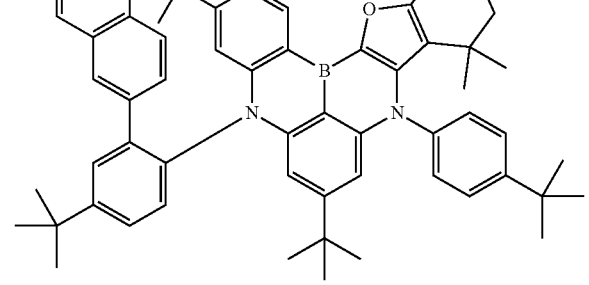
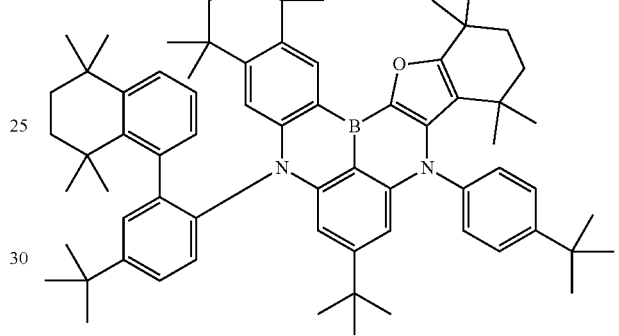
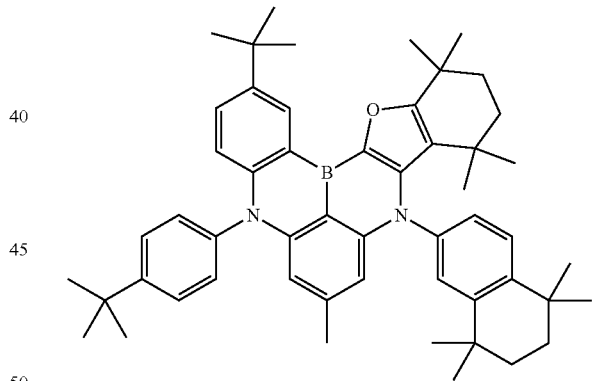
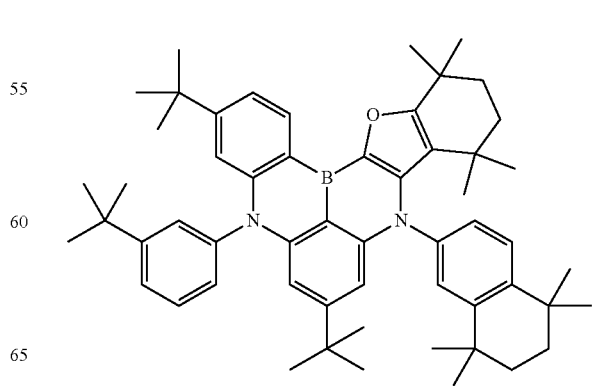

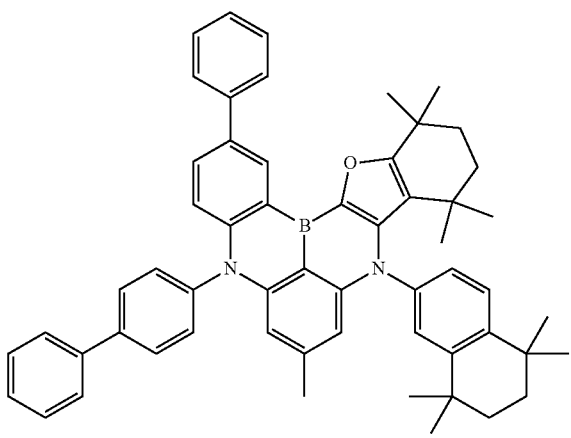
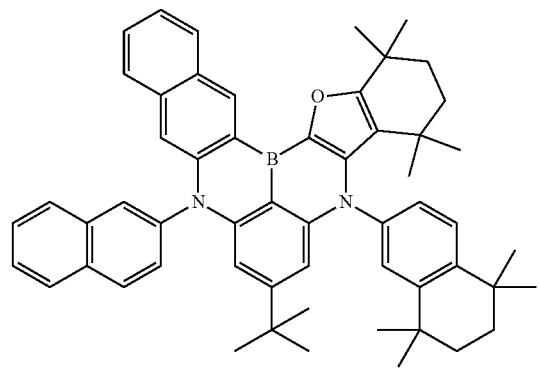
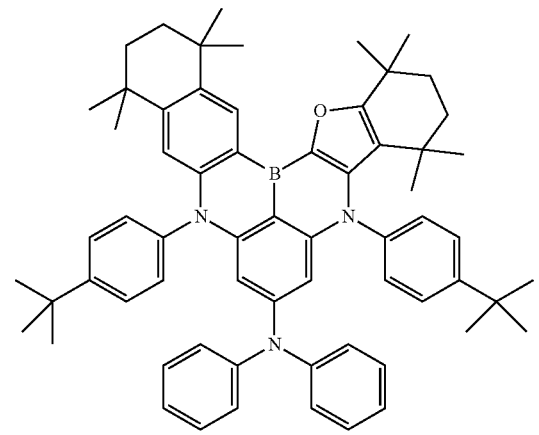
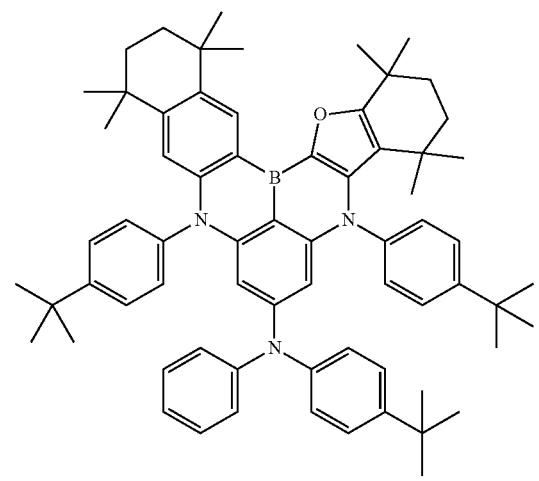
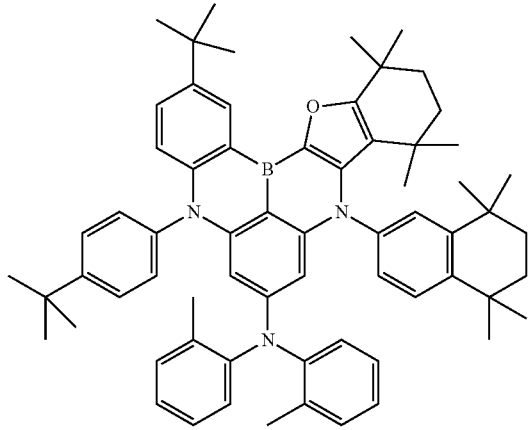
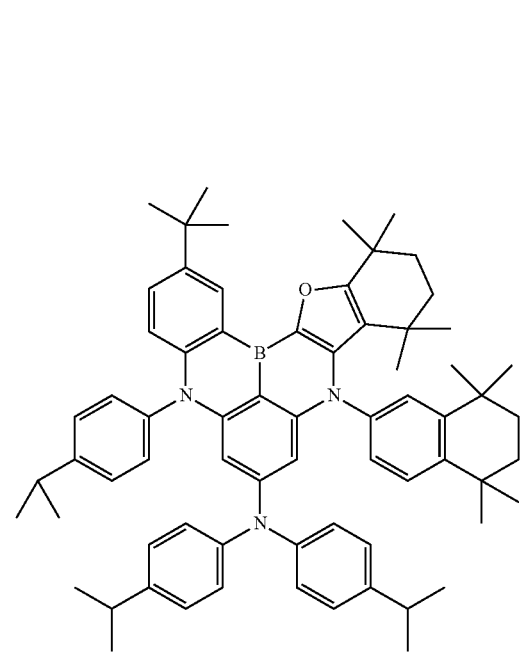
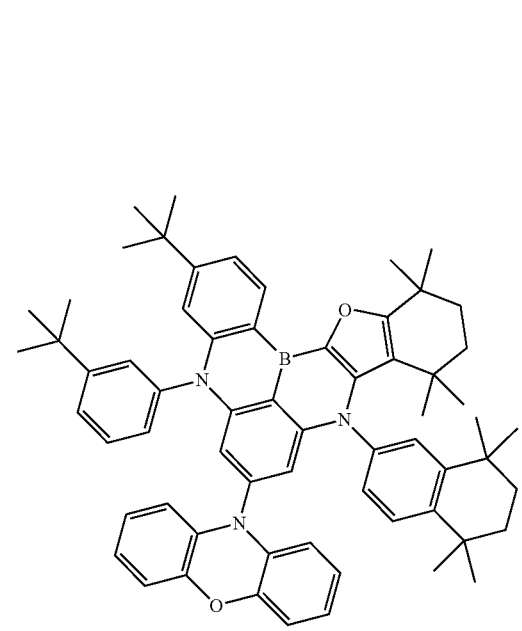

741
-continued
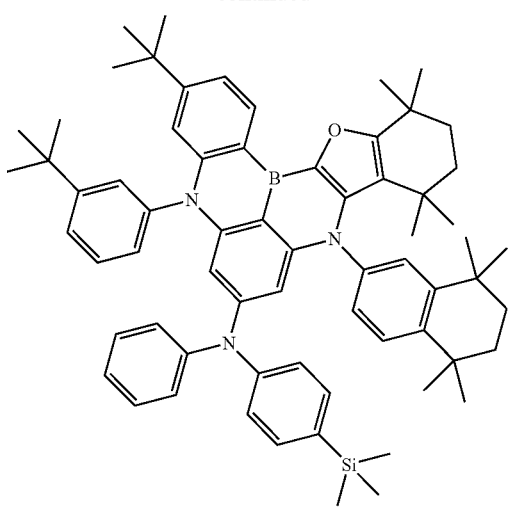
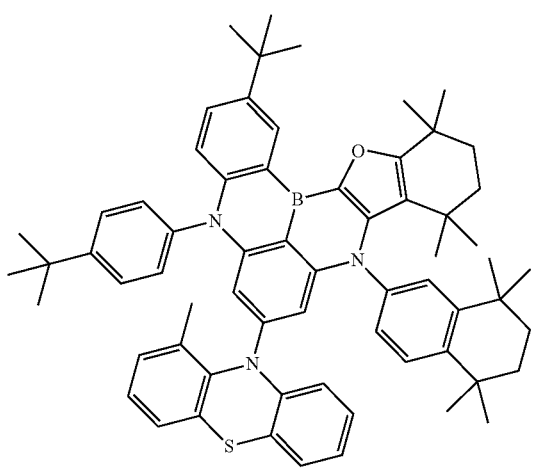
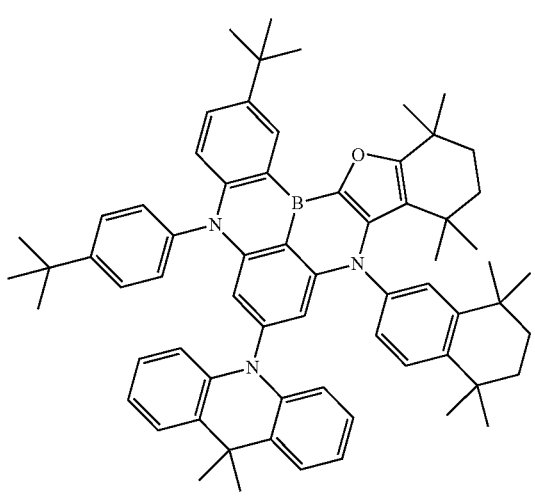
742
-continued
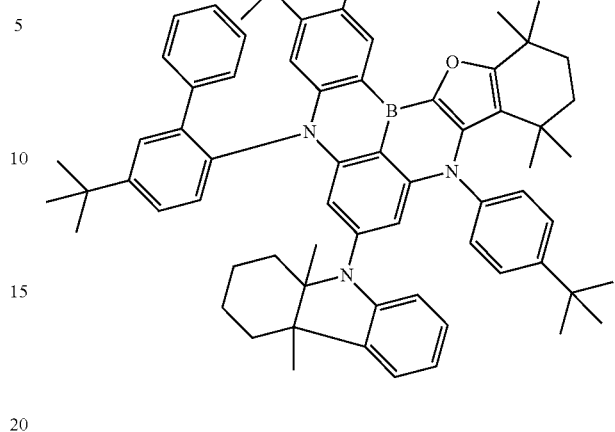
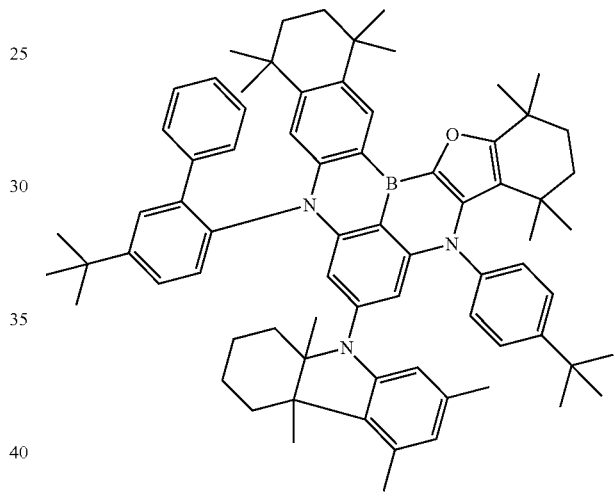
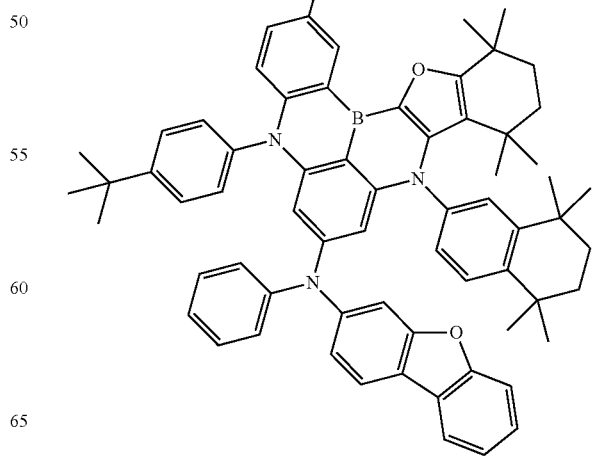

743
-continued
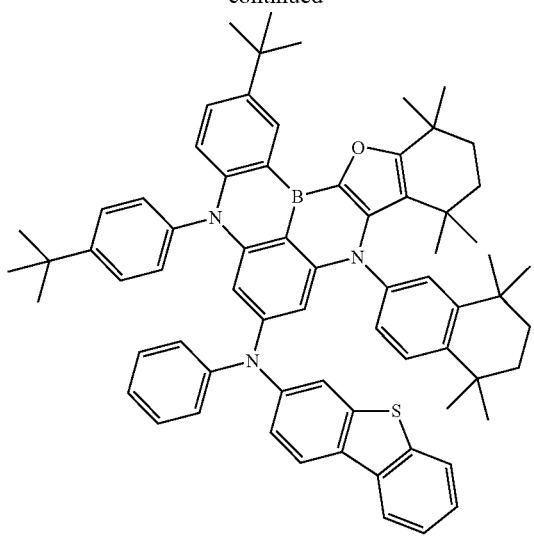
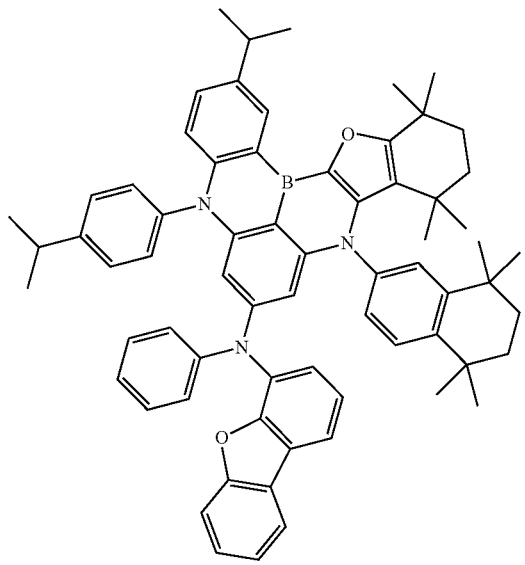
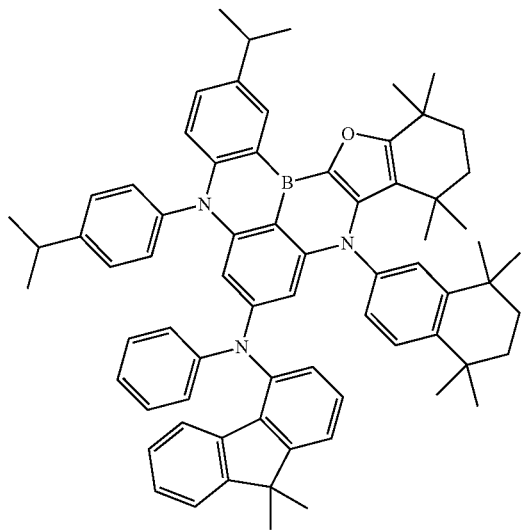
744
-continued
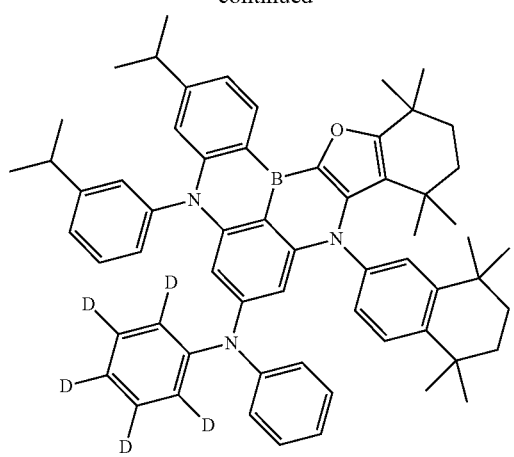
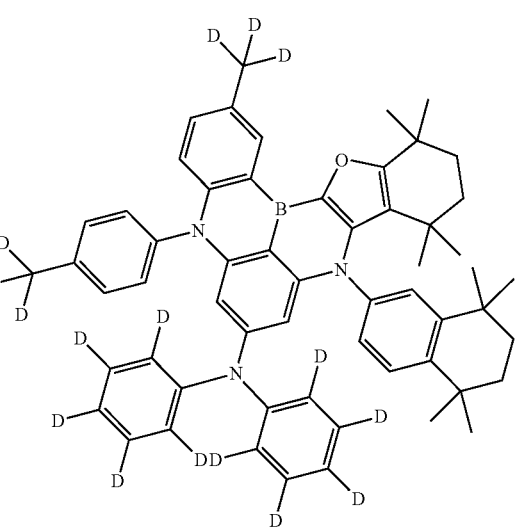
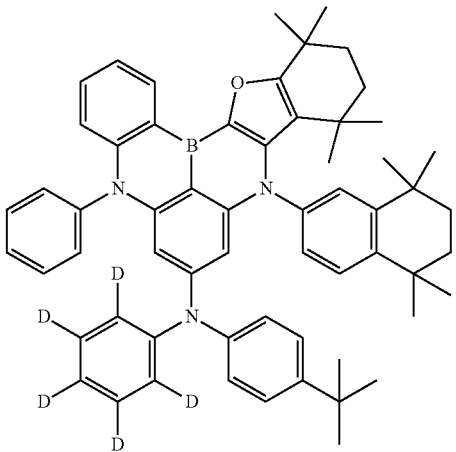

| 745 -continued | 746 -continued |
|---|---|
| 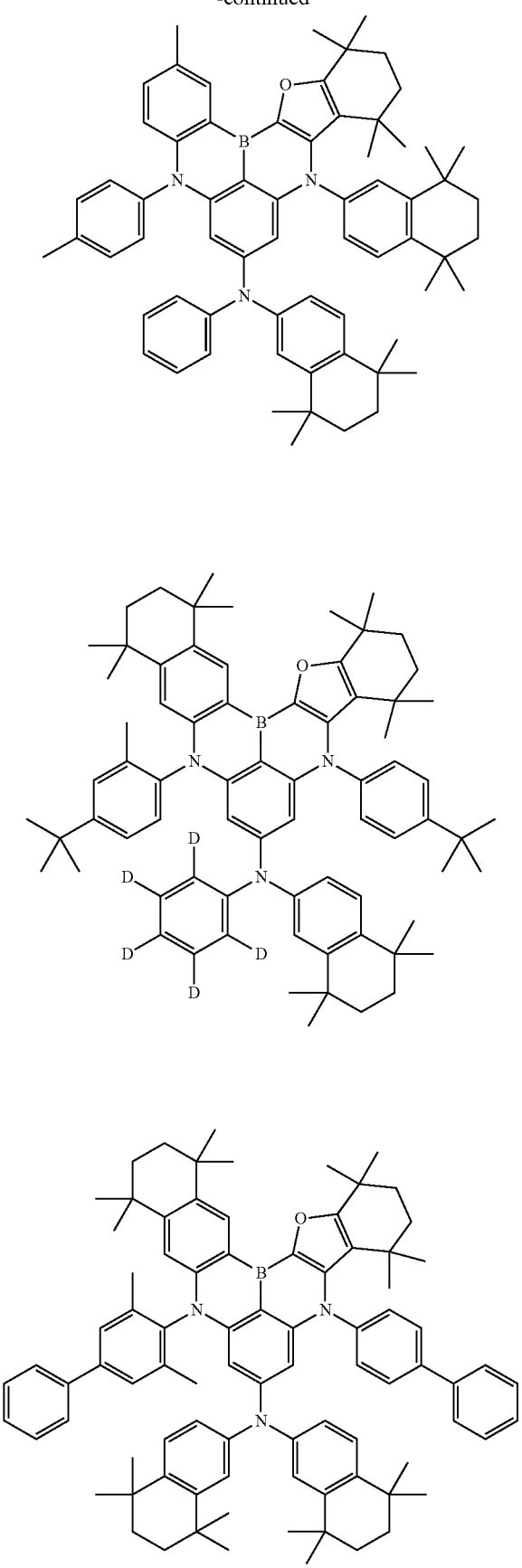 | 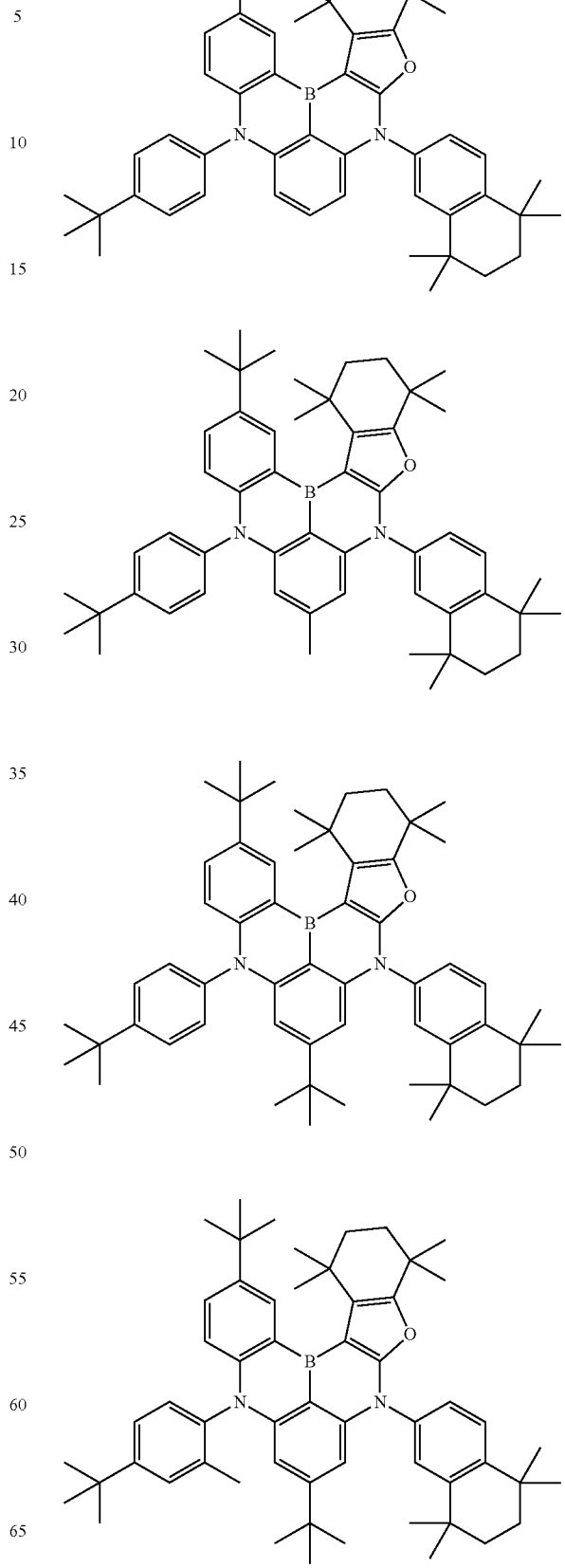 |

| 747 -continued | 748 -continued |
|---|---|
| 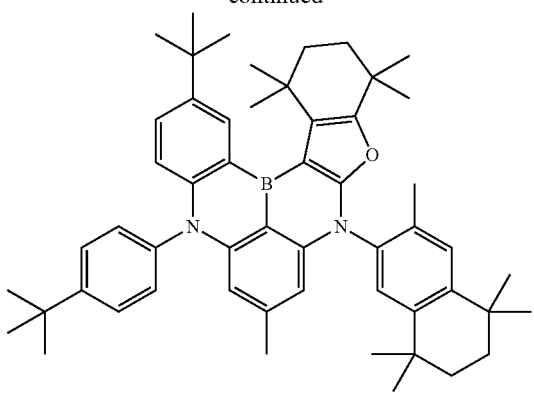 | 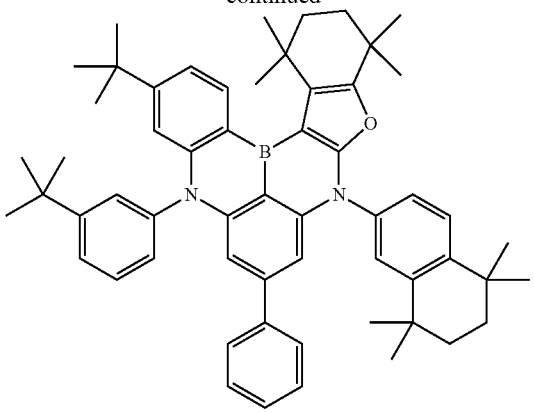 |
| 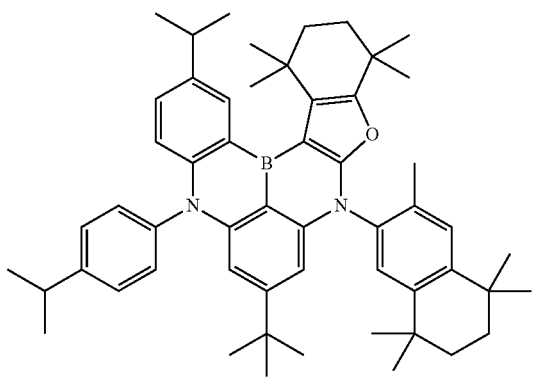 | 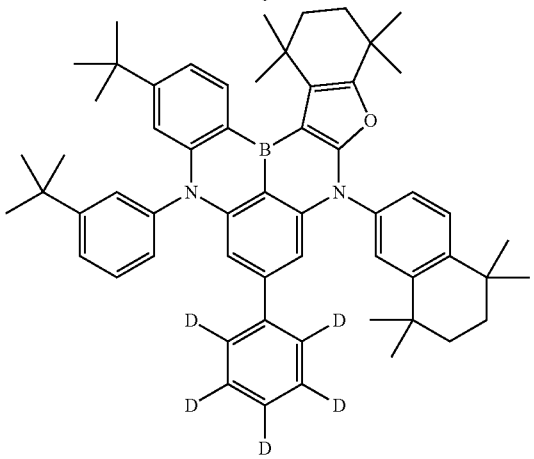 |
| 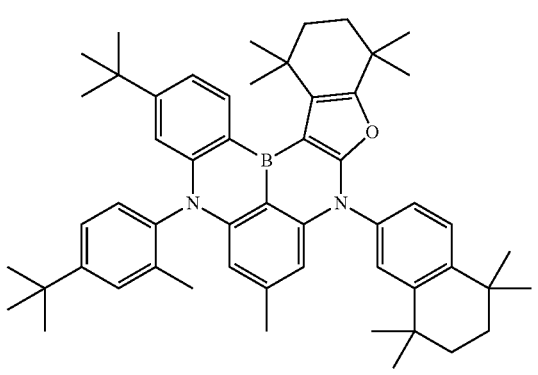 | 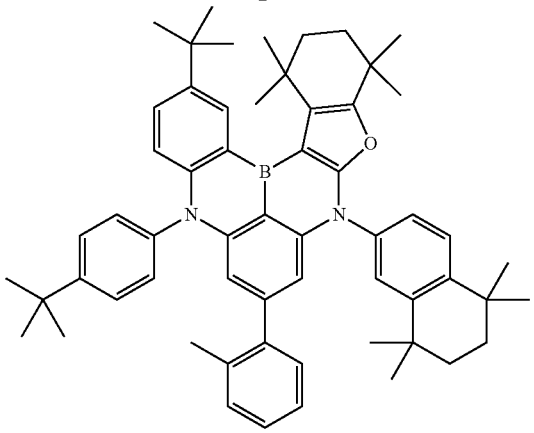 |
| 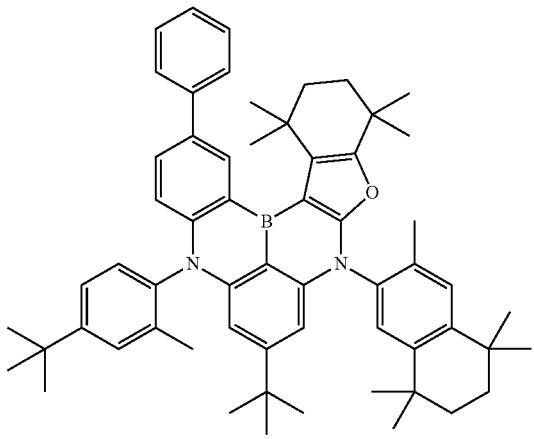 | 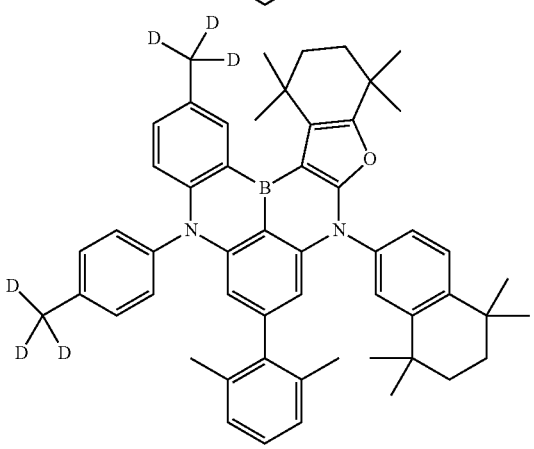 |

749
-continued
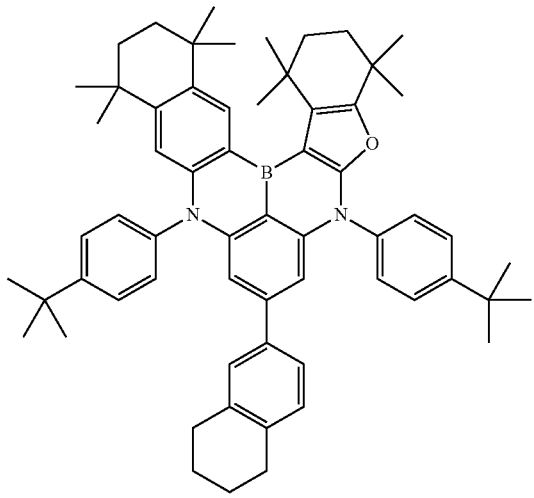
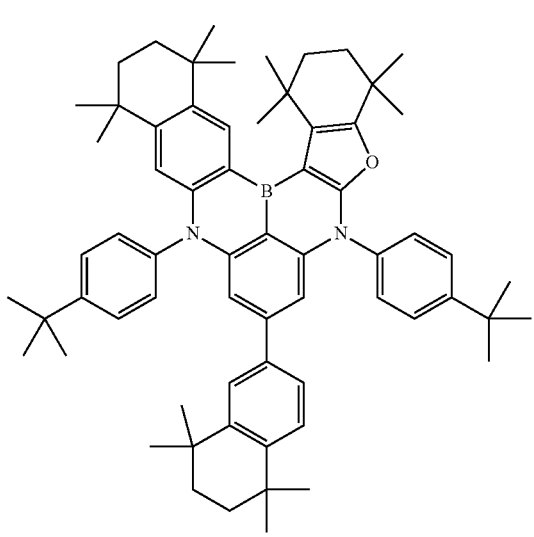
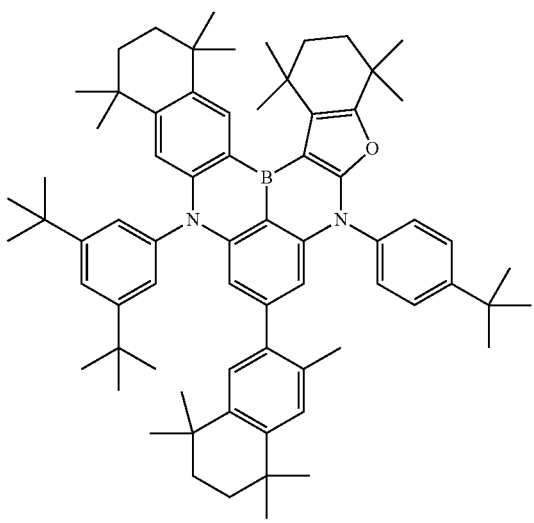
750
-continued
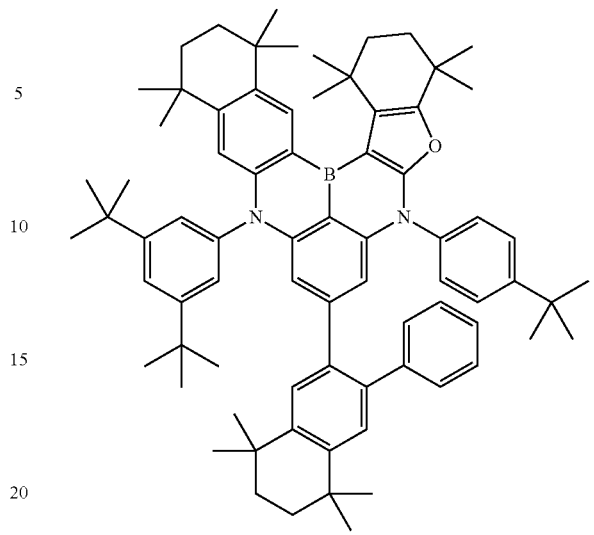
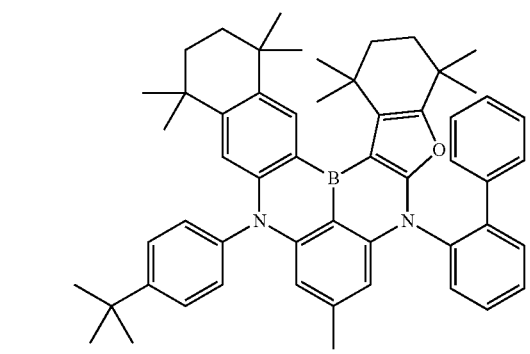
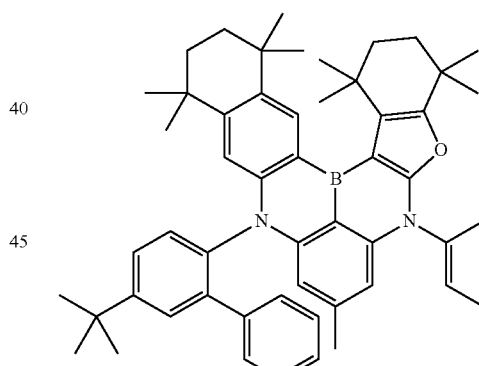
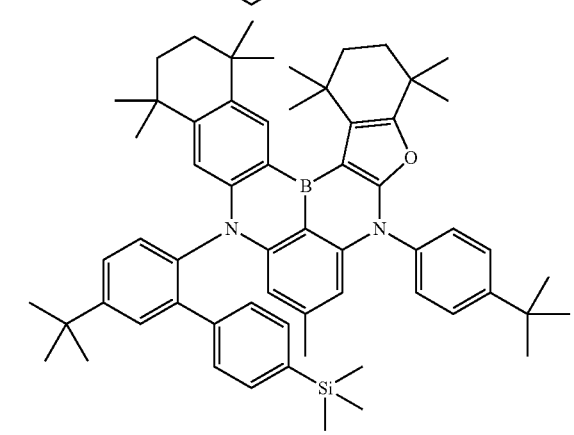

751
-continued
752
-continued
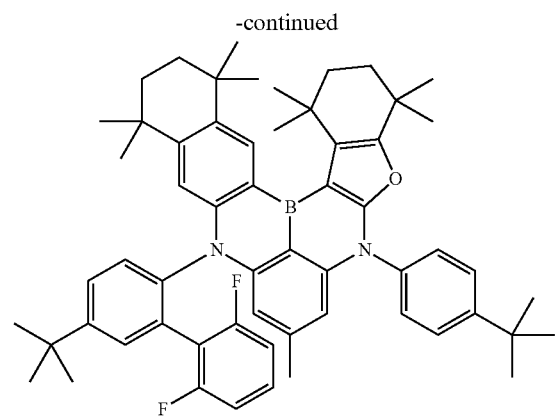
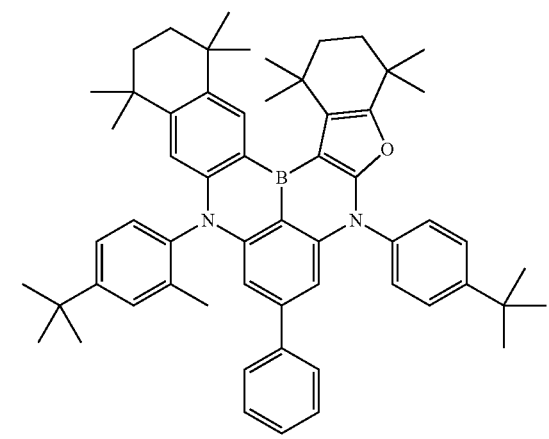
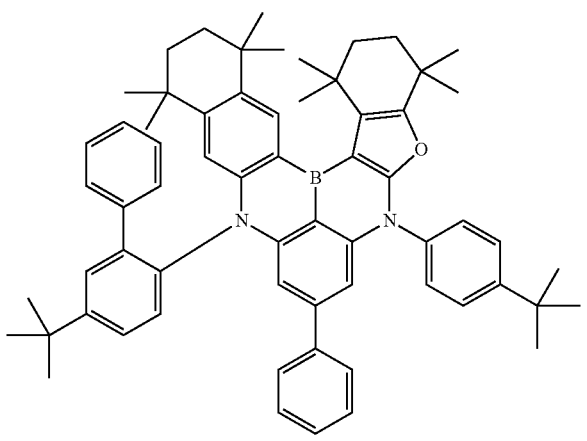
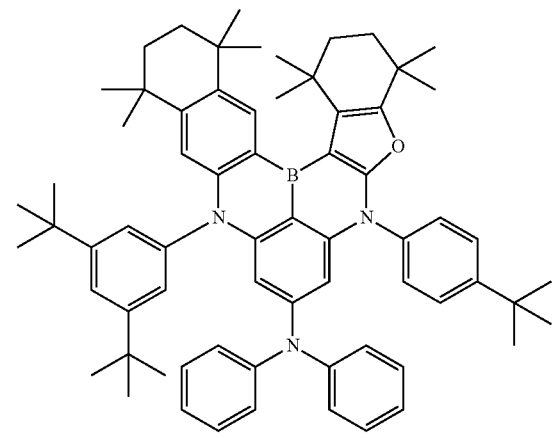
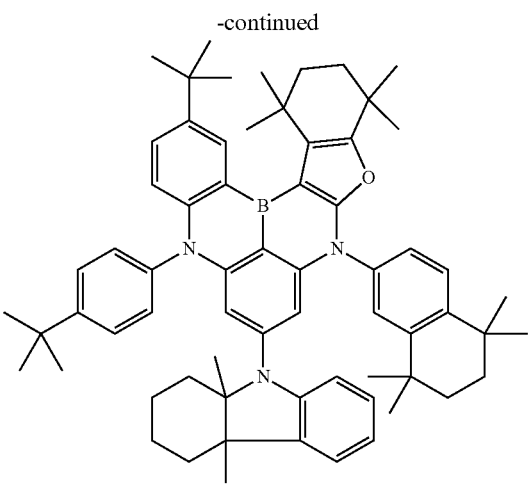
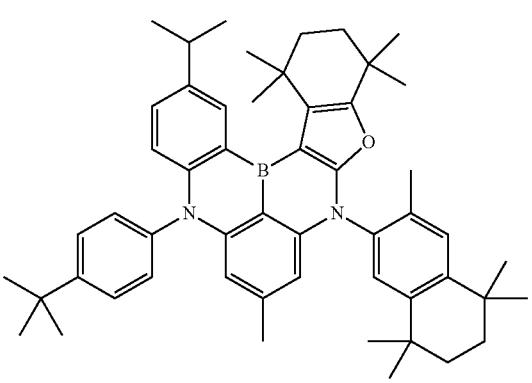
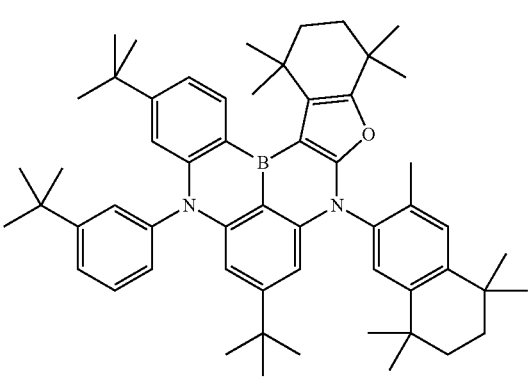
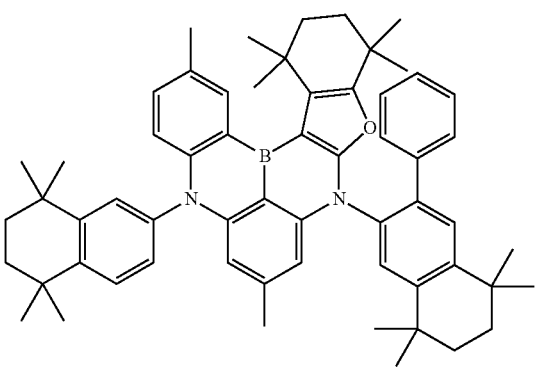

| 753 -continued | 754 -continued |
|---|---|
| 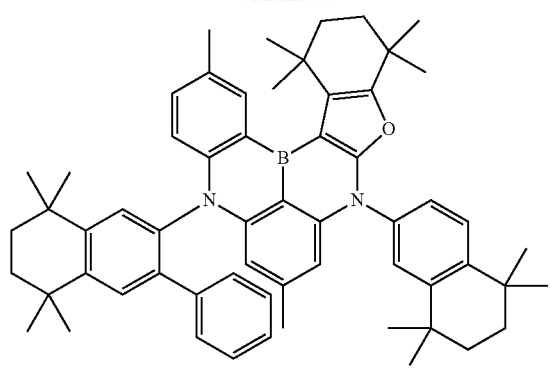 | 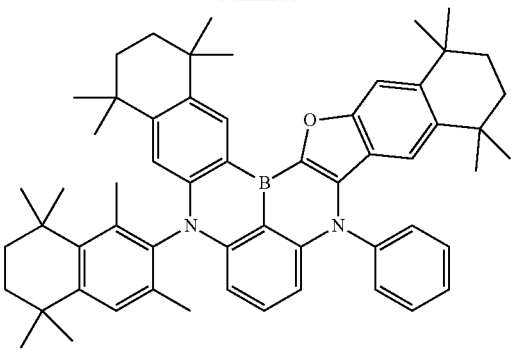 |
| 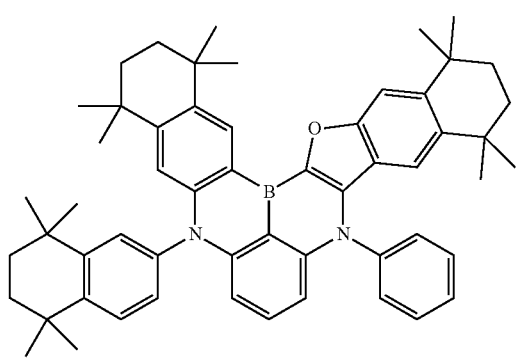 | 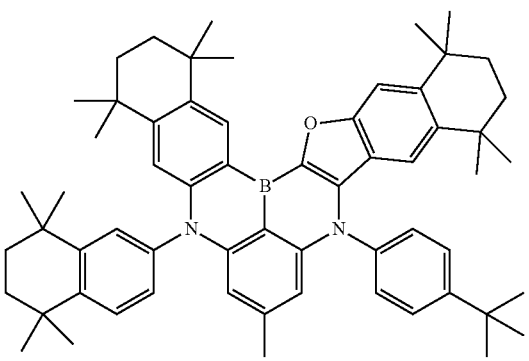 |
| 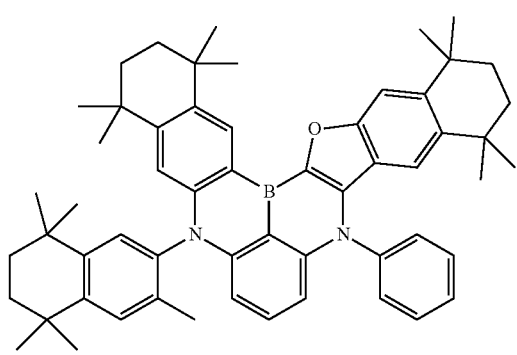 | 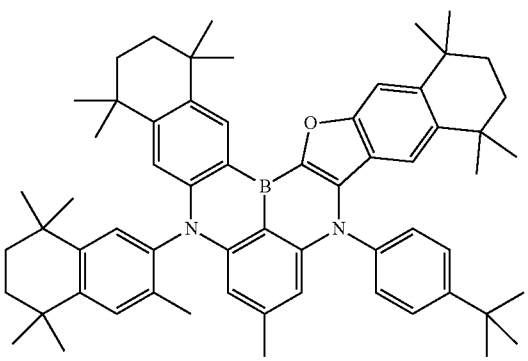 |
| 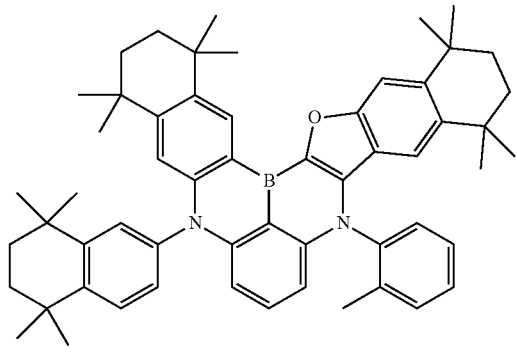 | 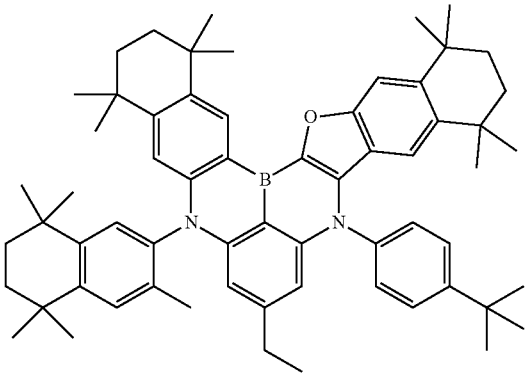 |

755
-continued

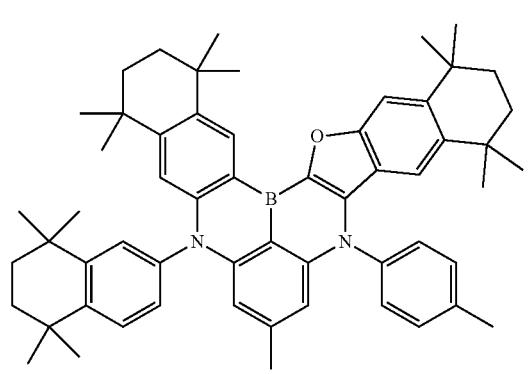
756
-continued
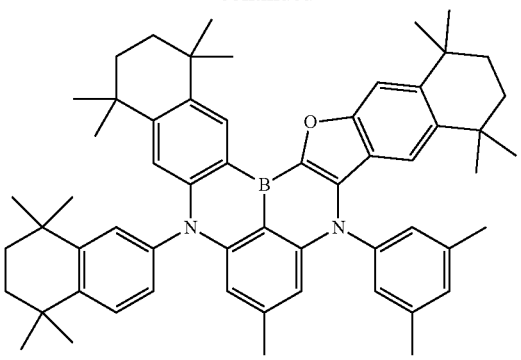
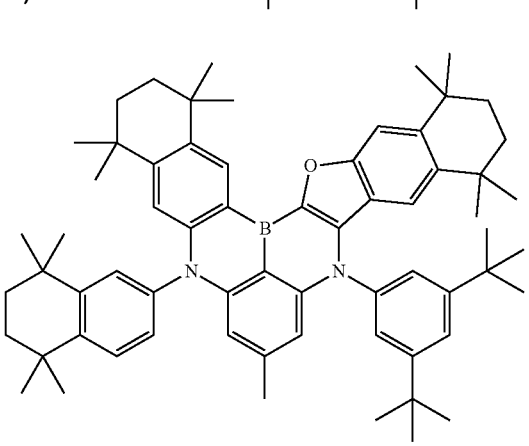
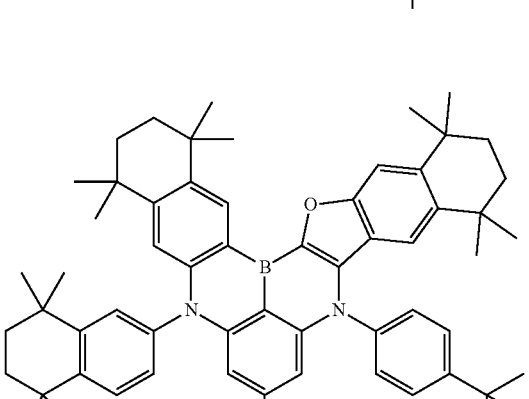
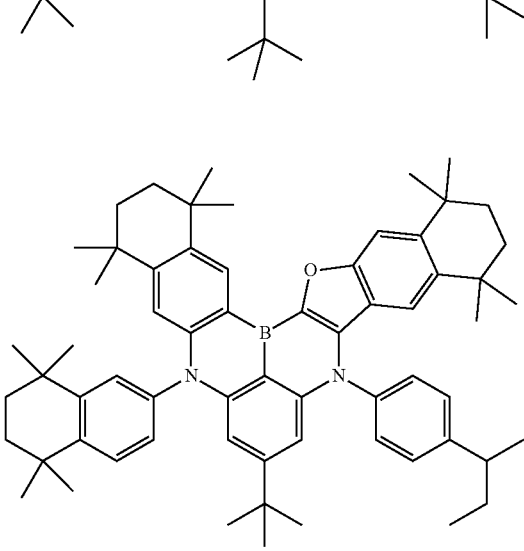

757
-continued
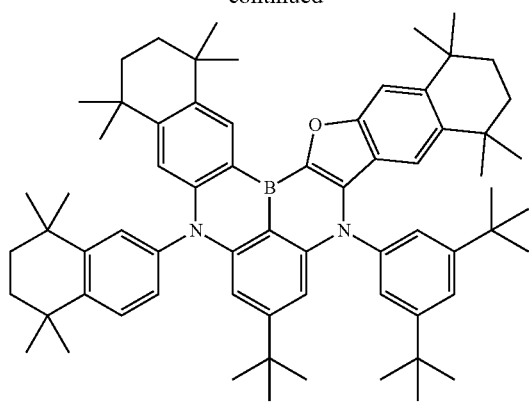
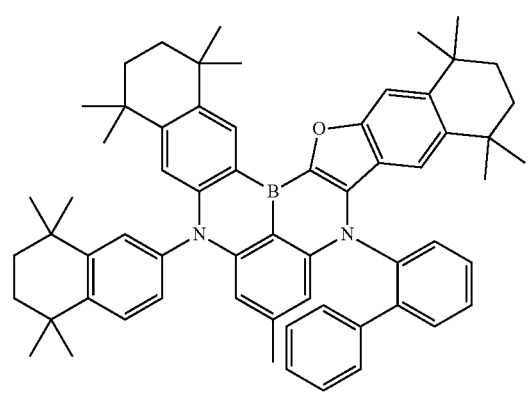
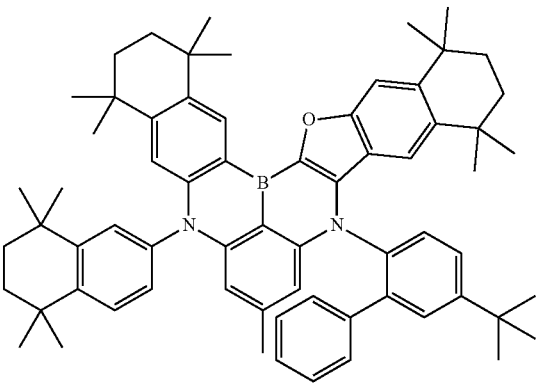
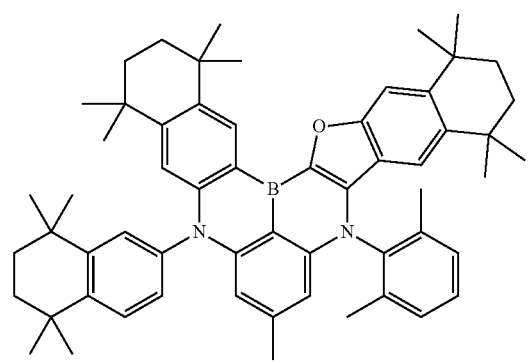
758
-continued
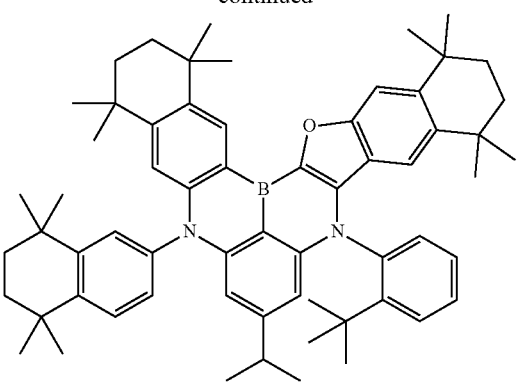
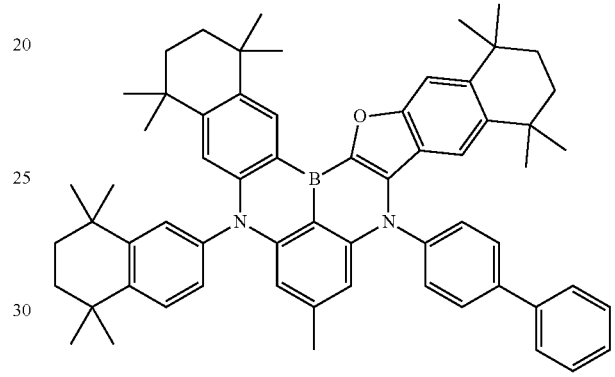
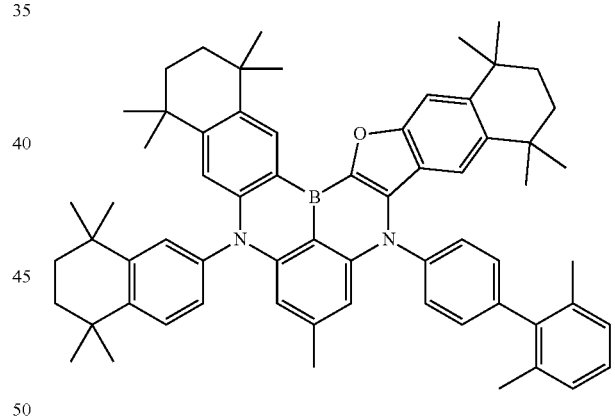
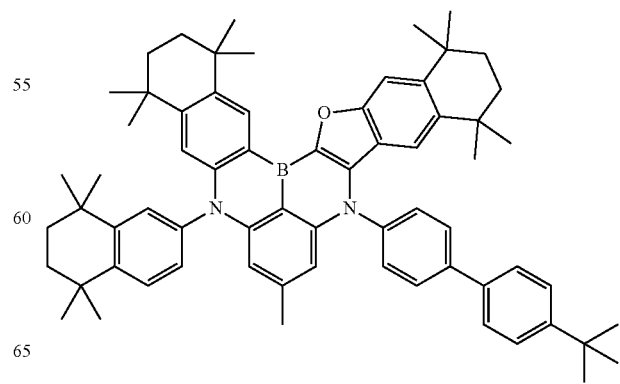

759
-continued
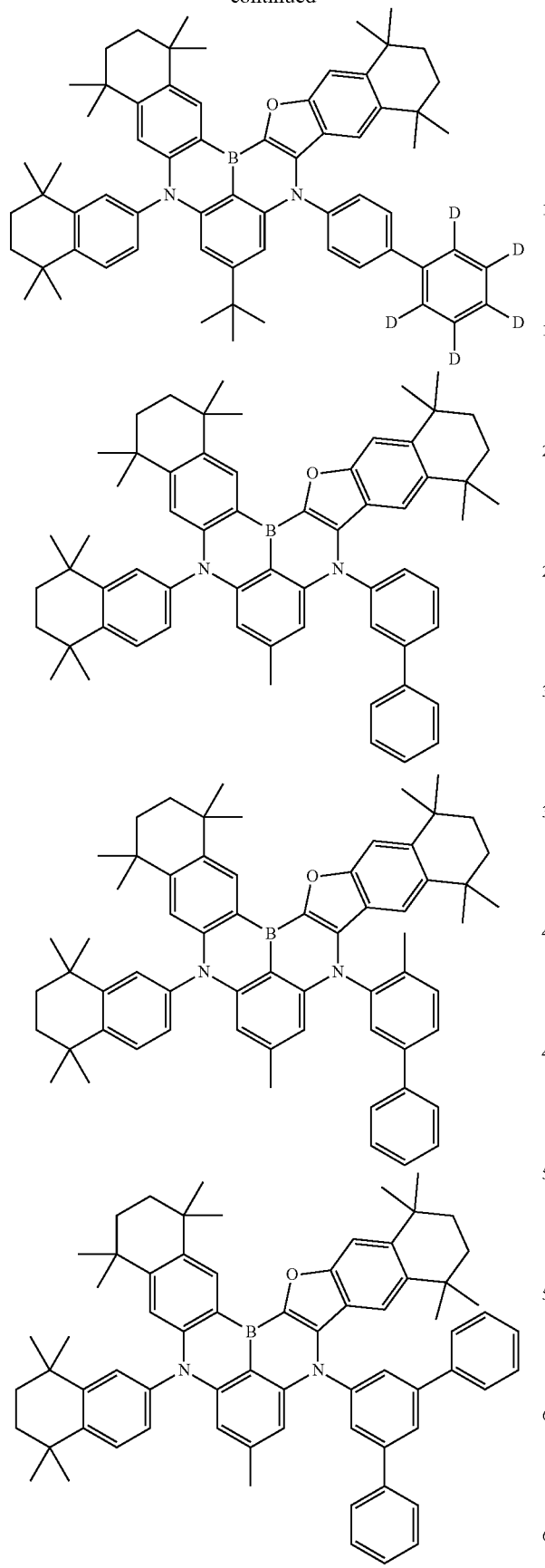
760
-continued
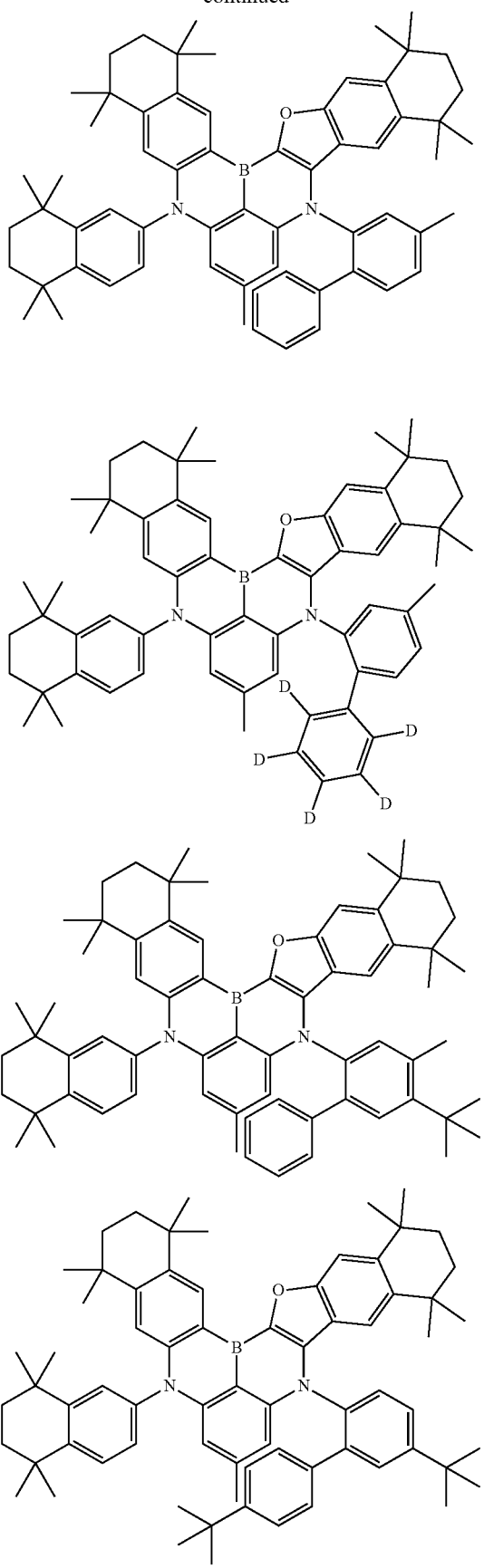

761
-continued

762
-continued

763
-continued
764
-continued
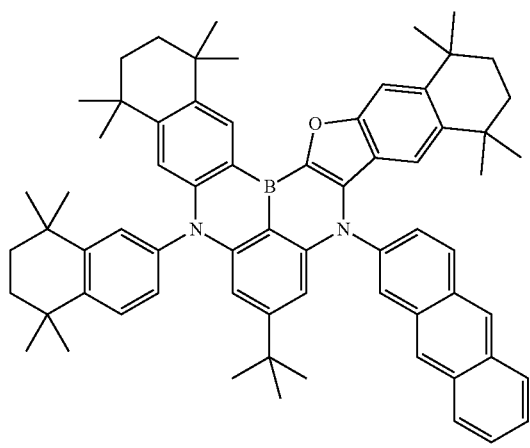
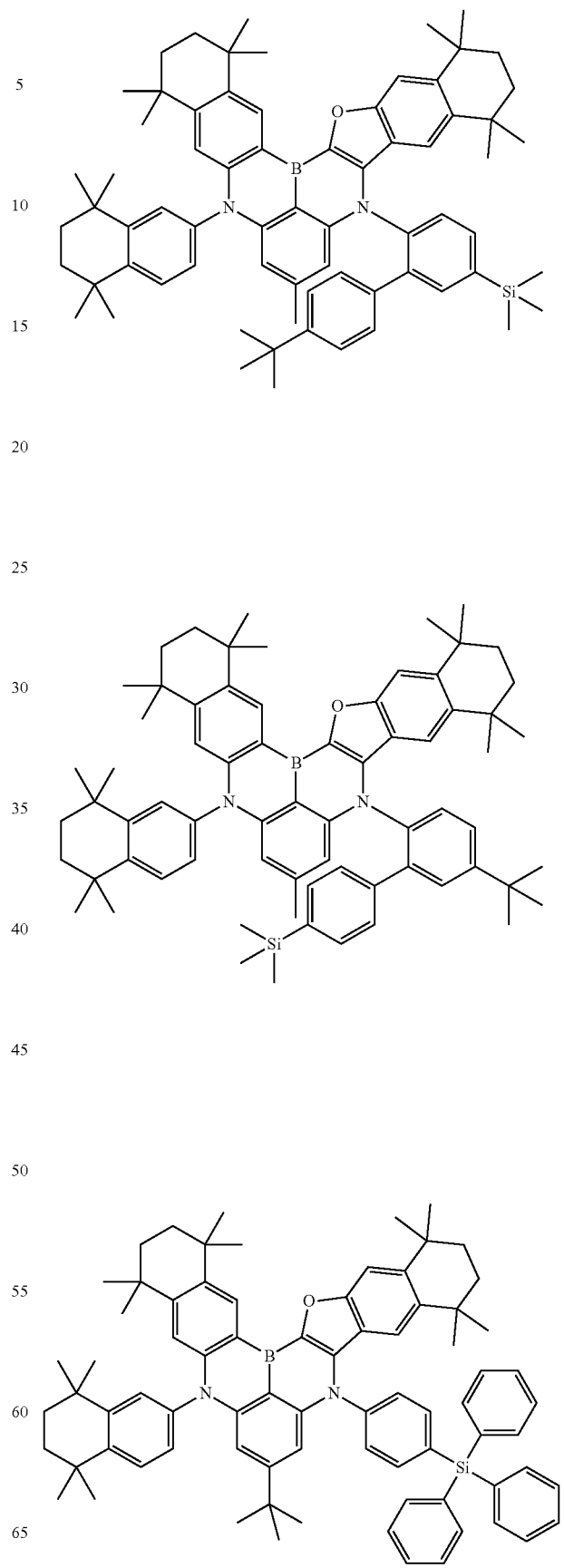

765 766
-continued -continued
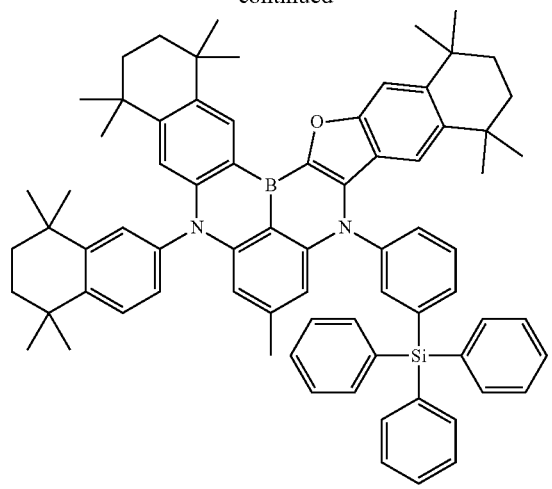
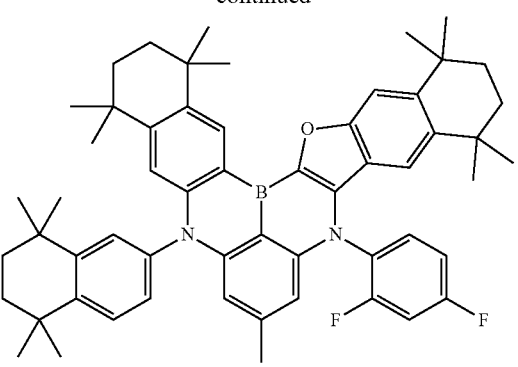
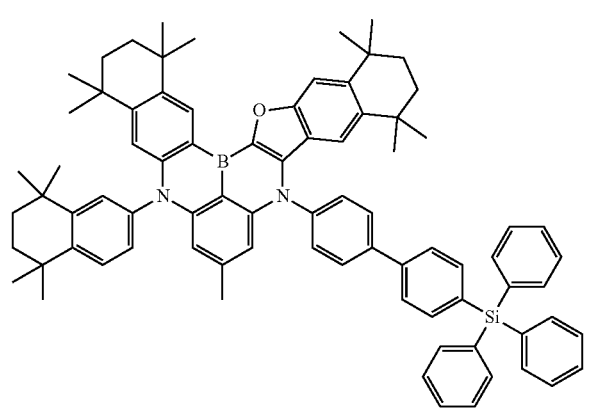
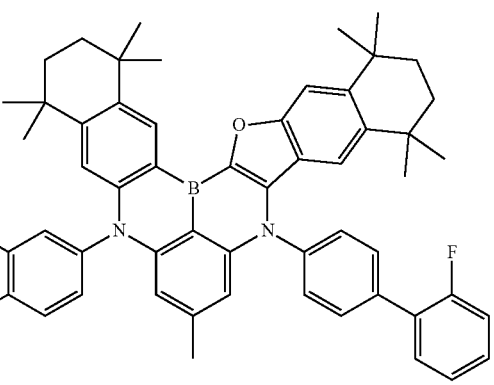
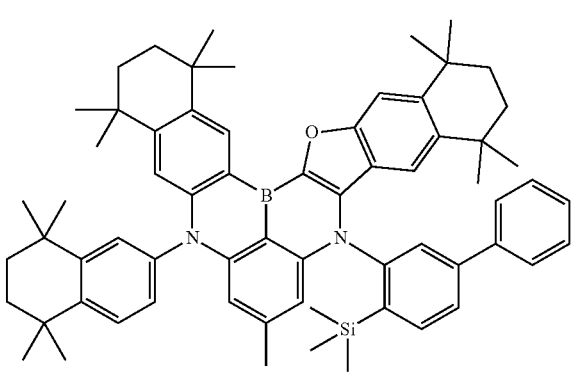
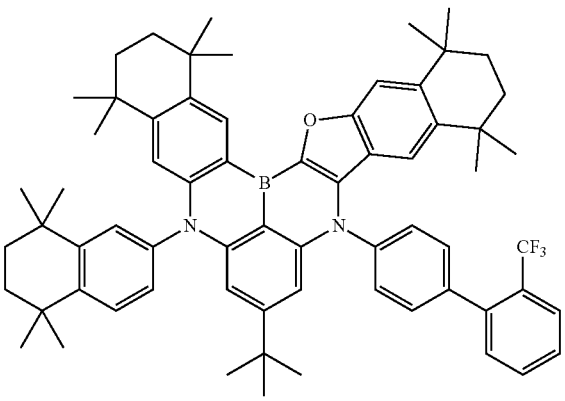
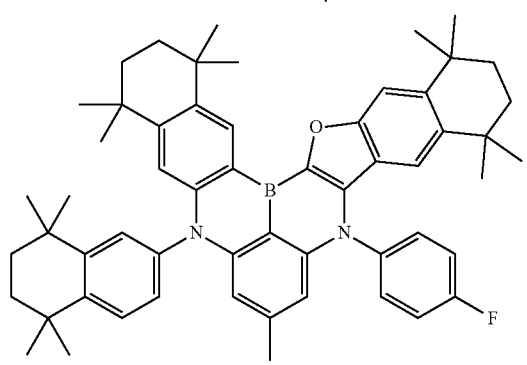

767
-continued
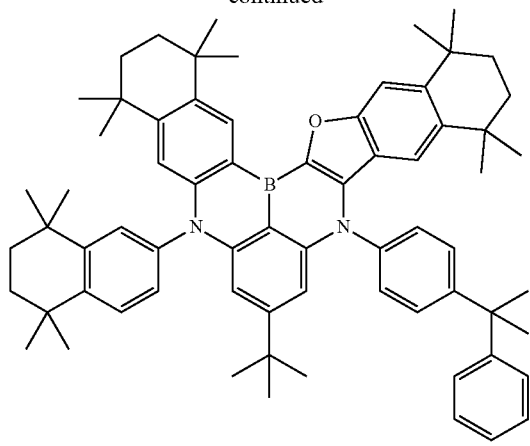
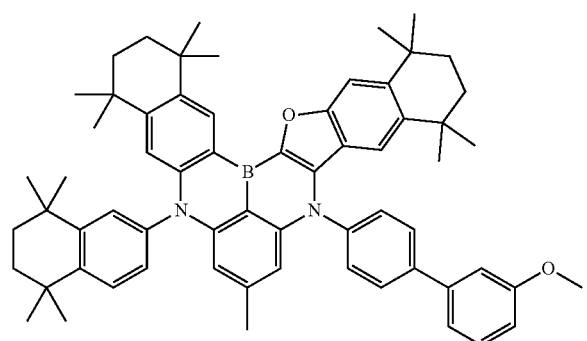
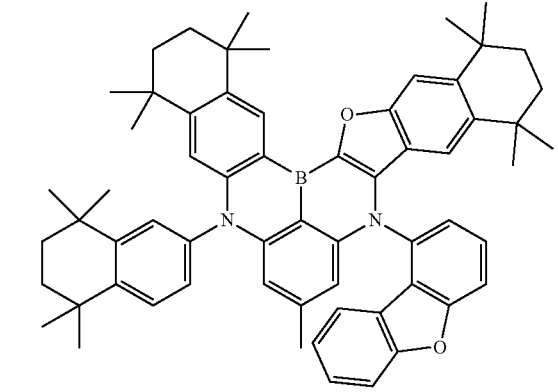
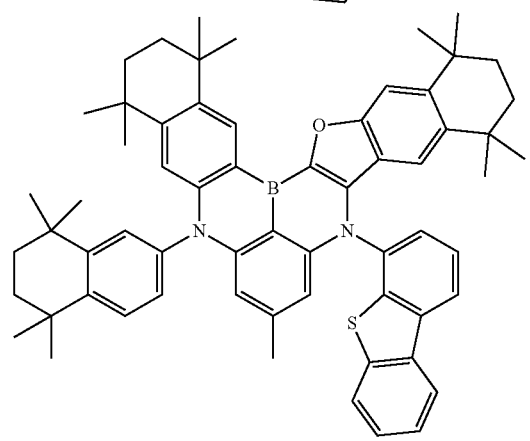
768
-continued
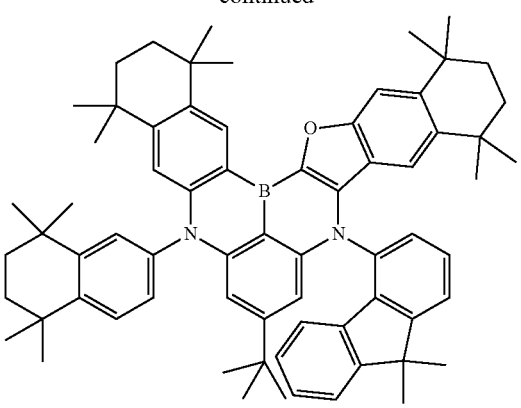
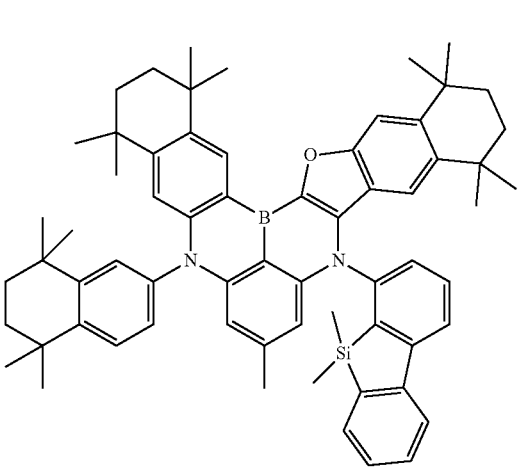
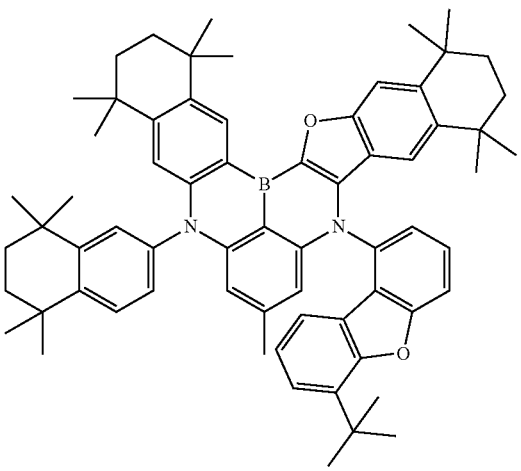

769
-continued
770
-continued
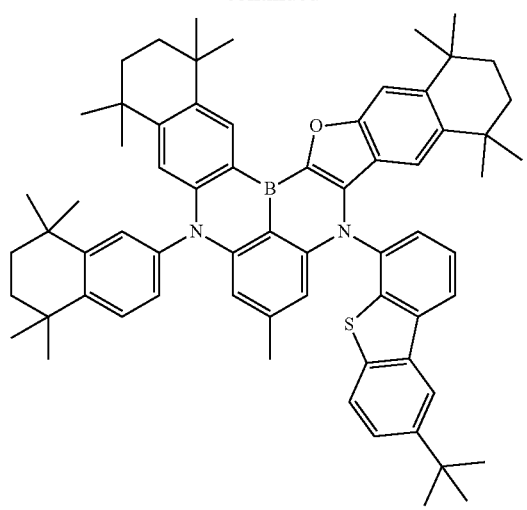
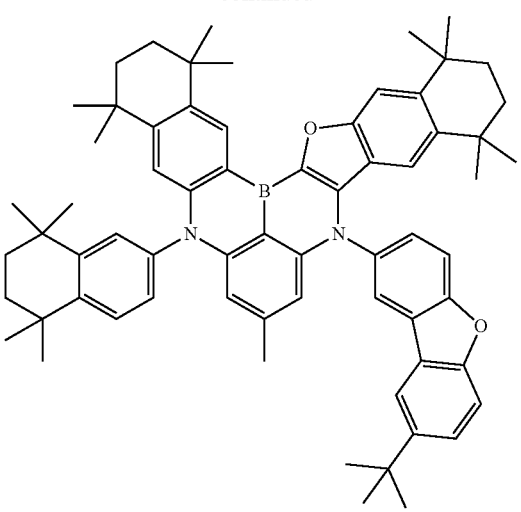
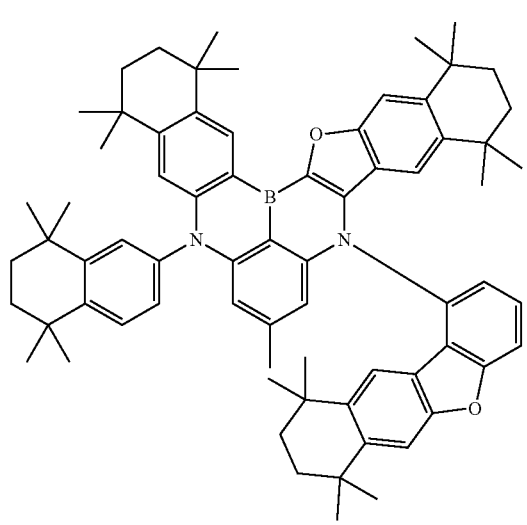
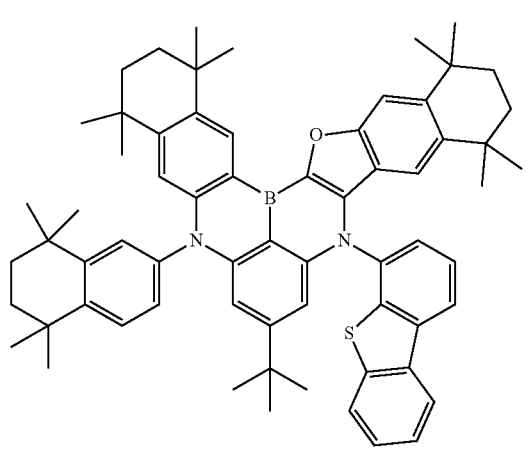
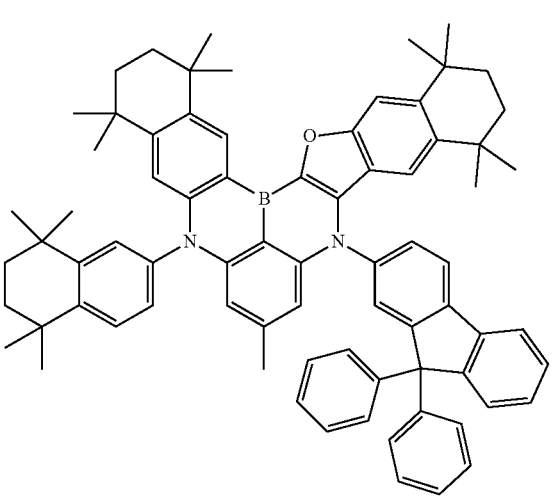

771
-continued
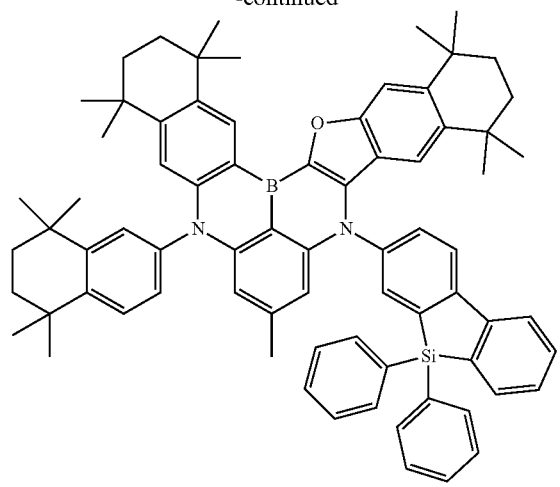
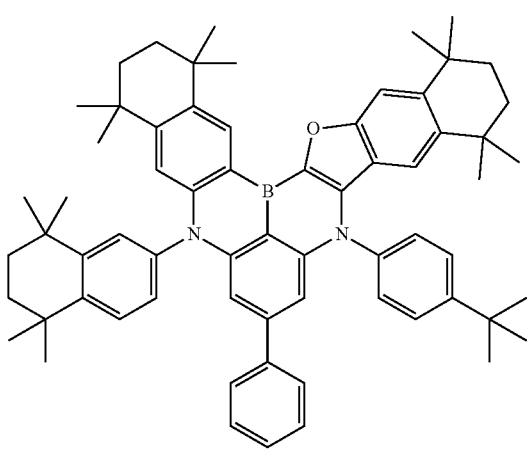
772
-continued
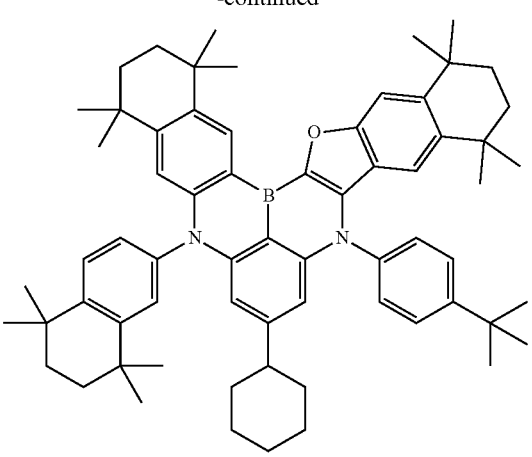
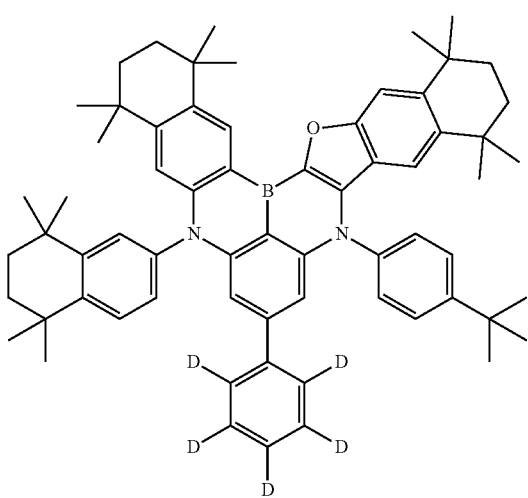
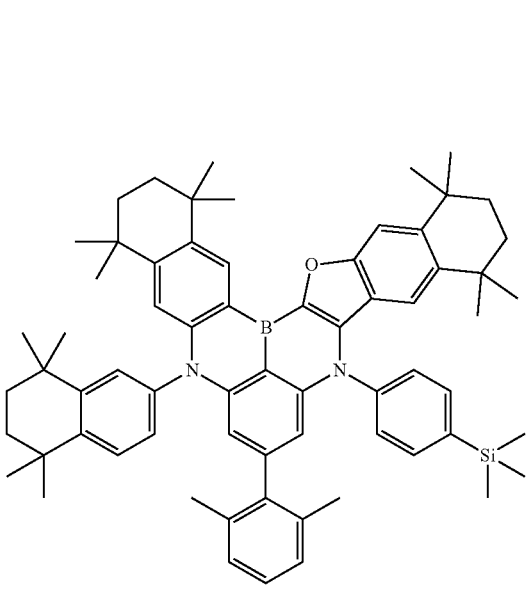

773
-continued
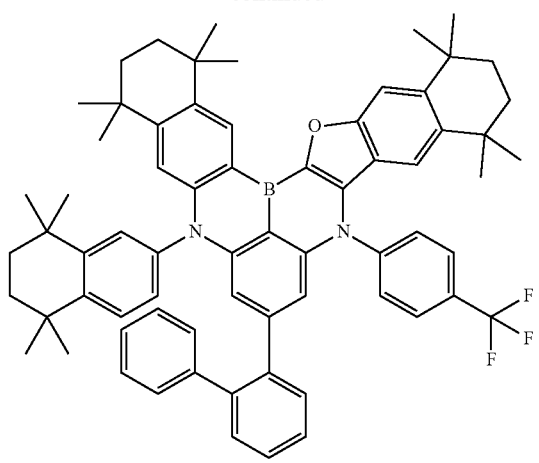
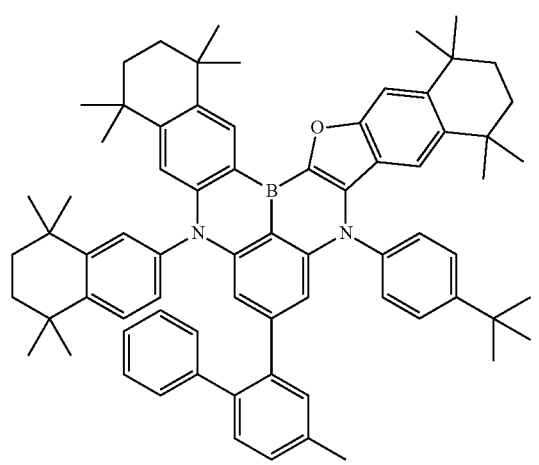
774
-continued
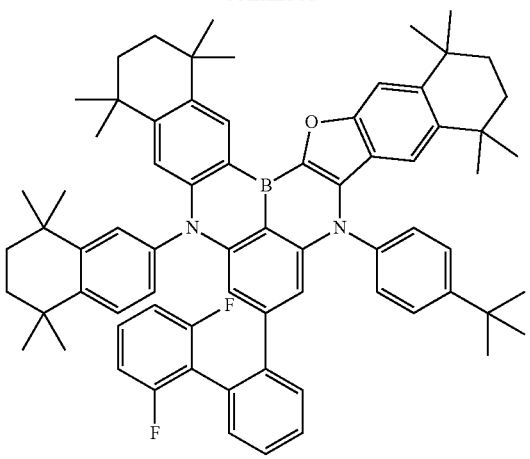
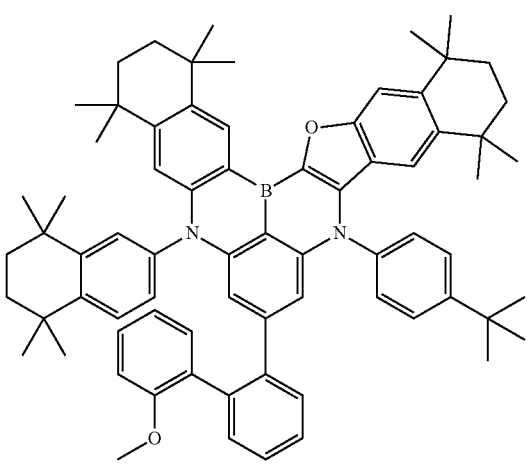

775
-continued
776
-continued
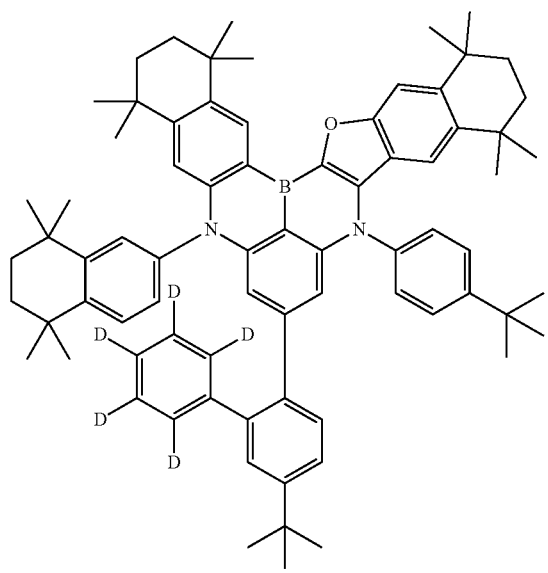
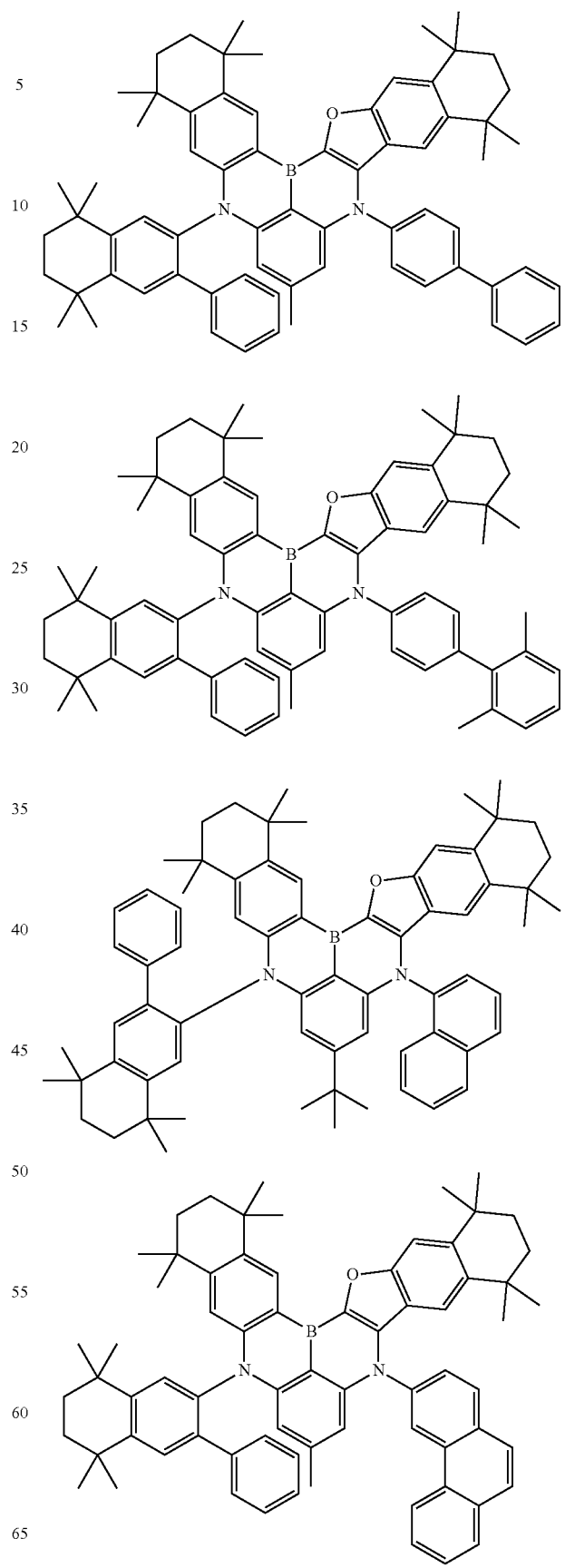

777
-continued
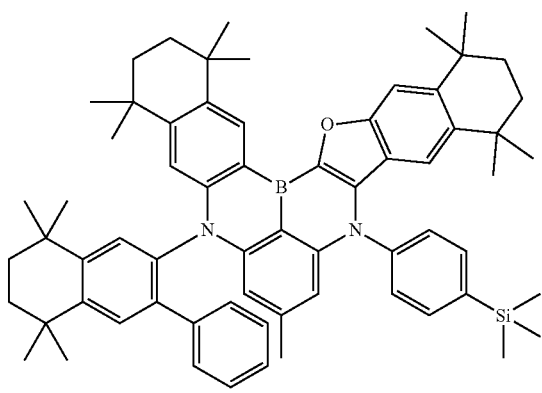
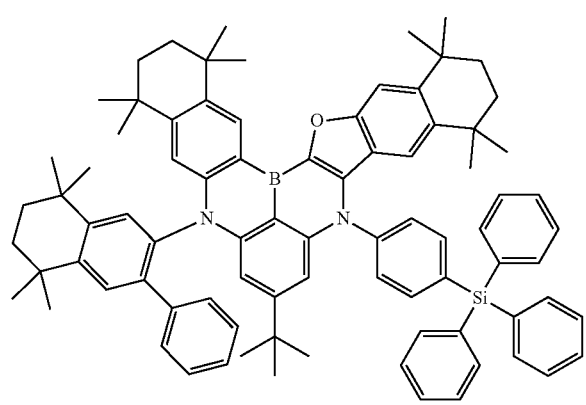
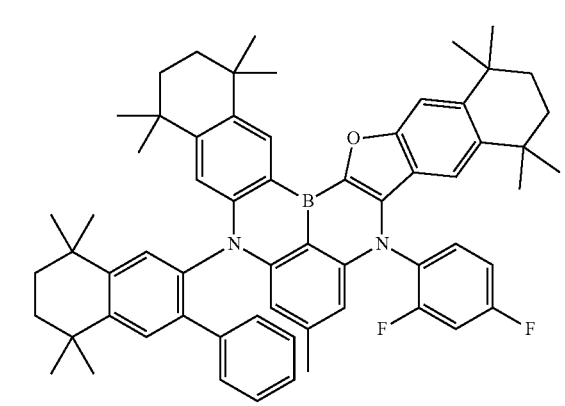
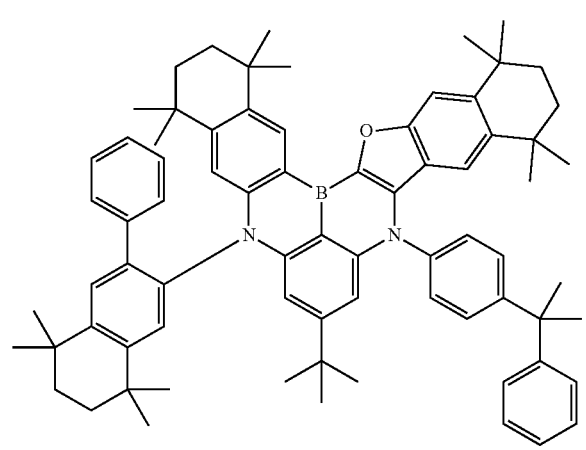
778
-continued
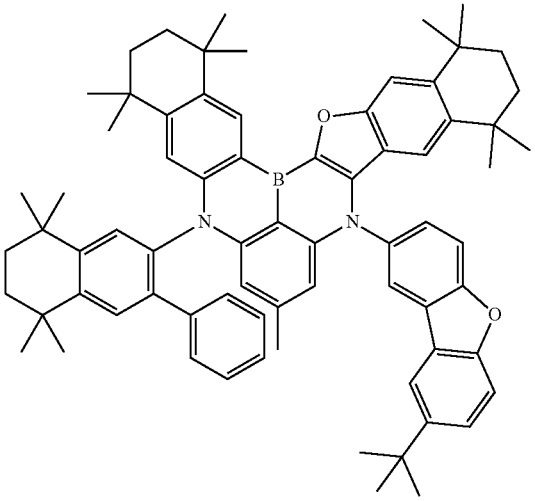
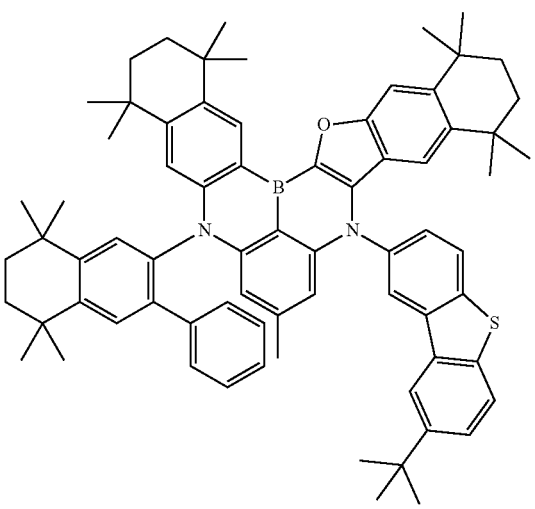
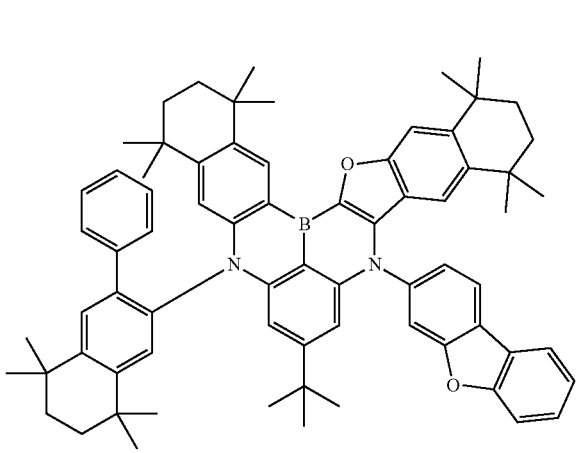

779
-continued
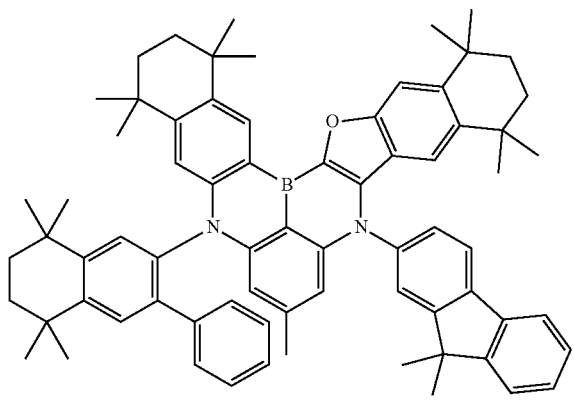
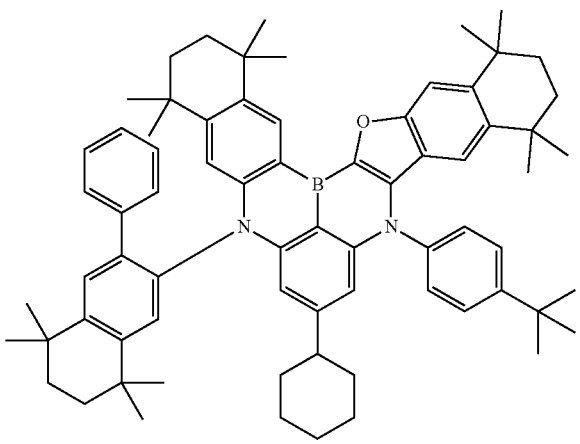
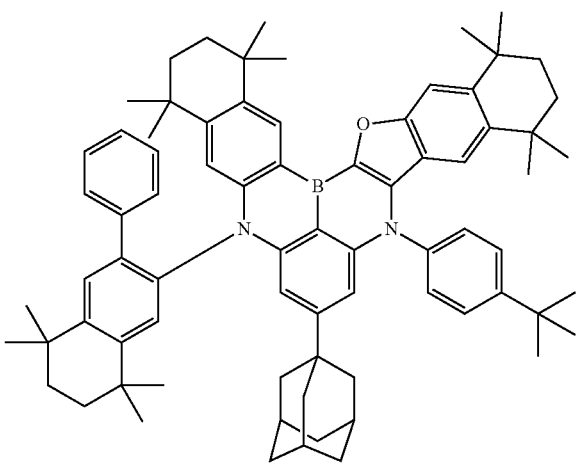
780
-continued
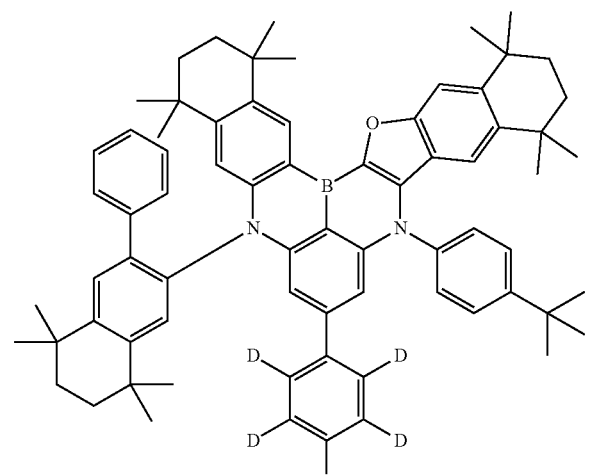
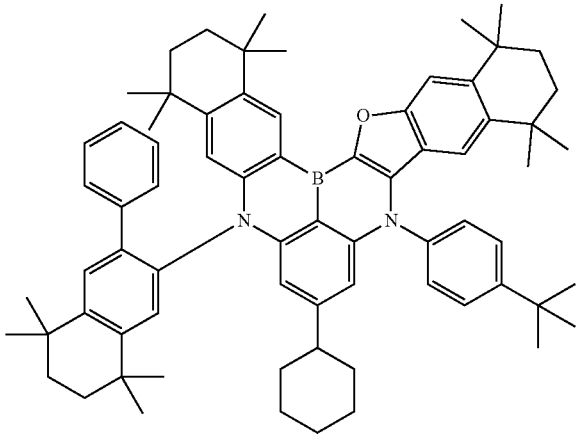
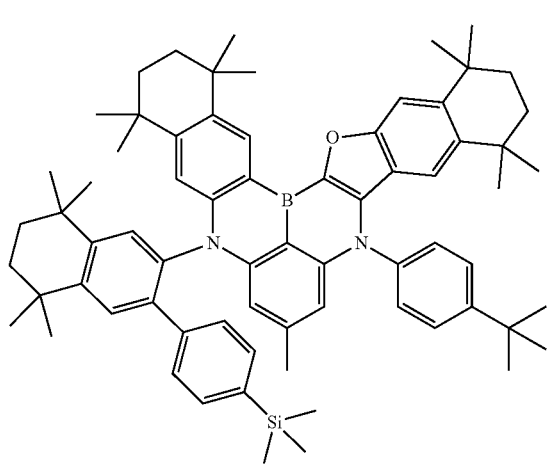

781
-continued
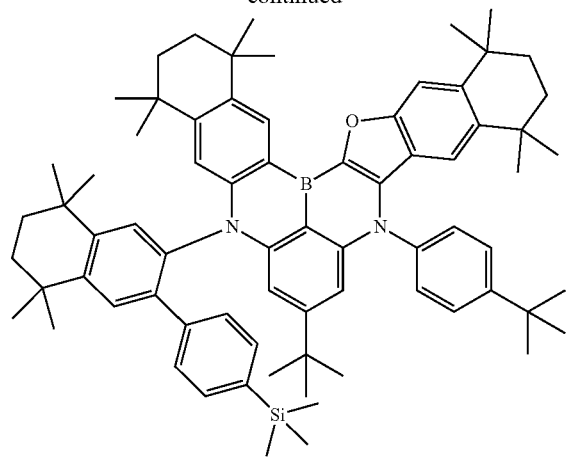
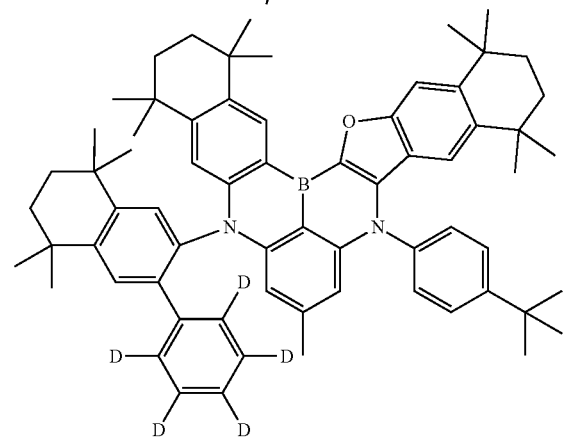
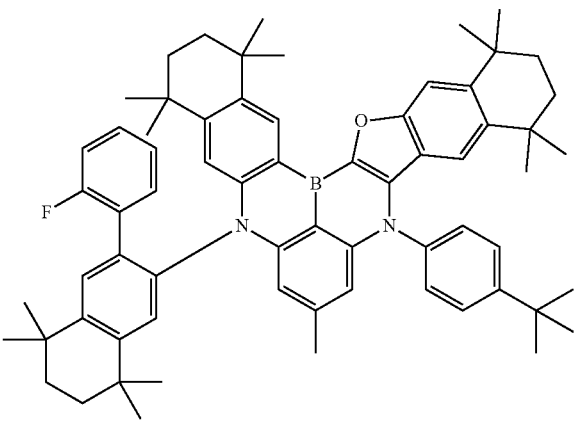
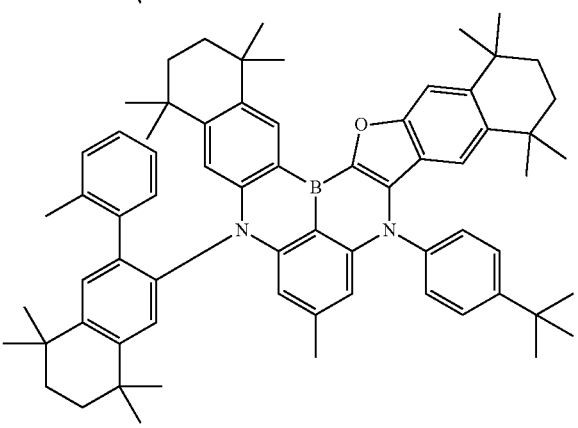
782
-continued
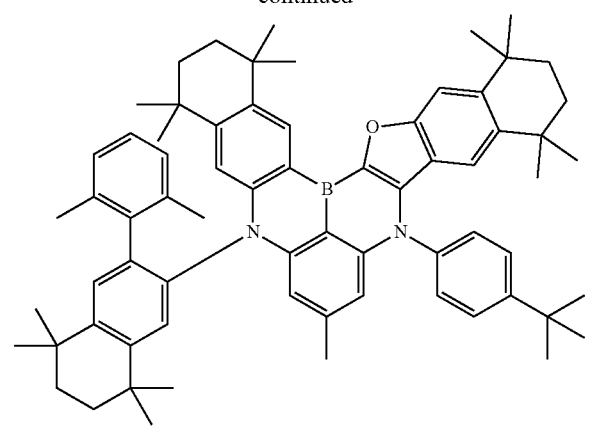

783
-continued
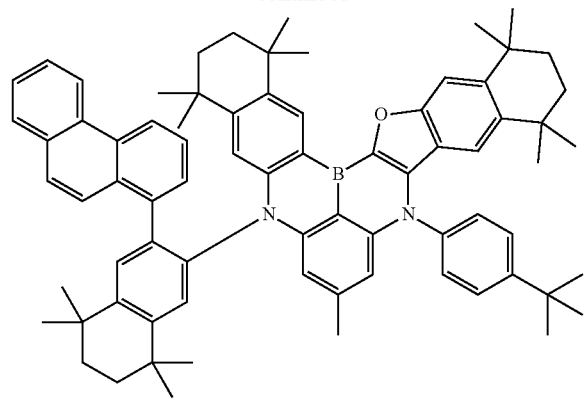
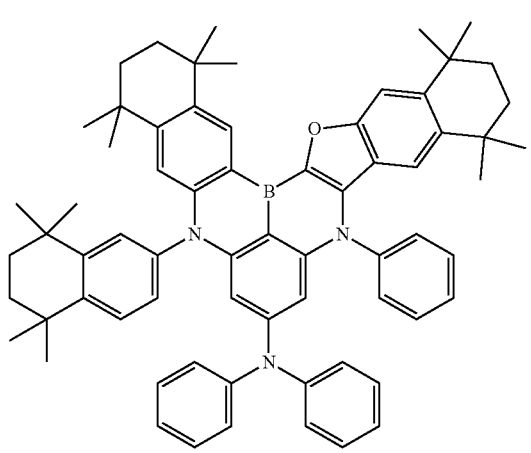
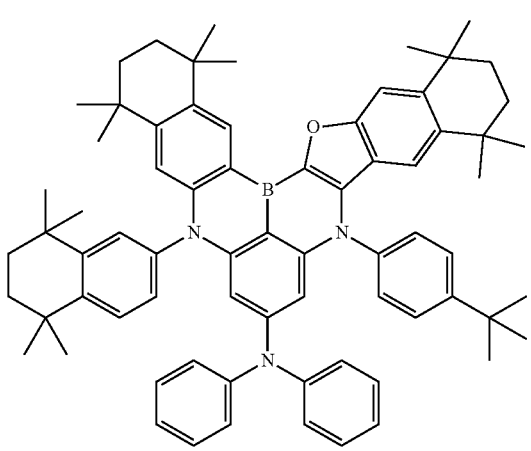
784
-continued
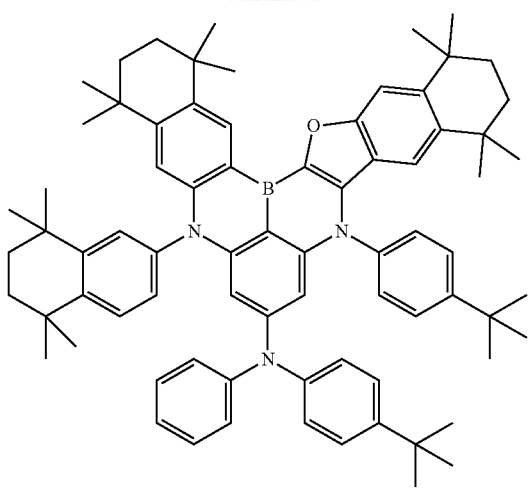
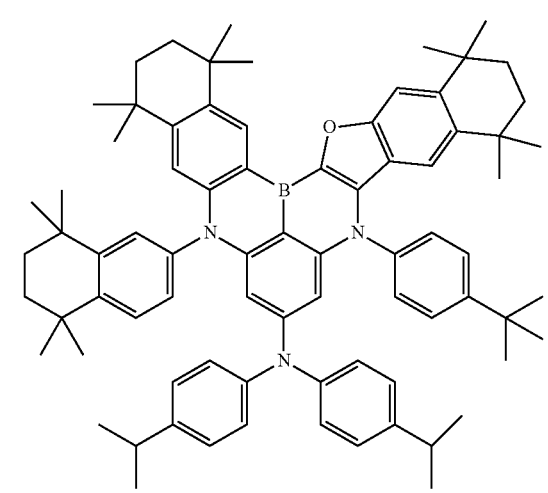
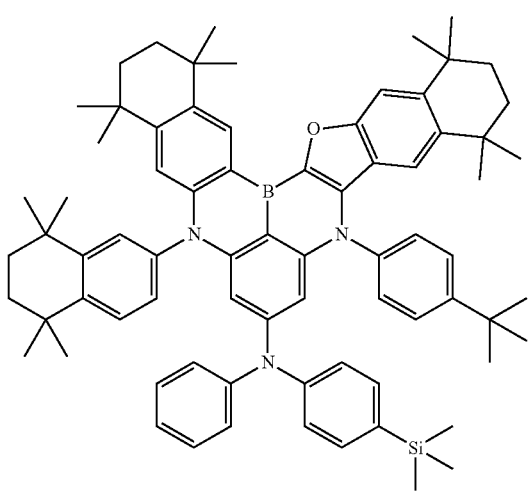

785
-continued
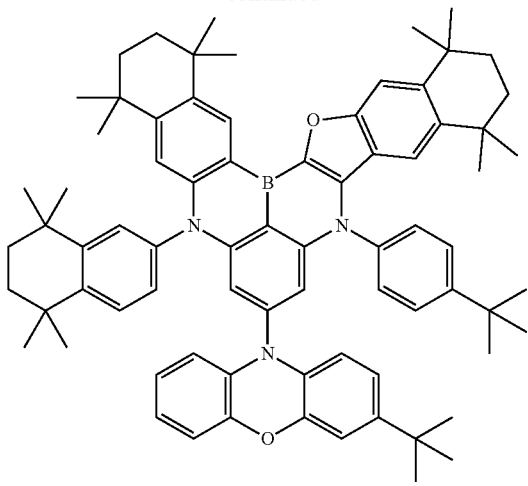
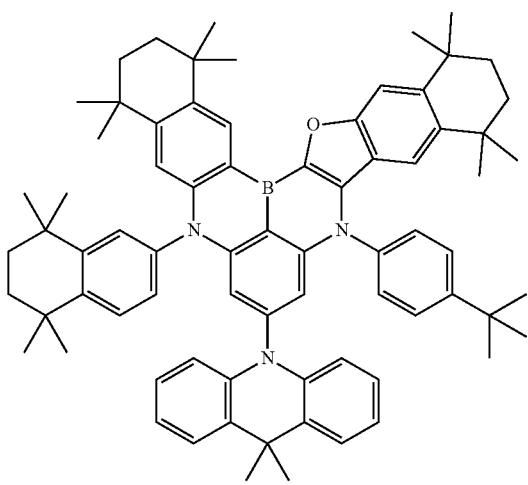
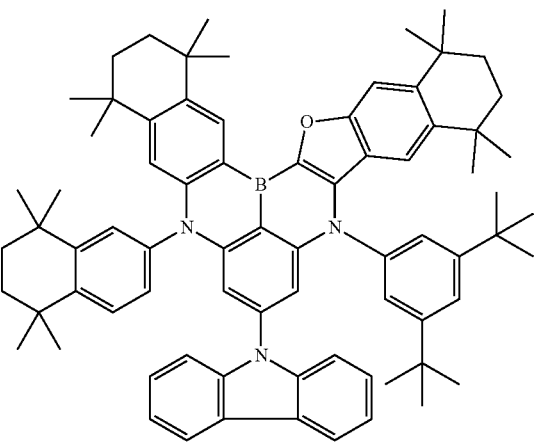
786
-continued
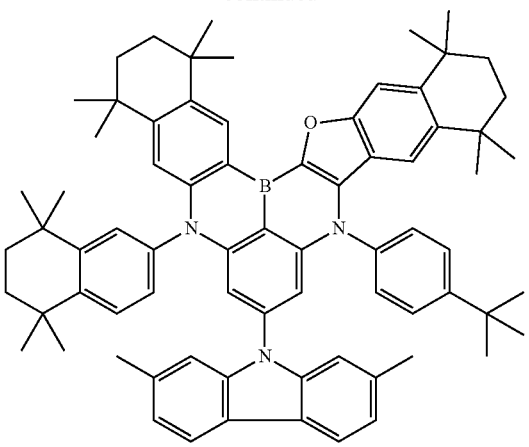
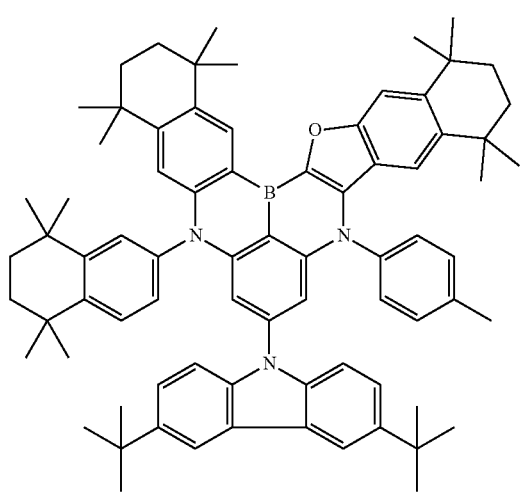
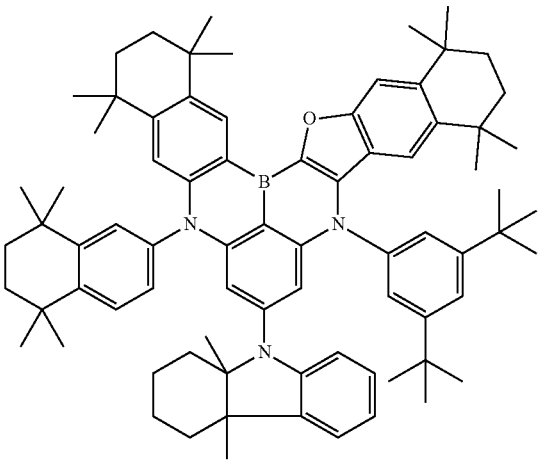

| 787 | 788 |
|---|---|
| 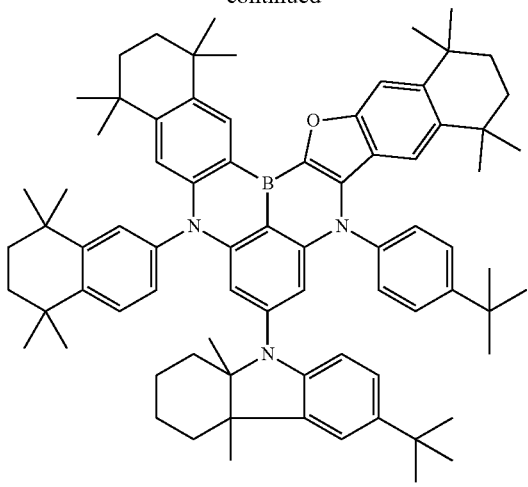 | 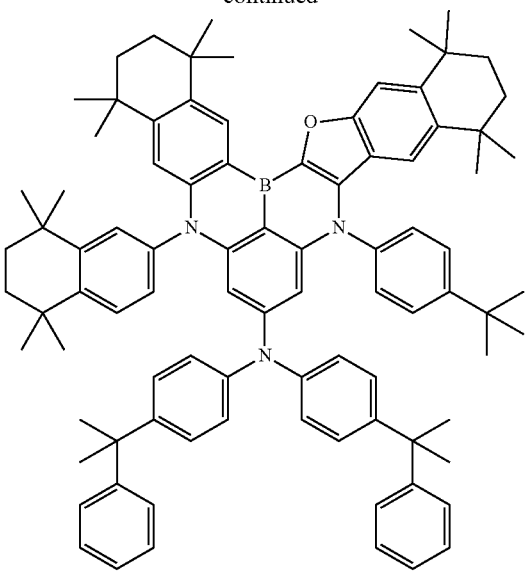 |
| 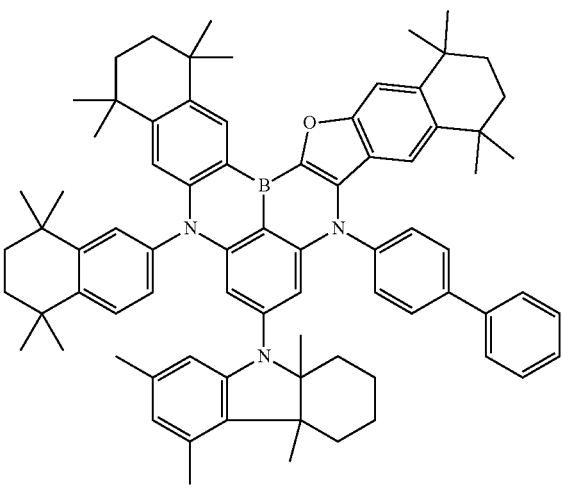 | 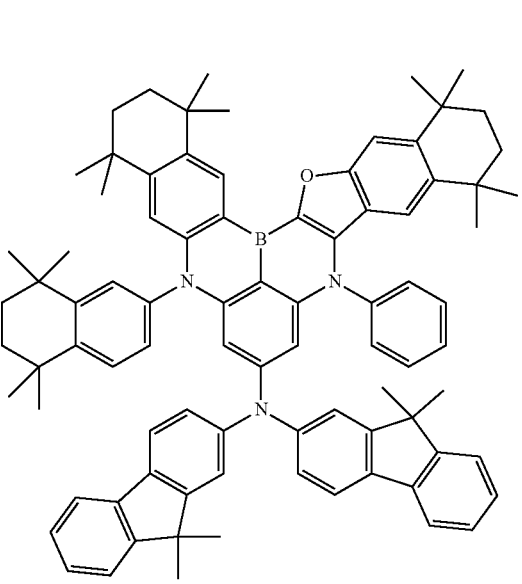 |
| 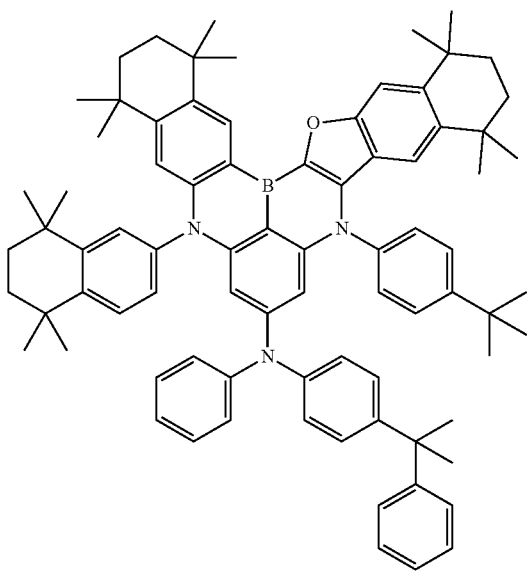 | 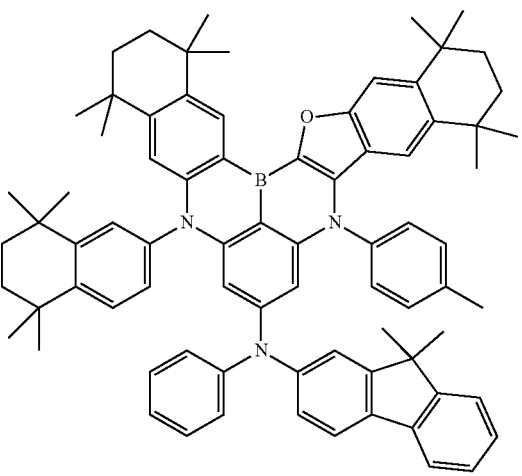 |

789
-continued
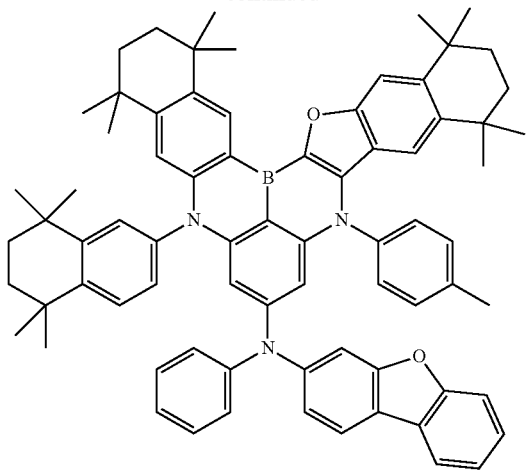
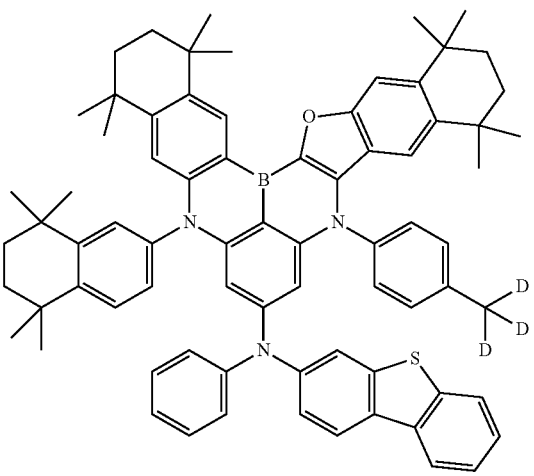
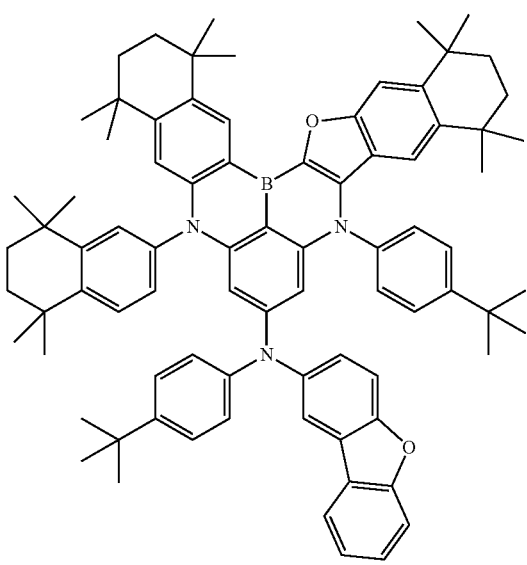
790
-continued
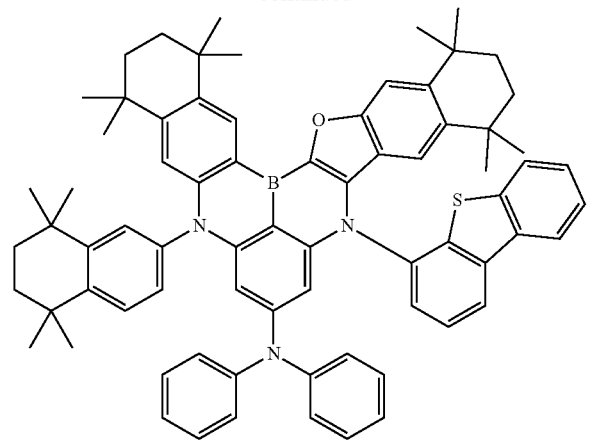
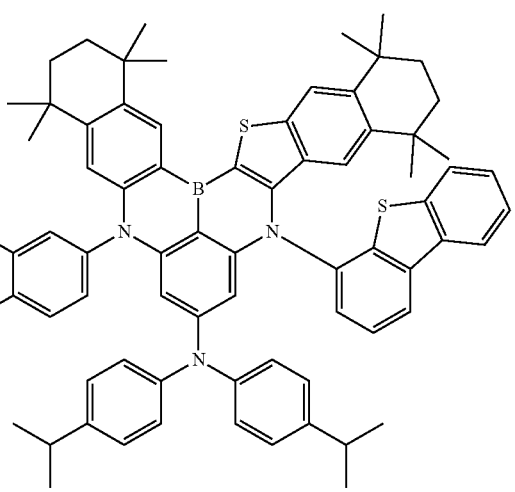
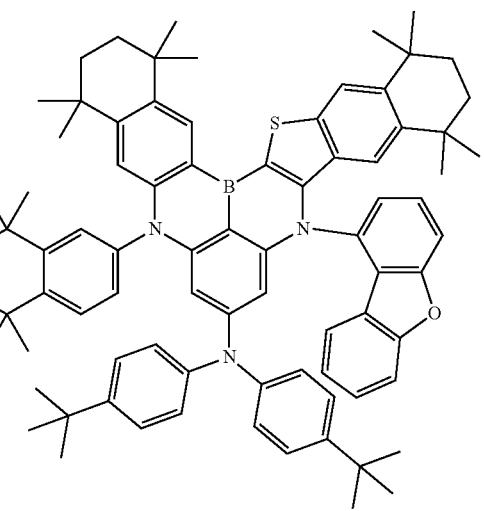

791
-continued
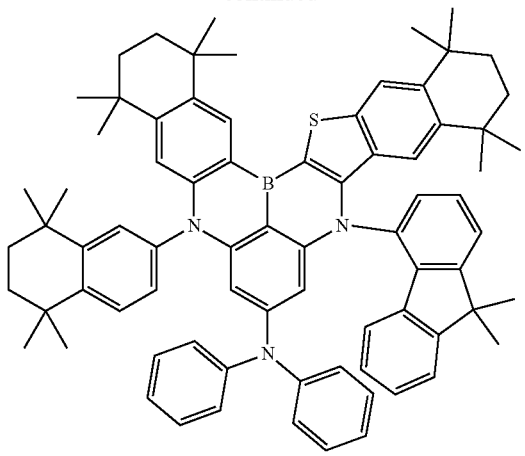
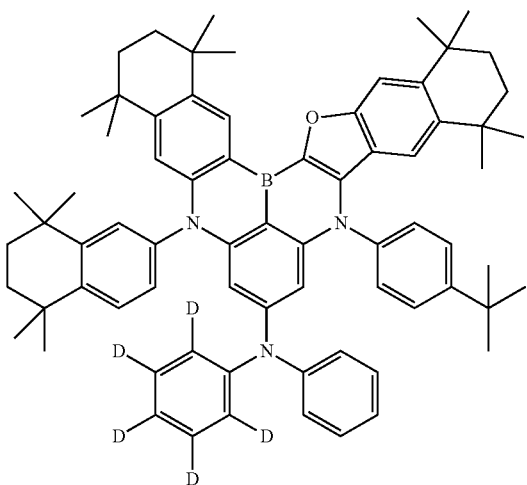
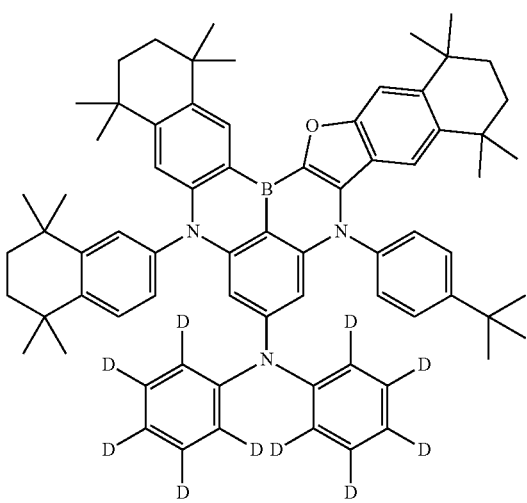
792
-continued
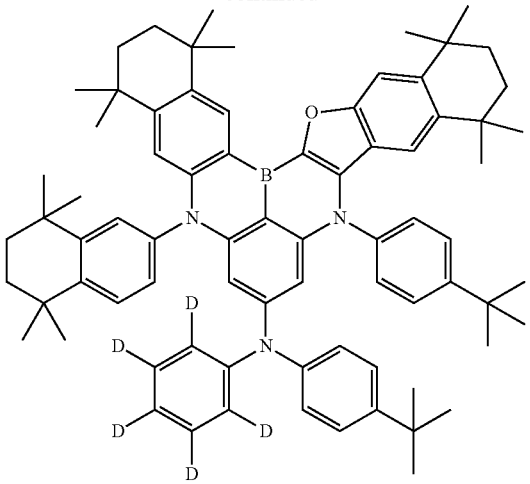
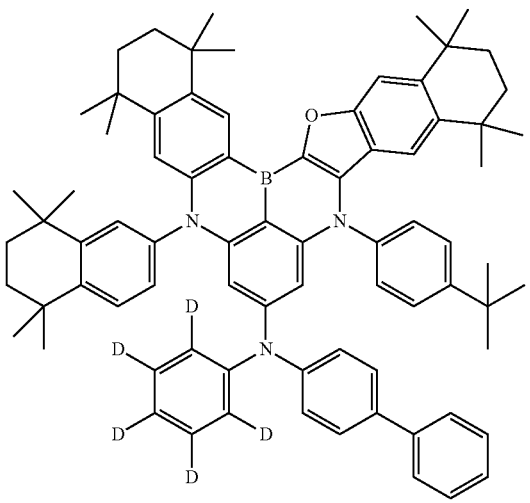

793
-continued
794
-continued
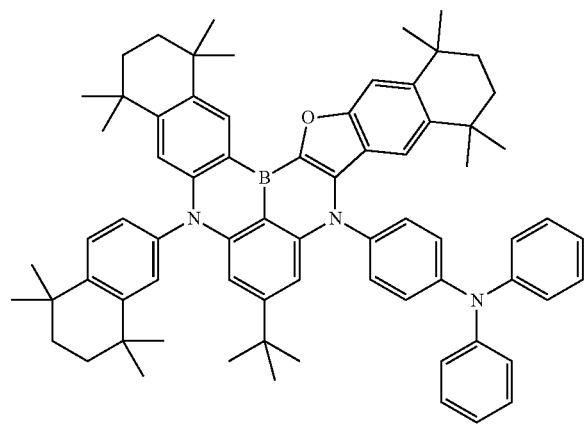
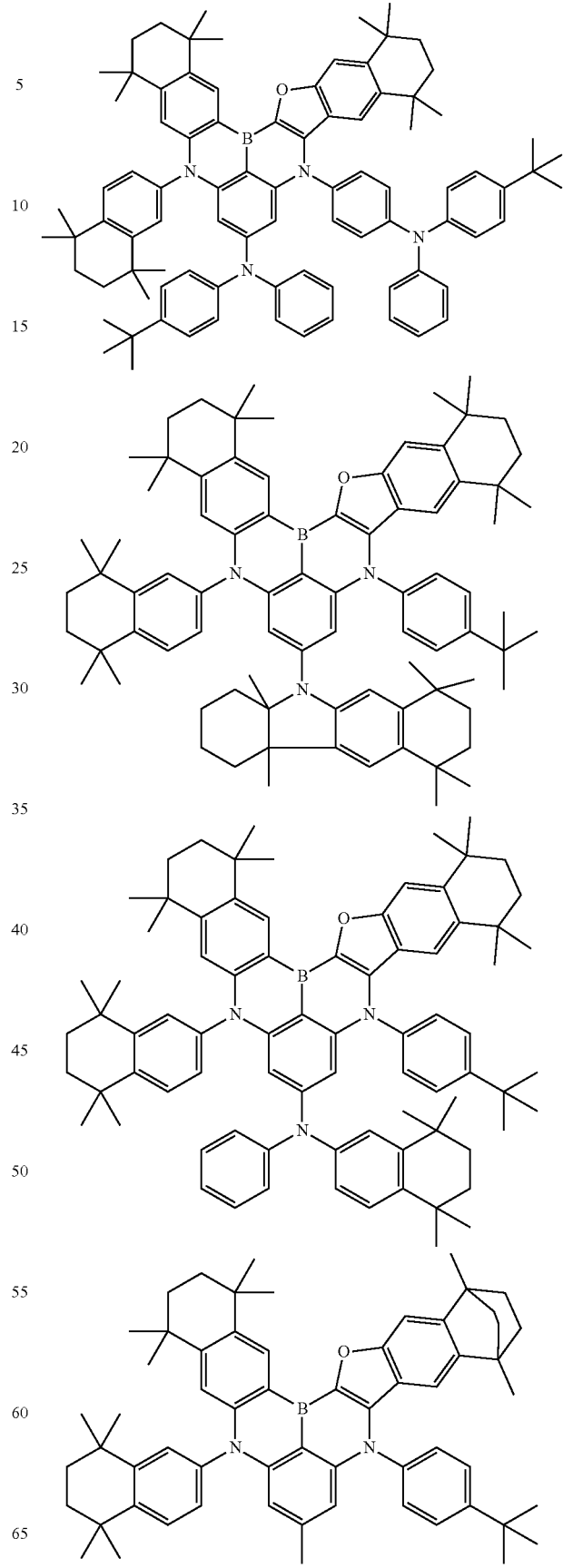

795
-continued
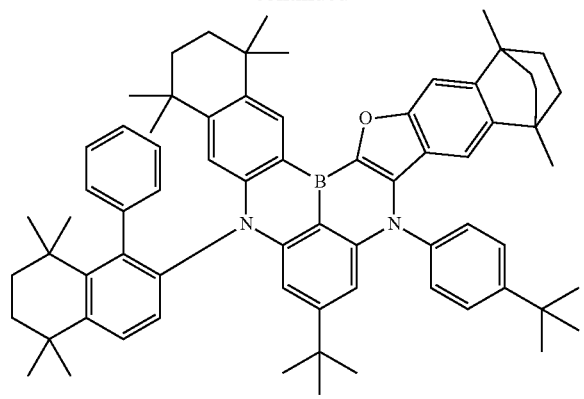
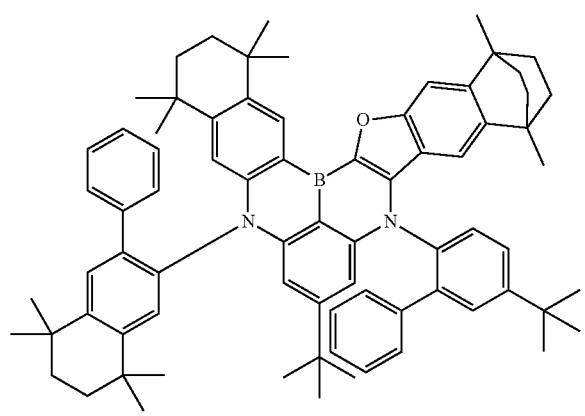
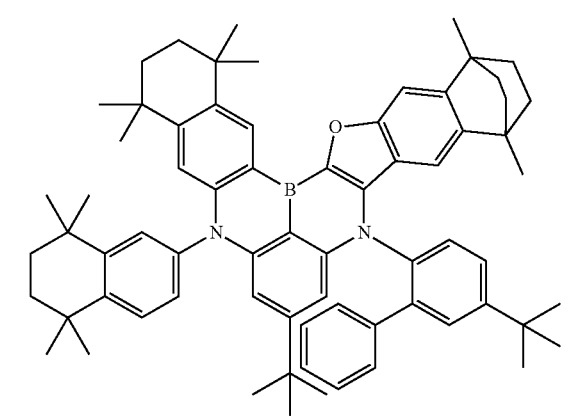
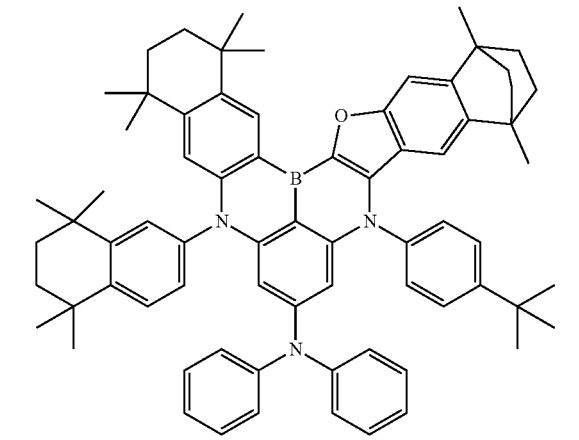
796
-continued
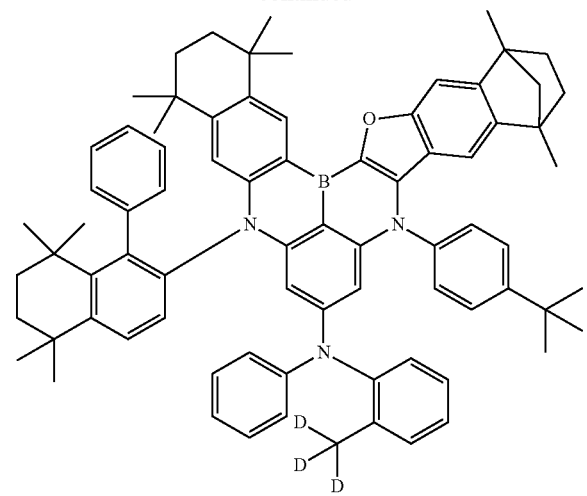
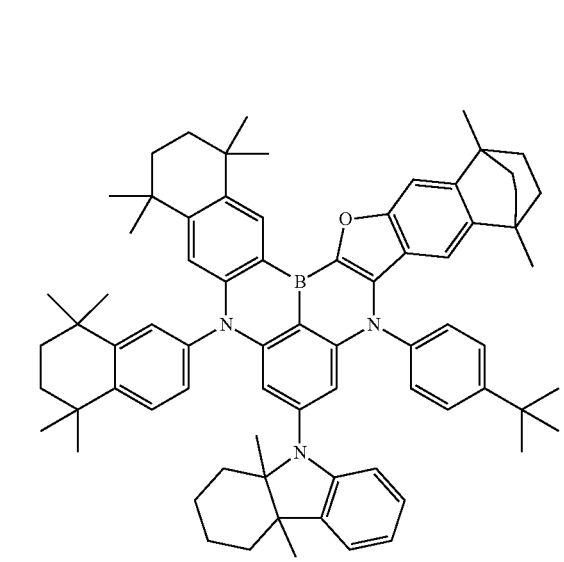
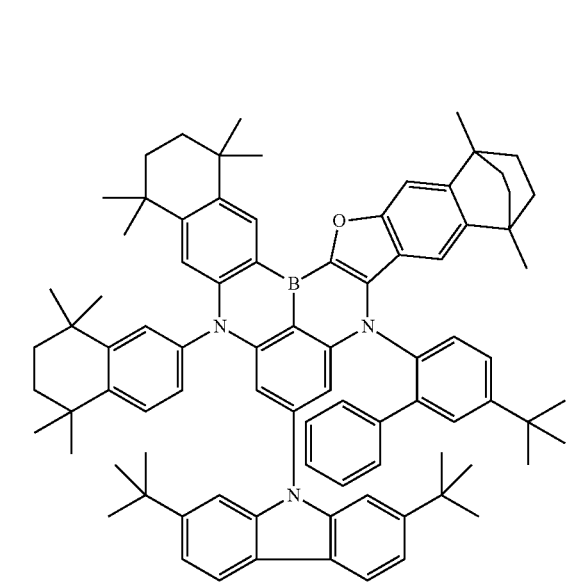

797
-continued
798
-continued
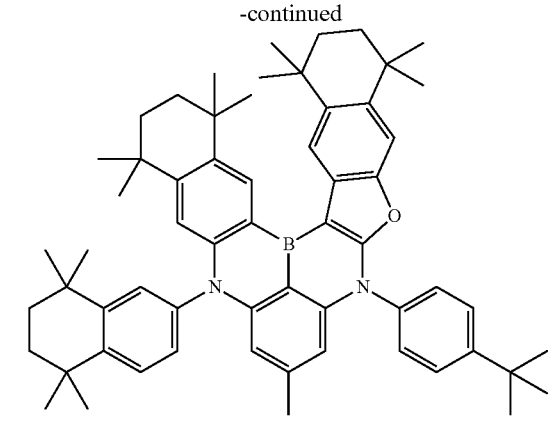
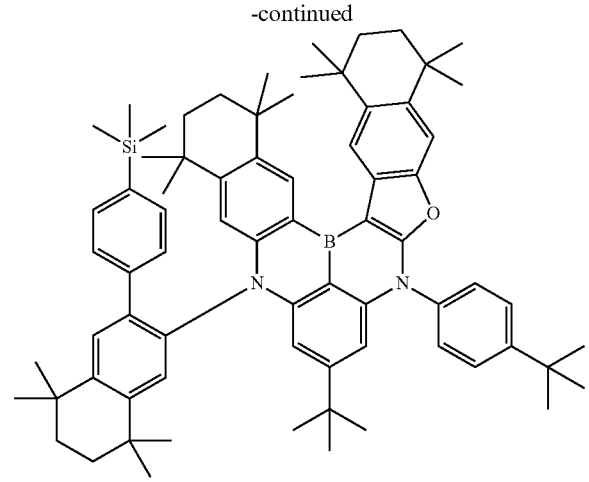
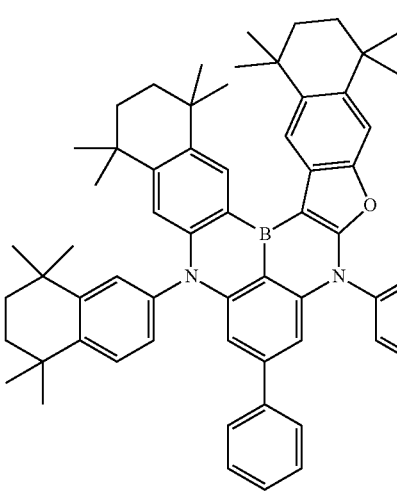
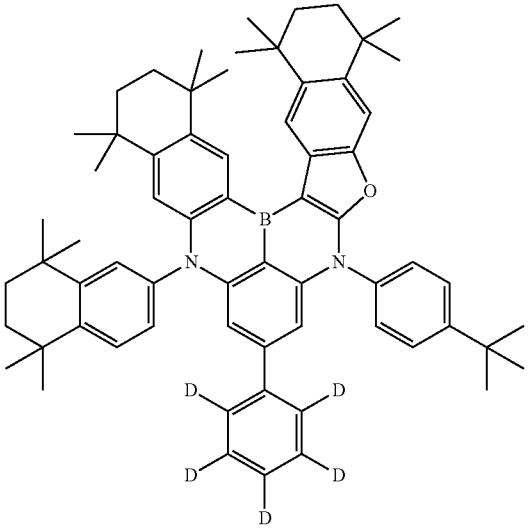

799
-continued
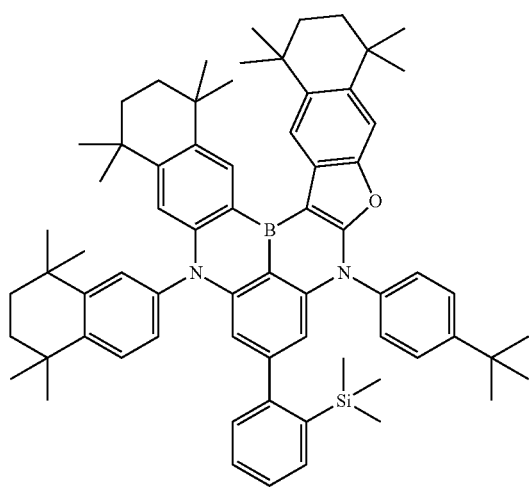
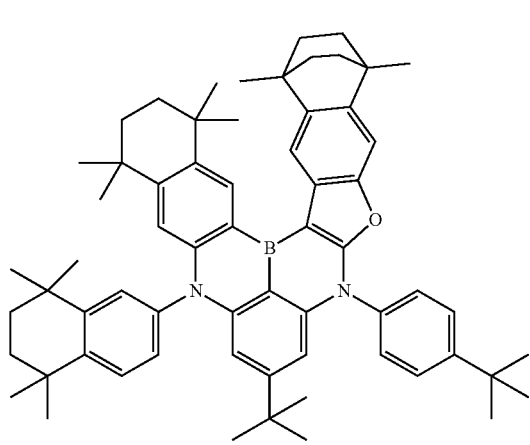
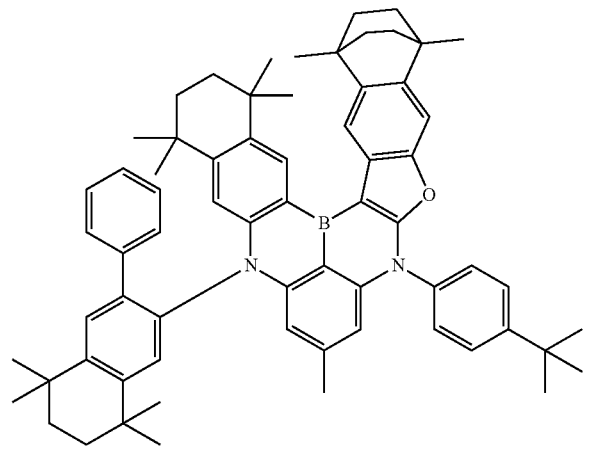
800
-continued
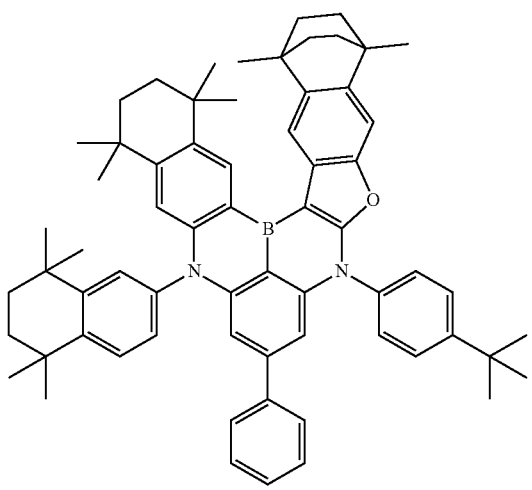

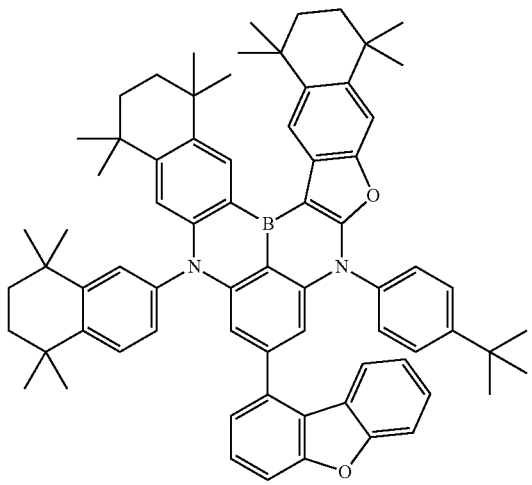

801
-continued
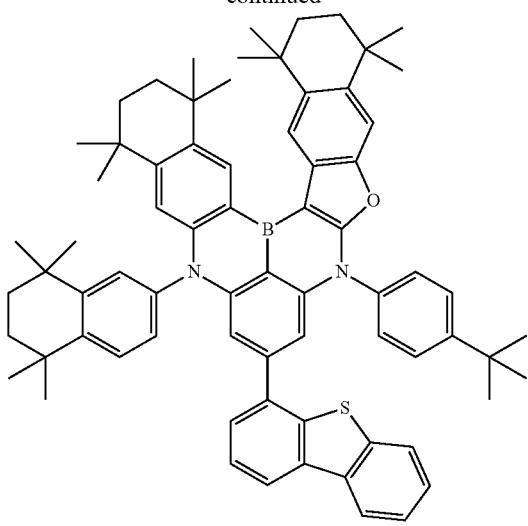
802
-continued
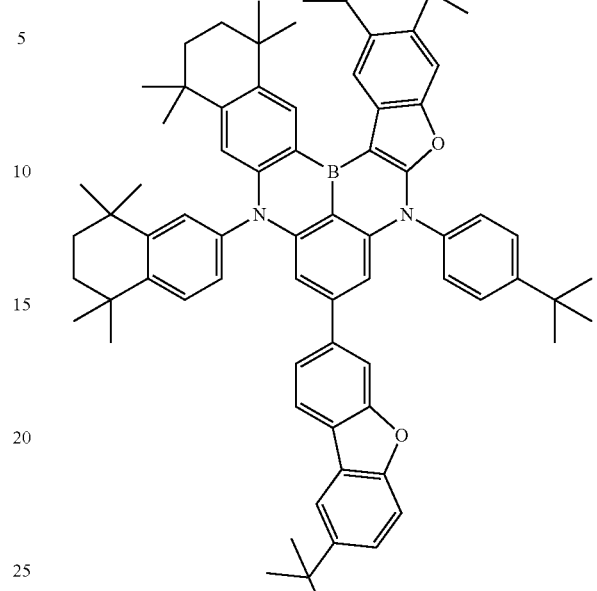
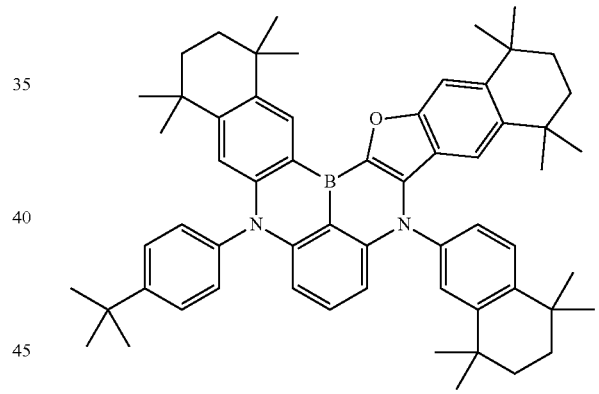
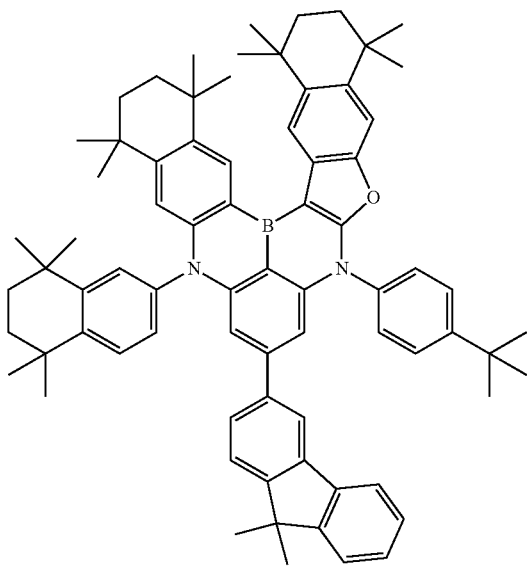
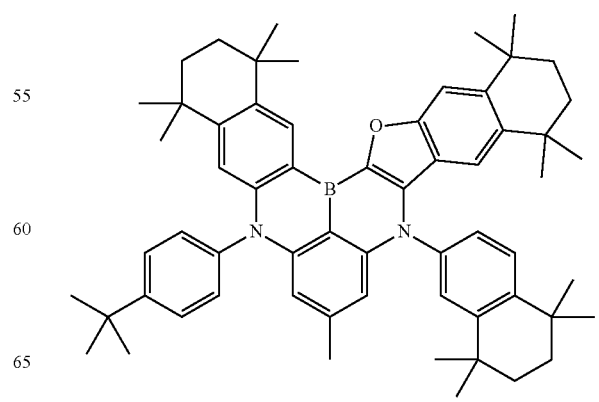

803
-continued
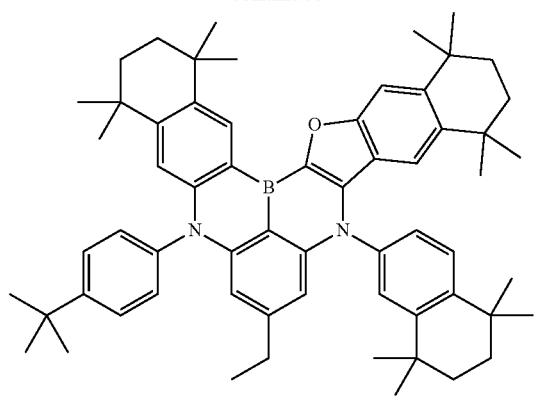
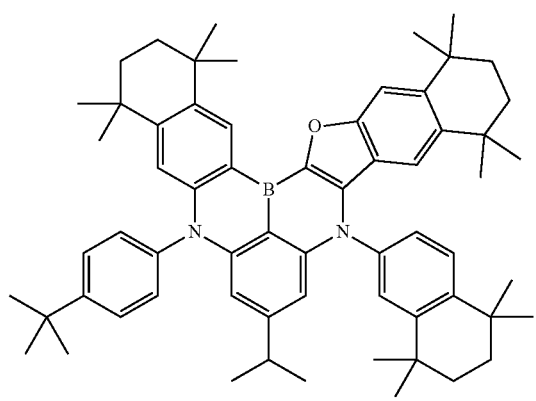
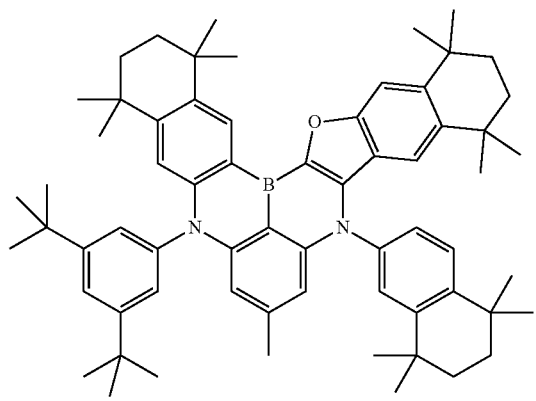
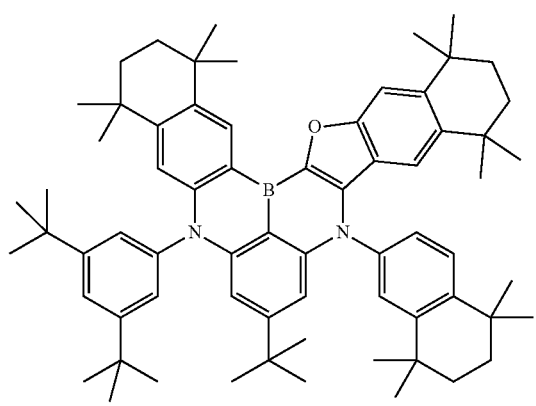
804
-continued
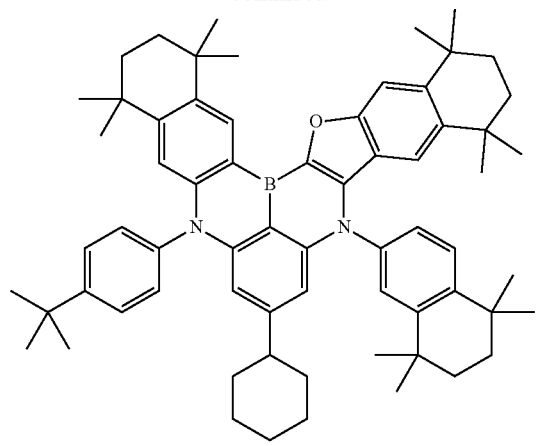
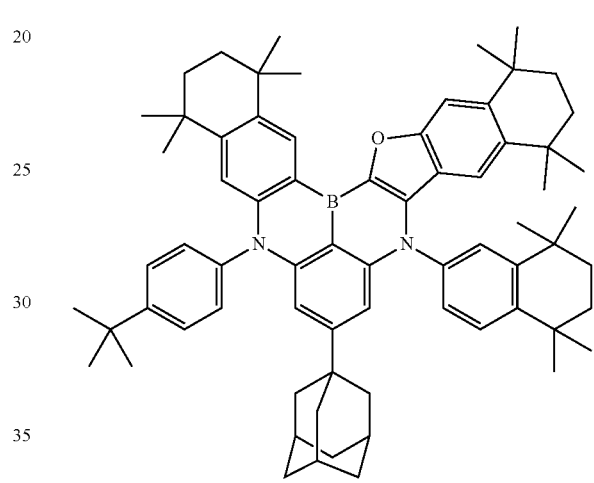
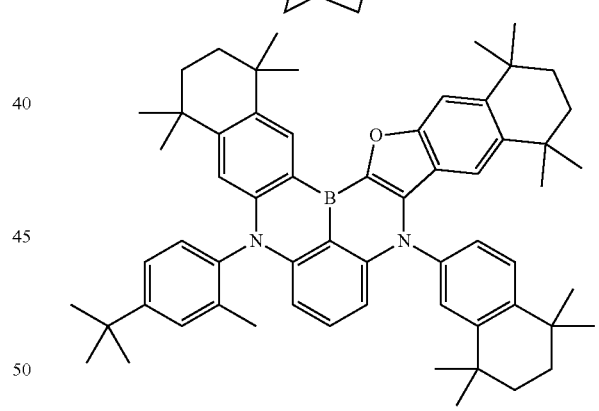
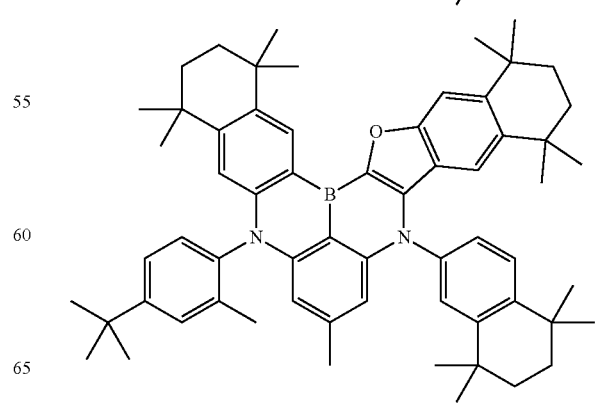

805
-continued
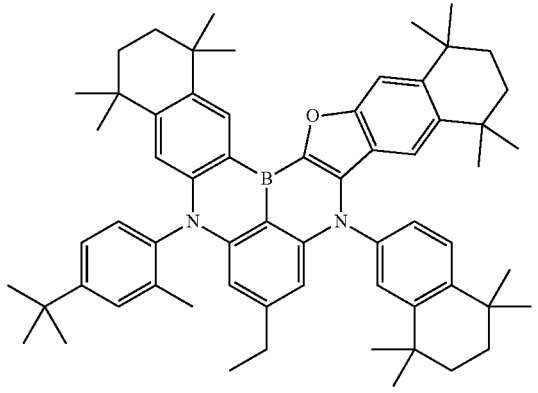
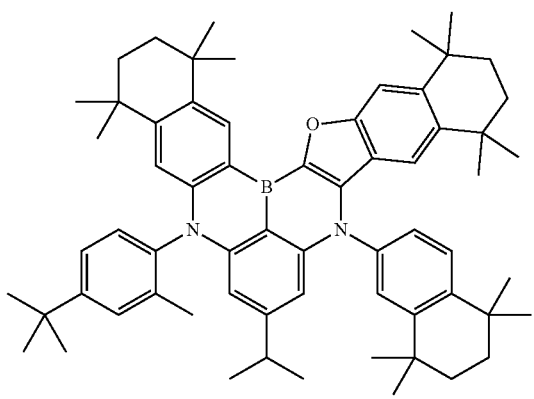
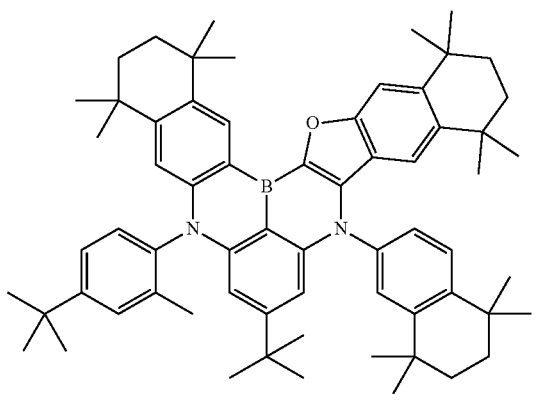
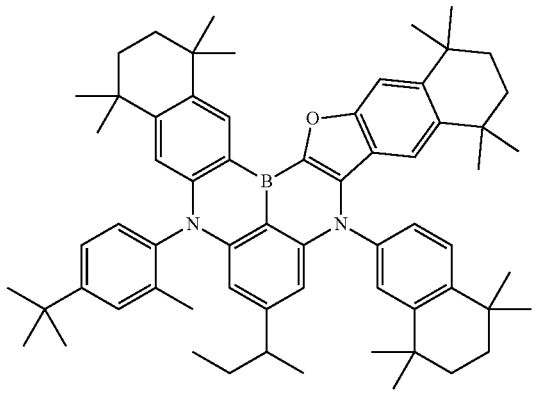
806
-continued
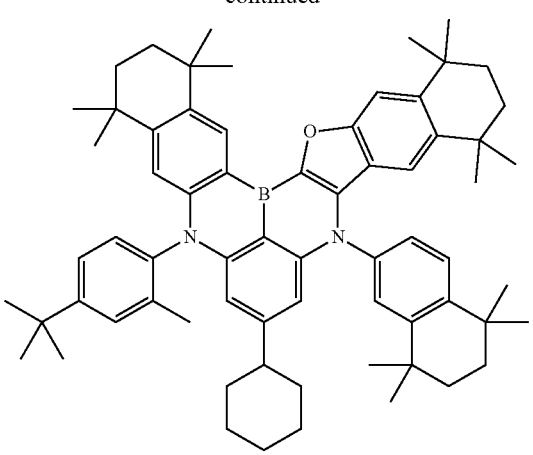
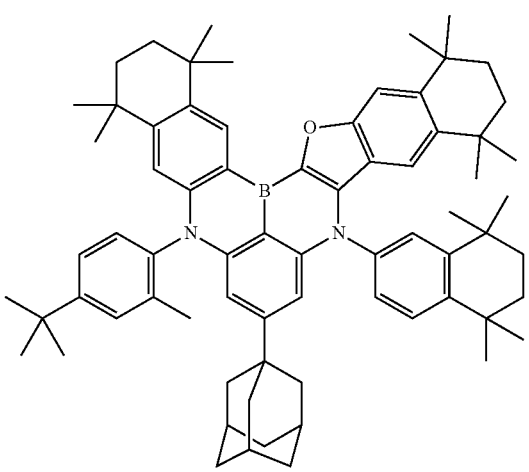
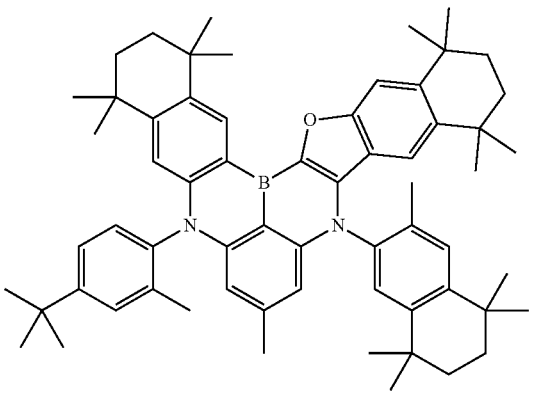
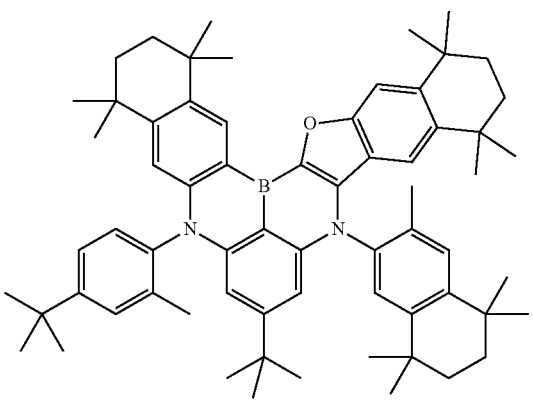

807
-continued
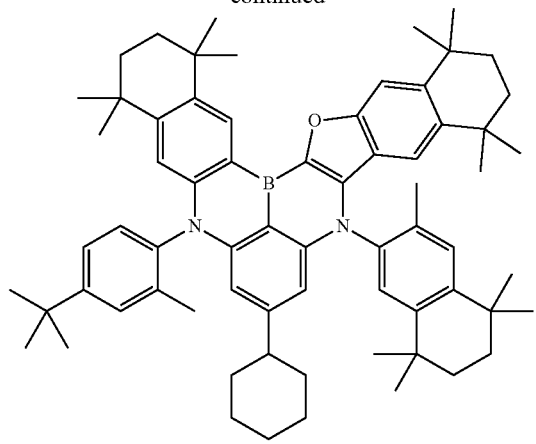
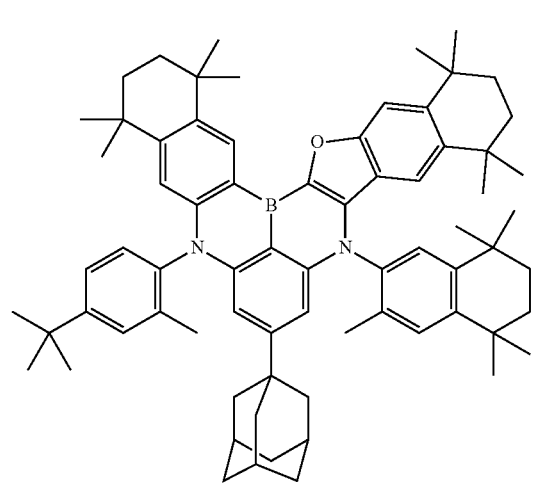
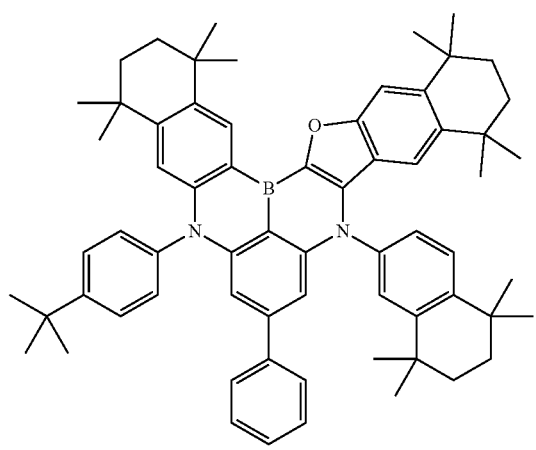
808
-continued
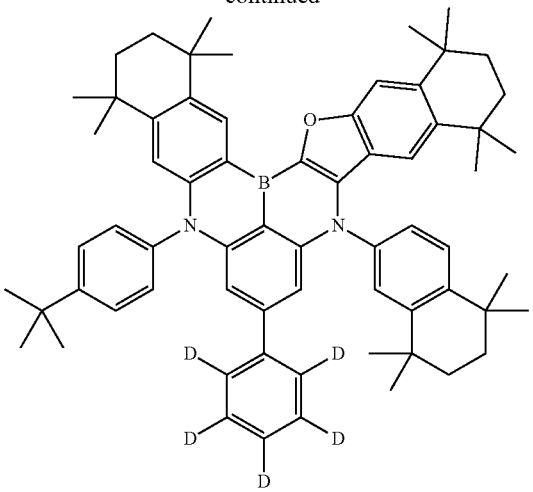
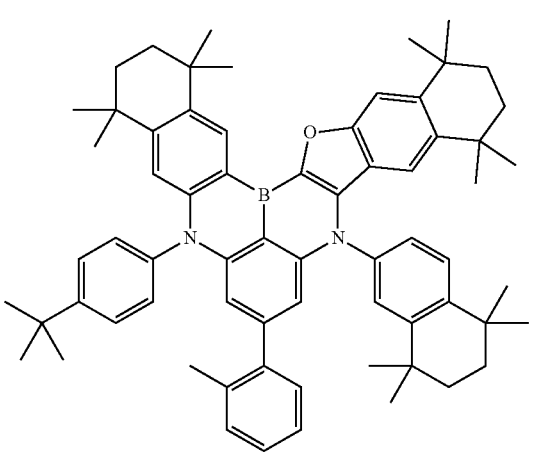
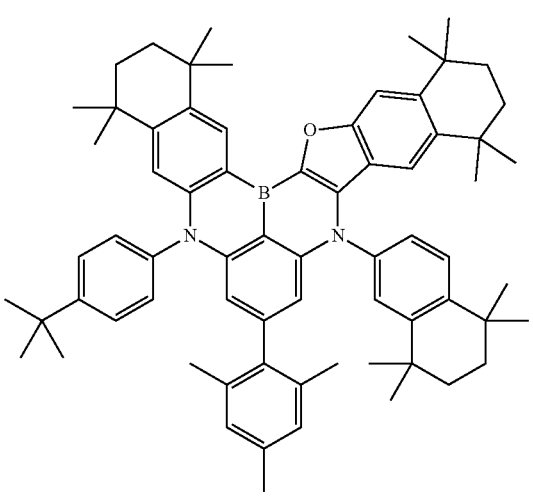

| 809 -continued | 810 -continued |
|---|---|
| 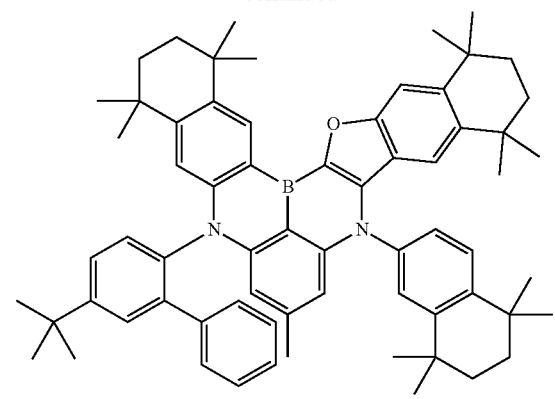 | 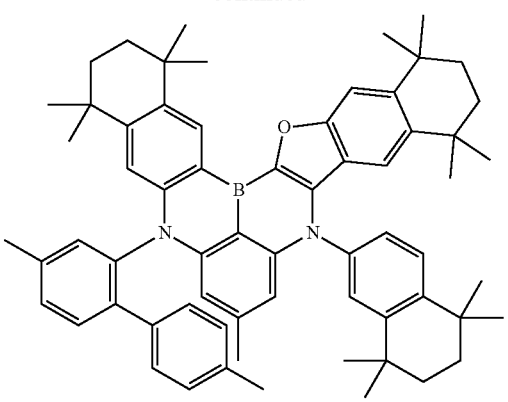 |
| 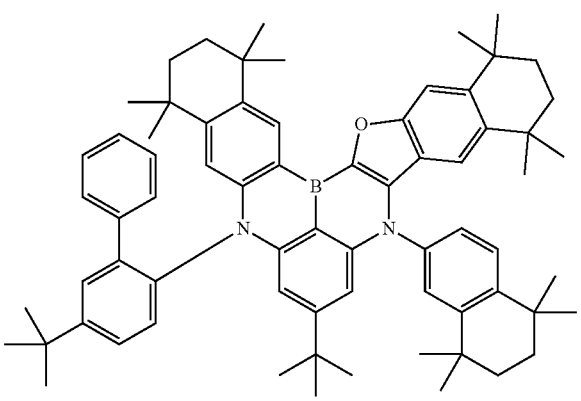 | |
| 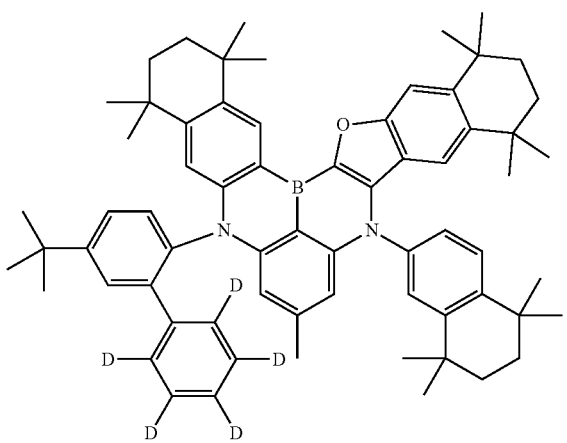 | 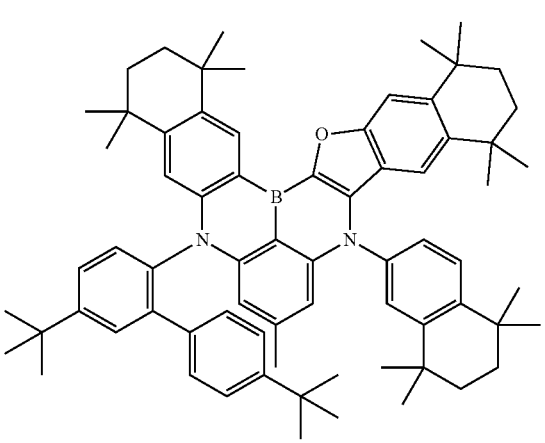 |
| 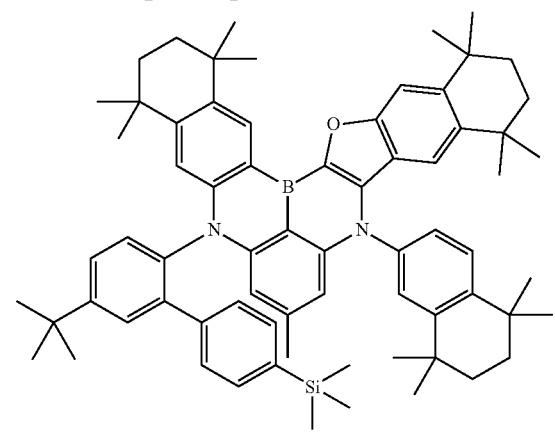 | 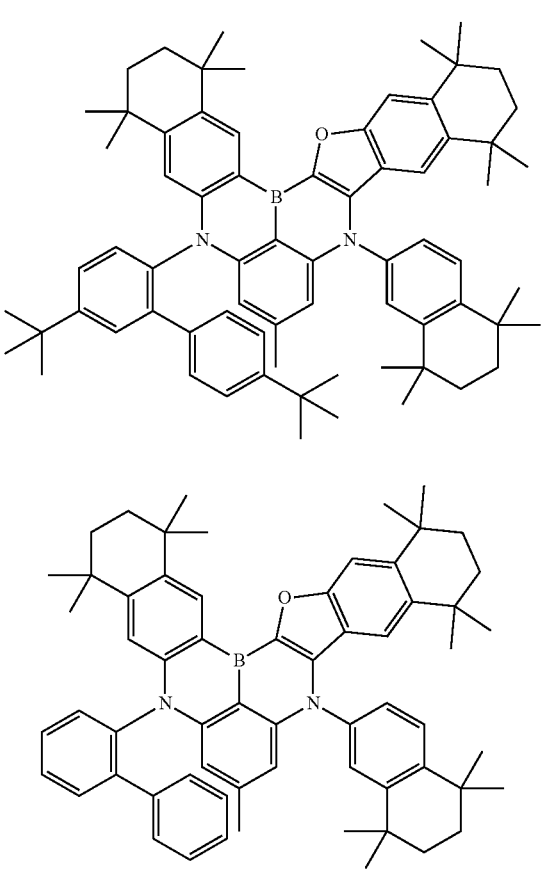 |

811
-continued
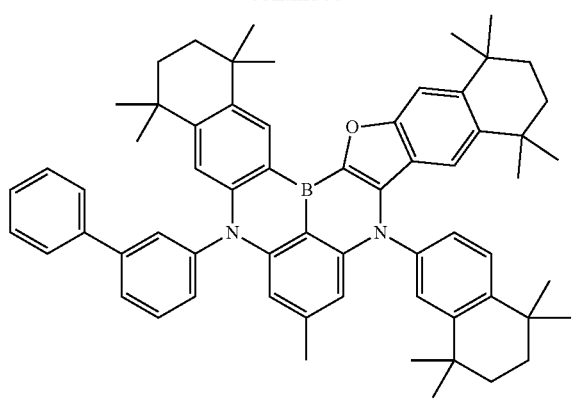
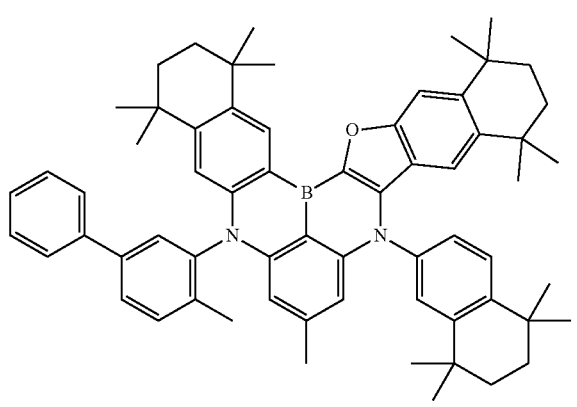
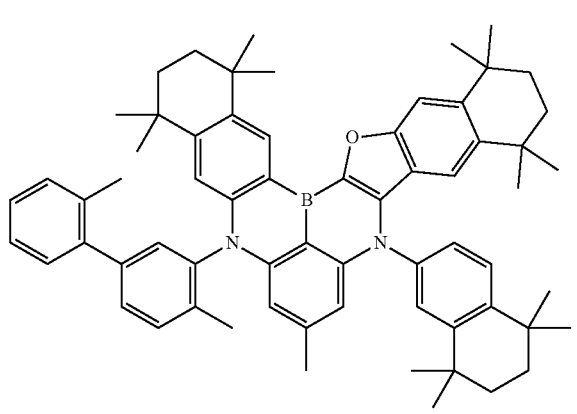
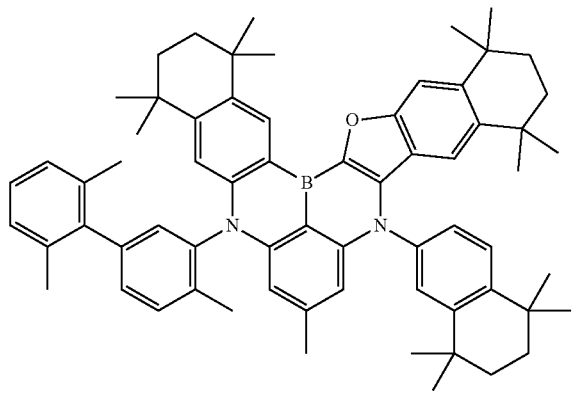
812
-continued
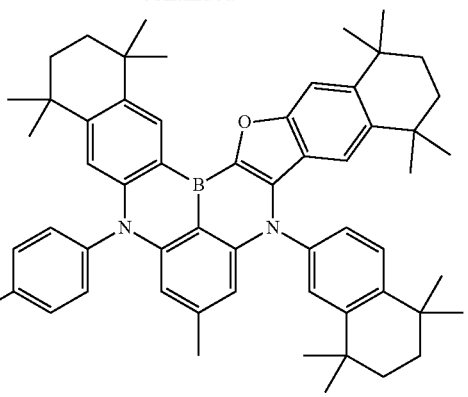
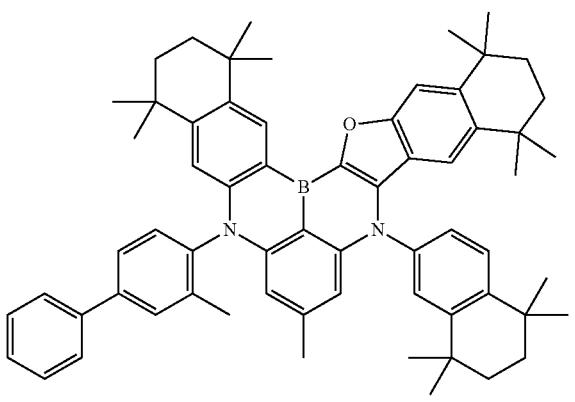
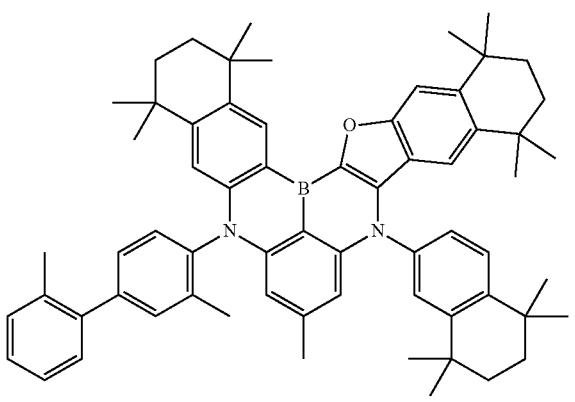
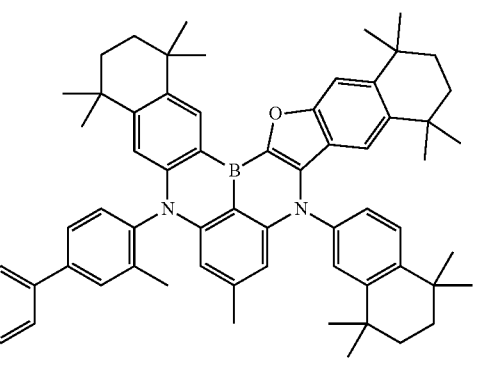

813
-continued
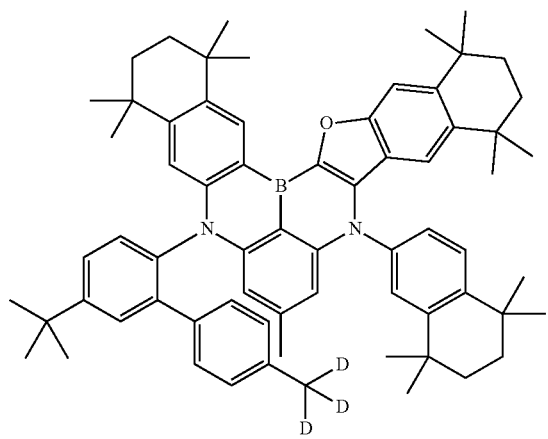
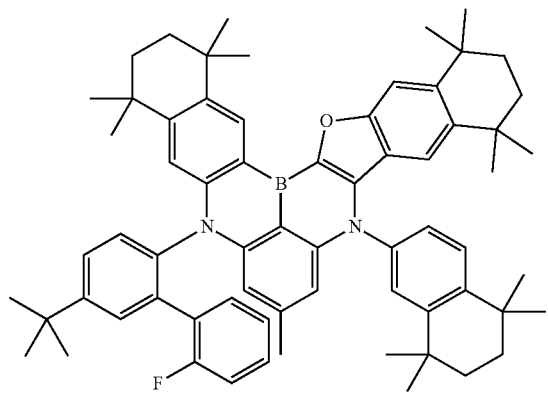
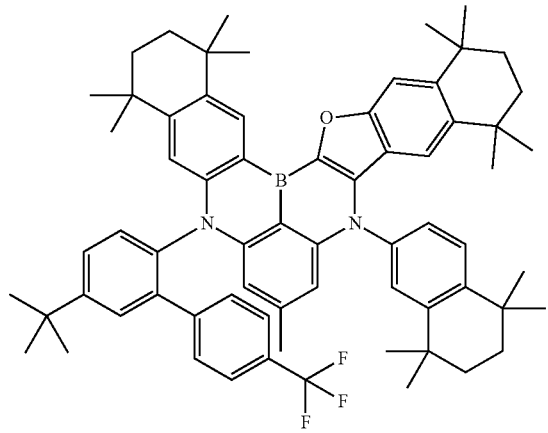
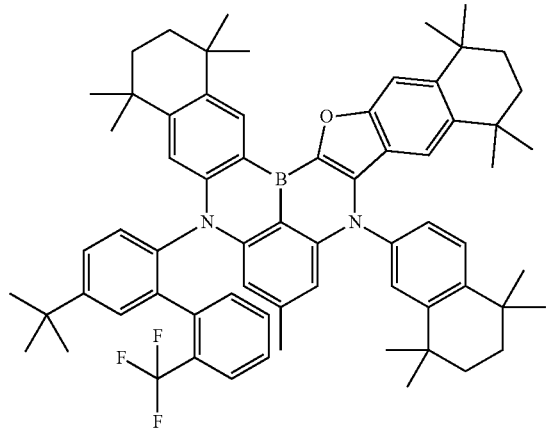
814
-continued

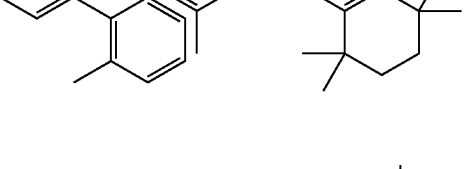
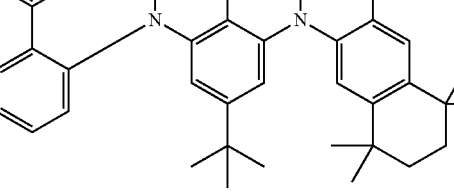
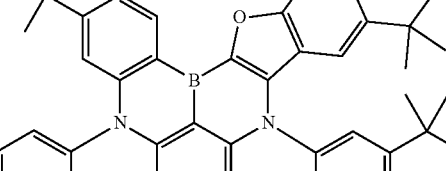

815
-continued
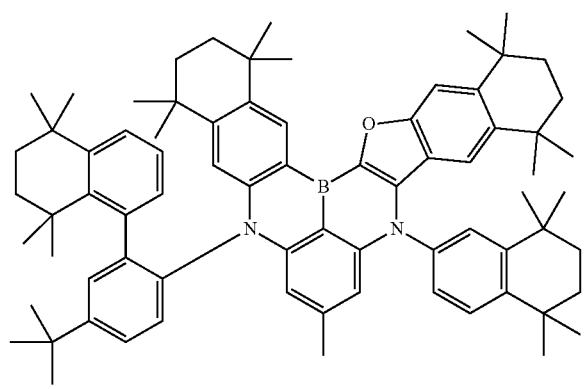
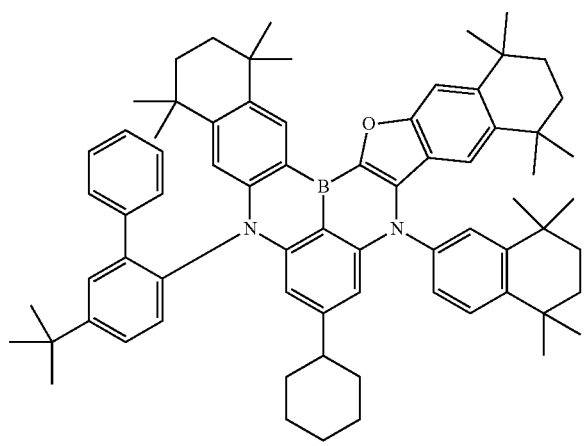
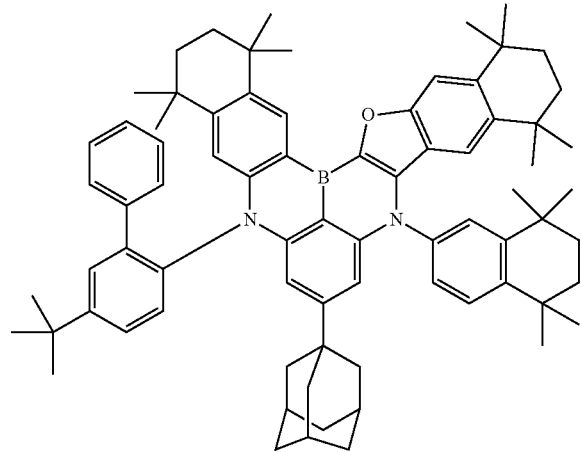
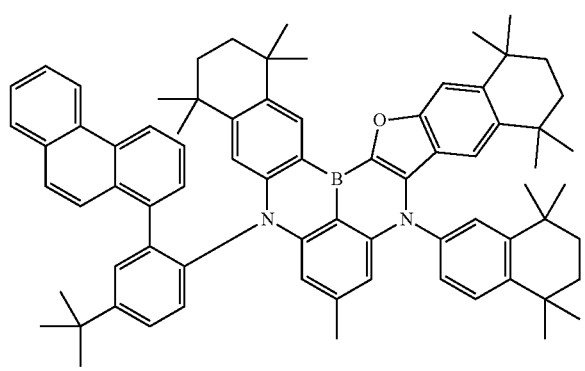
816
-continued
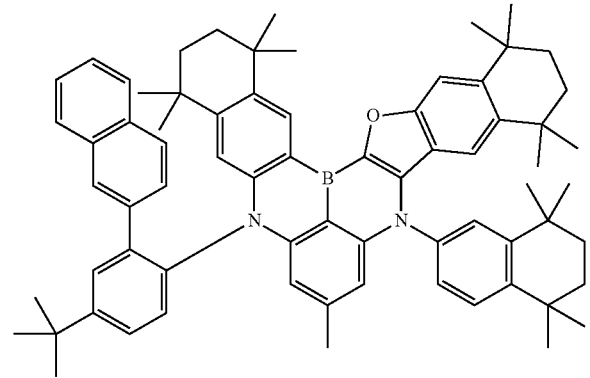
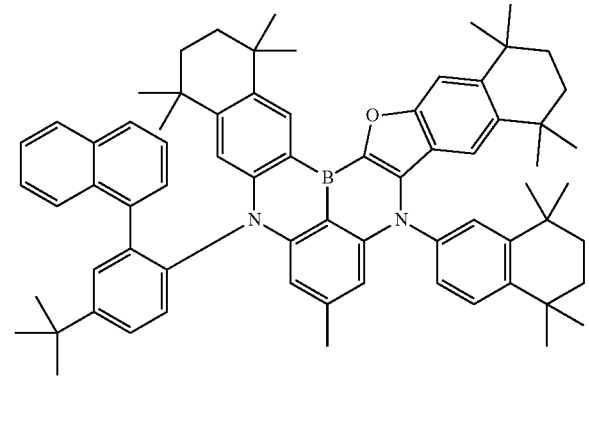
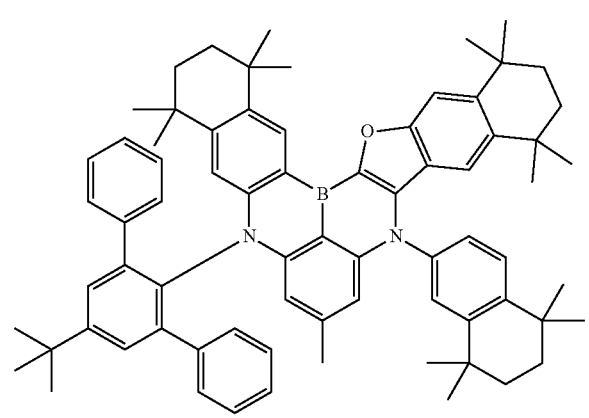
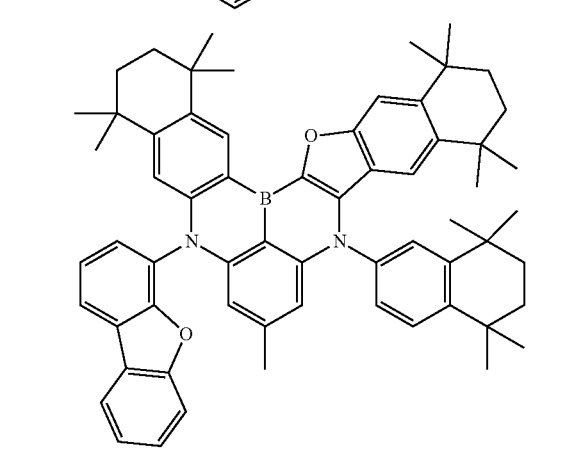

817
-continued
818
-continued
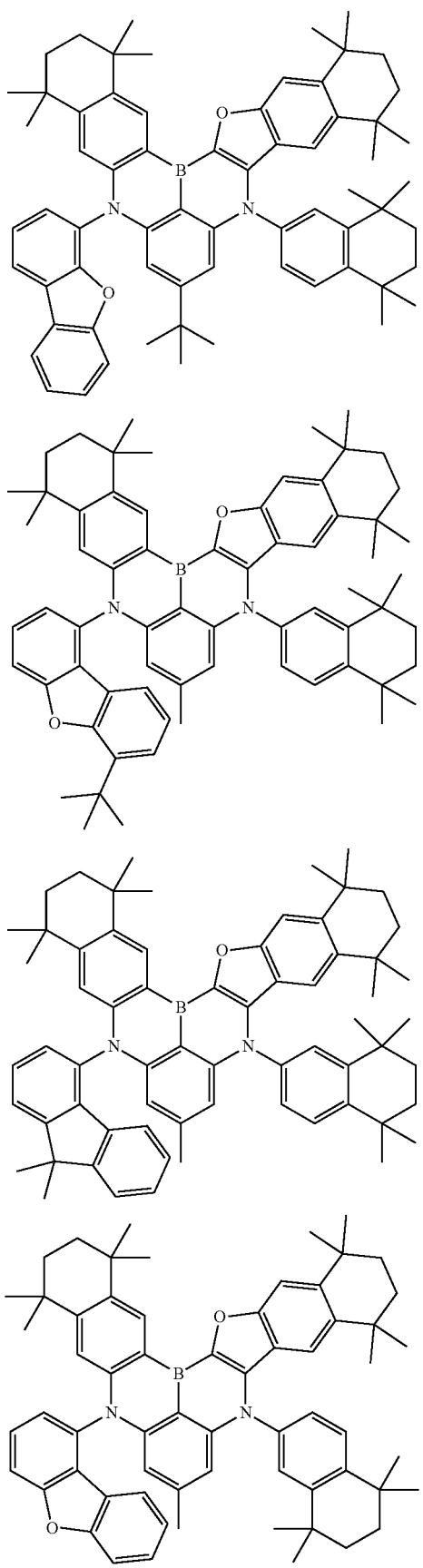
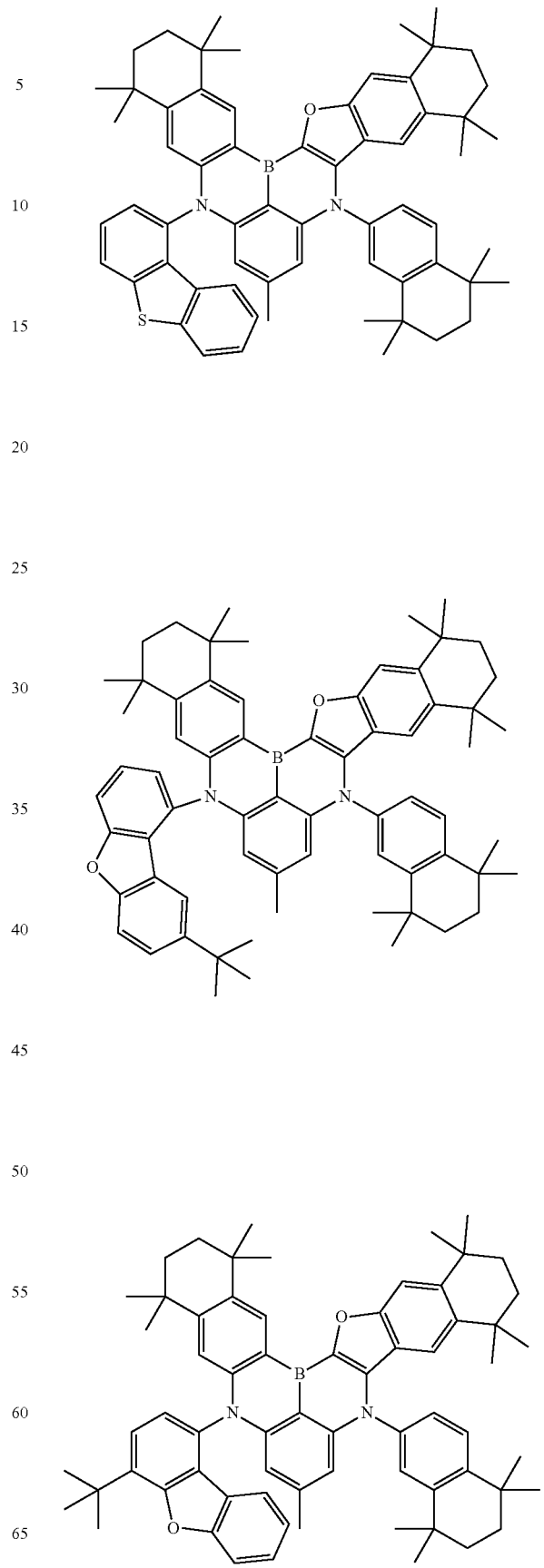

819
-continued
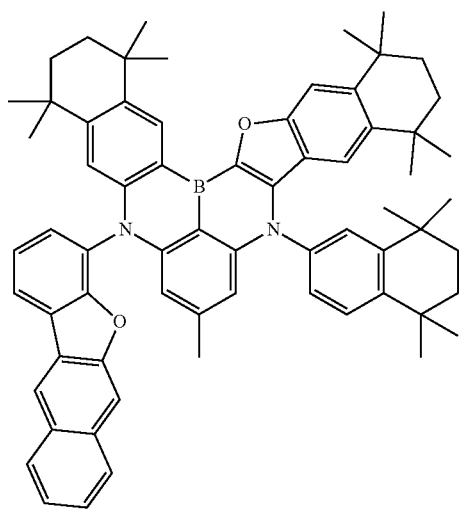
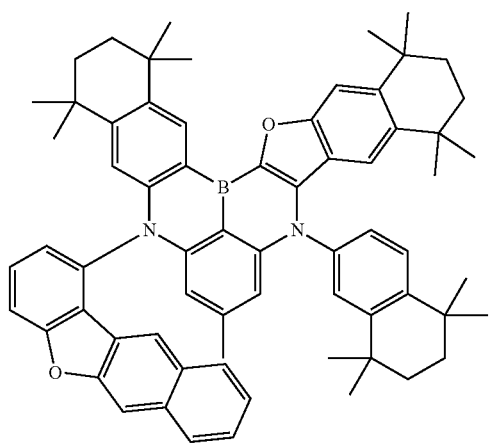
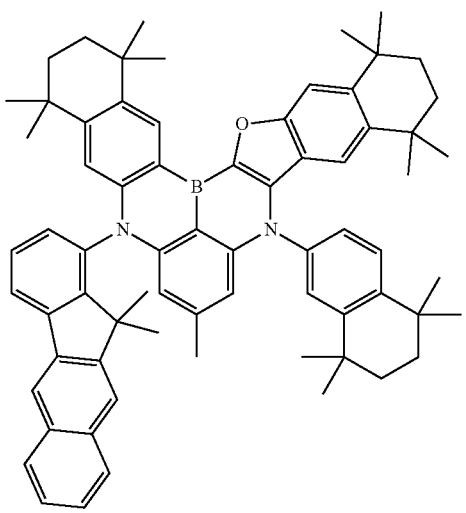
820
-continued
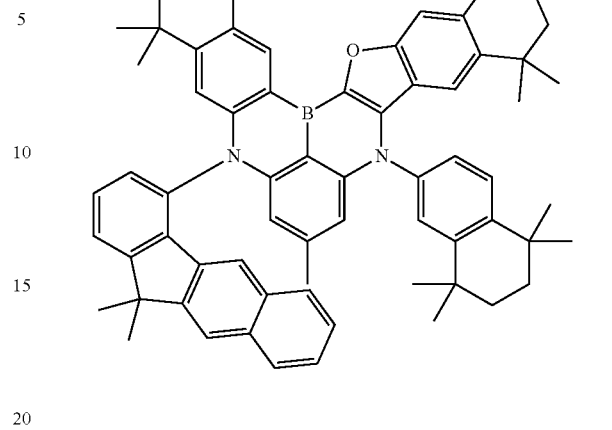

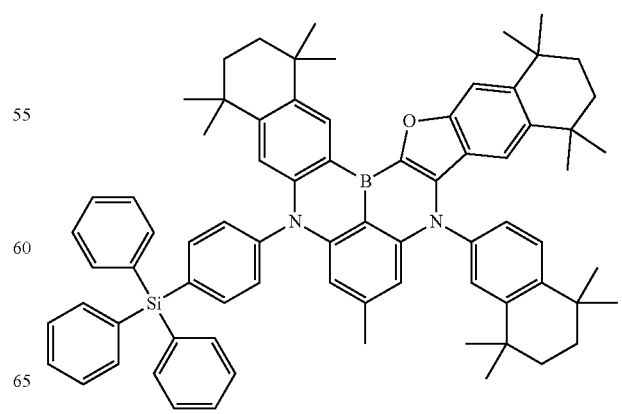

| 821 -continued | 822 -continued |
|---|---|
| 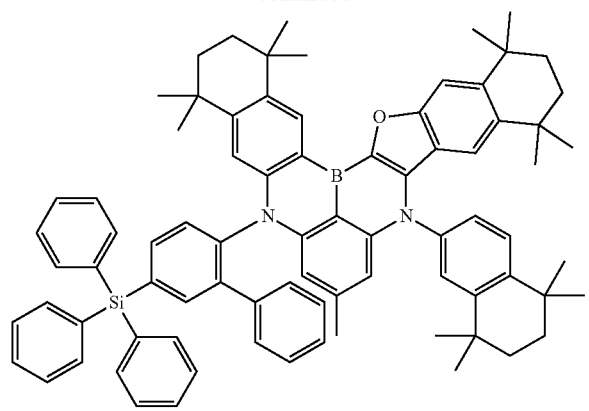 | 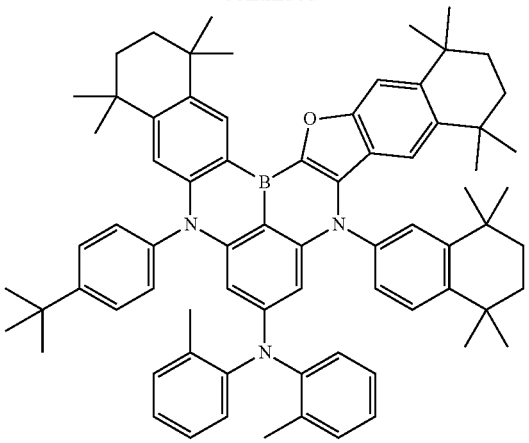 |
| 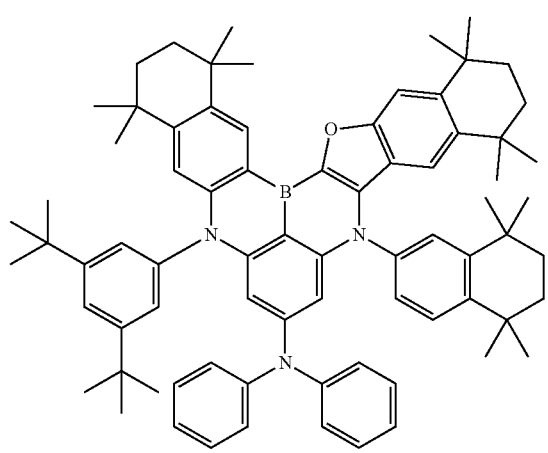 | 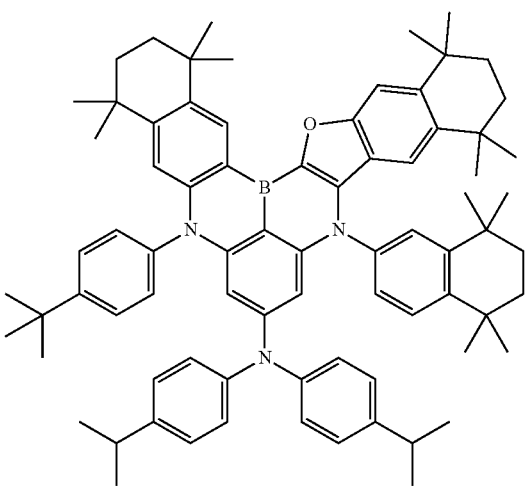 |
| 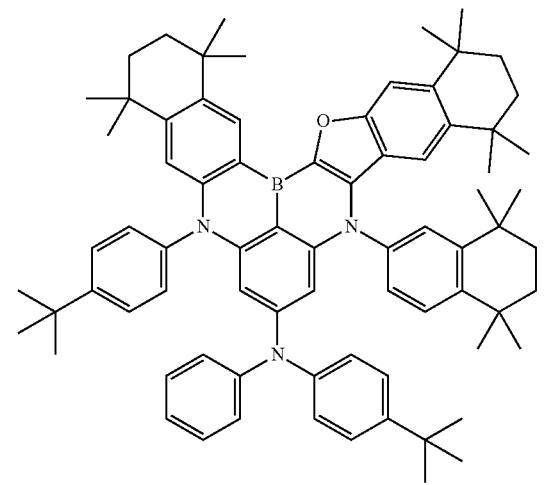 | 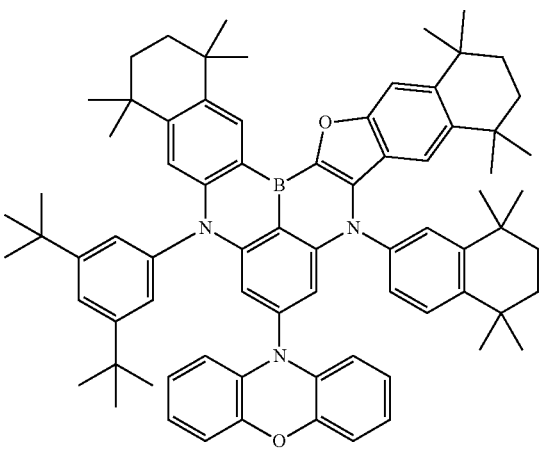 |

823
-continued
824
-continued
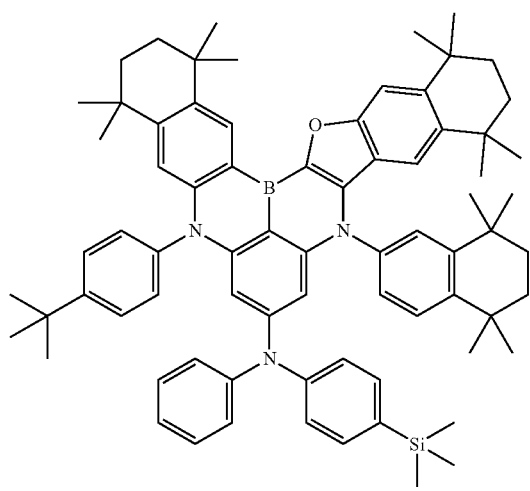
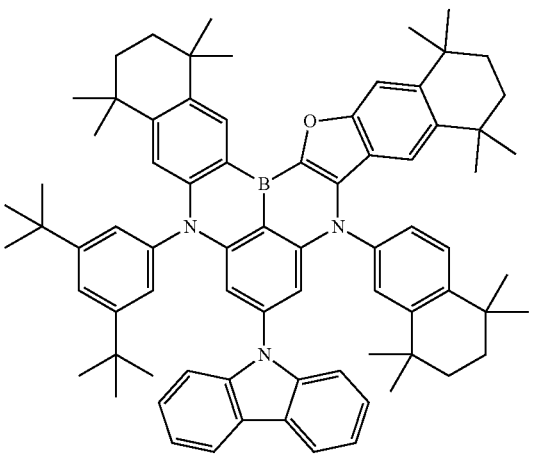
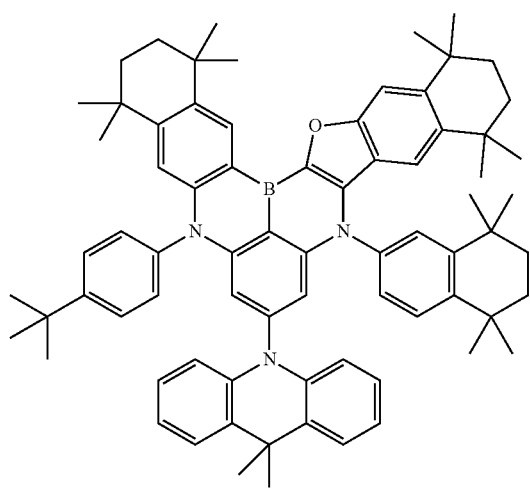
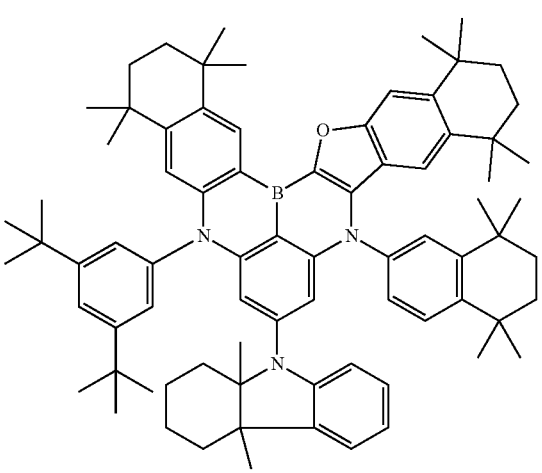
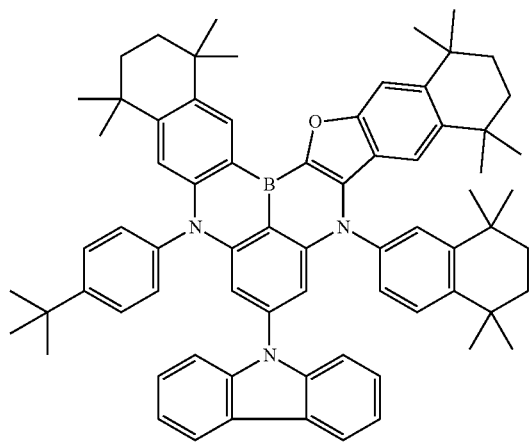

825
-continued
826
-continued
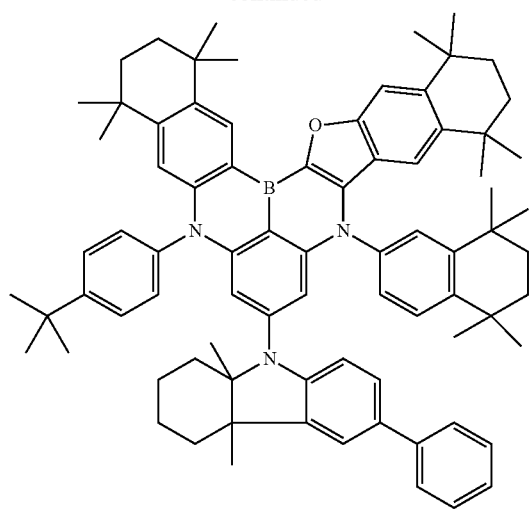
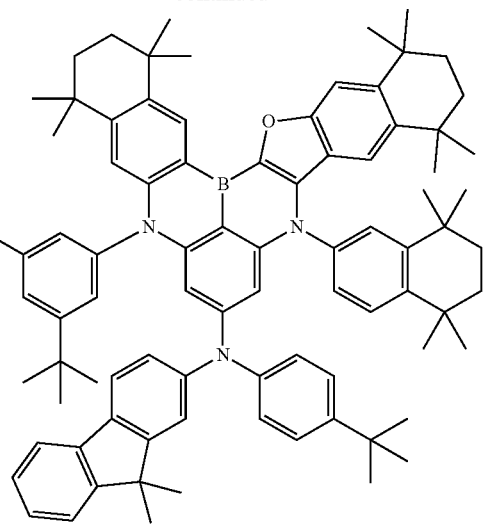
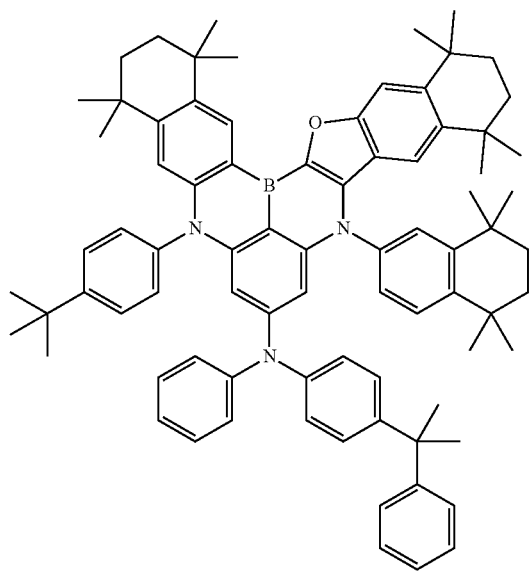
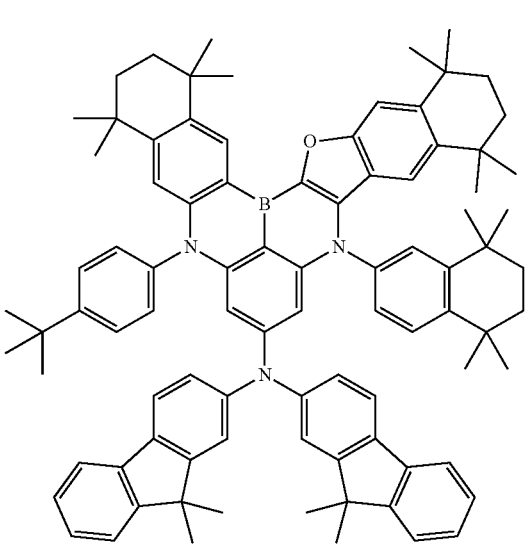
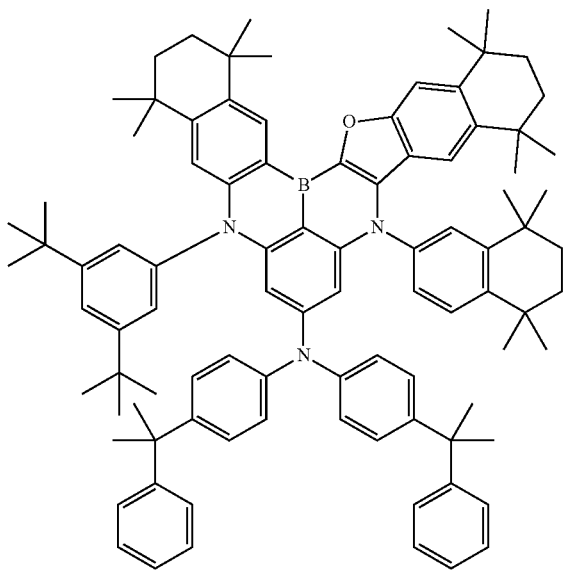
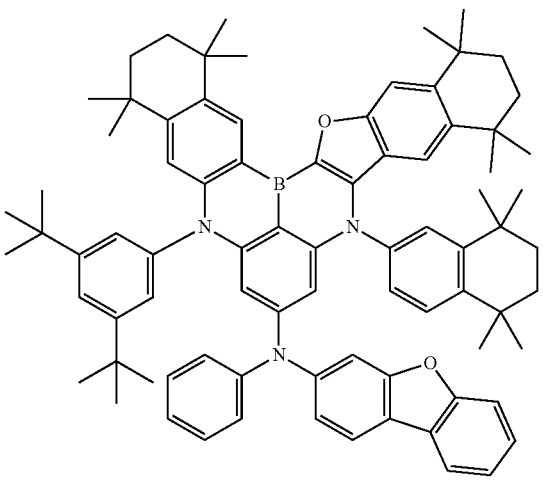

827
-continued
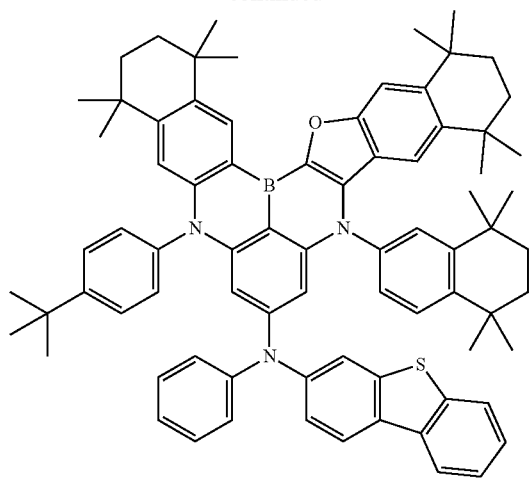
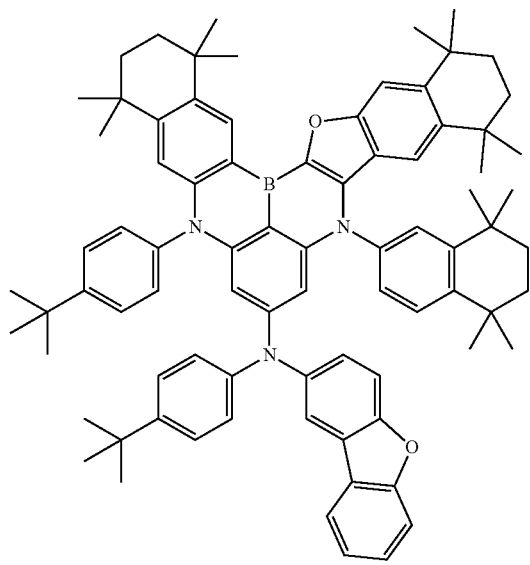
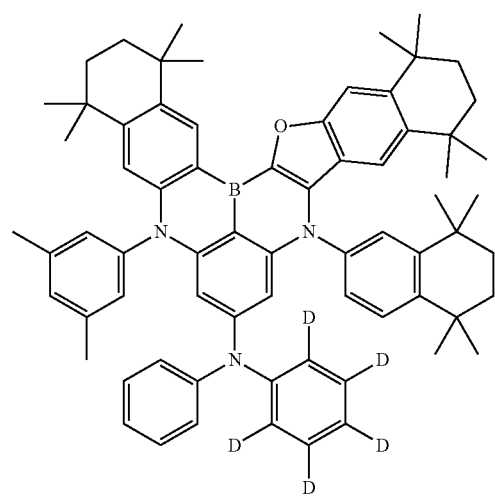
828
-continued
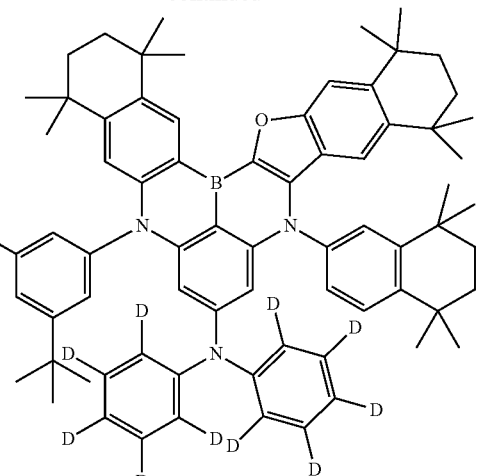
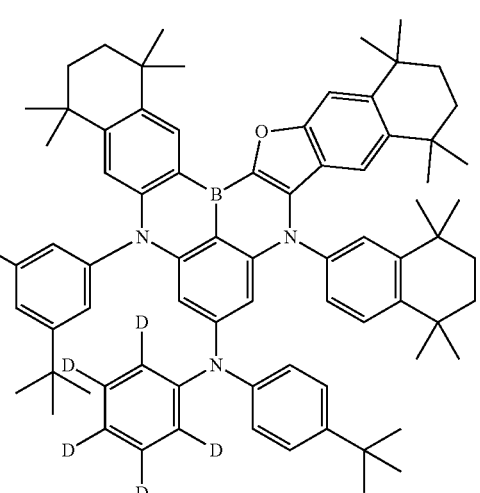
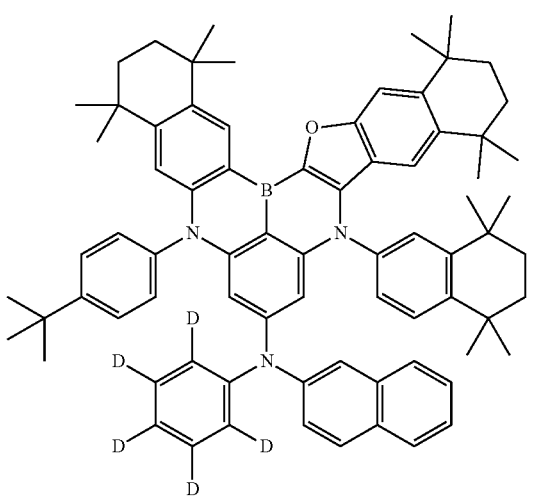

829
-continued
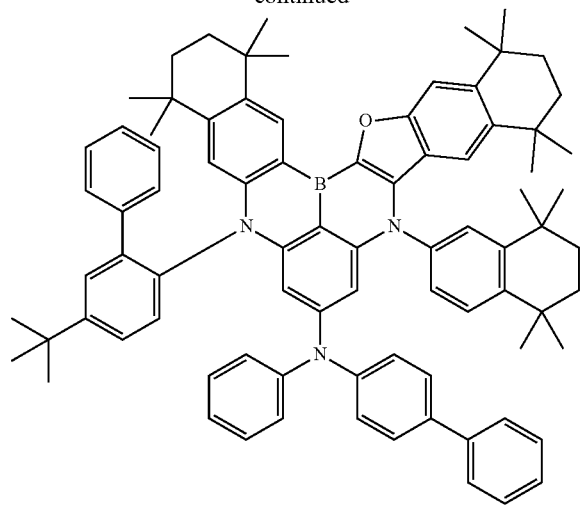
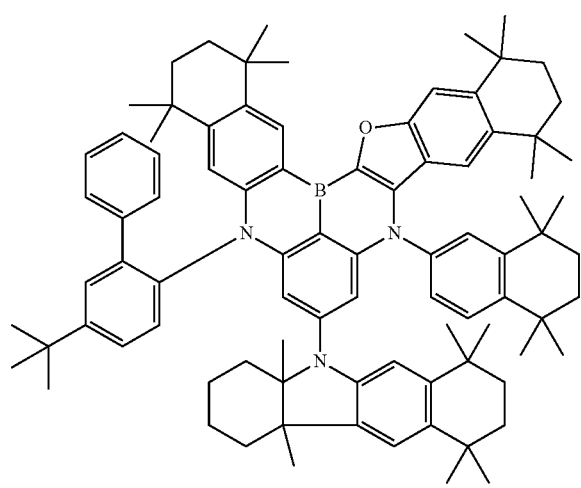
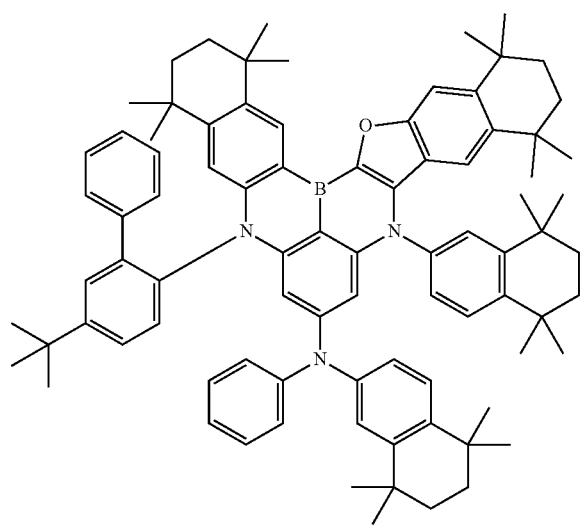
830
-continued
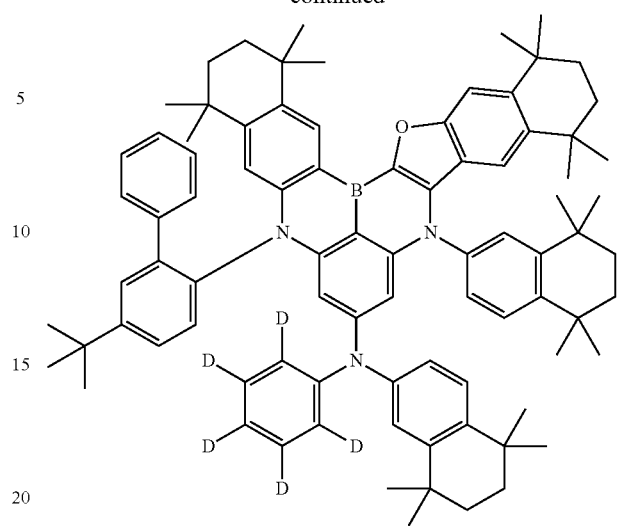
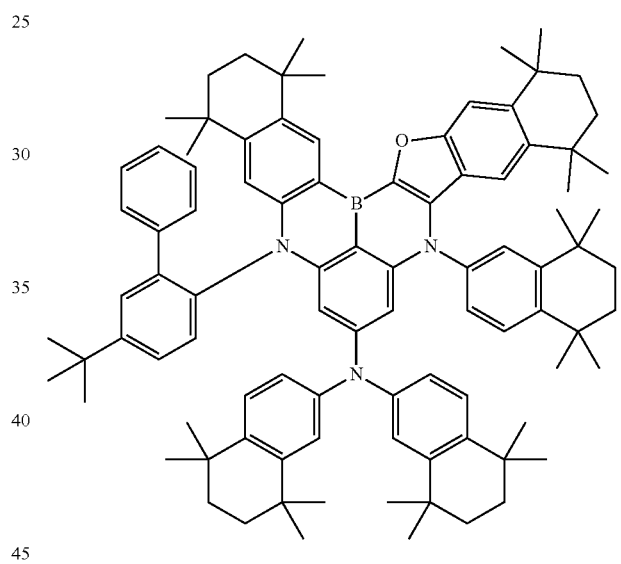
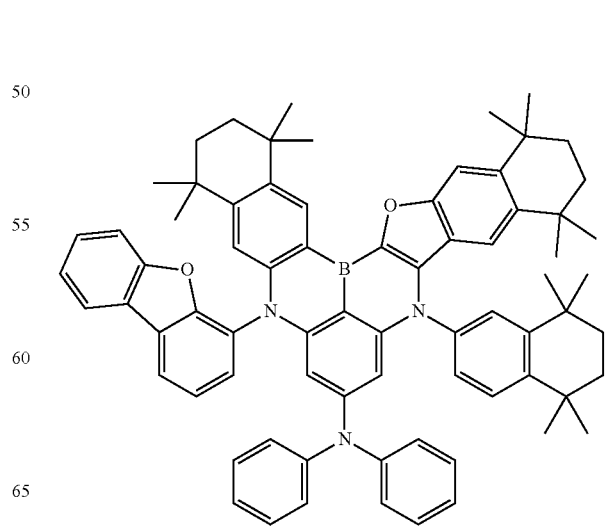

| 831 | 832 |
|---|---|
| -continued | -continued |
| 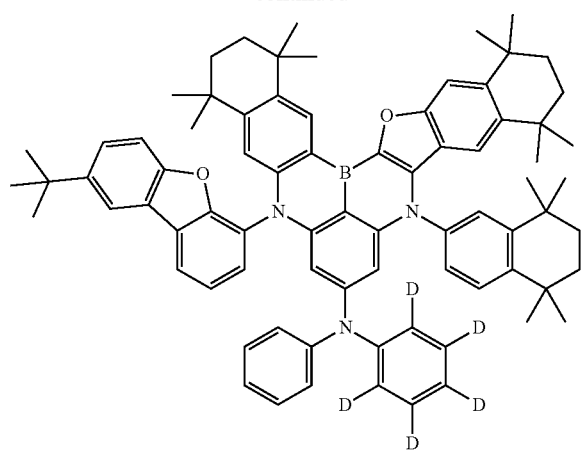 | 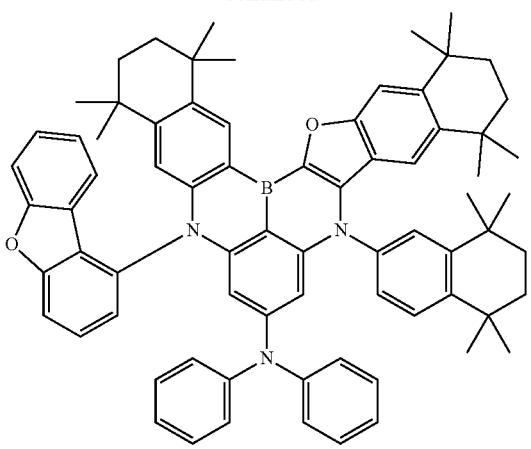 |
| 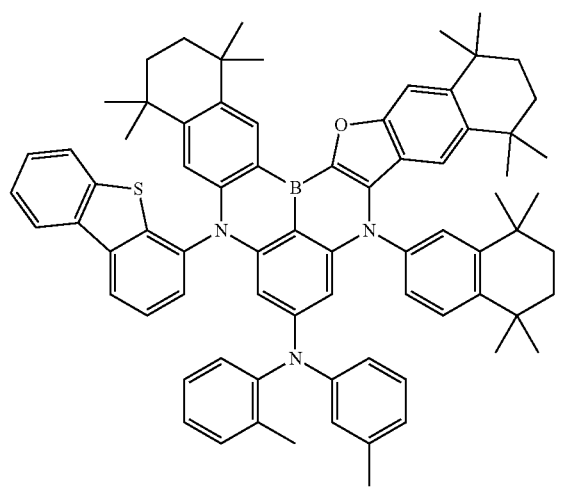 | 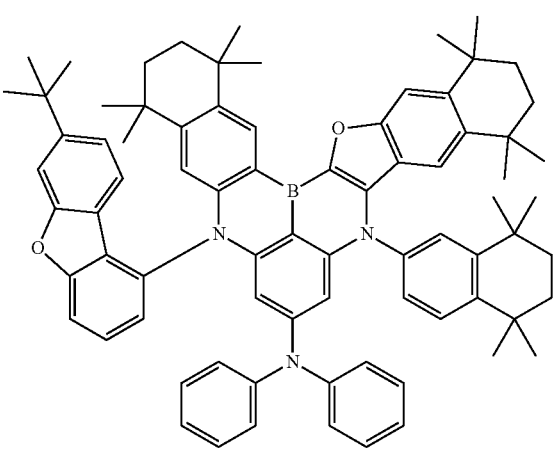 |
| 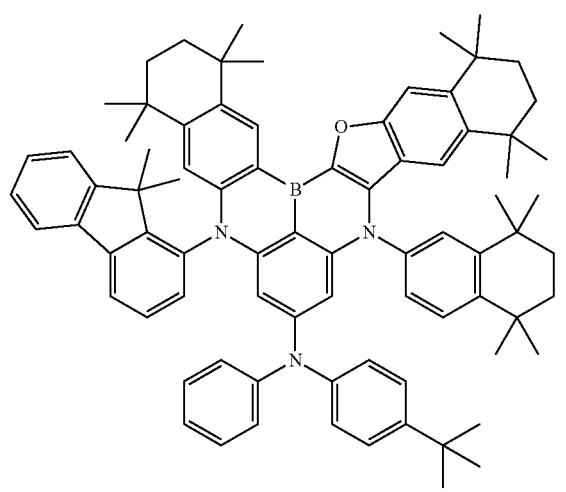 | 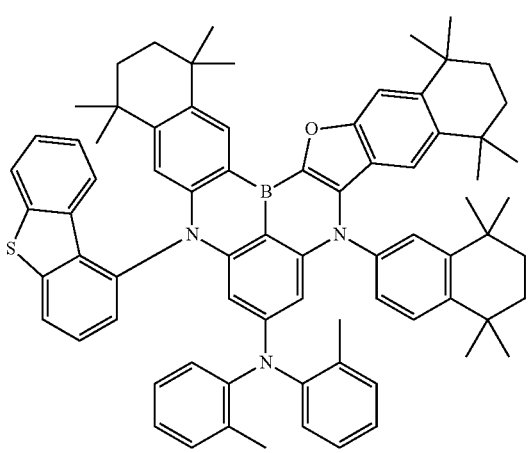 |

833
-continued
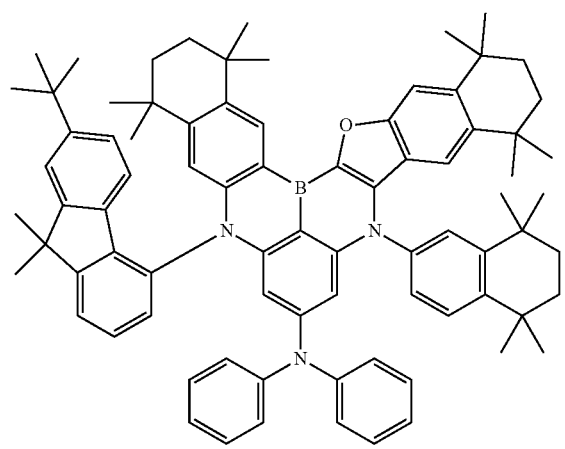
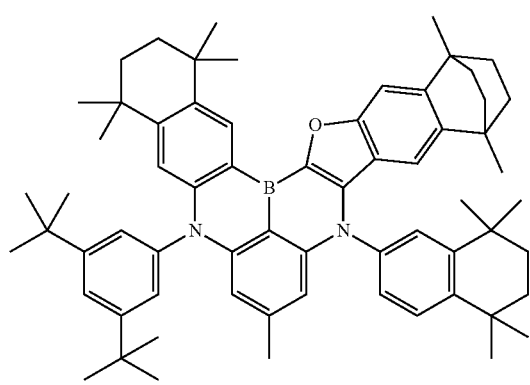
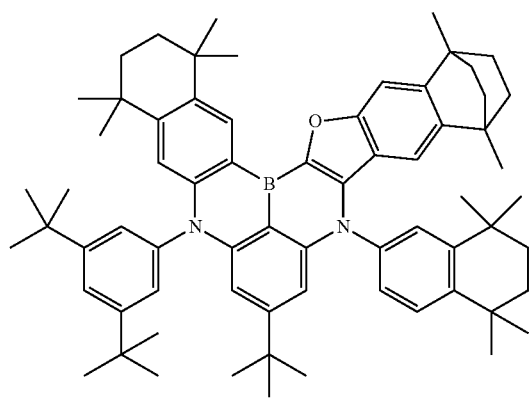
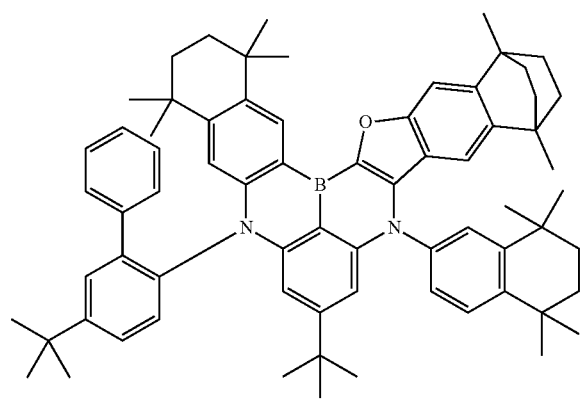
834
-continued
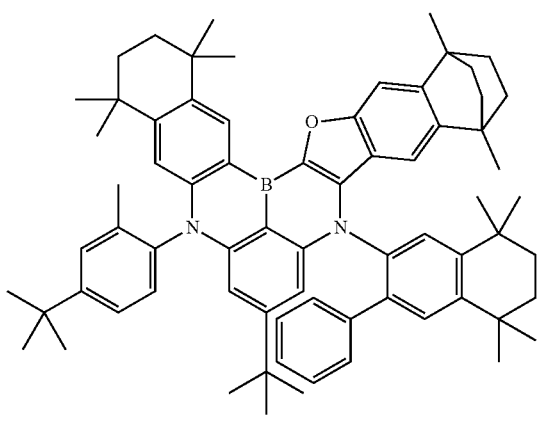
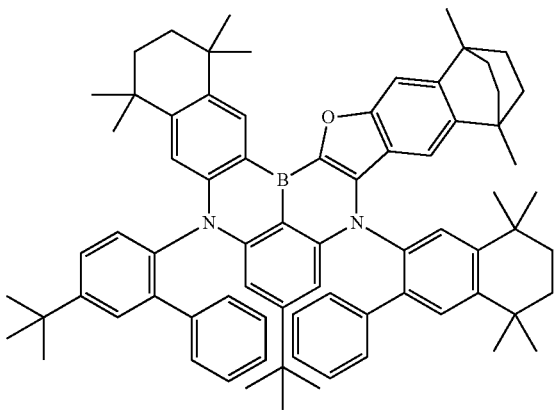
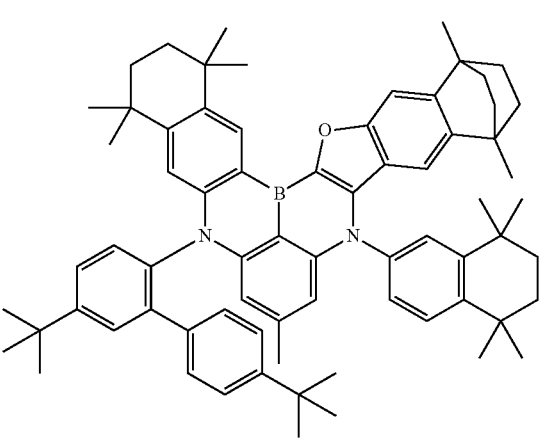
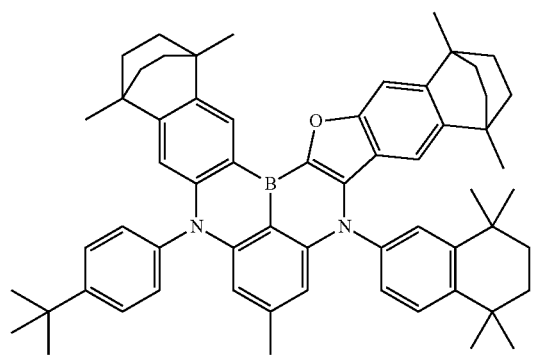

835
-continued
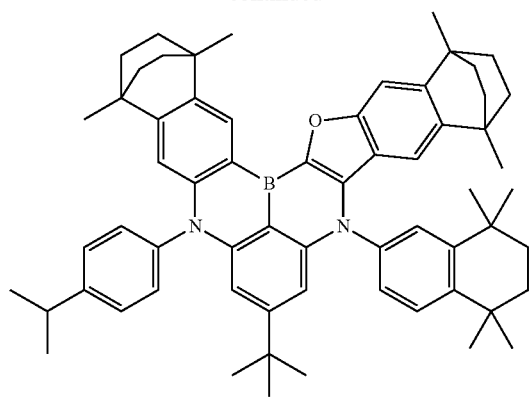
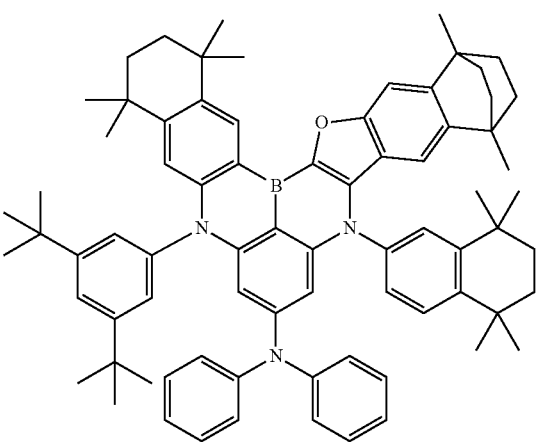
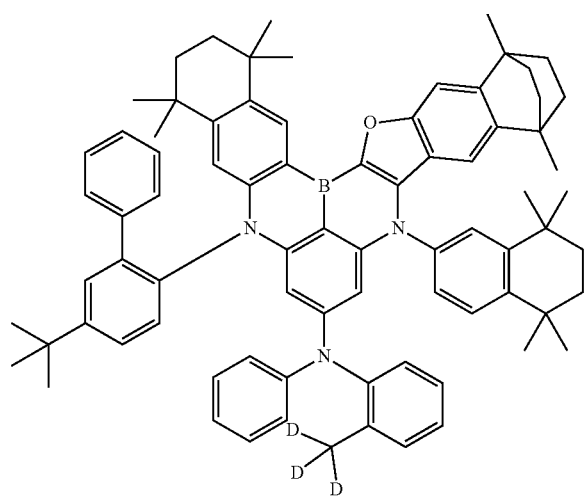
836
-continued
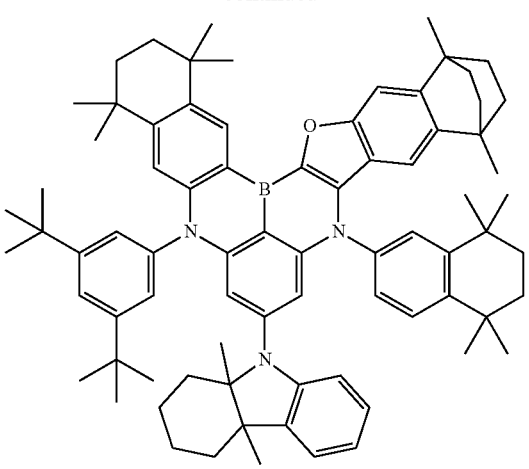
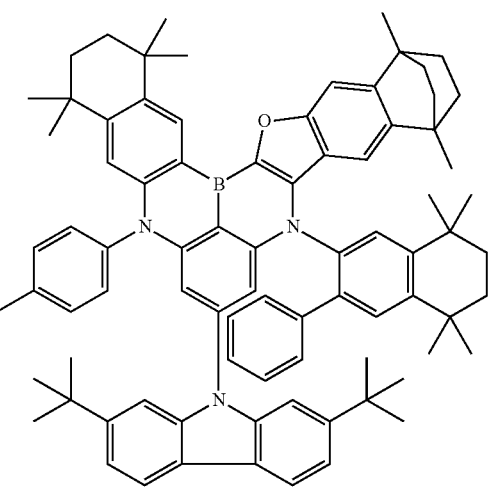
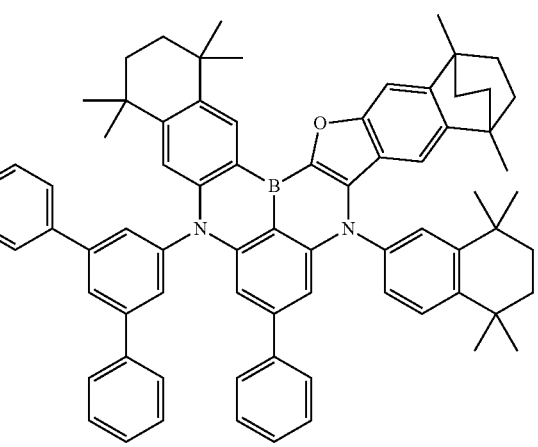

837
-continued
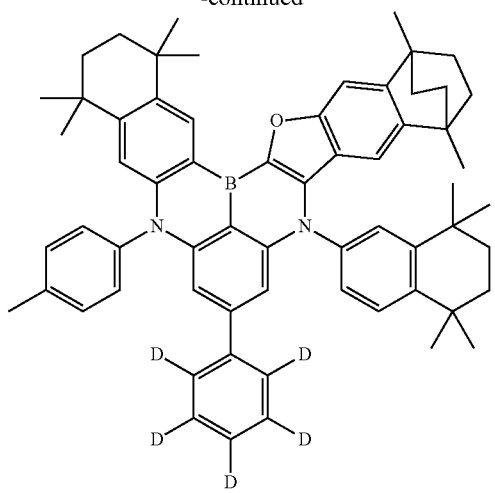
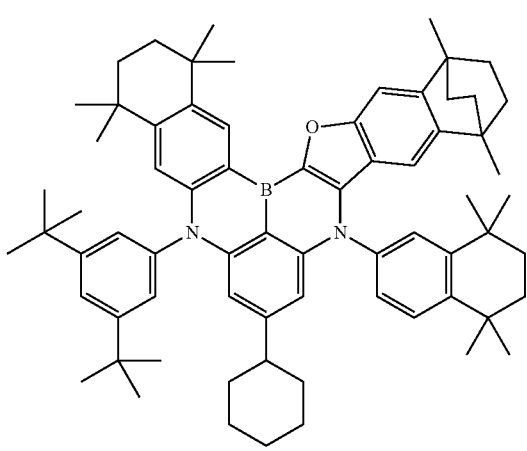
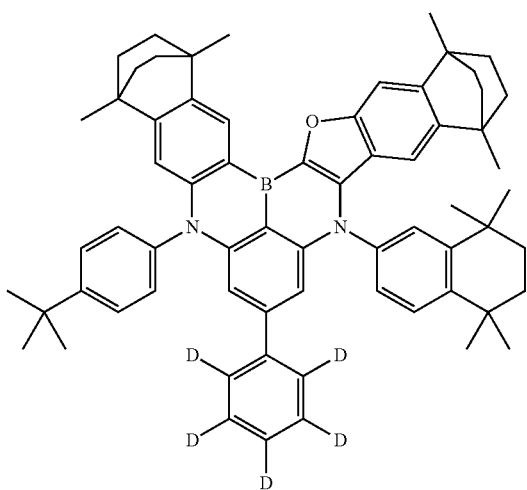
838
-continued
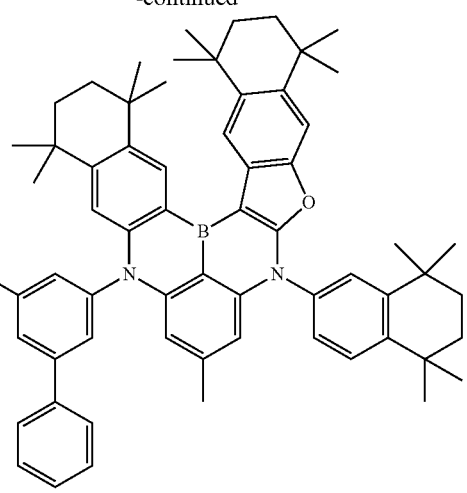
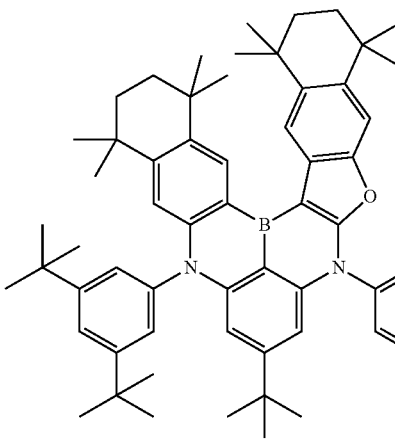
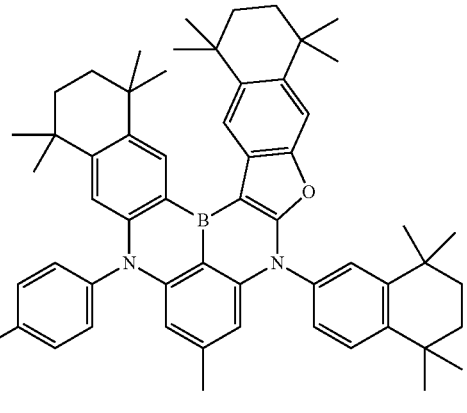

839
-continued
840
-continued
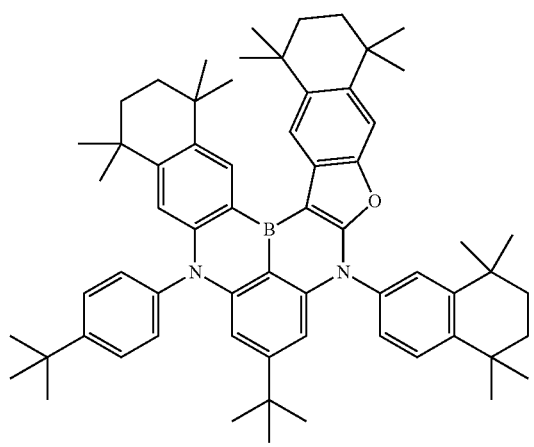
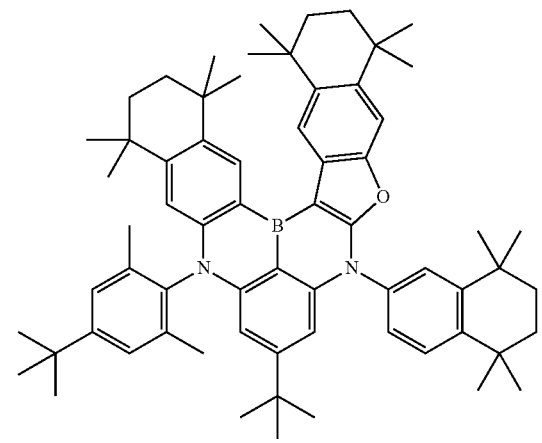
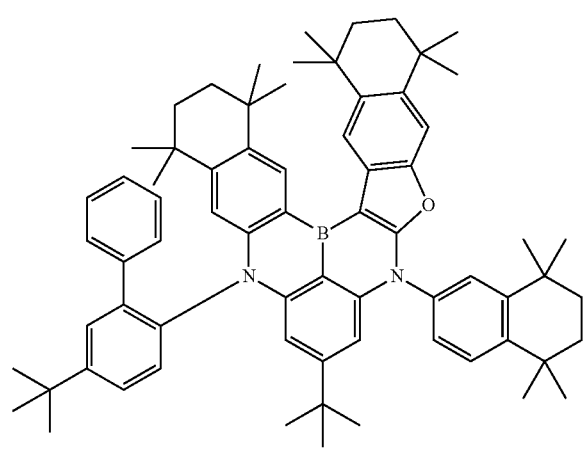
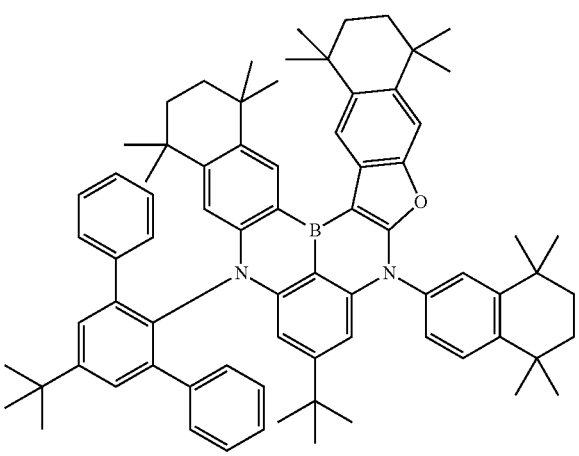
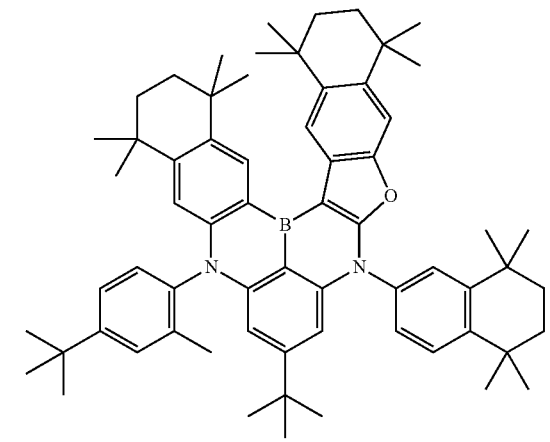
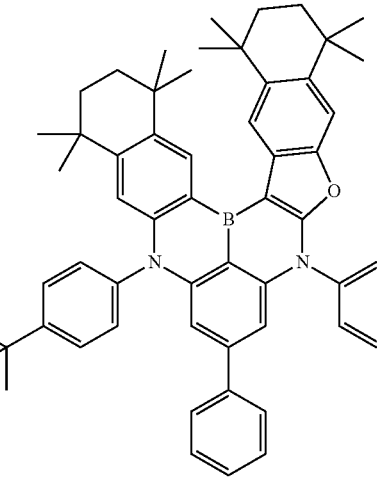

841
-continued
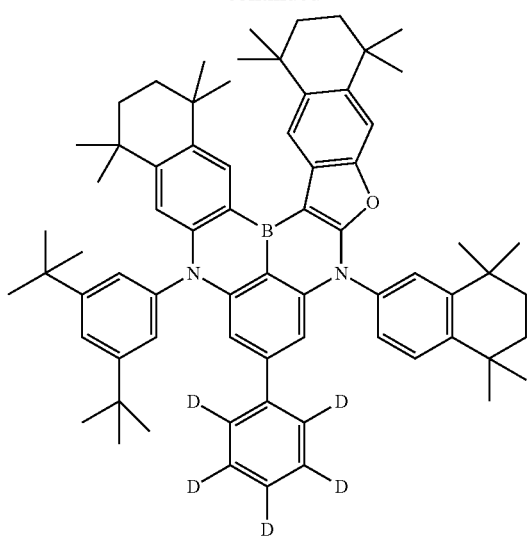
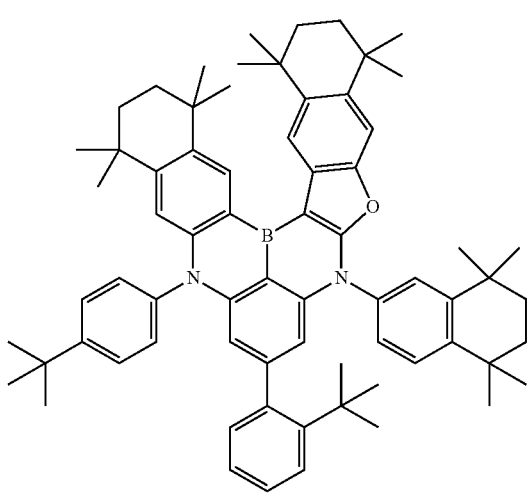
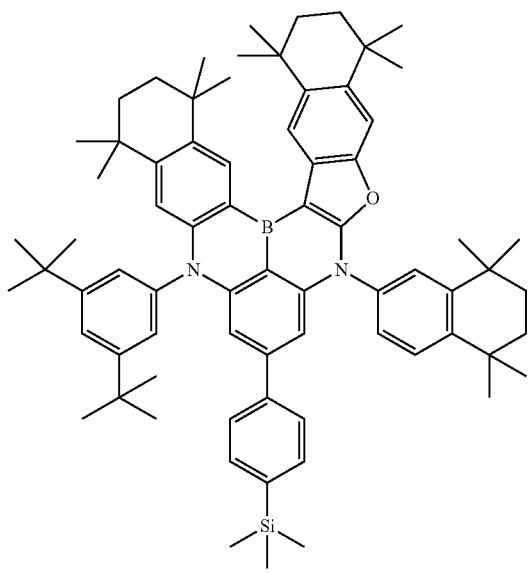
842
-continued
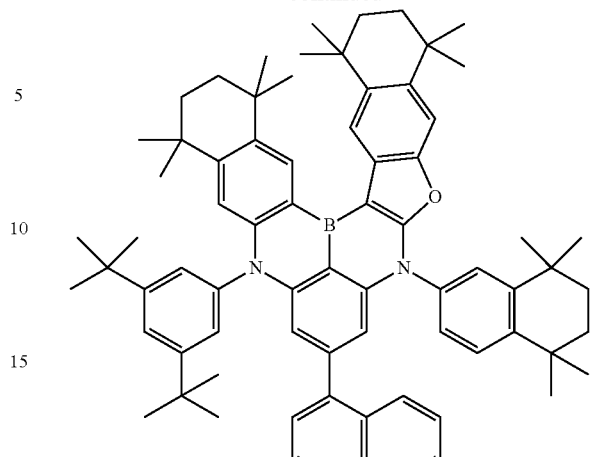
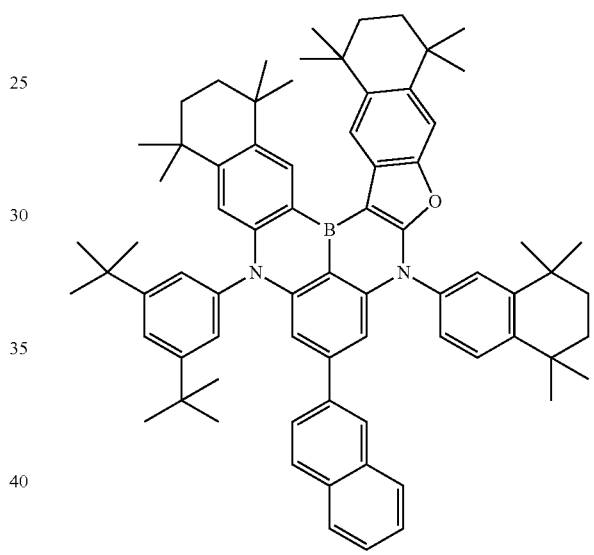
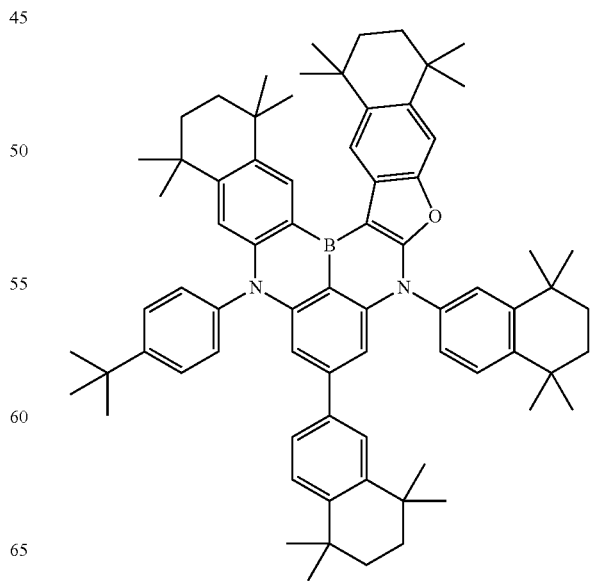

843
-continued
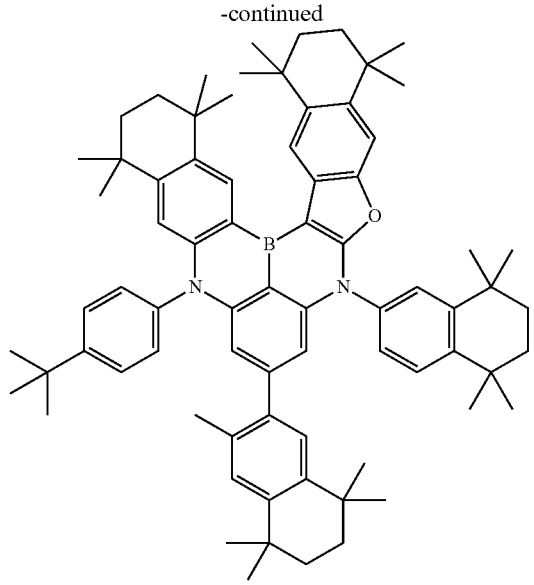
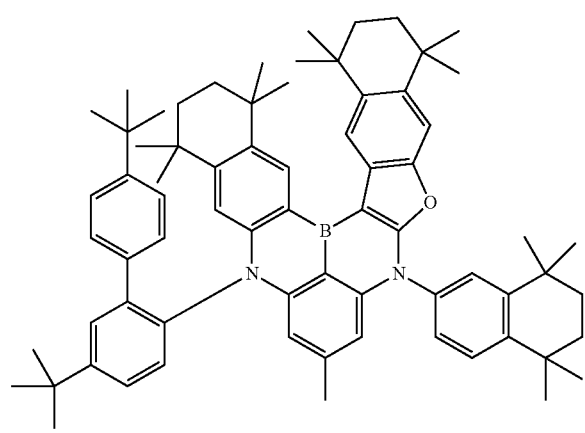
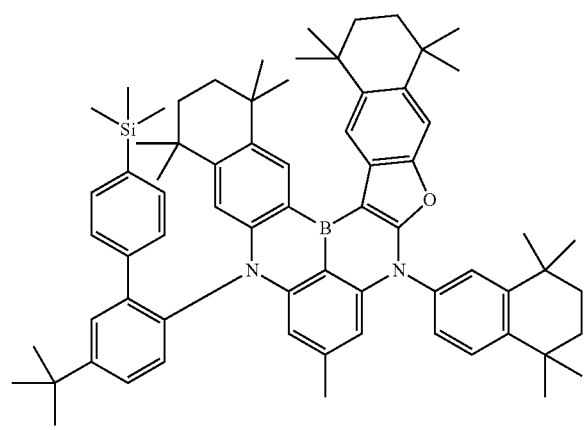
844
-continued
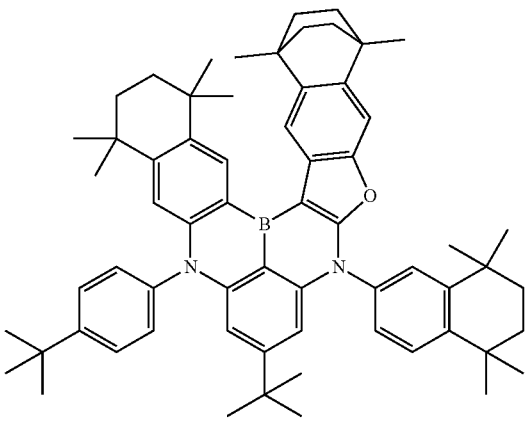
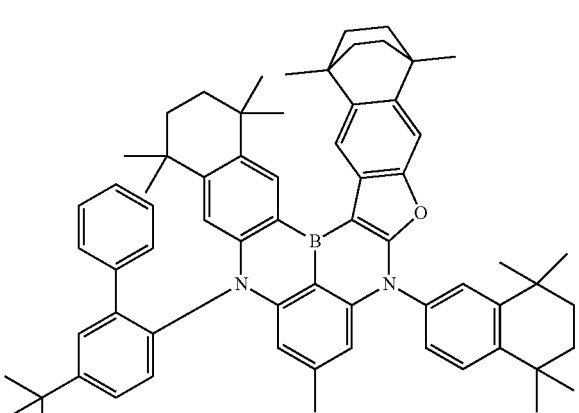
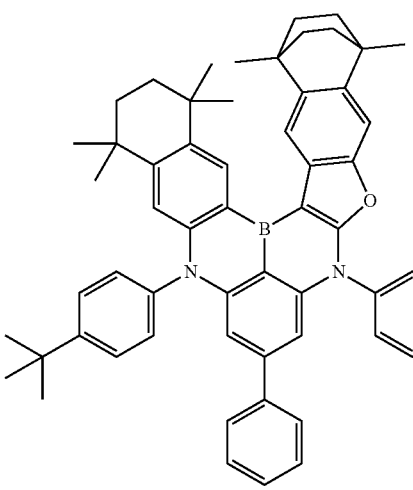

845
-continued
846
-continued
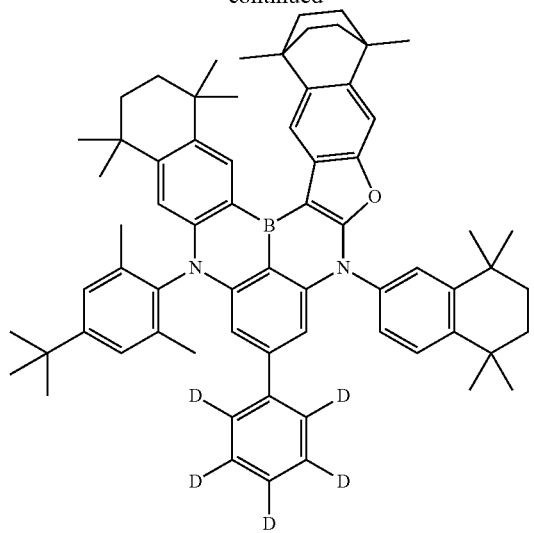
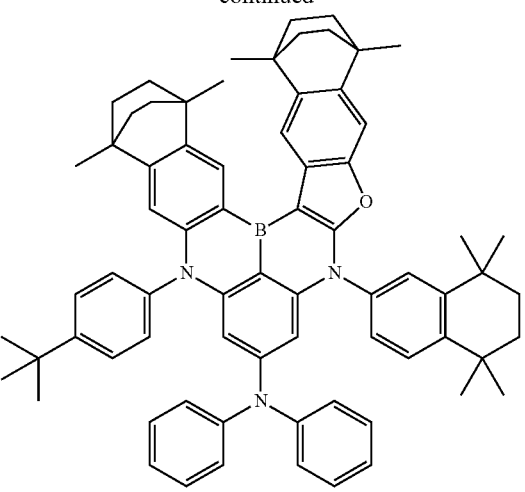
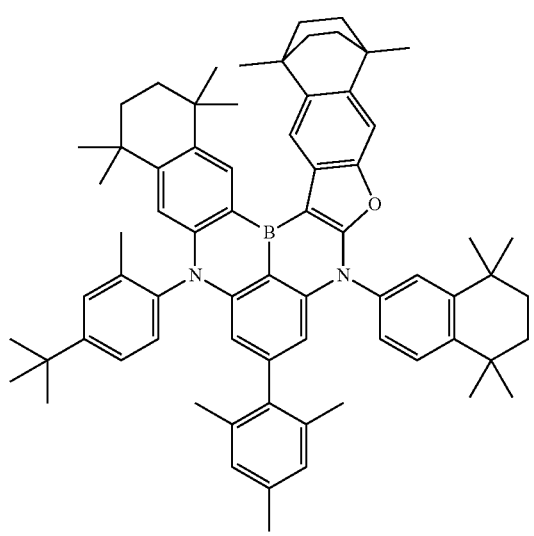
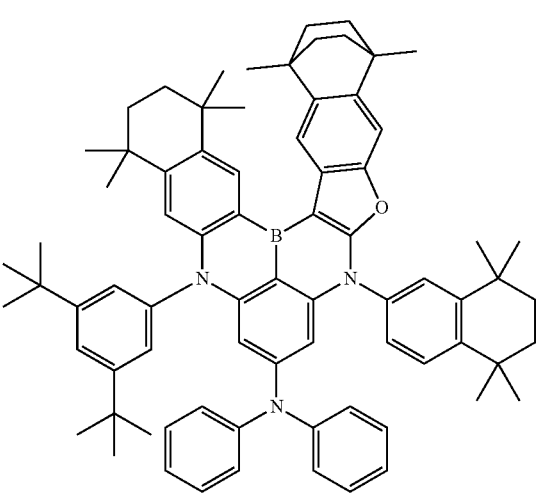
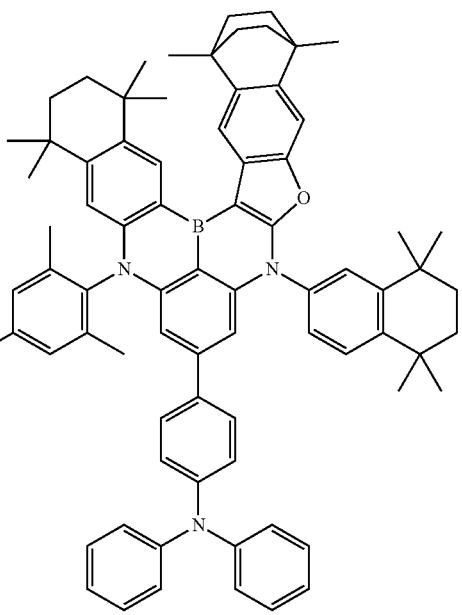

847
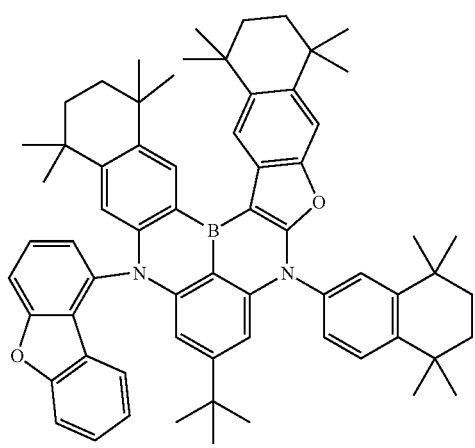
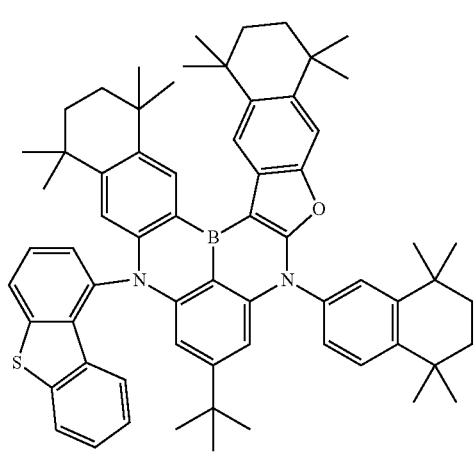
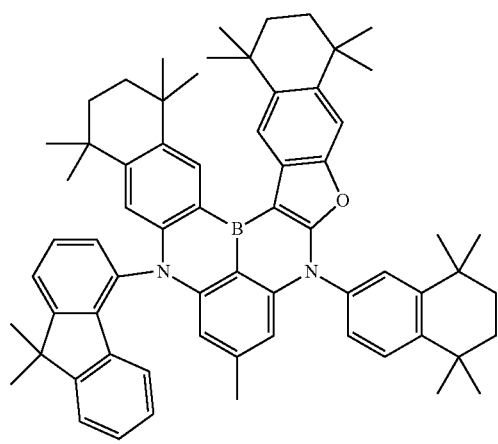
848
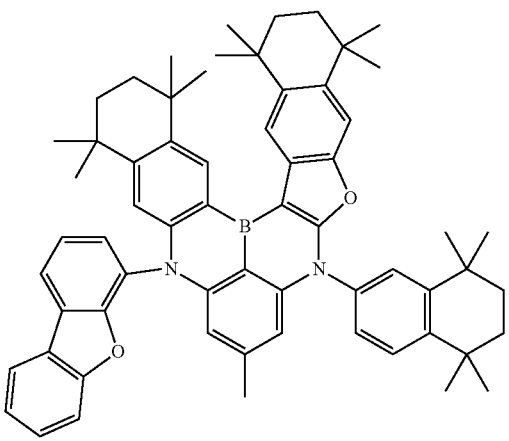
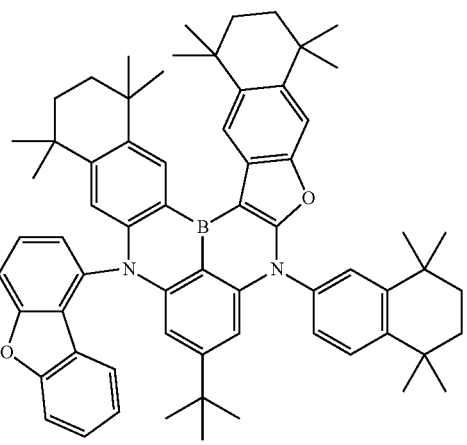
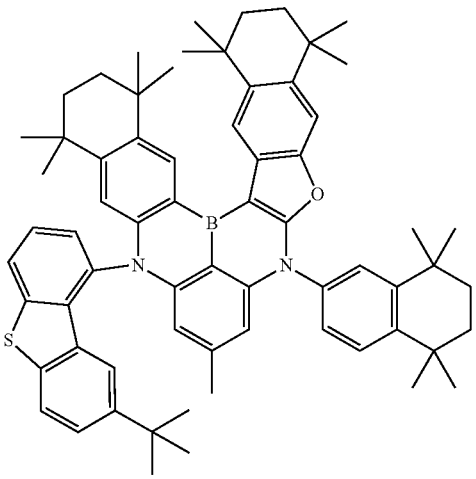

849
-continued
850
-continued
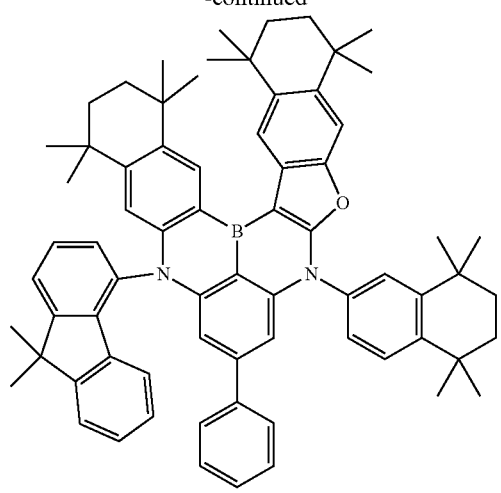
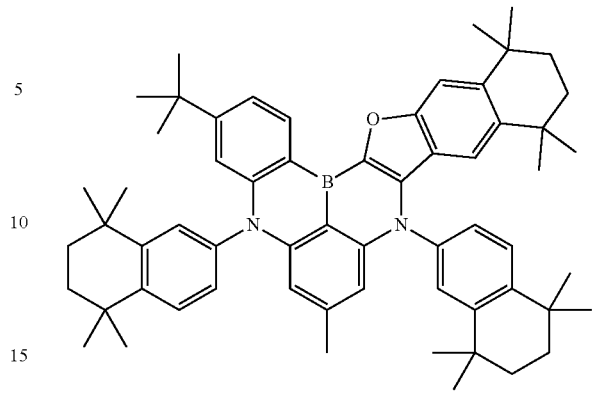
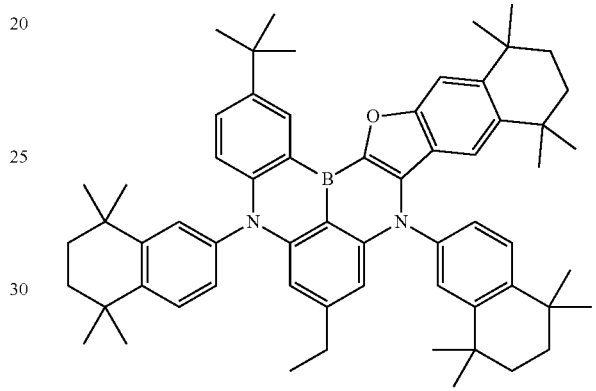
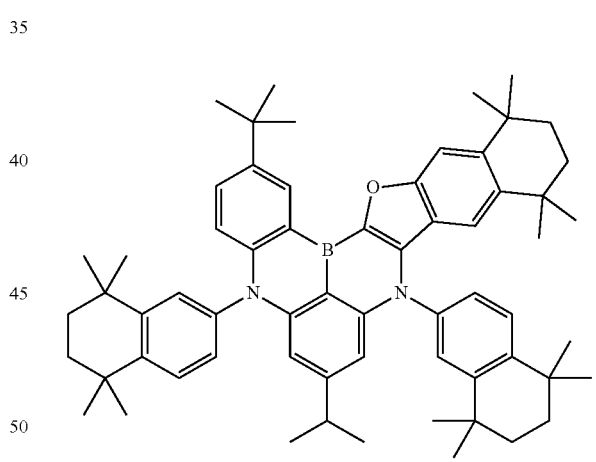
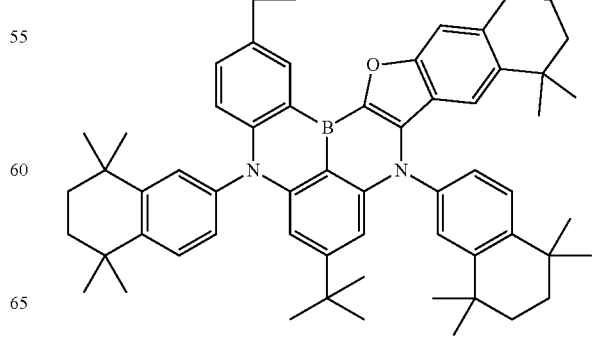
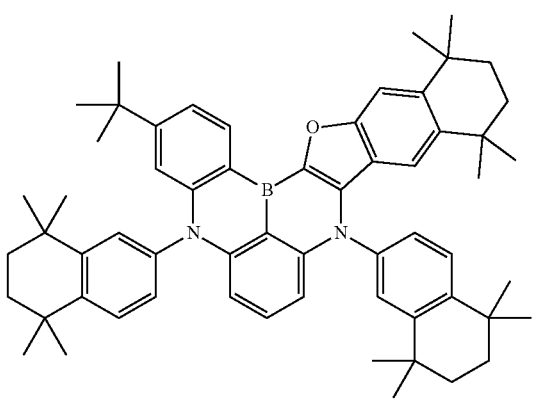

851
-continued
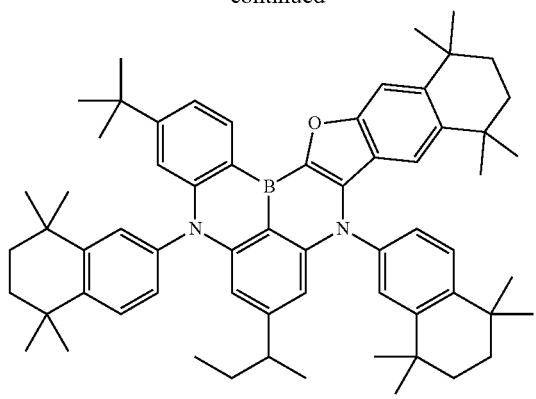
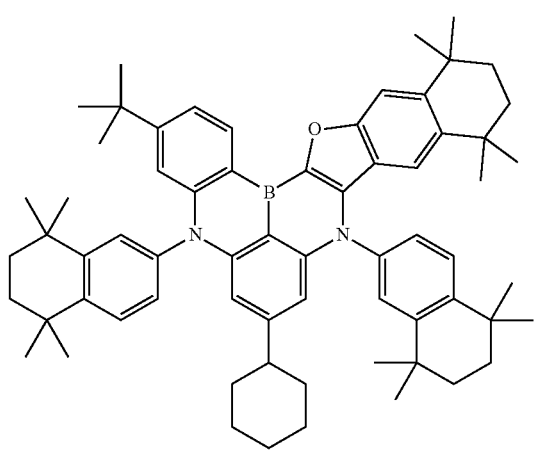
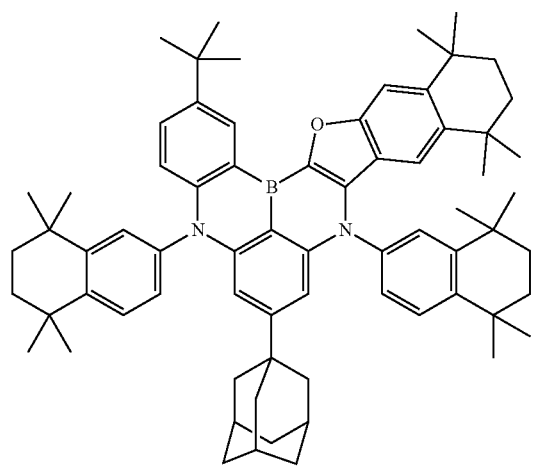
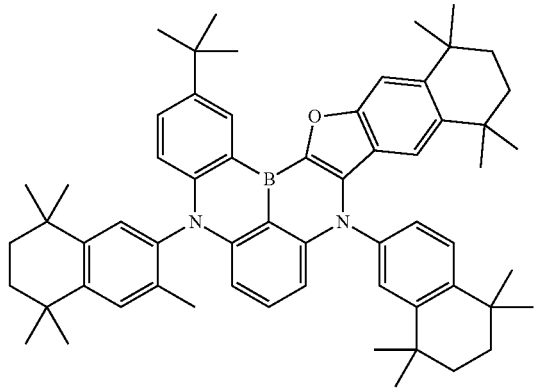
852
-continued
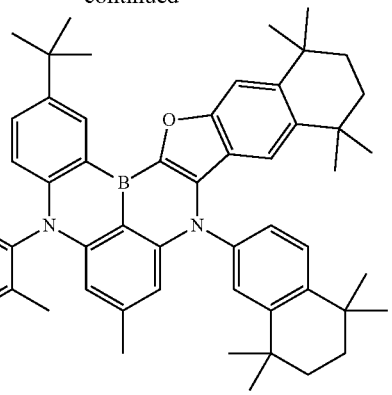
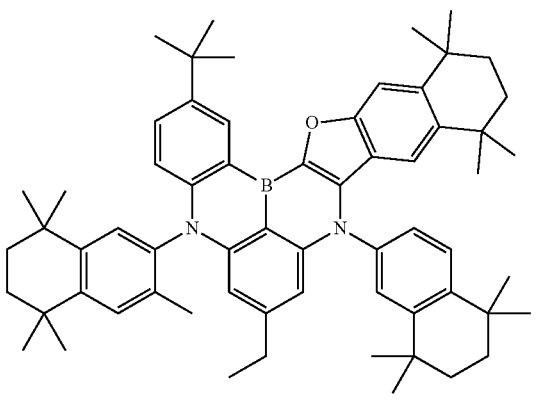
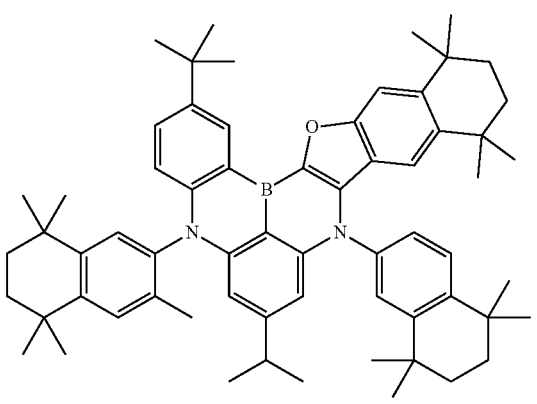
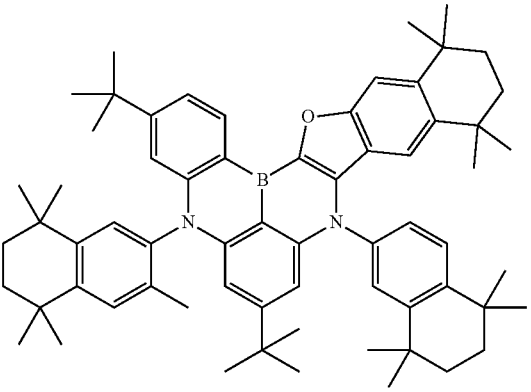

853
-continued
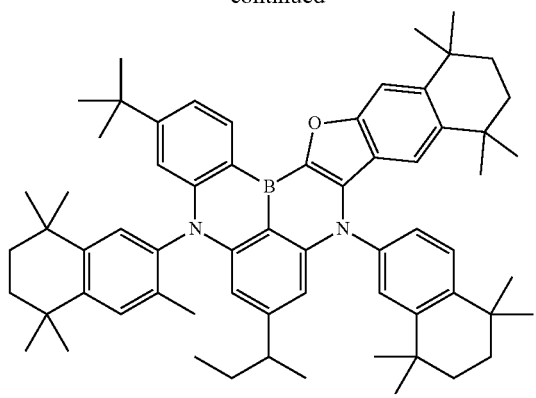
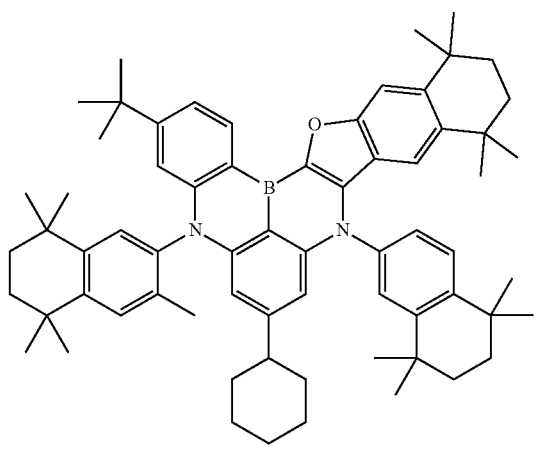
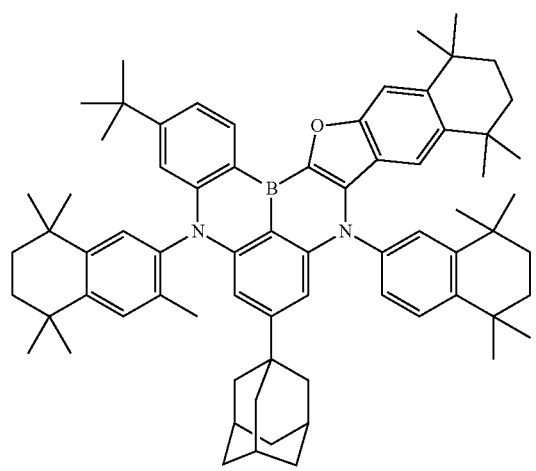
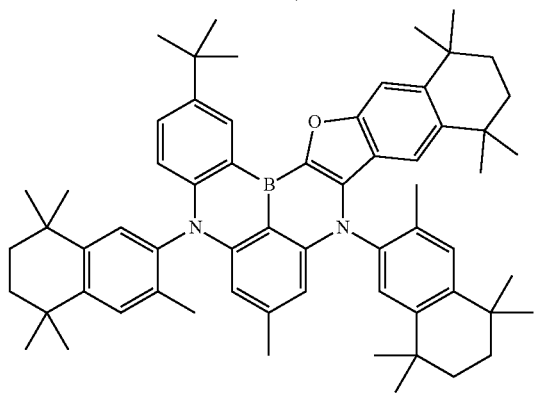
854
-continued
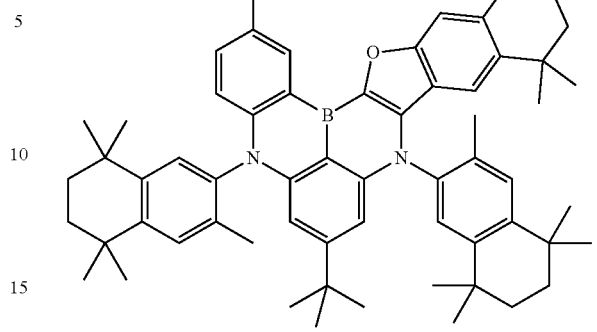
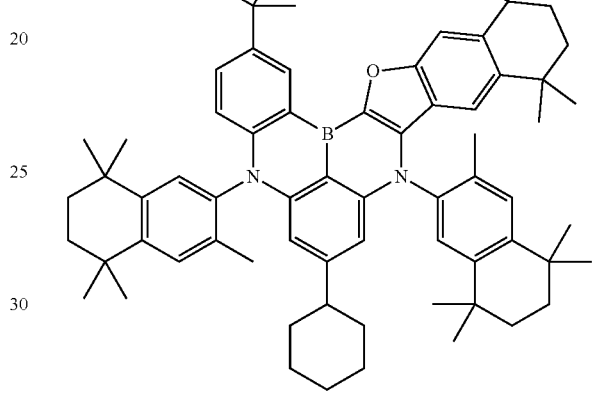
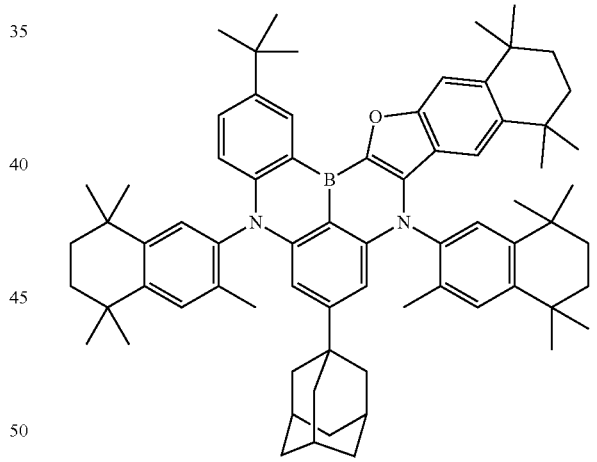
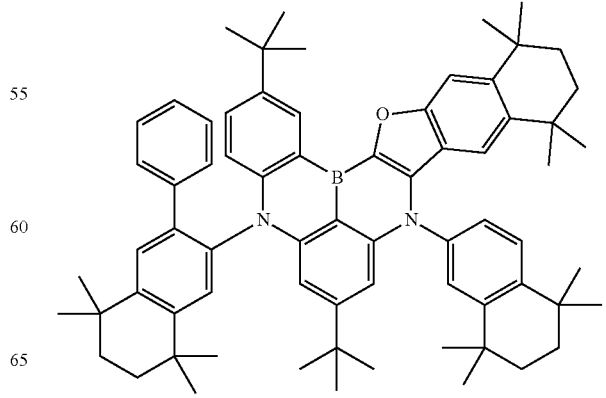

| 855 -continued | 856 -continued |
|---|---|
| 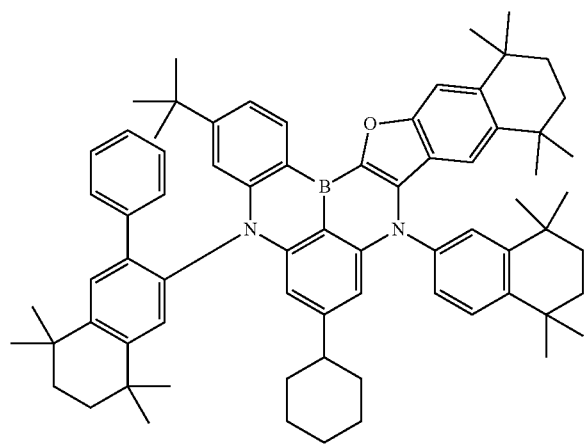 | 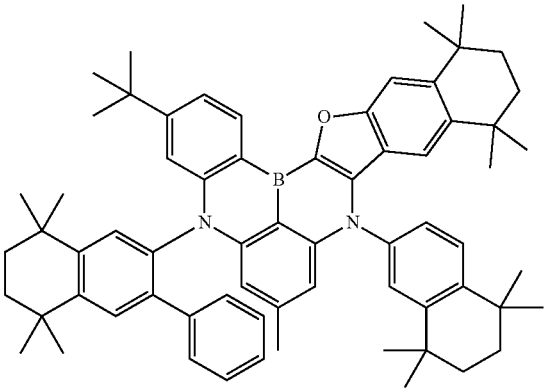 |
| 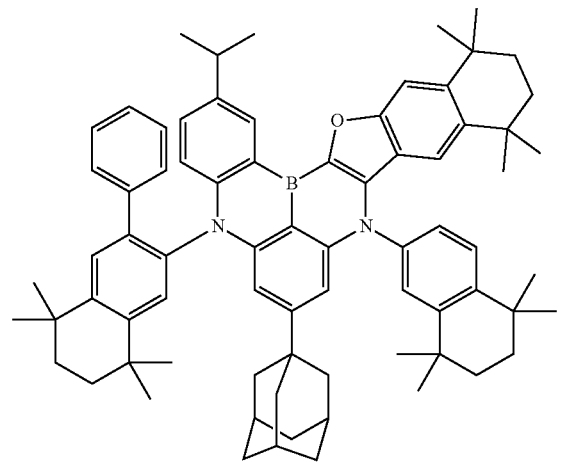 | 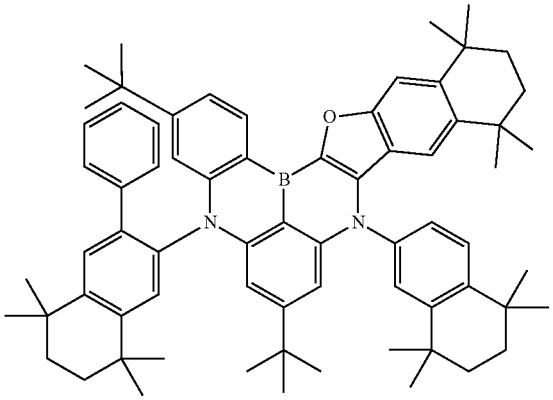 |
| 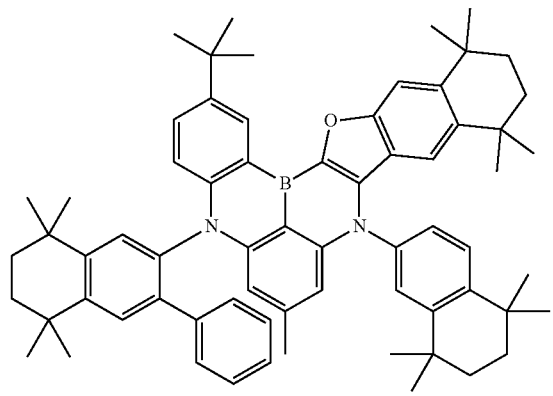 | 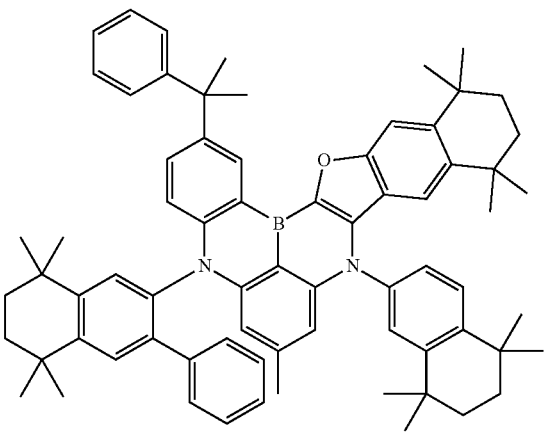 |
| 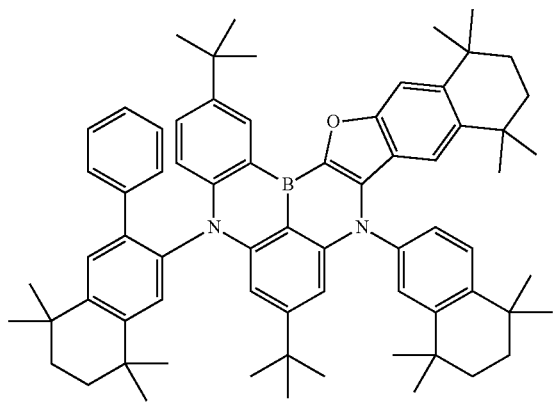 | 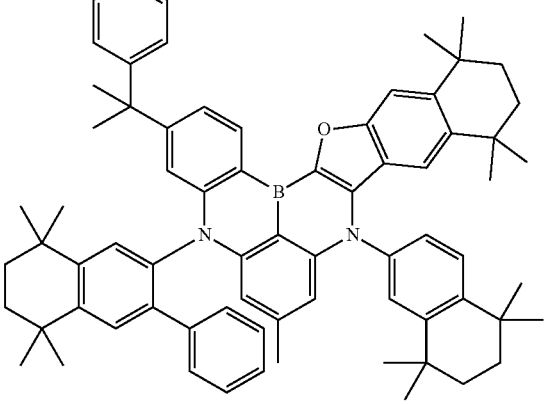 |

857
-continued
858
-continued
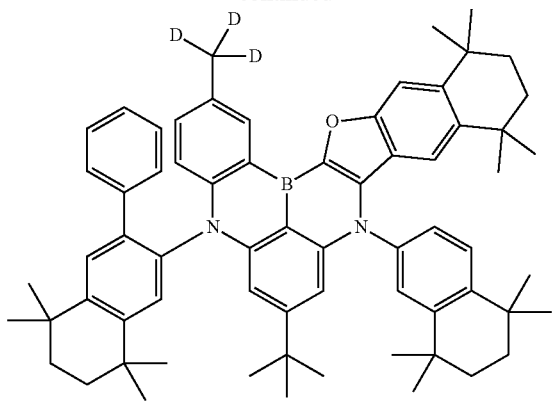
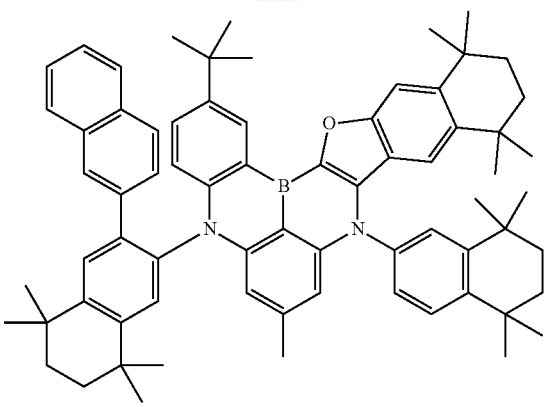

859
-continued
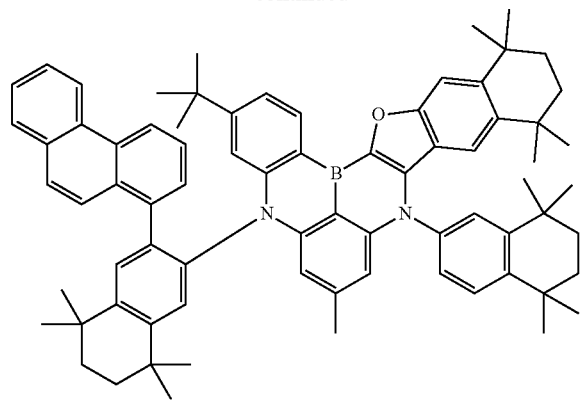
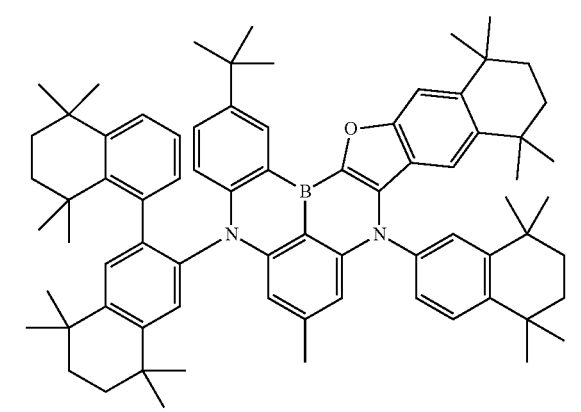
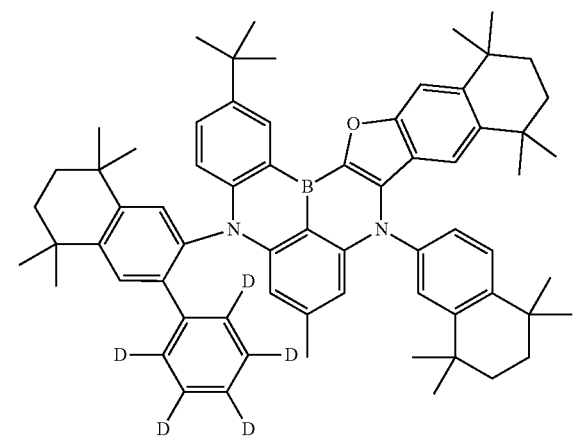
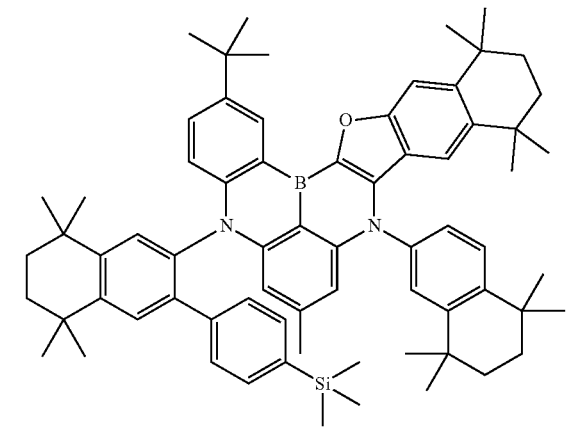
860
-continued
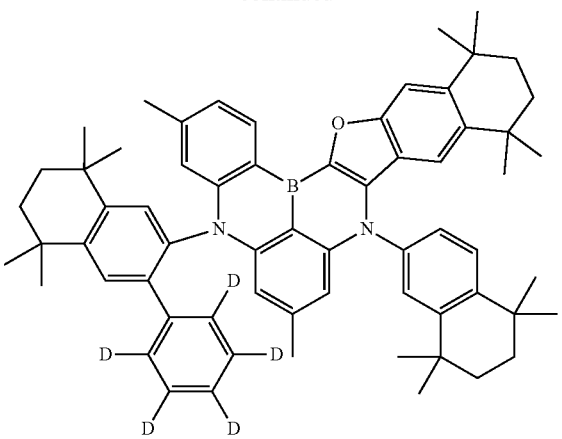
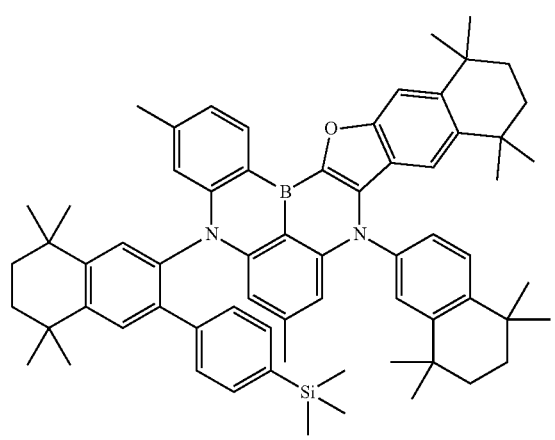
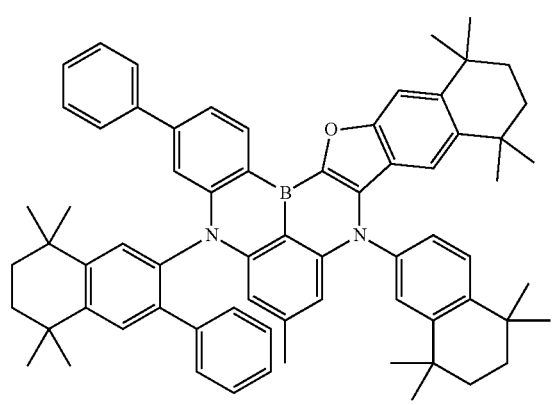
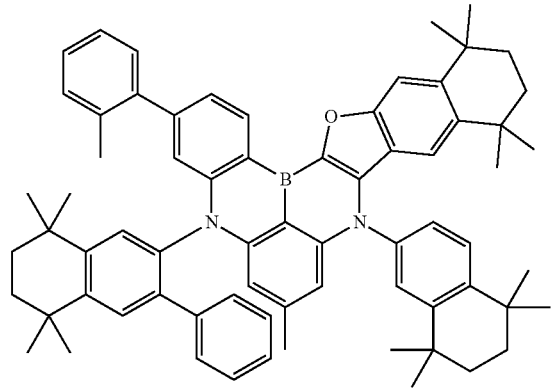

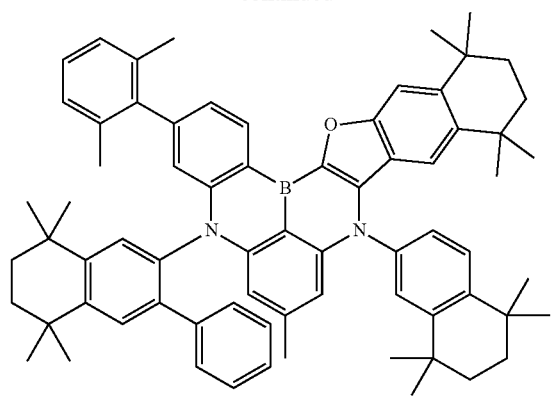
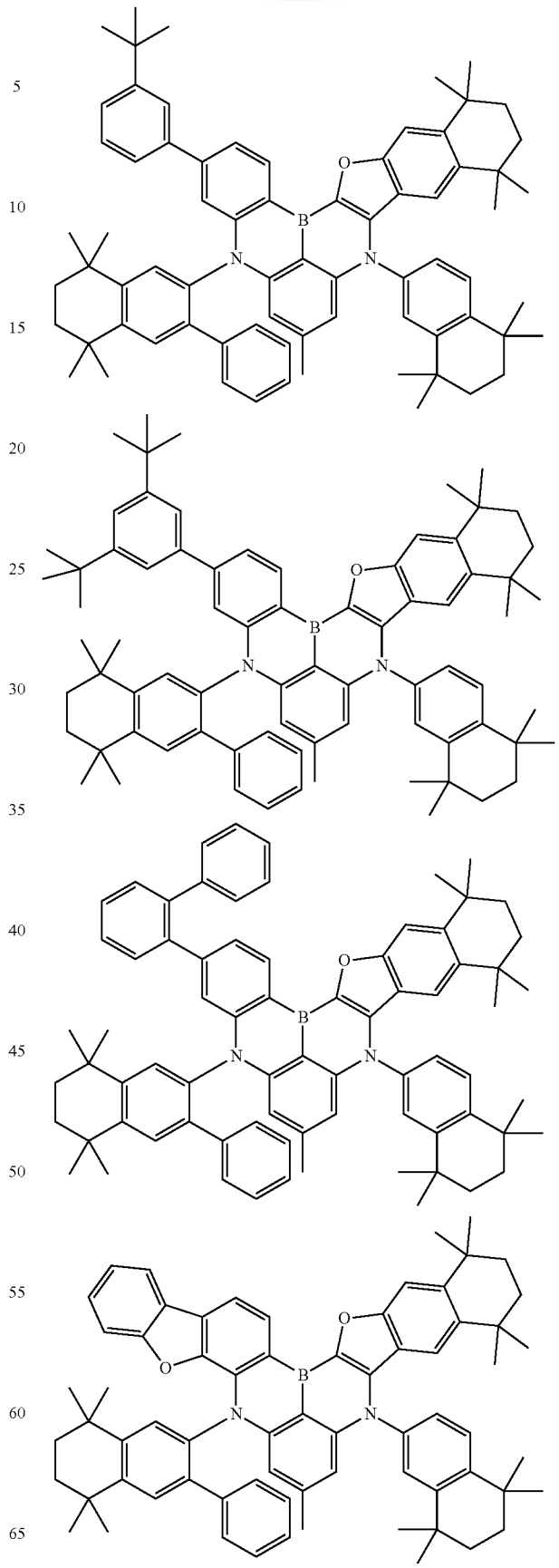

863
-continued
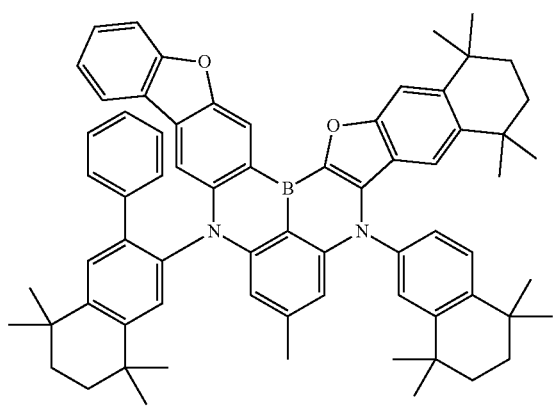
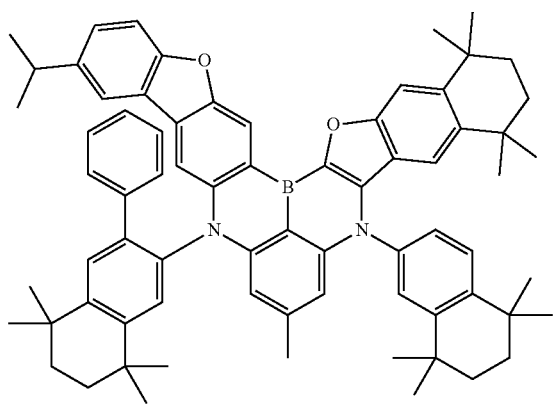
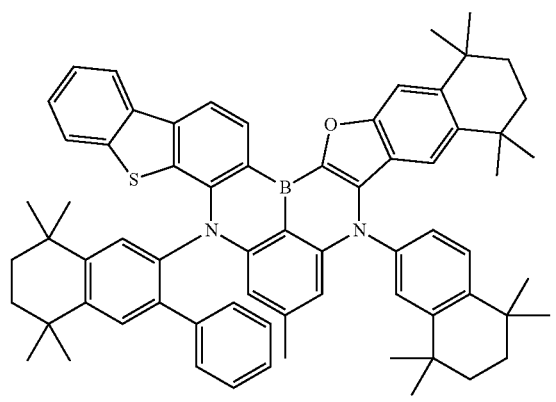
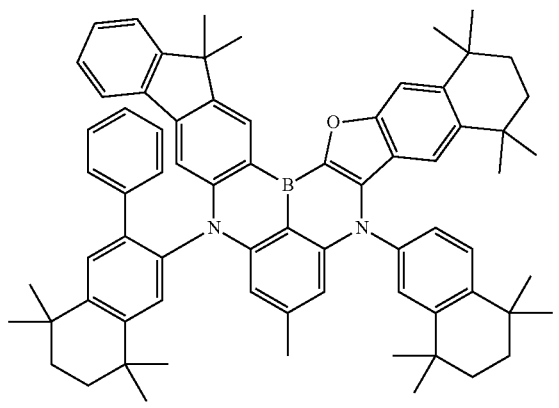
864
-continued
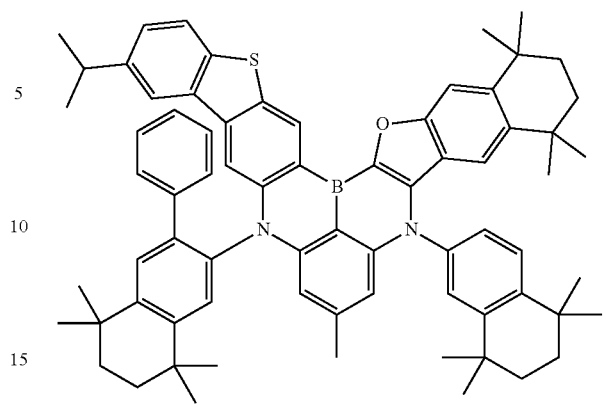
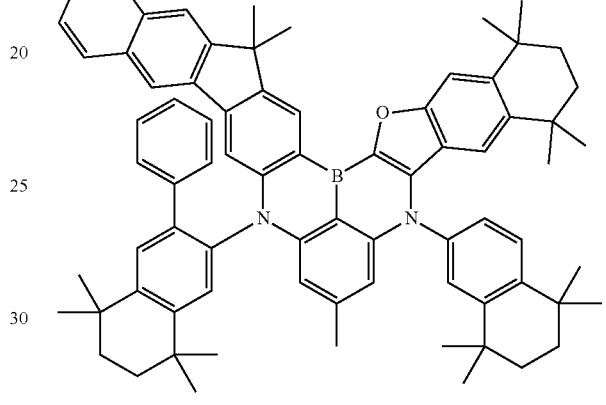

865
-continued
866
-continued
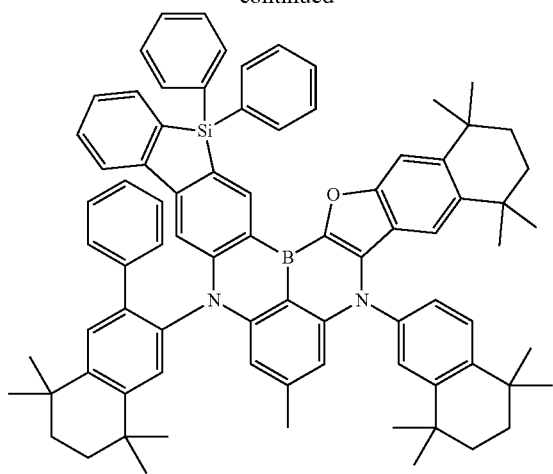
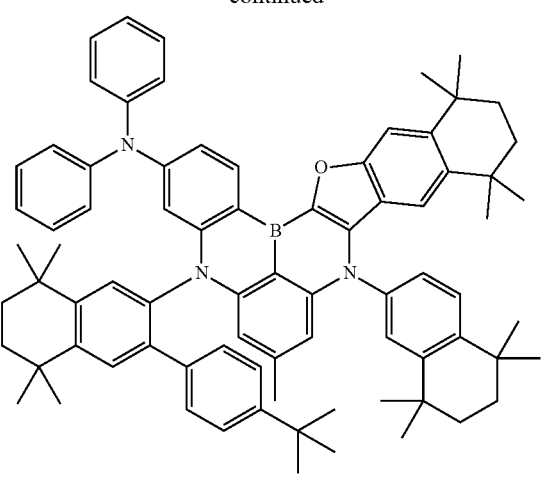
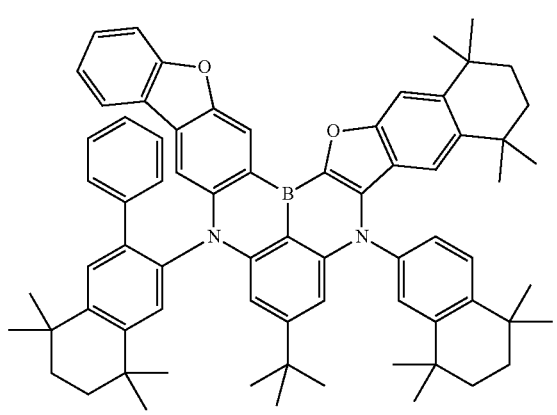
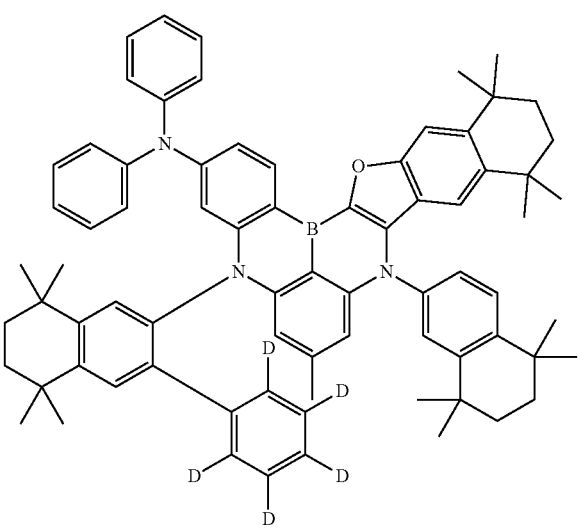
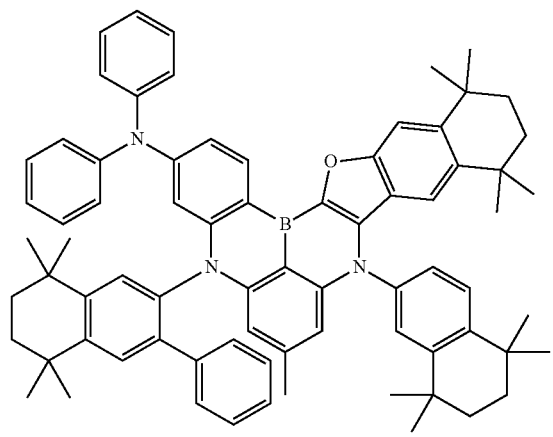
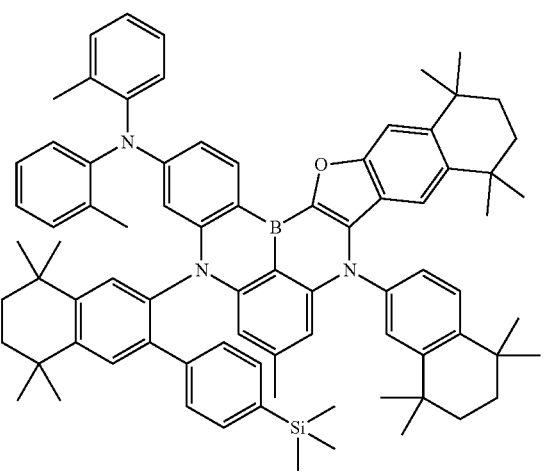

867
-continued
868
-continued
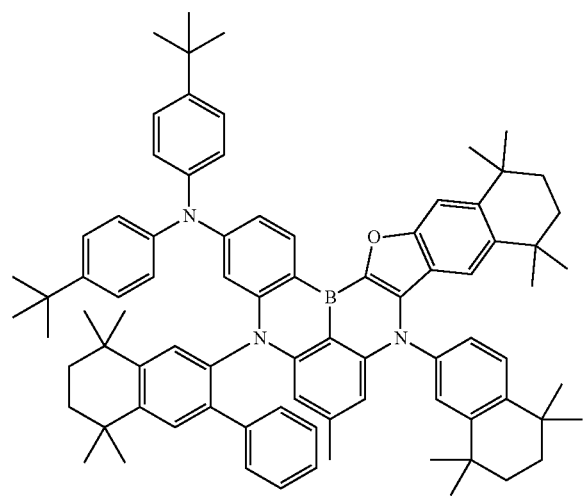
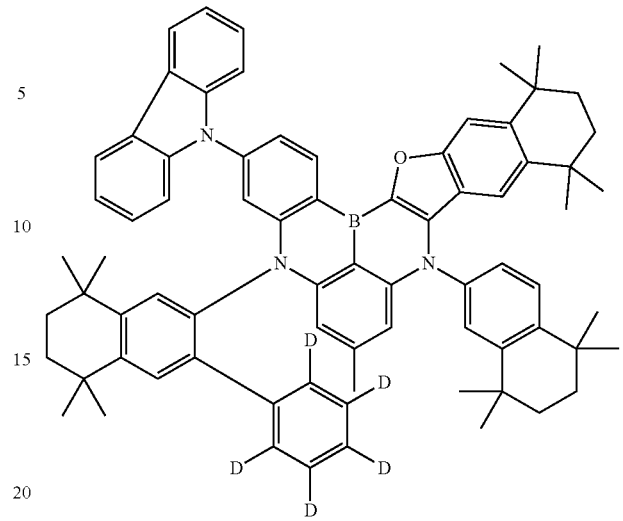
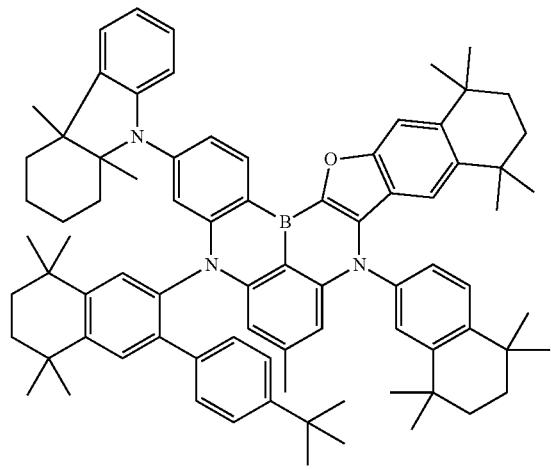
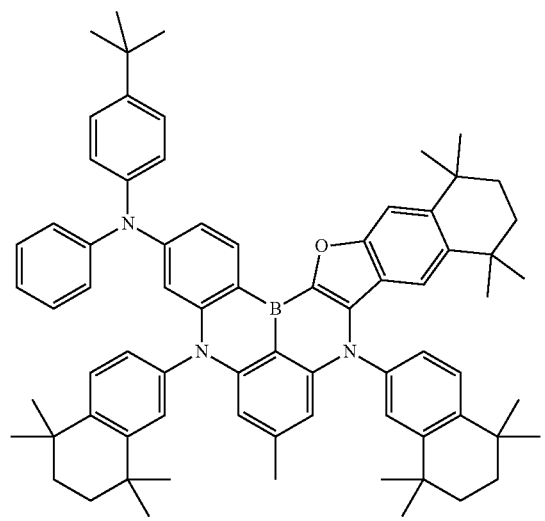
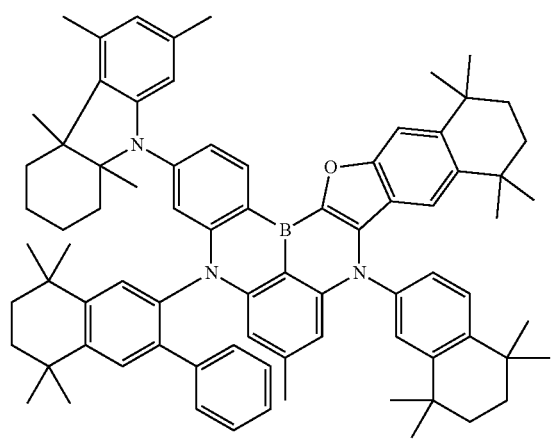

869
-continued
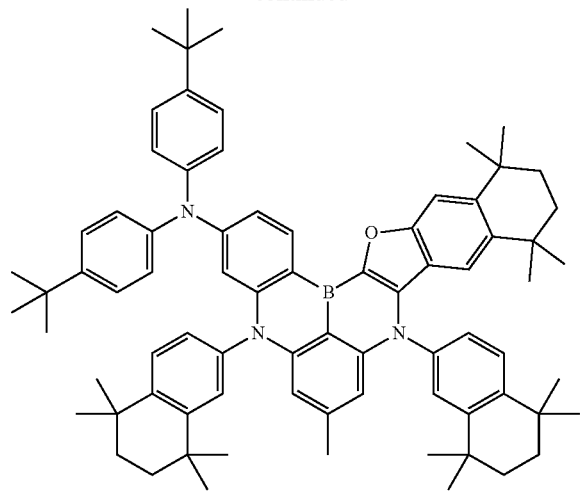
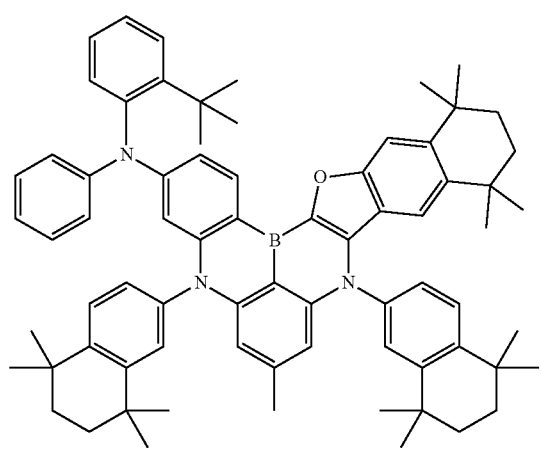
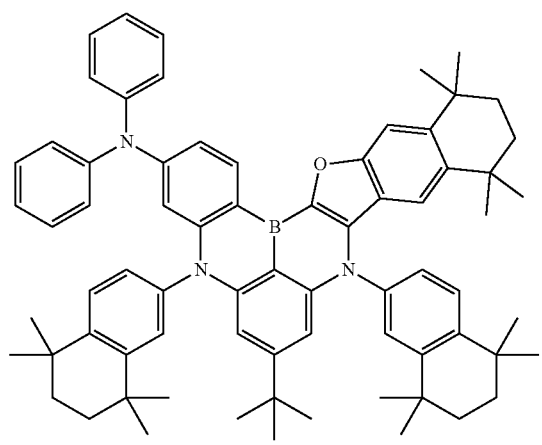
870
-continued
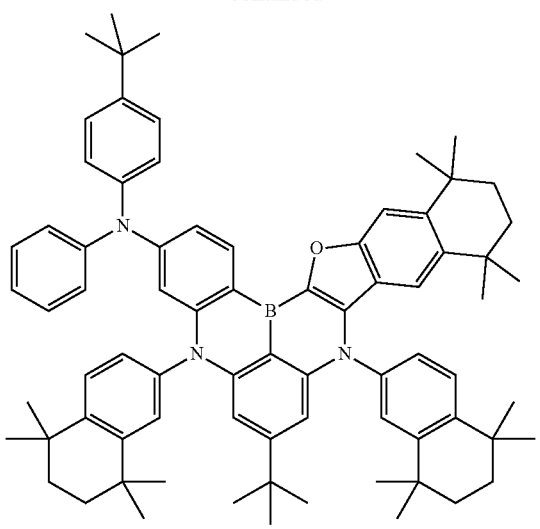
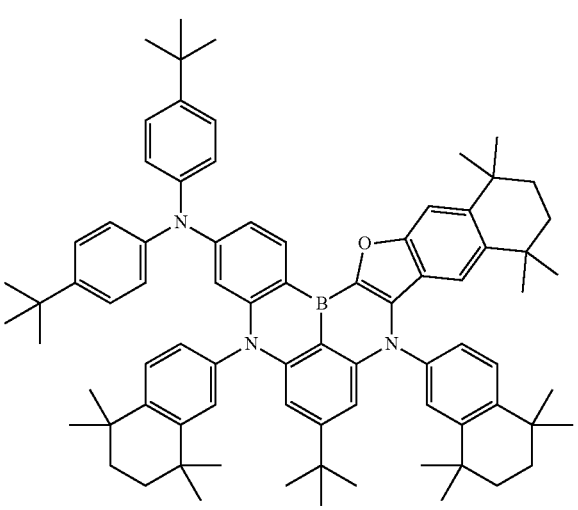
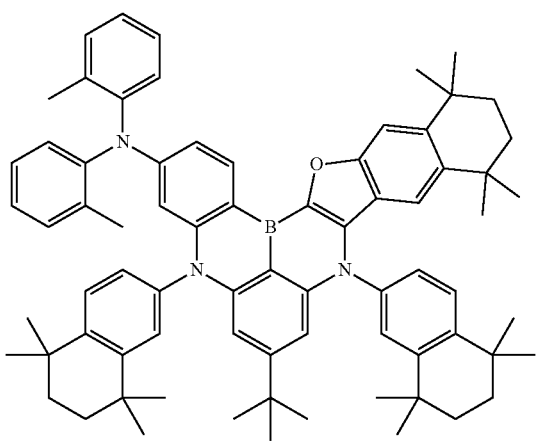

871
-continued
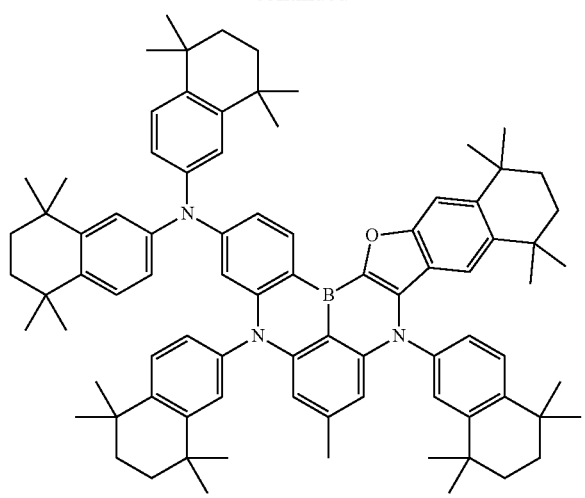
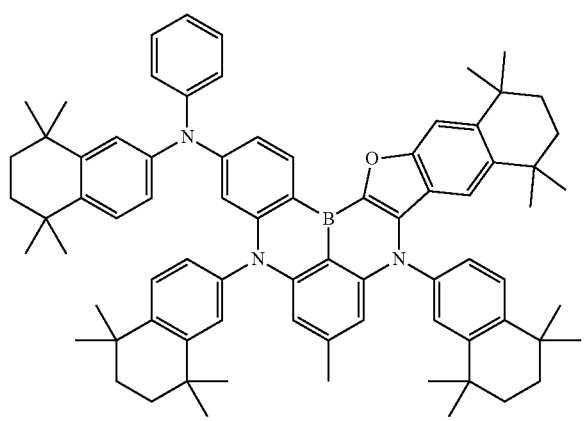
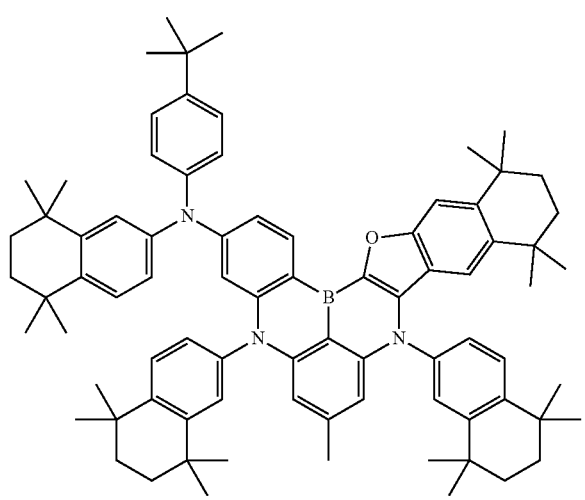
872
-continued
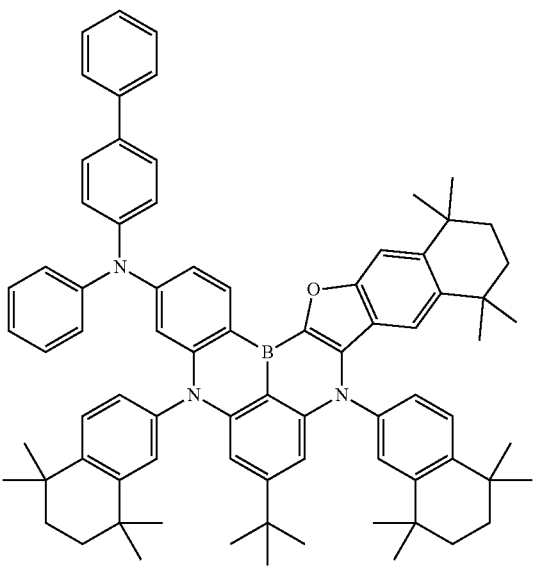
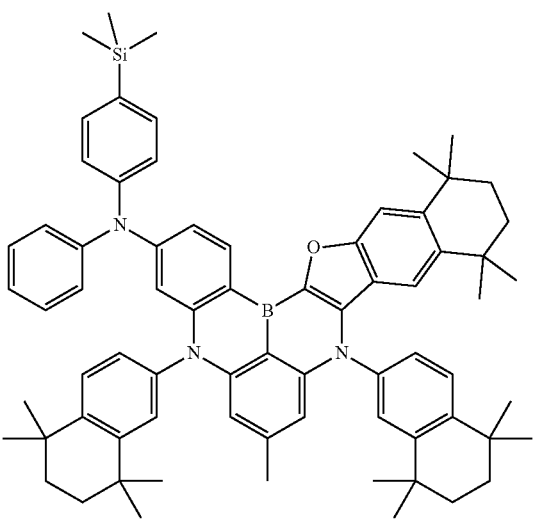
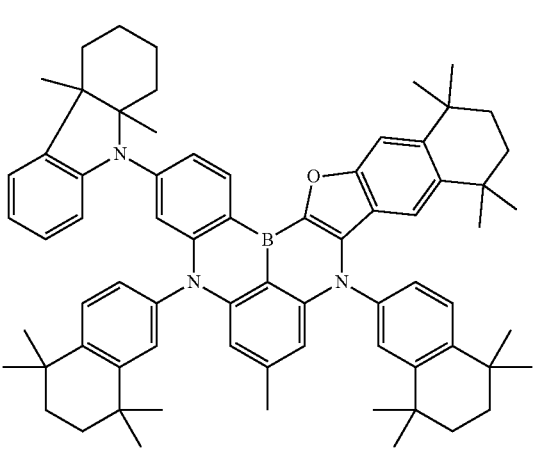

873
-continued
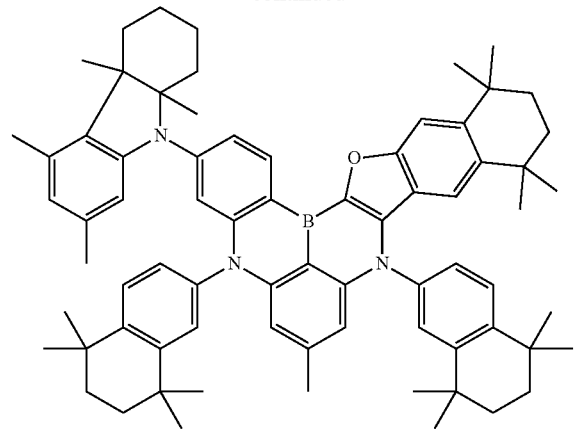
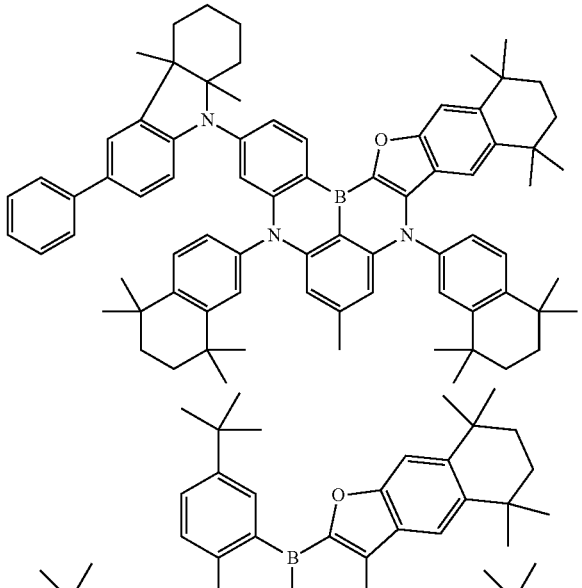
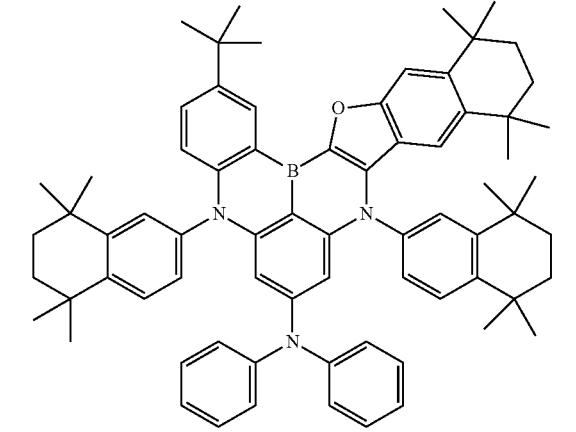
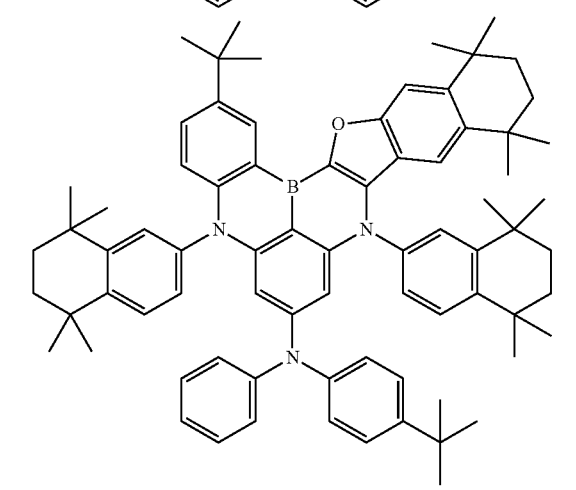
874
-continued
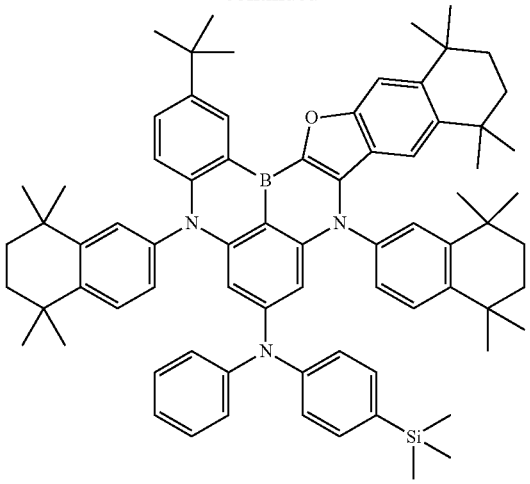
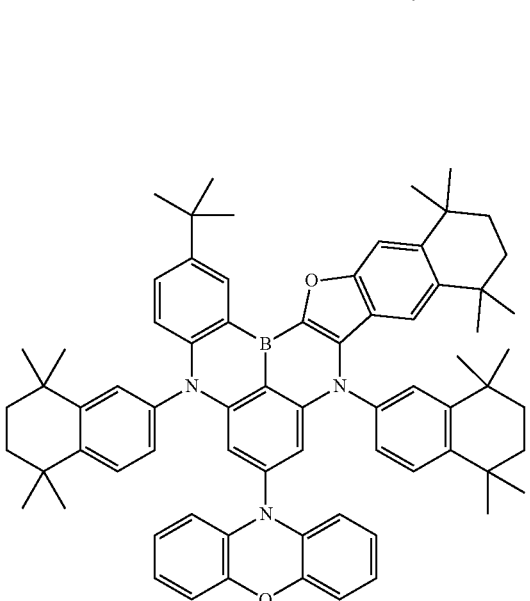
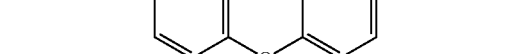
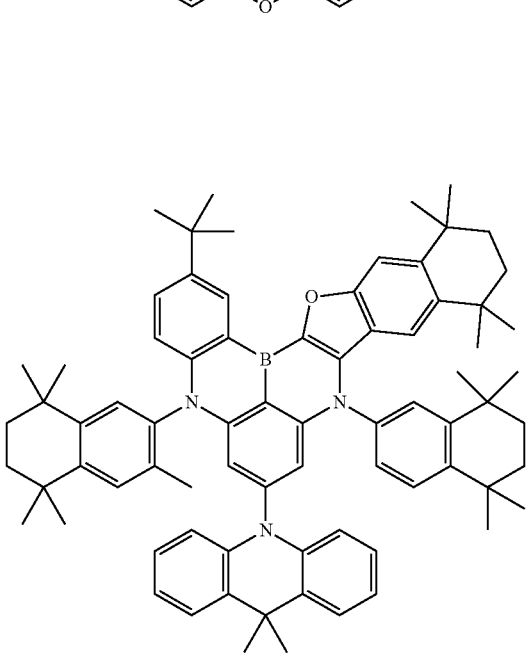

875
-continued
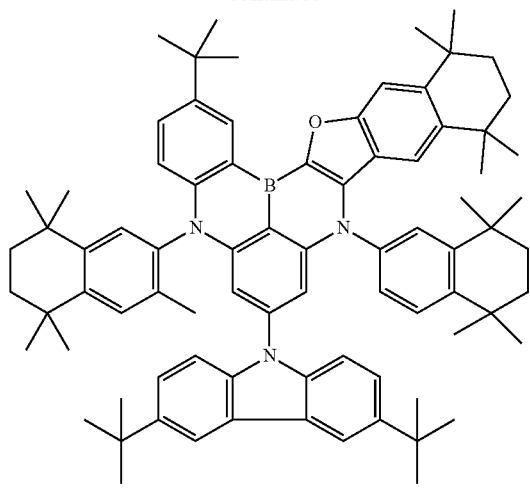
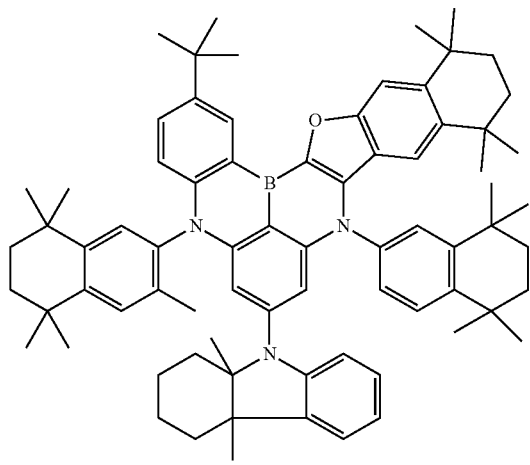
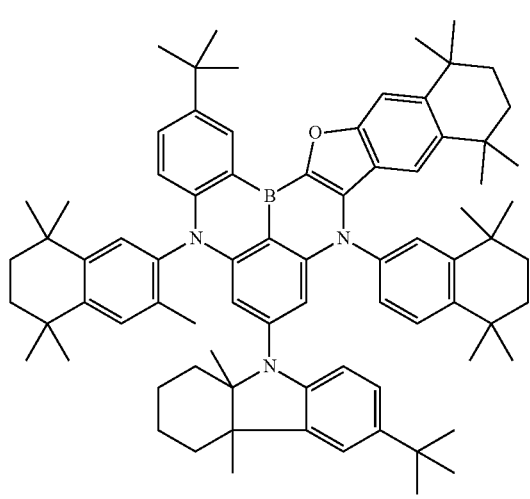
876
-continued
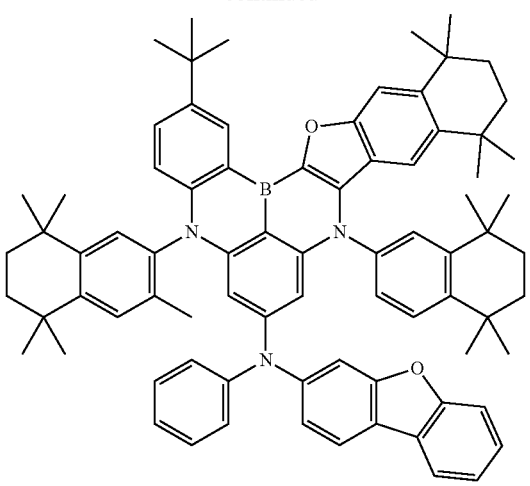
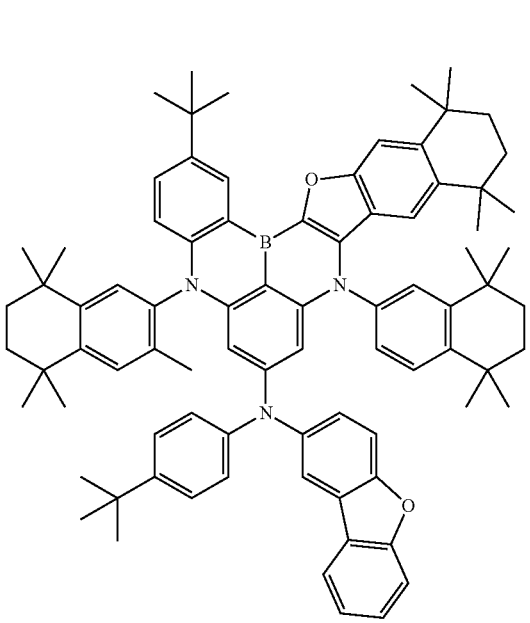

877
-continued
878
-continued
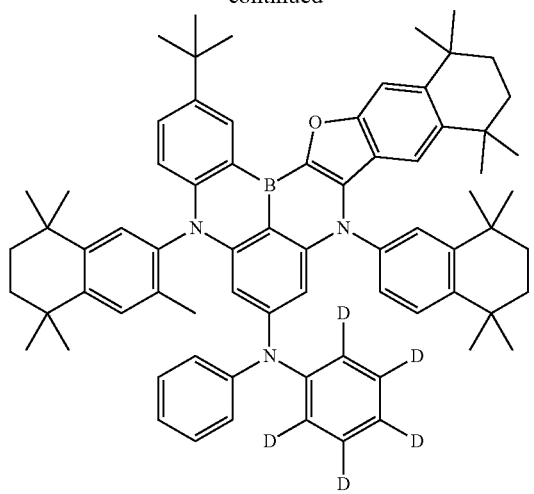
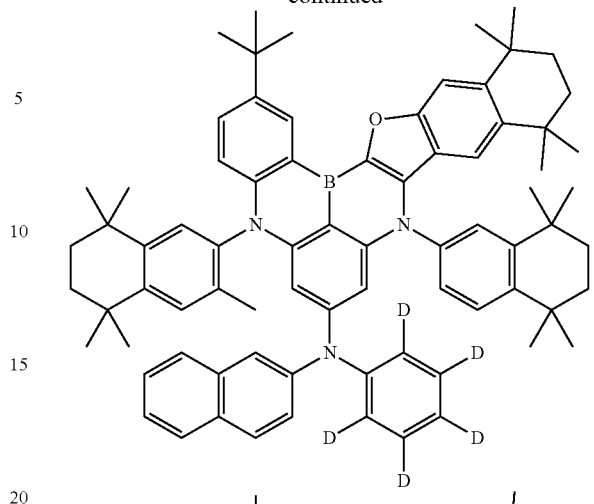
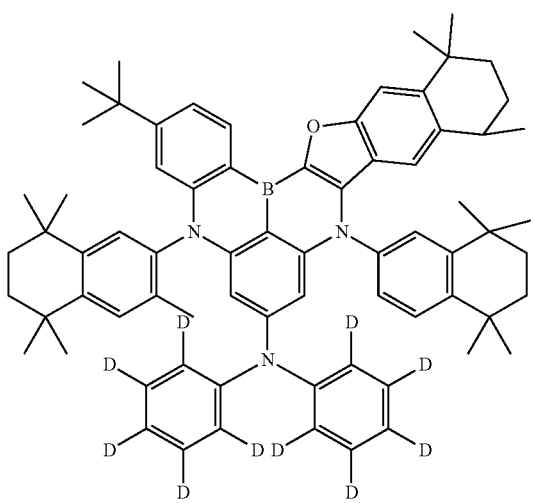
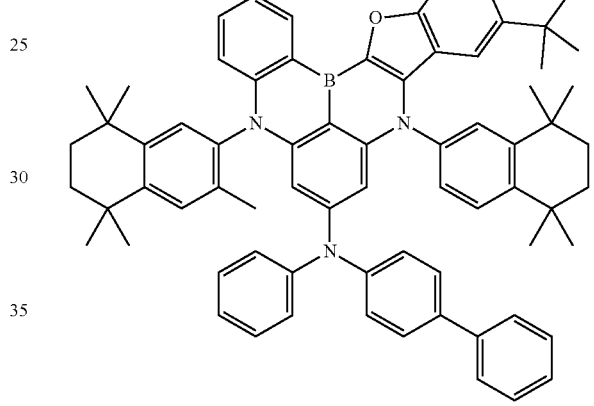
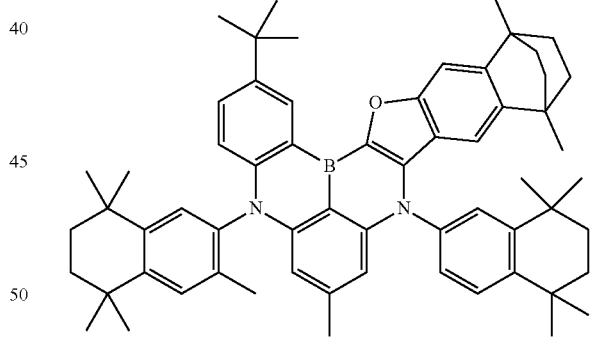
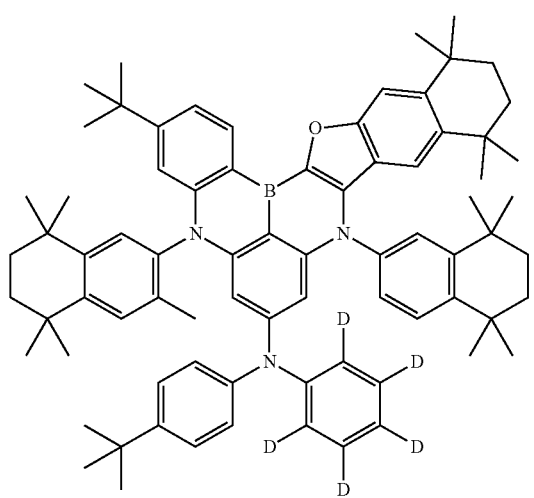
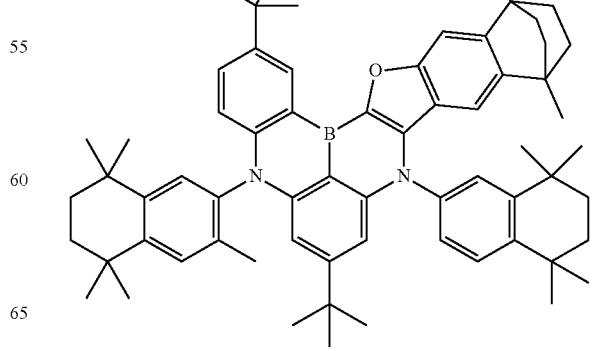

879
-continued
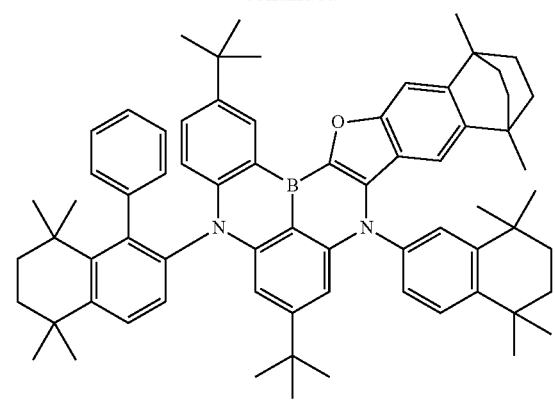
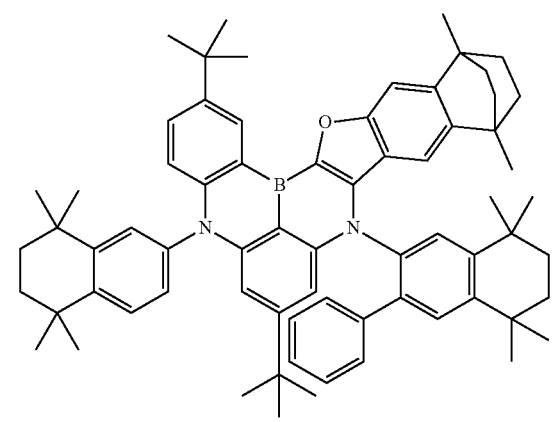
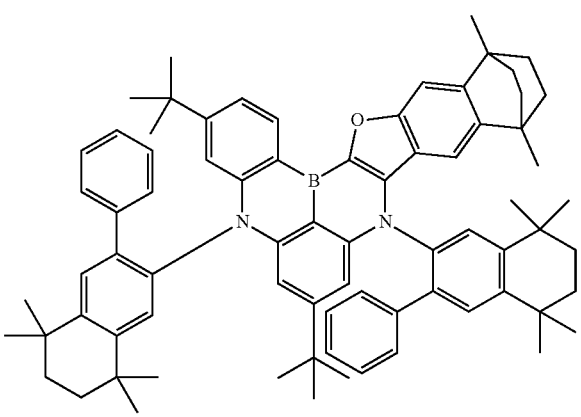
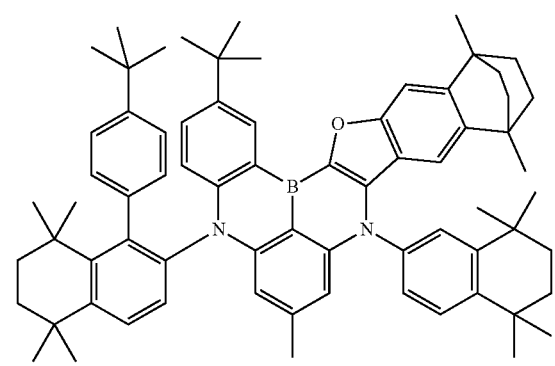
880
-continued
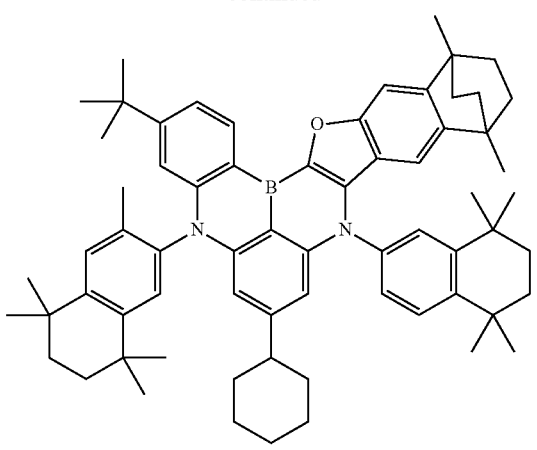
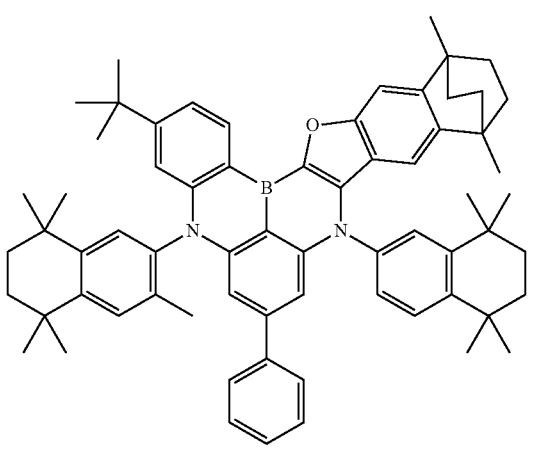
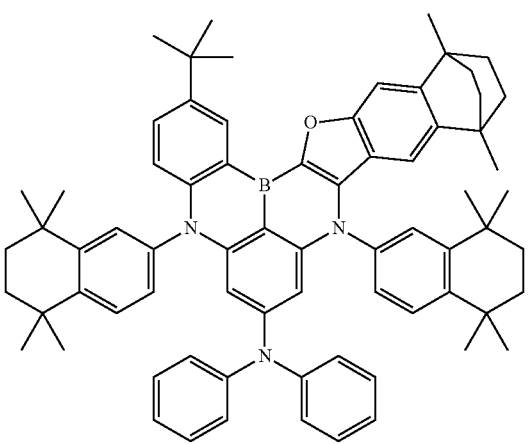

881
-continued
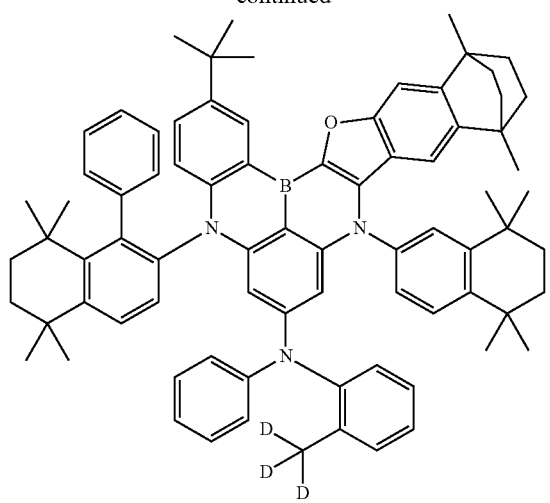
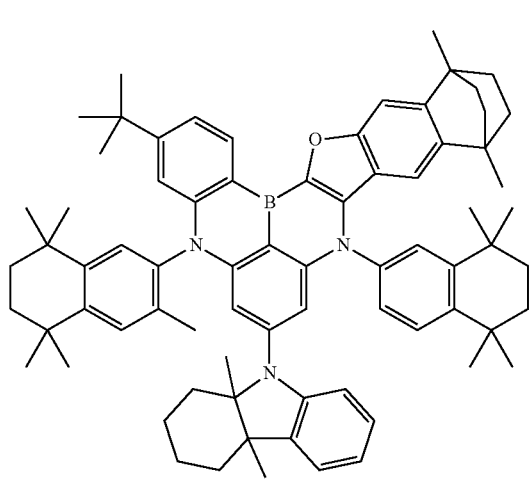
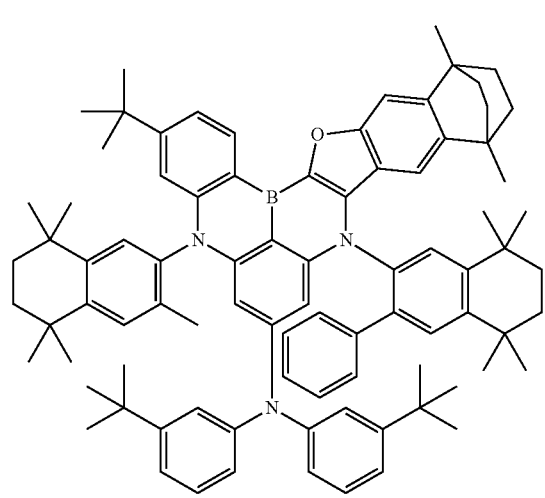
882
-continued
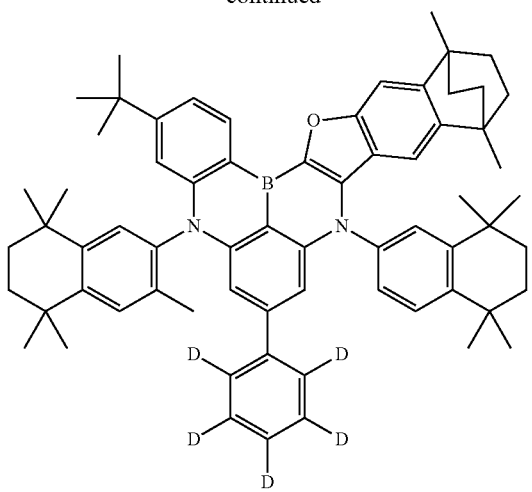
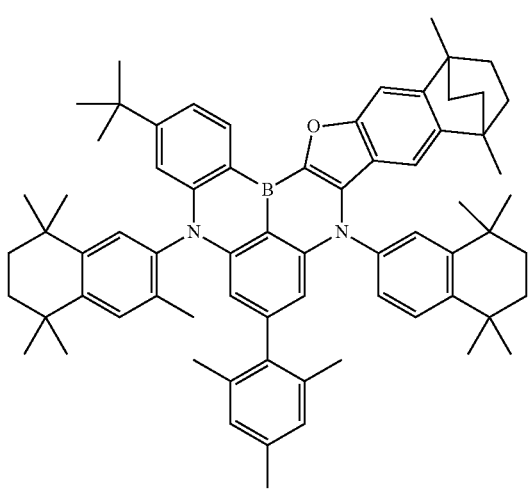
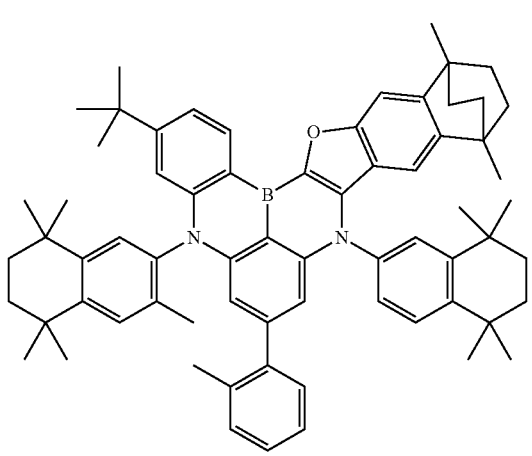

883
-continued
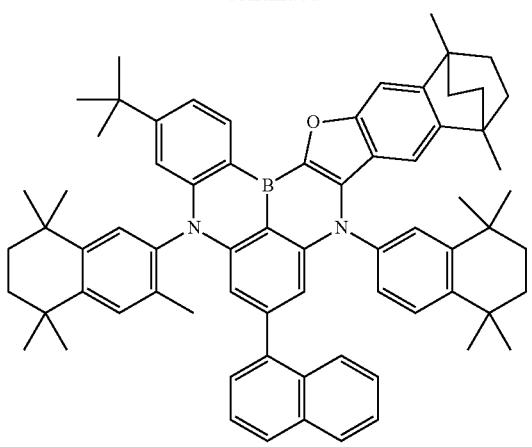
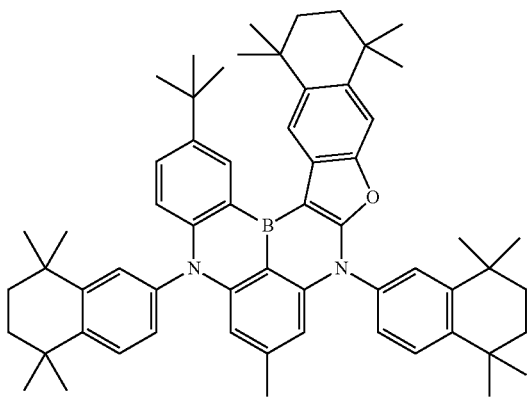
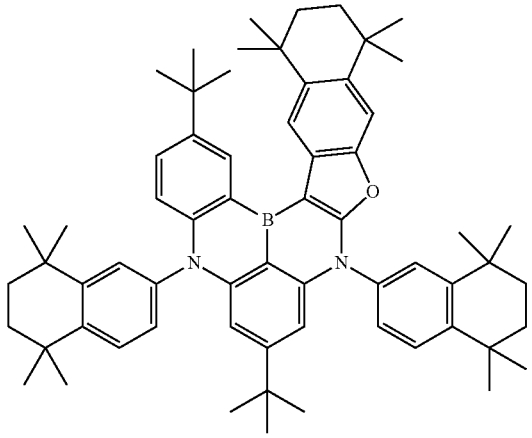
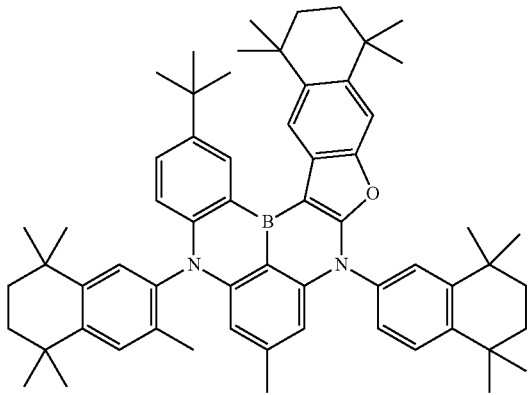
884
-continued
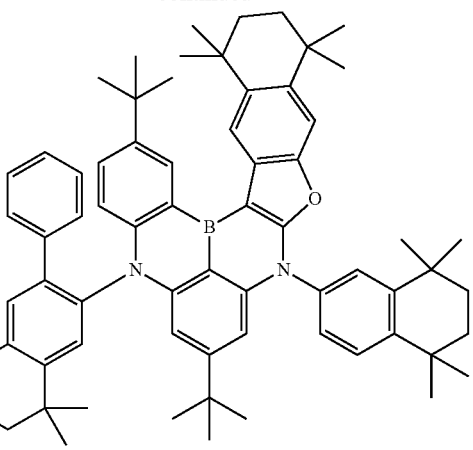
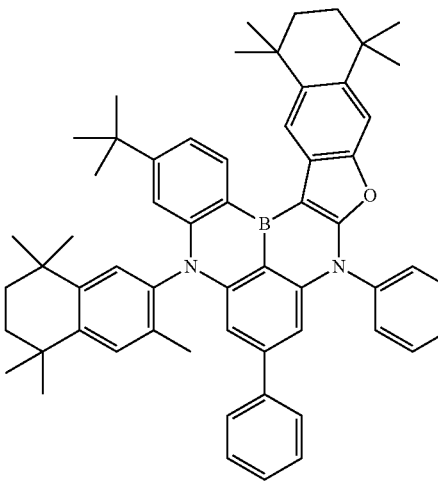
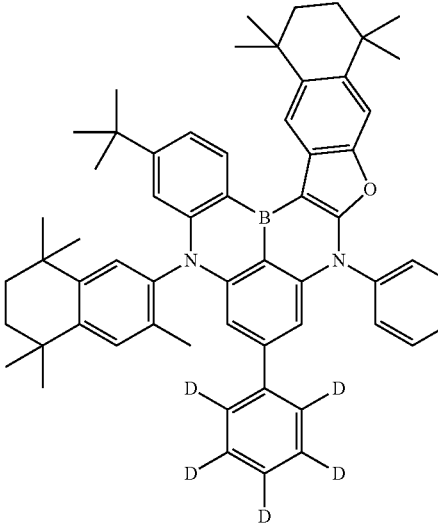

885
-continued
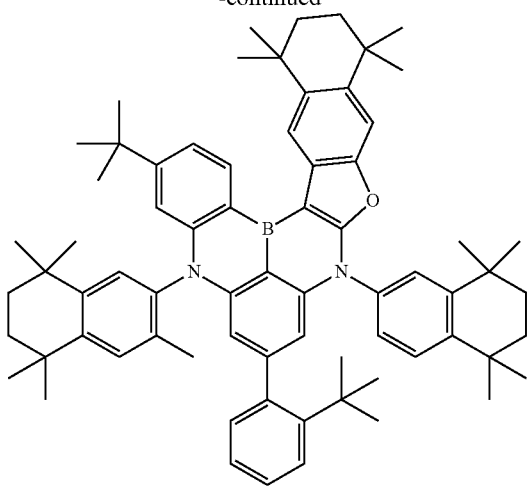
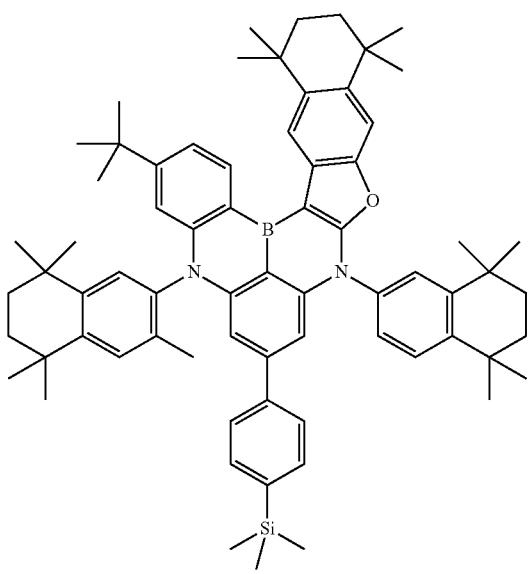
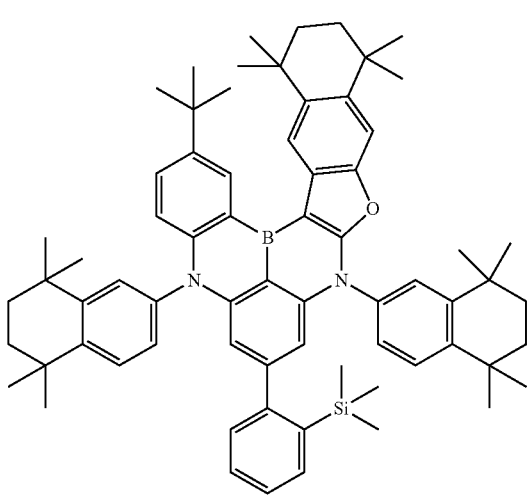
886
-continued
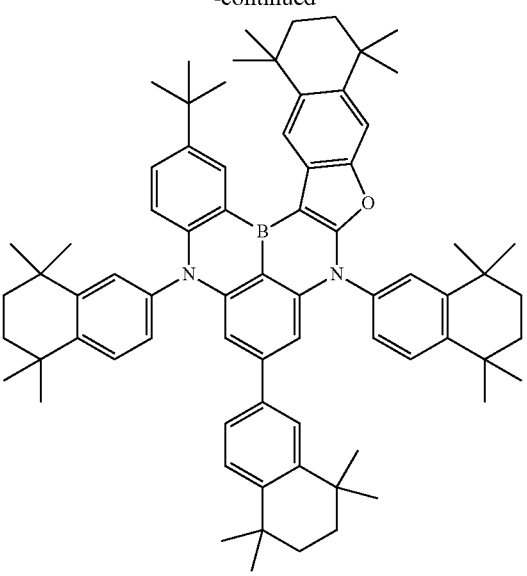
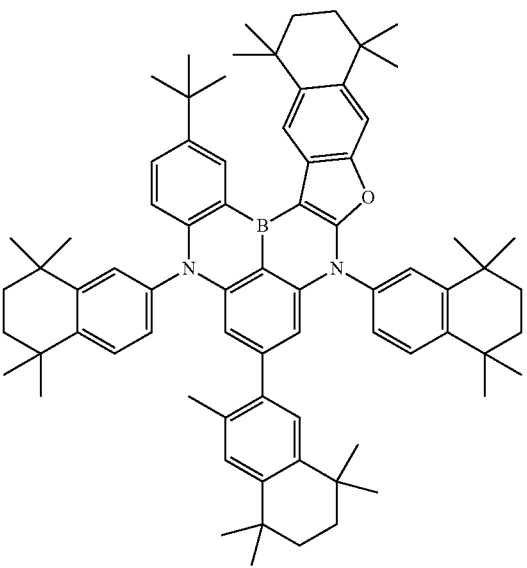
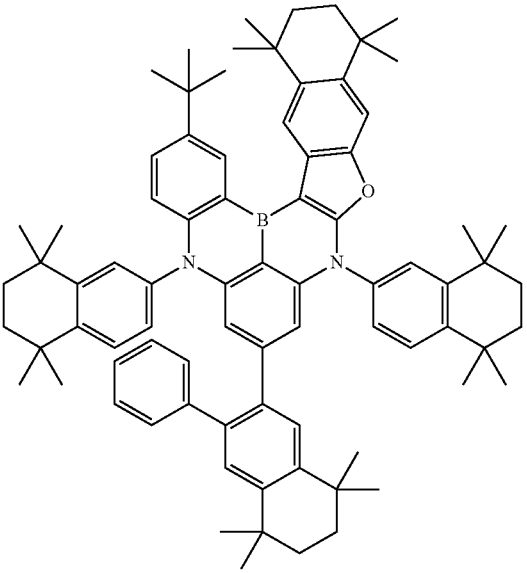

887
-continued
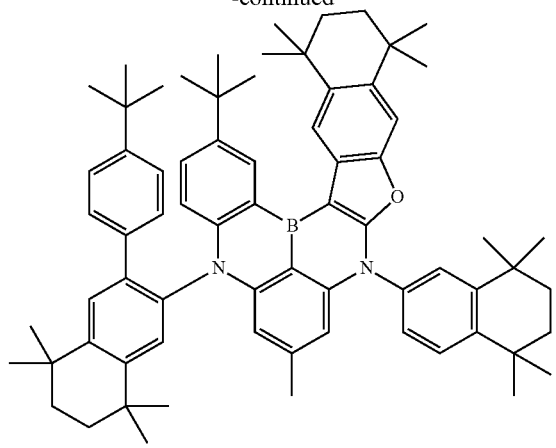
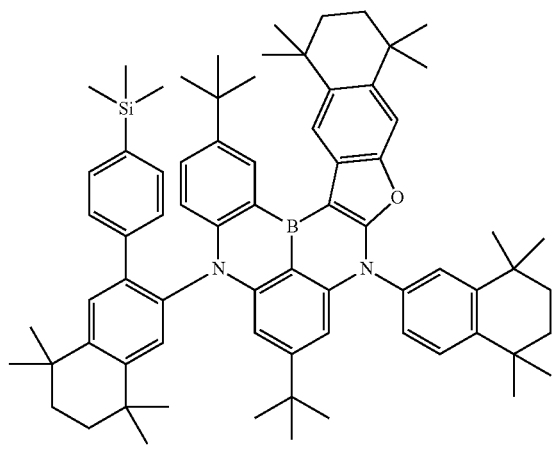
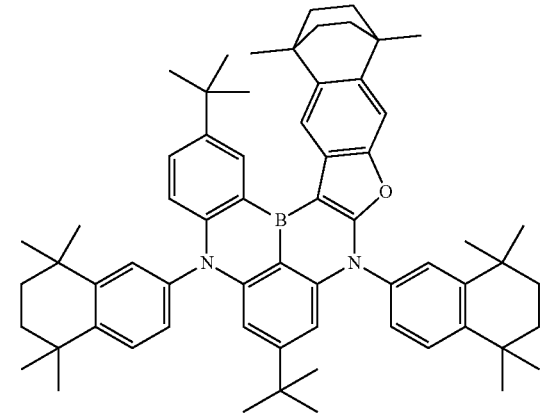
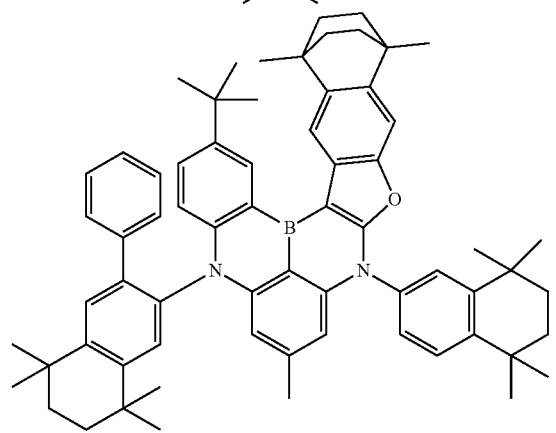
888
-continued
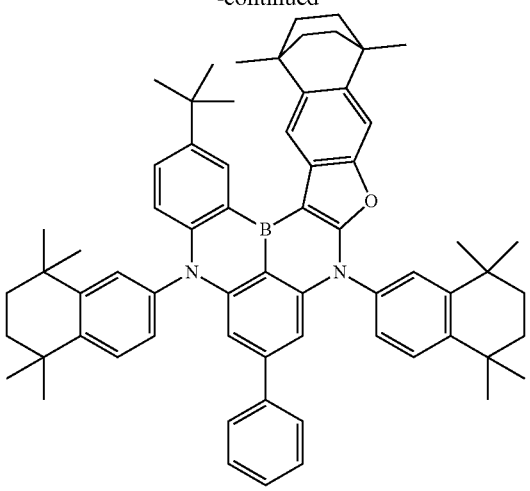
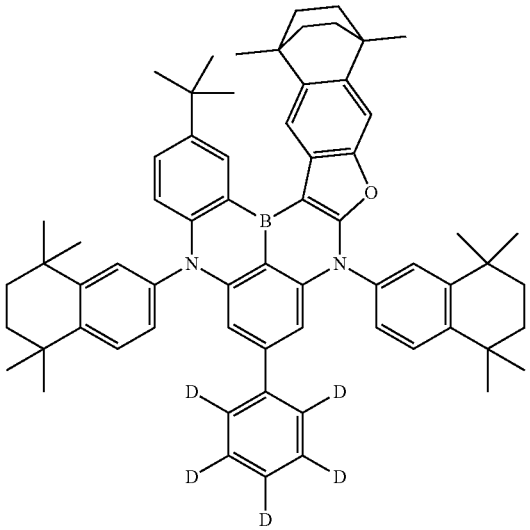
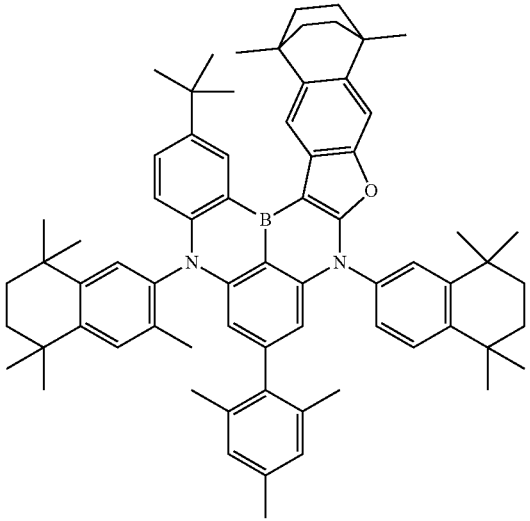

889
-continued
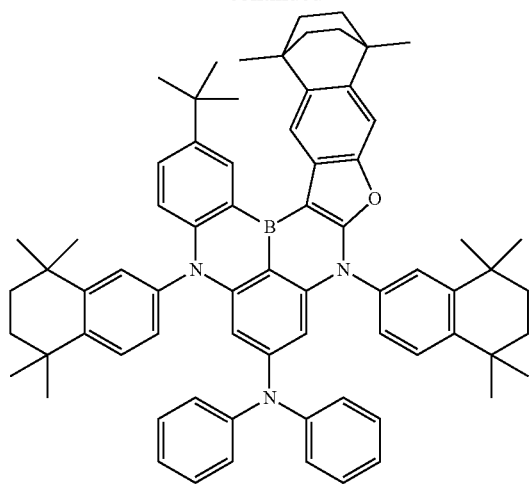
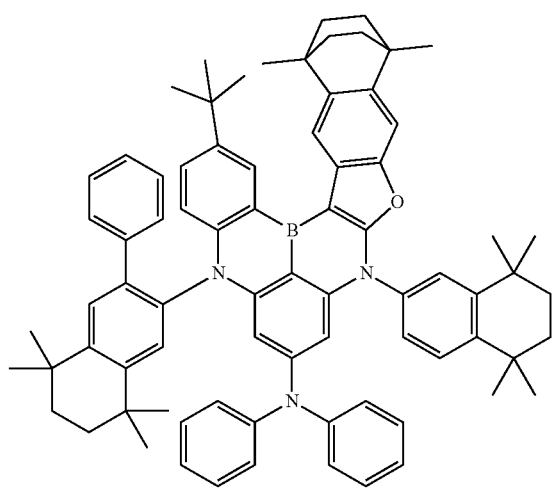
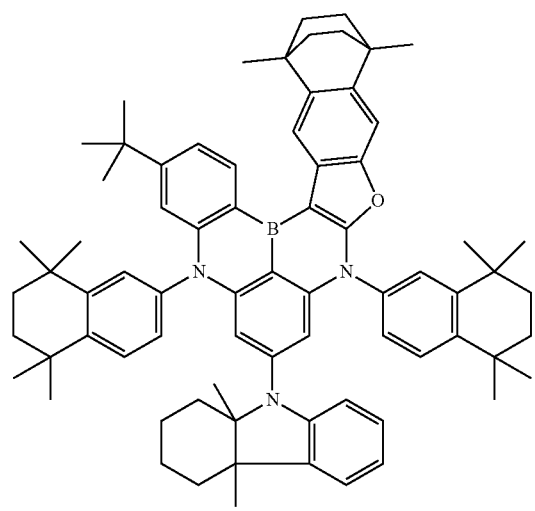
890
-continued
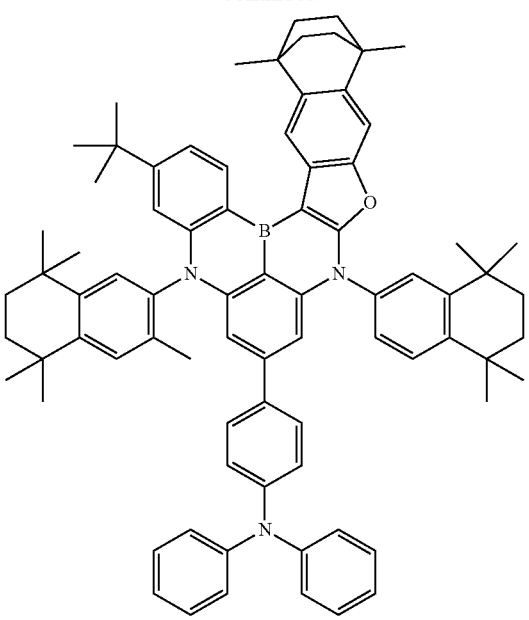
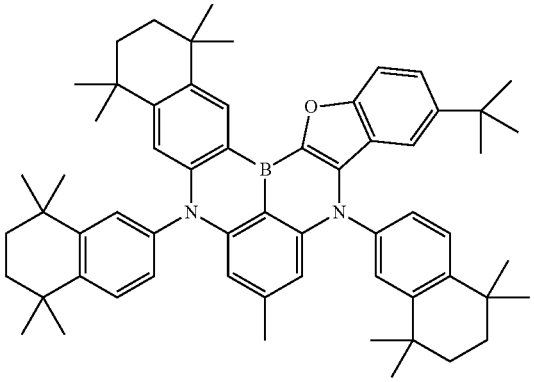
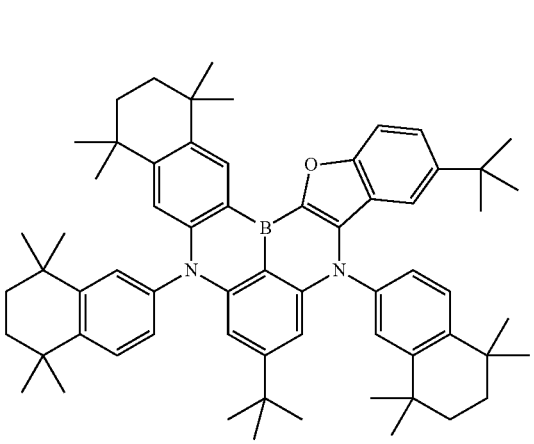

891
-continued
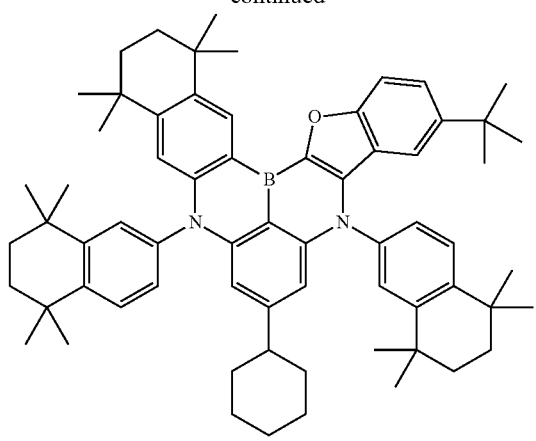
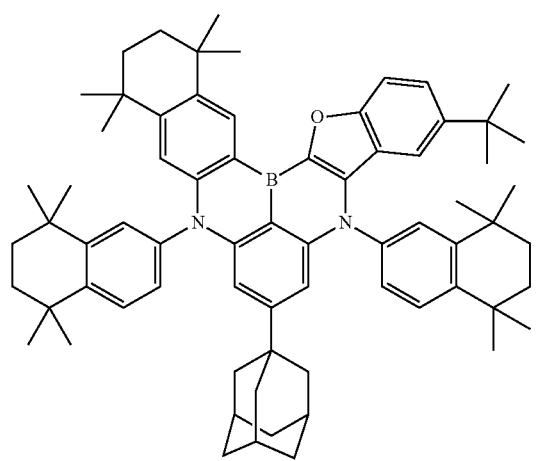
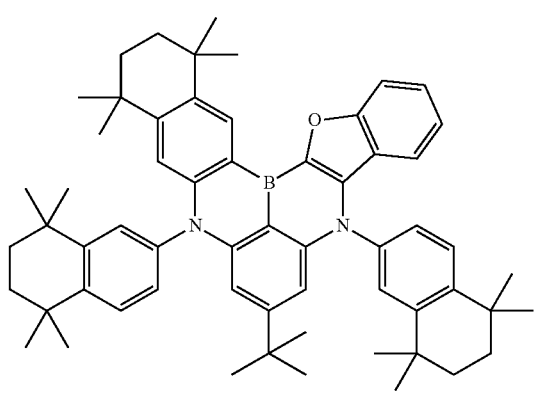
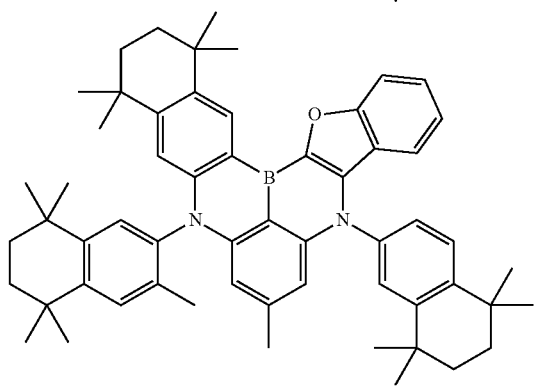
892
-continued
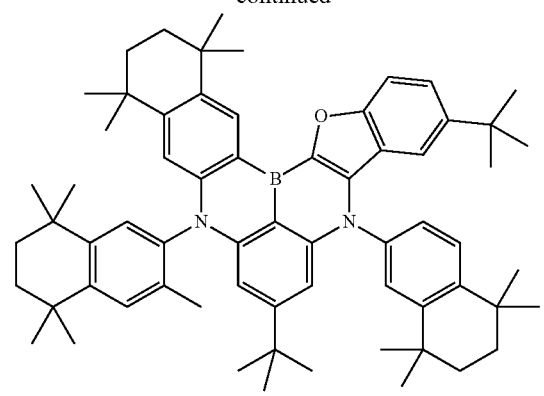
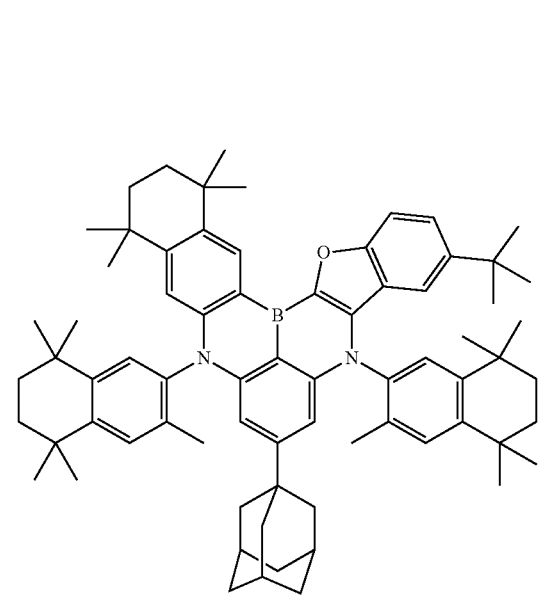
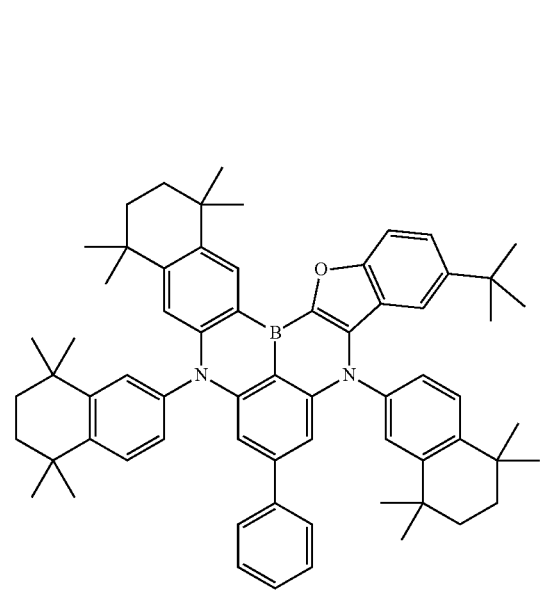

893
-continued
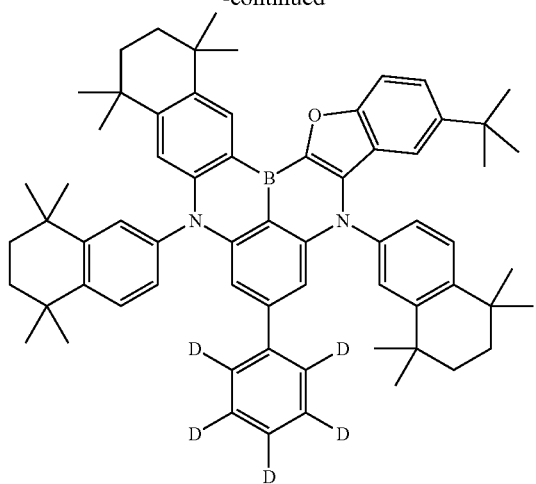
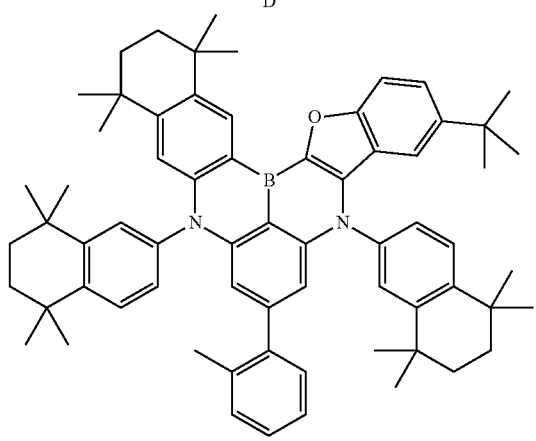
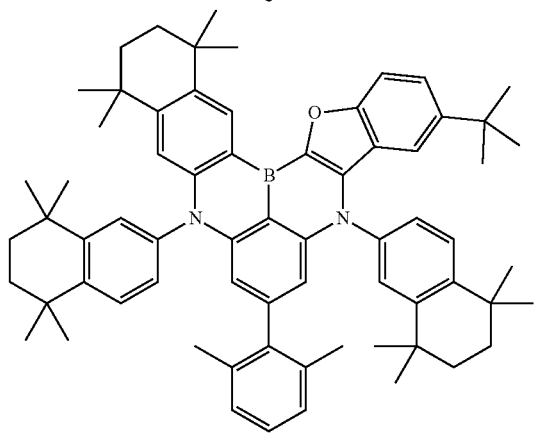
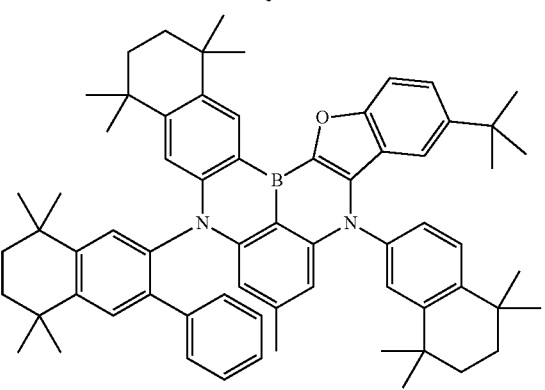
894
-continued
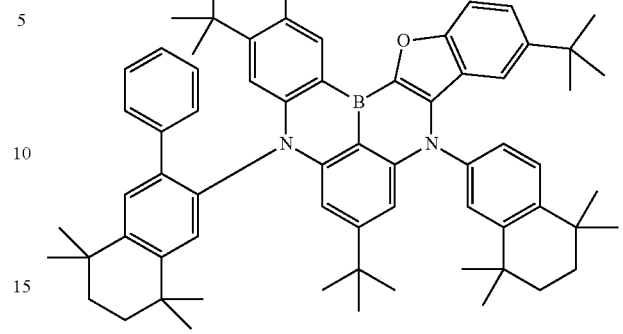

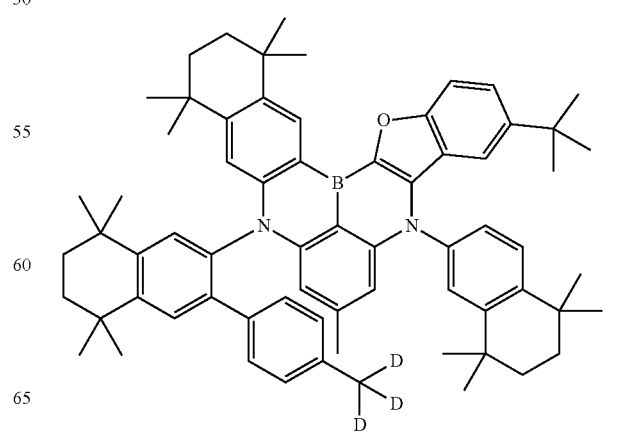

895
-continued
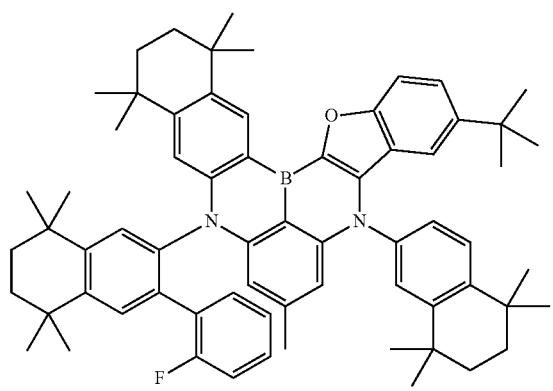
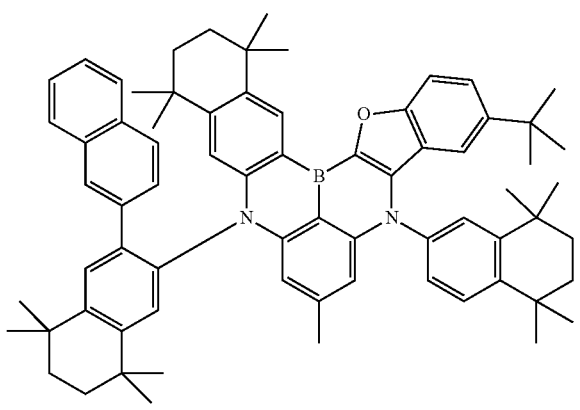
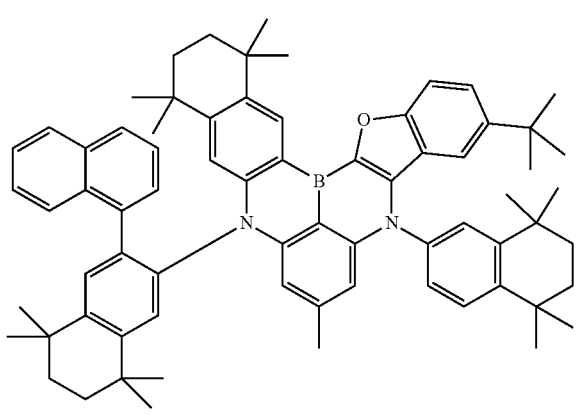
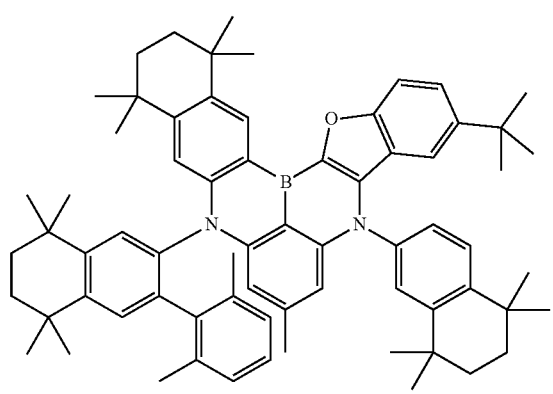
896
-continued
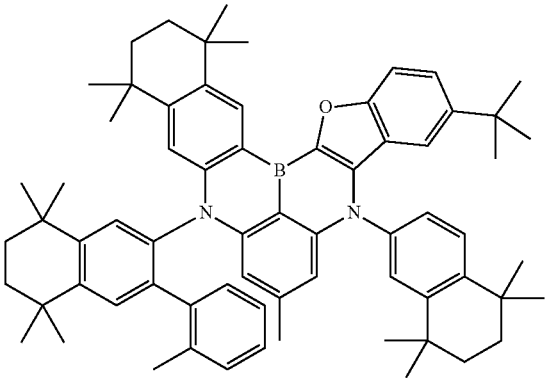
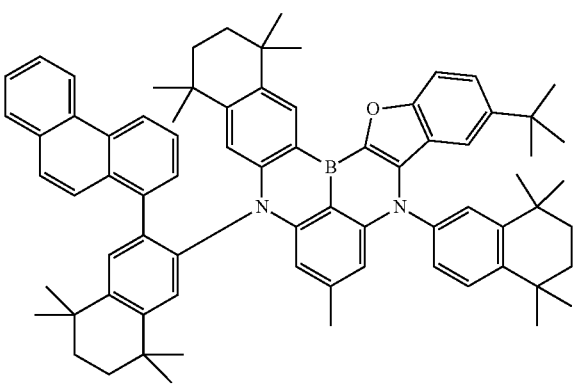
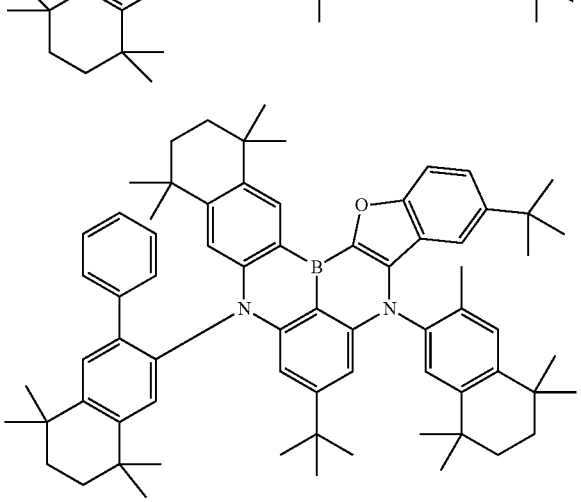

897
-continued
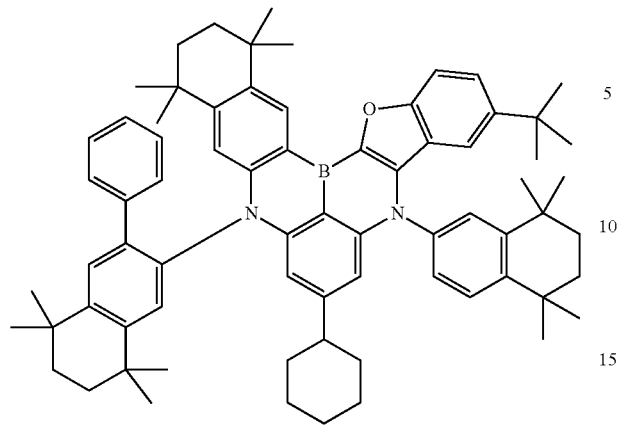
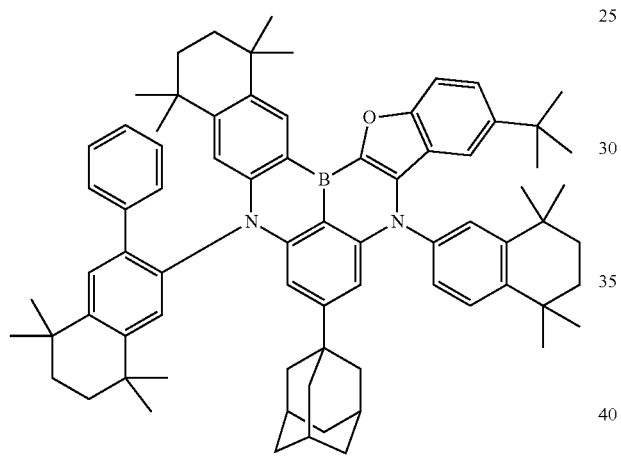
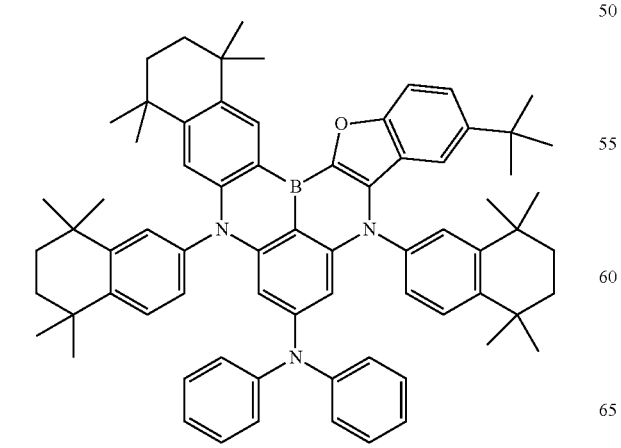
898
-continued
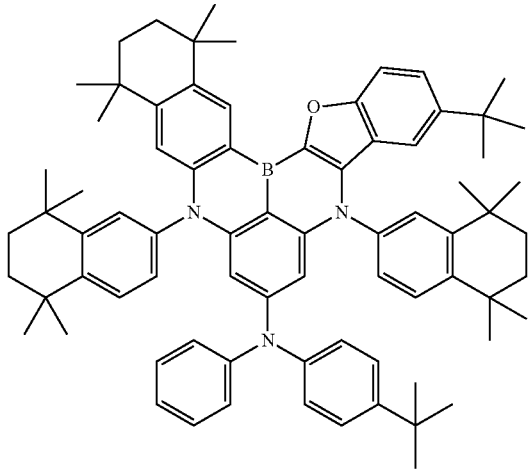
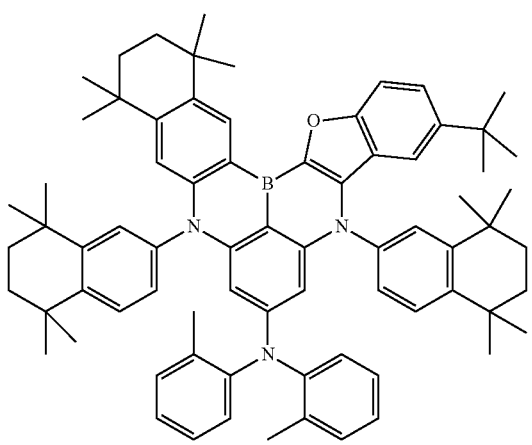
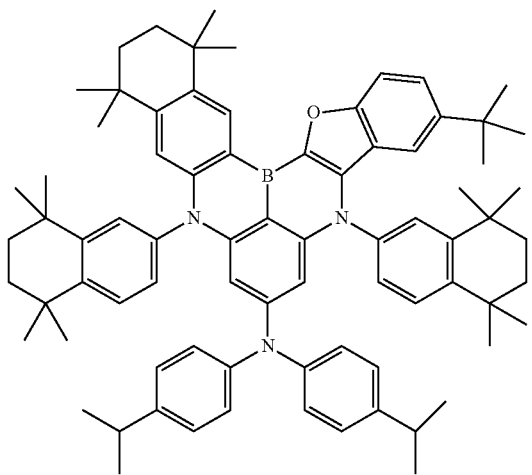

899
-continued
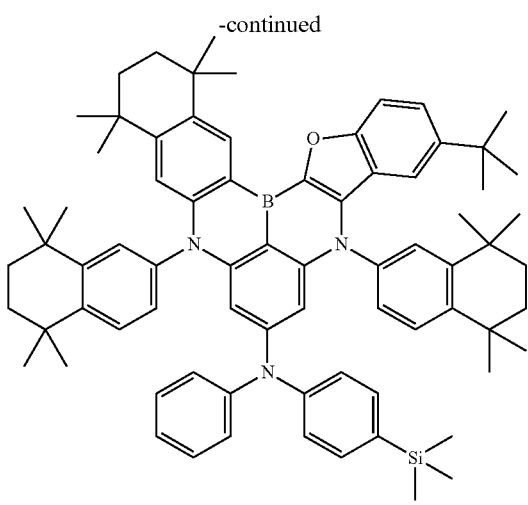
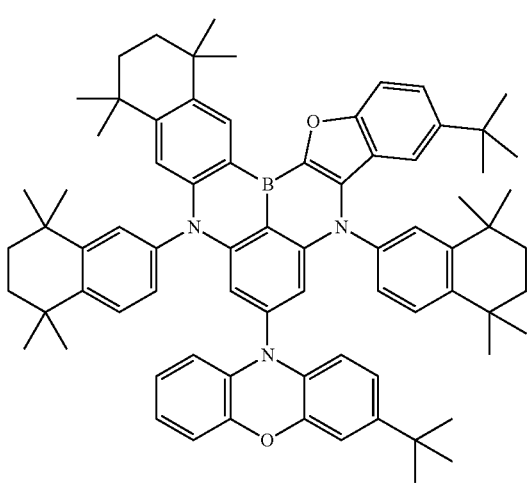
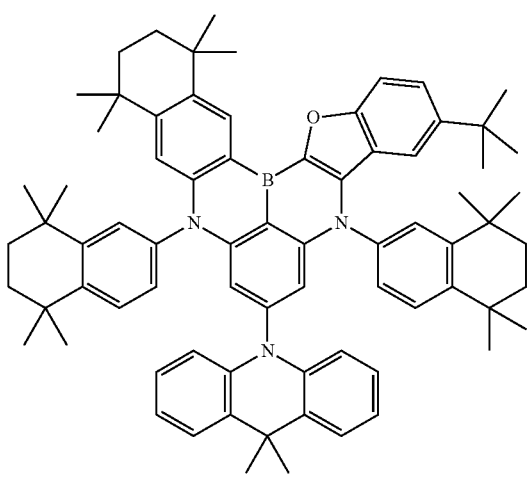
900
-continued
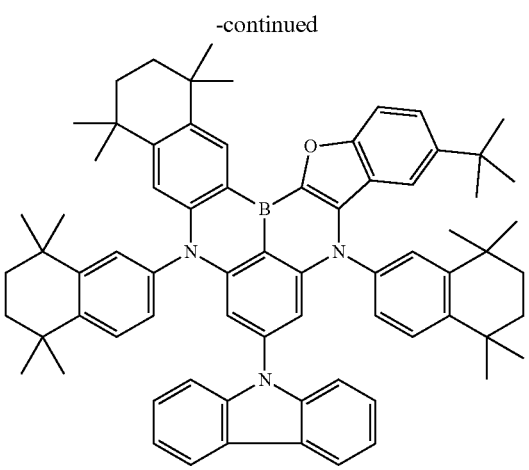
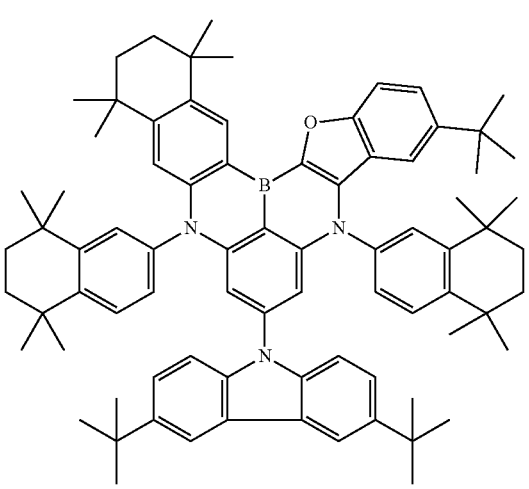
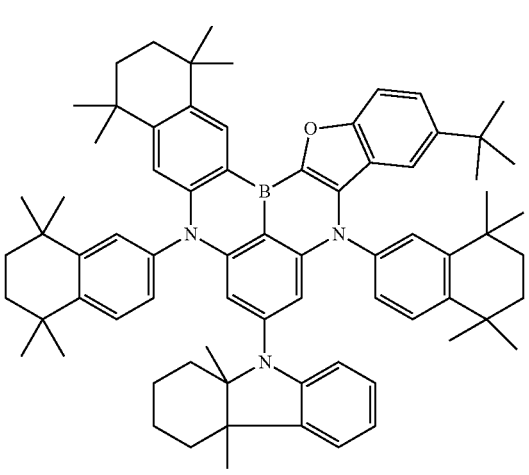

901
-continued
902
-continued
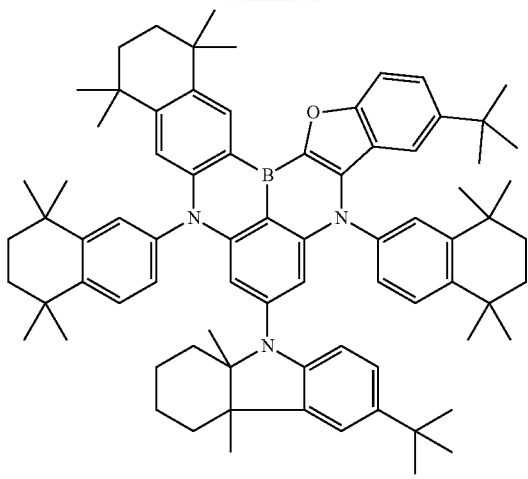
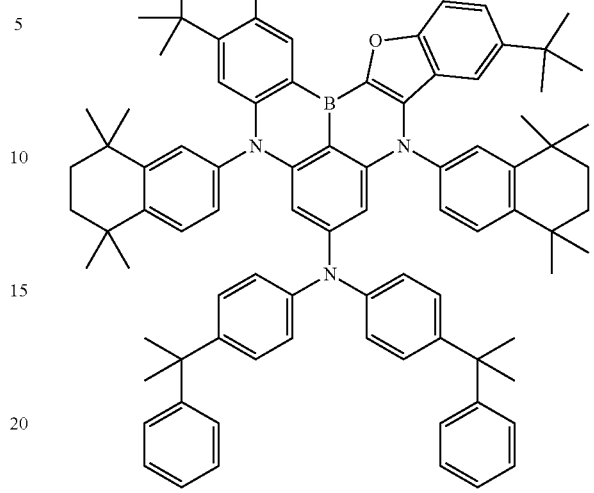
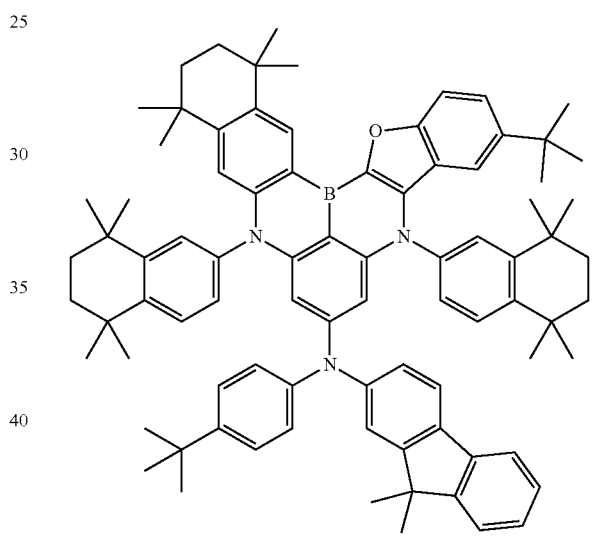
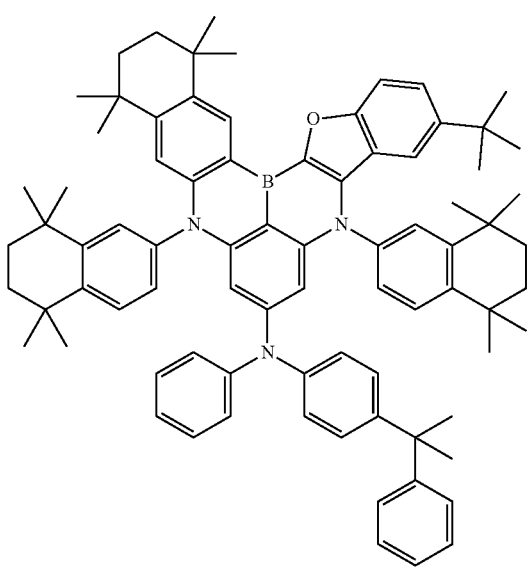
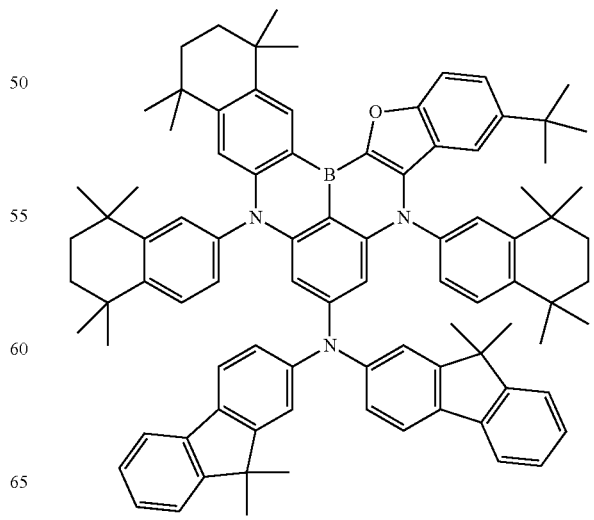

903 -continued
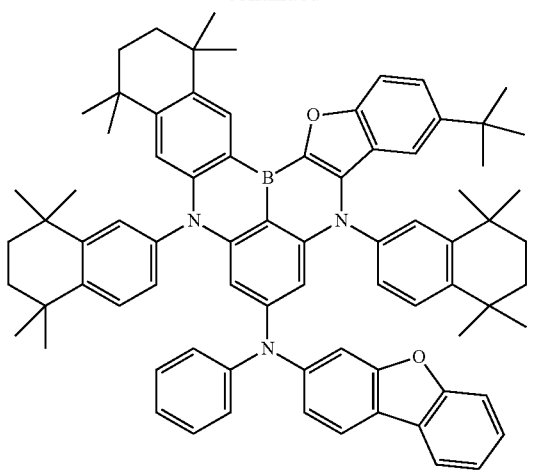
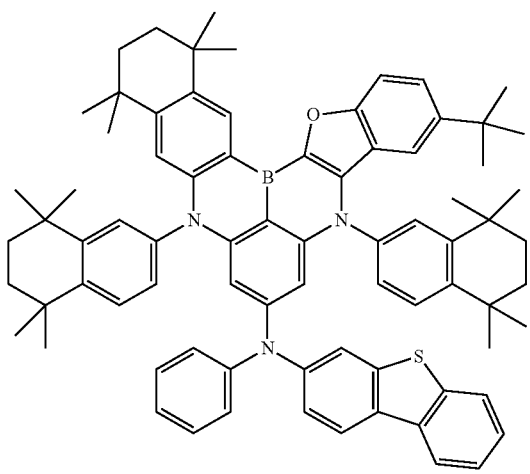
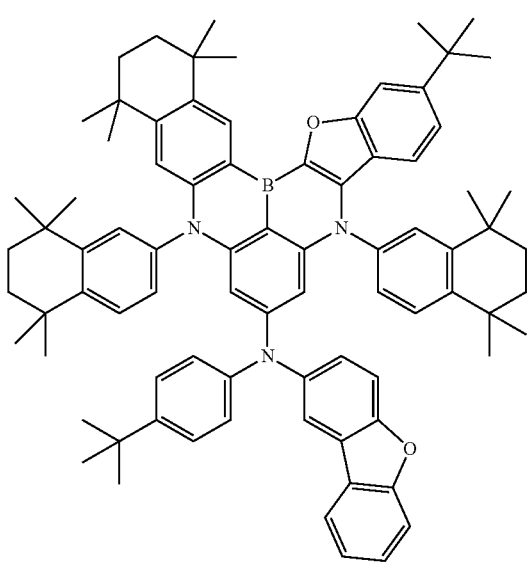
904 -continued
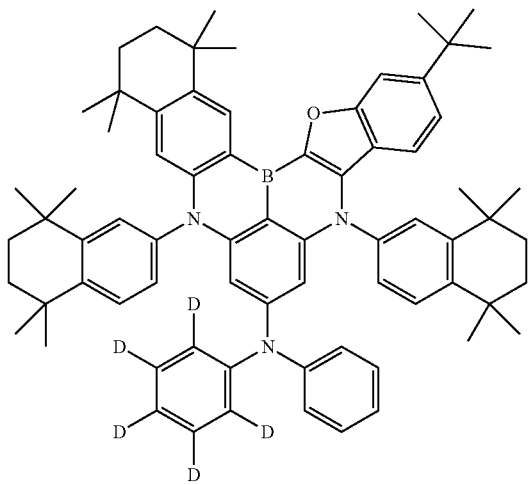
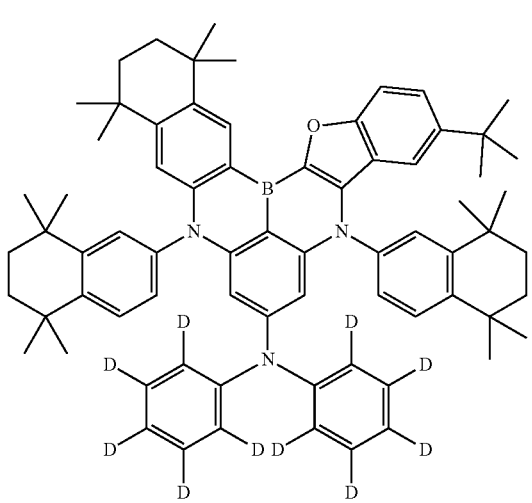
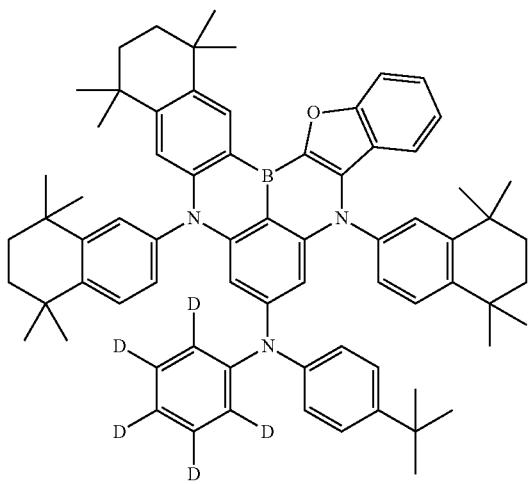

905
-continued
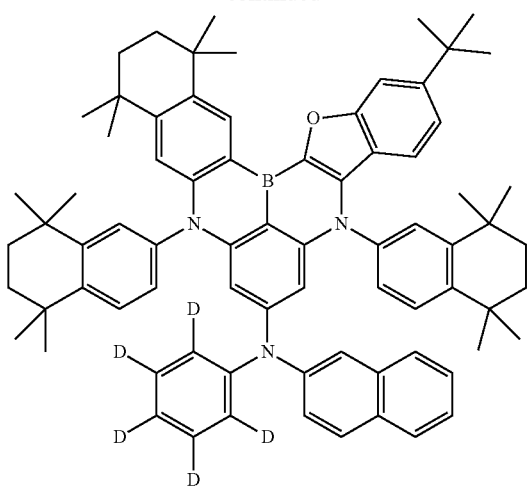
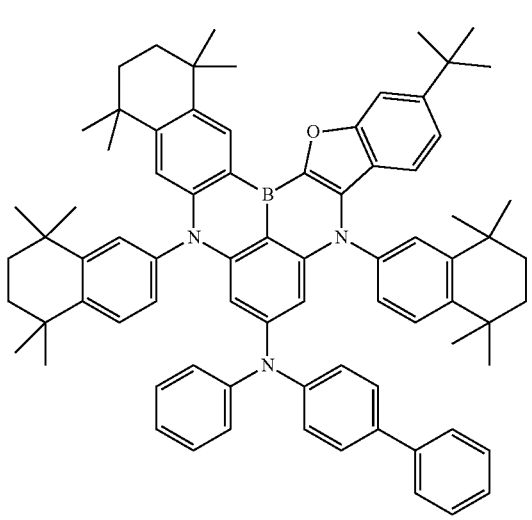
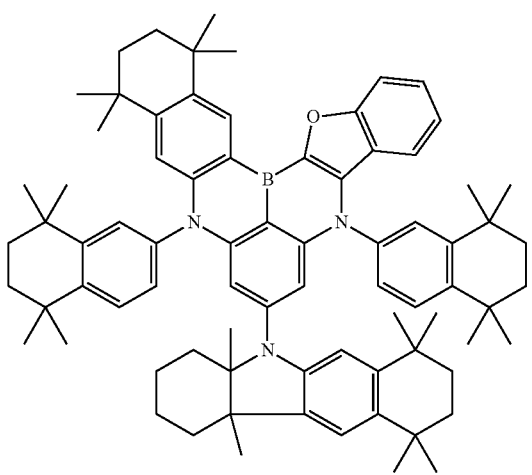
906
-continued
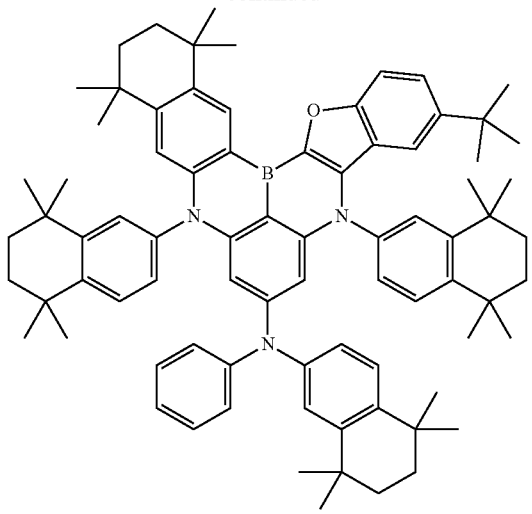
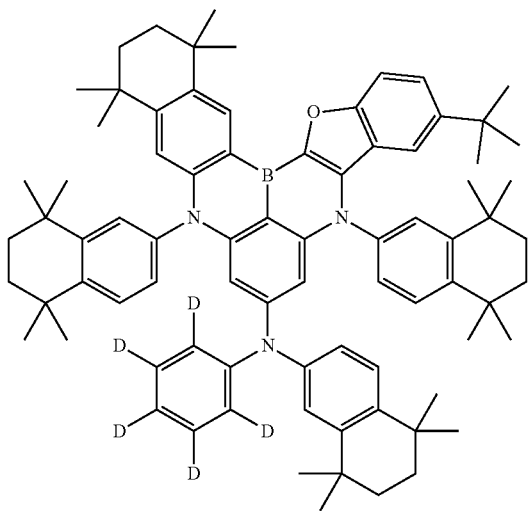
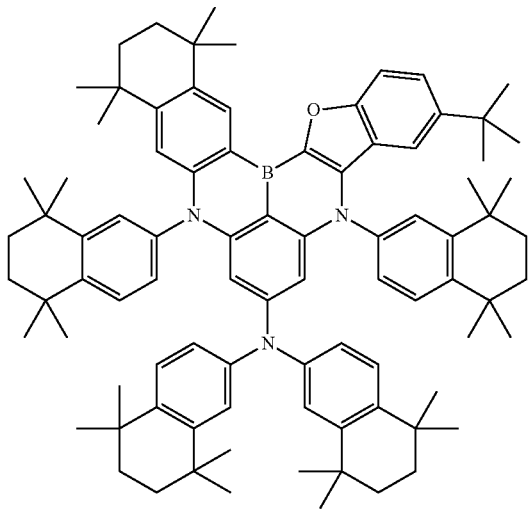

907
-continued
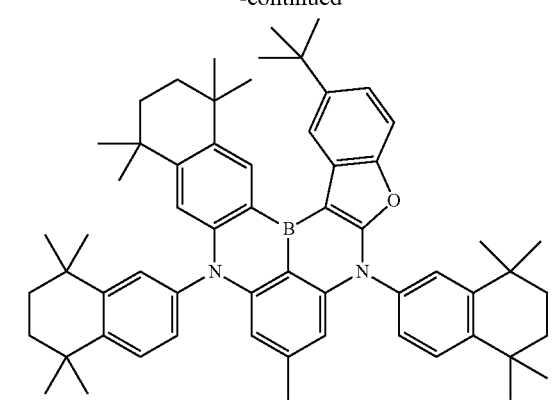
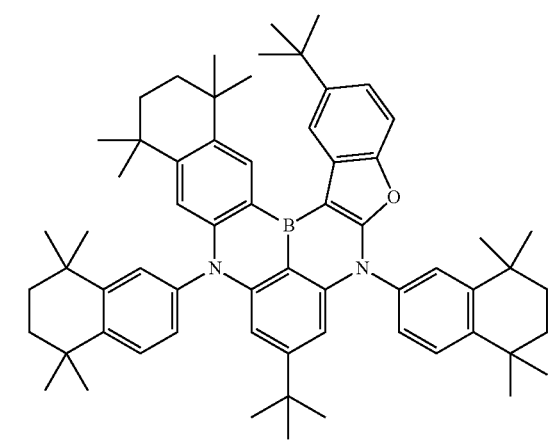
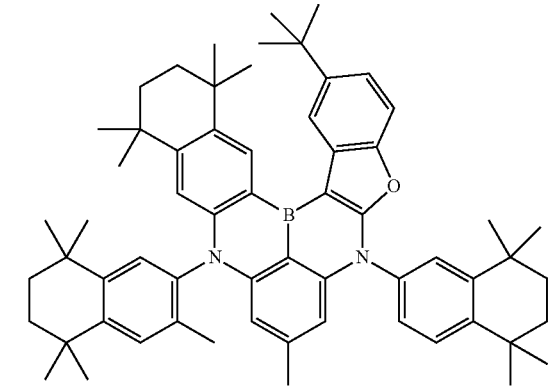
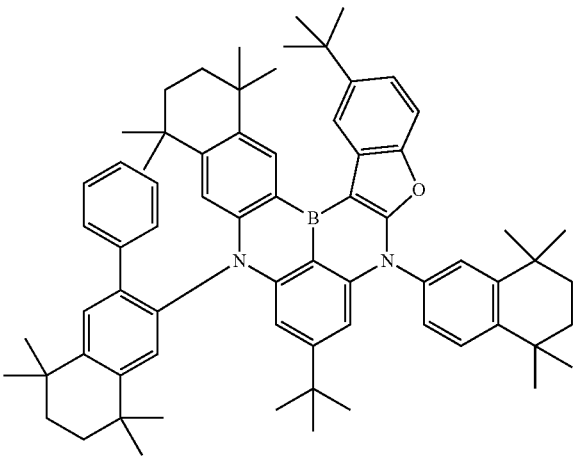
908
-continued
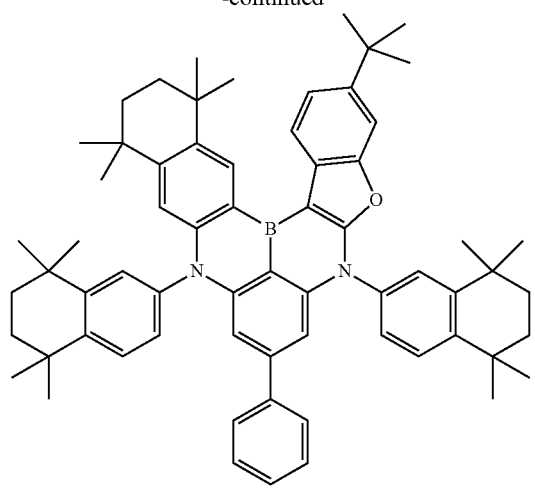
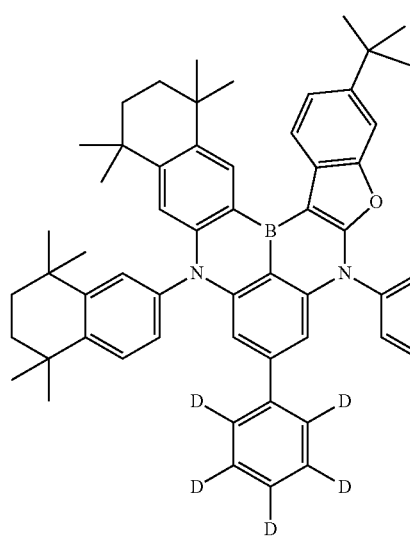
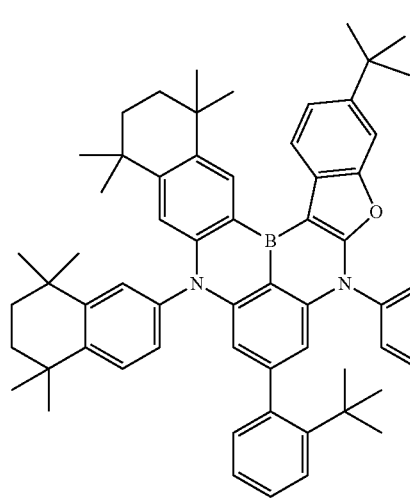

909
-continued
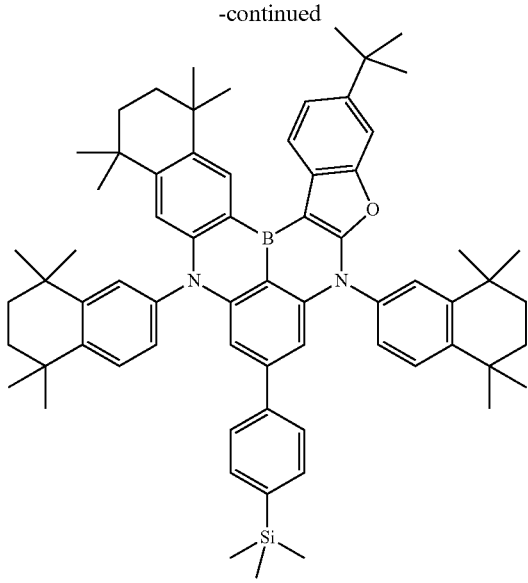
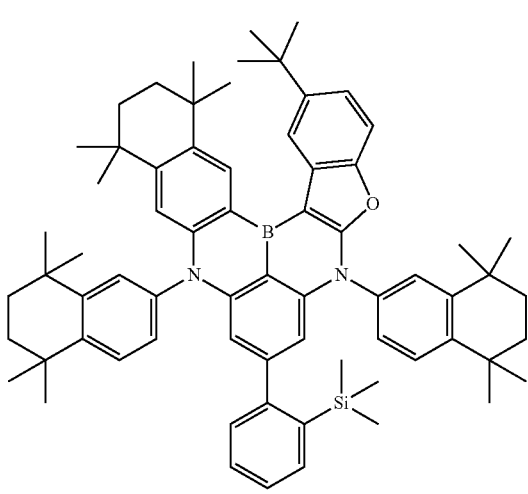
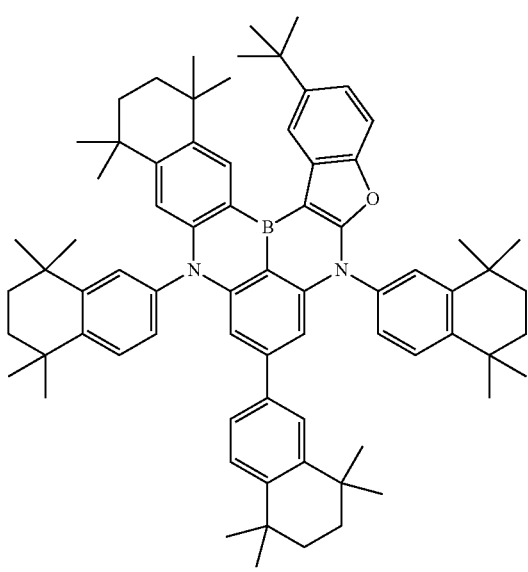
910
-continued
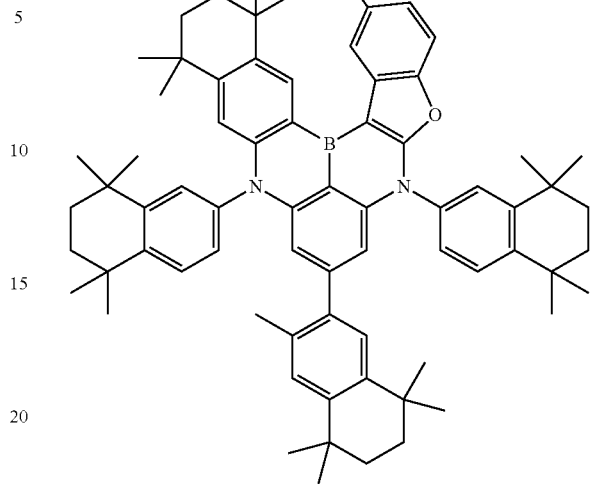
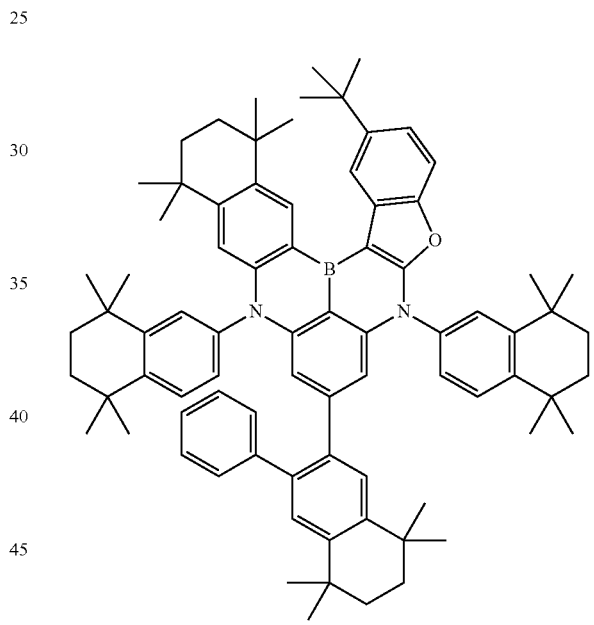
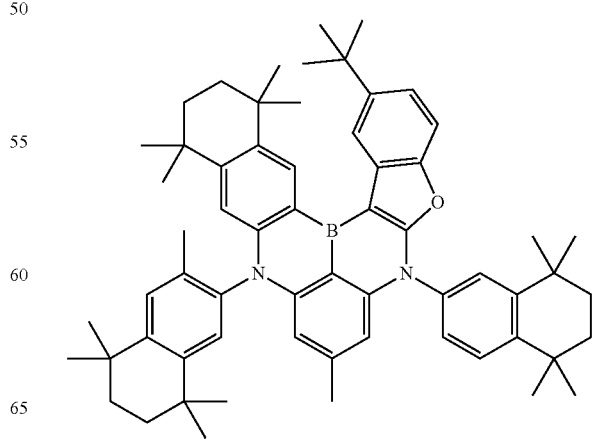

911
-continued
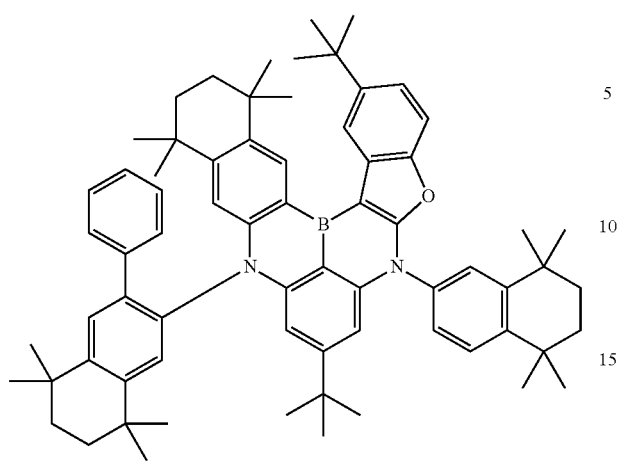
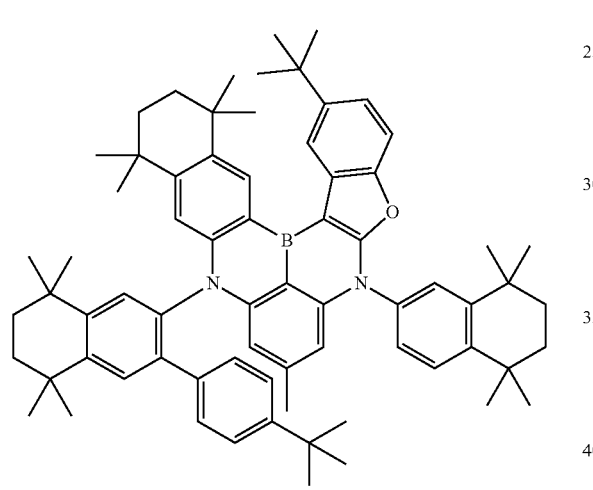
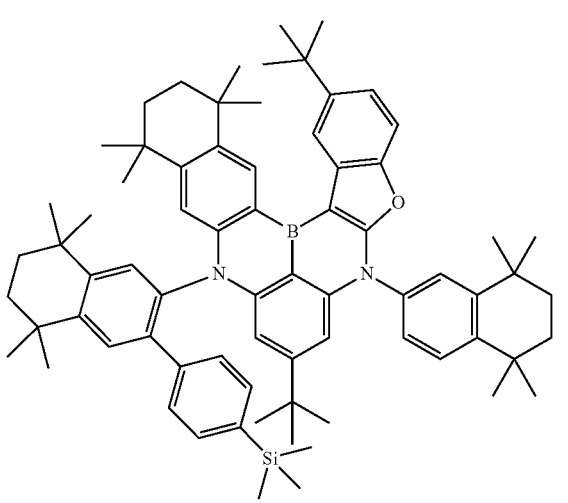
912
-continued
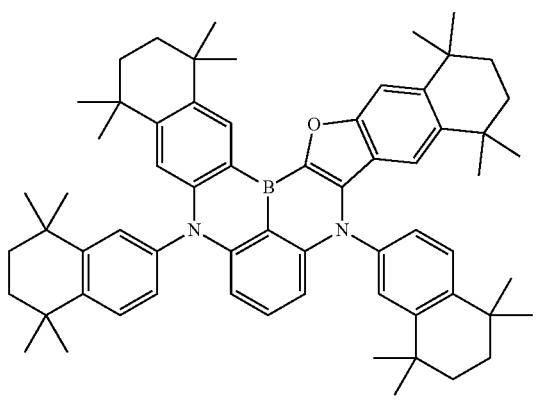
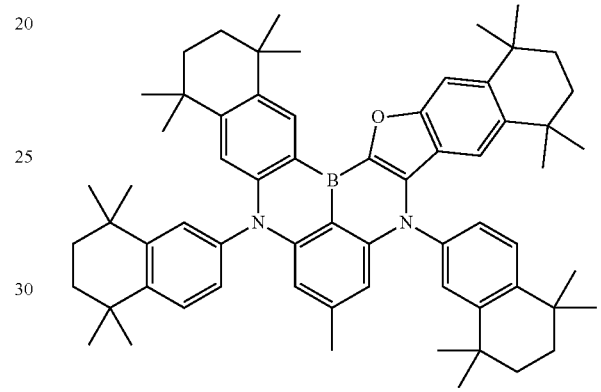
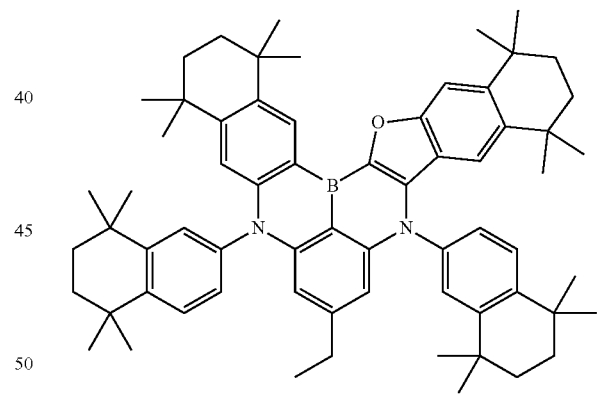
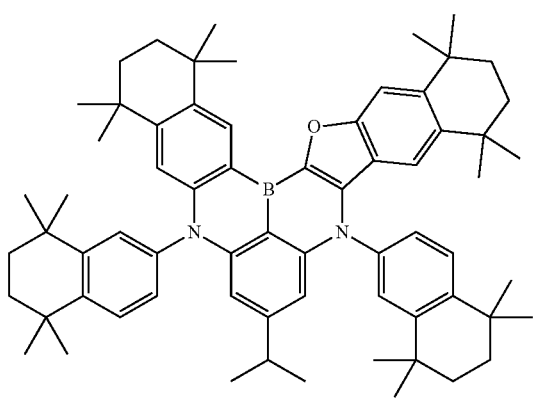

913
-continued
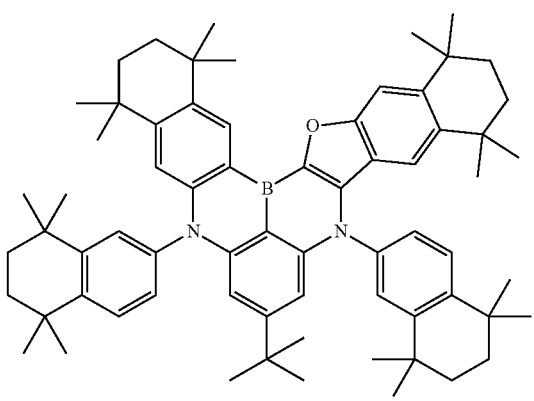
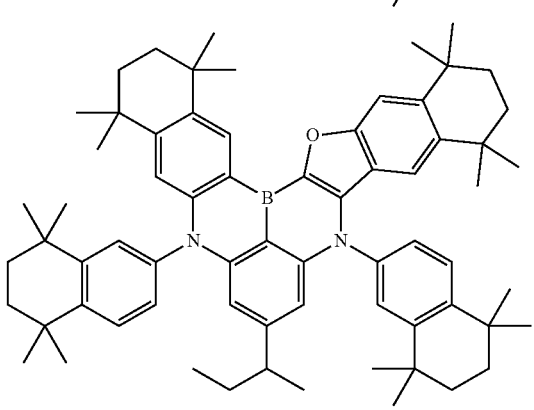
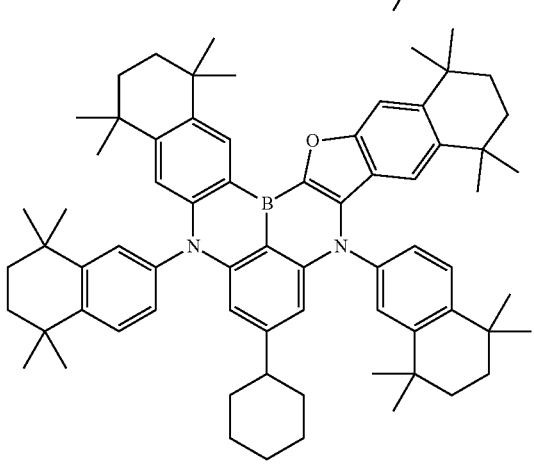
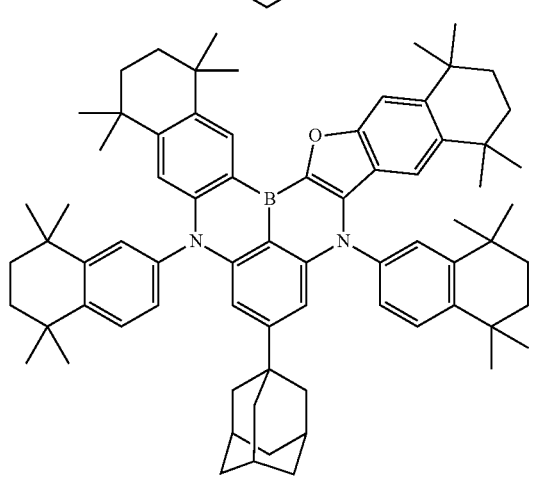
914
-continued
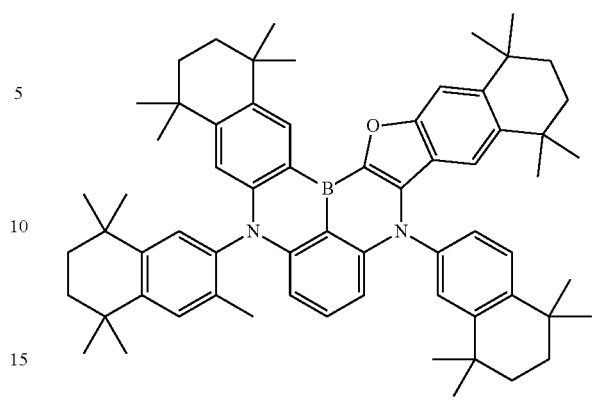
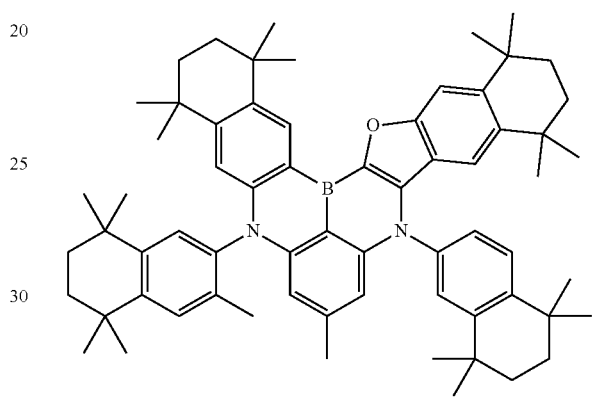
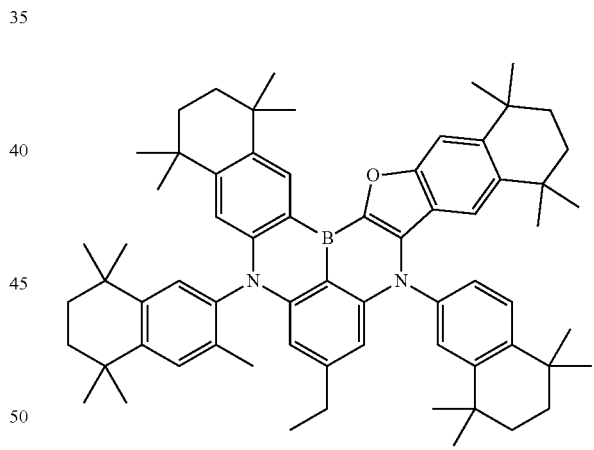
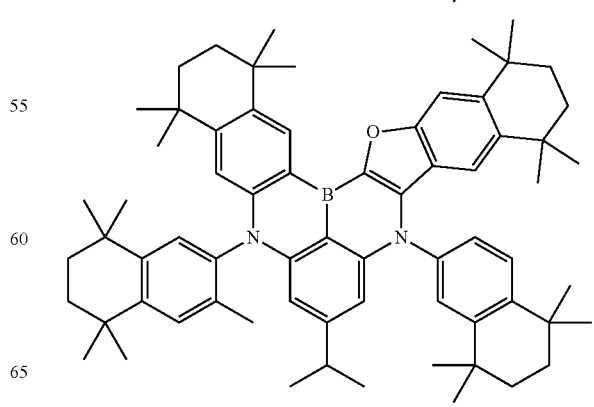

915
-continued
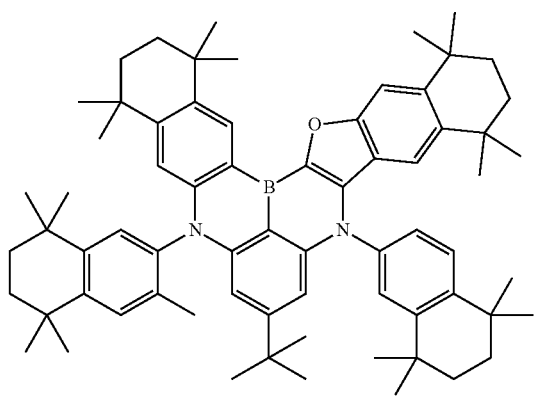
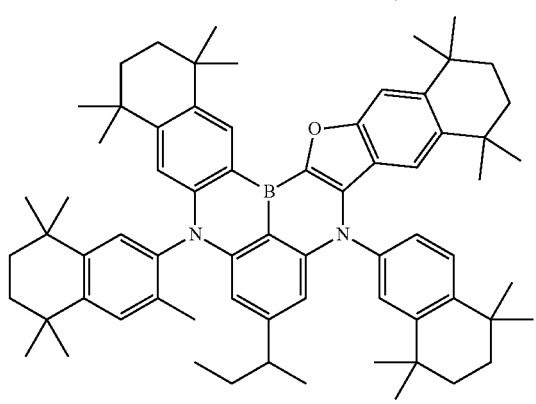
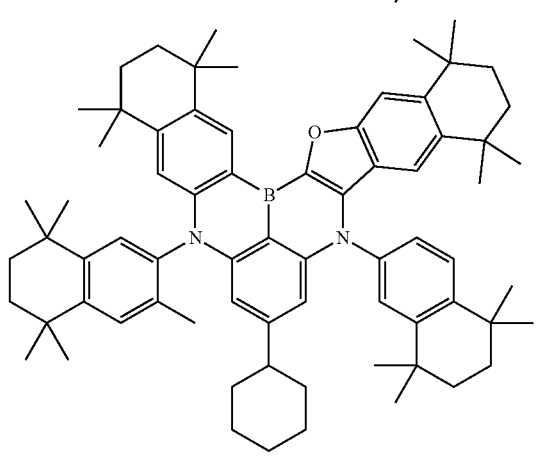
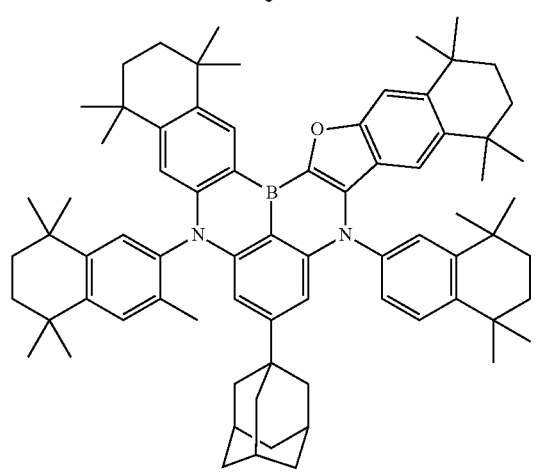
916
-continued
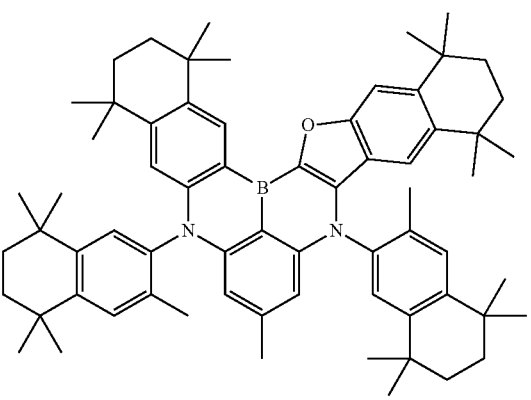
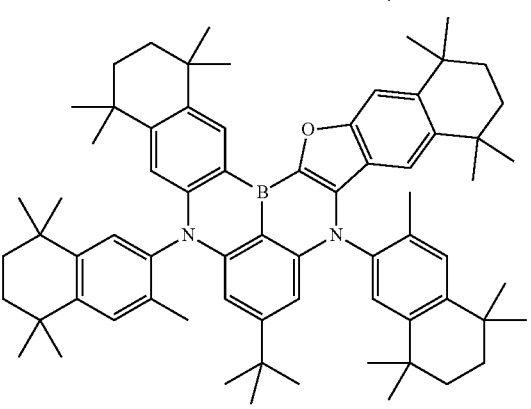
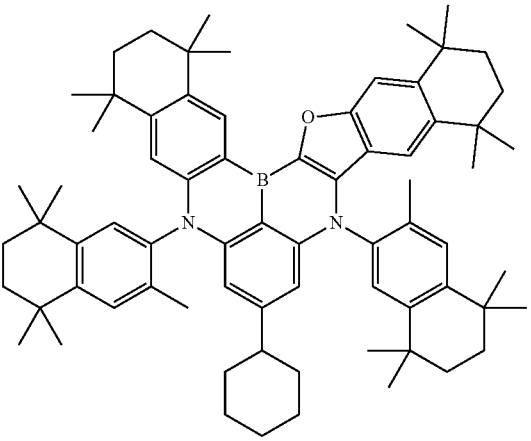
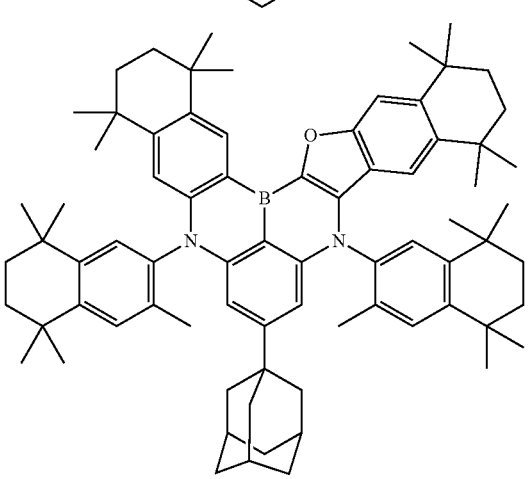

917
-continued
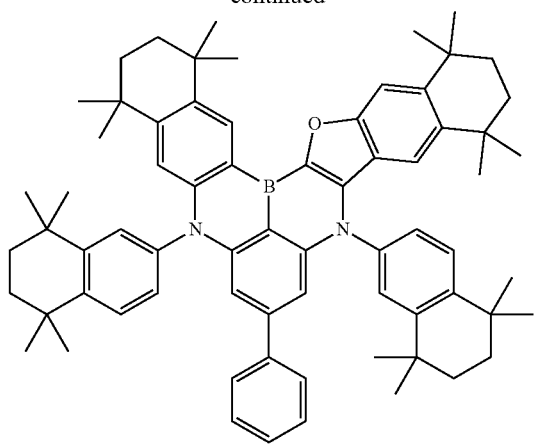
918
-continued
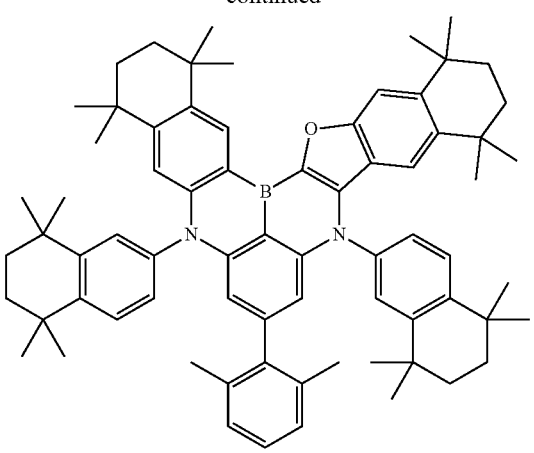
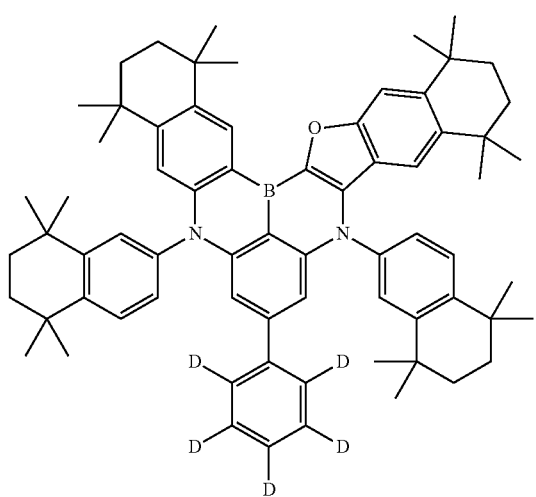
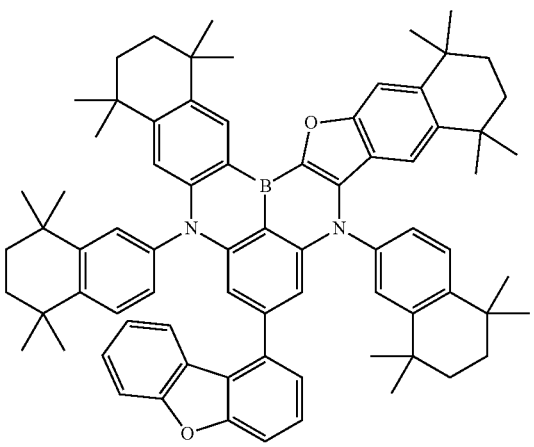
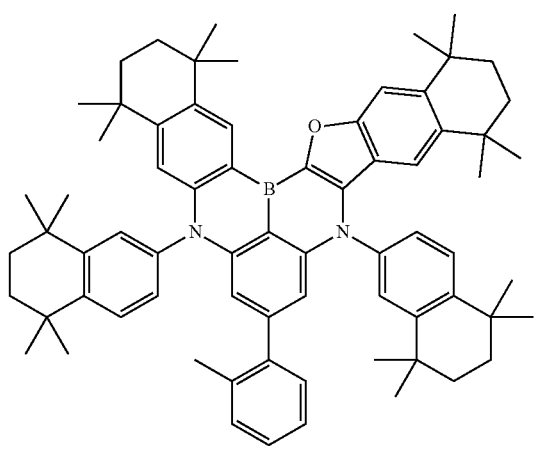
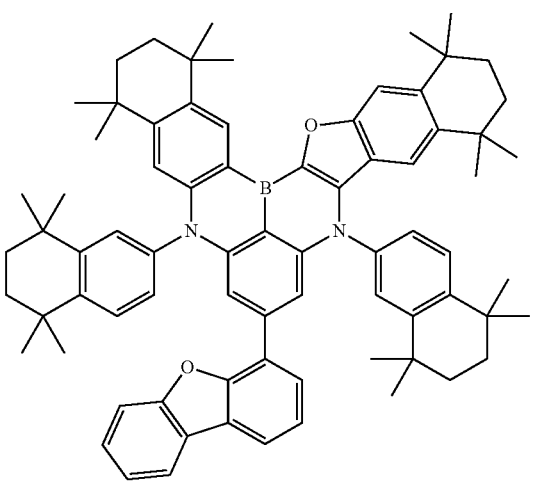

919
-continued
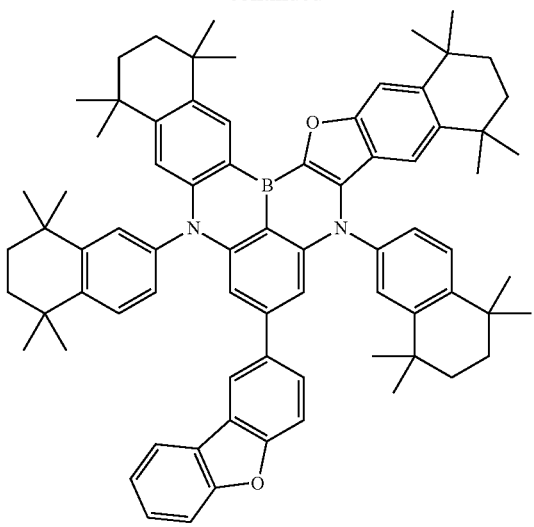
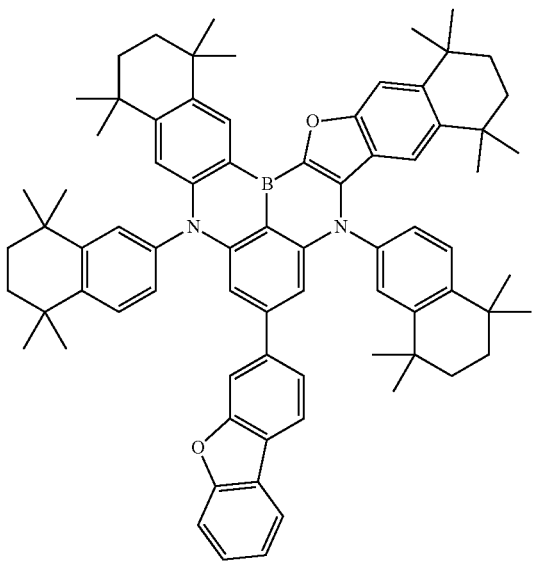
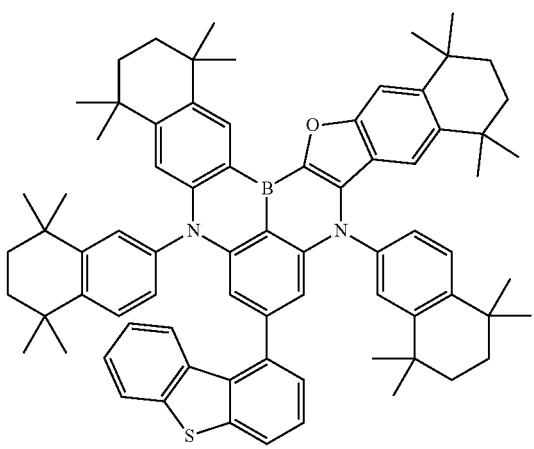
920
-continued
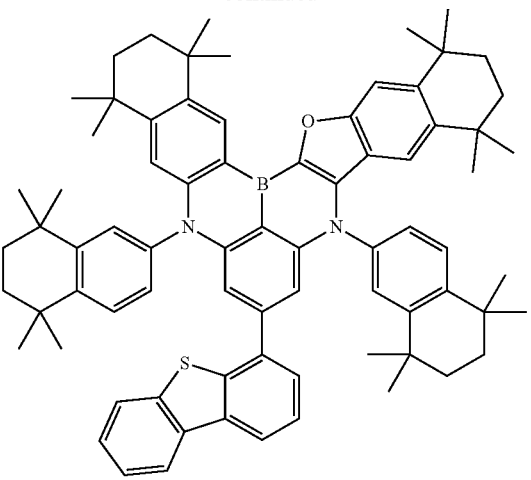
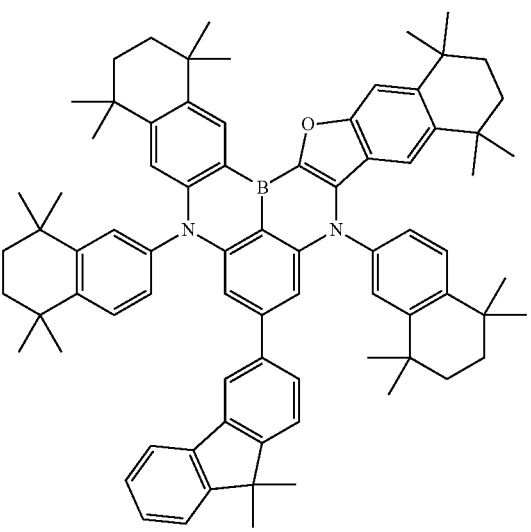
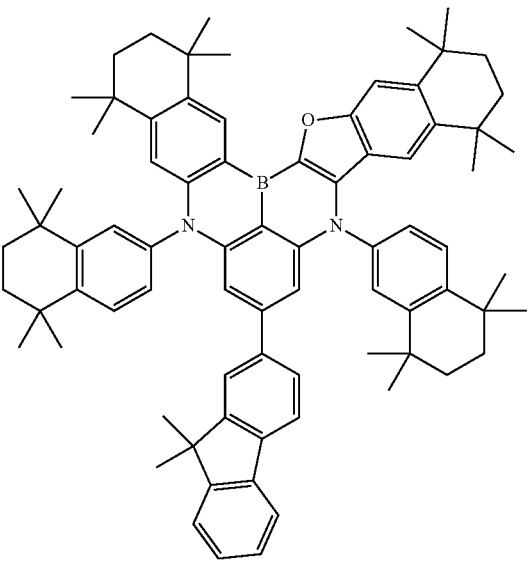

| 921 -continued | 922 -continued |
|---|---|
| 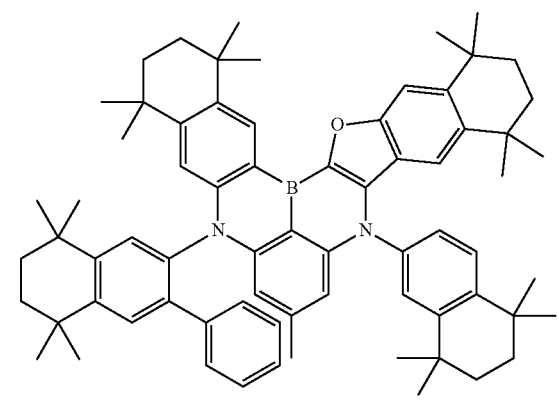 | 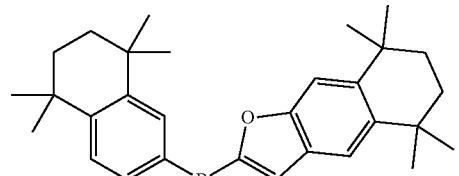 |
| 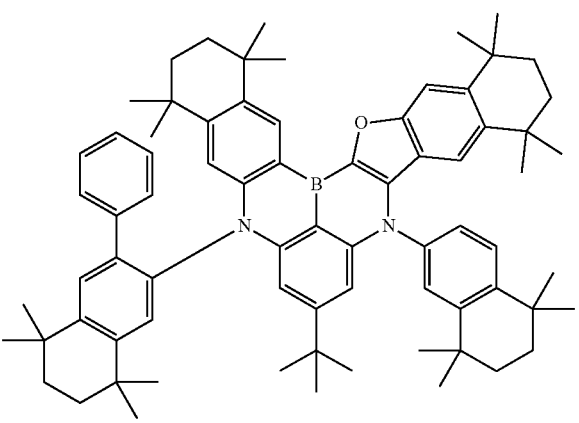 | 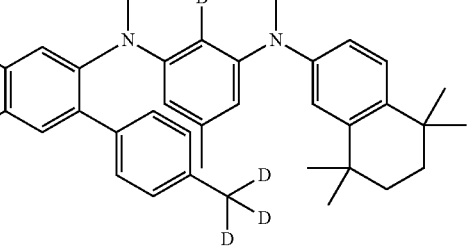 |
| 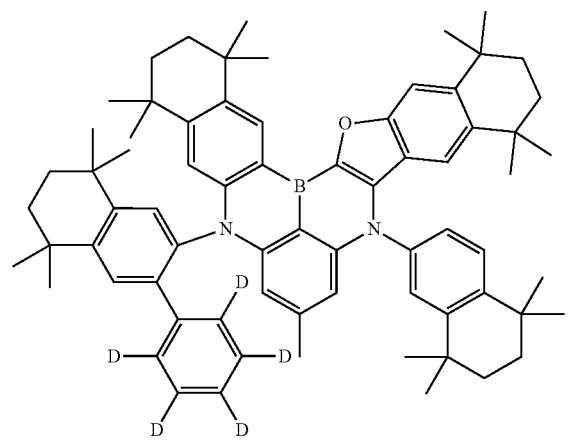 | 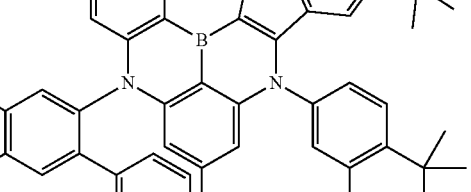 |
| 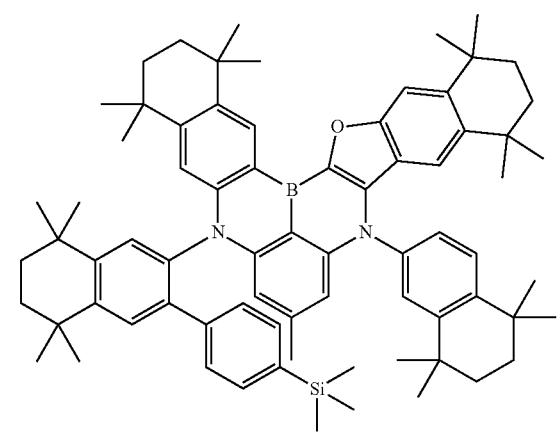 | 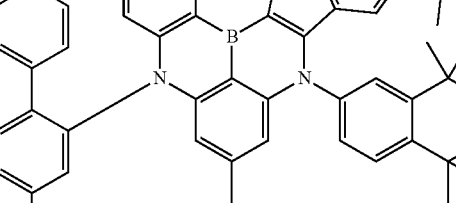 |

923
-continued
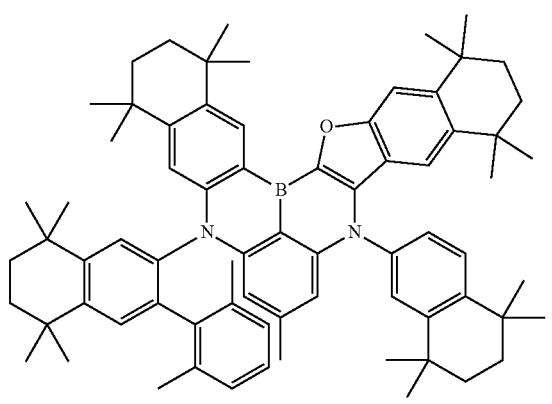
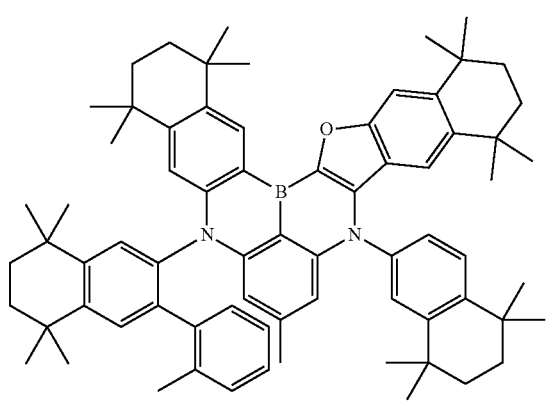
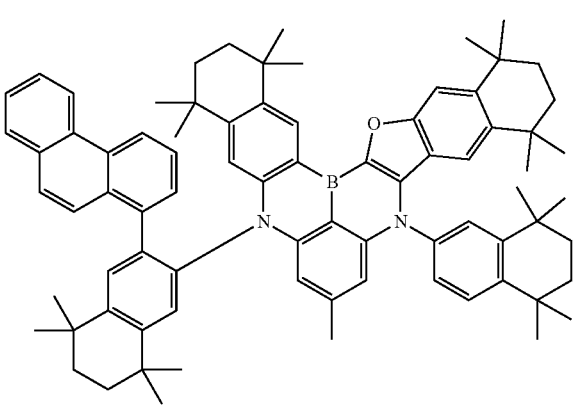
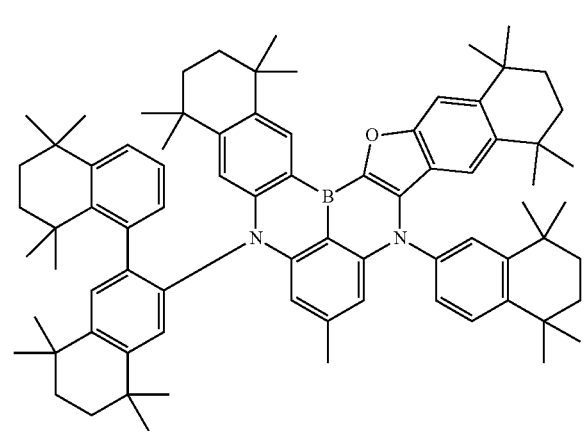
924
-continued
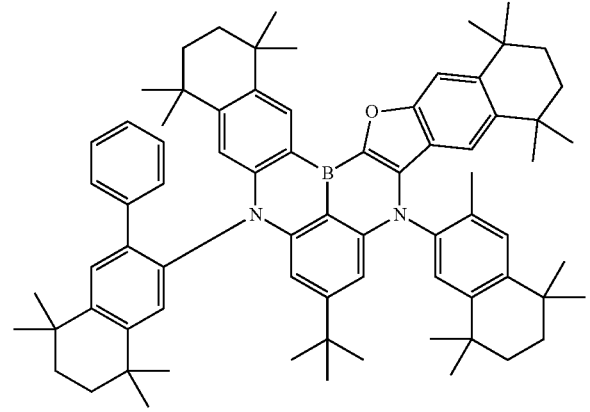
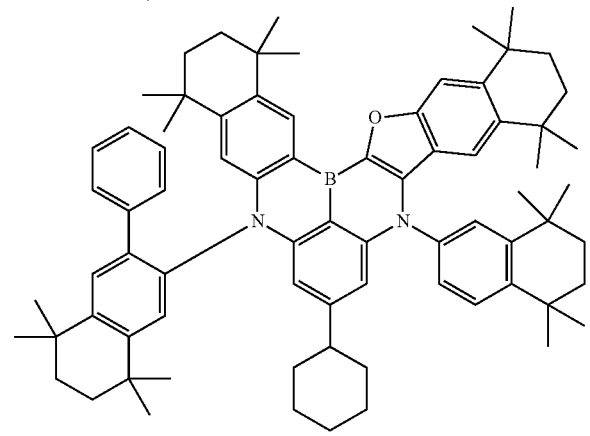
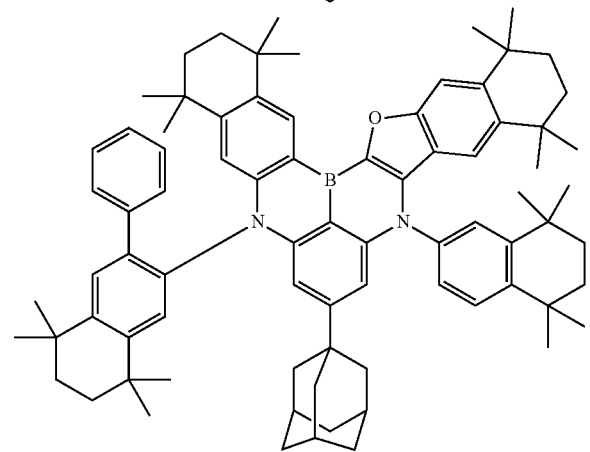
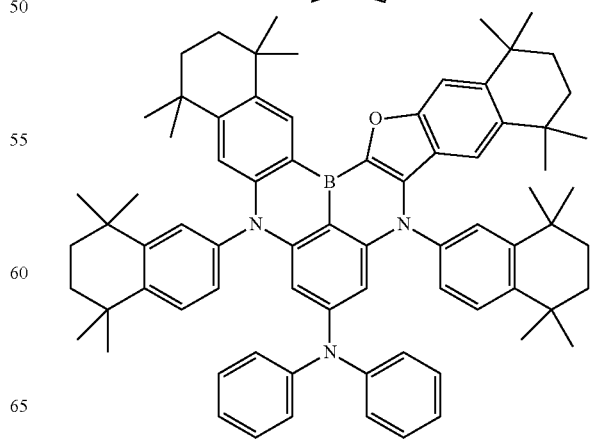

925
-continued
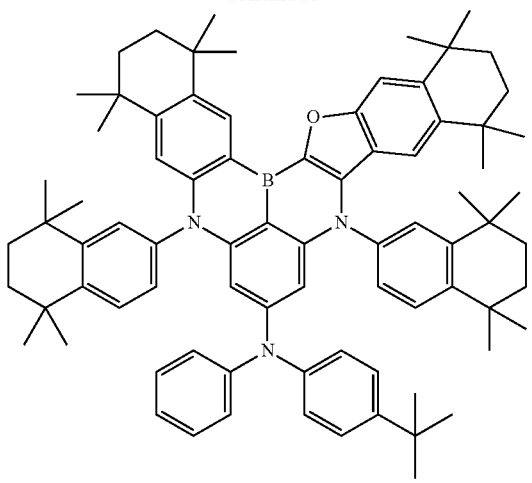
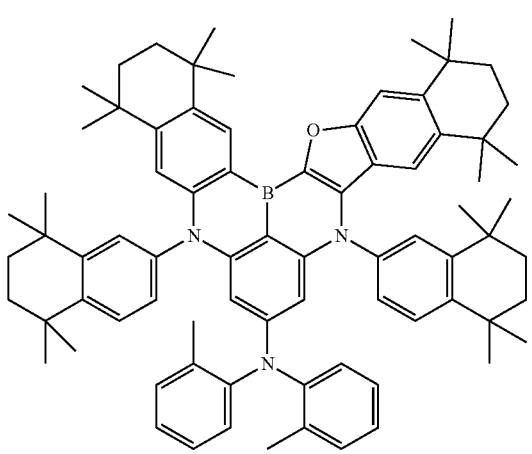
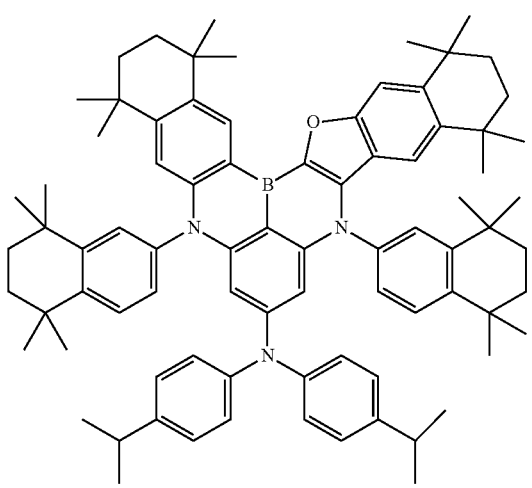
926
-continued
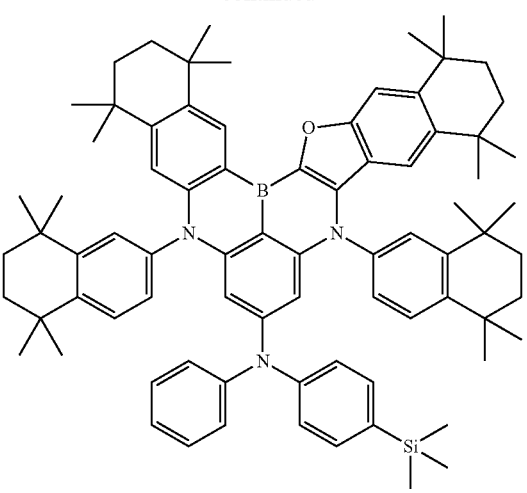
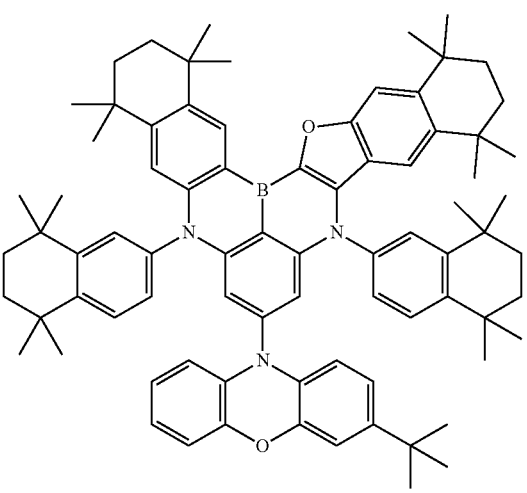
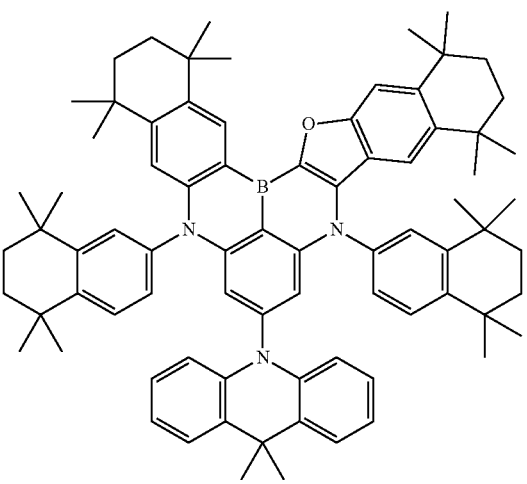

927
-continued
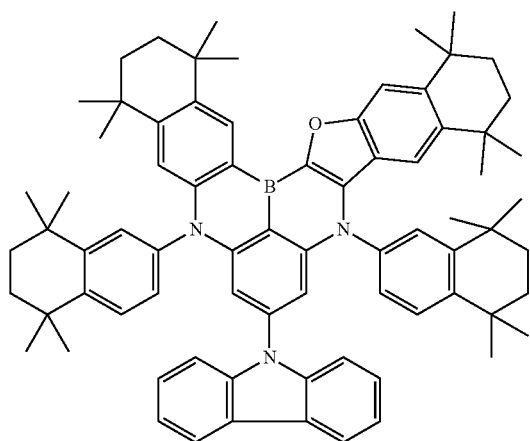
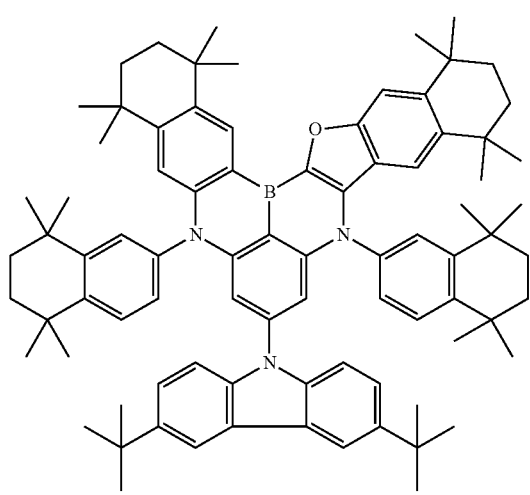
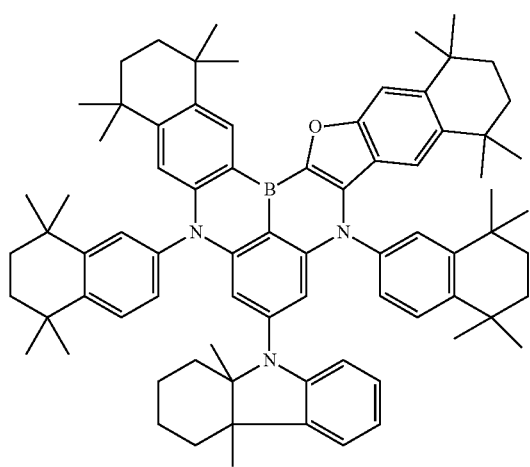
928
-continued
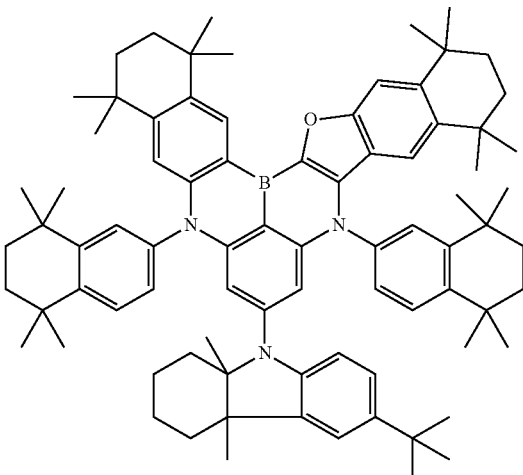
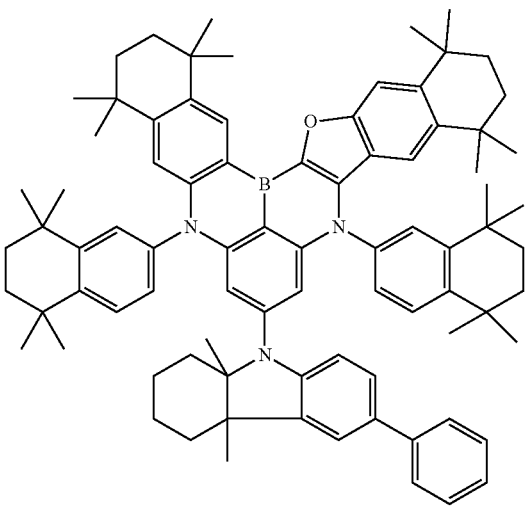
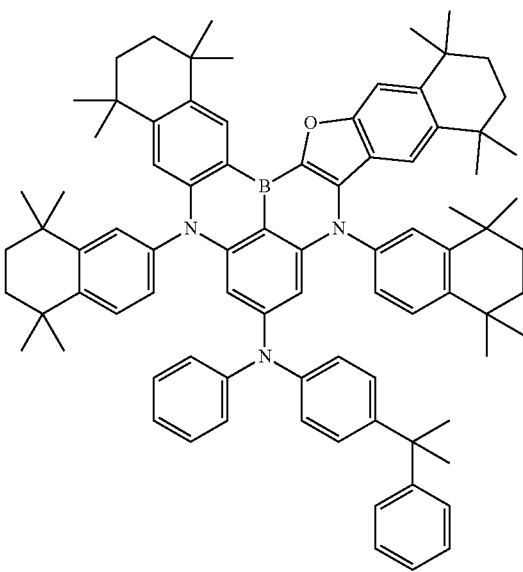

929
-continued
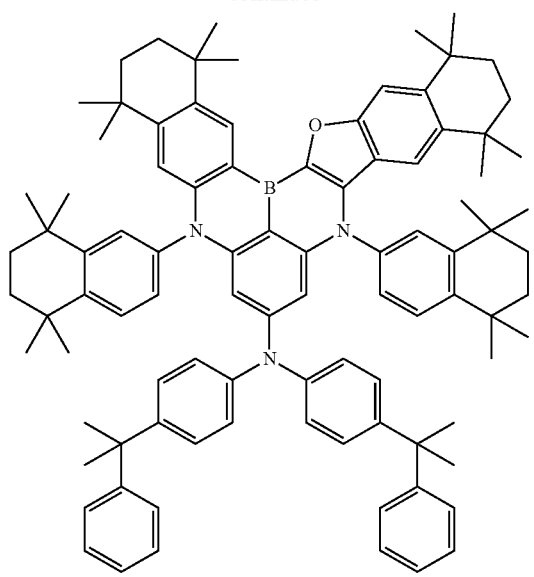
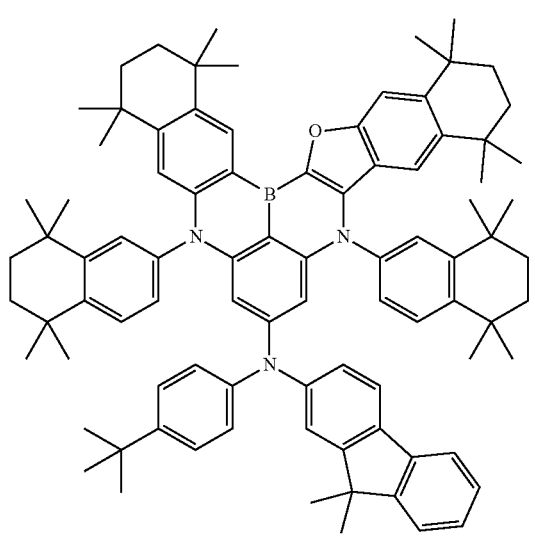
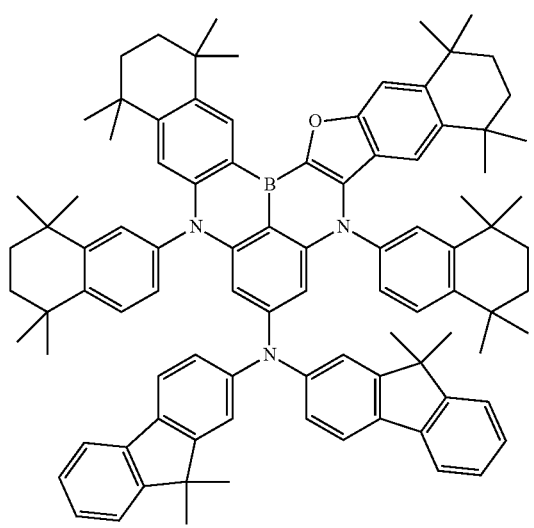
930
-continued
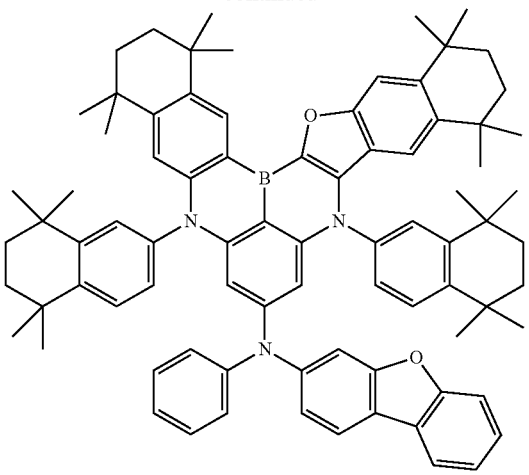
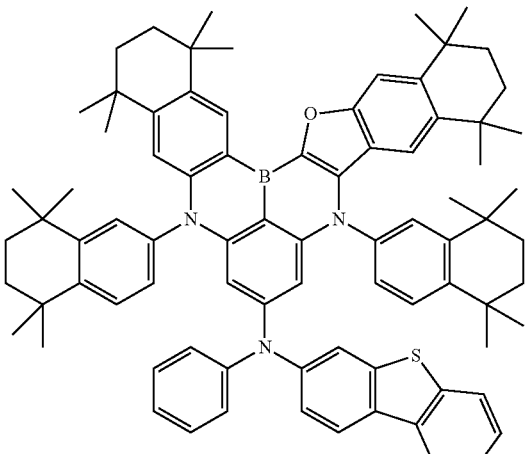
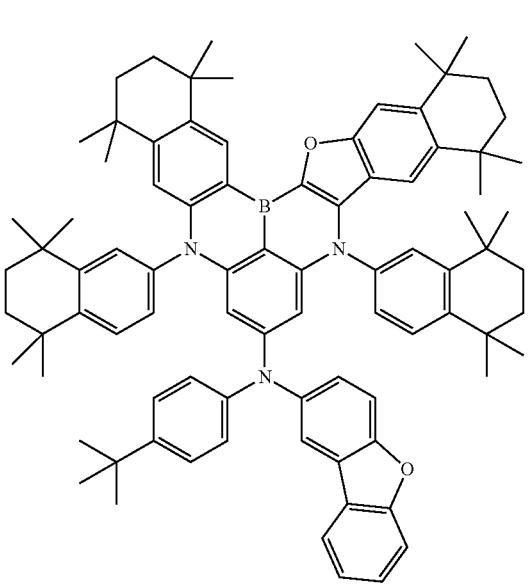

931
-continued
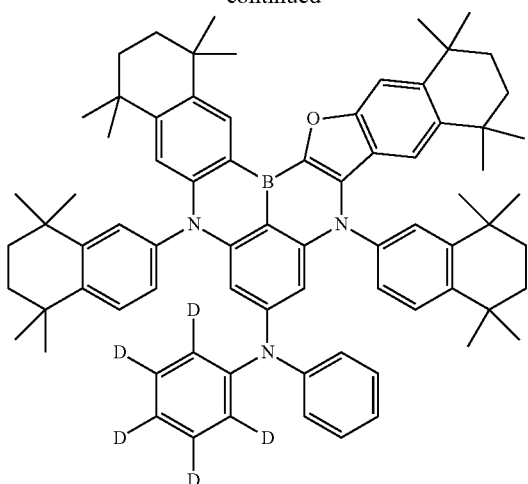
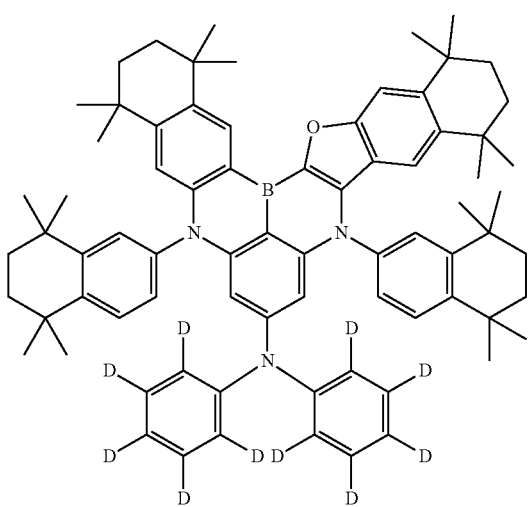
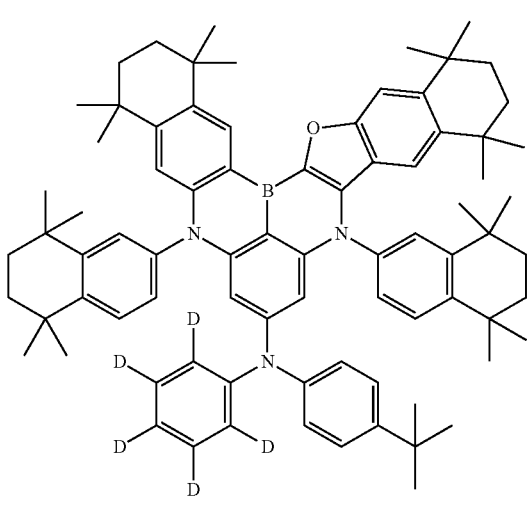
932
-continued
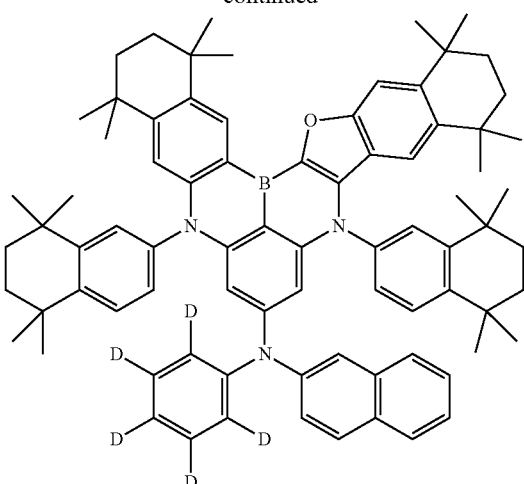
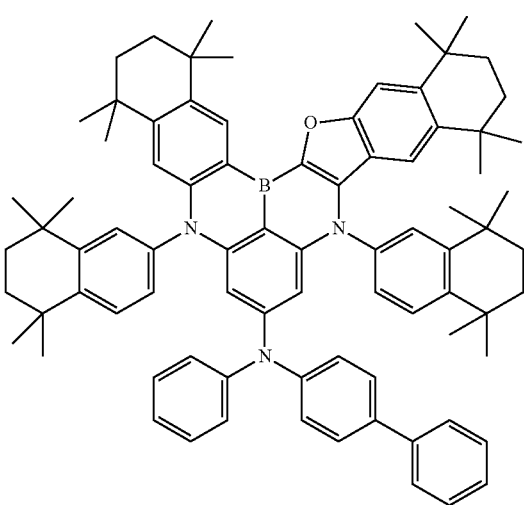
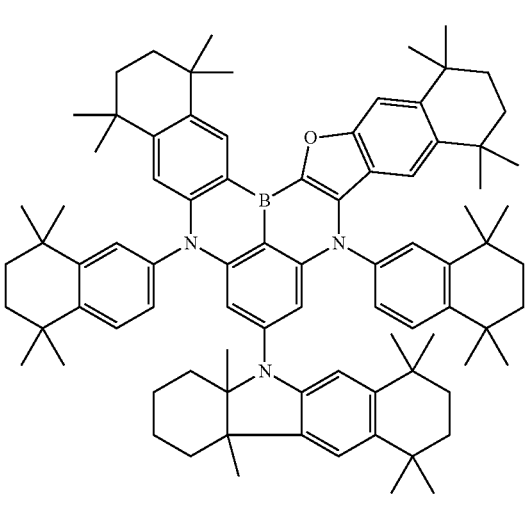

933
-continued
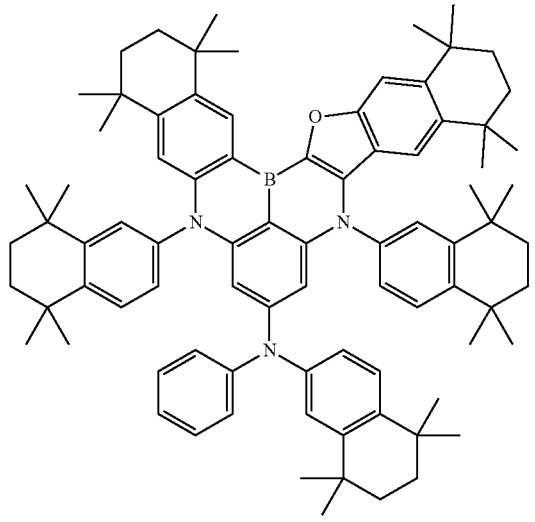
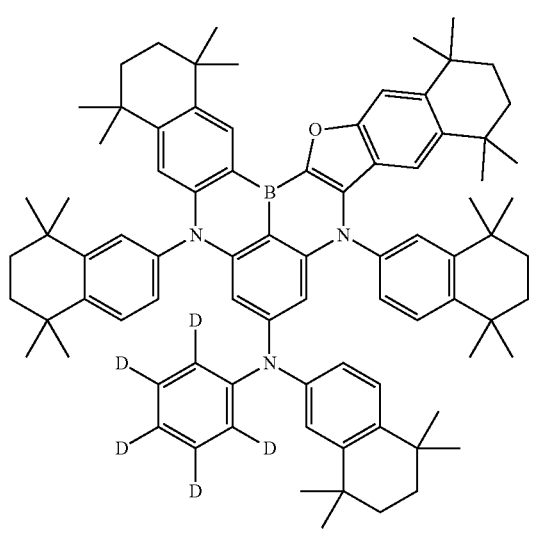
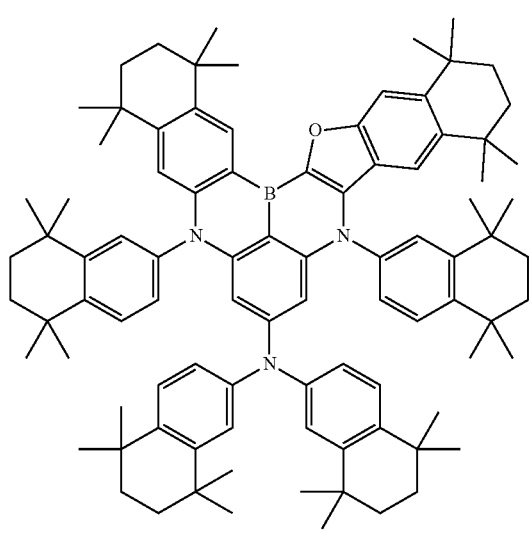
934
-continued
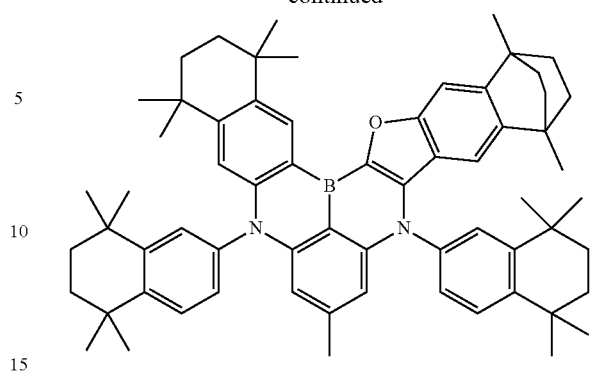
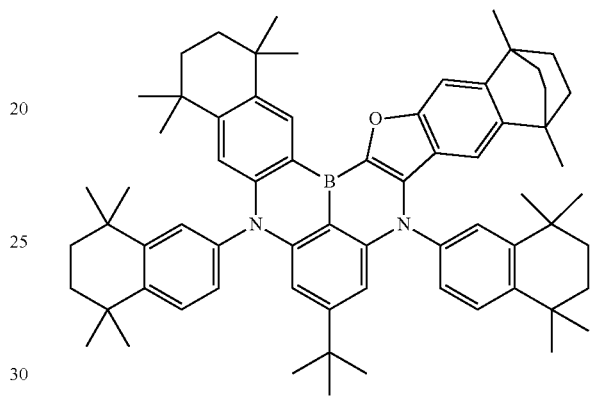
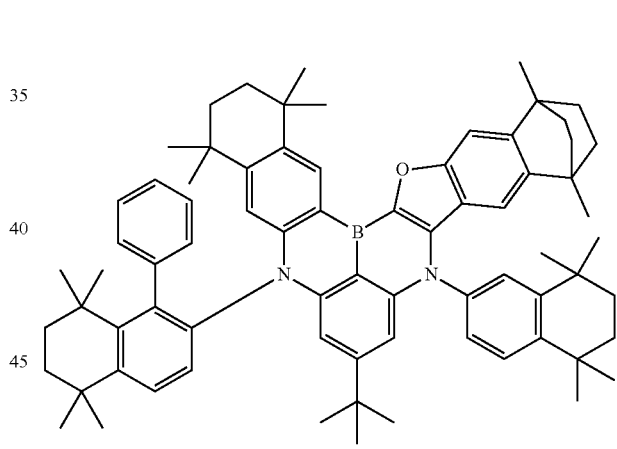
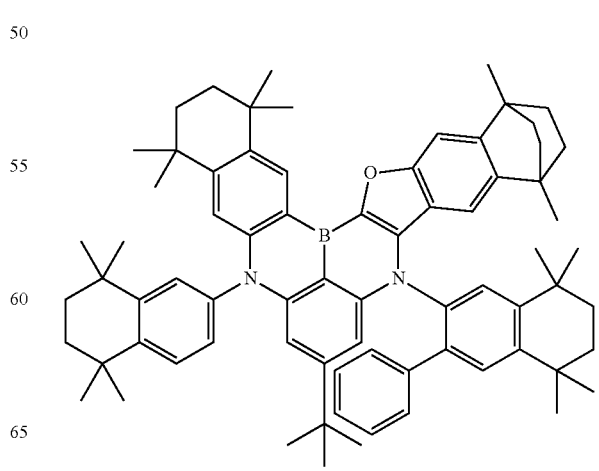

US 11,685,751 B2
| 935 -continued | 936 -continued |
|---|---|
| 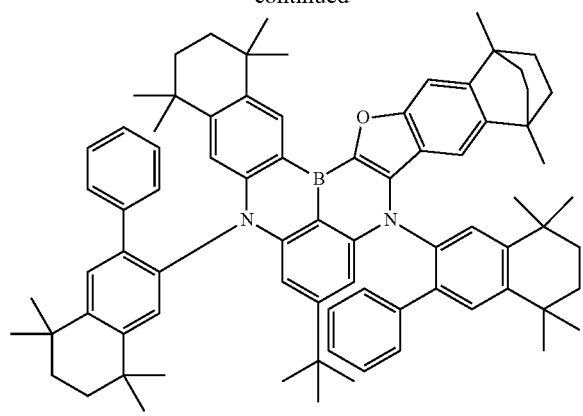 | 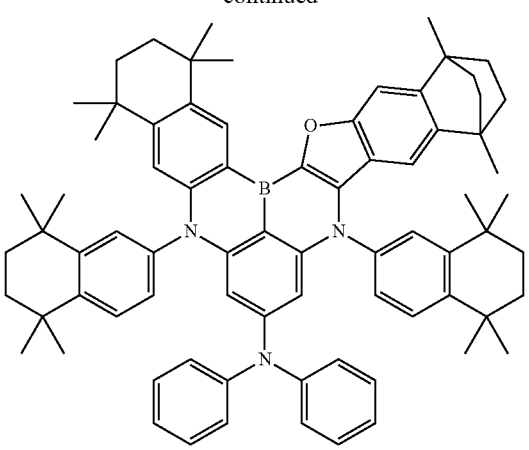 |
| 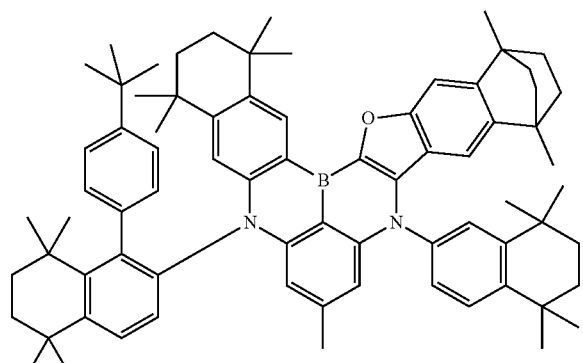 | 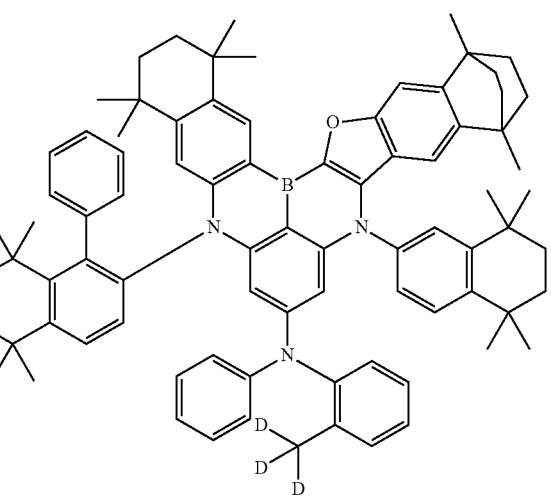 |
| 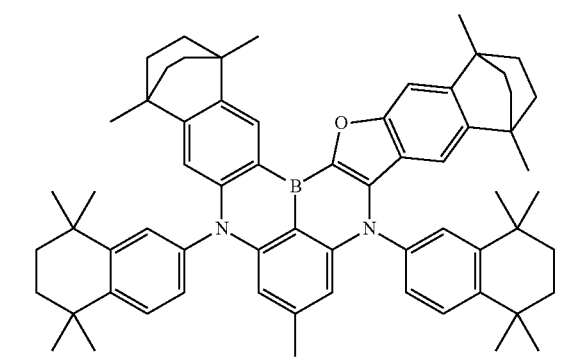 | |
| 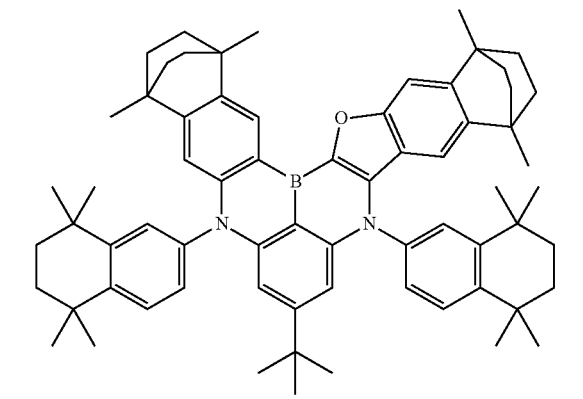 | 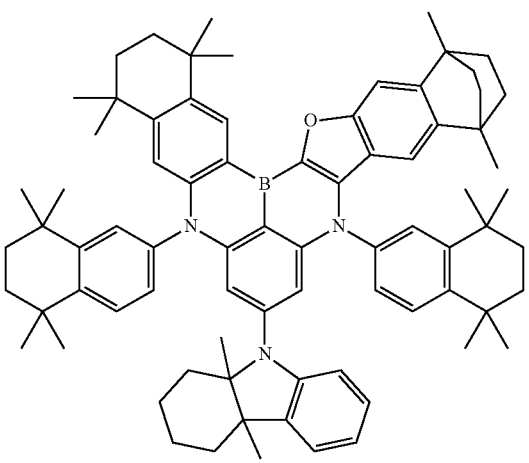 |

937
-continued
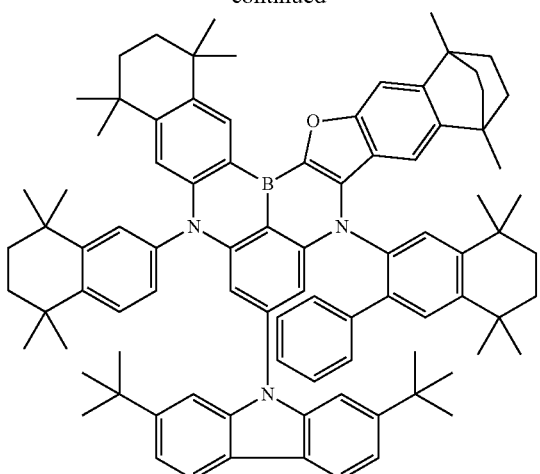
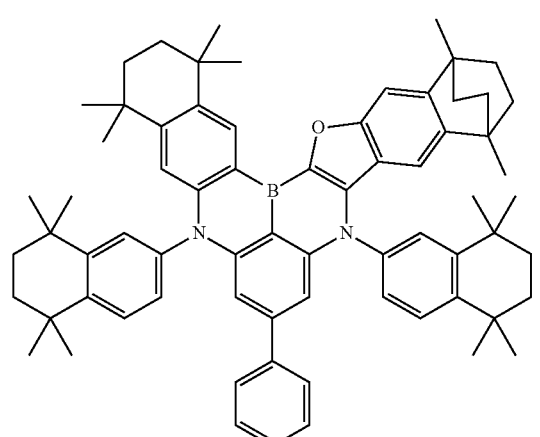
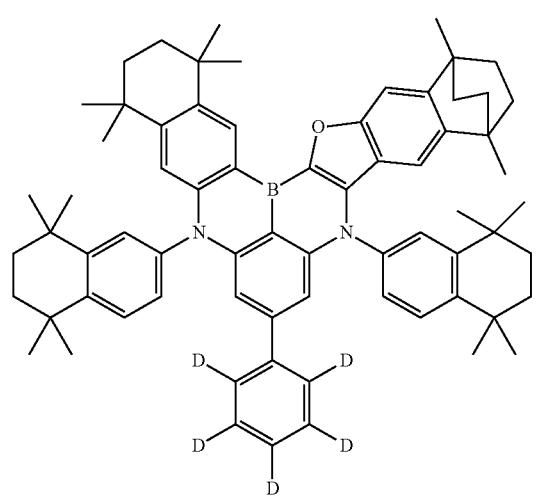
938
-continued
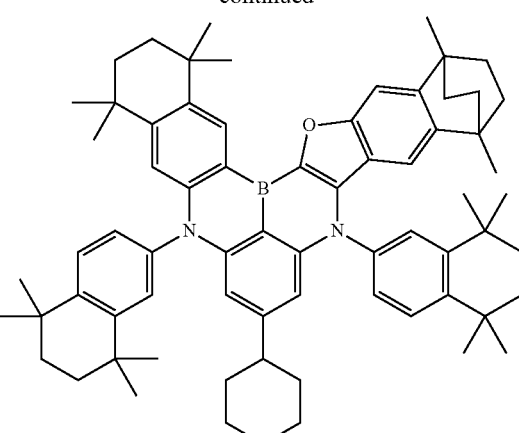
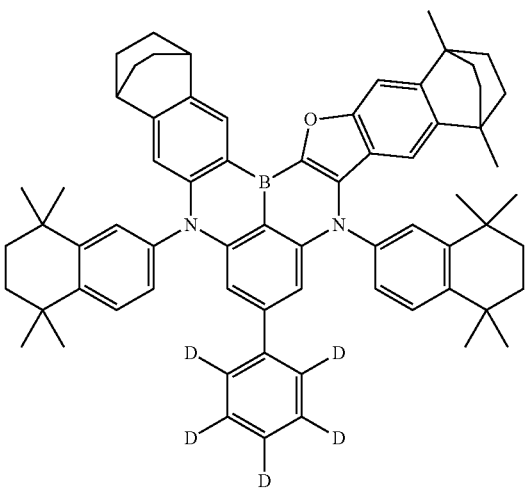
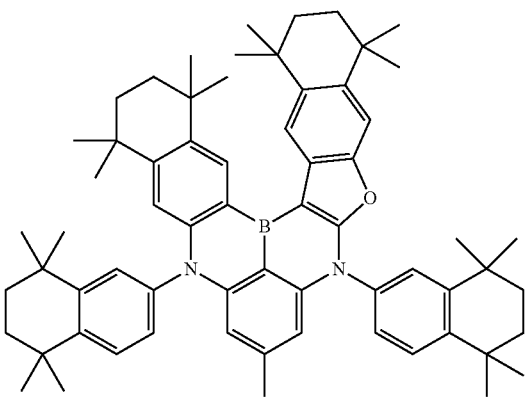

939
-continued
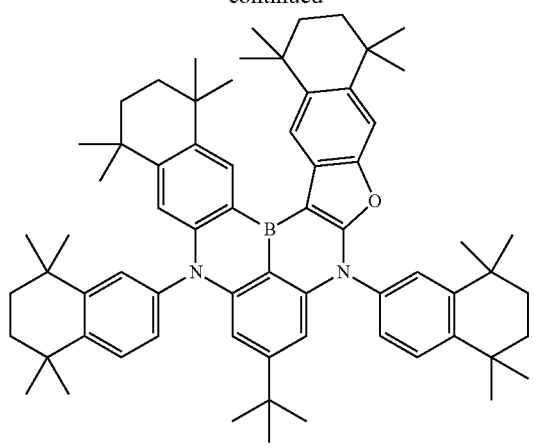
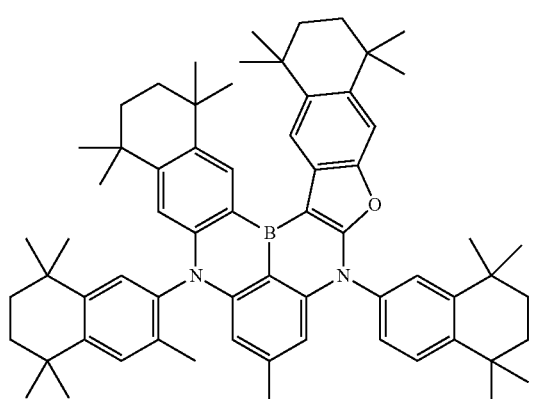
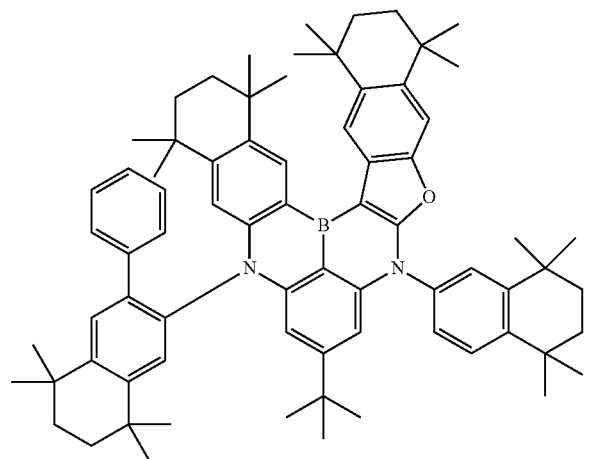
940
-continued
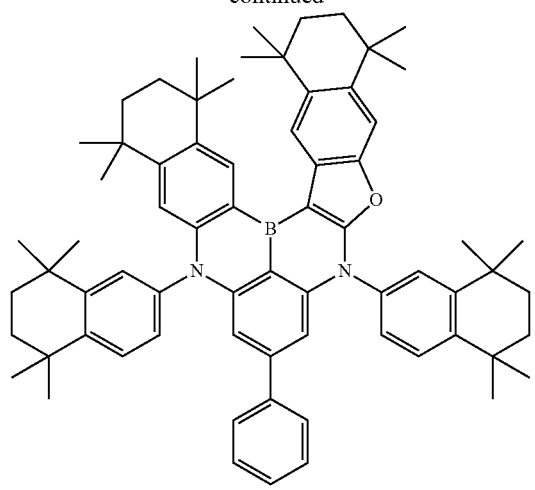
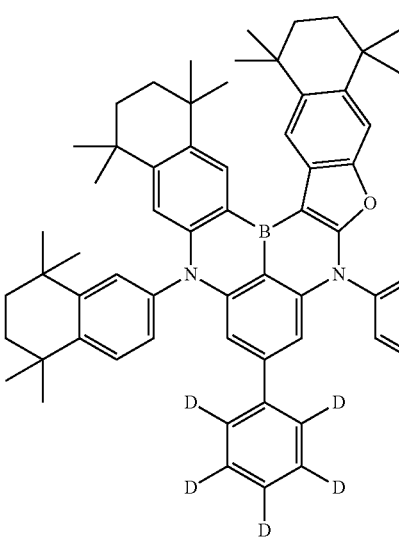
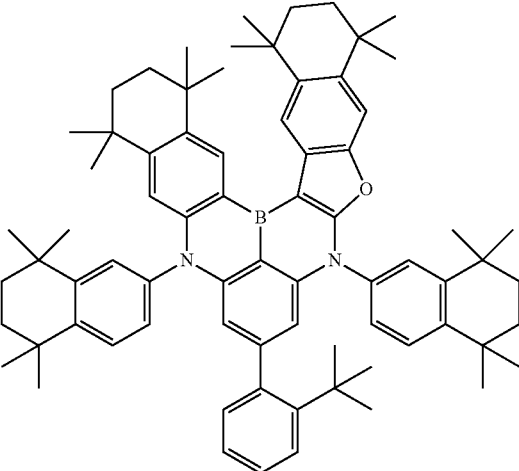

| 941 -continued | 942 -continued |
|---|---|
| 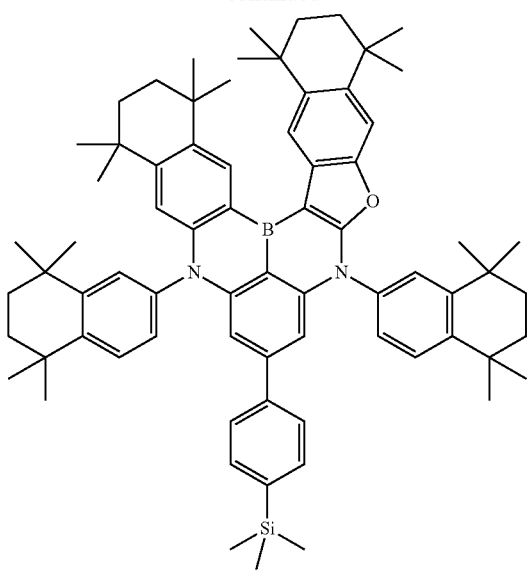 | 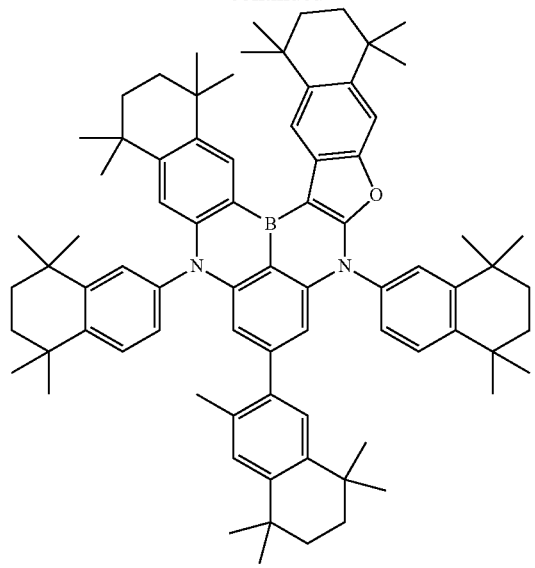 |
| 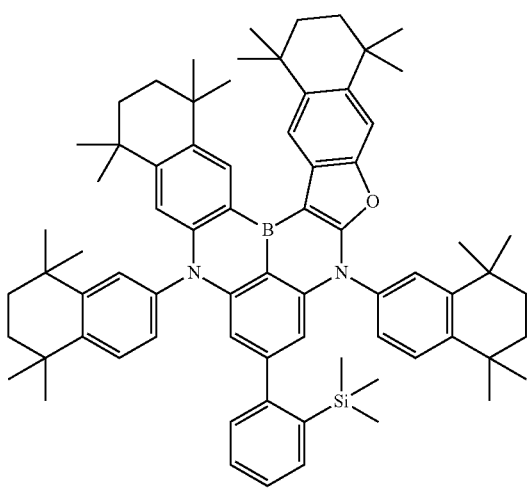 | 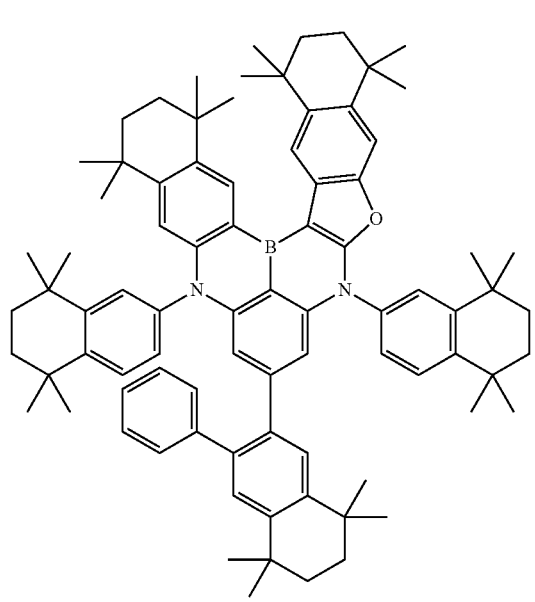 |
| 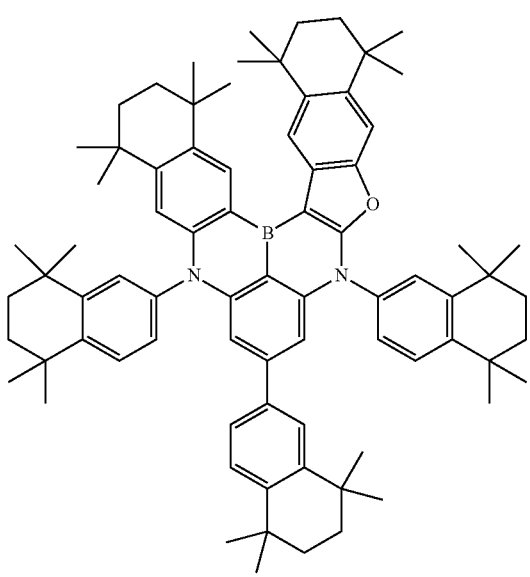 | 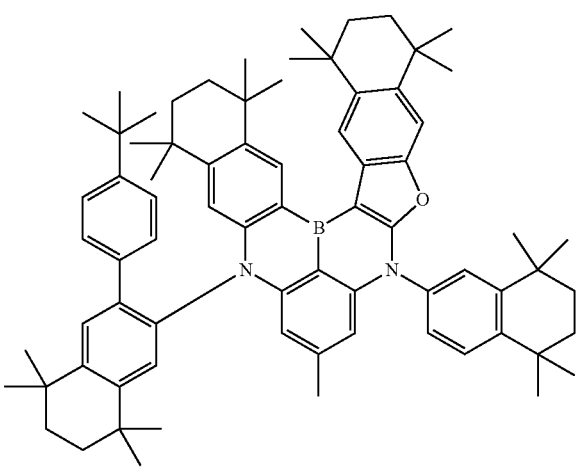 |

943
-continued
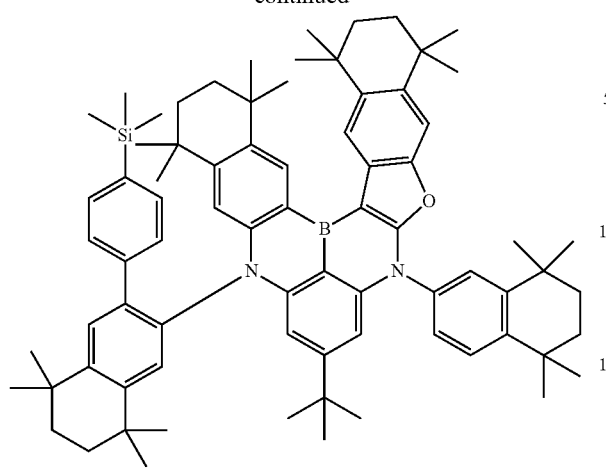
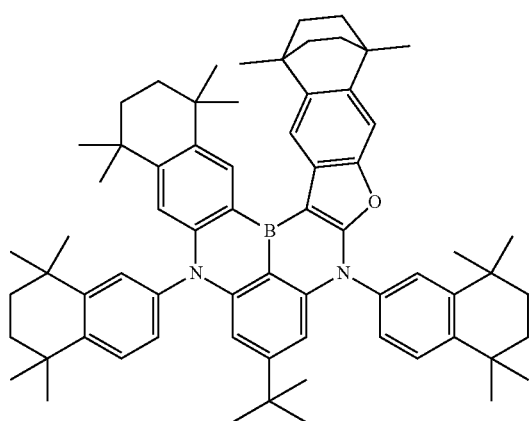
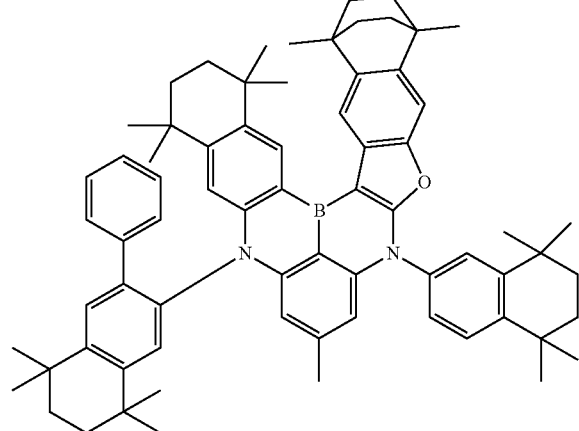
944
-continued
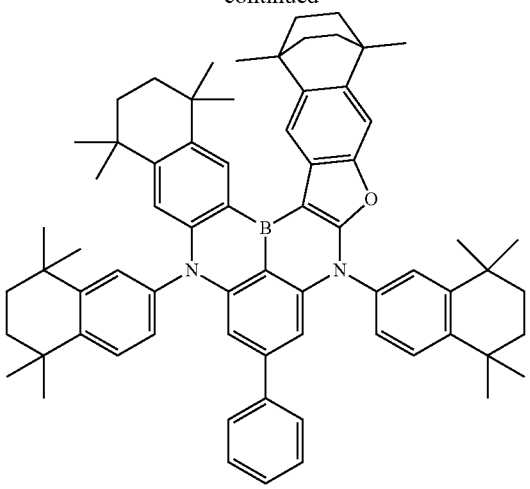
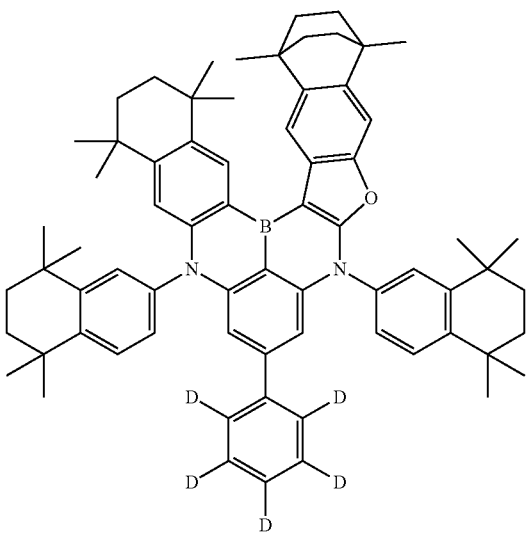
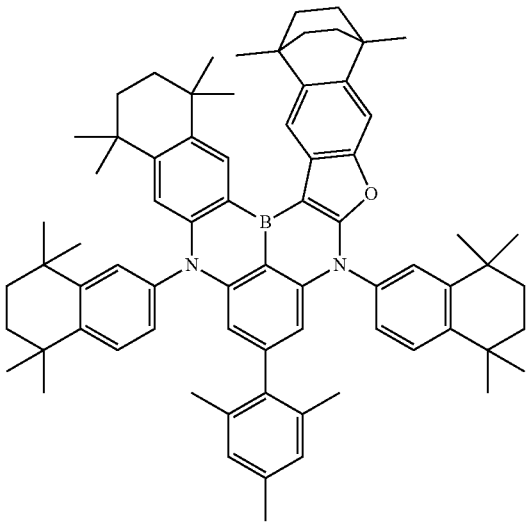

945
-continued
946
-continued
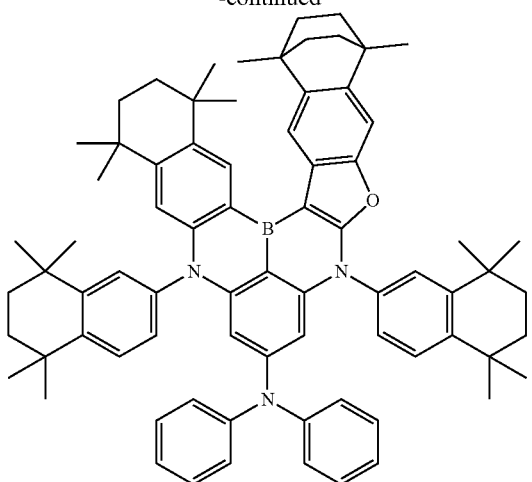
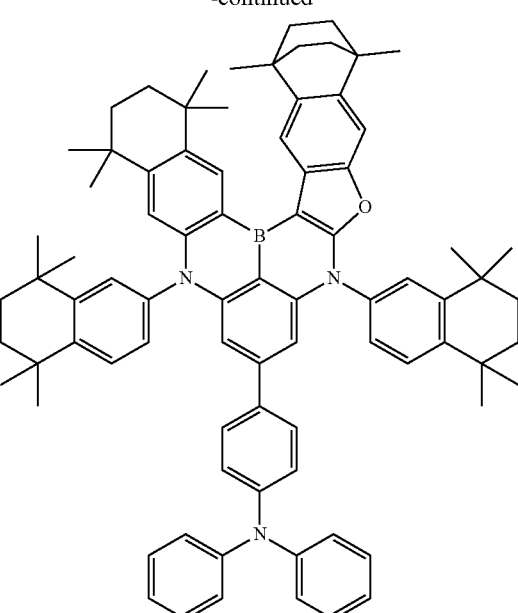
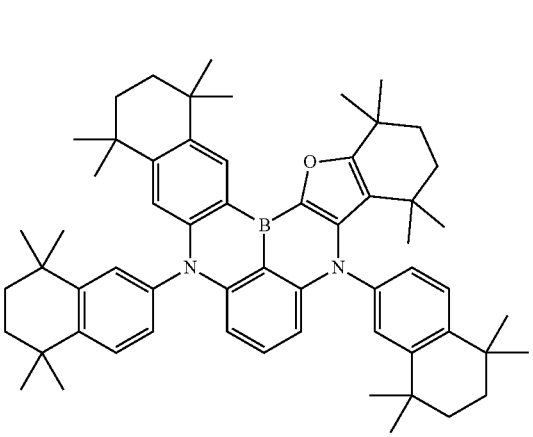
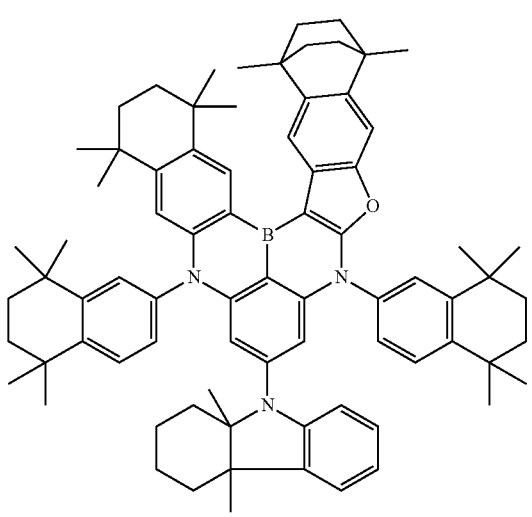
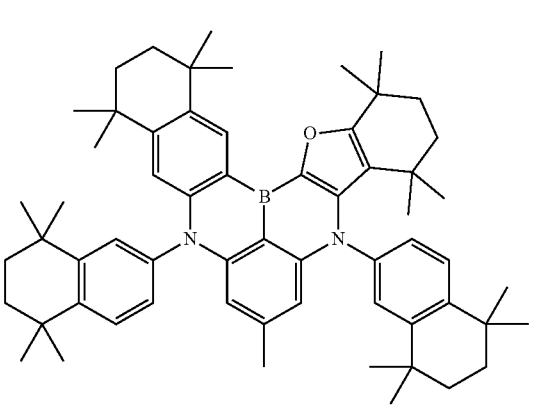

| 947 -continued | 948 -continued |
|---|---|
| 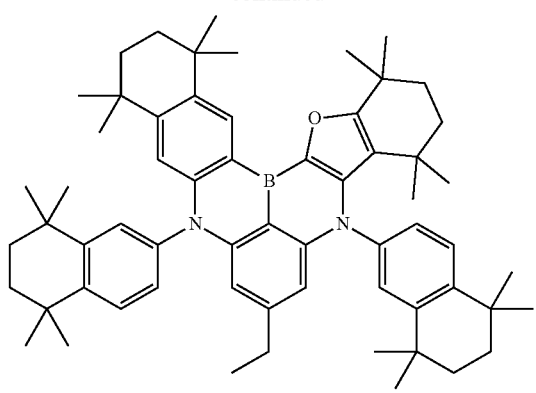 | 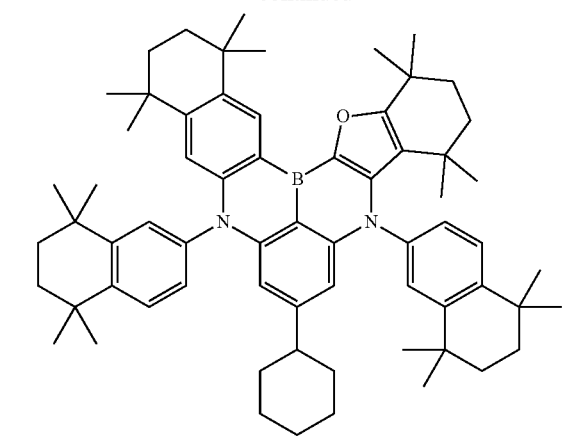 |
| 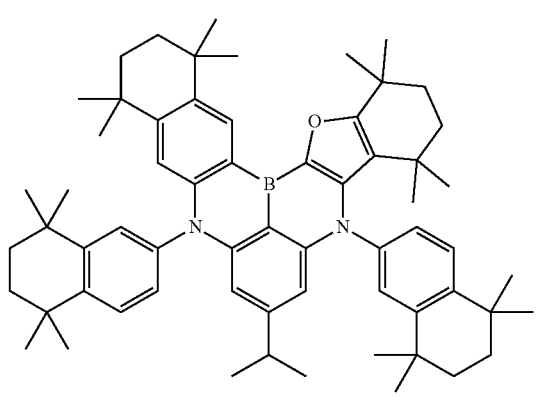 | 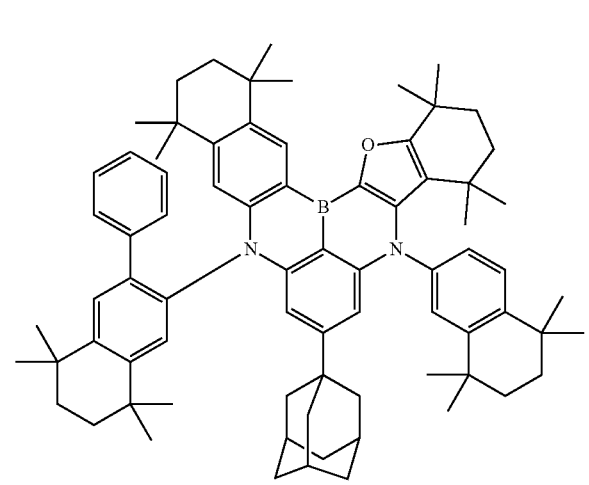 |
| 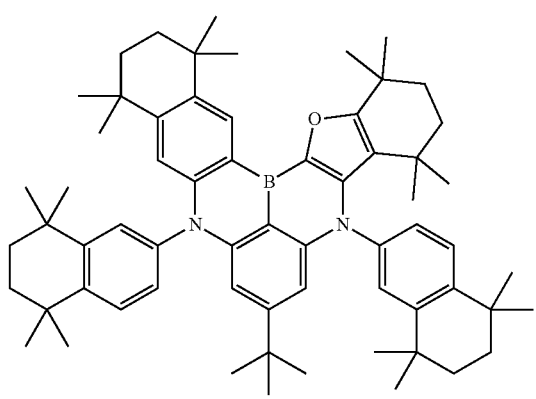 | 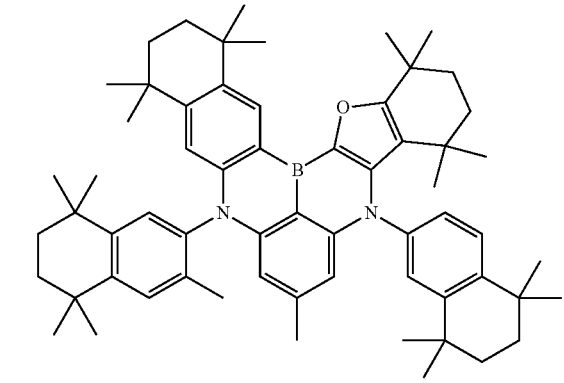 |
| 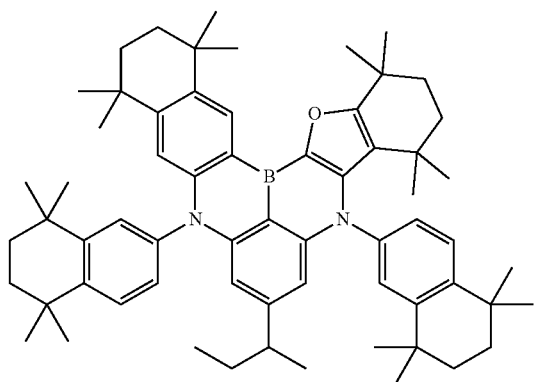 | 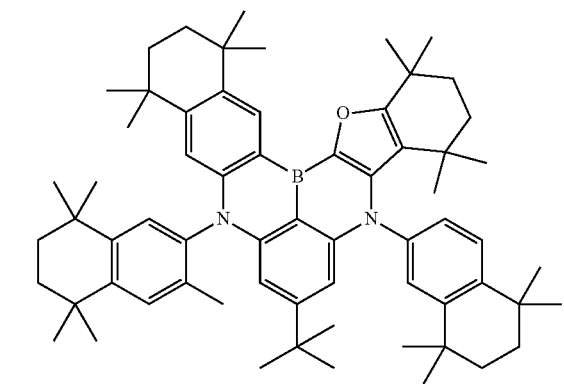 |

949
-continued
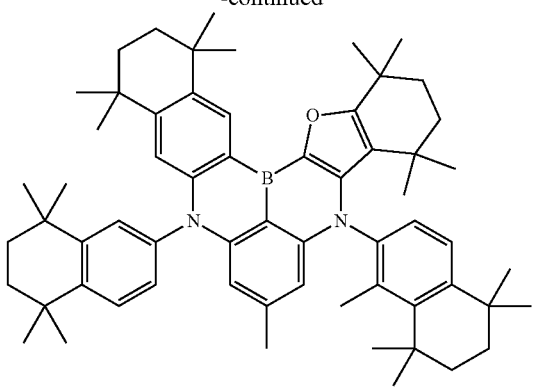
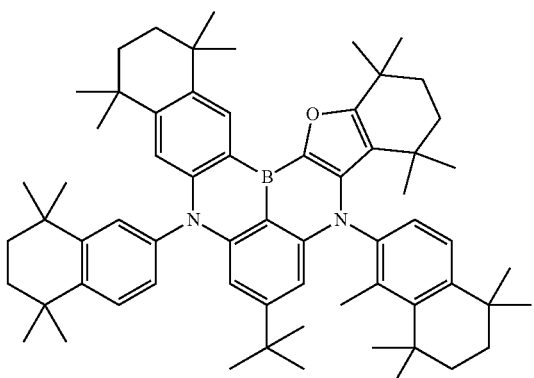
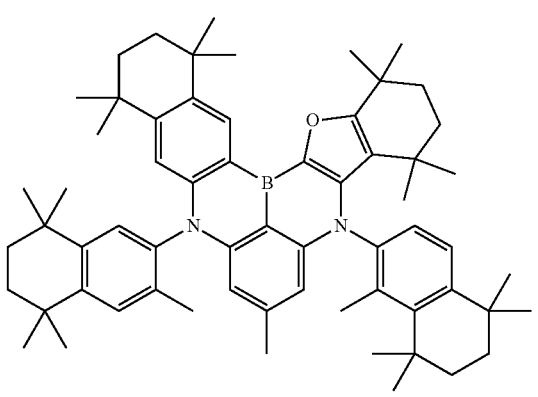
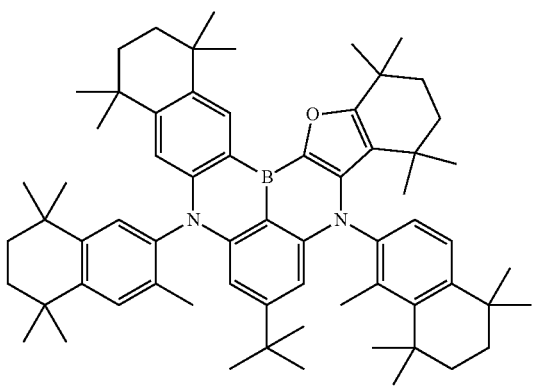
950
-continued
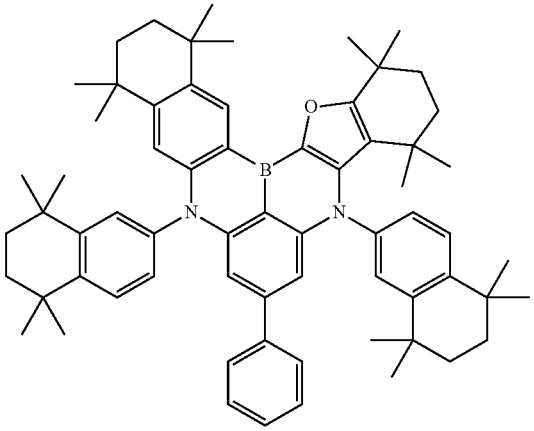
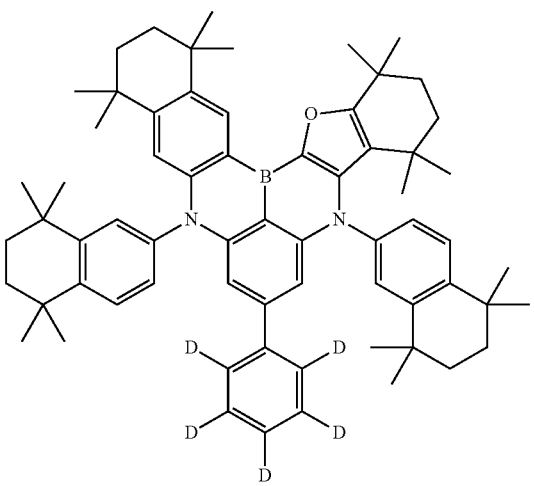
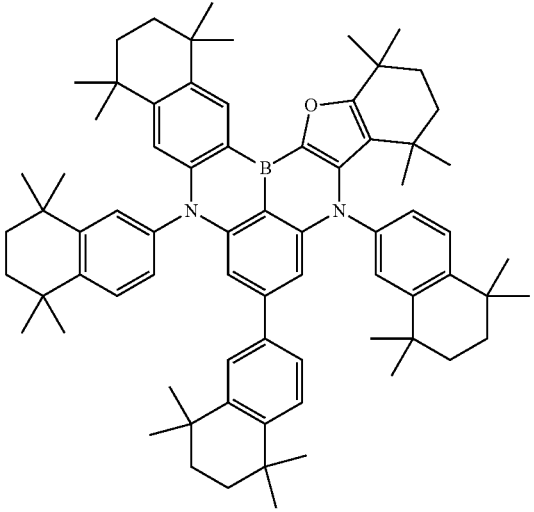

| 951 -continued | 952 -continued |
|---|---|
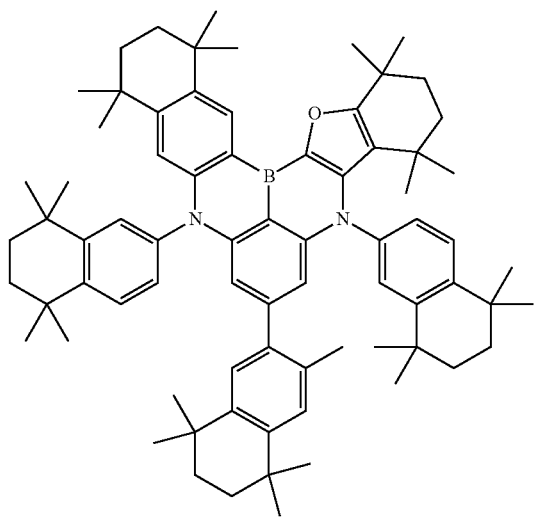
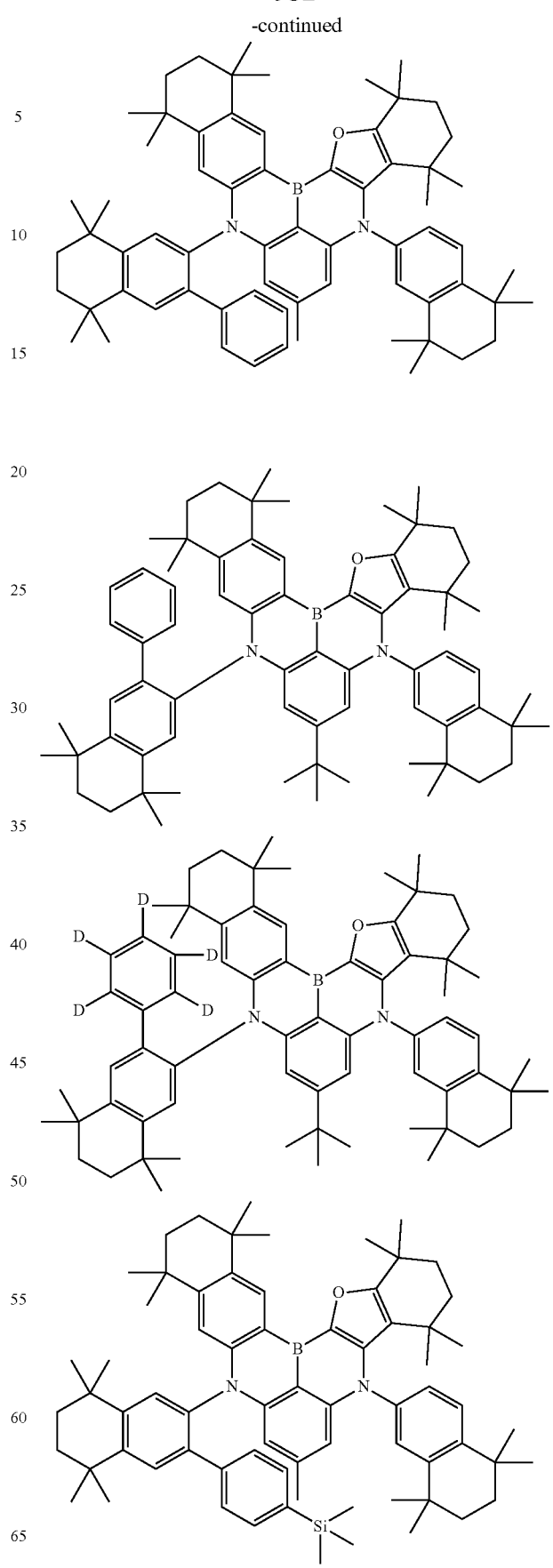

953
-continued
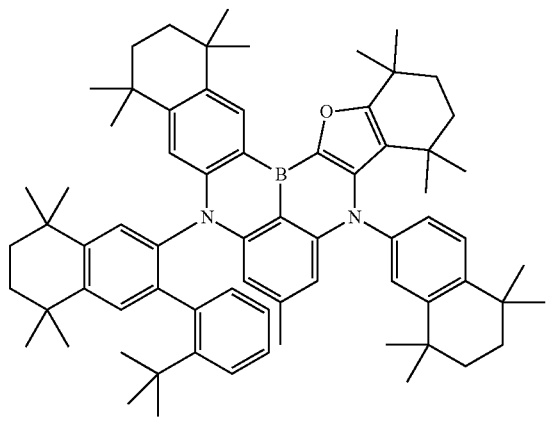
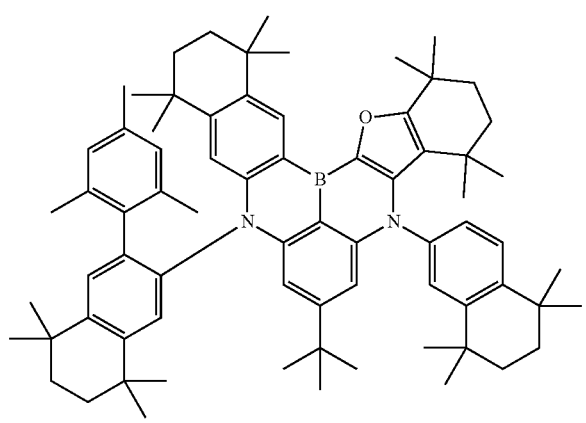
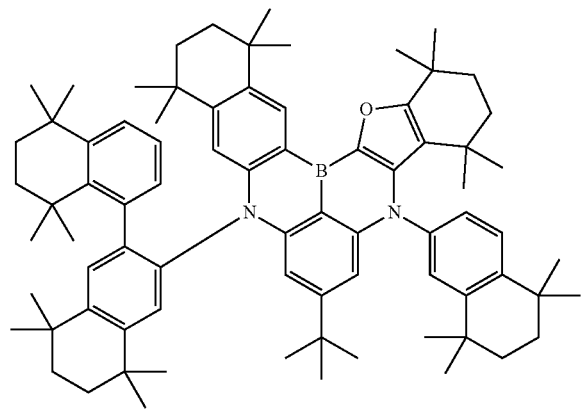
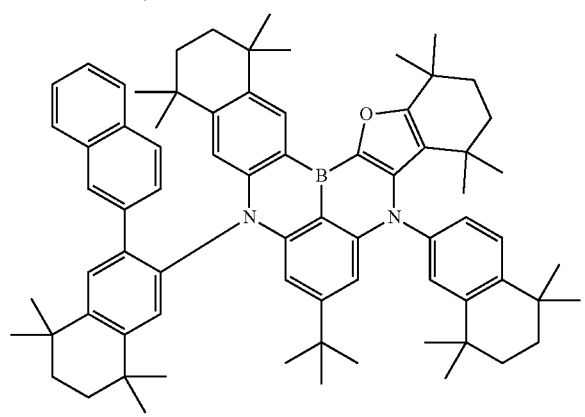
954
-continued
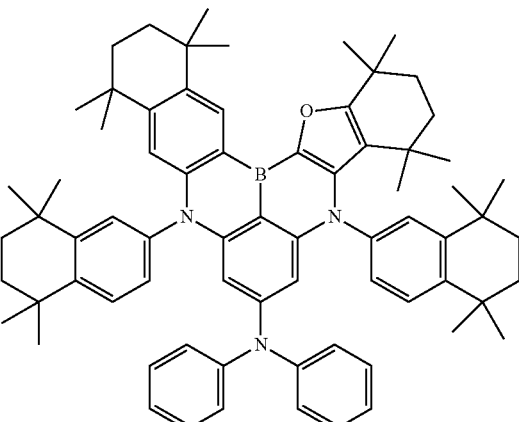
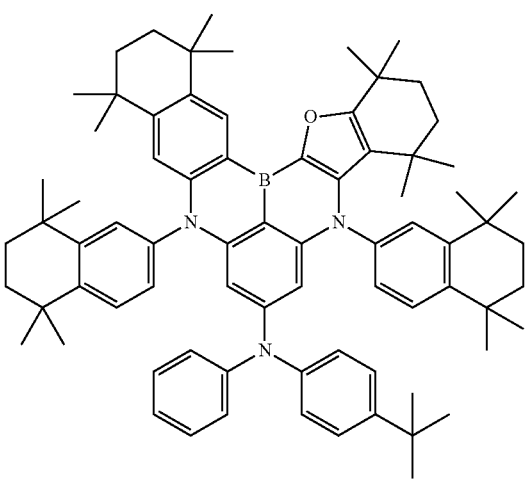
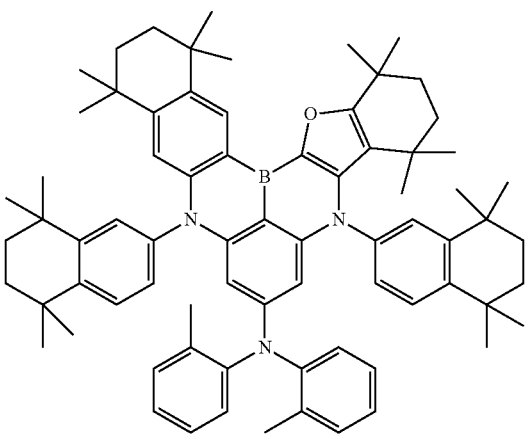

| 955 -continued | 956 -continued |
|---|---|
| 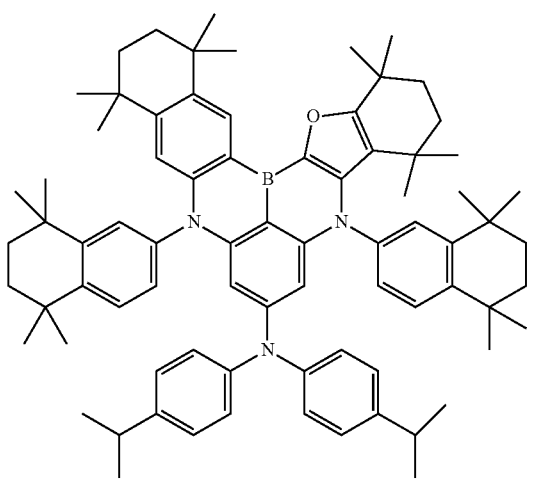 | 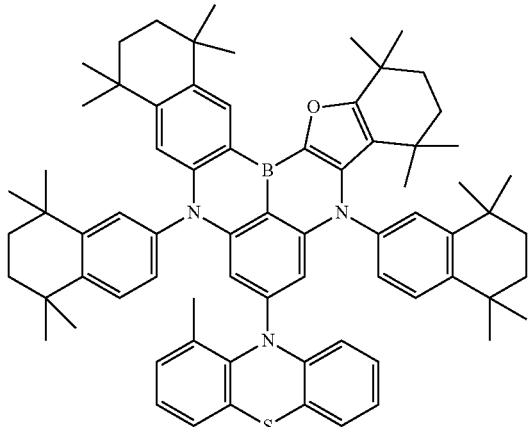 |
| 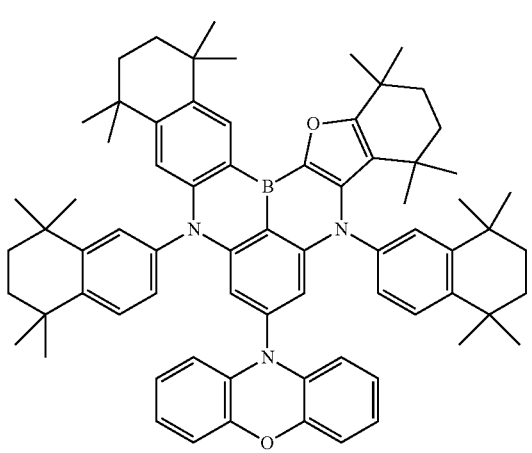 | 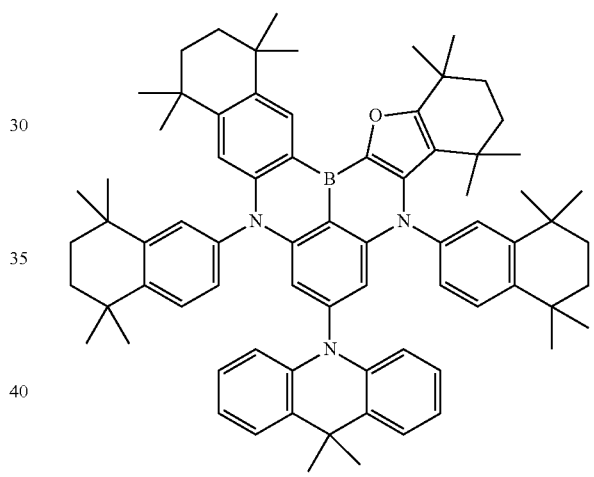 |
| 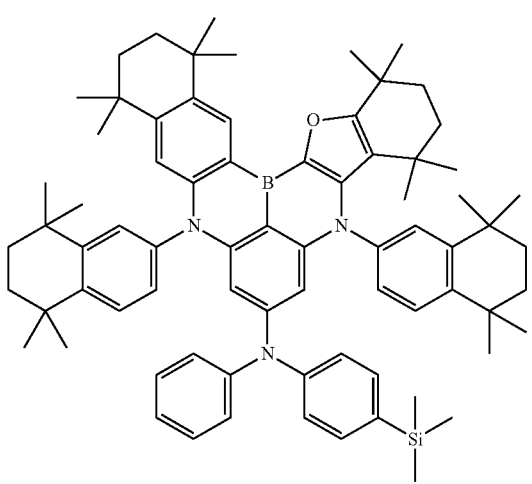 | 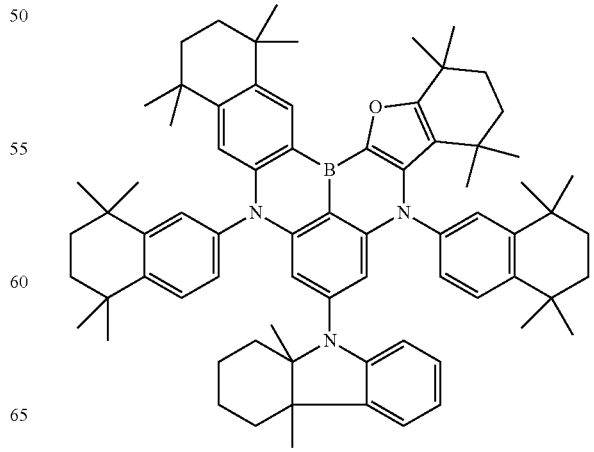 |

| 957 -continued | 958 -continued |
|---|---|
| 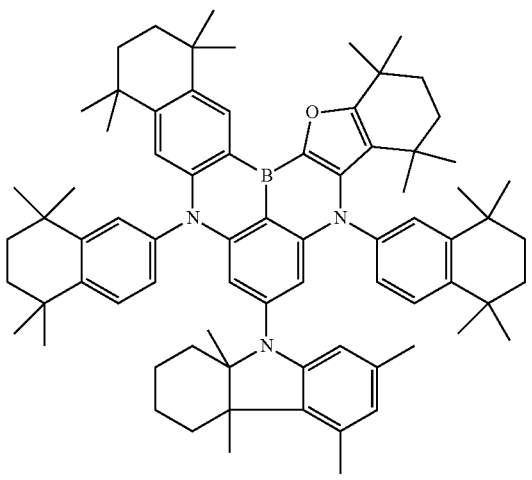 | 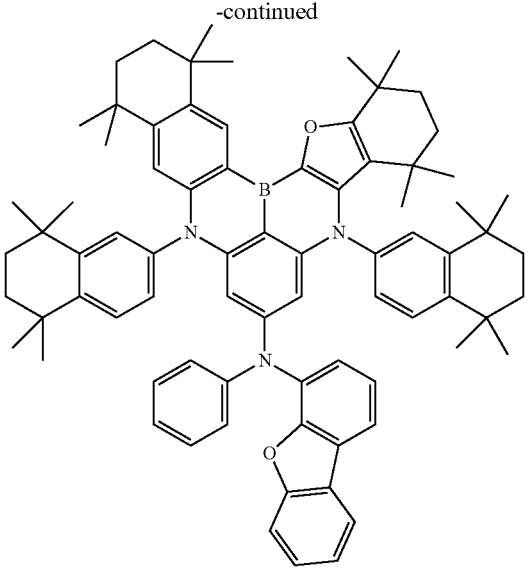 |
| 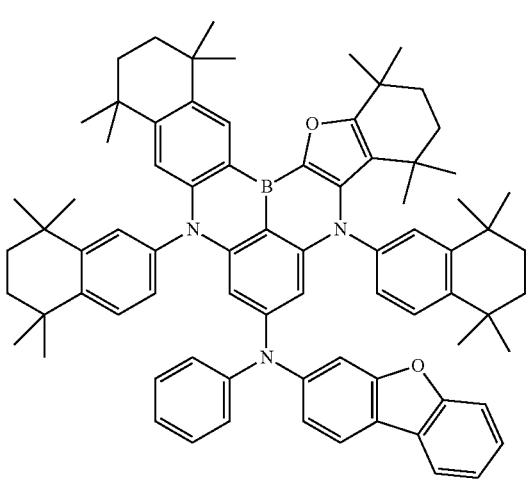 | 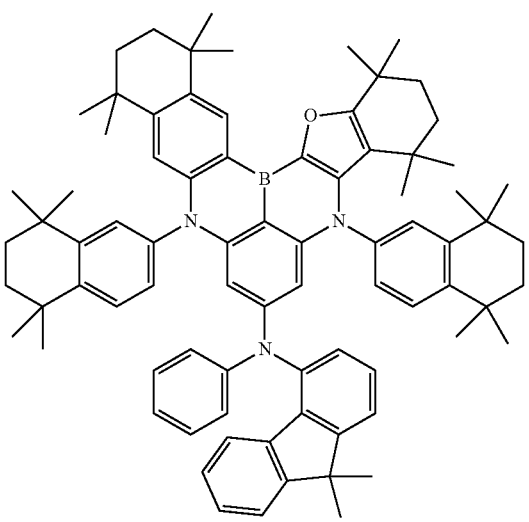 |
| 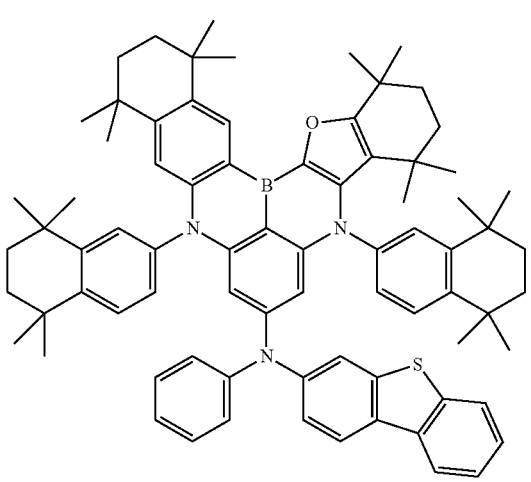 | 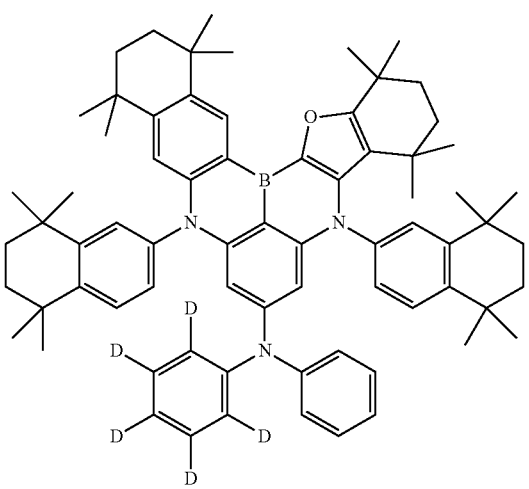 |

959
-continued
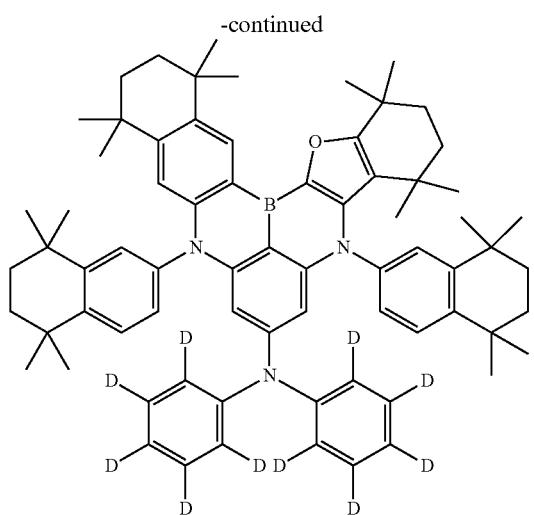
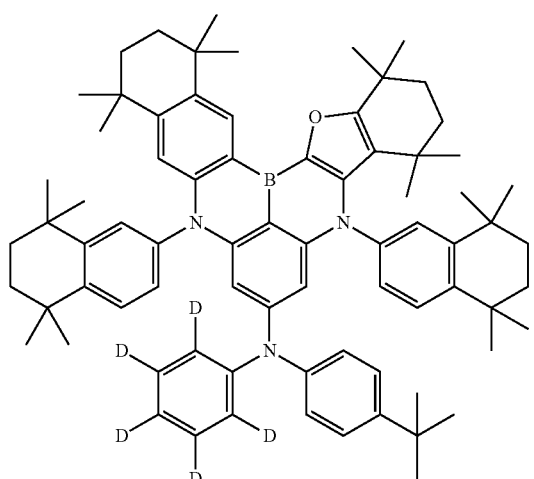
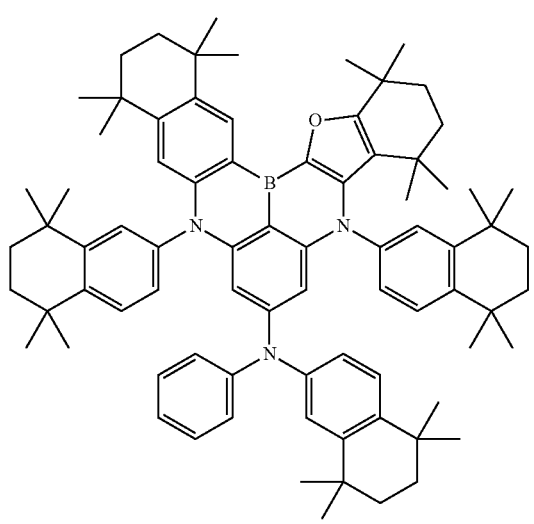
960
-continued
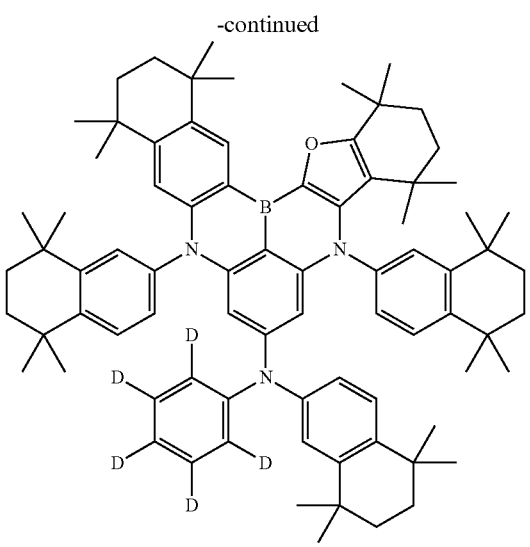
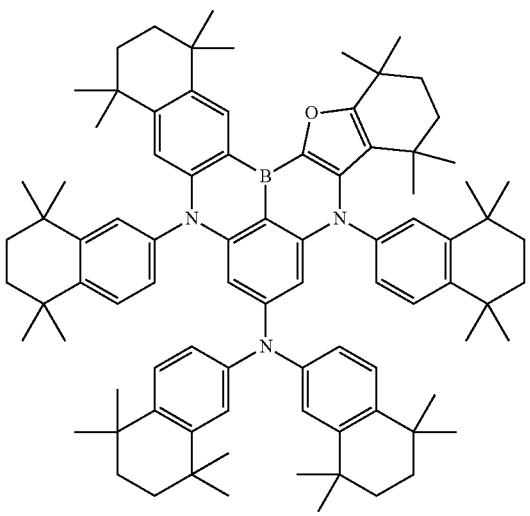
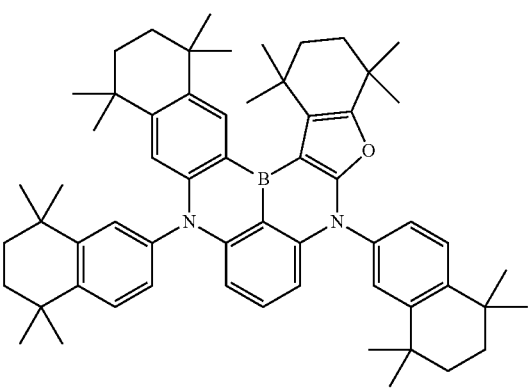

961
-continued
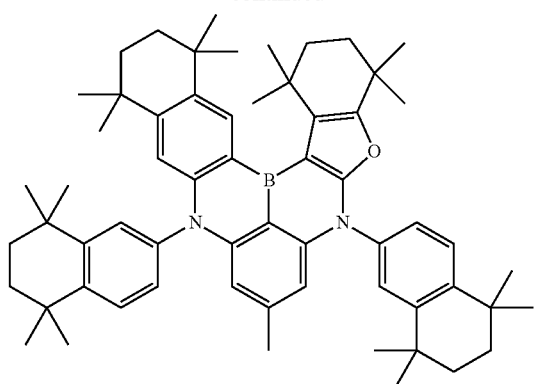
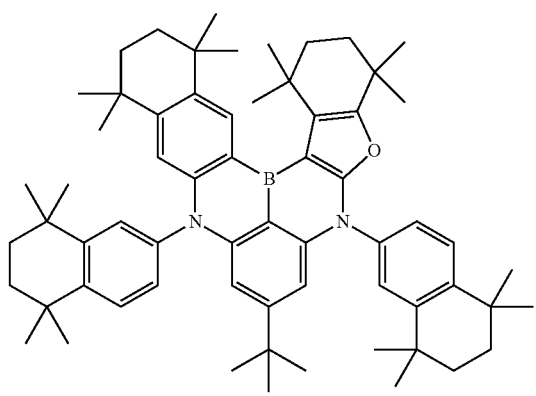
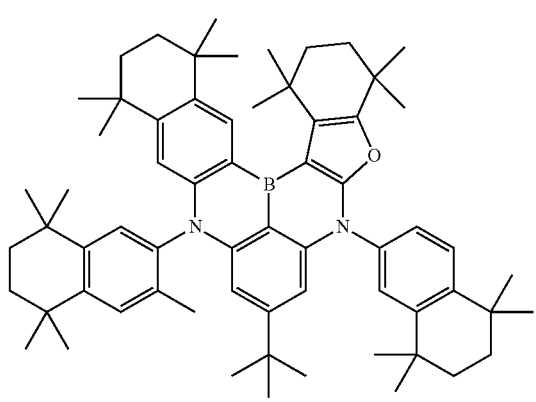
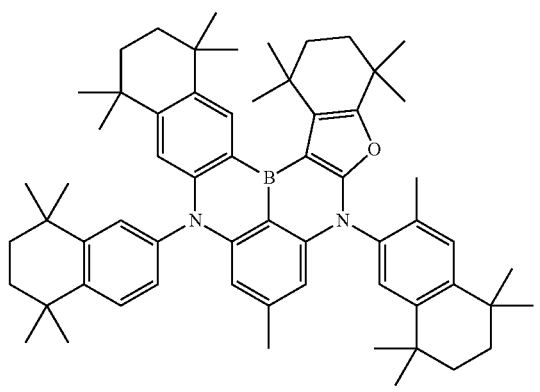
962
-continued
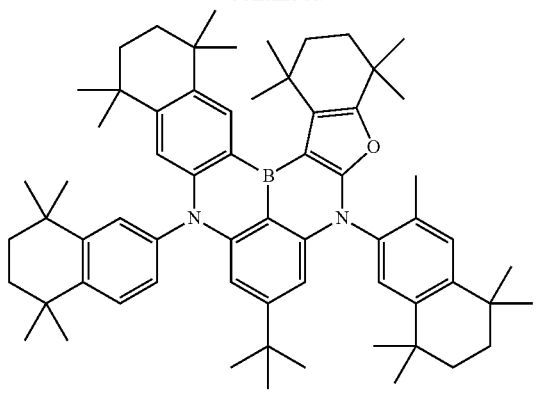
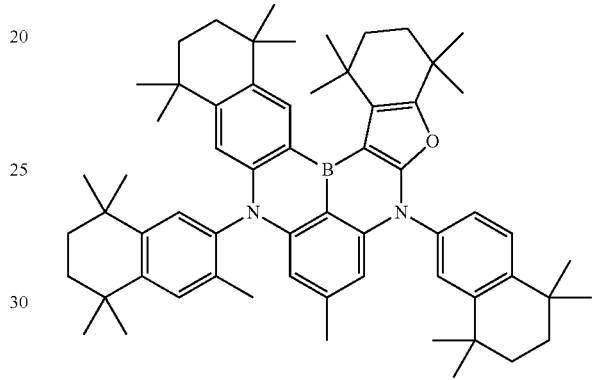
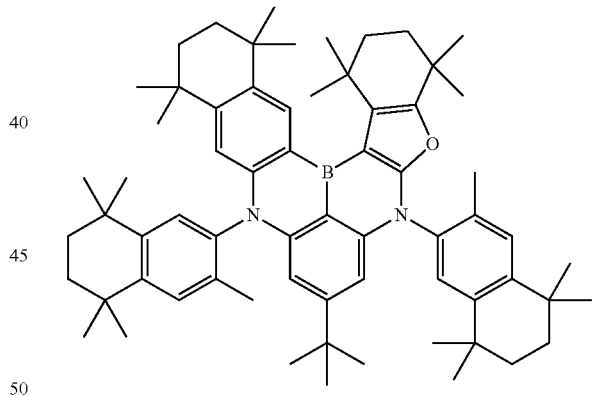
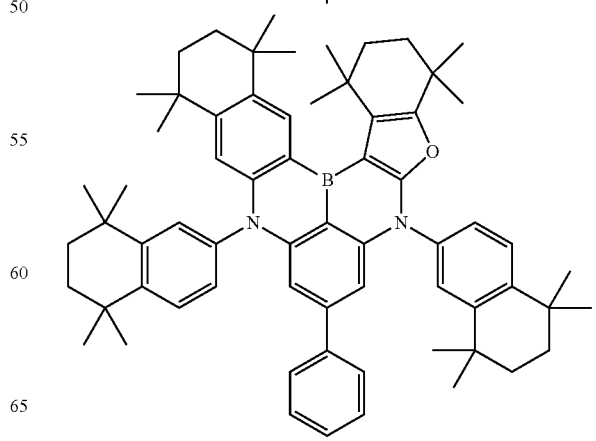

963
-continued
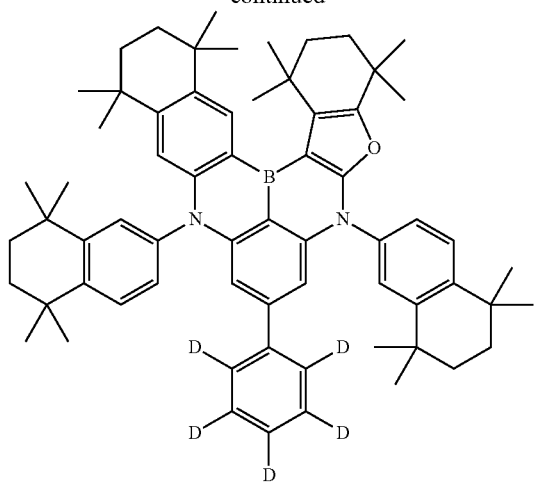
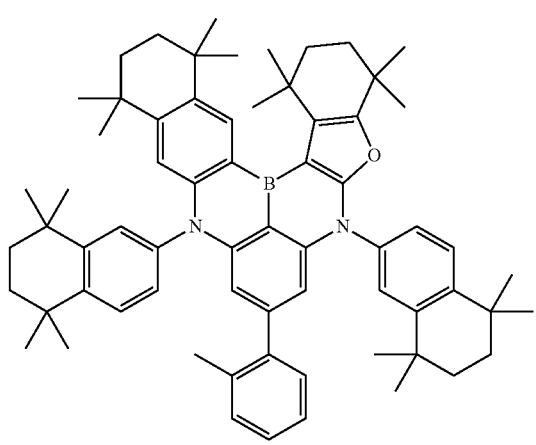
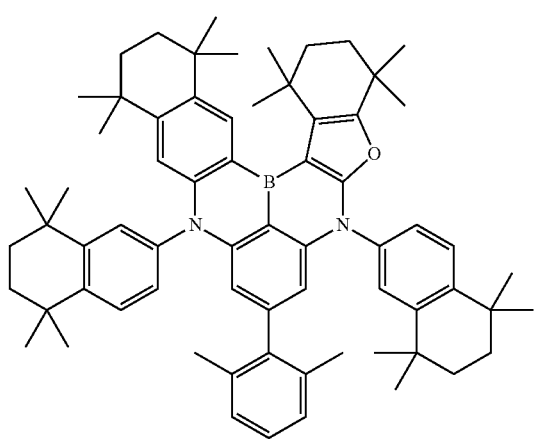
964
-continued
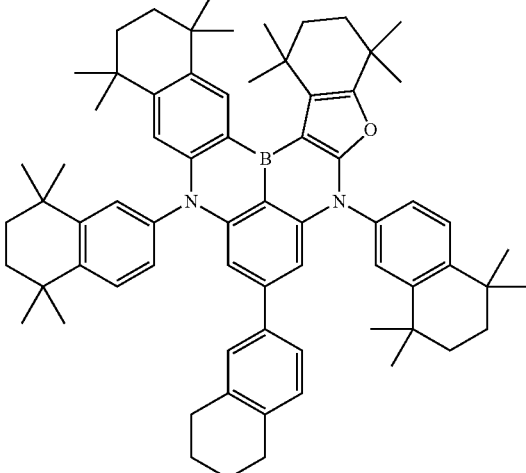
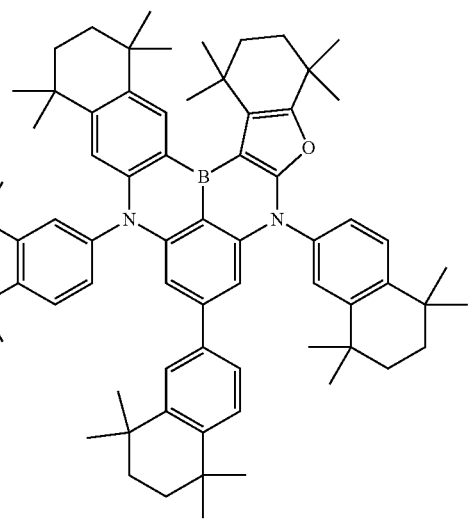
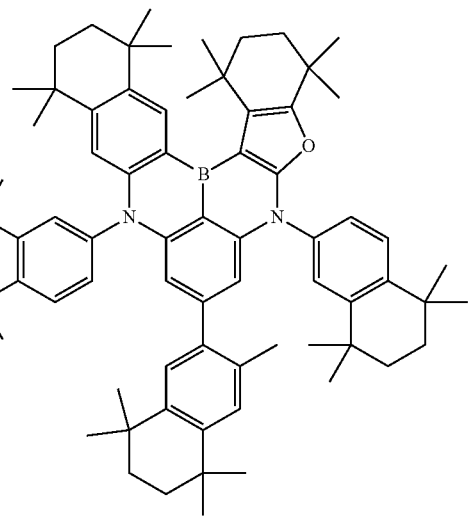

965
-continued
966
-continued
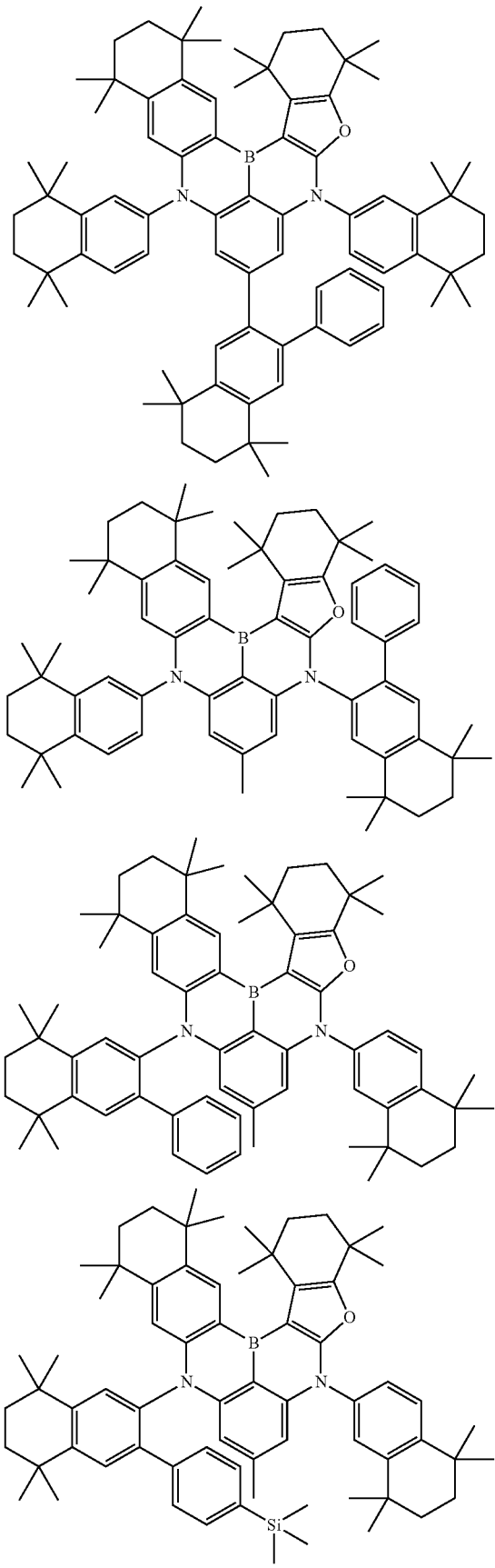
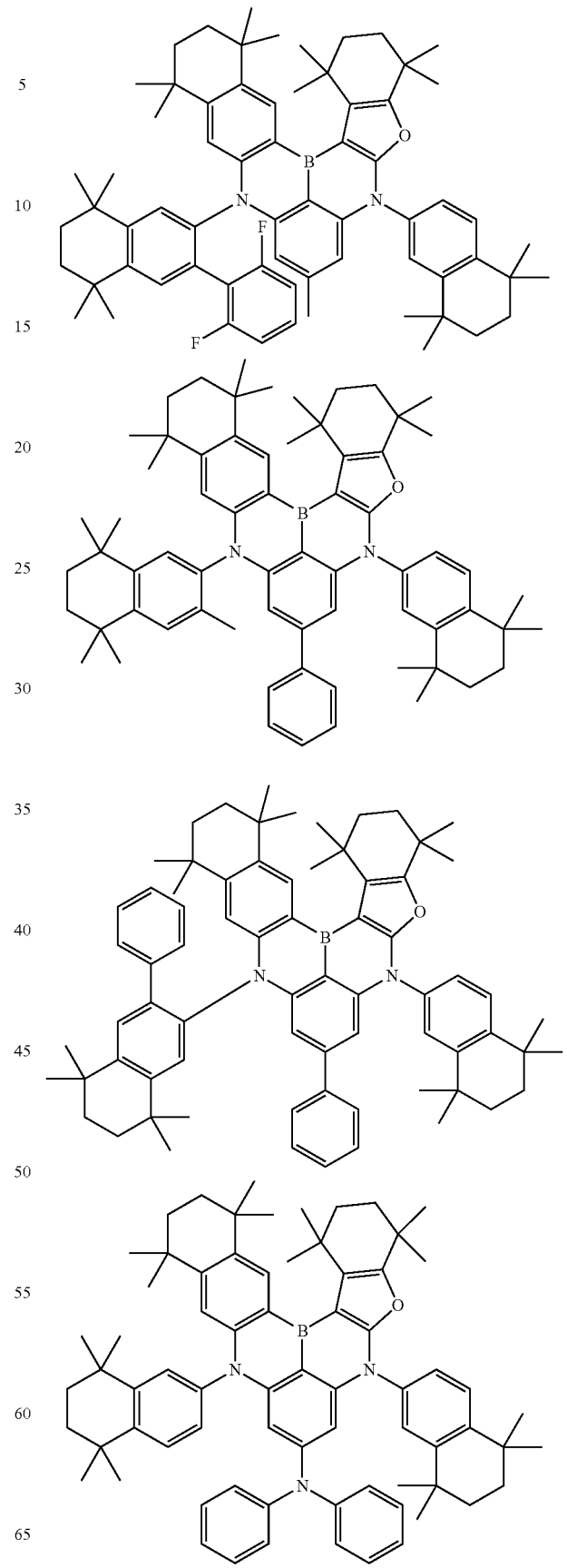

967

-continued

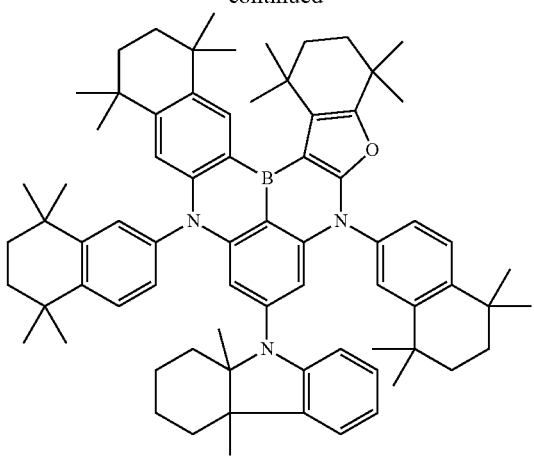

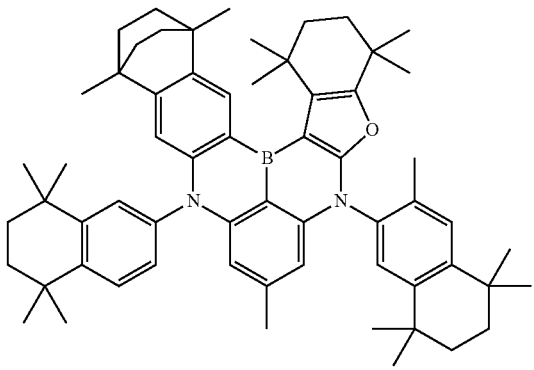

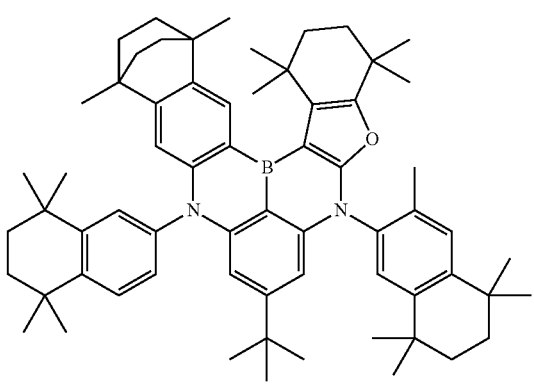

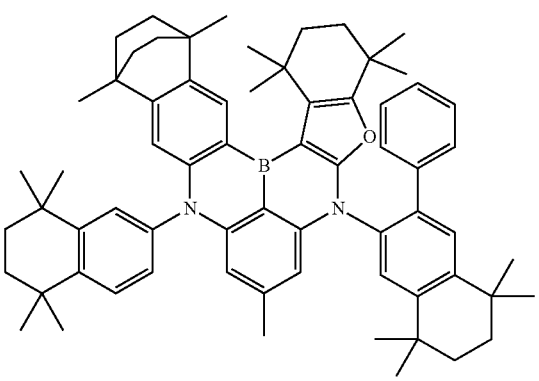

968

-continued

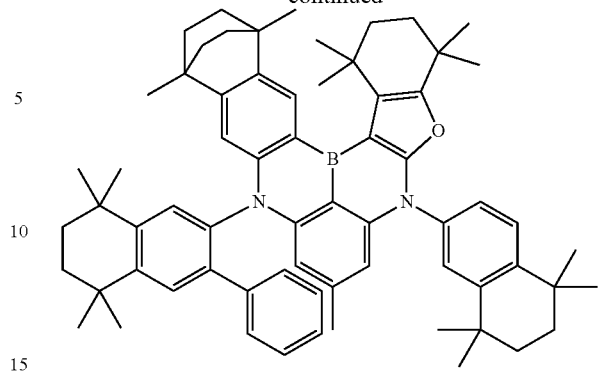

In the compounds, Ph is a phenyl group, and D is deuterium.

One embodiment of the present specification provides an organic light emitting device including the compound described above.

In the present specification, a description of a certain member being placed "on" another member includes not only a case of the one member being in contact with the another member but a case of still another member being present between the two members.

In the present specification, a description of a certain part "including" certain constituents means capable of further including other constituents, and does not exclude other constituents unless particularly stated on the contrary.

In the present specification, the "layer" has a meaning compatible with a 'film' mainly used in the art, and means coating covering a target area. The size of the "layer" is not limited, and each "layer" may have the same or a different size. According to one embodiment, the size of the "layer" may be the same as the whole device, may correspond to the size of a specific functional area, or may be as small as a single sub-pixel.

In the present specification, a meaning of a specific A material being included in a B layer includes both i) one or more types of A materials being included in one B layer, and ii) a B layer being formed in one or more layers, and an A material being included in one or more of the B layers that is a multilayer.

In the present specification, a meaning of a specific A material being included in a C layer or a D layer includes both i) being included in one or more layers of one or more C layers, ii) being included in one or more layers of one or more D layers, or iii) being included in each of one or more C layers and one or more D layers.

In the present specification, "deuteration", "substituted with deuterium" or "deuterated" means hydrogen at a substitutable position of a compound being substituted with deuterium.

In the present specification, "X % substituted with deuterium", "X % deuterated", "degree of deuteration of X %", or "deuterium substitution rate of X %" means, in the corresponding structure, X % of hydrogens at substitutable positions being substituted with deuterium. For example, when the corresponding structure is dibenzofuran, the dibenzofuran being "substituted with deuterium by 25%", the dibenzofuran being "25% deuterated", the dibenzofuran having a "degree of deuteration of 25%", or the dibenzofuran having a "deuterium substitution rate of 25%" means two of eight hydrogens at substitutable positions of the dibenzofuran being substituted with deuterium.

In the present specification, the degree of deuteration may be identified using known methods such as nuclear magnetic resonance spectroscopy ($^1$H NMR), TLC/MS (thin-layer chromatography/mass spectrometry) or MALDI-TOF MS (matrix assisted laser desorption/ionization time-of-flight mass spectrometry).

One embodiment of the present specification provides an organic light emitting device including a first electrode; a second electrode provided opposite to the first electrode; and an organic material layer including one or more layers provided between the first electrode and the second electrode, wherein one or more layers of the organic material layer include the compound represented by Chemical Formula 1.

The organic material layer of the organic light emitting device of the present specification may be formed in a single layer structure, but may also be formed in a multilayer structure in which two or more layers are stacked. For example, the organic light emitting device of the present specification may have a structure including a hole injection layer, a hole transfer layer, a light emitting layer, an electron transfer layer, an electron injection layer, an electron blocking layer, a hole blocking layer and the like. However, the structure of the organic light emitting device is not limited thereto, and may include a smaller number of organic layers.

In one embodiment of the present specification, the organic material layer includes a light emitting layer, and the light emitting layer includes the compound represented by Chemical Formula 1.

In one embodiment of the present specification, the organic material layer includes a light emitting layer, and the light emitting layer includes the compound represented by Chemical Formula 1 as a dopant of the light emitting layer.

In one embodiment of the present specification, the organic material layer includes a light emitting layer, and the light emitting layer includes the compound represented by Chemical Formula 1 as a blue fluorescent dopant of the light emitting layer.

In one embodiment of the present specification, the organic light emitting device further includes one, two or more layers selected from the group consisting of a hole injection layer, a hole transfer layer, a light emitting layer, an electron transfer layer, an electron injection layer, a hole blocking layer and an electron blocking layer.

In one embodiment of the present specification, the light emitting layer further includes a host compound.

In one embodiment of the present specification, the light emitting layer further includes a host compound, and in the host compound, at least one hydrogen at a substitutable position is substituted with deuterium.

In one embodiment of the present specification, when the host compound is substituted with deuterium, the host compound is substituted with deuterium by 30% or more. In another embodiment, the host compound is substituted with deuterium by 40% or more. In another embodiment, the host compound is substituted with deuterium by 60% or more. In another embodiment, the host compound is substituted with deuterium by 80% or more. In another embodiment, the host compound is substituted with deuterium by 100%.

In one embodiment of the present specification, the light emitting layer further includes a compound represented by the following Chemical Formula H.

[Chemical Formula H]

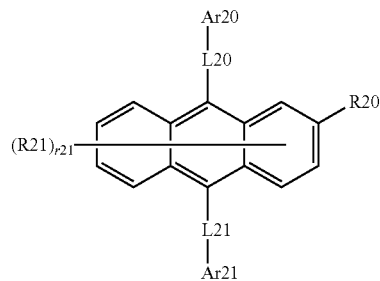

In Chemical Formula H,

L20 and L21 are the same as or different from each other, and each independently a direct bond; a substituted or unsubstituted arylene group; or a substituted or unsubstituted heteroarylene group, Ar20 and Ar21 are the same as or different from each other, and each independently hydrogen; deuterium; a substituted or unsubstituted aryl group; or a substituted or unsubstituted heterocyclic group, R20 and R21 are the same as or different from each other, and each independently hydrogen; deuterium; a halogen group; a substituted or unsubstituted alkyl group; a substituted or unsubstituted cycloalkyl group; a substituted or unsubstituted aryl group; or a substituted or unsubstituted heterocyclic group, and r21 is an integer of 1 to 7, and when r21 is 2 or greater, the two or more R21s are the same as or different from each other.

In one embodiment of the present specification, L20 and L21 are the same as or different from each other, and each independently a direct bond; a monocyclic or polycyclic arylene group having 6 to 30 carbon atoms; or a monocyclic or polycyclic heteroarylene group having 2 to 30 carbon atoms.

In one embodiment of the present specification, L20 and L21 are the same as or different from each other, and each independently a direct bond; a monocyclic or polycyclic arylene group having 6 to 20 carbon atoms; or a monocyclic or polycyclic heteroarylene group having 2 to 20 carbon atoms.

In one embodiment of the present specification, L20 and L21 are the same as or different from each other, and each independently a direct bond; a phenylene group unsubstituted or substituted with deuterium; a biphenylylene group unsubstituted or substituted with deuterium; a naphthylene group unsubstituted or substituted with deuterium; a divalent dibensofuran group; or a divalent dihenzothiophene group.

In one embodiment of the present specification, Ar20 and Ar21 are the same as or different from each other, and each independently a substituted or unsubstituted monocyclic or polycyclic aryl group having 6 to 30 carbon atoms; or a substituted or unsubstituted monocyclic or polycyclic heterocyclic group having 2 to 30 carbon atoms.

In one embodiment of the present specification, An20 and Ar21 are the same as or different from each other, and each independently a substituted or unsubstituted monocyclic or polycyclic aryl group having 6 to 20 carbon atoms; or a substituted or unsubstituted monocyclic or polycyclic heterocyclic group having 2 to 20 carbon atoms.

In one embodiment of the present specification, Ar20 and Ar21 are the same as or different from each other, and each independently a substituted or unsubstituted monocyclic to tetracyclic aryl group having 6 to 20 carbon atoms; or a substituted or unsubstituted monocyclic to tetracyclic heterocyclic group having 2 to 20 carbon atoms.

In one embodiment of the present specification, Ar20 and Ar21 are the same as or different from each other, and each independently a substituted or unsubstituted phenyl group; a substituted or unsubstituted biphenyl group; a substituted or unsubstituted terphenyl group; a substituted or unsubstituted naphthyl group; a substituted or unsubstituted anthracene group; a substituted or unsubstituted phenanthrene group; a substituted or unsubstituted phenalene group; a substituted or unsubstituted fluorene group; a substituted or unsubstituted benzofluorene group; a substituted or unsubstituted furan group; a substituted or unsubstituted thiophene group; a substituted or unsubstituted dibenzofuran group; a substituted or unsubstituted naphthobenzofuran group; a substituted or unsubstituted dibenzothiophene group; or a substituted or unsubstituted naphthobenzothiophene group.

In one embodiment of the present specification, Ar20 and Ar21 are the same as or different from each other, and each independently a phenyl group unsubstituted or substituted with deuterium, or a monocyclic or polycyclic aryl group having 6 to 20 carbon atoms; a biphenyl group unsubstituted or substituted with deuterium, or a monocyclic or polycyclic aryl group having 6 to 20 carbon atoms; a naphthyl group unsubstituted or substituted with a monocyclic or polycyclic aryl group having 6 to 20 carbon atoms; a dibenzofuran group unsubstituted or substituted with a monocyclic or polycyclic aryl group having 6 to 20 carbon atoms; a naphthobenzofuran group unsubstituted or substituted with a monocyclic or polycyclic aryl group having 6 to 20 carbon atoms; a dibenzothiophene group unsubstituted or substituted with a monocyclic or polycyclic aryl group having 6 to 20 carbon atoms; or a naphthobenzothiophene group unsubstituted or substituted with a monocyclic or polycyclic aryl group having 6 to 20 carbon atoms.

In one embodiment of the present specification, Ar20 and Ar21 are the same as or different from each other, and each independently a phenyl group unsubstituted or substituted with deuterium; a biphenyl group unsubstituted or substituted with deuterium; a terphenyl group; a naphthyl group unsubstituted or substituted with deuterium; a phenanthrene group; a dibenzofuran group; a naphthobenzofuran group; a dibenzothiophene group; or a naphthobenzothiophene group.

In one embodiment of the present specification, Ar20 is a substituted or unsubstituted heterocyclic group, and Ar21 is a substituted or unsubstituted aryl group.

In one embodiment of the present specification, R20 is hydrogen; deuterium; a halogen group; a substituted or unsubstituted linear or branched alkyl group having 1 to 30 carbon atoms; a substituted or unsubstituted monocyclic or polycyclic cycloalkyl group having 3 to 30 carbon atoms; a substituted or unsubstituted monocyclic or polycyclic aryl group having 6 to 30 carbon atoms; or a substituted or unsubstituted monocyclic or polycyclic heterocyclic group having 2 to 30 carbon atoms.

In one embodiment of the present specification, R20 is hydrogen; deuterium; fluorine; a substituted or unsubstituted linear or branched alkyl group having 1 to 10 carbon atoms; a substituted or unsubstituted monocyclic or polycyclic cycloalkyl group having 3 to 10 carbon atoms; a substituted or unsubstituted monocyclic or polycyclic aryl group having 6 to 30 carbon atoms; or a substituted or unsubstituted monocyclic or polycyclic heterocyclic group having 2 to 30 carbon atoms.

In one embodiment of the present specification, R20 is hydrogen; a substituted or unsubstituted monocyclic or polycyclic aryl group having 6 to 30 carbon atoms; or a substituted or unsubstituted monocyclic or polycyclic heterocyclic group having 2 to 30 carbon atoms.

In one embodiment of the present specification, R20 is hydrogen; a substituted or unsubstituted monocyclic or polycyclic aryl group having 6 to 20 carbon atoms; or a substituted or unsubstituted monocyclic or polycyclic heterocyclic group having 2 to 20 carbon atoms.

In one embodiment of the present specification, R20 is hydrogen; a substituted or unsubstituted monocyclic to tetracyclic aryl group having 6 to 20carbon atoms; or a substituted or unsubstituted monocyclic to tetracyclic heterocyclic group having 2 to 20 carbon atoms.

In one embodiment of the present specification, R20 is hydrogen; a substituted or unsubstituted phenyl group; a substituted or unsubstituted biphenyl group; a substituted or unsubstituted terphenyl group; a substituted or unsubstituted naphthyl group; a substituted or unsubstituted anthracene group; a substituted or unsubstituted phenanthrene group; a substituted or unsubstituted phenalene group; a substituted or unsubstituted fluorene group; a substituted or unsubstituted benzofluorene group; a substituted or unsubstituted furan group; a substituted or unsubstituted thiophene group; a substituted or unsubstituted dibenzofuran group; a substituted or unsubstituted naphthobenzofuran group; a substituted or unsubstituted dibenzothiophene group; or a substituted or unsubstituted naphthobenzothiophene group.

In one embodiment of the present specification, R20 is hydrogen; deuterium; a phenyl group unsubstituted or substituted with deuterium, or a monocyclic or polycyclic aryl group having 6 to 20 carbon atoms; a biphenyl group unsubstituted or substituted with a monocyclic or polycyclic aryl group having 6 to 20 carbon atoms; a naphthyl group unsubstituted or substituted with deuterium, or a monocyclic or polycyclic aryl group having 6 to 20 carbon atoms; a dibenzofuran group unsubstituted or substituted with a monocyclic or polycyclic aryl group having 6 to 20 carbon atoms; a naphthobenzofuran group unsubstituted or substituted with a monocyclic or polycyclic aryl group having 6 to 20 carbon atoms; a dibenzothiophene group unsubstituted or substituted with a monocyclic or polycyclic aryl group having 6 to 20 carbon atoms; or a naphthobenzothiophene group unsubstituted or substituted with a monocyclic or polycyclic aryl group having 6 to 20 carbon atoms.

In one embodiment of the present specification, R20 is hydrogen; deuterium; a phenyl group unsubstituted or substituted with deuterium, a phenyl group or a naphthyl group; a biphenyl group; a naphthyl group unsubstituted or substituted with deuterium, a phenyl group or a naphthyl group; a dibenzofuran group; a naphthobenzofuran group; a dibenzothiophene group; or a naphthobenzothiophene group.

According to one embodiment of the present specification, R21 is hydrogen.

According to one embodiment of the present specification, R21 is deuterium.

In one embodiment of the present specification, when the compound represented by Chemical Formula H is substituted with deuterium, hydrogen at a substitutable position may be substituted with deuterium by 30% or more. In another embodiment, hydrogen at a substitutable position is substituted with deuterium by 40% or more in the structure of Chemical Formula H. In another embodiment, hydrogen at a substitutable position is substituted with deuterium by 60% or more in the structure of Chemical Formula H.

In another embodiment, hydrogen at a substitutable position is substituted with deuterium by 80% or more in the structure of Chemical Formula H. In another embodiment, hydrogen at a substitutable position is substituted with deuterium by 100% in the structure of Chemical Formula H.

In one embodiment of the present specification, the compound represented by Chemical Formula H is any one selected from among the following compounds.

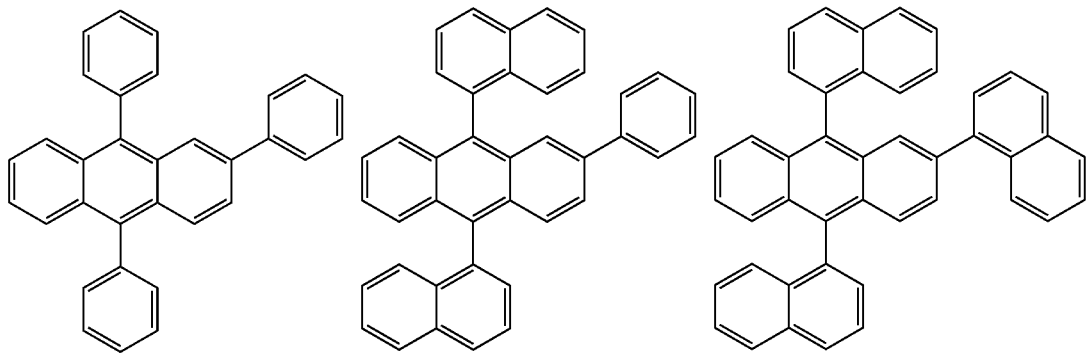

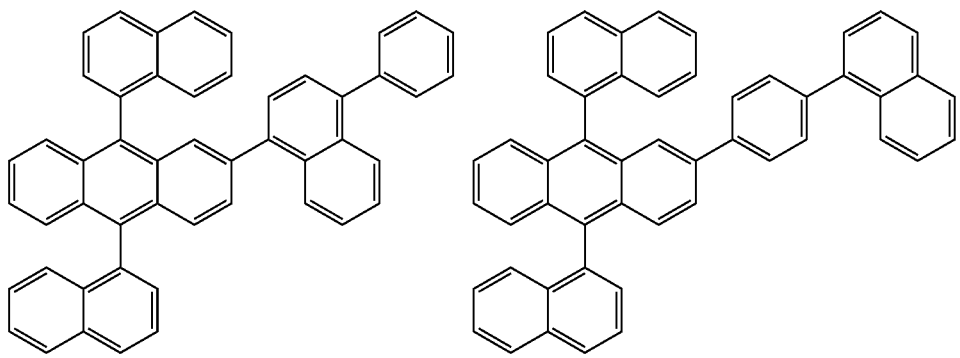

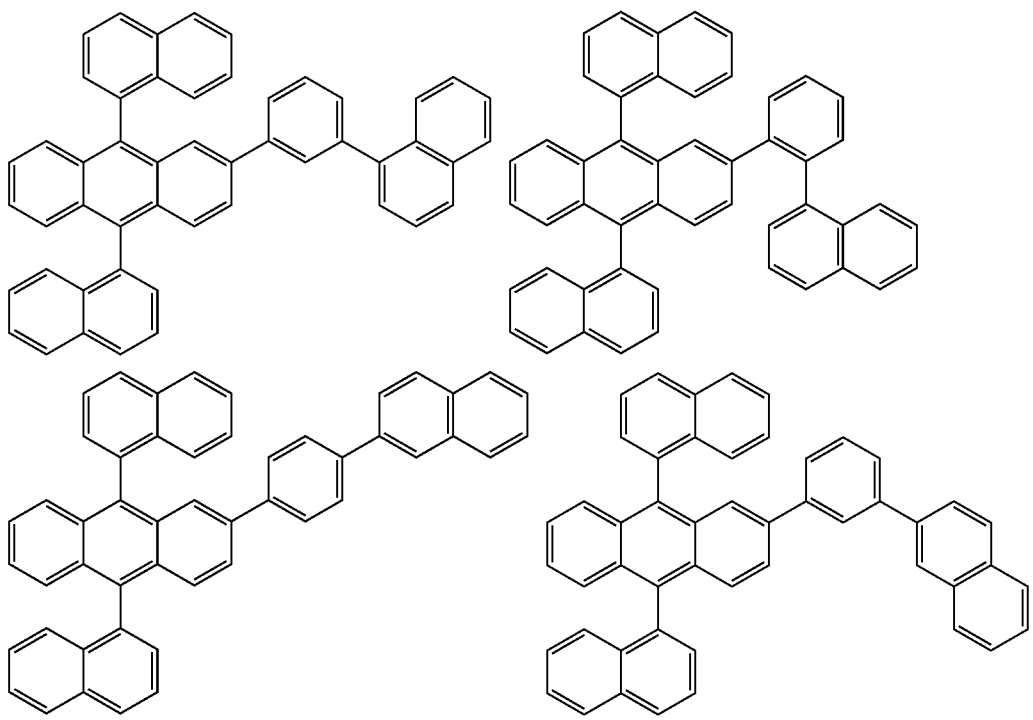

975 976
-continued
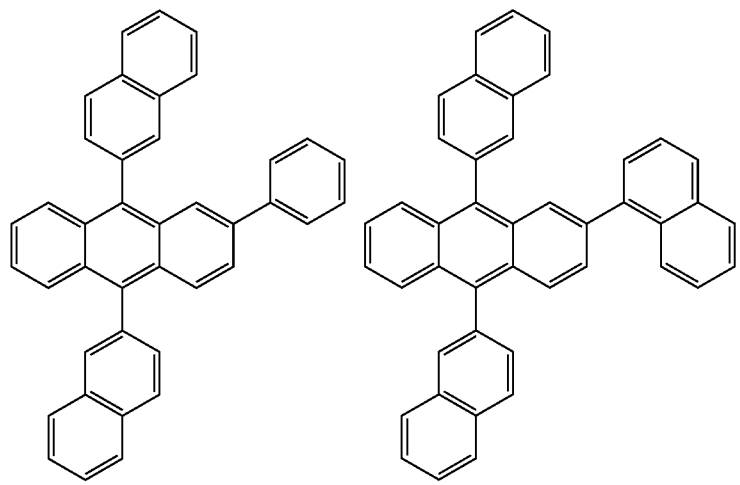
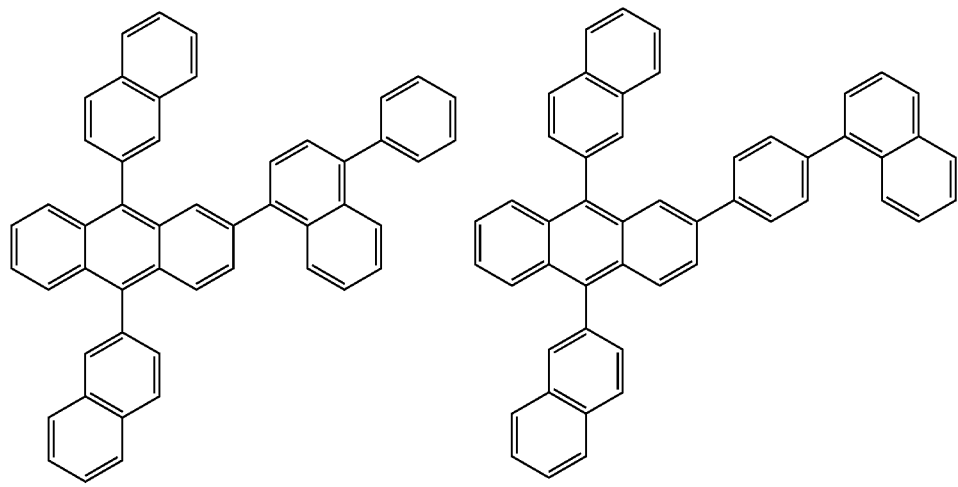
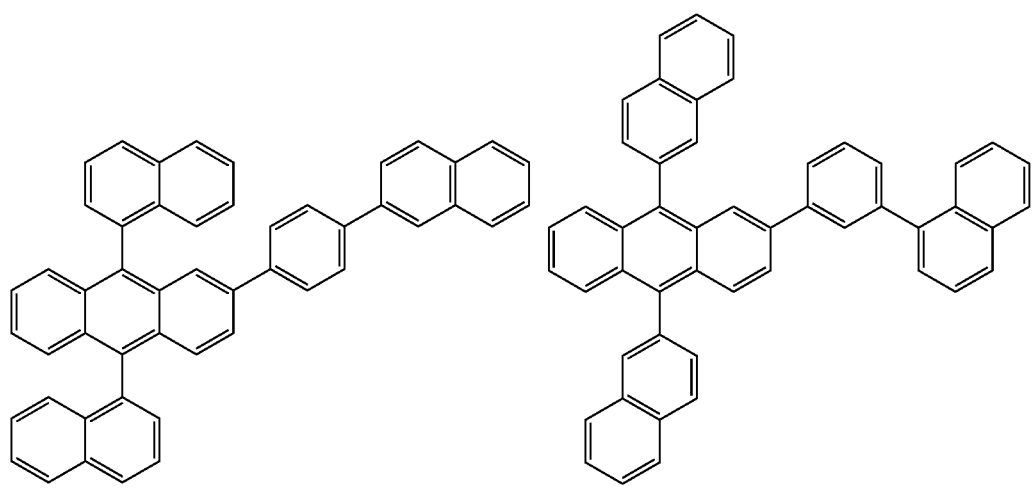

977 978
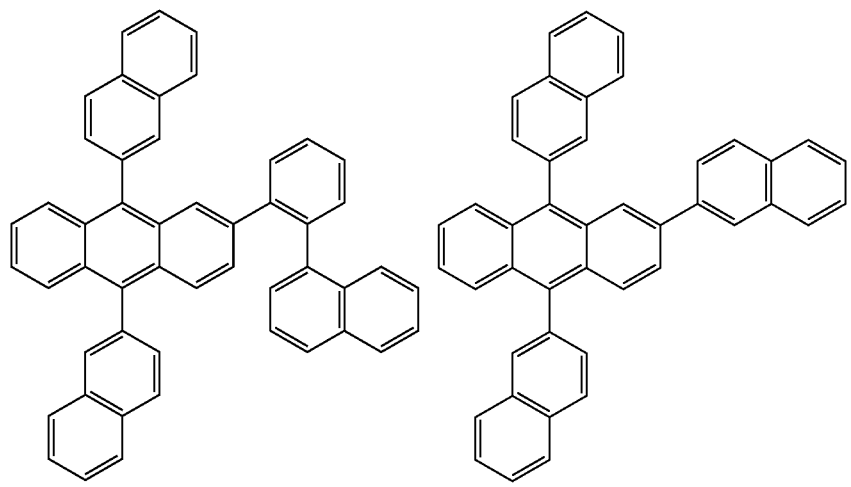
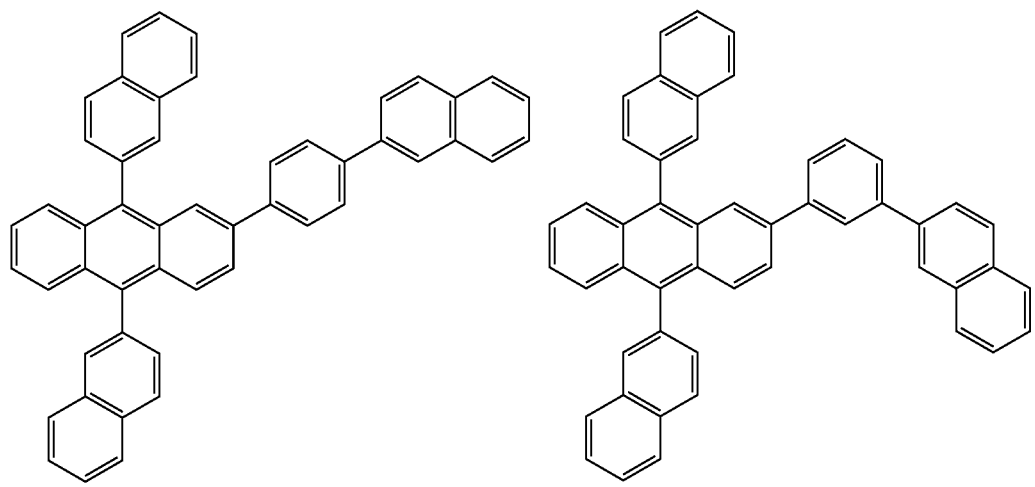
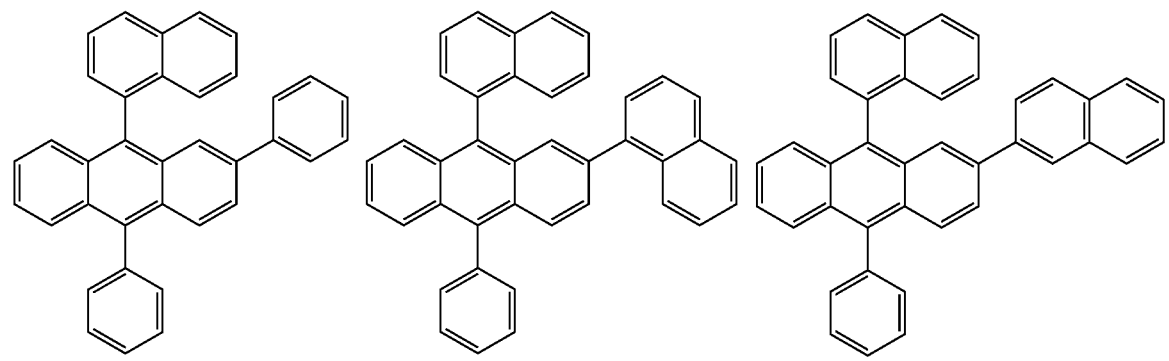

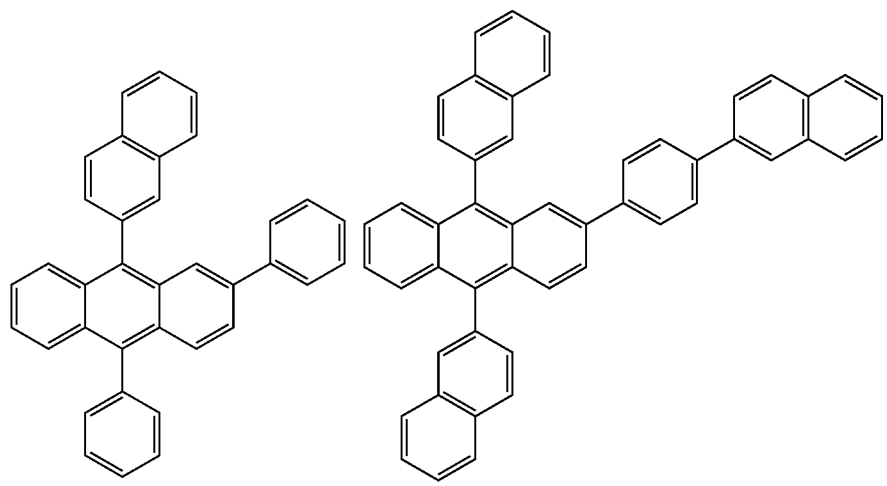
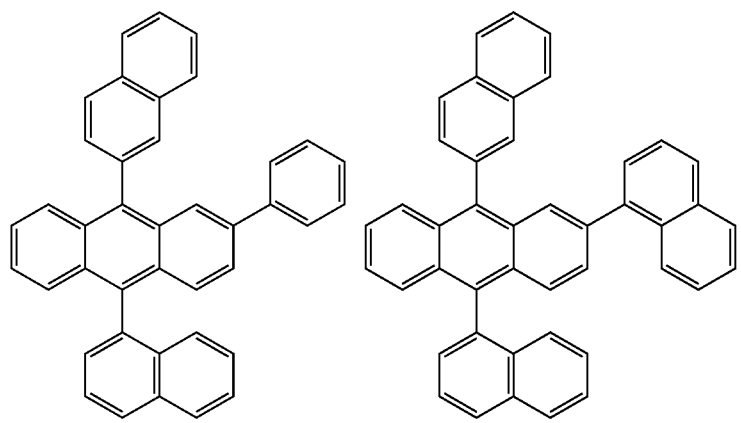
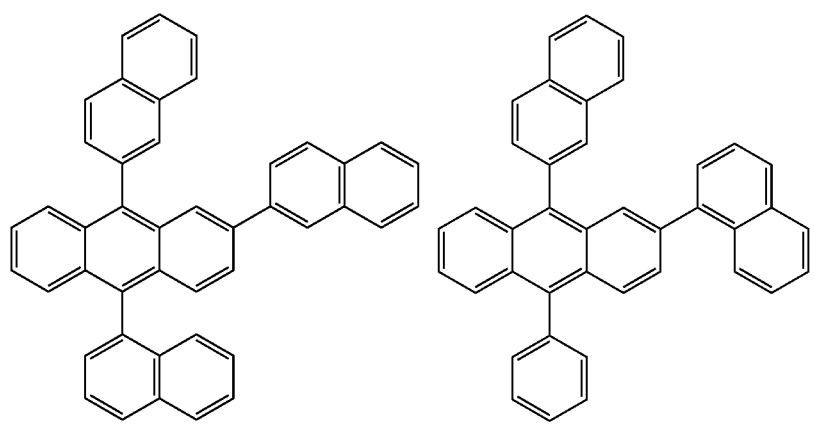

-continued
981
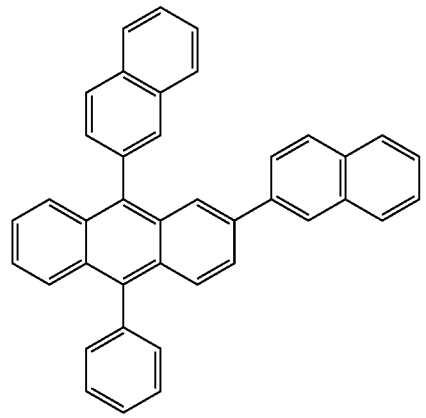 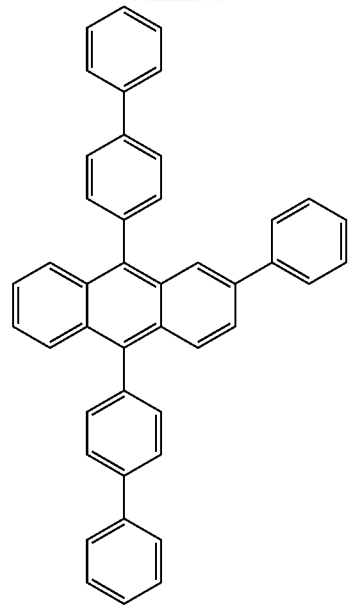 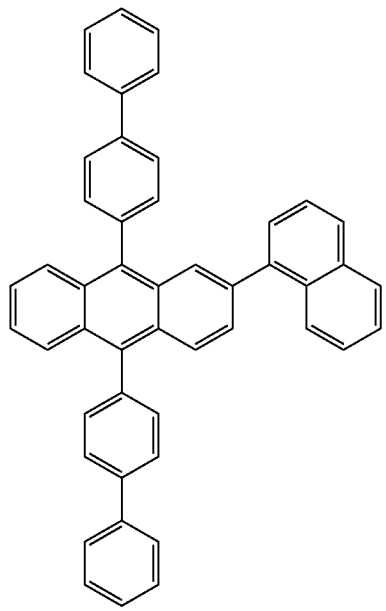
982
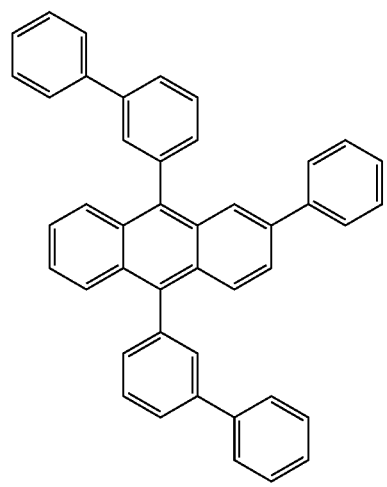 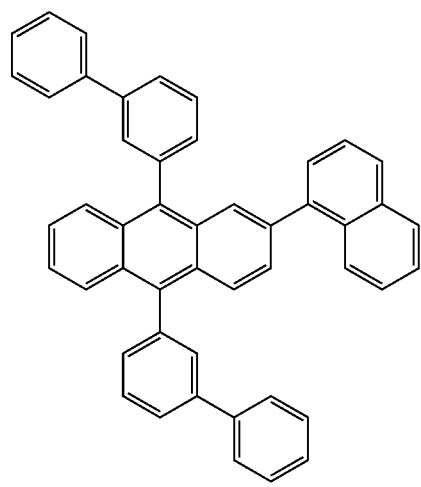
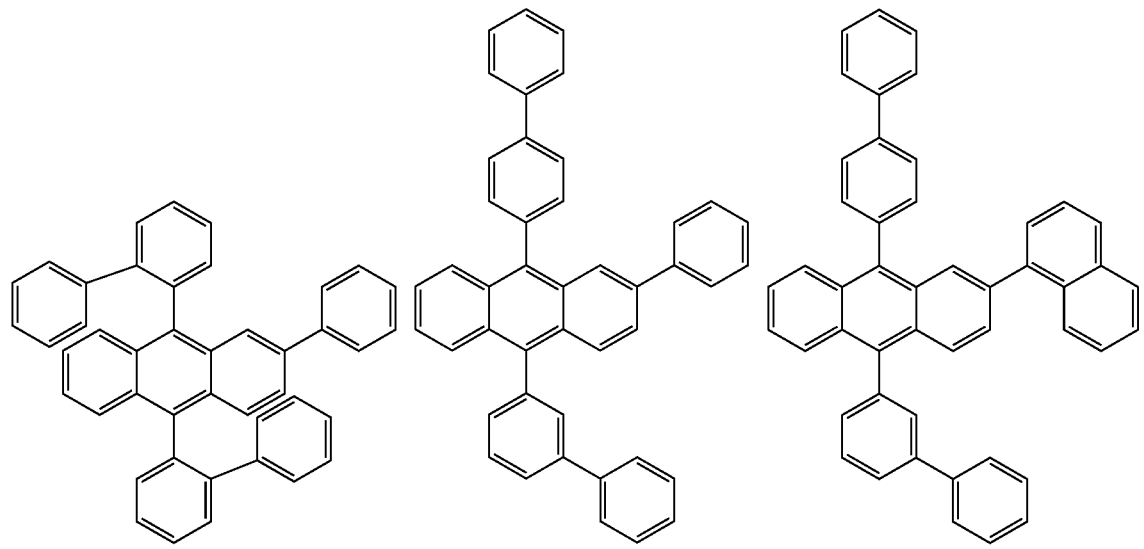

983 984
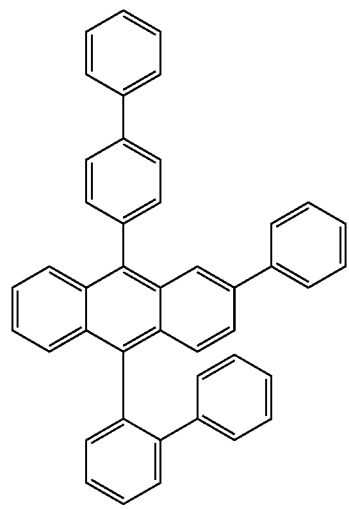

985
986
-continued
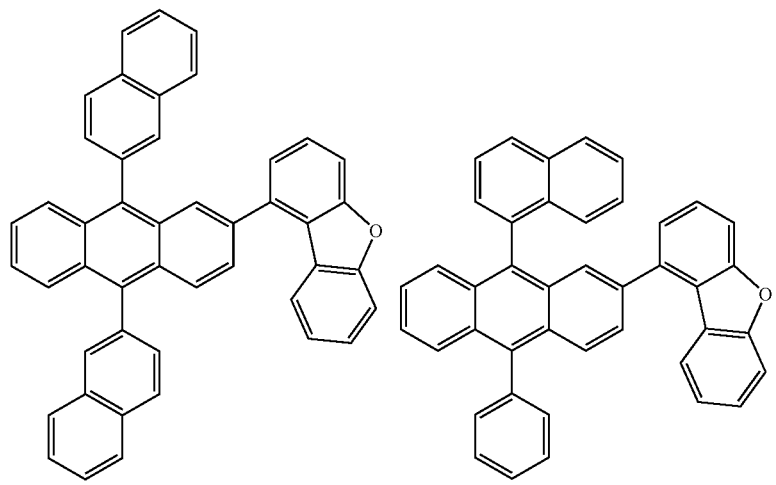
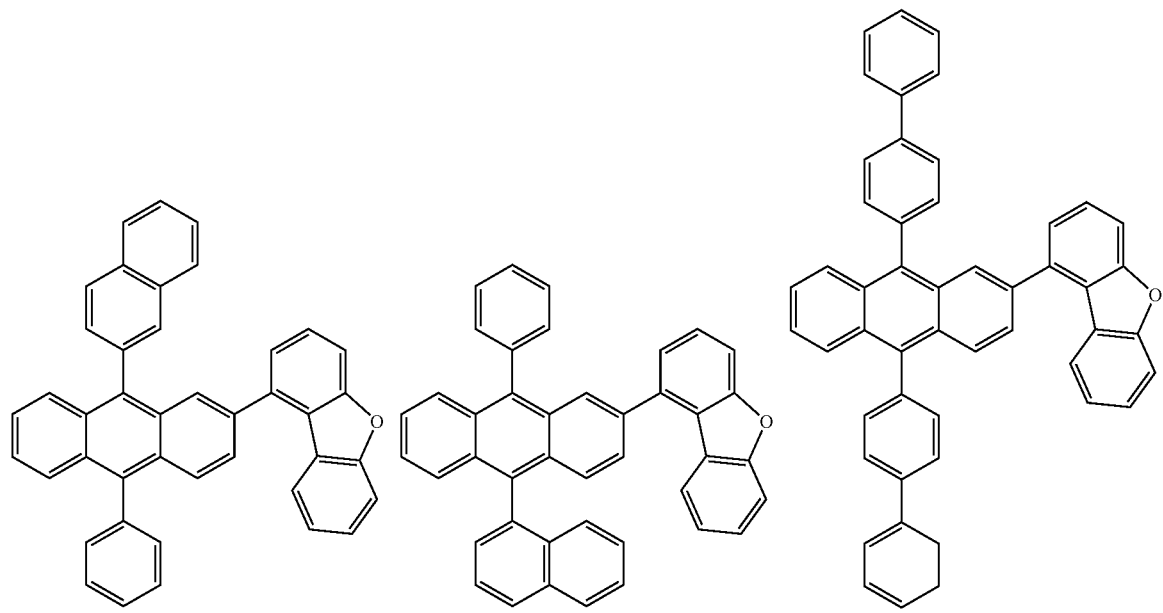
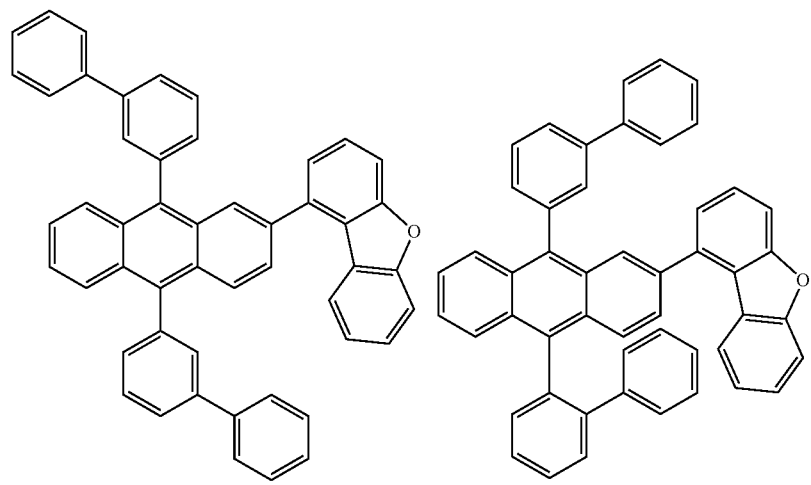

987
-continued
988
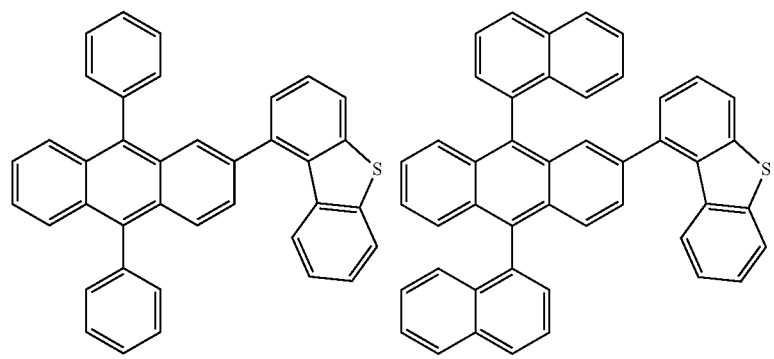
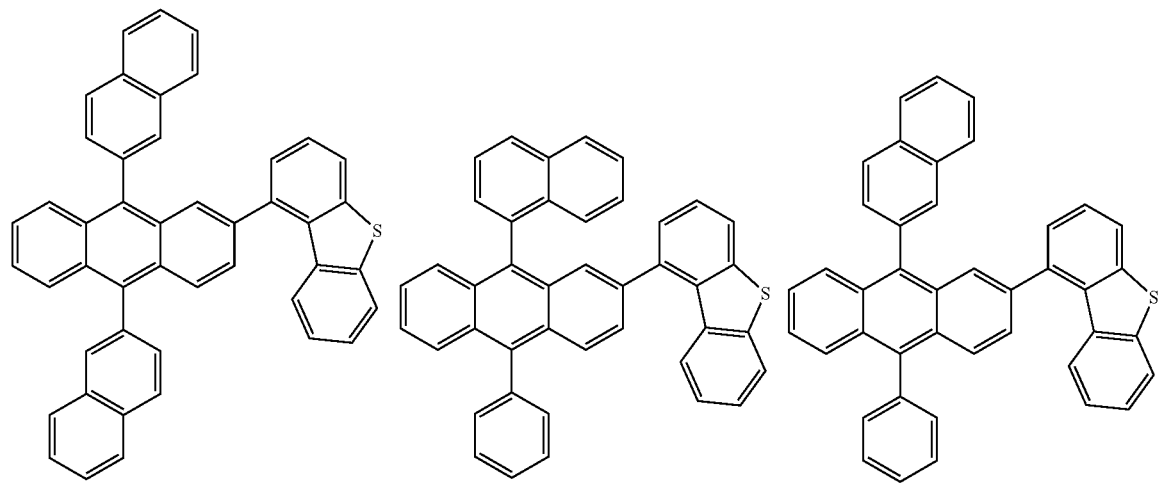
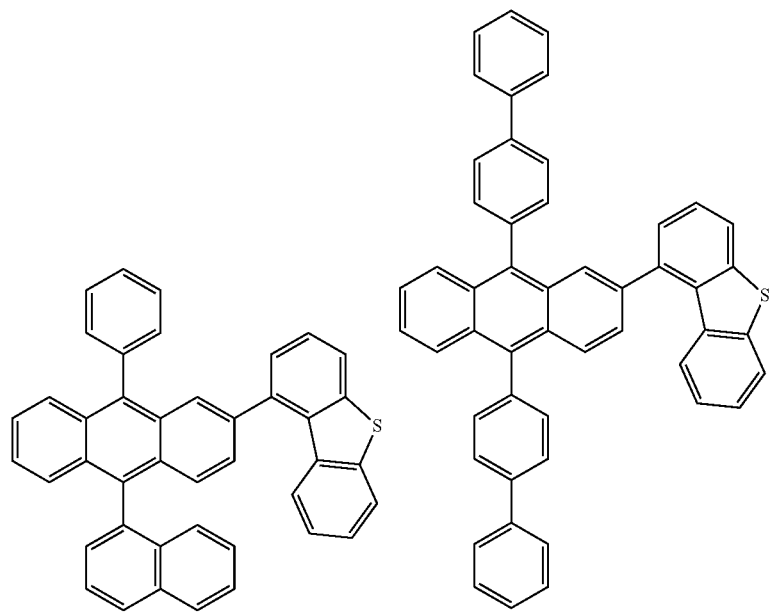

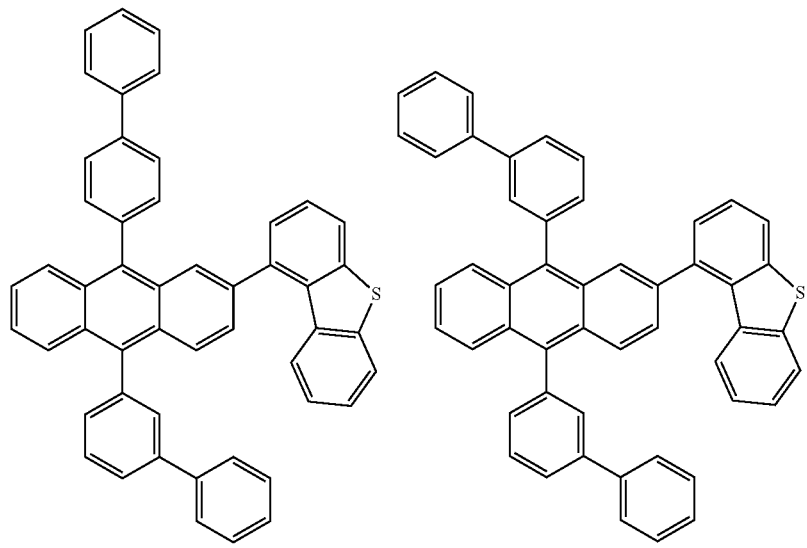
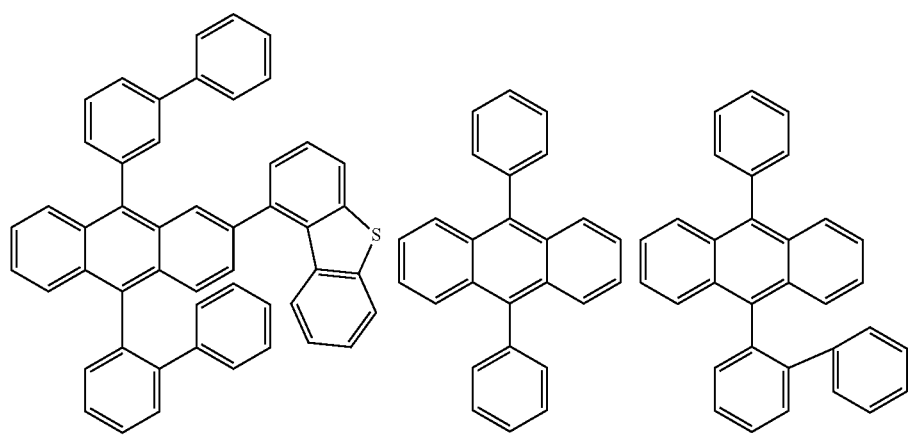
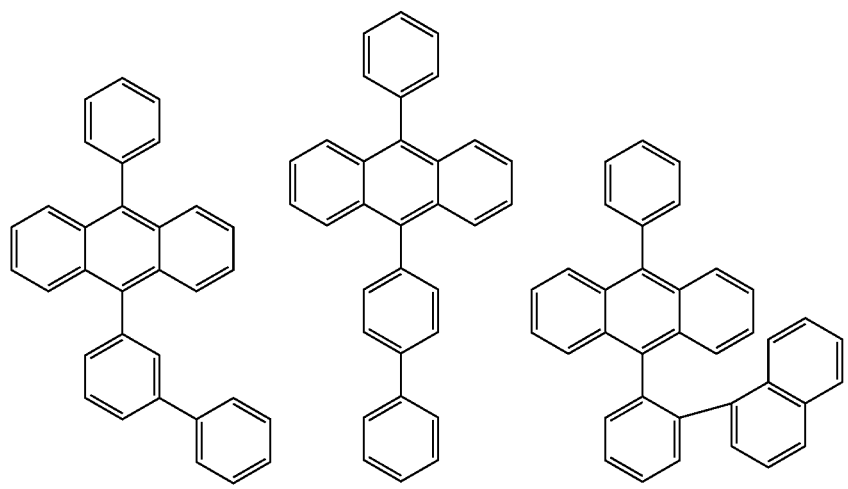

-continued
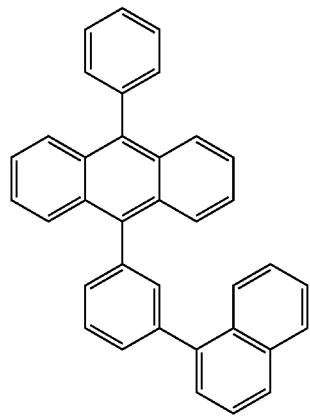
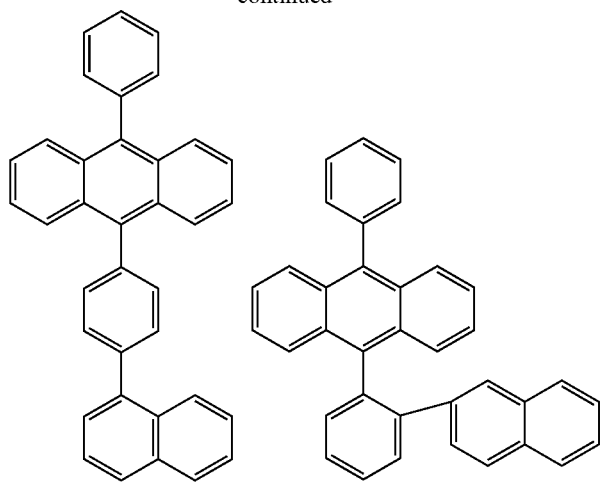
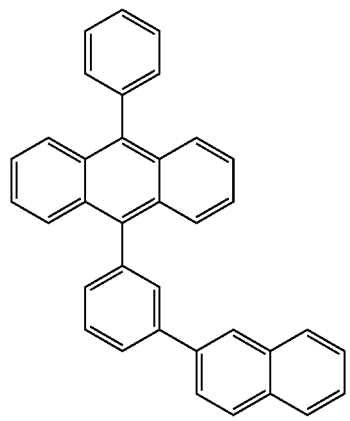
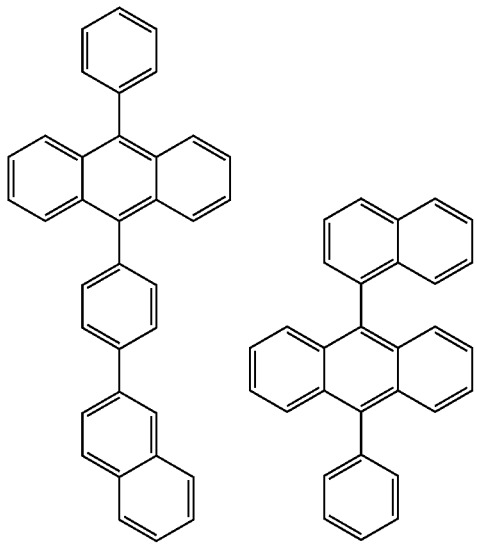
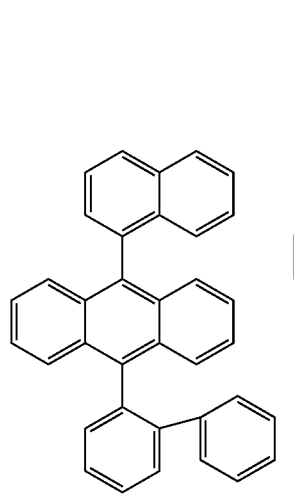
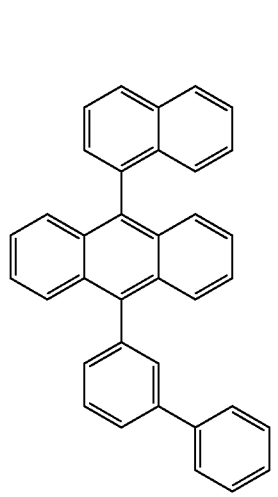
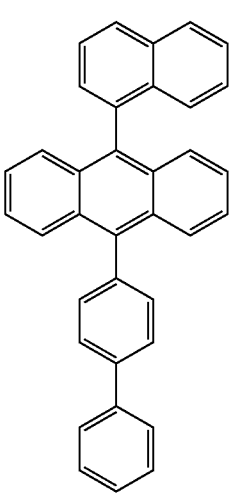

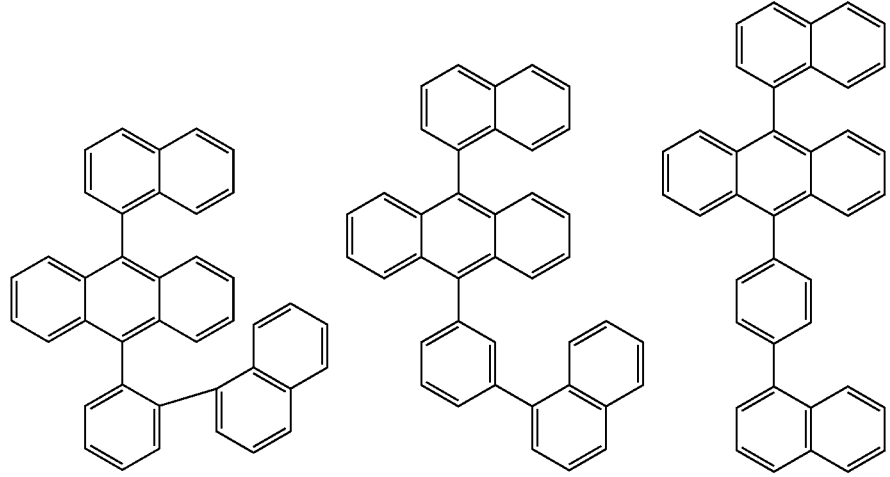
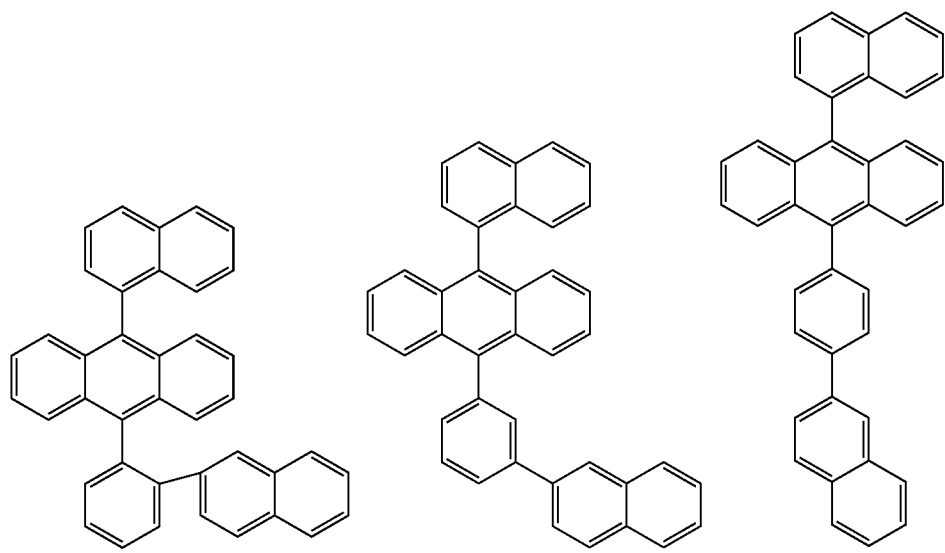
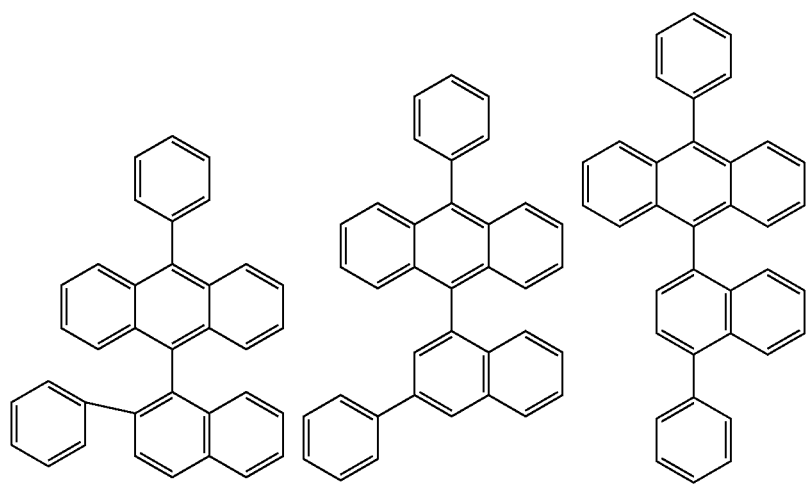

995
-continued
996
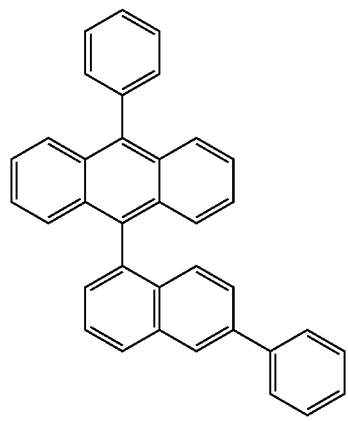
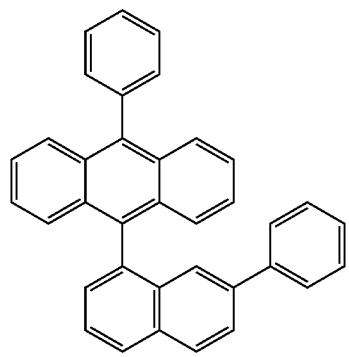
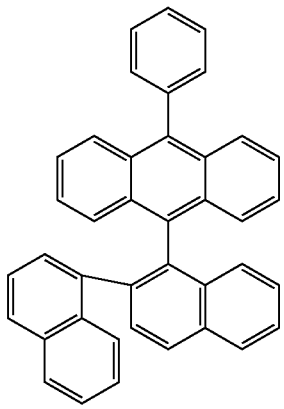
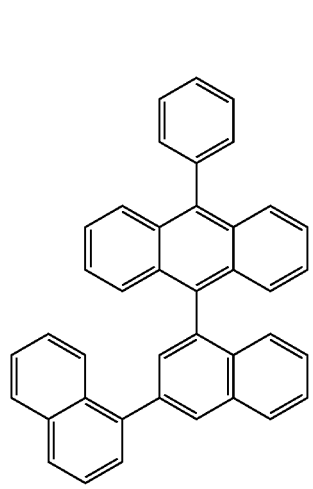
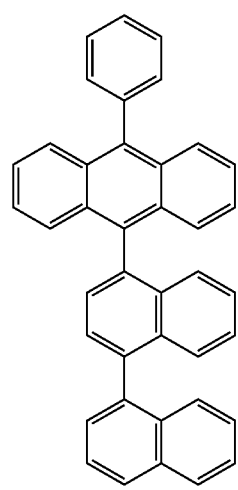
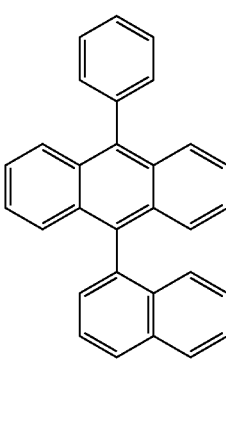
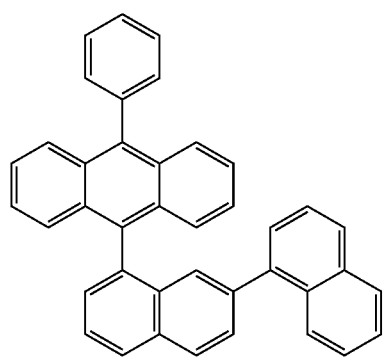
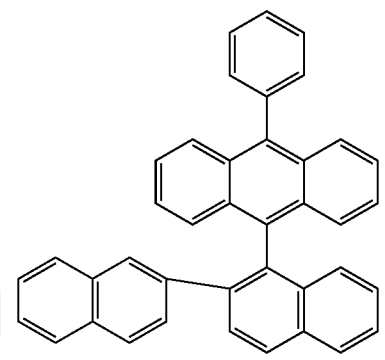

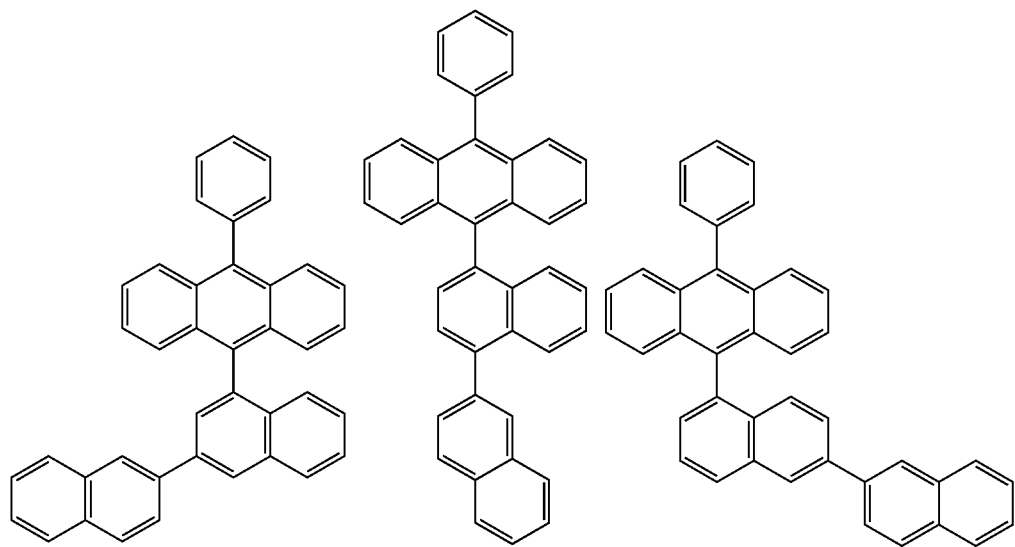
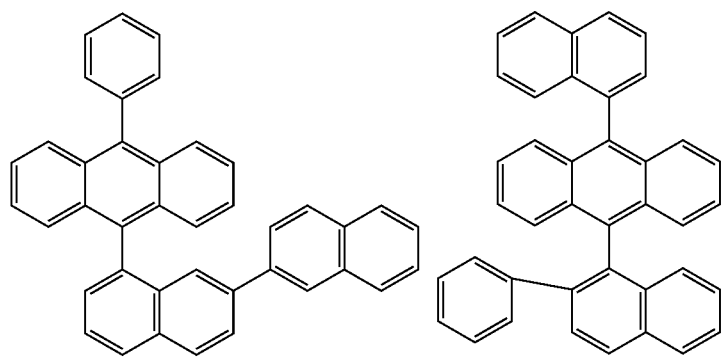
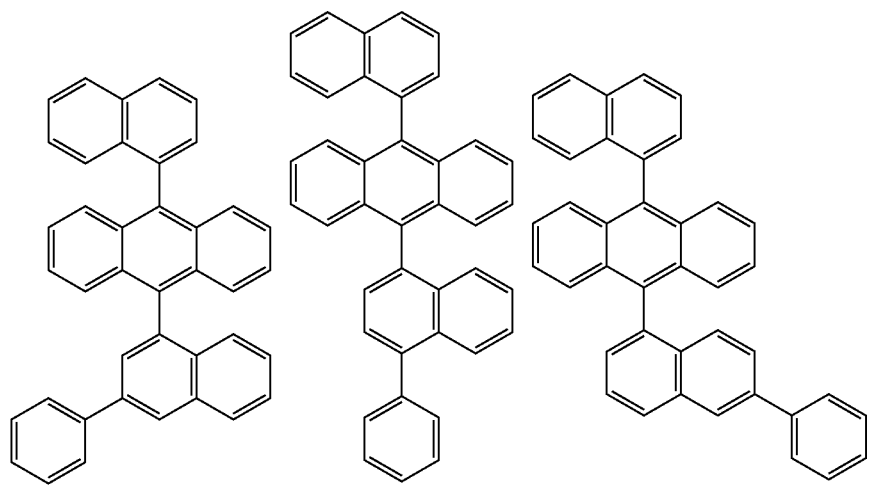

-continued
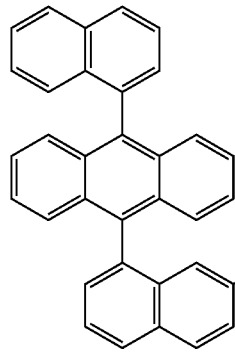
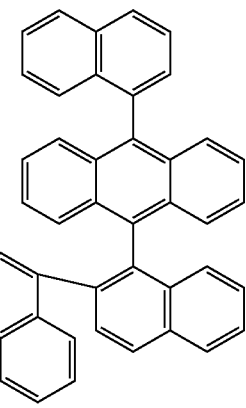
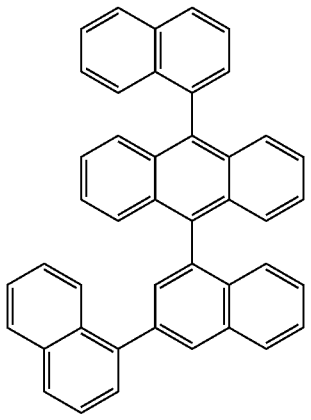
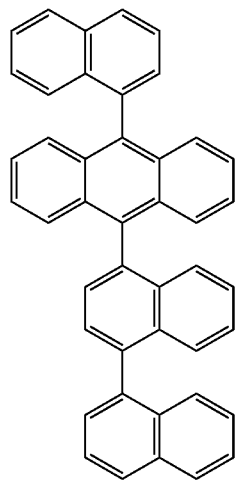
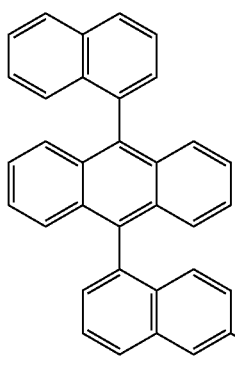
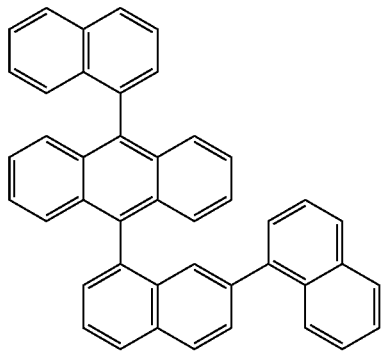
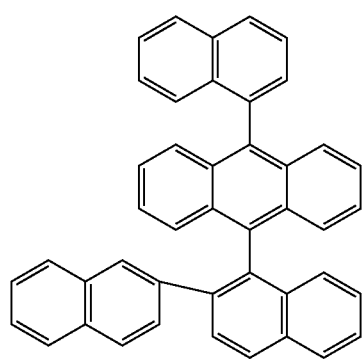
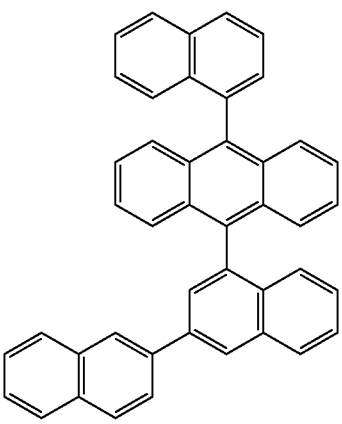
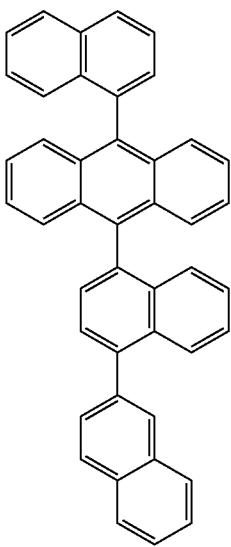

-continued
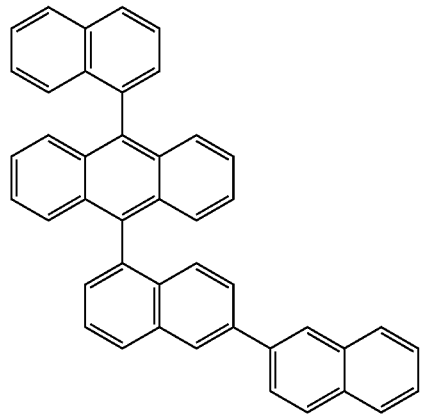
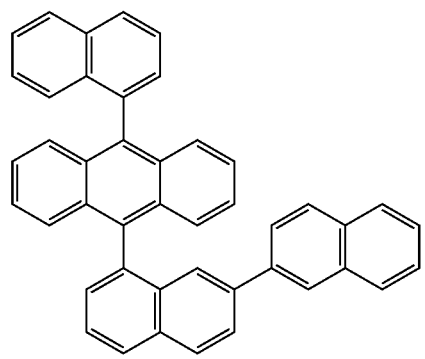
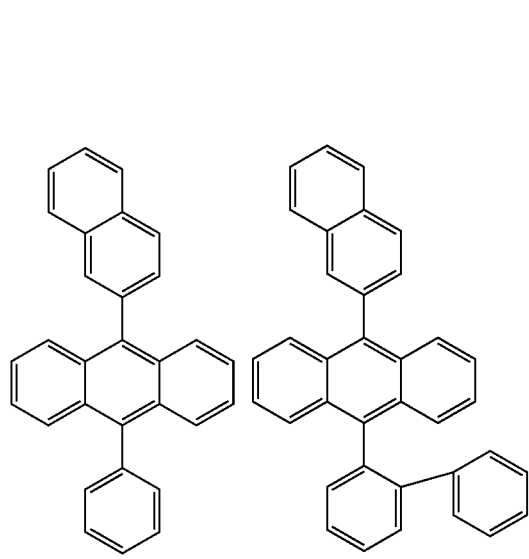
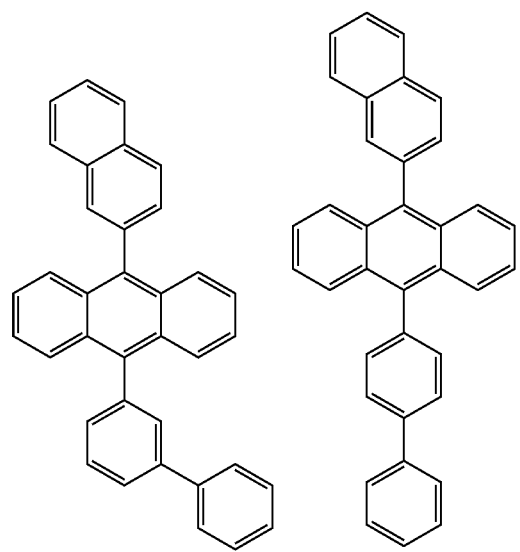
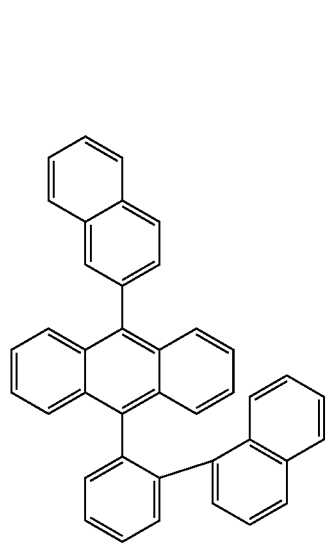
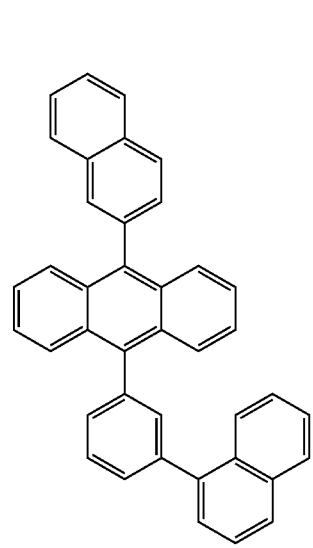
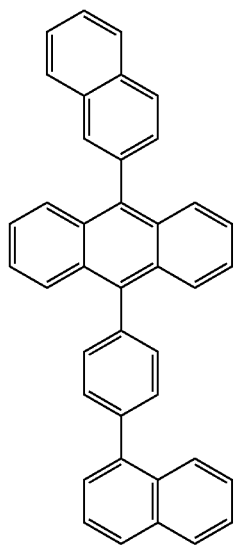

-continued
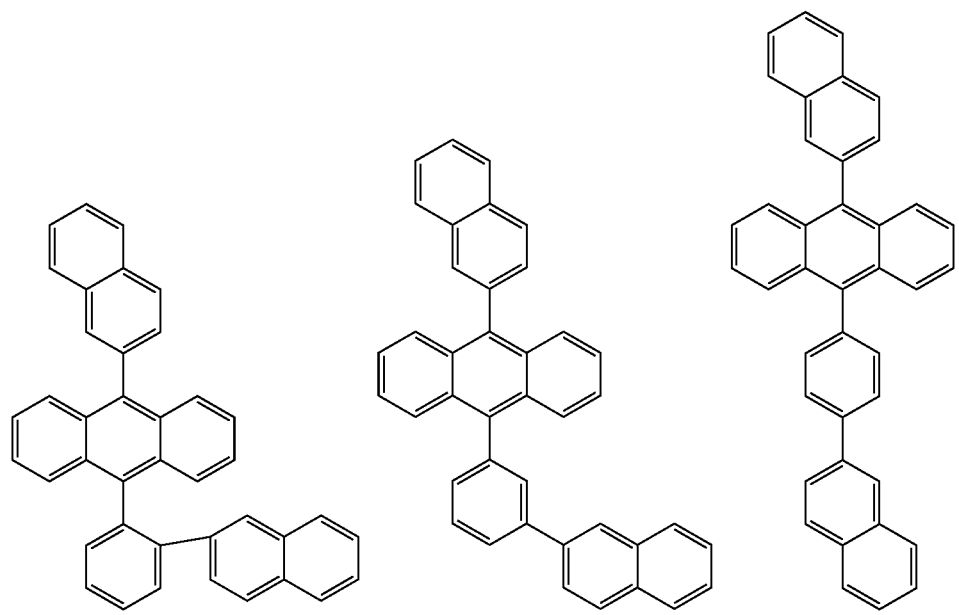
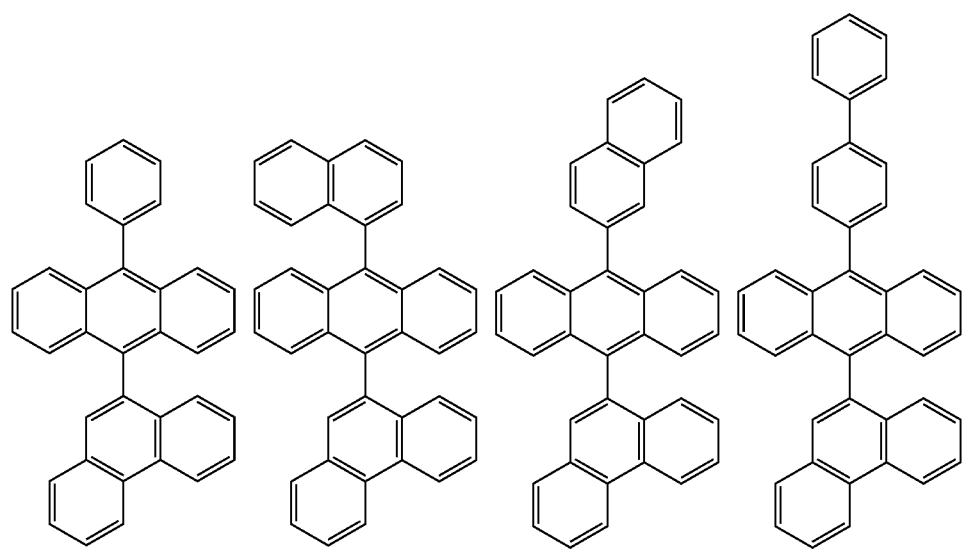
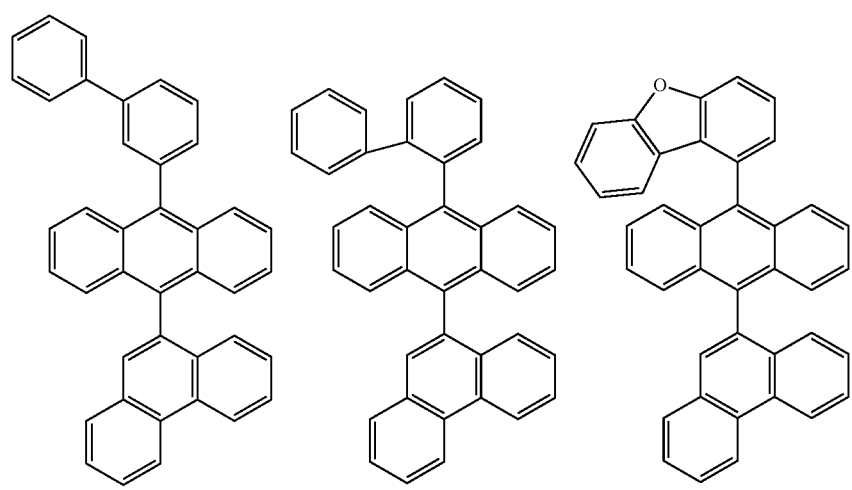

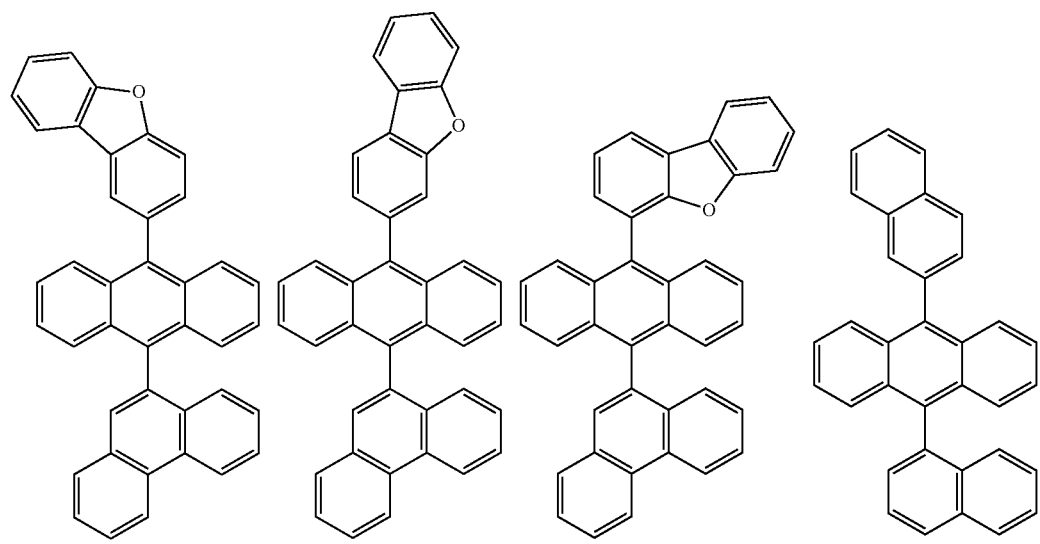
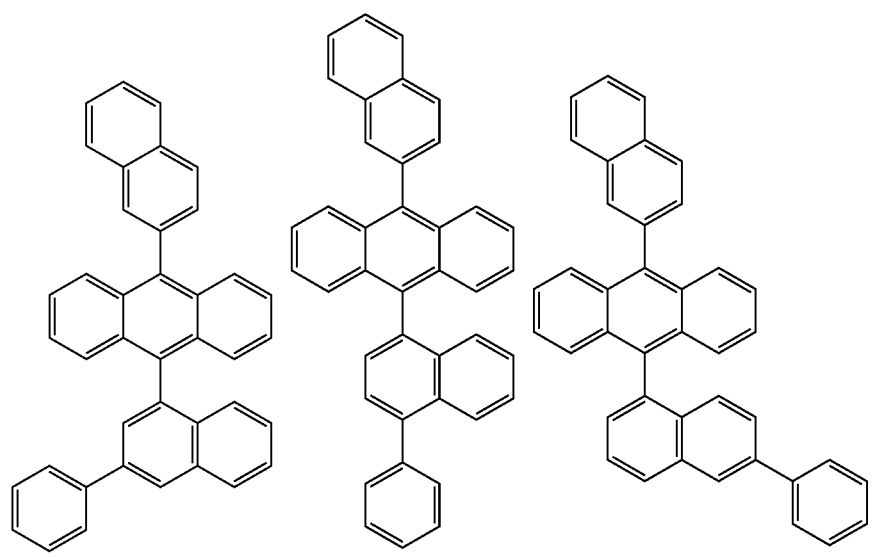
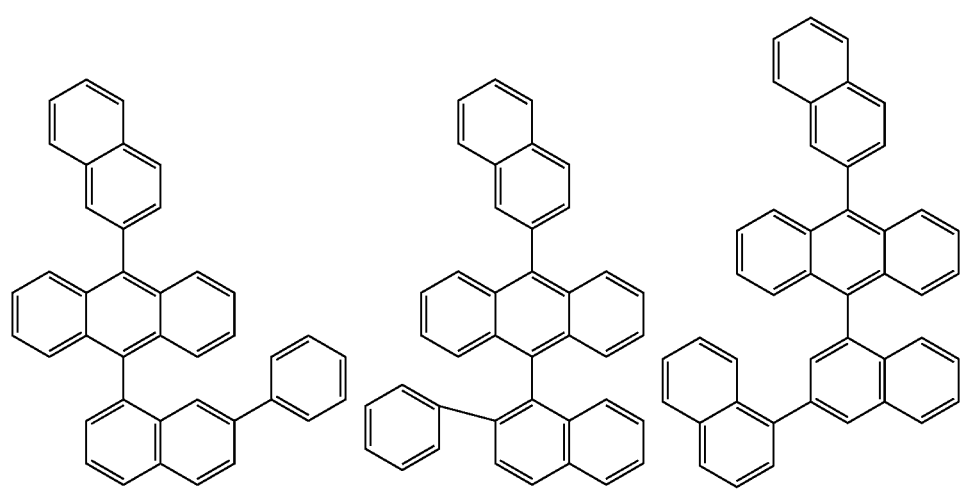

1007 1008
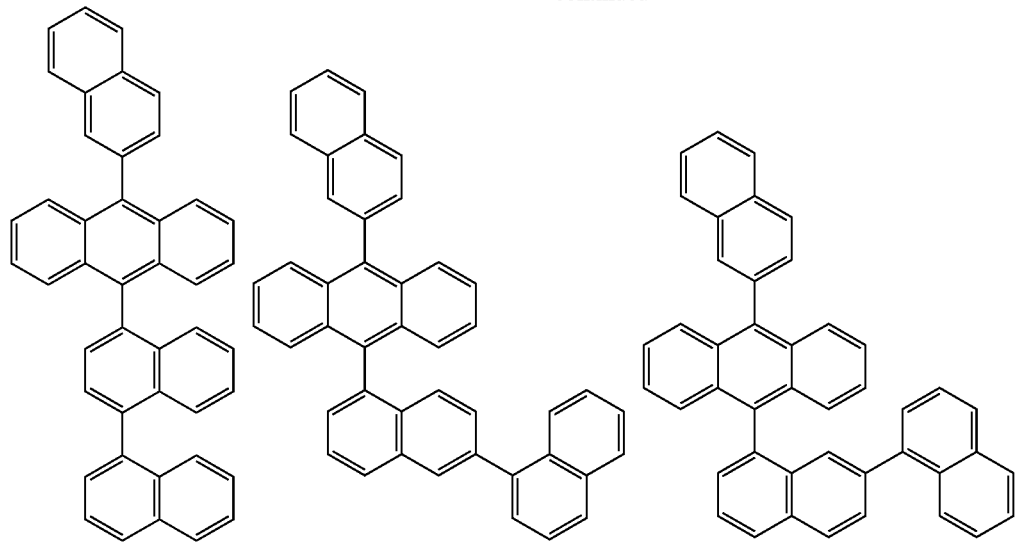
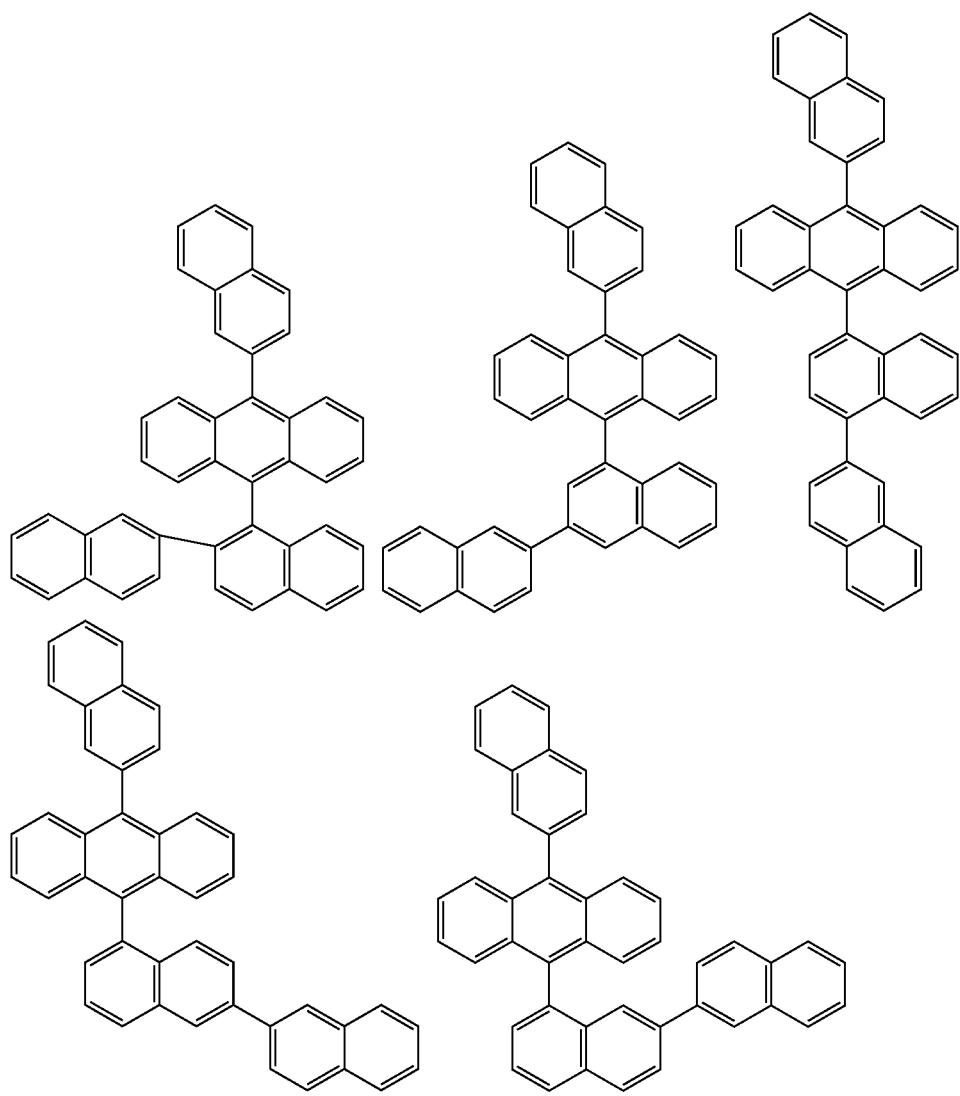

-continued
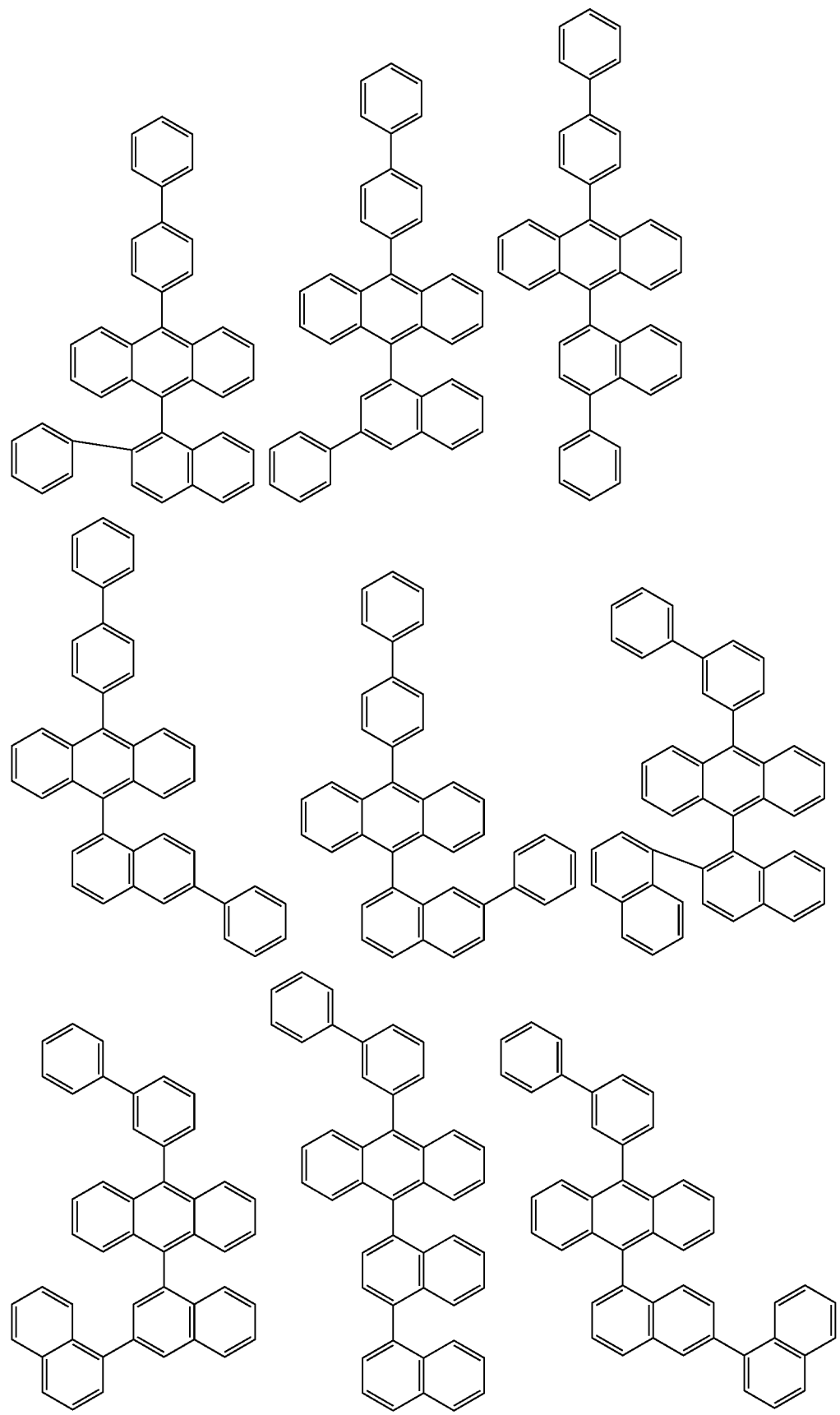

1011 1012
-continued
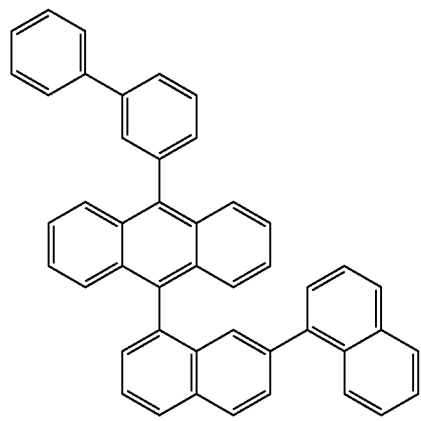
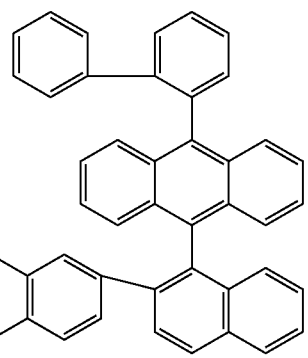
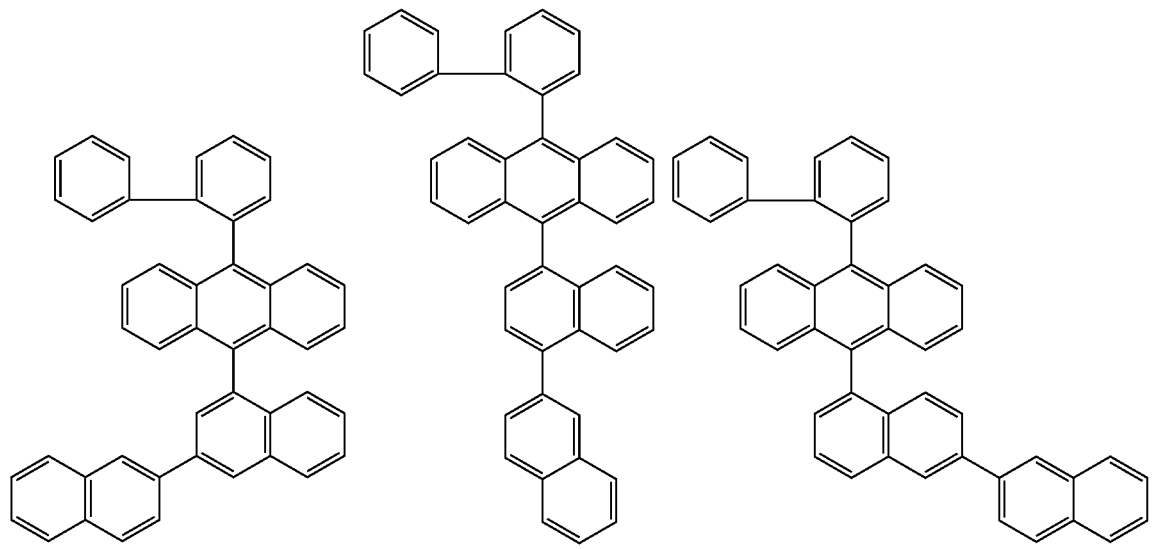
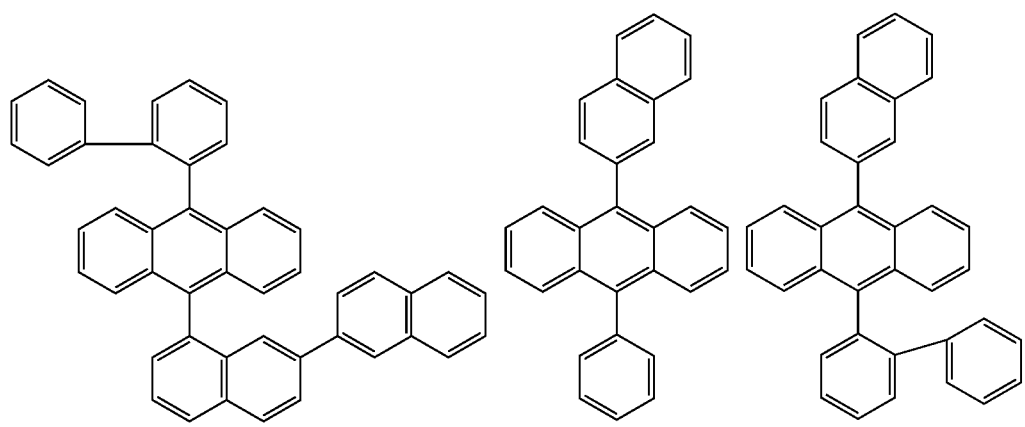

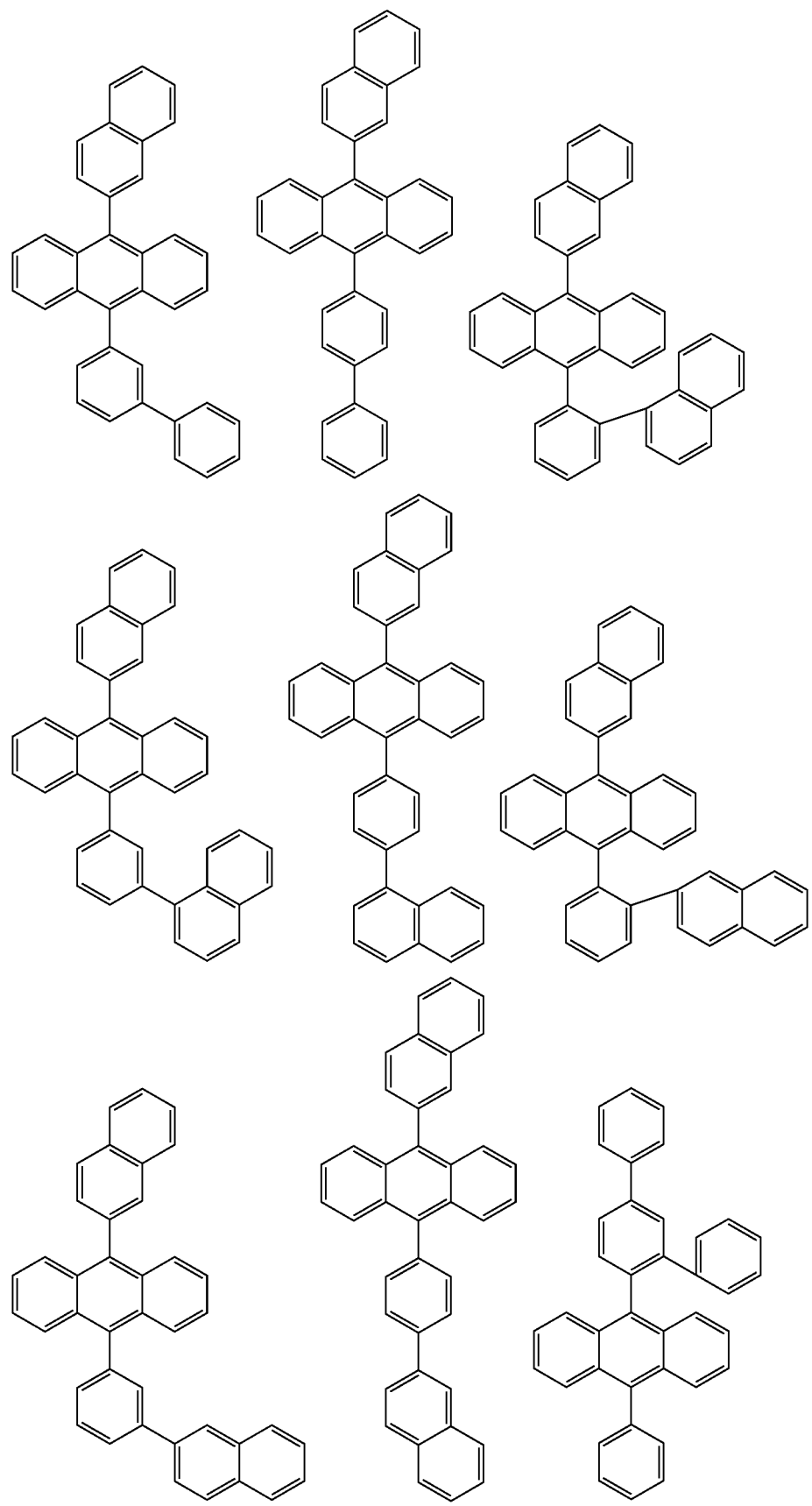

1015
-continued
1016
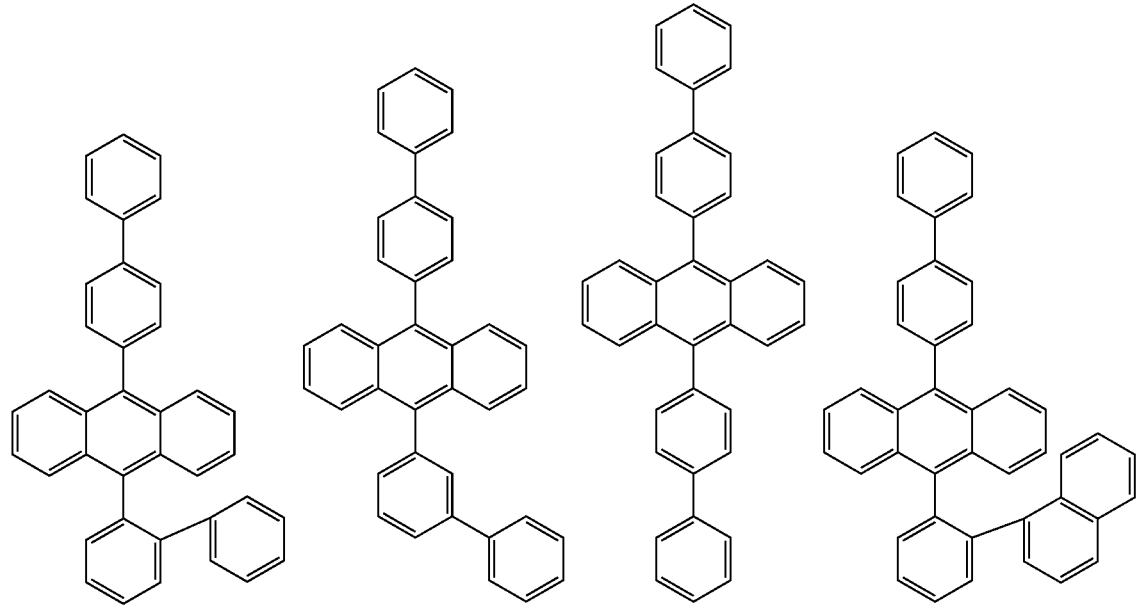
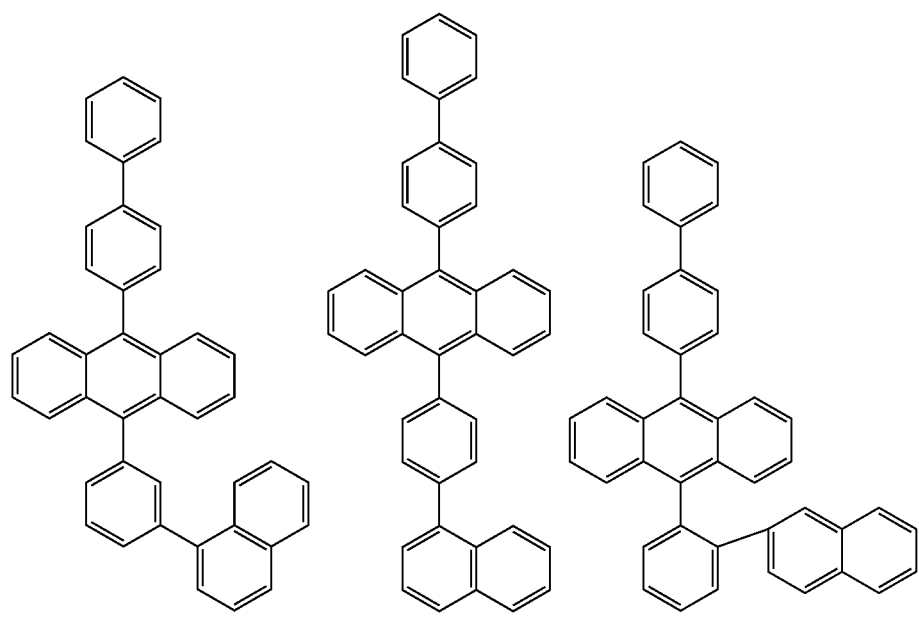

-continued
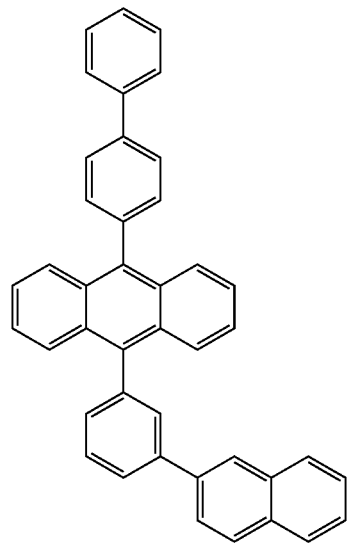
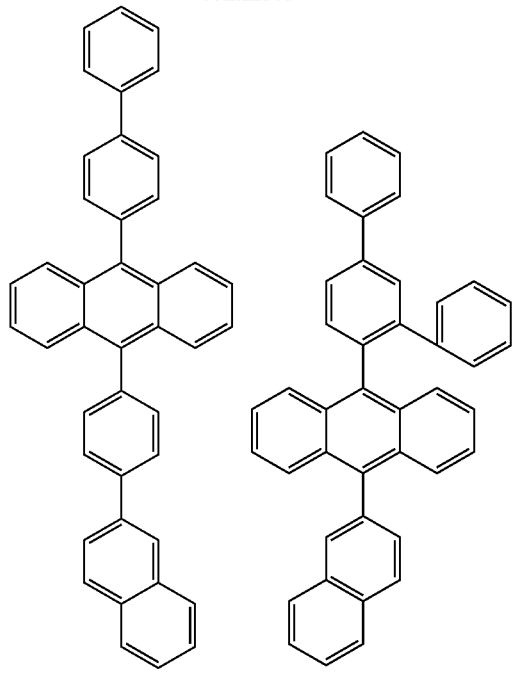
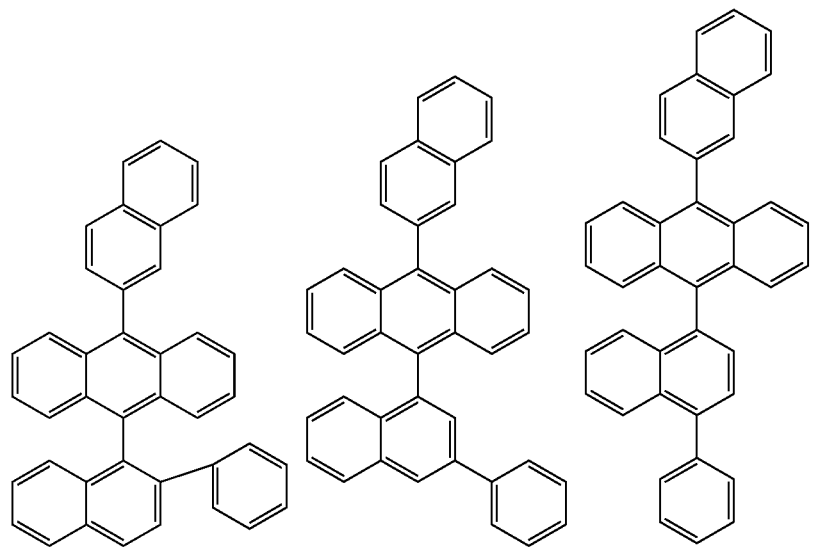

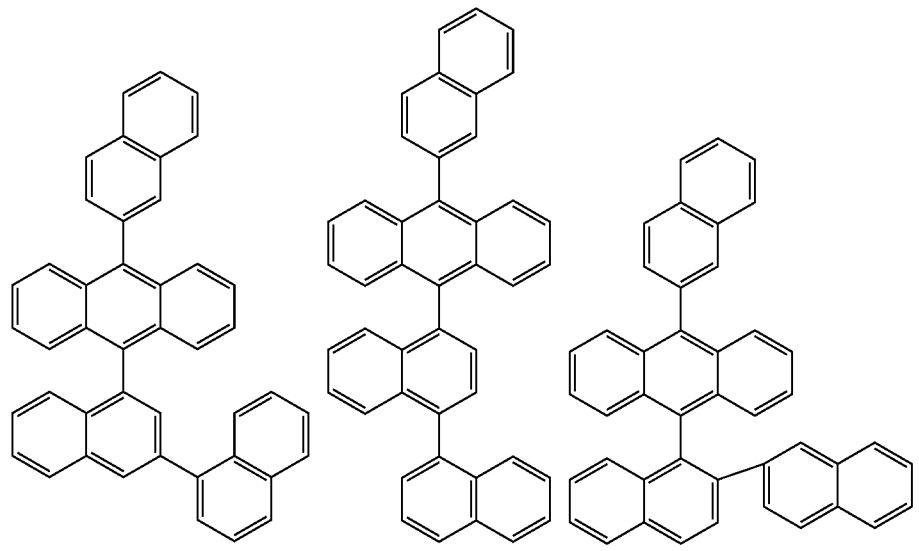
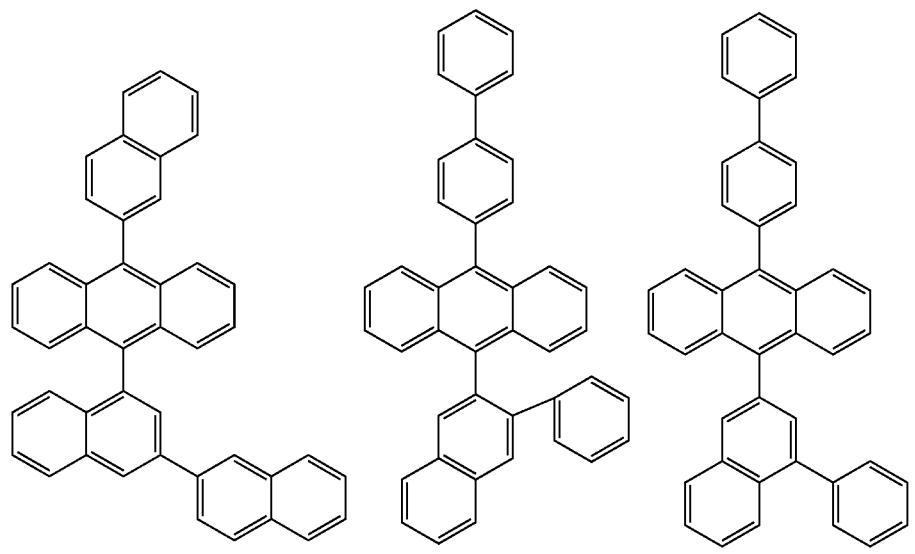
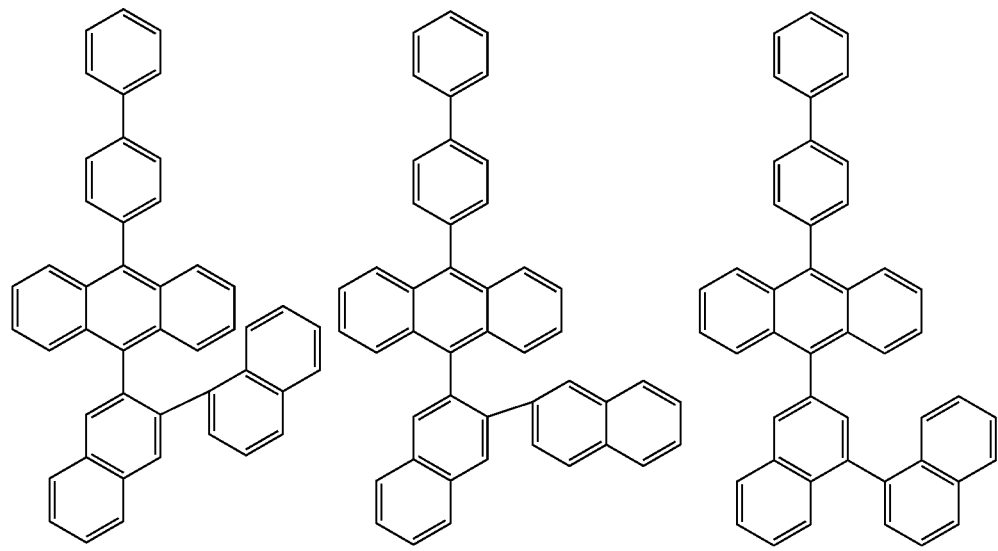

-continued
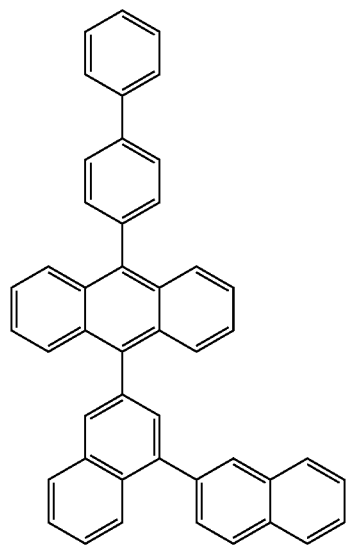

1023 1024
-continued
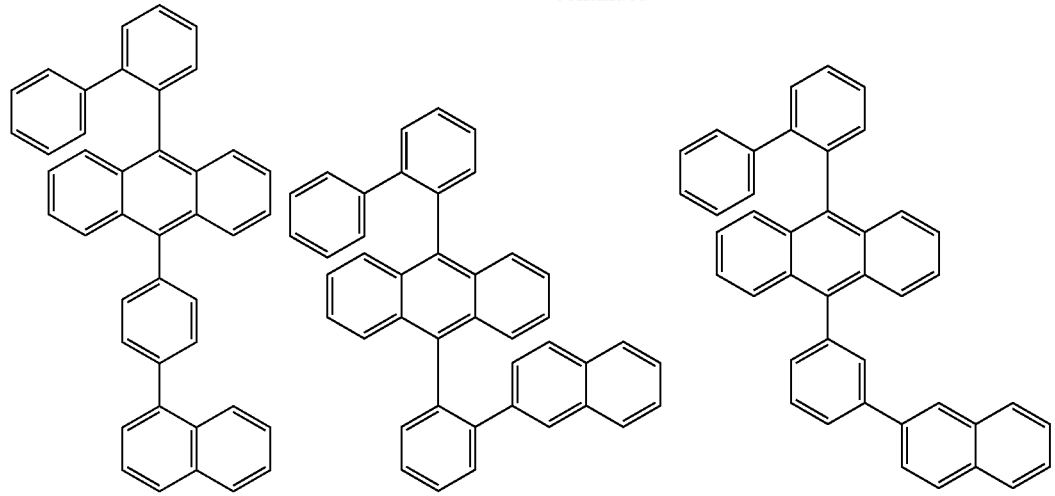
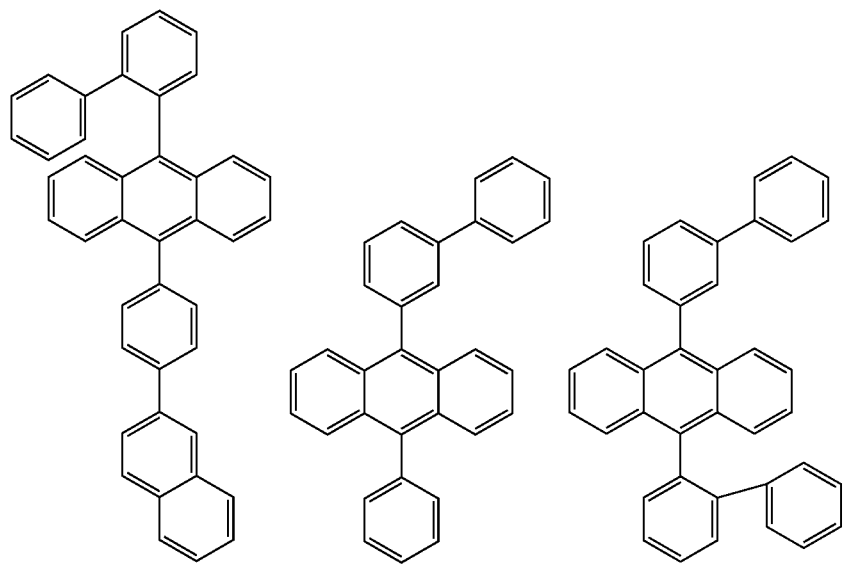
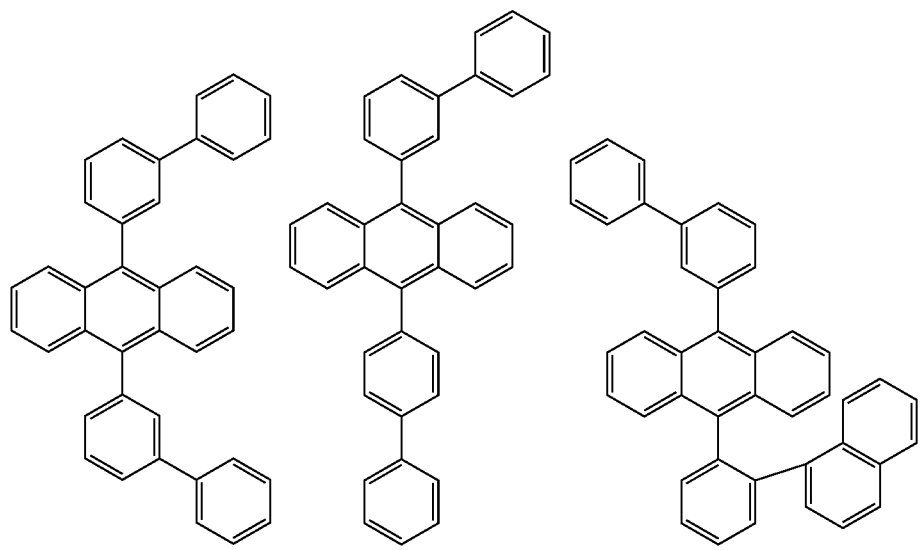

-continued
1025
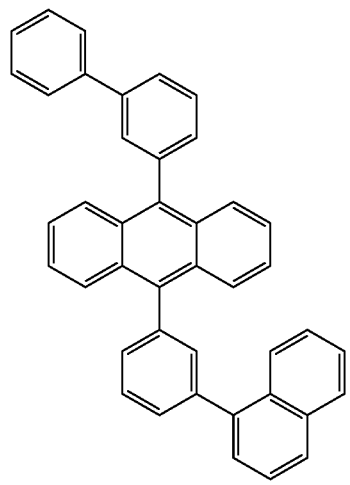
1026
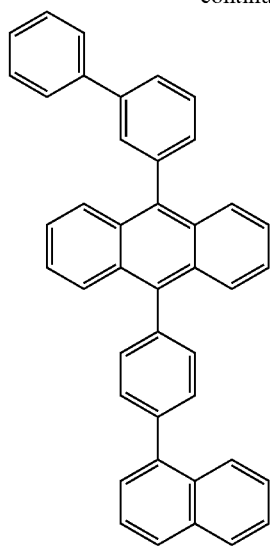
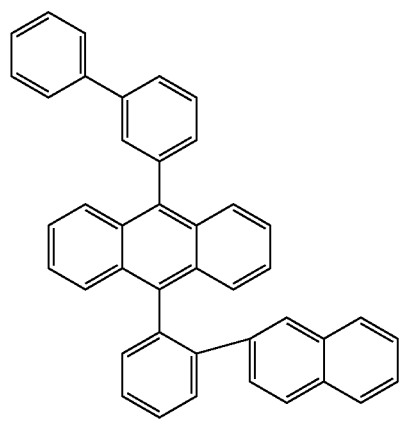
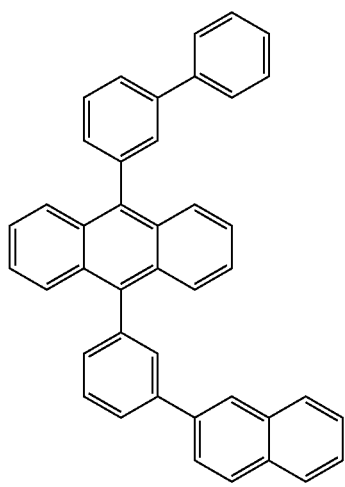
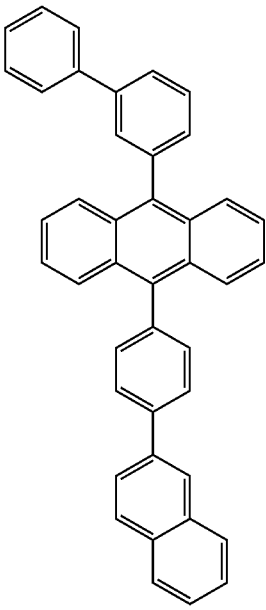
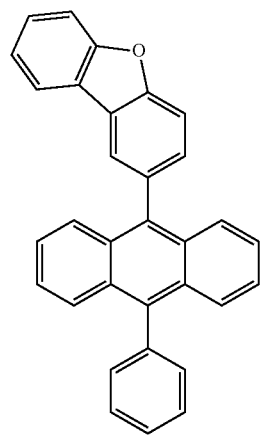
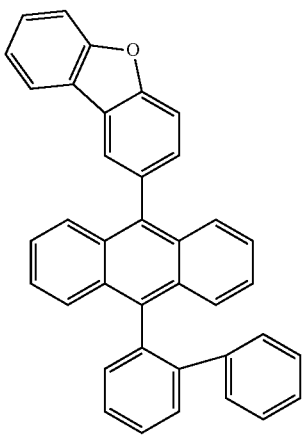
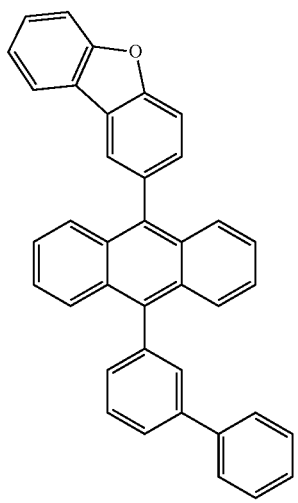

-continued
1027
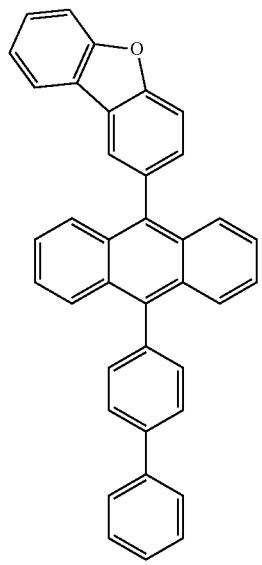
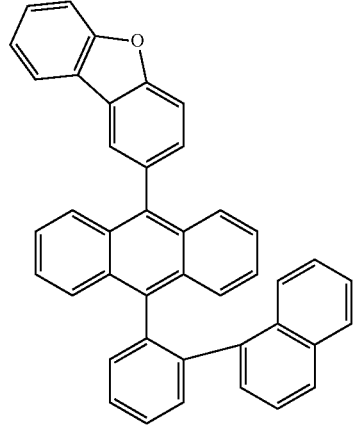
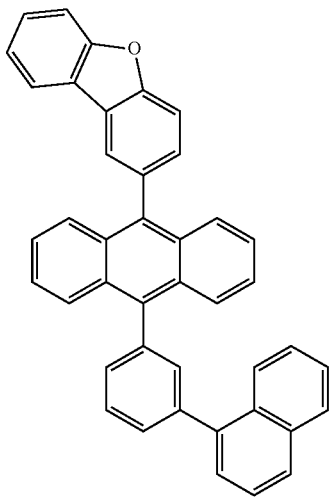
1028
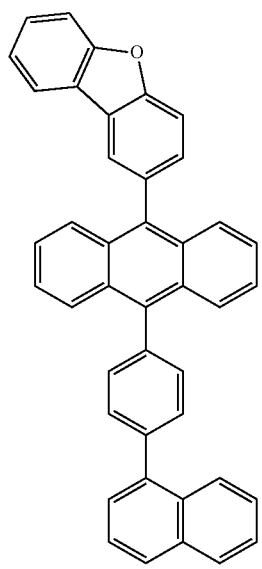
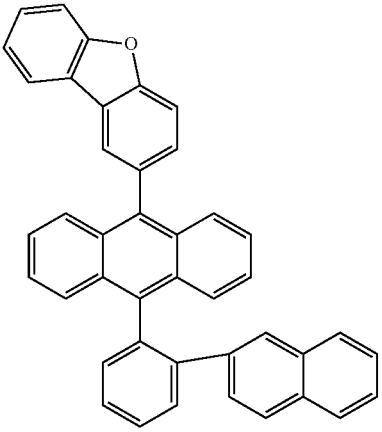
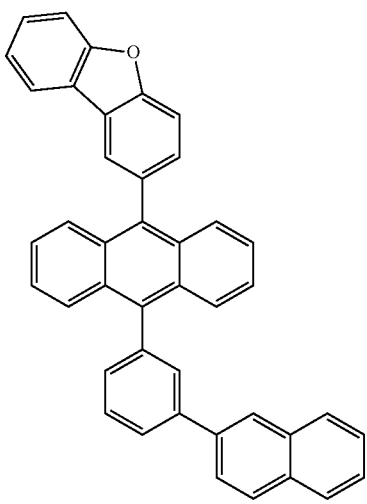

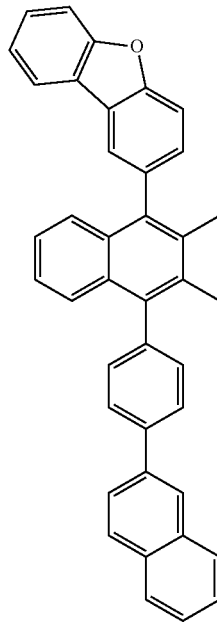
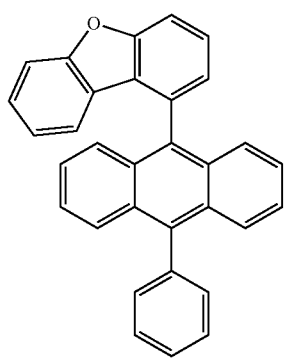
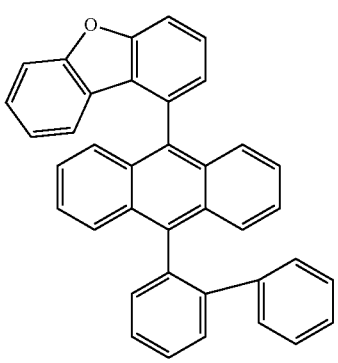
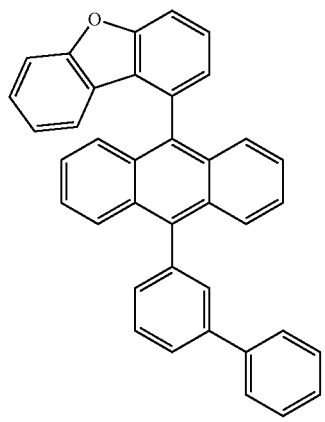
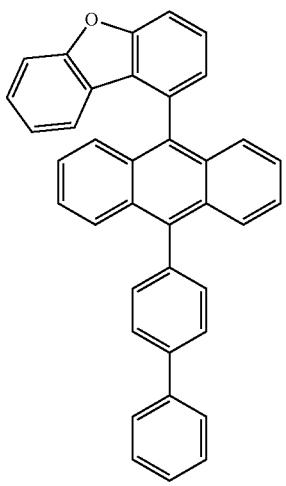
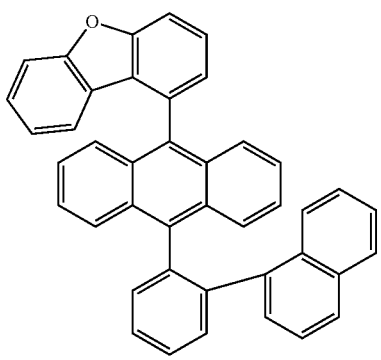
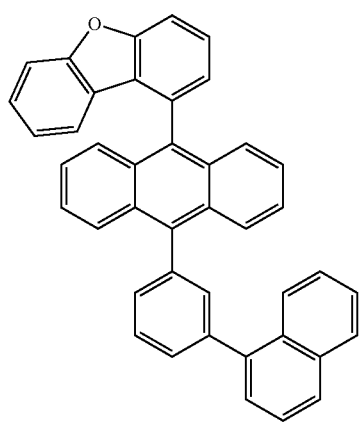
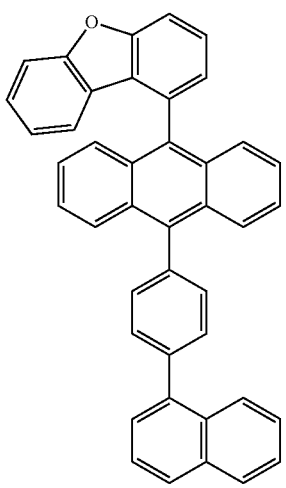
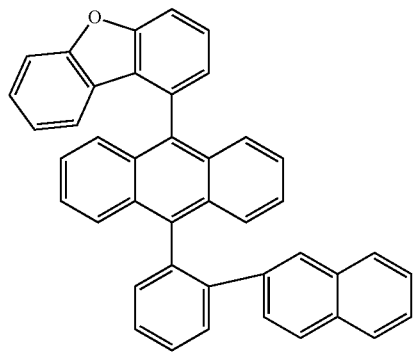

-continued
1031
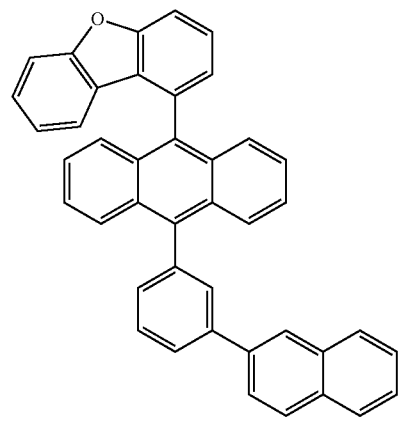
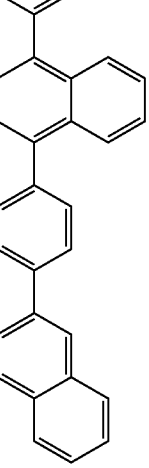
1032
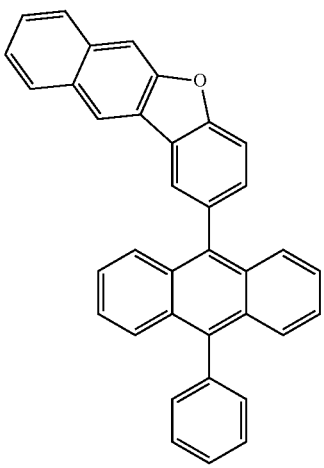
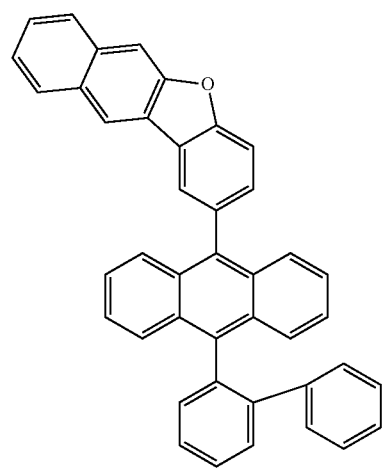
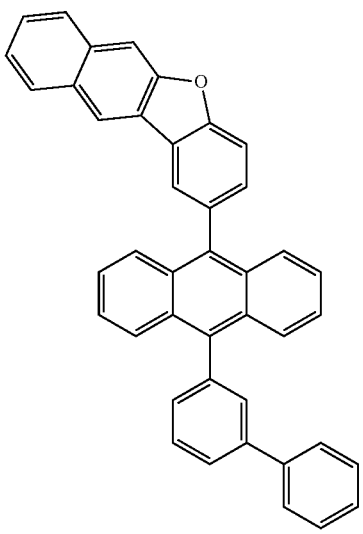
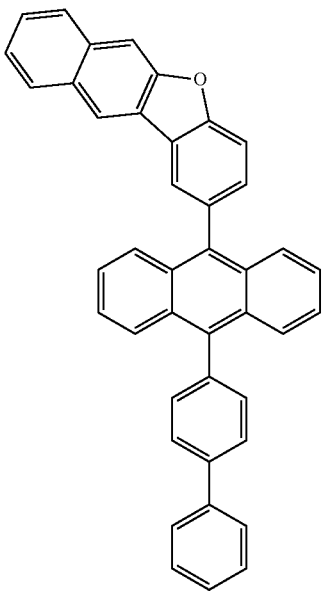
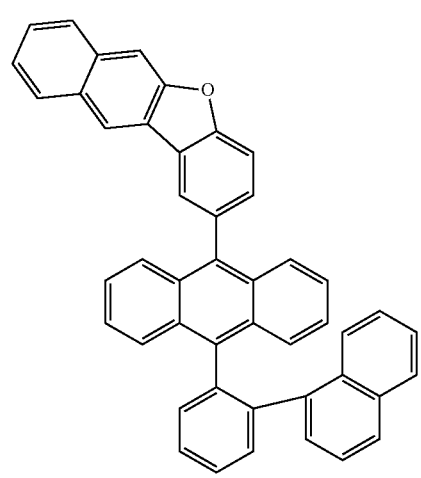
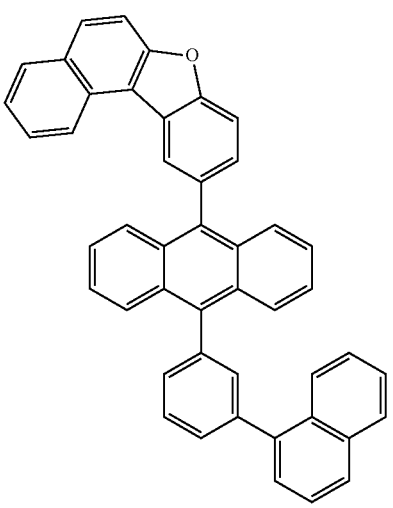
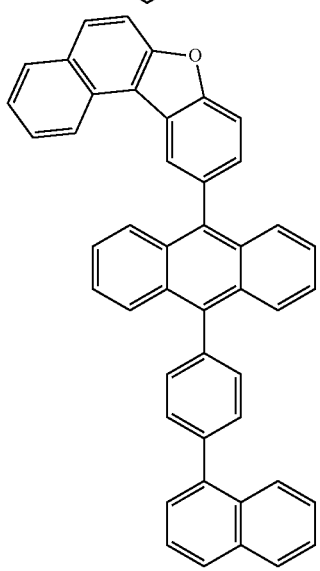

1033
1034
-continued
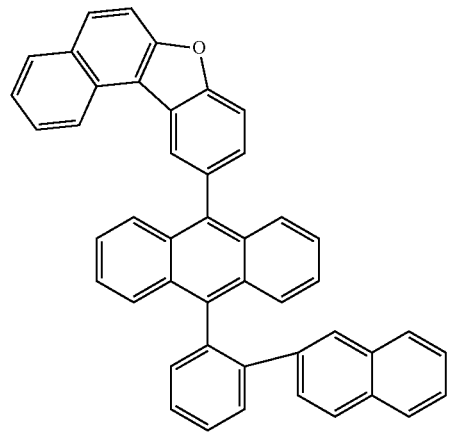
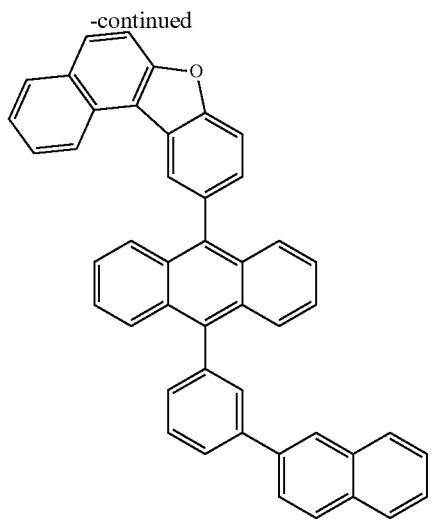
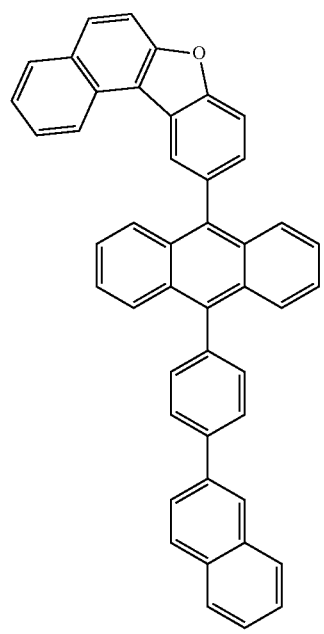
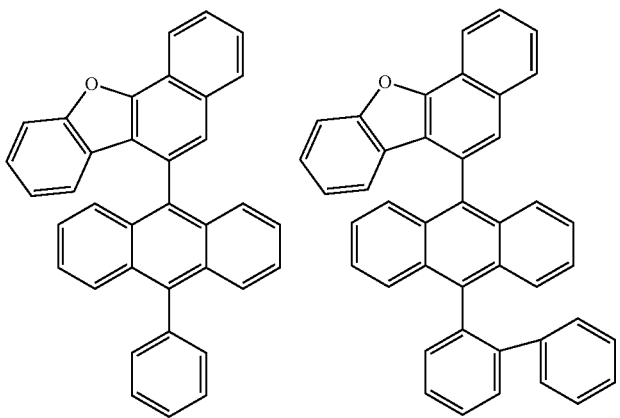
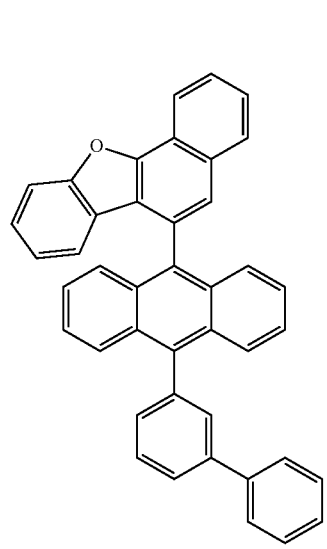
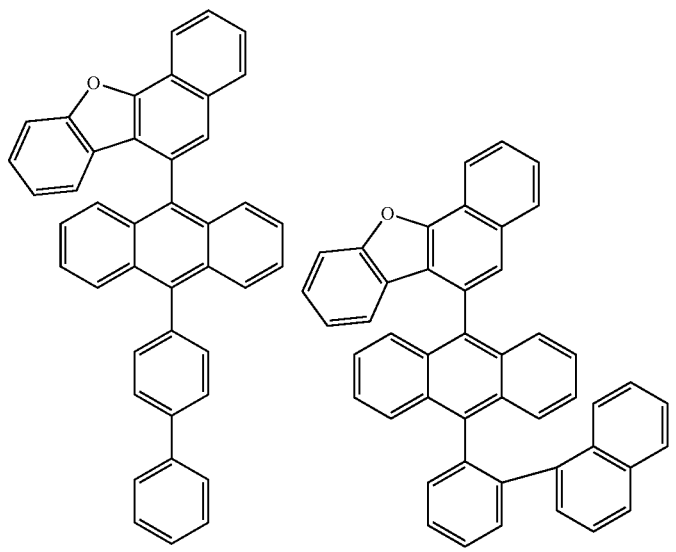

1035
-continued
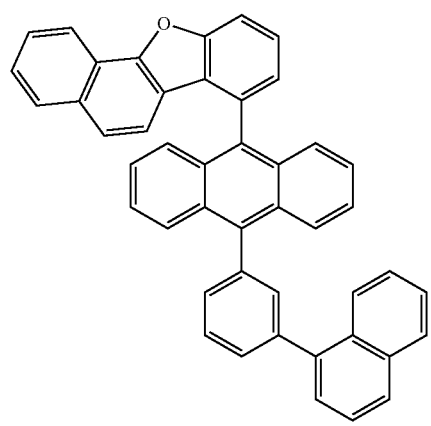
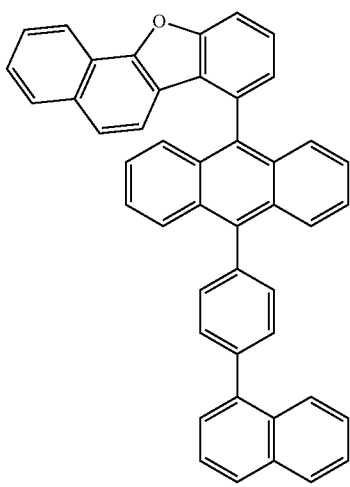
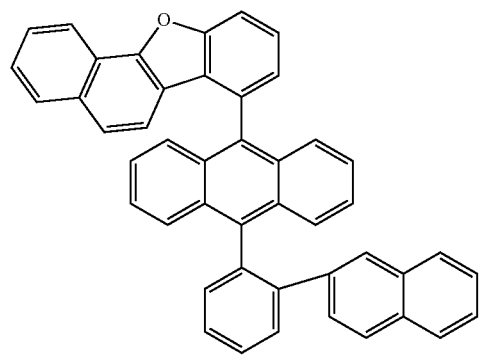
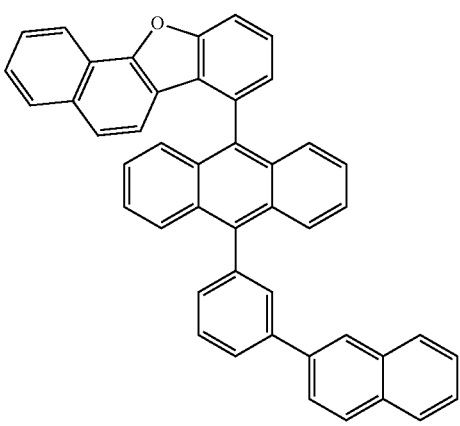
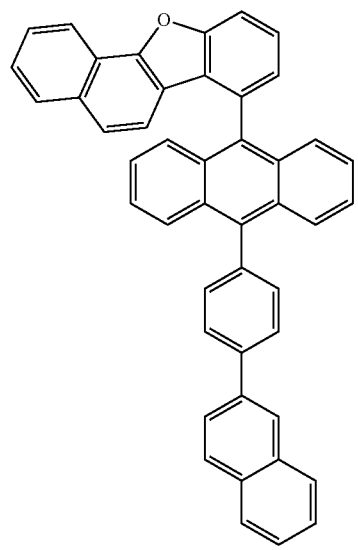
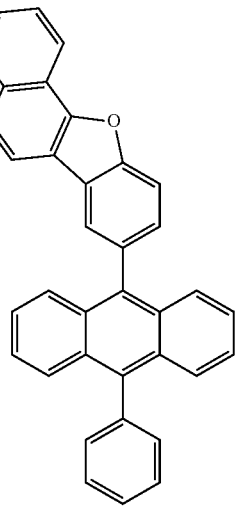
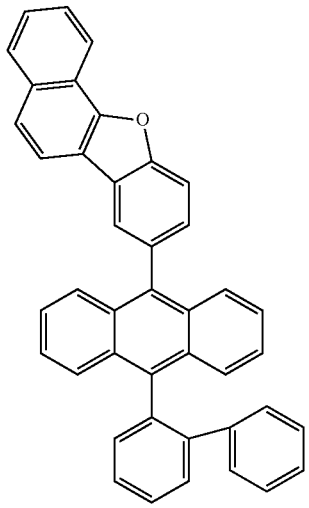
1036

1037 1038
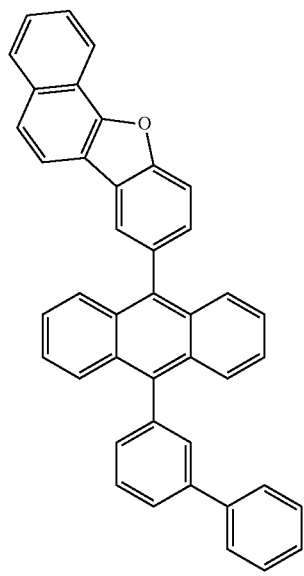
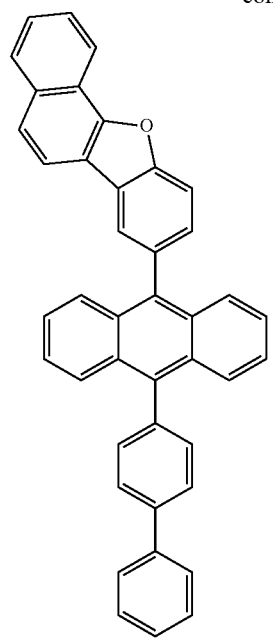
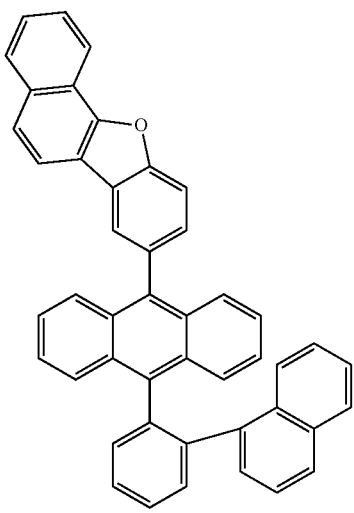
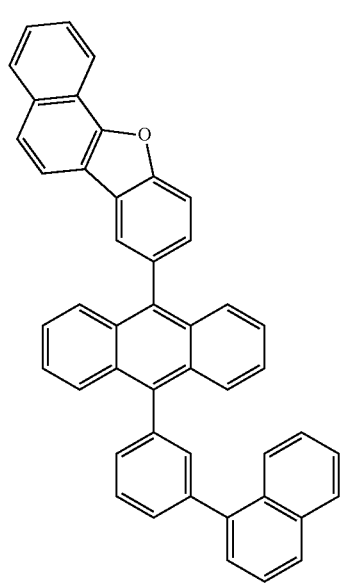
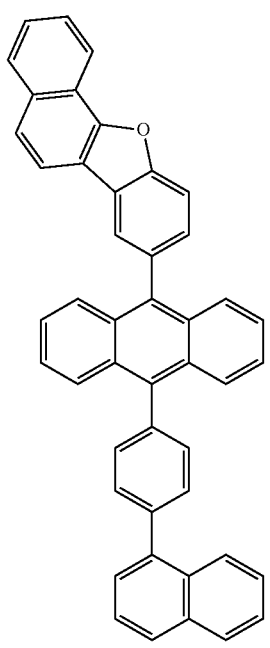
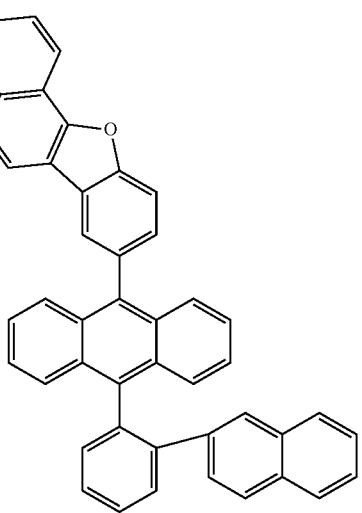

-continued
1039
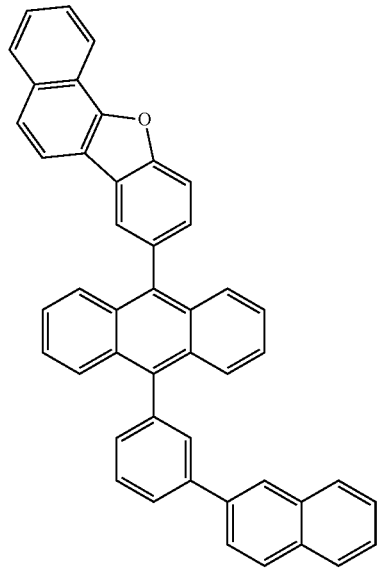
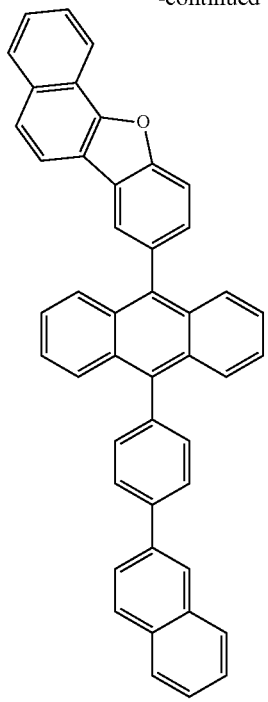
1040
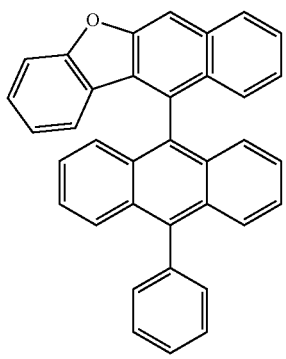
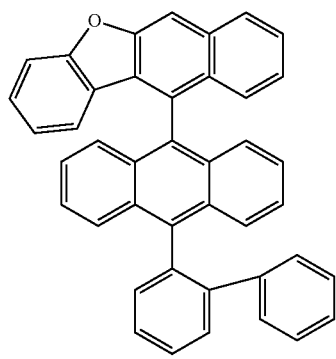
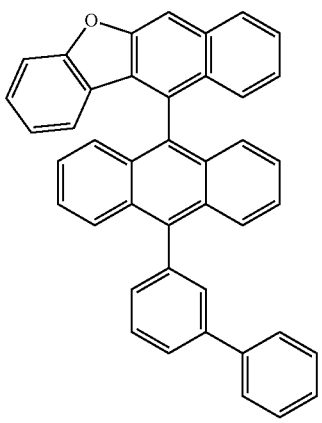
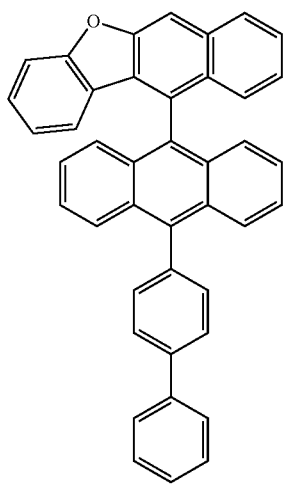
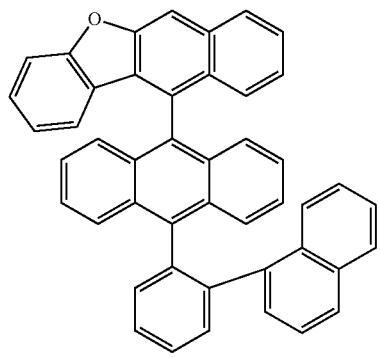
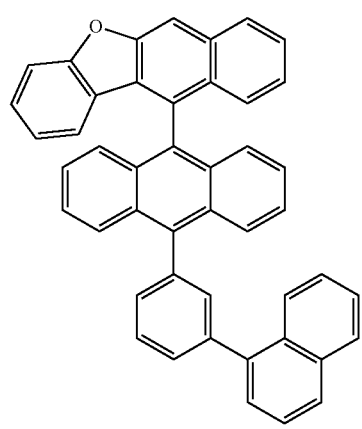

1041 1042
-continued
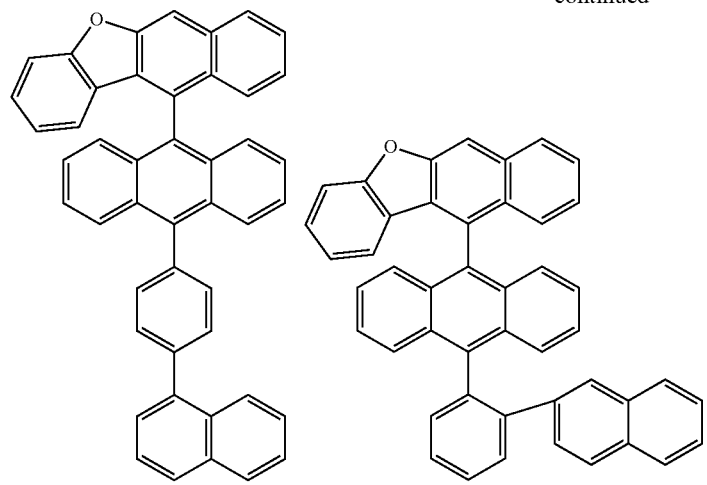
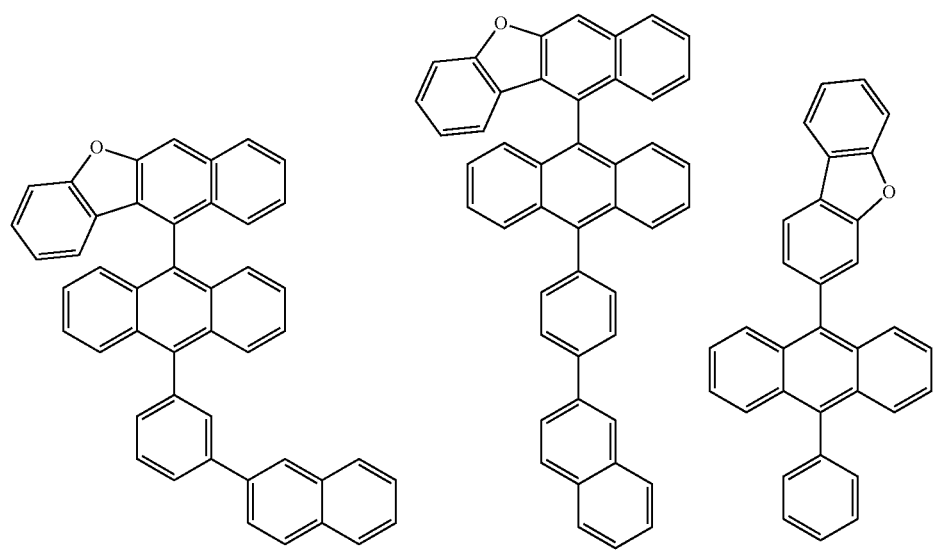
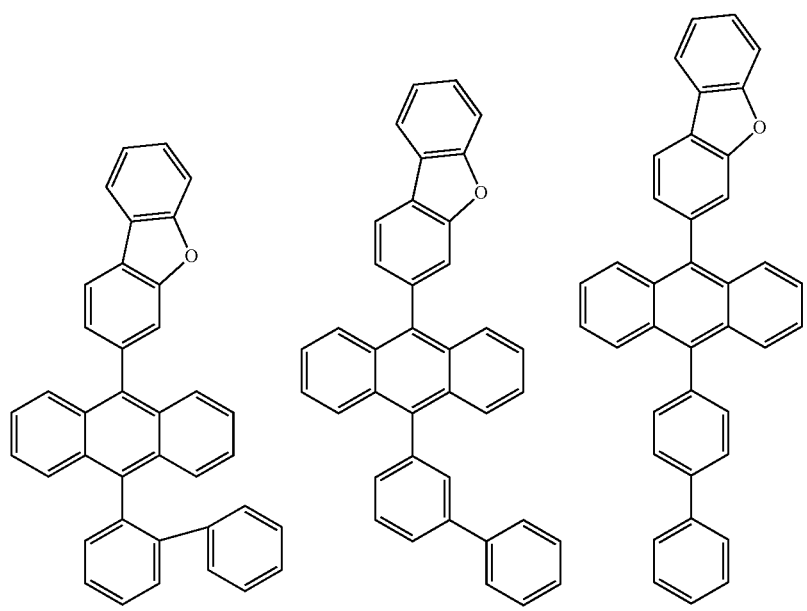

1043
-continued
1044
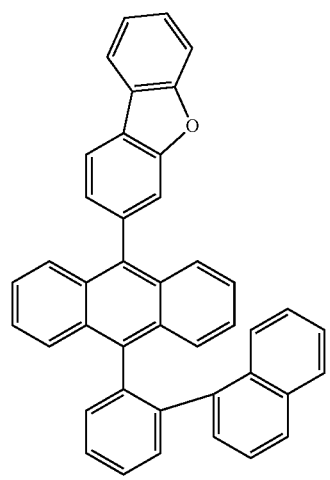
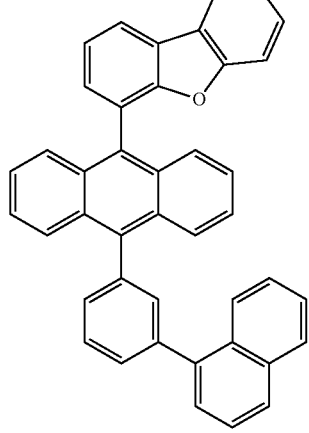
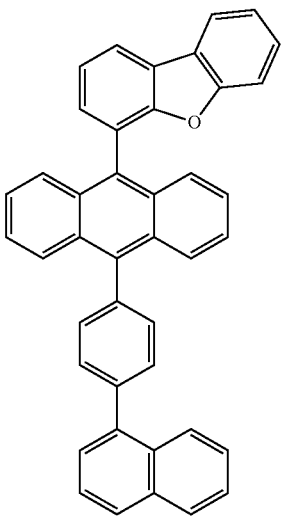
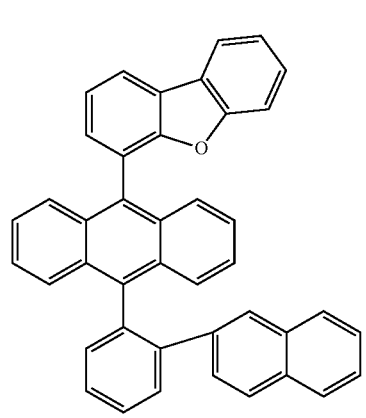
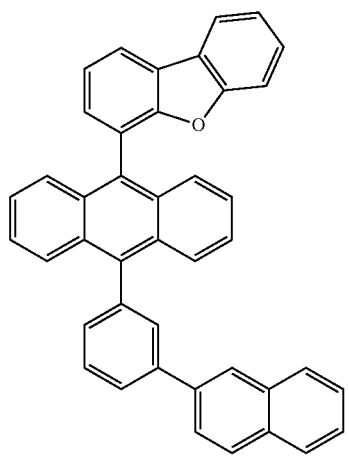
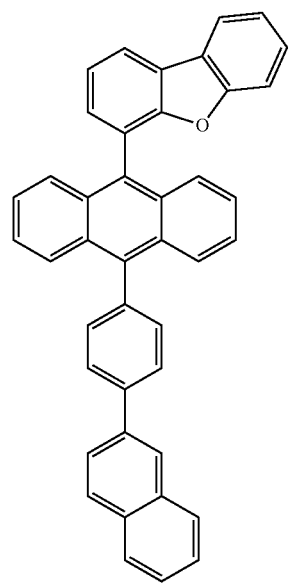
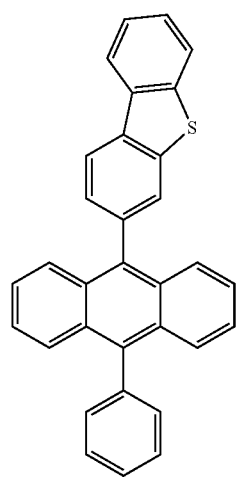
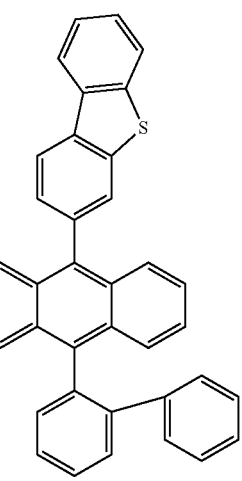
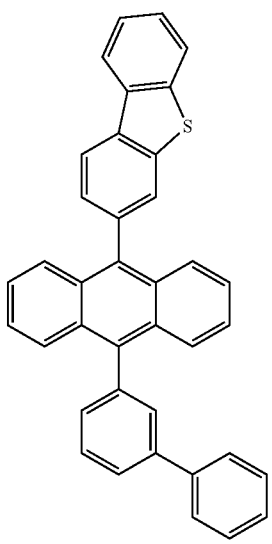

-continued
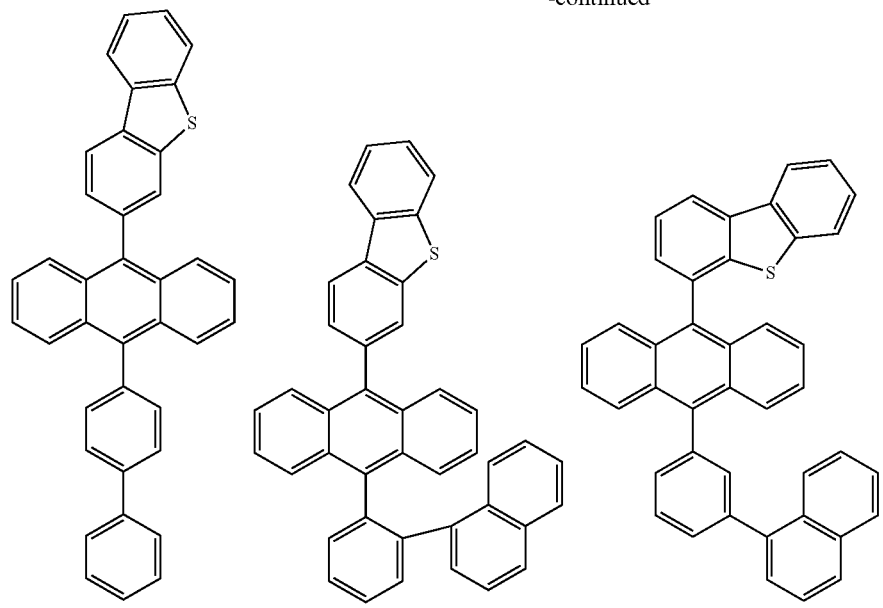
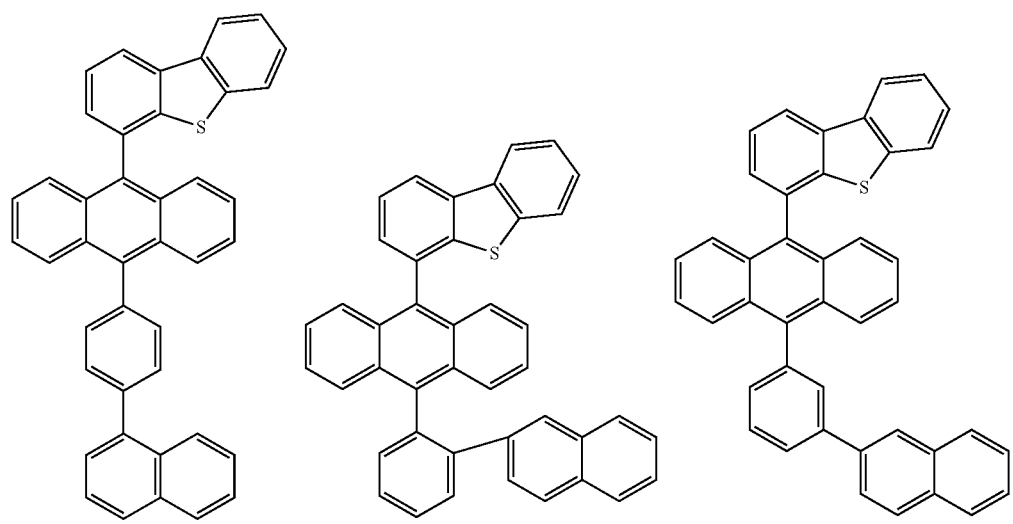
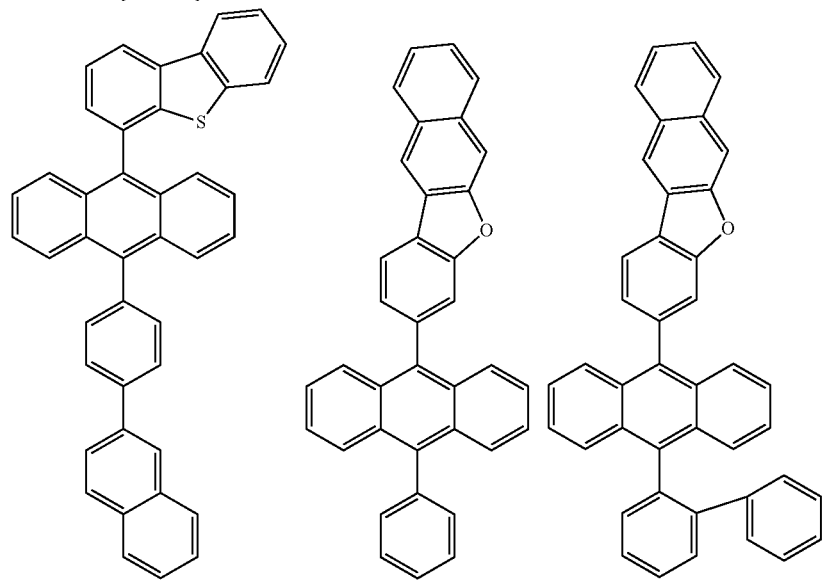

1047 1048
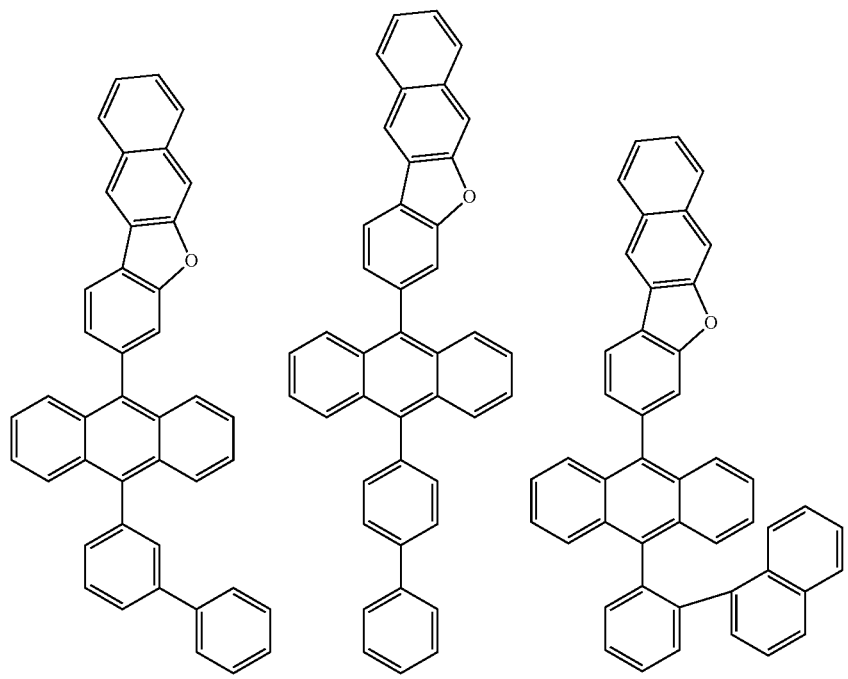
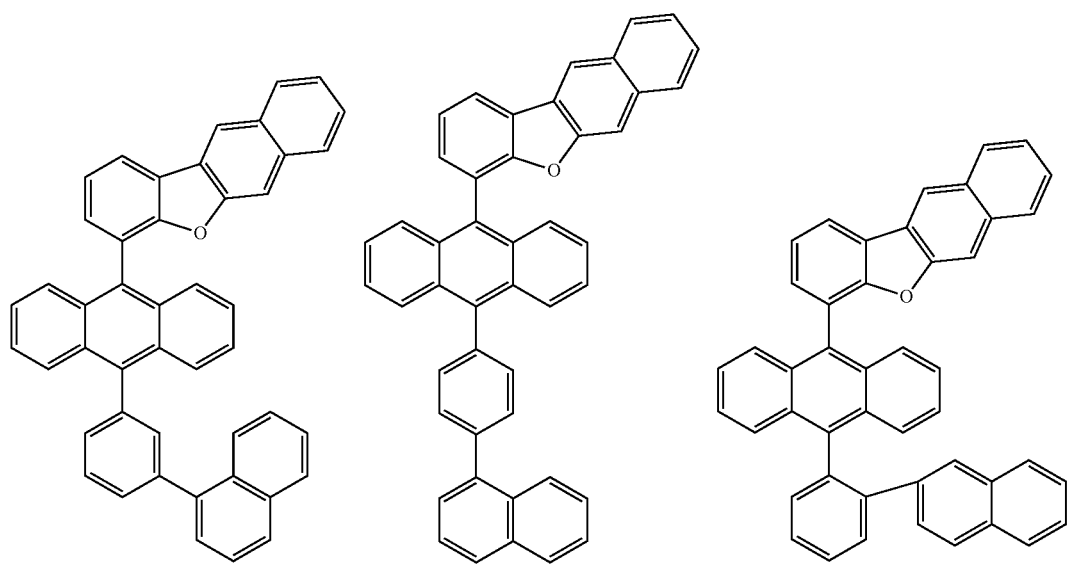

-continued
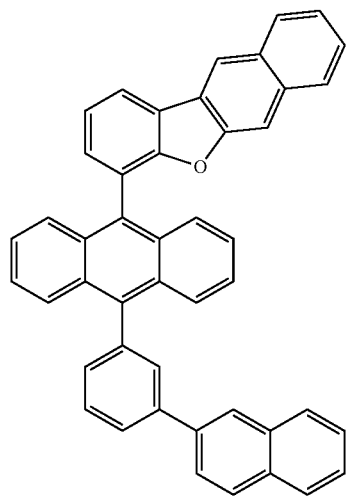
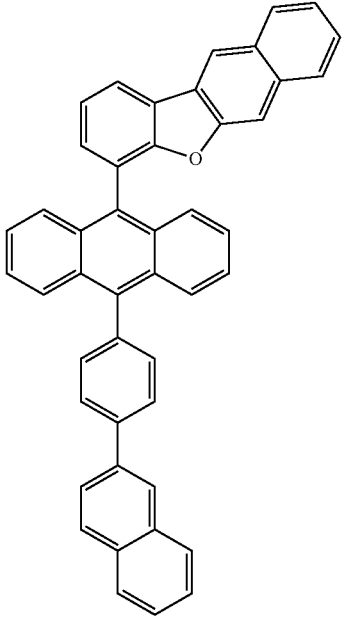
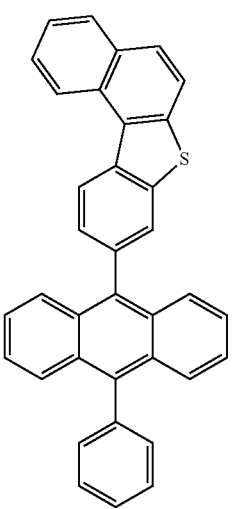
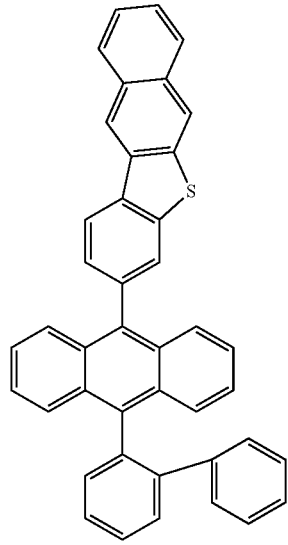
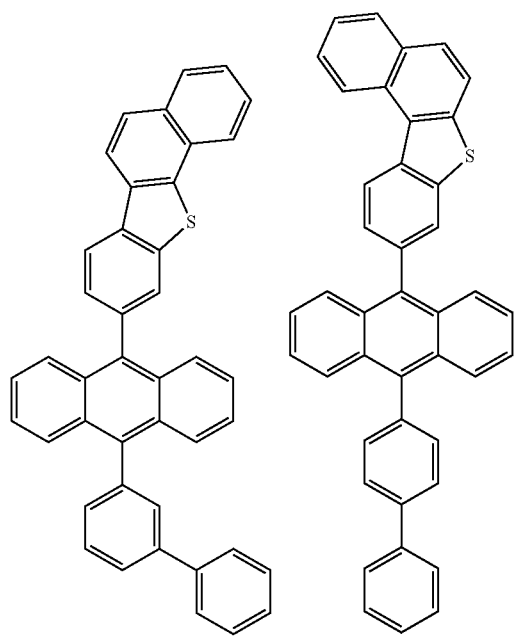

1051
1052
-continued
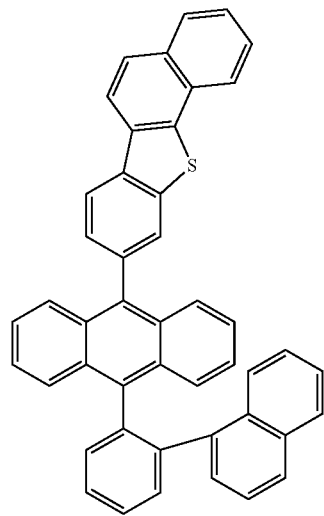
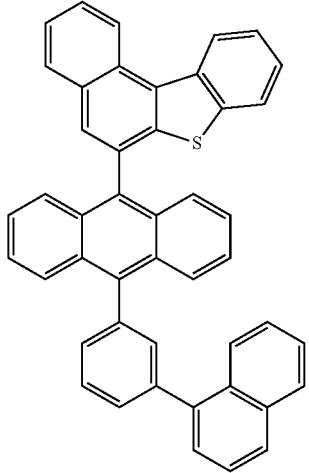
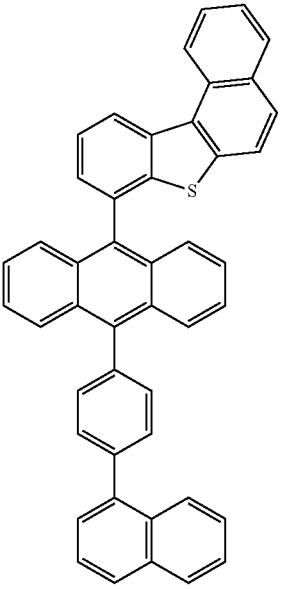
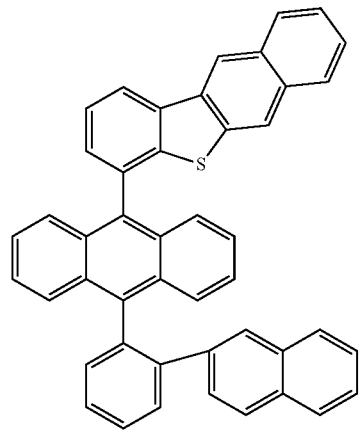
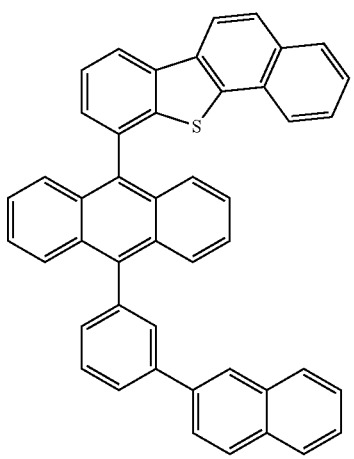
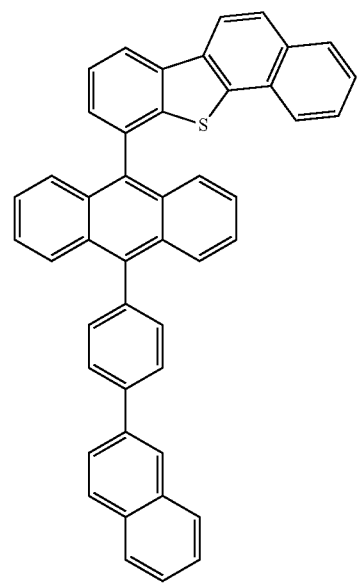
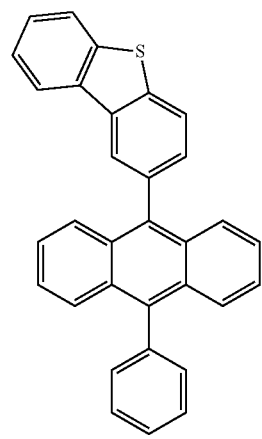
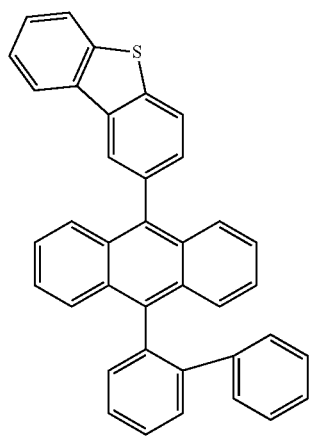
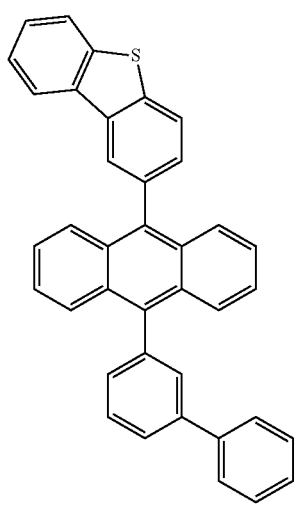

1053
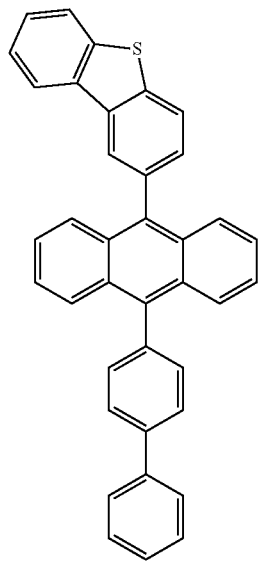
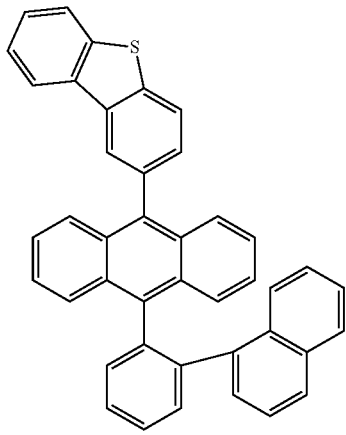
1054
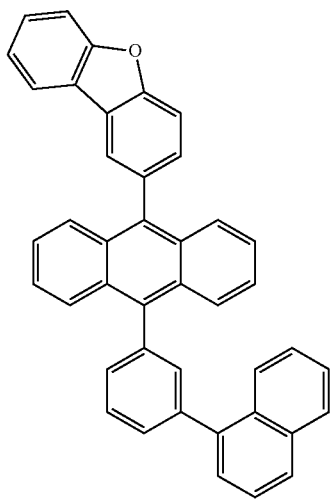
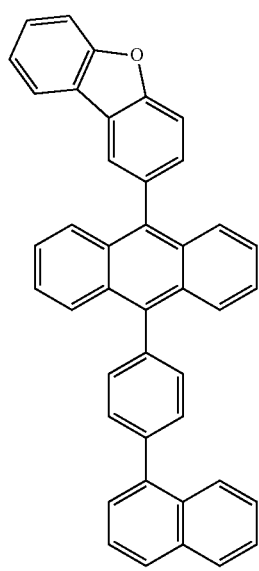
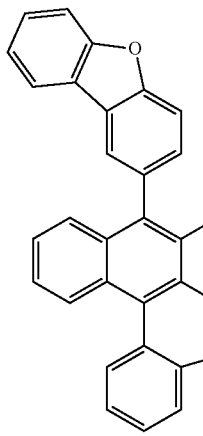
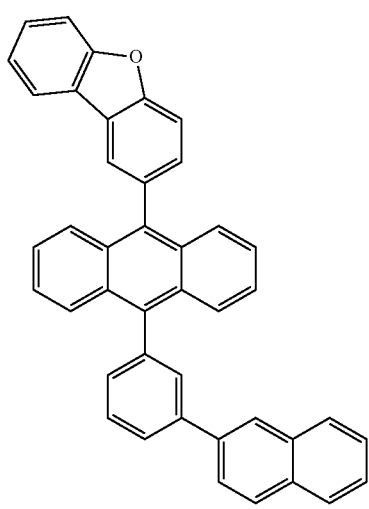

1055
1056
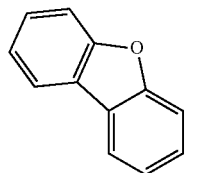
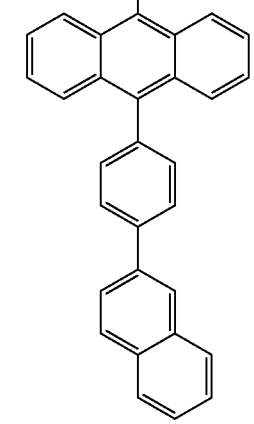
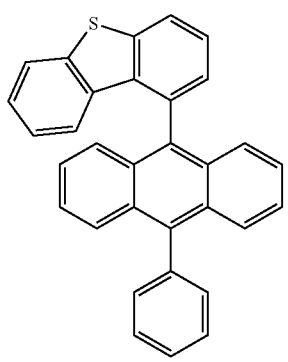
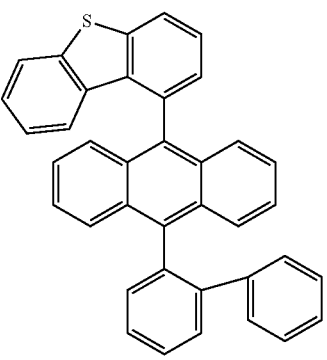
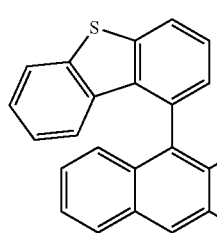
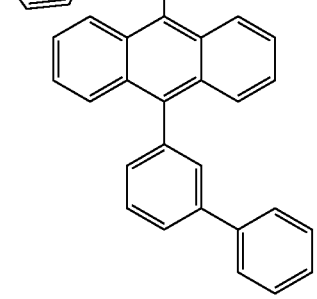
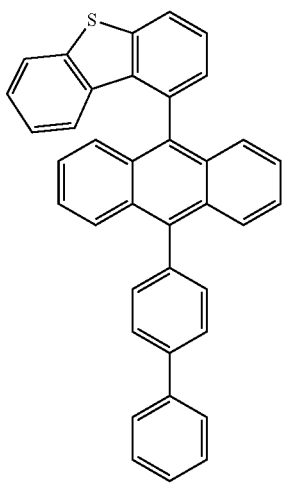
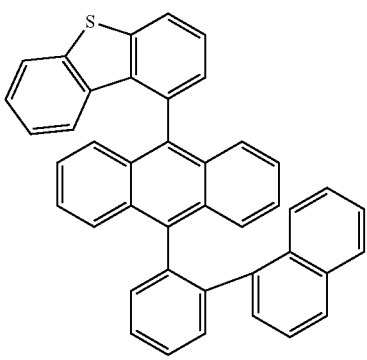
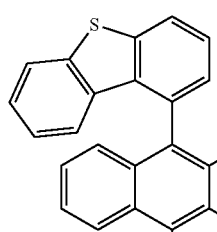
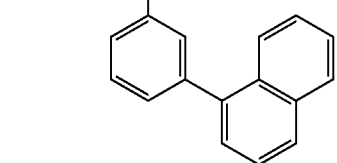
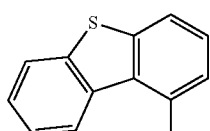
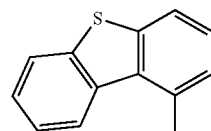
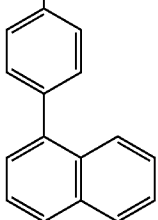
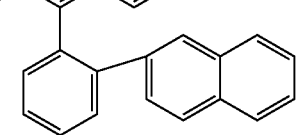

-continued
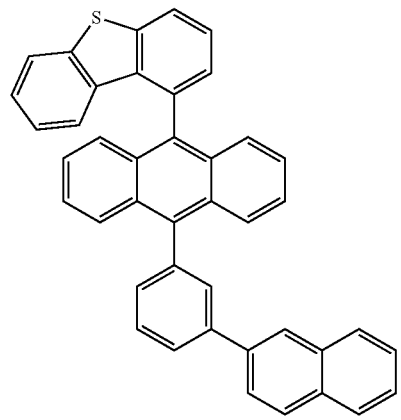
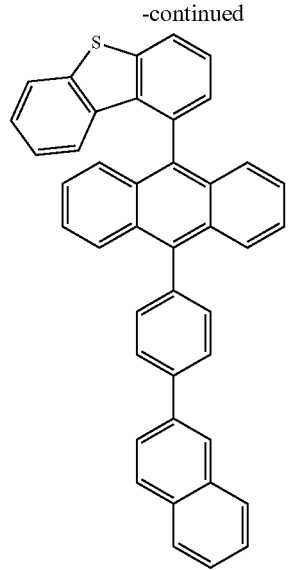
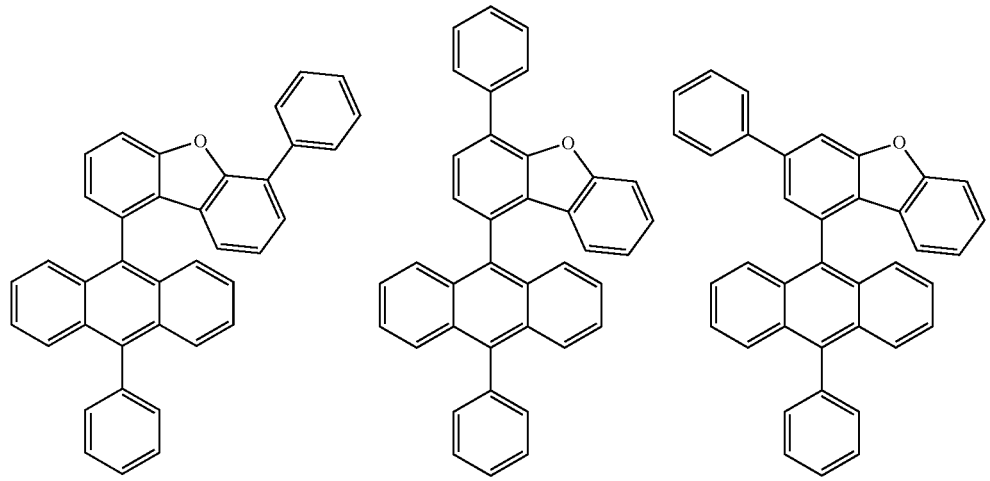
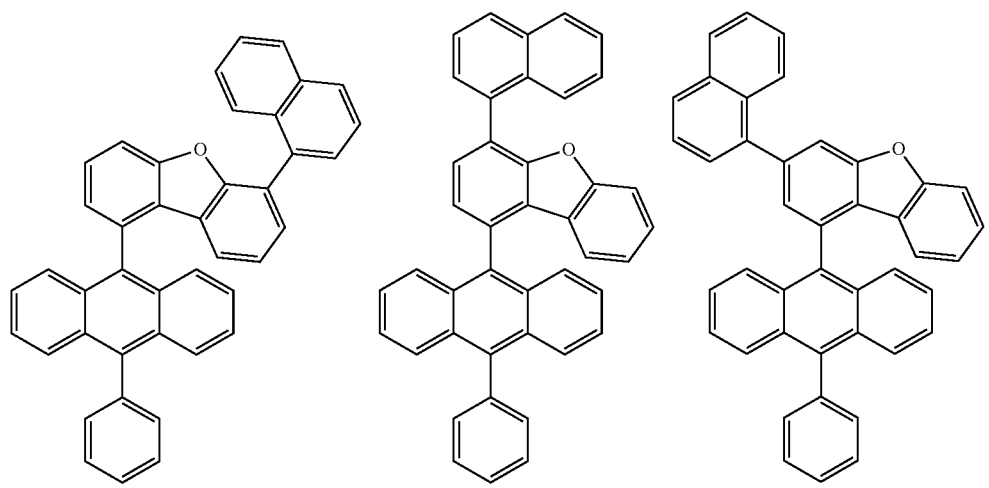

1059
1060
-continued
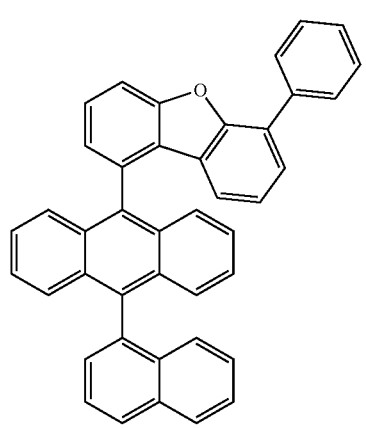
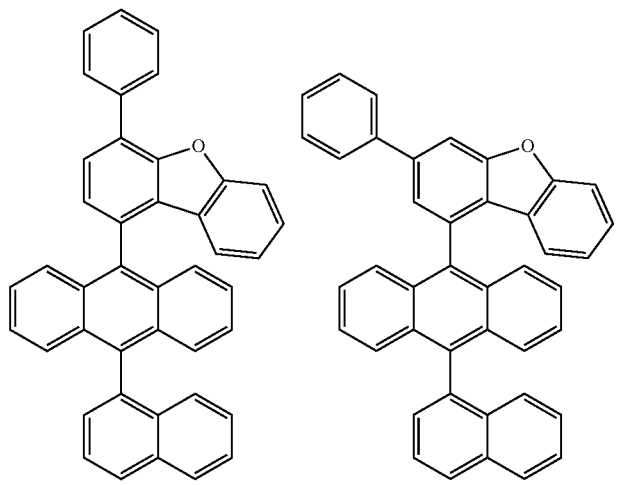
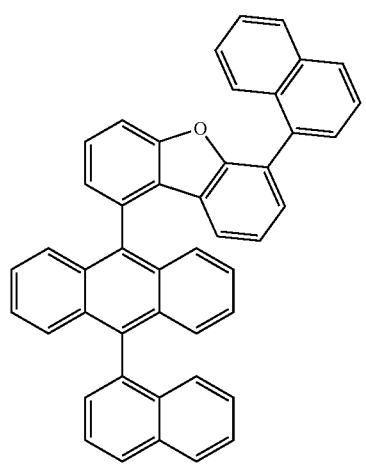
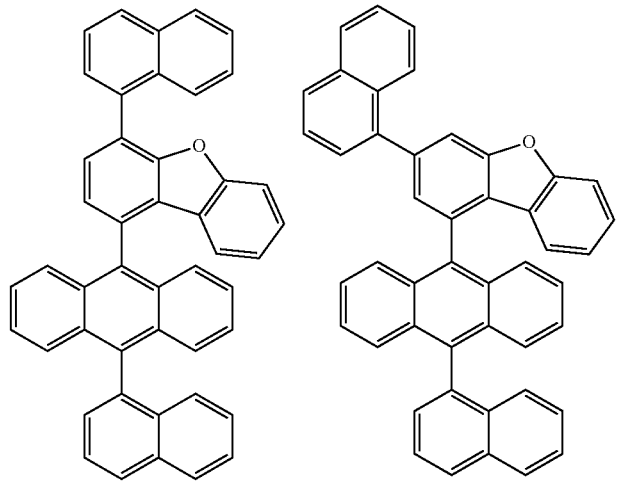
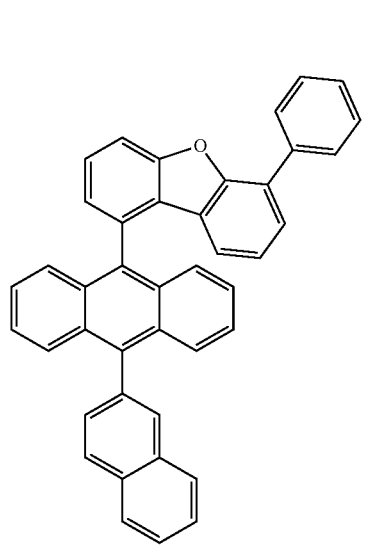
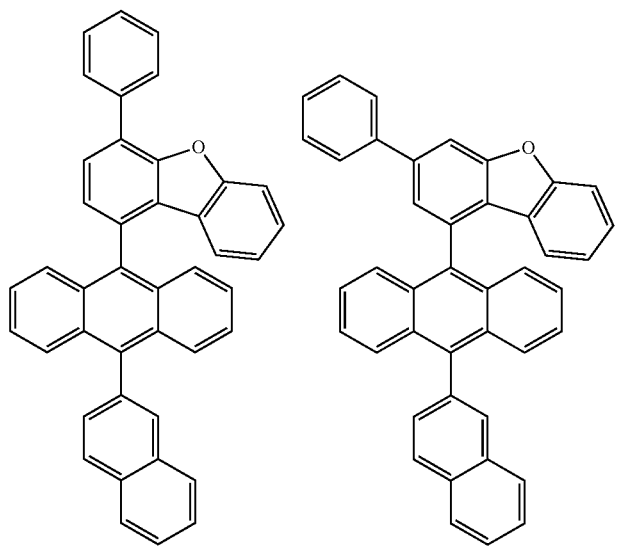

1061  1062
-continued
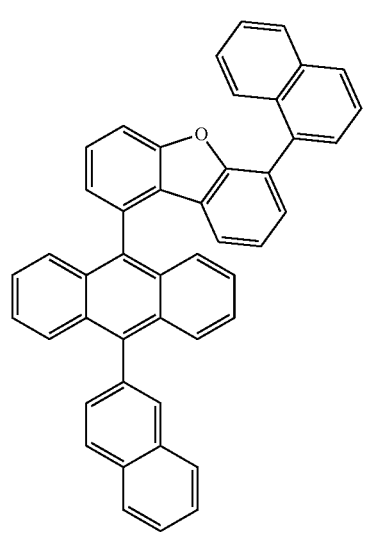
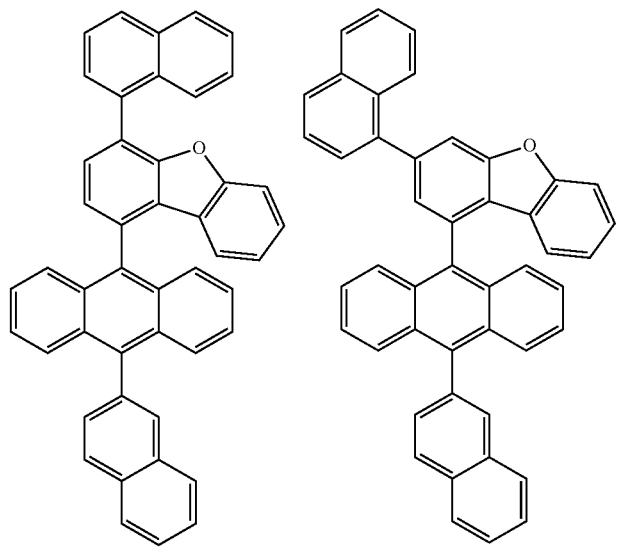
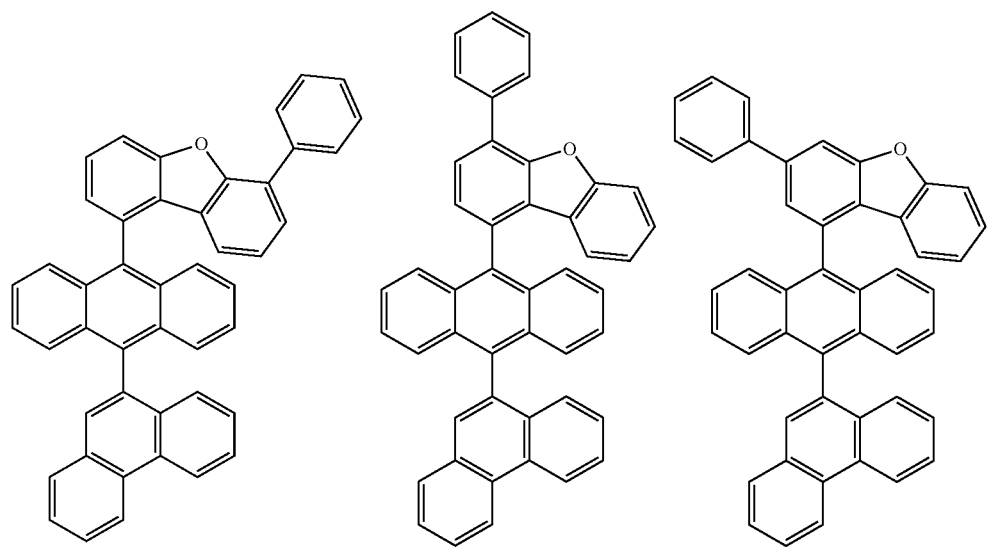
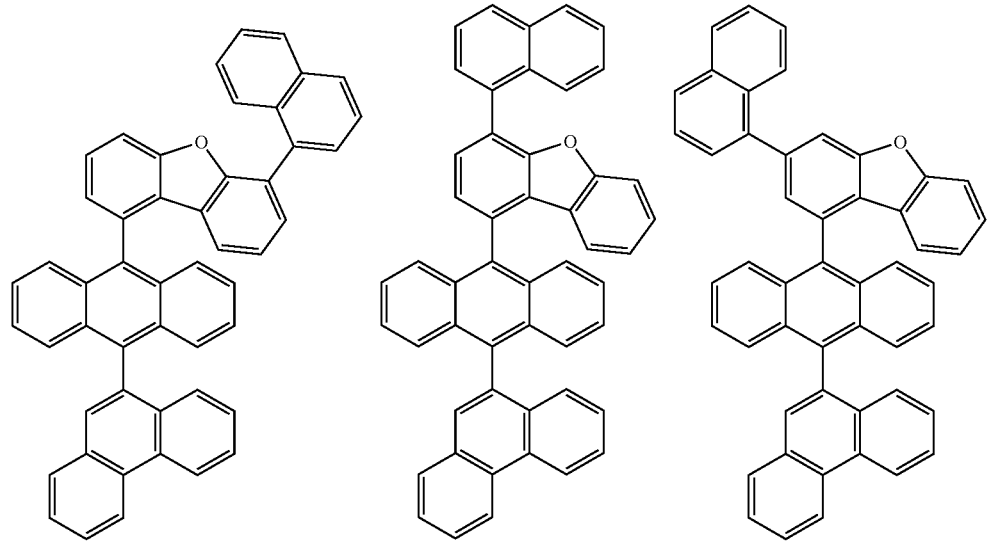

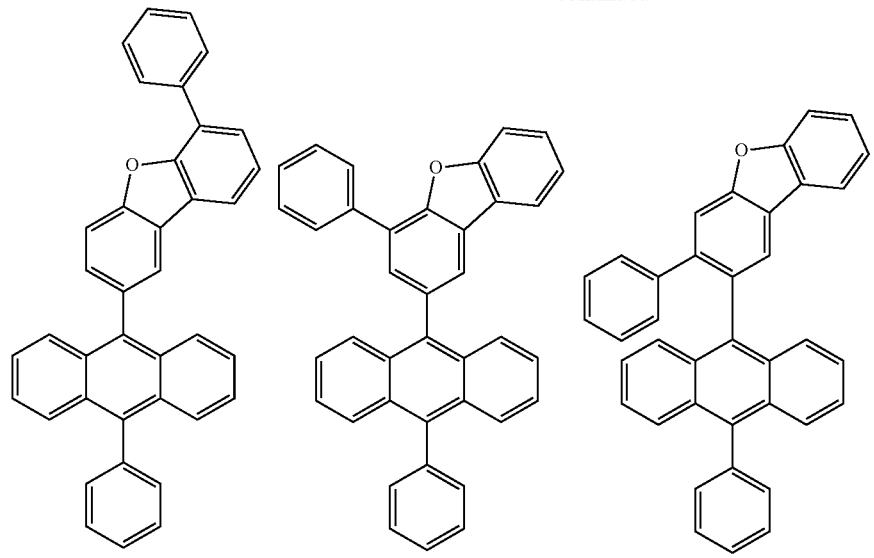
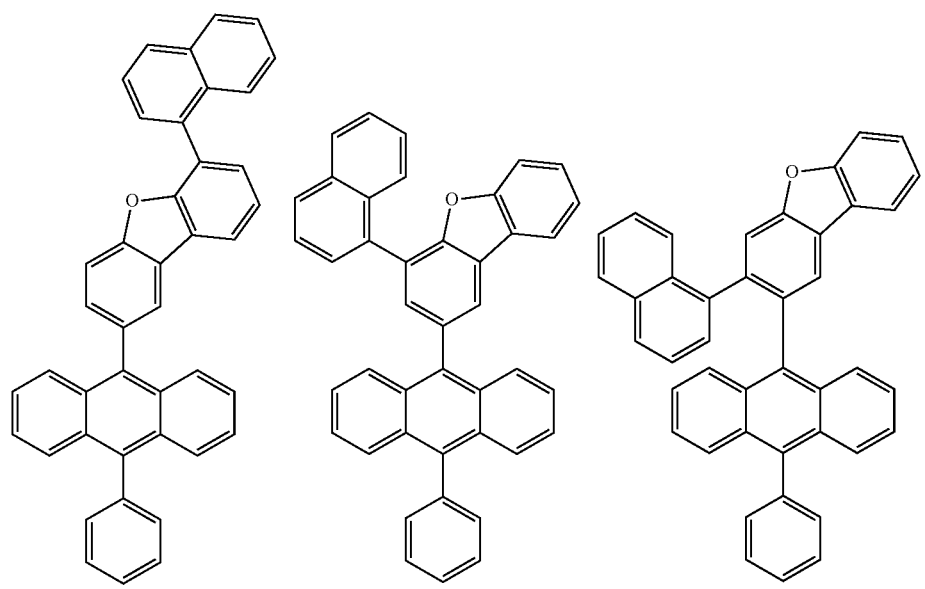
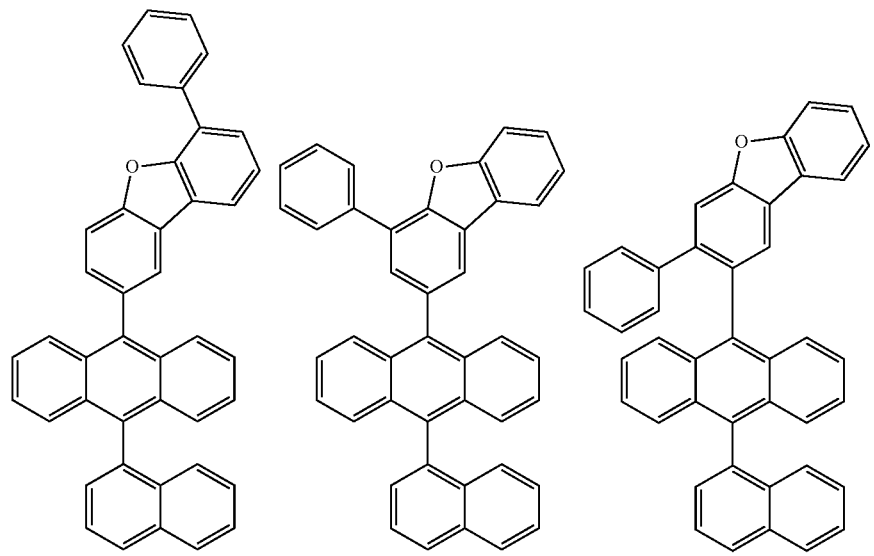

1065
1066
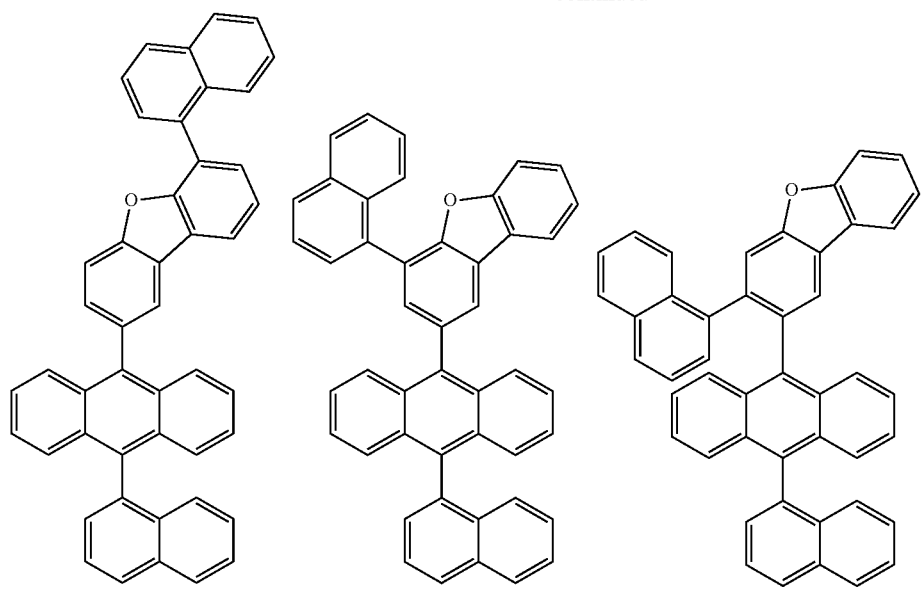
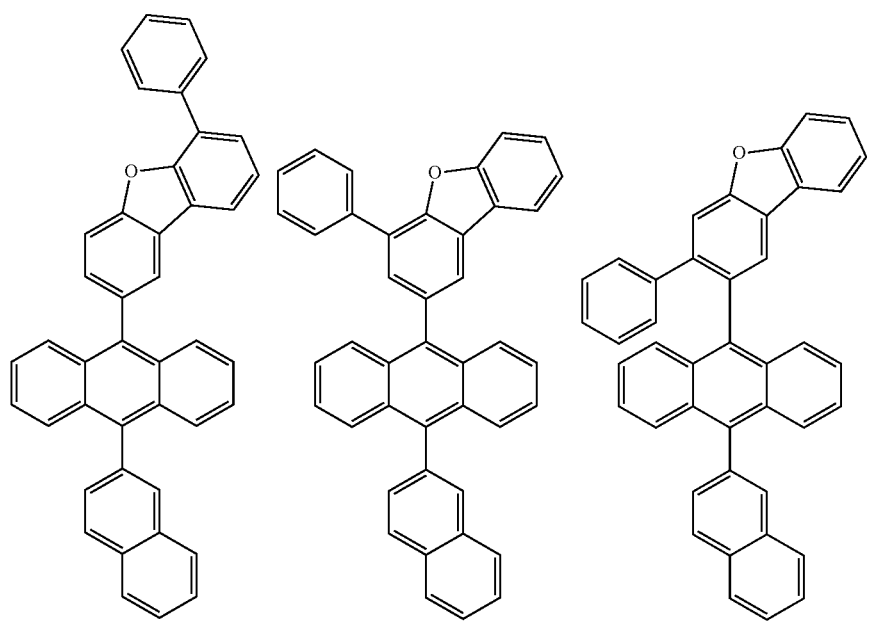

1067
1068
-continued
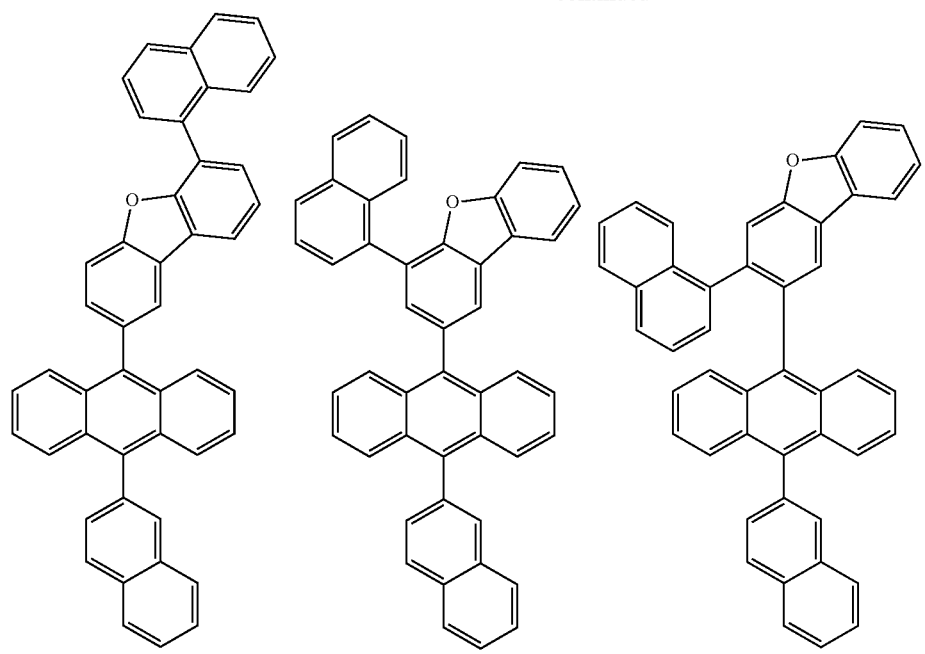
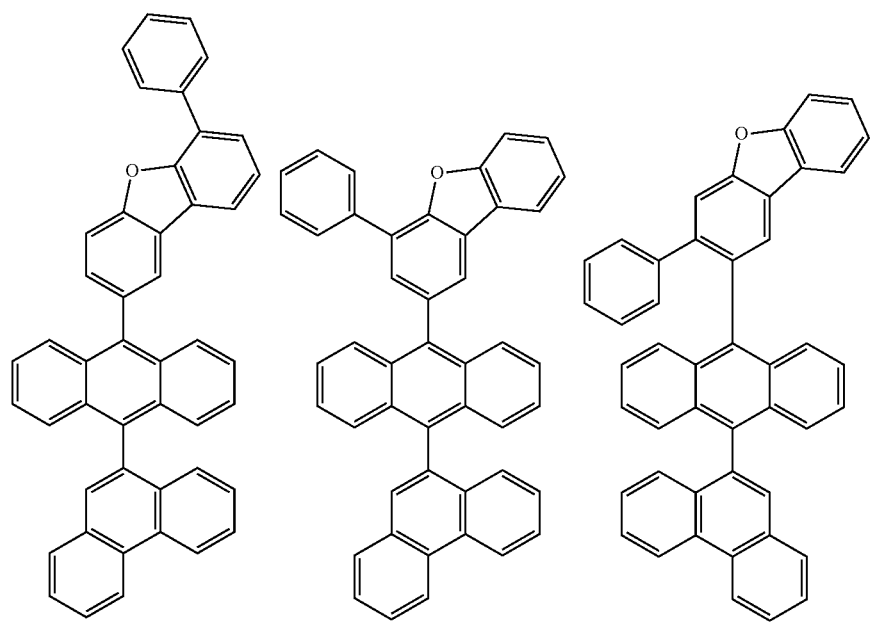

1069 -continued 1070
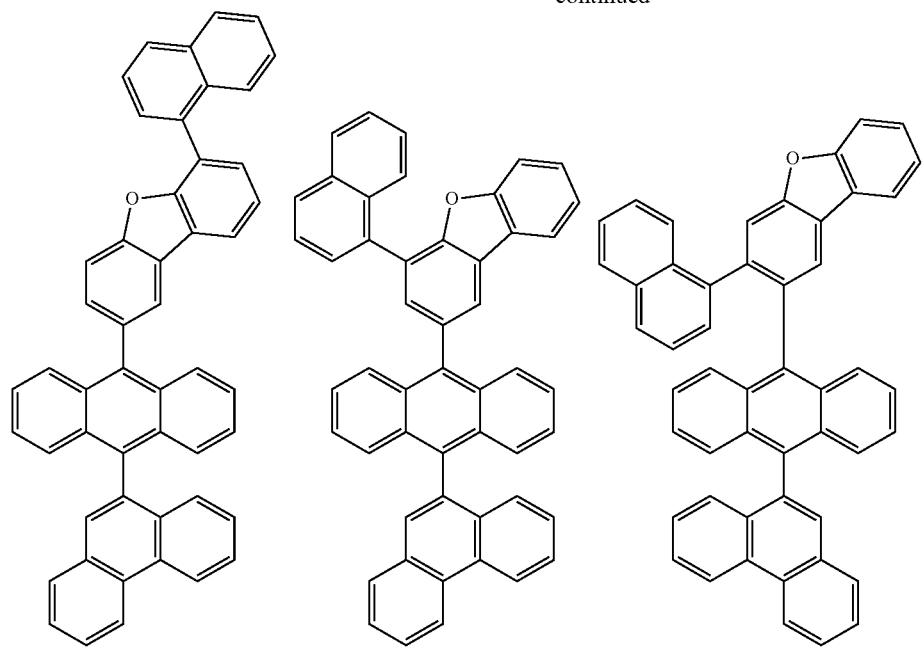
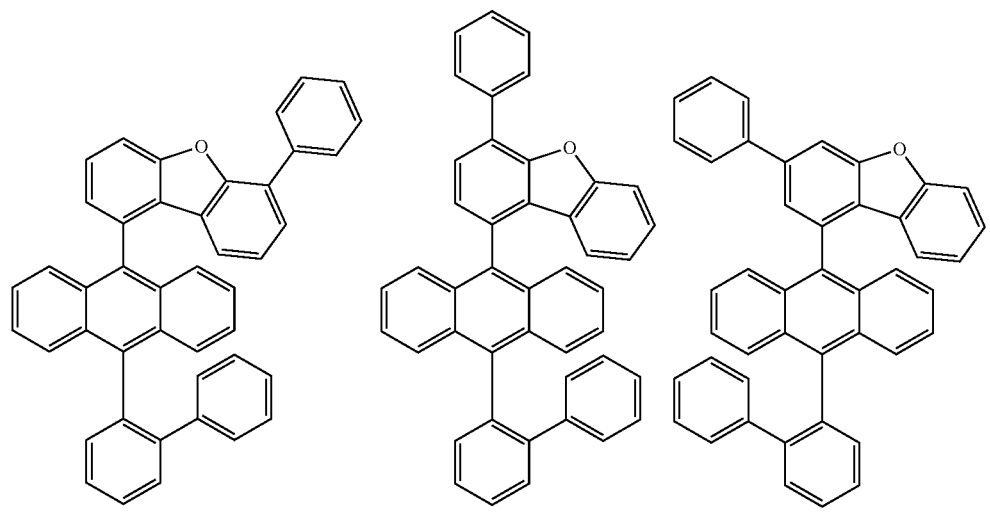
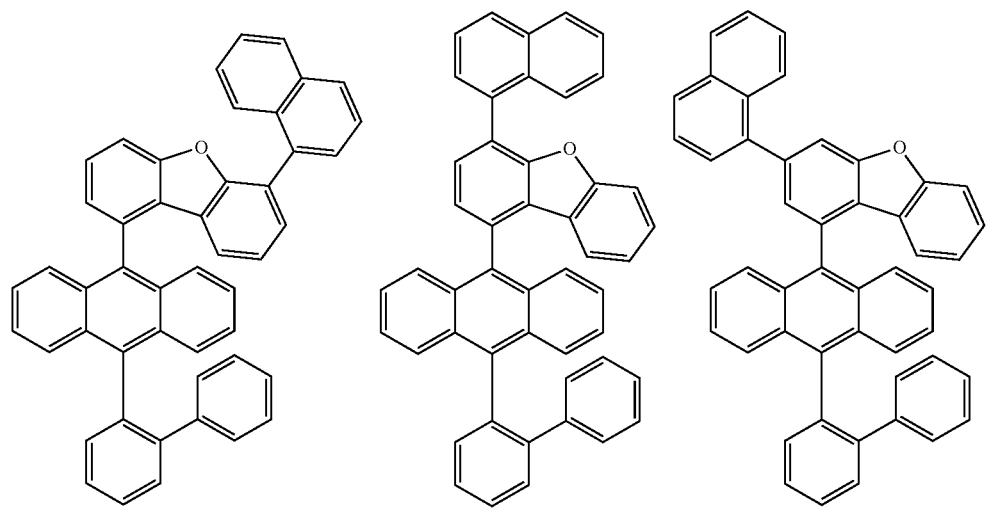

1071
1072
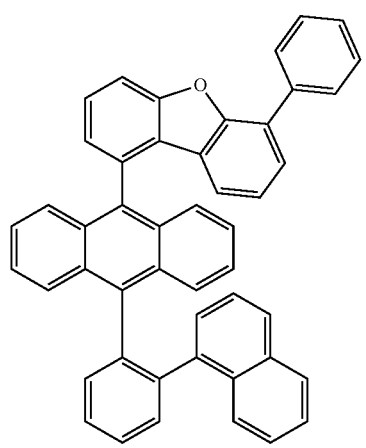
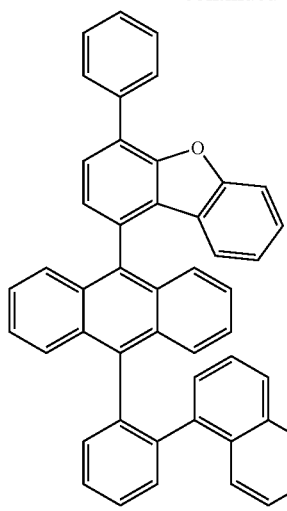
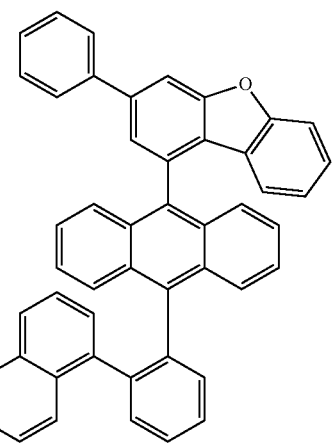
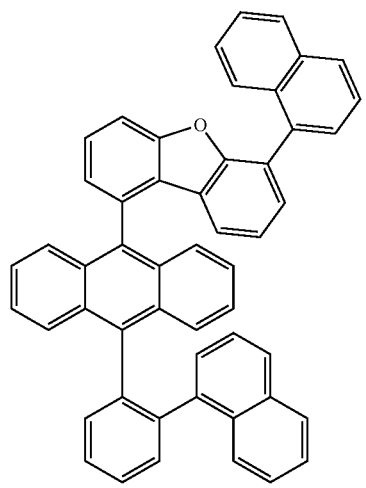
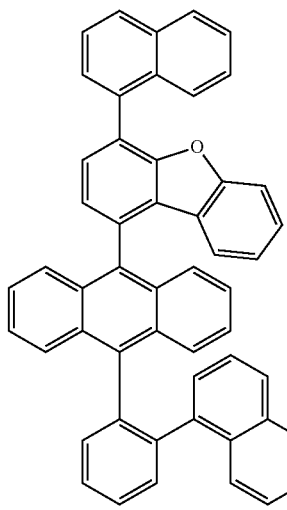
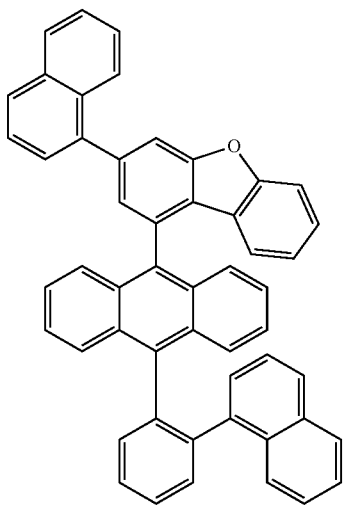
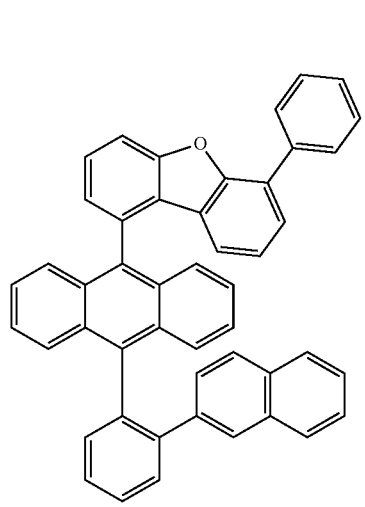
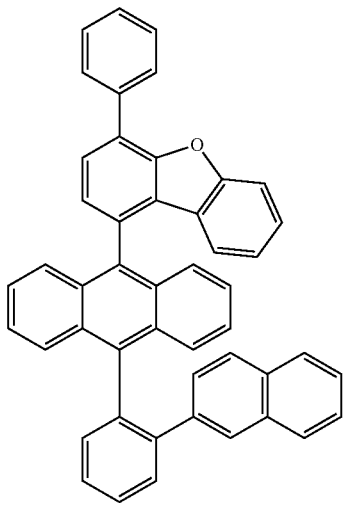
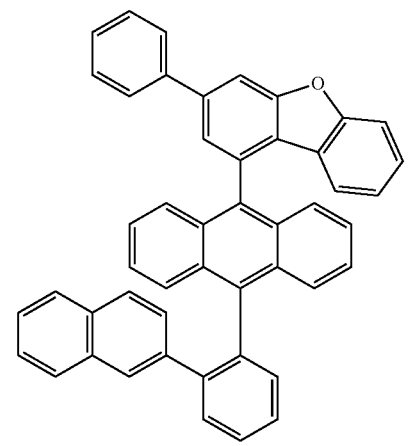

1073
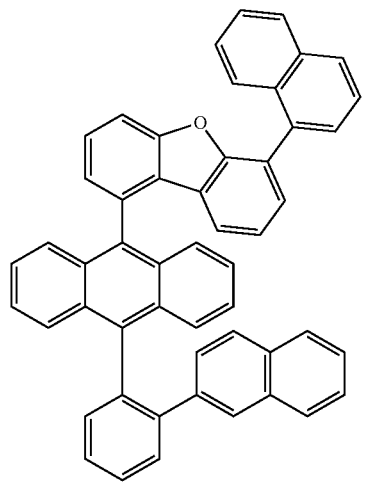 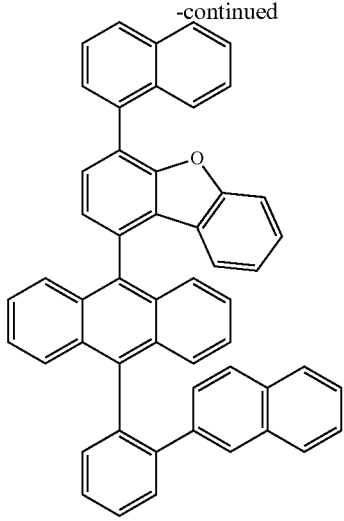
1074
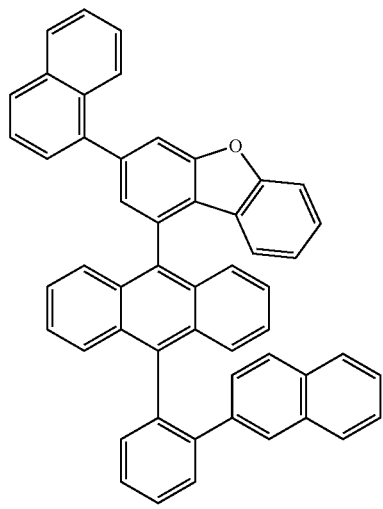
-continued
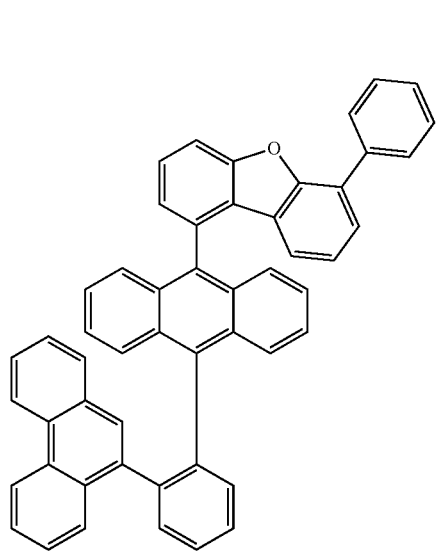 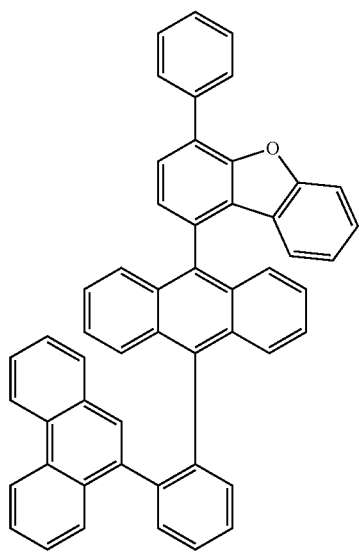 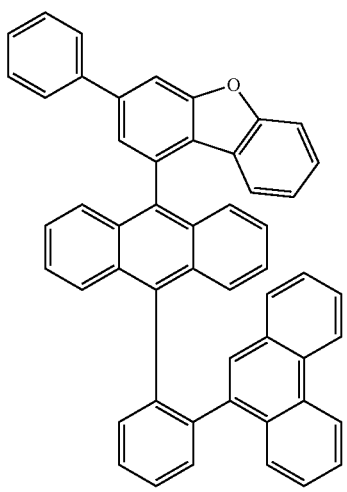
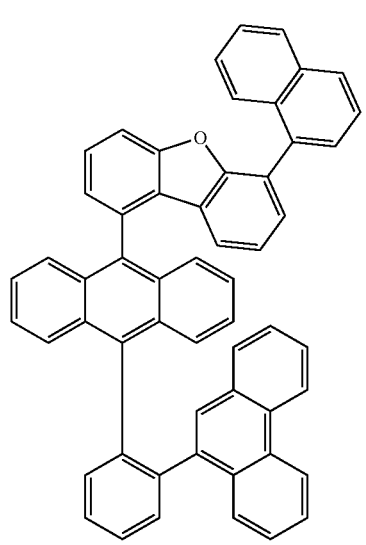 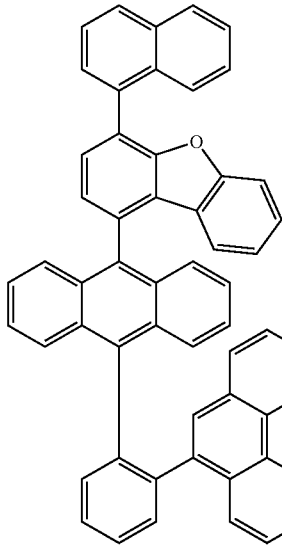 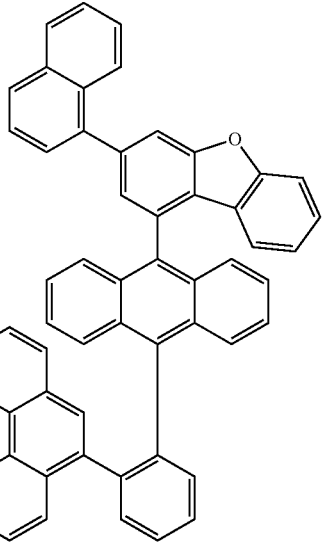

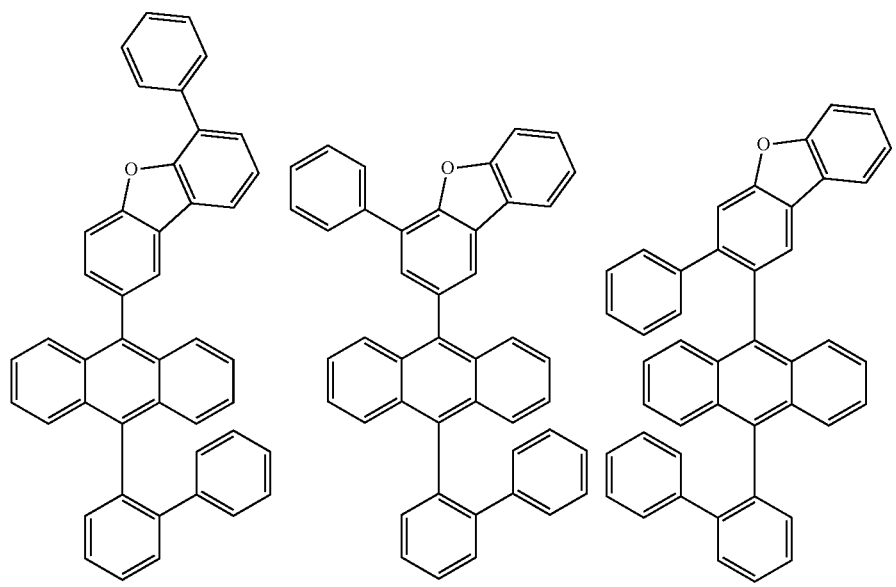
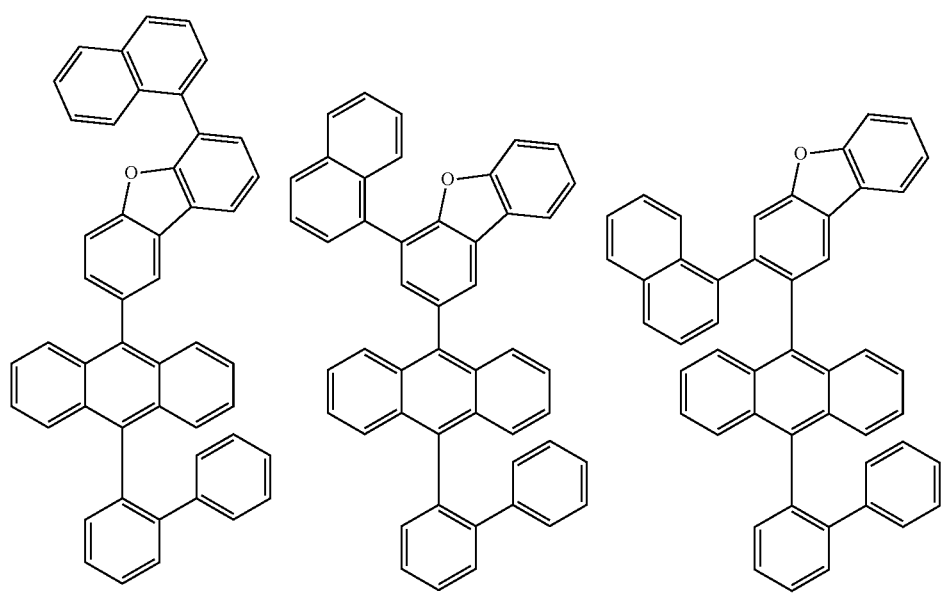

1077
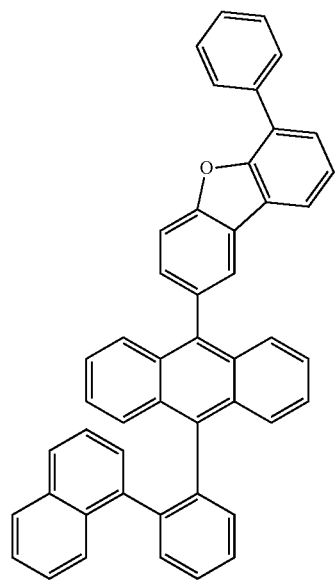
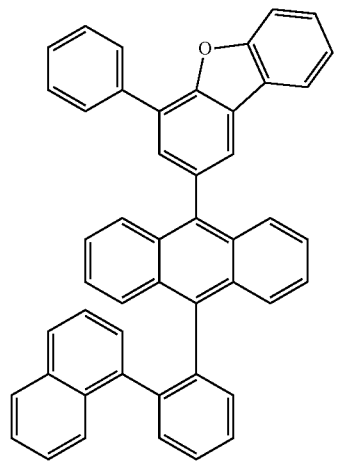
1078
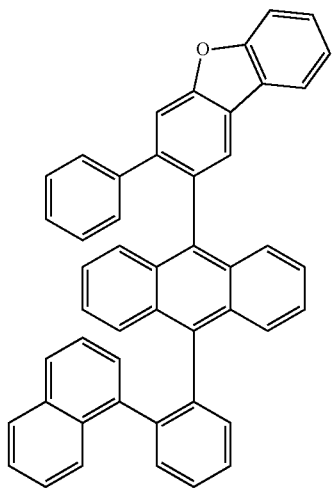
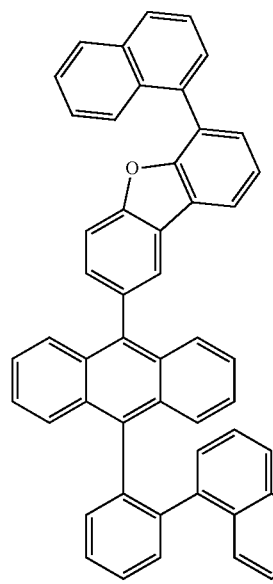
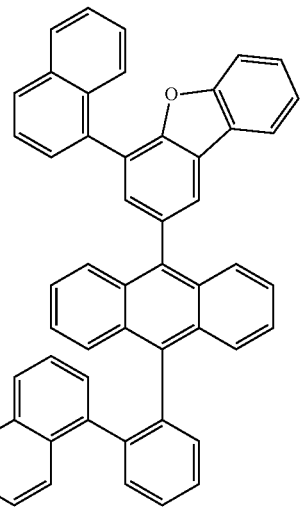
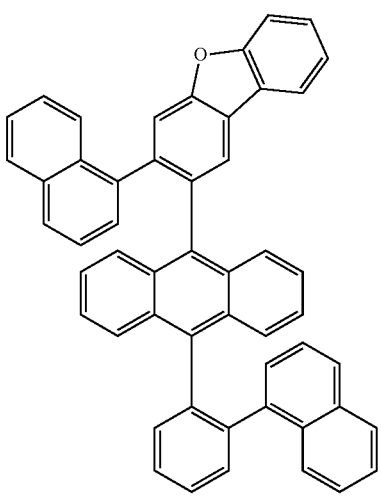

1079
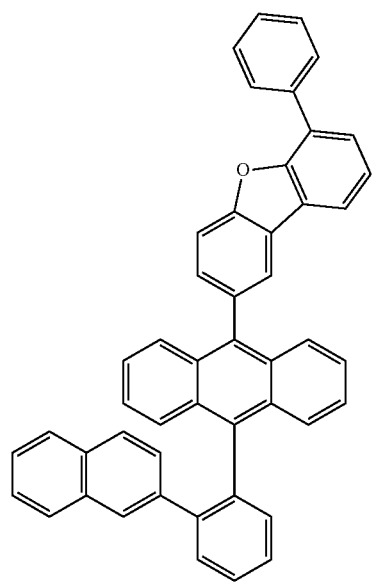
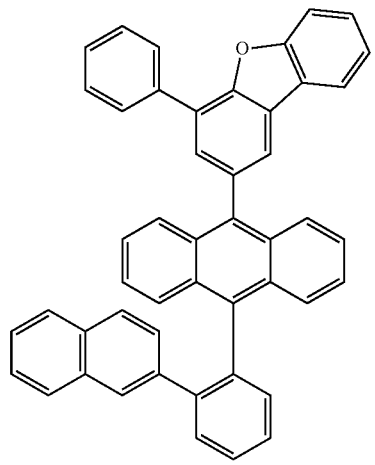
1080
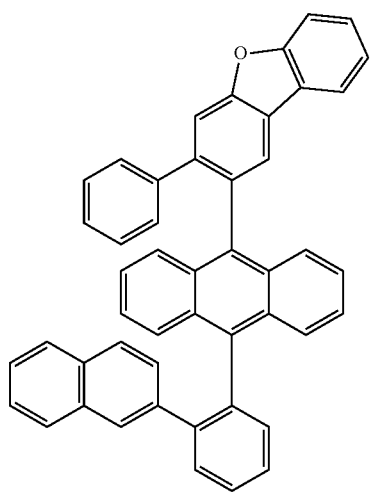
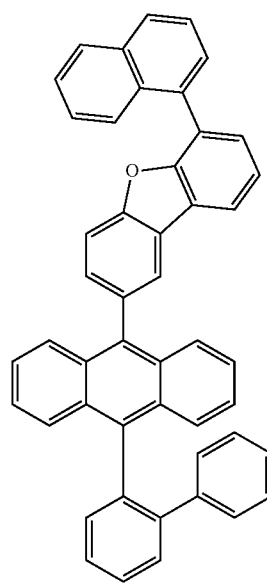
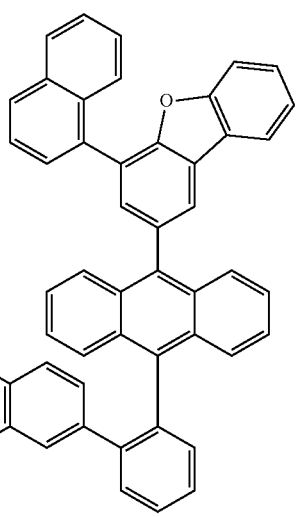
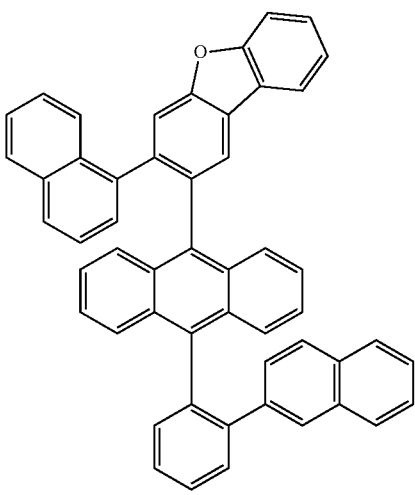

1081　　　　　　　　　　　　　　1082
-continued
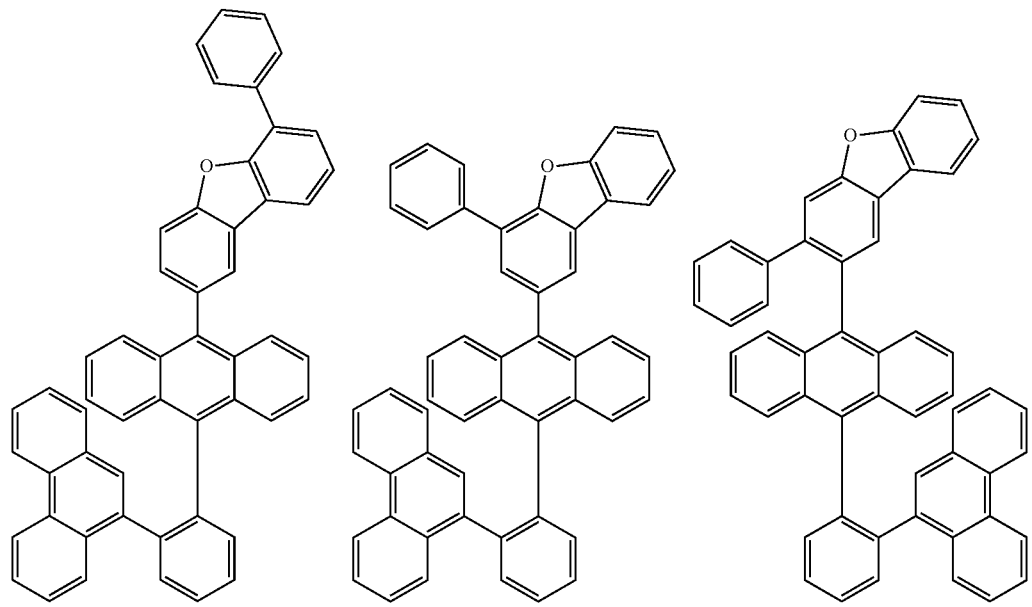
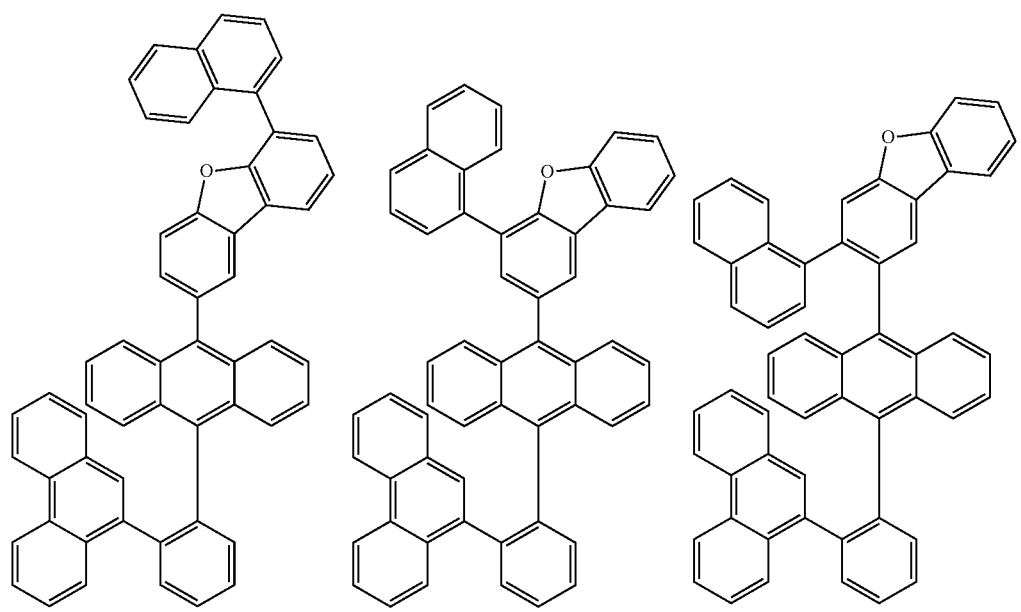

1083 1084
-continued
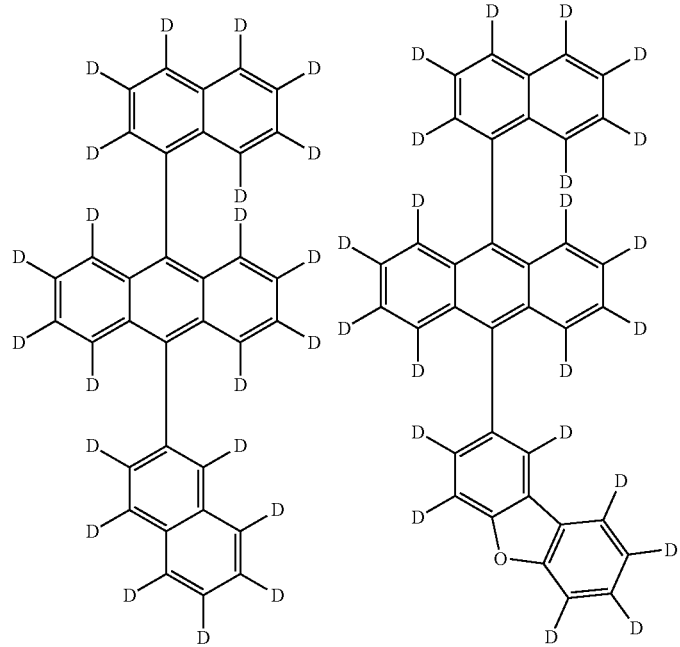
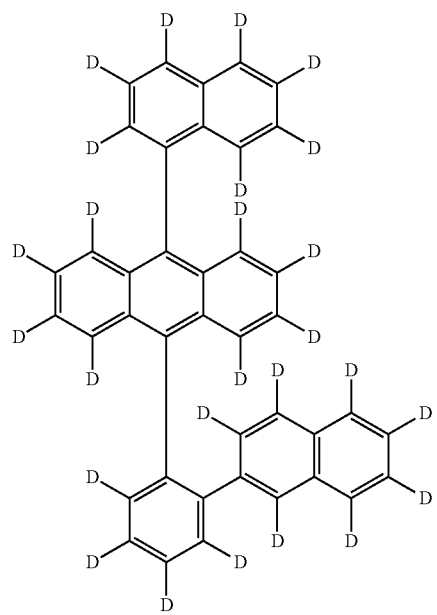
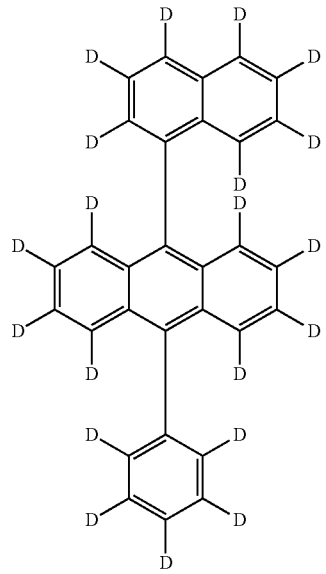
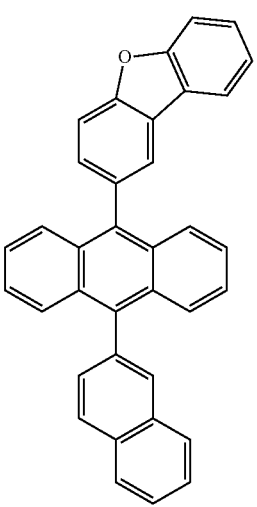

1085 1086
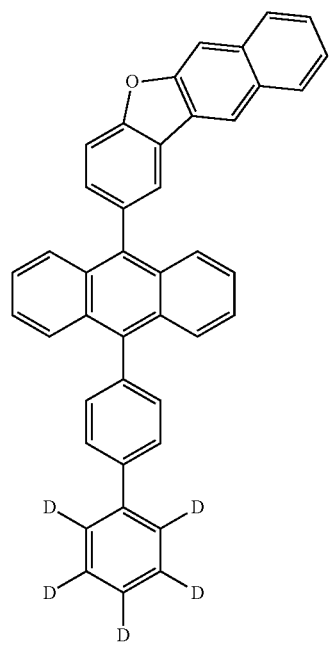
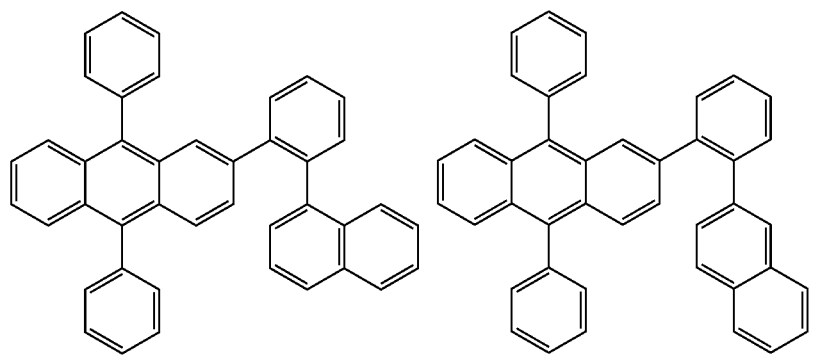
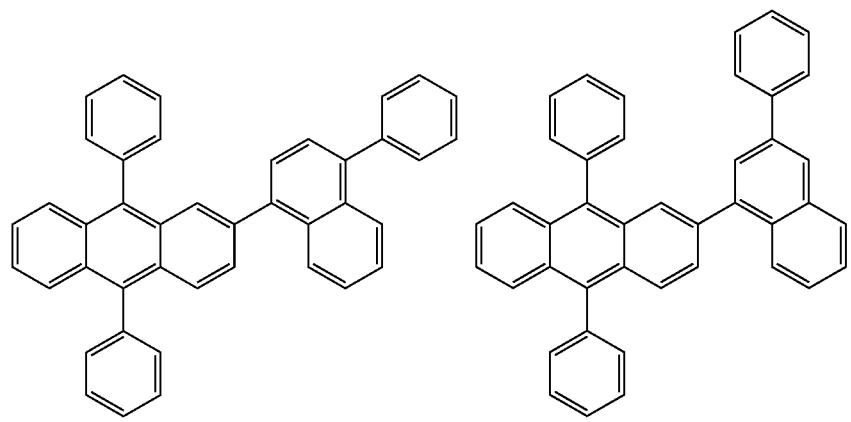
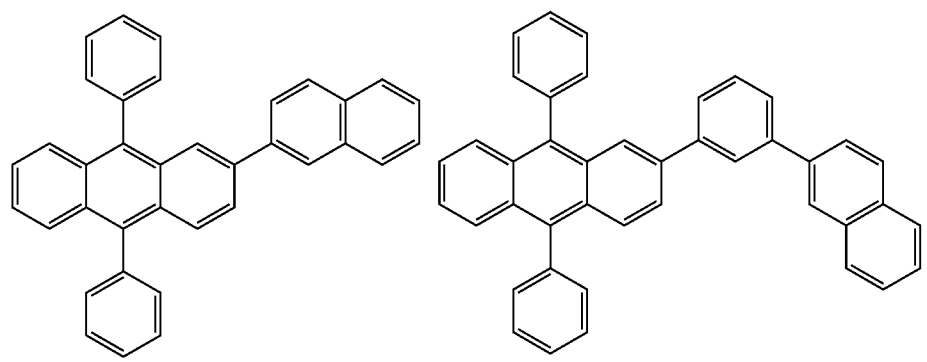

-continued
1087 1088
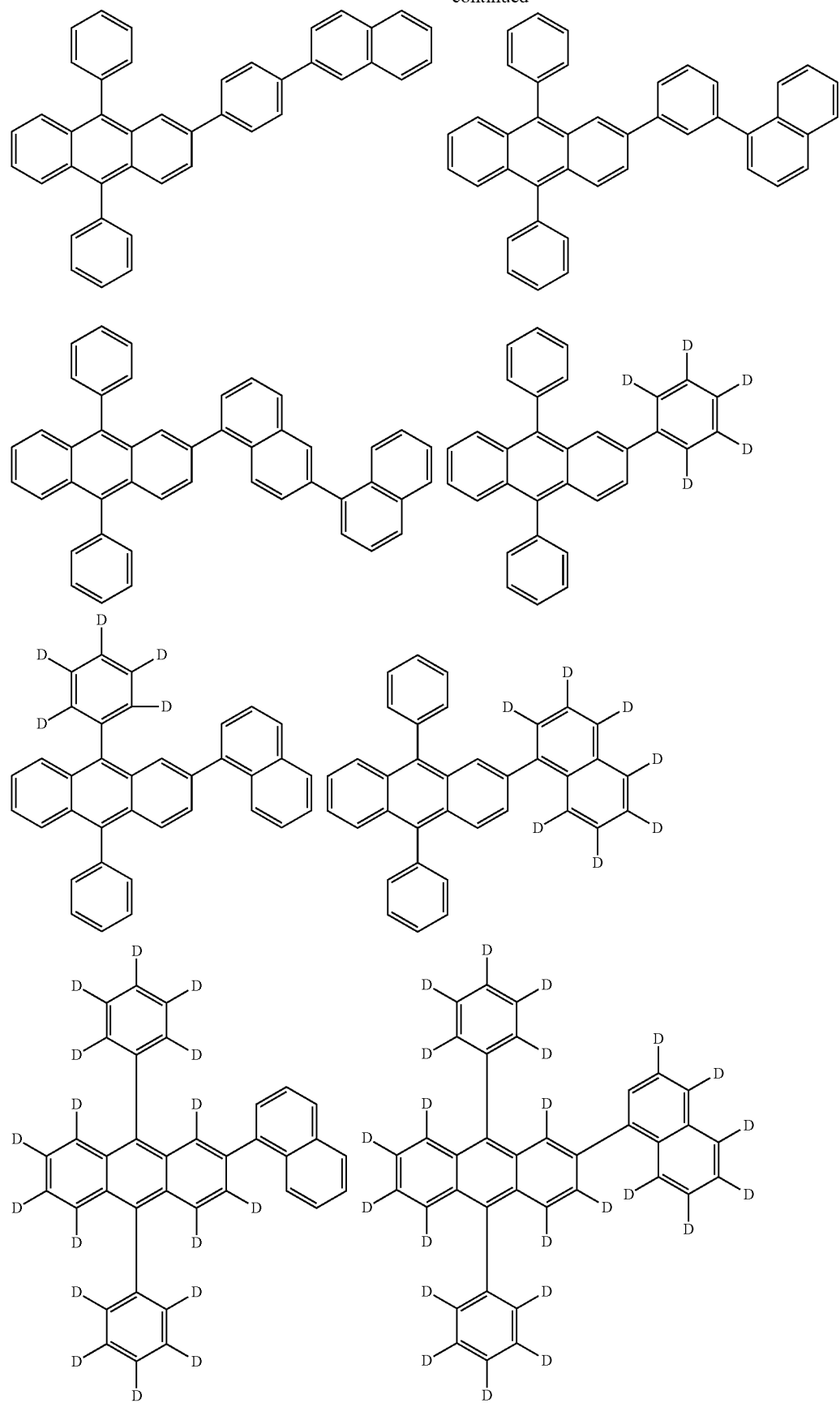

-continued
1089 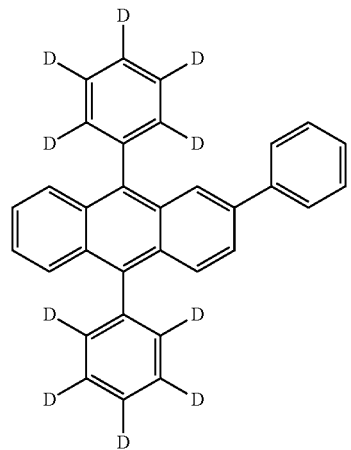 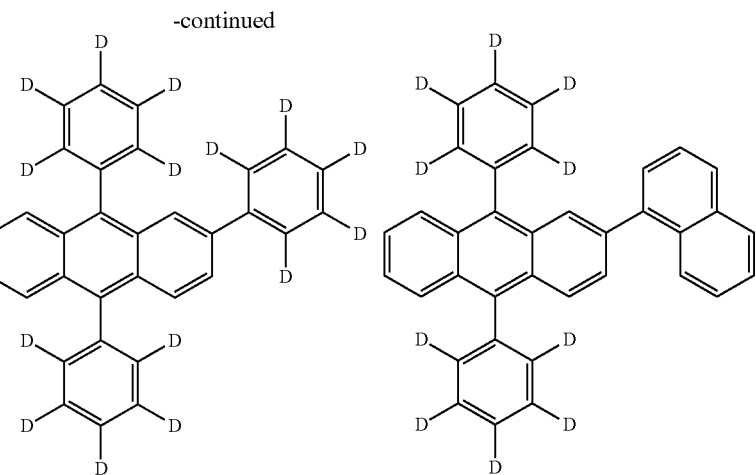 1090
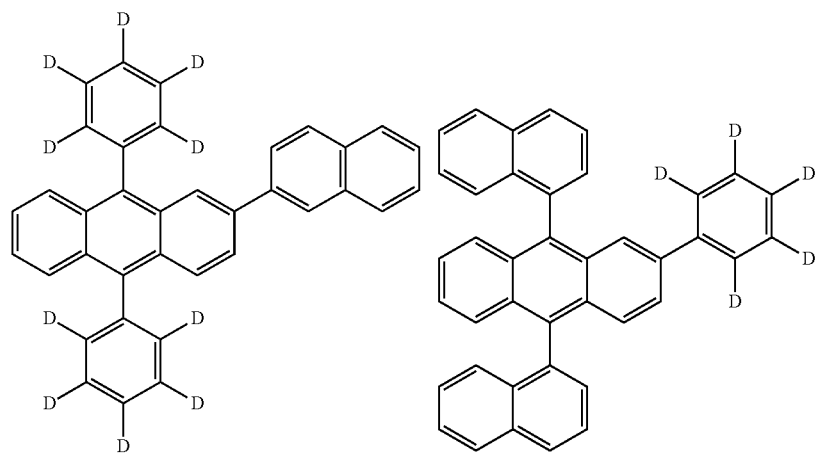
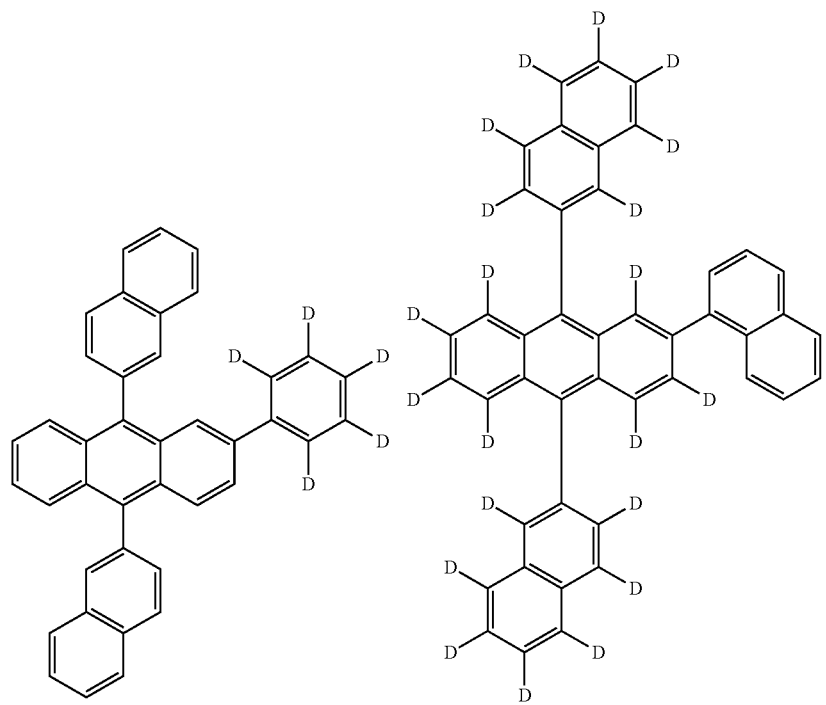

1091 1092
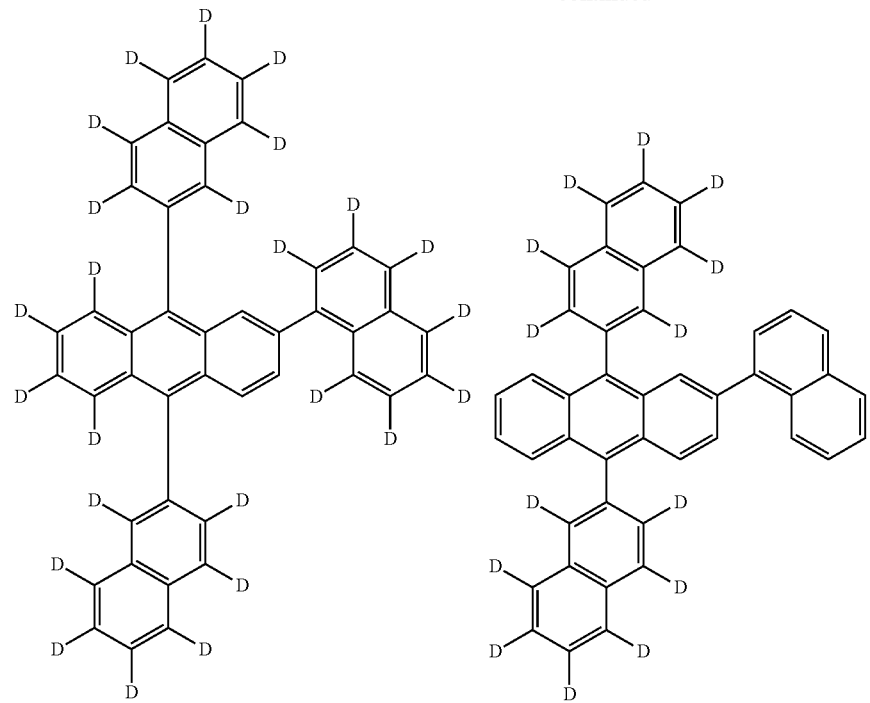
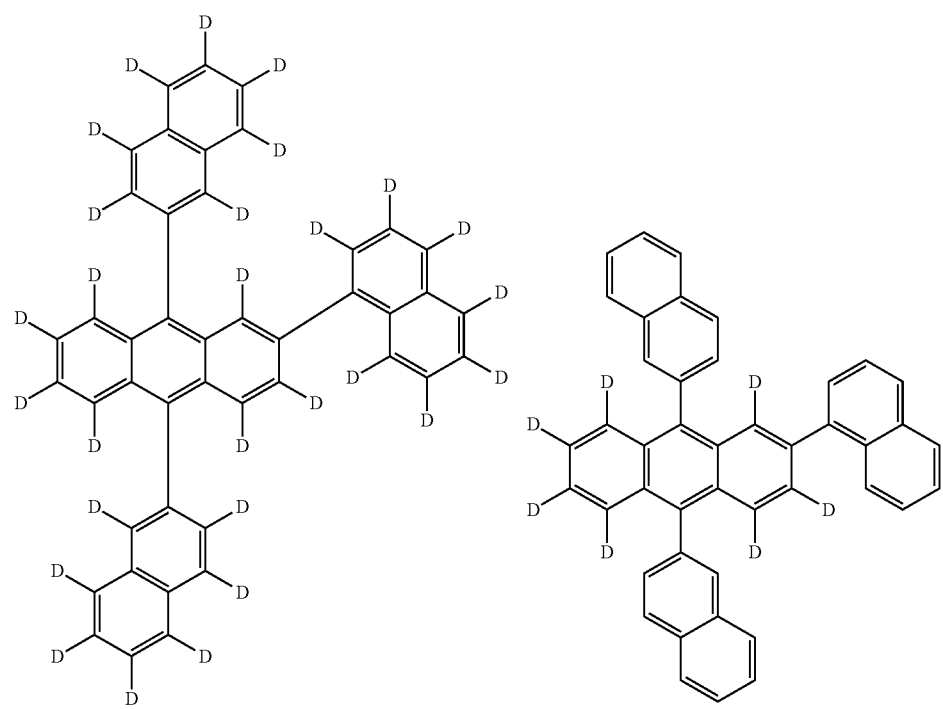

-continued
1093
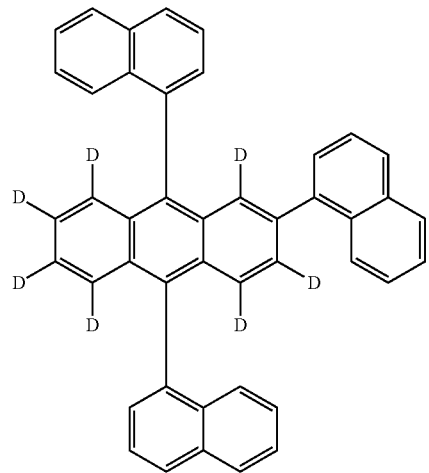
1094
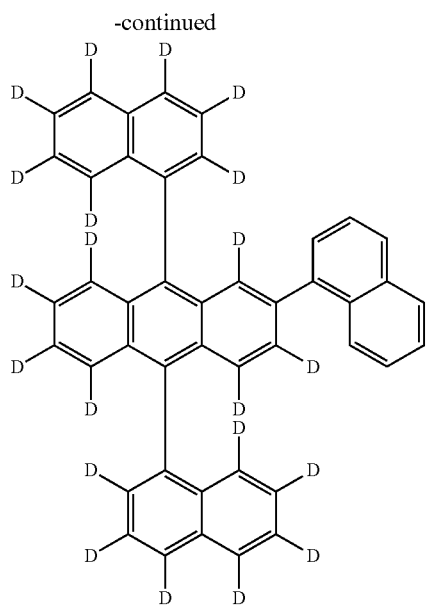
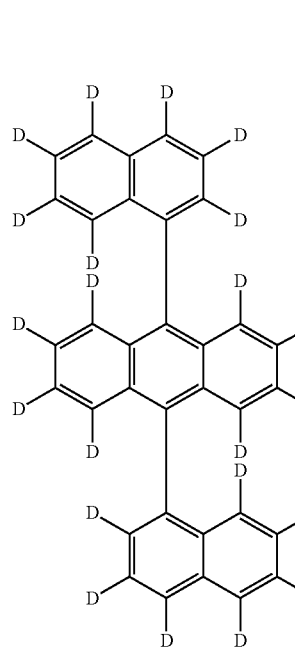
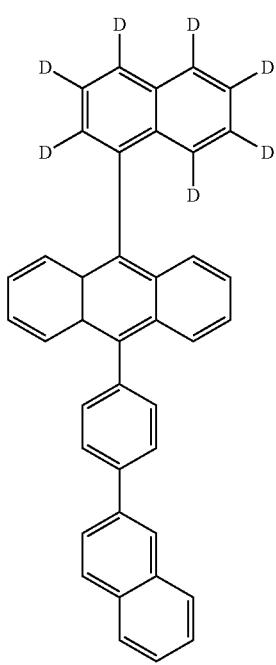
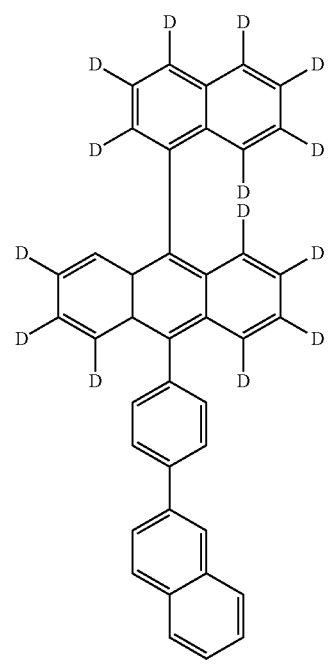

1095
-continued
1096
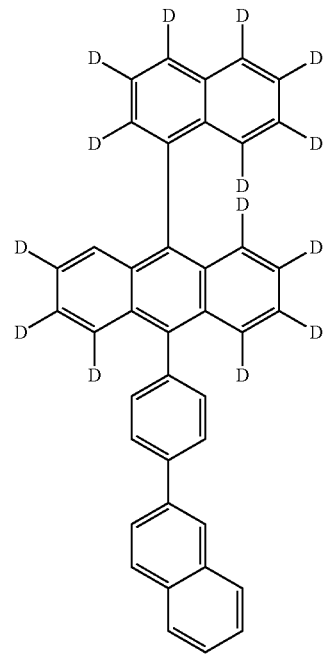
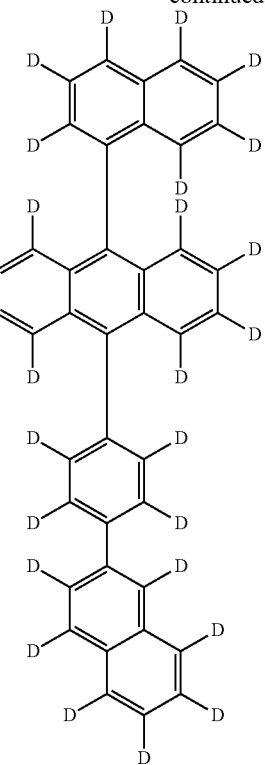
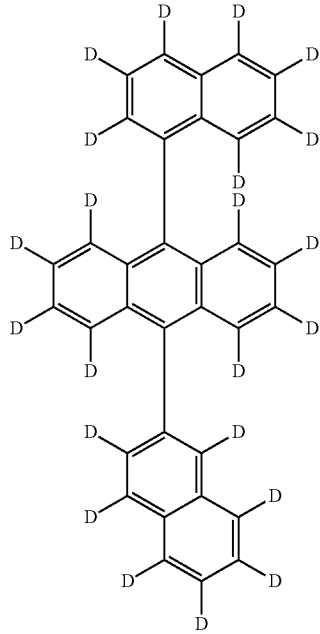
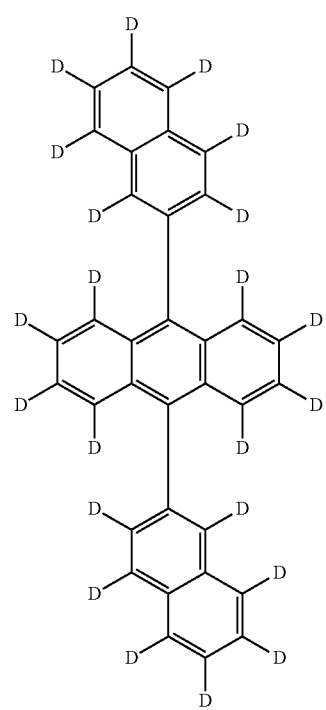
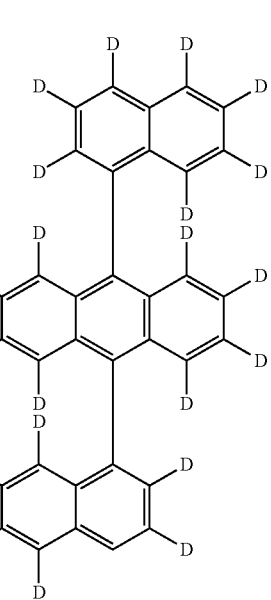
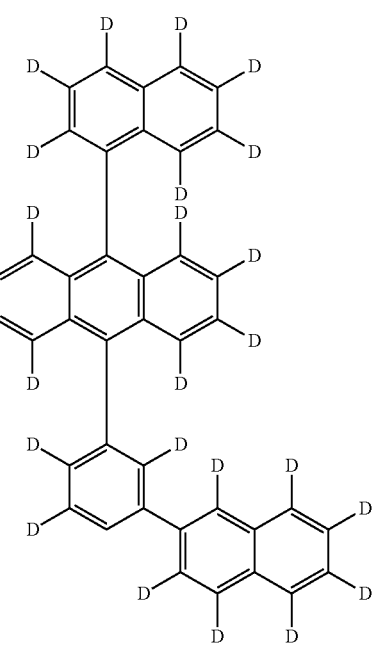

1097
1098
-continued
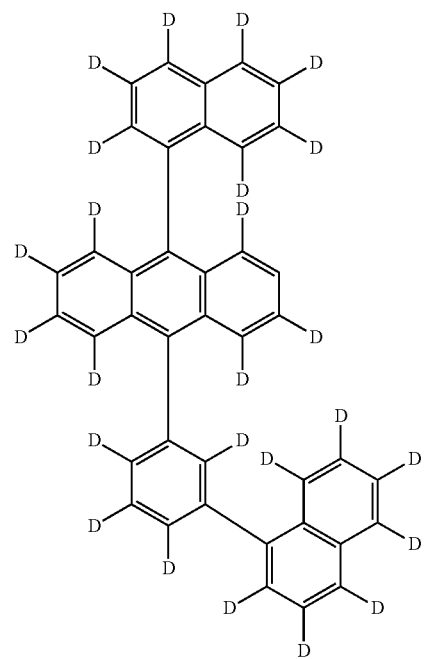
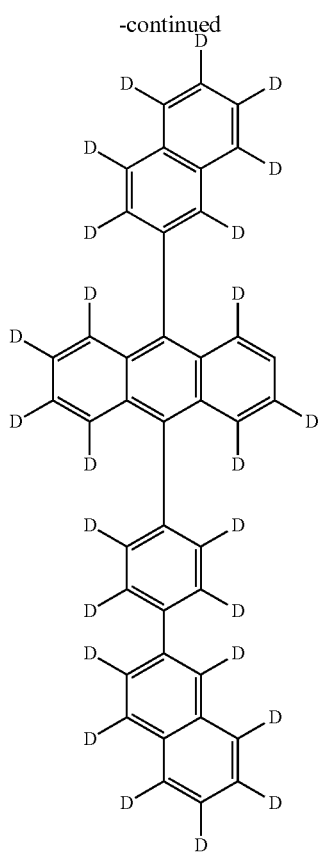
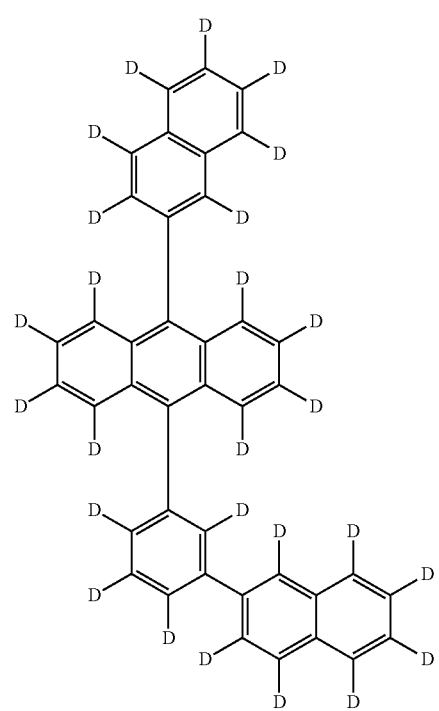
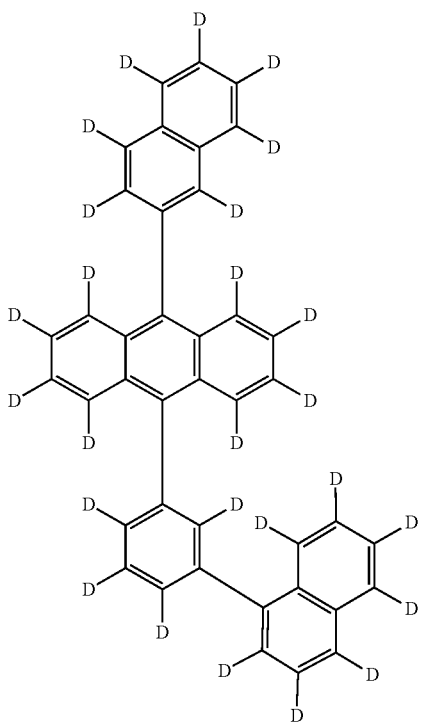
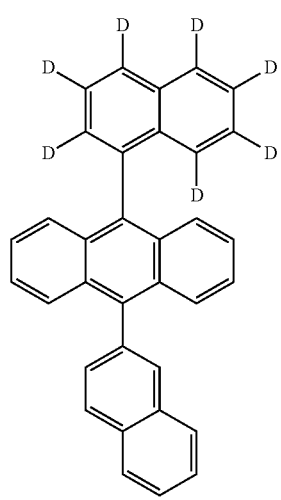

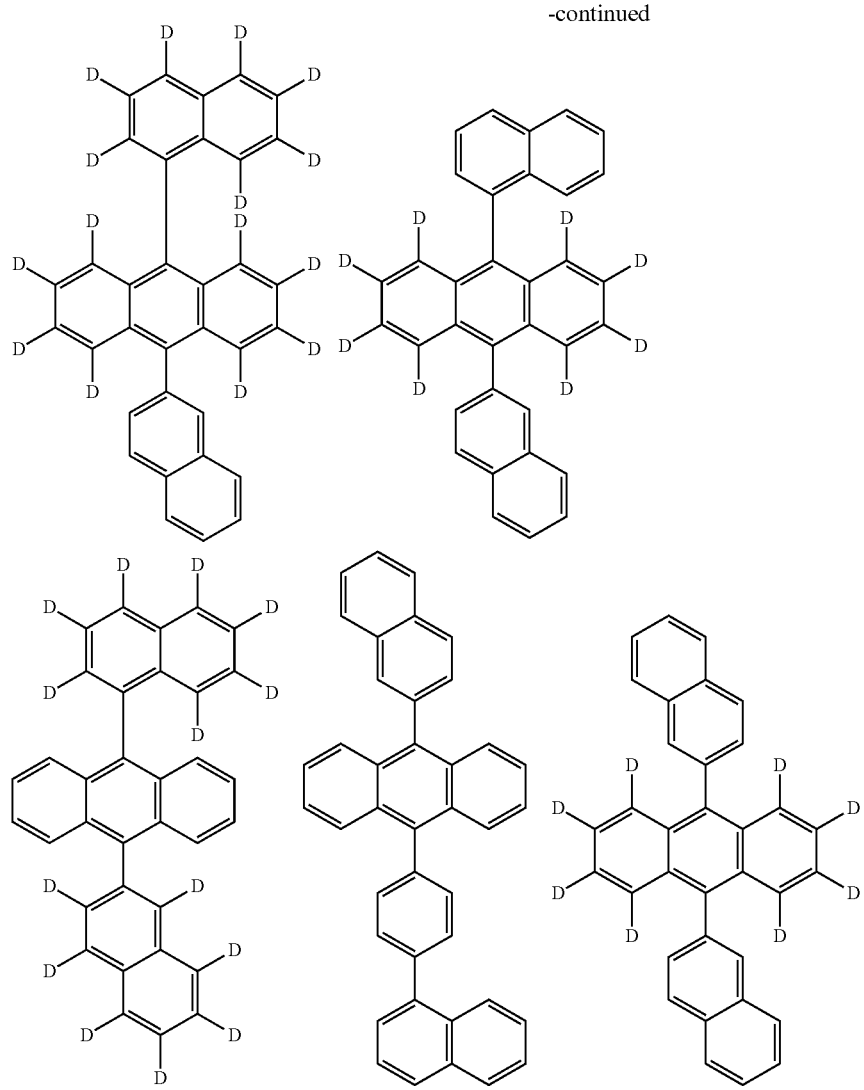

According to one embodiment of the present specification, the compound represented by Chemical Formula H may be prepared using the following General Formula 1, however, the method is not limited thereto.

[General Formula 1]

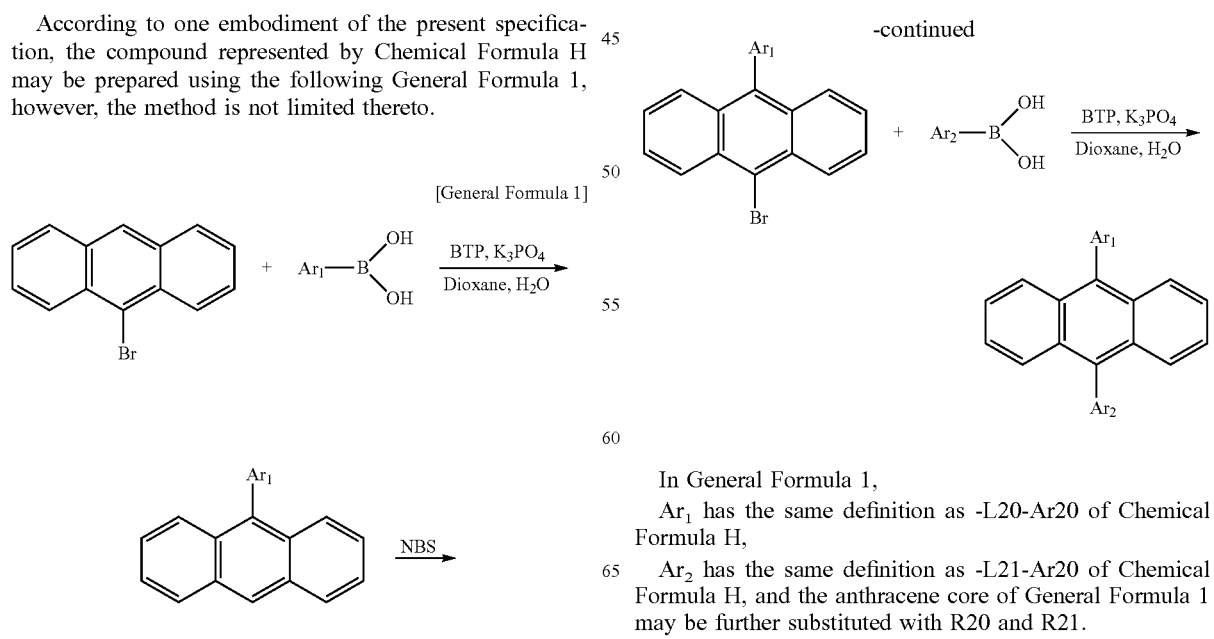

In General Formula 1,

Ar₁ has the same definition as -L20-Ar20 of Chemical Formula H,

Ar₂ has the same definition as -L21-Ar20 of Chemical Formula H, and the anthracene core of General Formula 1 may be further substituted with R20 and R21.

In one embodiment of the present specification, the compound represented by Chemical Formula 1 is used as a dopant, and the compound represented by Chemical Formula H is used as a host in the light emitting layer.

In one embodiment of the present specification, when the light emitting layer includes a host and a dopant, a content of the dopant may be selected in a range of 0.01 parts by weight to 10 parts by weight based on 100 parts by weight of the light emitting layer, however, the content is not limited thereto.

In one embodiment of the present specification, the light emitting layer includes a host and a dopant, and the host and the dopant are included in a weight ratio of 99:1 to 1:99, preferably in a weight ratio of 99:1 to 70:30, and more preferably in a weight ratio of 99:1 to 90:10.

The light emitting layer may further include a host material, and the host includes fused aromatic ring derivatives, heteroring-containing compounds or the like. Specifically, anthracene derivatives, pyrene derivatives, naphthalene derivatives, pentacene derivatives, phenanthrene compounds, fluoranthene compounds or the like may be included as the fused aromatic ring derivative, and carbazole derivatives, dibenzofuran derivatives, ladder-type furan compounds, pyrimidine derivatives, triazine derivatives or the like may be included as the heteroring-containing compound, and mixtures of two or more types thereof may be included, however, the host material is not limited thereto.

According to one embodiment of the present specification, the organic material layer includes a light emitting layer, and the light emitting layer includes one or more types of dopants and a host.

According to one embodiment of the present specification, the organic material layer includes a light emitting layer, and the light emitting layer includes two or more types of mixed dopants and a host.

According to one embodiment of the present specification, one or more of the two or more types of mixed dopants include Chemical Formula 1, and the host includes the compound represented by Chemical Formula H. One or more of the two or more types of mixed dopants include Chemical Formula 1, and as the rest, dopant materials known in the art may be used, however, the dopant is not limited thereto.

According to one embodiment of the present specification, one or more of the two or more types of mixed dopants include Chemical Formula 1, and as the rest, one or more of boron-based compounds, pyrone-based compounds and delayed fluorescence-based compounds different from Chemical Formula 1 may be used, however, the dopant is not limited thereto.

According to one embodiment of the present specification, the organic material layer includes a light emitting layer, and the light emitting layer includes one or more types of hosts.

According to one embodiment of the present specification, the organic material layer includes a light emitting layer, and the light emitting layer includes two or more types of mixed hosts.

According to one embodiment of the present specification, one or more of the two or more types of mixed hosts are the compound represented by Chemical Formula H.

According to one embodiment of the present specification, the two or more types of mixed hosts are different from each other, and each independently the compound represented by Chemical Formula H.

According to one embodiment of the present specification, the organic material layer includes a light emitting layer, and the light emitting layer includes two types of mixed hosts.

According to one embodiment of the present specification, the organic material layer includes a light emitting layer, the light emitting layer includes two types of mixed hosts, the two types of mixed hosts are different from each other, and the two types of hosts are the compound represented by Chemical Formula H.

According to one embodiment of the present specification, the organic material layer includes a light emitting layer, the light emitting layer includes a first host represented by Chemical Formula H; and a second host represented by Chemical Formula H, and the first host and the second host are different from each other.

According to one embodiment of the present specification, the first host:the second host are included in a weight ratio of 95:5 to 5:95, and preferably in a weight ratio of 70:30 to 30:70.

According to one embodiment of the present specification, the organic material layer includes a light emitting layer, and the light emitting layer includes one or more types of hosts and a dopant.

According to one embodiment of the present specification, the organic material layer includes a light emitting layer, the light emitting layer includes one or more types of hosts and a dopant, the hosts include the compound represented by Chemical Formula H, and the dopant includes the compound represented by Chemical Formula 1.

According to one embodiment of the present specification, the organic material layer includes a light emitting layer, and the light emitting layer includes two or more types of mixed hosts and a dopant.

According to one embodiment of the present specification, one or more of the two or more types of mixed hosts include the compound represented by Chemical Formula H, and the dopant includes the compound represented by Chemical Formula 1.

In the present specification, the two or more types of mixed hosts are different from each other.

According to one embodiment of the present specification, the organic material layer includes a light emitting layer, and the light emitting layer includes two types of mixed hosts and a dopant.

According to one embodiment of the present specification, the two types of mixed hosts are different from each other, and each independently include the compound represented by Chemical Formula H, and the dopant includes the compound represented by Chemical Formula 1.

According to one embodiment of the present specification, the organic material layer includes a light emitting layer, the light emitting layer includes a first host represented by Chemical Formula H; a second host represented by Chemical Formula H; and a dopant represented by Chemical Formula 1, and the first host and the second host are different from each other.

According to one embodiment of the present specification, the organic material layer uses one or more types of hosts and one or more types of dopants, the one or more types of hosts include the compound represented by Chemical Formula H, and the one or more types of dopants include the compound represented by Chemical Formula 1.

According to one embodiment of the present specification, the organic material layer uses two or more types of mixed hosts and two or more types of mixed dopants, the two or more types of mixed hosts may use the same materials as described above, and the two or more types of mixed dopants may use the same materials as described above.

In one embodiment of the present specification, the organic light emitting device includes a first electrode; a second electrode; a light emitting layer provided between the first electrode and the second electrode; and two or more layers of an organic material layer provided between the light emitting layer and the first electrode, or between the light emitting layer and the second electrode, wherein at least one of the two or more layers of an organic material layer includes the compound represented by Chemical Formula 1.

In one embodiment of the present specification, as the two or more layers of an organic material layer, the two or more layers may be selected from the group consisting of a light emitting layer, a hole transfer layer, a hole injection layer, a layer carrying hole transfer and hole injection at the same time, and an electron blocking layer.

In one embodiment of the present specification, the organic light emitting device may include two or more electron transfer layers, but is not limited thereto.

In one embodiment of the present specification, the organic material layer includes two or more electron transfer layers, and at least one of the two or more electron transfer layers includes the compound represented by Chemical Formula 1. Specifically, in one embodiment of the present specification, the compound represented by Chemical Formula 1 may be included in one of the two or more electron transfer layers, or may be included in each of the two or more electron transfer layers.

In addition, when the compound is included in each of the two or more electron transfer layers in one embodiment of the present specification, materials other than the compound represented by Chemical Formula 1 may be the same as or different from each other.

When the organic material layer including the compound represented by Chemical Formula 1 is an electron transfer layer, the electron transfer layer may further include an n-type dopant. As the n-type dopant, those known in the art may be used, and for example, metals or metal complexes may be used. For example, the electron transfer layer including the compound represented by Chemical Formula 1 may further include lithium quinolate (LiQ).

In one embodiment of the present specification, the organic material layer includes two or more hole transfer layers, and at least one of the two or more hole transfer layers includes the compound represented by Chemical Formula 1. Specifically, in one embodiment of the present specification, the compound represented by Chemical Formula 1 may be included in one of the two or more hole transfer layers, or may be included in each of the two or more hole transfer layers.

In addition, when the compound represented by Chemical Formula 1 is included in each of the two or more hole transfer layers in one embodiment of the present specification, materials other than the compound represented by Chemical Formula 1 may be the same as or different from each other.

In one embodiment of the present specification, the organic material layer may further include, in addition to the organic material layer including the compound represented by Chemical Formula 1, a hole injection layer or a hole transfer layer including a compound including an arylamine group, a carbazolyl group or a benzocarbazolyl group.

In one embodiment of the present specification, the first electrode is an anode or a cathode.

In one embodiment of the present specification, the second electrode is a cathode or an anode.

In one embodiment of the present specification, the organic light emitting device may have a structure in which an anode, one or more layers of an organic material layer and a cathode are consecutively disposed on a substrate (normal type).

In one embodiment of the present specification, the organic light emitting device may have a structure in a reverse direction in which a cathode, one or more layers of an organic material layer and an anode are consecutively disposed on a substrate (inverted type).

For example, structures of the organic light emitting device according to an exemplary embodiment of the present specification are illustrated in FIG. 1 and FIG. 2. FIG. 1 and FIG. 2 illustrate the organic light emitting device, and the organic light emitting device of the present disclosure is not limited thereto.

FIG. 1 illustrates a structure of the organic light emitting device in which a substrate (1), a first electrode (2), a light emitting layer (3) and a second electrode (4) are consecutively disposed. In such a structure, the compound may be included in the light emitting layer (3).

FIG. 2 illustrates a structure of the organic light emitting device in which a substrate (1), a first electrode (2), a hole injection layer (5), a hole transfer layer (6), an electron blocking layer (7), a light emitting layer (3), a first electron transfer layer (8), a second electron transfer layer (9), an electron injection layer (10) and a second electrode (4) are consecutively disposed. In such a structure, the compound may be included in the light emitting layer (3).

The organic light emitting device of the present specification may be manufactured using materials and methods known in the art, except that one or more layers of the organic material layer include the compound, that is, the compound represented by Chemical Formula 1.

When the organic light emitting device includes a plurality of layers in the organic material layer, the plurality of layers of the organic material layer may be formed with the same materials or different materials.

For example, the organic light emitting device of the present specification may be manufactured by consecutively disposing a first electrode, an organic material layer and a second electrode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material usable as a cathode thereon. In addition to such a method, the organic light emitting device may also be manufactured by consecutively depositing a cathode material, an organic material layer and an anode material on a substrate.

In addition, the compound represented by Chemical Formula 1 may be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device may also be manufactured by consecutively disposing a cathode material, an organic material layer and an anode material on a substrate (International Patent Application Laid Open Publication No. 2003/012890). However, the manufacturing method is not limited thereto.

As the first electrode material, materials having large work function are normally preferred so that hole injection to an organic material layer is smooth. Examples thereof include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the second electrode material, materials having small work function are normally preferred so that electron injection to an organic material layer is smooth. Examples thereof include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes dibenzofuran derivatives, ladder-type furan compounds, pyrimidine derivatives and the like, however, the material is not limited thereto.

The dopant material includes, when including an additional compound in addition to the compound represented by Chemical Formula 1, aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like. In addition, the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

In the present specification, when the compound represented by Chemical Formula 1 is included in an organic material layer other than the light emitting layer, or an additional light emitting layer is provided, a light emitting material of the light emitting layer is, as a material capable of emitting light in a visible region by receiving holes and electrons from a hole transfer layer and an electron transfer layer, respectively, and binding the holes and the electrons, preferably a material having favorable quantum efficiency for fluorescence or phosphorescence. Specific examples thereof include 8-hydroxy-quinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene; rubrene, and the like, but are not limited thereto.

The hole injection layer is a layer injecting holes from an electrode. The hole injection material preferably has, by having an ability to transfer holes, a hole injection effect in a first electrode and an excellent hole injection effect for a light emitting layer or a light emitting material. In addition, the hole injection material is preferably a material having an excellent ability to prevent excitons generated in the light emitting layer from moving to an electron injection layer or an electron injection material. In addition, a material having an excellent thin film forming ability is preferred. In addition, the highest occupied molecular orbital (HOMO) of the hole injection material is preferably in between the work function of a first electrode material and the HOMO of surrounding layers of an organic material layer. Specific examples of the hole injection material include metal porphyrins, oligothiophene, arylamine-based organic materials; carbazole-based organic materials; nitrile-based organic materials; hexanitrile hexaazatriphenylene-based organic materials; quinacridone-based organic materials; perylene-based organic materials; polythiophene-based conductive polymers such as anthraquinone or polyaniline, mixtures of two or more of the examples, and the like, but are not limited thereto.

The hole transfer layer is a layer receiving holes from a hole injection layer and transferring the holes to a light emitting layer. As the hole transfer material, materials having, as a material capable of receiving holes from a first electrode or a hole injection layer and moving the holes to a light emitting layer, high mobility for the holes are preferred. Specific examples thereof include arylamine-based organic materials, carbazole-based organic materials, conductive polymers, block copolymers having conjugated parts and non-conjugated parts together, and the like, but are not limited thereto.

The electron transfer layer is a layer receiving electrons from an electron injection layer and transferring the electrons to a light emitting layer. As the electron transfer material, materials capable of favorably receiving electrons from a second electrode, moving the electrons to a light emitting layer, and having high mobility for the electrons are preferred. Specific examples thereof include Al complexes of 8-hydroxyquinoline; complexes including $Alq_3$; organic radical compounds; hydroxyflavon-metal complexes; triazine derivatives; LiQ and the like, but are not limited thereto. The electron transfer layer may be used together with any desired first electrode material as used in the art. Particularly, the suitable first electrode material is a common material having low work function and having an aluminum layer or a silver layer following. Specifically, cesium, barium, calcium, ytterbium, samarium and the like are included, and in each case, an aluminum layer or a silver layer follows.

The electron injection layer is a layer injecting electrons from an electrode. As the electron injection material, materials having an excellent electron transferring ability, having an electron injection effect from a second electrode, and having an excellent electron injection effect for a light emitting layer or light emitting material are preferred. In addition, materials preventing excitons generated in the light emitting layer from moving to a hole injection layer, and having an excellent thin film forming ability are preferred. Specific examples thereof include fluorenone, anthraquinodimethane, diphenoquinone, thiopyran dioxide, oxazole, oxadiazole, triazole, triazine, midazole, perylene tetracarboxylic acid, fluorenylidene methane, anthrone or the like, and derivatives thereof, metal complex compounds, nitrogen-containing 5-membered ring derivatives, mixtures of two or more of the examples, and the like, but are not limited thereto.

The metal complex compound includes 8-hydroxyquinolinato lithium/bis(8-hydroxyquinolinato)zinc, bis(8-hydrozyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo(h)quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The electron blocking layer is a layer capable of enhancing lifetime and efficiency of a device by preventing electrons injected from an electron injection layer from passing through a light emitting layer and entering a hole injection layer. Known material may be used without limit, and the electron blocking layer may be formed between the light emitting layer and the hole injection layer, or between the light emitting layer and a layer carrying out hole injection and hole transfer at the same time.

The hole blocking layer is a layer blocking holes from passing a light emitting layer and reaching a cathode, and may be generally formed under the same condition as the electron injection layer. Specific examples thereof may include oxadiazole derivatives, triazole derivatives, phenanthroline derivatives, aluminum complexes, pyridine, pyrimidine or triazine derivatives and the like, but are not limited thereto.

The organic light emitting device according to the present specification may be a top-emission type, a bottom-emission type or a dual-emission type depending on the materials used.

In one embodiment of the present specification, the compound represented by Chemical Formula 1 may be included in, in addition to the organic light emitting device, an organic solar cell or an organic transistor.

The compound according to the present specification may also be used in an organic light emitting device including an organic phosphorescent device, an organic solar cell, an organic photo conductor, an organic transistor and the like under a similar principle used in the organic light emitting device. For example, the organic solar cell may have a structure including a cathode, an anode, and a photoactive layer provided between the cathode and the anode, and the photoactive layer may include the compound.

The organic light emitting device of the present specification may be manufactured using common organic light emitting device manufacturing methods and materials except that one or more layers of the organic material layer are formed using the compound described above.

EXAMPLES

Hereinafter, the present specification will be described in detail with reference to examples, comparative examples and the like. However, the examples and the comparative examples according to the present specification may be modified to various other forms, and the scope of the present specification is not to be construed as being limited to the examples and the comparative examples described below. Examples and comparative examples of the present specification are provided in order to more fully describe the present specification to those having average knowledge in the art.

Synthesis Example

Synthesis Example 1. Synthesis of Compound A-2-1

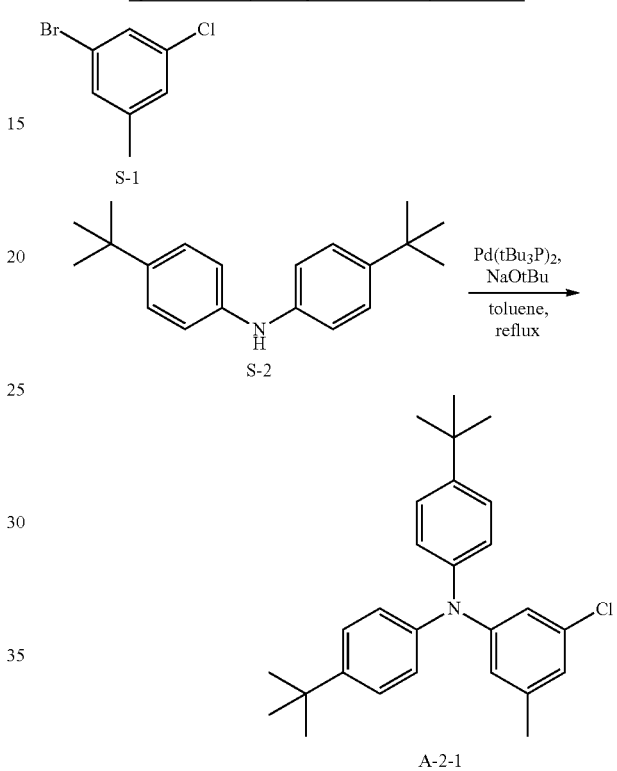

After dissolving 1-bromo-3-chloro-5-methylbenzene (S-1, 146 mmol, 30 g, 1 eq.) and bis(4-(tert-butyl)phenyl)amine (S-2, 146 mmol, 41.1 g, 1 eq.) in toluene (0.2 M, 730 ml) in a 3-neck flask, sodium tert-butoxide (219 mmol, 21 g, 1.5 eq.) and bis(tri-tert-butylphosphine)palladium(0) (1.46 mmol, 0.75 g, 0.01 eq.) were introduced thereto, and the result was stirred for 1 hour under reflux under the argon atmosphere. When the reaction was finished, the result was cooled to room temperature, then distilled water was introduced thereto, and the reaction solution was transferred to a separatory funnel and extracted. The extract was dried with MgSO$_4$ and concentrated, and the sample was purified using silica gel column chromatography to obtain Compound A-2-1 (49 g, yield 83%, MS[M+H]+=405).

Synthesis Example 2. Synthesis of Compound A-2-2

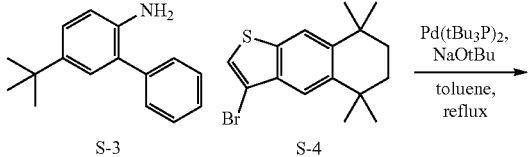

-continued

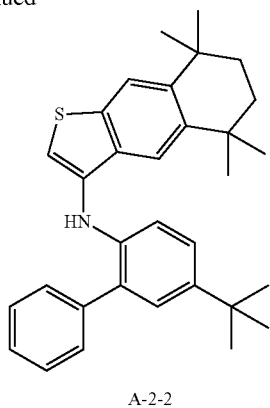

A-2-2

After dissolving 5-tert-butyl-[1,1'-biphenyl]-2-amine (S-3, 66.6 mmol, 15 g, 1 eq.) and 3-bromo-5,5,8,8-tetramethyl-5,6,7,8-tetrahydronaphtho[2,3-b]thiophene (S-4, 66.6 mmol, 21.5 g, 1 eq.) in toluene (0.2 M, 335 ml) in a 3-neck flask, sodium tert-butoxide (99.9 mmol, 9.60 g, 1.5 eq.) and bis(tri-tert-butylphosphine)palladium(0) (0.666 mmol, 0.340 g, 0.01 eq.) were introduced thereto, and the result was stirred for 12 hours under reflux under the argon atmosphere. When the reaction was finished, the result was cooled to room temperature, then $H_2O$ was introduced thereto, and the reaction solution was transferred to a separatory funnel and extracted. The extract was dried with $MgSO_4$ and concentrated, and the sample was purified using silica gel column chromatography to obtain Compound A-2-2 (24.2 g, yield 78%, MS[M+H]+=468).

Synthesis Example 3. Synthesis of Compound A-2-3

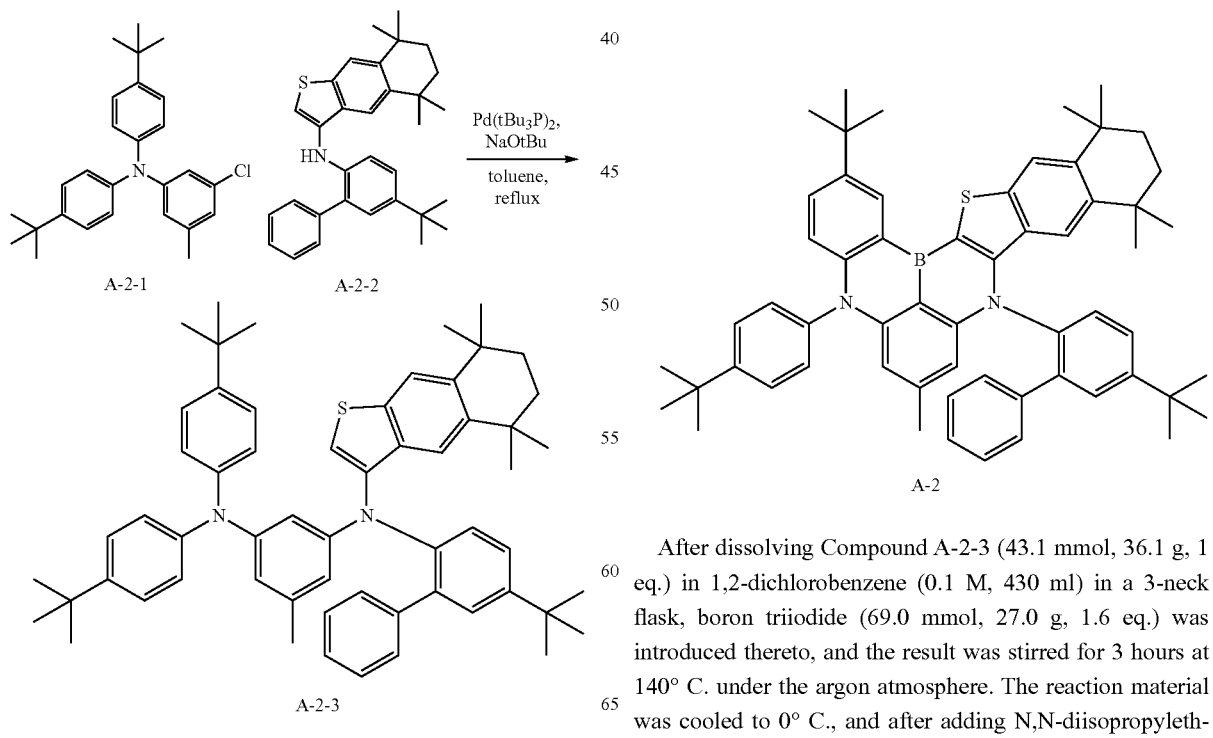

After dissolving Compound A-2-1 (49.3 mmol, 20 g, 1 eq.) and Compound A-2-2 (49.3 mmol, 23.0 g, 1 eq.) in toluene (0.2 M, 250 ml) in a 3-neck flask, sodium tert-butoxide (73.9 mmol, 7.10 g, 1.5 eq.) and bis(tri-tert-butylphosphine)palladium(0) (0.493 mmol, 0.252 g, 0.01 eq.) were introduced thereto, and the result was stirred for 12 hours under reflux under the argon atmosphere. When the reaction was finished, the result was cooled to room temperature, then $H_2O$ was introduced thereto, and the reaction solution was transferred to a separatory funnel and extracted. The extract was dried with $MgSO_4$ and concentrated, and the sample was purified using silica gel column chromatography to obtain Compound A-2-3 (36.1 g, yield 88%, MS[M+H]+=837).

Synthesis Example 4. Synthesis of Compound A-2

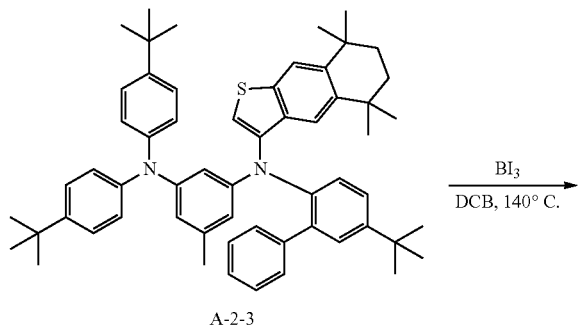

After dissolving Compound A-2-3 (43.1 mmol, 36.1 g, 1 eq.) in 1,2-dichlorobenzene (0.1 M, 430 ml) in a 3-neck flask, boron triiodide (69.0 mmol, 27.0 g, 1.6 eq.) was introduced thereto, and the result was stirred for 3 hours at 140° C. under the argon atmosphere. The reaction material was cooled to 0° C., and after adding N,N-diisopropylethylamine (388 mmol, 50.2 g, 9 eq.) thereto, the result was stirred for 1 hour. The result was extracted in a separatory funnel using toluene and H₂O. The extract was dried with MgSO₄ and concentrated, and the sample was purified using silica gel column chromatography and then went through sublimation purification to obtain Compound A-2 (7.1 g, yield 19%, MS[M+H]+=603).

Synthesis Example 5. Synthesis of Compound A-3-1

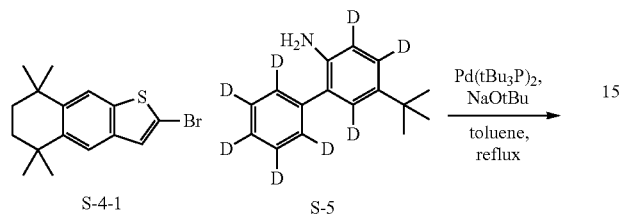

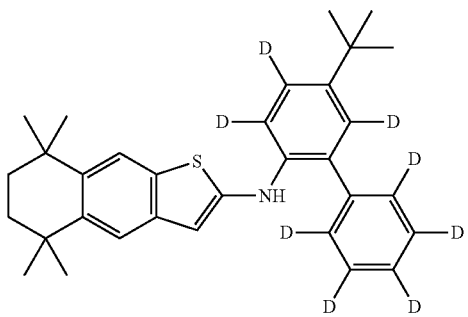

Compound A-3-1 (18.2 g, yield 95%, MS[M+H]+=476) was obtained in the same manner as in Synthesis Example 2 except that Compounds S-4-1 (13 g, 1 eq.) and S-5 were used instead of Compounds S-3 and S-4.

Synthesis Example 6. Syntheis of Compound A-3-2

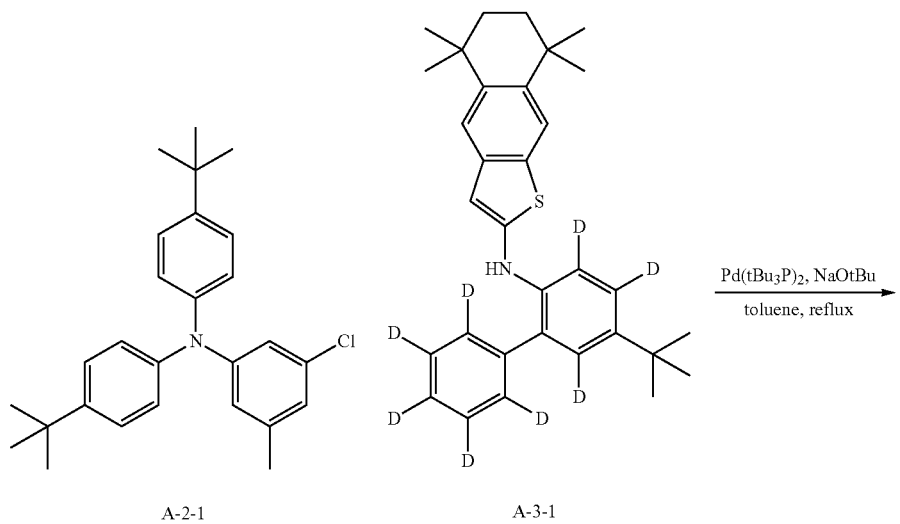

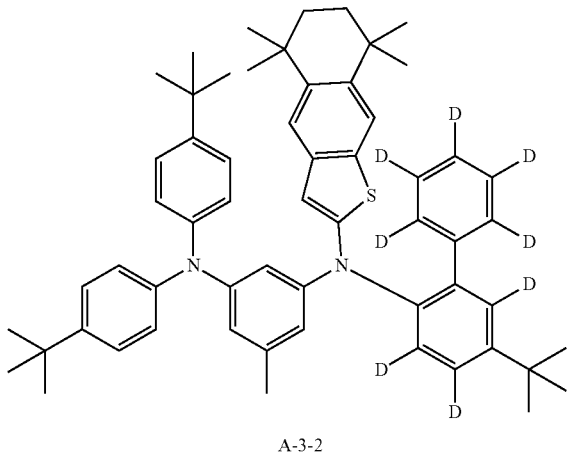

Compound A-3-2 (18.4 g, yield 59%, MS[M+H]+=845) was obtained in the same manner as in Synthesis Example 3 except that Compounds A-2-1 (15 g. 1 eq.) and A-3-1 were used instead of Compounds A-2-1 and A-2-2.

Compound A-3 (3.2 g, yield 59%, MS[M+H]+=853) was obtained in the same manner as in Synthesis Example 4 except that Compound A-3-2 (18.4 g. 1 eq.) was used instead of Compound A-2-3.

Synthesis Example 7. Synthesis of Compound A-3

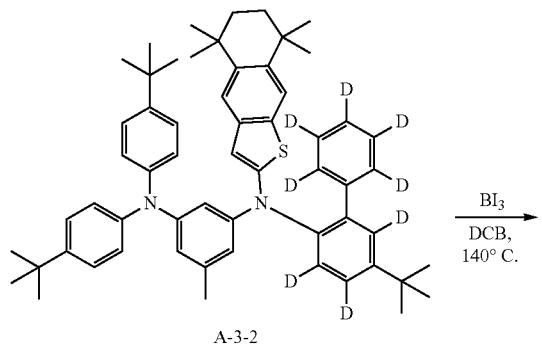

Syntheis Example 8. Synthesis of Compound A-7-1

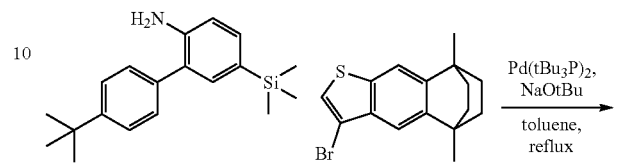

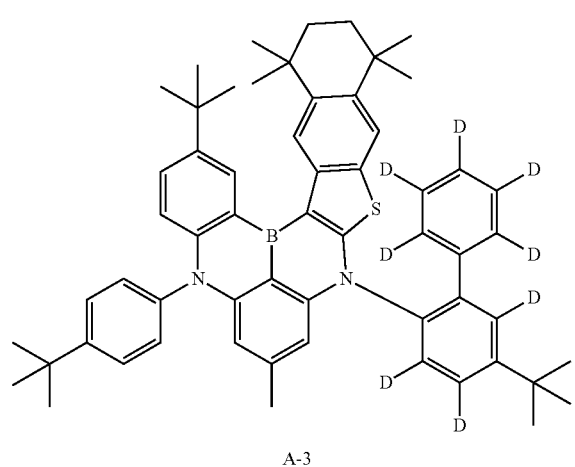

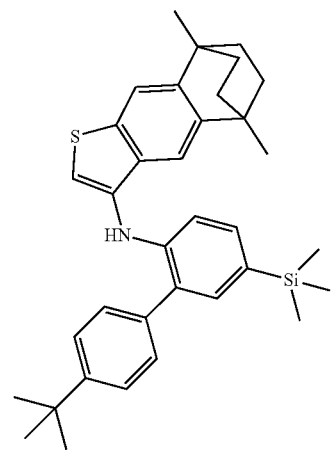

Compound A-7-1 (14.6 g, yield 62%, MS[M+H]+=538) was obtained in the same manner as in Synthesis Example 2 except that Compounds S-6 (13 g, 1 eq.) and S-7 were used instead of Compounds S-3 and S-4.

Synthesis Example 9. Synthesis of Compound A-7-2

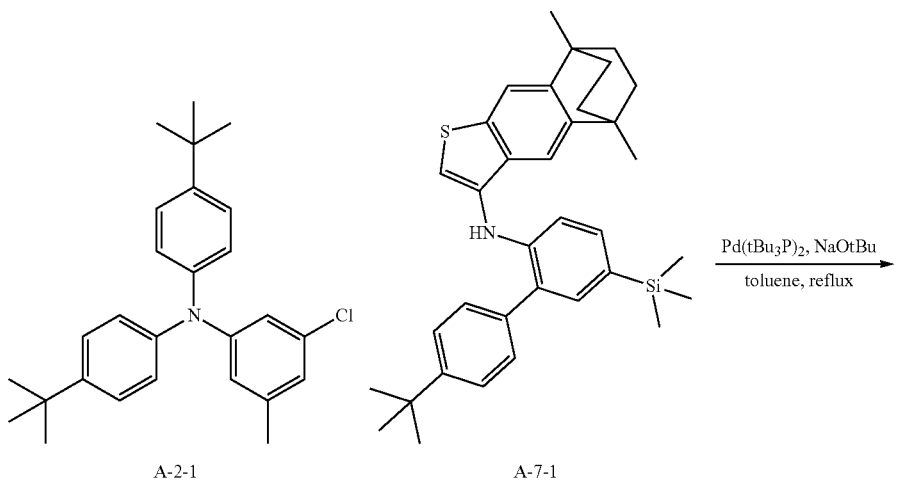

-continued

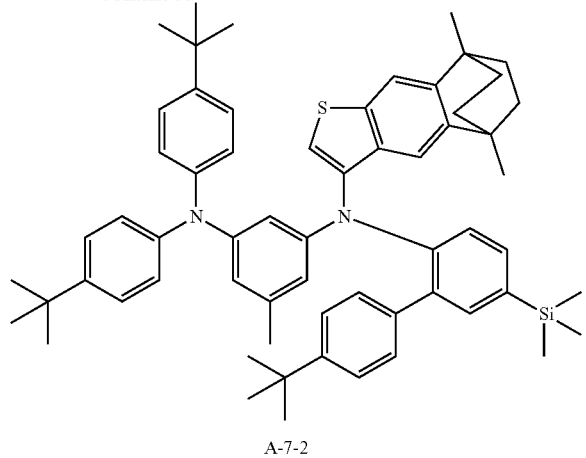

A-7-2

Compound A-7-2 (16.5 g, yield 74%, MS[M+H]+=907) was obtained in the same manner as in Synthesis Example 3 except that Compounds A-2-1 (10 g, 1 eq.) and A-7-1 were used instead of Compounds A-2-1 and A-2-2.

Synthesis Example 10. Synthesis of Compound A-7

Synthesis Example 11. Synthesis of Compound A-1-1

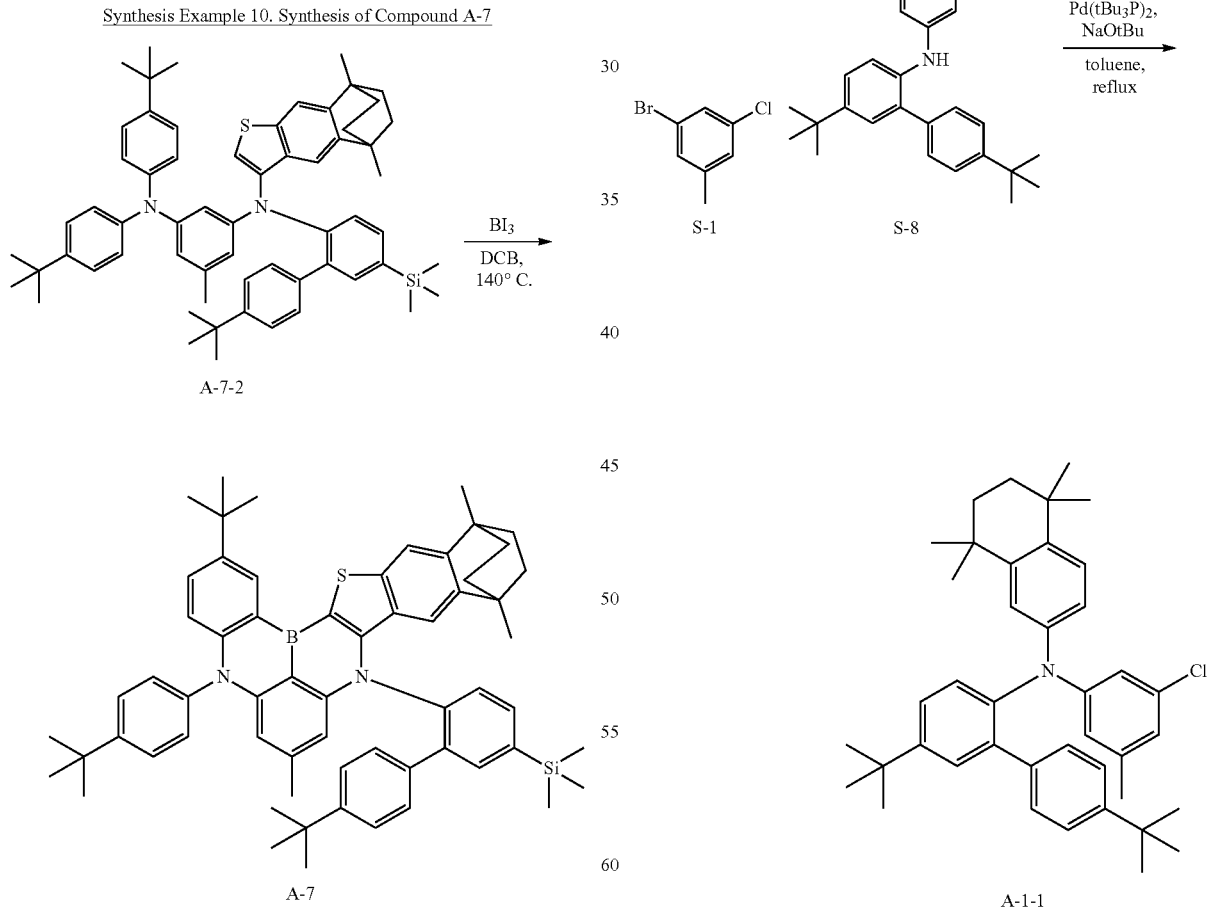

Compound A-7 (2.8 g, yield 17%, MS[M+H]+=915) was obtained in the same manner as in Synthesis Example 4 except that Compound A-7-2 (16.5 g, 1 eq.) was used instead of Compound A-2-3.

Compound A-1-1 (29.4 g, yield 75%, MS[M+H]+=592) was obtained in the same manner as in Synthesis Example 1 except that Compound S-8 (1 eq.) was used instead of Compound S-2.

Synthesis Example 12. Synthesis of Compound A-1-2

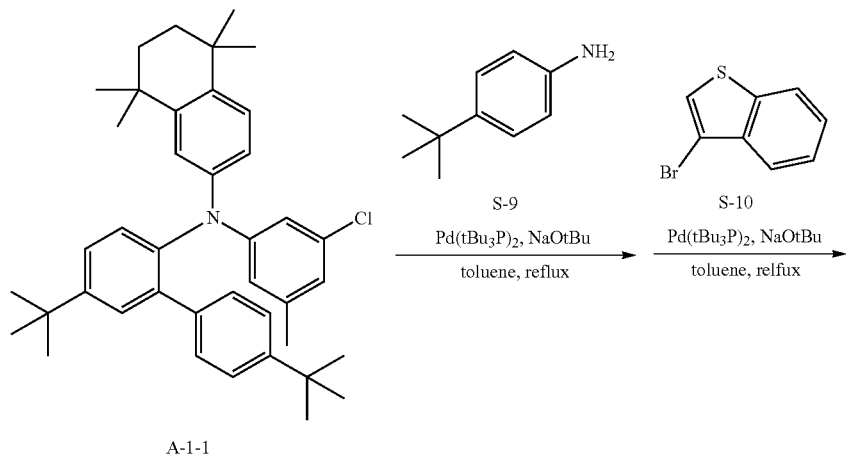

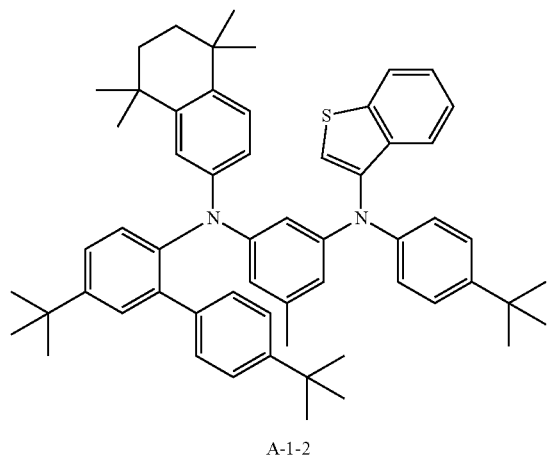

Compound A-1-1 (29.4 g, 49.6 mmol, 1 eq.), 4-(tert-butyl) aniline (S-9, 7.78 g, 52.1 mmol, 1.05 eq.), Pd(Pt-Bu₃)₂ (0.25 g, 0.01 eq.) and NaOt-Bu (7.2 g, 1.5 eq.) were dissolved in toluene (250 ml), and stirred under reflux. When the reaction was finished, the result was cooled to room temperature, and then the reaction solution was transferred to a separatory funnel and then extracted. The result was dried with MgSO₄, filtered and concentrated, and a next reaction proceeded without a further purification process.

Compound S-10 (11.1 g, 51.1 mmol, 1.5 eq.), Pd(Pt-BU₃)₂ (0.25 g, 0.1 eq.) and NaOt-Bu (7.2 g, 1.5 eq.) were dissolved in toluene (204 ml), and stirred under reflux. When the reaction was finished, the result was cooled to room temperature, and then the reaction solution was transferred to a separatory funnel and then extracted. The result was dried with MgSO₄, filtered, concentrated, and purified usingcolumn chromatography to obtain Compound A-1-2 (22.9 g, 55%).

MS:[M+H]⁺=837

Synthesis Example 13. Synthesis of Compound A-1

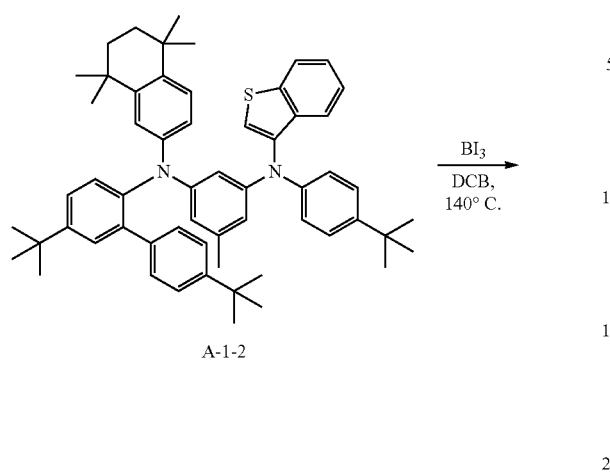

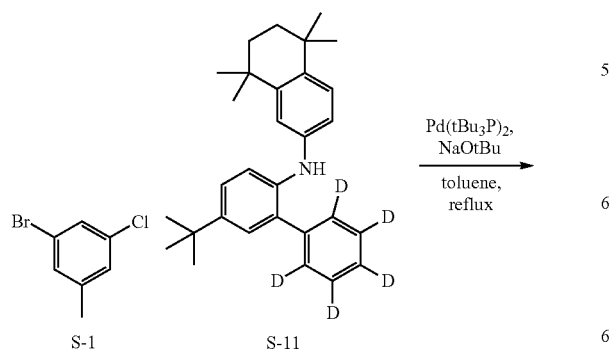

Compound A-1 (4.2 g, yield 28%, MS[M+H]+=846) was obtained in the same manner as in Synthesis Example 4 except that Compound A-1-2 (15 g, 1 eq.) was used instead of Compound A-2-3.

Synthesis Example 14. Synthesis of Compound A-4-1

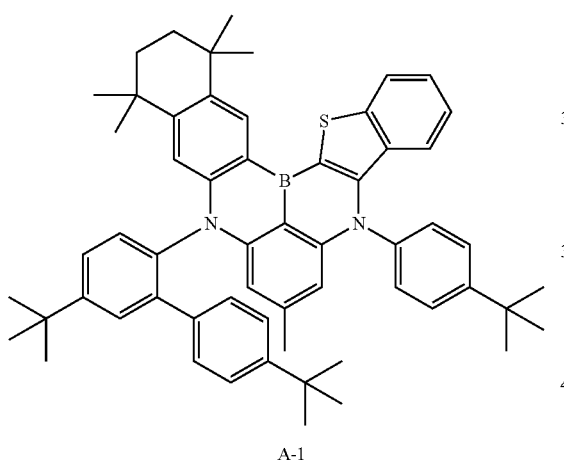

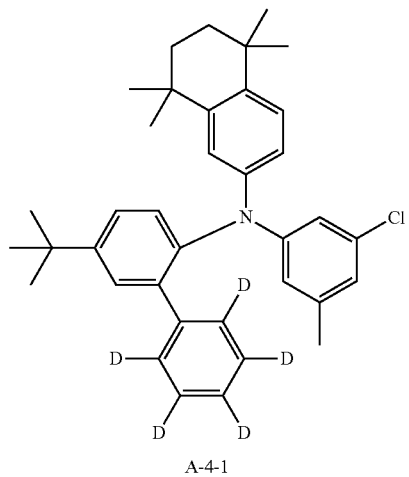

Compound A-4-1 (17.9 g, yield 68%, MS[M+H]+=541) was obtained in the same manner as in Synthesis Example 1 except that Compound S-11 (20.3 g, 1 eq.) was used instead of Compound S-2.

Synthesis Example 14-1. Synthesis of Compound A-4-2

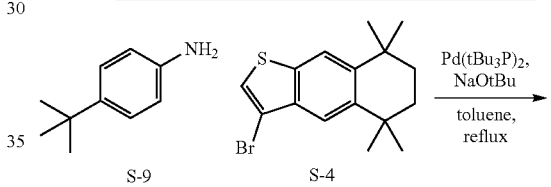

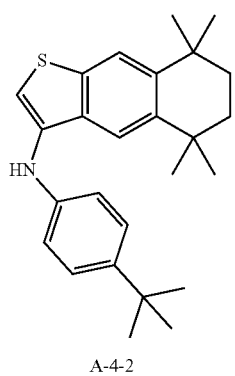

Compound A-4-2 (15.5 g, yield 59%, MS[M+H]+=392) was obtained in the same manner as in Synthesis Example 2 except that Compound S-9 (10 g, 1 eq.) was used instead of Compound S-3.

Synthesis Example 15. Synthesis of Compound A-4-3

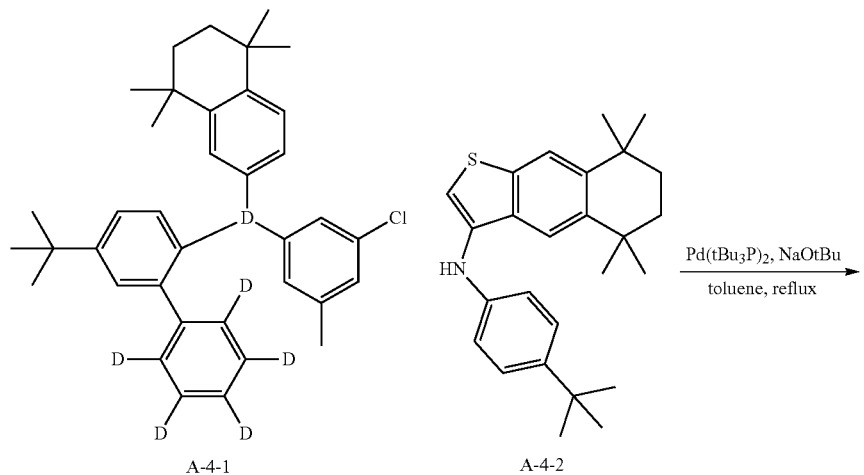

Compound A-4-3 (18.8 g, yield 71%, MS[M+H]+=857) was obtained in the same manner as in Synthesis Example 3 except that Compounds A-4-1 (16 g. 1 eq.) and A-4-2 (11.6 q. 1 eq.) were used instead of Compounds A-2-1 and A-2-2.

Synthesis Example 16. Synthesis of Compound A-4

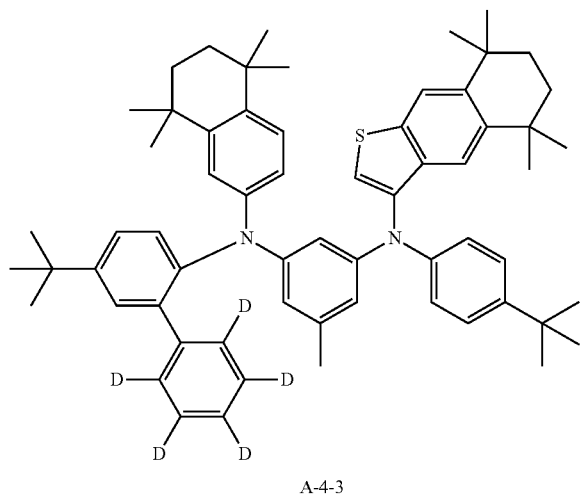

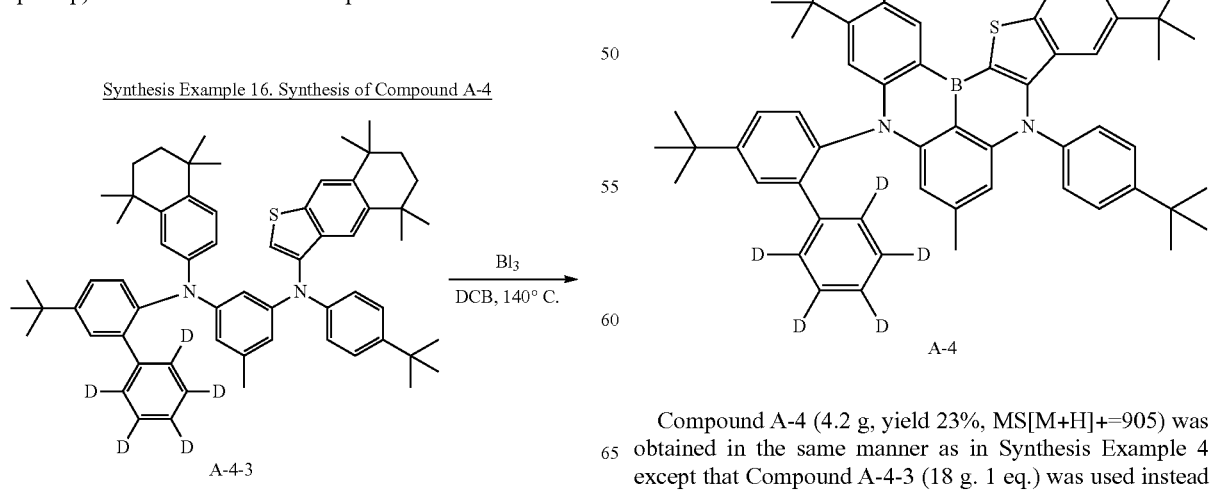

Compound A-4 (4.2 g, yield 23%, MS[M+H]+=905) was obtained in the same manner as in Synthesis Example 4 except that Compound A-4-3 (18 g. 1 eq.) was used instead of Compound A-2-3.

Synthesis Example 17. Synthesis of Compound A-5-1

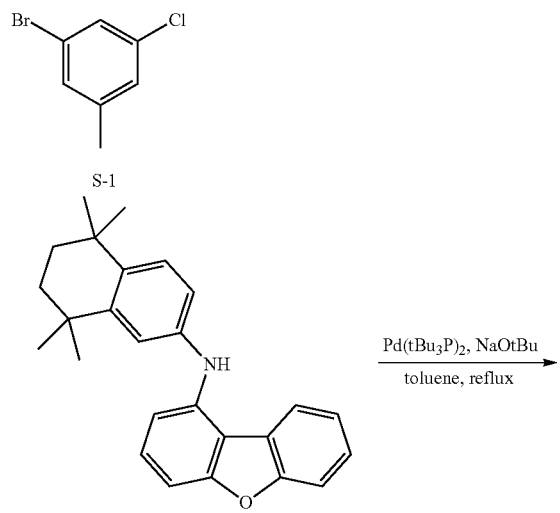

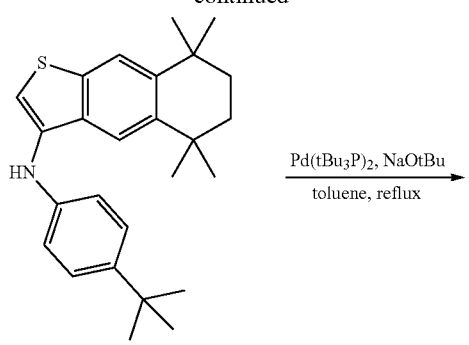

Compound A-5-1 (18.5 g, yield 77%, MS[M+H]+=494) was obtained in the same manner as in Synthesis Example 1 except that Compound S-12 (18 g, 1 eq.) was used instead of Compound S-2, and xylene was used instead of toluene.

Synthesis Example 28. Synthesis of Compound A-5-2

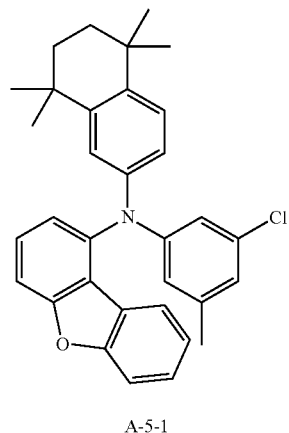

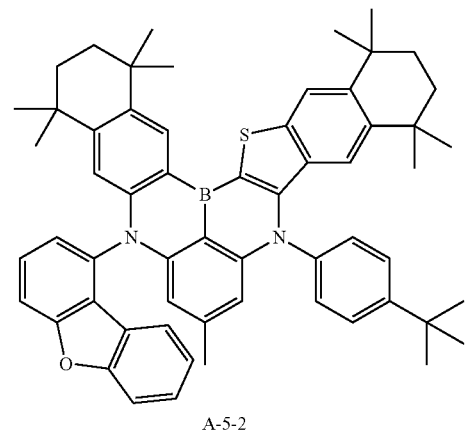

Compound A-5-2 (9.9 g, yield 64%, MS[M+H]+=849) was obtained in the same manner as in Synthesis Example 3 except that Compounds A-5-1 (9 g, 1 eq.) and A-4-2 (7.1 g, 1 eq.) were used instead of Compounds A-2-1 and A-2-2.

Synthesis Example 19. Synthesis of Compound A-5

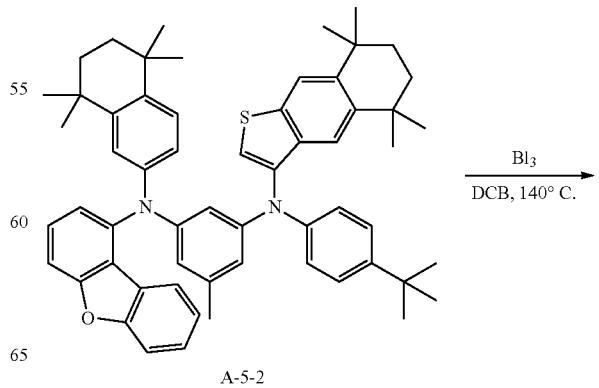

1125

-continued

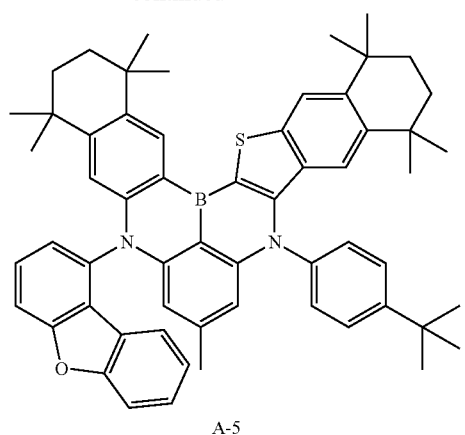

A-5

Compound A-5 (3.5 g, yield 35%, MS[M+H]+=857) was obtained in the same manner as in Synthesis Example 4 except that Compound A-5-2 (9.9 g. 1 eq.) was used instead of Compound A-2-3.

Synthesis Example 20. Synthesis of Compound A-6-1

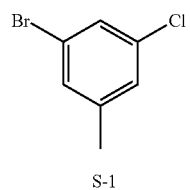

S-1

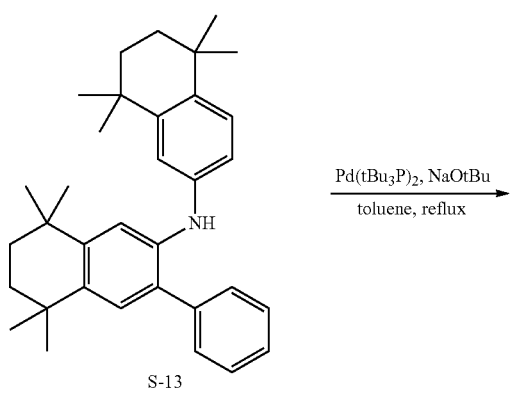

S-13

A-6-1

1126

Compound A-6-1 (124.1 g, yield 84%, MS[M+H]+=590) was obtained in the same manner as in Synthesis Example 1 except that Compound S-13 (22.7 g. 1 eq.) was used instead of Compound S-2.

Sythesis Example 21. Synthesis of Compound A-6-2

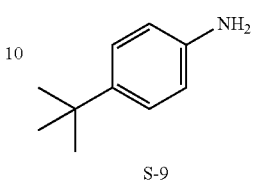

S-9

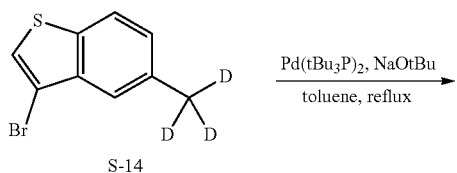

S-14

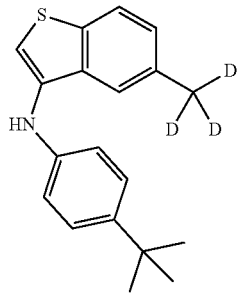

A-6-2

Compound A-6-2 (8.8 g, yield 55%, MS[M+H]+=299) was obtained in the same manner as in Synthesis Example 2 except that Compounds S-9 (8 g, 1 eq.) and S-14 (12.3 g) were used instead of Compounds S-3 and S-4.

Synthesis Example 22. Synthesis of Compound A-6-3

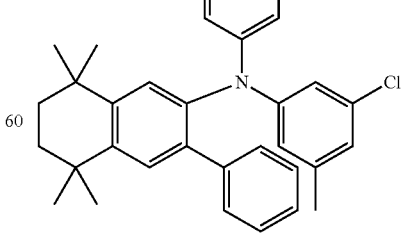

A-6-1

1127

-continued

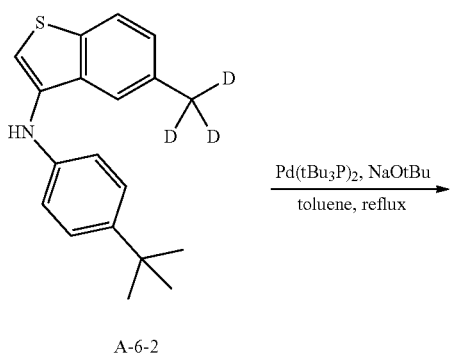

A-6-2

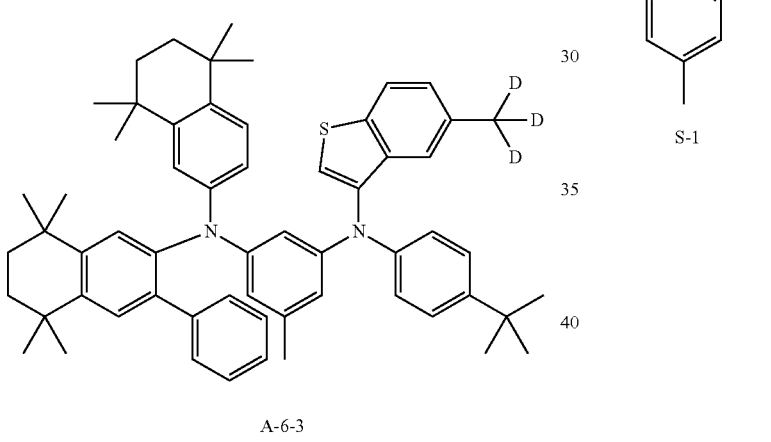

A-6-3

Compound A-6-3 (10.6 g, yield 61%, MS[M+H]+=523) was obtained in the same manner as in Synthesis Example 3 except that Compounds A-6-1 (12 g. 1 eq.) and A-6-2 (6.1 g) were used instead of Compounds A-2-1 and A-2-2.

Synthsis Example 23. Synthesis of Compound A-6

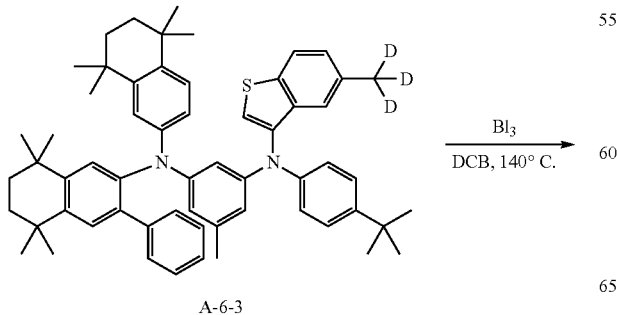

A-6-3

1128

-continued

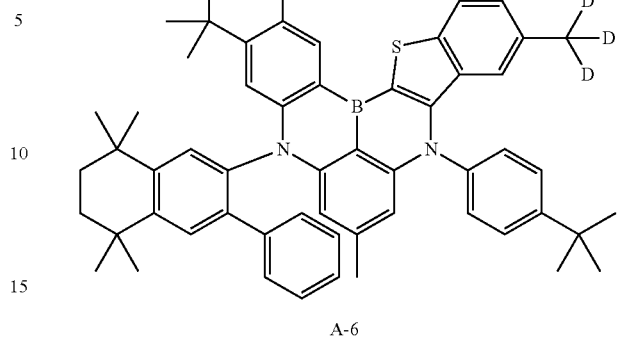

A-6

Compound A-6 (2.5 g, yield 26%, MS[M+H]+=861) was obtained in the same manner as in Synthesis Example 4 except that Compound A-6-3 (9.5 g. 1 eq.) was used instead of Compound A-2-3.

Synthesis Example 24. Synthesis of Compound A-11-1

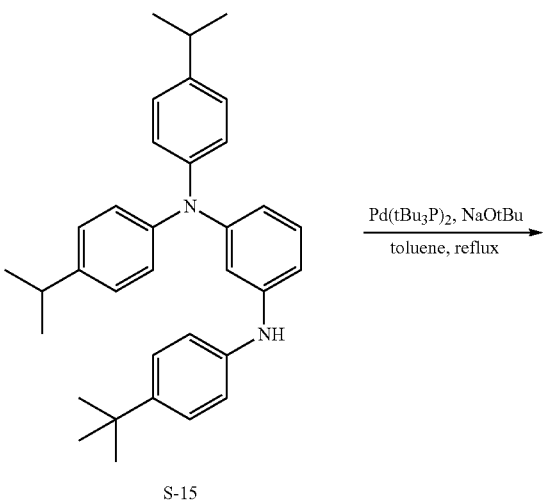

S-1

S-15

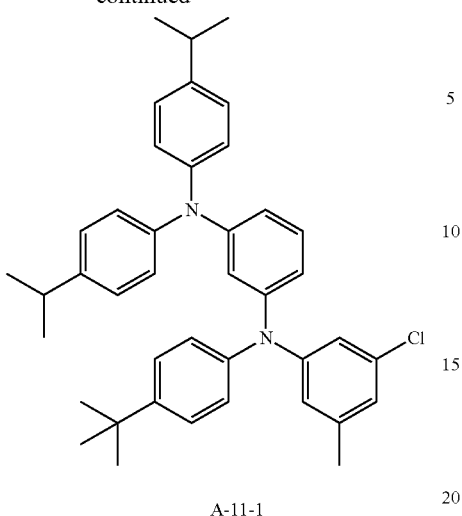

A-11-1

Compound A-11-1 (18.0 g, yield 77%, MS[M+H]+=601) was obtained in the same manner as in Synthesis Example 1 except that Compound S-15 (18.6 g. 1 eq.) was used instead of Compound S-2.

Synthesis Example 25. Synthesis of Compound A-11-2

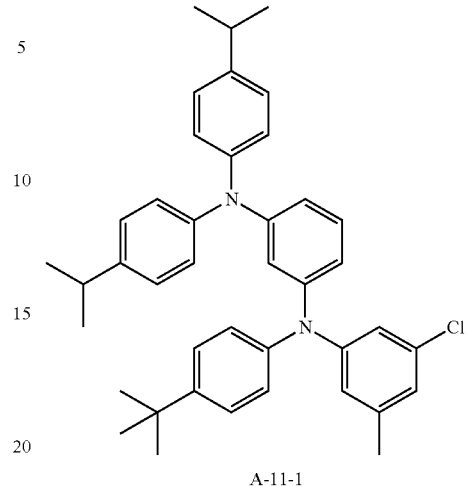

A-11-1

Synthesis Example 25. Synthesis of Compound A-11-2

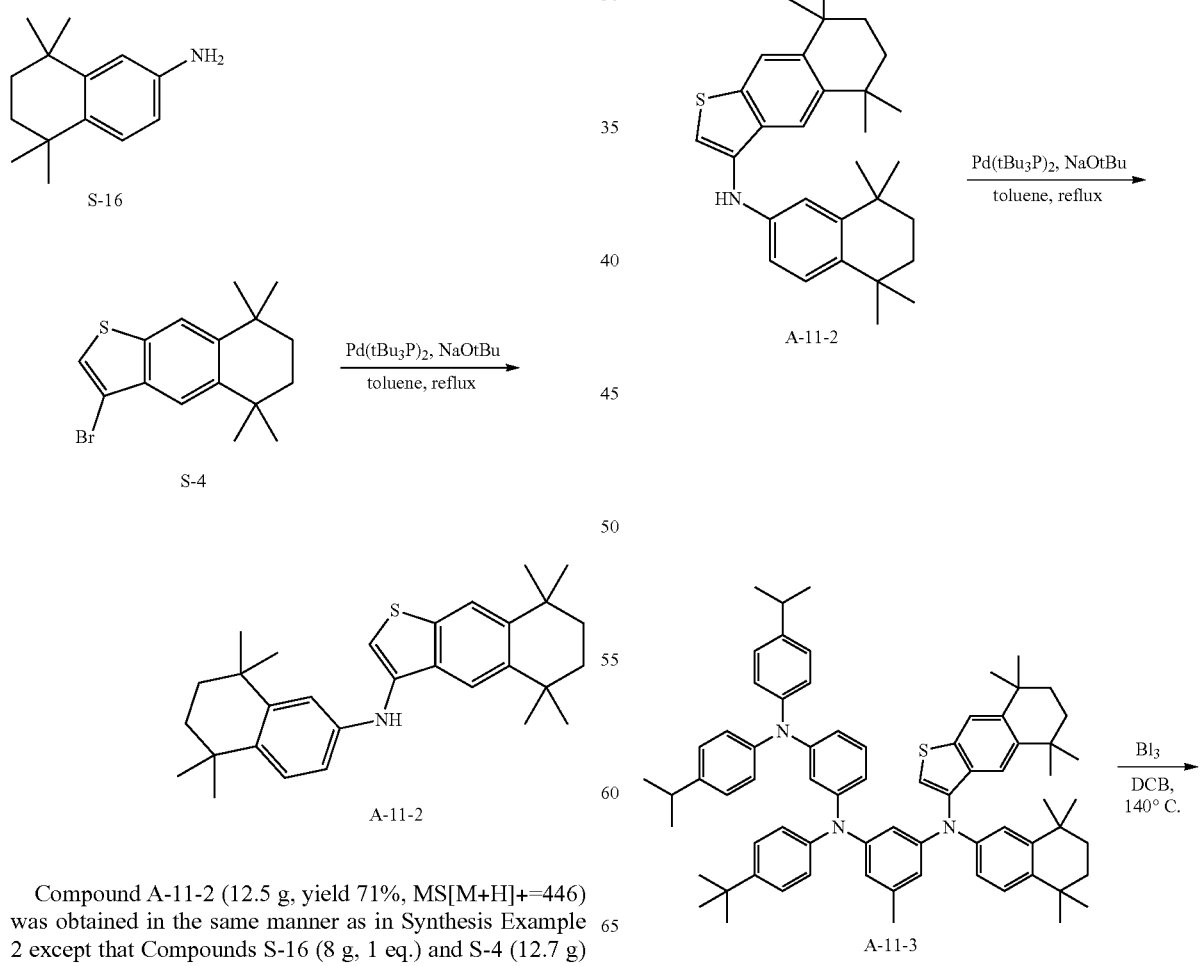

A-11-2

Compound A-11-2 (12.5 g, yield 71%, MS[M+H]+=446) was obtained in the same manner as in Synthesis Example 2 except that Compounds S-16 (8 g, 1 eq.) and S-4 (12.7 g) were used instead of Compounds S-3 and S-4.

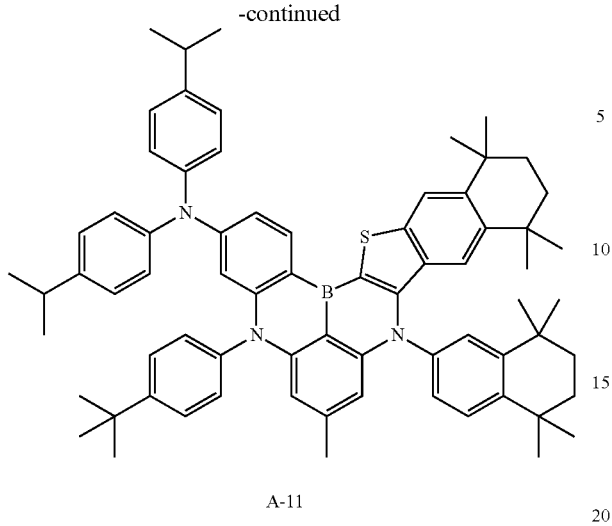

A-11

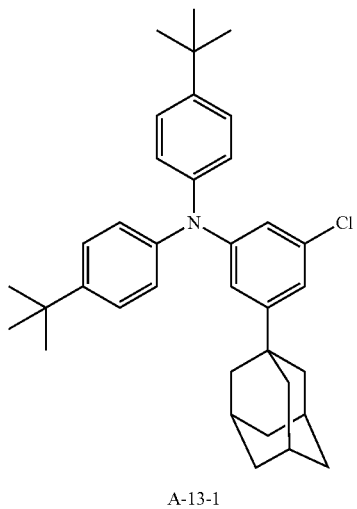

A-13-1

Compound A-11-3 (18.5 g, yield 71%, MS[M+H]+=1010) was obtained in the same manner as in Synthesis Example 3 except that Compounds A-11-1 (15.5 g. 1 eq.) and A-11-2 (11.5 g) were used instead of Compounds A-2-1 and A-2-2.

Compound A-11 (3.2 g, yield 22%, MS[M+H]+=1017) was obtained in the same manner as in Synthesis Example 4 except that Compound A-11-3 (14.5 g. 1 eq.) was used instead of Compound A-2-3.

Compound A-13-1 (13.5 g, yield 84%, MS[M+H]+=526) was obtained in the same manner as in Synthesis Example 1 except that Compound, S-17 (10 g. 1 eq.) was used instead of Compound S-1.

Synthesis Example 27. Synthesis of Compound A-13-1

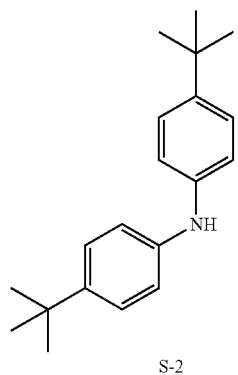

S-2

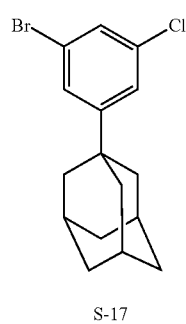

S-17

Pd(tBu₃P)₂, NaOtBu
toluene, reflux
⟶

Synthesis Example 28. Synthesis of Compound A-13-2

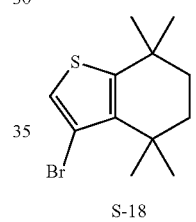

S-18

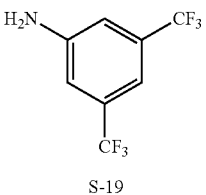

S-19

Pd(tBu₃P)₂, NaOtBu
toluene, reflux
⟶

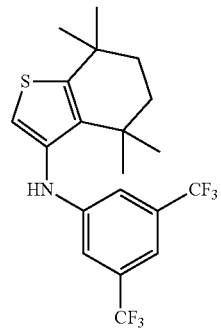

A-13-2

Compound A-13-2 (9.0 g, yield 49%, MS[M+H]+=422) was obtained in the same manner as in Synthesis Example 2 except that Compounds S-19 (10 g, 1 eq.) and S-18 (11.9 g) were used instead of Compounds S-3 and S-4.

Synthesis Example 29. Synthesis of Compound A-13

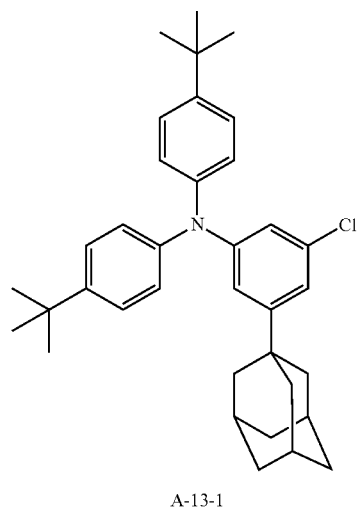

A-13-1

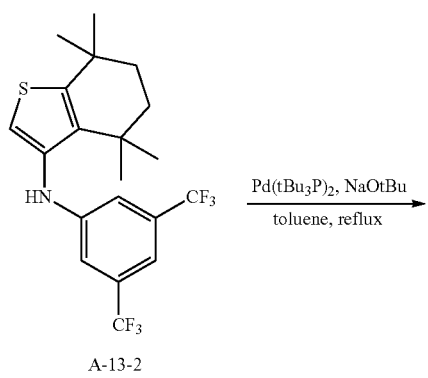

A-13-2

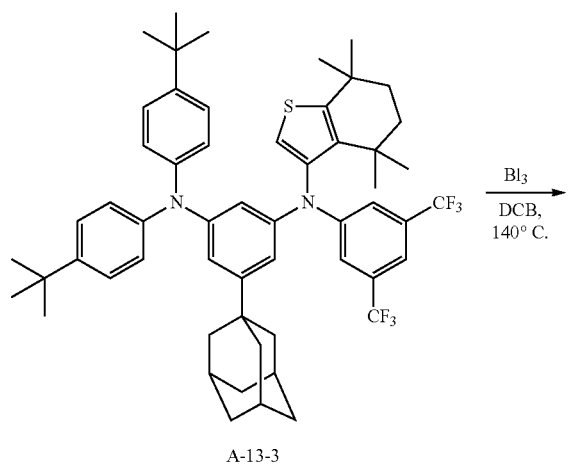

A-13-3

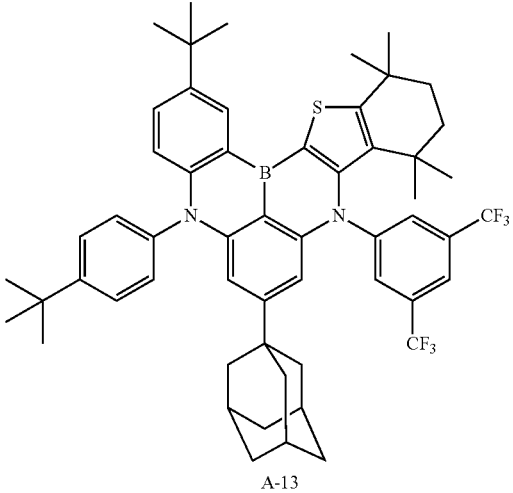

A-13

Compound A-13-3 (10.8 g, yield 61%, MS[M+H]+=911) was obtained in the same manner as in Synthesis Example 3 except that Compounds A-13-3 (10.2 g, 1 eq.) and A-13-2 (8.2 g) were used instead or Compounds A-2-1 and A-2-2.

Compound A-13 (1.9 g, yield 19%, MS[M+H]+=919) was obtained in the same manner as in Synthesis Example 4 except that Compound A-13-3 (9.7 g. 1 eq.) was used instead of Compound A-2-3.

Synthesis Example 30. Synthesis of Compound A-12-1

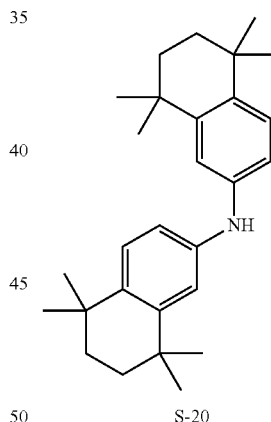

S-20

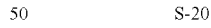

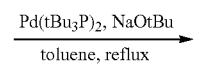

S-21

1135
-continued

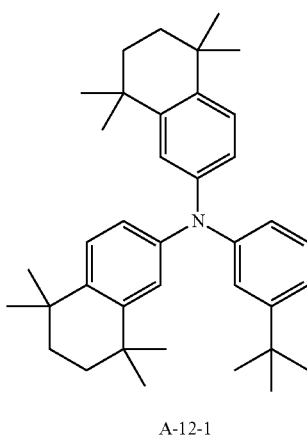

A-12-1

Compound A-12-1 (35.5 g, yield 79%, MS[M+H]+=556) was obtained in the same manner as in Synthesis Example 1 except that Compounds S-21 (20 g, 1 eq.) and S-20 (31.5 g) were used instead of Compounds S-1 and S-2.

Synthesis Example 31. Synthesis of Compound A-12

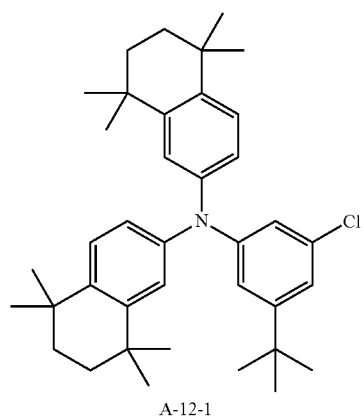

A-12-1

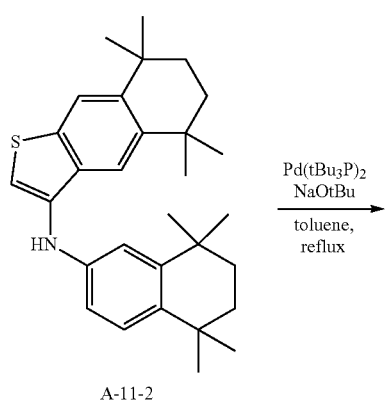

A-11-2

1136
-continued

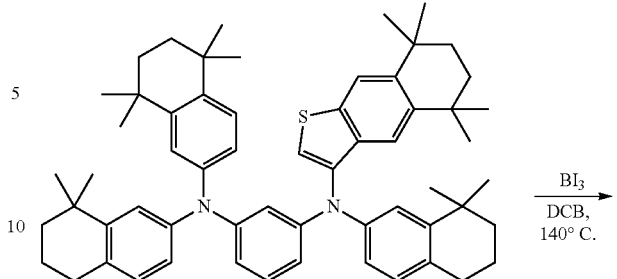

A-12-2

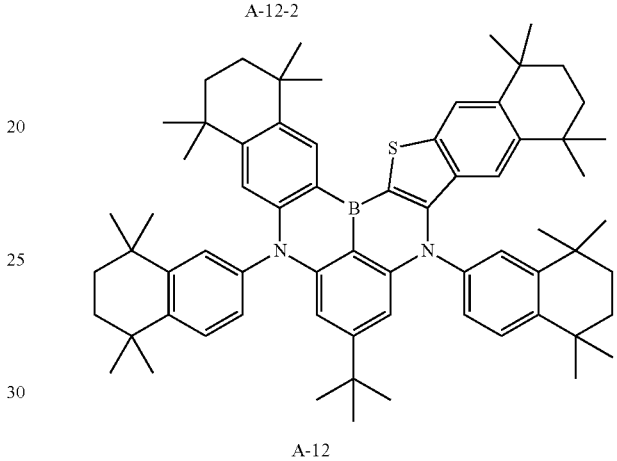

A-12

Compound A-12-2 (11.8 g, yield 68%, MS[M+H]+=966) was obtained in the same manner as in Synthesis Example 3 except that Compounds A-12-1 (10 g, 1 eq.) and A-11-2 (8 g) were used instead of Compounds A-2-1 and A-2-2.

Compound A-12 (3.9 g, yield 39%, MS[M+H]+=973) was obtained in the same manner as in Synthesis Example 4 except that Compound A-12-2 (10 g, 1 eq.) was used instead of Compound A-2-3.

Synthesis Example 32. Synthesis of Compound A-8-1

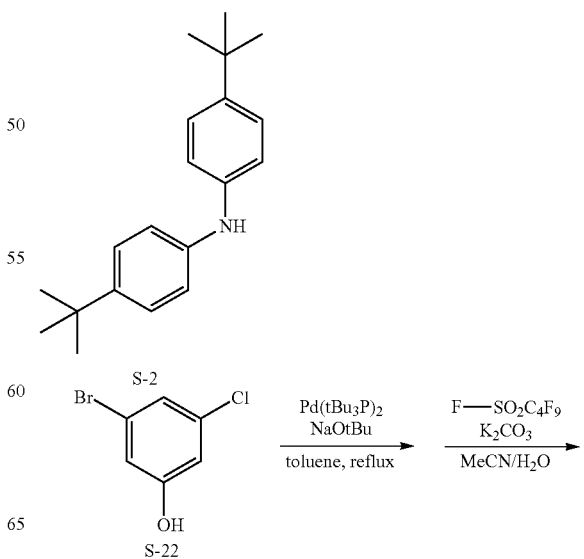

S-22

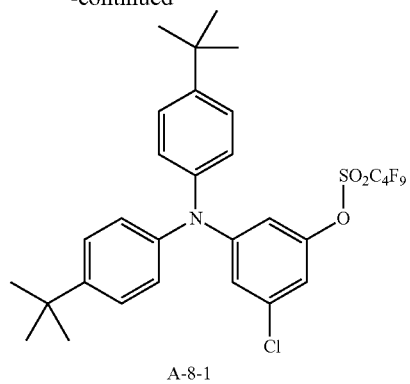

A-8-1

A reaction product was prepared in the same manner as in Synthesis Example 1 except that Compounds S-22 (20 g. 1 eq.) and S-2 (27.1 g) were used instead of Compounds S-1 and S-2, and a next reaction proceeded without a further purification process.

The reaction product that did not go through a purification process was dissolved in tetrahydrofuran (THF) (240 mL), and then potassium carbonate (17.3 g, 1.3 eq.) dissolved in water (80 mL) was slowly added thereto. Perfluorobutanesulfonyl fluoride (43.7 g, 1.5 eq.) was added thereto, and the result was stirred for 2 hours at room temperature. After the reaction was completed, the result was separated by adding water and ethyl acetate thereto, then treated with MgSO$_4$ (anhydrous), and filtered. The filtered solution was removed by distillation under vacuum, and purified using a column chromatography method to obtain Compound A-8-1 (44.7 g, yield 67%).

Synthesis Example 33. Synthesis of Compound A-8-2

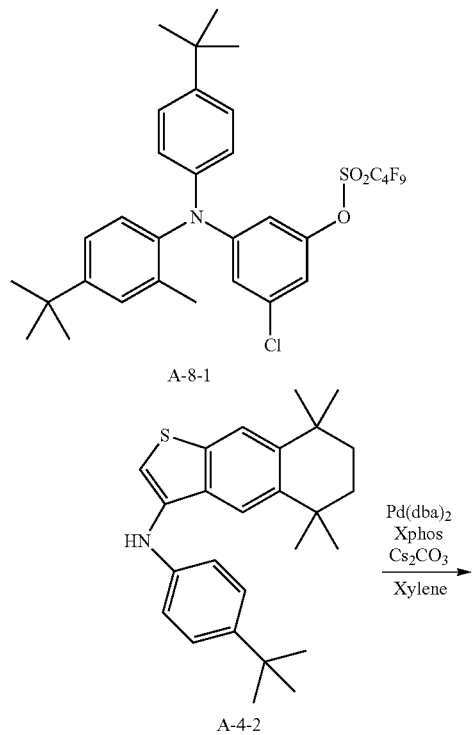

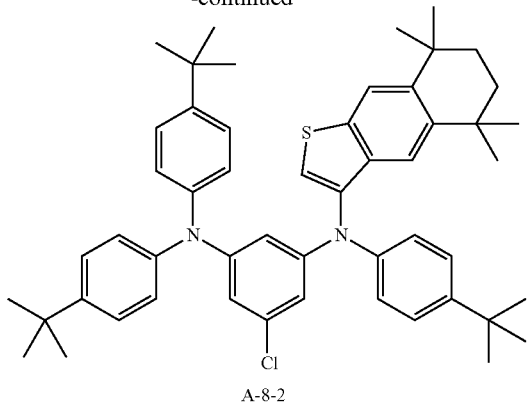

A-8-2

A flask holding Compound A-8-1 (12 g, 17.4 mmol, 1 eq.), Compound A-4-2 (7.2 g, 1.05 eq.), palladium(0) bis (dibenzylideneacetone) (Pd(dba)$_2$) (0.1 g, 0.01 eq.), 2-dicyclohexylphosphino-2',4',6'-triisopropylbiphenyl (Xphos) (0.17 g, 0.02 eq.), Cs$_2$CO$_3$ (17 g, 3 eq.) and xylene (90 ml) was heated to 140° C., and the mixture was stirred for 12 hours. The reaction solution was cooled to room temperature, separated by adding sat. aq. NH$_4$Cl and toluene thereto, and the solvent was removed by distillation under vacuum. The result was purified using silica gel column chromatography (ethyl acetate/hexane) to obtain Compound A-6-2 (9.6 g, yield 72%, MS[M+H]+=781).

Synthesis Example 34. Synthesis of Compound A-8-3

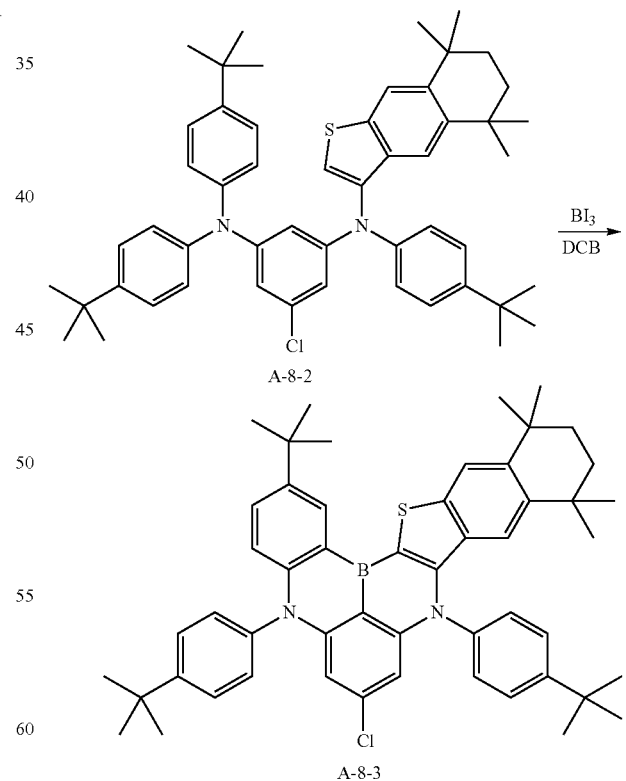

Compound A-8-3 (4.0 g, yield 42%, MS[M+H]+=775) was obtained in the same manner as in Synthesis Example 4 except that Compound A-3-2 (9.7 g. 1 eq.) was used instead of Compound A-2-3.

Synthesis Example 35. Synthesis of Compound A-8

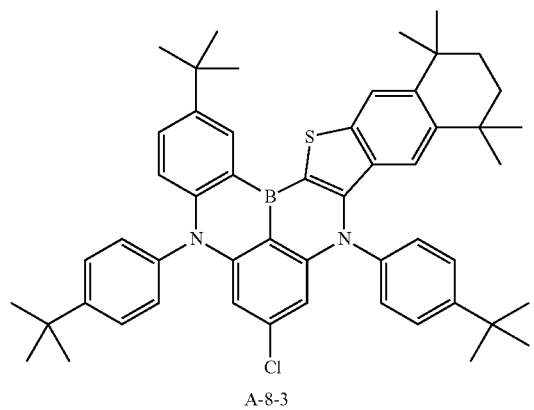

Synthesis Example 36. Synthesis of Compound A-9-2

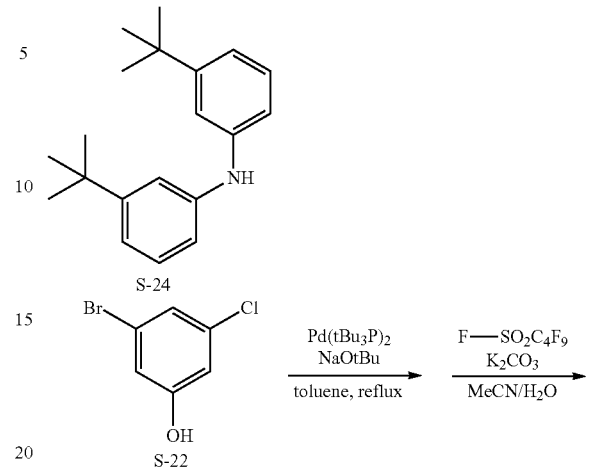

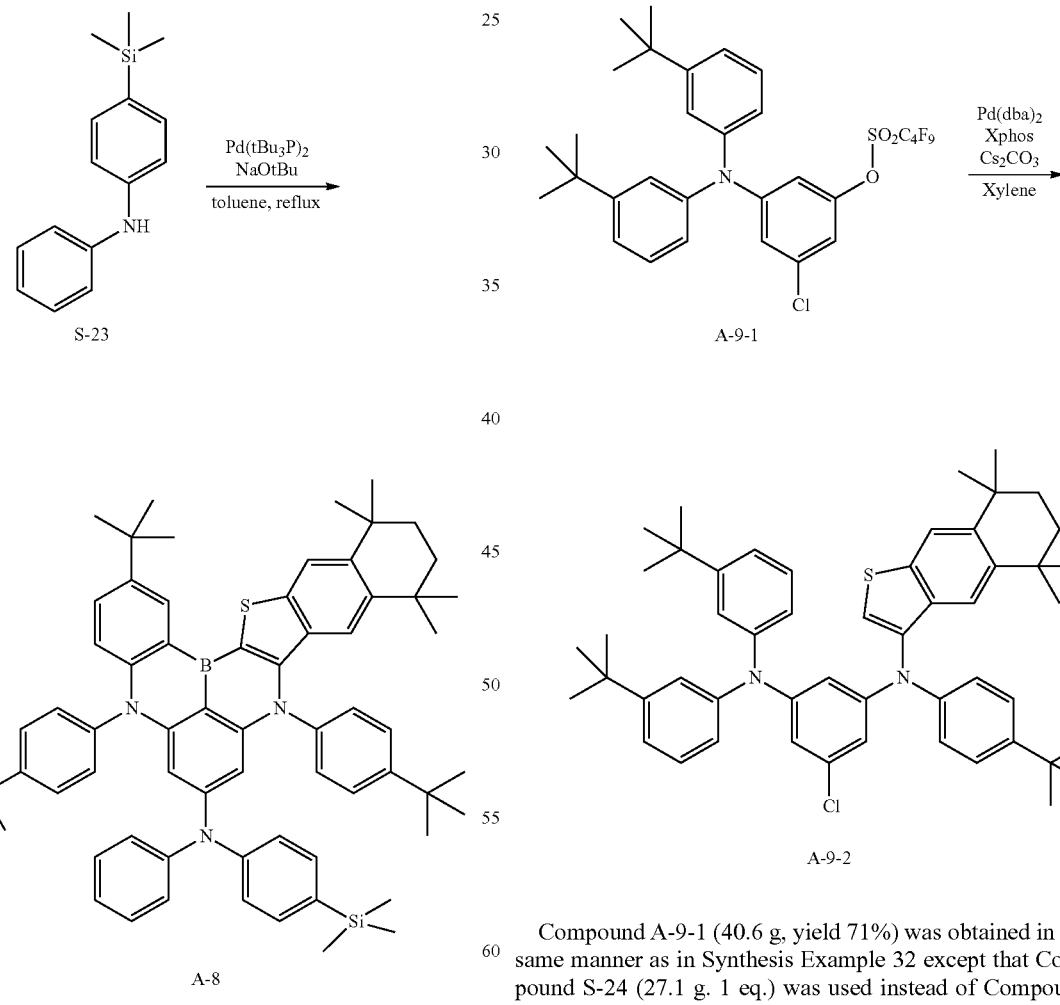

Compound A-8 (3.8 g, yield 74%, MS[M+H]+=995) was obtained in the same manner as in Synthesis Example 3 except that Compounds A-8-3 (4 g. 1 eq.) and S-23 (1.5 g, 1.2 eq.) were used instead of Compounds A-2-1 and A-2-2.

Compound A-9-1 (40.6 g, yield 71%) was obtained in the same manner as in Synthesis Example 32 except that Compound S-24 (27.1 g. 1 eq.) was used instead of Compound S-2.

Compound A-9-2 (11.6 g, yield 68%, MS[M+H]+=781) was obtained in the same manner as in Synthesis Example 33 except that Compound A-9-1 (15 g, 1 eq.) was used instead of Compound A-8-1.

Synthesis Example 37. Synthesis of Compound A-9

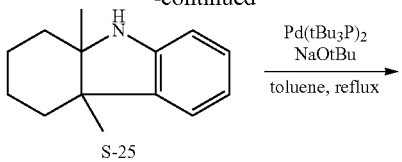

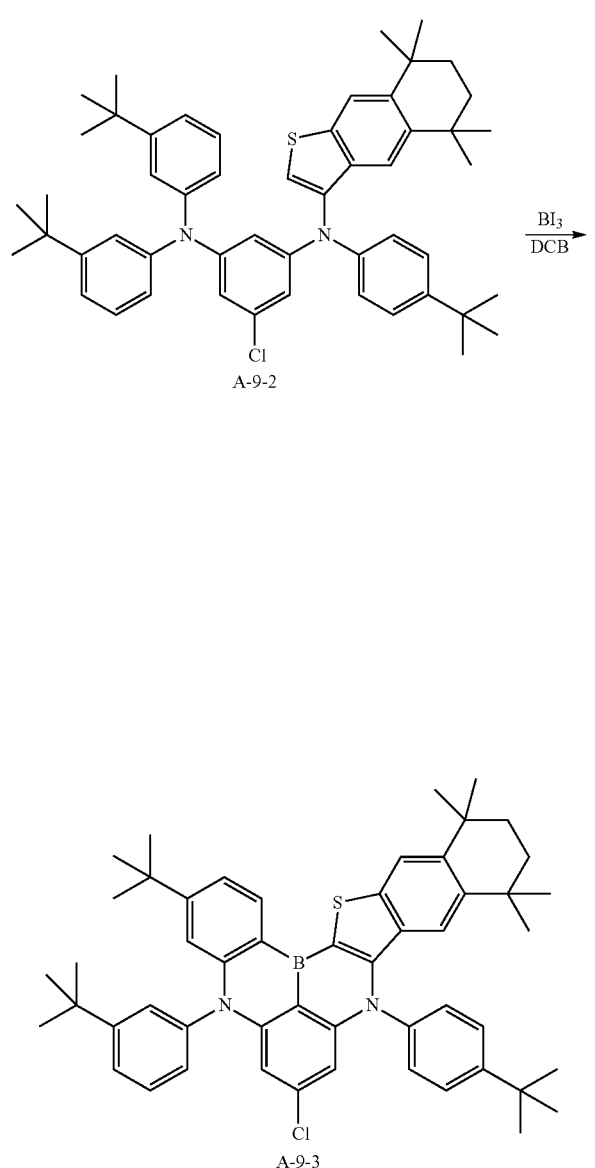

Compound A-9-3 (4.2 g, yield 40%, MS[M+H]+=775) was obtained in the same manner as in Synthesis Example 4 except that Compound A-9-2 (10.5 g. 1 eq.) was used instead of Compound A-2-3.

Compound A-9 (3.4 g, yield 66%, MS[M+H]+=955) was obtained in the same manner as in Synthesis Example 3 except that Compounds A-9-3 (4.2 g. 1 eq.) and S-25 (1.3 g) were used instead of Compounds A-2-1 and A-2-2.

Synthesis Example 38. Synthesis of Compound A-10-2

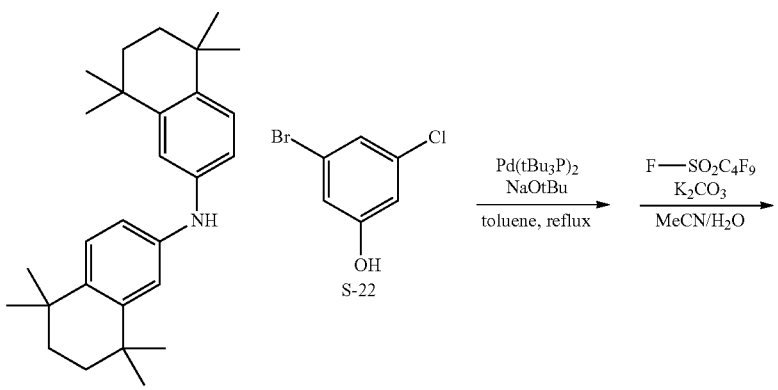

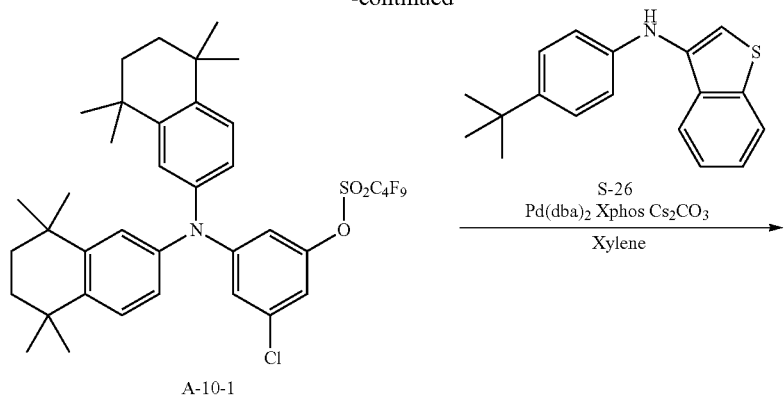
Compound A-10-1 (51 g, yield 66%) was obtained in the same manner as in Synthesis Example 32 except that Compound S-20 (37.6 g. 1 eq.) was used instead of Compound S-2.
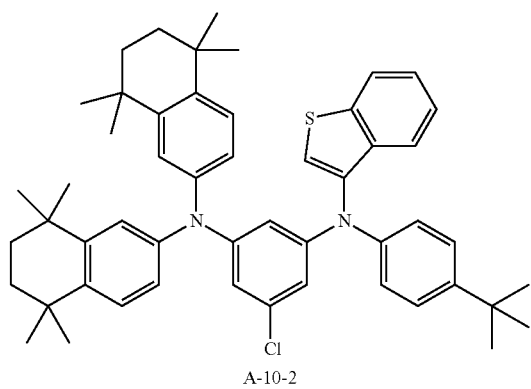
Compound A-10-2 (8.4 g, yield 66%, MS[M+H]+=779) was obtained in the same manner as in Synthesis Example 33 except that Compound A-10-1 (13 g, 1 eq.) was used instead of Compound A-8-1.
Synthesis Example 39. Synthesis of Compound A-10
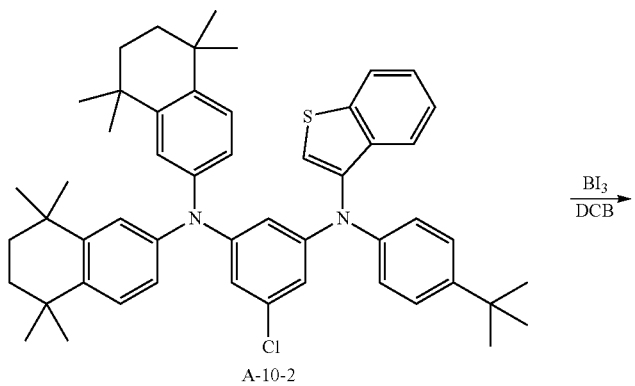

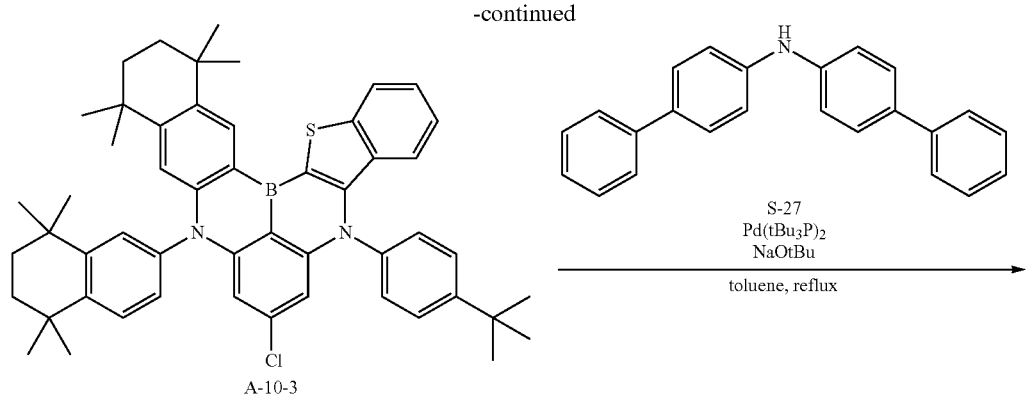

A-10-3

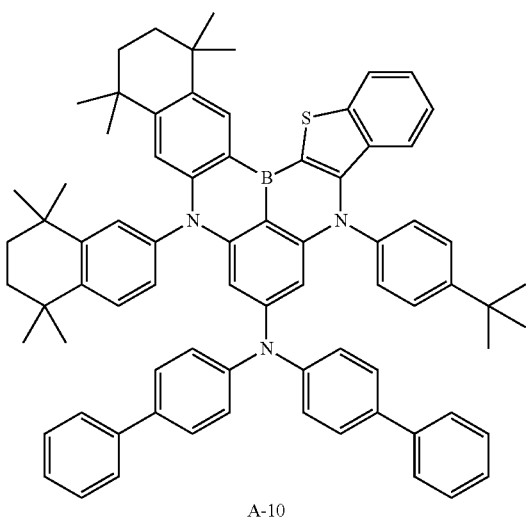

A-10

Compound A-10-3 (3.5 g, yield 42%, MS[M+H]+=787) was obtained in the same manner as in Synthesis Example 4 except that Compound A-10-2 (8.3 g. 1 eq.) was used instead of Compound A-2-3.

Compound A-10 (3.7 g, yield 77%, MS[M+H]+=1073) was obtained in the same manner as in Synthesis Example 3 except that Compounds A-10-3 (3.5 g. 1 eq.) and S-27 (1.7 g) were used Instead of Compounds A-2-1 and A-2-2.

Synthesis Example 40. Synthesis of Compound A-14-1

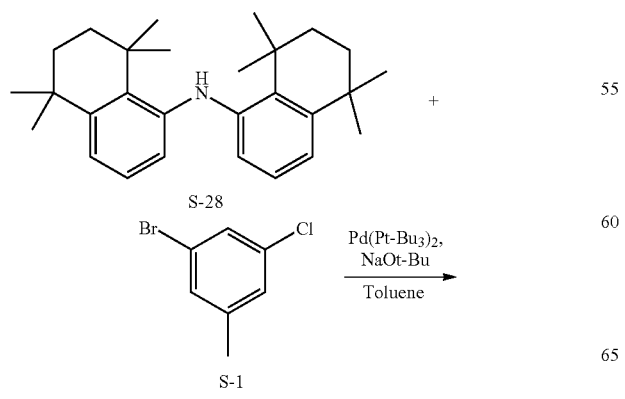

-continued

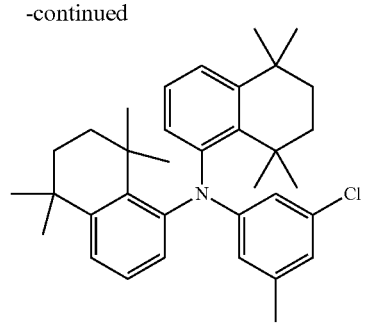

A-14-1

Compound A-14-1 (12.4 g, yield 59%, MS[M+H]+=515) was obtained in the same manner as in Synthesis Example 1 except that Compound S-28 was used instead of Compound S-2.

Synthesis Example 40-1. Synthesis of Compound A-14-3
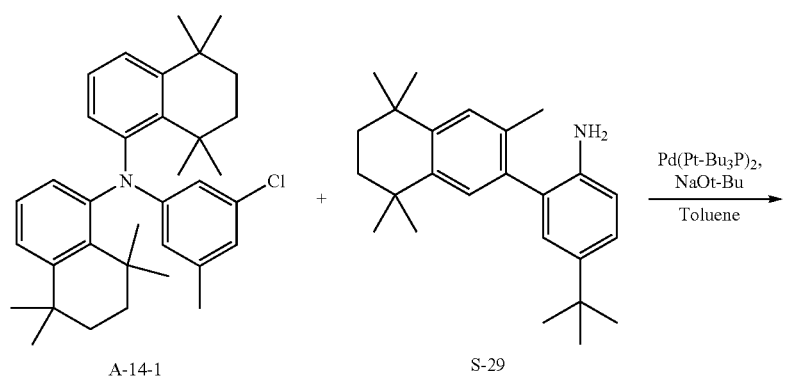
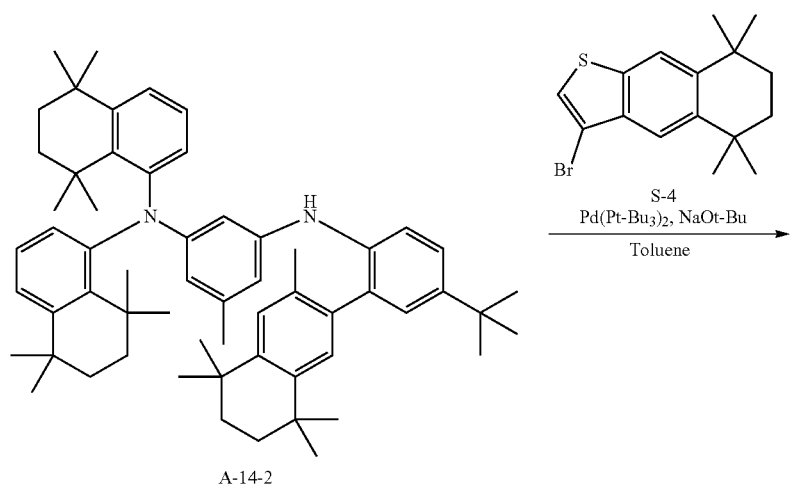
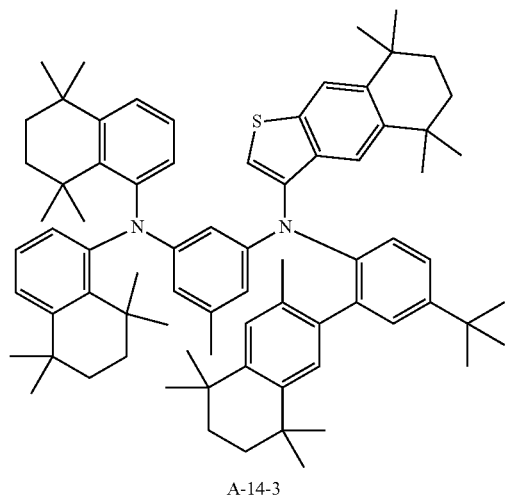
Compound A-14-3 (10.8 g, yield 42%, MS[M+H]+= 1070) was obtained in the same manner, as in Synthesis Example 12 except that Compounds A-14-1 (12.4 g, 1 eq.), S-29 and S-4 were used instead of Compounds A-1-1, S-9 and S-10

Synthesis Example 41. Synthesis of Compound A-14

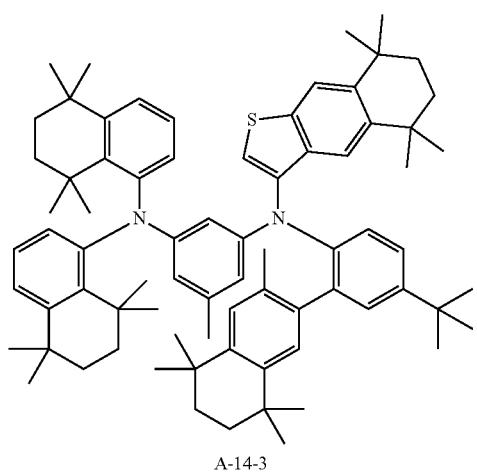

A-14-3

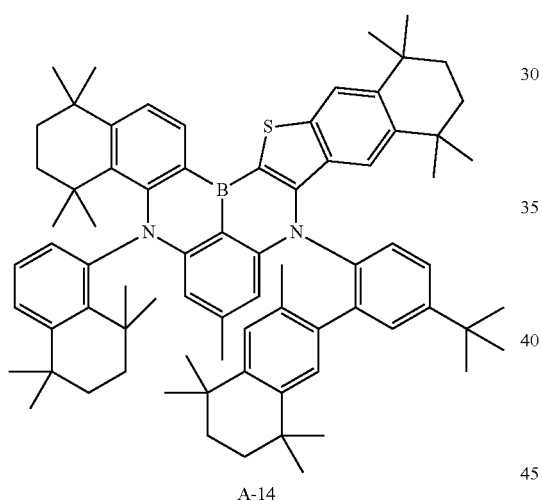

A-14

Compound A-14 (2.6 g, yield 24%, MS[M+H]+=1078) was obtained in the same manner as in Synthesis Example 4 except that Compound A-14-3 (10.8 g, 1 eq.) was used instead of Compound A-2-3.

Synthesis Example 42. Synthesis of Compound A-15-1

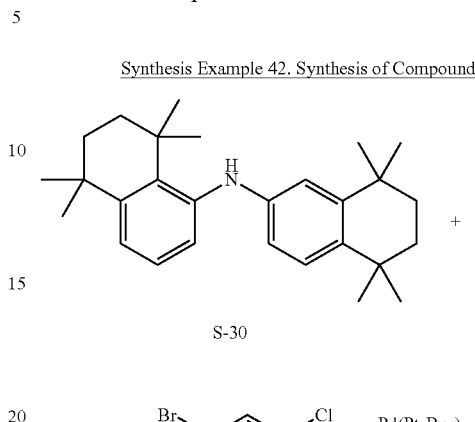

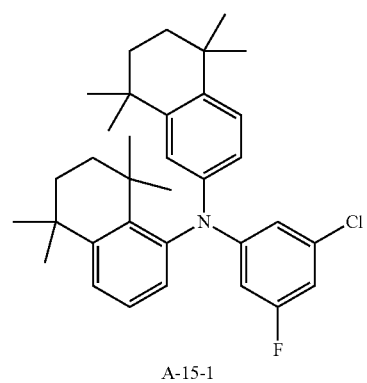

A-15-1

Compound A-15-1 (20.1 g, yield 68%, MS[M+H]+=519) was obtained in the same manner as in Synthesis Example 1 except that Compounds S-30 and 1-bromo-3-chloro-5-fluorobenzene were used instead of Compounds S-2 and S-1.

Synthesis Example 43. Synthesis of Compound A-15-3

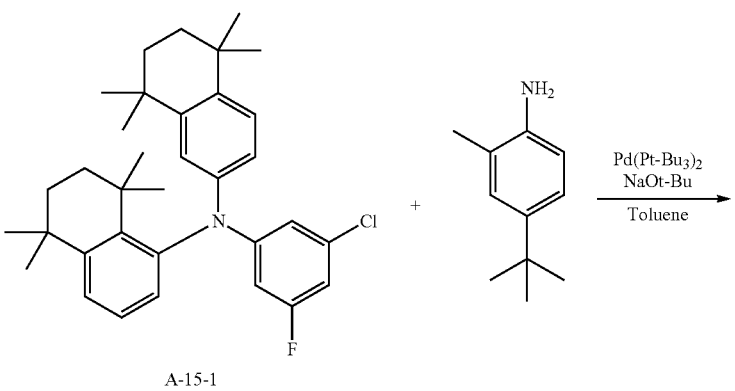

A-15-1

-continued

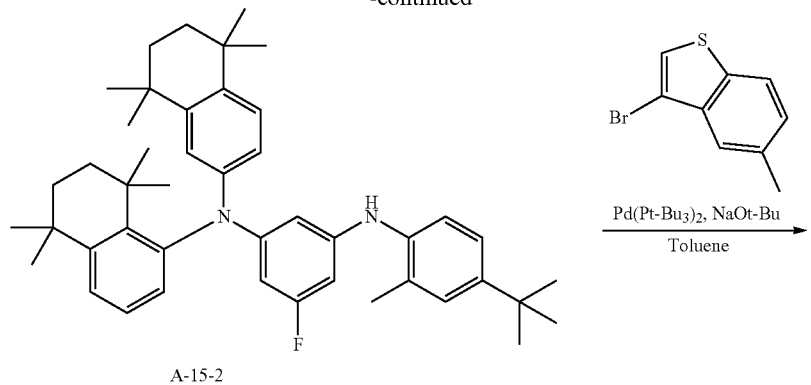

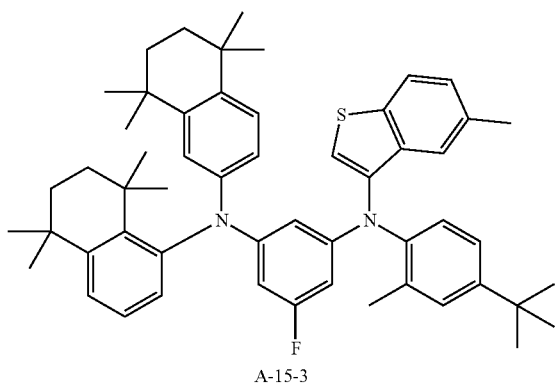

Compound A-15-3 (11.2 g, yield 49%, MS[M+H]+=792) was obtained in the same manner as in Synthesis Example 12 except that Compounds A-15-1 (15 g, 1 eq.), 4-(tert-butyl)-2-methylaniline and 3-bromo-5-methylbenzo[b]thiophene were used instead of Compounds A-1-1, S-9 and S-10.

Synthesis Example 44. Synthesis of Compound A-15

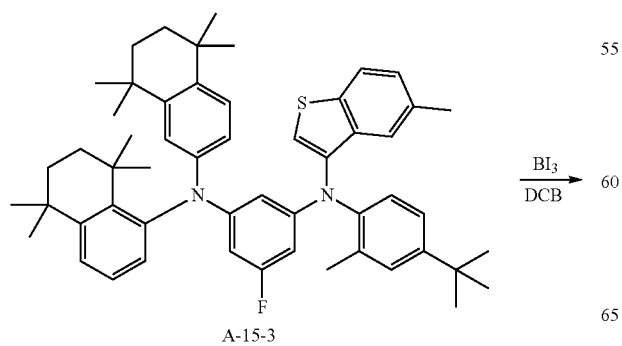

-continued

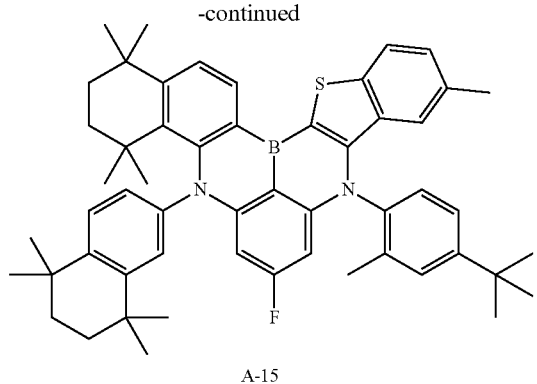

Compound A-15 (1.8 g, yield 18%, MS[M+H]+=799) was obtained in the same manner as in Synthesis Example 4 except that Compound A-15-3 (10 g. 1 eq.) was used instead of Compound A-2-3.

Synthesis Example 45. Synthesis of Compound A-16-1

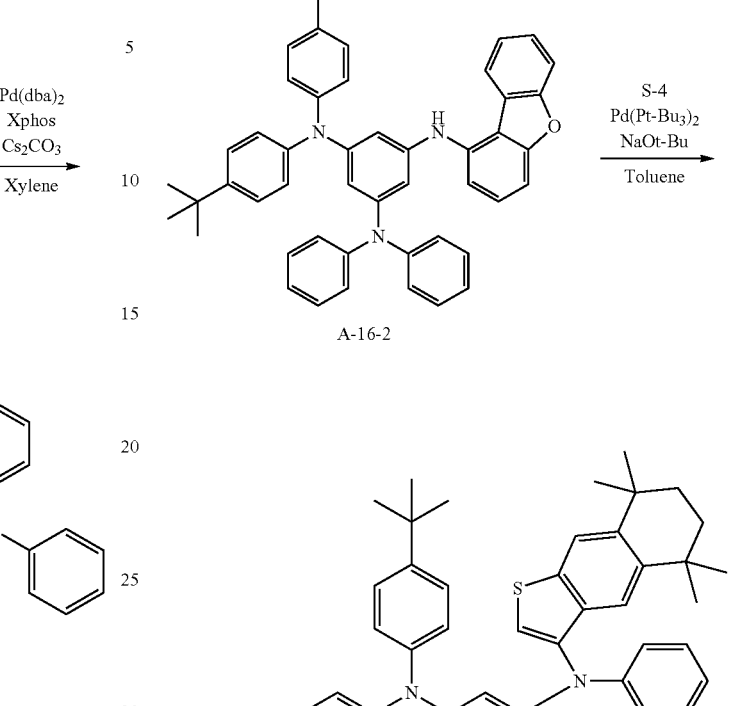

Compound A-16-1 (18.7 g, yield 73%, MS[M+H]+=559) was obtained in the same manner as in Synthesis Example 33 except that diphenylamine was used instead of Compound A-4-2.

Synthesis Example 46. Synthesis of Compound A-16-3

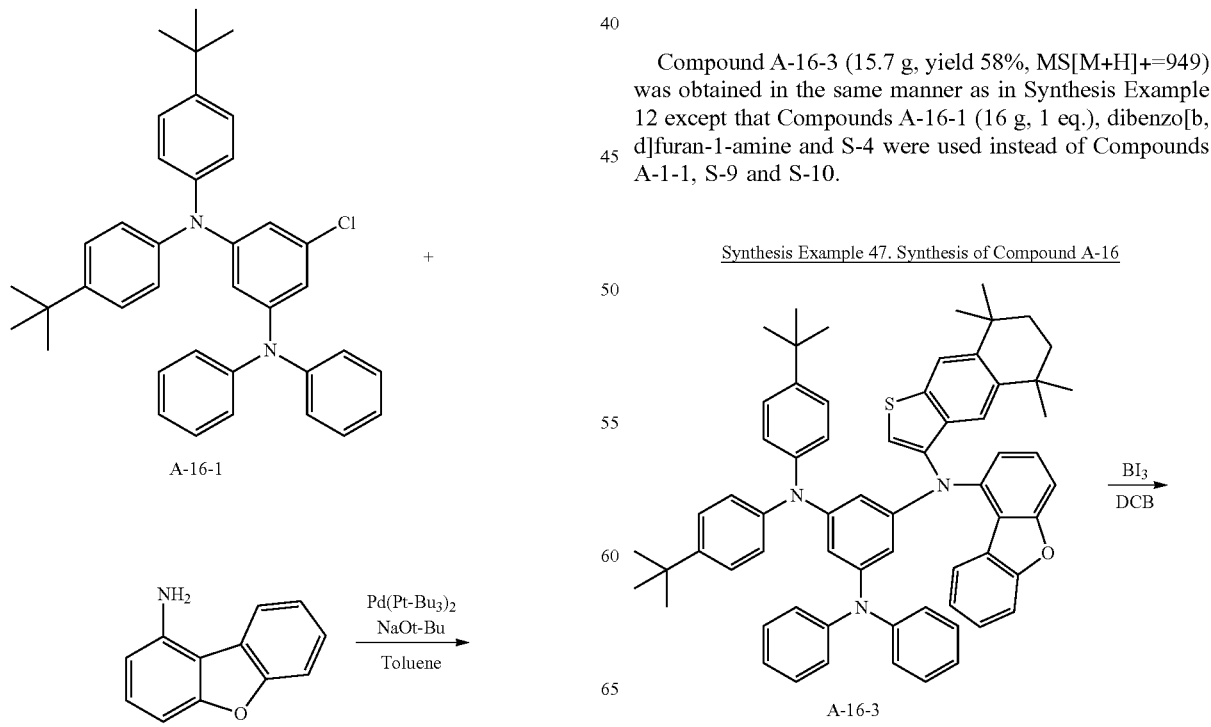

Compound A-16-3 (15.7 g, yield 58%, MS[M+H]+=949) was obtained in the same manner as in Synthesis Example 12 except that Compounds A-16-1 (16 g, 1 eq.), dibenzo[b,d]furan-1-amine and S-4 were used instead of Compounds A-1-1, S-9 and S-10.

Synthesis Example 47. Synthesis of Compound A-16

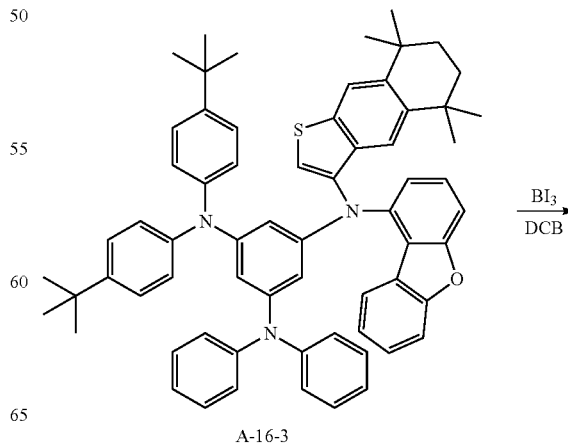

-continued

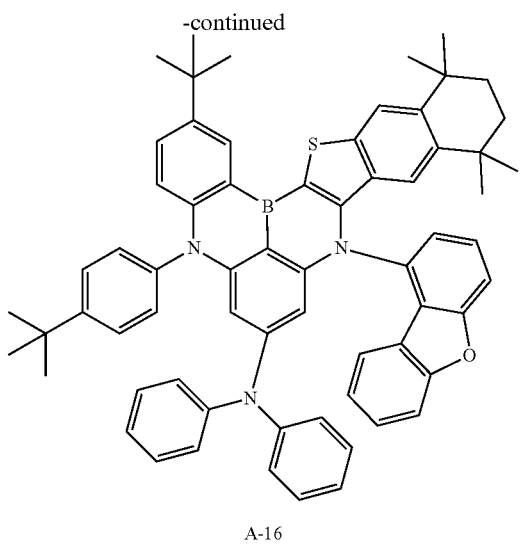

A-16

Compound A-16 (2.1 g, yield 21%, MS[M+H]+=957) was obtained in the same manner as in Synthesis Example 4 except that Compound A-16-3 (10 g. 1 eq.) was used instead of Compound A-2-3.

Synthesis Example 48. Synthesis of Compound B-1-1

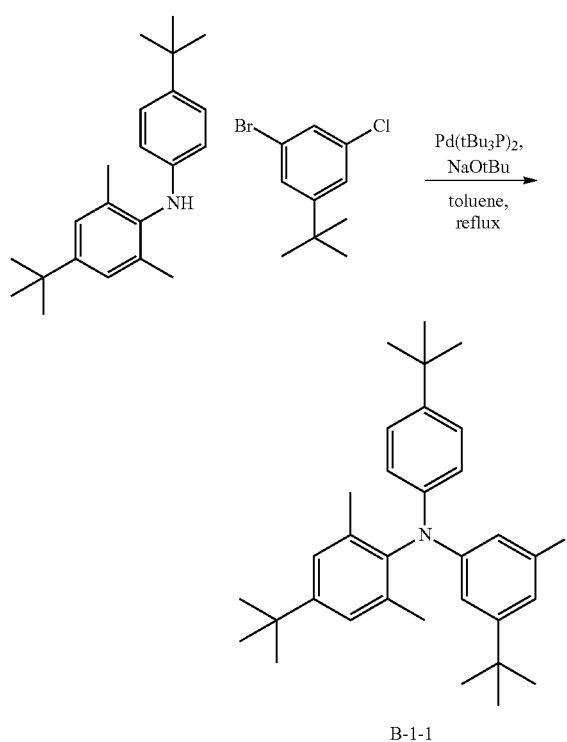

B-1-1

After dissolving 1-bromo-3-chloro-5-tert-butylbenzene (121 mmol, 30 g) and 4-tert-butyl-N-(4-tert-butylphenyl)-2,6-dimethylaniline (121 mmol, 37.5 g) in toluene (0.2 M, 605 ml) in a 3-neck flask, sodium tert-butoxide (182 mmol, 17.5 g) and bis(tri-tert-butylphosphine)palladium(0) (1.2 mmol, 0.62 g) were introduced thereto, and the result was stirred for 4 hours under reflux under the argon atmosphere. When the reaction was finished, the result was cooled to room tem-perature, then H$_2$O was introduced thereto, and the reaction solution was transferred to a separatory funnel and extracted. The extract was dried with MgSO$_4$ and concentrated, and the sample was purified using silica gel column chromatography to obtain Compound B-1-1 (51.2 g, yield 89%, MS[M+H]+=476).

Synthesis Example 49. Synthesis of Compound B-1-2

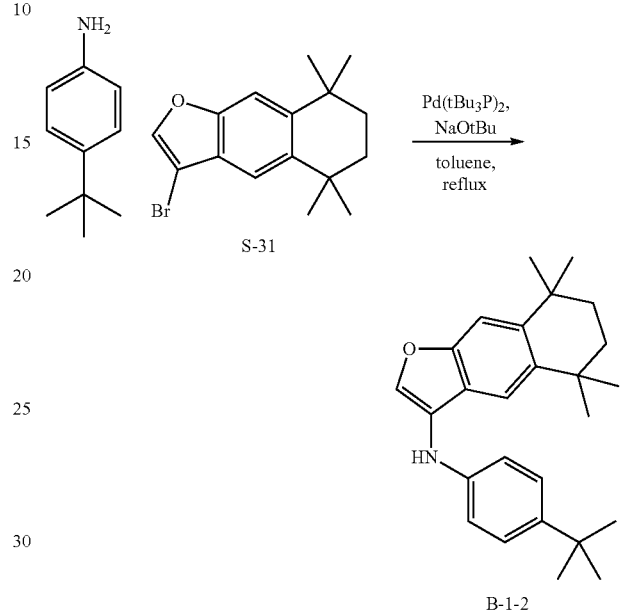

B-1-2

After dissolving Compound S-31 (97.6 mmol, 30 g) and 4-tert-butylaniline (97.6 mmol, 14.6 g) in toluene (0.2 M, 488 ml) in a 3-neck flask, sodium tert-butoxide (146.5 mmol, 14.1 g) and bis(tri-tert-butylphosphine)palladium(0) (0.98 mmol, 0.5 g) were introduced thereto, and the result was stirred for 6 hours under reflux under the argon atmosphere. When the reaction was finished, the result was cooled to room temperature, then H$_2$O was introduced thereto, and the reaction solution was transferred to a separatory funnel and extracted. The extract was dried with MgSO$_4$ and concentrated, and the sample was purified using silica gel column chromatography to obtain Compound B-1-2 (35.4 g, yield 97%, MS[M+H]+=376).

Synthesis Example 50. Synthesis of Compound B-1-3

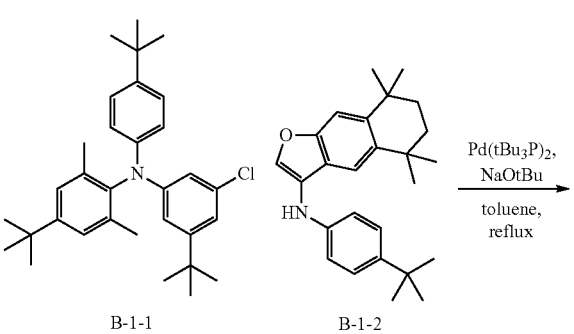

-continued

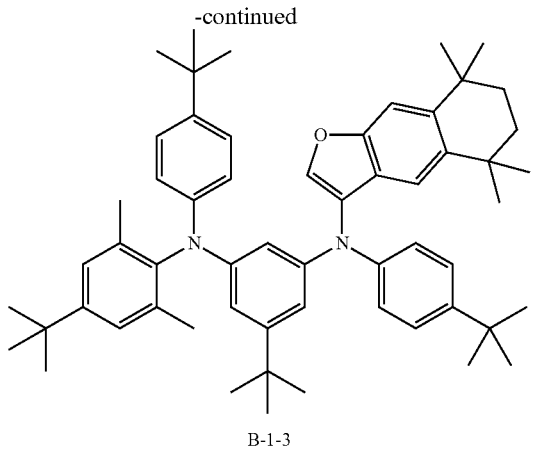

B-1-3

After dissolving Compound B-1-1 (44.1 mmol, 21 g) and Compound B-1-2 (44.1 mmol, 16.6 g) in toluene (0.2 M, 220 ml) in a 3-neck flask, sodium tert-butoxide (66.2 mmol, 6.4 g) and bis(tri-tert-butylphosphine)palladium(0) (0.44 mmol, 0.23 g) were introduced thereto, and the result was stirred for 6 hours under reflux under the argon atmosphere. When the reaction was finished, the result was cooled to room temperature, then $H_2O$ was introduced thereto, and the reaction solution was transferred to a separatory funnel and extracted. The extract was dried with $MgSO_4$ and concentrated, and the sample was purified using silica gel column chromatography to obtain Compound B-1-3 (21.8 g, yield 61%, MS[M+H]+= 815).

Synthesis Example 51. Synthesis of Compound B-1

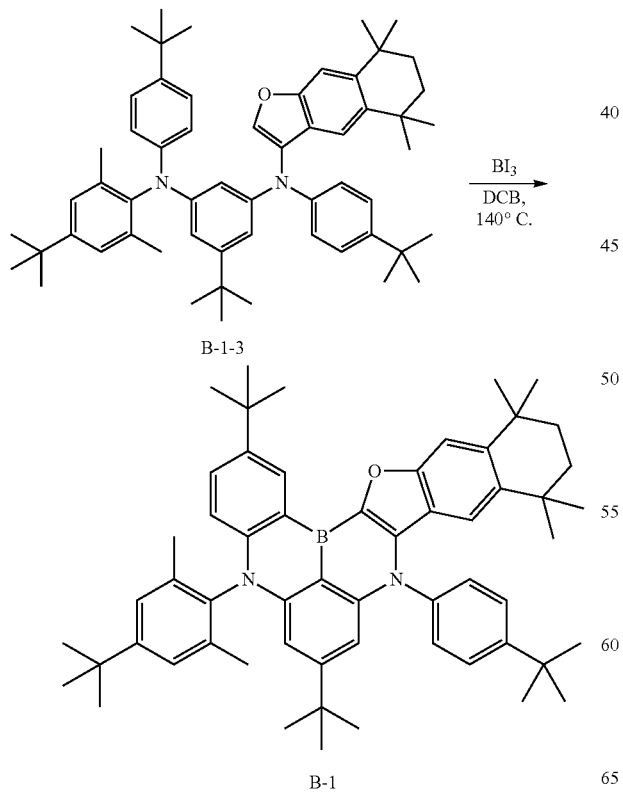

B-1

Compound B-1 (5.3 g, yield 21%, MS[M+H]+=957) was obtained in the same manner as in Synthesis Example 4 except that Compound B-1-3 (21.8 g. 1 eq.) was used instead of Compound A-2-3, and the stirring was conducted at 140° C.

Synthesis Example 52. Synthesis of Compound B-8-1

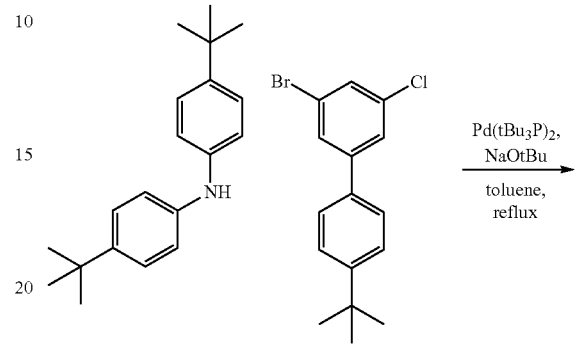

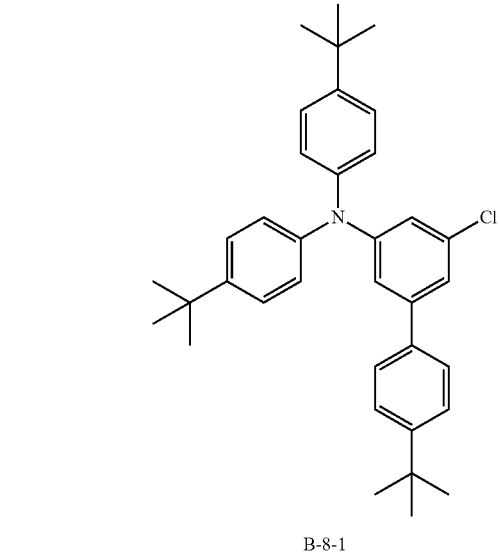

B-8-1

Compound B-8-1 (19.4 g, yield 80%, MS[M+H]+=524) was obtained in the same manner as in Synthesis Example 1 except that 3-bromo-4'-tert-butyl-5-chloro-1,1'-biphenyl was used instead of Compound S-1.

Synthesis Example 53. Synthesis of Compound B-8-2

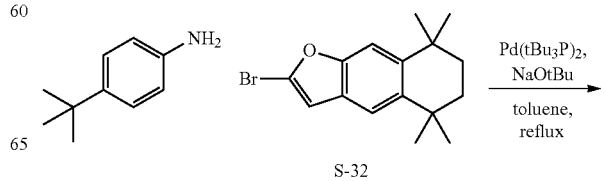

S-32

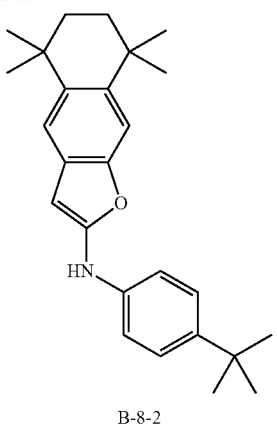

B-8-2

Compound B-8-2 (20.6 g, yield 70%, MS[M+H]+=376) was obtained in the same manner as in Synthesis Example 49 except that Compound S-32 was used instead of Compound S-31.

Synthesis Example 54. Synthesis of Compound B-8

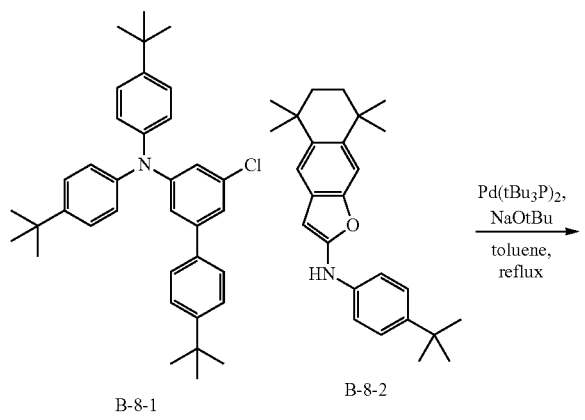

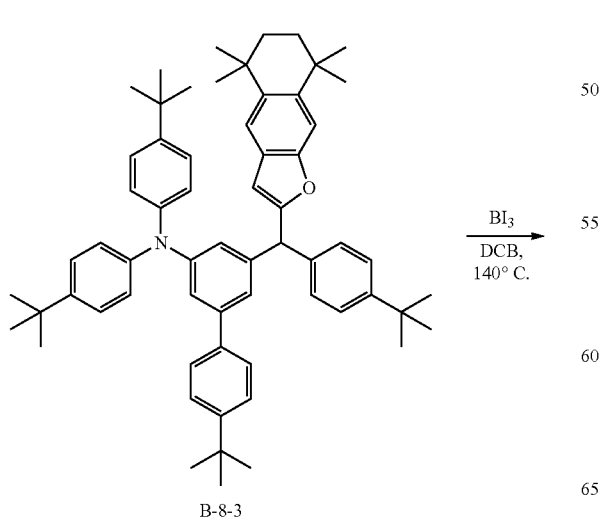

B-8-3

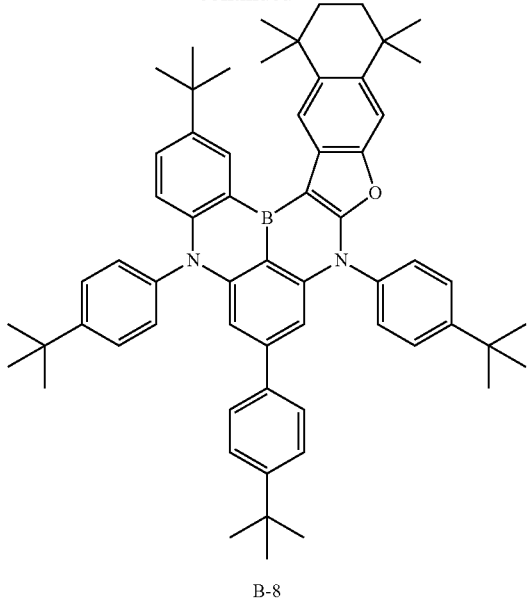

B-8

Compound B-8-3 (22 g, yield 69%, MS[M+H]+=863) was obtained in the same manner as in Synthesis Example 3 except that Compounds B-8-1 (19.4 g. 1 eq.) and B-8-2 were used instead of Compounds A-2-1 and A-2-2.

Compound B-8 (4.8 g, yield 22%, MS[M+H]+=871) was obtained in the same manner as in Synthesis Example 51 except that Compound B-8-3 (11 g. 1 eq.) was used instead of Compound B-1-3.

Synthesis Example 55. Synthesis of Compound B-9-1

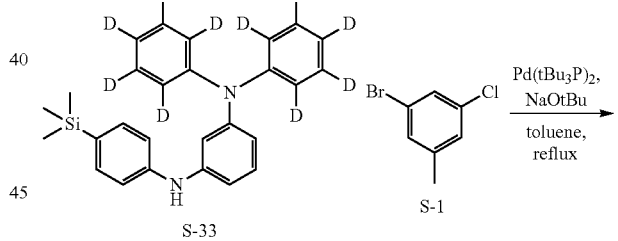

B-9-1

Compound B-9-1 (24.5 g, yield 94%, MS[M+H]+=543) was obtained in the same manner as in Synthesis Example 1 except that Compound S-33 was used instead of Compound S-2.
Synthesis Example 56. Synthesis of Compound B-9-2
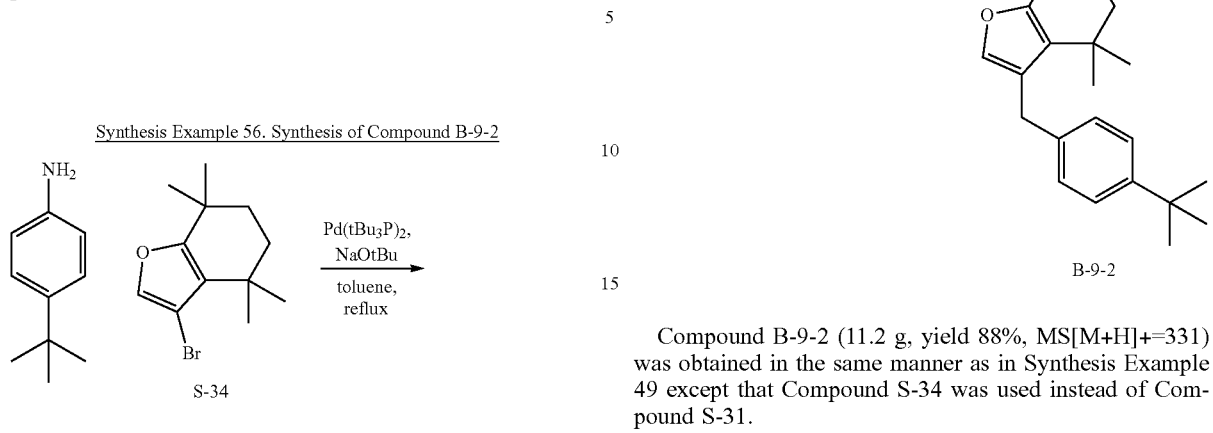
Compound B-9-2 (11.2 g, yield 88%, MS[M+H]+=331) was obtained in the same manner as in Synthesis Example 49 except that Compound S-34 was used instead of Compound S-31.
Synthesis Example 57. Synthesis of Compound B-9-3
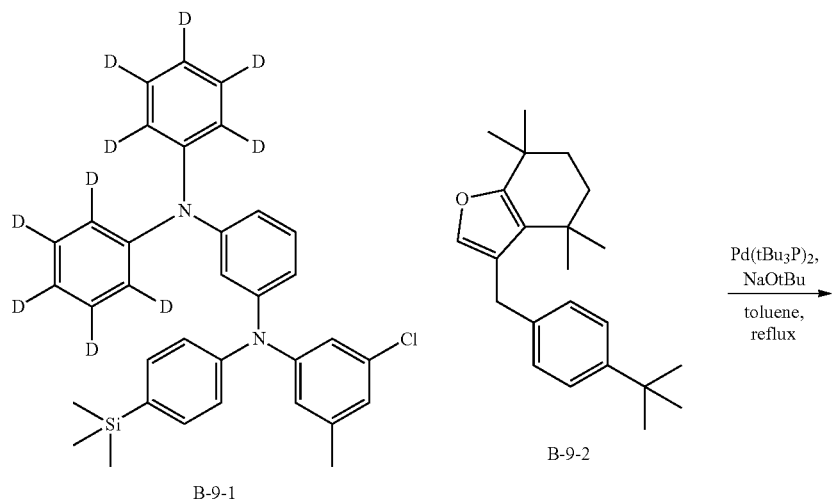
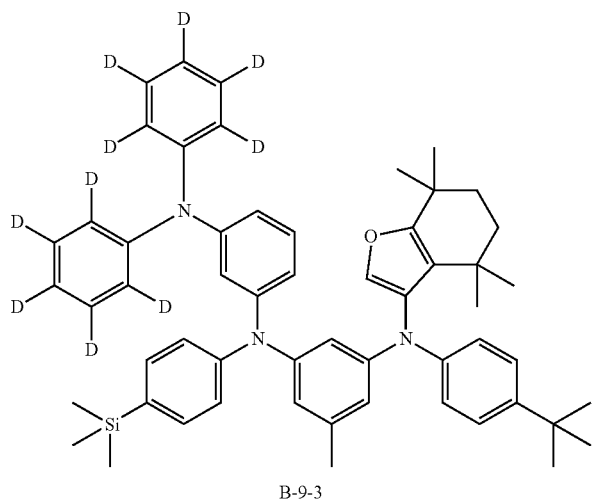

Compound B-9-3 (21.2 g, yield 77%, MS[M+H]+=832) was obtained in the same manner as in Synthesis Example 3 except that Compounds B-9-1 (18 g. 1 eq.) and B-8-2 were used instead of Compounds A-2-1 and A-2-2.

Compound B-9 (3.8 g, yield 19%, MS[M+H]+=859) was obtained in the same manner as in Synthesis Example 51 except that Compound B-9-3 (11 g. 1 eq.) was used instead of Compound B-1-3.

Synthesis Example 58. Synthesis of Compound B-9

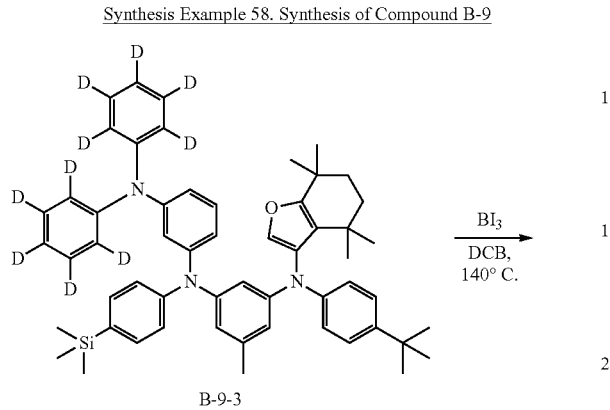

Synthesis Example 59. Synthesis of Compound B-2-1

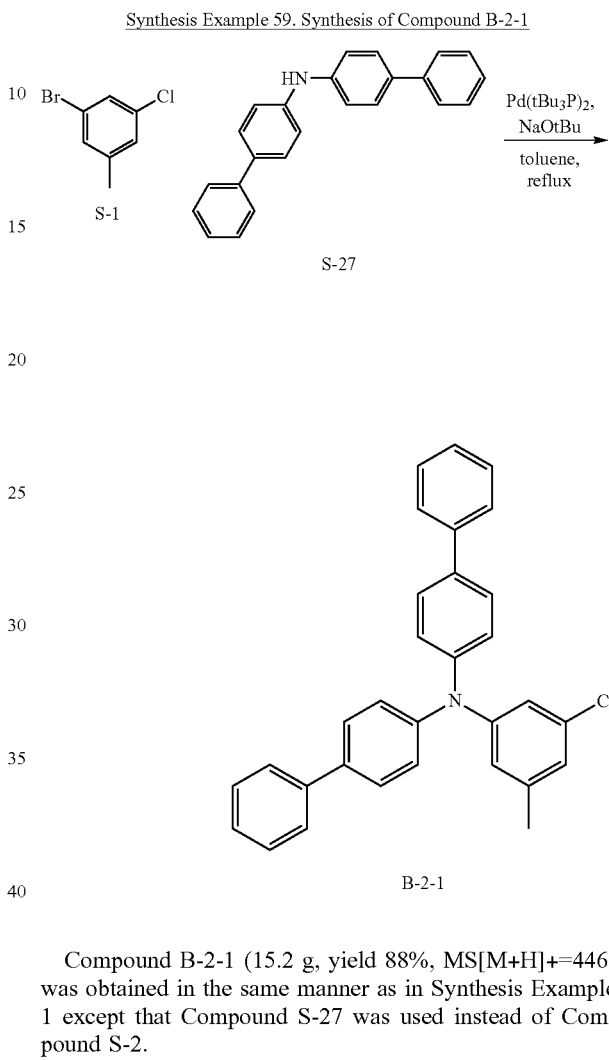

Compound B-2-1 (15.2 g, yield 88%, MS[M+H]+=446) was obtained in the same manner as in Synthesis Example 1 except that Compound S-27 was used instead of Compound S-2.

Synthesis Example 60. Synthesis of Compound B-2

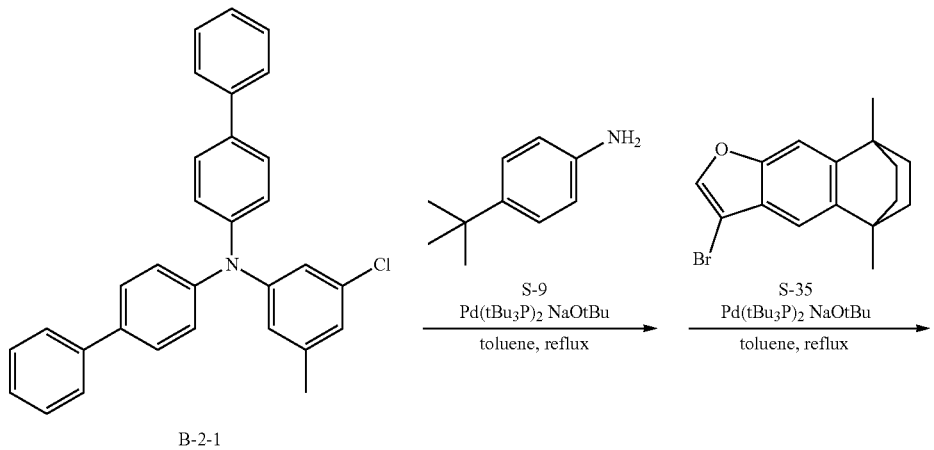

-continued

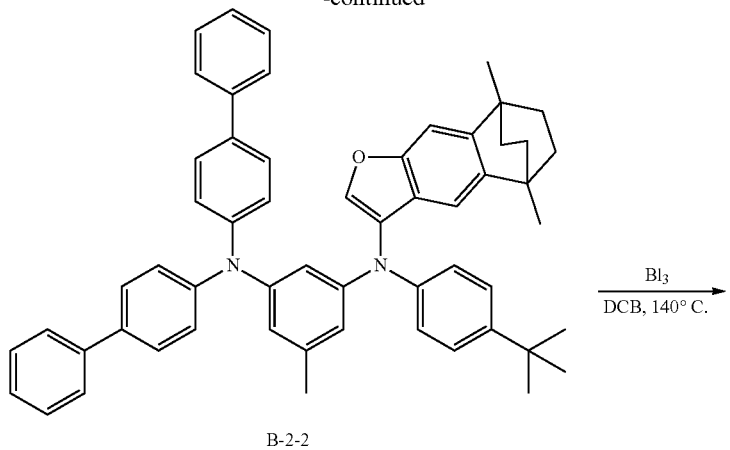

B-2-2

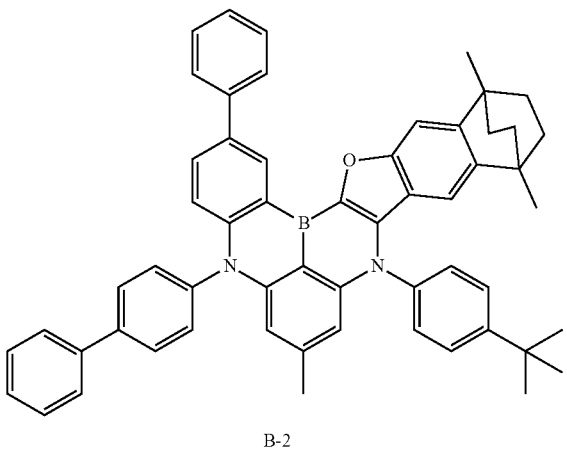

B-2

Compound B-2-2 (12.2 g, yield 47%, MS[M+H]+=783) was obtained in the same manner as in Synthesis Example 12 except that Compounds B-2-1 (15 g, 1 eq.) and S-35 were used instead of Compounds A-1-1 and S-10.

Compound B-2 (3.5 g, yield 38%, MS[M+H]+=791) was obtained in the same manner as in Synthesis Example 51 except that Compound B-2-2 (9 g. 1 eq.) was used instead of Compound B-1-3.

Synthesis Example 61. Synthesis of Compound B-3-1

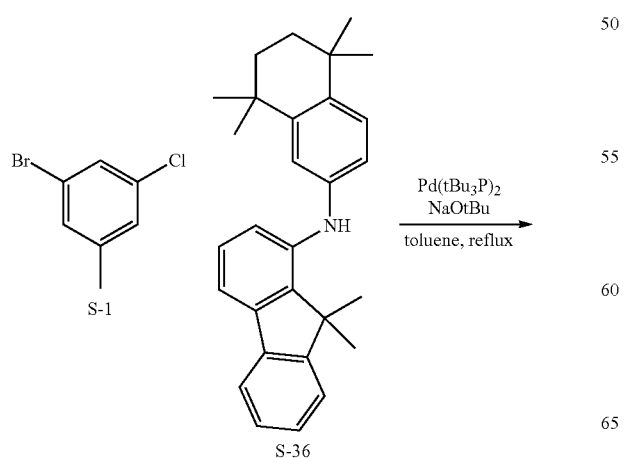

-continued

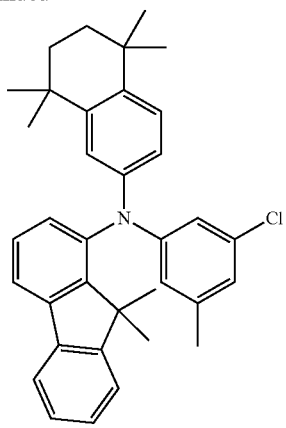

B-3-1

Compound B-3-1 (11.1 g, yield 78%, MS[M+H]+=520) was obtained in the same manner as in Synthesis Example 1 except that Compound S-36 was used instead of Compound S-2.

Synthesis Example 62. Synthesis of Compound B-3
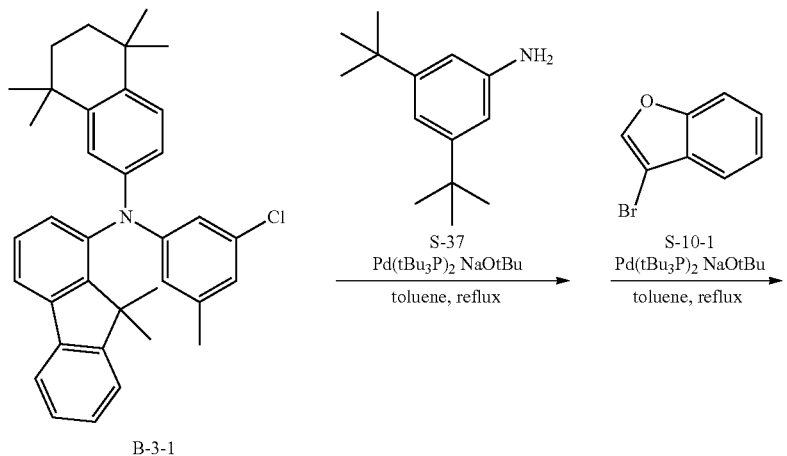
B-3-1
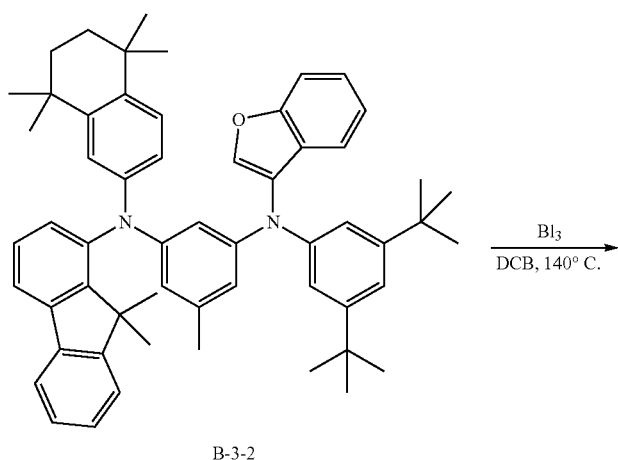
B-3-2
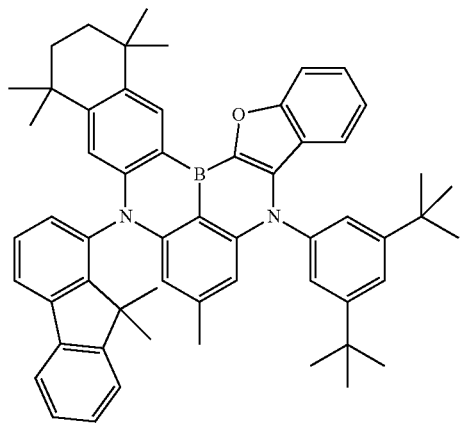
B-3
Compound B-3-2 (8.7 g, yield 56%, MS[M+H]+=806) was obtained in the same manner as in Synthesis Example 12 except, that Compounds B-3-1 (10 g, 1 eq.), S-37 and S-10-1 were used instead of Compounds A-1-1, S-9 and S-10.
Compound 2-3 (2.3 g, yield 26%, MS[M+H]+=813) was obtained in the same manner as in Synthesis Example 51 except that Compound B-3-2 (8.7 g. 1 eq.) was used instead of Compound B-1-3.

Synthesis Example 63. Synthesis of Compound B-4-1
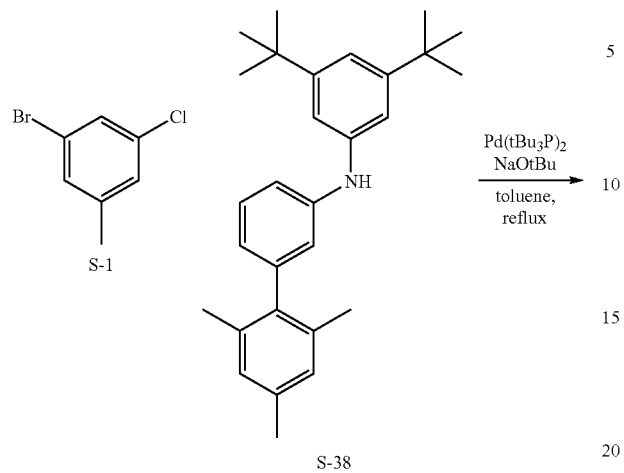
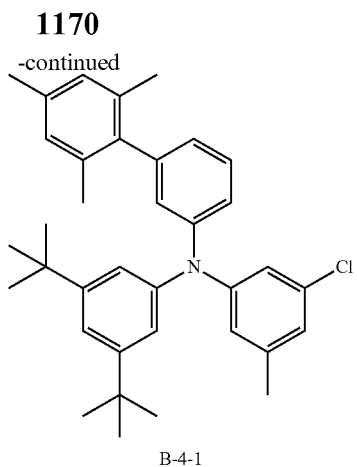
Compound B-4-1 (16.3 g, yield 73%, MS[M+H]+=524) was obtained in the same manner as in Synthesis Example 1 except that Compound S-38 was used instead of Compound S-2.
Synthesis Example 64. Synthesis of Compound B-4
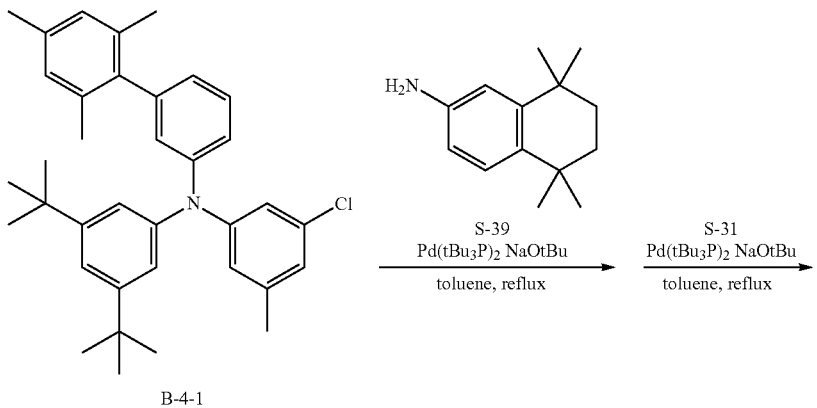
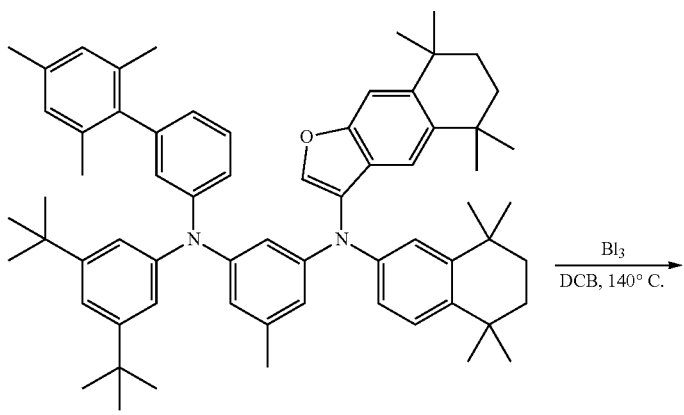

-continued

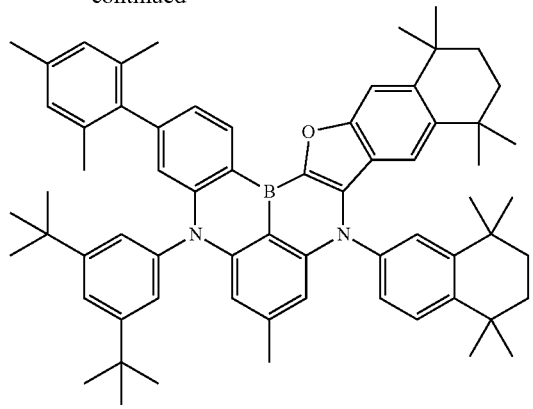

B-4

Compound B-4-2 (12.8 g, yield 52%, MS[M+H]+=918) was obtained in the same manner as in Synthesis Example 12 except that Confounds B-4-1 (14 g, 1 eq.), S-39 and S-31 were used instead of Compounds A-1-1, S-9 and S-10.

Compound B-4 (2.8 g, yield 25%, MS[M+H]+=926) was obtained in the same manner as in Synthesis Example 51 except that Compound B-4-2 (11 g. 1 eq.) was used instead of Compound B-1-3.

Synthesis Example 65. Synthesis of Compound B-5-1

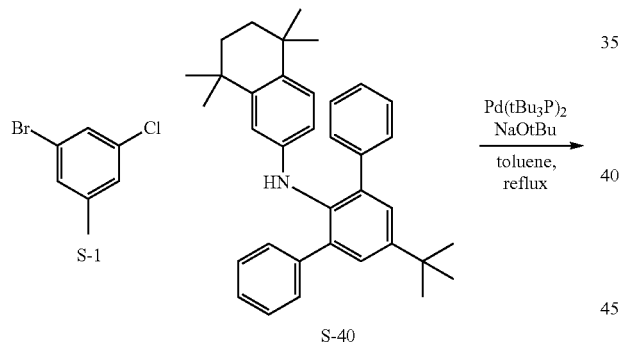

S-1    S-40

$\xrightarrow{\text{Pd(tBu}_3\text{P)}_2 \text{ NaOtBu}}_{\text{toluene, reflux}}$ -continued

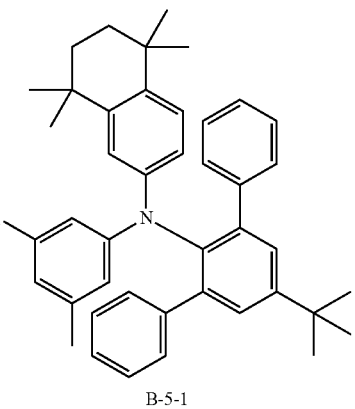

B-5-1

Compound B-5-1 (17.8 g, yield 65%, MS[M+H]+=612) was obtained in the same manner as in Synthesis Example 1 except that Compound S-40 was used instead of Compound S-2.

Synthesis Example 66. Synthesis of Compound B-5

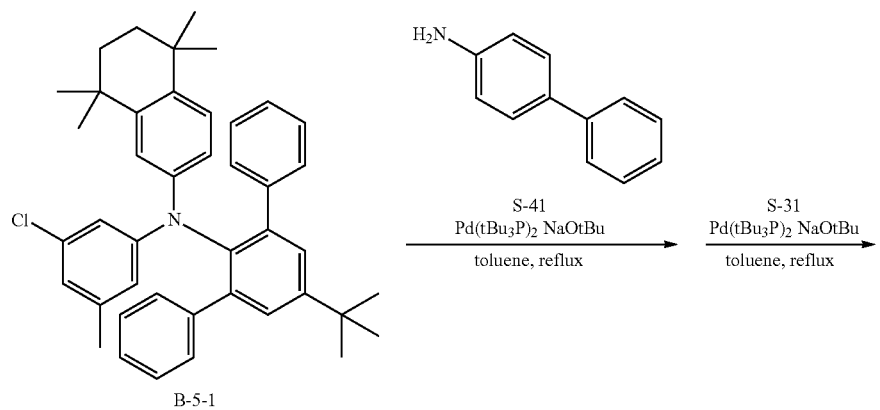

B-5-1    S-41    S-31

$\xrightarrow{\text{Pd(tBu}_3\text{P)}_2 \text{ NaOtBu}}_{\text{toluene, reflux}}$ $\xrightarrow{\text{Pd(tBu}_3\text{P)}_2 \text{ NaOtBu}}_{\text{toluene, reflux}}$ -continued

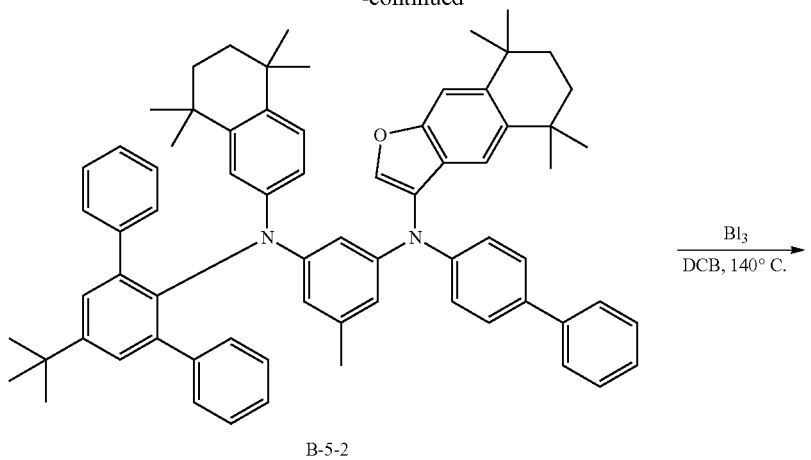

B-5-2

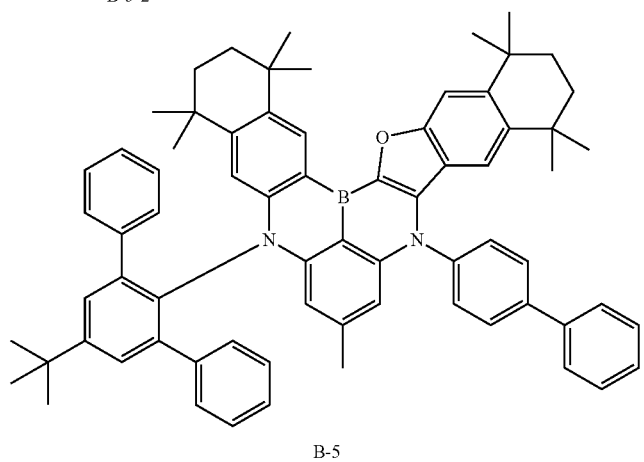

B-5

Compound B-5-2 (12.7 g, yield 47%, MS[M+H]+=972) was obtained in the same manner as in Synthesis Example 12 except that Compounds B-5-1 (17 g, 1 eq.), S-41 and S-31 were used instead of Compounds A-1-1, S-9 and S-10.

Compound B-5 (2.2 g, yield 19%, MS[M+H]+=980) was obtained in the same manner as in Synthesis Example 51 except that Compound B-5-2 (11.7 g. 1 eq.) was used instead of Compound B-1-3.

Synthesis Example 67. Synthesis of Compound B-6-1

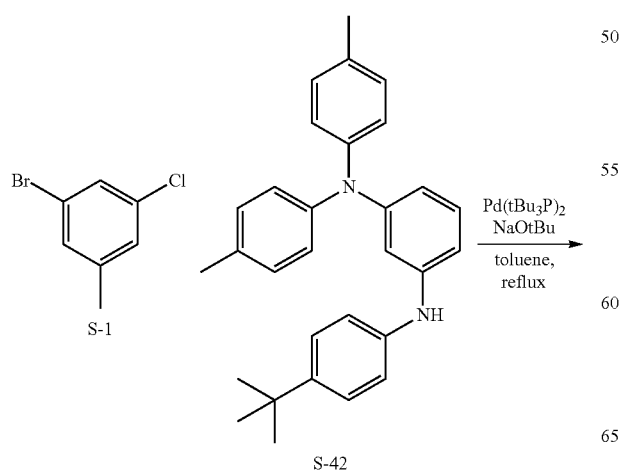

-continued

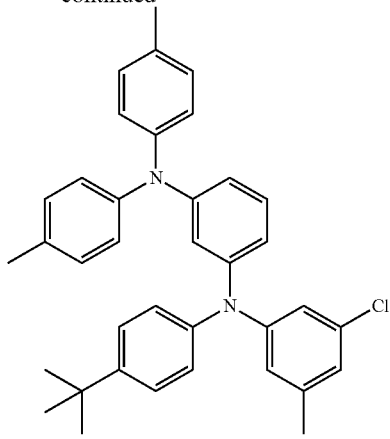

B-6-1

Compound B-6-1 (13.2 g, yield 82%, MS[M+H]+=545) was obtained in the same manner as in Synthesis Example 1 except that Compound S-42 was used instead of Compound S-2.

Synthesis Example 68. Synthesis of Compound B-6
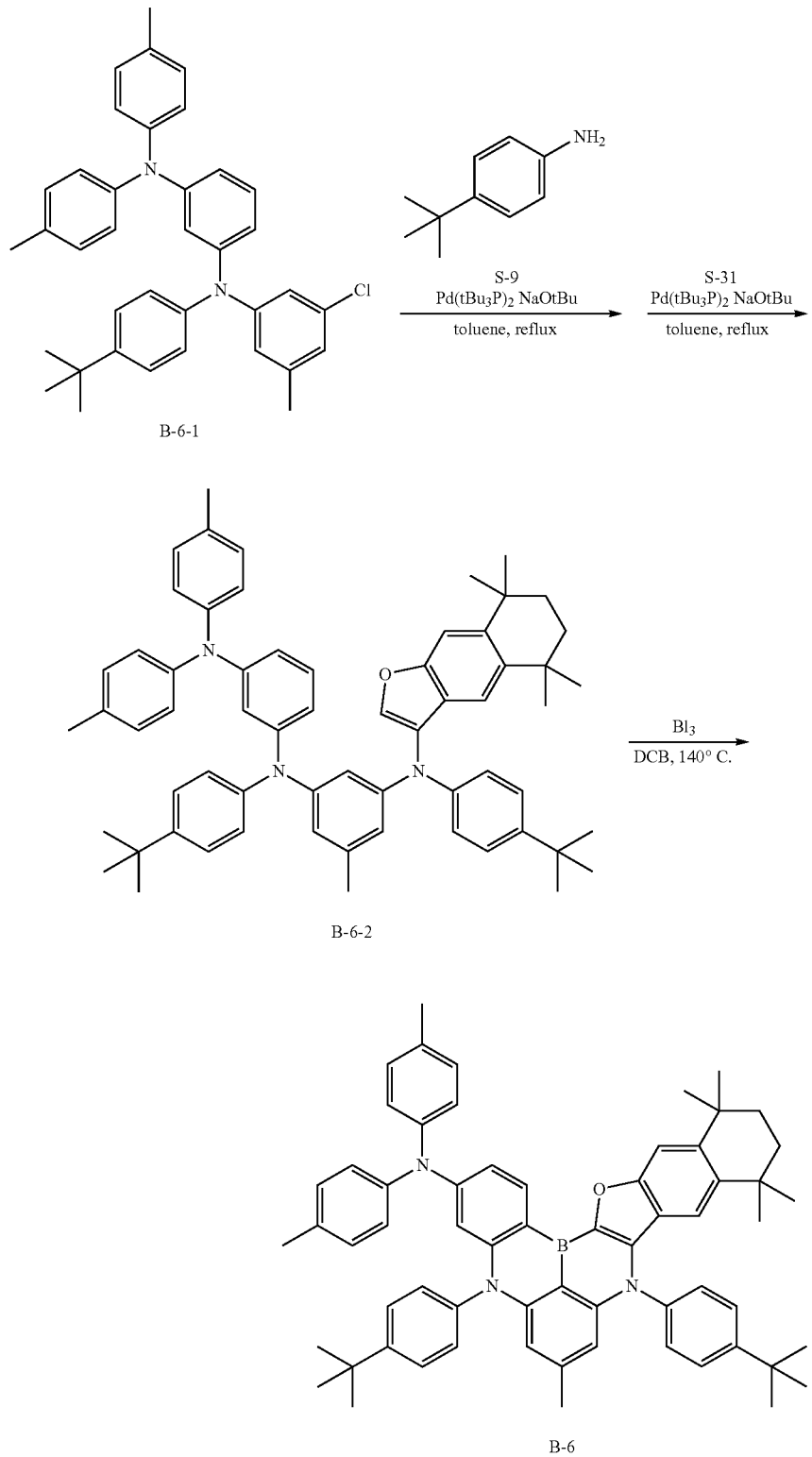
Compound B-6-2 (11.8 g, yield 61%, MS[M+H]+=885) was obtained in the same manner as in Synthesis Example 12 except that Compounds B-6-1 (12 g, 1 eq.) and S-31 were used instead of Compounds A-1-1 and S-10.
Compound B-6 (2.7 g, yield 24%, MS[M+H]+=893) was obtained in the same manner as in Synthesis Example 51 except that Compound B-6-2 (11.7 g. 1 eq.) was used instead of Compound B-1-3.

Synthesis Example 69. Synthesis of Compound B-7-1
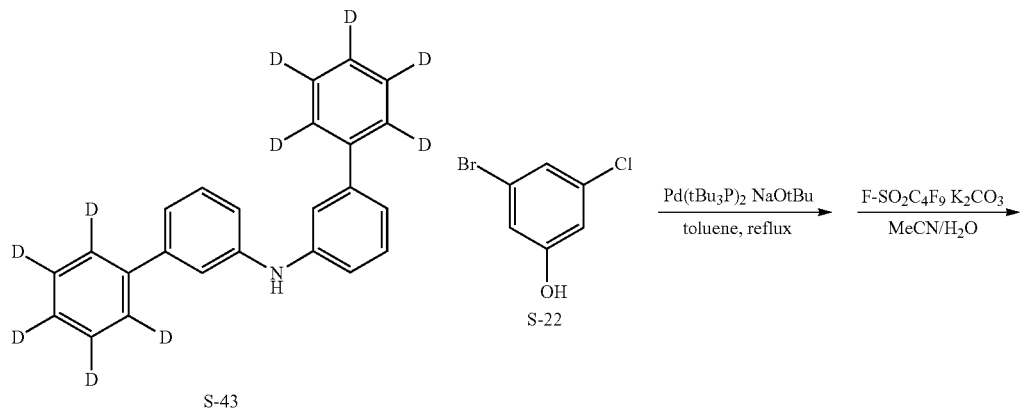
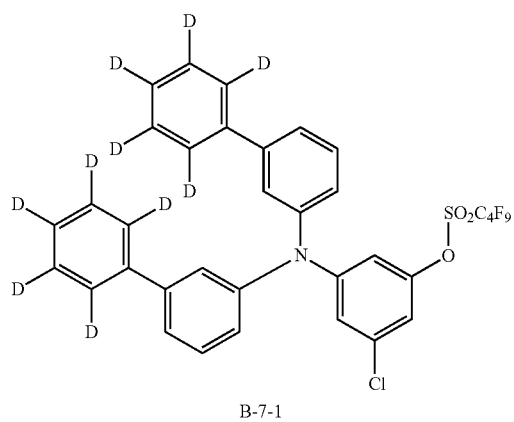
Compound B-7-3 (19.1 g, yield 79%) was obtained in the same manner as in Synthesis Example 32 except that Compound S-43 was used instead of Compound S-2.
Synthesis Example 70. Synthesis of Compound B-7-2
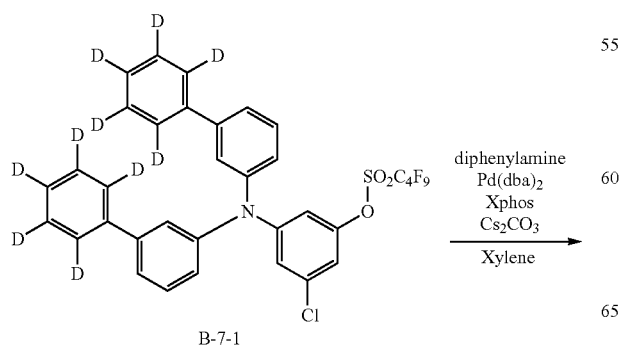
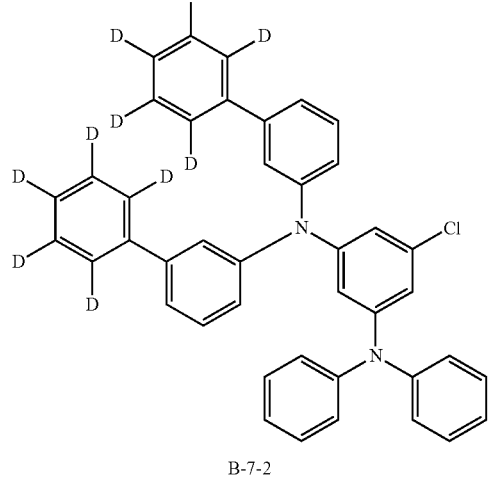
Compound B-7-2 (10.7 g, yield 72%, MS[M+H]+=609) was obtained in the same manner as in Synthesis Example 33 except that Compound B-7-1 (13 g, 1 eq.) was used instead of Compound A-8-1.

Synthesis Example 71. Synthesis of Compound B-7
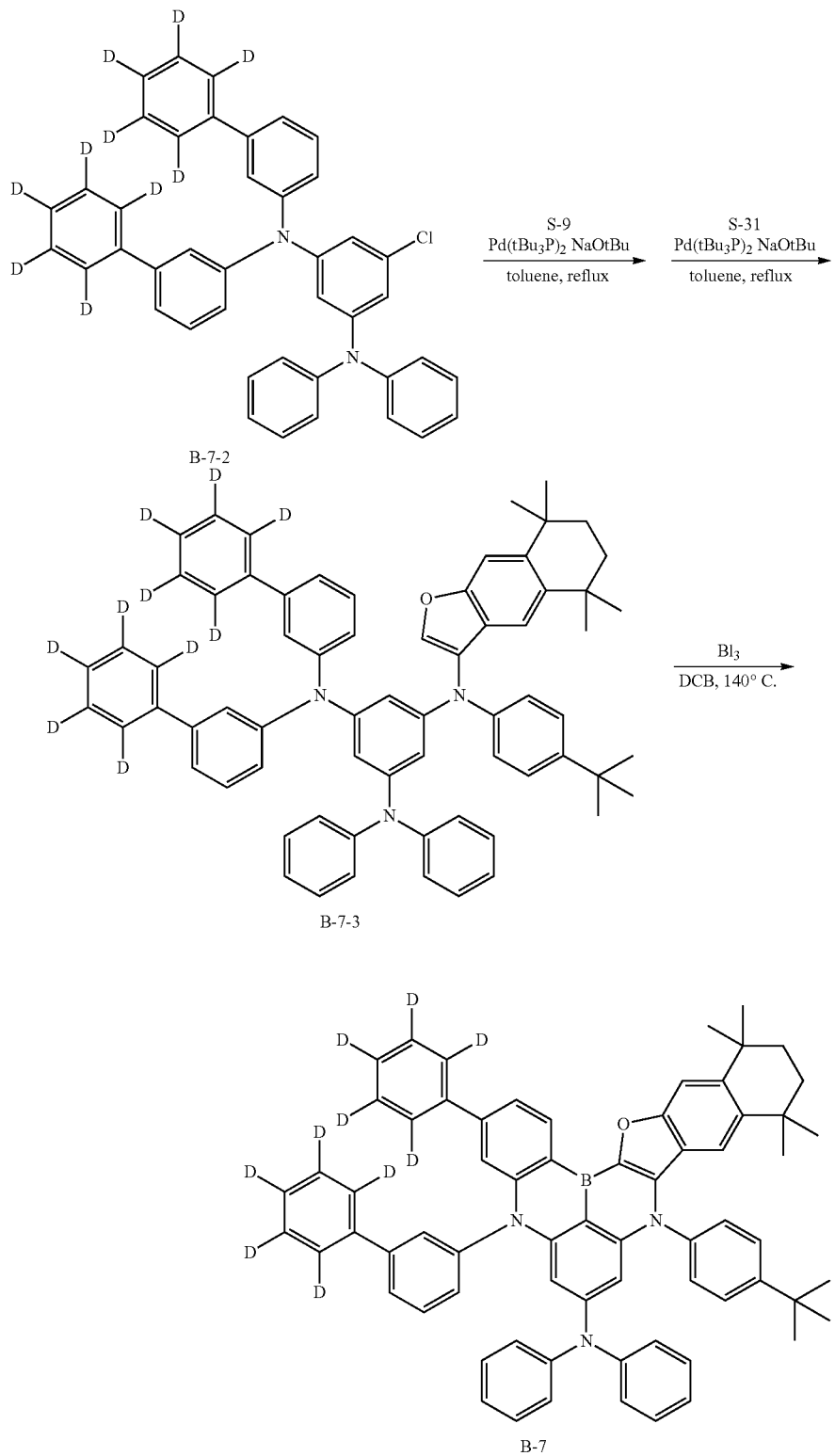
Compound B-7-3 (7.8 g, yield 47%, MS[M+H]+=949) was obtained in the same manner as in Synthesis Example 12 except that Compounds B-7-2 (10.7 g, 1 eq.) and S-31 were used instead of Compounds A-1-1 and S-10.
Compound B-7 (1.7 g, yield 21%, MS[M+H]+=957) was obtained in the same manner as in Synthesis Example 51 except that Compound B-7-3 (7.8 g. 1 eq.) was used instead of Compound B-1-3.

Synthesis Example 72. Synthesis of Compound A-17

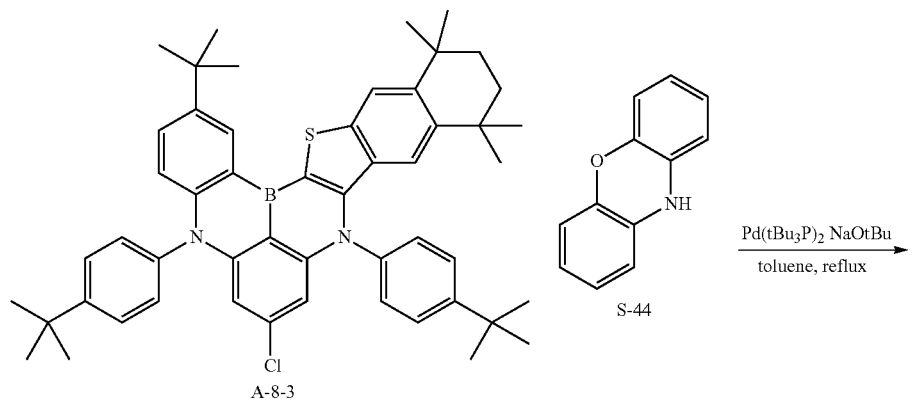

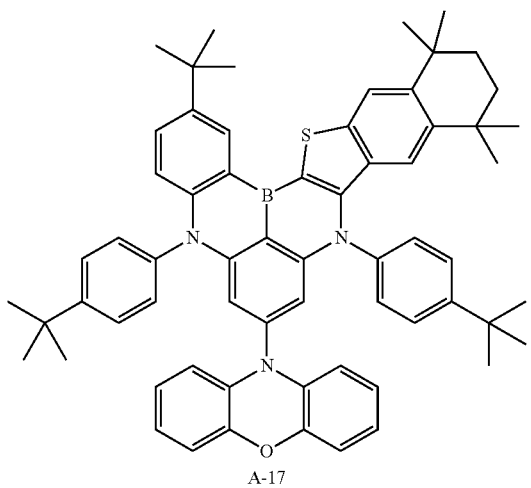

Compound A-17 (1.9 g, yield 78%, MS[M+H]+=937) was obtained in the same manner as in Synthesis Example 3 except that Compounds A-8-3 (2 g. 1 eq.) and S-44 (0.6 g, 1.2 eq.) were used instead of Compounds A-2-1 and A-2-2.

Synthesis Example 73. Synthesis of Compound A-18-1

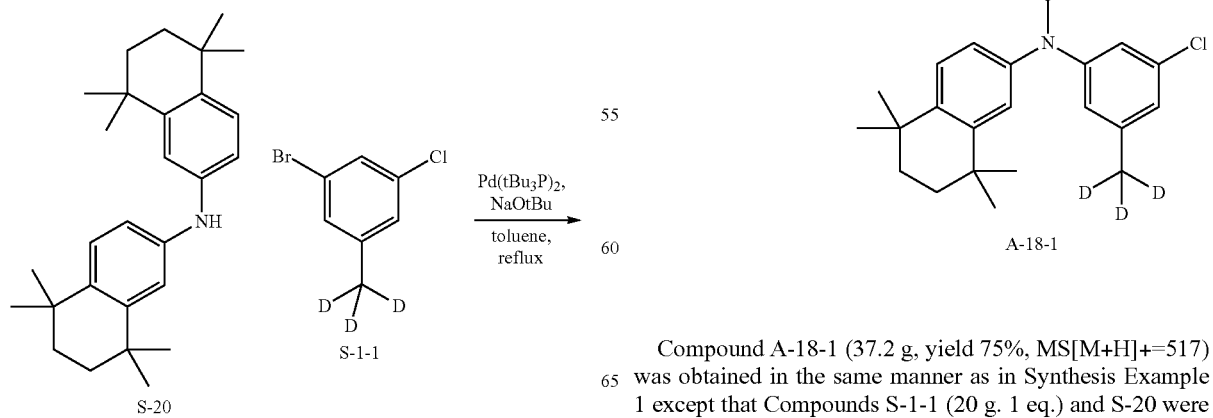

Compound A-18-1 (37.2 g, yield 75%, MS[M+H]+=517) was obtained in the same manner as in Synthesis Example 1 except that Compounds S-1-1 (20 g. 1 eq.) and S-20 were used instead of Compounds S-1 and S-2.

Synthesis Example 74. Synthesis of Compound A-18
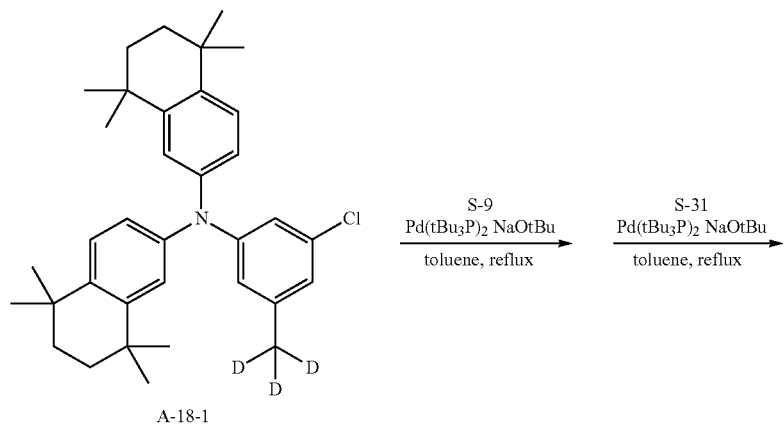
A-18-1
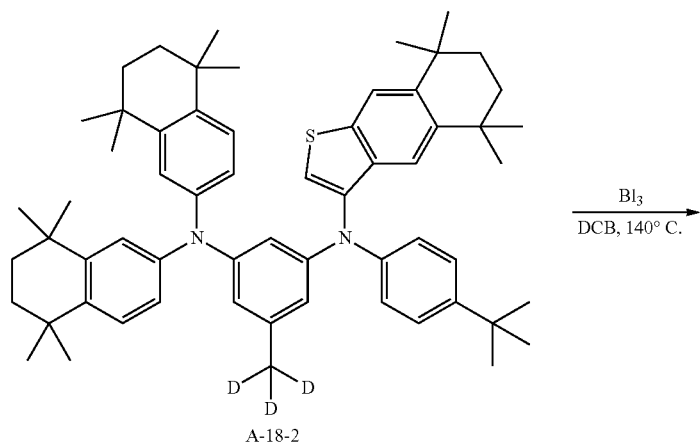
A-18-2
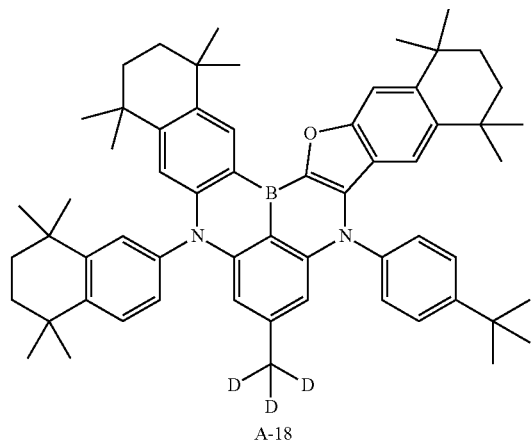
A-18
Compound A-18-2 (9.7 g, yield 58%, MS[M+H]+=873) was obtained in the same manner as in Synthesis Example 12 except that Compounds A-18-1 (g, 1 eq.) and S-4 were used instead of Compounds A-1-1 and S-10.
Compound A-18 (2.2 g, yield 33%, MS[M+H]+=881) was obtained in the same manner as in Synthesis Example 51 except that Compound A-18-2 (6.5 g. 1 eq.) was used instead of Compound B-1-3.

Synthesis Example 75. Synthesis of Compound A-19-1

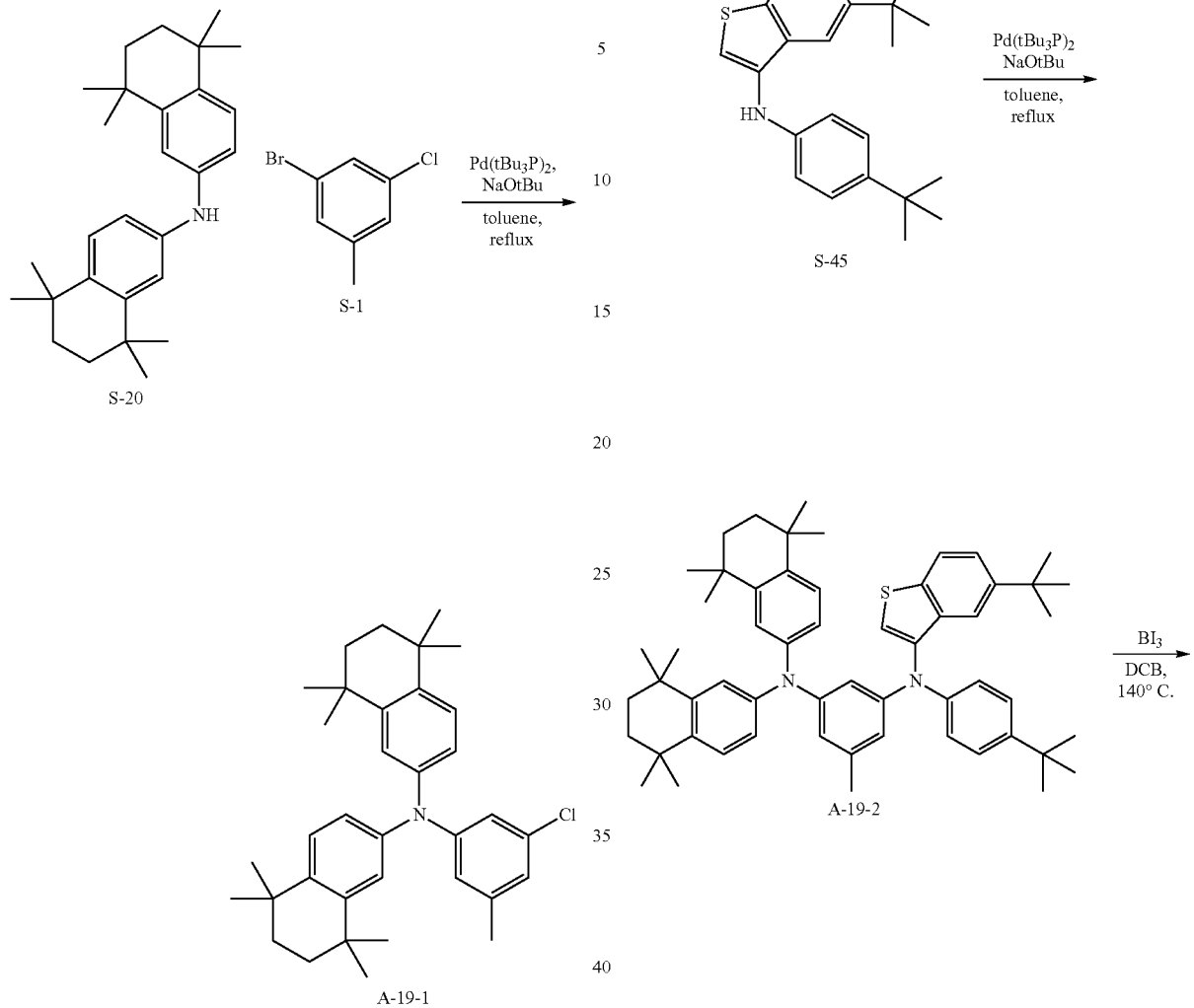

Compound A-19-1 (20.5 g, yield 82%, MS[M+H]+=514) was obtained in the same manner as in Synthesis Example 1 except that Compound S-20 (19 g) was used instead of Compound S-2.

Synthesis Example 76. Synthesis of Compound A-19

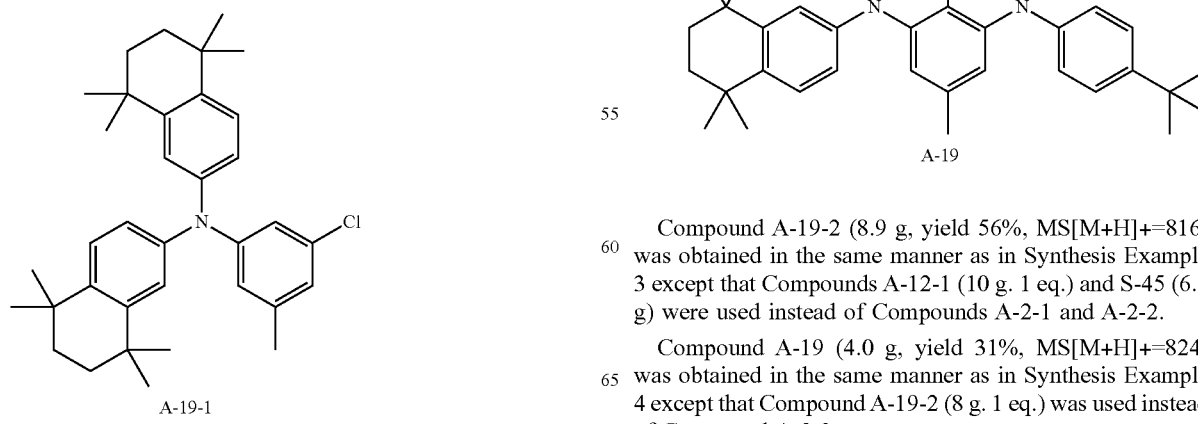

Compound A-19-2 (8.9 g, yield 56%, MS[M+H]+=816) was obtained in the same manner as in Synthesis Example 3 except that Compounds A-12-1 (10 g. 1 eq.) and S-45 (6.6 g) were used instead of Compounds A-2-1 and A-2-2.

Compound A-19 (4.0 g, yield 31%, MS[M+H]+=824) was obtained in the same manner as in Synthesis Example 4 except that Compound A-19-2 (8 g. 1 eq.) was used instead of Compound A-2-3.

Synthesis Example 77. Synthesis of Compound A-20-1

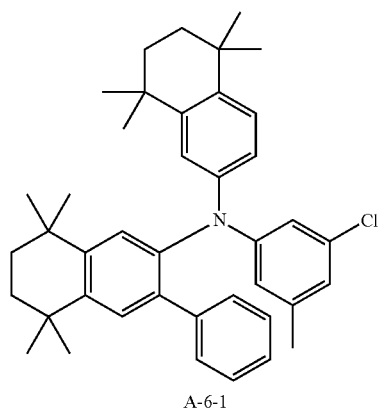

A-6-1

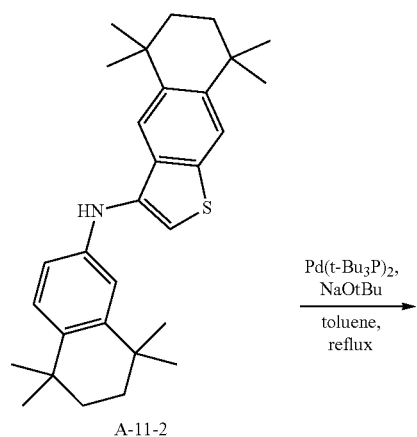

A-11-2

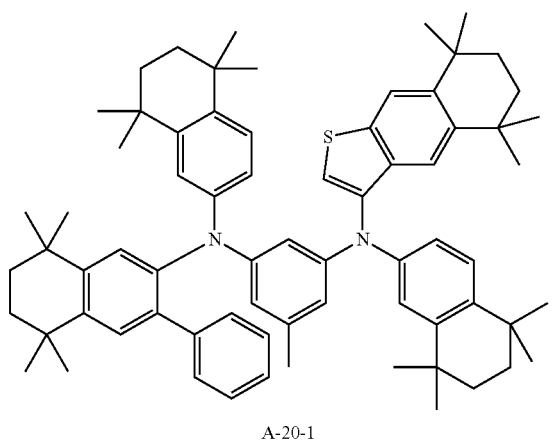

A-20-1

Compound A-20-1 (8 g, yield 59%, MS[M+H]+=1000) was obtained in the same manner as in Synthesis Example 3 except that Compounds A-6-1 (8 g. 1 eq.) and A-11-2 (6 g) were used instead of Compounds A-2-1 and A-2-2.

Synthesis Example 78. Synthesis of Compound A-20

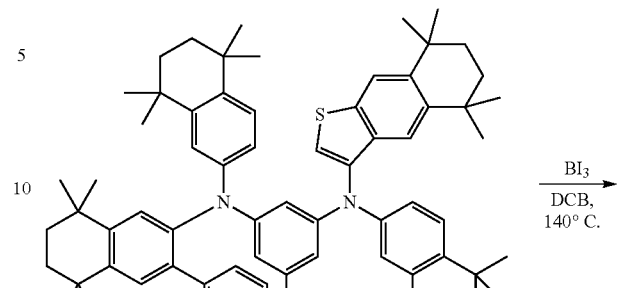

A-20-1

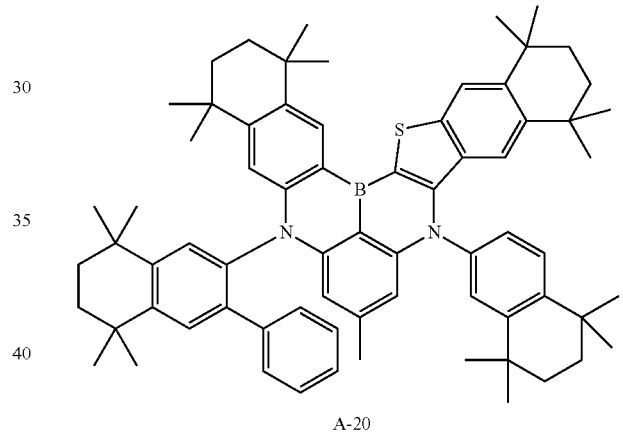

A-20

Compound A-20 (2.7 g, yield 35, MS[M+H]+=1008) was obtained in the same manner as in Synthesis Example 4 except that Compound A-20-1 (8 g. 1 eq.) was used instead of Compound A-2-3.

Synthesis Example 79. Synthesis of Compound A-21-1

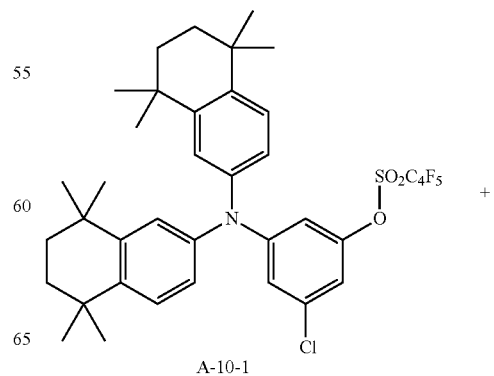

A-10-1

-continued

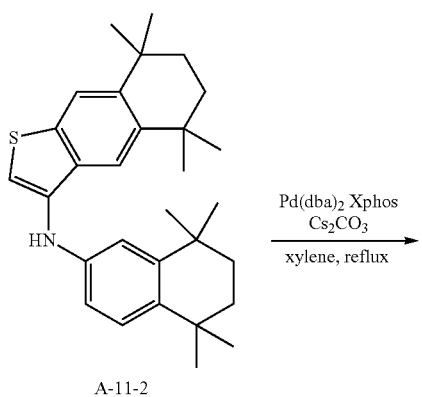

A-11-2

Compound A-21-1 (7.1 g, yield 71%, MS[M+H]+944) was obtained in the same manner as in Synthesis Example 33 except that Compound A-10-1 (8.5 g, 1 eq.) was used instead of Compound A-8-1, and Compound A-11-2 was used instead of Compound A-4-2.

Synthesis Example 80. Synthesis of Compound A-21-2

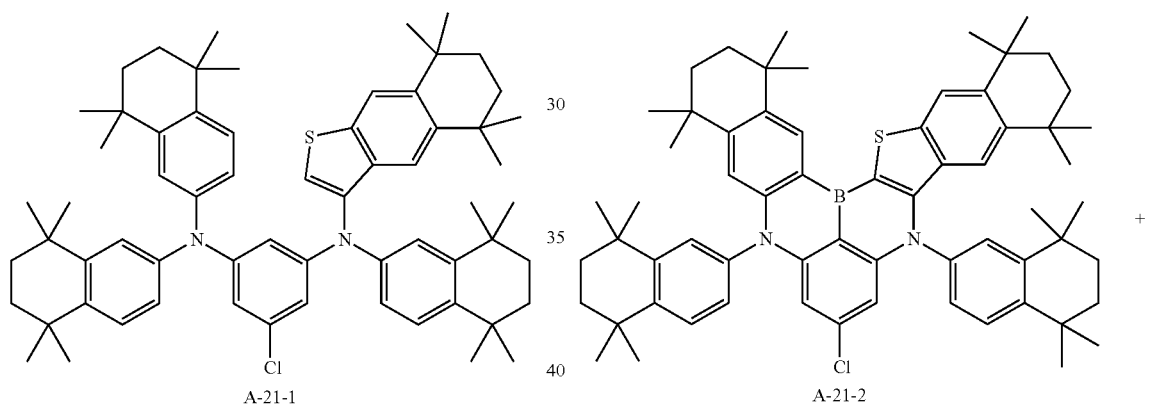

A-21-1

-continued

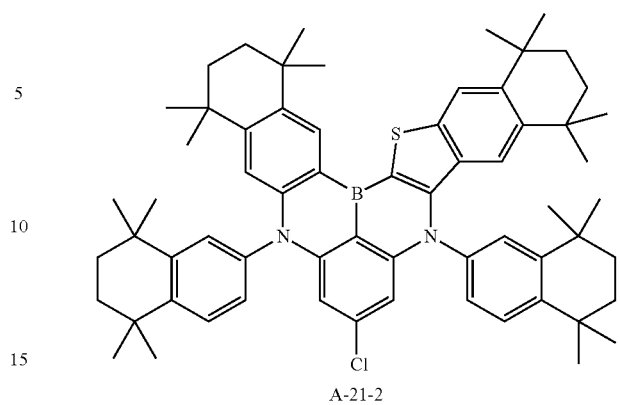

A-21-2

Compound A-21-2 (2.9 g, yield 45%, MS[M+H]+=952) was obtained in the same manner as in Synthesis Example 4 except that Compound A-21-1 (6.5 g. 1 eq.) was used instead of Compound A-2-3.

Synthesis Example 81. Synthesis of Compound A-21

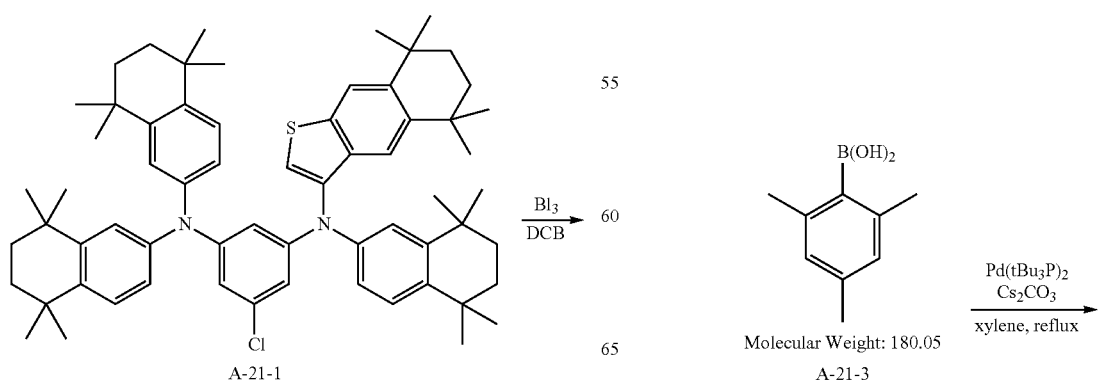

A-21-2

Molecular Weight: 180.05
A-21-3

1191
-continued

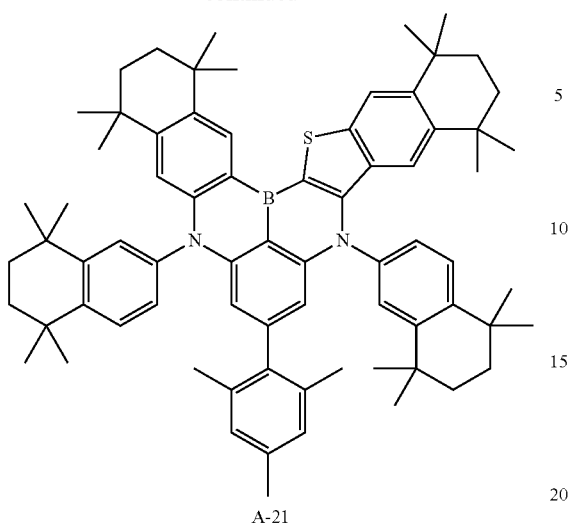

A-21

After introducing Intermediate A-21-2 (2.9 g, 1 eq.), Intermediate A-21-3 (0.82 g, 1.5 eq.), $Cs_2CO_3$ (2.9 g, 3 eq.) and bis(tri-tert-butylphosphine)palladium(0) (0.03 g, 0.02 eq.) to toluene (30 ml) under the nitrogen atmosphere, the result was stirred under reflux for 4 hours. After the reaction was finished, the result was extracted, and recrystallized to obtain Compound A-21 (1.9 g, yield 62%, MS[M+H]+= 1036).

Synthesis Example 82. Synthesis of Compound A-22-1

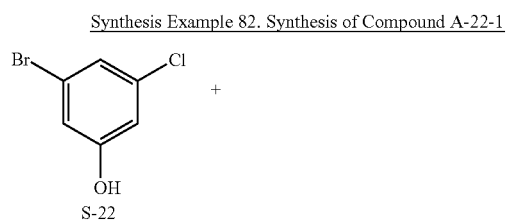

S-22

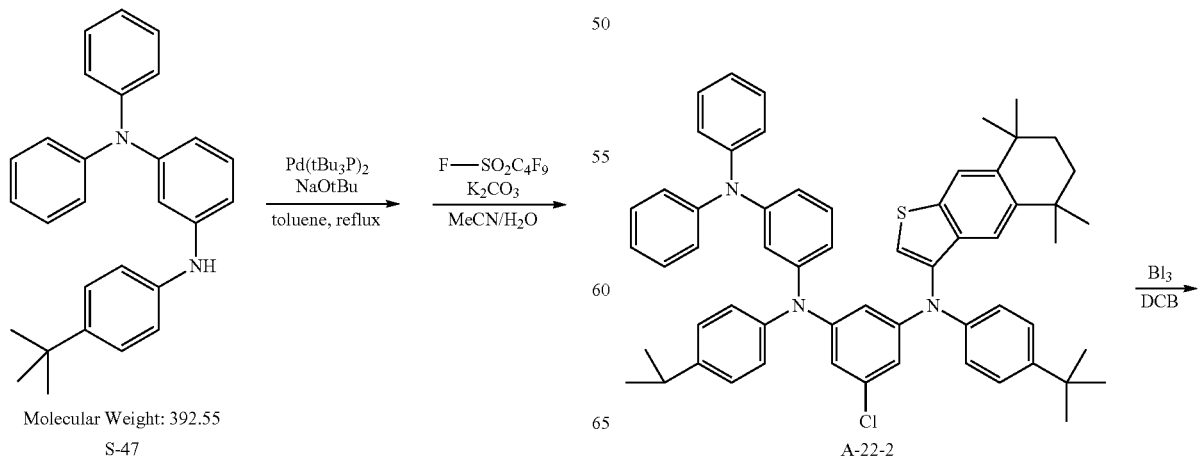

S-47
Molecular Weight: 392.55

1192
-continued

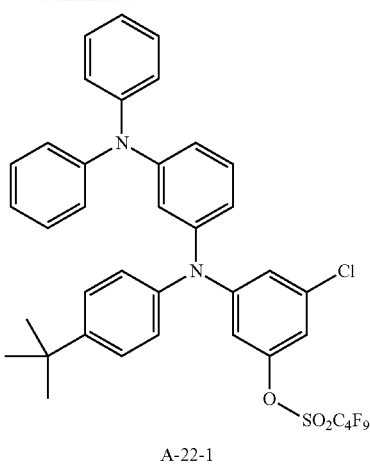

A-22-1

Compound A-22-1 (22.8 g, yield 59%) was obtained in the same manner as in Synthesis Example 32 except that Compound S-47 (18.9 g) was used instead of Compound S-2.

Synthesis Example 83. Synthesis of Compound A-22-3

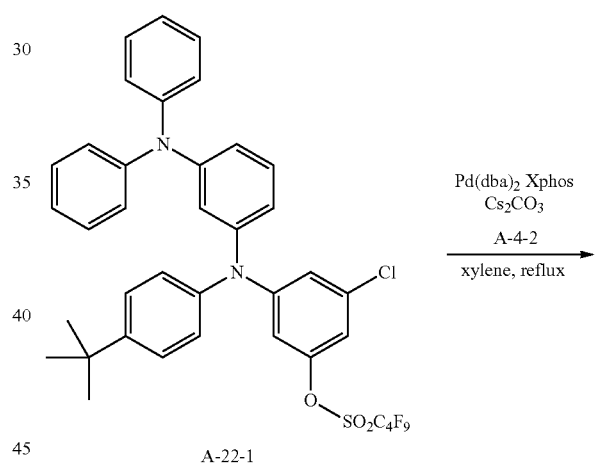

A-22-1

A-22-2

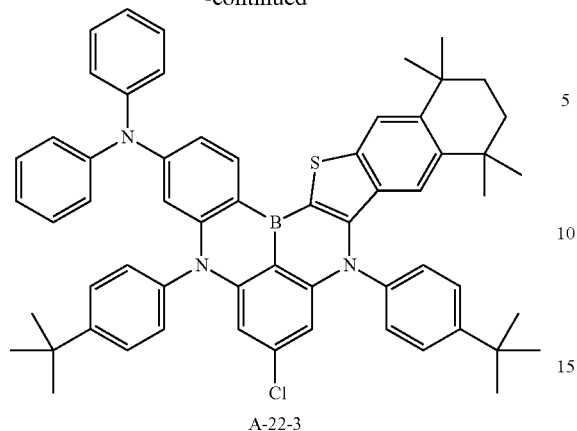
A-22-3
Compound A-22-2 (10.2 g, yield 61%, MS[M+H]+=892) was obtained in the same manner as in Synthesis Example 33 except that Compound A-22-1 (15 g, 1 eq.) was used instead of Compound A-8-1.
Compound A-22-3 (4.5 g, yield 50%, MS[M+H]+=900) was obtained in the same manner, as in Synthesis Example 4 except that Compound A-22-2 (9 g. 1 eq.) was used instead of Compound A-2-3.
Synthesis Example 84. Synthesis of Compound A-22
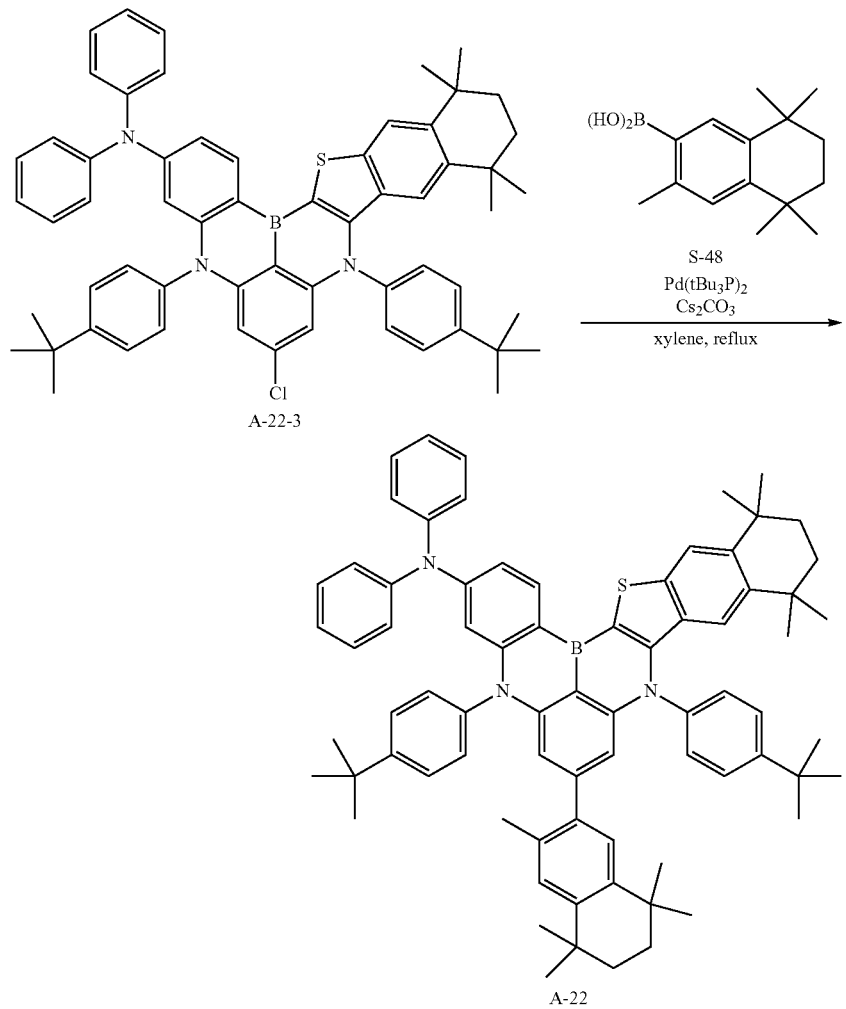

Compound A-22 (2.9 g, yield 62%, MS[M+H]+=1067) was obtained in the same manner as in Synthesis Example 81 except that Compound A-22-3 (4 g, 1 eq.) was used instead of Compound A-21-2.

Synthesis Example 85. Synthesis of Compound A-23-2

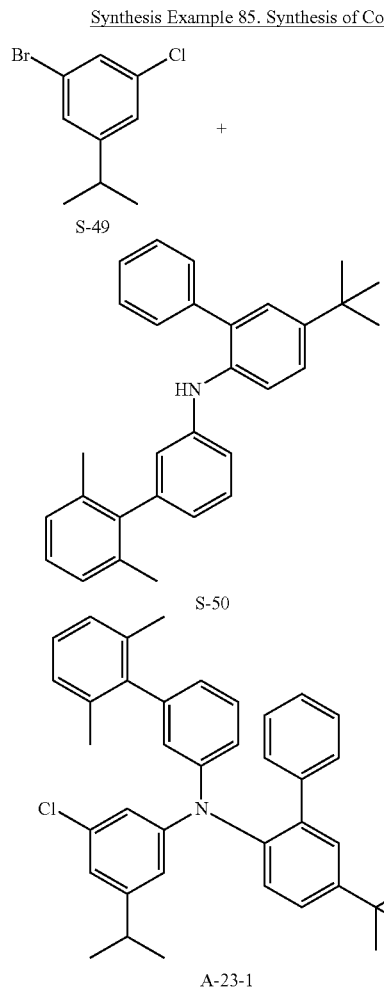

Compound A-23-1 (18.2 g, yield 76%, MS[M+H]+=558) was obtained in the same manner as in Synthesis Example 1 except that Compound S-49 (10 g) was used instead of Compound S-1, and Compound S-50 was used instead of Compound S-2.

Compound A-23-2 (17.7 g, yield 63%, MS[M+H]+=968) was obtained in the same manner as in Synthesis Example 3 except that Compounds A-23-1 (15 g. 1 eq.) and A-11-2 were used instead of Compounds A-2-1 and A-2-2.

Synthesis Example 86. Synthesis of Compound A-23

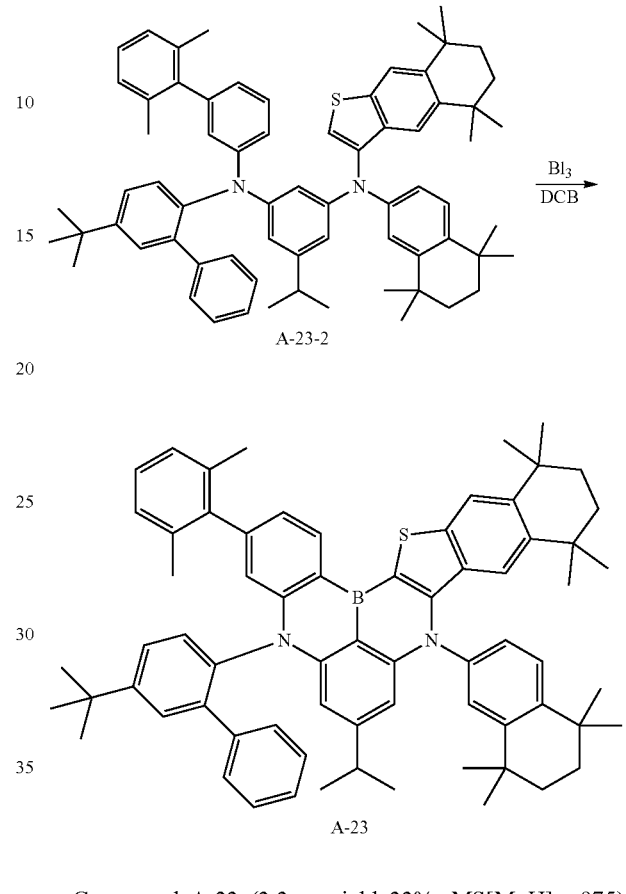

Compound A-23 (3.3 g, yield 33%, MS[M+H]+=975) was obtained in the same manner as in Synthesis Example 4 except that Compound A-23-2 (10 g. 1 eq.) was used instead of Compound A-2-3.

Synthesis Example 87. Synthesis of Compound A-24-2

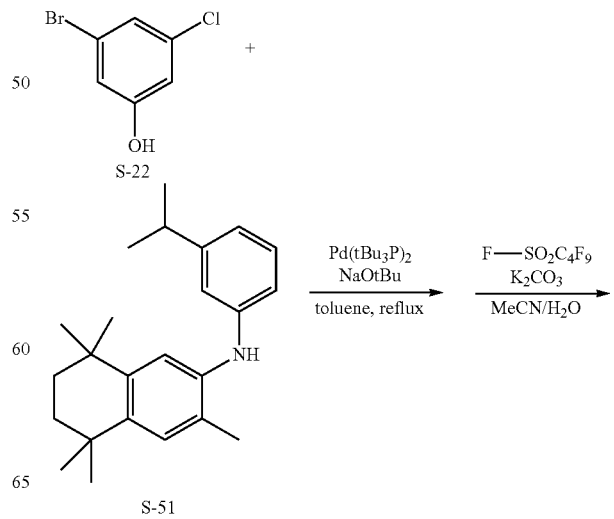

1197
-continued

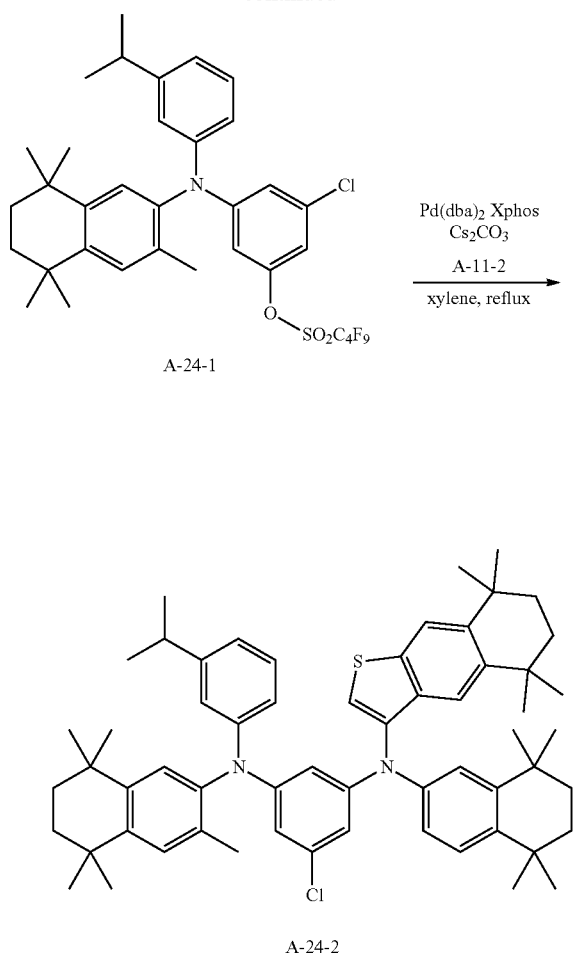

Compound A-24-1 (22.9 g, yield 64%) was obtained in the same manner as in Synthesis Example 32 except that Compound S-51 was used instead of Compound S-2.

Compound A-24-2 (15 g, yield 63%, MS[M+H]+=890) was obtained in the same manner as in Synthesis Example 33 except that Compound A-24-1 (20 g, 1 eq.) was used instead of Compound A-8-1, and Compound A-11-2 was used instead of Compound A-4-2.

Synthesis Example 88. Synthesis of Compound A-24

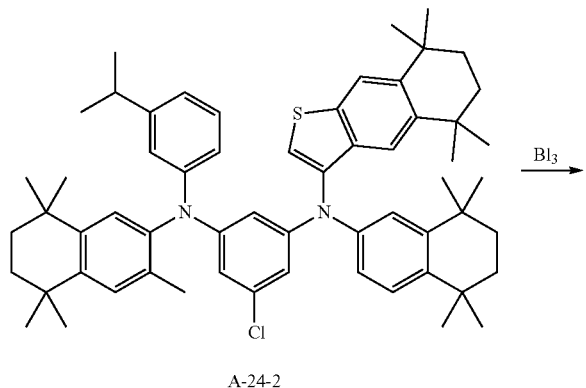

1198
-continued

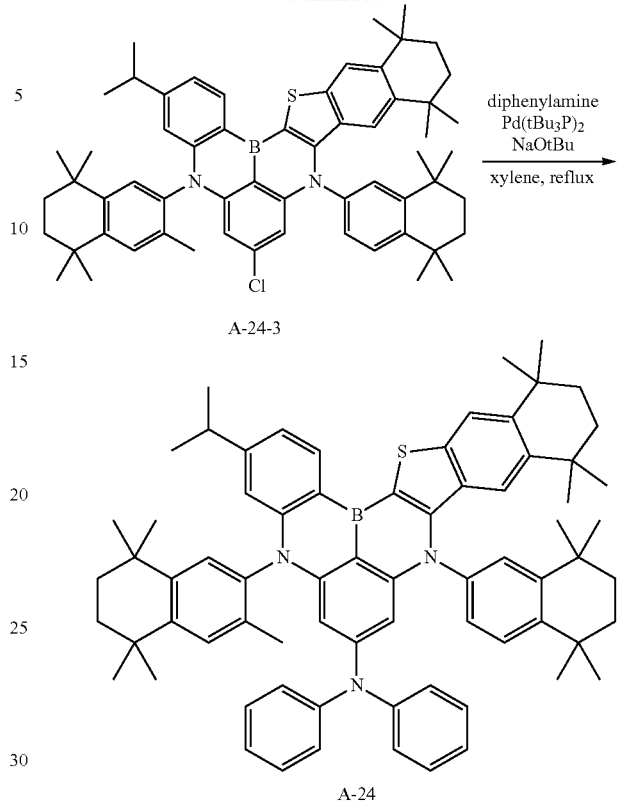

Compound A-24-3 (5.6 g, yield 43%, MS[M+H]+=897) was obtained in the same manner as in Synthesis Example 4 except that Compound A-24-2 (13 g. 1 eq.) was used instead of Compound A-2-3.

Compound A-24(3.4 g, yield 59%, MS[M+H]+=1031) was obtained in the same manner as in Synthesis Example 3 except that Compounds A-24-3 (5 g. 1 eq.) and diphenylamine were used instead of Compounds A-2-1 and A-2-2

Experimental Example 1: Simulation

Example 1

A system in which Compounds BD-1 and BH-B are included in a weight ratio of 5:95 was prepared. Specifically, using an OPLS3e force field, molecular dynamics calculation was performed through NPT calculation employing 300 molecules (BH-B 95%, A-1 5% ratio), a temperature of 300 K, and NVT and 30 ns with a simulation time of 3 ns, and as a result, an environment of a doped device was computational chemically obtained. The obtained molecular model is shown in FIG. 8.

Volume and density of the whole molecule, and an average distance between different molecules herein were obtained by calculation. The results are as shown in the following Table 1.

Examples 2 to 5

Molecular systems calculation was performed in the same manner as in Example 1 except that dopants described in Table 1 were used instead of Compound A-1.

Comparative Examples 1 to 4

Molecular systems calculation was performed in the same manner as in Example 1 except that dopants described in Table 1 were used instead of Compound A-1.

Specifically, molecular models obtained by Examples 1 to 5 and Comparative Examples 1 to 3 are shown in FIG. 4 to FIG. 12.

Specifically, FIG. 4 is a diagram showing a molecular model obtained through a simulation of the system of X-1 and BH-B of Comparative Example 1.

FIG. 5 is a diagram showing a molecular model obtained through a simulation of the system of X-2 and BH-B of Comparative Example 2.

FIG. 6 is a diagram showing a molecular model obtained through a simulation of the system of X-3 and BH-B of Comparative Example 3.

FIG. 7 is a diagram showing a molecular model obtained through a simulation of the system of X-4 and BH-B of Comparative Example 4.

FIG. 8 is a diagram showing a molecular model obtained through a simulation of the system of BD-1 and BH-B of Example 1.

FIG. 9 is a diagram showing a molecular model obtained through a simulation of the system of BD-2 and BH-B of Example 2.

FIG. 10 is a diagram showing a molecular model obtained through a simulation of the system of BD-3 and BH-B of Example 3.

FIG. 11 is a diagram showing a molecular model obtained through a simulation of the system of BD-4 and BH-B of Example 4.

FIG. 12 is a diagram showing a molecular model obtained through a simulation of the system of BD-5 and BH-B of Example 5.

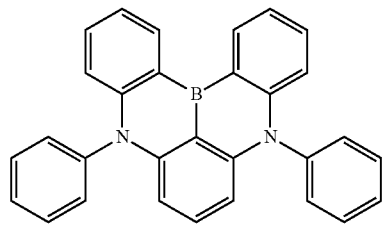

X-1

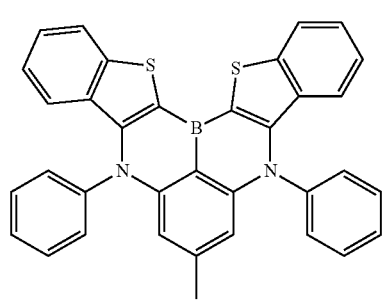

X-2

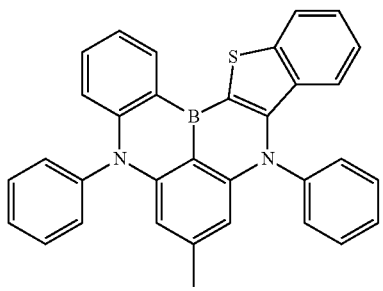

X-3

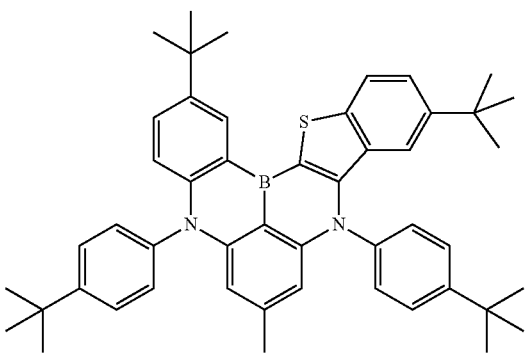

X-4

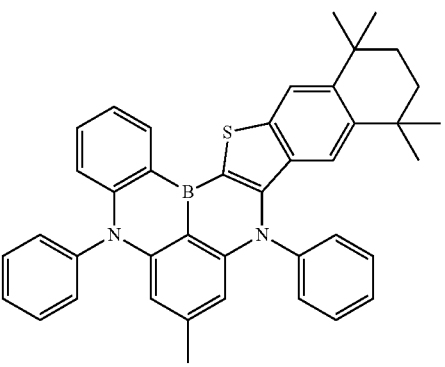

BD-1

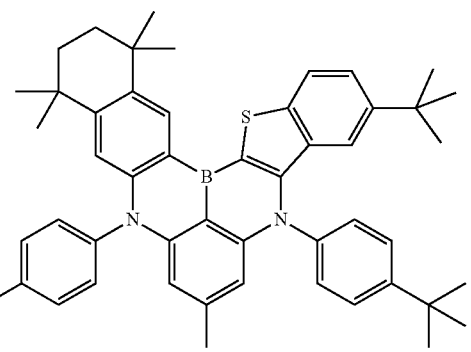

BD-2

-continued

BD-3
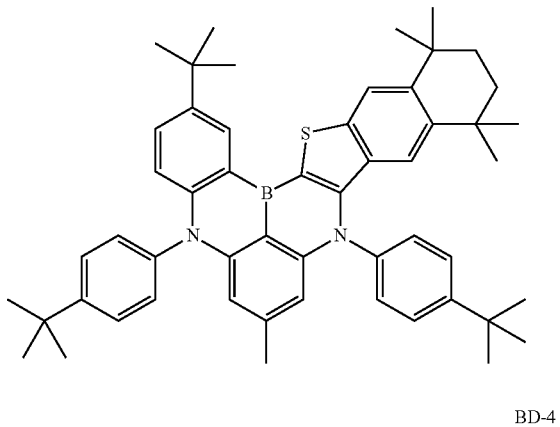

BD-4
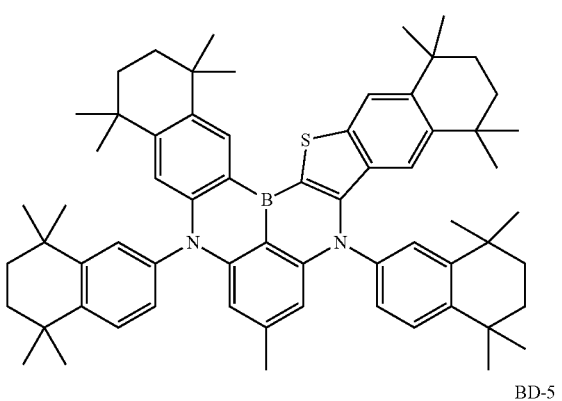

BD-5
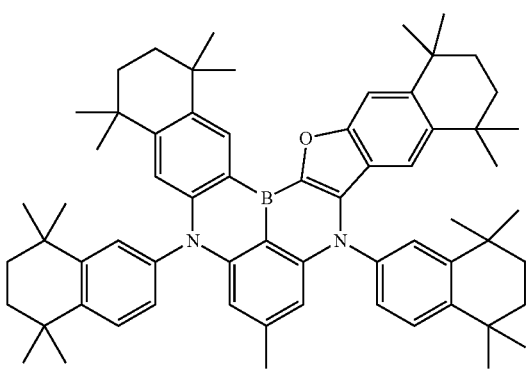

BH-B
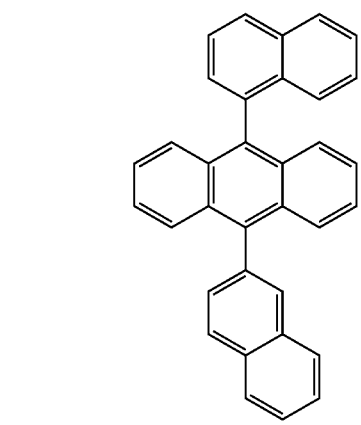

| Entry | System | Total Volume (cm³) | Total Density (g/cm³) | Intermolecular Distance (Å) |
|---|---|---|---|---|
| Comparative Example 1 | System of X-1 and BH-B | 193.60 × 10⁻²⁷ | 1.107 | 7.1 |
| Comparative Example 2 | System of X-2 and BH-B | 196.32 × 10⁻²⁷ | 1.107 | 14.75 |
| Comparative Example 3 | System of X-3 and BH-B | 195.07 × 10⁻²⁷ | 1.107 | 14.88 |
| Comparative Example 4 | System of X-4 and BH-B | 202.66 × 10⁻²⁷ | 1.093 | 15.10 |
| Example 1 | System of BD-1 and BH-B | 198.49 × 10⁻²⁷ | 1.102 | 14.95 |
| Example 2 | System of BD-2 and BH-B | 203.71 × 10⁻²⁷ | 1.094 | 15.15 |
| Example 3 | System of BD-3 and BH-B | 203.84 × 10⁻²⁷ | 1.094 | 15.19 |
| Example 4 | System of BD-4 and BH-B | 208.18 × 10⁻²⁷ | 1.090 | 15.26 |
| Example 5 | System of BD-5 and BH-B | 208.14 × 10⁻²⁷ | 1.089 | 15.39 |

From Table 1 and FIG. 4 to FIG. 12, it was identified that the distance between the host and the dopant in Example 1, a system using Compound BD-1 including a fused aliphatic hydrocarbon ring substituted with an alkyl group as a dopant and BH-B as a host, increased by 2.1 times compared to the system of Compounds X-1 and BH-B, and when comparing Comparative Example 3 and Example 1, it was identified that the compound including a fused aliphatic hydrocarbon ring substituted with an alkyl group had a more increased intermolecular distance in the molecular model with the host. In addition, it was identified that, even when compared with the system of Compound X-4 in which the compound is all substituted with a tert-butyl group, the distance between the host and the dopant increased as a fused aliphatic hydrocarbon ring substituted with an alkyl group was introduced. Accordingly, it may be expected that device efficiency increases when manufacturing a device by introducing the compound according to one embodiment of the present specification including one or more fused aliphatic hydrocarbon rings substituted with an alkyl group as a dopant of a light emitting layer since a dexter energy transfer with triplet energy of the host occurs less.

Experimental Example 2: Experiment of Spectroscopic Analysis

Examples 6 and 7 and Comparative Examples 5 to 7

A maximum emission wavelength of each of compounds of the following Table 2 was measured and described in the following Table 2, and a measurement device used herein was a JASCO FP-8600 fluorescence spectrophotometer.

The maximum emission wavelength in a solution state of each of compounds of the following Table 2 was obtained as follows. Using toluene as a solvent, the compound to measure was dissolved in a concentration of 1 μM (microM) to prepare a sample for measurement. The sample solution was introduced to a quartz cell, and degassed using nitrogen gas ($N_2$) to remove oxygen in the solution, and using the measurement device, a fluorescence spectrum was measured at room temperature (300 K). Herein, a wavelength value (nm) of the maximum emission peak was obtained.

The maximum emission wavelength in a film state of each of the compounds was obtained as follows. On a glass substrate, a host Compound BH-1 and a dopant compound of the following Table 2 were vacuum deposited in a weight ratio of 98:2 to prepare a light emitting layer film having a thickness of 1000 Å. In the above-mentioned process, the deposition rate of the organic material was maintained at 0.1 nm/sec. For each of the prepared films, a fluorescence spectrum was measured at room temperature (300 K) using the measurement device. Herein, a wavelength value (nm) of the maximum emission peak was obtained, and the measurement graph is shown in FIG. 3.

X-4

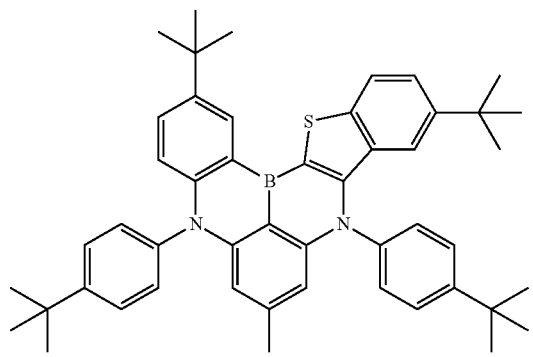

X-5

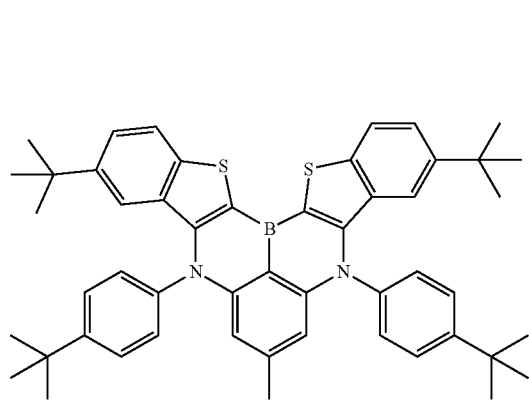

X-6

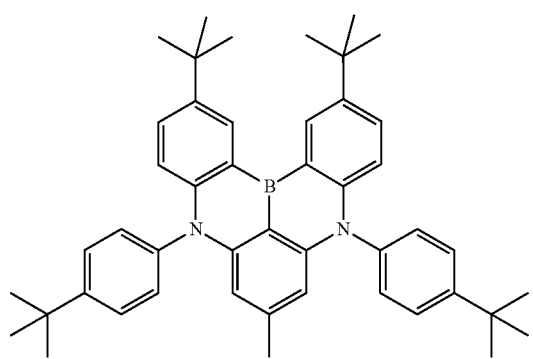

-continued

BD-6

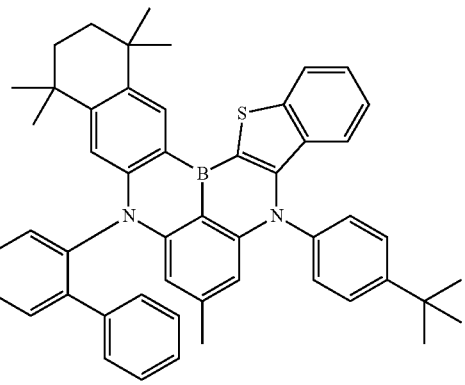

BD-7

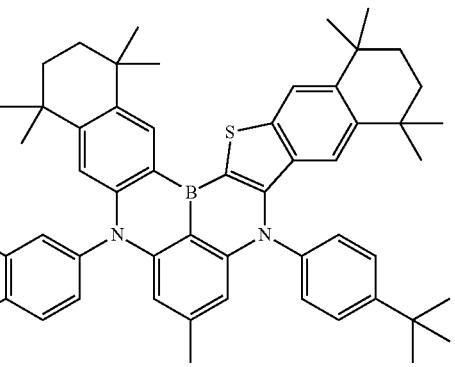

BH-1

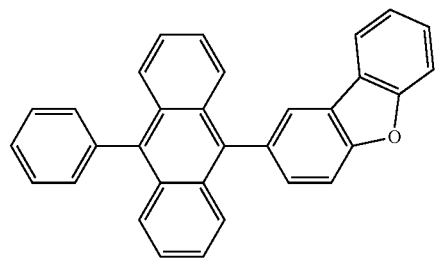

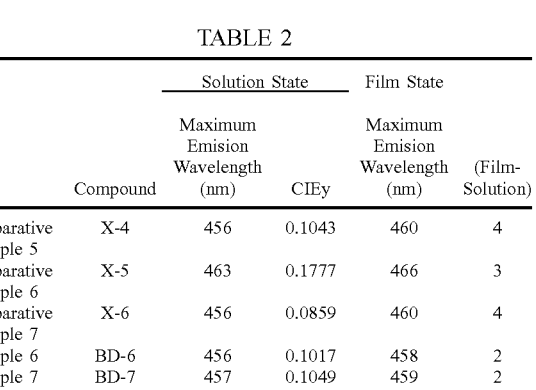

TABLE 2

| | | Solution State | | Film State | |
|---|---|---|---|---|---|
| Entry | Compound | Maximum Emision Wavelength (nm) | CIEy | Maximum Emision Wavelength (nm) | (Film-Solution) |
| Comparative Example 5 | X-4 | 456 | 0.1043 | 460 | 4 |
| Comparative Example 6 | X-5 | 463 | 0.1777 | 466 | 3 |
| Comparative Example 7 | X-6 | 456 | 0.0859 | 460 | 4 |
| Example 6 | BD-6 | 456 | 0.1017 | 458 | 2 |
| Example 7 | BD-7 | 457 | 0.1049 | 459 | 2 |

When comparing emission spectra in a solution state of Compounds X-4, X-5 and X-6 in Table 2 and FIG. 3, it was identified that the second peak formed in a long wavelength region had its intensity increased compared to the main peak as the heteroring increased by one based on Compound X-6. When looking at the CIEy value representing color purity, the value of Compound X-5 having the strongest second peak was the largest. However, it was identified that Compound BD-6 represented by Chemical Formula 1 of the present specification had more improved color purity (CIEy) than X-4 although the maximum emission wavelength value in a solution state was the same as the value of Compound X-4. In addition, when comparing the maximum emission wavelength values in a film state between the compound of Chemical Formula 1 according to one embodiment of the present specification, that is, Compounds BD-6 and BD-7 including one or more fused aliphatic hydrocarbon rings substituted with an alkyl group, and Compound X-4 that does not include a fused aliphatic hydrocarbon ring substituted with an alkyl group, a shorter wavelength was observed when introducing a fused aliphatic hydrocarbon ring substituted with an alkyl group compared to the compounds with no fused aliphatic hydrocarbon ring substituted with an alkyl group. This is due to the fact that intermolecular interaction is minimized between the host and the dopant as shown in the experimental results of the simulation of Experimental Example 1. Therefore, an organic light emitting device with high color purity and high efficiency is obtained using the compound of Chemical Formula 1 of the present specification.

Experimental Example 3: Device Example

Example 8

A glass substrate on which indium tin oxide (ITO) was coated as a thin film to a thickness of 1,400 Å was placed in detergent-dissolved distilled water and ultrasonic cleaned. Herein, a product of Fischer Co. was used as the detergent, and as the distilled water, distilled water filtered twice with a filter manufactured, by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum deposition apparatus.

On the transparent ITO electrode prepared as above, the following HI-A and LG-101 were thermal vacuum deposited to thicknesses of 650 Å and 50 Å, respectively, to form a hole injection layer. On the hole injection layer, a hole transfer layer was formed by vacuum depositing the following HT-A to a thickness of 600 Å. The following HT-B was vacuum deposited to a thickness of 50 Å on the hole transfer layer to form an electron blocking layer. Subsequently, on the electron blocking layer, a light emitting layer was formed to a thickness of 200 Å by vacuum depositing the following Compound A-1 as a blue light emitting dopant in 4 parts by weight based on 100 parts by weight of the light emitting layer, and the following BH-A as a host. Then, on the light emitting layer, the following Compound ET-A was vacuum deposited to 50 Å as a first electron transfer layer, and subsequently, the following ET-B and LiQ were vacuum deposited in a weight ratio of 1:1 to a thickness of 360 Å to form a second electron transfer layer. An electron injection layer was formed on the second electron transfer layer by vacuum depositing LiQ to a thickness of 5 Å. On the electron injection layer, a cathode was formed by depositing aluminum and silver in a weight ratio of 10:1 to a thickness of 220 Å, and then depositing aluminum thereon to a thickness of 1000 Å.

In the above-described process, the deposition rates of the organic materials were maintained at 0.4 Å/sec to 0.9 Å/sec, the deposition rate of the aluminum of the cathode was maintained at 2 Å/sec, and the degree of vacuum during the deposition was maintained at $5\times10^{-8}$ torr to $1\times10^{-7}$ torr, and as a result, an organic light emitting device was manufactured.

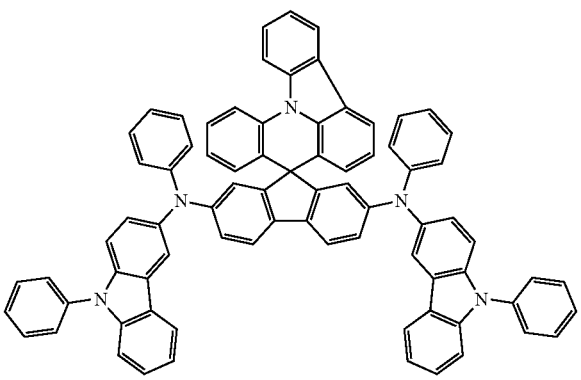

HI-A

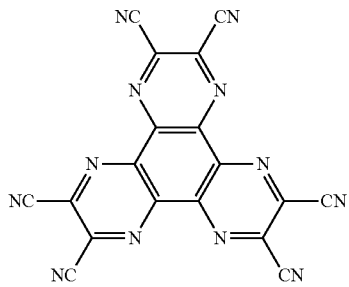

LG-101

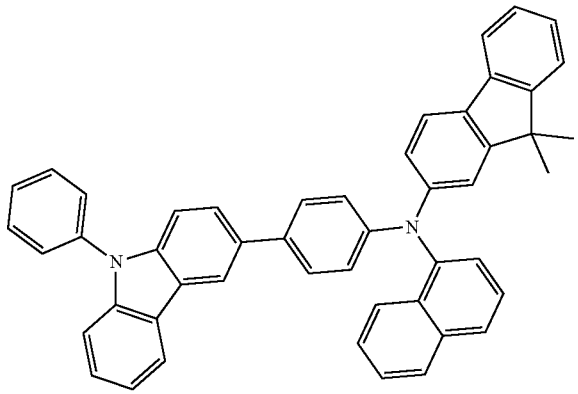

HT-A

HT-B

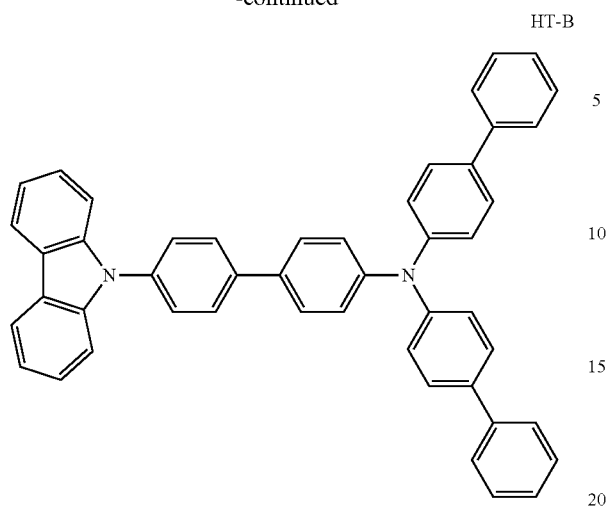

ET-A

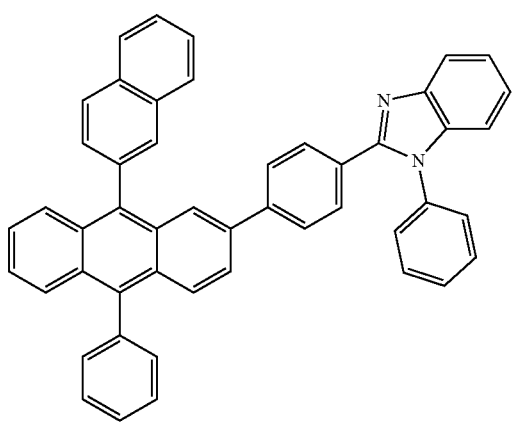

BH-A

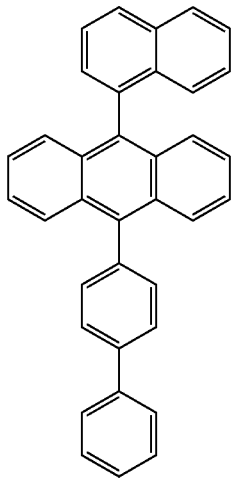

ET-B

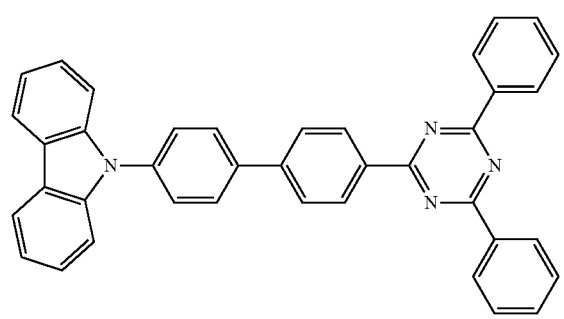

A-1

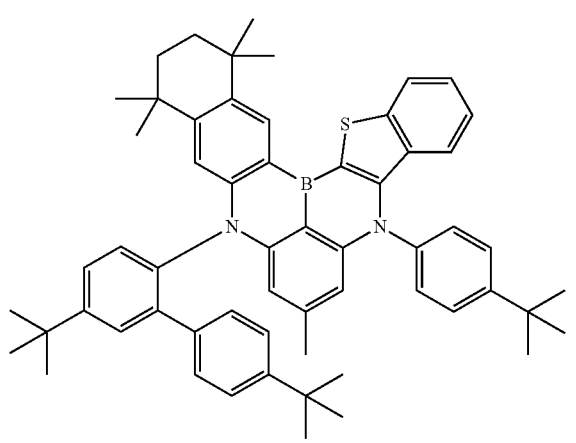

LiQ

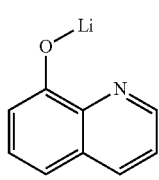

Examples 9 to 32 and Comparative Examples 3 to 11

Organic light emitting devices of Example 9 to Example 32 and Comparative Examples 8 to 11 were each manufactured in the same manner as in Example 8 except that compounds described in the following Table 3 were each used as the dopant of the light emitting layer instead of Compound A-1, and compounds described in the following Table 3 were each used as the host material instead of BH-A.

BH-B
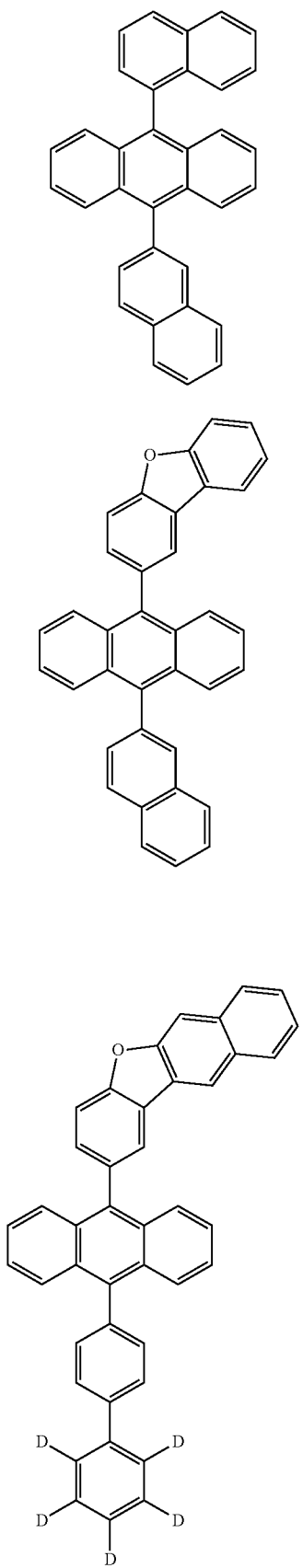
BH-C
BH-D
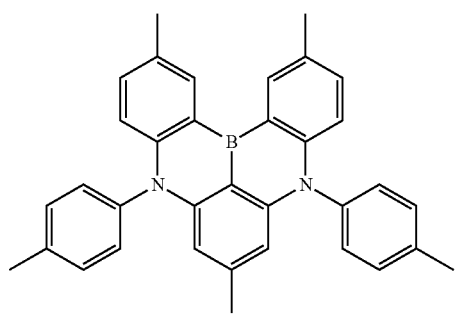
X-7
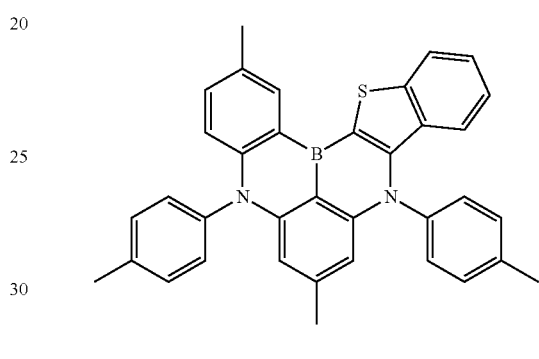
X-8
X-9
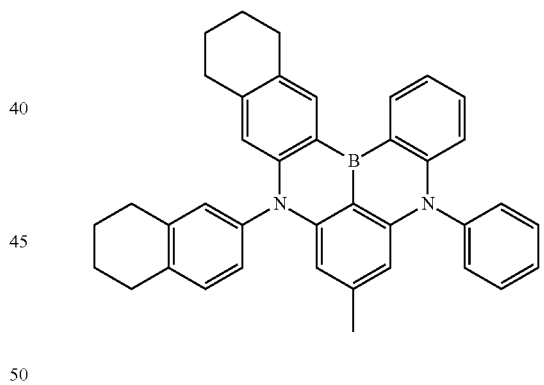
X-10

-continued
A-1
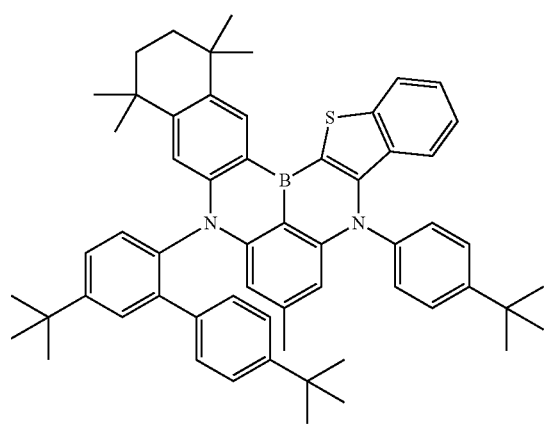
A-2
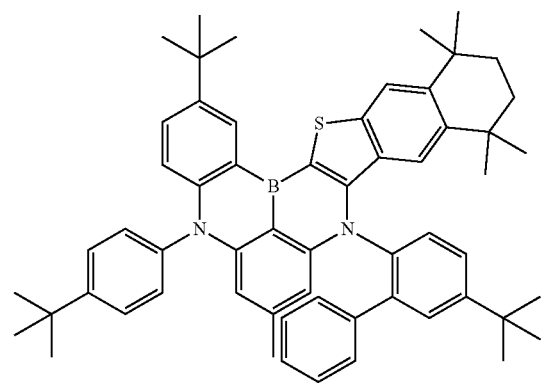
A-3
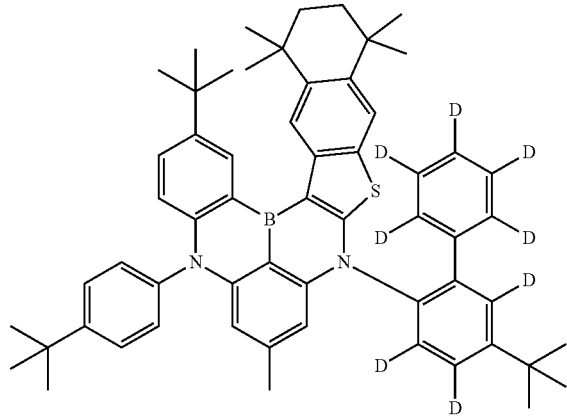
-continued
A-4
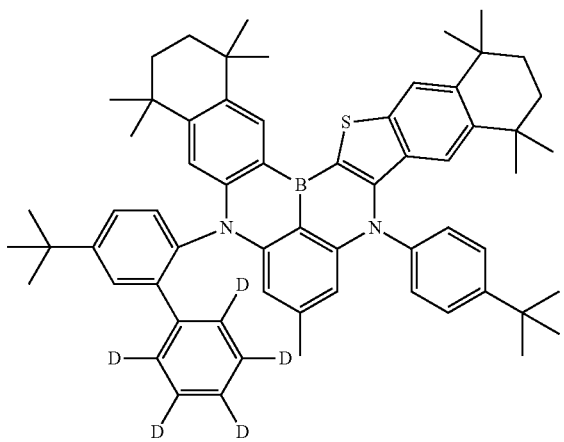
A-5
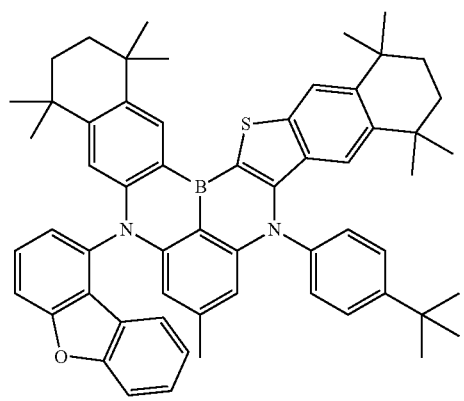
A-6
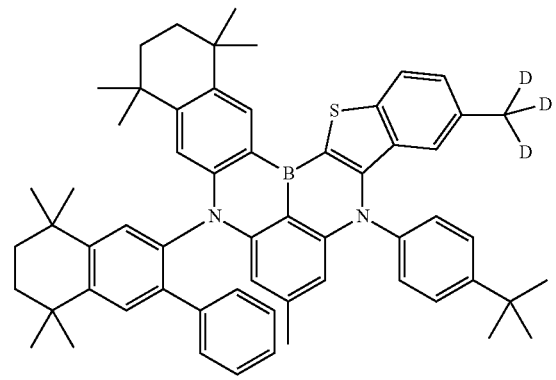

-continued
A-7
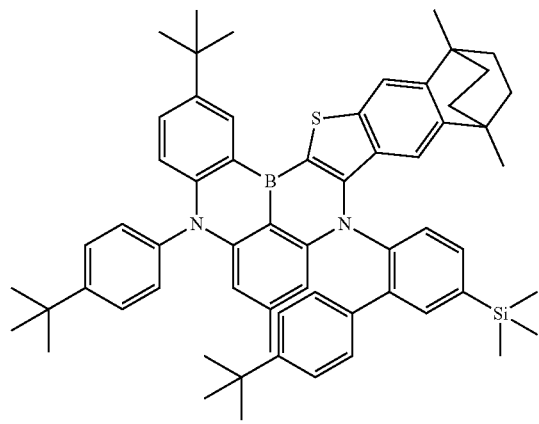
A-8
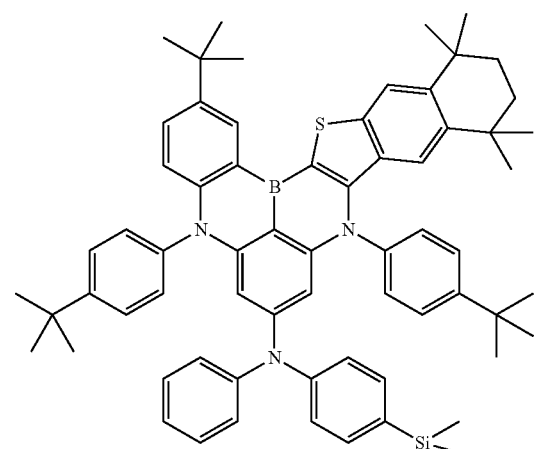
A-9
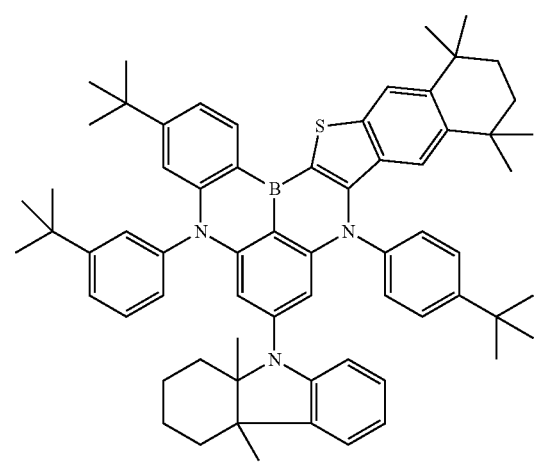
-continued
A-10
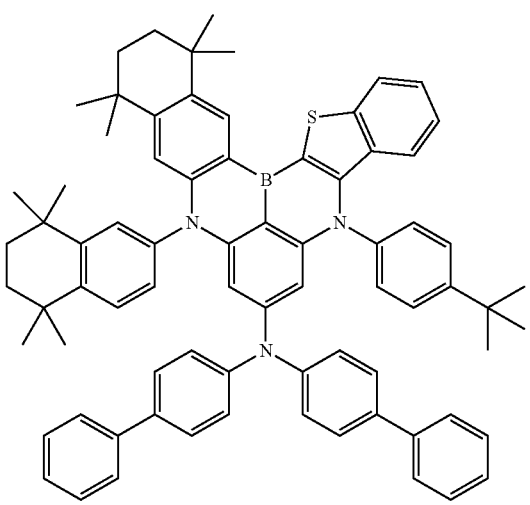
A-11
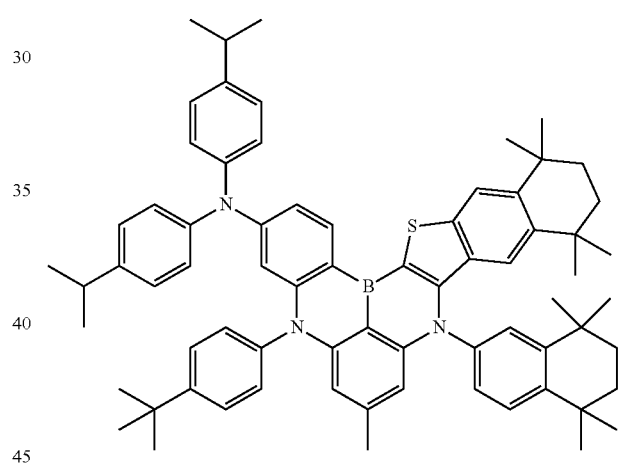
A-12
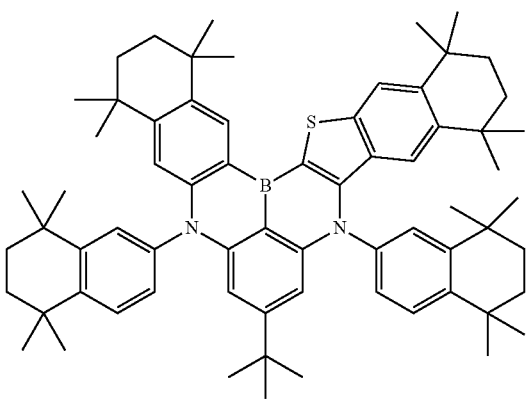

-continued
B-1
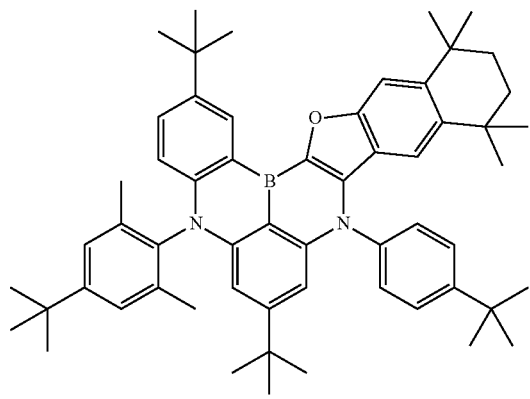
B-2
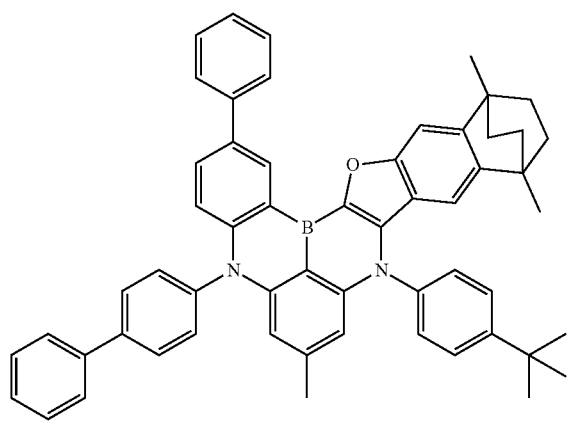
B-3
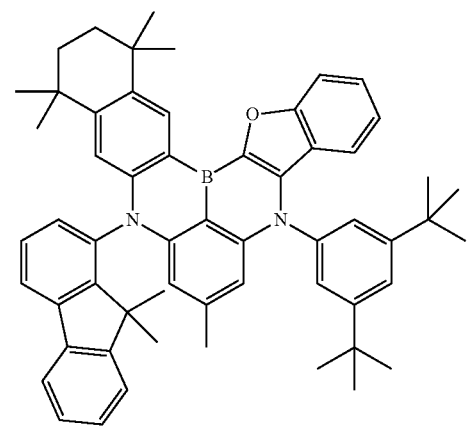
-continued
B-4
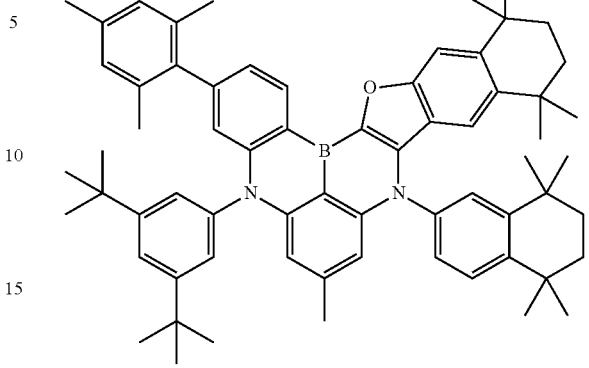
B-5
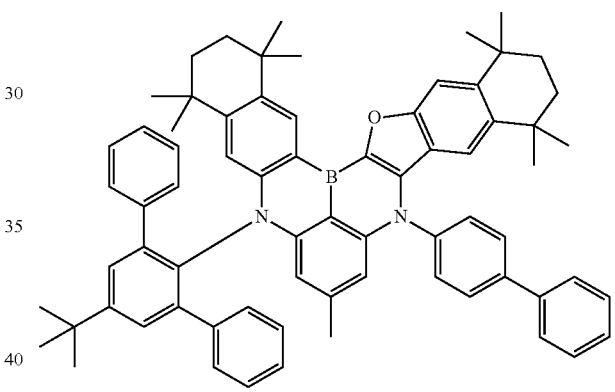
B-6
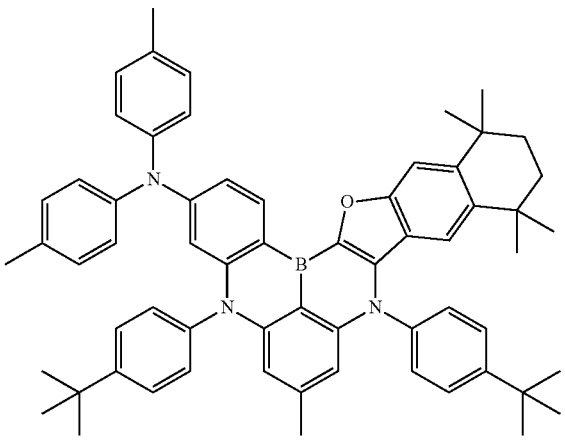

1217
-continued

B-7
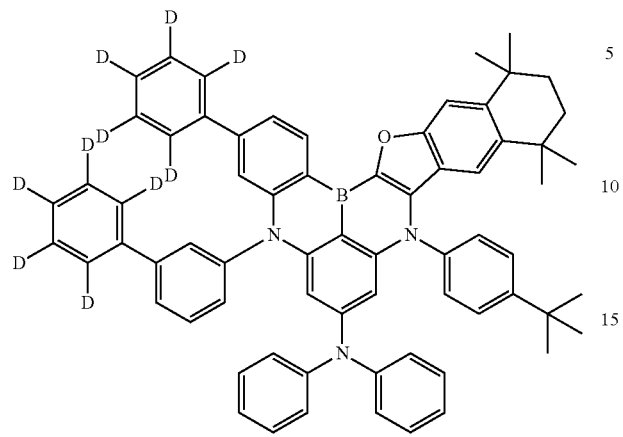

B-8
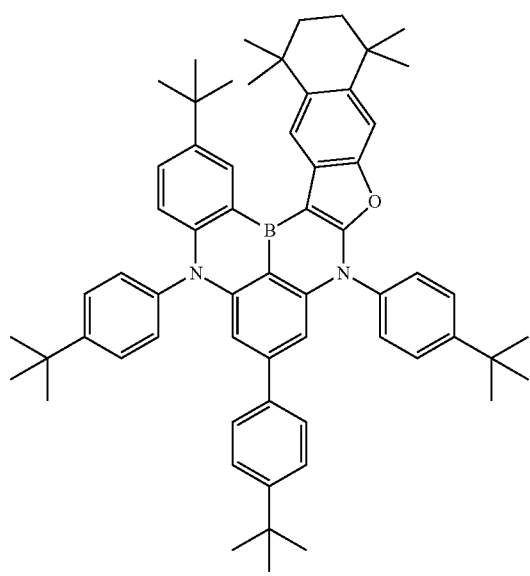

B-9
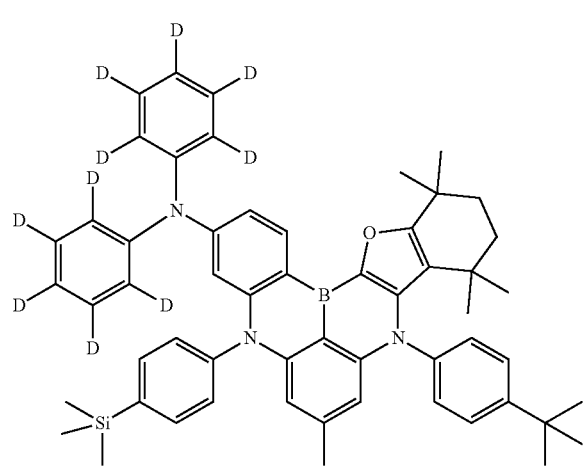

1218
-continued

A-21
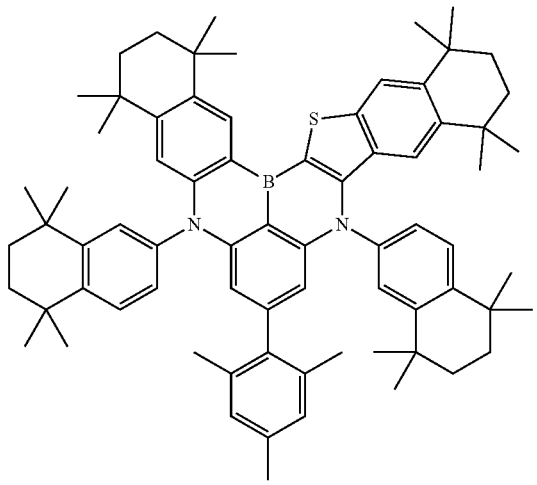

A-23
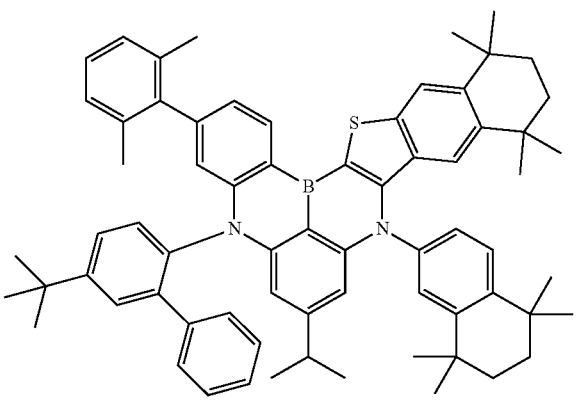

A-24

For each of the organic light emitting devices of Example 8 to Example 32 and Comparative Examples 8 to 11, voltage and conversion efficiency (cd/A/y) when applying current density of 10 mA/cm² and a lifetime ($T_{95}$) when applying current density of 20 mA/cm² were measured, and the results are shown in the following Table 3. Herein, $T_{95}$ means time taken for luminance to decrease to 95% when employing initial luminance at current density of 20 mA/cm² as 100%, and the percentage is shown based on Comparative Example 8.

TABLE 3

| | Light Emitting Layer | | Driving Voltage | 10 mA/cm² Conversion Efficiency | 20 mA/cm² LT95 |
|---|---|---|---|---|---|
| Entry | Host | Dopant | (V) | (cd/A/y) | (Ratio) |
| Example 8 | BH-A | A-1 | 3.87 | 44.7 | 1.20 |
| Example 9 | BH-A | A-2 | 3.86 | 45.4 | 1.52 |
| Example 10 | BH-A | A-3 | 3.88 | 45.3 | 1.50 |
| Example 11 | BH-A | A-7 | 3.89 | 45.9 | 1.45 |
| Example 12 | BH-A | A-12 | 3.90 | 46.7 | 1.53 |
| Example 13 | BH-A | A-13 | 3.85 | 46.1 | 1.45 |
| Example 14 | BH-B | A-5 | 3.85 | 46.0 | 1.30 |
| Example 15 | BH-B | A-6 | 3.90 | 45.1 | 1.25 |
| Example 16 | BH-B | A-11 | 3.89 | 46.4 | 1.42 |
| Example 17 | BH-C | A-9 | 3.89 | 45.5 | 1.33 |
| Example 18 | BH-D | A-4 | 3.79 | 45.9 | 1.55 |
| Example 19 | BH-D | A-8 | 3.78 | 45.1 | 1.30 |
| Example 20 | BH-E | A-10 | 3.83 | 45.0 | 1.28 |
| Example 21 | BH-A | B-1 | 3.86 | 45.1 | 1.38 |
| Example 22 | BH-A | B-8 | 3.87 | 45.6 | 1.35 |
| Example 23 | BH-A | B-9 | 3.77 | 45.8 | 1.36 |
| Example 24 | BH-B | B-2 | 3.89 | 45.2 | 1.27 |
| Example 25 | BH-B | B-4 | 3.85 | 45.4 | 1.34 |
| Example 26 | BH-B | B-5 | 3.85 | 45.5 | 1.32 |
| Example 27 | BH-C | B-7 | 3.82 | 45.1 | 1.33 |
| Example 28 | BH-D | B-3 | 3.77 | 44.5 | 1.11 |
| Example 29 | BH-E | B-6 | 3.77 | 45.6 | 1.30 |
| Example 30 | BH-D | A-21 | 3.78 | 45.8 | 1.16 |
| Example 31 | BH-C | A-23 | 3.81 | 44.9 | 1.27 |
| Example 32 | BH-B | A-24 | 3.86 | 45.2 | 1.18 |
| Comparative Example 8 | BH-A | X-7 | 3.99 | 43.2 | 1.00 |
| Comparative Example 9 | BH-A | X-8 | 3.97 | 41.0 | 1.15 |
| Comparative Example 10 | BH-A | X-9 | 4.00 | 44.1 | 0.75 |
| Comparative Example 11 | BH-B | X-10 | 3.97 | 42.3 | 1.03 |

Examples 33 to 40 and Comparative Examples 12 and 13

Organic light emitting devices of Examples 33 to 40 and Comparative Examples 12 and 13 were each manufactured in the same manner as in Example 8 except that compounds described in the following Table 4 were each used as the dopant of the light emitting layer instead of Compound A-1, and compounds described in the following Table 4 were each used as the host material instead of BH-A.

In Examples 30 to 36 and Comparative Examples 12 and 13, the first host and the second host had a weight ratio of 50:50 in the light emitting layer.

For each of the organic light emitting devices of Examples 33 to 40 and Comparative Examples 12 and 13, voltage and conversion efficiency (cd/A/y) when applying current density of 10 mA/cm² and a lifetime ($T_{95}$) when applying current density of 20 mA/cm² were measured, and the results are shown in the following Table 4. Herein, $T_{95}$ means time taken for luminance to decrease to 95% when employing initial luminance at current density of 20 mA/cm² as 100%, and the percentage is shown based on Comparative Example 3.

A-22

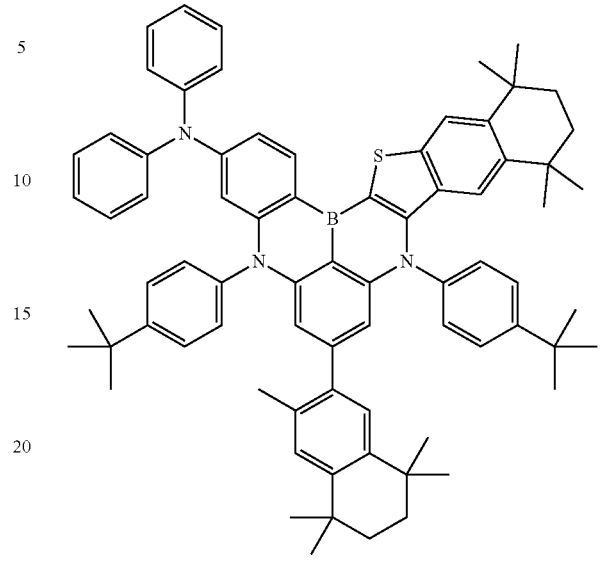

TABLE 4

| | Light Emitting Layer | | | Driving Voltage | 10 mA/cm² Conversion Efficiency | 20 mA/cm² LT95 |
|---|---|---|---|---|---|---|
| Entry | First Host | Second Host | Dopant | (V) | (cd/A/y) | (Ratio) |
| Example 33 | BH-A | BH-D | A-2 | 3.82 | 44.49 | 1.37 |
| Example 34 | BH-A | BH-E | A-4 | 3.81 | 46.13 | 1.51 |
| Example 35 | BH-B | BH-D | A-8 | 3.8 | 46.00 | 1.30 |
| Example 36 | BH-D | BH-E | A-11 | 3.74 | 45.01 | 1.24 |
| Example 37 | BH-A | BH-E | B-5 | 3.81 | 44.64 | 1.25 |
| Example 38 | BH-B | BH-D | B-6 | 3.78 | 46.49 | 1.35 |
| Example 39 | BH-B | BH-E | B-9 | 3.73 | 44.20 | 1.20 |
| Example 40 | BH-B | BH-D | A-22 | 3.78 | 46.3 | 1.22 |
| Comparative Example 12 | BH-A | BH-D | X-7 | 3.94 | 41.90 | 0.94 |
| Comparative Example 13 | BH-B | BH-D | X-8 | 3.91 | 40.18 | 1.10 |

The conversion efficiency (cd/A/y) considers color purity (CIEy) of the material as well in addition to current efficiency (cd/A), and is an important reference value for efficiency in small and large organic light emitting devices aiming for high luminance and high color gamut. As seen from the device results of Tables 3 and 4, the compounds including at least one fused aliphatic hydrocarbon ring substituted with an alkyl group, which is Chemical Formula 1 according to one embodiment of the present specification, were superior in both device conversion efficiency and lifetime compared to the compounds that did not include a fused aliphatic hydrocarbon ring substituted with an alkyl group. Particularly, when comparing with Compounds X-9 and X-10 including an unsubstituted fused aliphatic hydrocarbon ring, superior efficiency and lifetime were identified with the dopant introducing a fused aliphatic hydrocarbon ring substituted with an alkyl group. In addition, better device efficiency was observed as more fused aliphatic hydrocarbon rings substituted with an alkyl group were introduced, which was consistent with the experimental results of the simulation of Experimental Example 1.

Examples 41 to 43 and Comparative Examples 14 and 15

Organic light emitting devices of Examples 41 to 43 and Comparative Examples 14 and 15 were each manufactured in the same manner as in Example 8 except that dopant compounds described in the following Table 5 were each used as the light emitting layer dopant instead of Compound A-1 (parts by weight of dopant based on 100 parts by weight of light emitting layer).

TABLE 5

| Entry | Dopant (Light Emitting Layer) | Doping Concentration | 10 mA/cm² Conversion Efficiency (cd/A) | Conversion Efficiency (cd/A/y) | CIEy | 20 mA/cm² LT95 (Ratio) |
|---|---|---|---|---|---|---|
| Example 41 | A-1 | 0.5 Parts by Weight | 3.77 | 42.9 | 0.088 | — |
| | | 2 Parts by Weight | 4.01 | 44.6 | 0.090 | — |
| | | 4 Parts by Weight | 4.29 | 44.7 | 0.096 | 1.20 |
| Example 42 | A-2 | 0.5 Parts by Weight | 3.85 | 43.8 | 0.088 | — |
| | | 2 Parts by Weight | 4.43 | 45.2 | 0.098 | — |
| | | 4 Parts by Weight | 4.86 | 45.4 | 0.107 | 1.52 |
| Example 43 | A-12 | 0.5 Parts by Weight | 3.75 | 45.1 | 0.083 | — |
| | | 2 Parts by Weight | 4.12 | 46.3 | 0.089 | — |
| | | 4 Parts by Weight | 4.39 | 46.7 | 0.094 | 1.53 |
| Comparative Example 14 | X-7 | 0.5 Parts by Weight | 3.35 | 41.9 | 0.080 | — |
| | | 2 Parts by Weight | 3.83 | 45.0 | 0.085 | — |
| | | 4 Parts by Weight | 3.93 | 43.2 | 0.091 | 1.00 |
| Comparative Example 15 | X-5 | 0.5 Parts by Weight | 4.19 | 29.5 | 0.142 | — |
| | | 2 Parts by Weight | 4.79 | 30.7 | 0.156 | — |
| | | 4 Parts by Weight | 5.02 | 30.1 | 0.167 | 1.40 |

In Table 5, it was identified that the compounds including at least one fused aliphatic hydrocarbon ring substituted with an alkyl group, which is Chemical Formula 1 according to one embodiment of the present specification, had no decrease in efficiency even with high doping in the device, and had increased efficiency. In addition, when comparing with the case of using Compound X-7 of Comparative Example 14 as a dopant of a light emitting layer of an organic light emitting device in a low doping concentration (0.5 parts by weight of dopant based on 100 parts by weight of light emitting layer) region, higher efficiency was obtained when using Compounds A-1, A-2 and A-12, Chemical Formula 1 of the present specification, as a dopant of a light emitting layer of an organic light emitting device. When using Compound X-5 of Comparative Example 15 as a dopant of a light emitting layer of an organic light emitting device, current efficiency was highly superior, however, conversion efficiency was low due to a decrease in color purity (CIEy) caused by light emission in the long wavelength region.

Through the various experiments, it was identified that the compound of Chemical Formula 1 according to one embodiment of the present specification had superior performance of high efficiency and long lifetime.

Experimental Example 4: Thermos Gravimetric Analysis

Examples 44 to 46 and Comparative Examples 16 and 17

A thermos gravimetric analyzer (TGA) is a device measuring, after applying a temperature to a sample, changes in the mass of the sample as a function of time or temperature. A mass loss of a material is caused by evaporation or a chemical reaction producing gaseous products. Using Q-500, 3 mg or more and less than 5 mg of compounds of the following Table 6 completed with sublimation purification were each put on a Pt pan, and heated from room temperature to 700° C. at a rate of 10° C./min. Herein, a temperature at which the mass of the compound was reduced by 5% with respect to the total weight (=Td-5% loss) and the amount (percent) of the residue remaining on the pan after heating to 700° C. were measured. The TGA graph of Compound A-20 of Example 46 is shown in FIG. 13, and the TGA graphs of Compounds X-5 and X-4 of Comparative Examples 16 and 17 are respectively shown in FIG. 14 and FIG. 15.

TABLE 6

| Entry | Comparative Example 16 | Comparative Example 17 | Example 44 | Example 45 | Example 46 |
|---|---|---|---|---|---|
| Compound | X-5 | X-4 | A-2 | A-19 | A-20 |
| Molecular Weight | 770.95 | 714.86 | 845.05 | 823.05 | 1007.33 |
| Td-5% Loss (° C.) | 459 | 386 | 375 | 390 | 397 |
| Residue (%) | 30.1 | 22.7 | 4.2 | 0.6 | 2.2 |

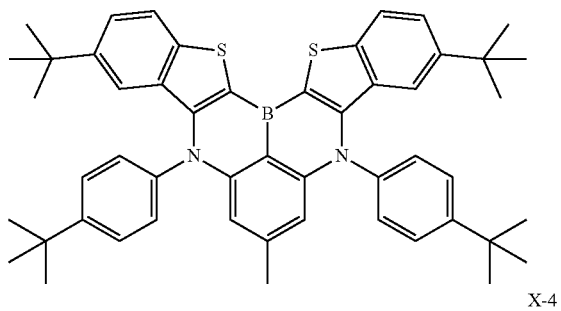

X-5

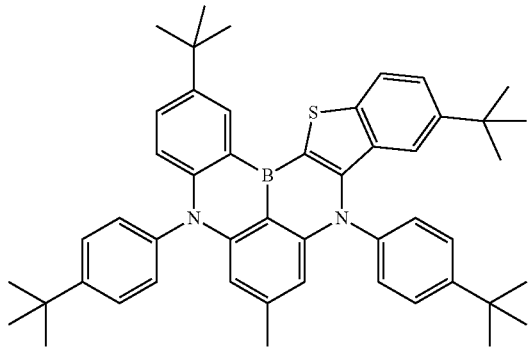

X-4

-continued

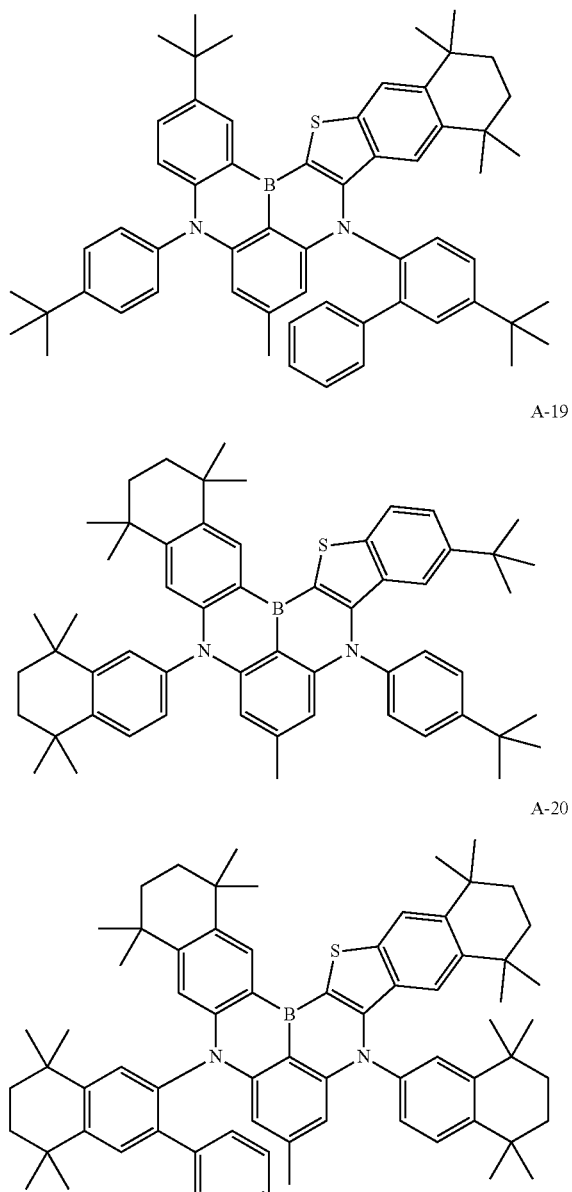

A-1

A-19

A-20

In Table 6 and FIG. 13 to FIG. 15, the Td-5% loss value was measured to be very high of 459° C. from the experimental result of the thermos gravimetric analysis on symmetric Compound X-5 of Comparative Example 16, and after the analysis, 30% of the compound remained on the pan. In addition, although the Td-5% loss value of asymmetric Compound X-4 including a heteroring of Comparative Example 17 somewhat decreased, the percentage of the compound remaining on the pan after the analysis was measured to be approximately 23%. On the other hand, Compounds A-2, A-19 and A-20 including at least one fused aliphatic hydrocarbon ring substituted with an alkyl group of Examples 44 to 46, that is, Chemical Formula 1 of the present specification, had a lower or similar Td-5% loss value even with a higher molecular weight compared to Compound X-4.

Through the experiment, it was identified that the compound of Chemical Formula 1 according to one embodiment of the present specification was superior in terms of thermal stability by having a low a Td-5% loss value compared to compounds with similar molecular weights and thereby having a low sublimation temperature, and was an organic material suited for a deposition device as well.

The invention claimed is:

1. A compound represented by the following Chemical Formula 1:

[Chemical Formula 1]

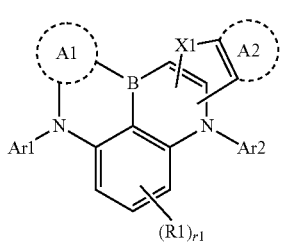

wherein in Chemical Formula 1,

X1 is O or S,

A1 is a substituted or unsubstituted heteroring; a substituted or unsubstituted aromatic hydrocarbon ring; or a substituted or unsubstituted fused ring of aromatic hydrocarbon ring and aliphatic hydrocarbon ring, A2 is a substituted or unsubstituted aliphatic hydrocarbon ring; or a substituted or unsubstituted fused ring of aromatic hydrocarbon ring and aliphatic hydrocarbon ring having 6 to 30 carbon atoms, Ar1 and Ar2 are the same as or different from each other, and each independently a substituted or unsubstituted cycloalkyl group; a substituted or unsubstituted aryl group; a substituted or unsubstituted heterocyclic group; or a substituted or unsubstituted fused ring group of aromatic hydrocarbon ring and aliphatic hydrocarbon ring, R1 is hydrogen; deuterium; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; a substituted or unsubstituted fused ring group of aromatic hydrocarbon ring and aliphatic hydrocarbon ring; or a substituted or unsubstituted heterocyclic group, r1 is an integer of 1 to 3, when r1 is 2 or greater, the two or more R1s are the same as or different from each other, the compound of Chemical Formula 1 includes at least one fused aliphatic hydrocarbon ring having 6 to 10 carbon atoms substituted with a substituted or unsubstituted alkyl group having 1 to 10 carbon atoms.

2. The compound of claim 1, wherein the compound of Chemical Formula 1 is represented by the following Chemical Formula 1-3 or 1-4:

[Chemical Formula 1-3]

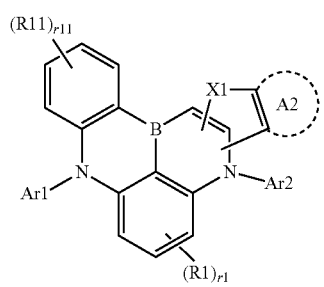

[Chemical Formula 1-4]

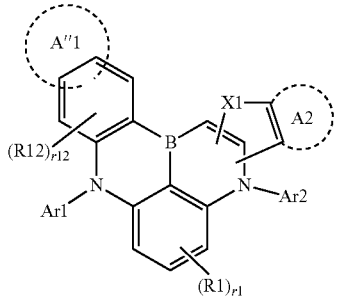

wherein in Chemical Formulae 1-3 and 1-4,
X1, A2, Ar1, Ar2, R1 and r1 are the same as defined in Chemical Formula 1,
A″1 is a substituted or unsubstituted aliphatic hydrocarbon ring,
R11 and R12 are the same as or different from each other, and each independently hydrogen; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; or a substituted or unsubstituted heterocyclic group, or adjacent groups bond to each other to form a substituted or unsubstituted ring,
r11 is an integer of 1 to 4, and when r11 is 2 or greater, the two or more R11s are the same as or different from each other, and
r12 is 1 or 2, and when r12 is 2, the two R12s are the same as or different from each other.

3. The compound of claim 2, wherein the compound of Chemical Formula 1-4 is represented by the following Chemical Formula 1-4-1 or 1-4-2:

[Chemical Formula 1-4-1]

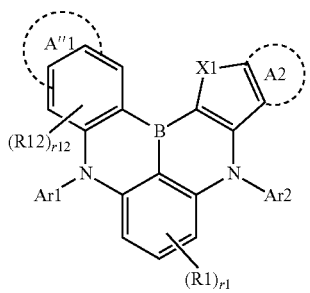

-continued

[Chemical formula 1-4-2]

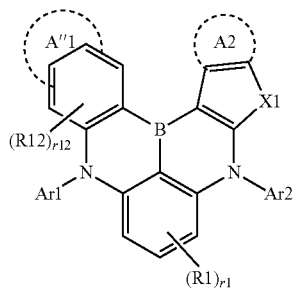

wherein in Chemical Formulae 1-4-1 and 1-4-2,
X1, A2, Ar1, Ar2, R1 and r1 are the same as defined in Chemical Formula 1,
A″1 is a substituted or unsubstituted aliphatic hydrocarbon ring,
R12 is hydrogen; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; or a substituted or unsubstituted heterocyclic group, and
r12 is 1 or 2, and when r12 is 2, the two R12s are the same as or different from each other.

4. The compound of claim 1, wherein the compound of Chemical Formula 1 includes at least one monocyclic or polycyclic fused aliphatic hydrocarbon ring having 3 to 10 carbon atoms substituted with a linear or branched alkyl group having 1 to 30 carbon atoms unsubstituted or substituted with deuterium.

5. The compound of claim 1, wherein A1 is a substituted or unsubstituted monocyclic or polycyclic heteroring having 2 to 30 carbon atoms; a substituted or unsubstituted monocyclic or polycyclic aromatic hydrocarbon ring having 6 to 30 carbon atoms; a substituted or unsubstituted monocyclic or polycyclic aliphatic hydrocarbon ring having 3 to 30 carbon atoms; or a substituted or unsubstituted fused ring of monocyclic or polycyclic aromatic hydrocarbon ring having 6 to 30 carbon atoms and monocyclic or polycyclic aliphatic hydrocarbon ring having 3 to 30 carbon atoms,
A2 is a substituted or unsubstituted monocyclic or polycyclic aliphatic hydrocarbon ring having 3 to 30 carbon atoms; or a substituted or unsubstituted fused ring of monocyclic or polycyclic aromatic hydrocarbon ring having 6 to 30 carbon atoms and monocyclic or polycyclic aliphatic hydrocarbon ring having 6 to 30 carbon atoms,
Ar1 and Ar2 are the same as or different from each other, and each independently a substituted or unsubstituted monocyclic or polycyclic aryl group having 6 to 30 carbon atoms; a substituted or unsubstituted monocyclic or polycyclic heterocyclic group having 2 to 30 carbon atoms; or a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms, and
R1 is hydrogen; a substituted or unsubstituted linear or branched alkyl group having 1 to 30 carbon atoms; a substituted or unsubstituted monocyclic or polycyclic cycloalkyl group having 3 to 30 carbon atoms; a substituted or unsubstituted amine group; a substituted or unsubstituted monocyclic or polycyclic aryl group having 6 to 30 carbon atoms; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a monocyclic or polycyclic heterocyclic group having 2 to 30 carbon atoms.

6. A compound selected from the followings:

1229
-continued
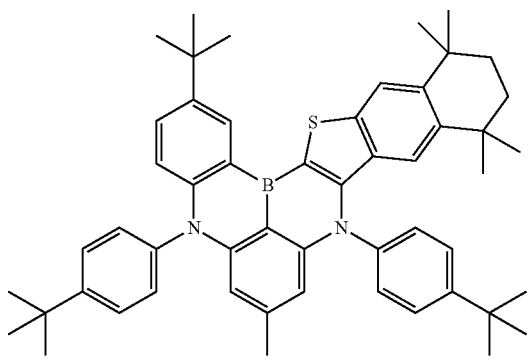
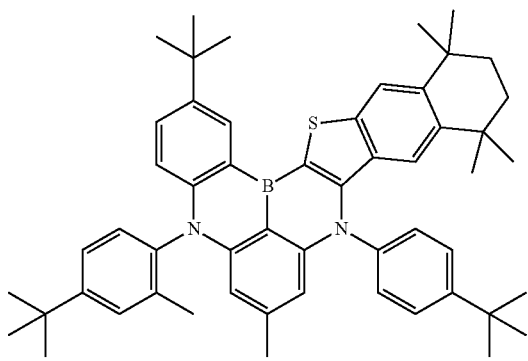
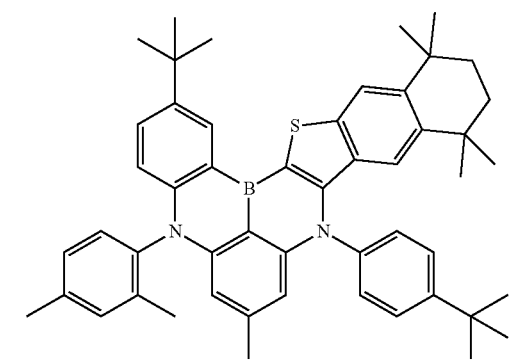
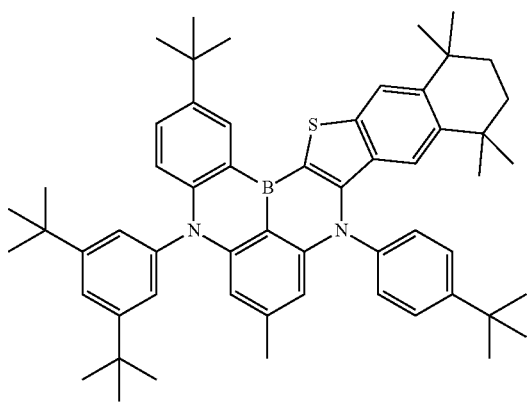
1230
-continued
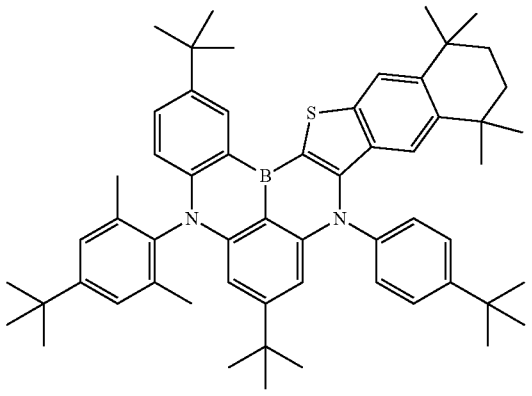
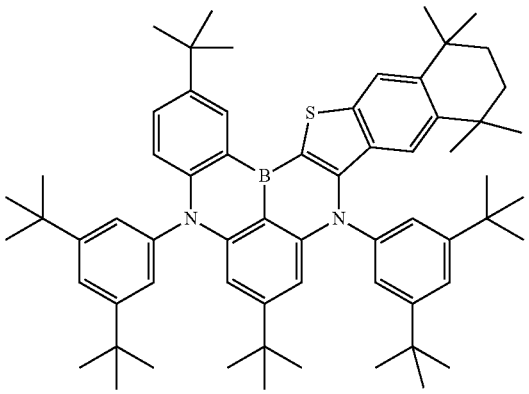
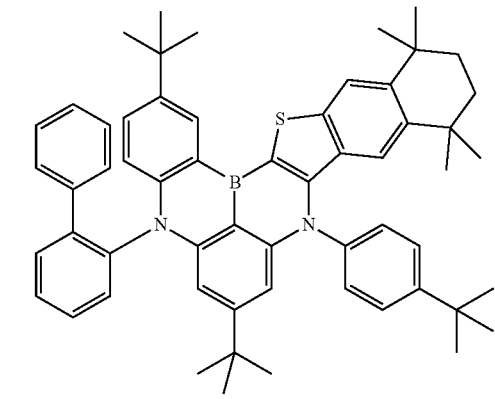
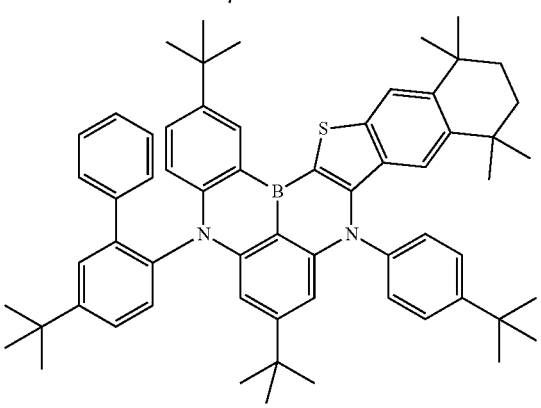

1231
-continued
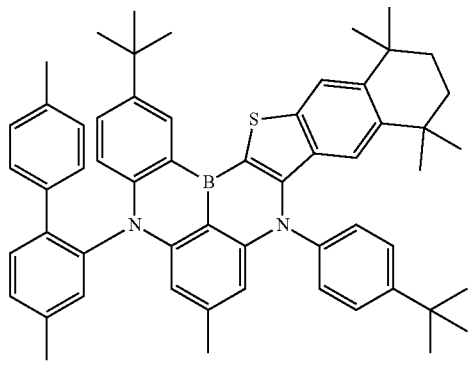
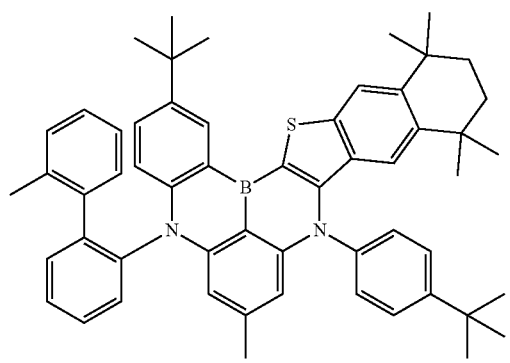
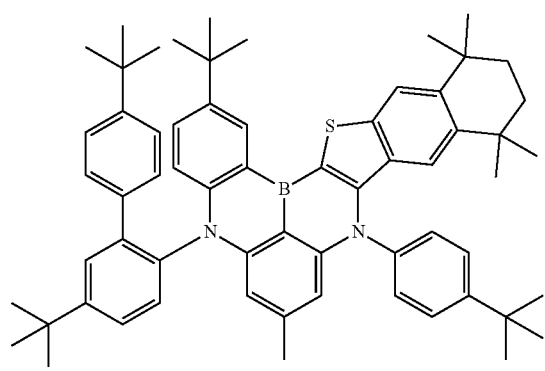
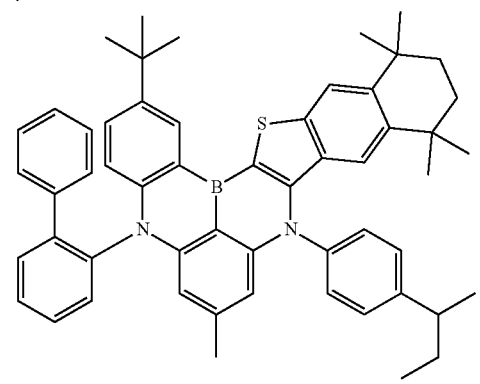
1232
-continued
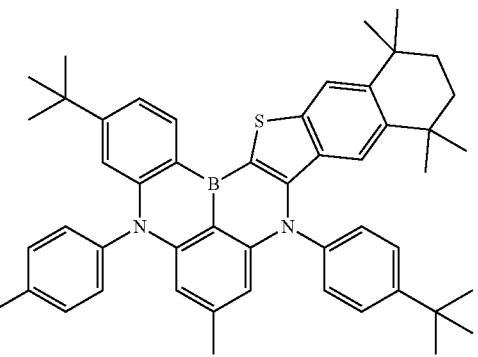
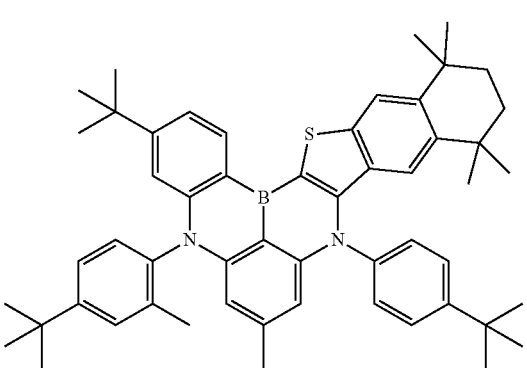
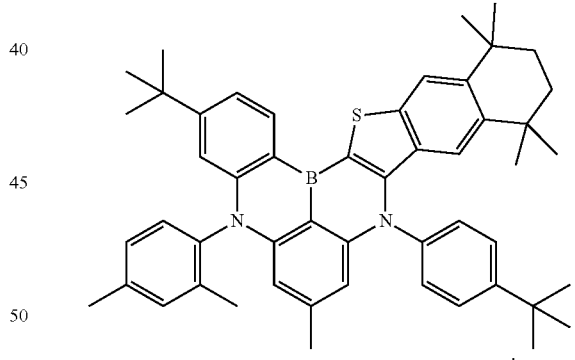
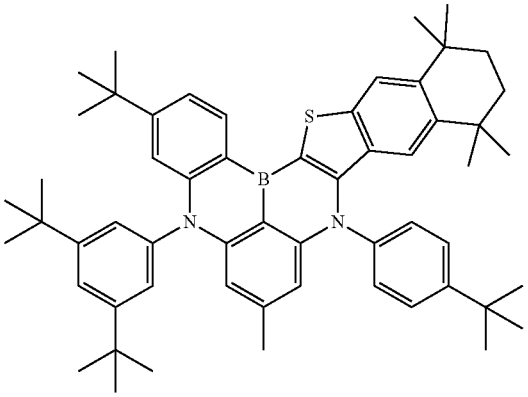

1233
-continued
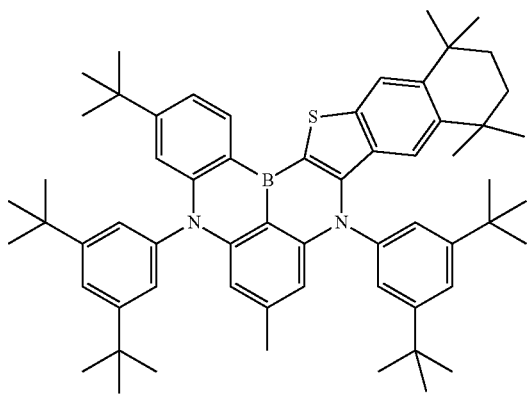
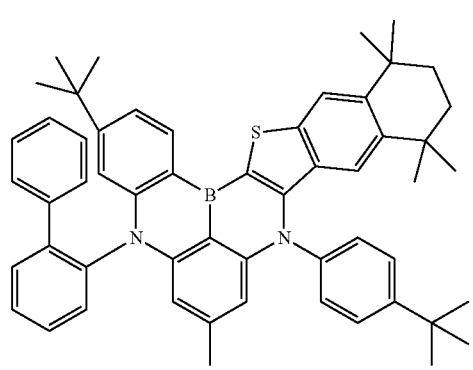
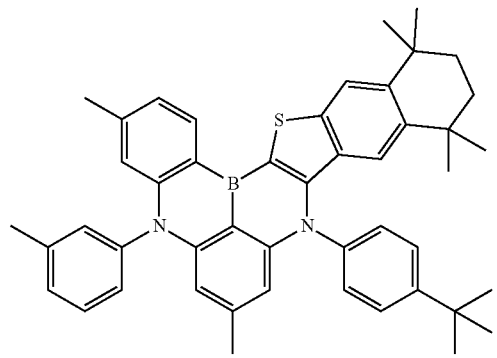
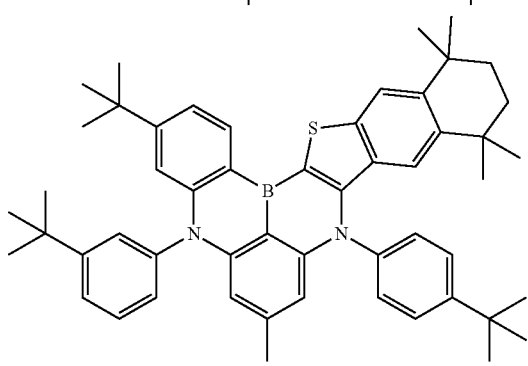
1234
-continued
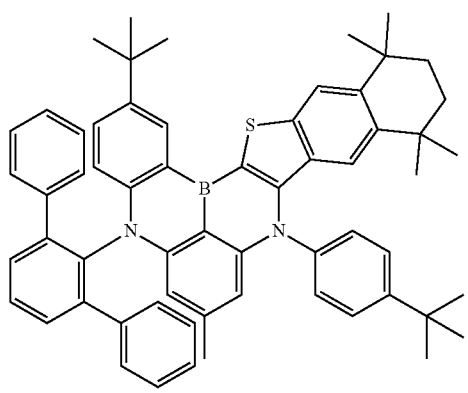
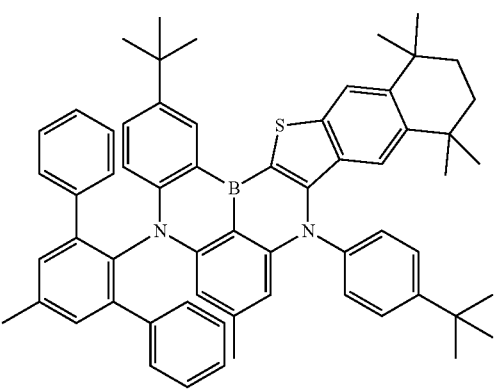
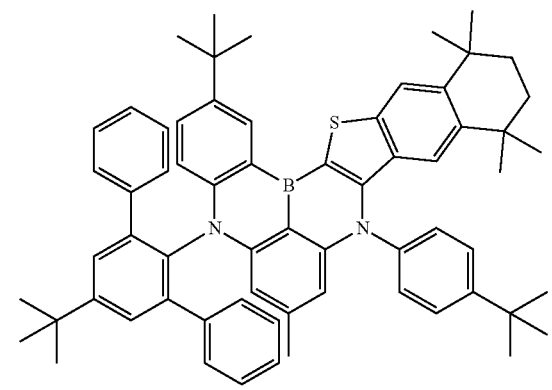
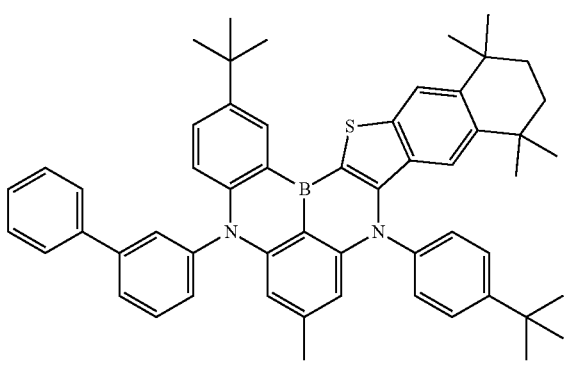

1235
-continued
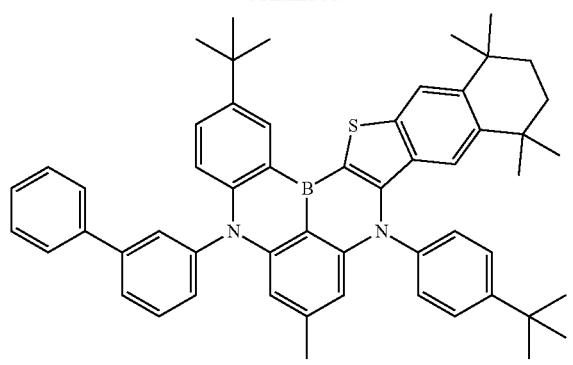
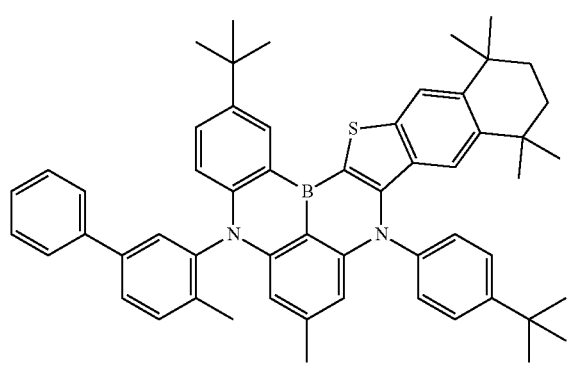
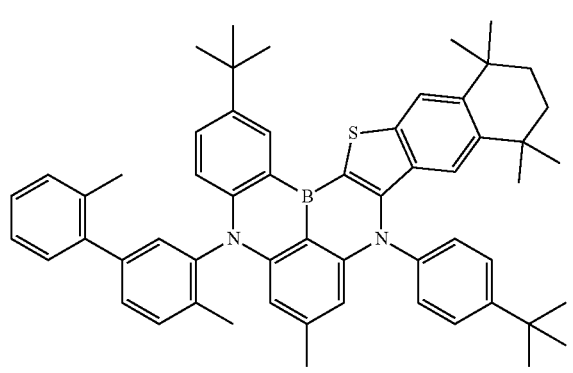
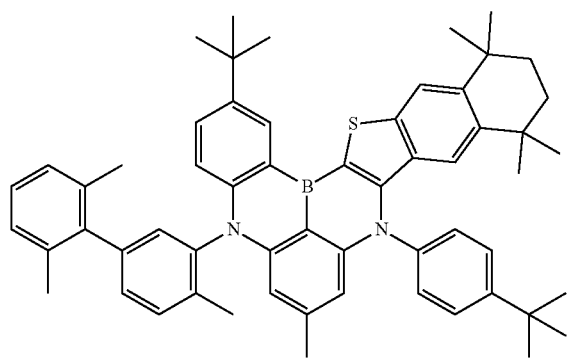
1236
-continued
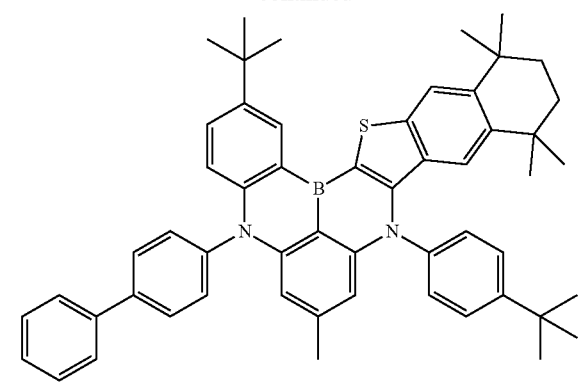
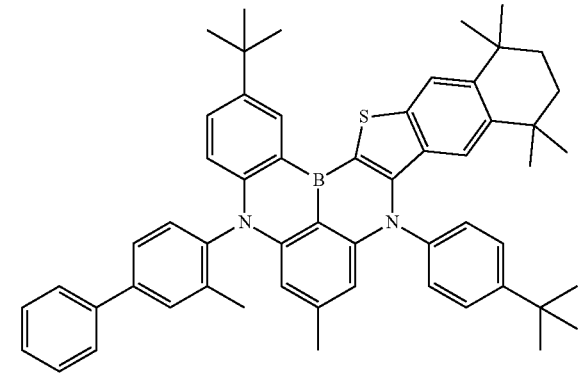
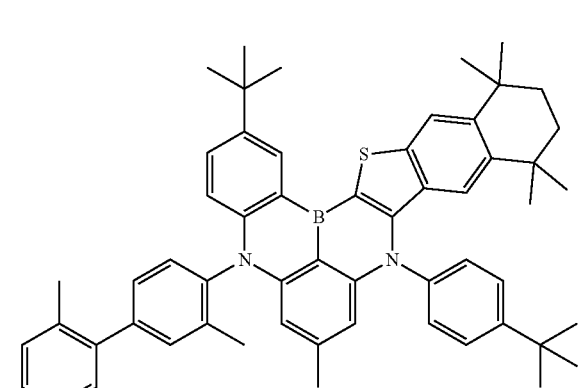
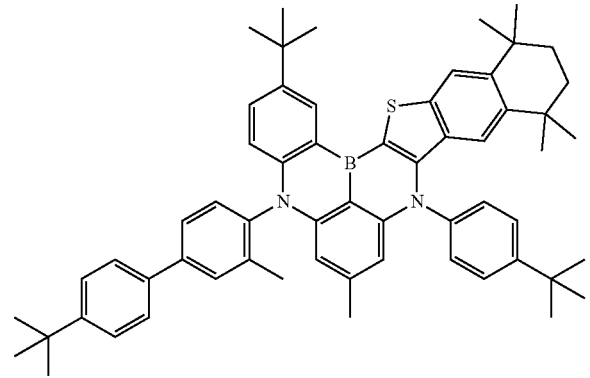

1237
-continued
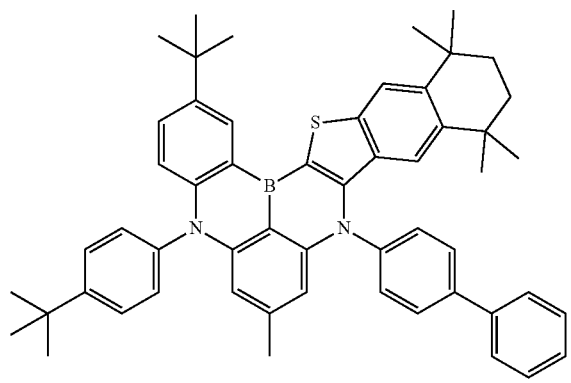
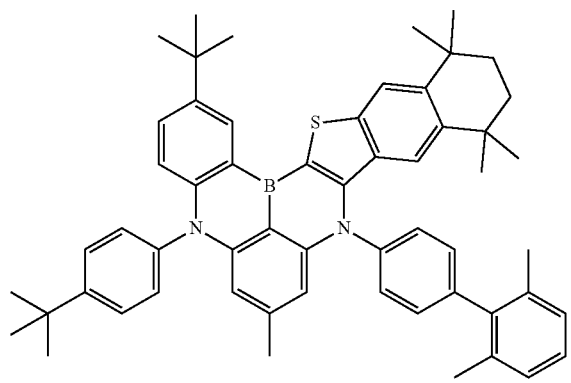

1238
-continued
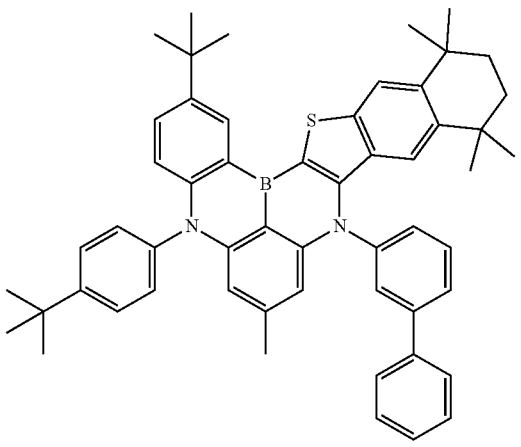
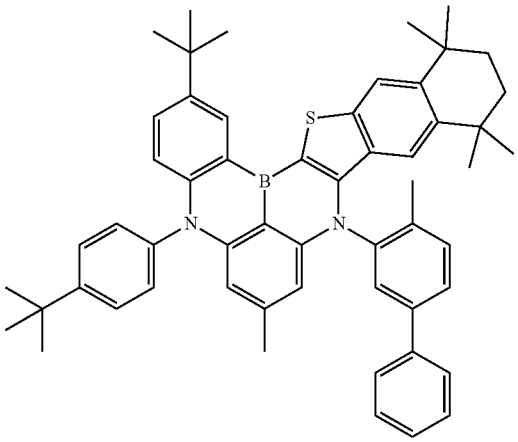

1239
-continued
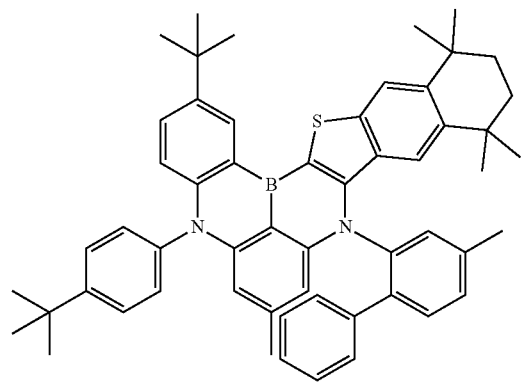
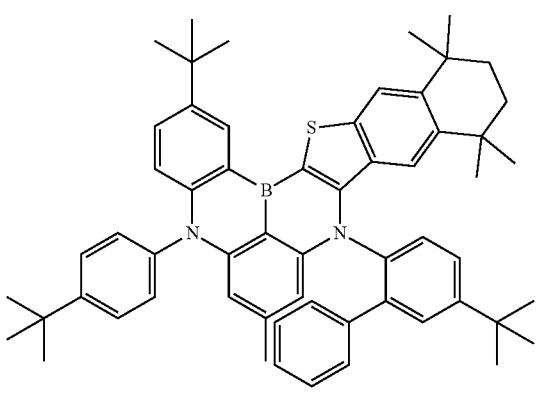
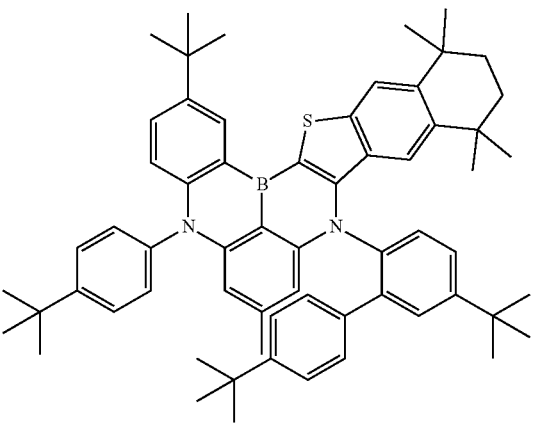
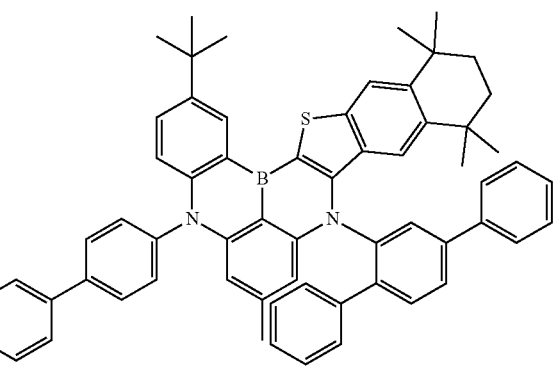
1240
-continued
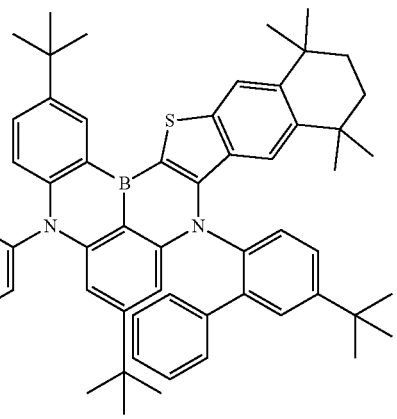
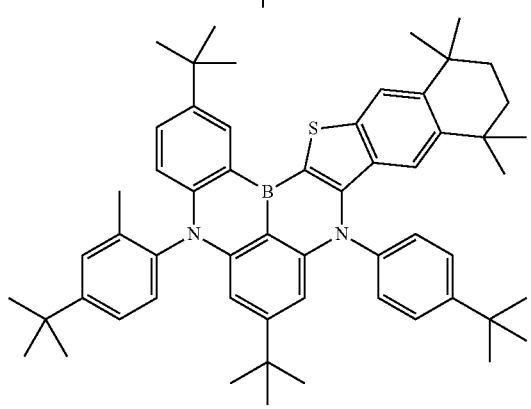
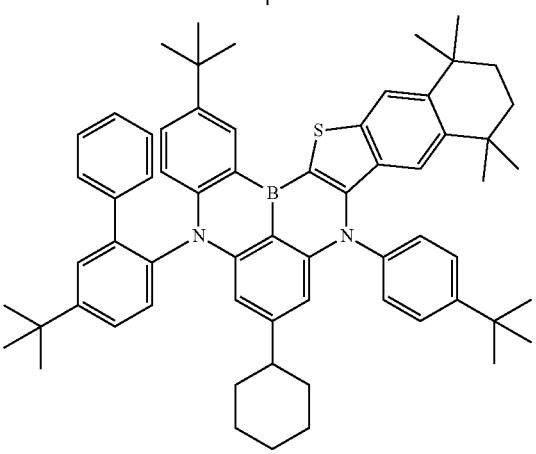
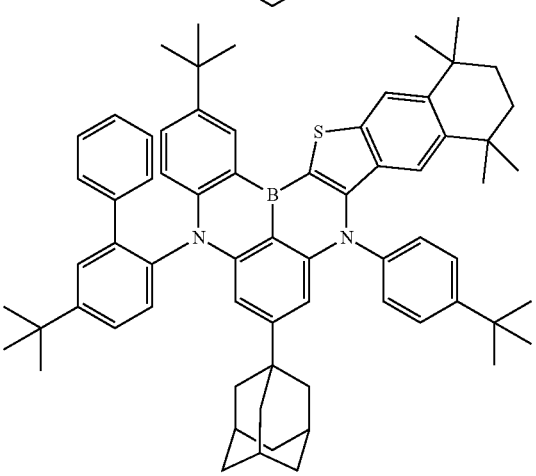

1241
-continued
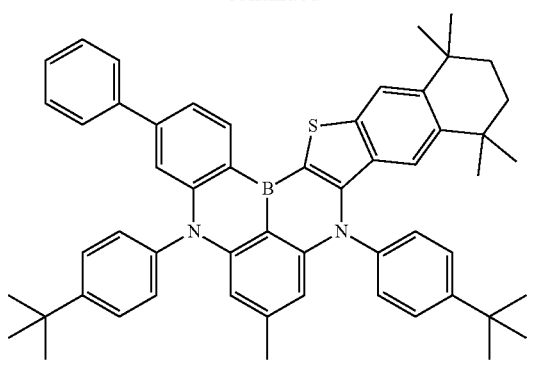
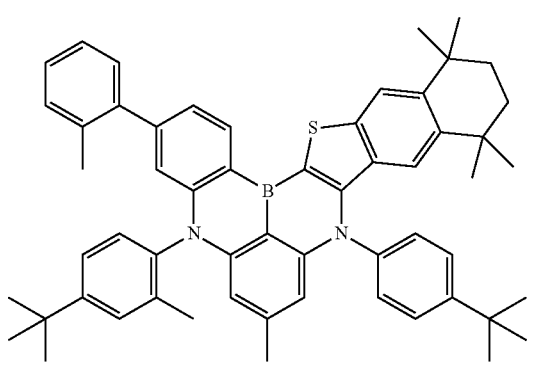
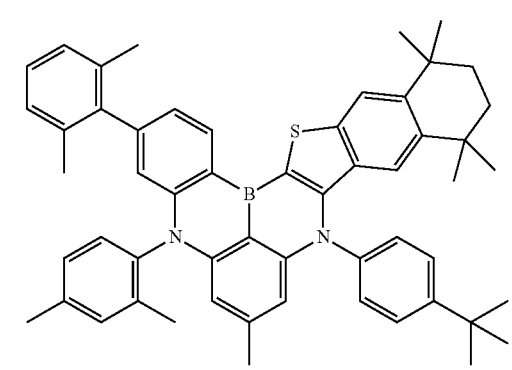
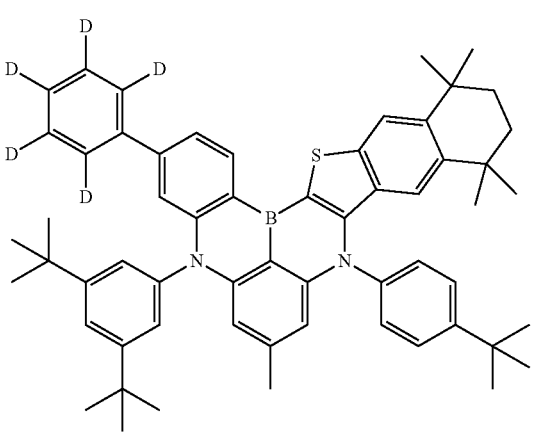
1242
-continued
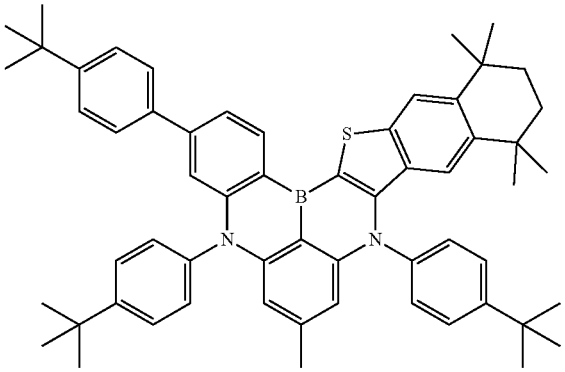
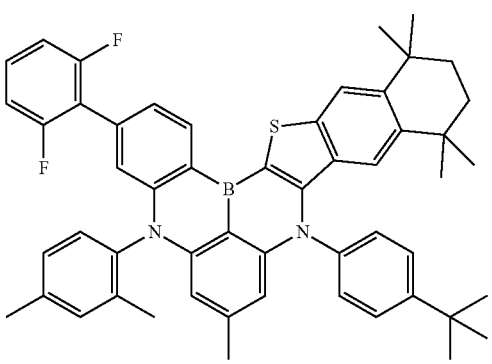
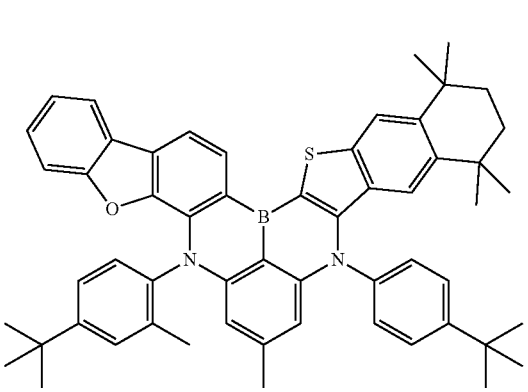
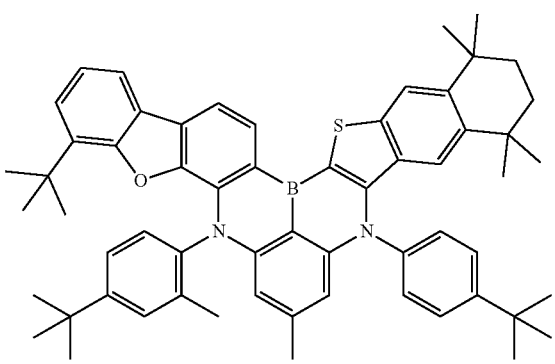

1243
-continued
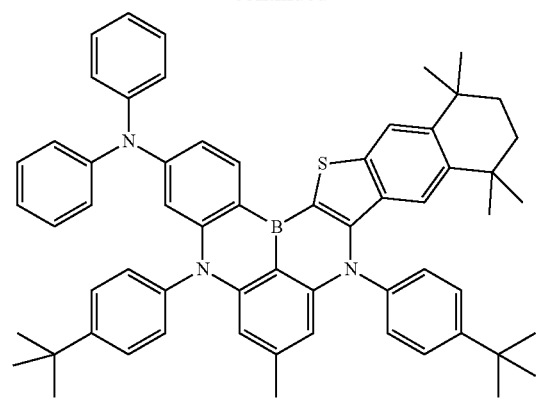
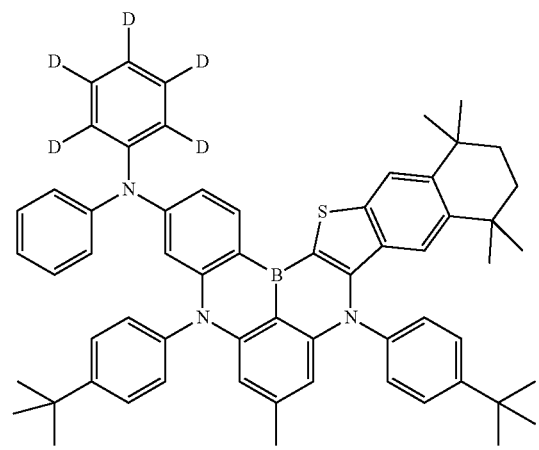
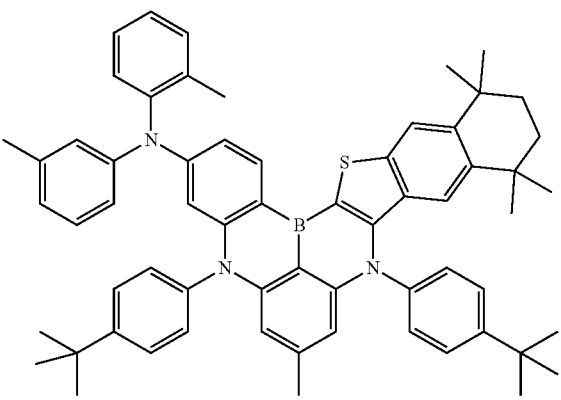
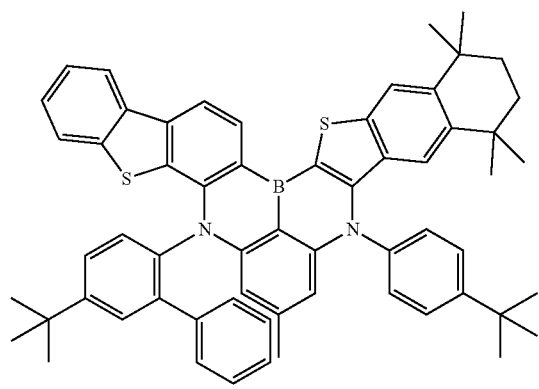
1244
-continued
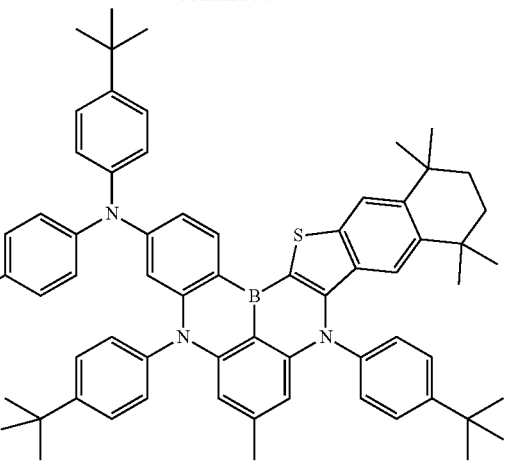
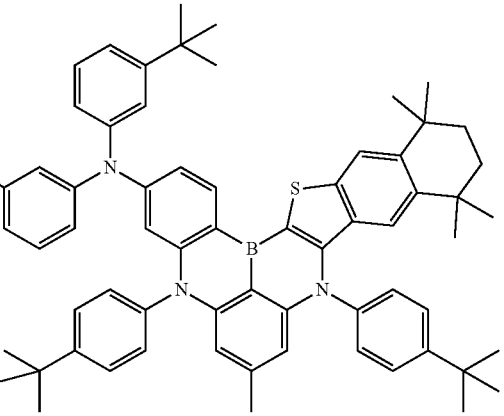
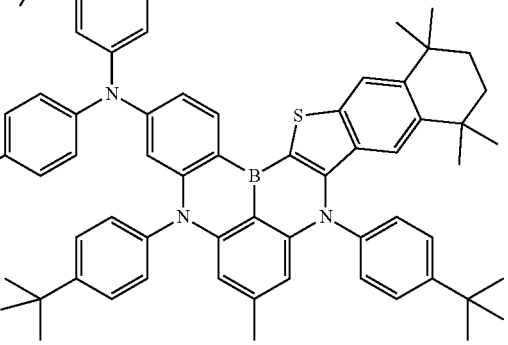

1245
-continued
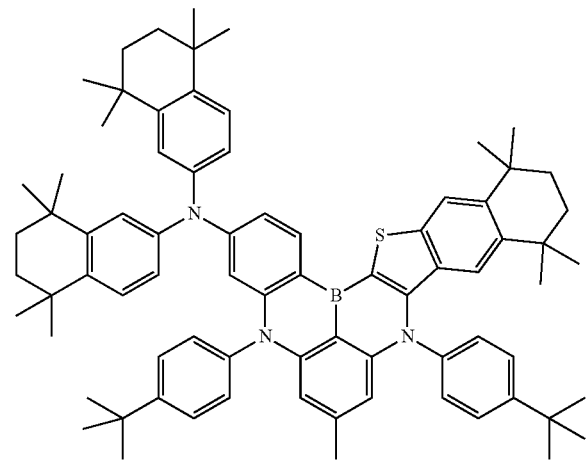
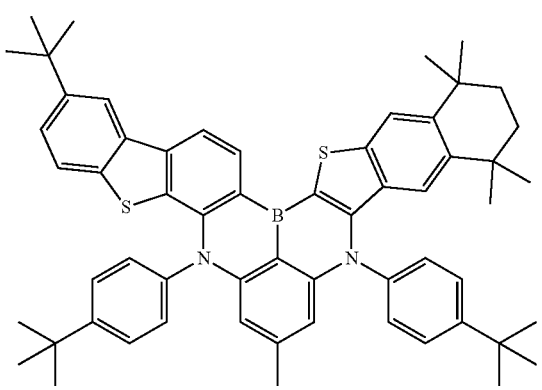
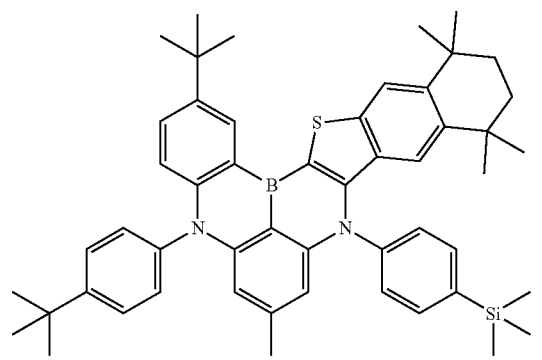
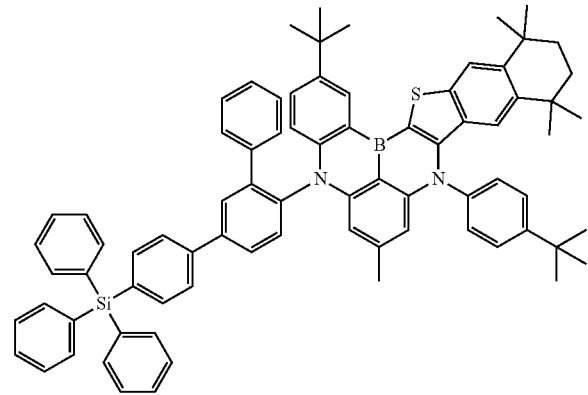
1246
-continued
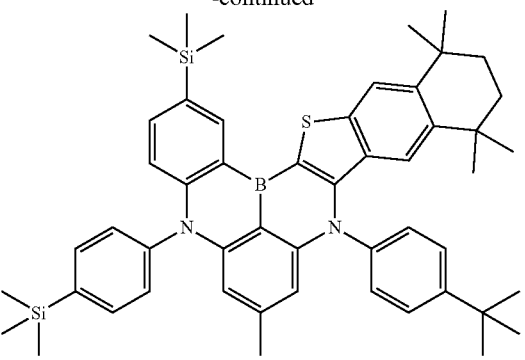
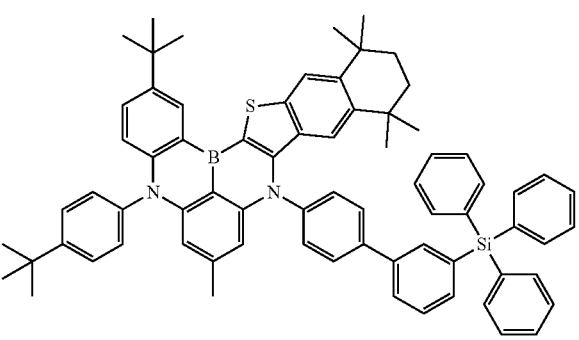
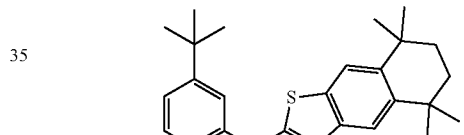
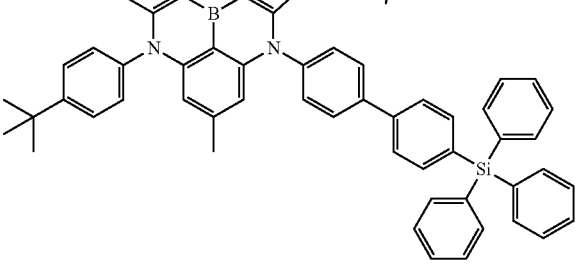
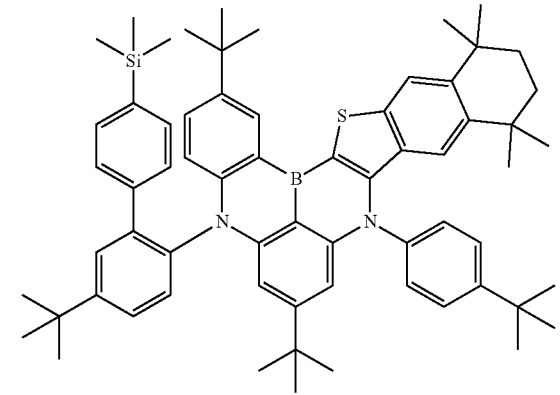

1247
-continued
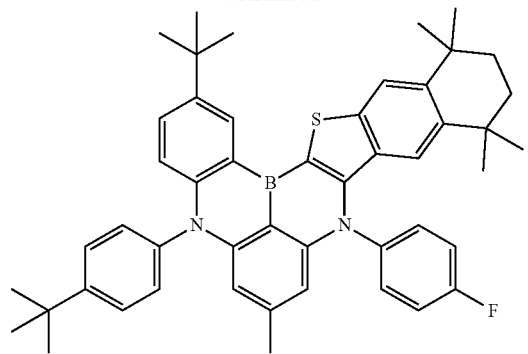
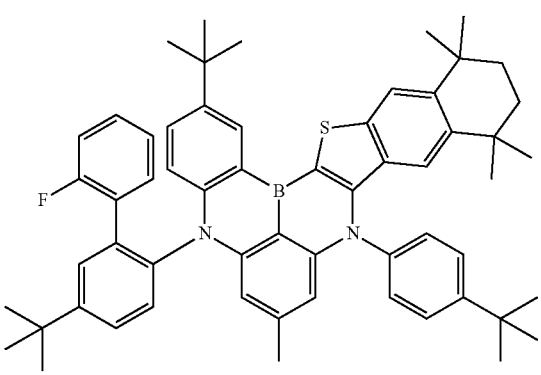
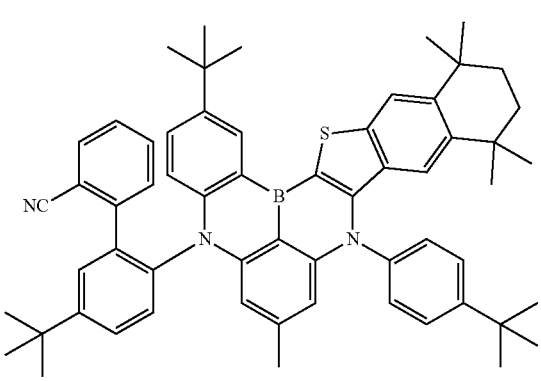
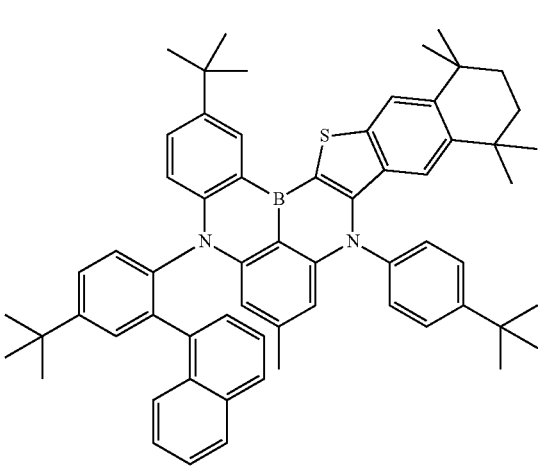
1248
-continued
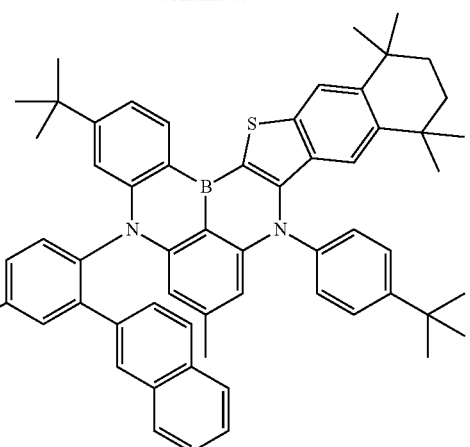

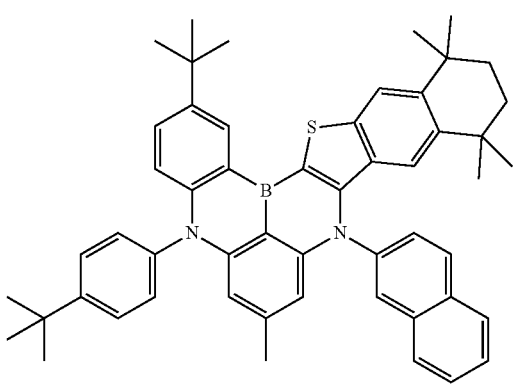
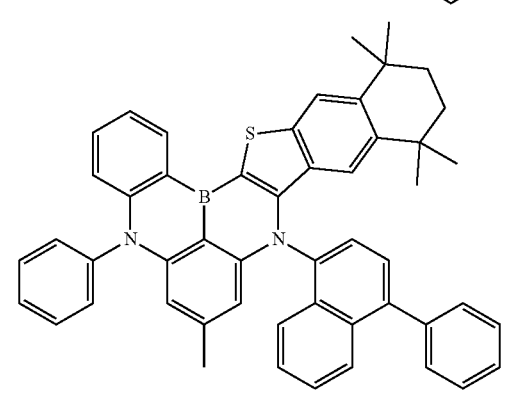

1249
-continued
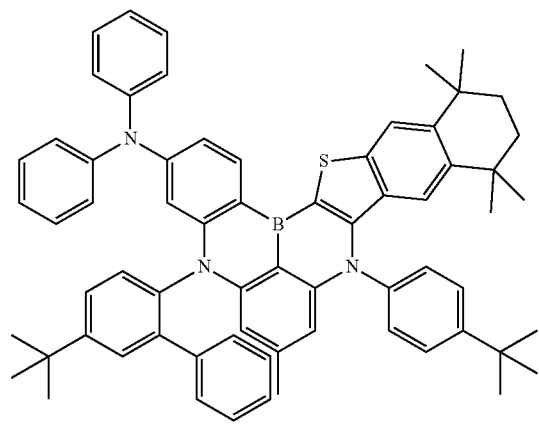
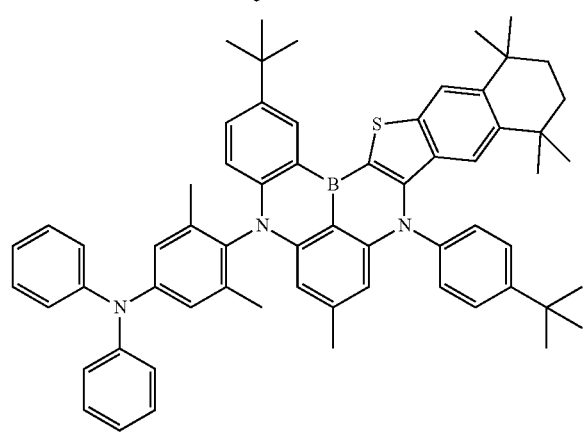
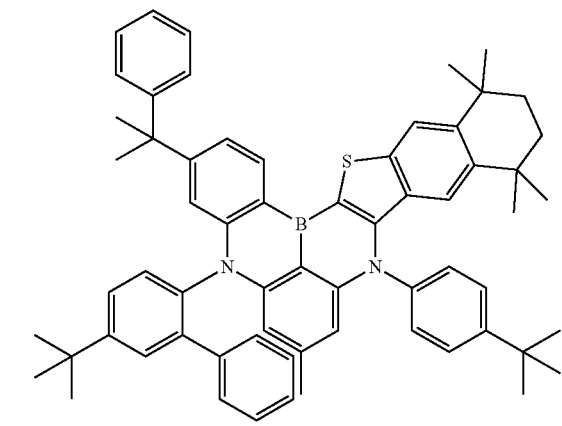
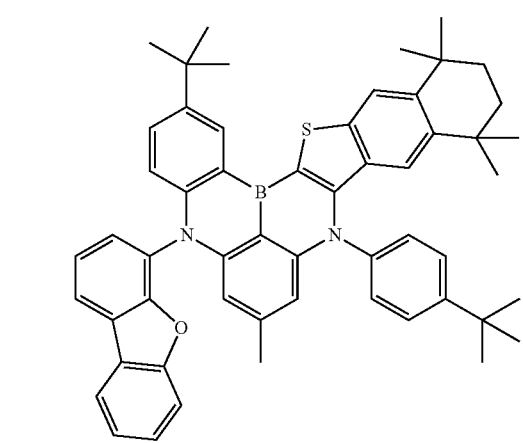
1250
-continued
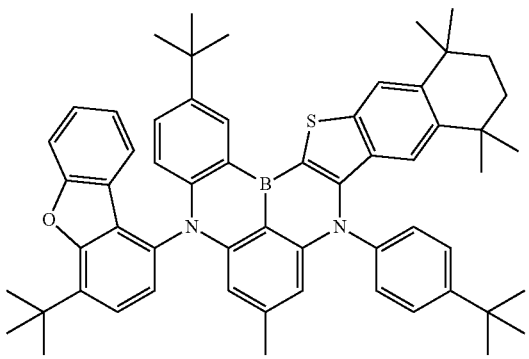
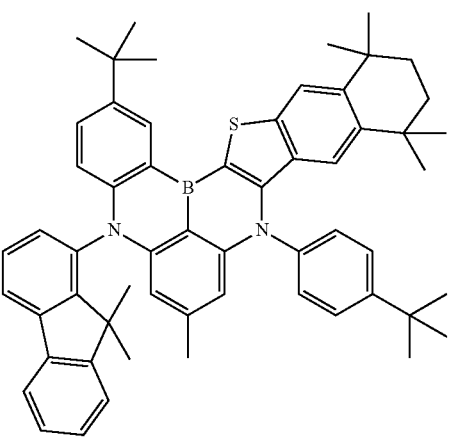
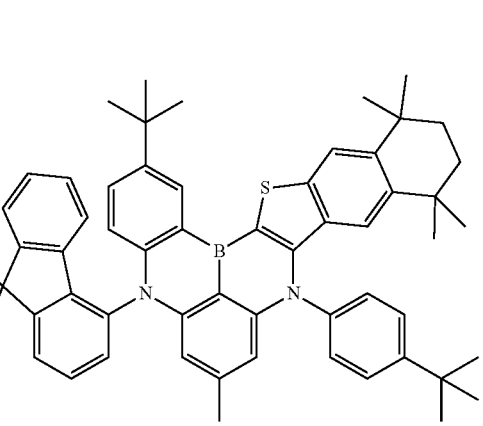
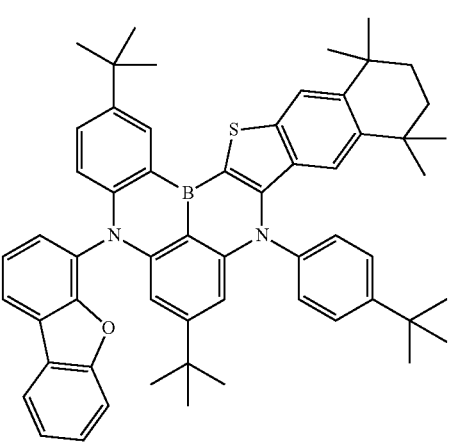

1251
-continued
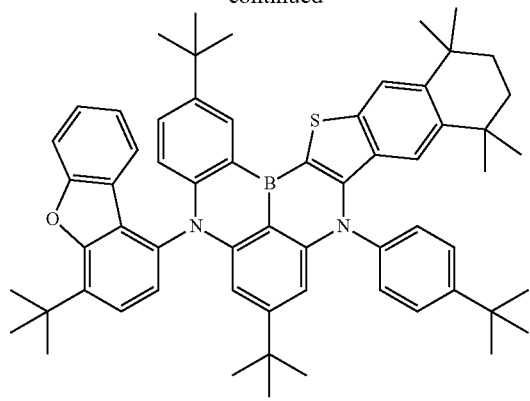
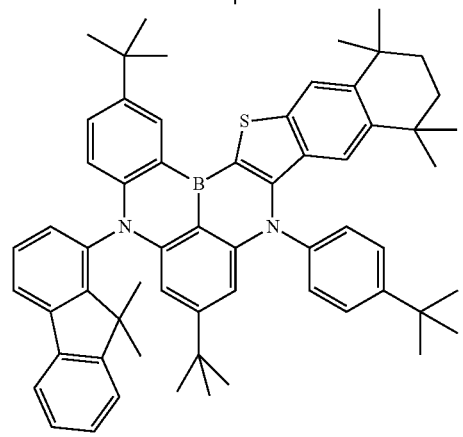
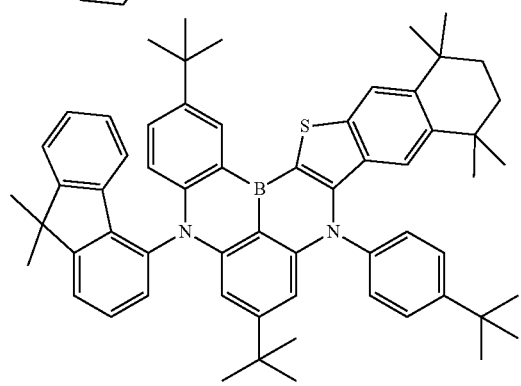
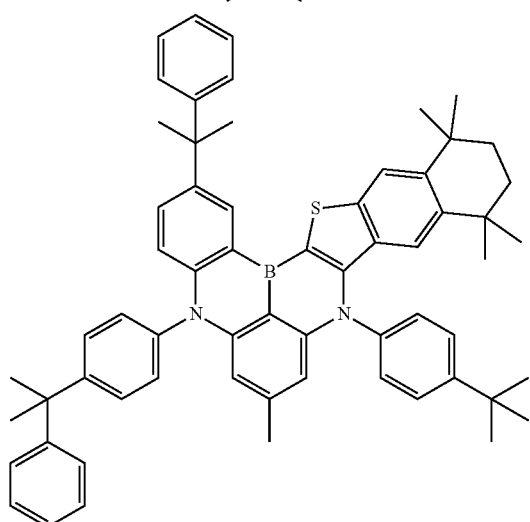
1252
-continued
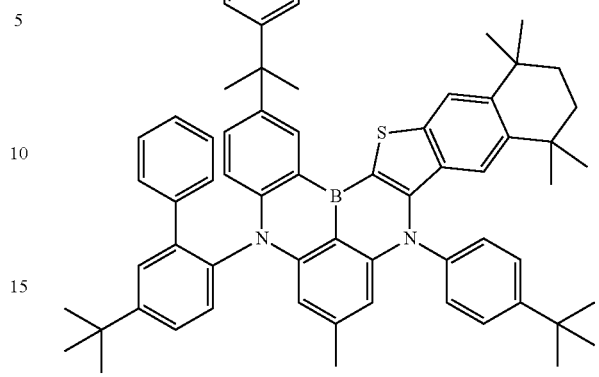
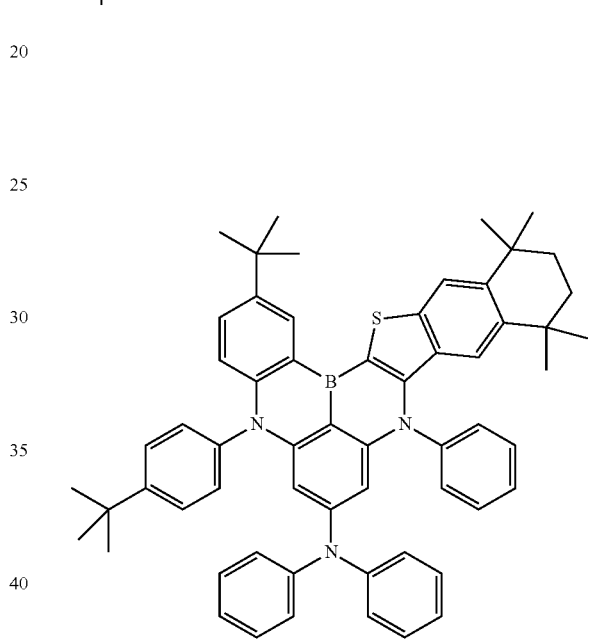
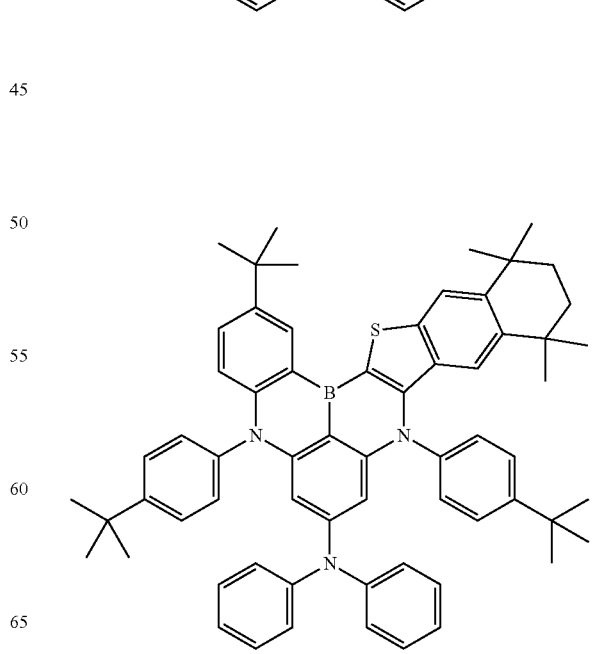

1253
-continued
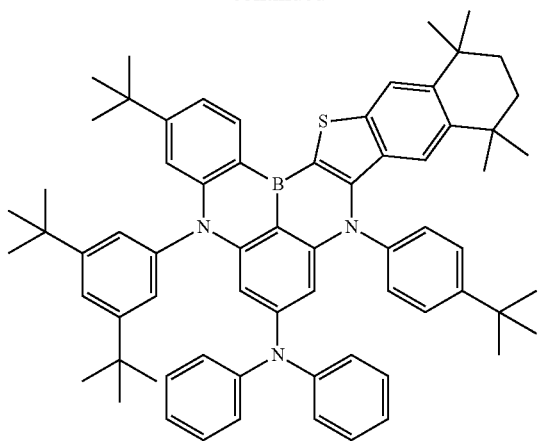
1254
-continued
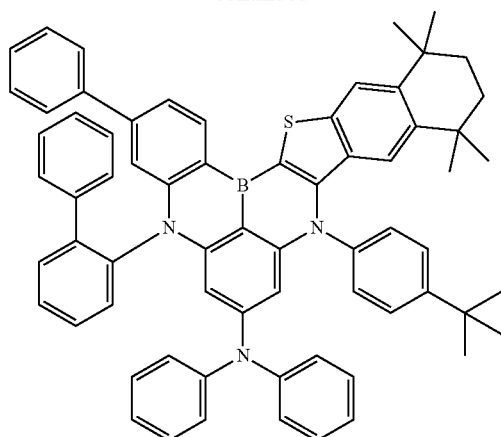
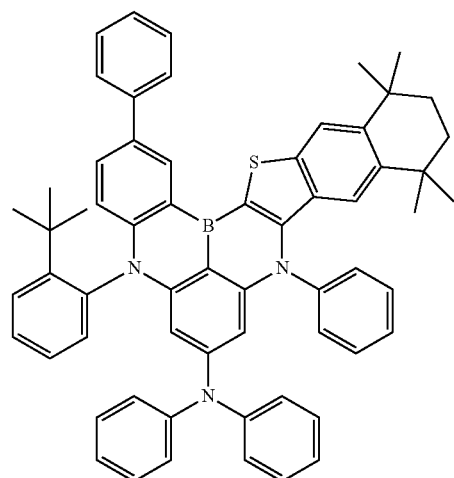
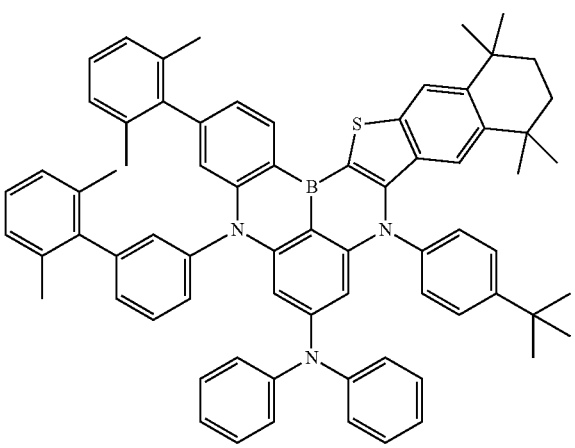
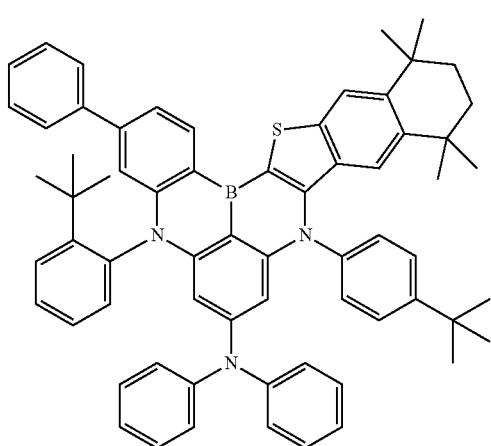
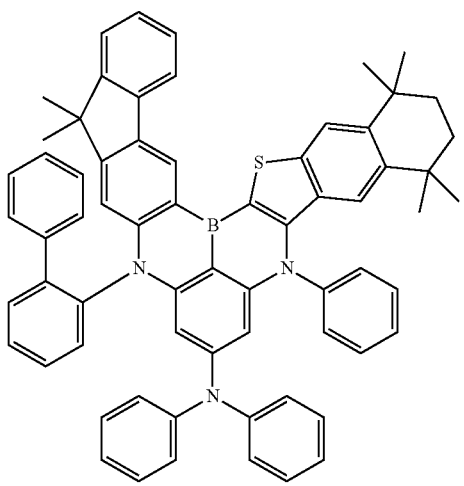

1255
-continued
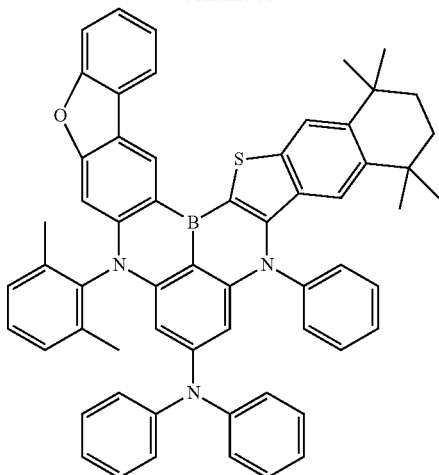
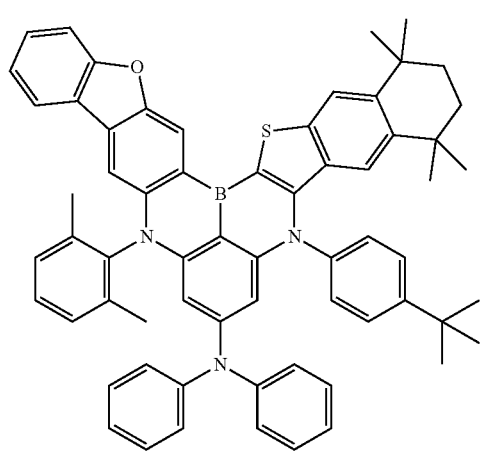
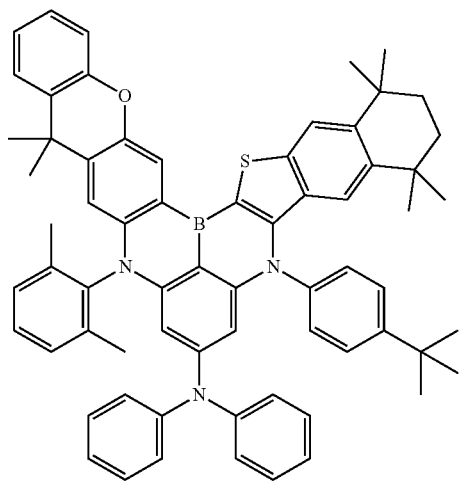
1256
-continued
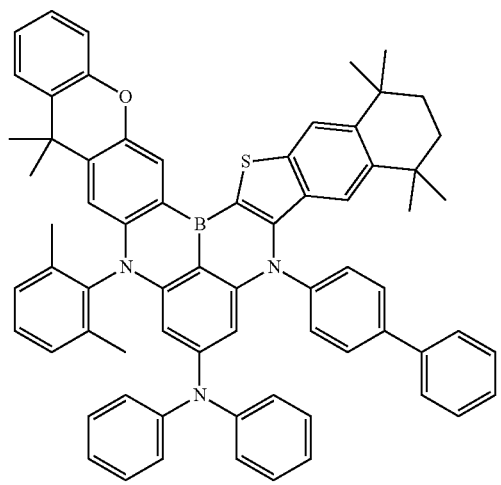
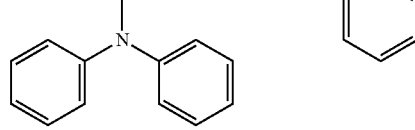
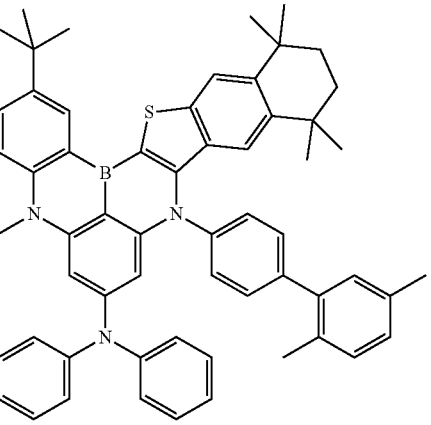

1257
-continued
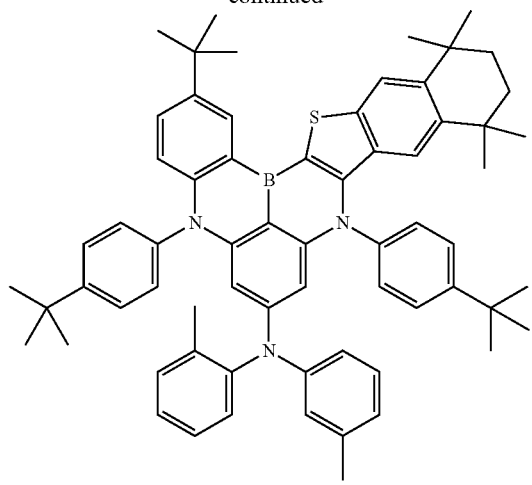
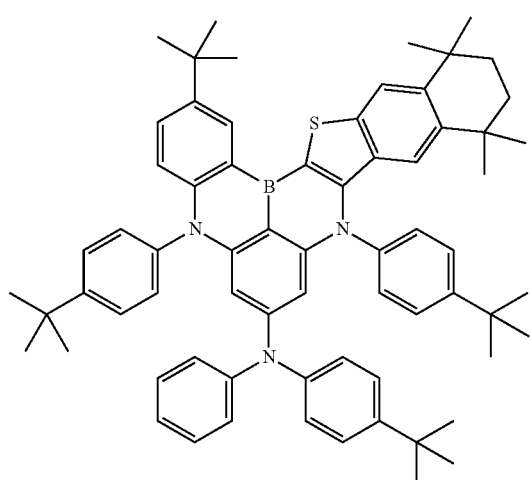
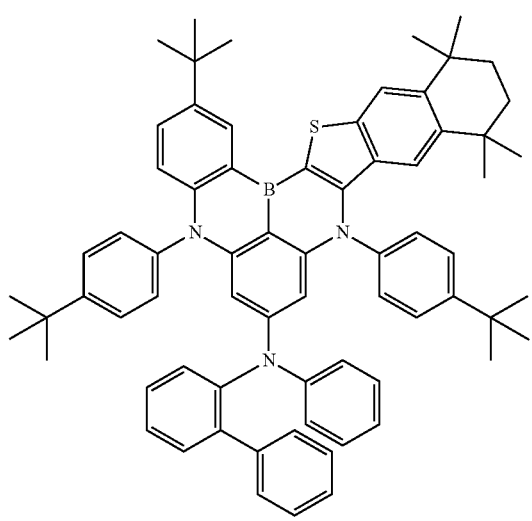
1258
-continued
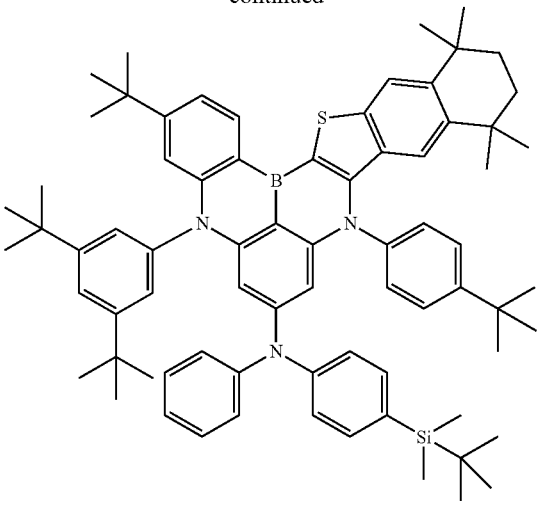
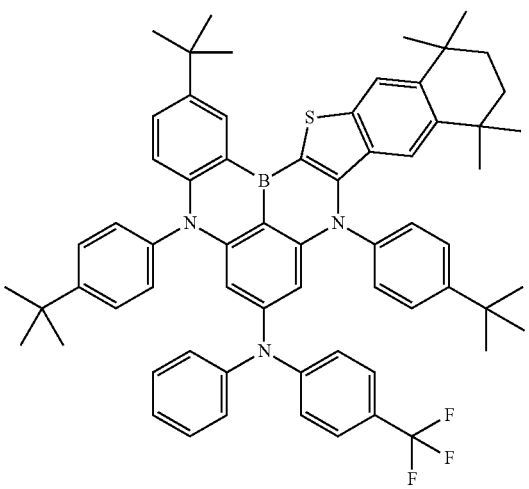
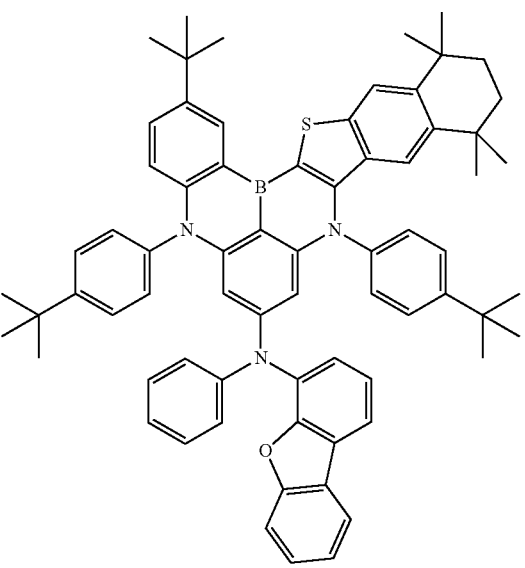

1259
-continued
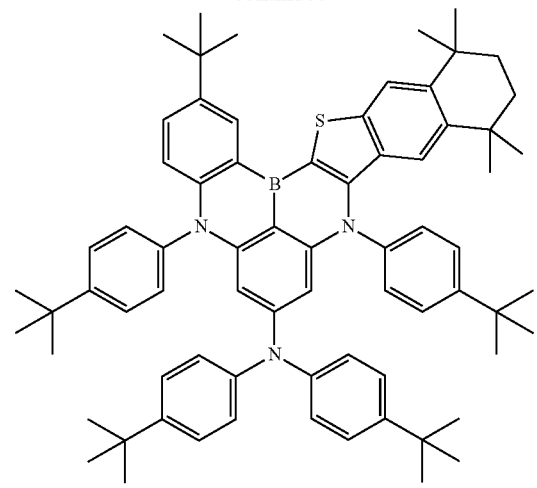
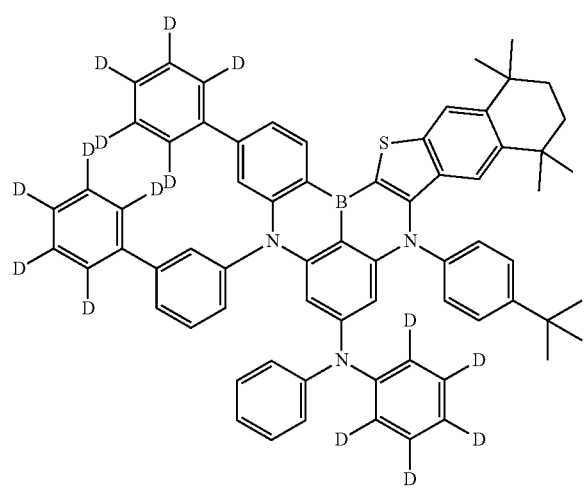
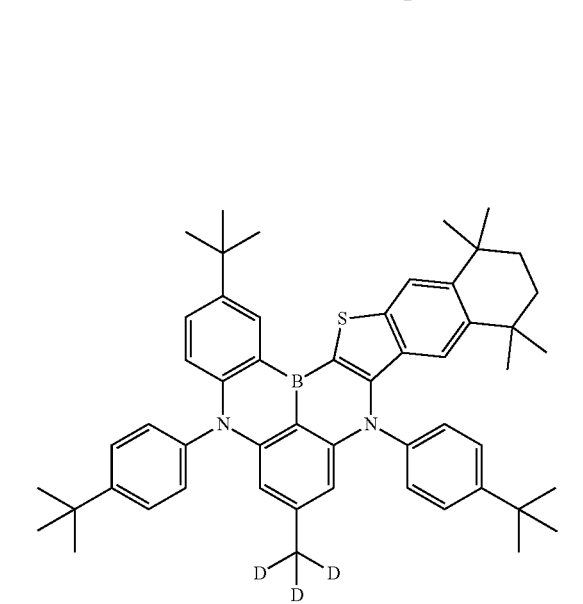
1260
-continued
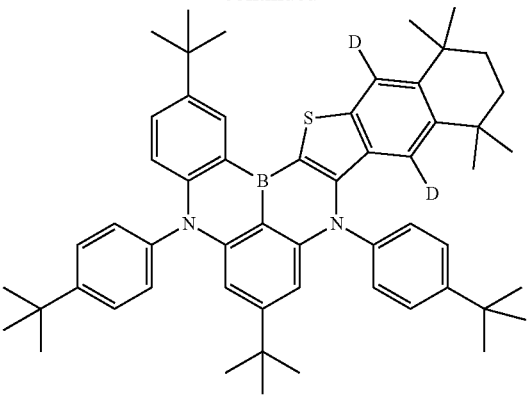
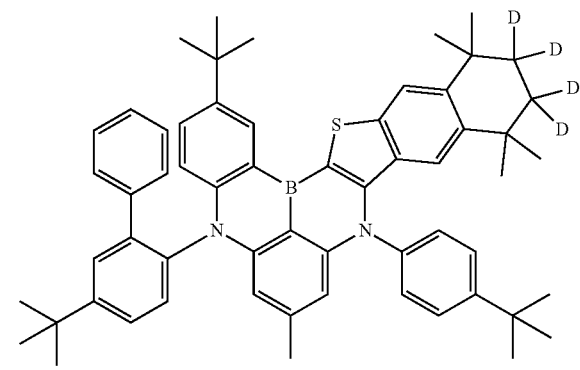
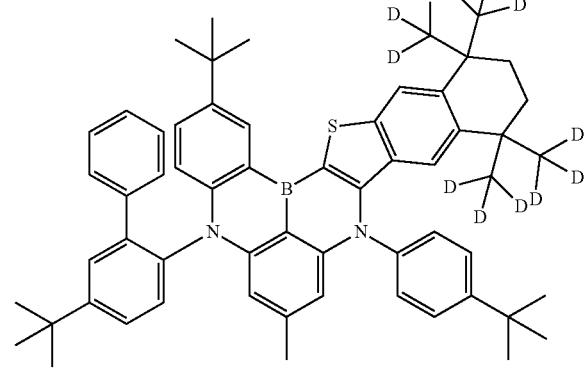
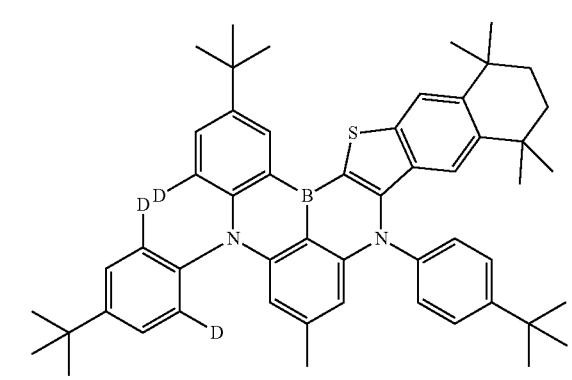

1261
-continued
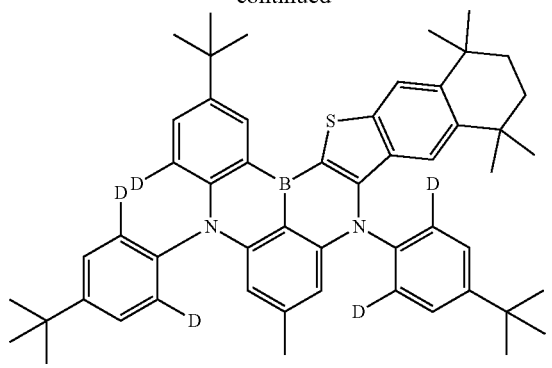
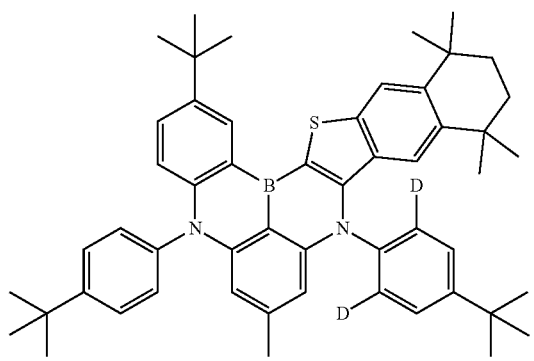
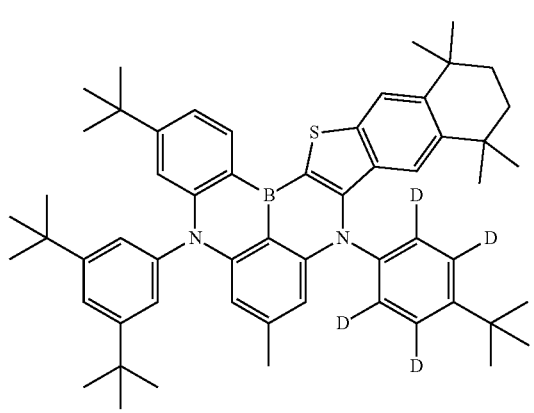
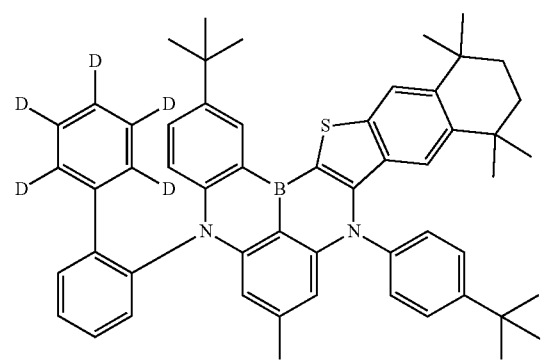
1262
-continued
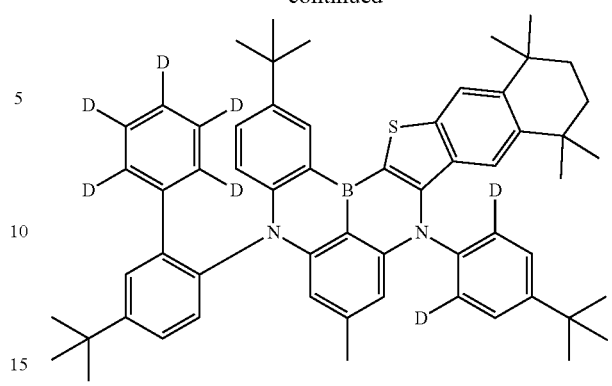
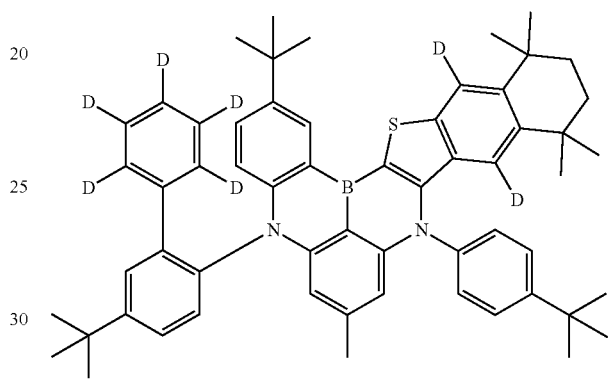
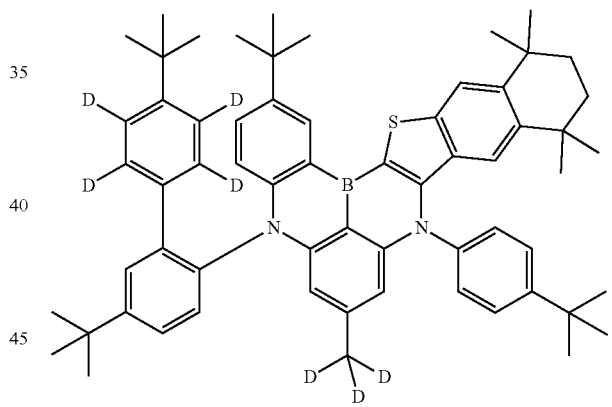
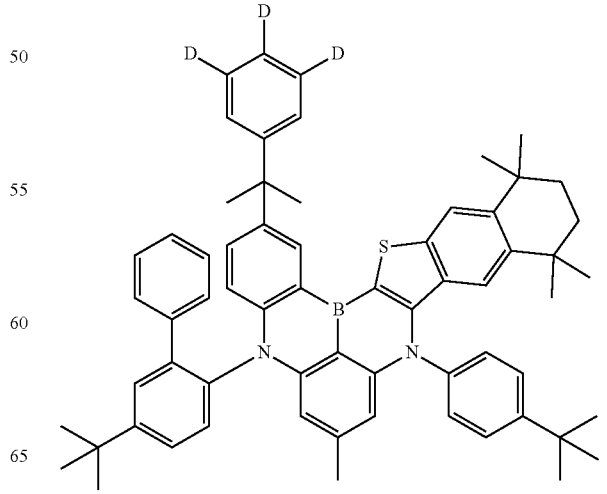

1263
-continued
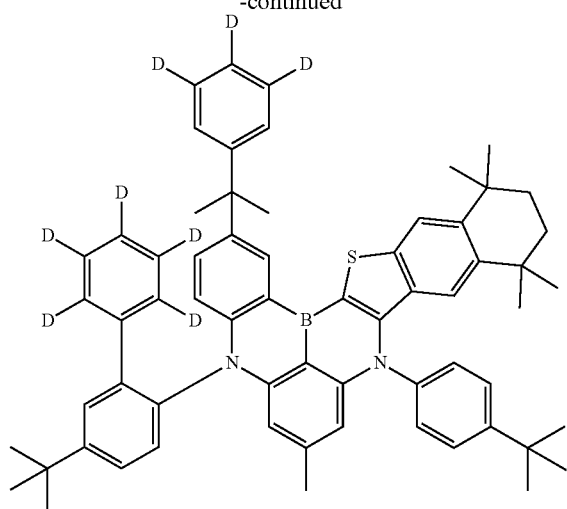
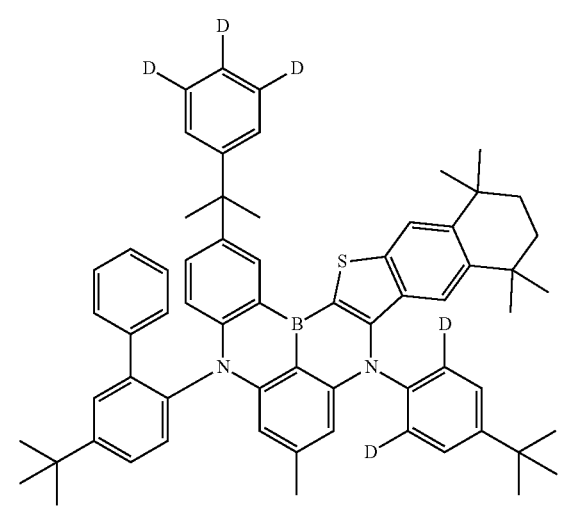
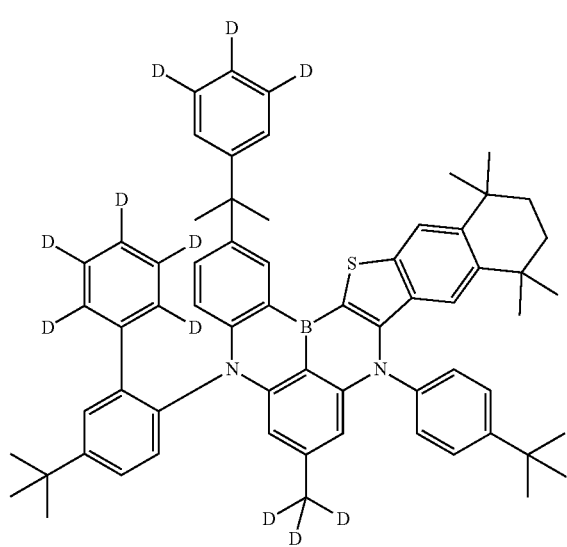
1264
-continued
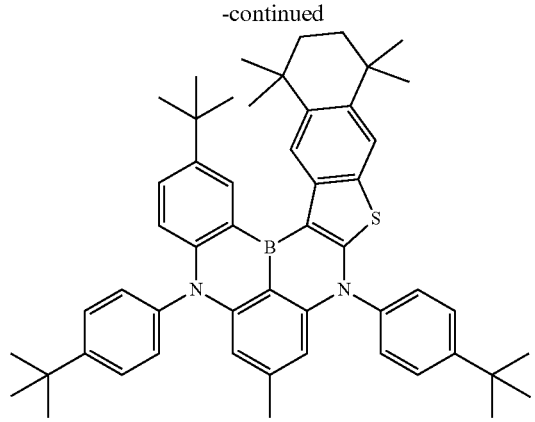
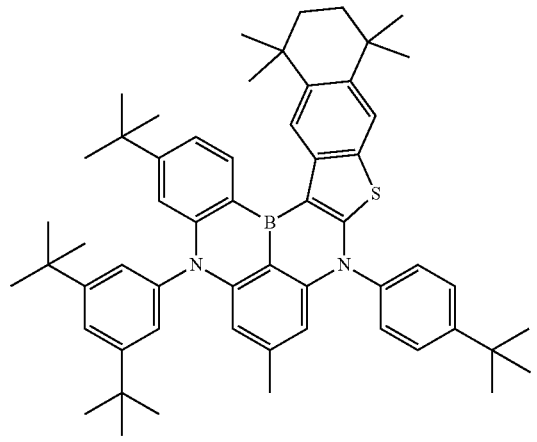
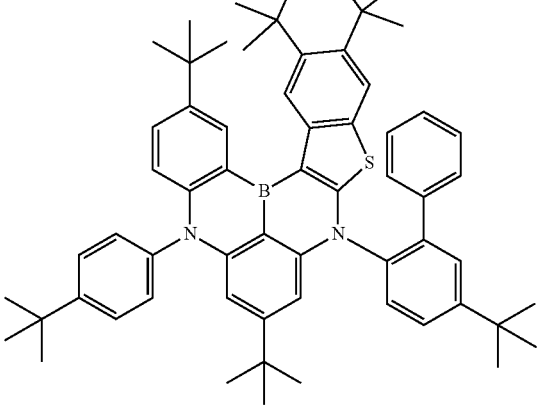

1265
-continued
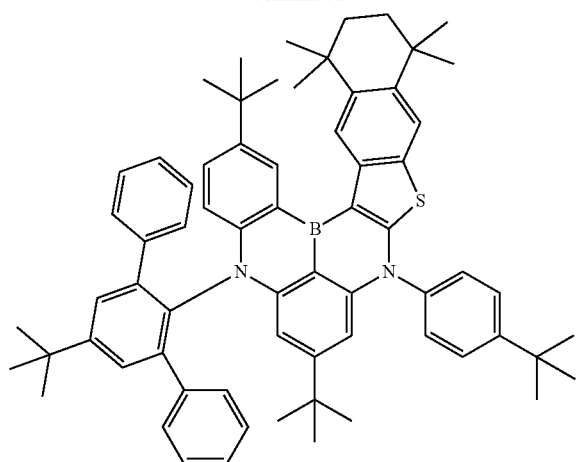
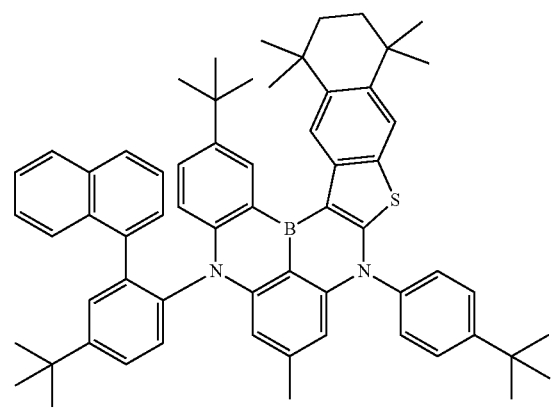
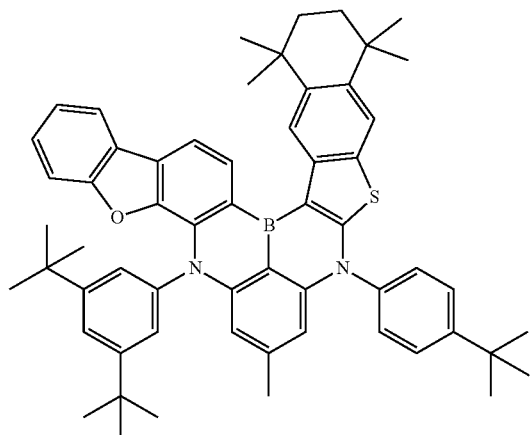
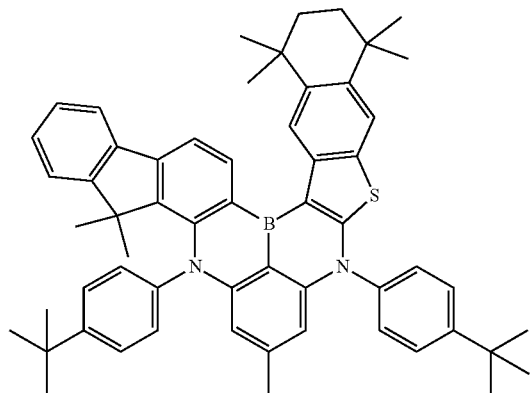
1266
-continued
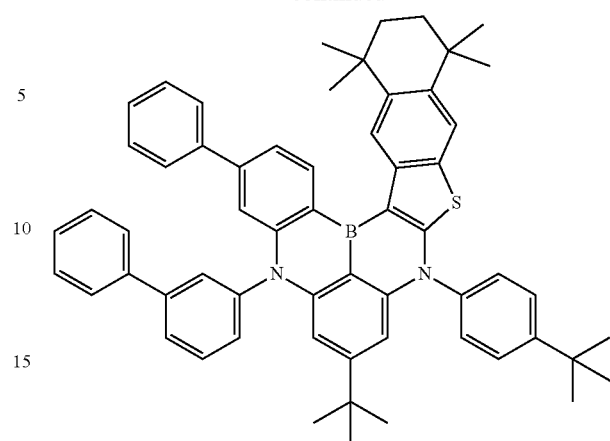
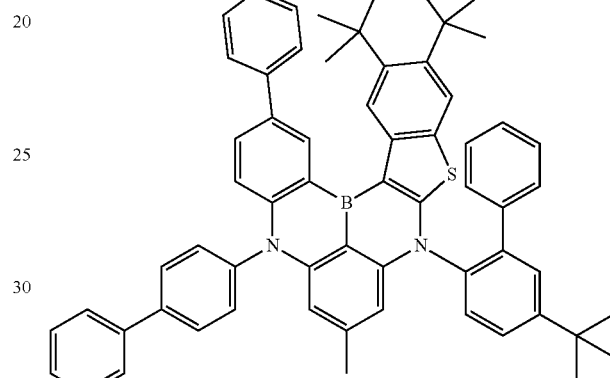
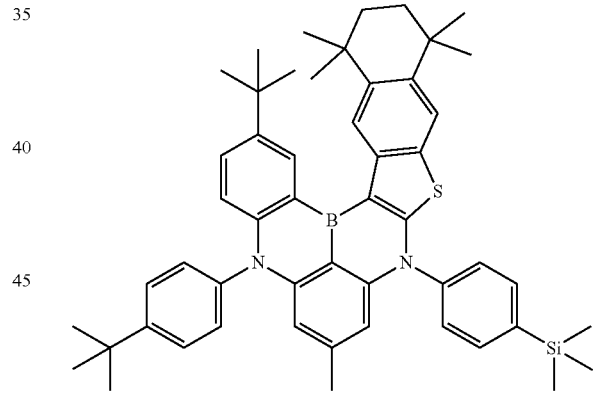
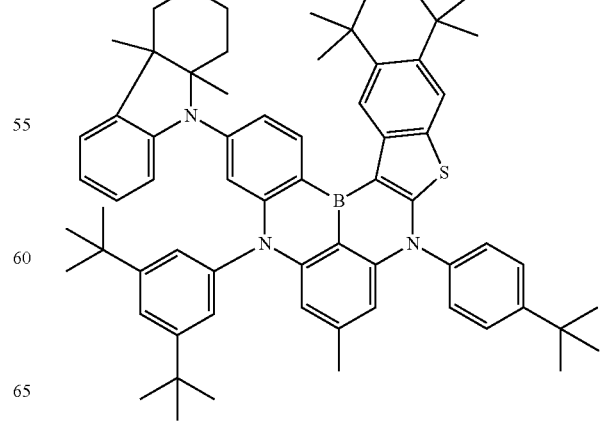

1267
-continued
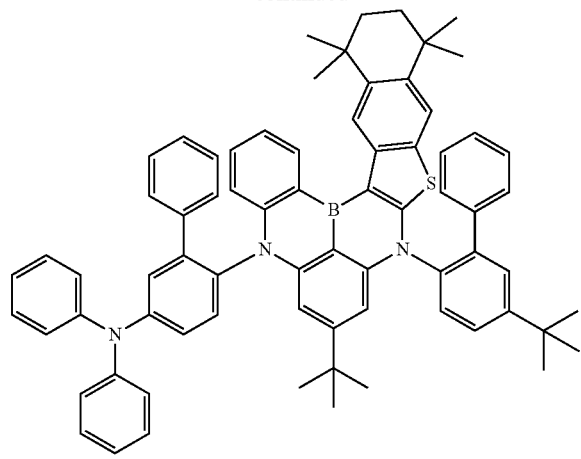
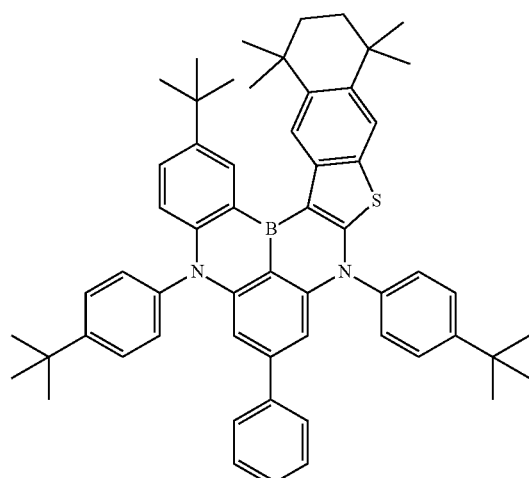
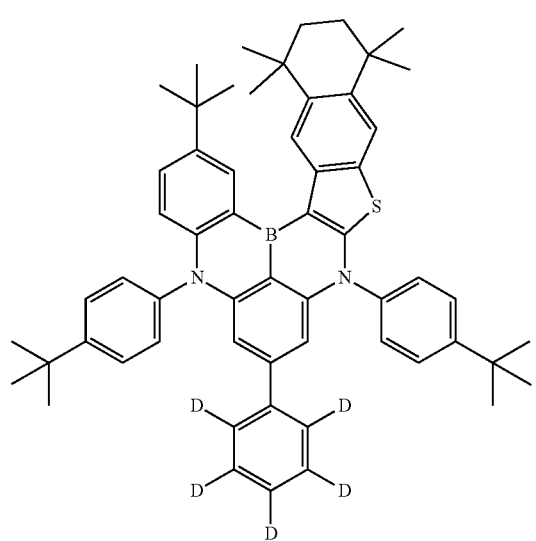
1268
-continued
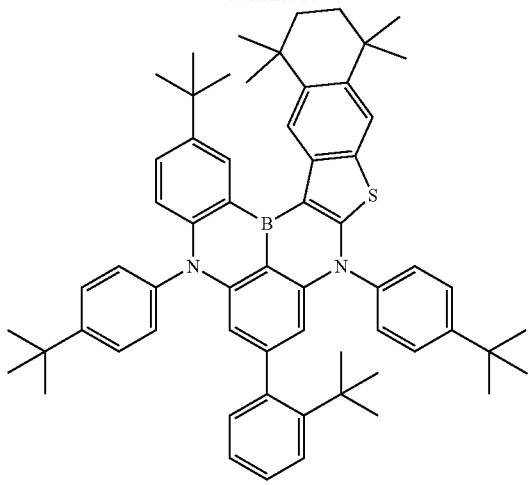
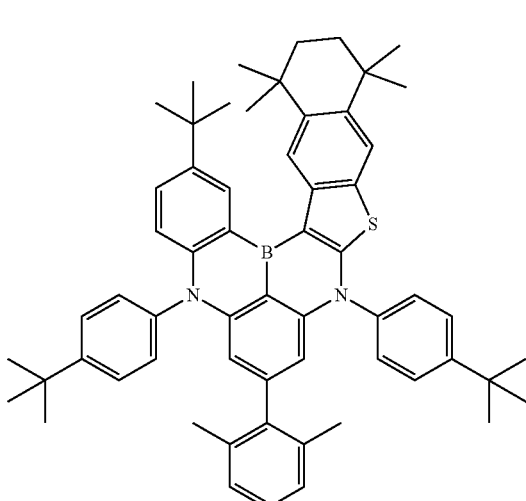
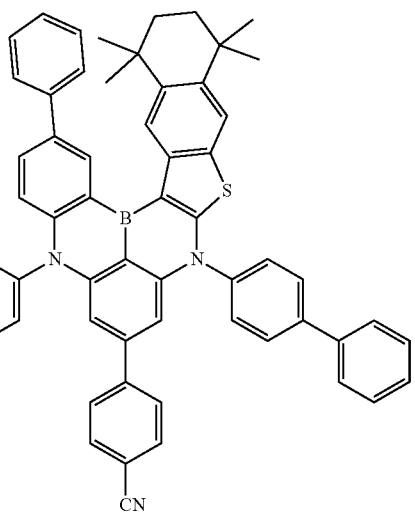

1269
-continued
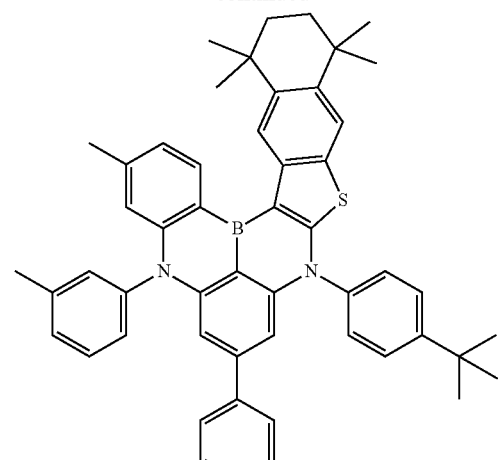
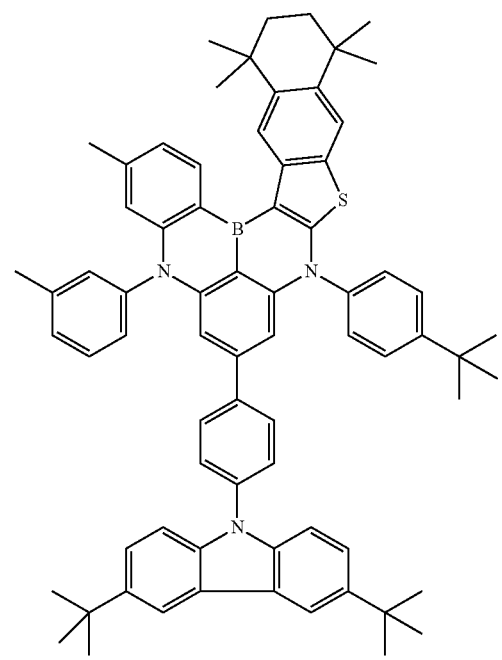
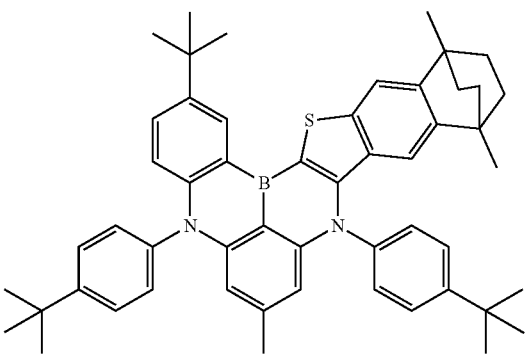
1270
-continued
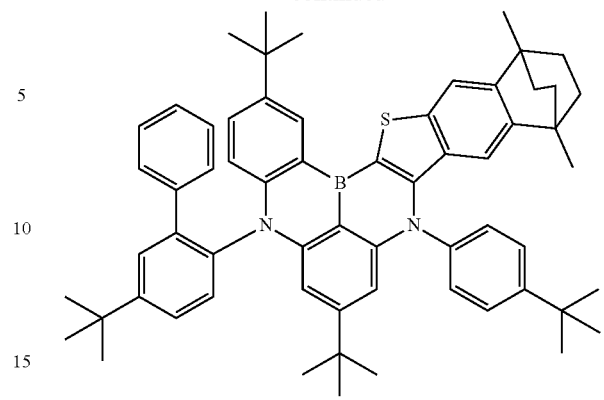
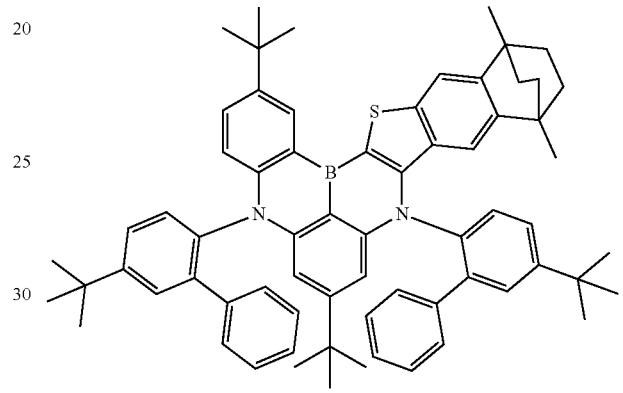
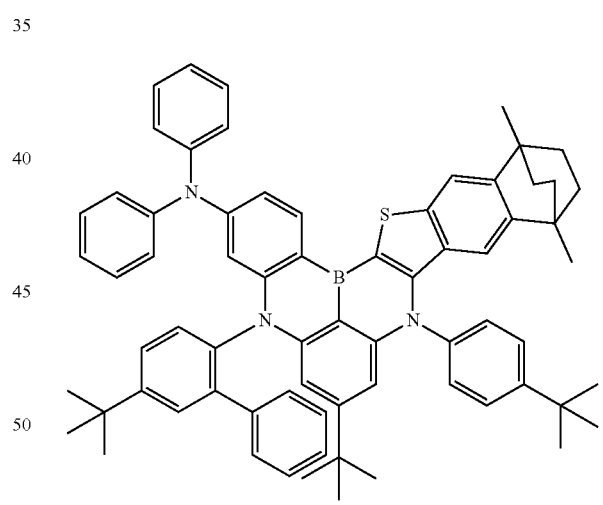
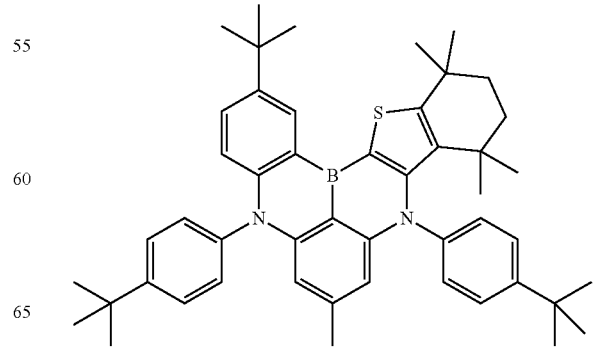

1271
-continued
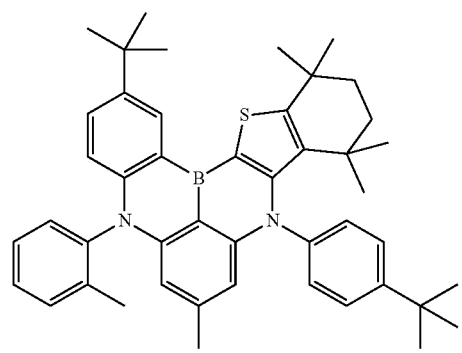
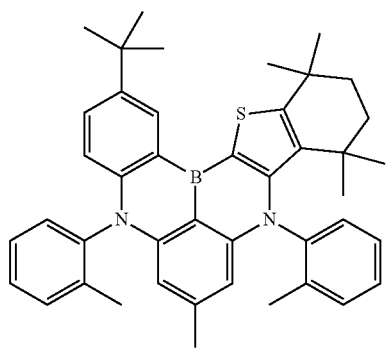
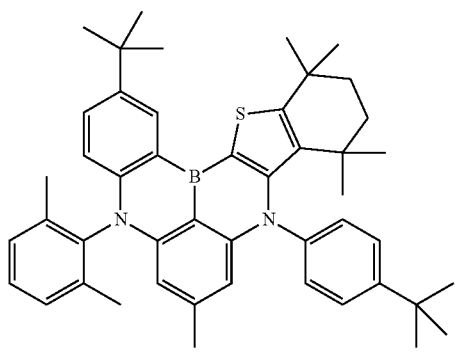
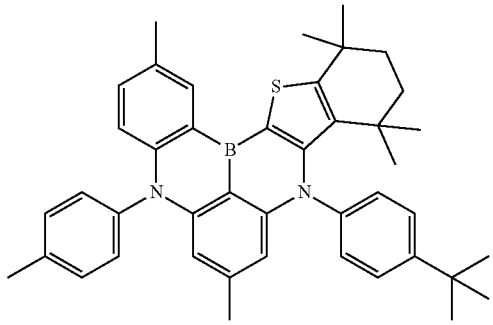
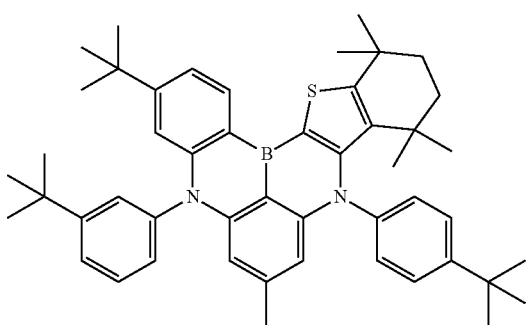
1272
-continued
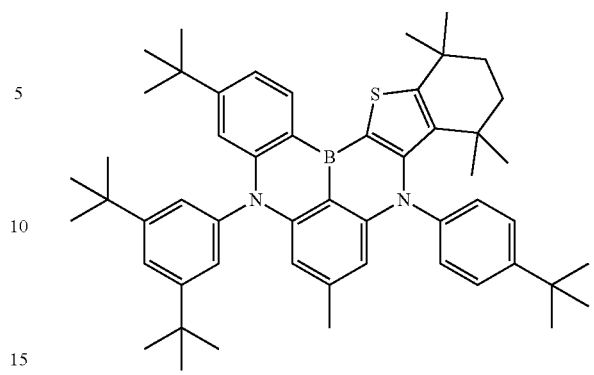
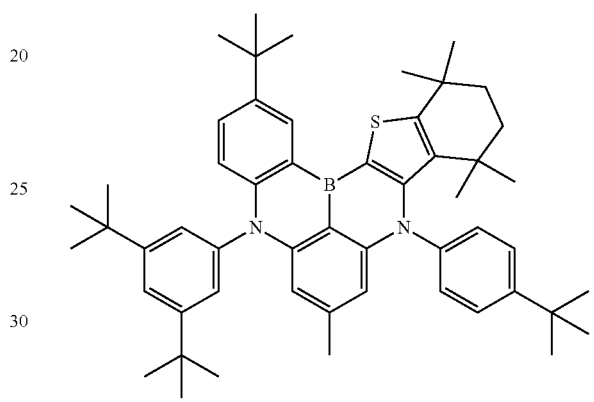
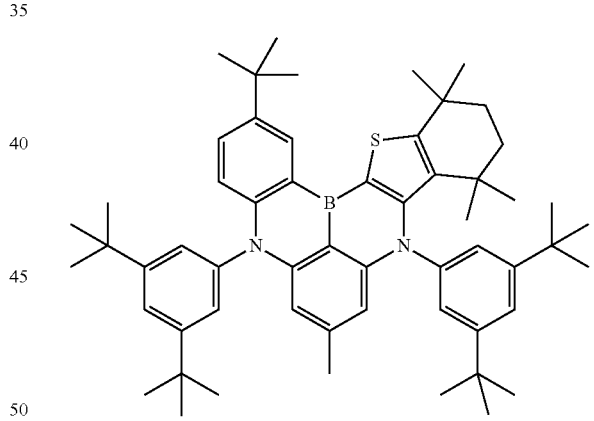
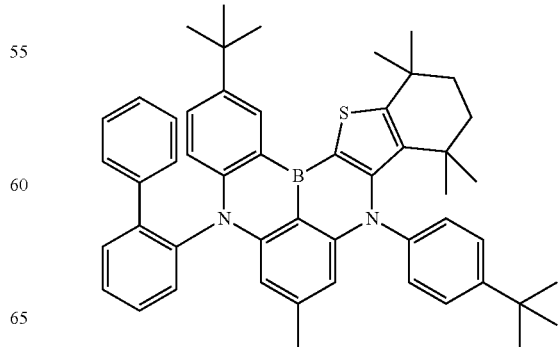

1273
-continued
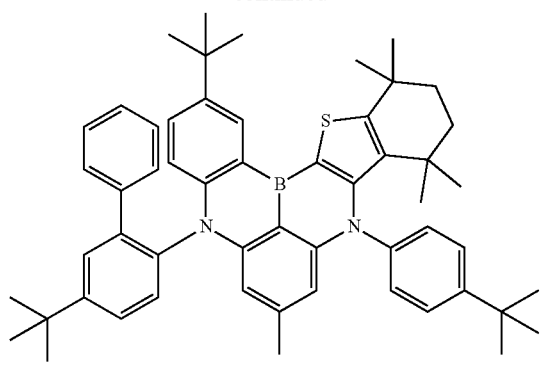
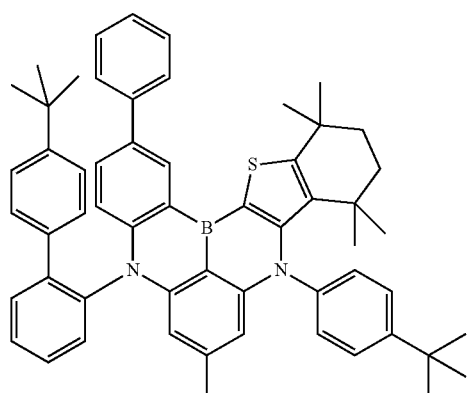
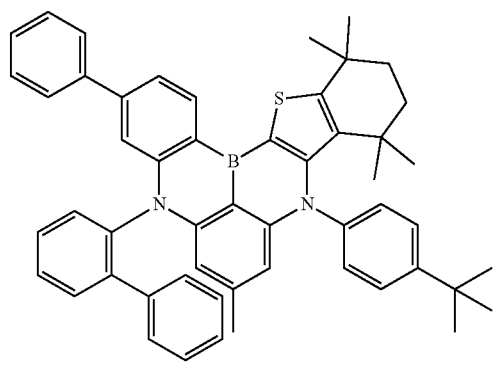
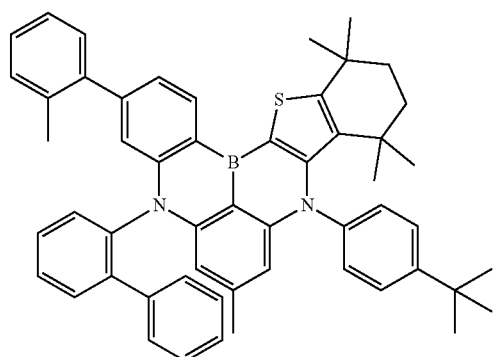
1274
-continued
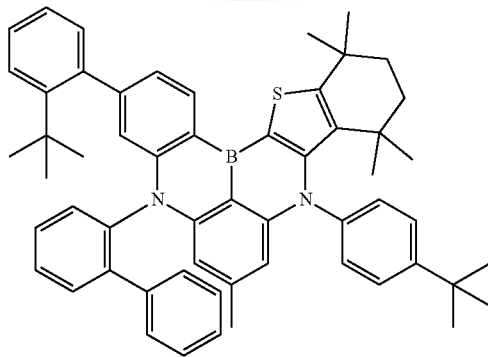
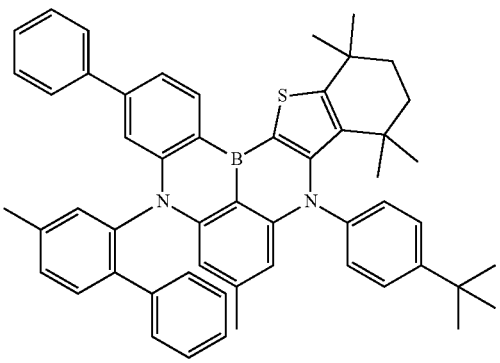
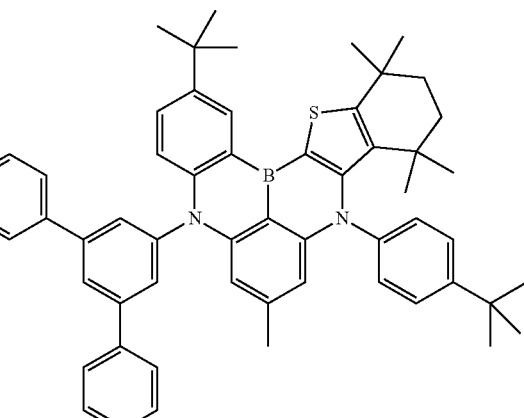
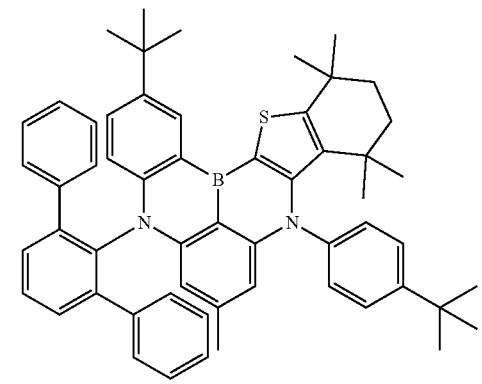

1275
-continued
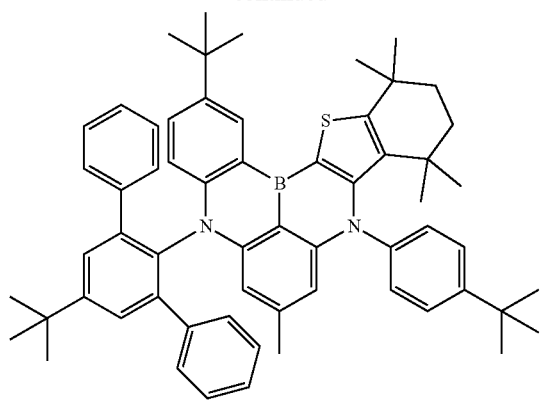
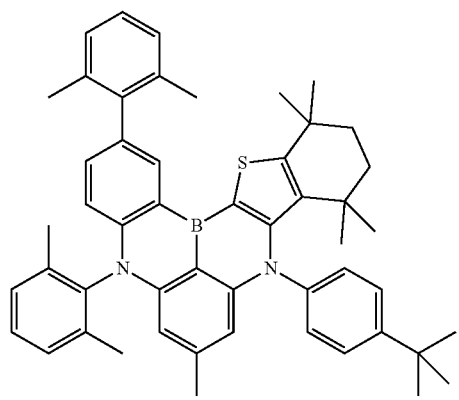
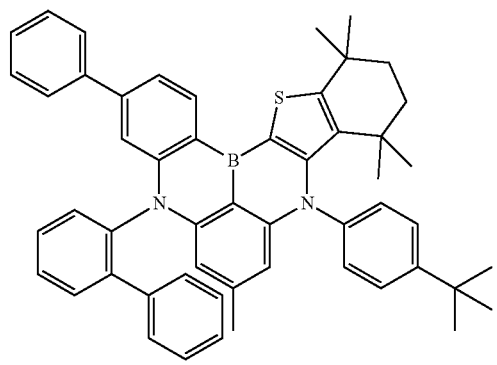
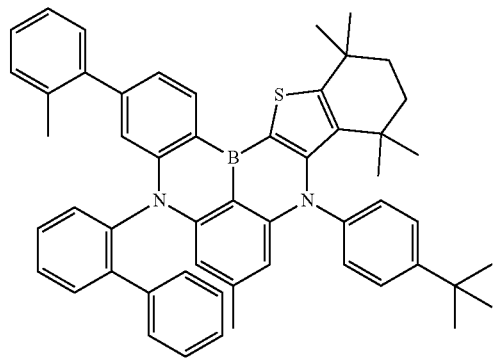
1276
-continued
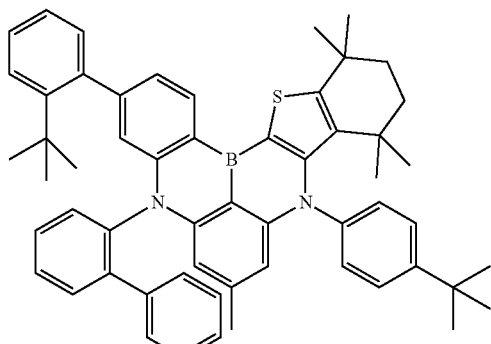
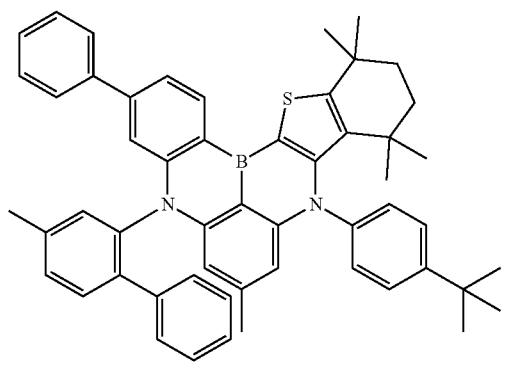
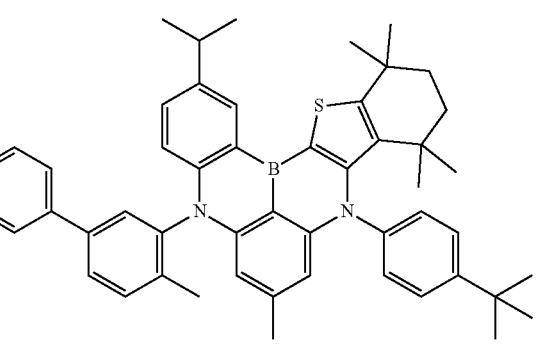
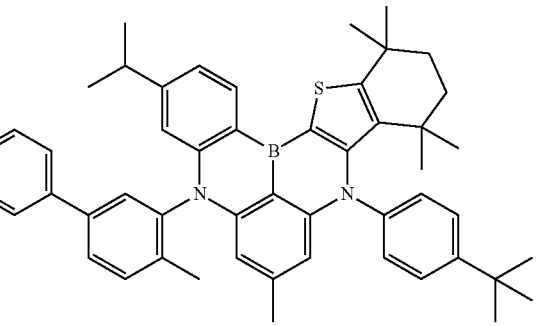

1277
1278
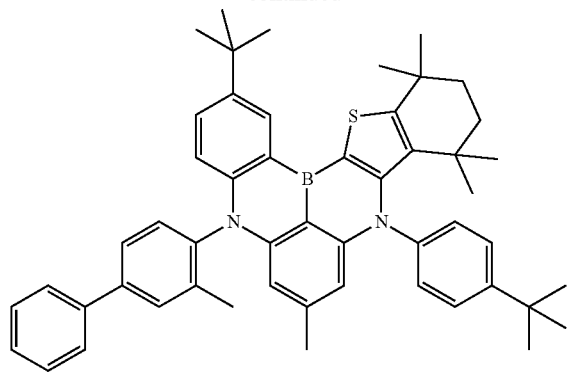
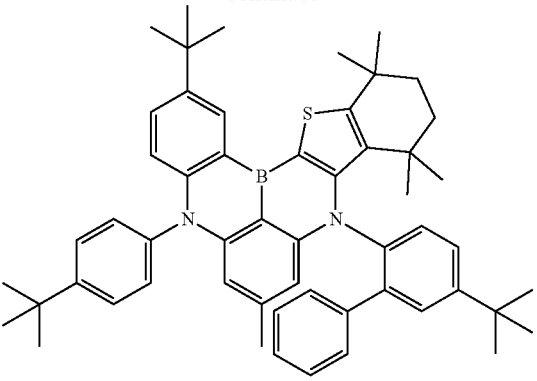

1279
-continued
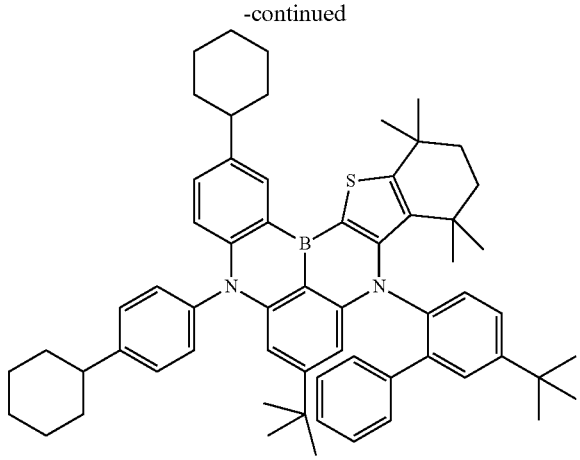
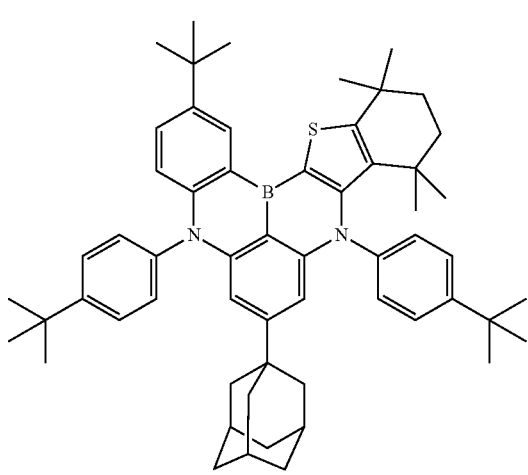
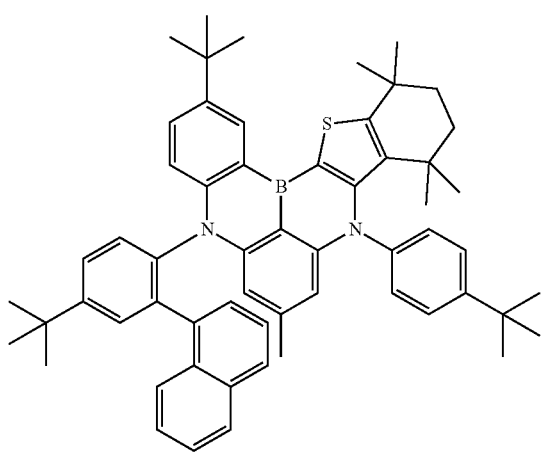
1280
-continued
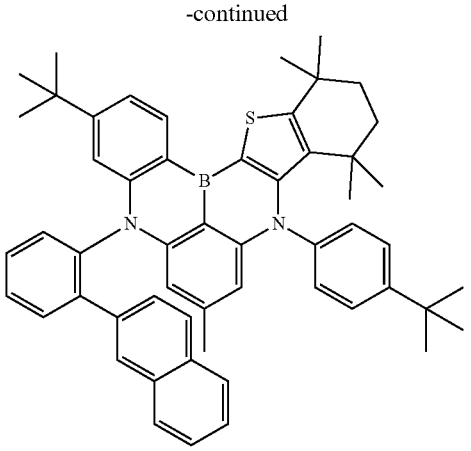
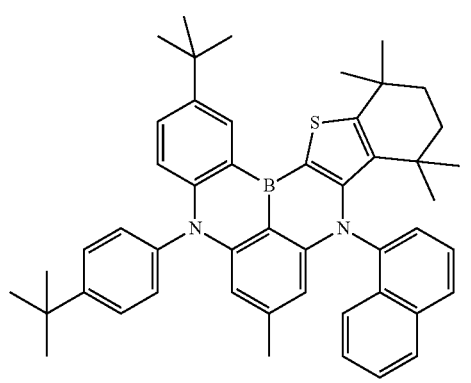
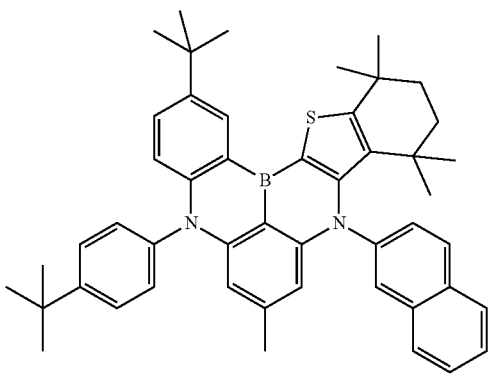
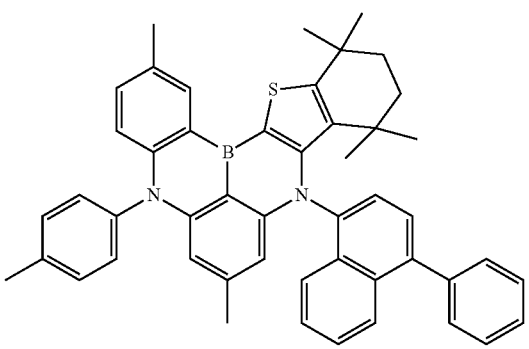

1281
-continued
1282
-continued
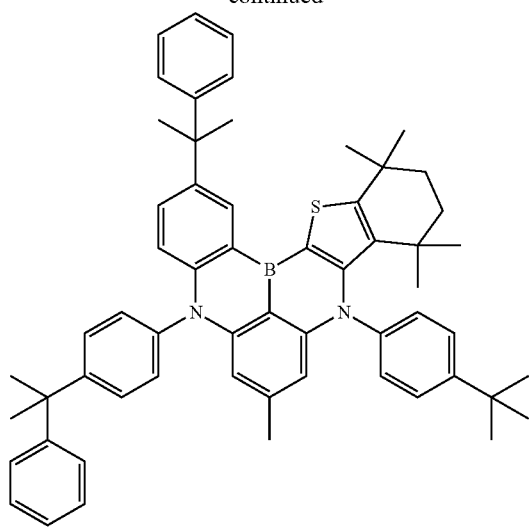
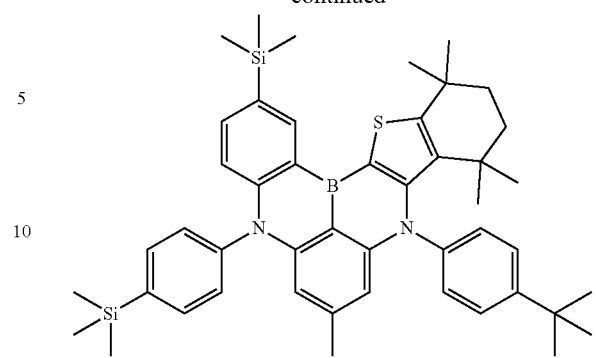
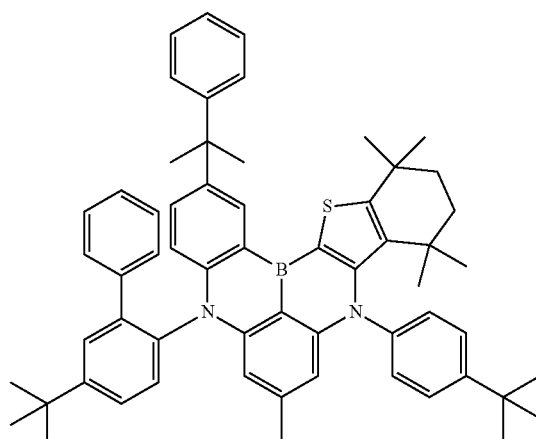
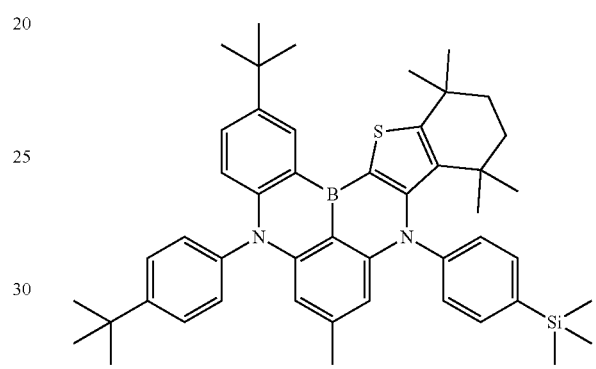
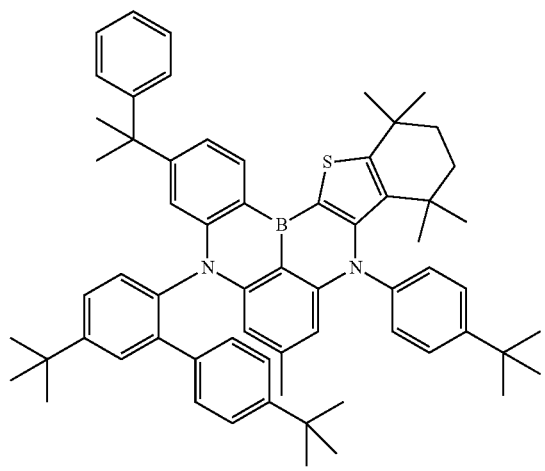
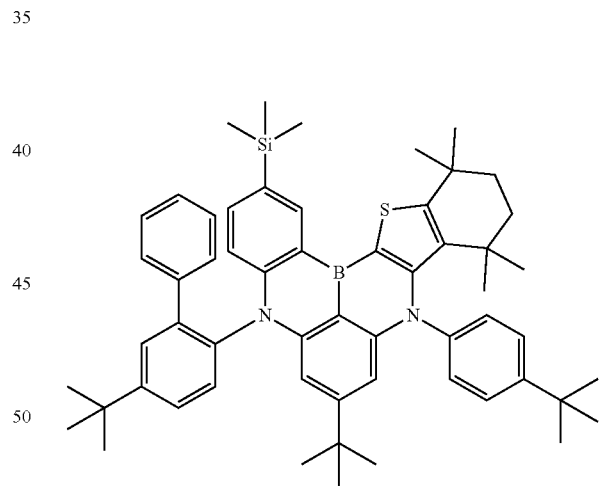
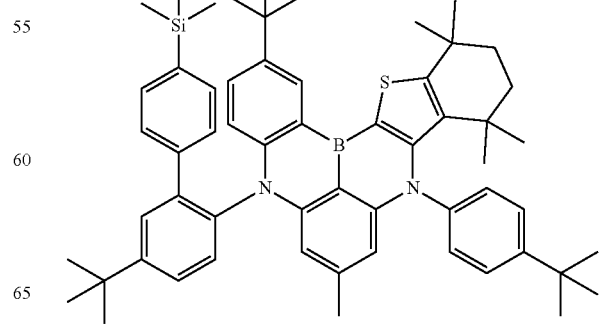

1283
-continued
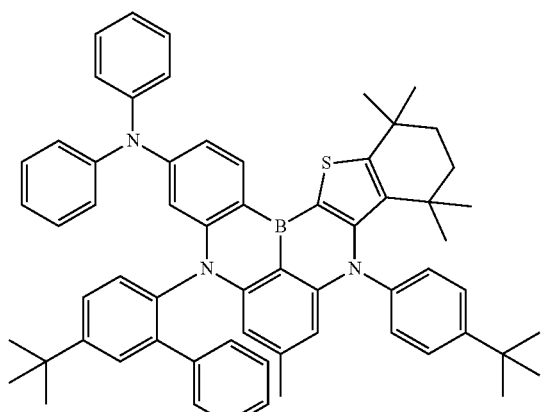
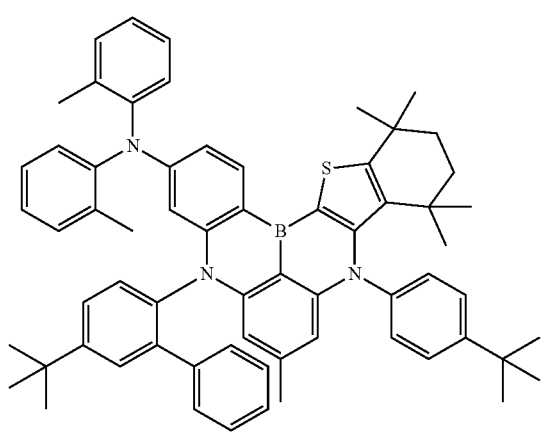
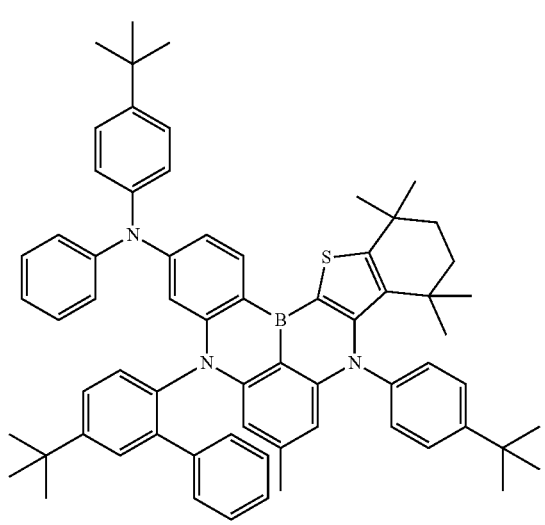
1284
-continued
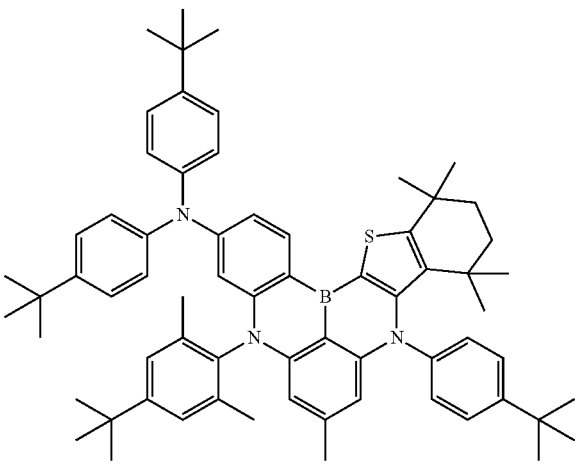
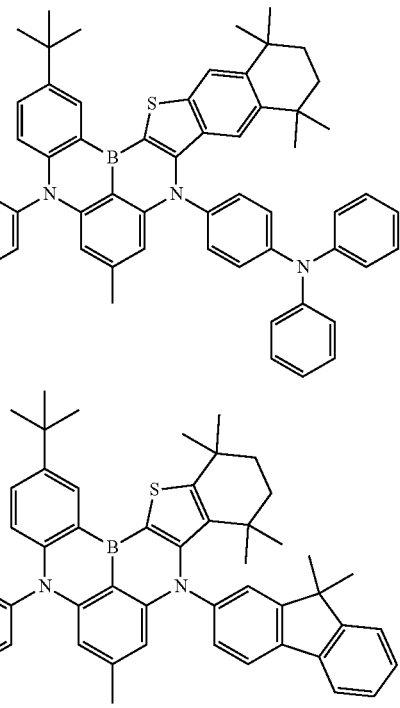

1285
-continued
1286
-continued
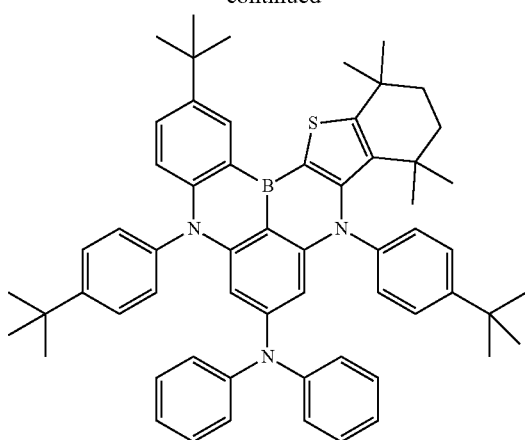
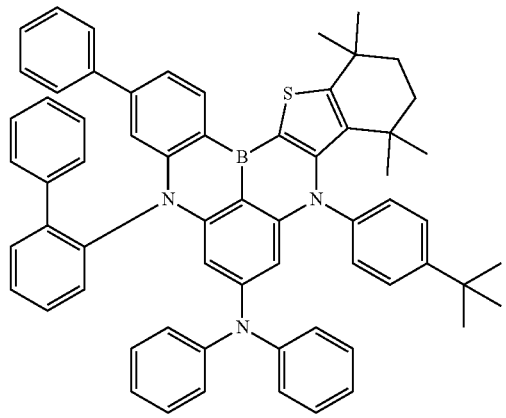
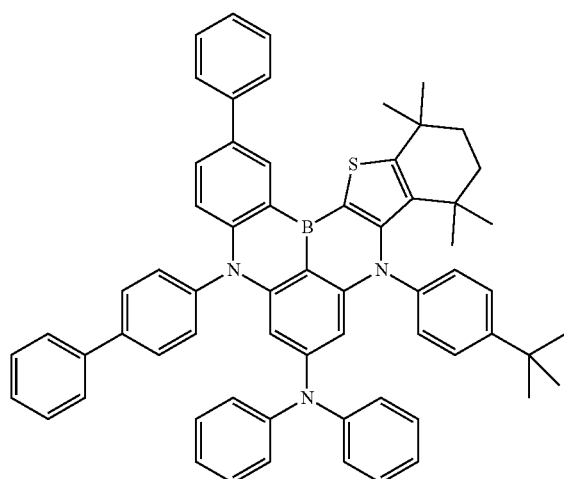
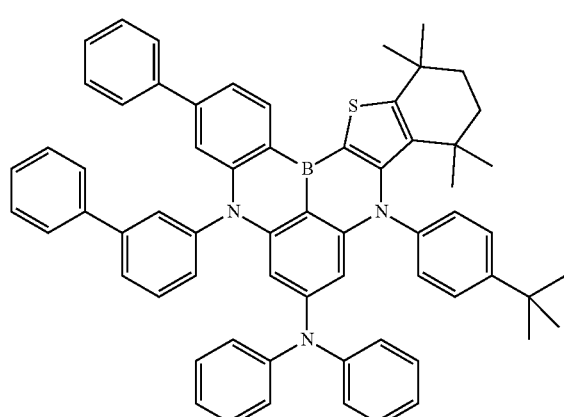
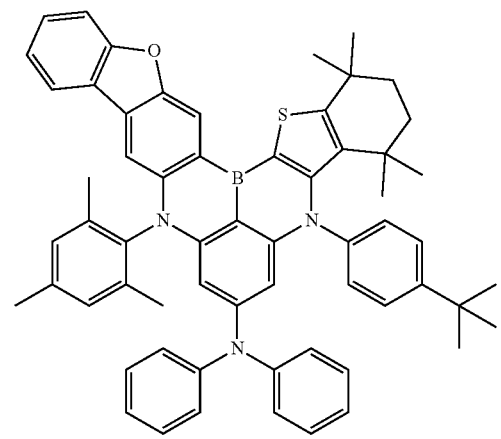

1287
-continued
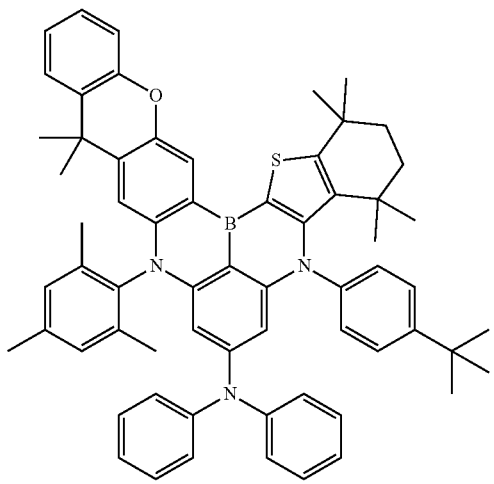
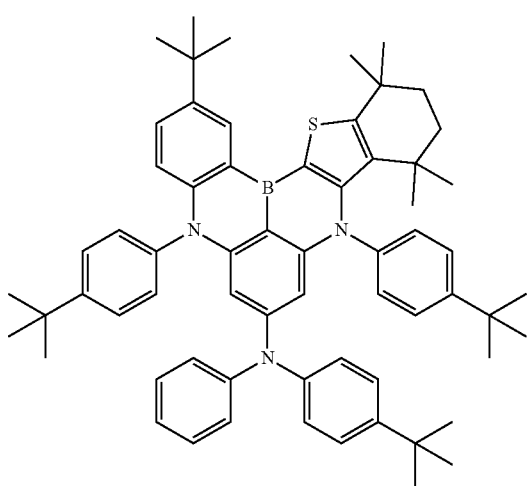
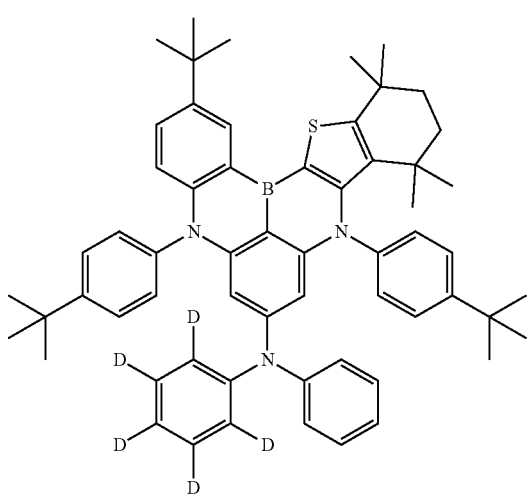
1288
-continued
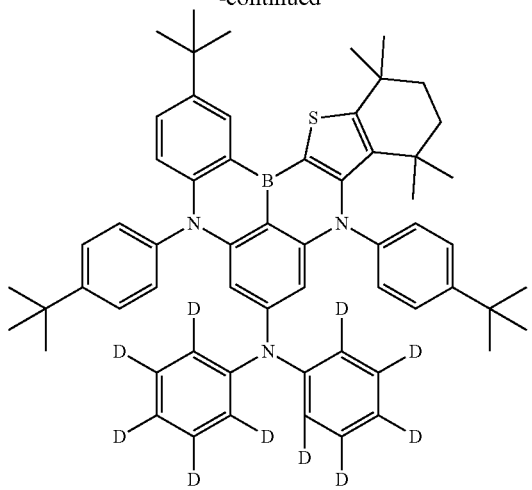
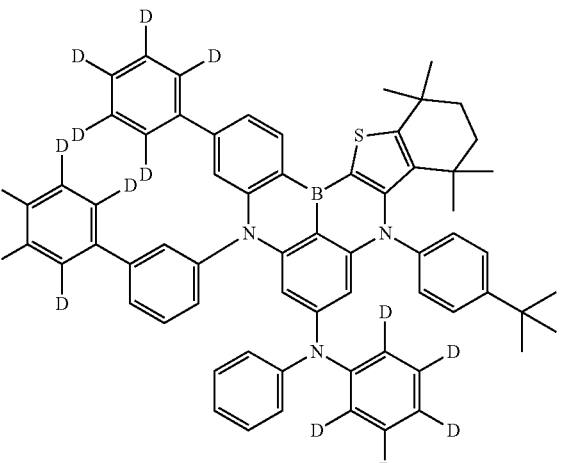
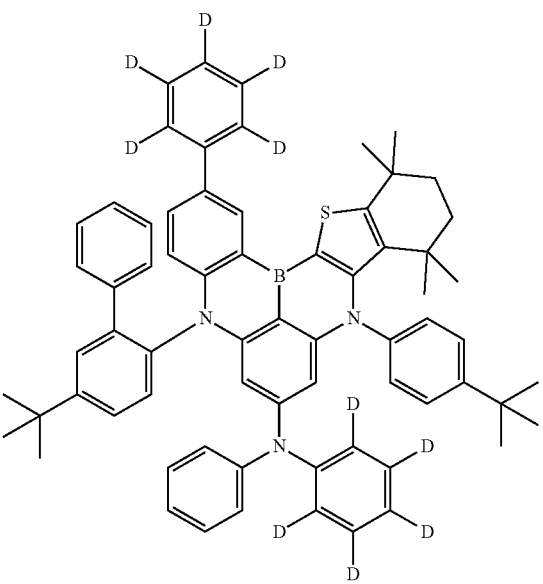

1289
-continued
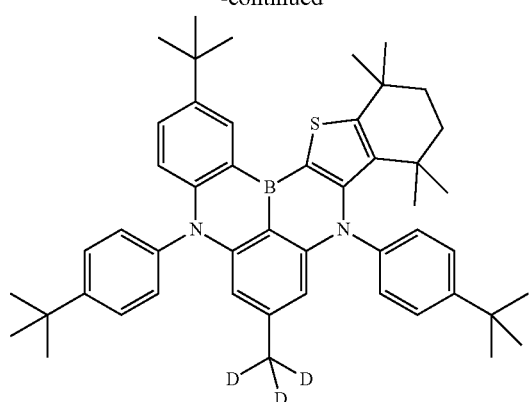
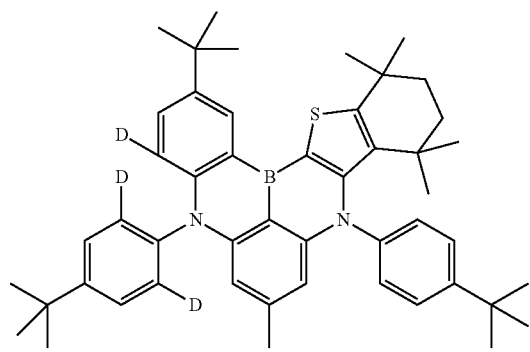
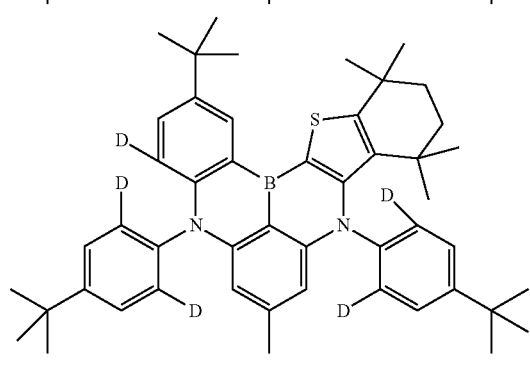
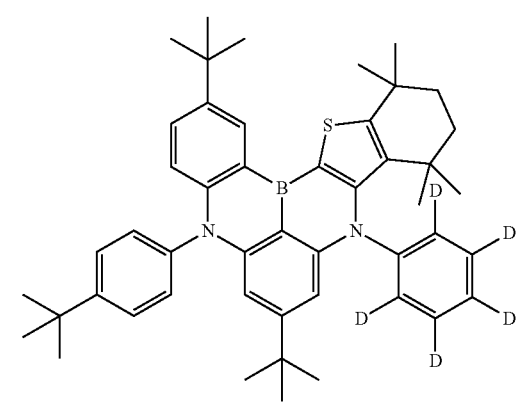
1290
-continued
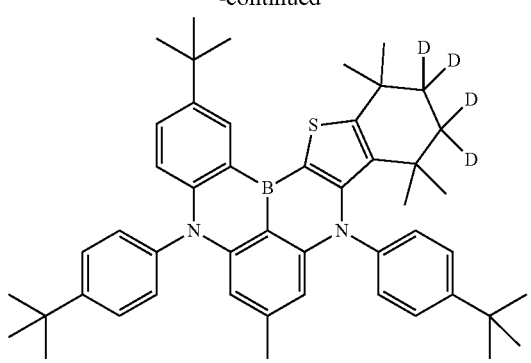
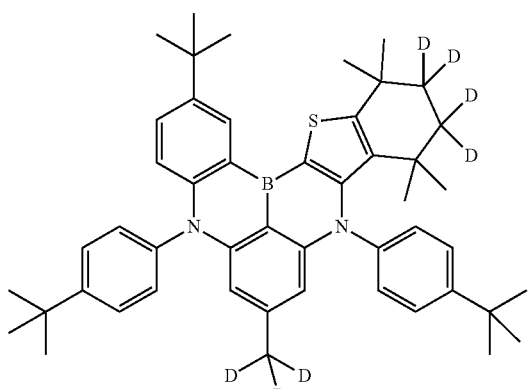
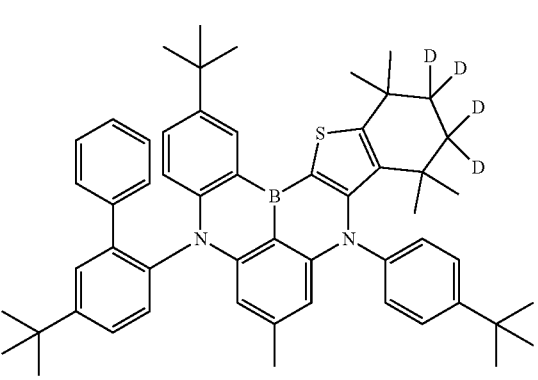
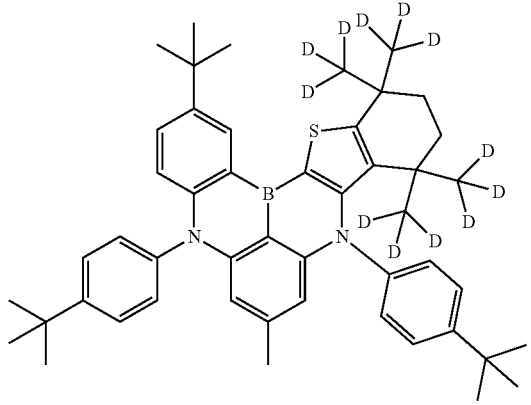

1291
-continued
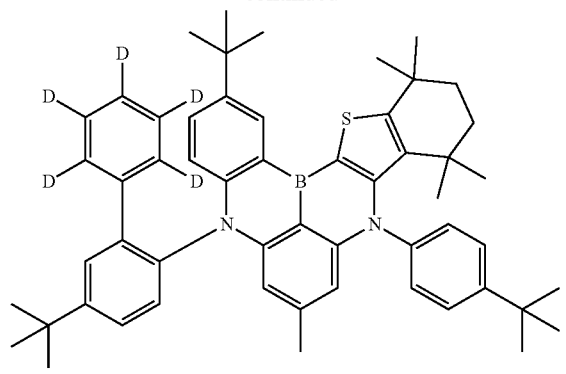
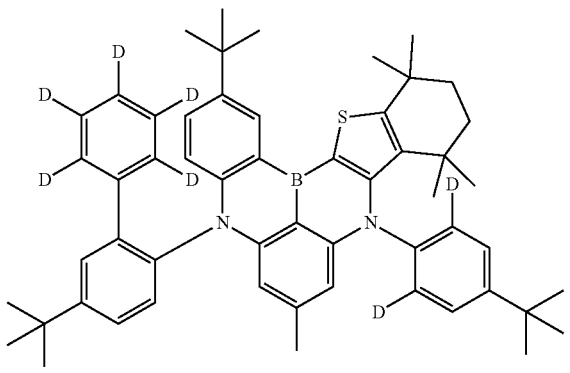
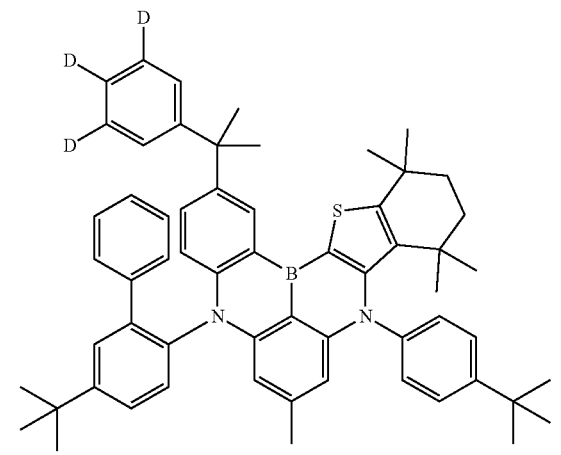
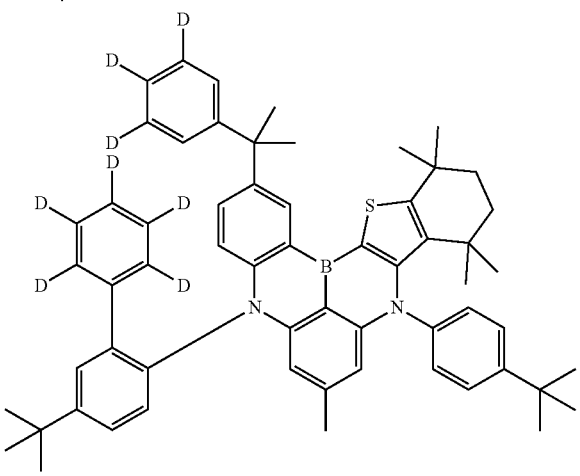
1292
-continued
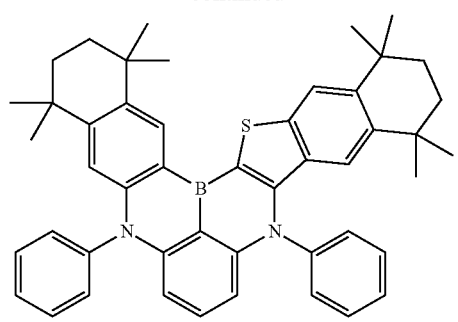
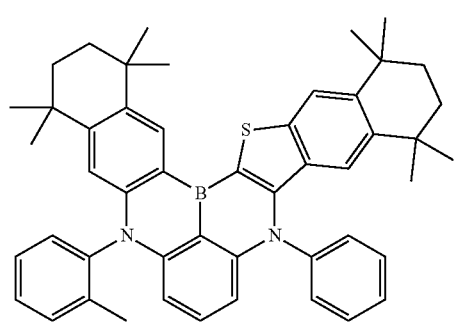
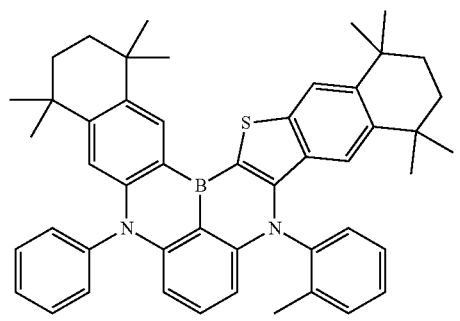
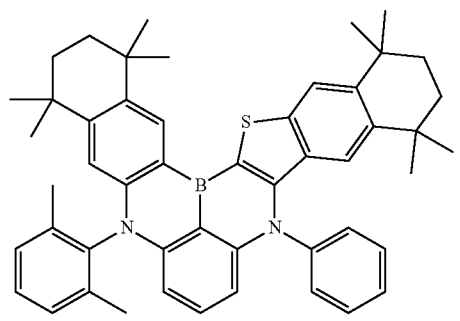
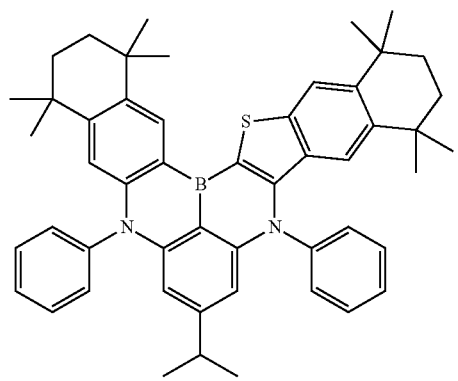

1293
-continued
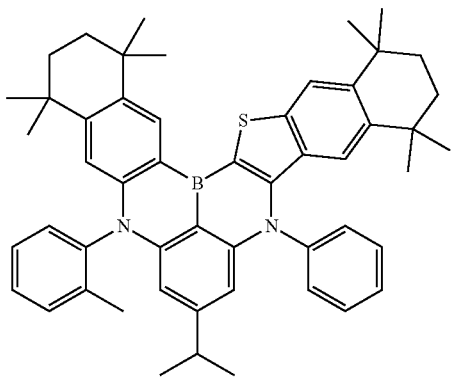
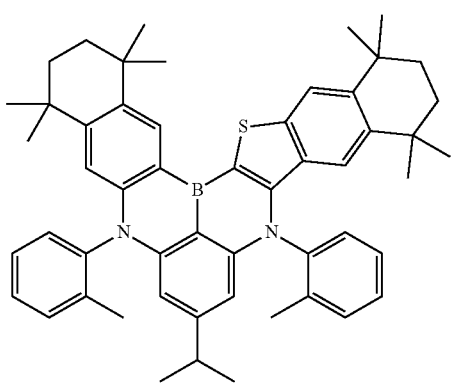
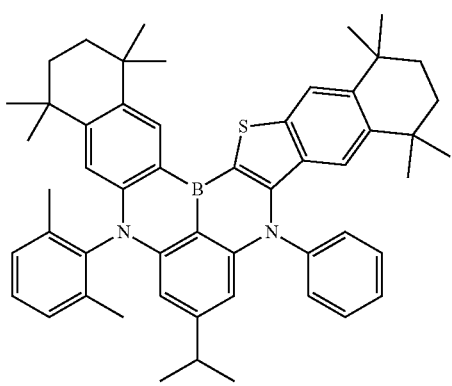
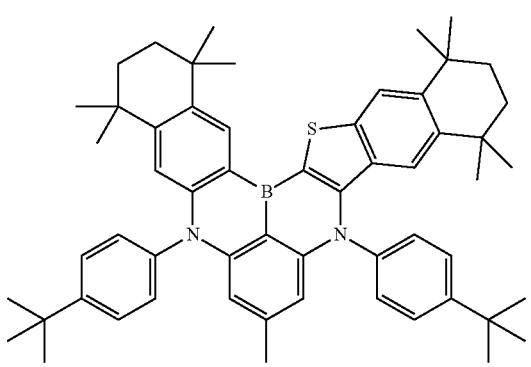
1294
-continued
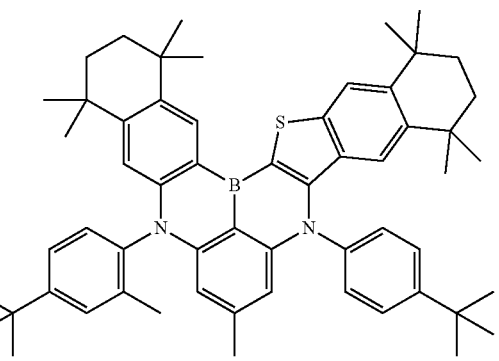
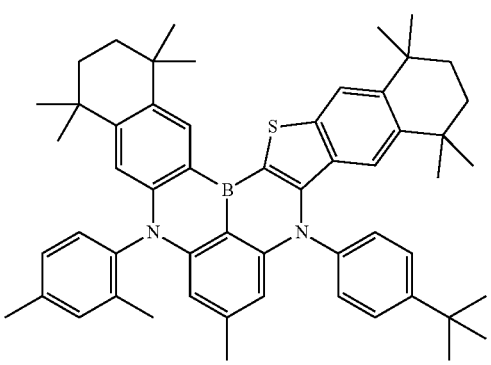
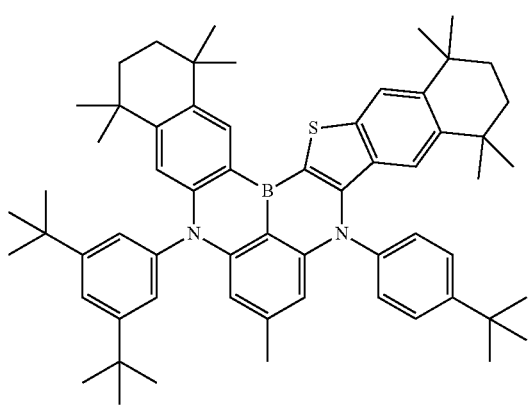
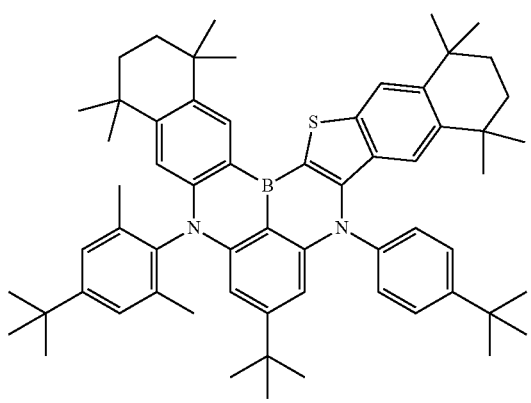

1295
-continued
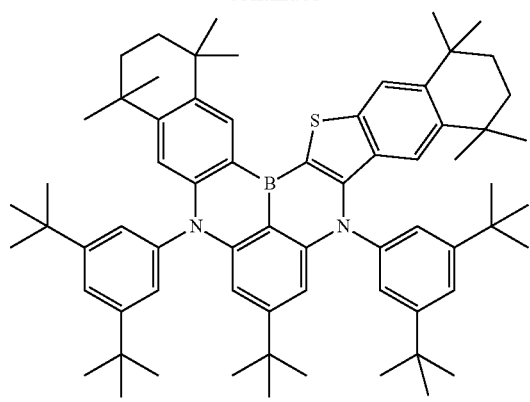
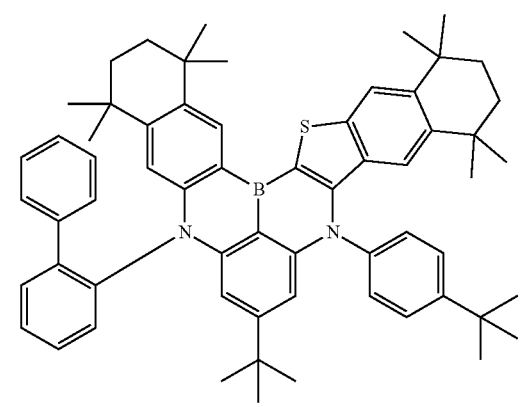
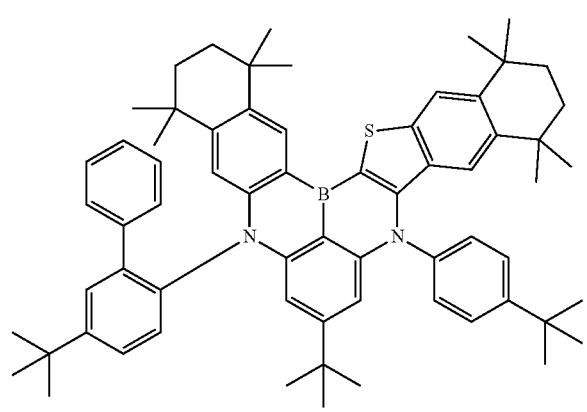
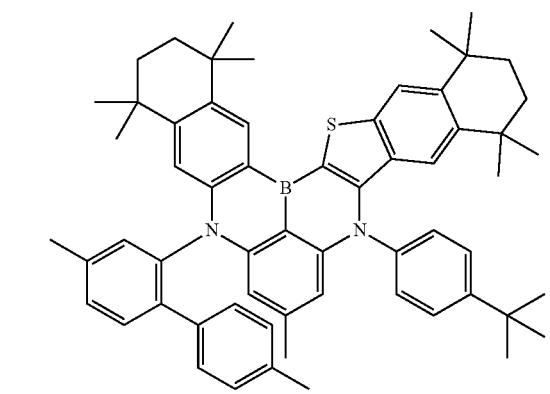
1296
-continued
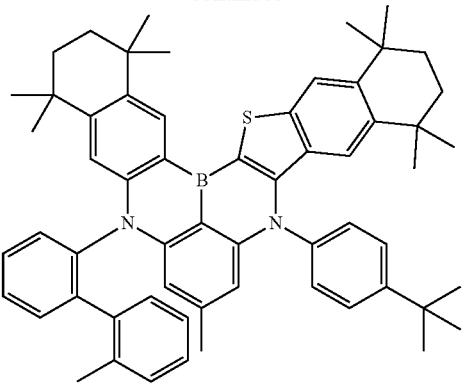
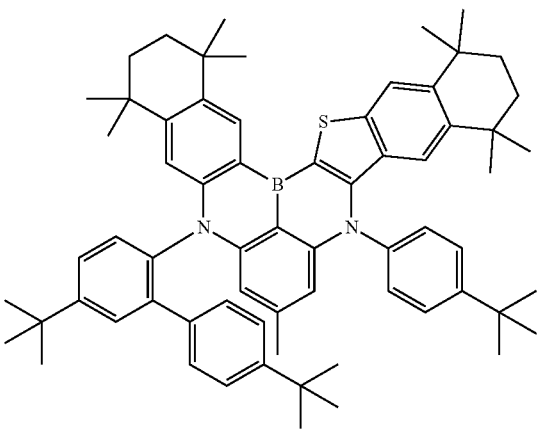
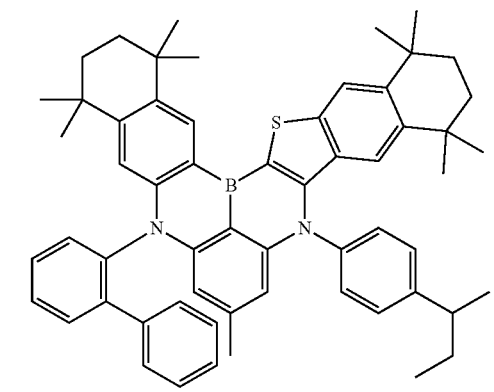
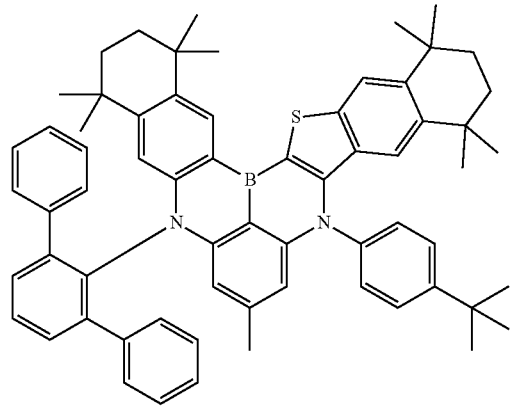

1297
-continued
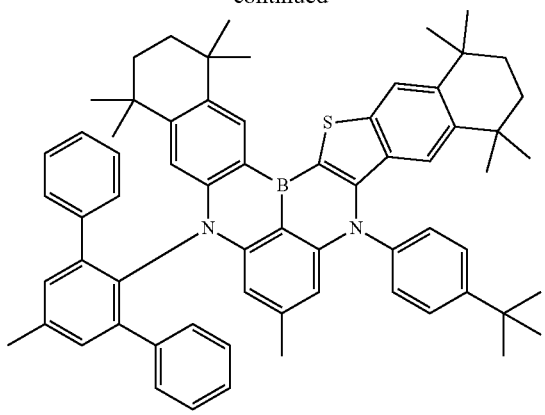
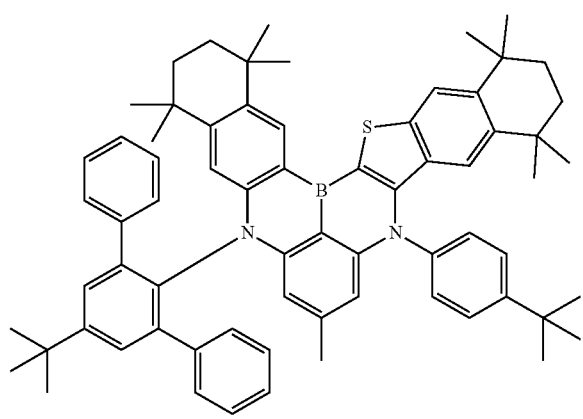
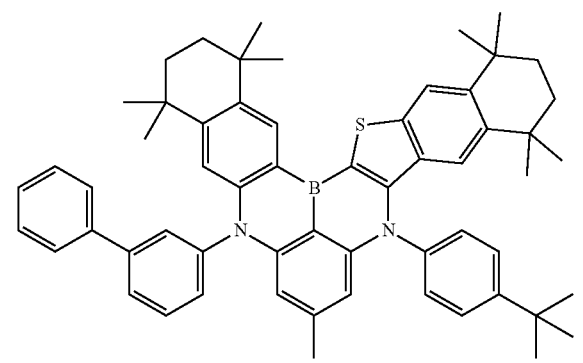
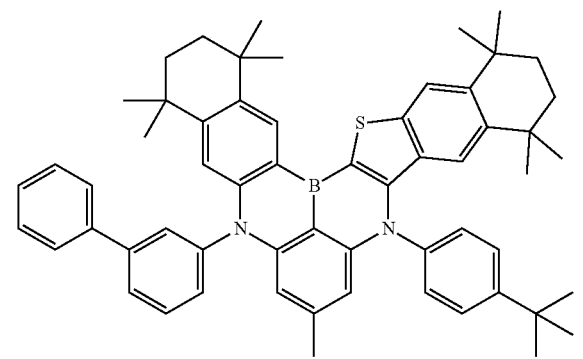
1298
-continued
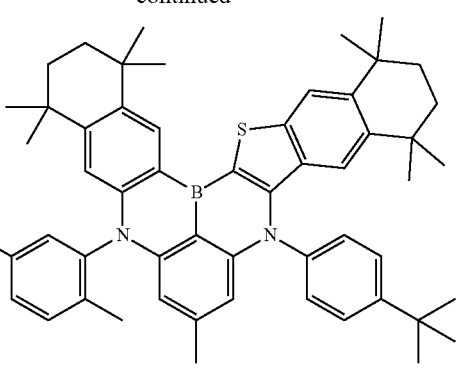
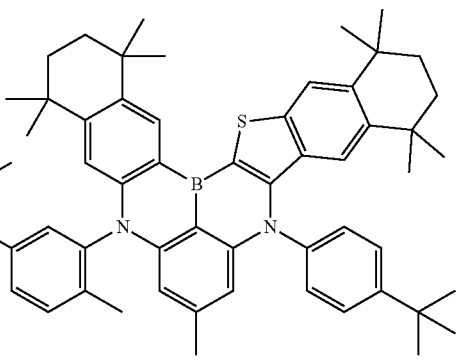
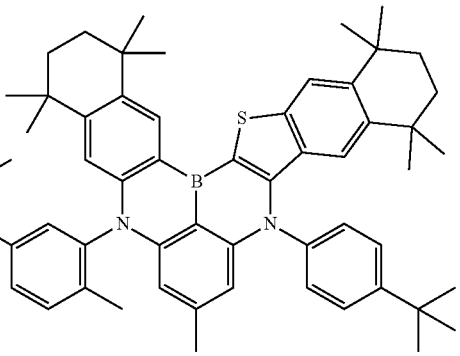
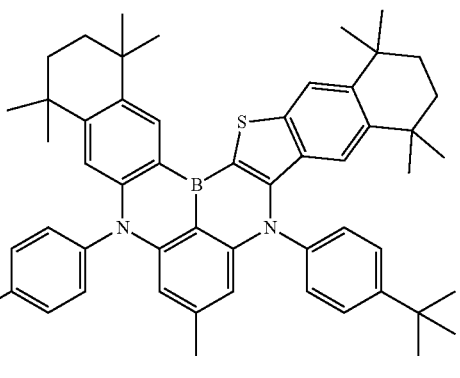

1299
-continued
1300
-continued
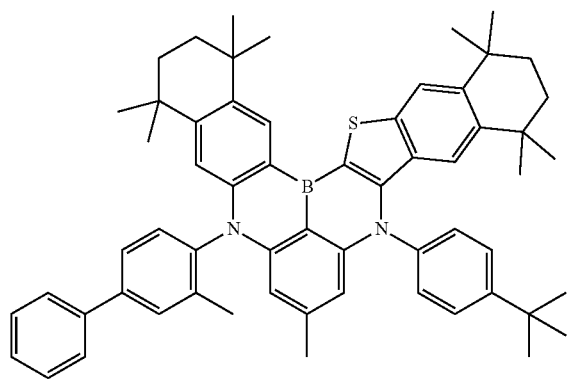
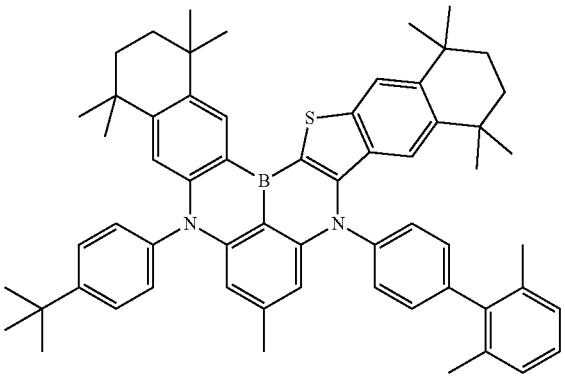

| 1301 | 1302 |
|---|---|
| -continued | -continued |
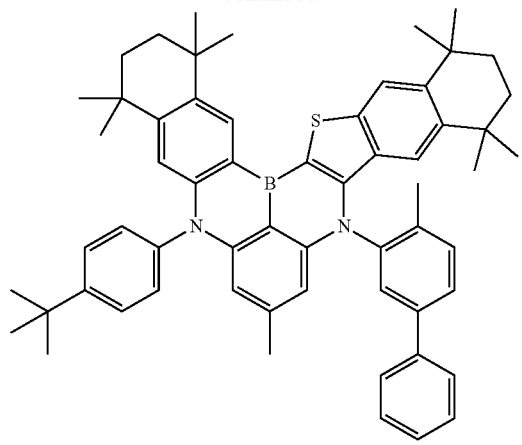
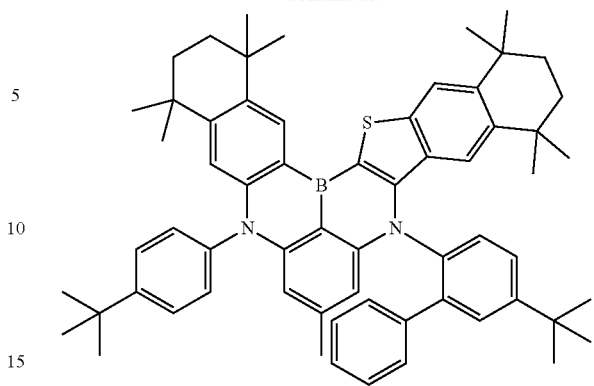
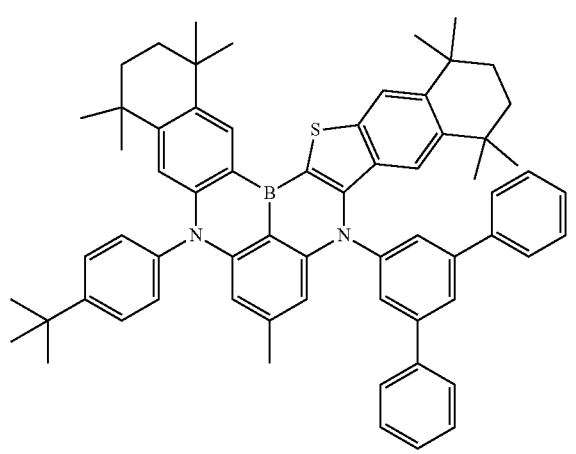
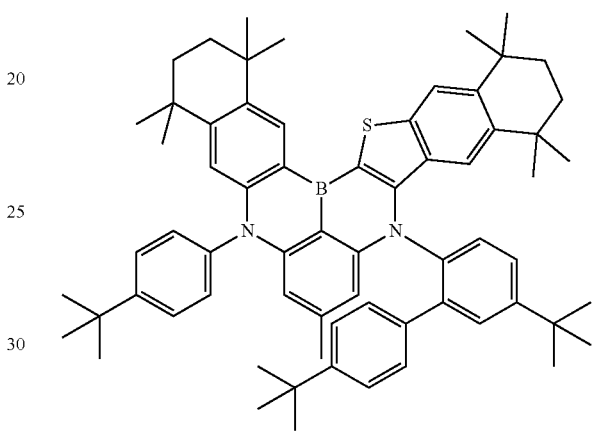
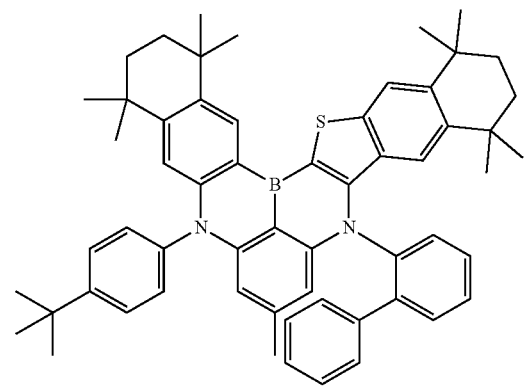
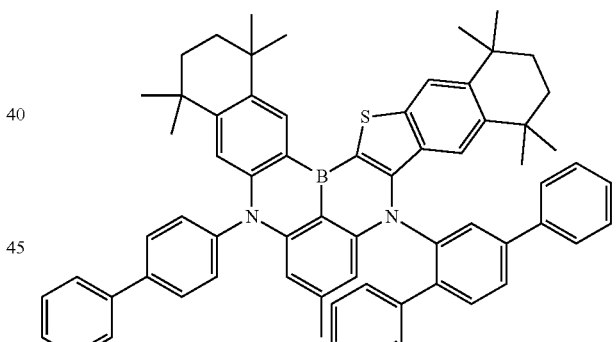
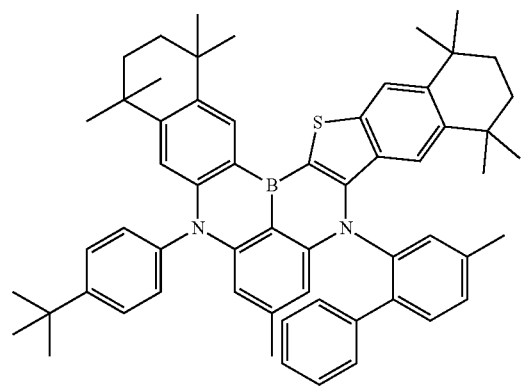
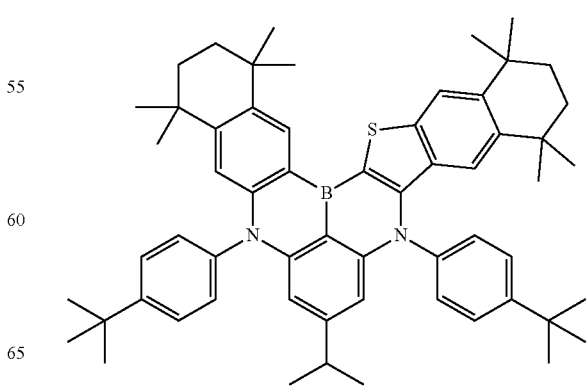

US 11,685,751 B2
1303
-continued
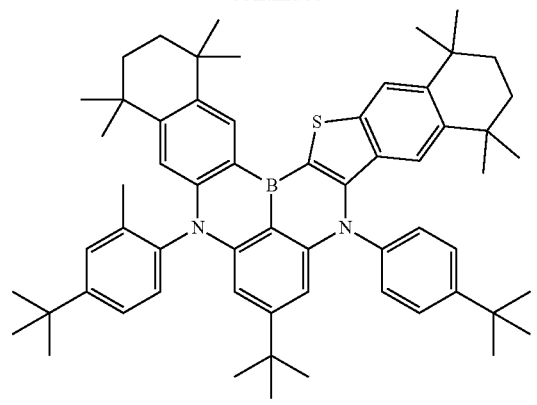
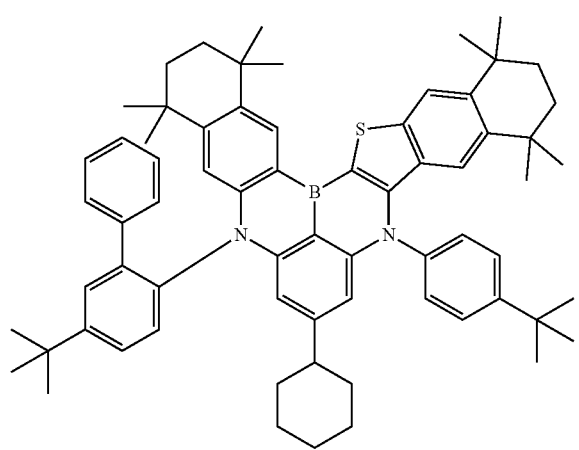
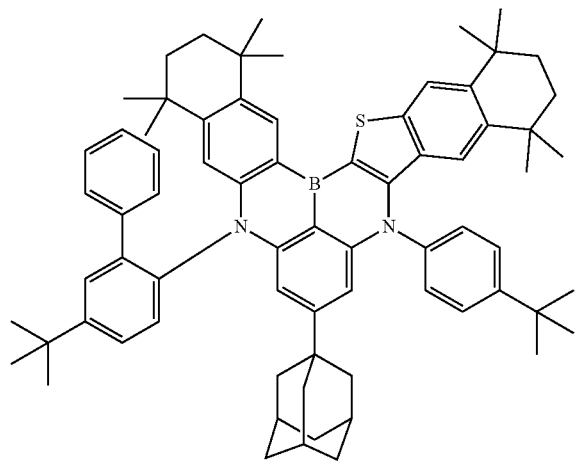
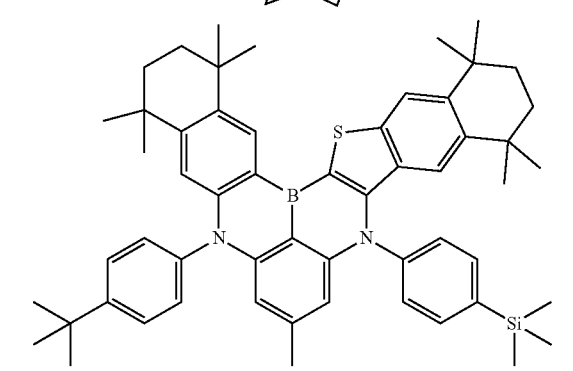
1304
-continued
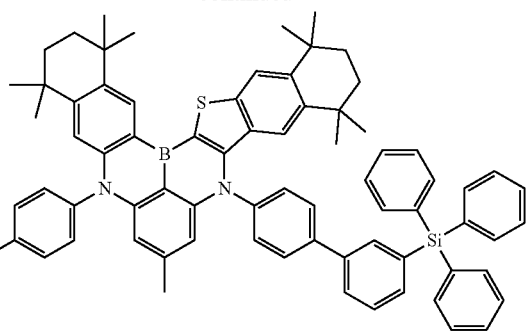
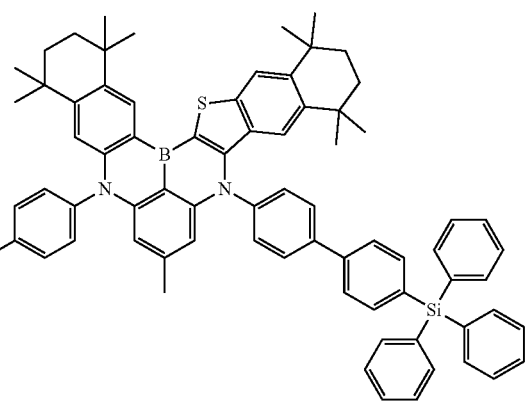
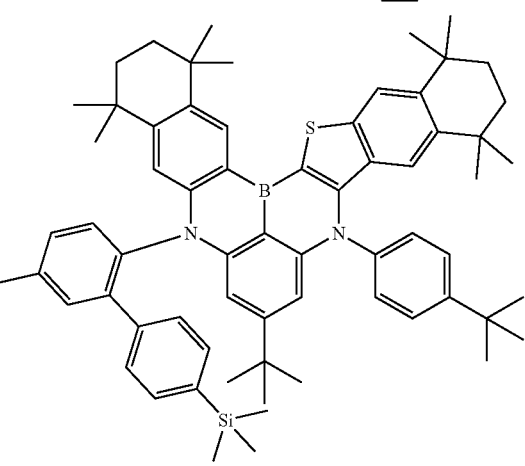
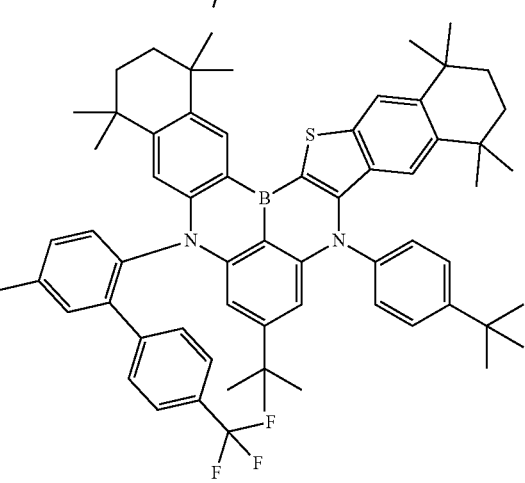

1305
-continued
1306
-continued
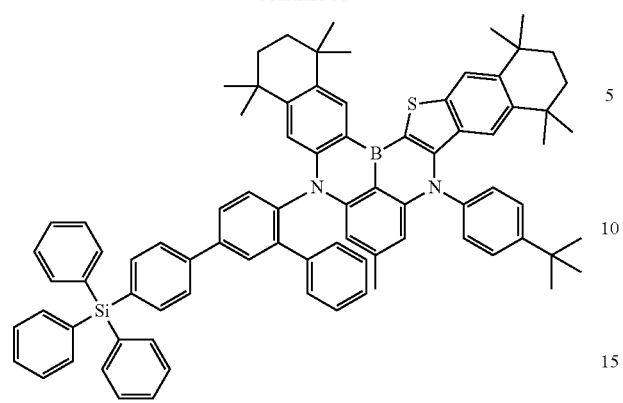
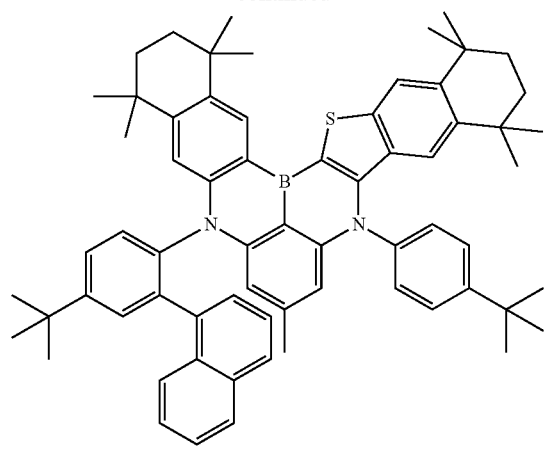
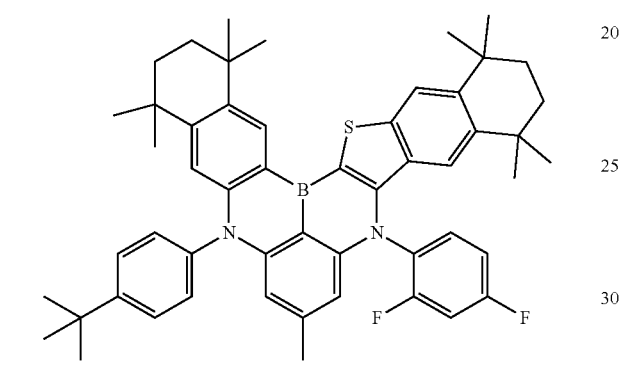
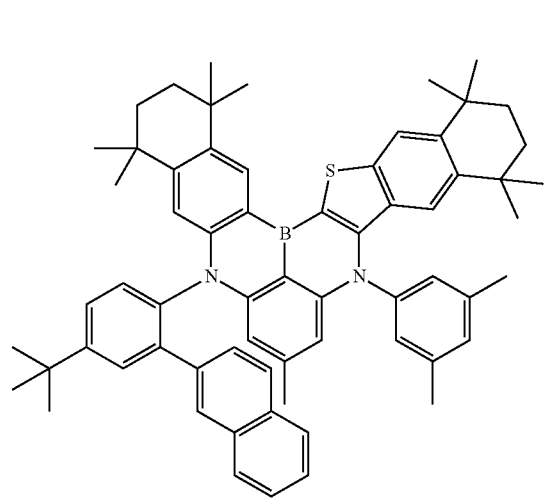
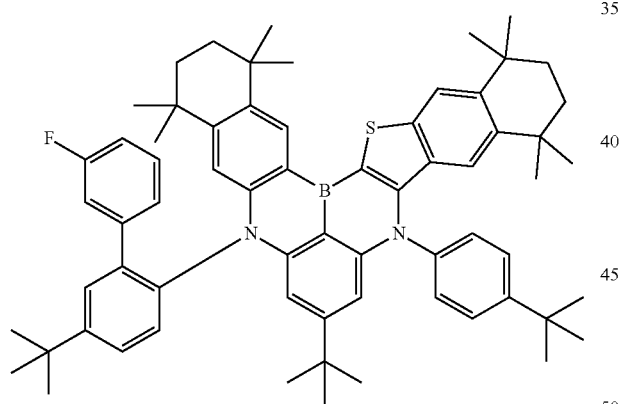
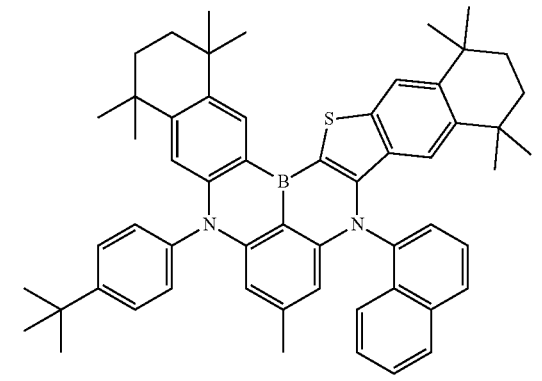
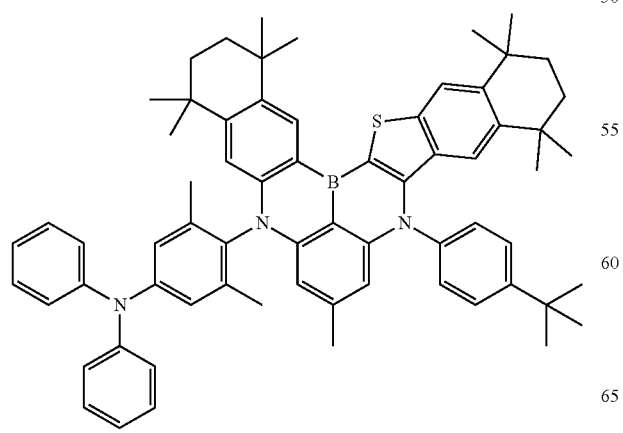
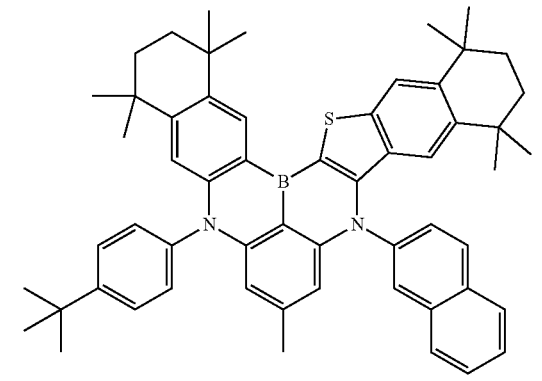

1307
-continued
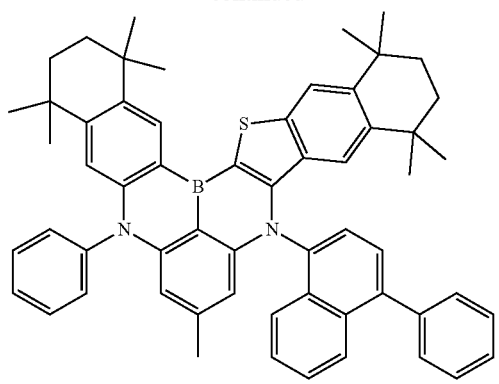
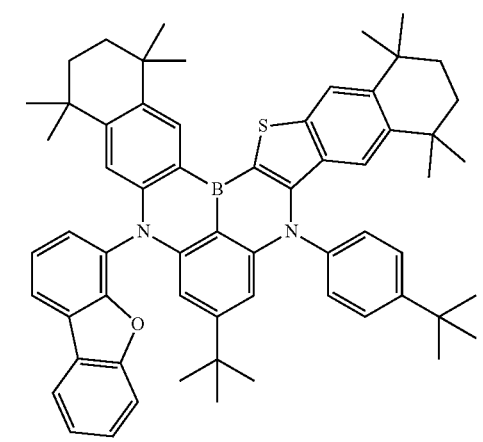
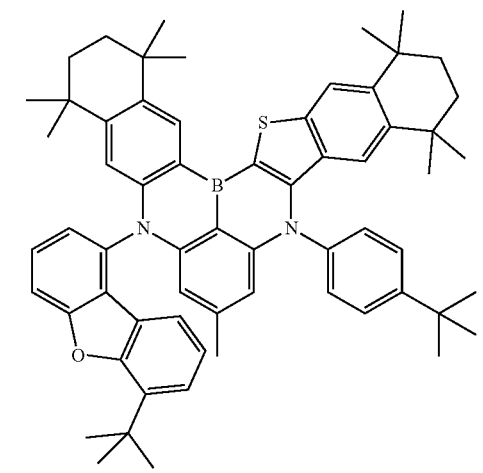
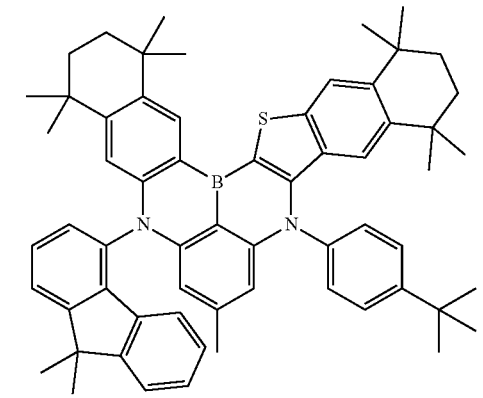
1308
-continued
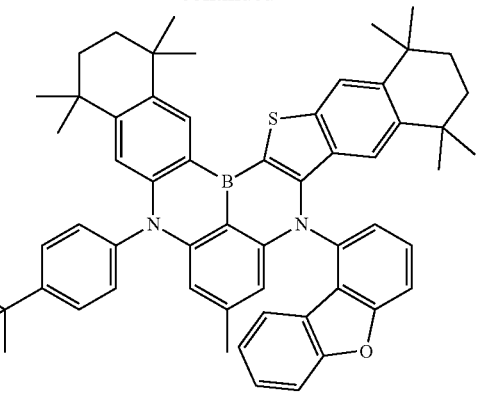
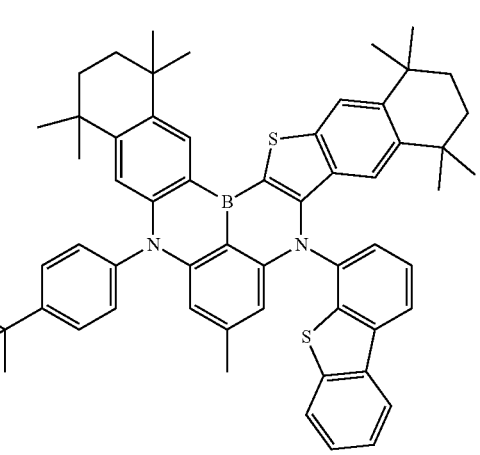
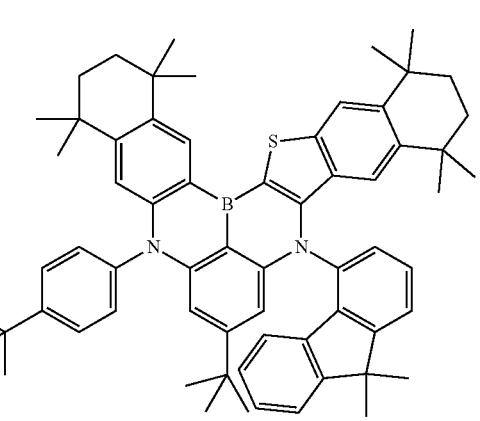
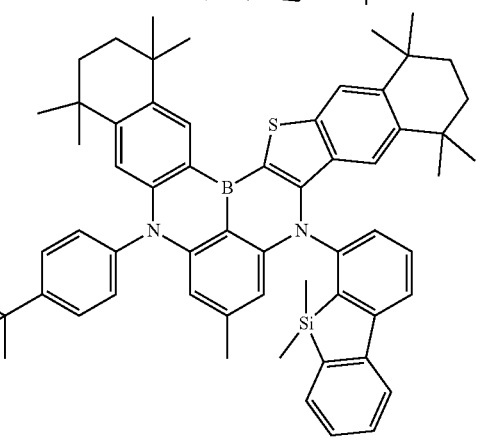

1309
-continued
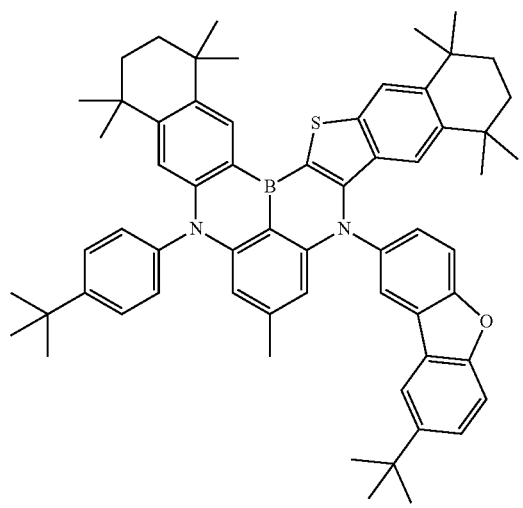
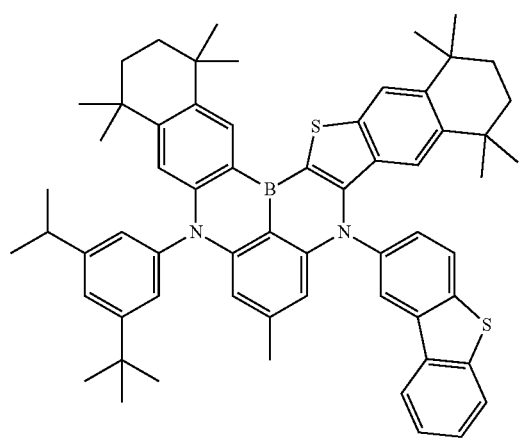
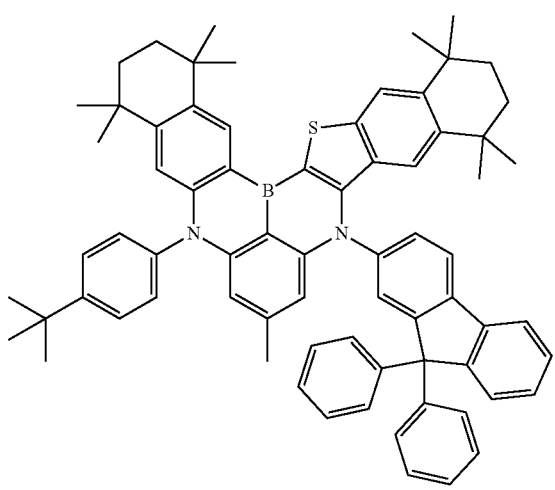
1310
-continued
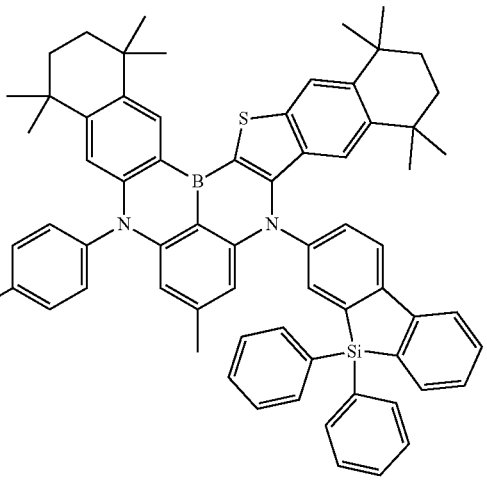
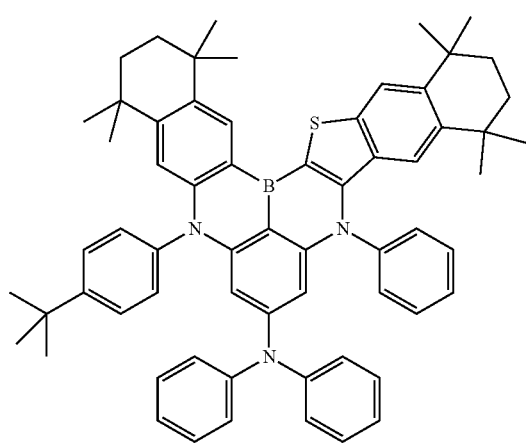
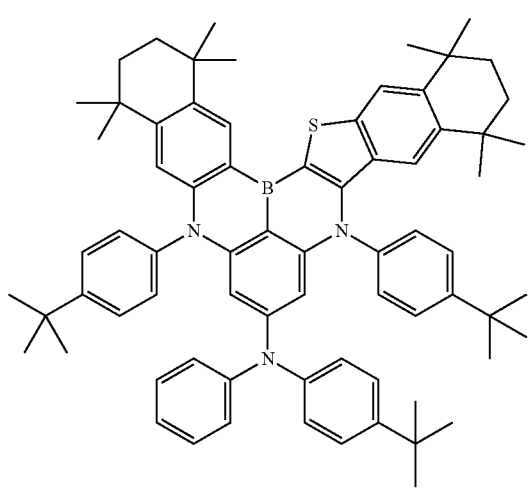

1311
-continued
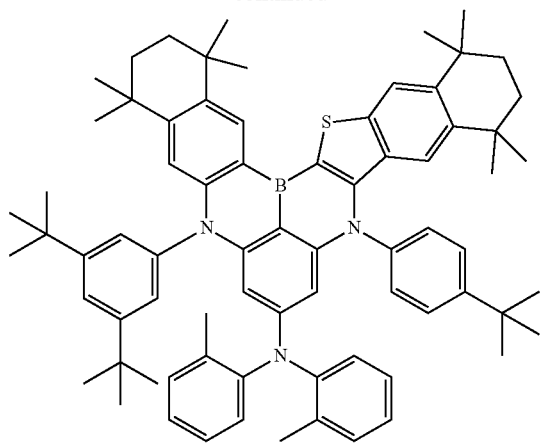
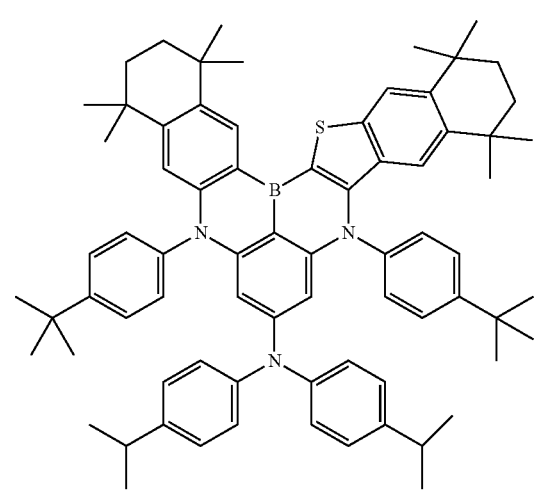
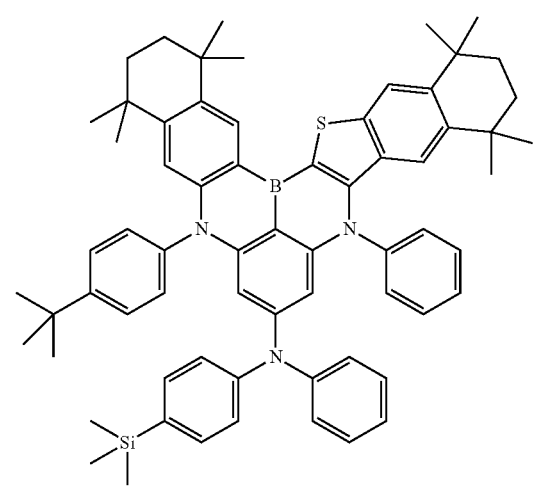
1312
-continued
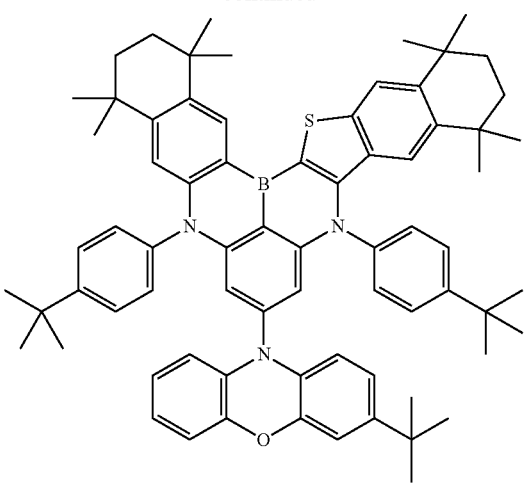
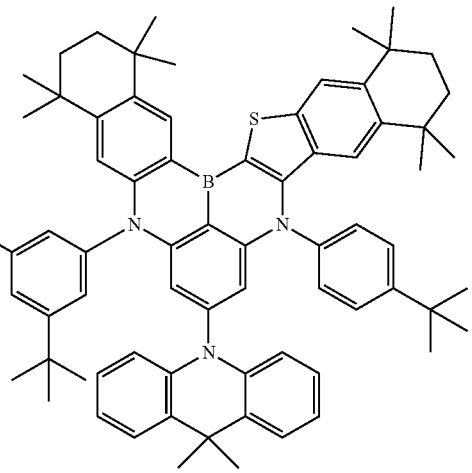
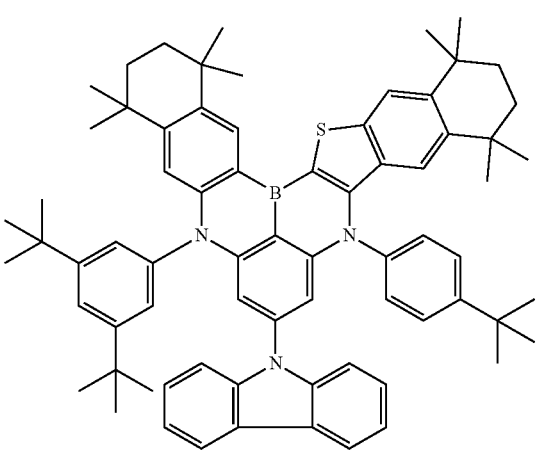

1313
-continued
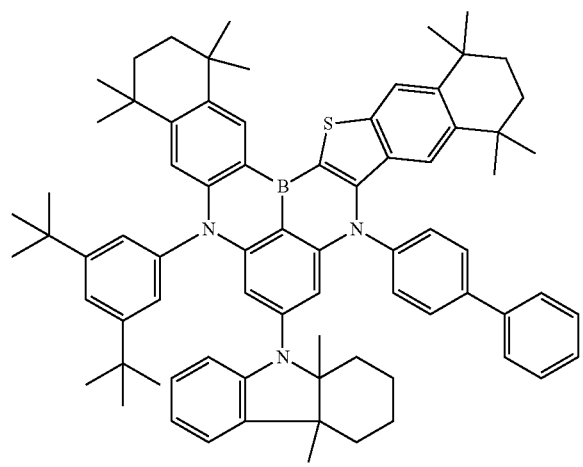
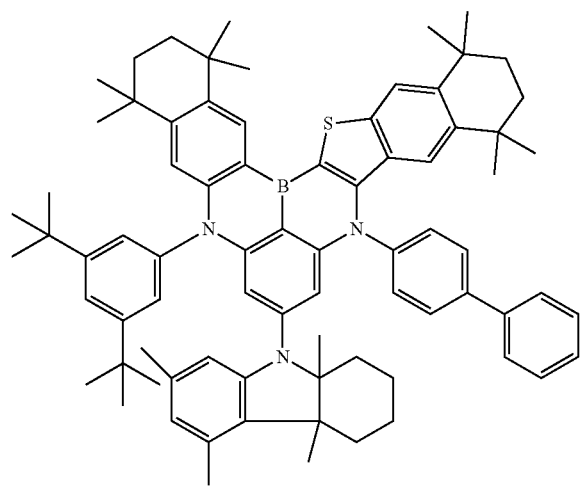
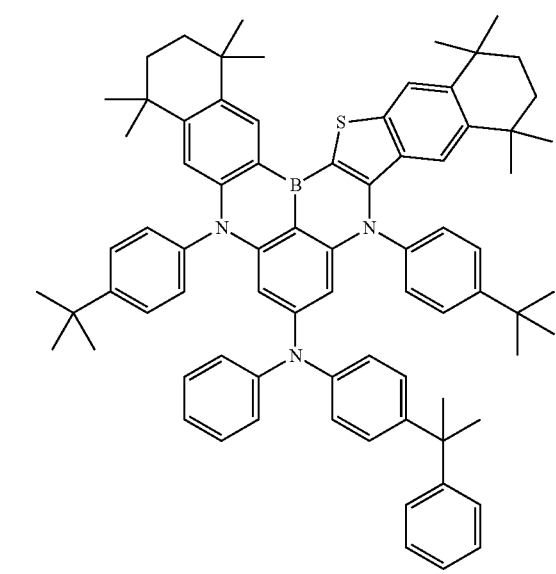
1314
-continued
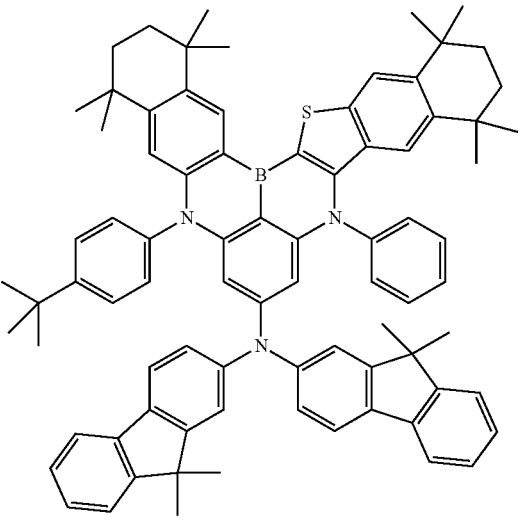
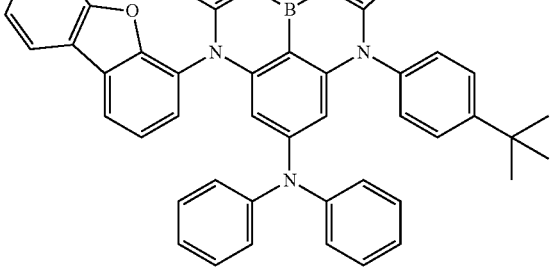
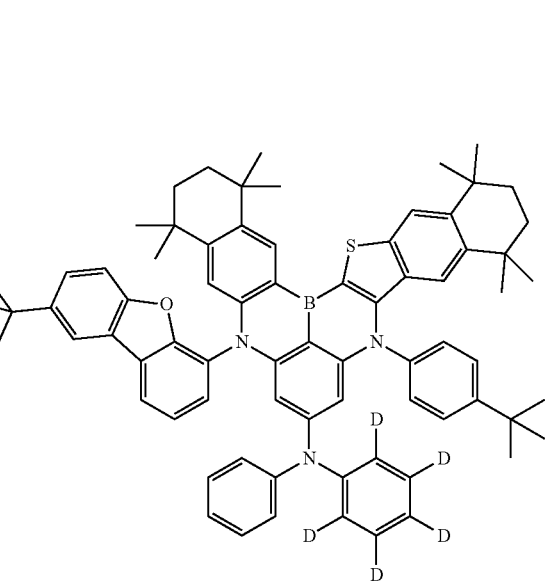

1315
-continued
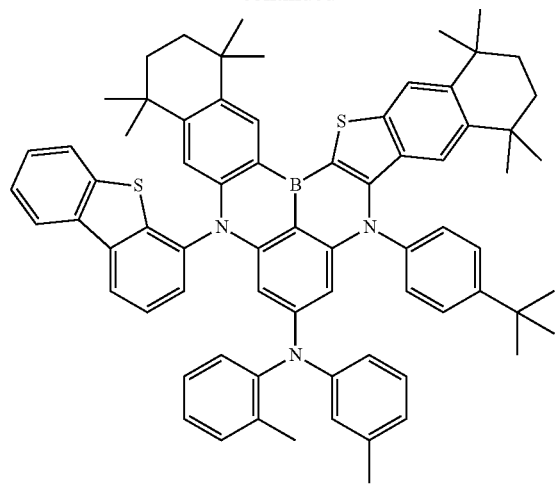
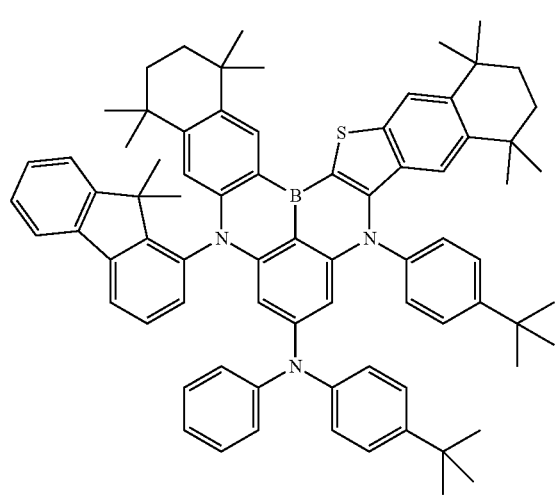
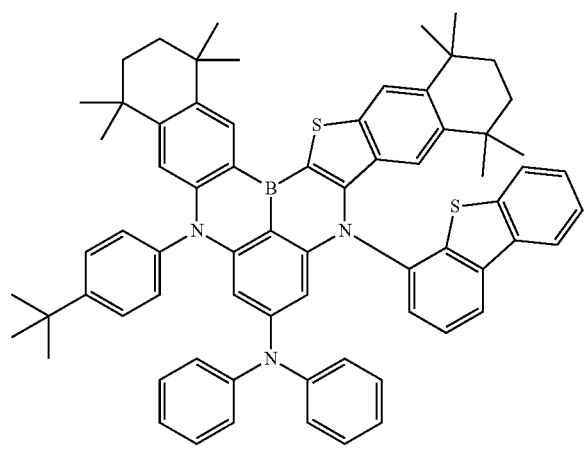
1316
-continued
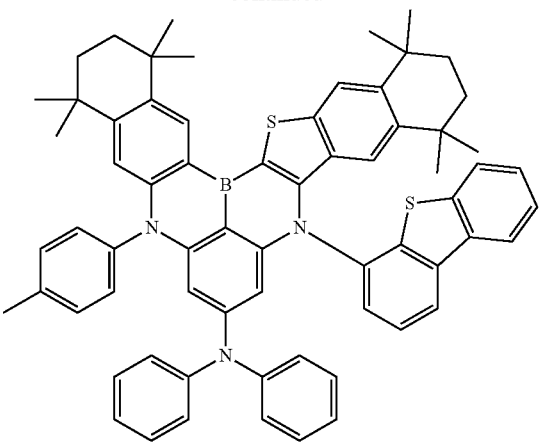
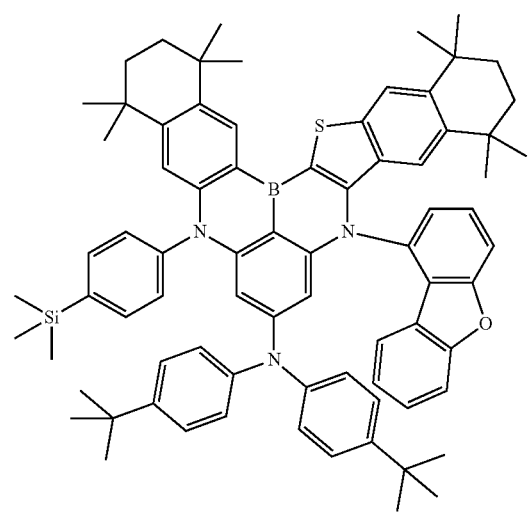
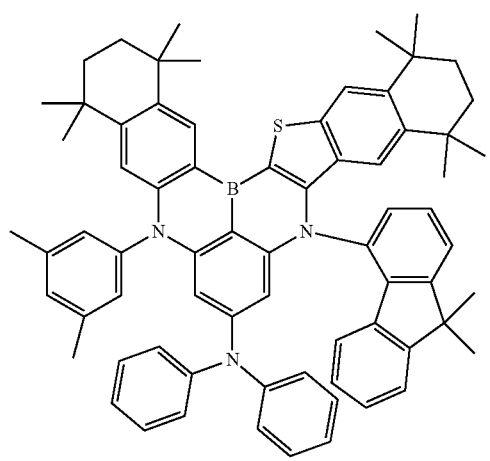

1317
-continued
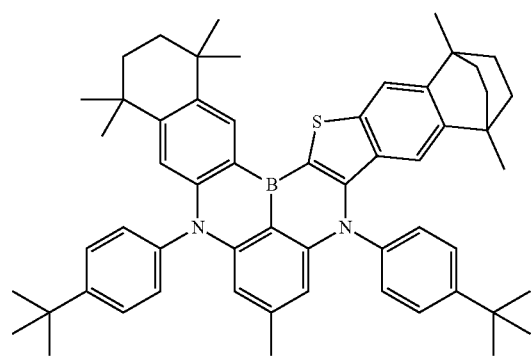
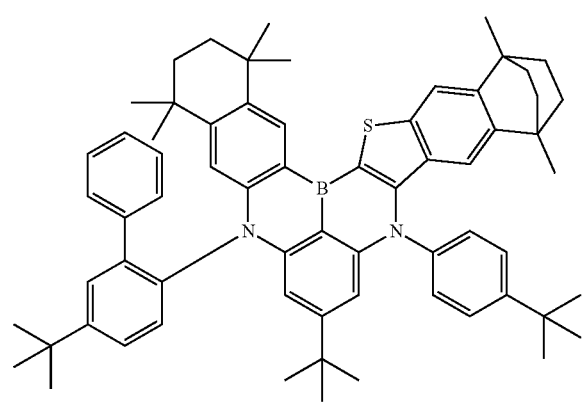
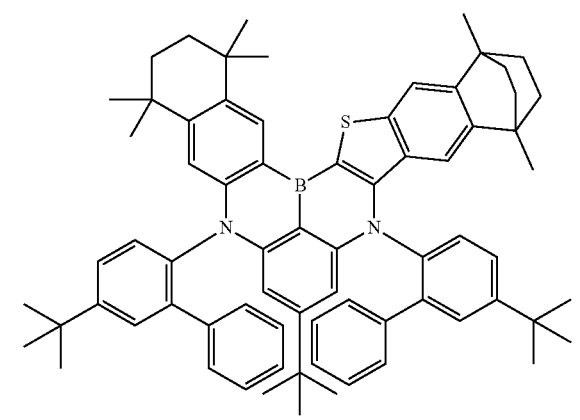
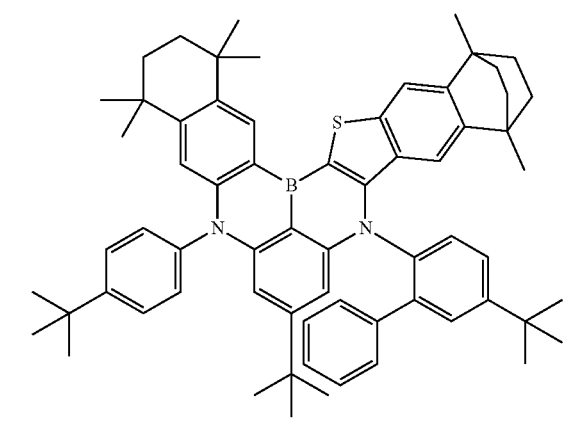
1318
-continued
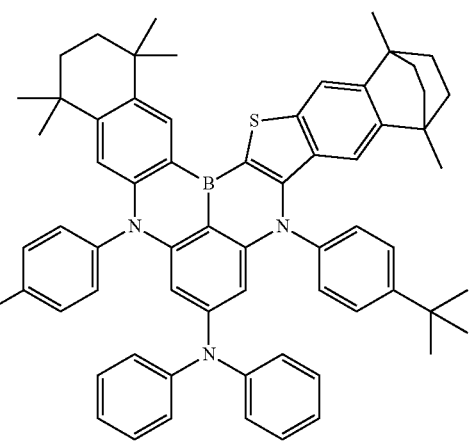
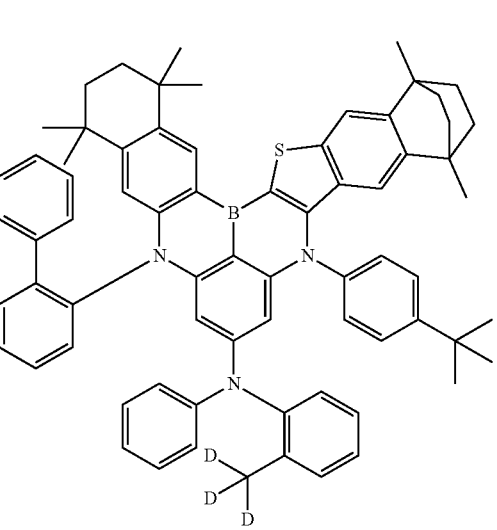
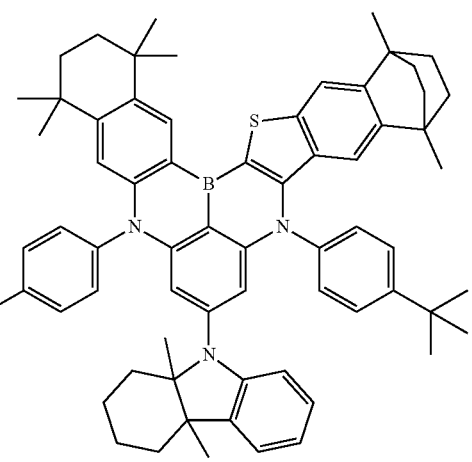

1319
-continued
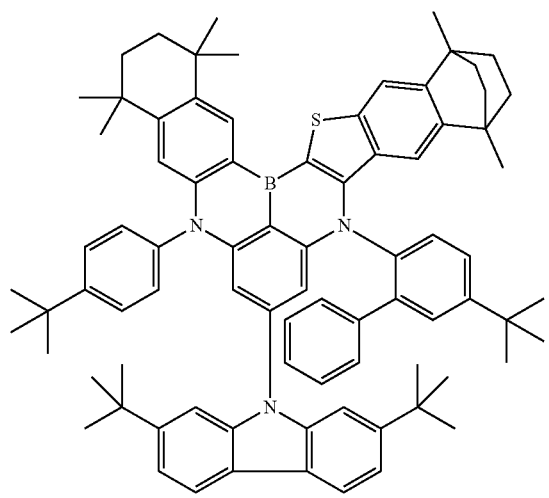
1320
-continued
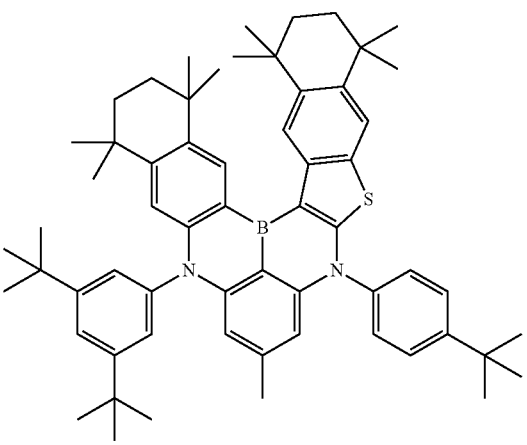
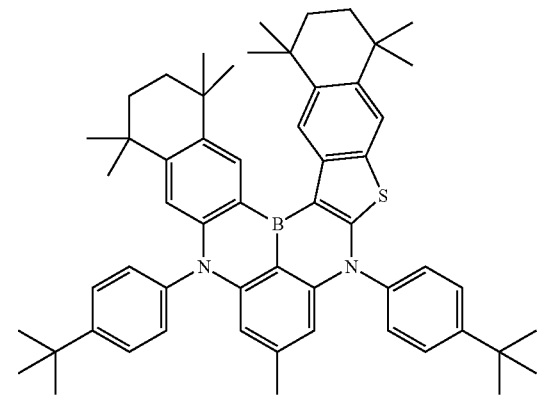
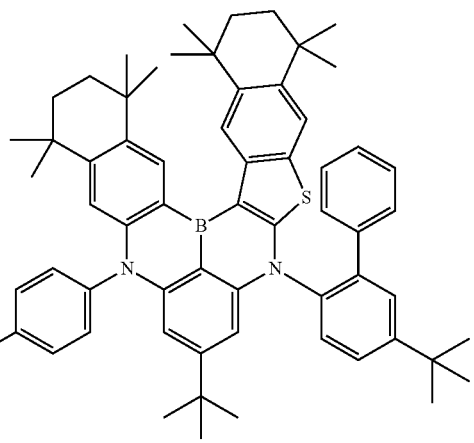
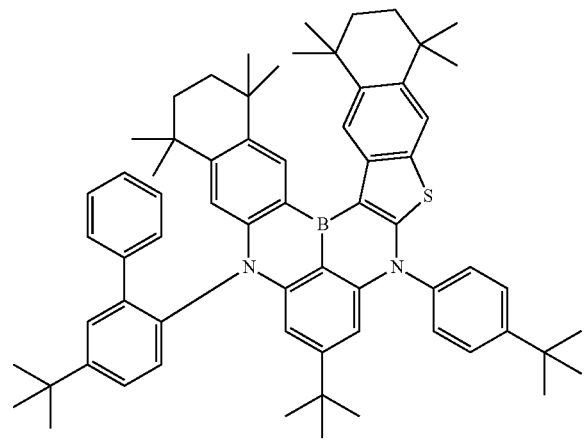
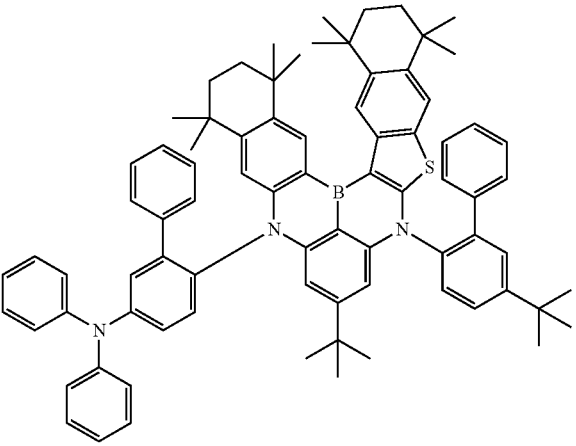

1321
-continued
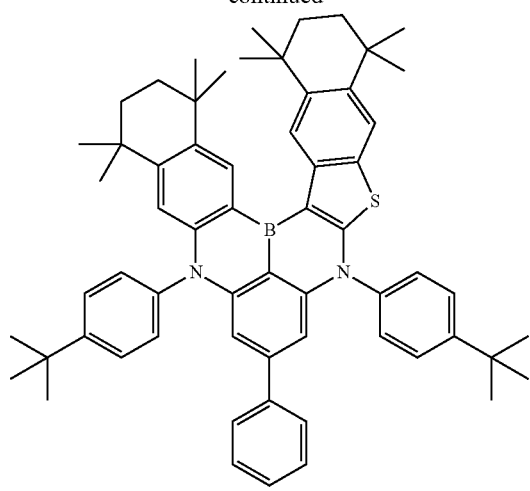
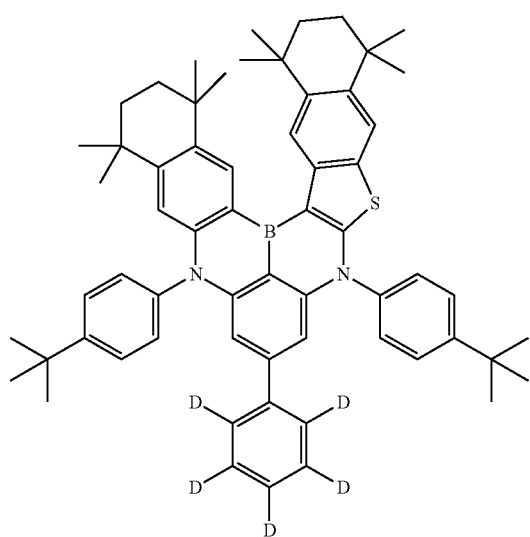
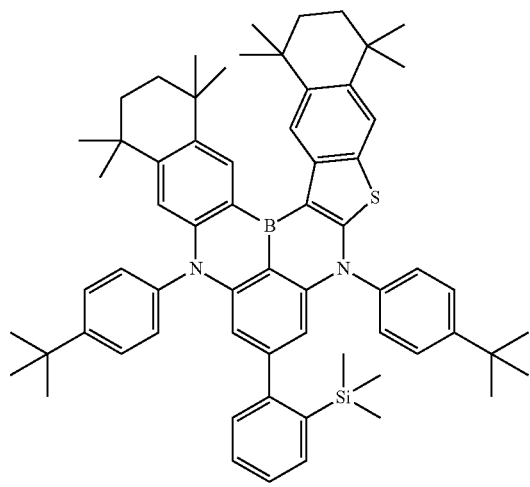
1322
-continued
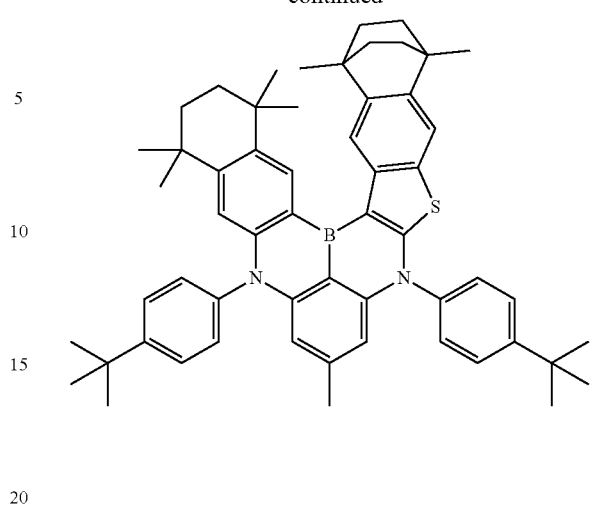
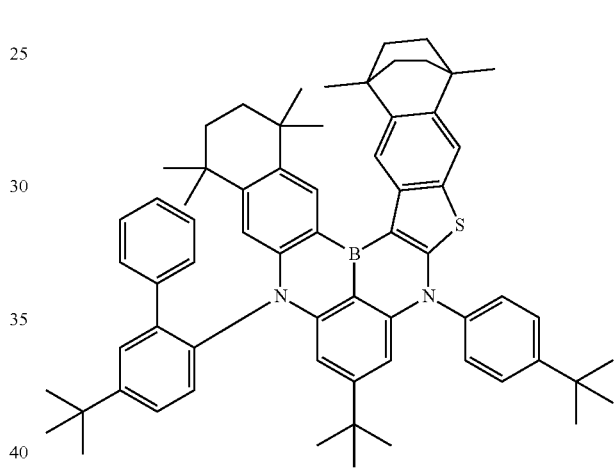
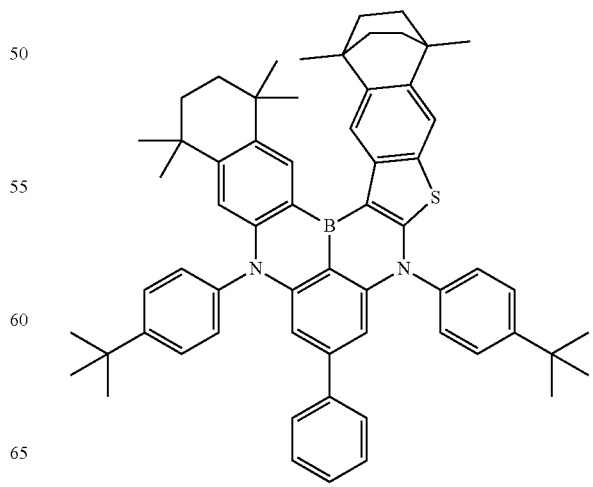

1323
-continued
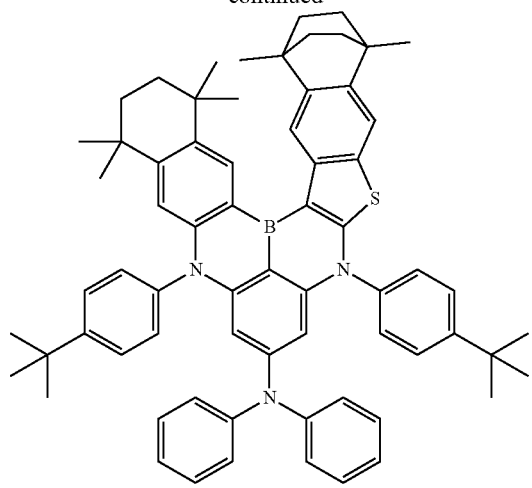
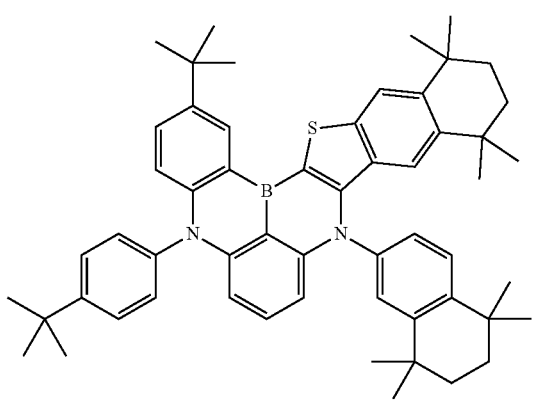
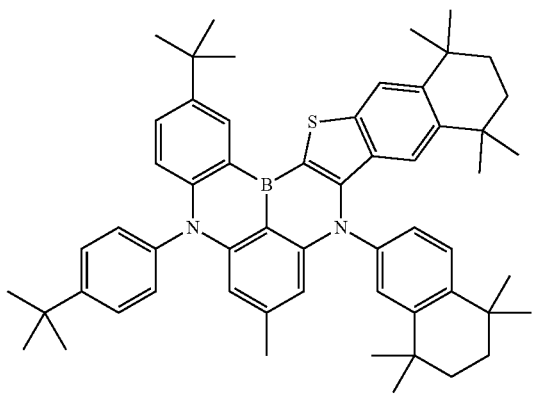
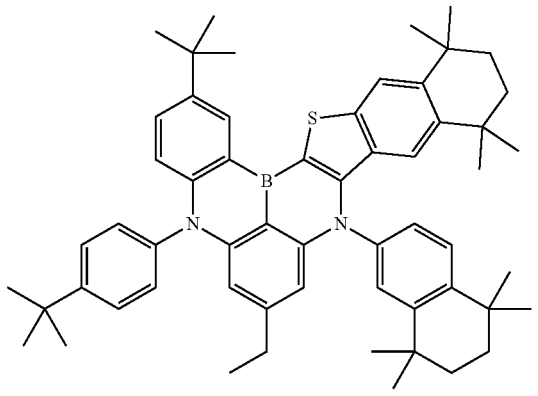
1324
-continued
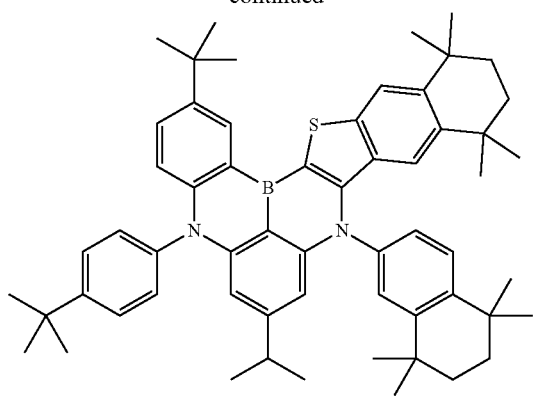
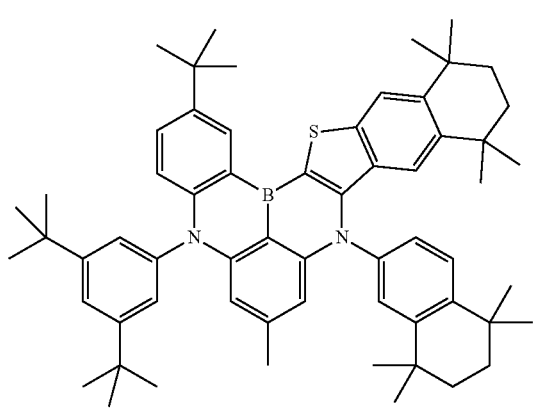
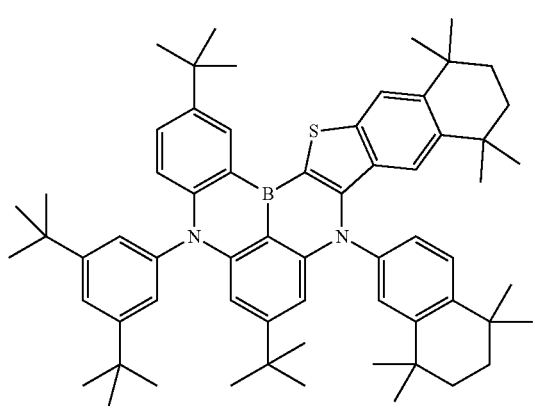
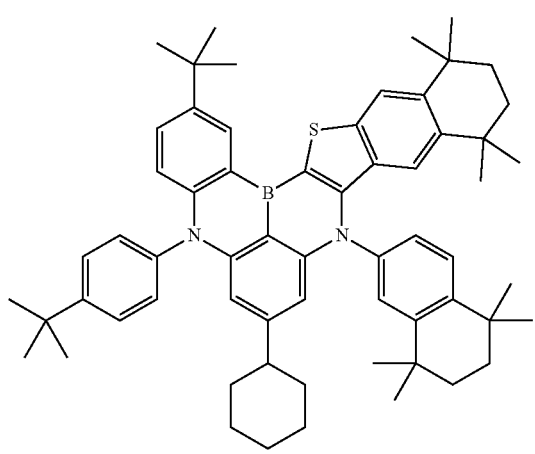

1325
-continued
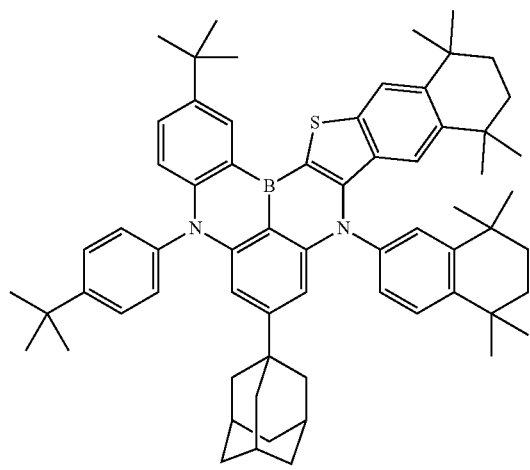
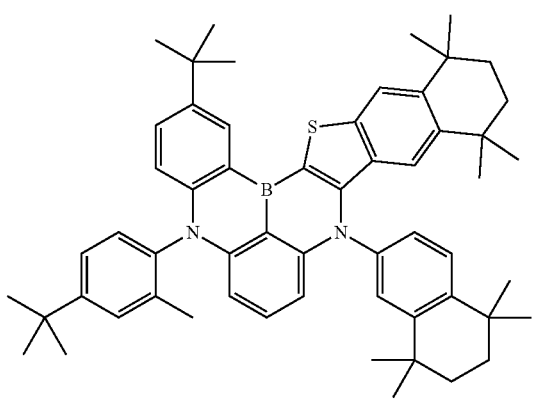
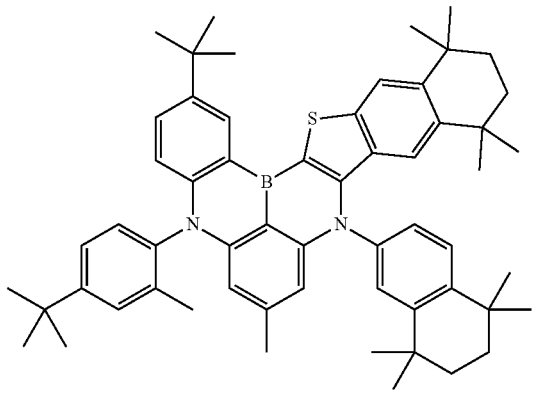
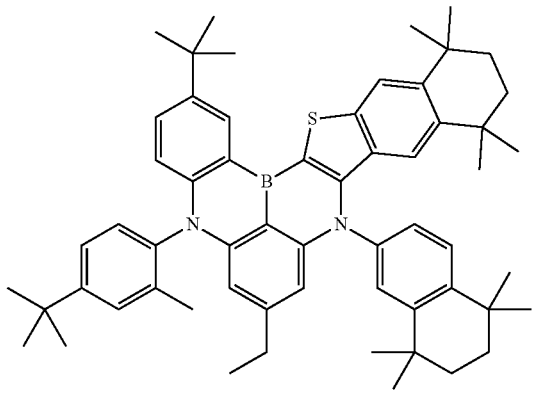
1326
-continued
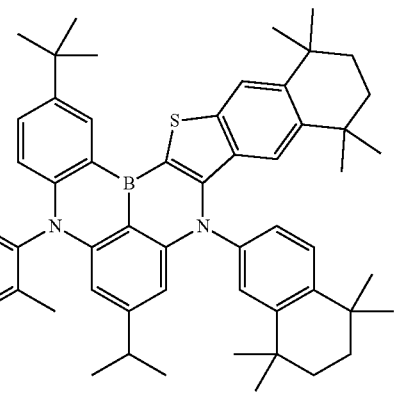
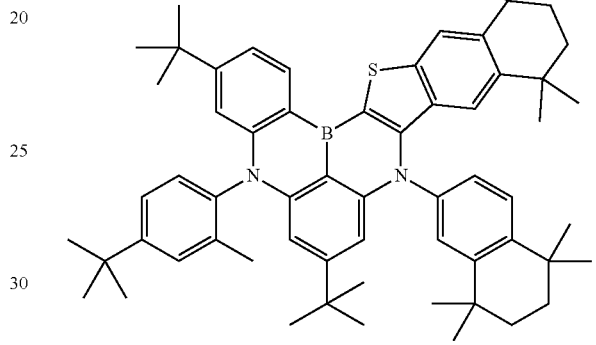
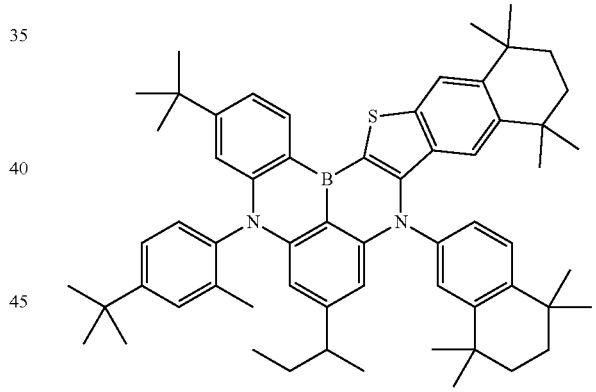
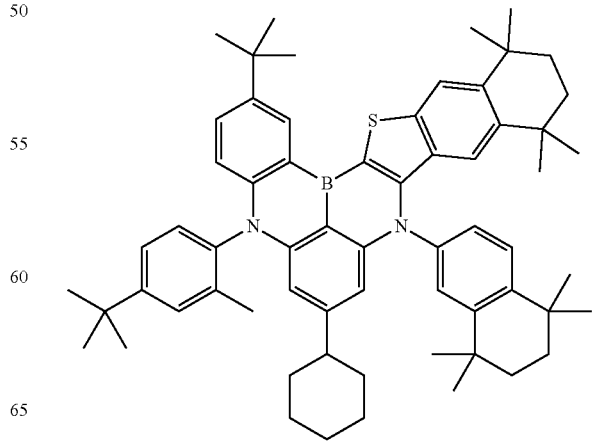

1327
-continued
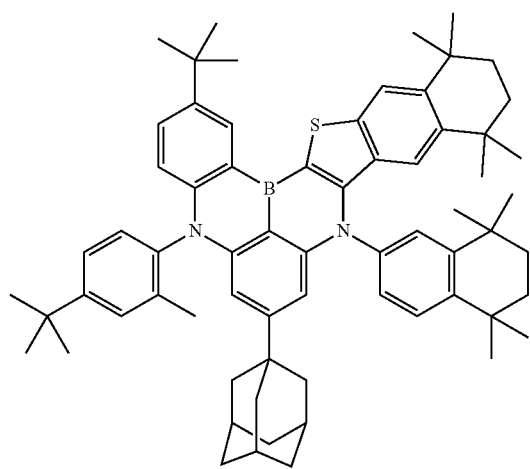
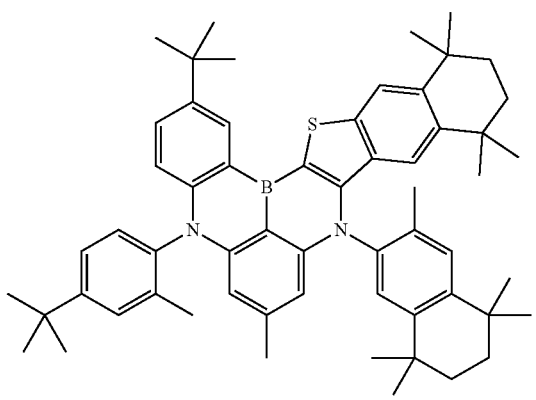
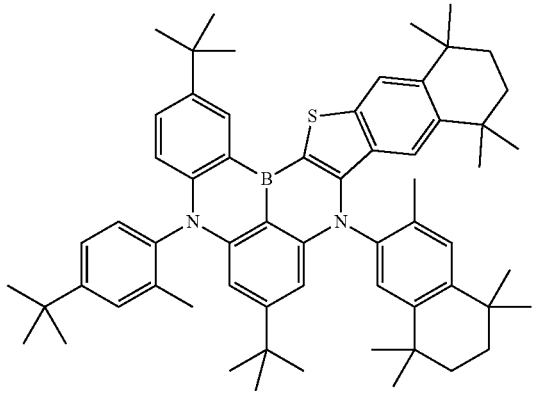
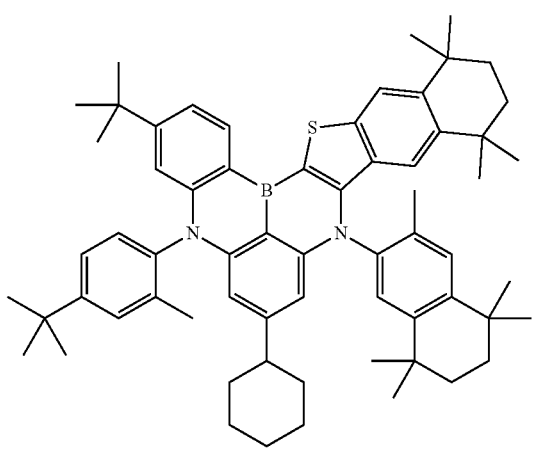
1328
-continued
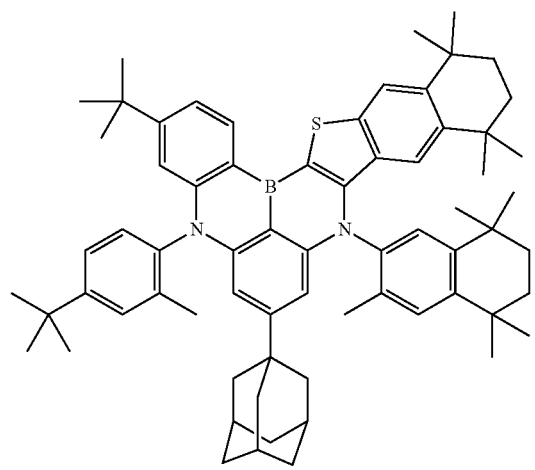
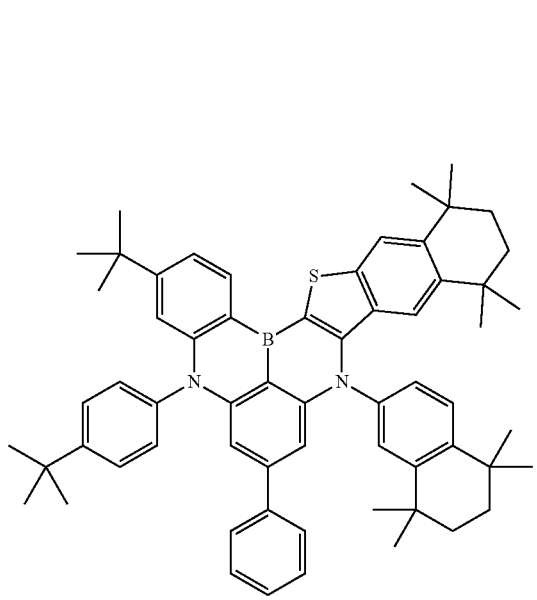

1329
-continued
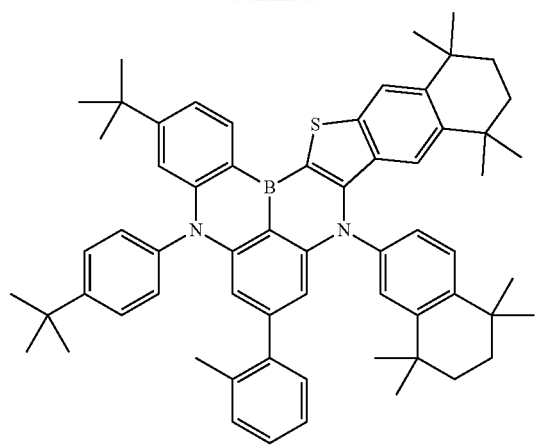
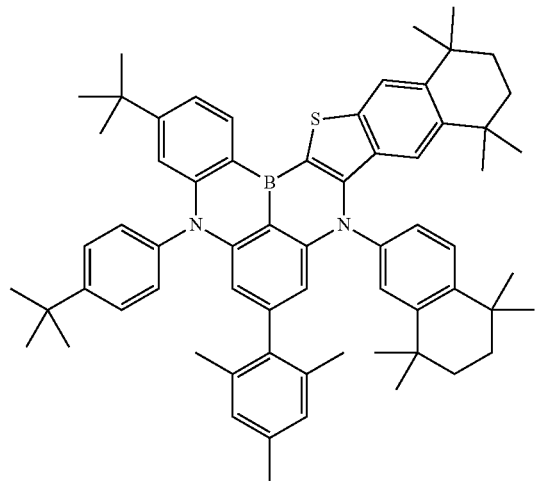
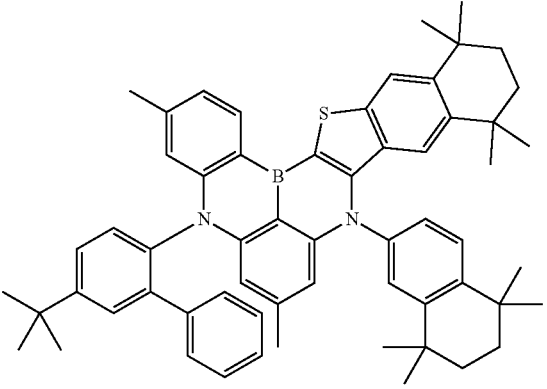
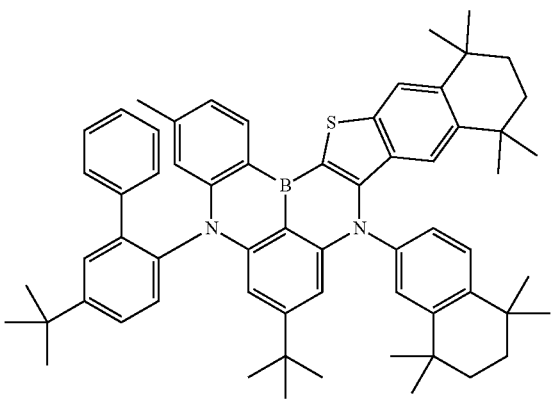
1330
-continued
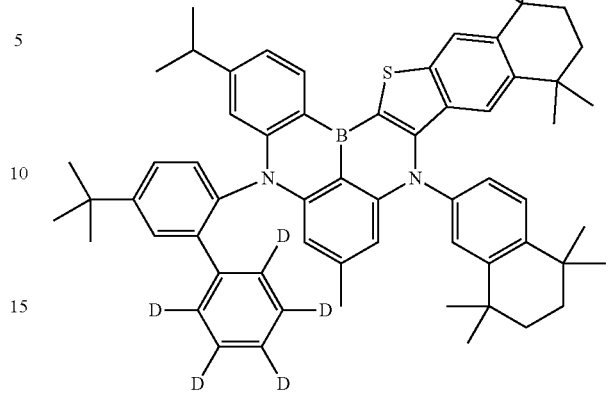
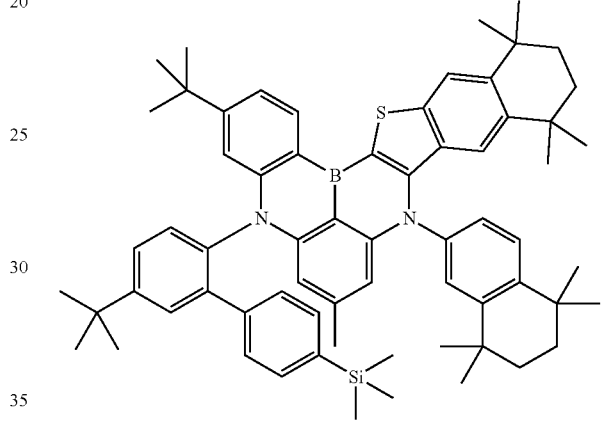
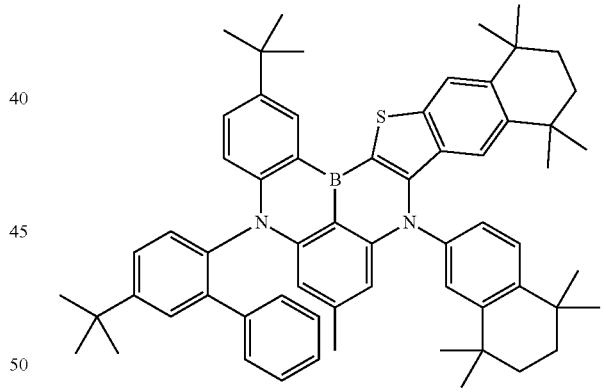
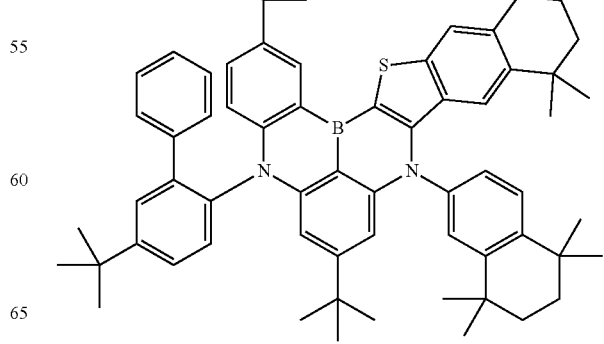

| 1331 -continued | 1332 -continued |
|---|---|
| 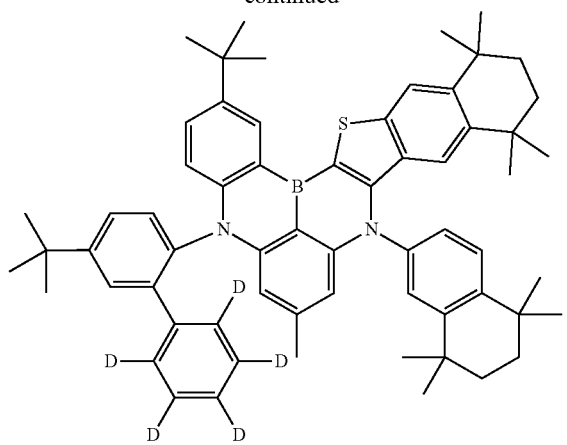 | 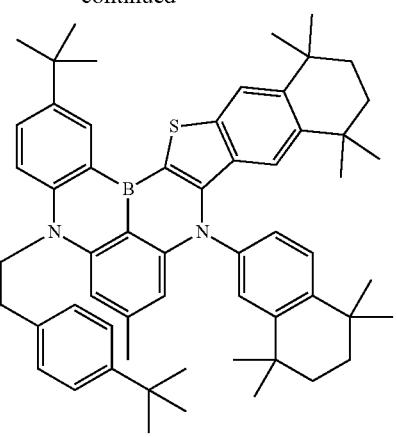 |
| 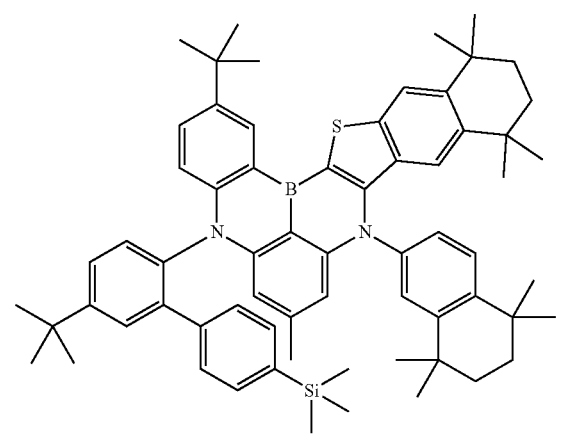 | 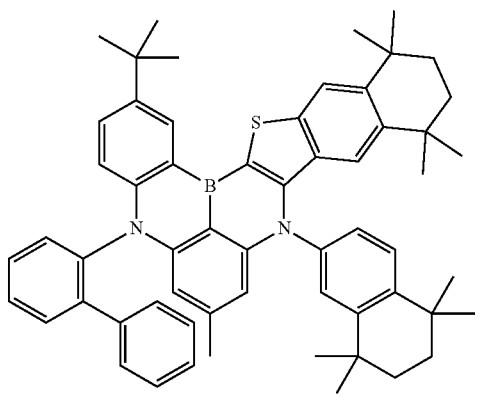 |
| 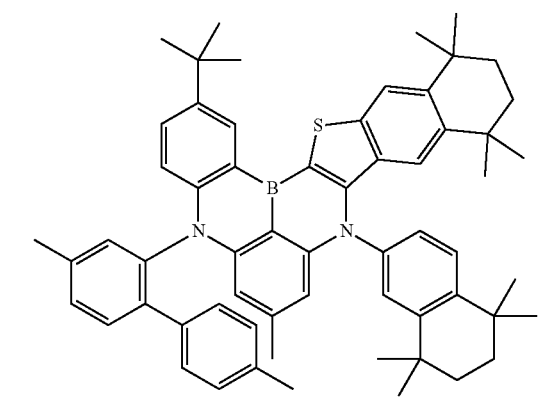 | 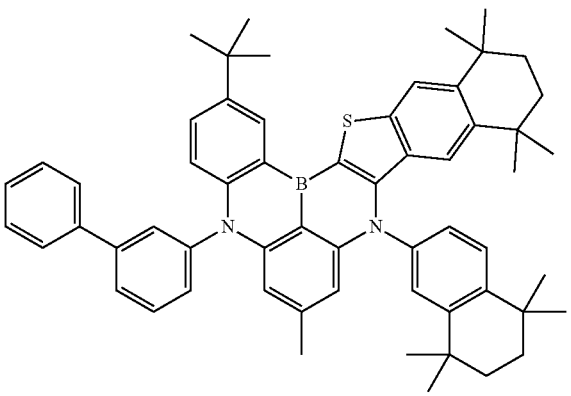 |
| 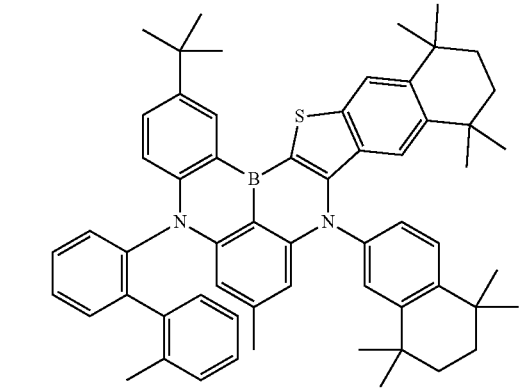 | 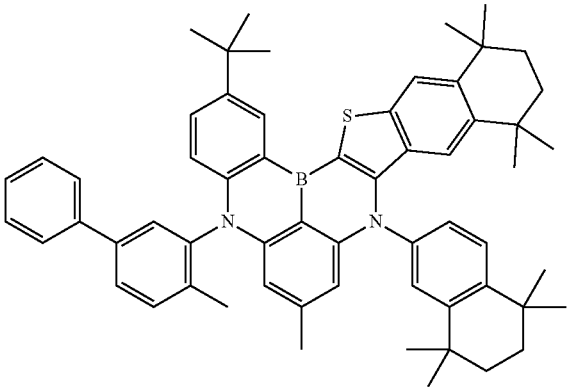 |

1333
-continued
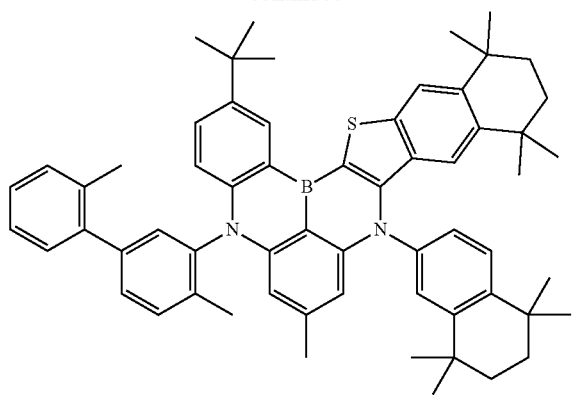
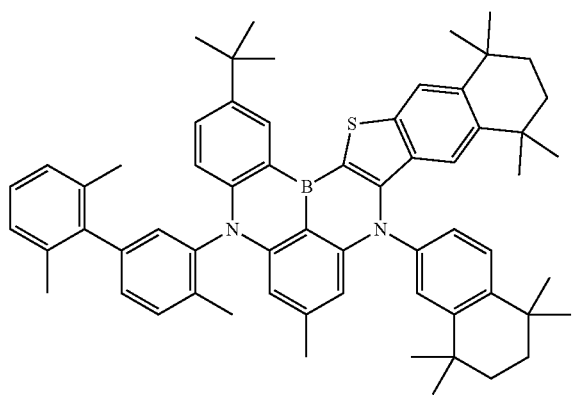
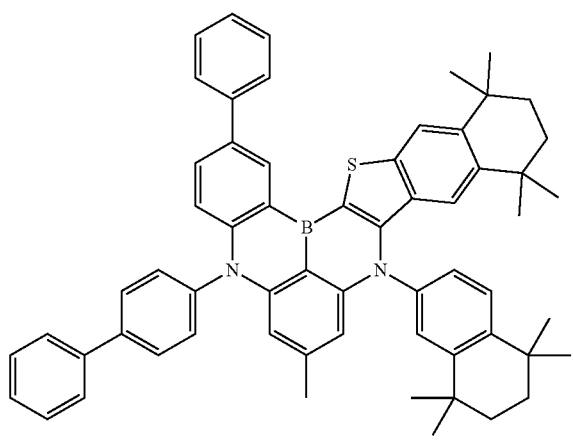
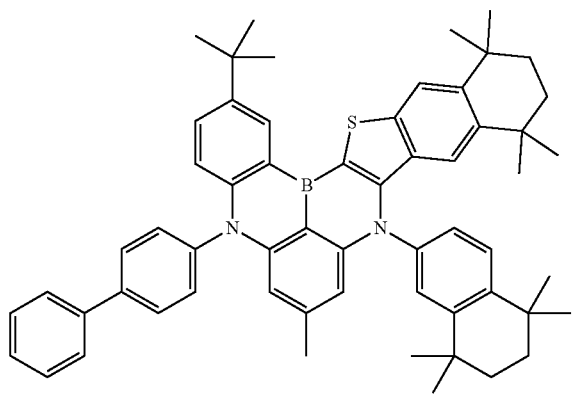
1334
-continued
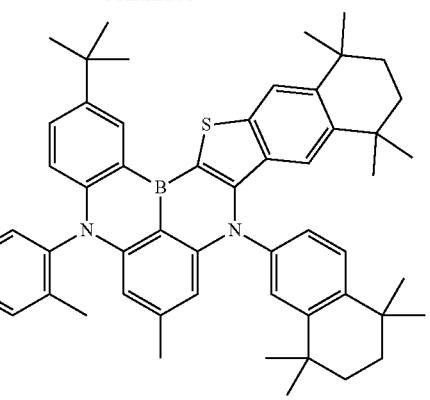
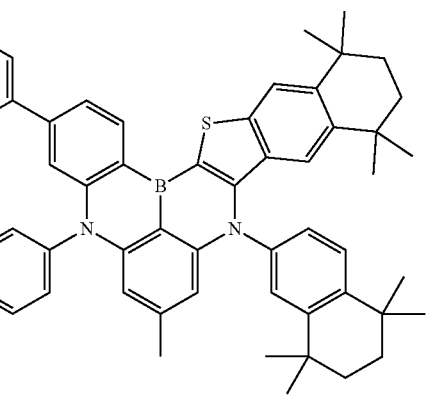
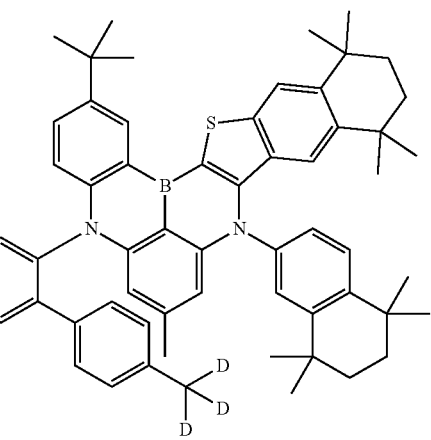
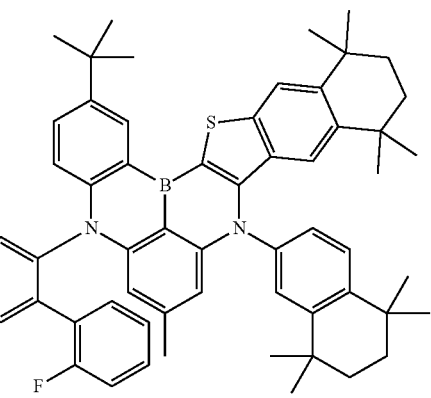

1335
-continued
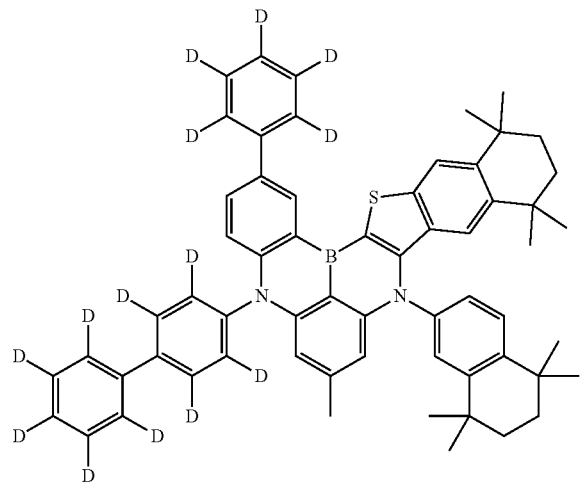
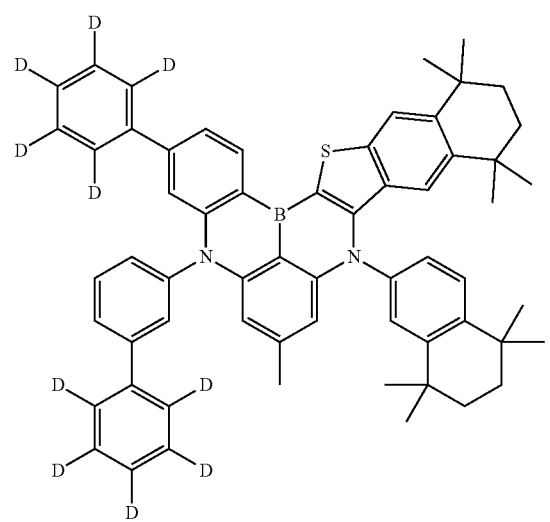
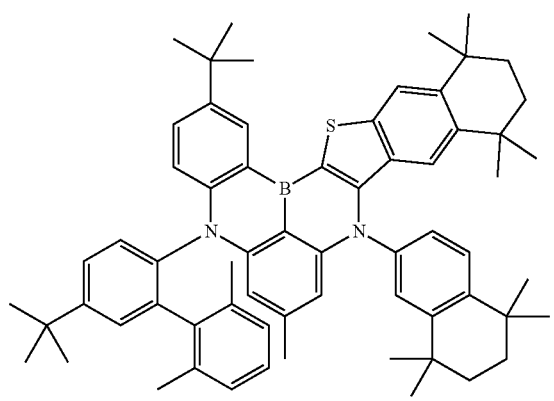
1336
-continued
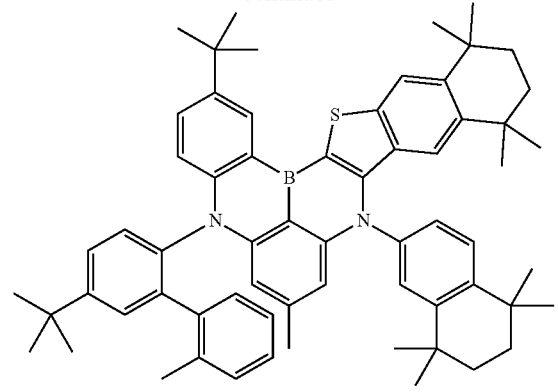
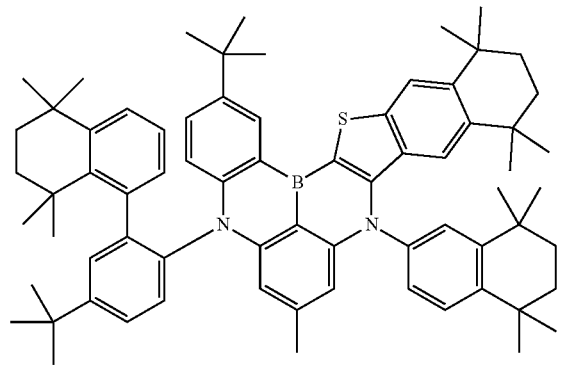

1337
-continued
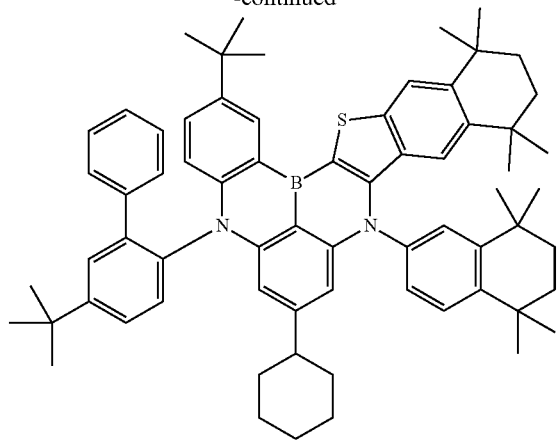
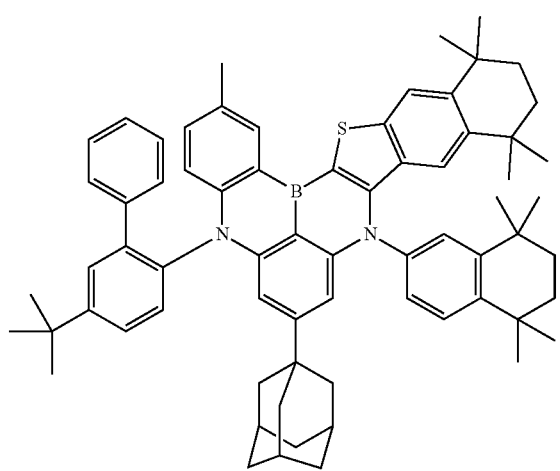
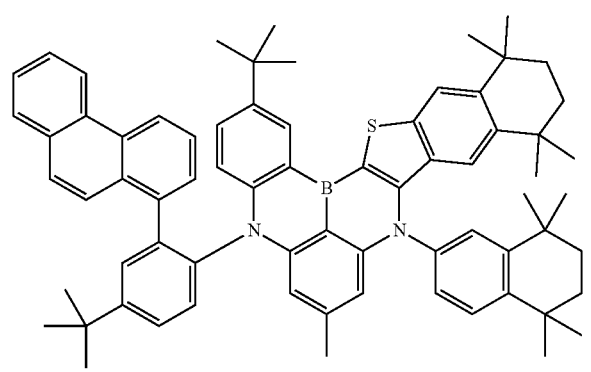
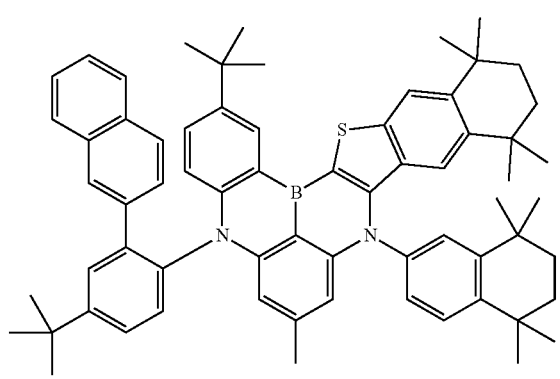
1338
-continued
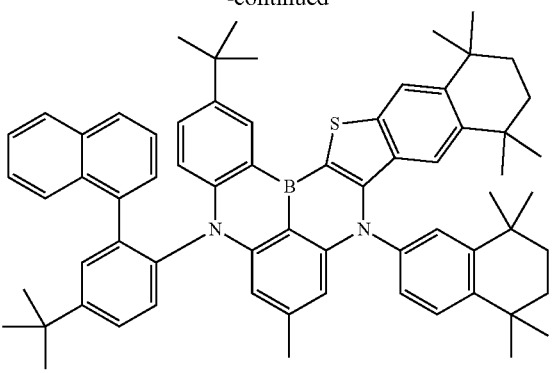
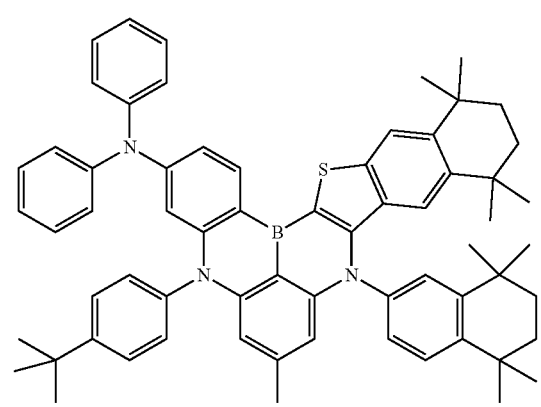
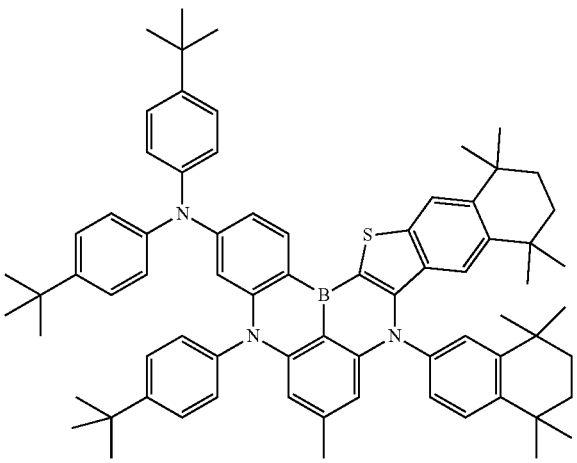
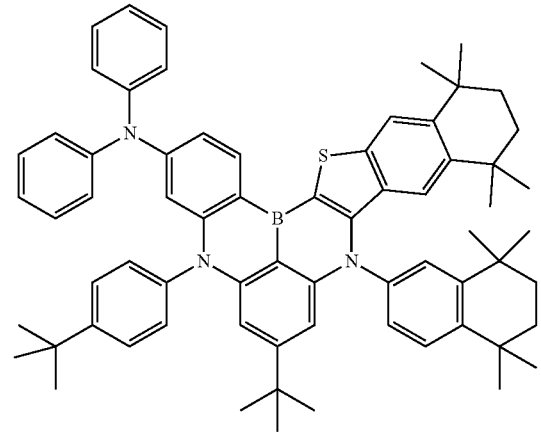

1339
-continued
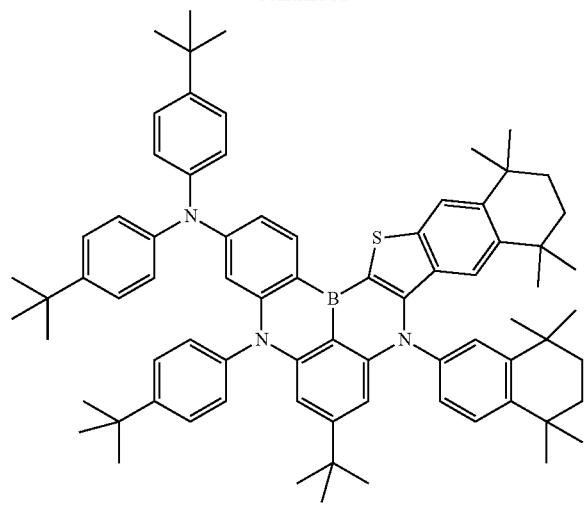
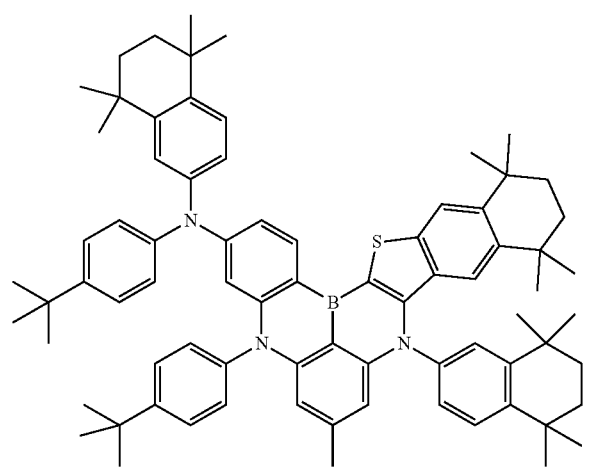
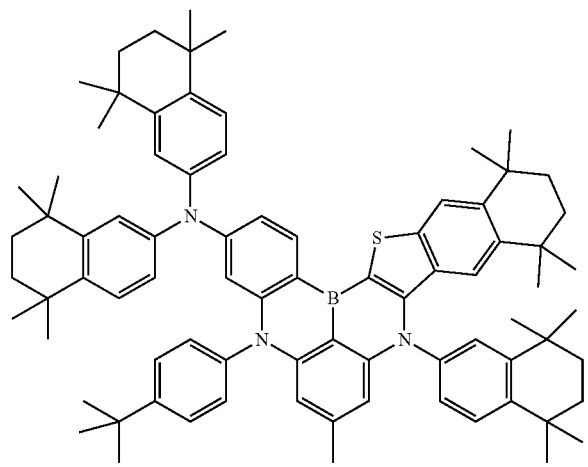
1340
-continued
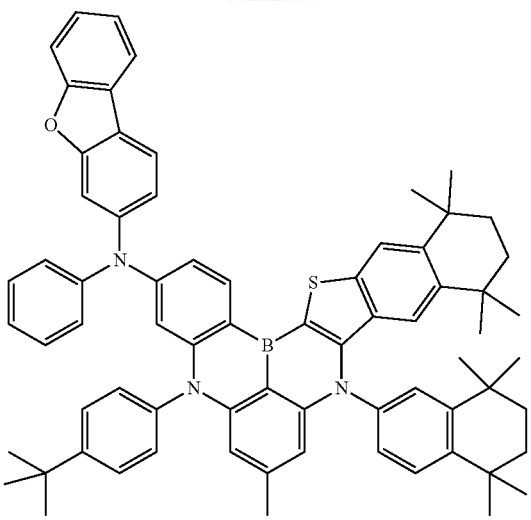
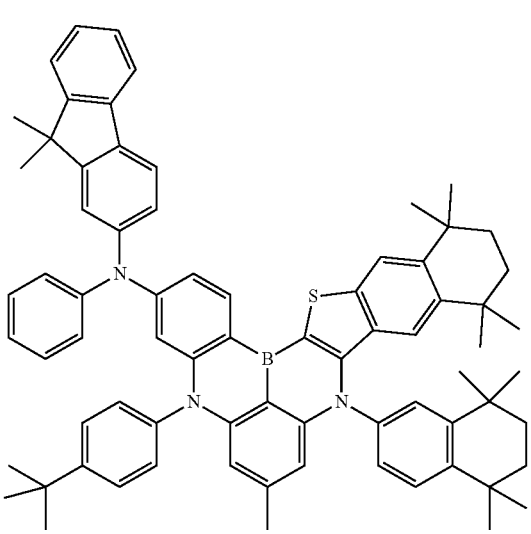
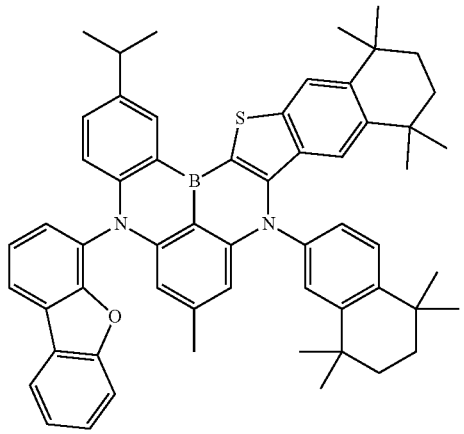

1341
-continued
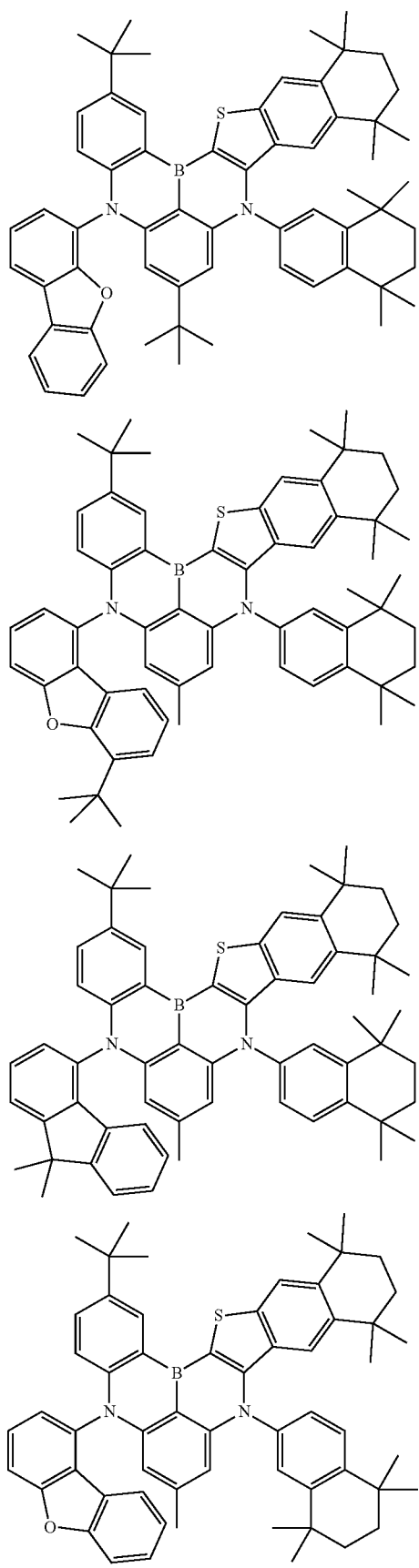
1342
-continued
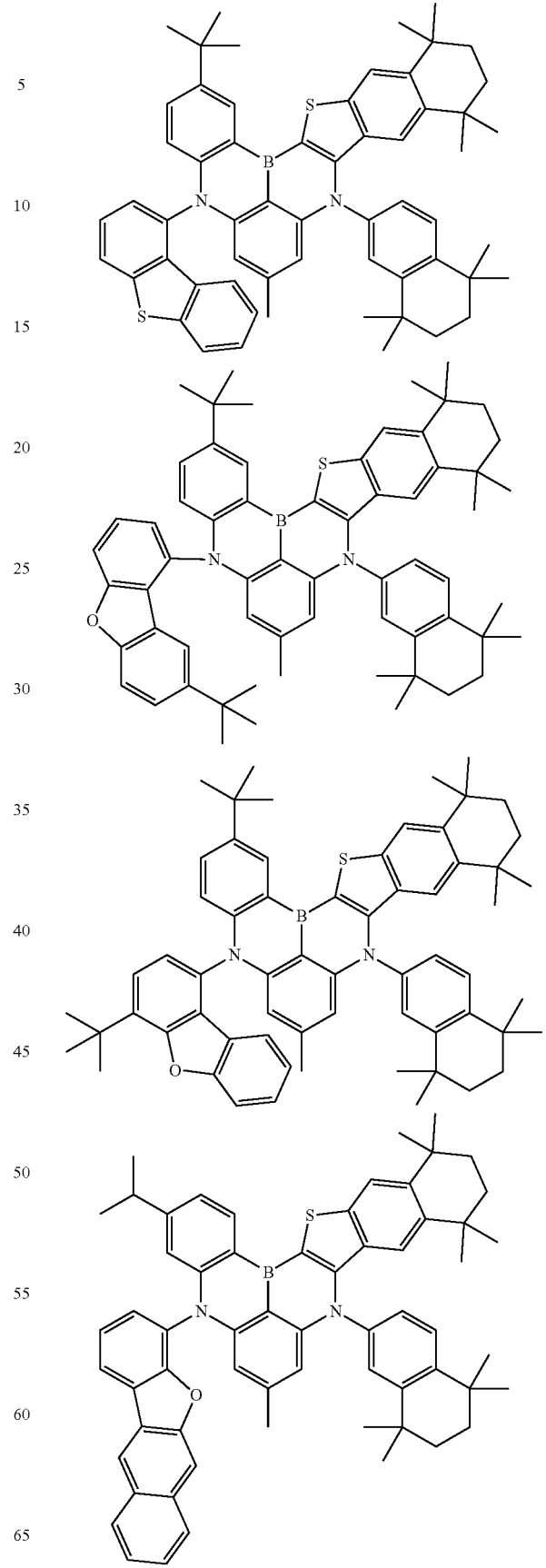

1343
-continued
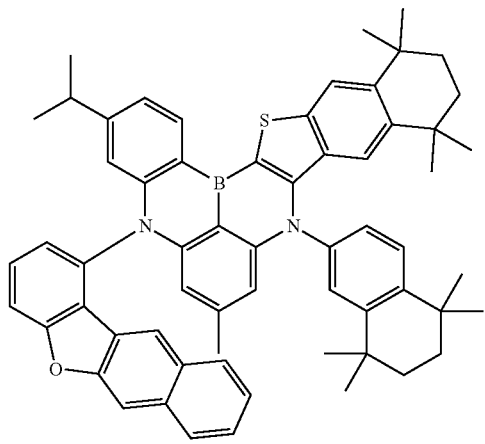
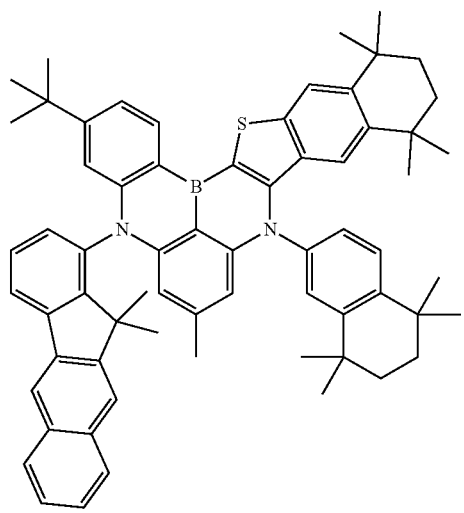
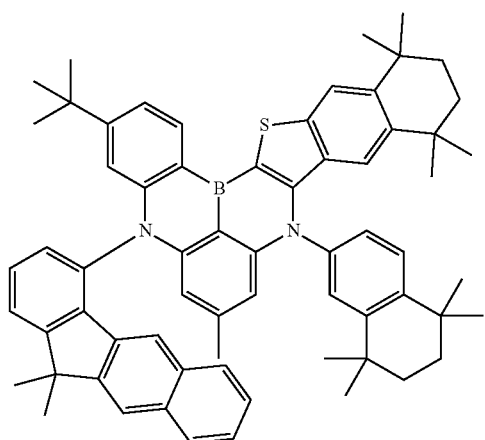
1344
-continued
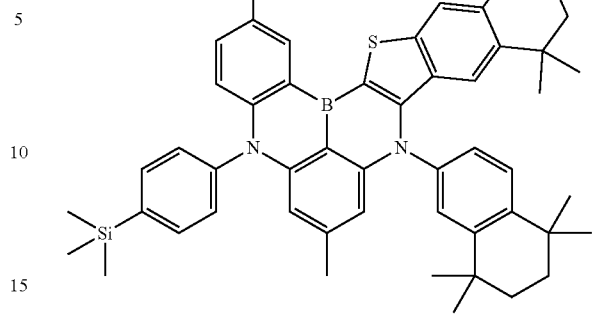
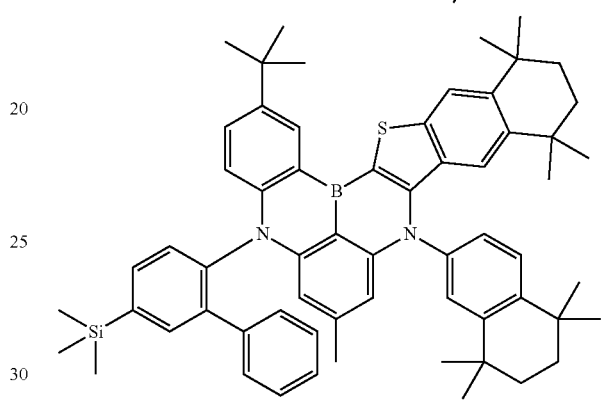
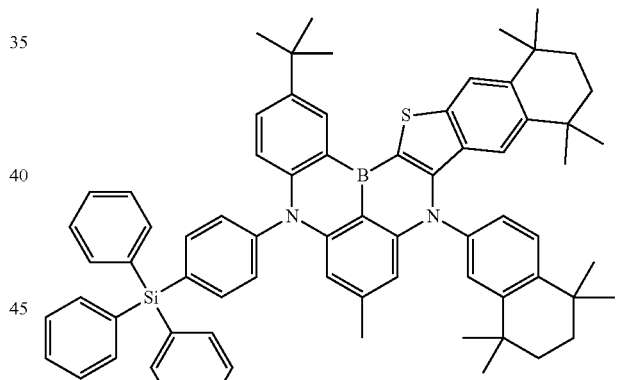
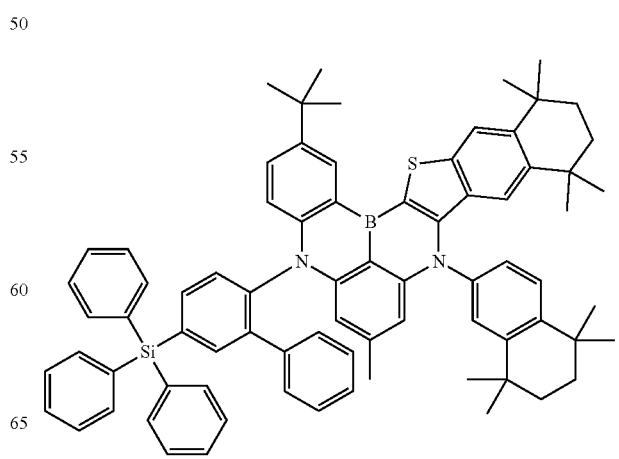

1345
-continued
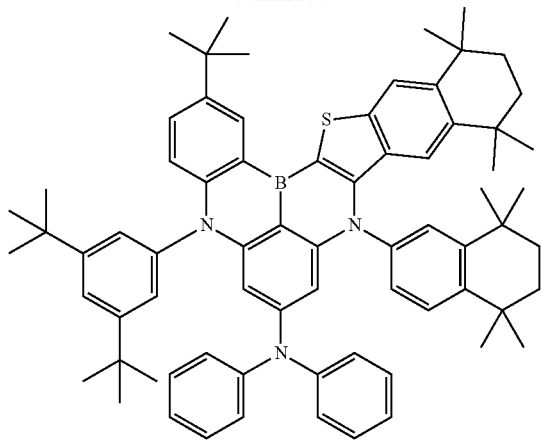
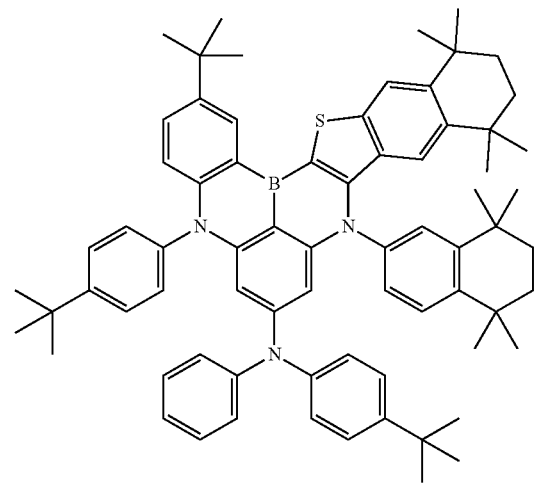
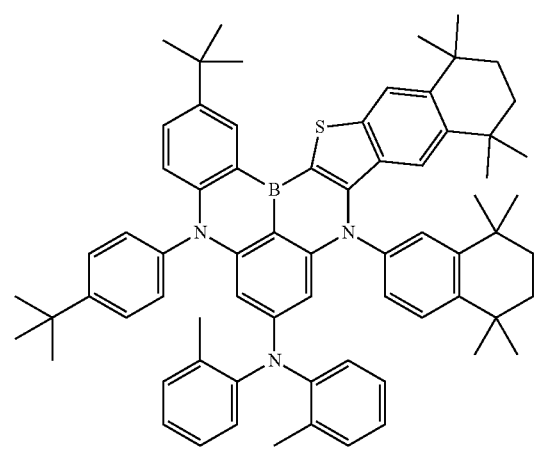
1346
-continued
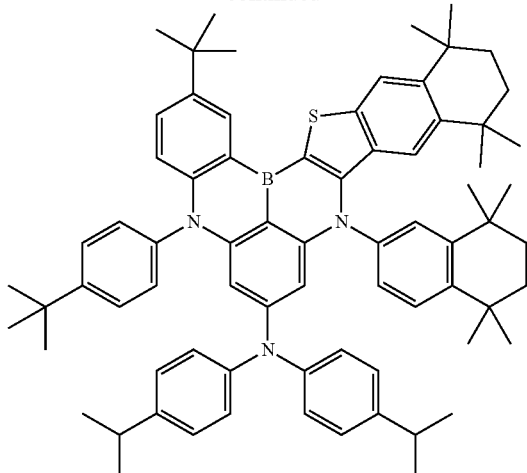
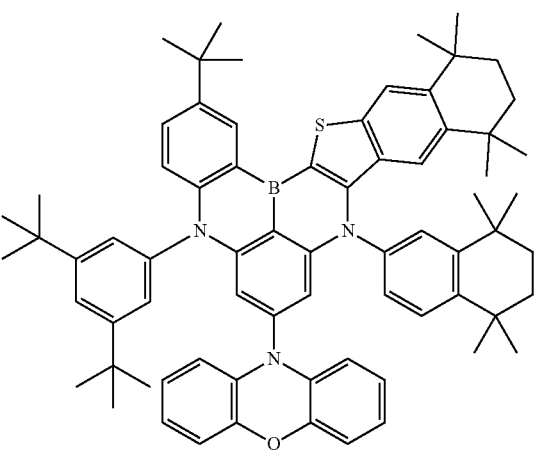
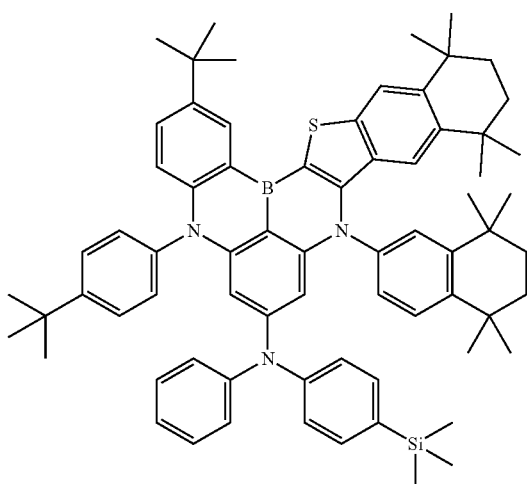

1347
-continued
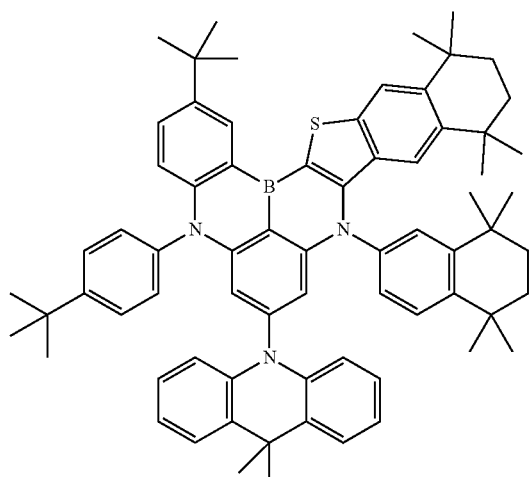
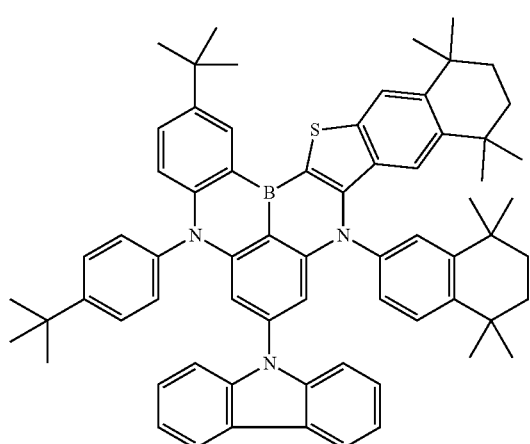
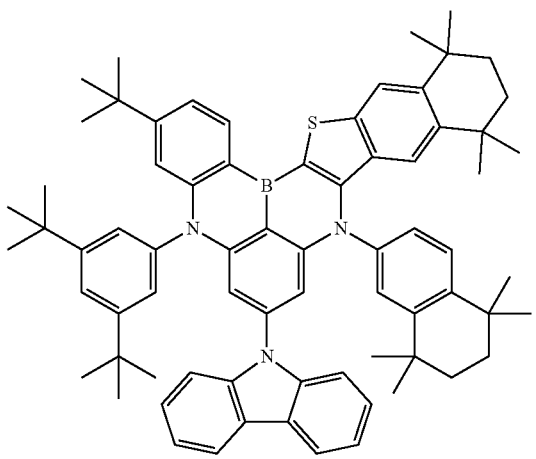
1348
-continued
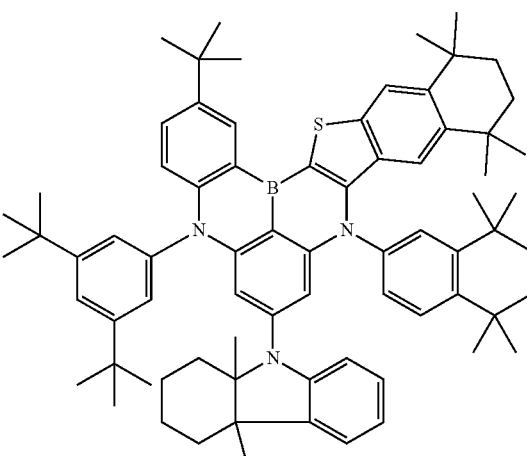
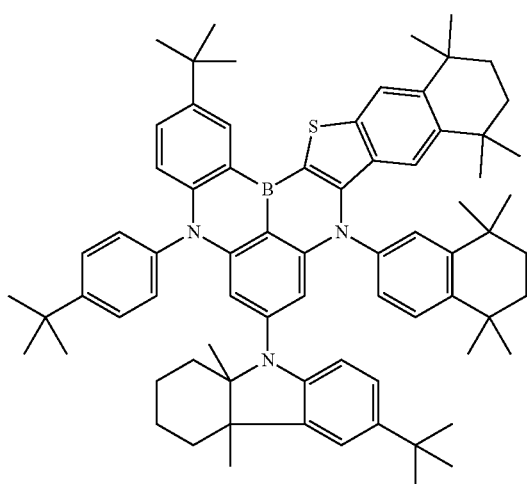
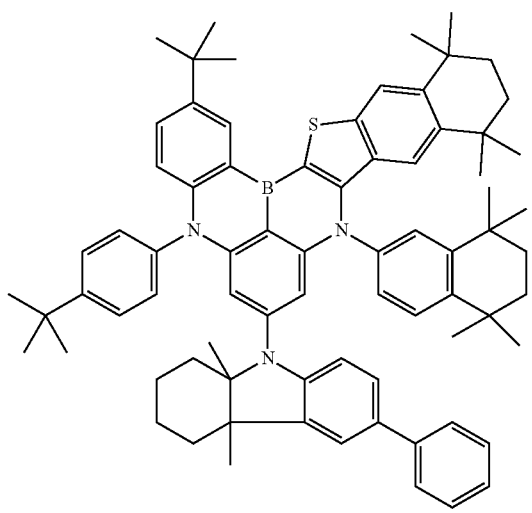

1349
-continued
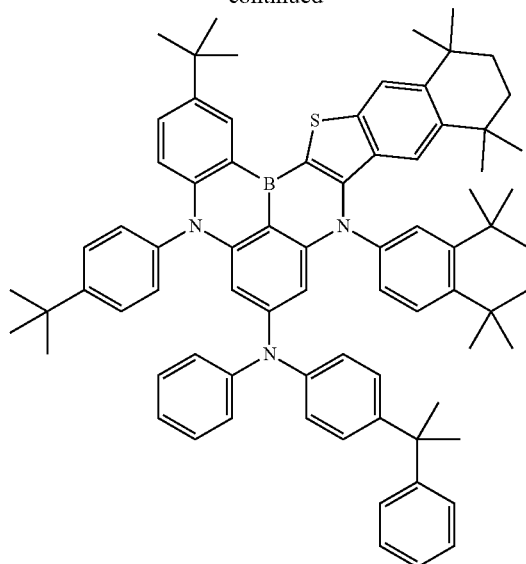
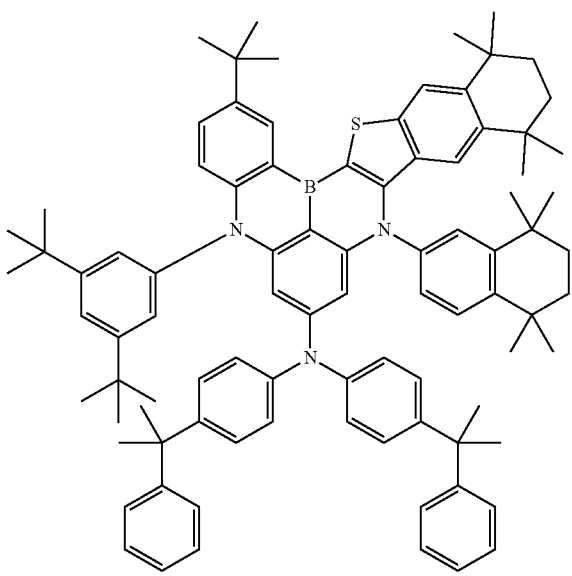
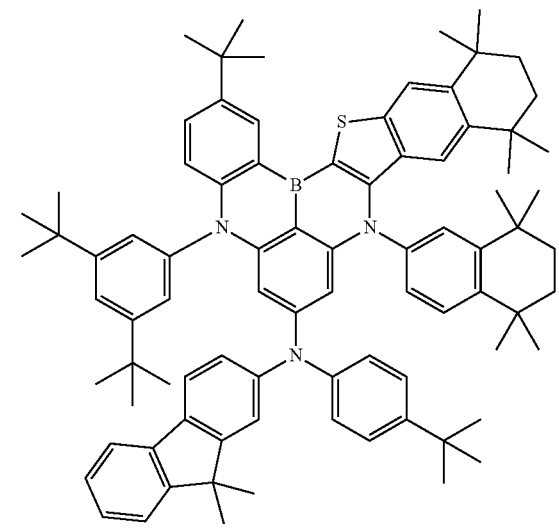
1350
-continued
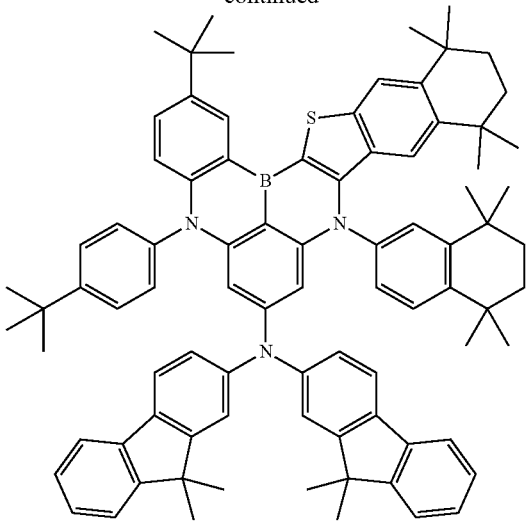
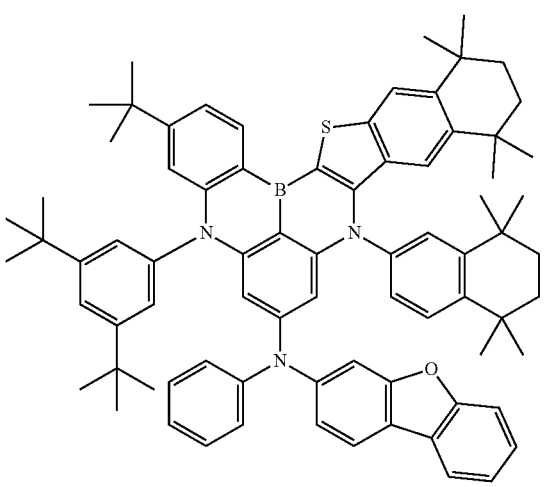
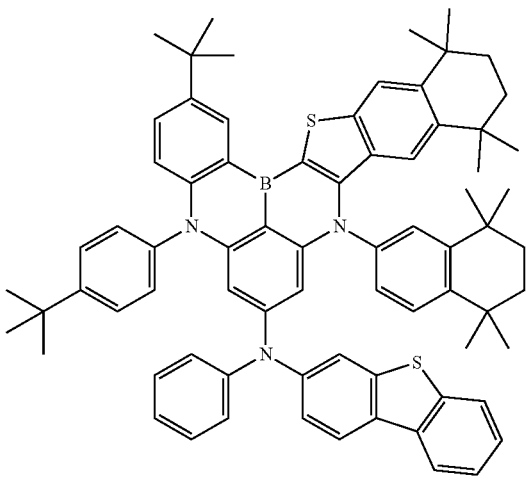

1351
-continued
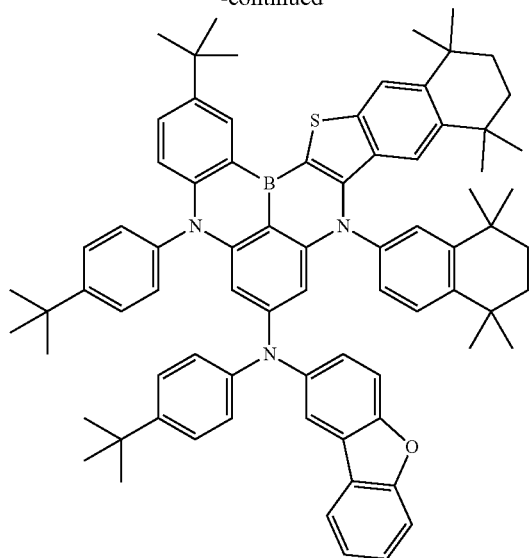
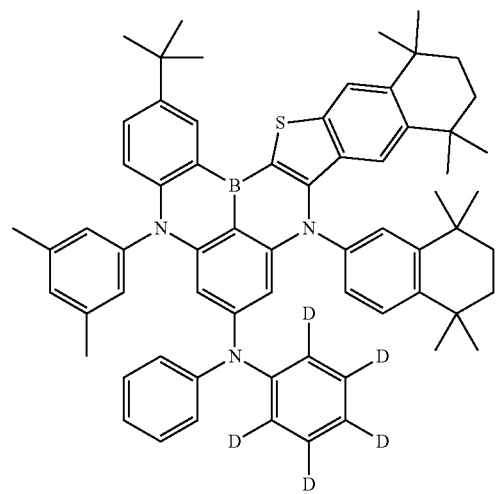
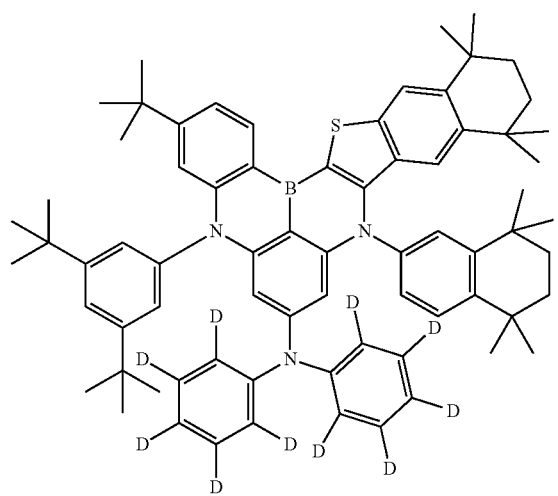
1352
-continued
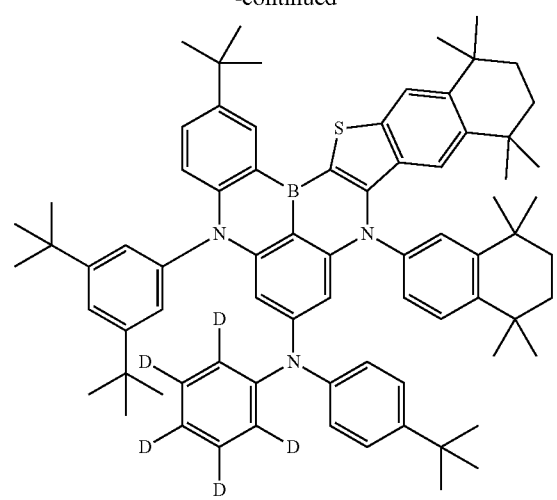
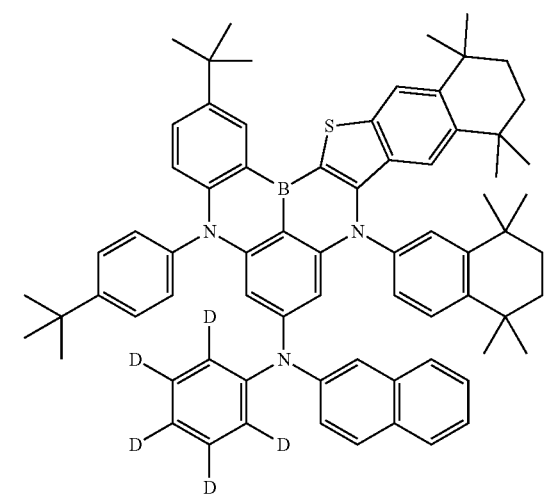
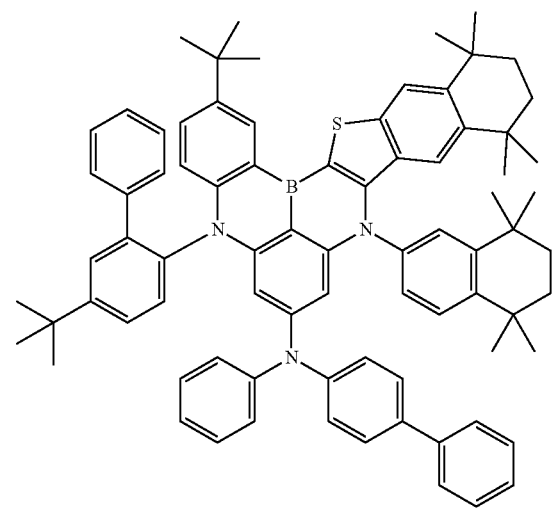

1353
-continued
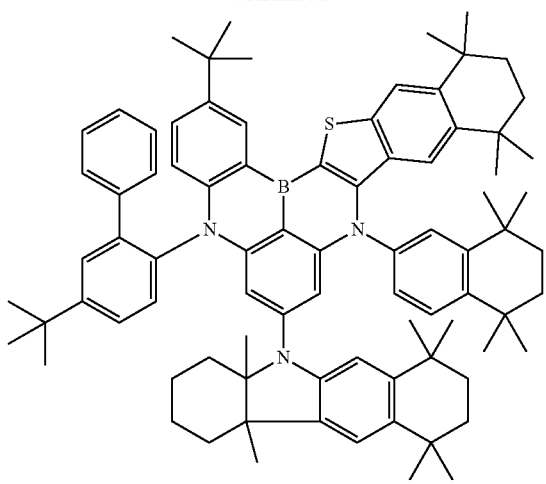
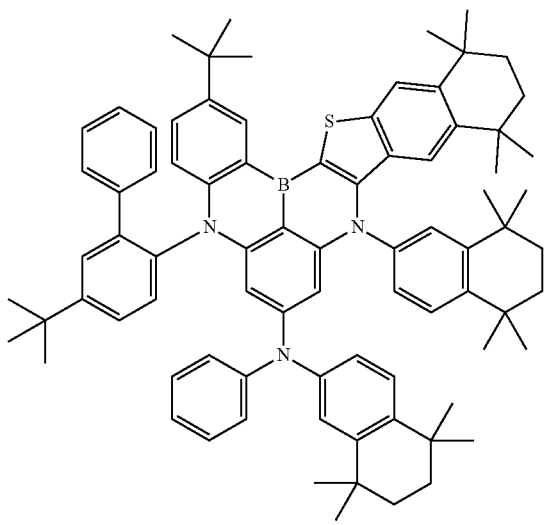
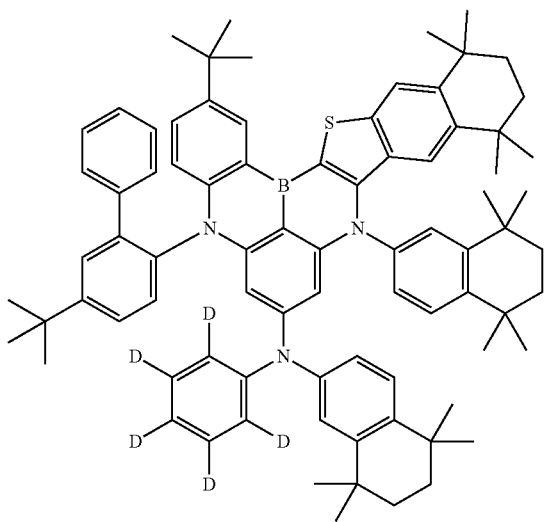
1354
-continued
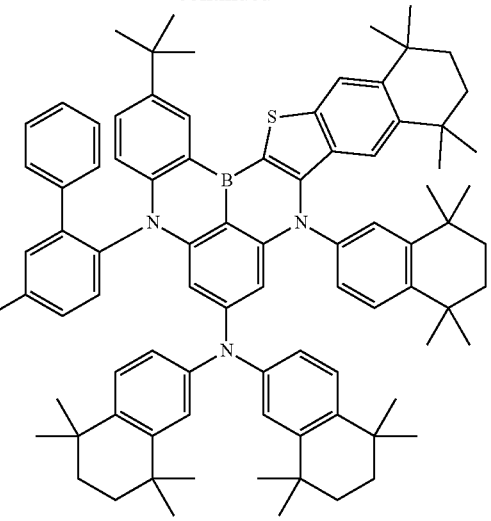
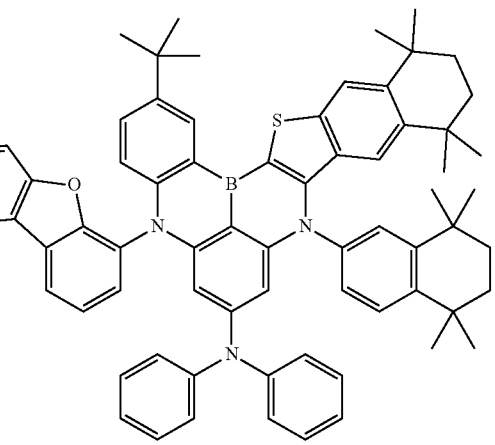
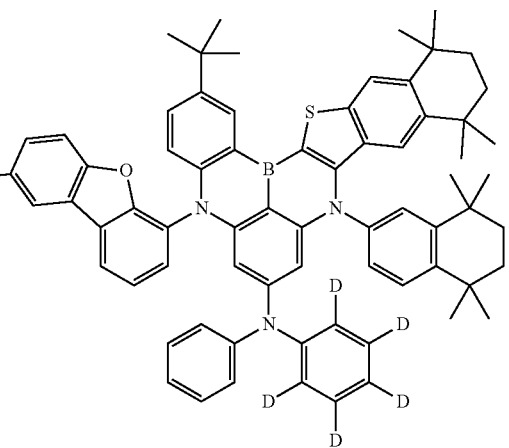

1355
-continued
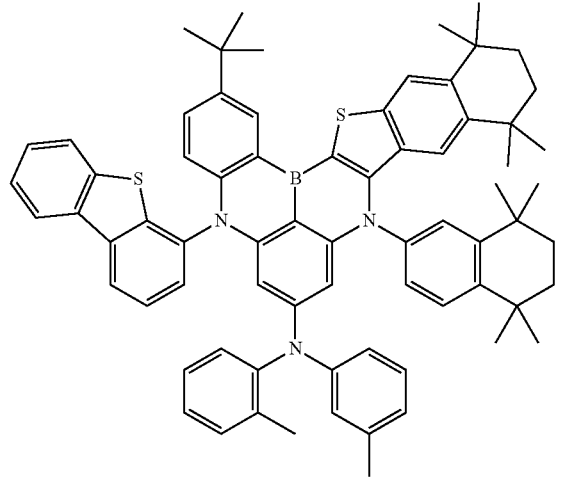
1356
-continued
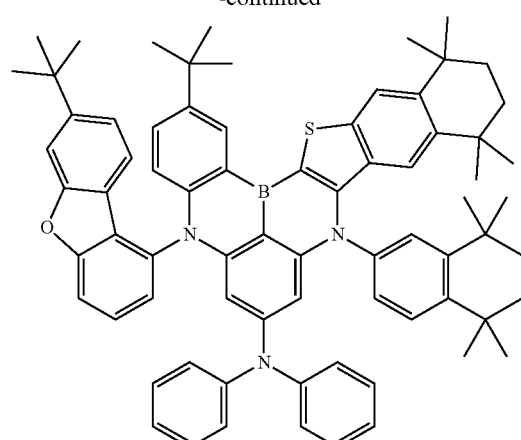
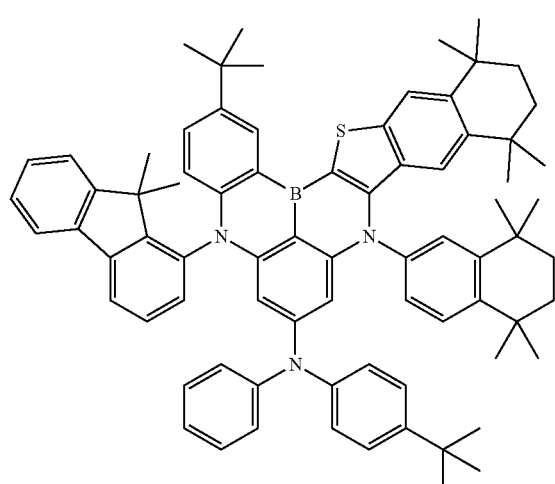
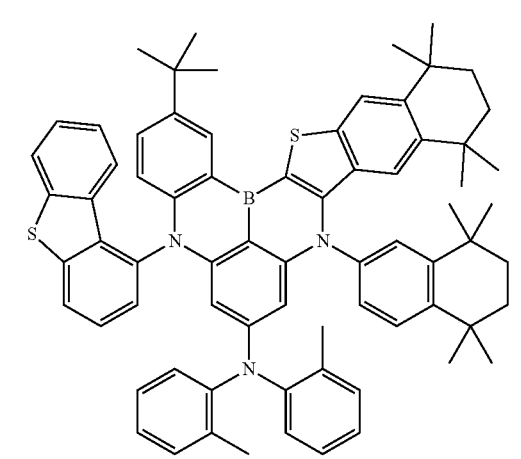
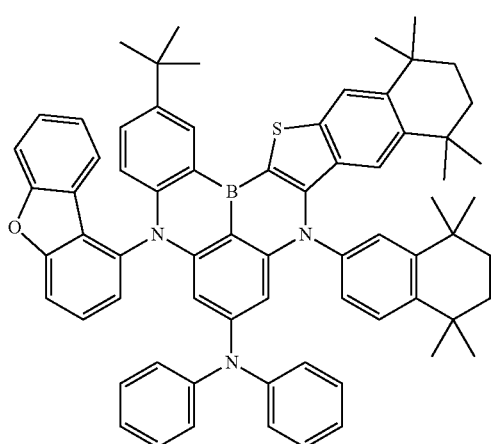
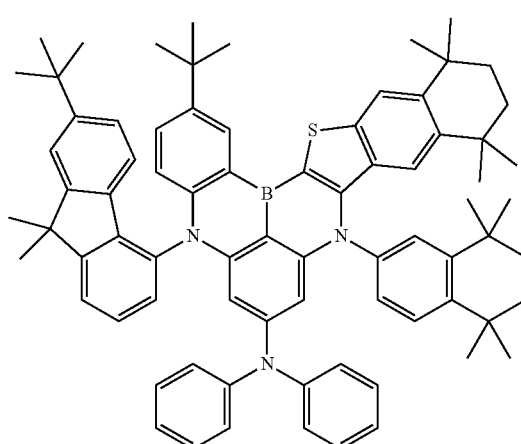

1357
-continued
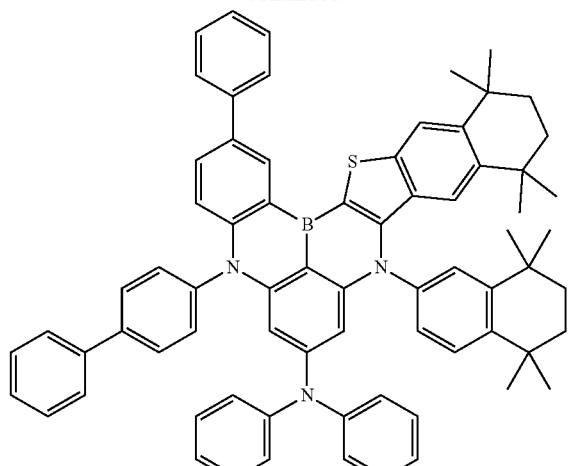
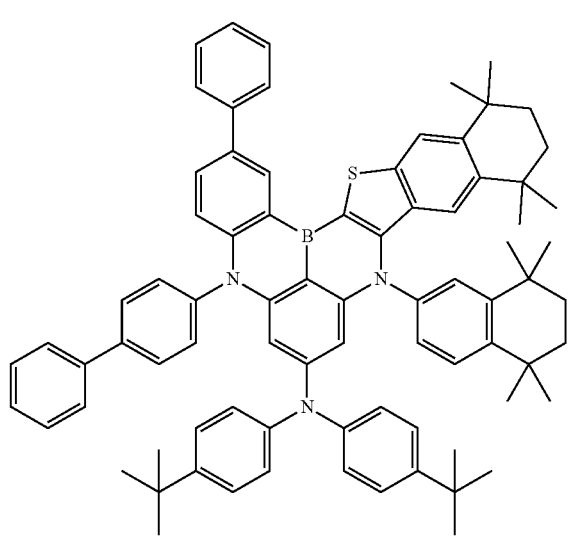
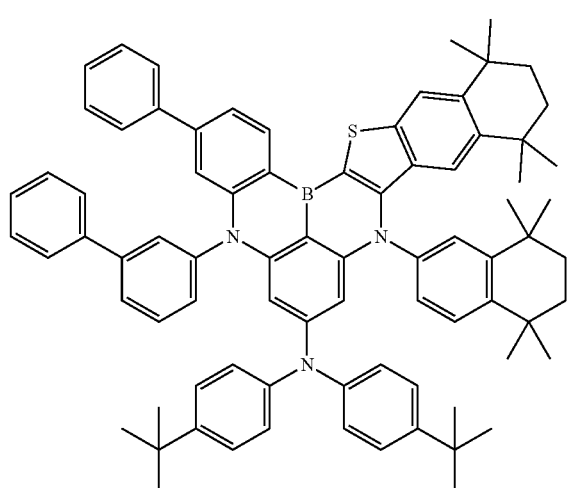
1358
-continued
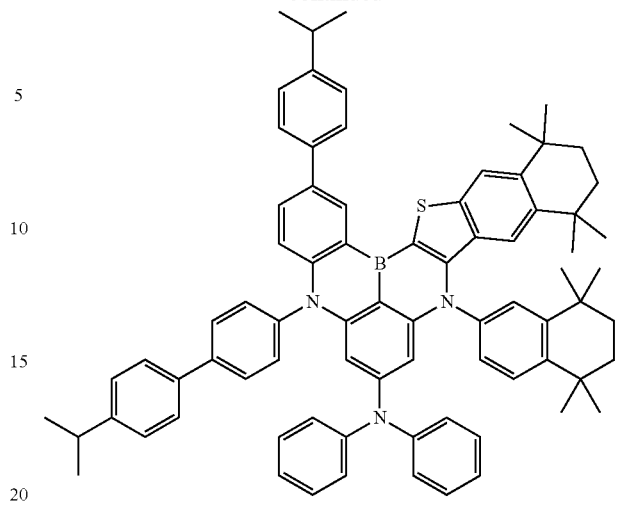
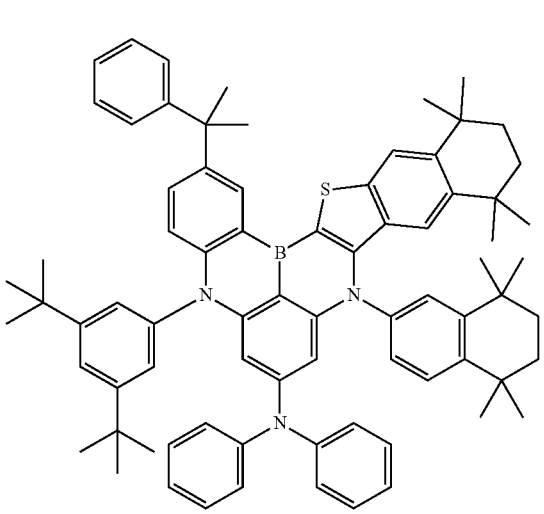
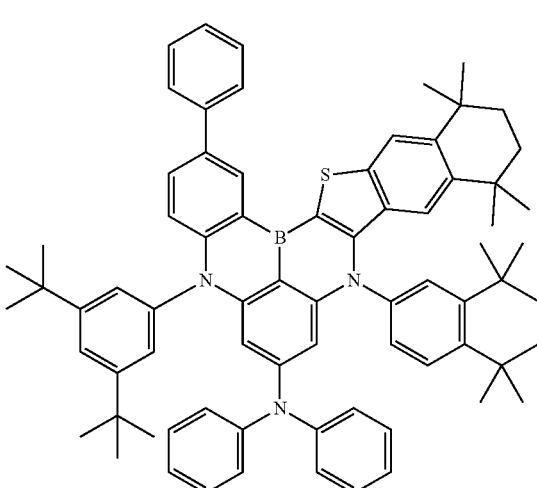

1359
-continued
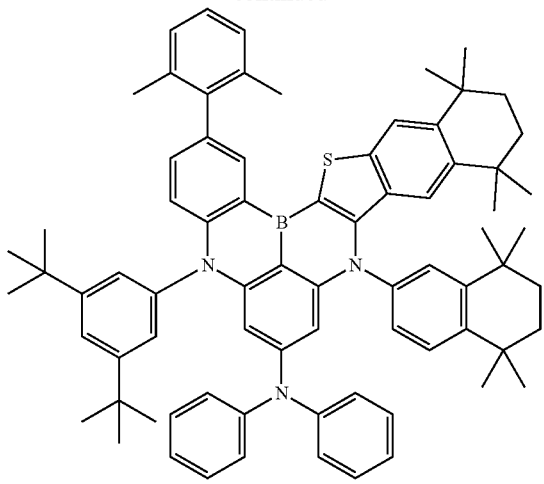
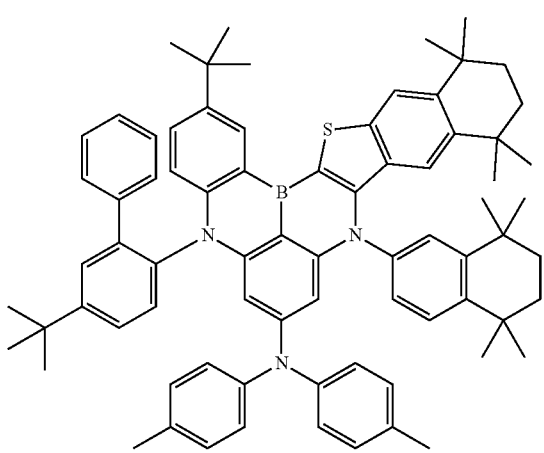
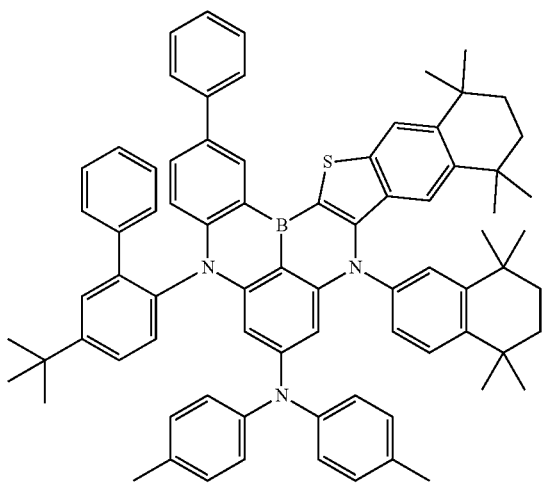
1360
-continued
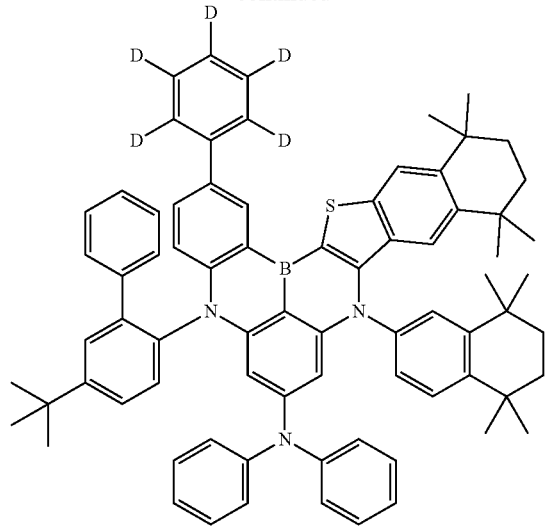
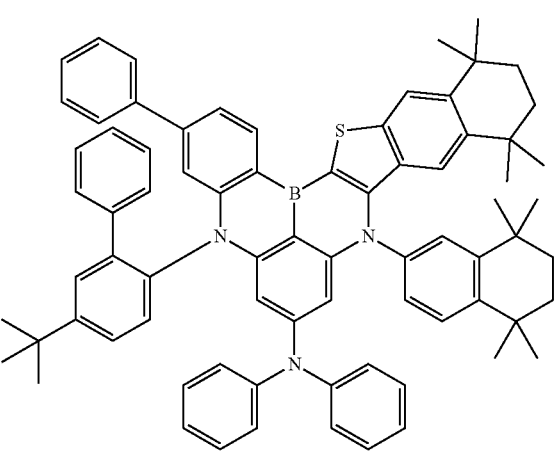
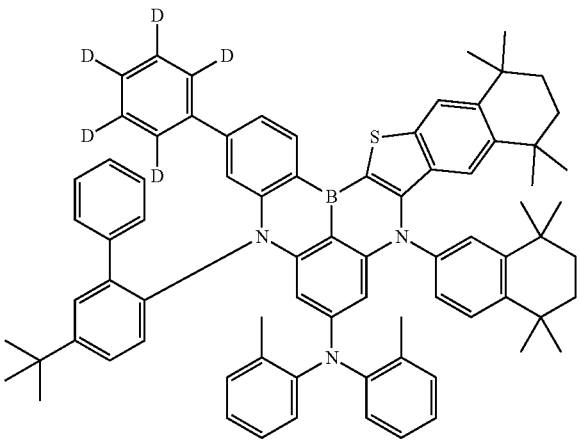

| 1361 -continued | 1362 -continued |
|---|---|
| 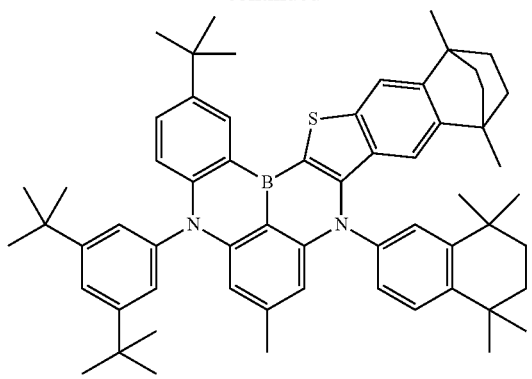 | 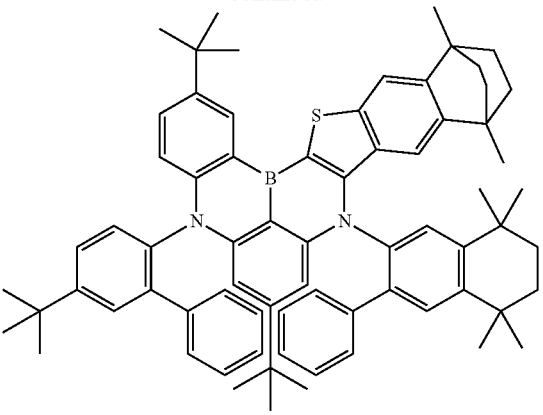 |
| 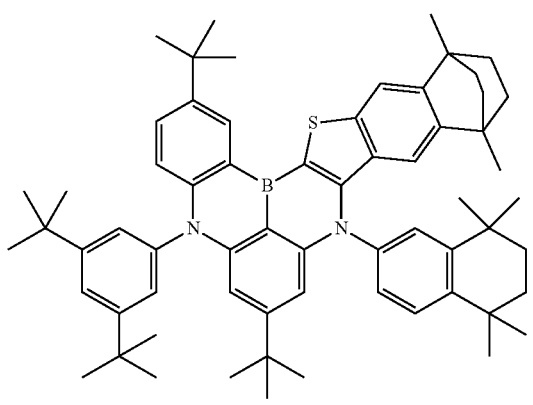 | 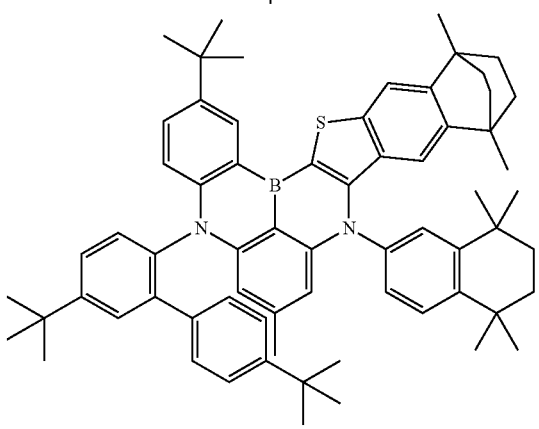 |
| 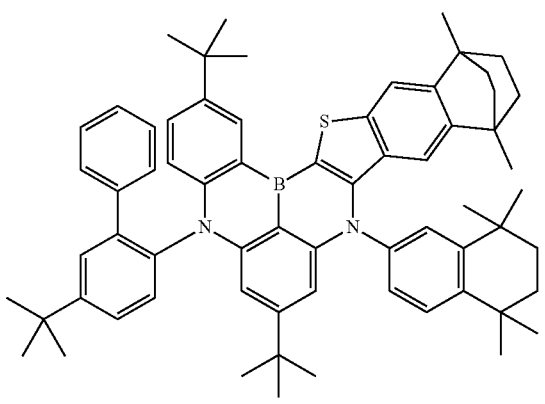 | 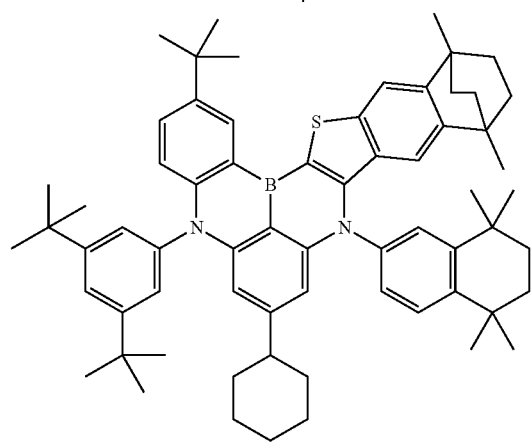 |
| 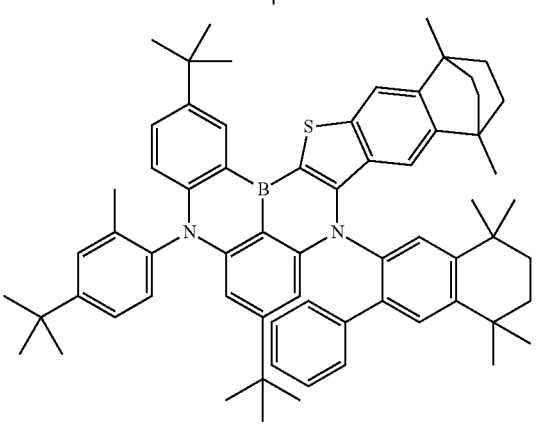 | 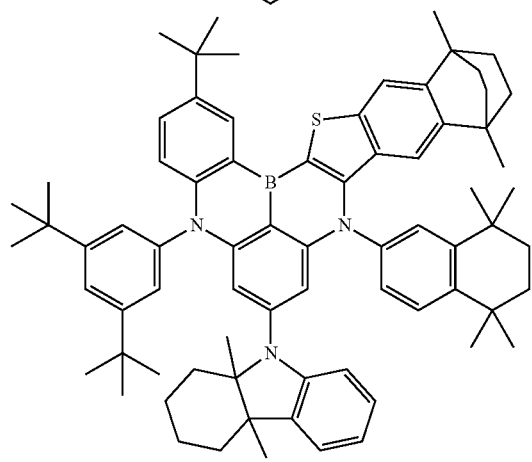 |

1363
-continued
1364
-continued
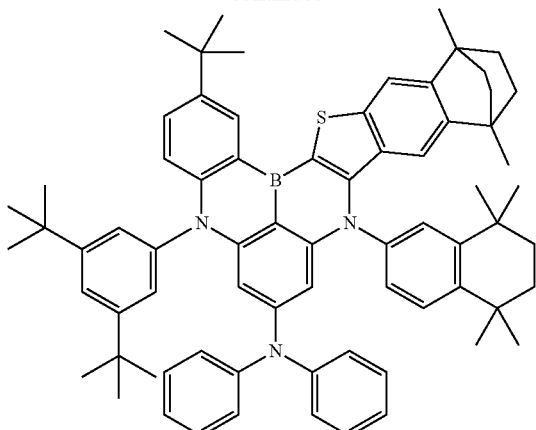
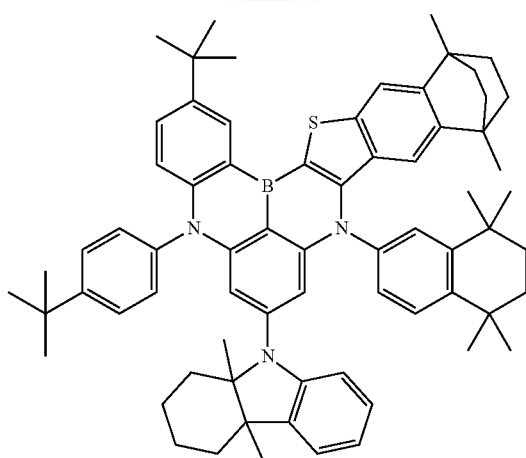
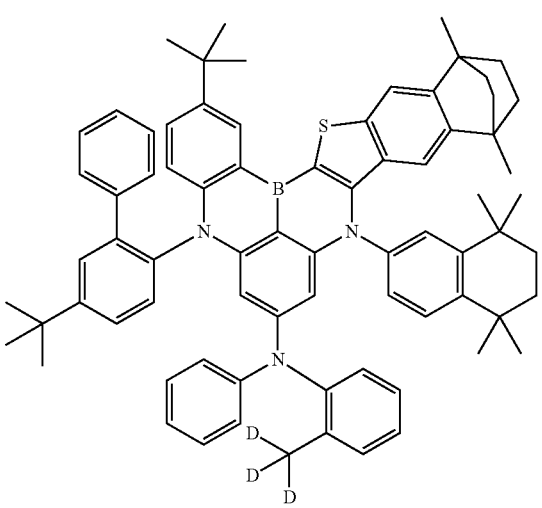
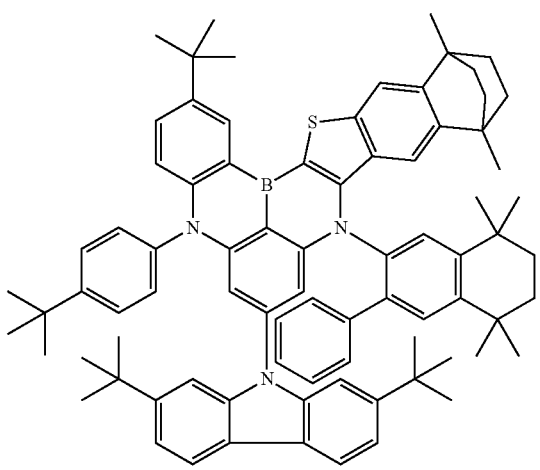
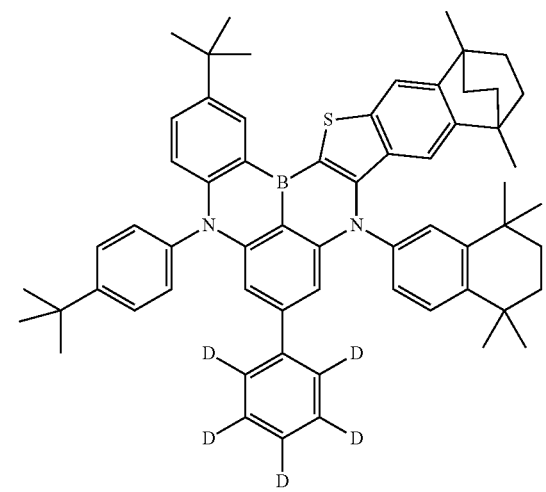

1365
-continued
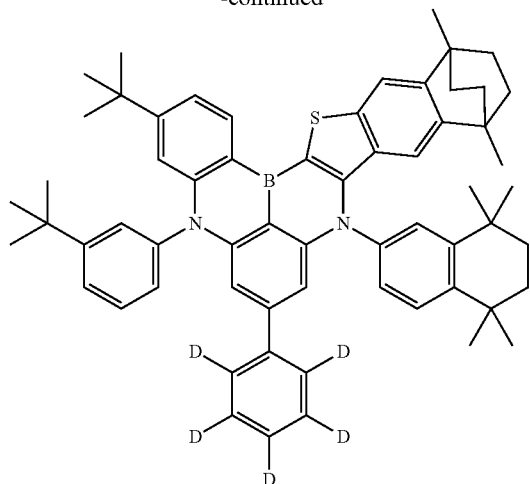
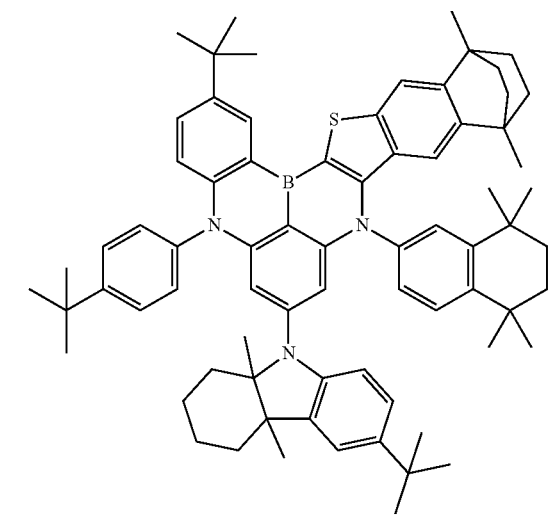
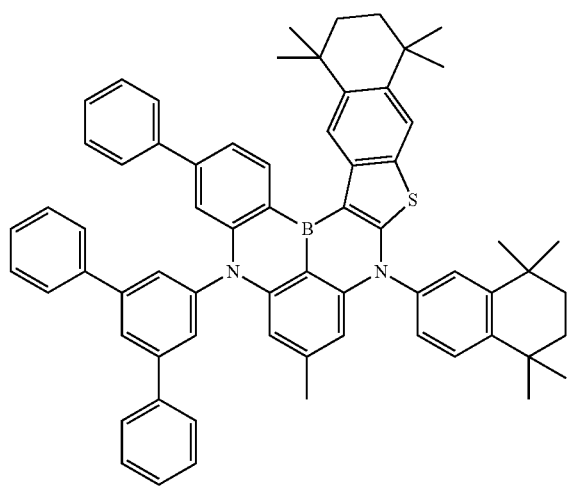
1366
-continued
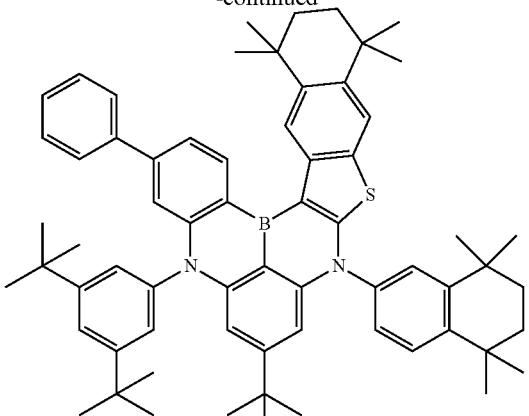
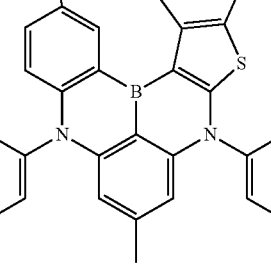
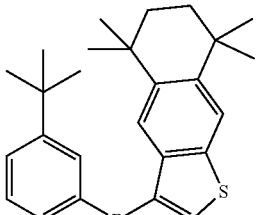
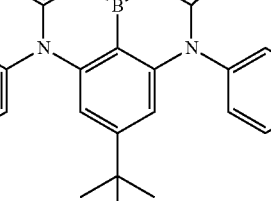

1367
-continued
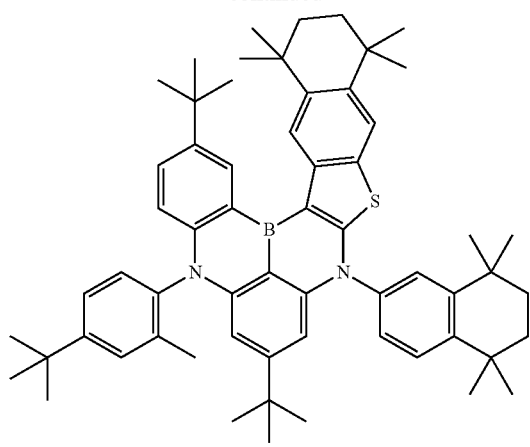
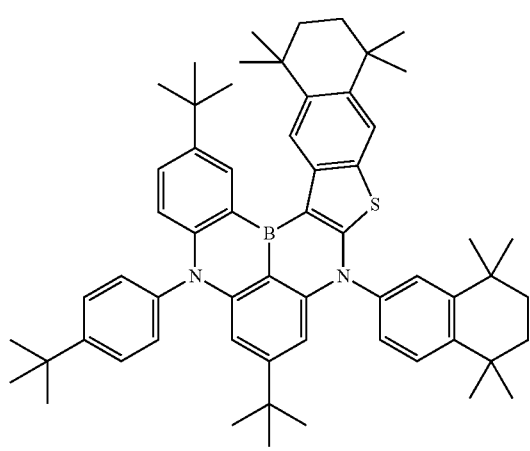
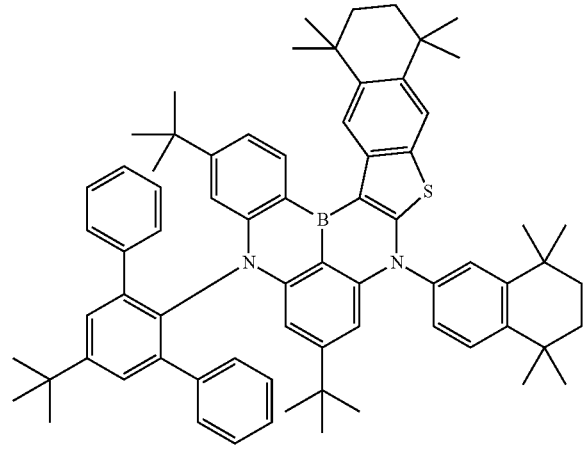
1368
-continued
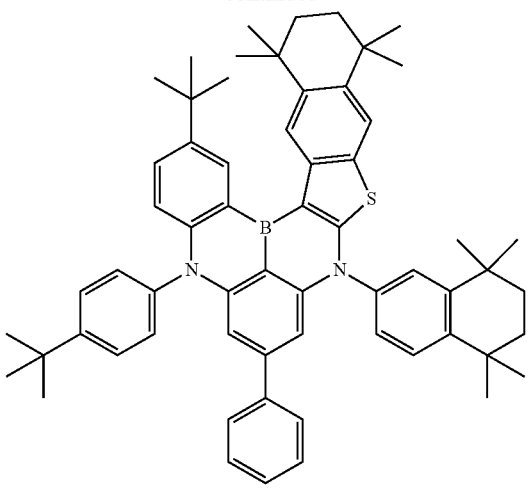
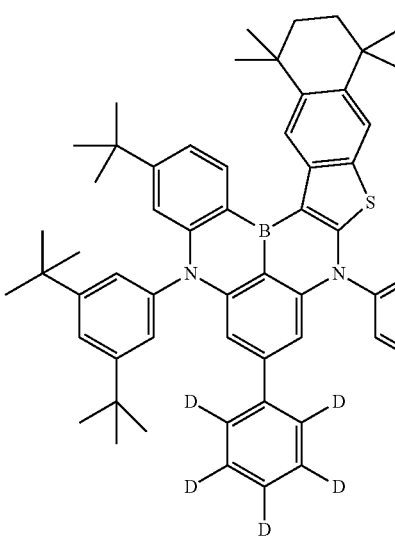
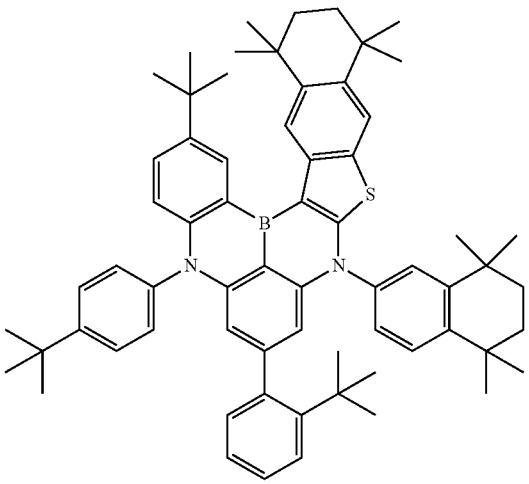

1369
-continued
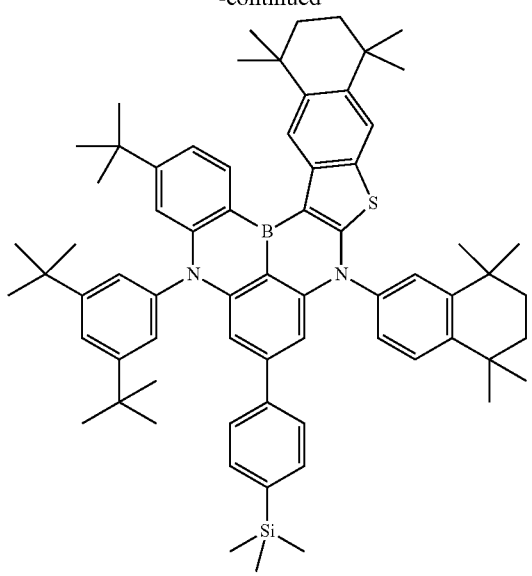
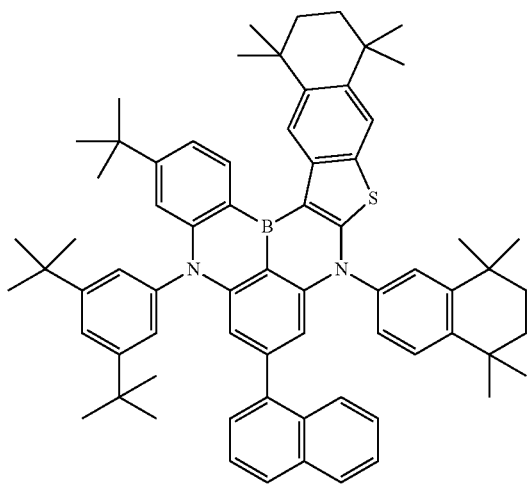
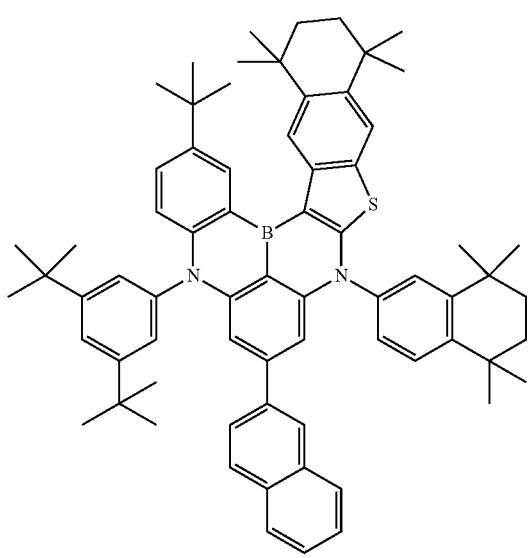
1370
-continued
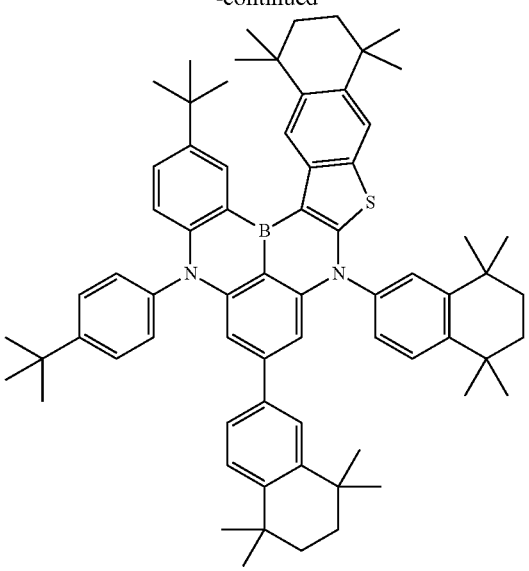
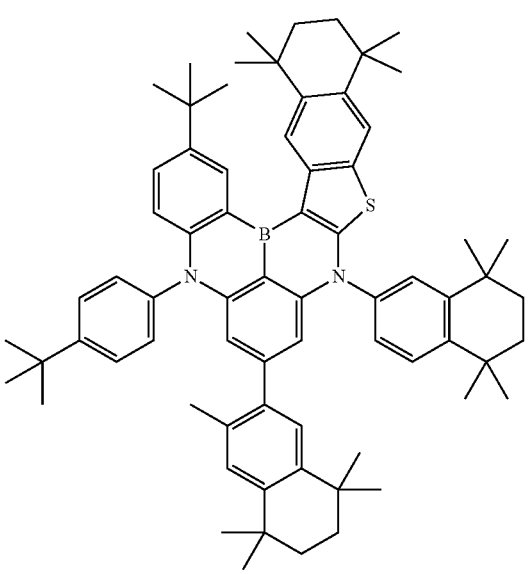
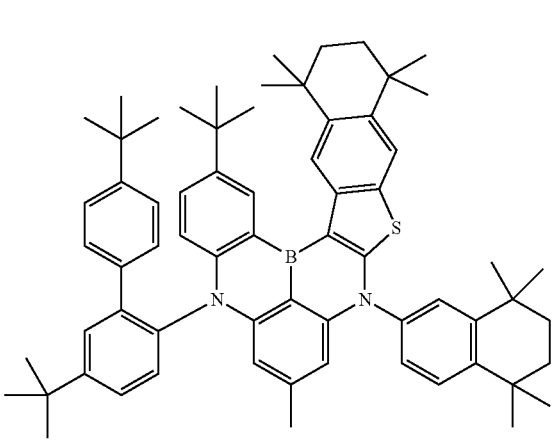

1371
-continued
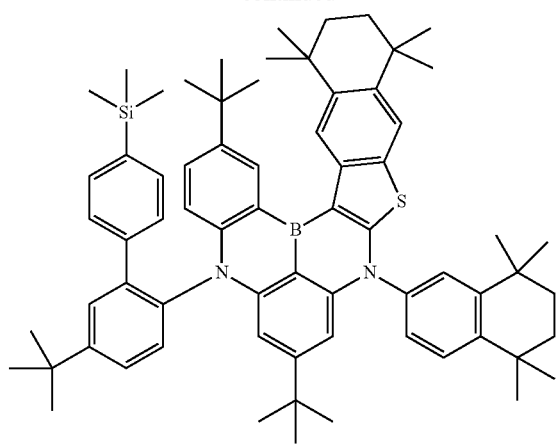
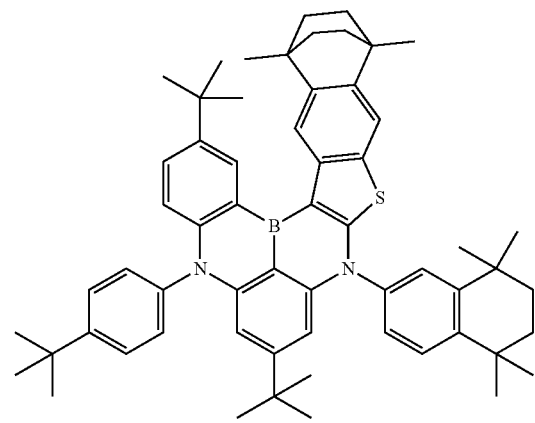
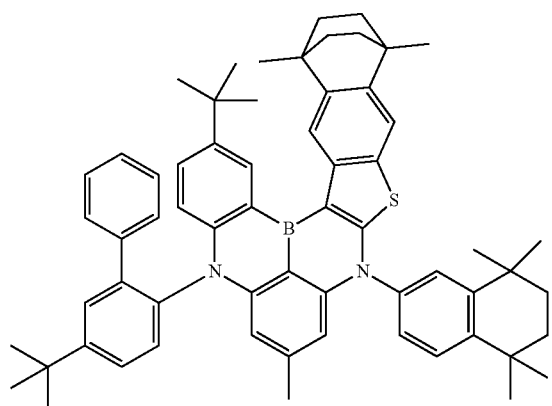
1372
-continued
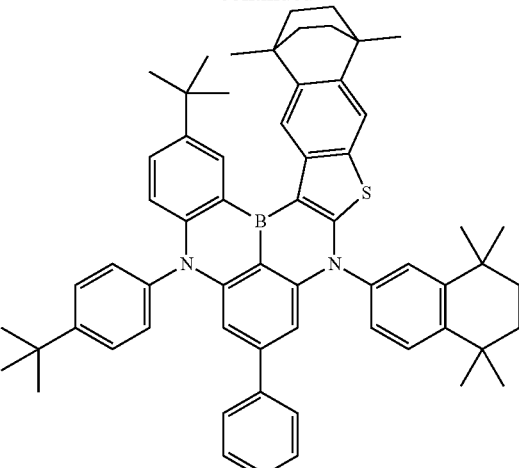
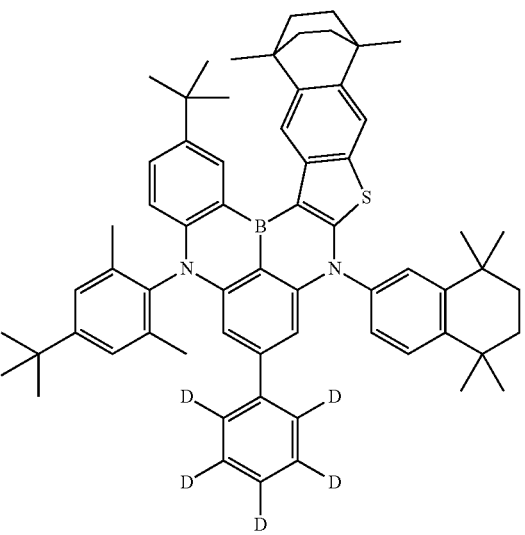
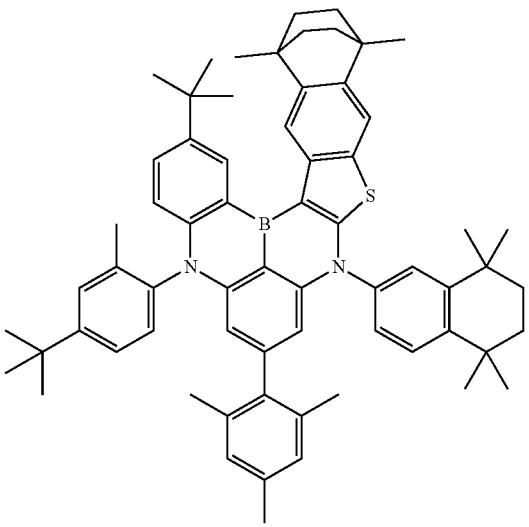

1373
-continued
1374
-continued
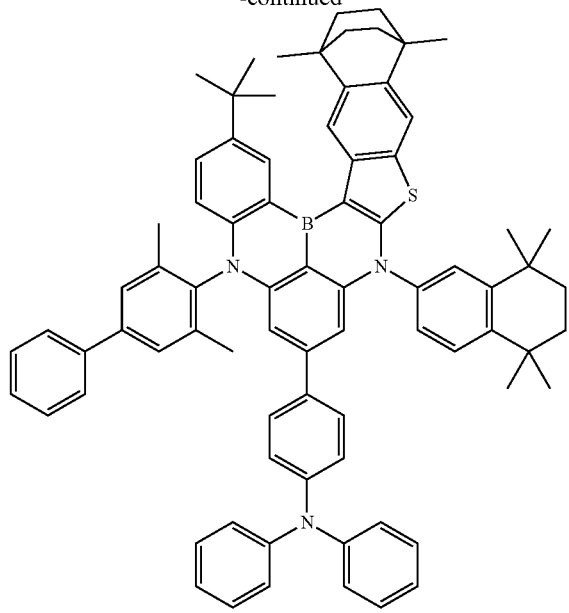
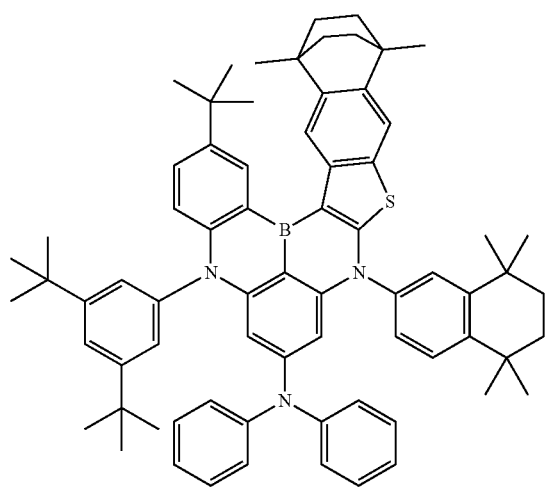
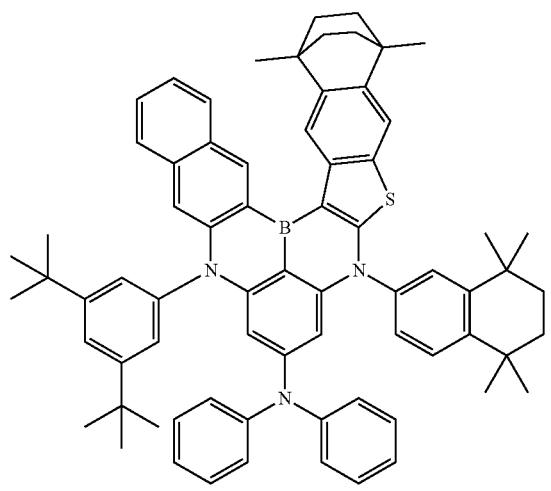
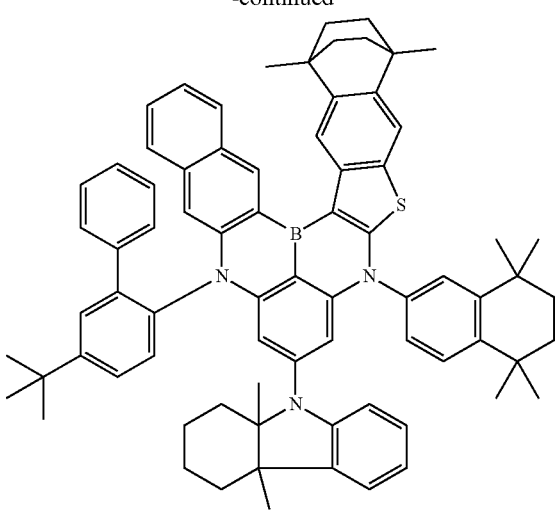
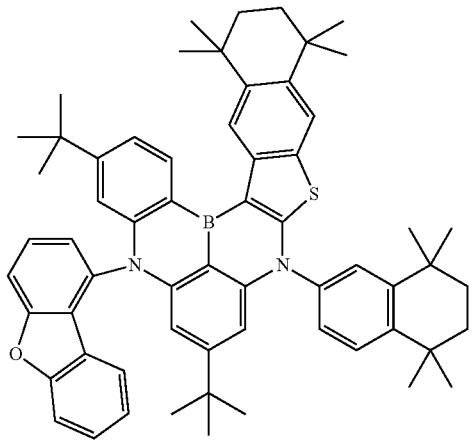
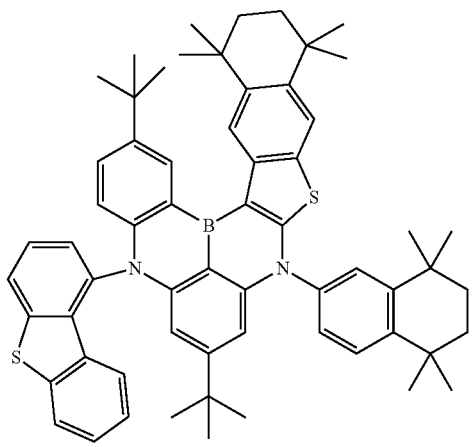

1375
-continued
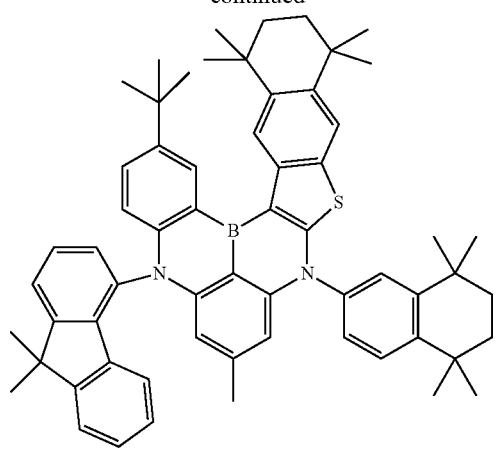
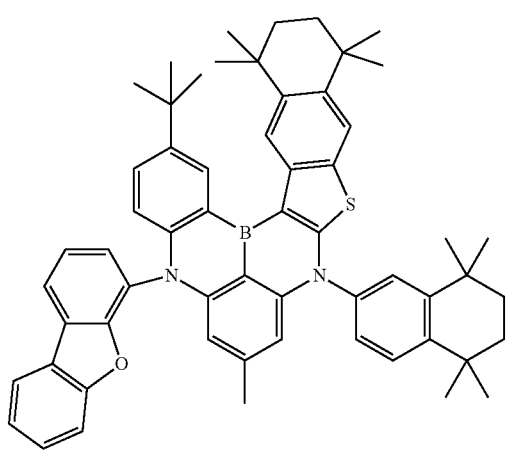
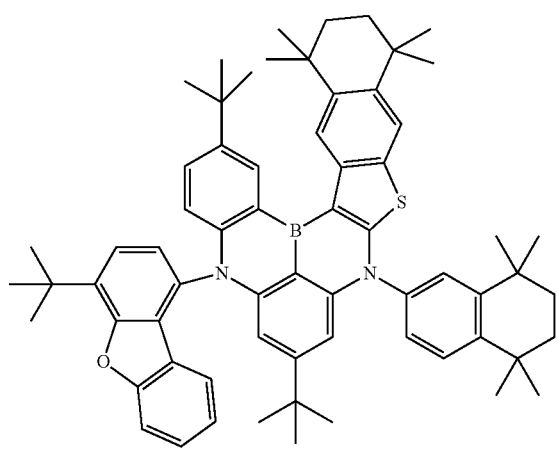
1376
-continued
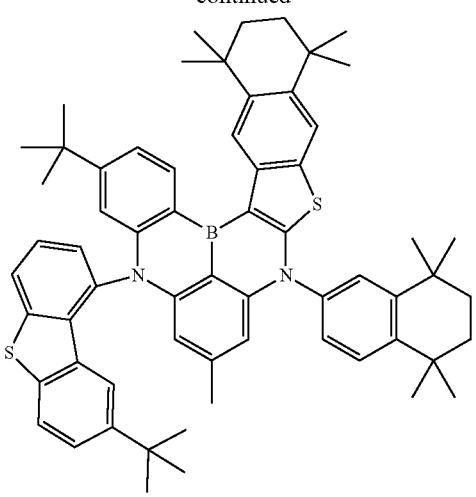
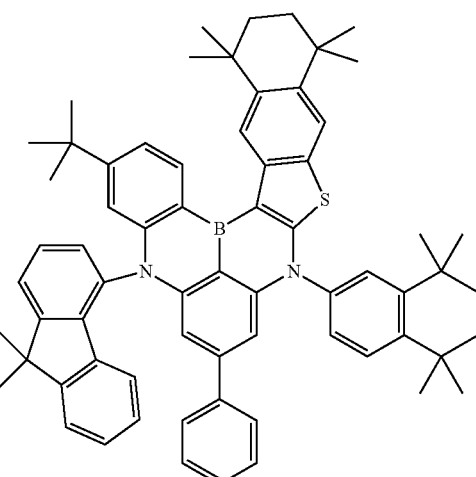
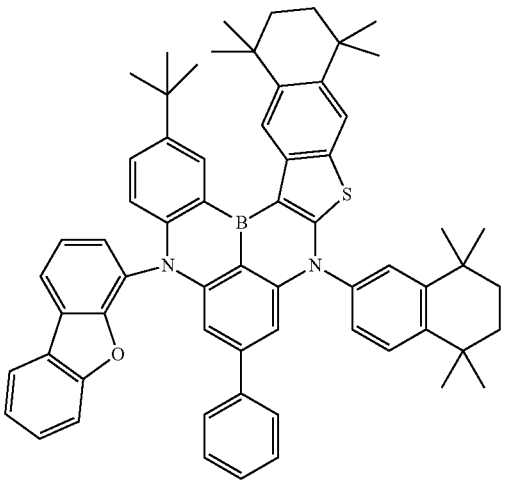

1377
-continued
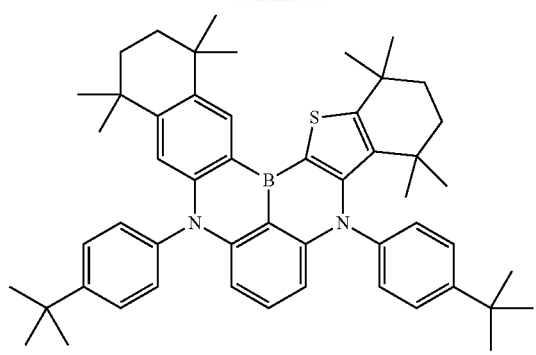
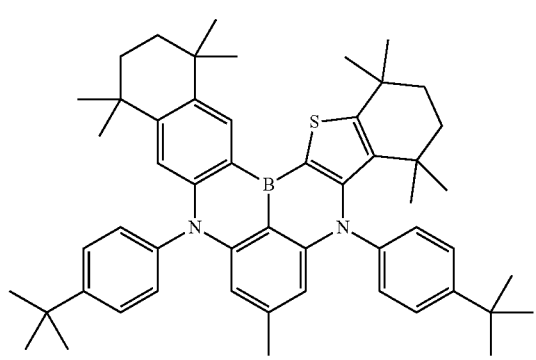
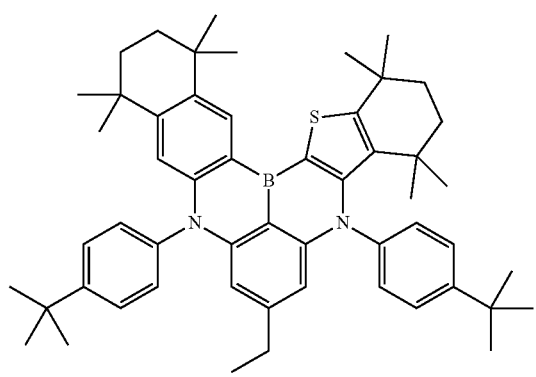
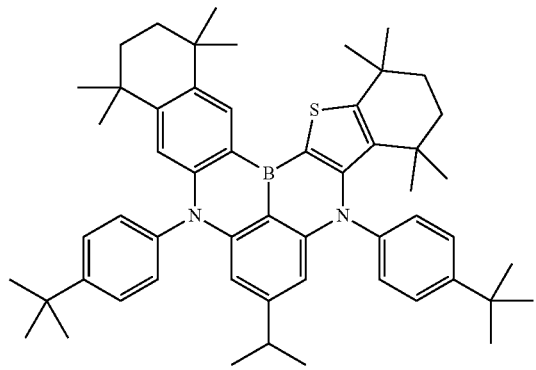
1378
-continued
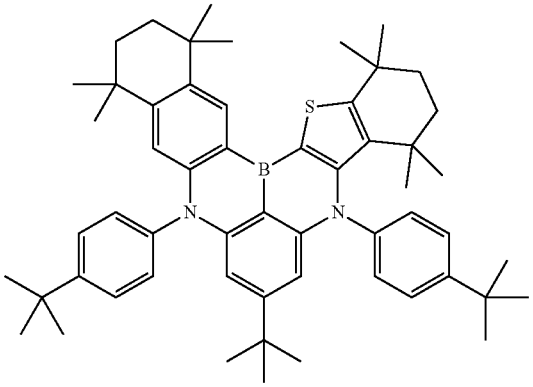
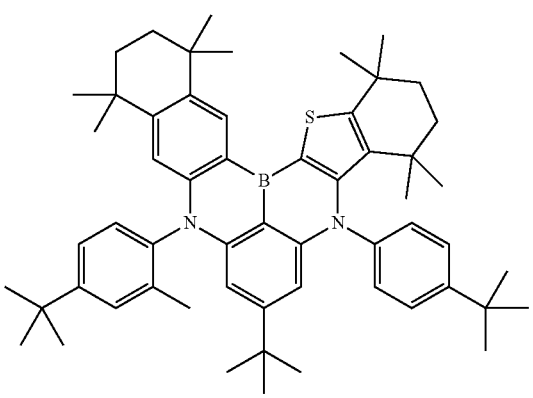
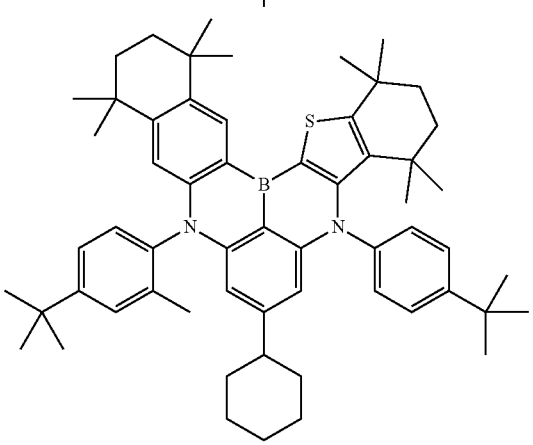
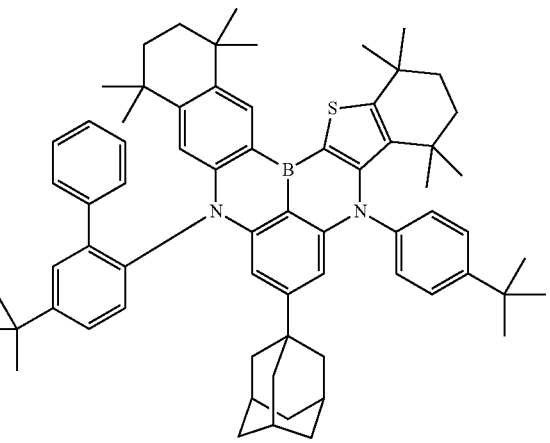

| 1379 -continued | 1380 -continued |
|---|---|
| 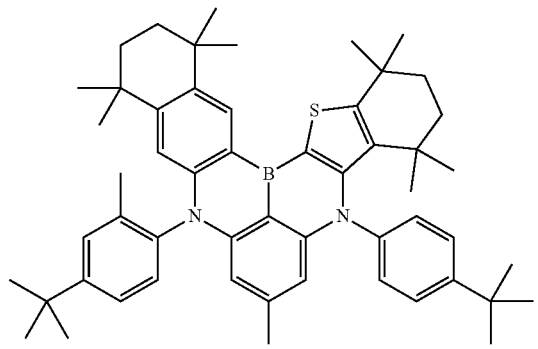 | 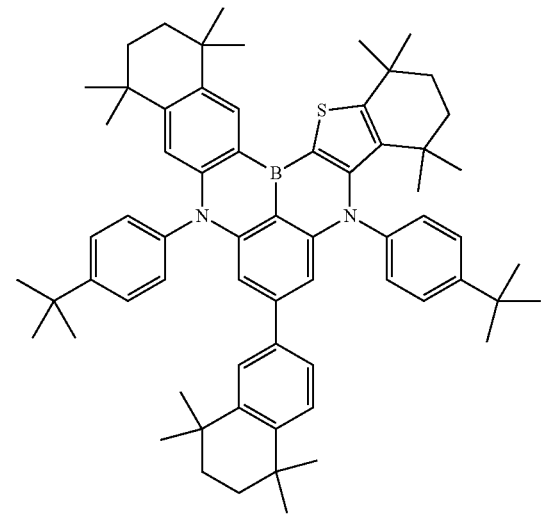 |
| 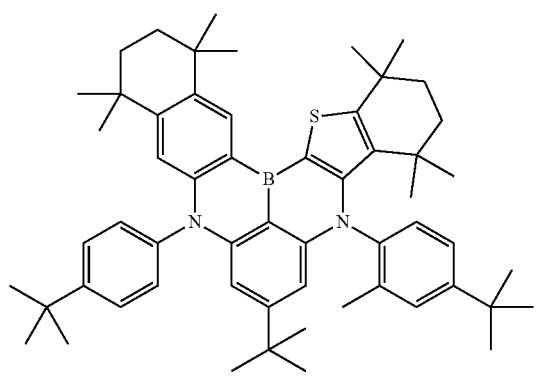 | 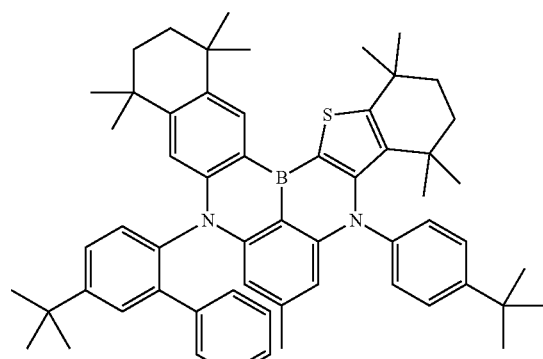 |
| 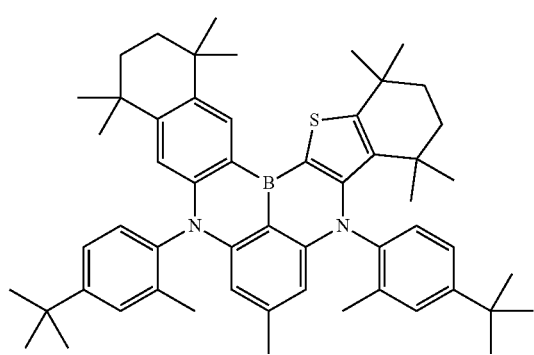 | 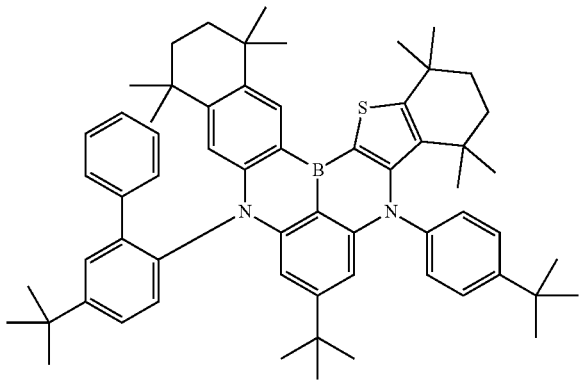 |
| 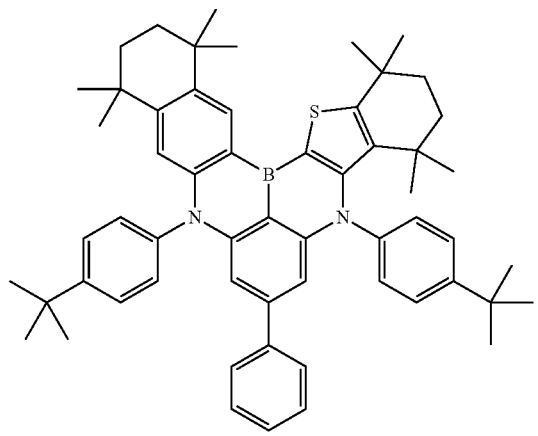 | 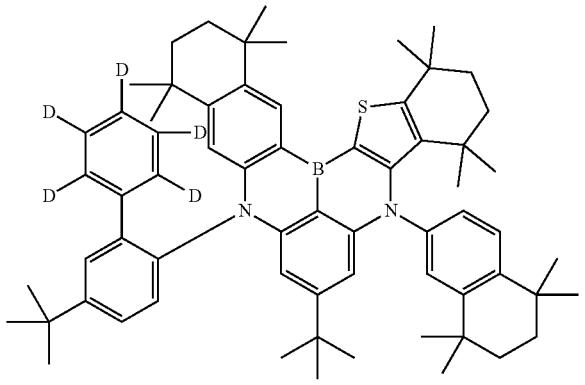 |

1381
-continued
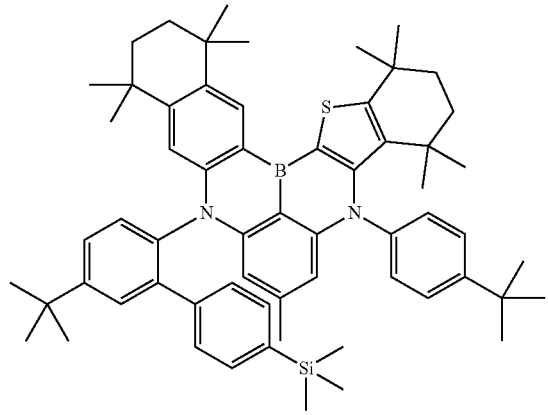
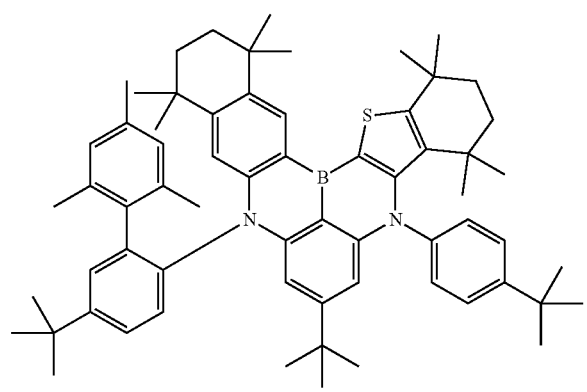
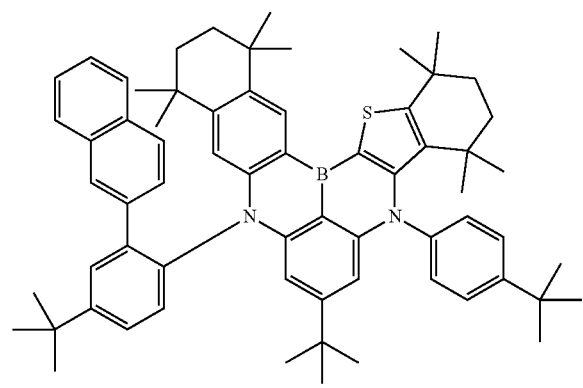
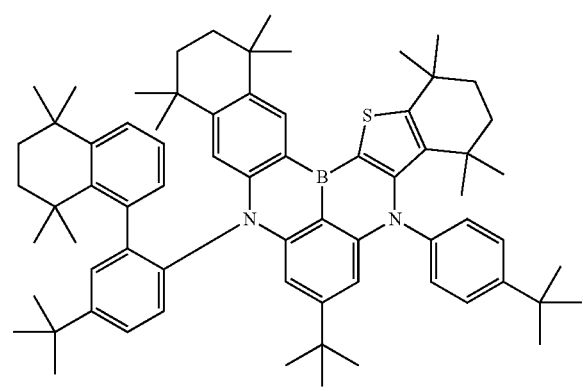
1382
-continued
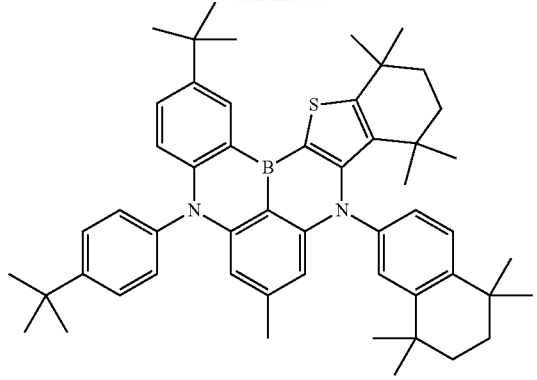
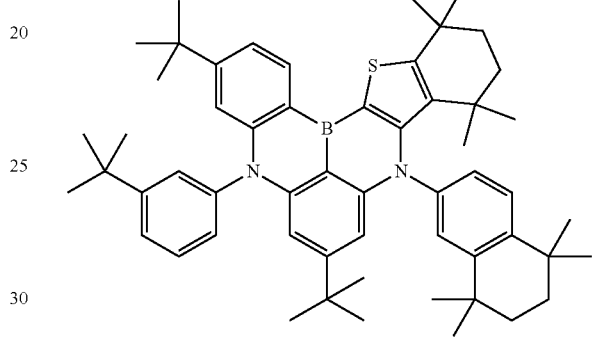
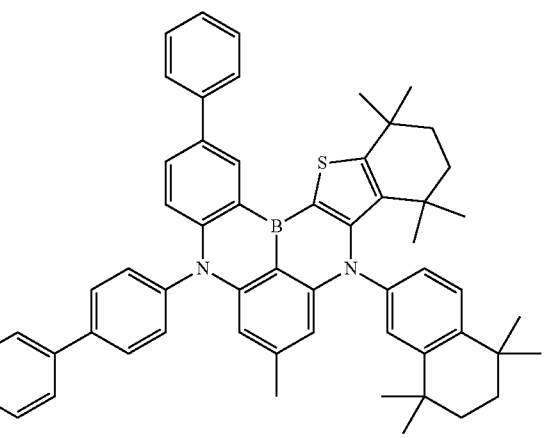
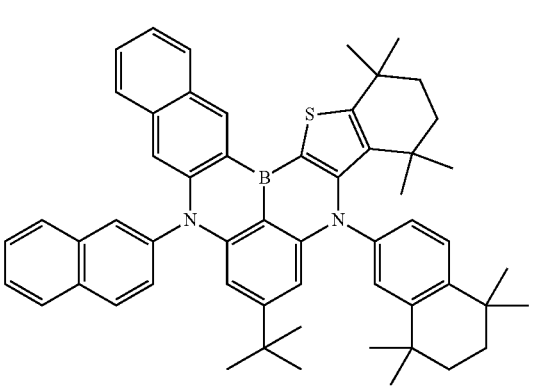

1383
-continued
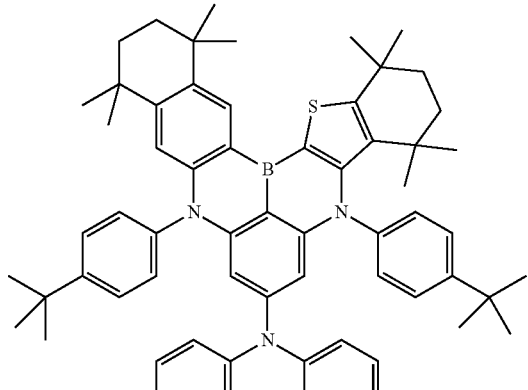
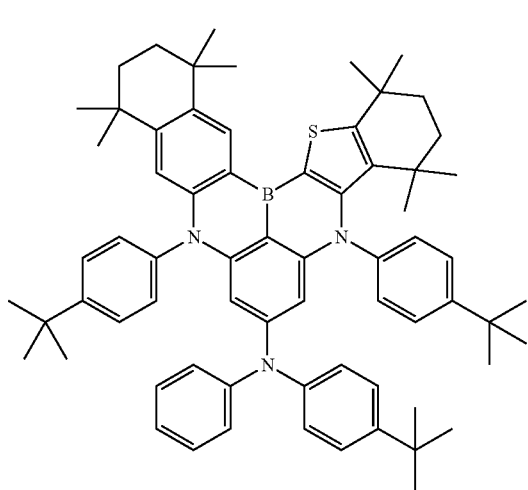
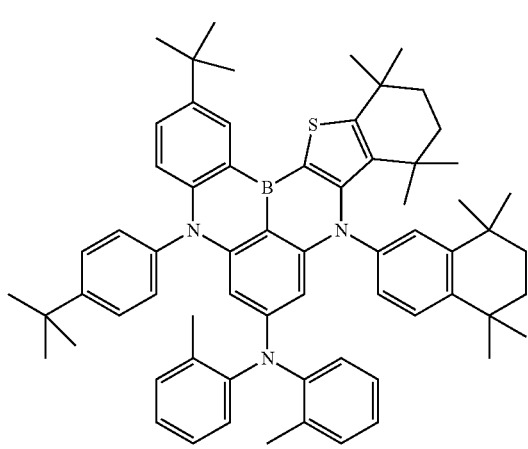
1384
-continued
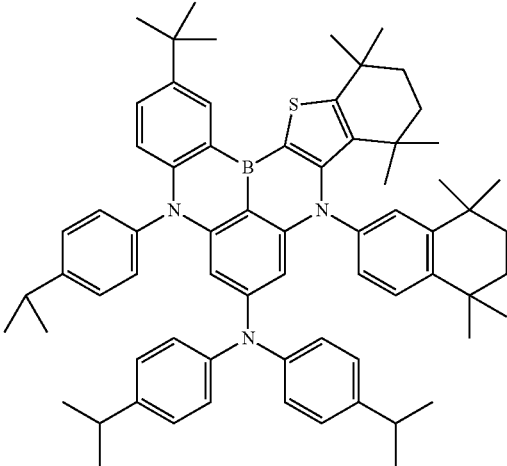
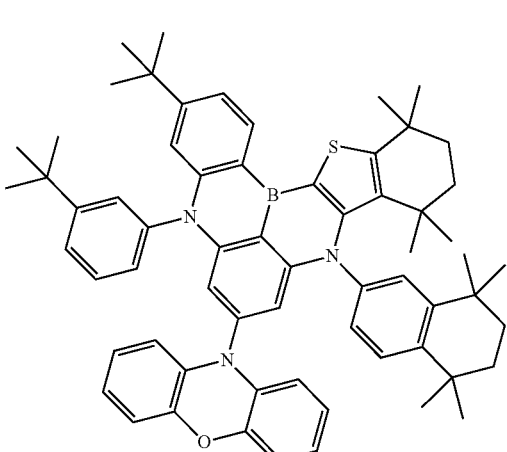
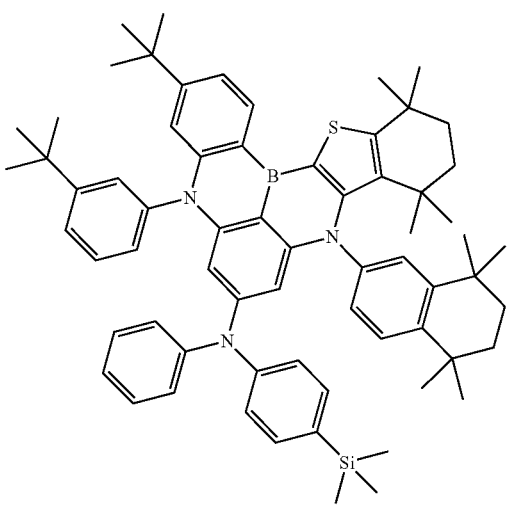

1385
-continued
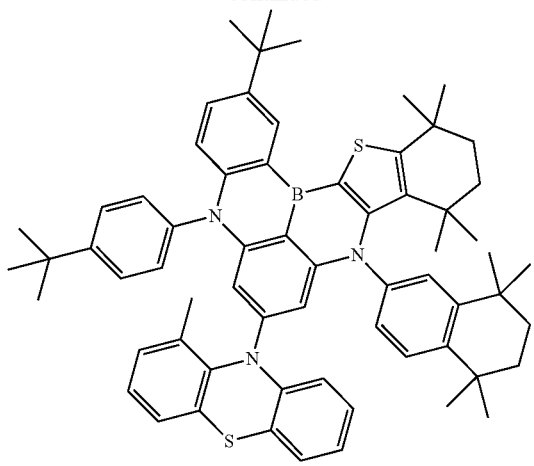
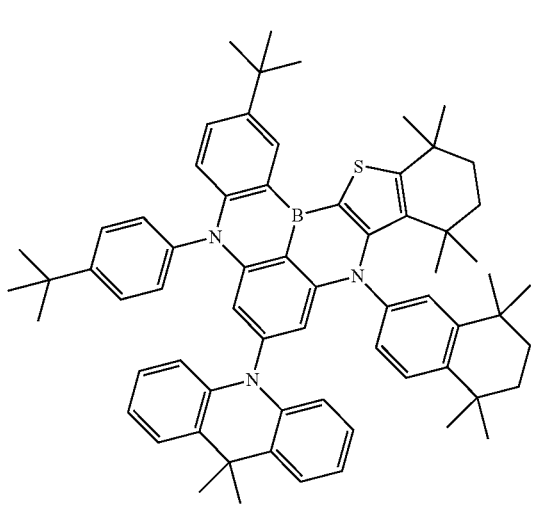
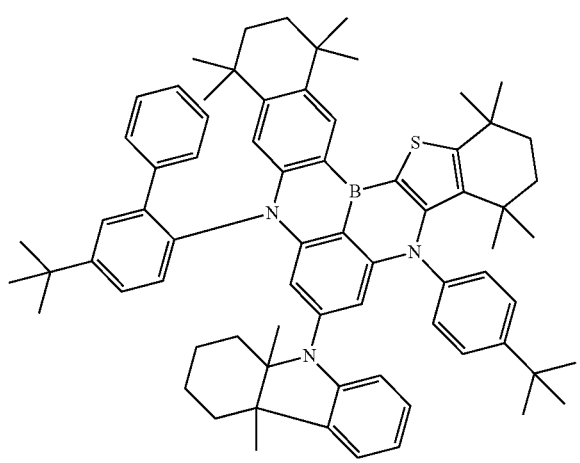
1386
-continued
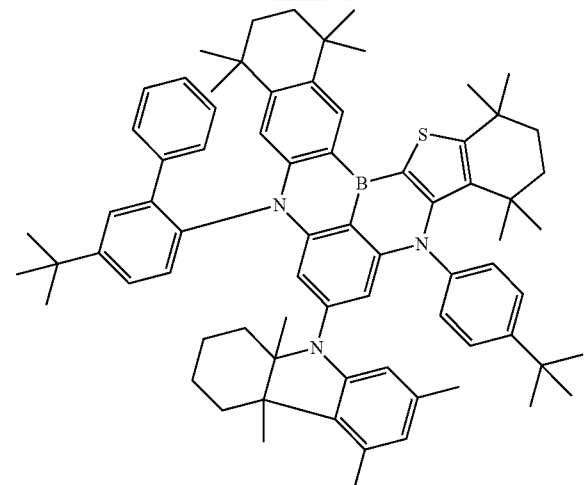
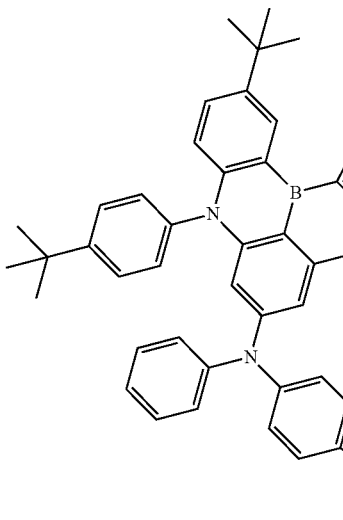
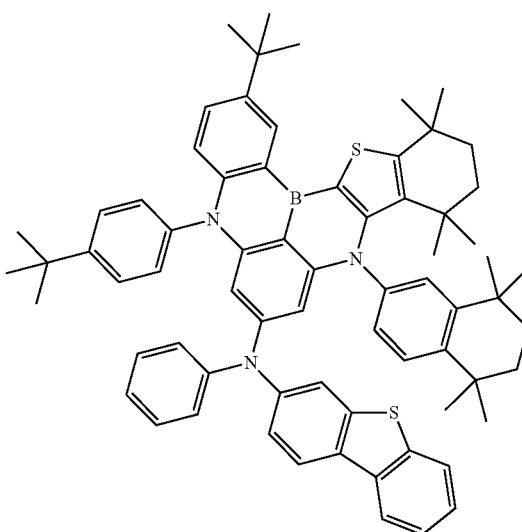

1387
-continued
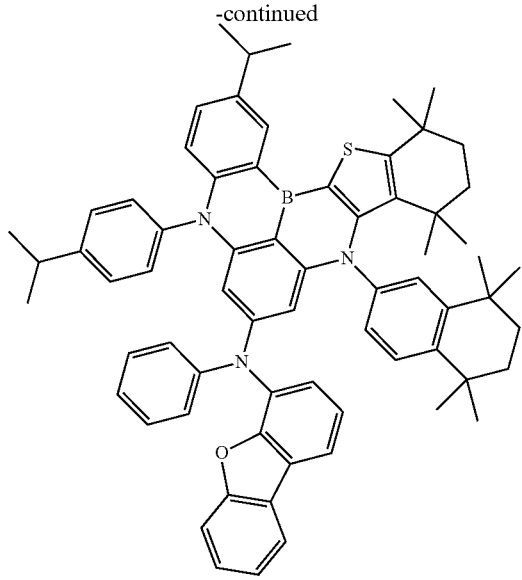
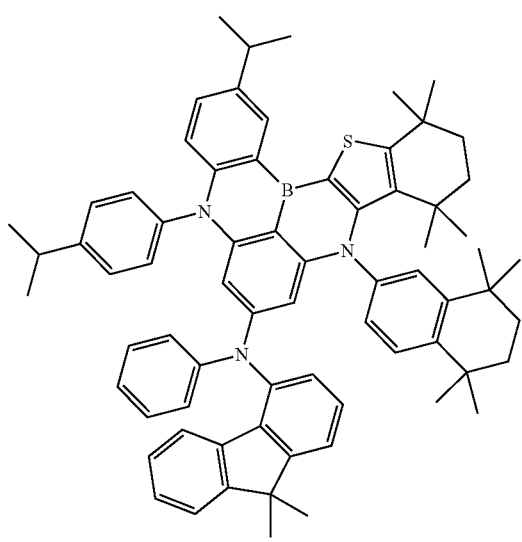
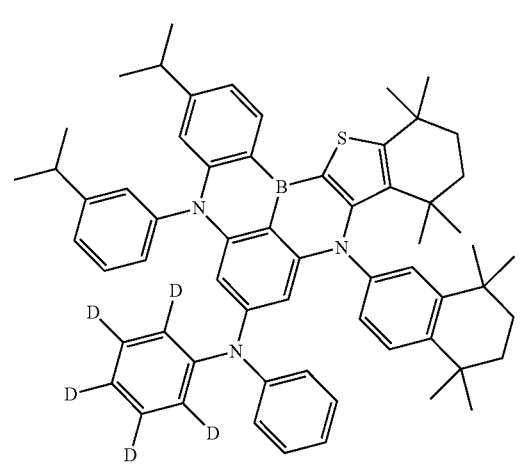
1388
-continued
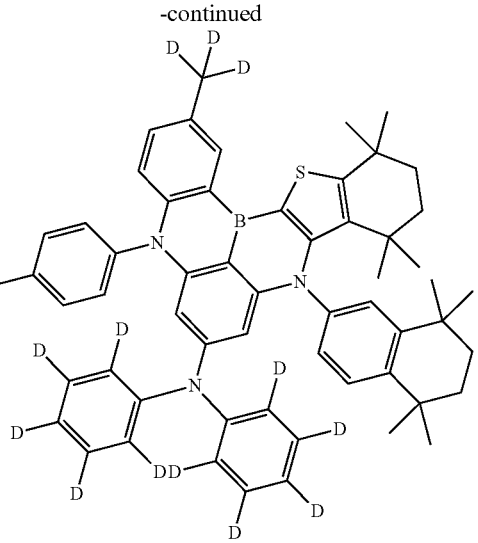
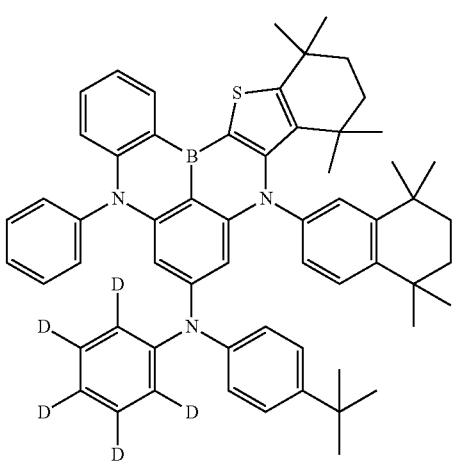
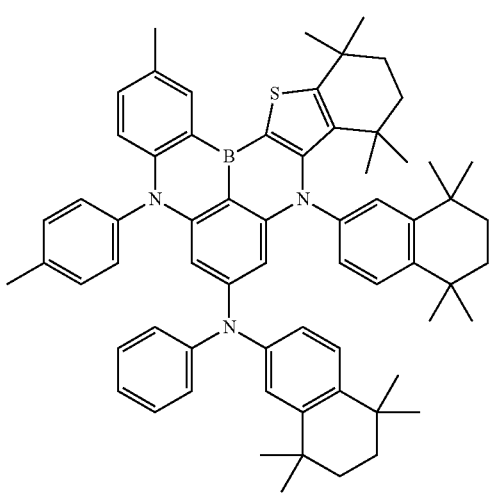

1389
-continued
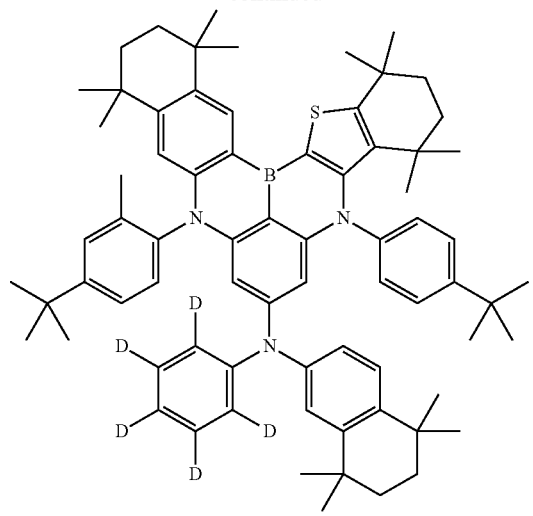
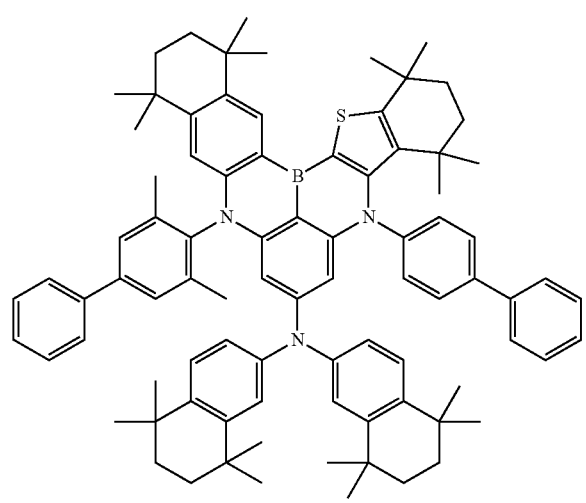
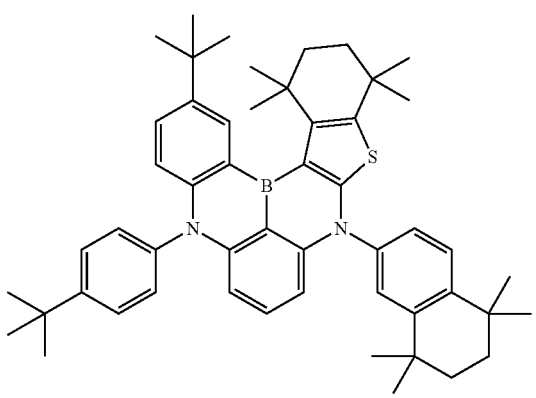
1390
-continued
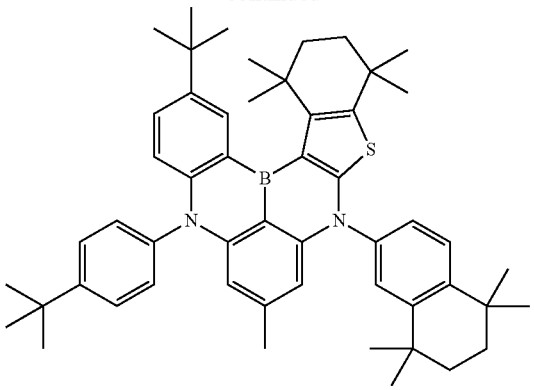
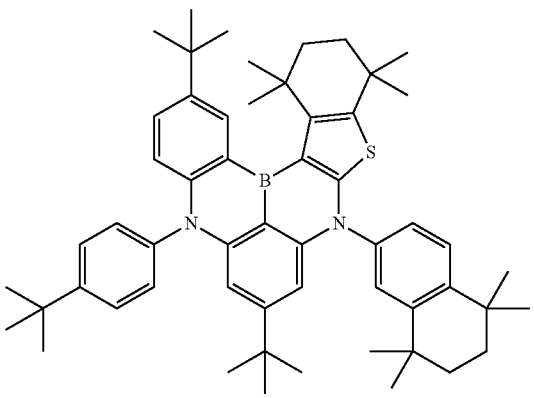
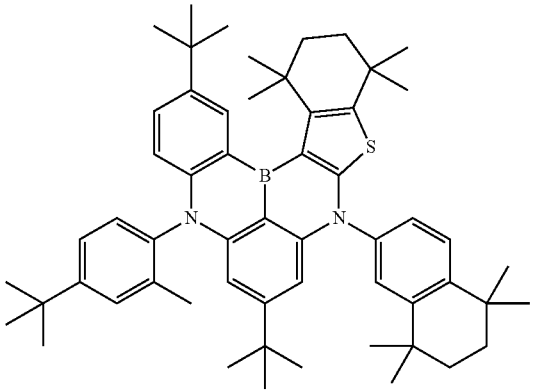
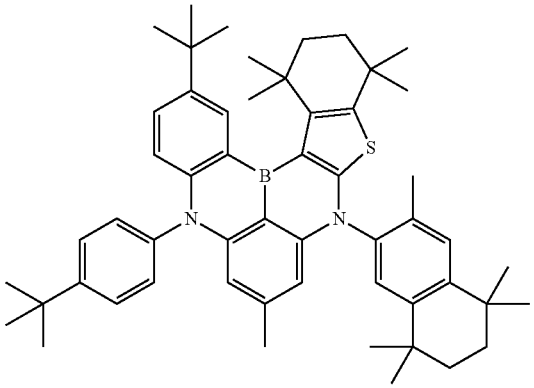

1391
-continued
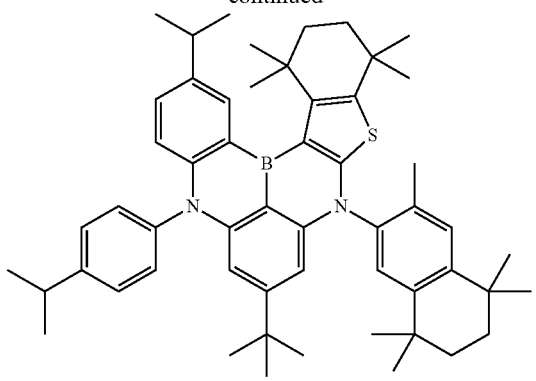
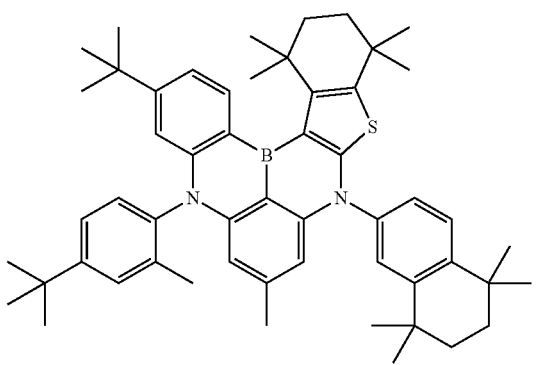
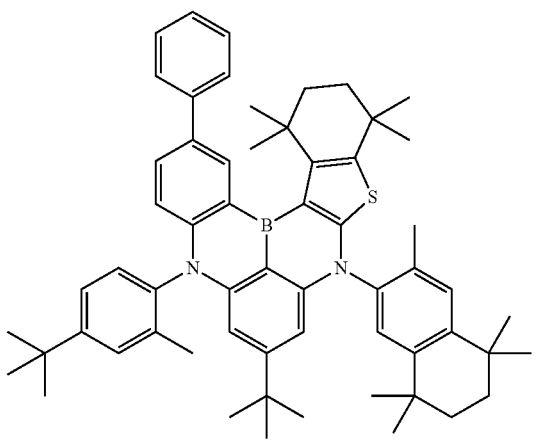
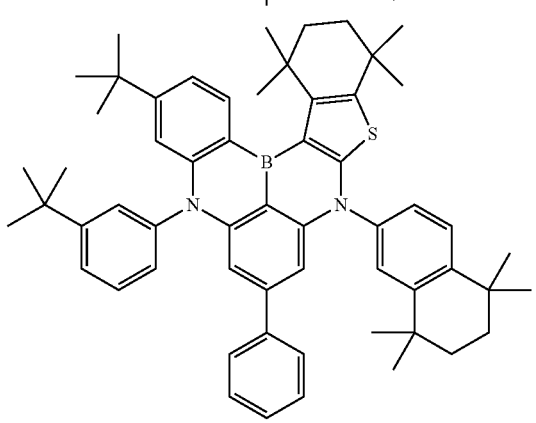
1392
-continued
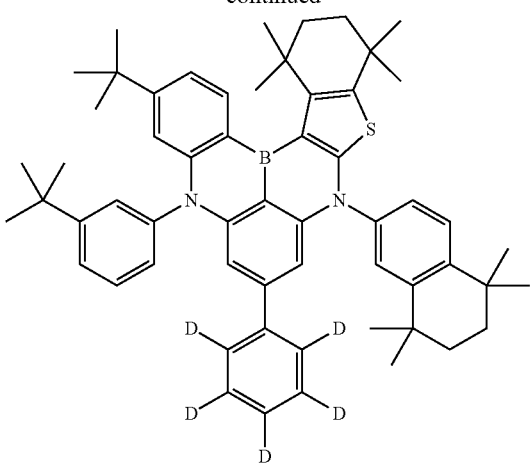
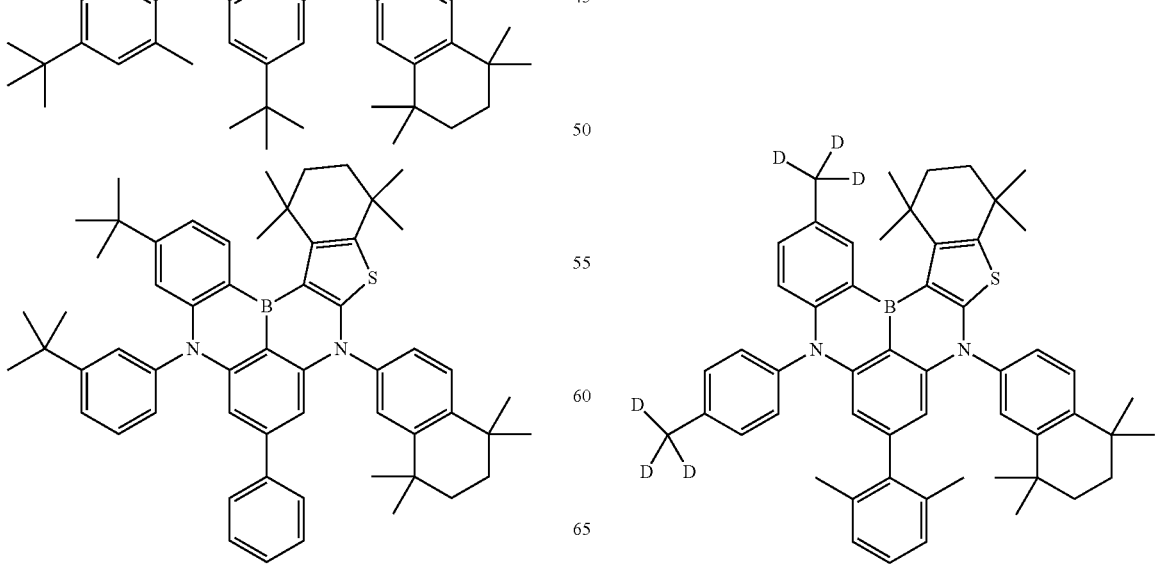

1393
-continued
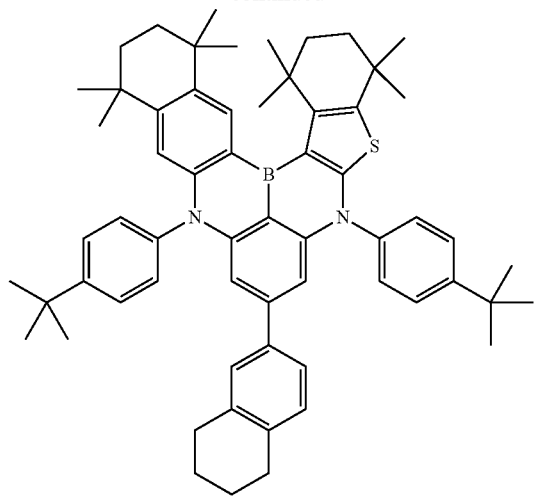
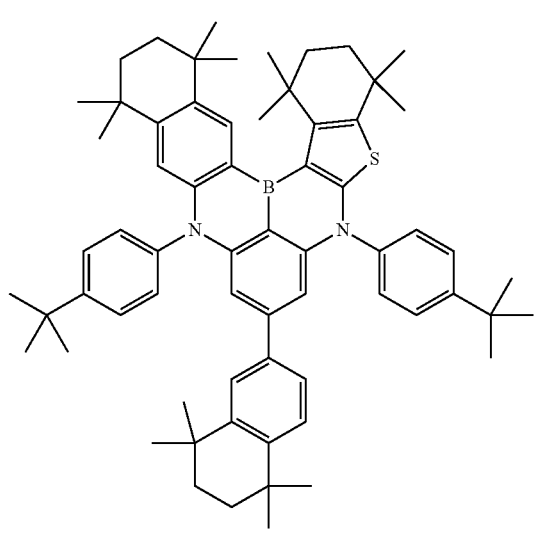
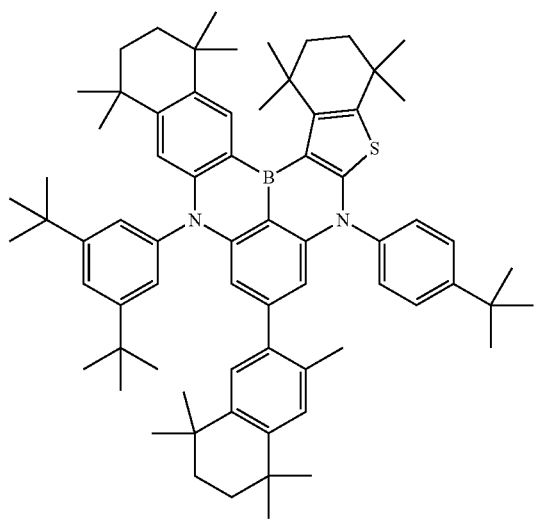
1394
-continued
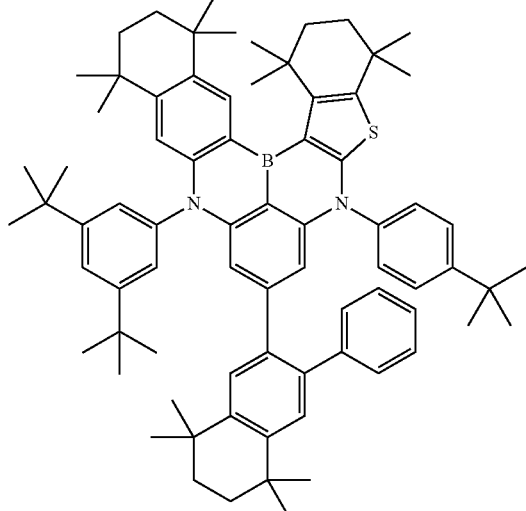
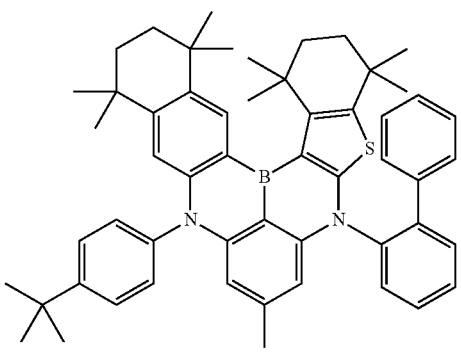
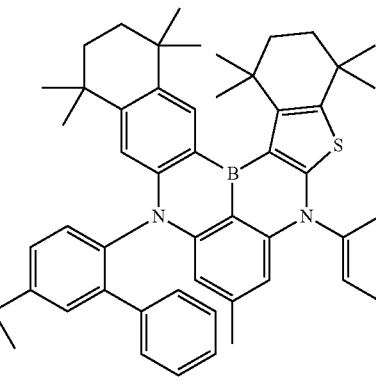
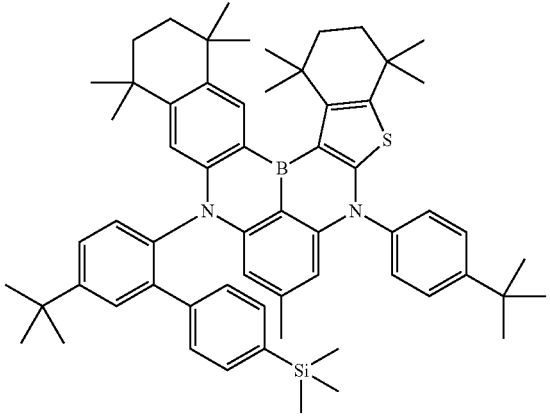

1395
-continued
1396
-continued
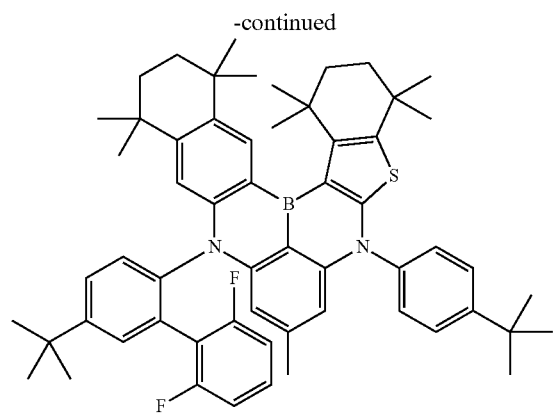
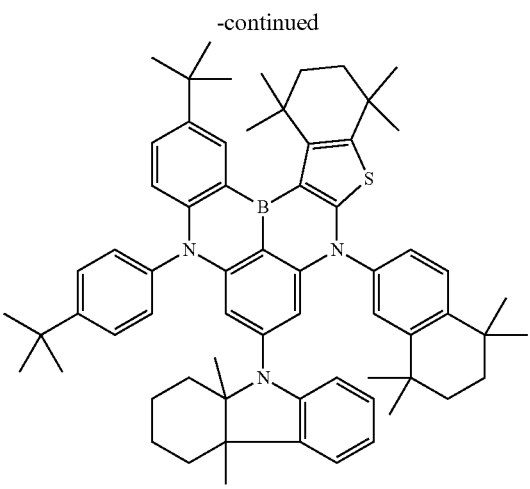

1397
-continued
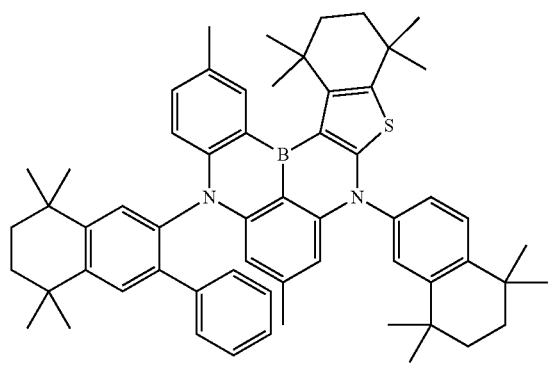
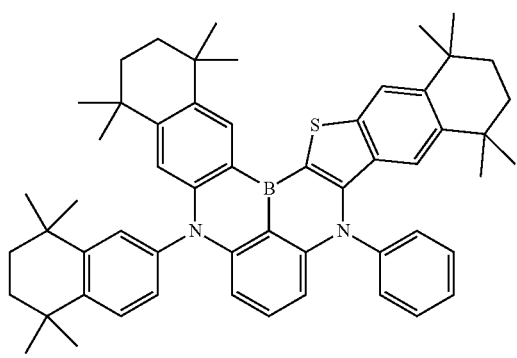
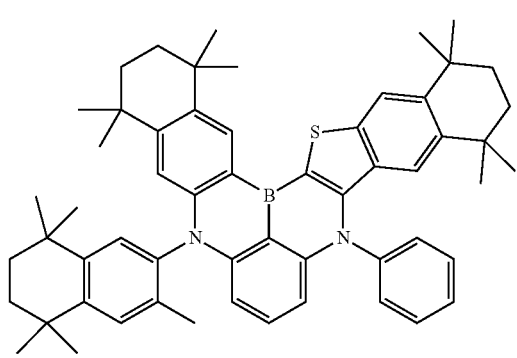
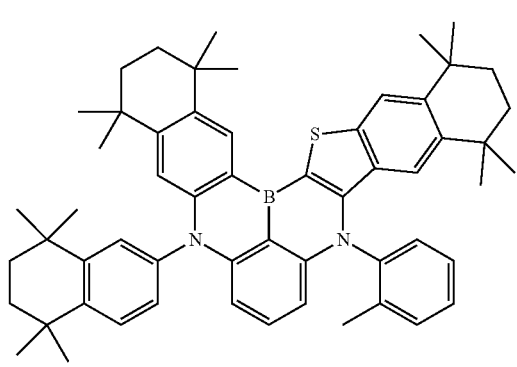
1398
-continued
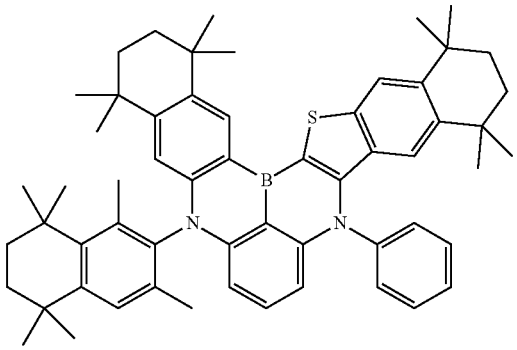
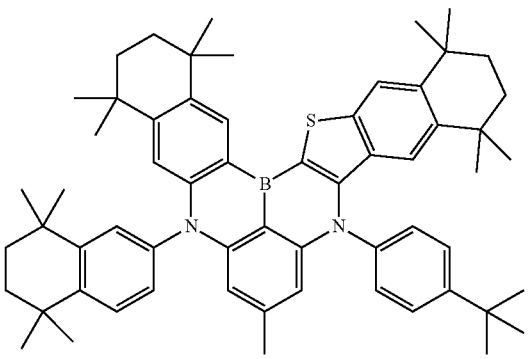
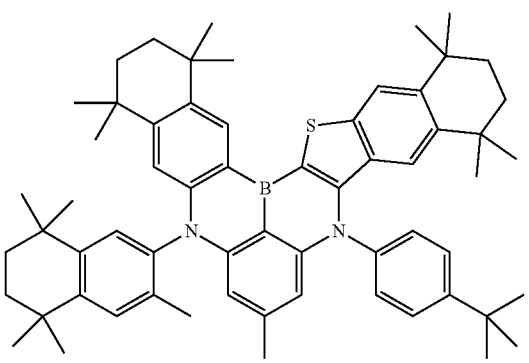
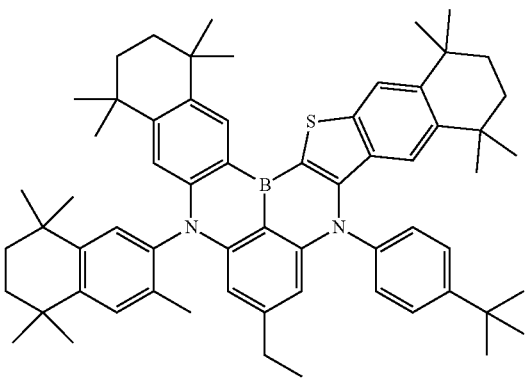

| 1399 -continued | 1400 -continued |
|---|---|
| 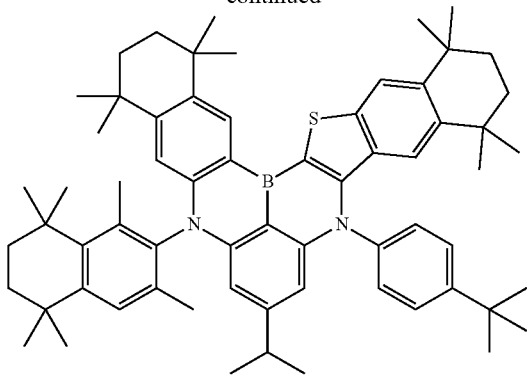 | 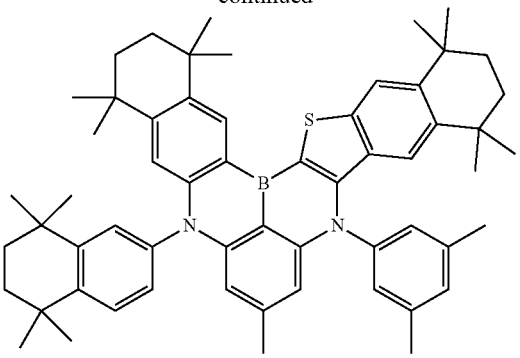 |
| 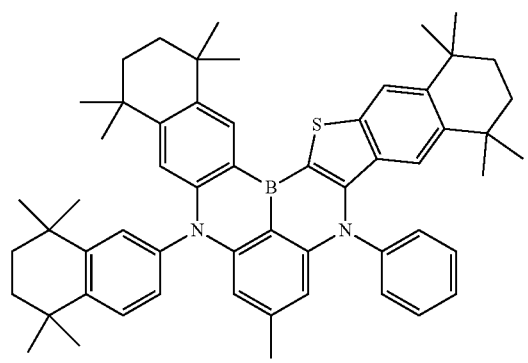 | 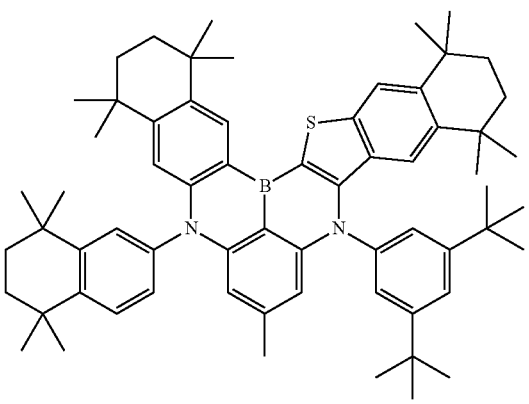 |
| 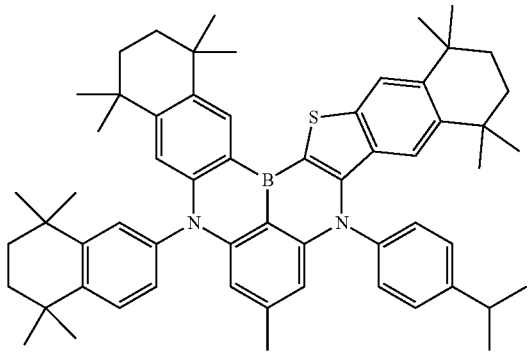 | 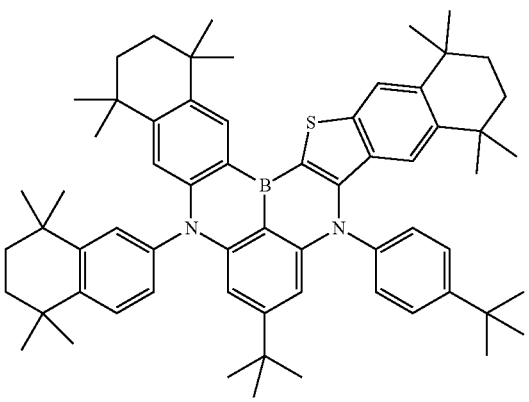 |
| 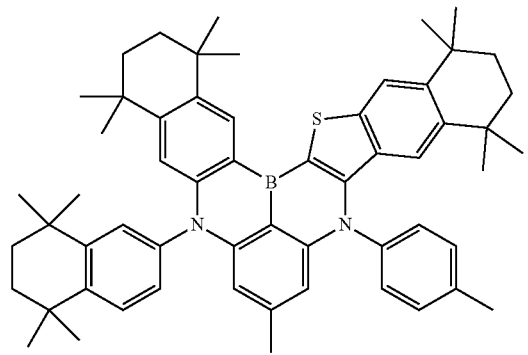 | 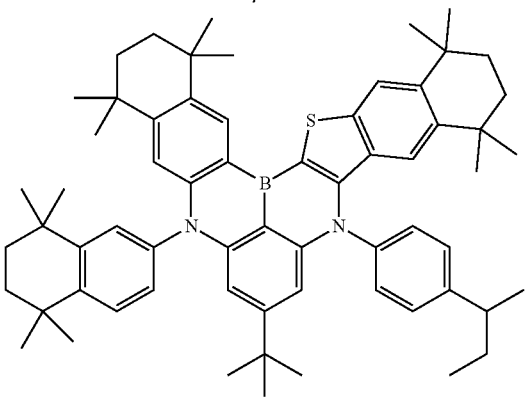 |

1401
-continued
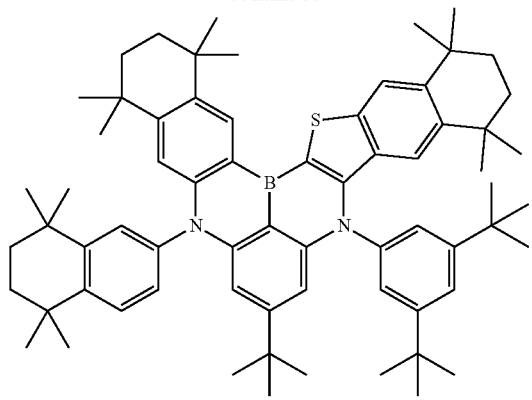
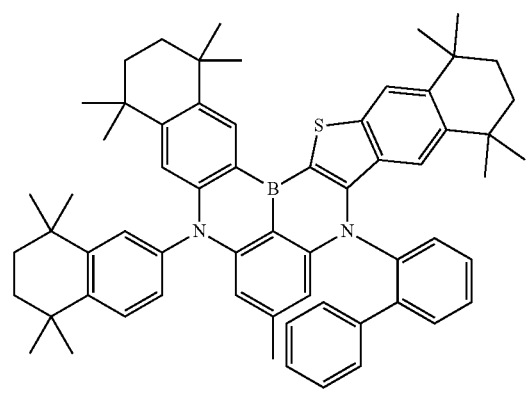
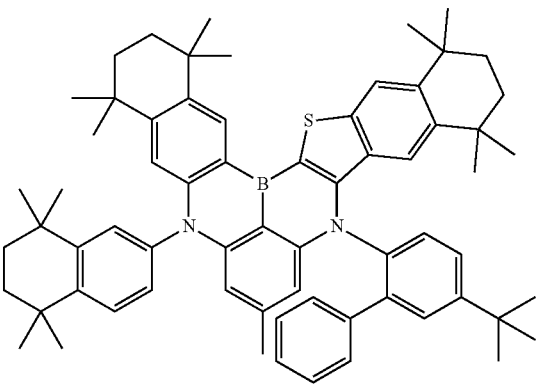
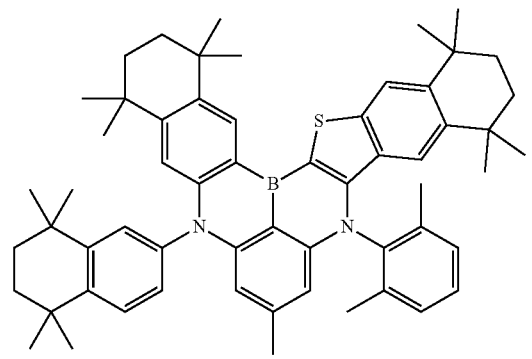
1402
-continued
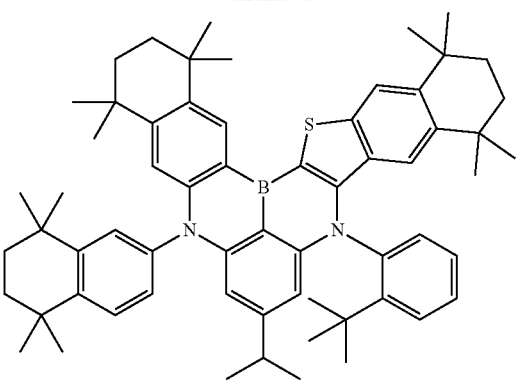
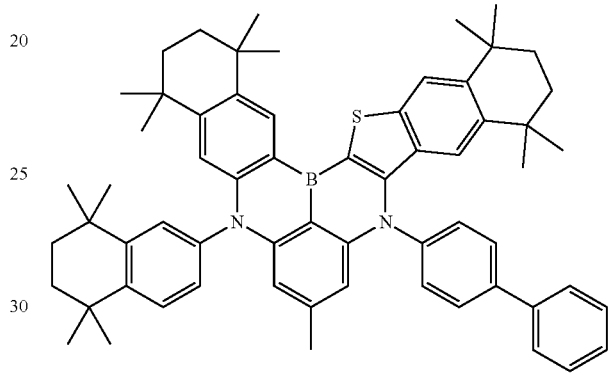
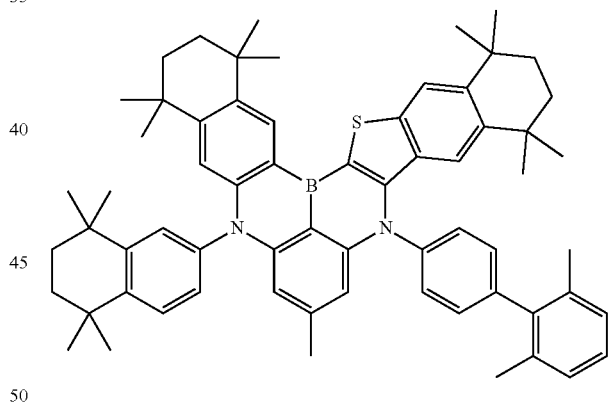
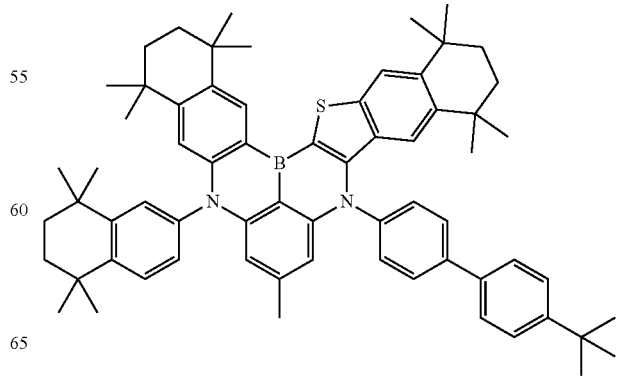

1403
-continued
1404
-continued
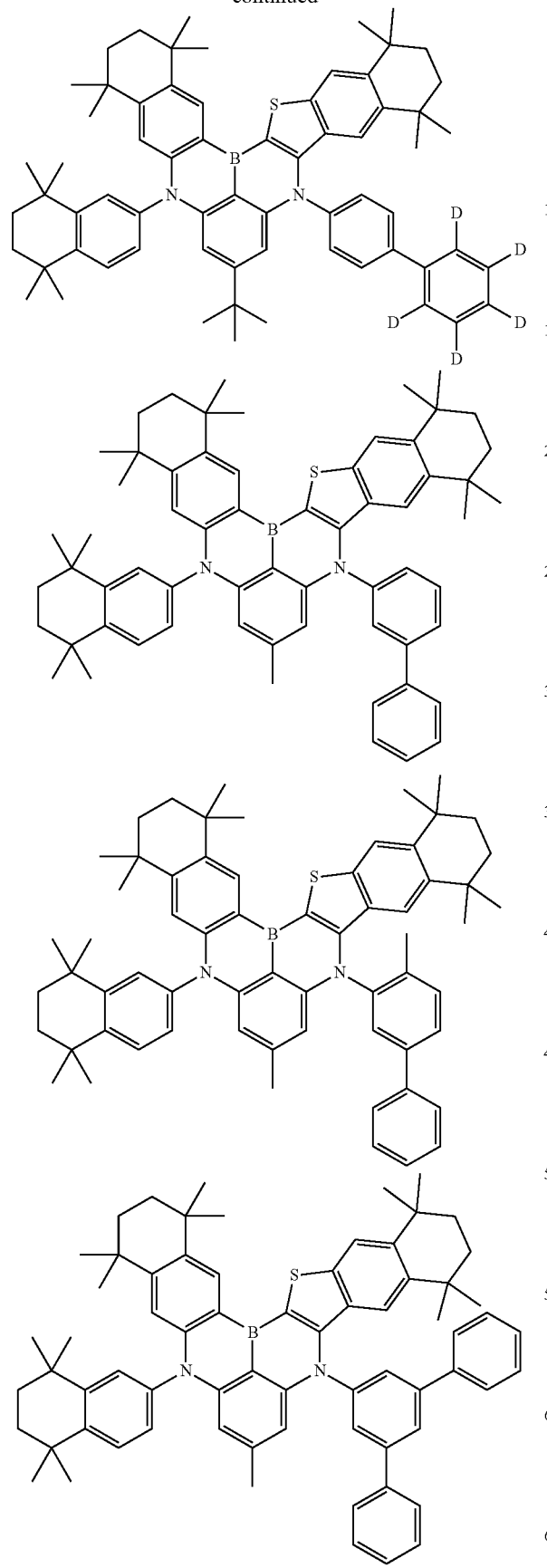
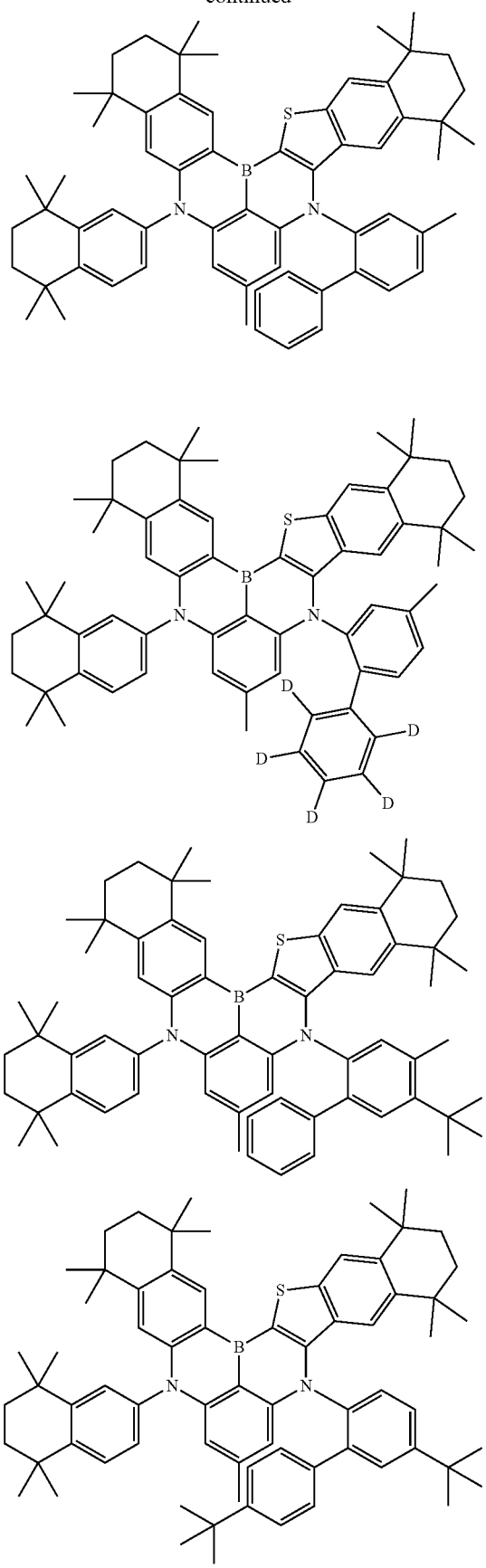

1405
-continued

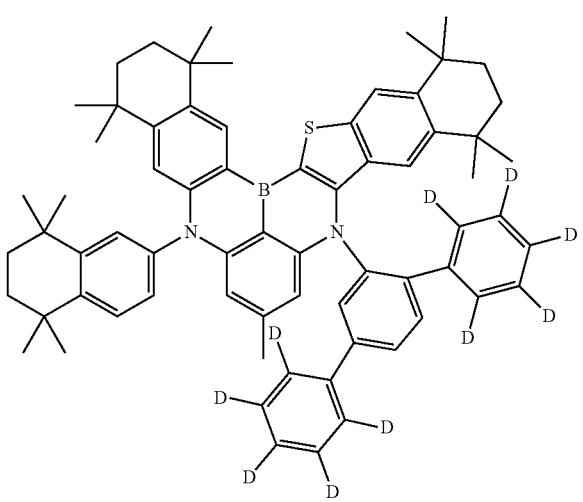
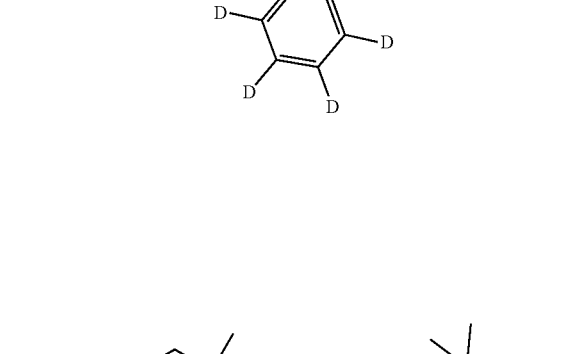
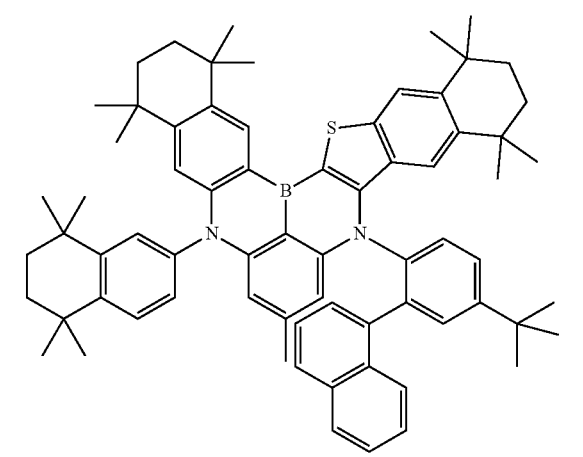
1406
-continued
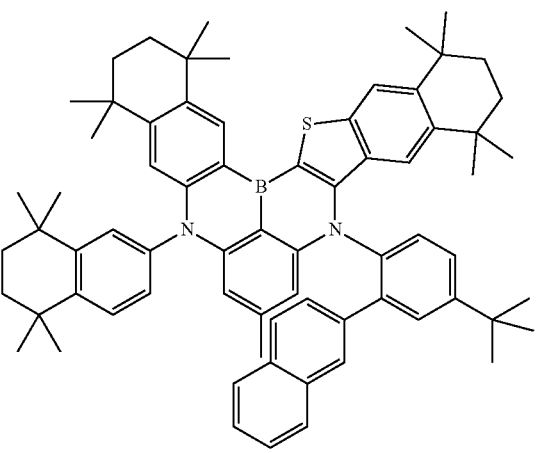
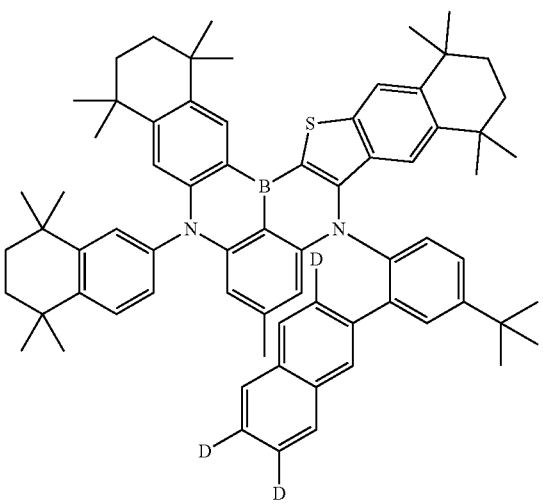
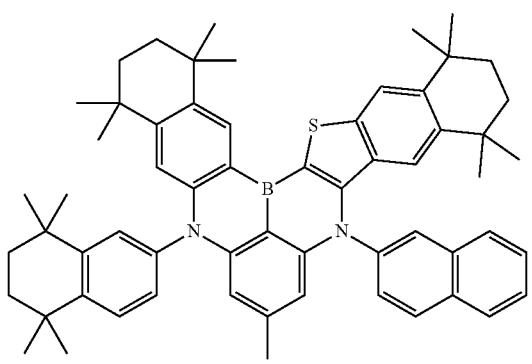
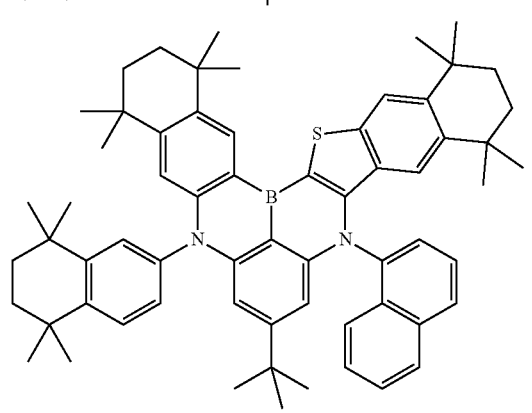

1407
-continued
1408
-continued
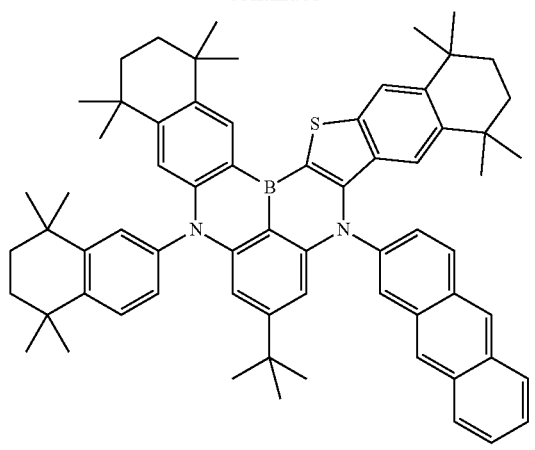
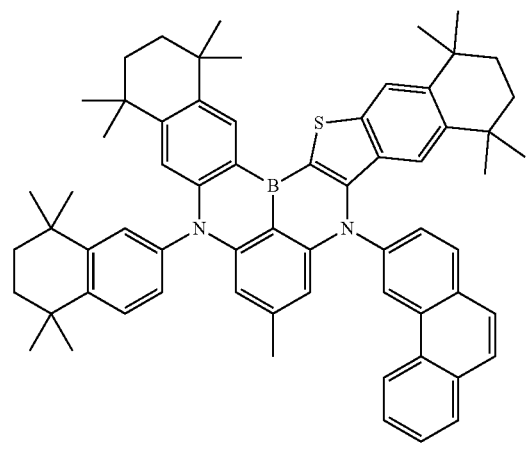
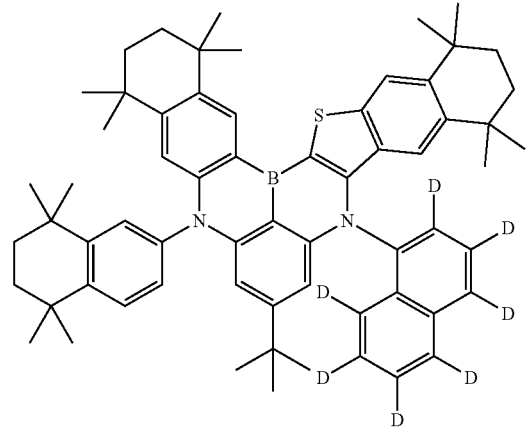
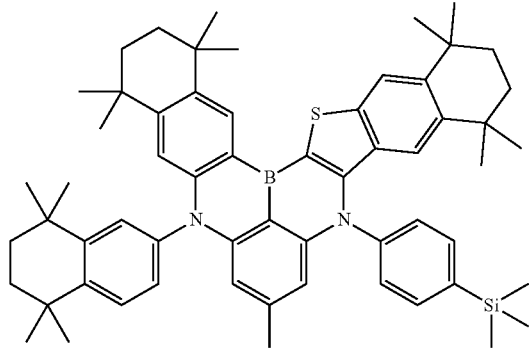
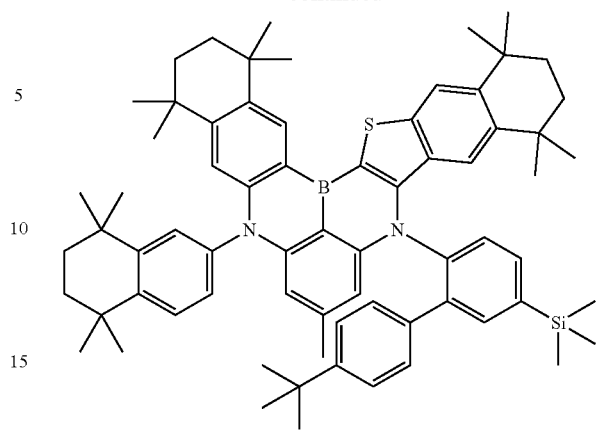
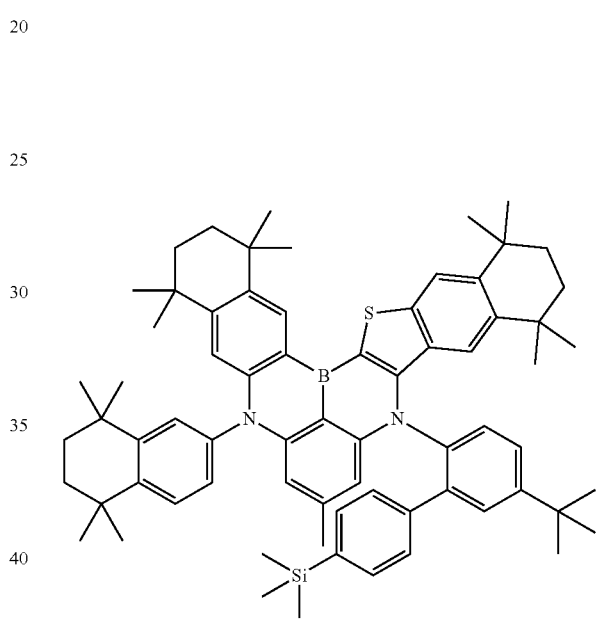
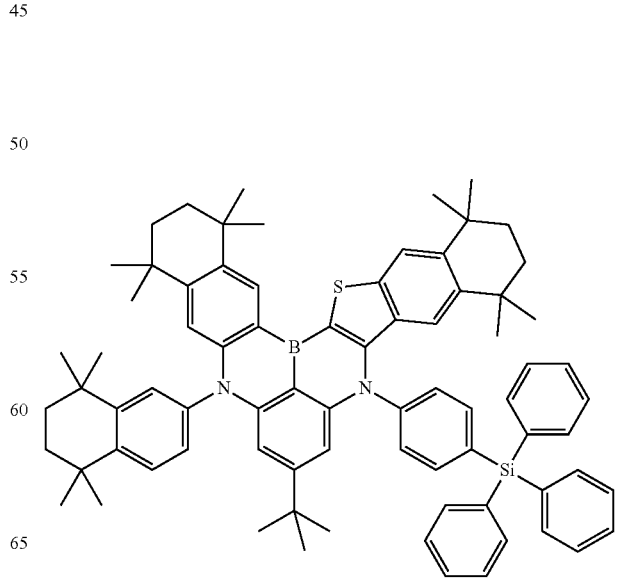

1409
-continued
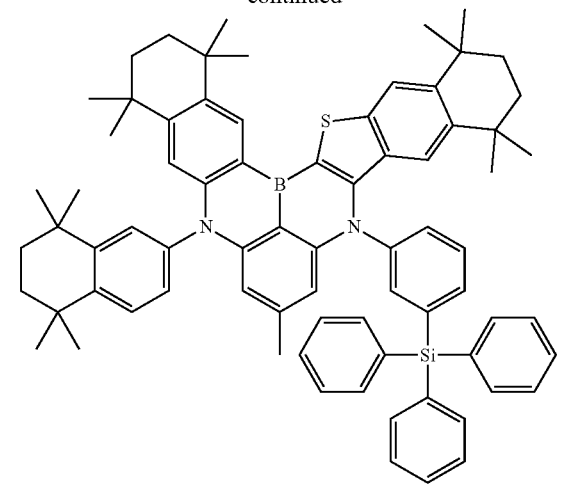
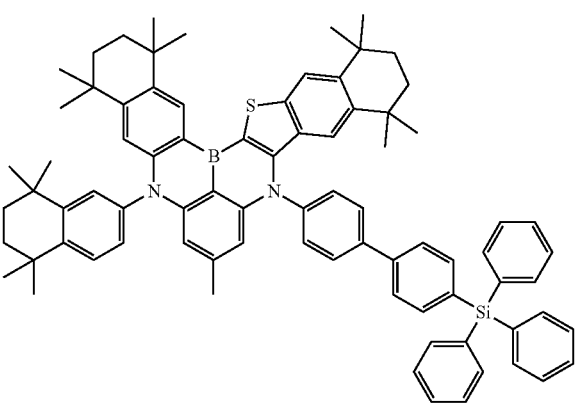
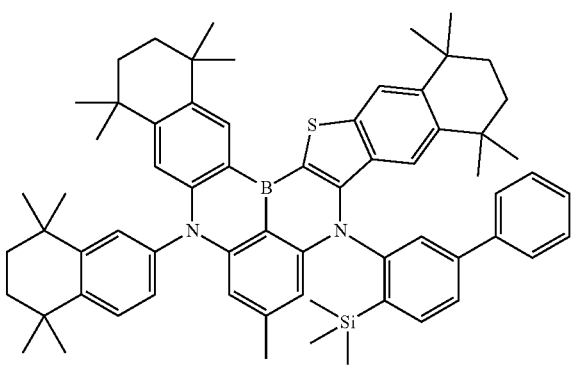
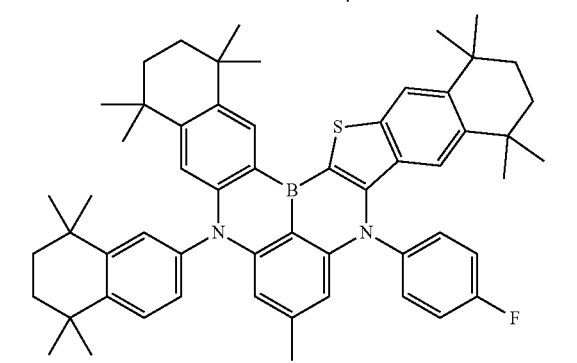
1410
-continued
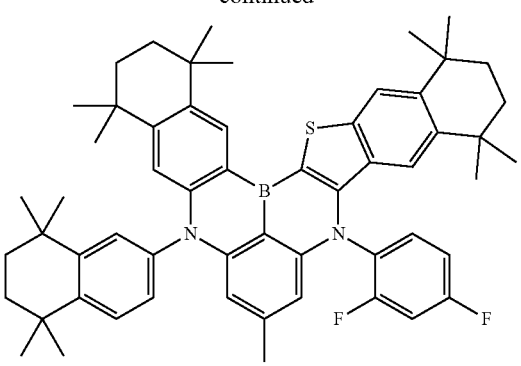
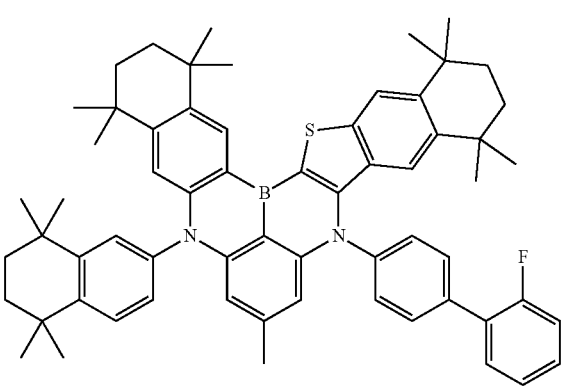
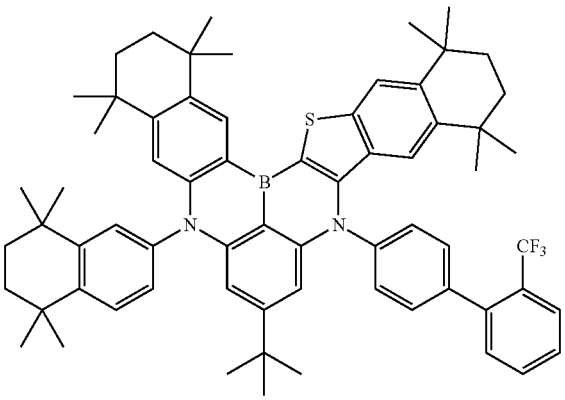
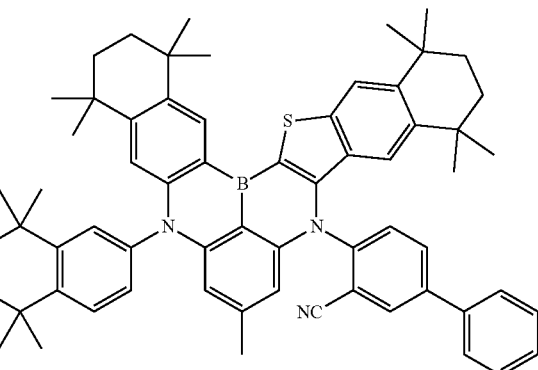

1411
-continued
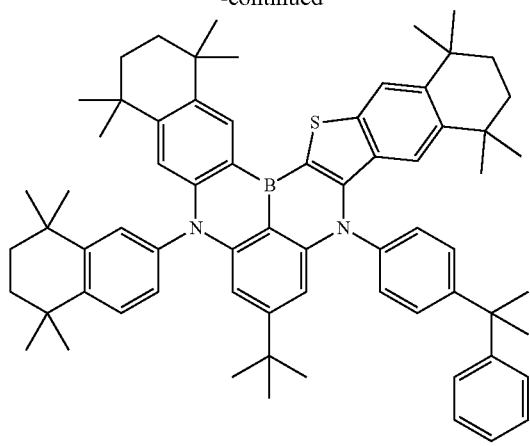
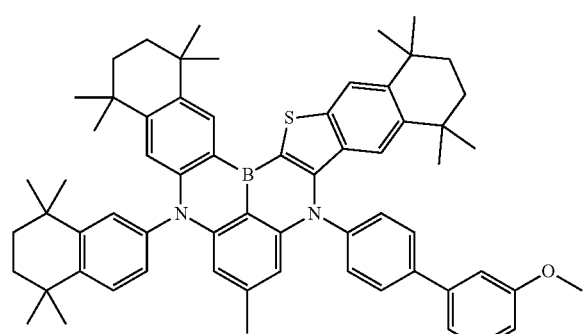
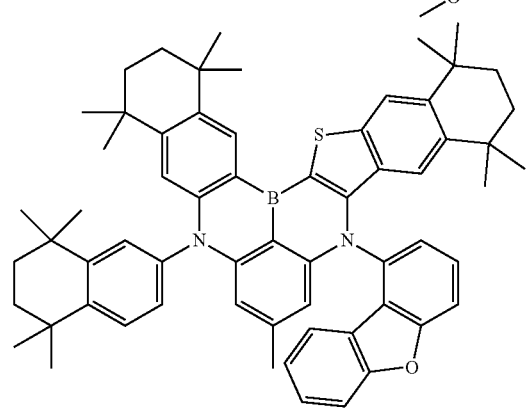
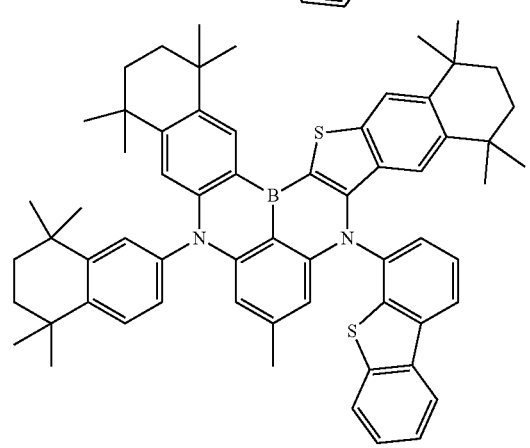
1412
-continued
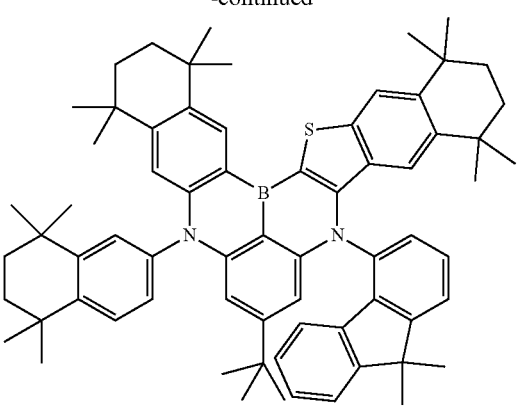
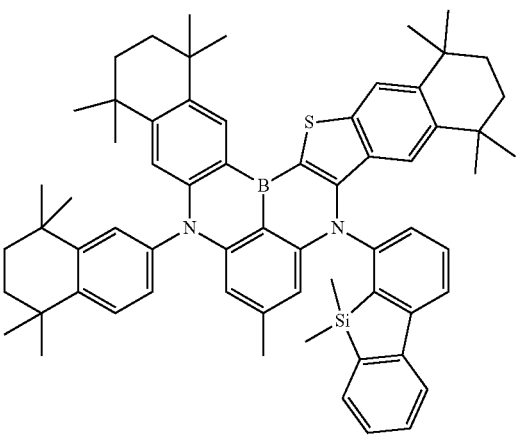
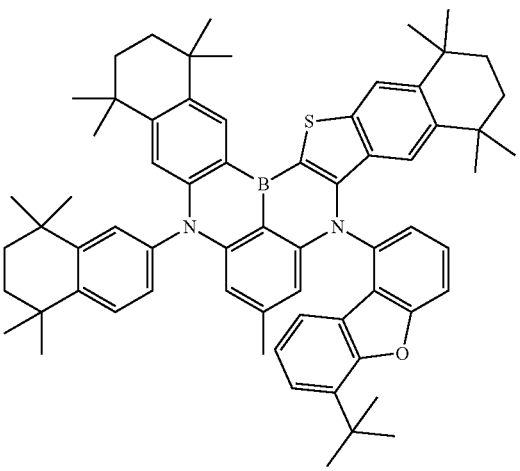

1413
-continued
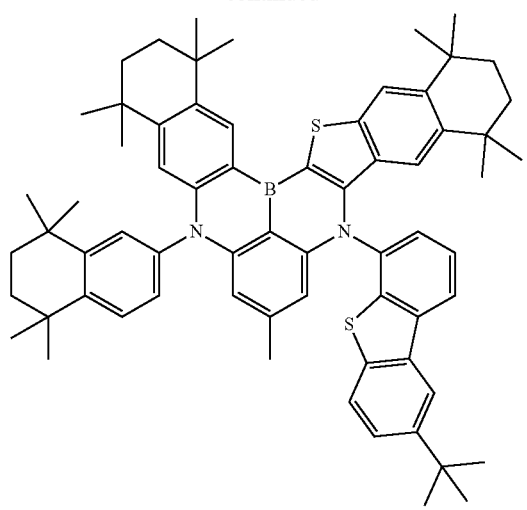
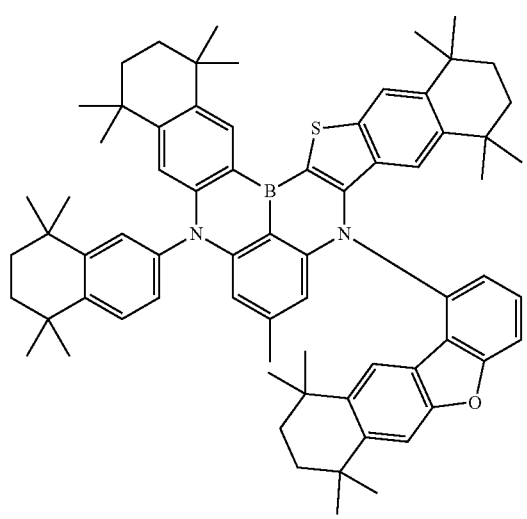
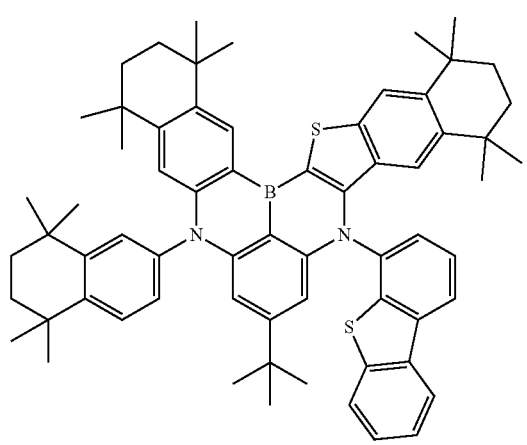
1414
-continued
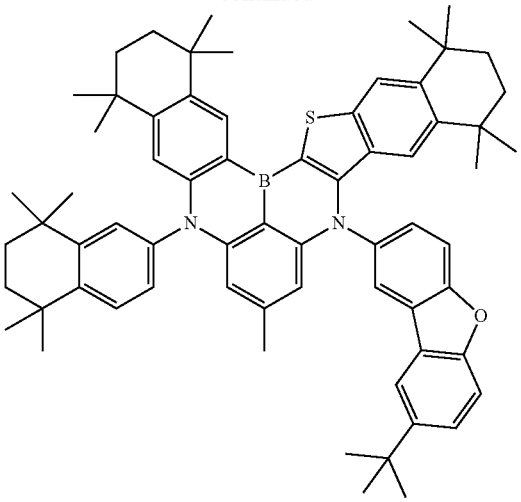
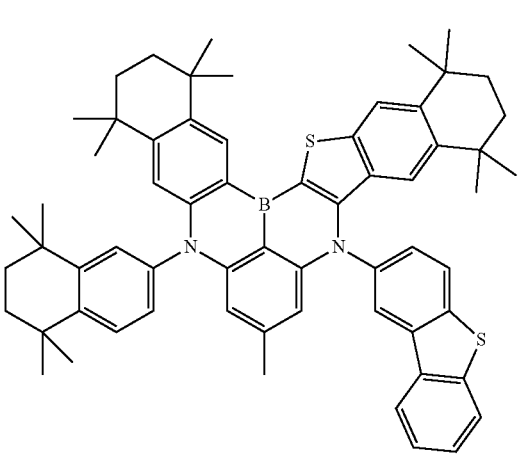
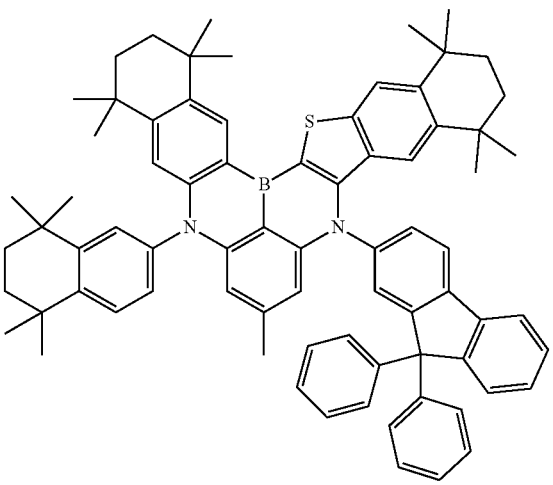

1415
-continued
1416
-continued
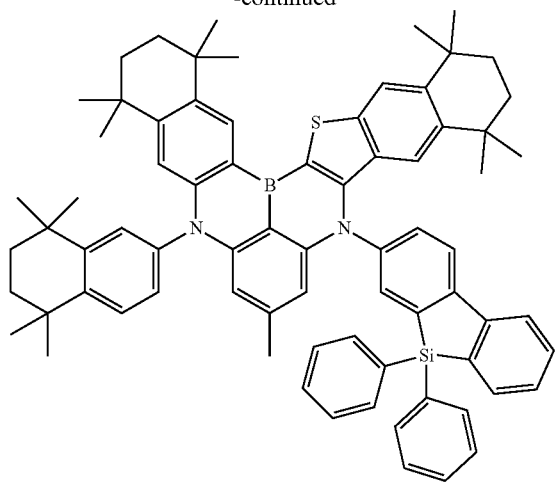
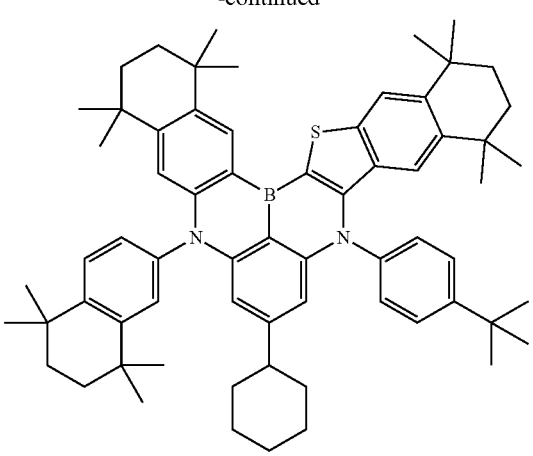
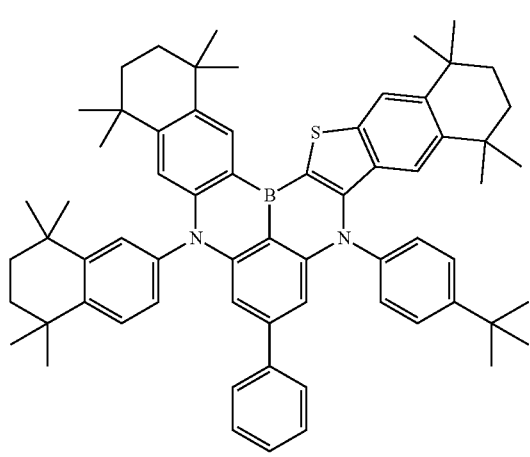
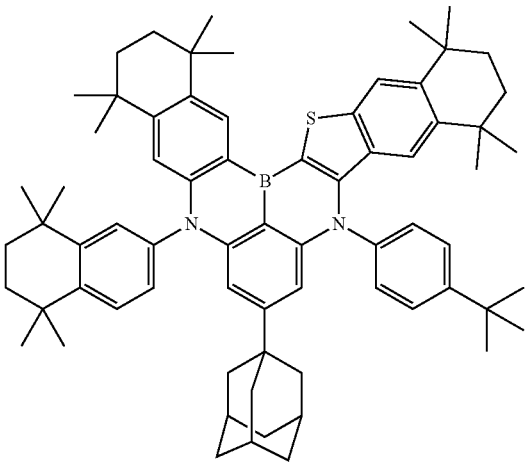
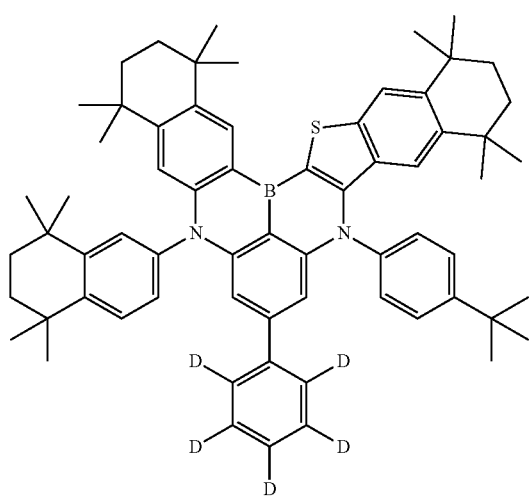
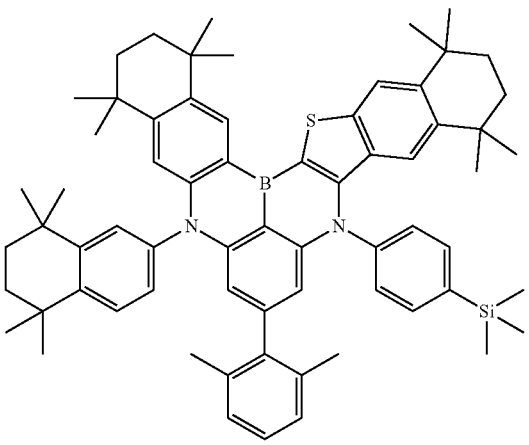

1417                                                    1418
-continued                                             -continued
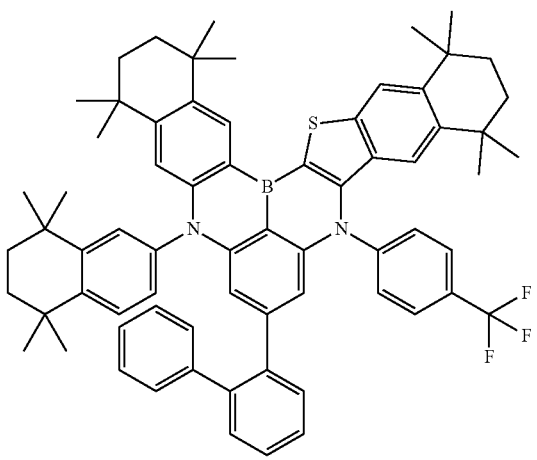
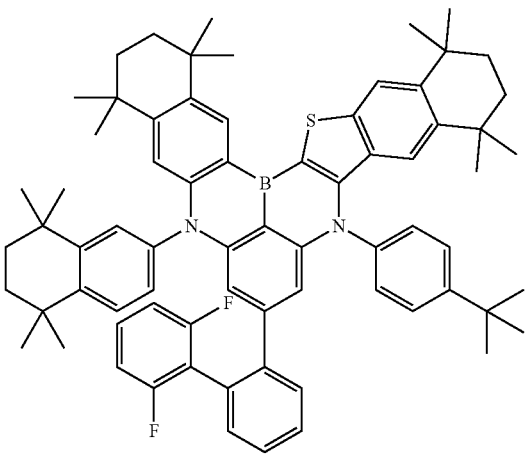
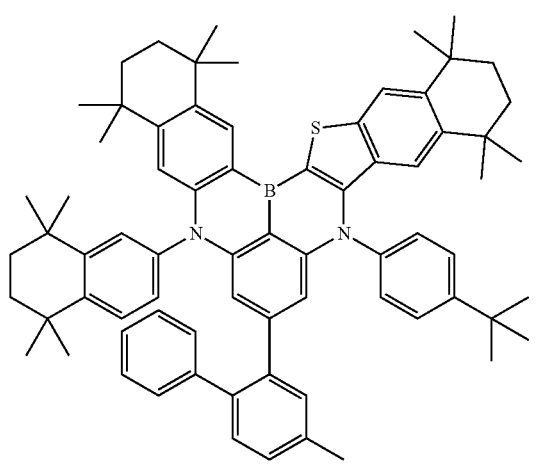

1419
-continued
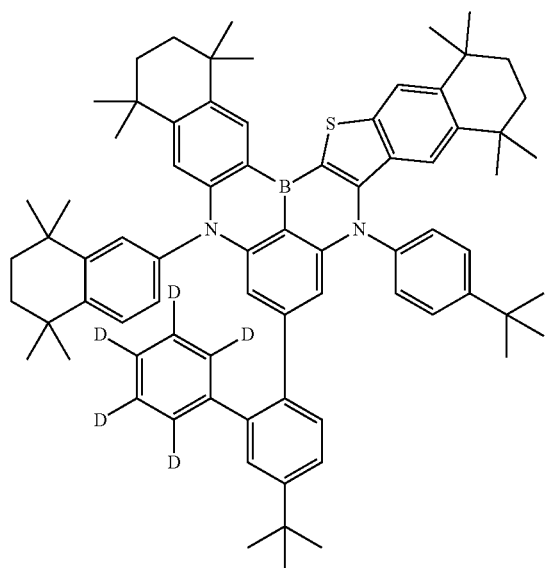
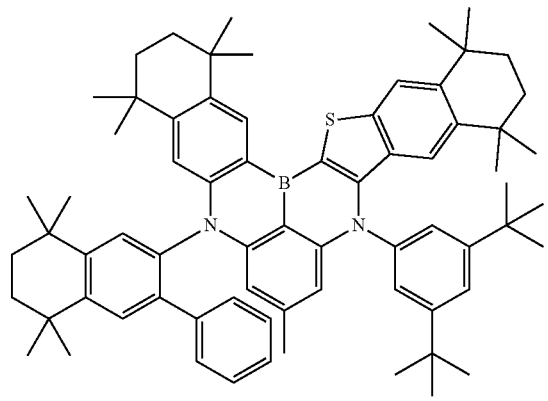
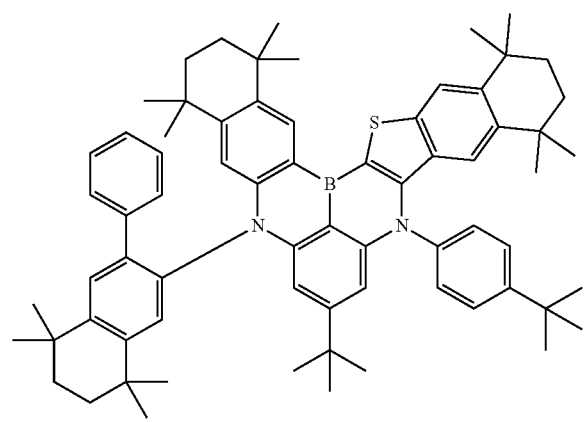
1420
-continued
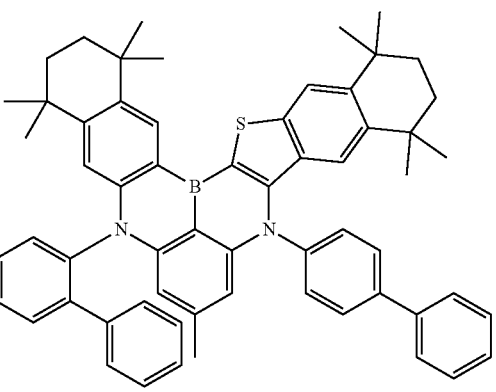
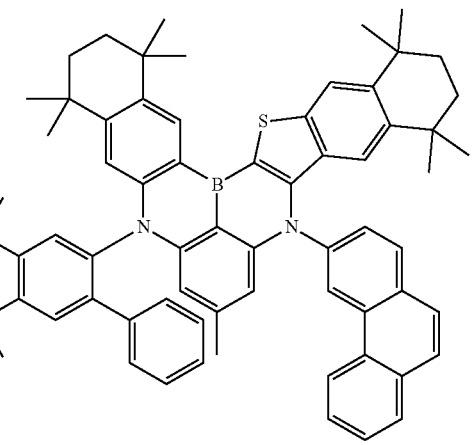

| 1421 -continued | 1422 -continued |
|---|---|
| 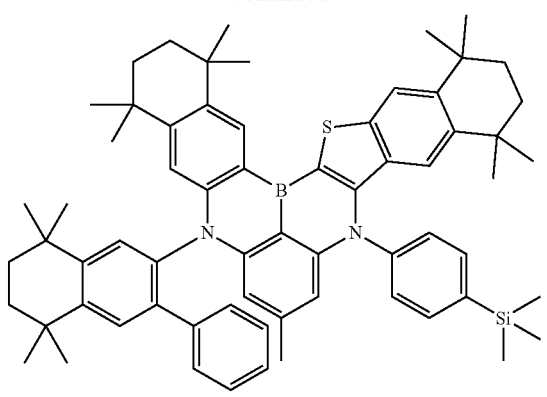 | 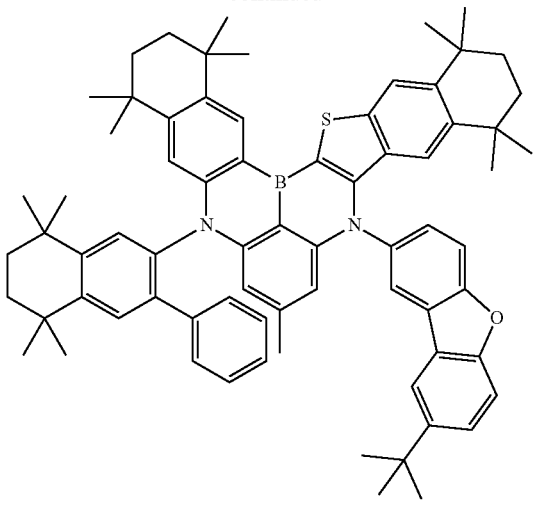 |
| 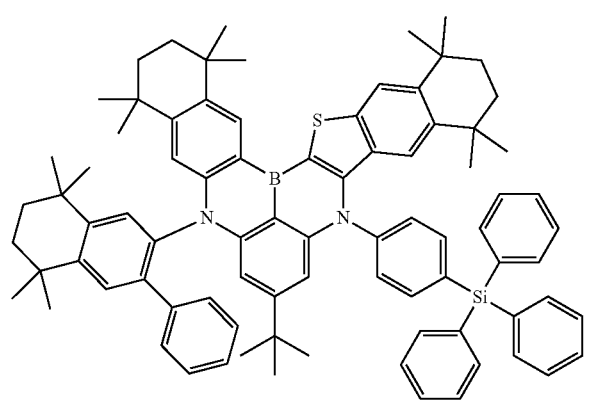 | |
|  |  |
| 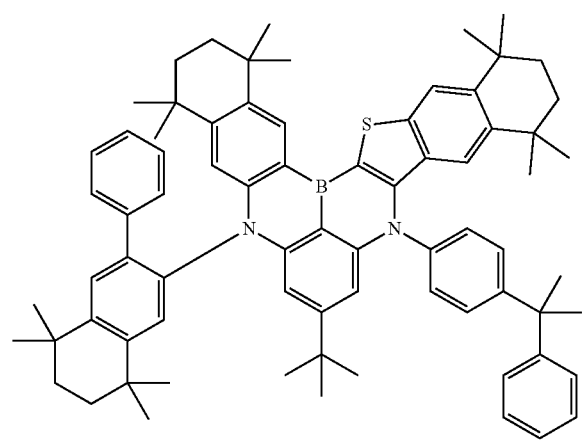 | 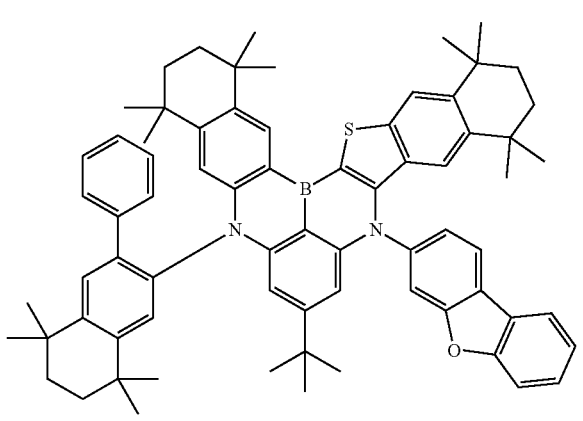 |

1423
-continued
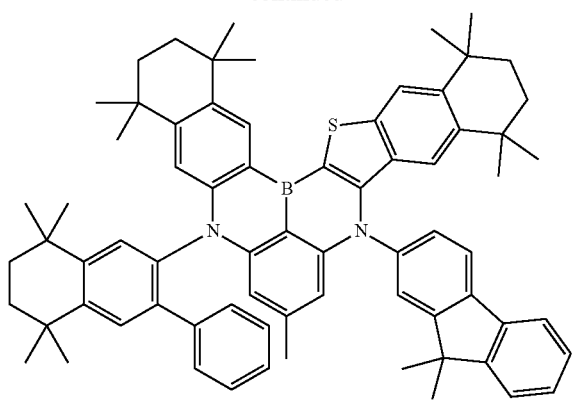
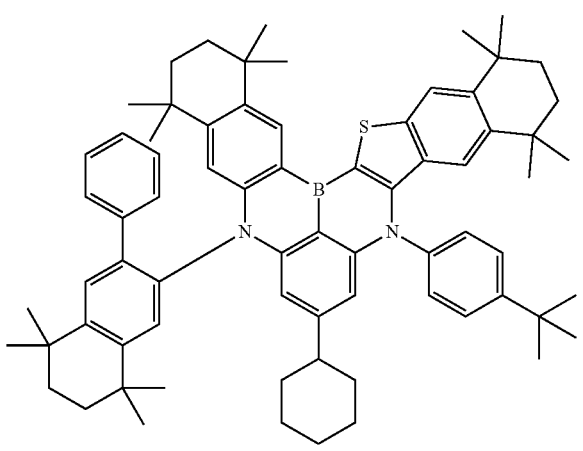
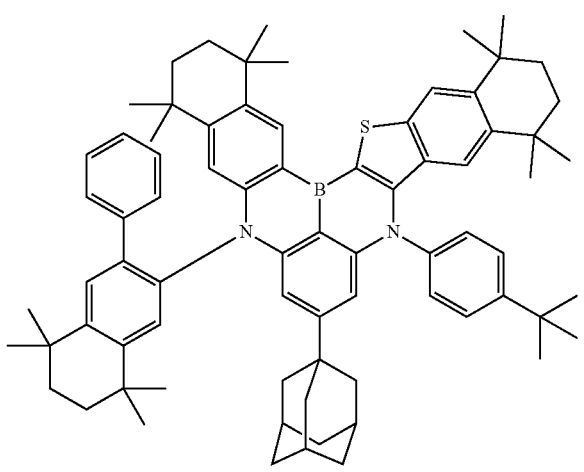
1424
-continued
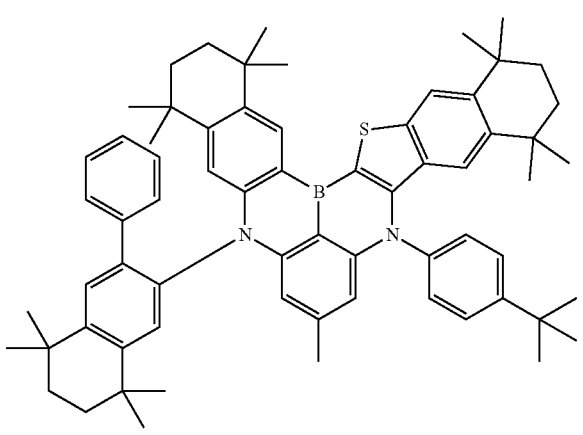
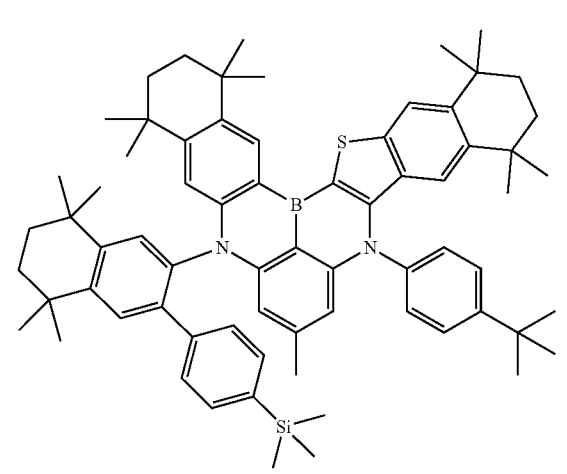

1425
-continued
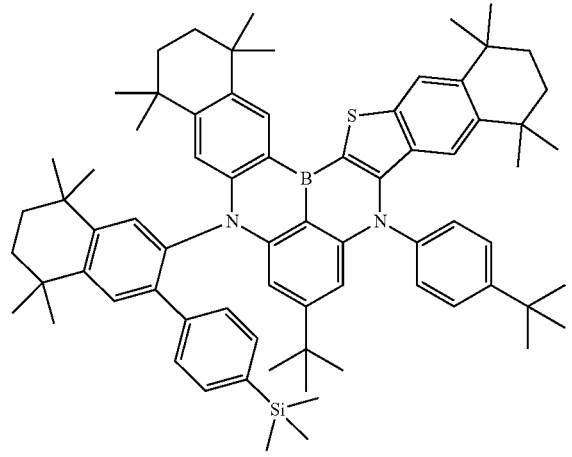
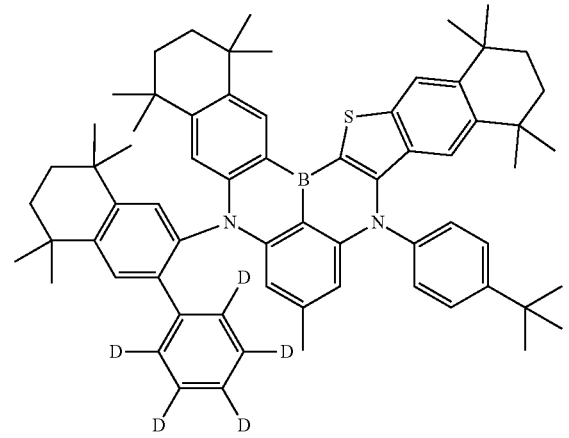
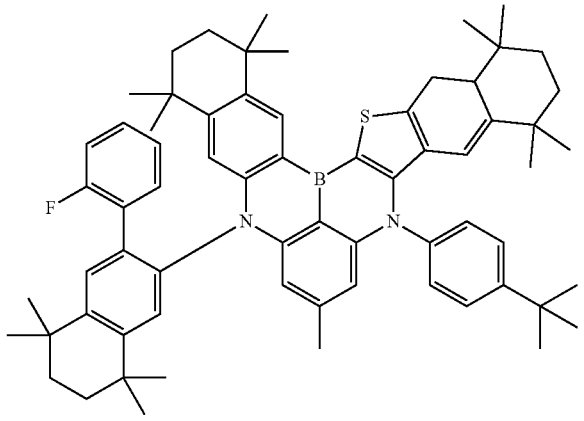
1426
-continued
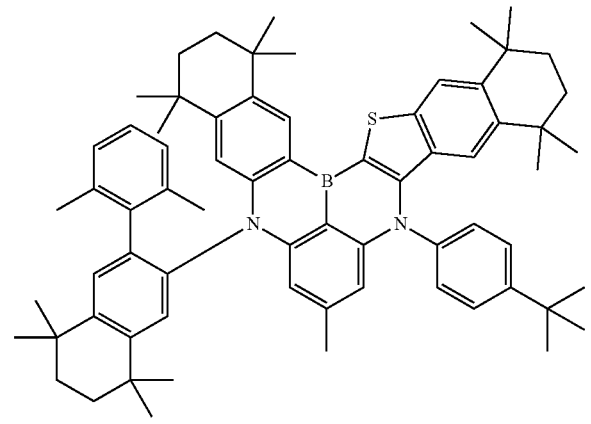
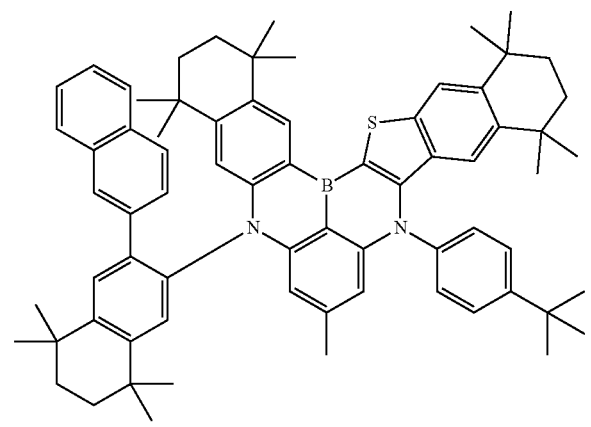

1427
-continued
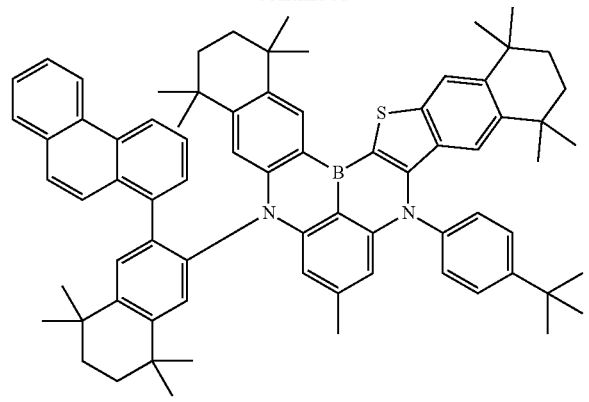
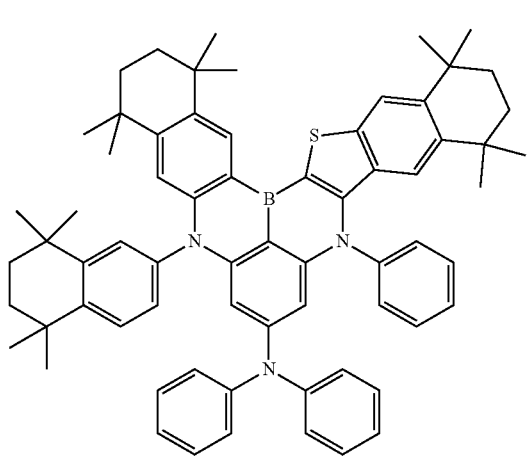
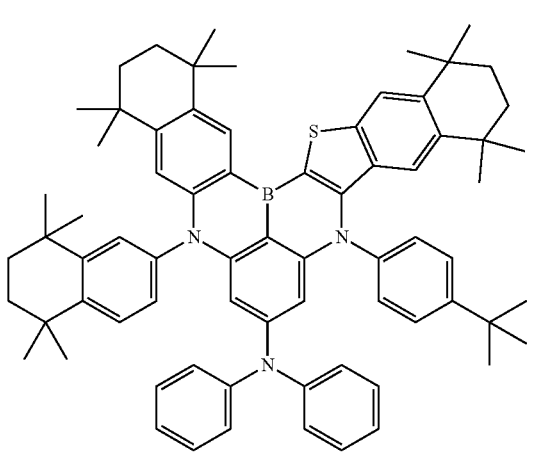
1428
-continued
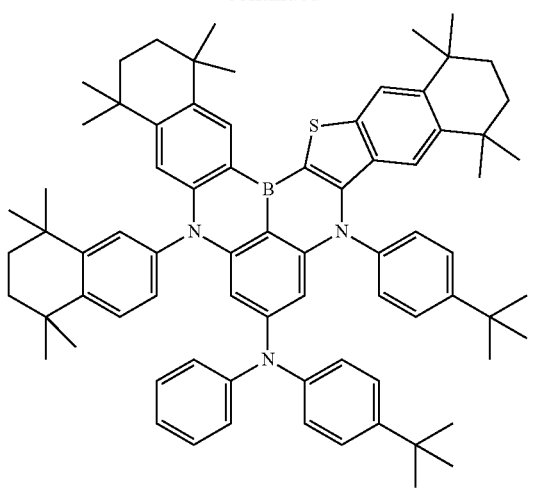
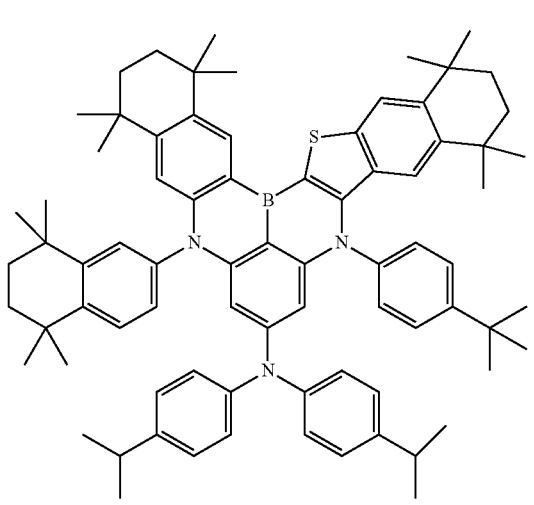
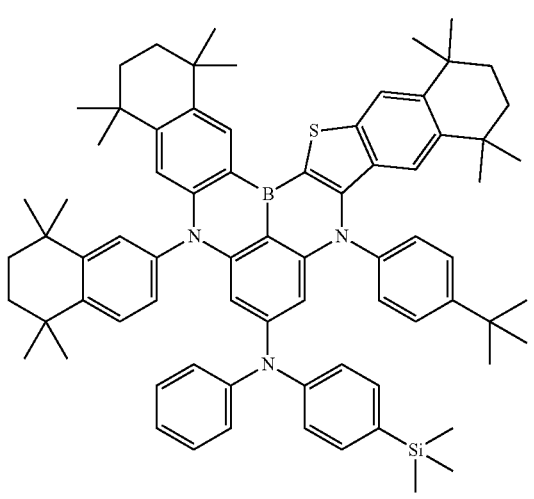

1429
-continued
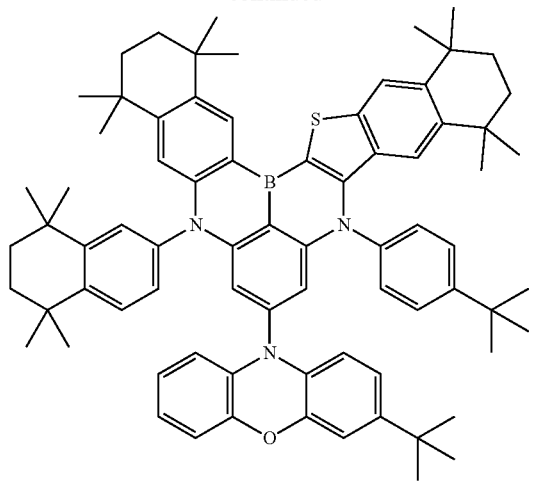
1430
-continued
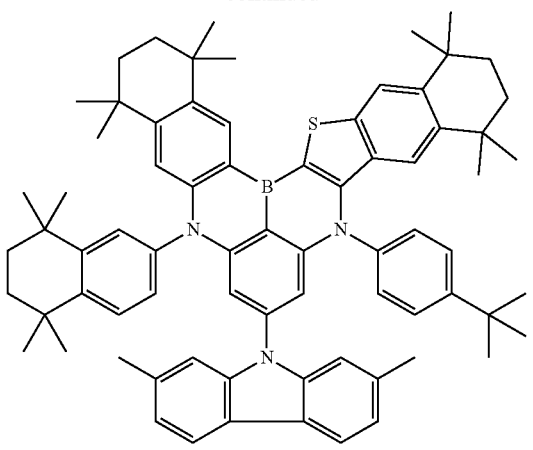
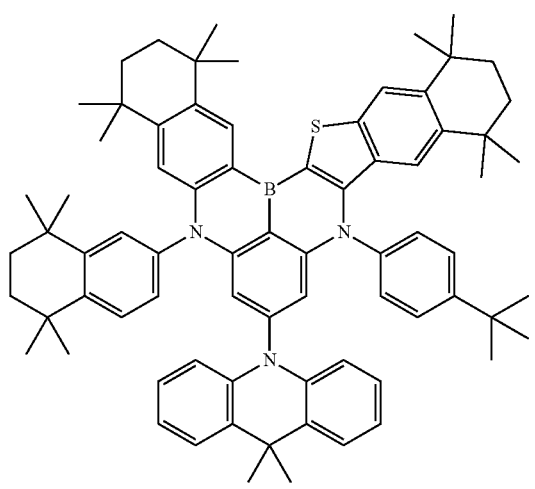
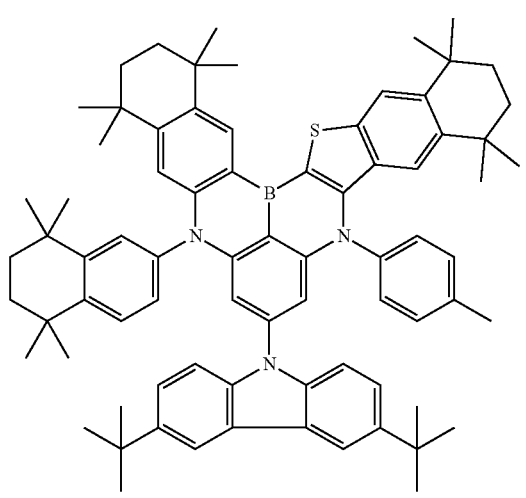
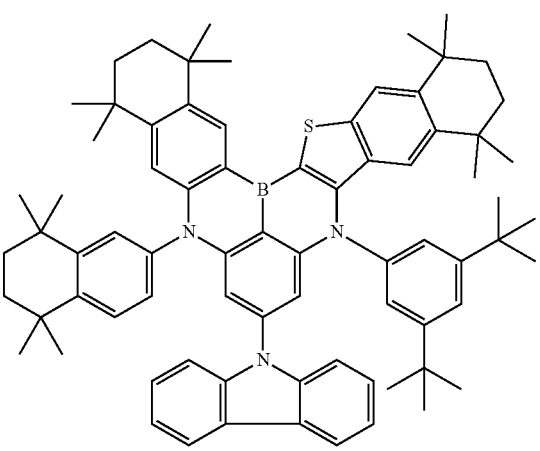
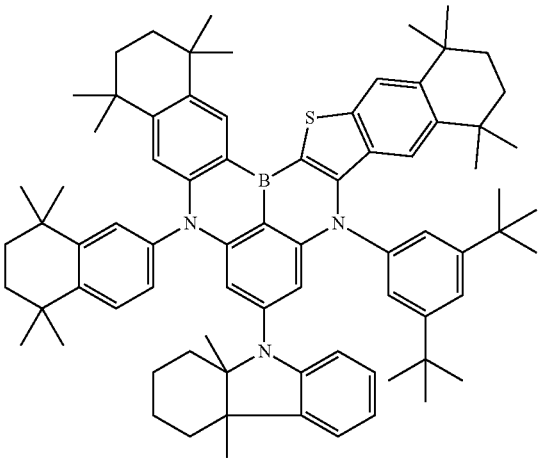

1431
-continued
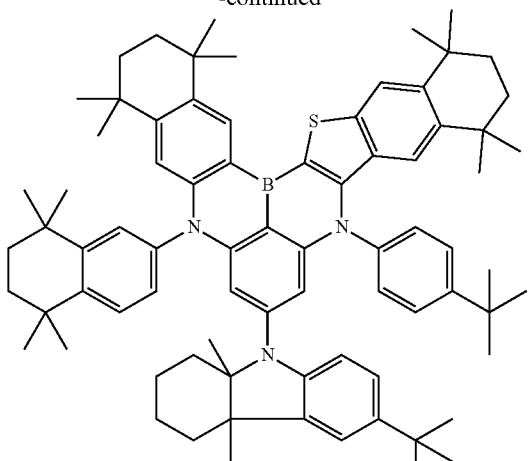
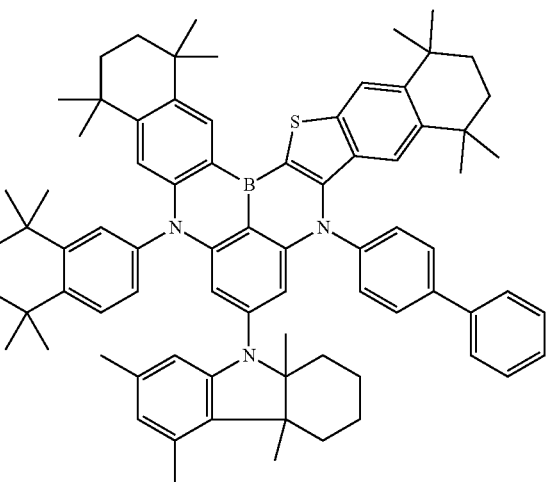
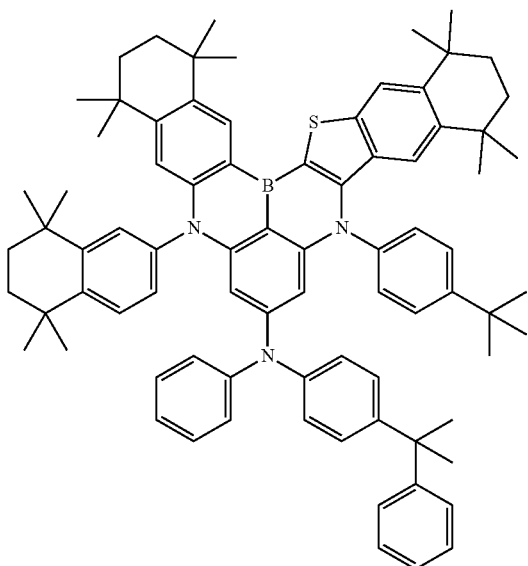
1432
-continued
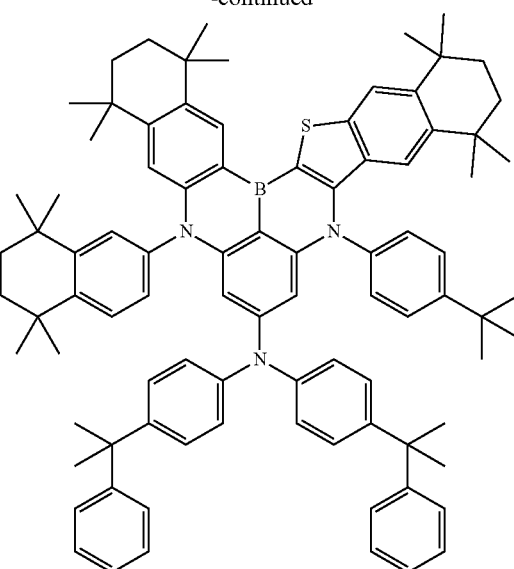
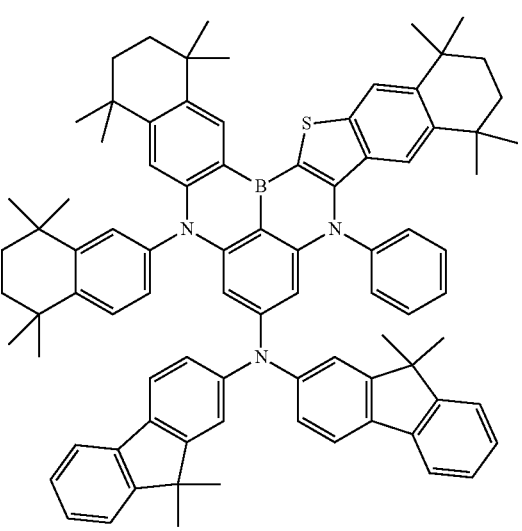
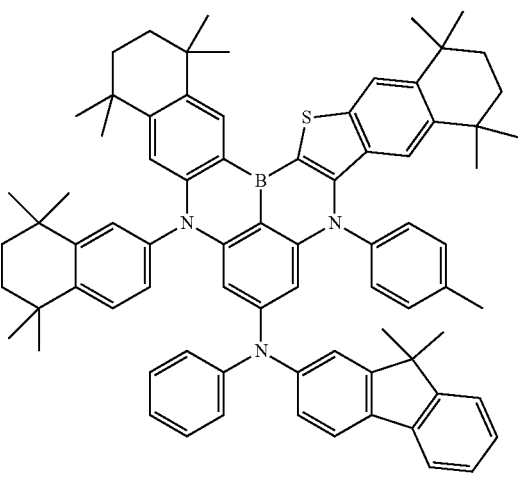

1433
-continued
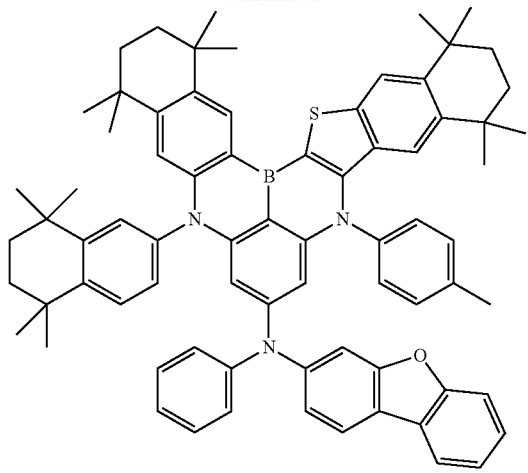
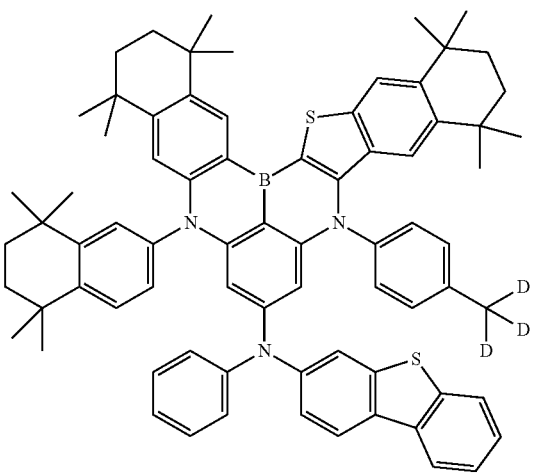
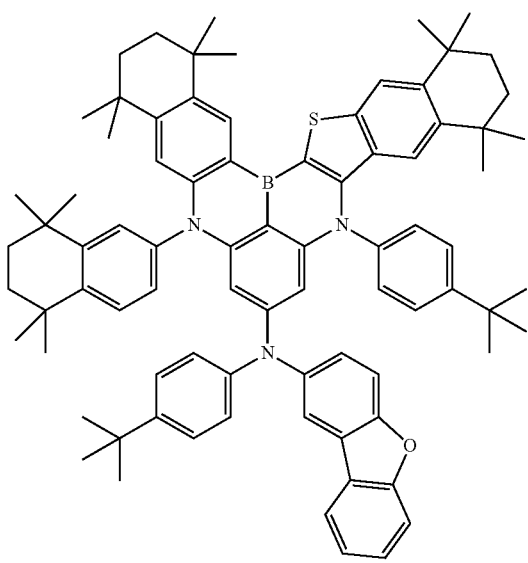
1434
-continued
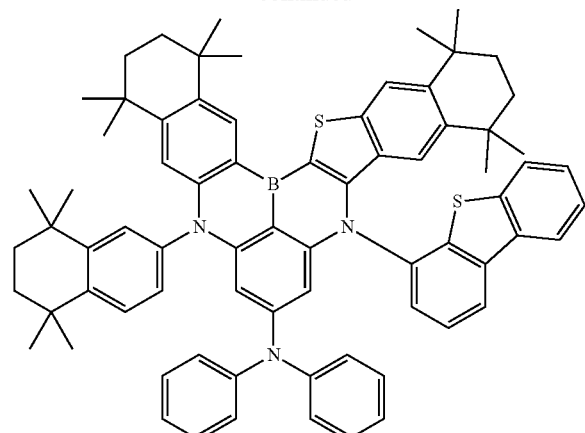
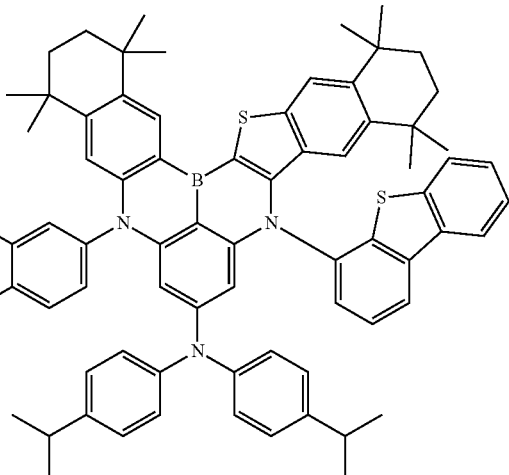
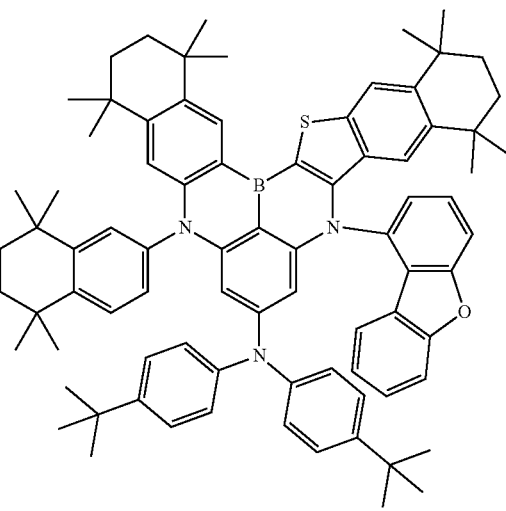

| 1435 | 1436 |
|---|---|
| -continued | -continued |
| 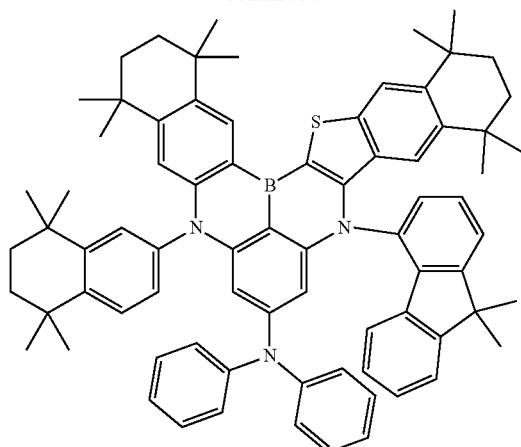 | 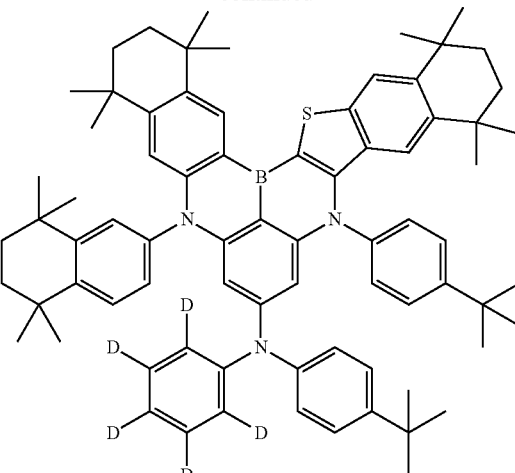 |
| 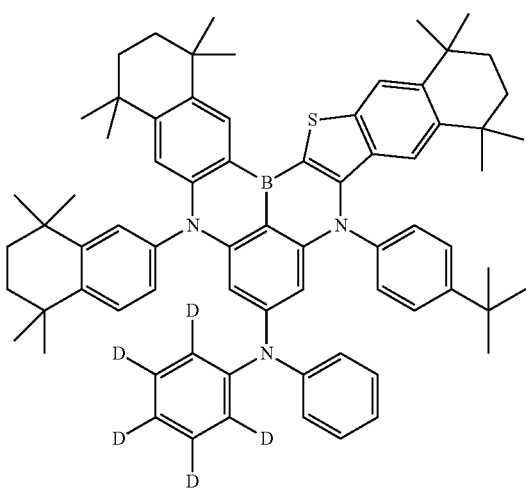 | 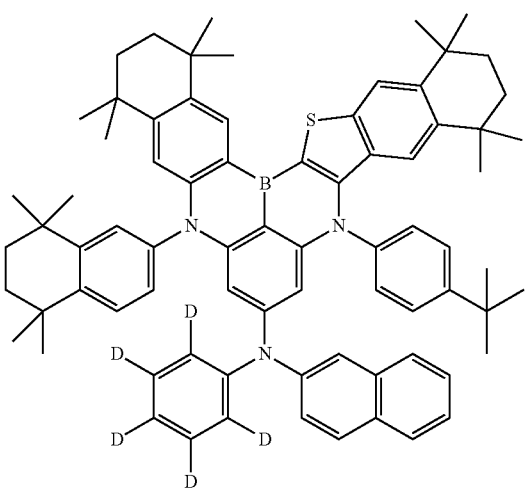 |
| 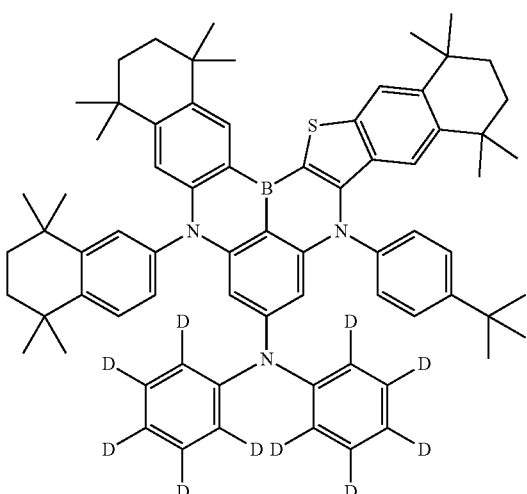 | 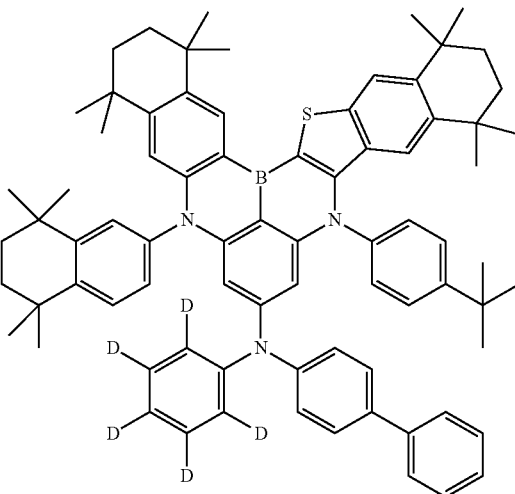 |

1437
-continued
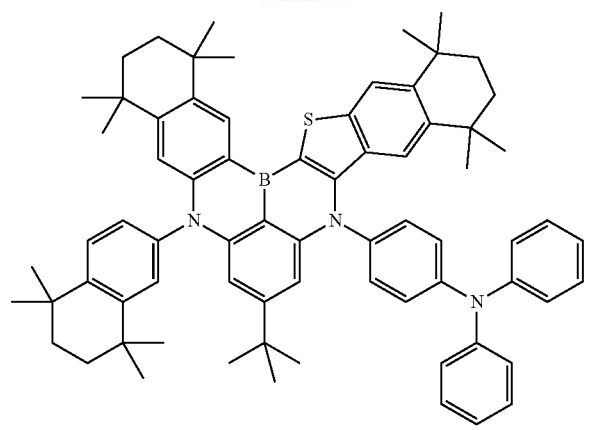
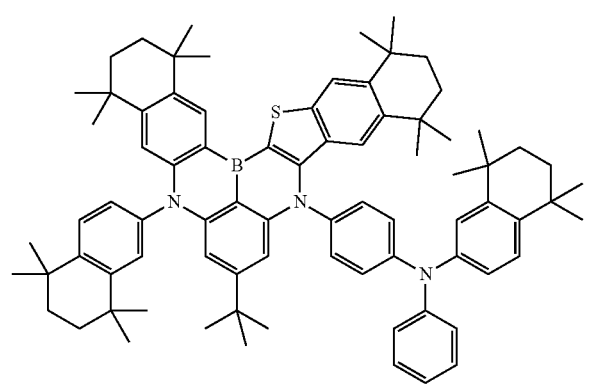
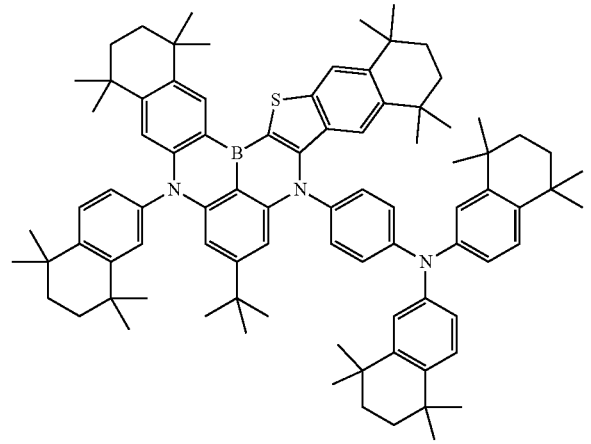
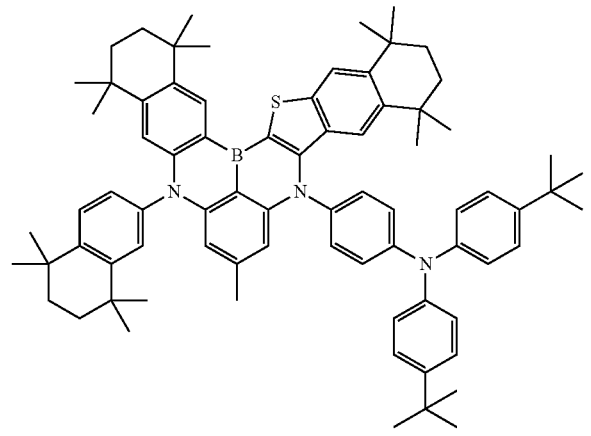
1438
-continued
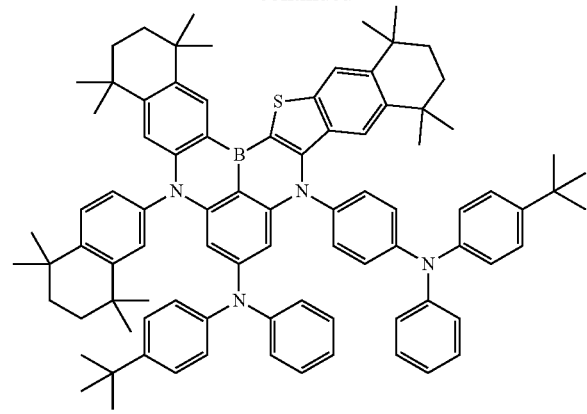
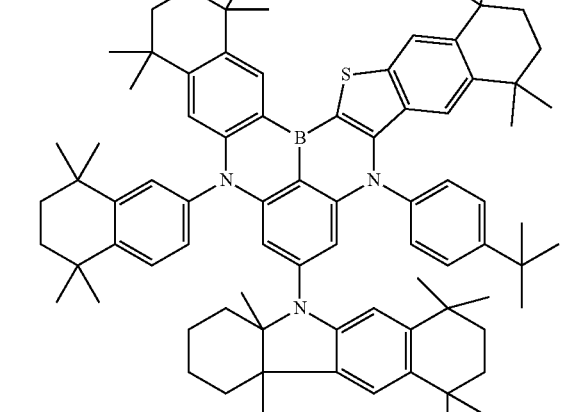
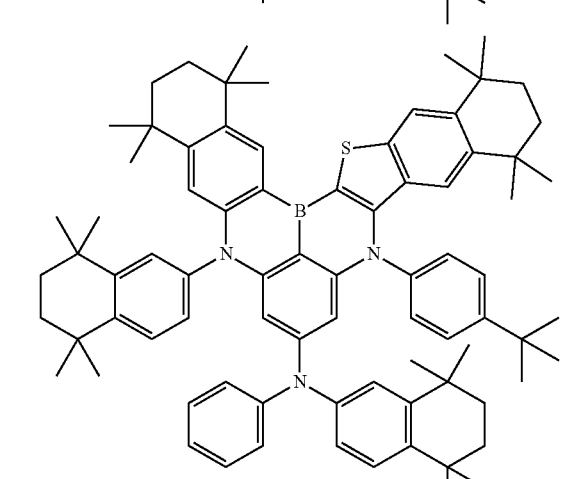
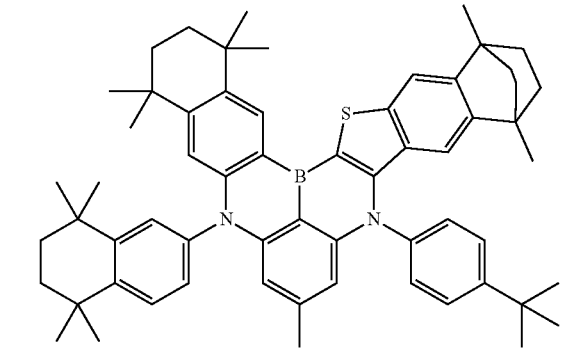

1439
-continued
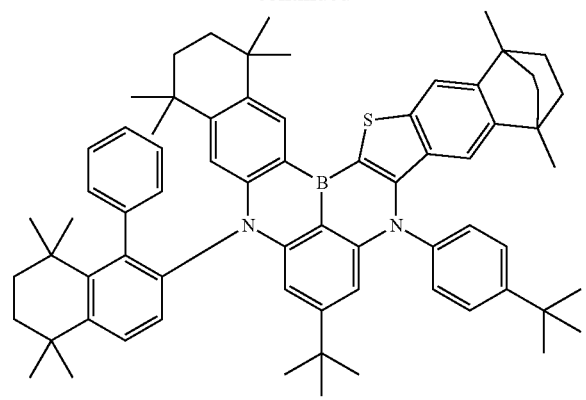
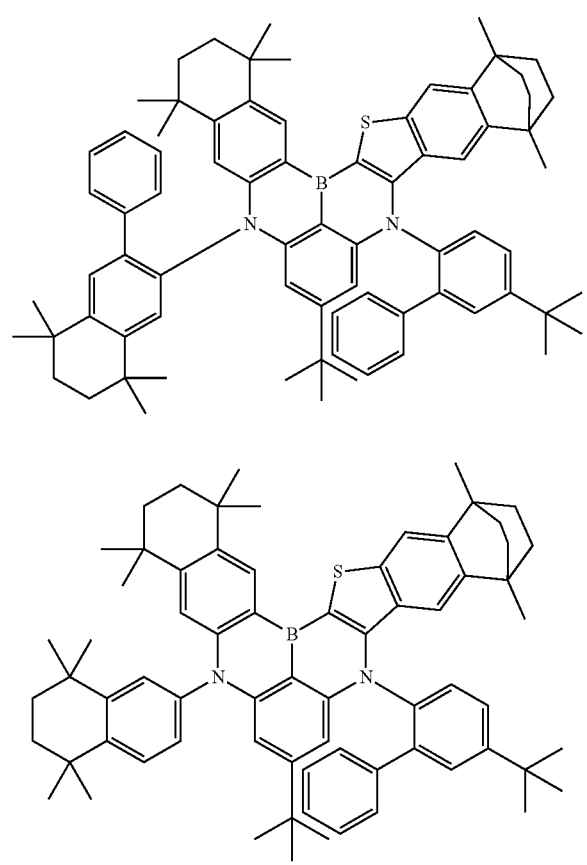
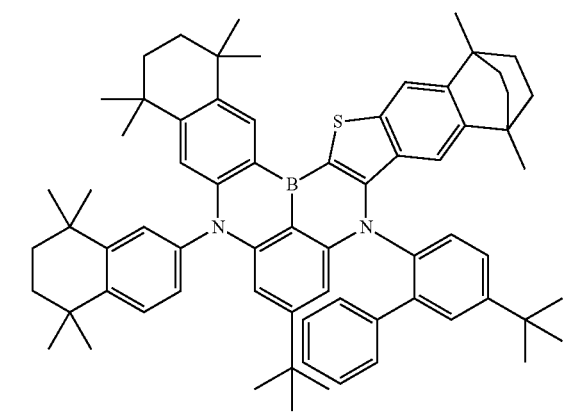
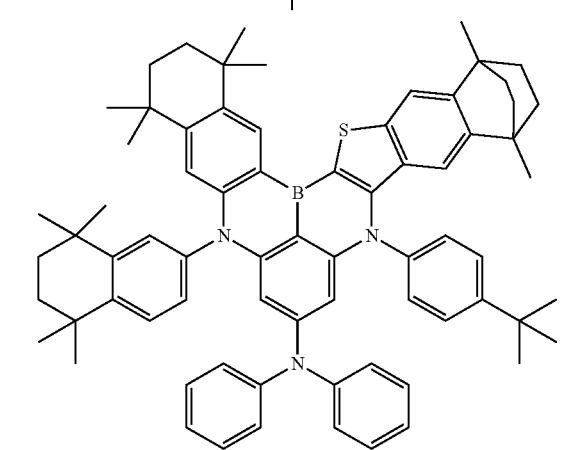
1440
-continued
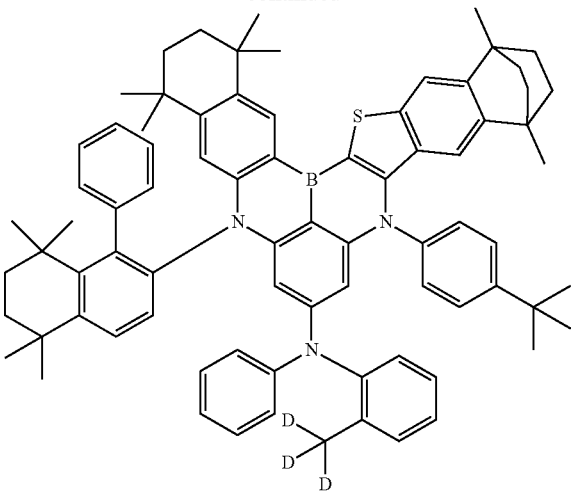
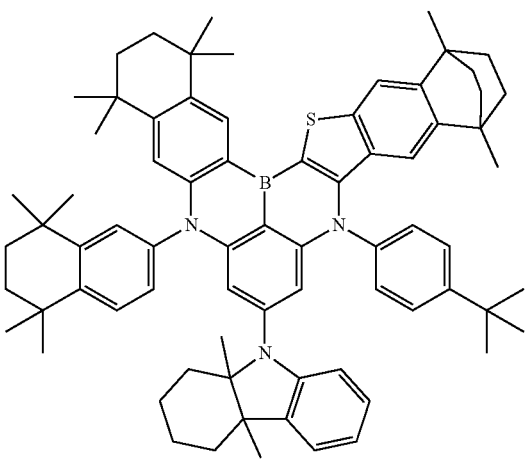
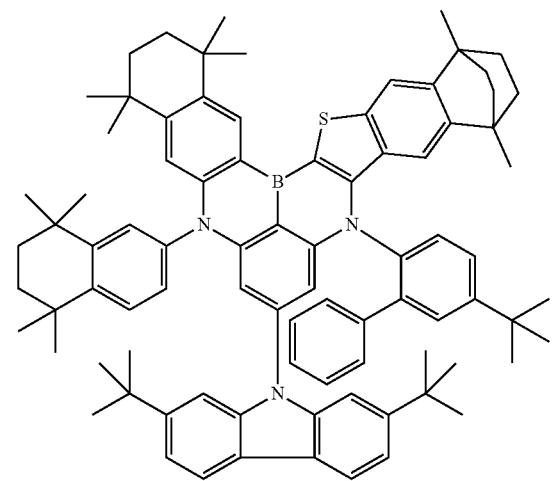

1441
-continued
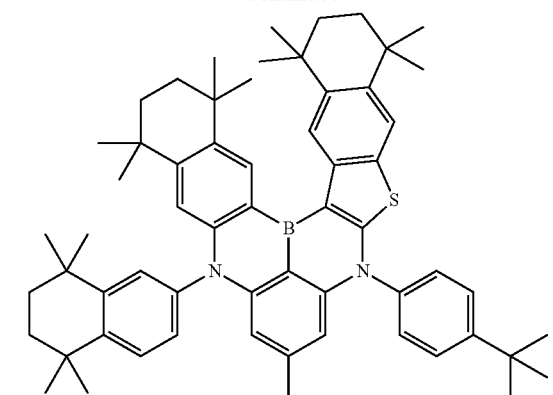
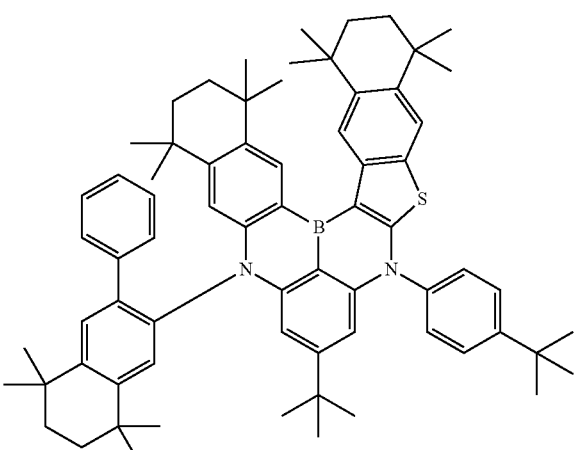
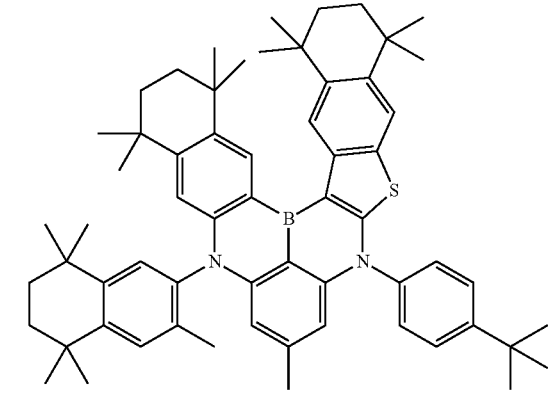
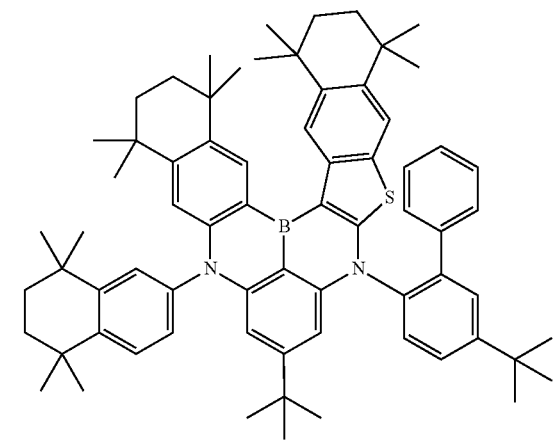
1442
-continued
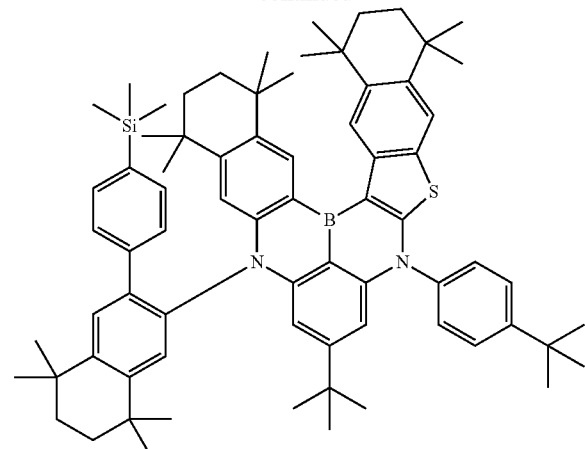
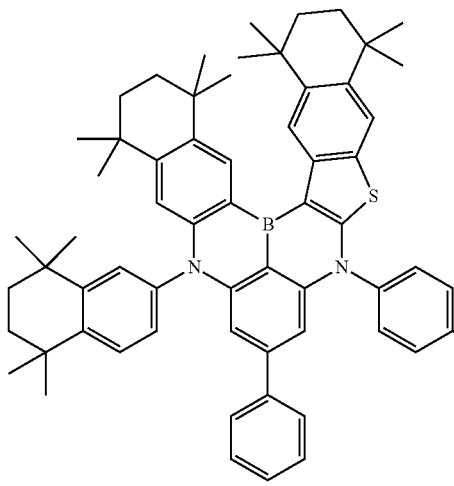
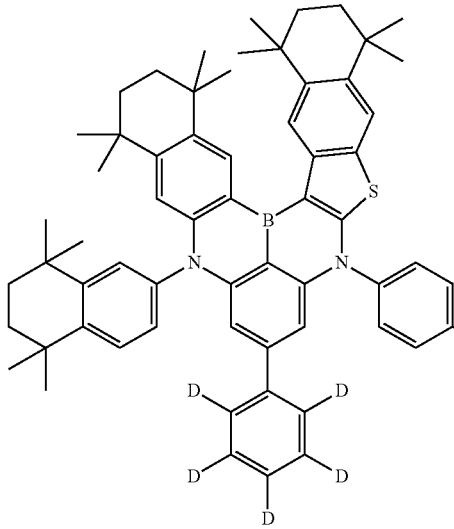

1443
-continued
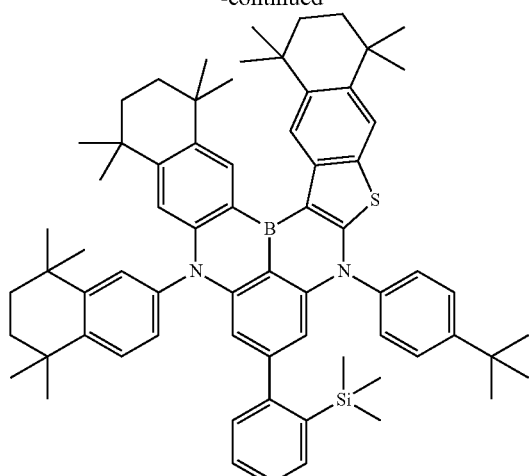
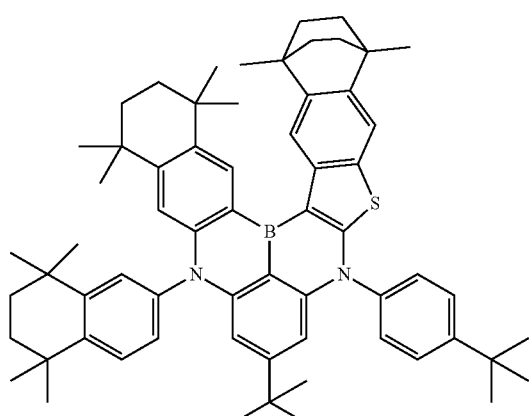
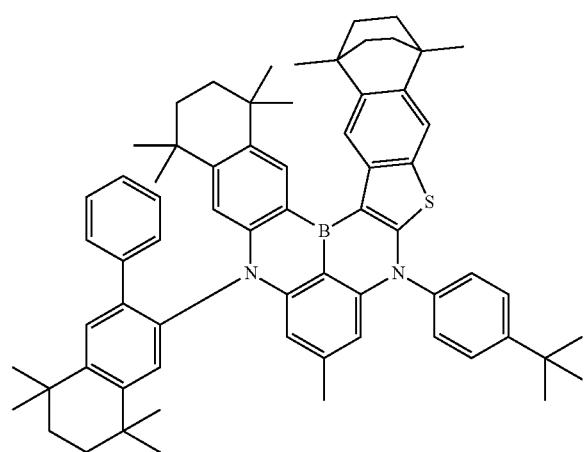
1444
-continued
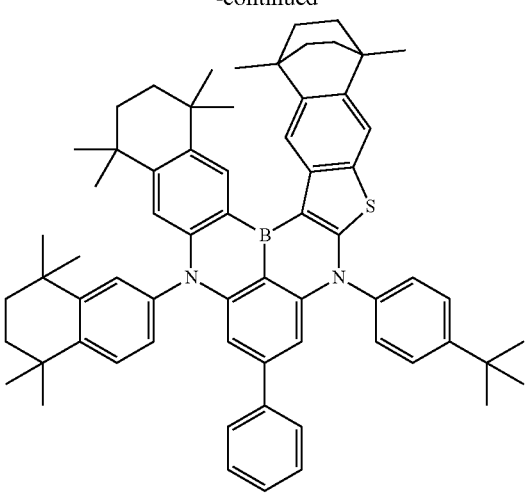
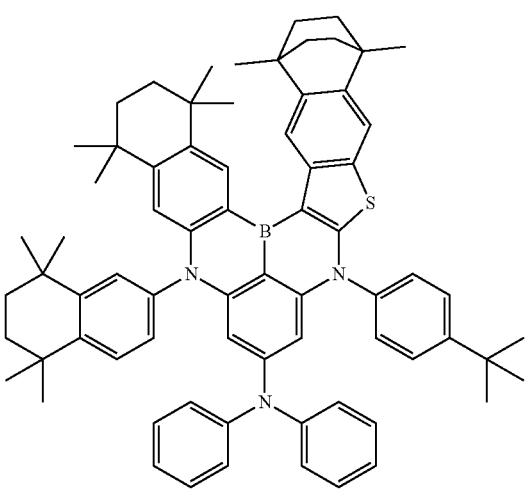
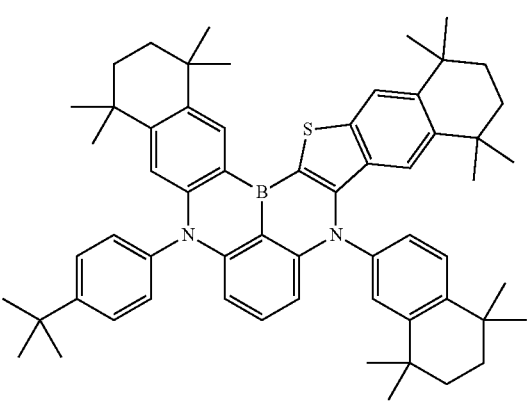

1445
-continued
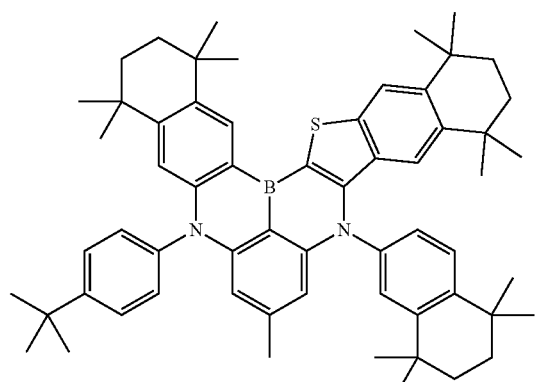
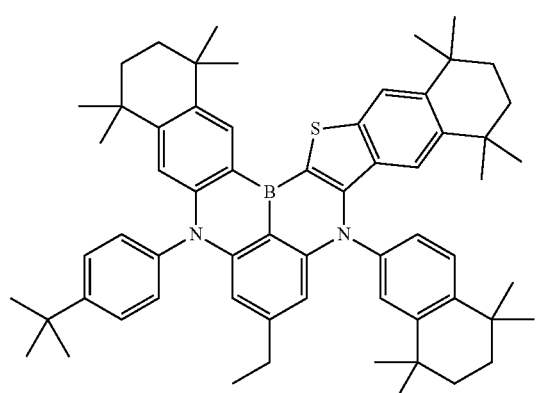
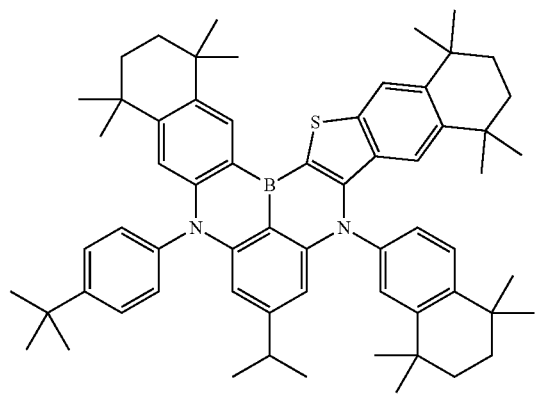
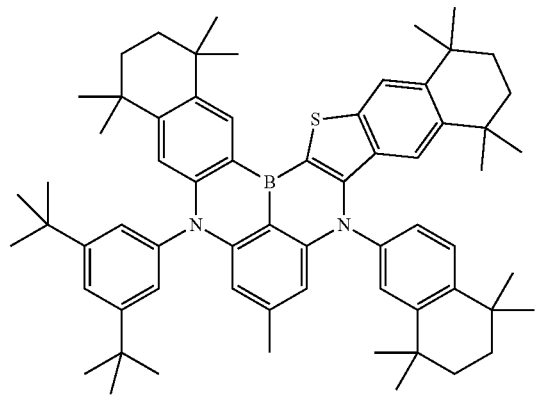
1446
-continued
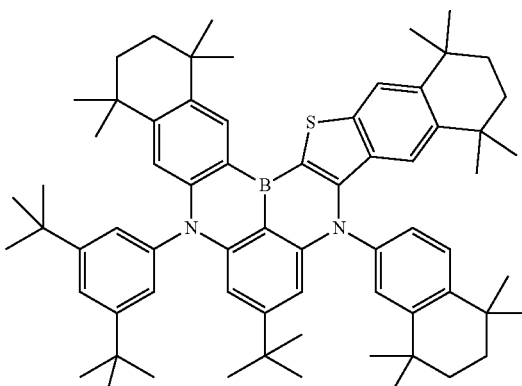
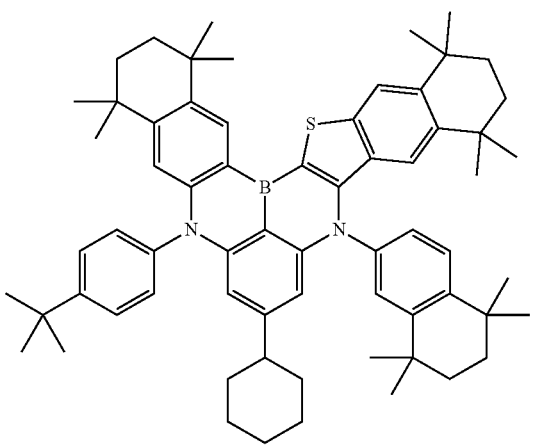
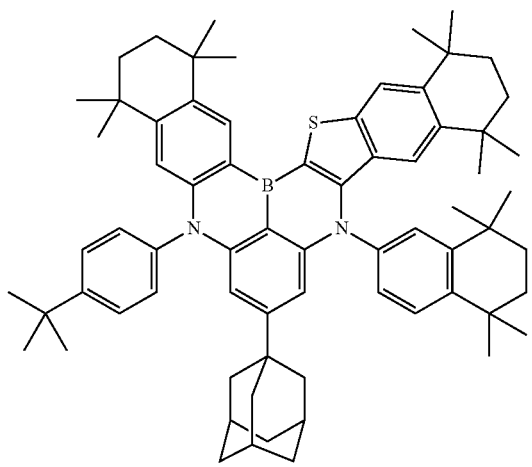
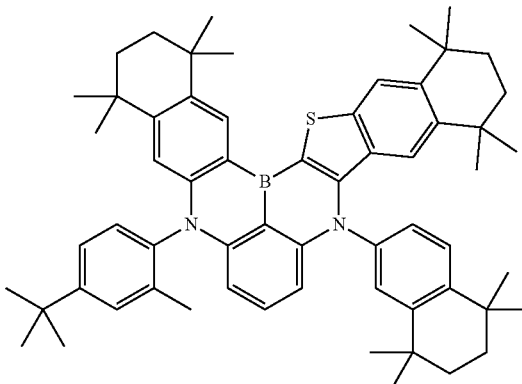

1447
-continued
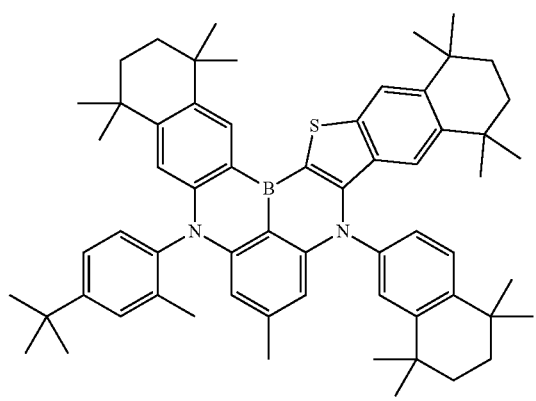
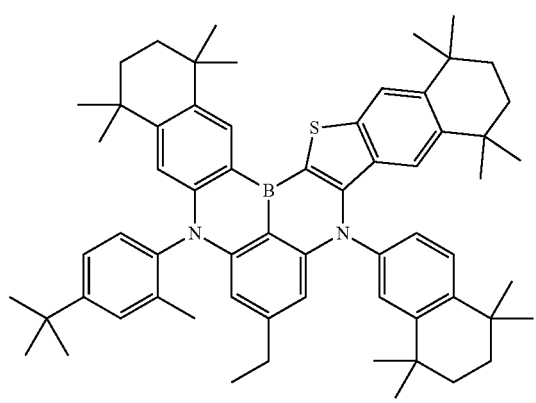
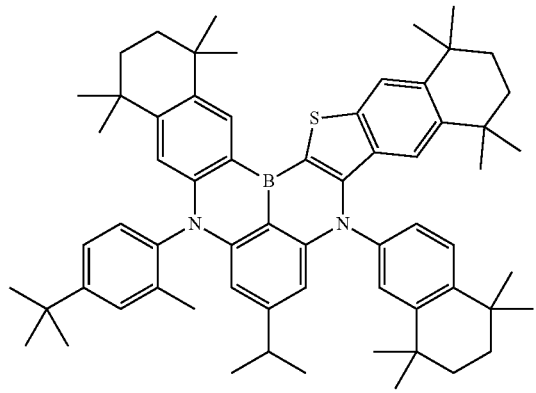
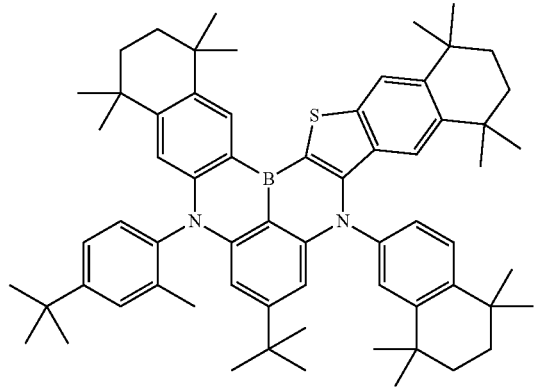
1448
-continued
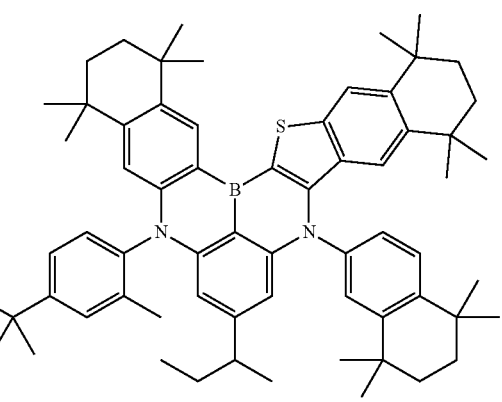
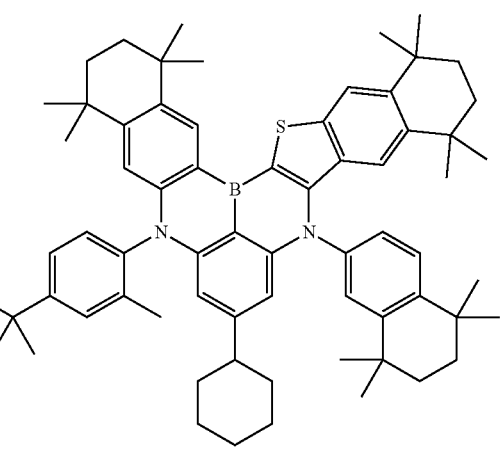
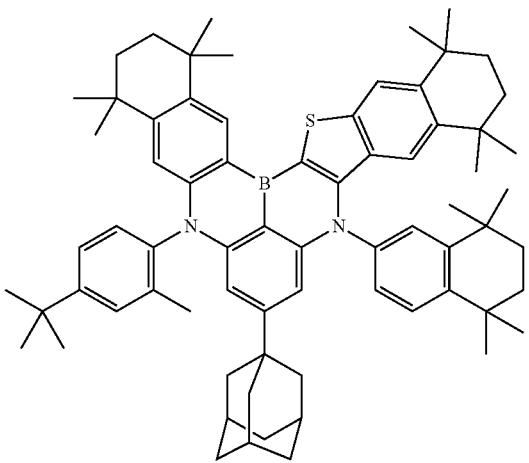
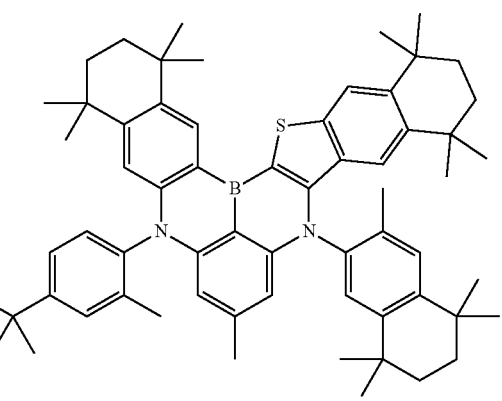

1449
-continued
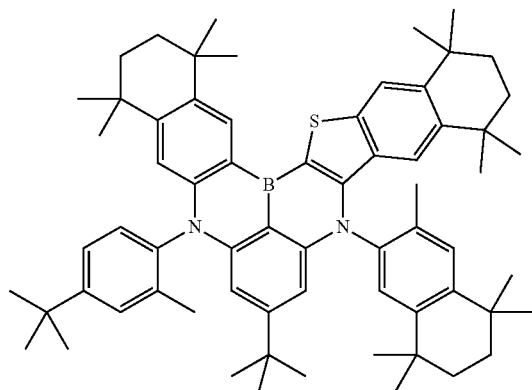
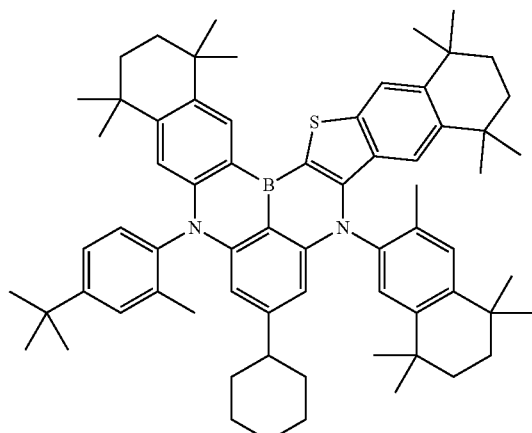
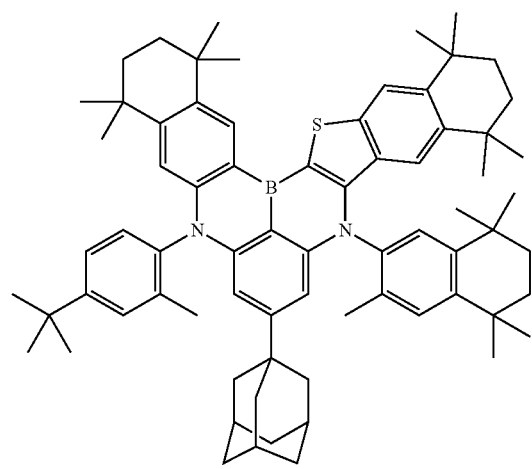
1450
-continued
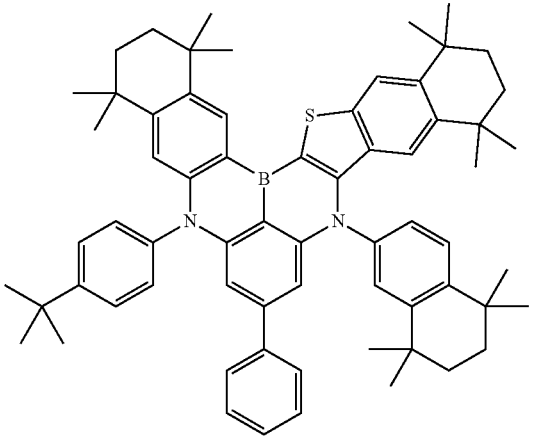
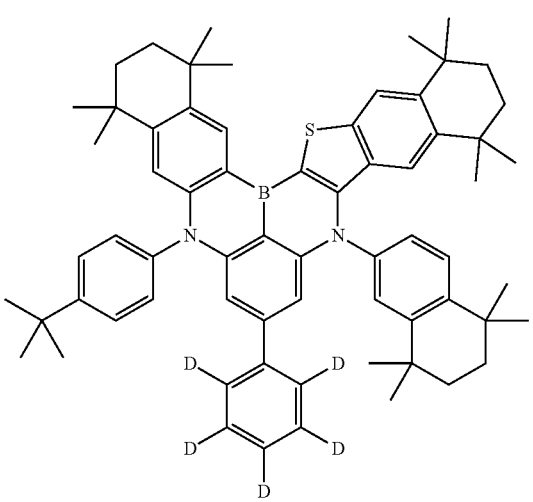
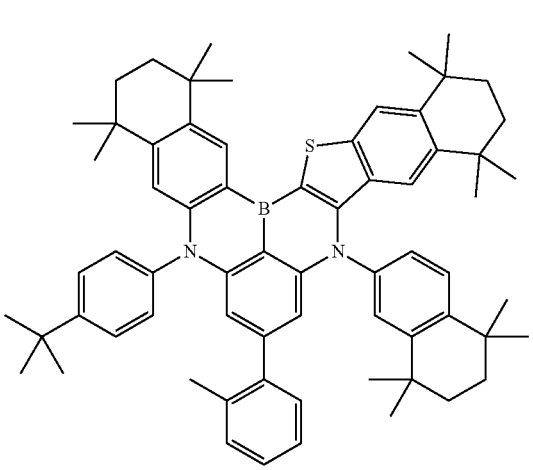

1451
-continued
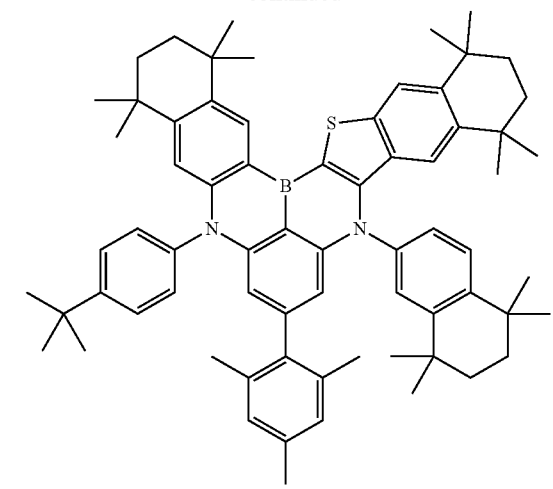
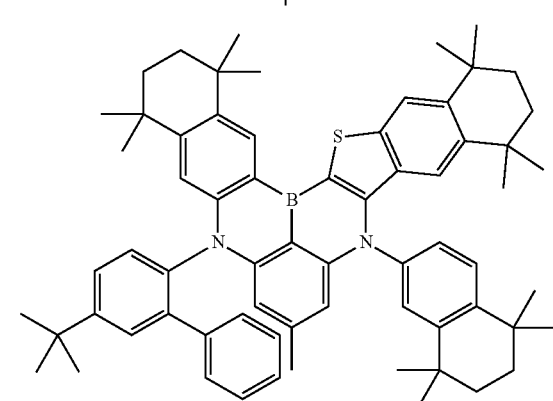
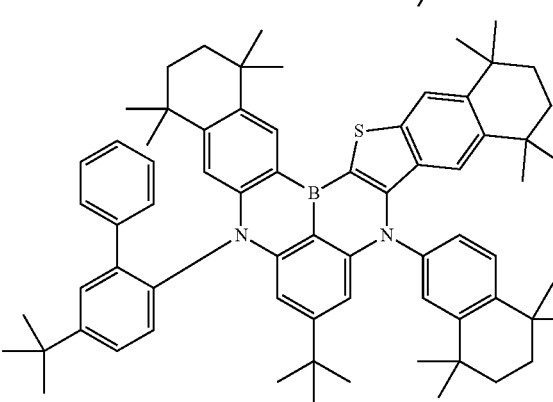
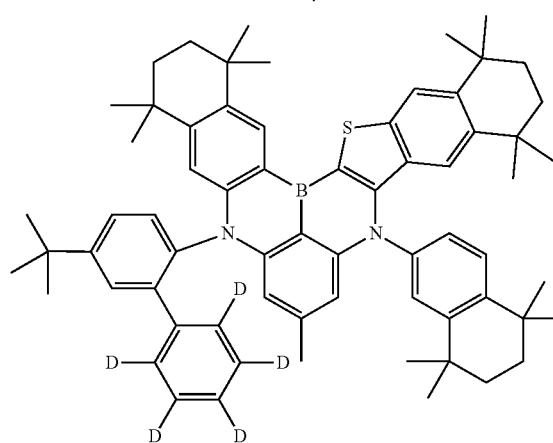
1452
-continued
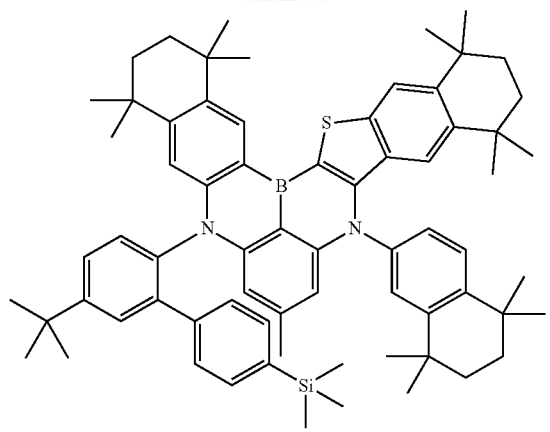
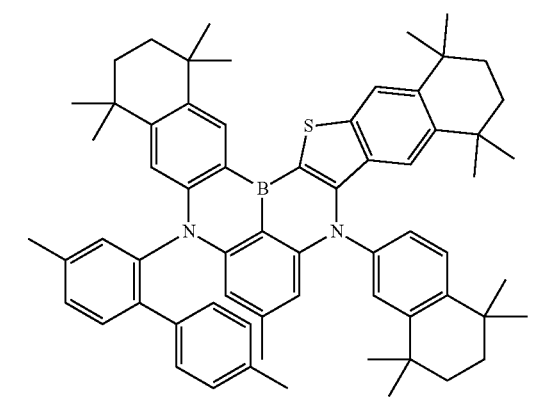
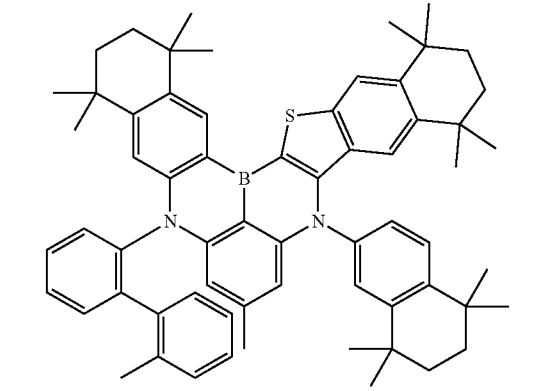
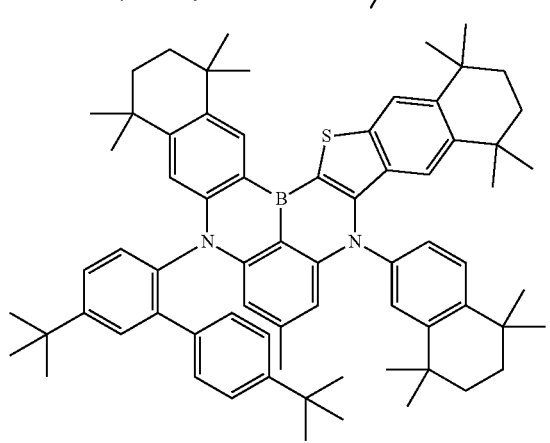

1453
-continued
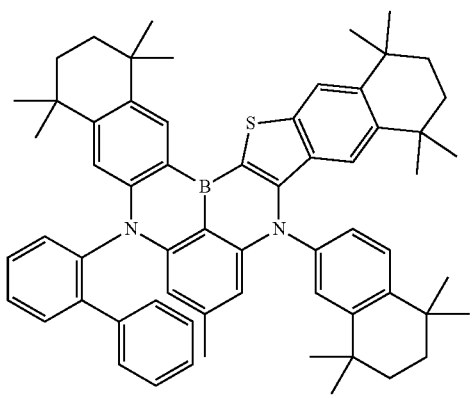
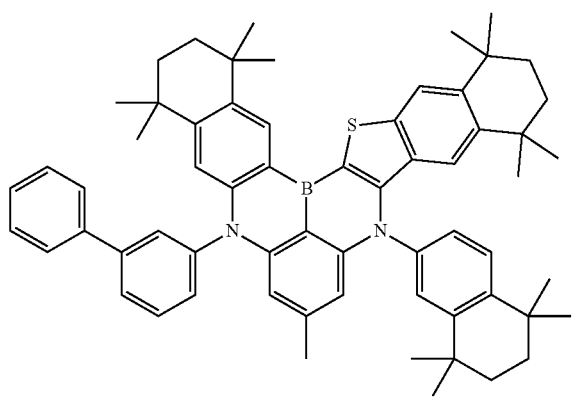
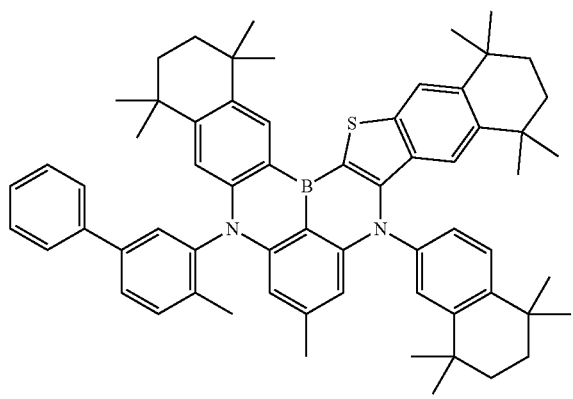
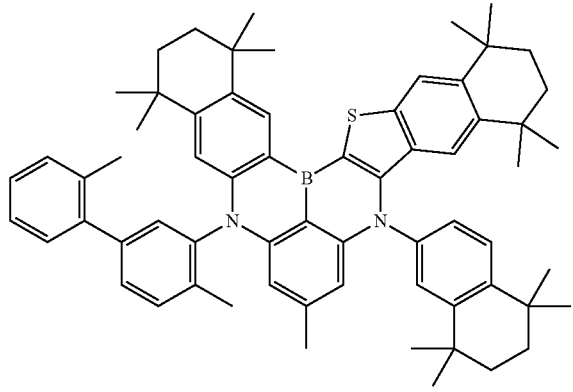
1454
-continued
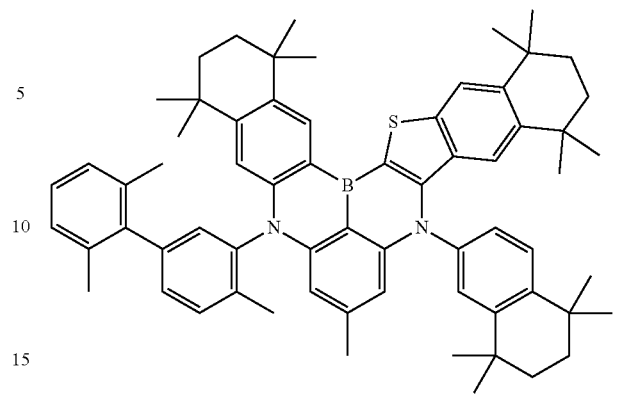
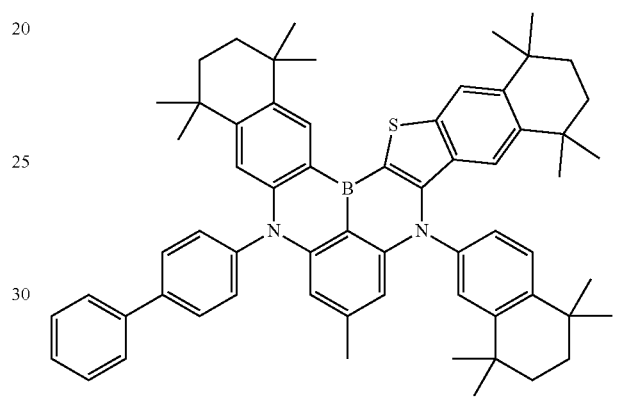
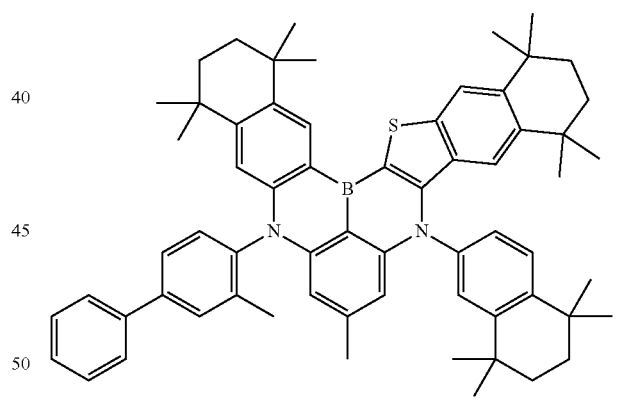
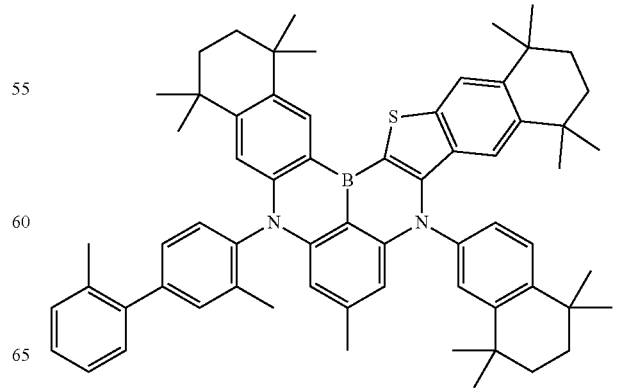

| 1455 -continued | 1456 -continued |
|---|---|
| 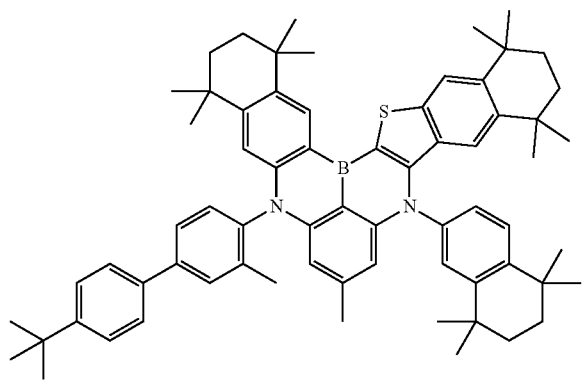 | 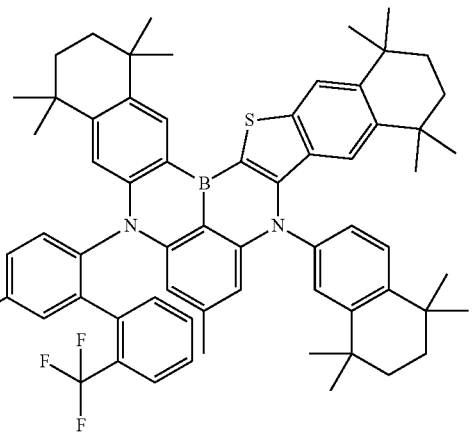 |
| 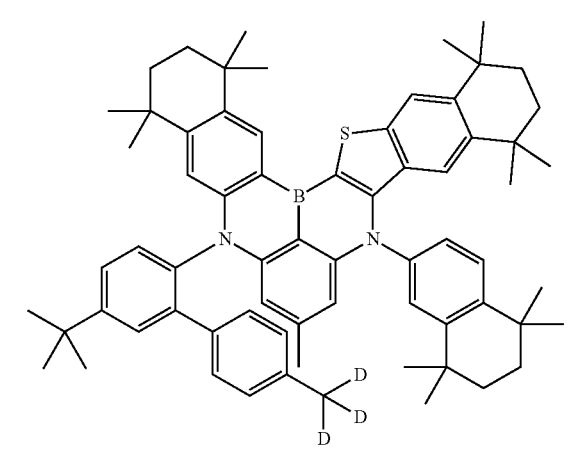 |  |
| 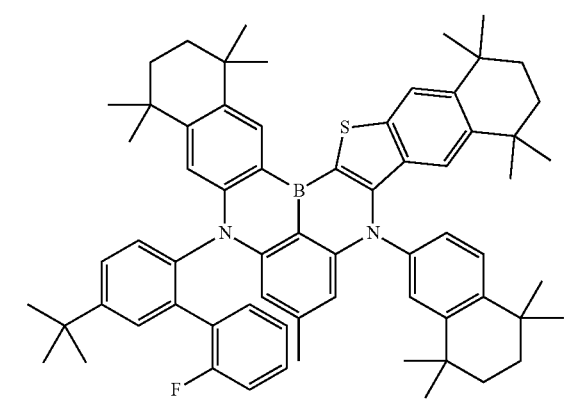 | 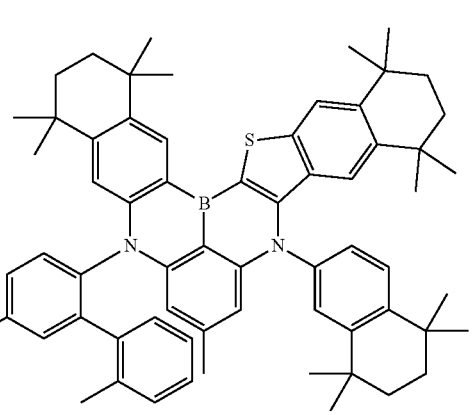 |
| 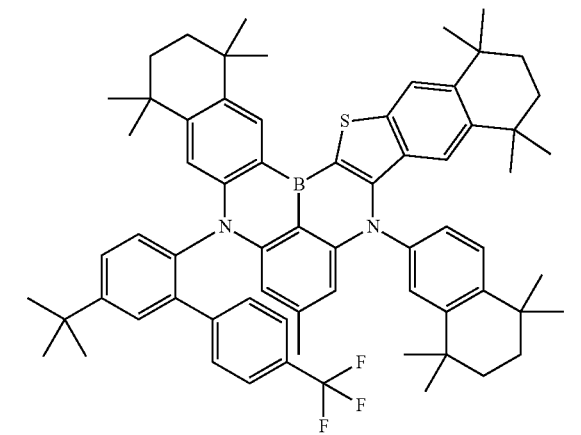 | 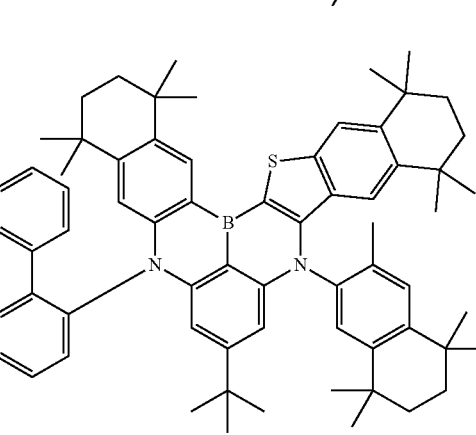 |

1457
-continued
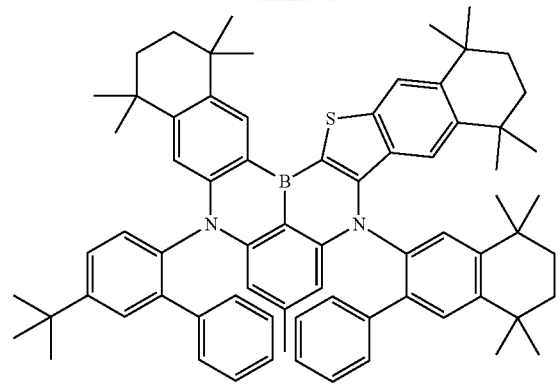
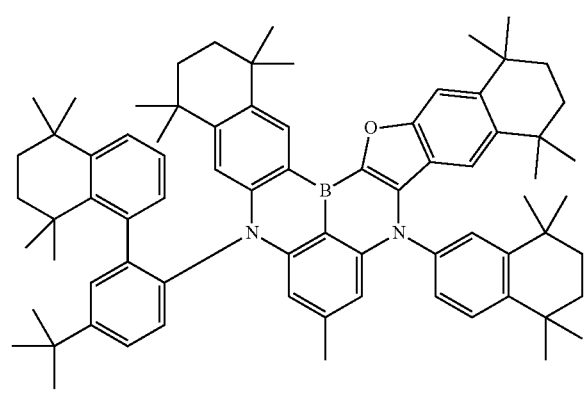
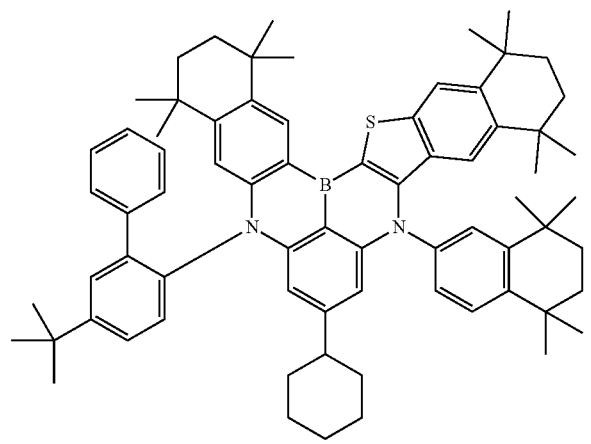
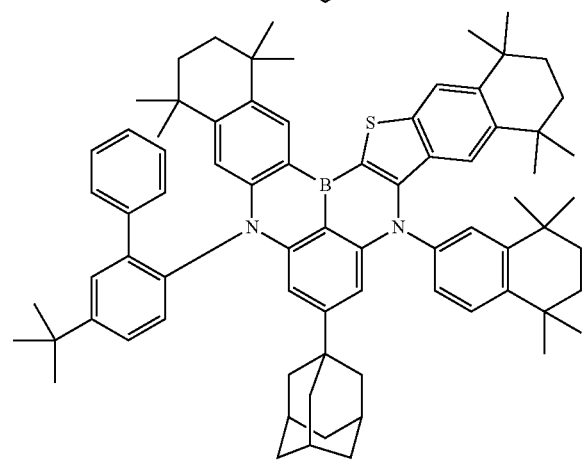
1458
-continued
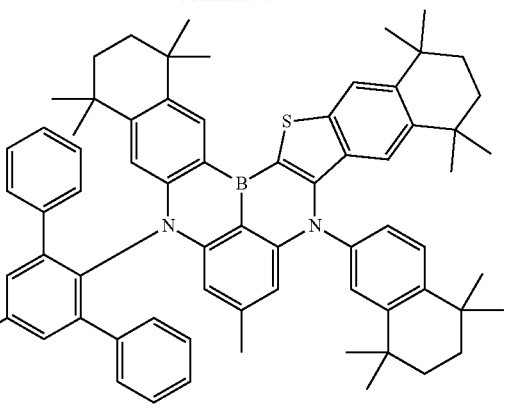
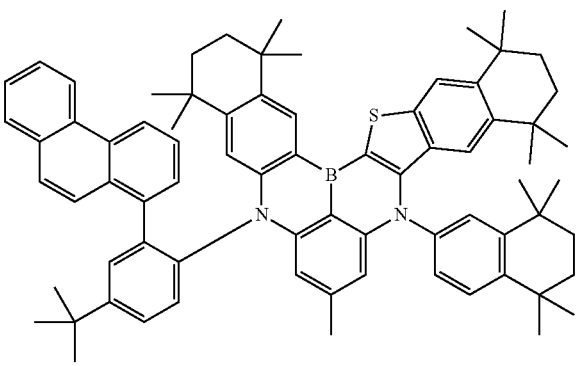
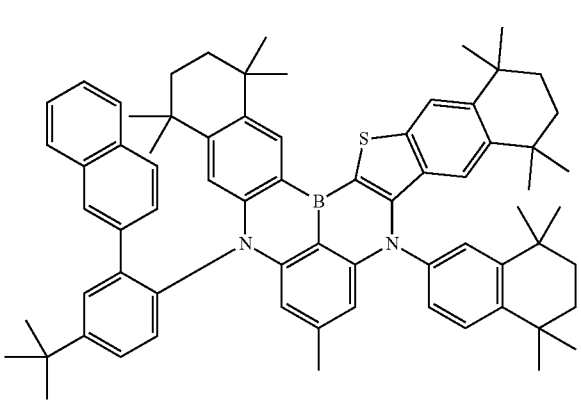
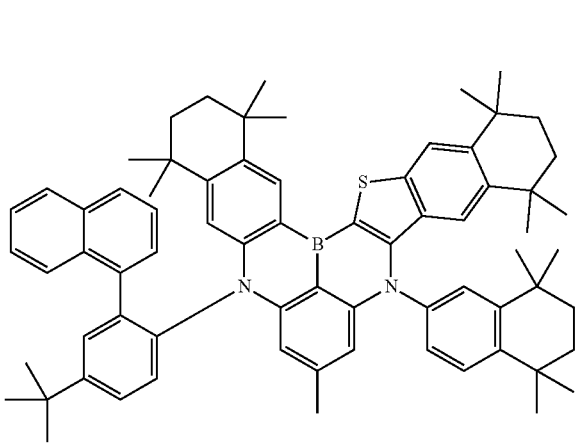

| 1459 -continued | 1460 -continued |
|---|---|
| 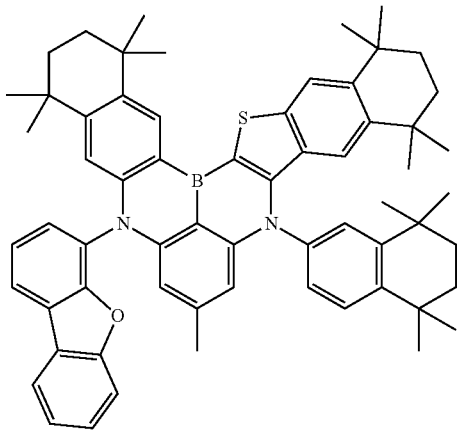 | 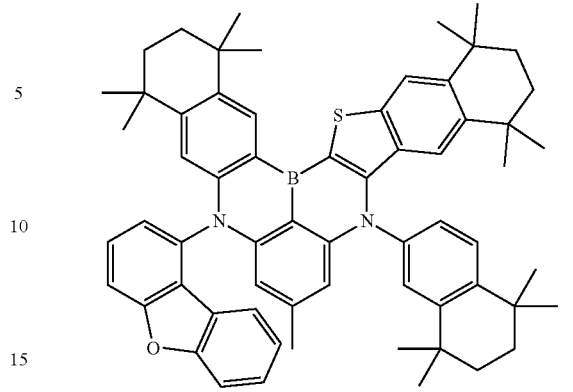 |
| 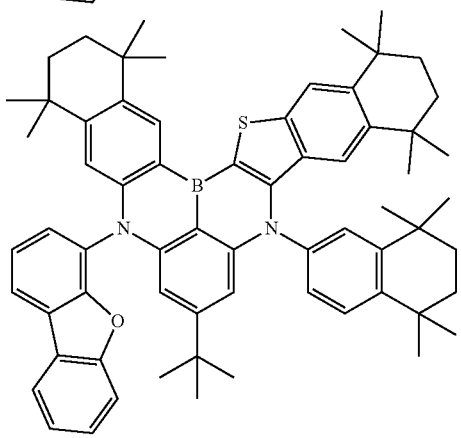 | 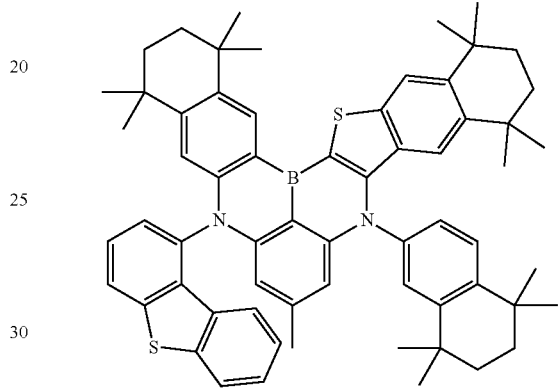 |
| 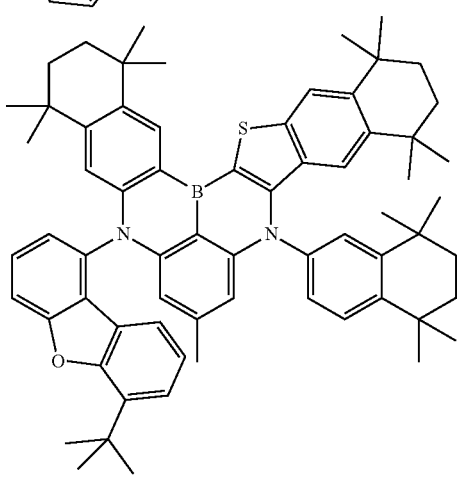 | 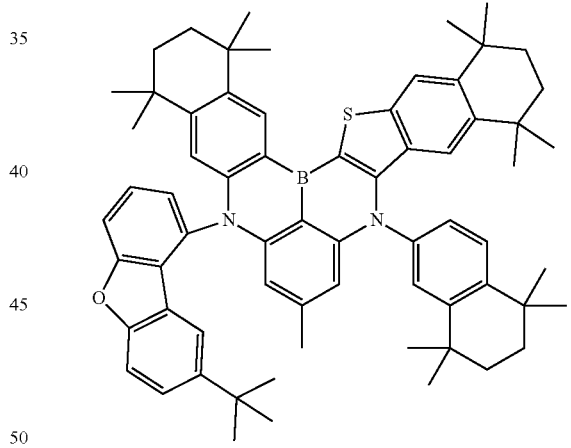 |
| 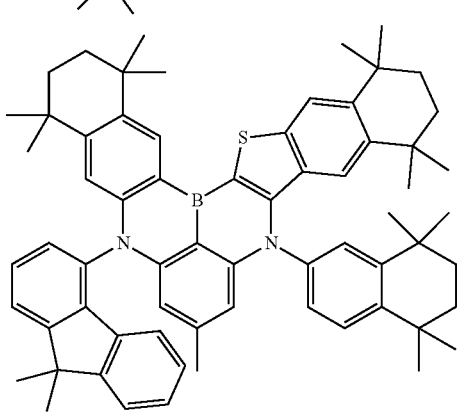 | 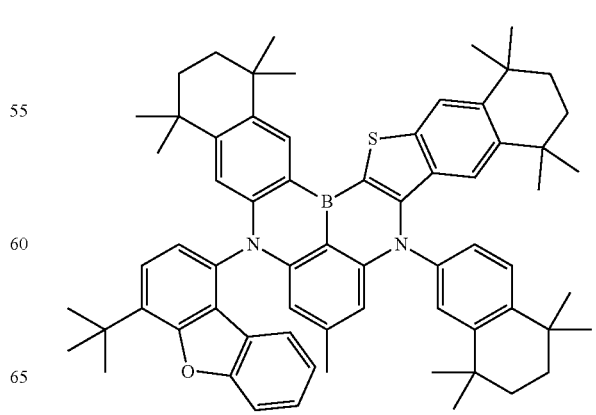 |

1461
-continued
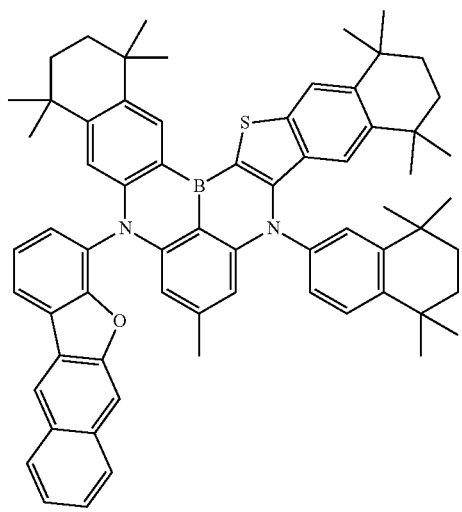
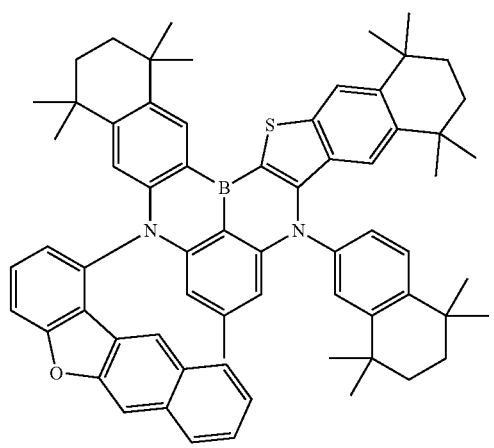
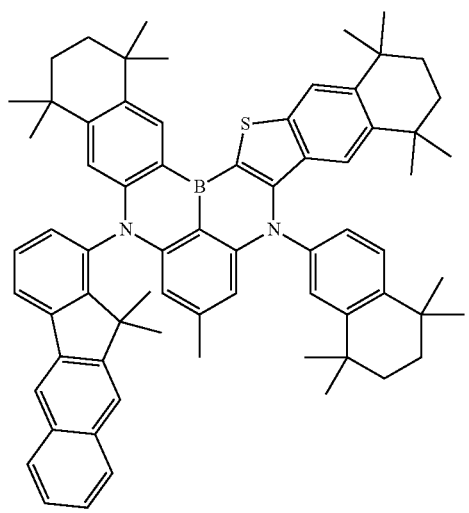
1462
-continued
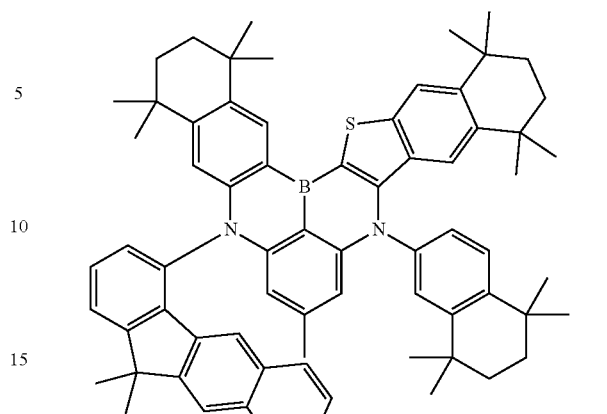
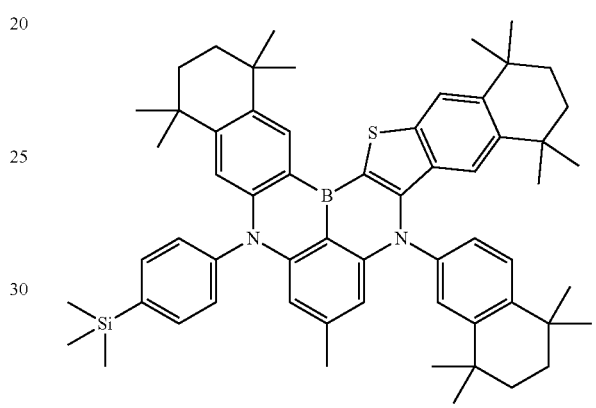
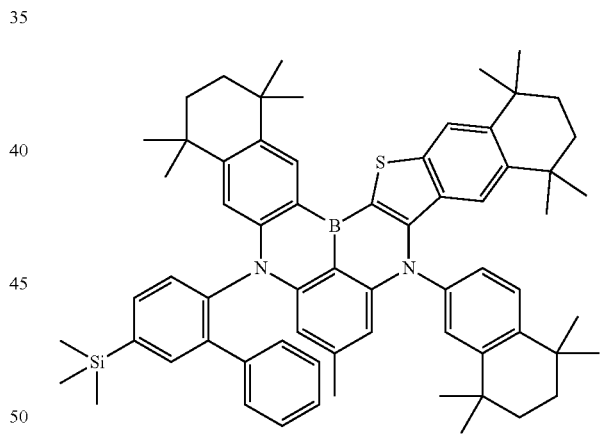
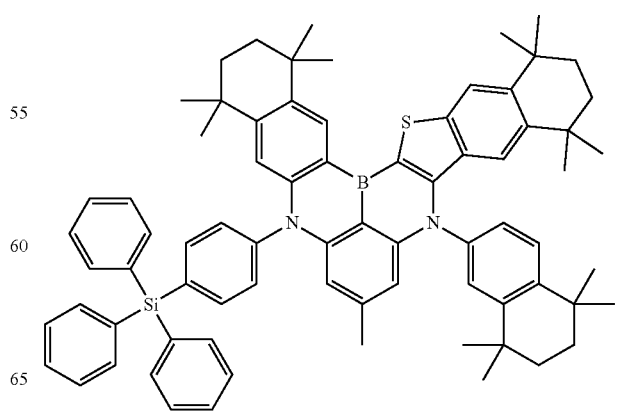

1463
-continued
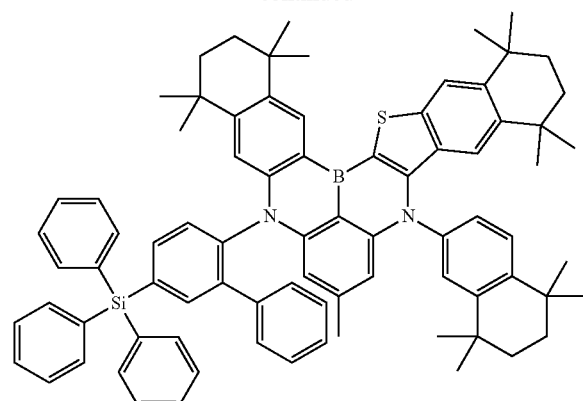
1464
-continued
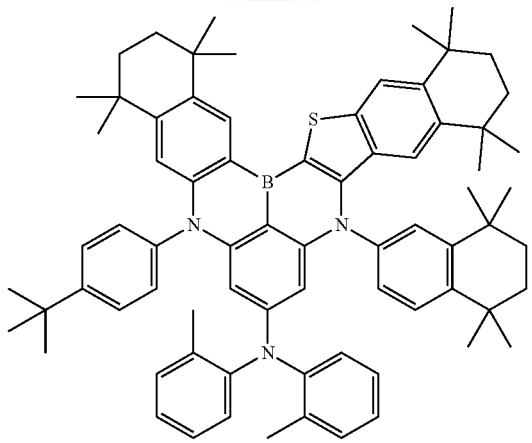
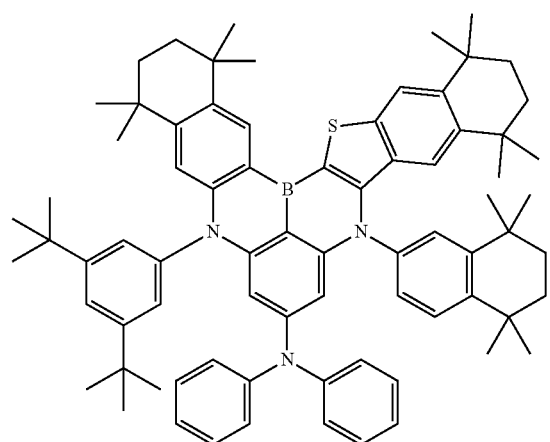
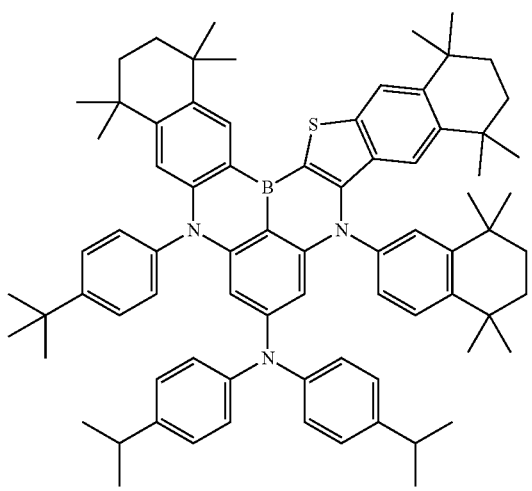
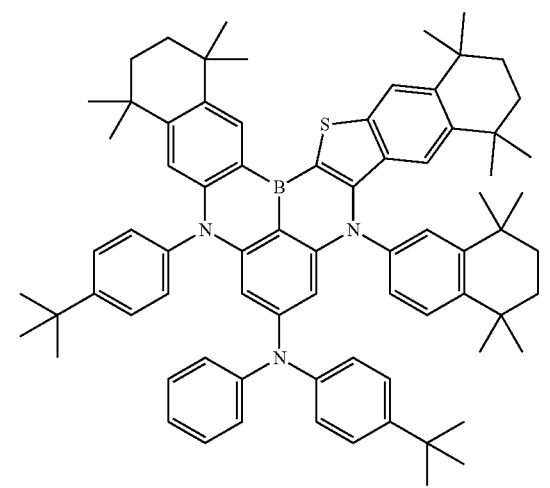
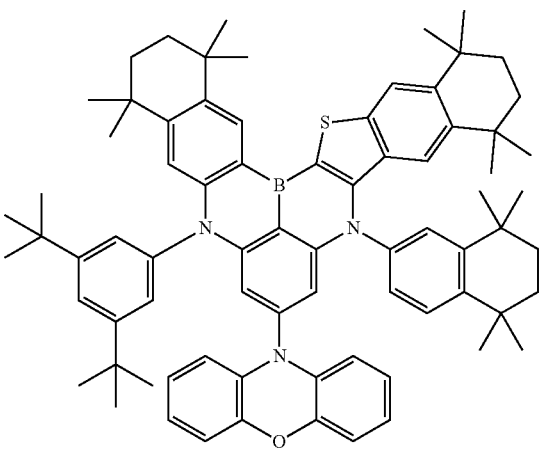

1465
-continued
1466
-continued
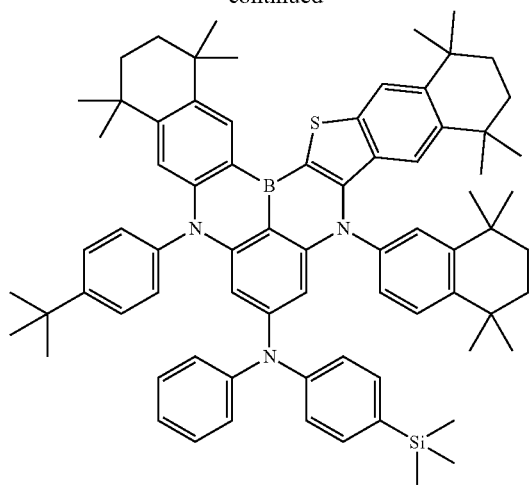
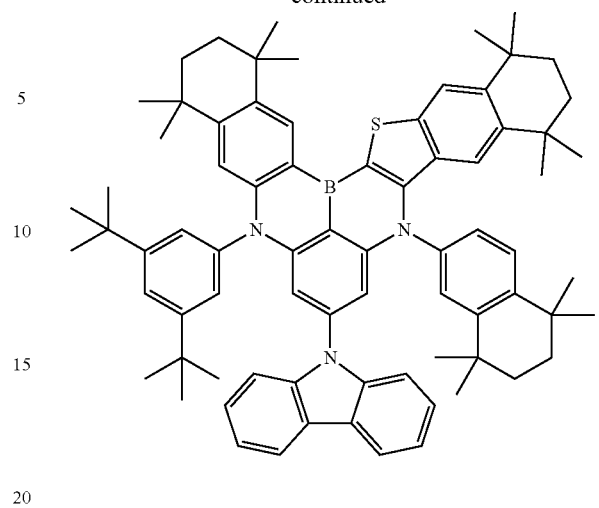
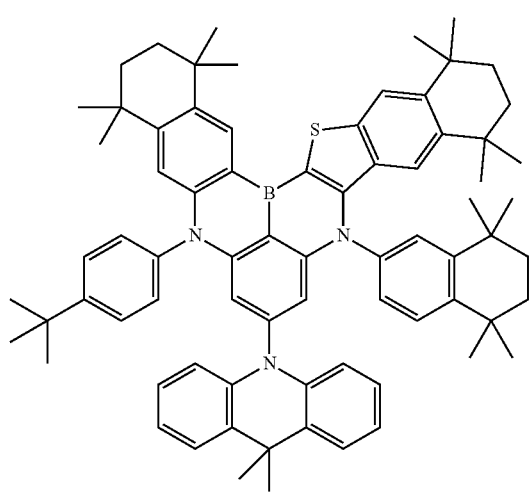
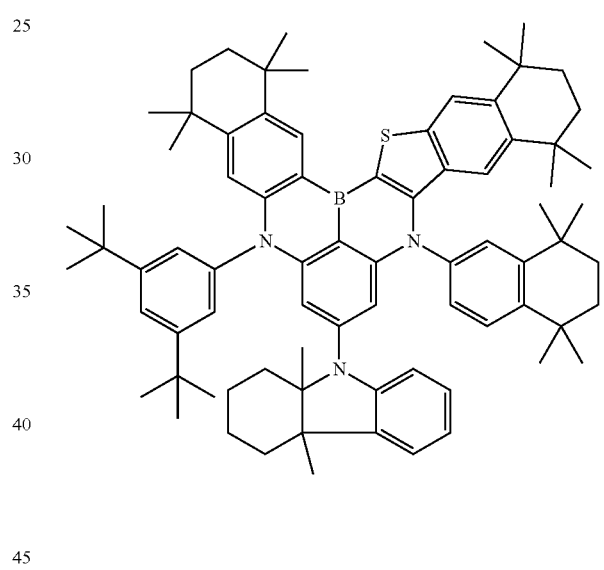
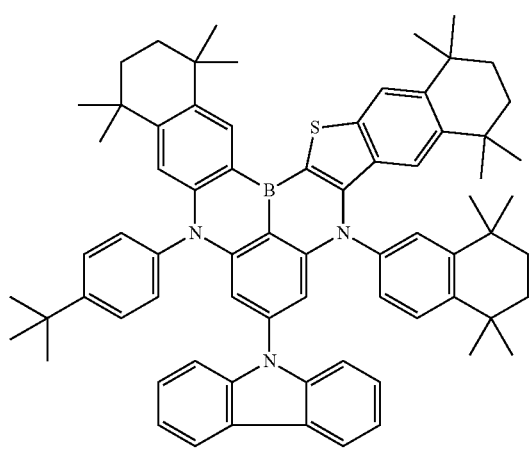
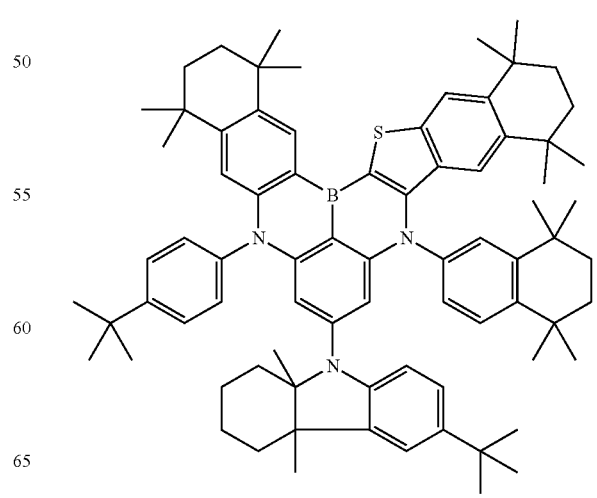

1467
-continued
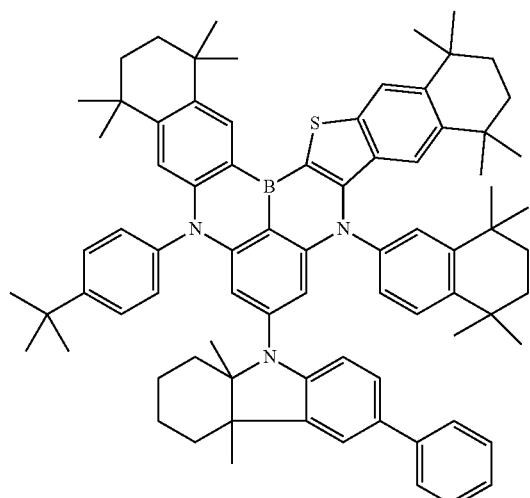
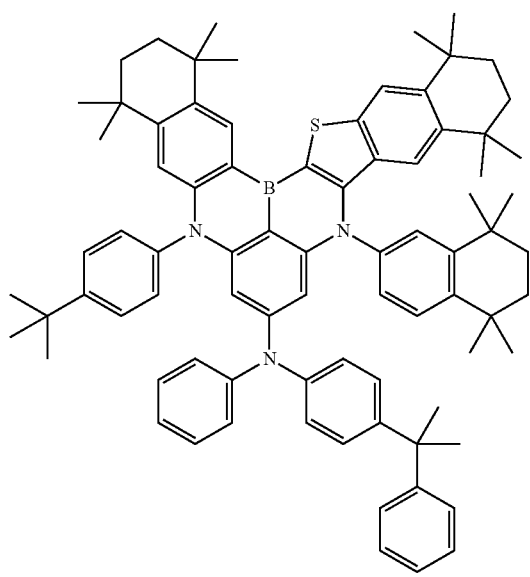
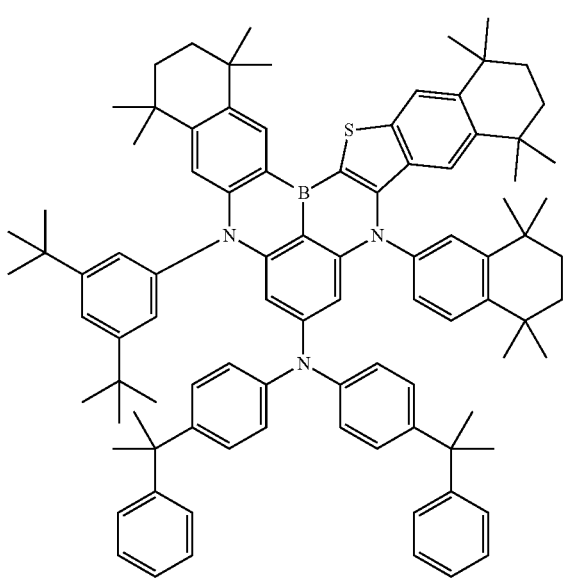
1468
-continued
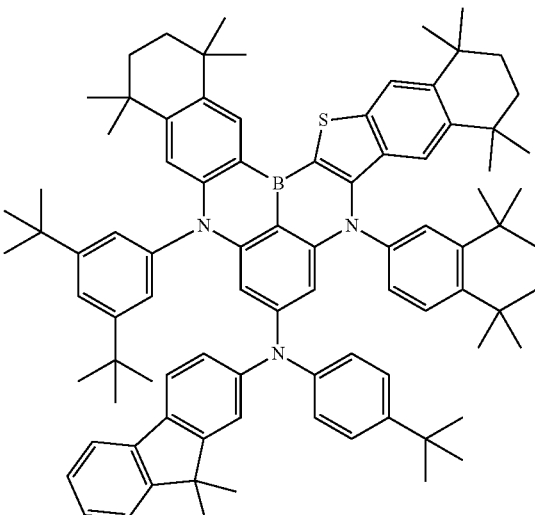
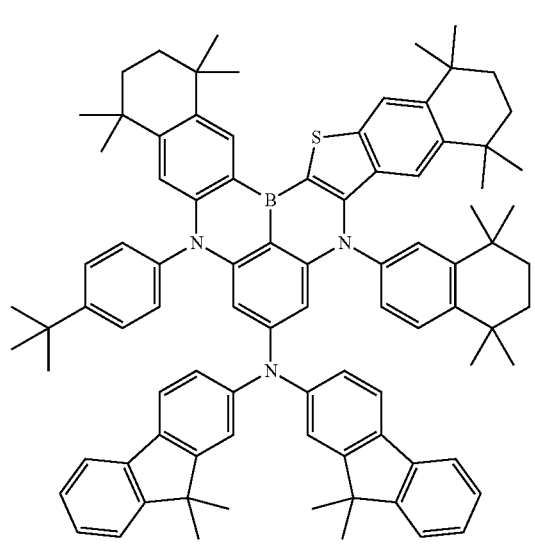
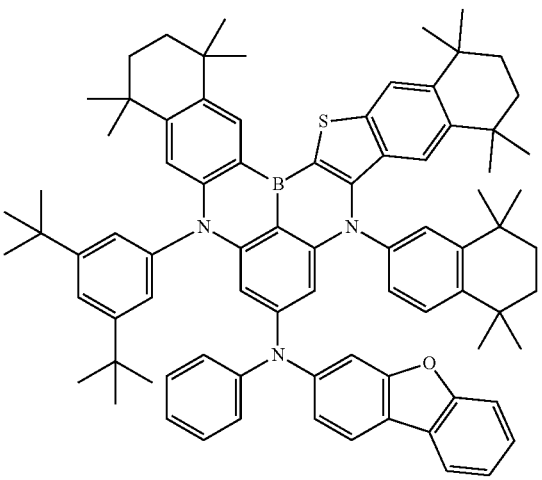

1469
-continued
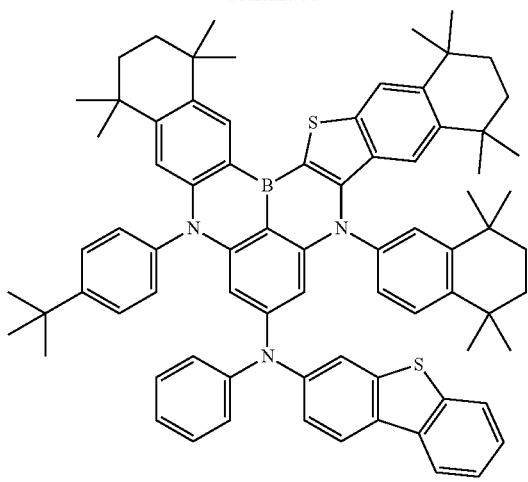
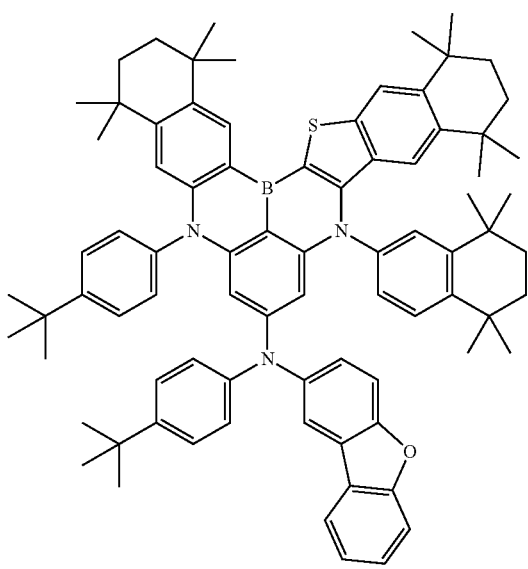
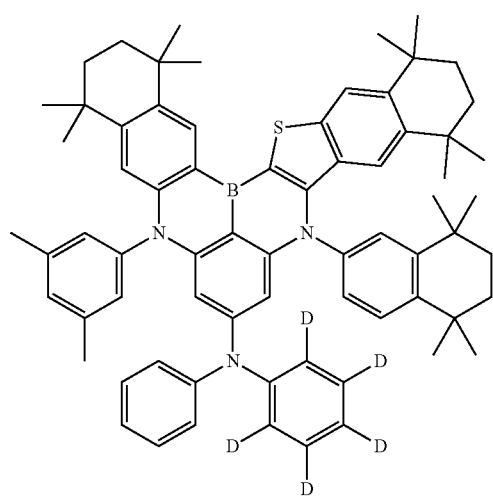
1470
-continued
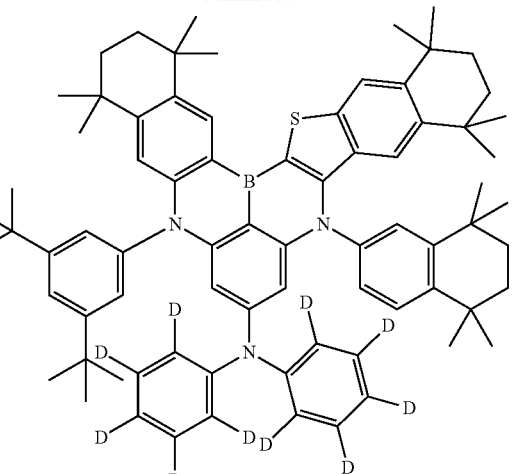
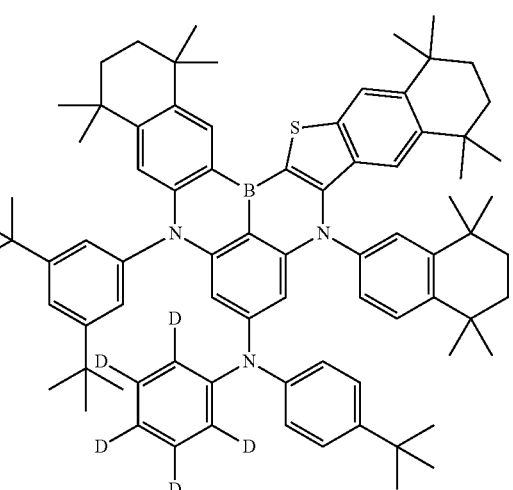
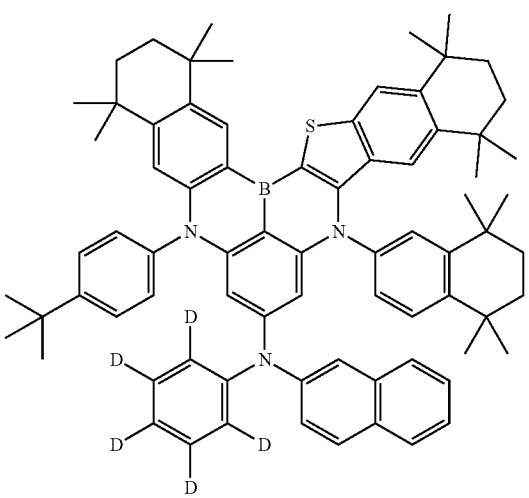

1471
-continued
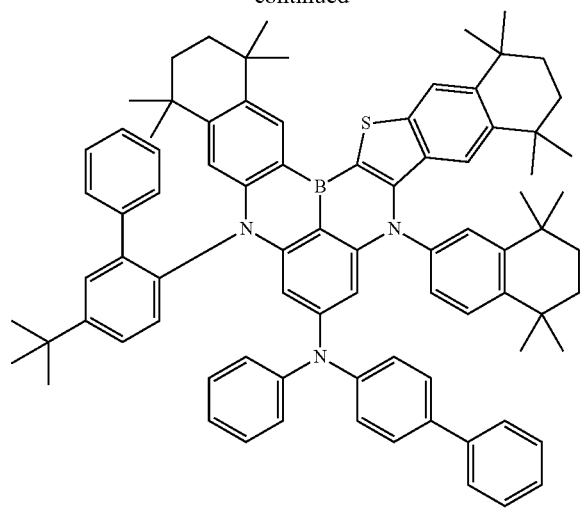
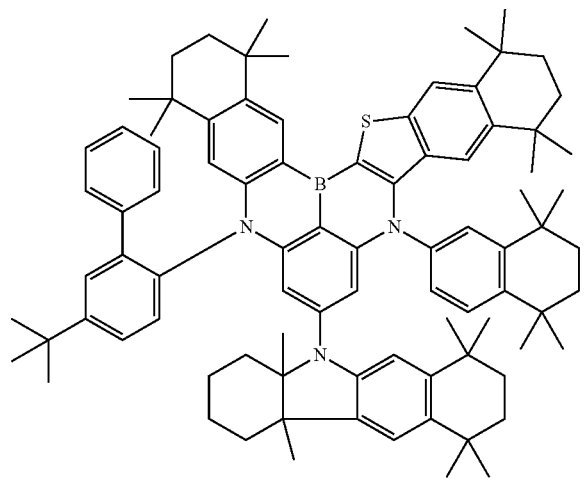
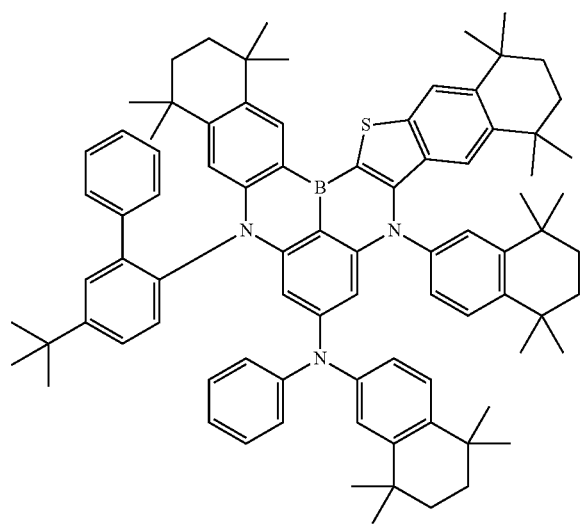
1472
-continued
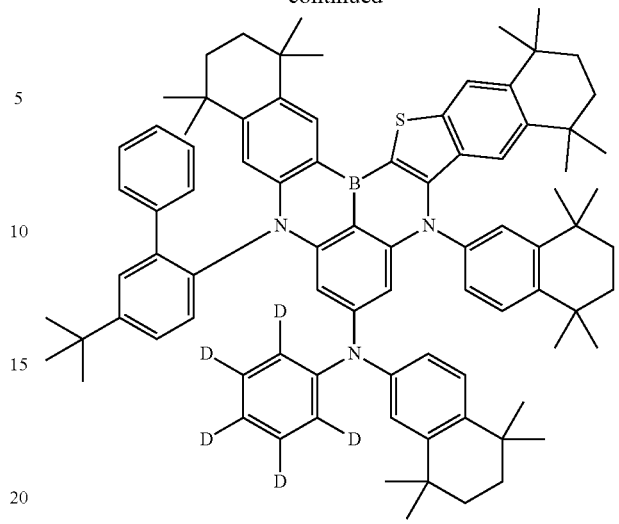
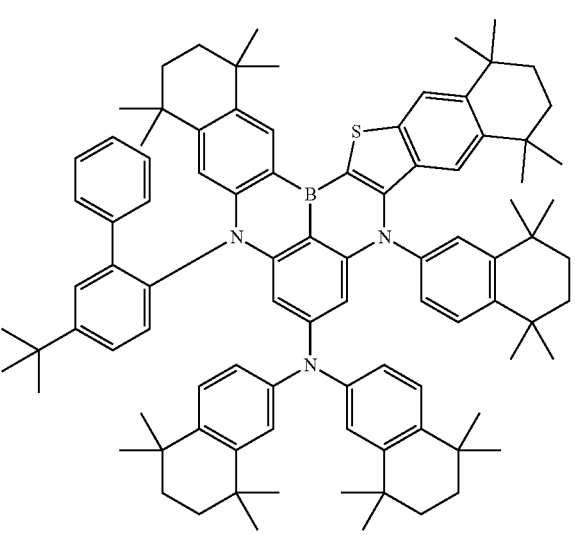
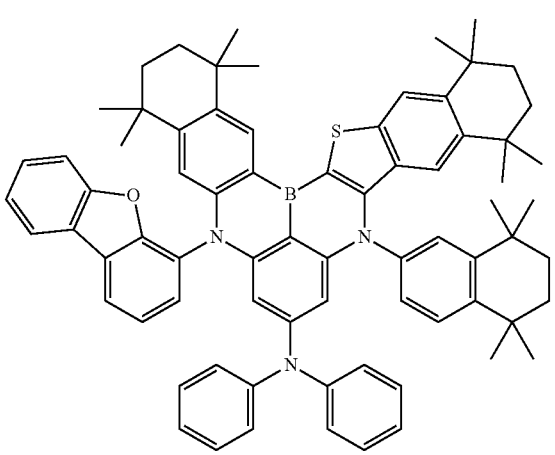

1473
-continued
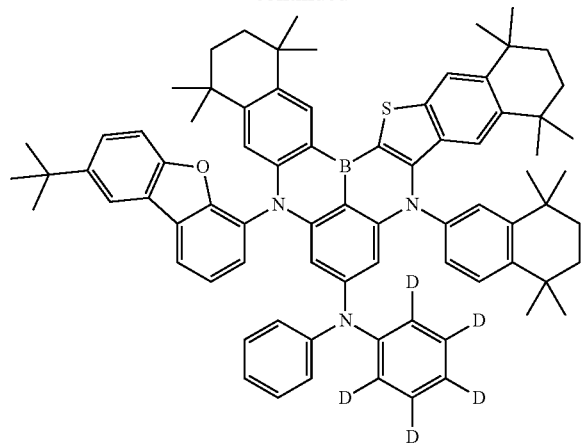
1474
-continued
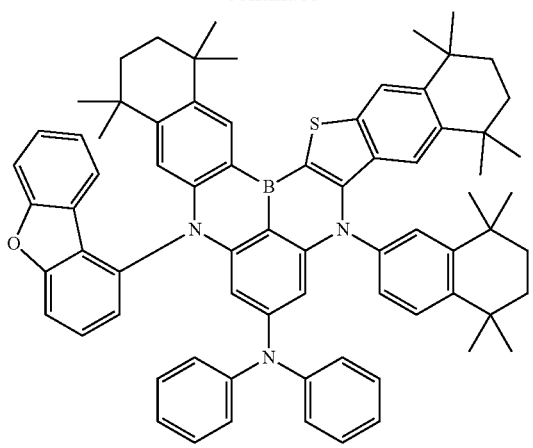
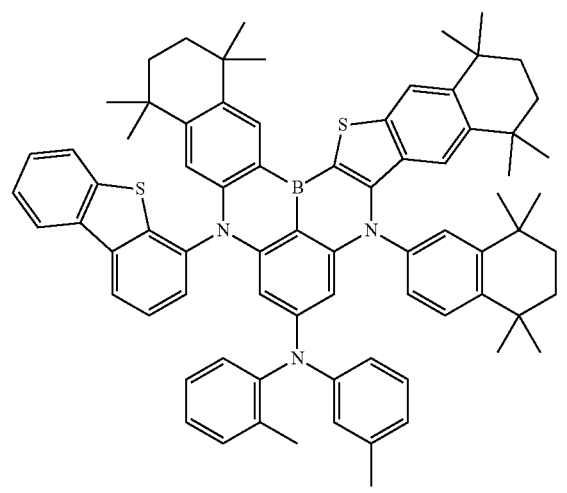
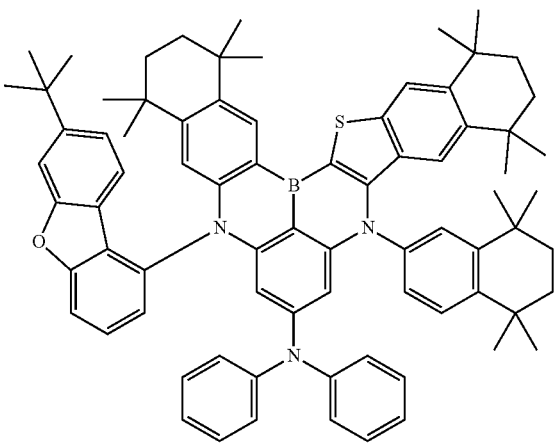
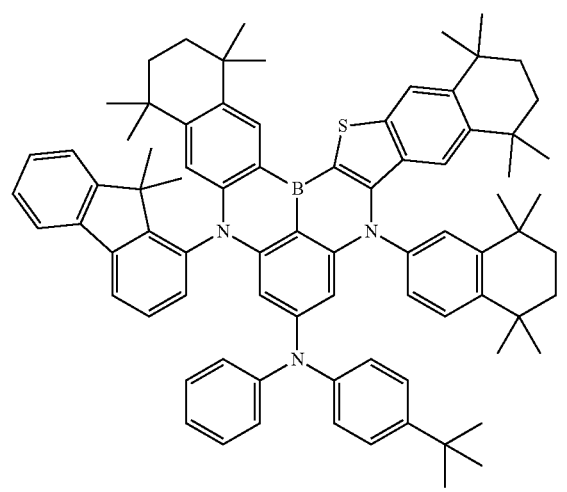
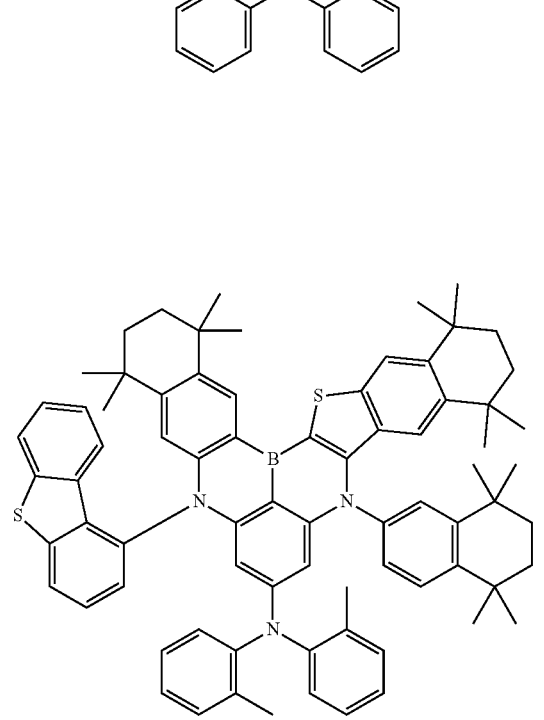

1475
-continued
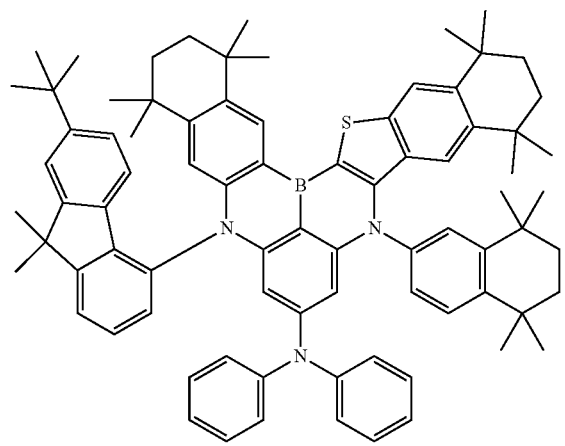
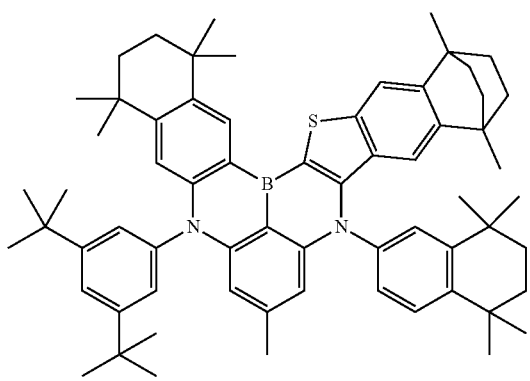
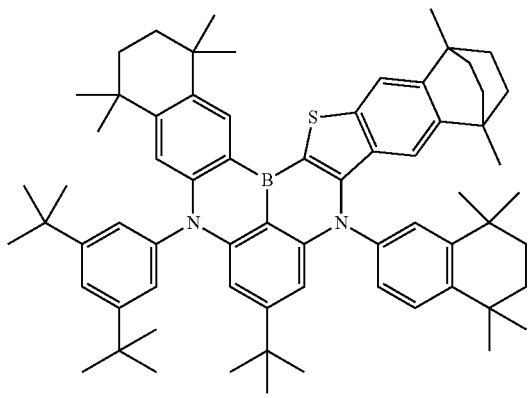
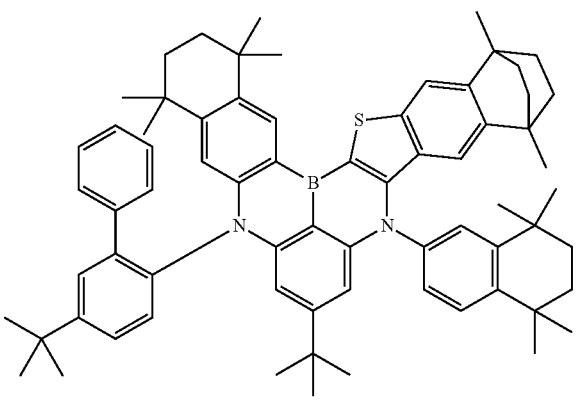
1476
-continued
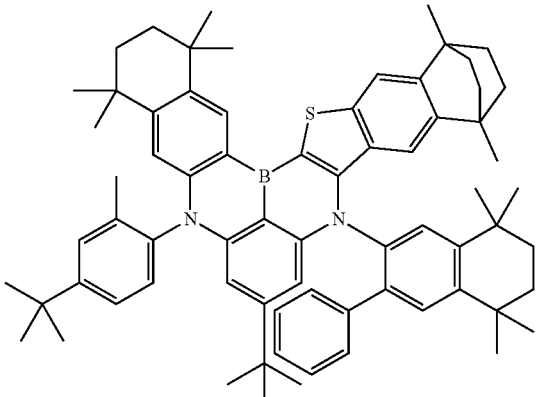
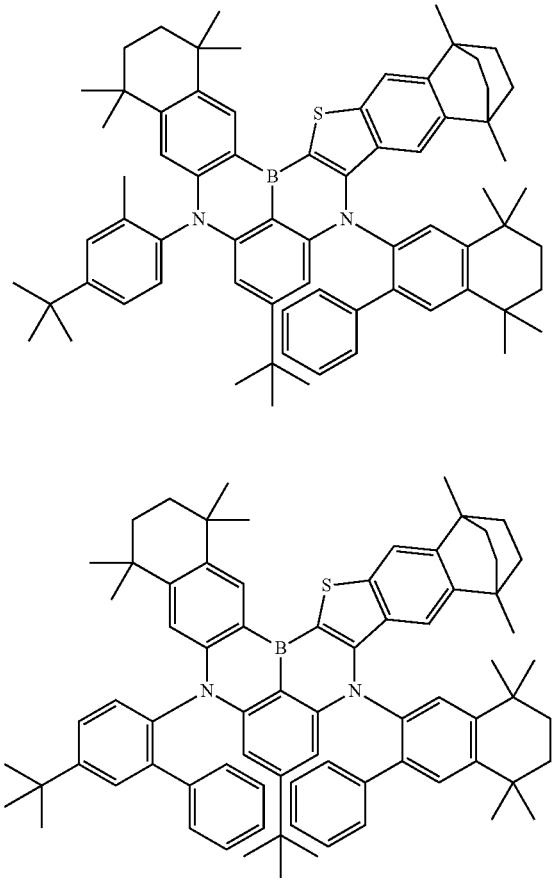
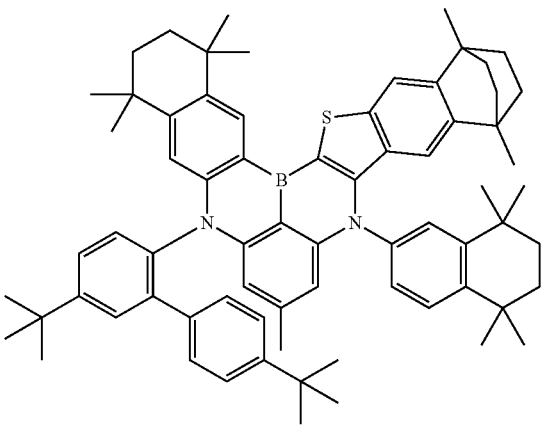
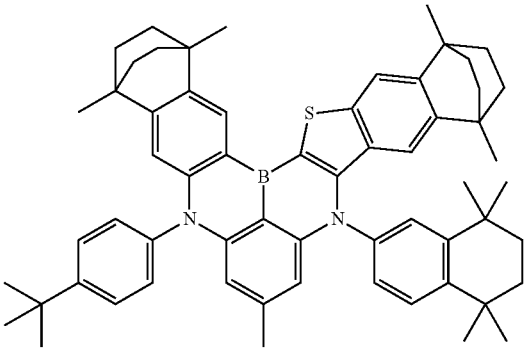

1477
-continued
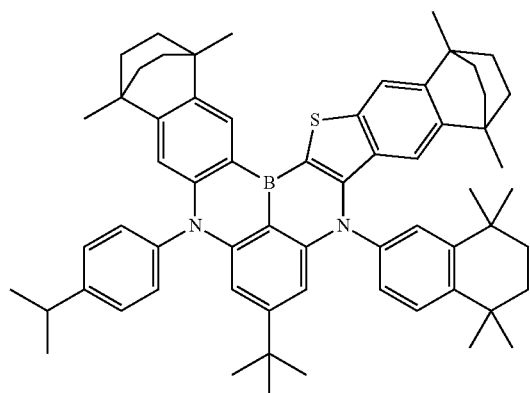
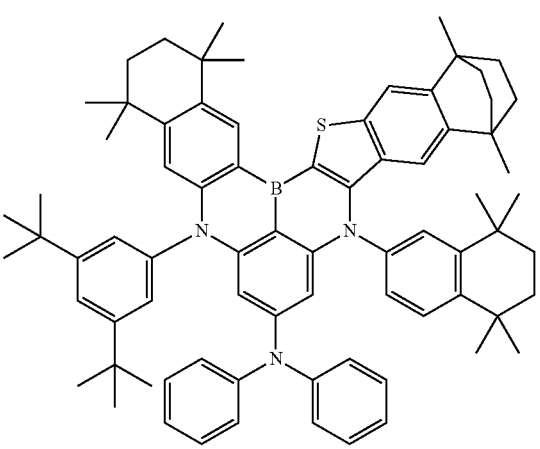
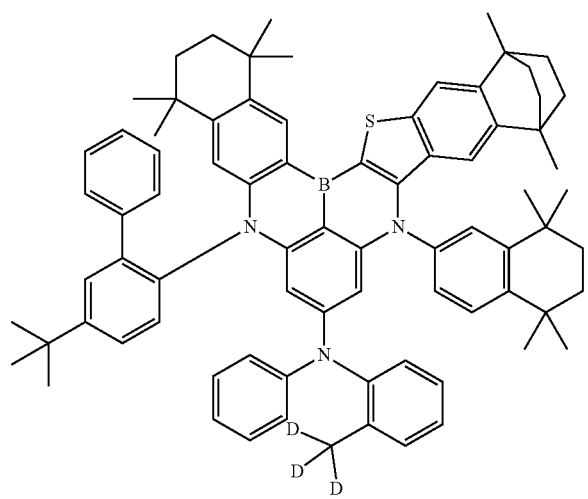
1478
-continued
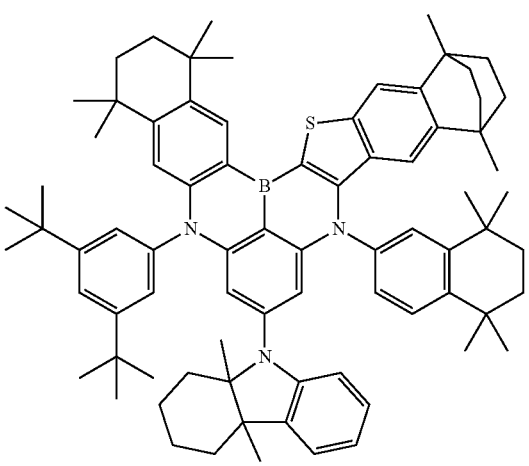
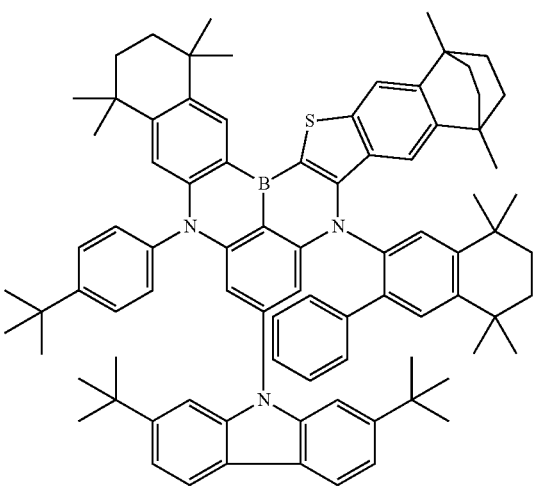
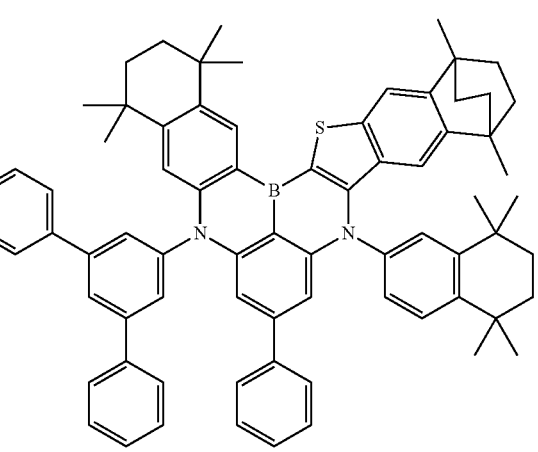

1479
-continued
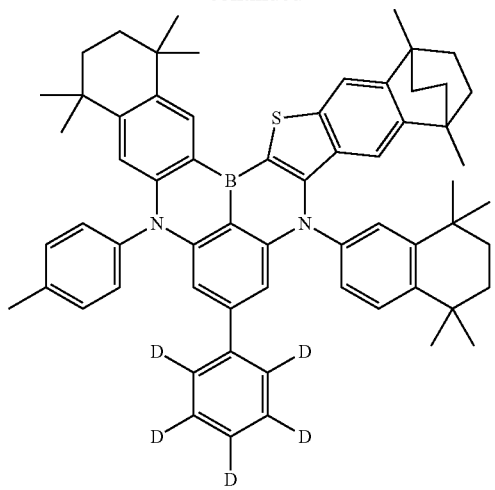
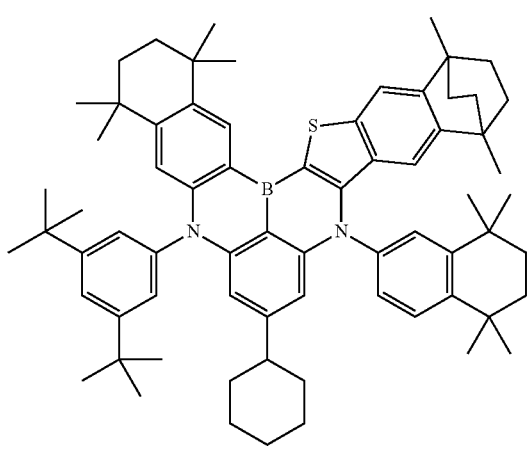
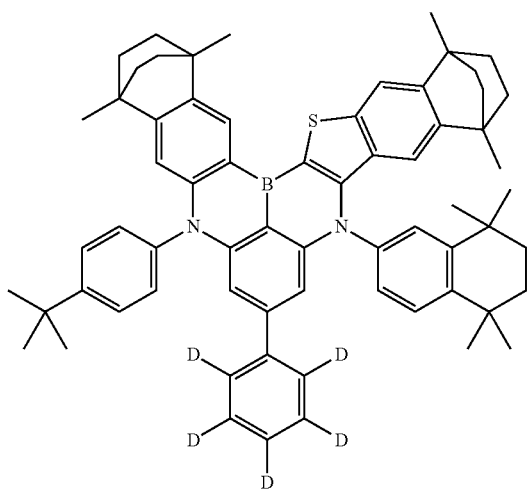
1480
-continued
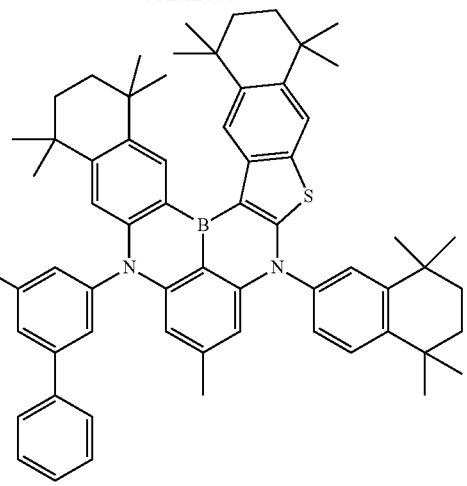
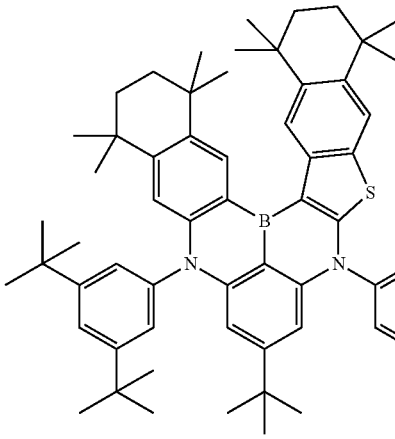
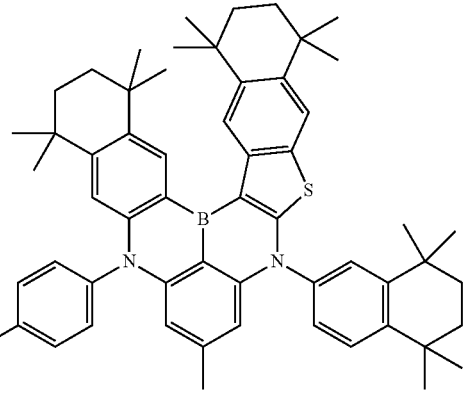

1481
-continued
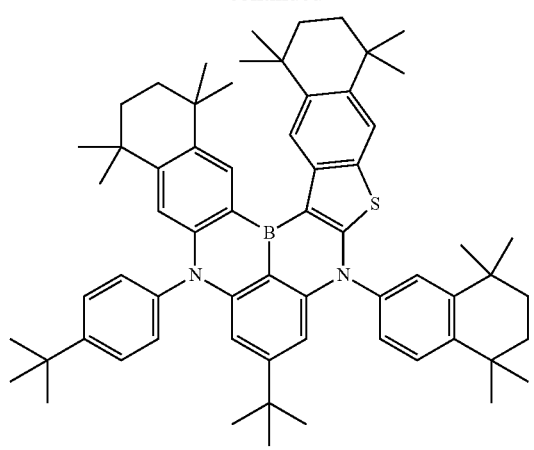
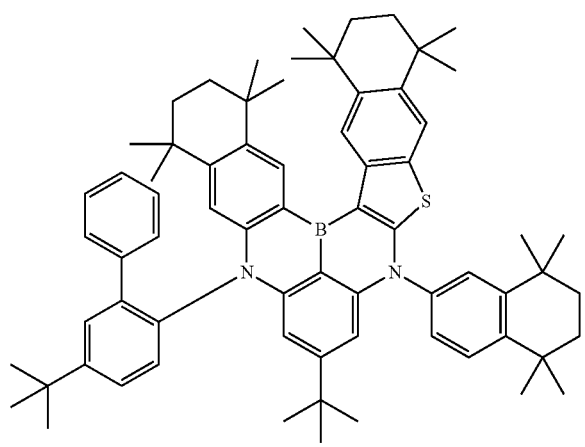
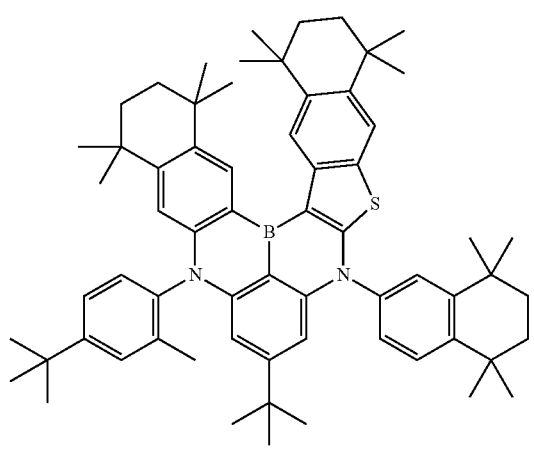
1482
-continued
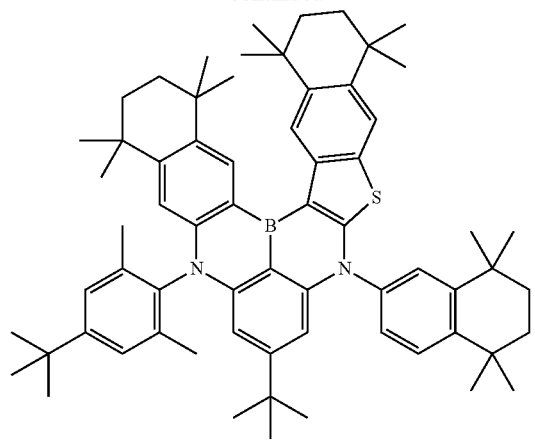
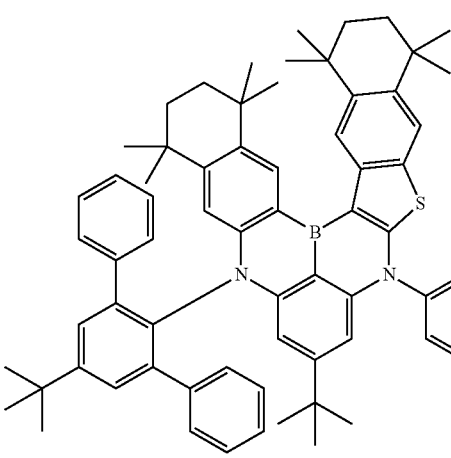
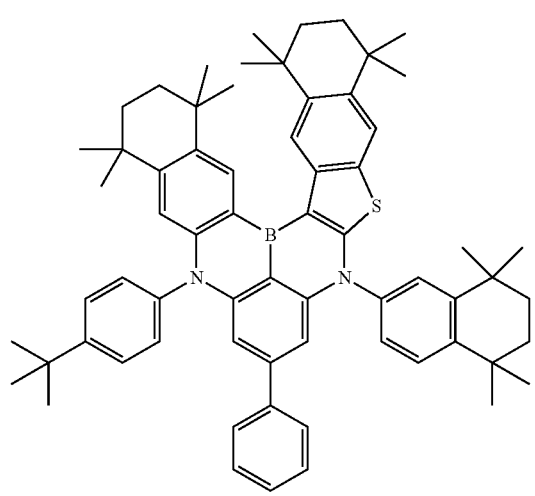

1483
-continued
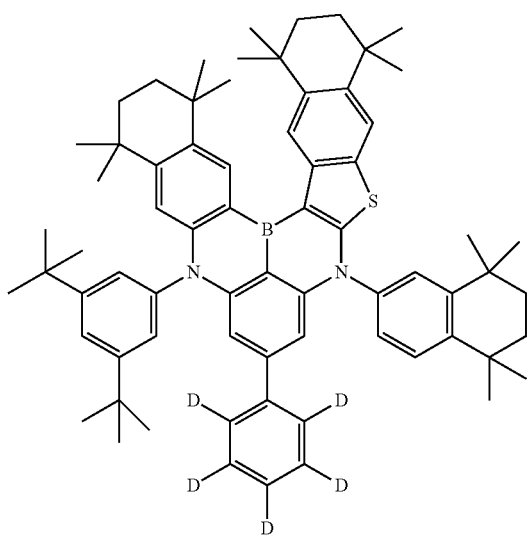
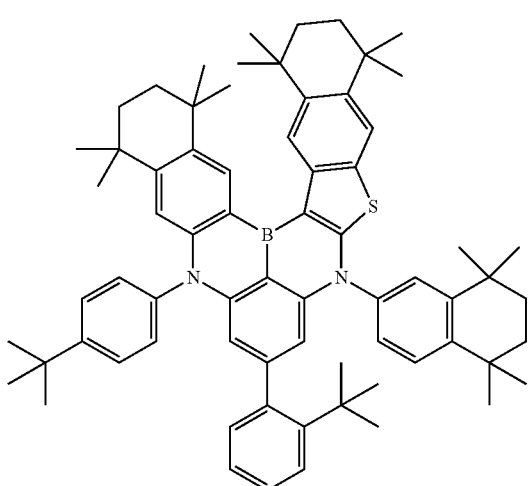
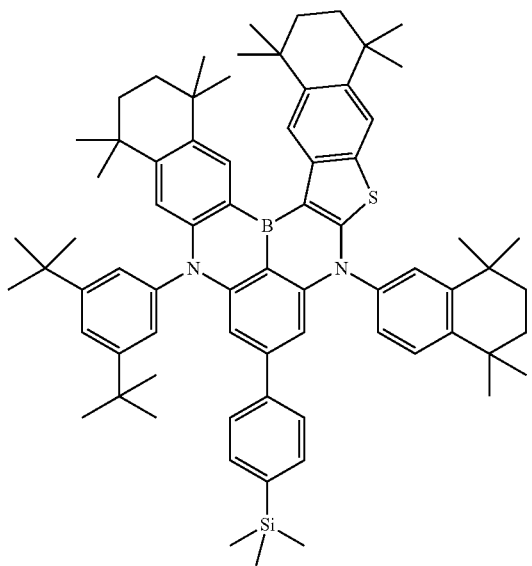
1484
-continued
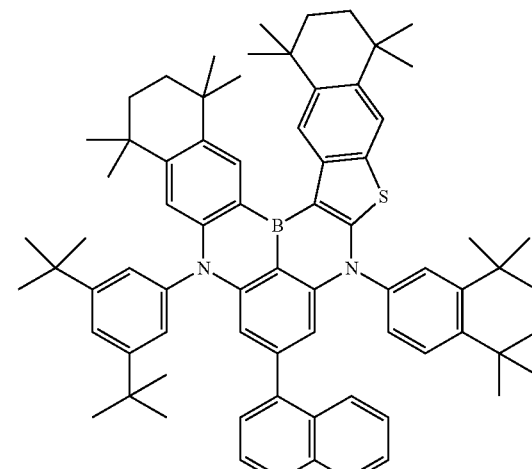
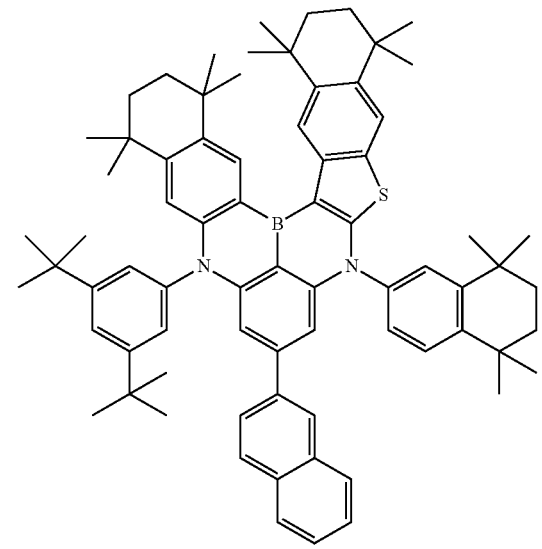
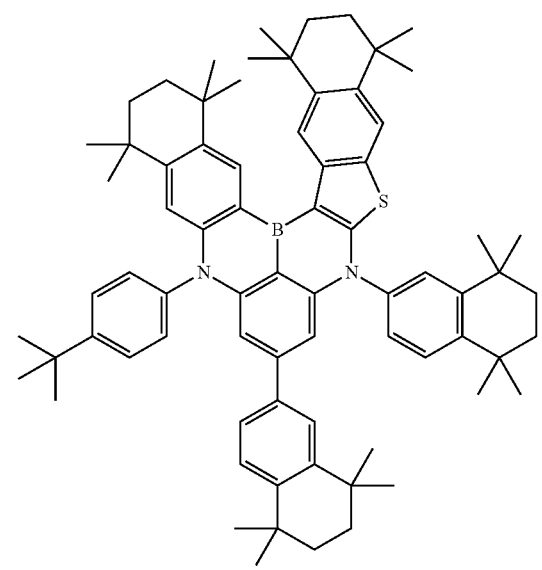

1485
-continued
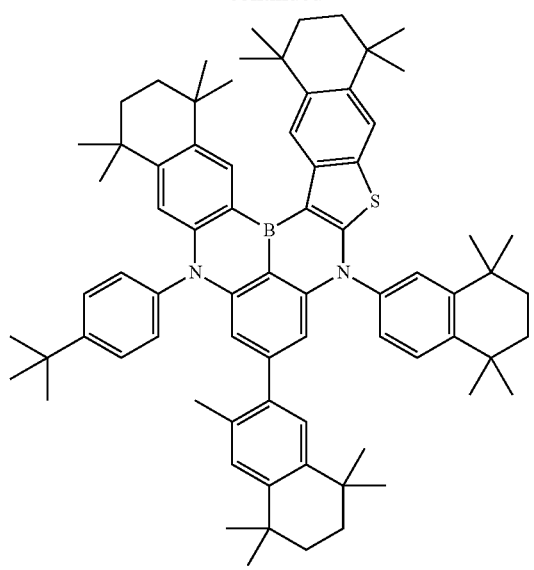
1486
-continued
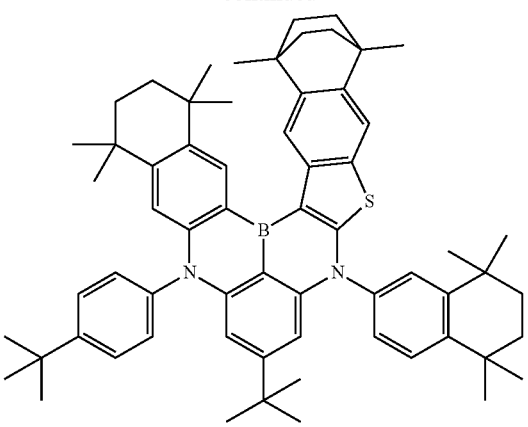
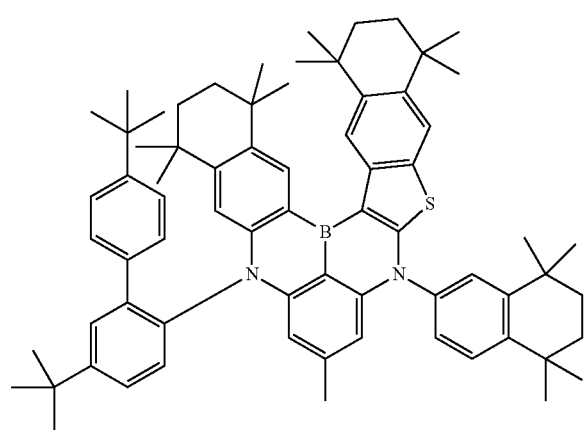
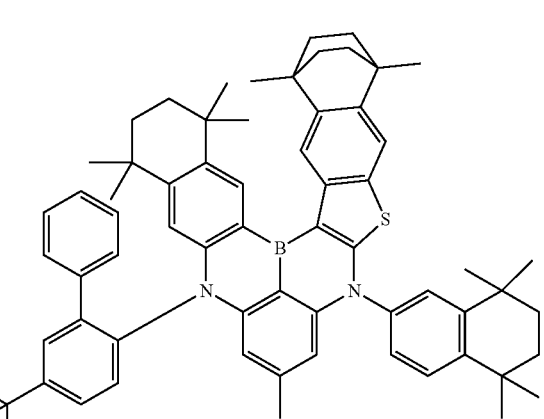
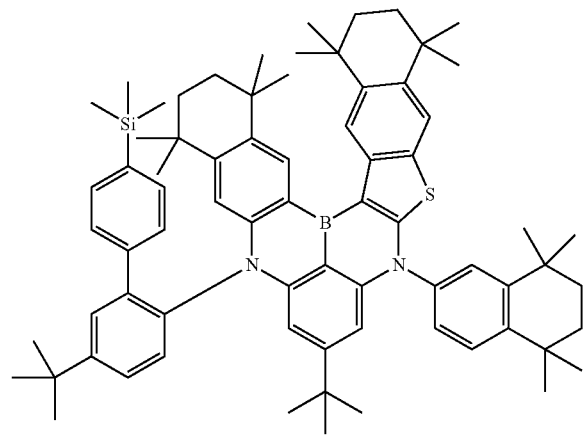
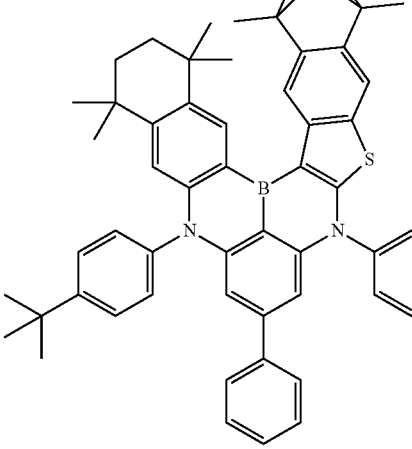

1487
-continued
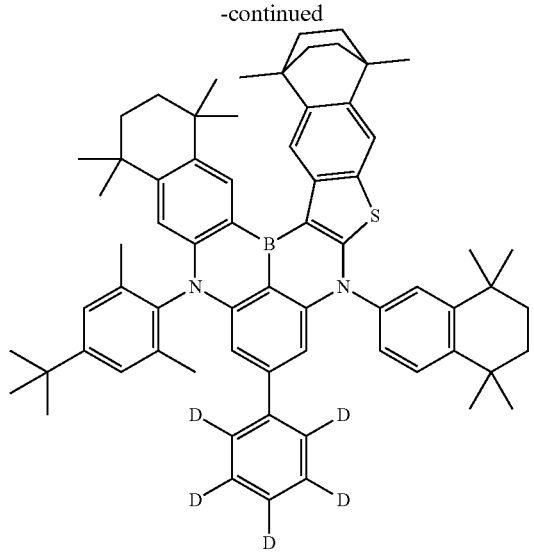
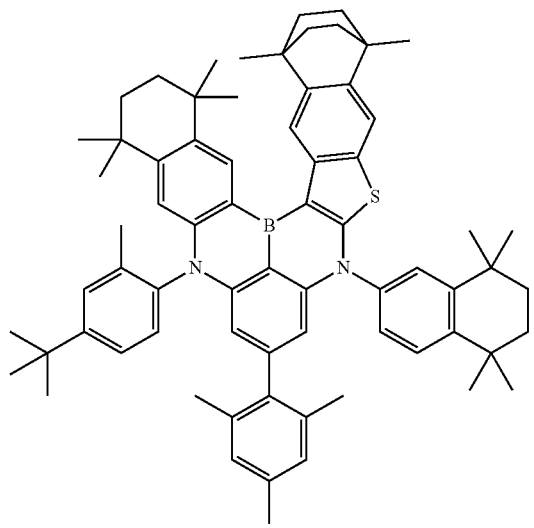
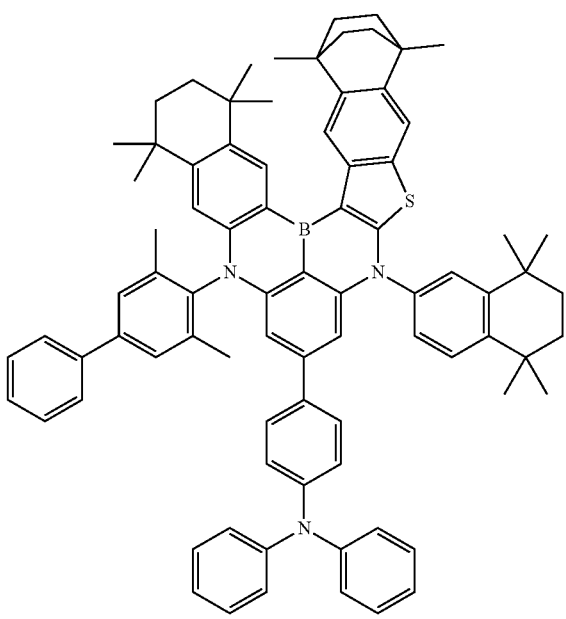
1488
-continued
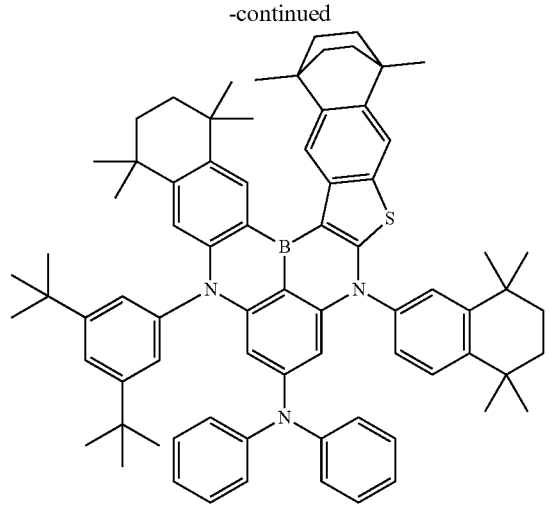
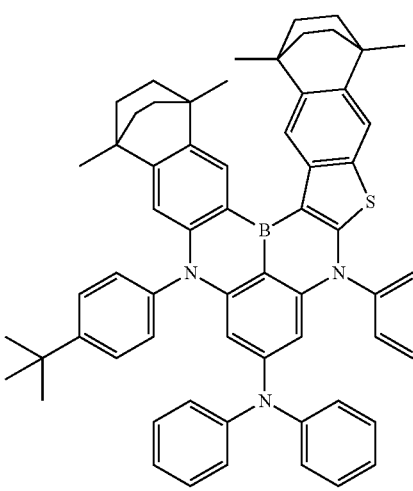
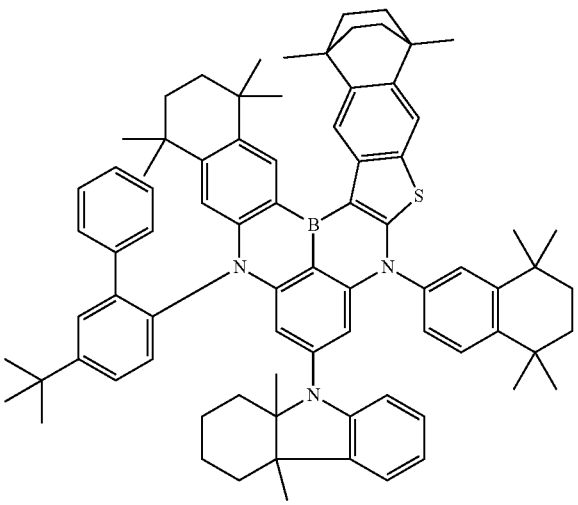

1489
-continued
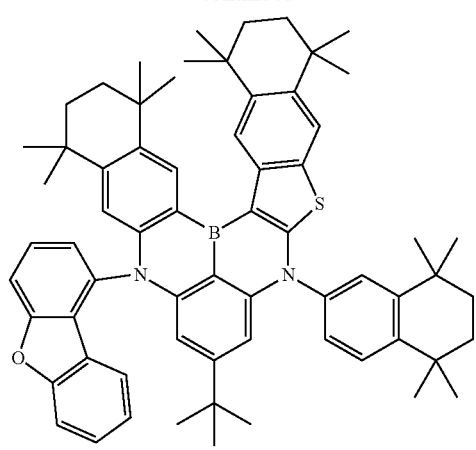
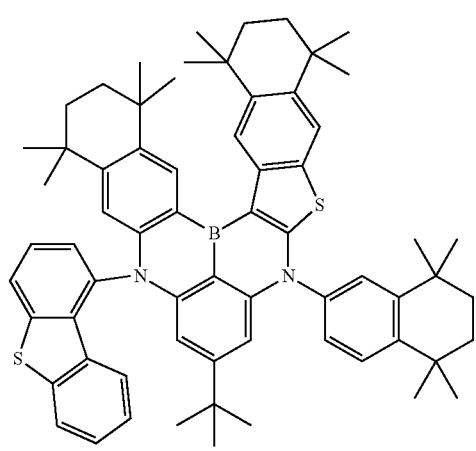
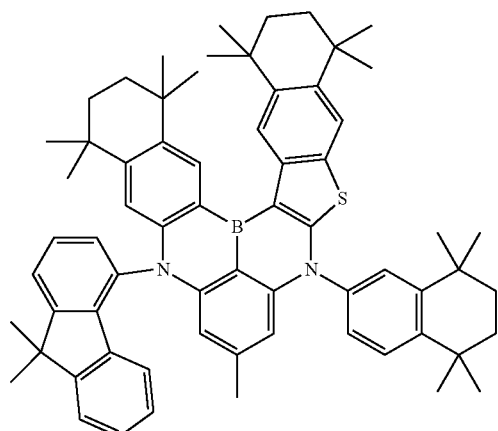
1490
-continued
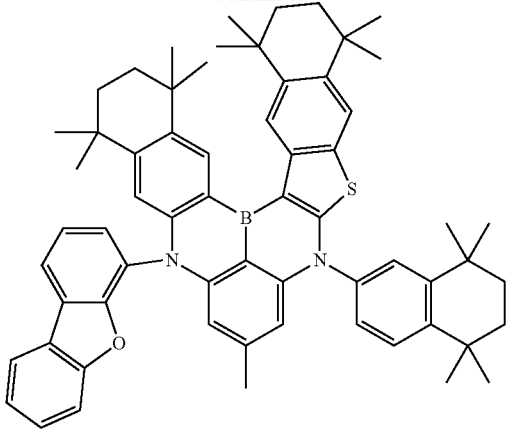
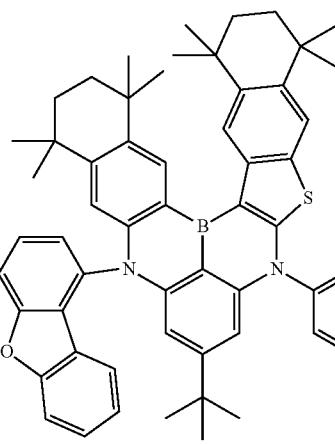
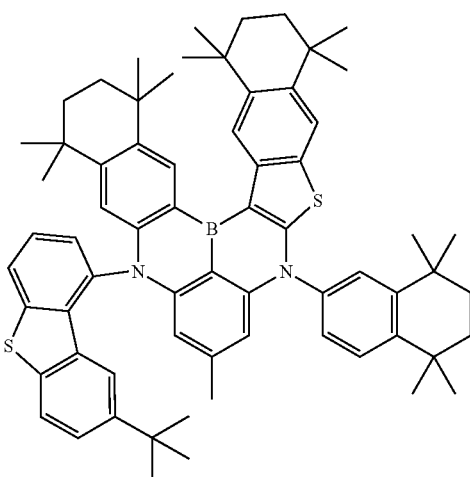

1491
-continued
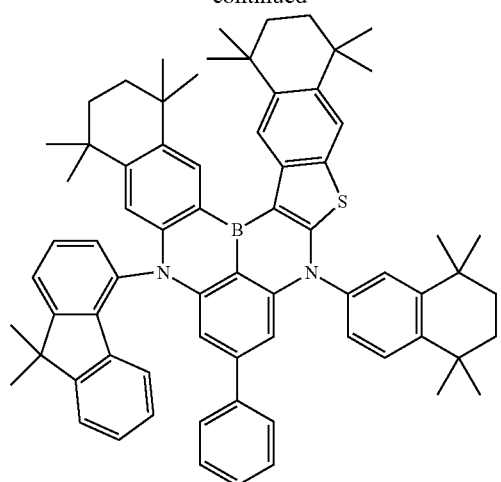
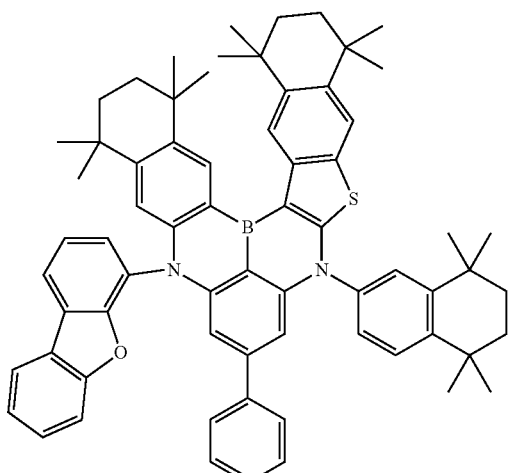
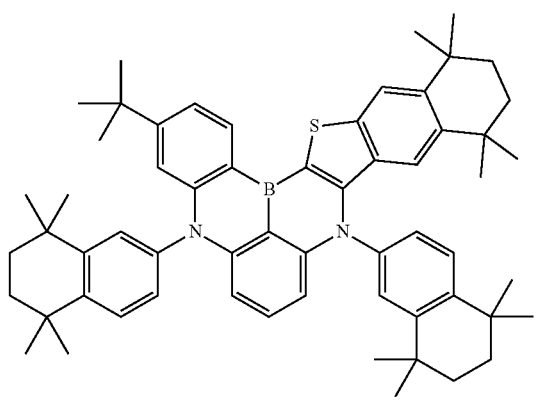
1492
-continued
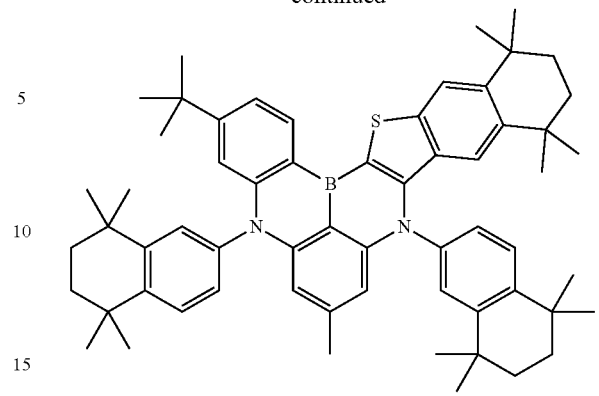
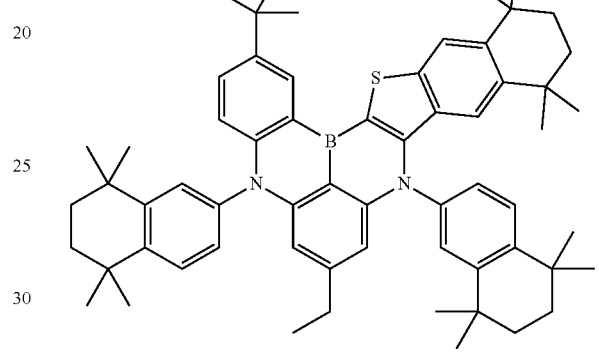
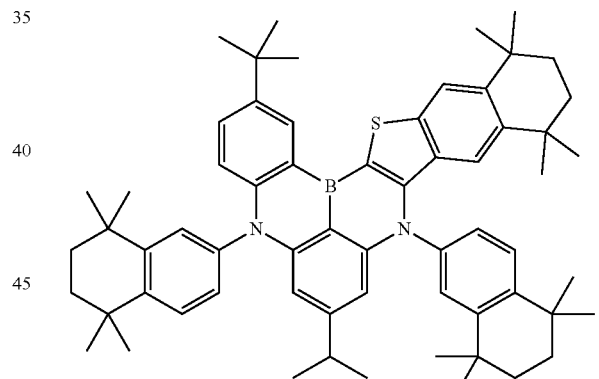
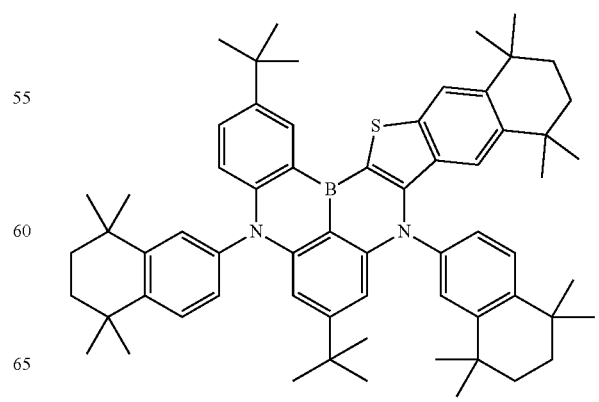

1493
-continued
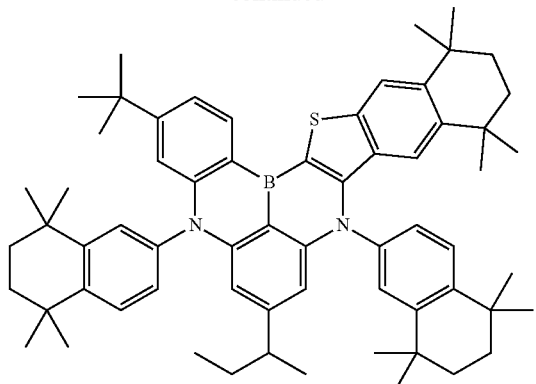
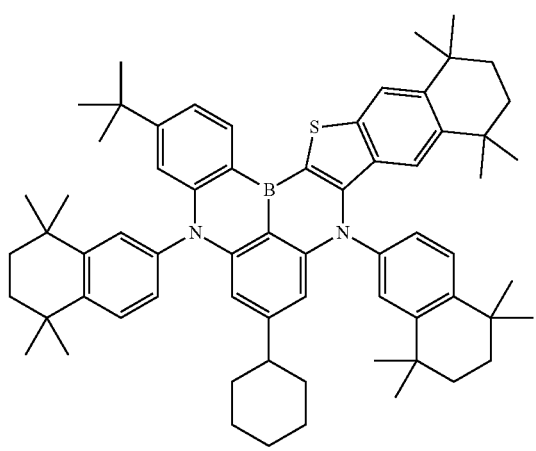
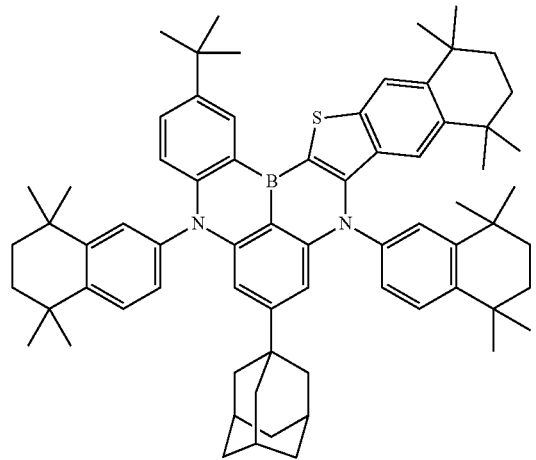
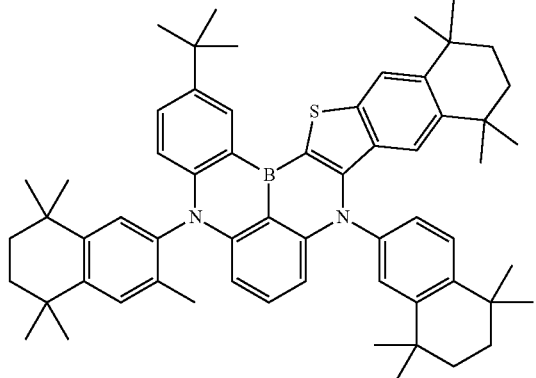
1494
-continued
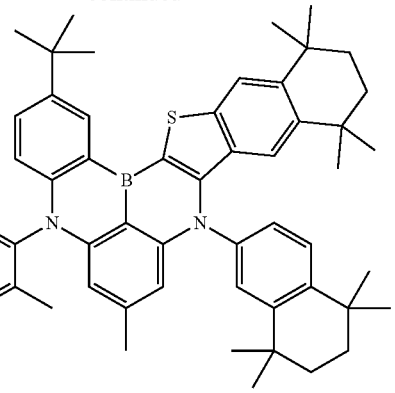
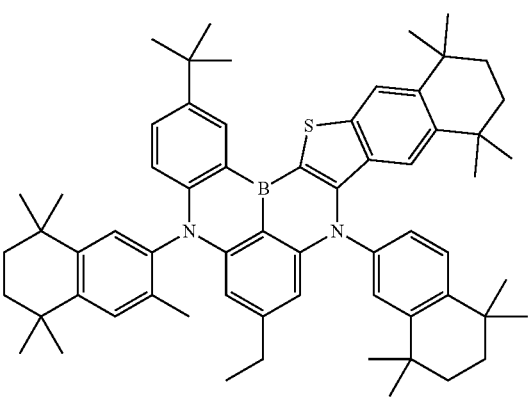
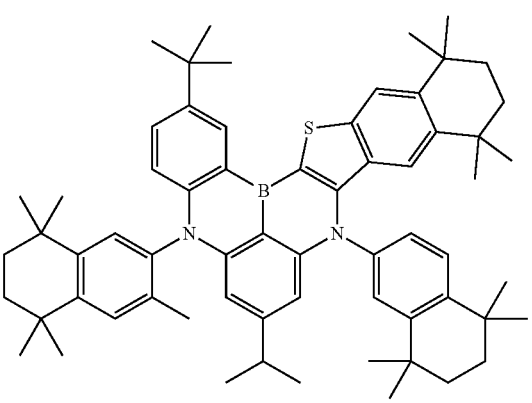
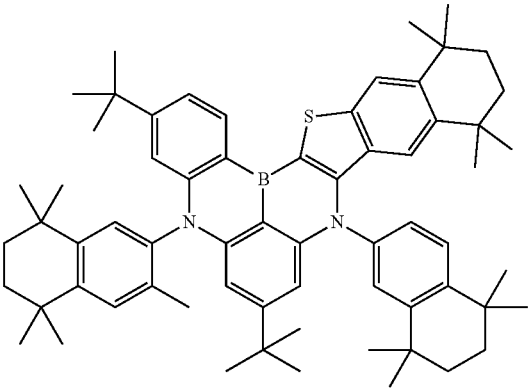

1495
-continued
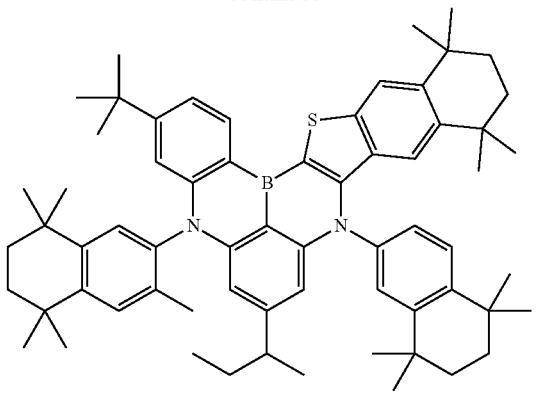
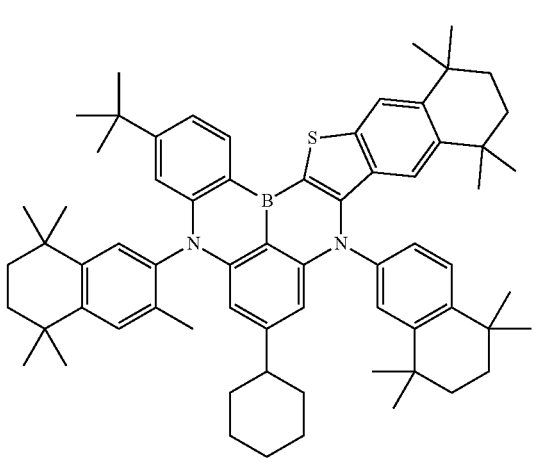
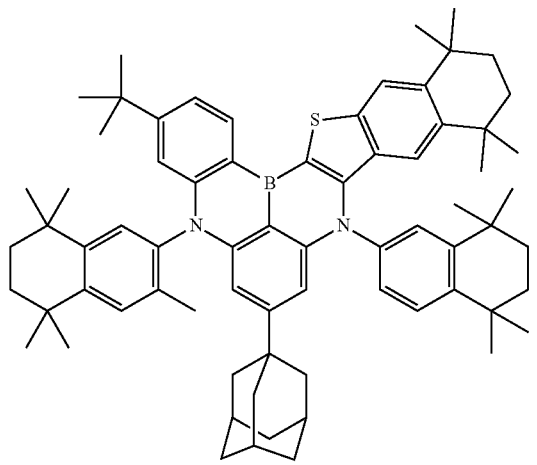
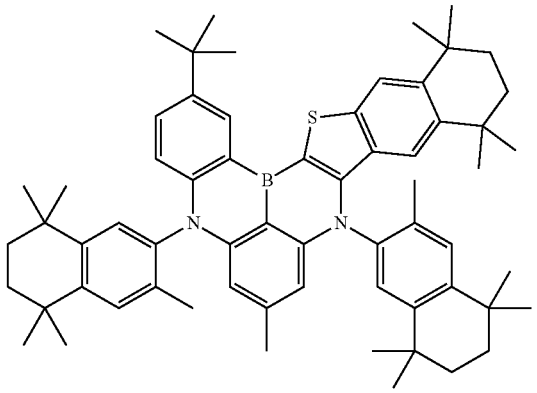
1496
-continued
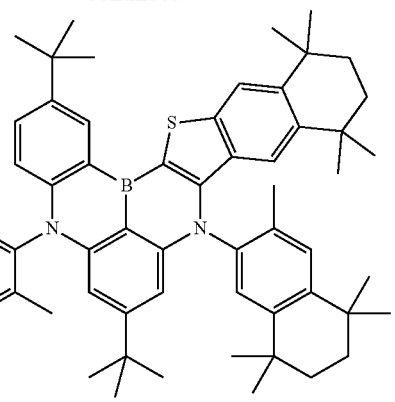
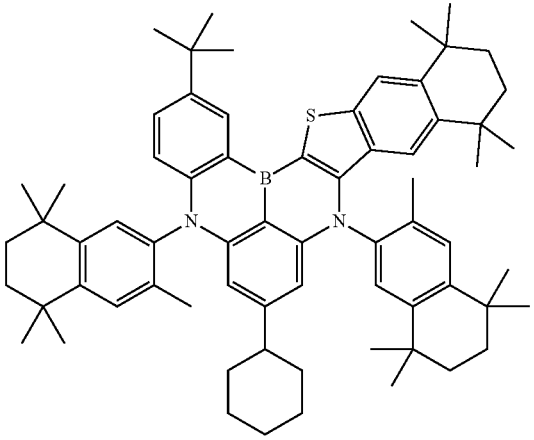

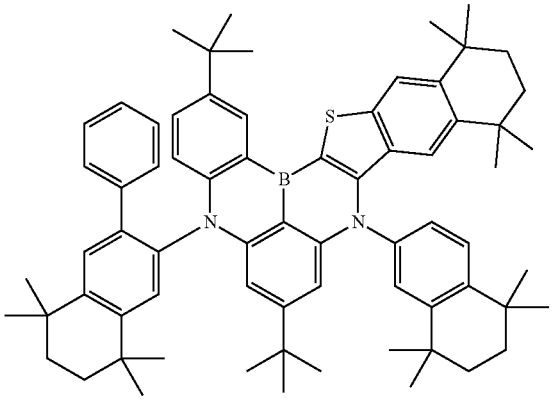

1497
-continued
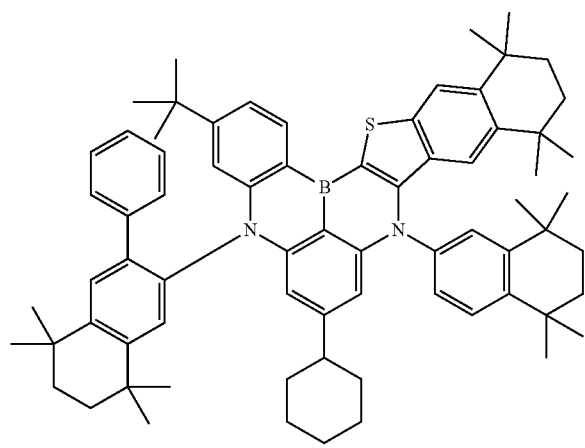
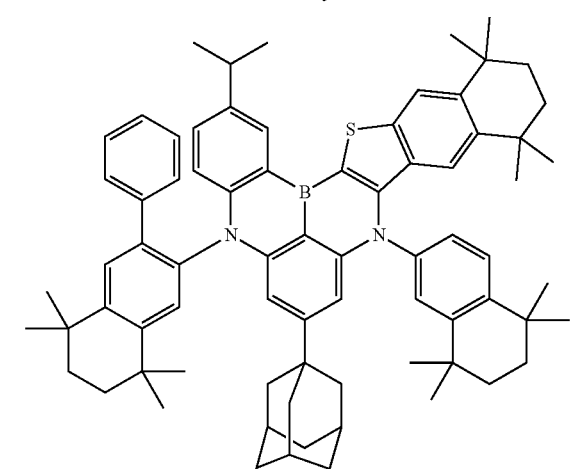
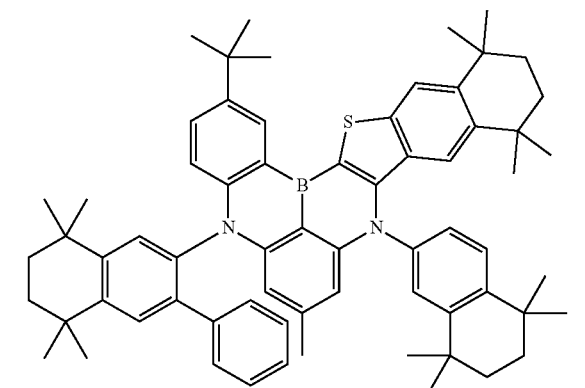
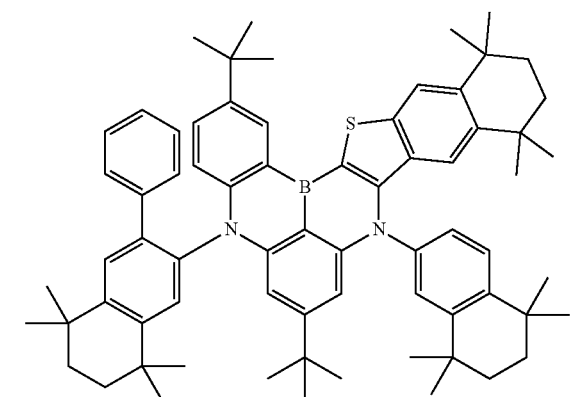
1498
-continued
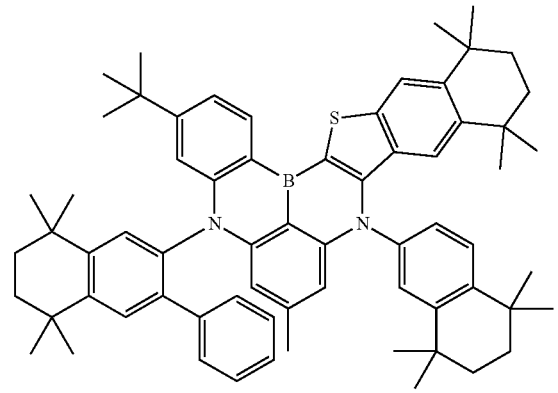
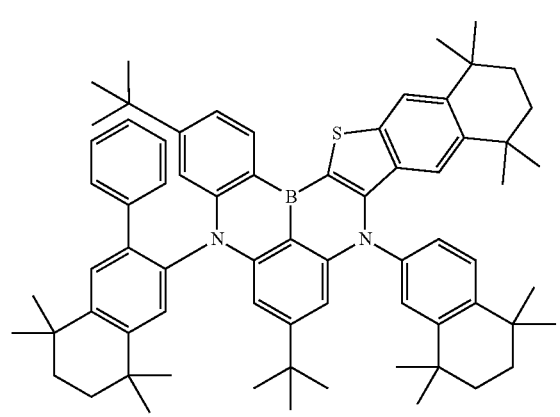
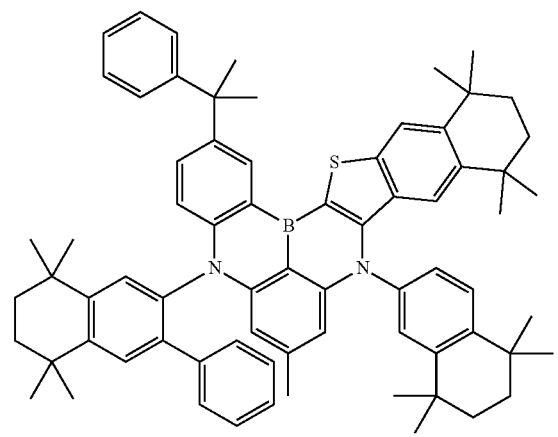
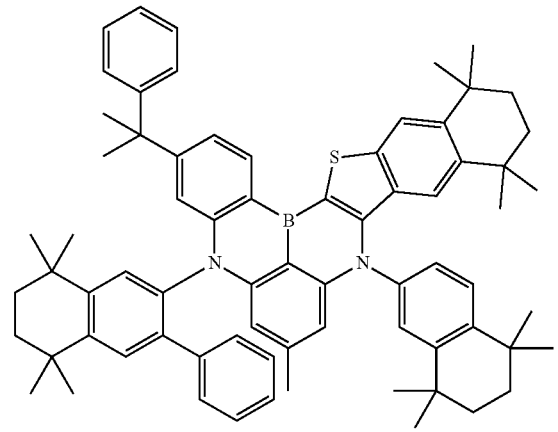

| 1499 | 1500 |
|---|---|
| -continued | -continued |
| 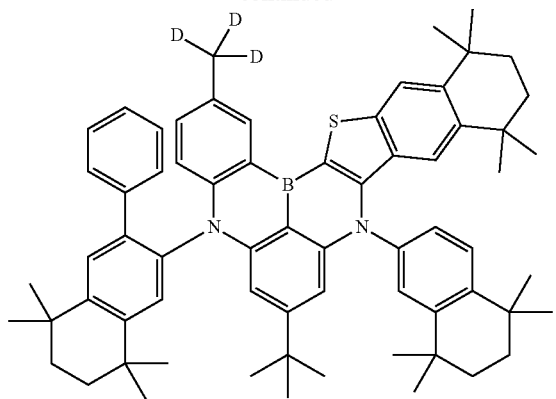 | 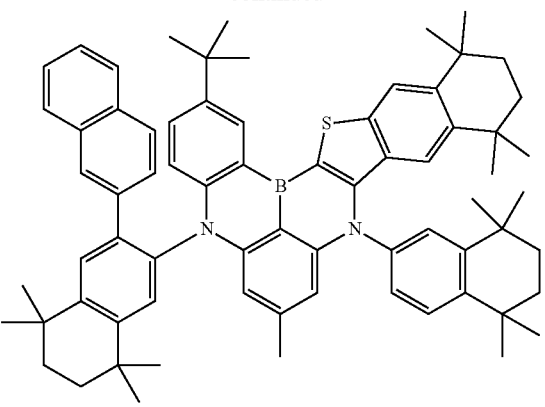 |
| 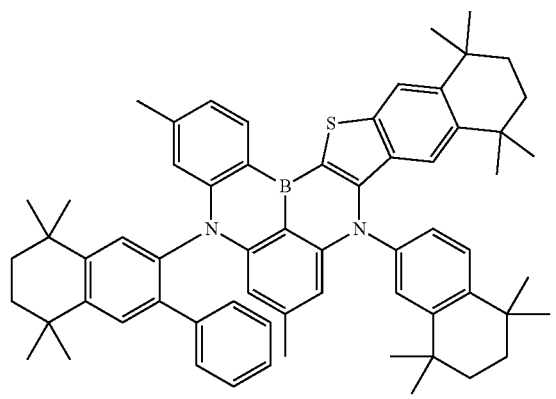 | 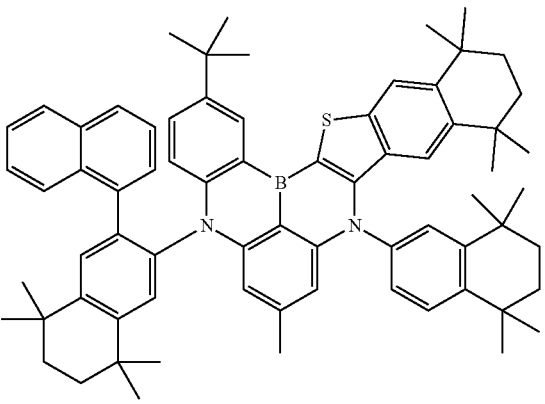 |
| 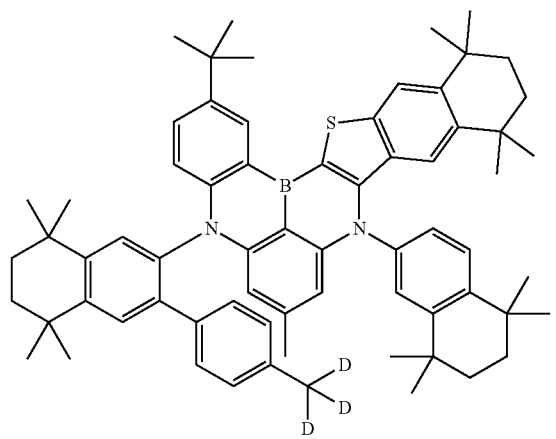 |  |
| 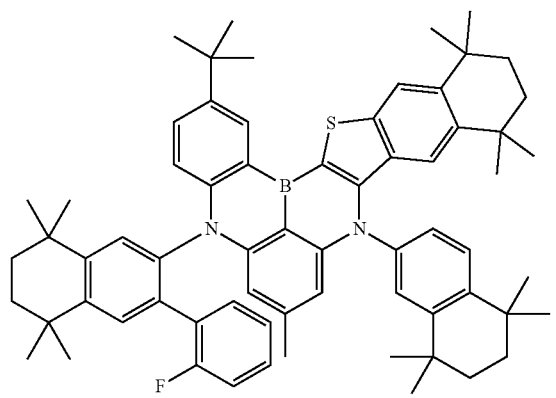 | 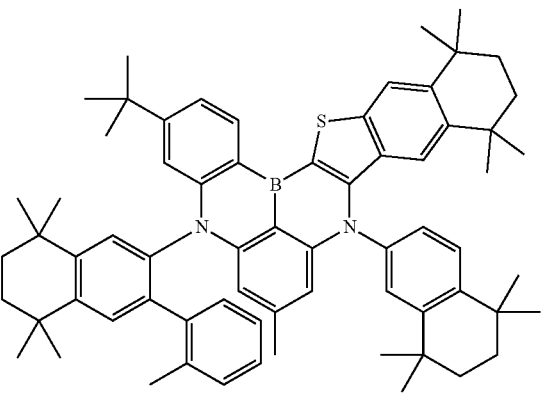 |

1501
-continued
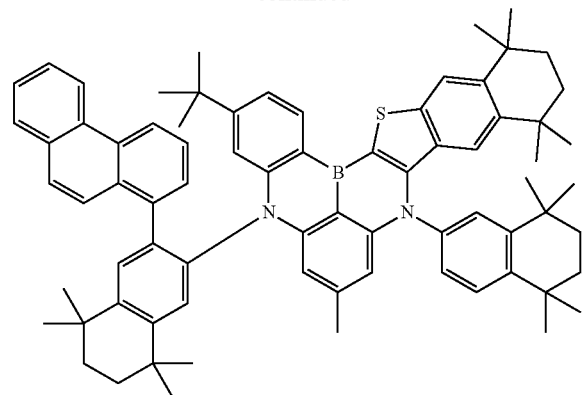
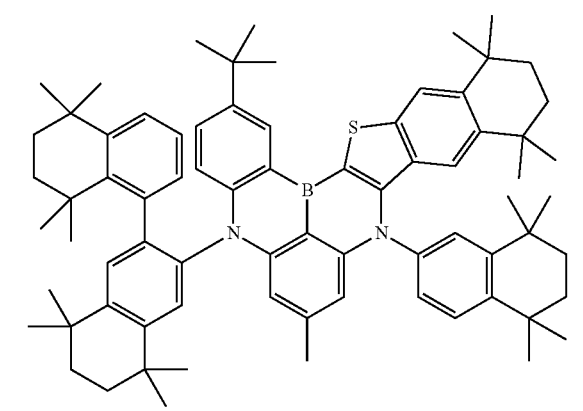
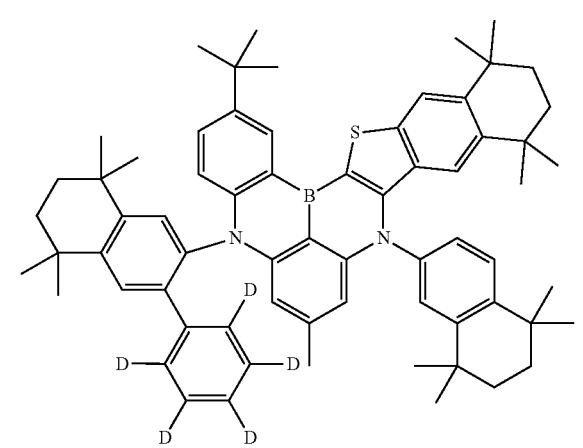
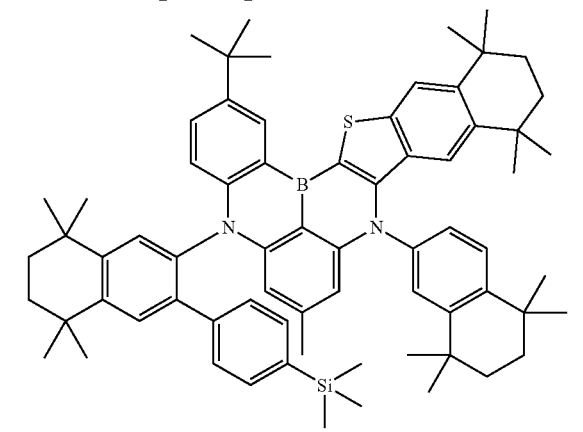
1502
-continued
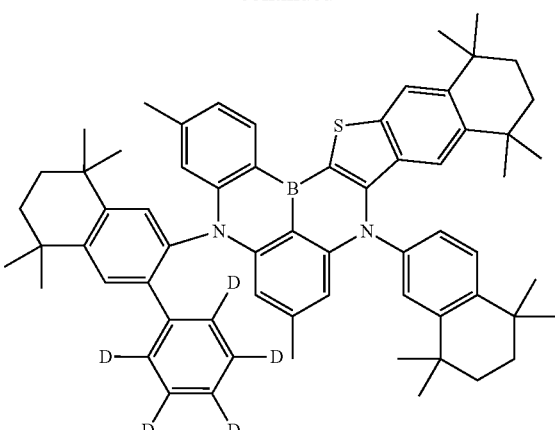
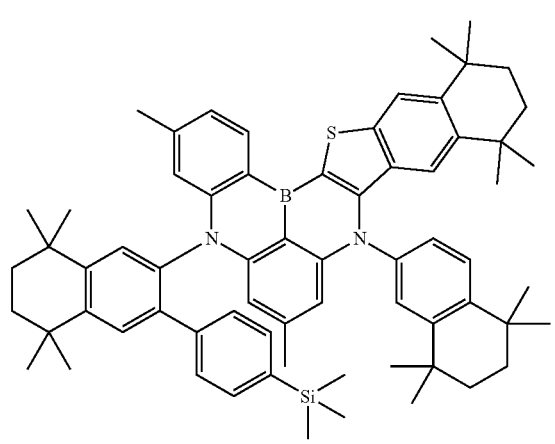
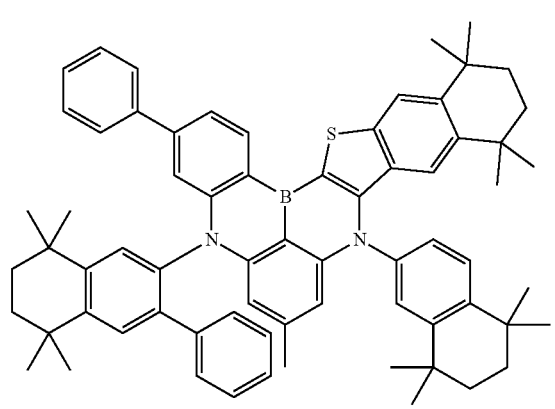
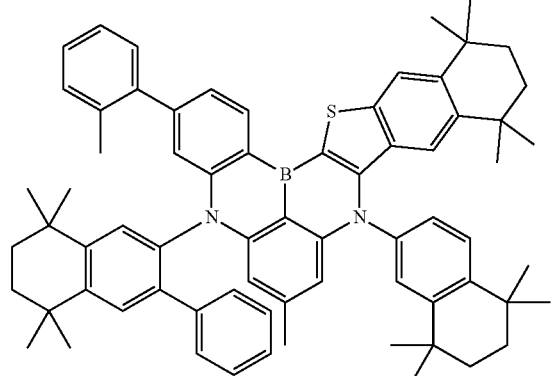

| 1503 -continued | 1504 -continued |
|---|---|
| 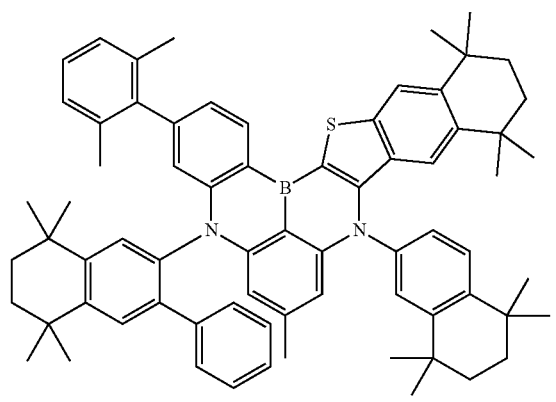 | 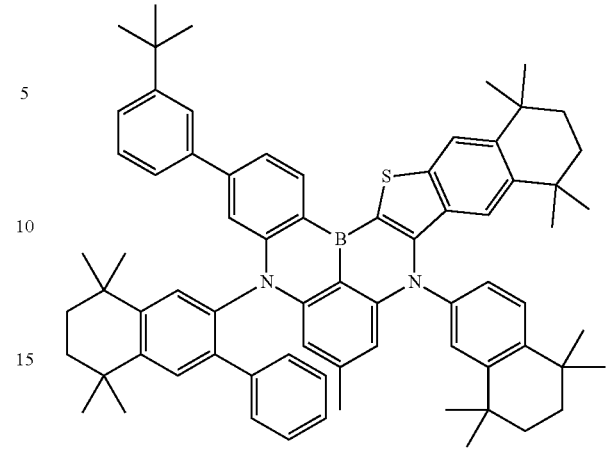 |
| 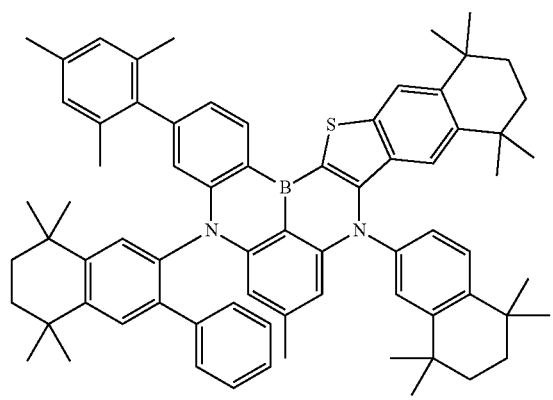 | 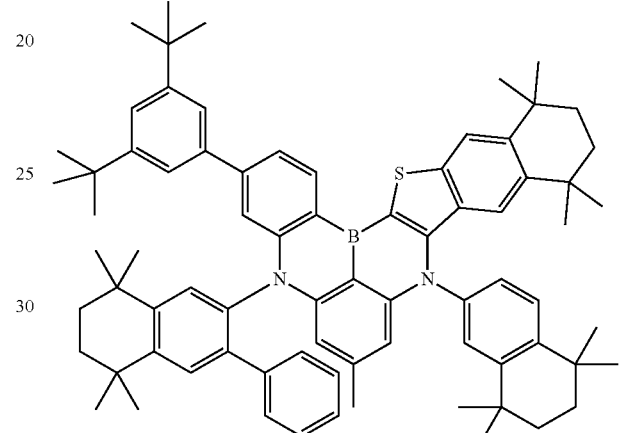 |
| 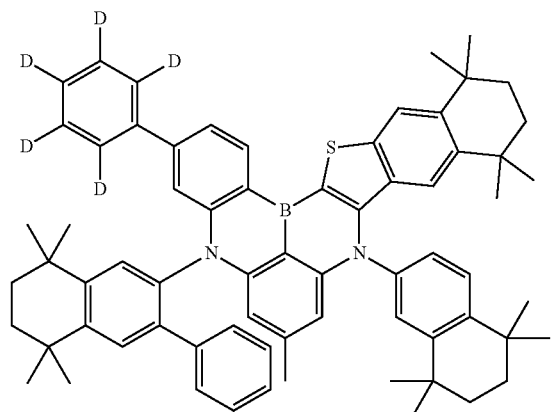 | 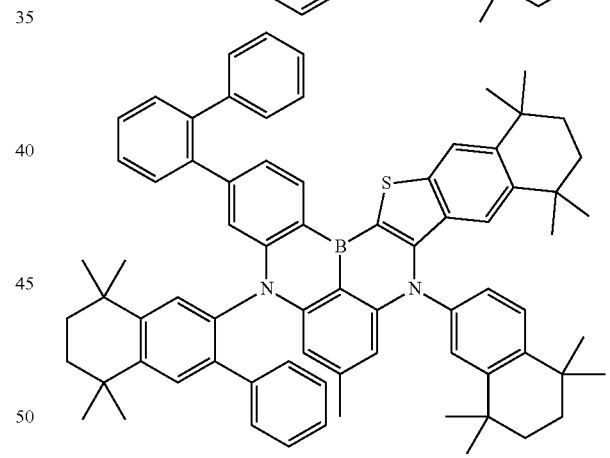 |
| 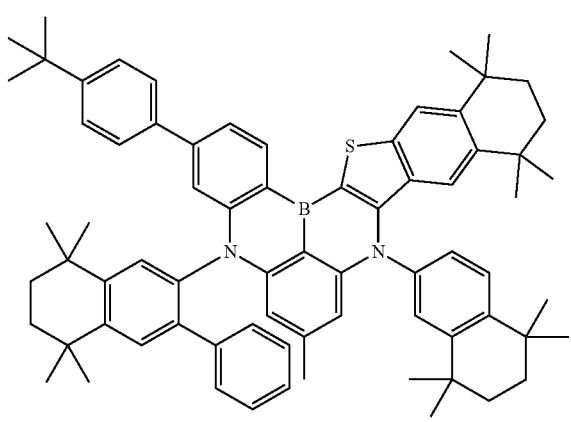 | 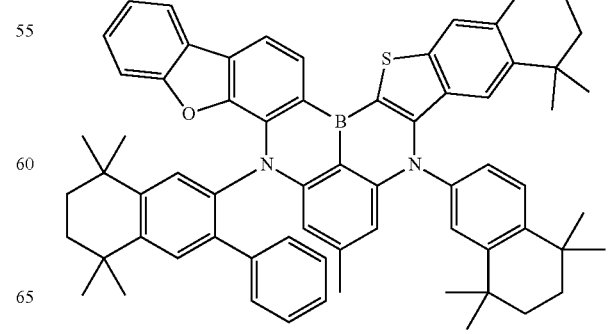 |

1505
-continued
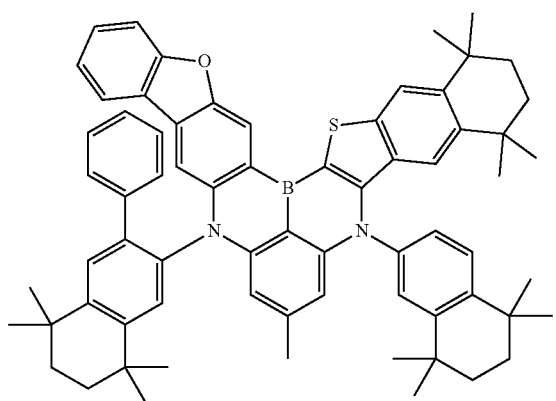
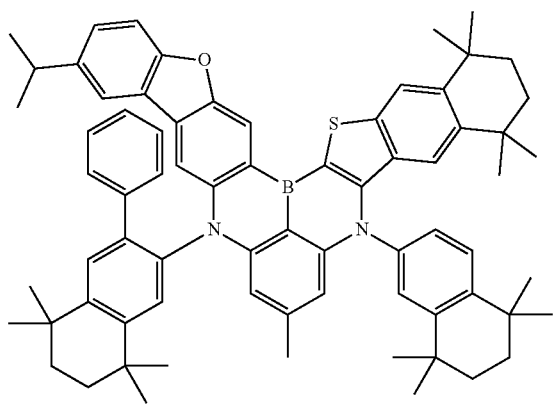
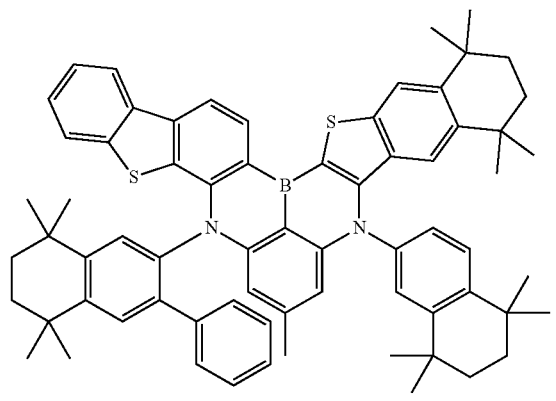
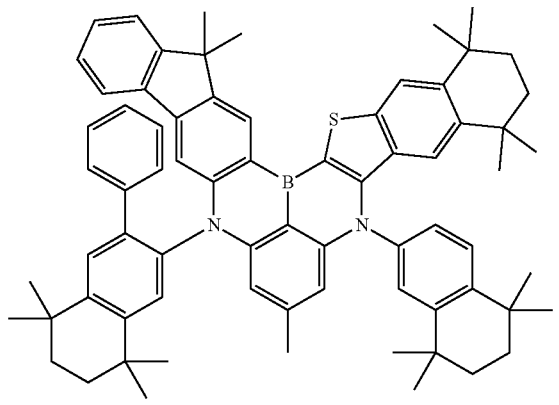
1506
-continued
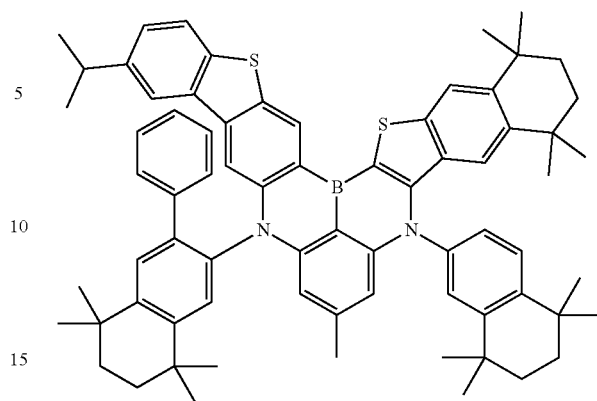
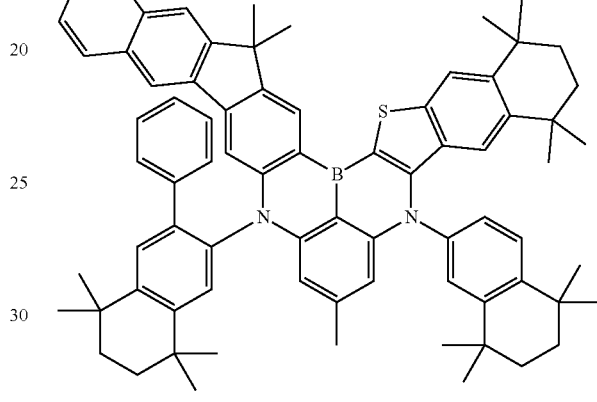

1507
-continued
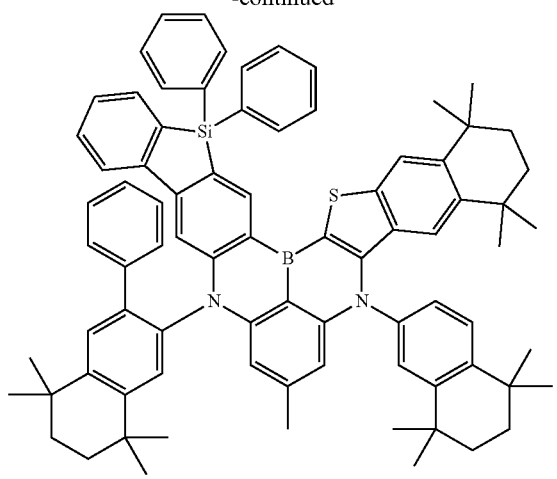
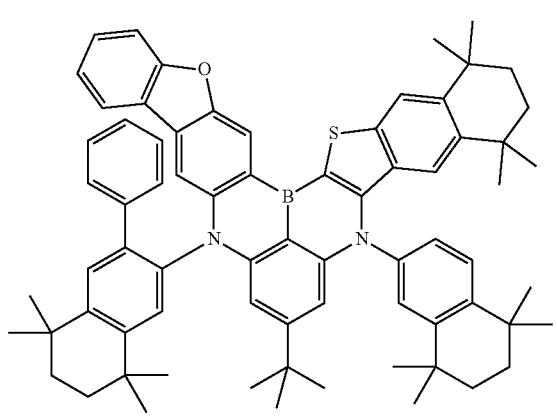
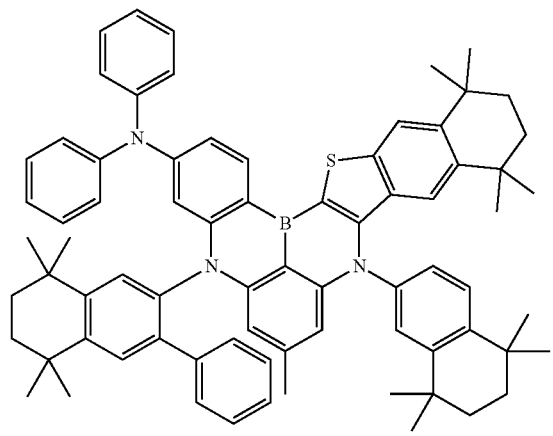
1508
-continued
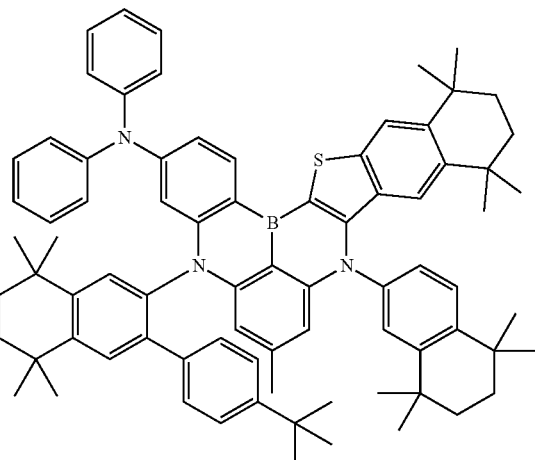
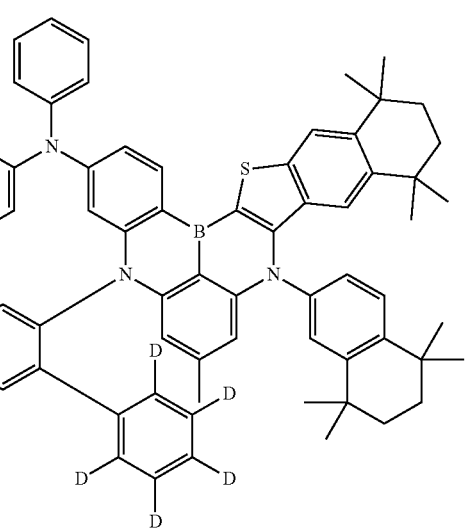
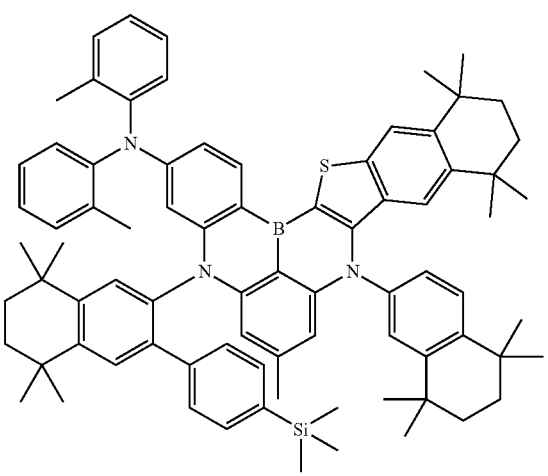

1509
-continued
1510
-continued
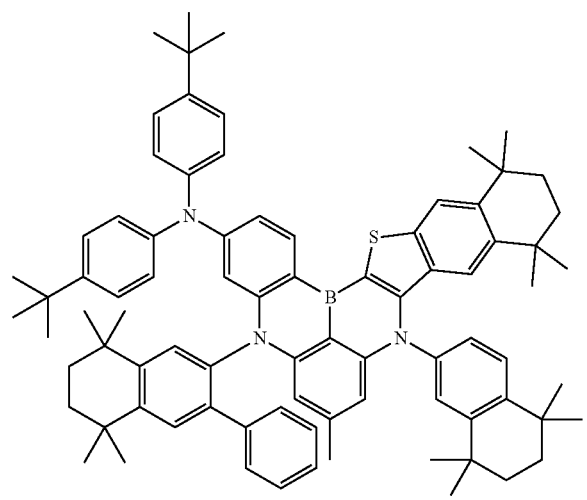
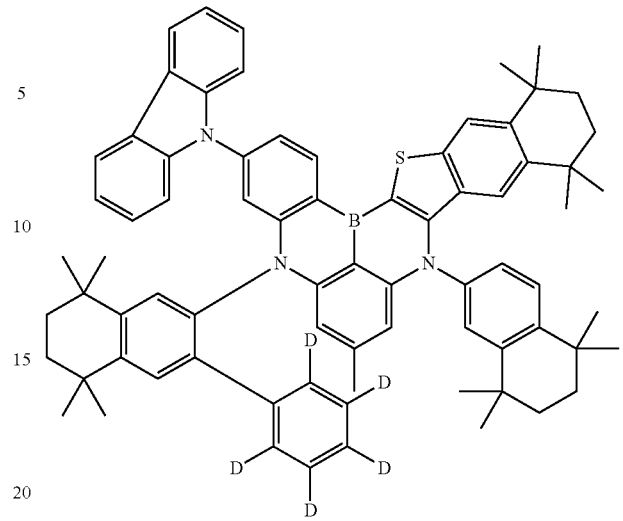
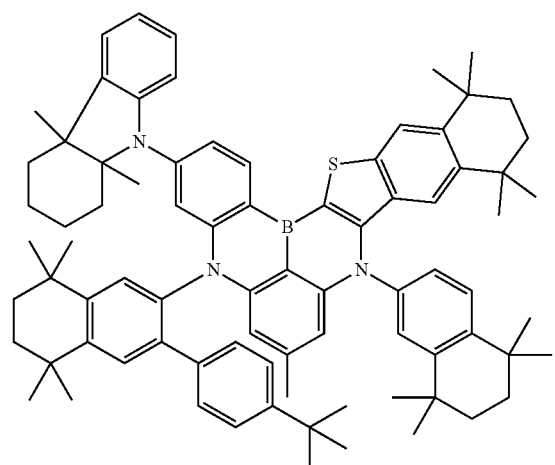
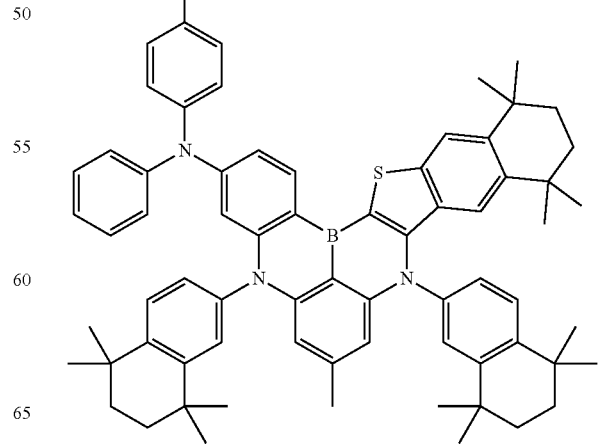
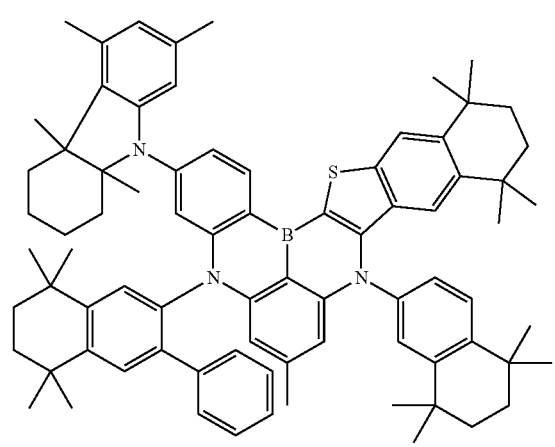

1511
-continued
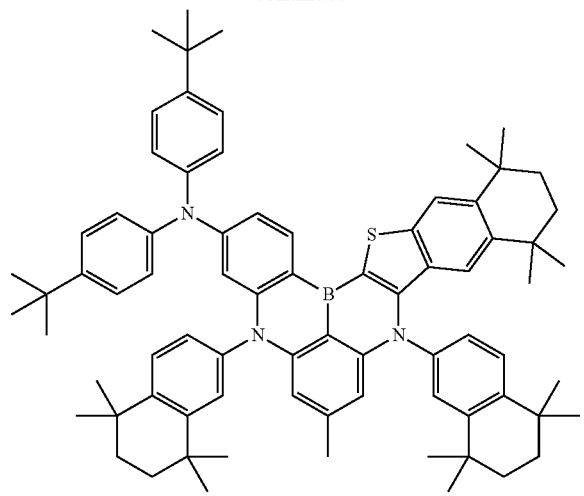
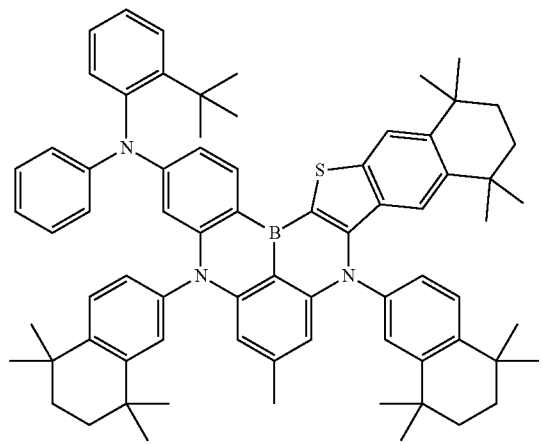
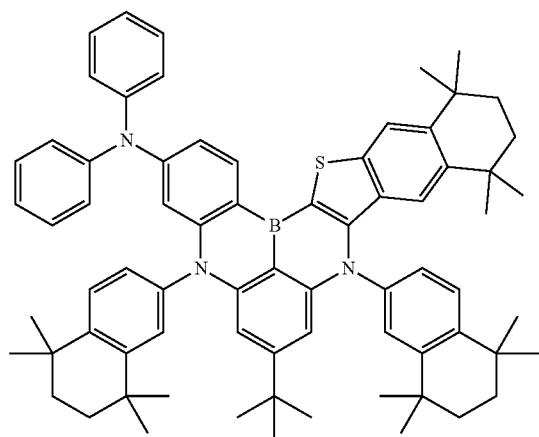
1512
-continued
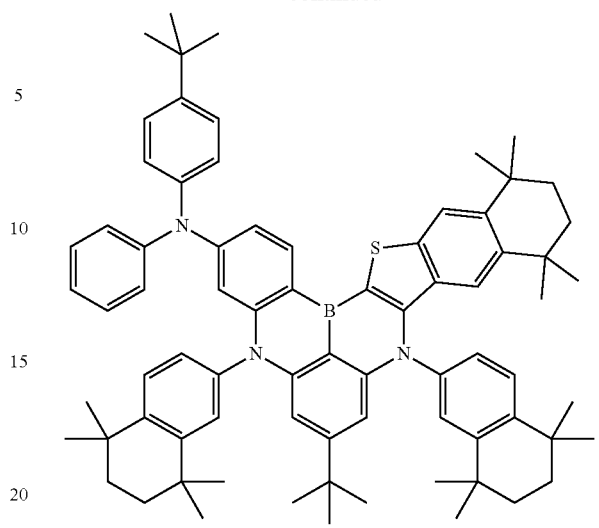
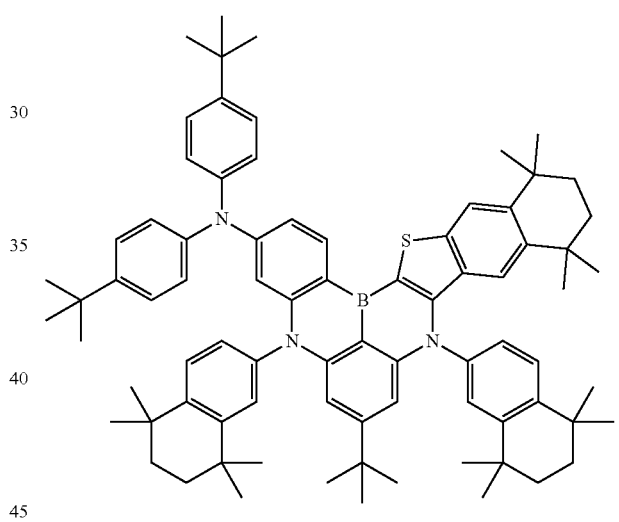
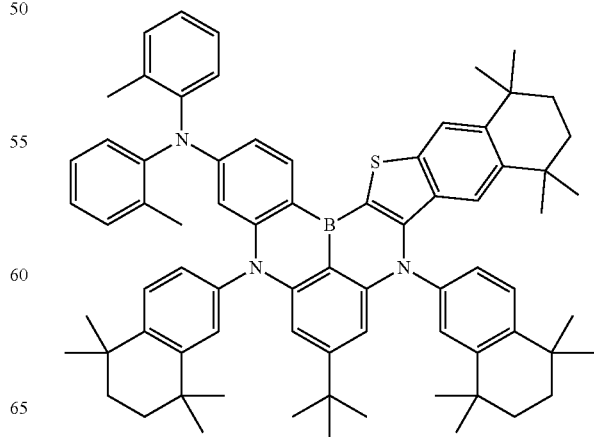

1513
-continued
1514
-continued
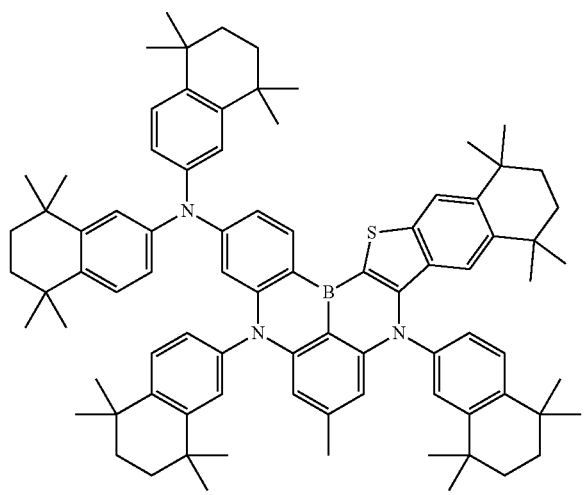
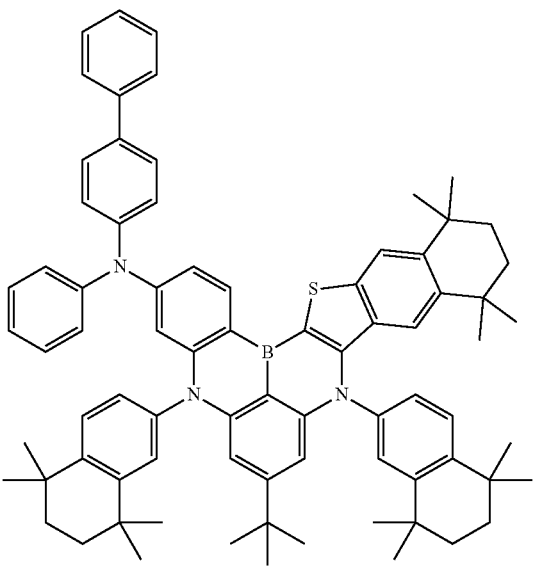
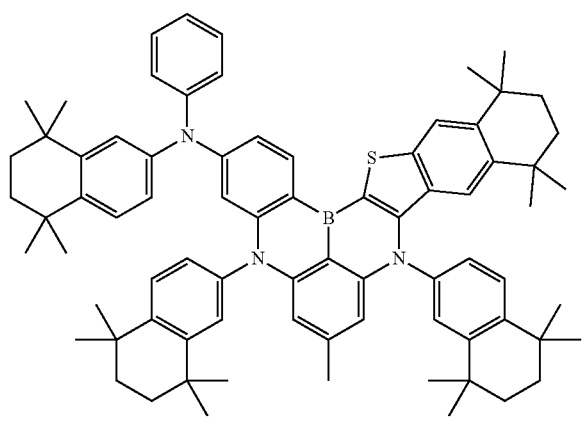
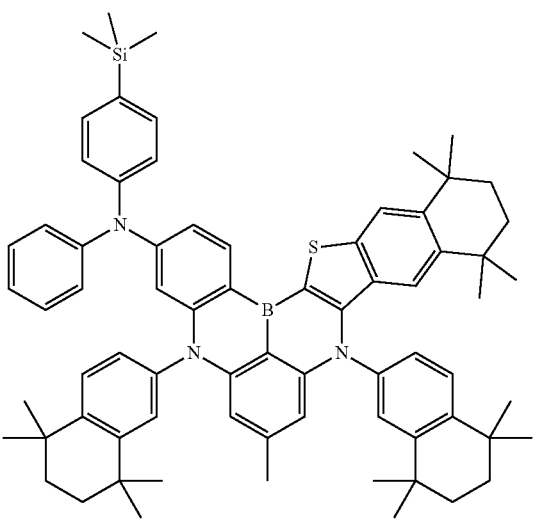
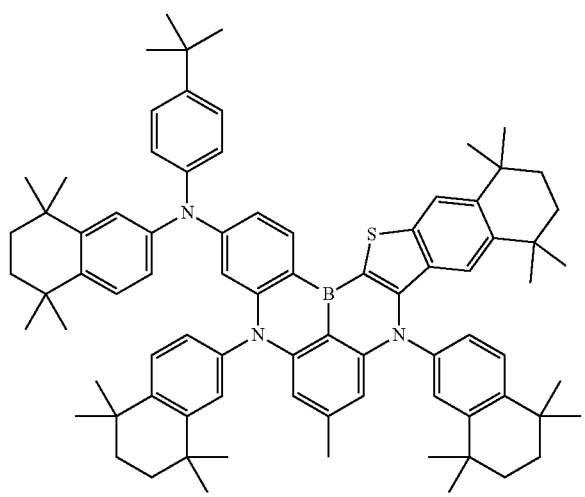
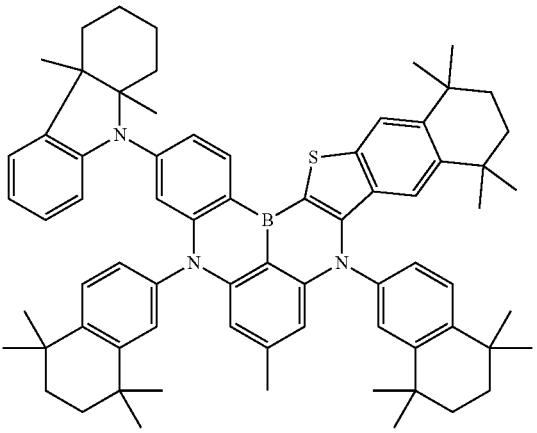

1515
-continued
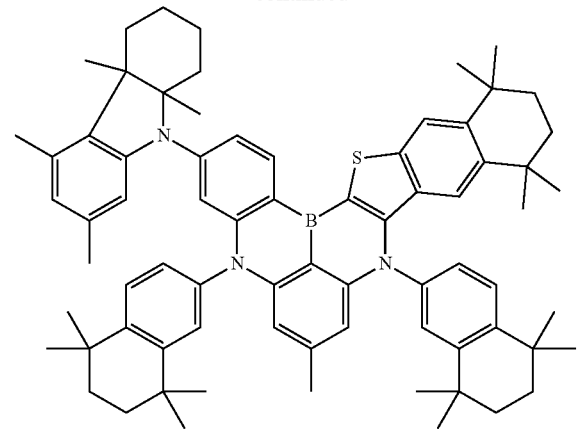
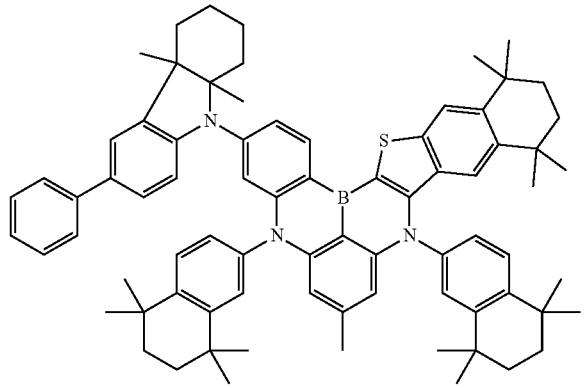
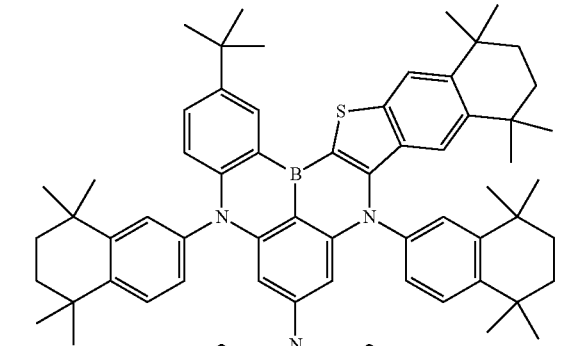

1516
-continued
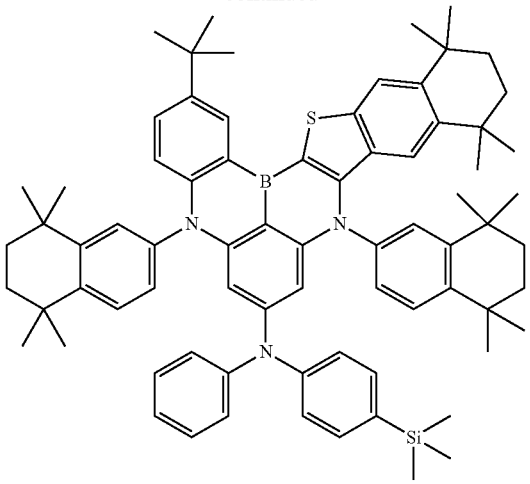
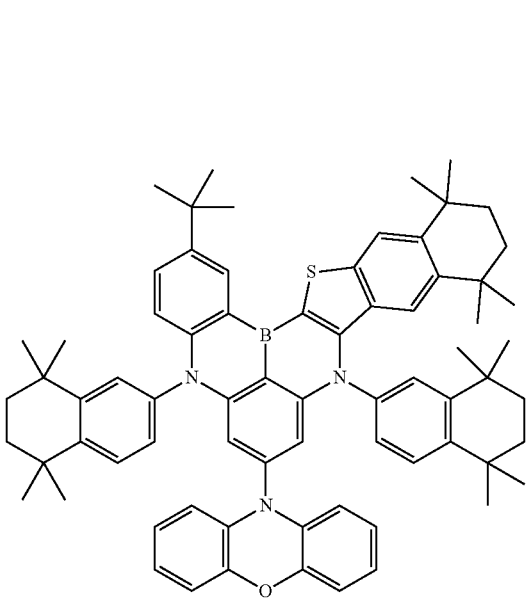
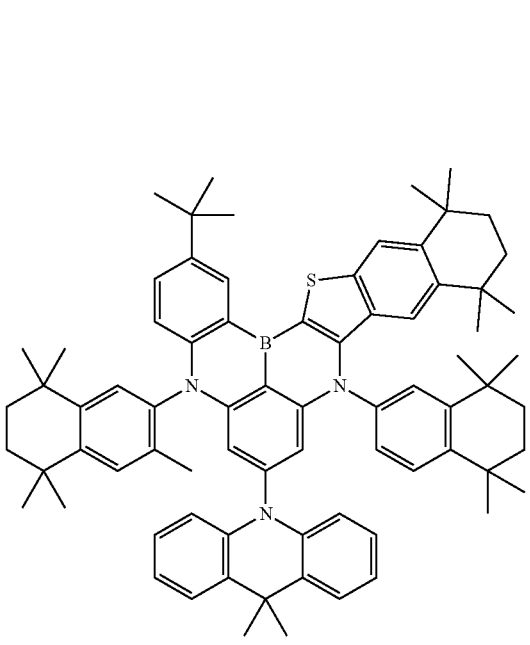

1517
-continued
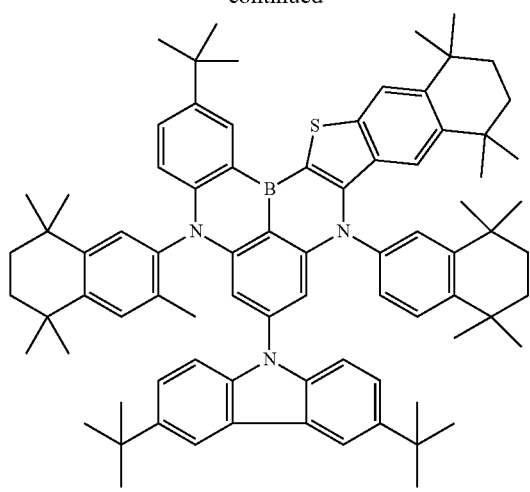
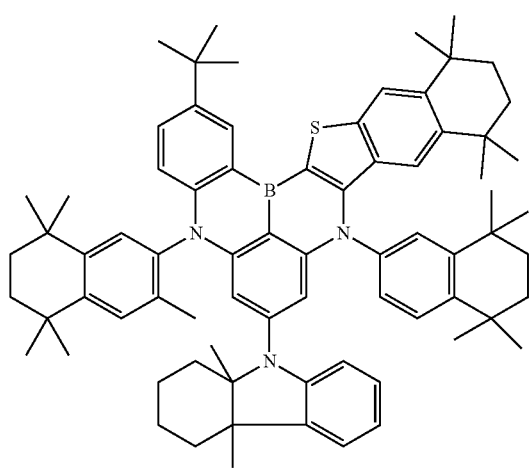
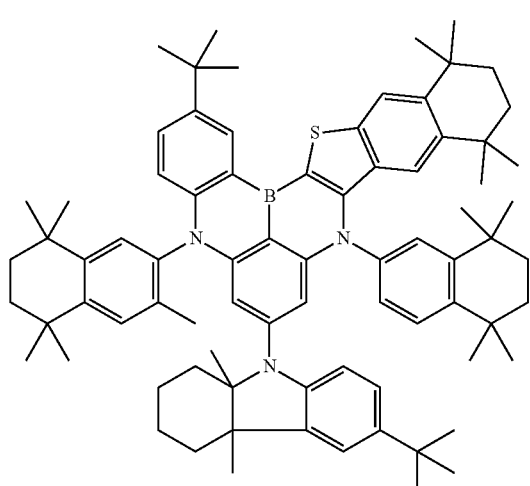
1518
-continued
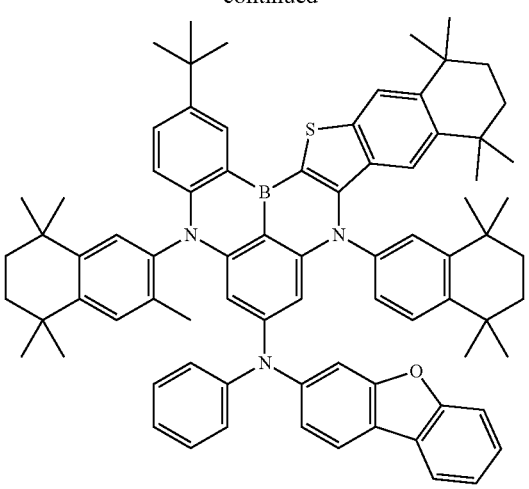
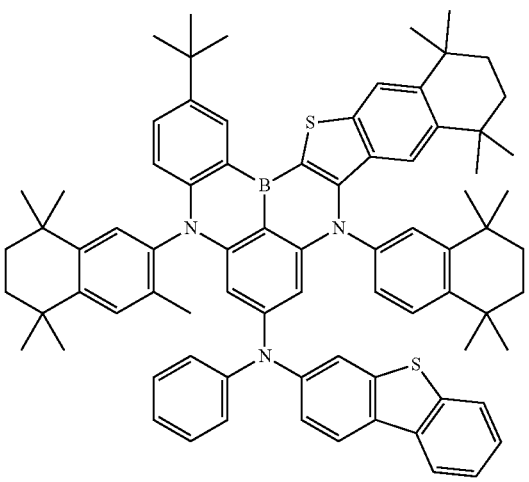
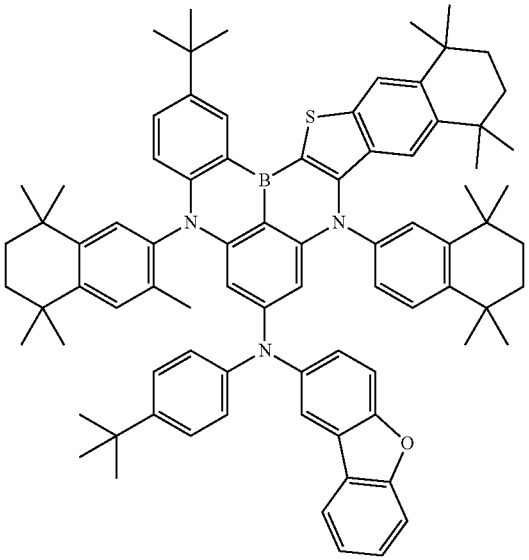

1519
-continued
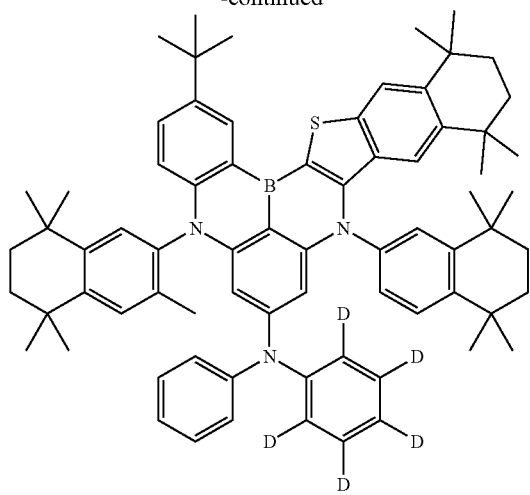
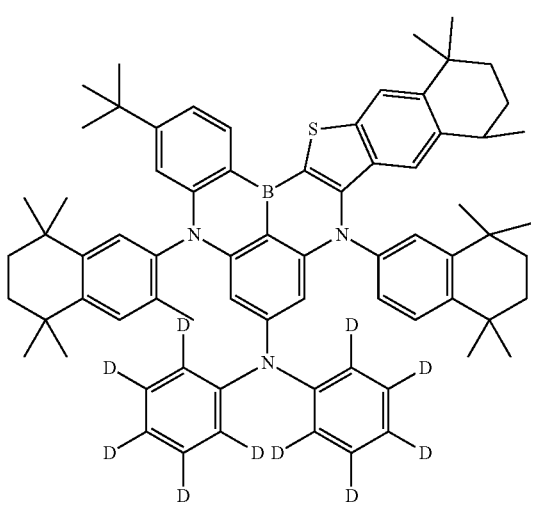
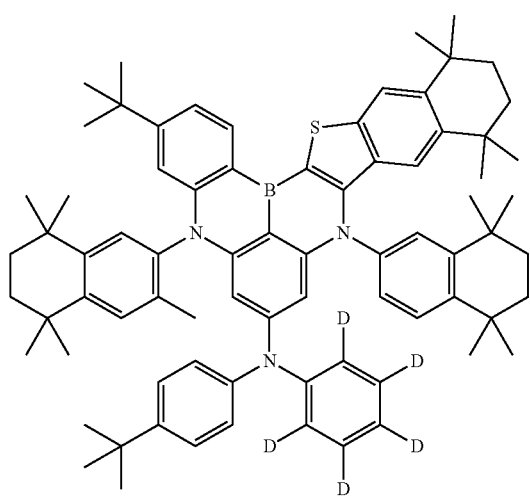
1520
-continued
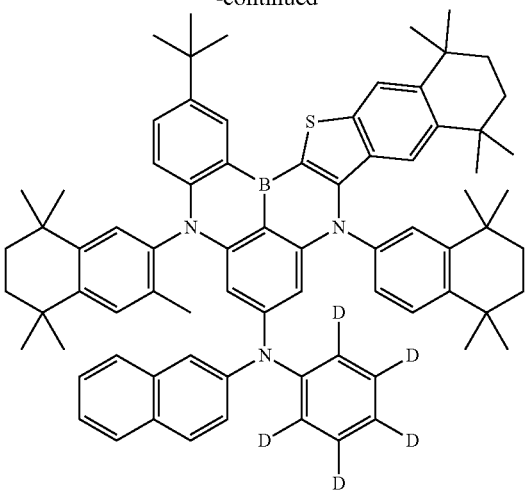
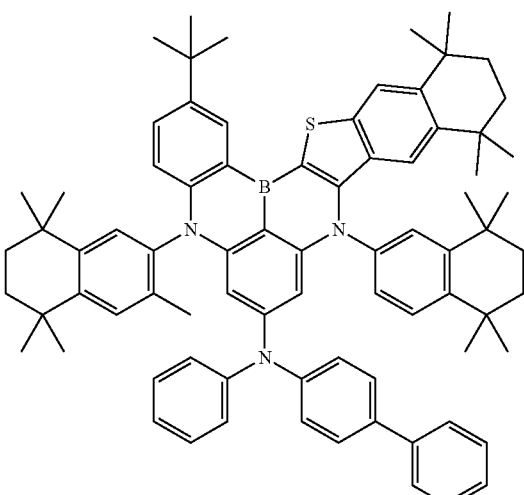
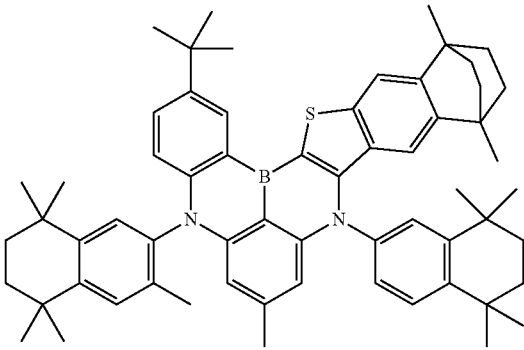

| 1521 -continued | 1522 -continued |
|---|---|
| 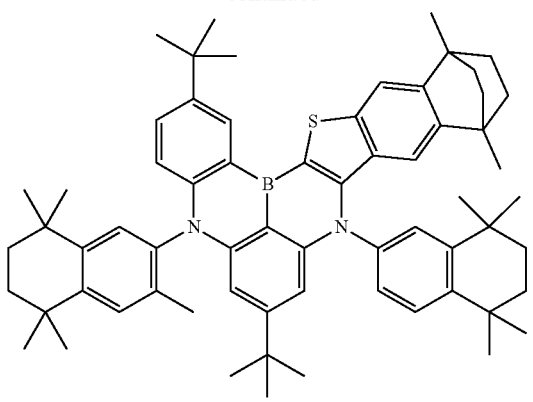 | 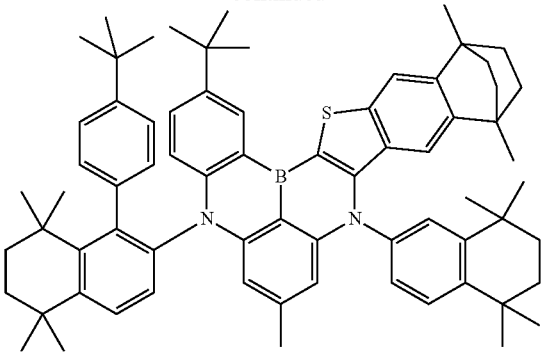 |
| 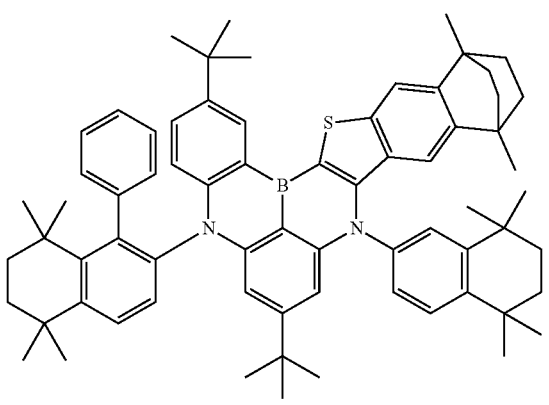 | 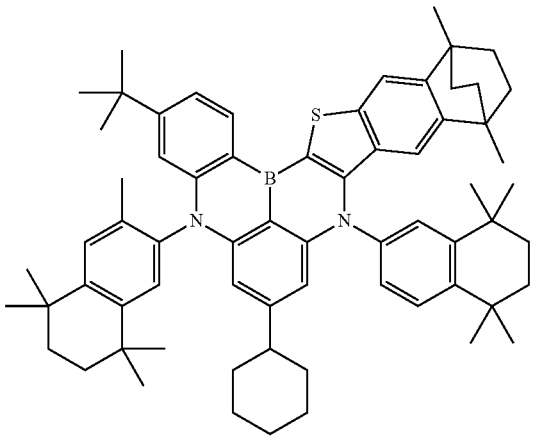 |
| 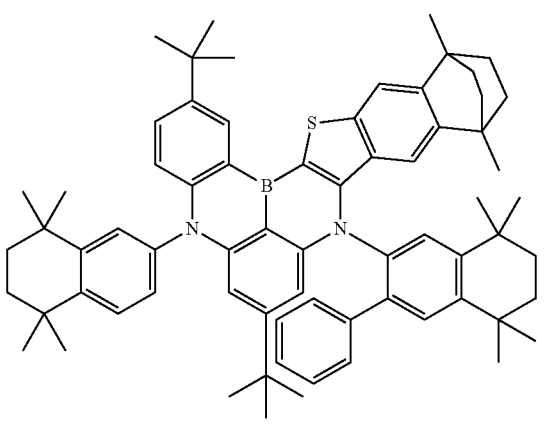 | 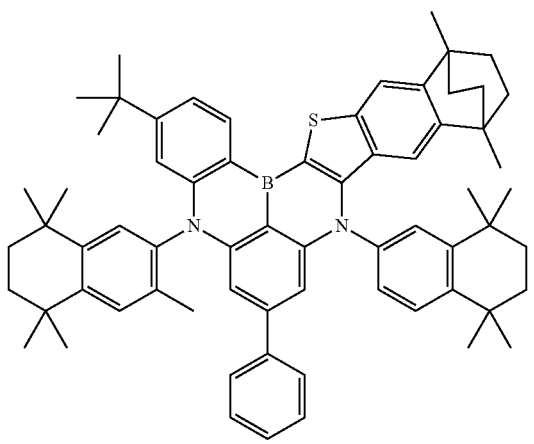 |
| 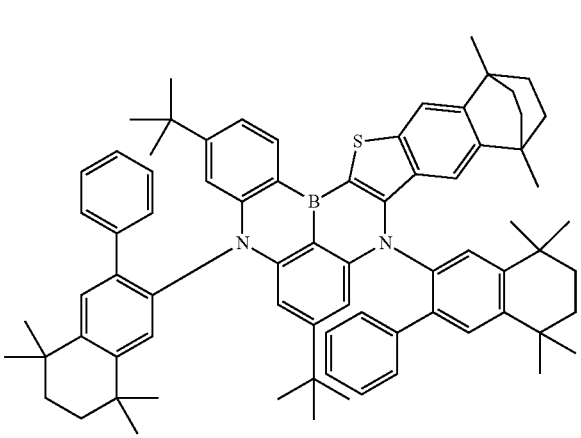 | 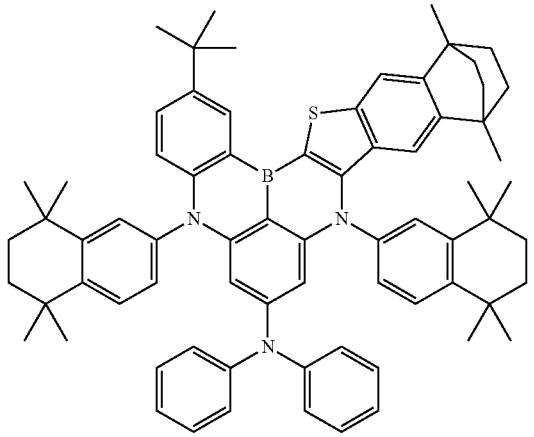 |

1523
-continued
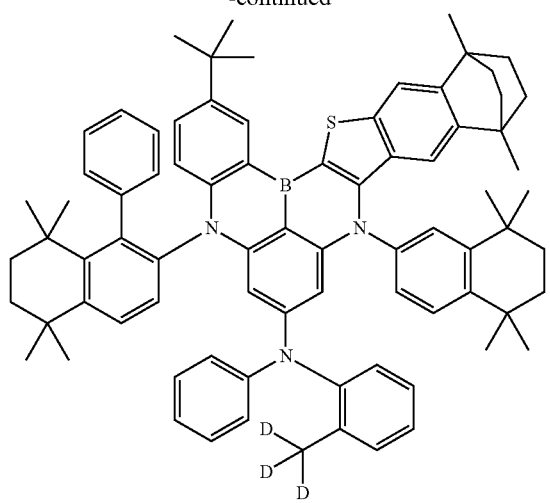
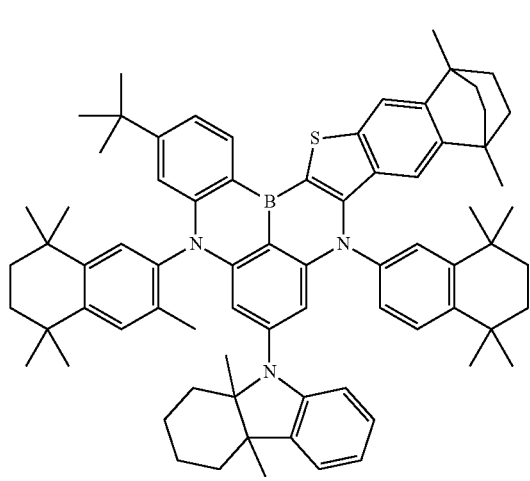
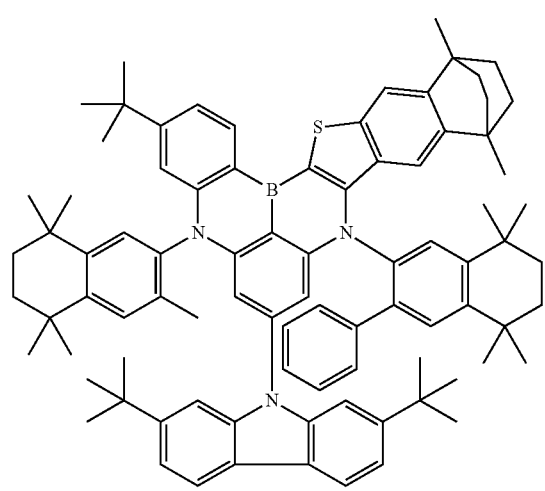
1524
-continued
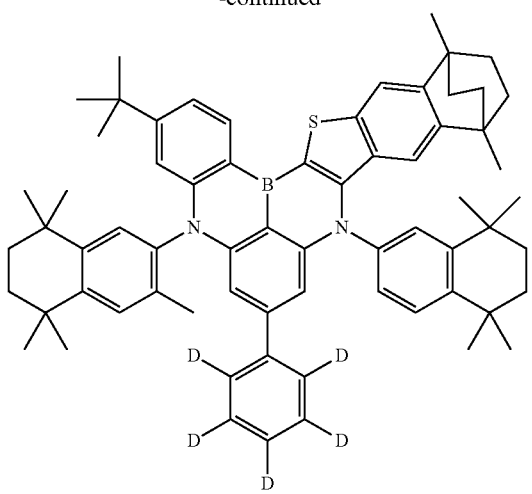
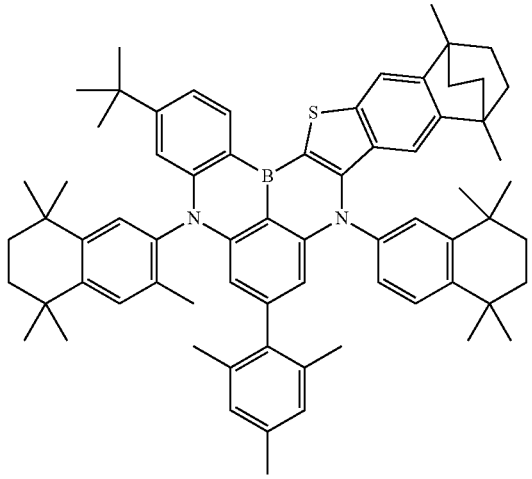
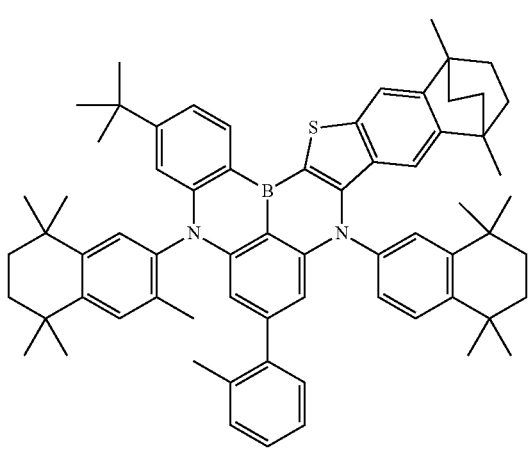

1525
-continued
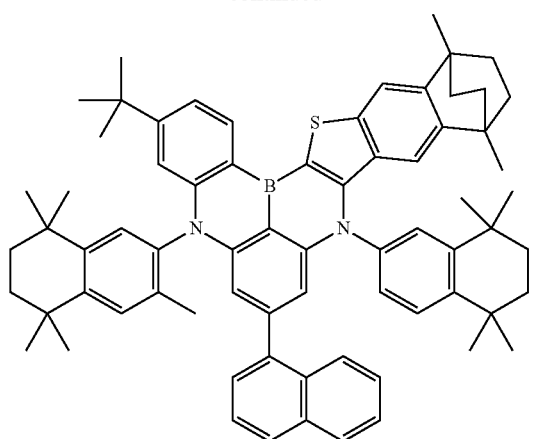
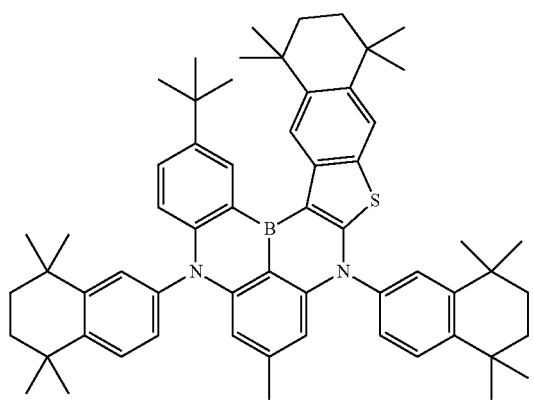
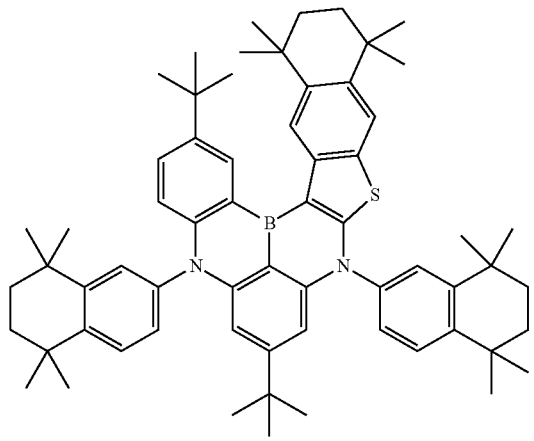
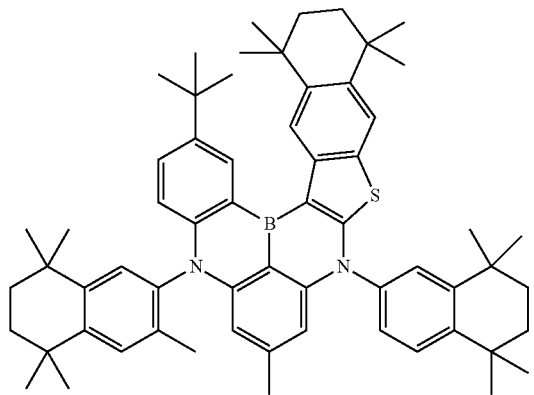
1526
-continued
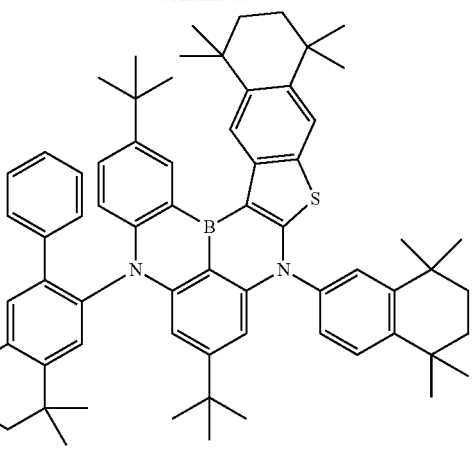
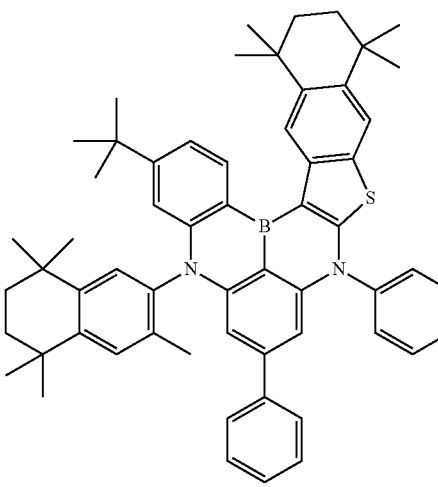
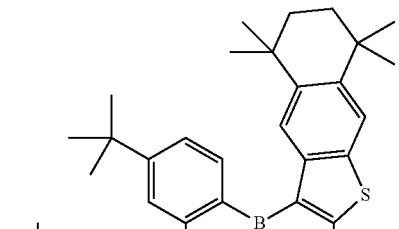
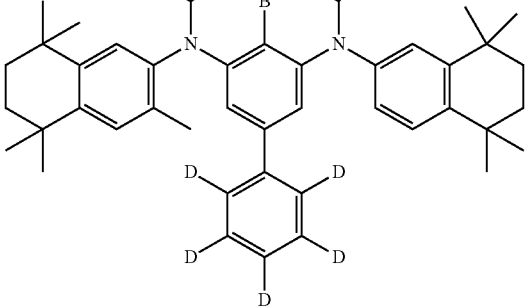

1527
-continued
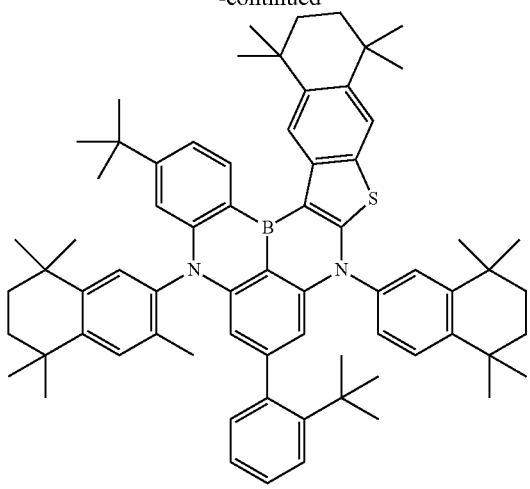
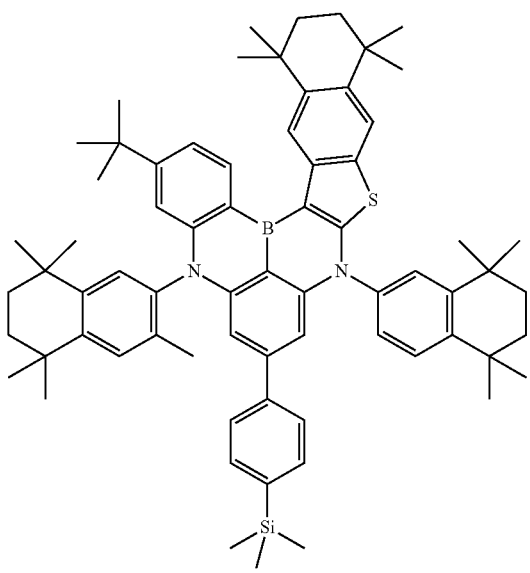
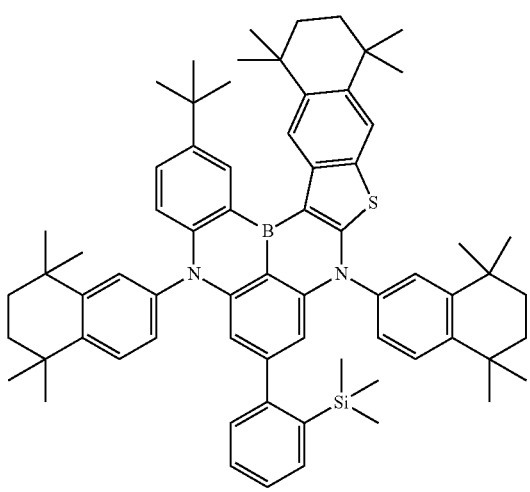
1528
-continued
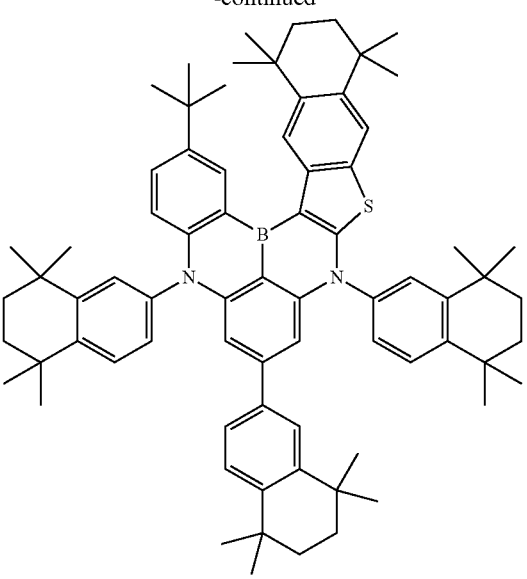
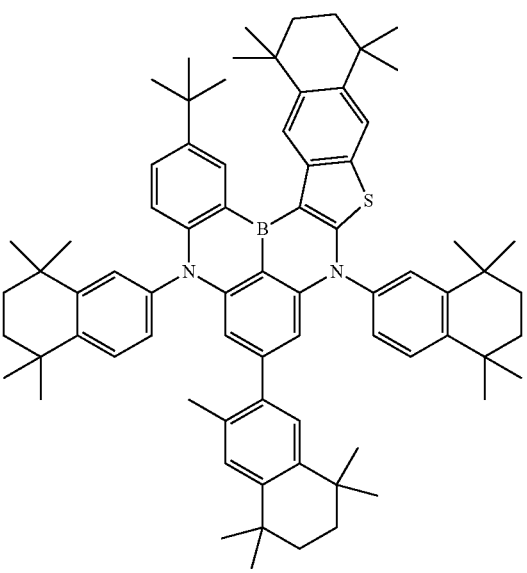
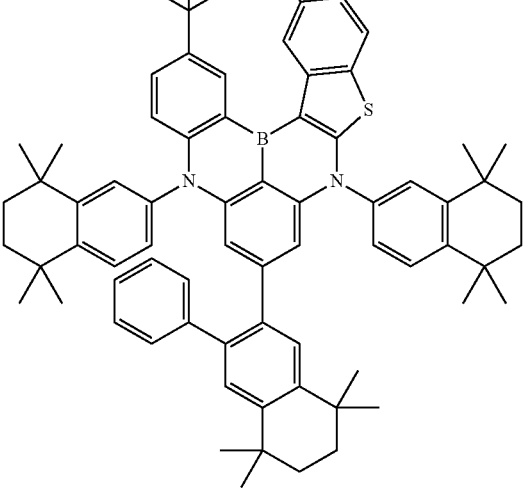

1529
-continued
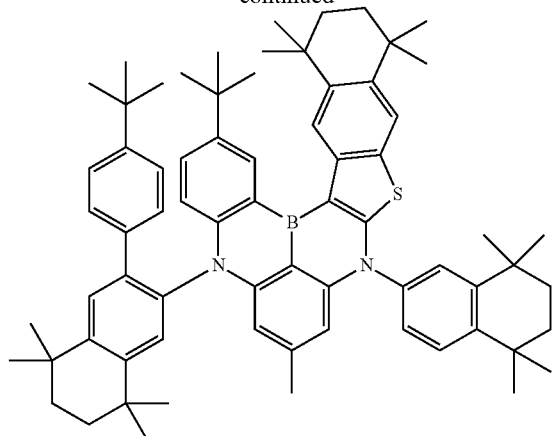
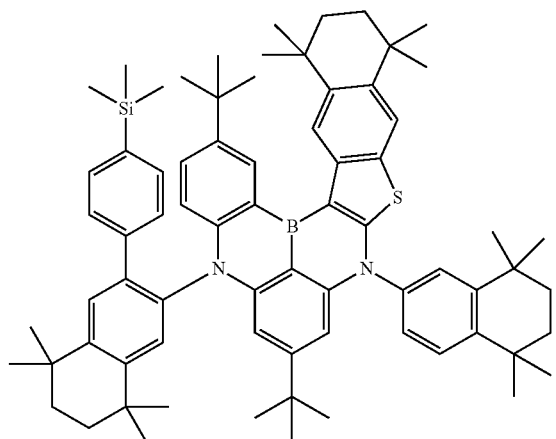
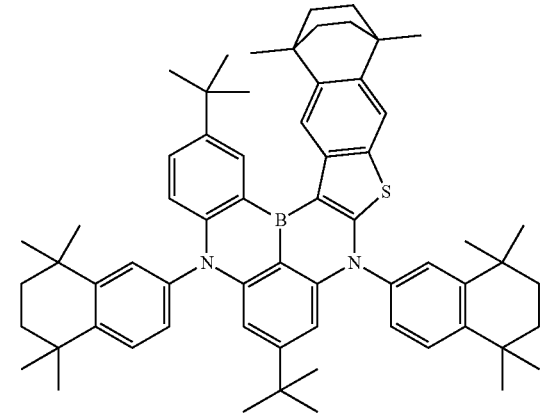
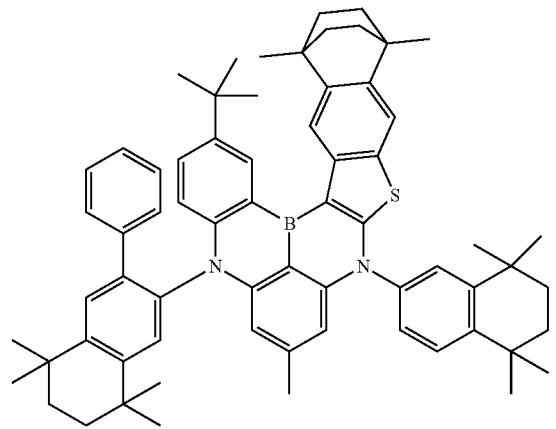
1530
-continued
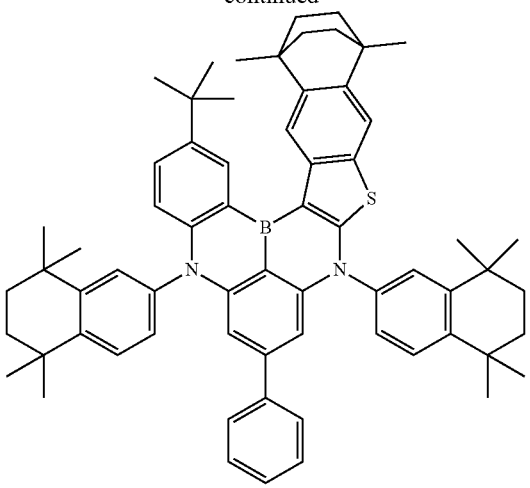
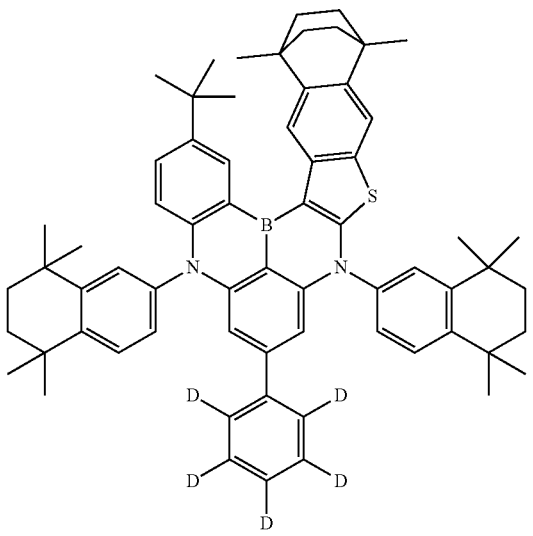
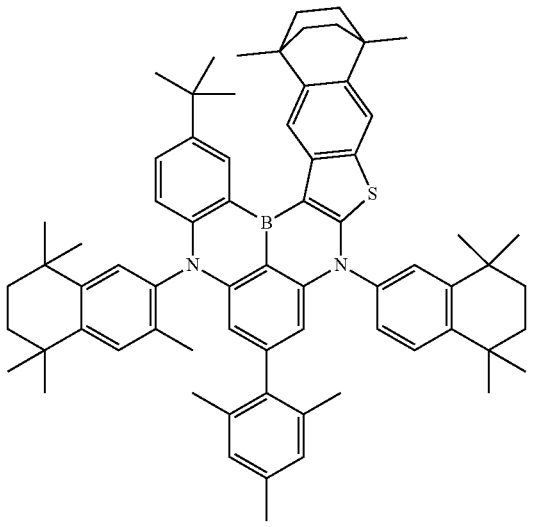

1531
-continued
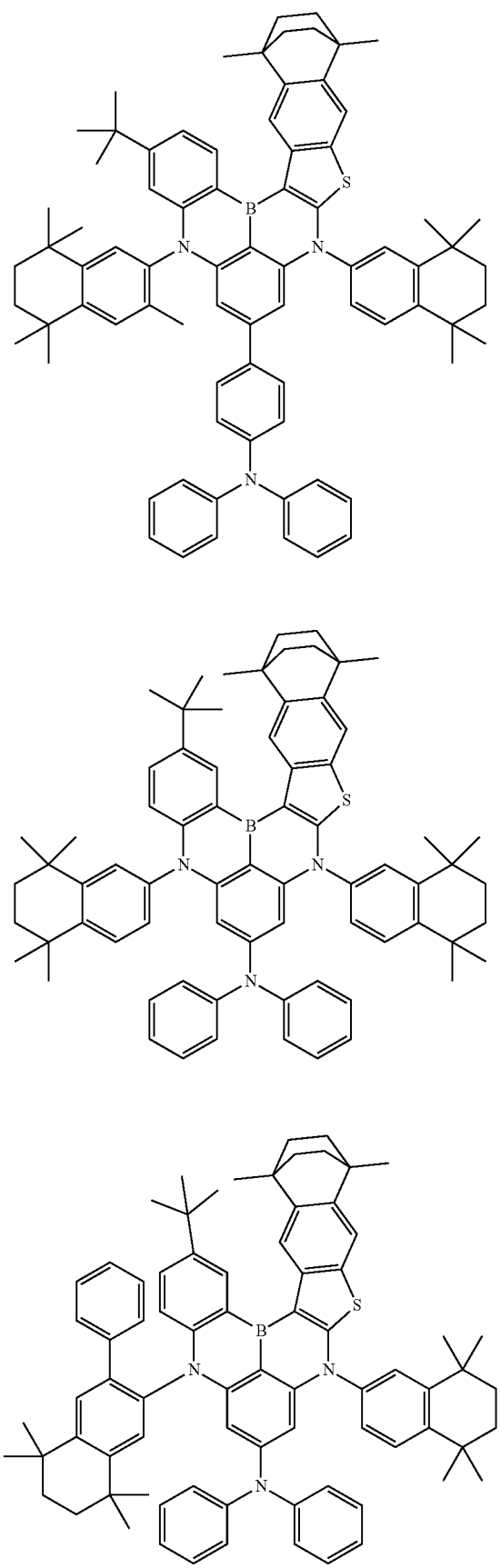
1532
-continued
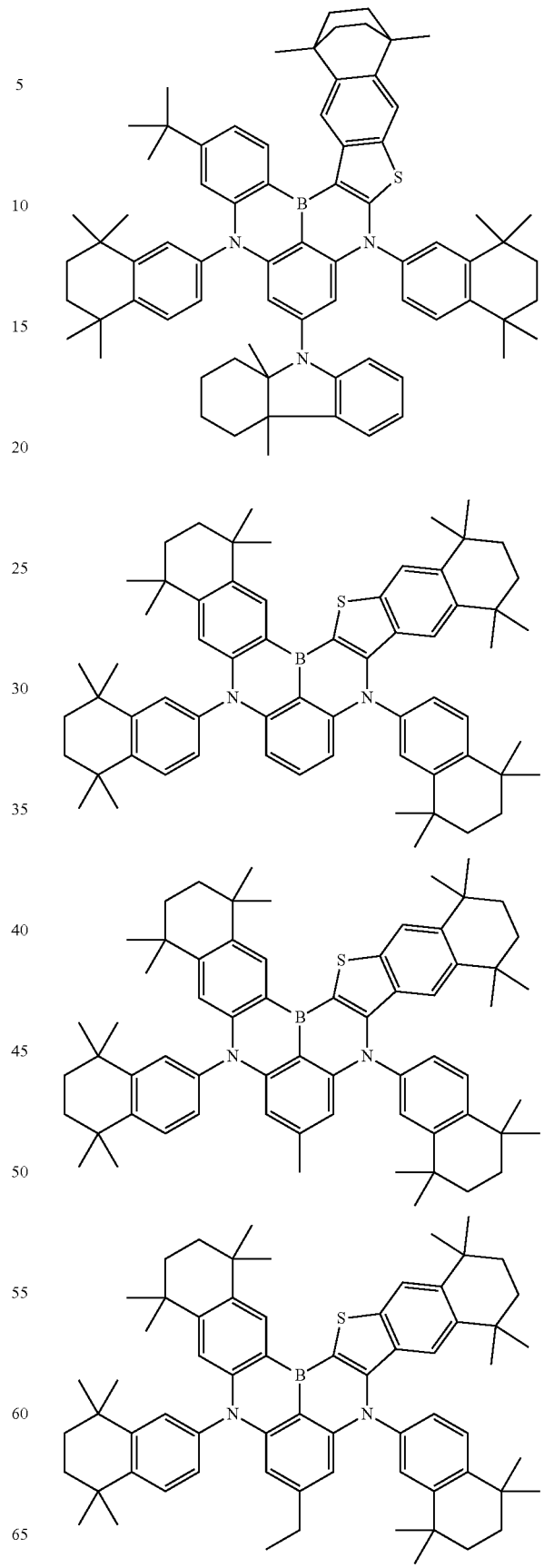

1533
-continued
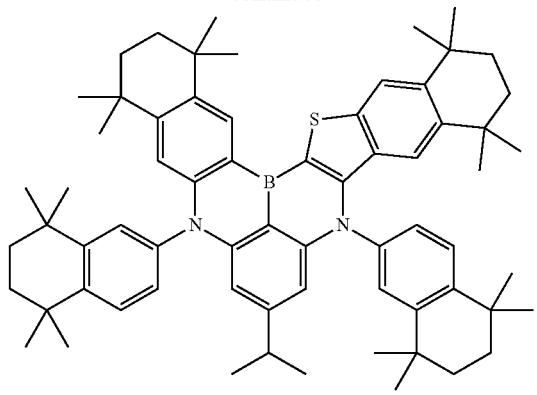
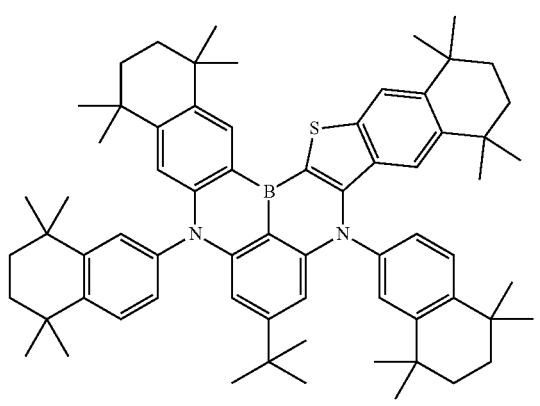
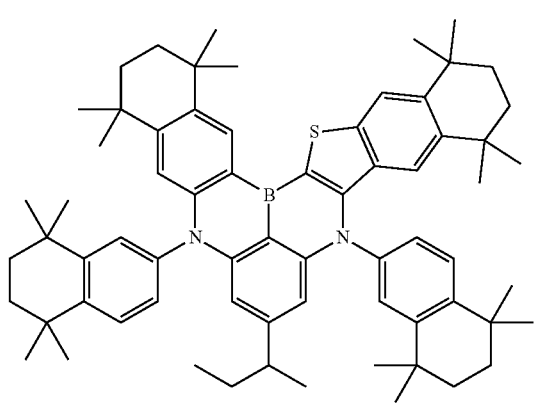
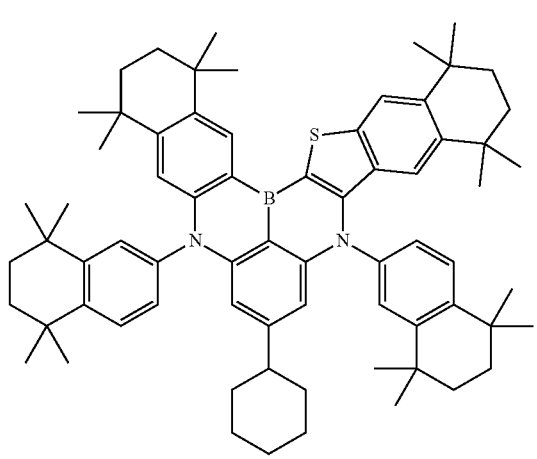
1534
-continued
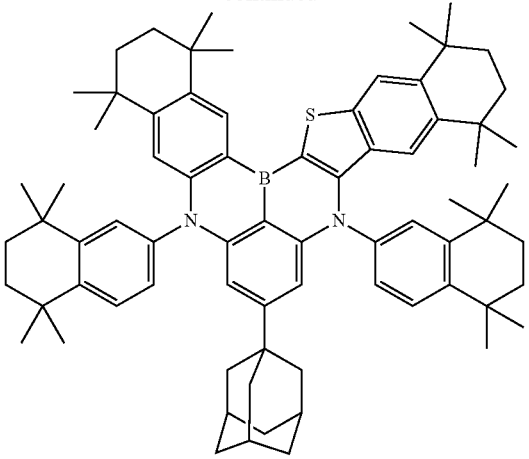
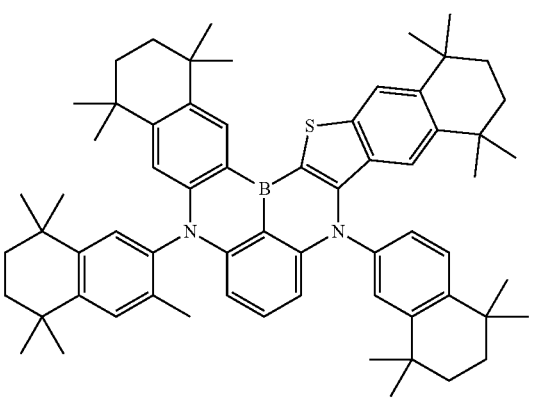
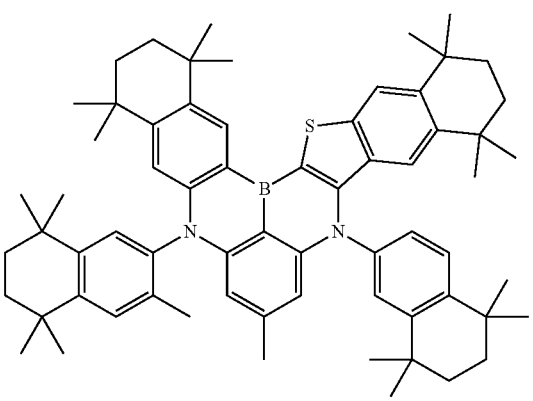
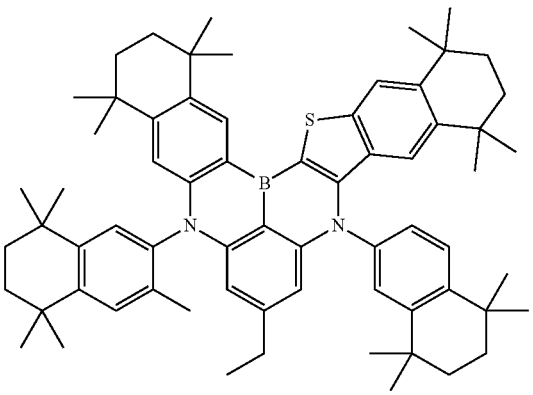

1535
-continued
1536
-continued
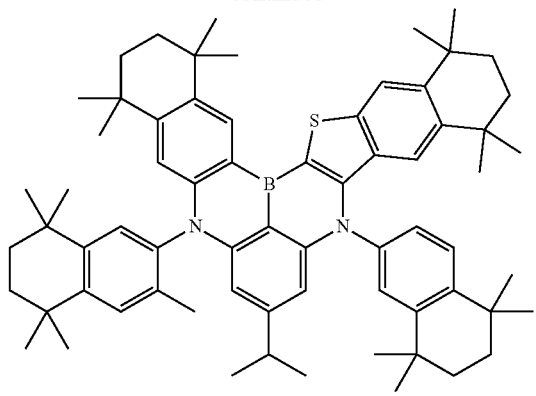
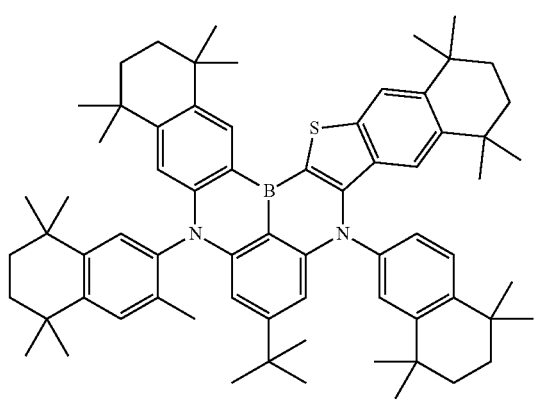
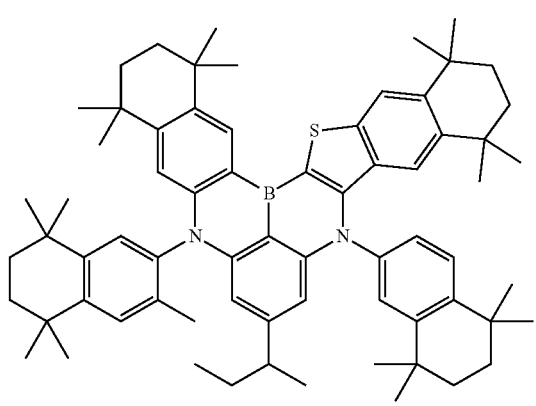
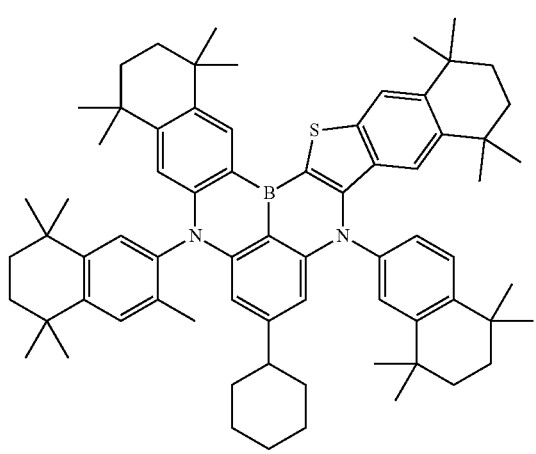
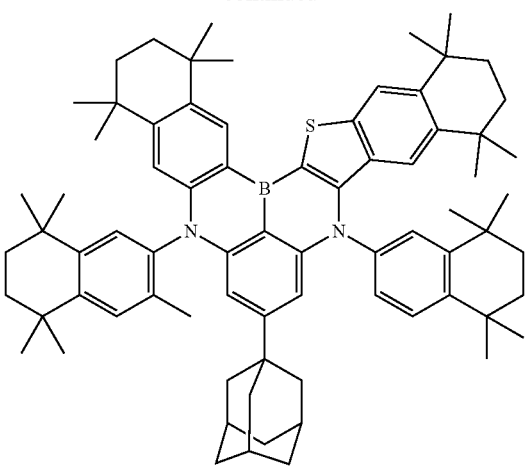
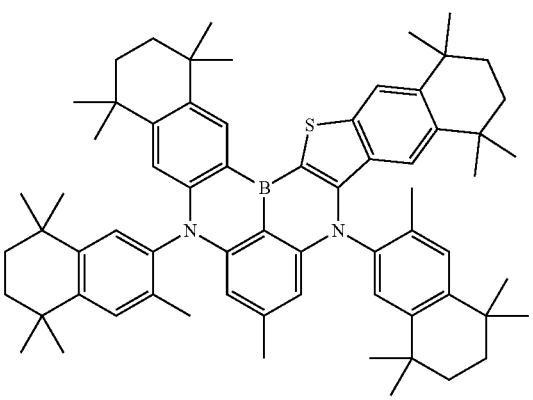
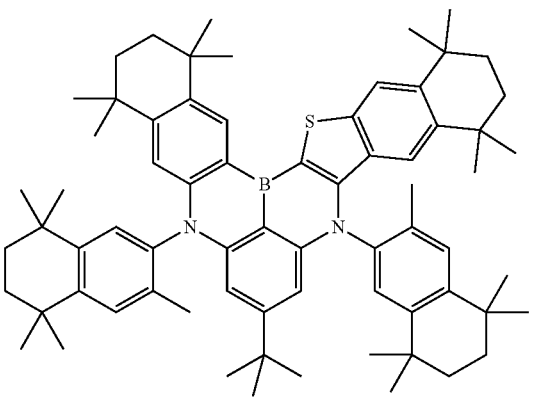
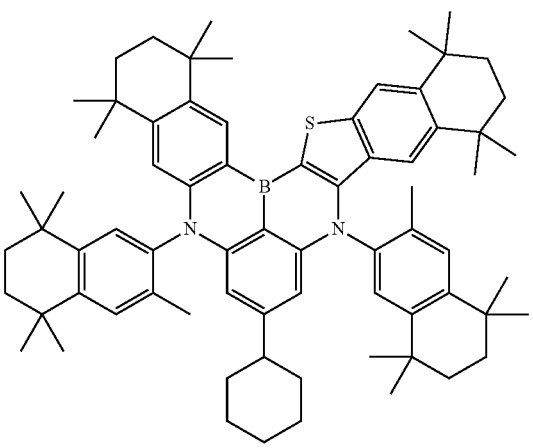

1537
-continued
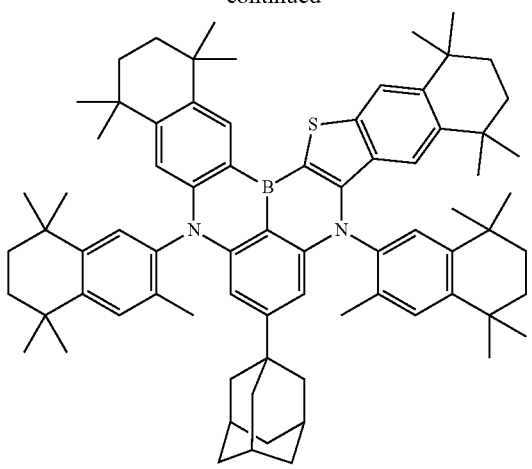
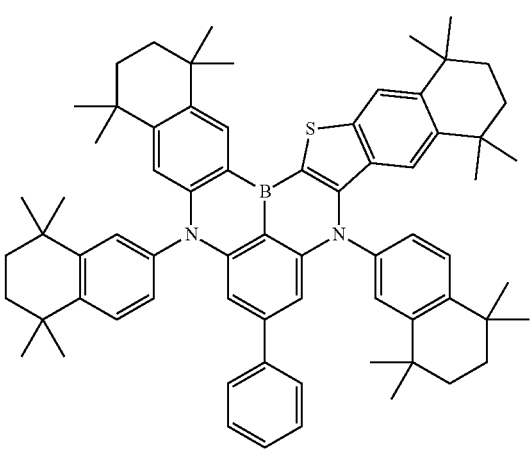
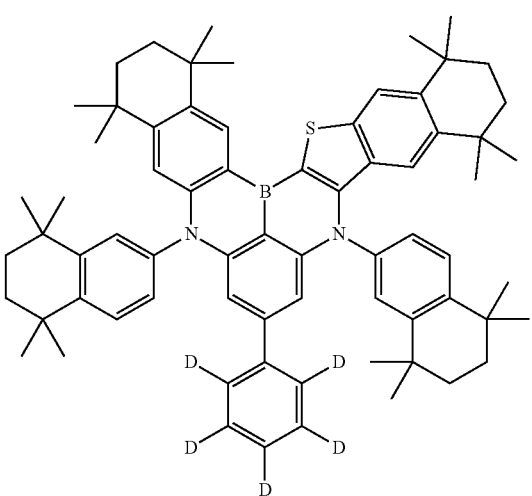
1538
-continued
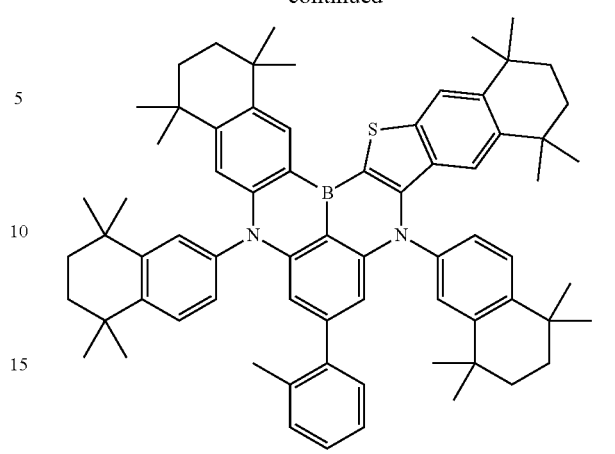
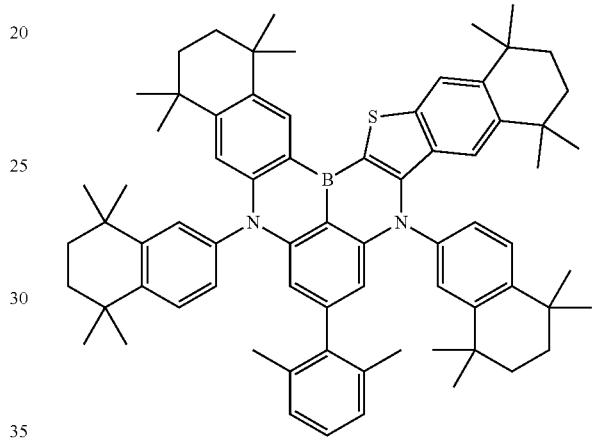
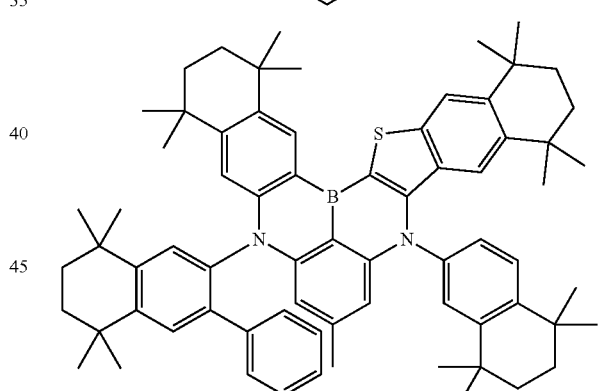
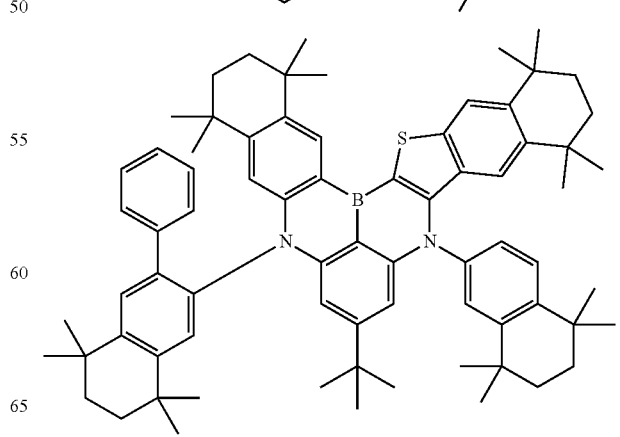

1539
-continued
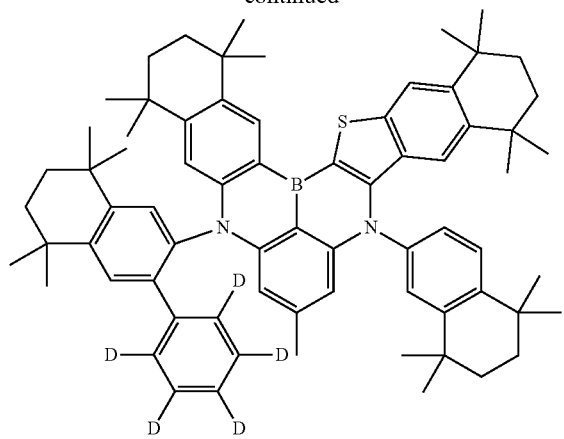
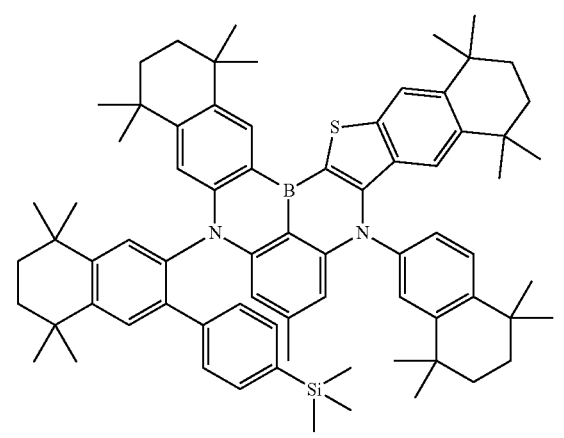
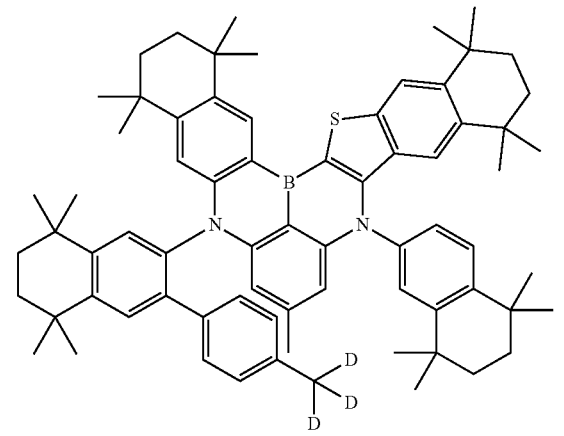
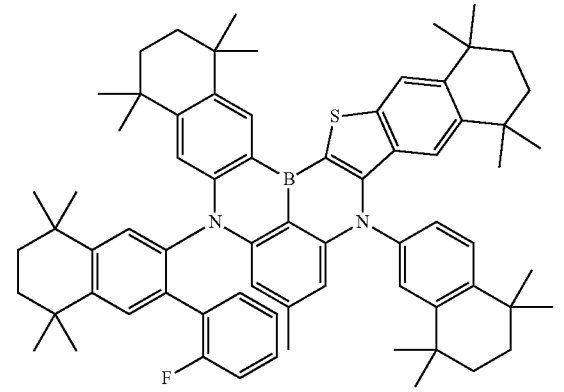
1540
-continued
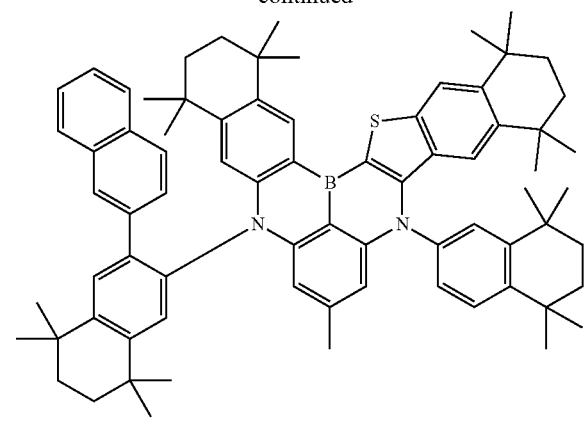
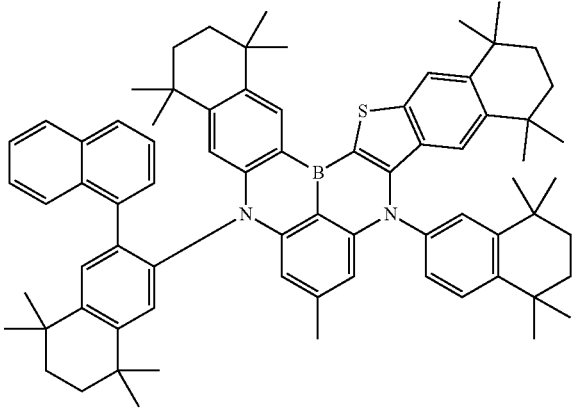
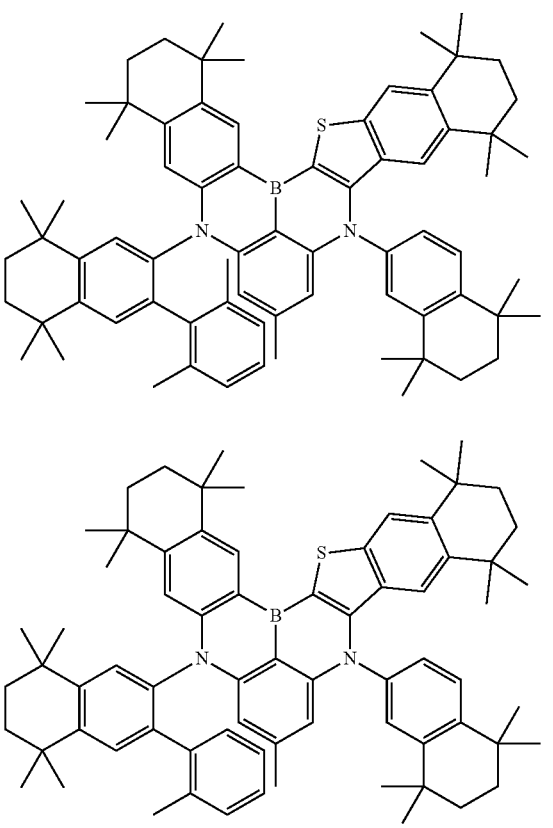

1541
-continued
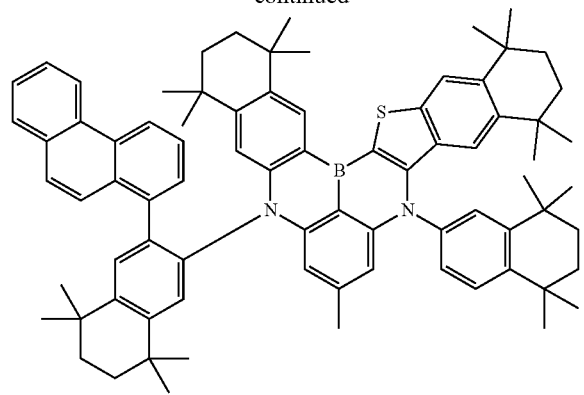
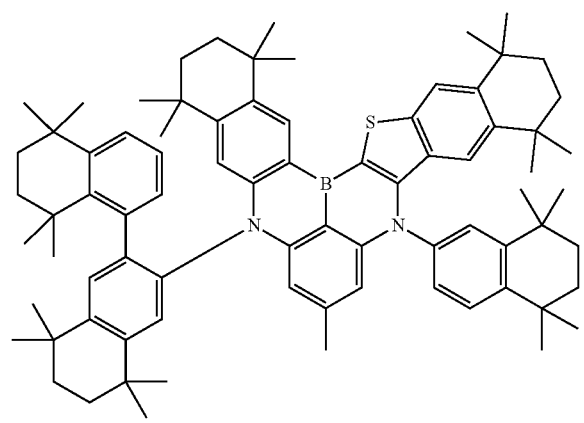
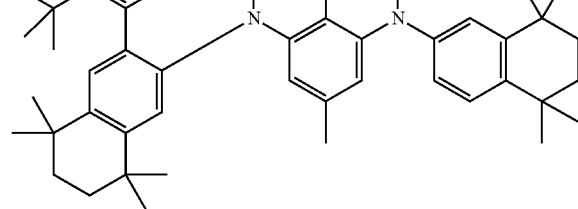
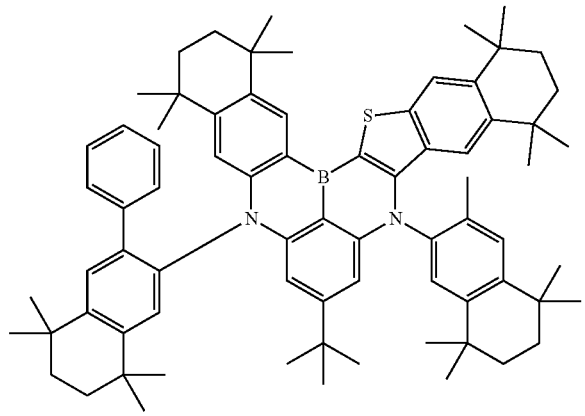
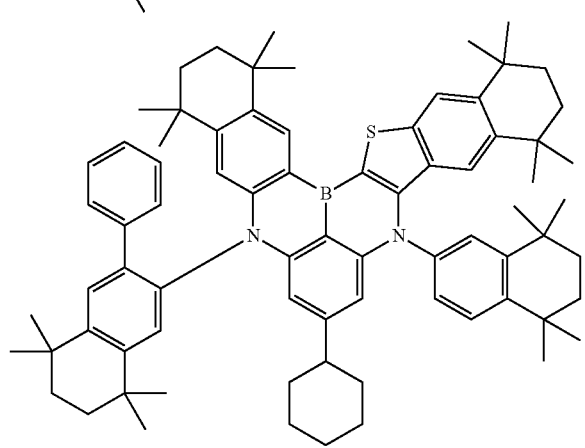
1542
-continued
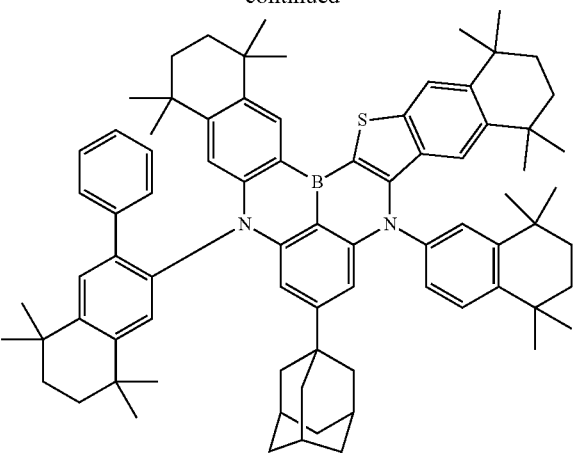
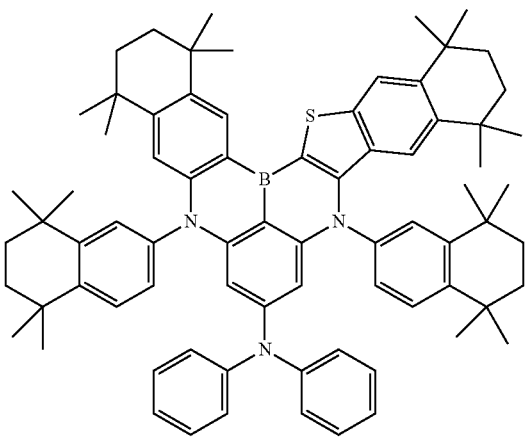
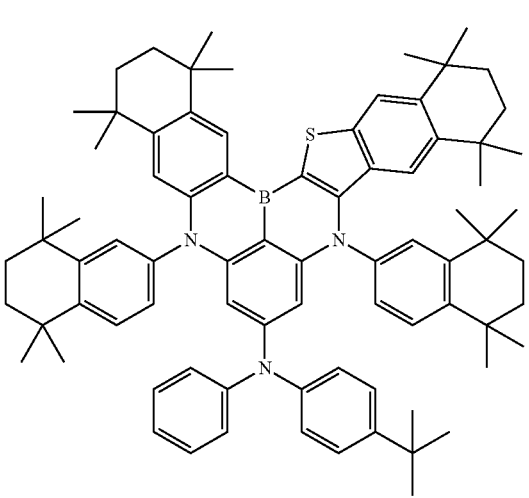

1543
-continued
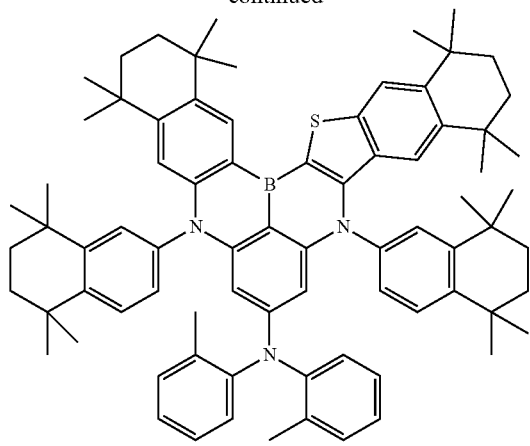
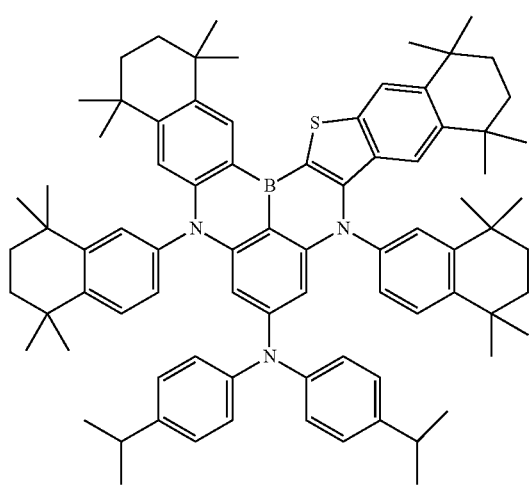
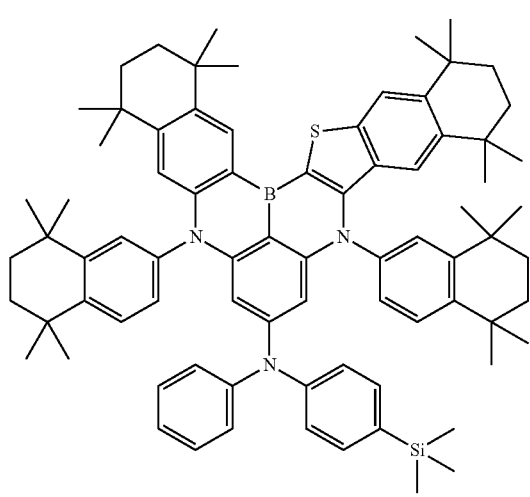
1544
-continued
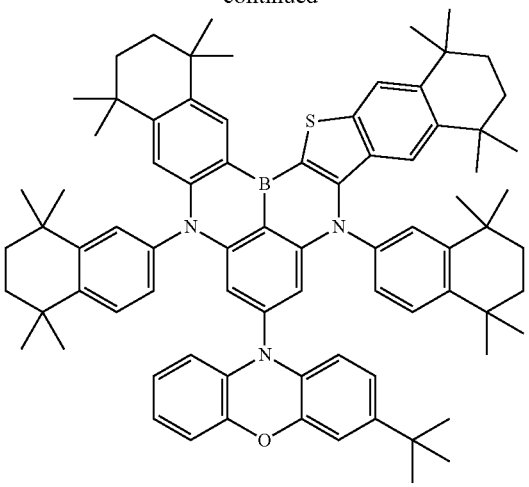
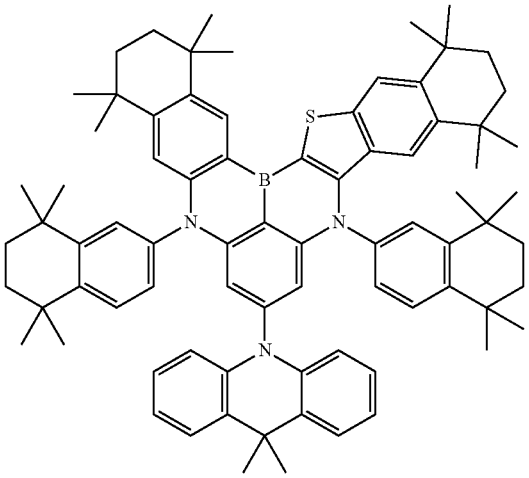
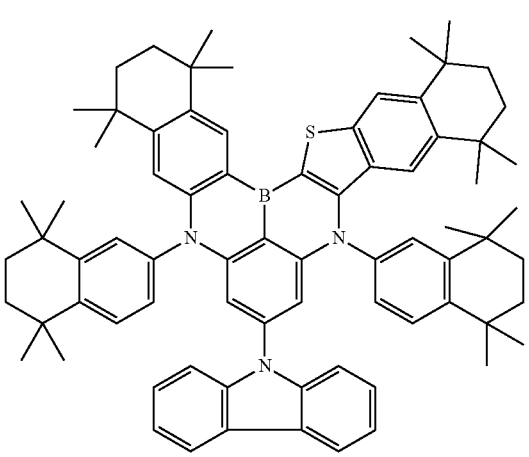

1545
-continued
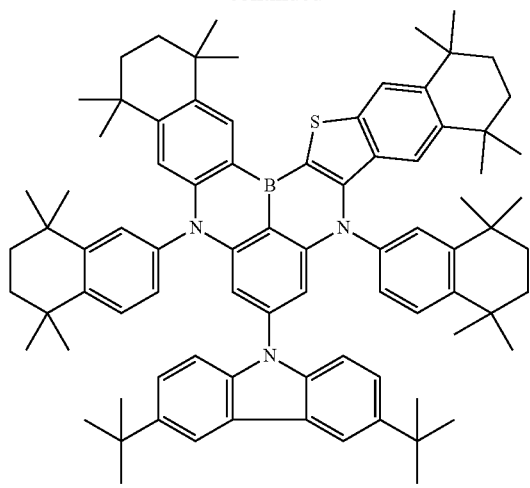
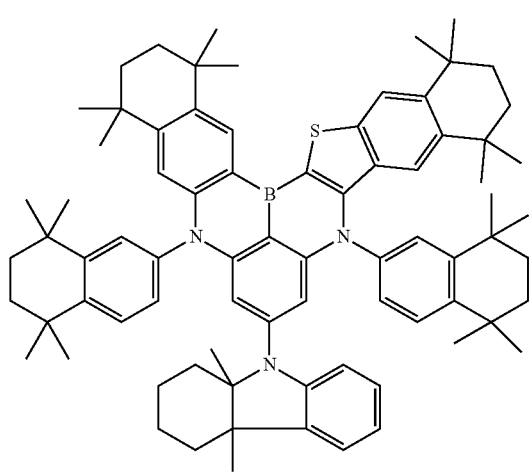
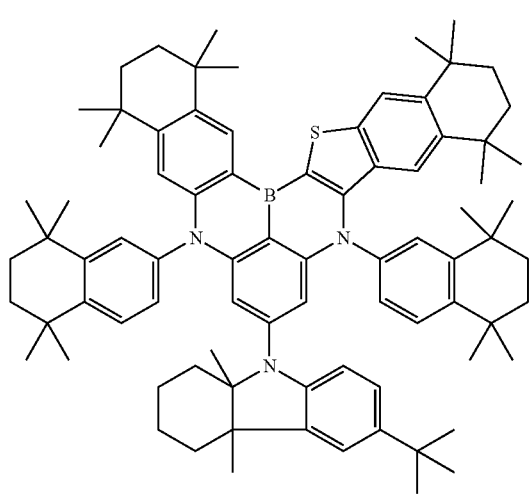
1546
-continued
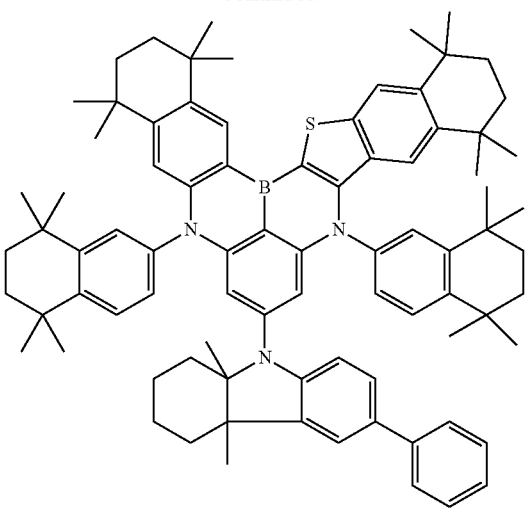
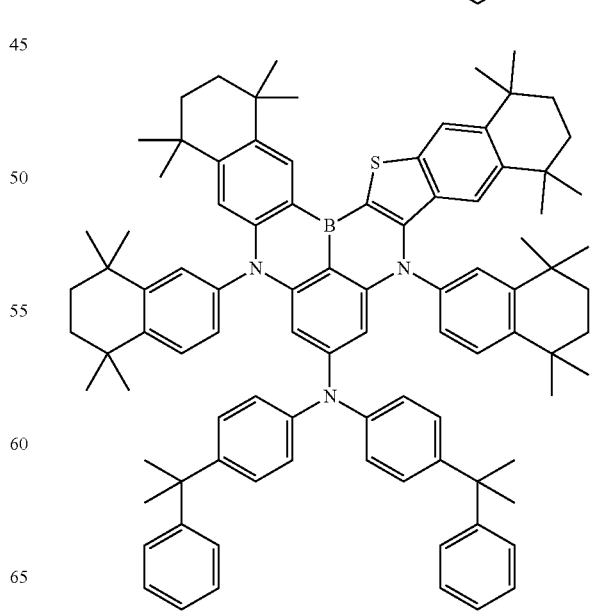

1547
-continued
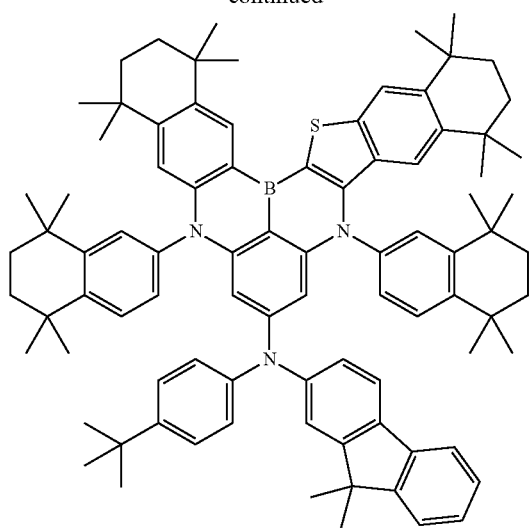
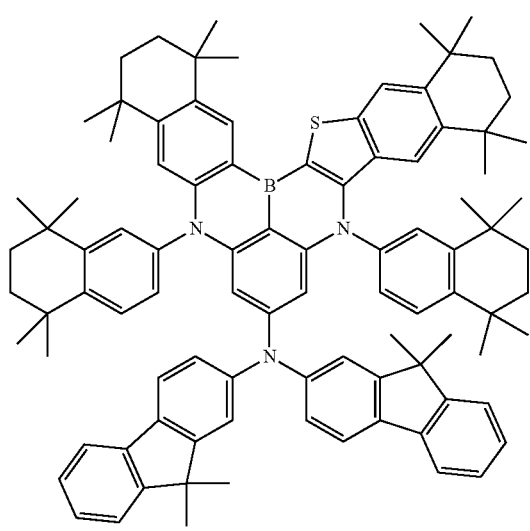
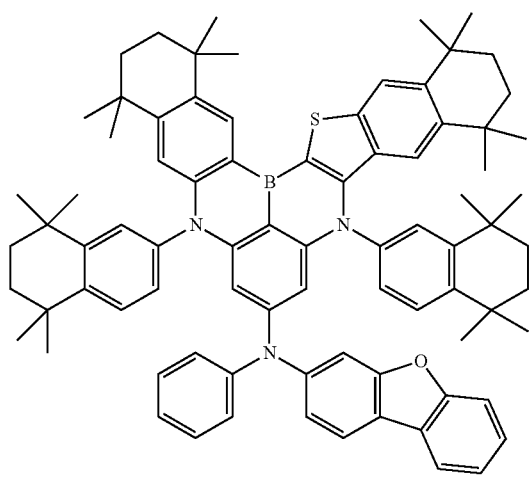
1548
-continued
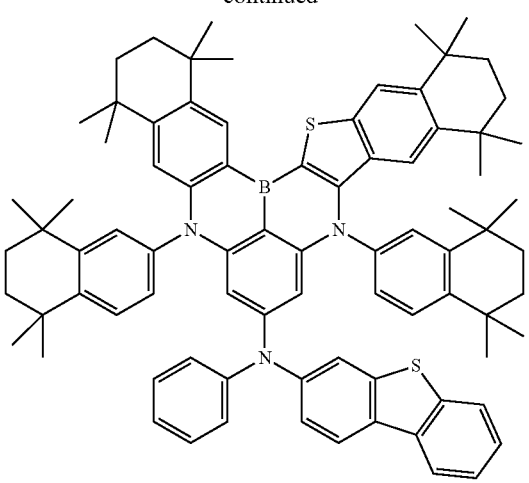
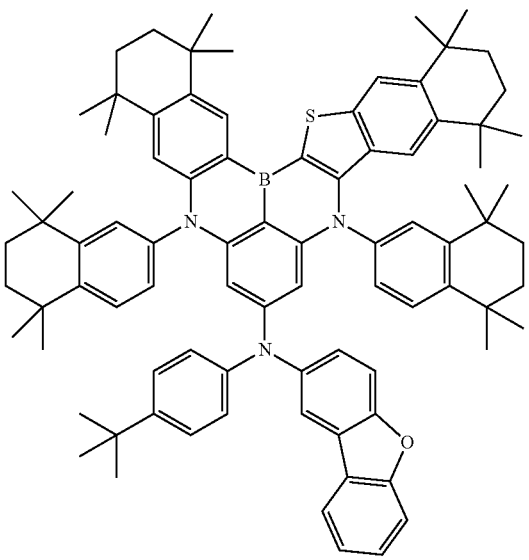
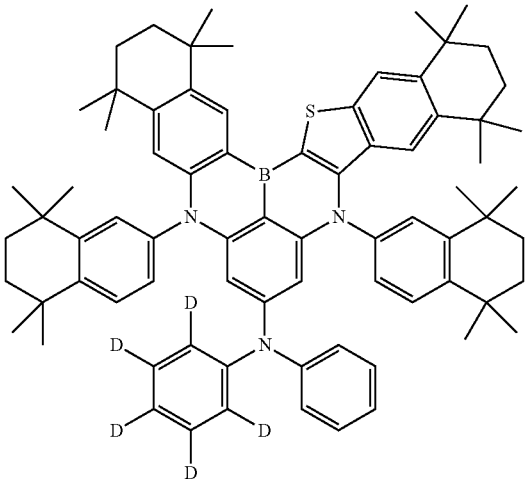

1549
-continued
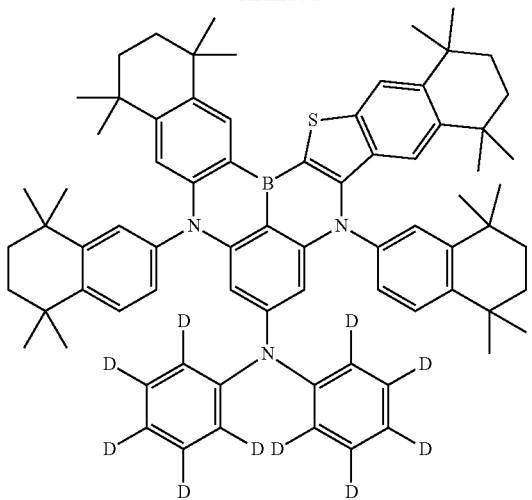
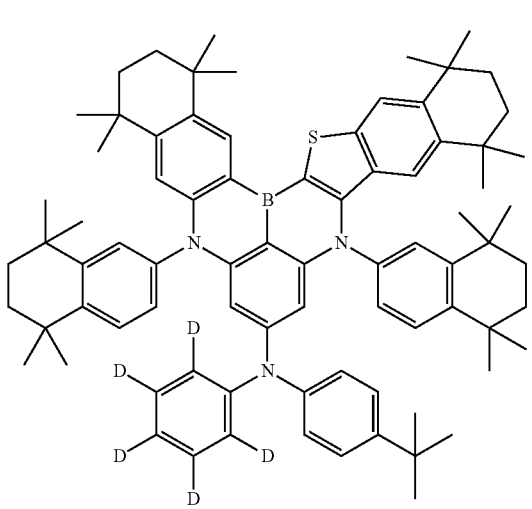
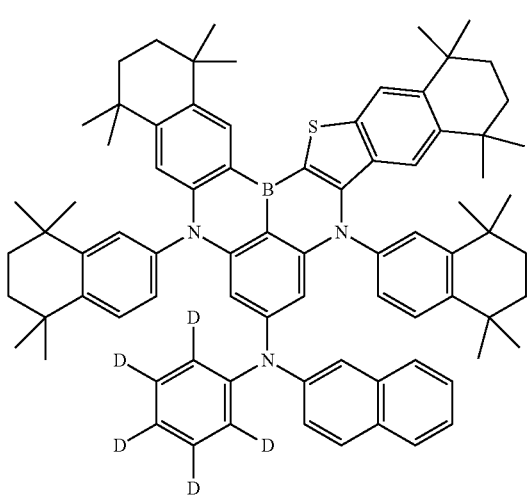
1550
-continued
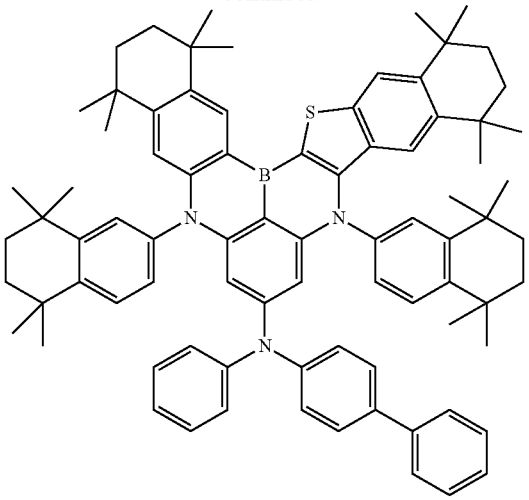
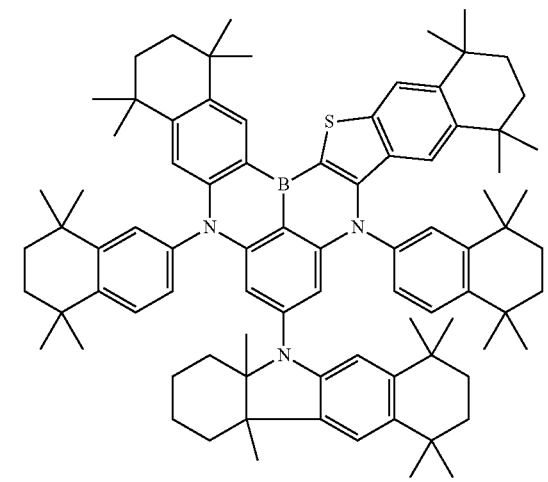
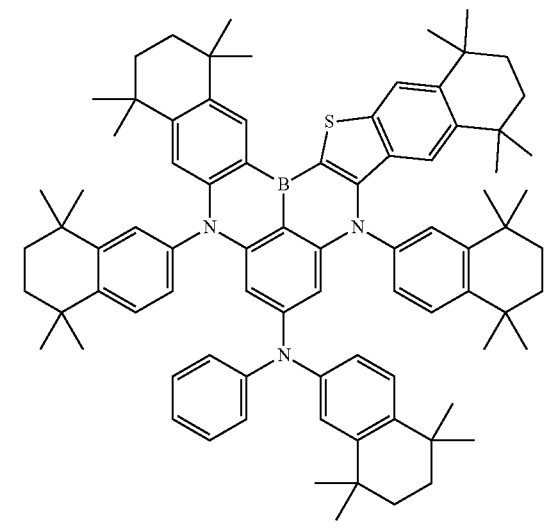

1551
-continued
1552
-continued
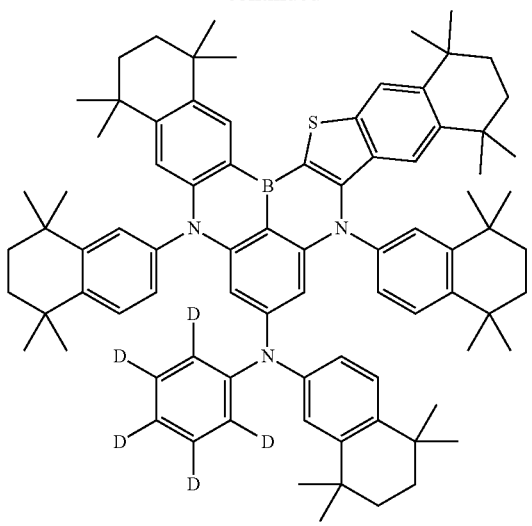
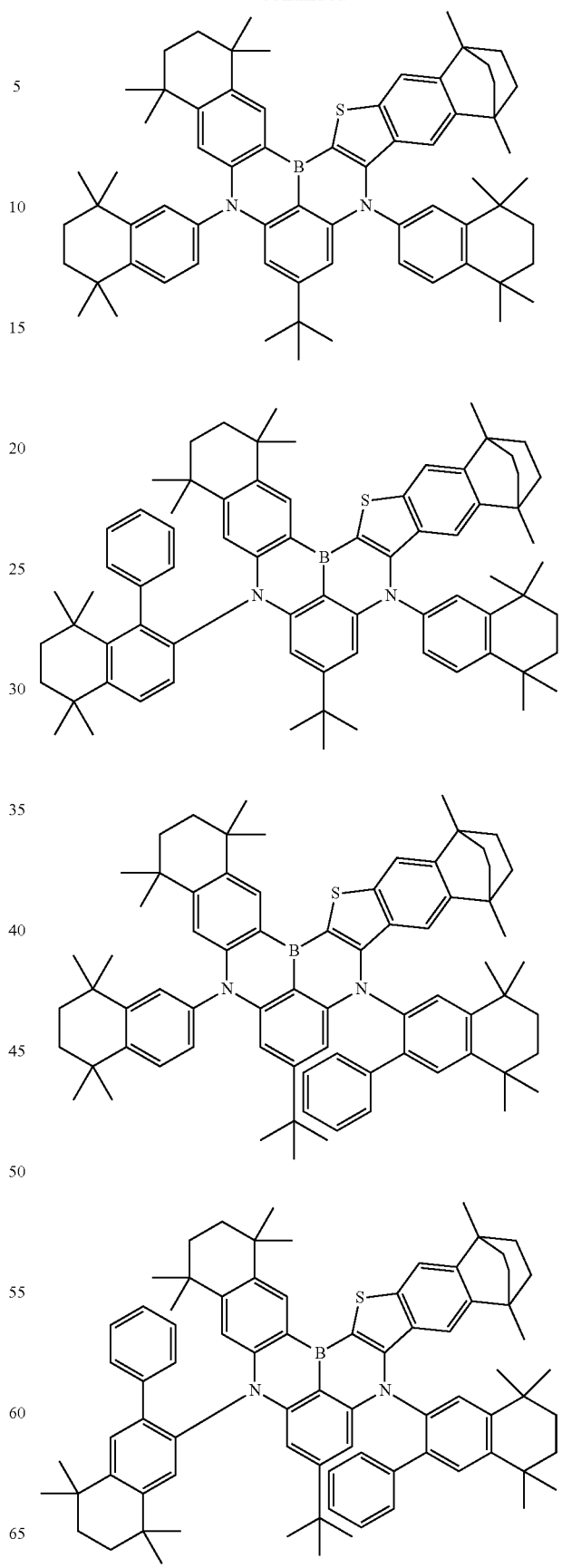

1553
-continued
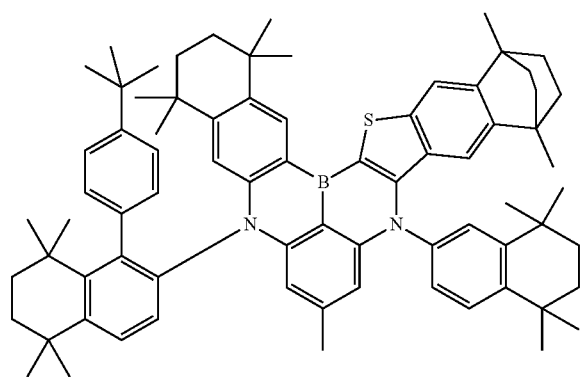
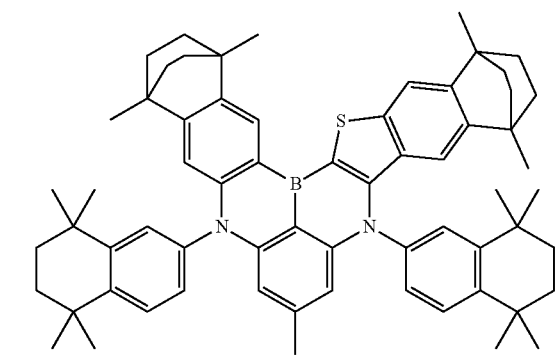
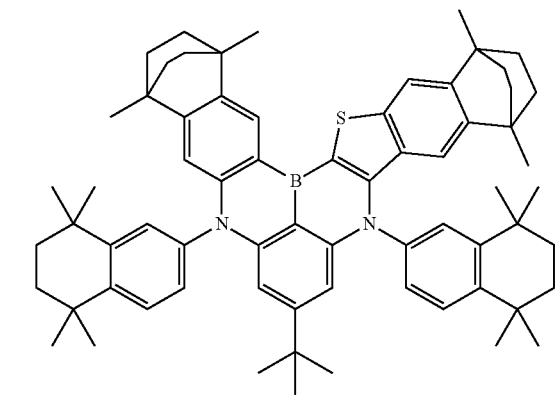
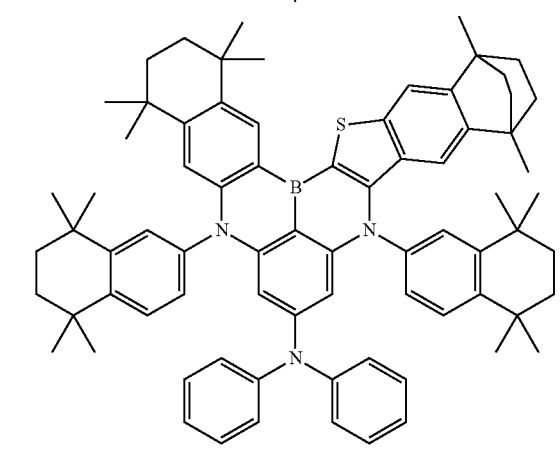
1554
-continued
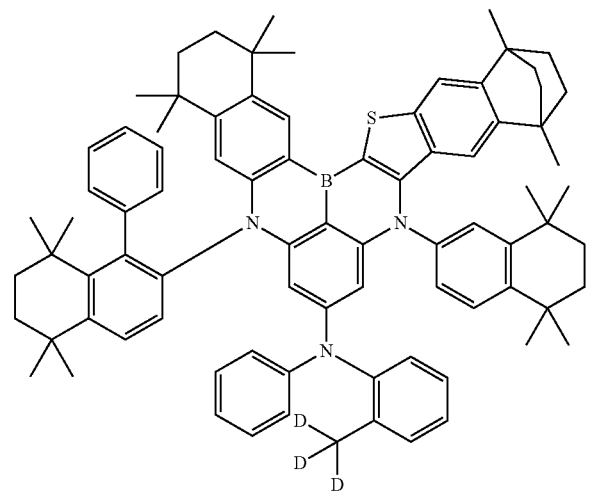
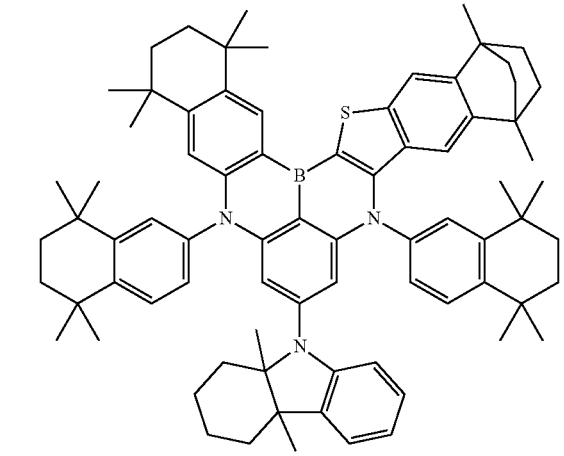
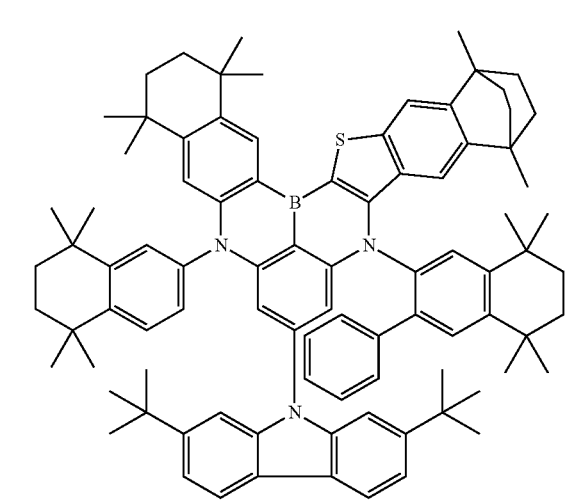

1555
-continued
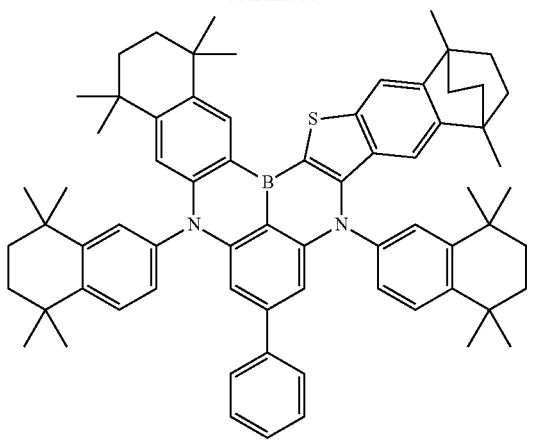
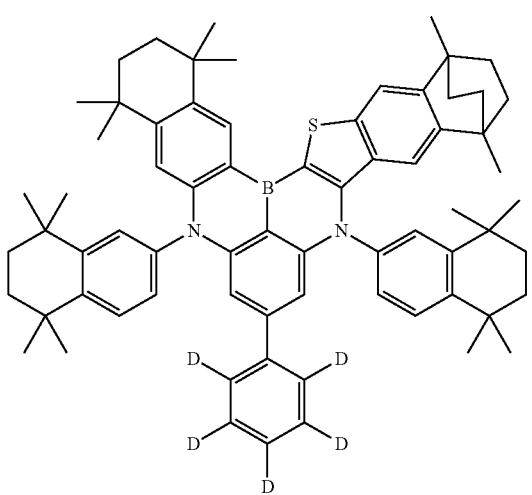
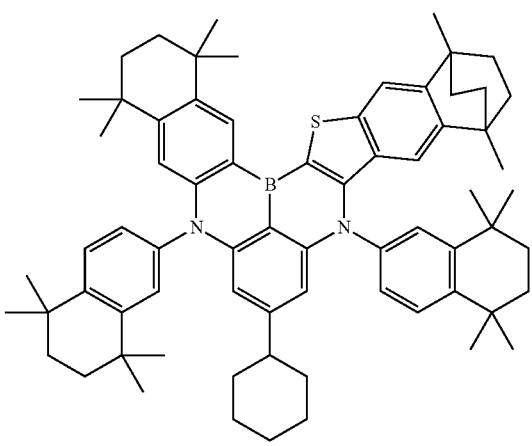
1556
-continued
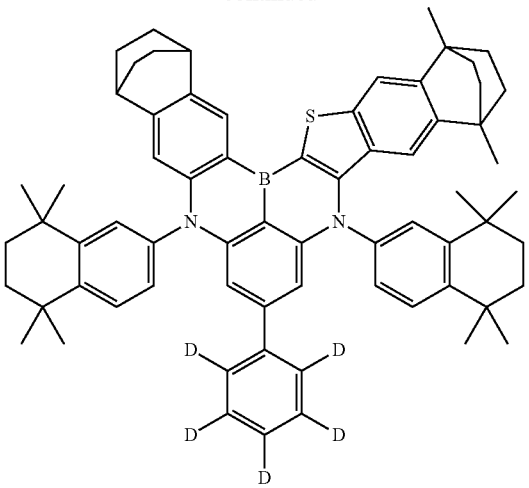
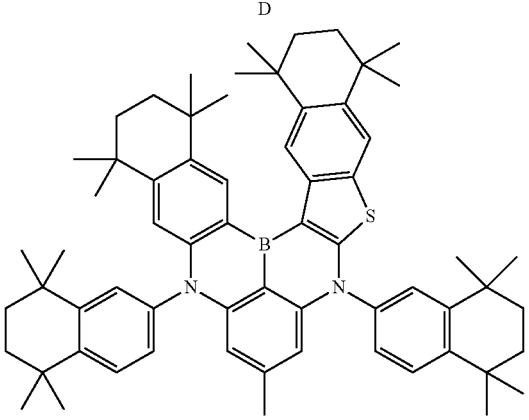
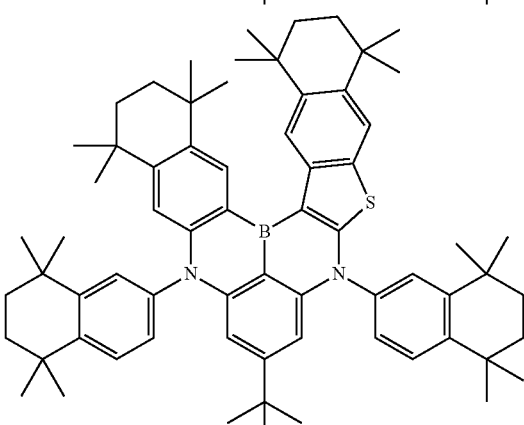
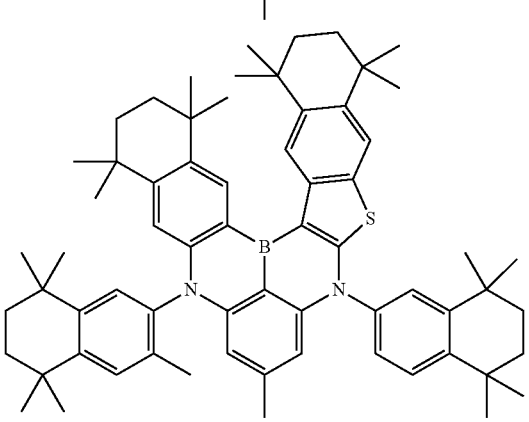

1557
-continued
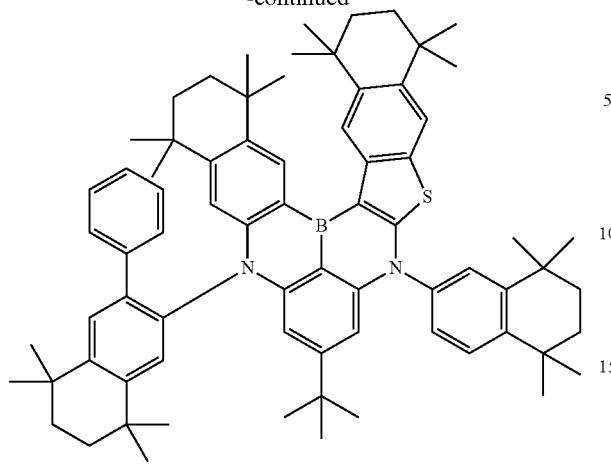
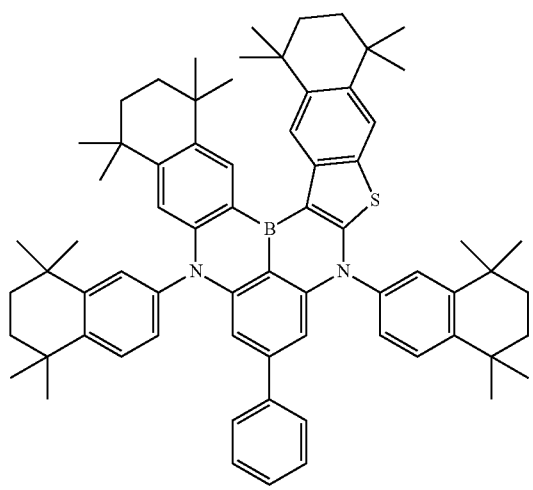
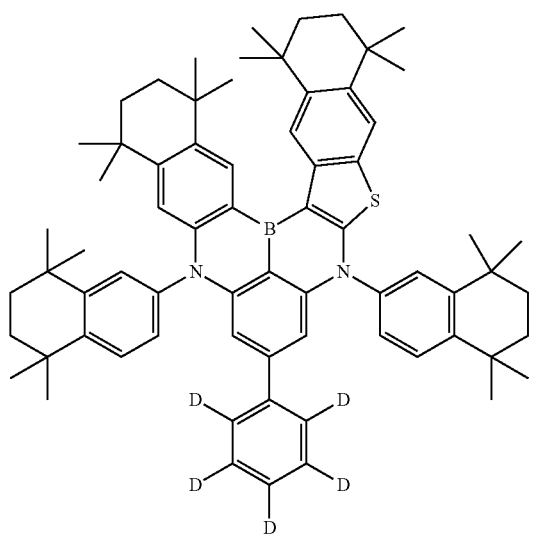
1558
-continued
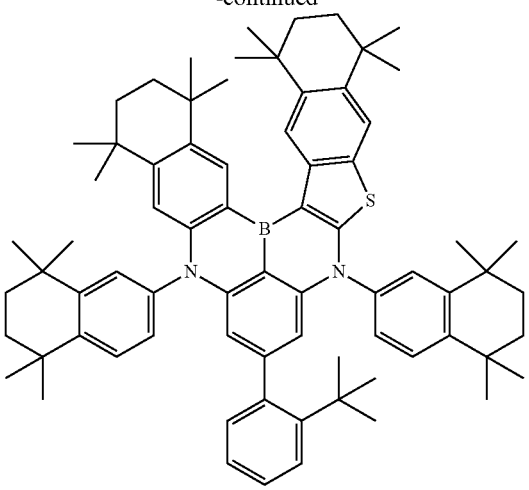
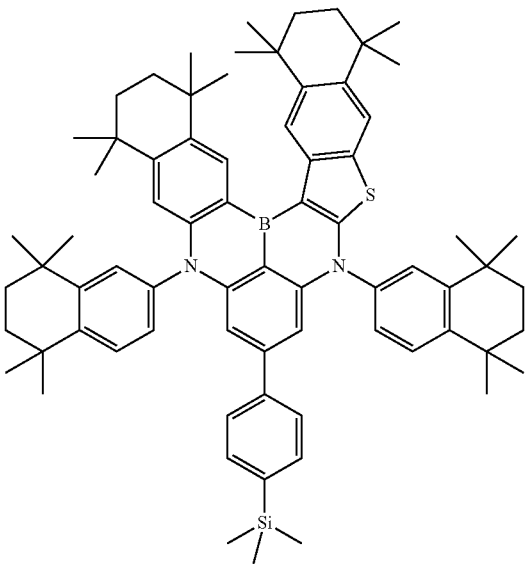
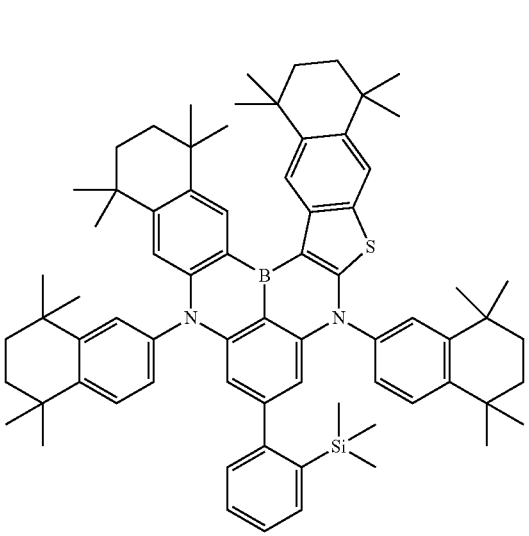

1559
-continued
1560
-continued
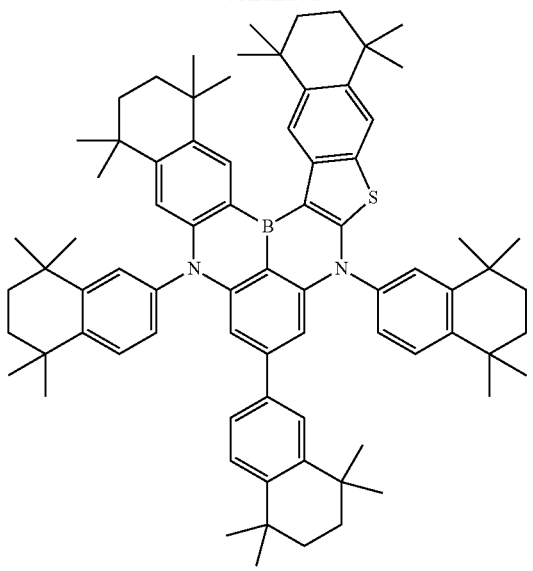
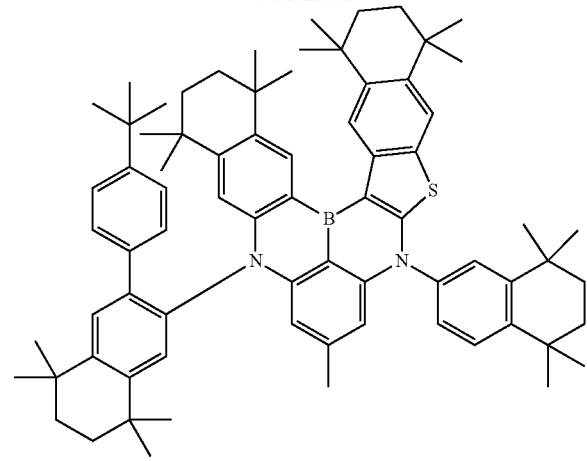
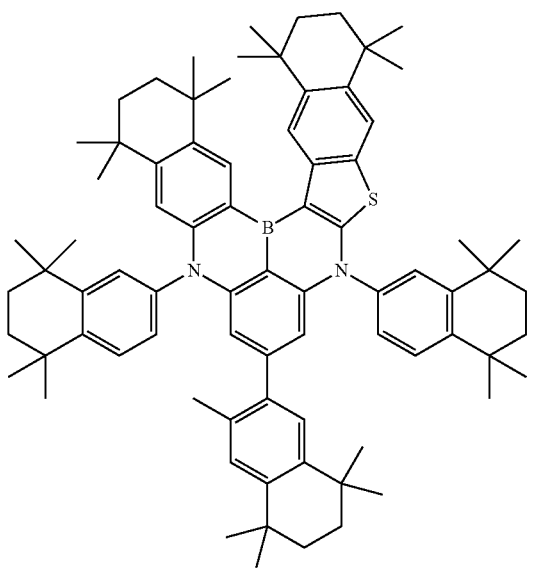
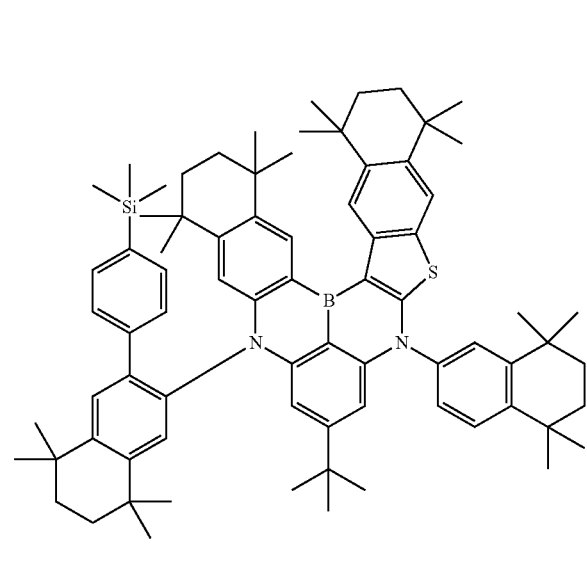
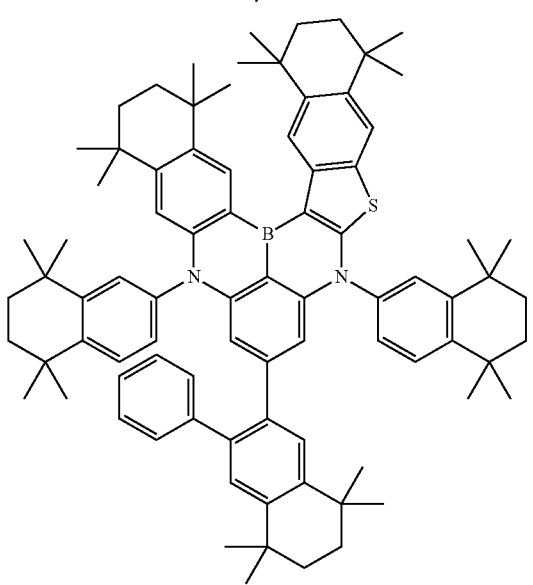
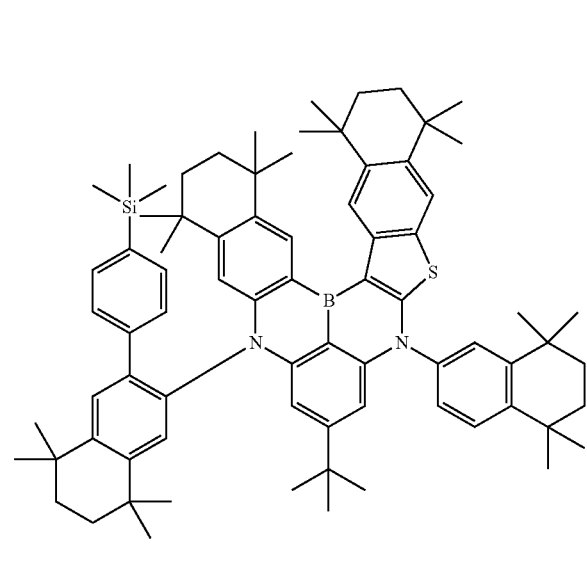

| 1561 -continued | 1562 -continued |
|---|---|
| 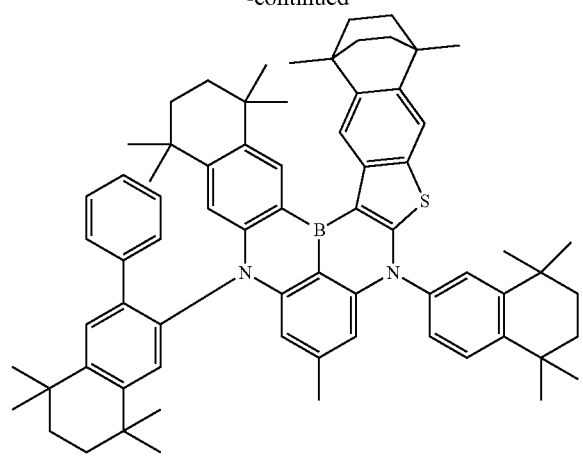 | 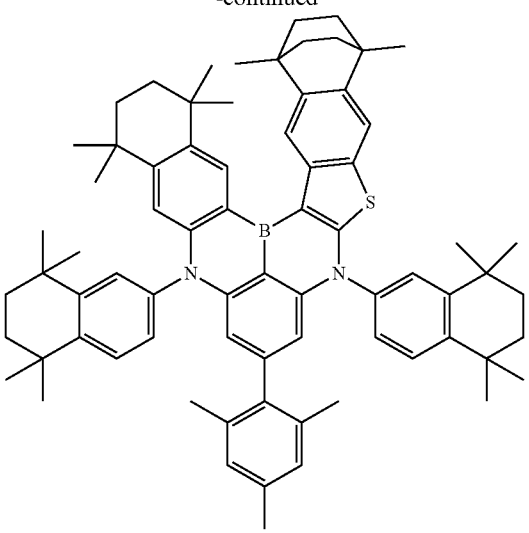 |
| 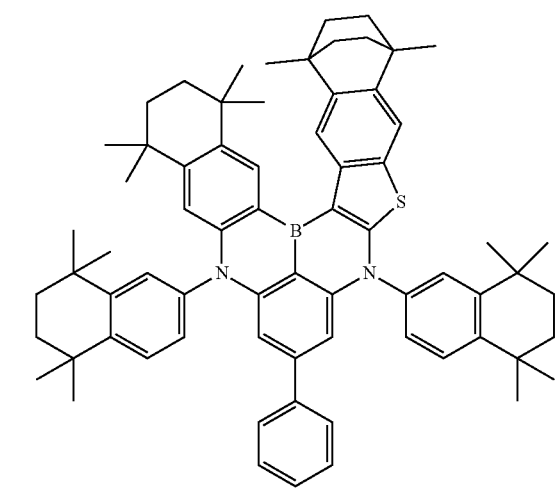 | 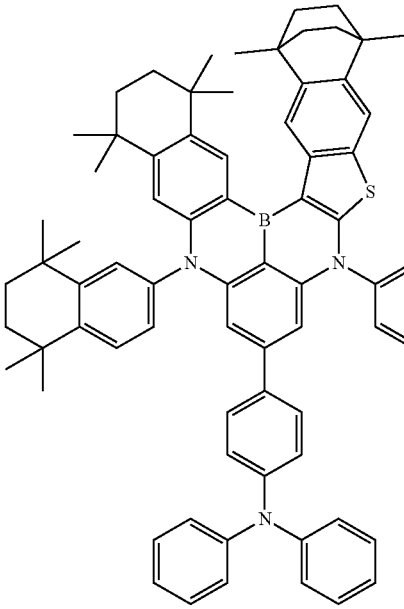 |
| 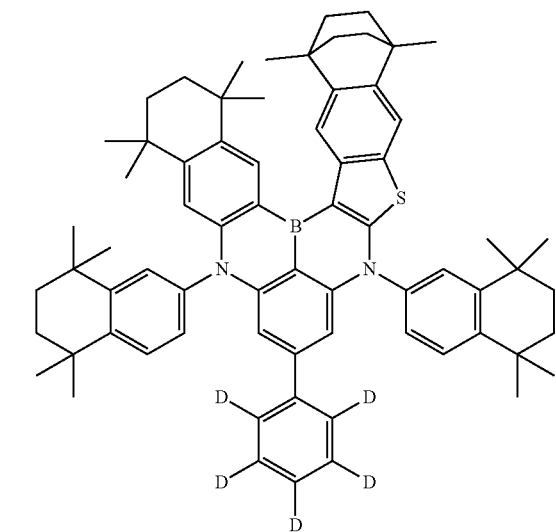 | 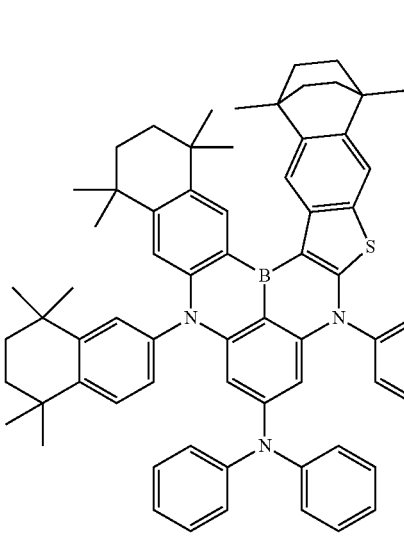 |

1563
-continued
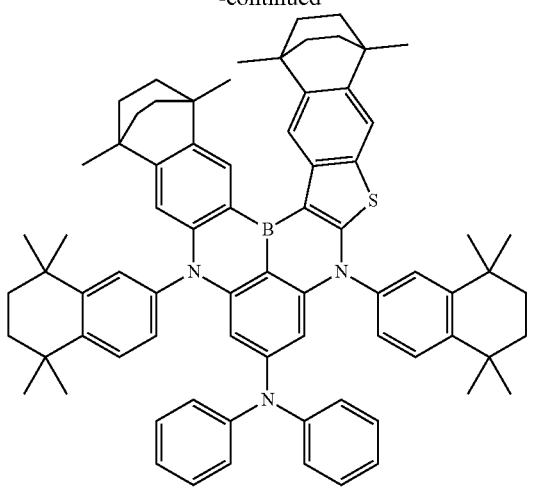
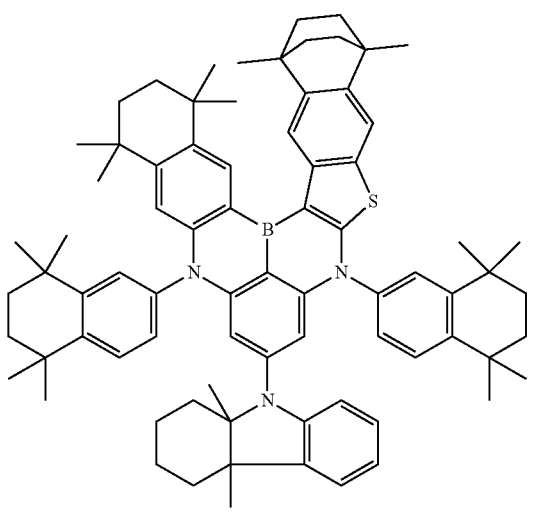
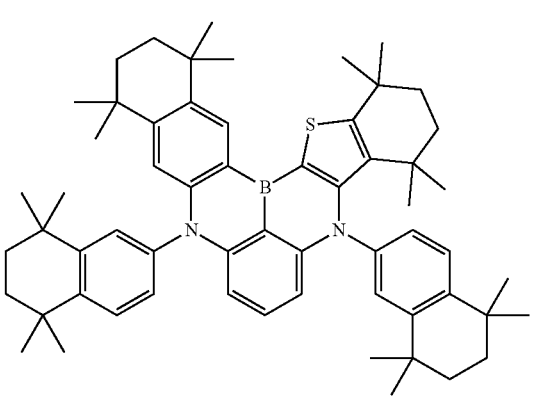
1564
-continued
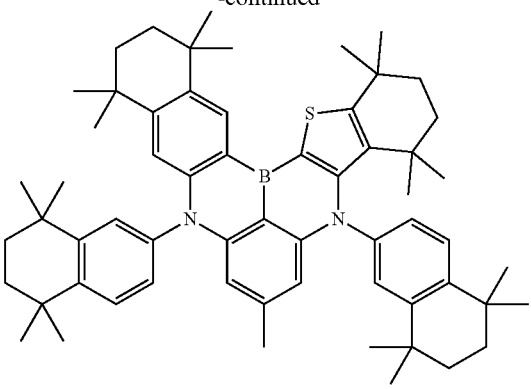
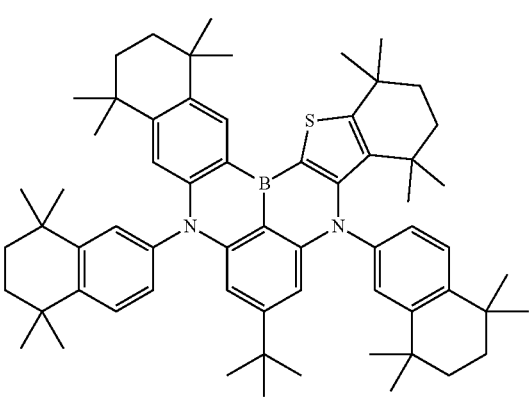

1565
-continued
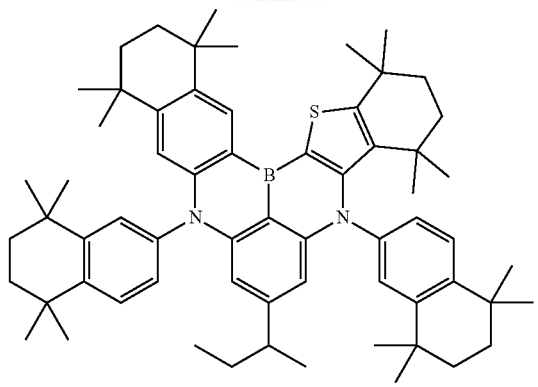
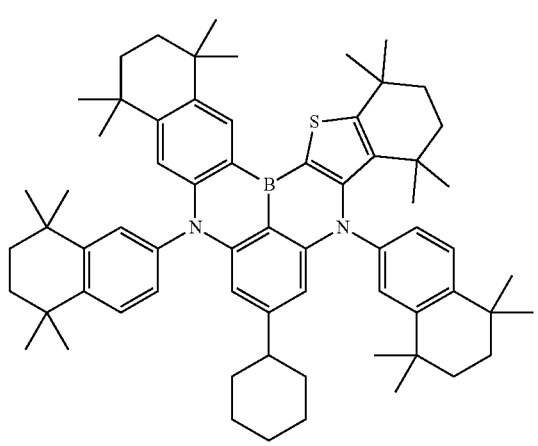
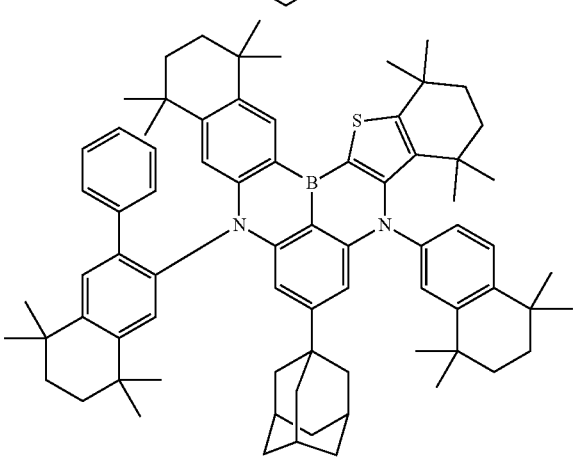
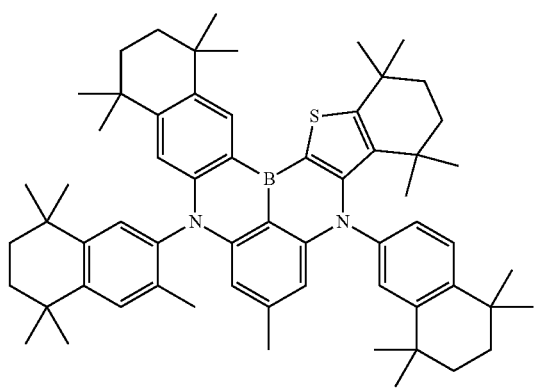
1566
-continued
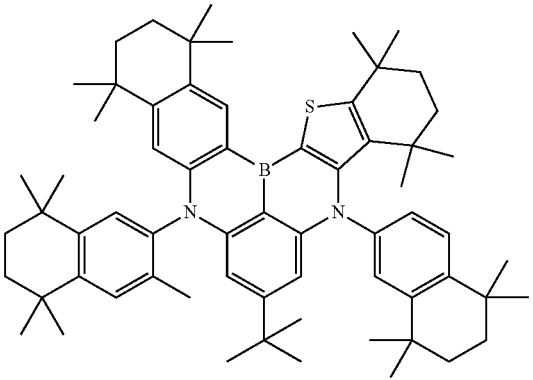
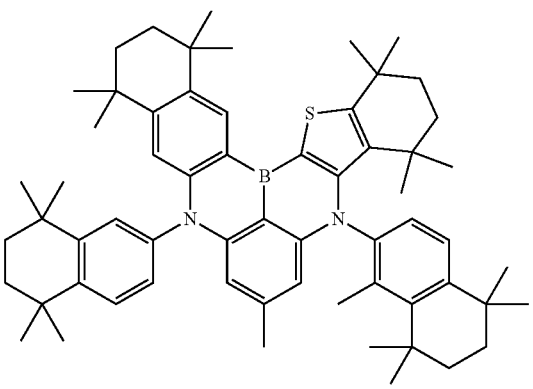
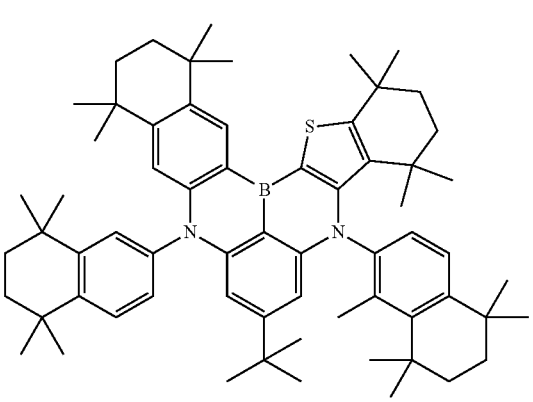
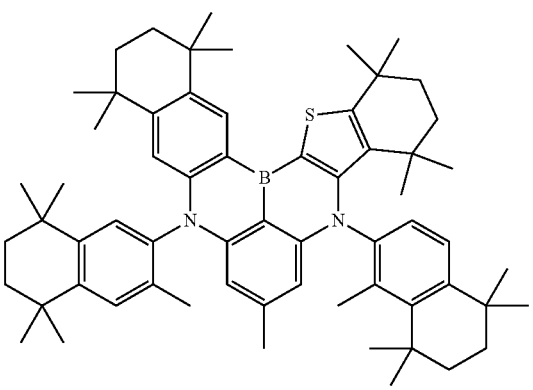

1567
-continued
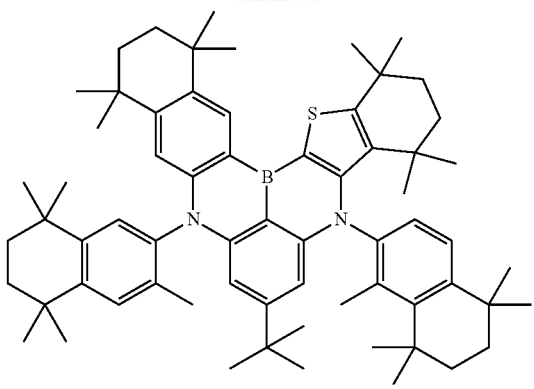
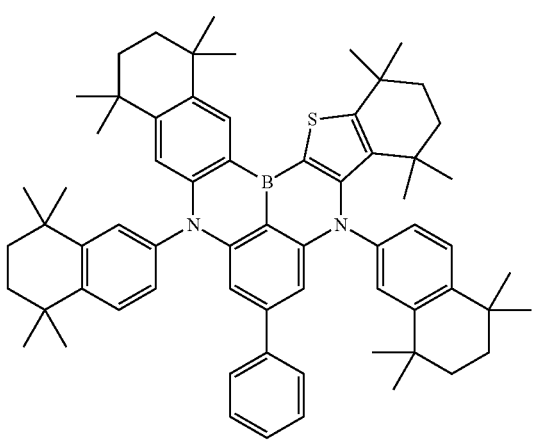
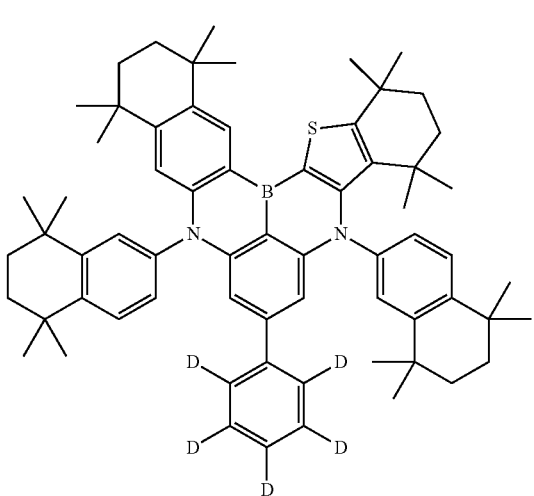
1568
-continued

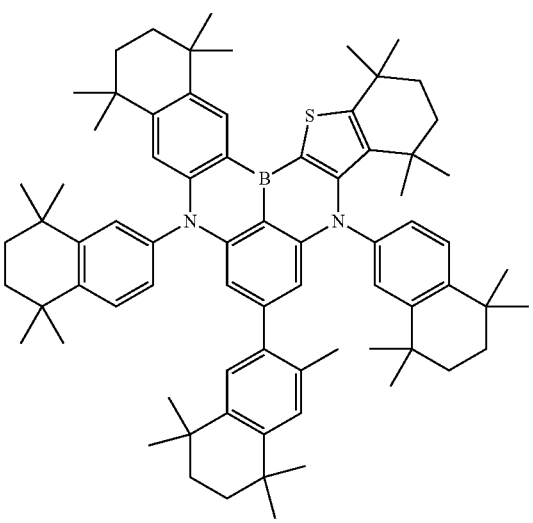
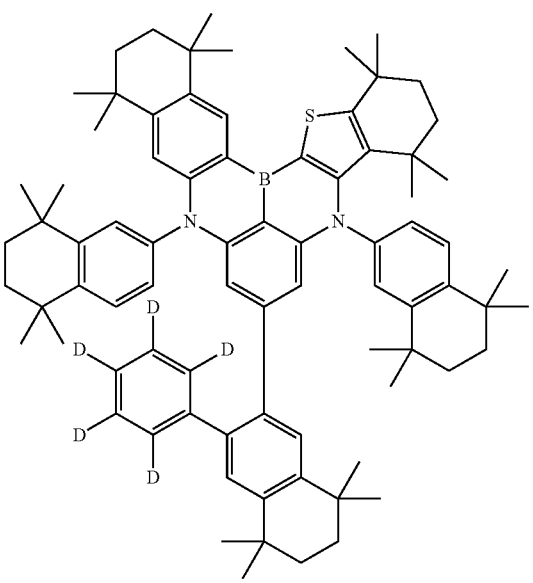

1569
-continued
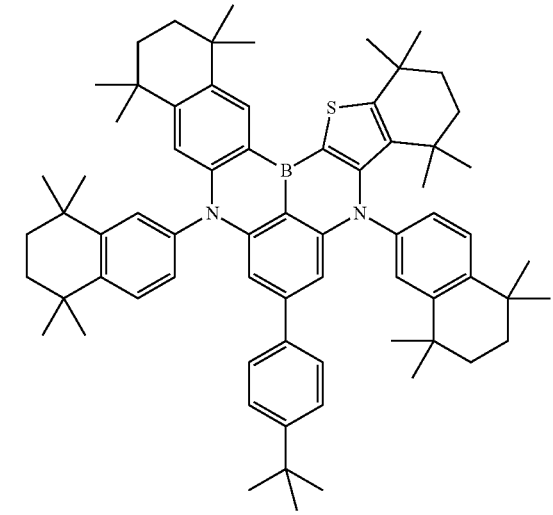
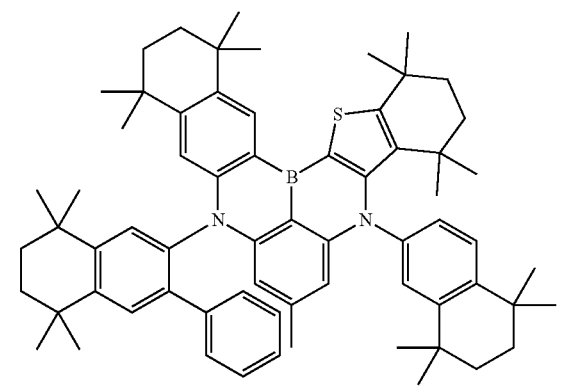
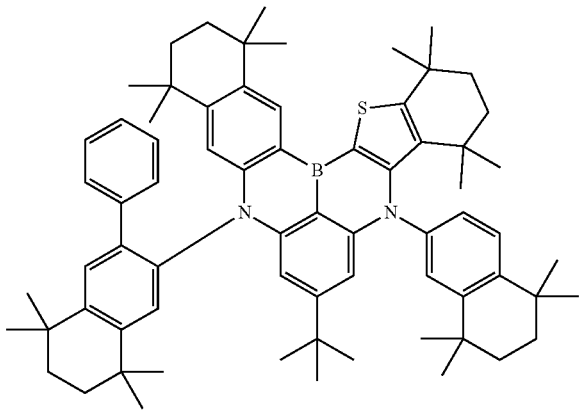
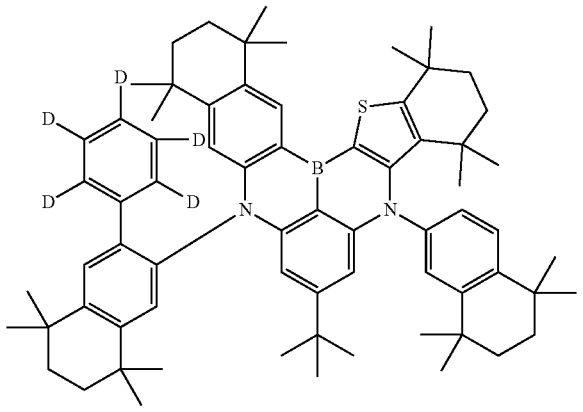
1570
-continued
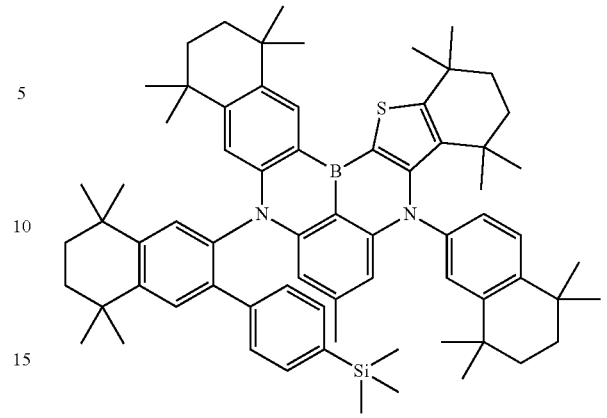
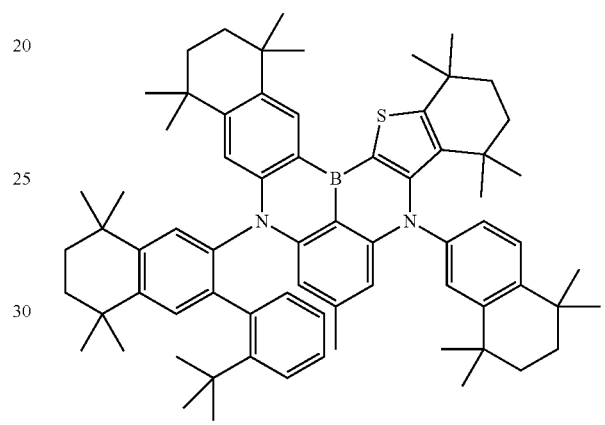

1571
-continued
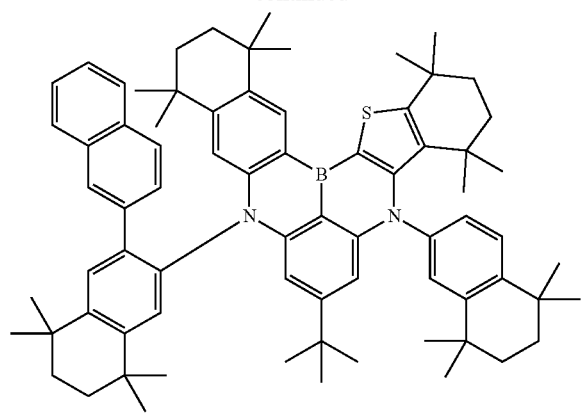
1572
-continued
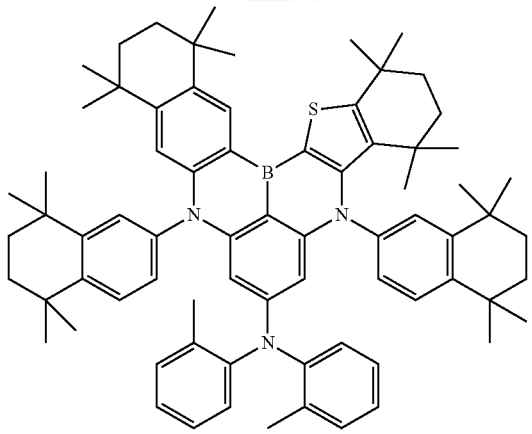
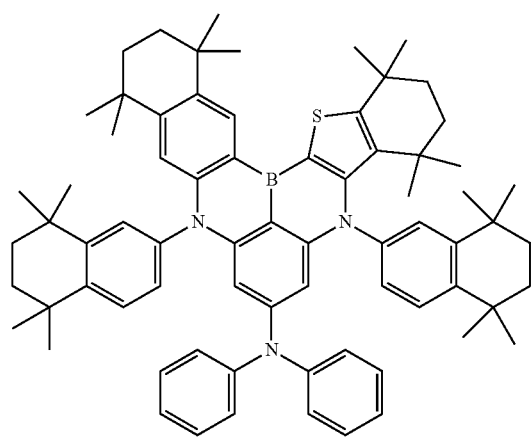
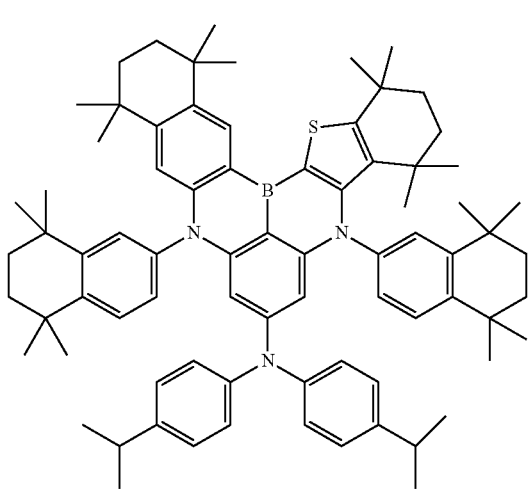
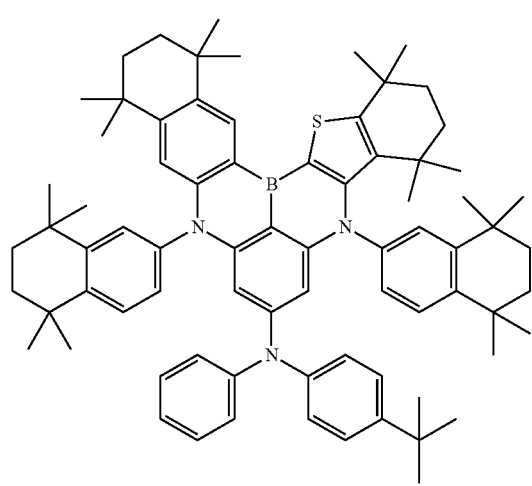
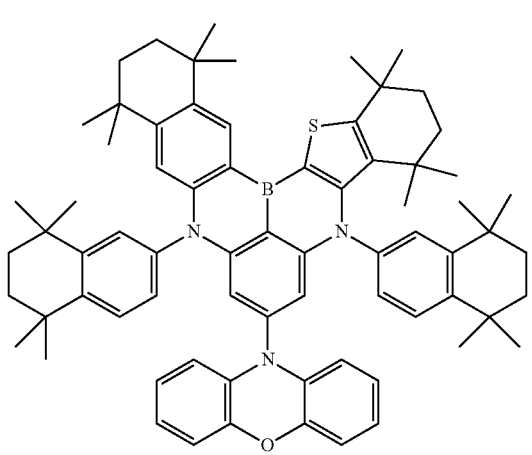

1573
-continued
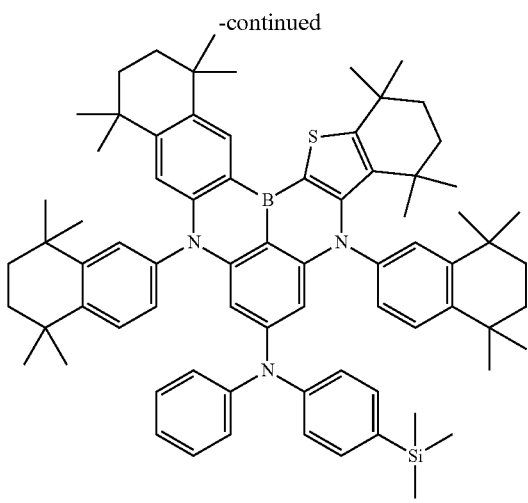
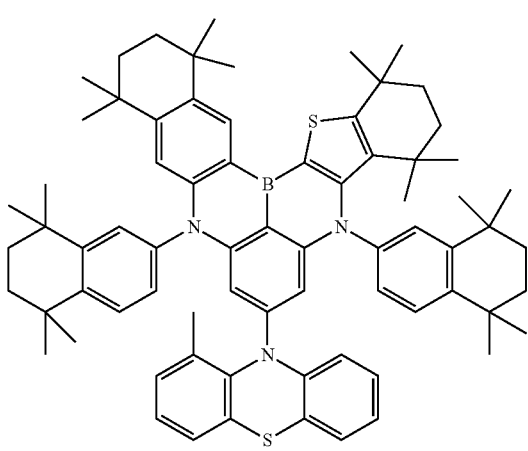
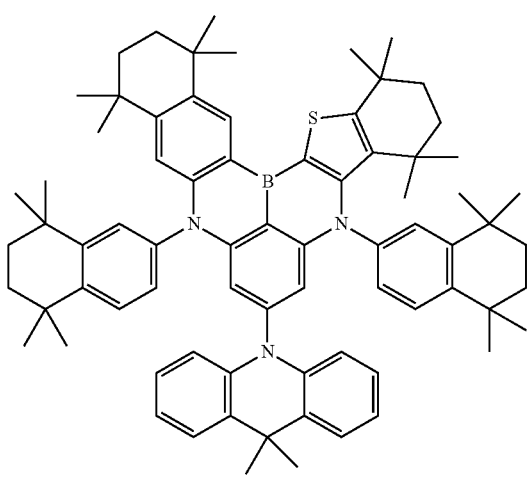
1574
-continued
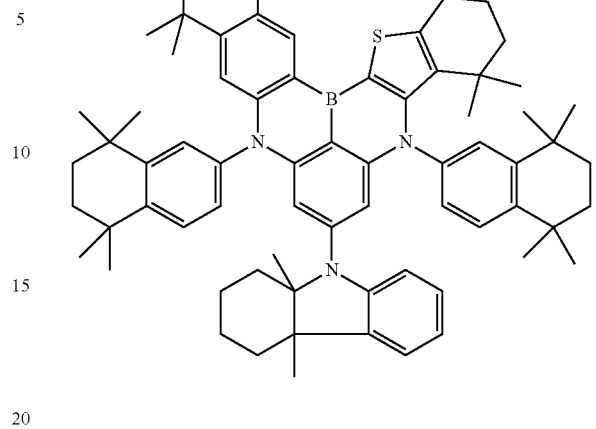
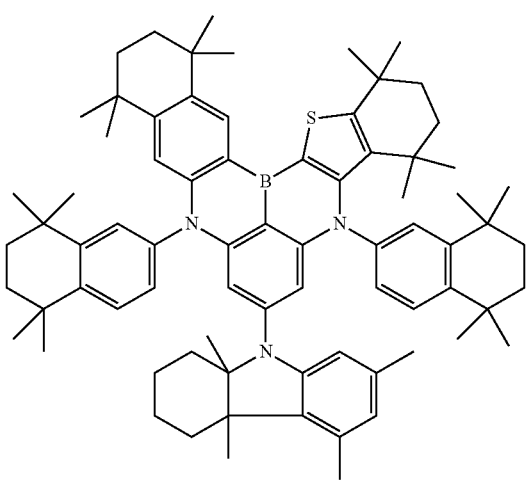
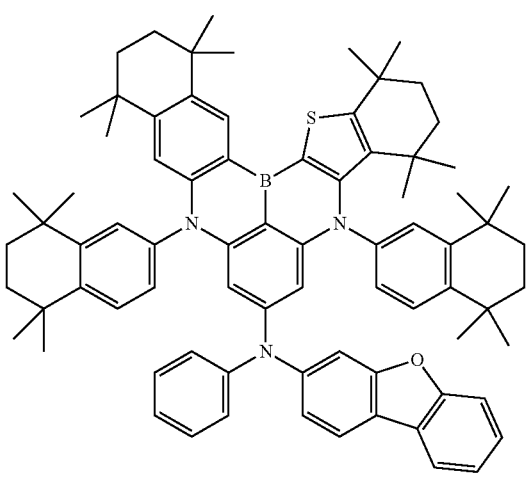

1575
-continued
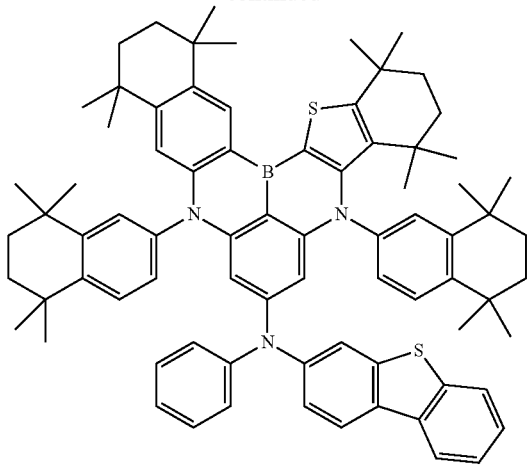
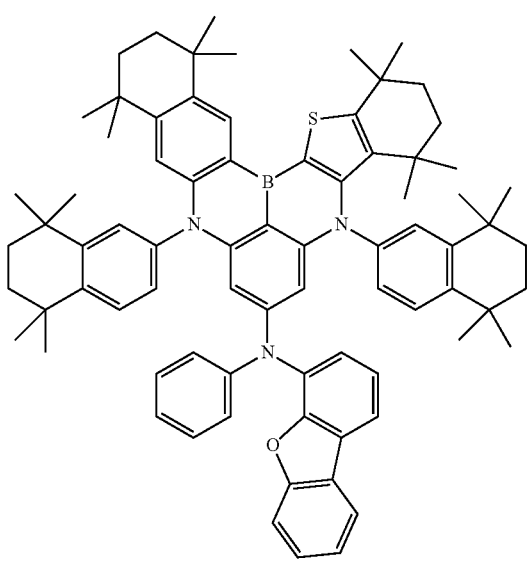
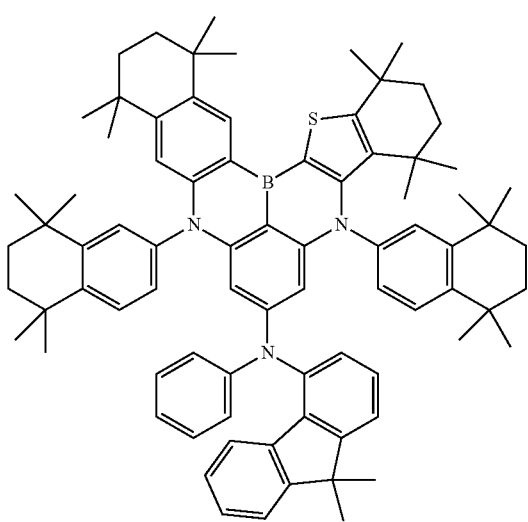
1576
-continued
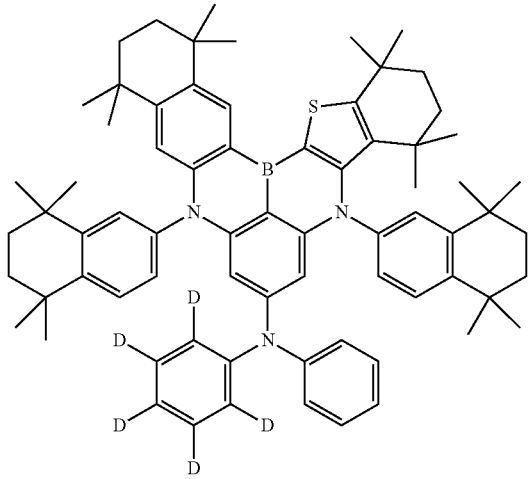
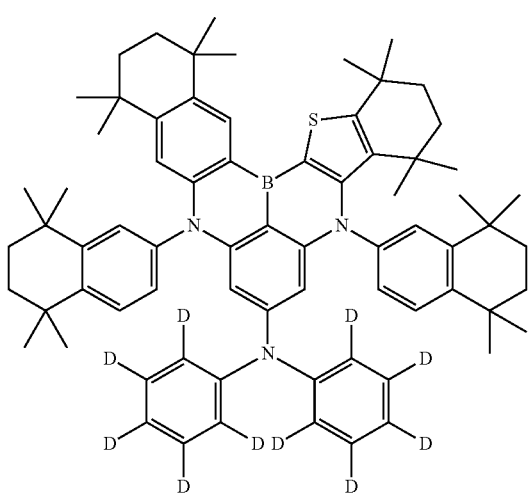

1577
-continued
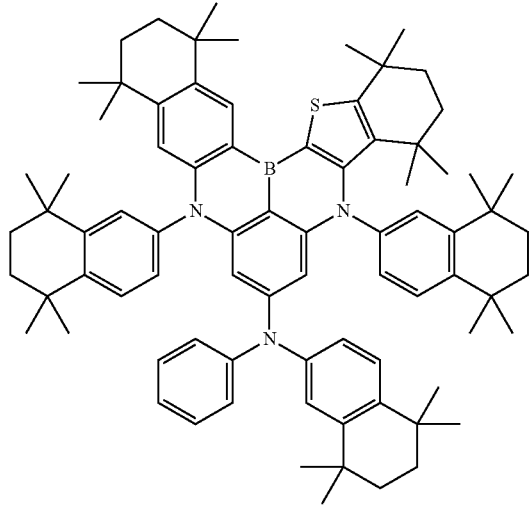
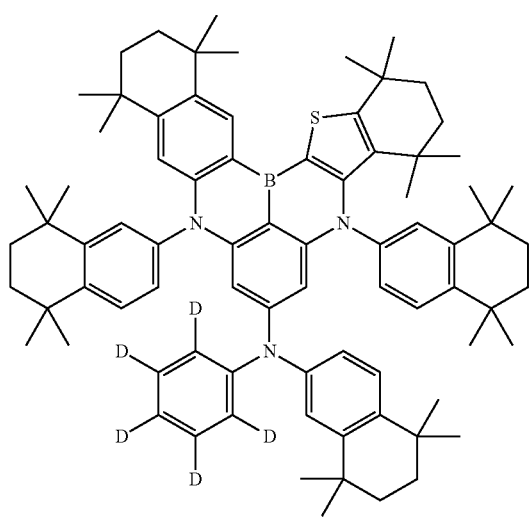
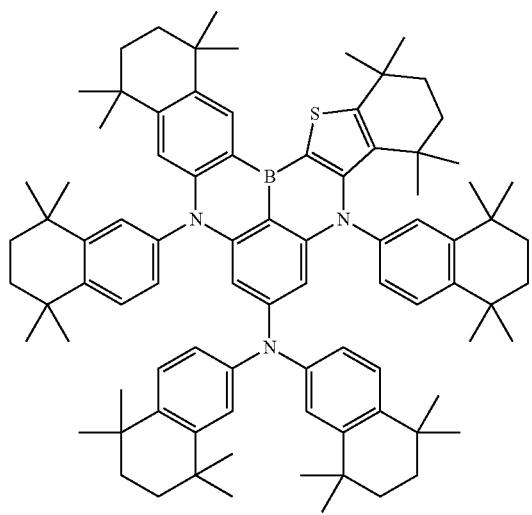
1578
-continued
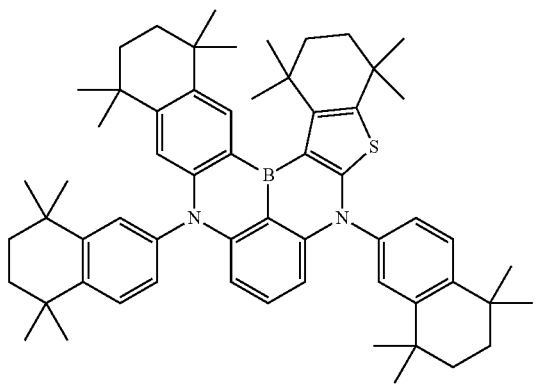
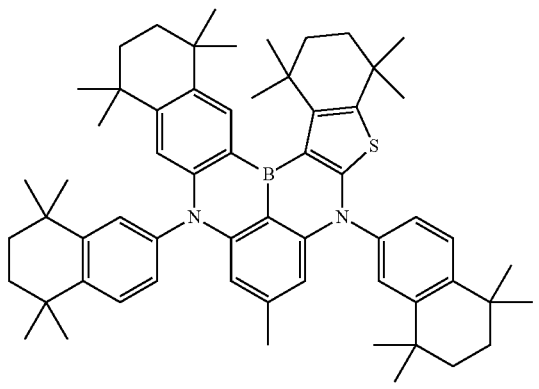
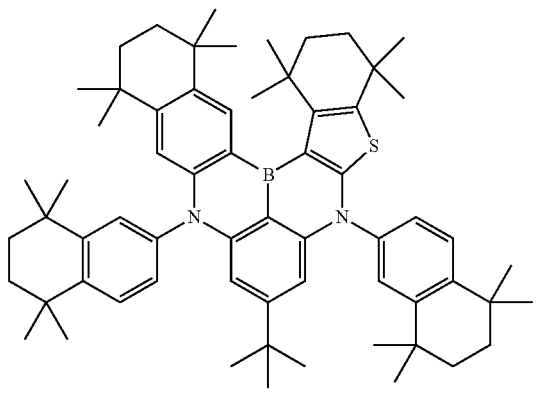
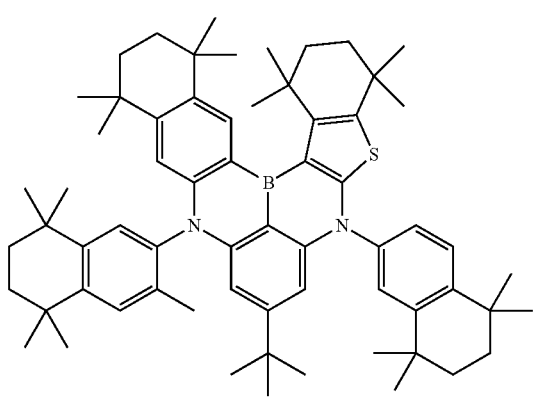

1579
-continued
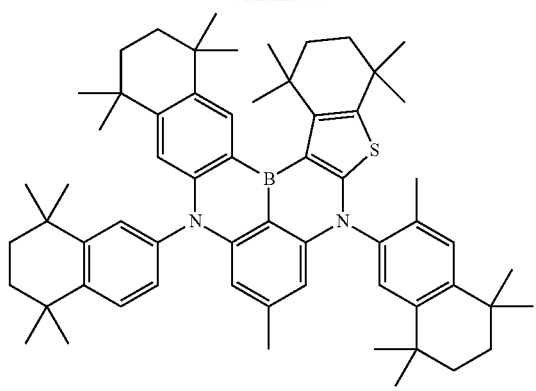
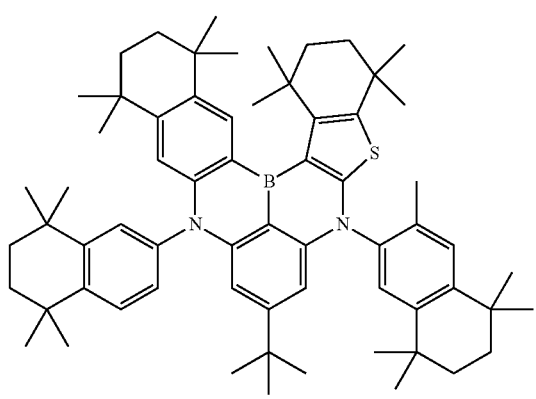
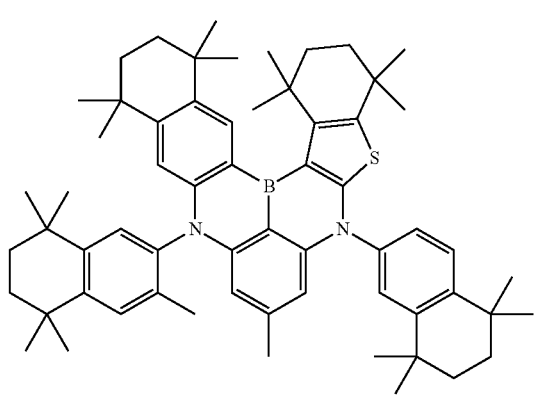
1580
-continued
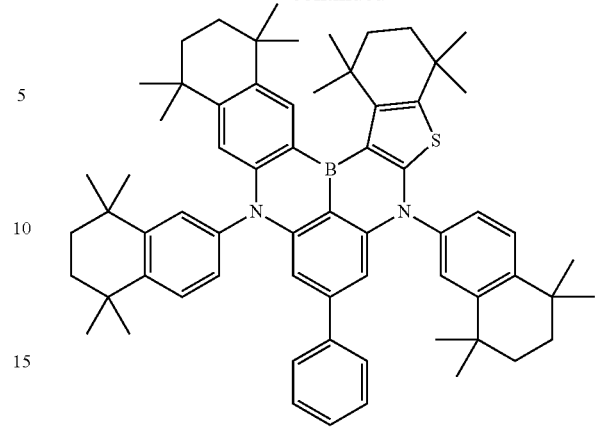
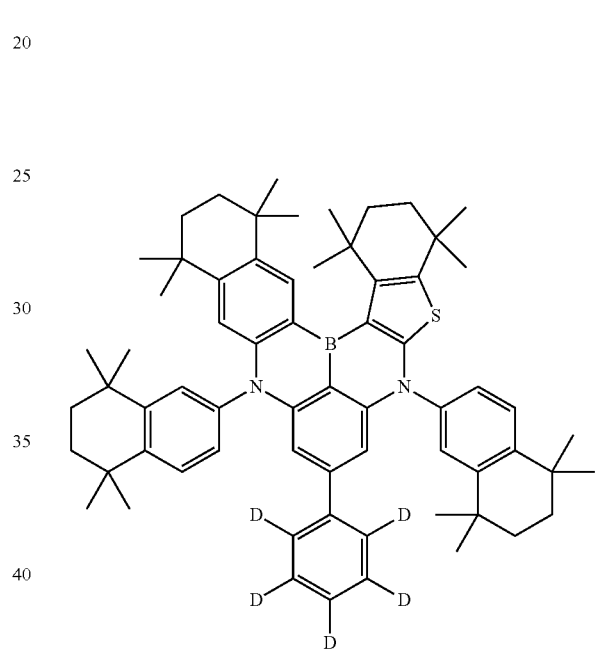
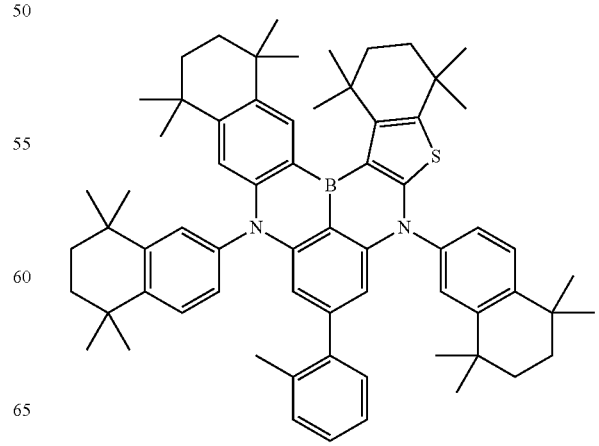

1581
-continued
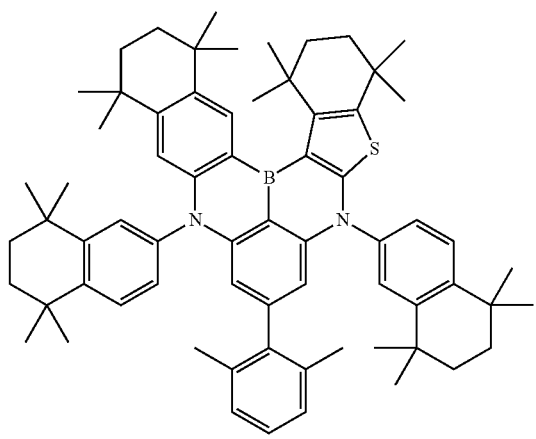
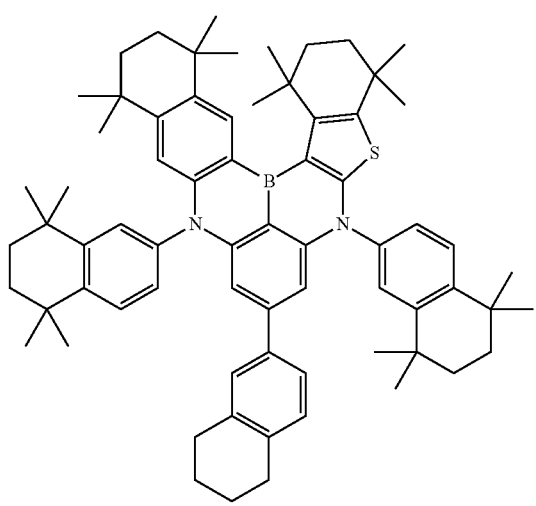
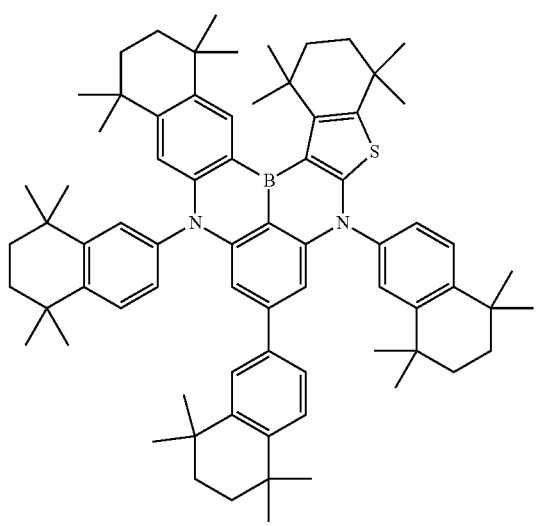
1582
-continued
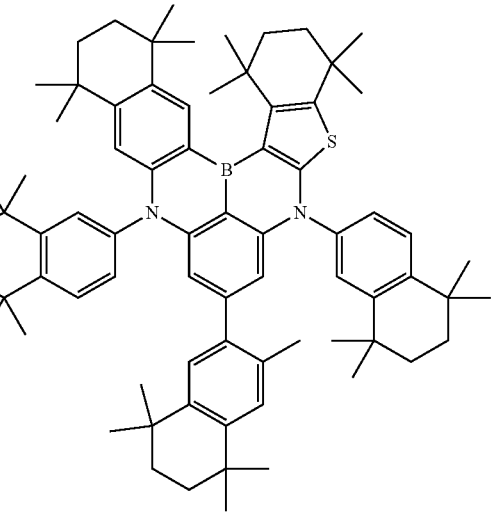
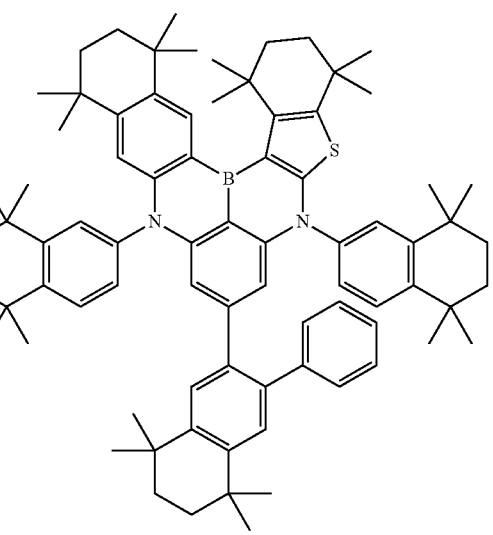
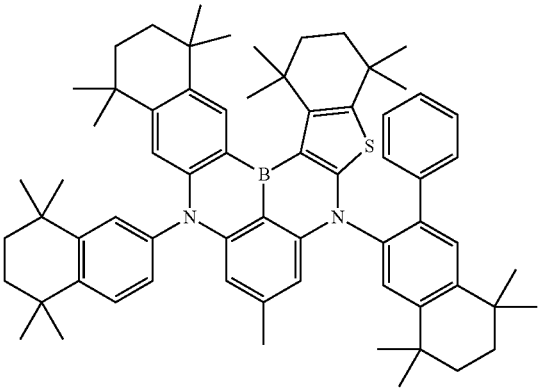

-continued
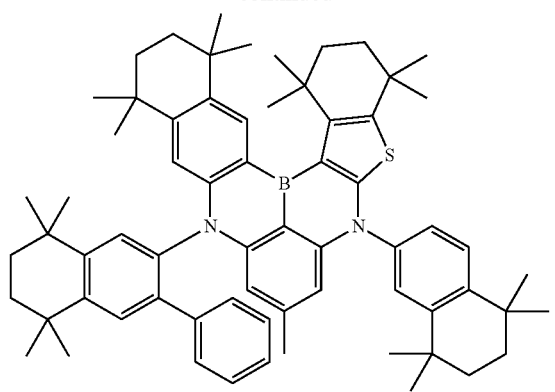
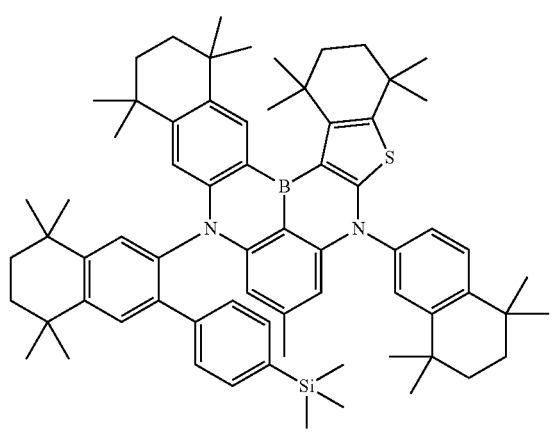
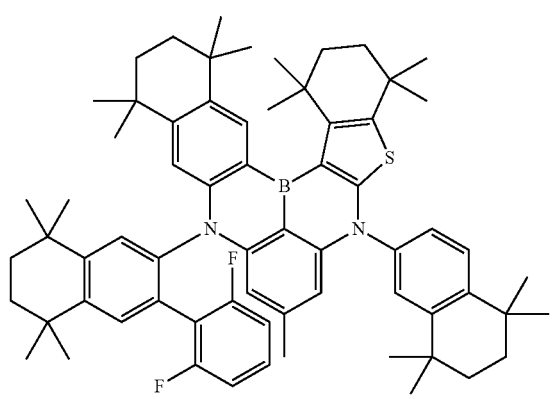
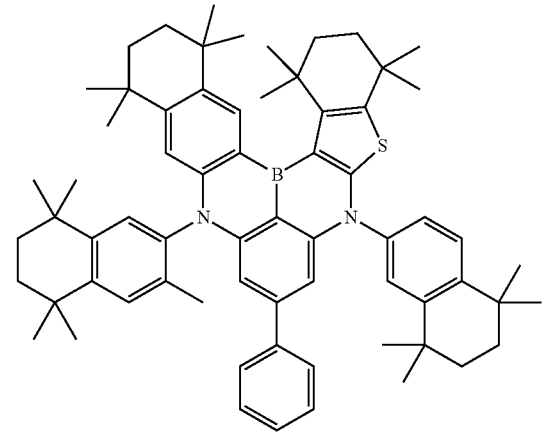
-continued
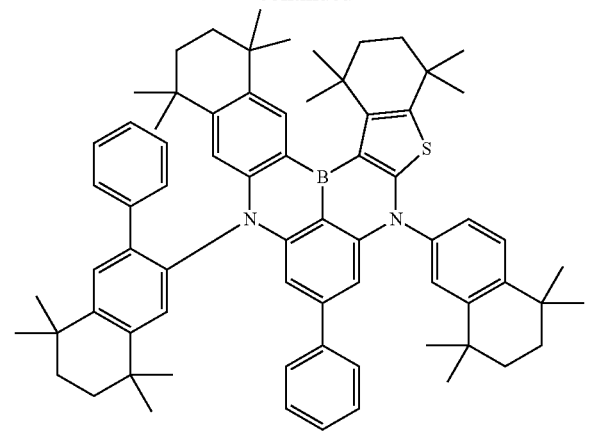
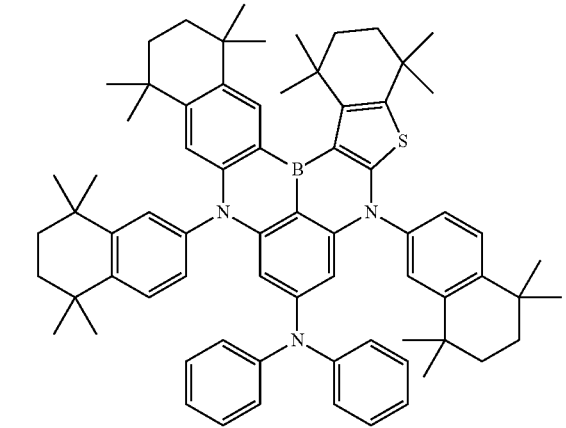
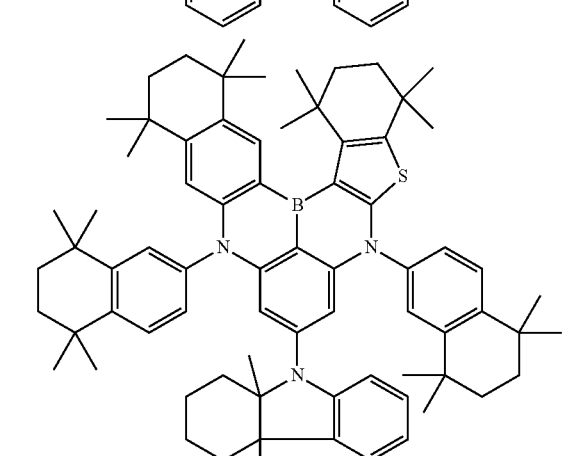
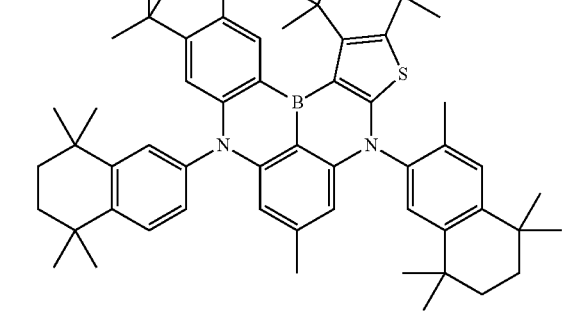

1585
-continued
1586
-continued
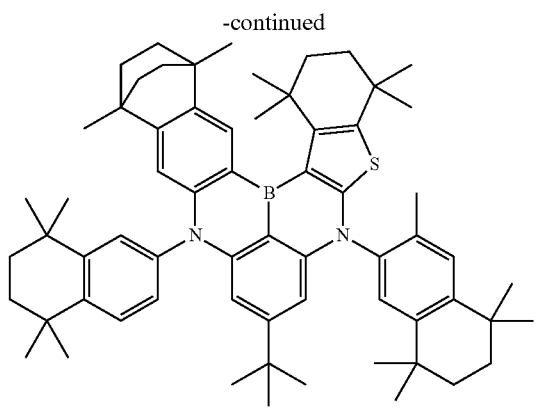
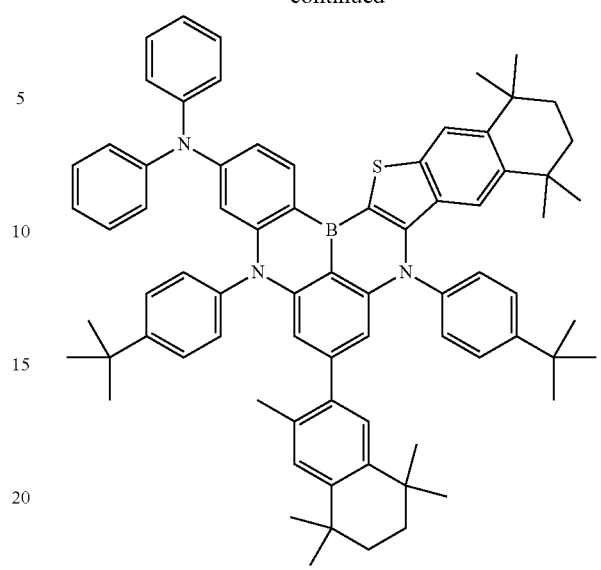
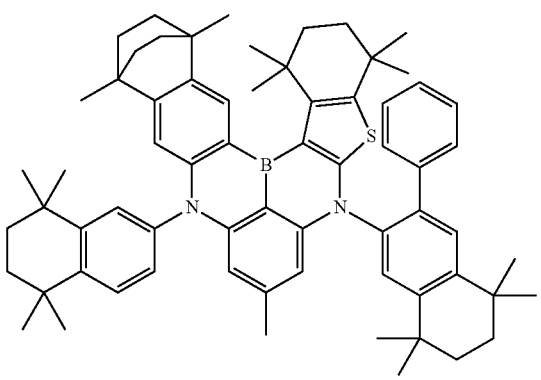
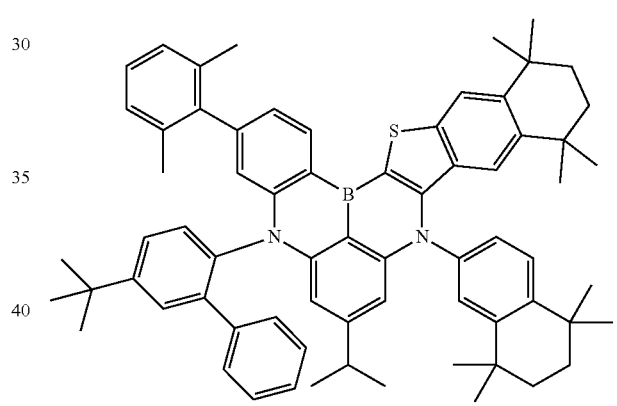
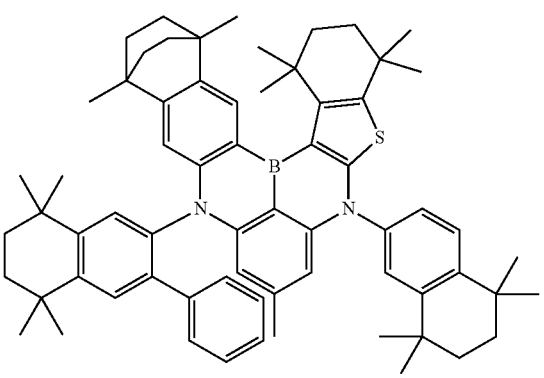
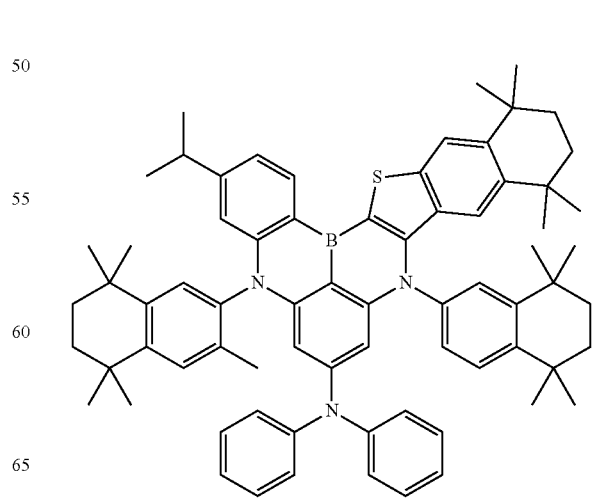

| 1587 -continued | 1588 -continued |
|---|---|
| 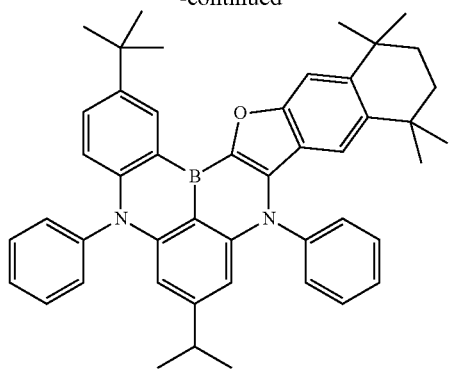 | 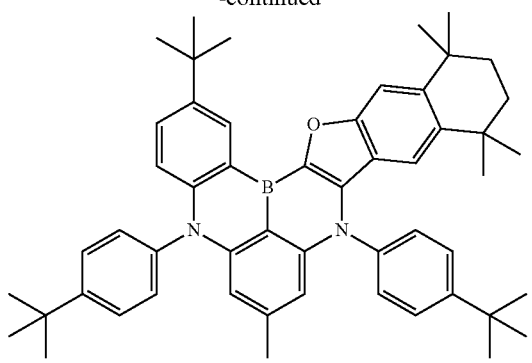 |
| 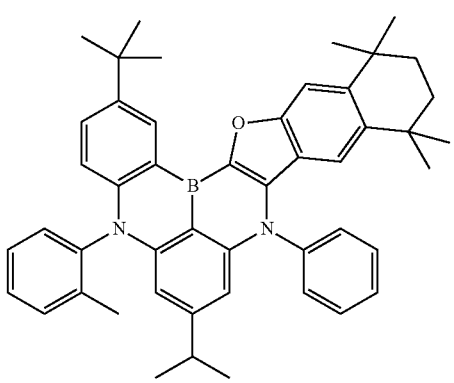 | 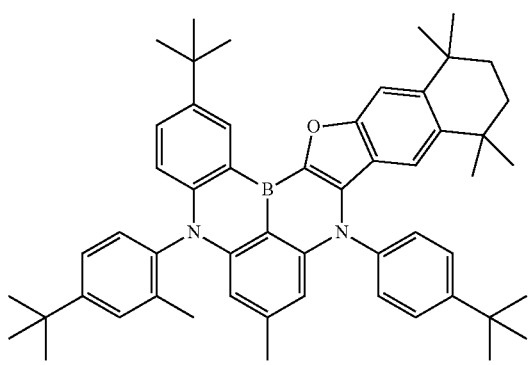 |
| 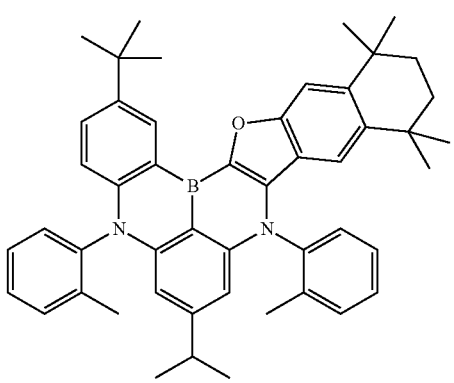 | 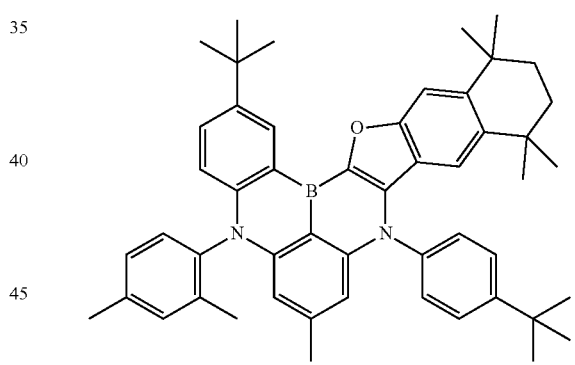 |
| 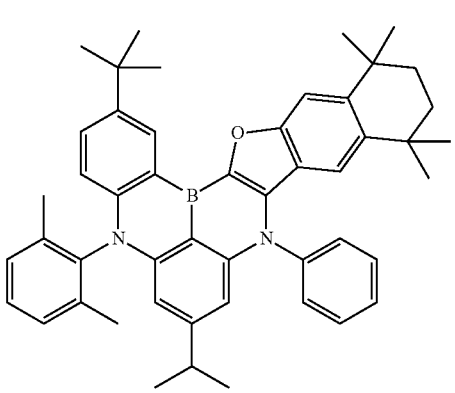 | 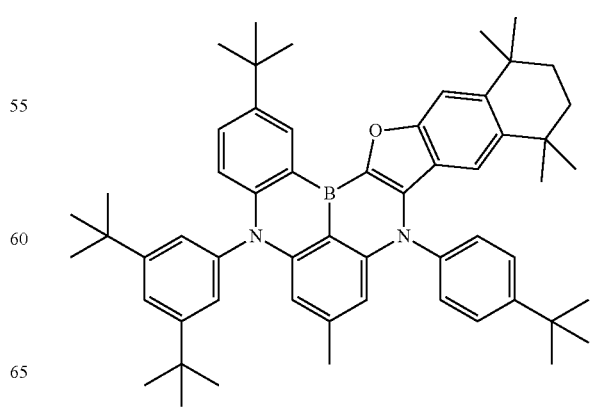 |

1589
-continued

1590
-continued

| 1591 -continued | 1592 -continued |
|---|---|
| 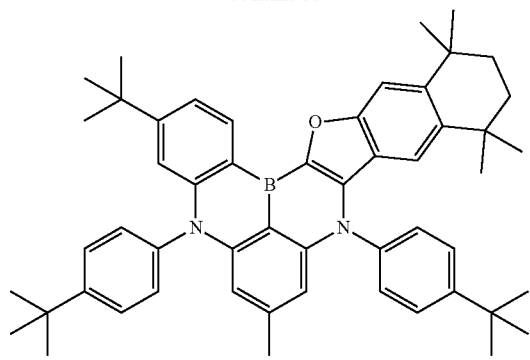 | 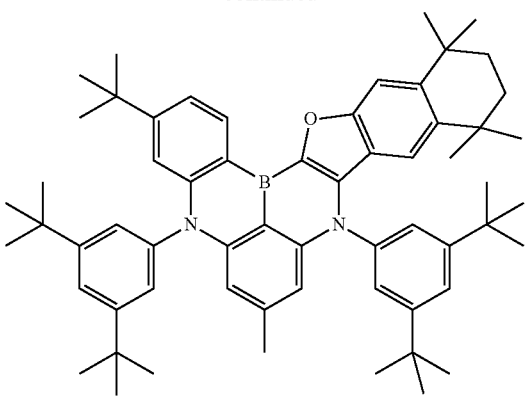 |
| 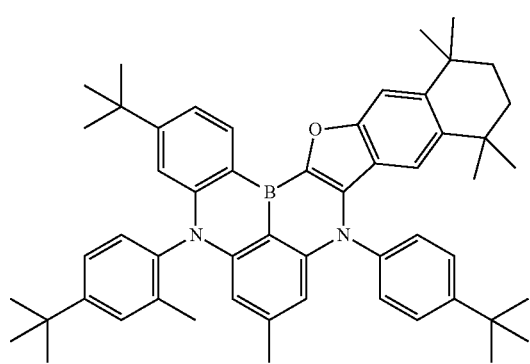 | 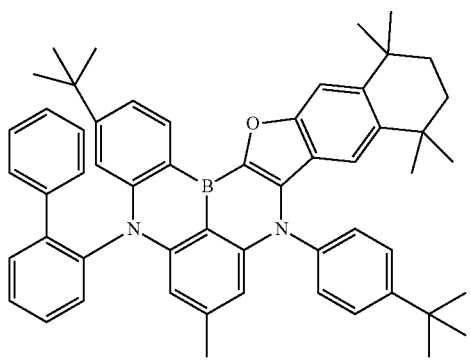 |
| 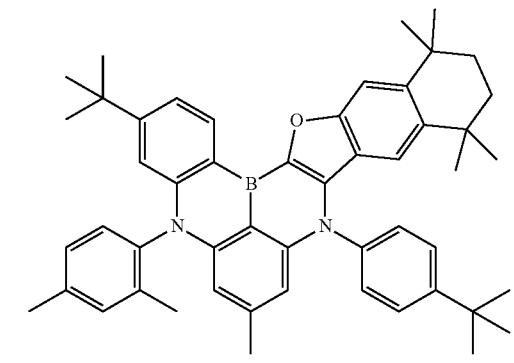 | 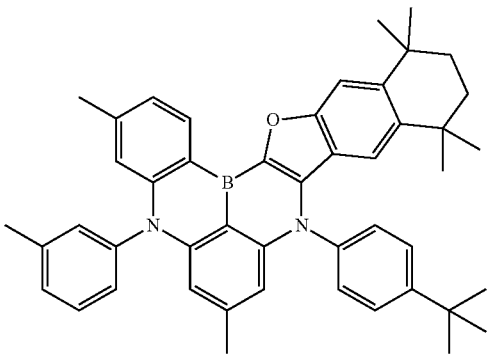 |
| 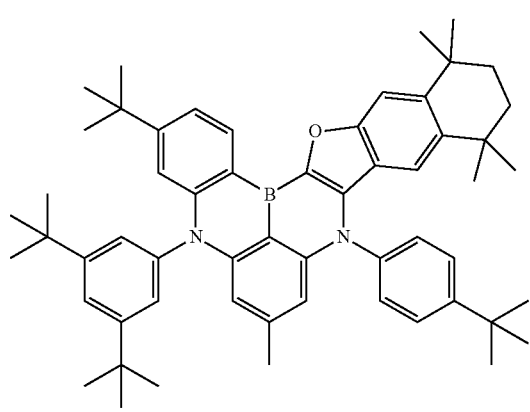 | 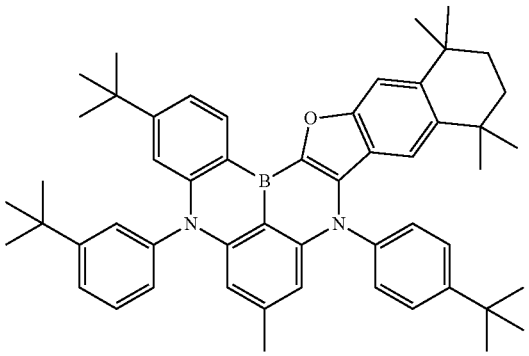 |

1593
-continued
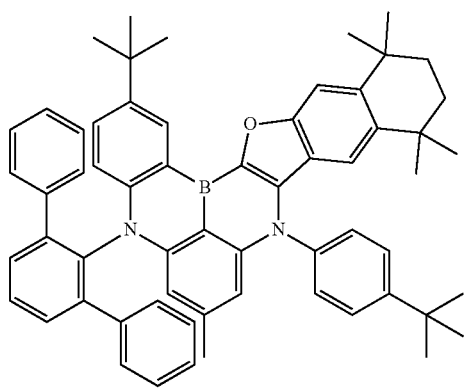
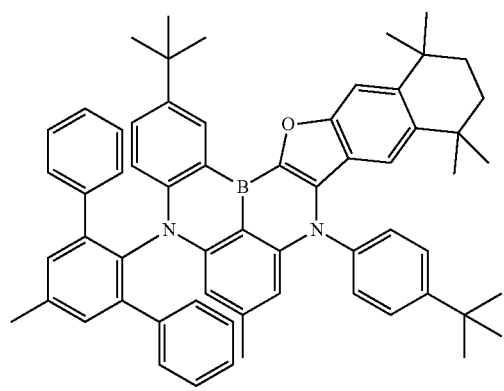
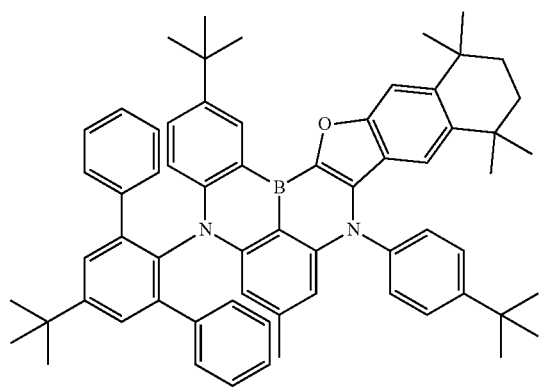
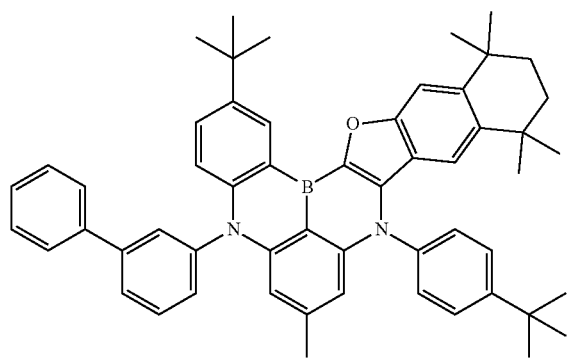
1594
-continued
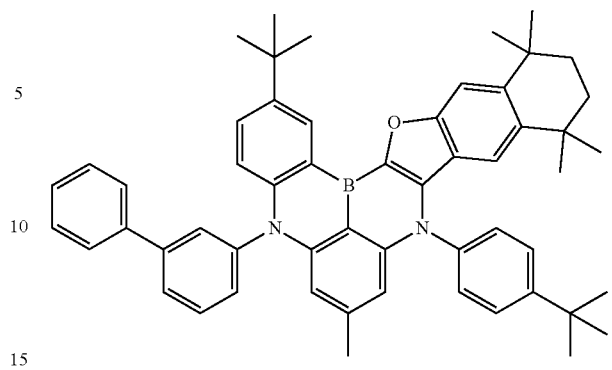
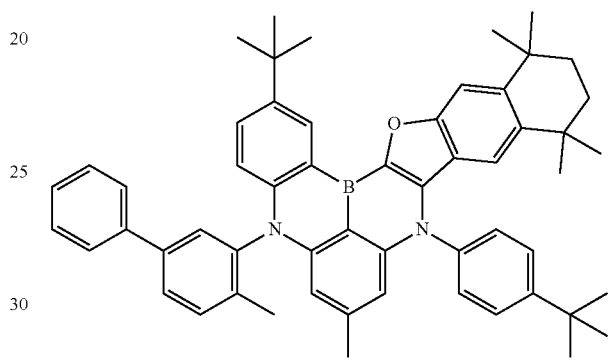
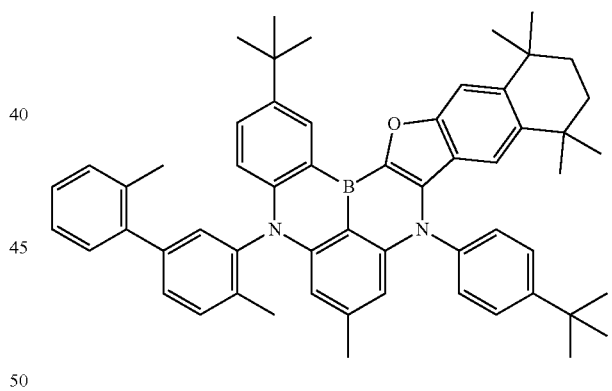
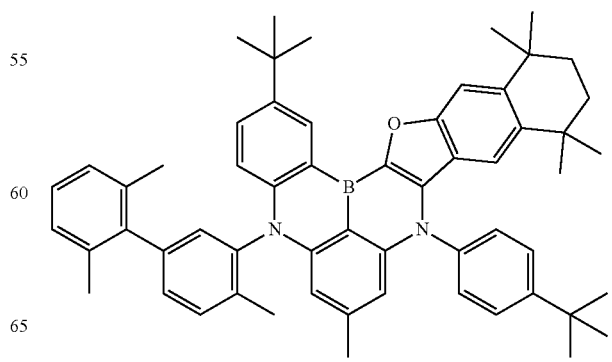

1595
-continued
1596
-continued
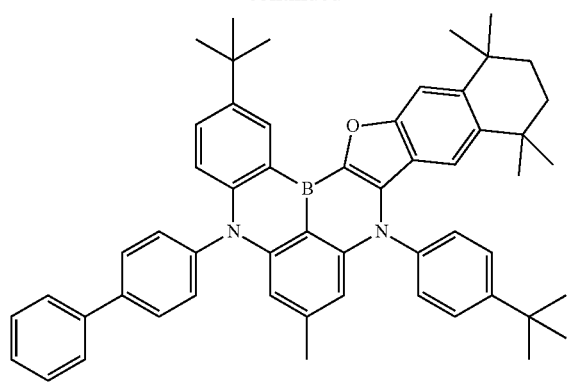
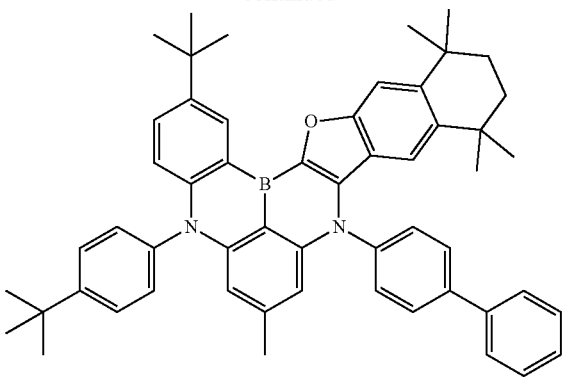

| 1597 | 1598 |
|---|---|
| -continued | -continued |
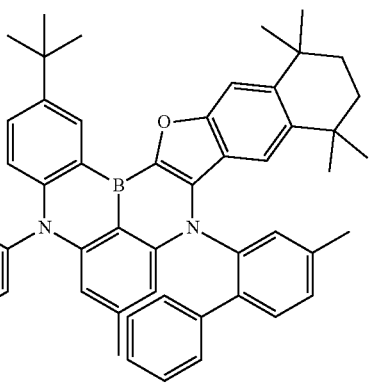
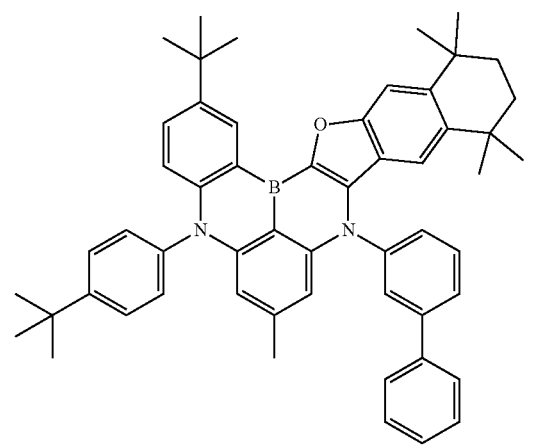
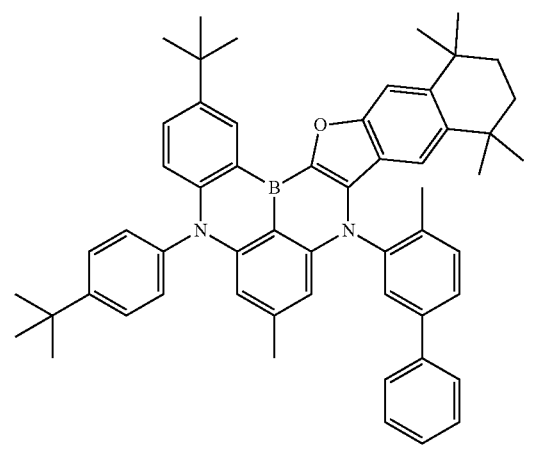
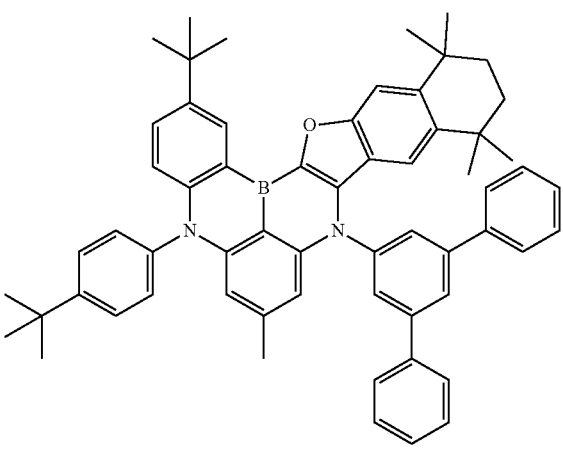
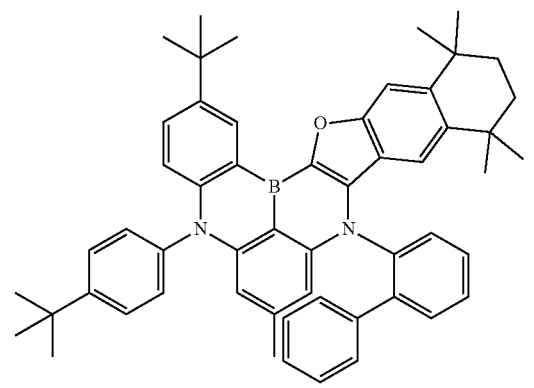
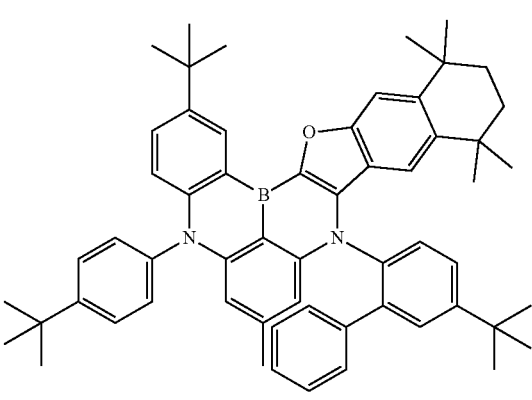
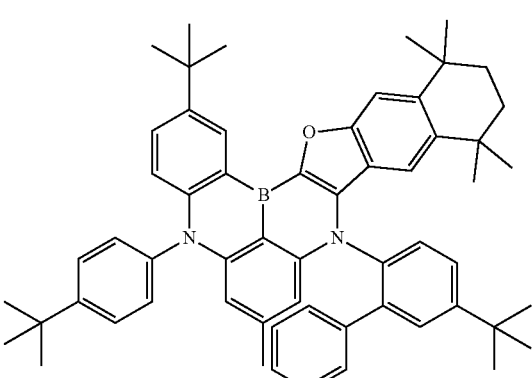

1599
-continued
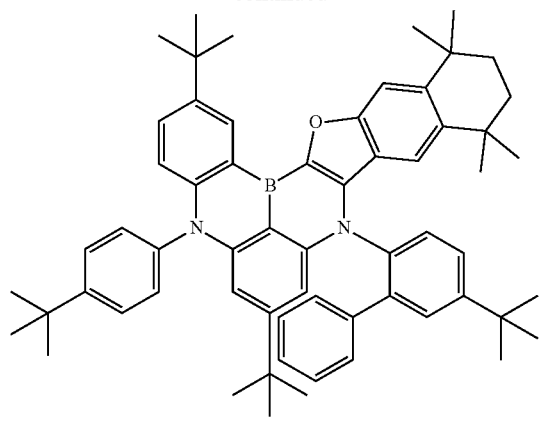
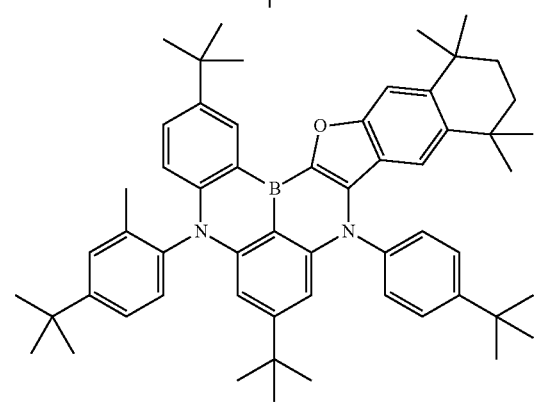
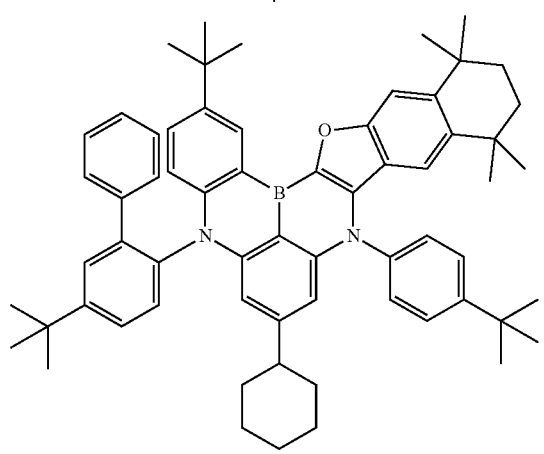
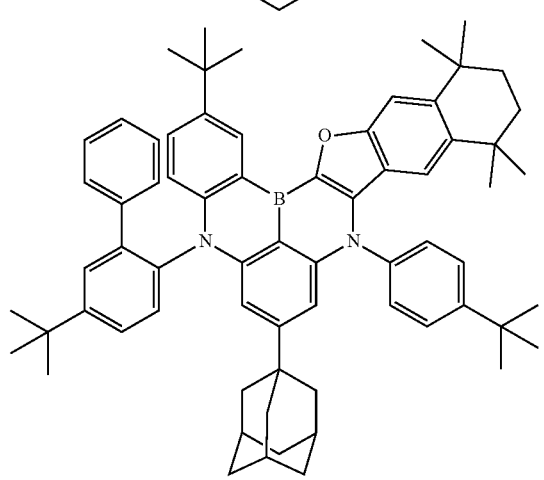
1600
-continued
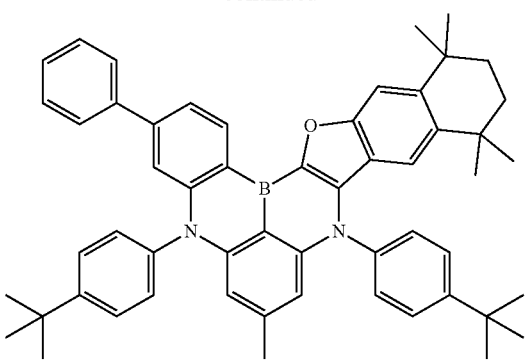
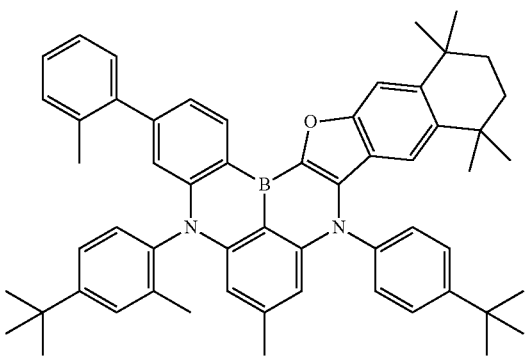
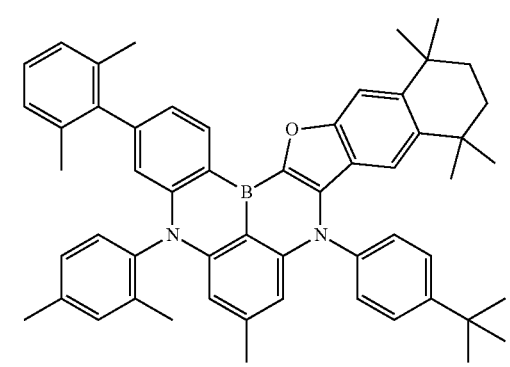
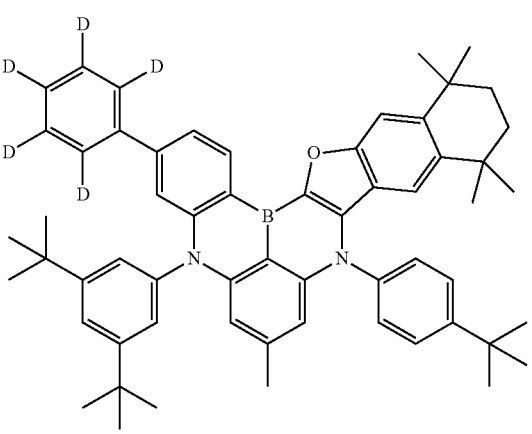

1601
-continued
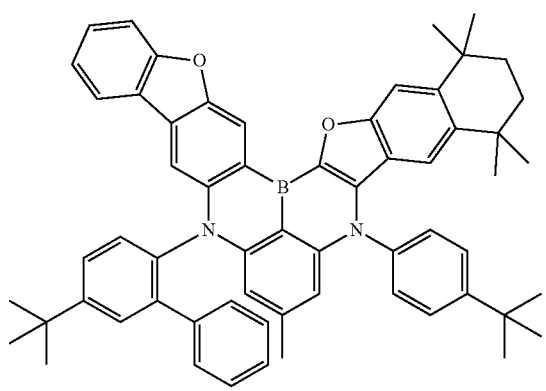
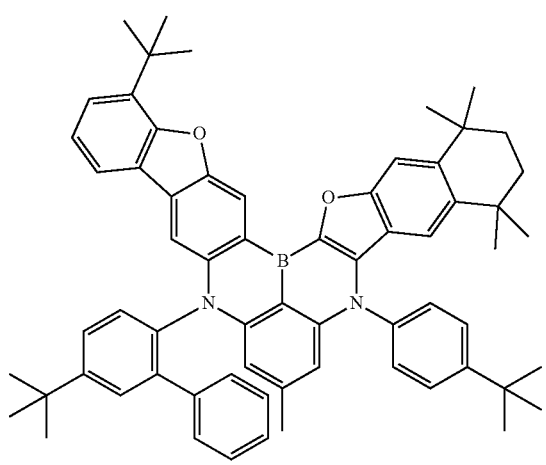
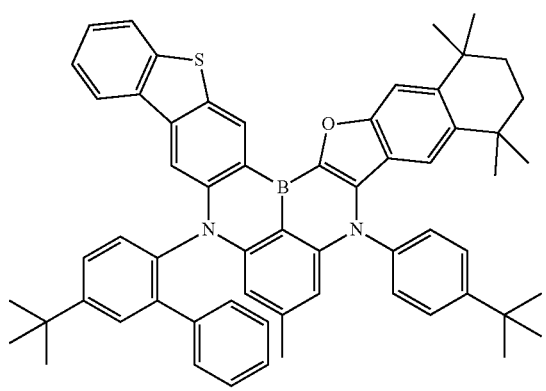
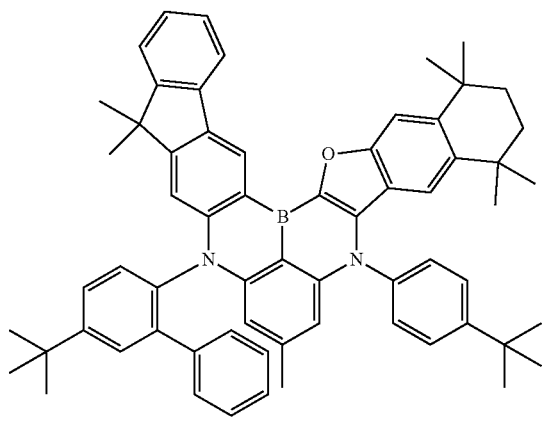
1602
-continued
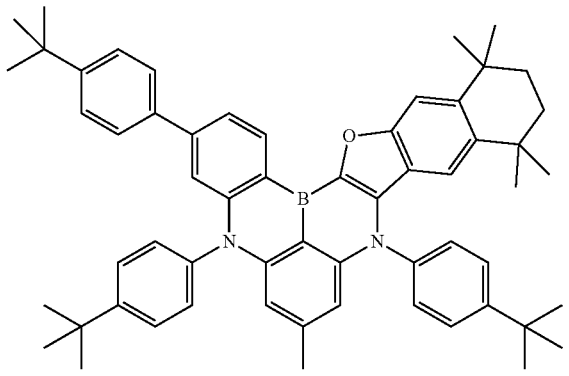
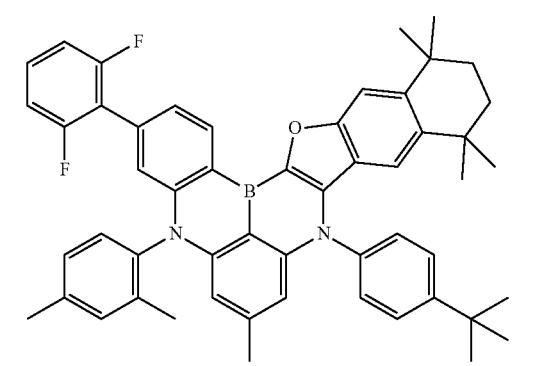
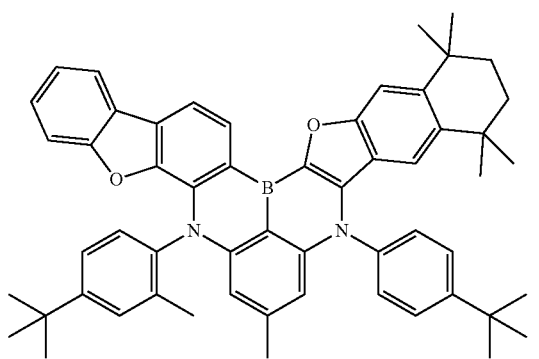
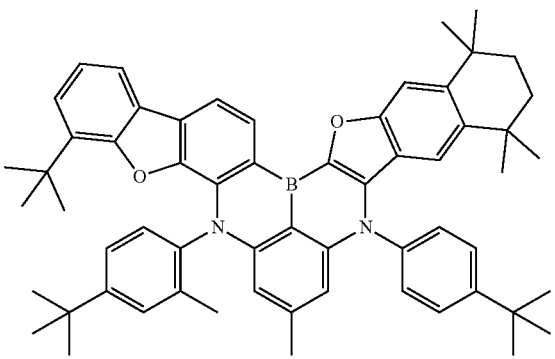

1603
-continued
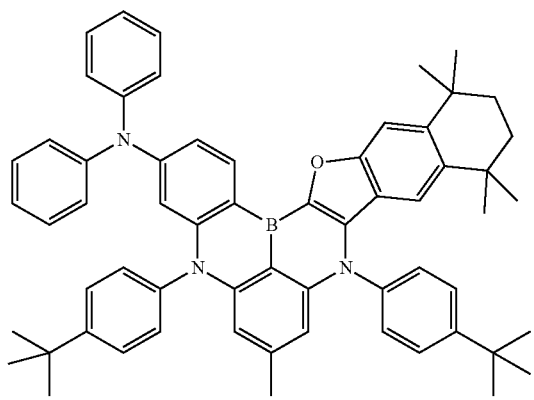
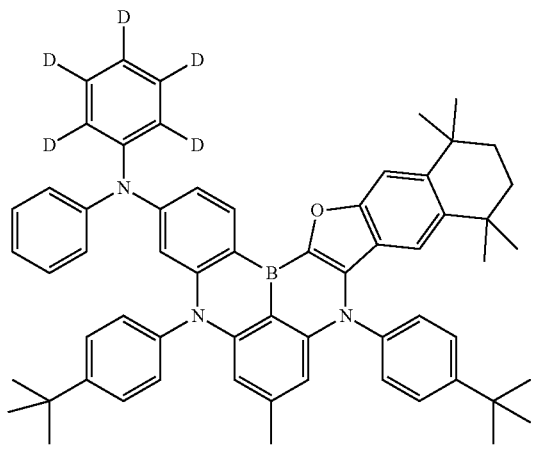
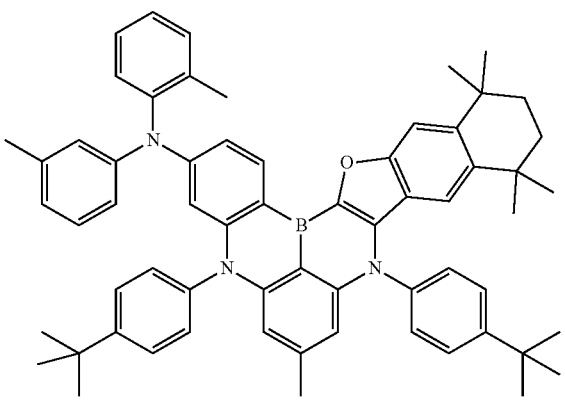
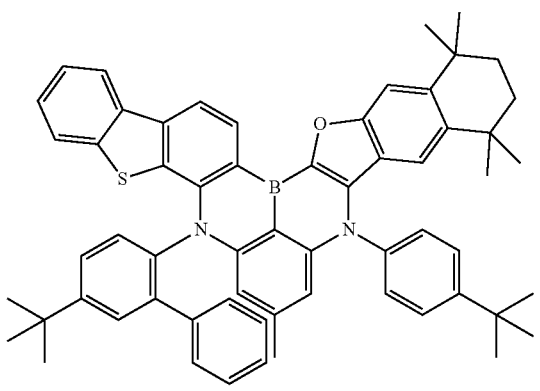
1604
-continued
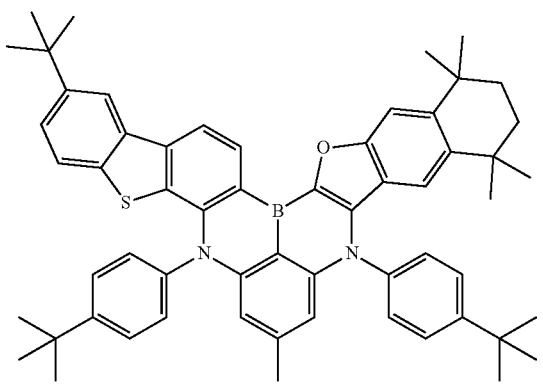
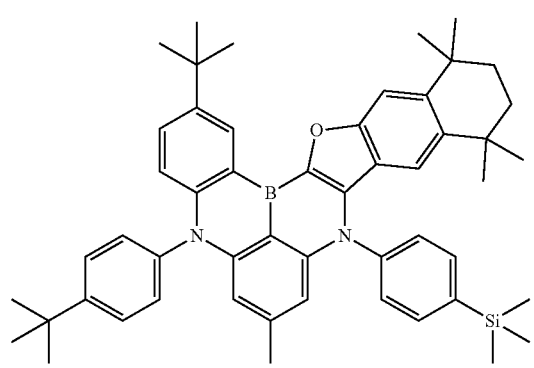
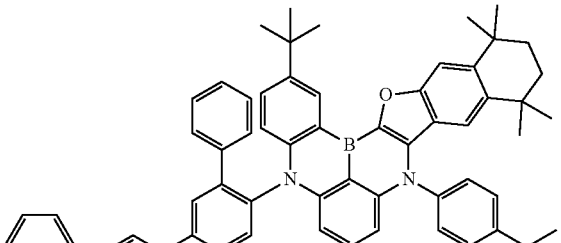
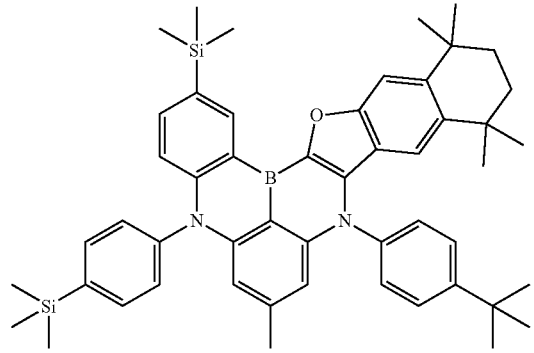

1605
-continued
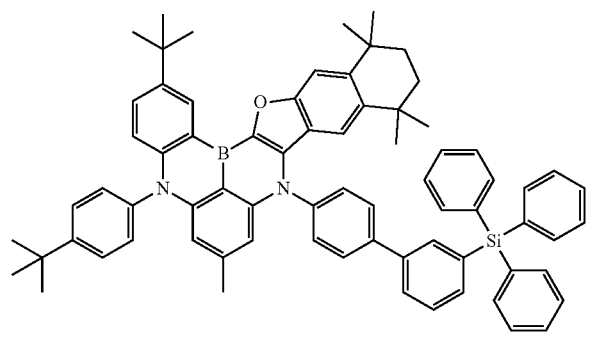
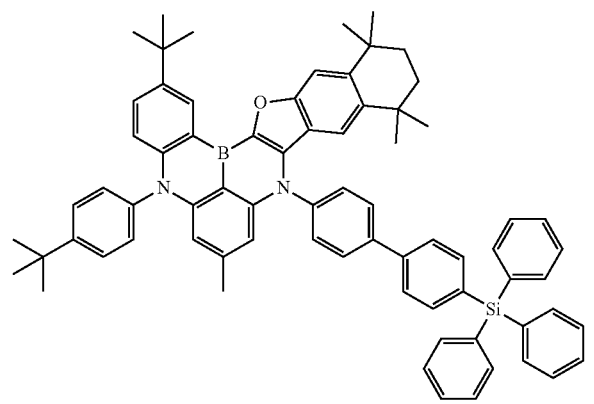
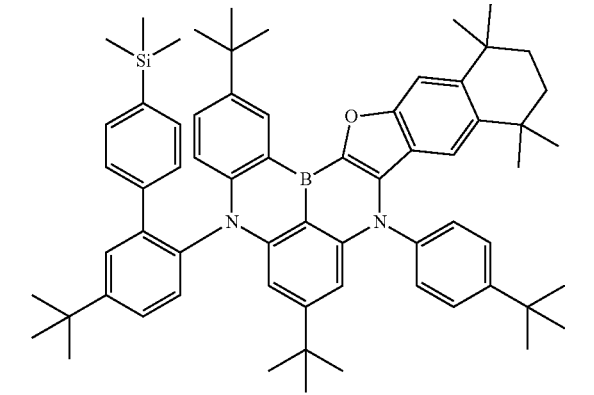
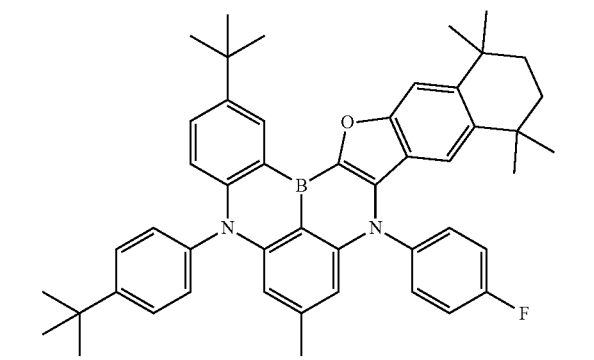
1606
-continued
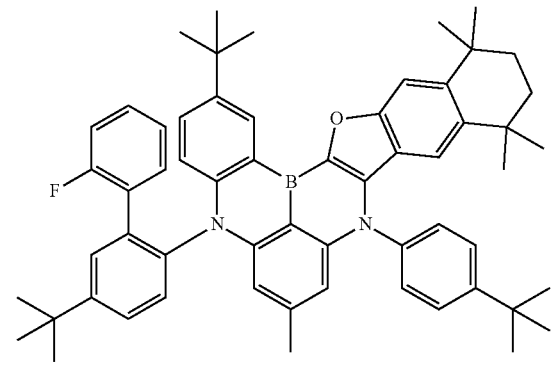
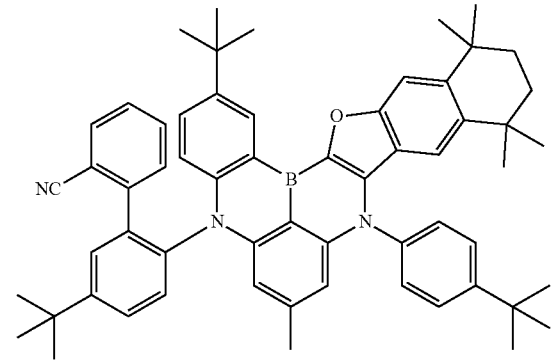
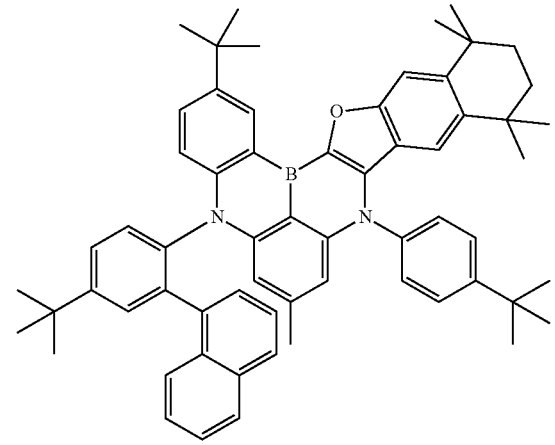
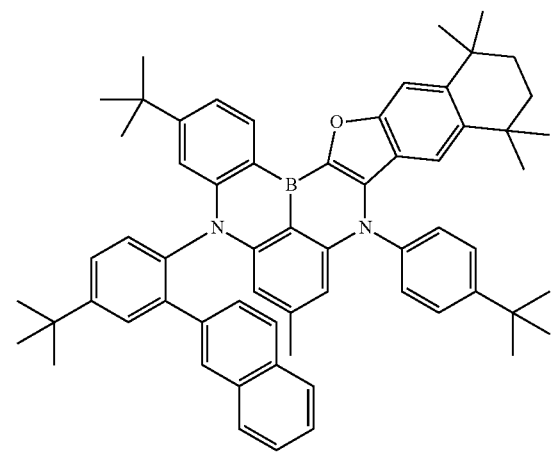

1607
-continued
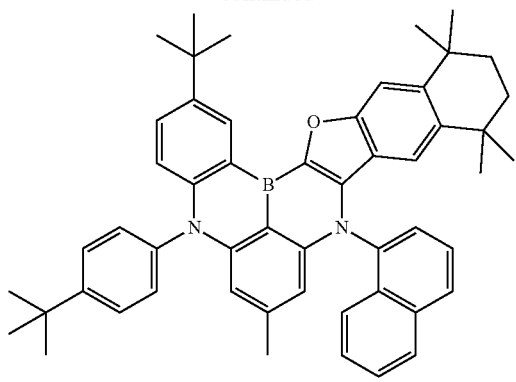
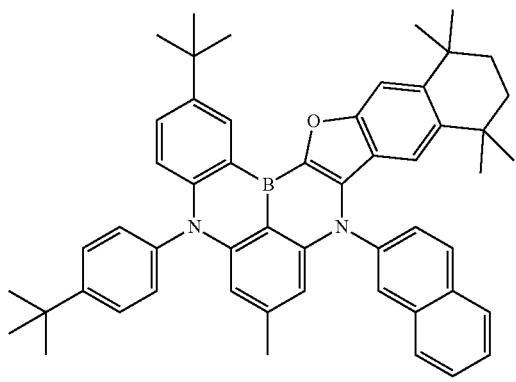
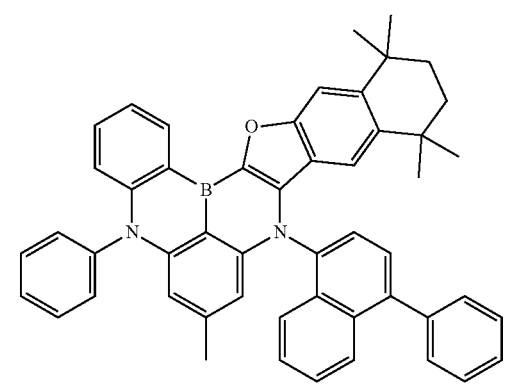
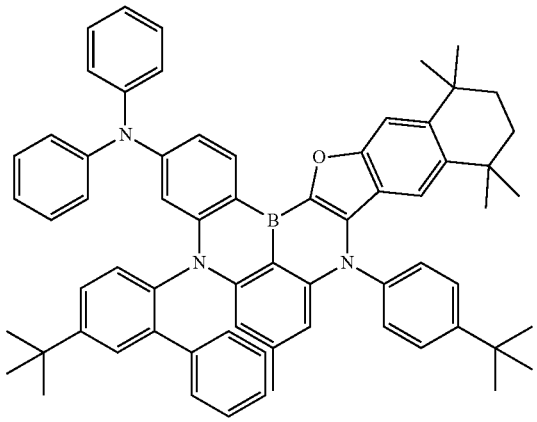
1608
-continued
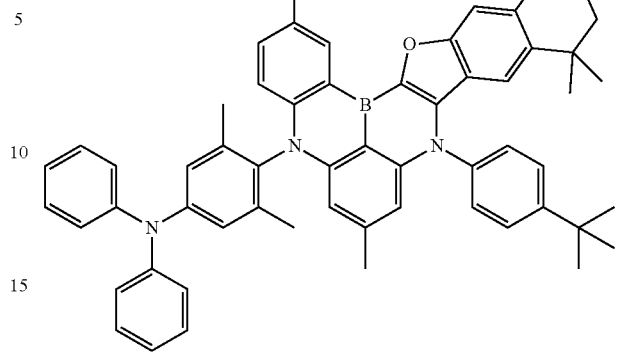
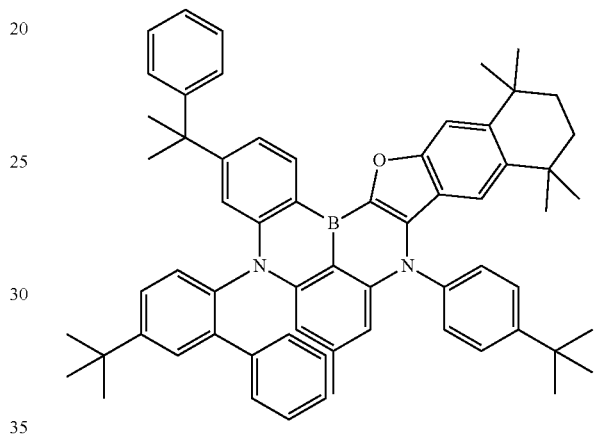
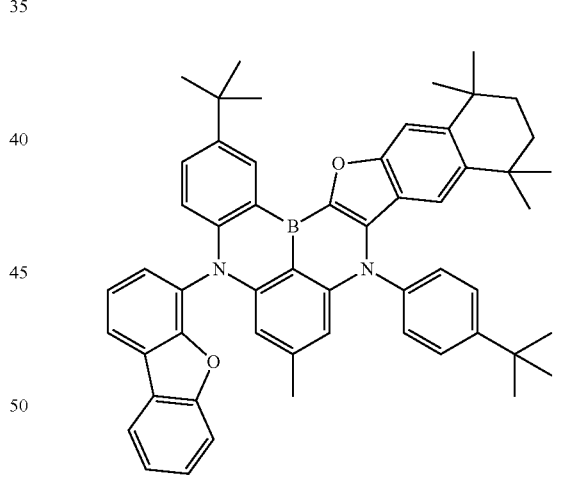
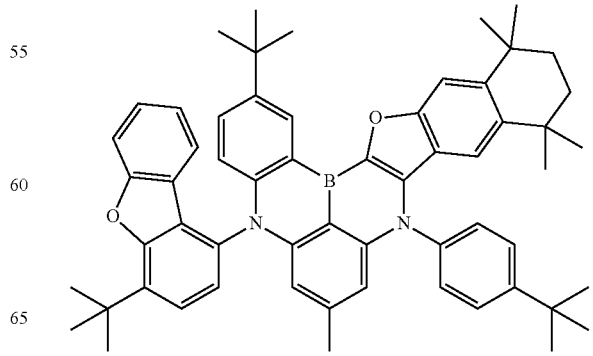

1609
-continued
1610
-continued
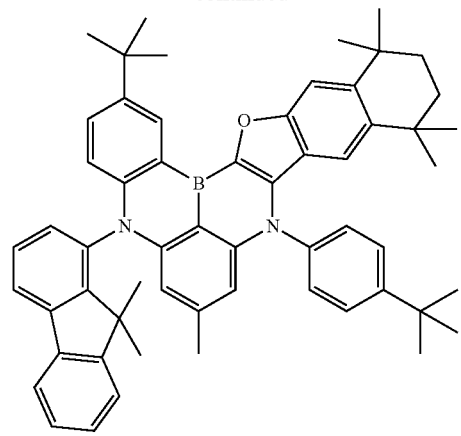
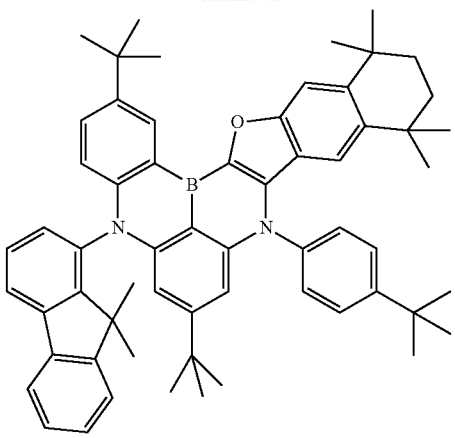

1611
-continued
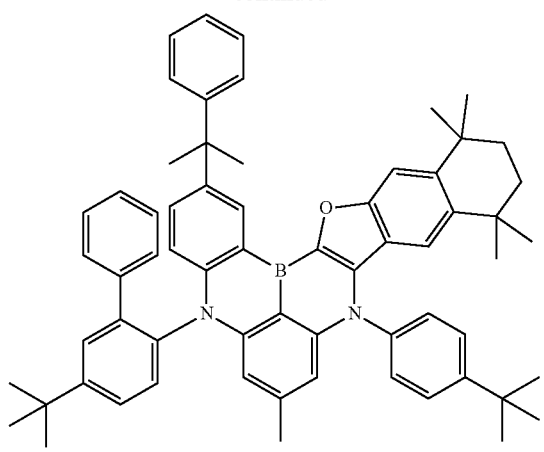
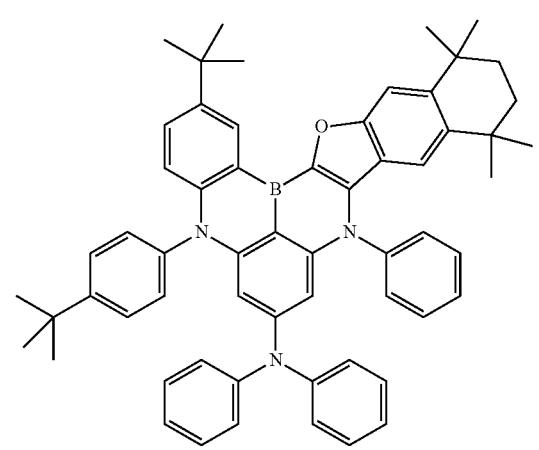
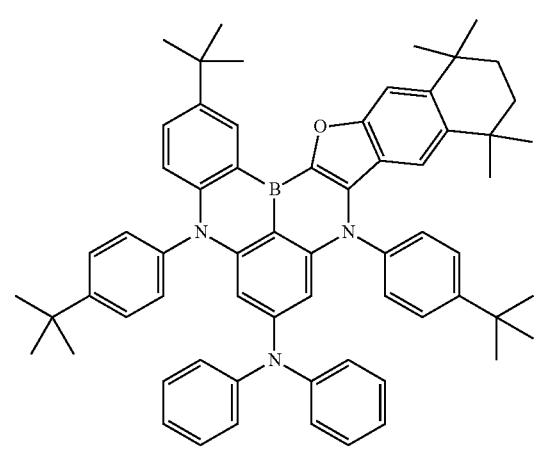
1612
-continued
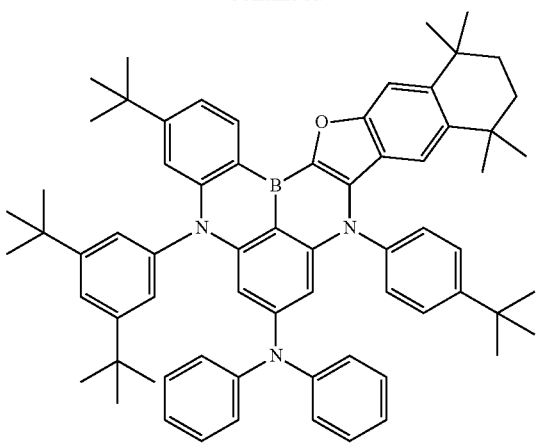
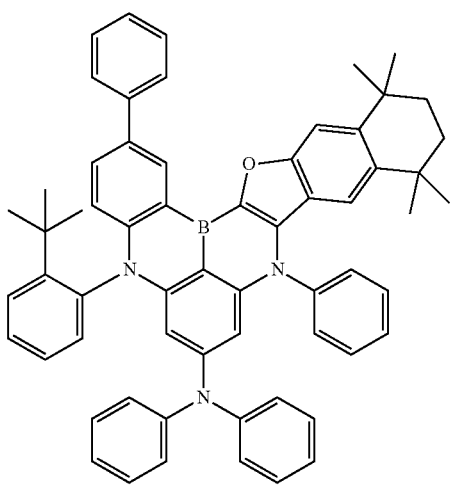
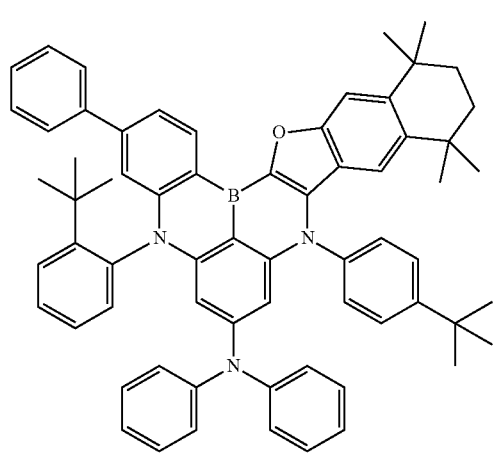

1613
-continued
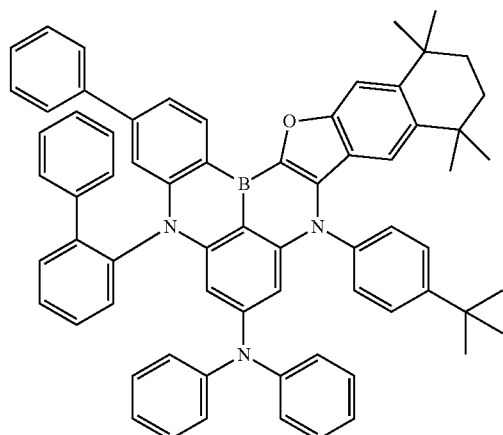
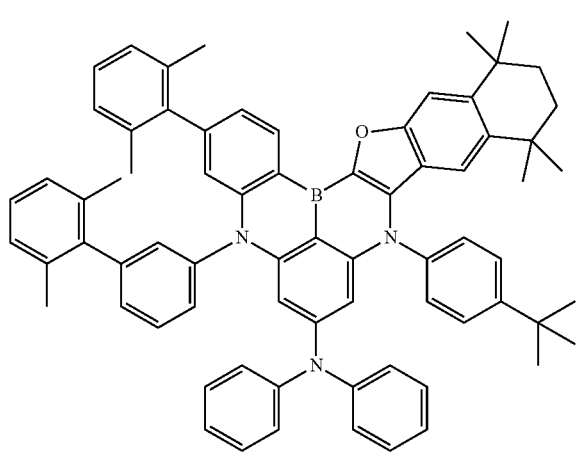
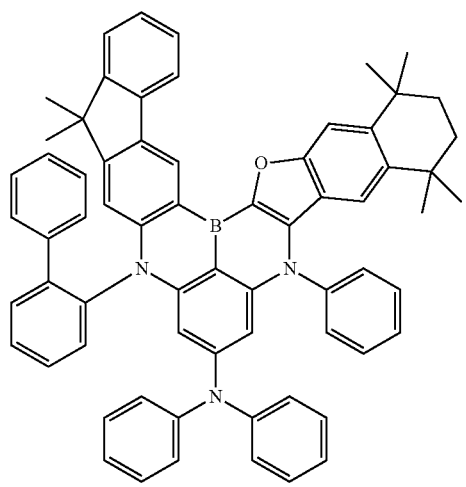
1614
-continued
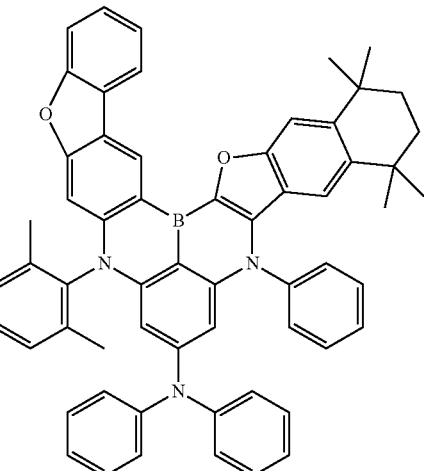
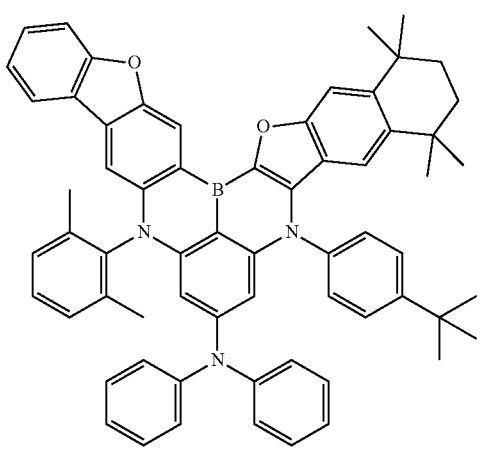
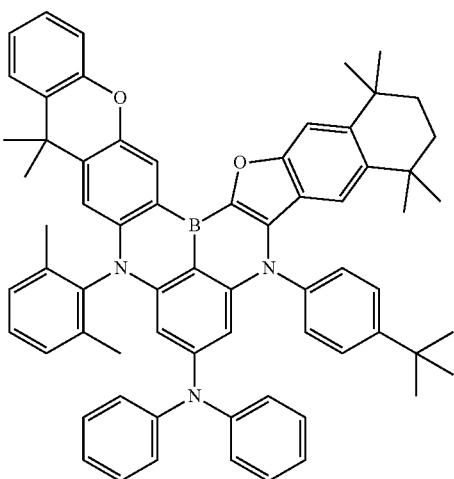

1615
-continued
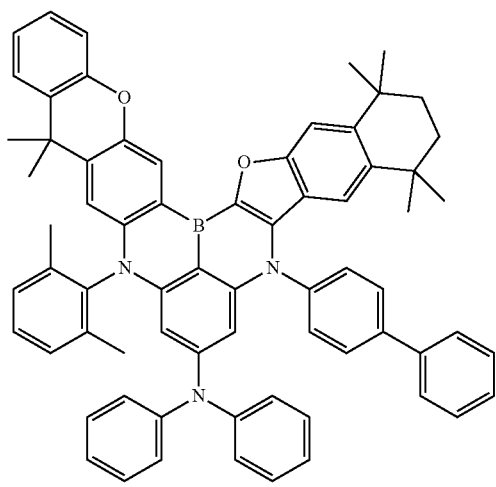
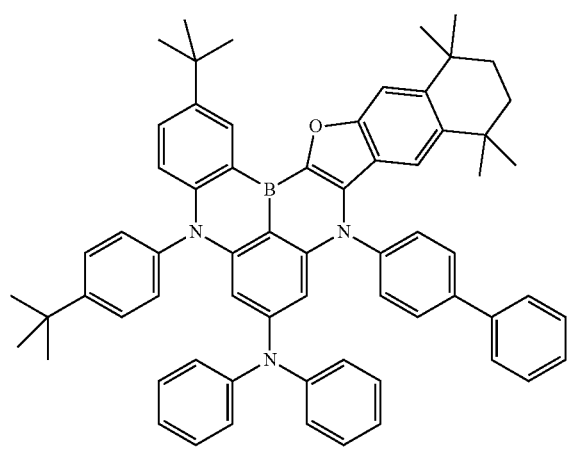
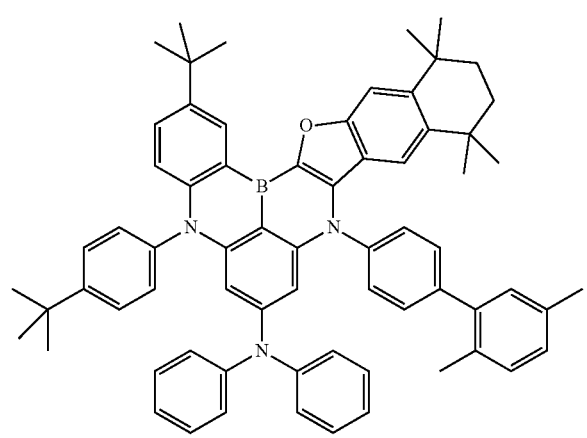
1616
-continued
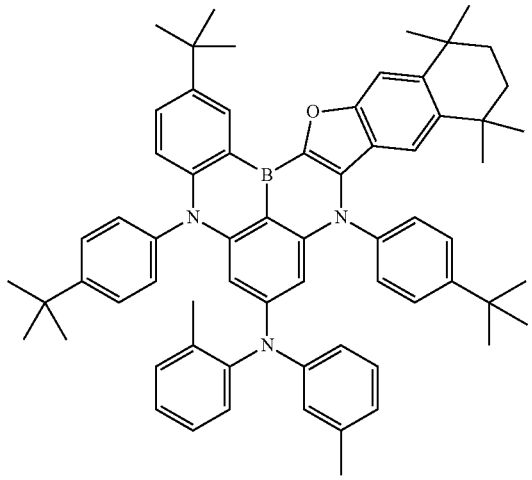
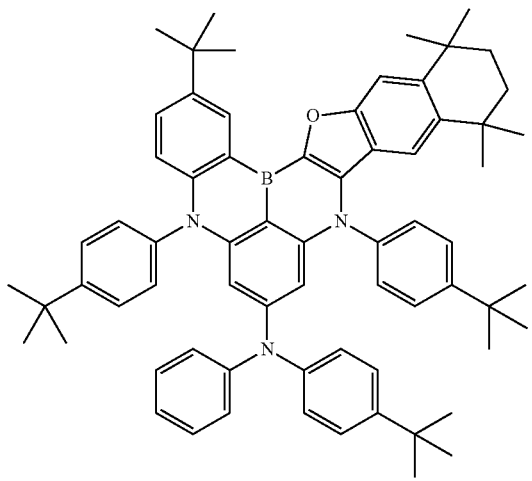
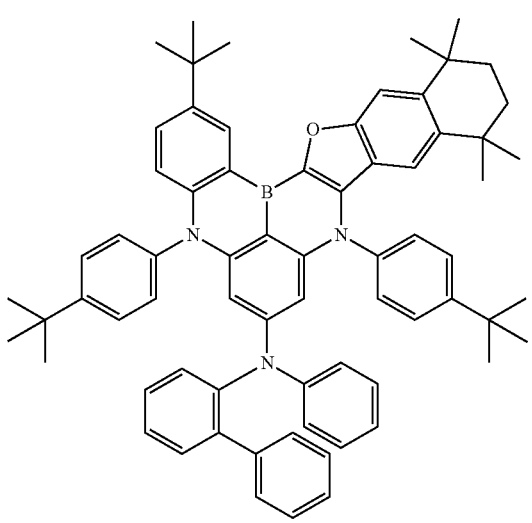

1617
-continued
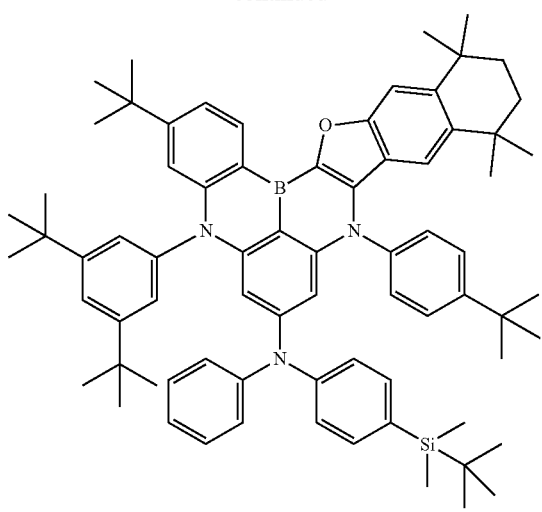
1618
-continued
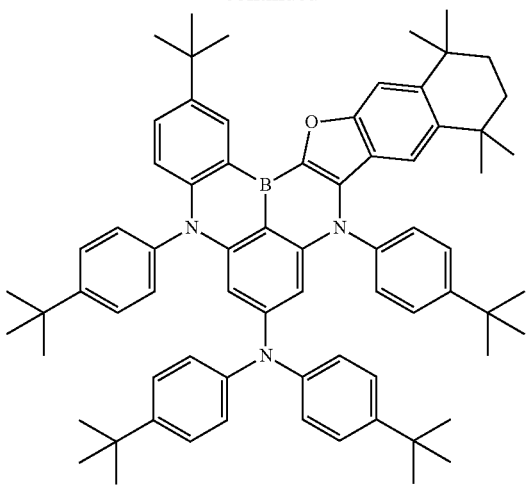
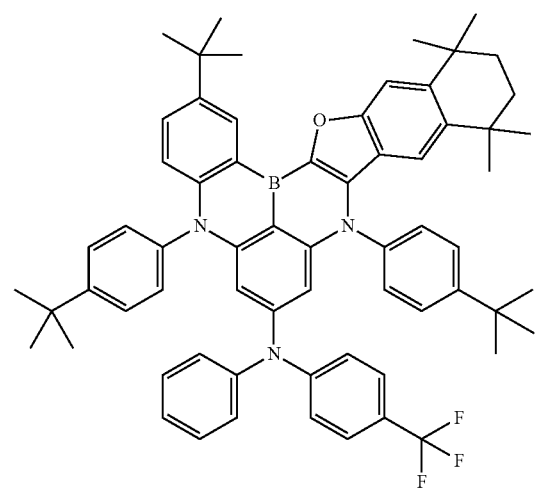
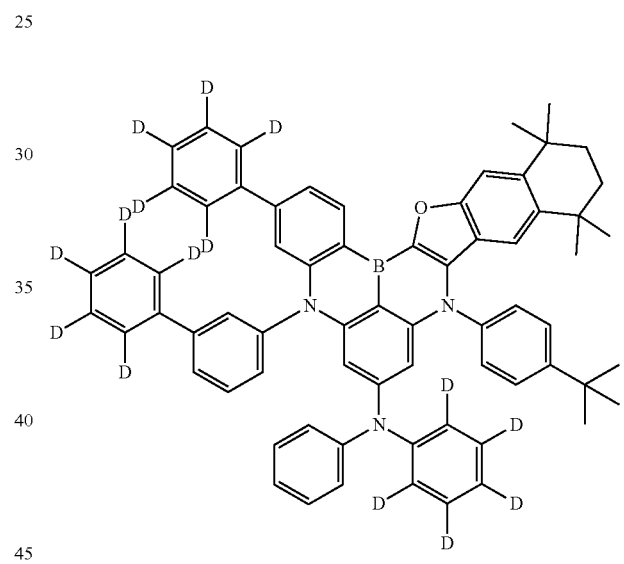
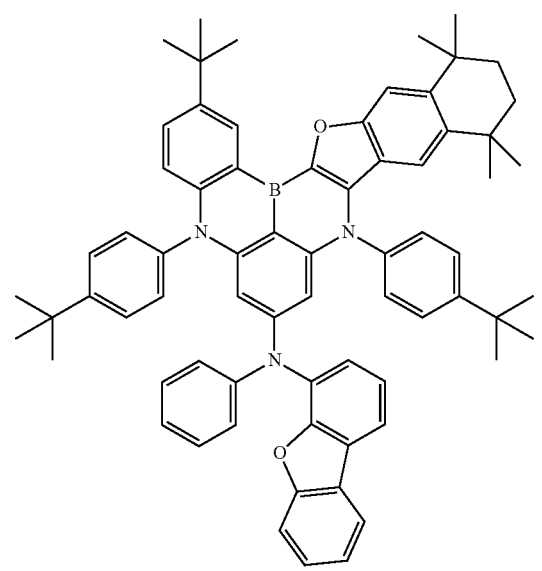
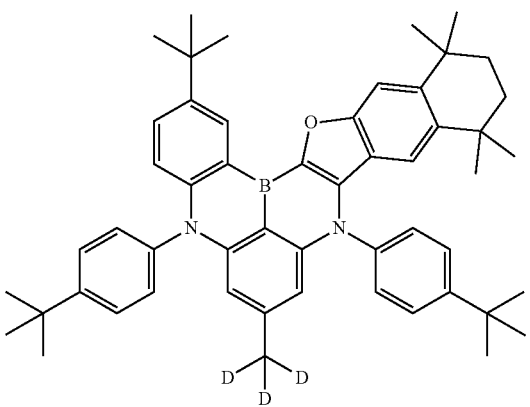

| 1619 -continued | 1620 -continued |
|---|---|
| 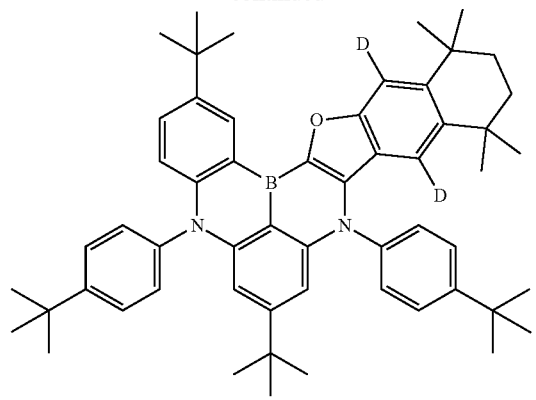 | 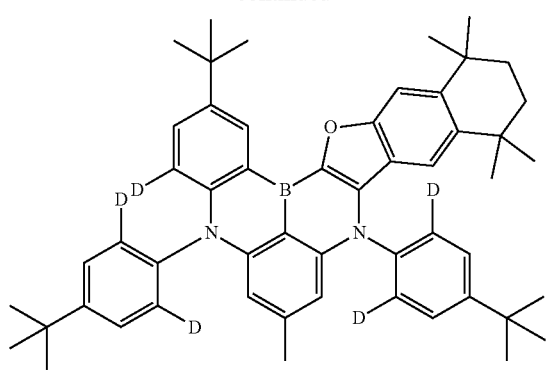 |
| 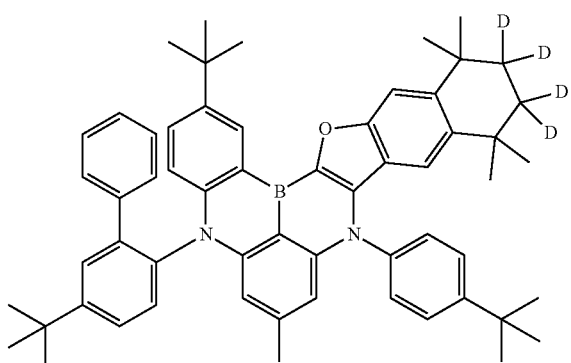 | 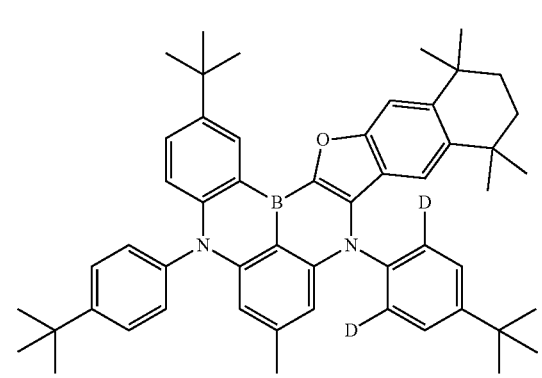 |
| 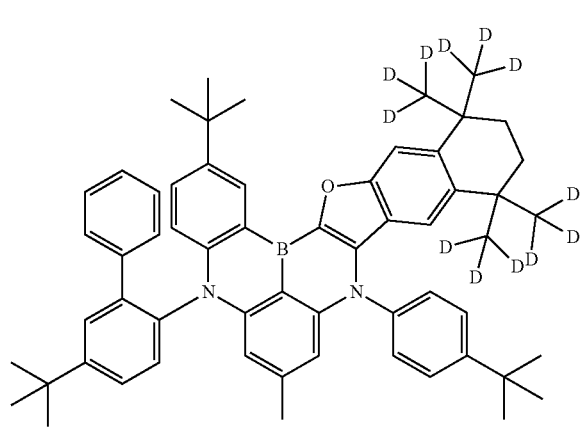 | 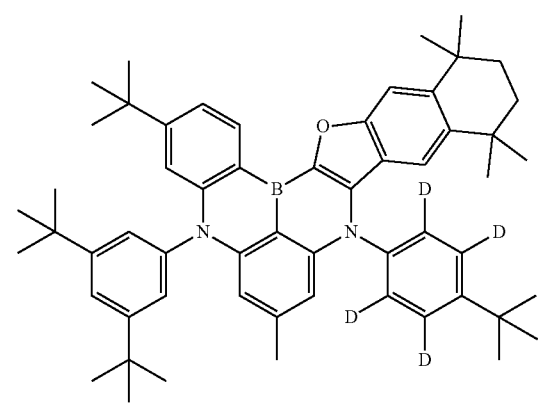 |
| 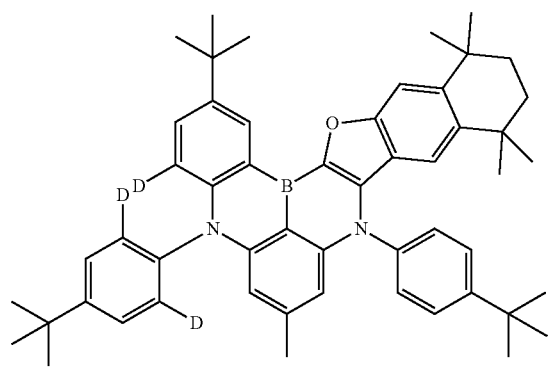 | 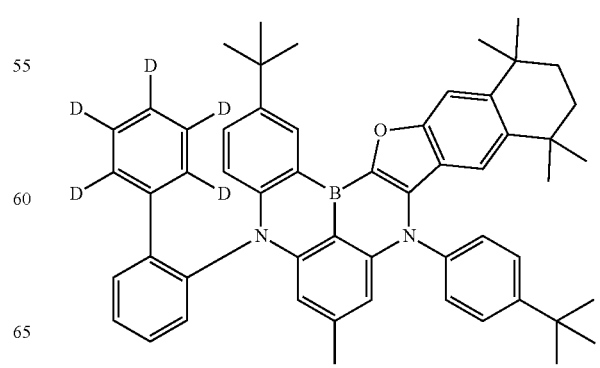 |

| 1621 -continued | 1622 -continued |
|---|---|
| 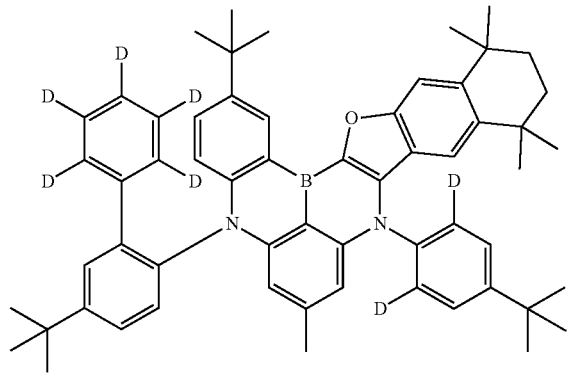 | 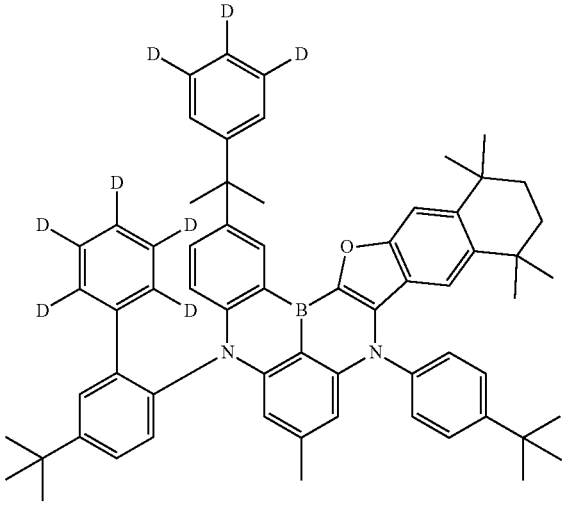 |
| 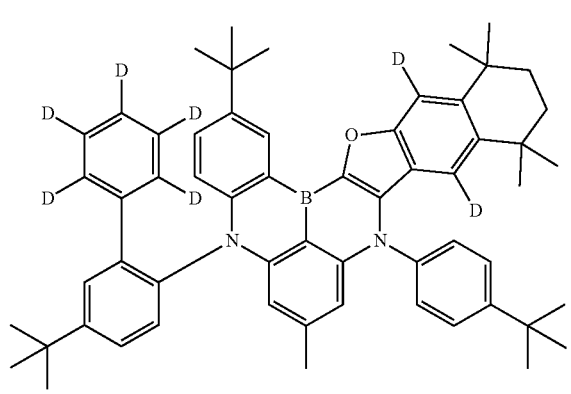 | |
| 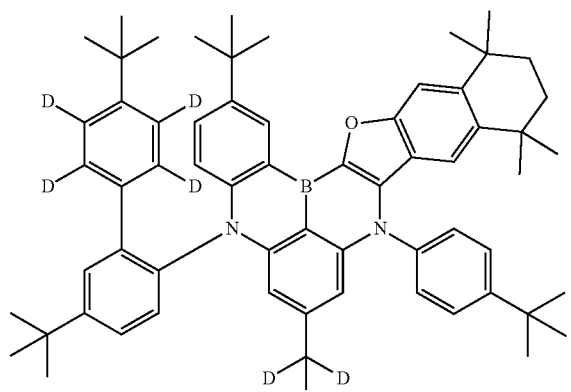 | 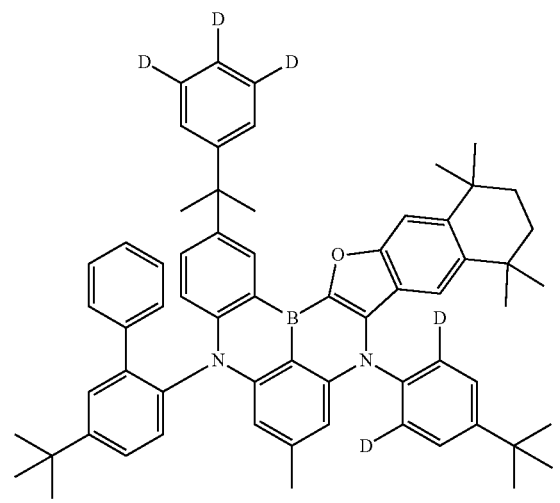 |
| 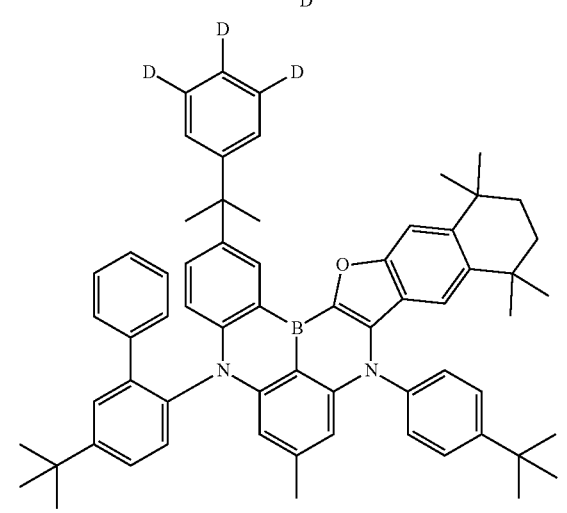 | 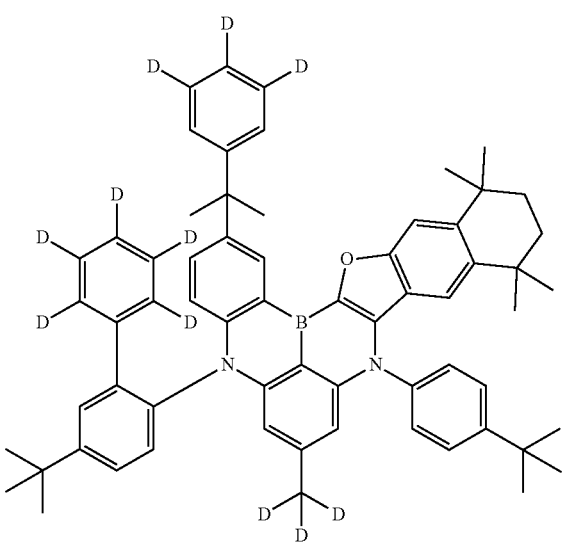 |

1623
-continued
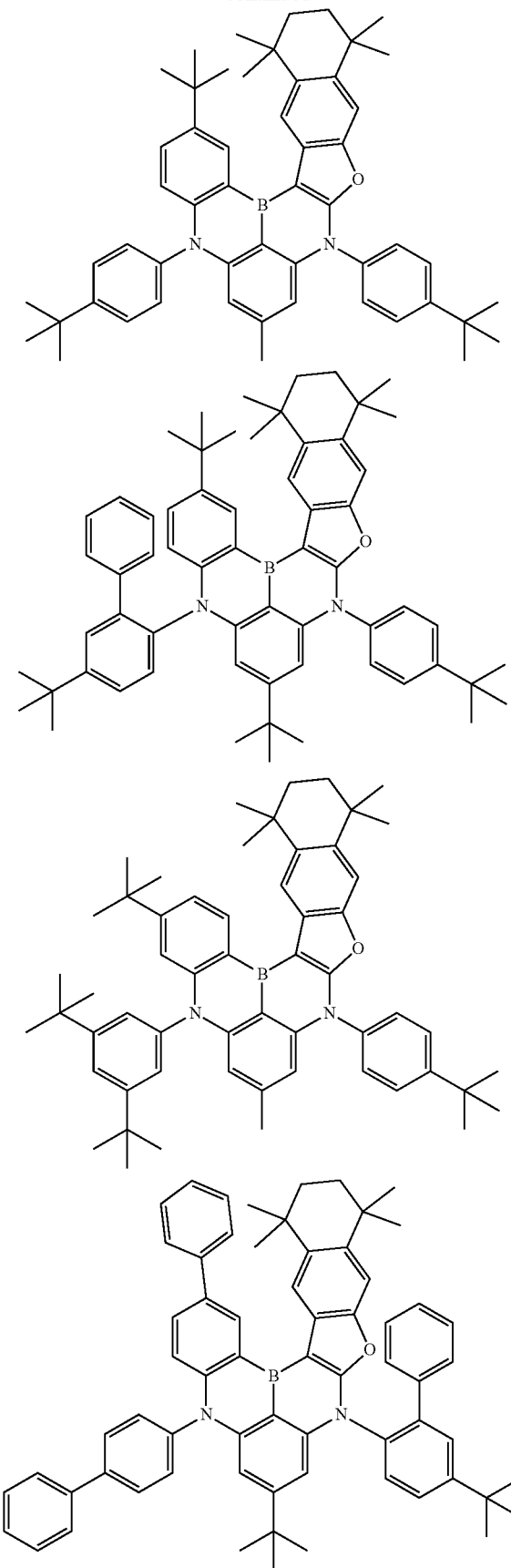
1624
-continued
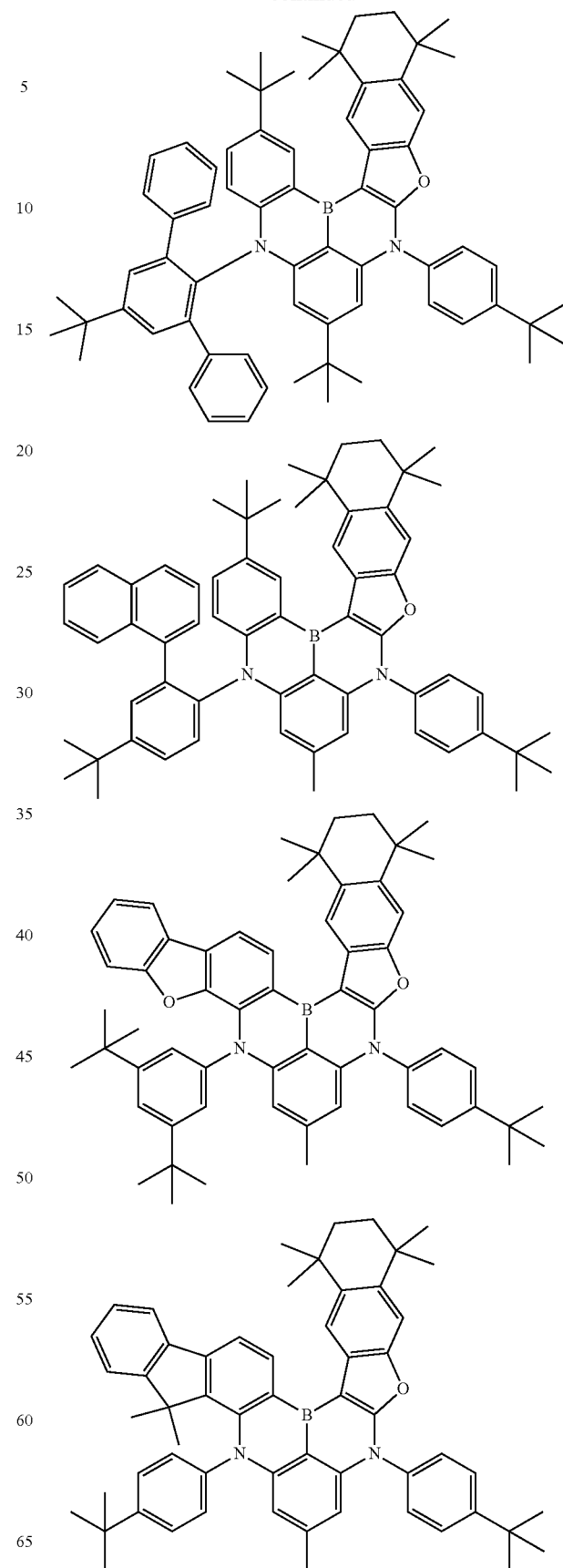

| 1625 | 1626 |
|---|---|
| -continued | -continued |
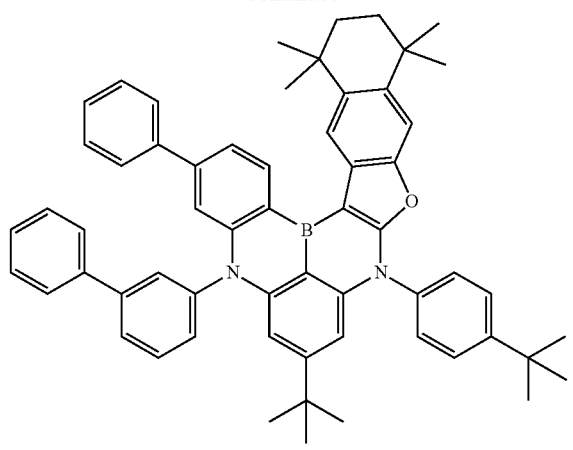
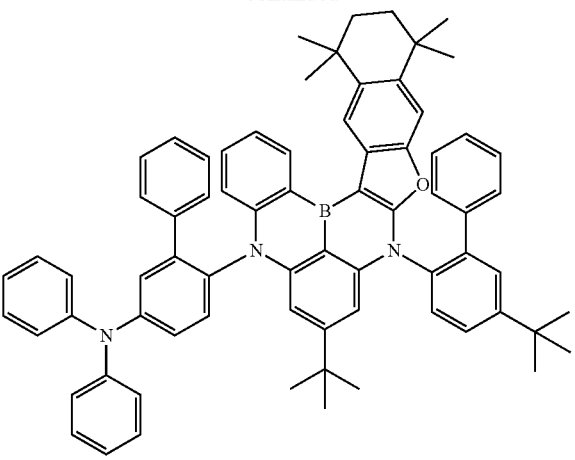
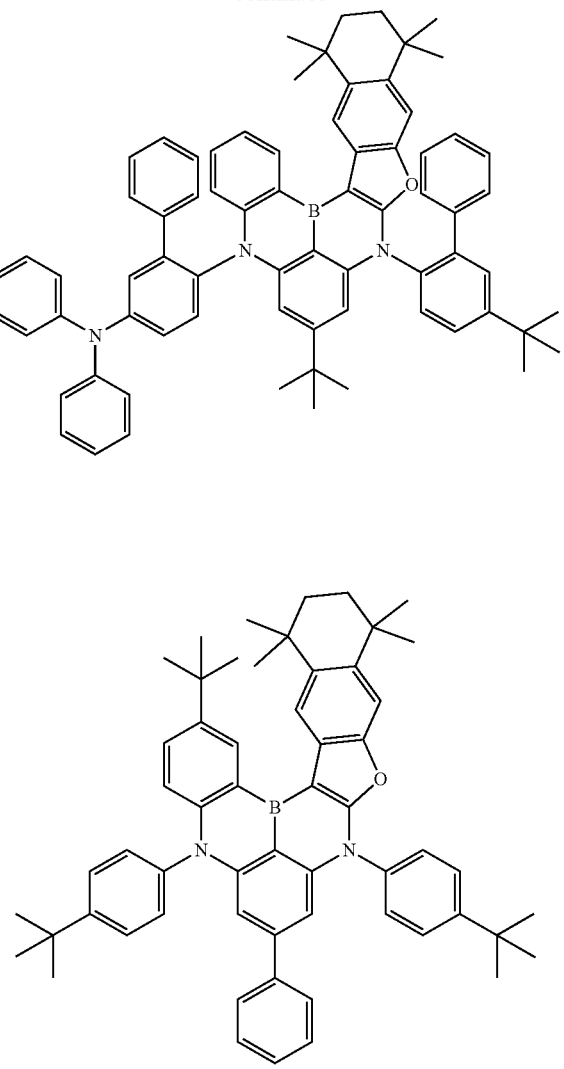
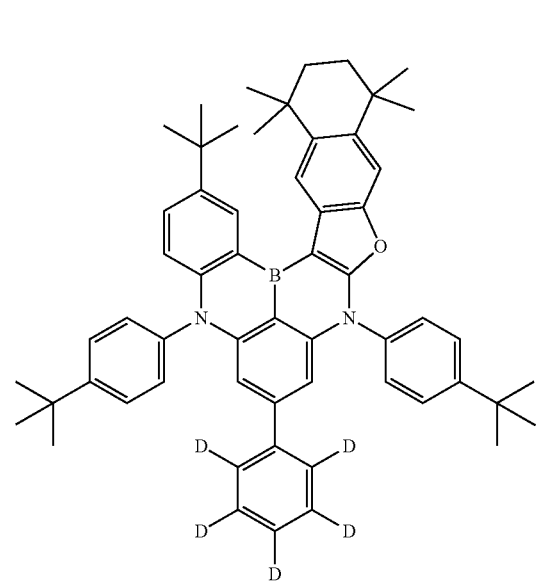

1627
-continued
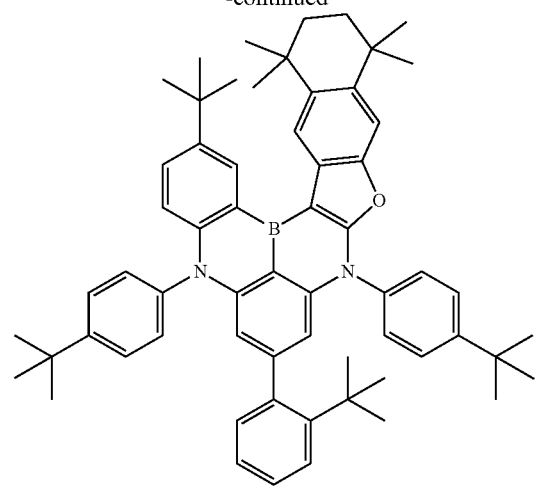
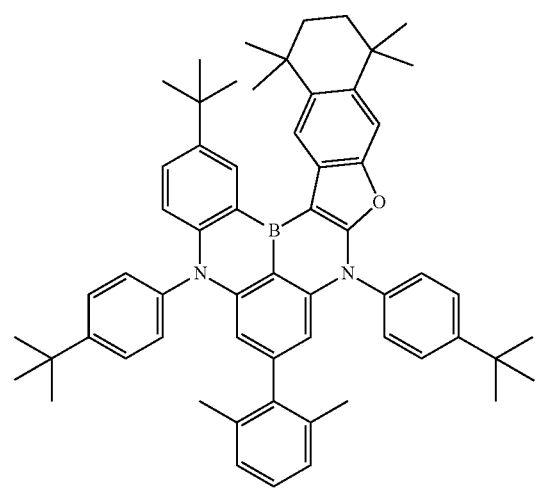
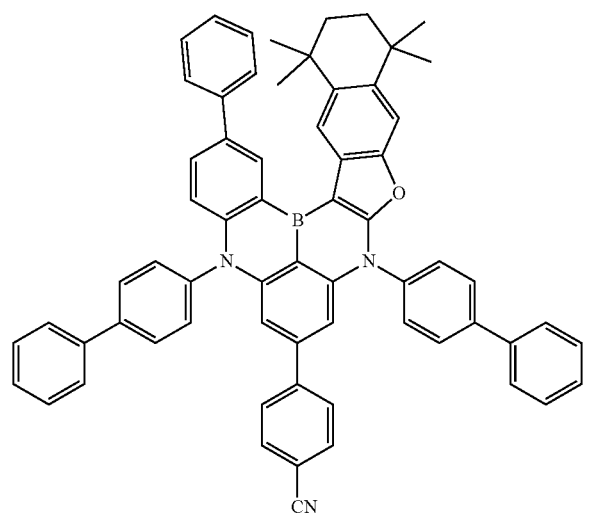
1628
-continued
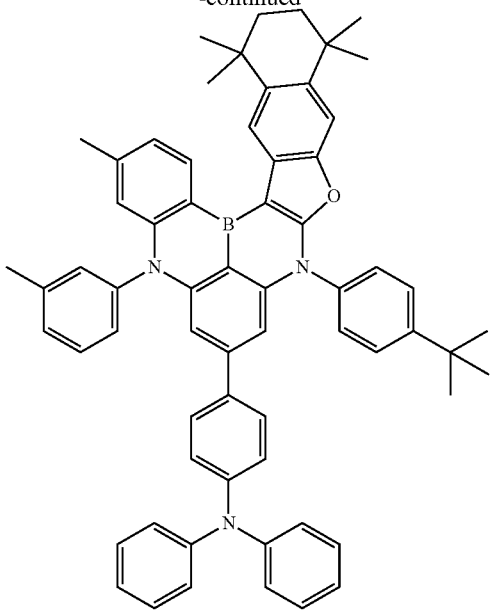
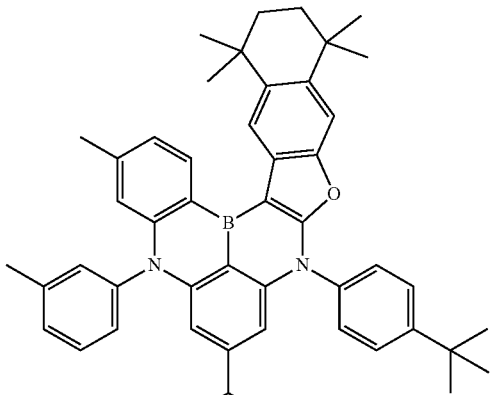
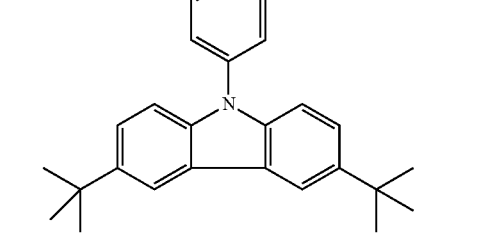
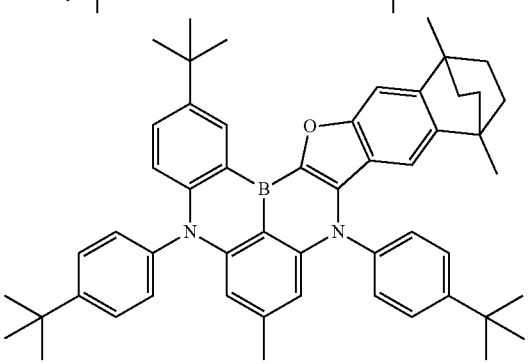

1629
-continued
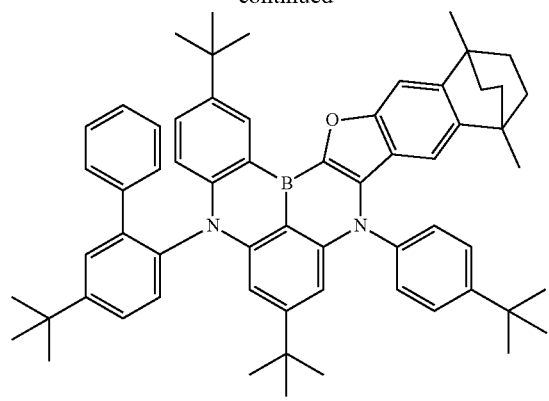
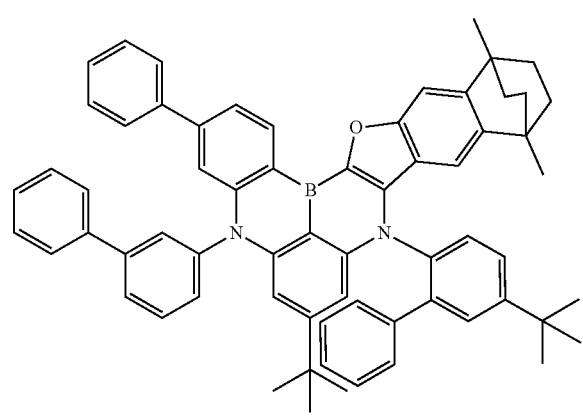
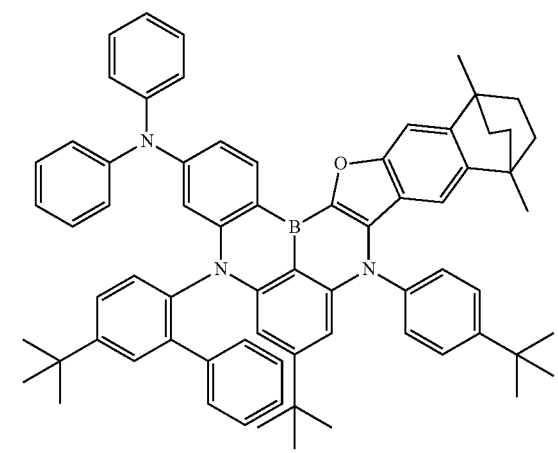
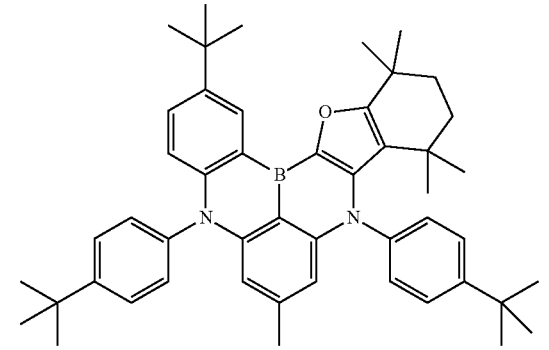
1630
-continued
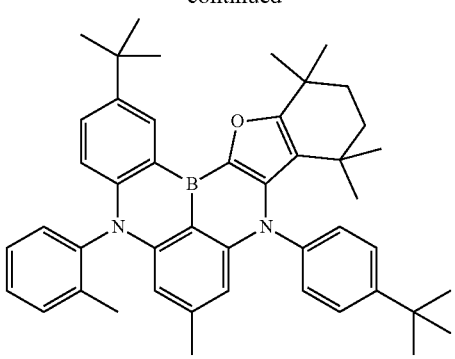
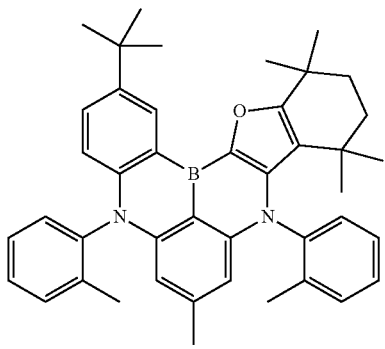
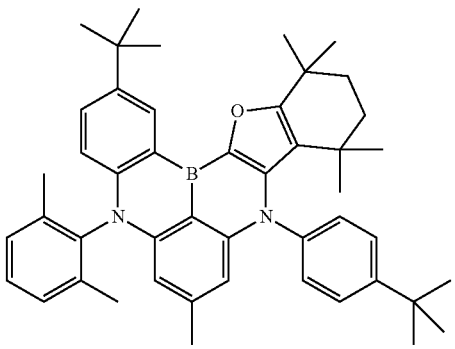
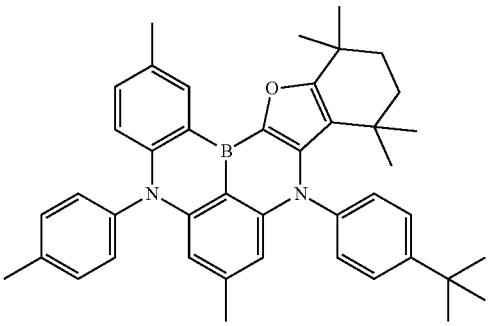
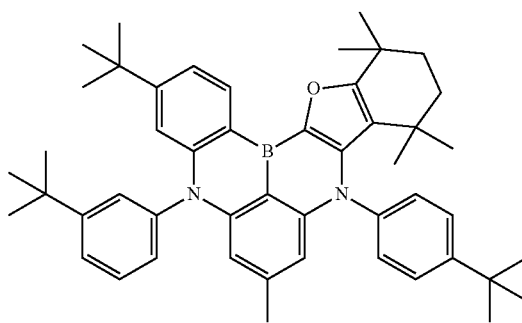

1631
-continued
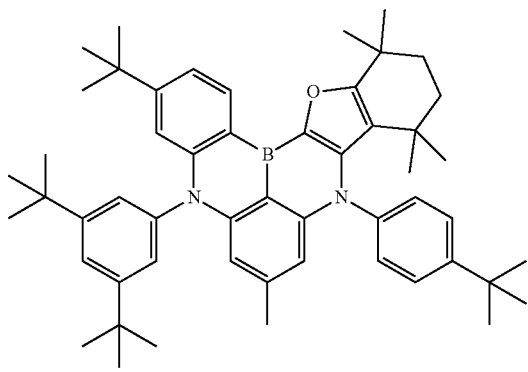
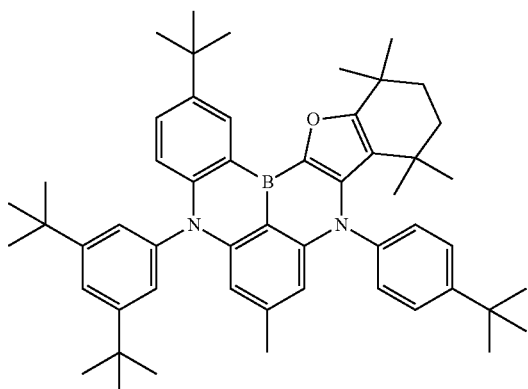
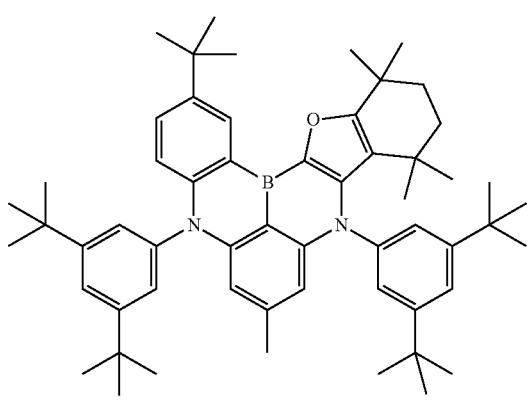
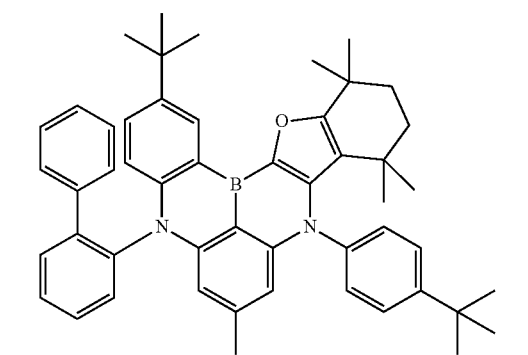
1632
-continued
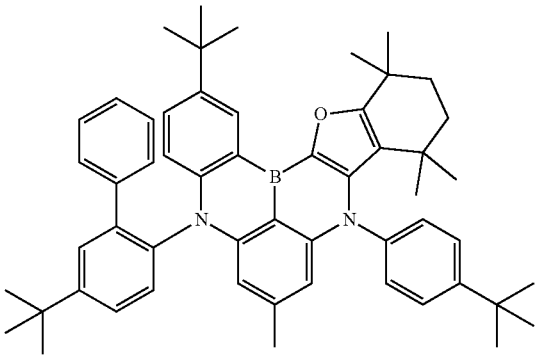
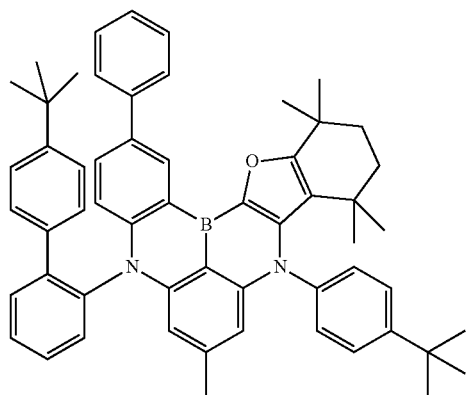
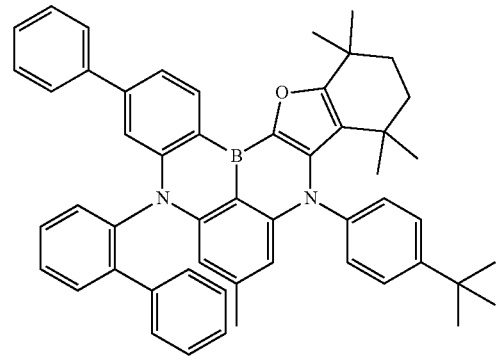
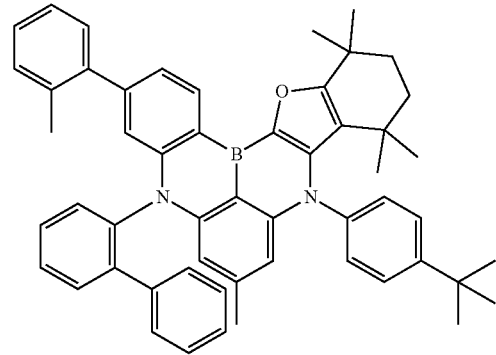

| 1633 | 1634 |
|---|---|
| -continued | -continued |
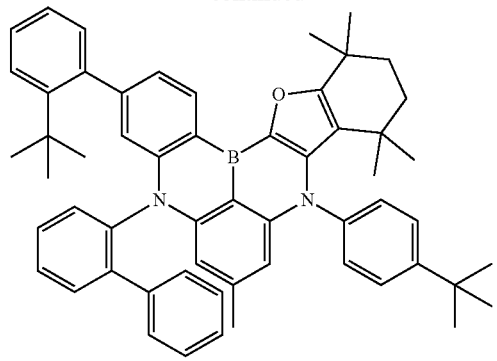
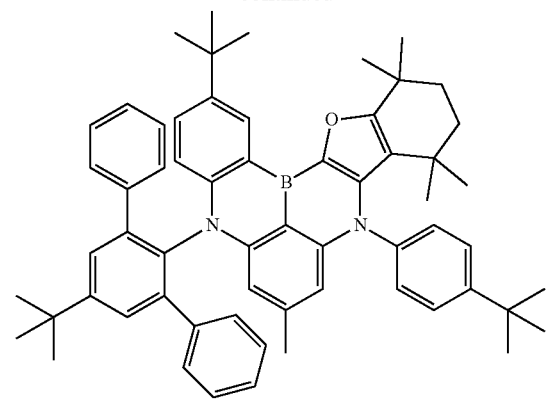
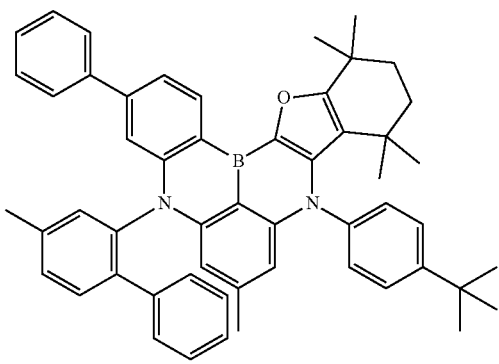
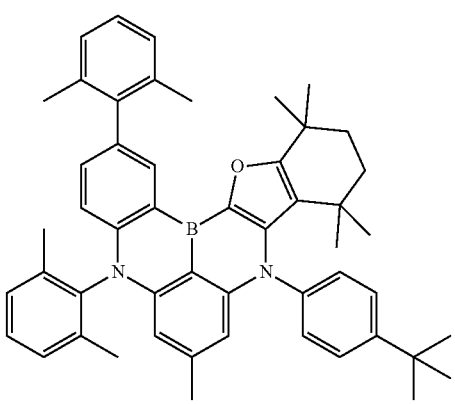
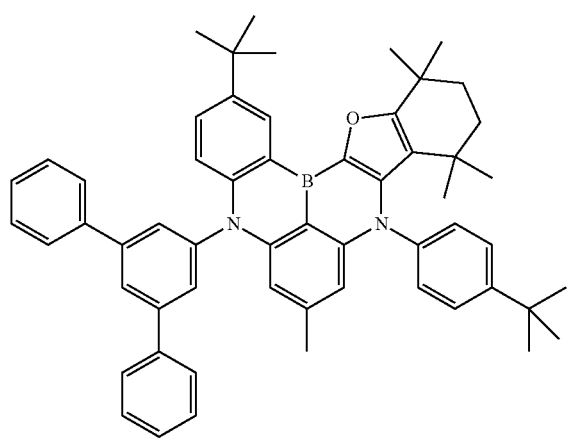
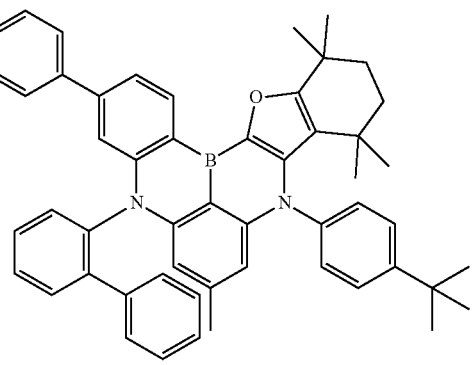
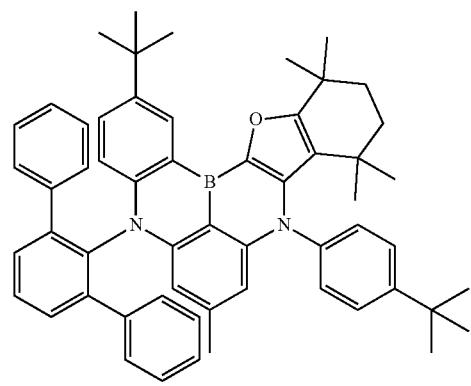
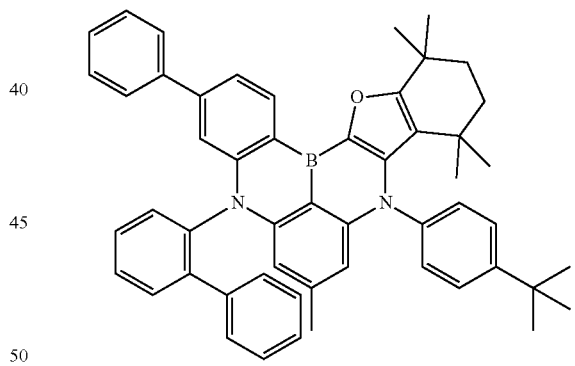
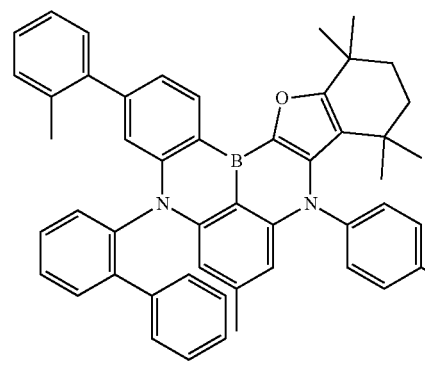

1635
-continued
1636
-continued
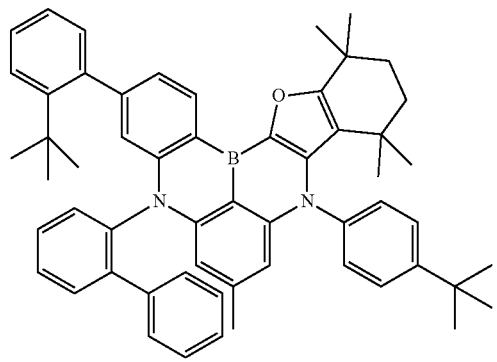
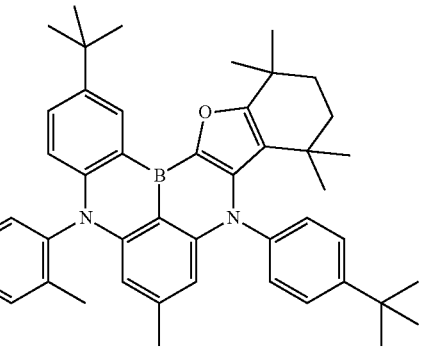
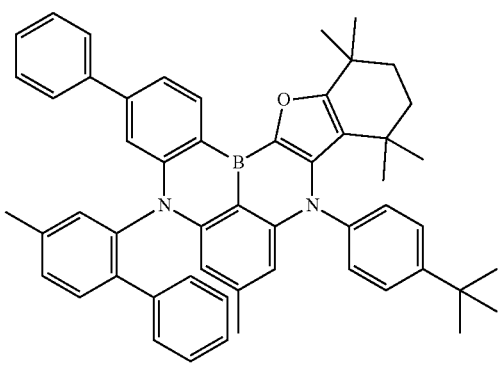
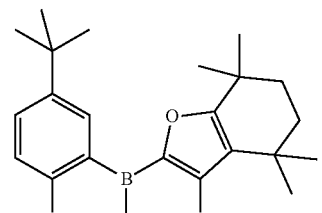
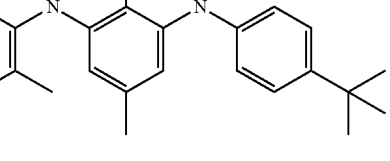
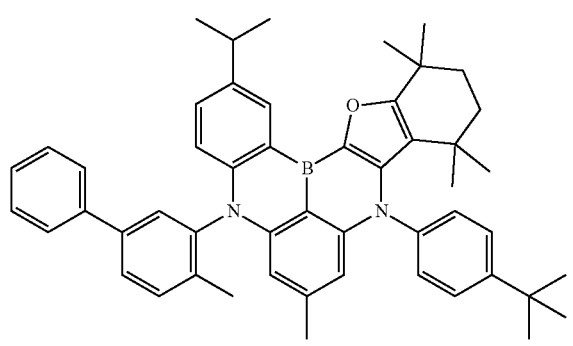
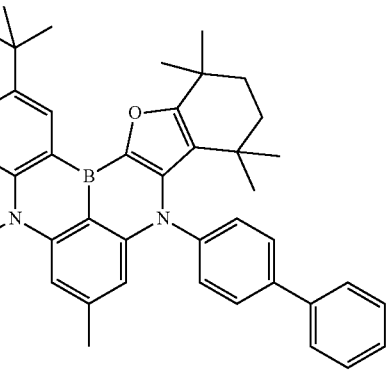
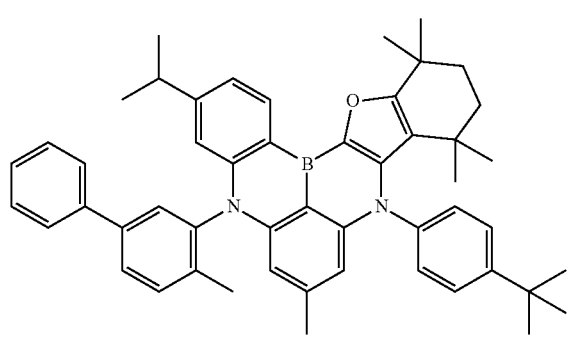
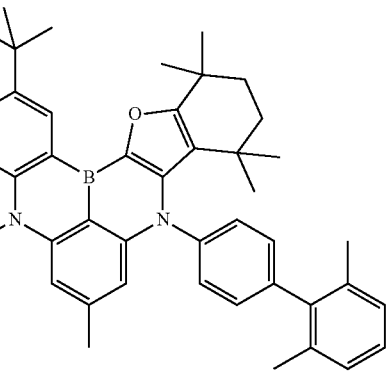

1637
-continued
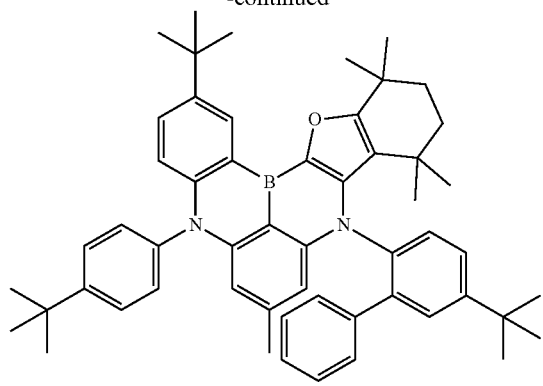
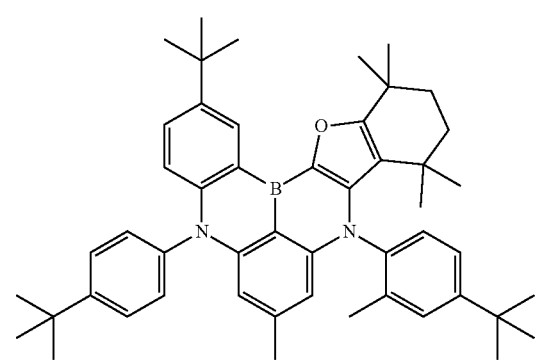
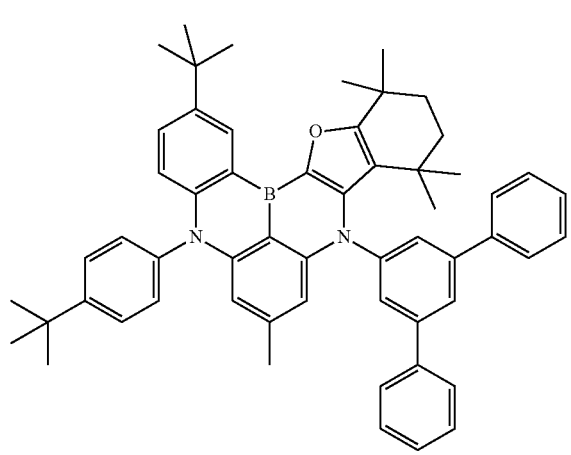
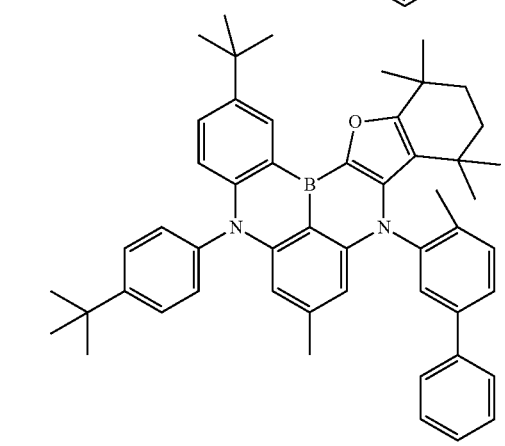
1638
-continued
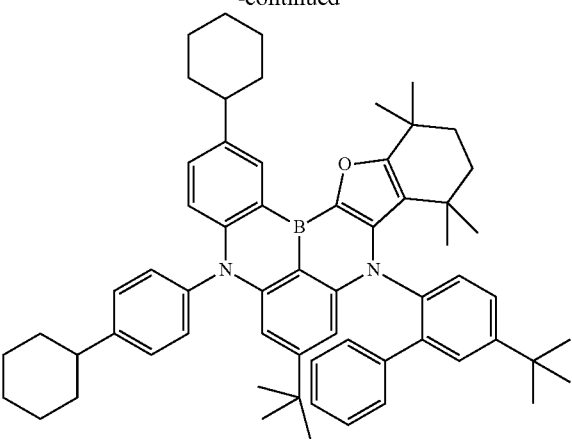
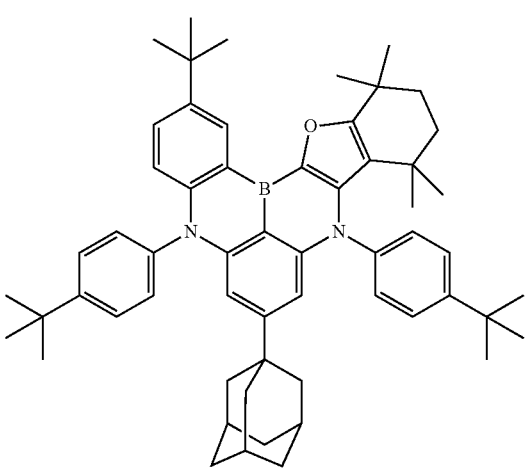
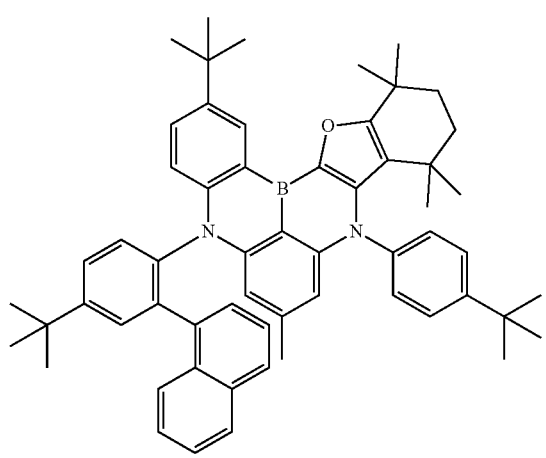

1639
-continued
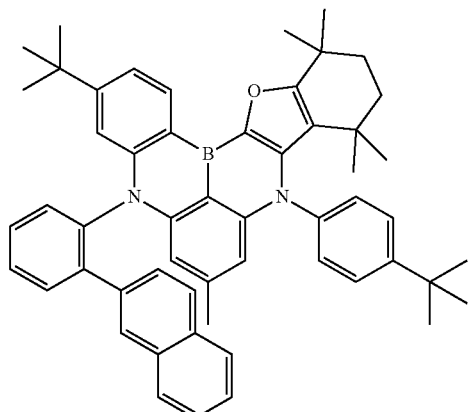
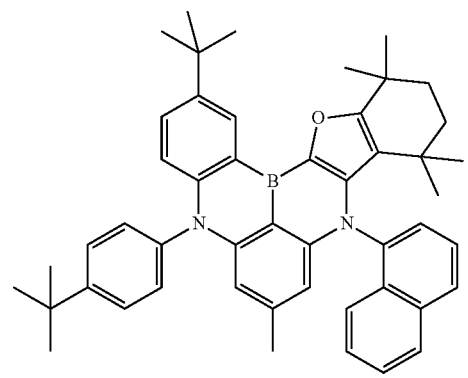
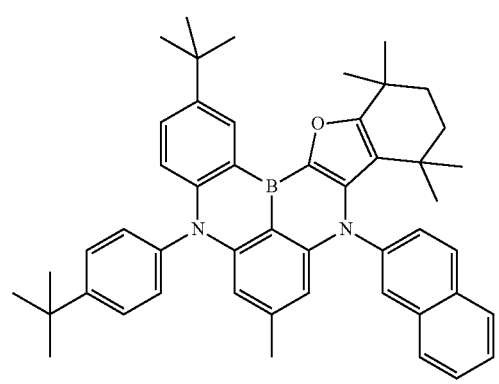
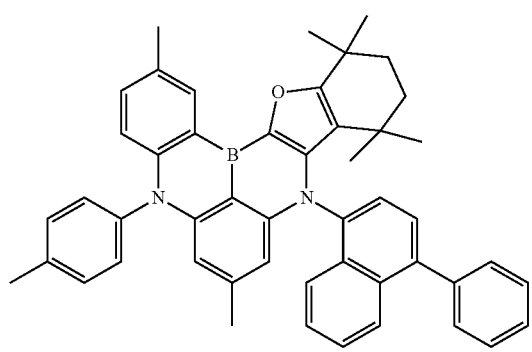
1640
-continued
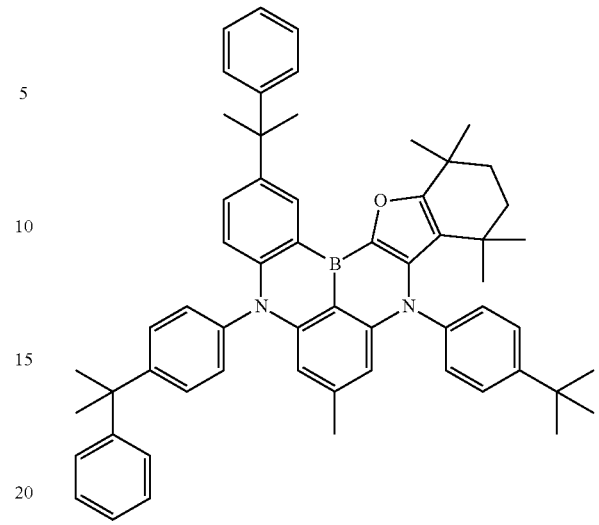
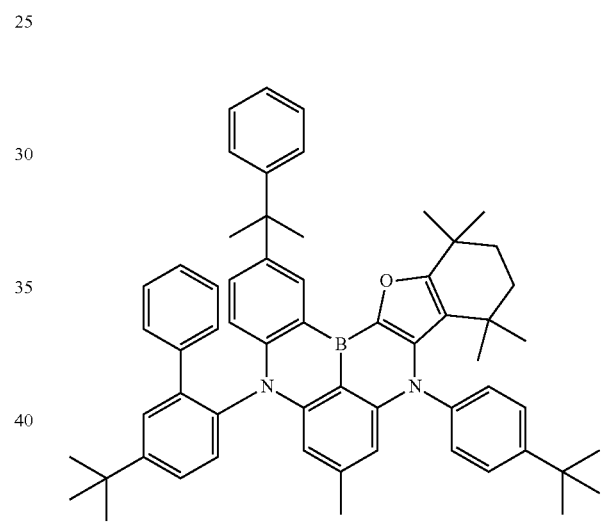
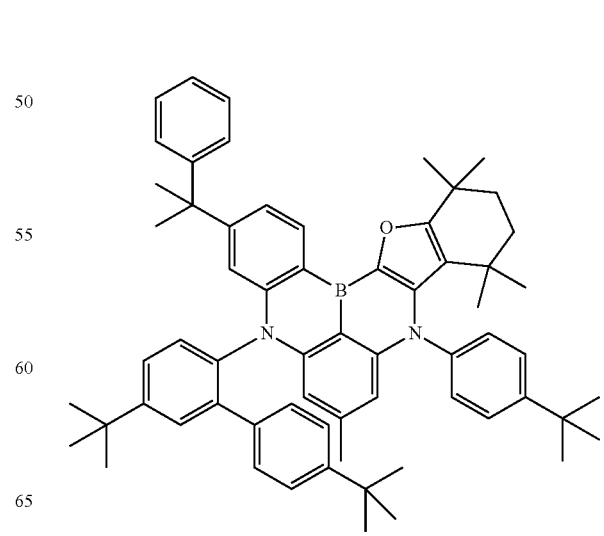

1641
-continued
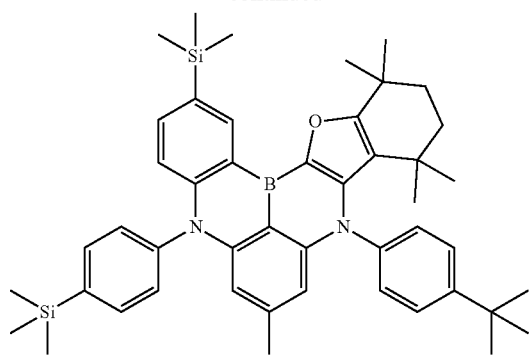
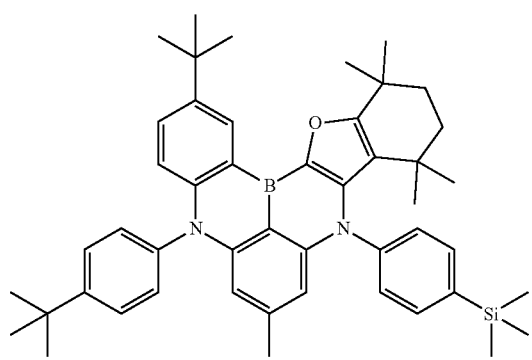
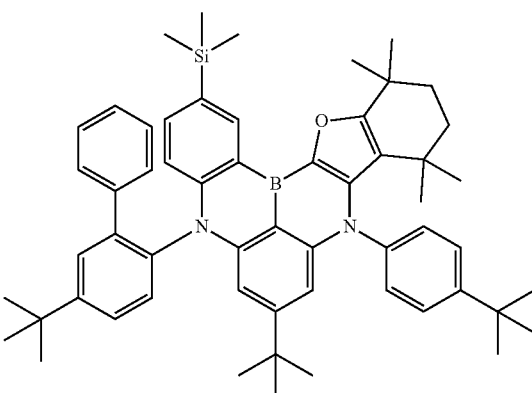
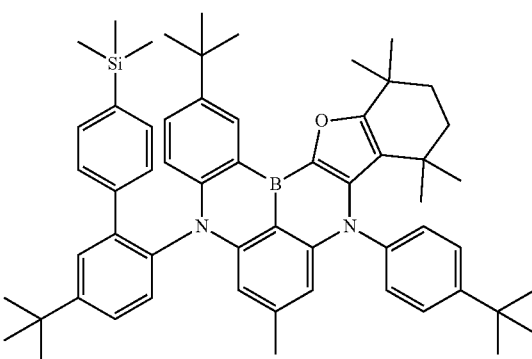
1642
-continued
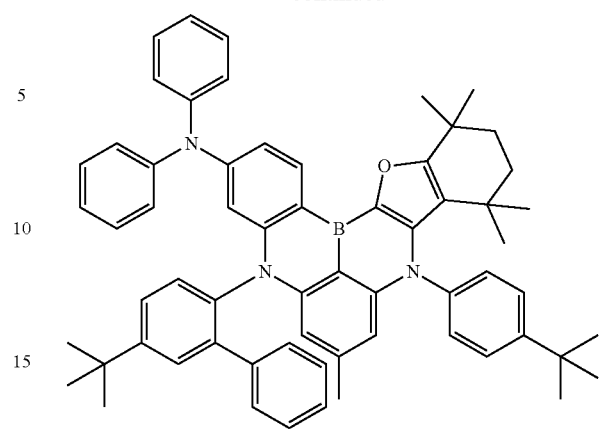
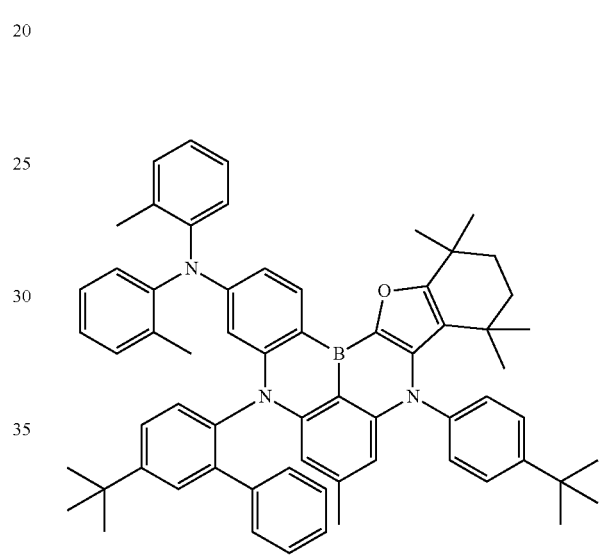
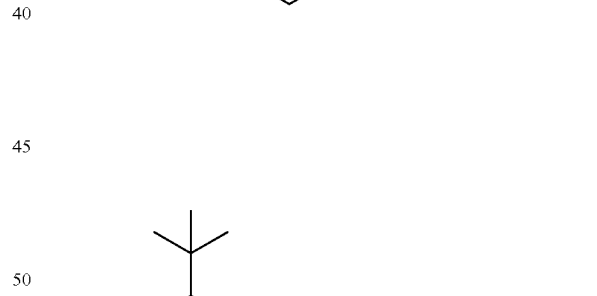
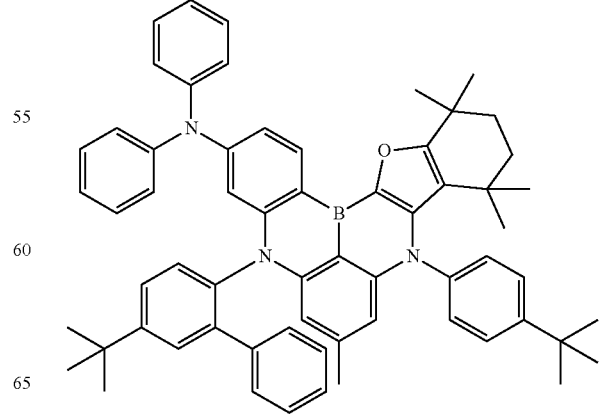

1643
-continued
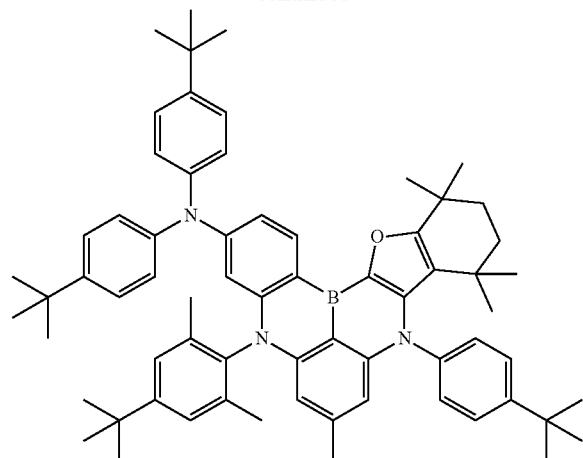
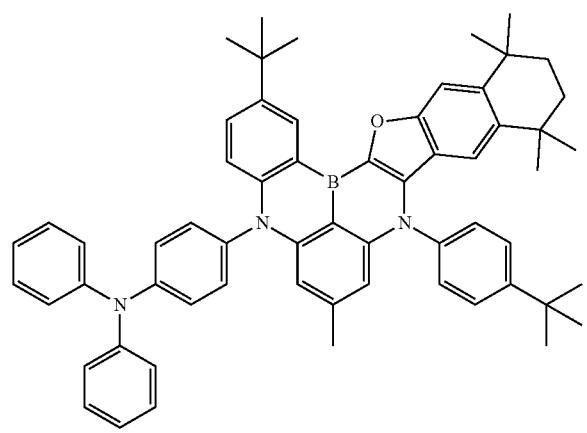
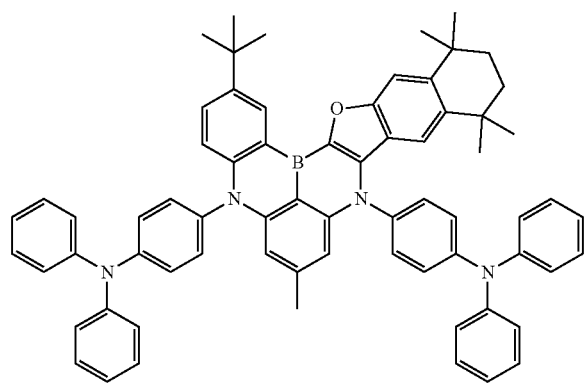
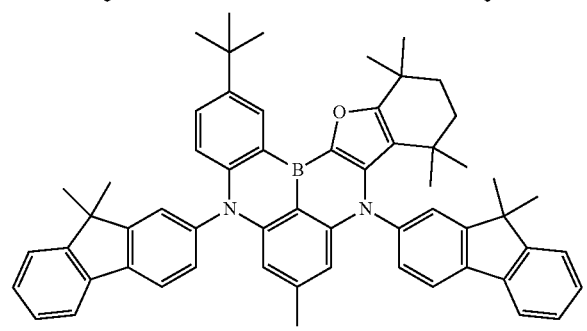
1644
-continued
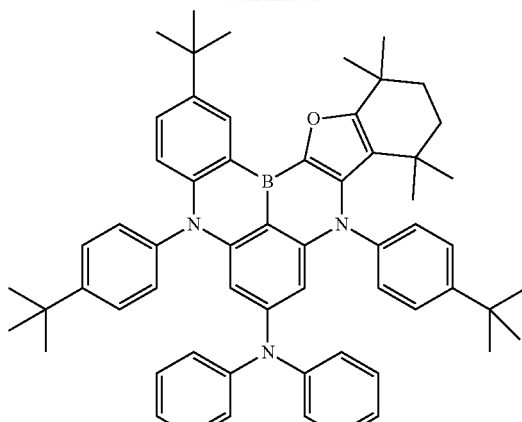
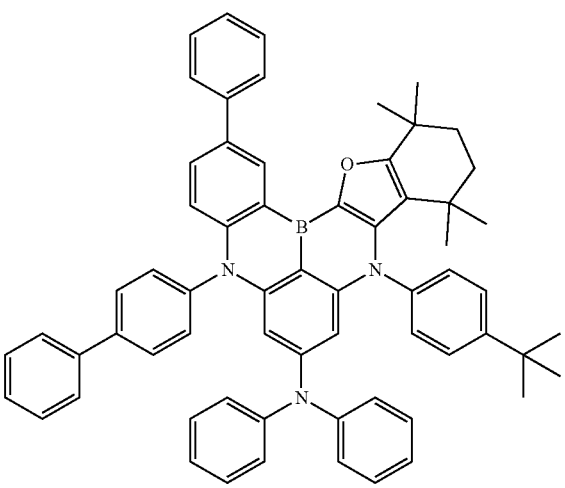
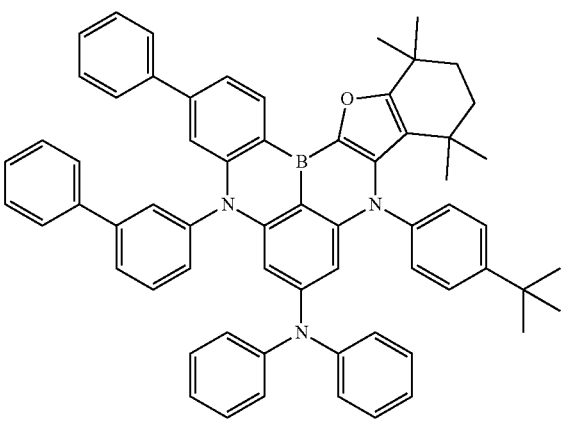

1645
-continued
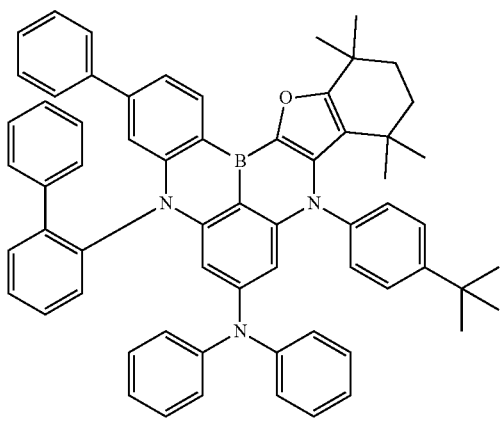
1646
-continued
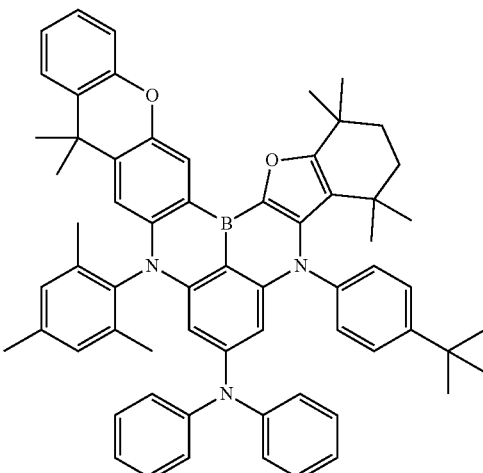
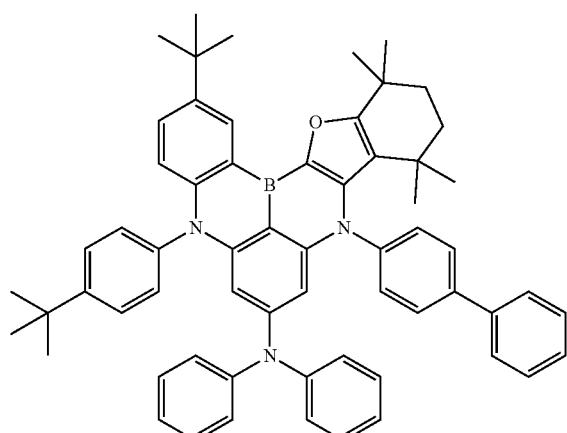
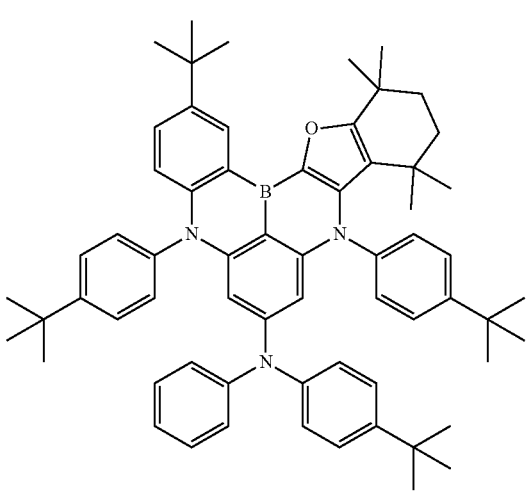
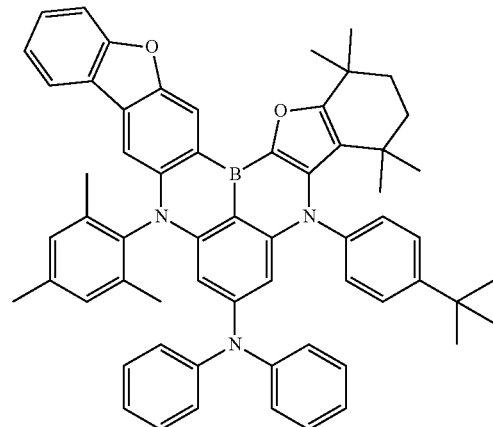
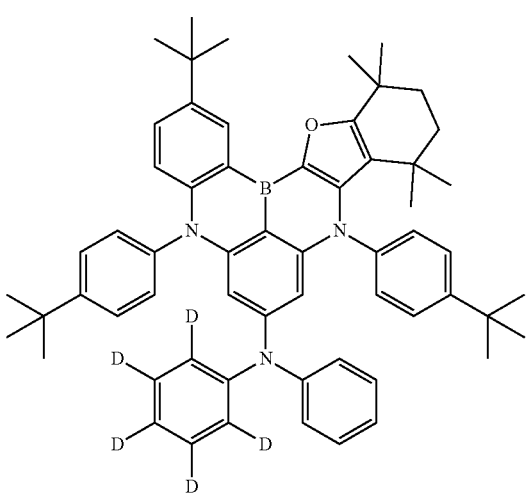

1647
-continued
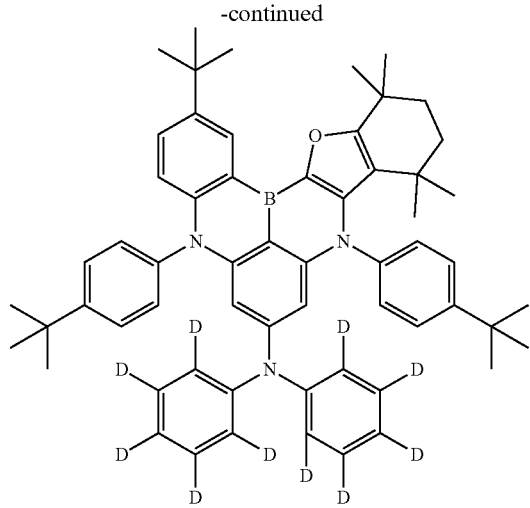
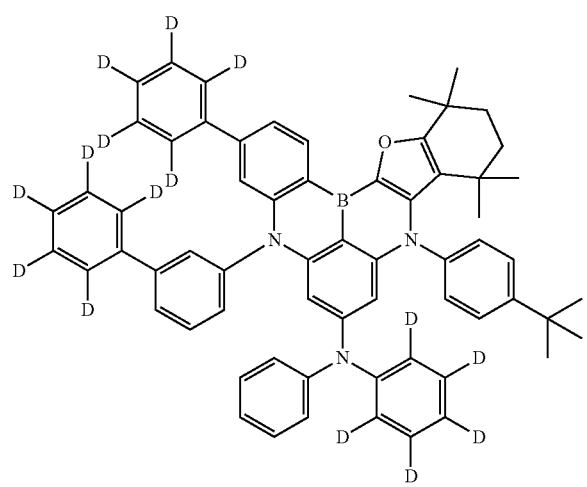
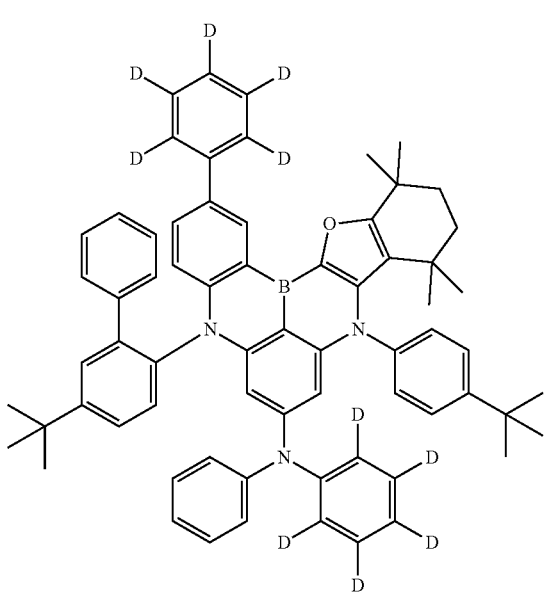
1648
-continued
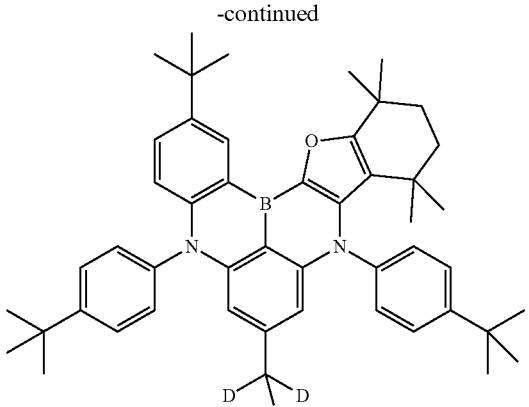
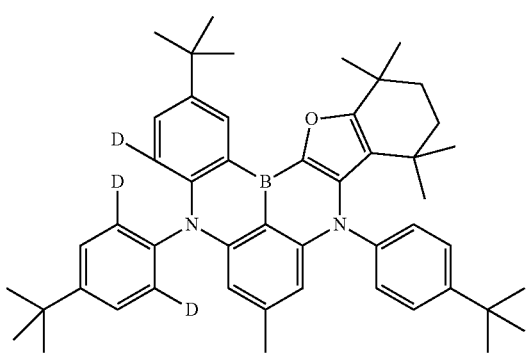
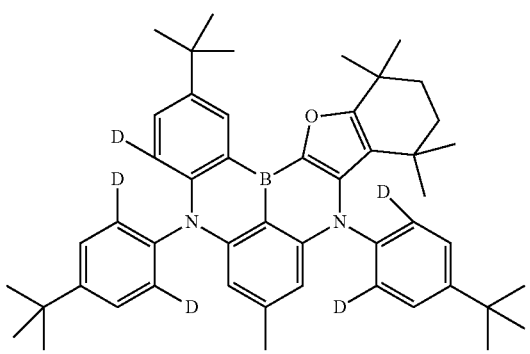
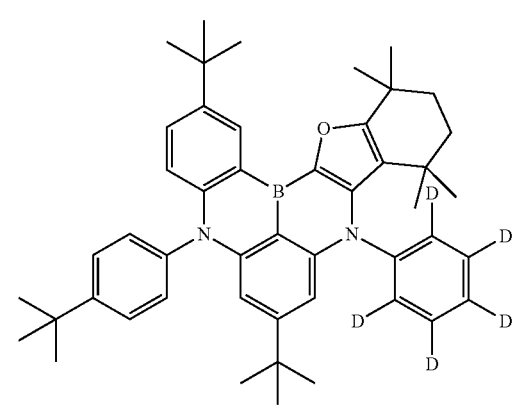

1649
-continued
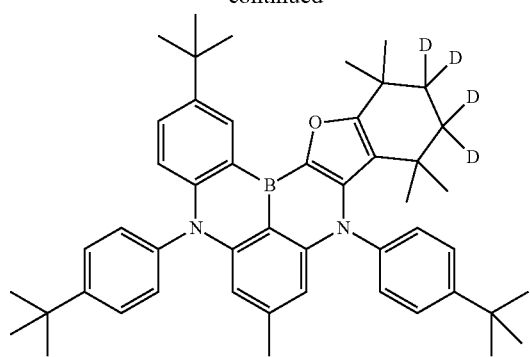
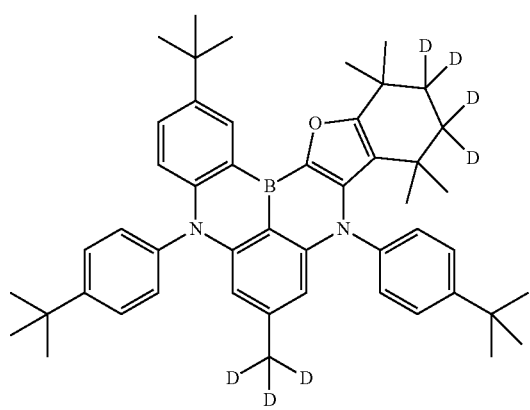
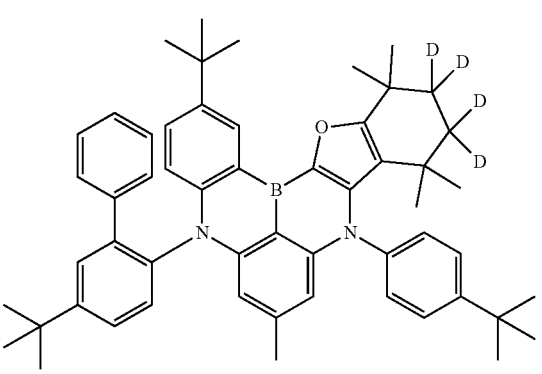
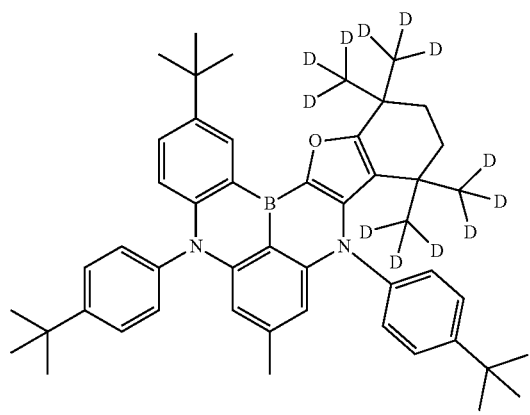
1650
-continued
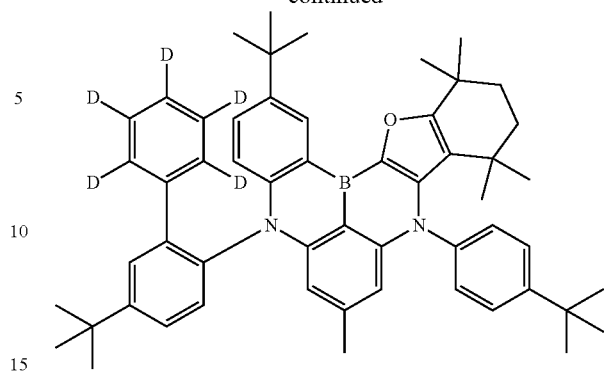
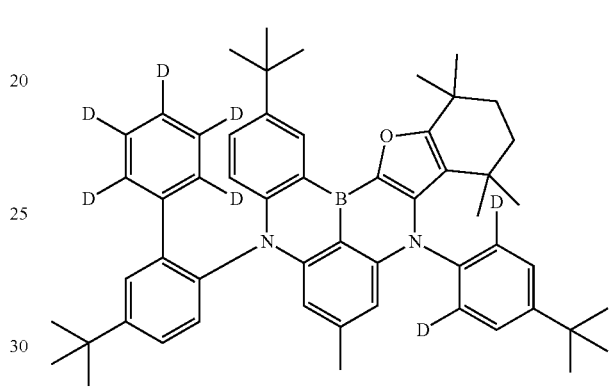
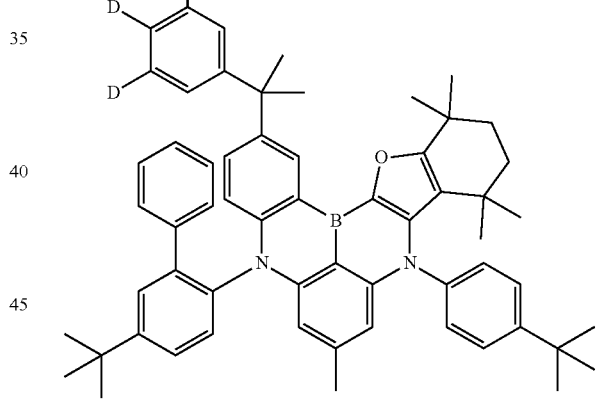
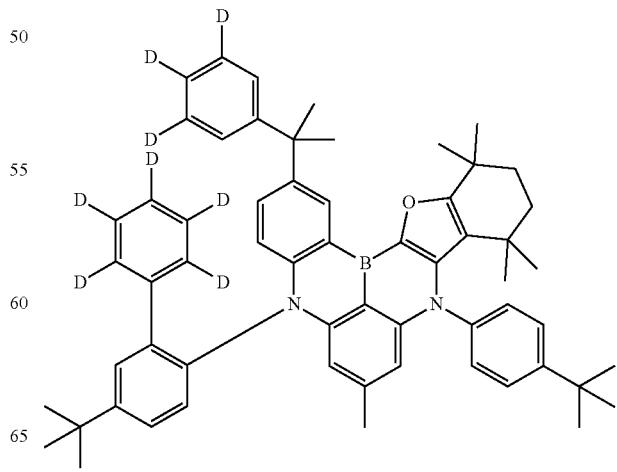

1651
-continued
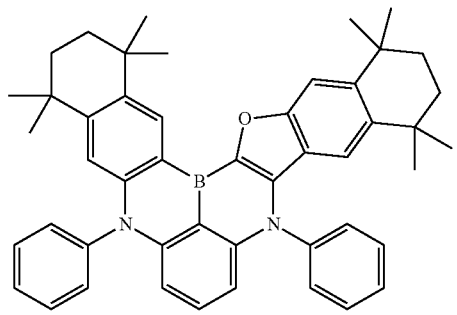
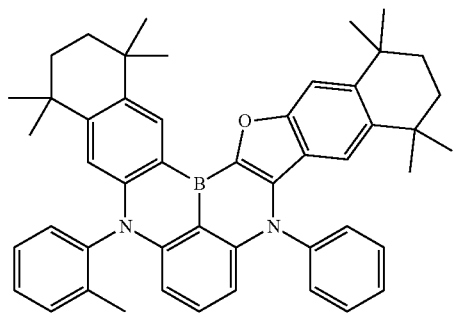
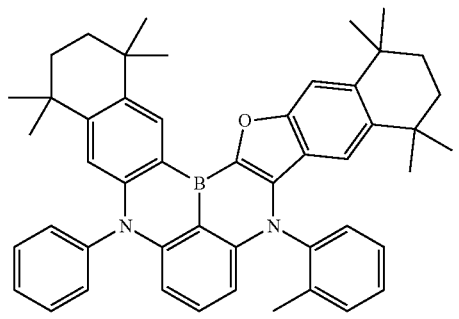
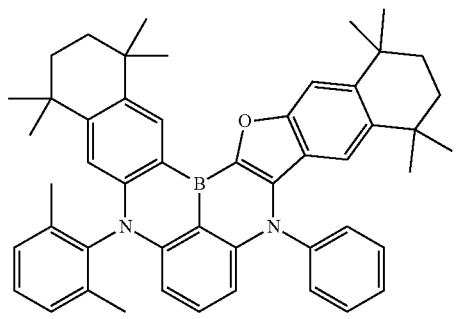
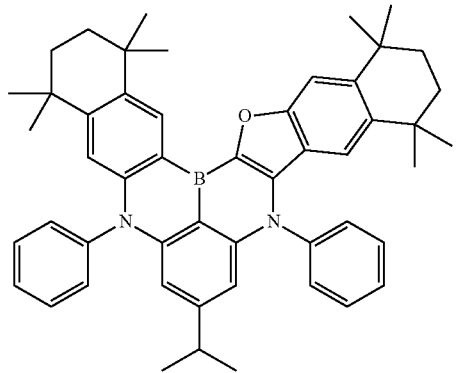
1652
-continued
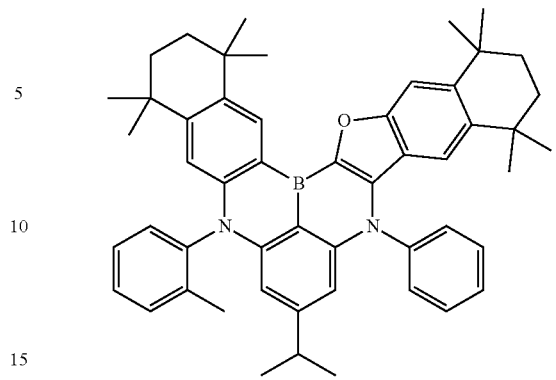
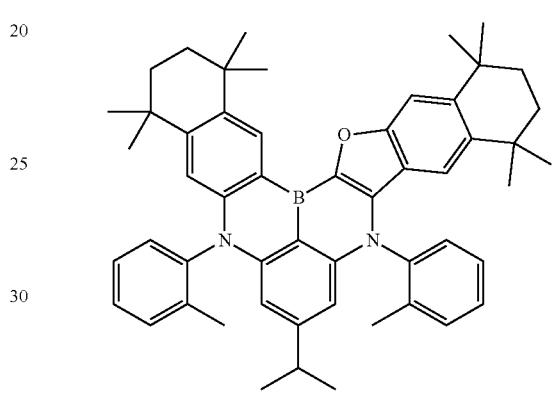
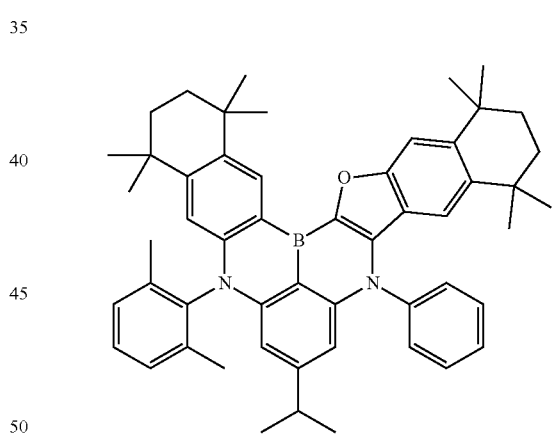
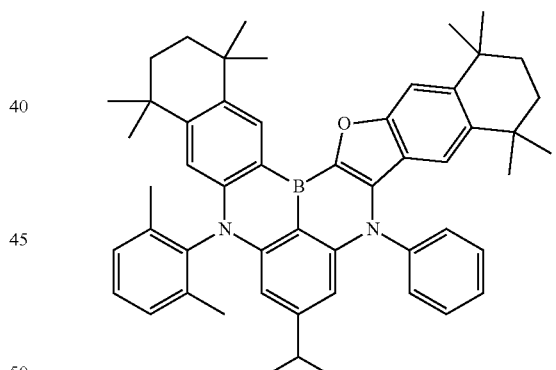
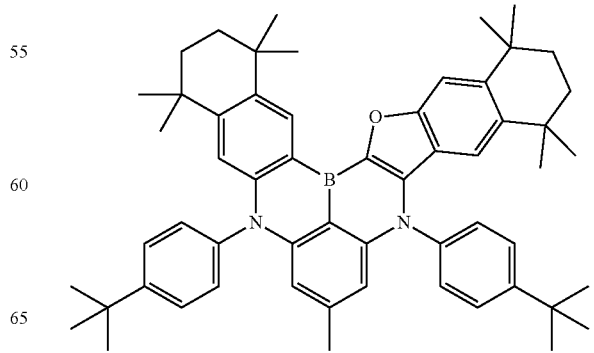

1653
-continued
1654
-continued
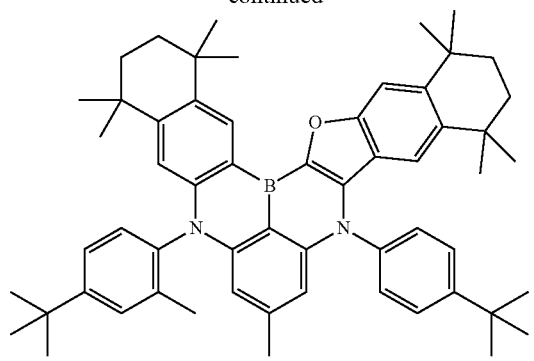
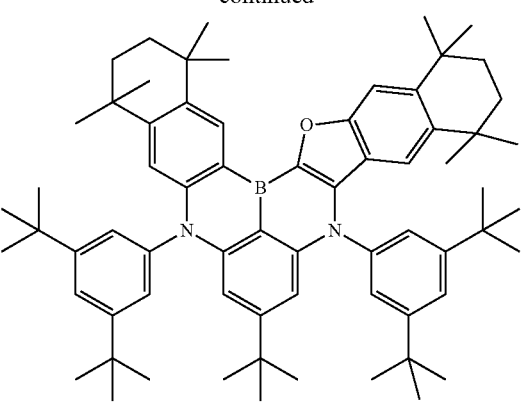
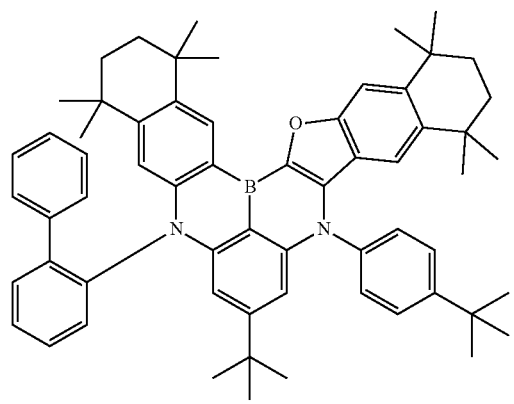
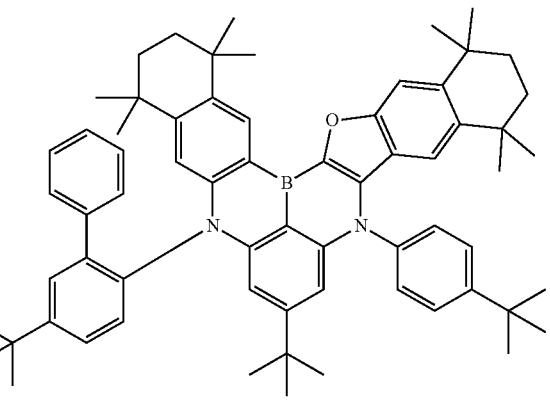
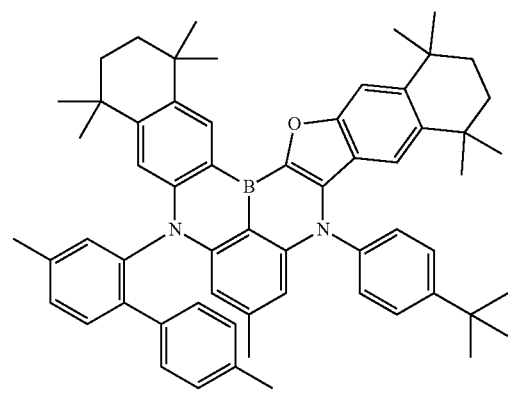

| 1655 -continued | 1656 -continued |
|---|---|
| 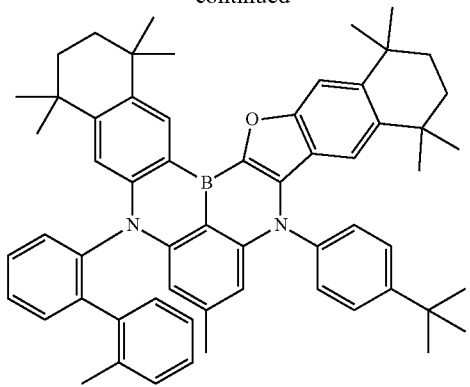 | 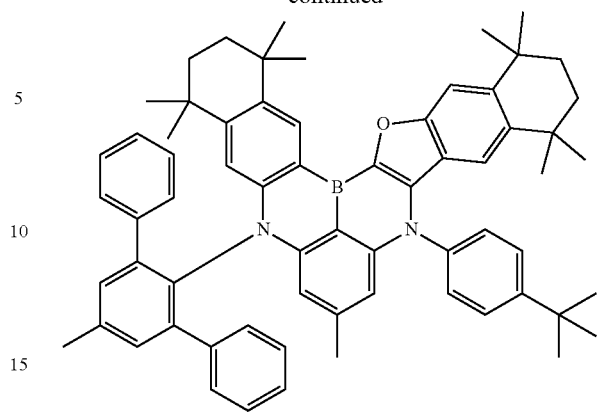 |
| 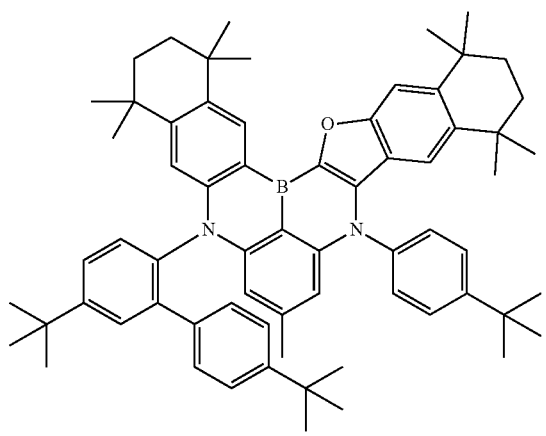 | 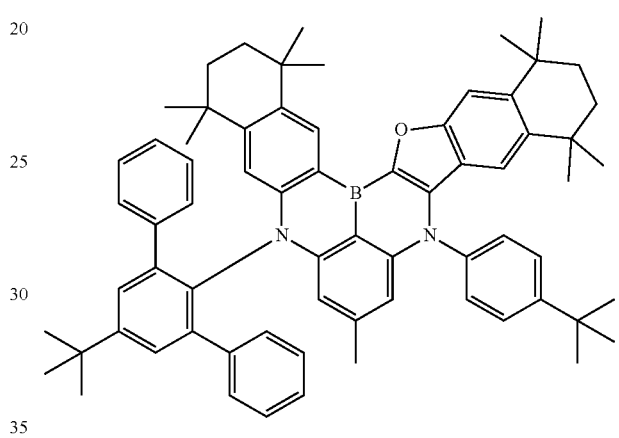 |
| 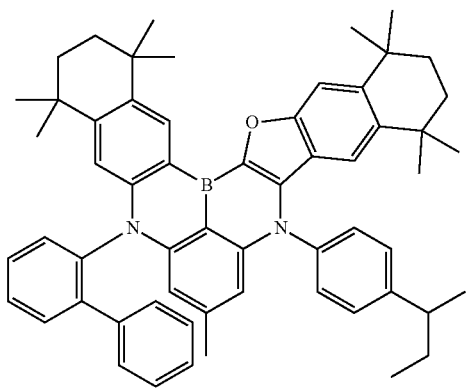 | 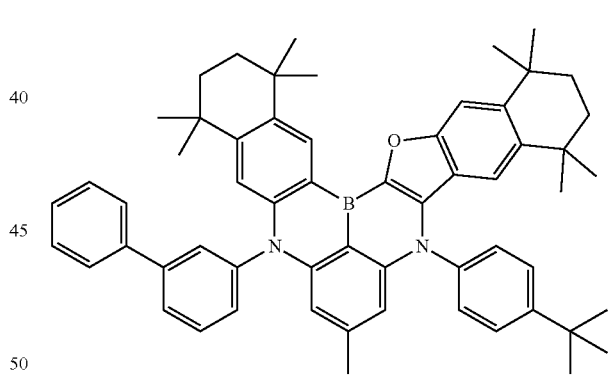 |
| 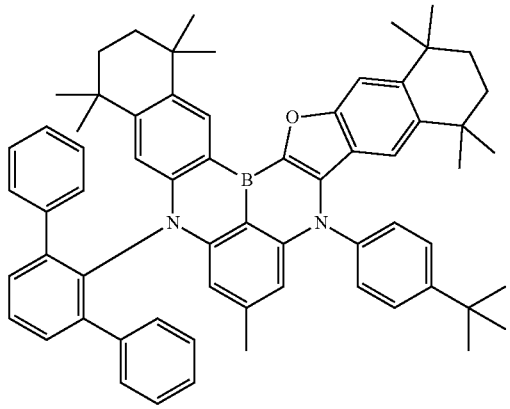 | 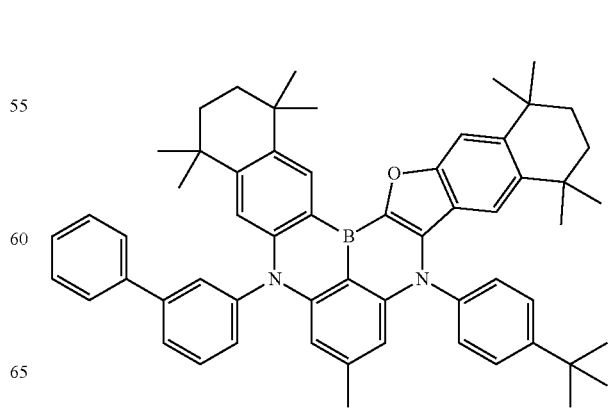 |

1657
-continued
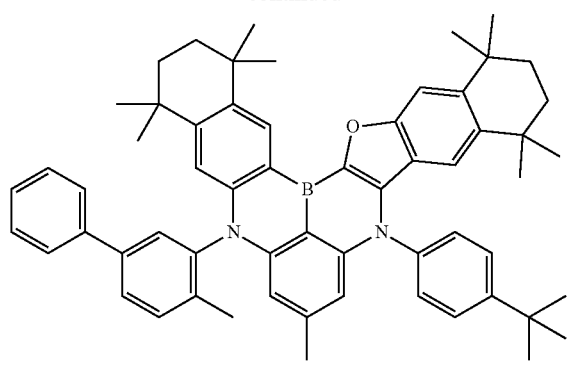
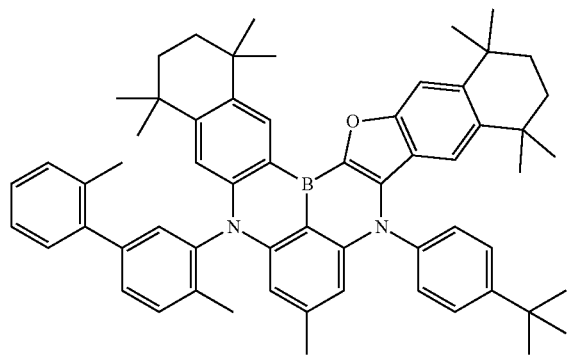
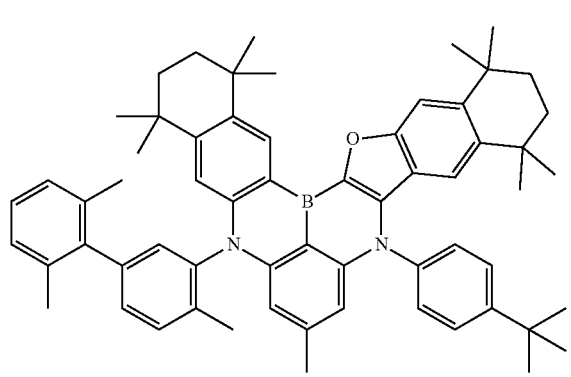
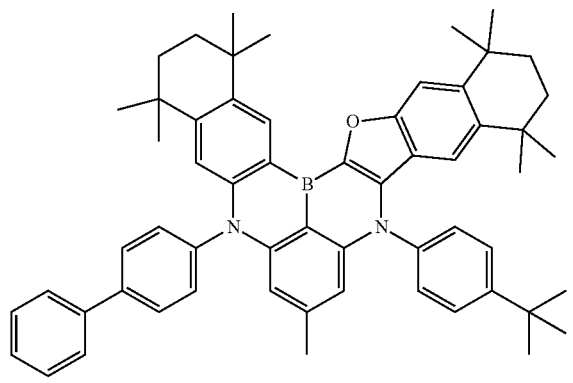
1658
-continued
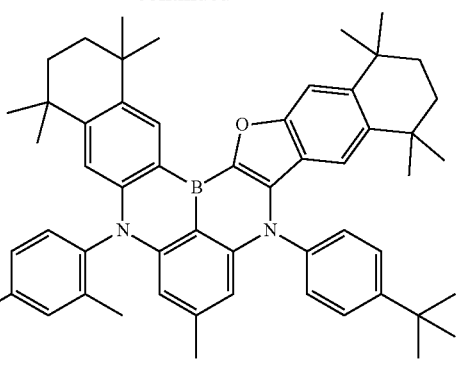
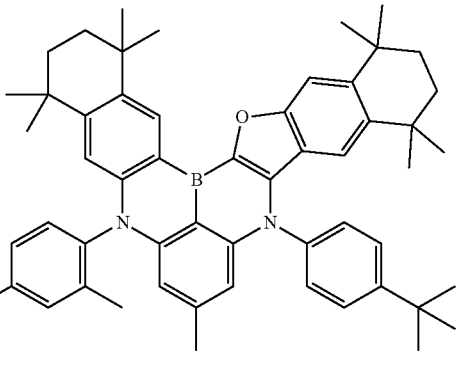
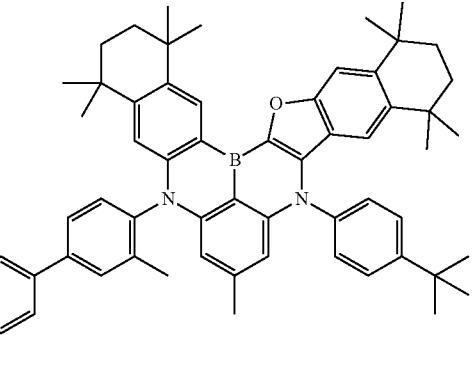
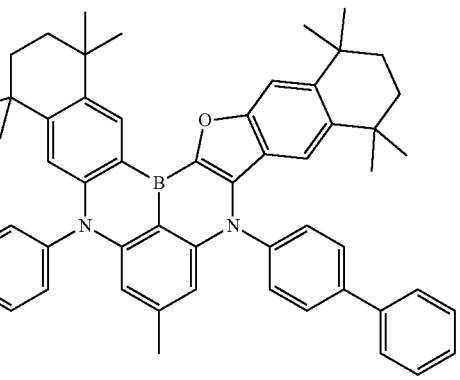

1659
-continued
1660
-continued
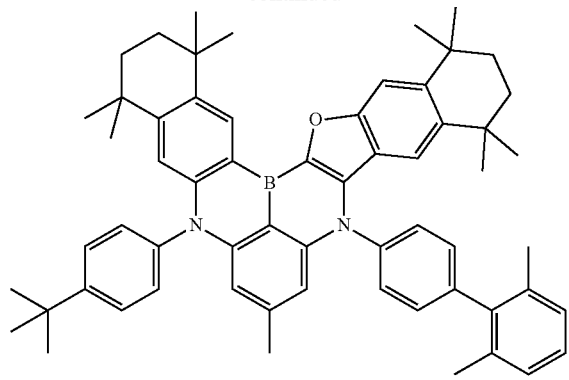
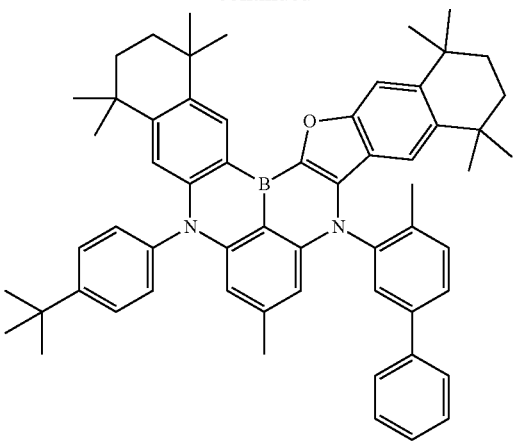
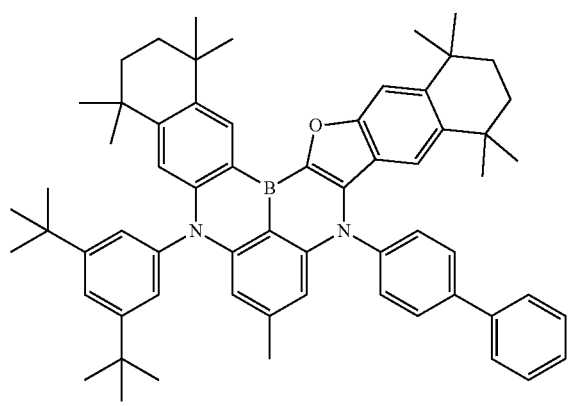
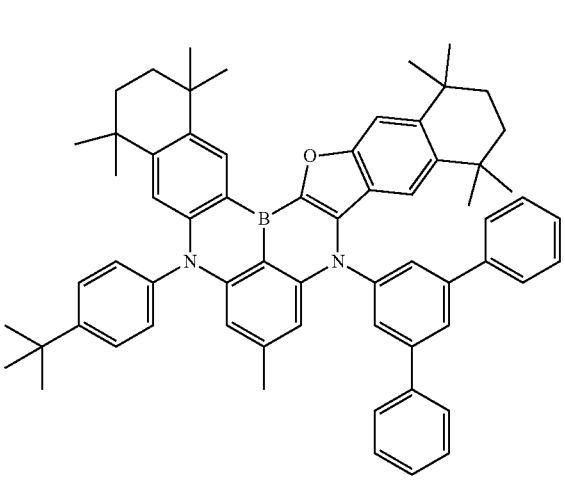
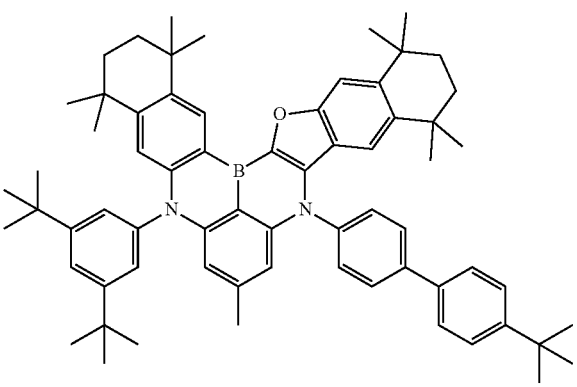
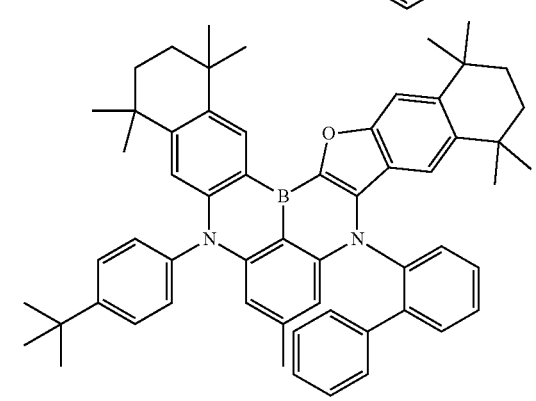
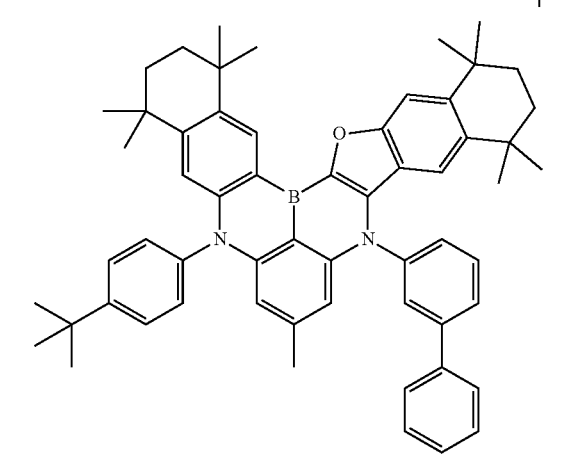
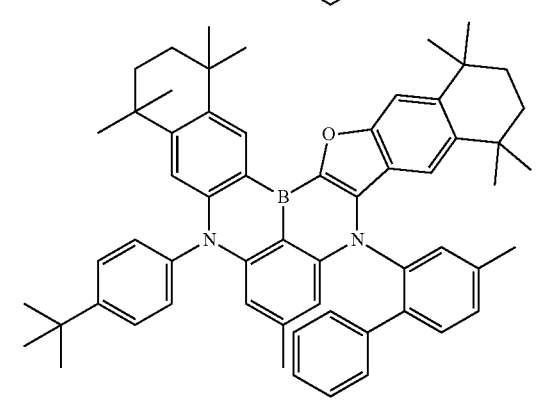

1661
-continued
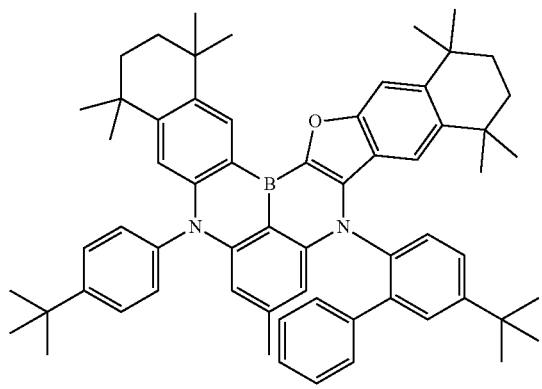
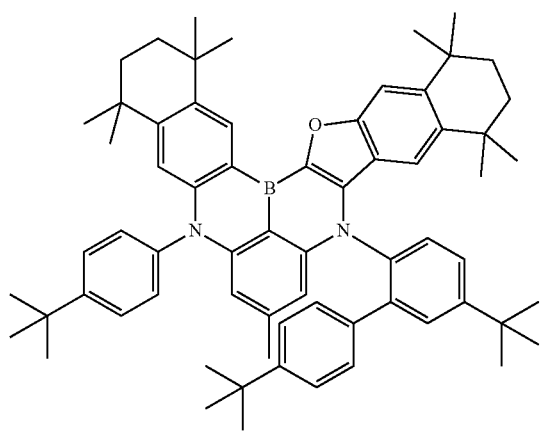
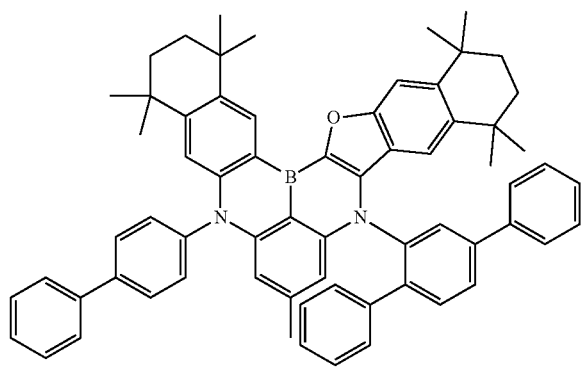
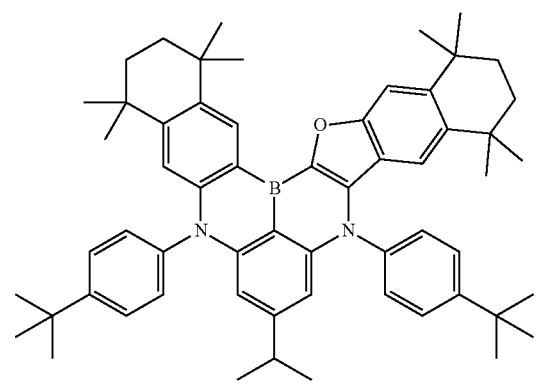
1662
-continued
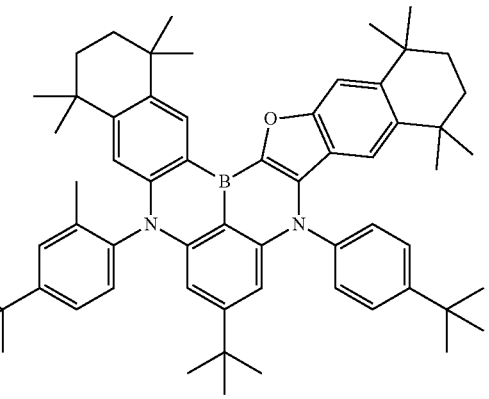
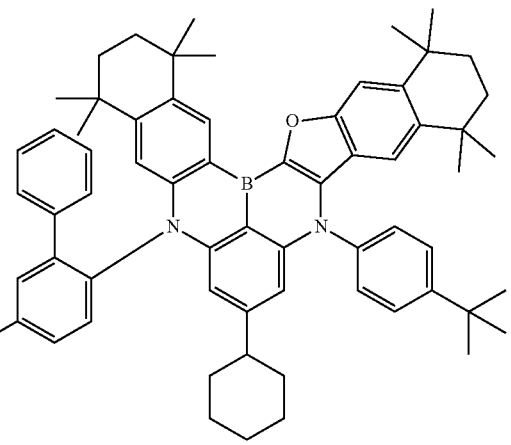
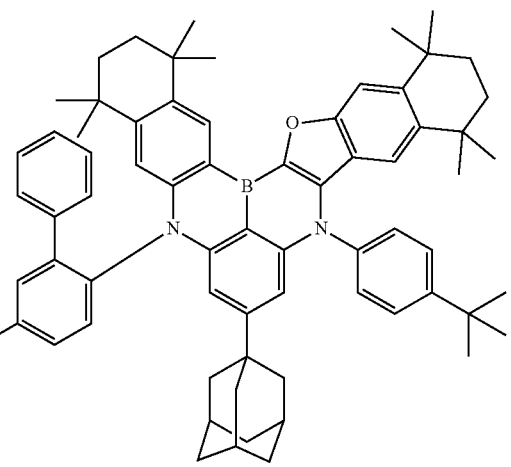
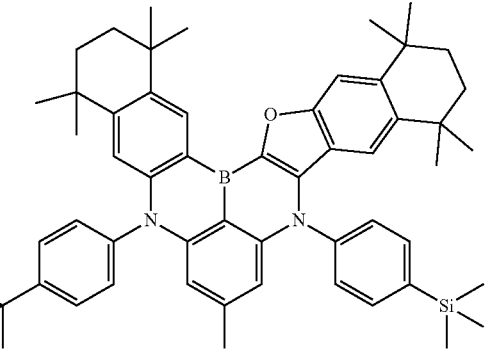

1663
-continued
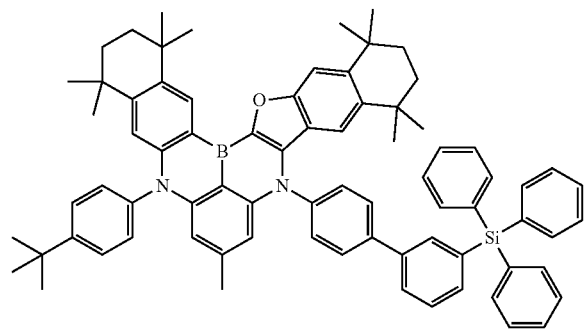
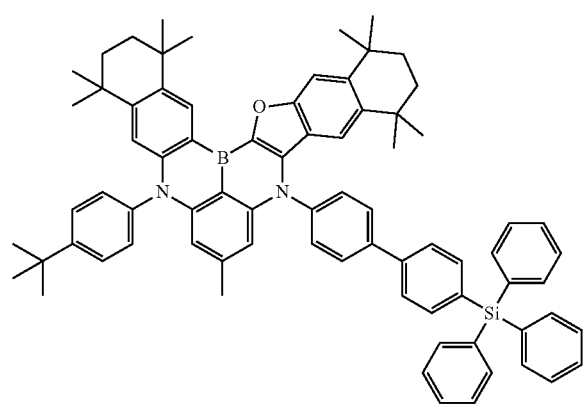
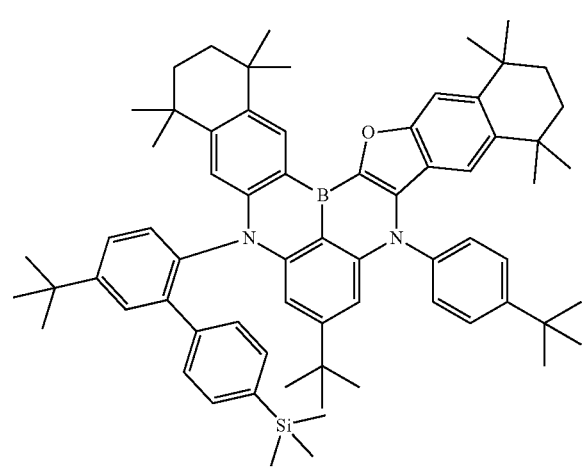
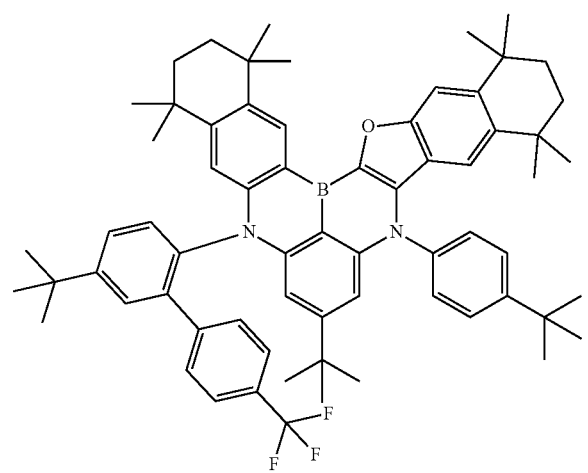
1664
-continued
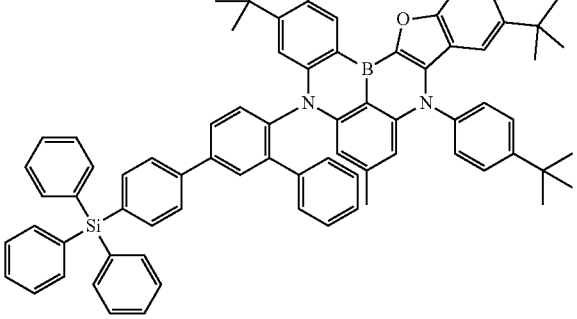
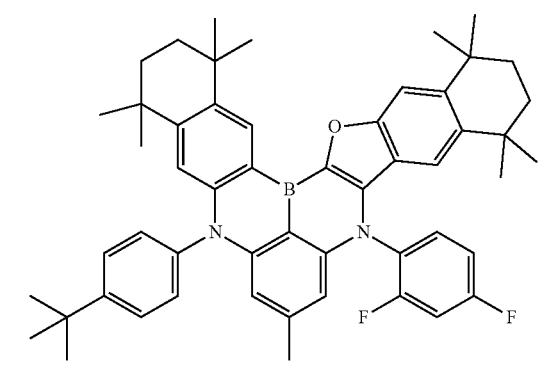
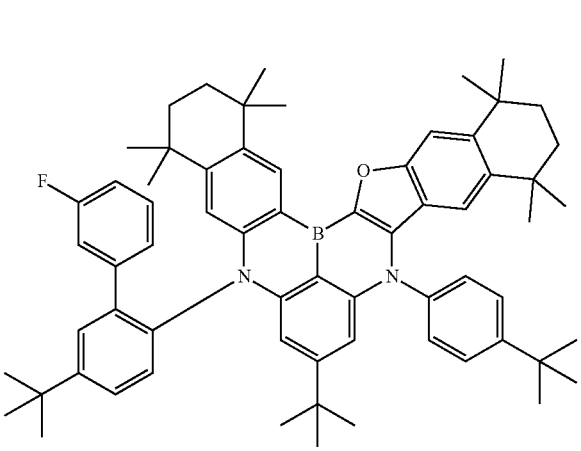
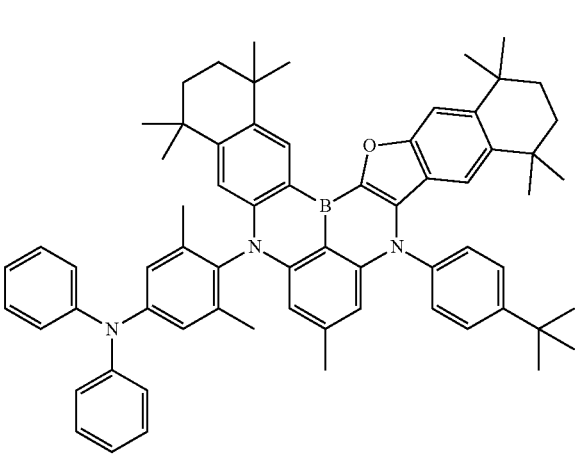

1665
-continued
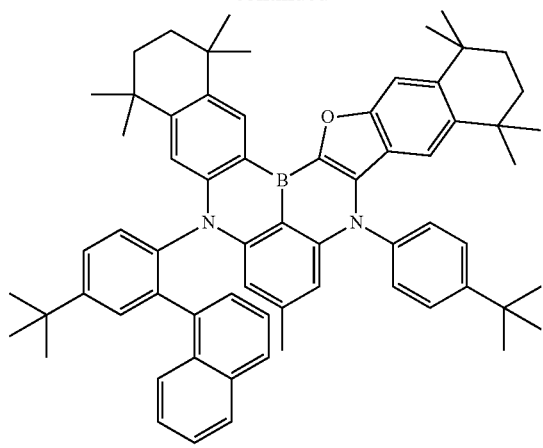
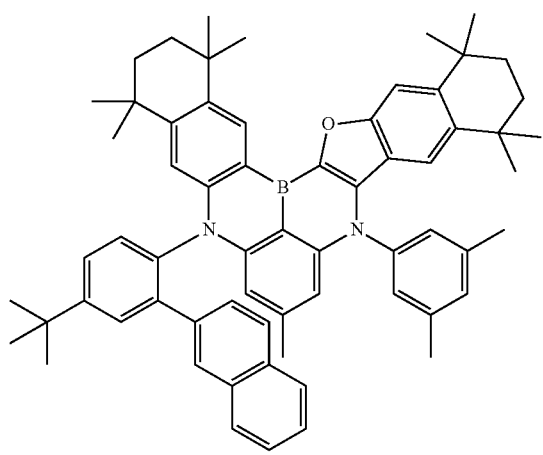
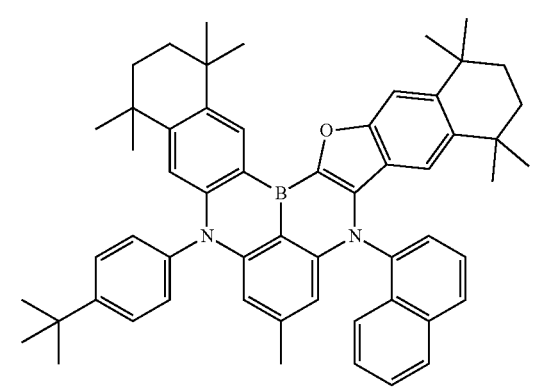
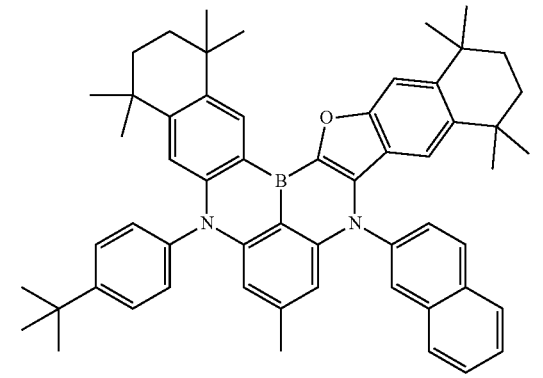
1666
-continued
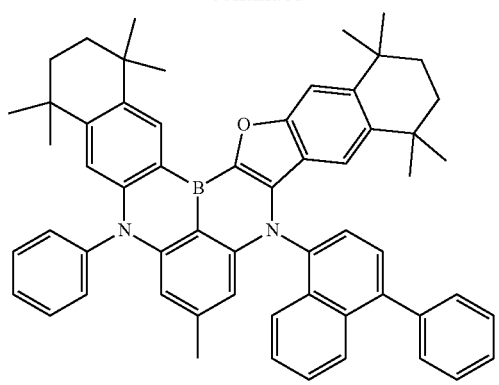
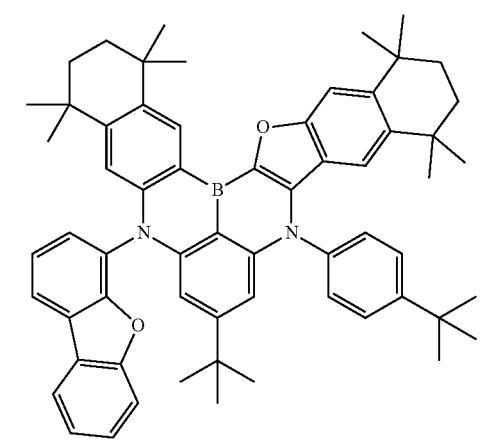
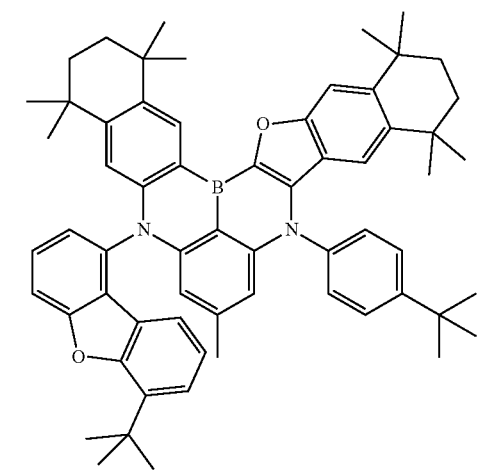
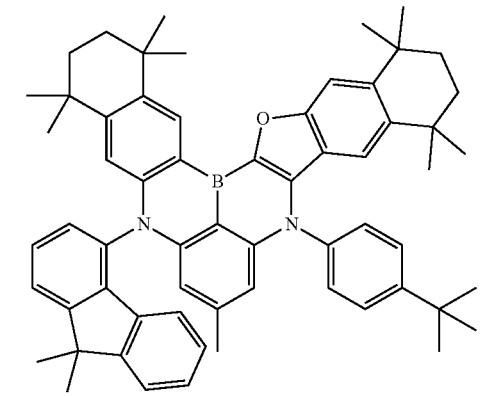

1667
-continued
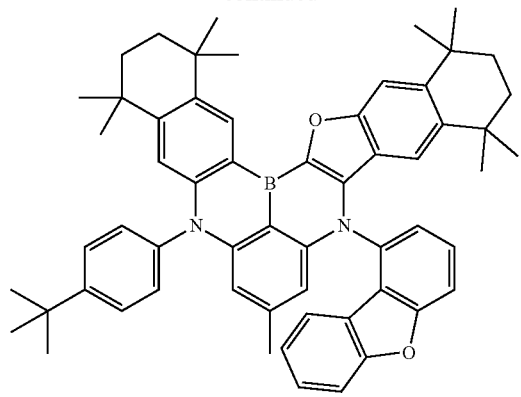
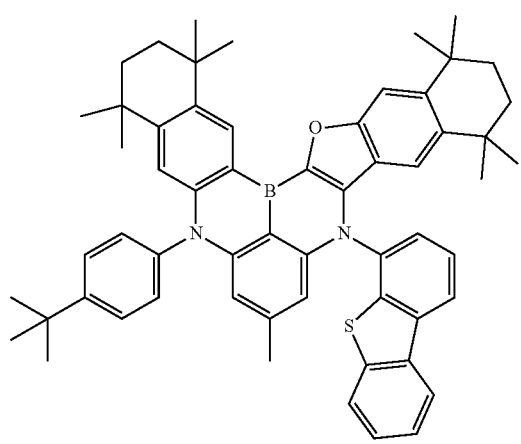
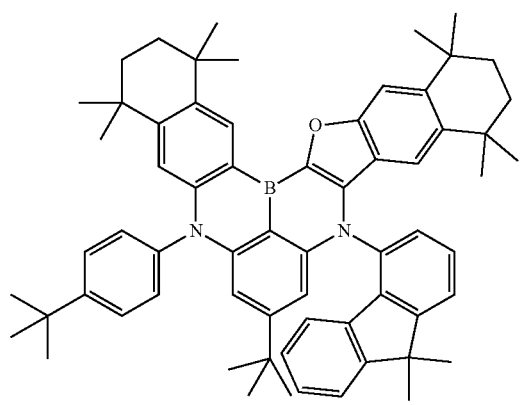
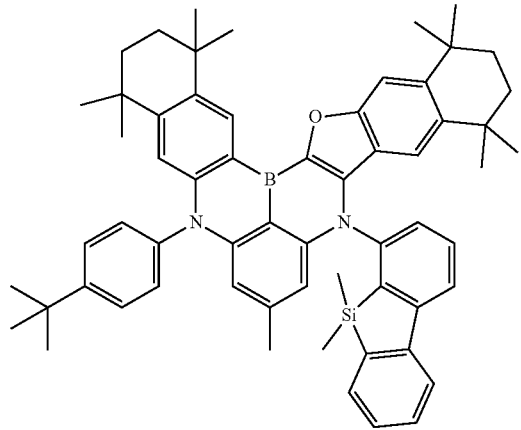
1668
-continued
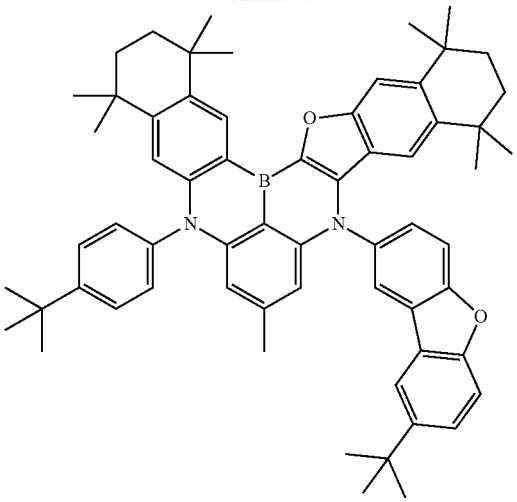
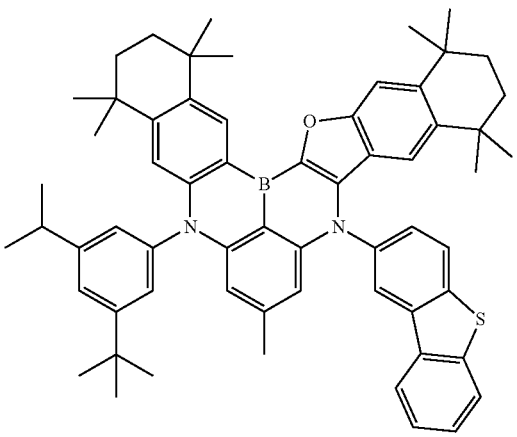
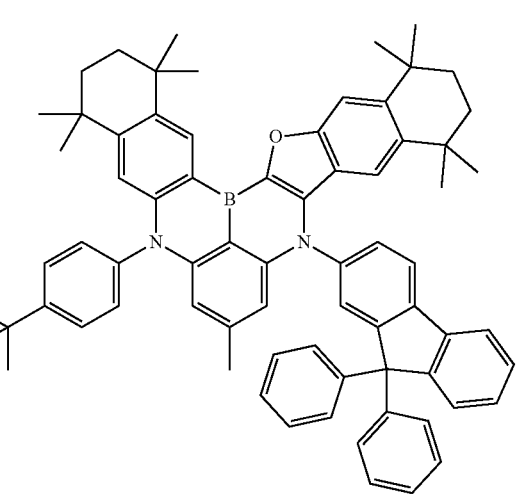

1669
-continued
1670
-continued
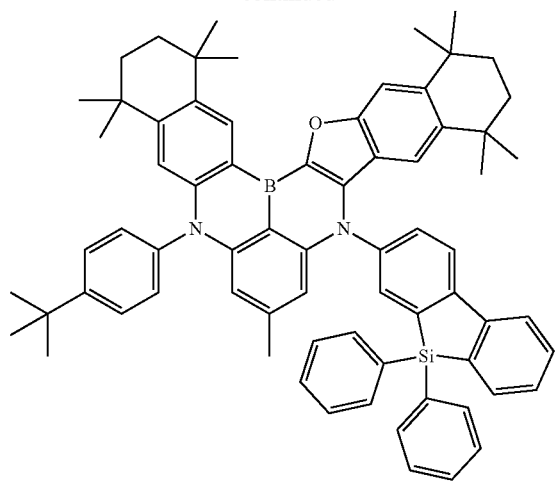
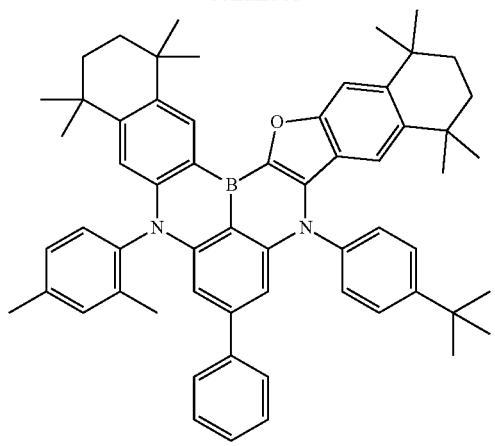
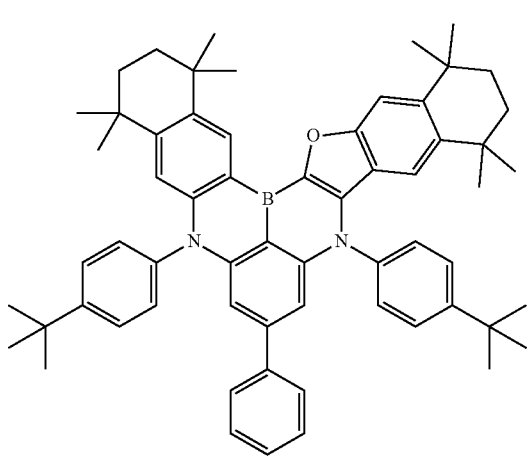
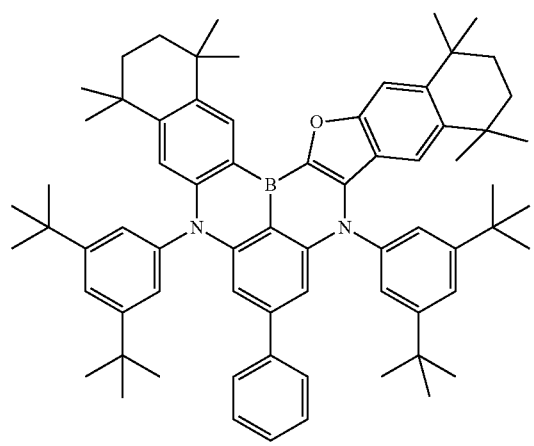
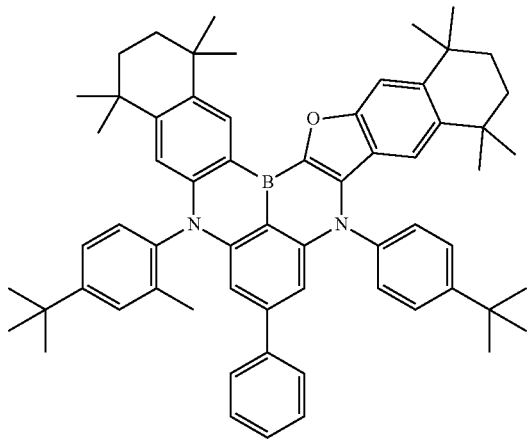
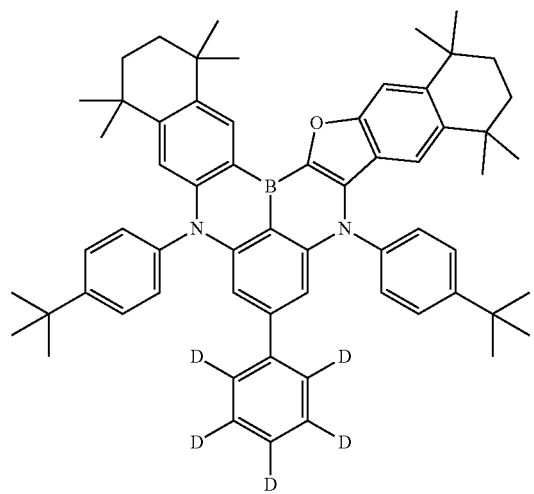

1671
-continued
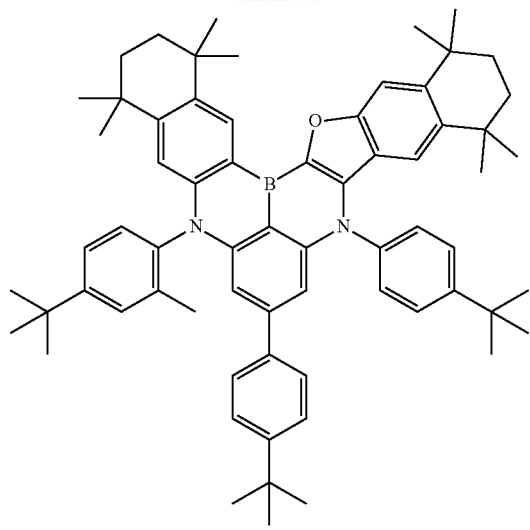
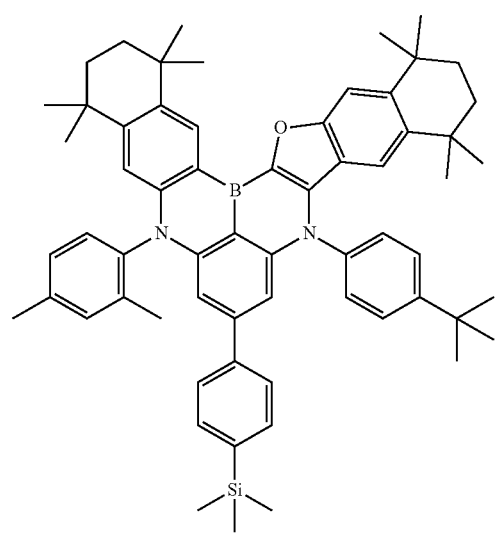
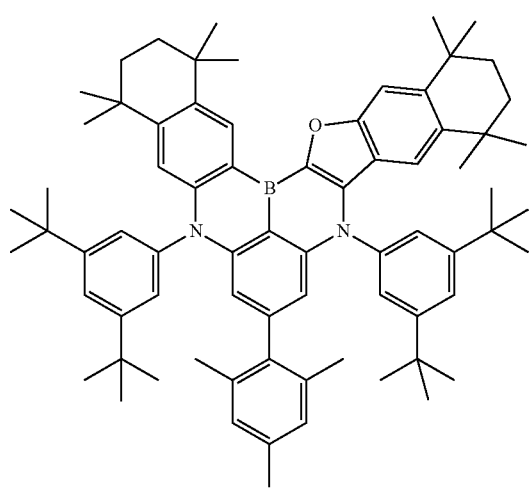
1672
-continued
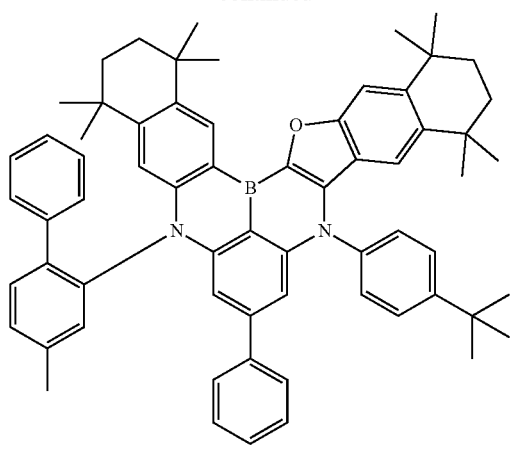
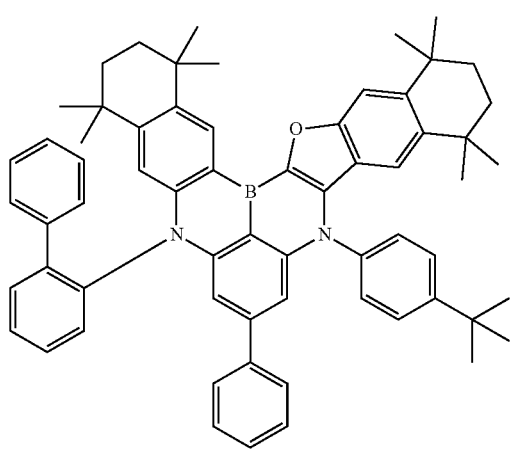
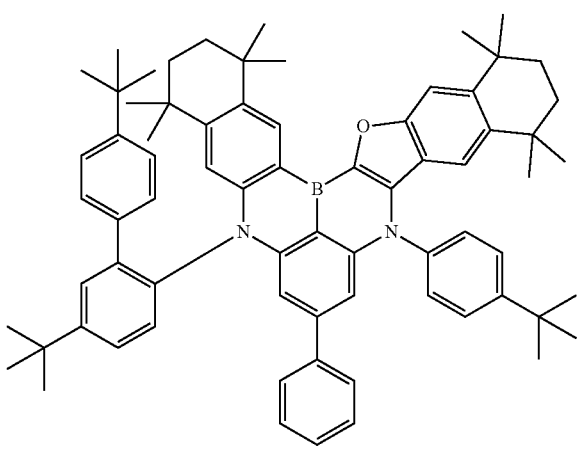

1673
-continued
1674
-continued
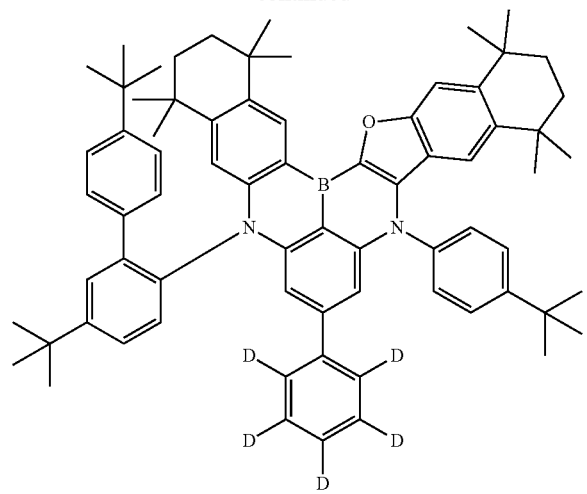
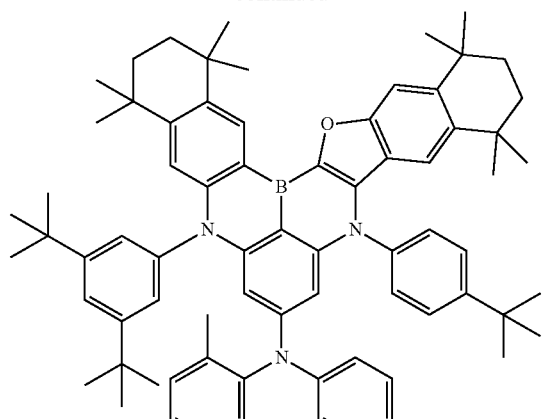
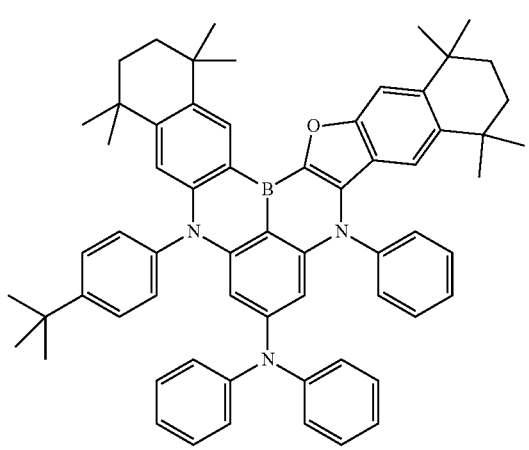
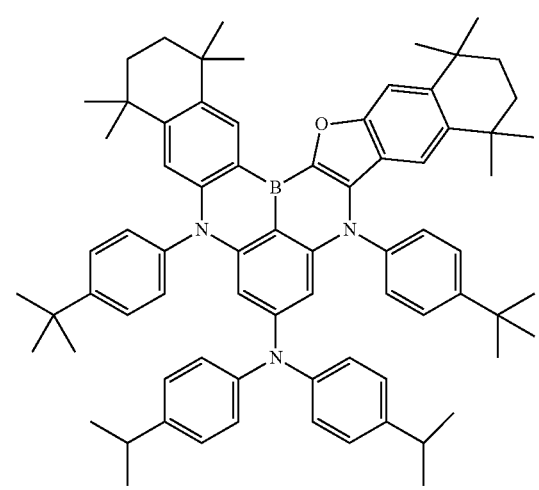
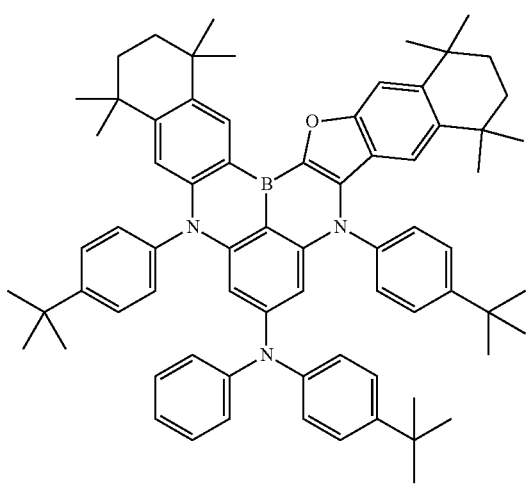
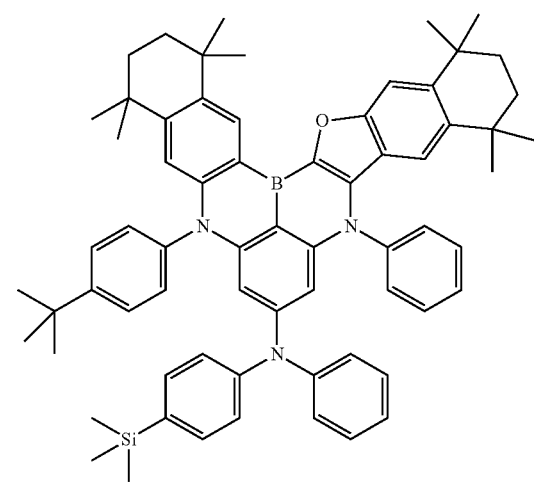

1675
-continued
1676
-continued
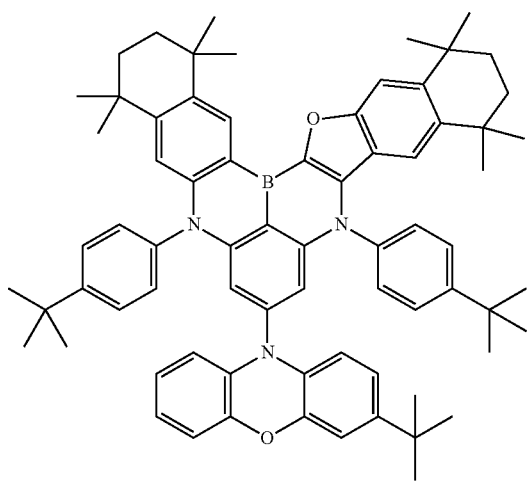
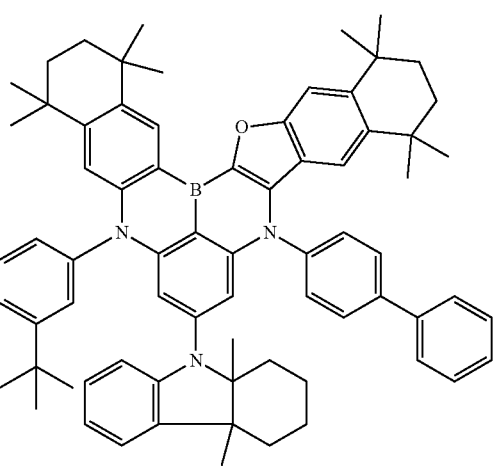
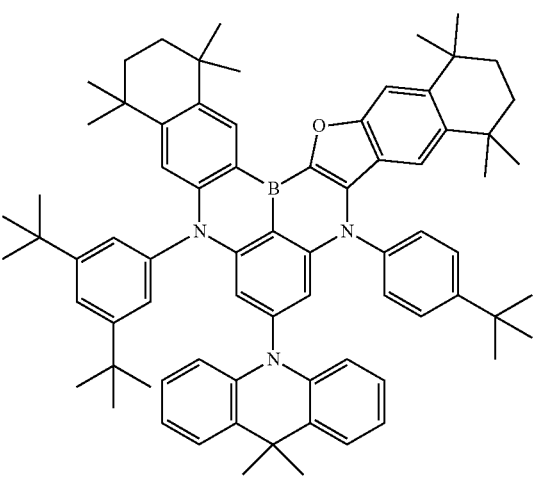
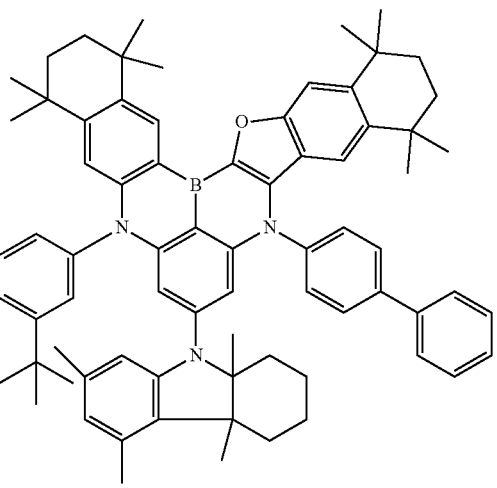
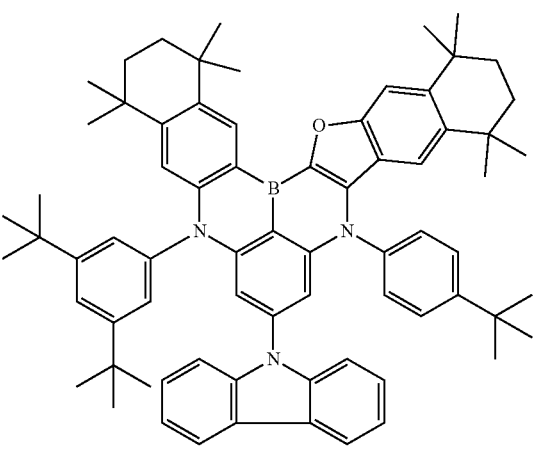
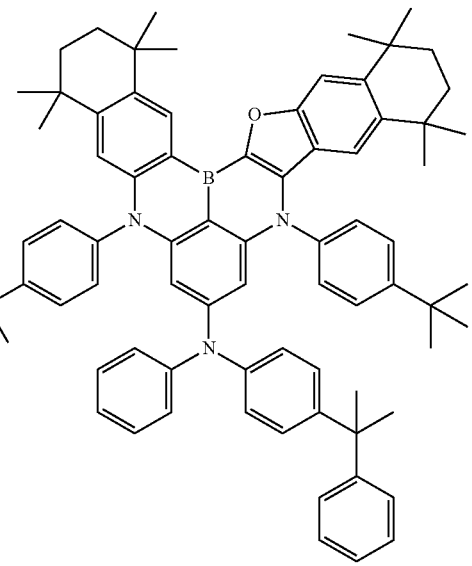

1677
-continued
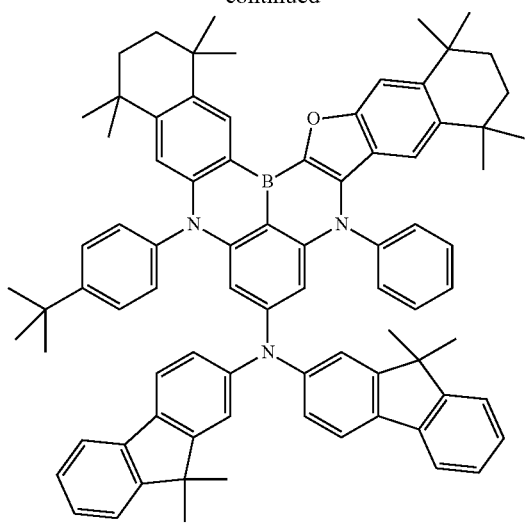
1678
-continued
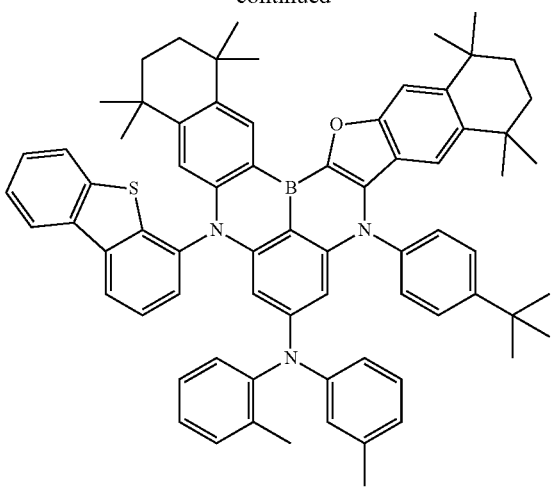
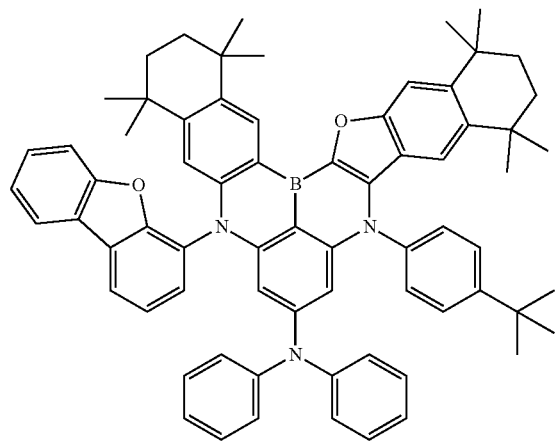
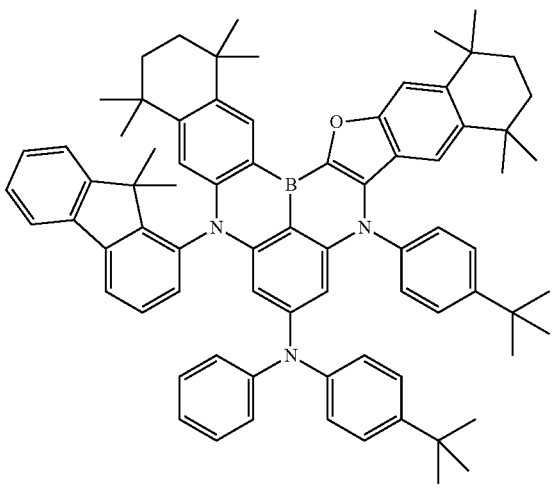
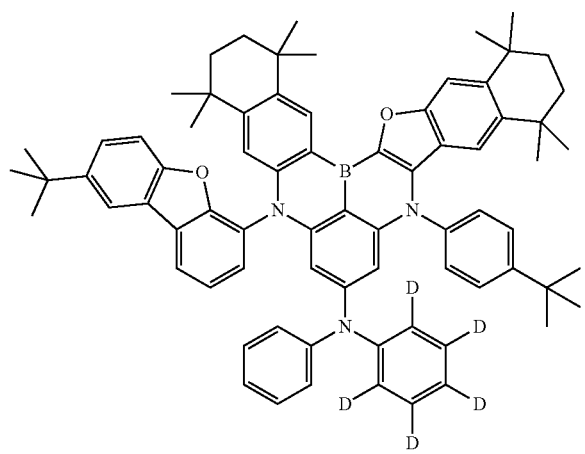
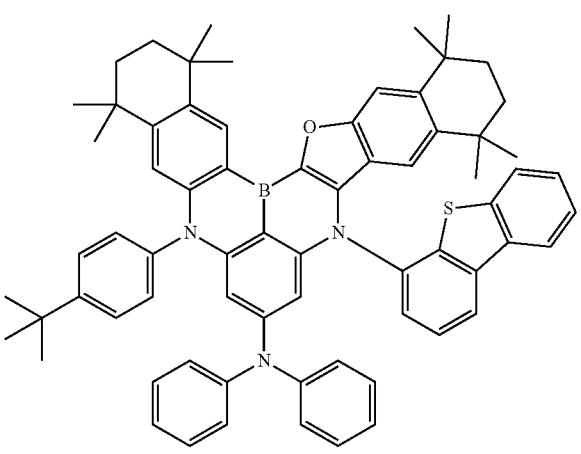

1679
-continued
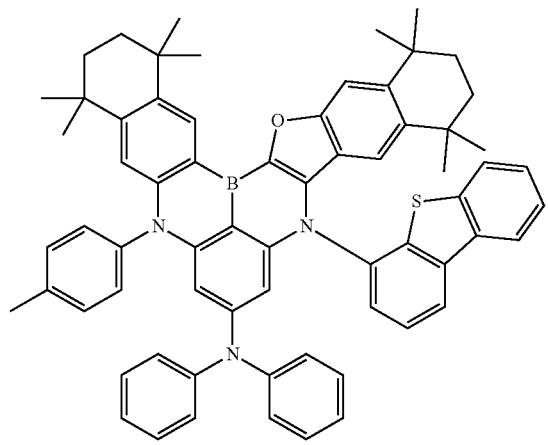
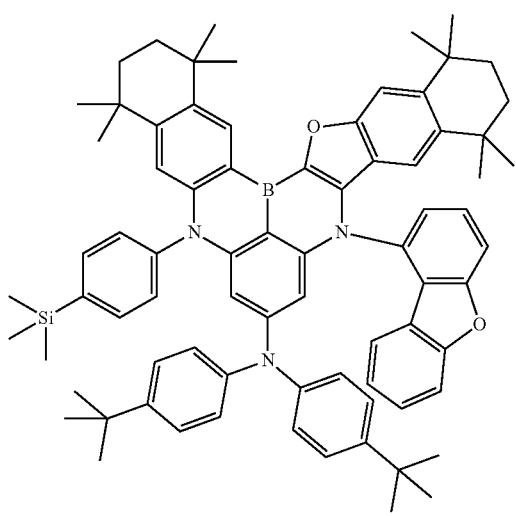
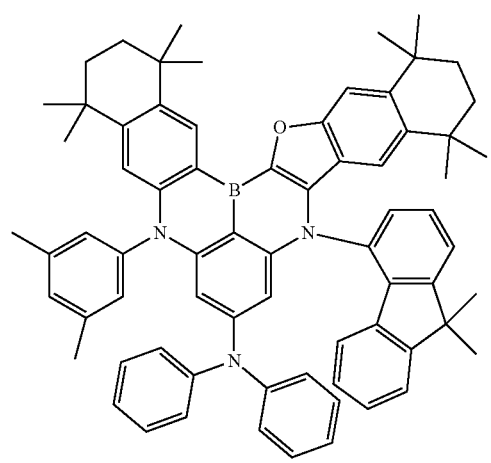
1680
-continued
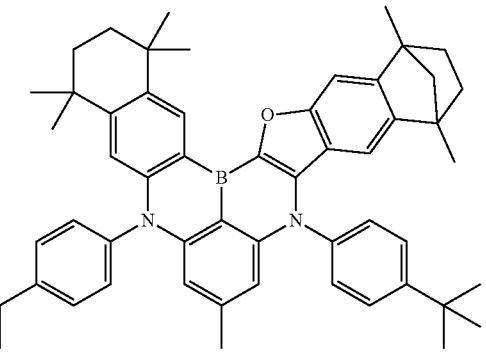
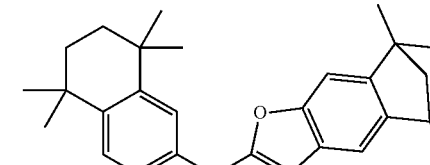
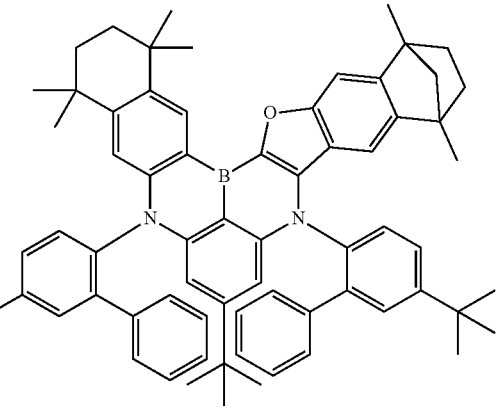
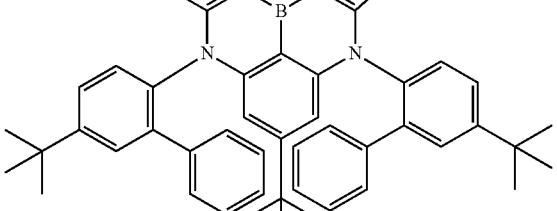

1681
-continued
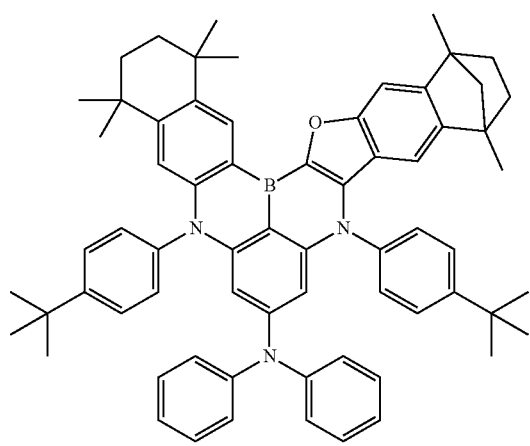
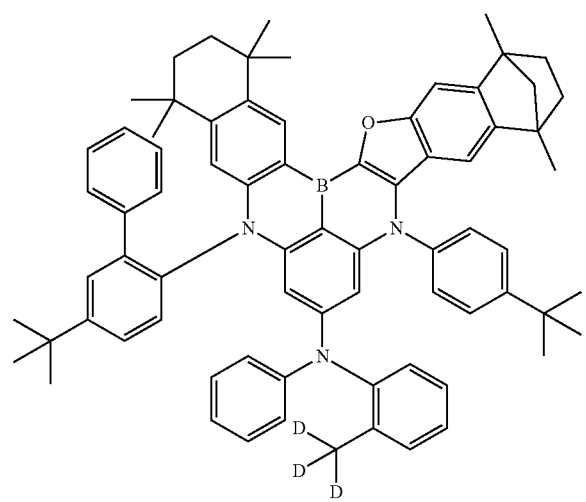
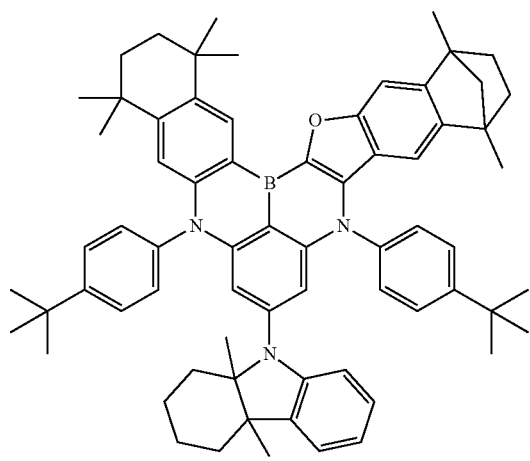
1682
-continued
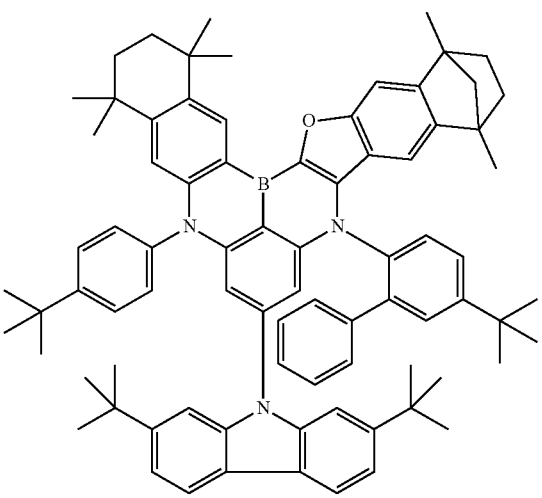
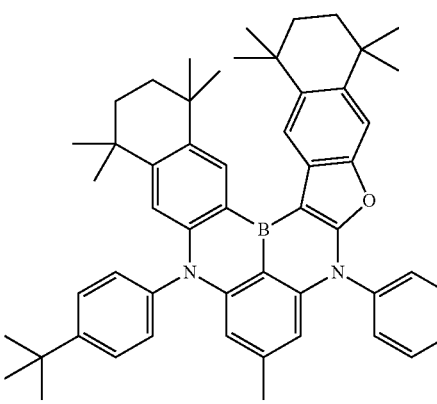
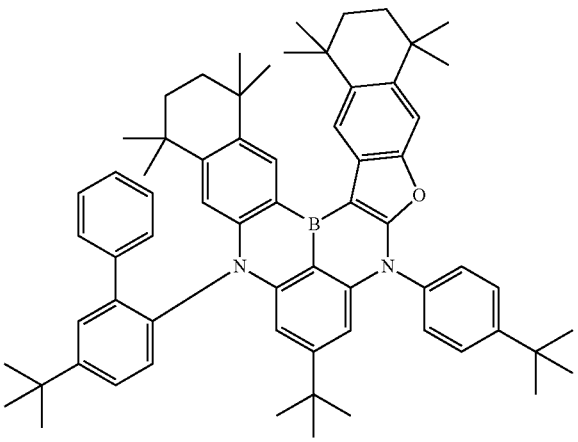

1683
-continued
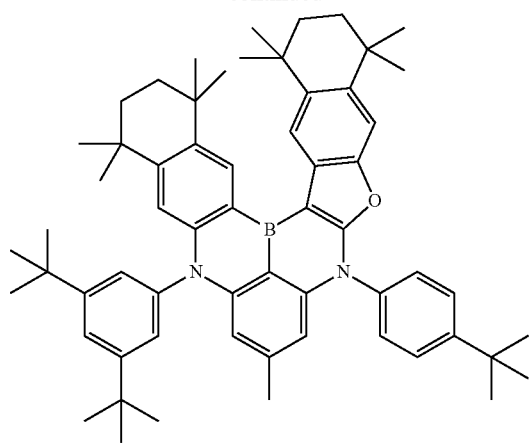
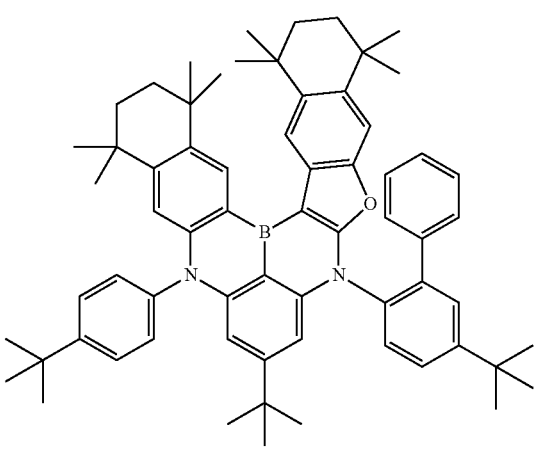
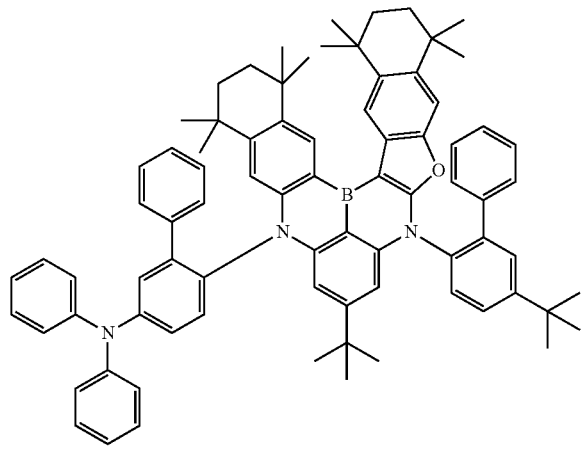
1684
-continued
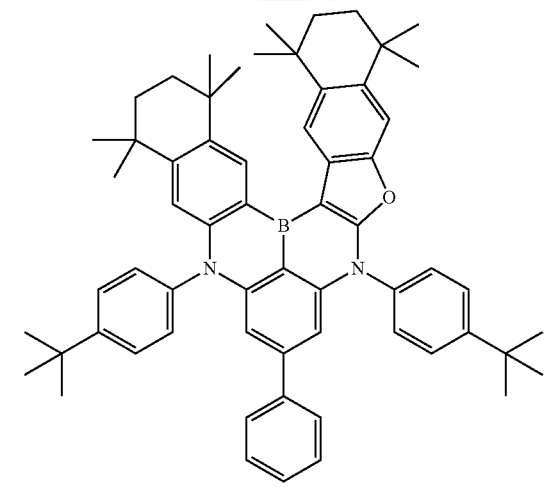
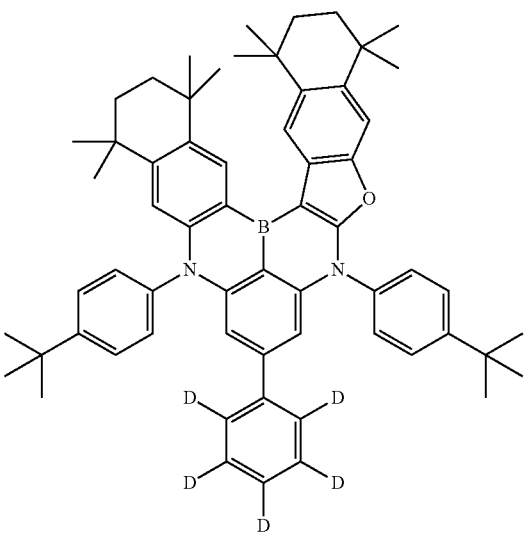
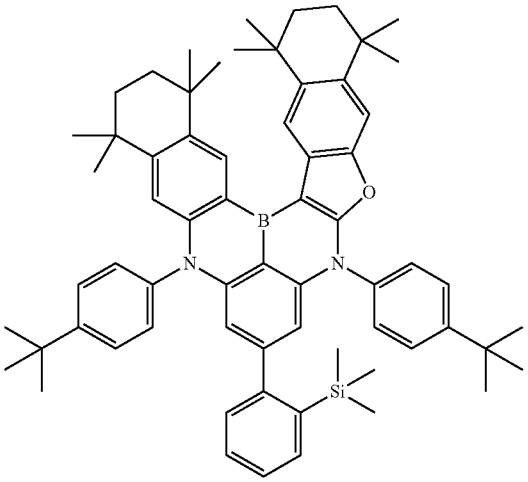

1685
-continued
1686
-continued
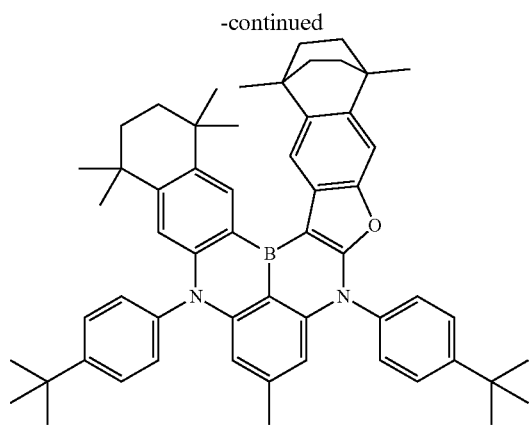
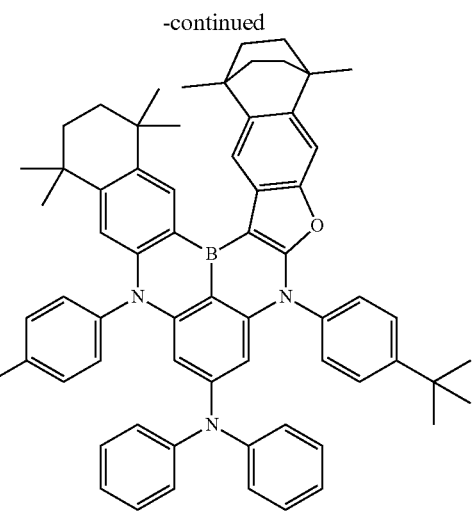
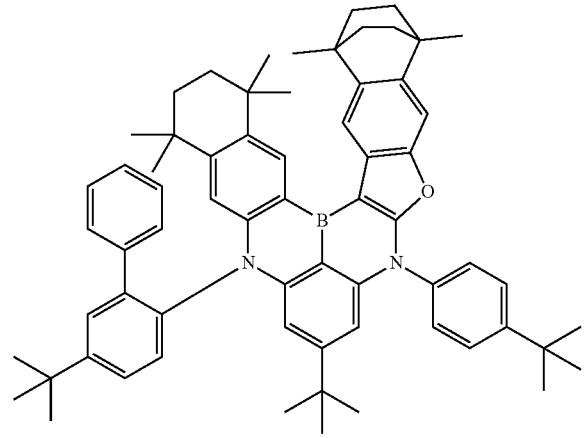
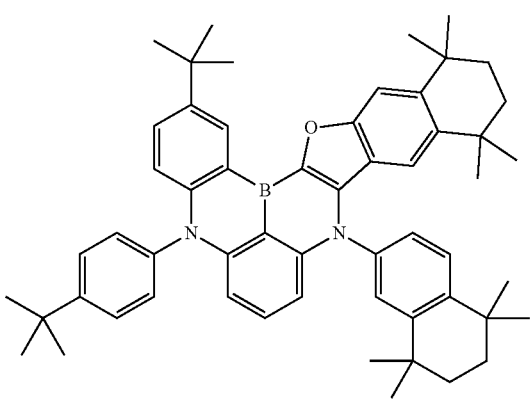
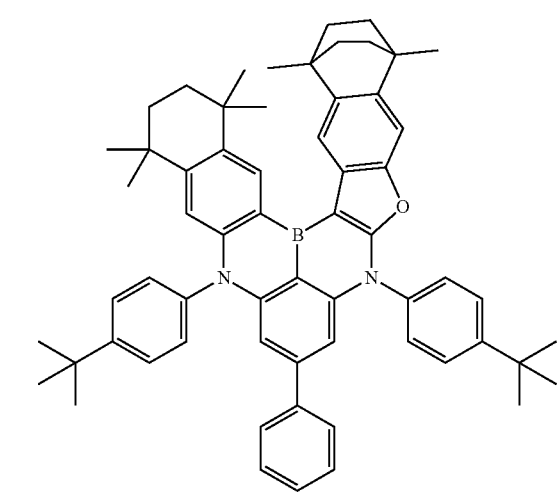
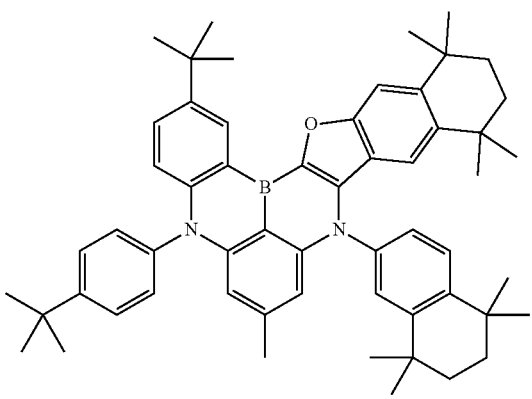
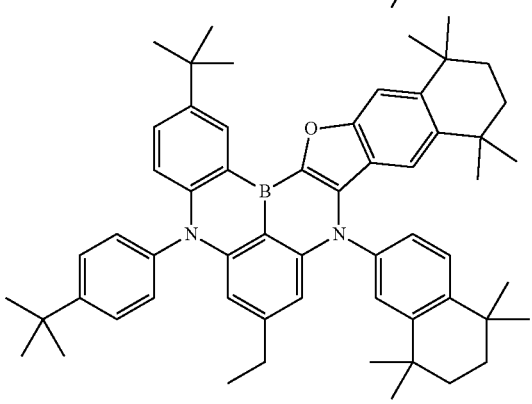

1687
-continued
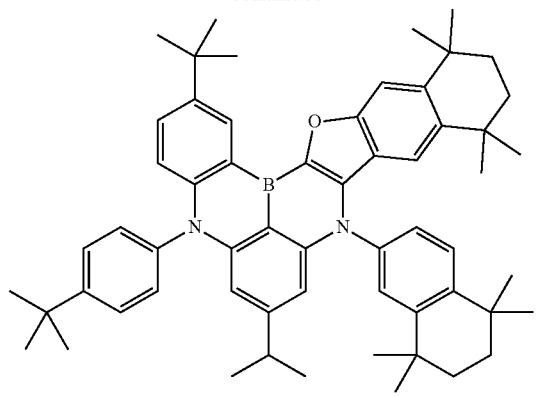
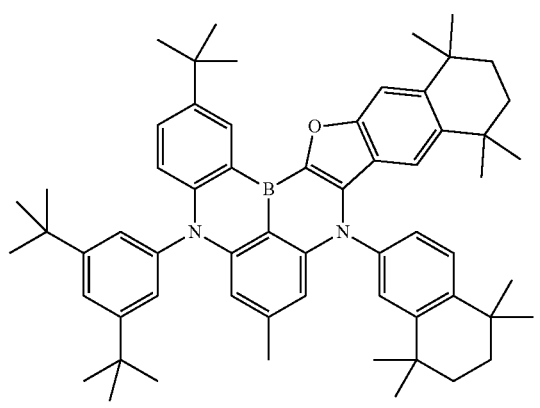
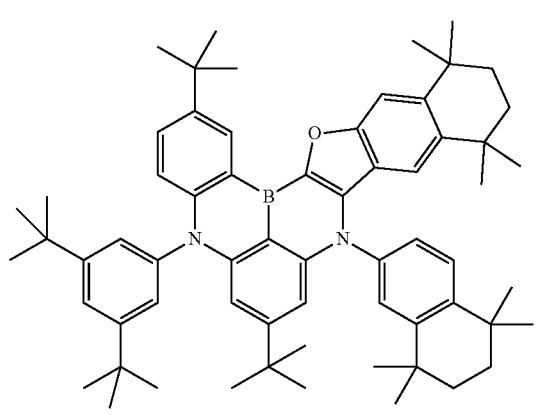
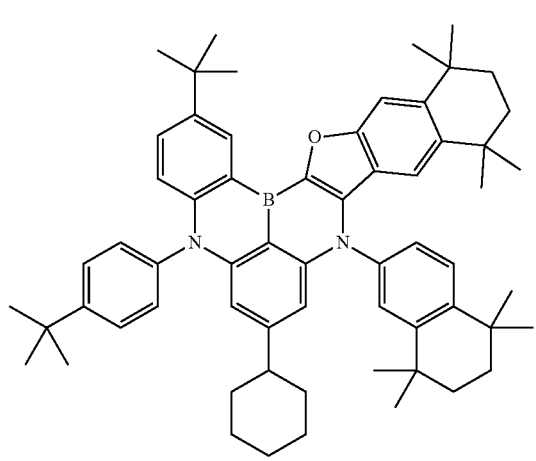
1688
-continued
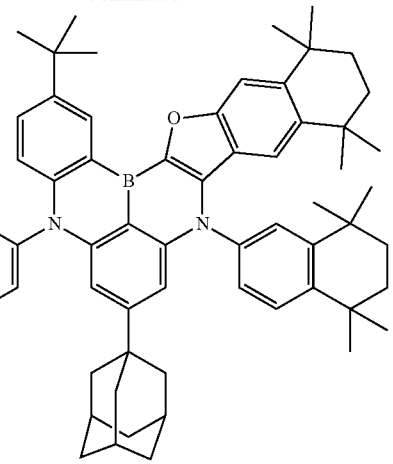

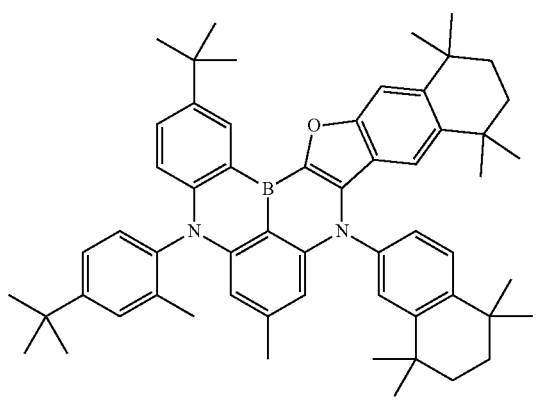

1689
-continued
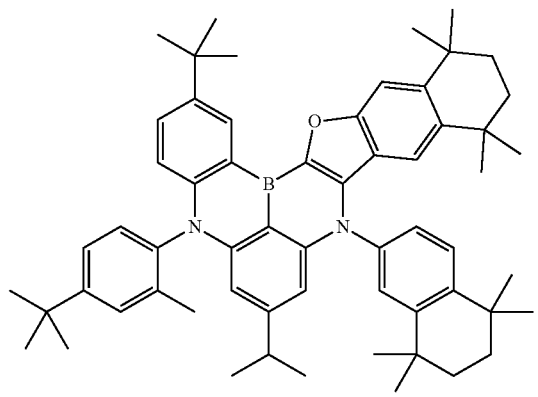
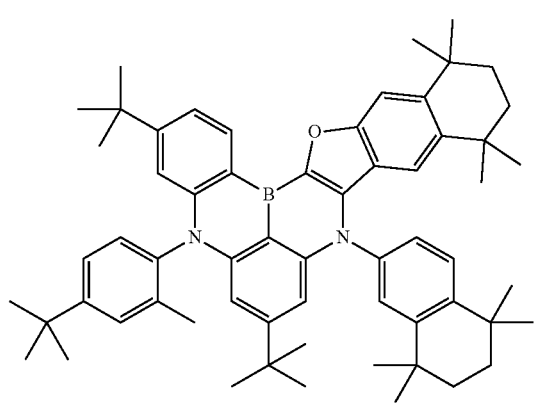
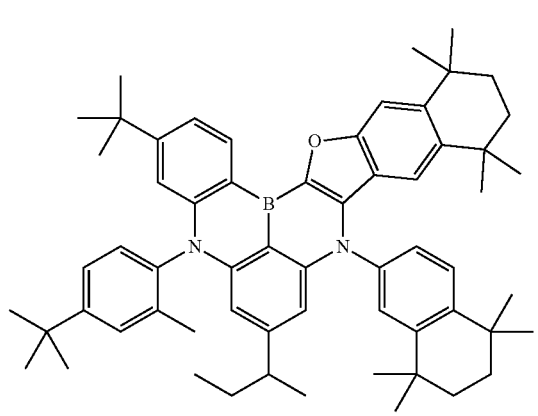
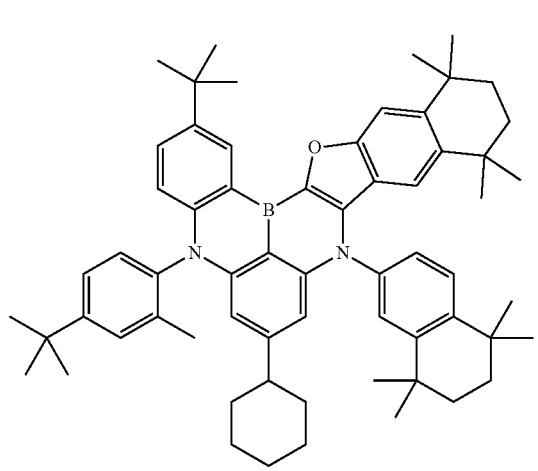
1690
-continued
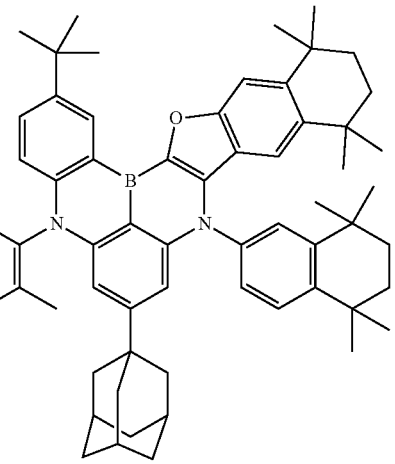
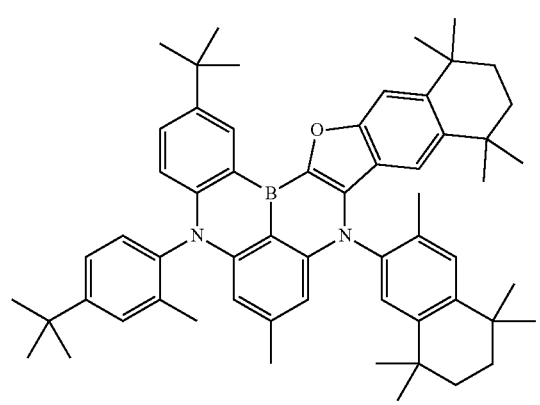

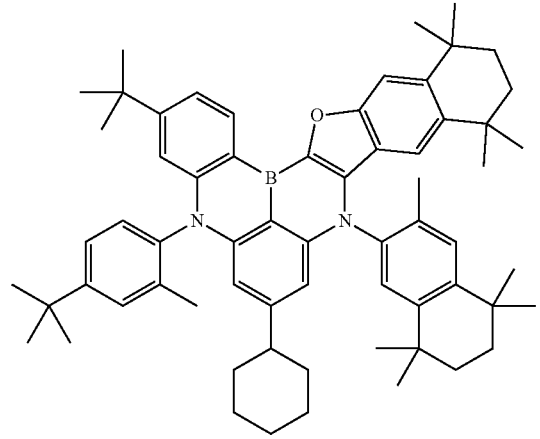

1691
-continued
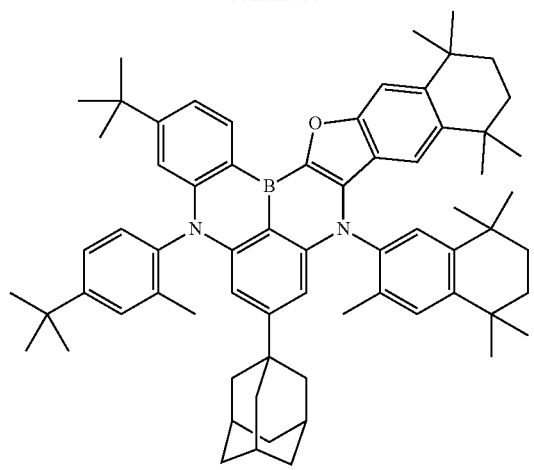
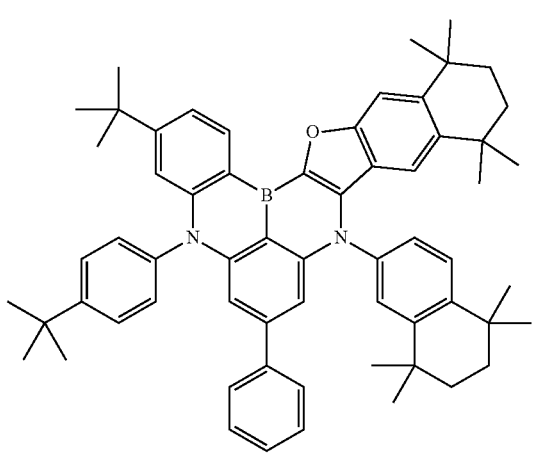
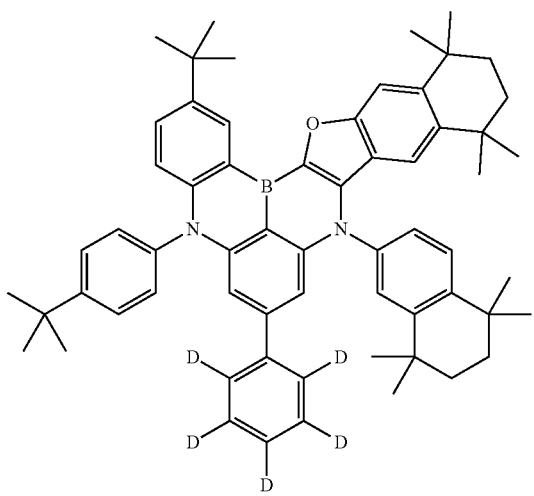
1692
-continued
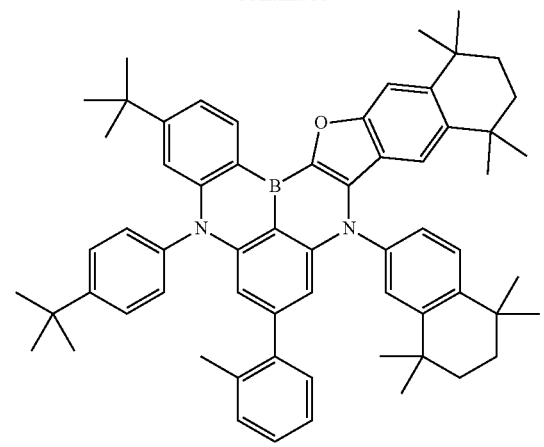
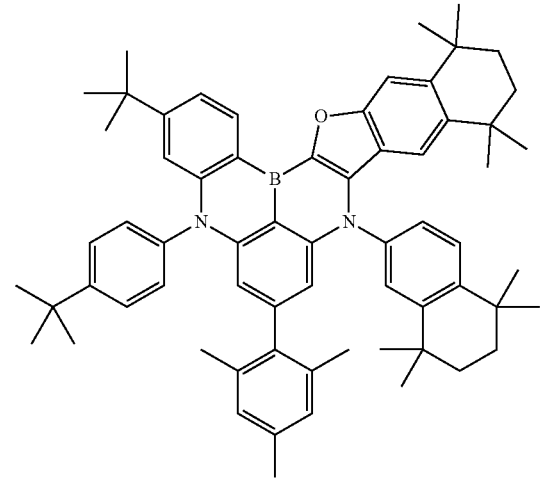
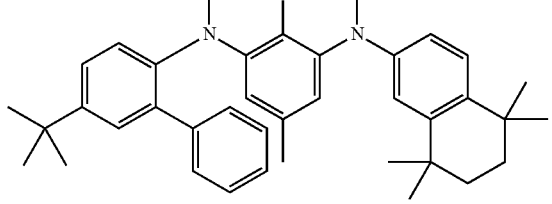
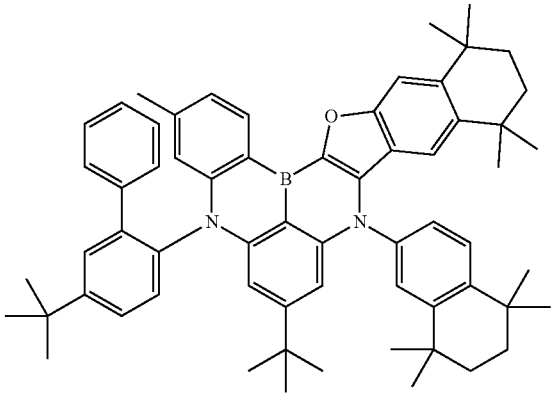

1693
-continued
1694
-continued
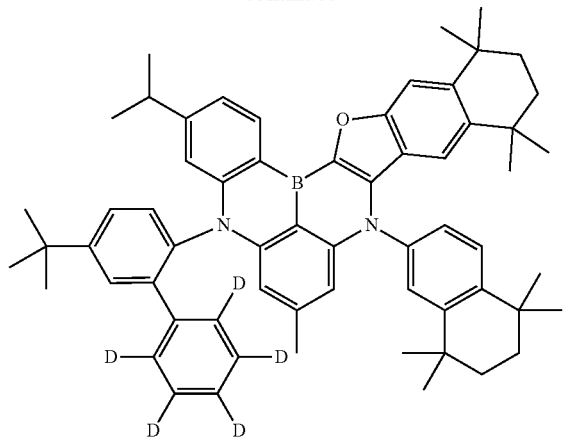
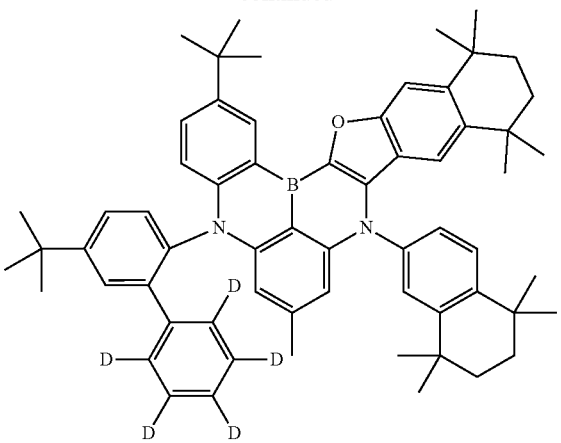

1695
-continued
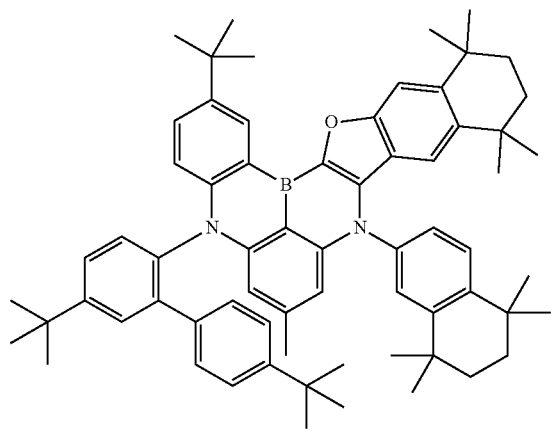
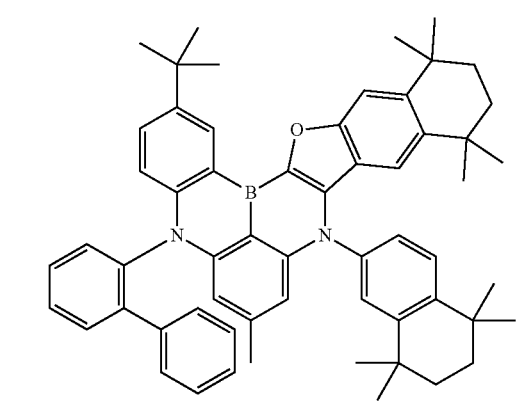
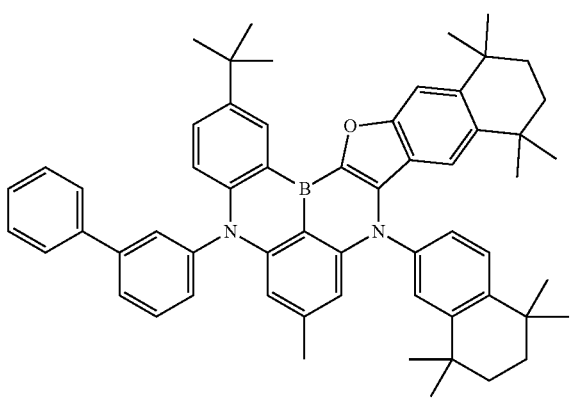
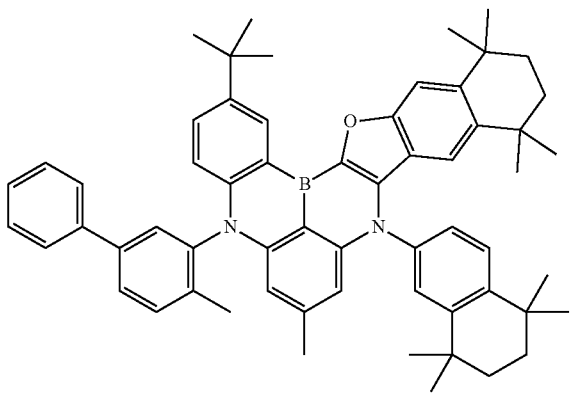
1696
-continued
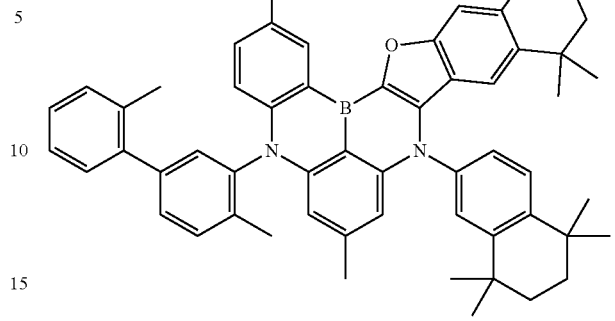
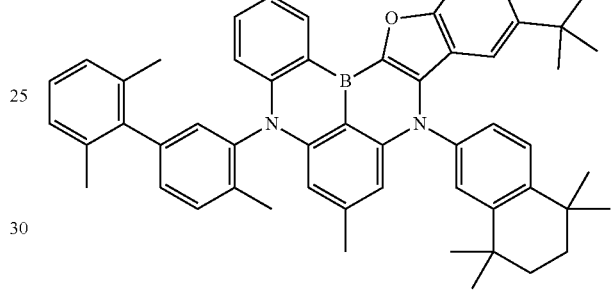
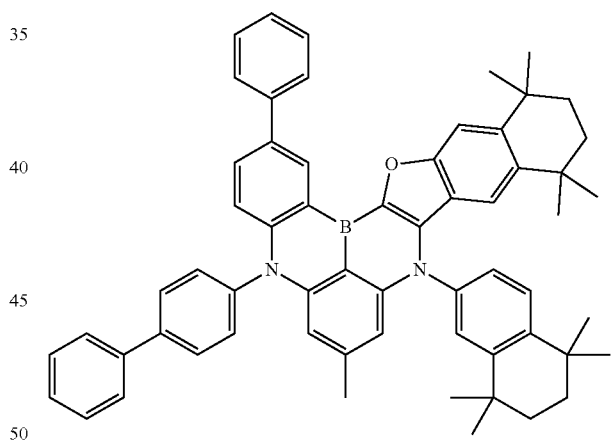
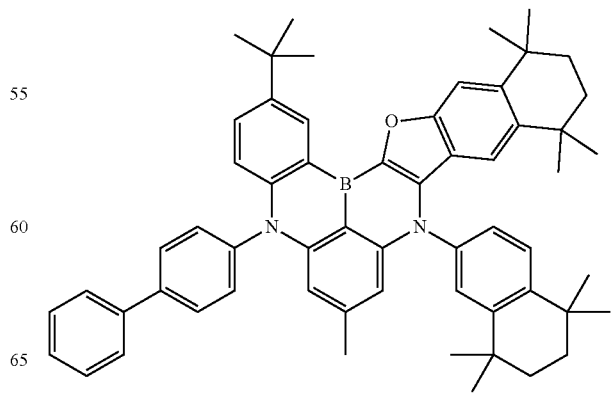

1697
-continued
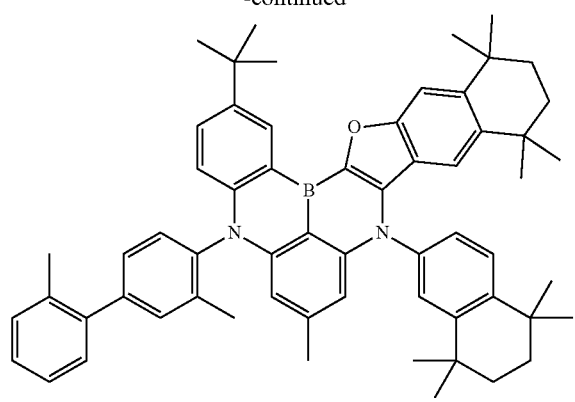
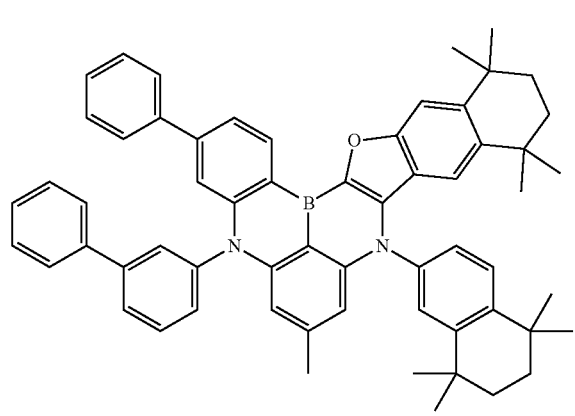
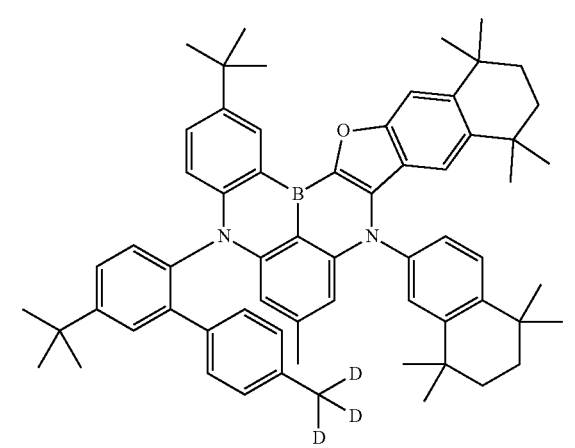
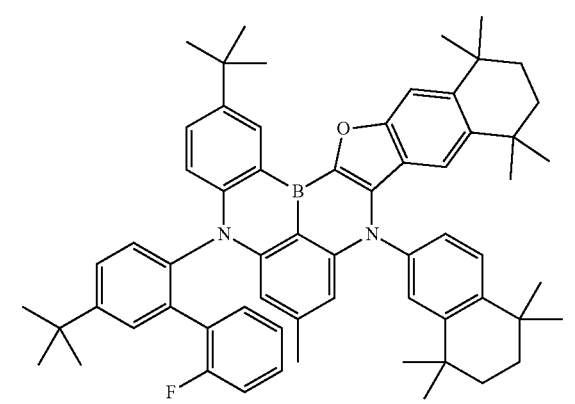
1698
-continued
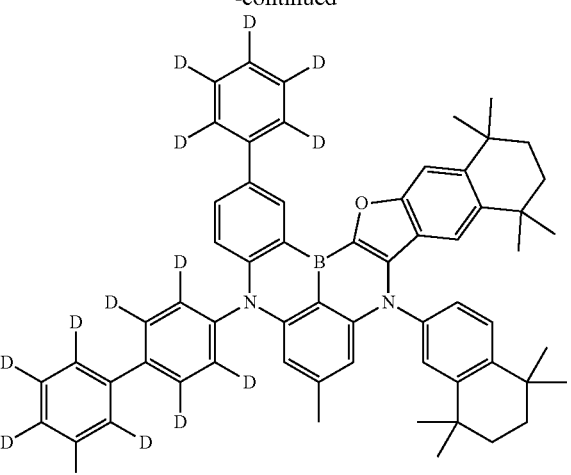
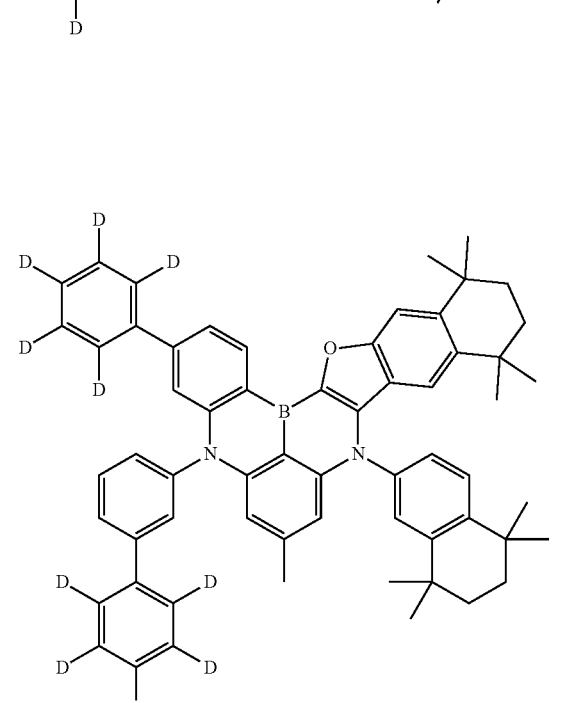
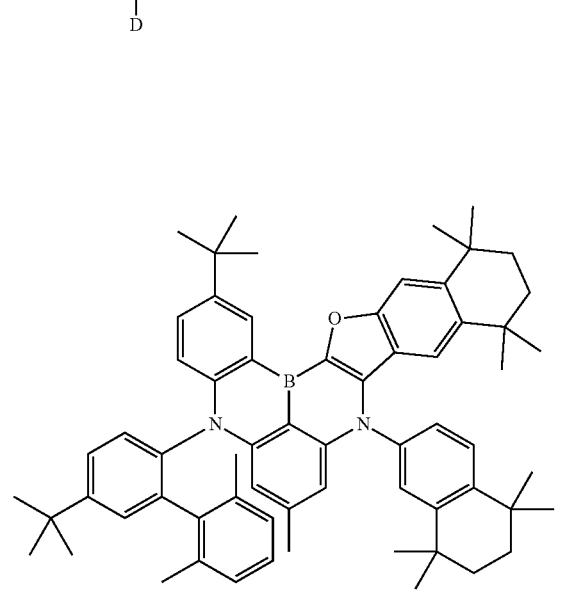

1699
-continued
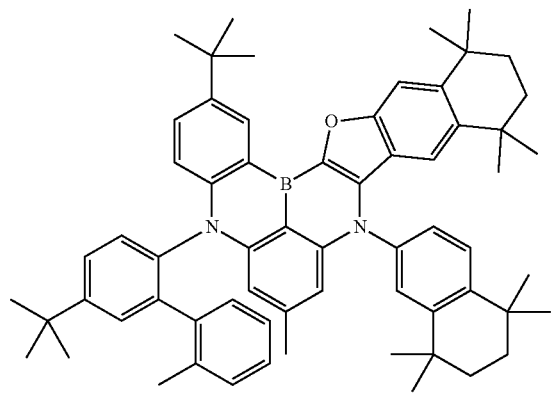
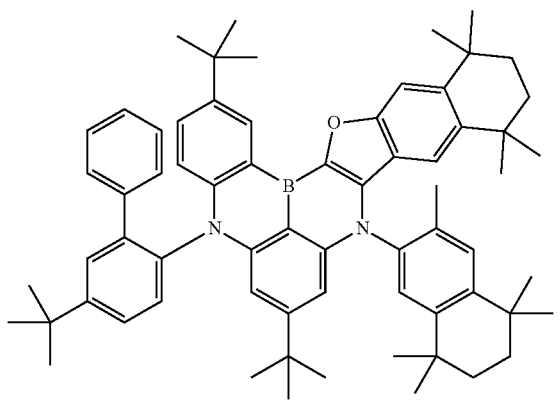
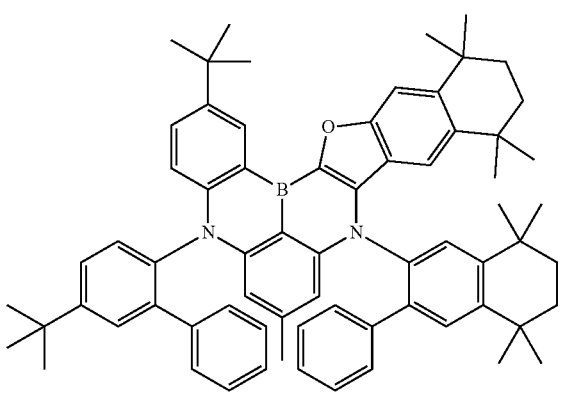
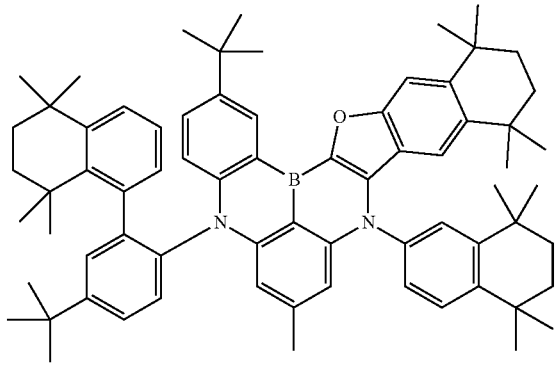
1700
-continued
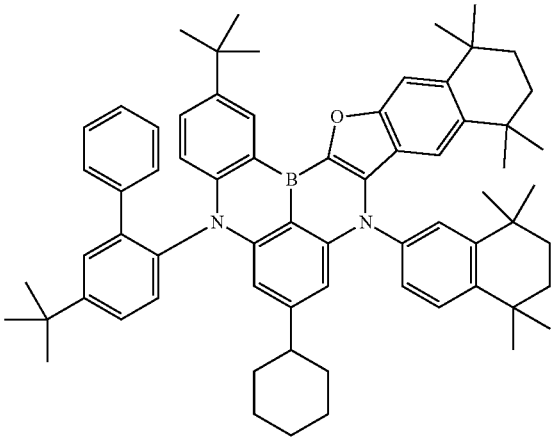
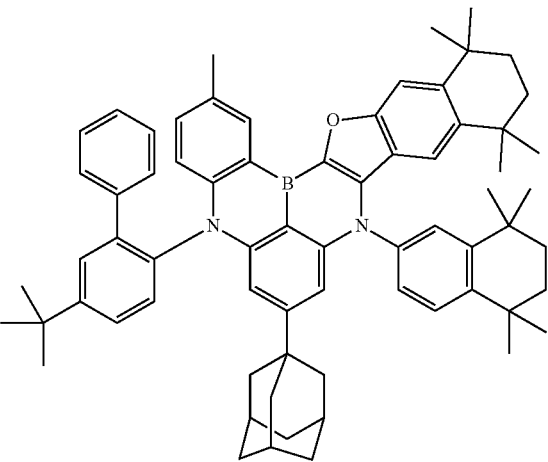
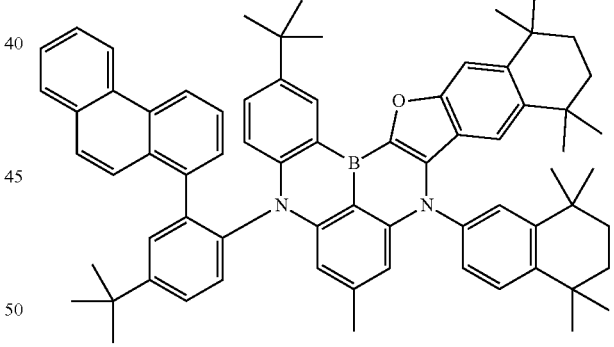
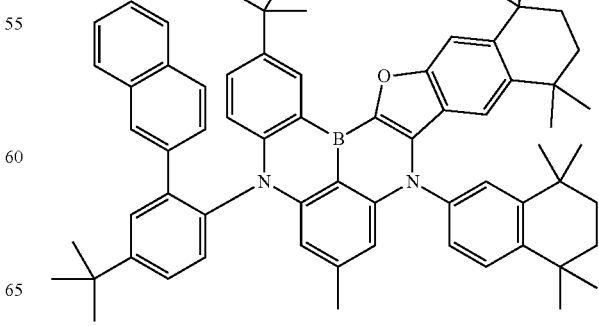

1701
-continued
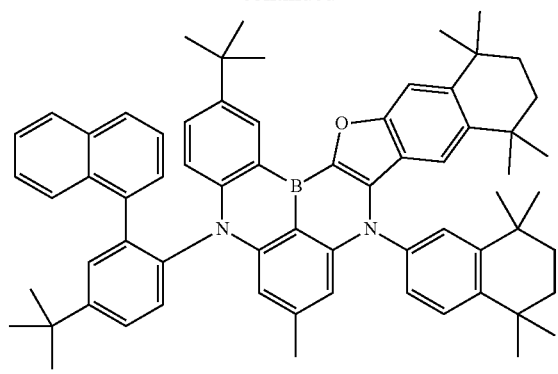
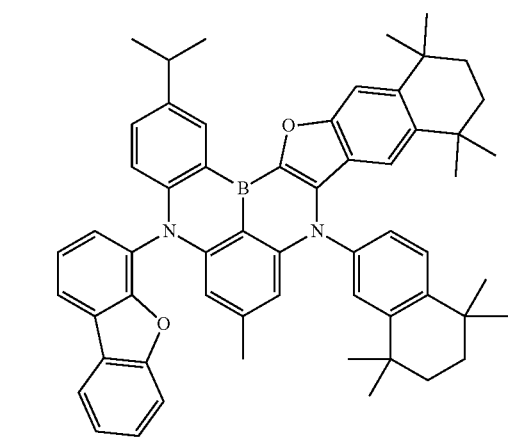
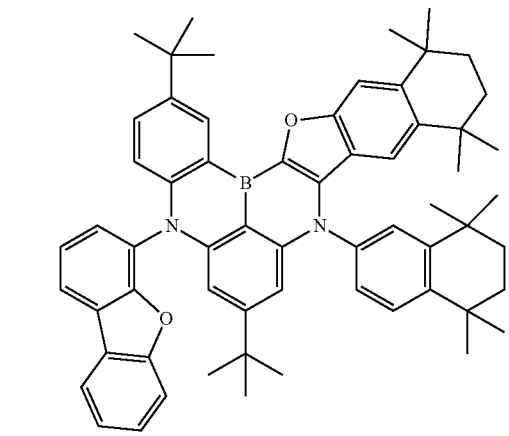
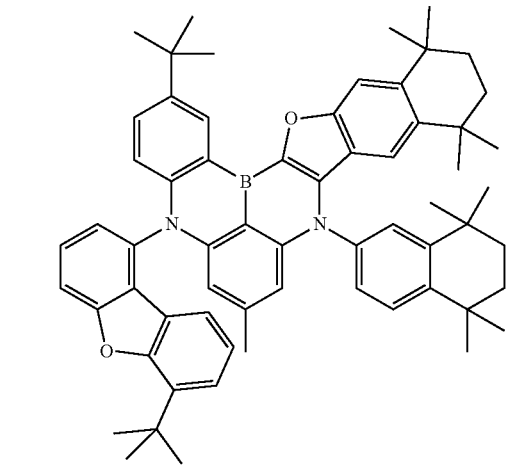
1702
-continued
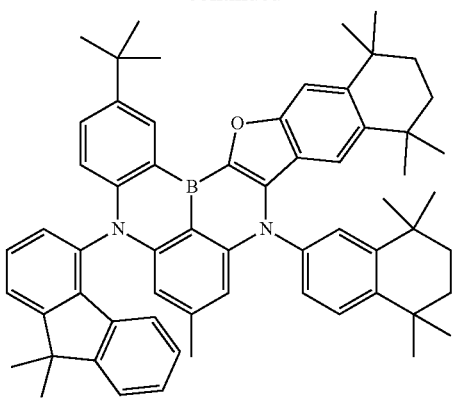
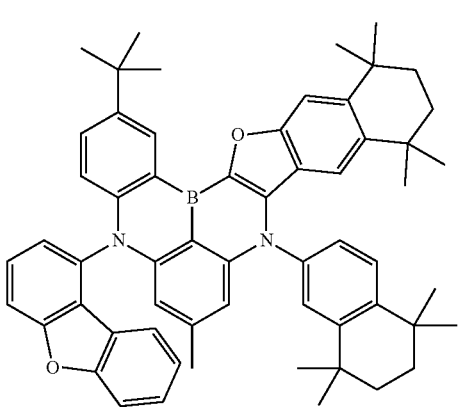
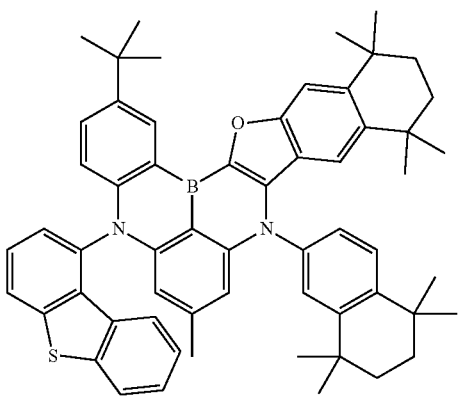
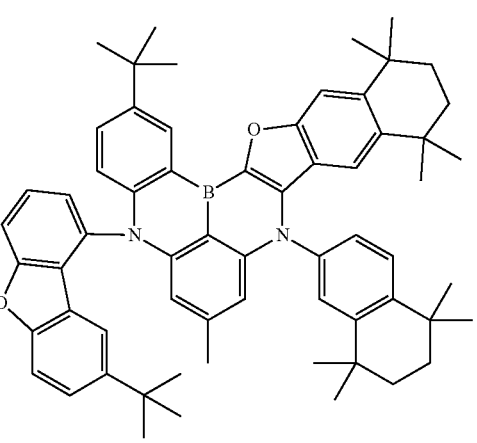

1703
-continued
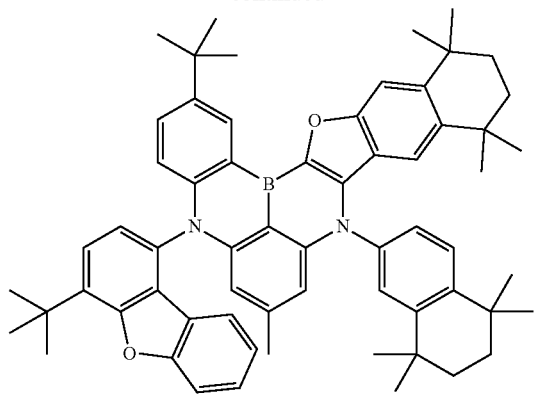
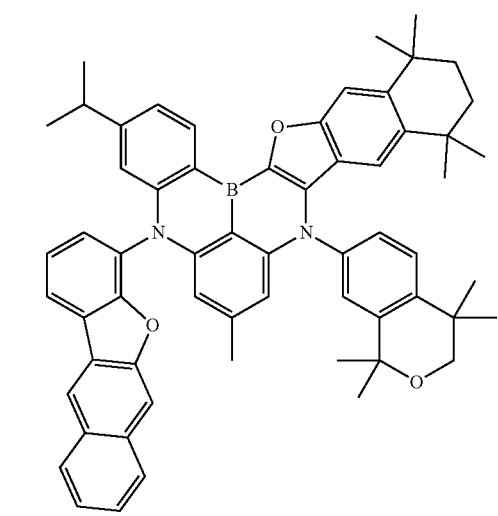
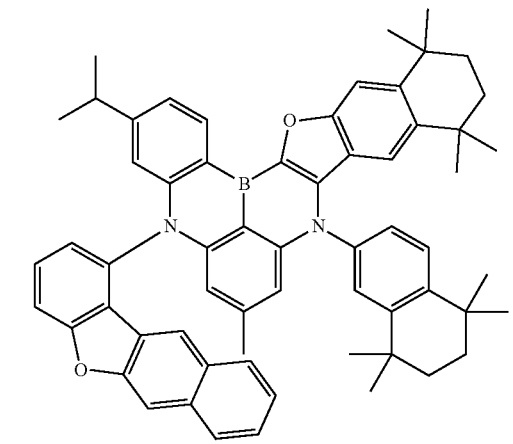
1704
-continued
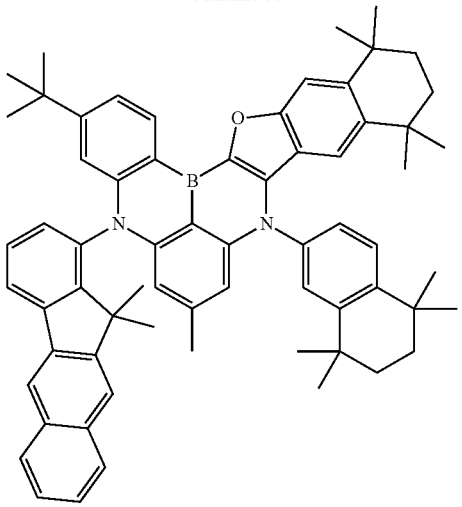
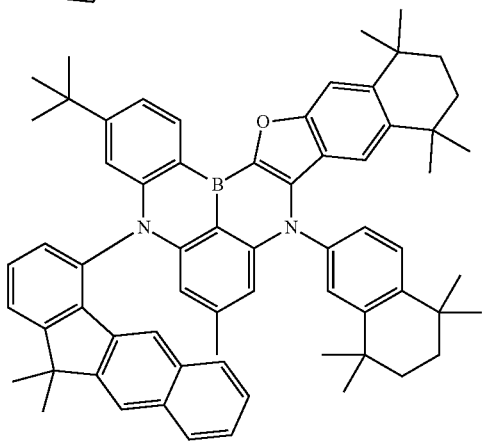
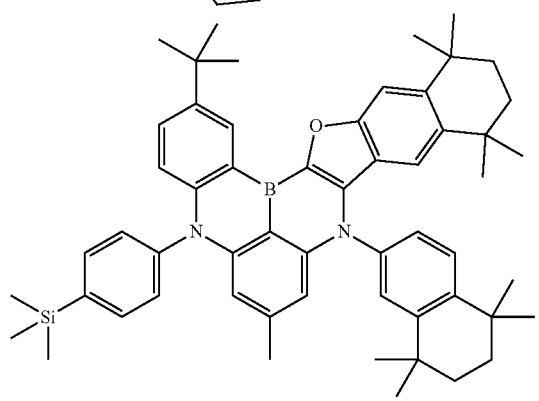
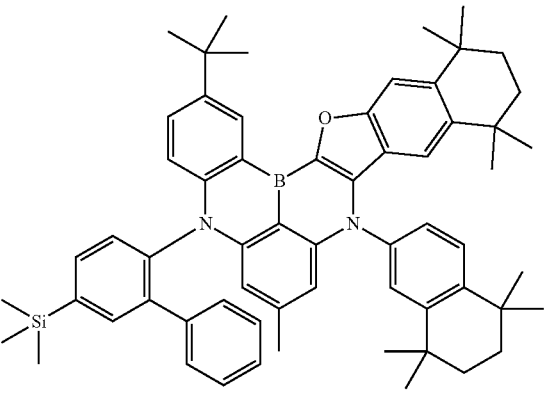

1705
-continued
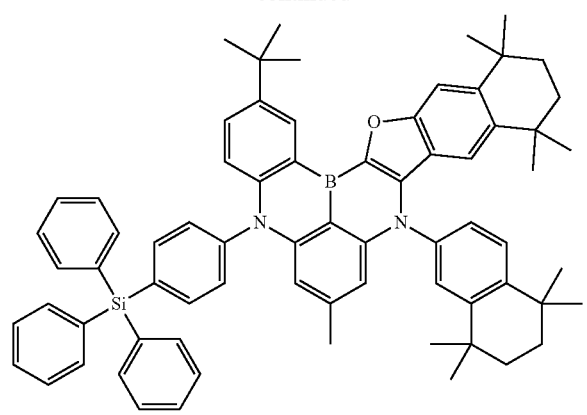
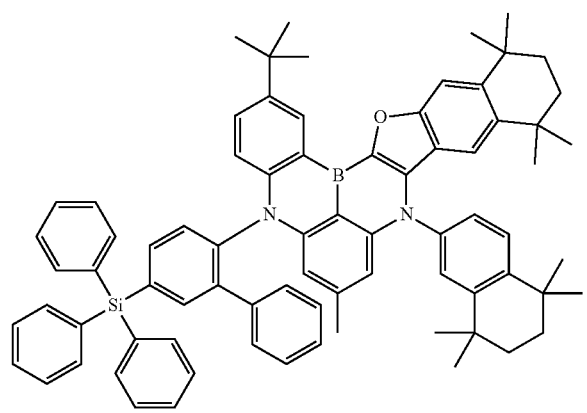
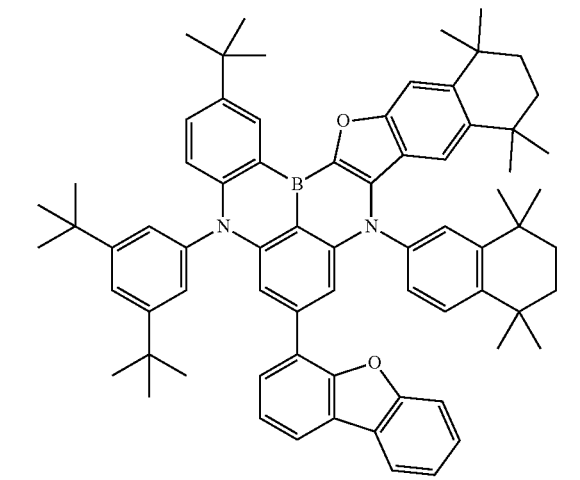
1706
-continued
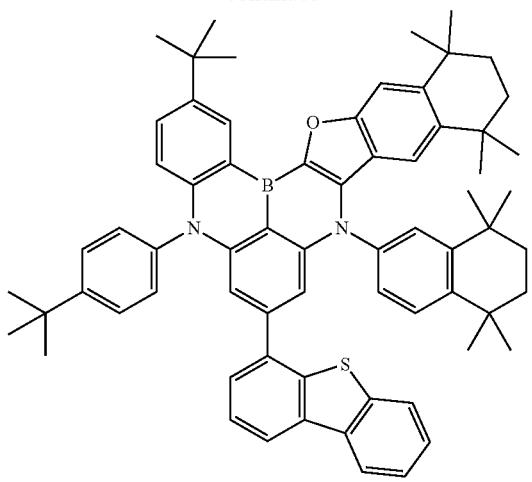
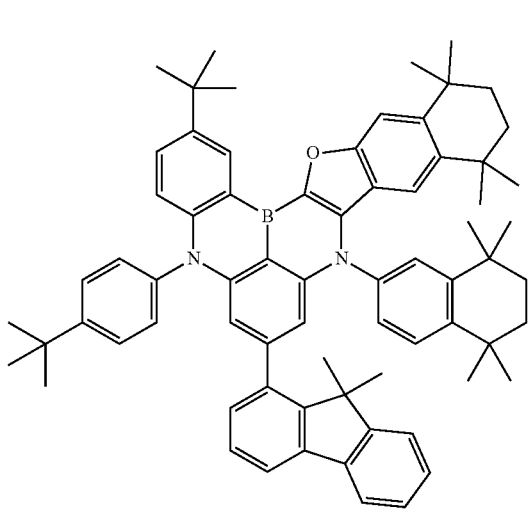
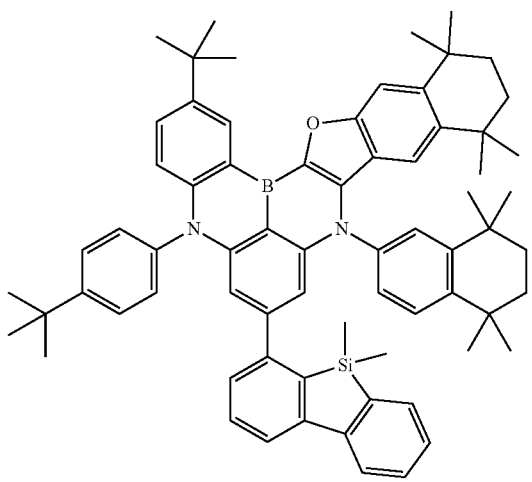

1707
-continued
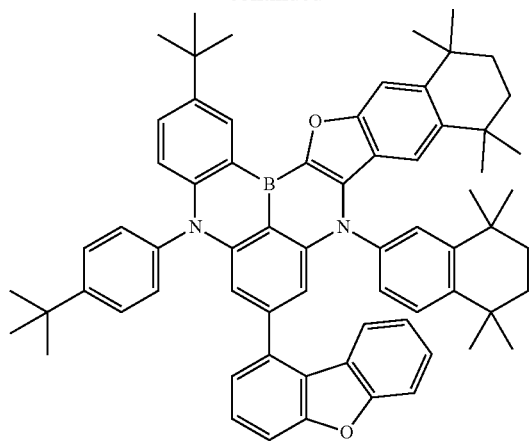
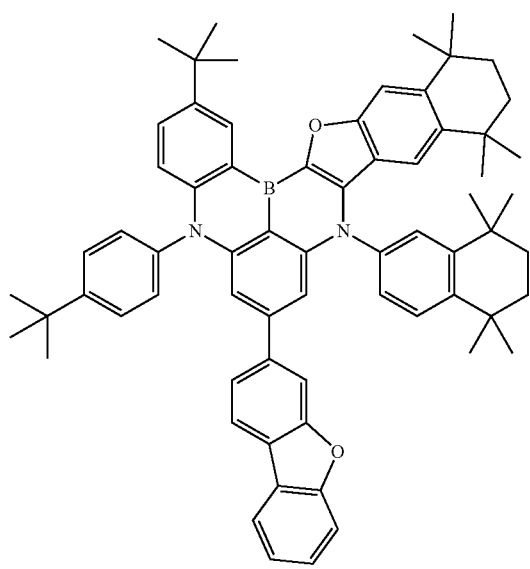
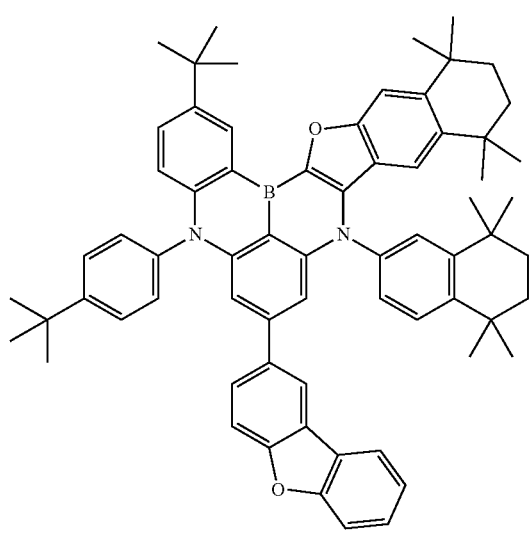
1708
-continued
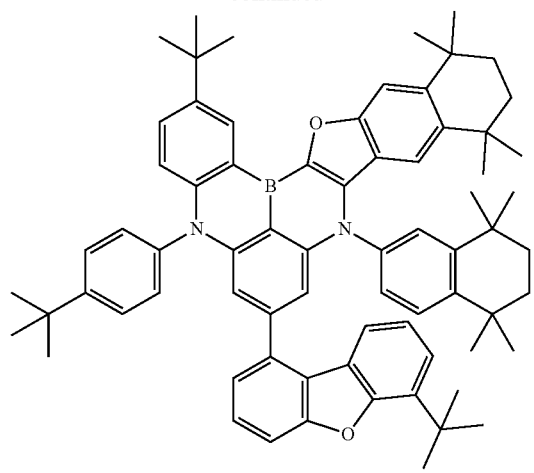
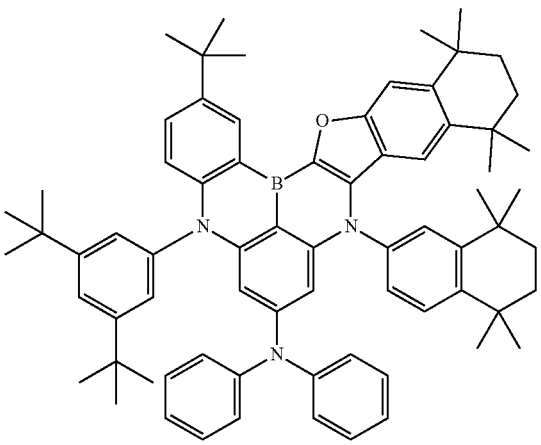
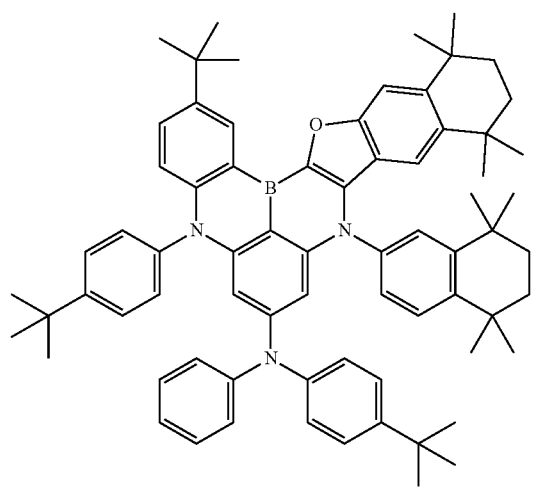

1709
-continued
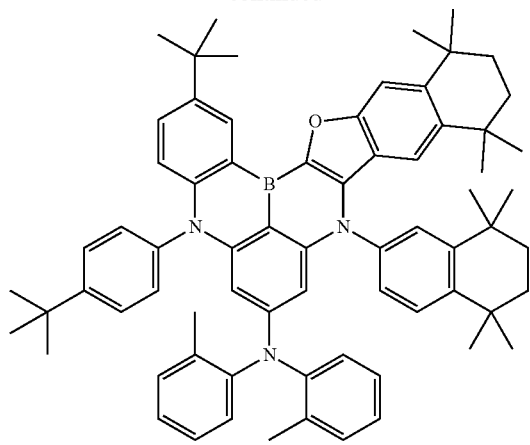
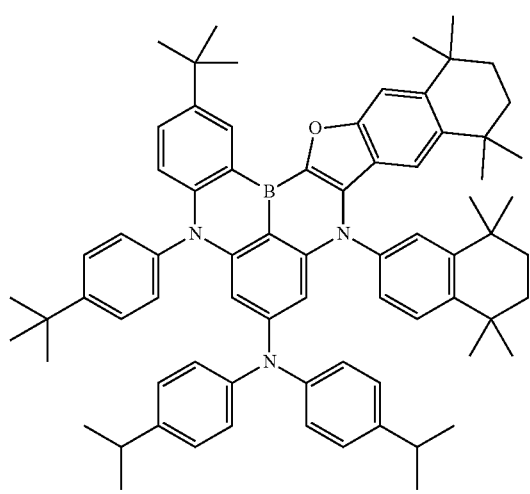
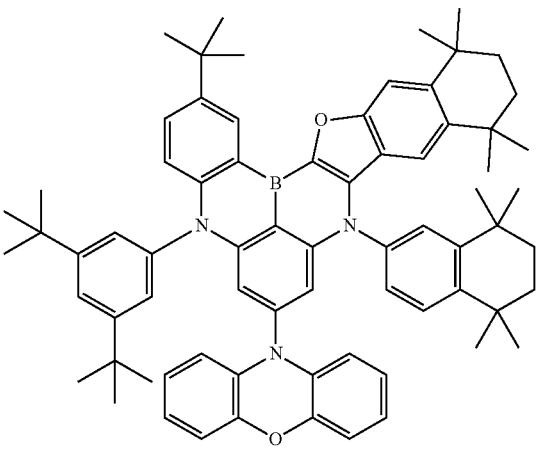
1710
-continued
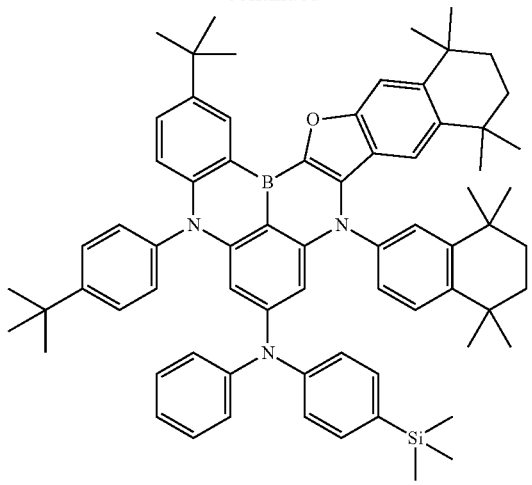
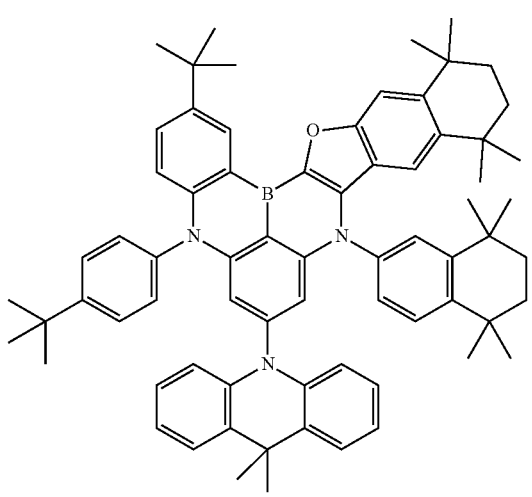
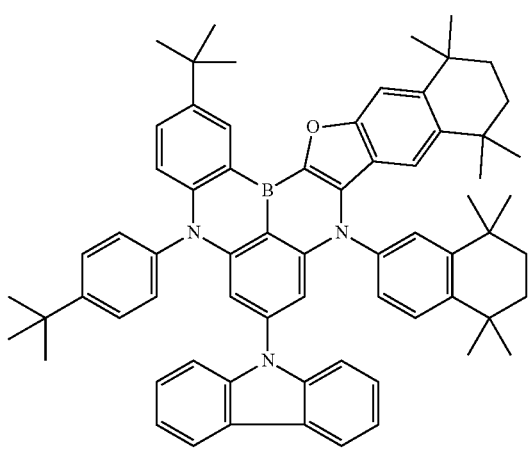

1711
-continued
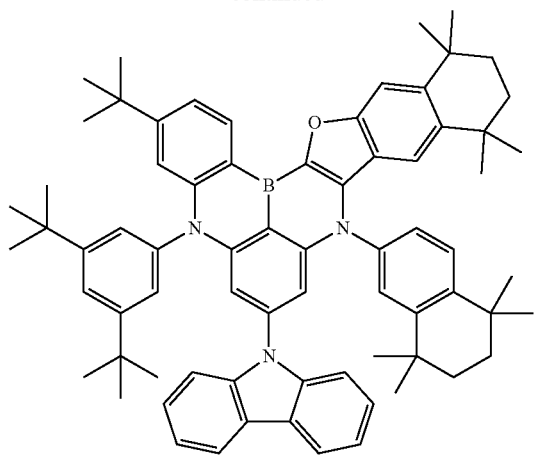
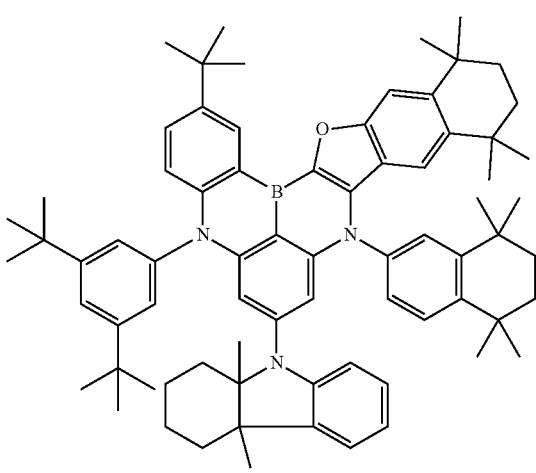
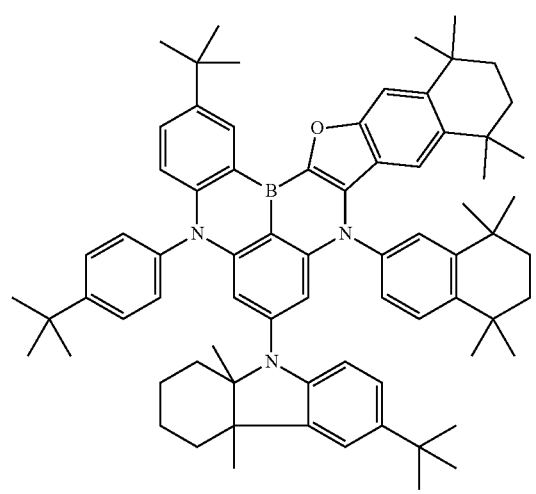
1712
-continued
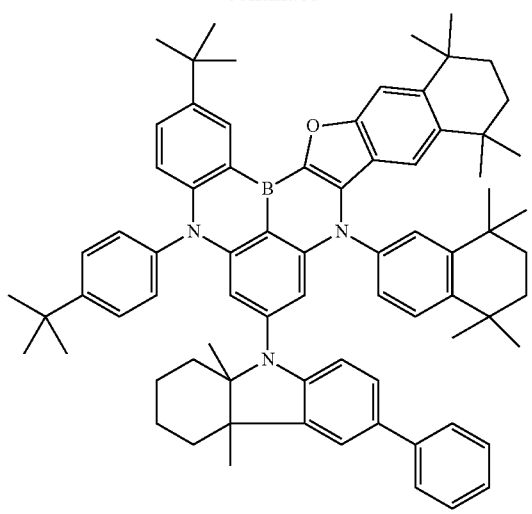
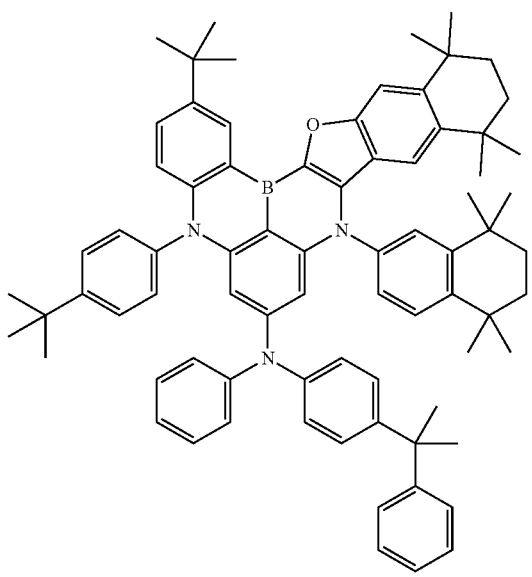
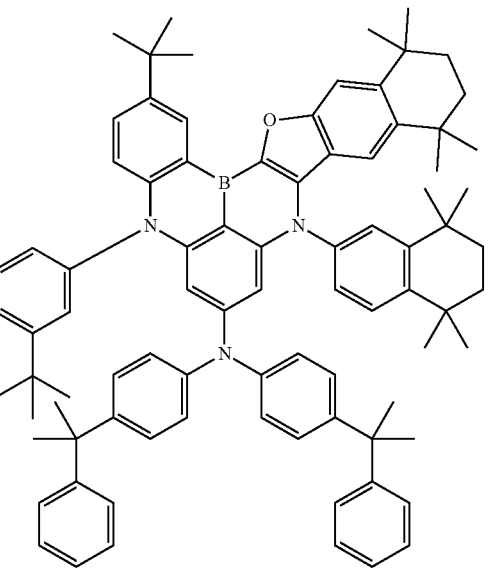

1713
-continued
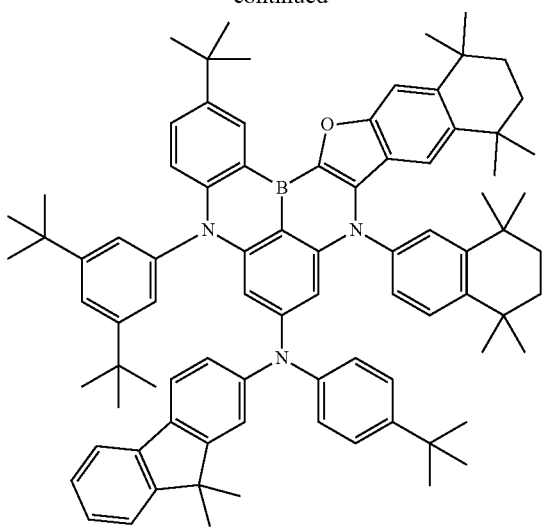
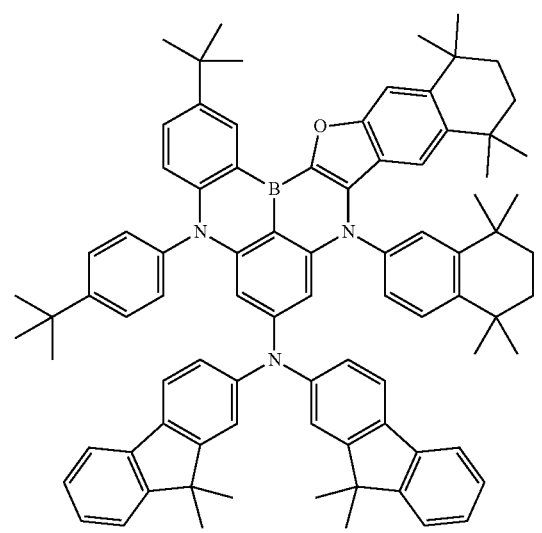
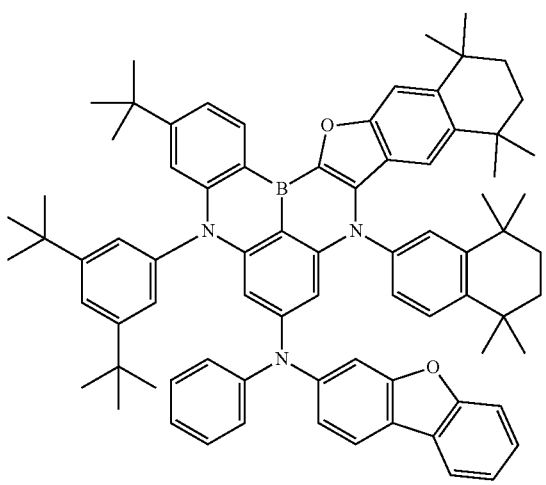
1714
-continued
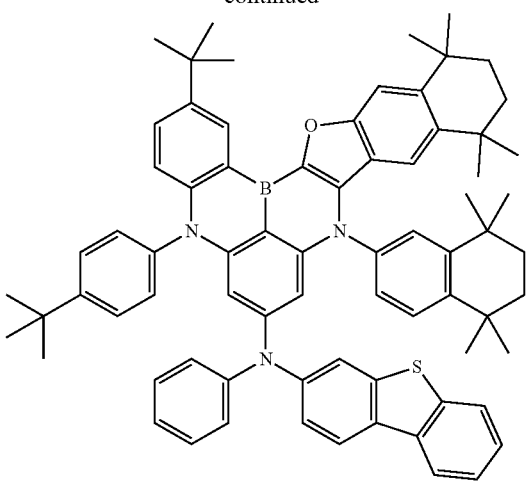
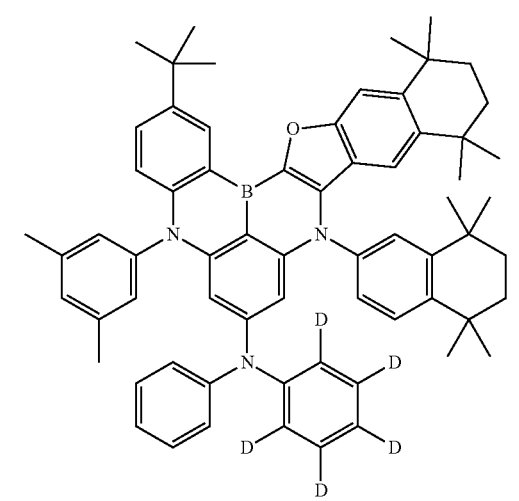

1715
-continued
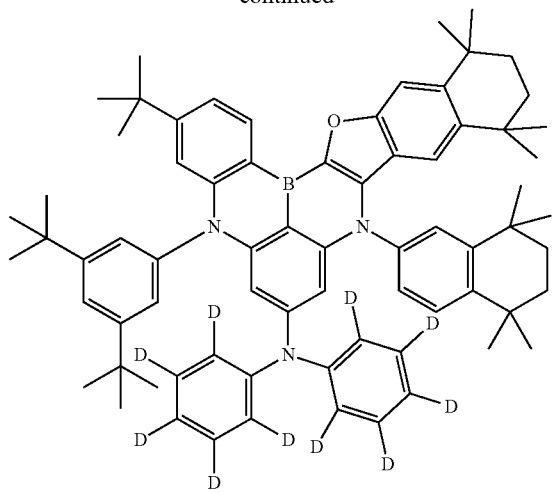
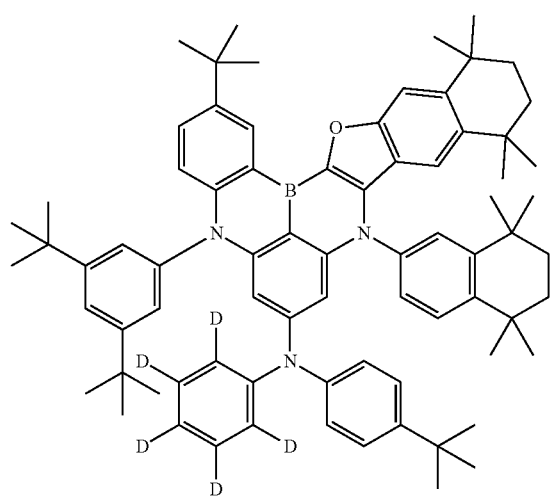
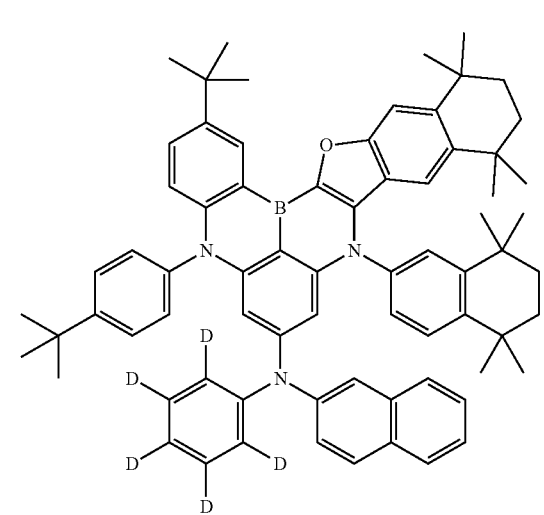
1716
-continued
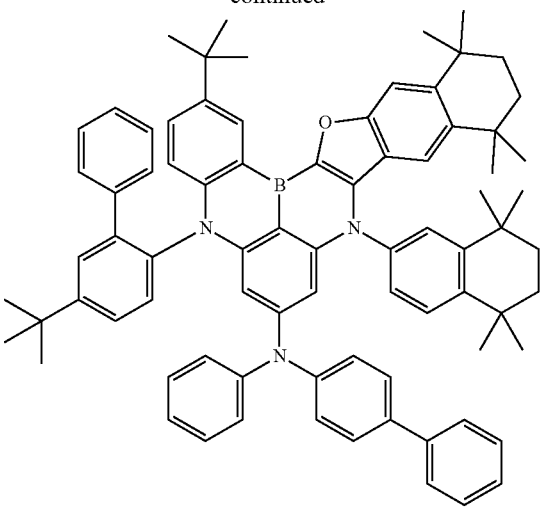
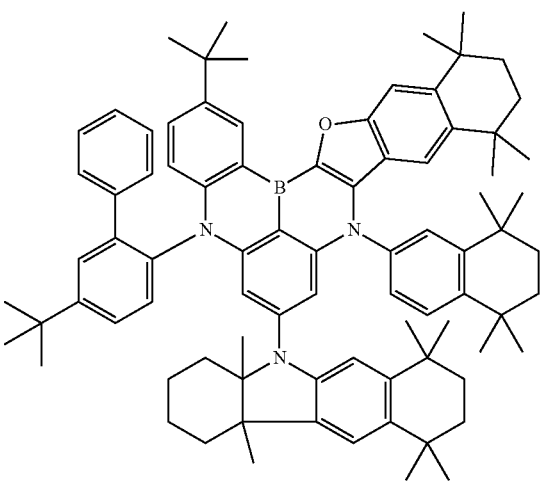
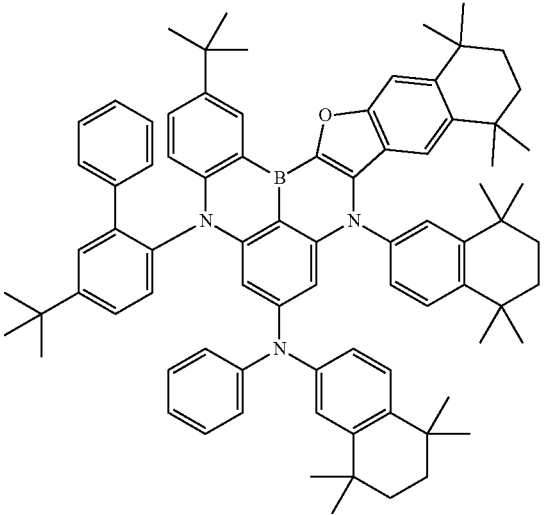

1717
-continued
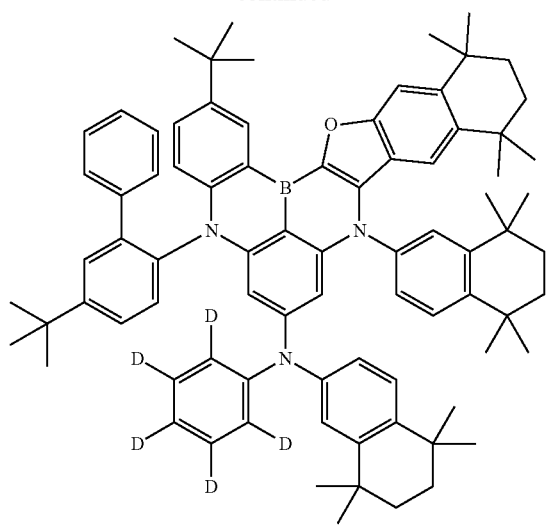
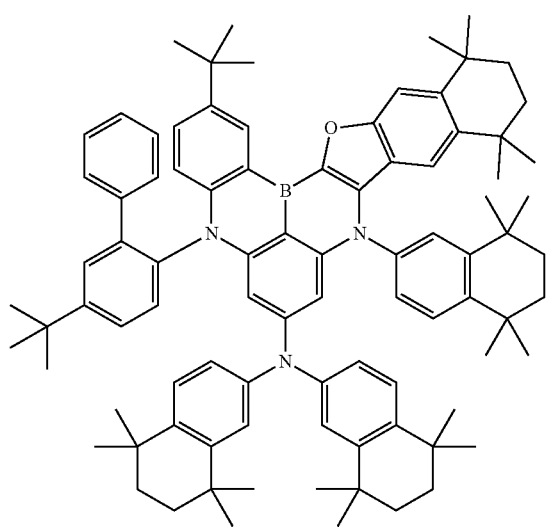
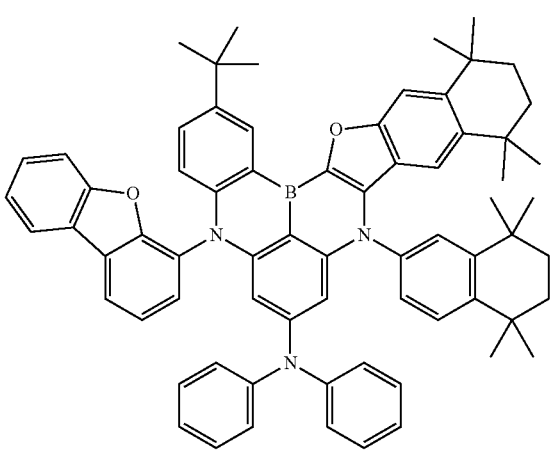
1718
-continued
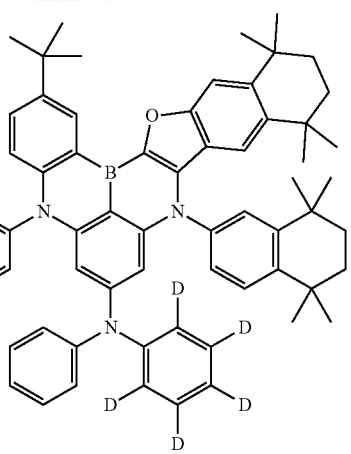
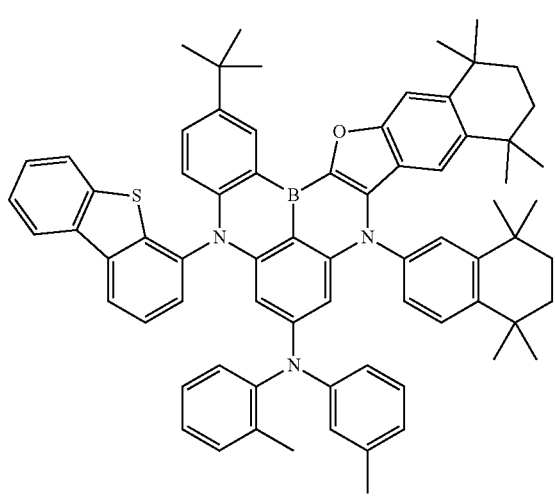
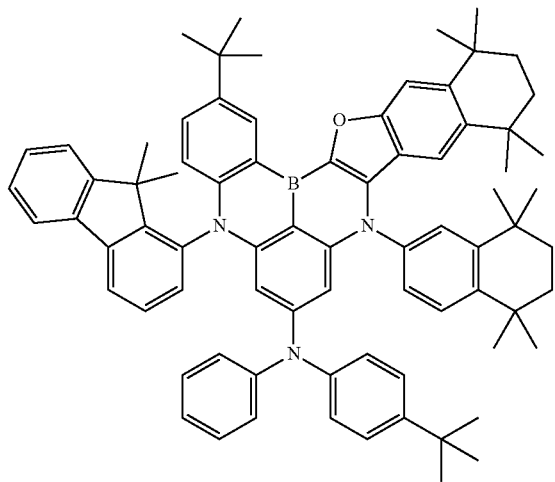

1719
-continued
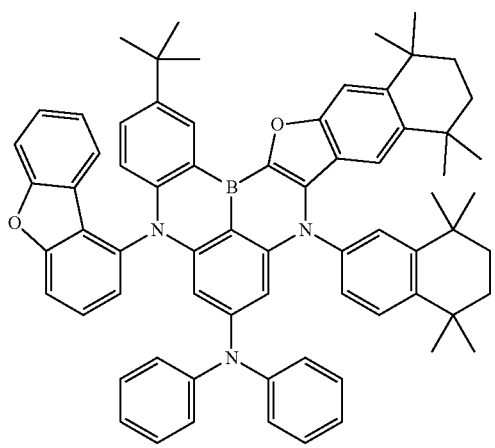
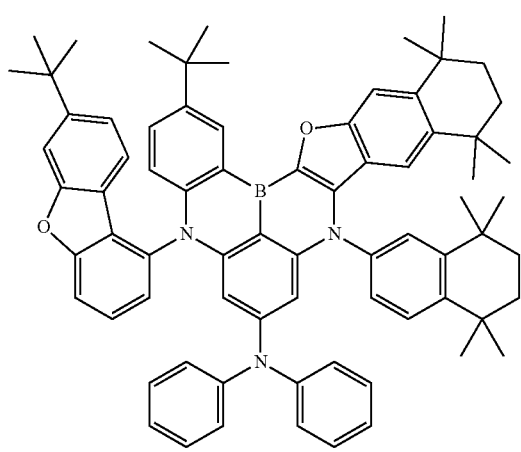
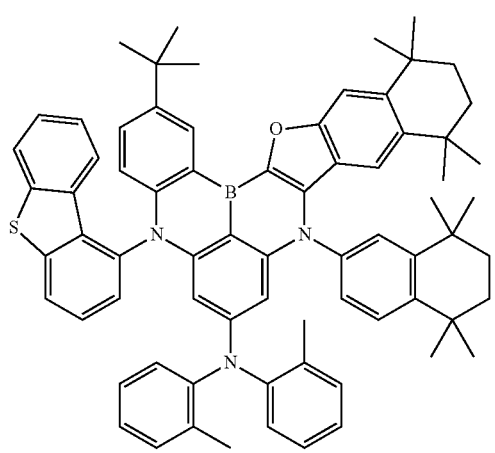
1720
-continued
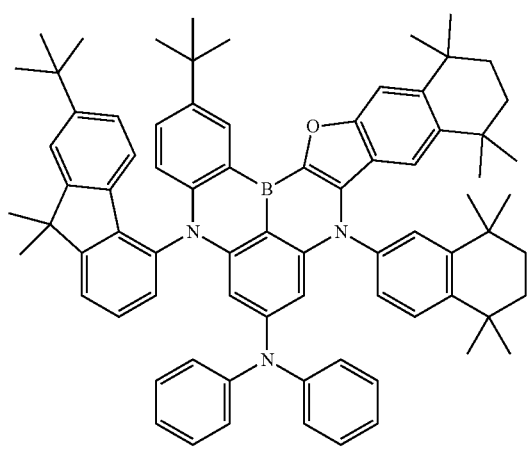
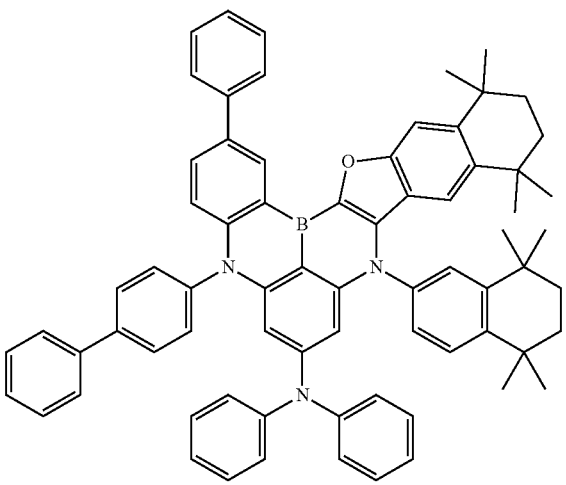
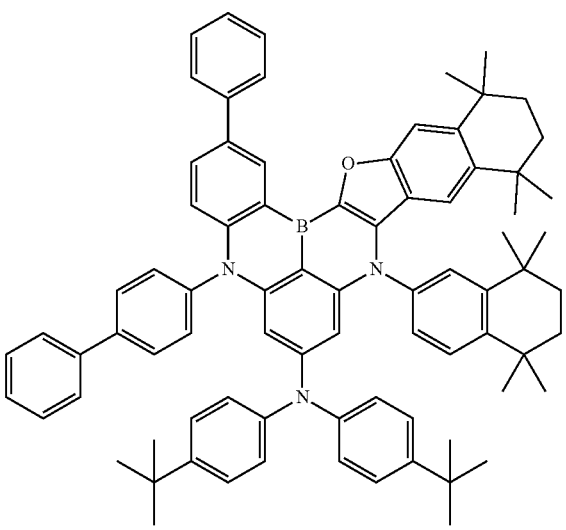

1721
-continued
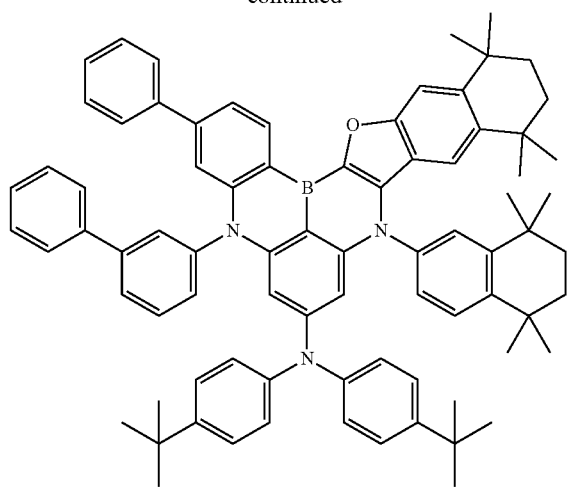
1722
-continued
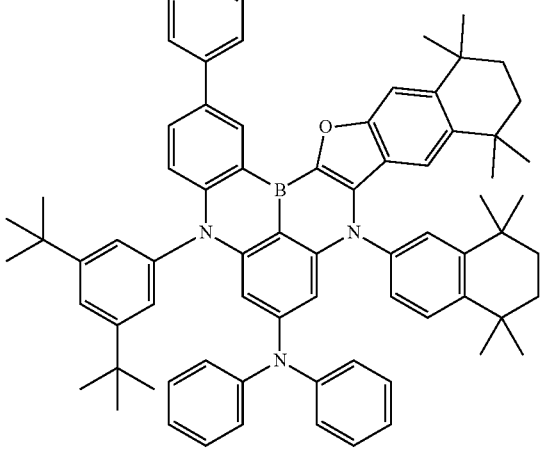
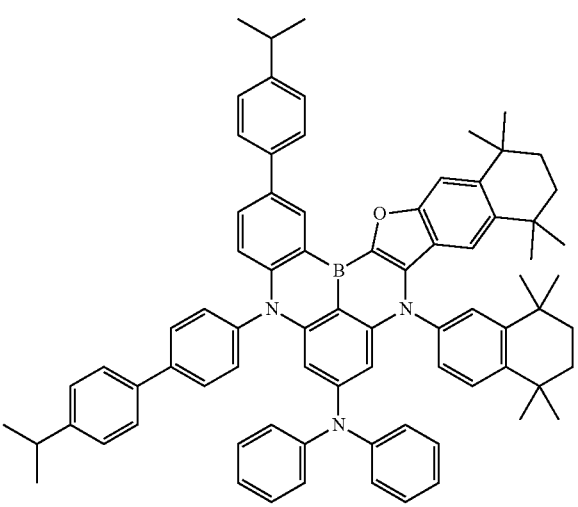
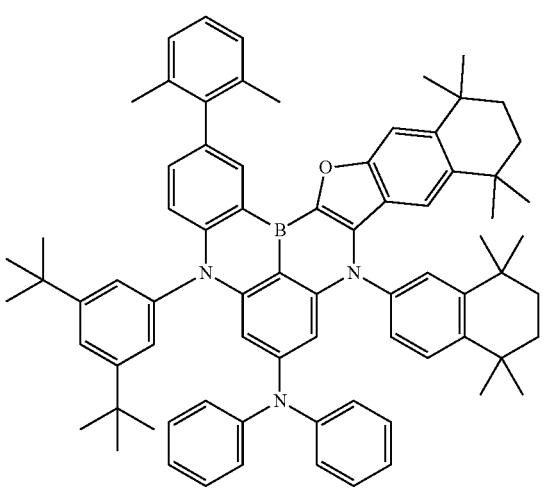
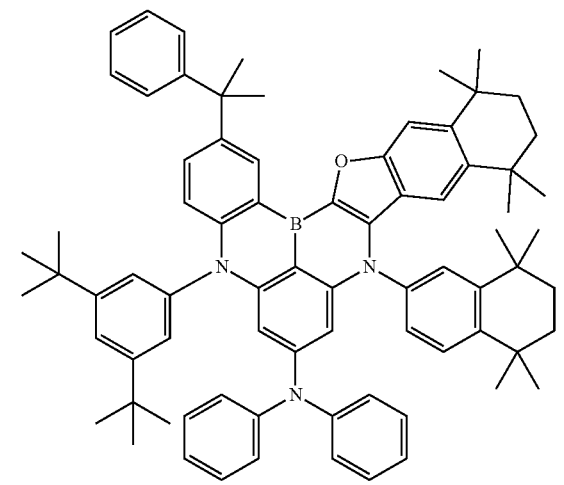

1723
-continued
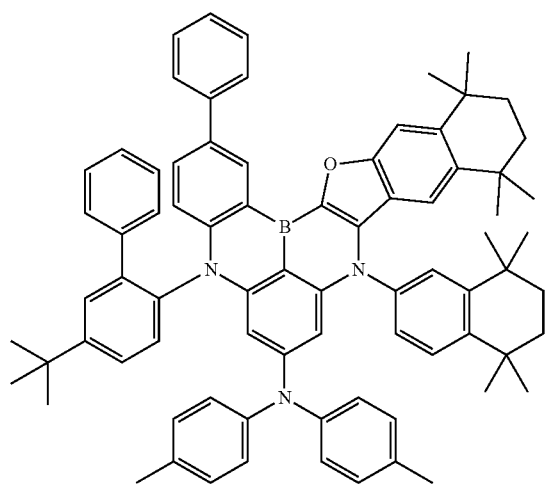
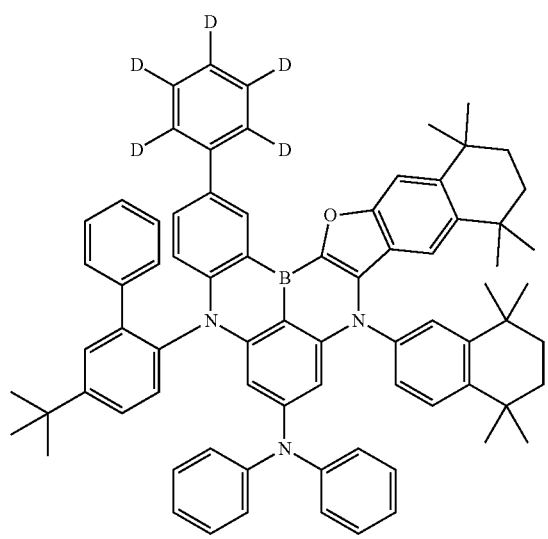
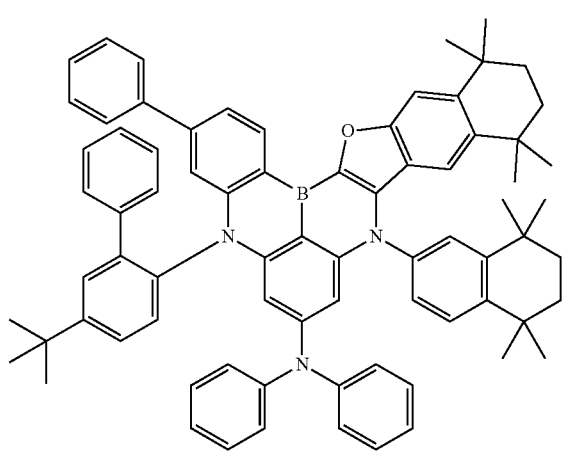
1724
-continued
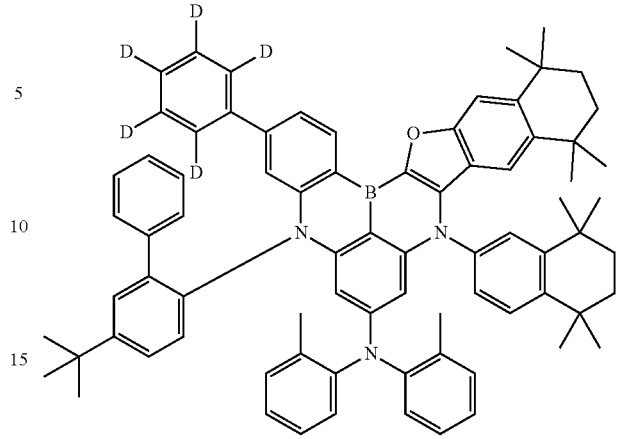
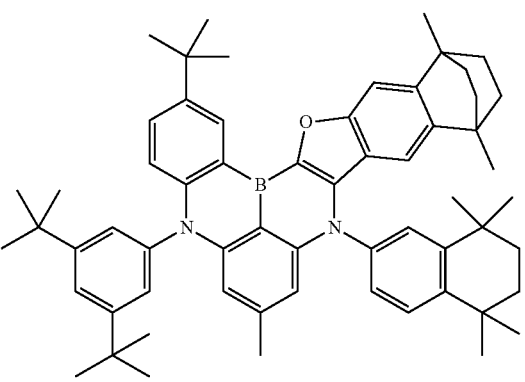
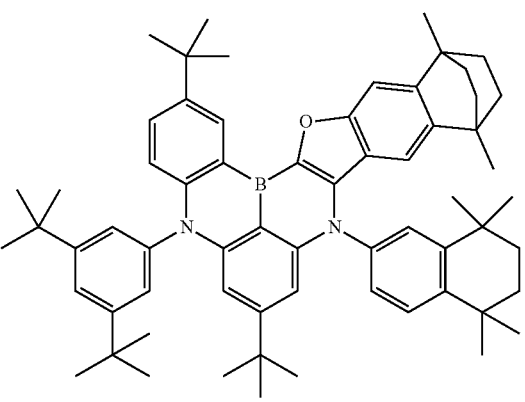
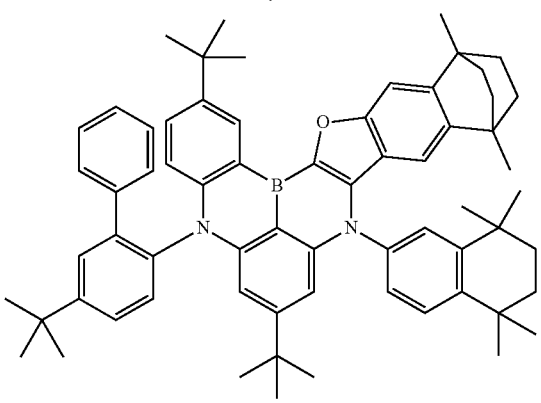

1725
-continued
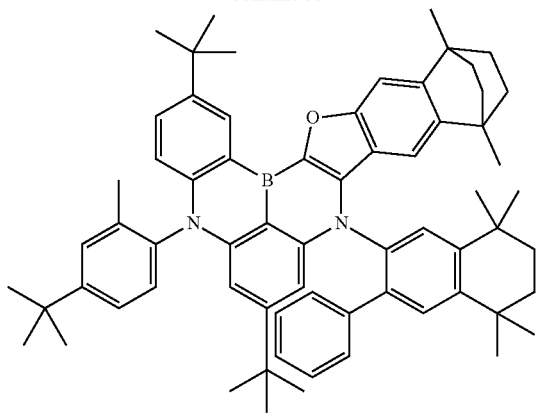
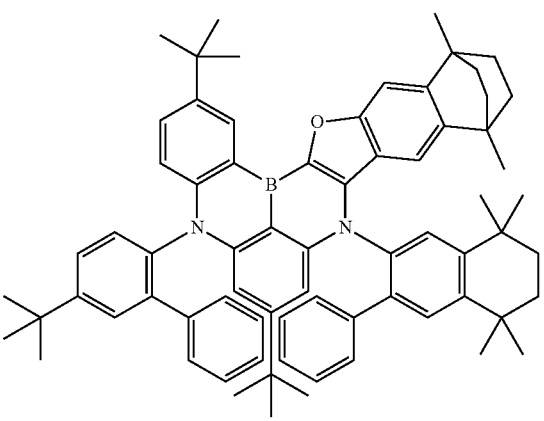
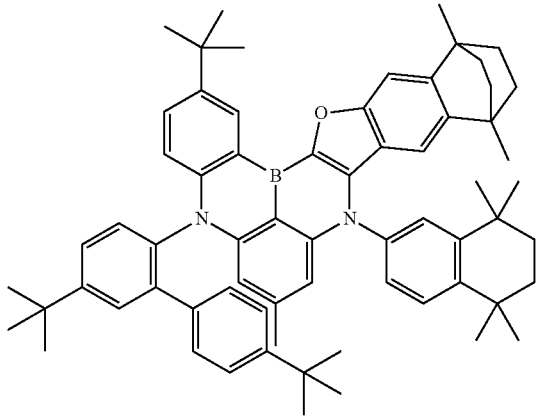
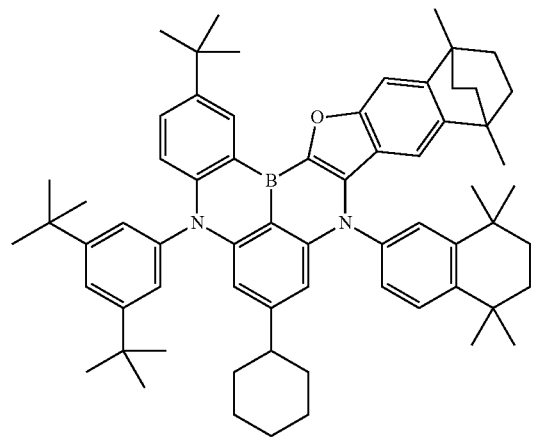
1726
-continued
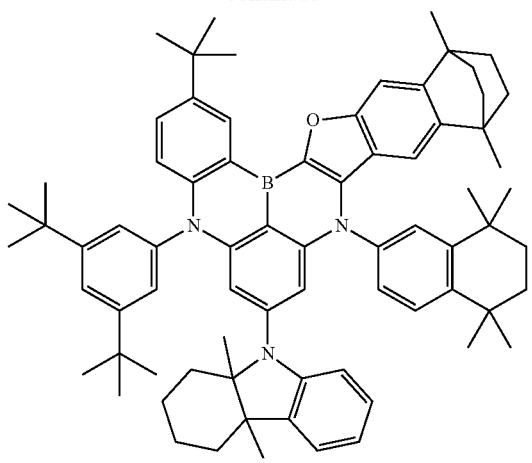
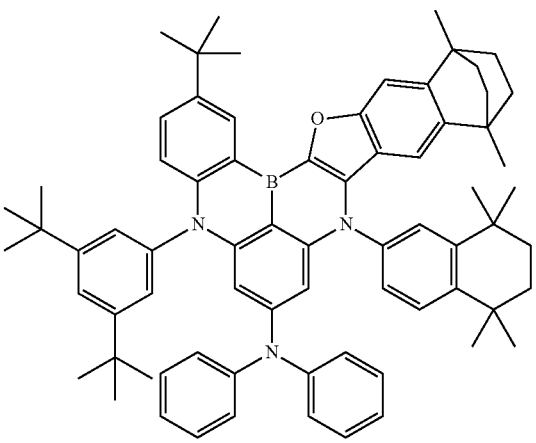
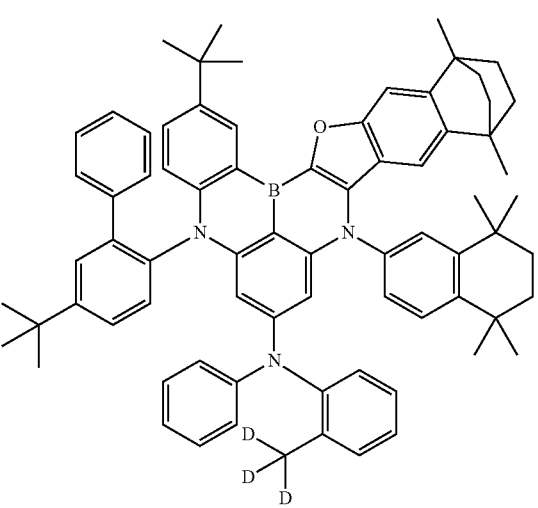

1727
-continued
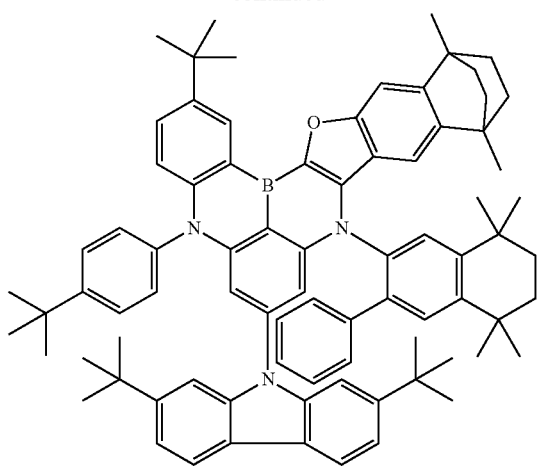
1728
-continued
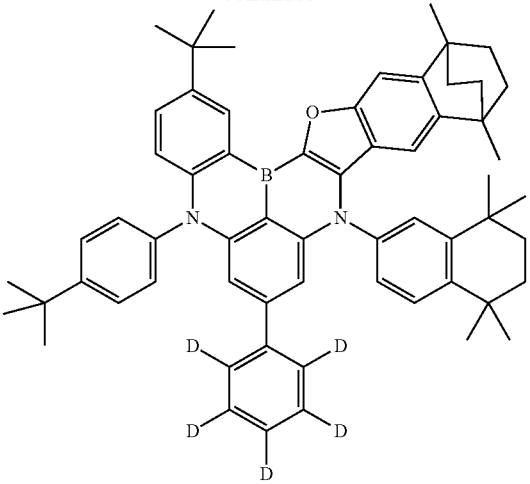
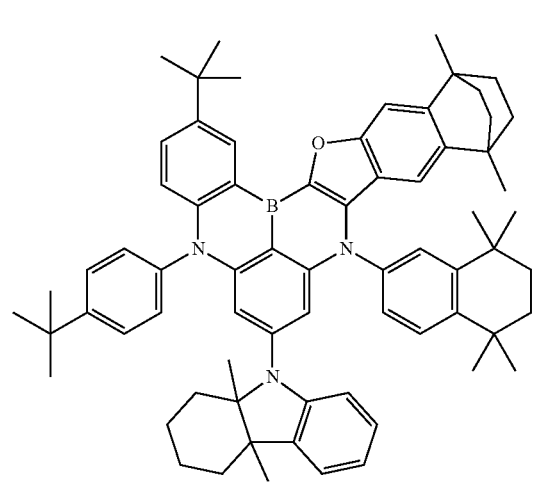
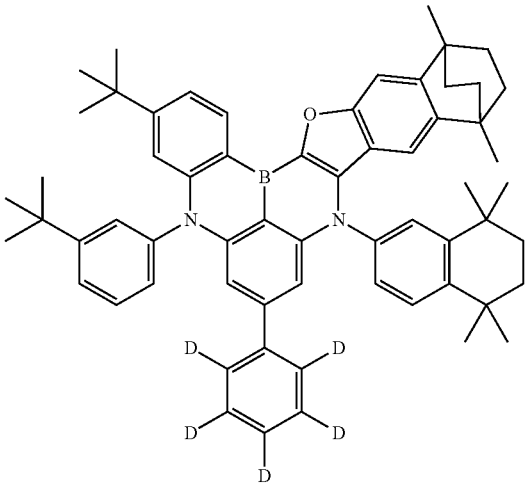
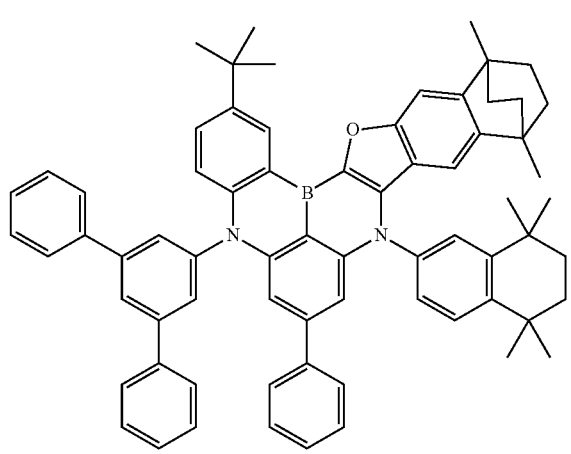
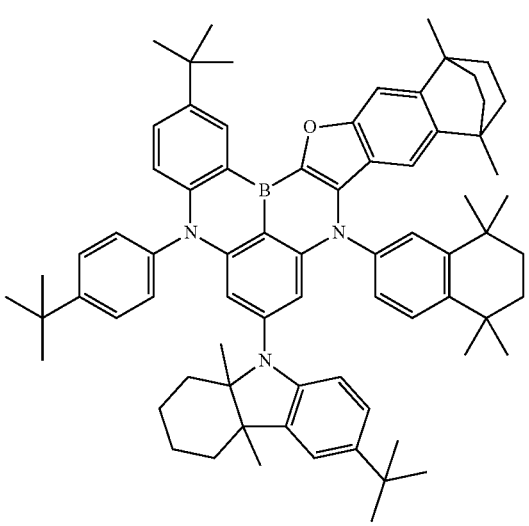

1729
-continued
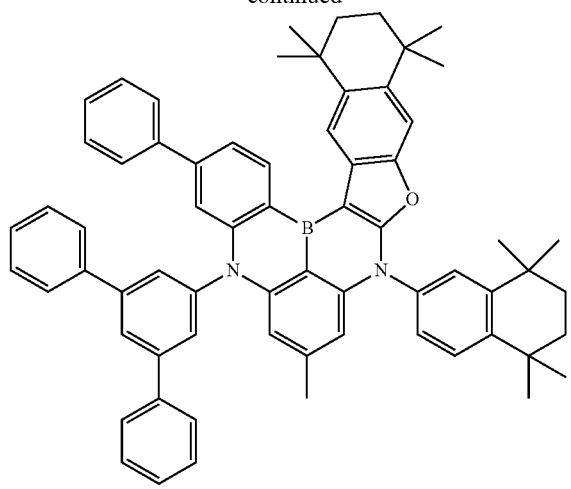
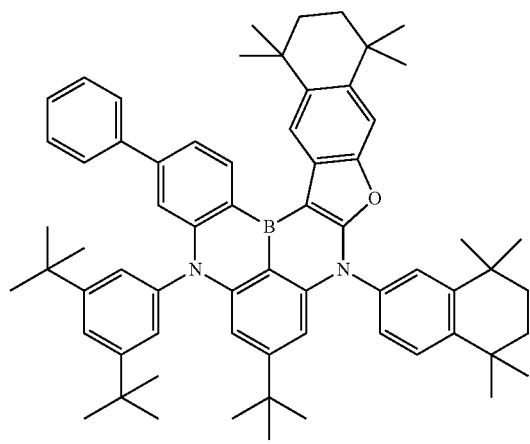
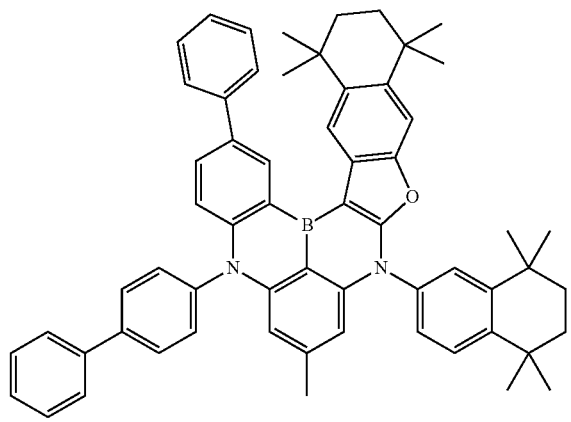
1730
-continued
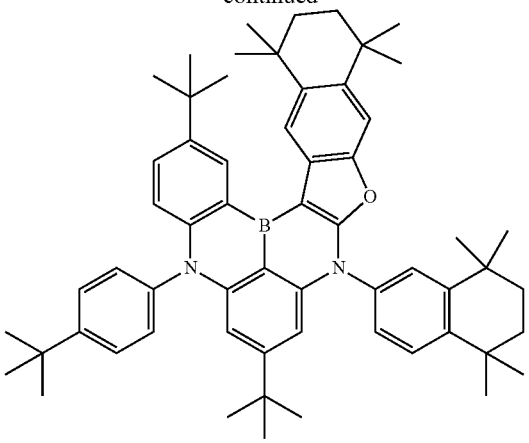
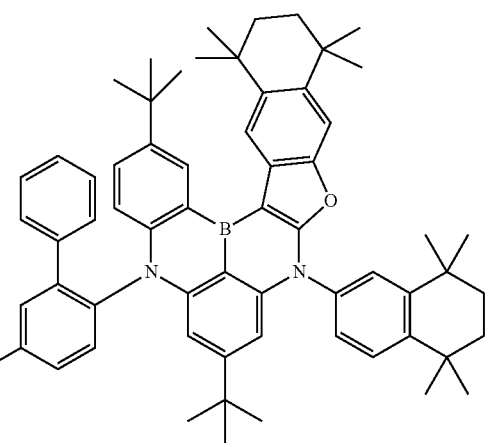
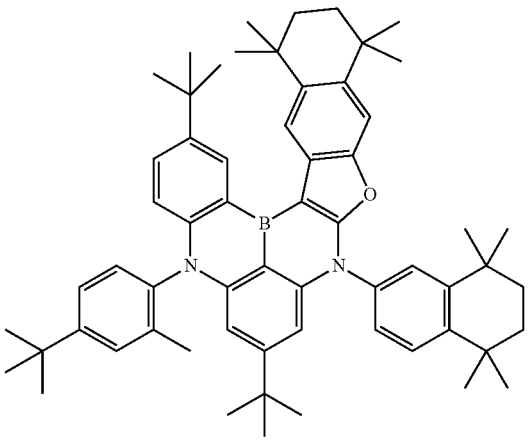

1731
-continued
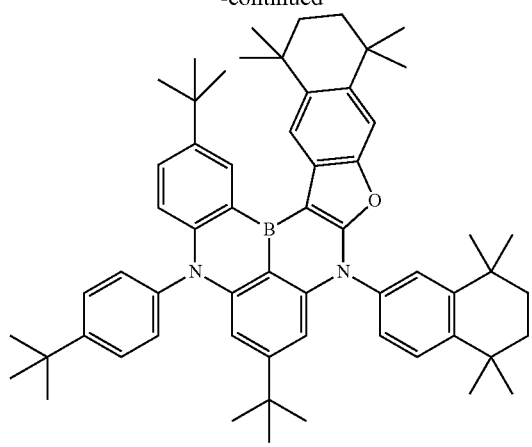
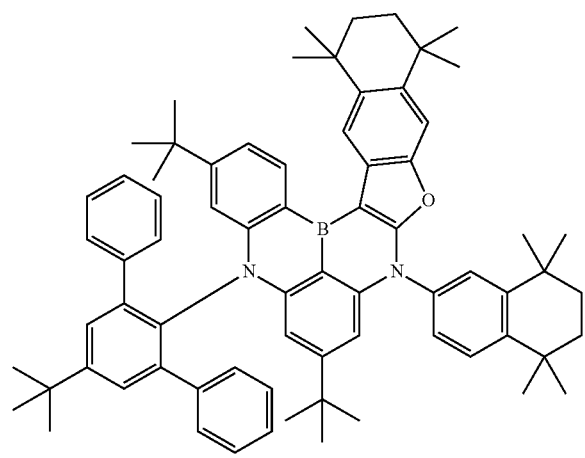
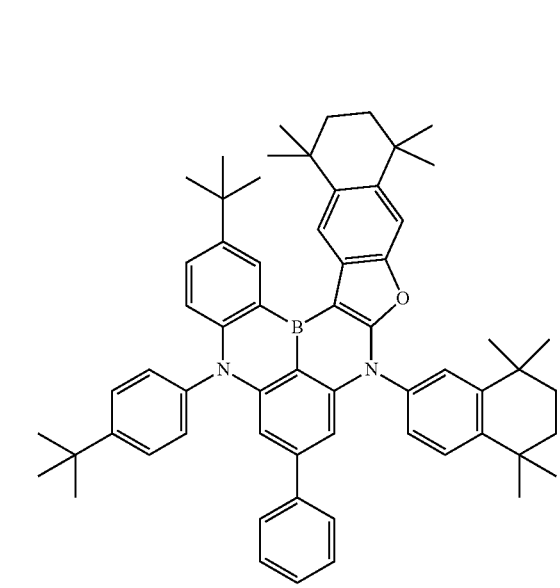
1732
-continued
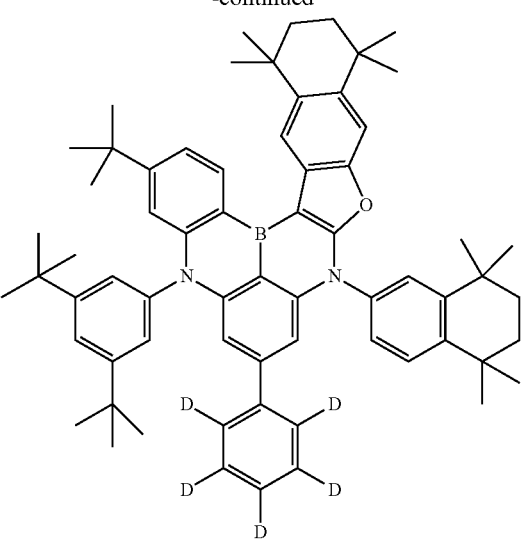
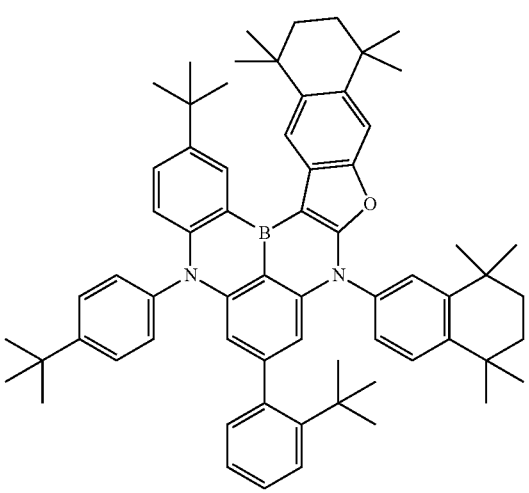
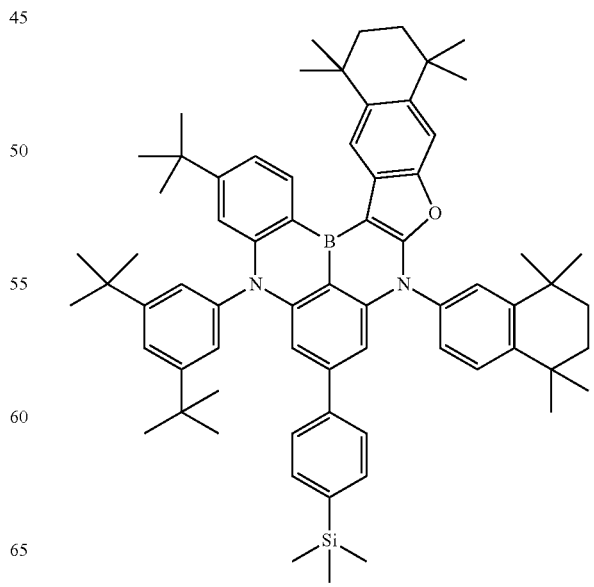

1733
-continued
1734
-continued
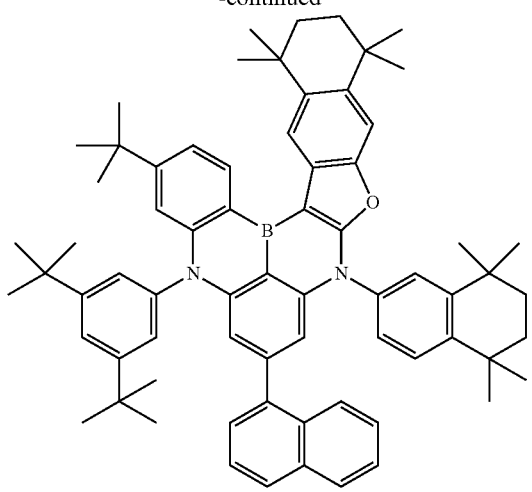
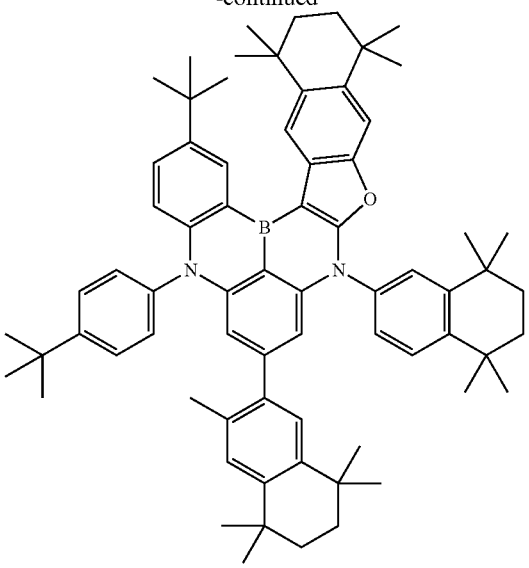
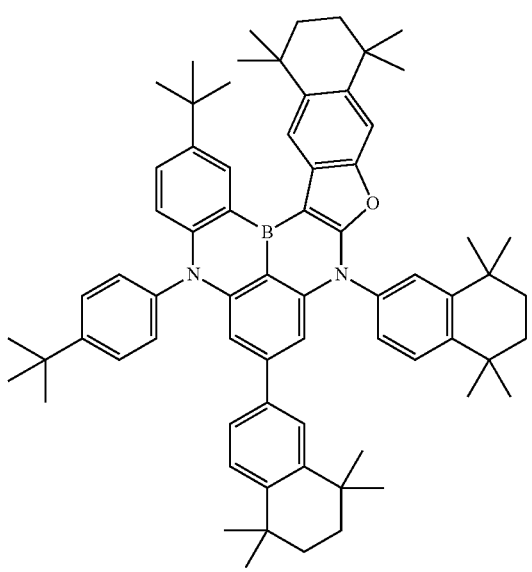
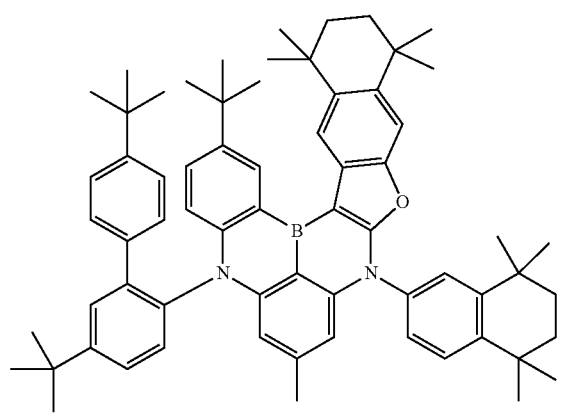

1735
-continued
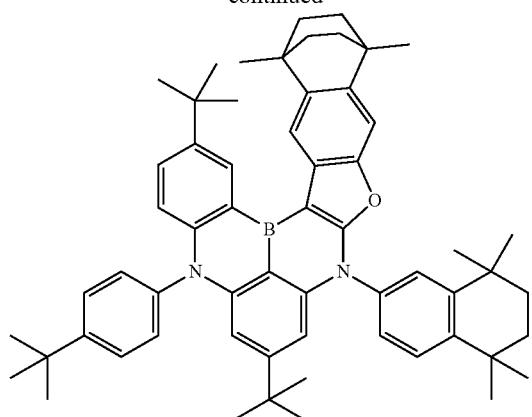
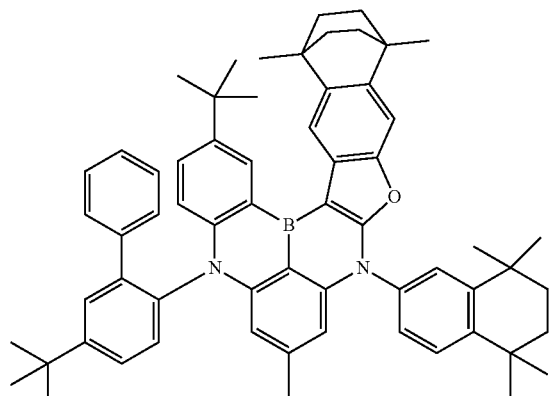
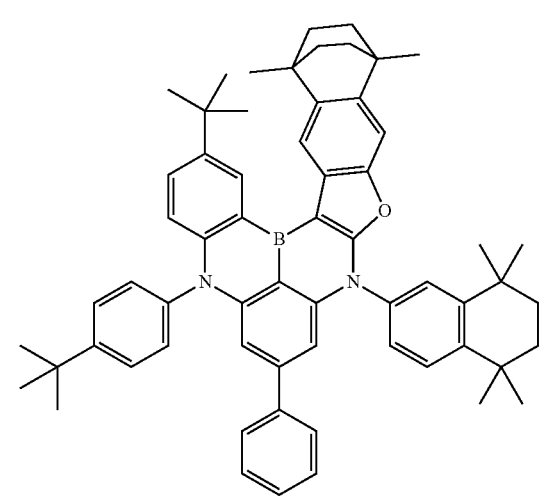
1736
-continued
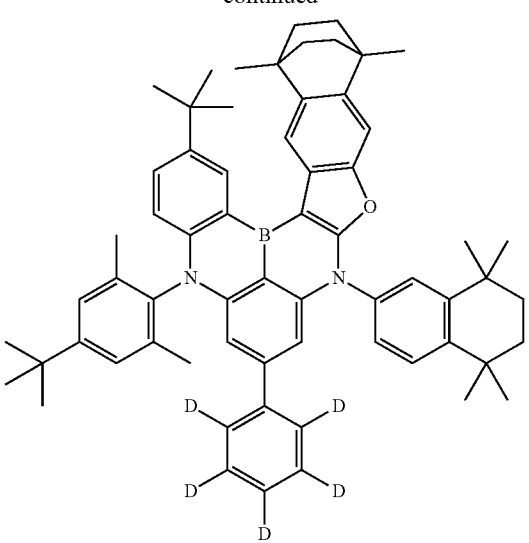
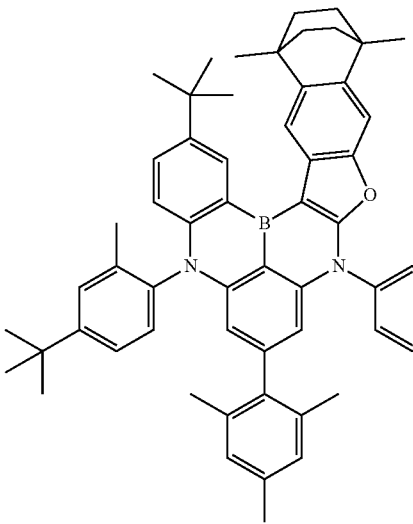
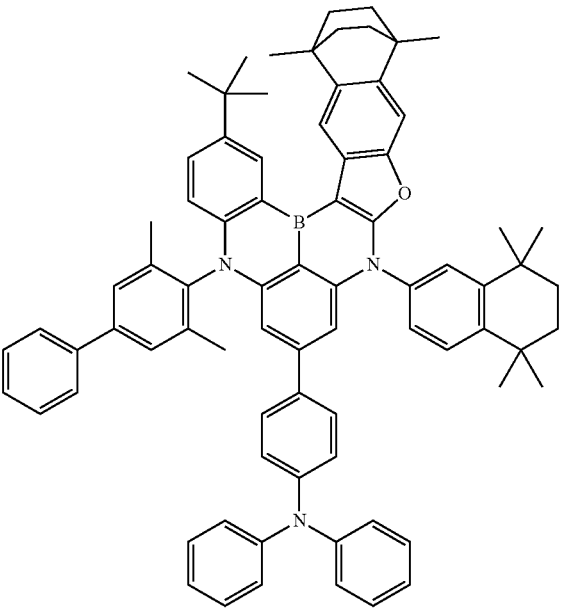

1737
-continued
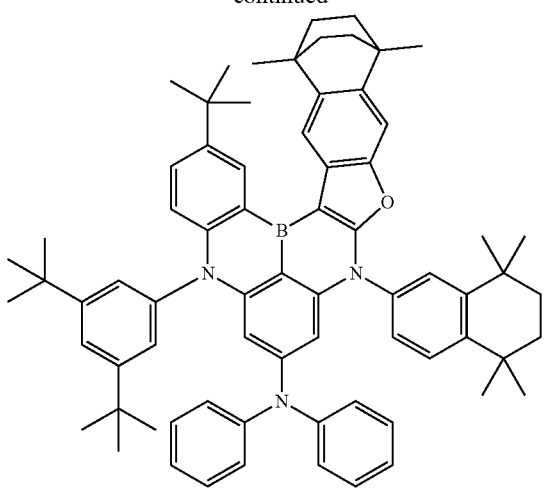
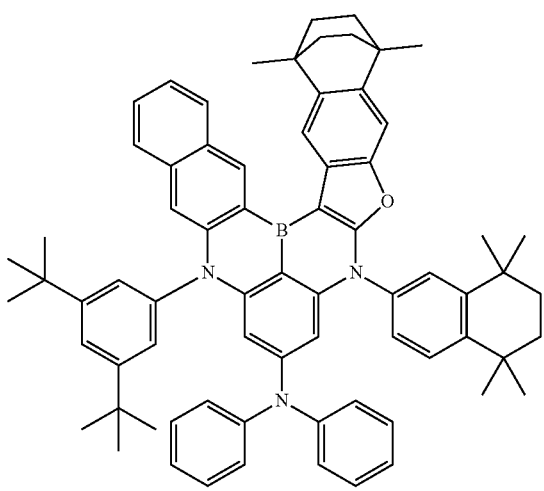
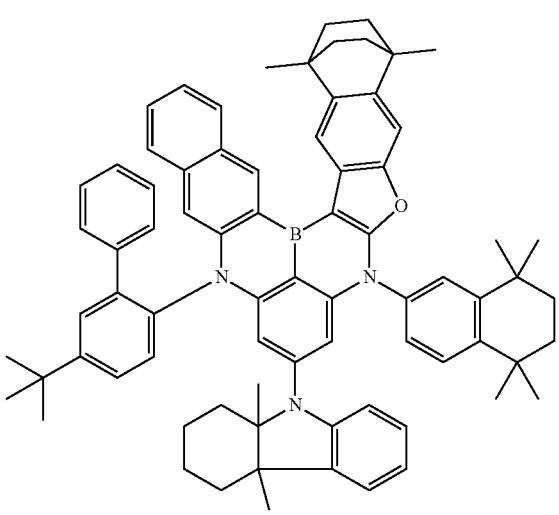
1738
-continued
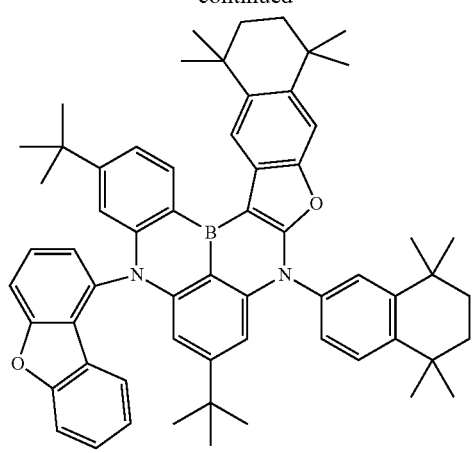
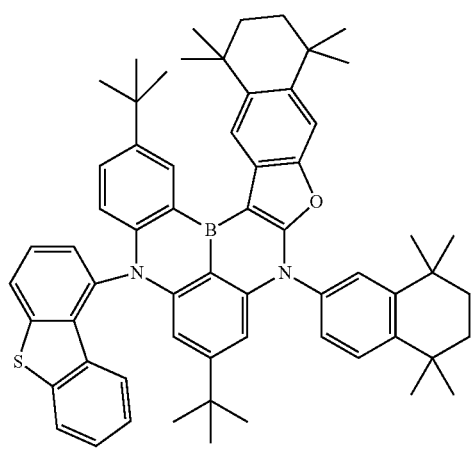
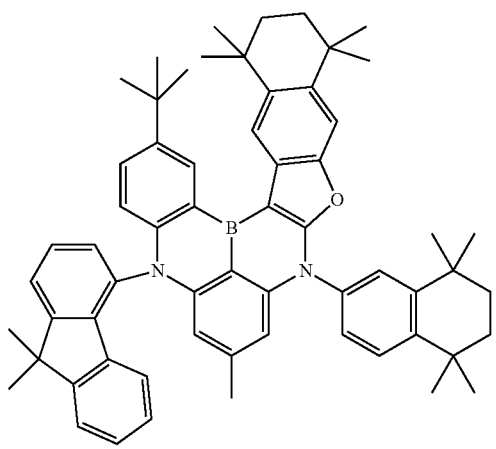

| 1739 | 1740 |
|---|---|
| -continued | -continued |
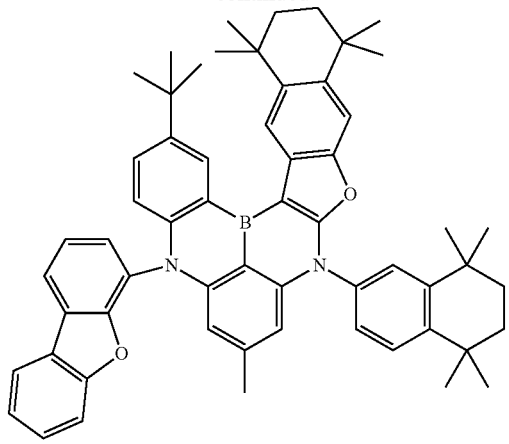
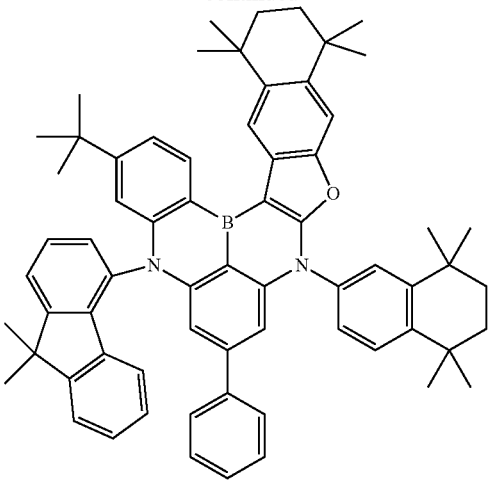
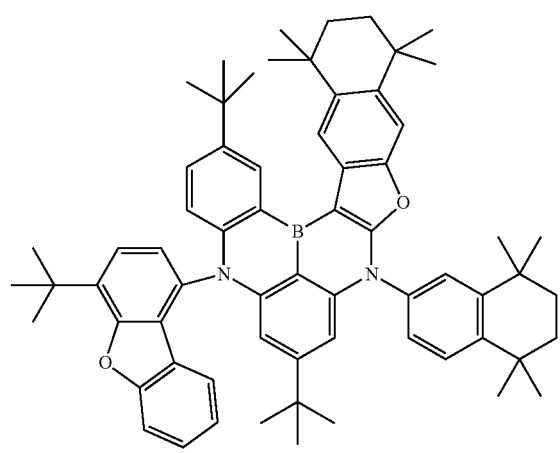
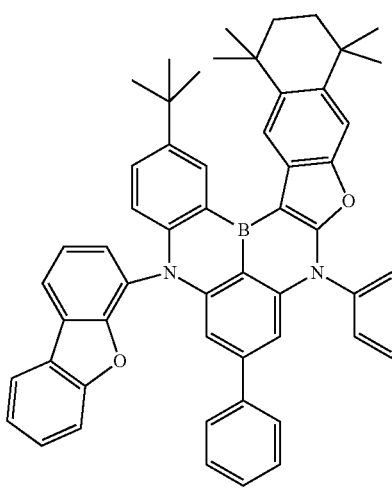
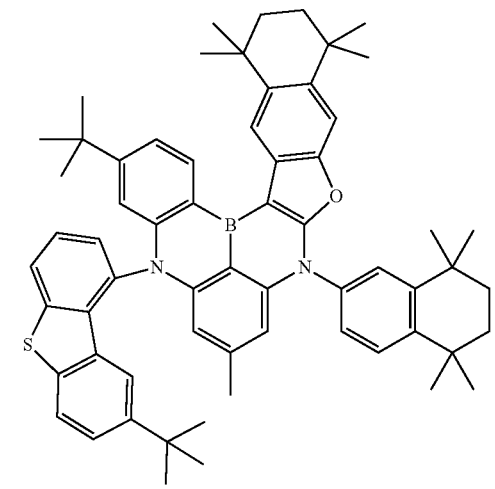
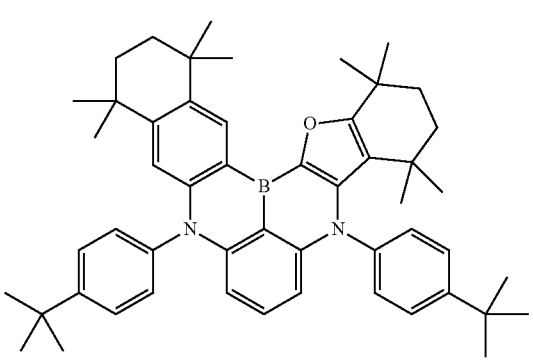
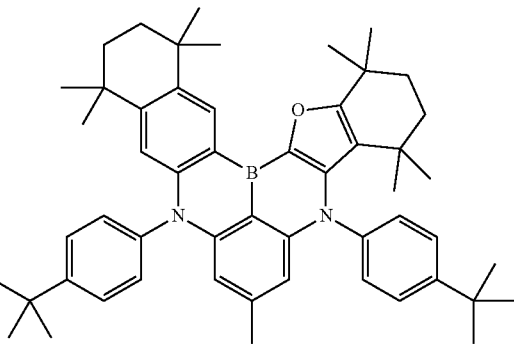

1741
-continued
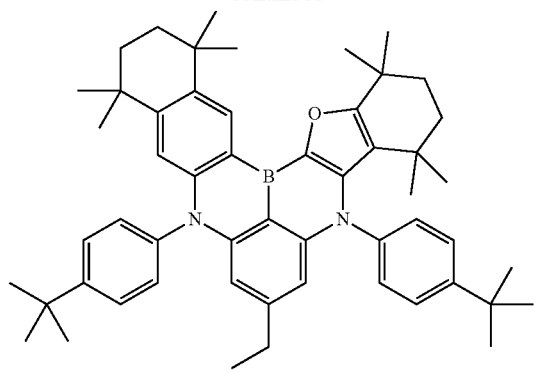
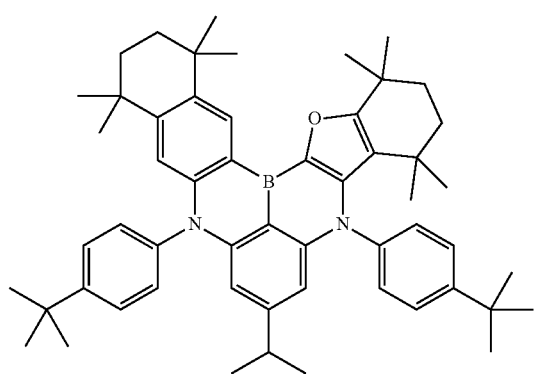
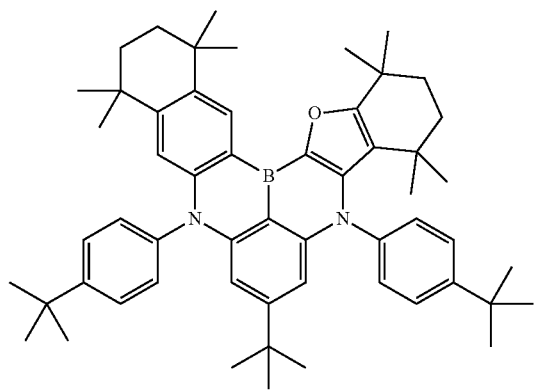
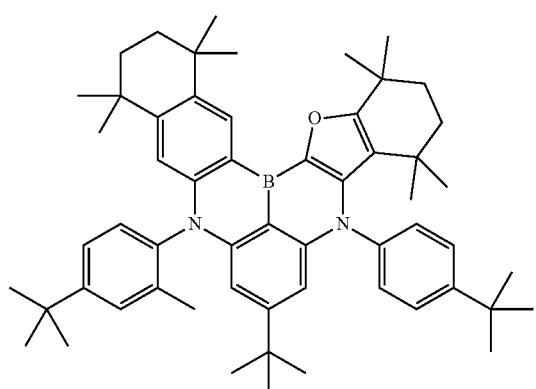
1742
-continued
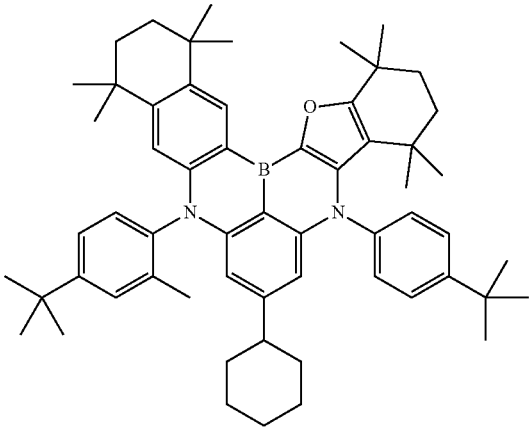
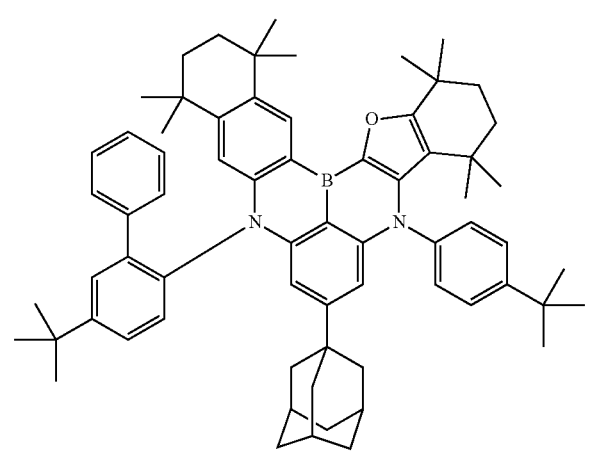
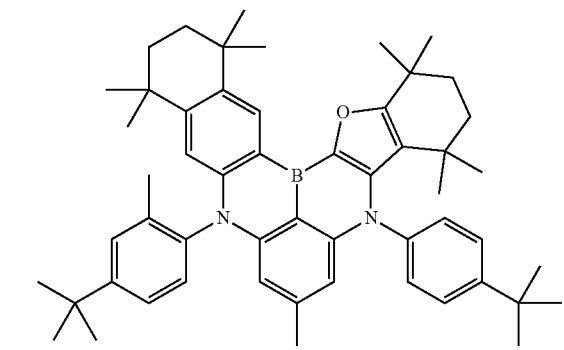
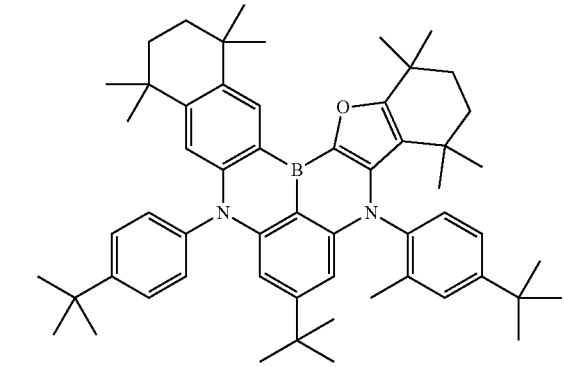

1743
-continued
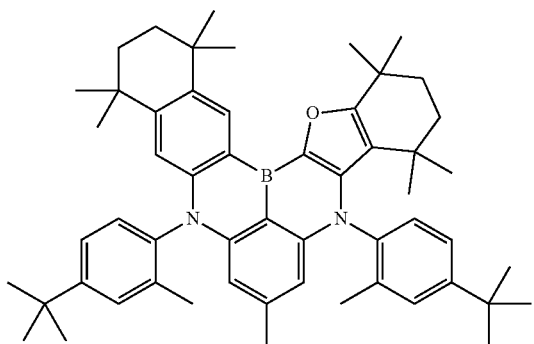
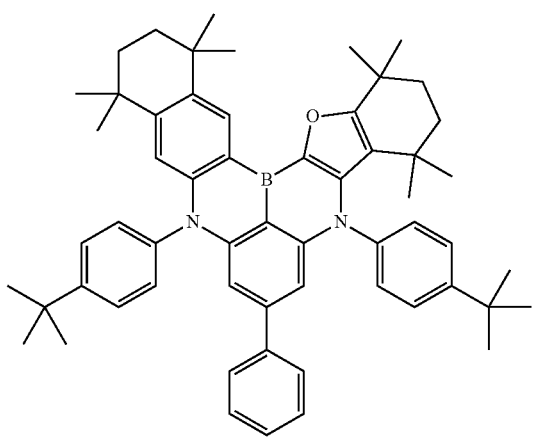
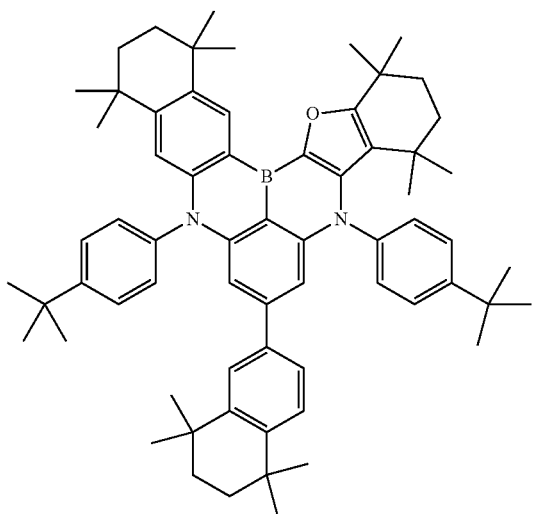
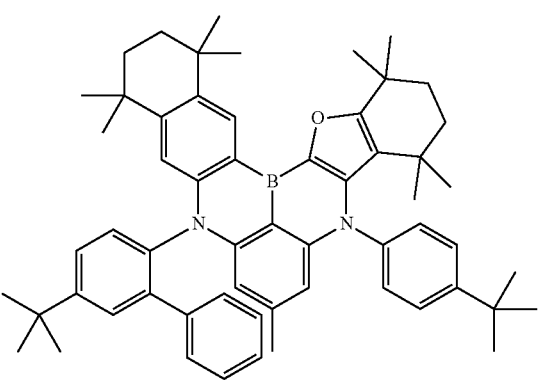
1744
-continued
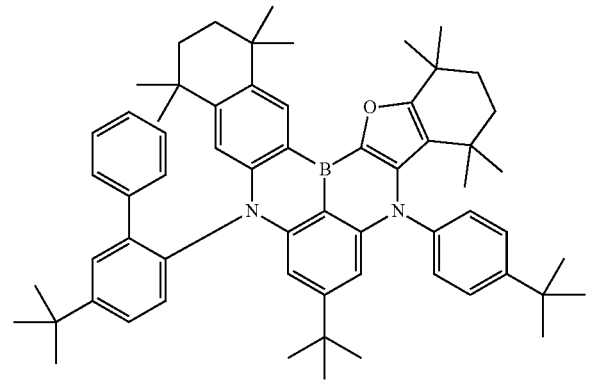
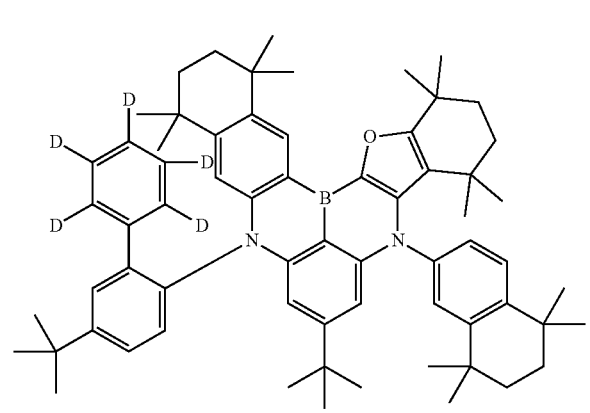
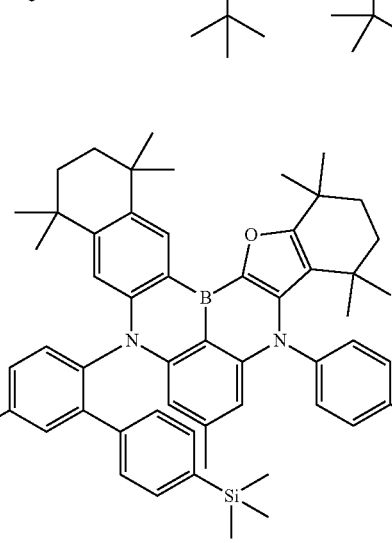
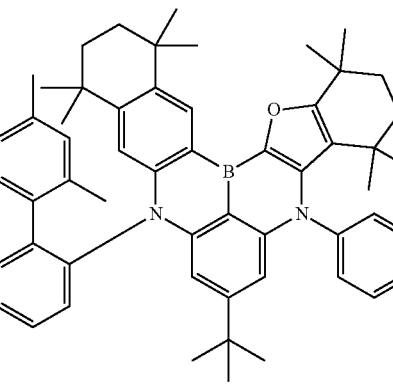

1745
-continued
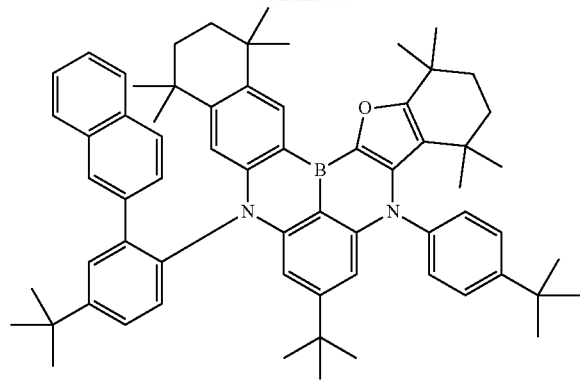
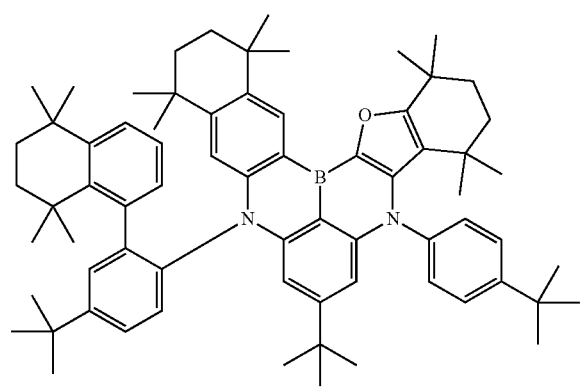
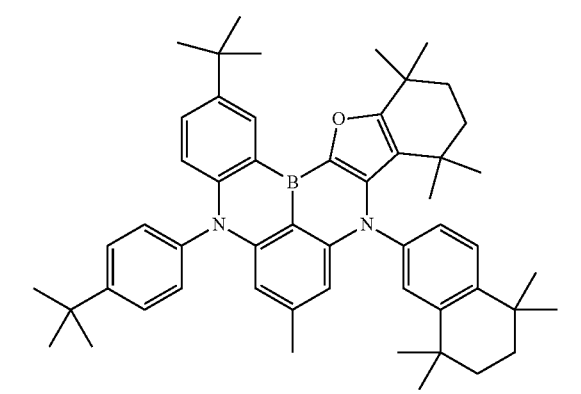
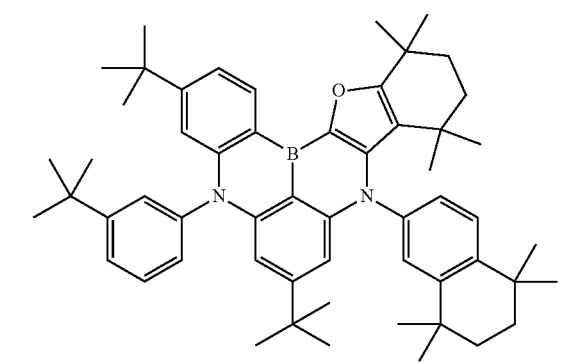
1746
-continued
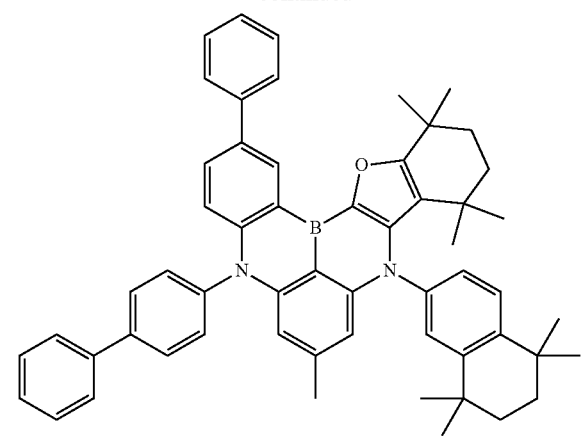
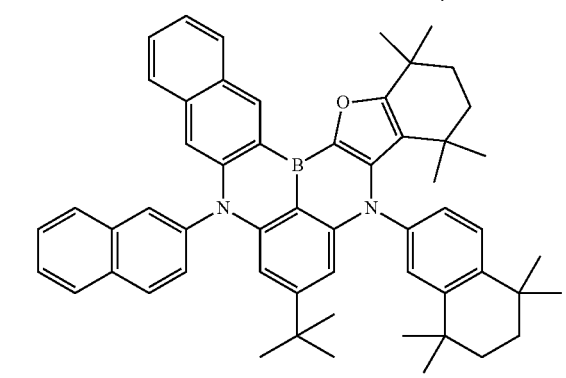
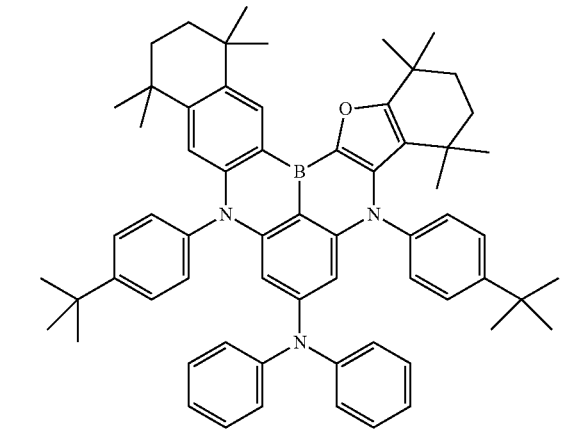
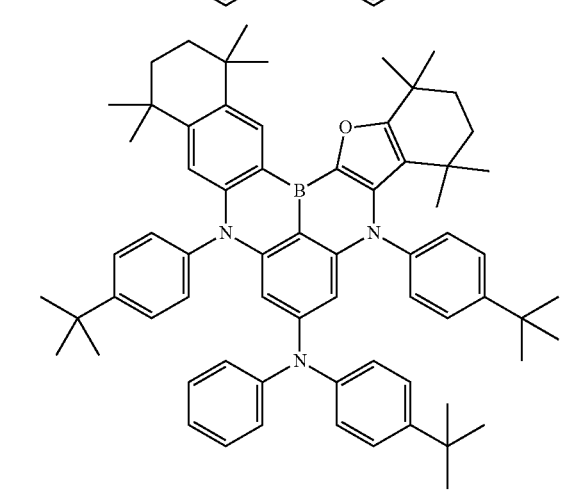

1747
-continued
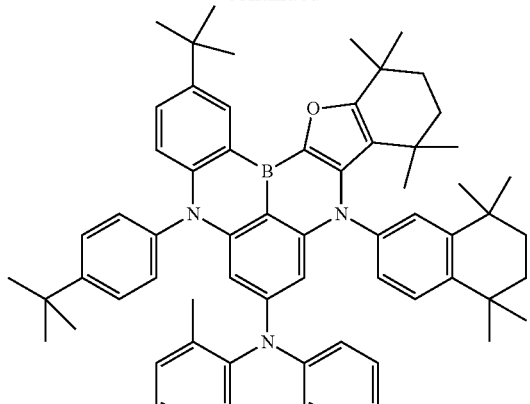
1748
-continued
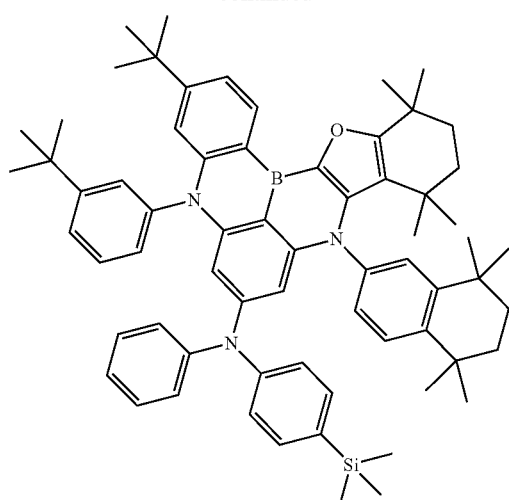
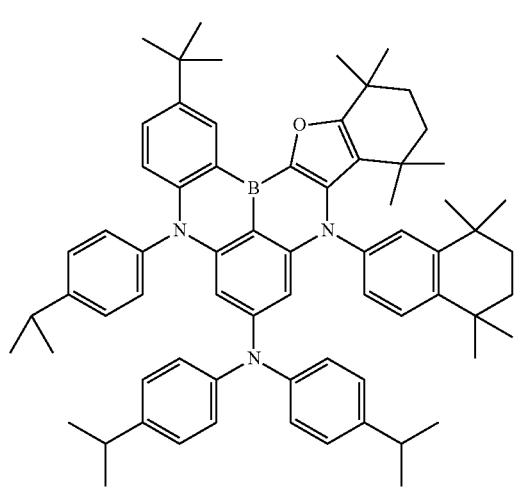
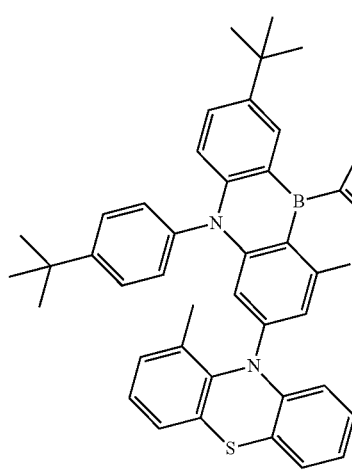
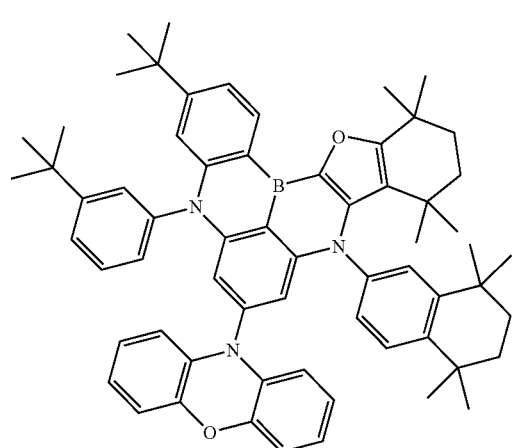
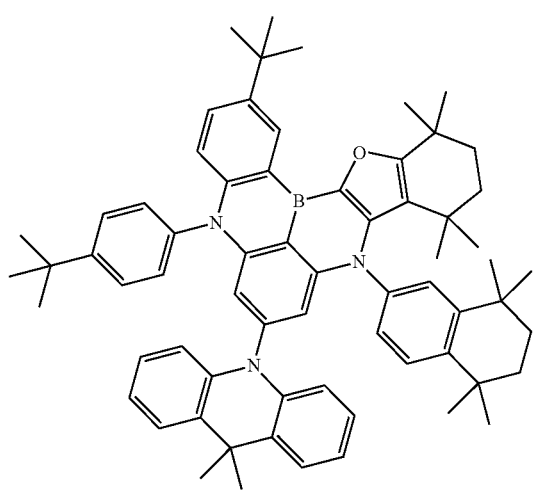

-continued
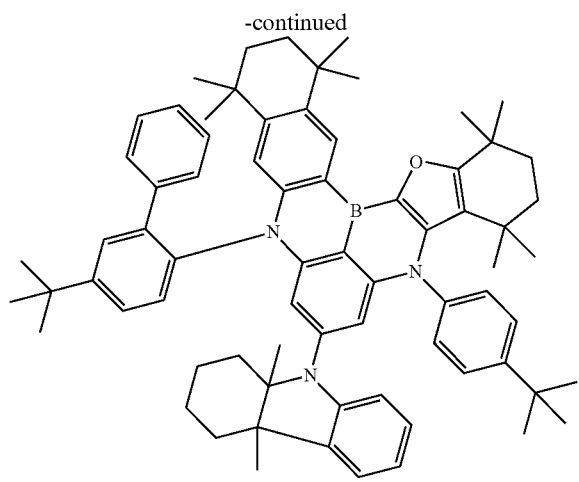
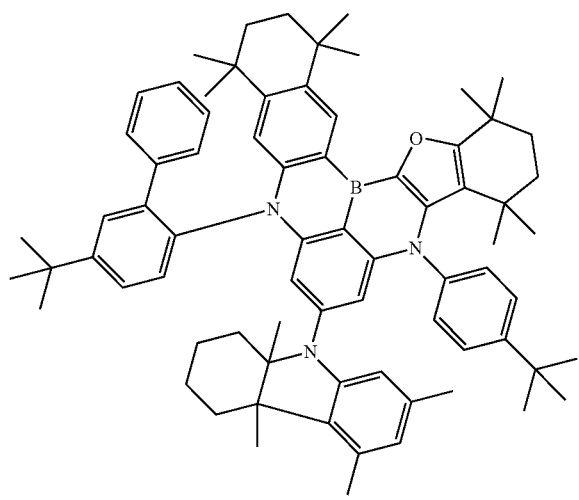
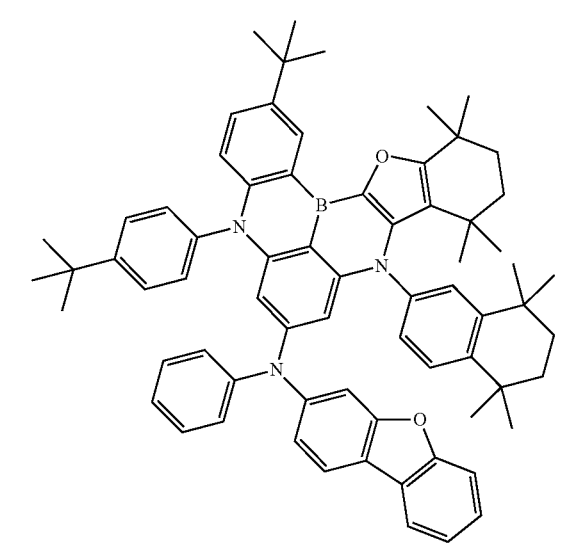
-continued
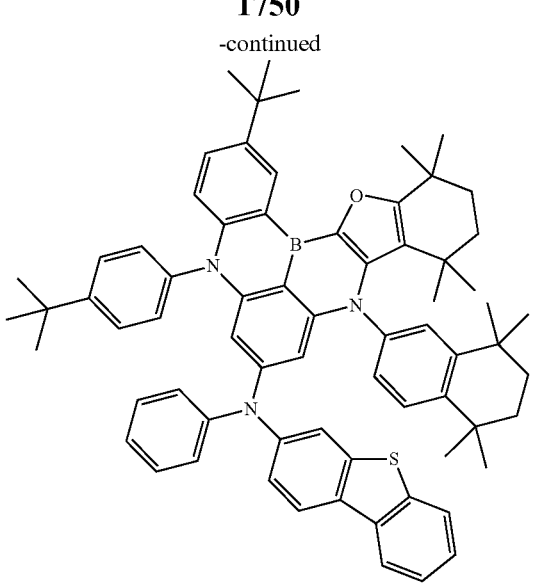
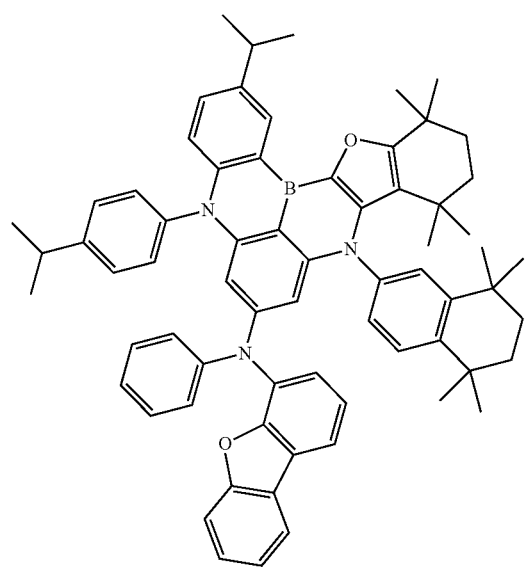
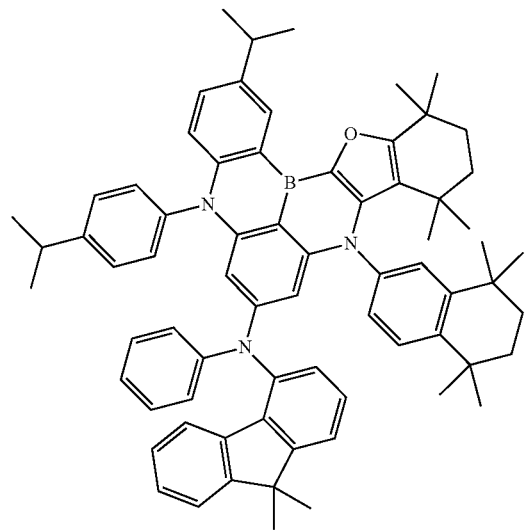

1751
-continued
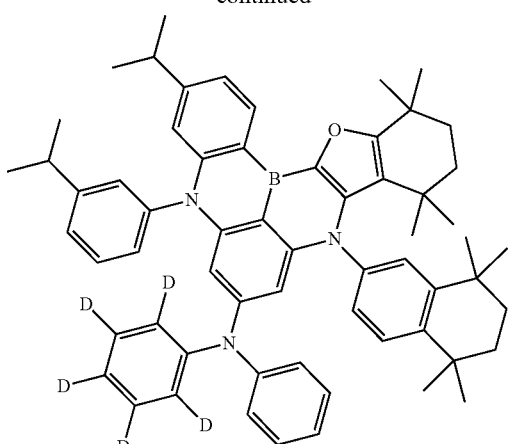
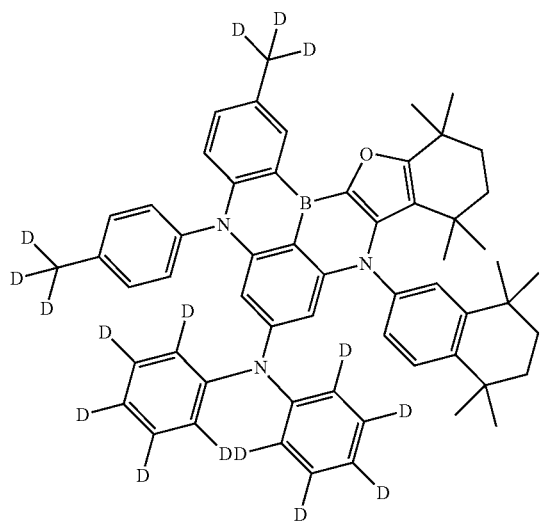
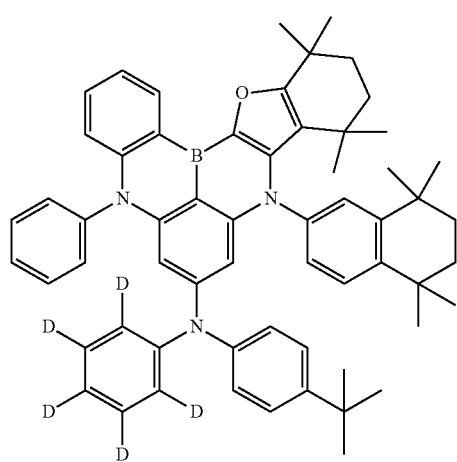
1752
-continued
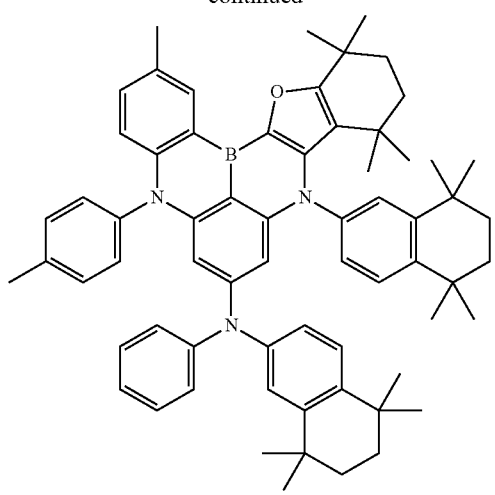
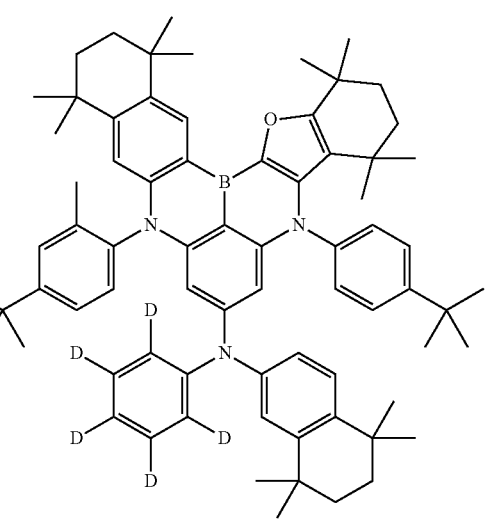
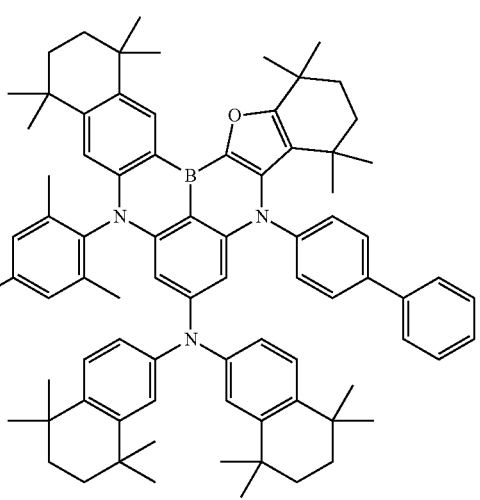

1753
-continued
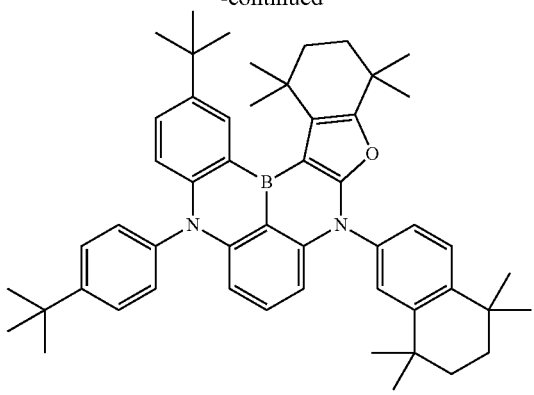
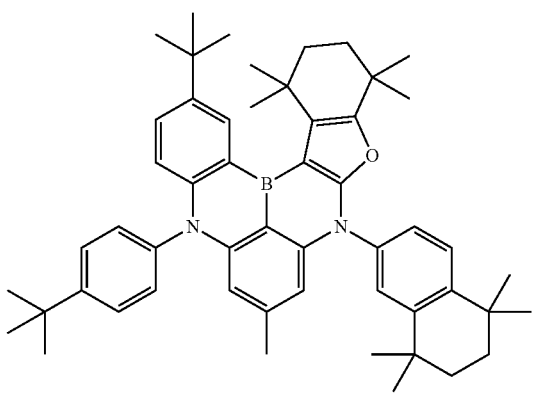
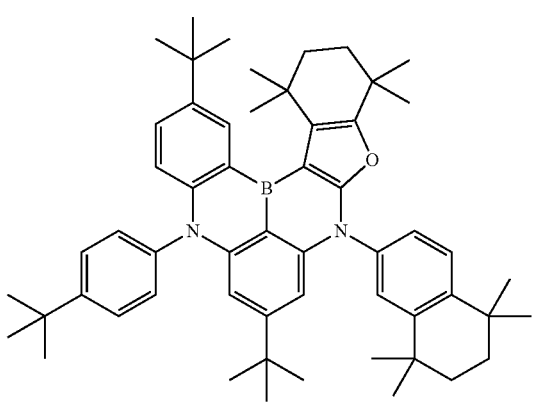
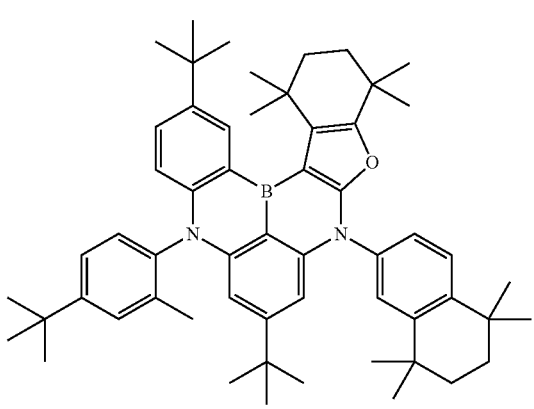
1754
-continued
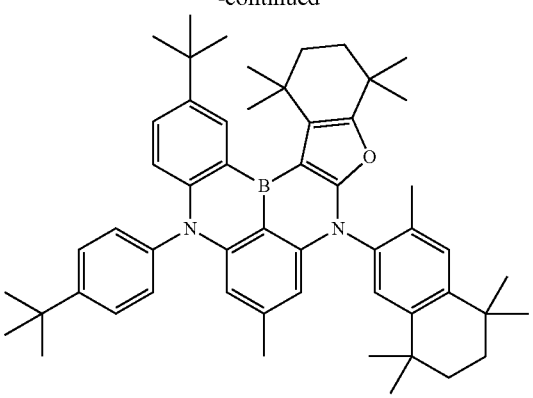
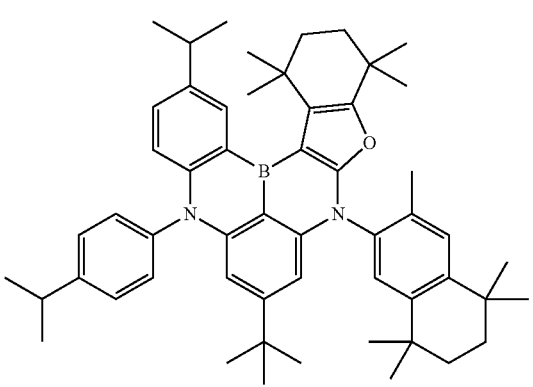
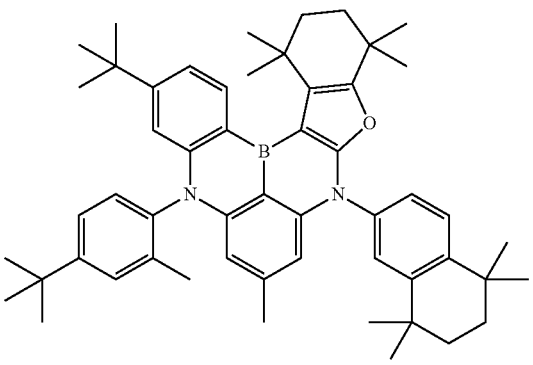

1755
-continued

1756
-continued
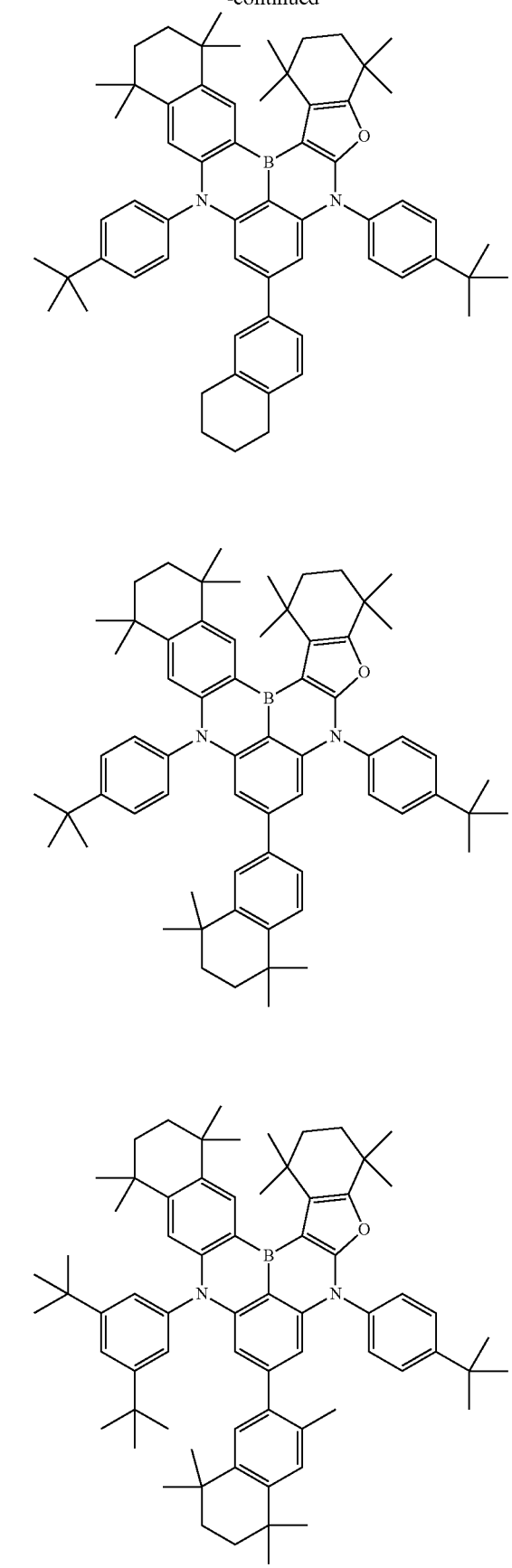

1757
-continued
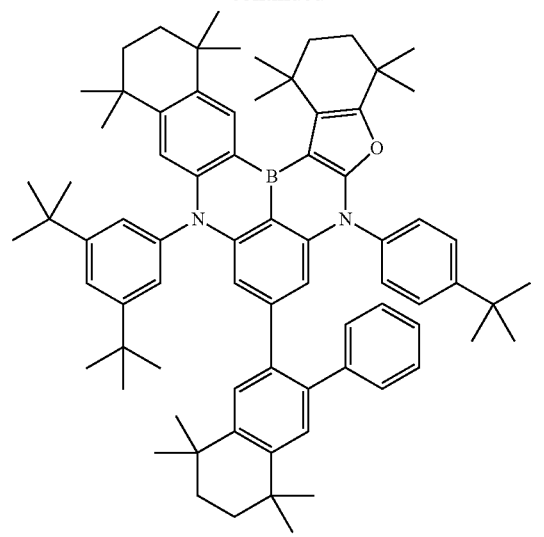
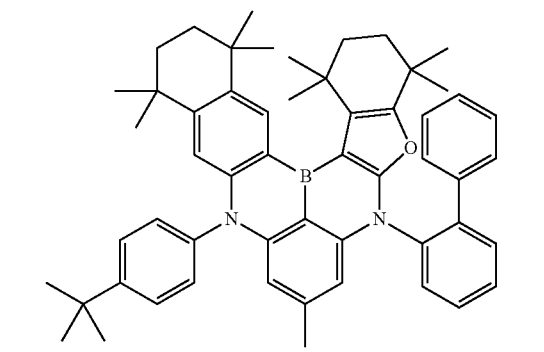
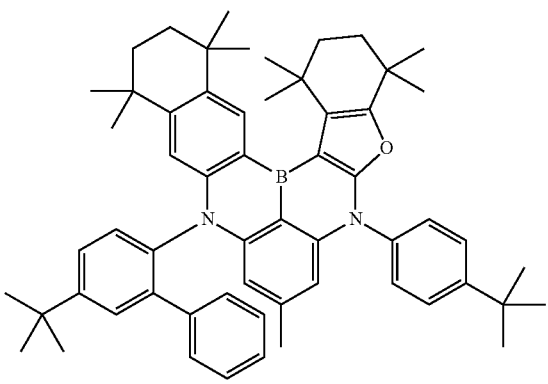
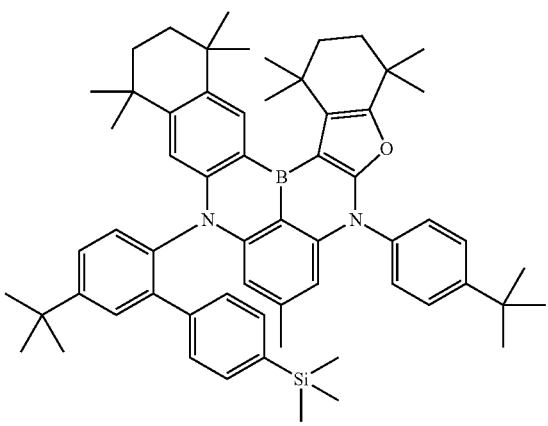
1758
-continued
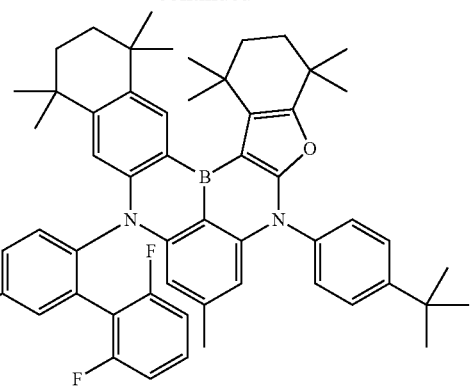

1759
-continued
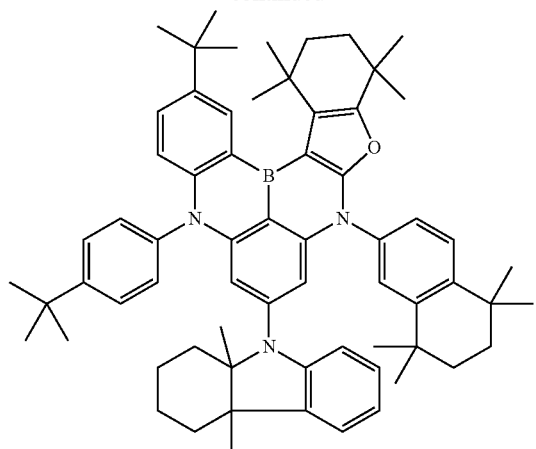
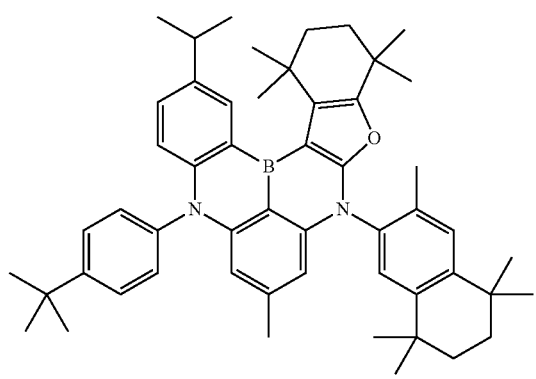
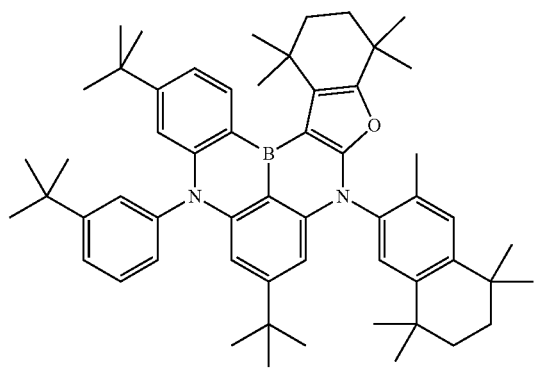
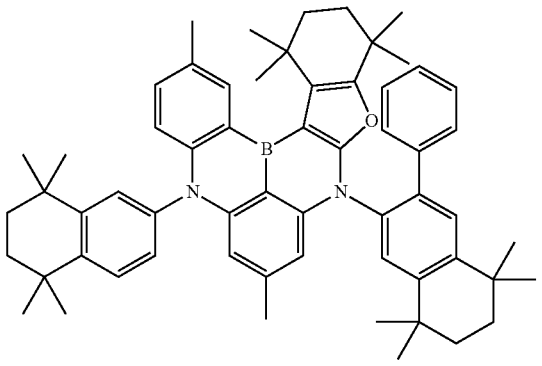
1760
-continued
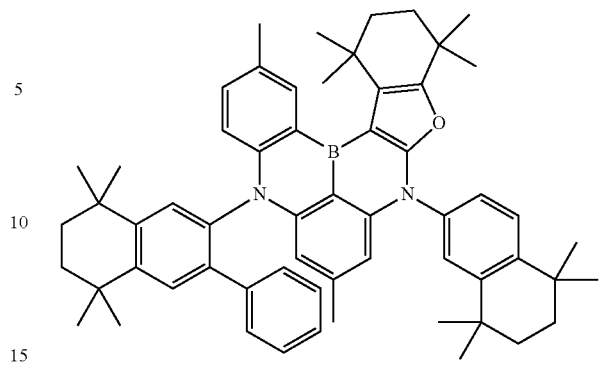

1761
-continued
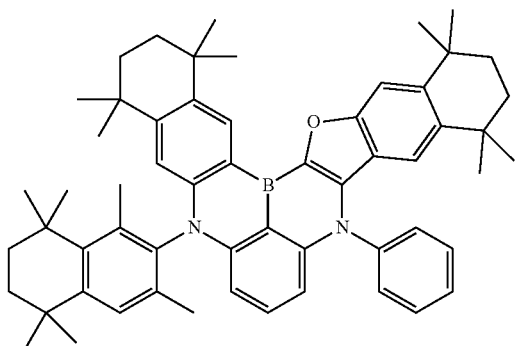
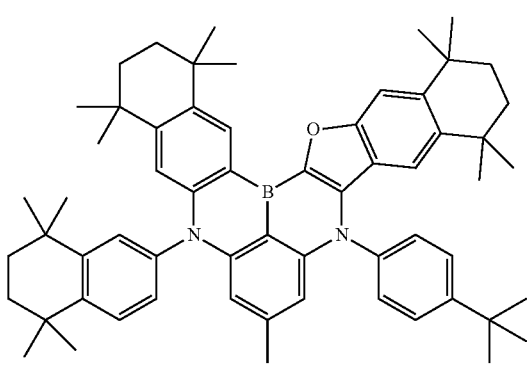
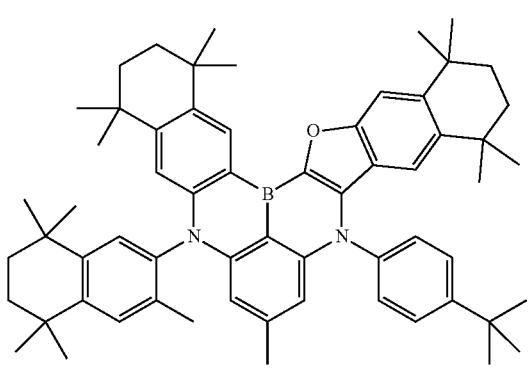
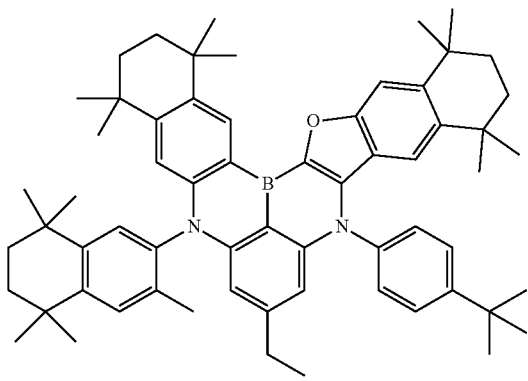
1762
-continued
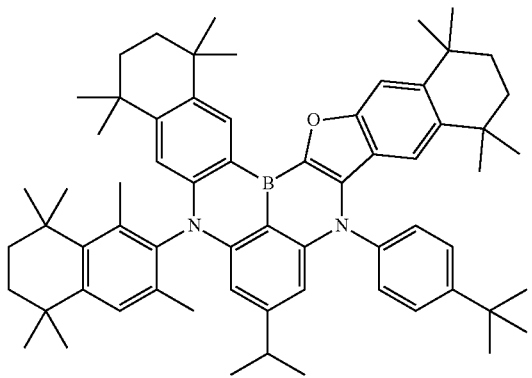
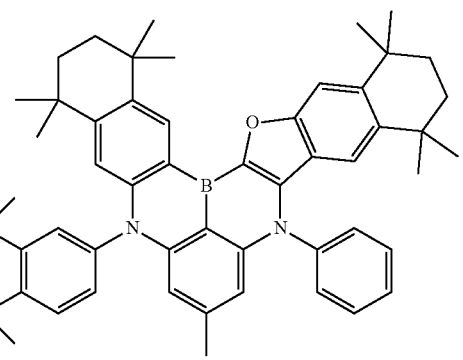
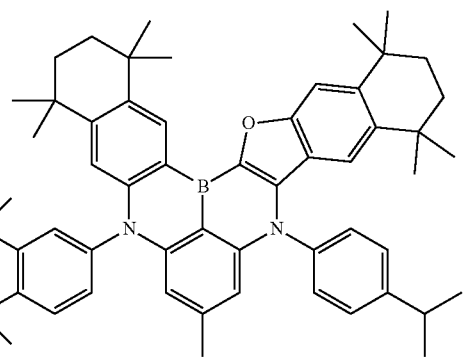
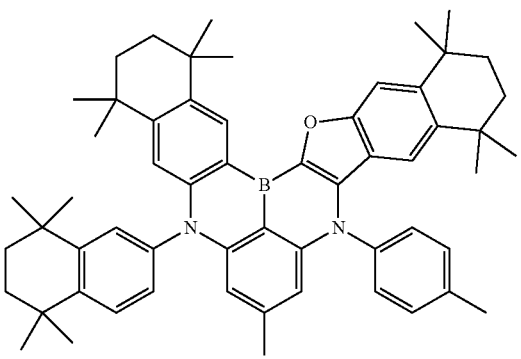

1763
-continued
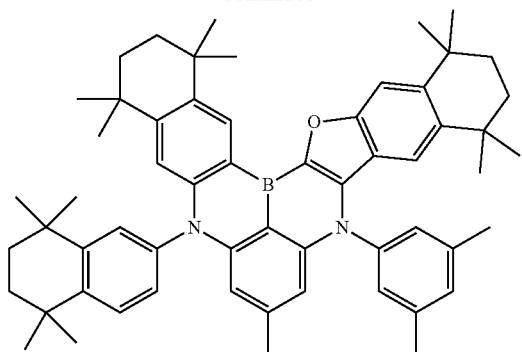
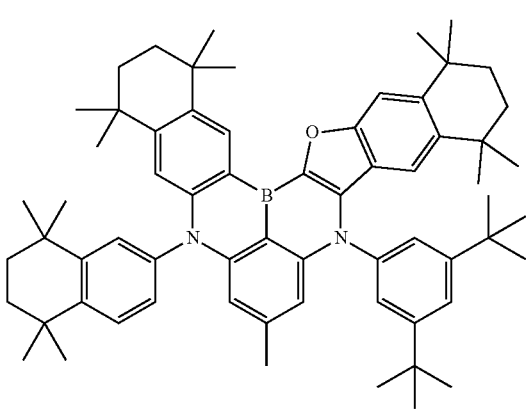
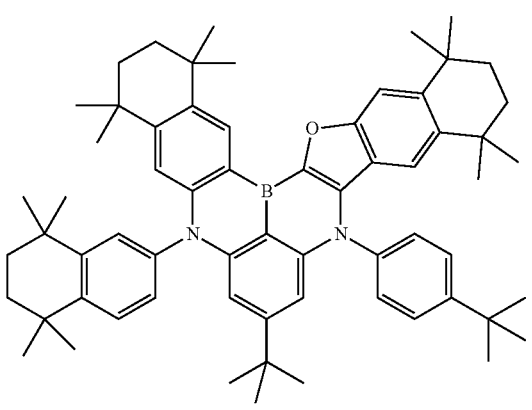
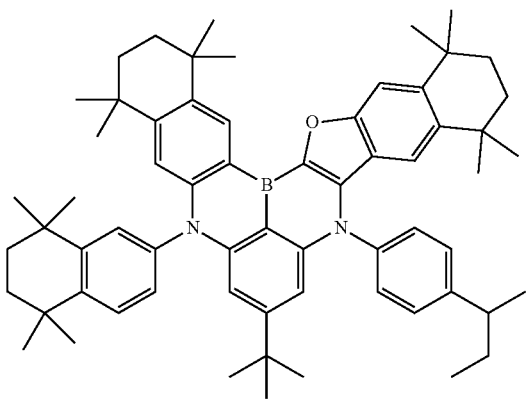
1764
-continued
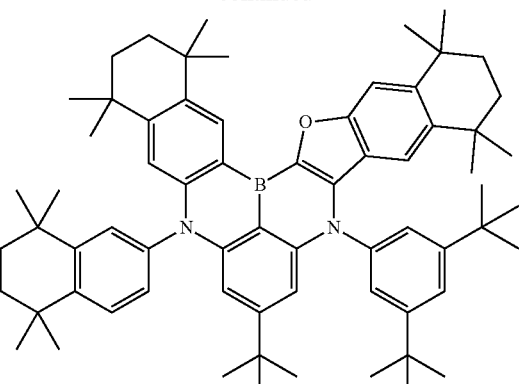
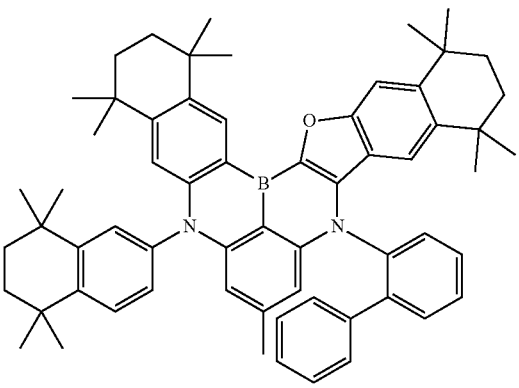
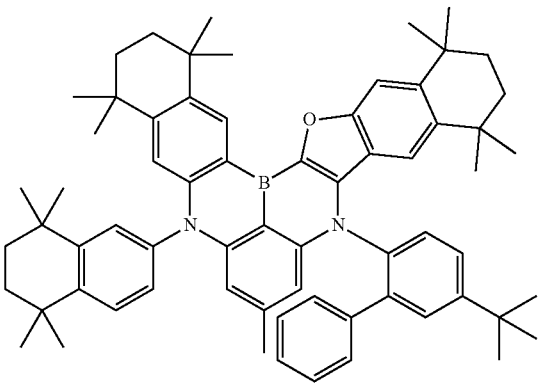
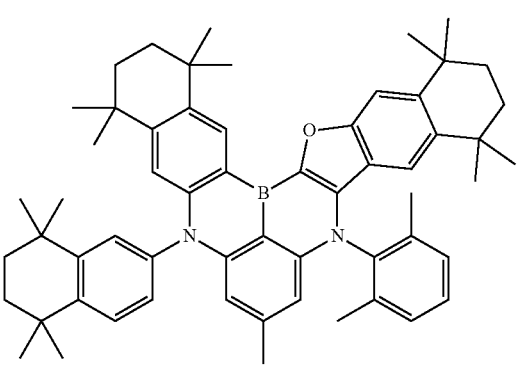

1765
-continued
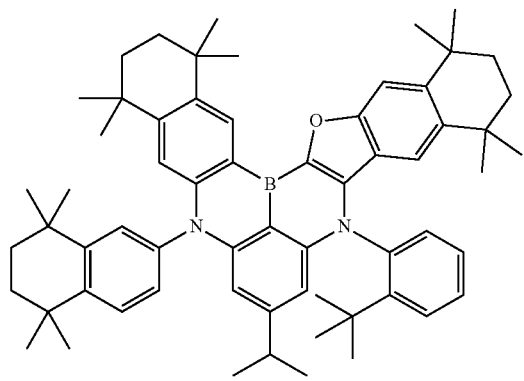
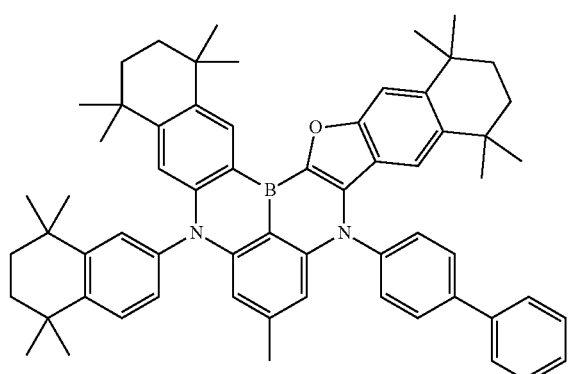
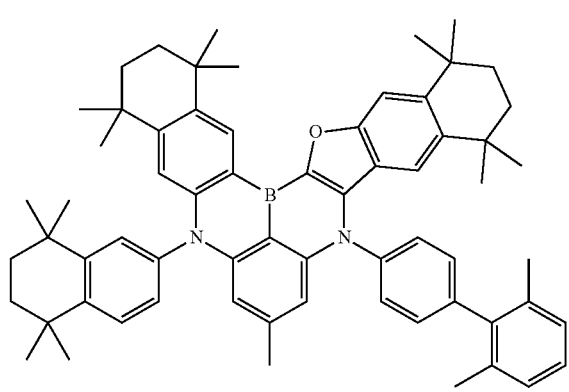
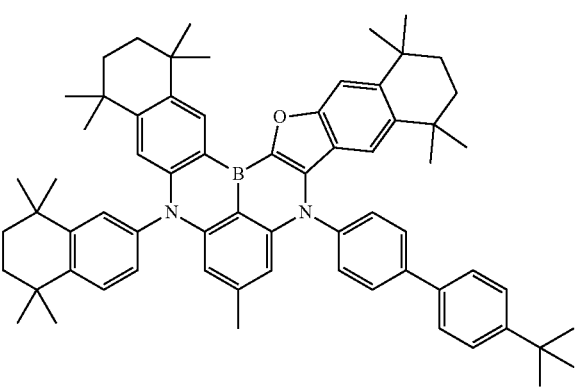
1766
-continued
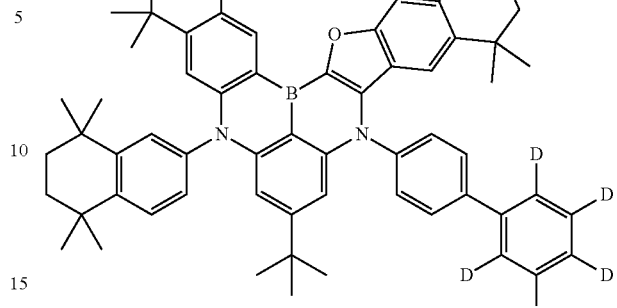
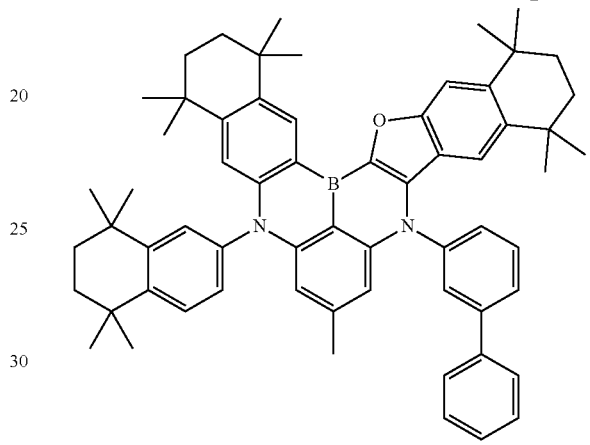
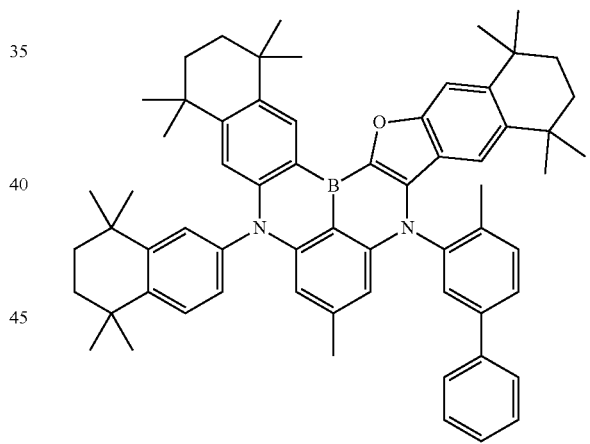
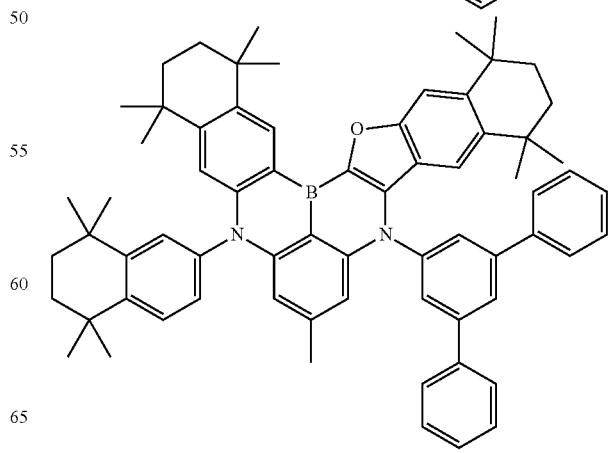

1767
-continued
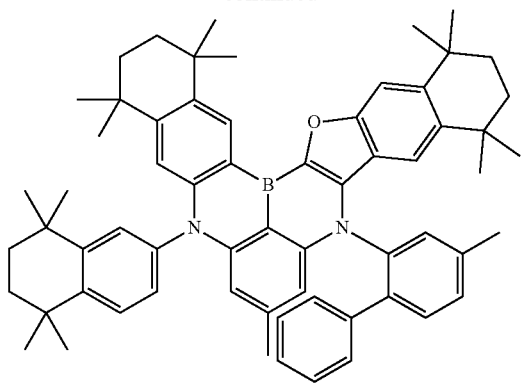
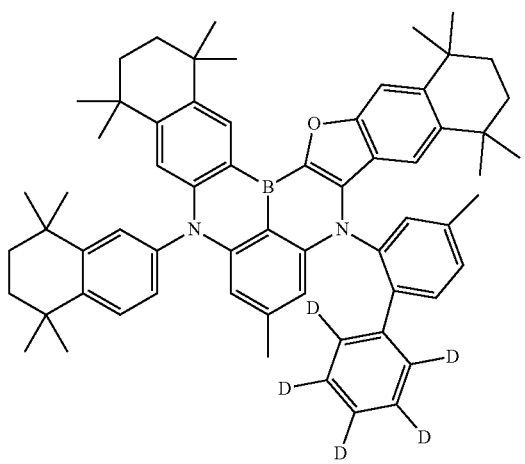
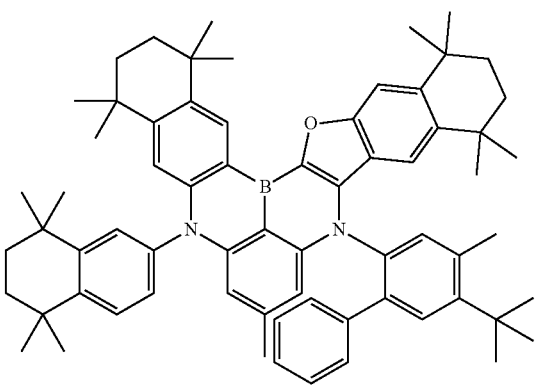
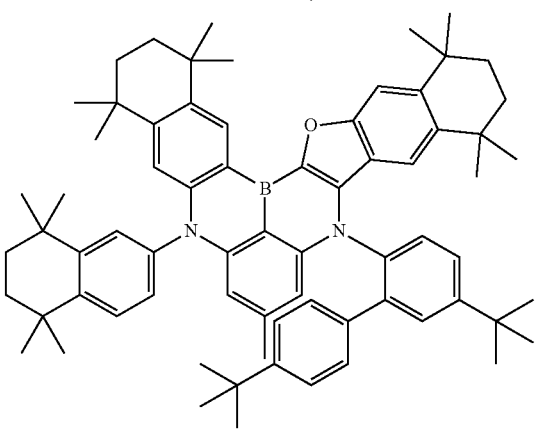
1768
-continued
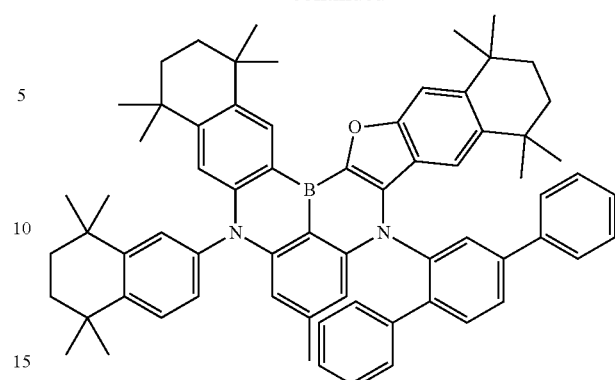
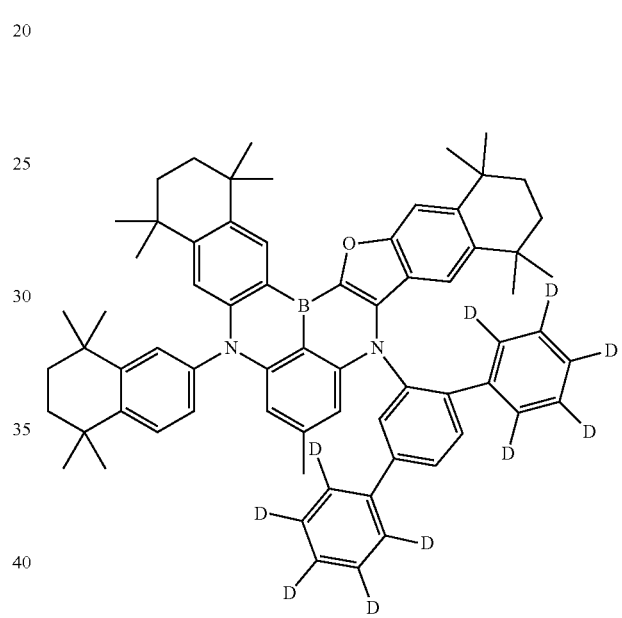
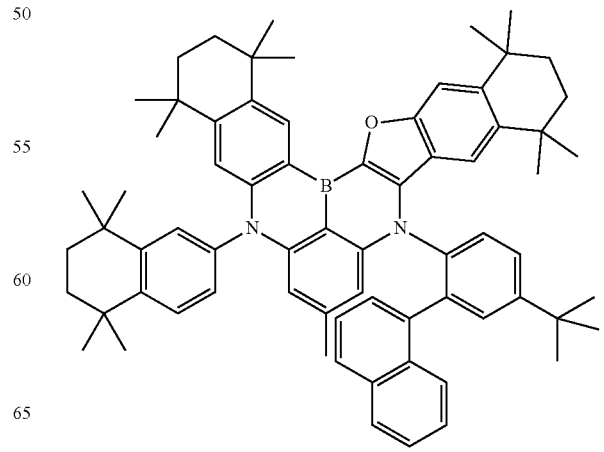

1769
-continued
1770
-continued
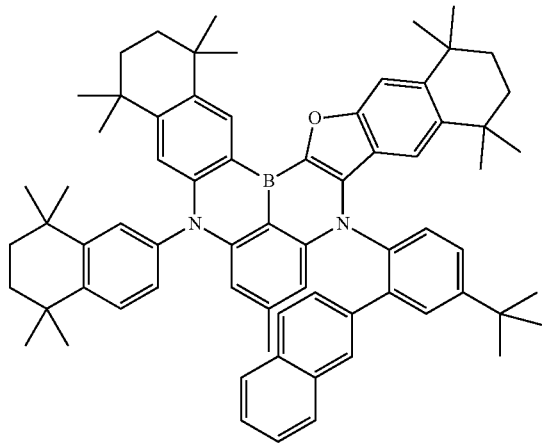
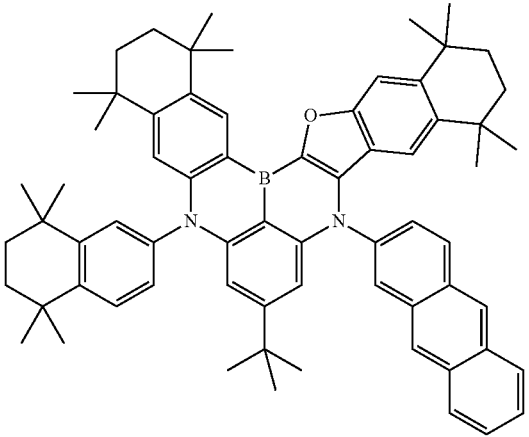
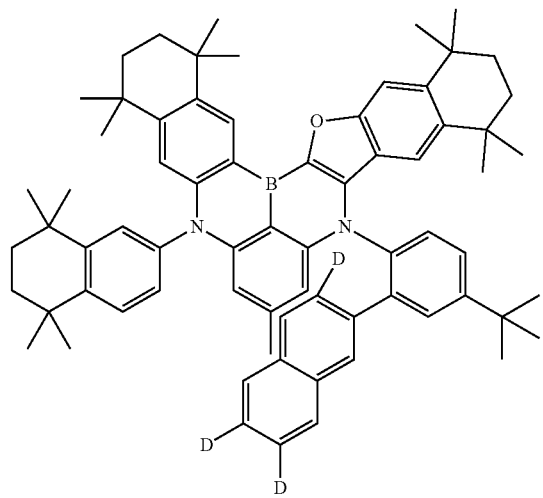
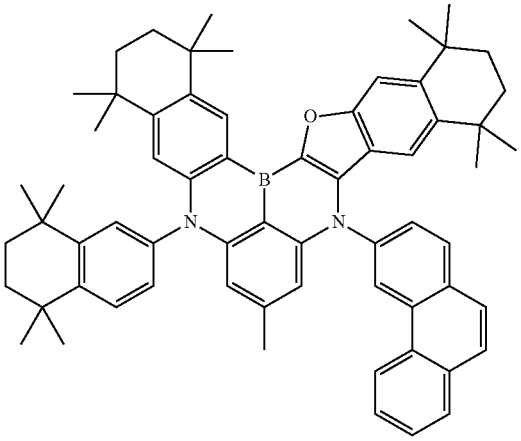
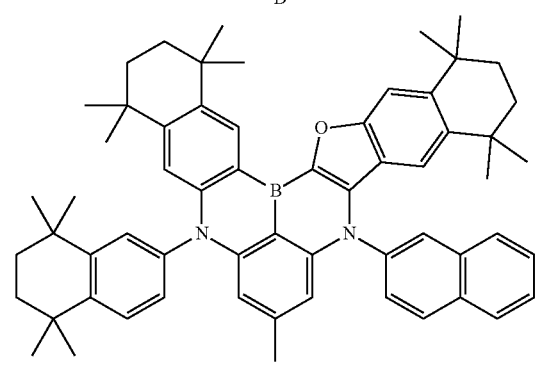
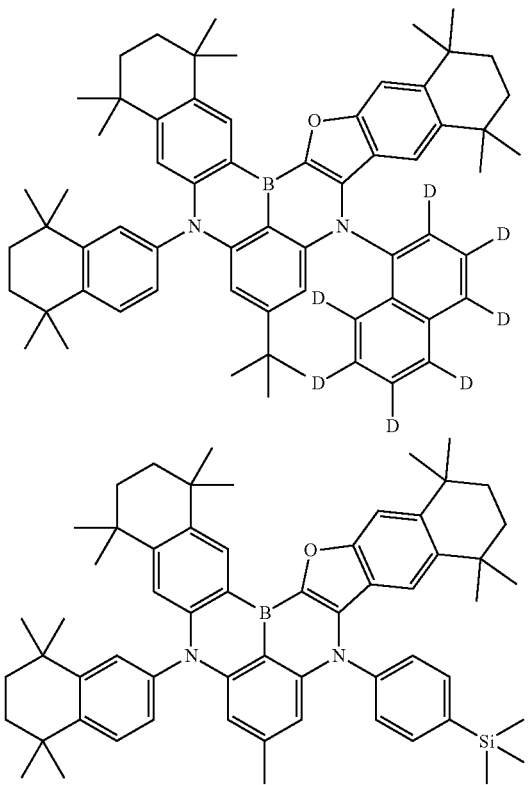
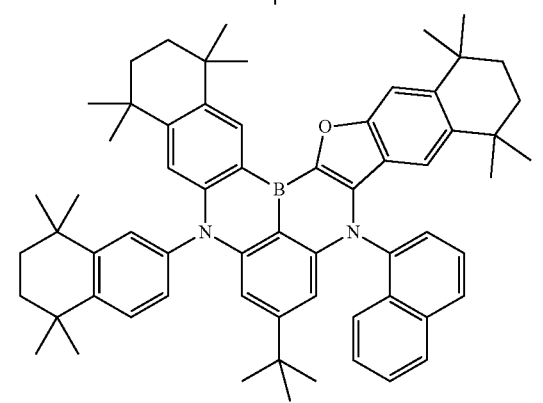

1771
-continued
1772
-continued
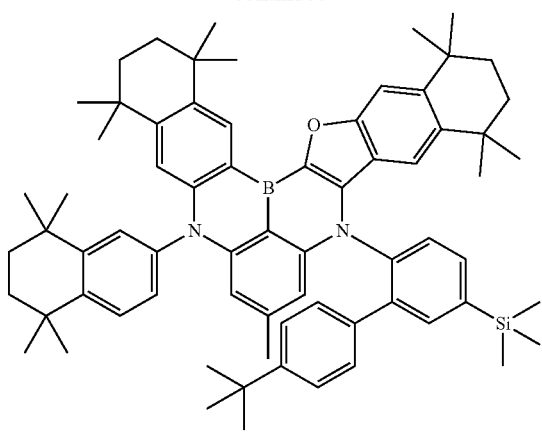
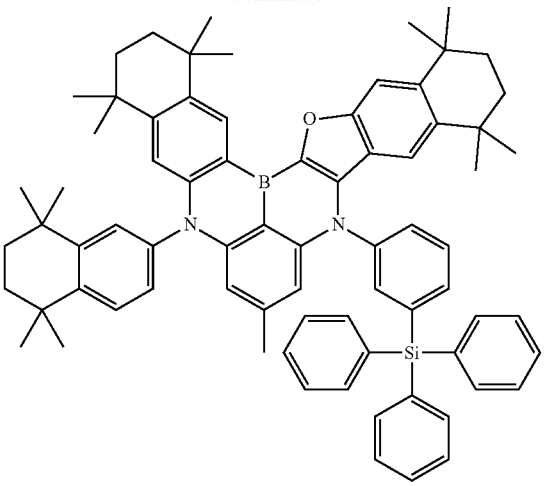
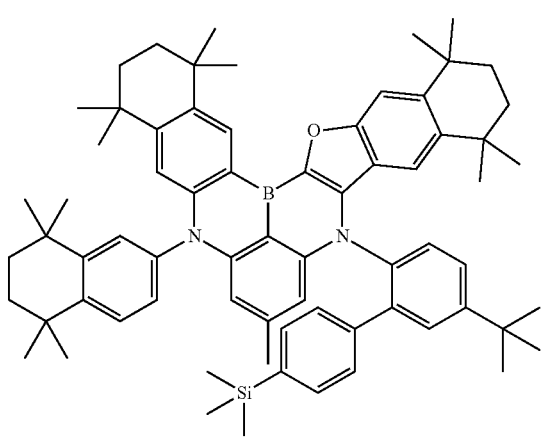
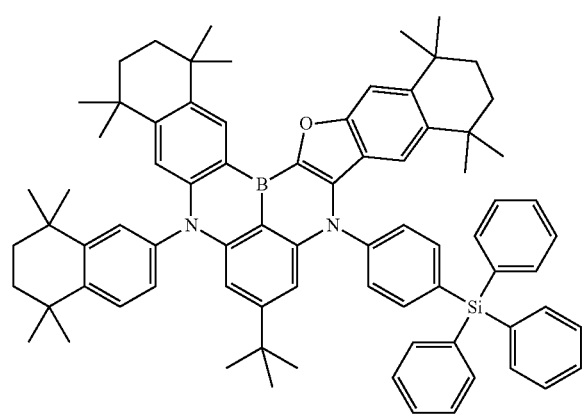

1773
-continued
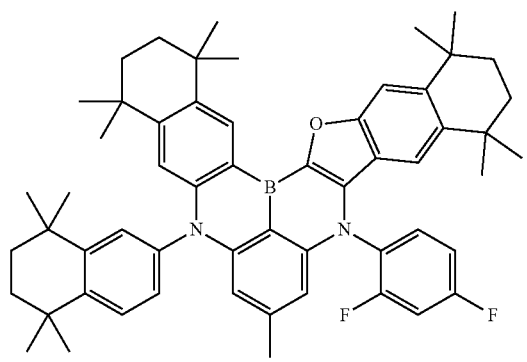
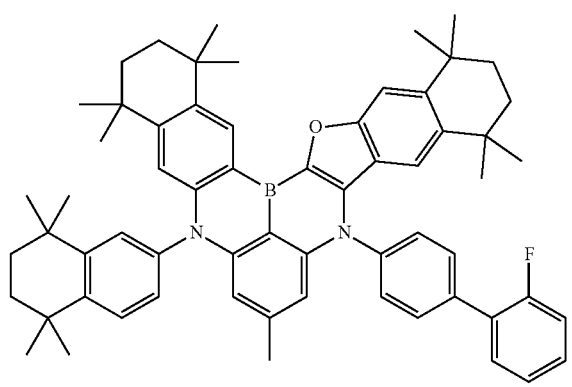
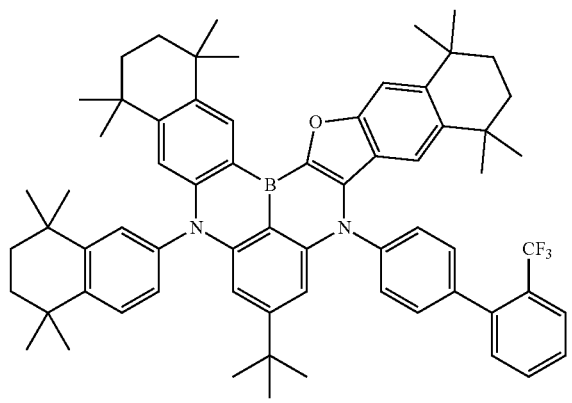
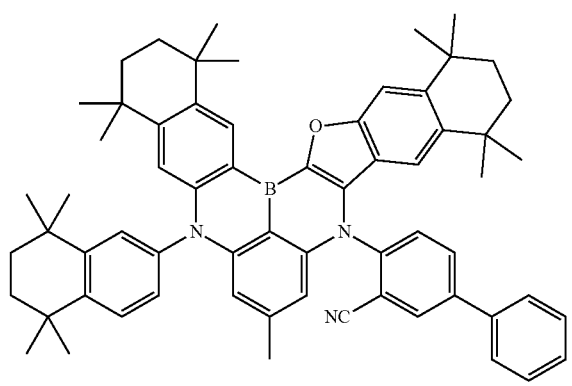
1774
-continued
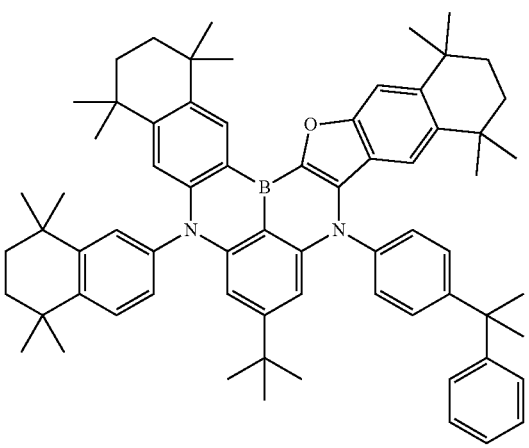
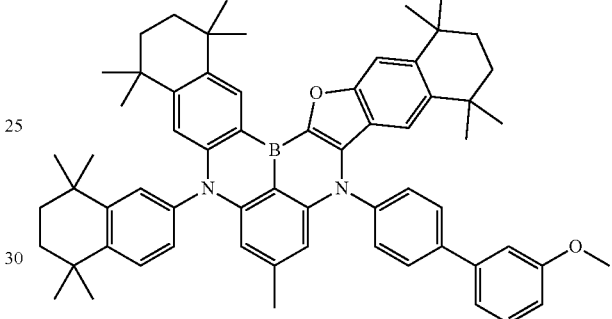
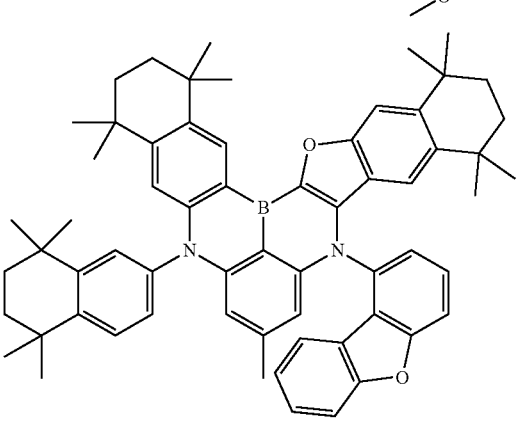
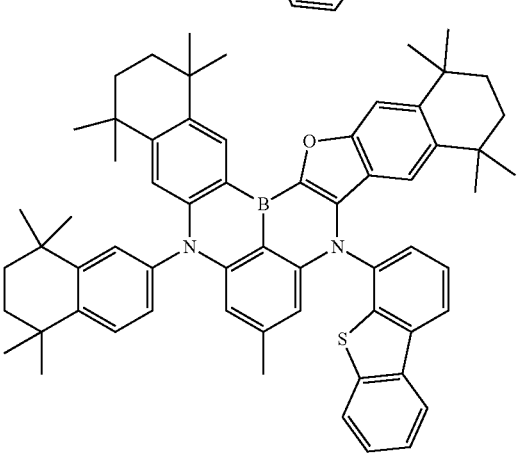

1775
-continued
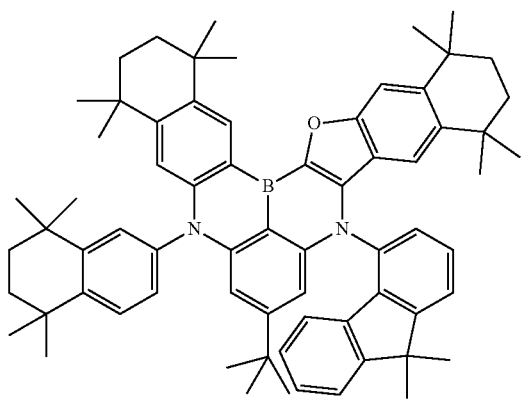
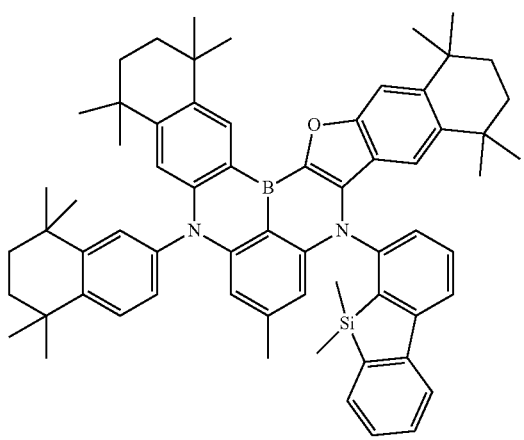
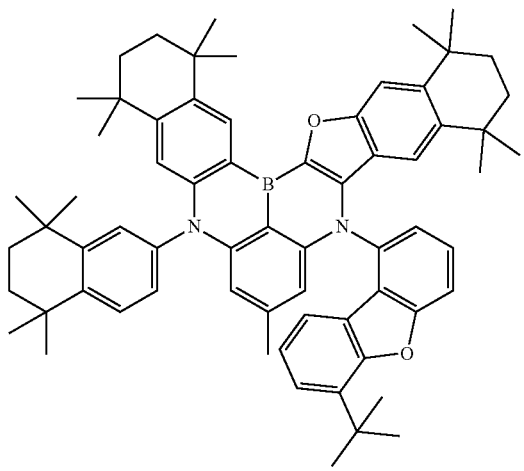
1776
-continued
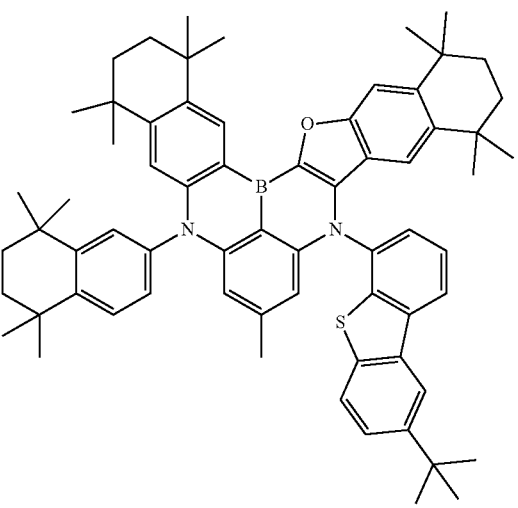
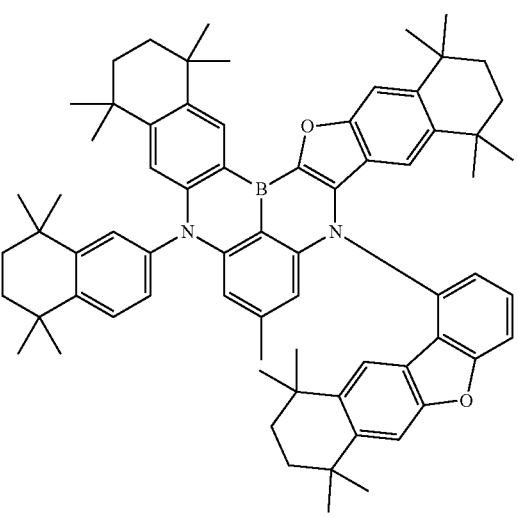
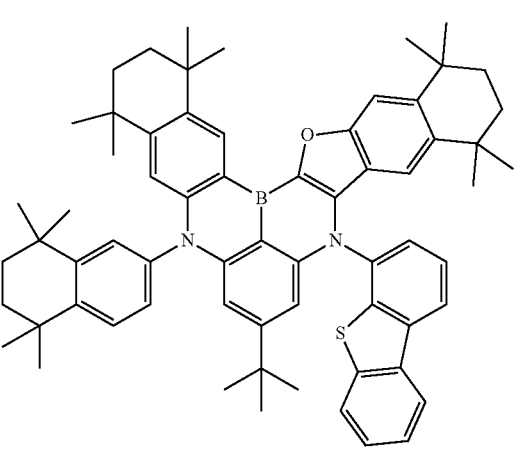

1777
-continued
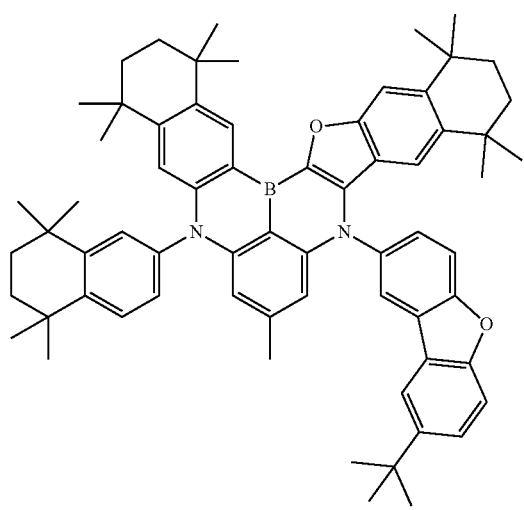
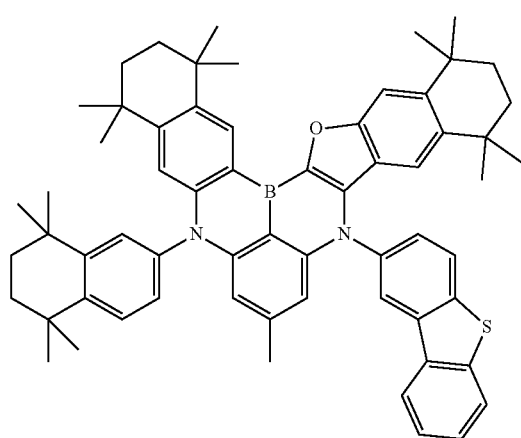
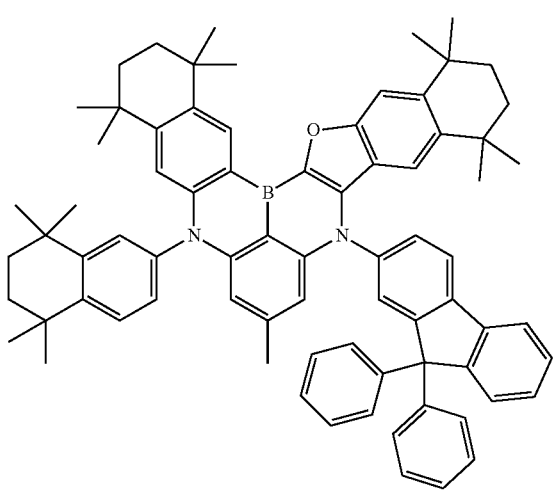
1778
-continued
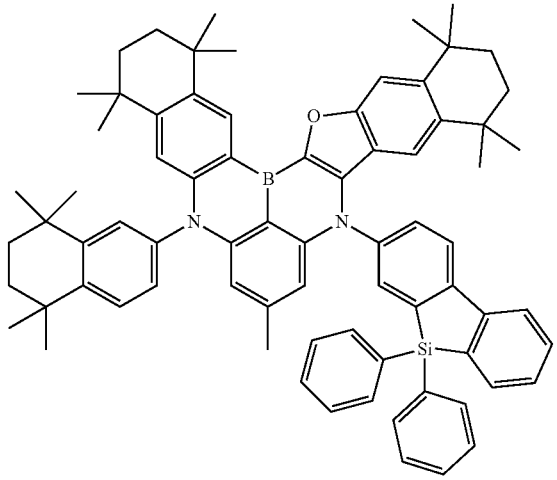
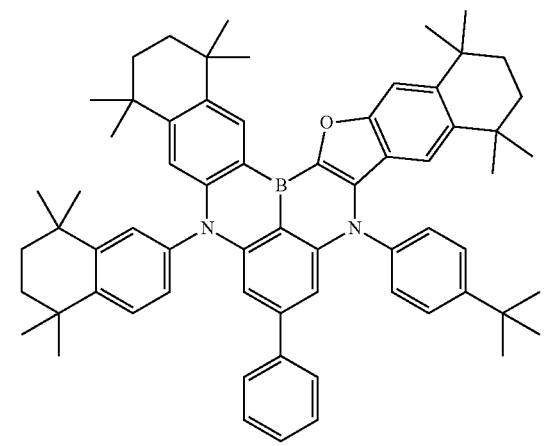
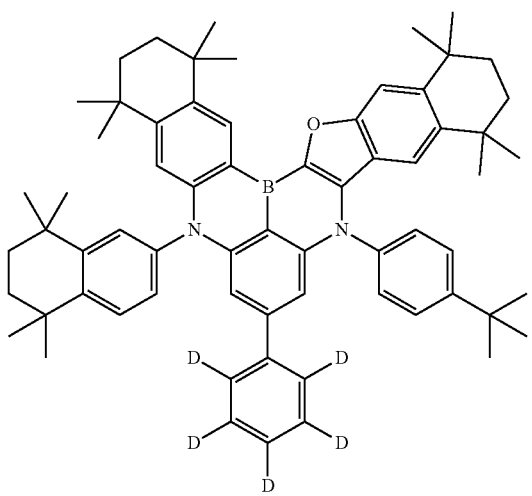

1779
-continued
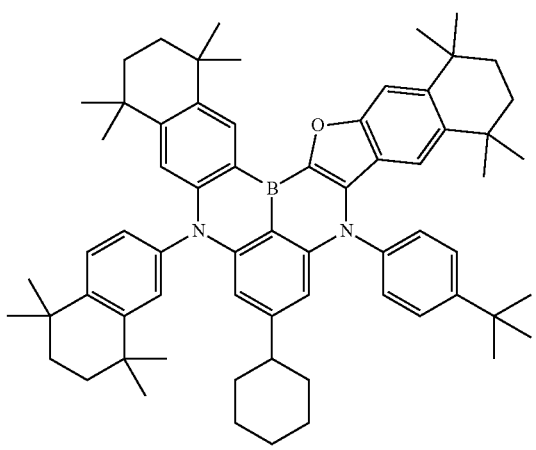
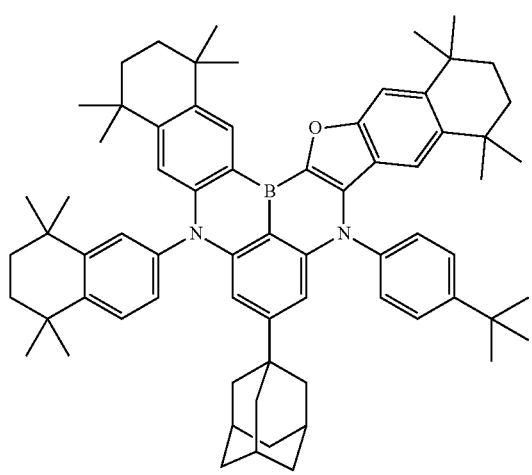
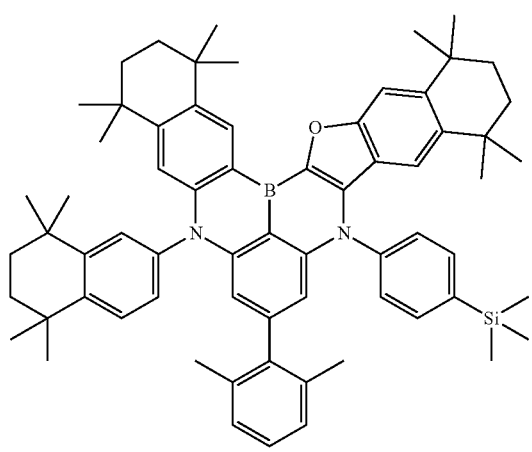
1780
-continued
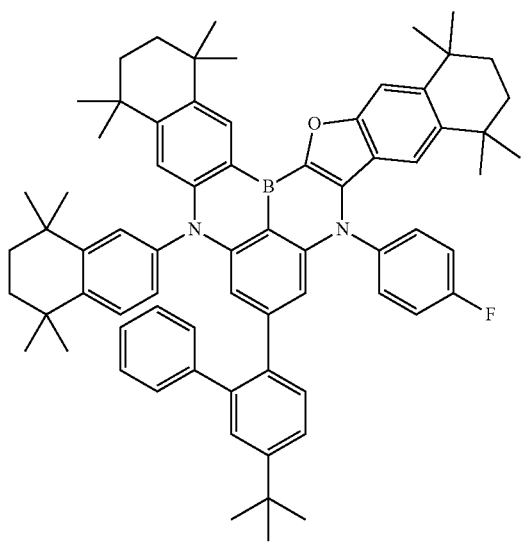
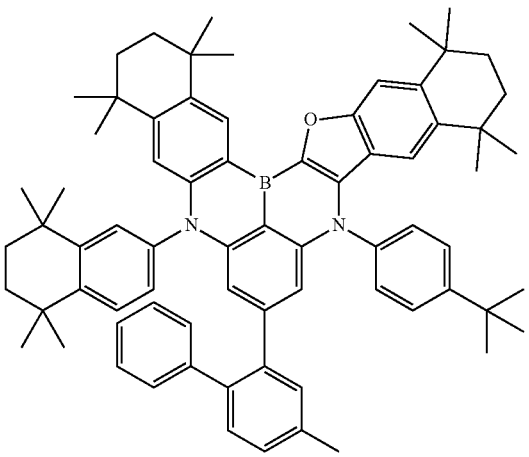

1781
-continued
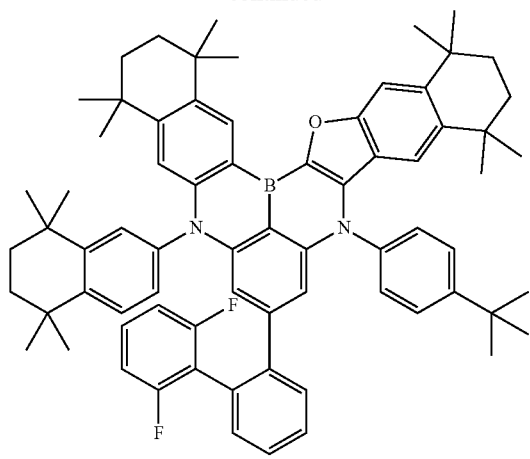
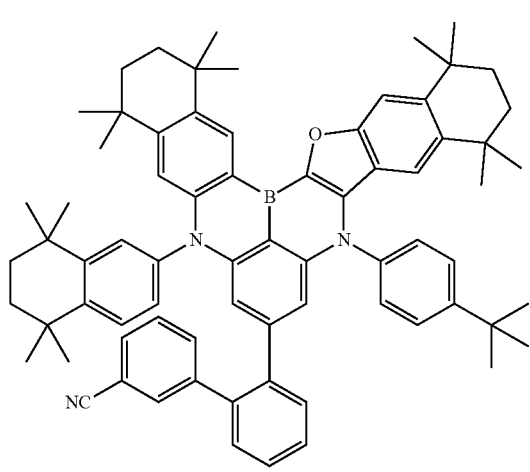
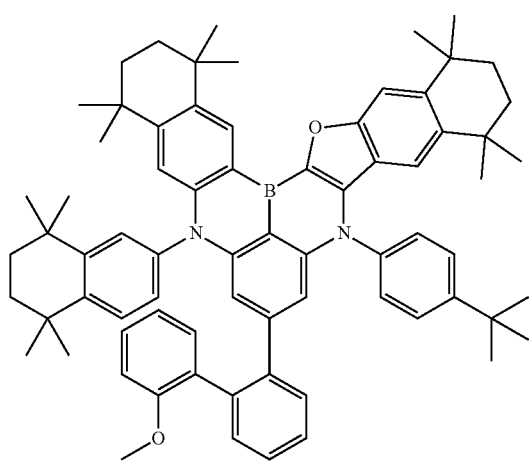
1782
-continued
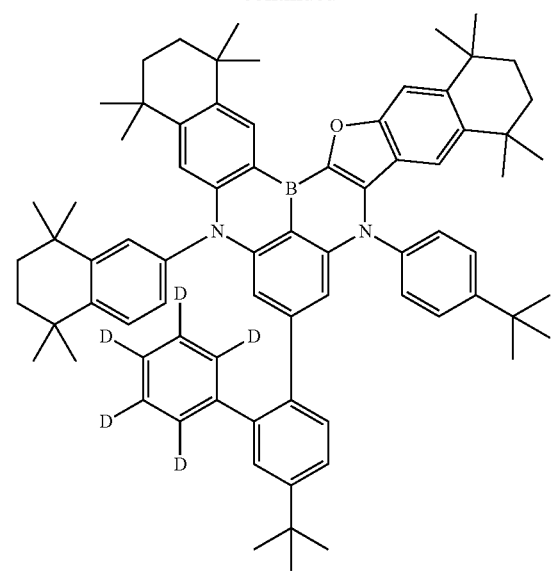
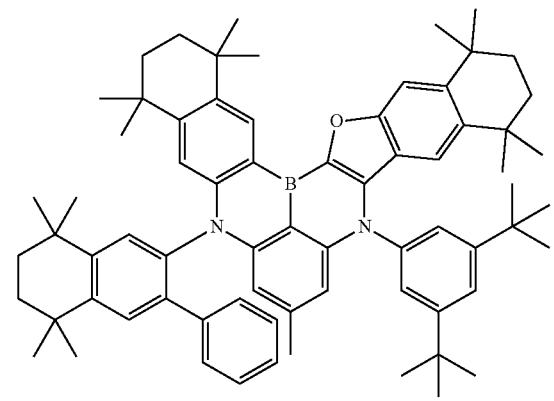
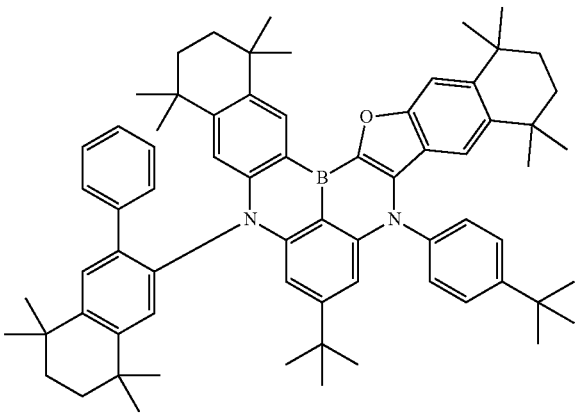

1783
-continued
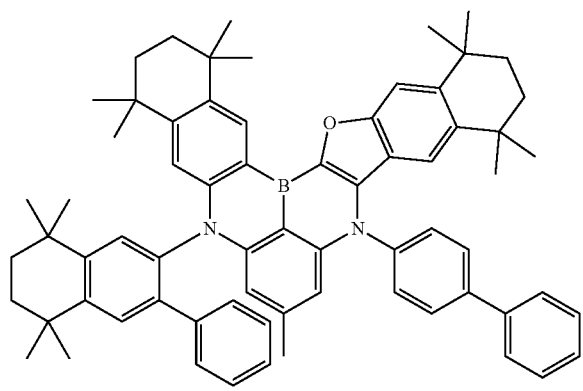
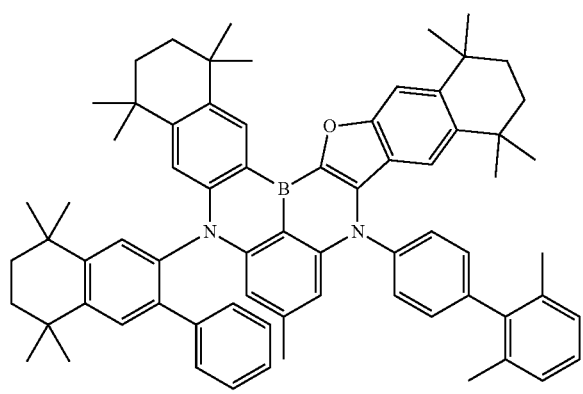
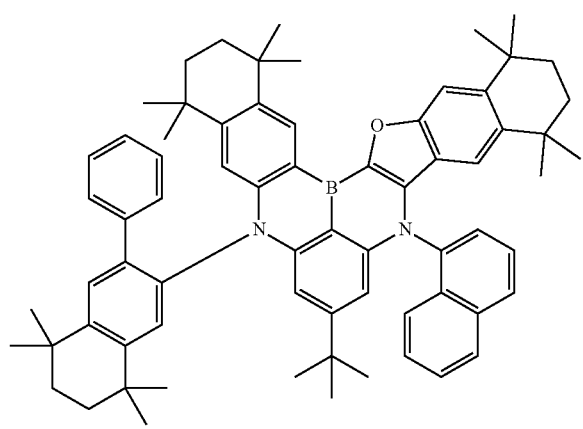
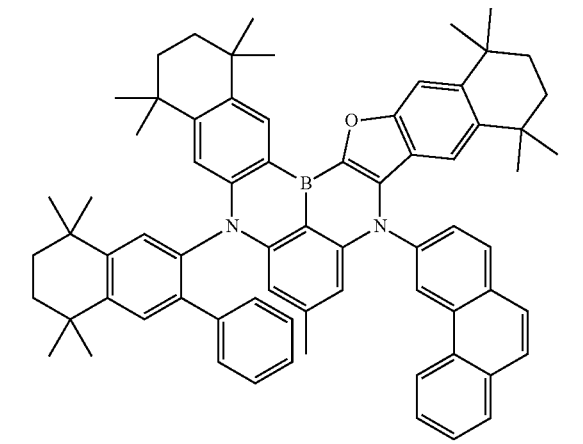
1784
-continued
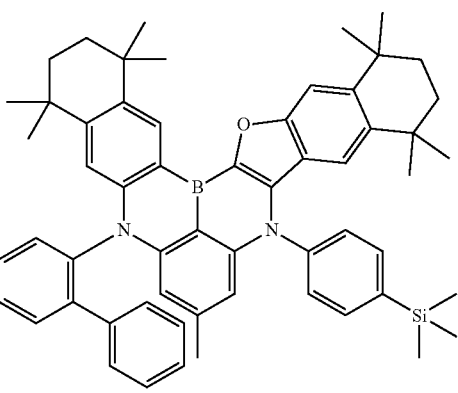
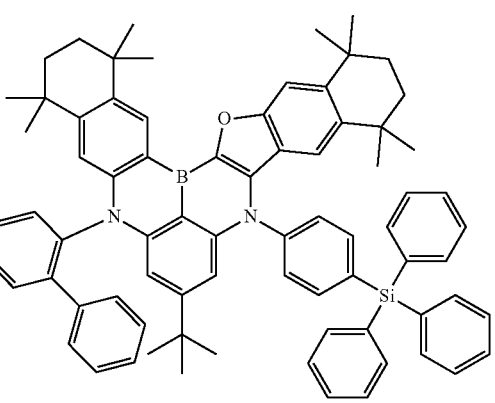
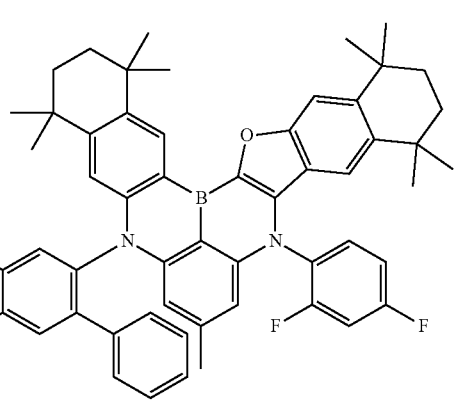
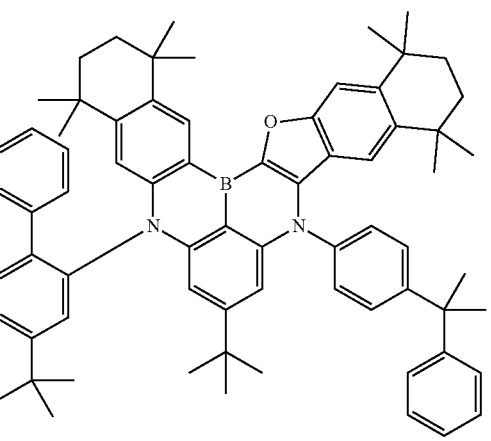

1785
-continued
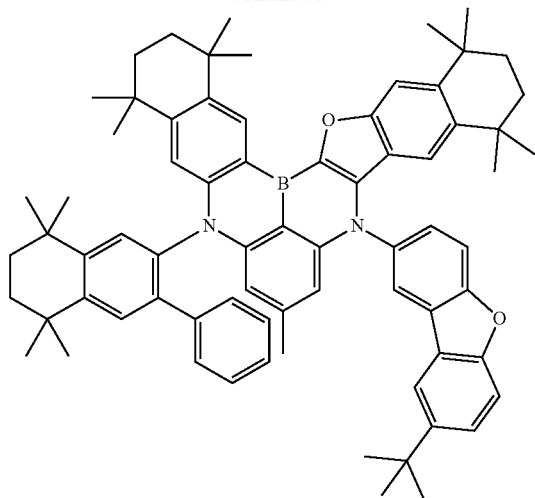
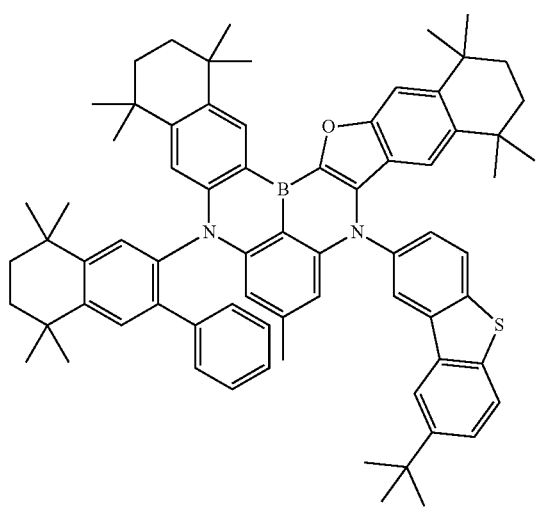
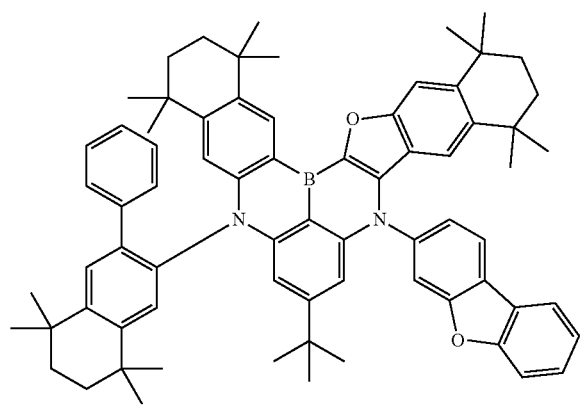
1786
-continued
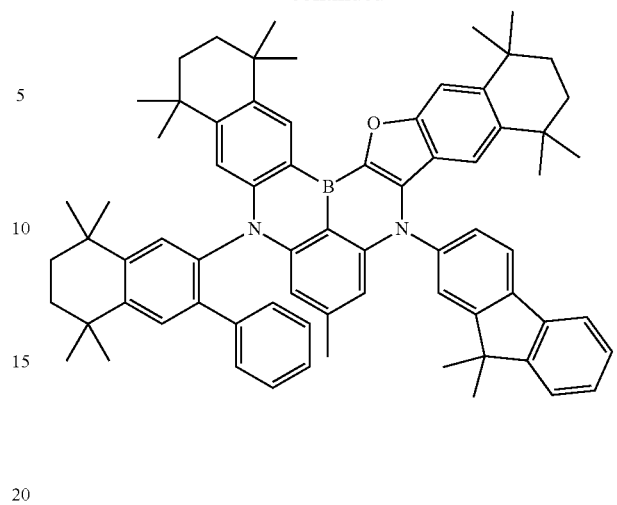
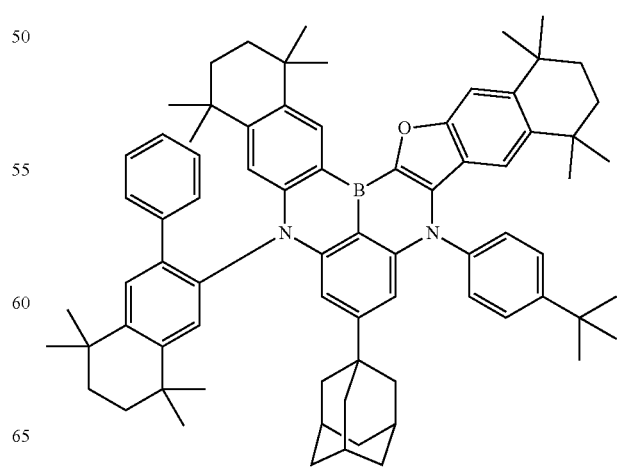

1787
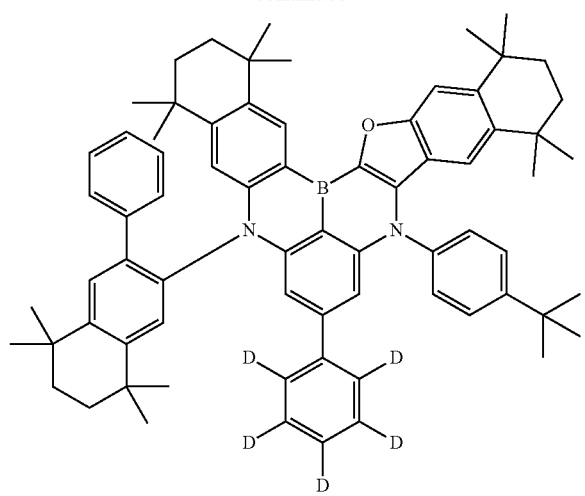
1788
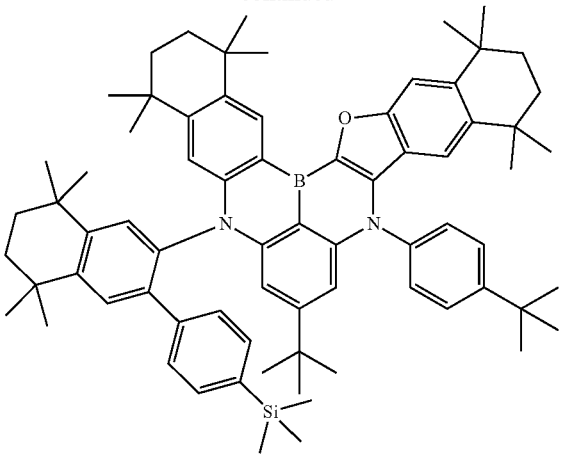
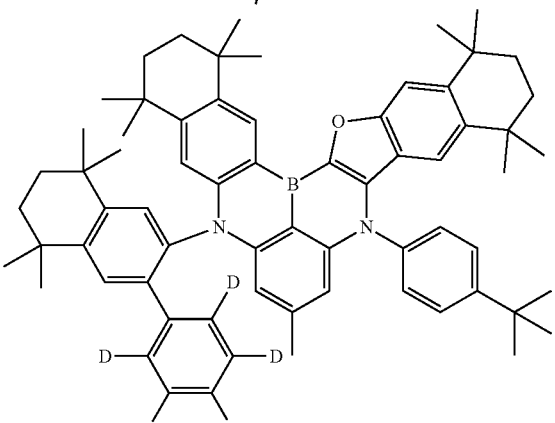
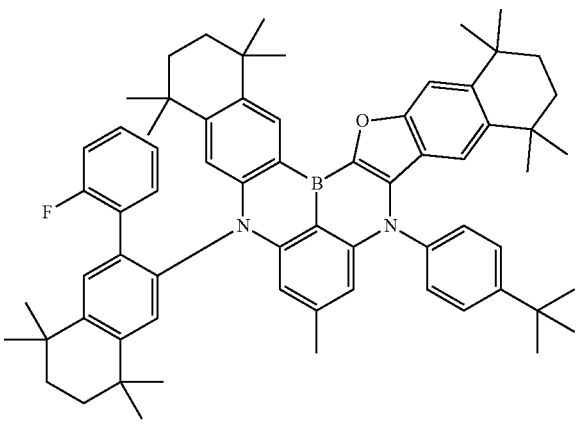
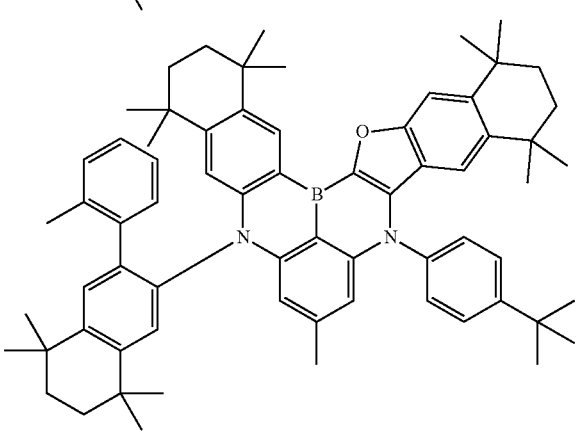

1789
-continued
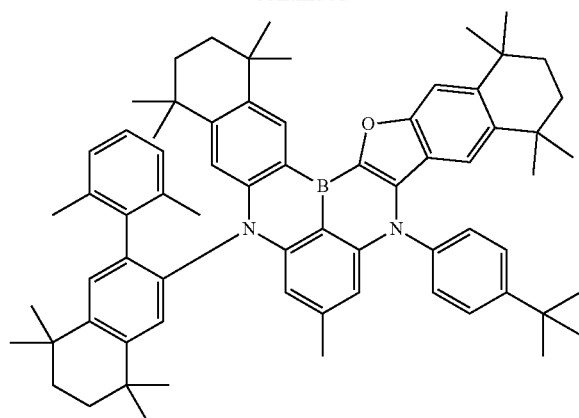
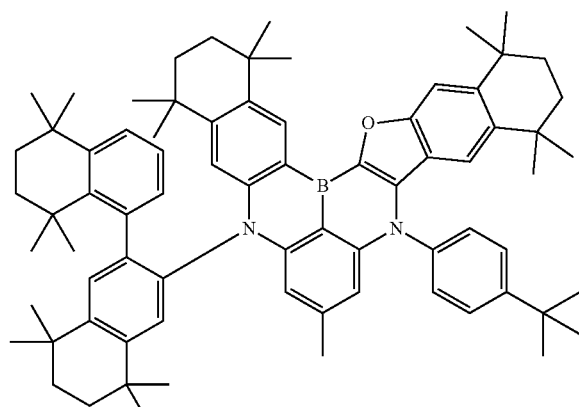
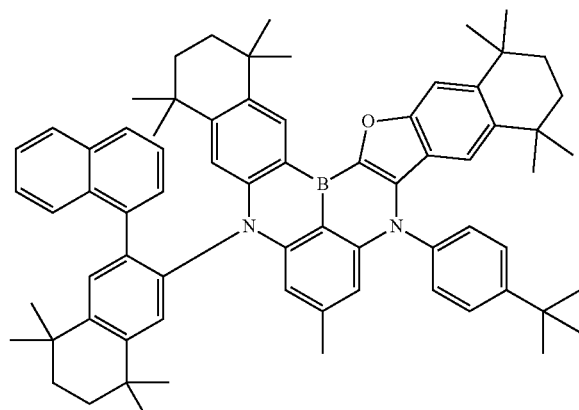
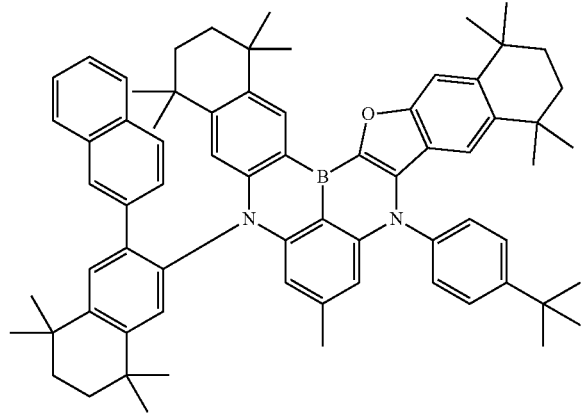
1790
-continued
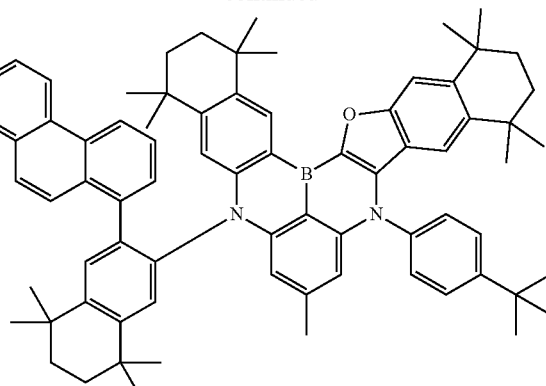
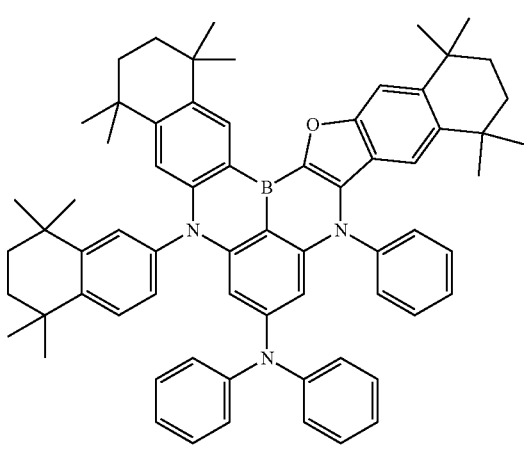
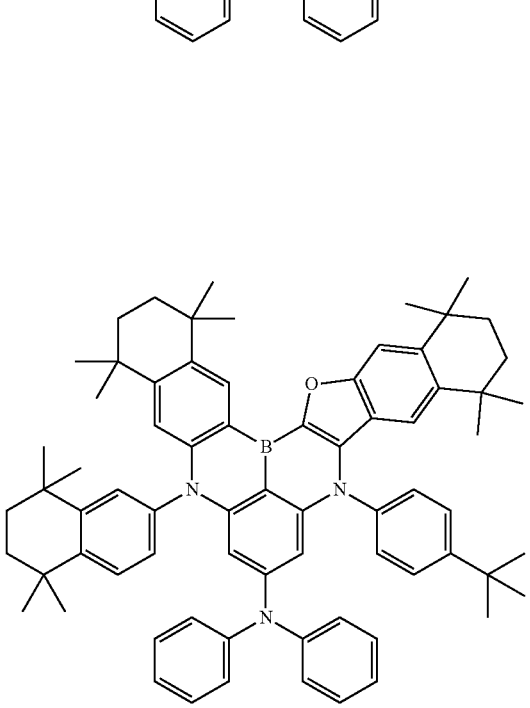

1791
-continued
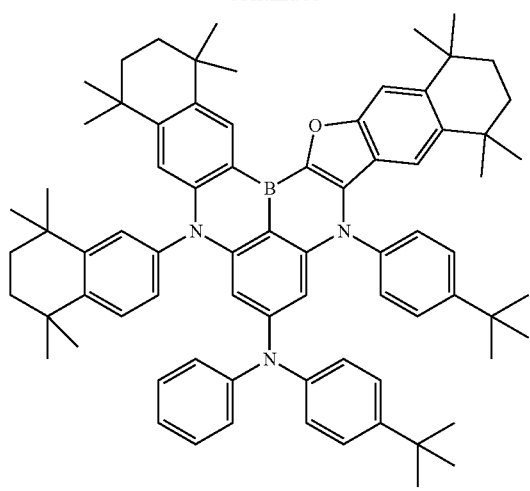
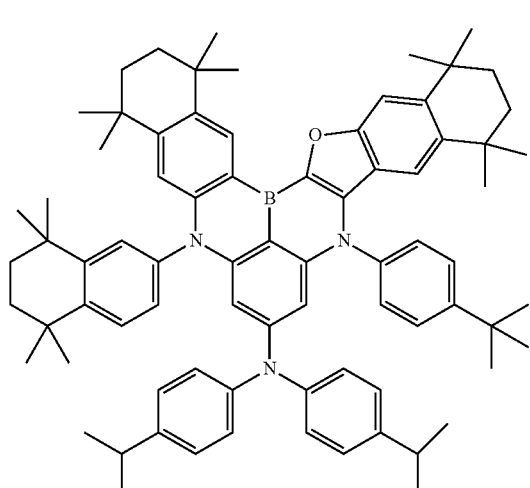
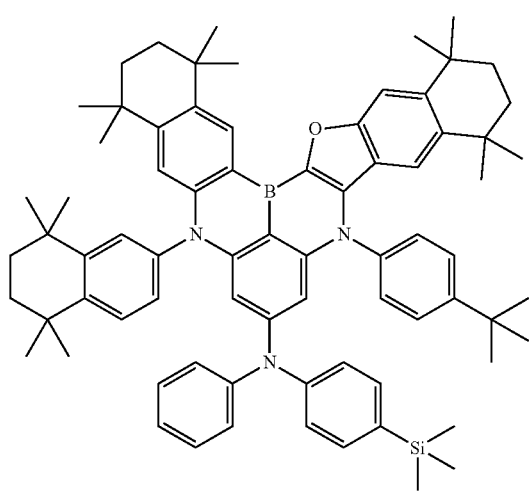
1792
-continued
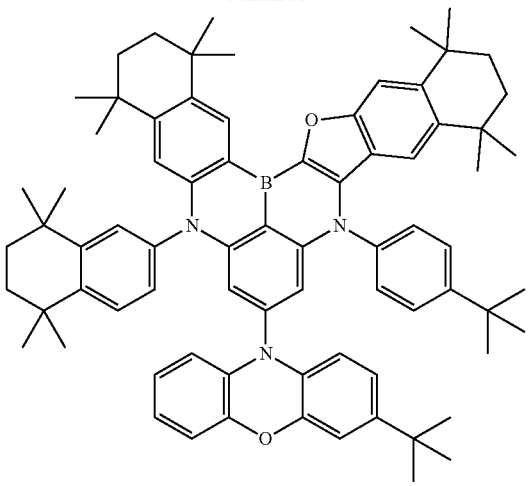
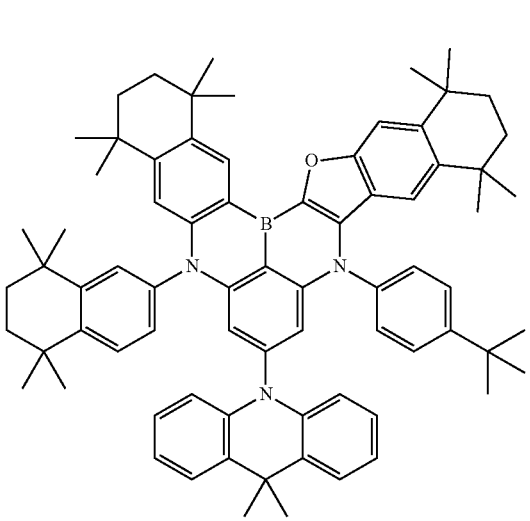
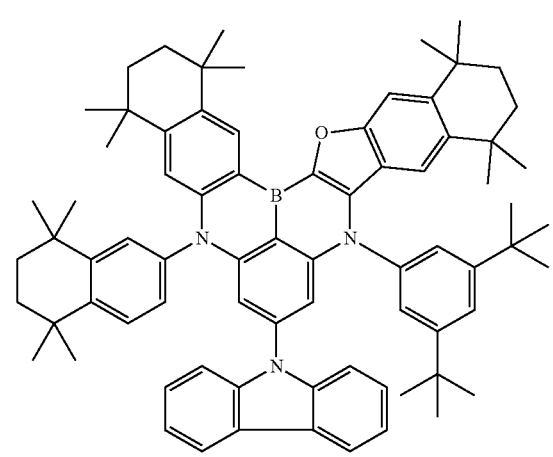

1793
-continued
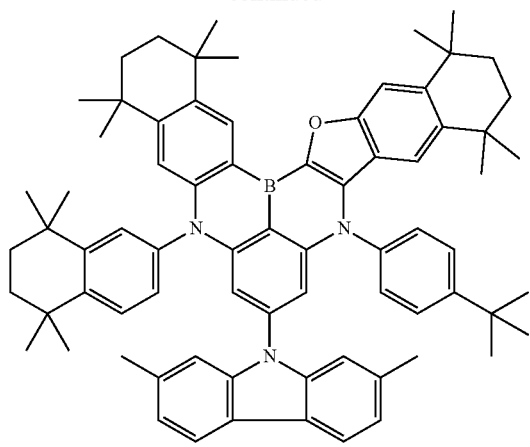
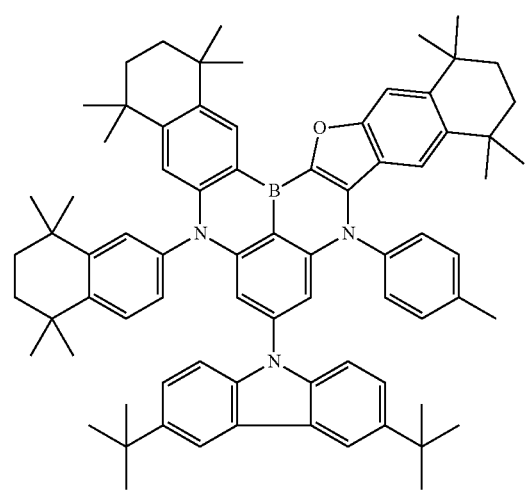
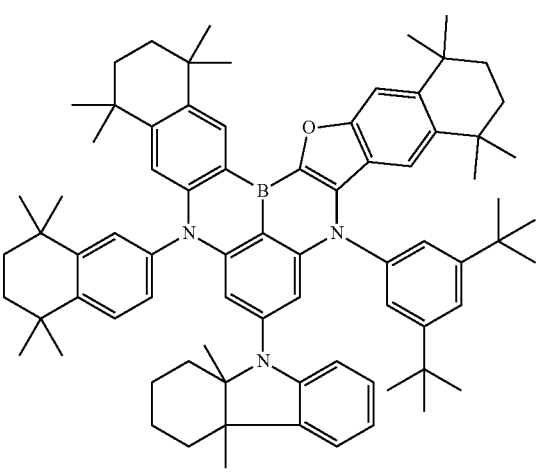
1794
-continued
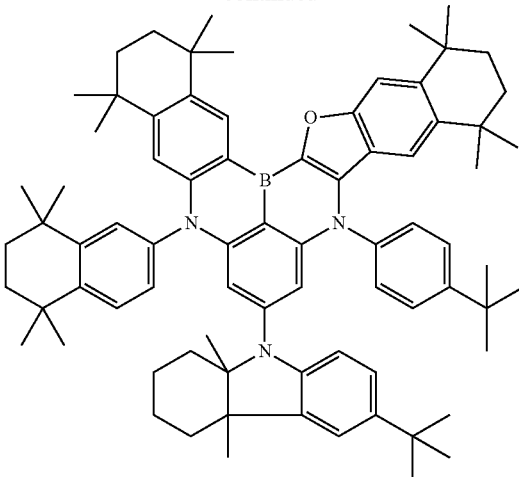
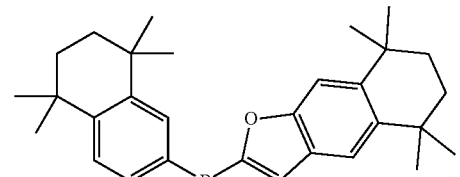
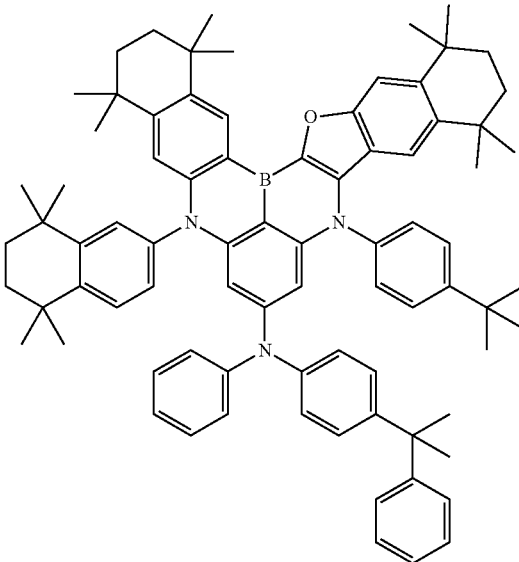

1795
-continued
1796
-continued
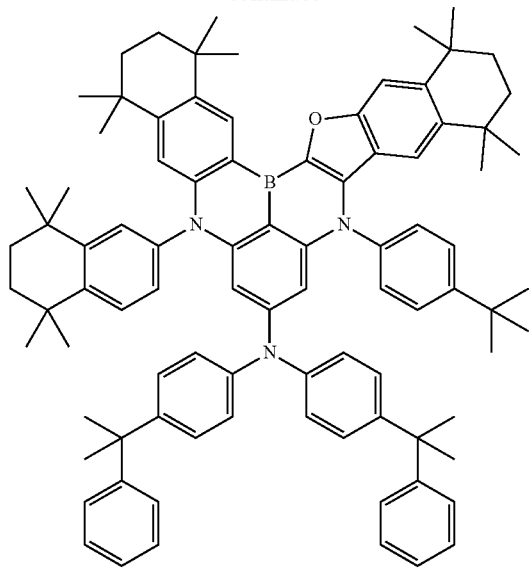
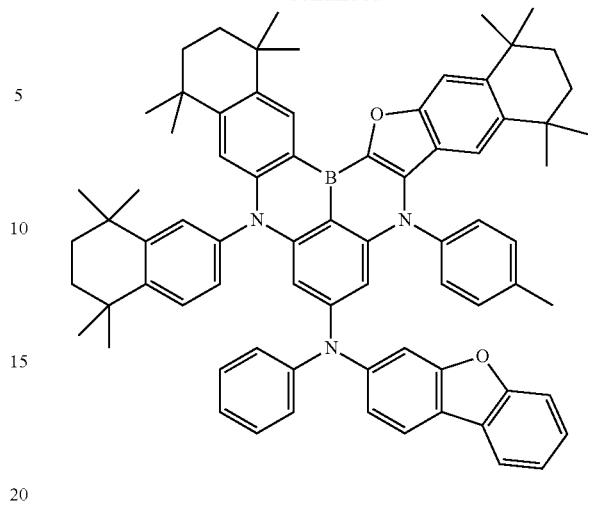
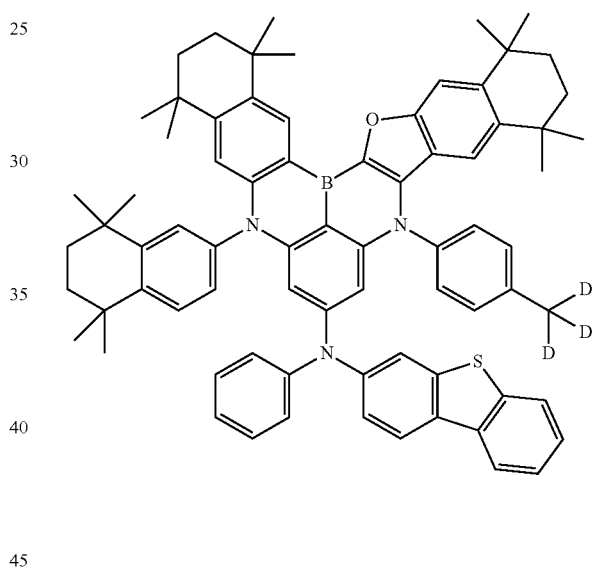
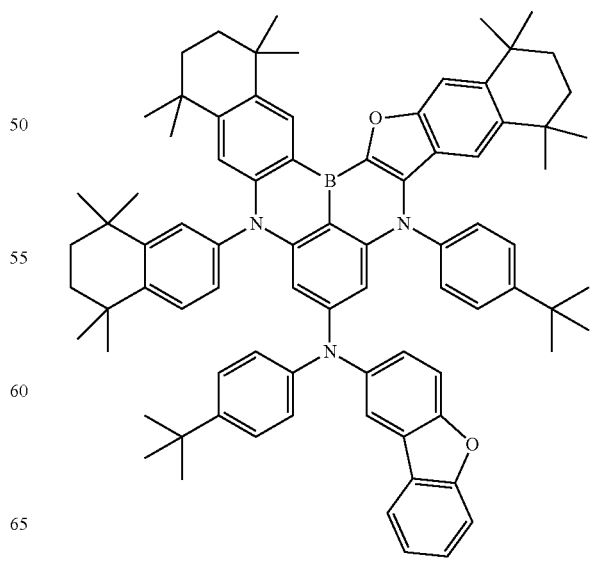

1797
-continued
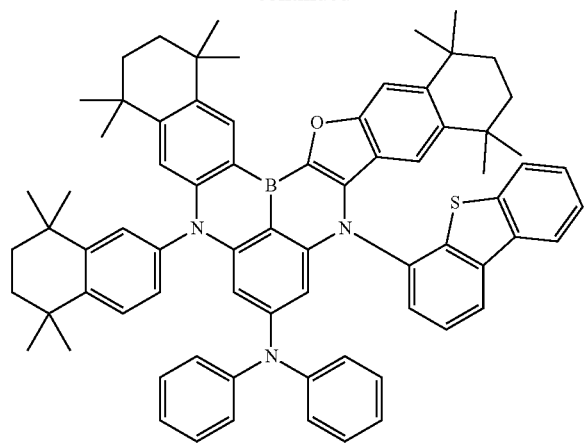
1798
-continued
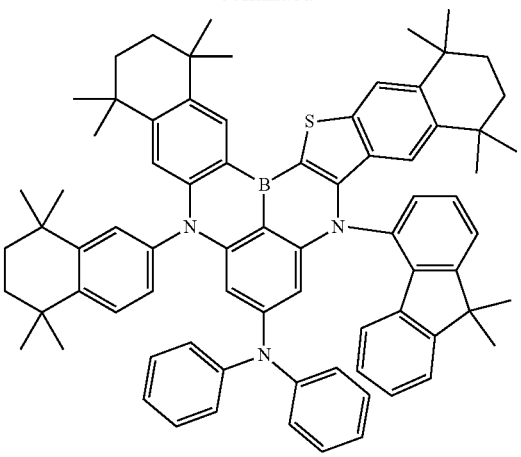
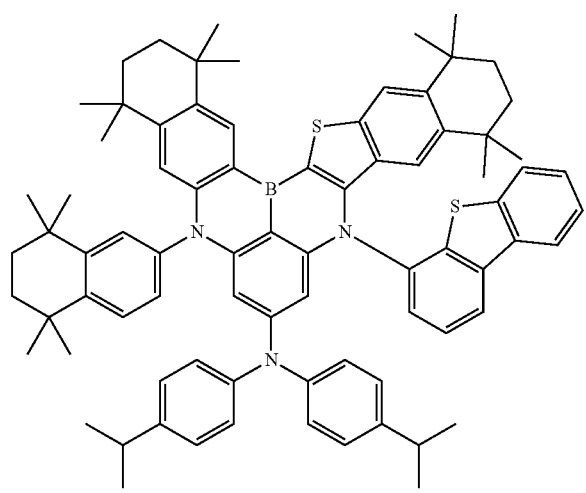
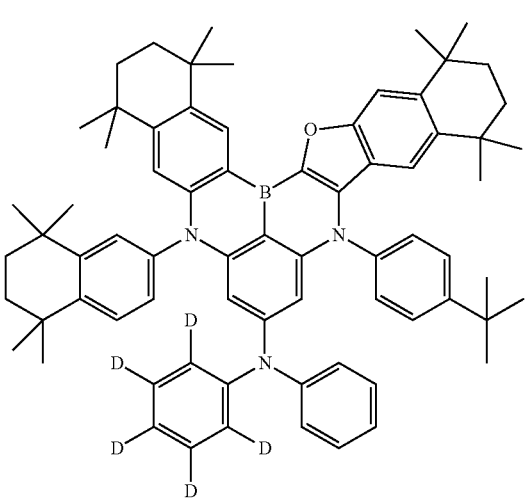
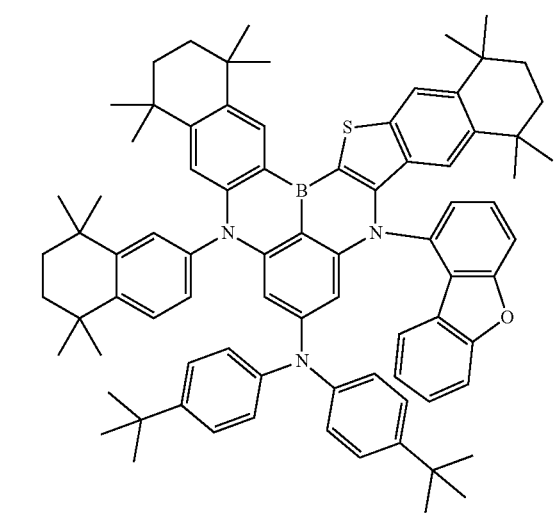
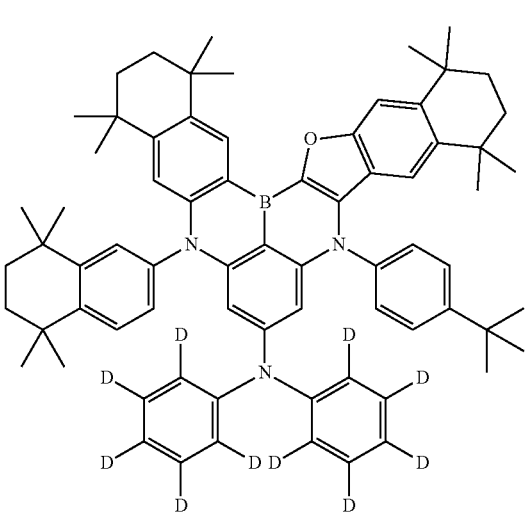

1799
-continued
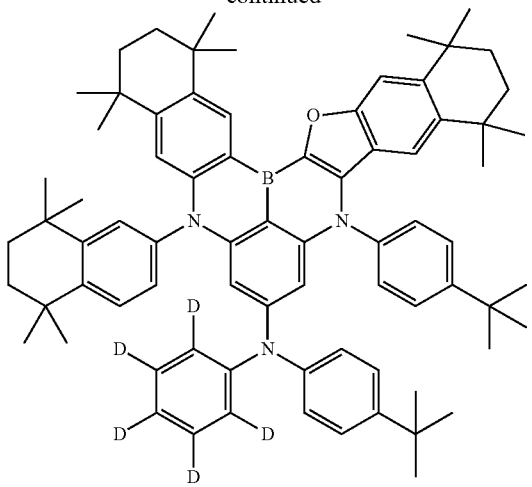
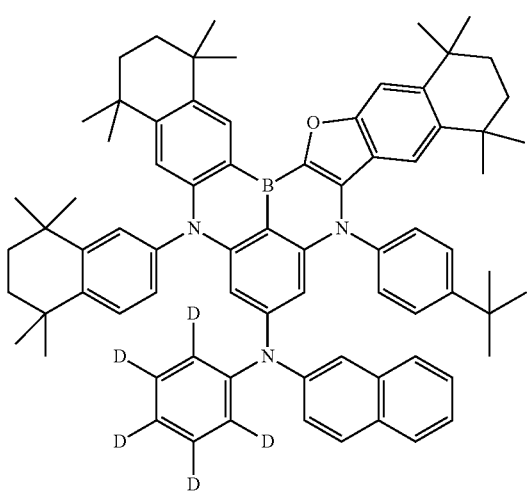
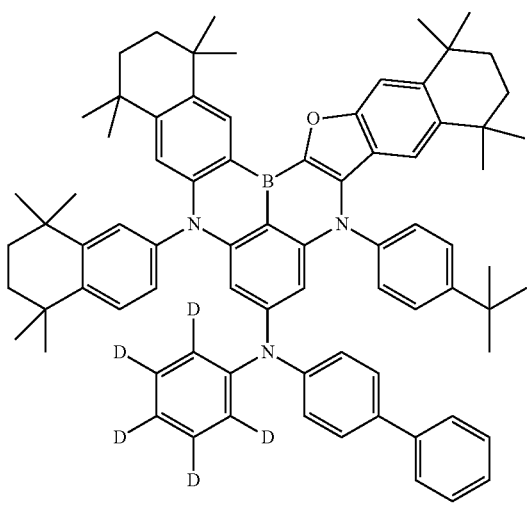
1800
-continued
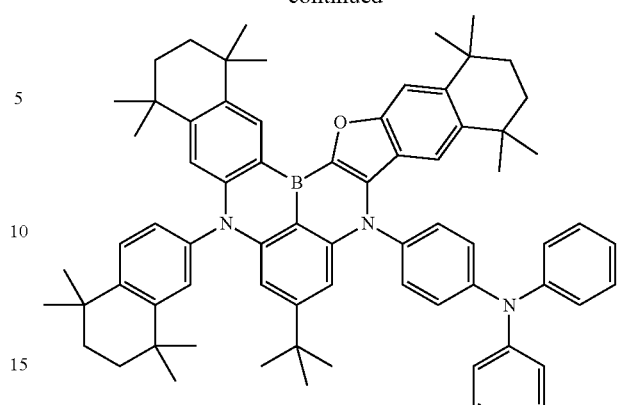
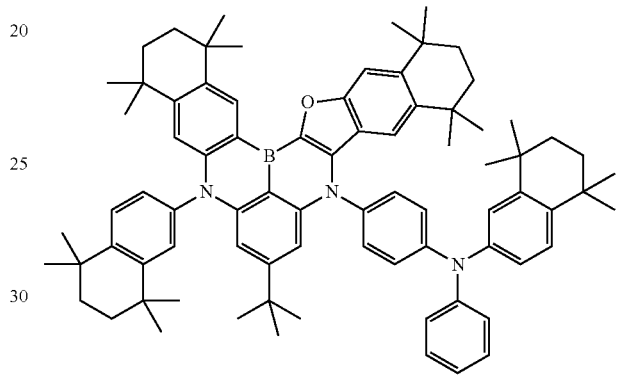
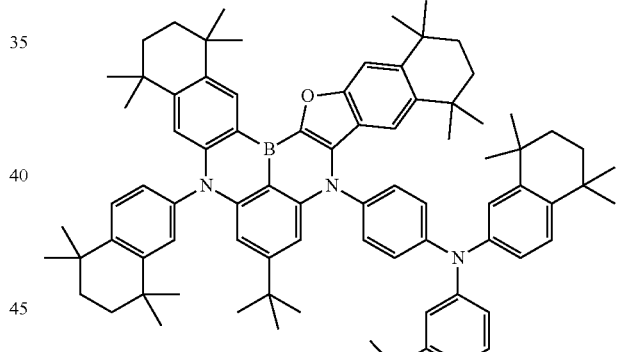
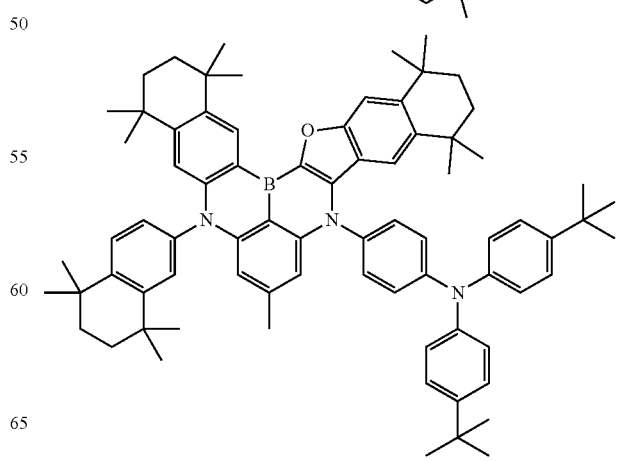

1801
-continued
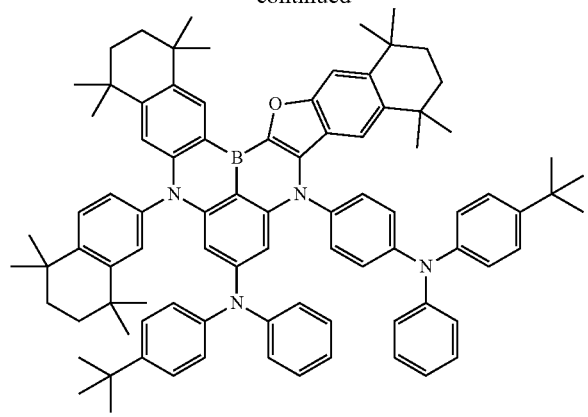
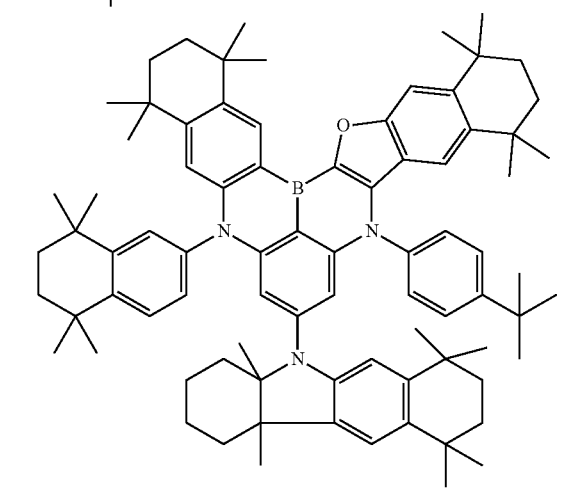
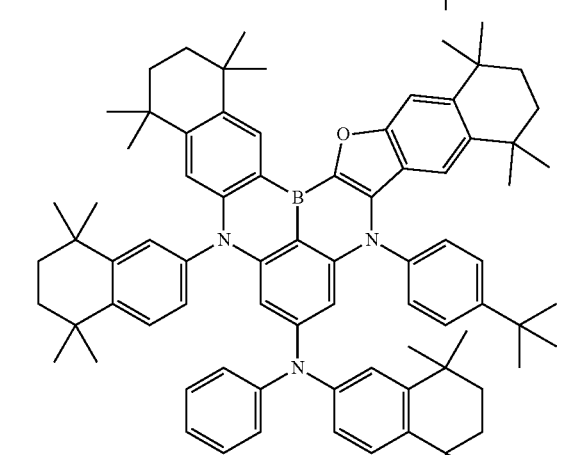
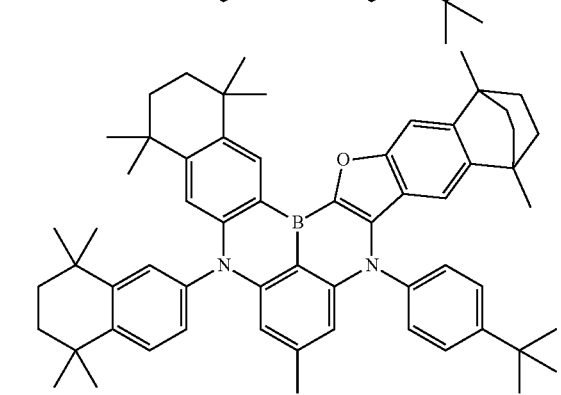
1802
-continued
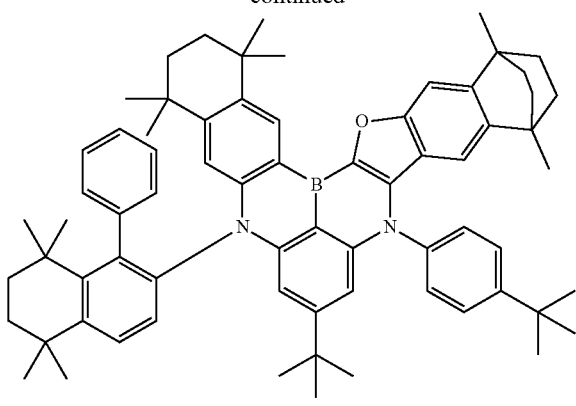
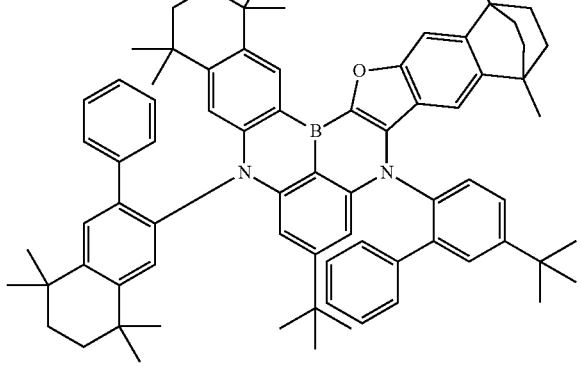
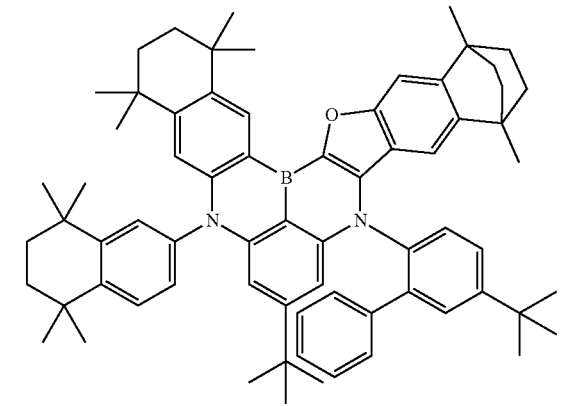
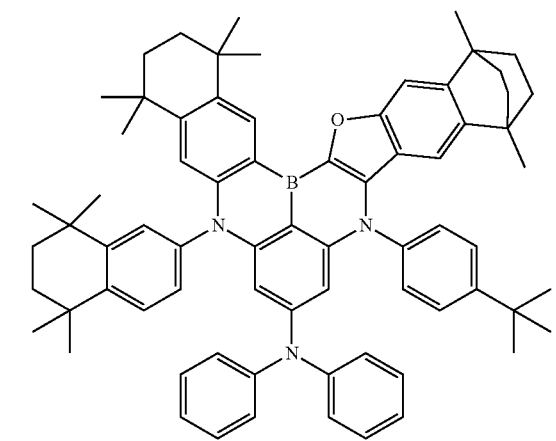

1803
-continued
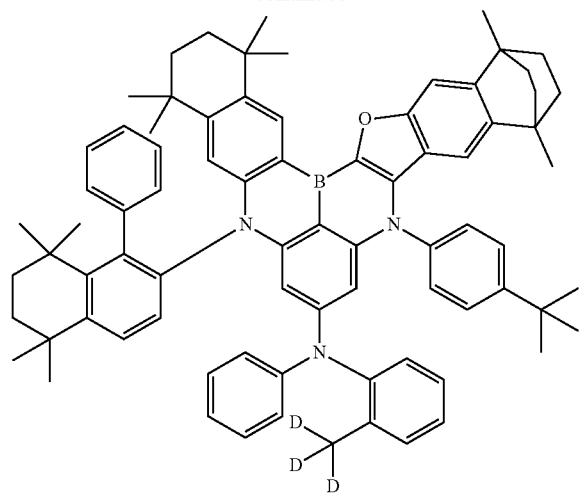
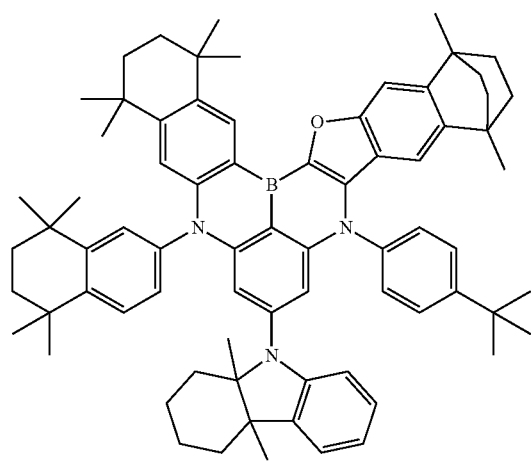
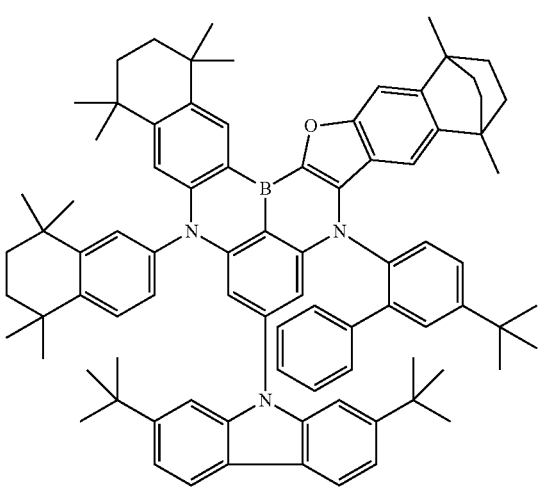
1804
-continued
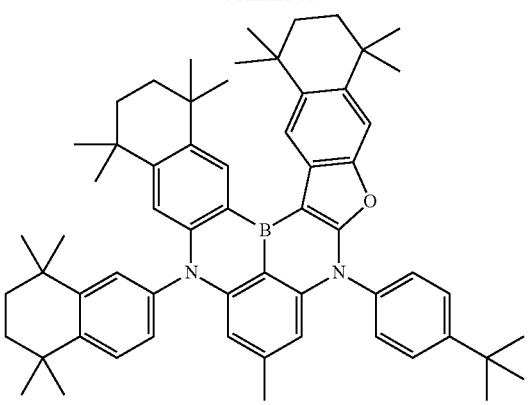
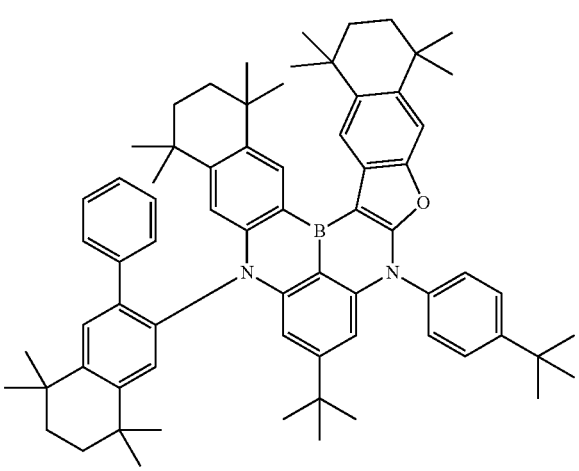
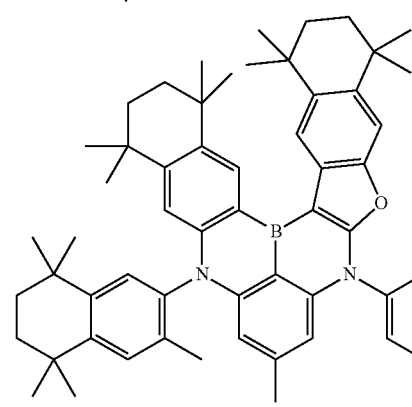

1805
-continued

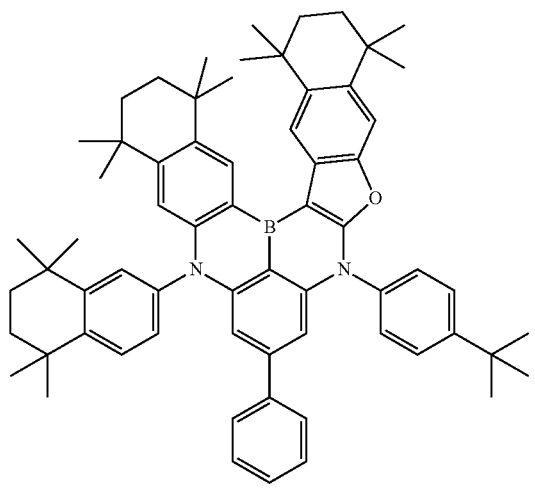
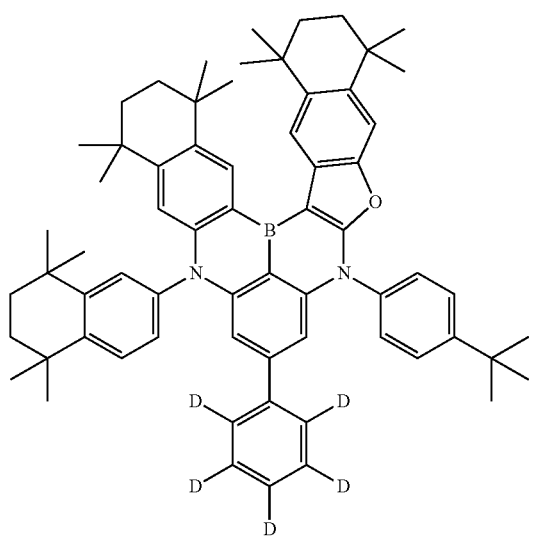
1806
-continued
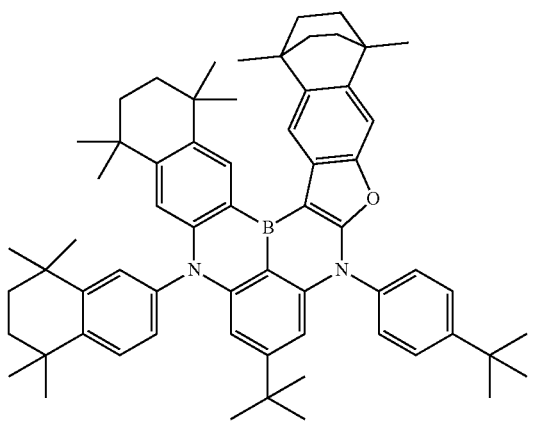
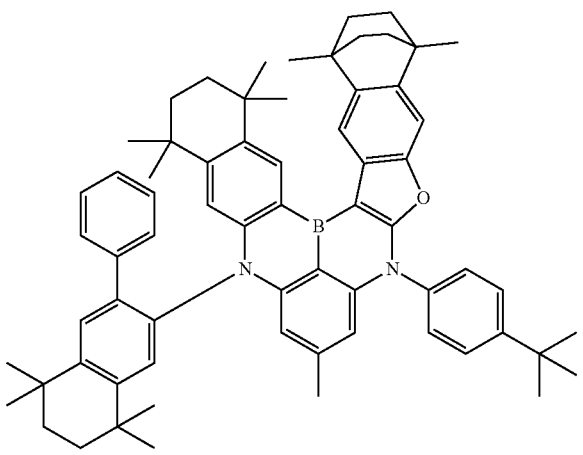

1807
-continued
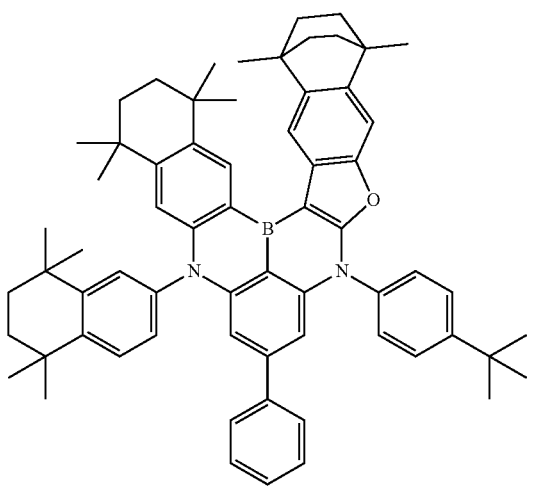
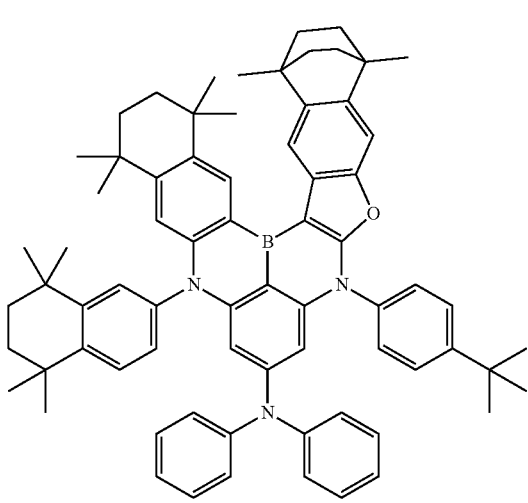
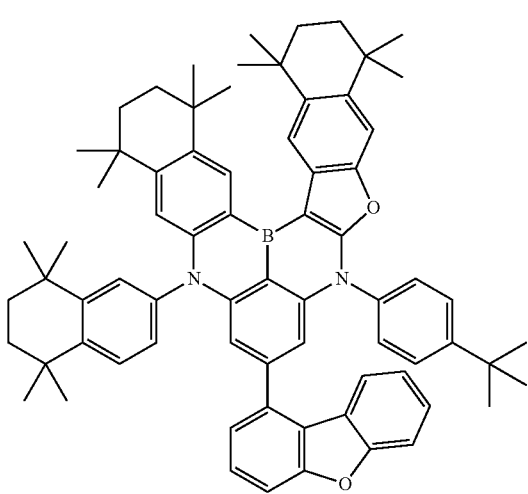
1808
-continued

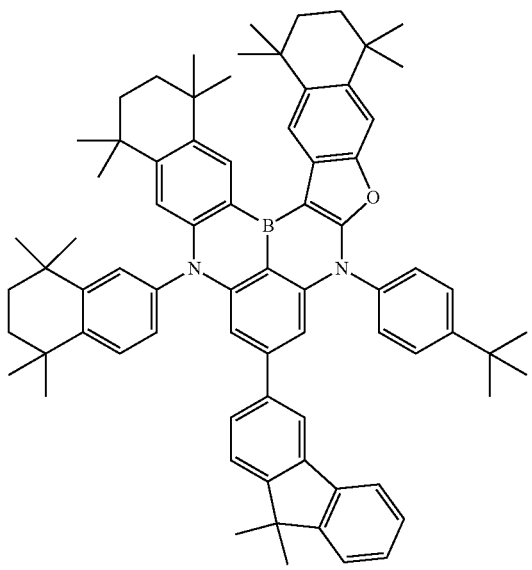

1809
-continued
1810
-continued
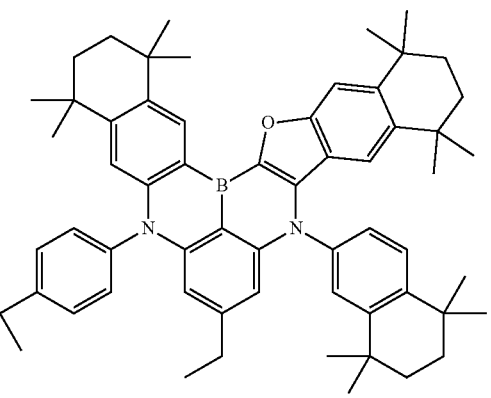
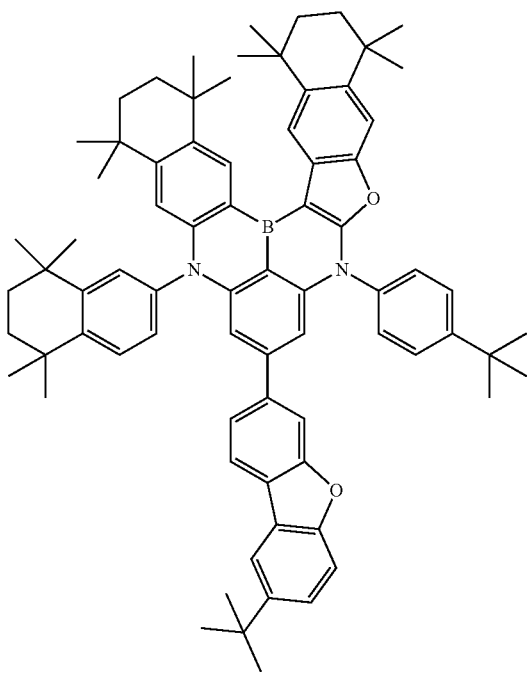
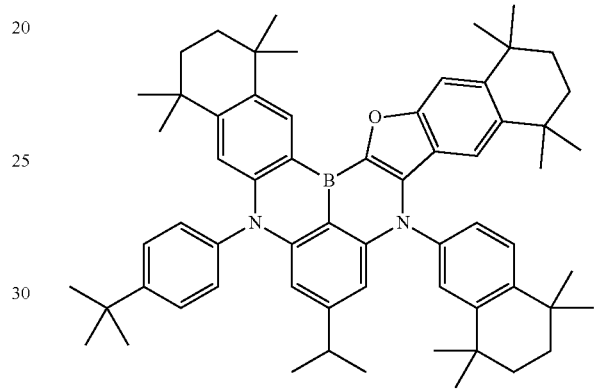
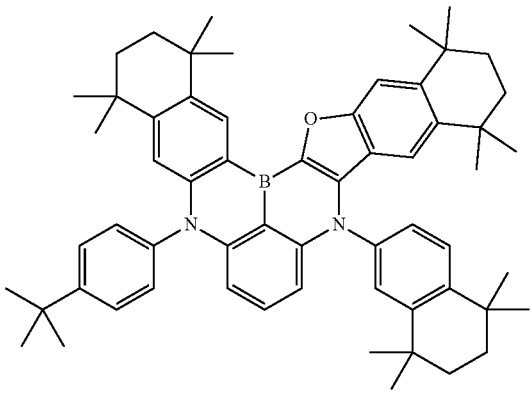
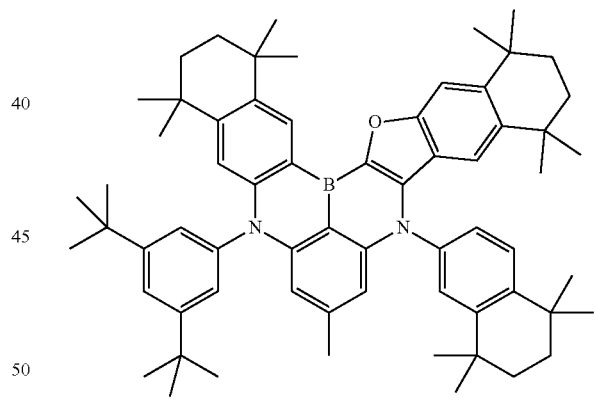
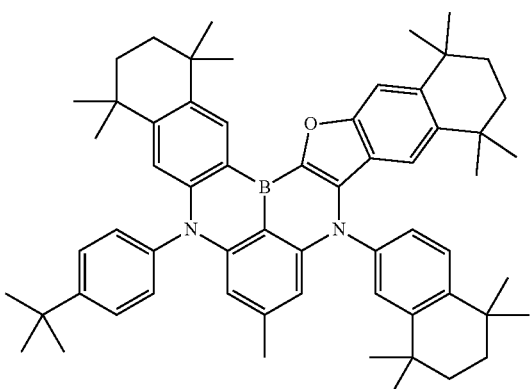
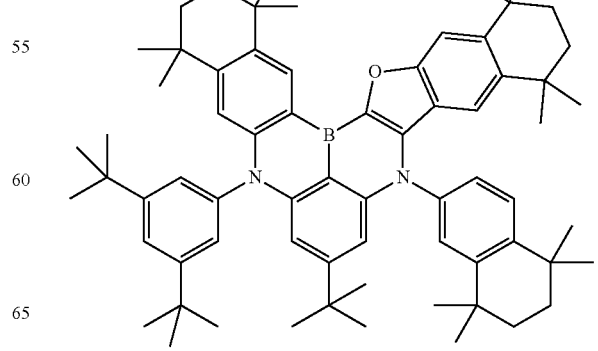

1811
-continued
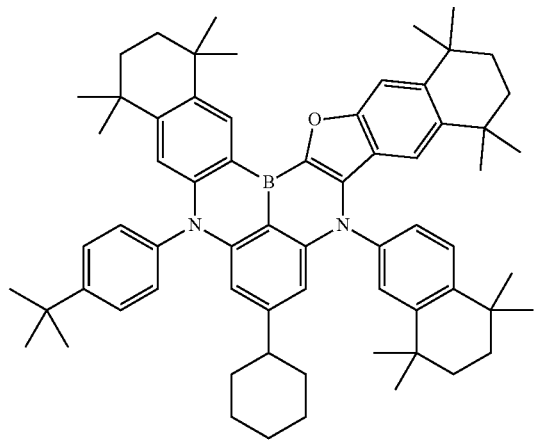
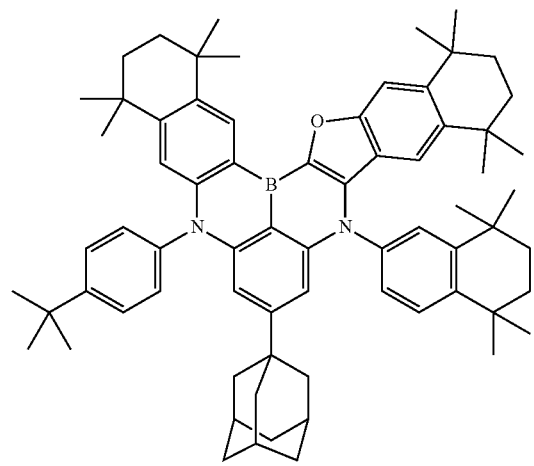
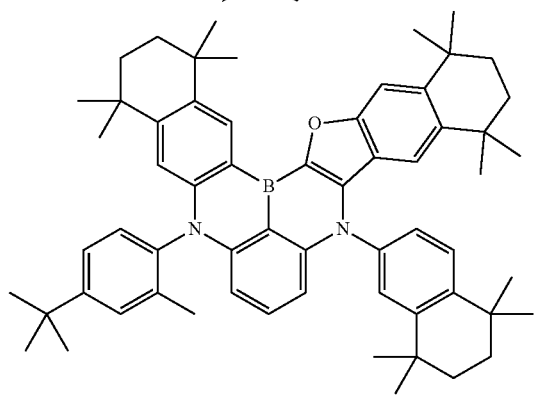
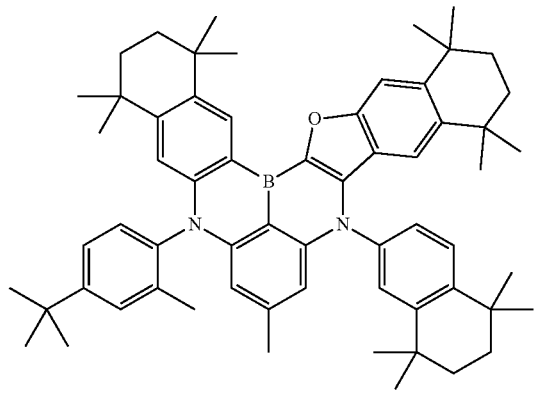
1812
-continued
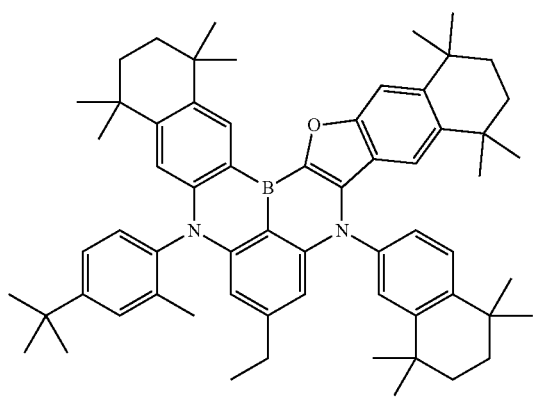
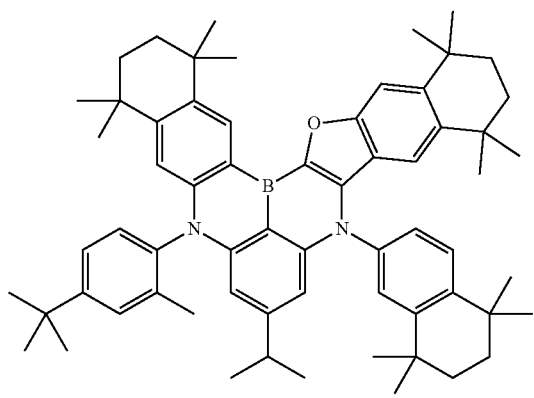
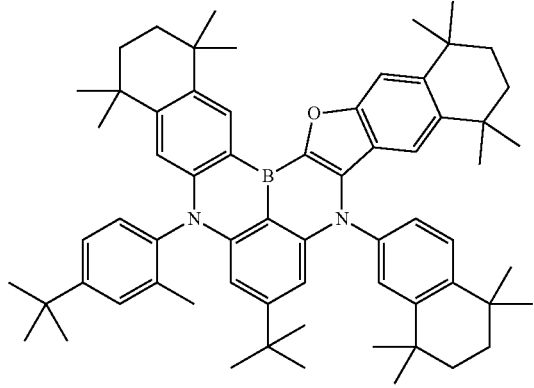
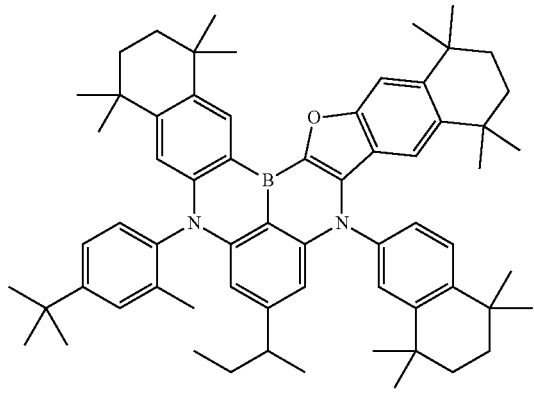

1813
-continued
1814
-continued
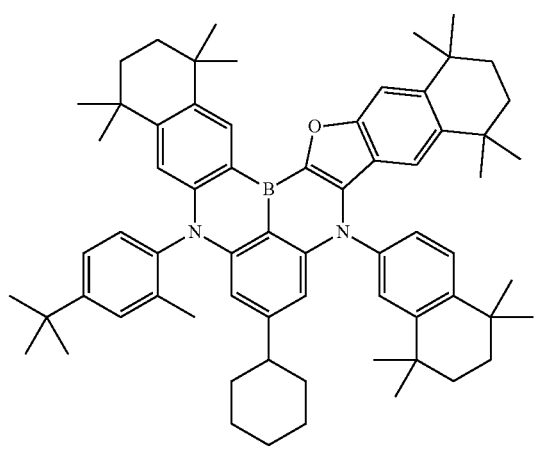
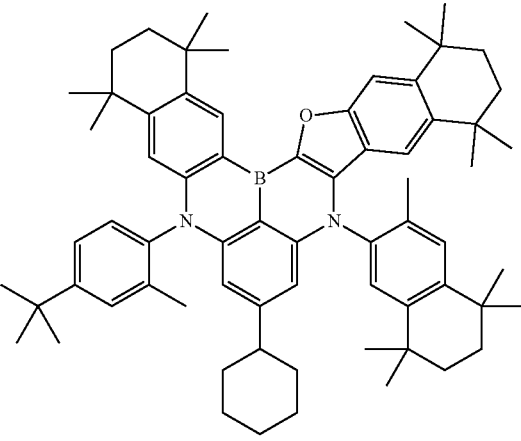

1815
-continued
1816
-continued
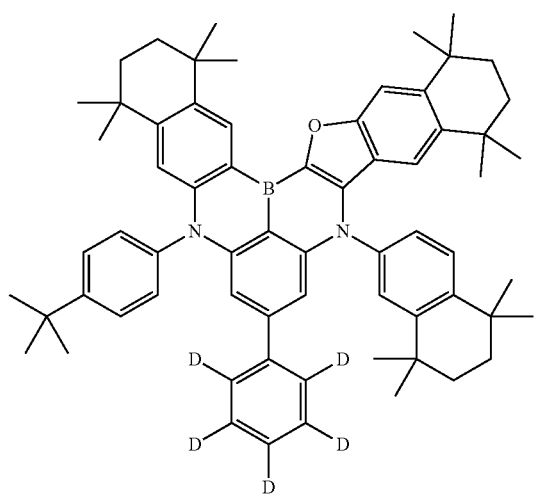
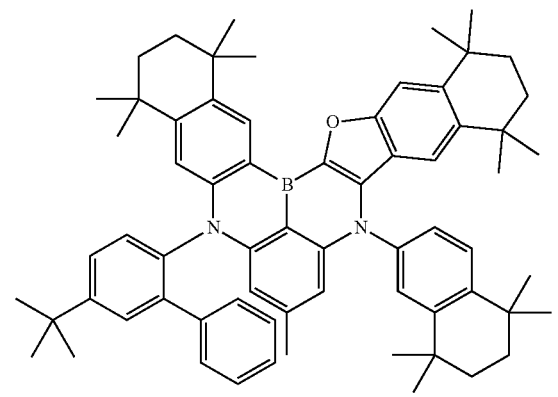
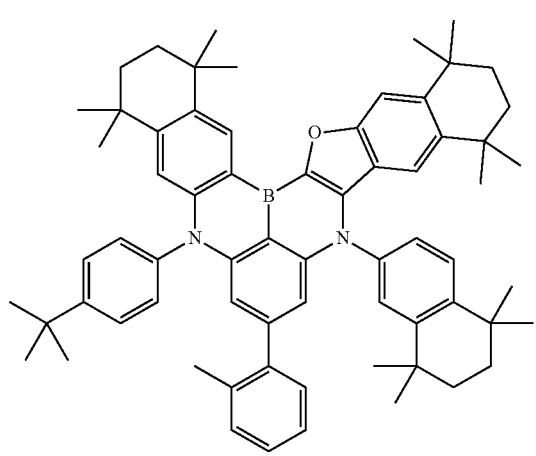
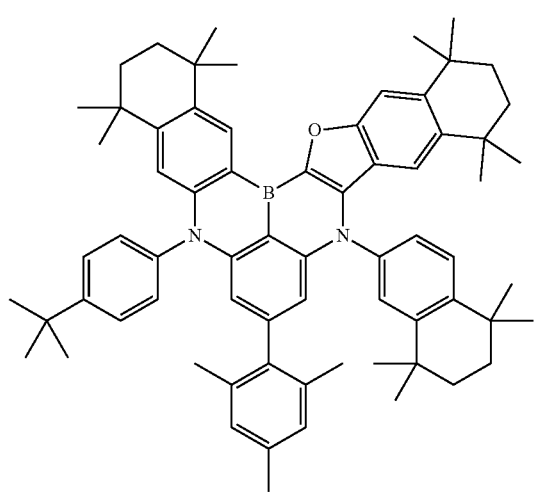

1817
-continued
1818
-continued
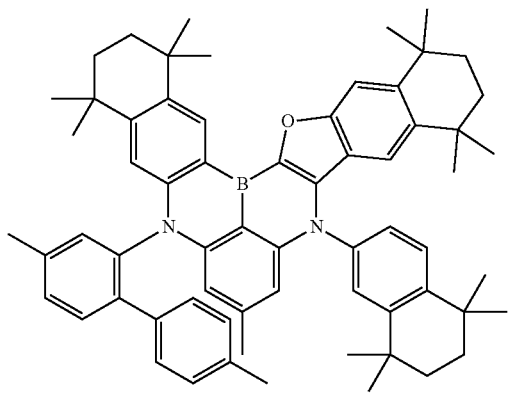
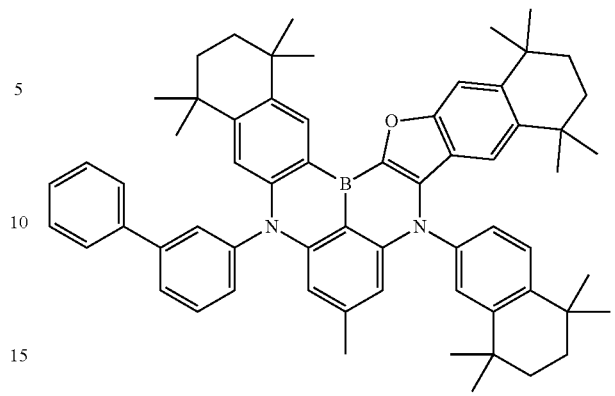
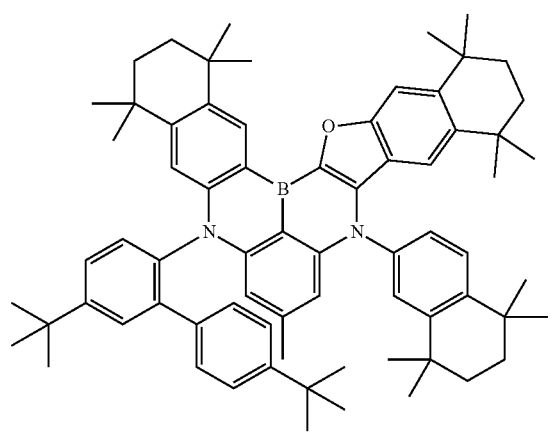
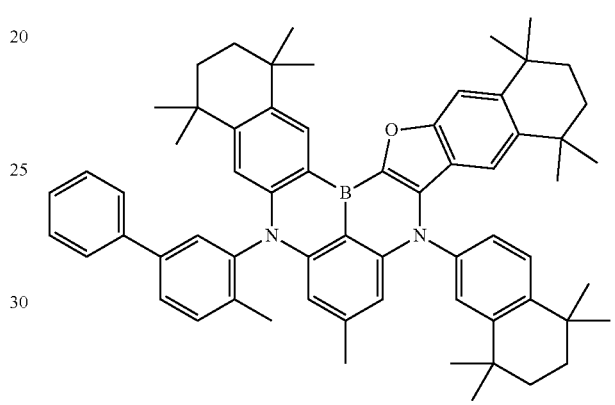
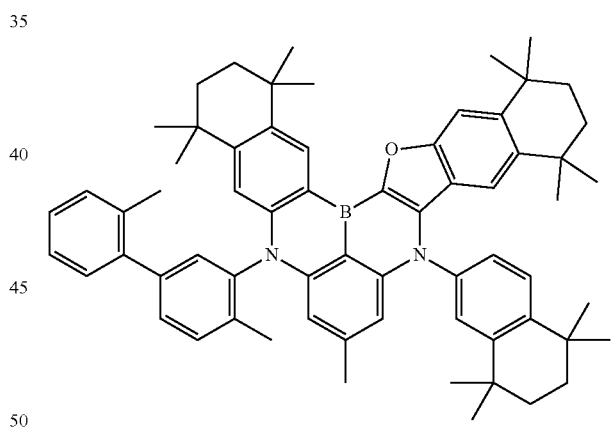
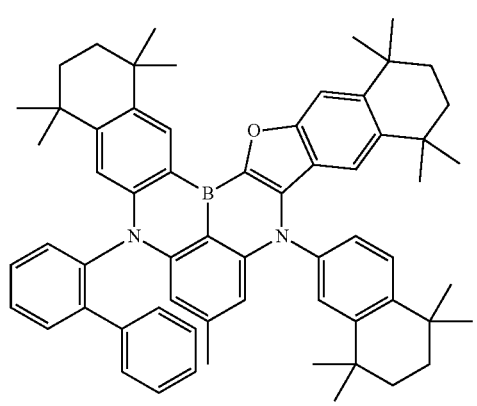
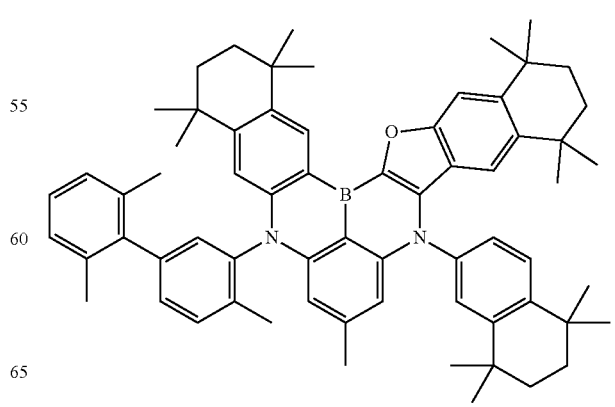

| 1819 -continued | 1820 -continued |
|---|---|
| 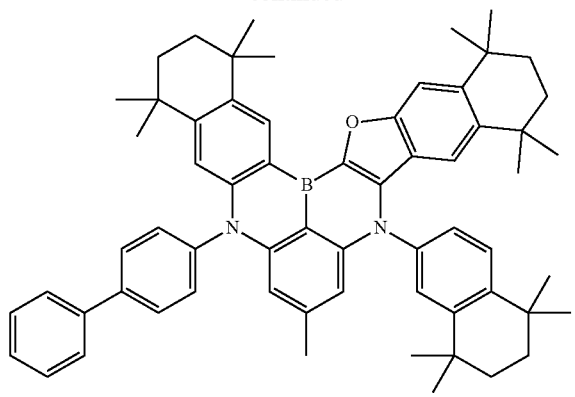 |  |
| 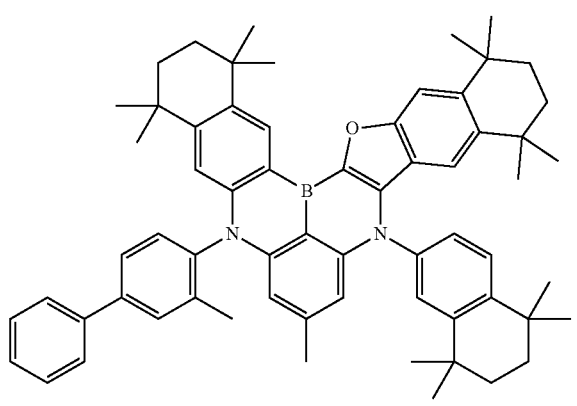 | 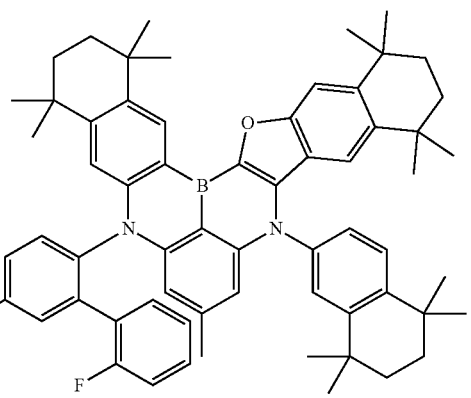 |
| 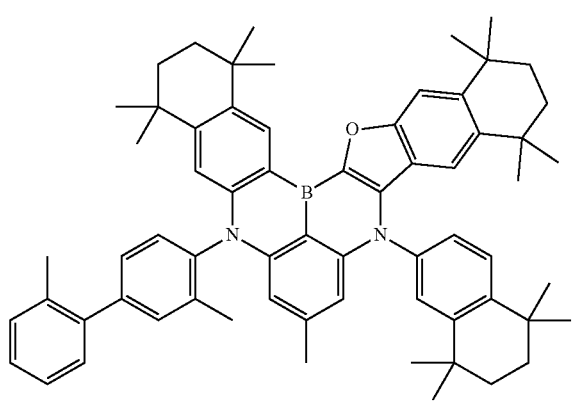 | 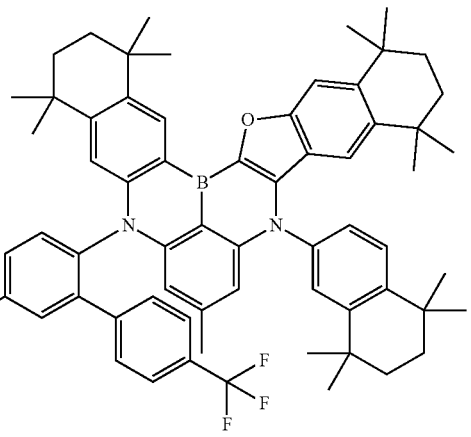 |
| 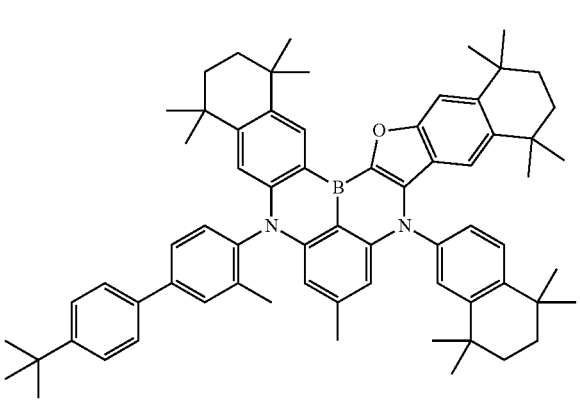 | 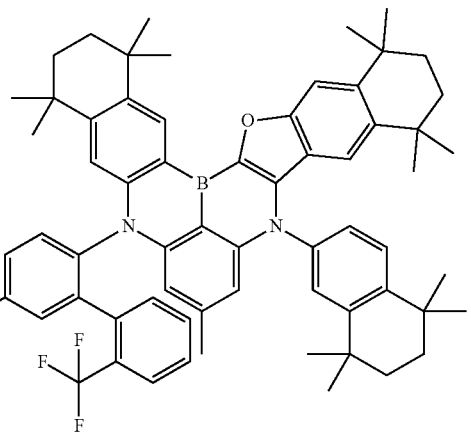 |

| 1821 -continued | 1822 -continued |
|---|---|
| 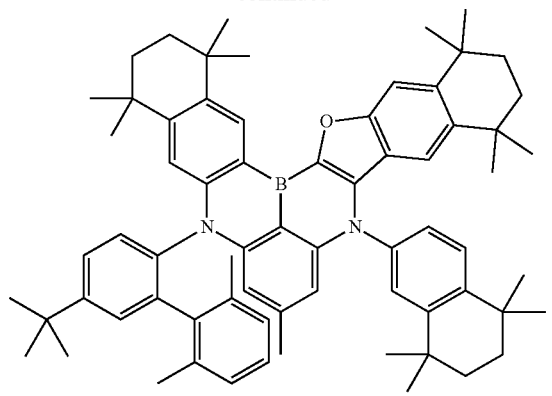 | 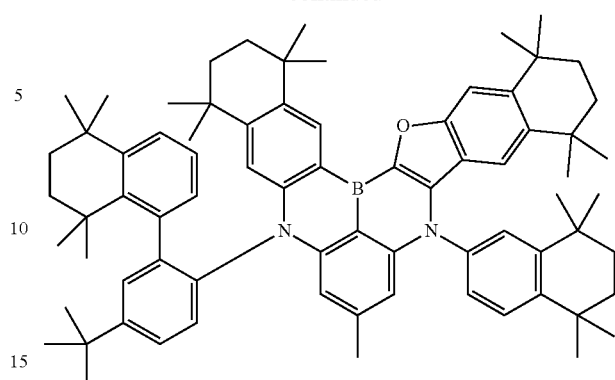 |
| 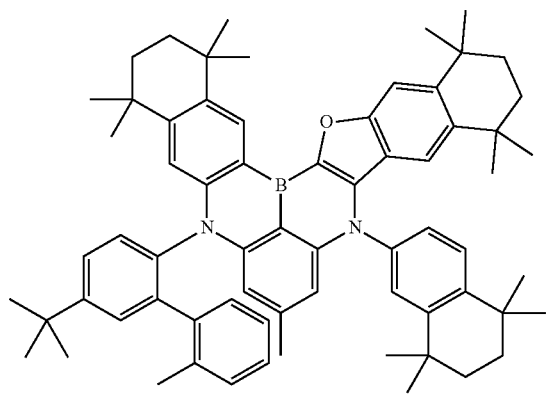 | 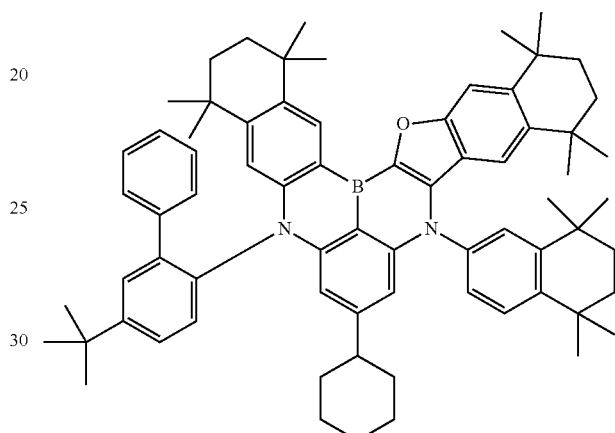 |
| 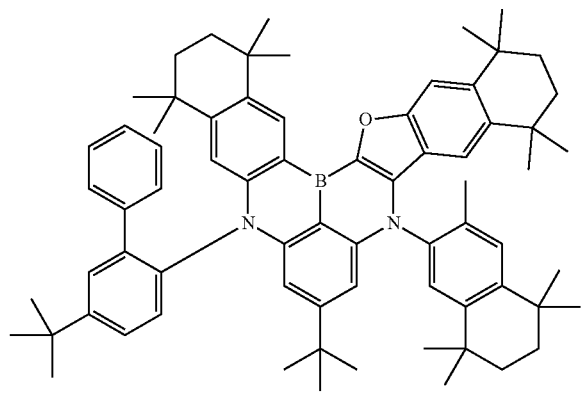 | 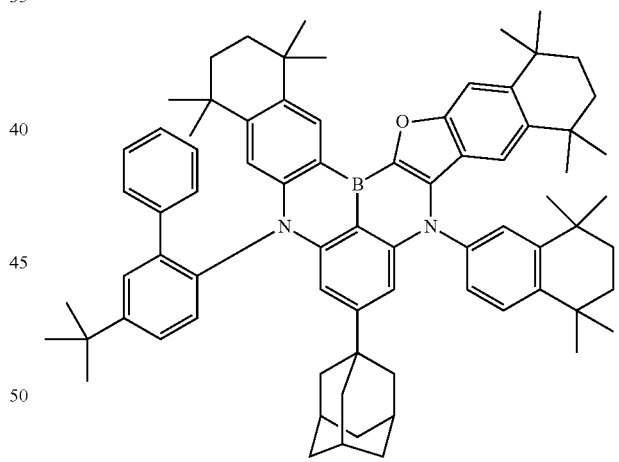 |
| 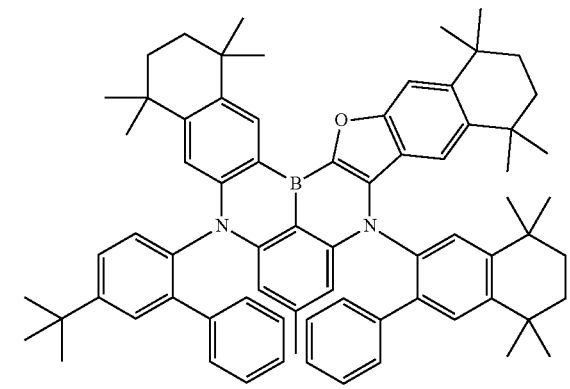 | 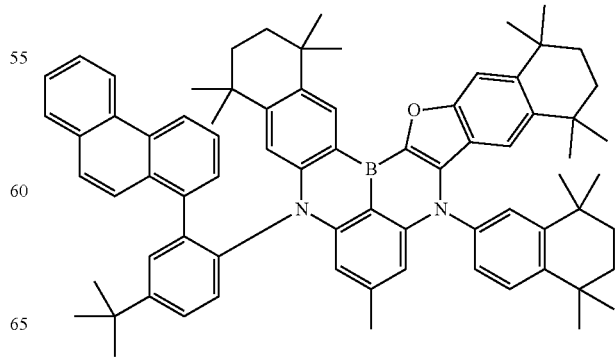 |

1823
-continued

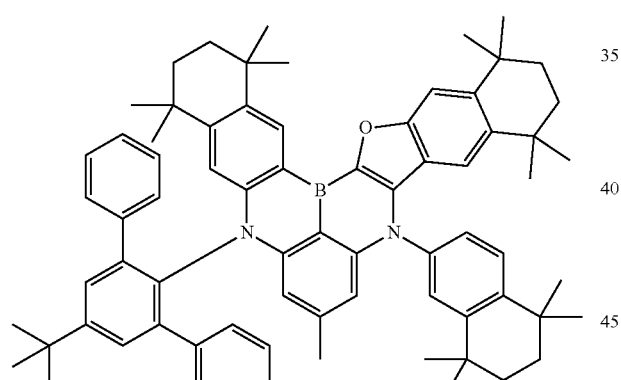
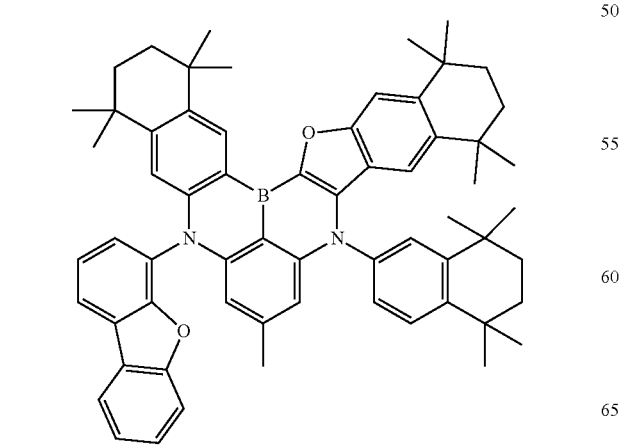
1824
-continued
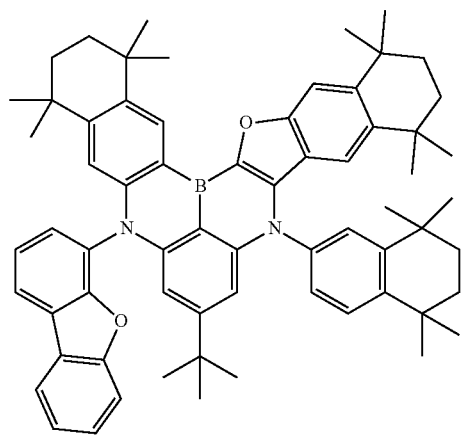
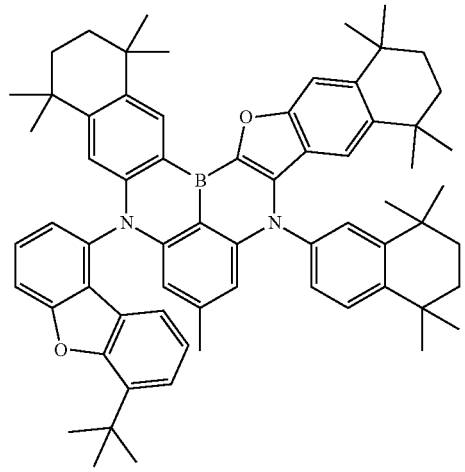
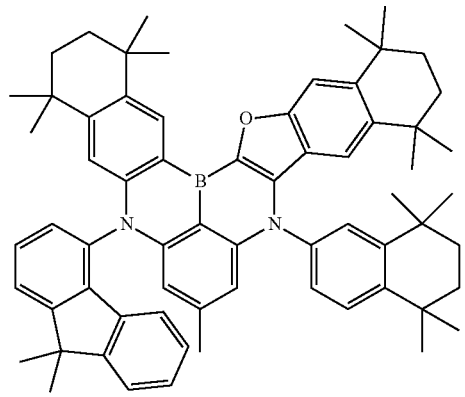
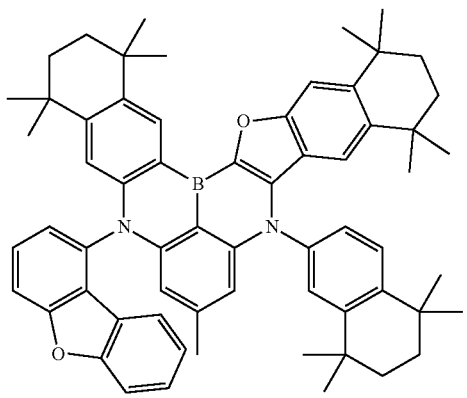

1825
-continued
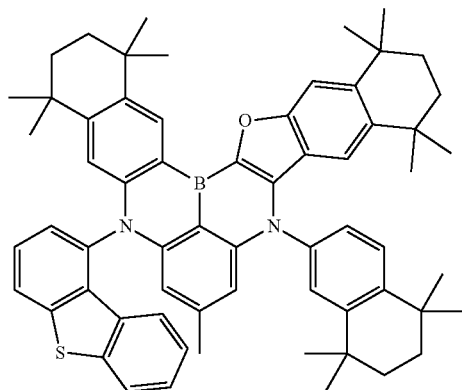
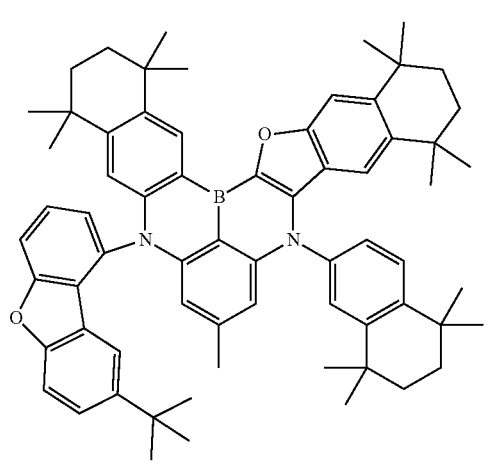
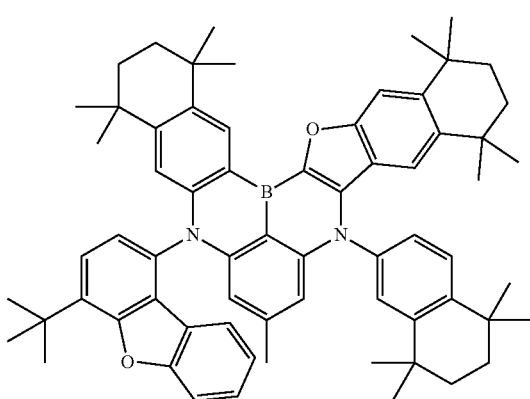
1826
-continued
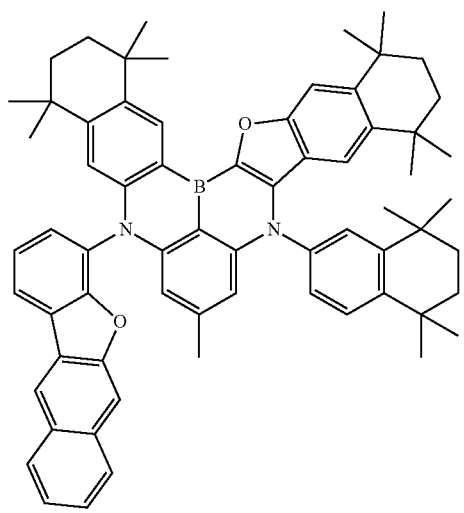
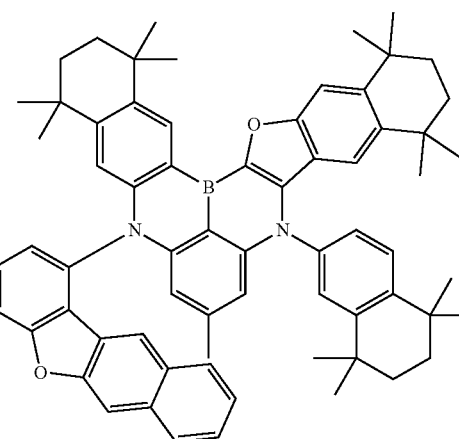
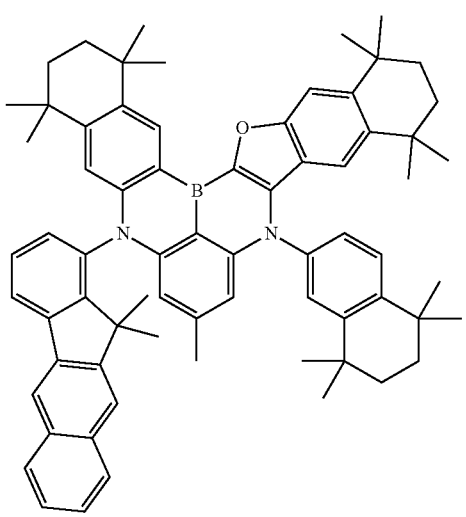

1827
-continued
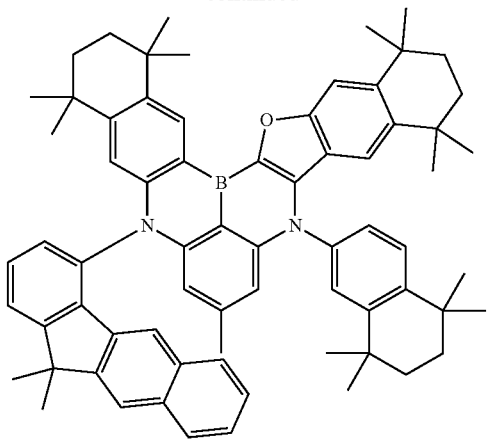
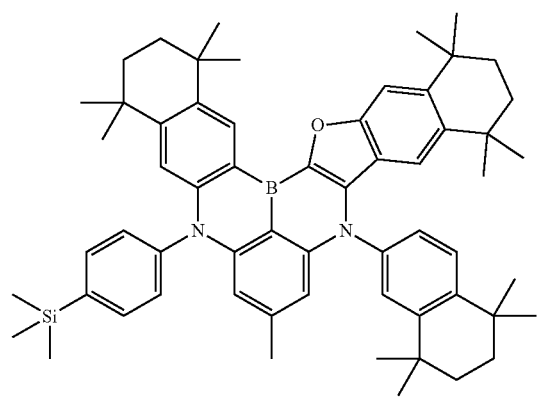
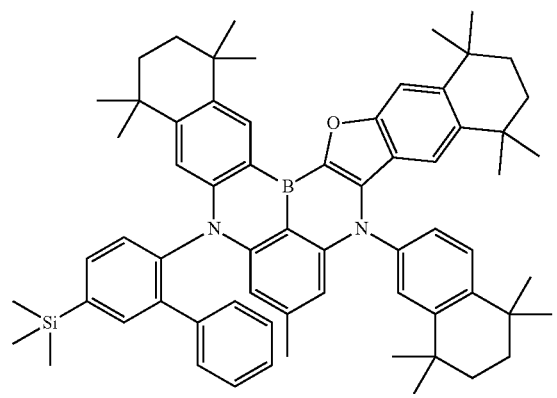
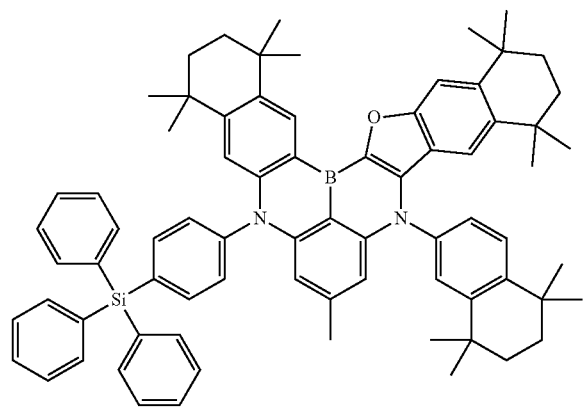
1828
-continued
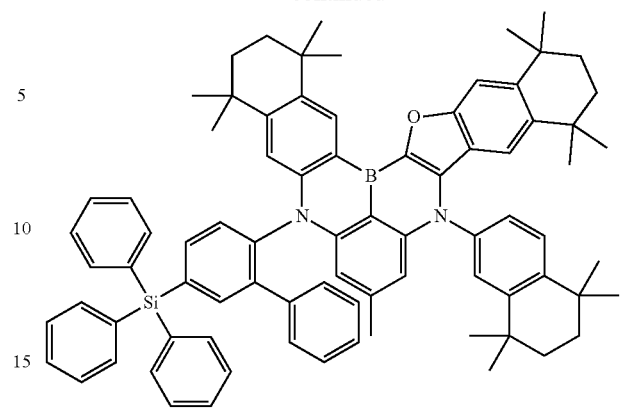
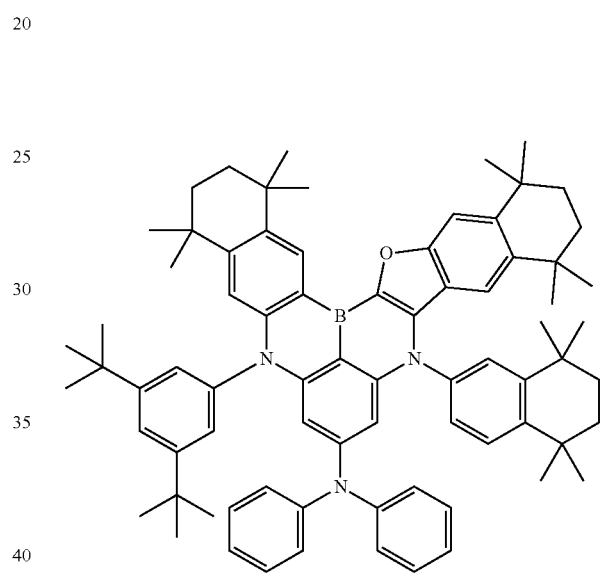
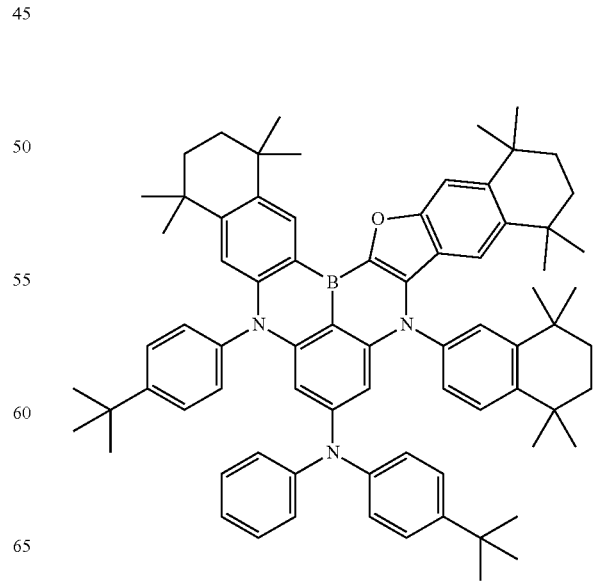

1829
-continued
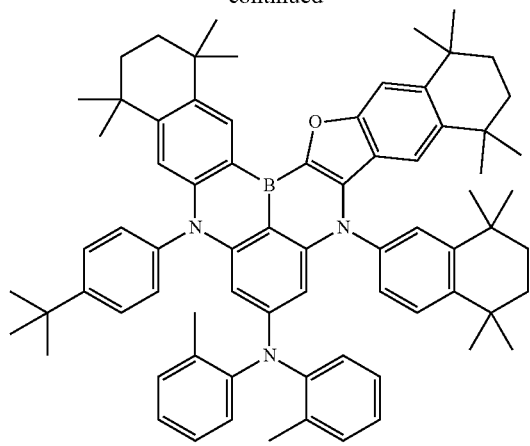
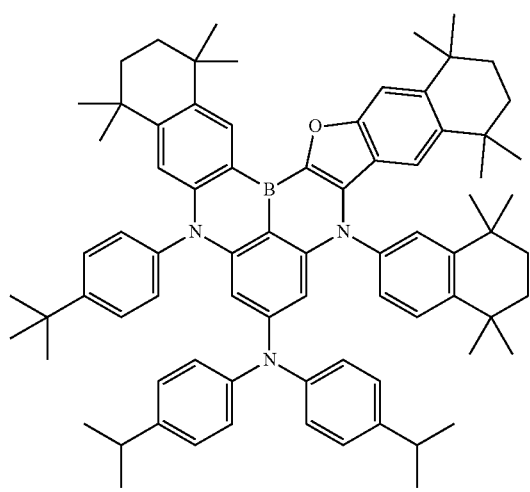
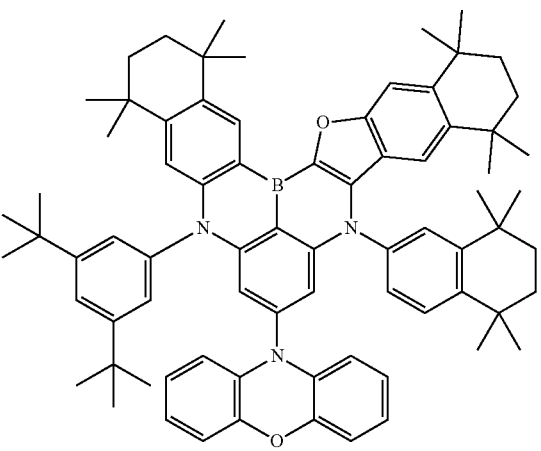
1830
-continued
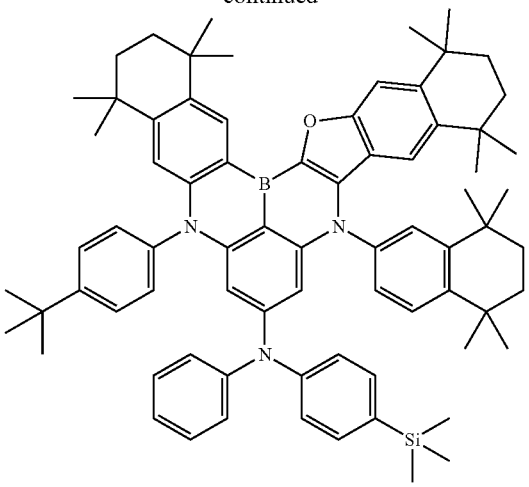
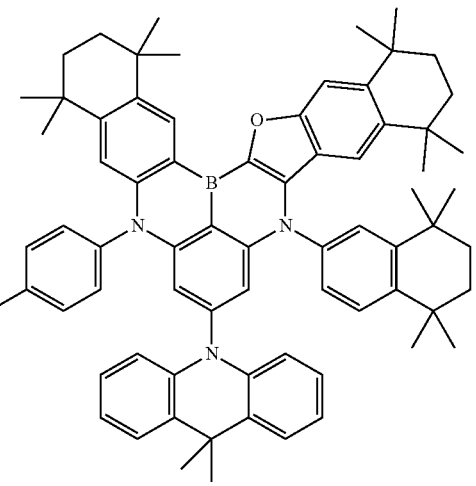
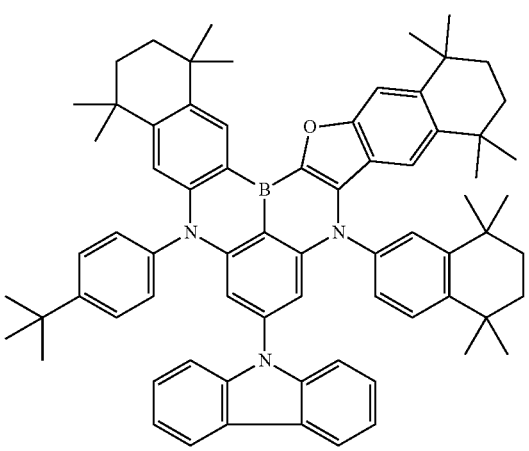

1831
-continued
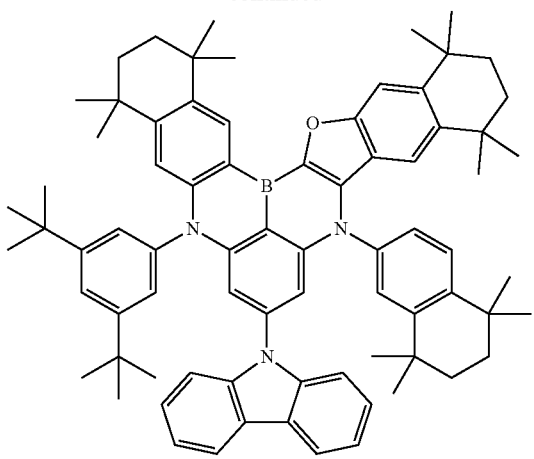
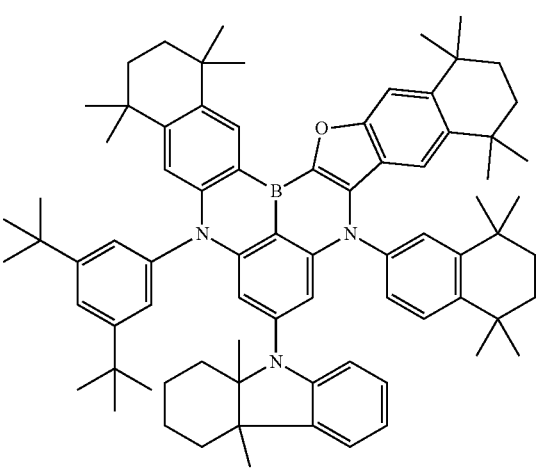
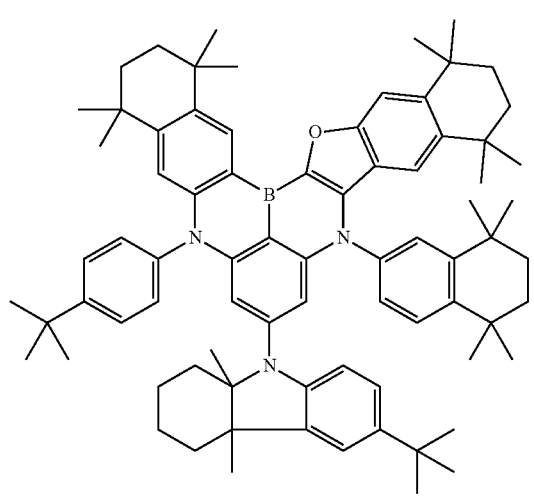
1832
-continued
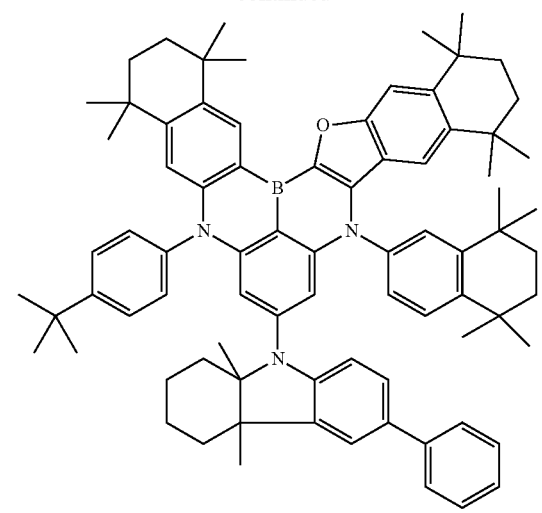
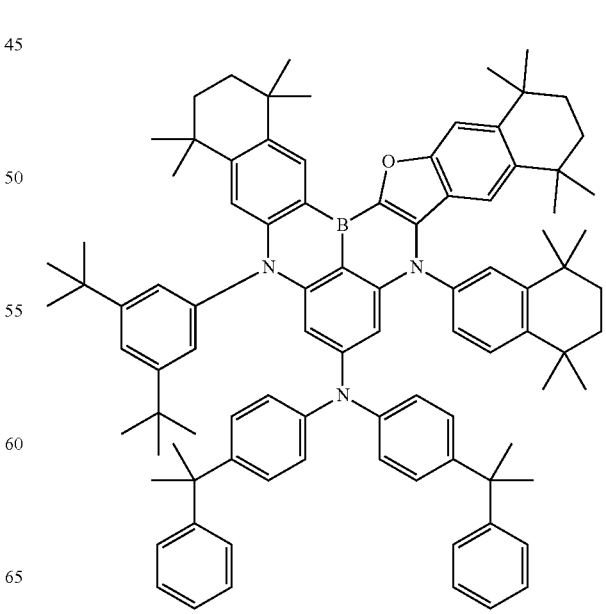

1833
-continued
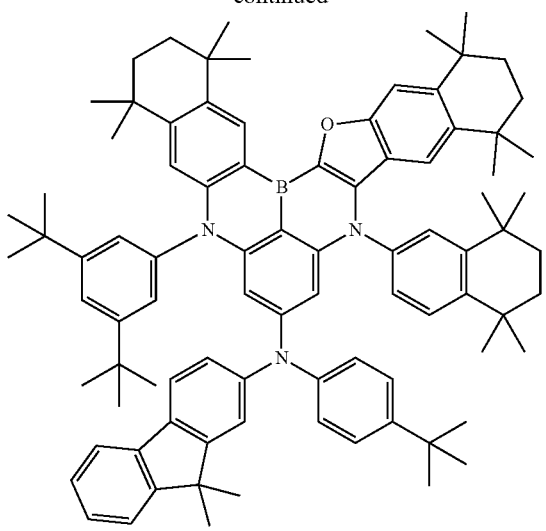
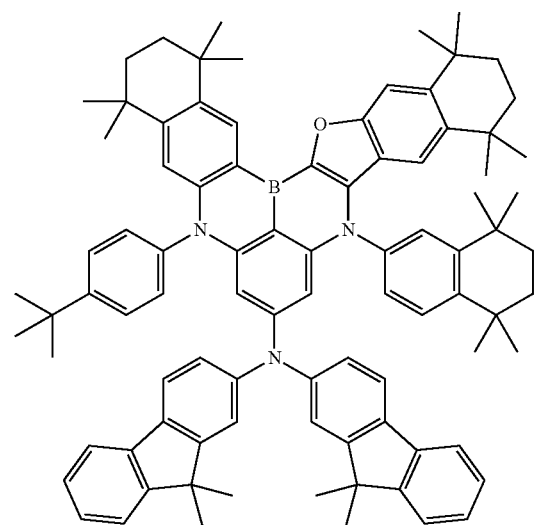
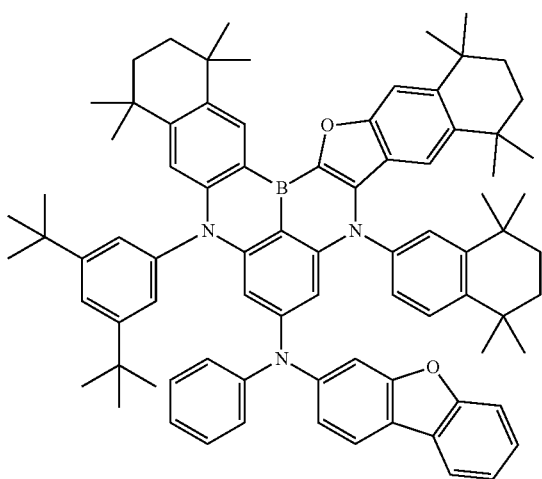
1834
-continued
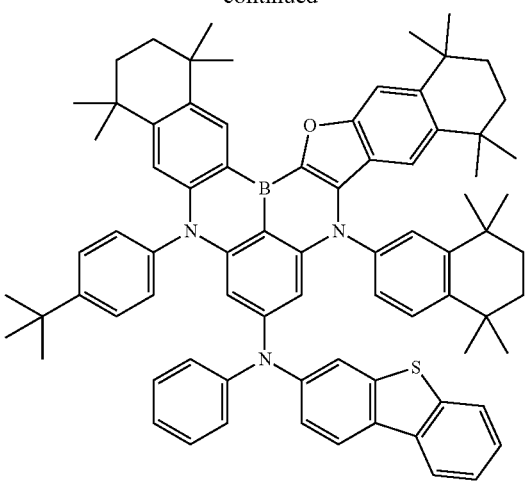
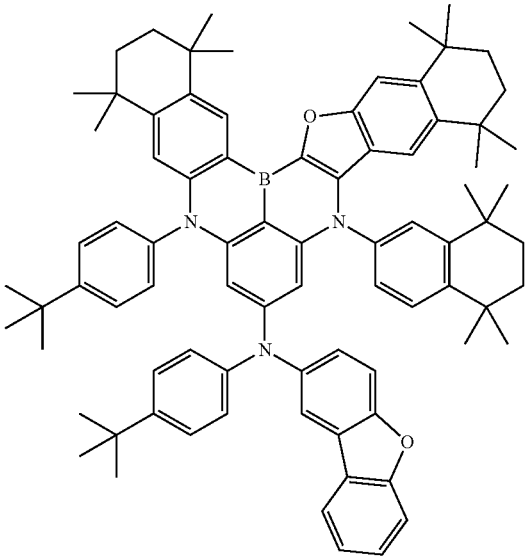
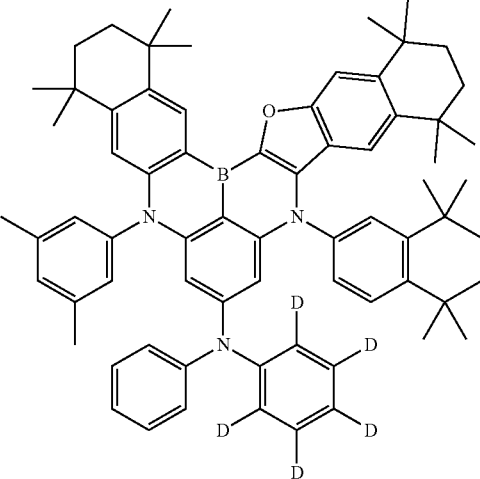

1835
-continued
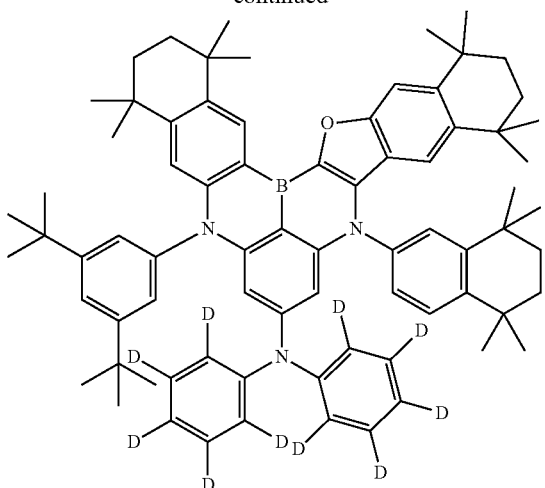
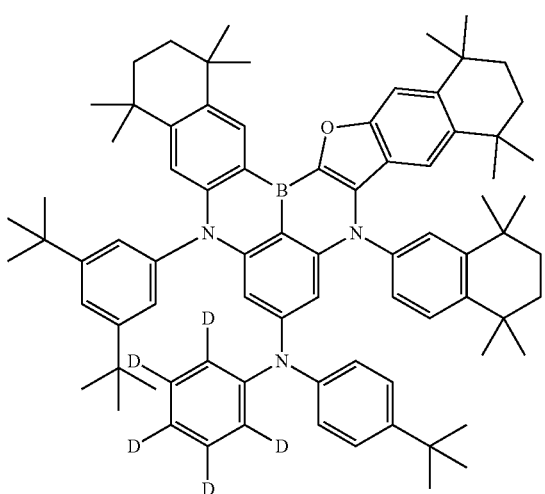
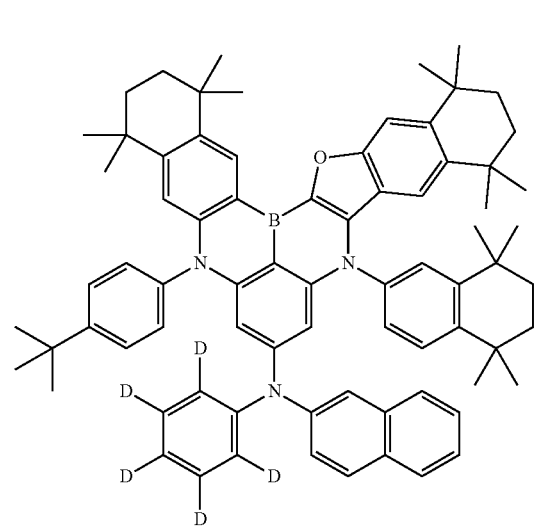
1836
-continued
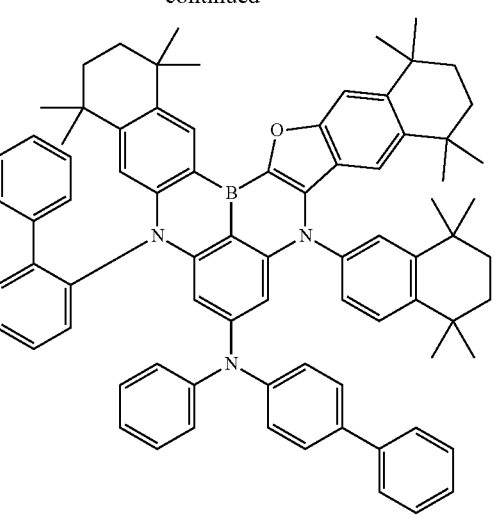
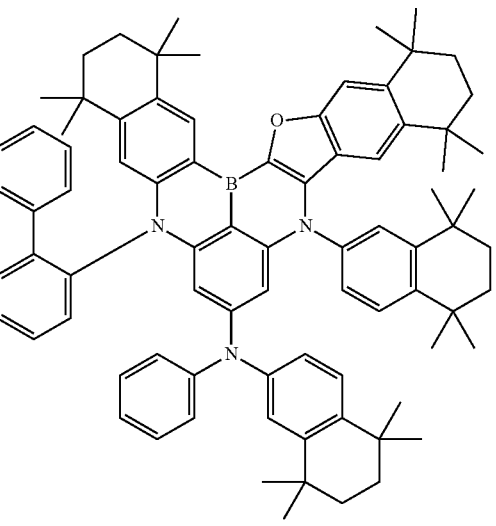

1837
-continued
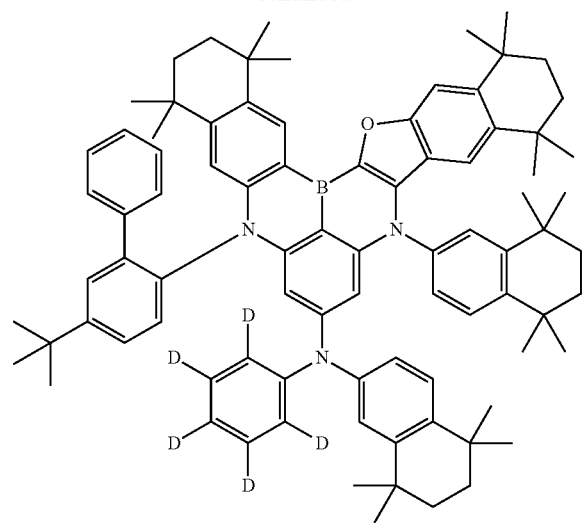
1838
-continued
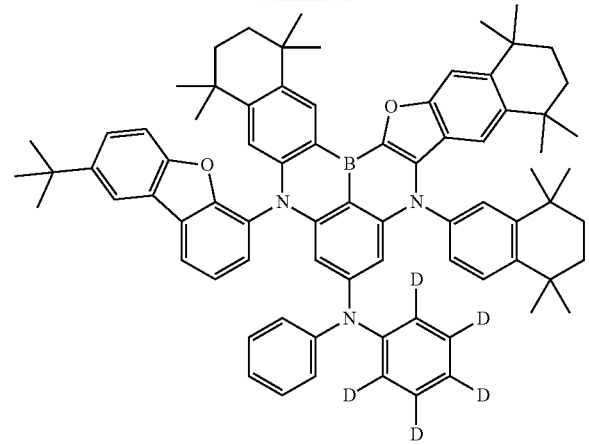
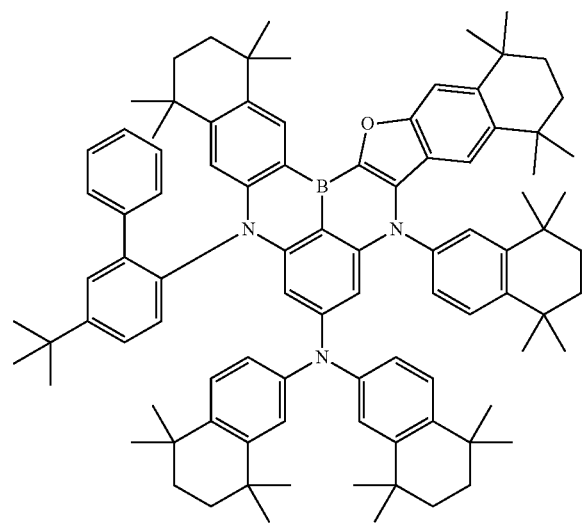
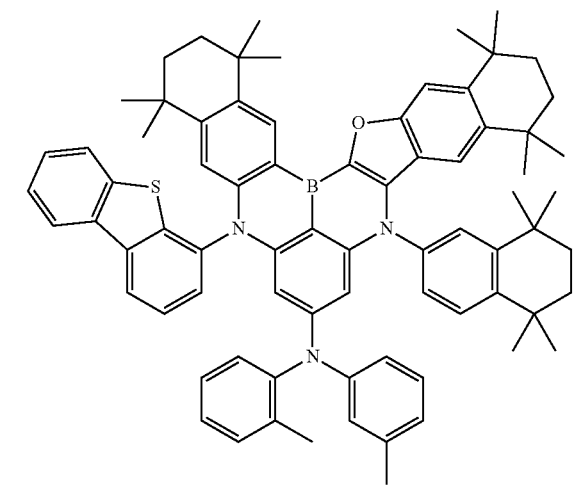
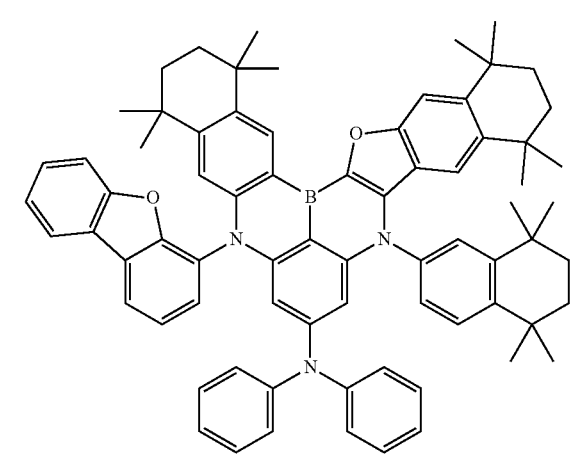
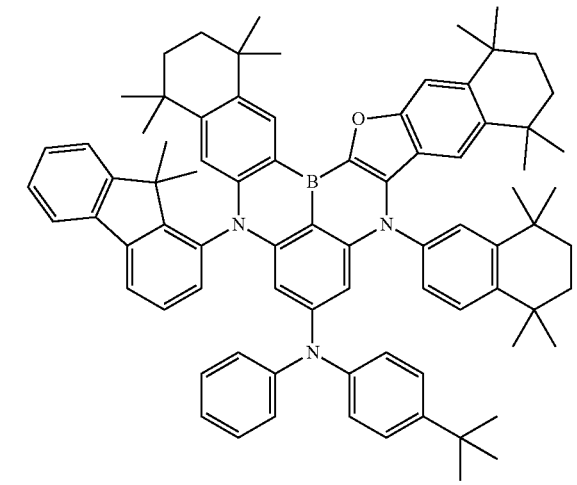

1839
-continued
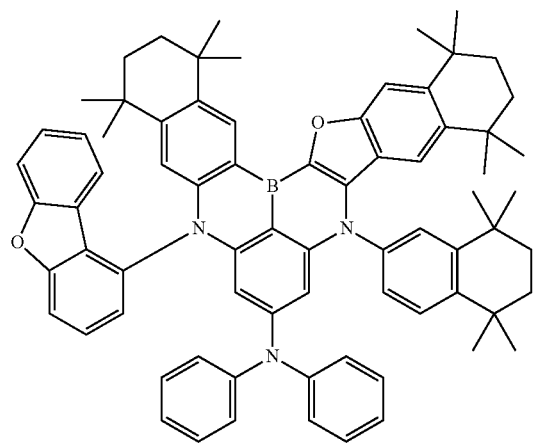
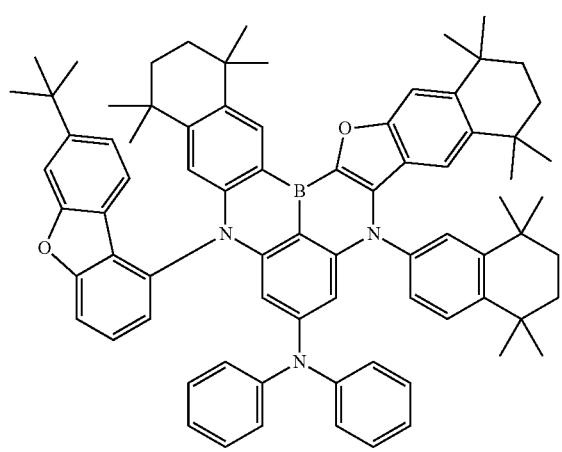
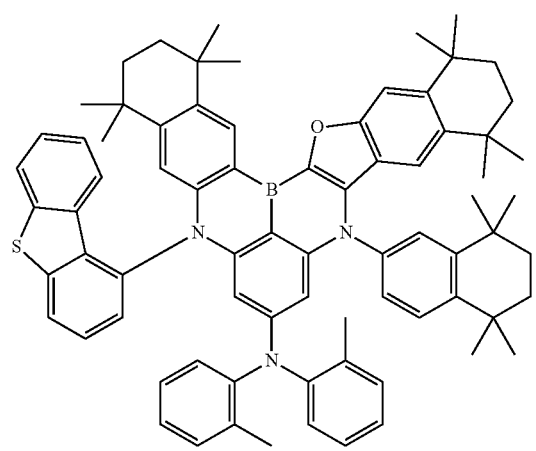
1840
-continued
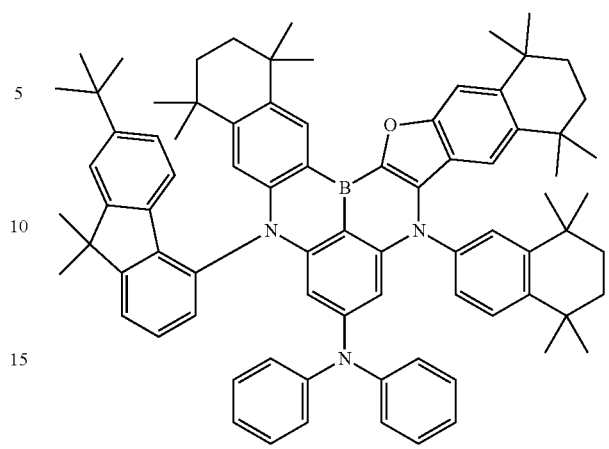
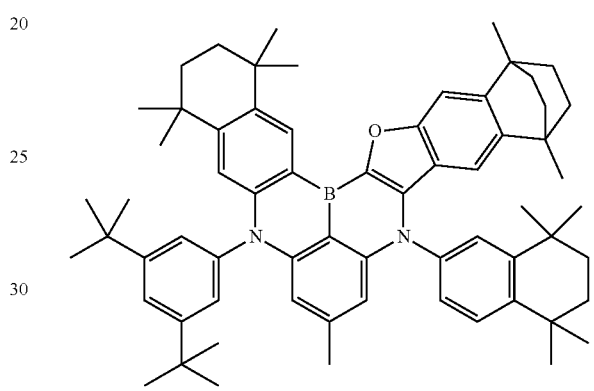
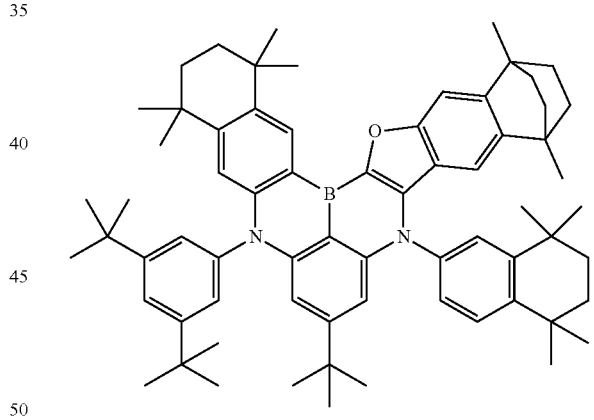
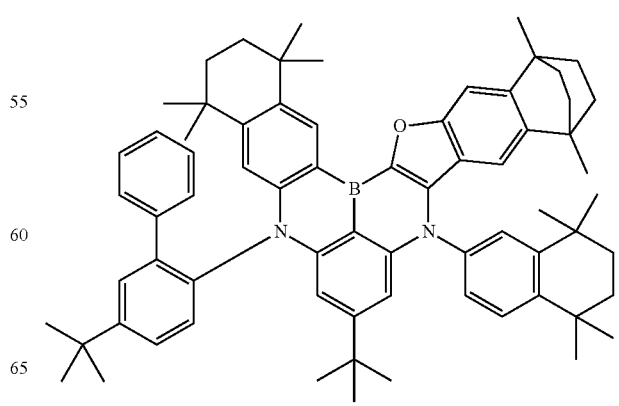

1841
-continued
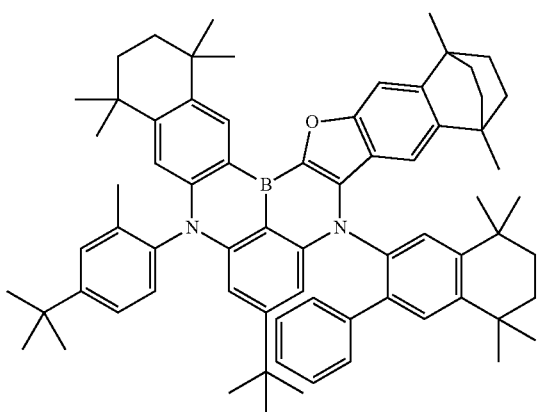
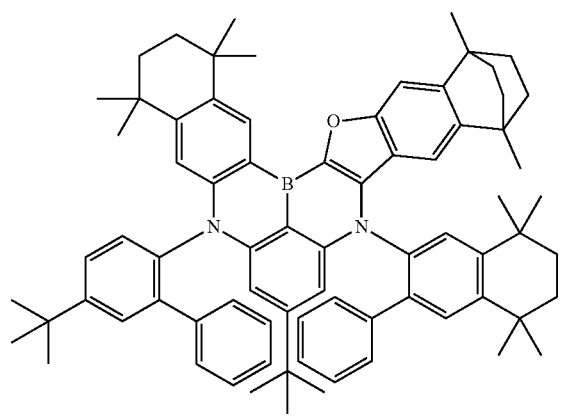
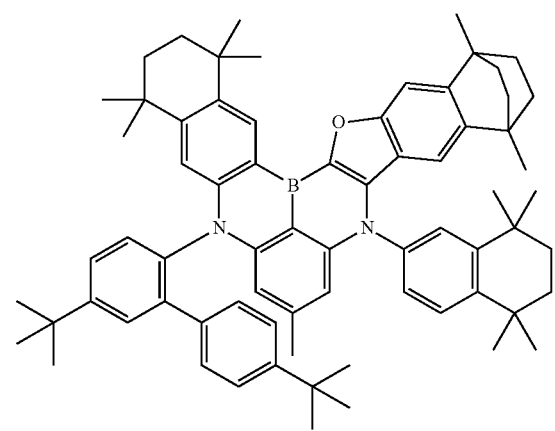
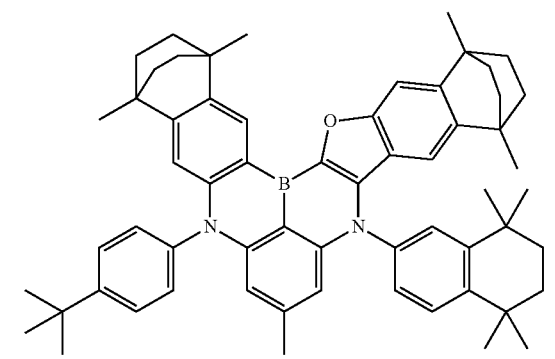
1842
-continued
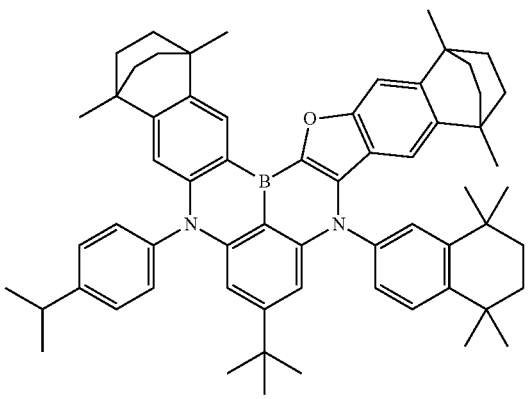
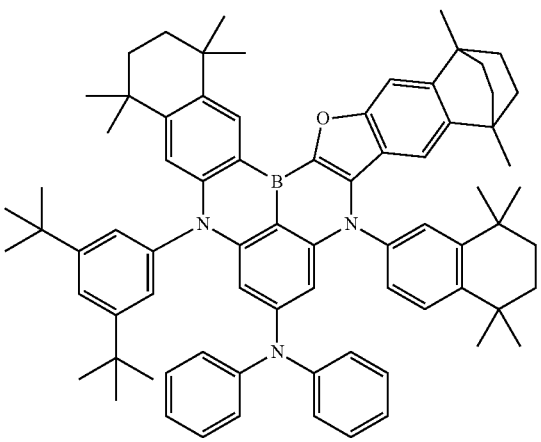

1843
-continued
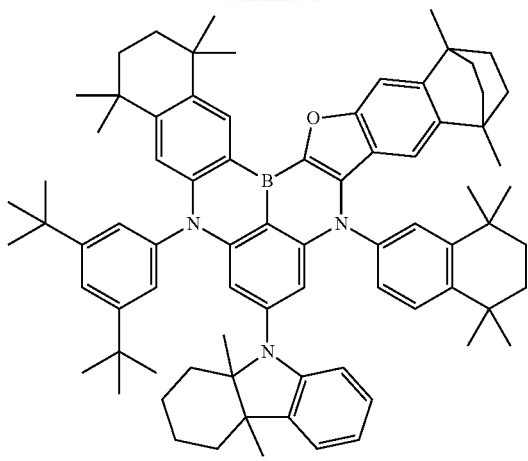
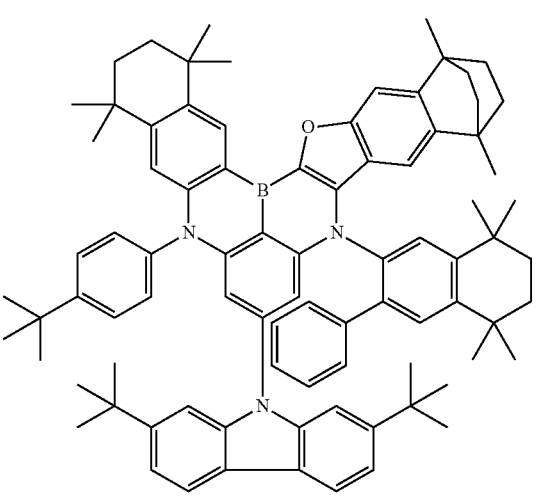
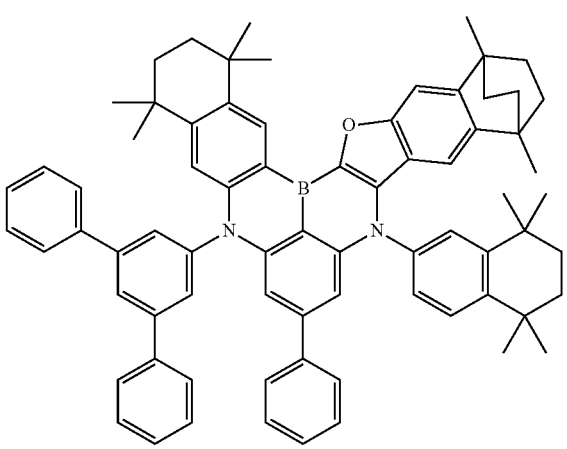
1844
-continued
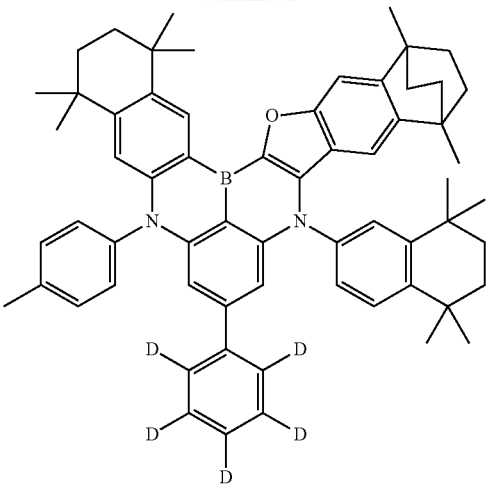
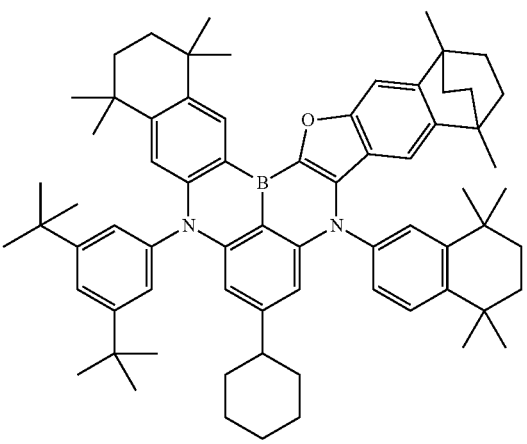
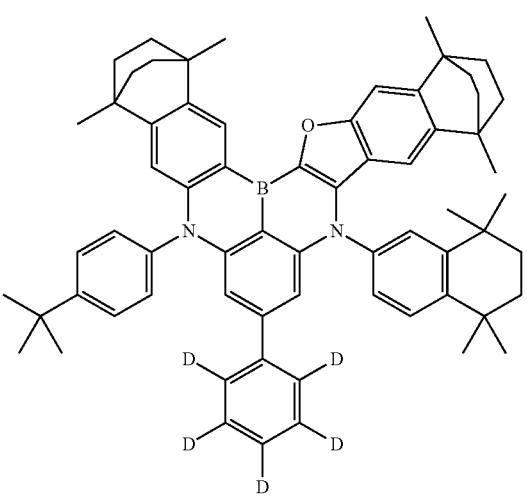

1845
-continued
1846
-continued
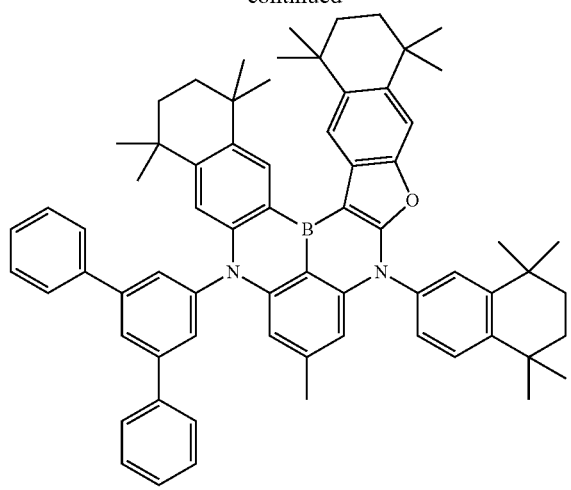
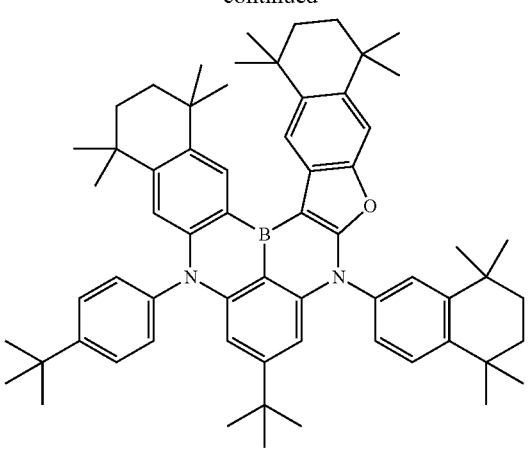
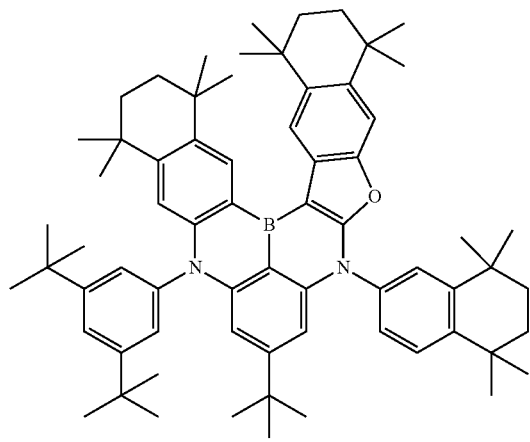
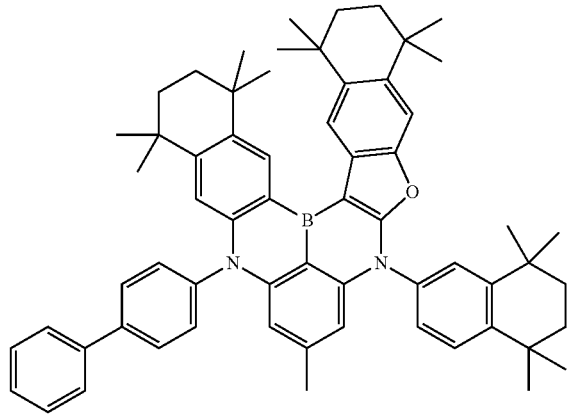
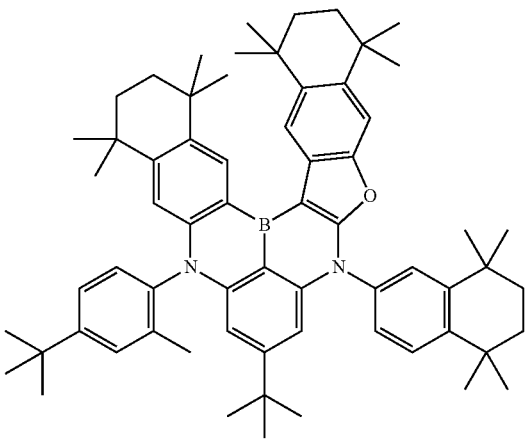

-continued
1847
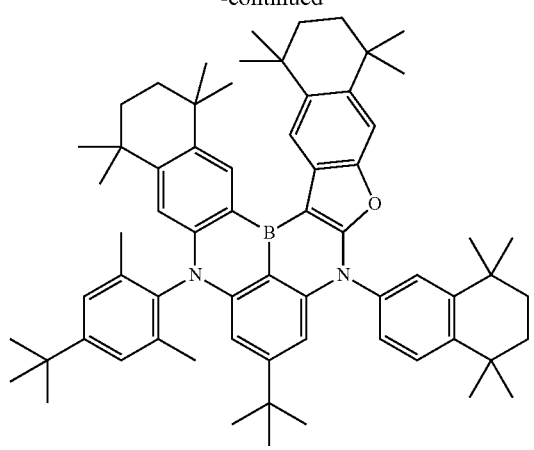
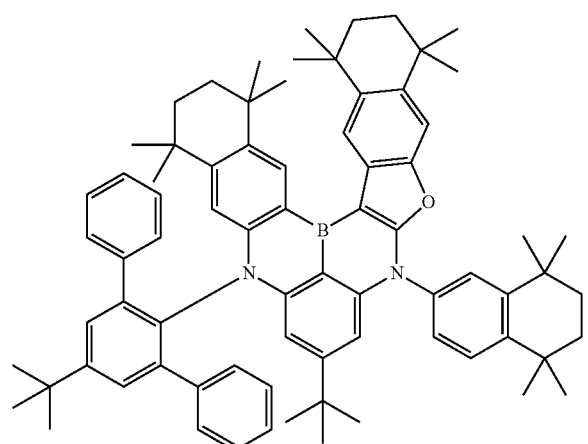
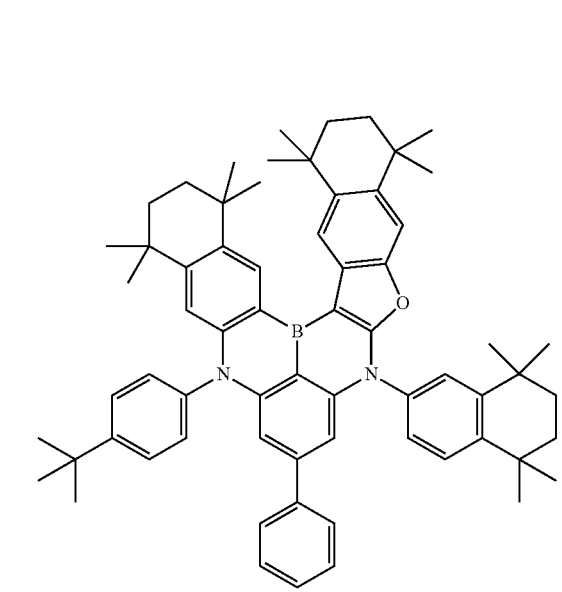
-continued
1848
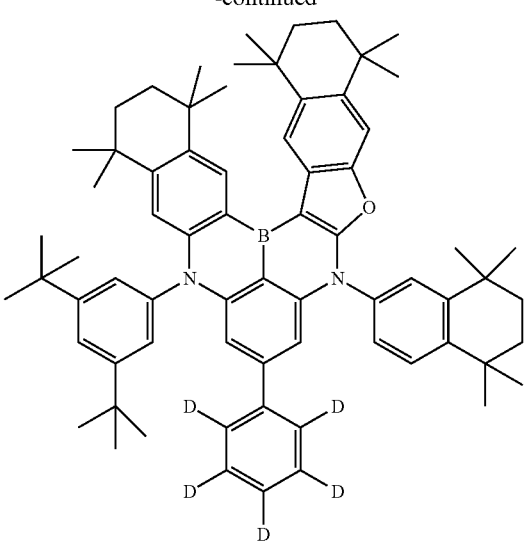
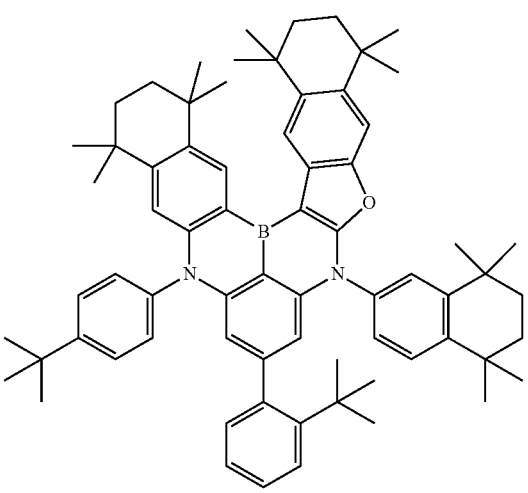
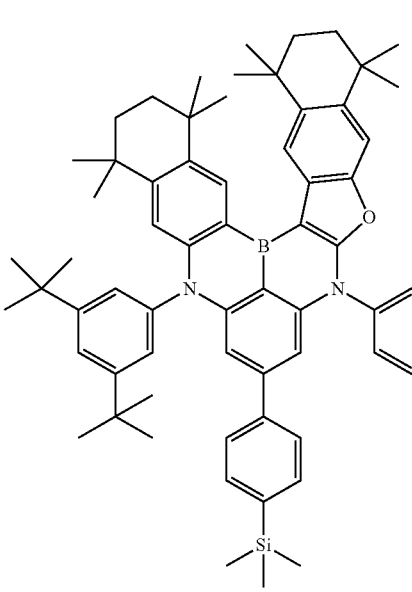

1849
-continued
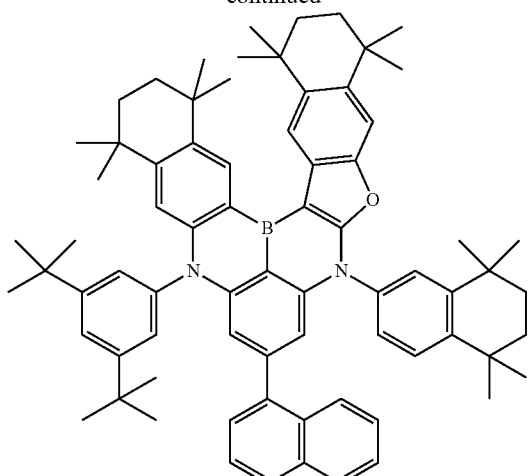
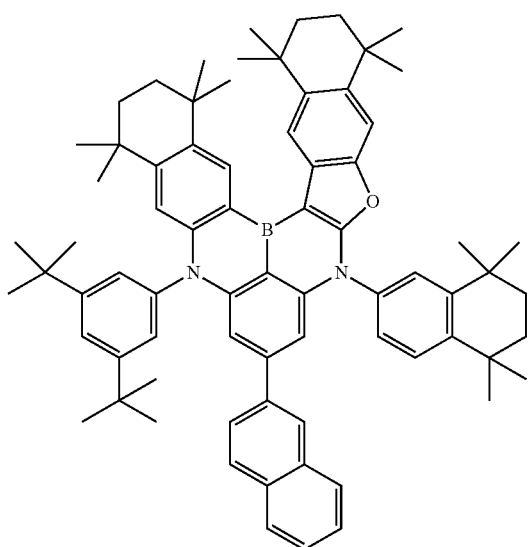
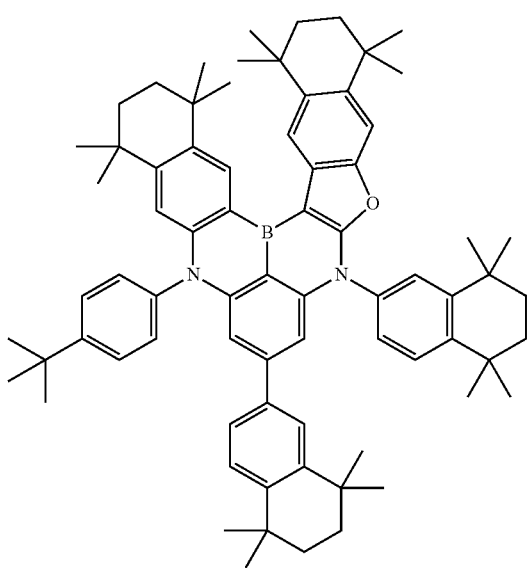
1850
-continued
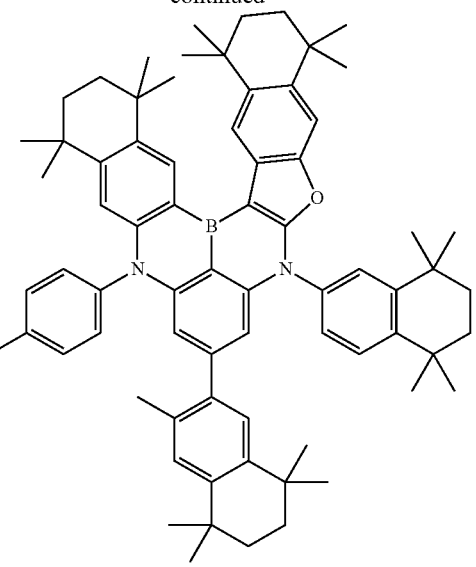
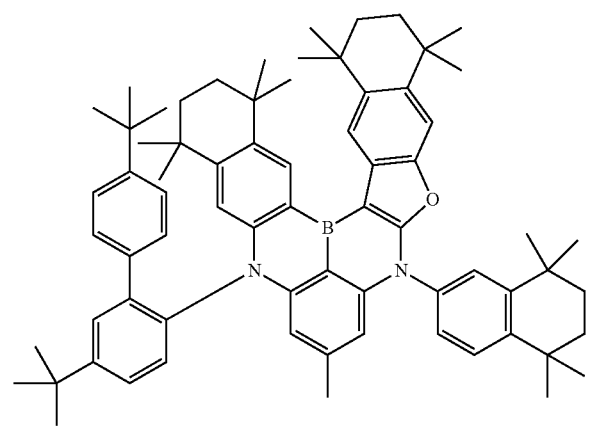
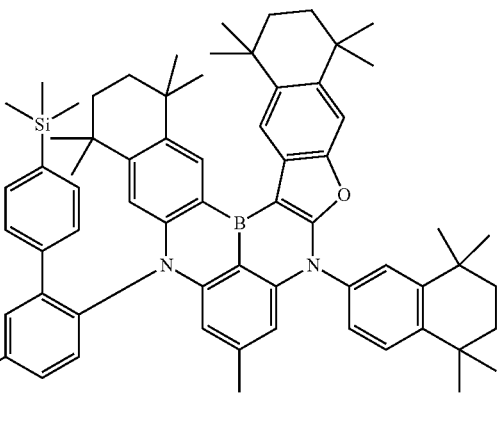

1851
-continued
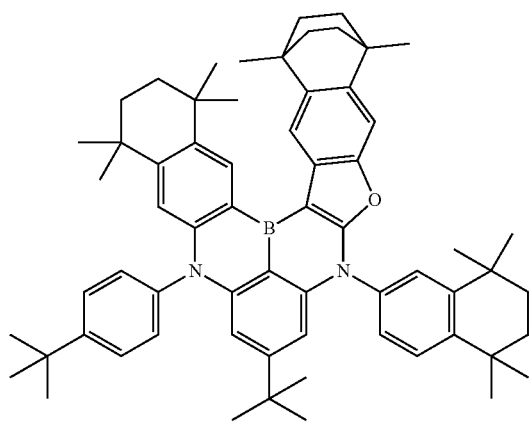
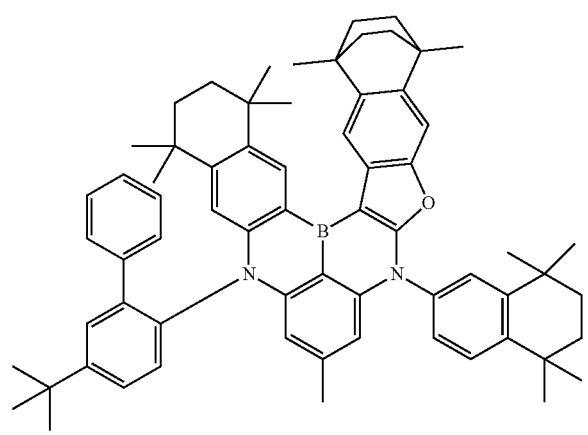
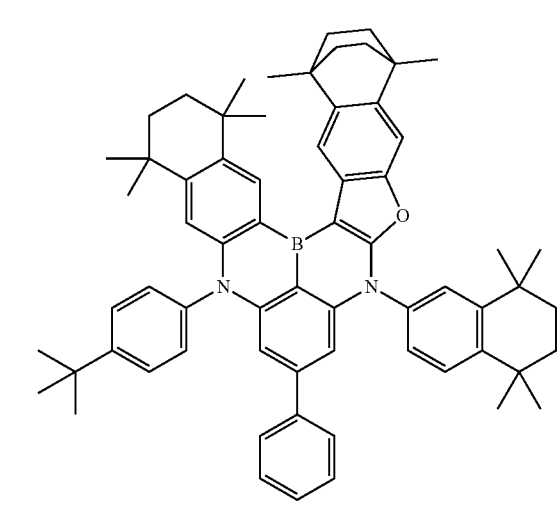
1852
-continued
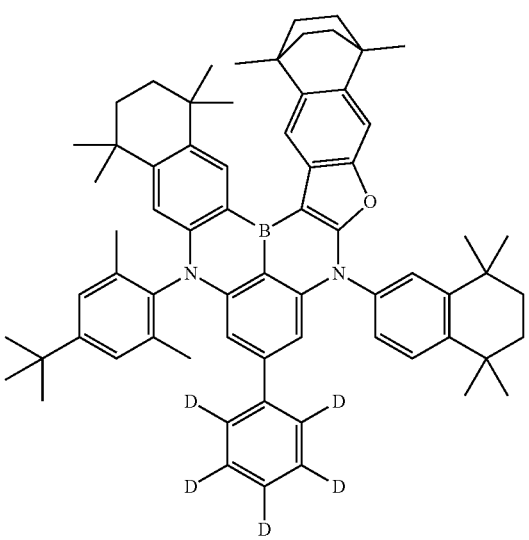
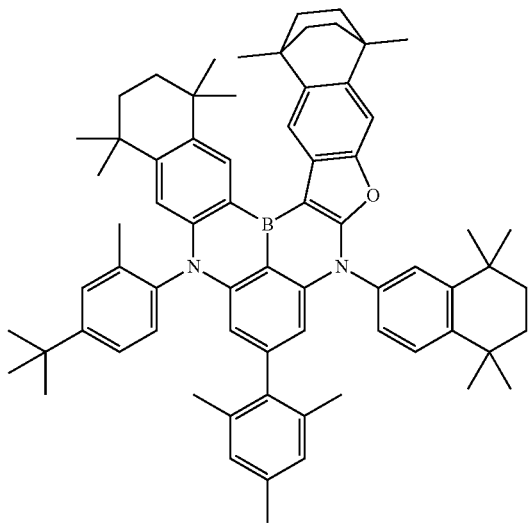
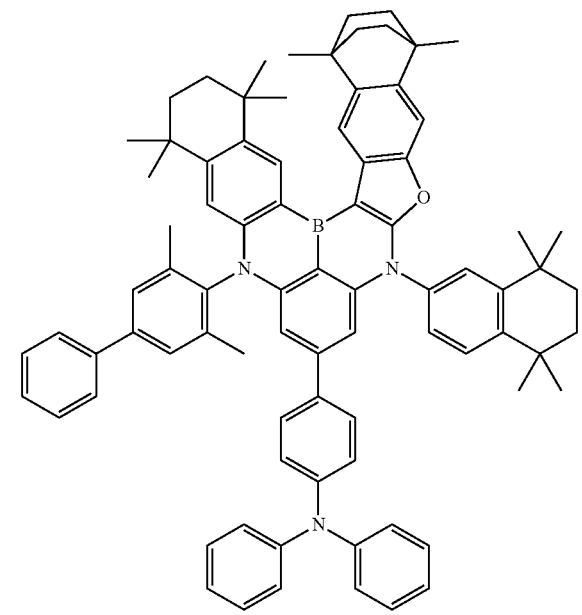

-continued
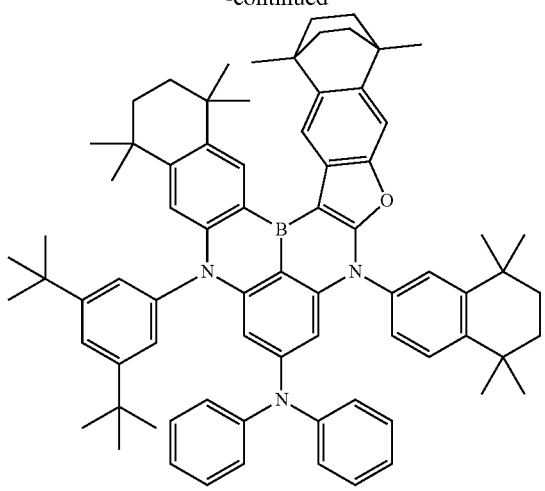
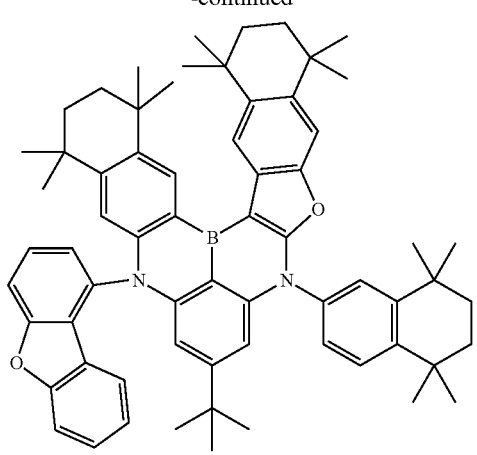
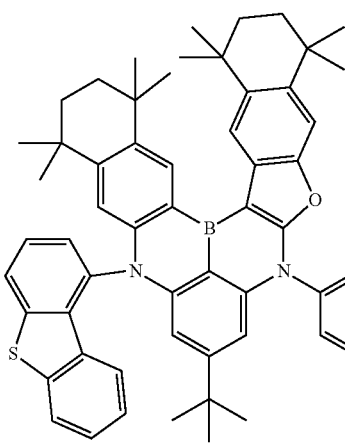
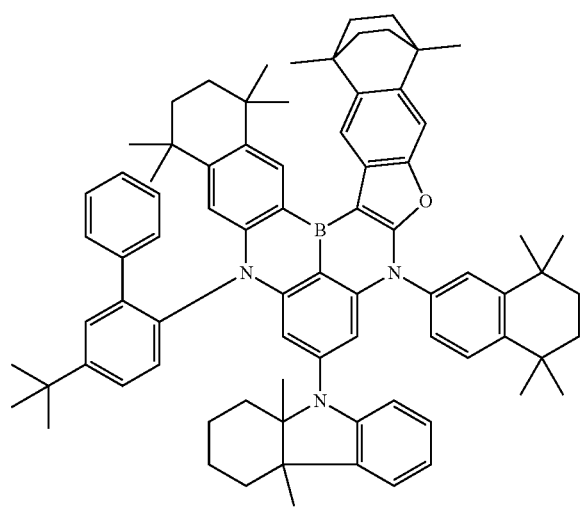
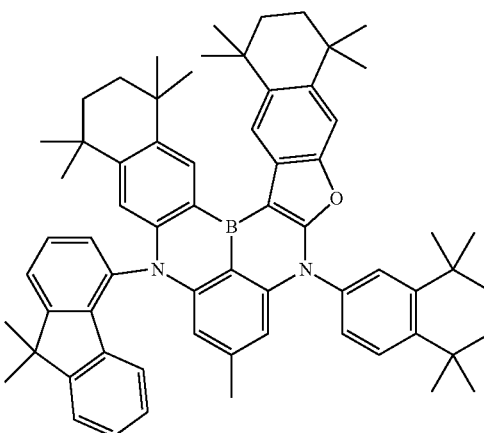

1855
-continued
1856
-continued
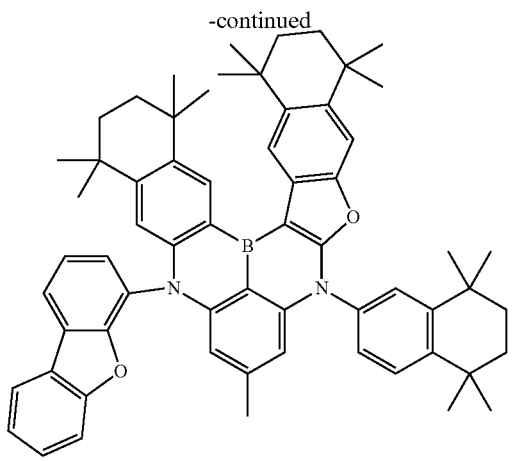
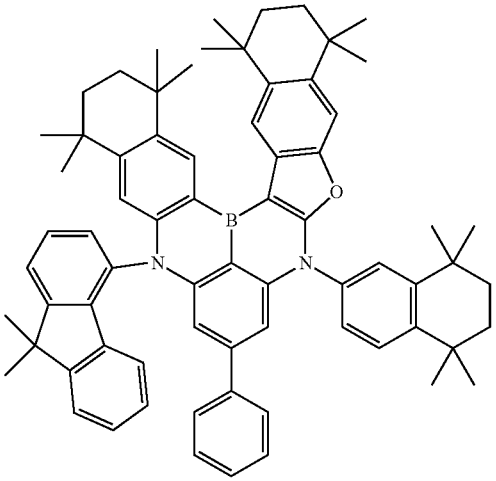
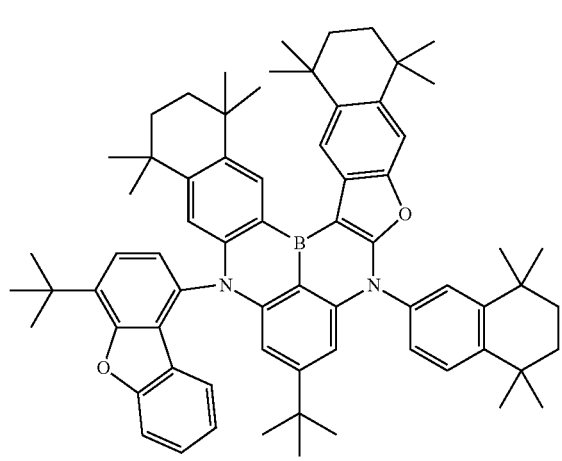
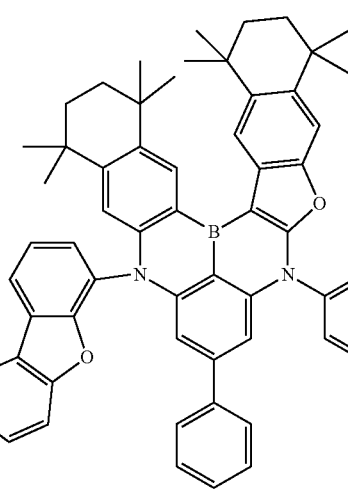
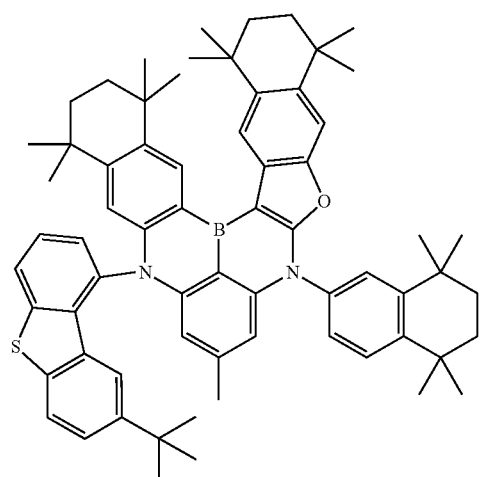
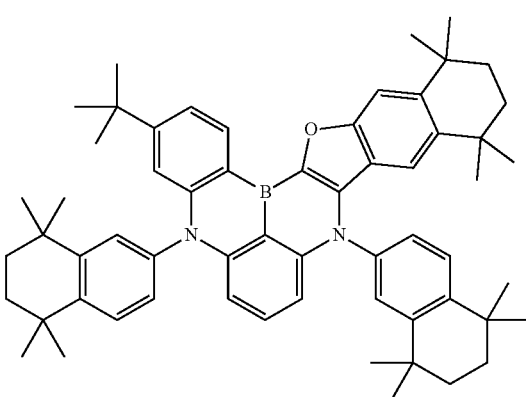

1857
-continued
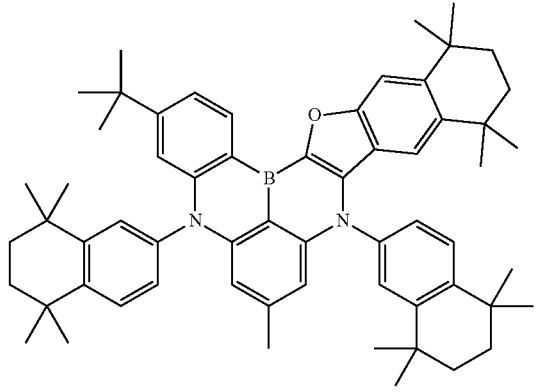
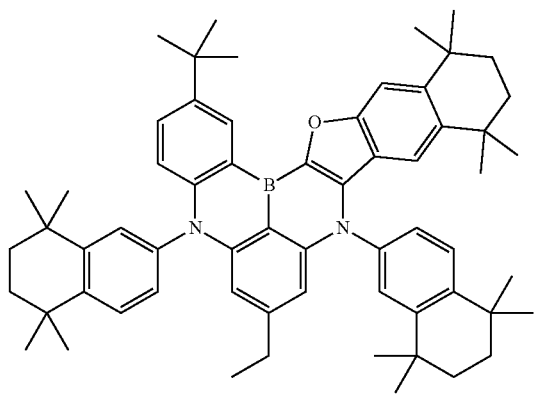
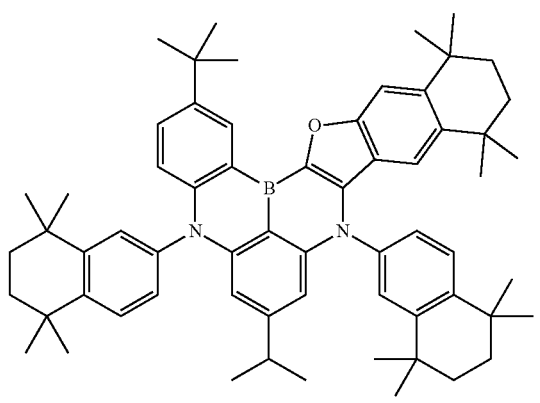
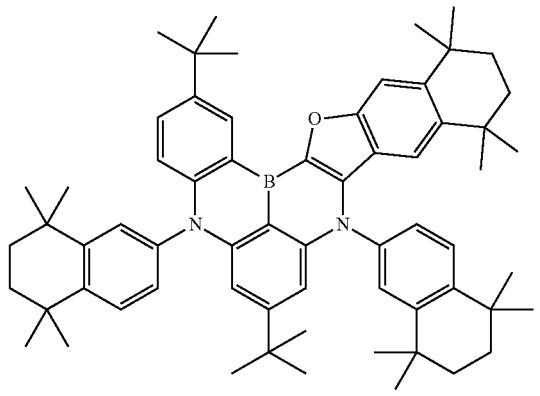
1858
-continued
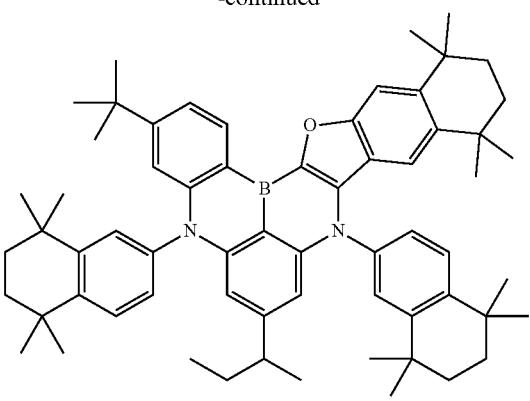
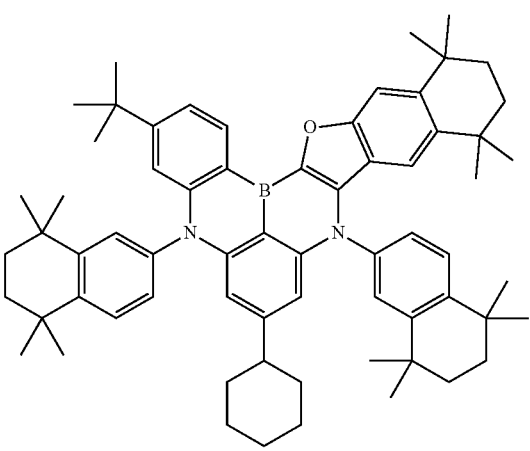
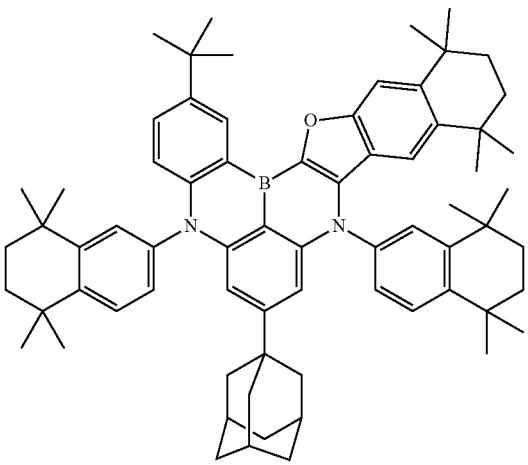
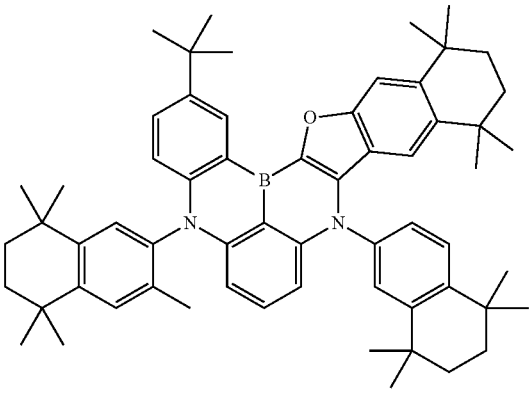

1859
-continued
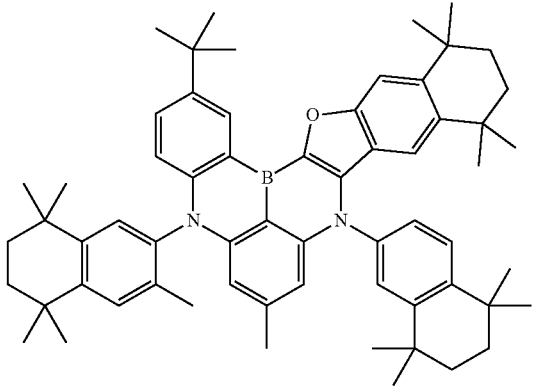
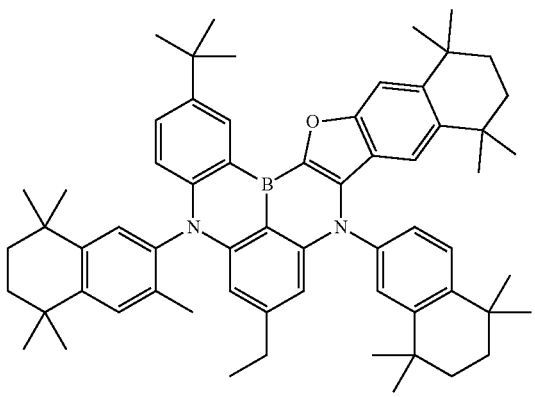
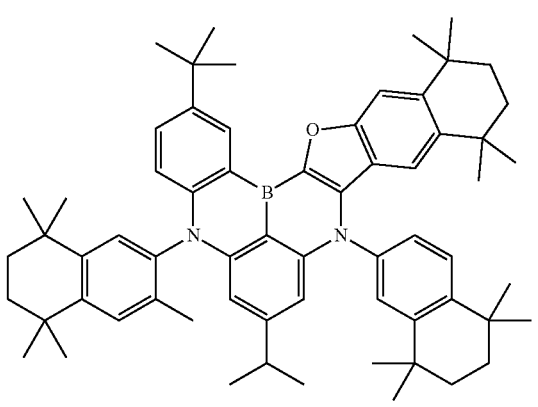
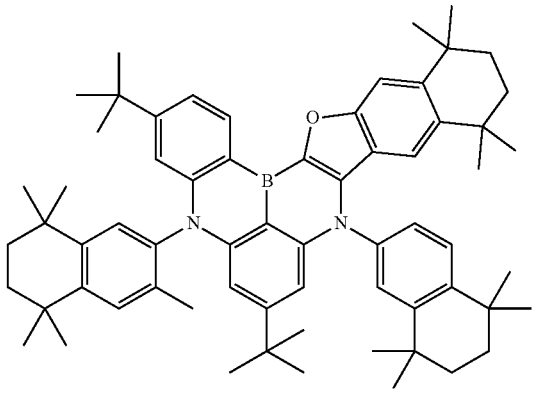
1860
-continued
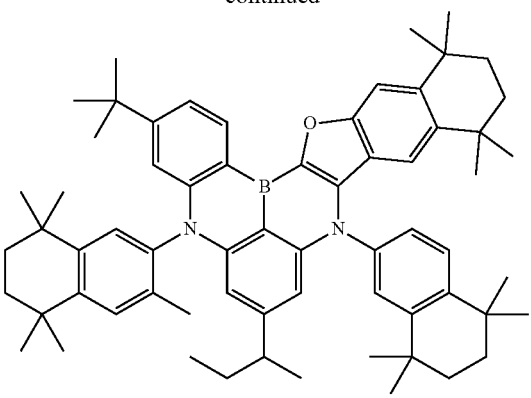
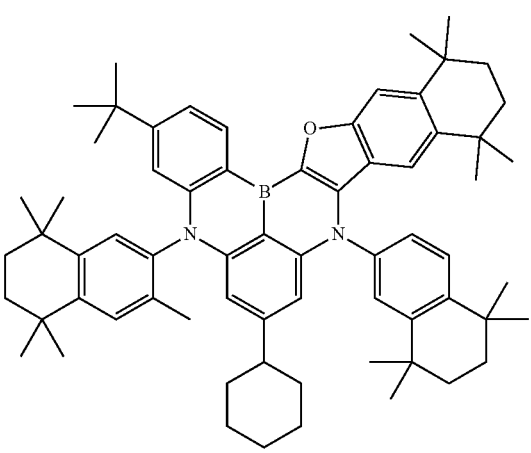
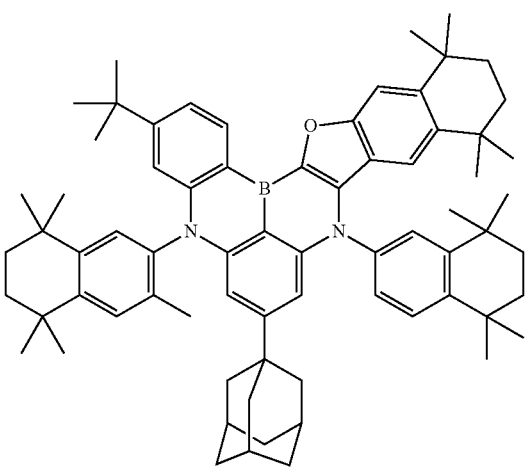
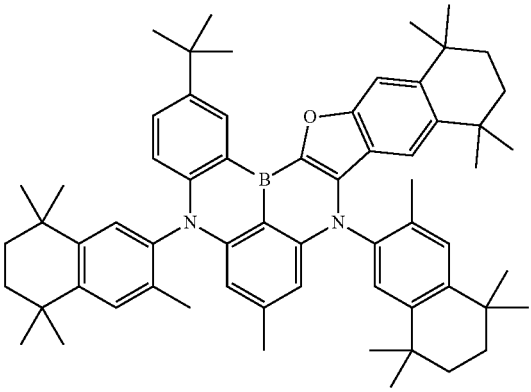

| 1861 -continued | 1862 -continued |
|---|---|
| 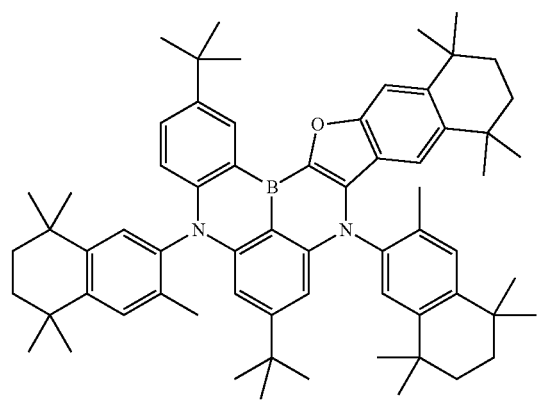 | 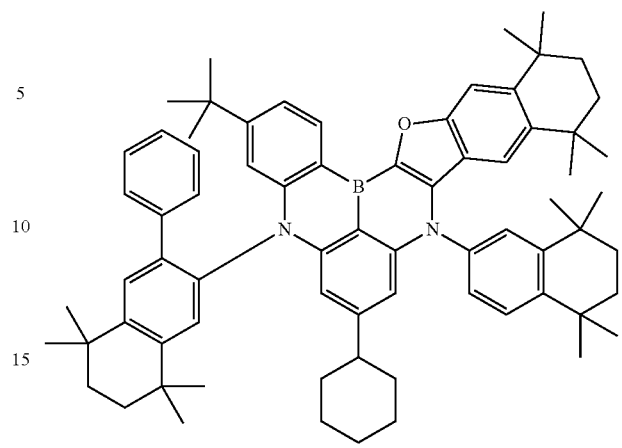 |
| 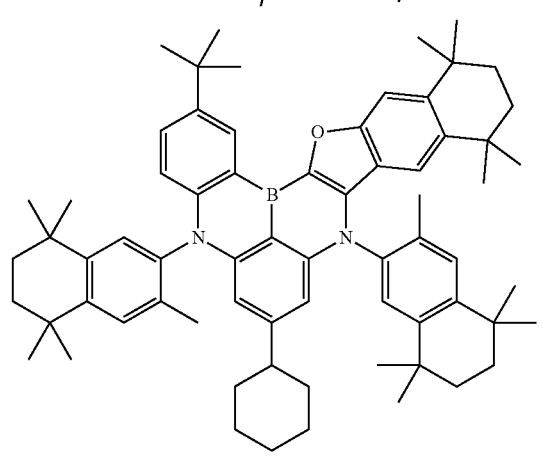 | 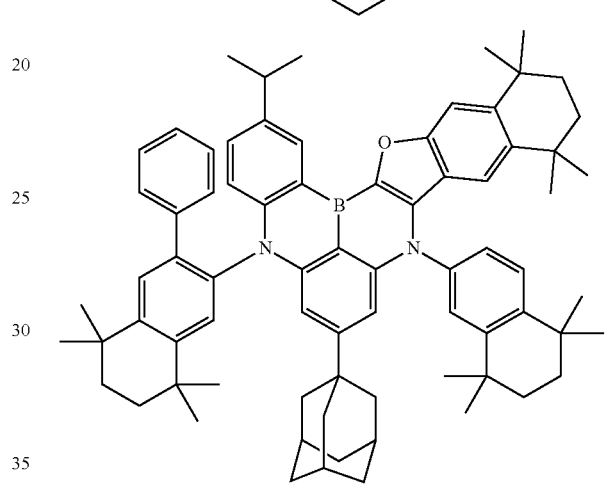 |
| 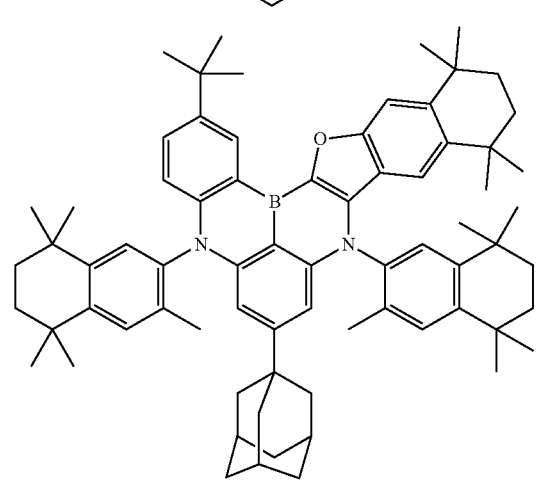 | 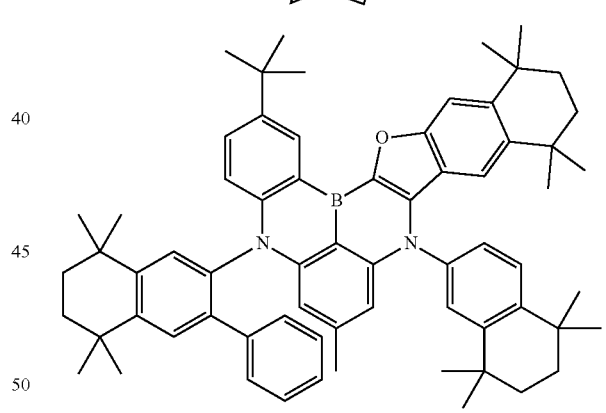 |
| 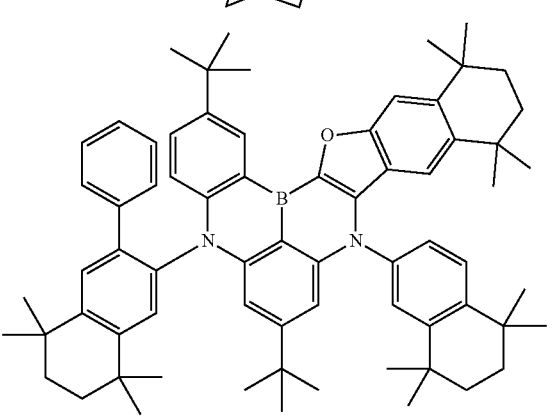 | 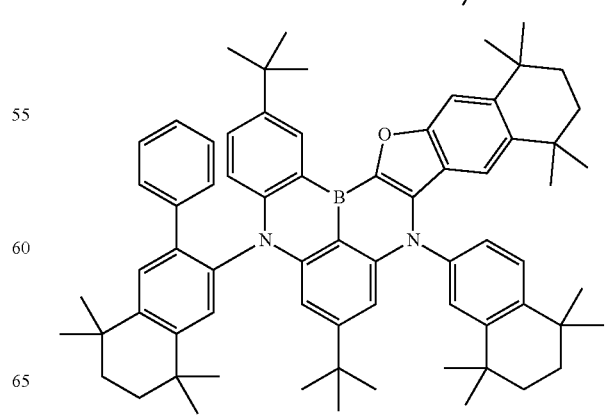 |

1863
-continued
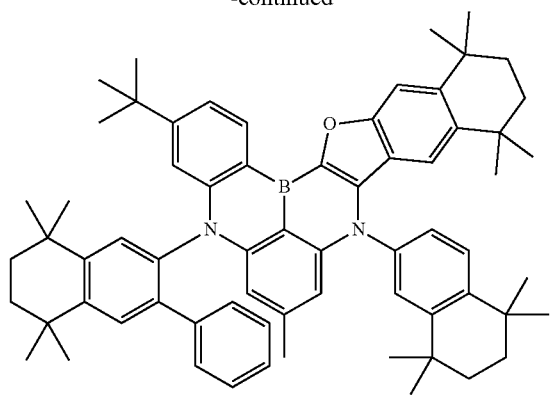
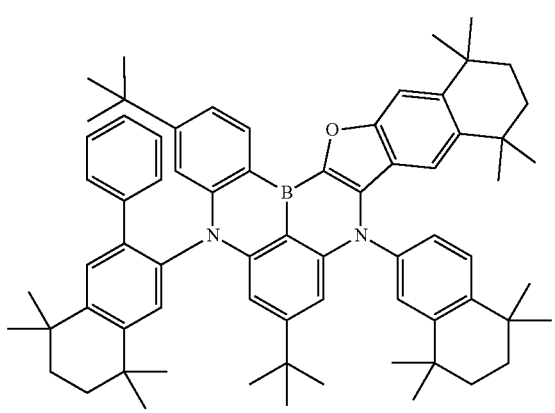
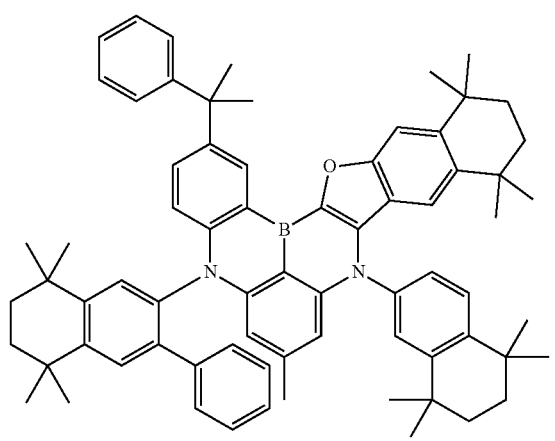
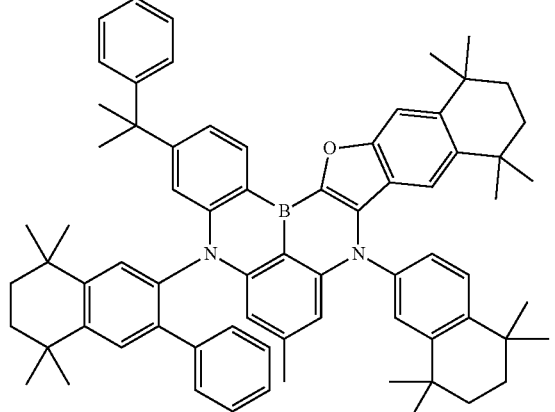
1864
-continued
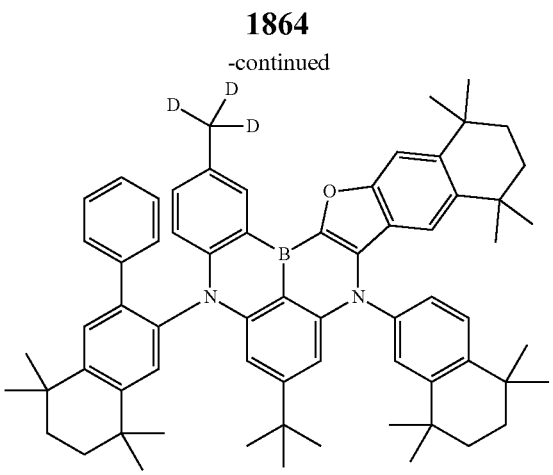
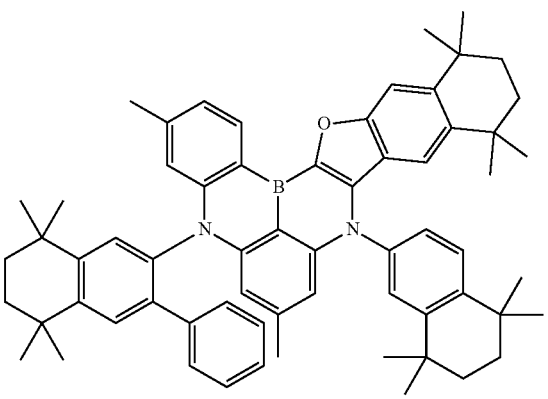
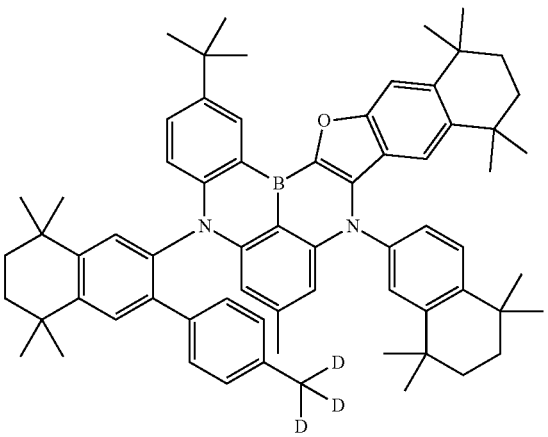
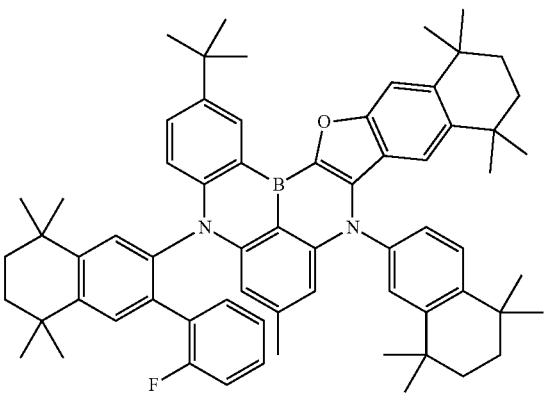

1865
-continued
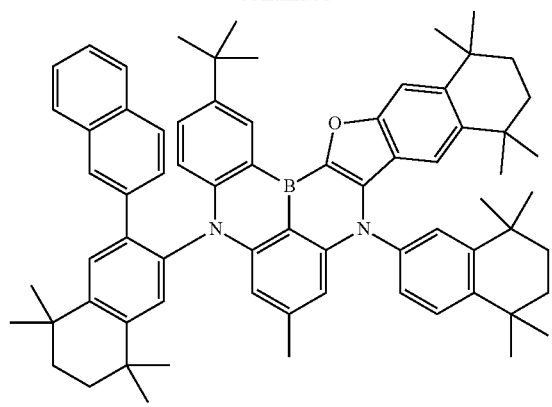
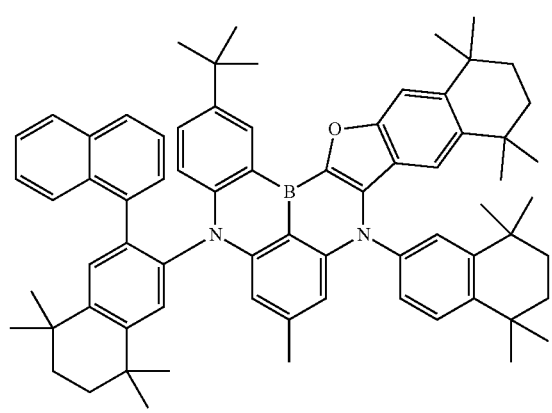
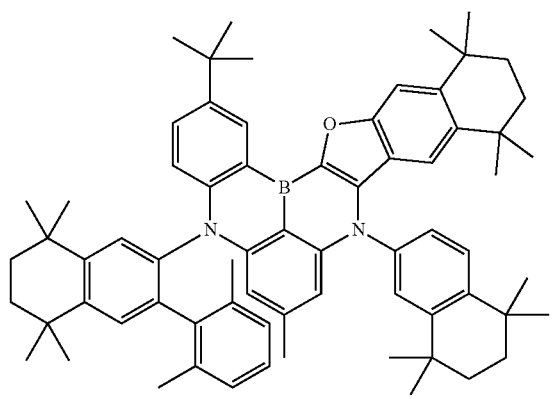
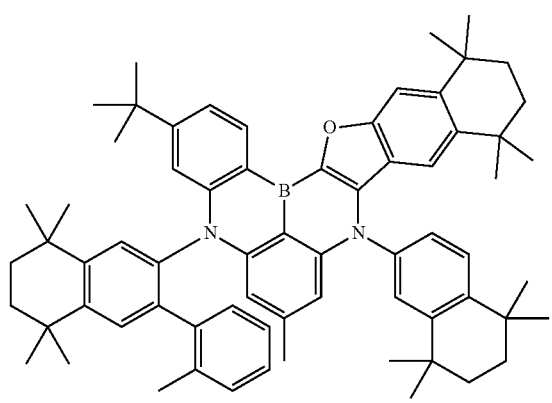
1866
-continued
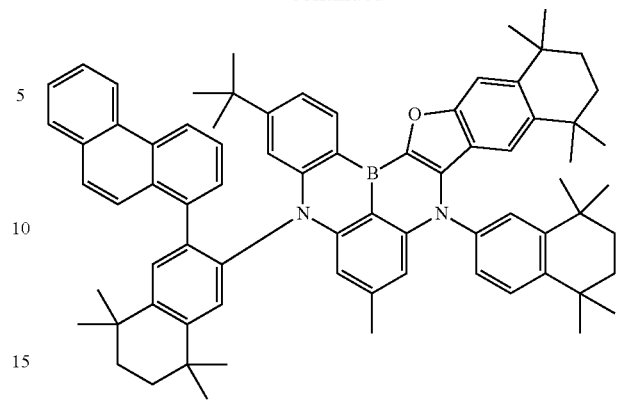
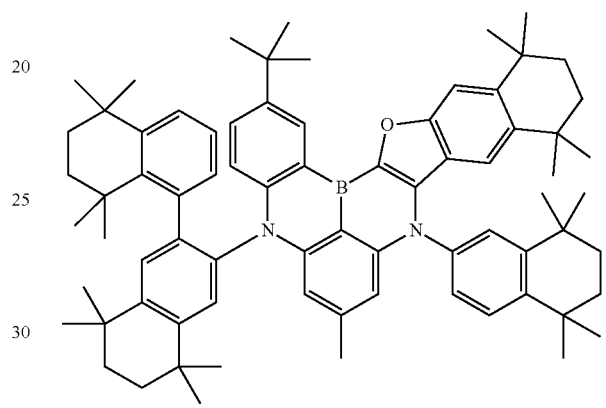
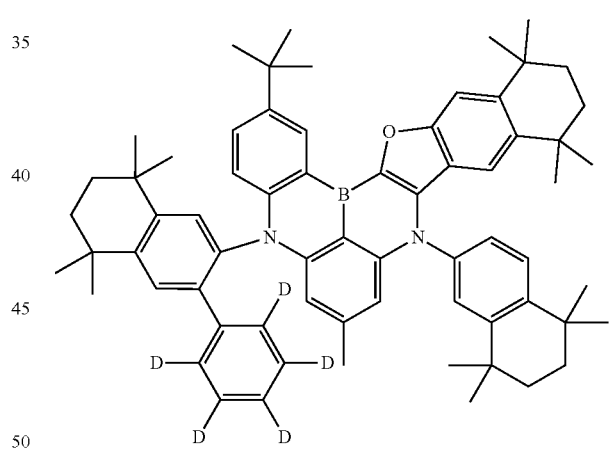
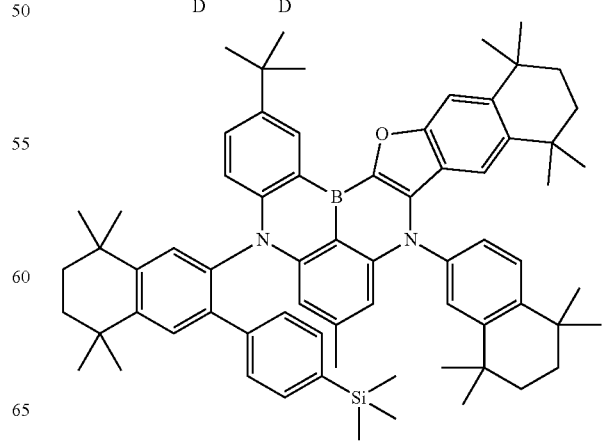

1867
-continued
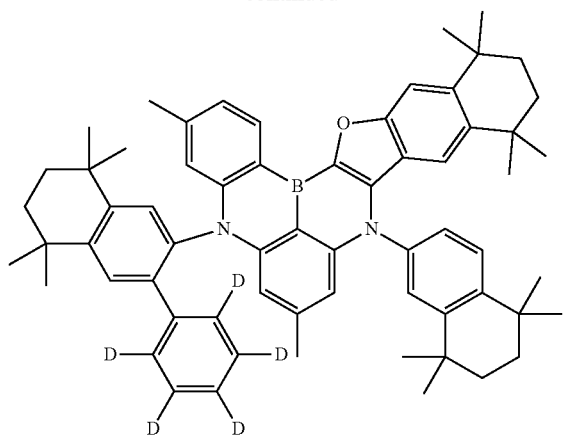
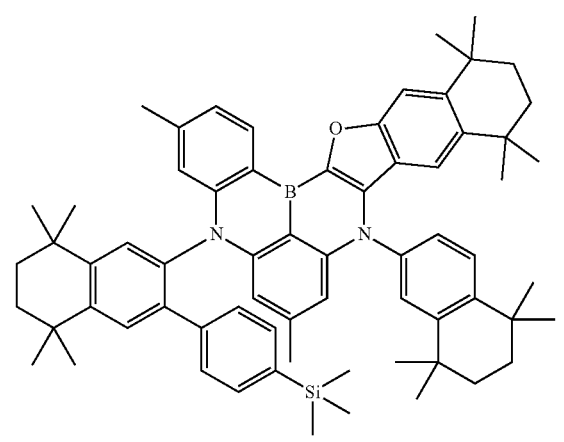
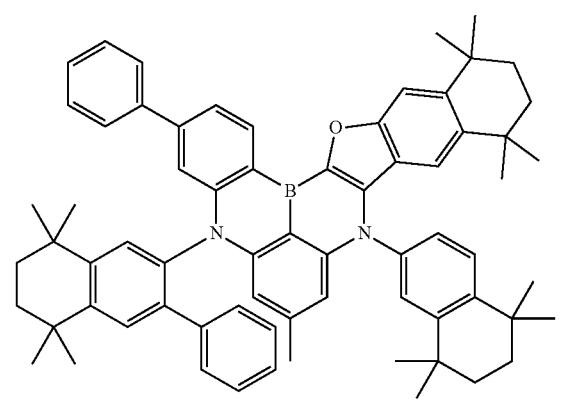
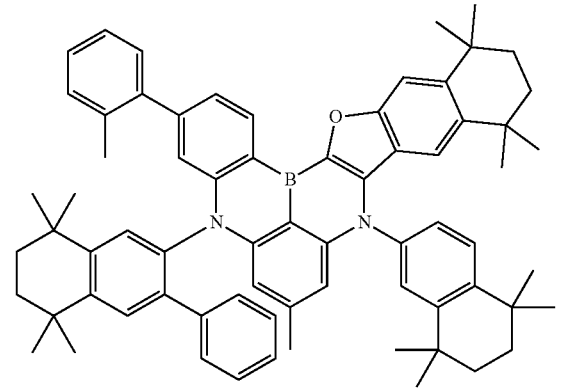
1868
-continued
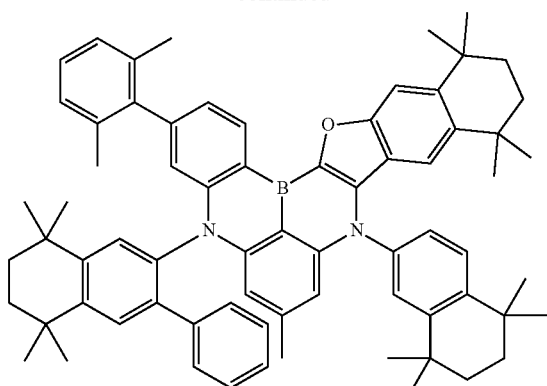
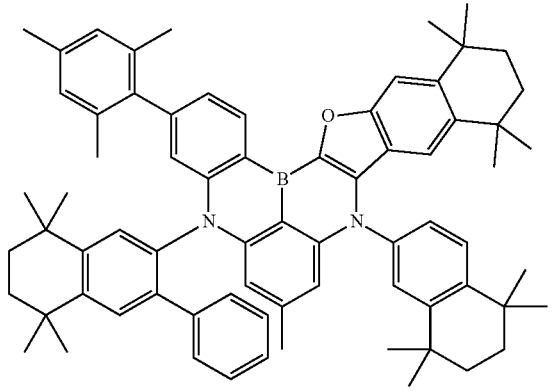
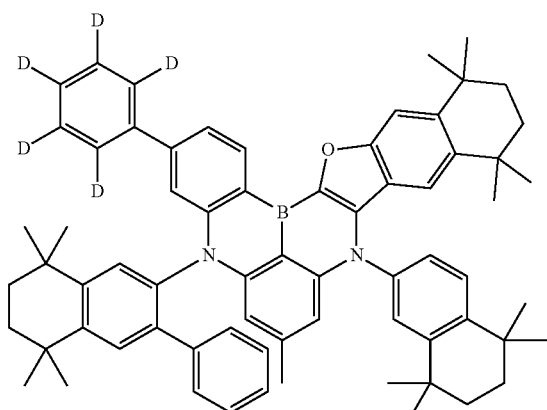
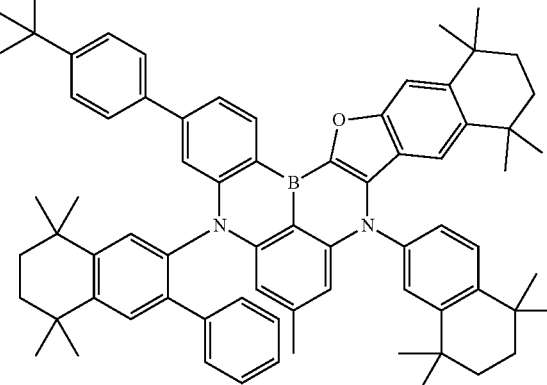

1869
-continued
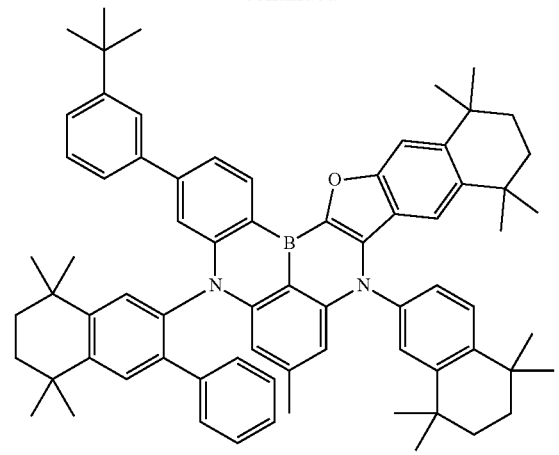
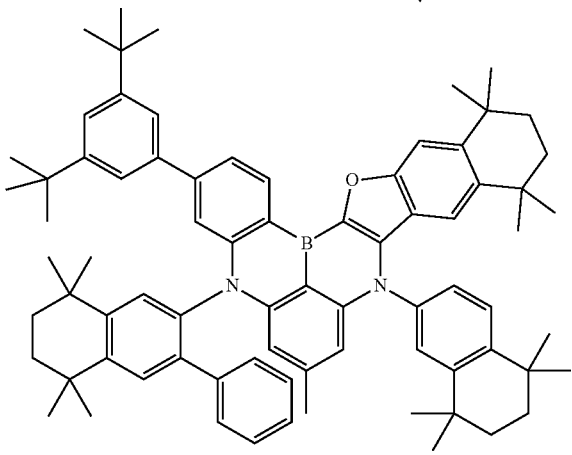
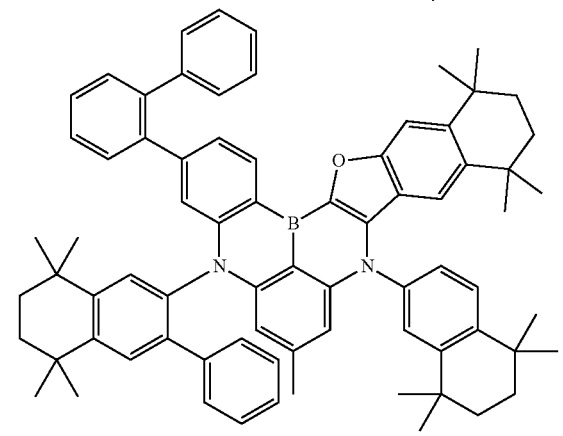
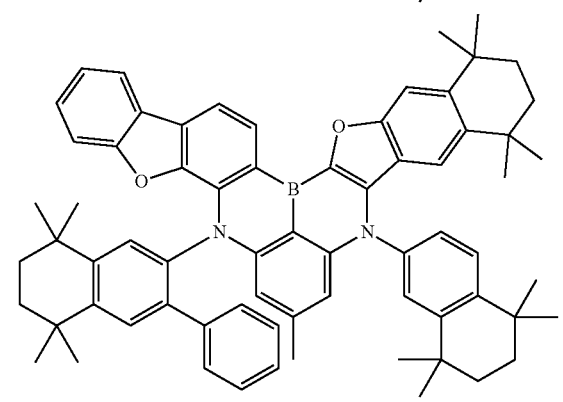
1870
-continued
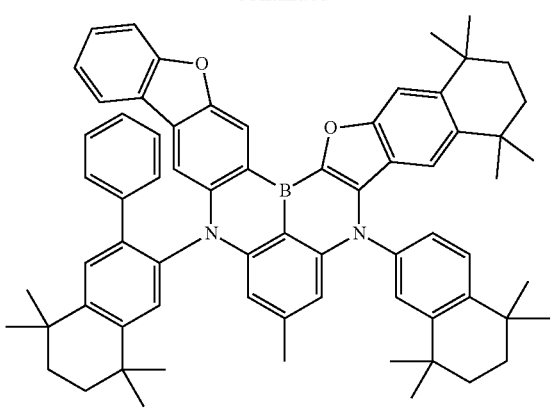
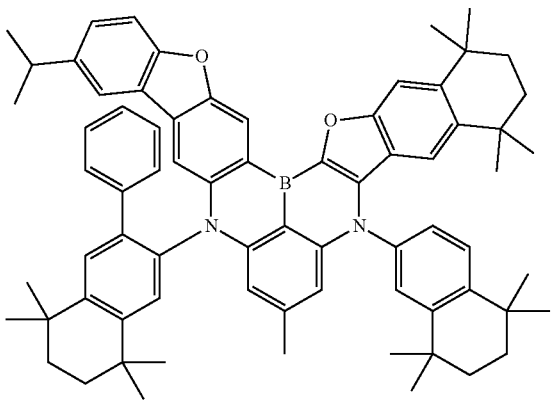
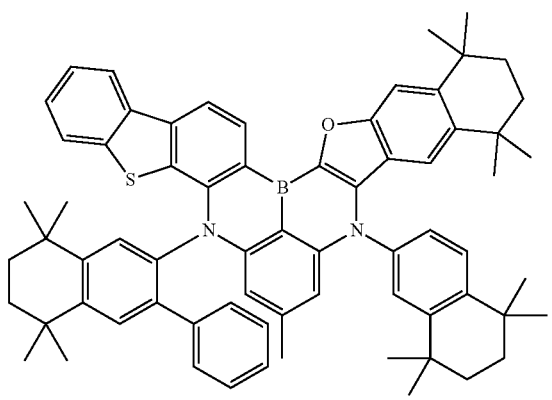
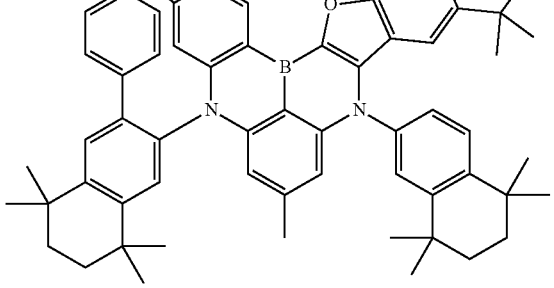

1871
-continued
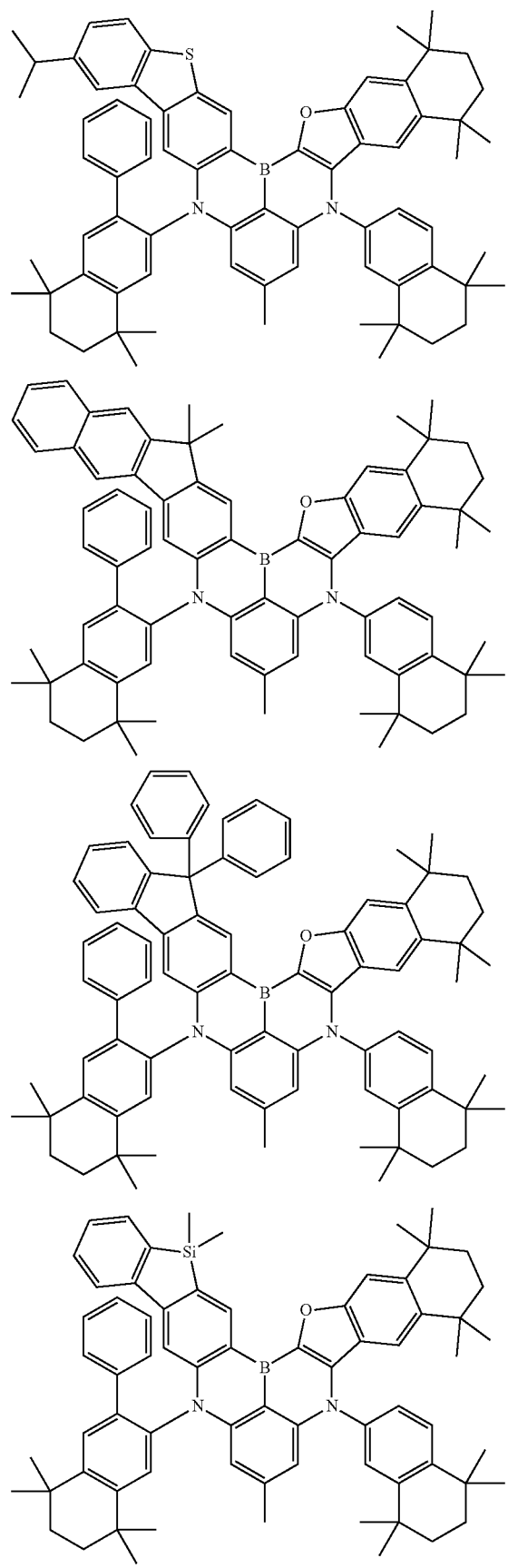
1872
-continued
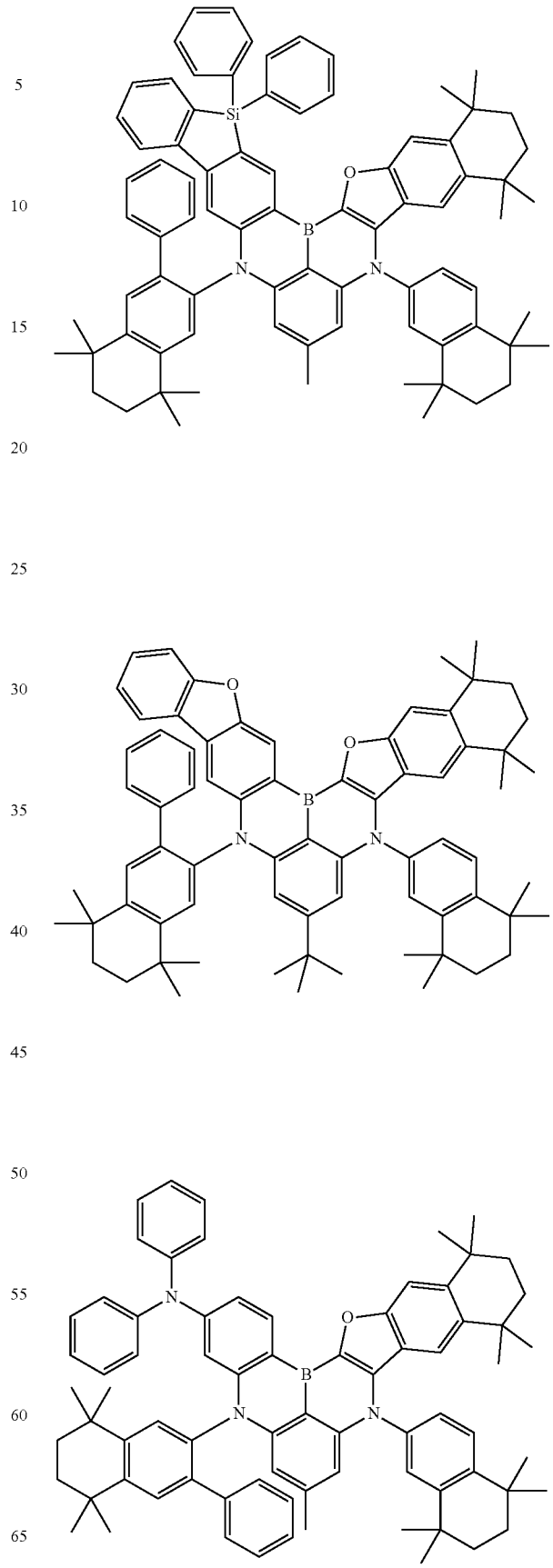

1873
-continued
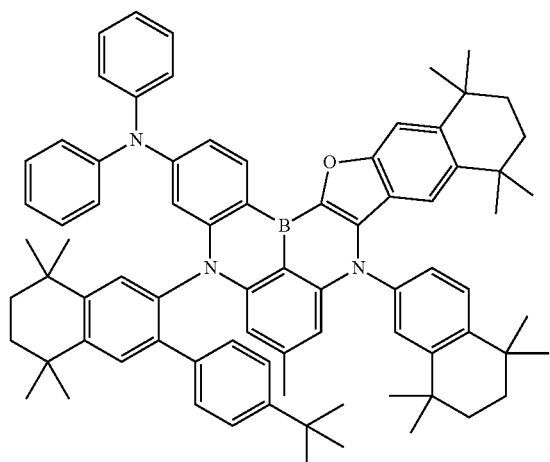
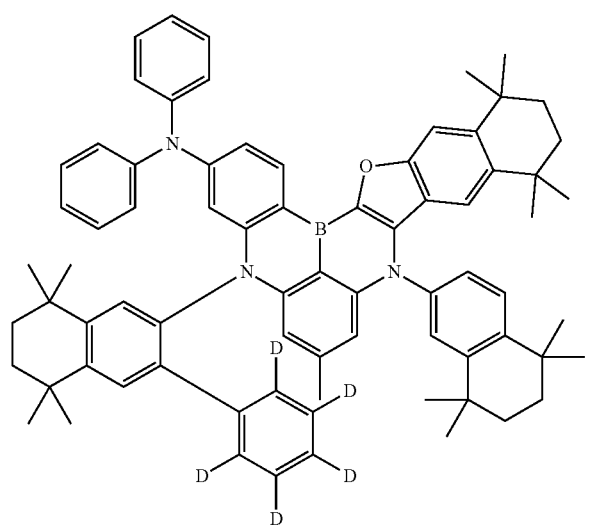
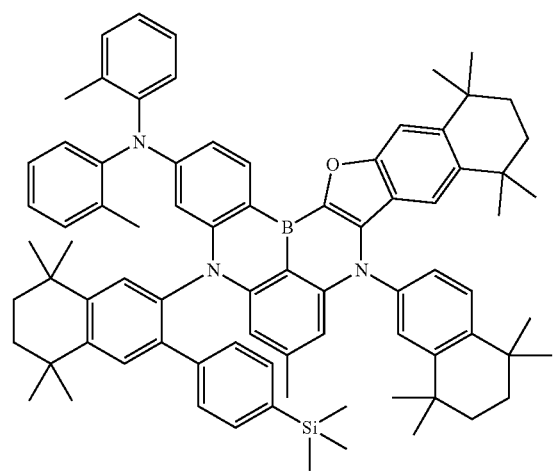
1874
-continued
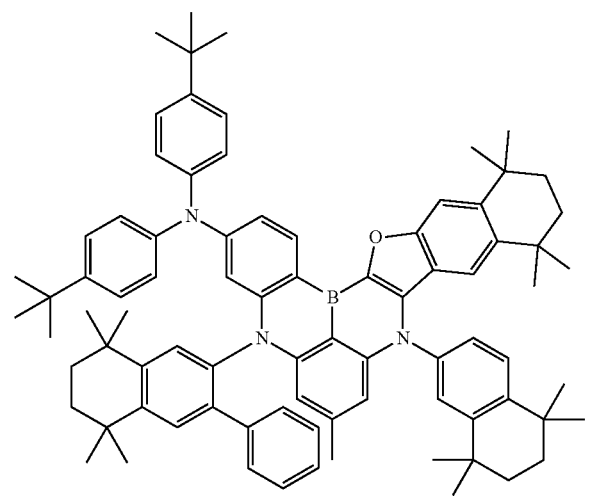
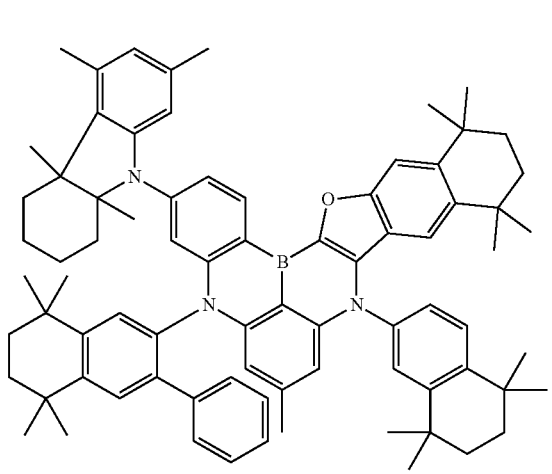

1875
-continued
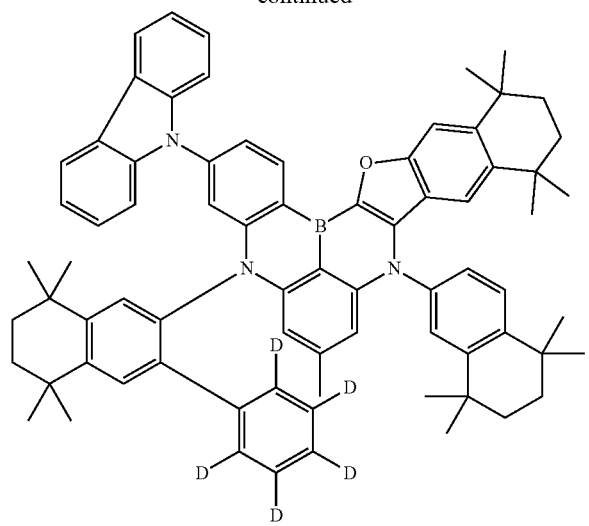
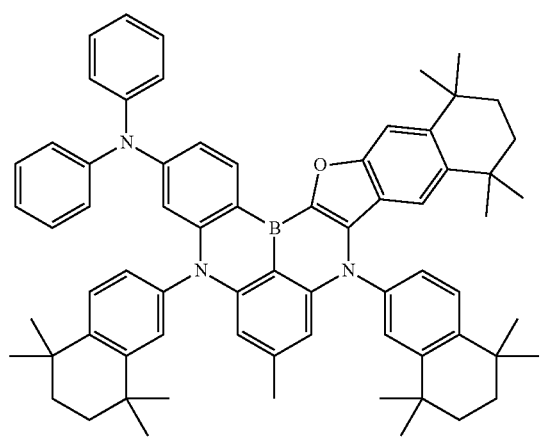
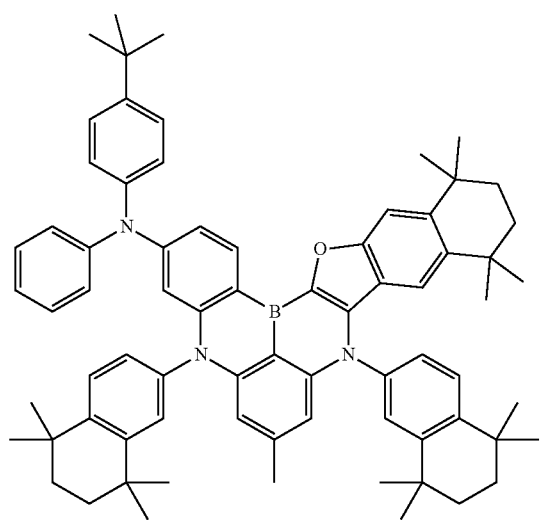
1876
-continued
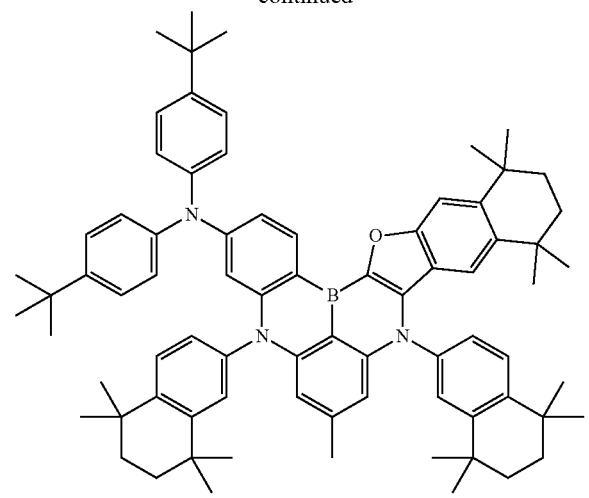
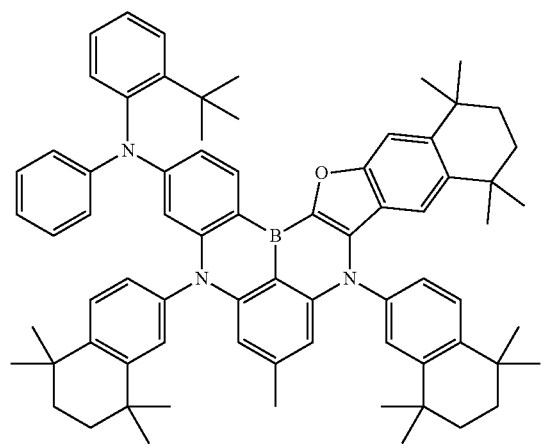
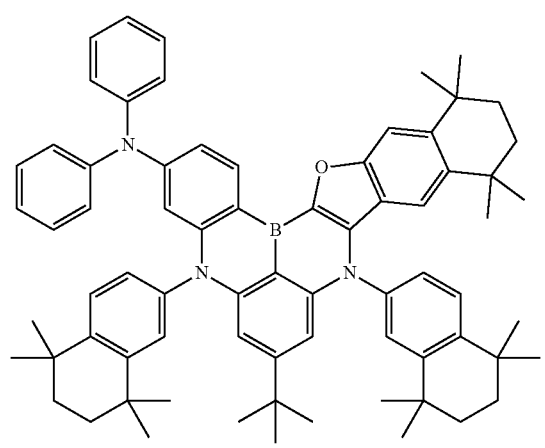

1877
-continued
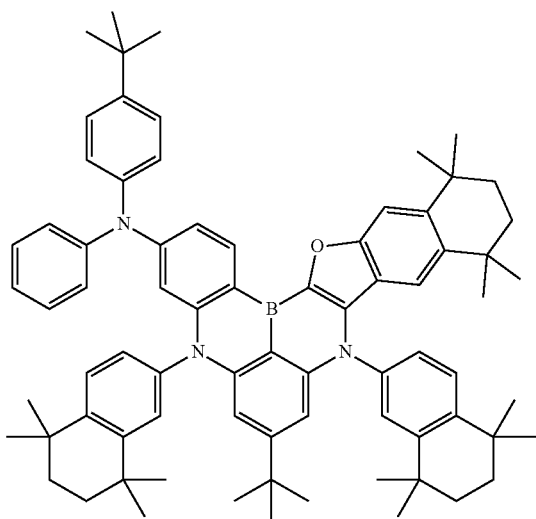
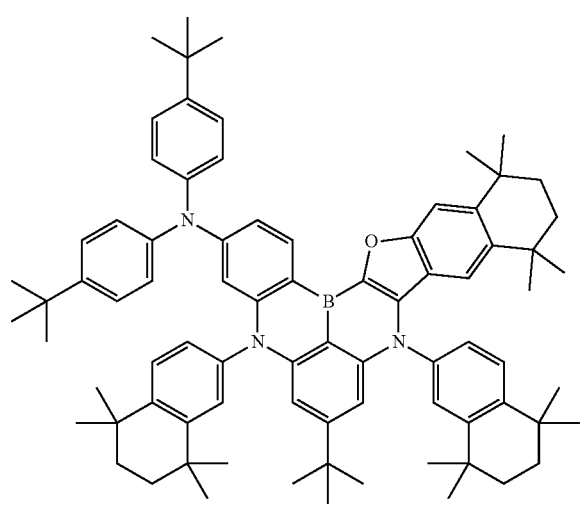
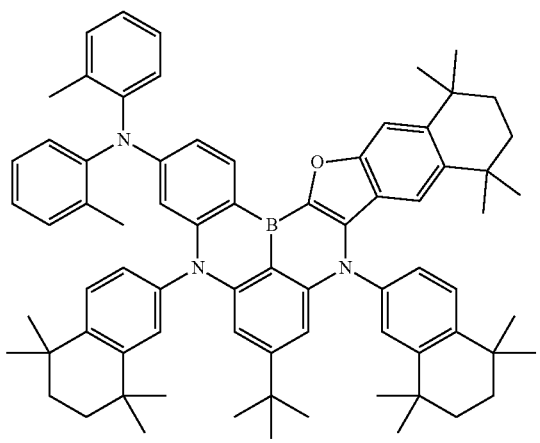
1878
-continued
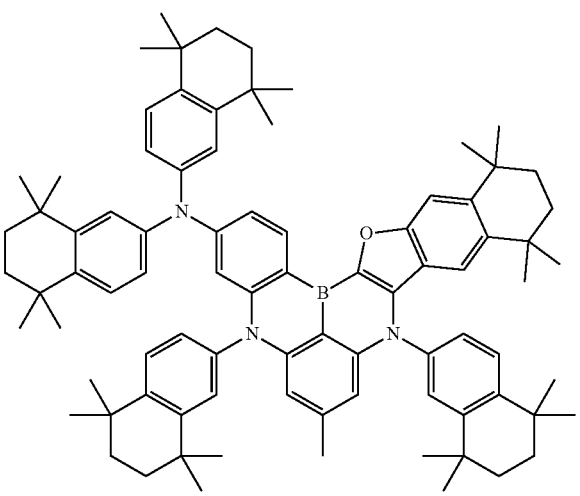
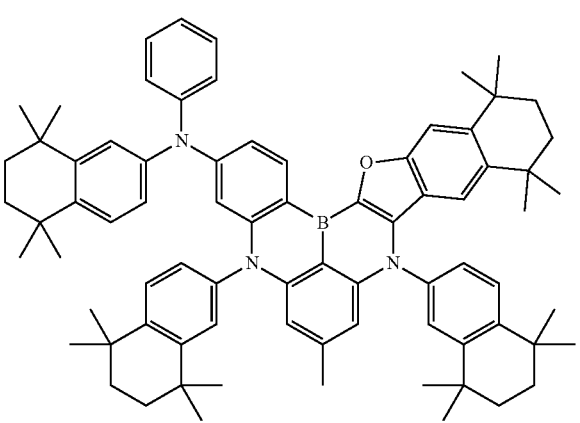
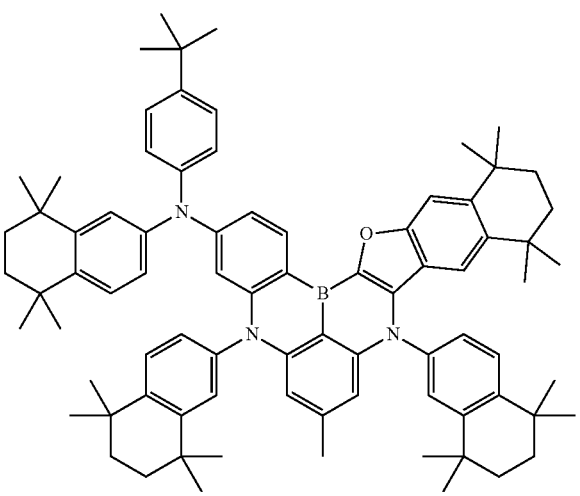

1879
-continued
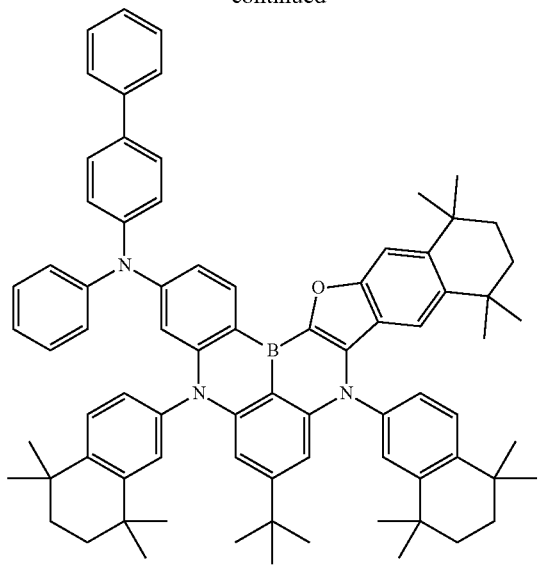
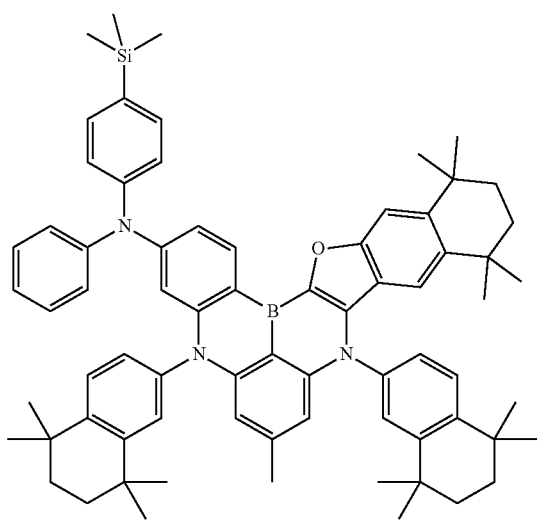
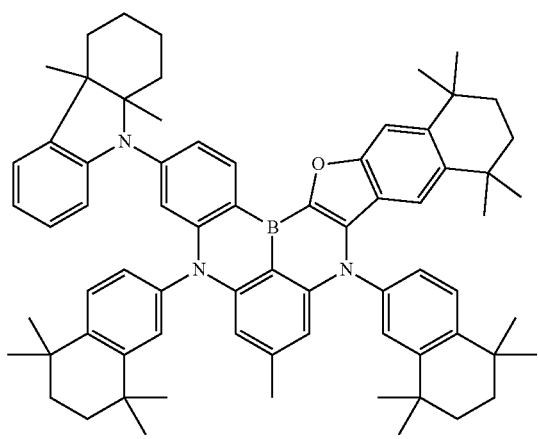
1880
-continued
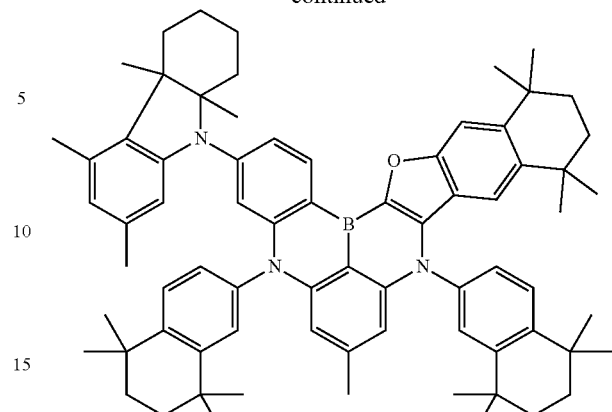
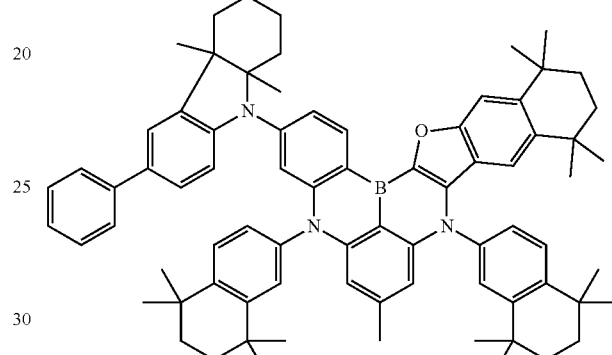
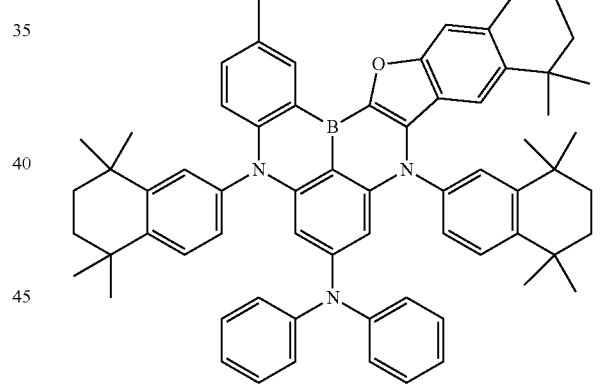
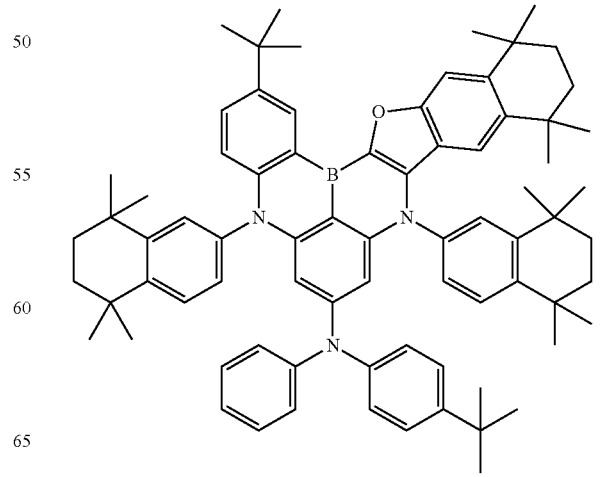

1881
-continued
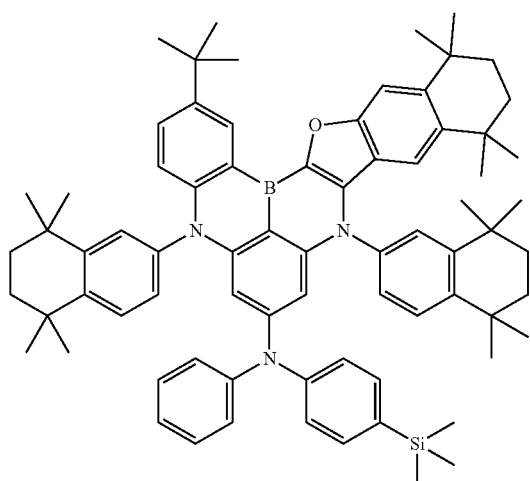
1882
-continued
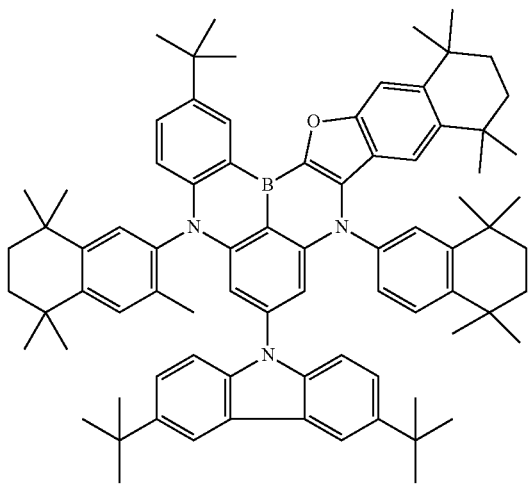
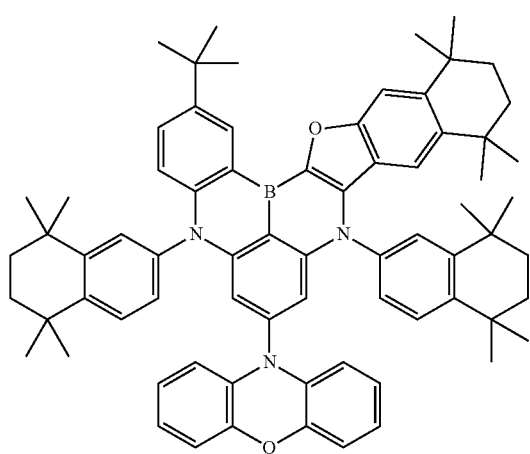
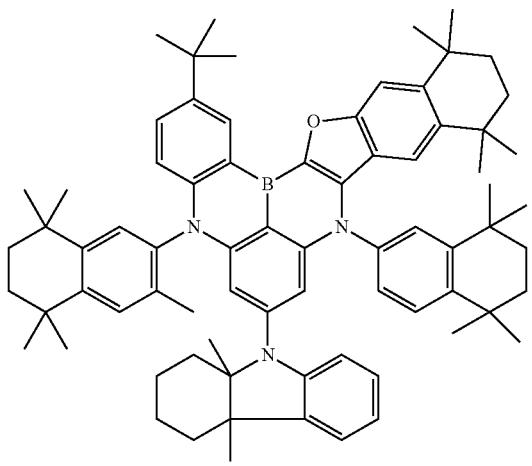
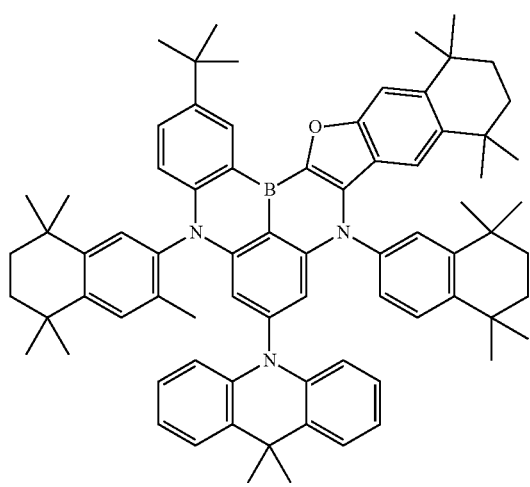
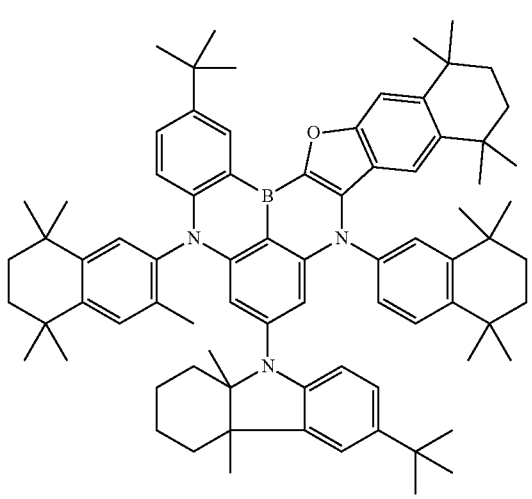

1883
-continued
1884
-continued
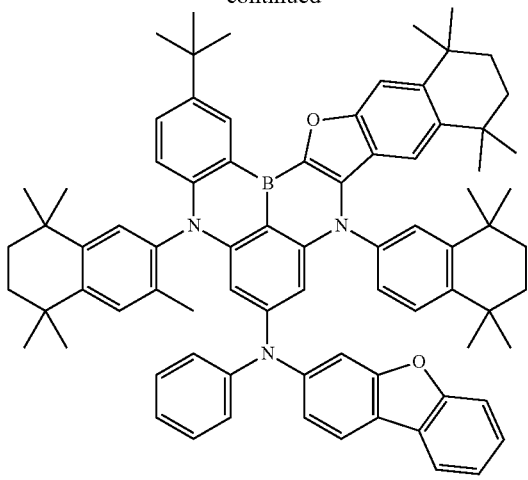
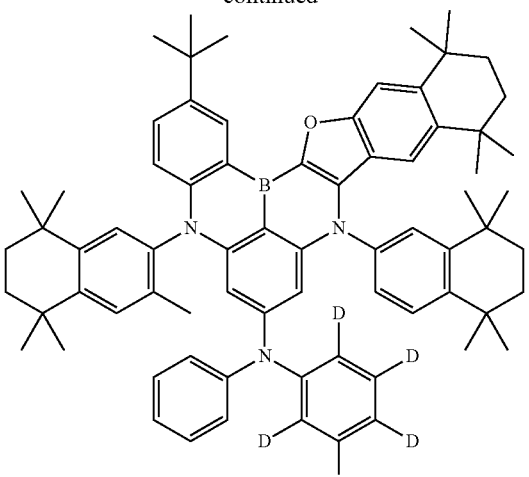
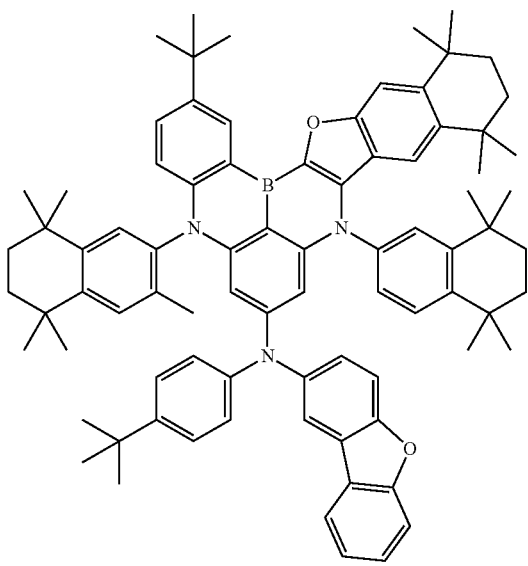

1885
-continued
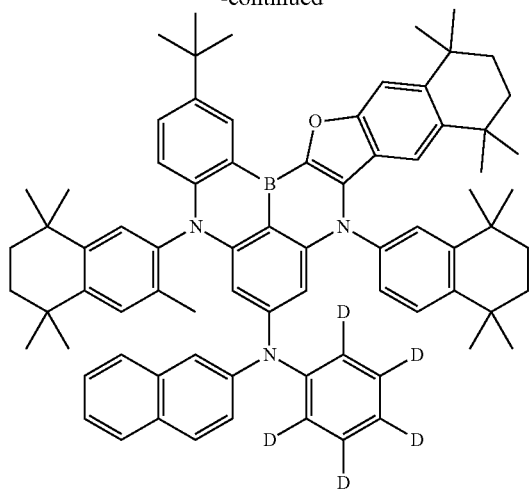
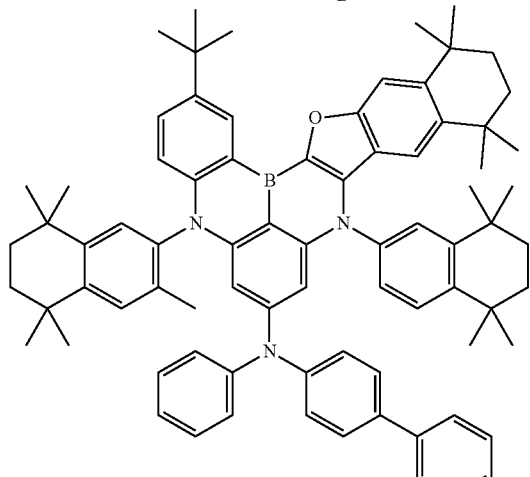
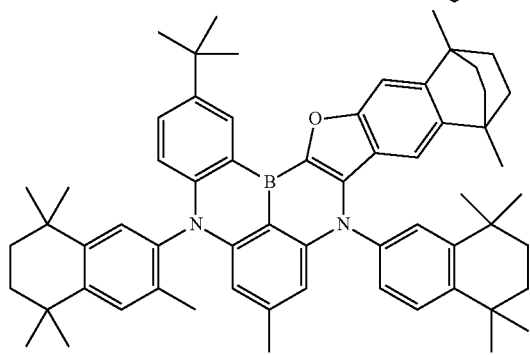
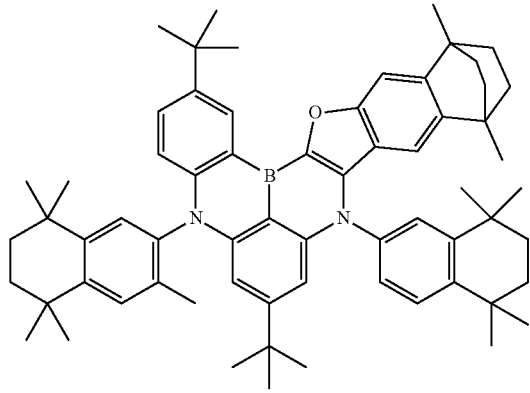
1886
-continued
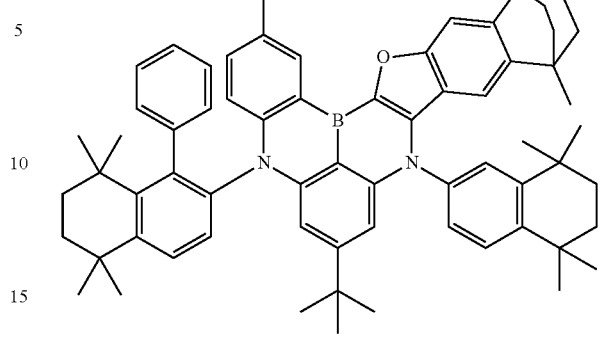
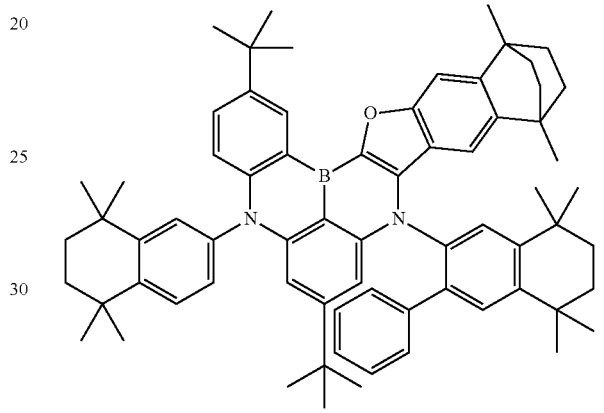
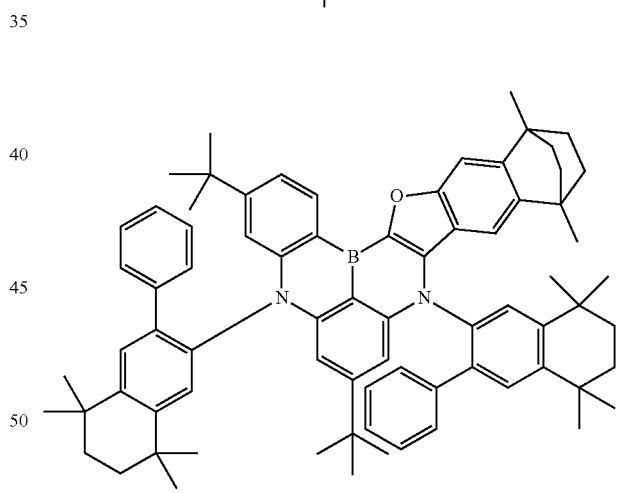
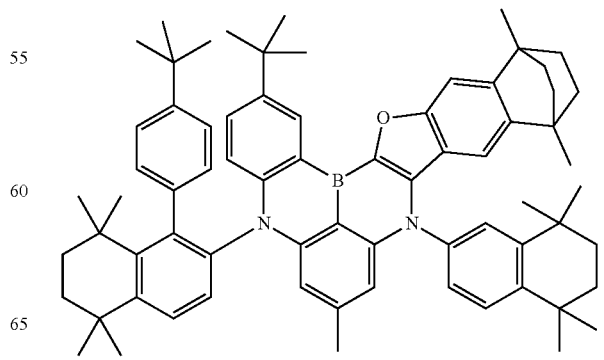

1887
-continued
1888
-continued
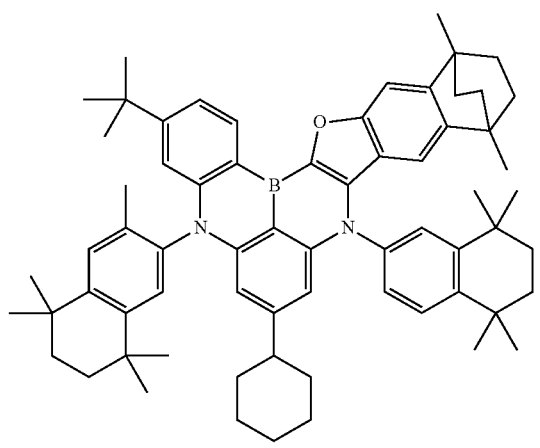
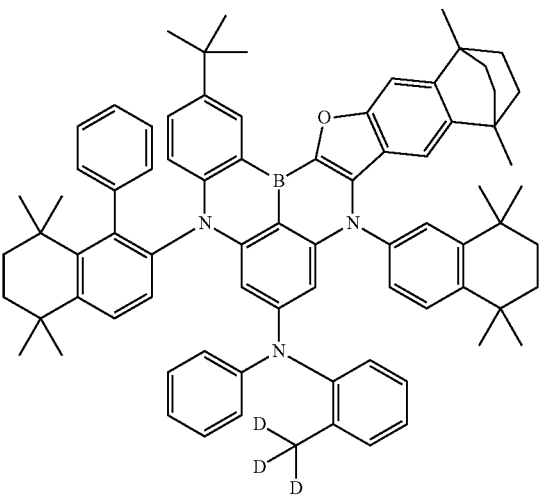
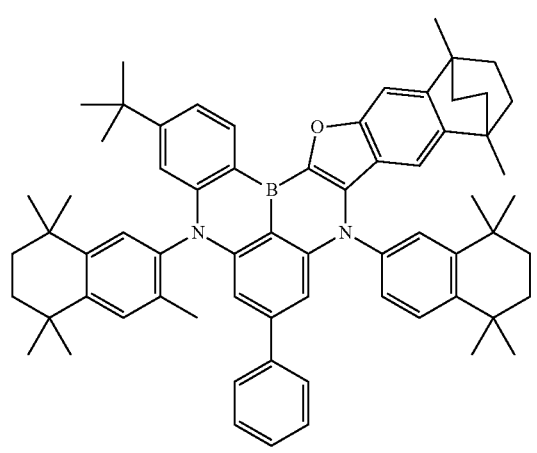
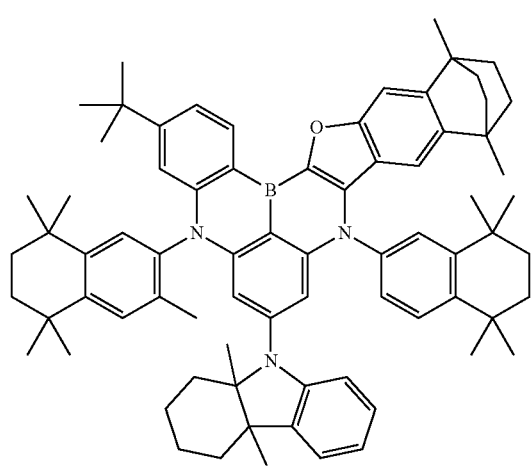
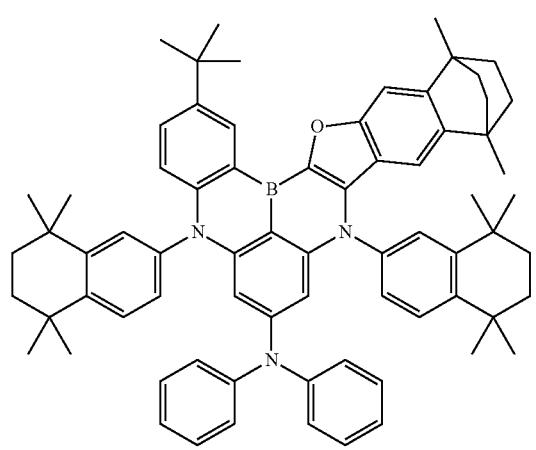

1889
-continued
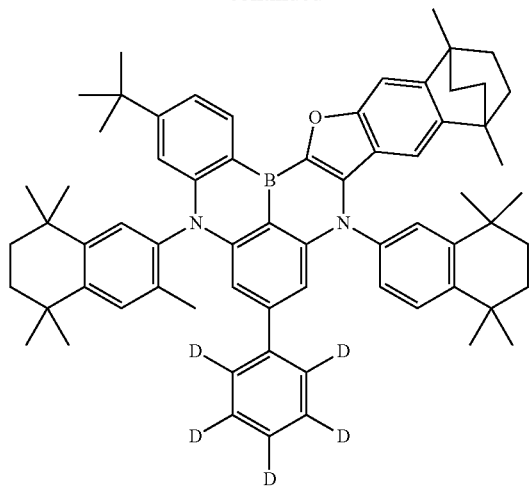
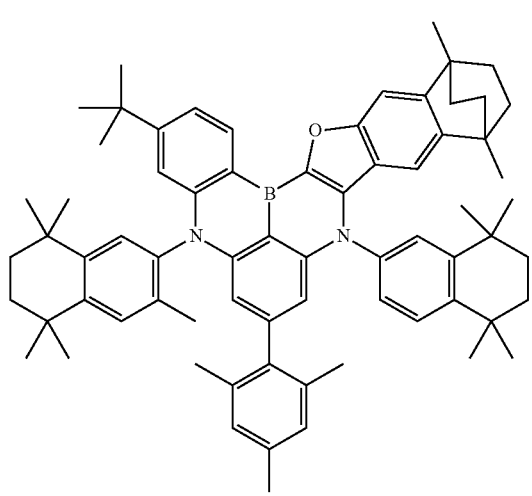
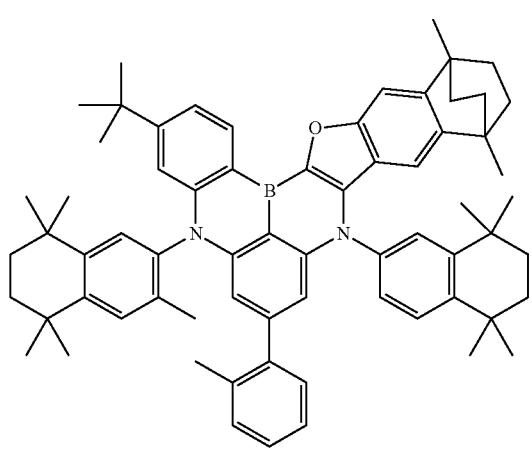
1890
-continued
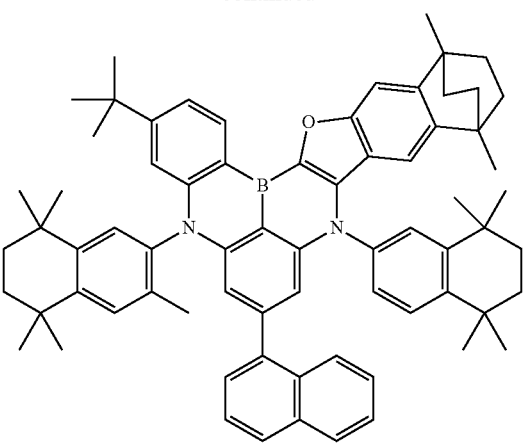
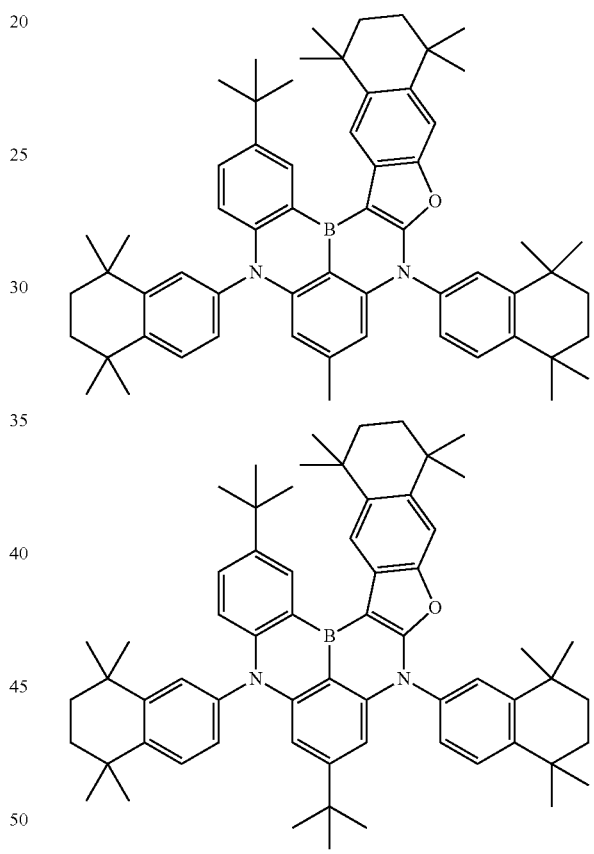
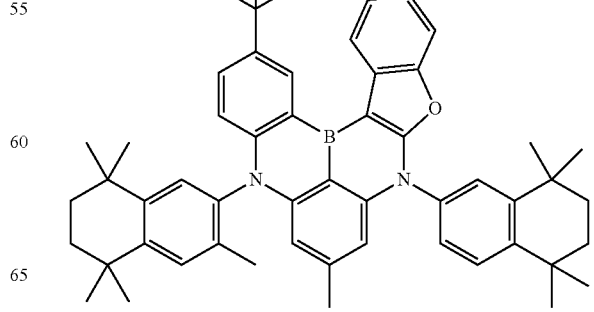

1891
-continued
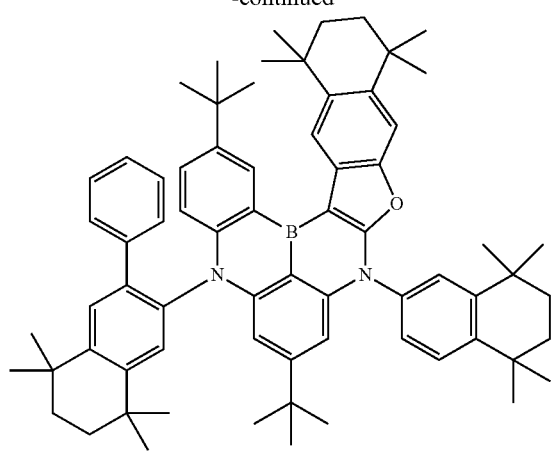
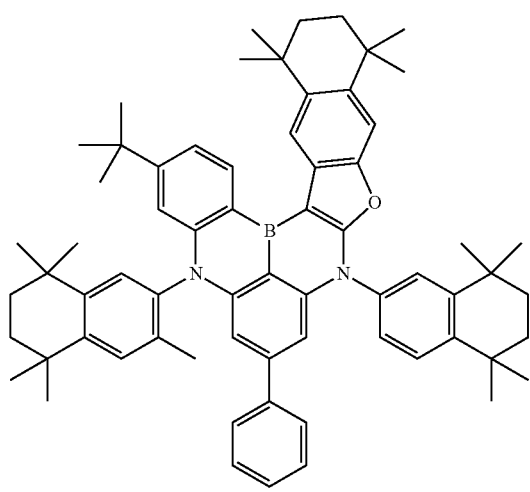
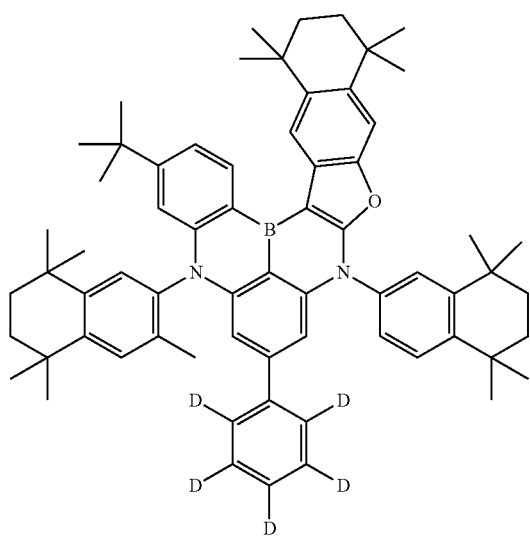
1892
-continued
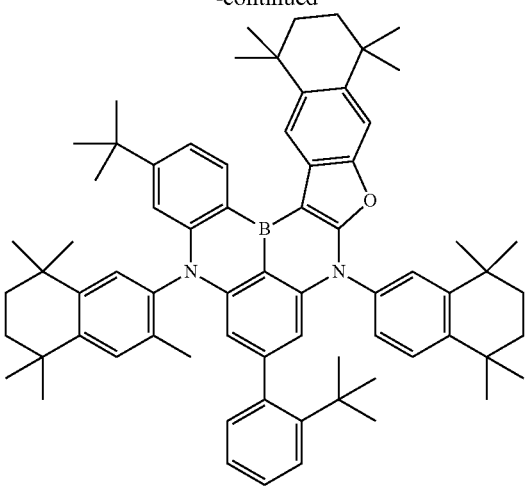
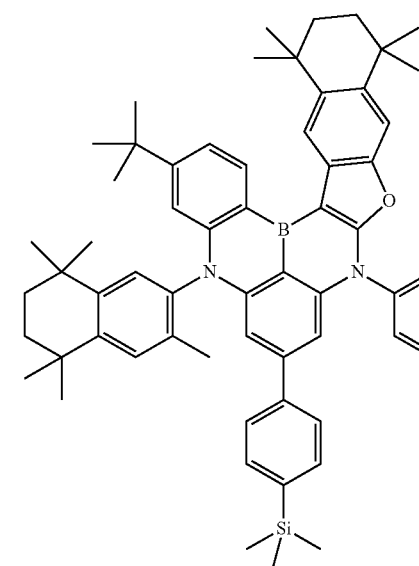
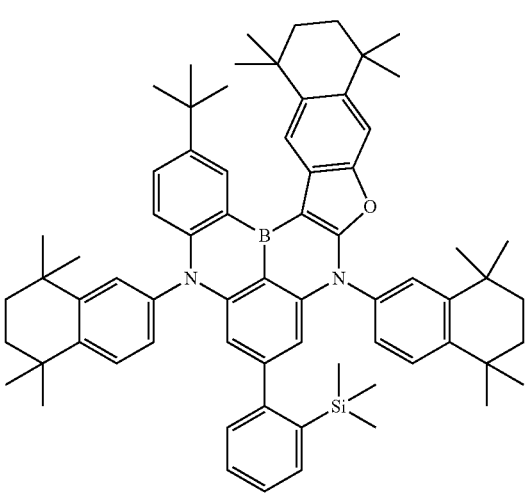

1893
-continued
1894
-continued
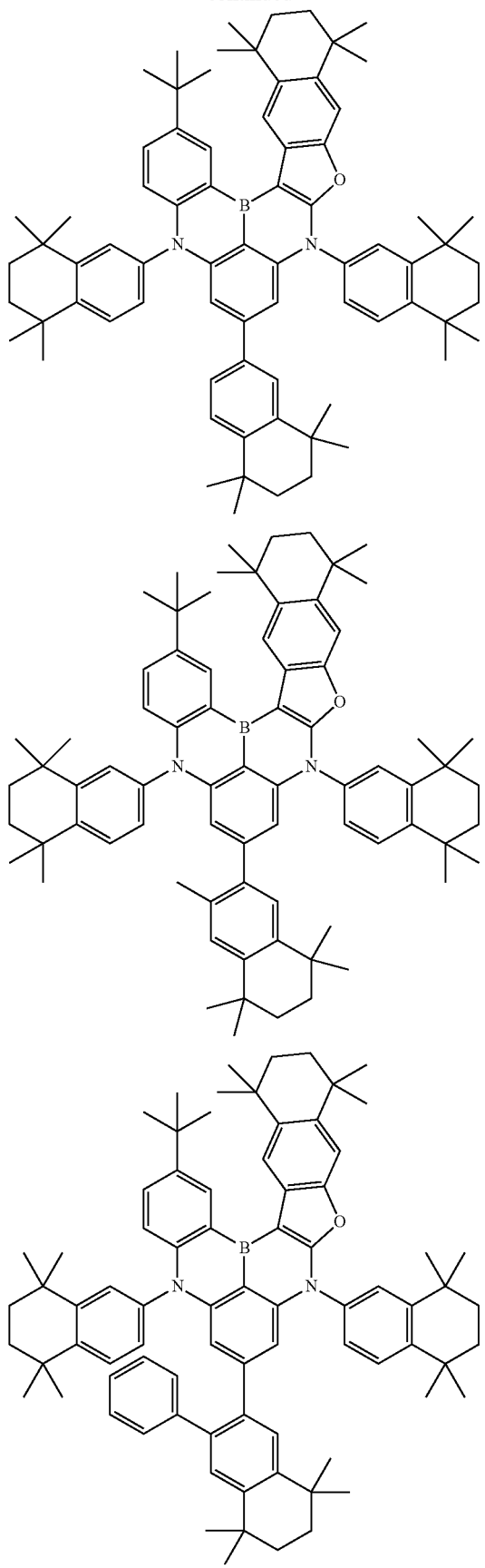
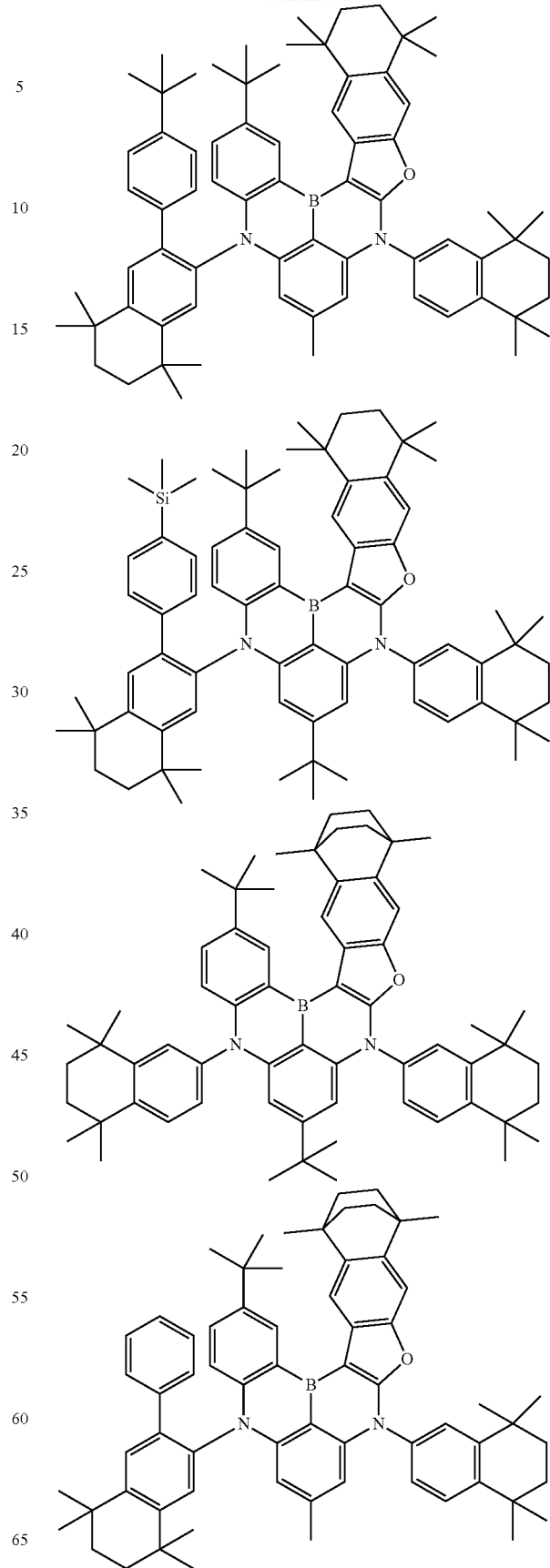

1895
-continued
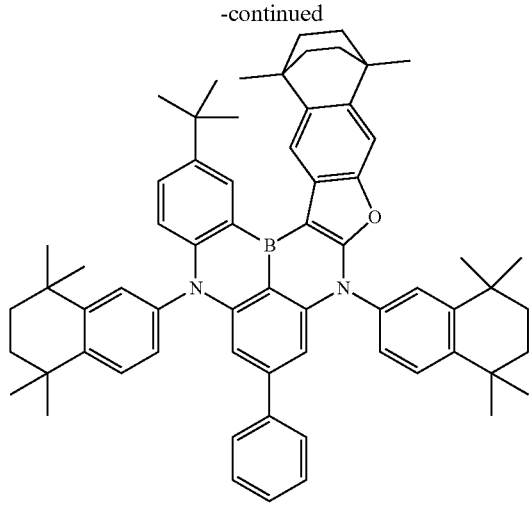
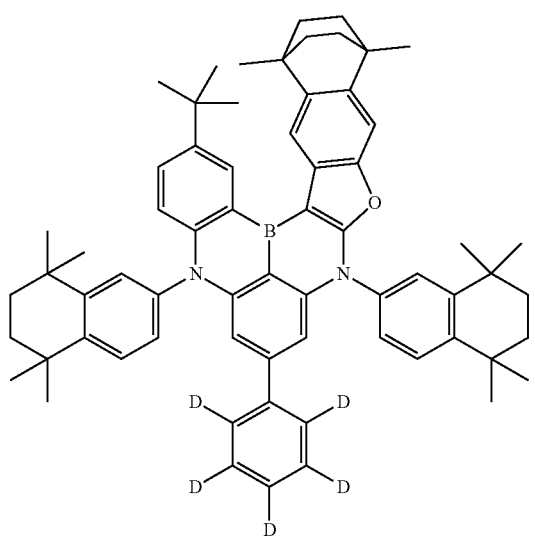
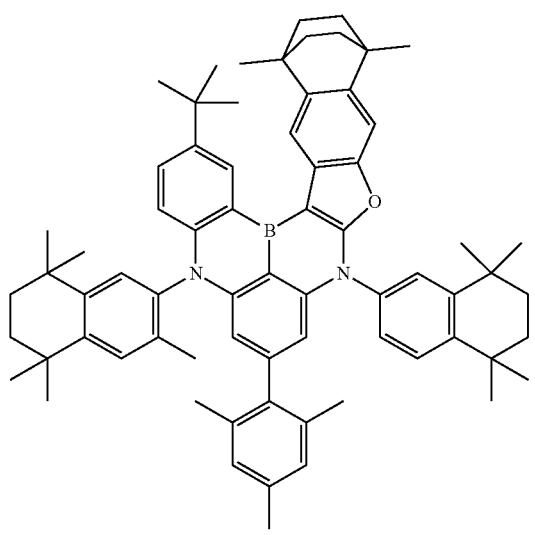
1896
-continued
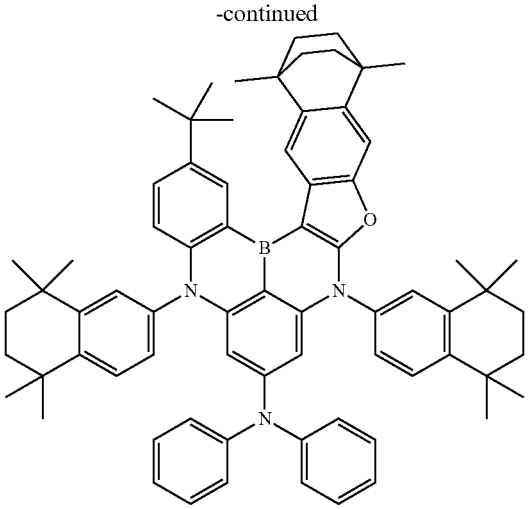
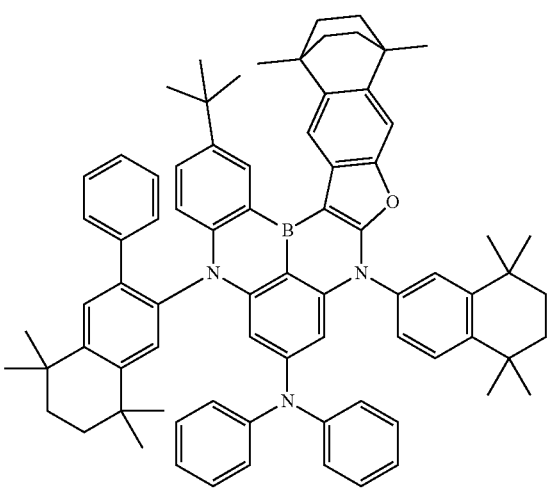
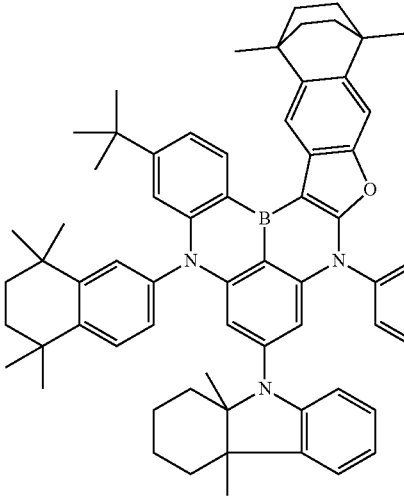

1897
-continued
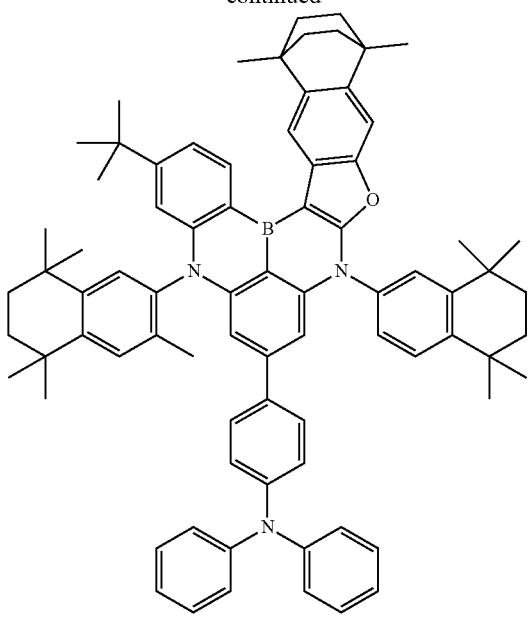
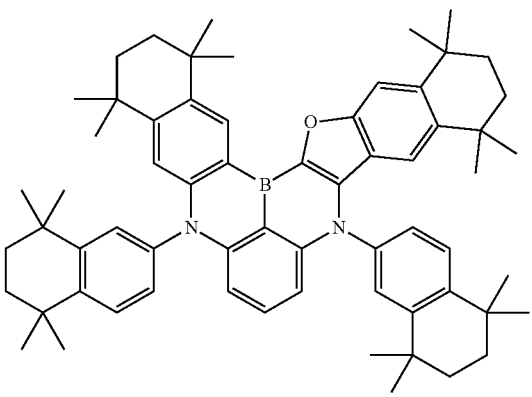
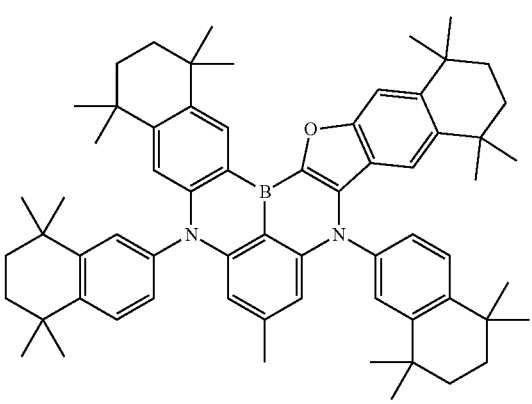
1898
-continued
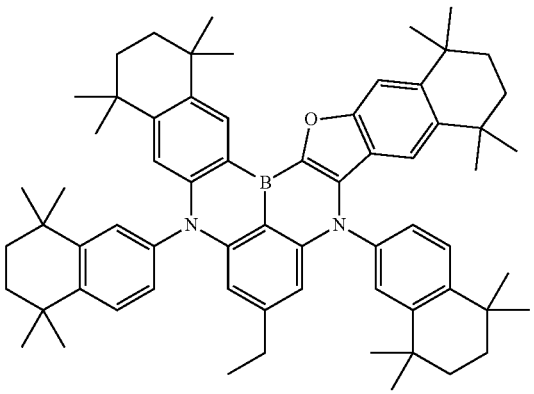
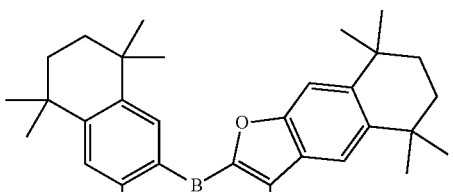
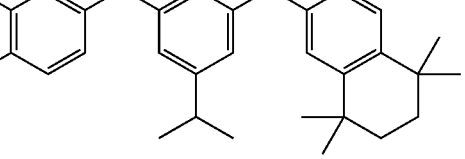
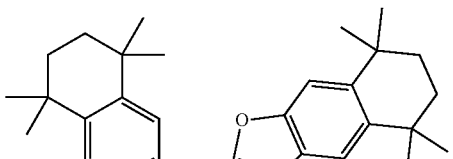
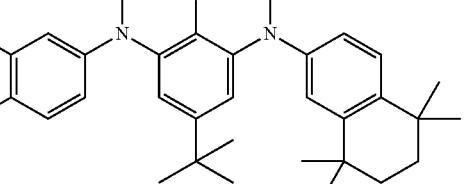
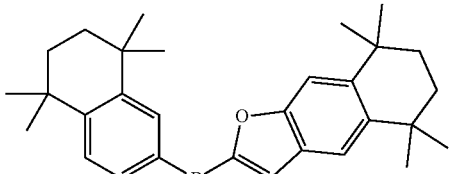

1899
-continued
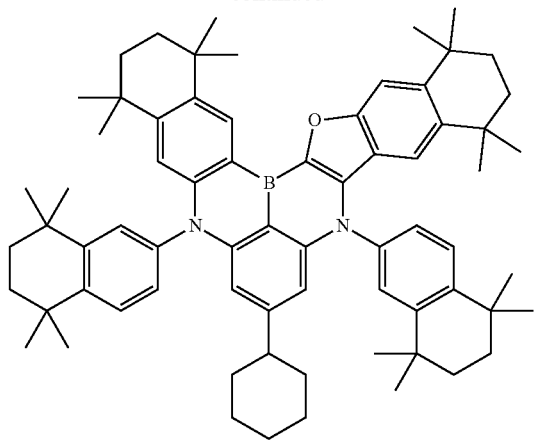
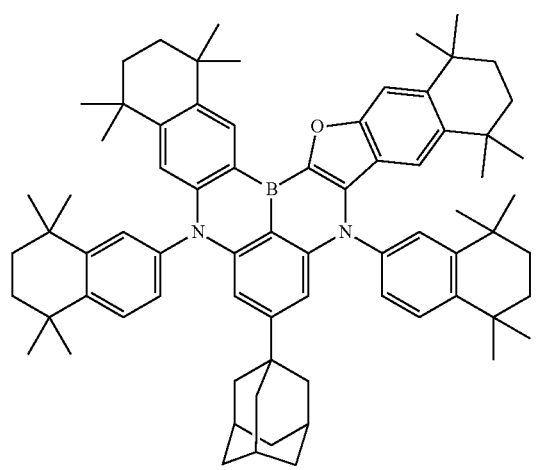
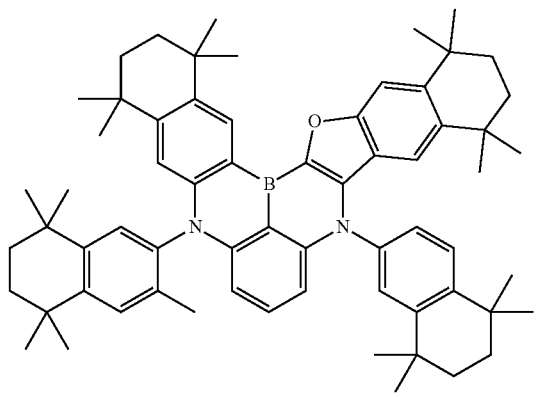
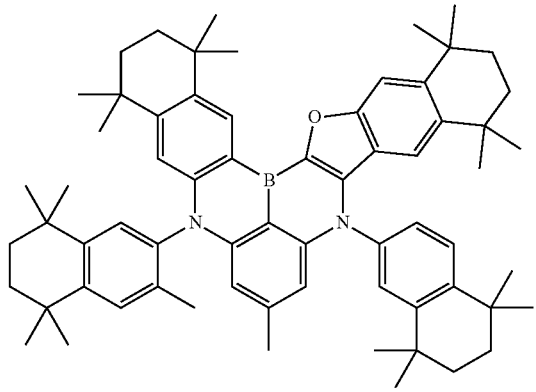
1900
-continued
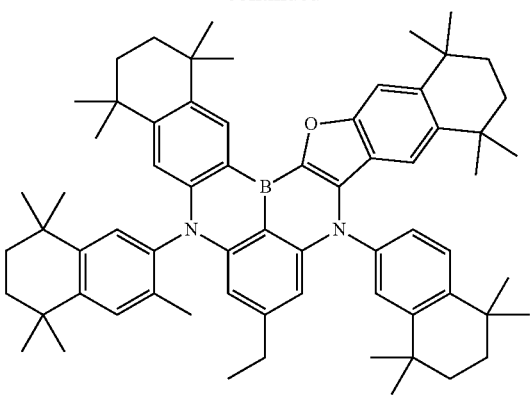
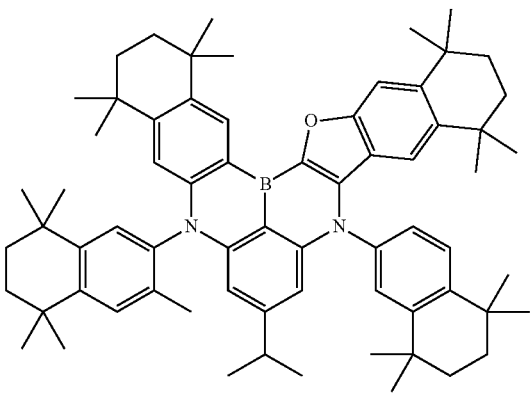
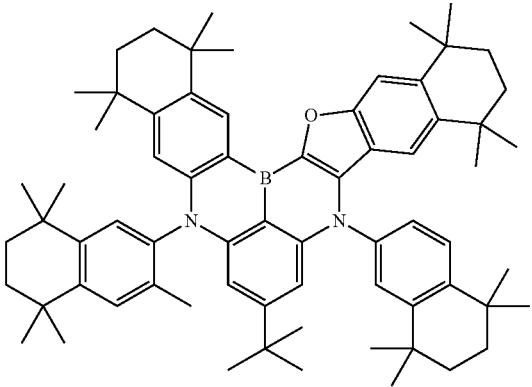
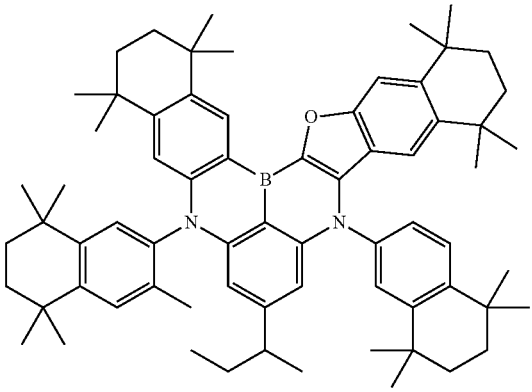

1901
-continued
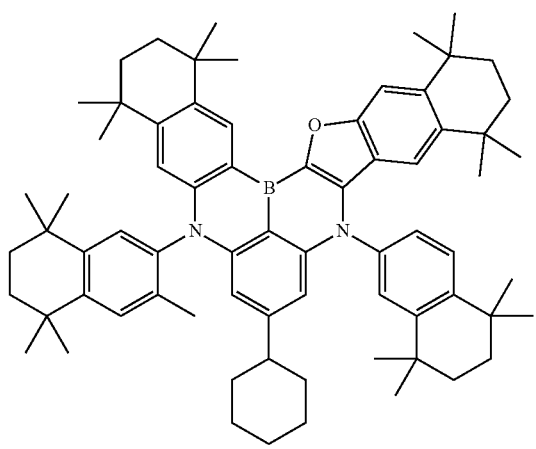
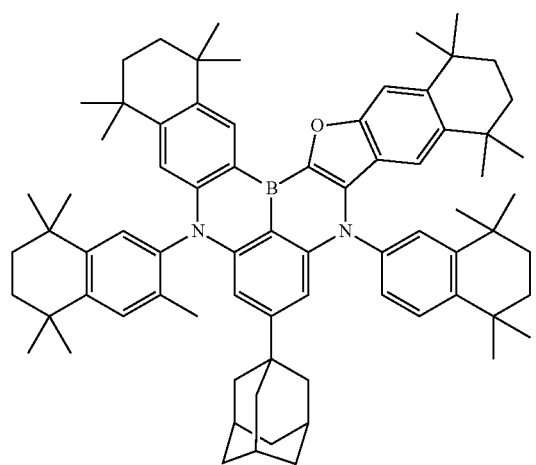
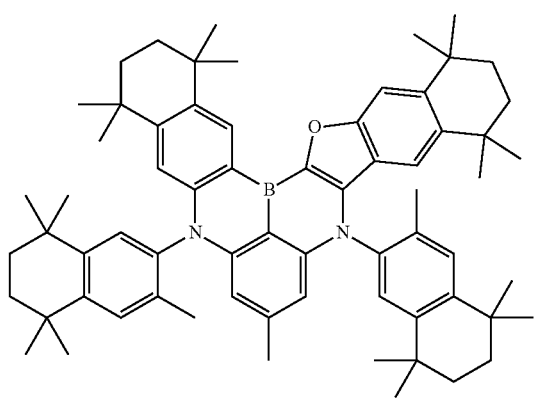
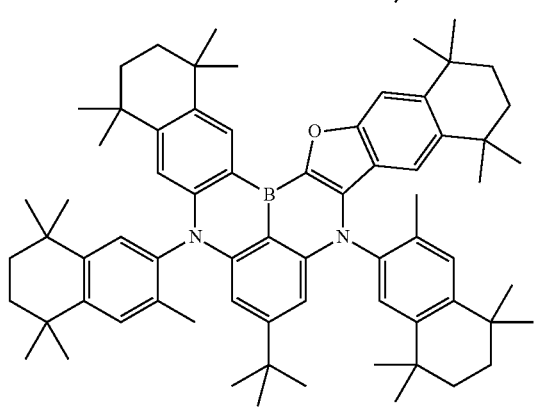
1902
-continued
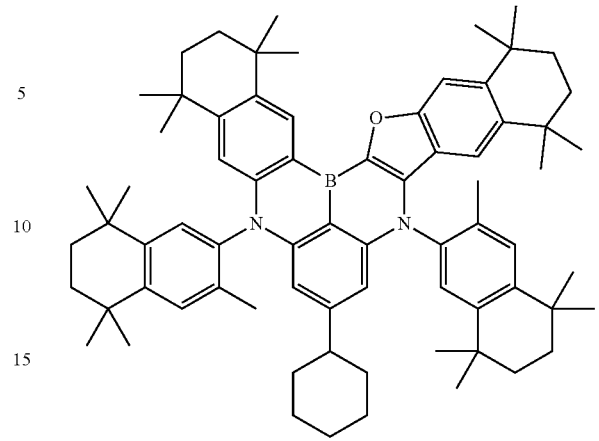
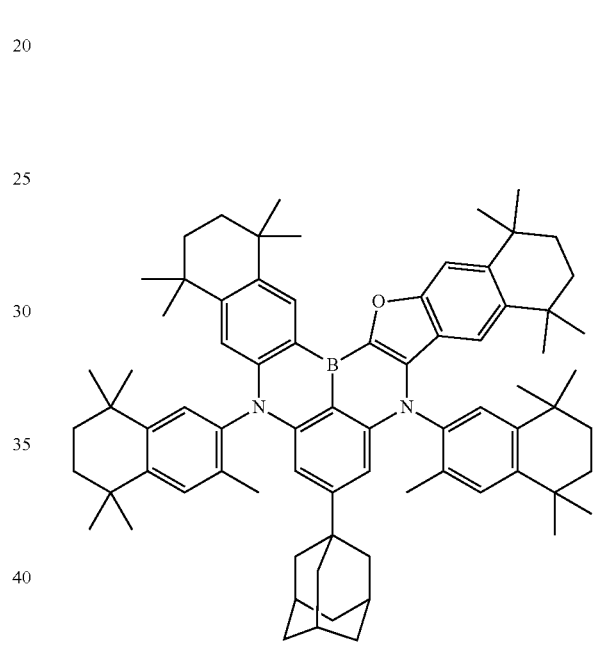
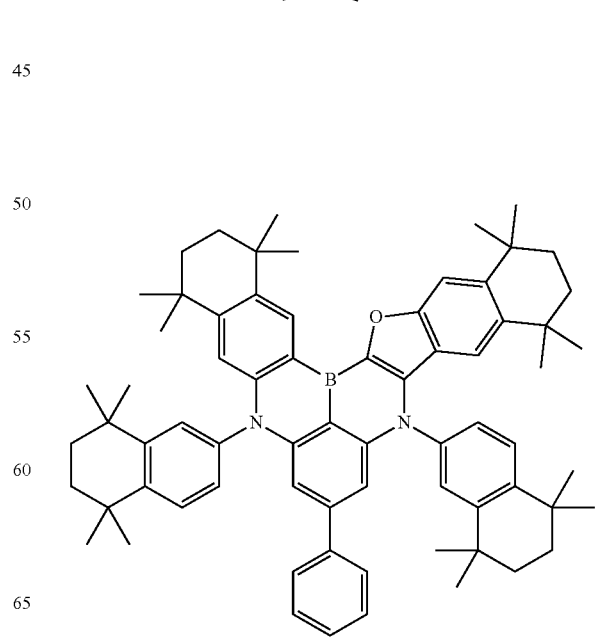

1903
-continued
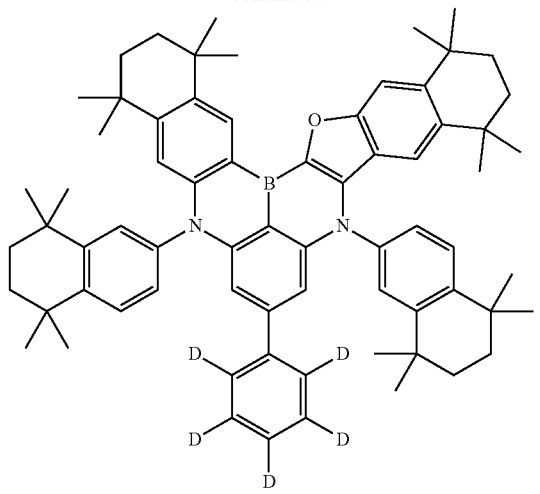
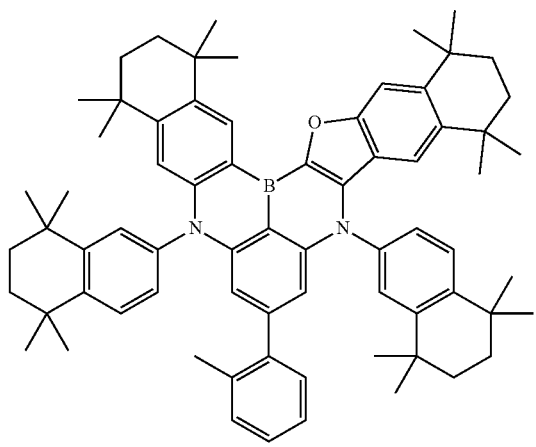
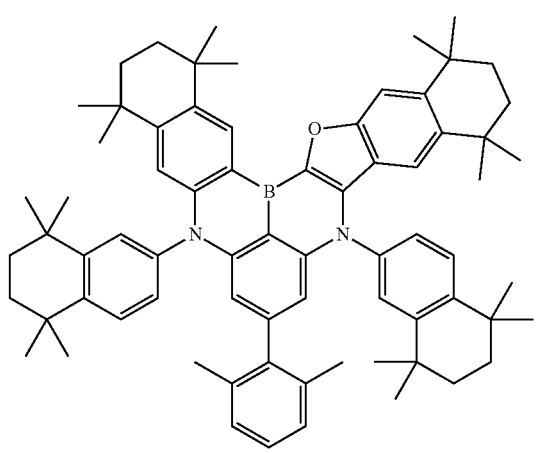
1904
-continued
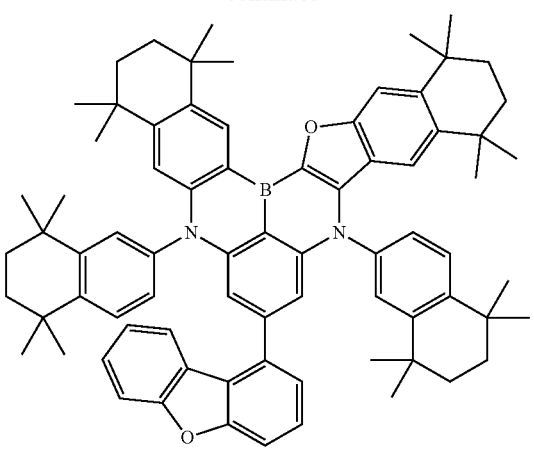
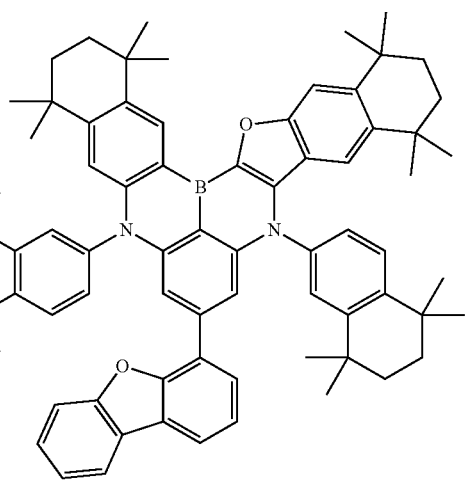
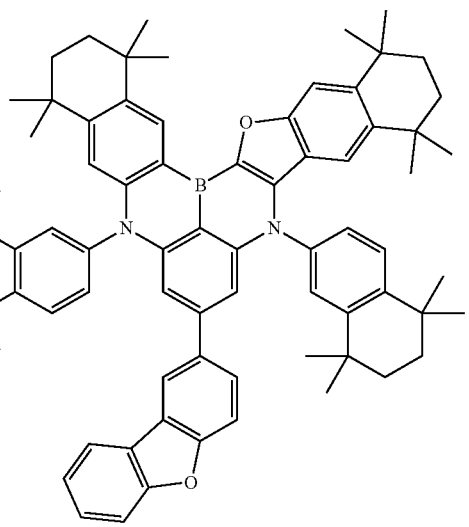

1905
-continued
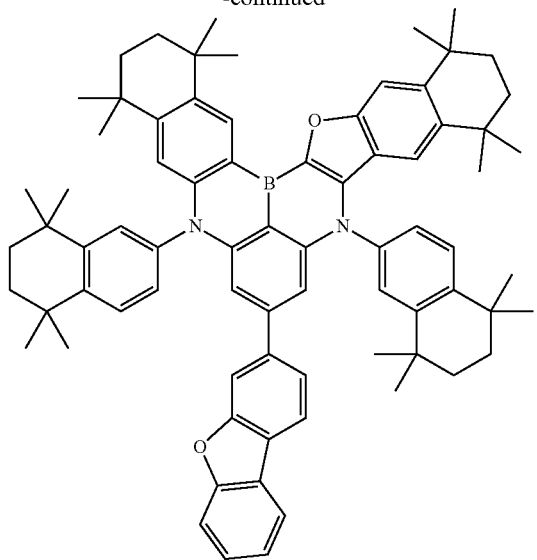
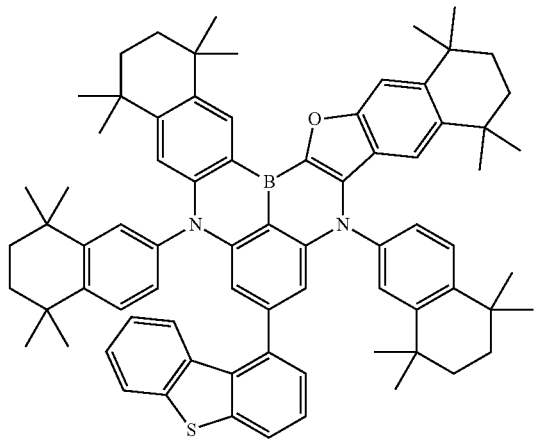
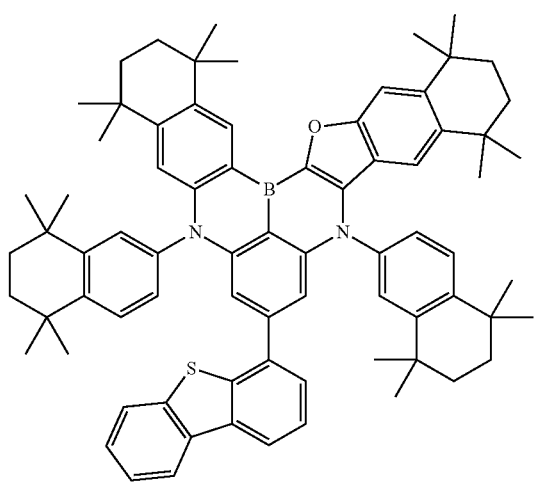
1906
-continued
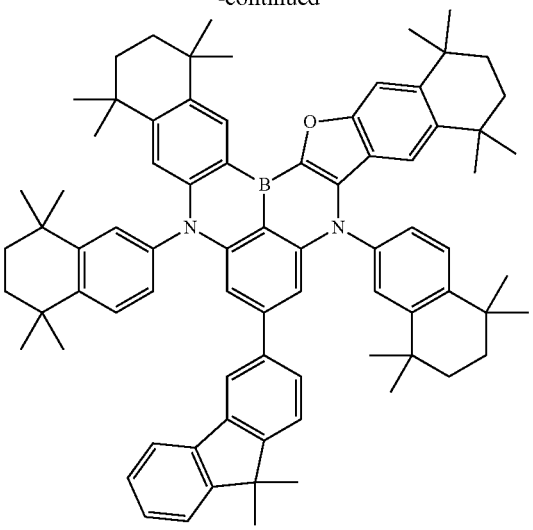
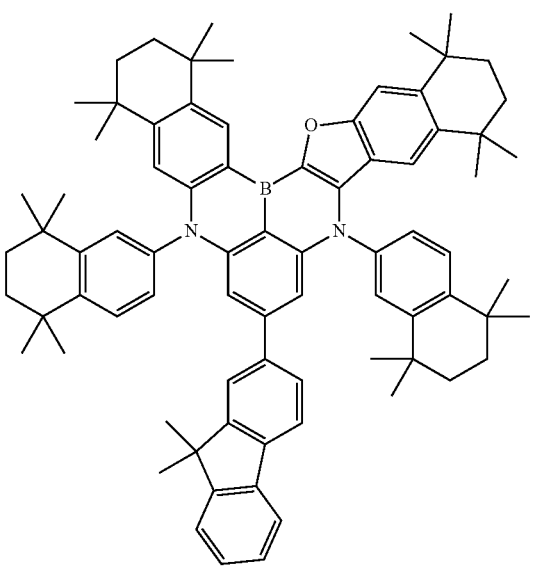
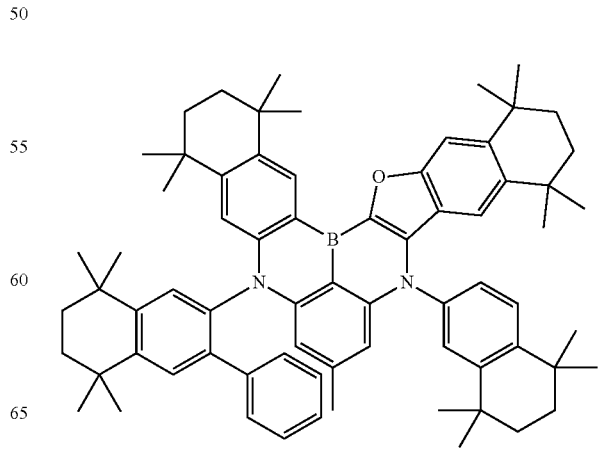

1907
-continued
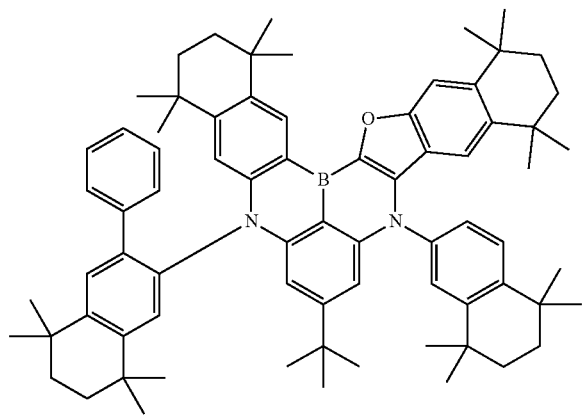

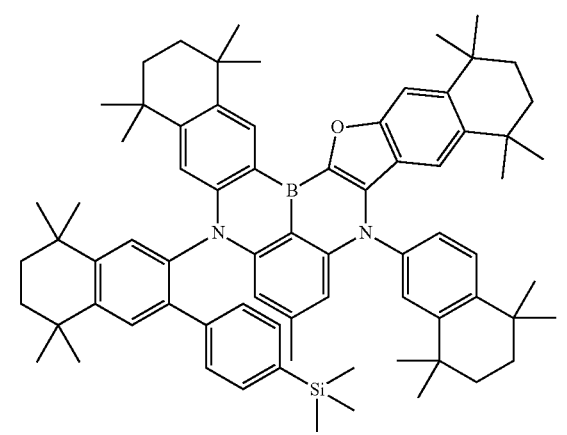
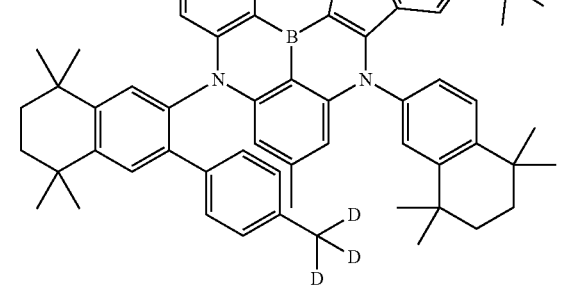
1908
-continued
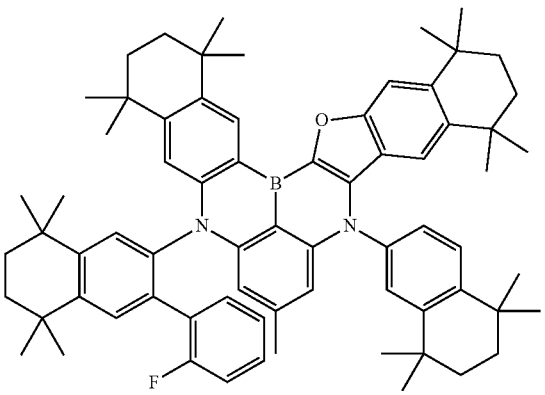
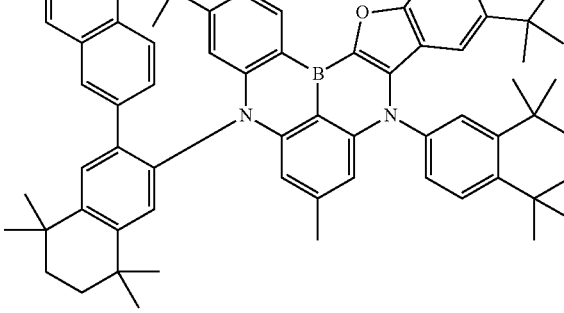
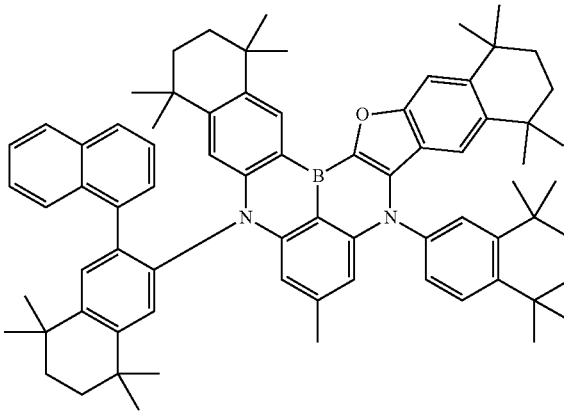
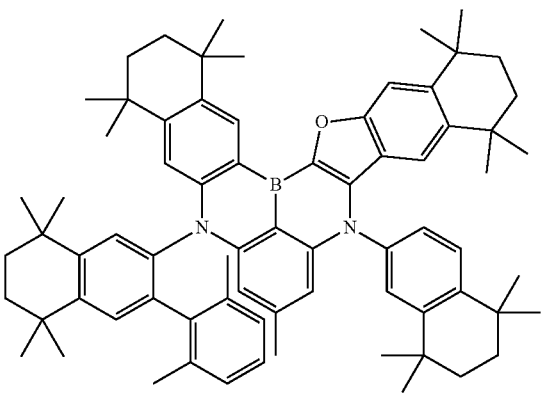

1909
-continued
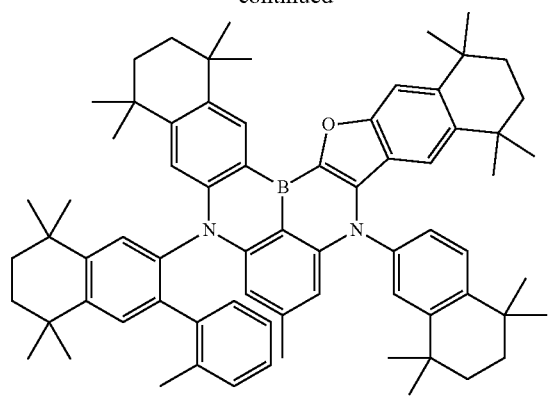
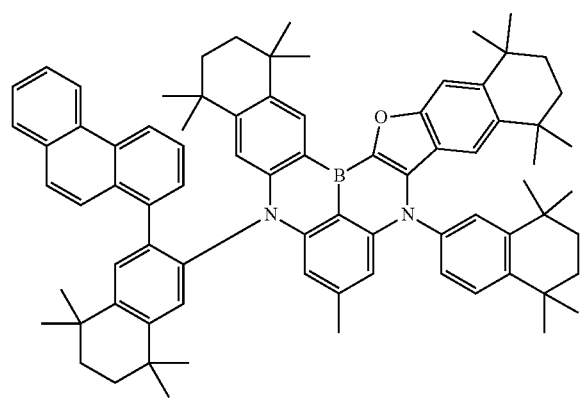
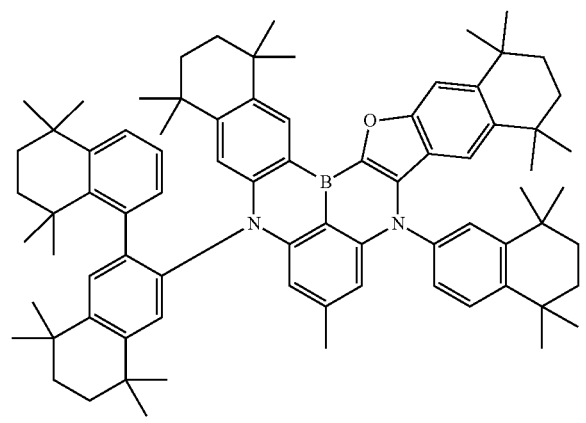
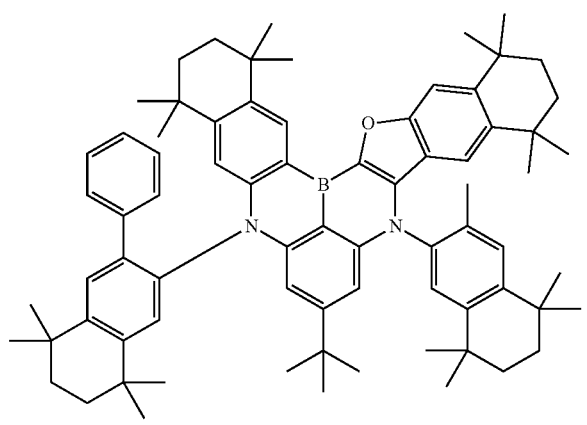
1910
-continued
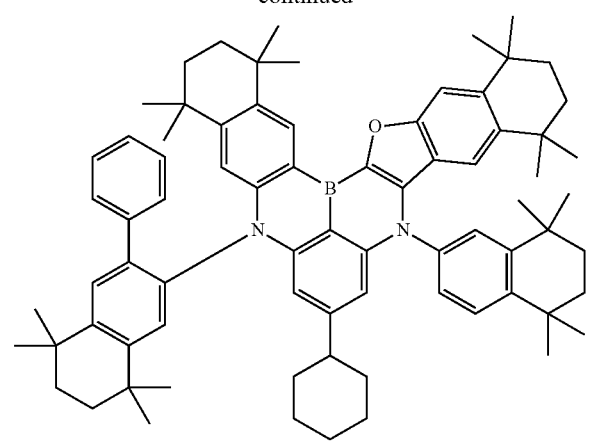
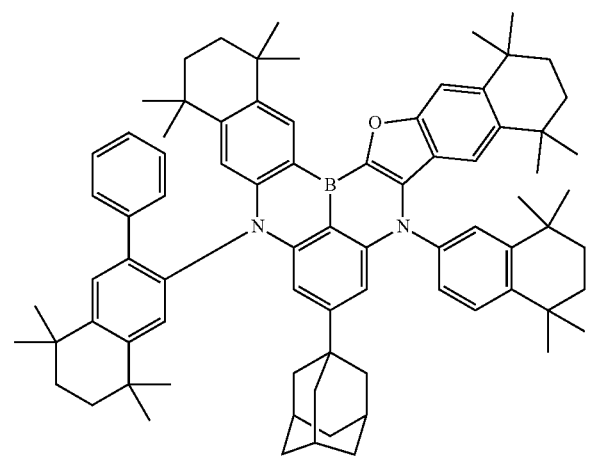
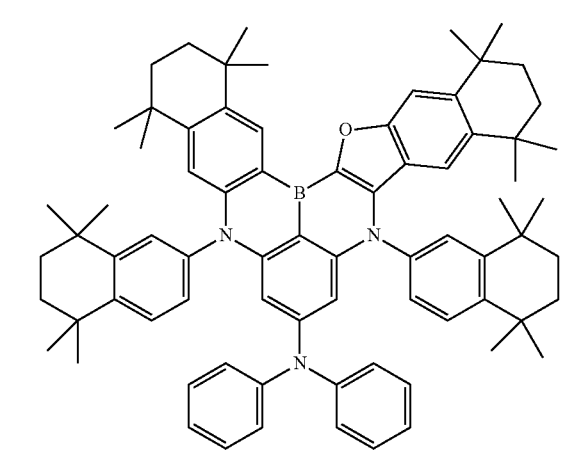

1911
-continued
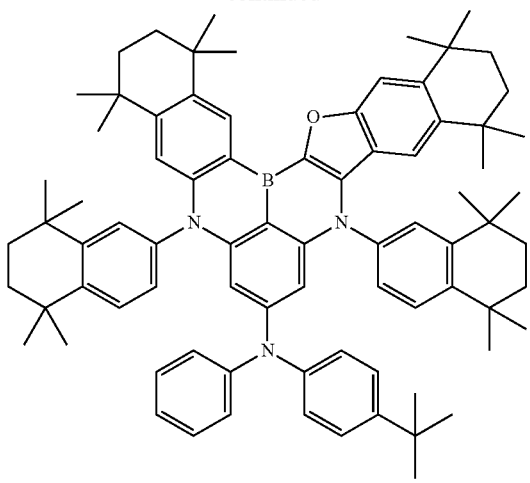
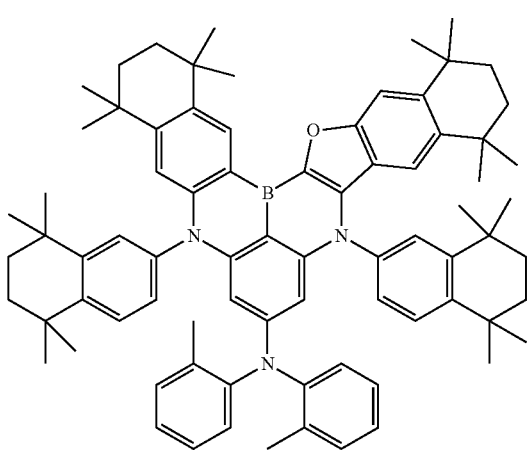
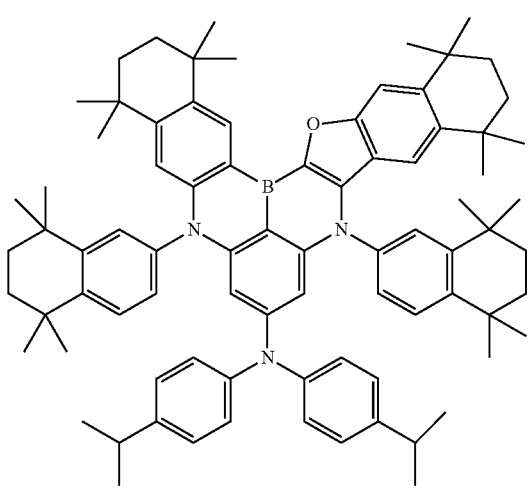
1912
-continued
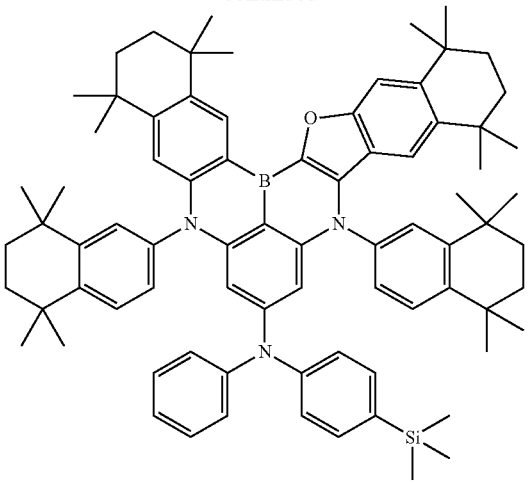
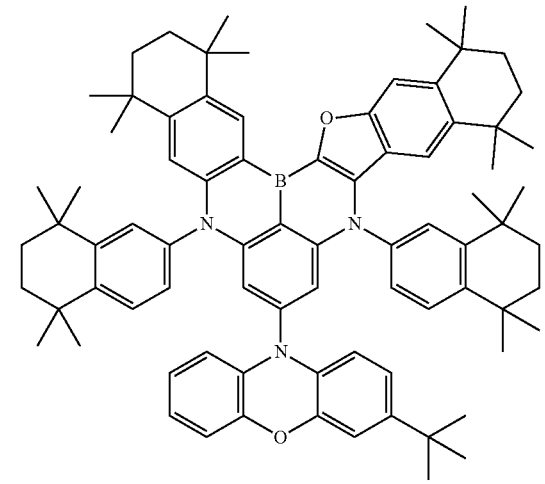
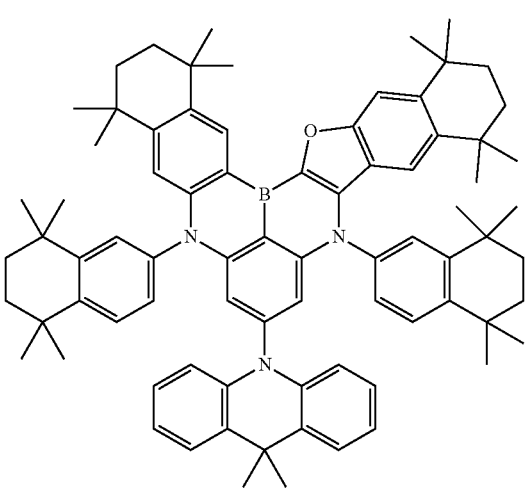

1913
-continued
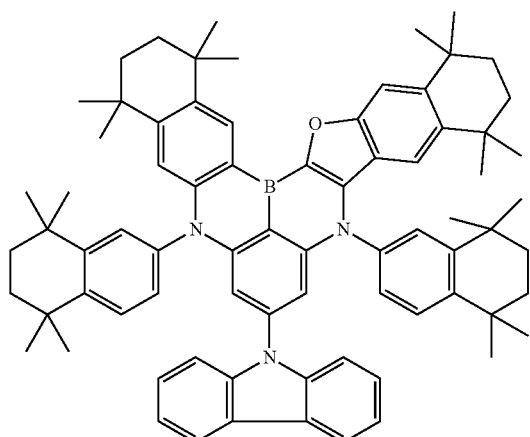
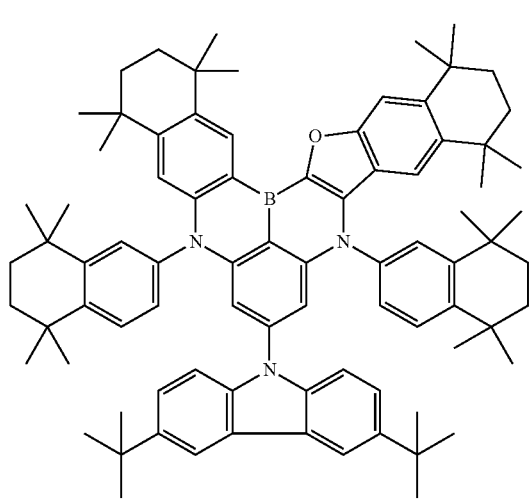
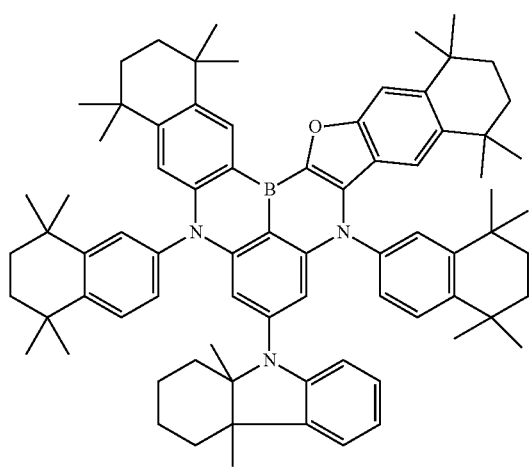
1914
-continued
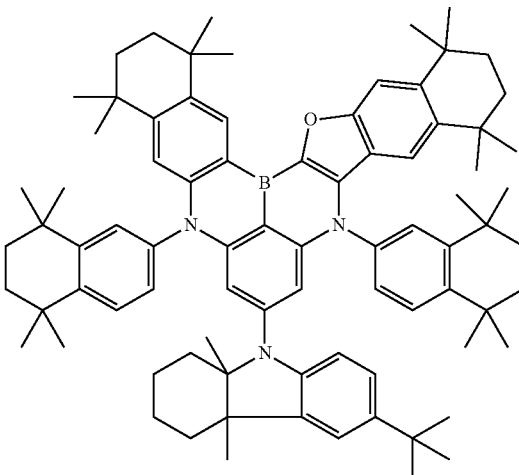
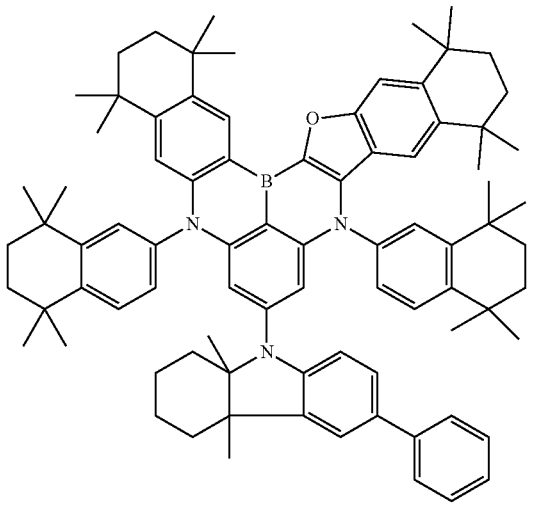
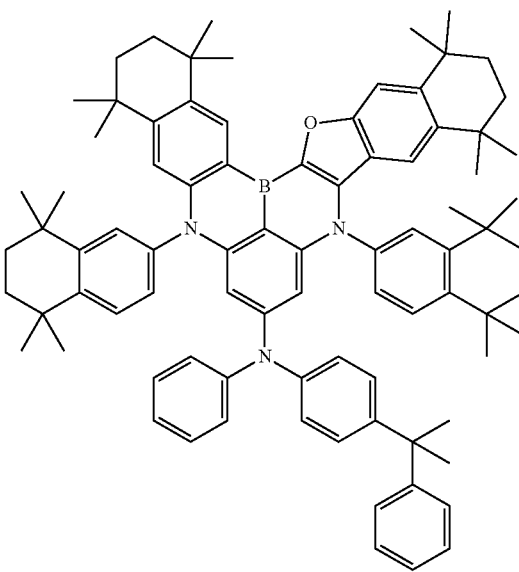

1915
-continued
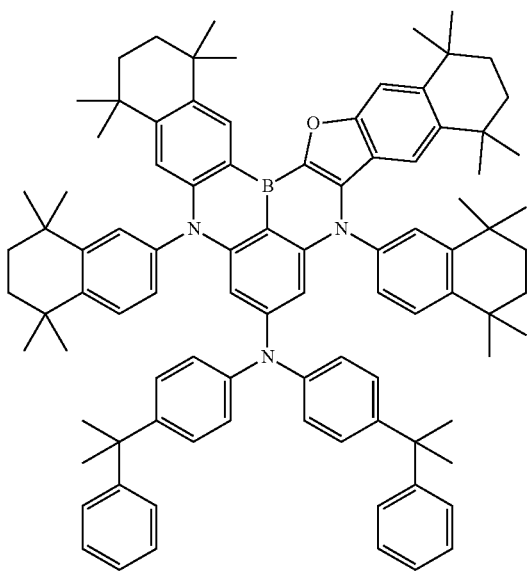
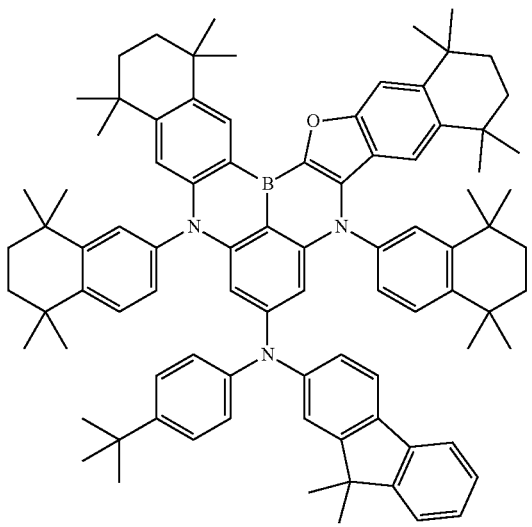
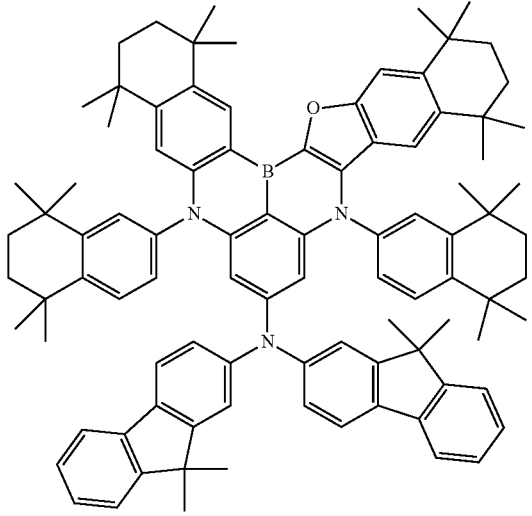
1916
-continued
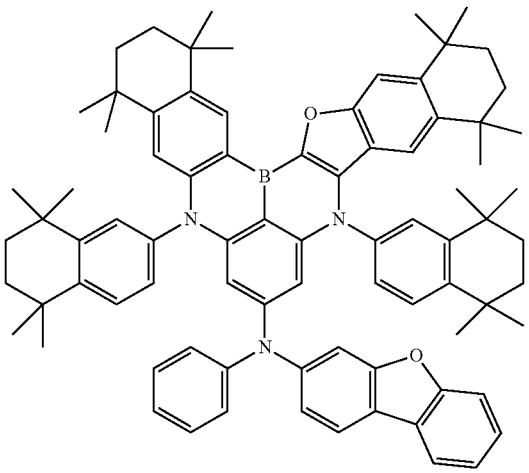
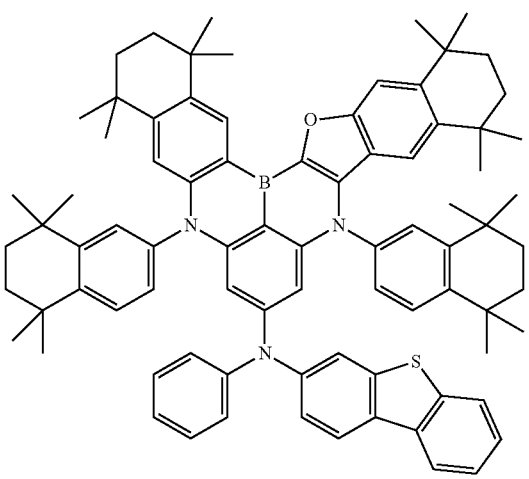
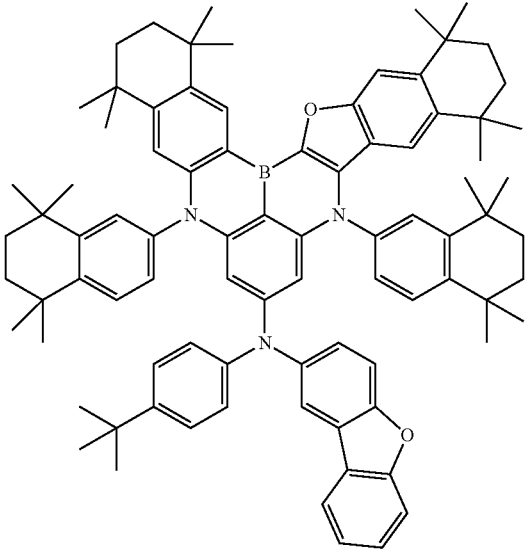

-continued
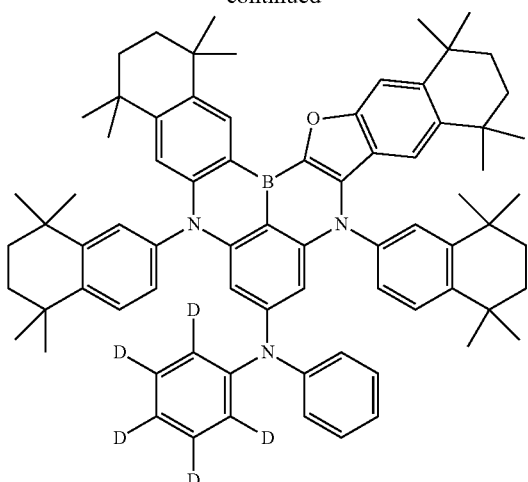 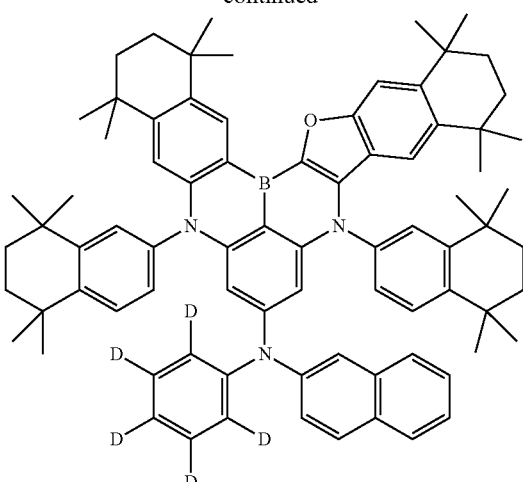
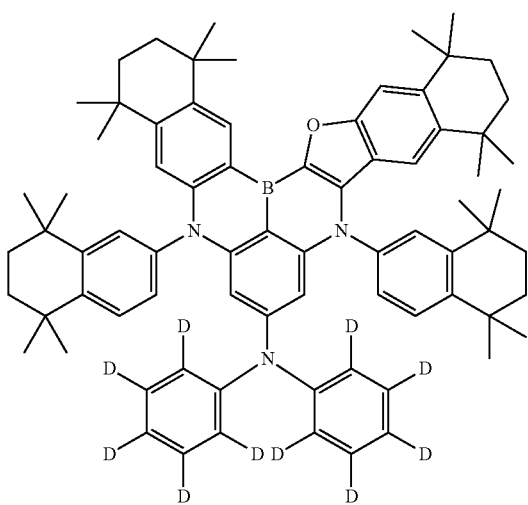 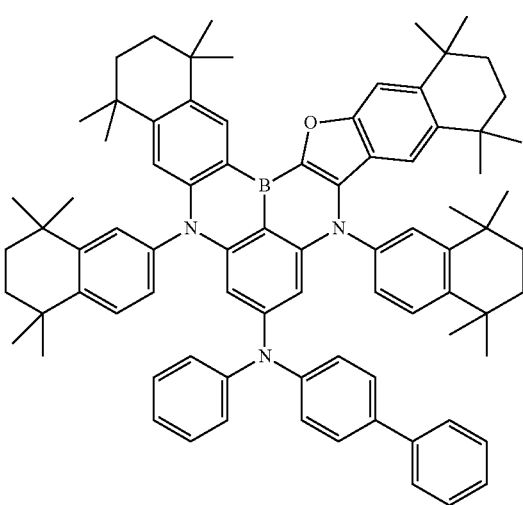
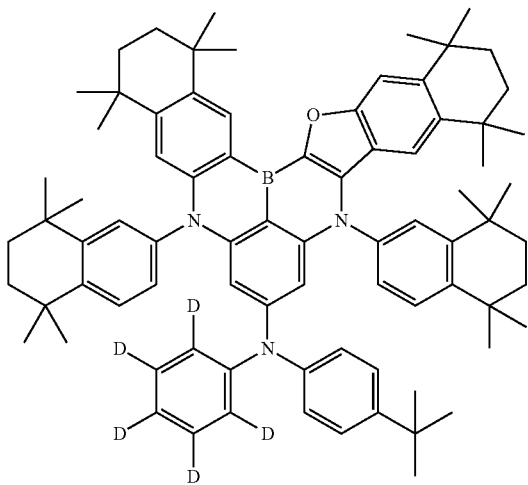 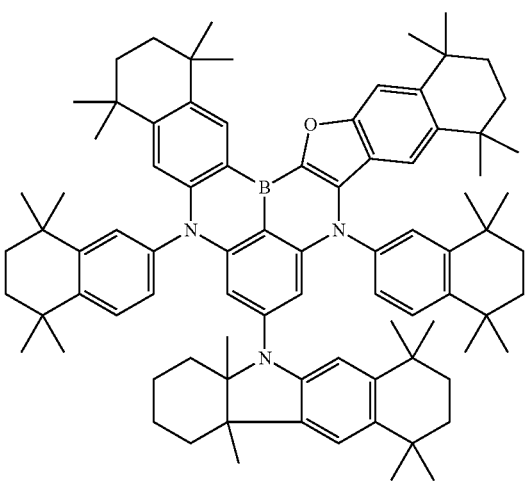

1919
-continued
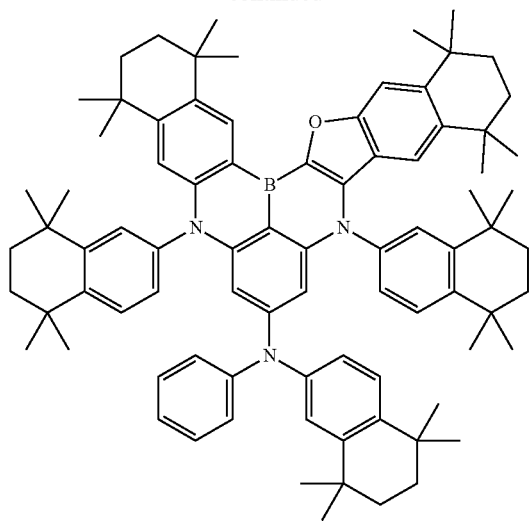
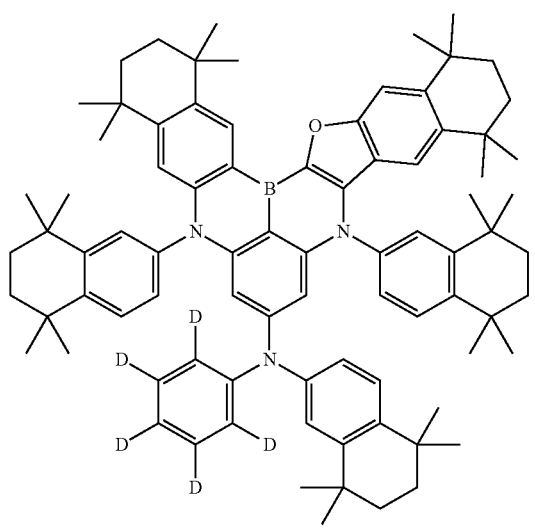
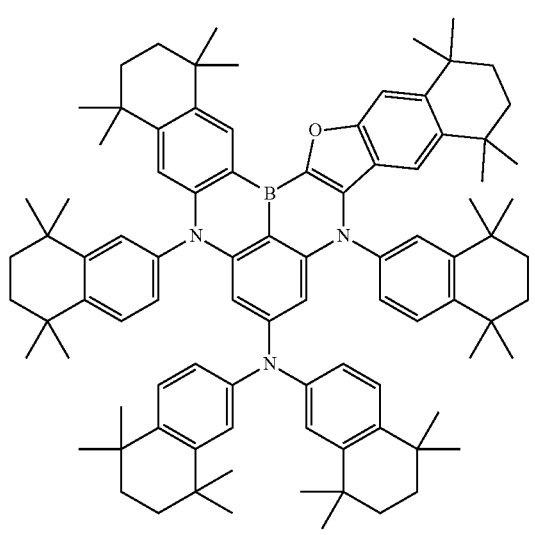
1920
-continued
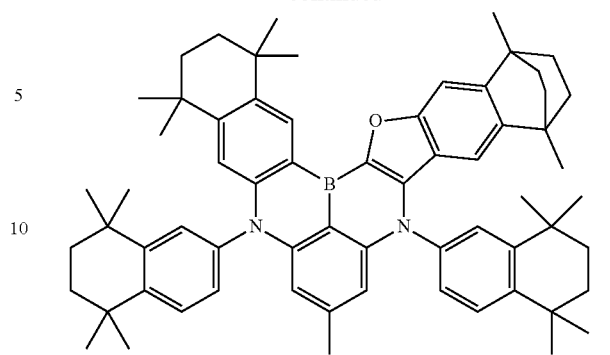
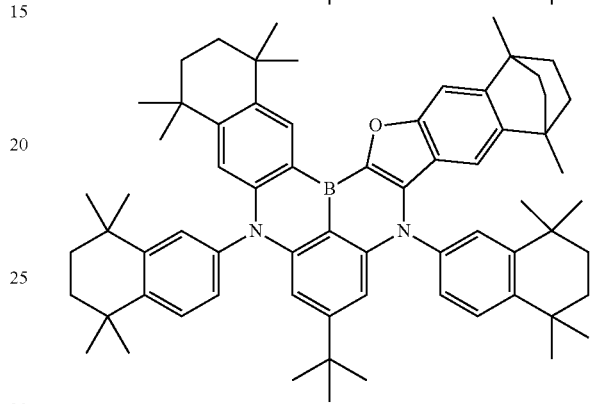
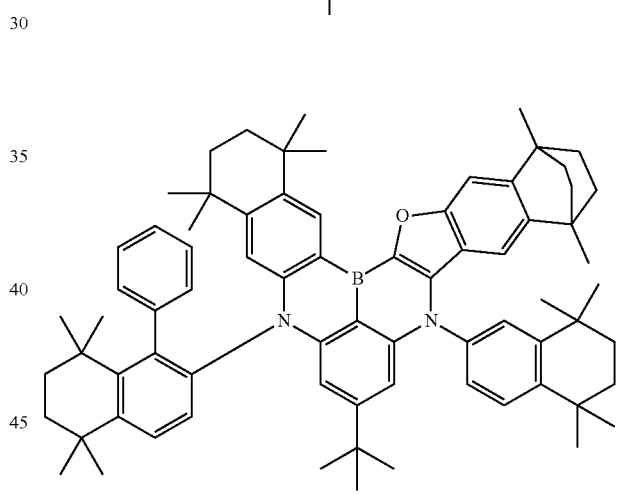
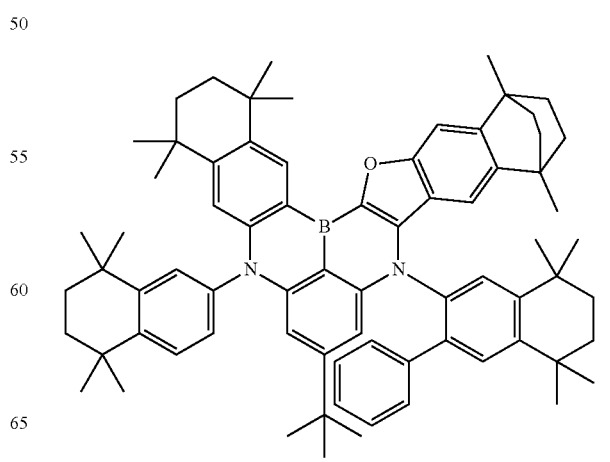

1921
-continued
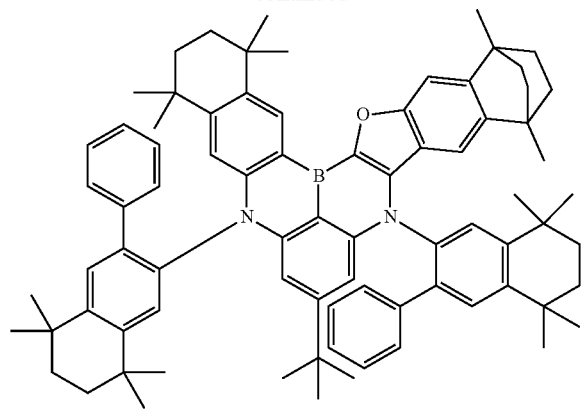
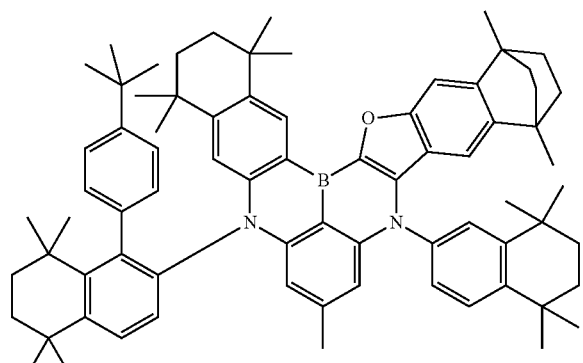
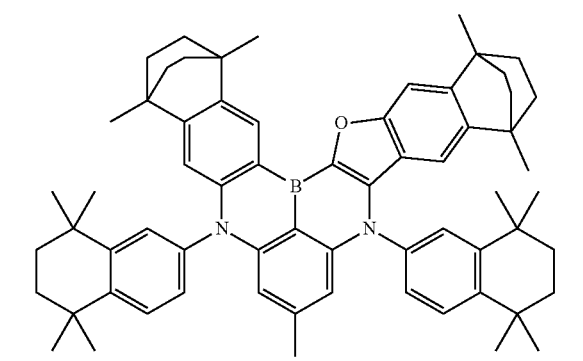
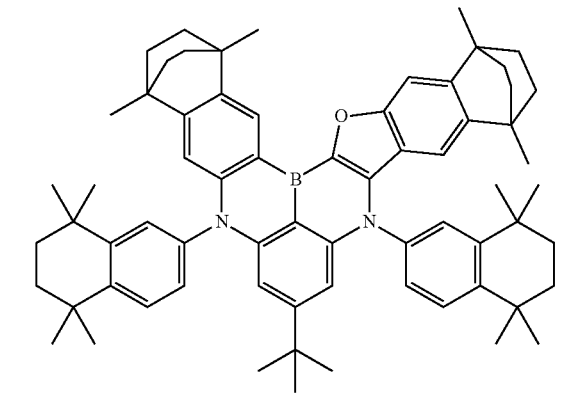
1922
-continued
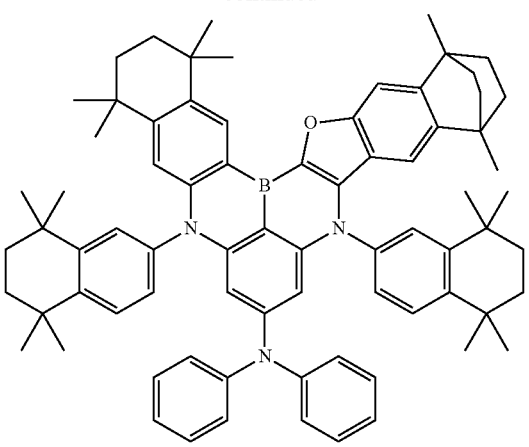
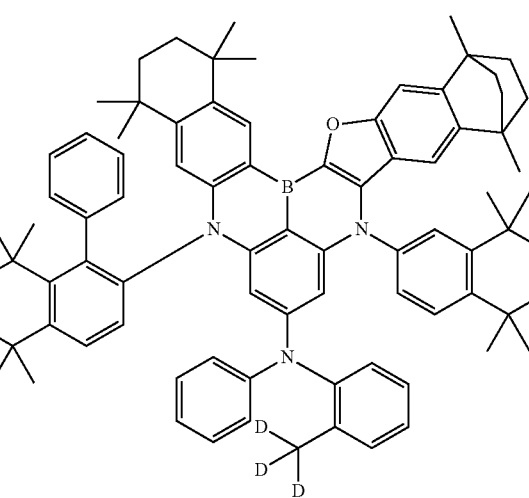
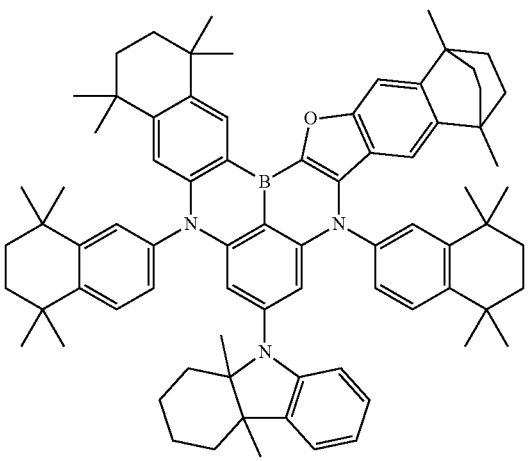

1923
-continued
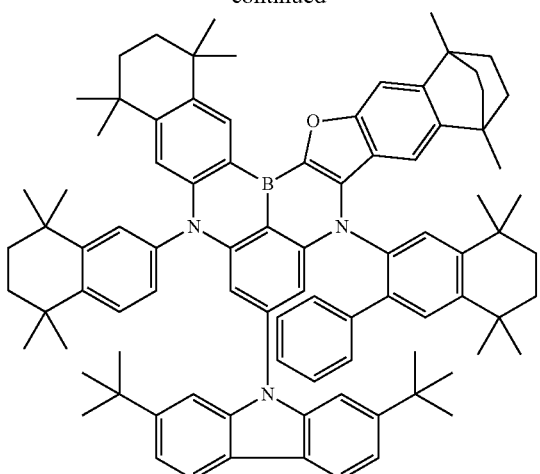
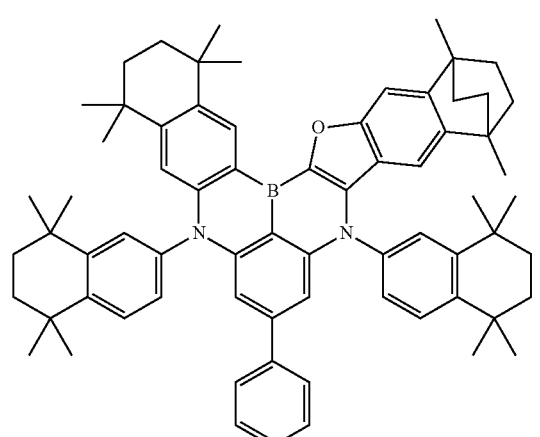
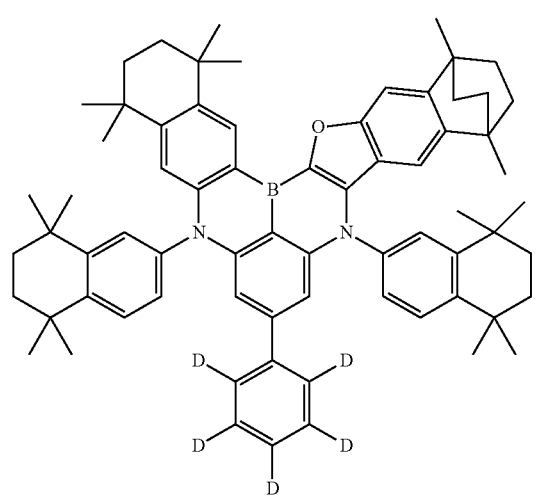
1924
-continued
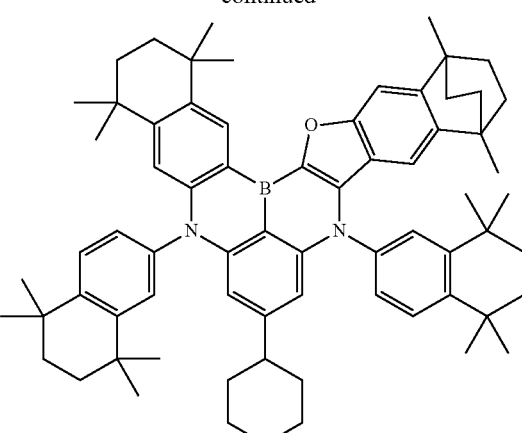
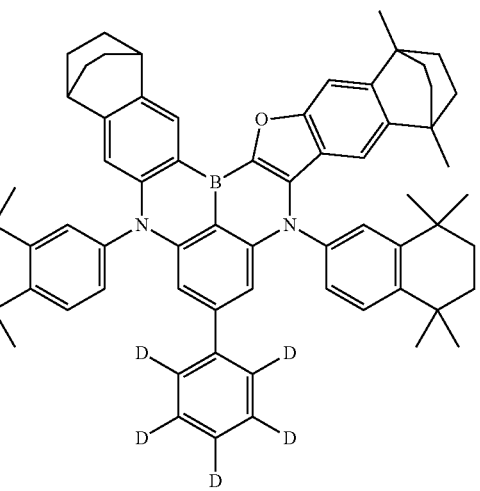
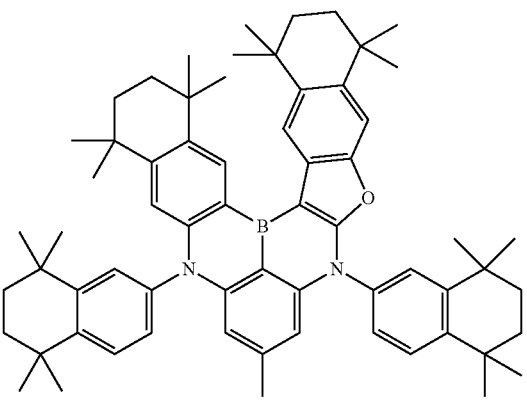

1925
-continued
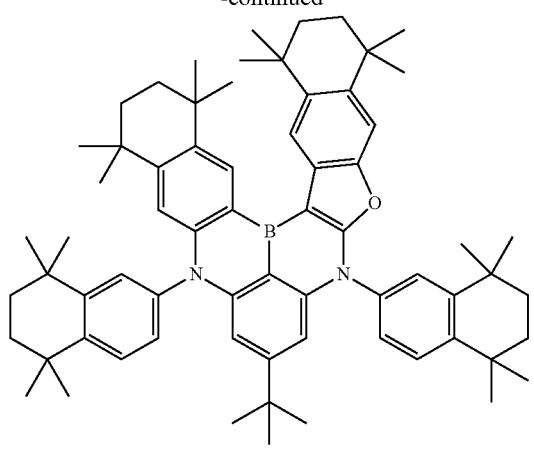
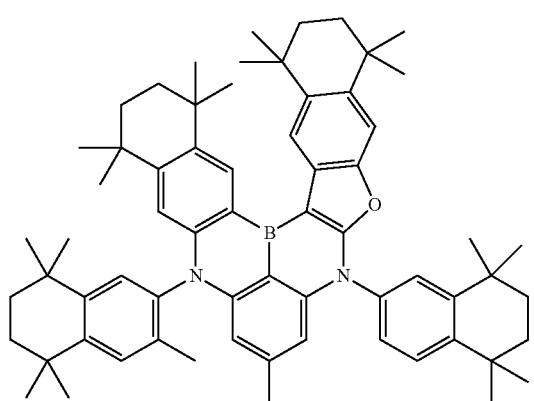
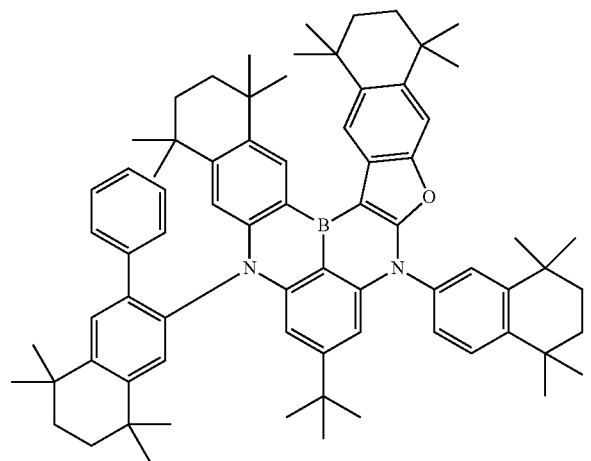
1926
-continued
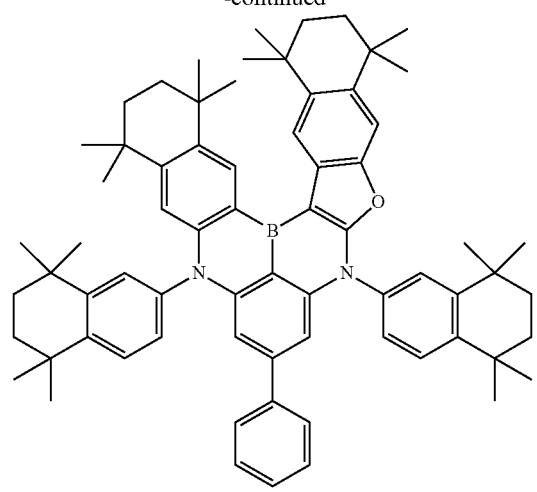
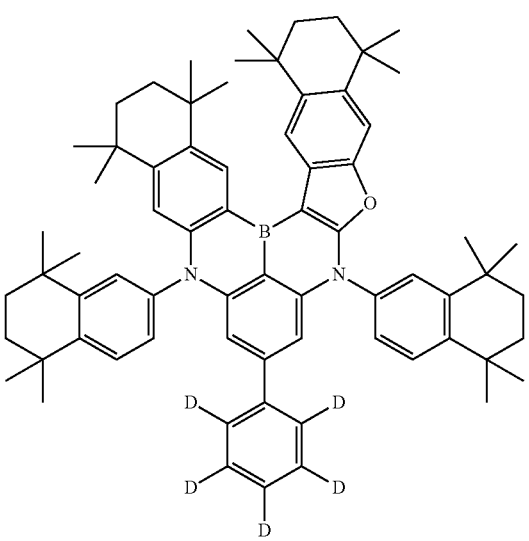
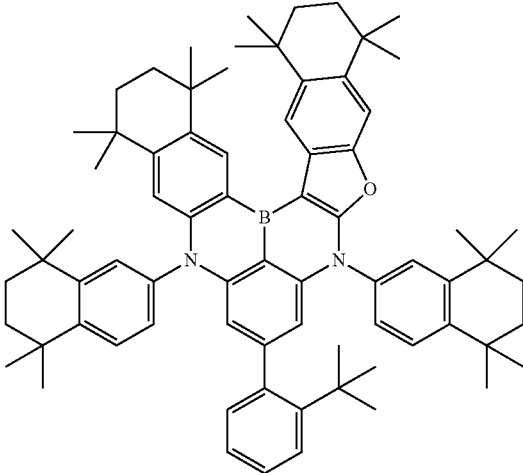

1927
-continued
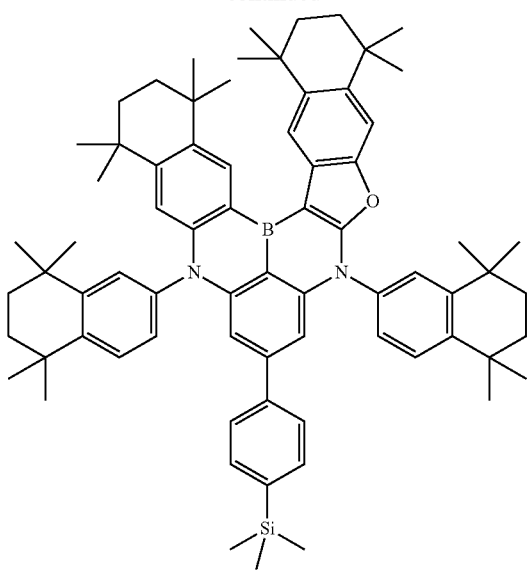
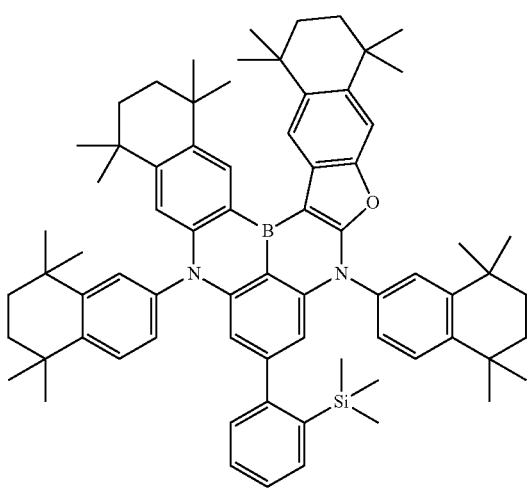
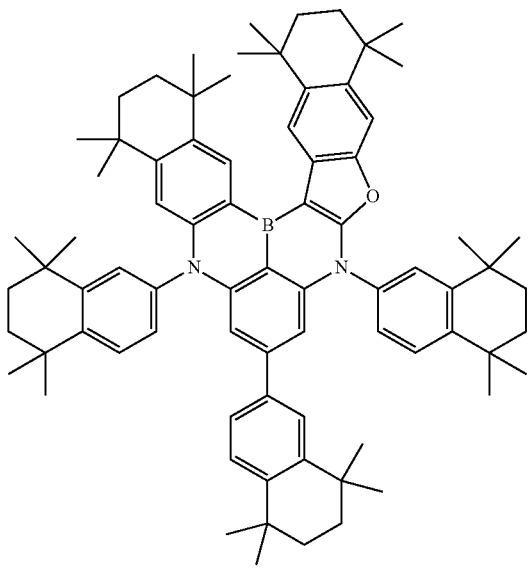
1928
-continued
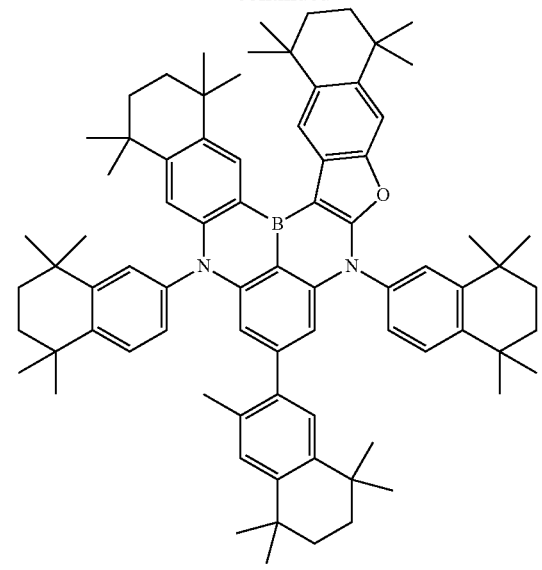
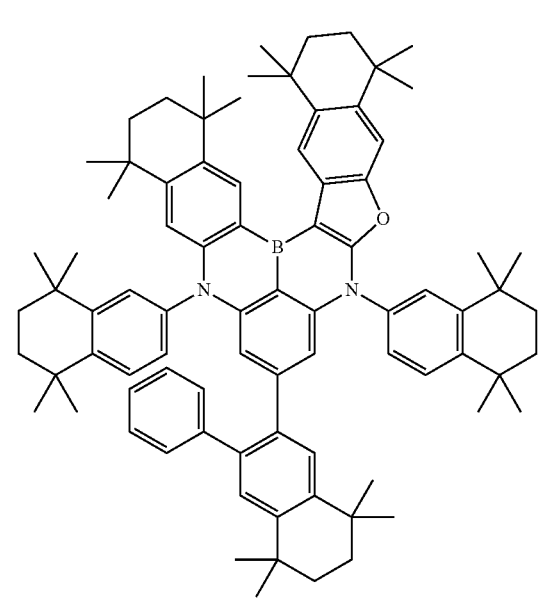
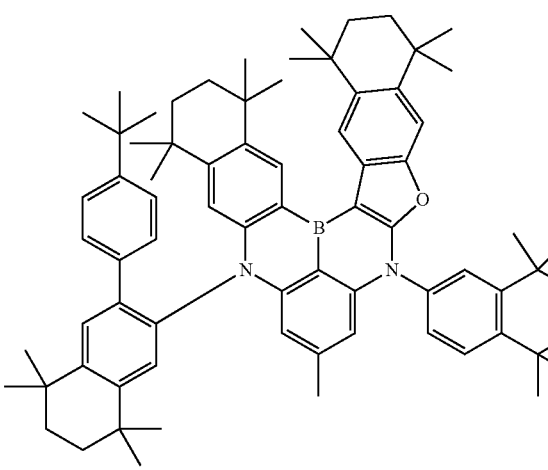

1929
-continued
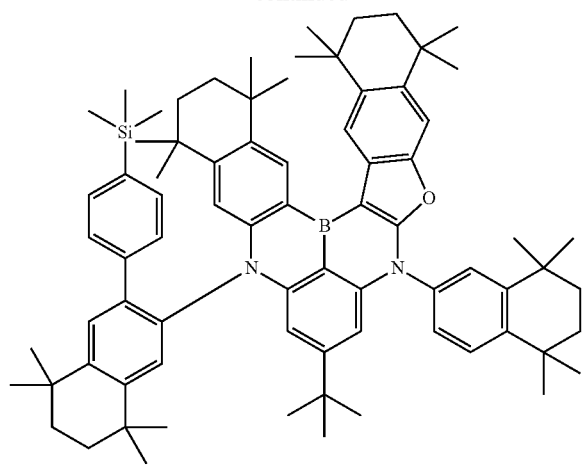
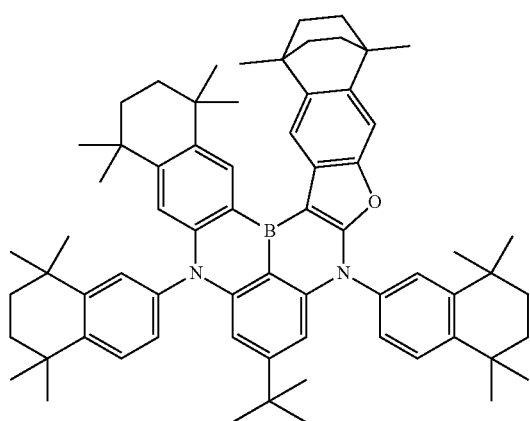
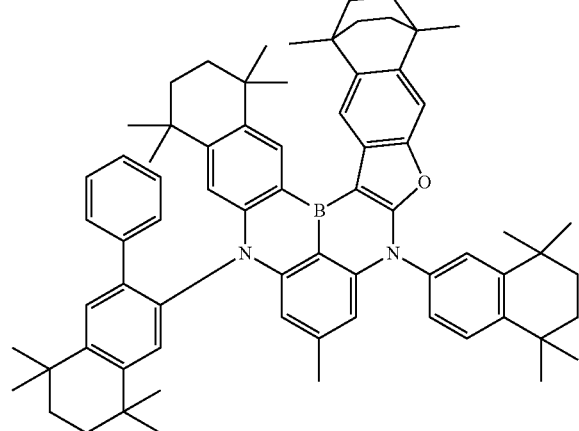
1930
-continued
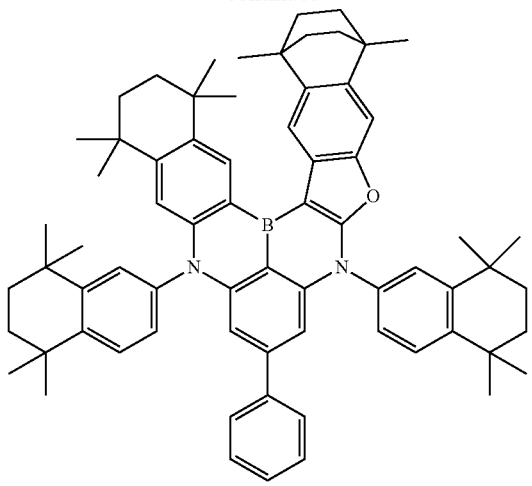
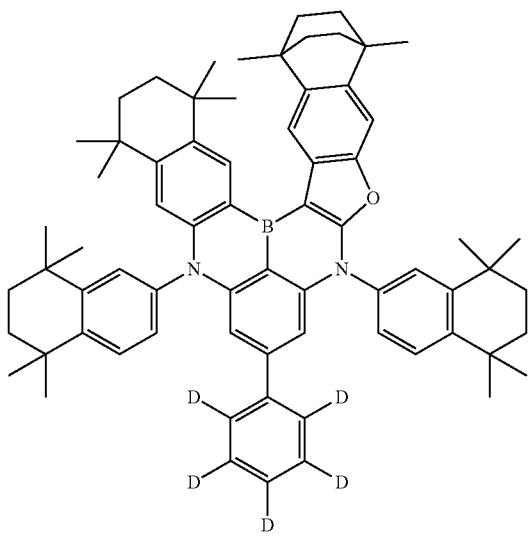
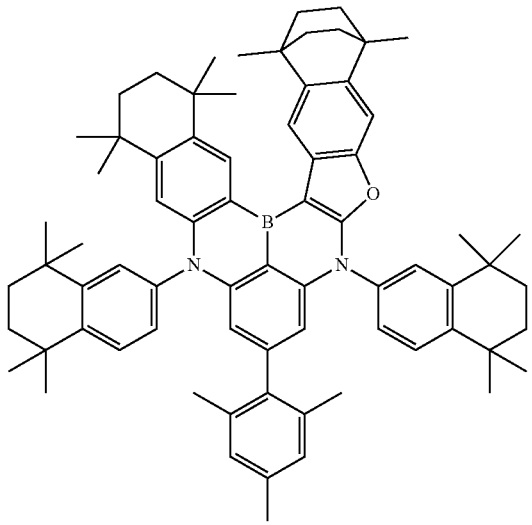

1931
-continued
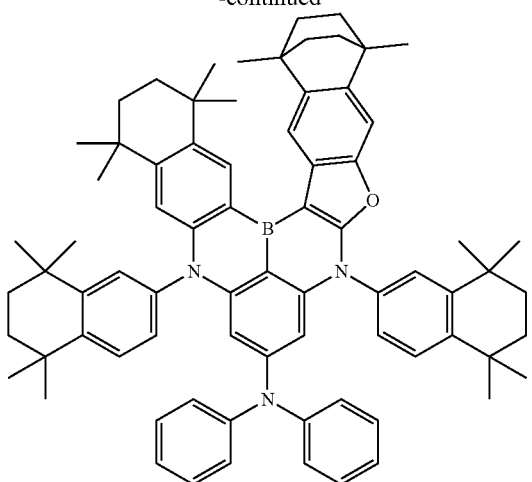
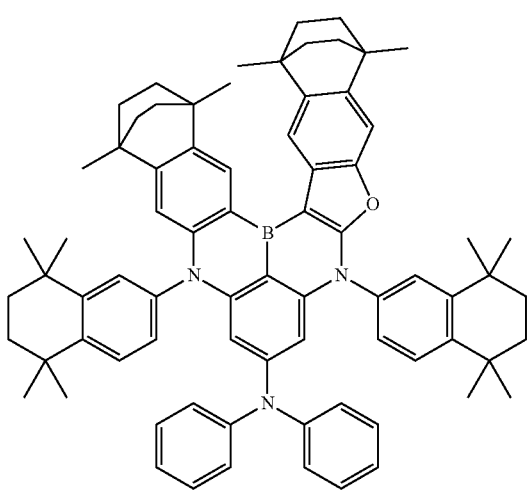
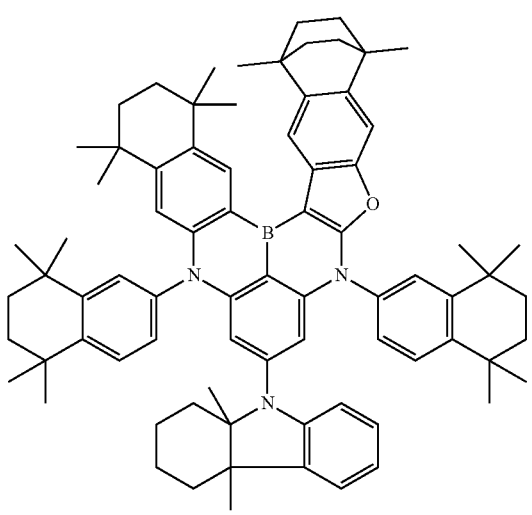
1932
-continued
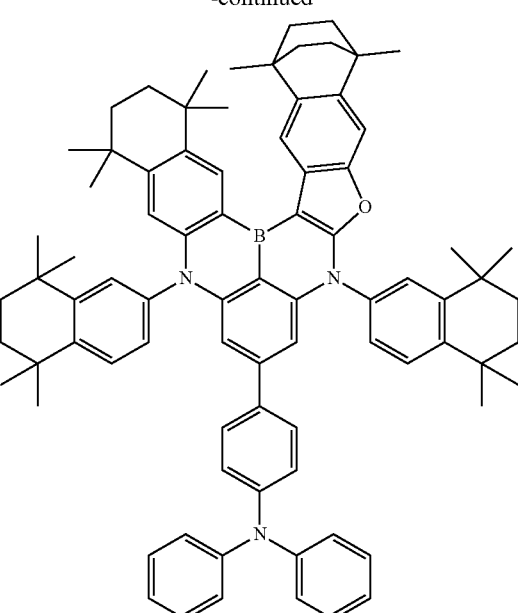
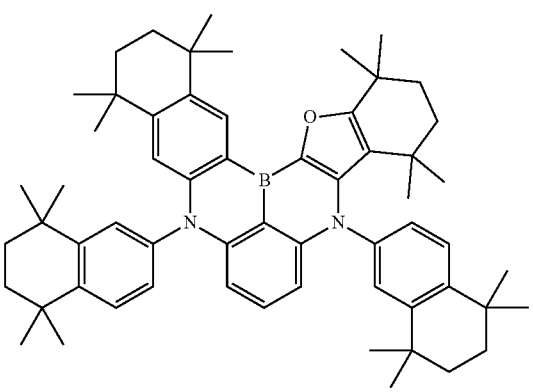
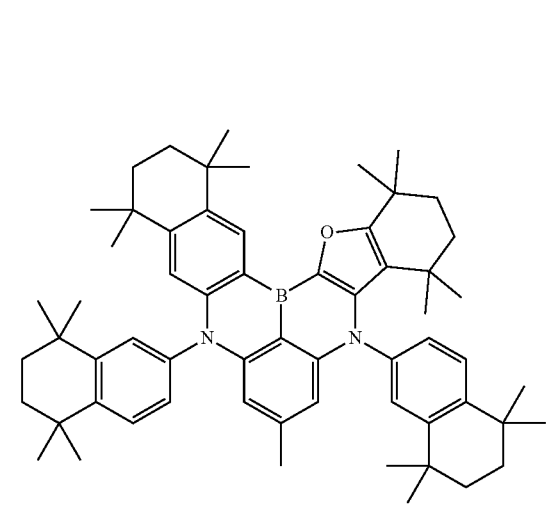

1933
-continued
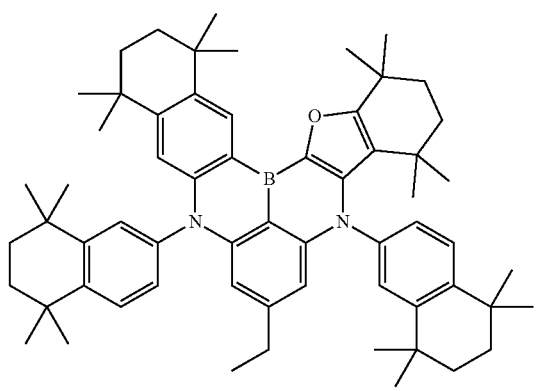
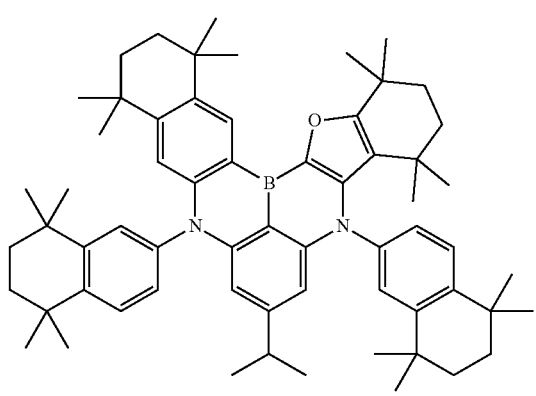
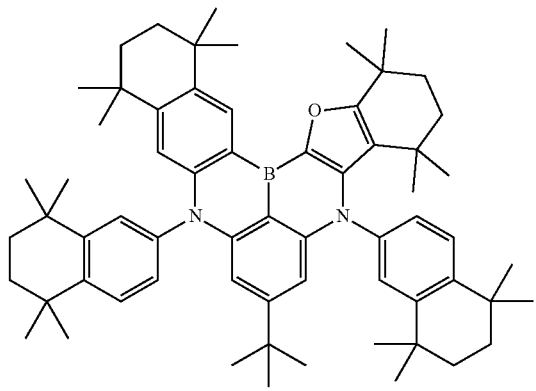
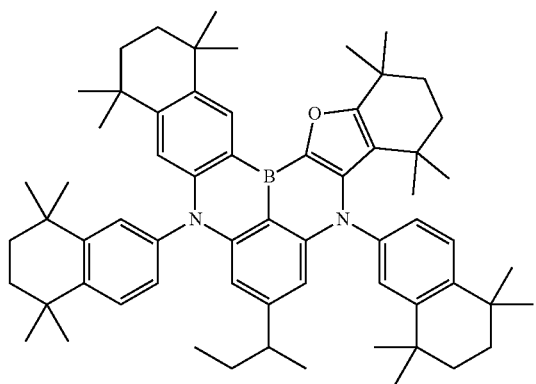
1934
-continued
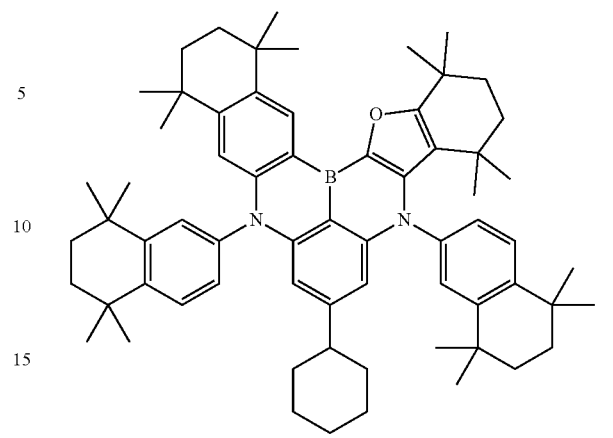
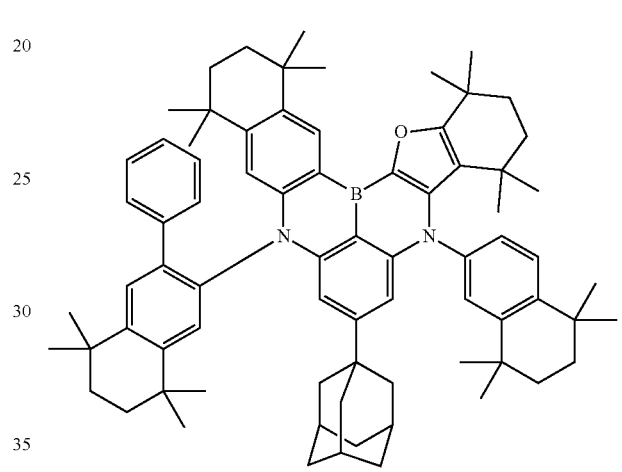
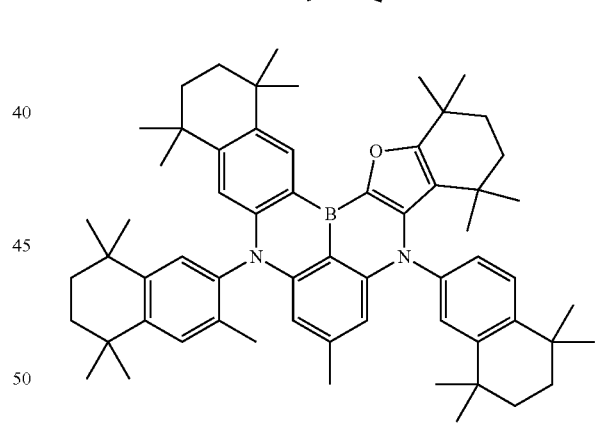
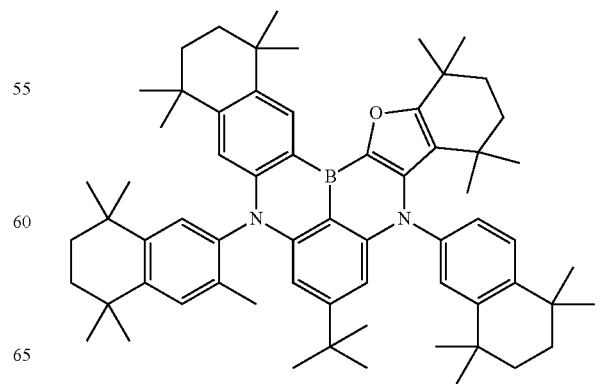

1935
-continued
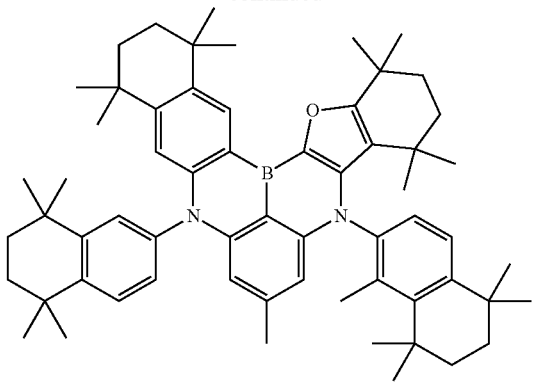
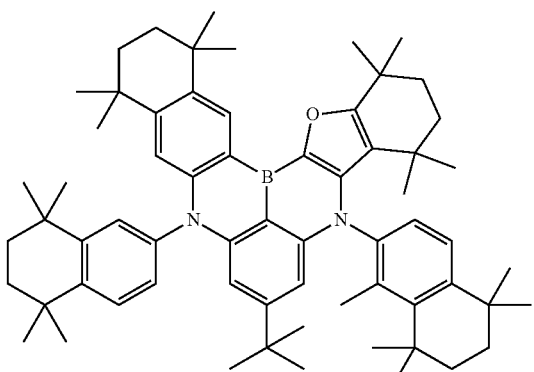
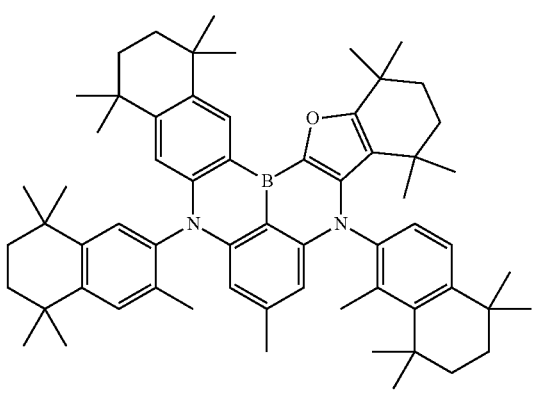
1936
-continued
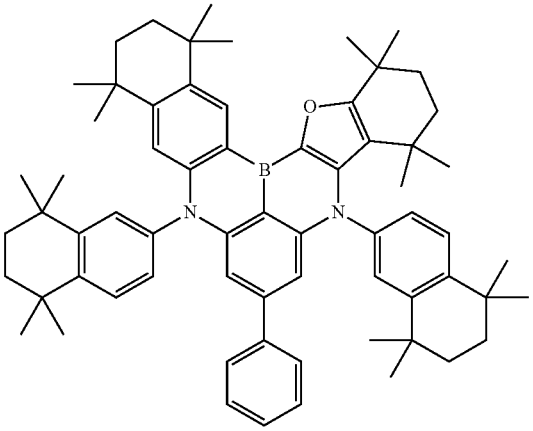
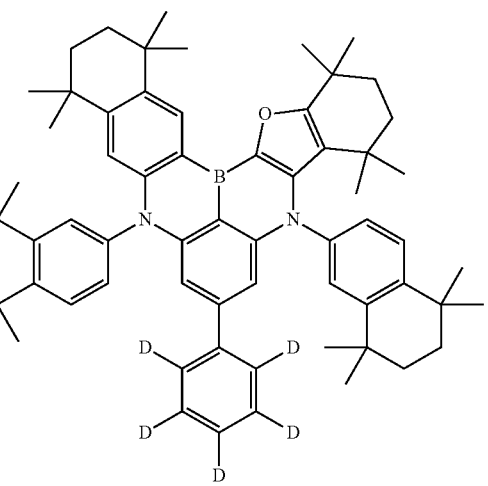
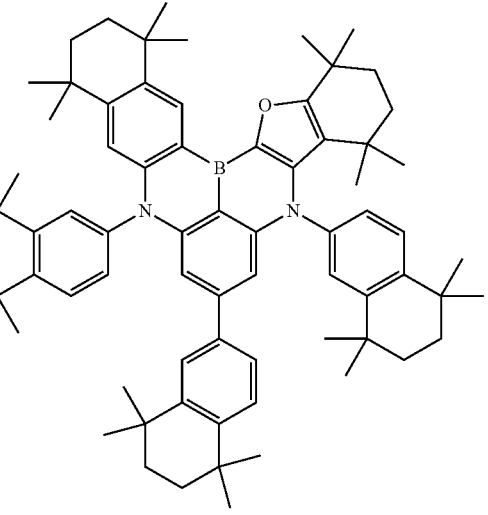

| 1937 -continued | 1938 -continued |
|---|---|
| 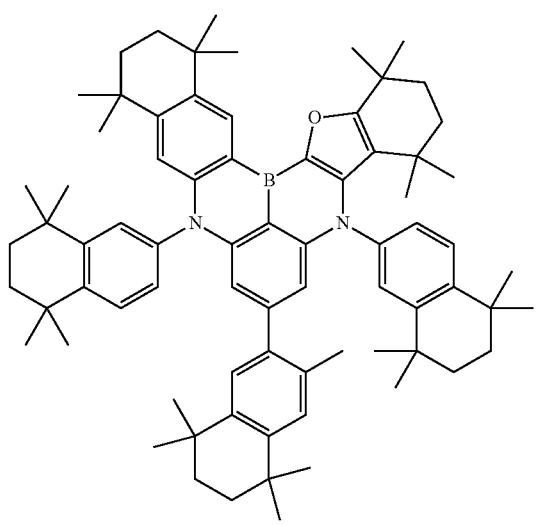 | 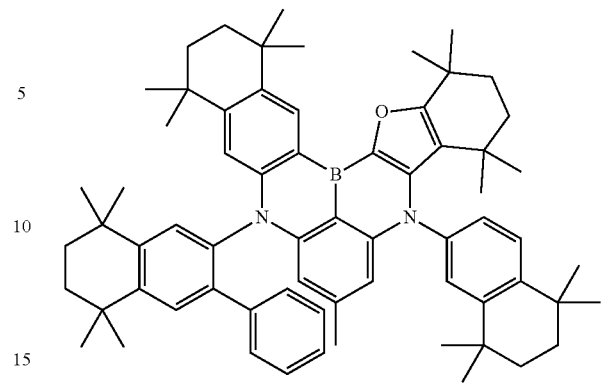 |
| 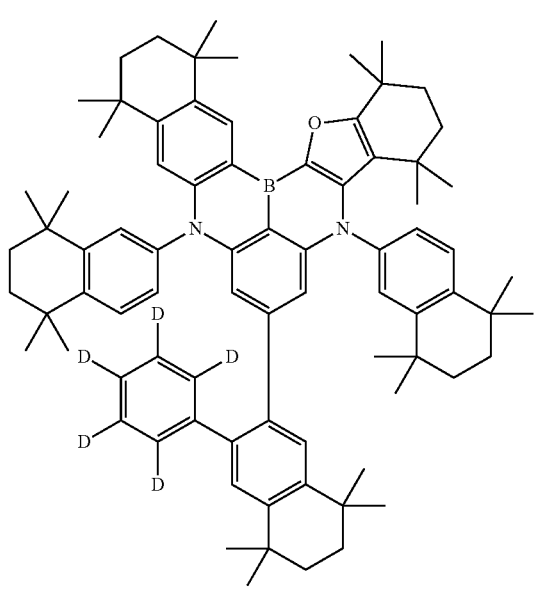 | 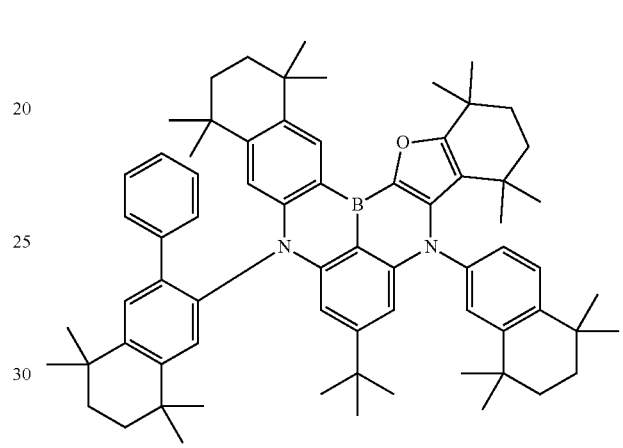 |
| 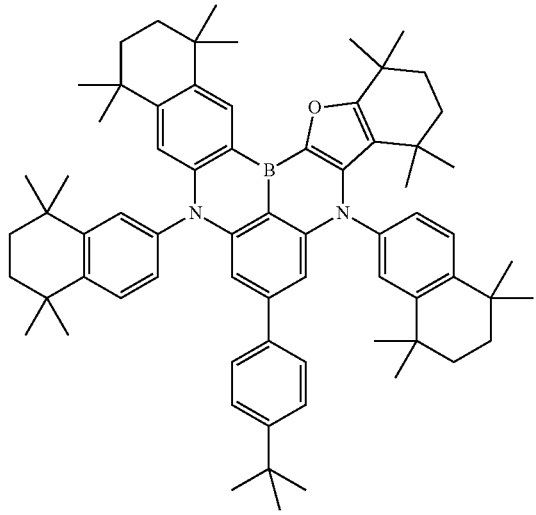 |  |
| |  |

1939
-continued
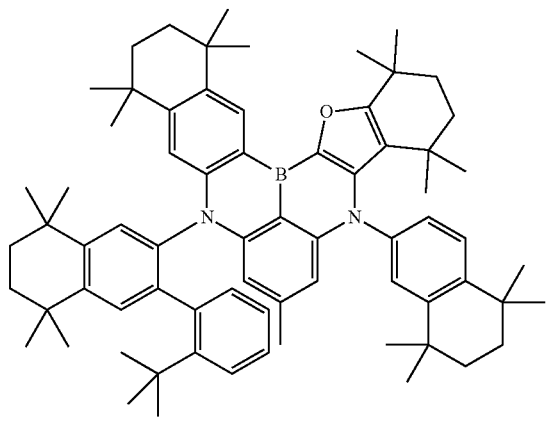
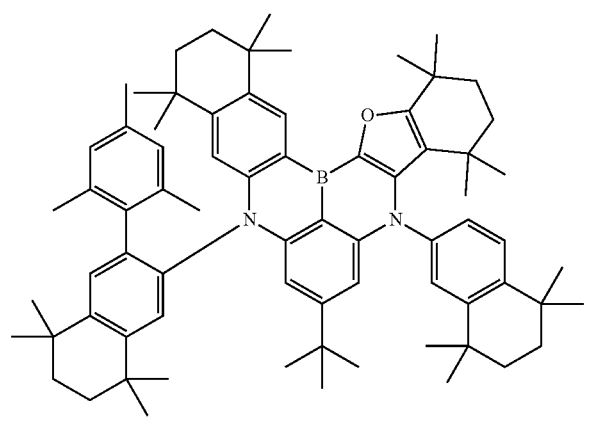
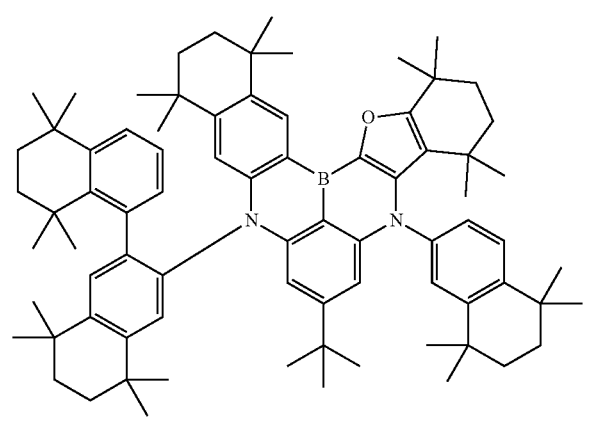
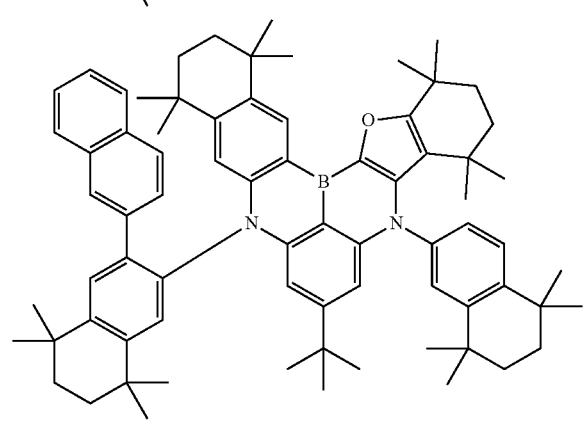
1940
-continued
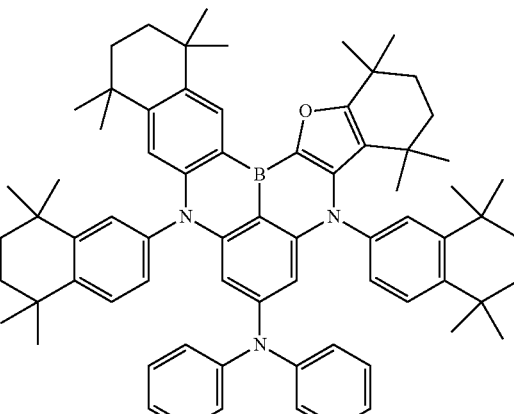
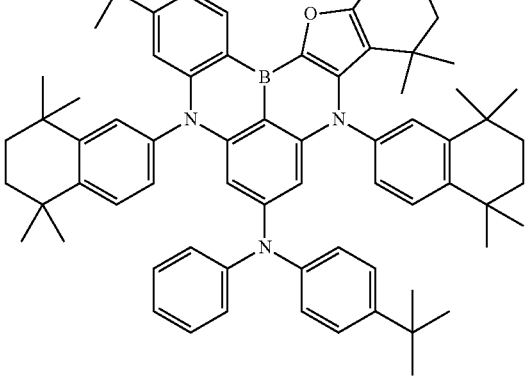
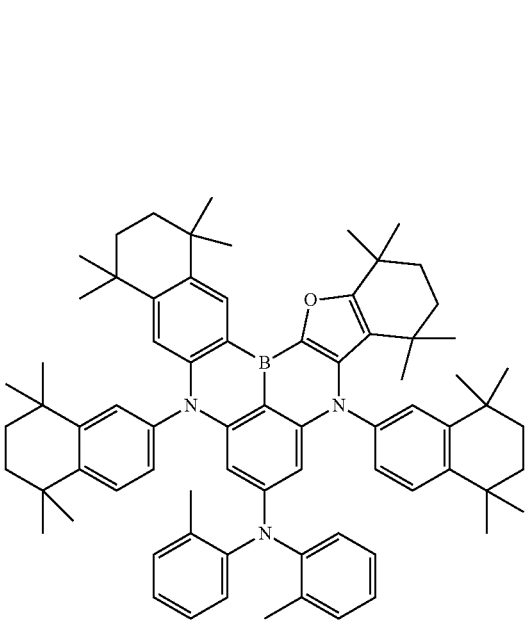

1941
-continued
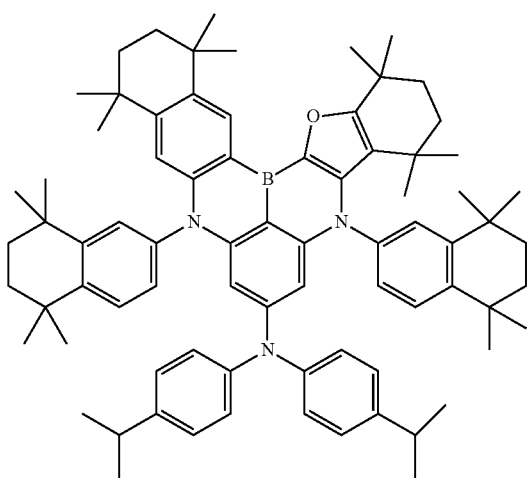
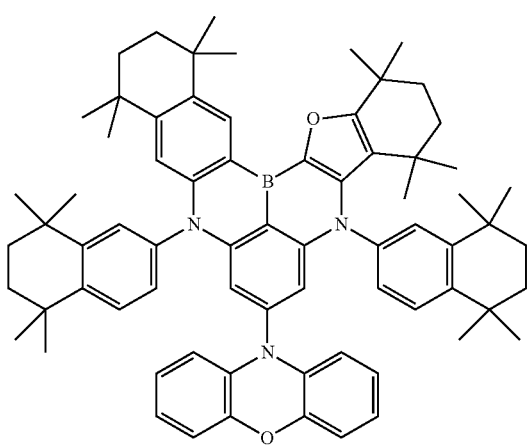
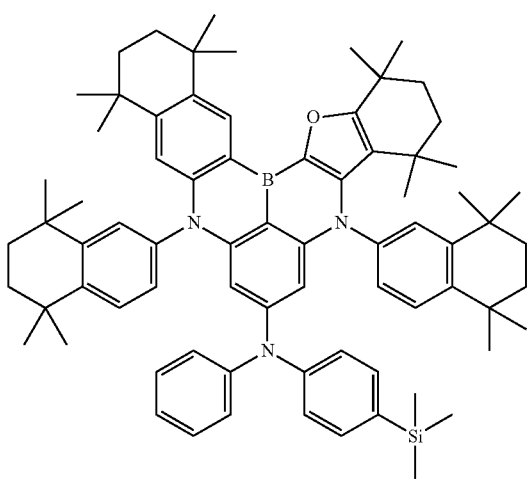
1942
-continued
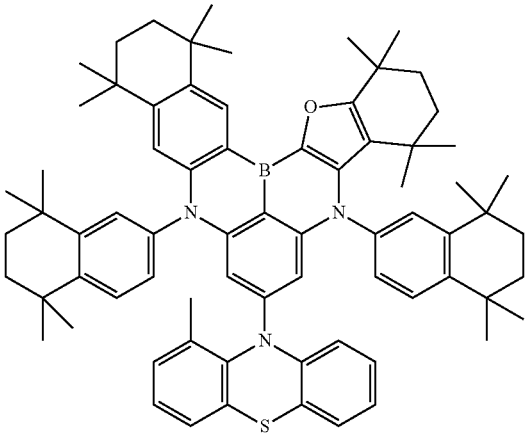
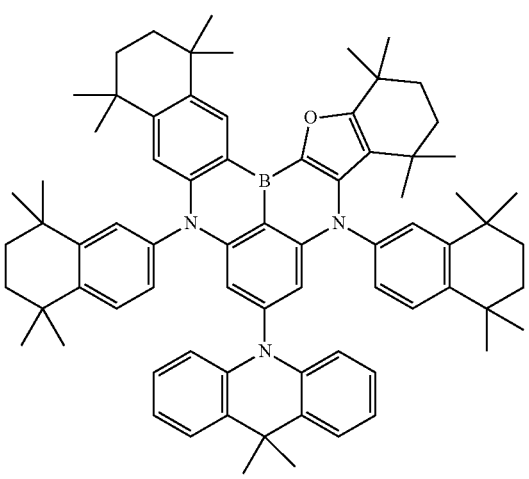
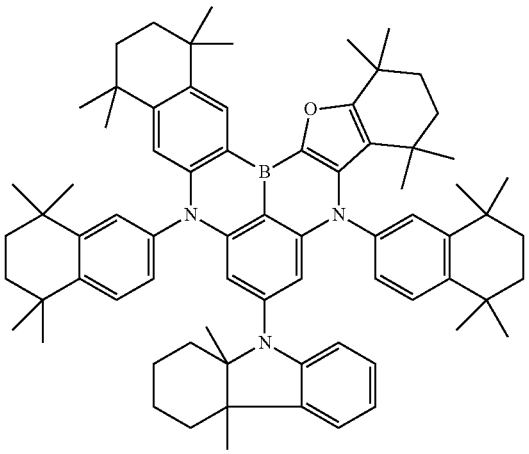

1943
-continued
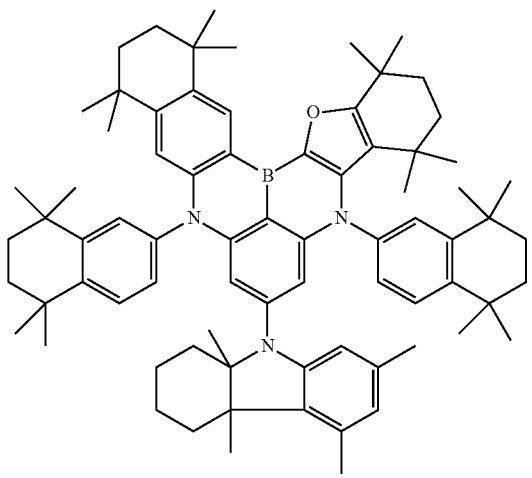
1944
-continued
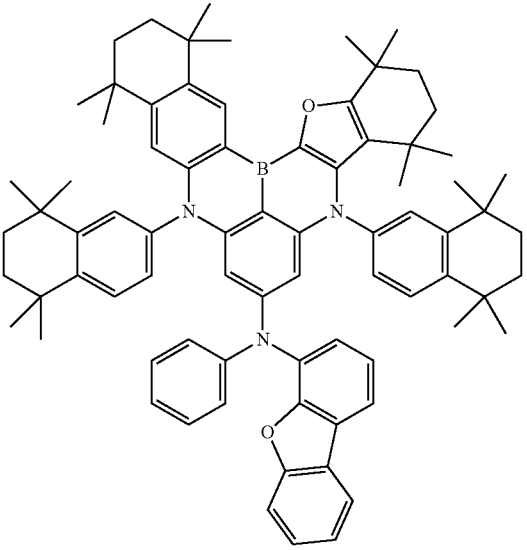
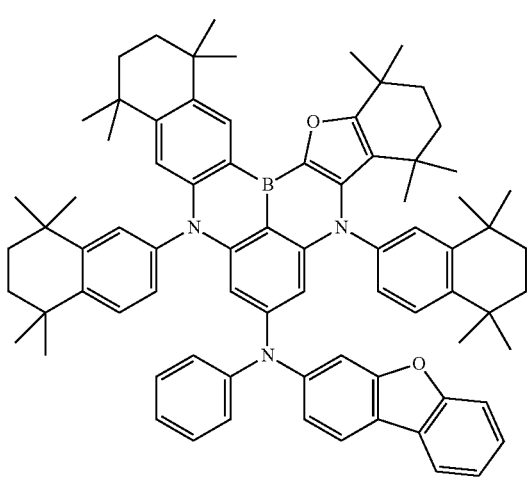
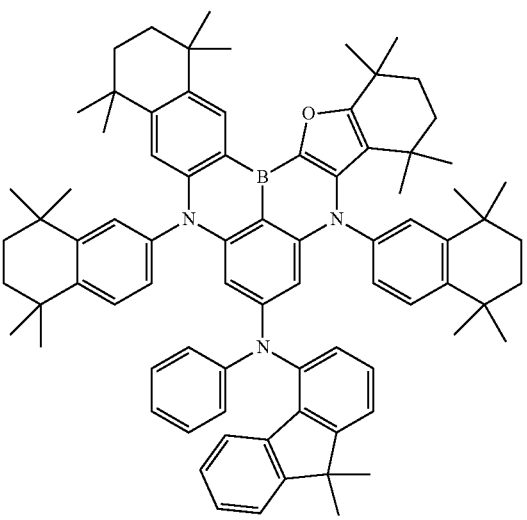
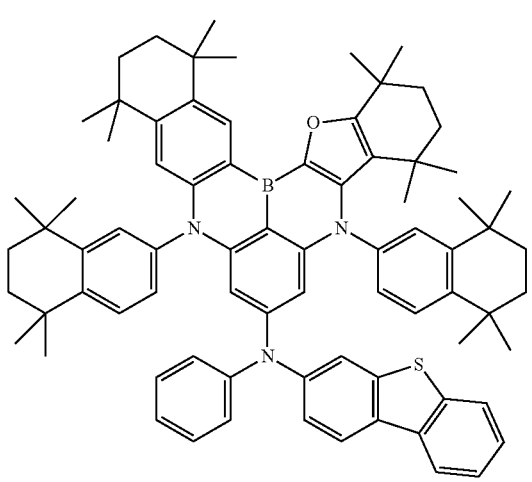
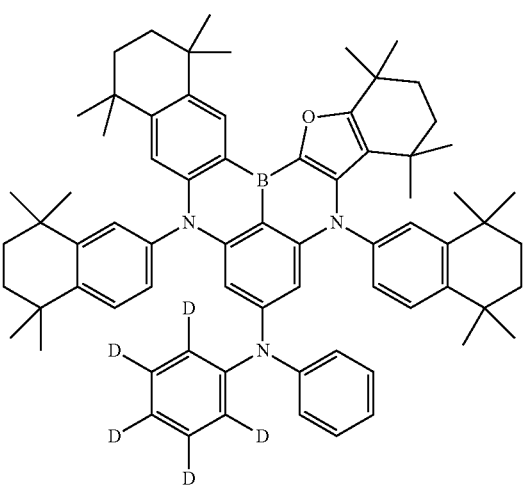

1945
-continued
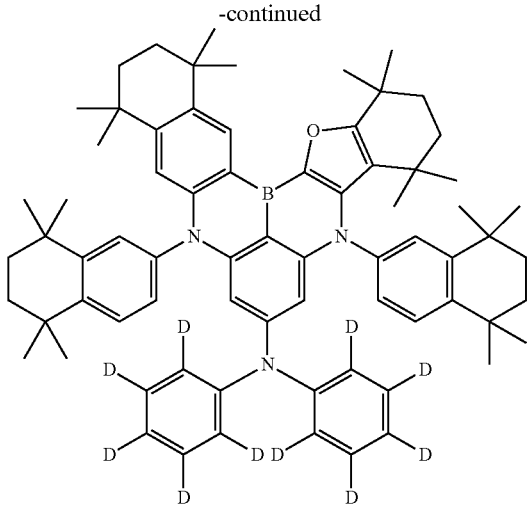
1946
-continued
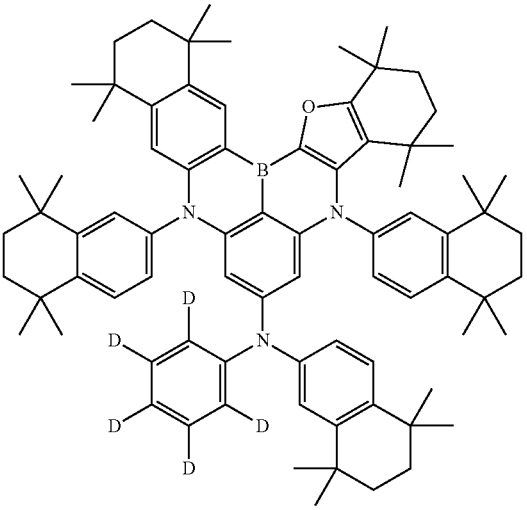
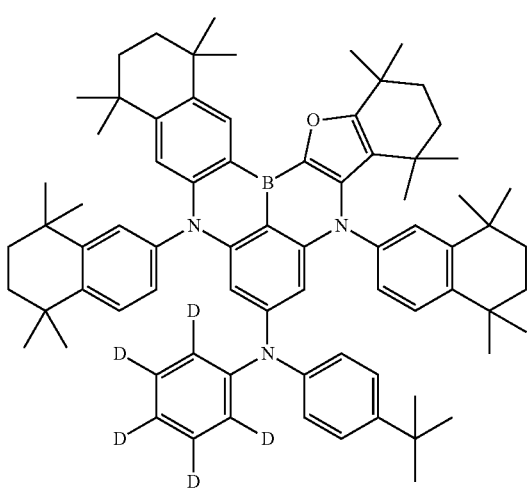
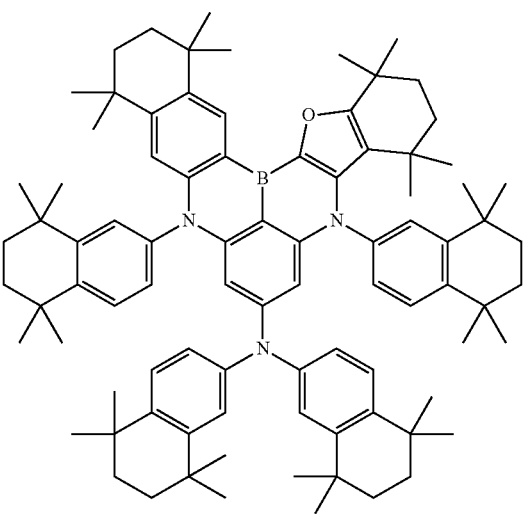
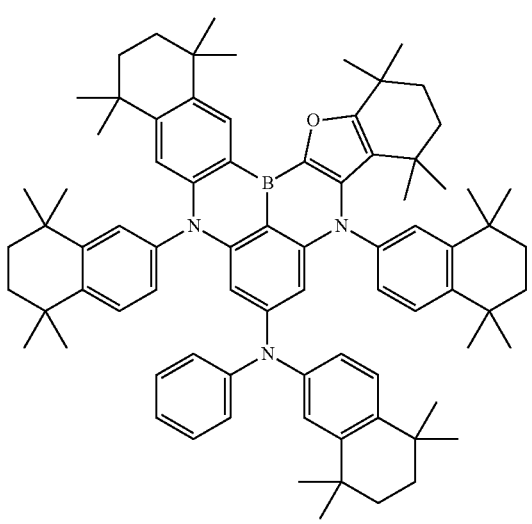
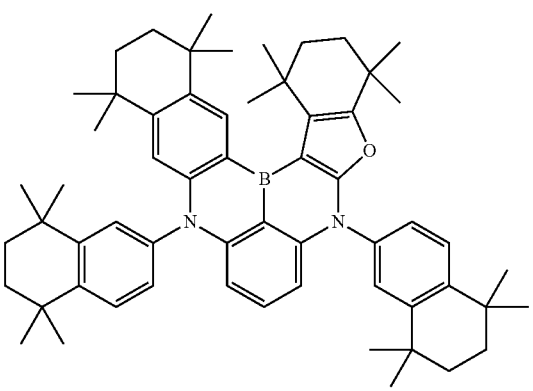

1947
-continued
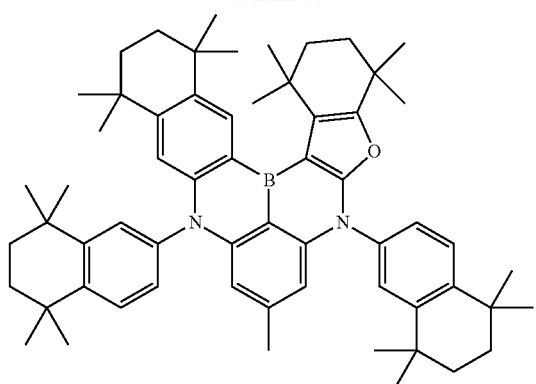
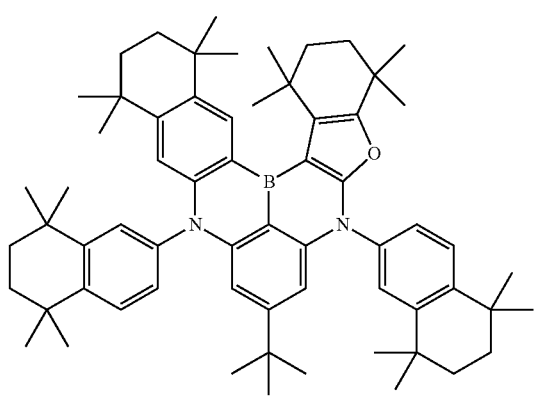
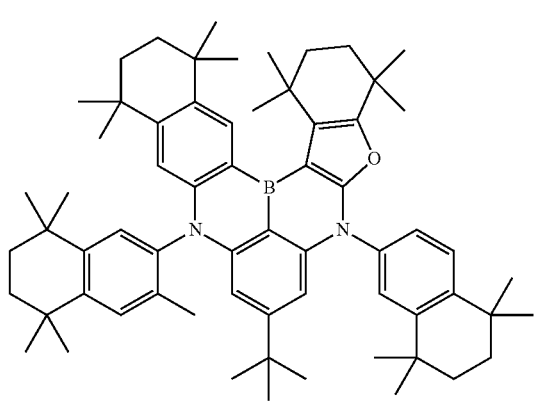
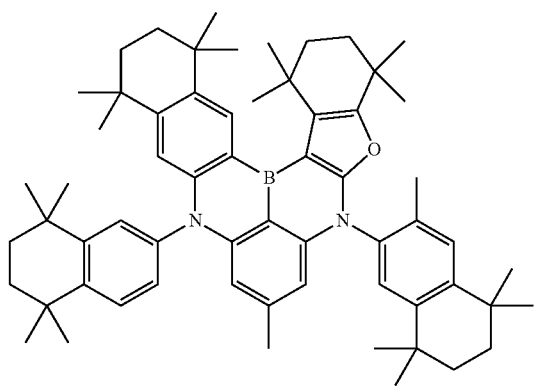
1948
-continued
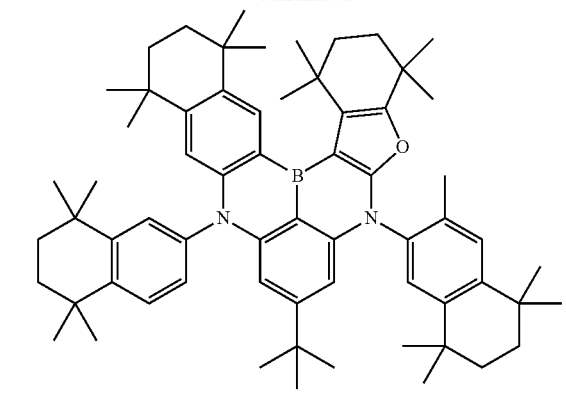
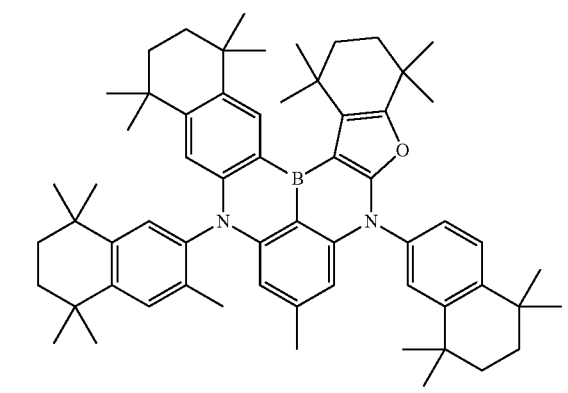
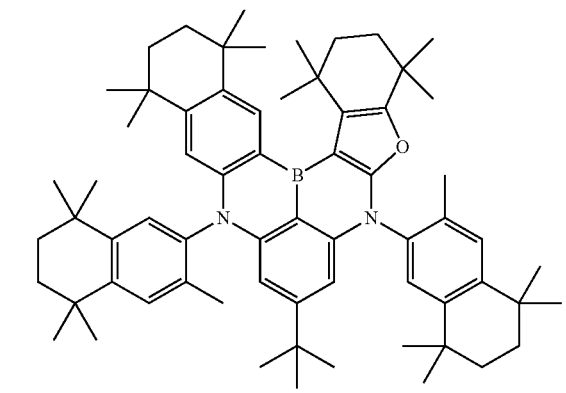
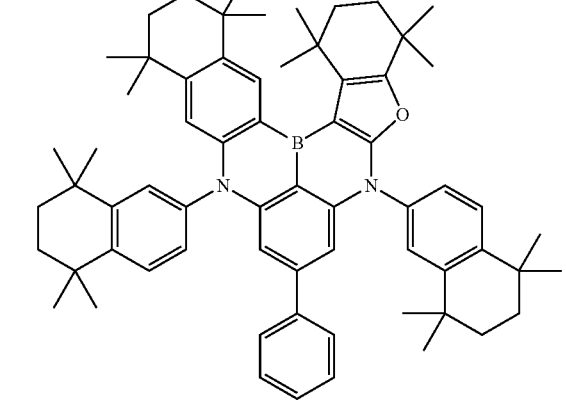

-continued
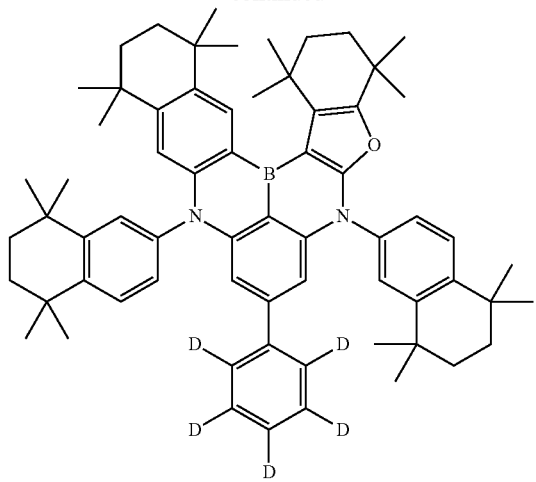
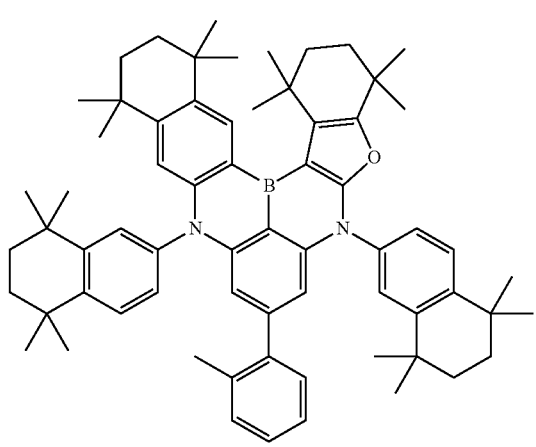
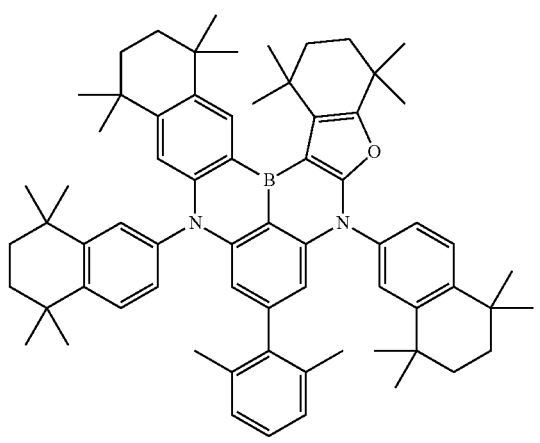
-continued
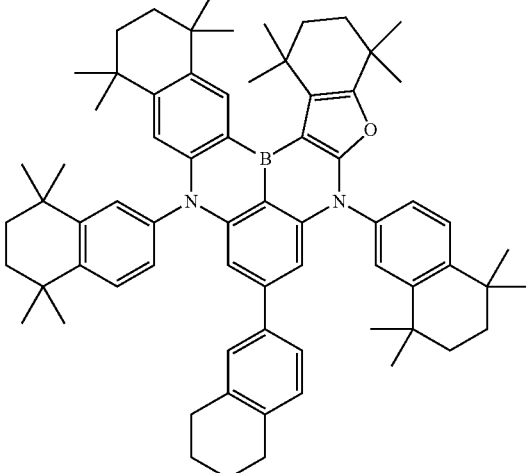
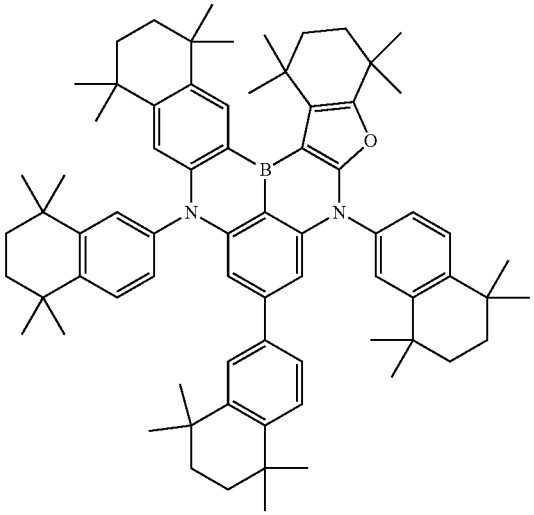
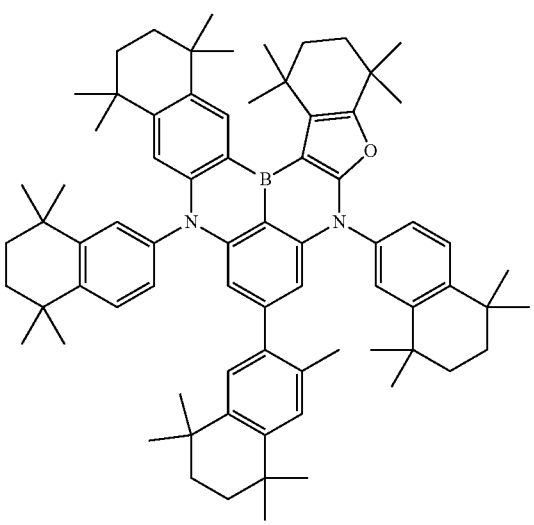

1951
-continued
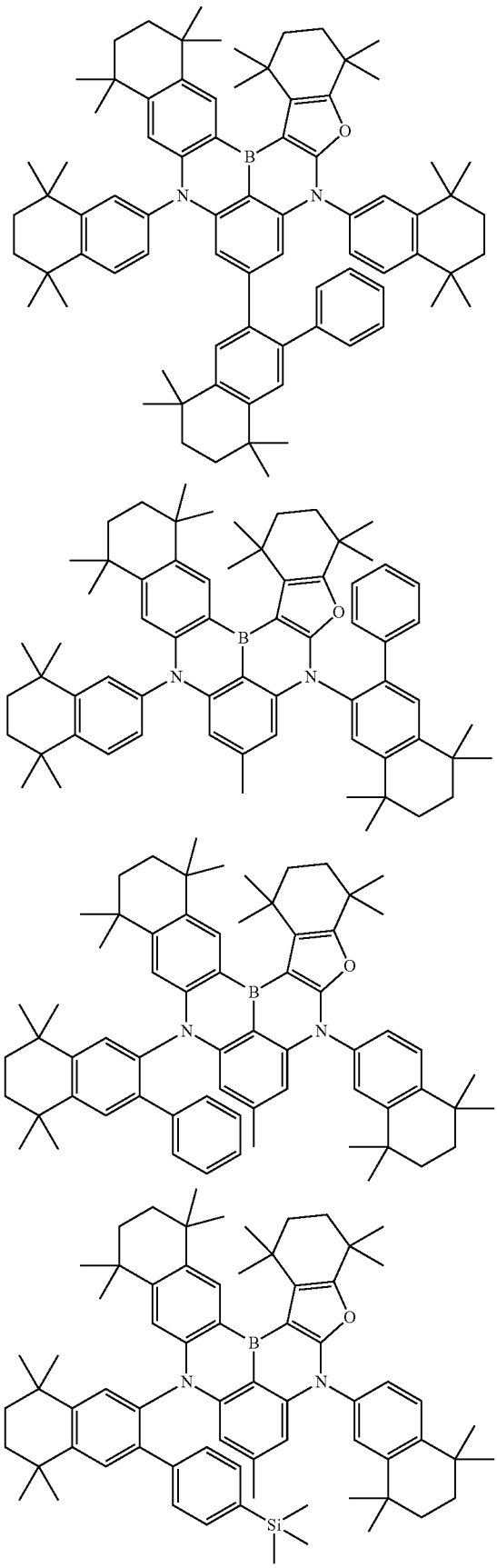
1952
-continued
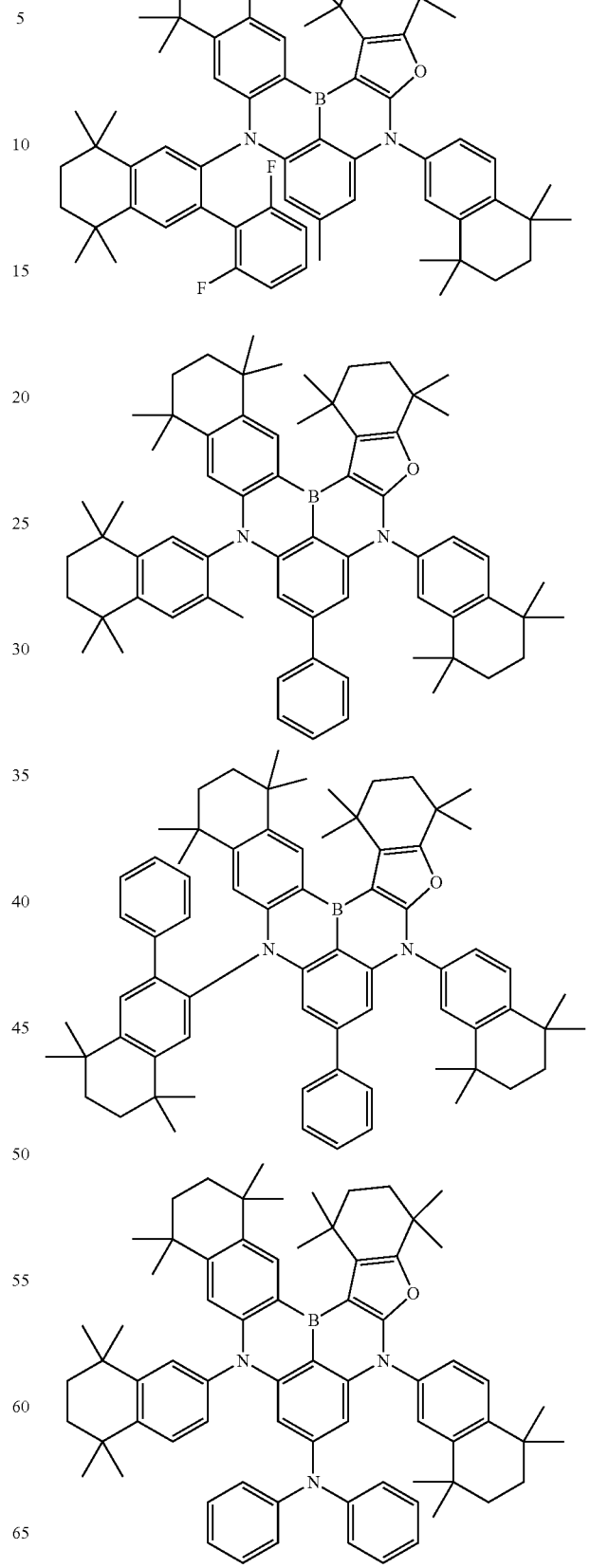

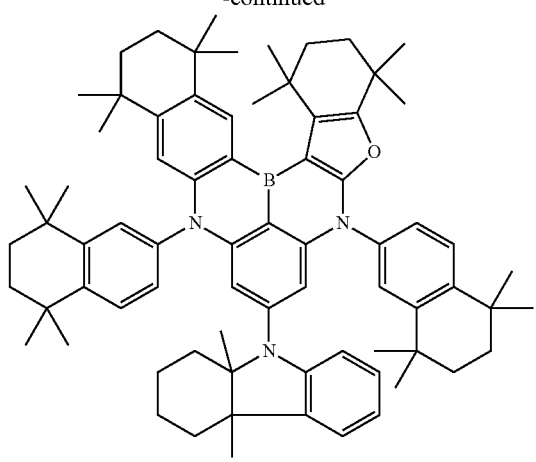

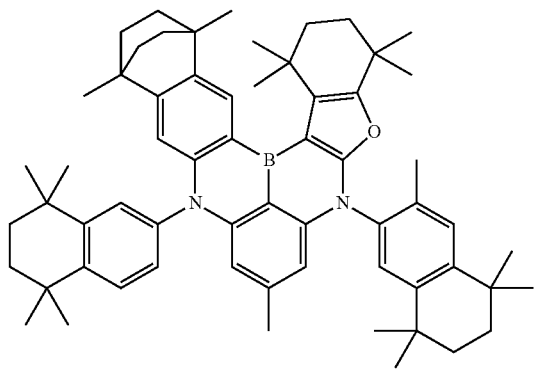

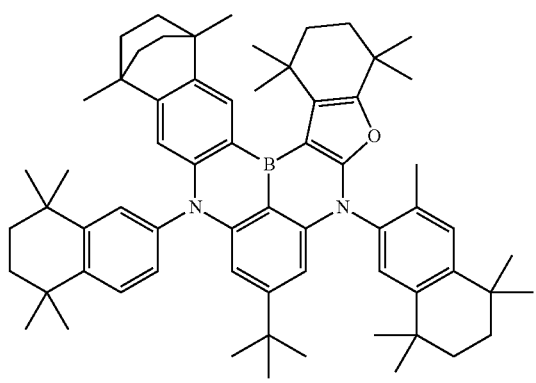

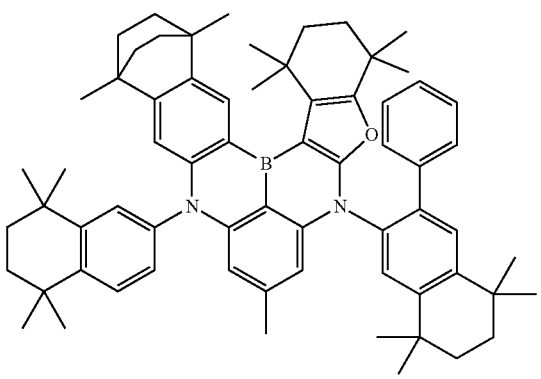

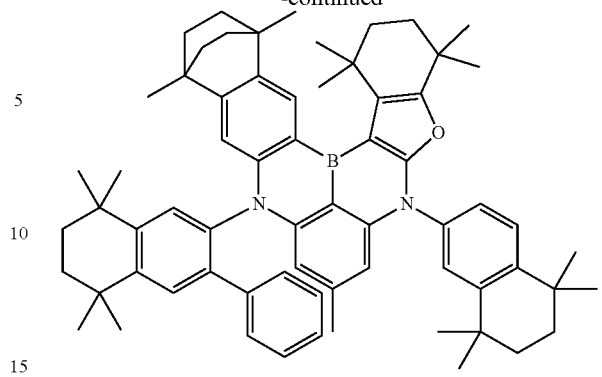

wherein,
Ph is a phenyl group, and D is deuterium.

7. An organic light emitting device comprising:
a first electrode;
a second electrode; and
an organic material layer including one or more layers provided between the first electrode and the second electrode,
wherein the organic material layer includes a light emitting layer, and the light emitting layer includes a compound represented by the following Chemical Formula 1 as a dopant material, and two or more types of compounds represented by the following Chemical Formula H as the host compound:

[Chemical Formula 1]

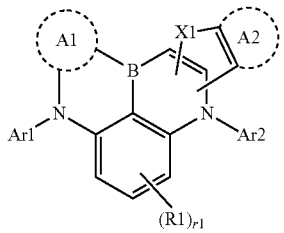

in Chemical Formula 1,
X1 is O or S,
A1 is a substituted or unsubstituted heteroring; a substituted or unsubstituted aromatic hydrocarbon ring; or a substituted or unsubstituted fused ring of aromatic hydrocarbon ring and aliphatic hydrocarbon ring;
A2 is a substituted or unsubstituted aromatic hydrocarbon ring; a substituted or unsubstituted aliphatic hydrocarbon ring; or a substituted or unsubstituted fused ring of aromatic hydrocarbon ring and aliphatic hydrocarbon ring;
Ar1 and Ar2 are the same as or different from each other; and each independently a substituted or unsubstituted cycloalkyl group; a substituted or unsubstituted aryl group; a substituted or unsubstituted heterocyclic group; or a substituted or unsubstituted fused ring group of aromatic hydrocarbon ring and aliphatic hydrocarbon ring;
R1 is hydrogen; deuterium; a halogen group; a cyano group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted silyl group; a substituted or unsubstituted amine group; a substituted or unsubstituted aryl group; a substituted or unsubstituted fused ring group of aromatic hydrocarbon ring and aliphatic hydrocarbon ring; or a substituted or unsubstituted heterocyclic group;

r1 is an integer of 1 to 3;

when r1 is 2 or greater, the two or more R1s are the same as or different from each other; and the compound of Chemical Formula 1 includes at least one fused aliphatic hydrocarbon ring substituted with a substituted or unsubstituted alkyl group,

[Chemical Formula H]

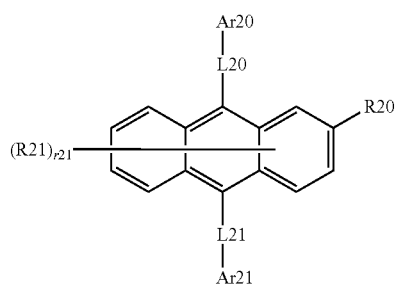

wherein in Chemical Formula H,

L20 and L21 are the same as or different from each other, and each independently a direct bond; a substituted or unsubstituted arylene group; or a substituted or unsubstituted heteroarylene group, Ar20 and Ar21 are the same as or different from each other, and each independently hydrogen; deuterium; a substituted or unsubstituted aryl group; or a substituted or unsubstituted heterocyclic group, R20 and R21 are the same as or different from each other, and each independently hydrogen; deuterium; a halogen group; a substituted or unsubstituted alkyl group; a substituted or unsubstituted cycloalkyl group; a substituted or unsubstituted aryl group; or a substituted or unsubstituted heterocyclic group, and r21 is an integer of 1 to 7, and when r21 is 2 or greater, the two or more R21s are the same as or different from each other.

8. The organic light emitting device of claim 7, wherein the compound of Chemical Formula 1 is any one selected from the following compounds:

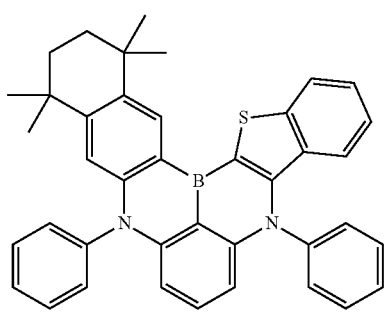

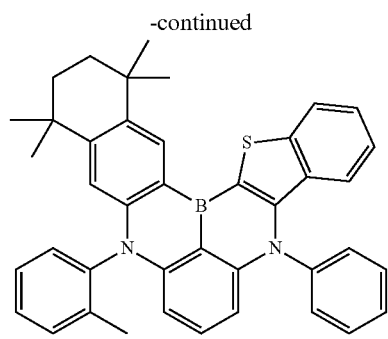

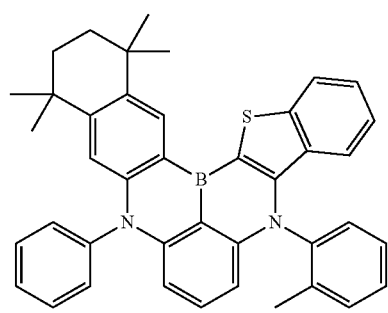

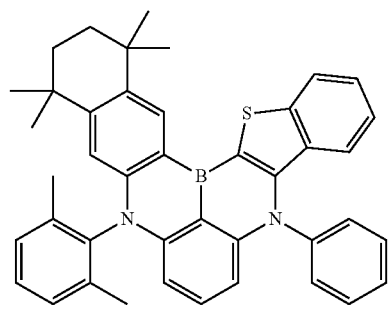

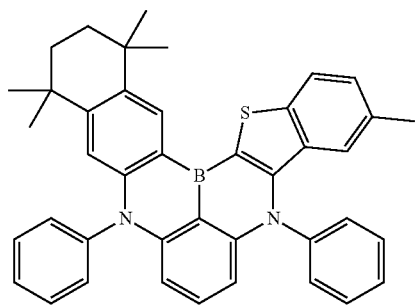

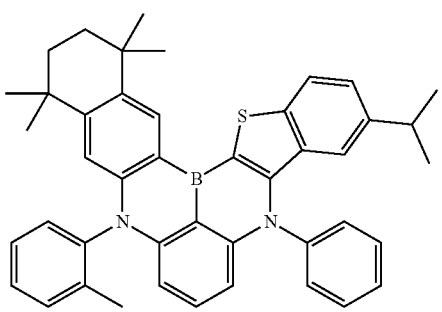

1957
-continued
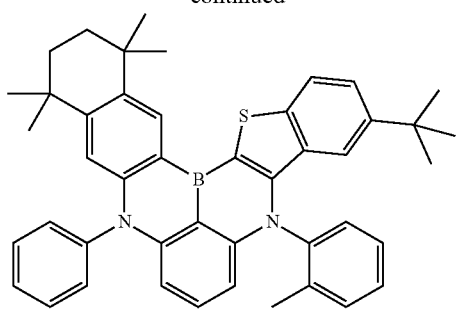
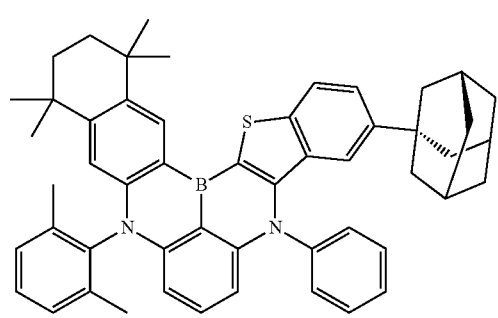
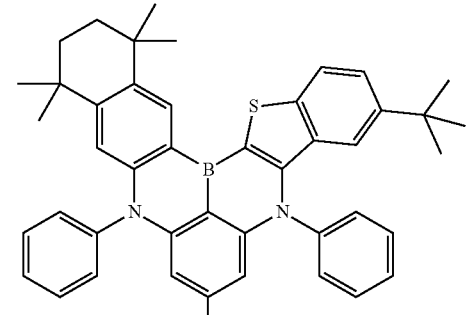
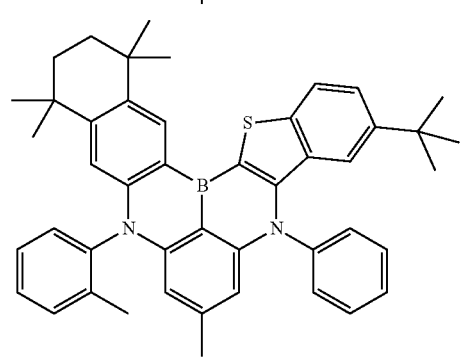
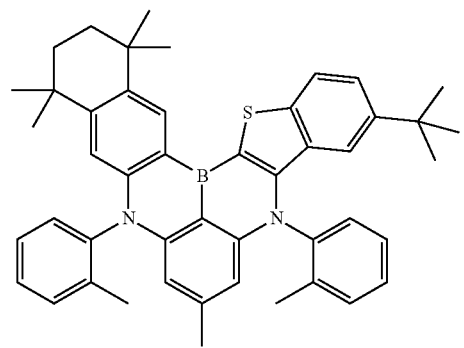
1958
-continued
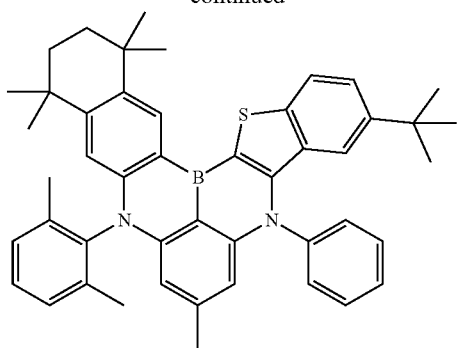
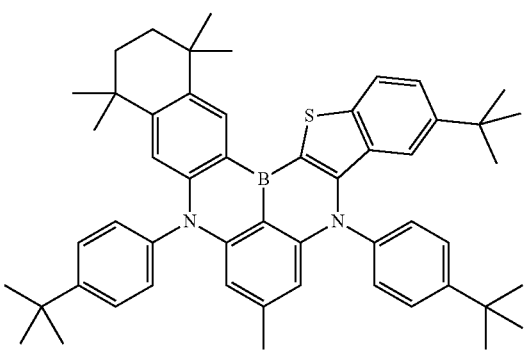
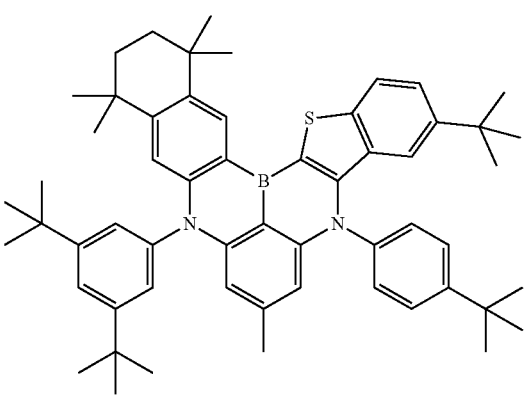
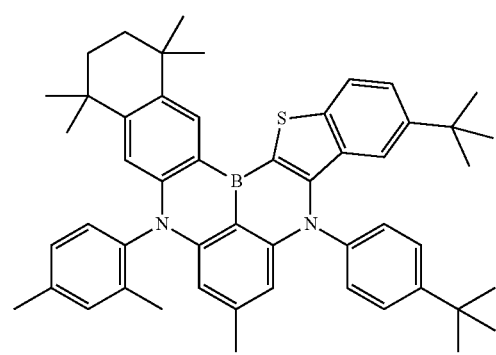

| 1959 -continued | 1960 -continued |
|---|---|
| 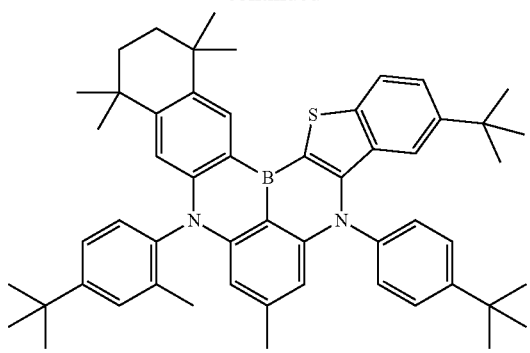 | 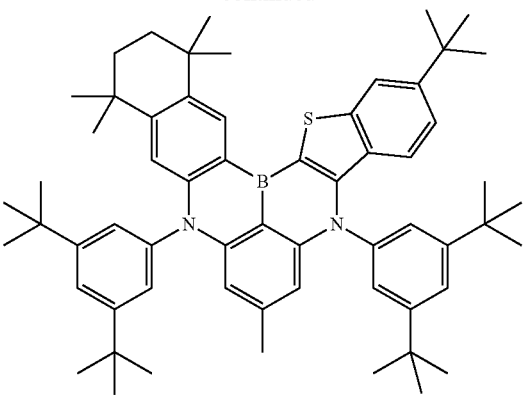 |
| 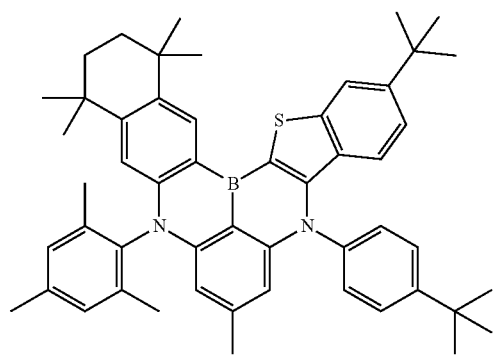 | 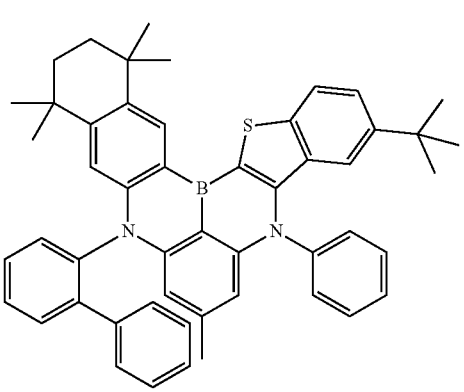 |
| 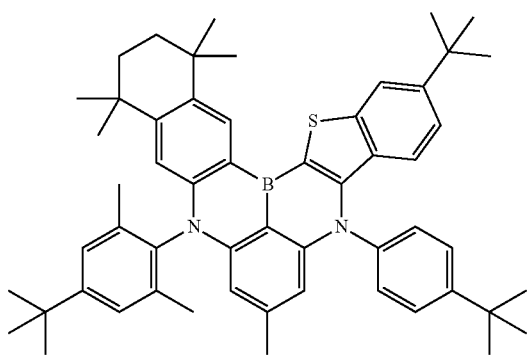 | 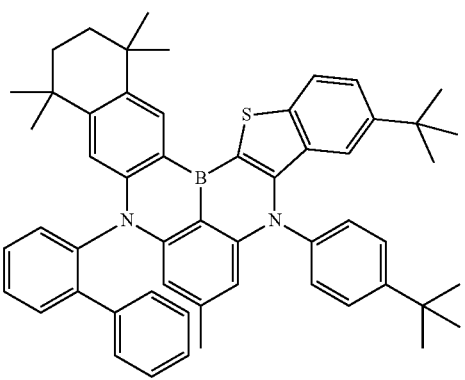 |
| 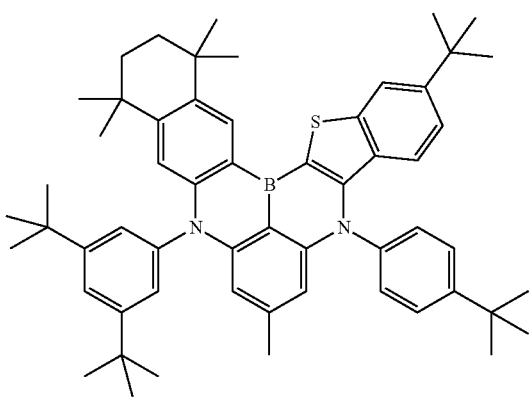 | 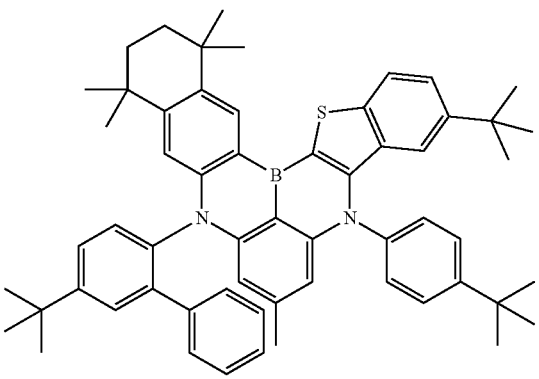 |

| 1961 -continued | 1962 -continued |
|---|---|
| 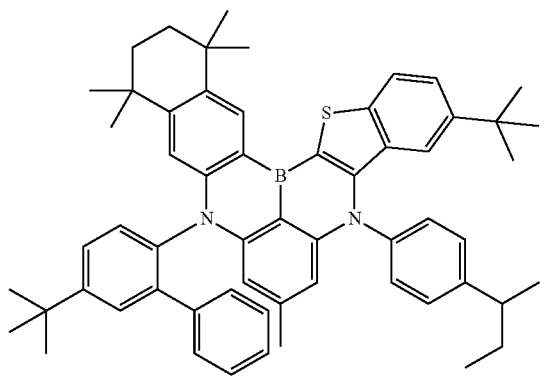 | 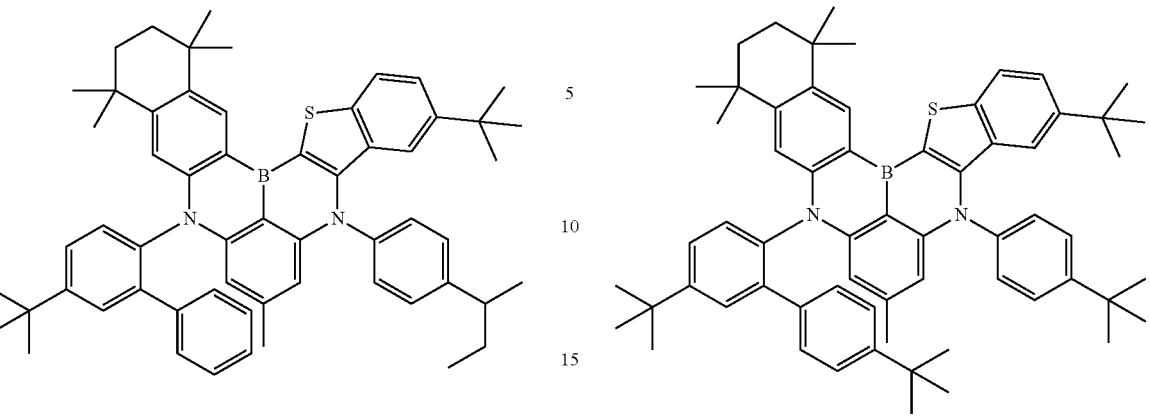 |
| 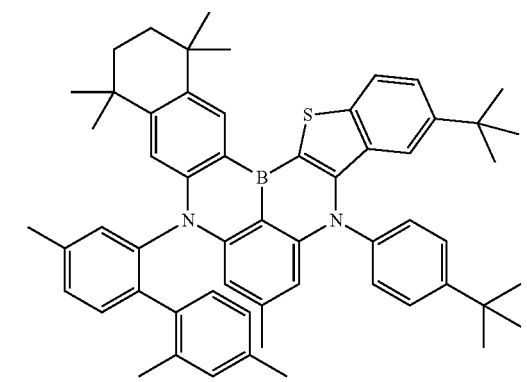 | 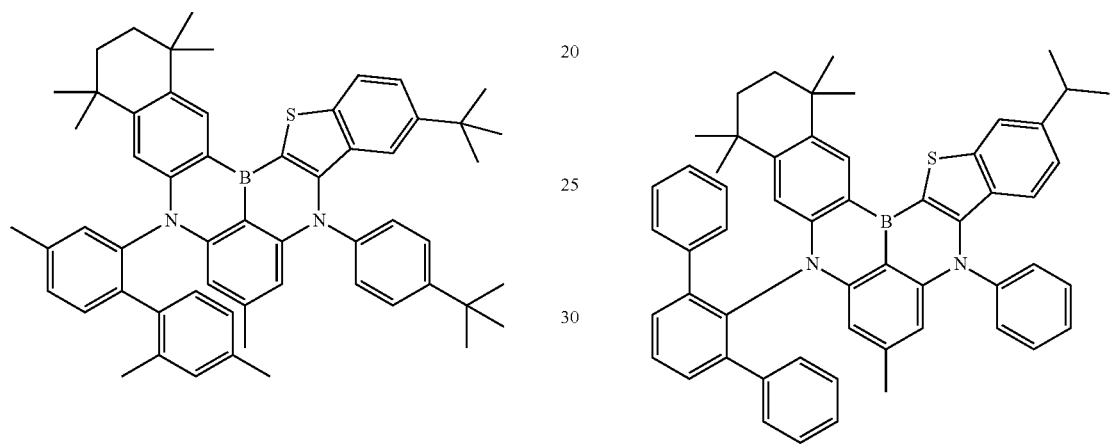 |
| 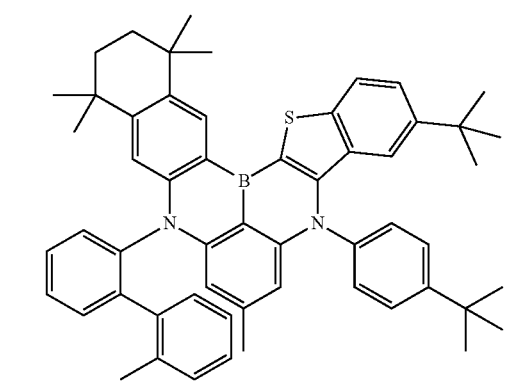 | 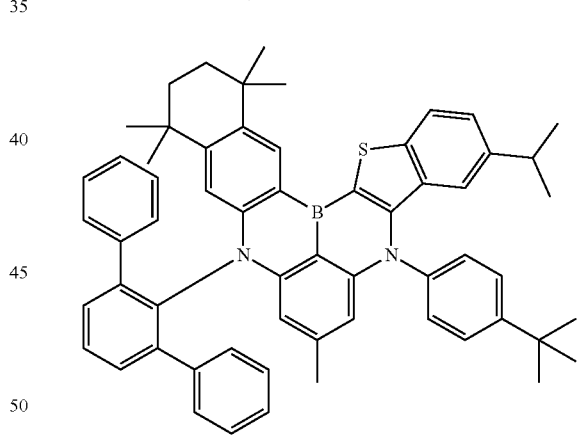 |
| 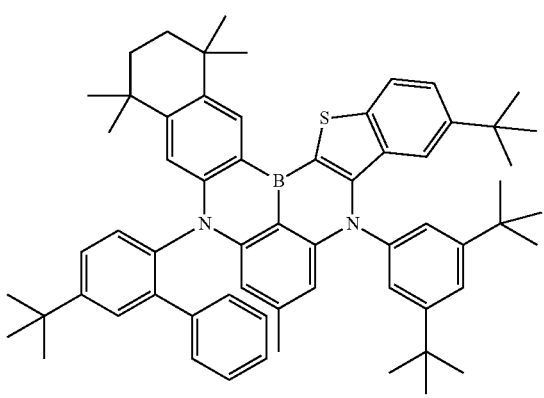 | 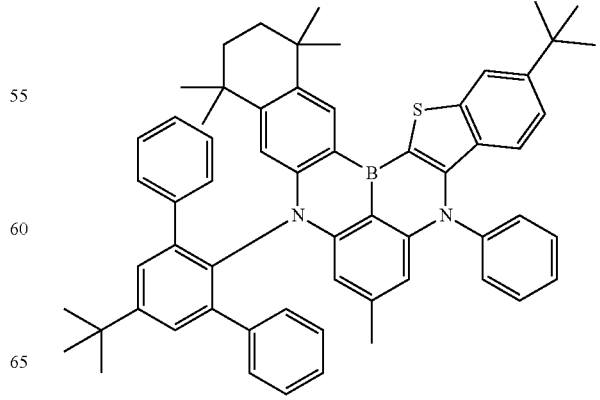 |

1963
-continued
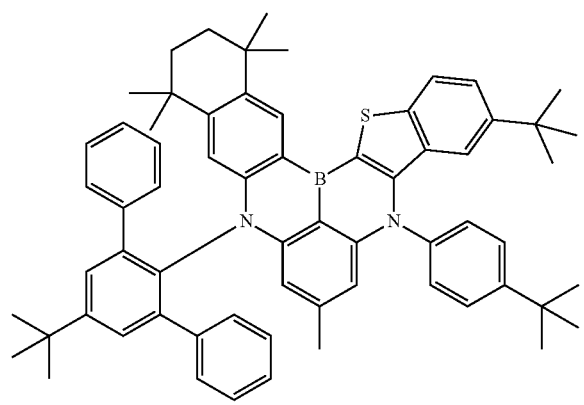
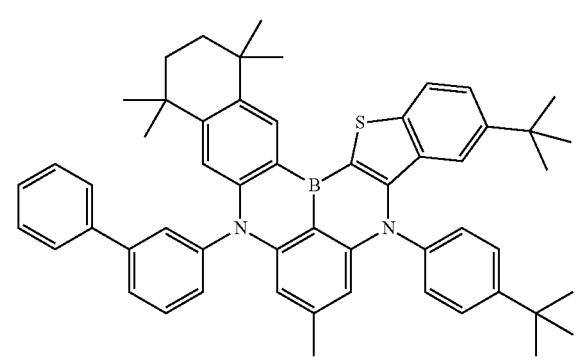
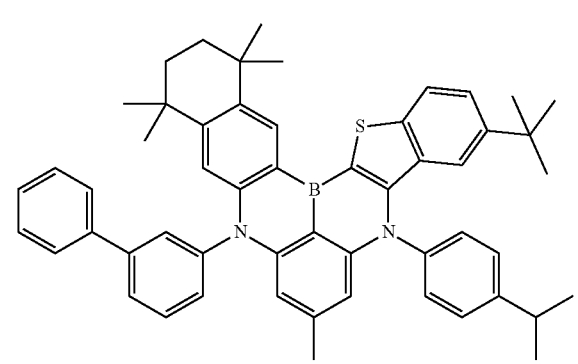
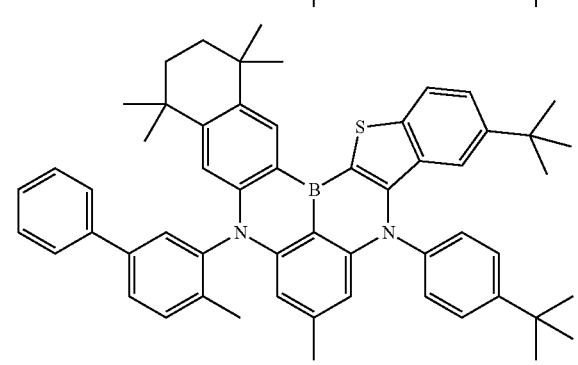
1964
-continued
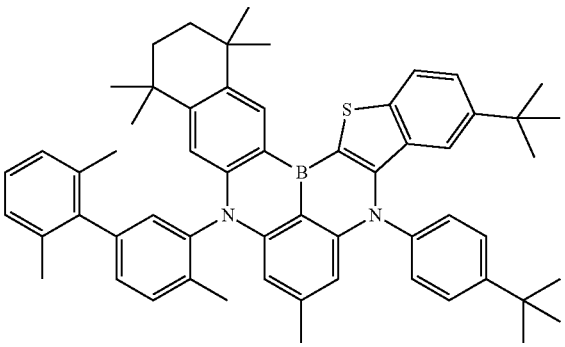
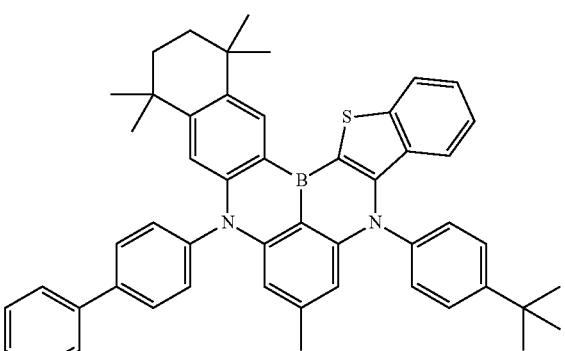
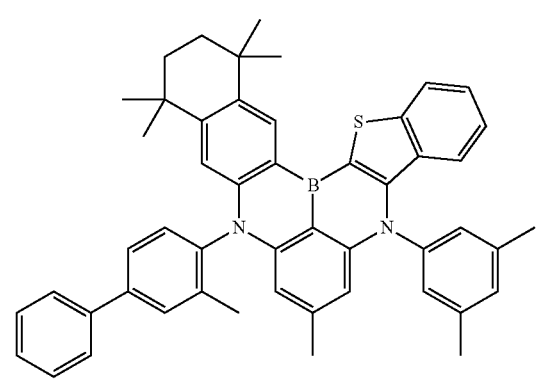
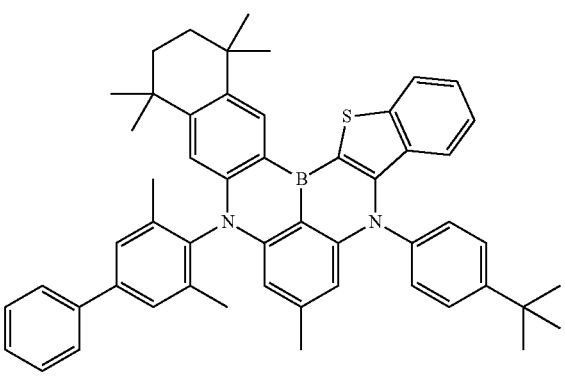

1965
-continued
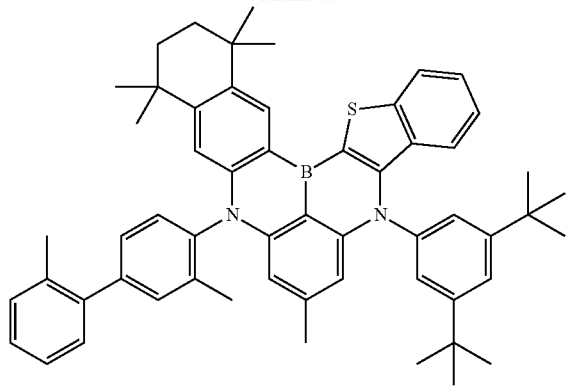
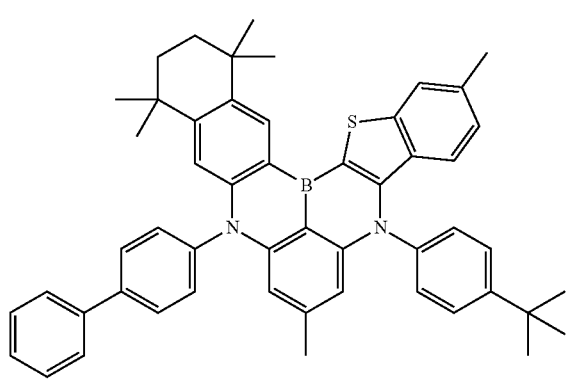
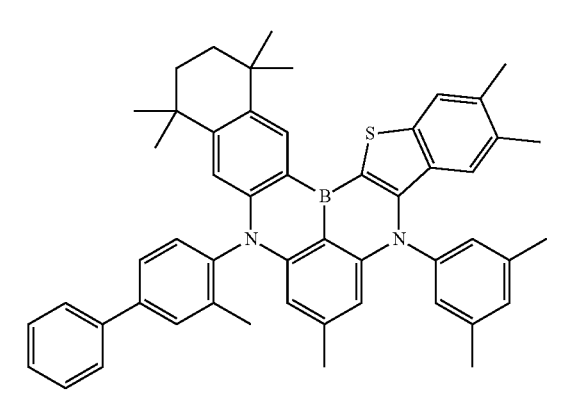
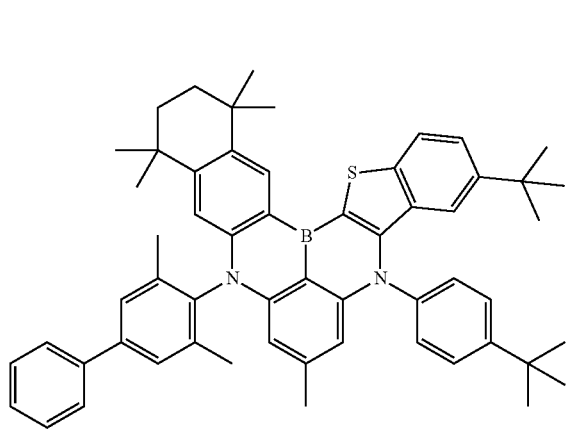
1966
-continued
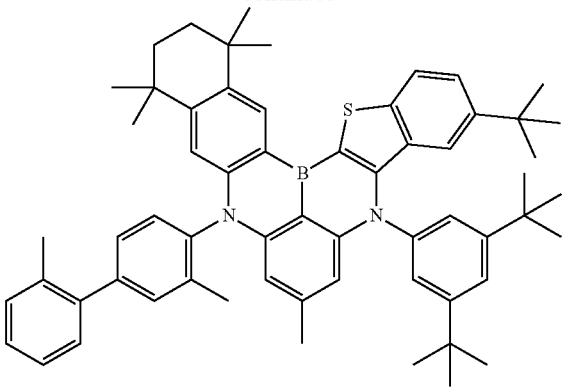
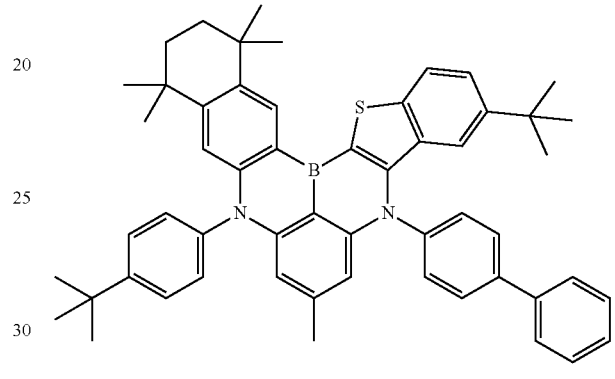
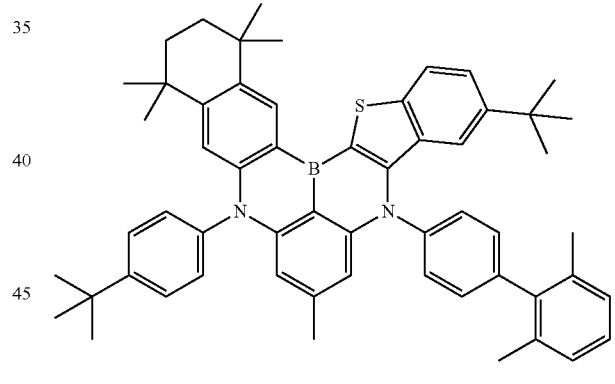
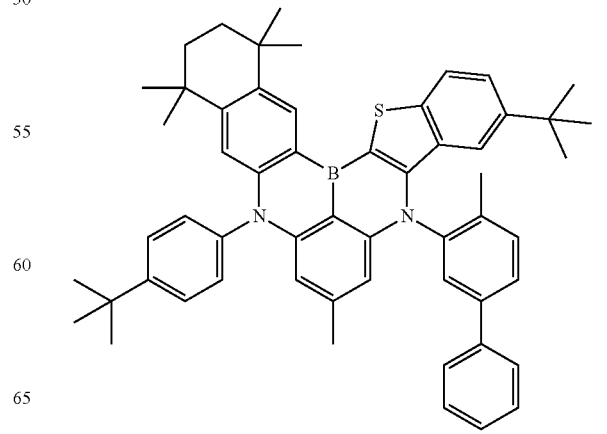

1967
-continued
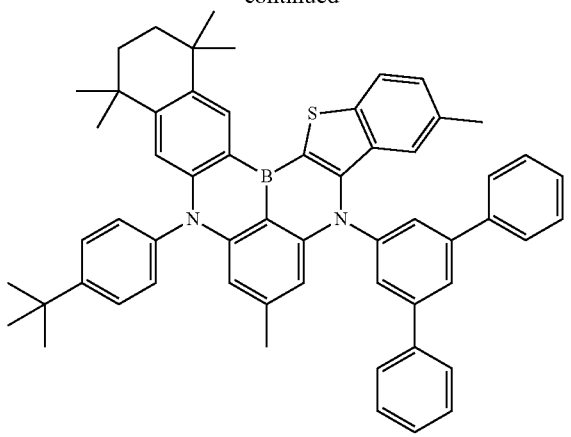
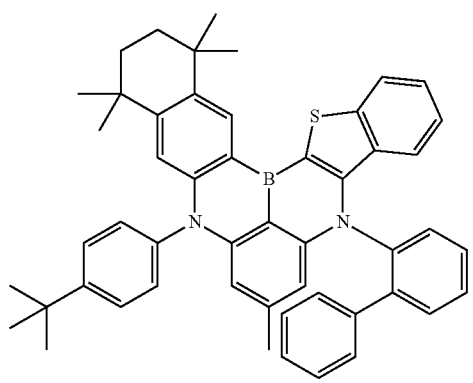
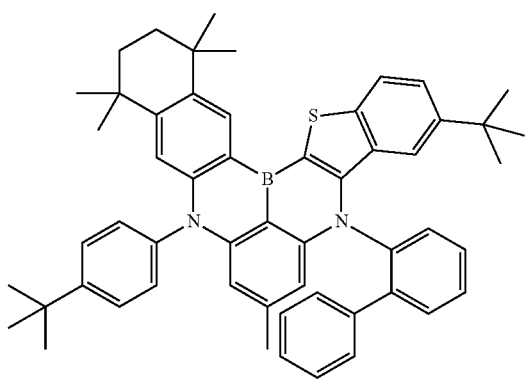
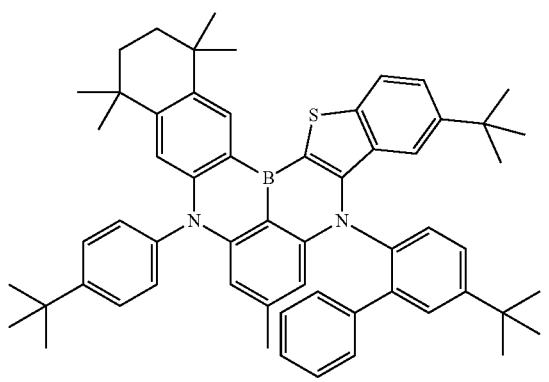
1968
-continued
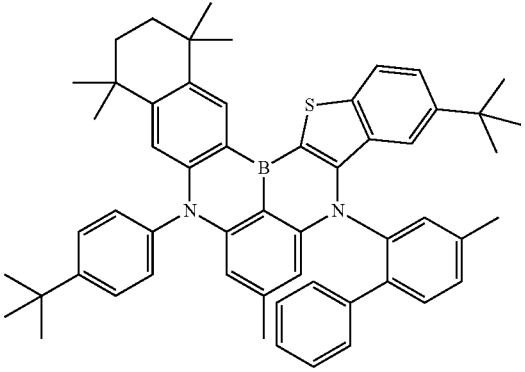
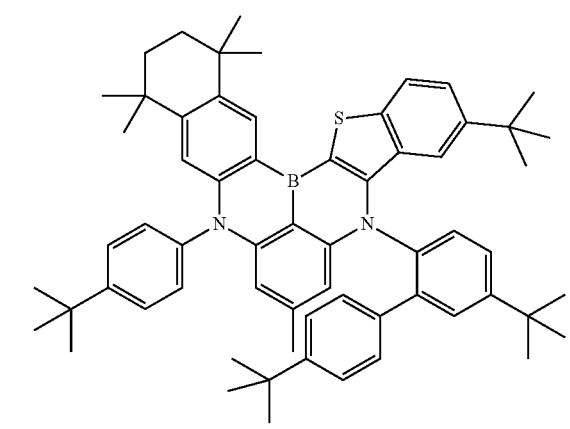
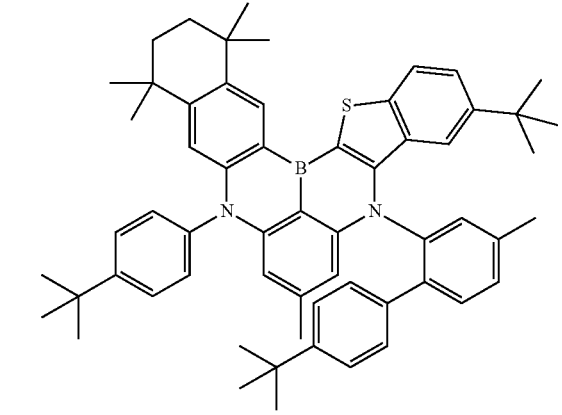
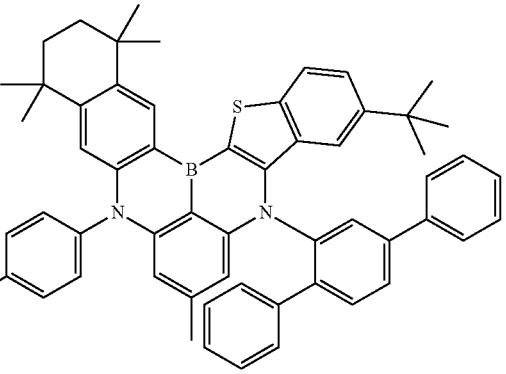

1969
-continued

1970
-continued

1971
-continued
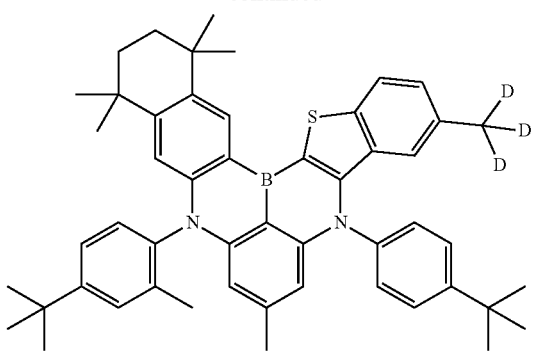
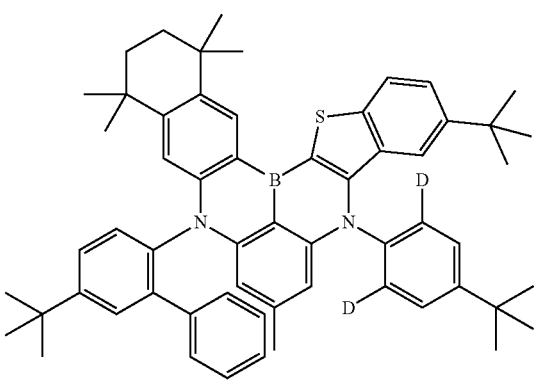
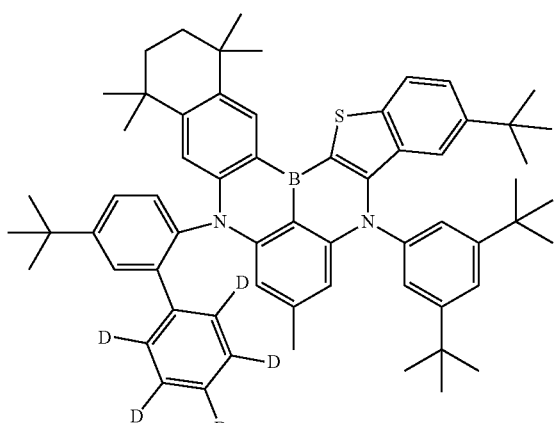
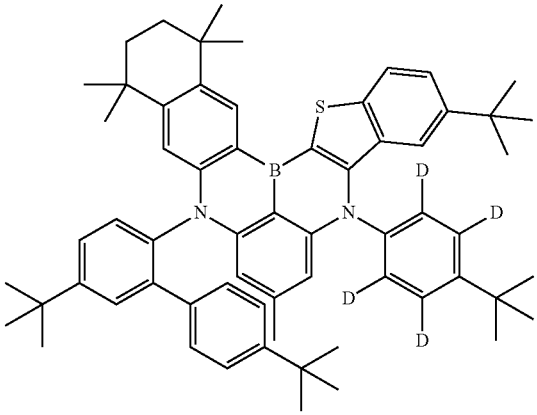
1972
-continued
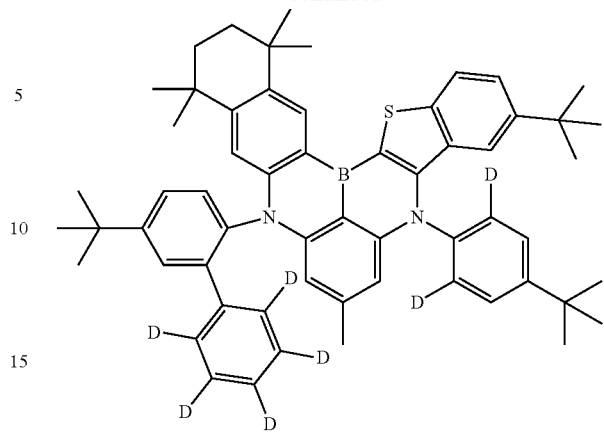
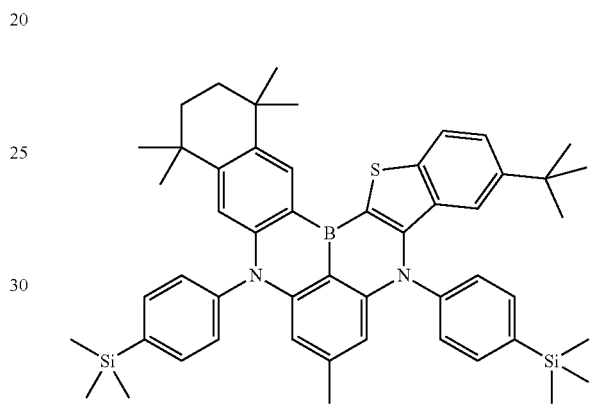
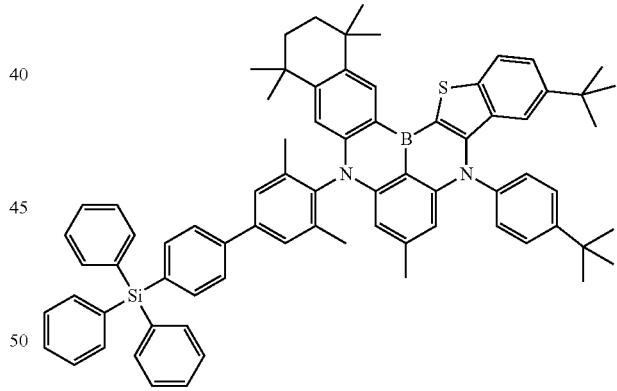
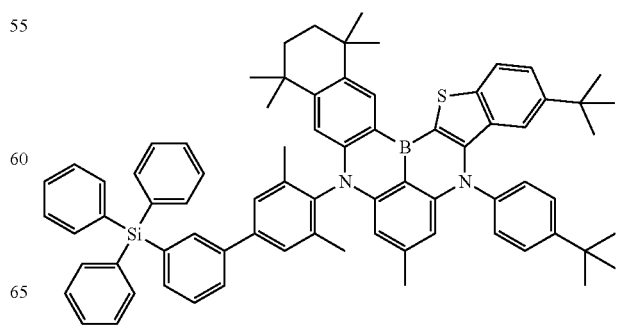

| 1973 -continued | 1974 -continued |
|---|---|
| 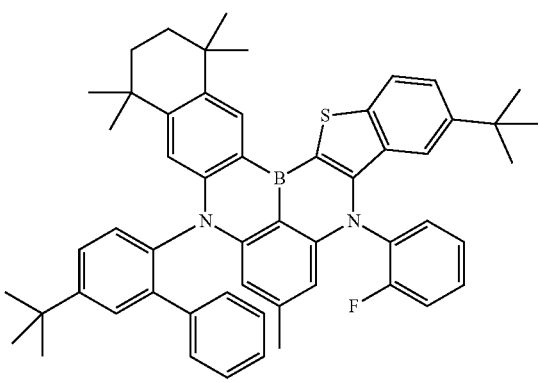 | 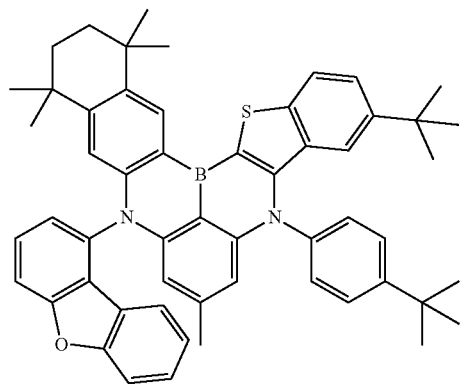 |
| 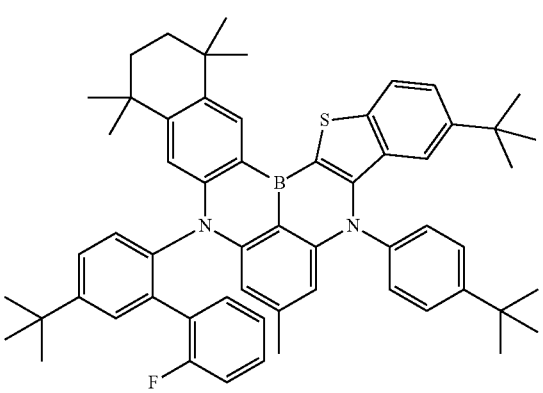 | 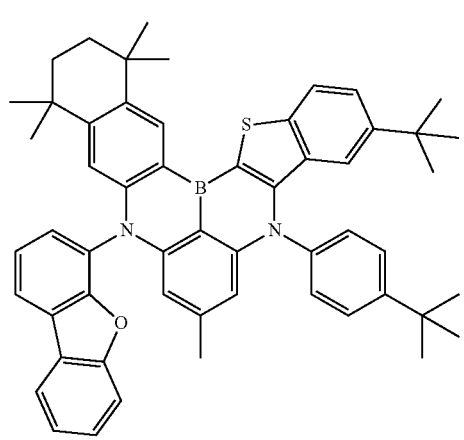 |
| 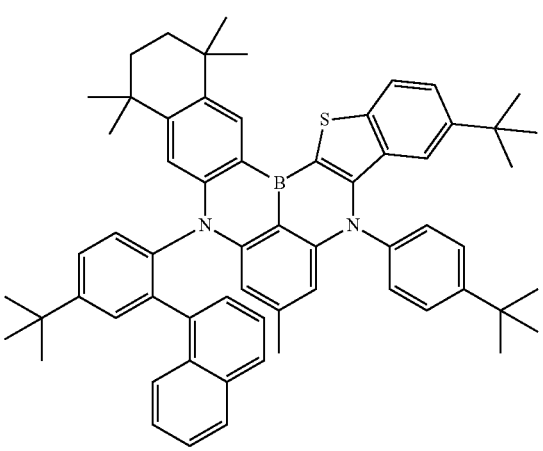 | 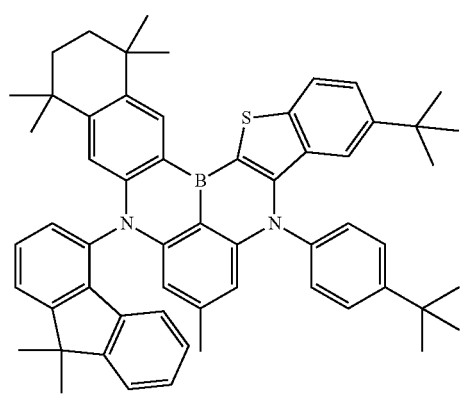 |
| 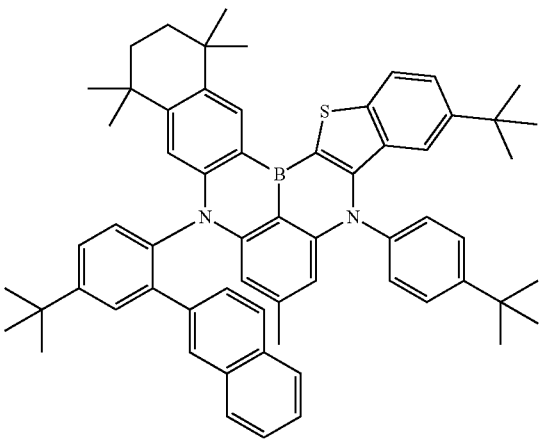 | 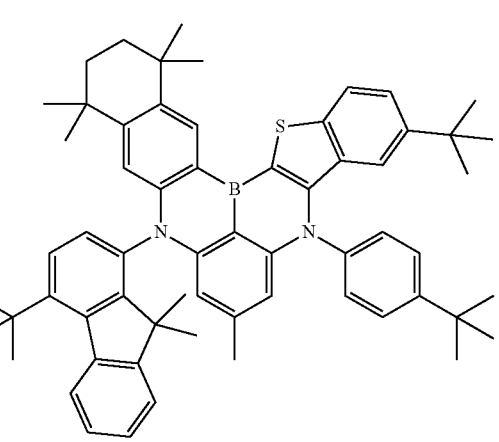 |

1975
-continued

1976
-continued

1977
-continued
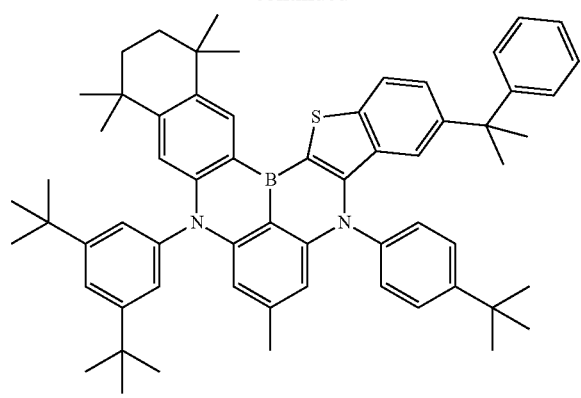
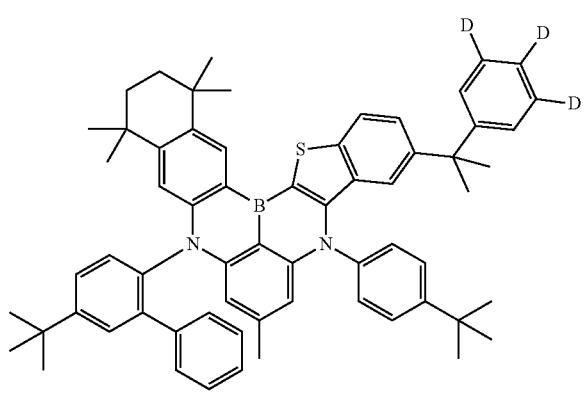
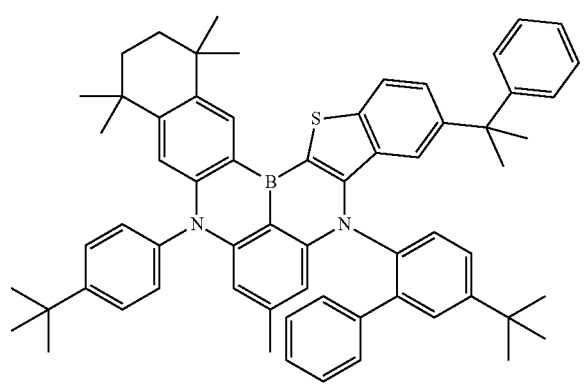
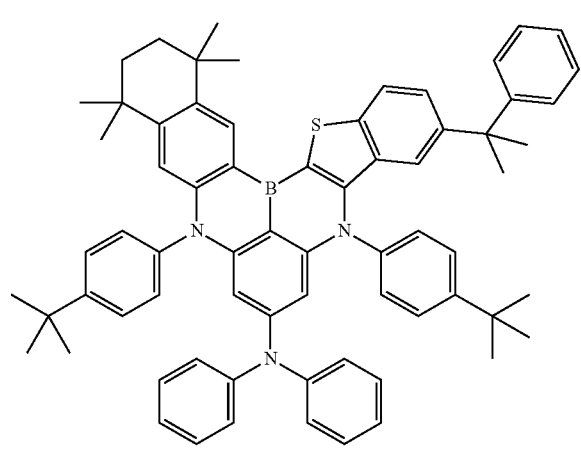
1978
-continued
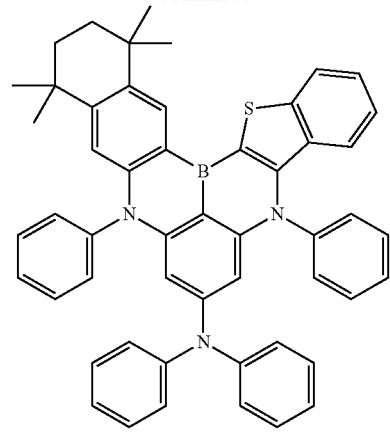
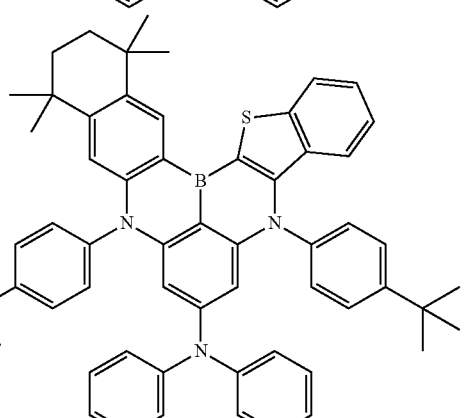
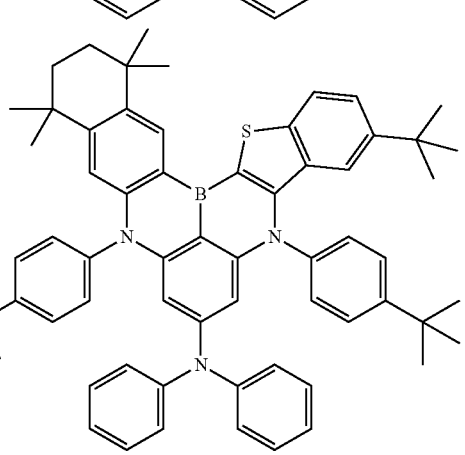
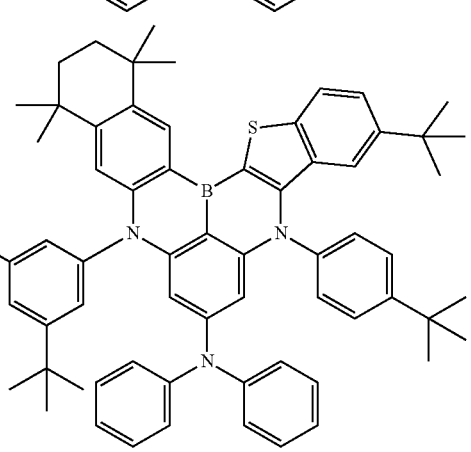

1979
-continued
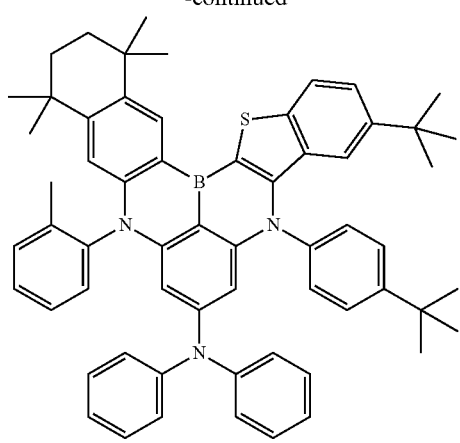
1980
-continued
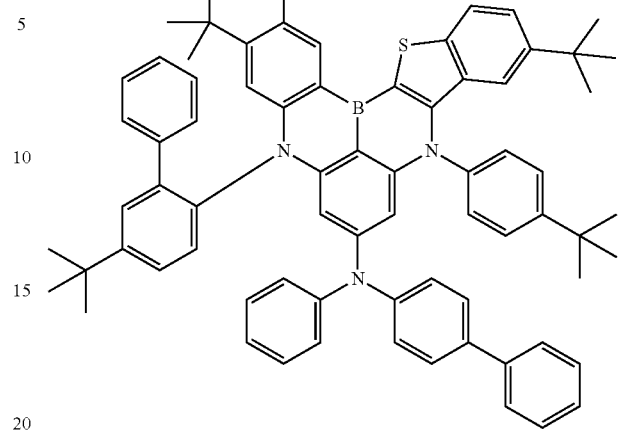
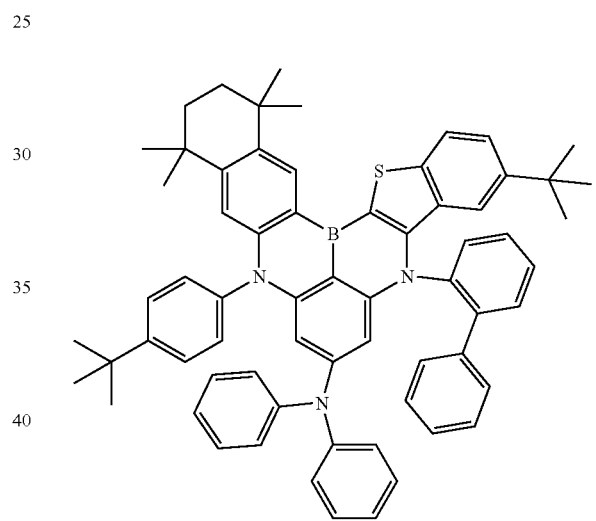
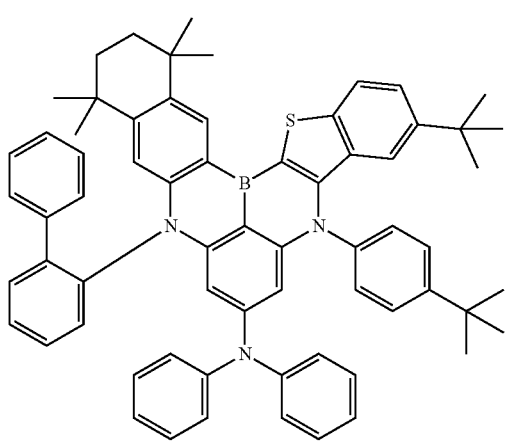
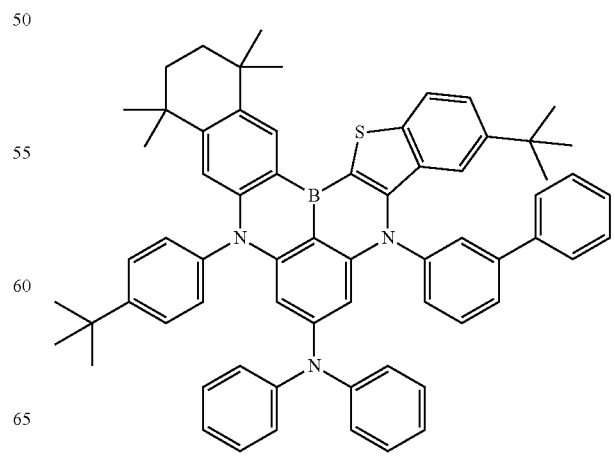

1981
-continued
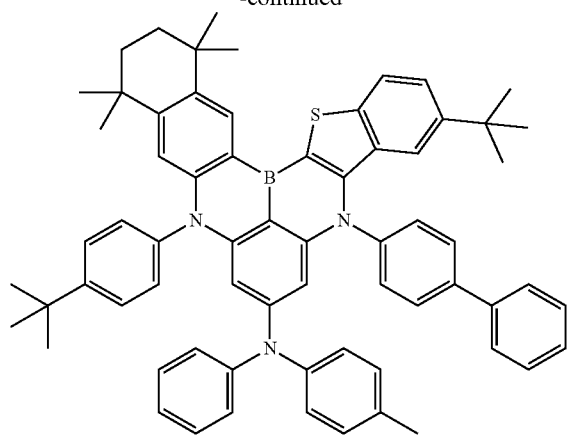
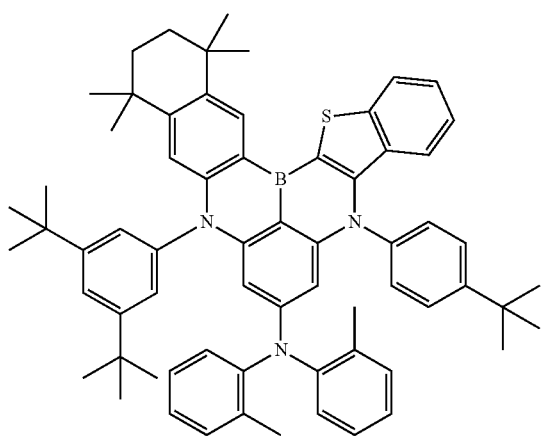
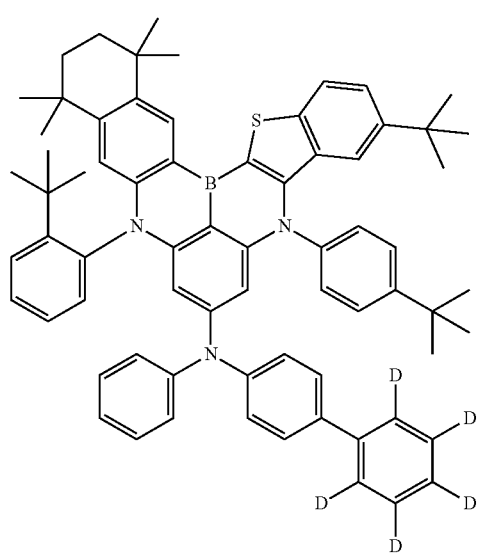
1982
-continued
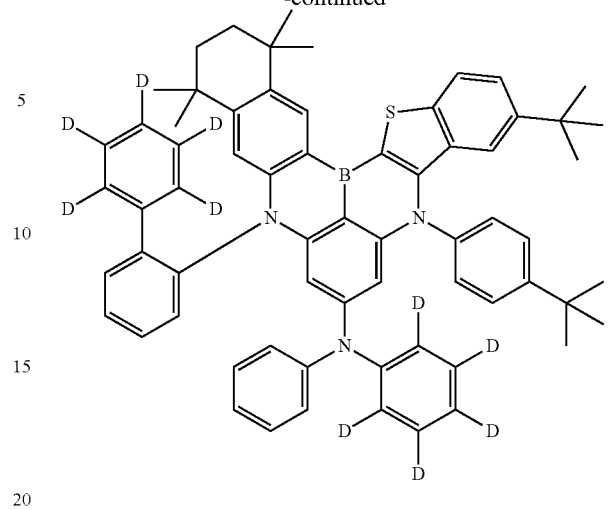
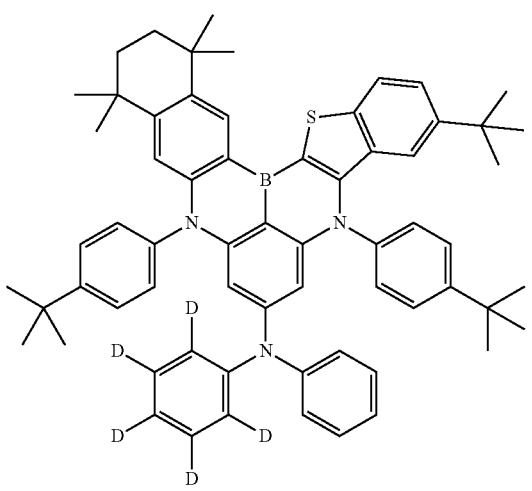
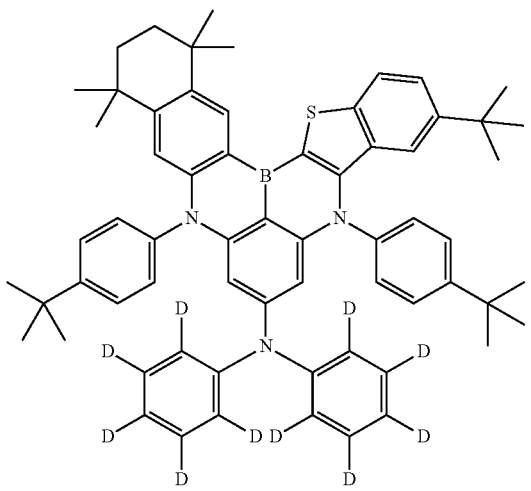

1983
-continued
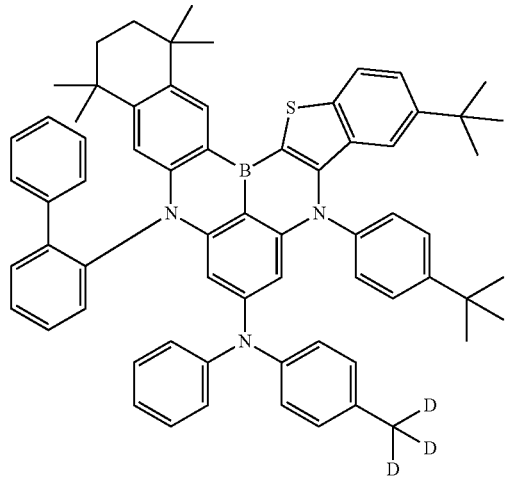
1984
-continued
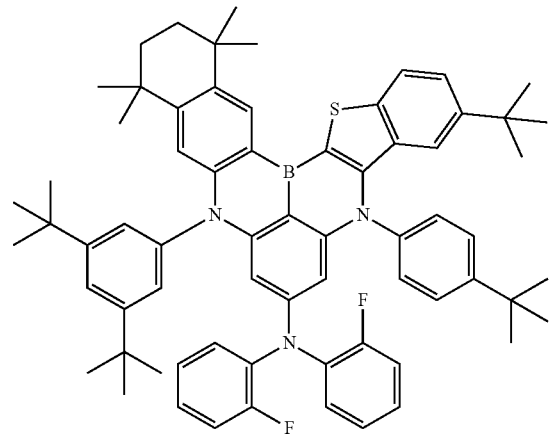
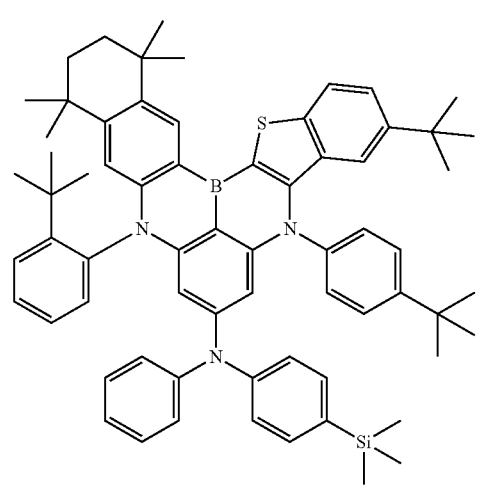
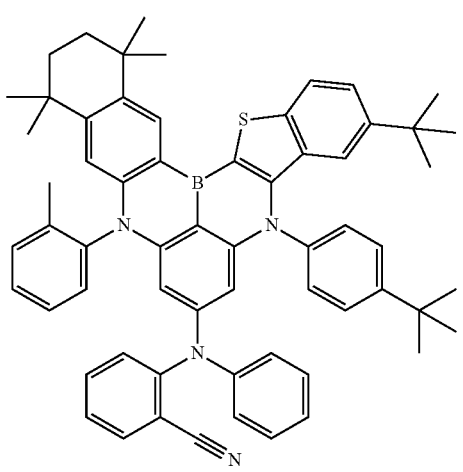
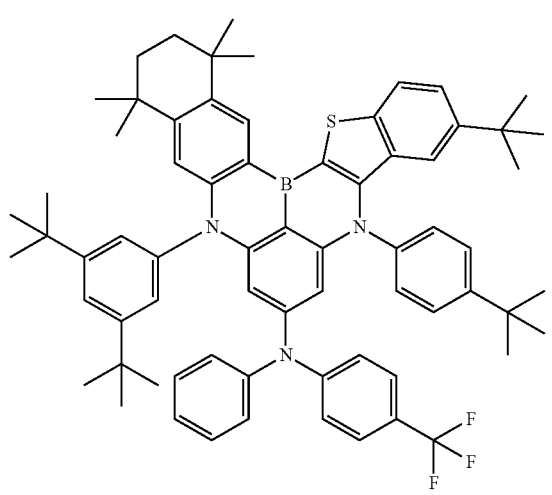
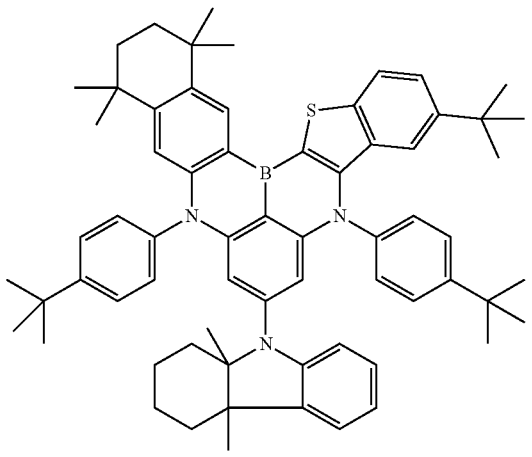

| 1985 | 1986 |
|---|---|
| 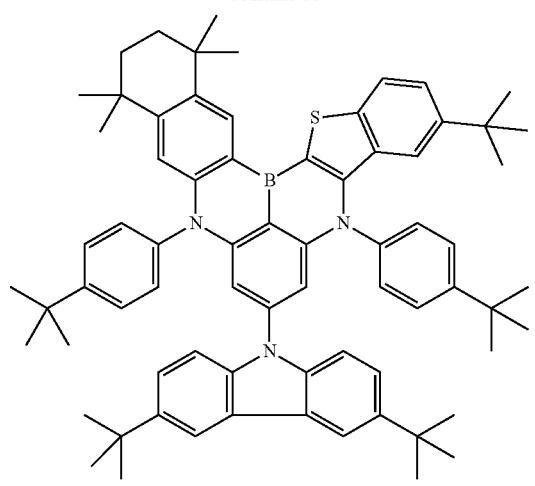 | 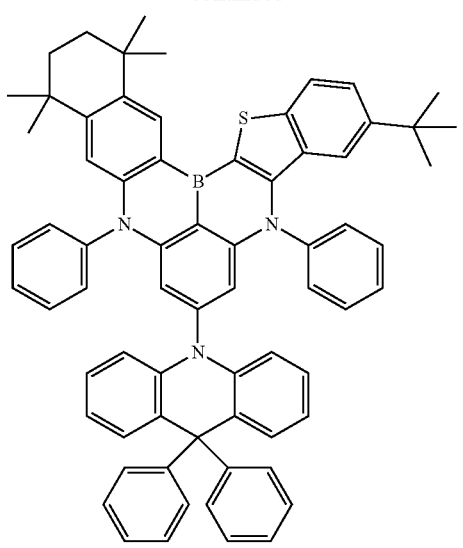 |
|  | 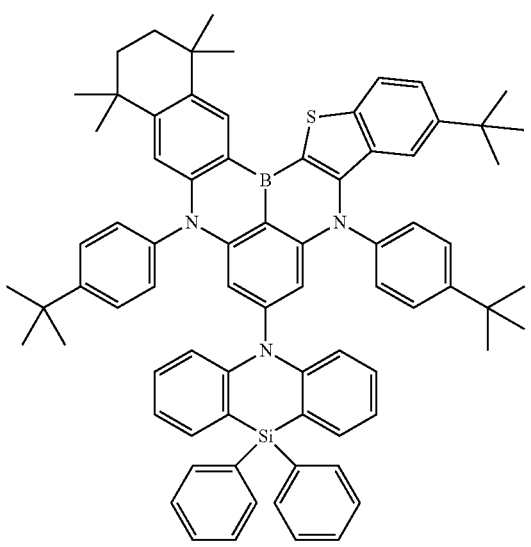 |
| 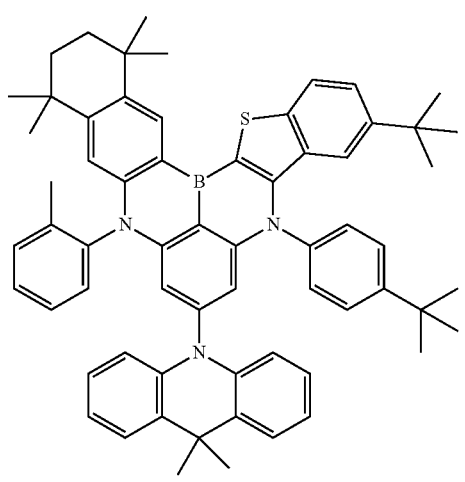 | 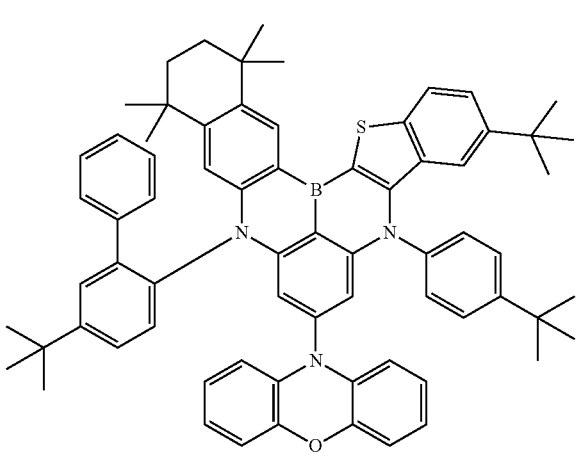 |

1987
-continued
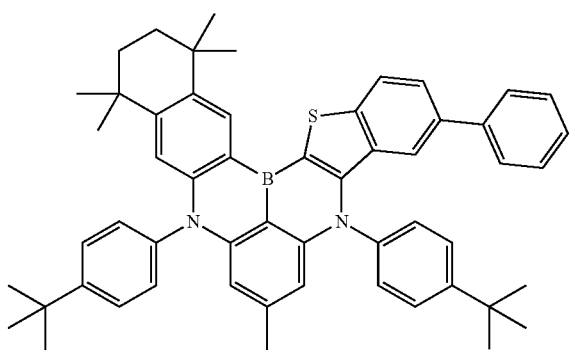
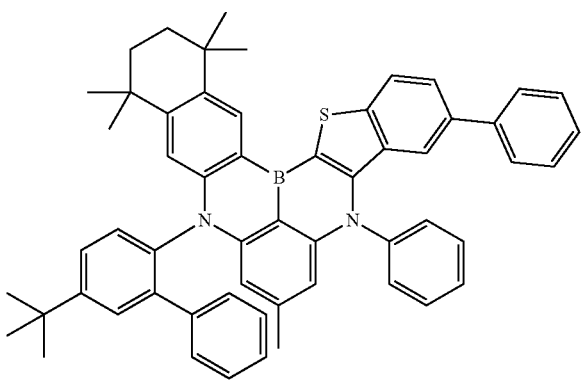
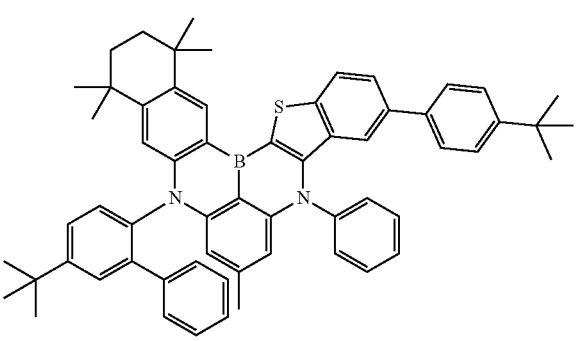
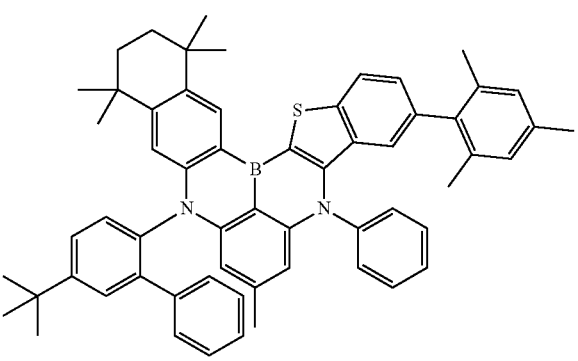
1988
-continued
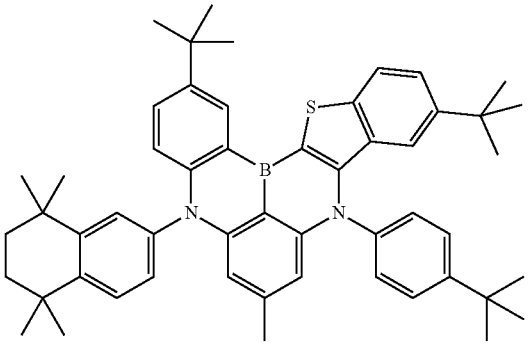
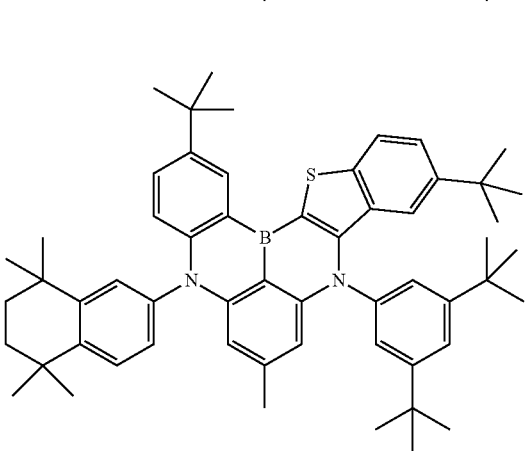
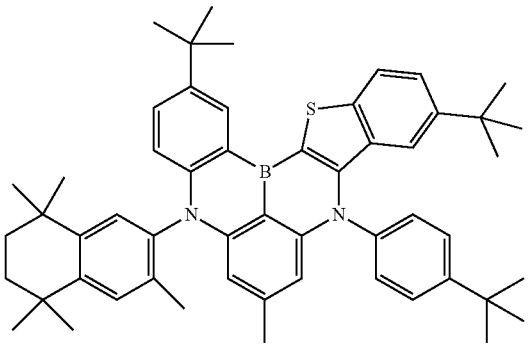
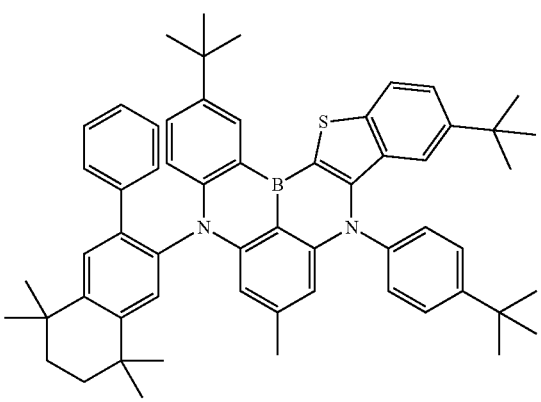

-continued
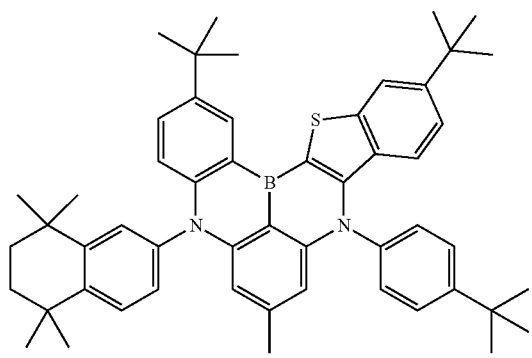
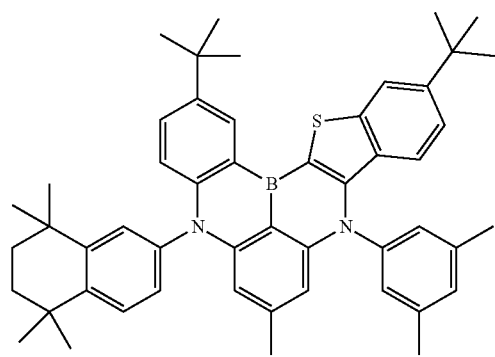
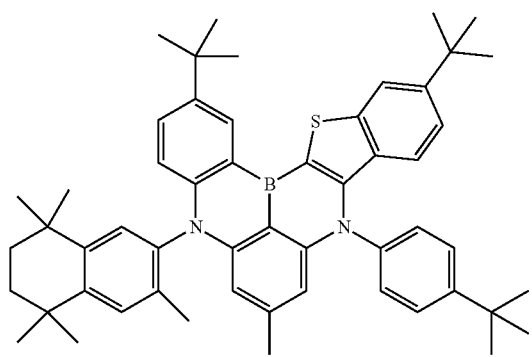
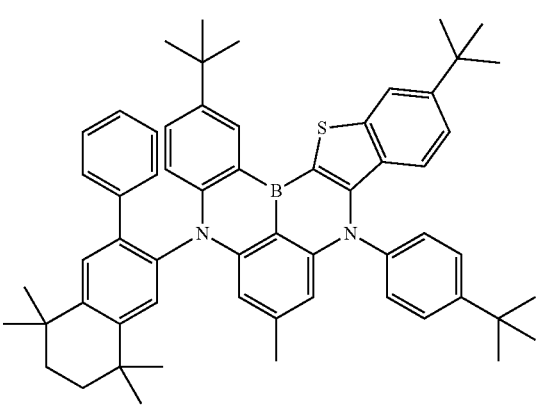
-continued
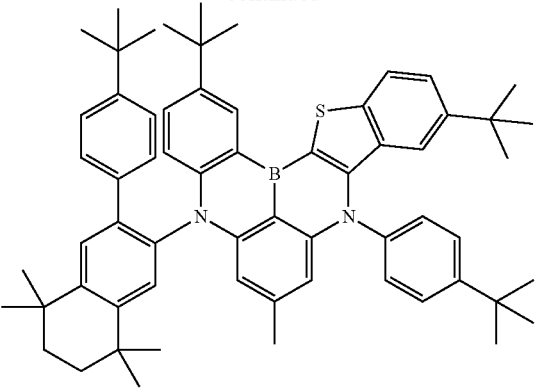
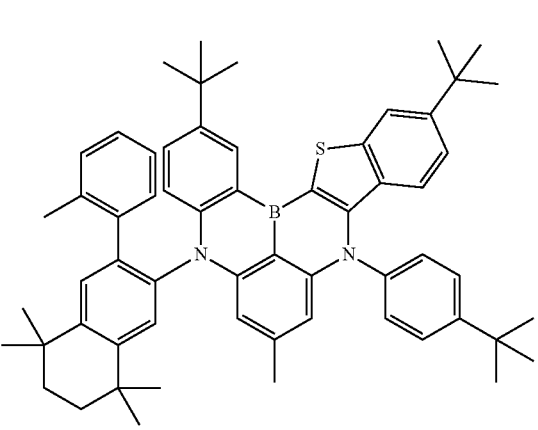
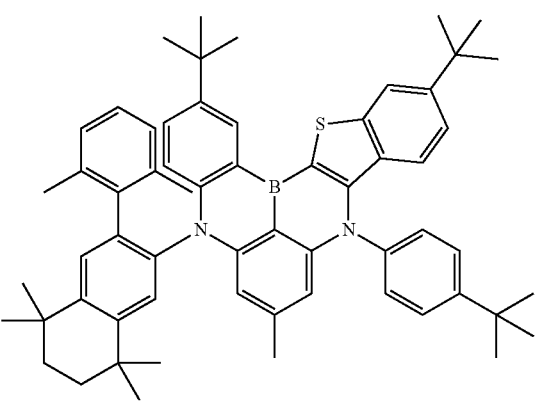
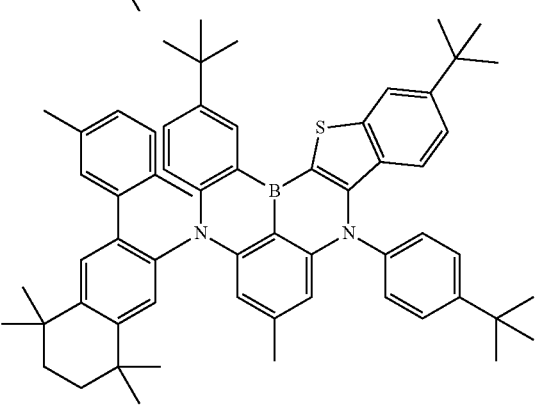

| 1991 -continued | 1992 -continued |
|---|---|
| 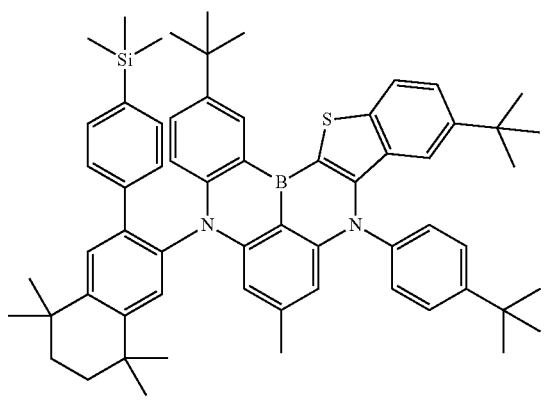 | 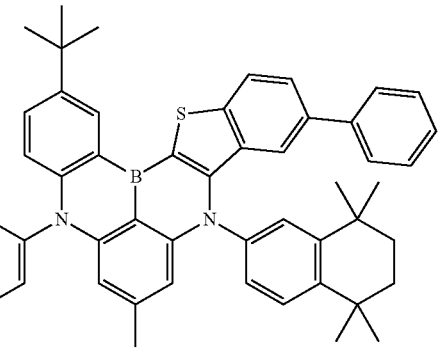 |
| 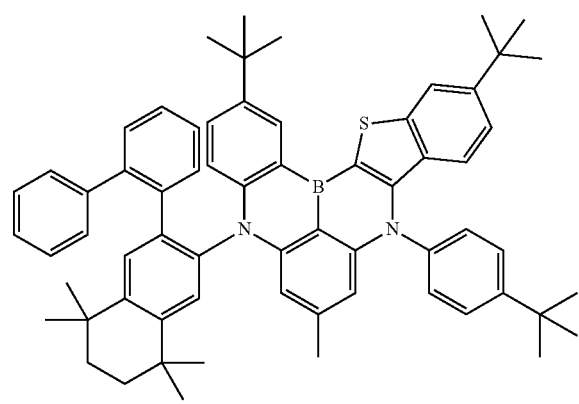 | 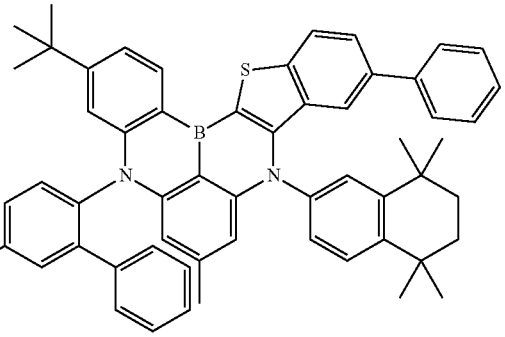 |
| 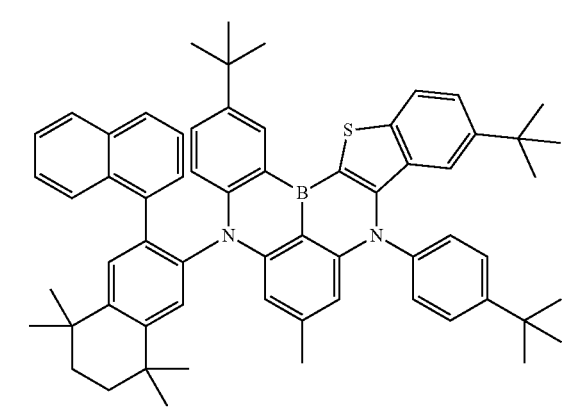 | 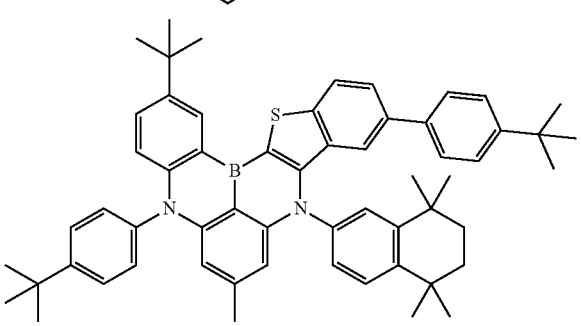 |
| 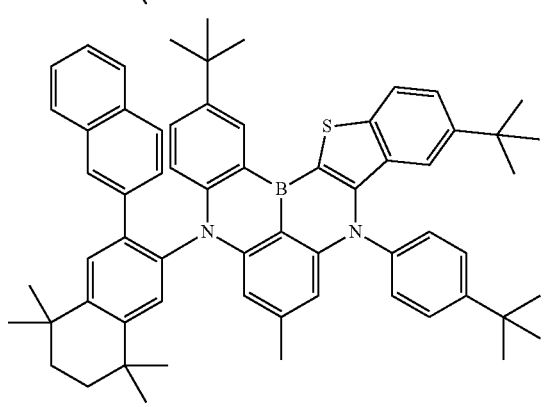 | 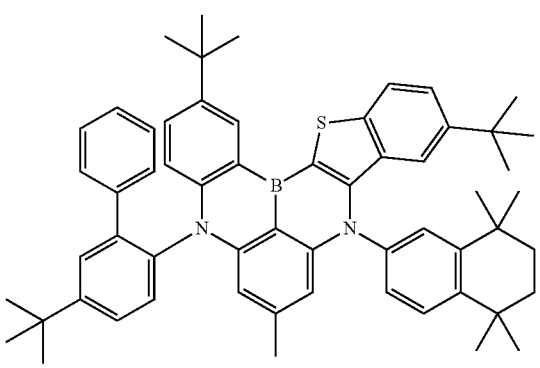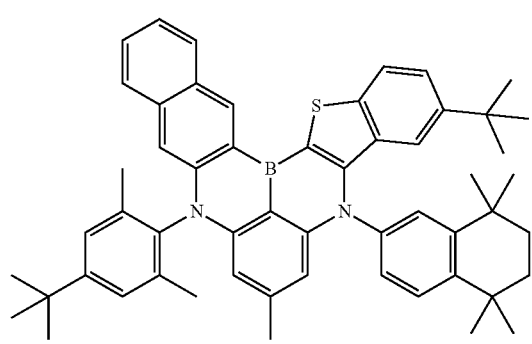 |

| 1993 | 1994 |
|---|---|
| -continued | -continued |
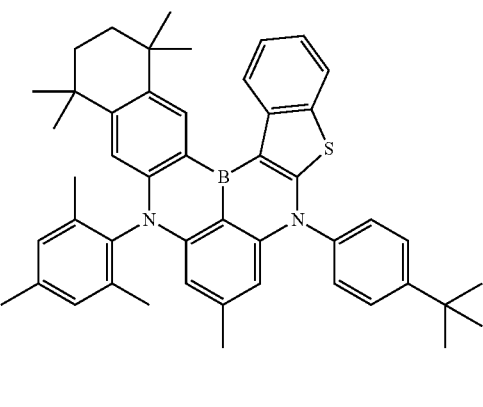
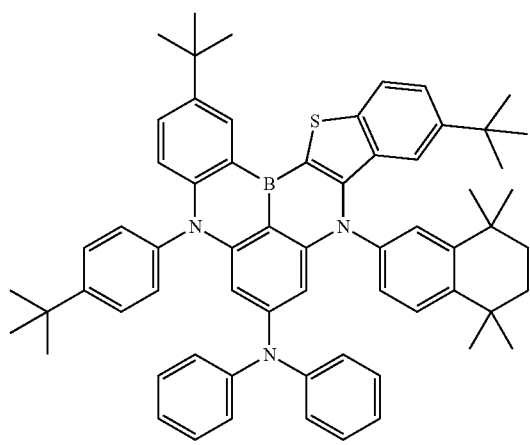
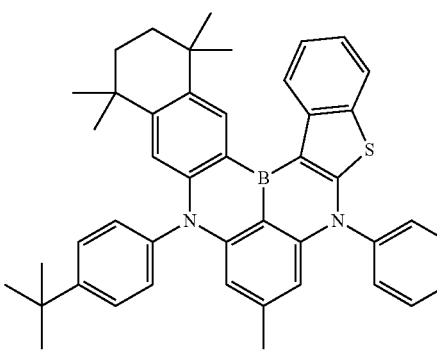
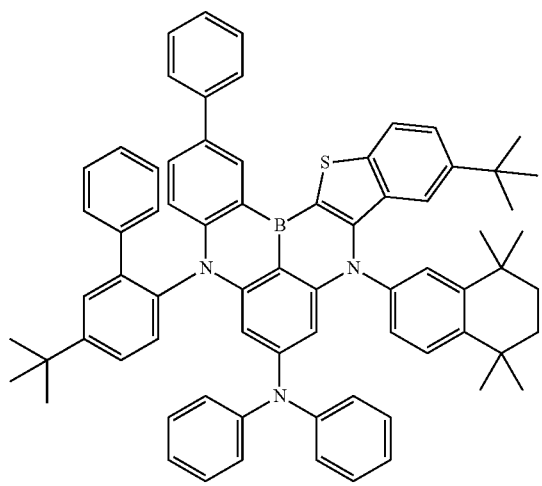
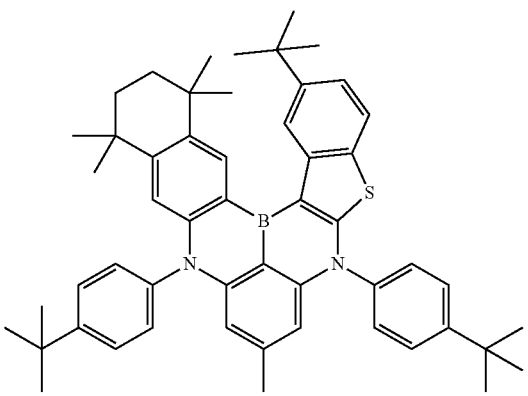
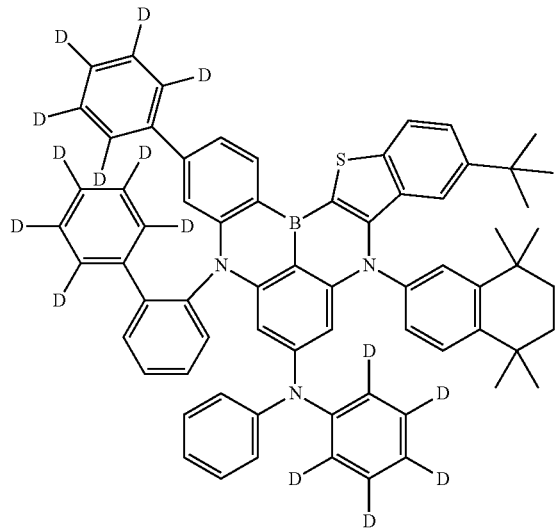
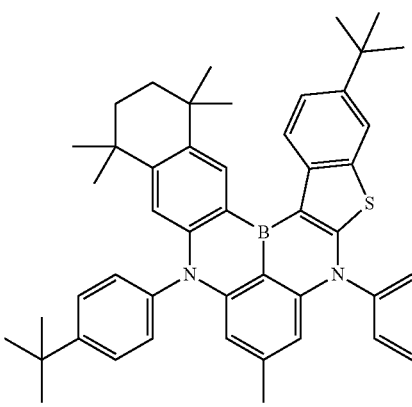

| 1995 -continued | 1996 -continued |
|---|---|
| 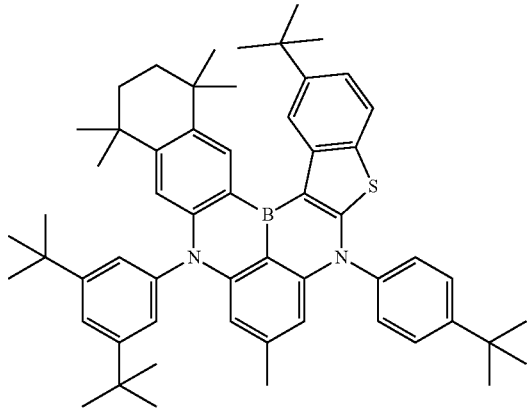 | 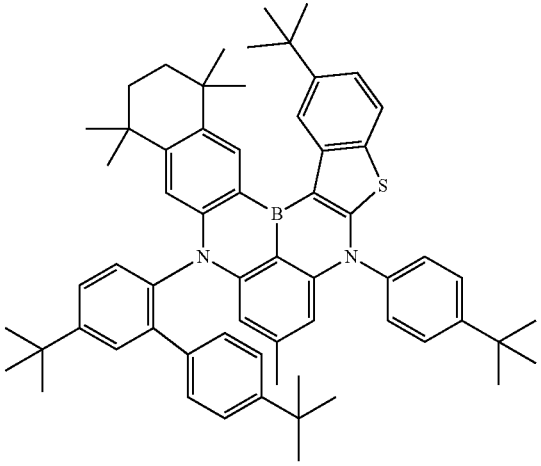 |
| 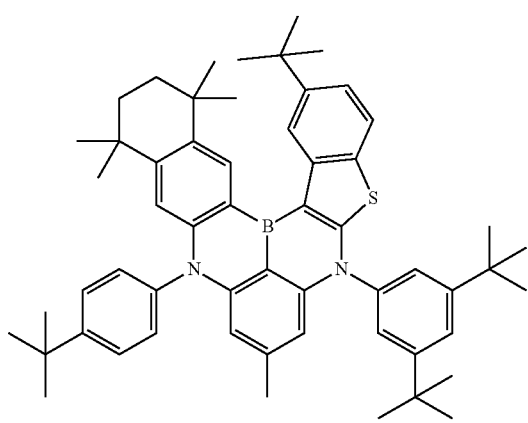 | 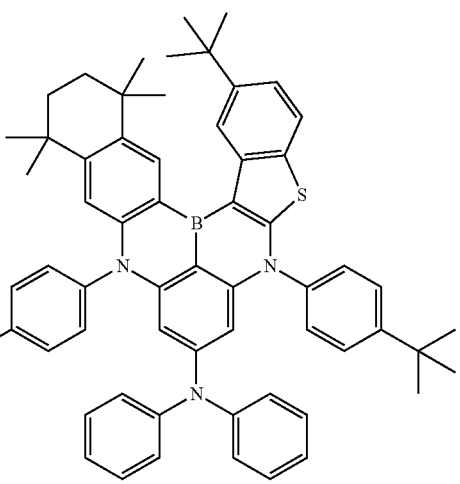 |
| 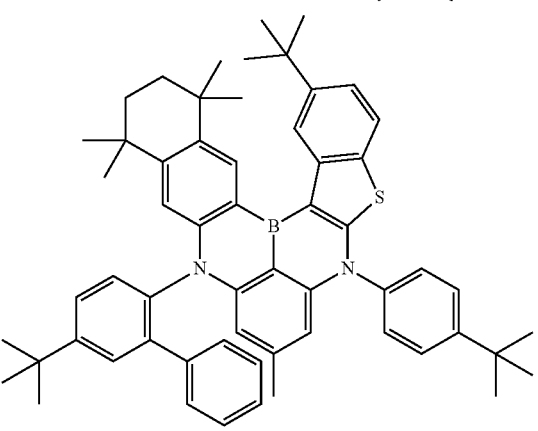 | 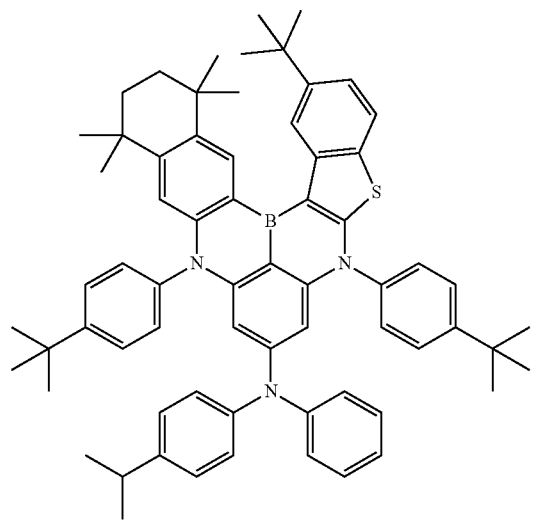 |
| 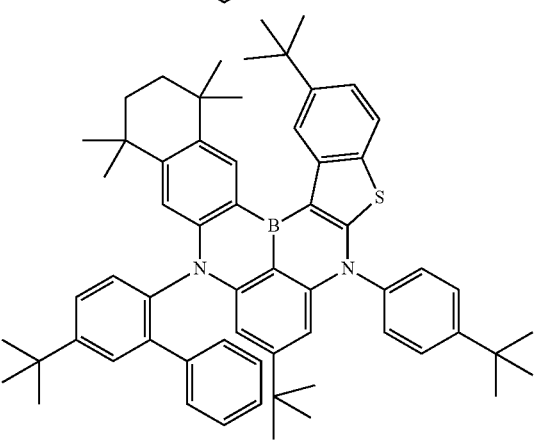 | |

1997
-continued
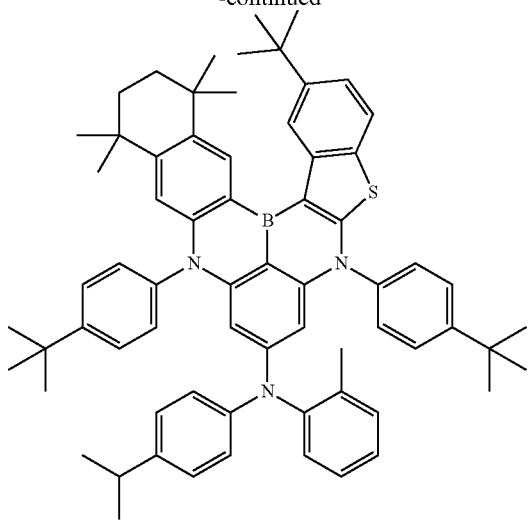
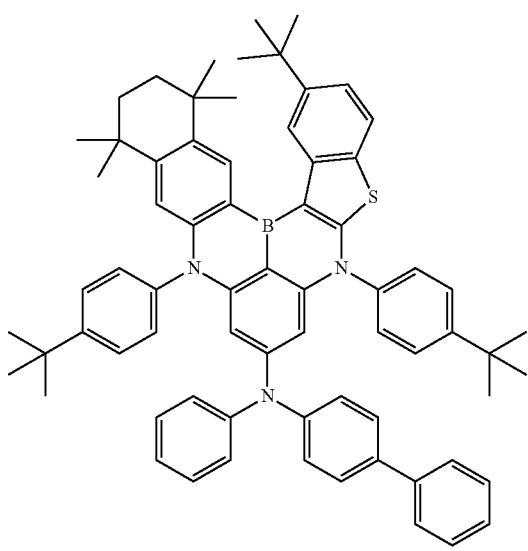
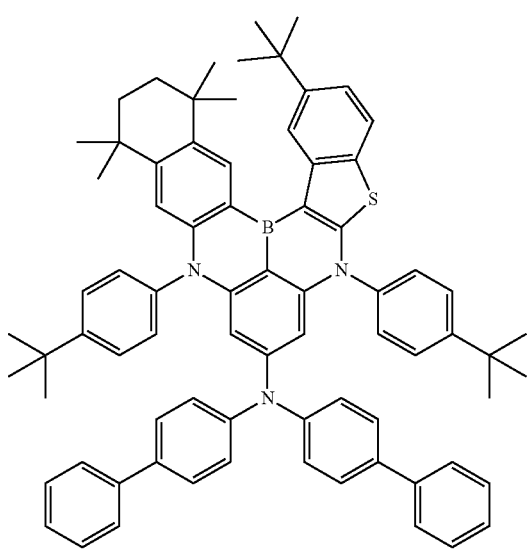
1998
-continued
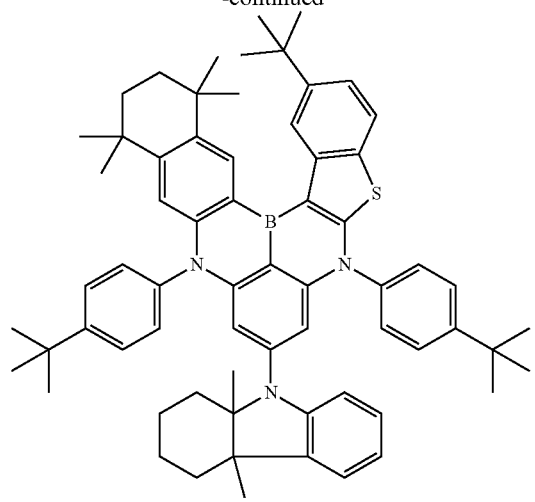
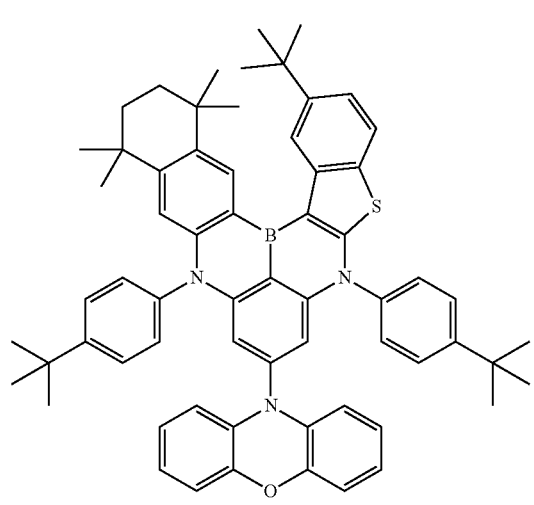
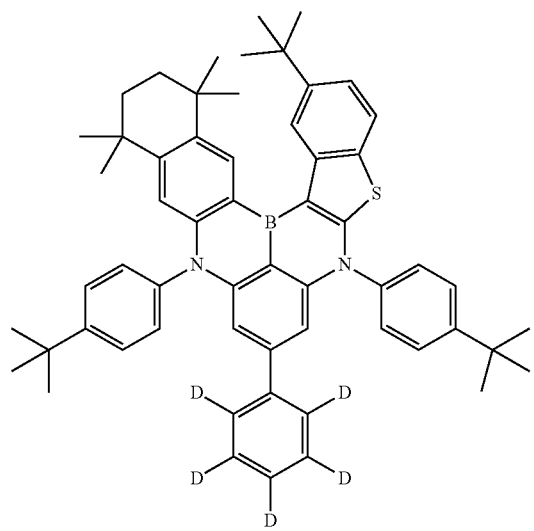

1999
-continued
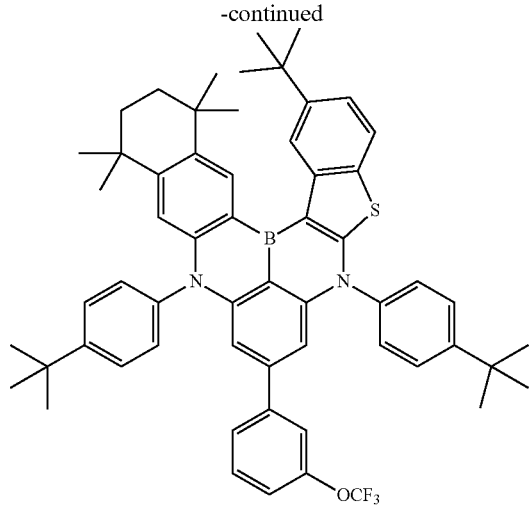
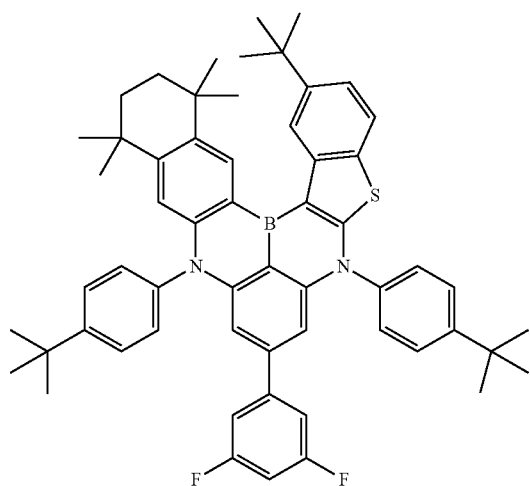
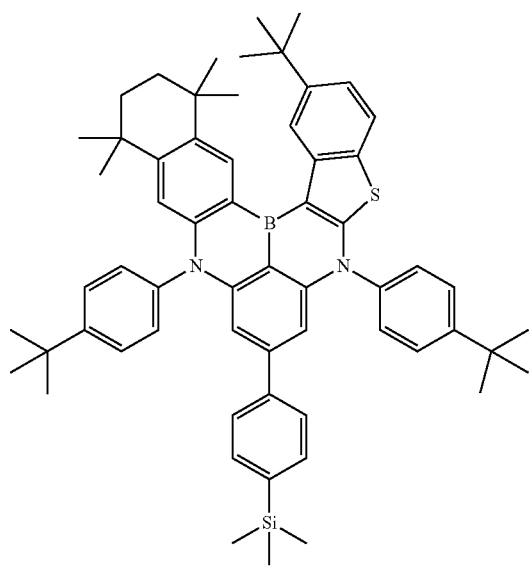
2000
-continued

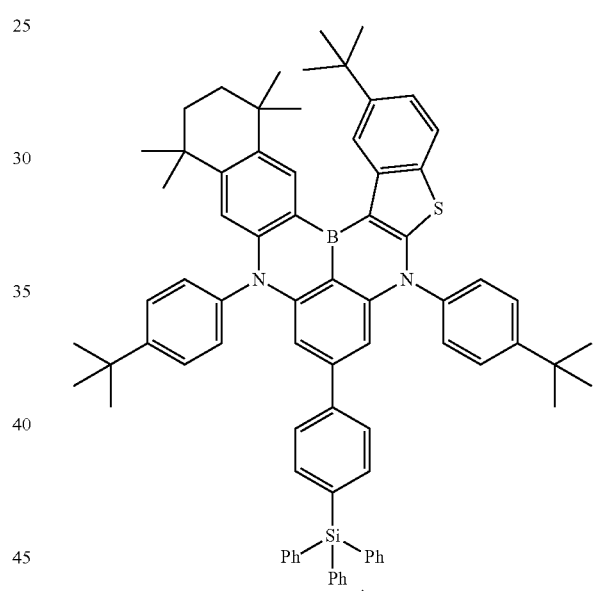
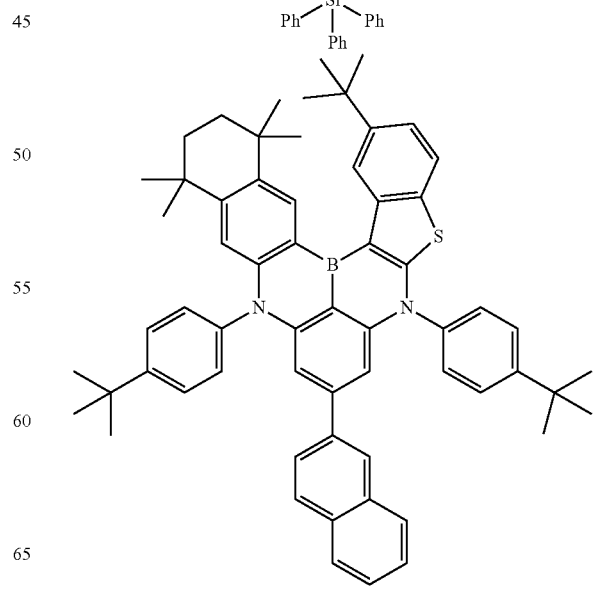

2001
-continued
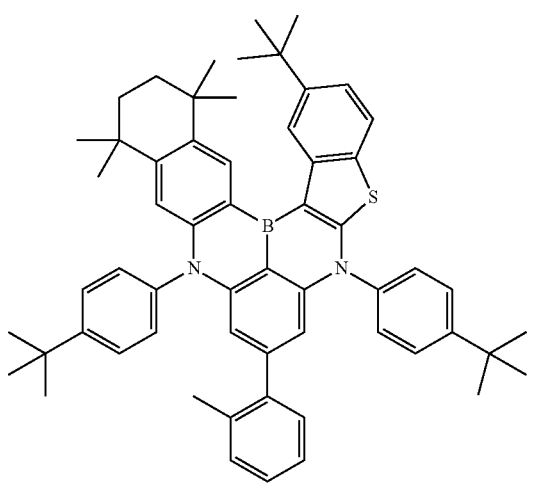
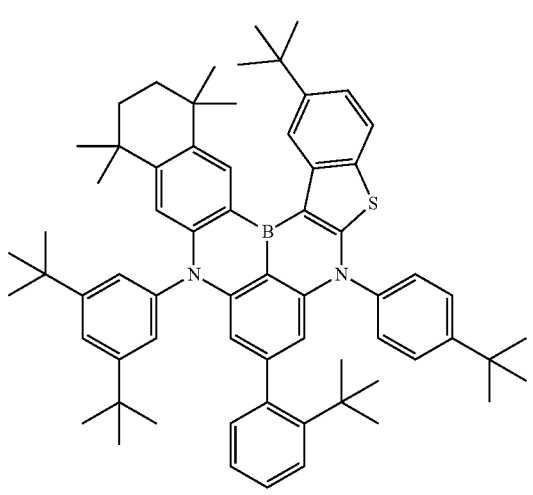
2002
-continued
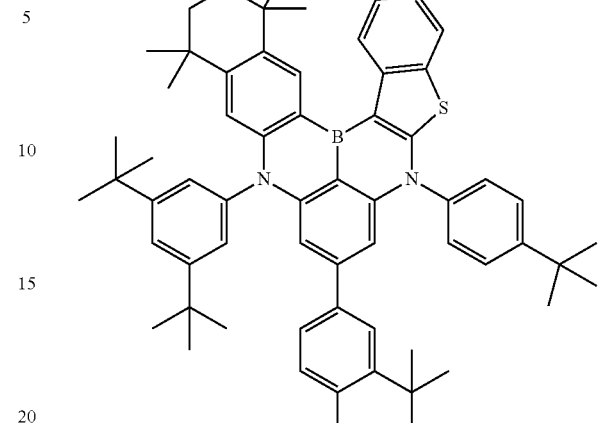
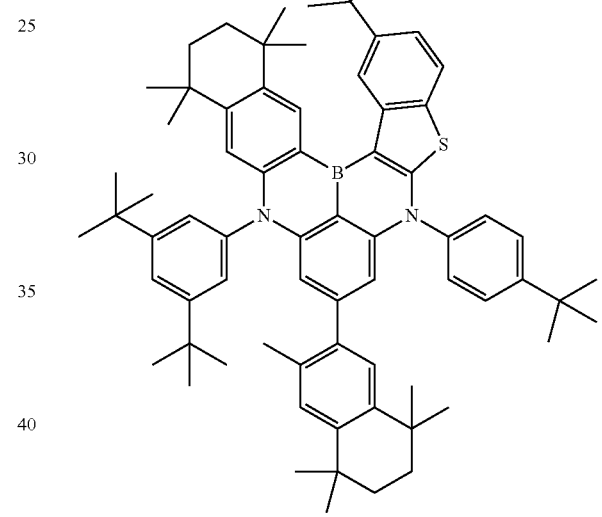
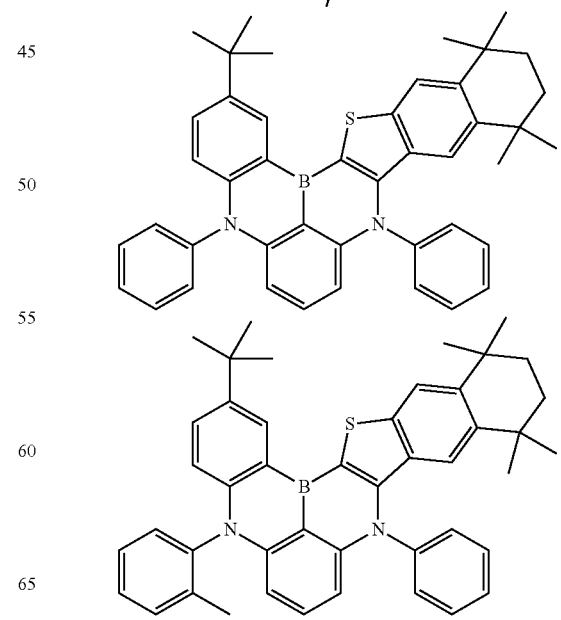

2003
-continued
2004
-continued
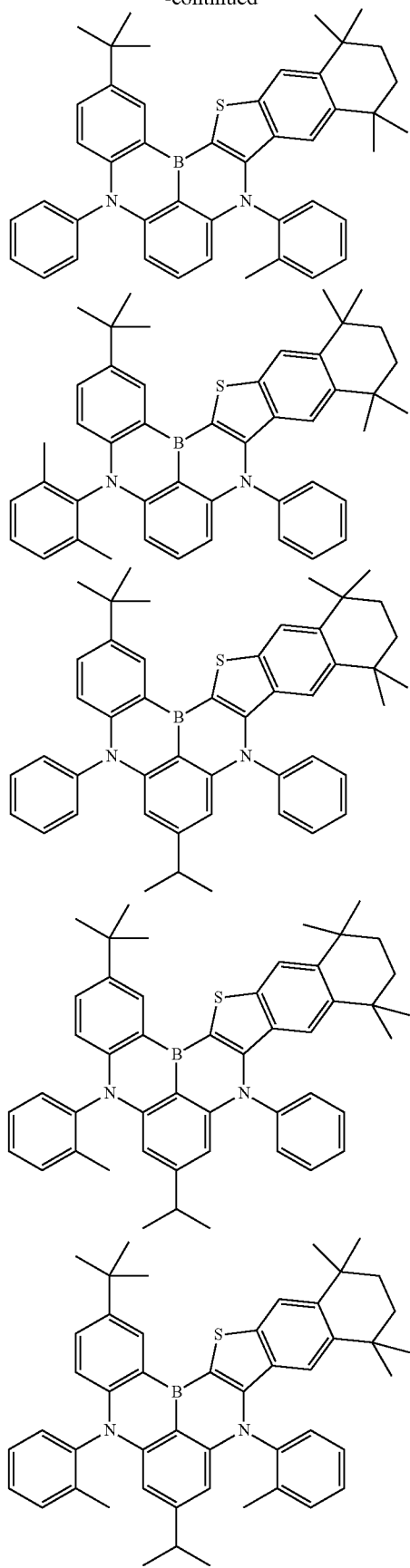
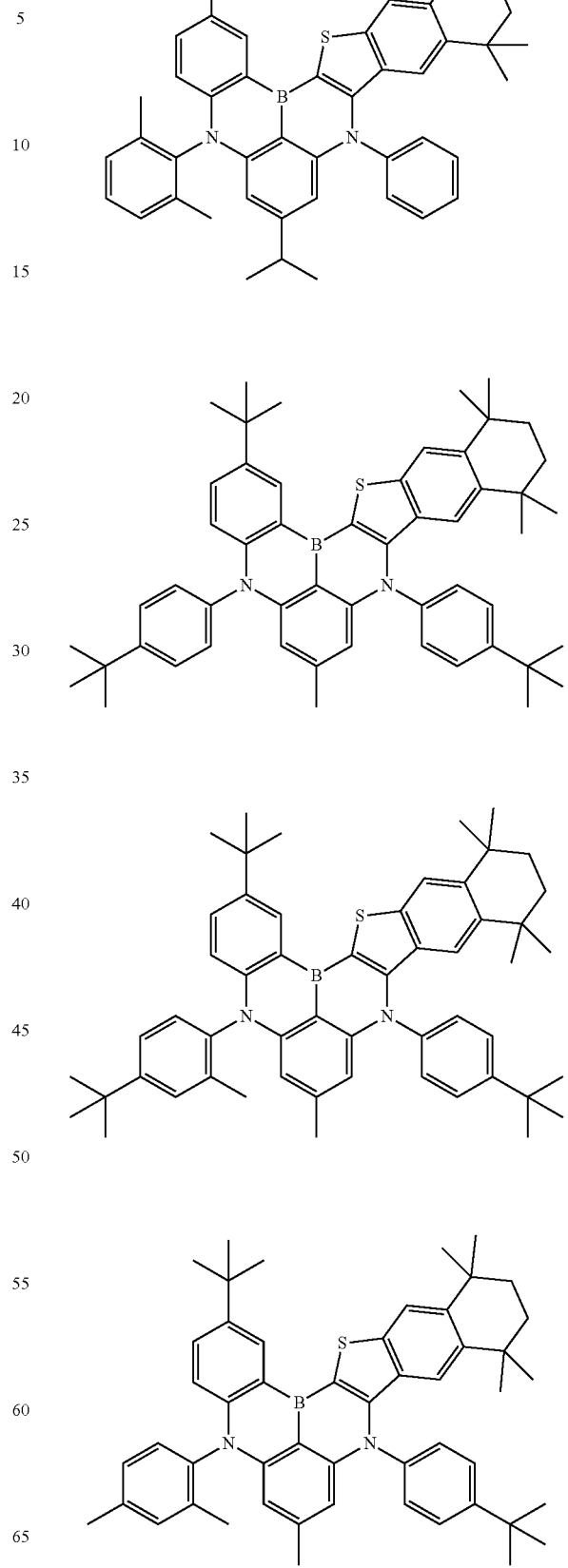

| 2005 -continued | 2006 -continued |
|---|---|
| 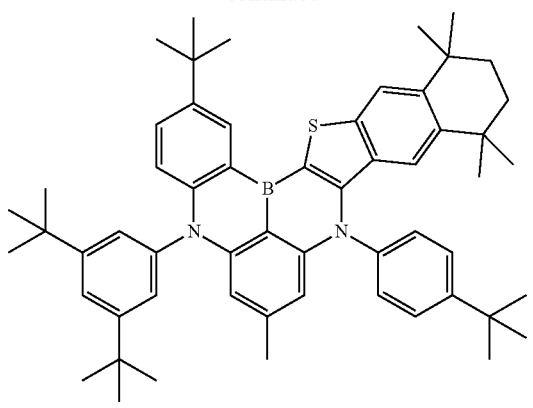 | 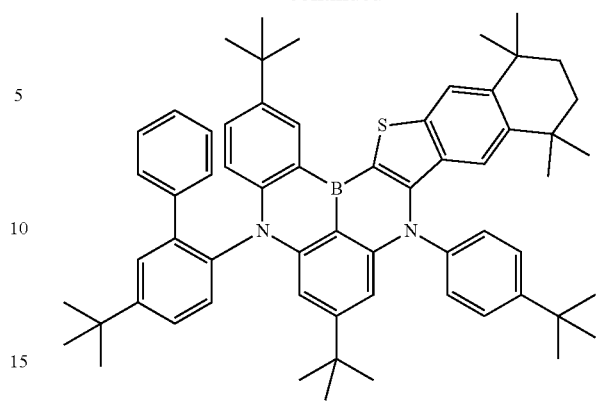 |
| 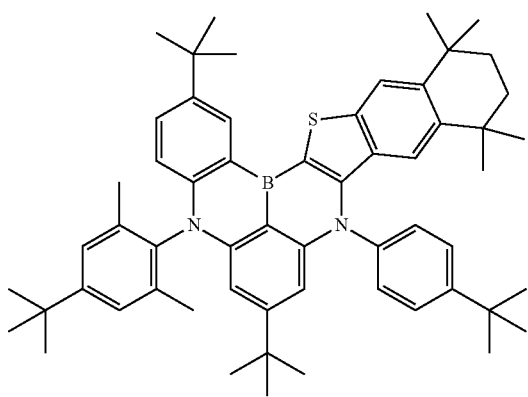 | 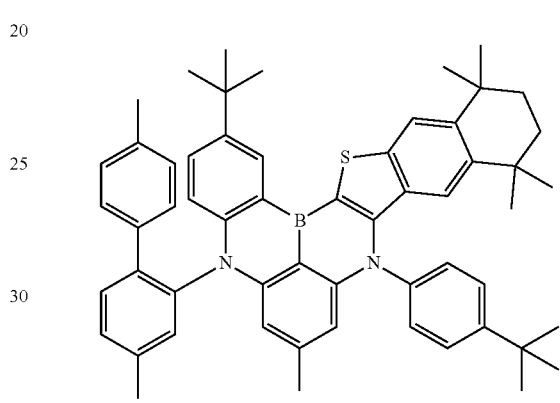 |
| 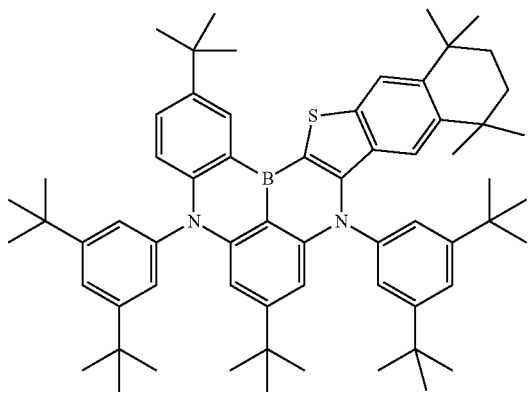 | 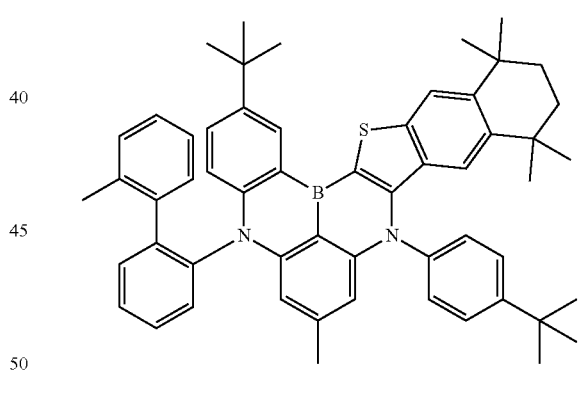 |
| 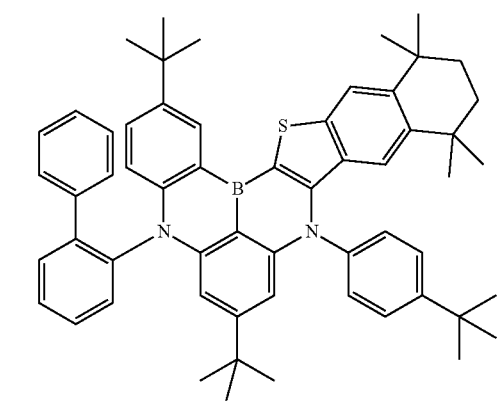 | 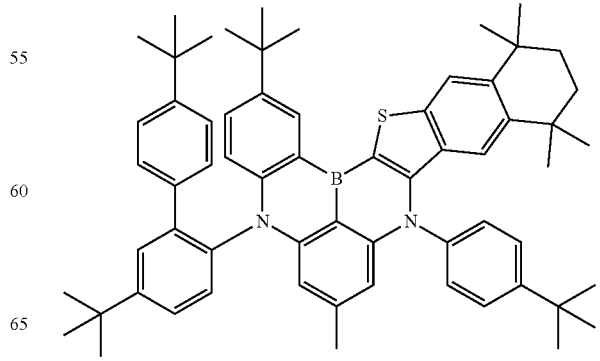 |

2007
-continued
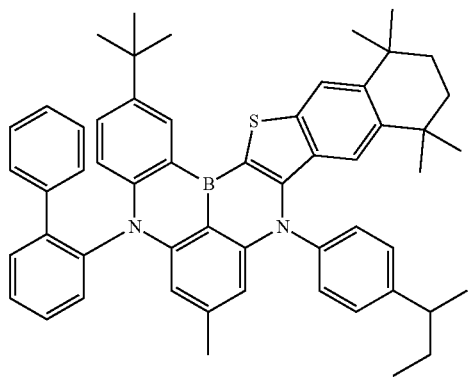
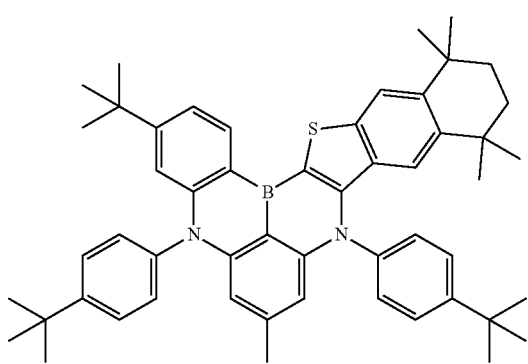
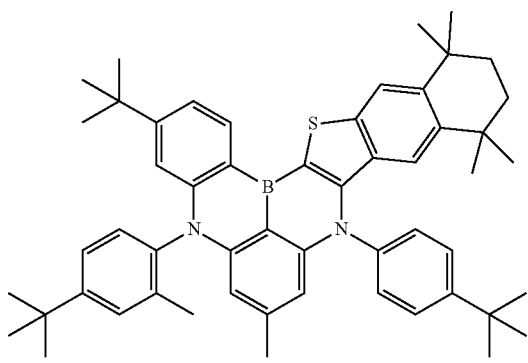
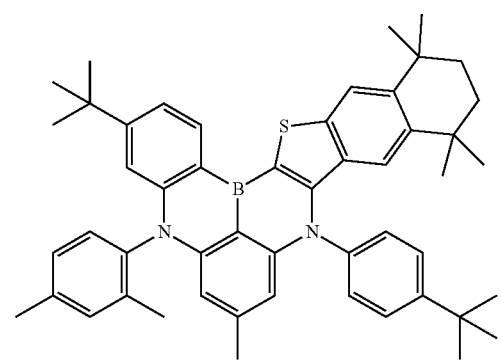
2008
-continued
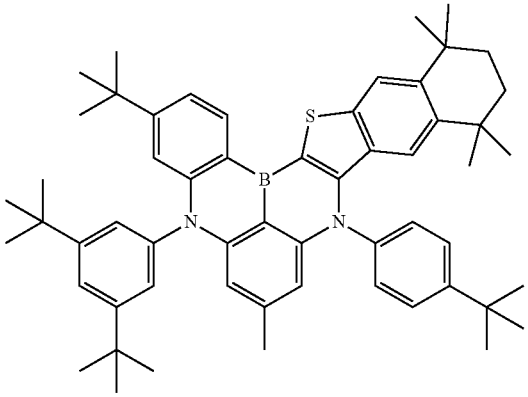
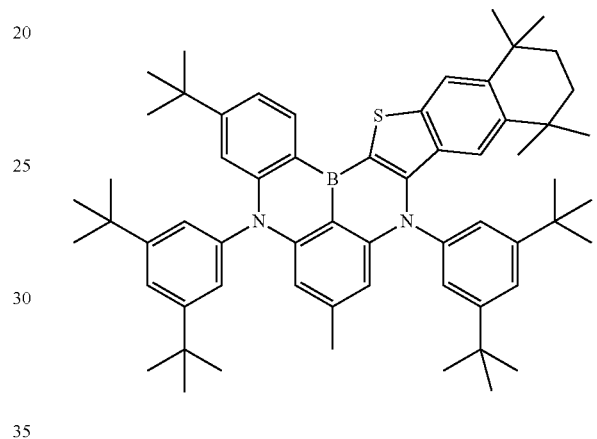
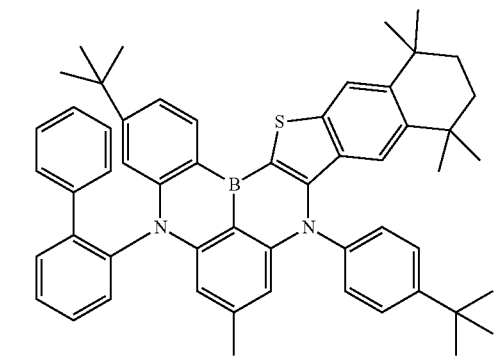
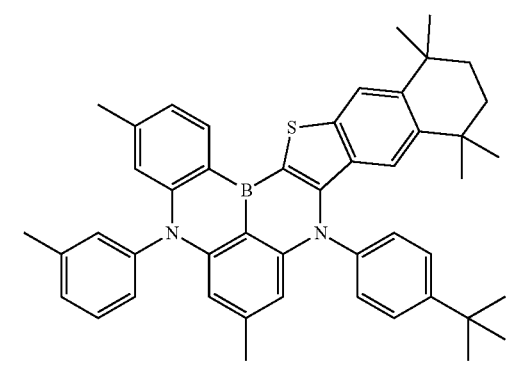

2009
-continued
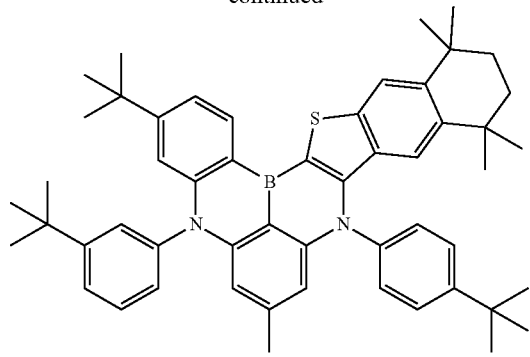
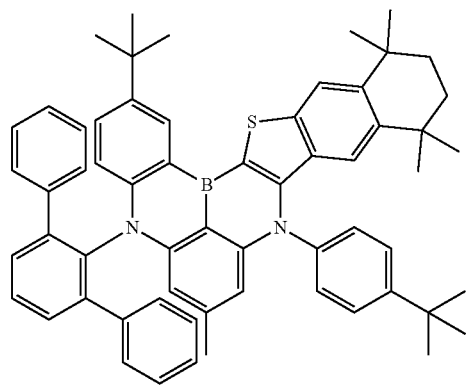
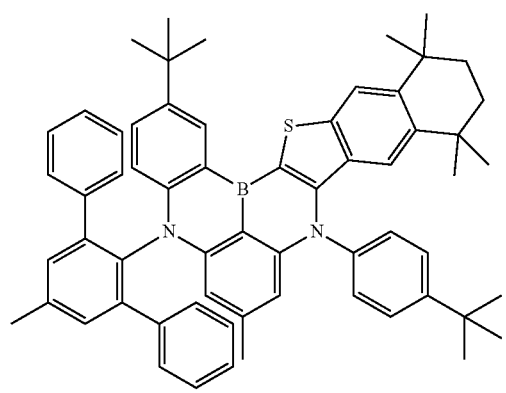
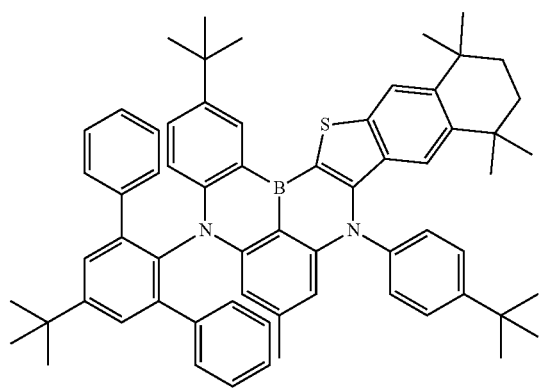
2010
-continued
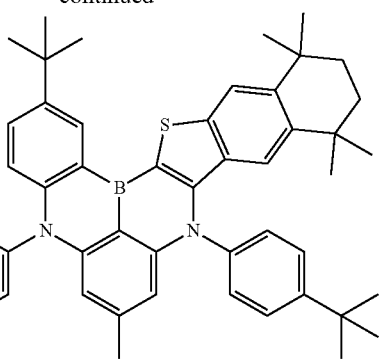
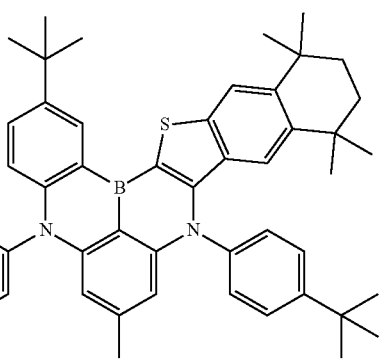
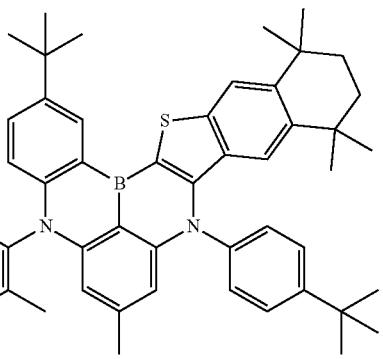
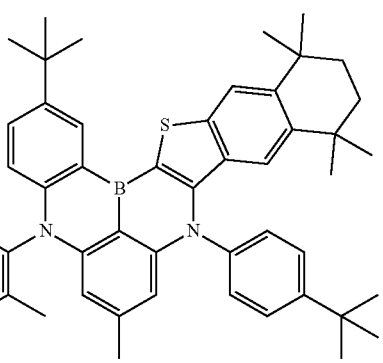

2011
-continued
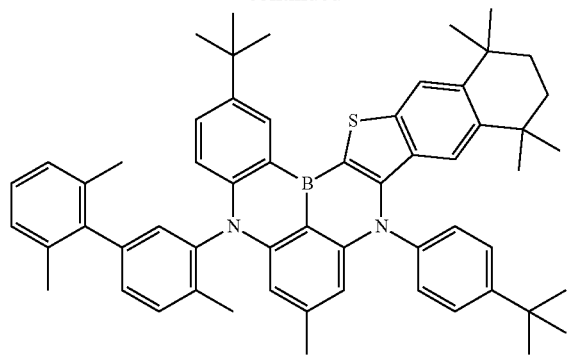
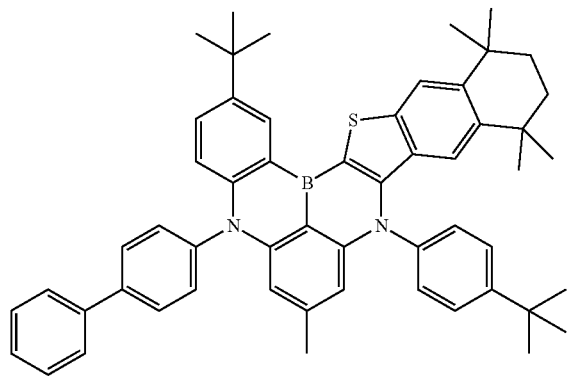
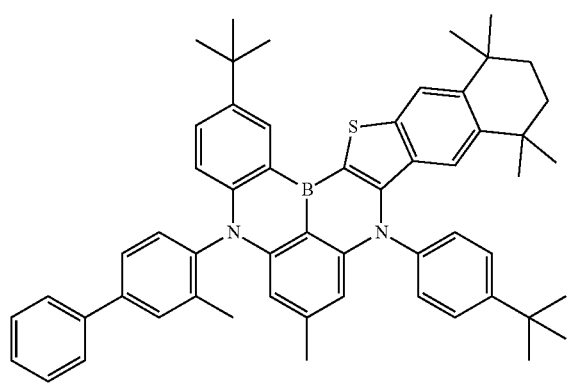
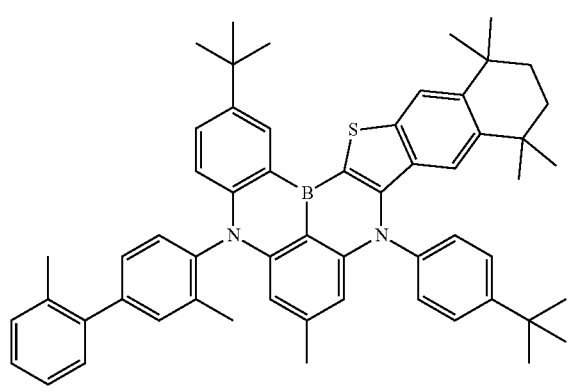
2012
-continued
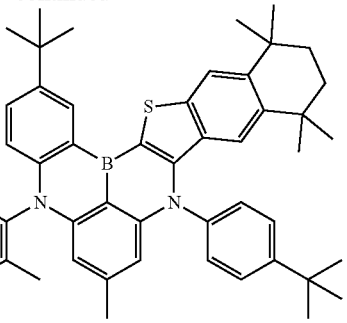
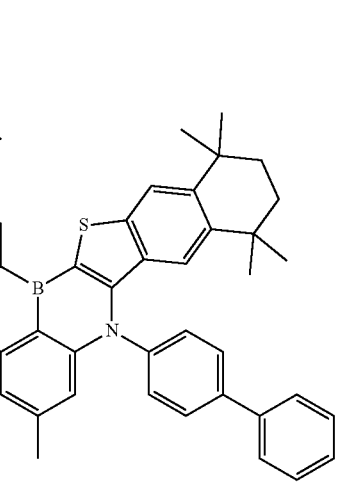
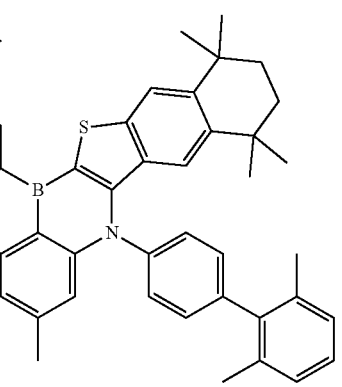
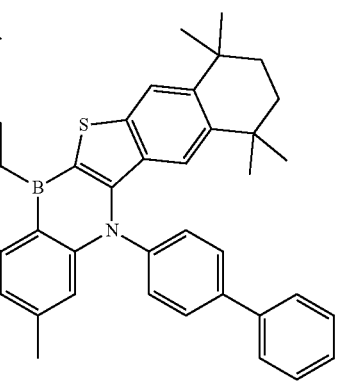

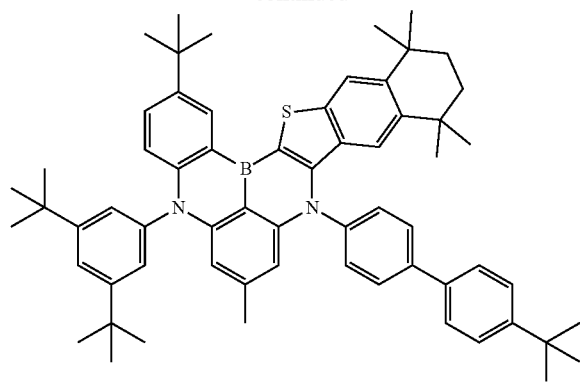
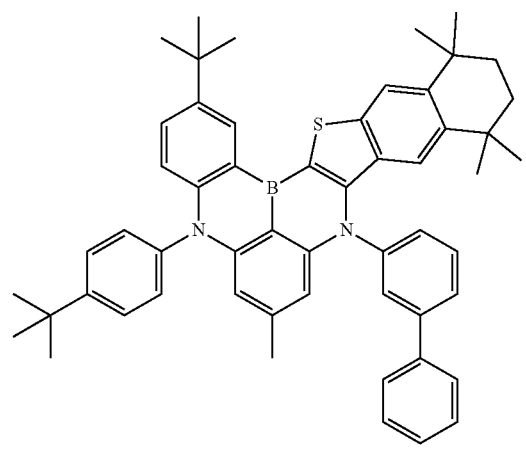
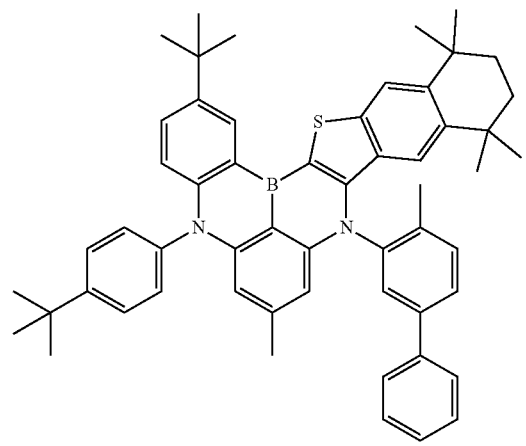
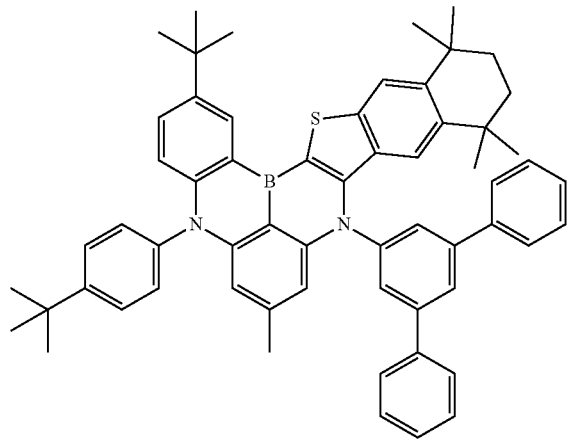
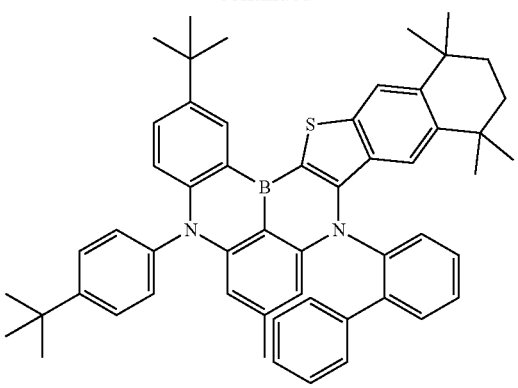
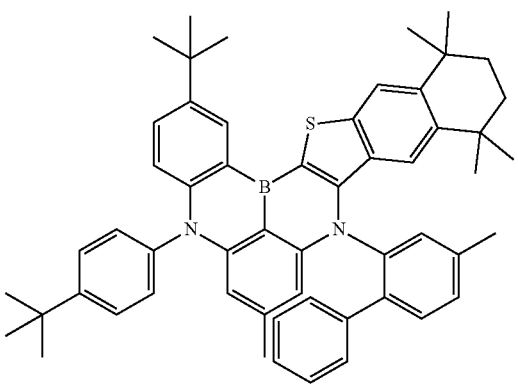
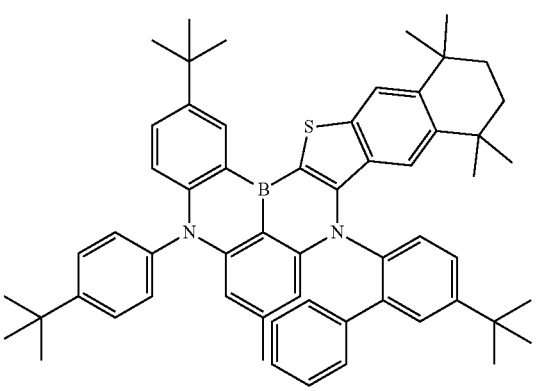
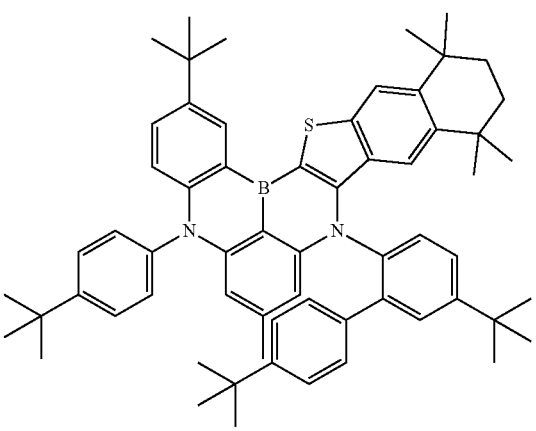

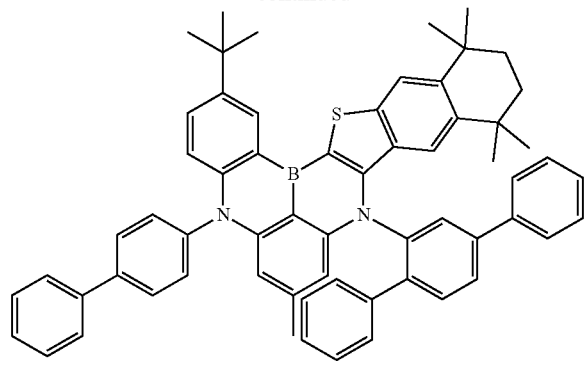
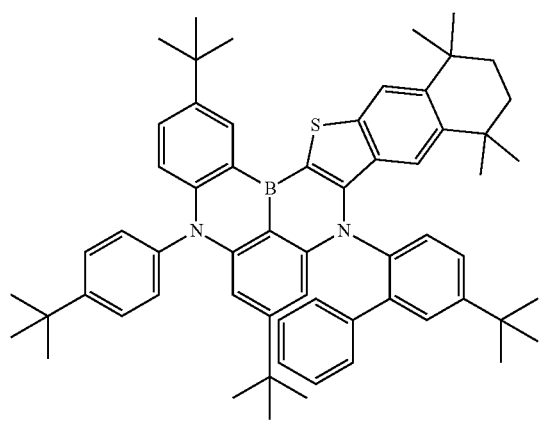
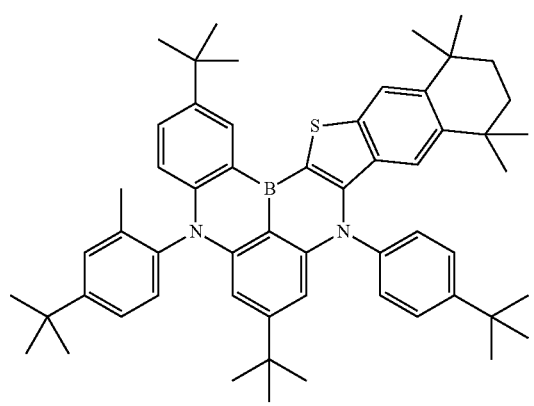
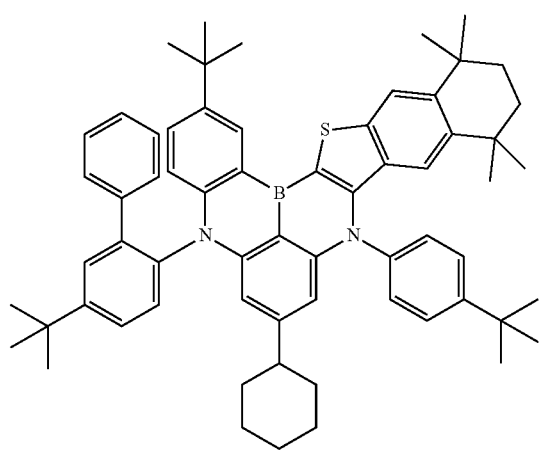
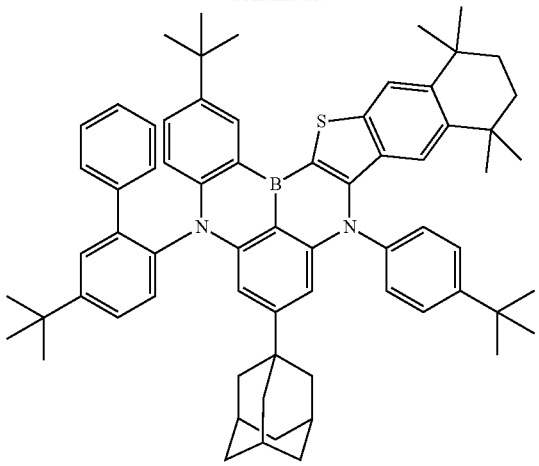
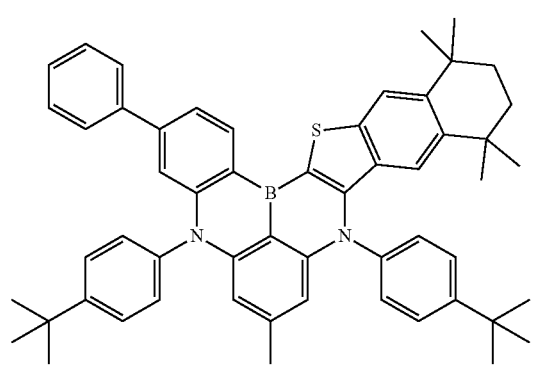
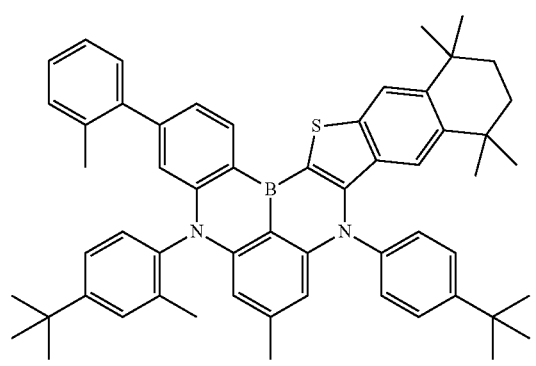
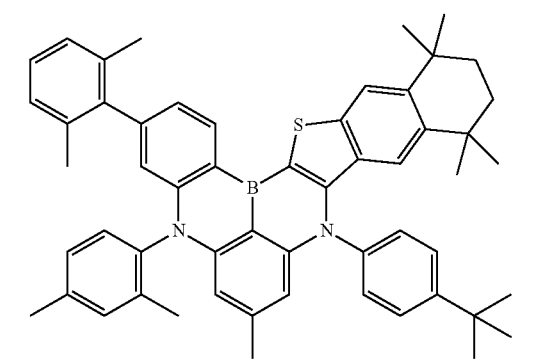

2017
-continued
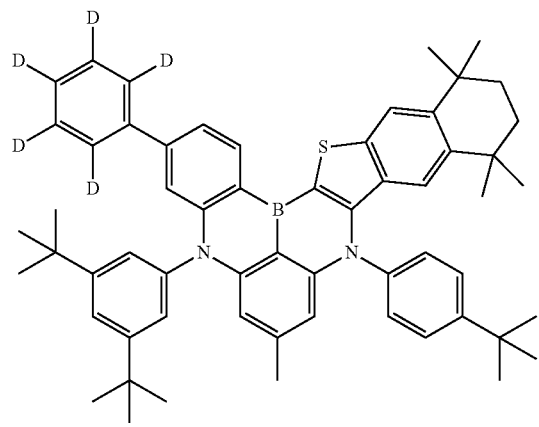
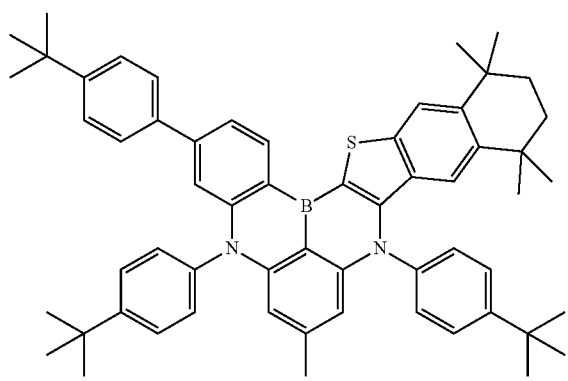
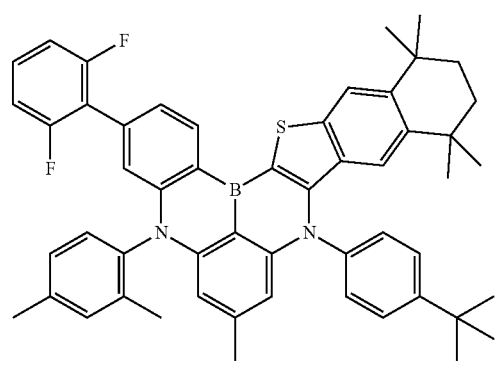
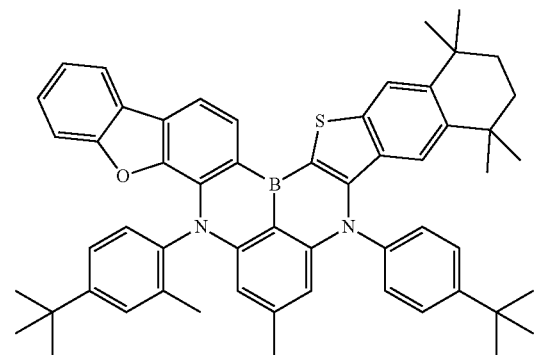
2018
-continued
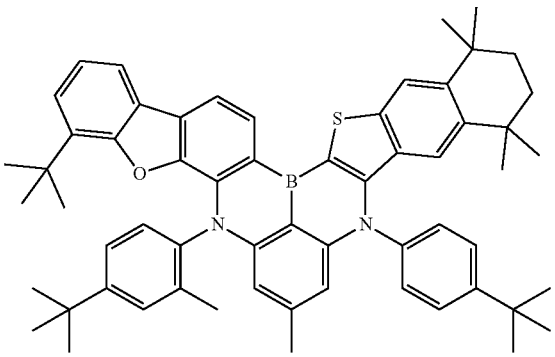
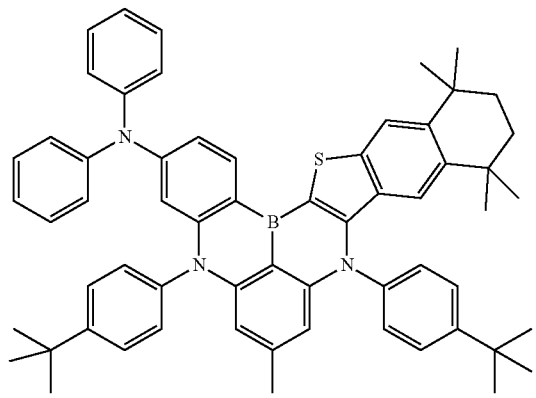
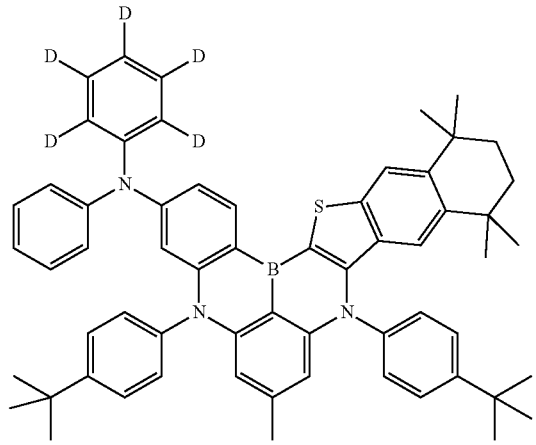
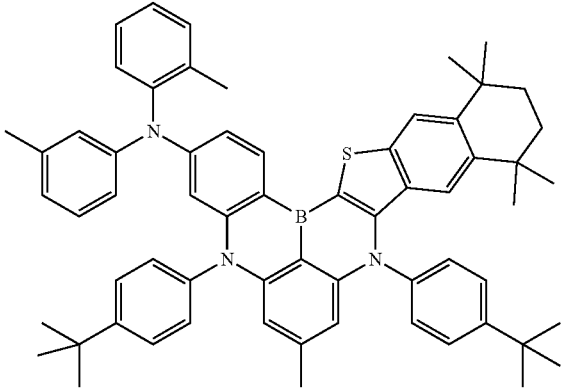

2019
-continued
2020
-continued
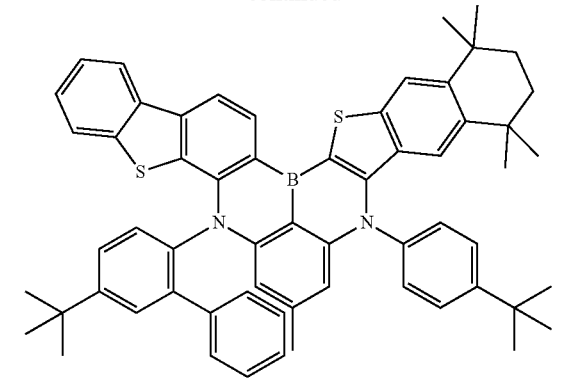
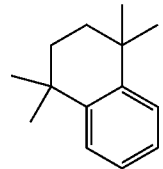
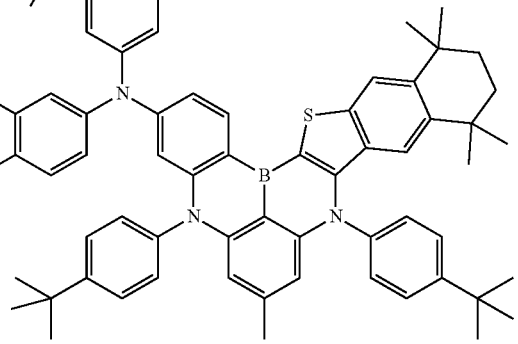
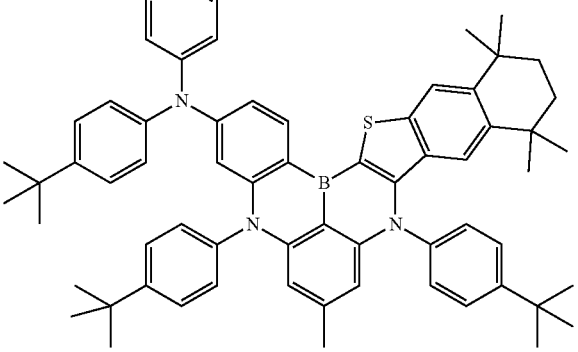
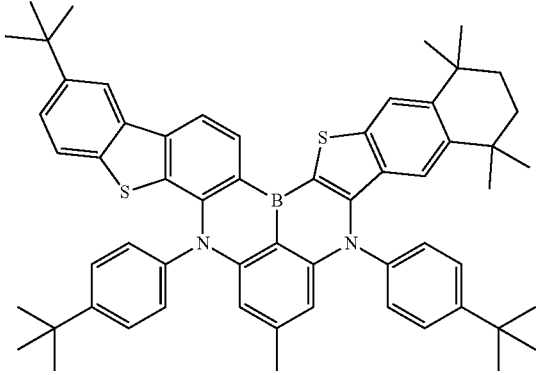
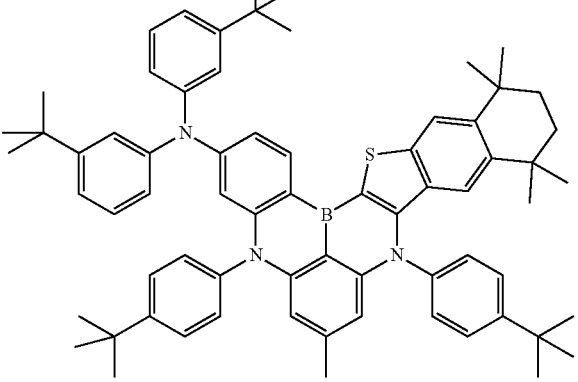
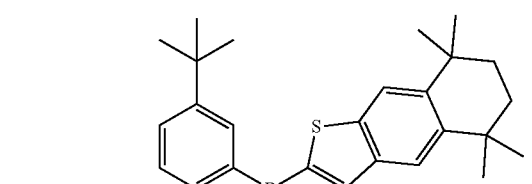
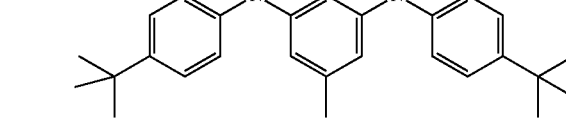
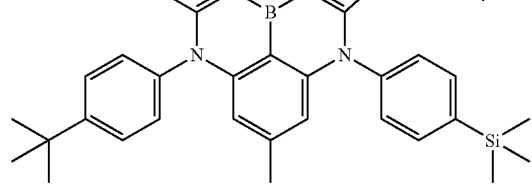
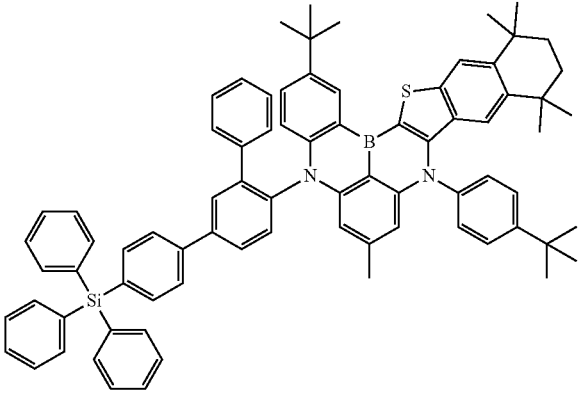

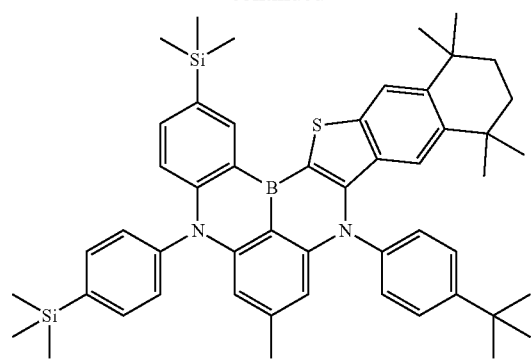
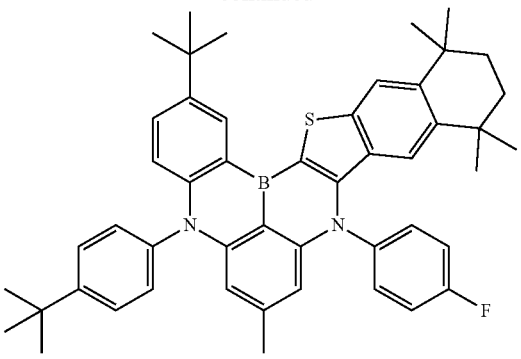
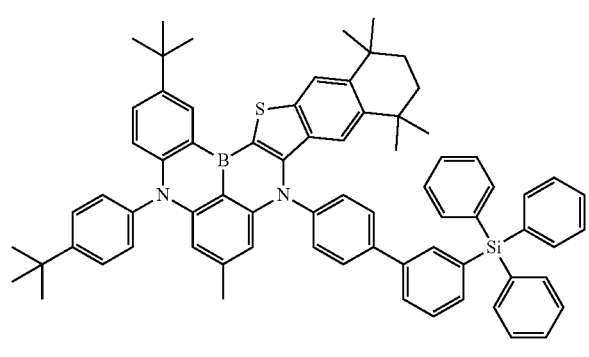
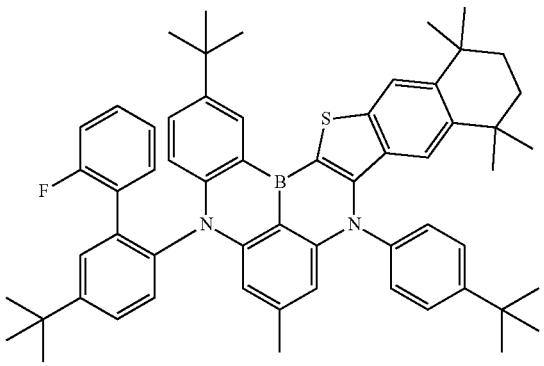
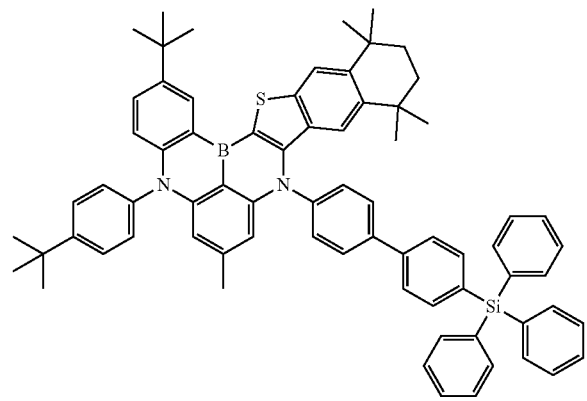
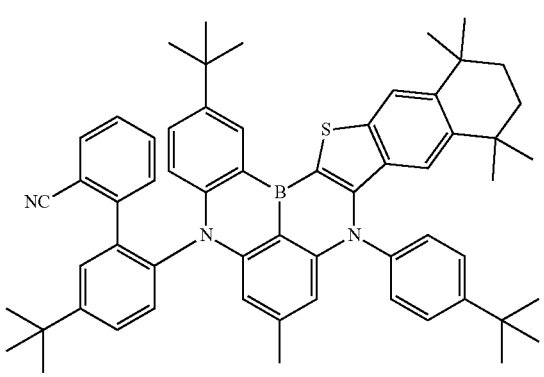
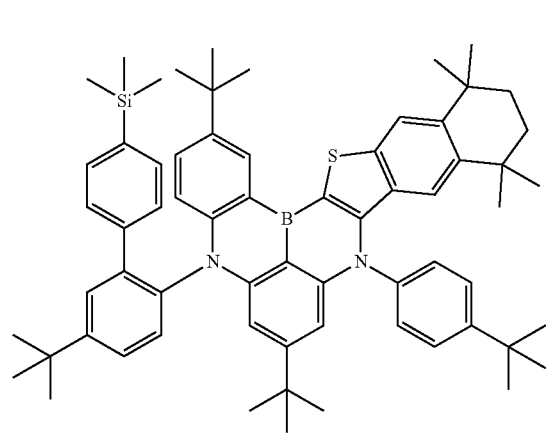
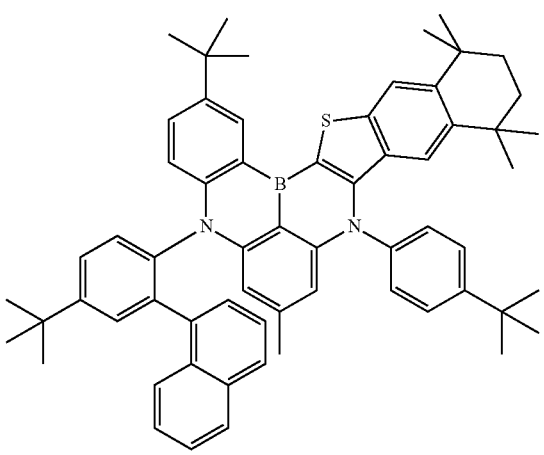

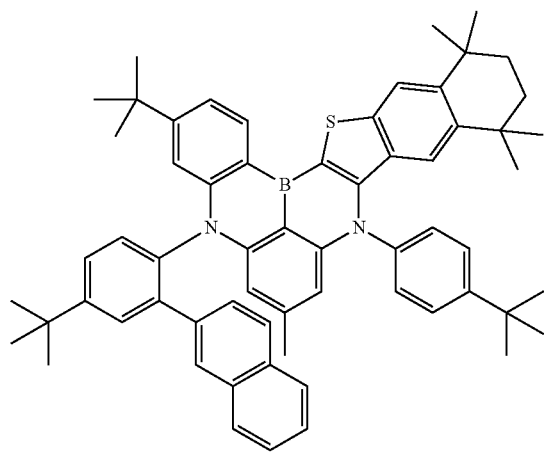

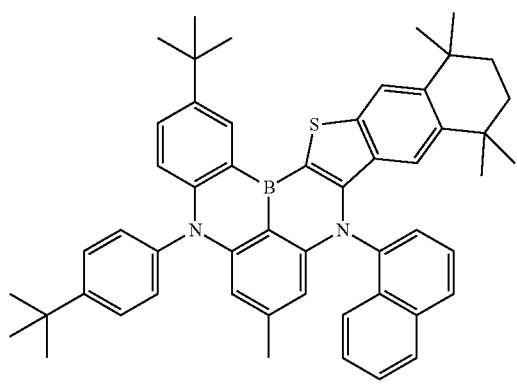

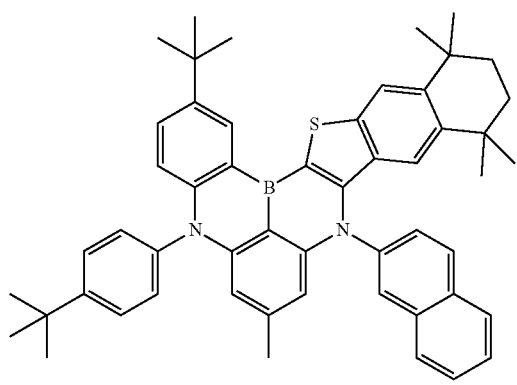
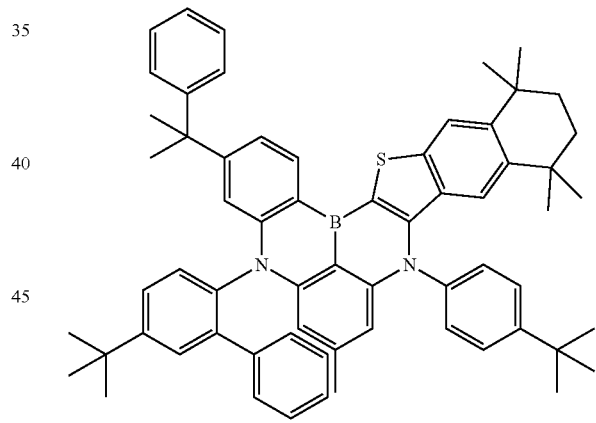
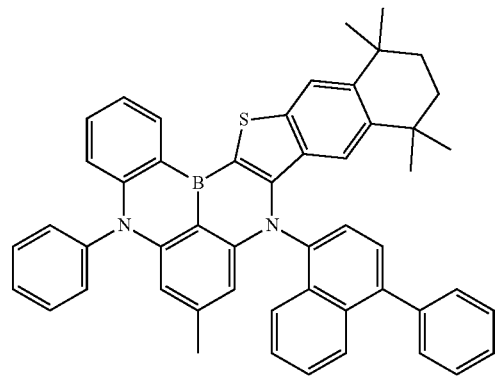
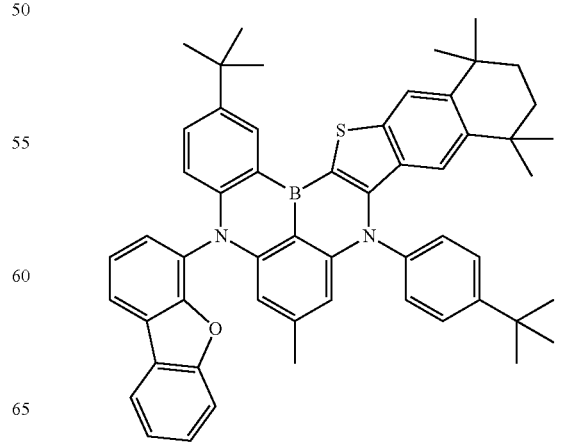

2025
-continued
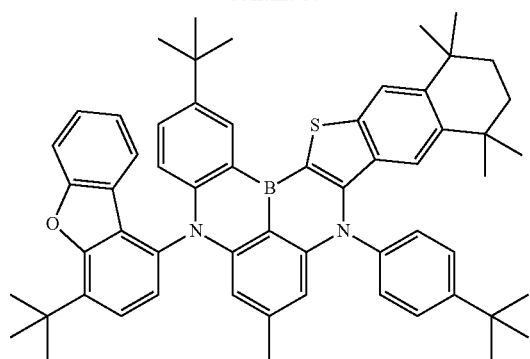
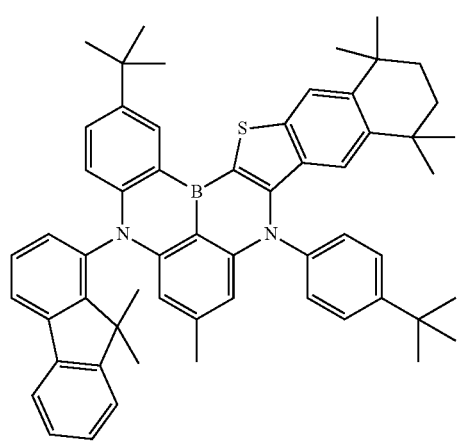
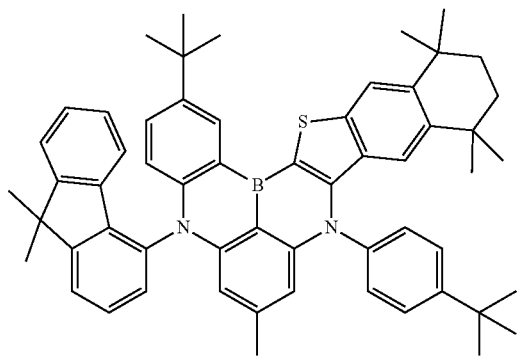
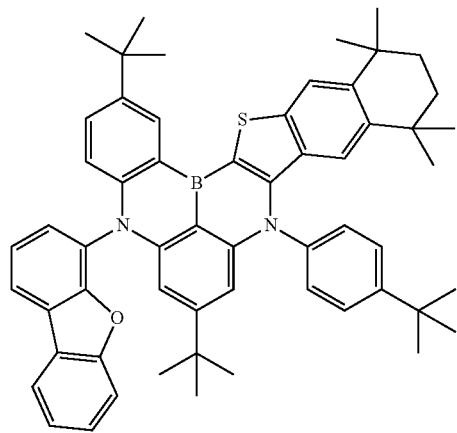
2026
-continued
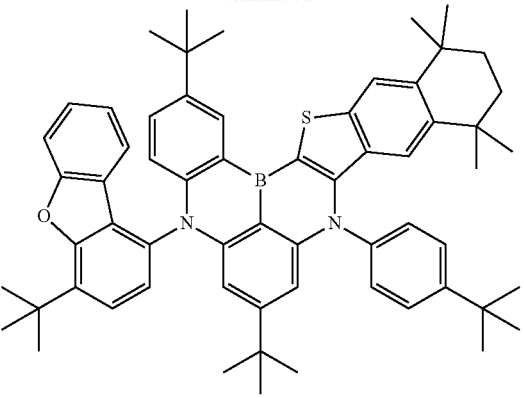
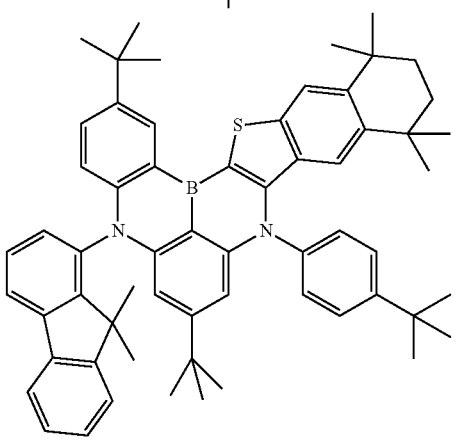
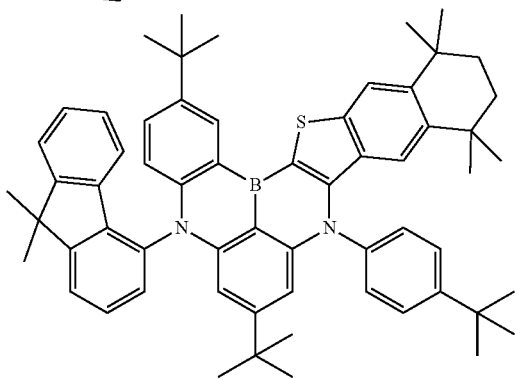
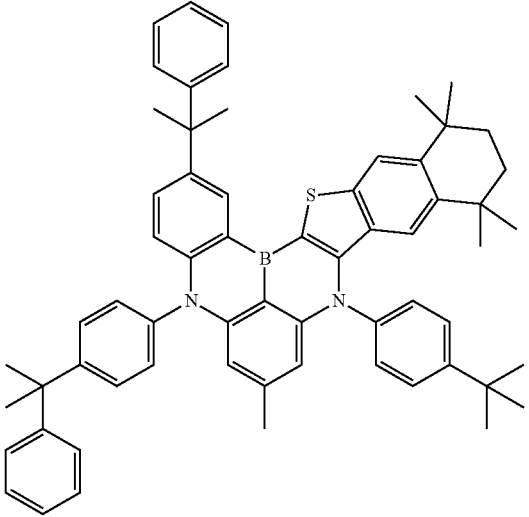

| 2027 | 2028 |
|---|---|
| -continued | -continued |
| 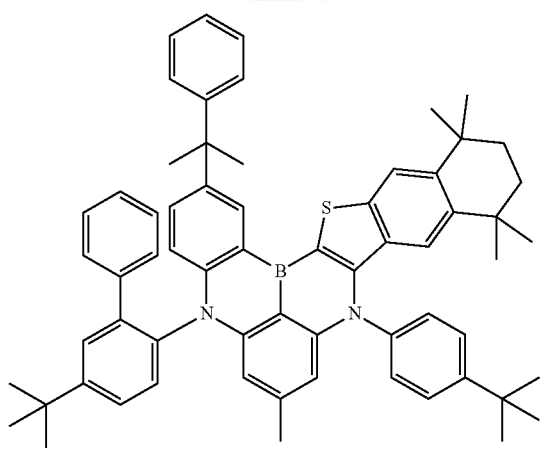 | 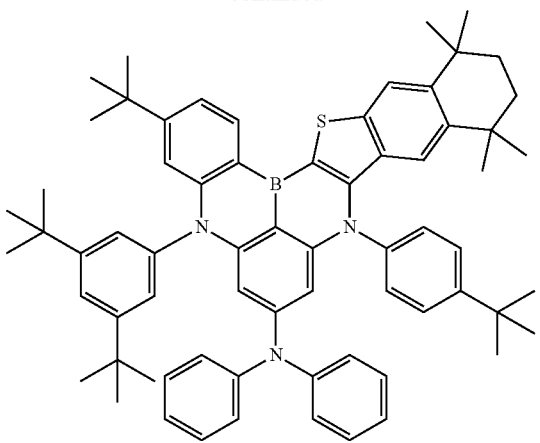 |
| 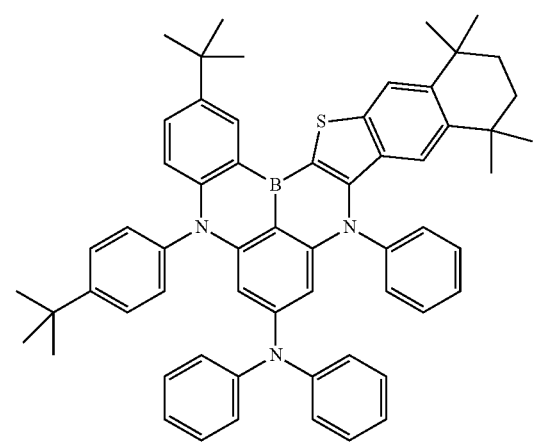 | 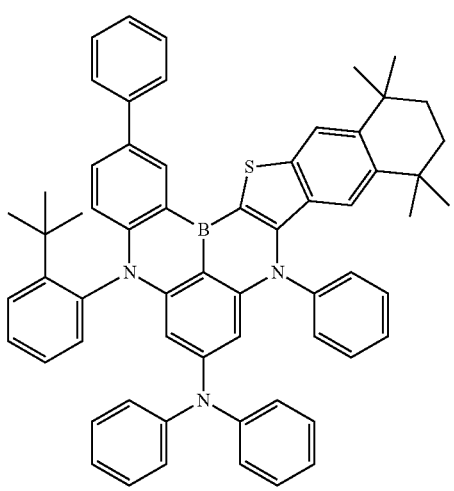 |
| 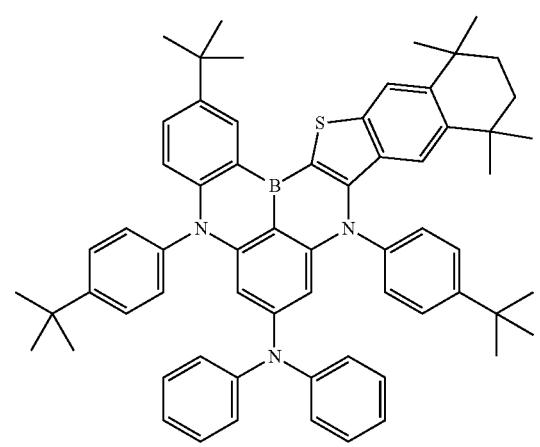 | 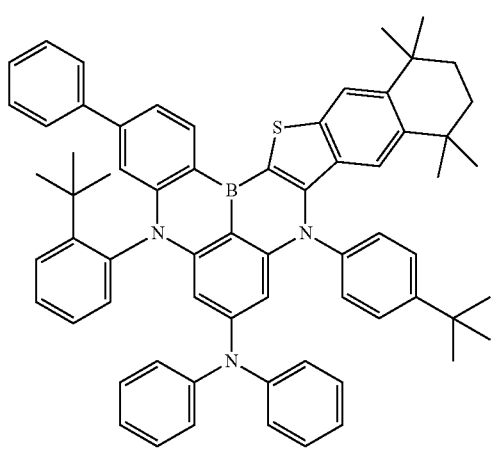 |

2029
-continued
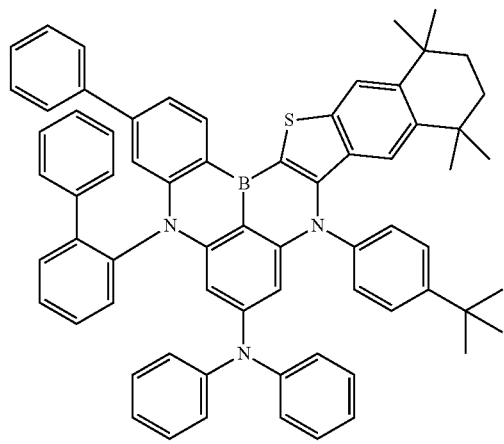
2030
-continued
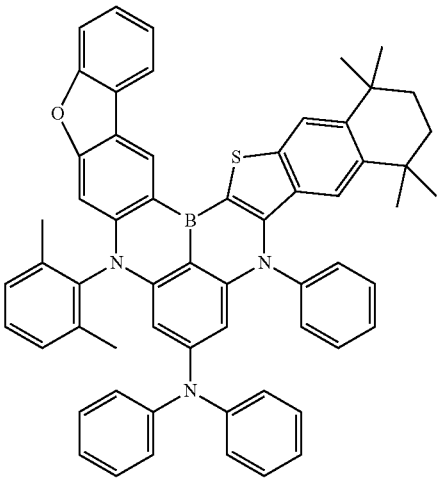
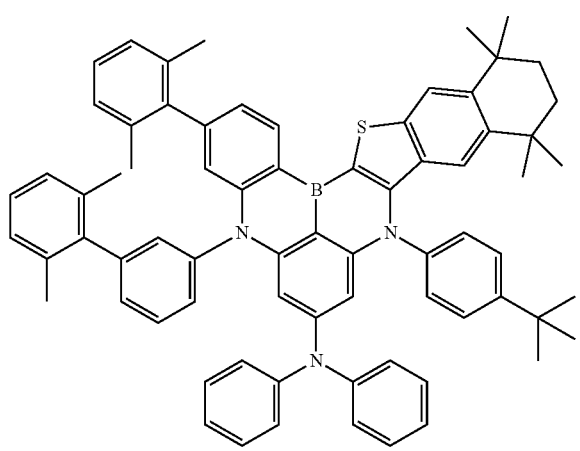
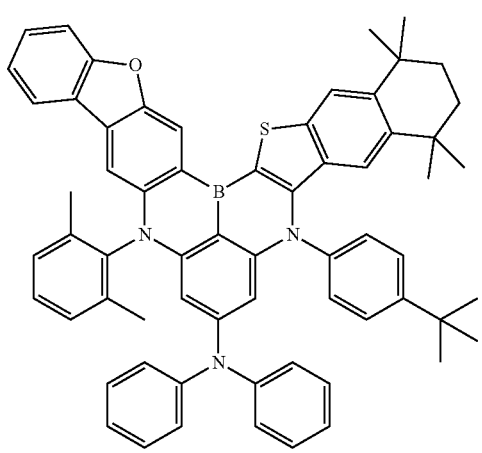
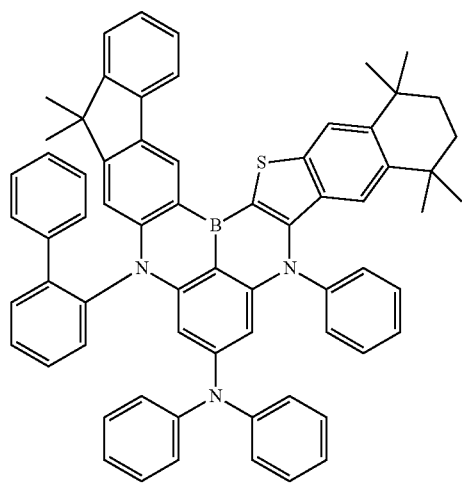
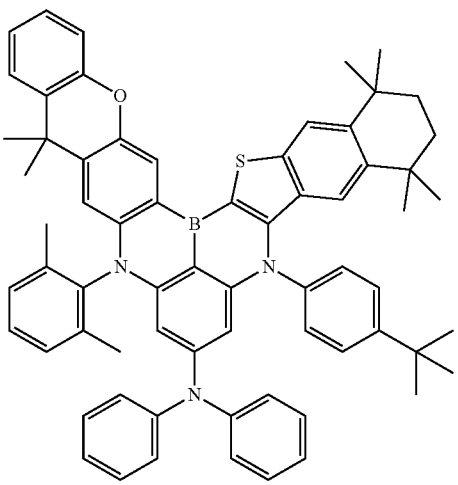

2031
-continued
2032
-continued
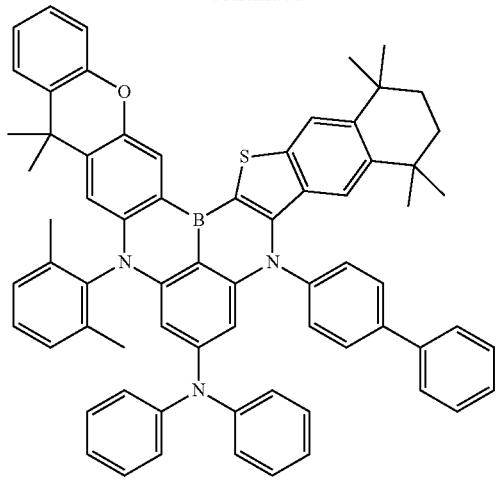
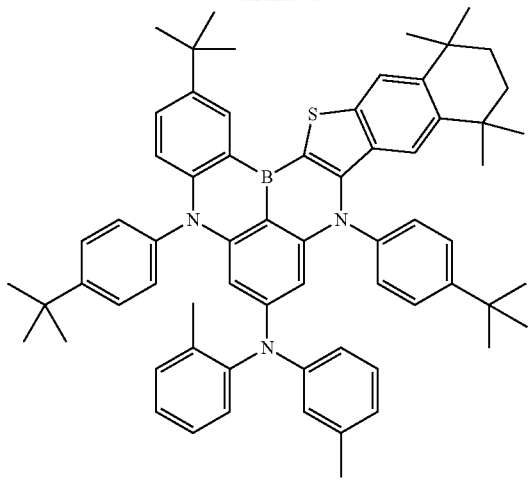
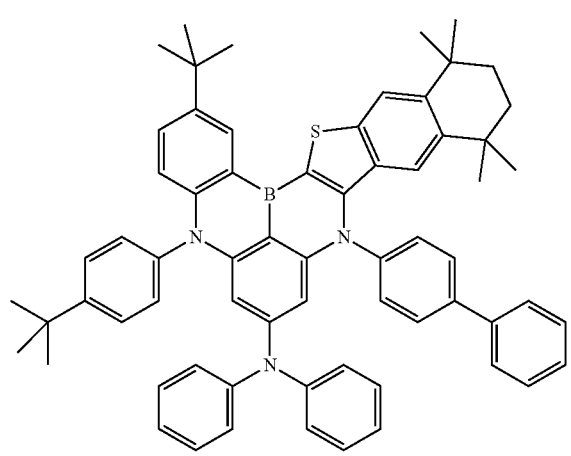
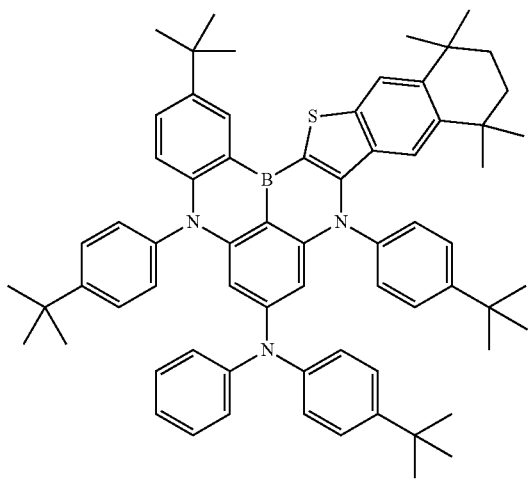
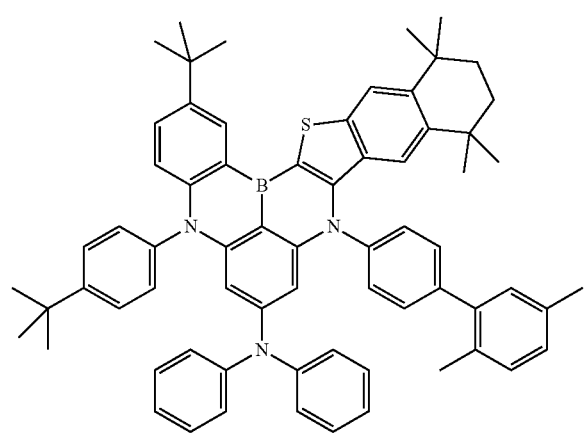
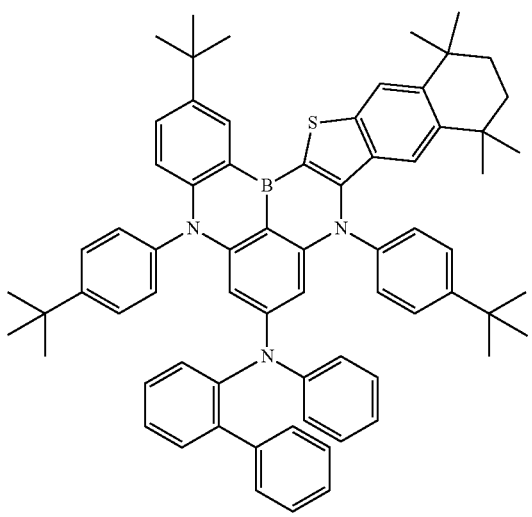

| 2033 -continued | 2034 -continued |
|---|---|
| 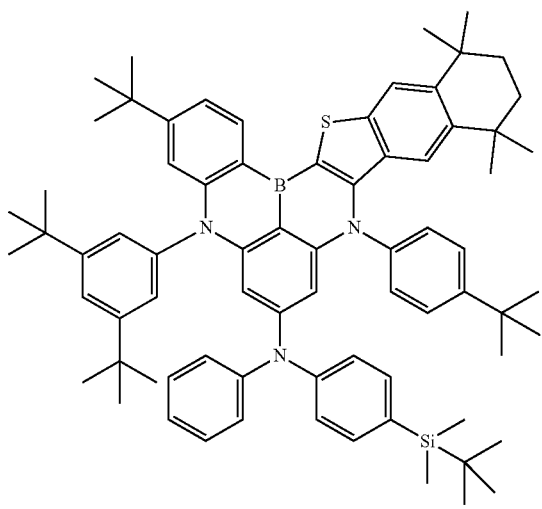 | 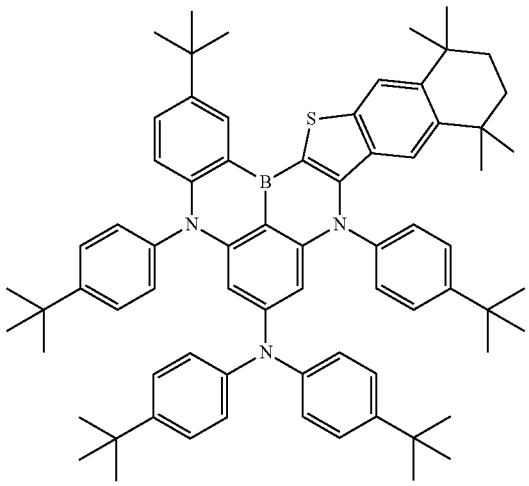 |
| 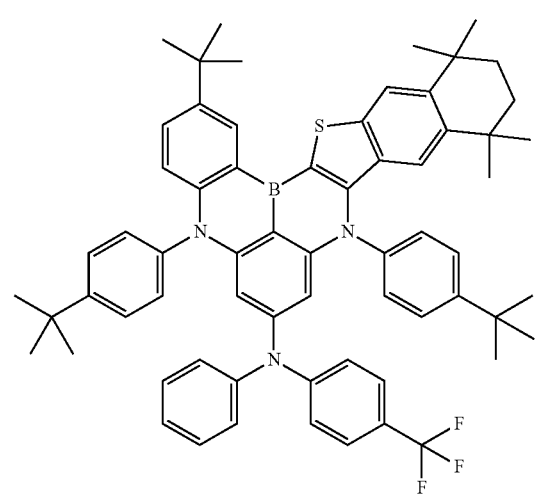 | 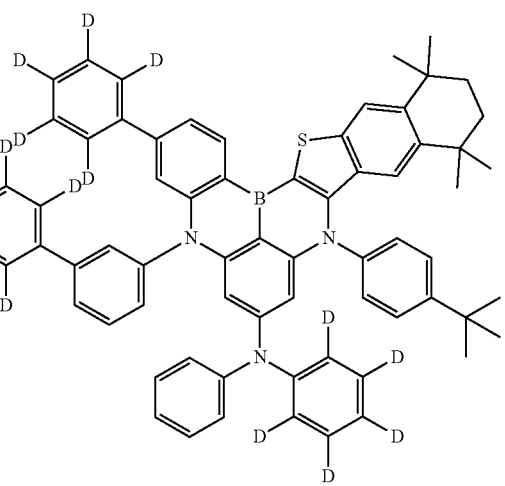 |
| 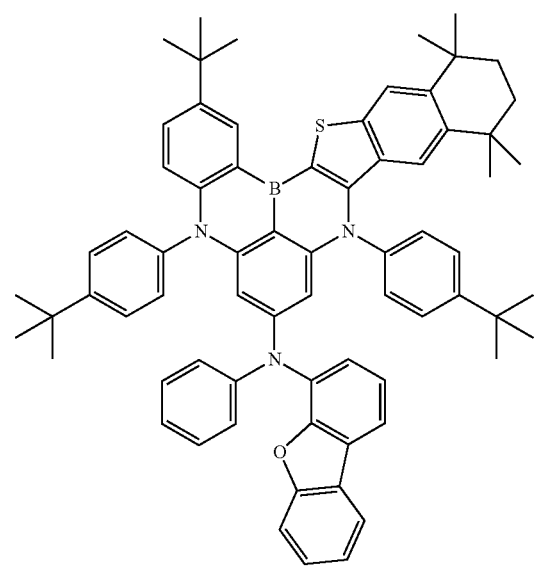 | 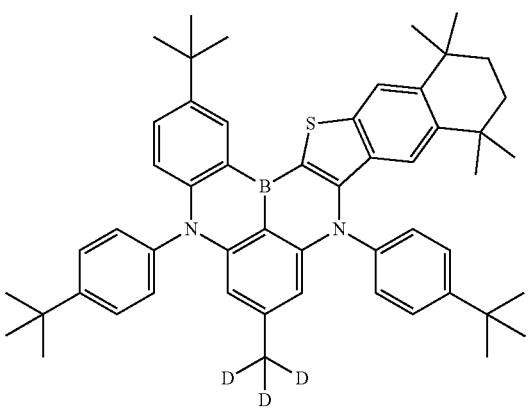 |

2035
-continued
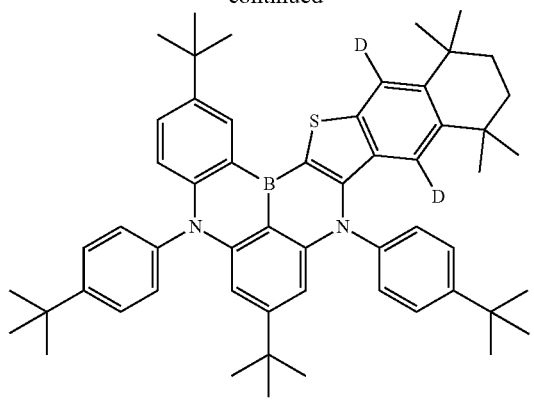
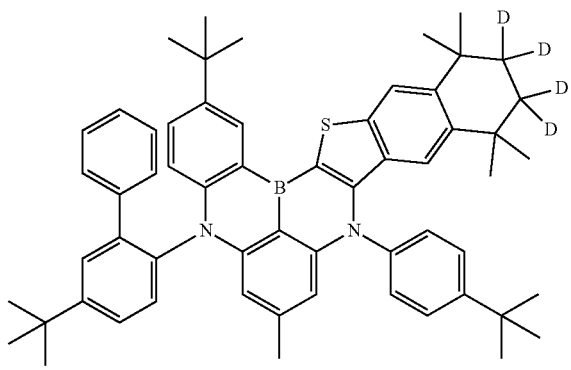
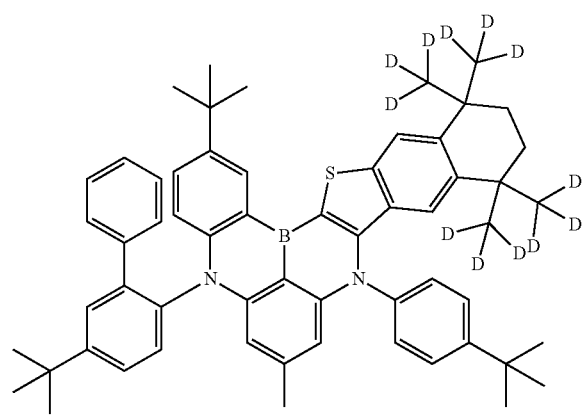
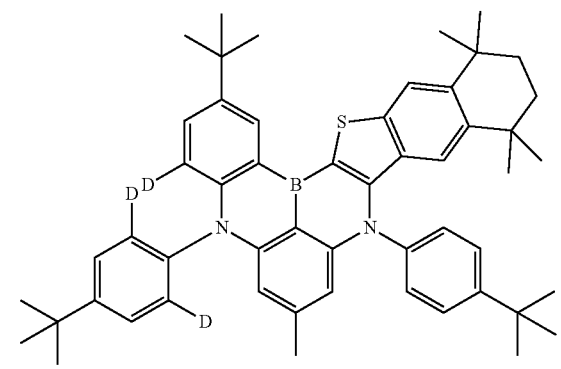
2036
-continued
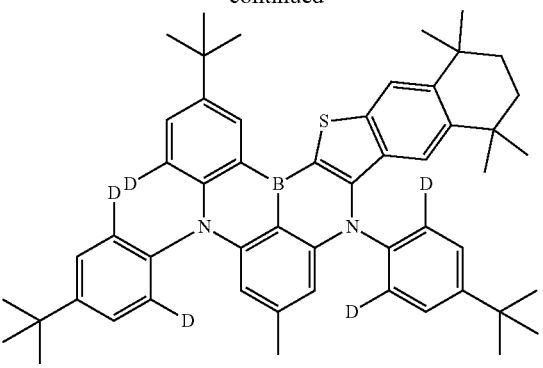
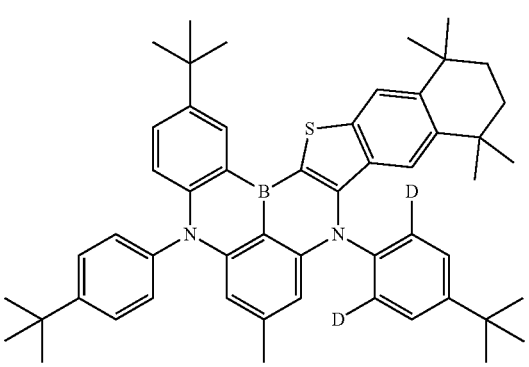
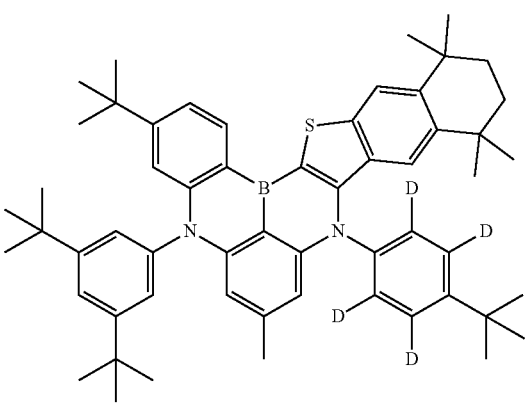
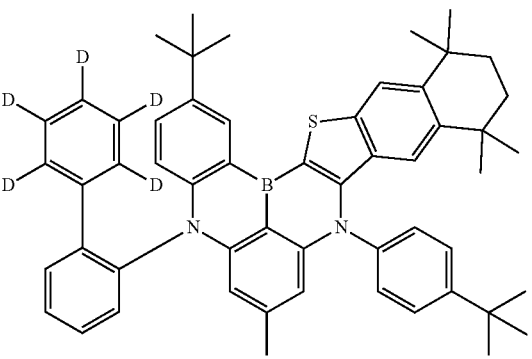

2037
-continued
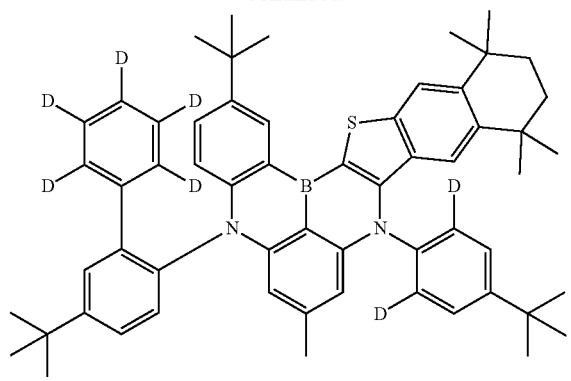
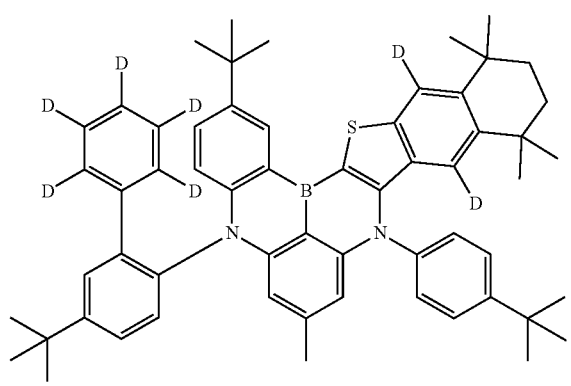
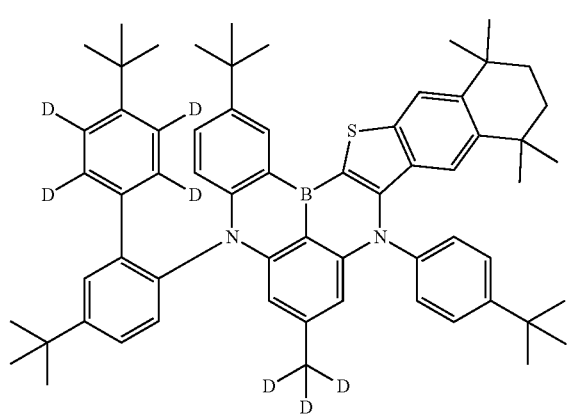
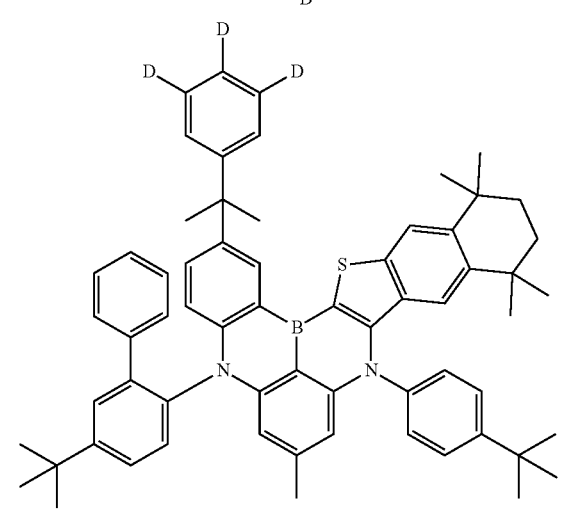
2038
-continued
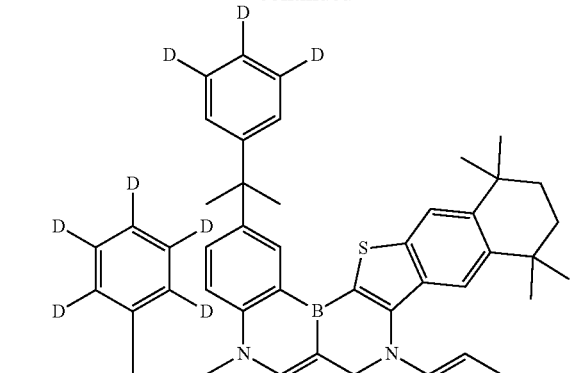
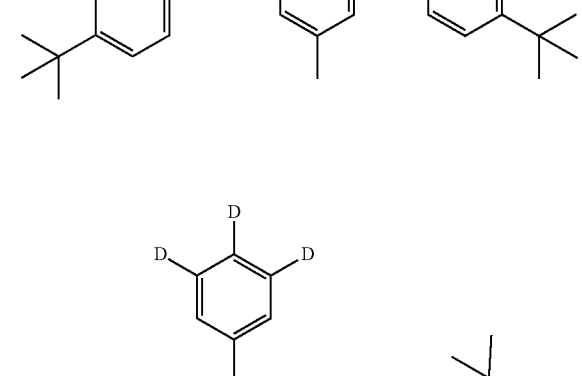
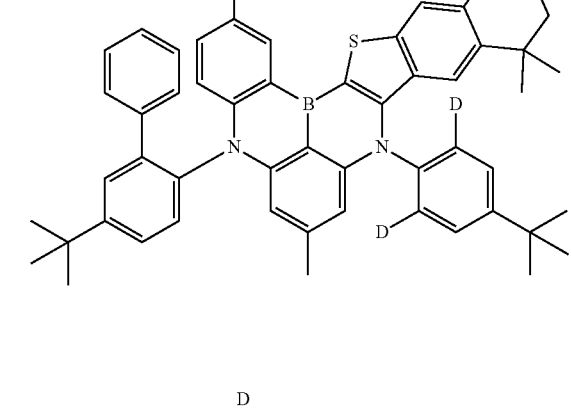
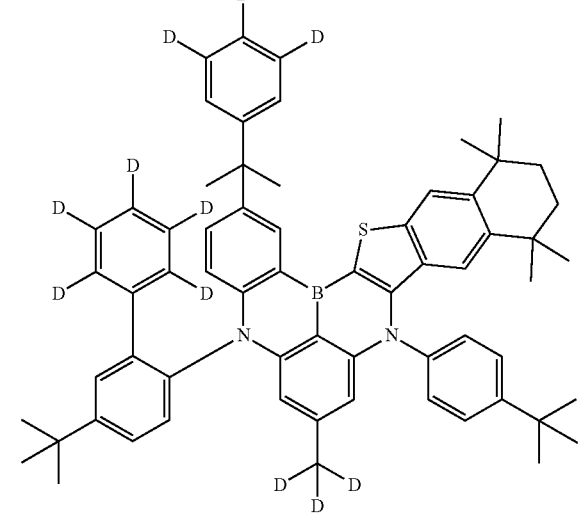

2039
-continued
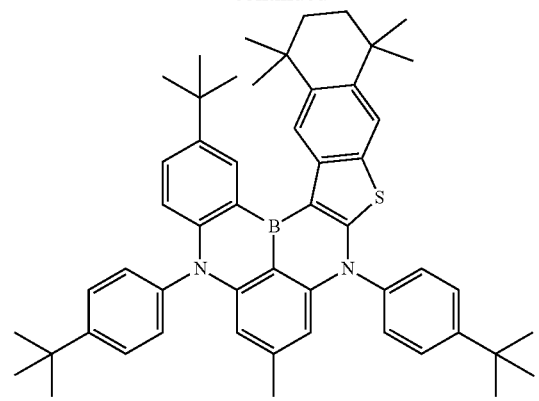
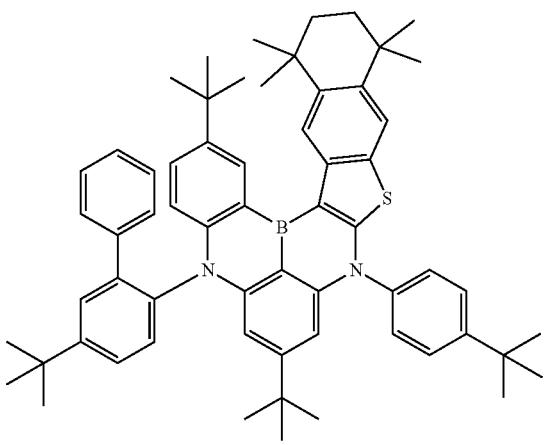
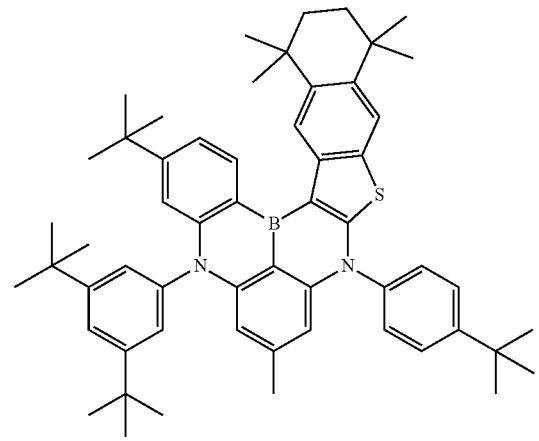
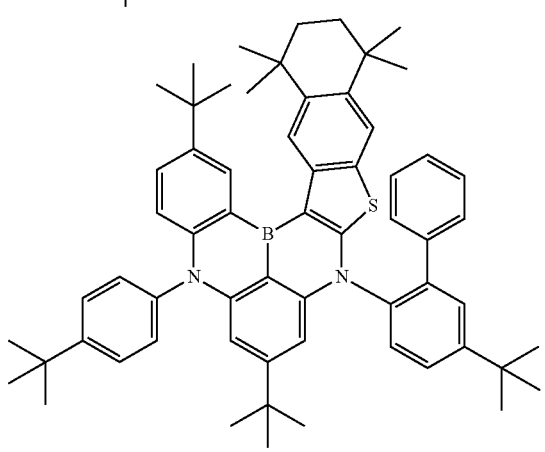
2040
-continued
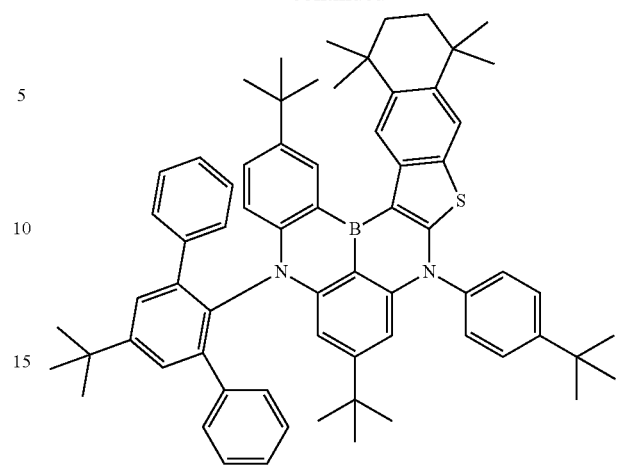
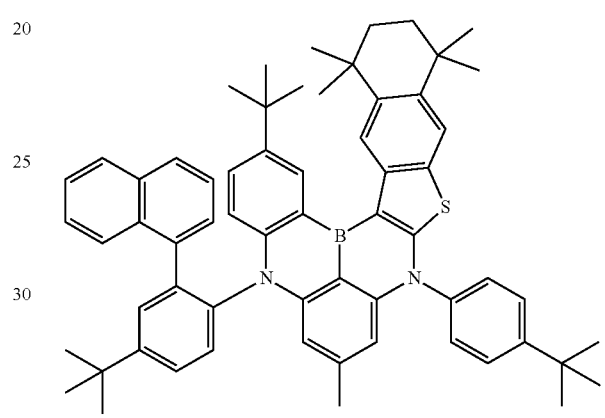
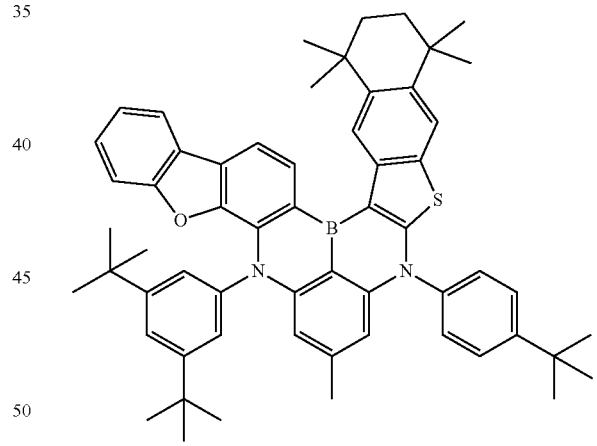
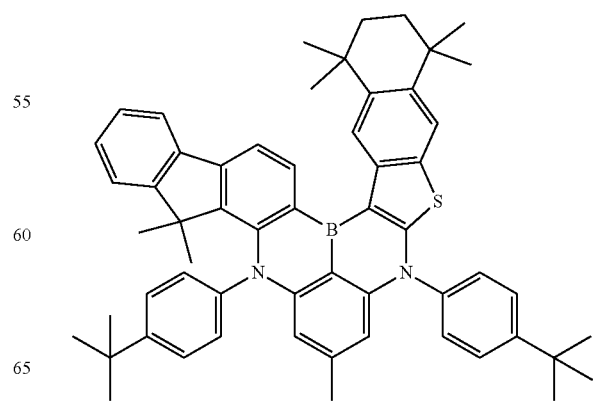

US 11,685,751 B2
2041
-continued
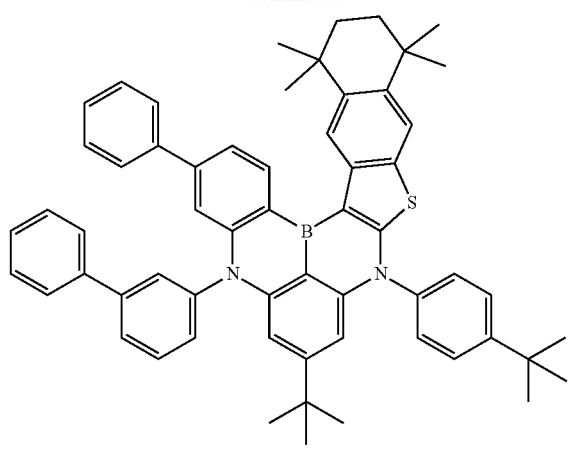
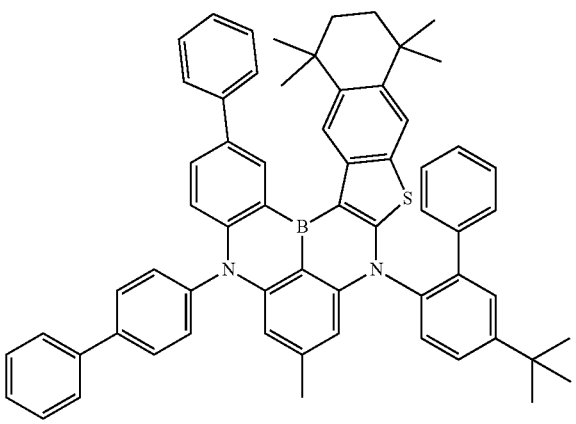

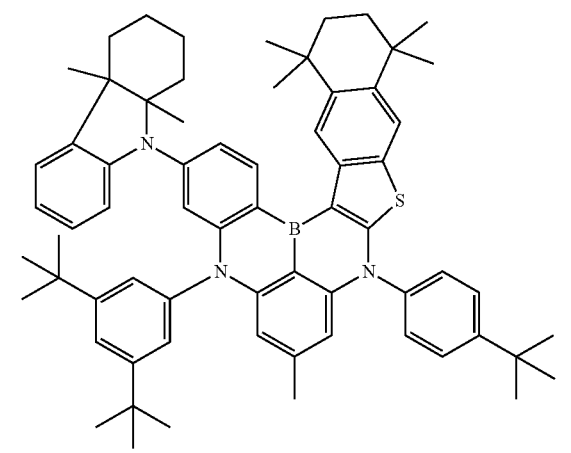
2042
-continued
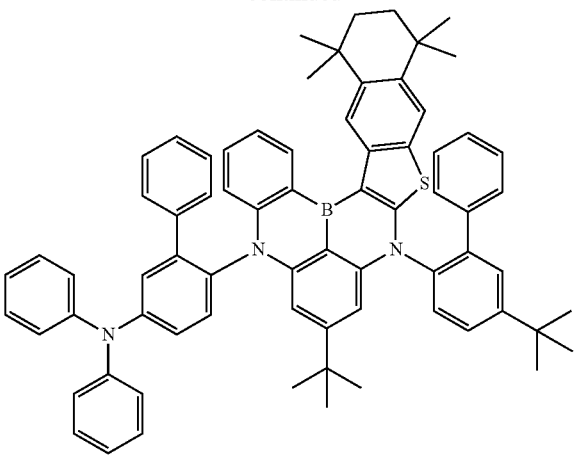

2043 -continued

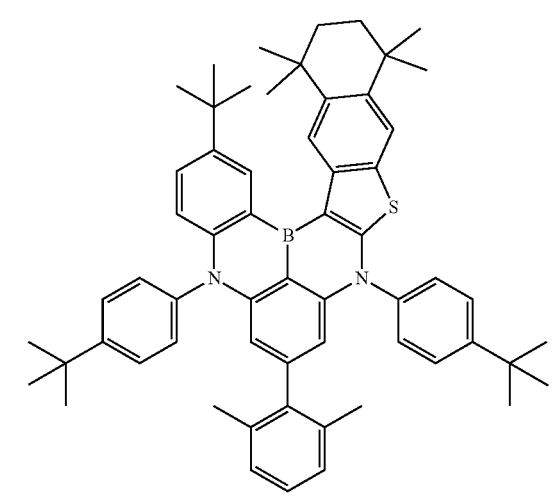
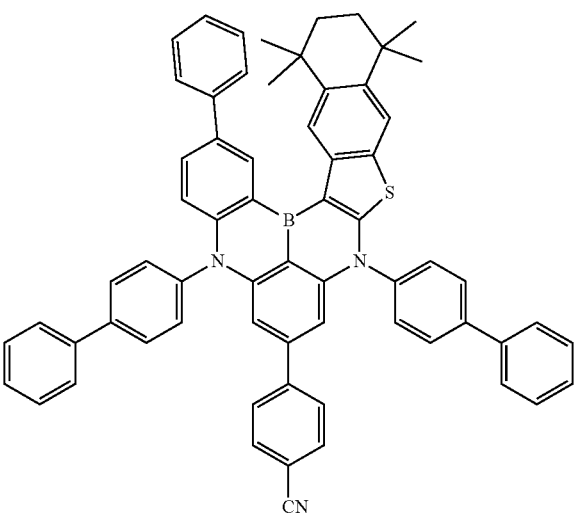
2044 -continued
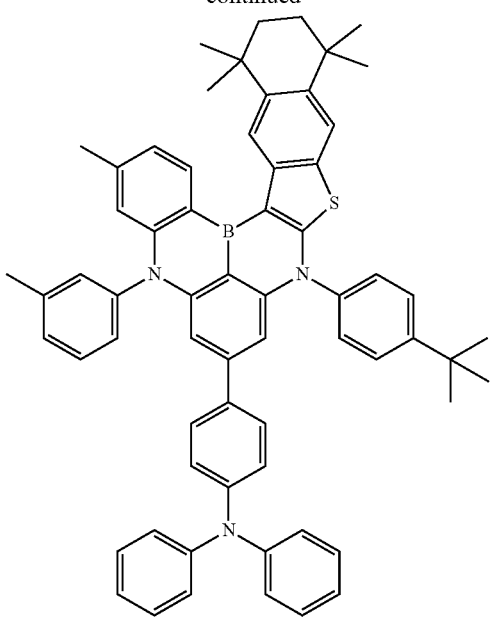
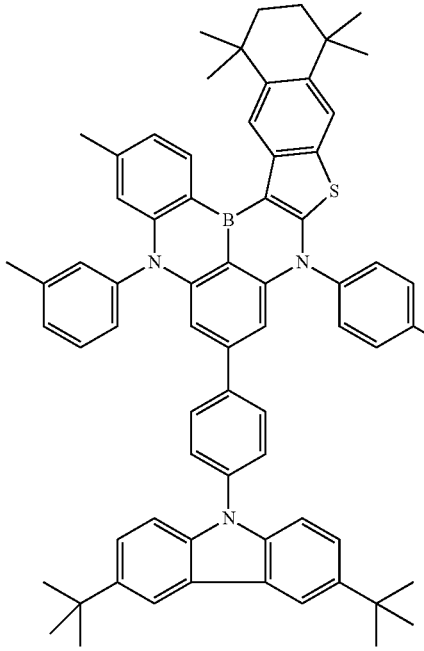
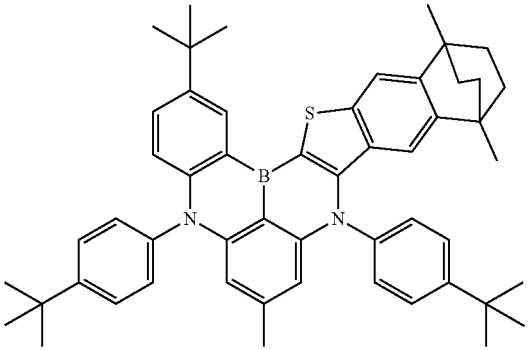

2045
-continued
2046
-continued
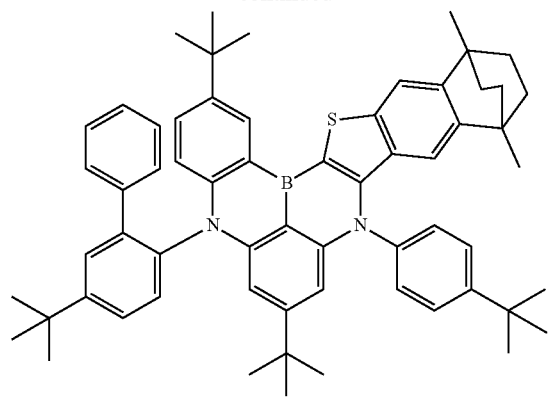
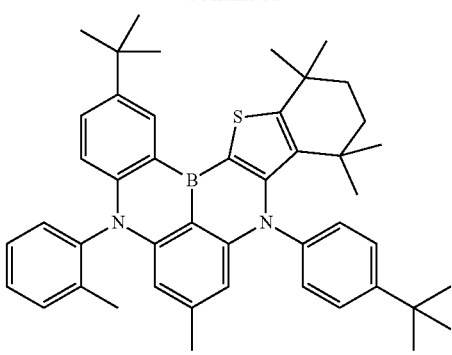
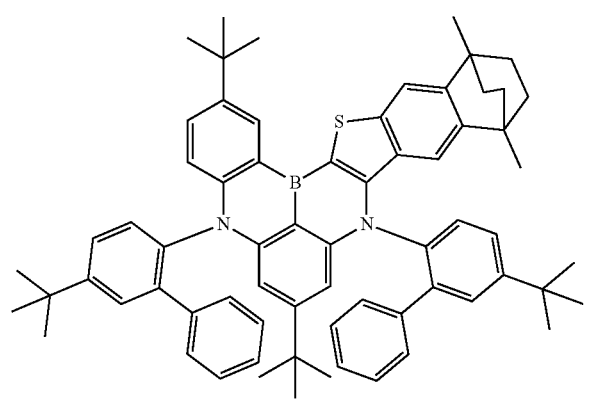
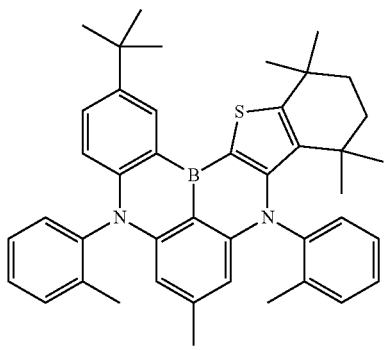
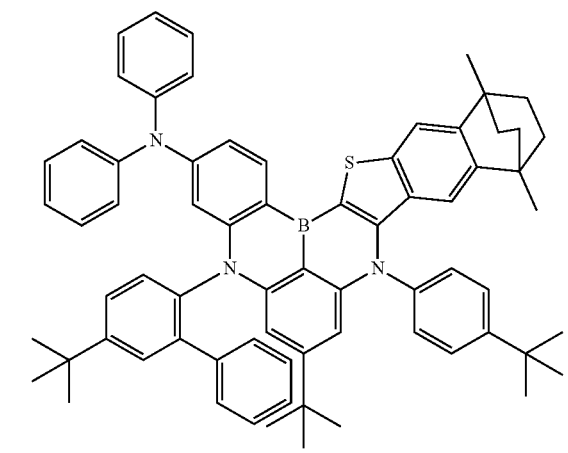
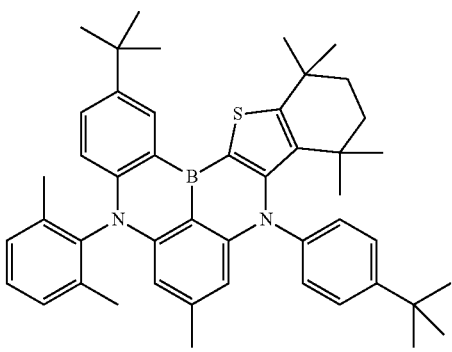
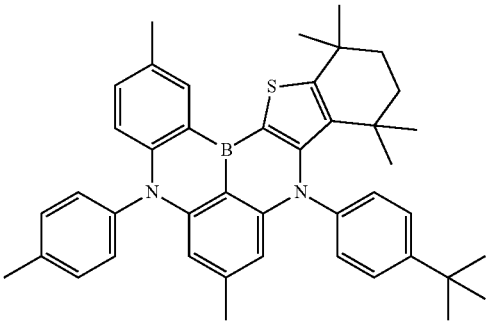
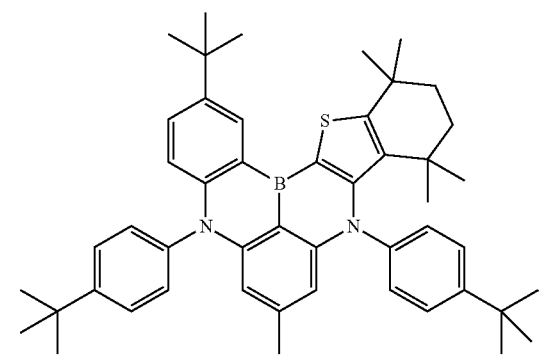
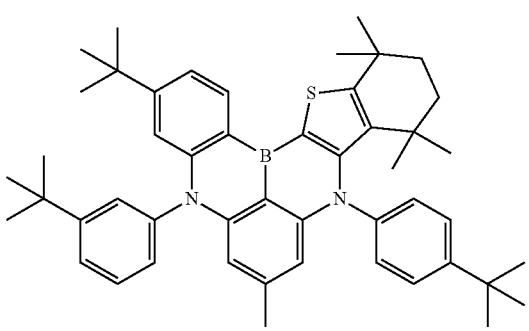

| 2047 -continued | 2048 -continued |
|---|---|
| 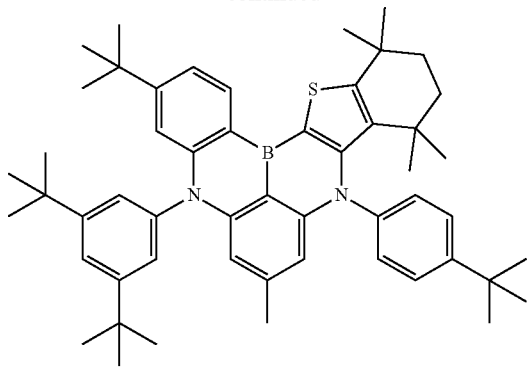 | 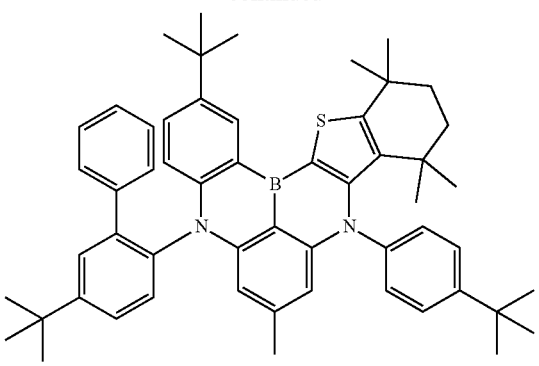 |
| 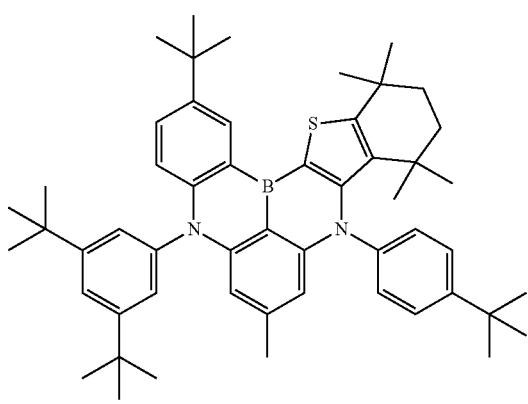 | 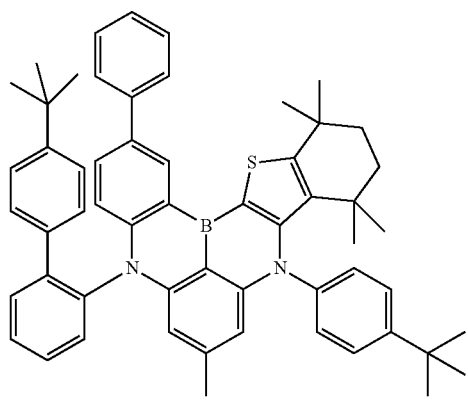 |
| 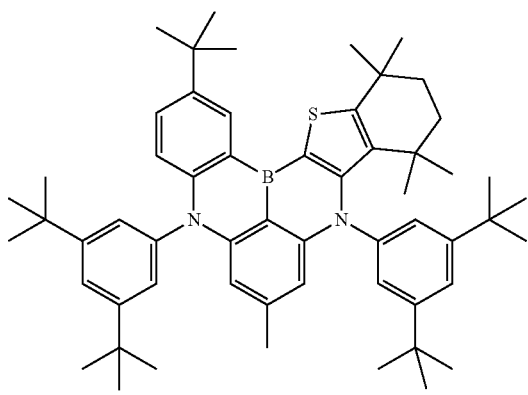 | 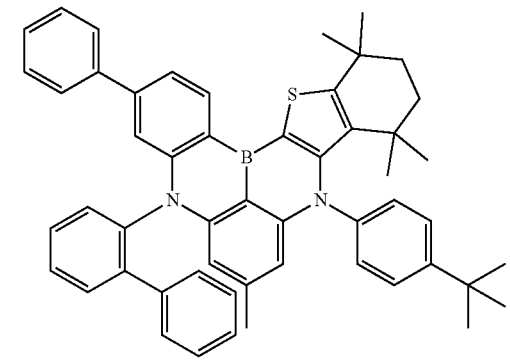 |
| 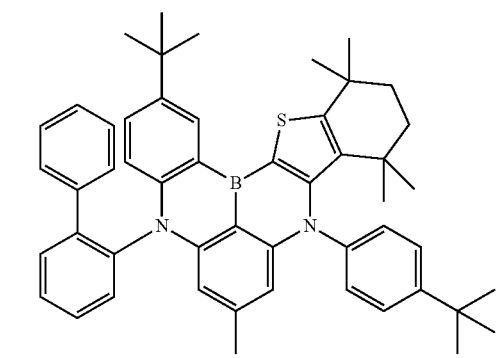 | 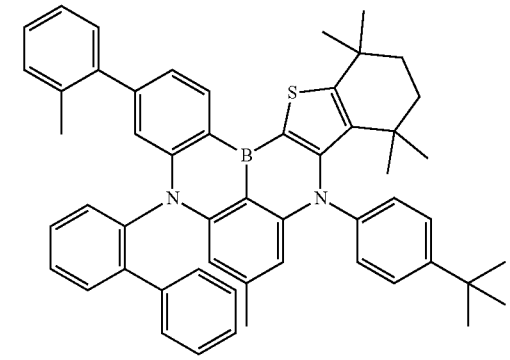 |

| 2049 -continued | 2050 -continued |
|---|---|
| 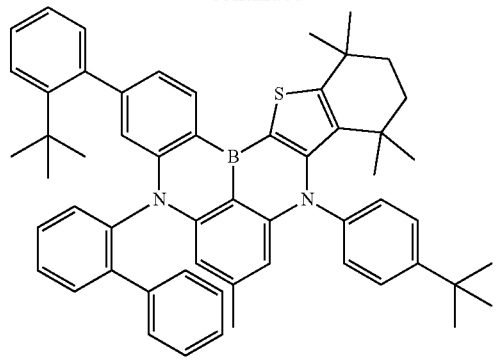 | 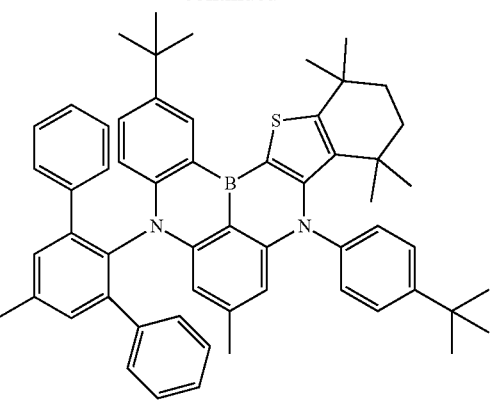 |
| 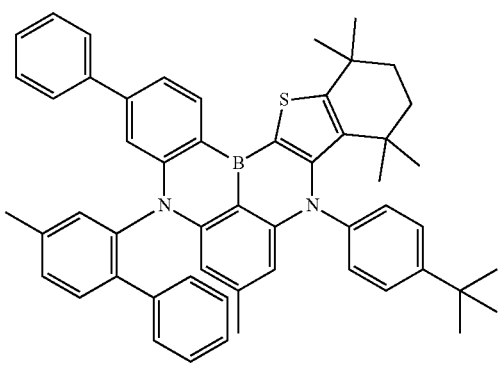 | 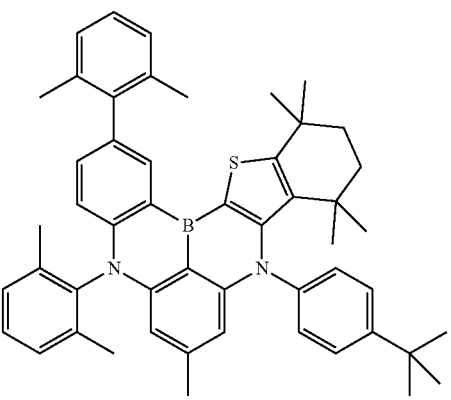 |
| 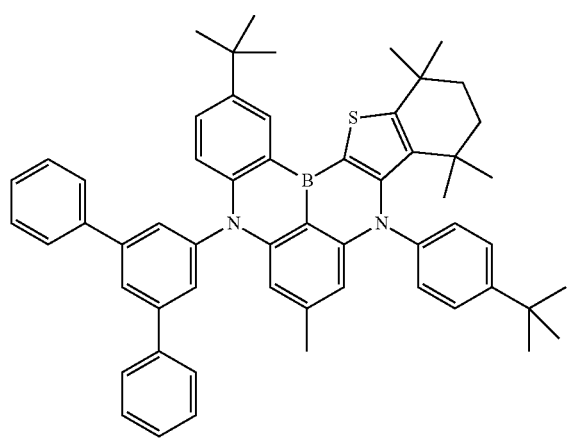 | 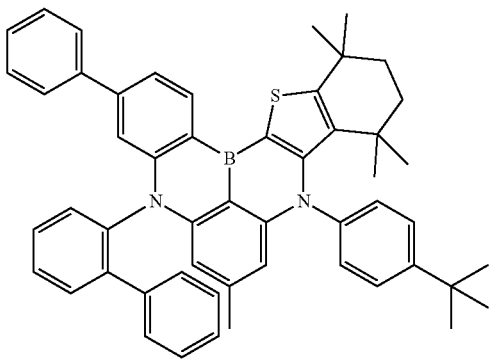 |
| 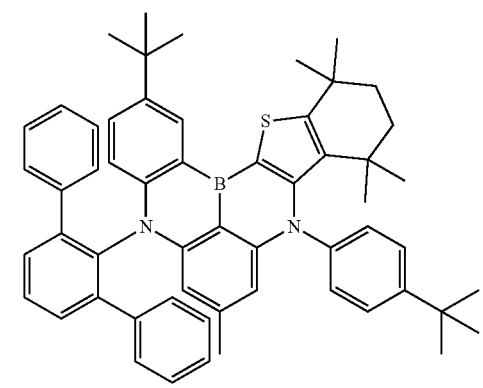 | 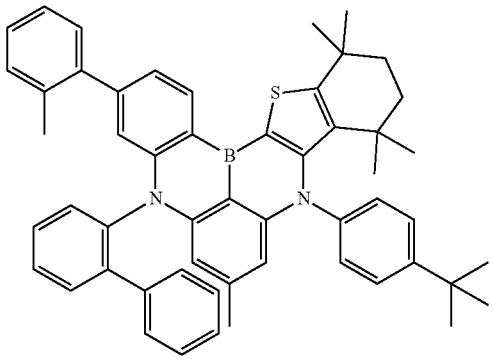 |

2051
-continued
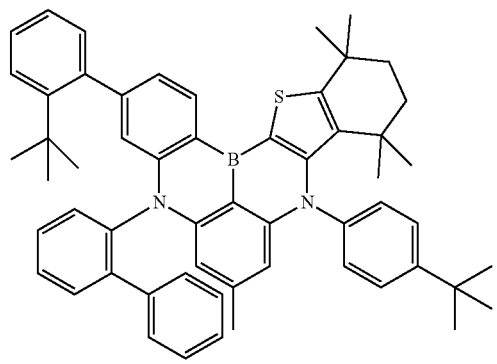
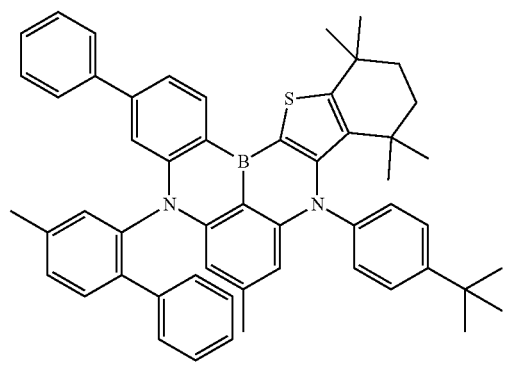
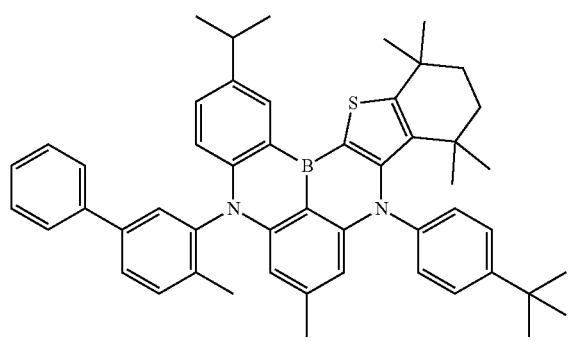
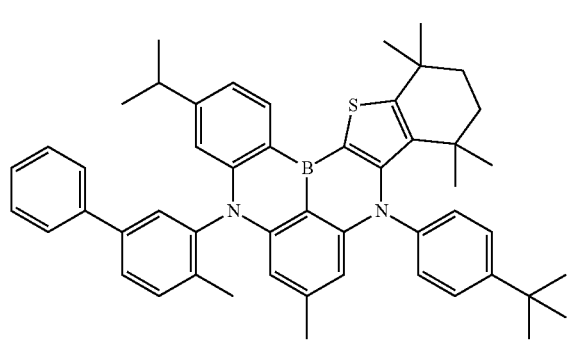
2052
-continued
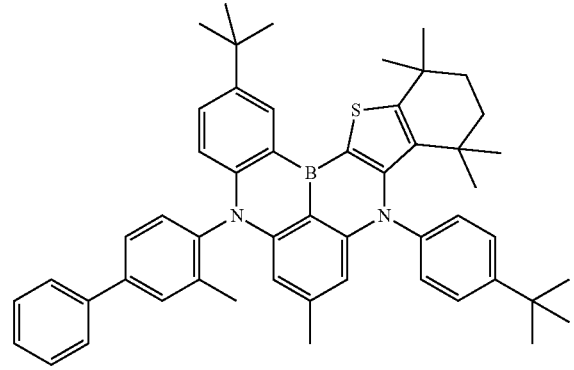
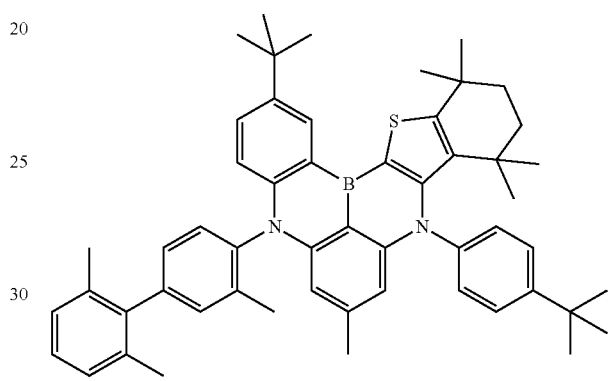
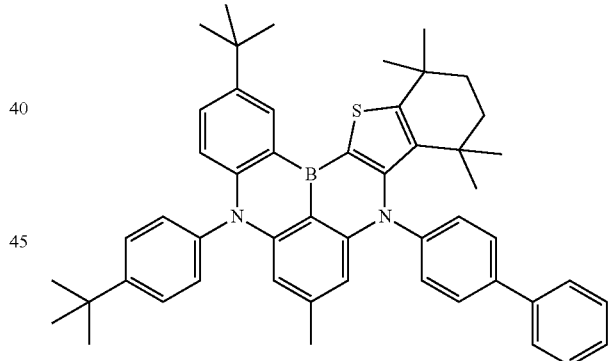
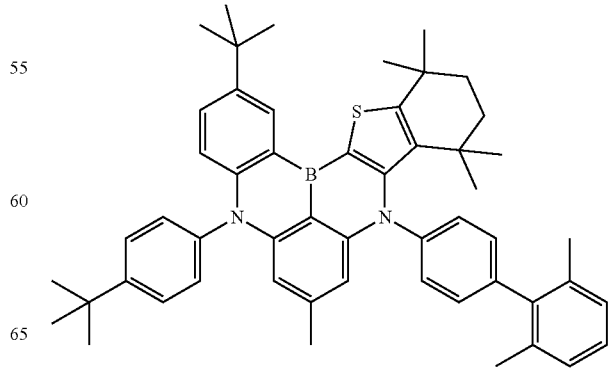

2053
-continued
2054
-continued
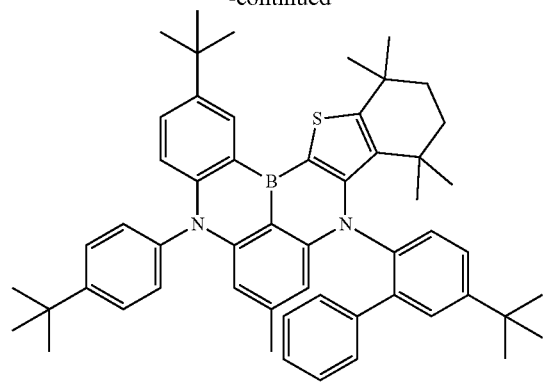
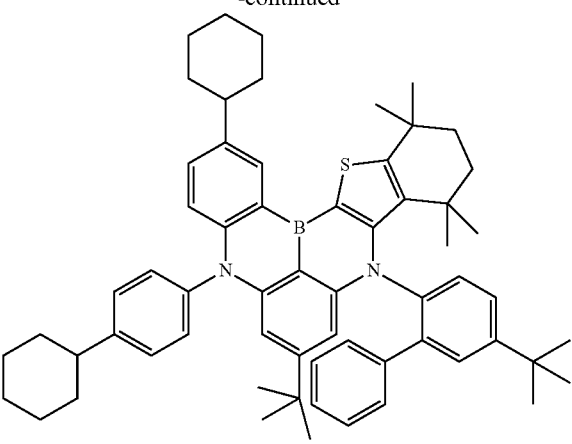
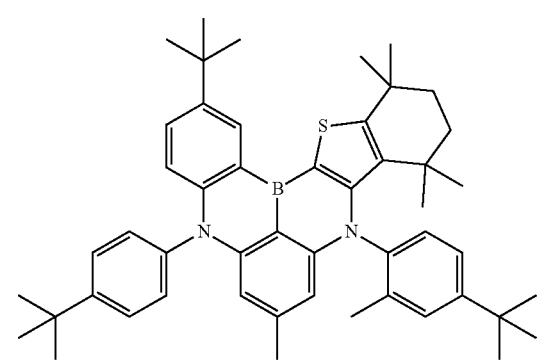
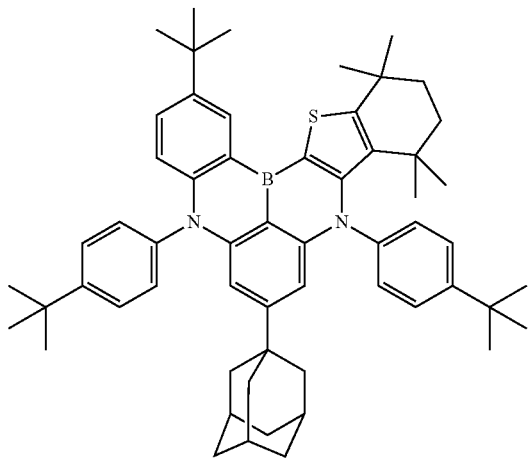
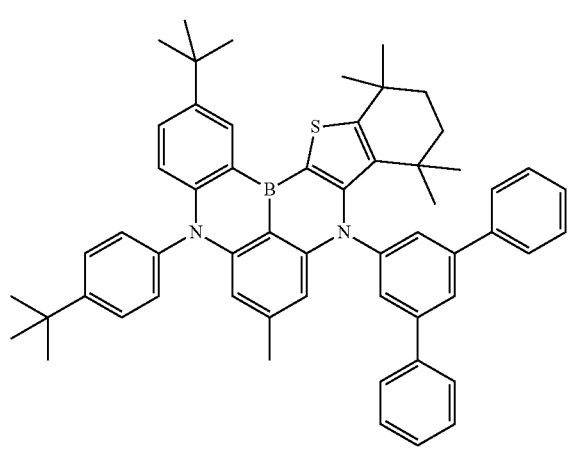
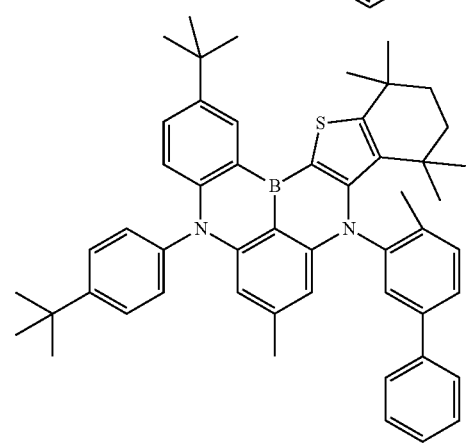
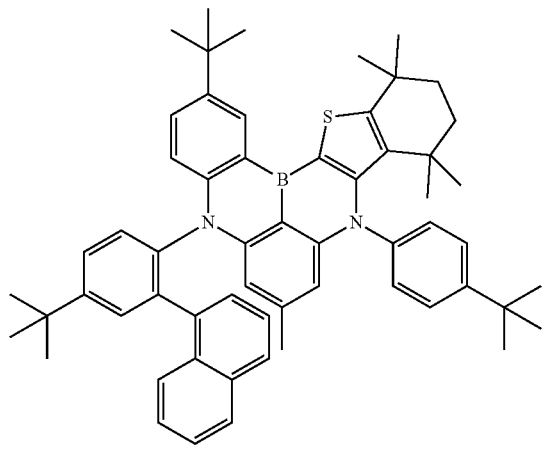

| 2055 -continued | 2056 -continued |
|---|---|
| 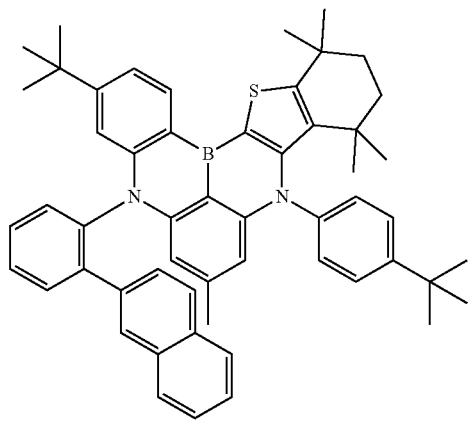 | 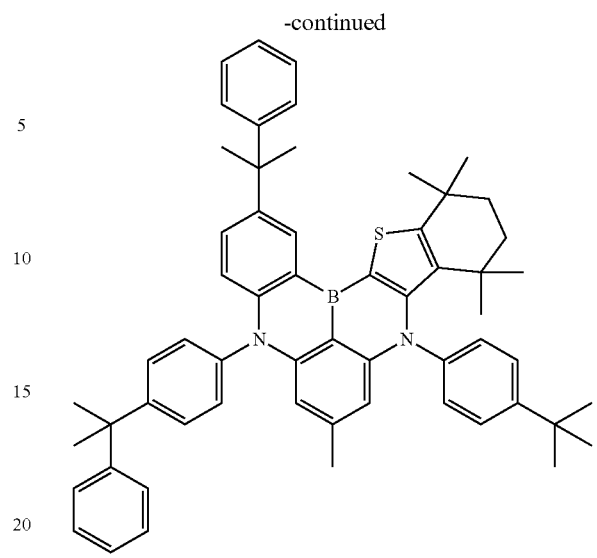 |
| 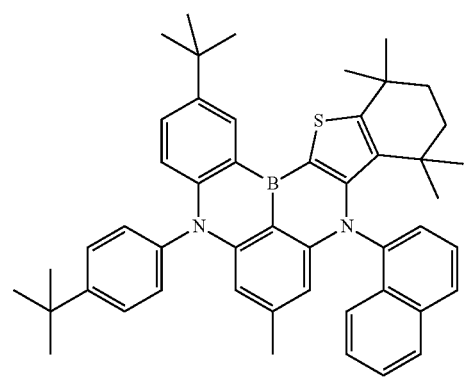 | 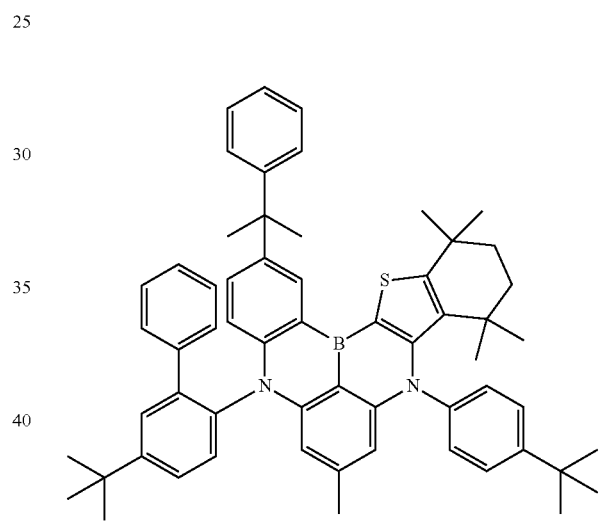 |
| 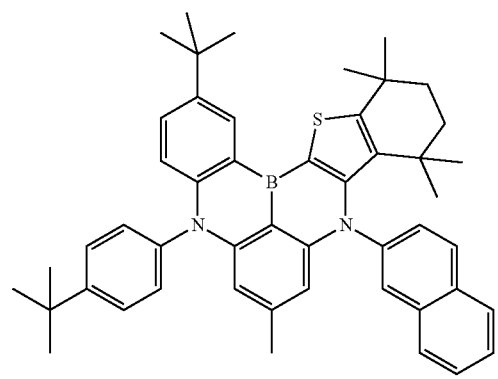 | 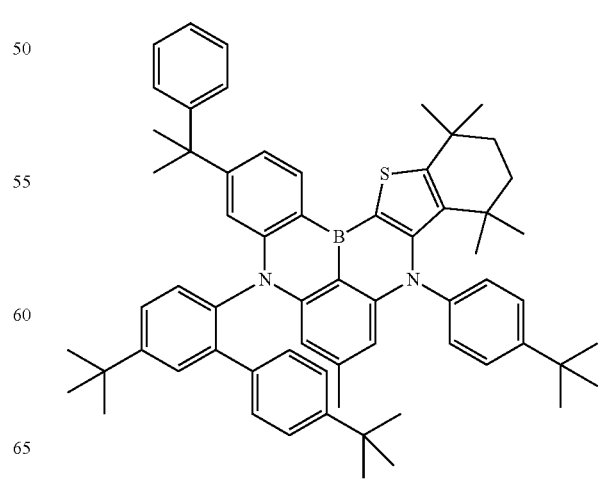 |
| 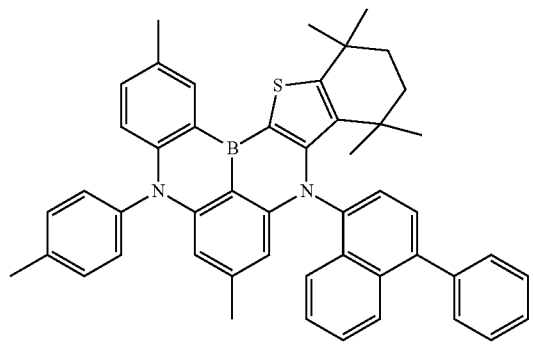 | |

2057
-continued
2058
-continued
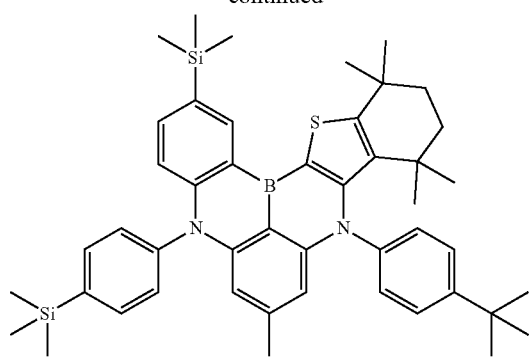
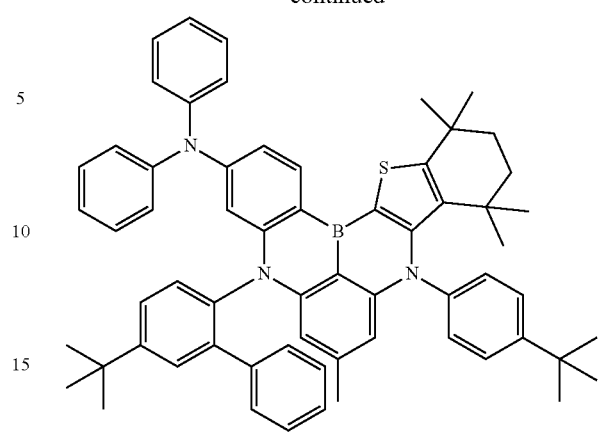
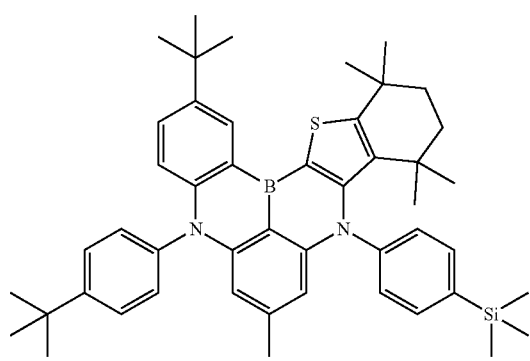
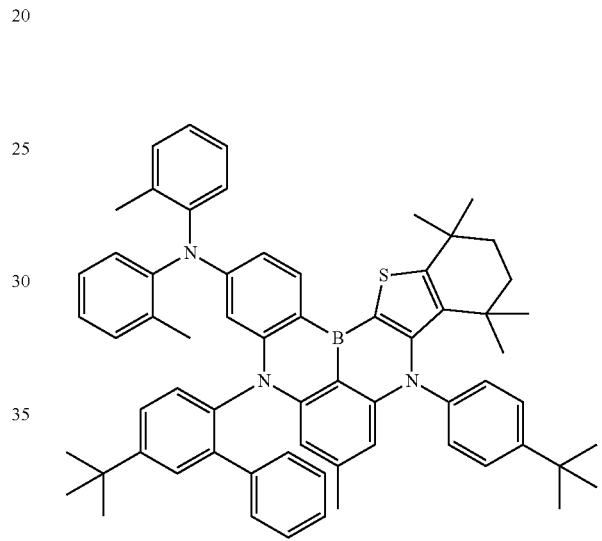
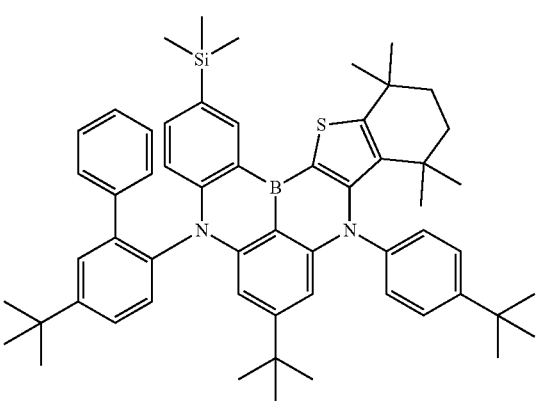
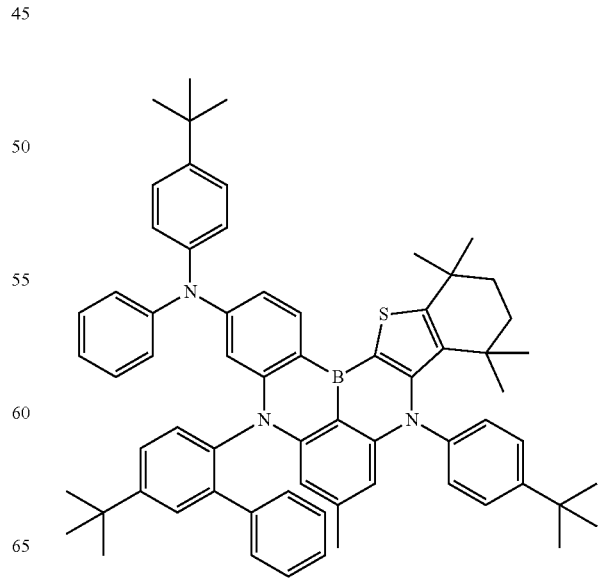
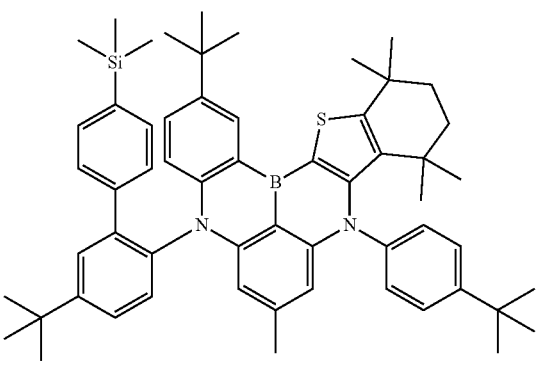

2059
-continued
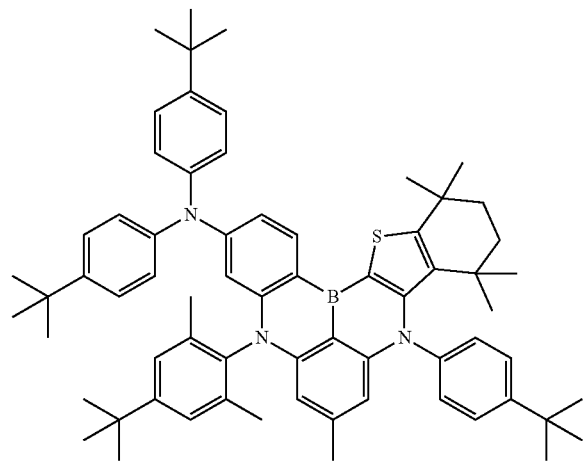
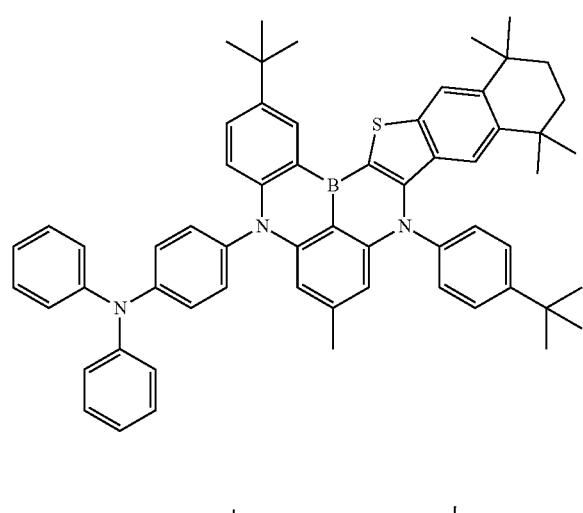
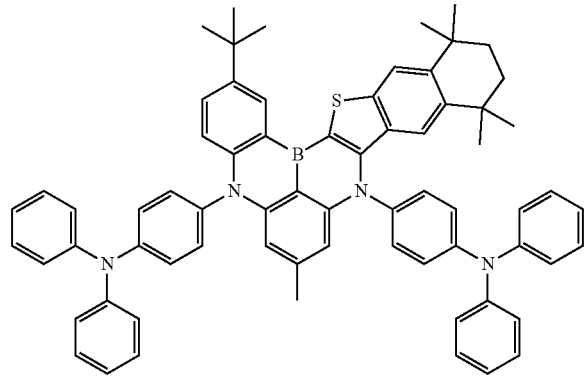
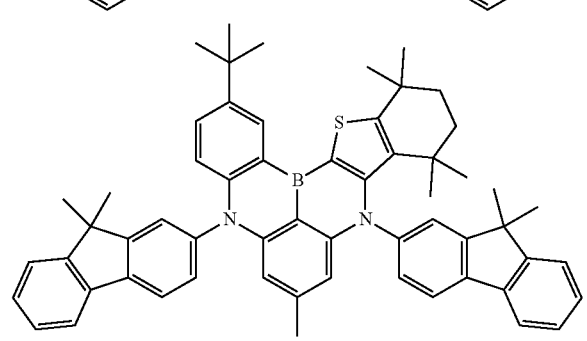
2060
-continued
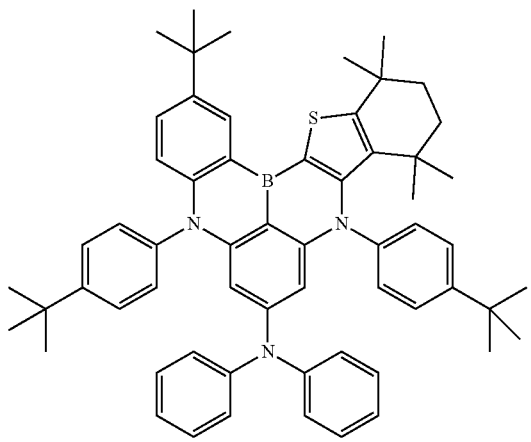
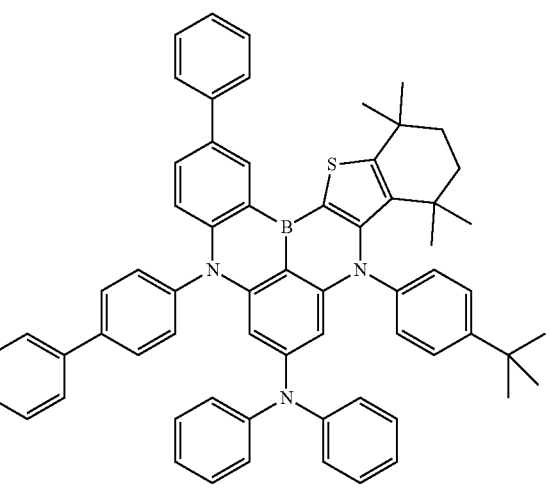
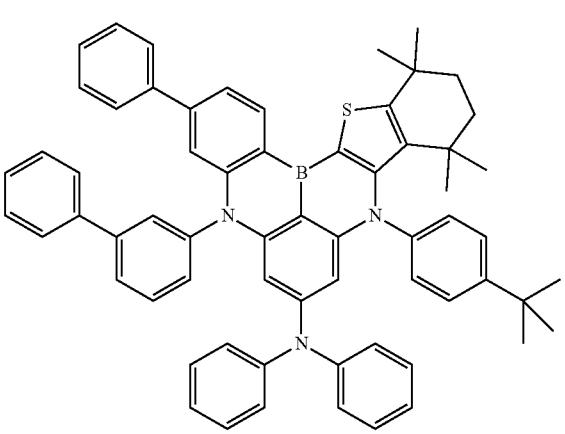

2061
-continued
2062
-continued
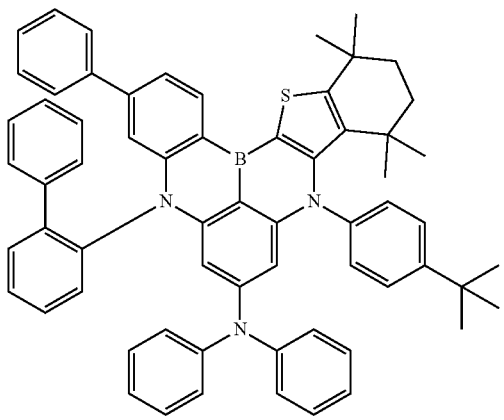
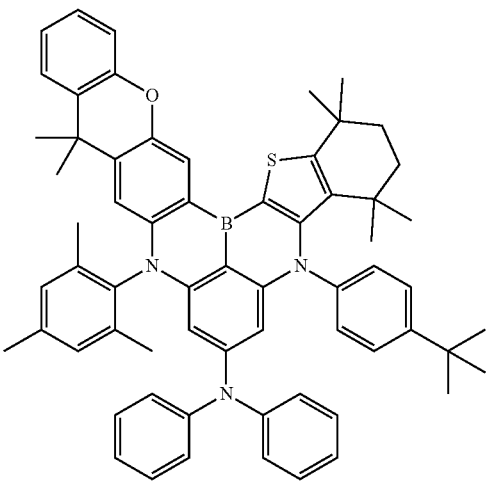
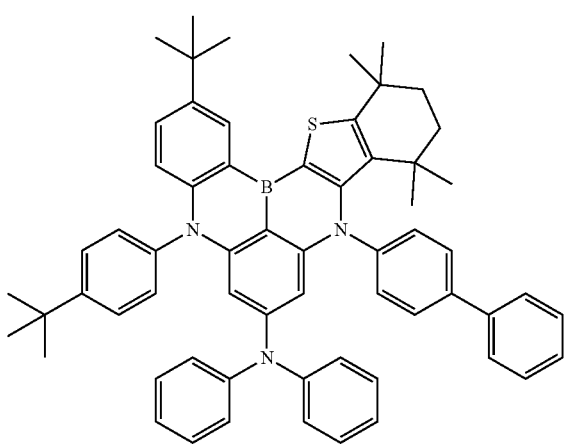
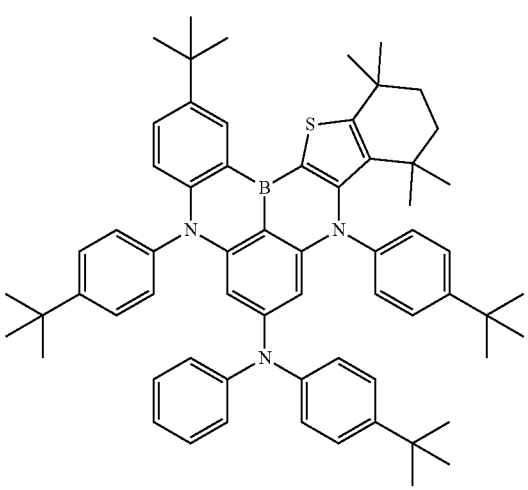
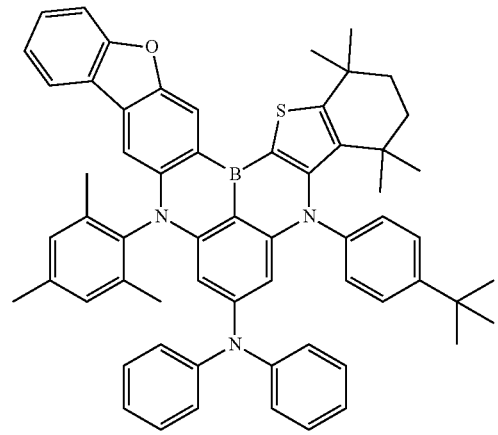
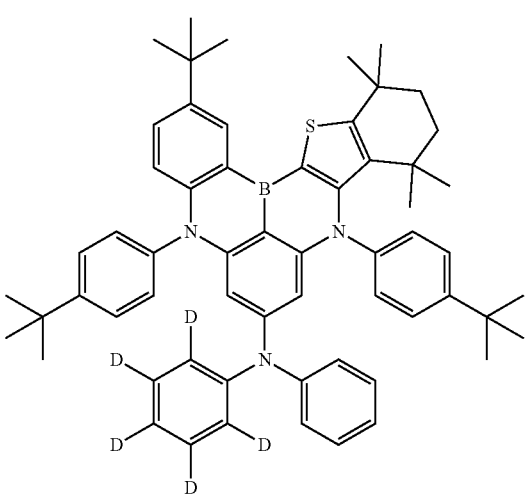

2063
-continued
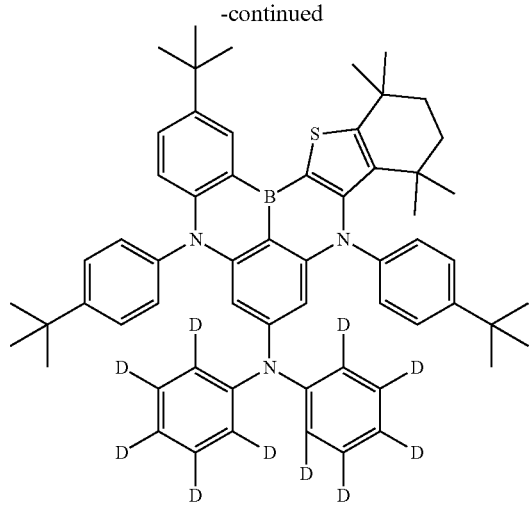
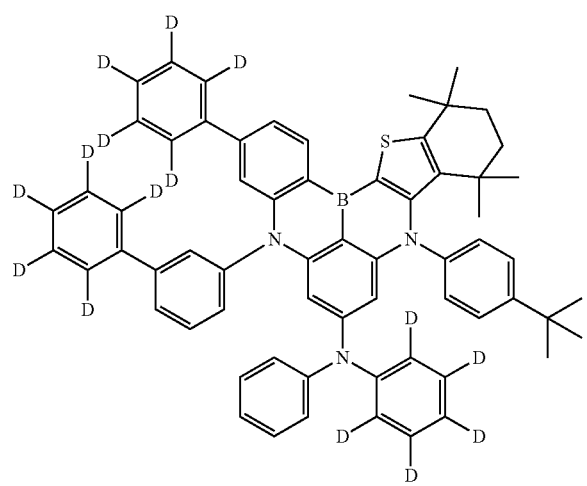
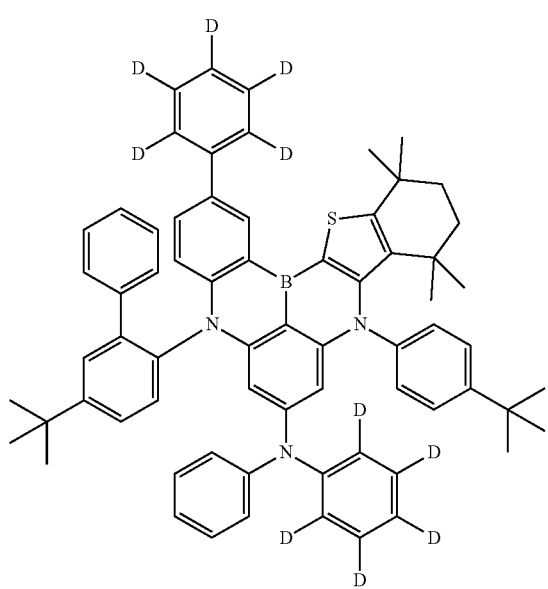
2064
-continued
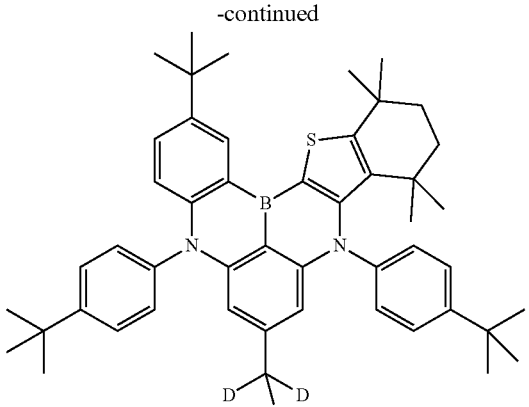
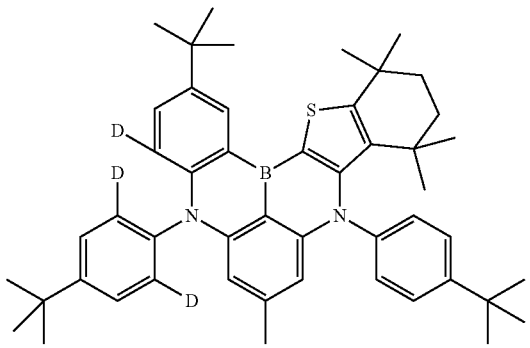
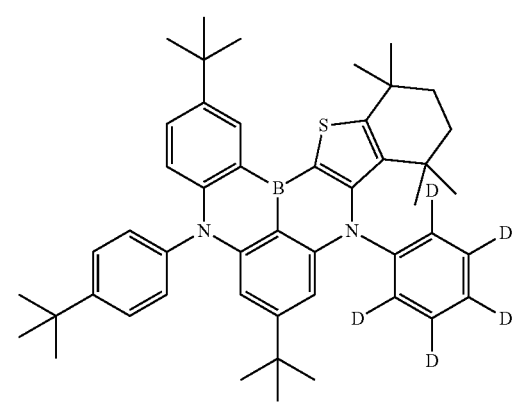

2065
-continued
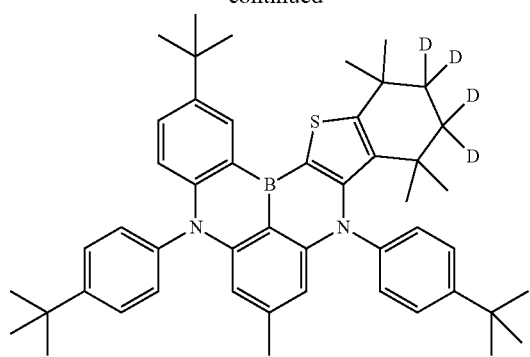
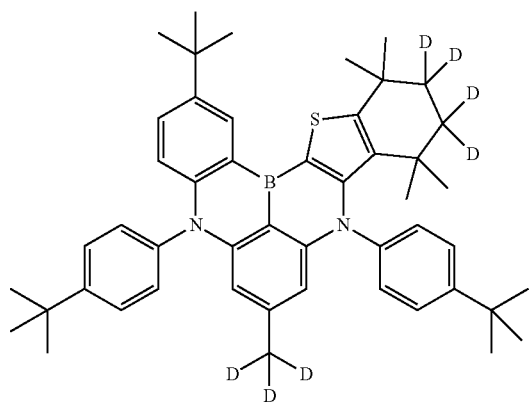
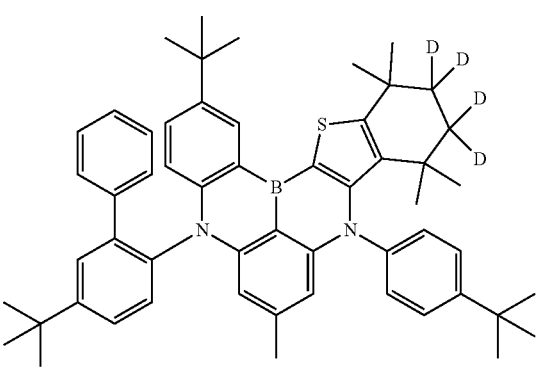
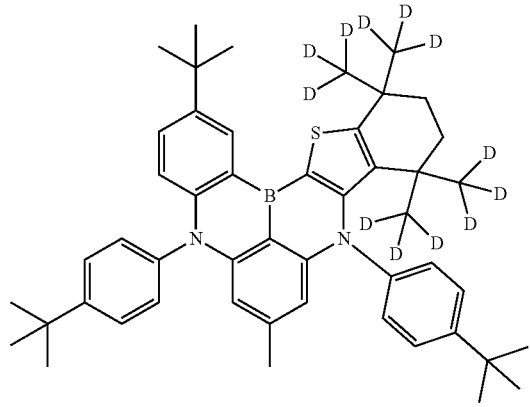
2066
-continued
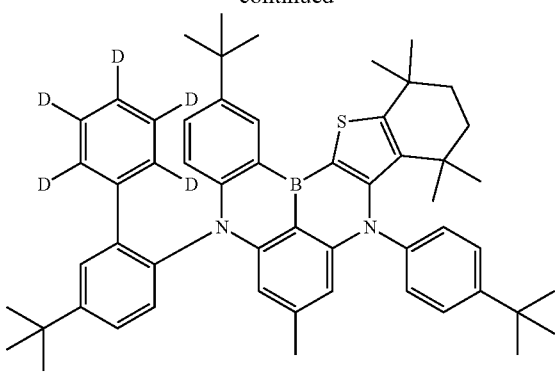
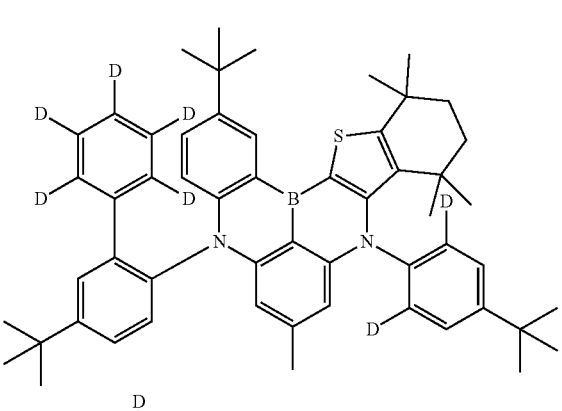
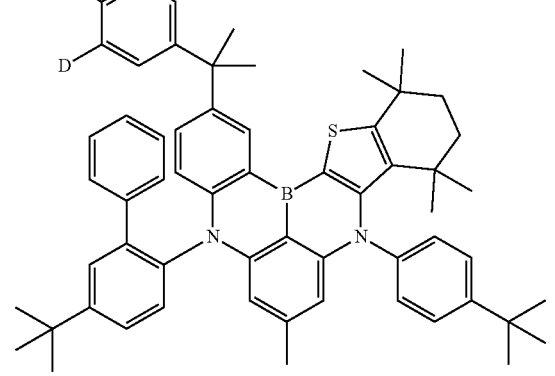
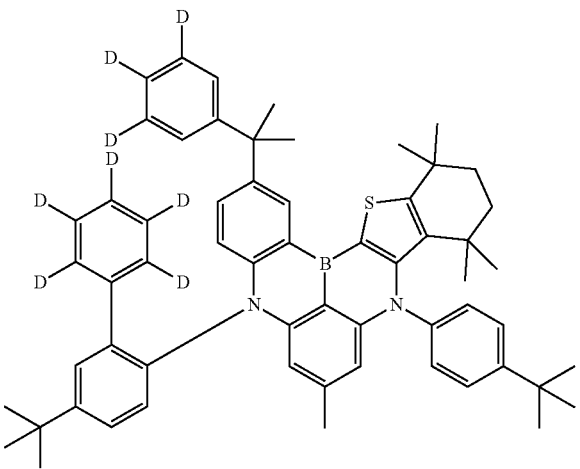

2067
-continued
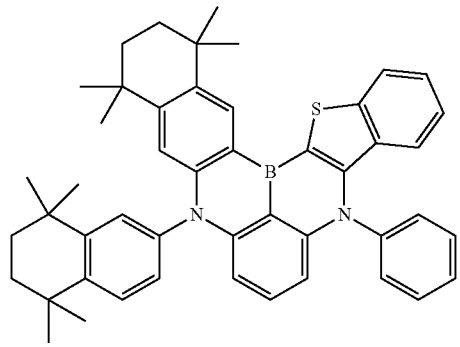
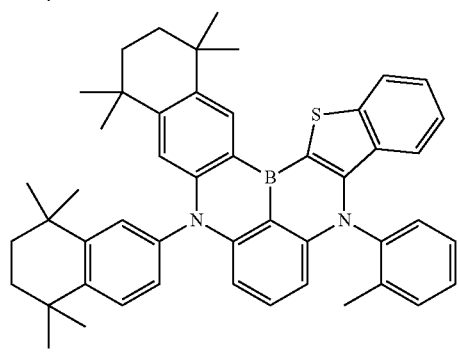
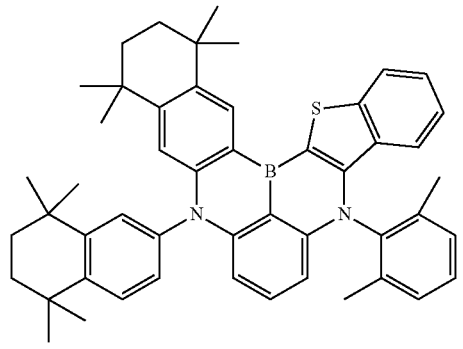
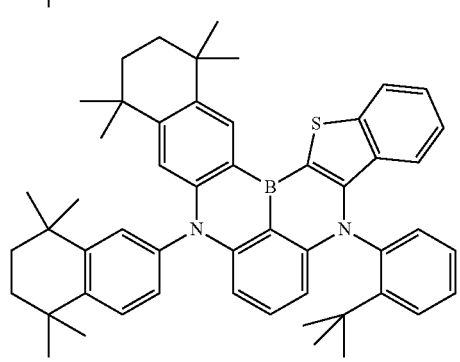
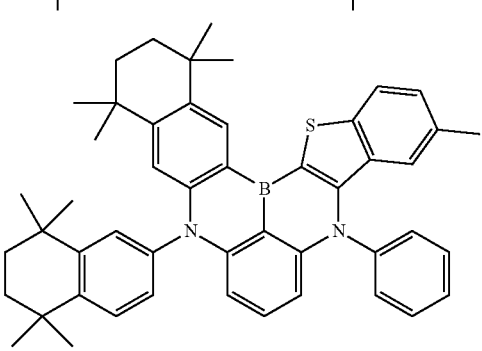
2068
-continued
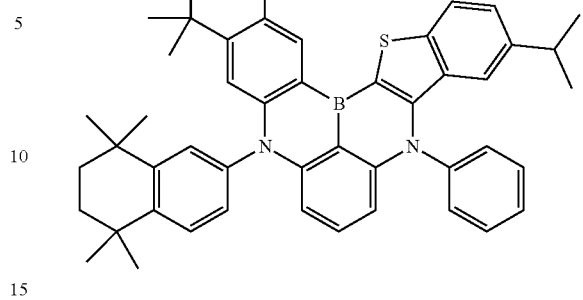
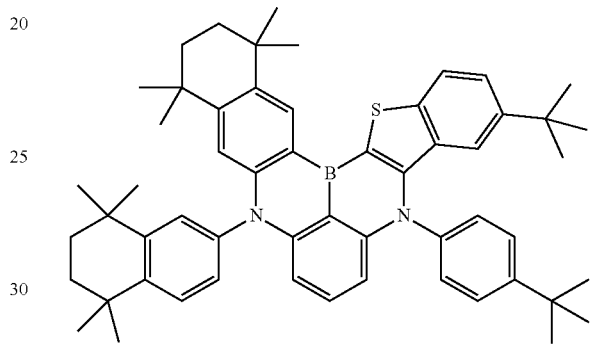
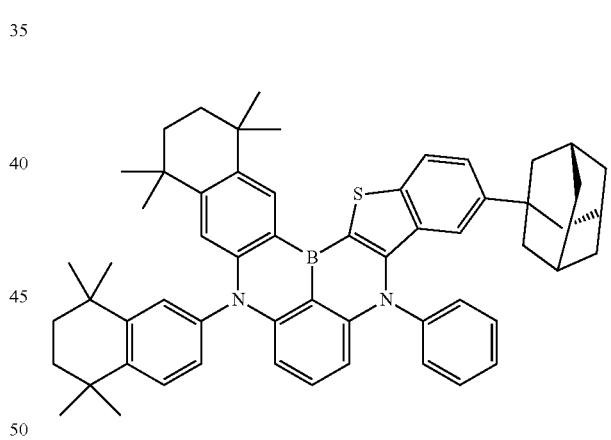
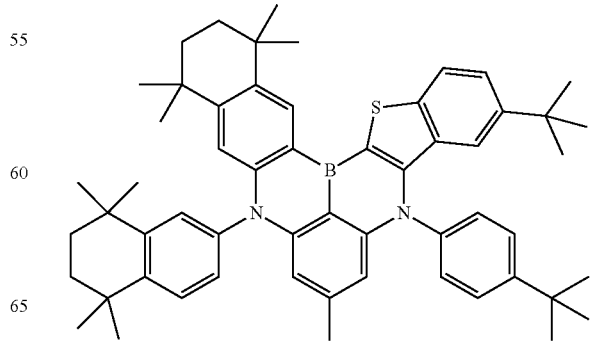

2069
-continued
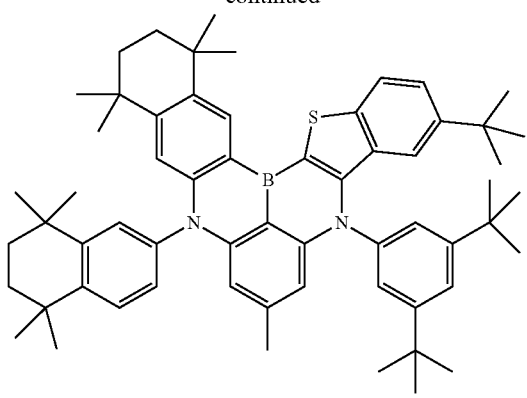
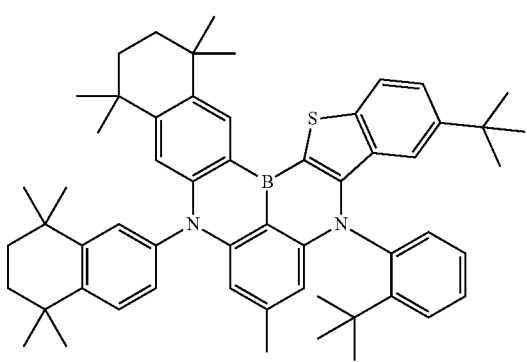
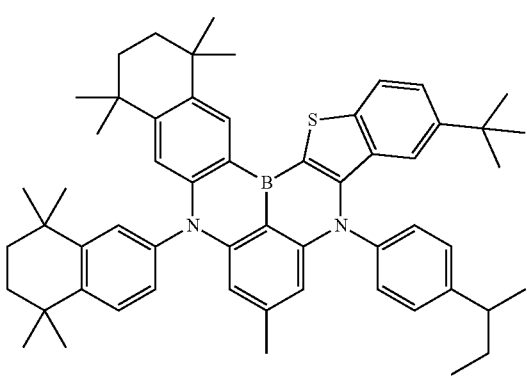
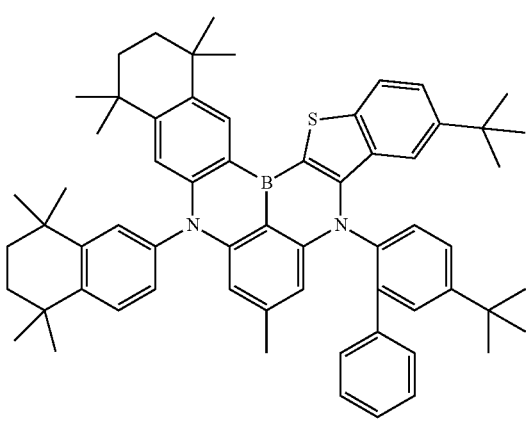
2070
-continued
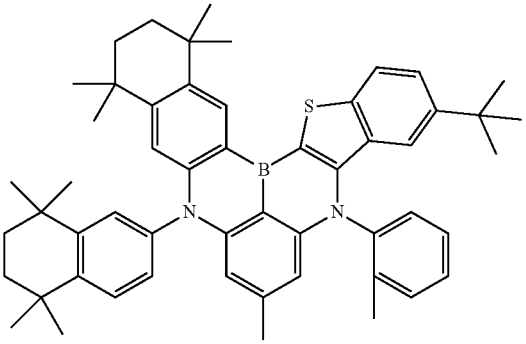
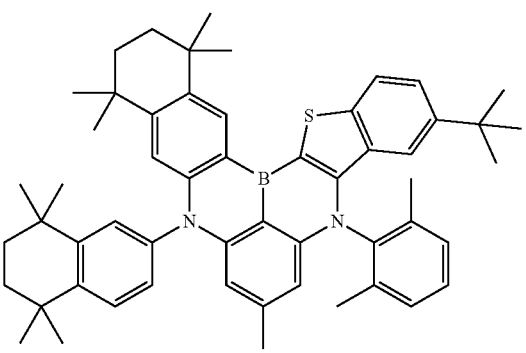
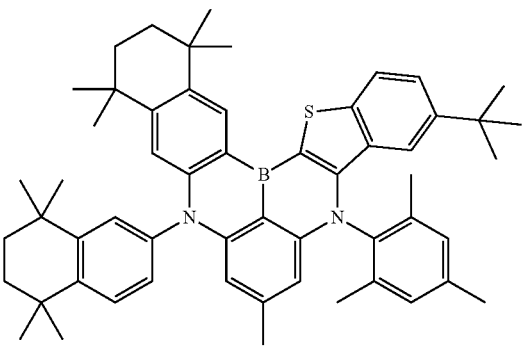
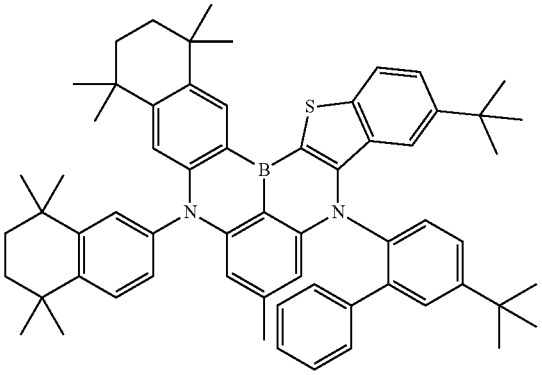

| 2071 -continued | 2072 -continued |
|---|---|
| 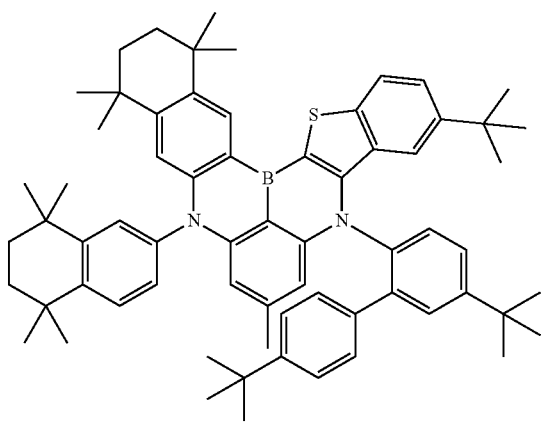 | 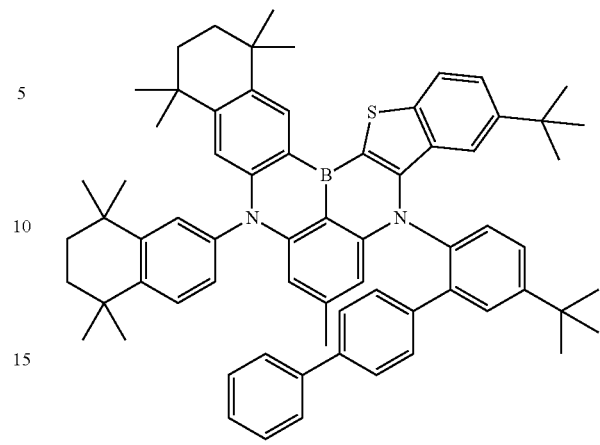 |
| 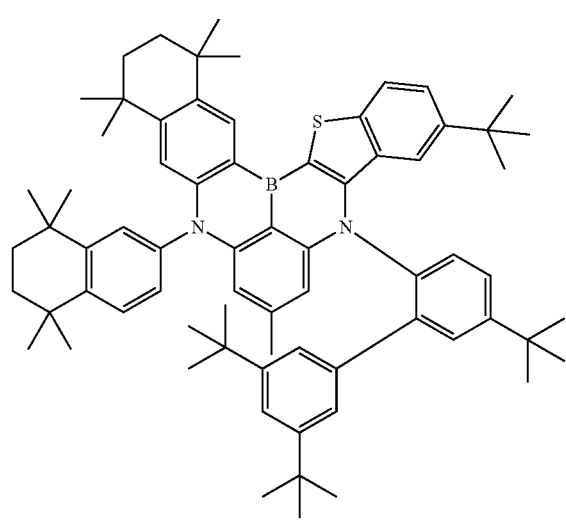 | 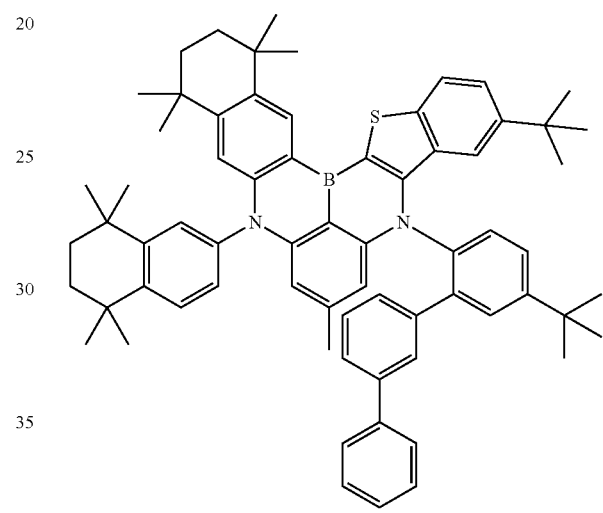 |
|  | 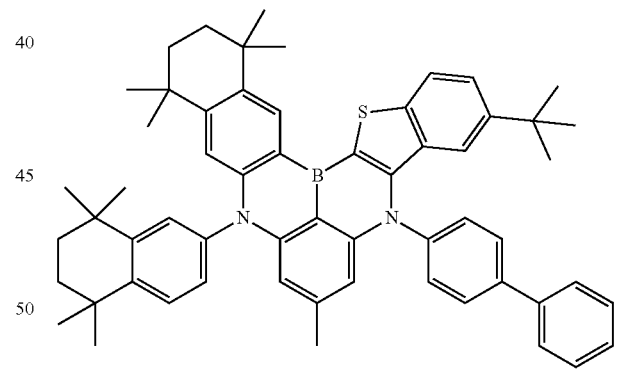 |
| 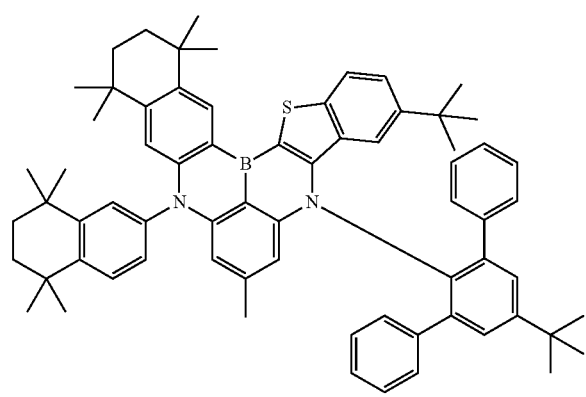 | 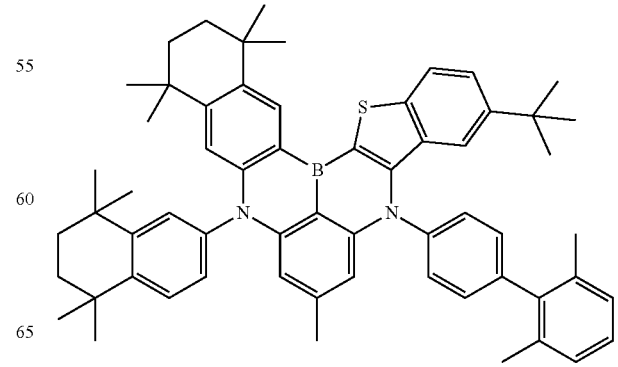 |

2073
-continued
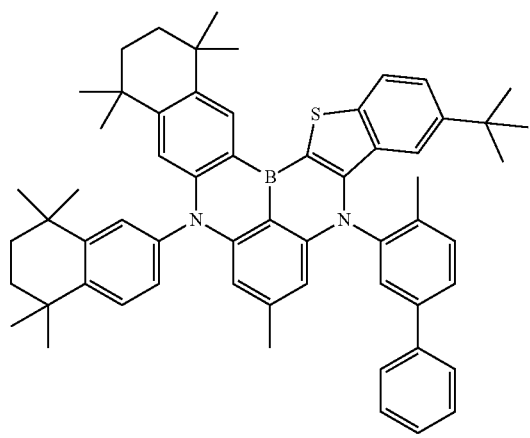
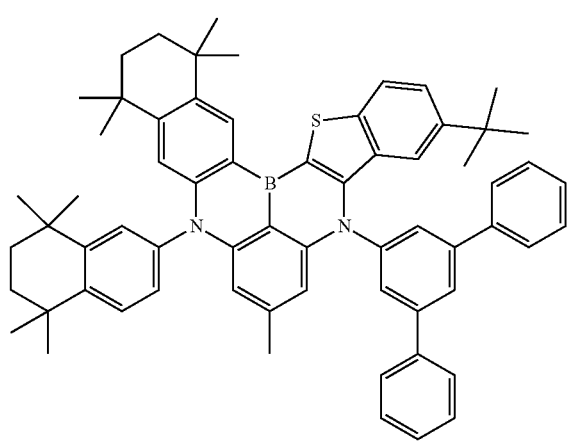
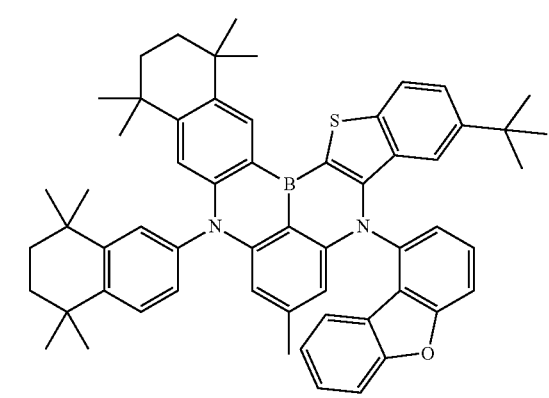
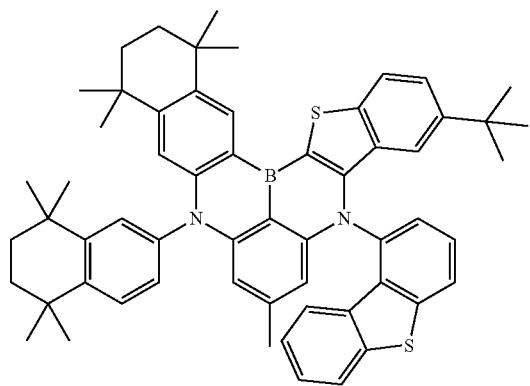
2074
-continued
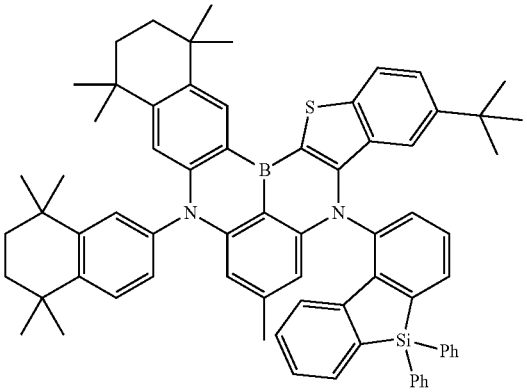
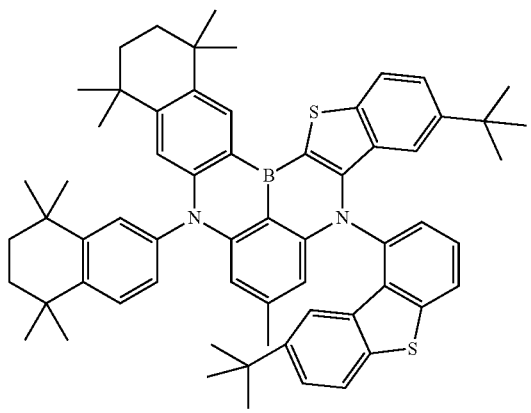
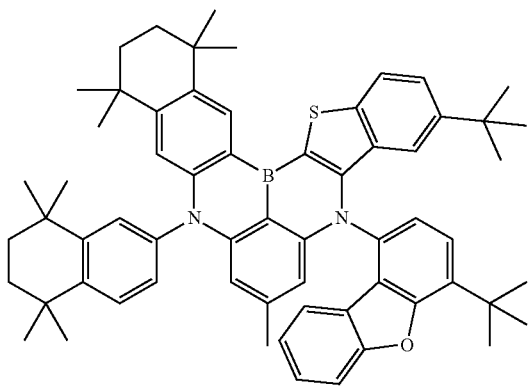

2075
-continued
2076
-continued
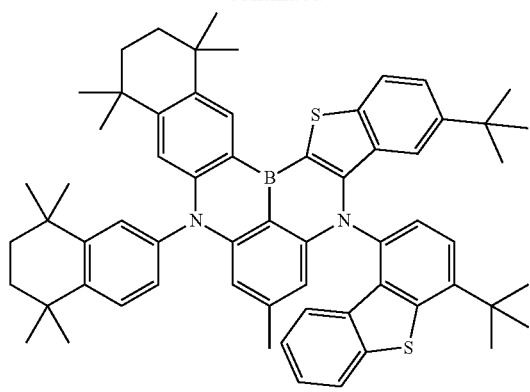
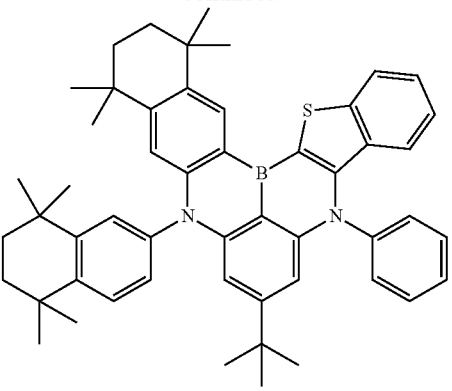
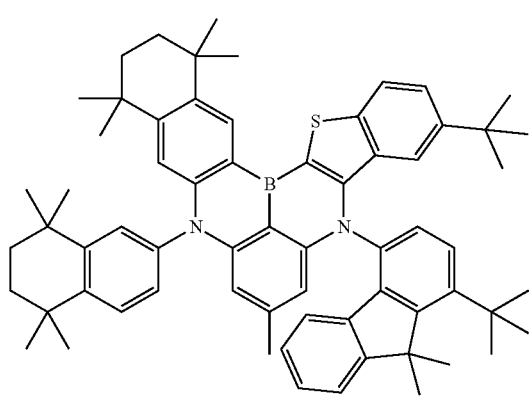
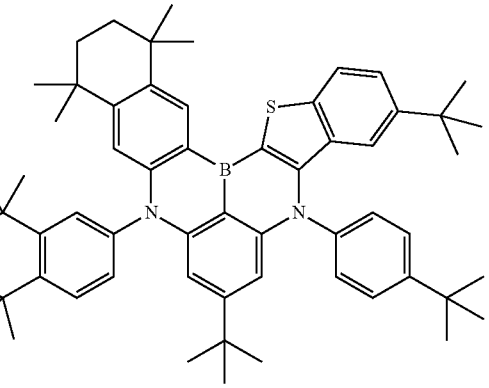
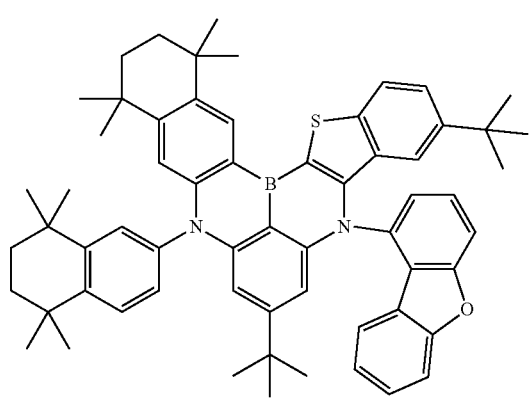
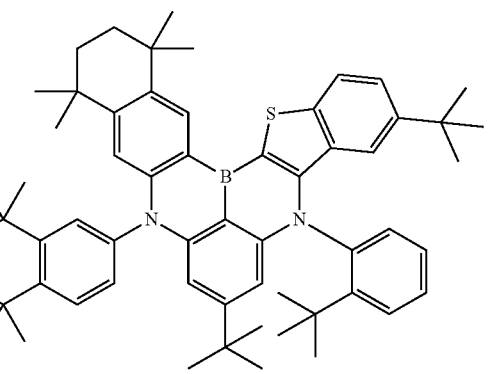
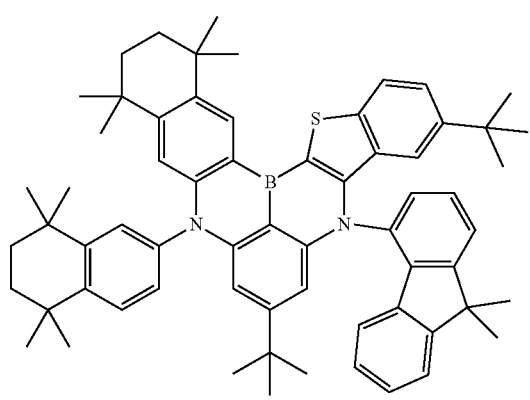

| 2077 -continued | 2078 -continued |
|---|---|
| 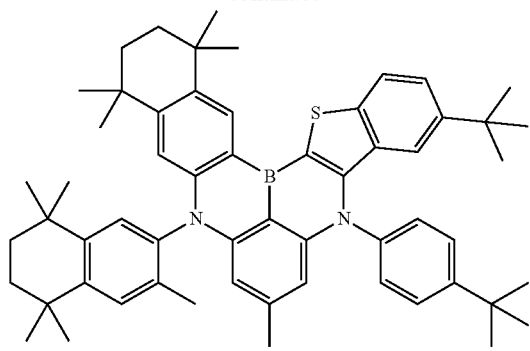 | 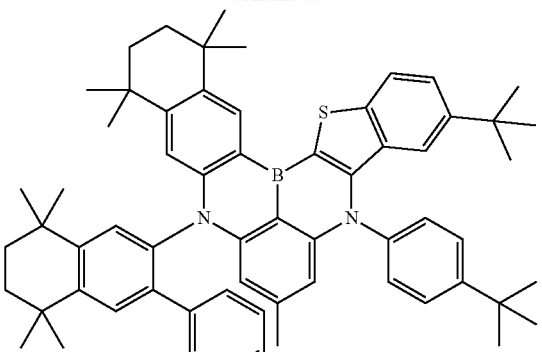 |
| 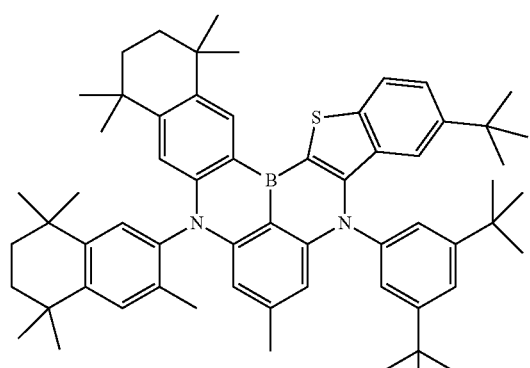 | 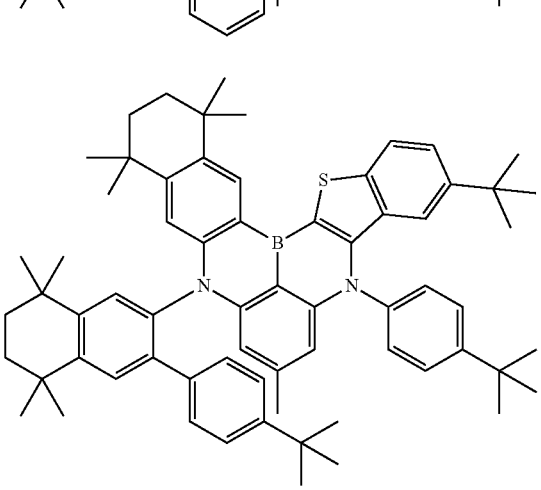 |
| 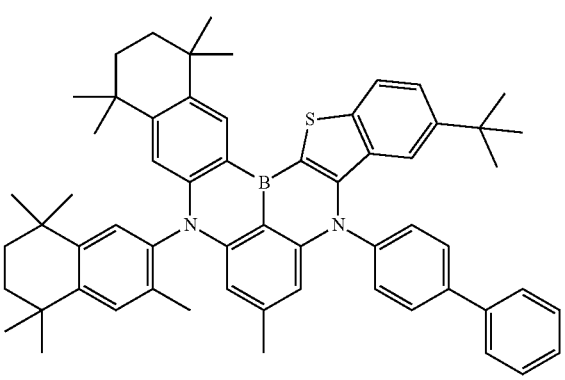 | 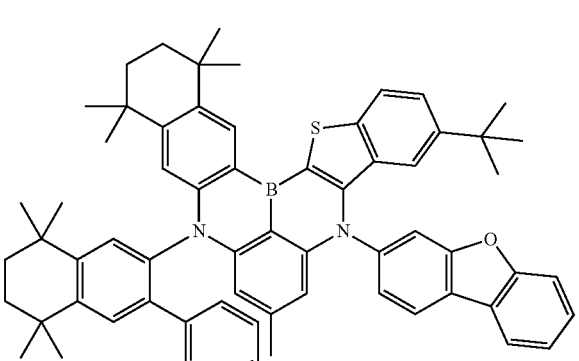 |
| 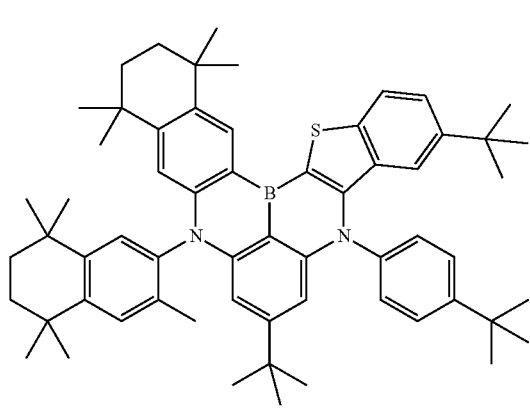 | 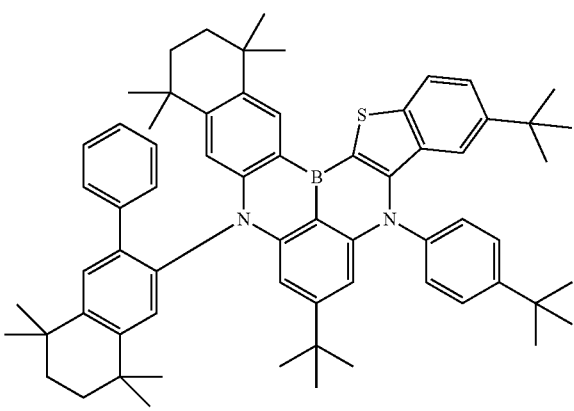 |

| 2079 | 2080 |
|---|---|
| 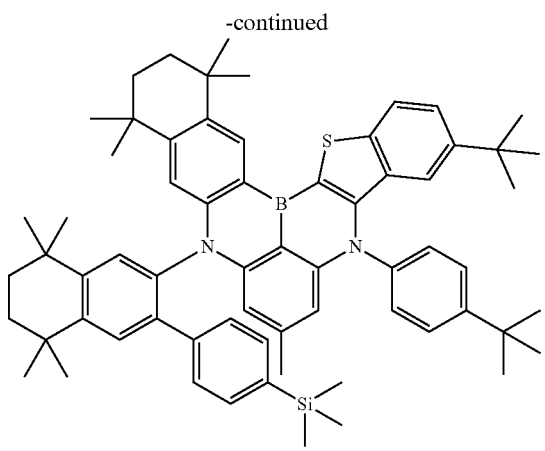 | 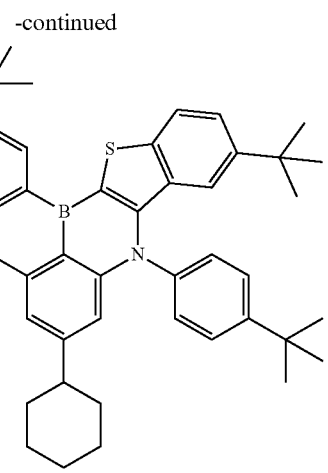 |
| 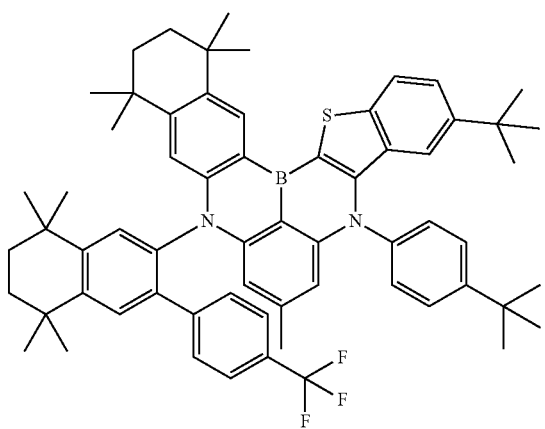 | 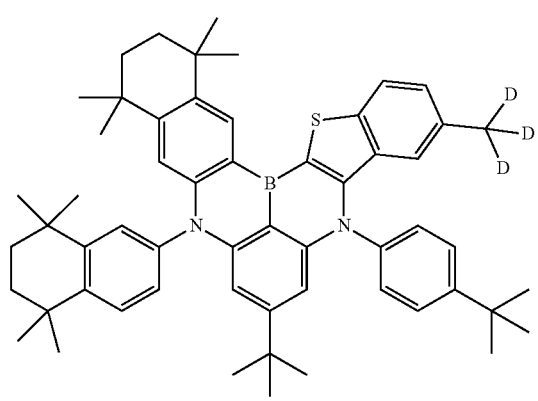 |
| 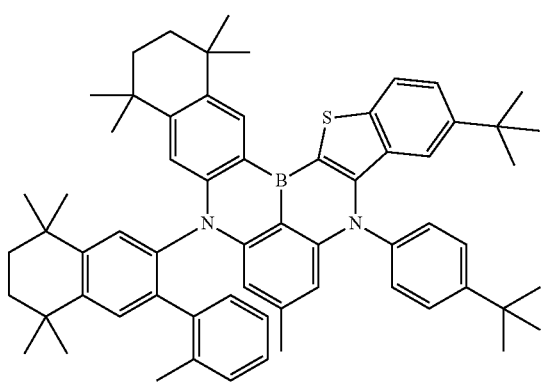 | 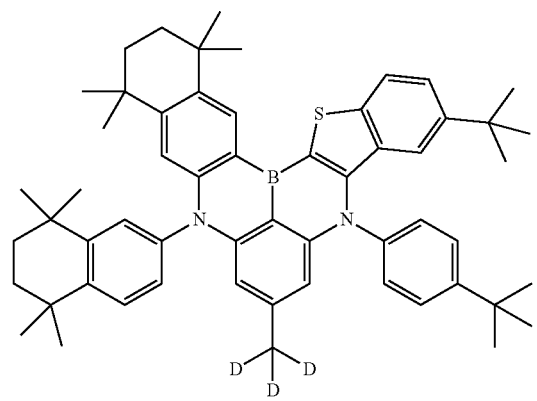 |
| 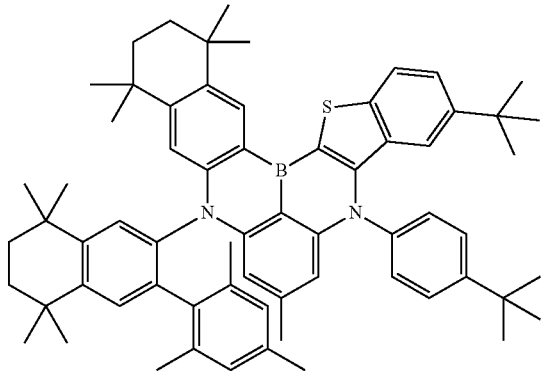 | 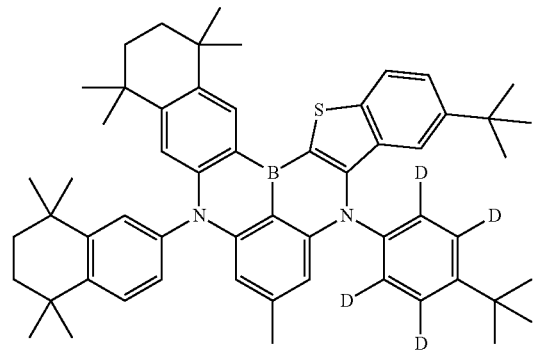 |

2081
-continued
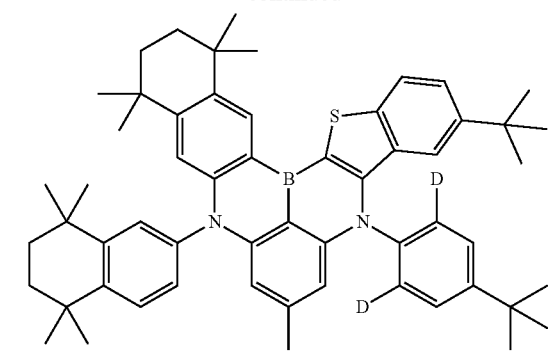
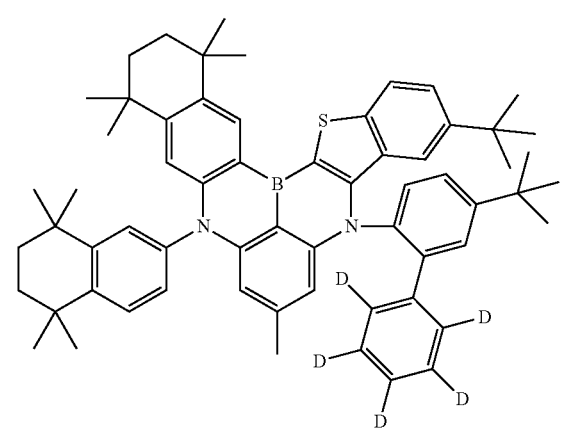
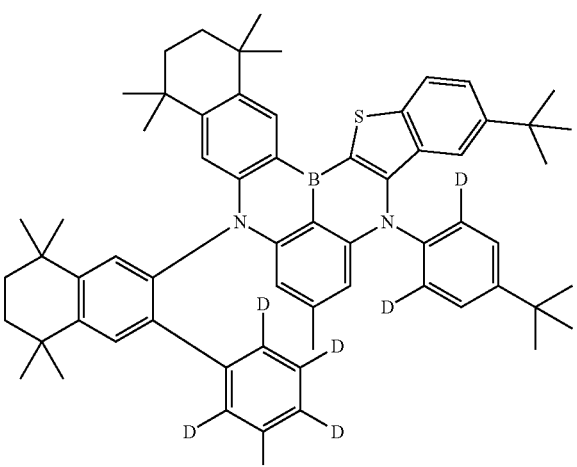
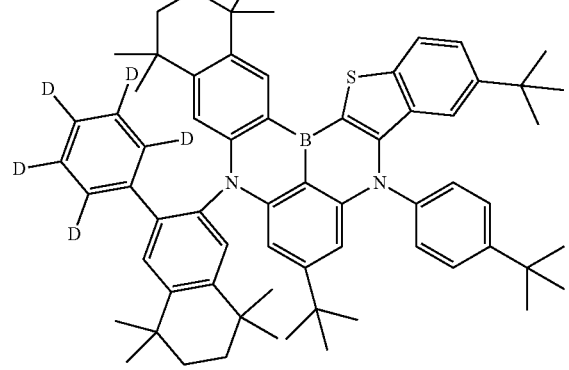
2082
-continued
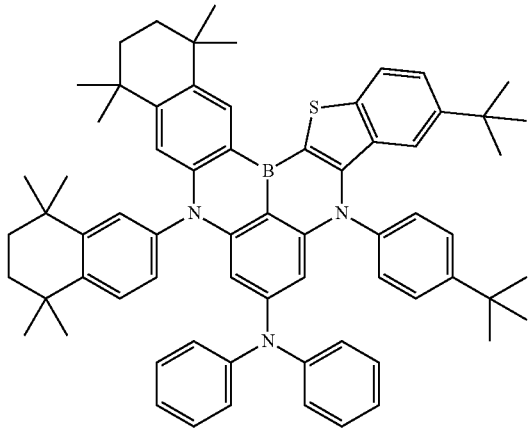
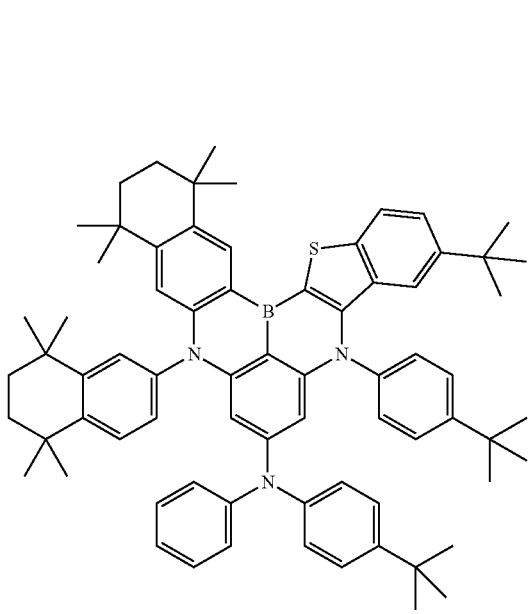
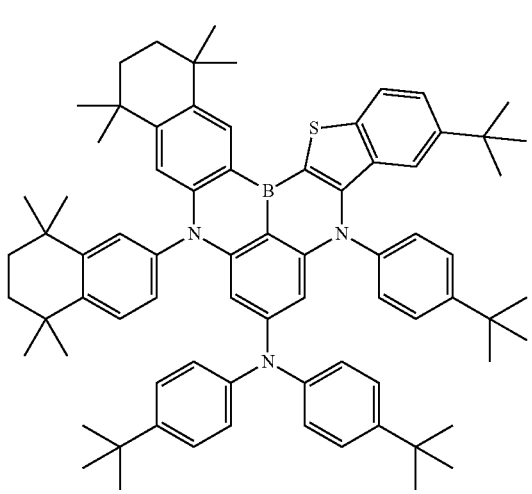

2083
-continued
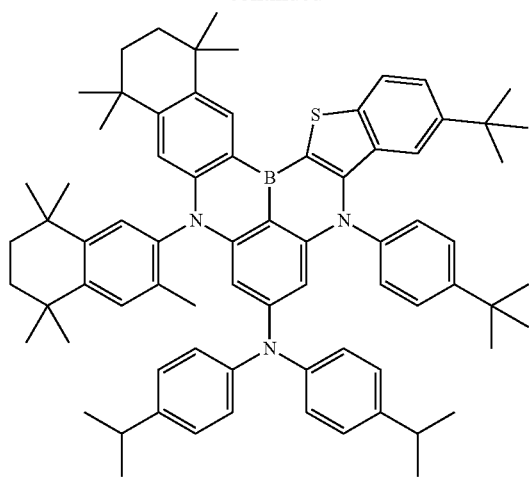
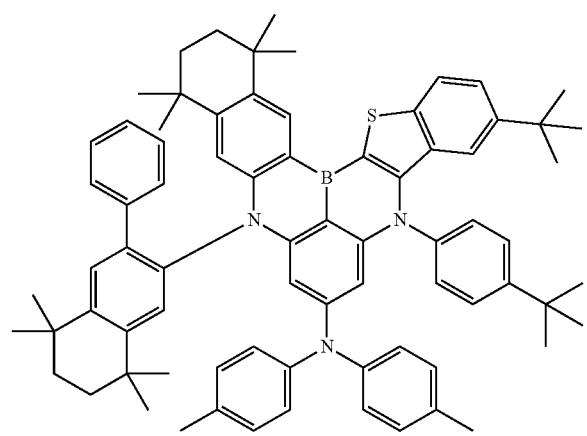
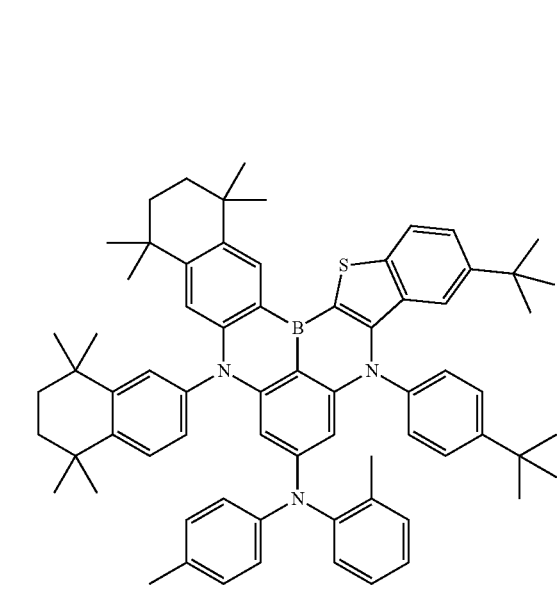
2084
-continued
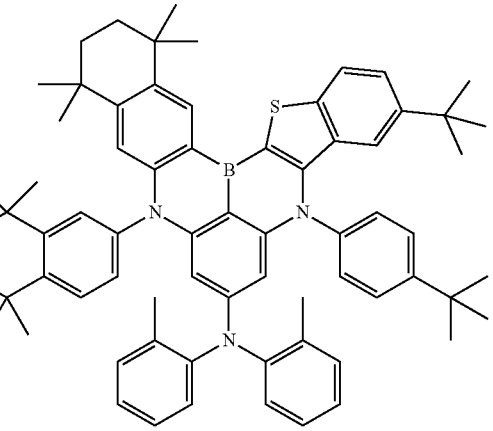
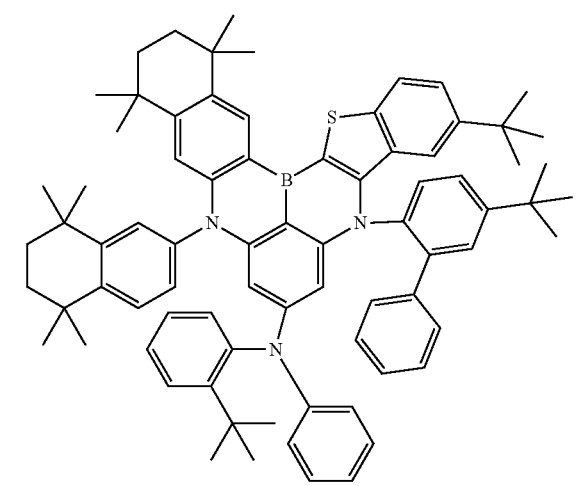
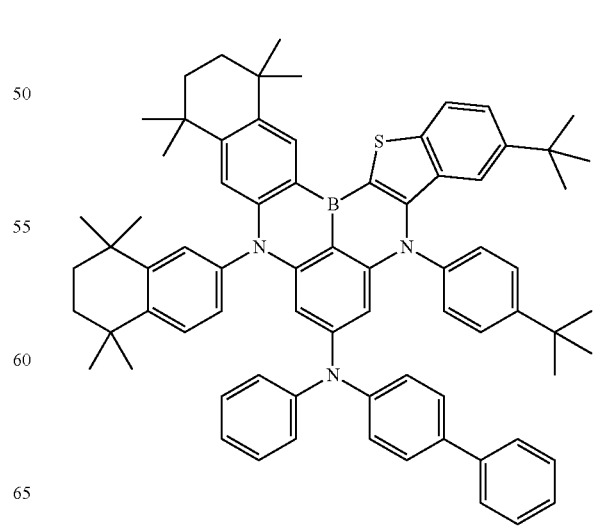

2085
-continued
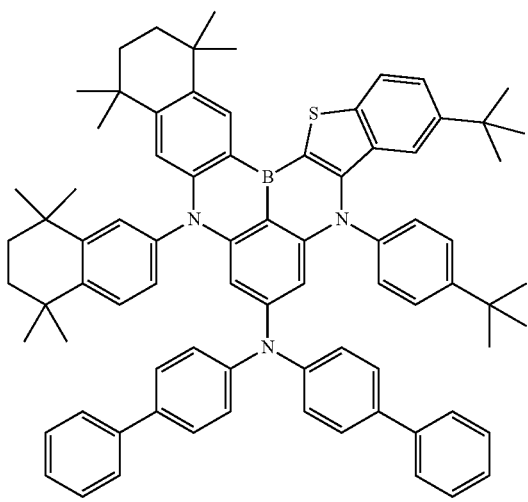
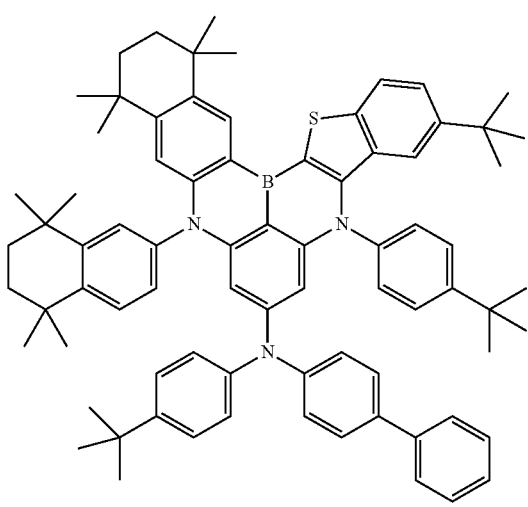
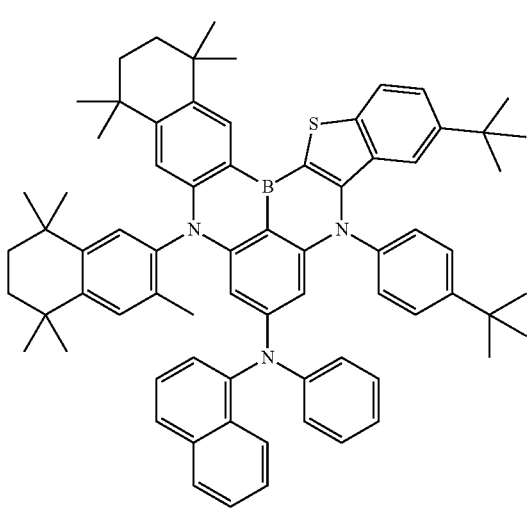
2086
-continued
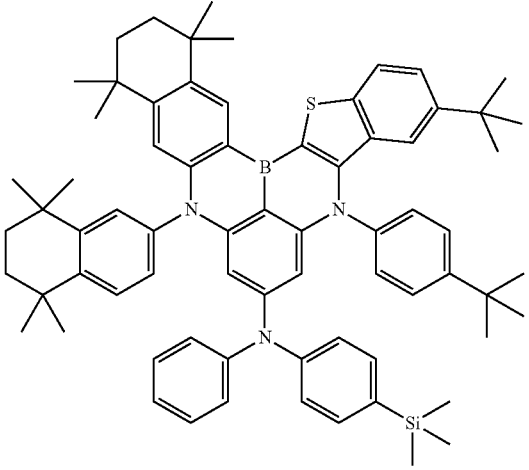
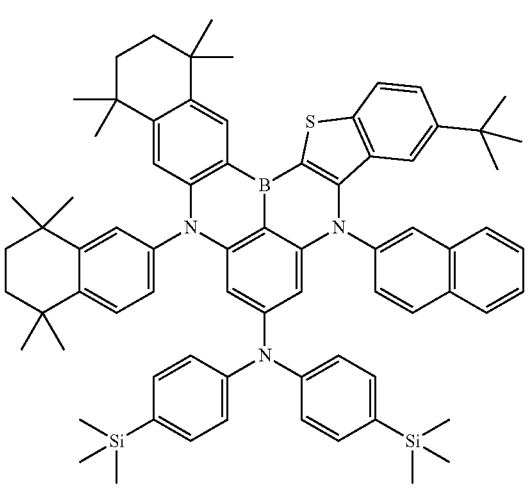
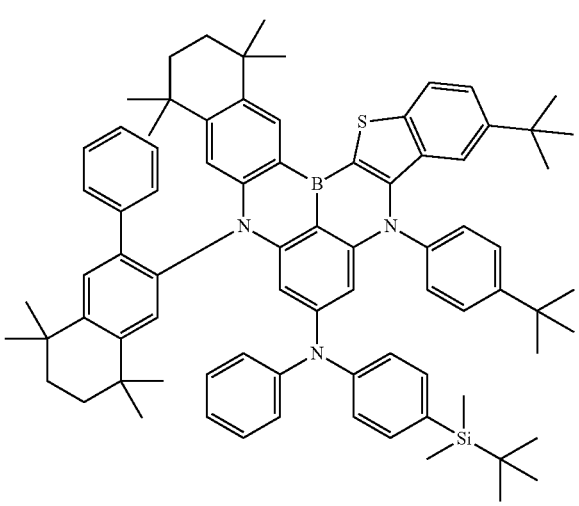

2087
-continued
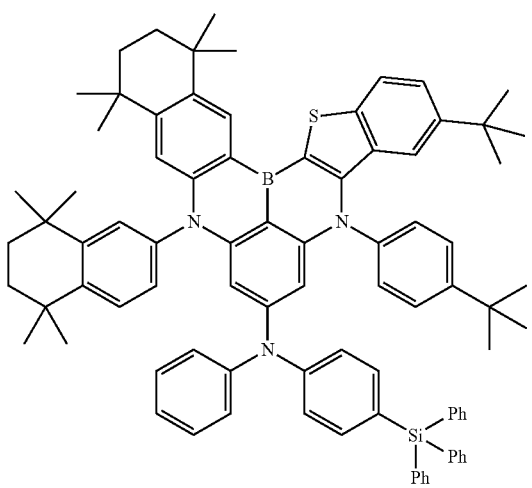
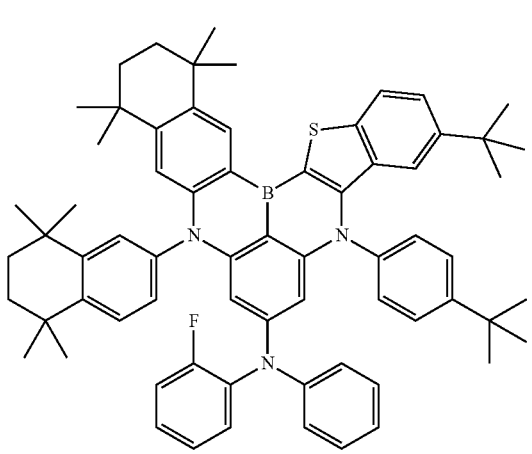
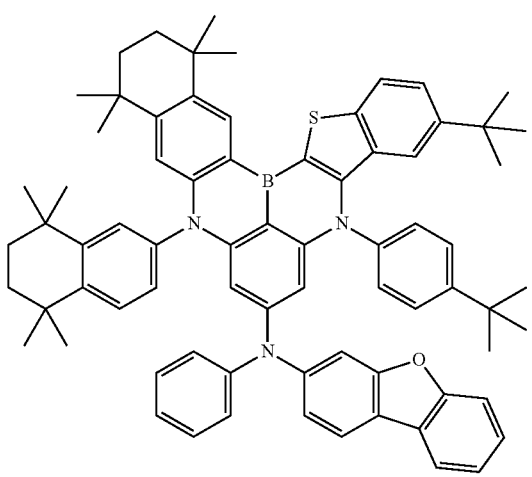
2088
-continued
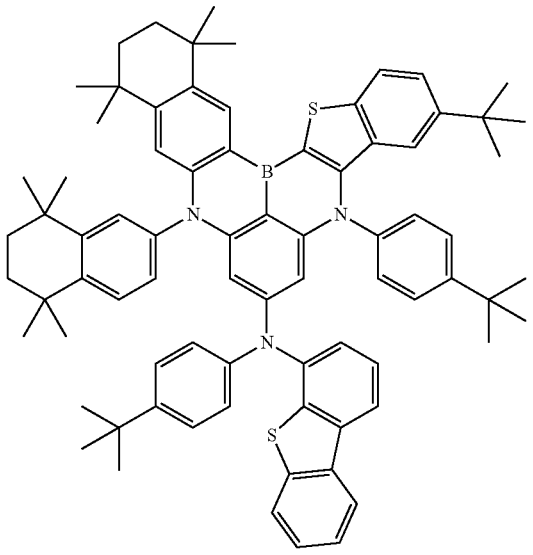
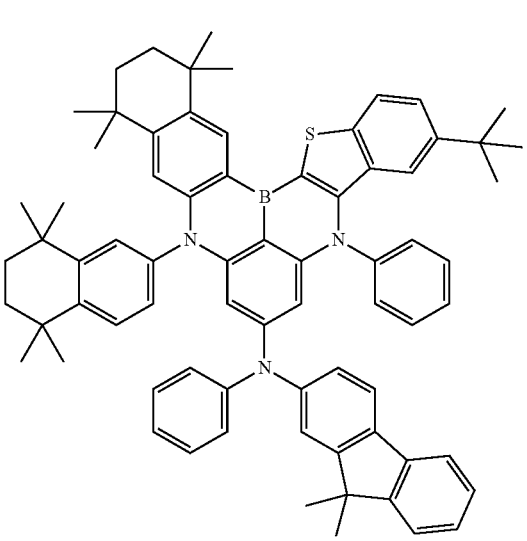
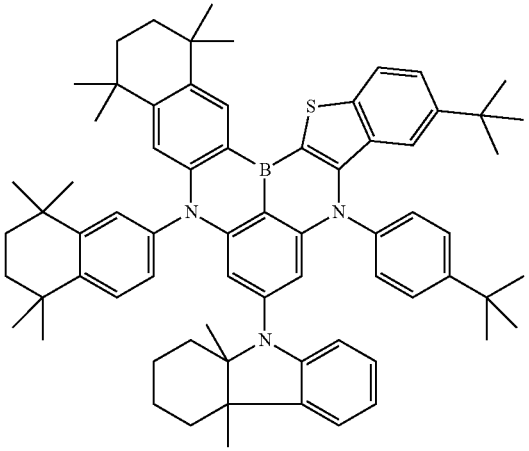

2089
-continued
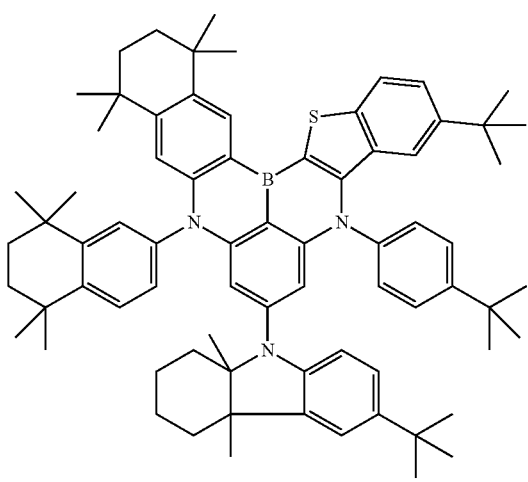
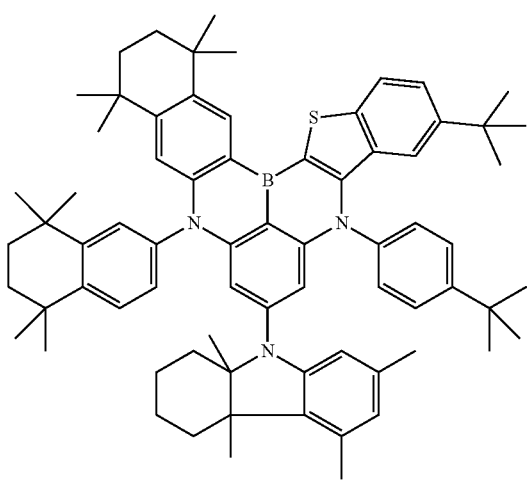
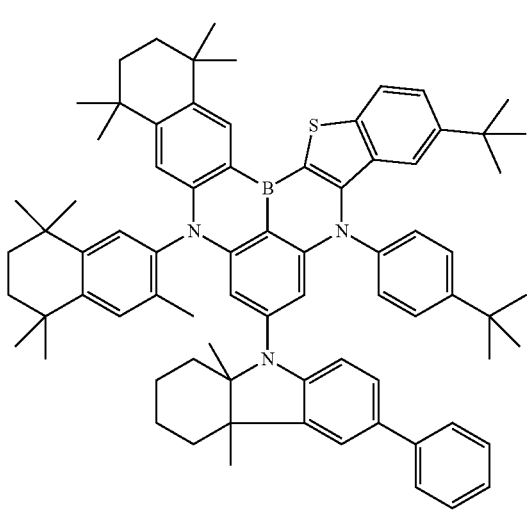
2090
-continued
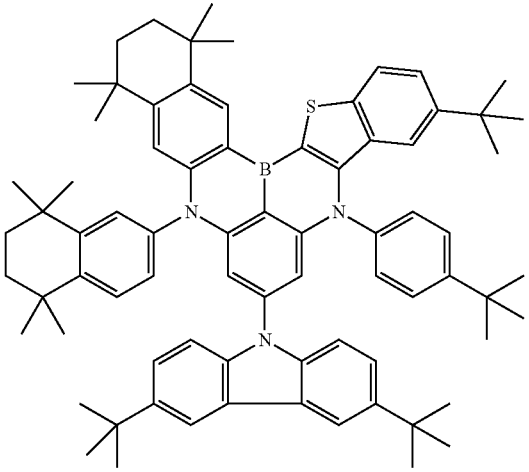
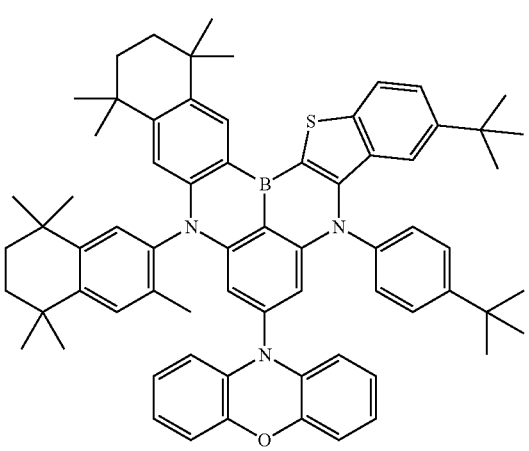
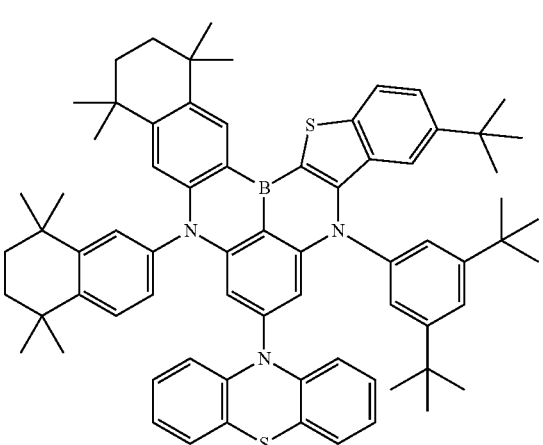

2091
-continued
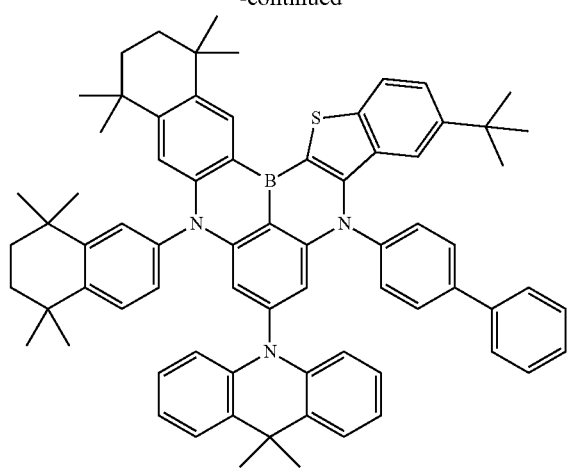
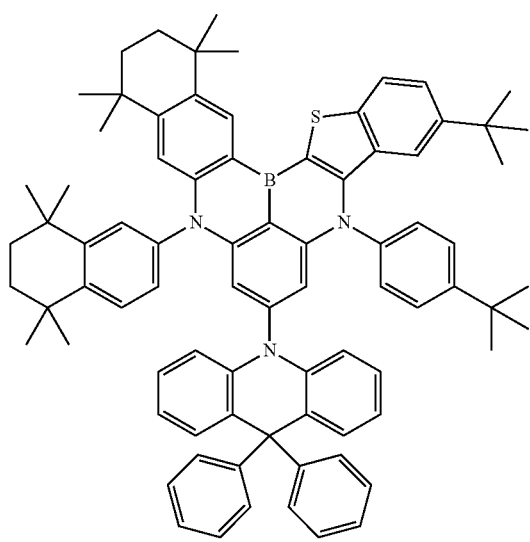
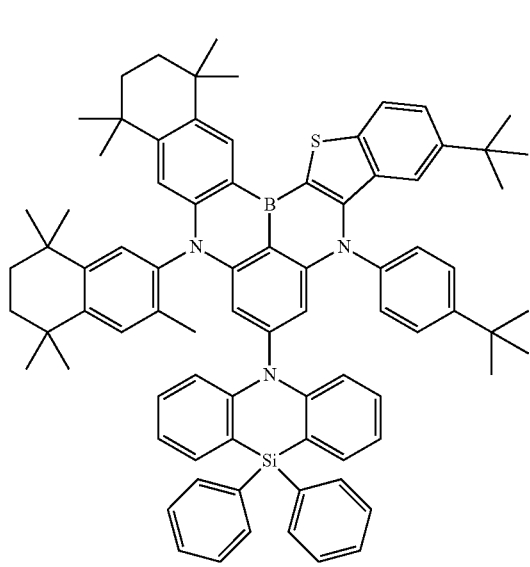
2092
-continued
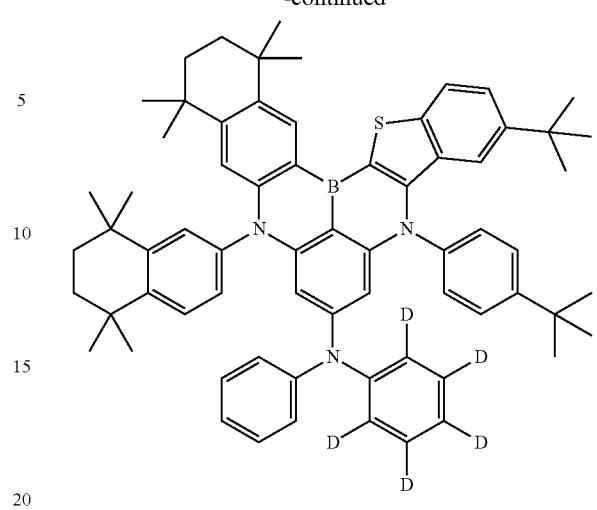
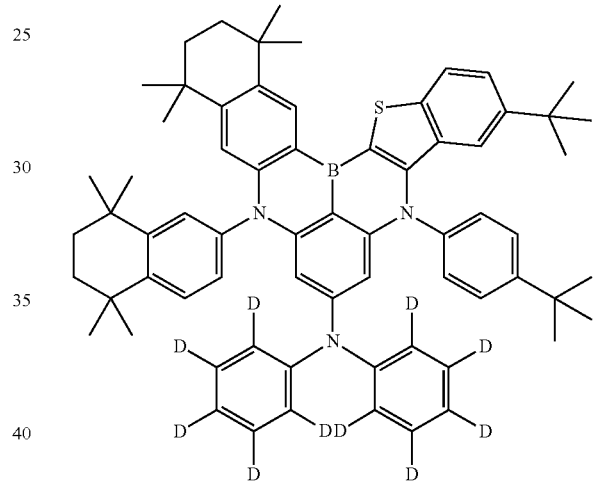
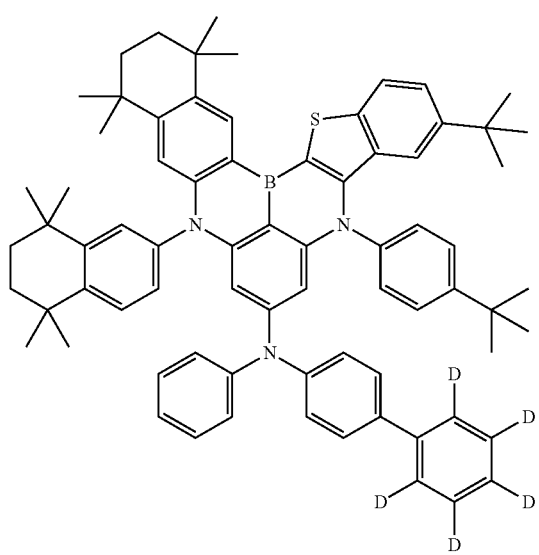

2093
-continued
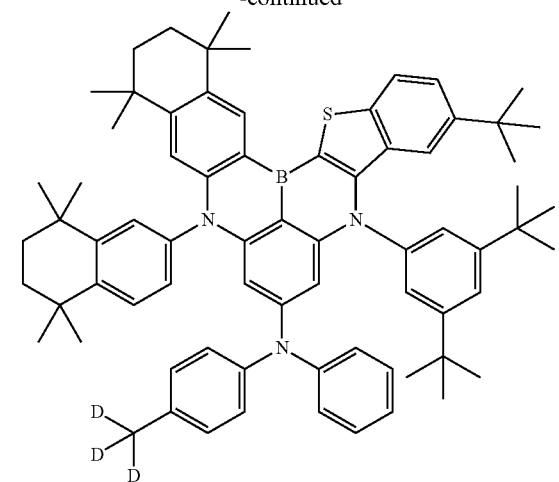
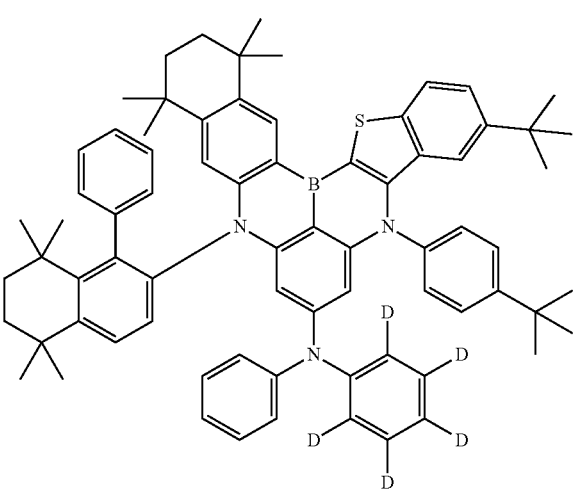
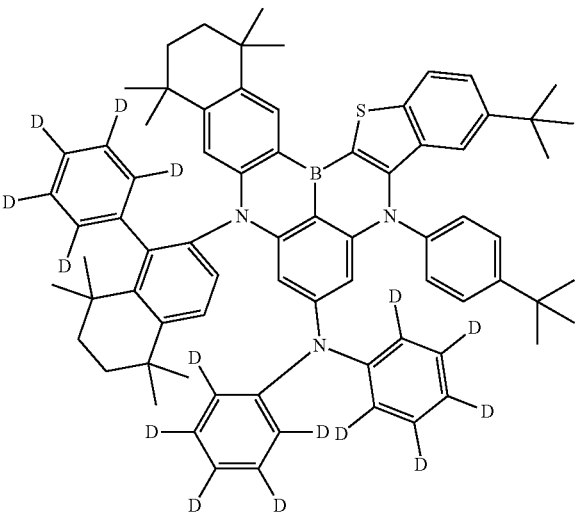
2094
-continued
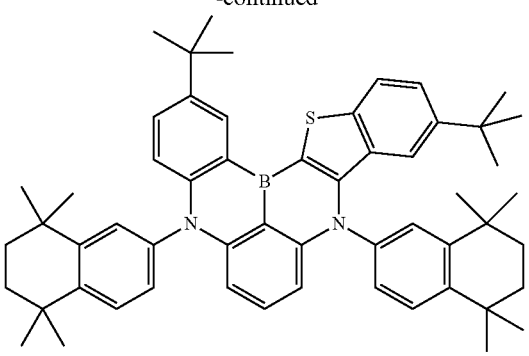
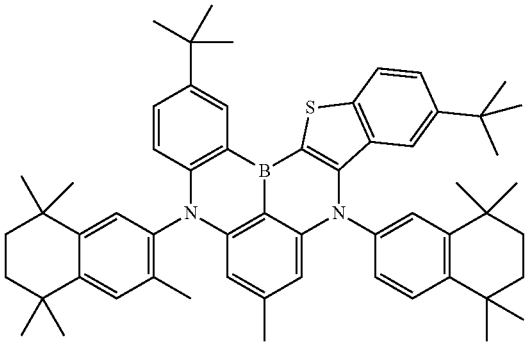
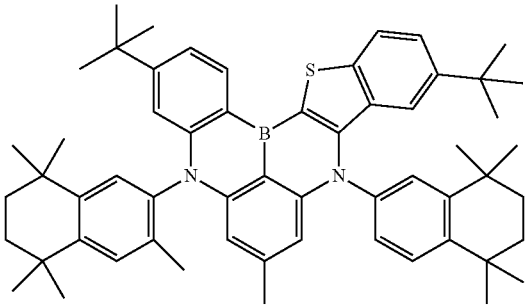
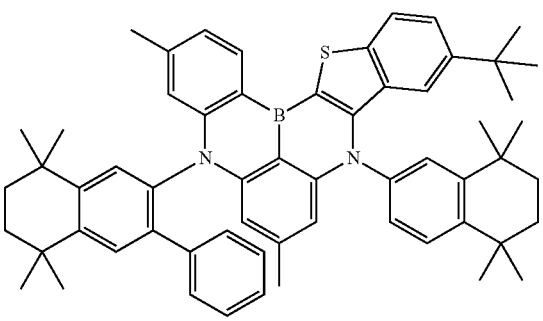
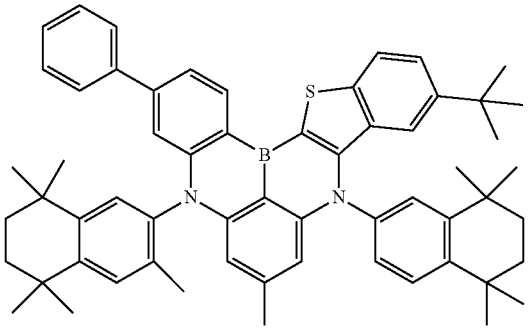

2095
-continued
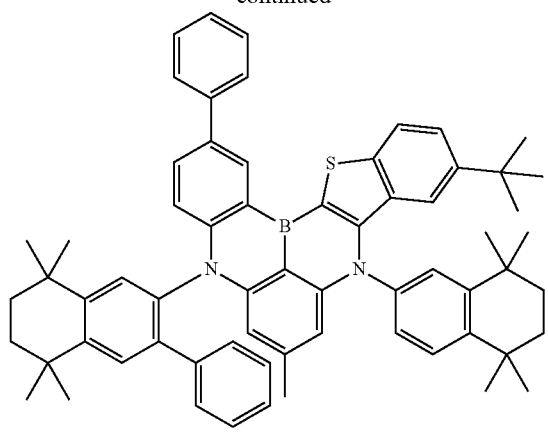
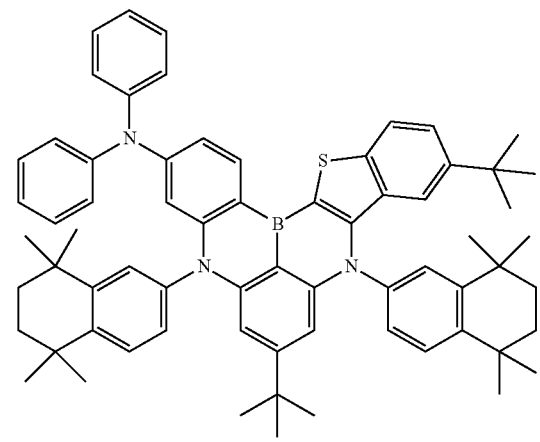
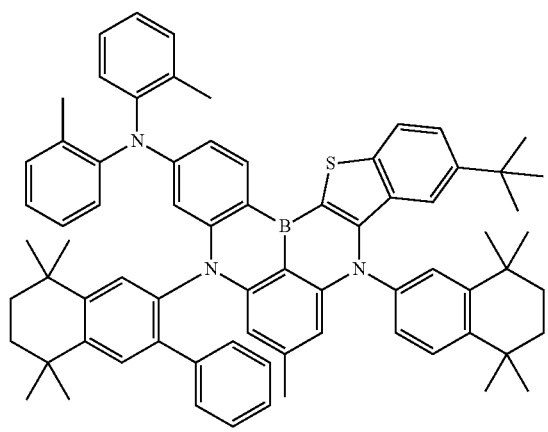
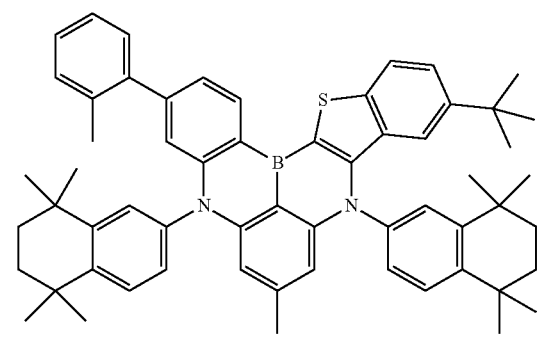
2096
-continued
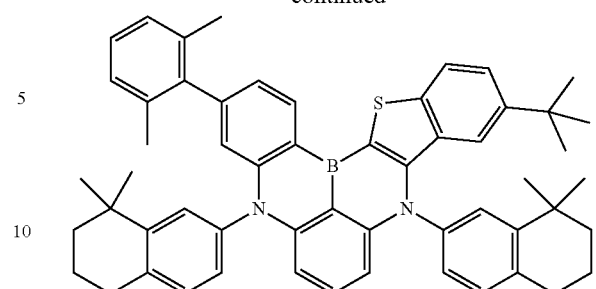

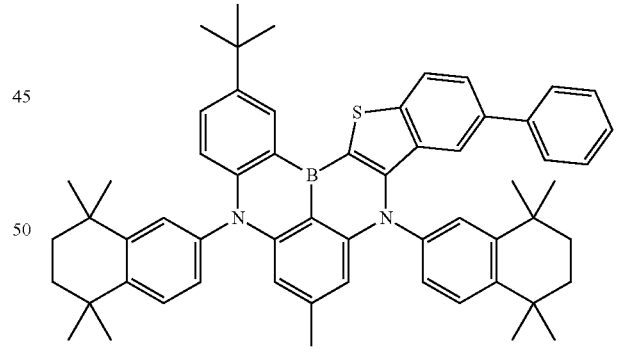
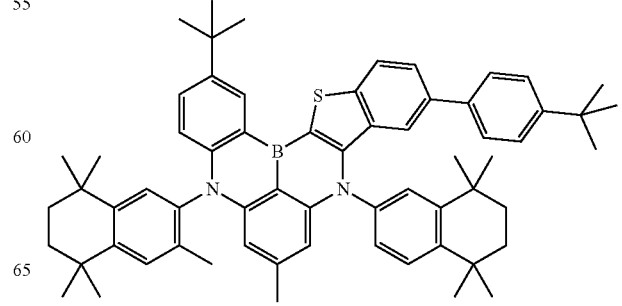

| 2097 | 2098 |
|---|---|
| 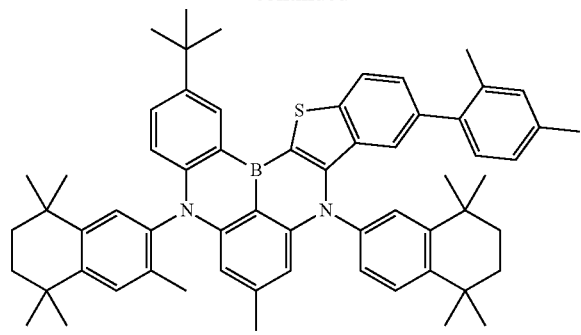 | 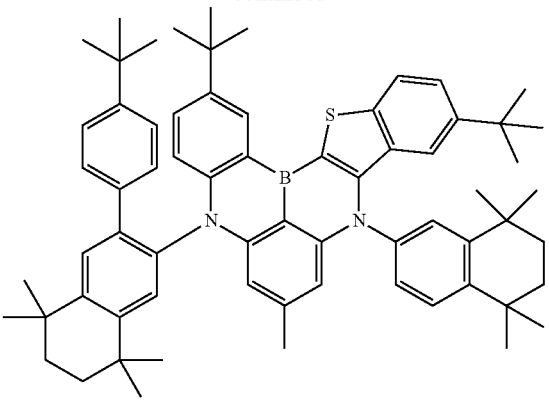 |
| 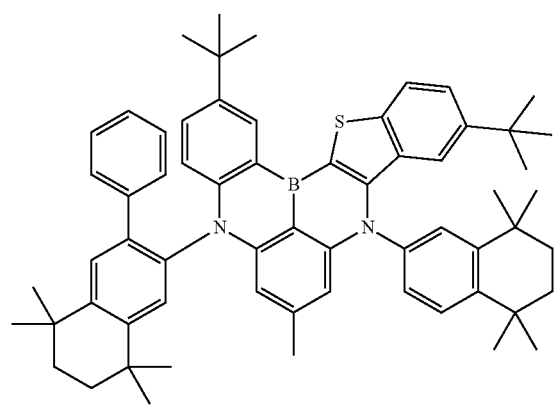 | 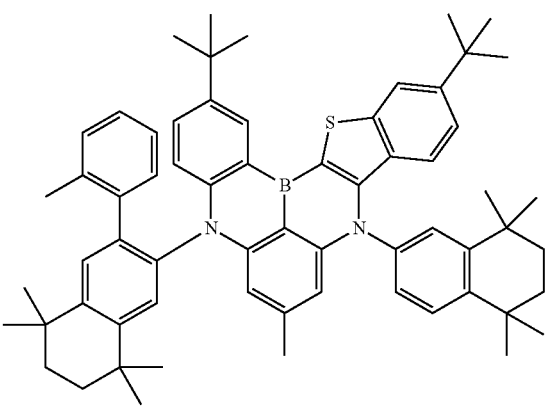 |
| 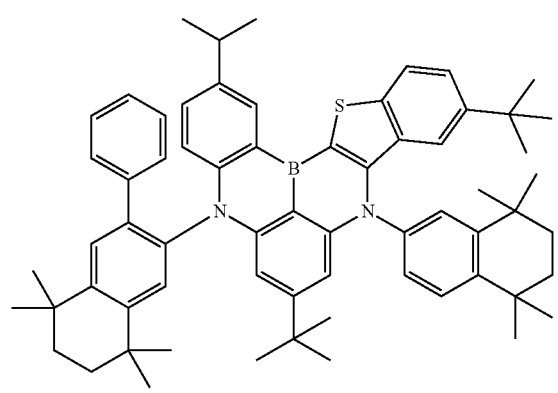 | 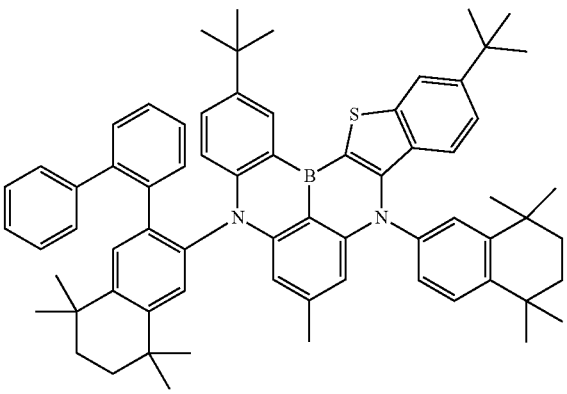 |
| 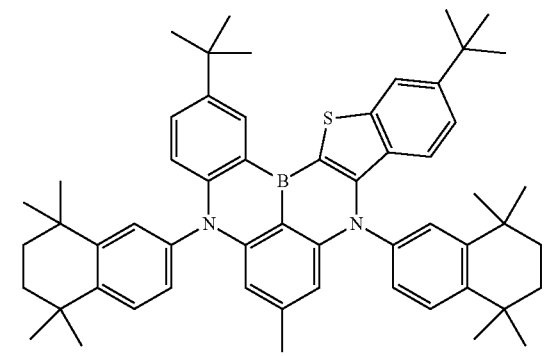 | 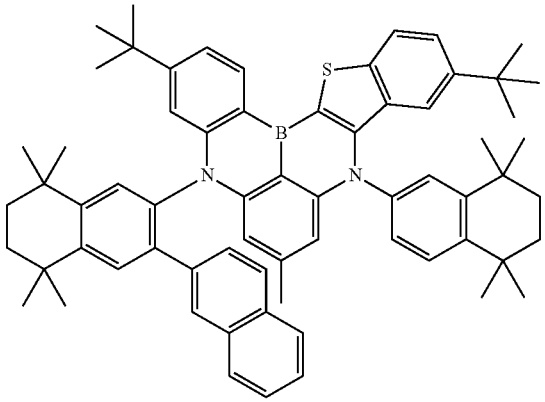 |

2099
-continued
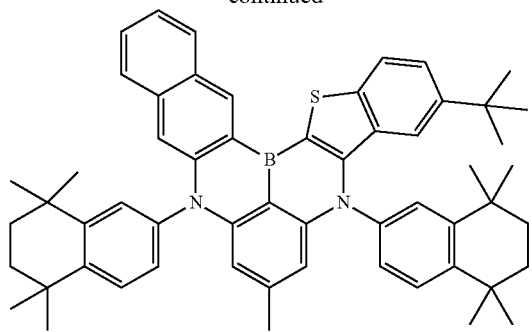
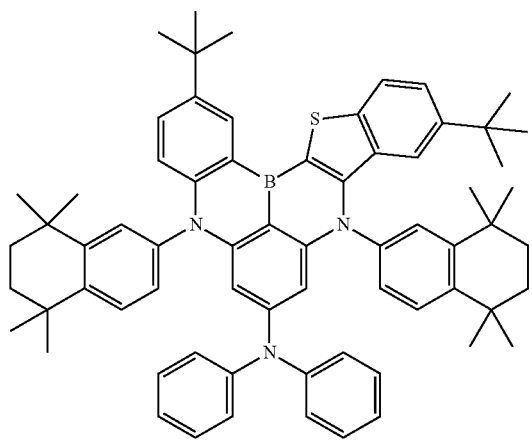
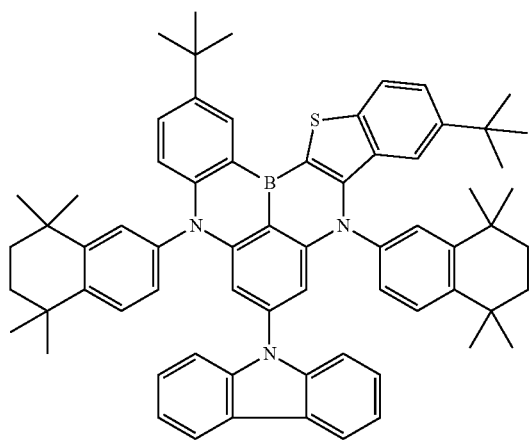
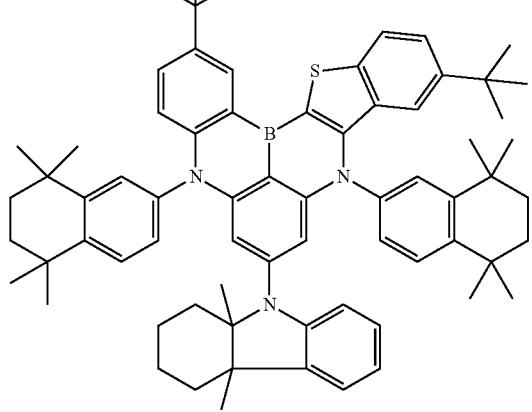
2100
-continued
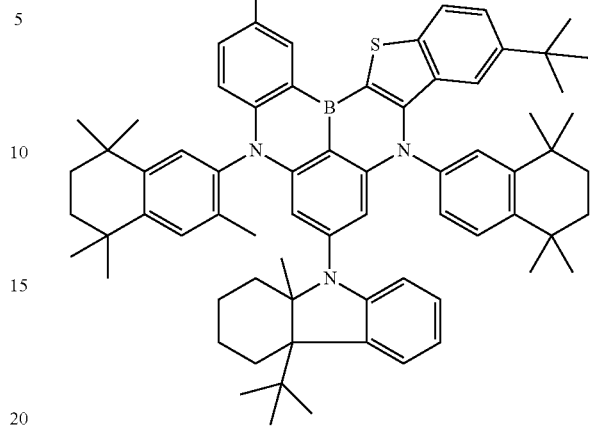
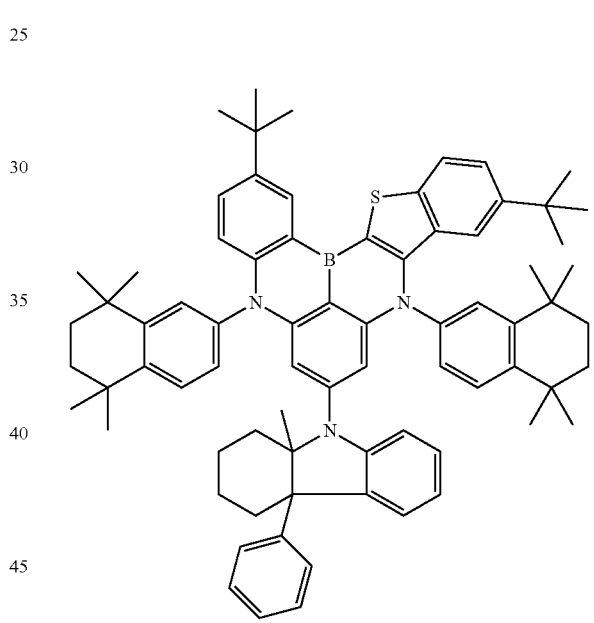

2101
-continued
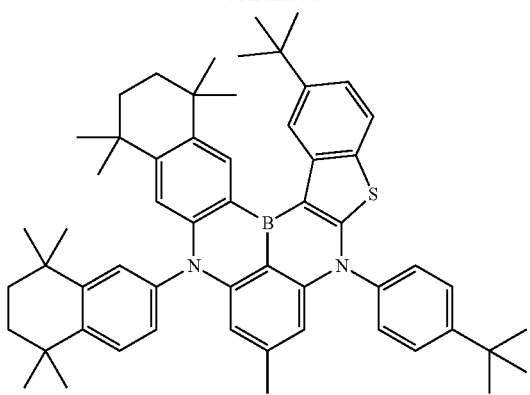
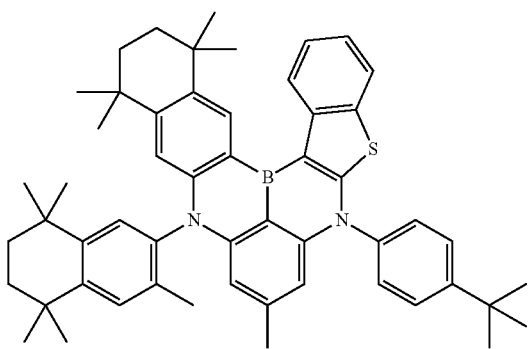
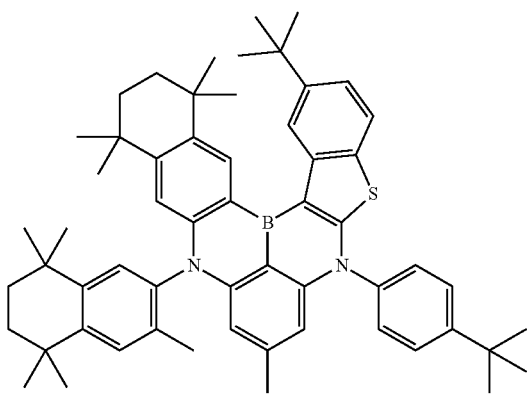
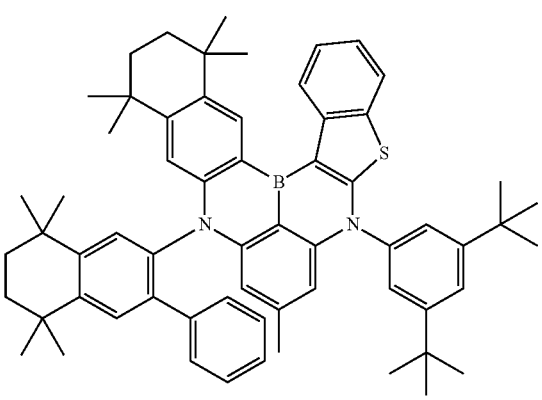
2102
-continued
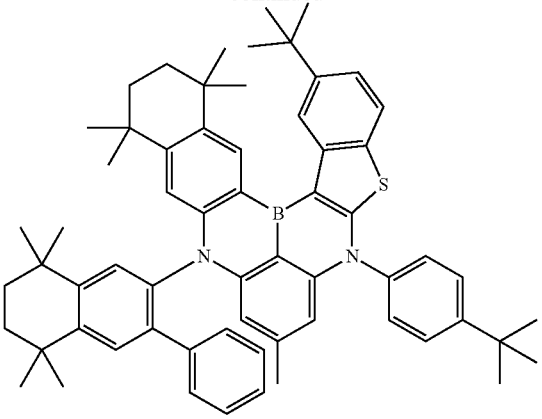
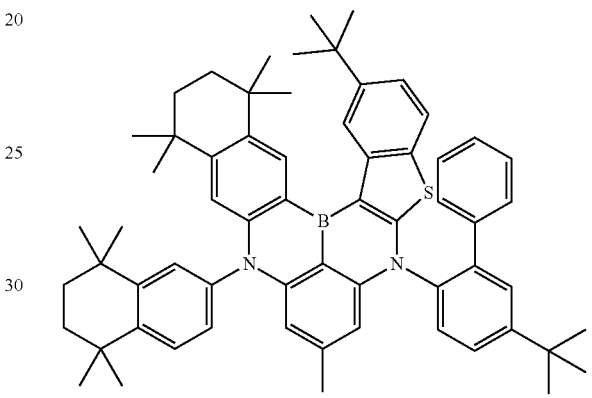
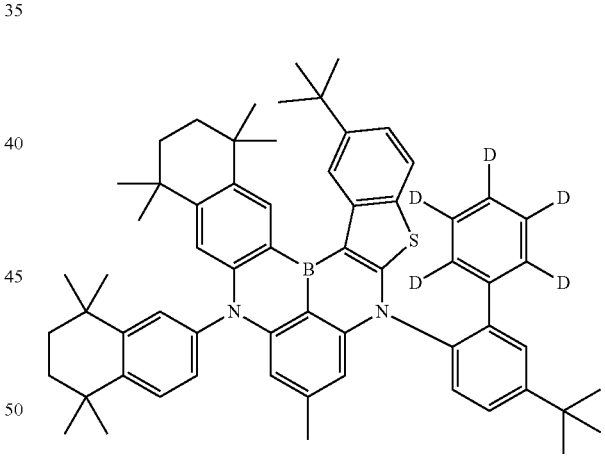
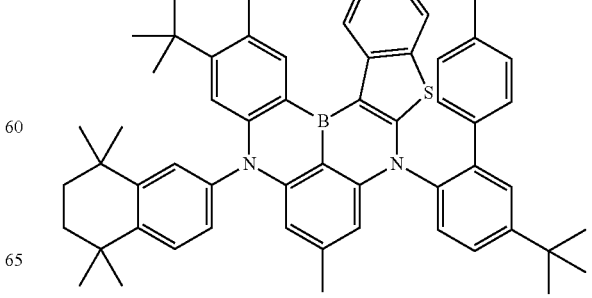

2103
-continued

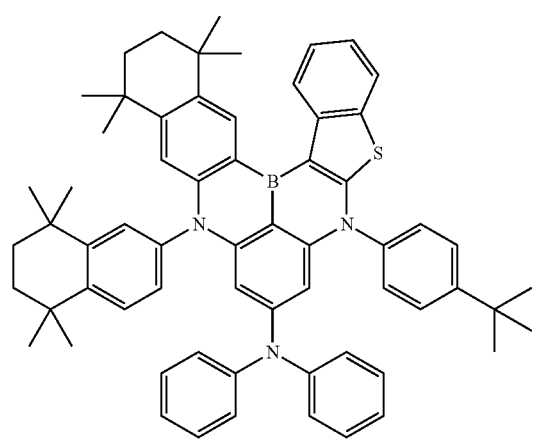
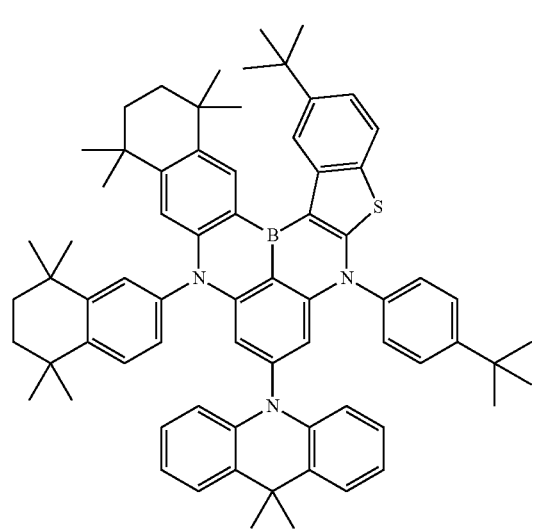
2104
-continued
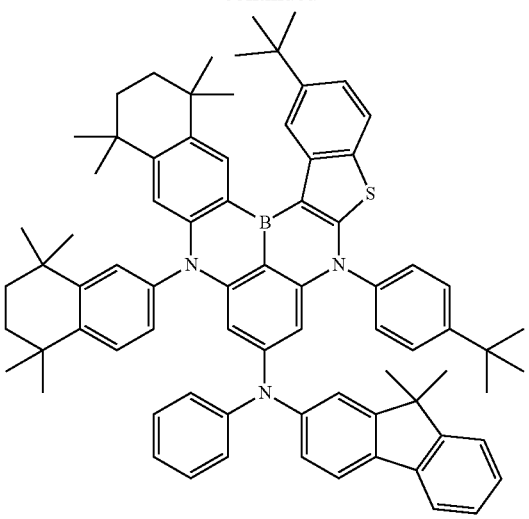
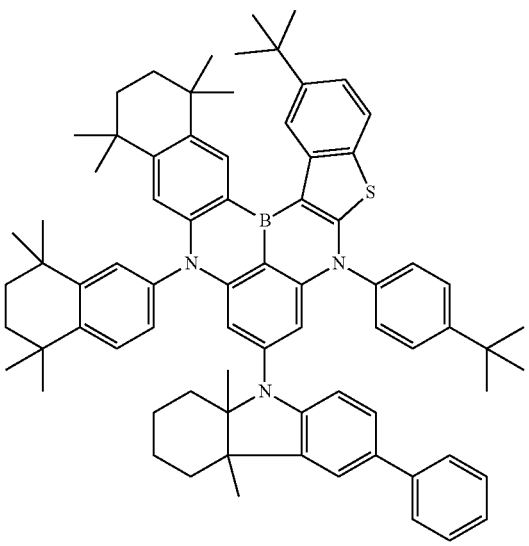
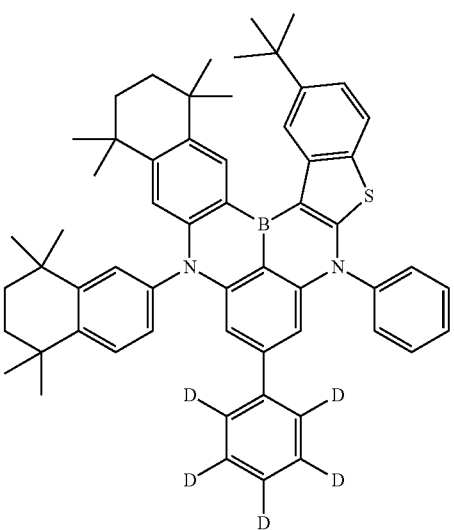

2105
-continued
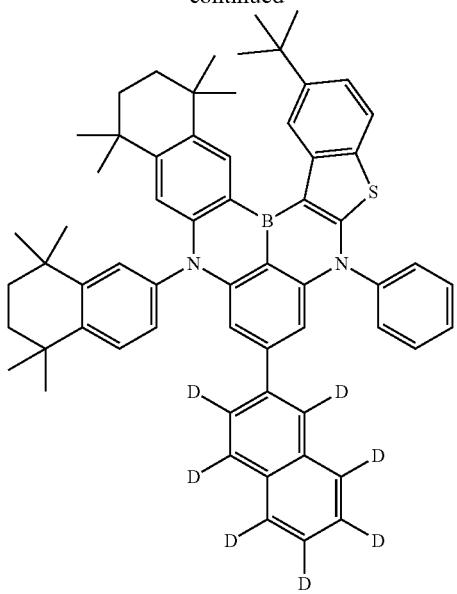
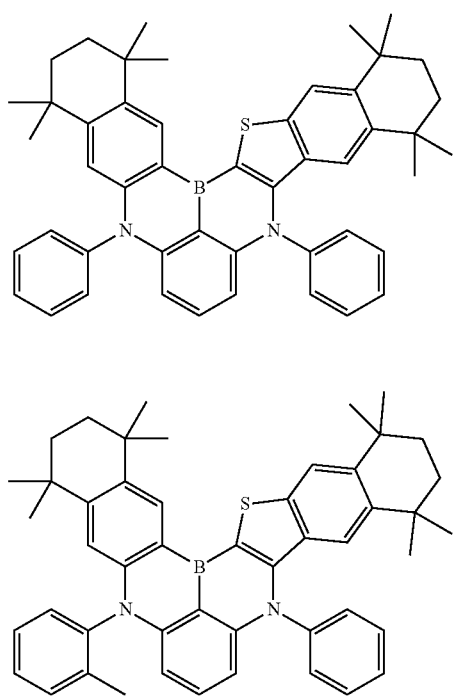
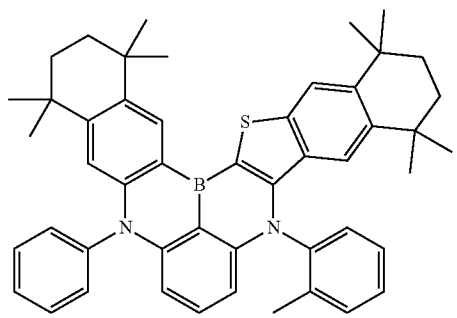
2106
-continued
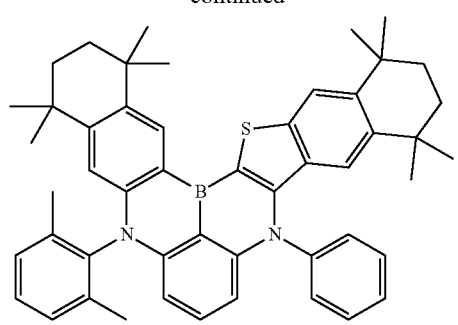
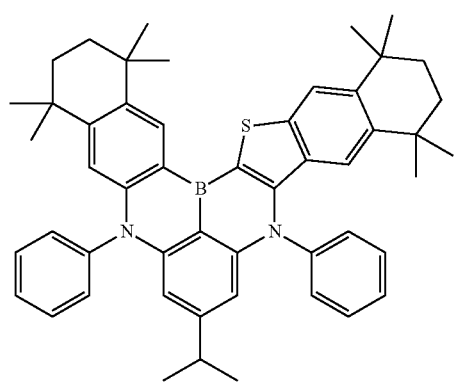
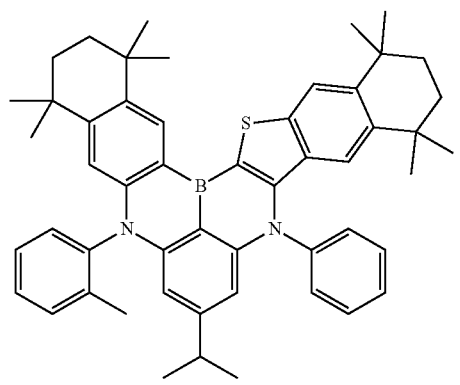
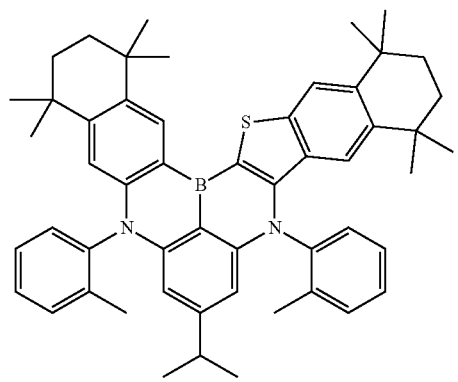

| 2107 -continued | 2108 -continued |
|---|---|
| 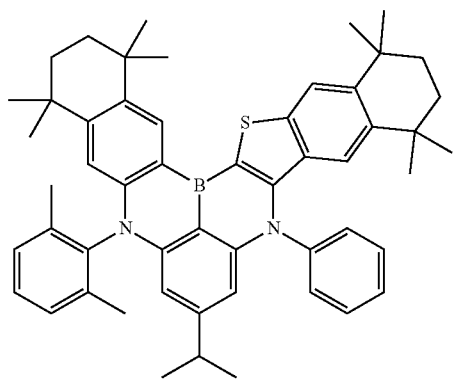 | 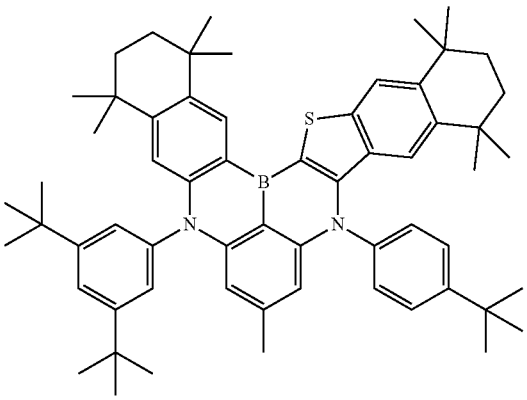 |
| 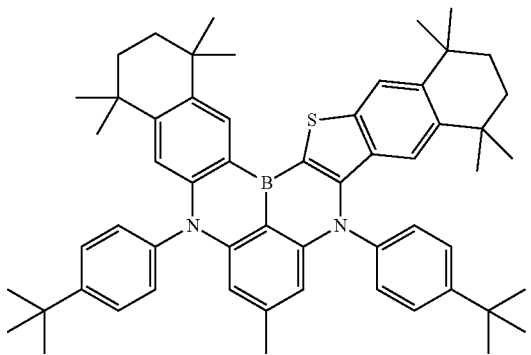 | 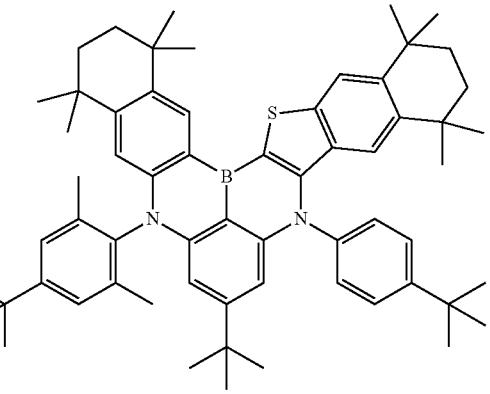 |
| 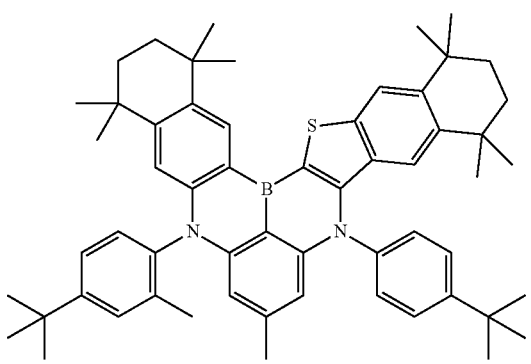 | 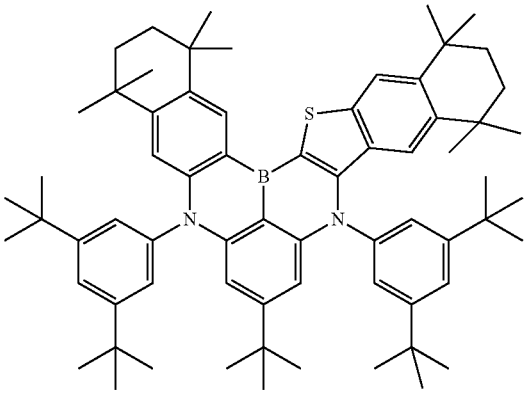 |
| 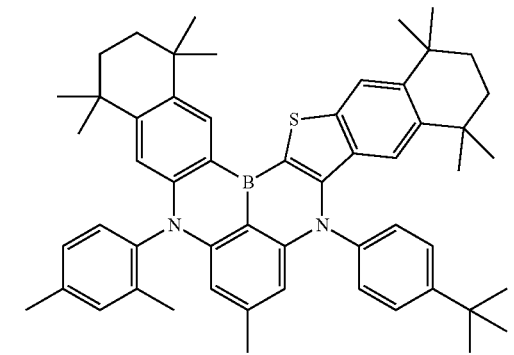 | 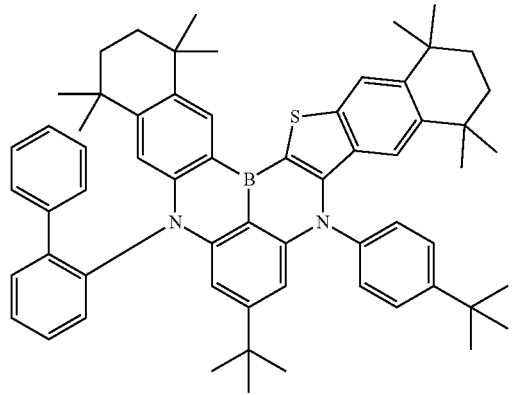 |

2109
-continued
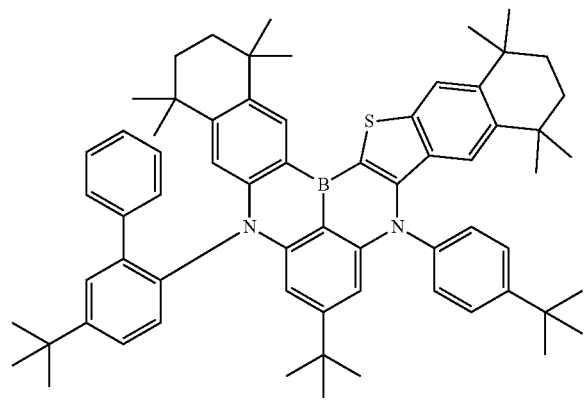
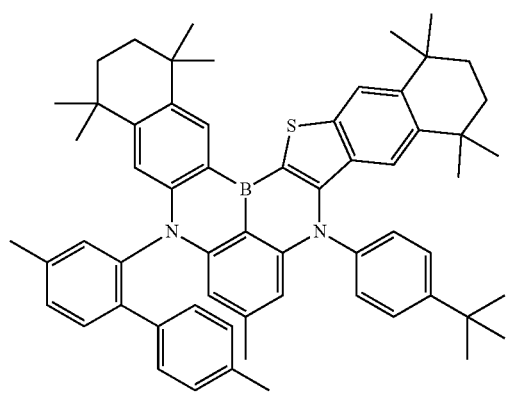
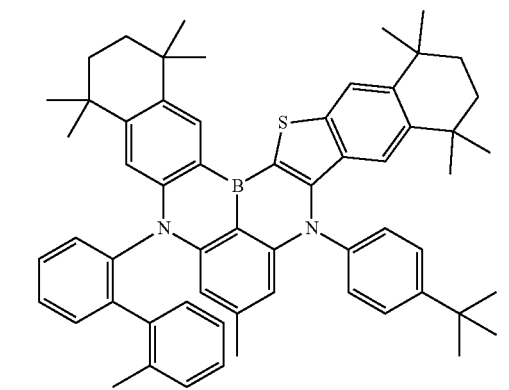
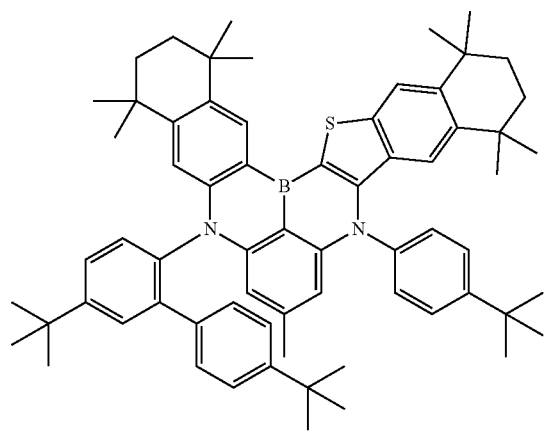
2110
-continued
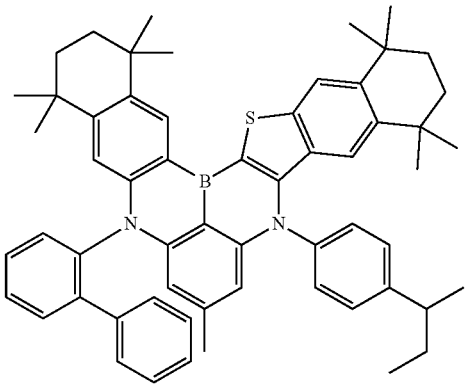
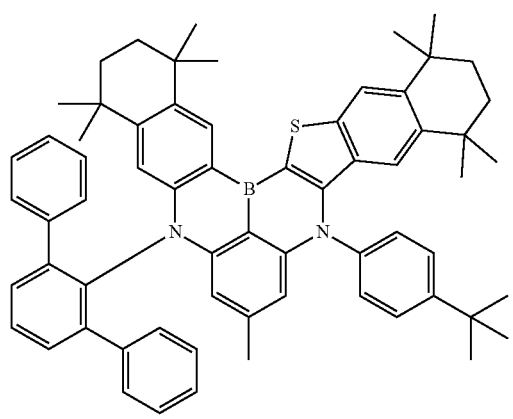

2111
-continued
2112
-continued
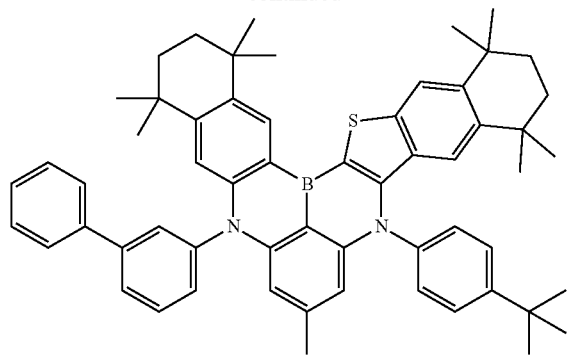
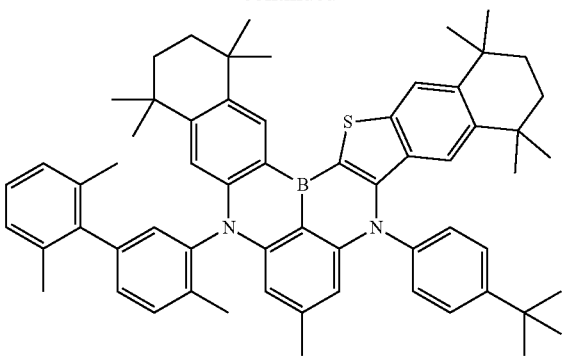

2113
-continued
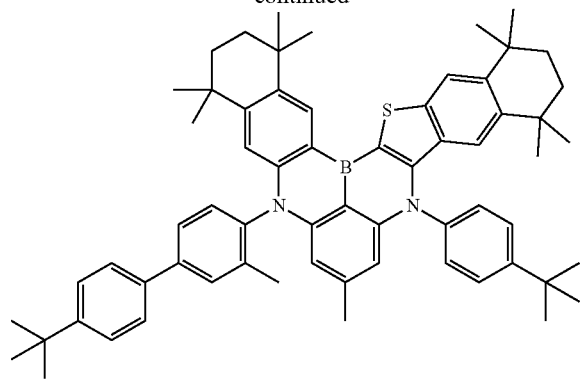
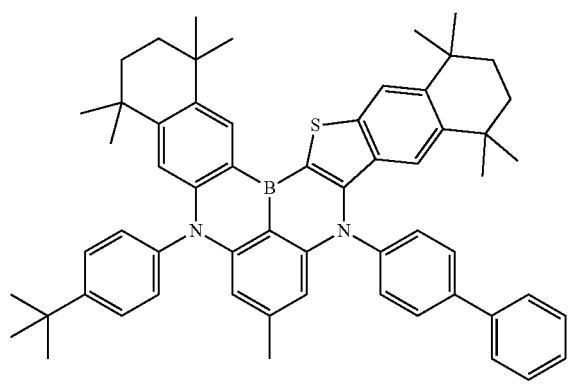
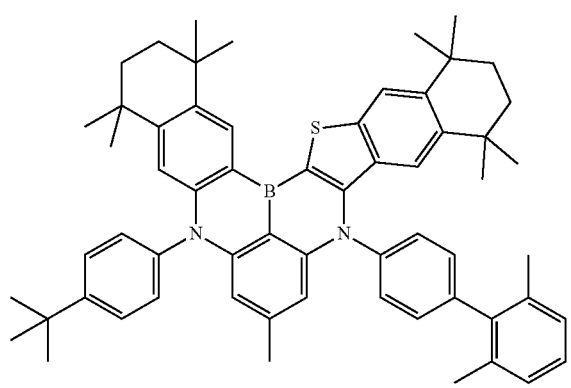
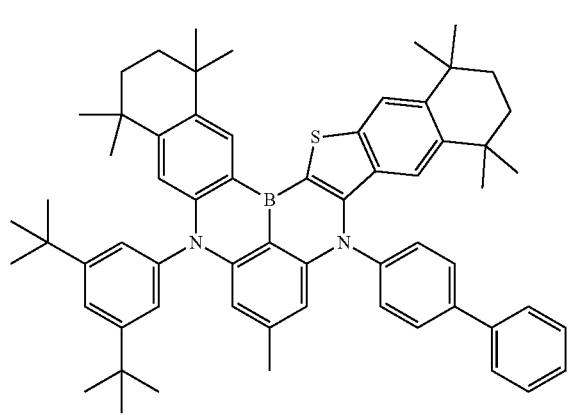
2114
-continued
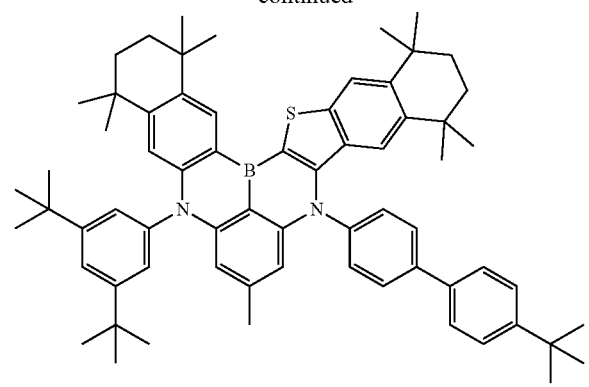
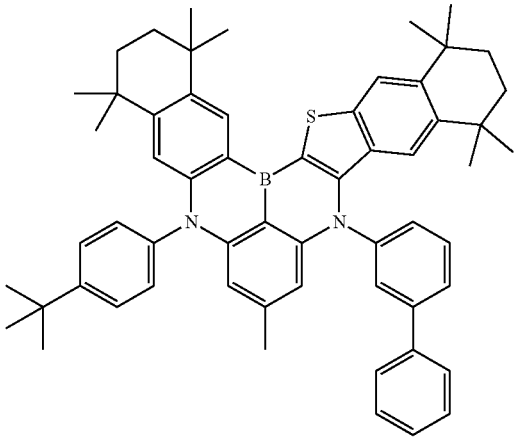
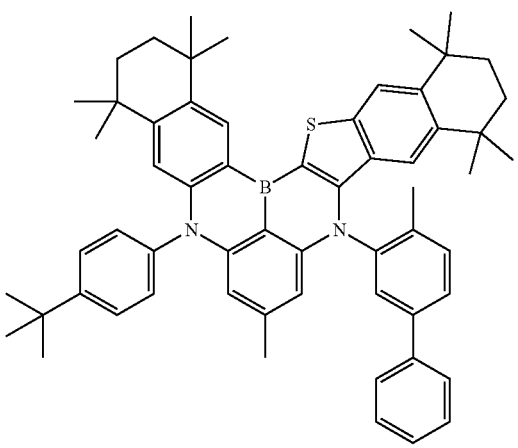
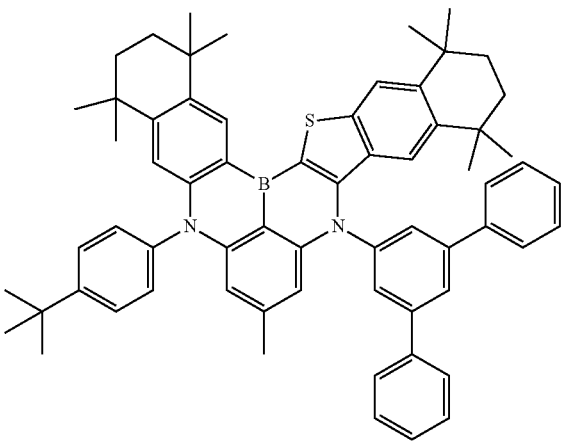

2115
-continued
2116
-continued
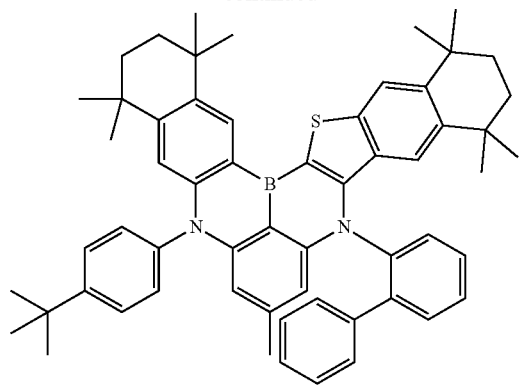
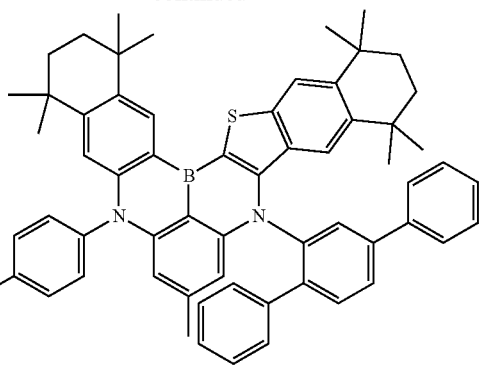
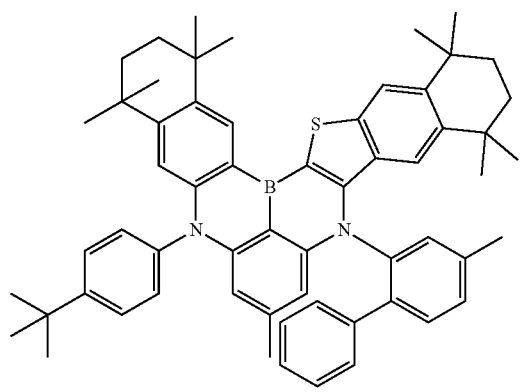
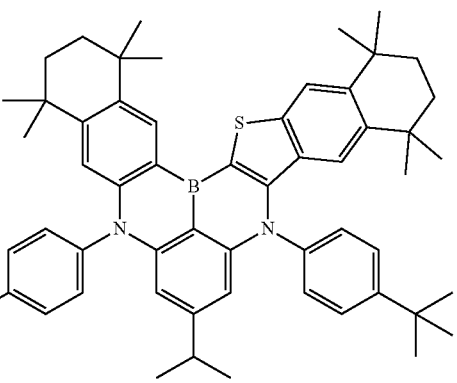
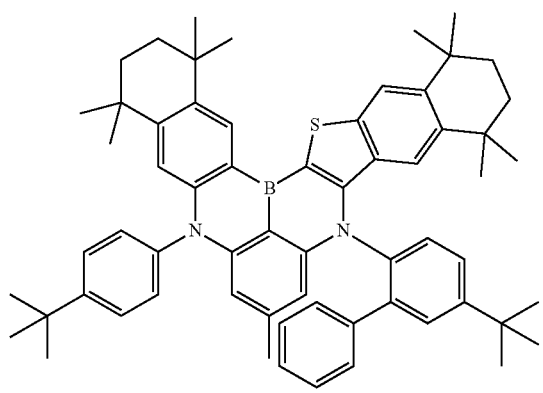
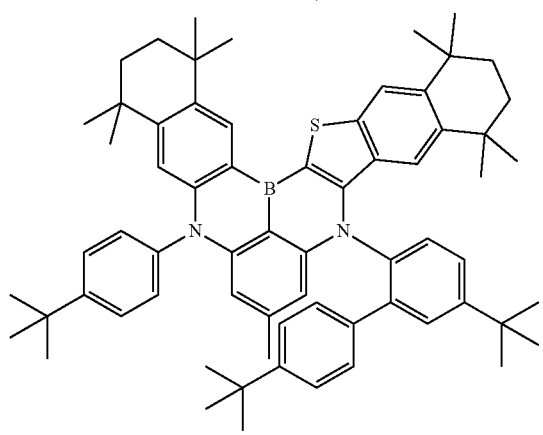
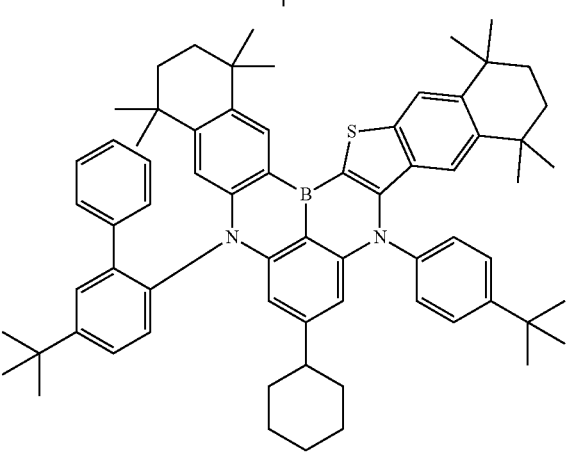

US 11,685,751 B2
2117
-continued
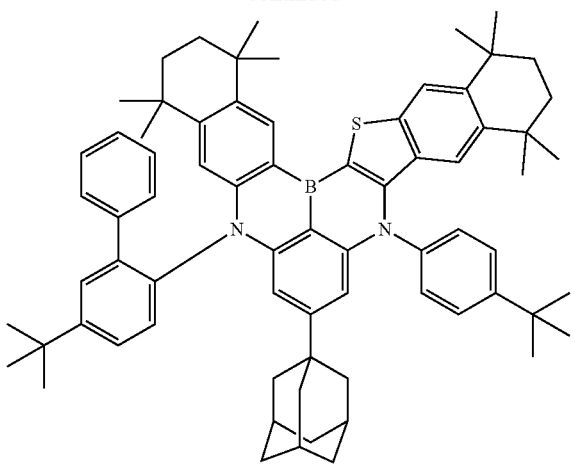
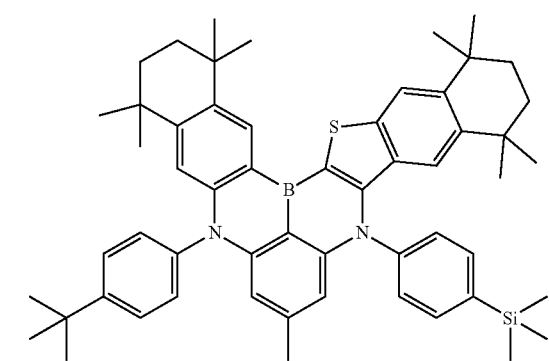
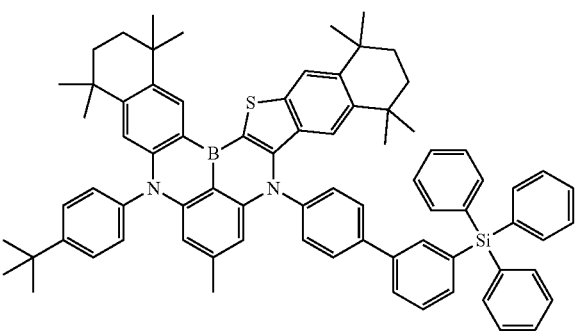
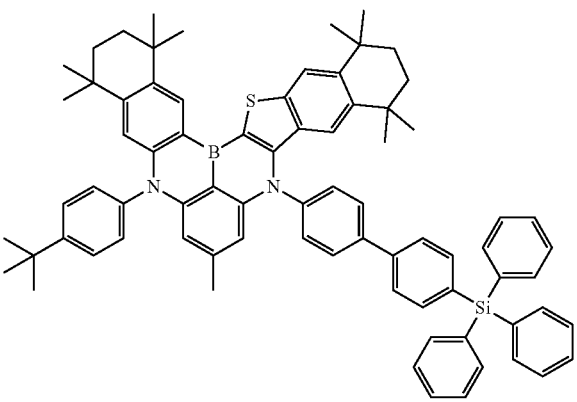
2118
-continued
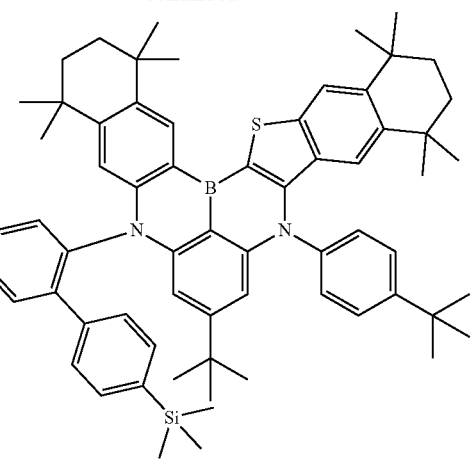
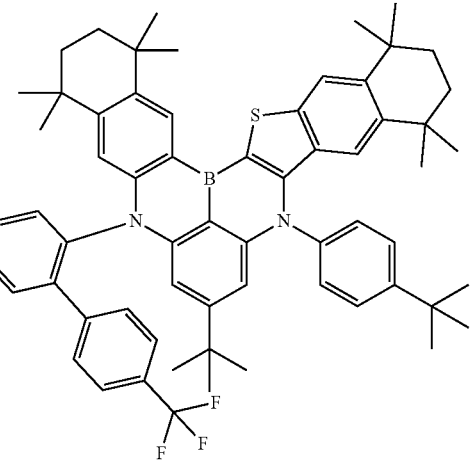
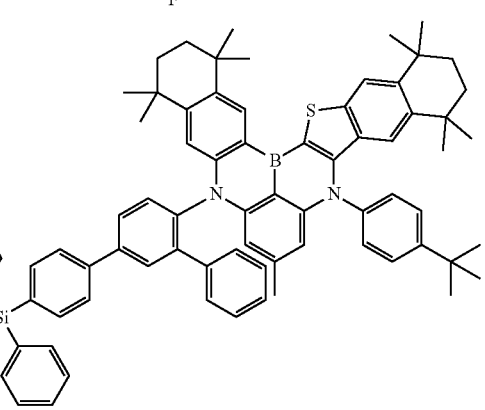
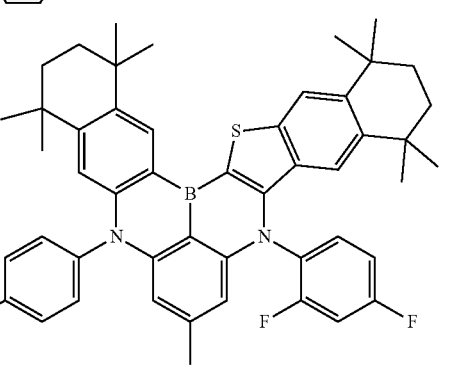

2119
-continued
2120
-continued
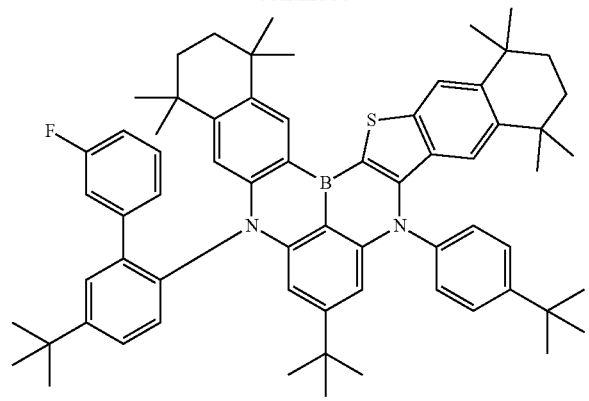
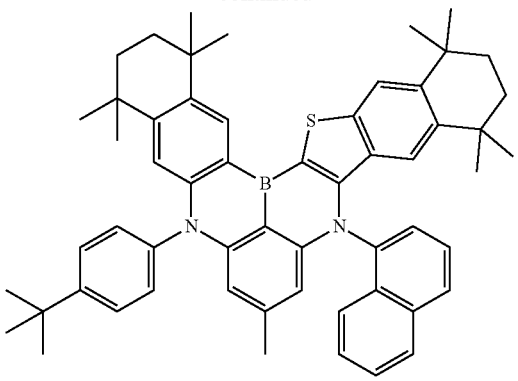
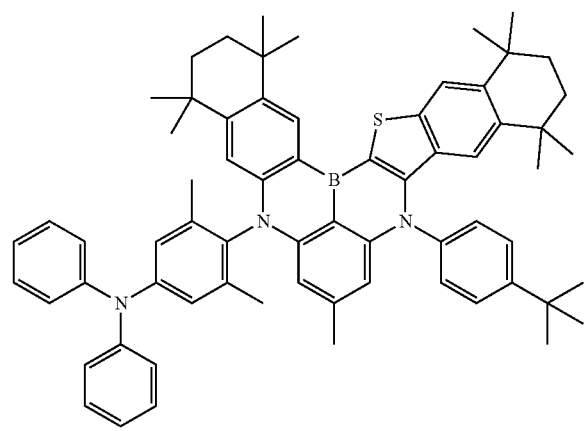
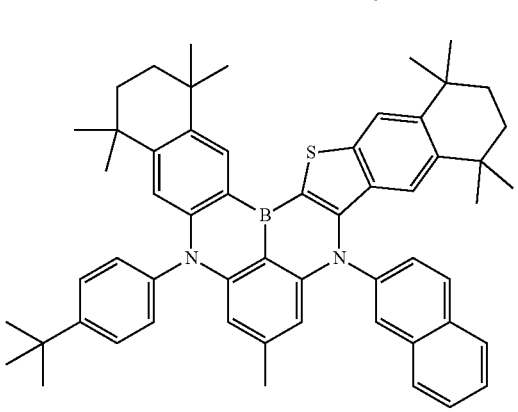
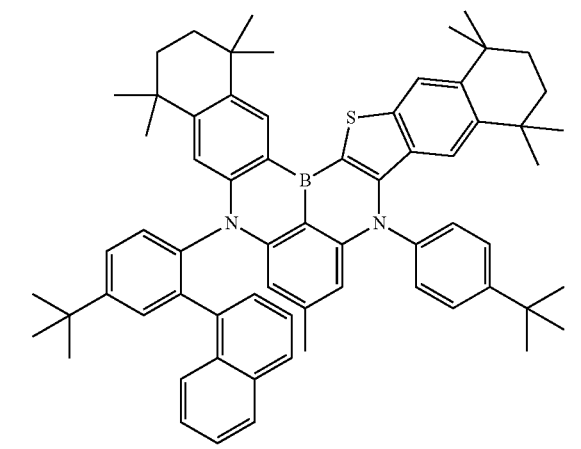
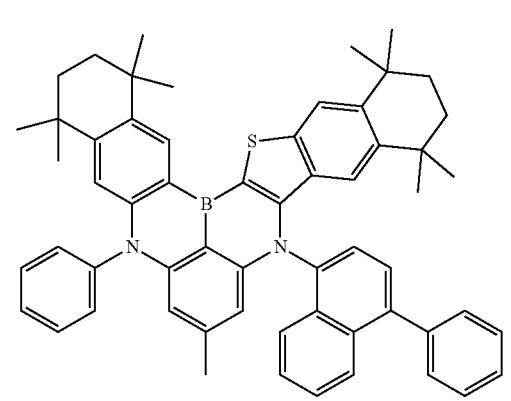
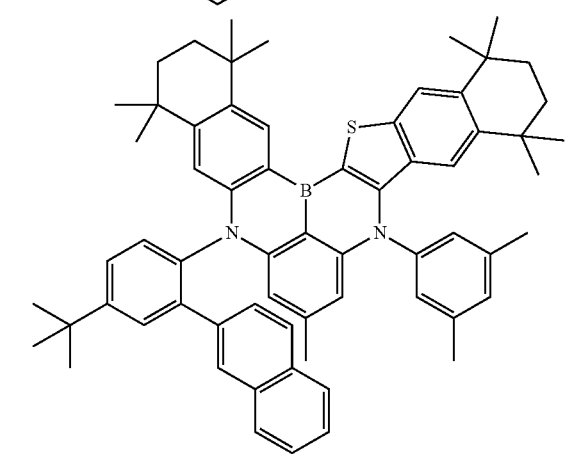
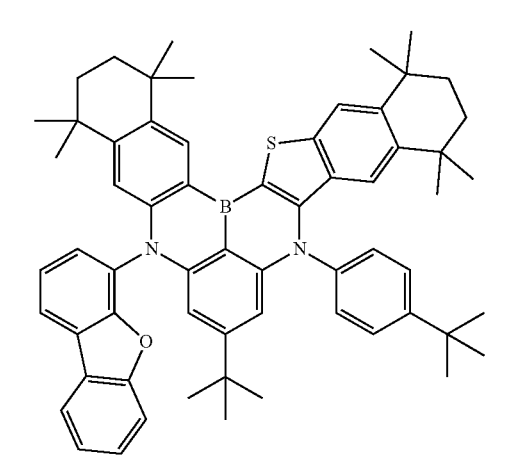

2121
-continued
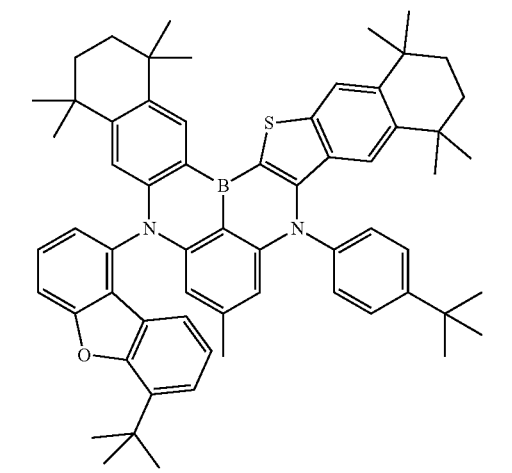
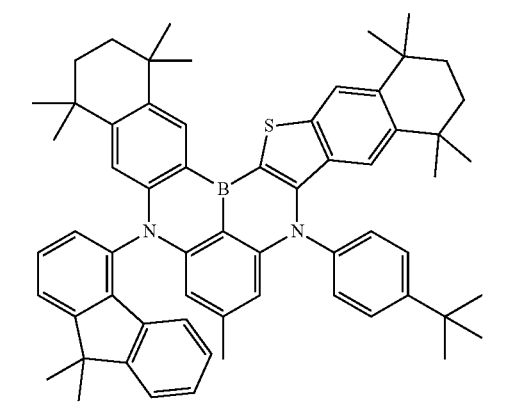
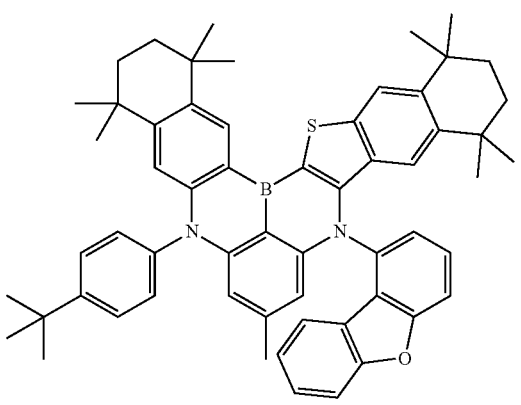
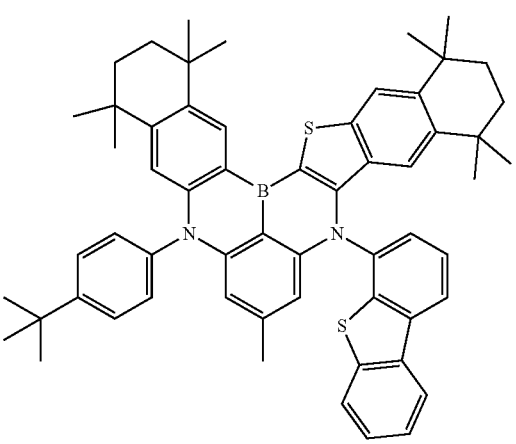
2122
-continued
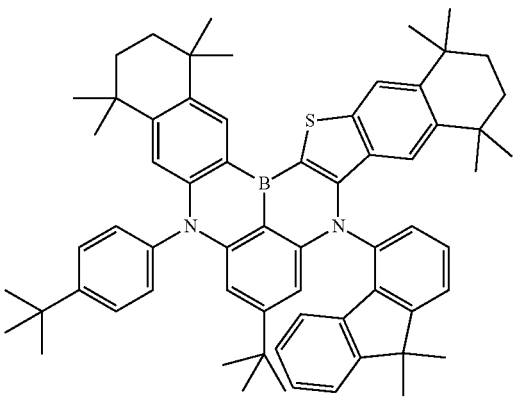
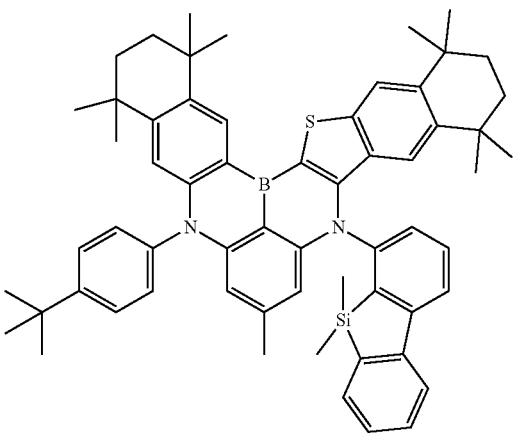
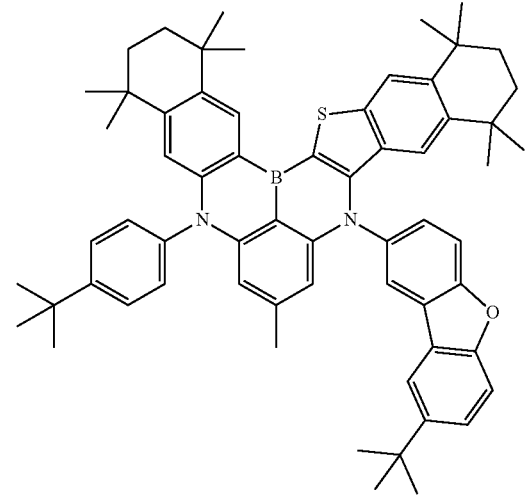

2123
-continued
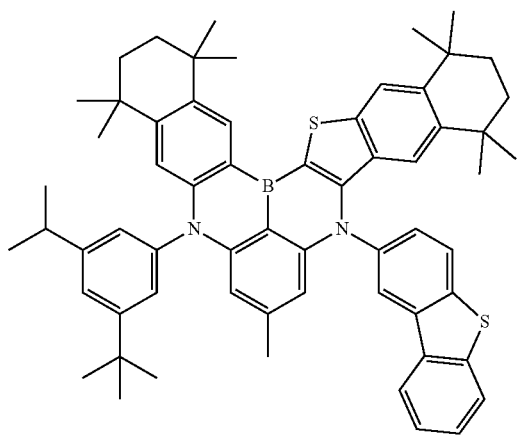
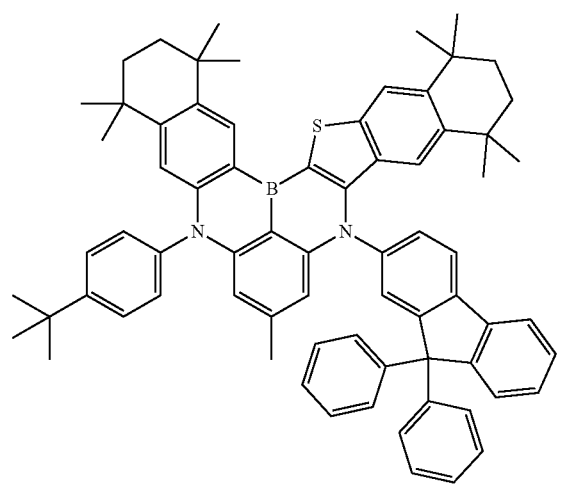
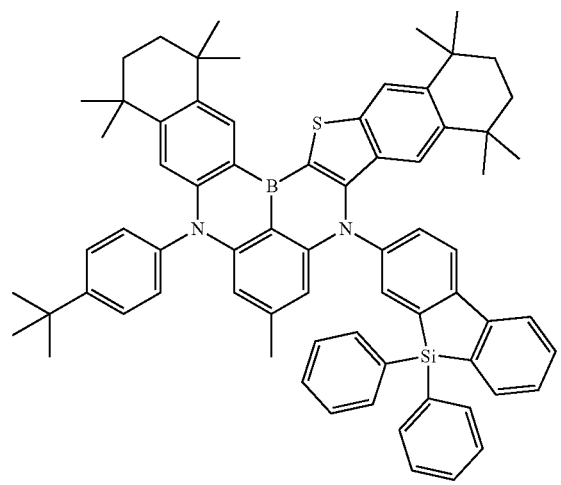
2124
-continued
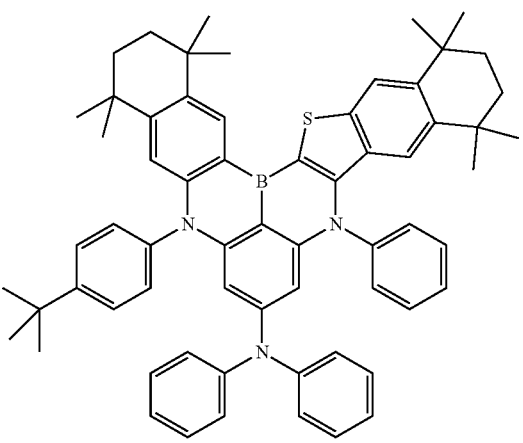
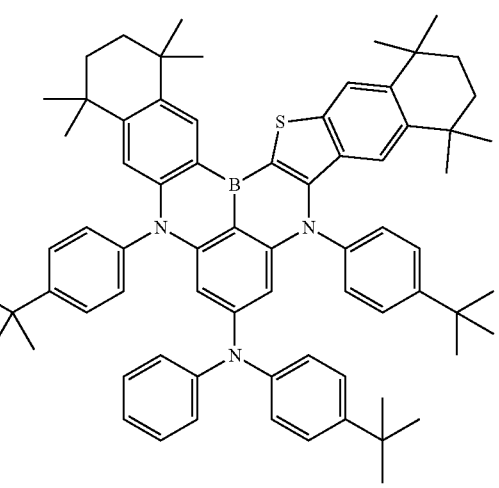
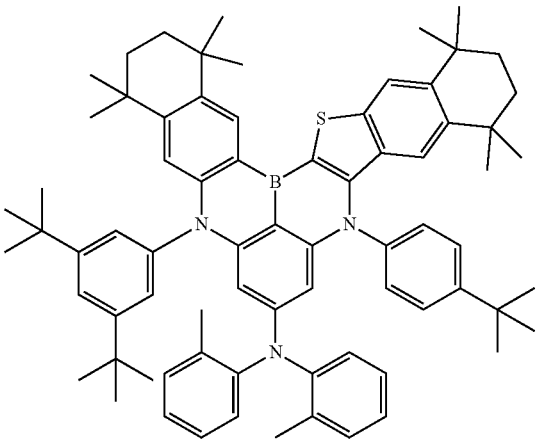

2125
-continued
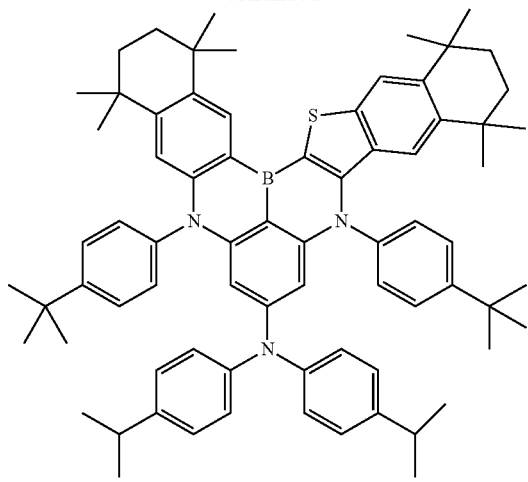
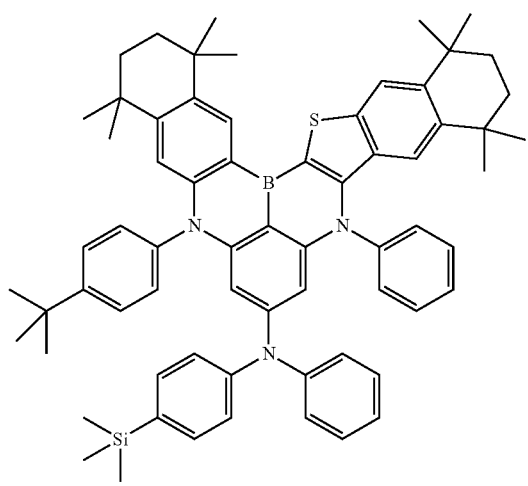
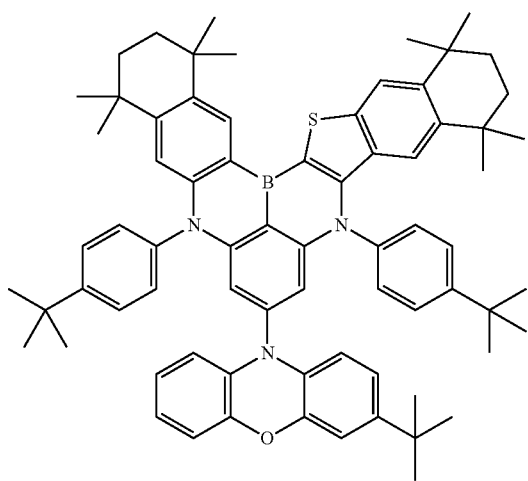
2126
-continued
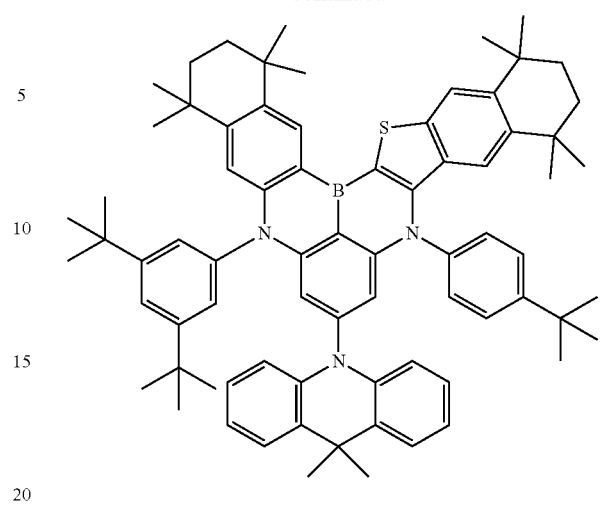
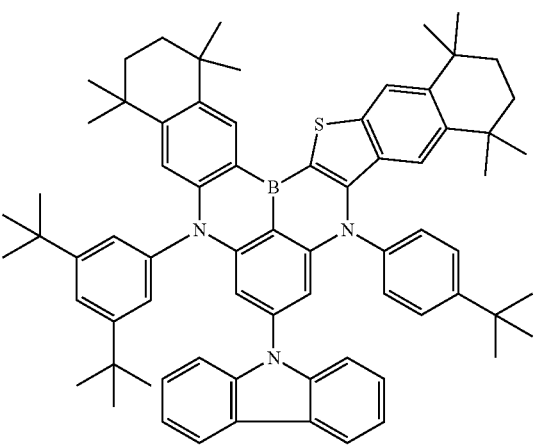
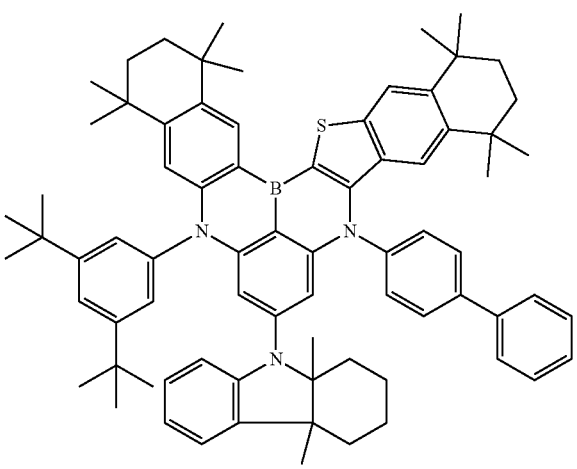

2127
-continued
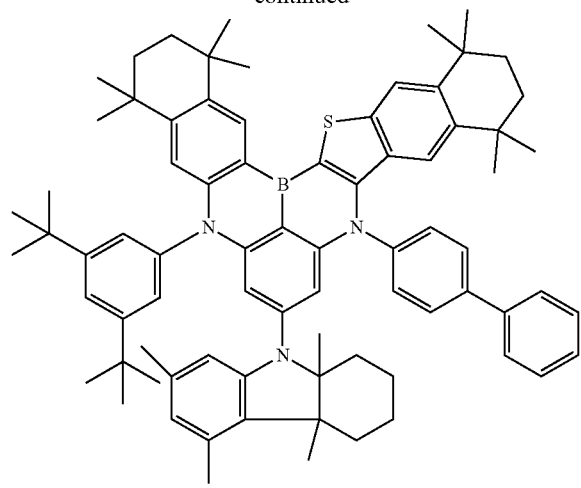
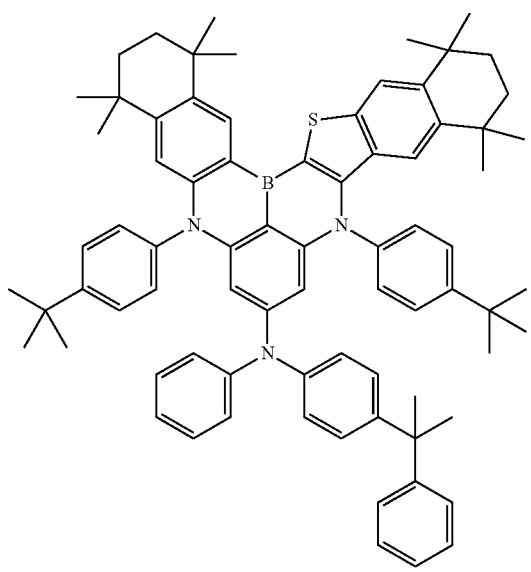
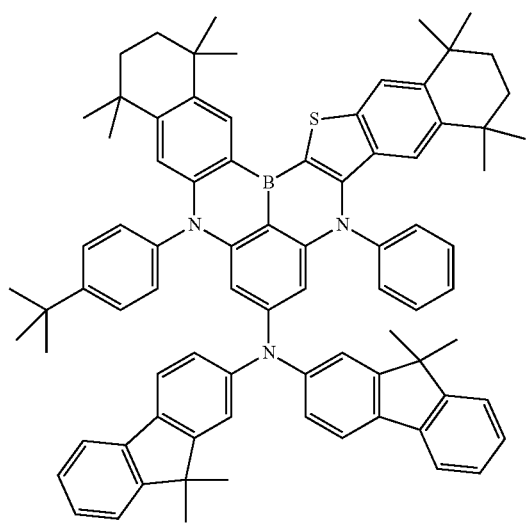
2128
-continued
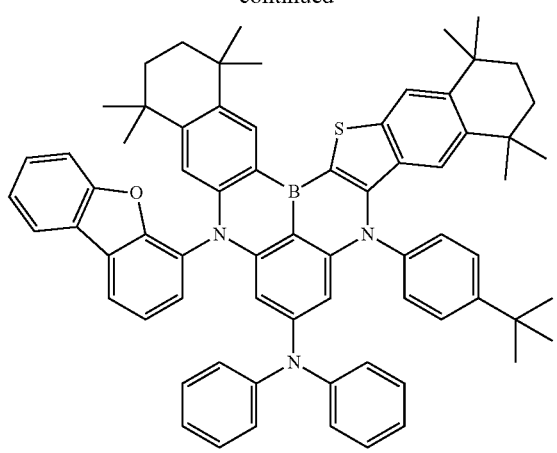
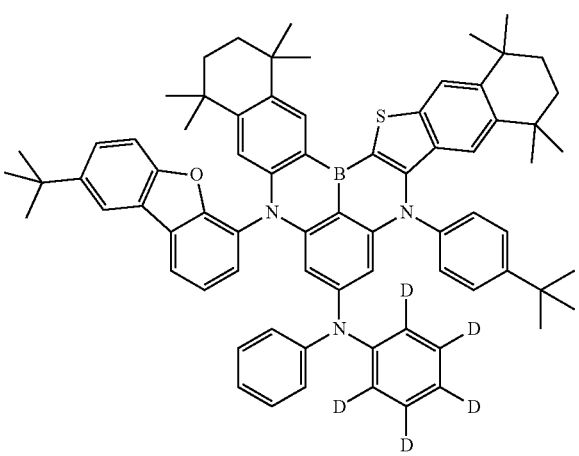
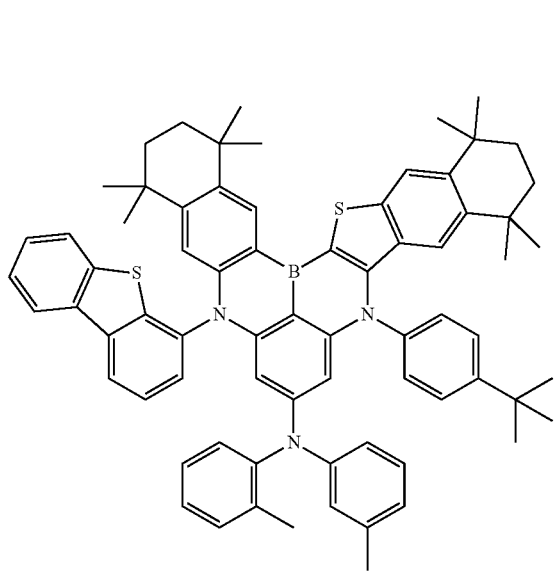

2129
-continued
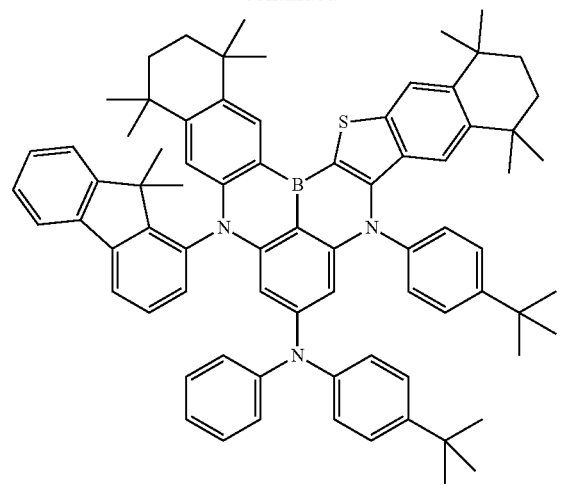
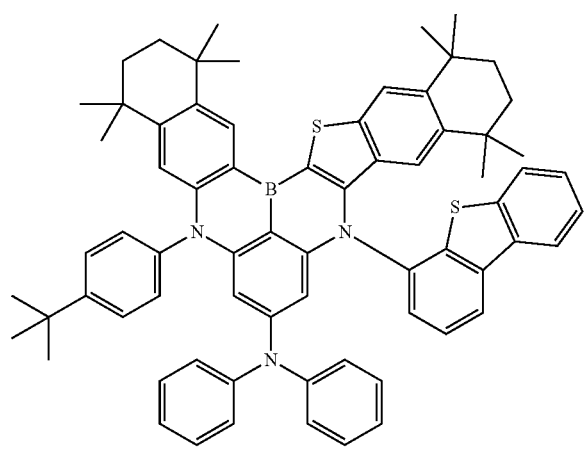
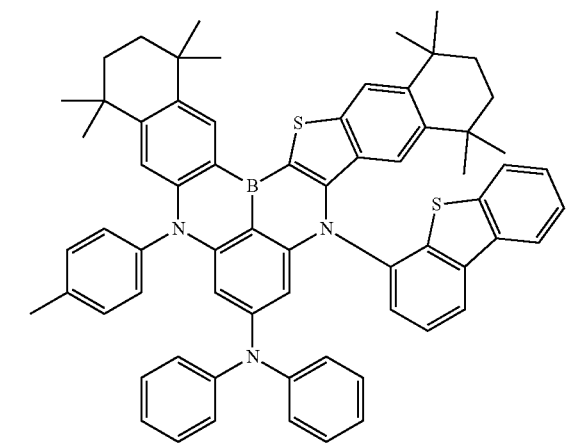
2130
-continued
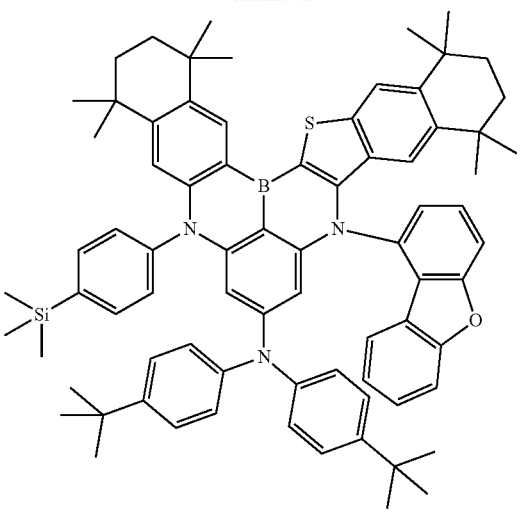
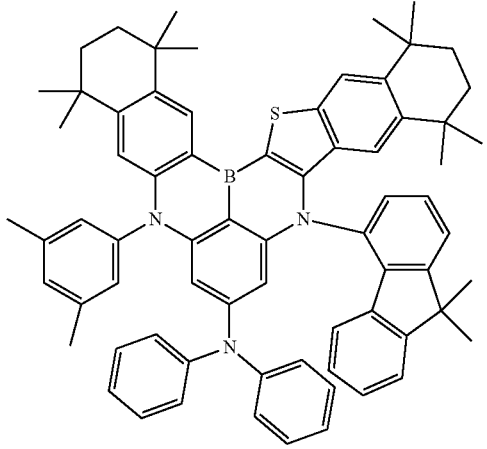
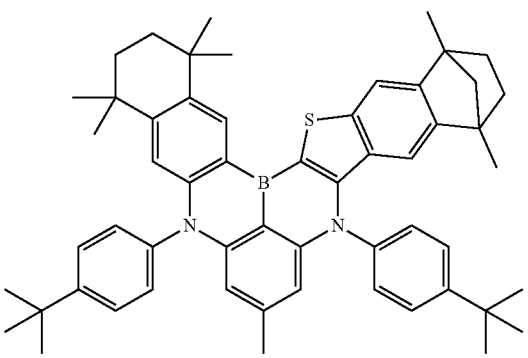
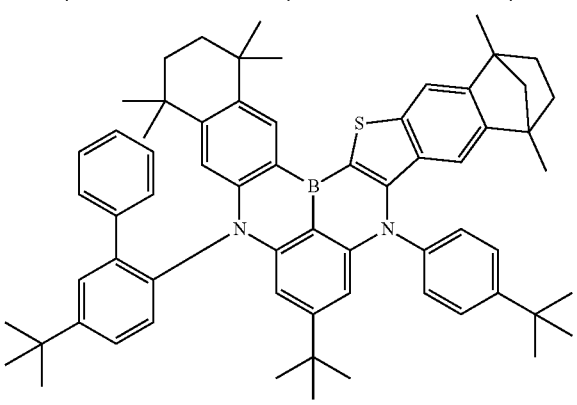

2131
-continued
2132
-continued
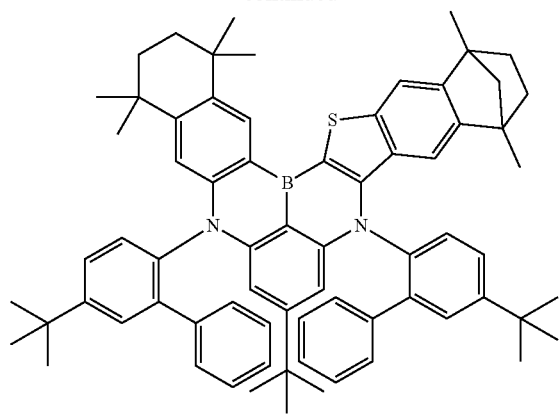
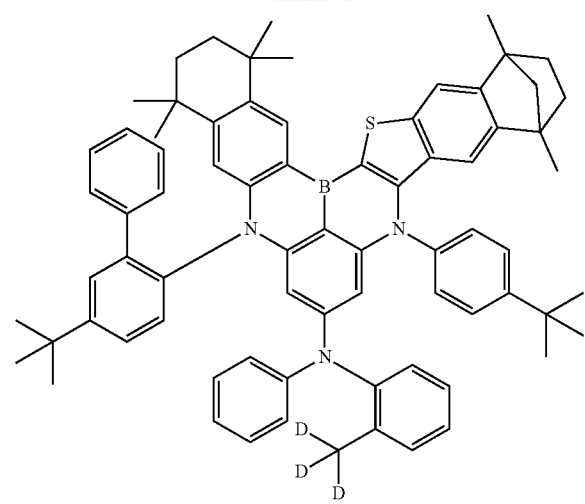
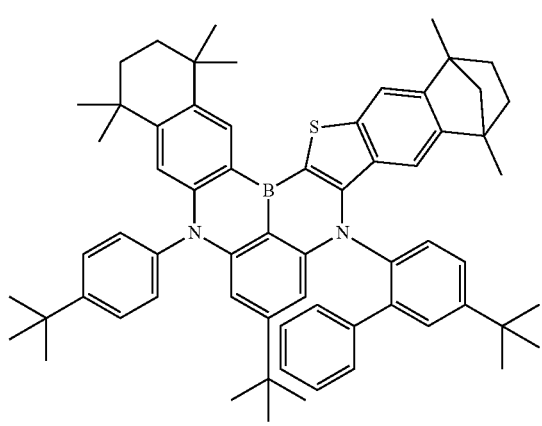
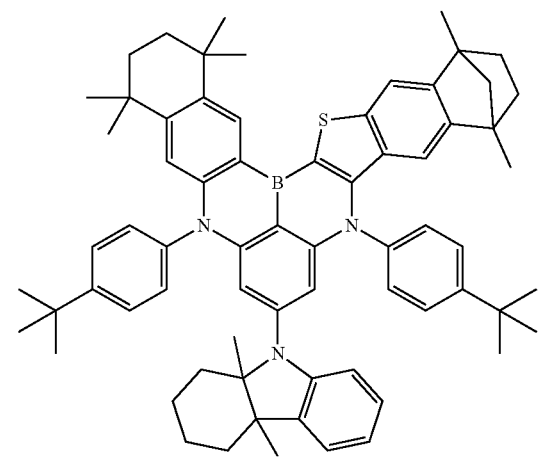
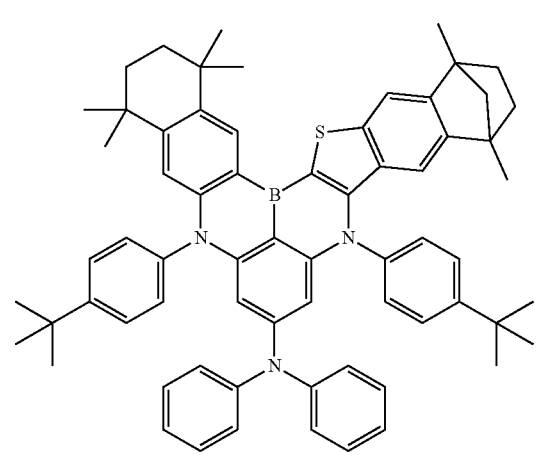
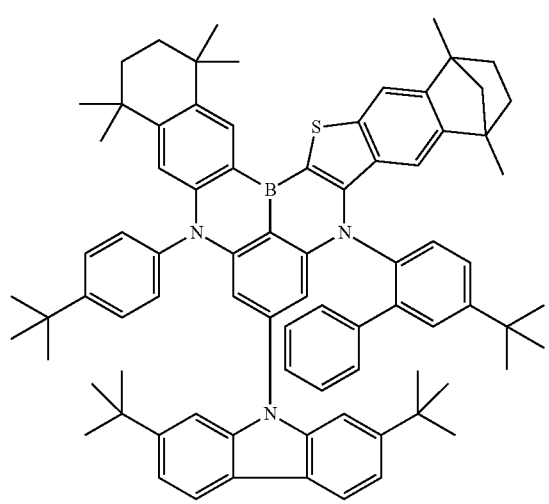

2133
-continued
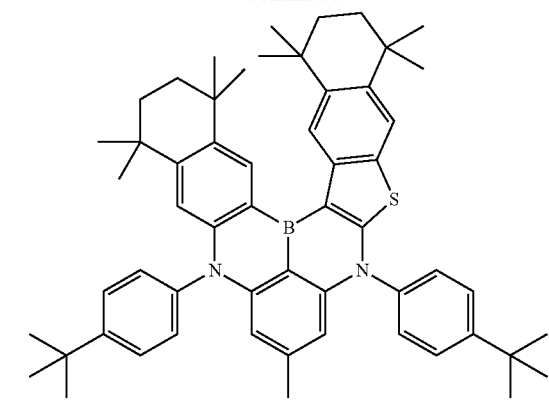
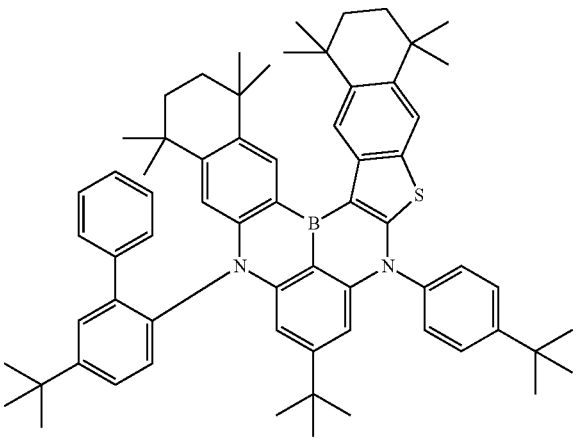
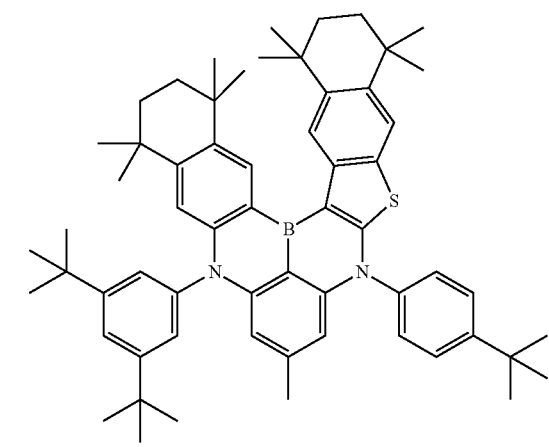
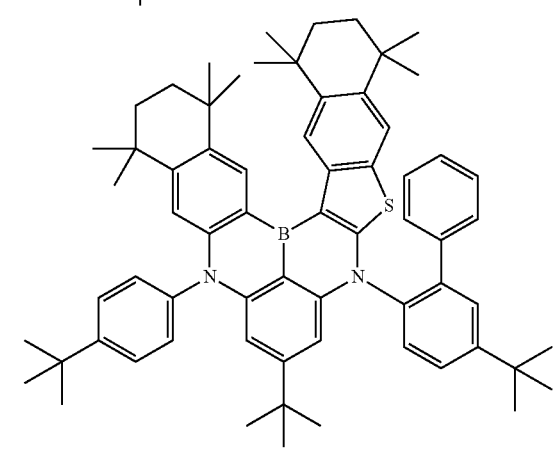
2134
-continued
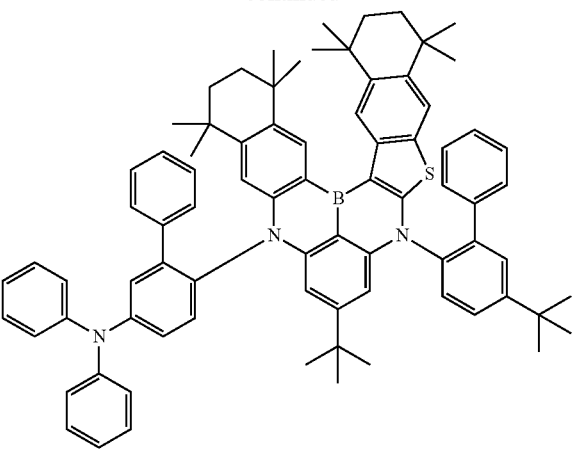
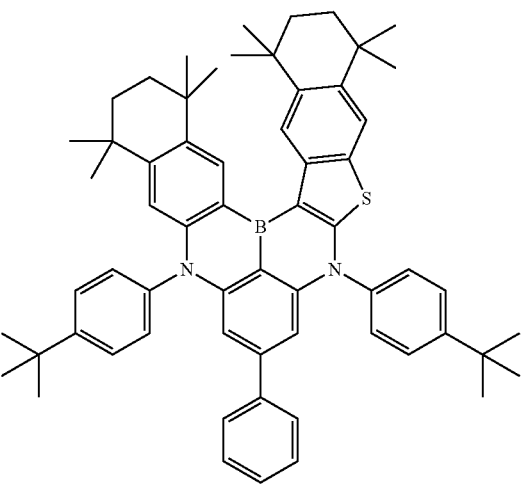
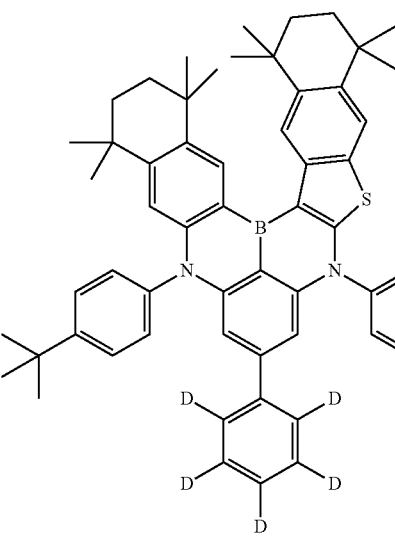

2135
-continued
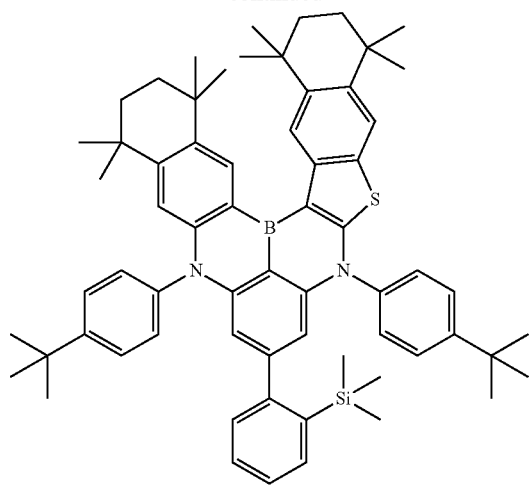
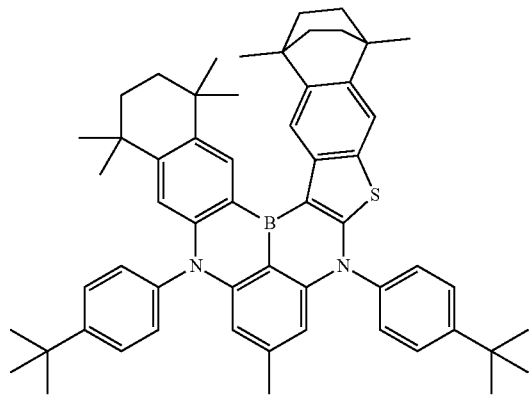
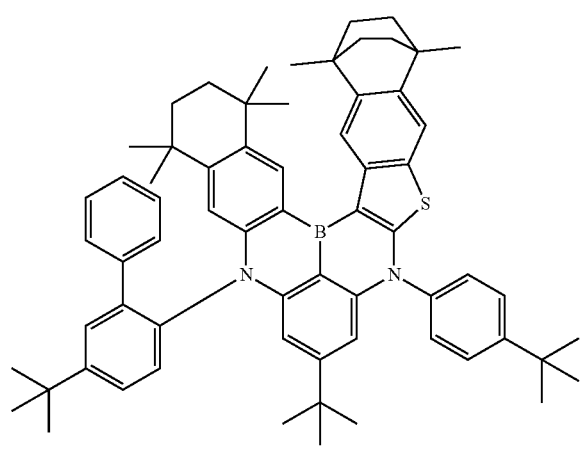
2136
-continued
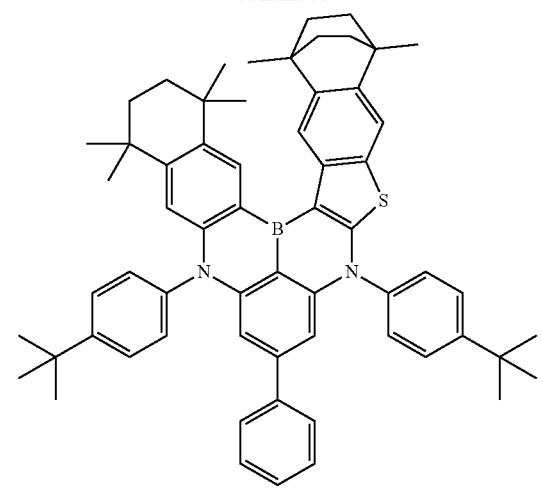
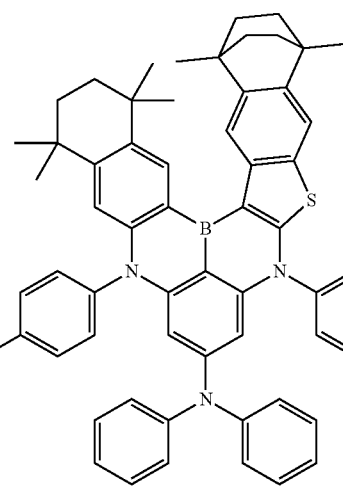
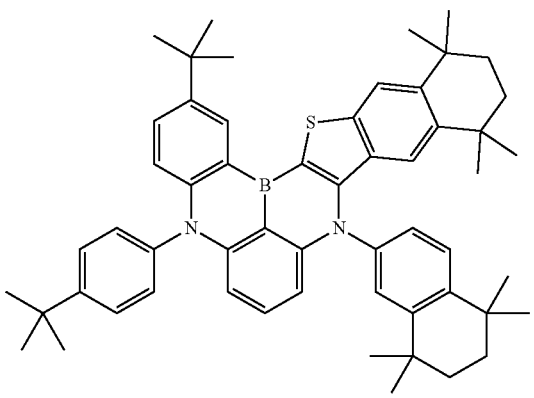

2137
-continued
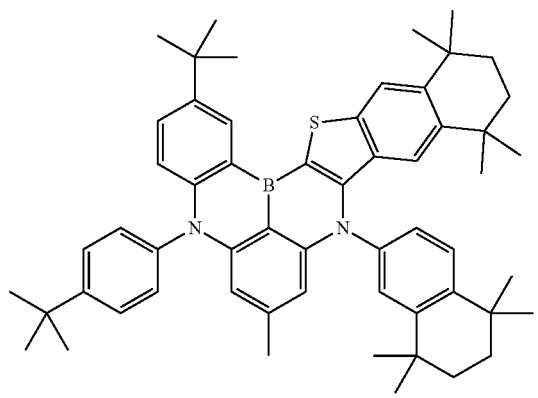
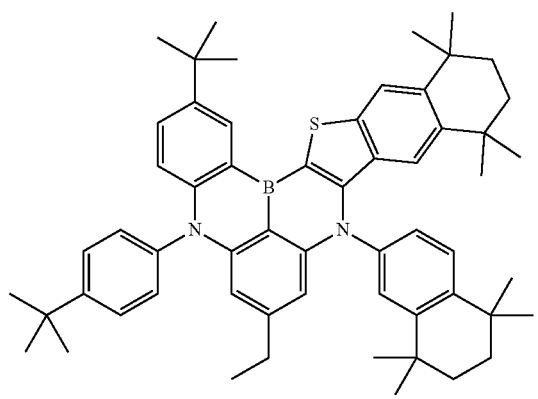
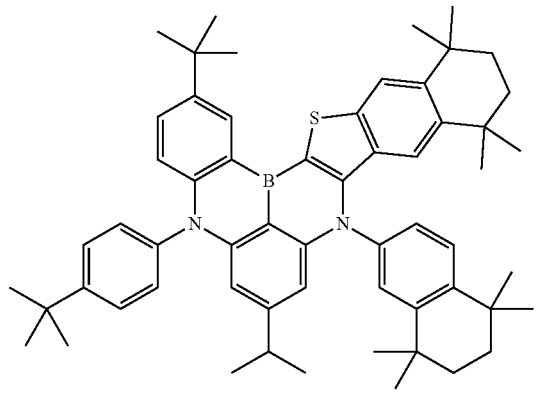
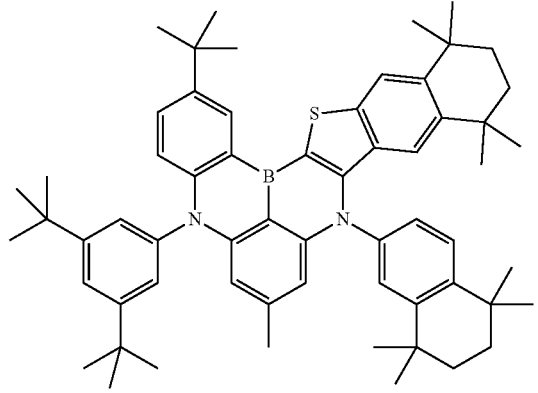
2138
-continued
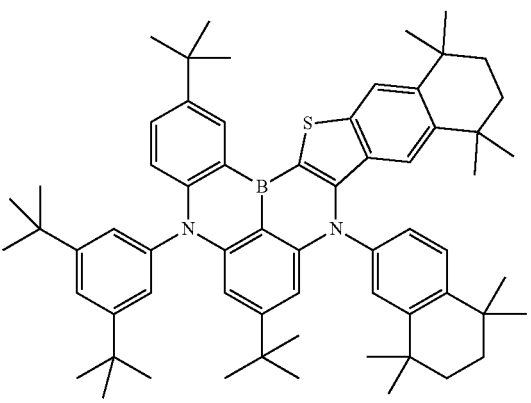
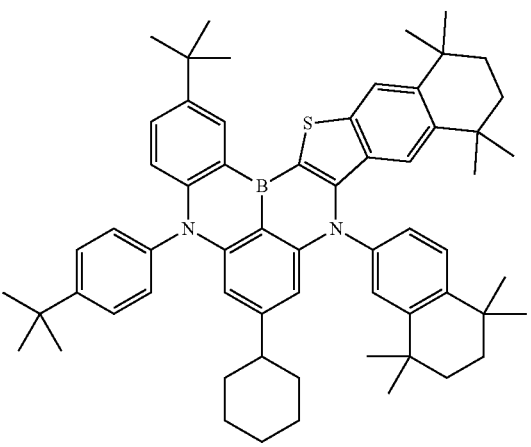
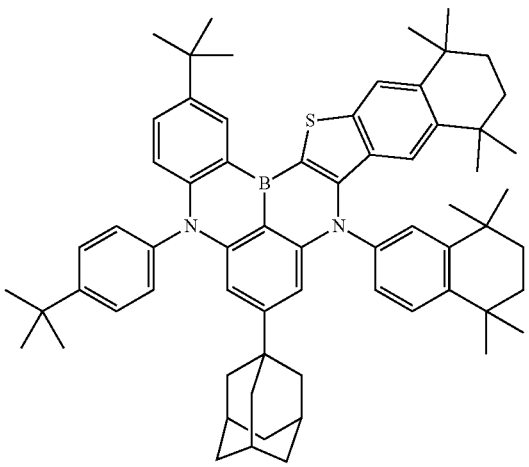
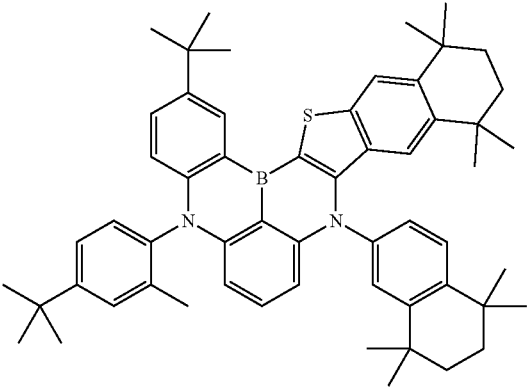

2139
-continued
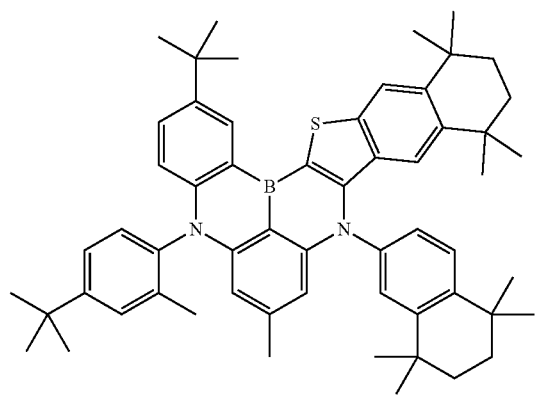
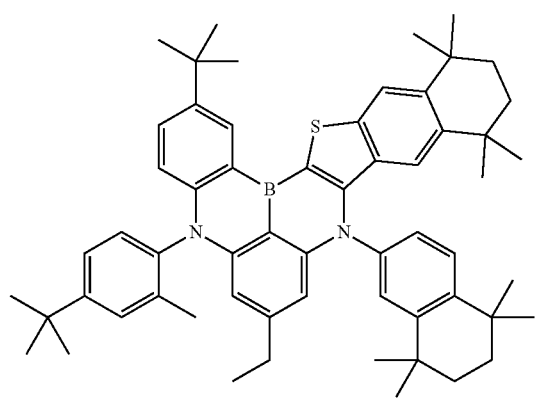
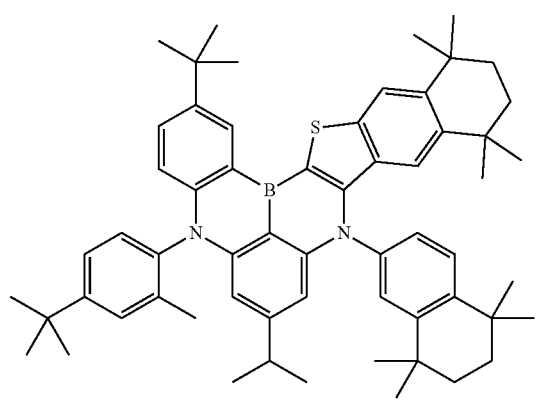
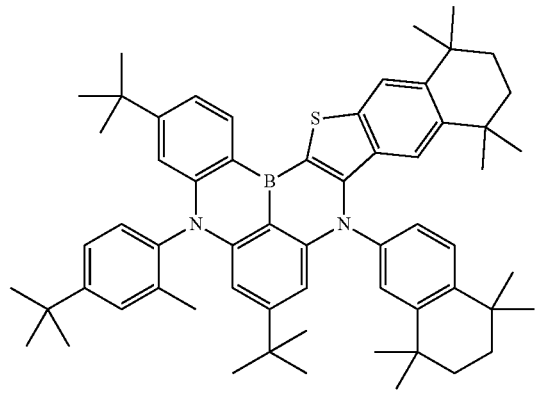
2140
-continued
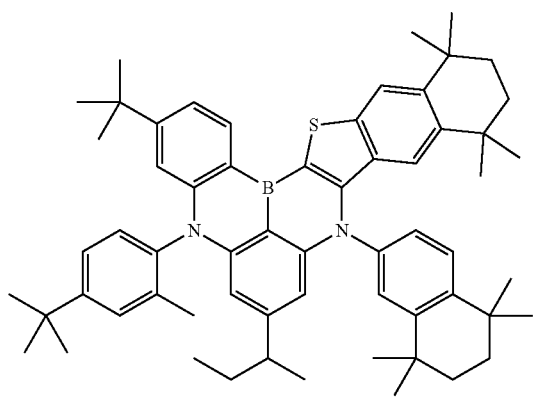
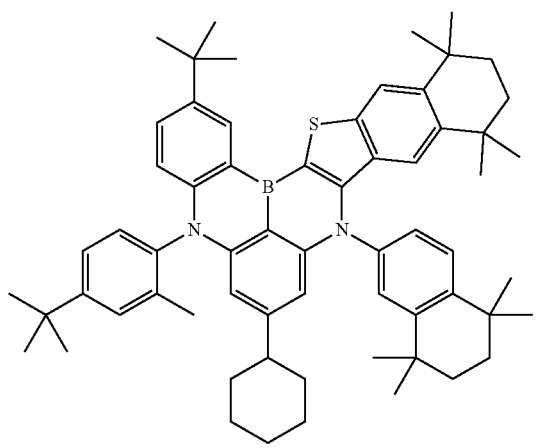
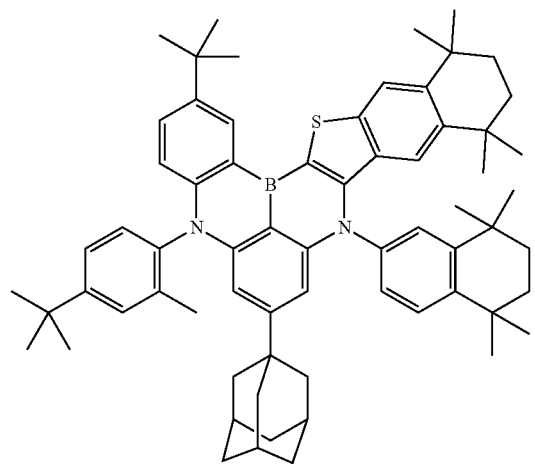
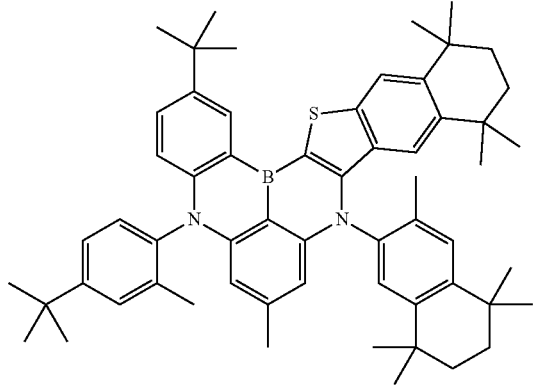

2141
-continued
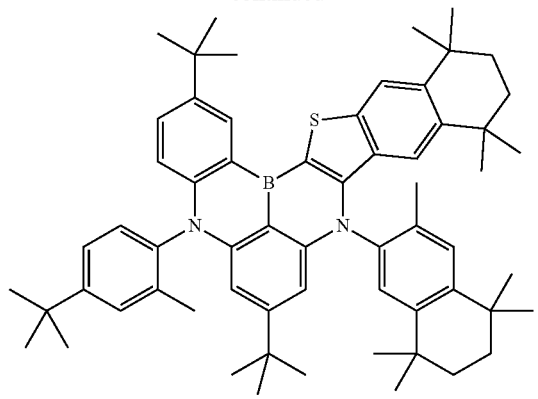
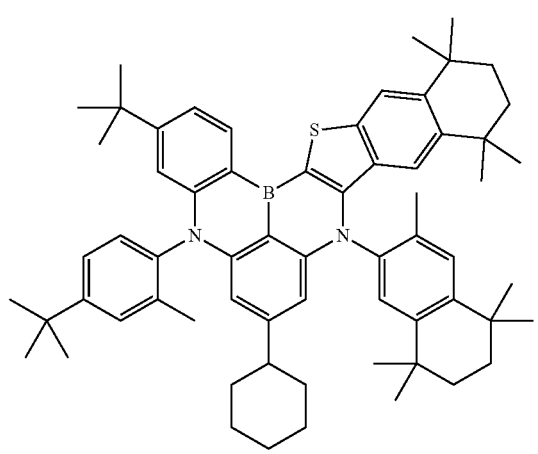
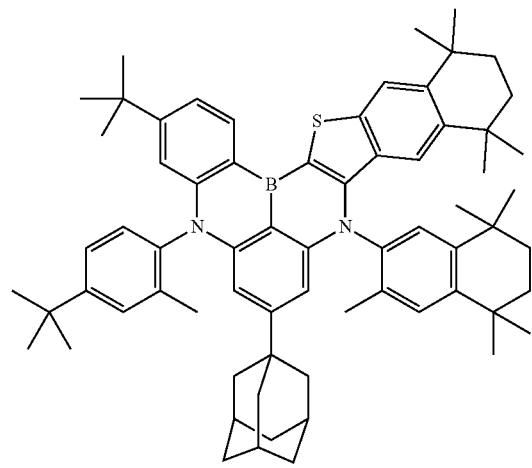
2142
-continued
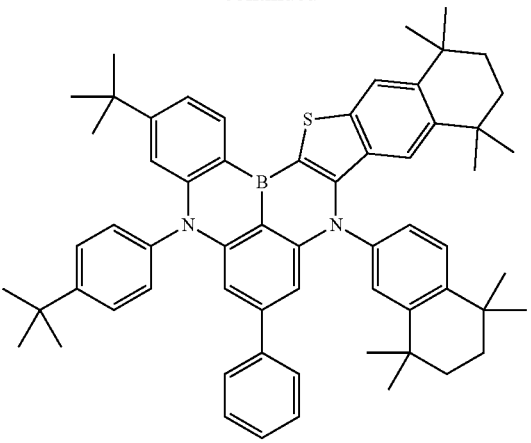
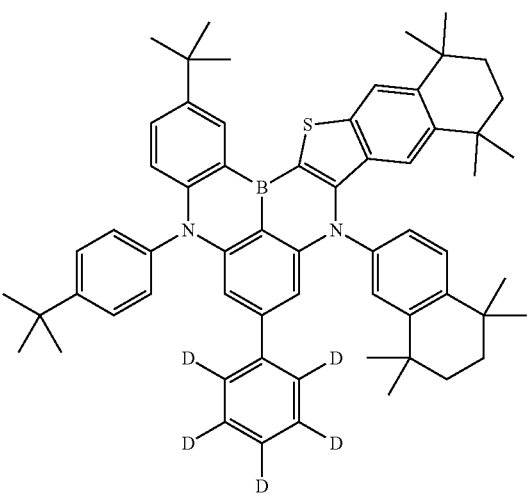
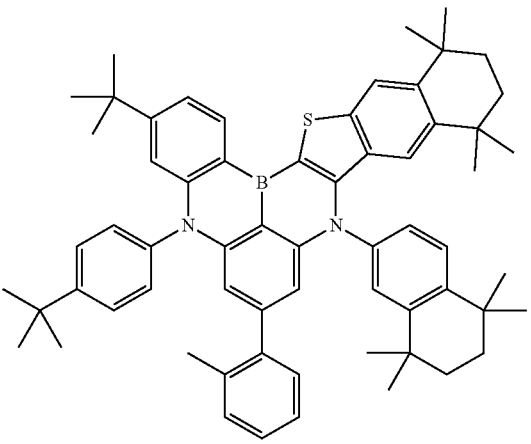

2143
-continued
2144
-continued
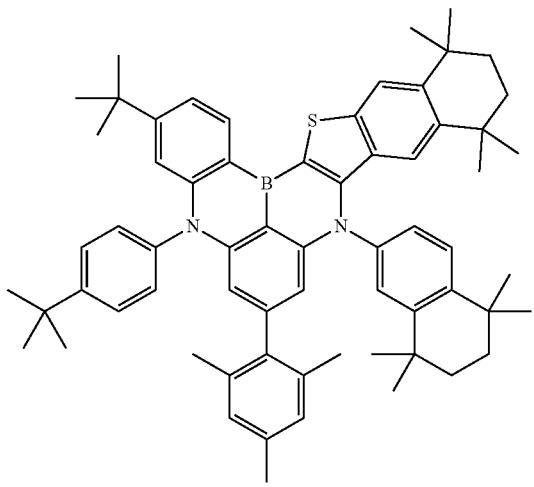
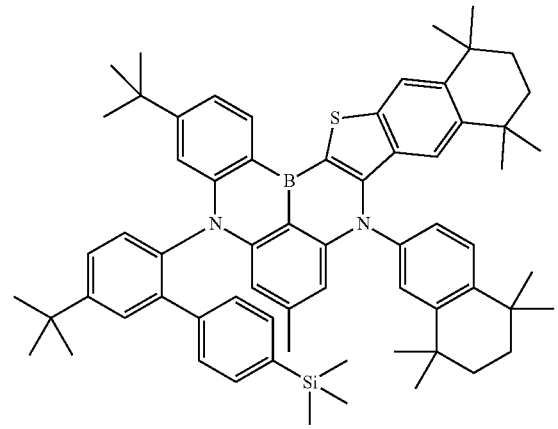

2145
-continued
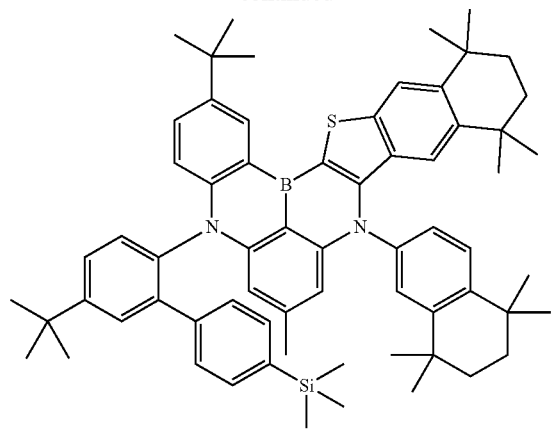
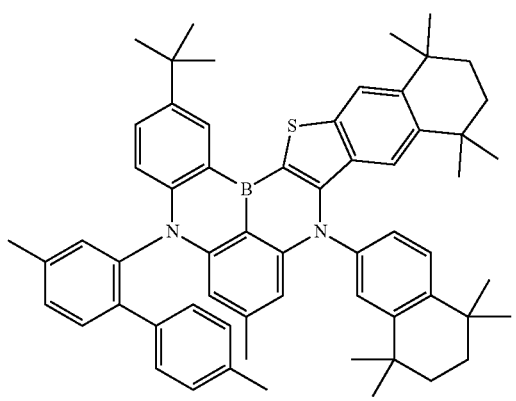
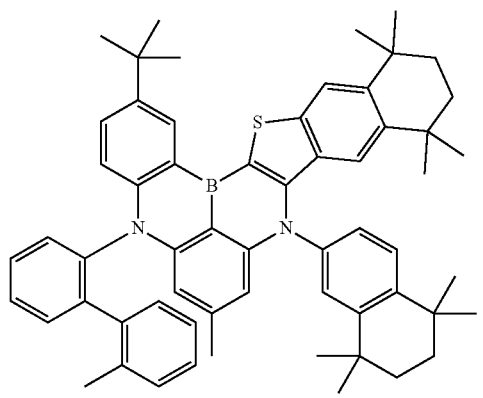
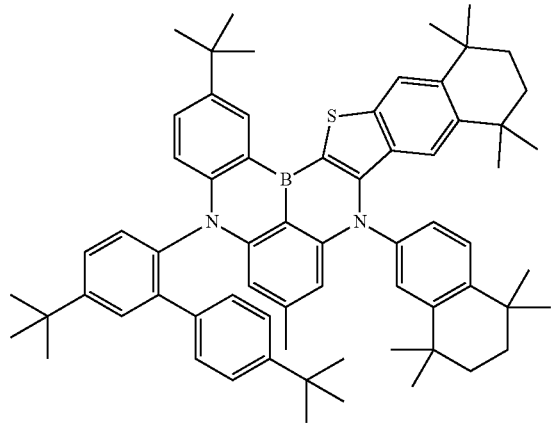
2146
-continued
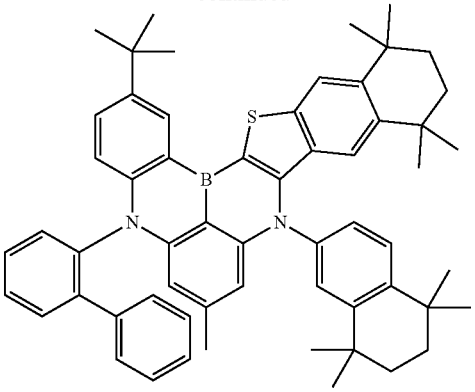
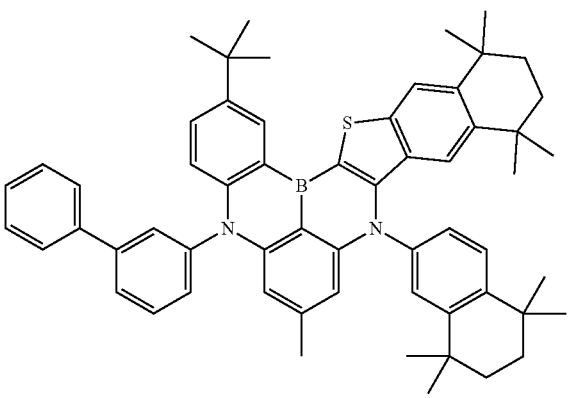
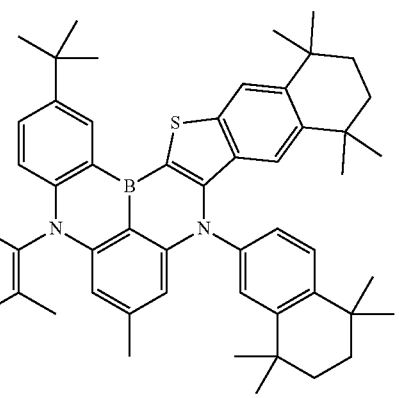
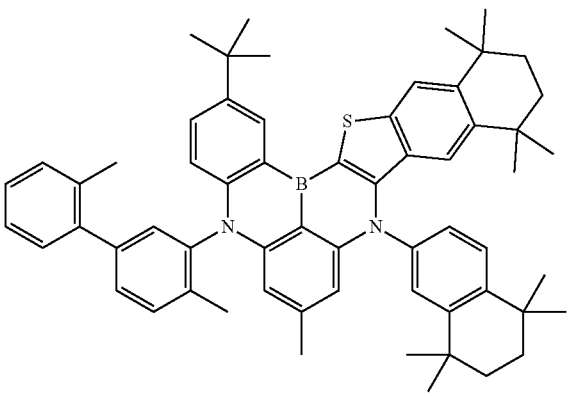

2147
-continued
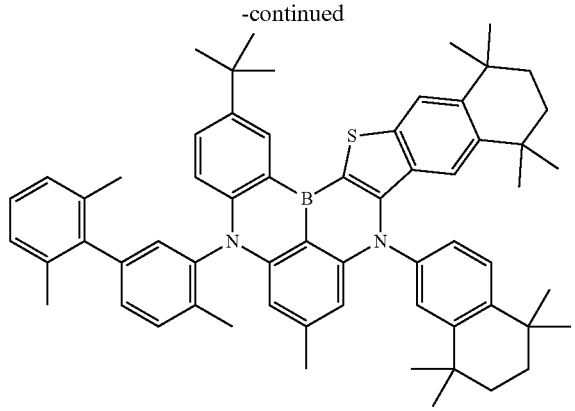
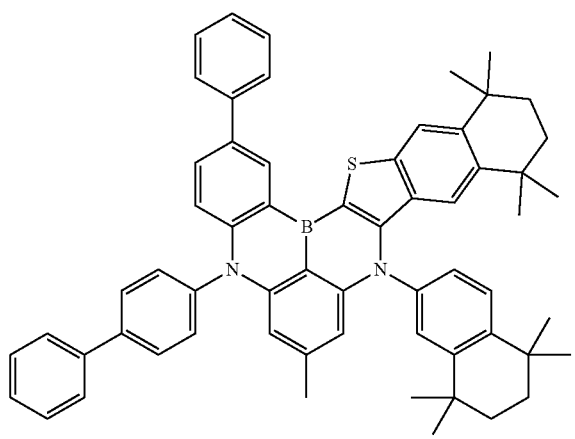
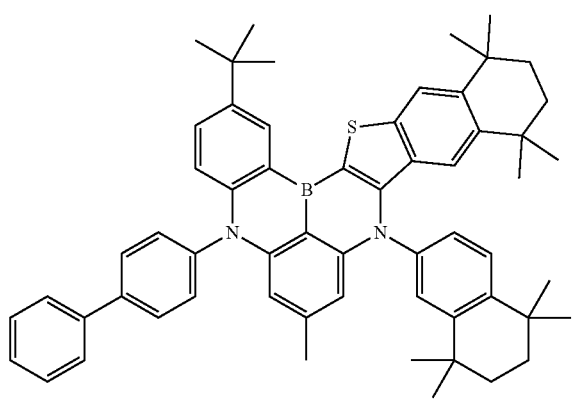
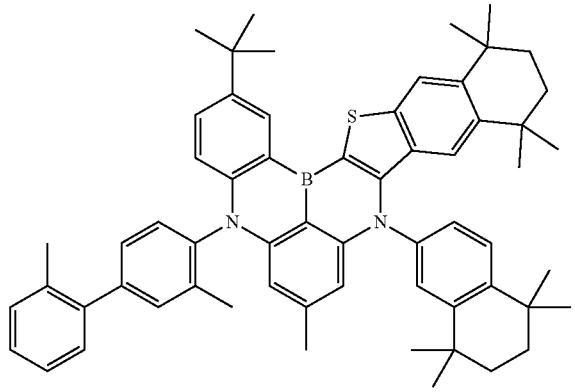
2148
-continued
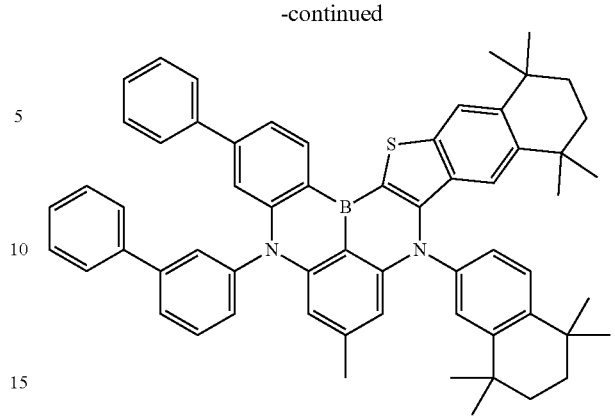
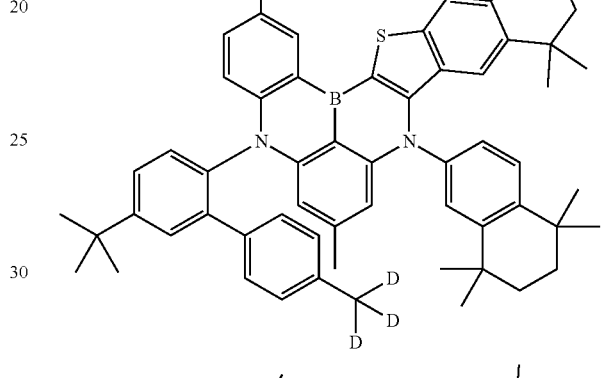
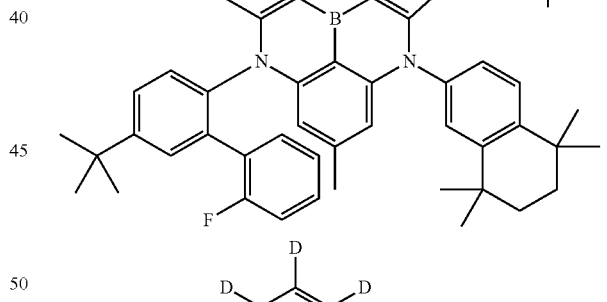
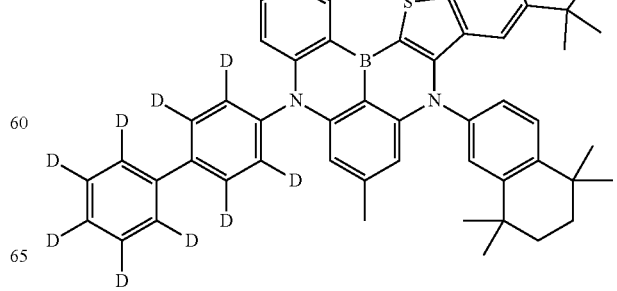

2149
-continued
2150
-continued
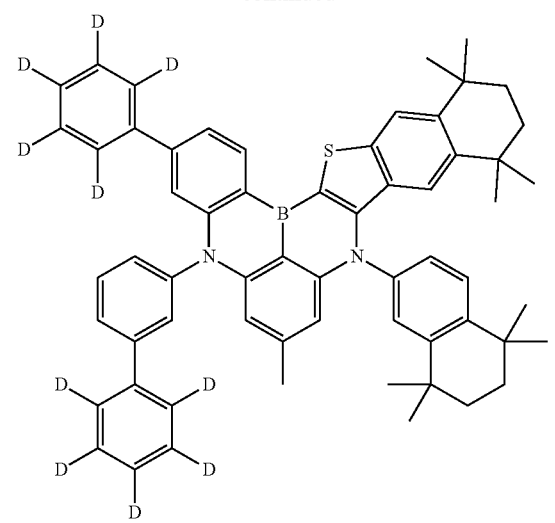
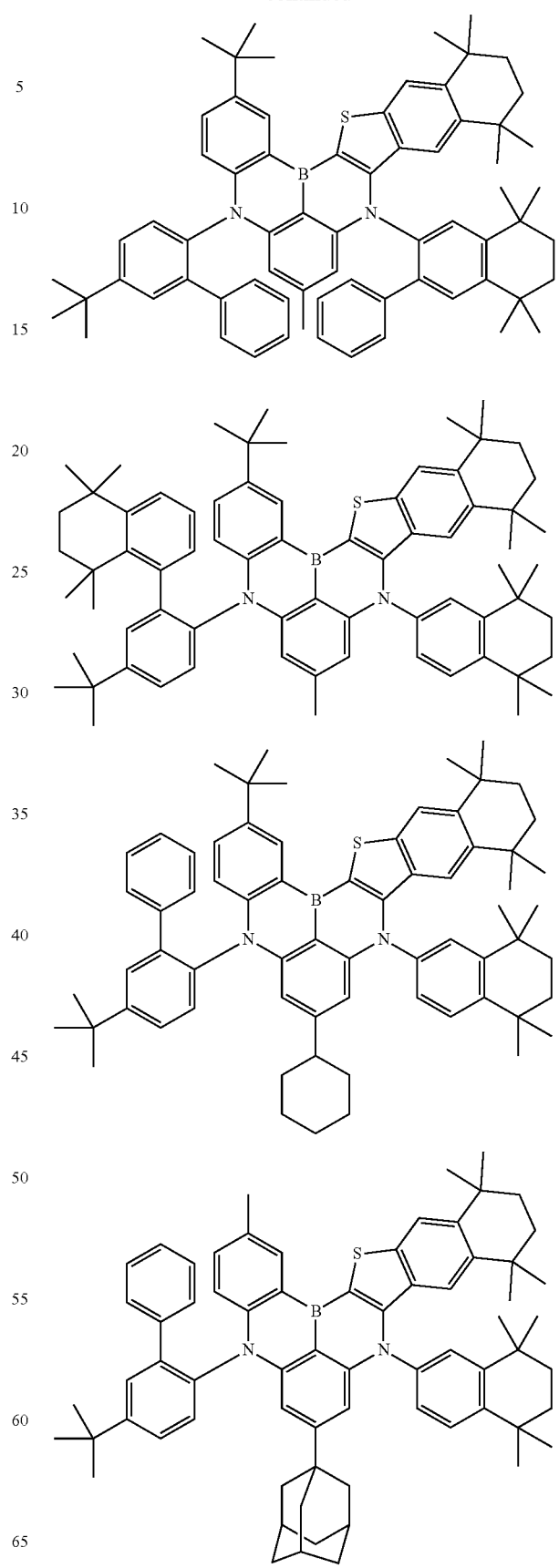

2151
-continued
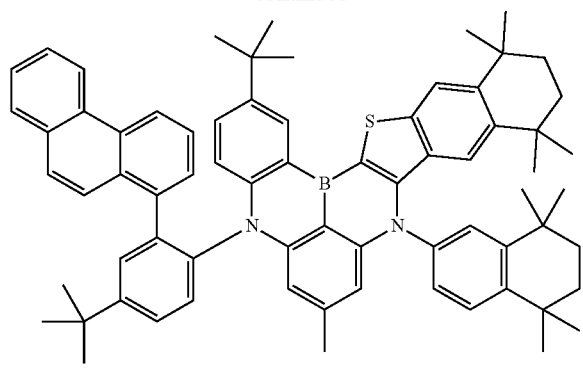
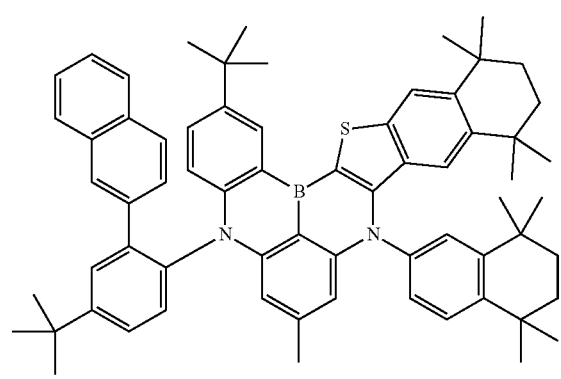
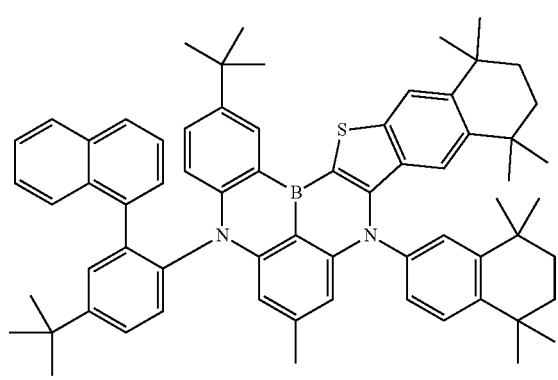
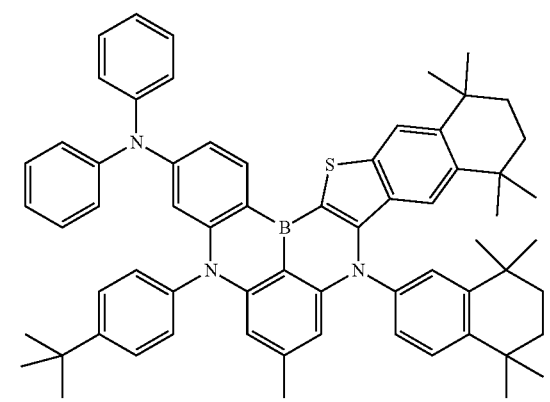
2152
-continued
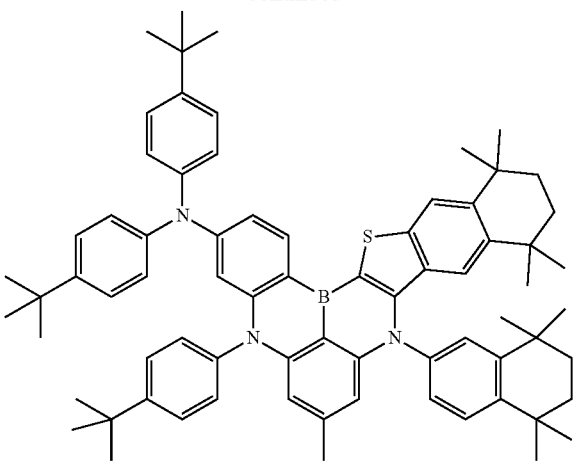
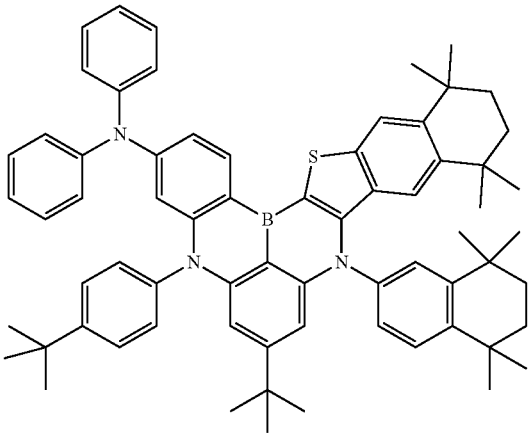
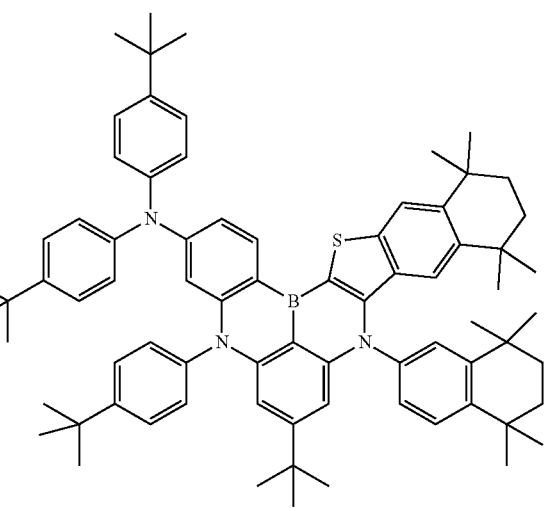

2153
-continued
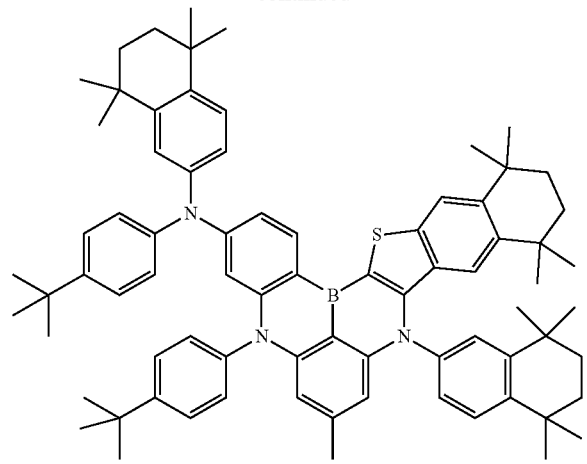
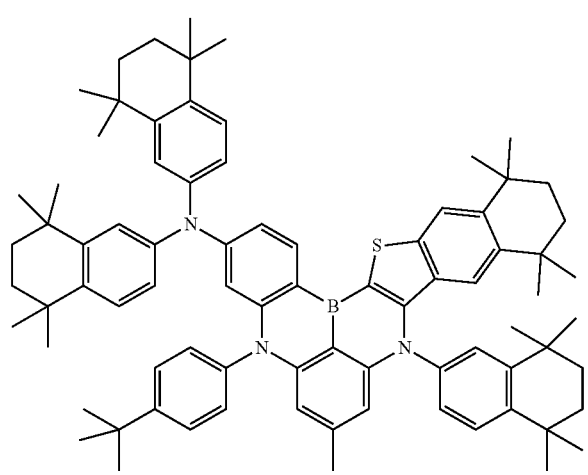
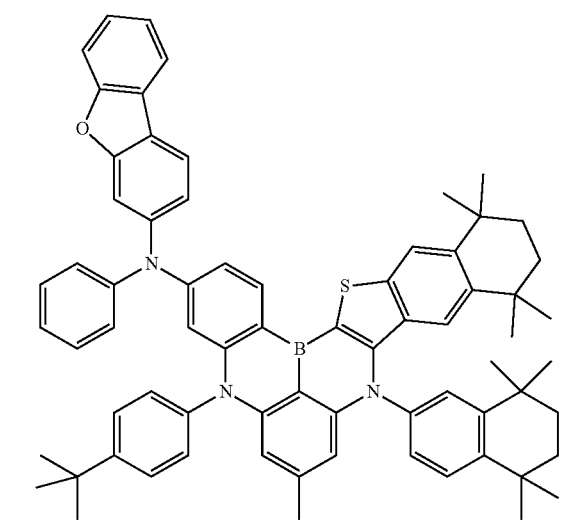
2154
-continued
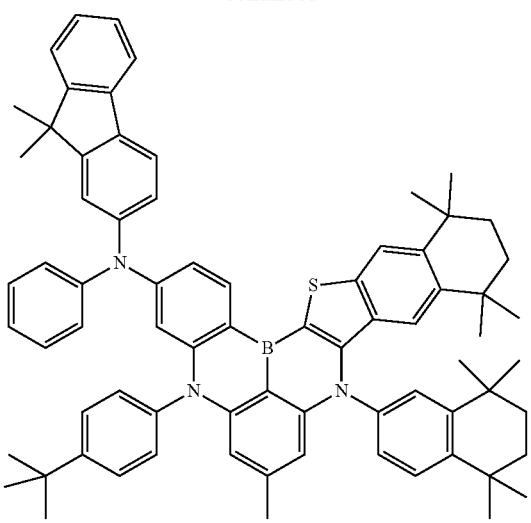
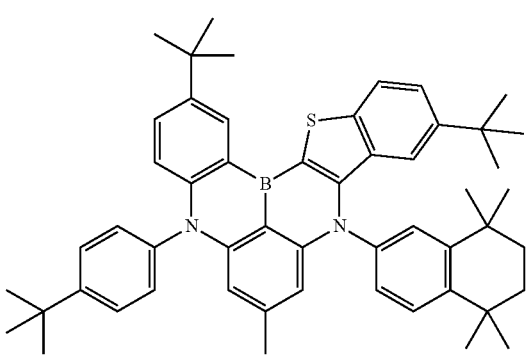
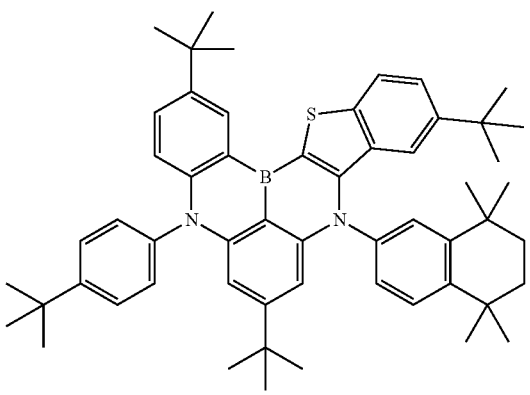
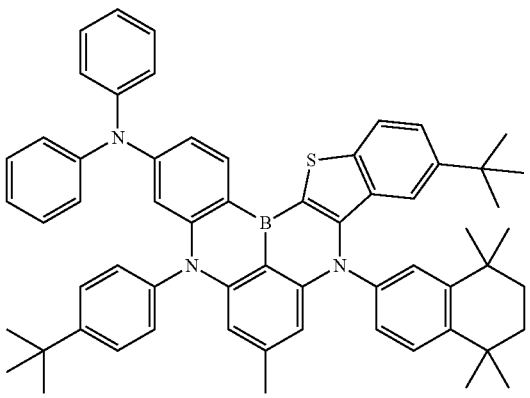

2155
-continued
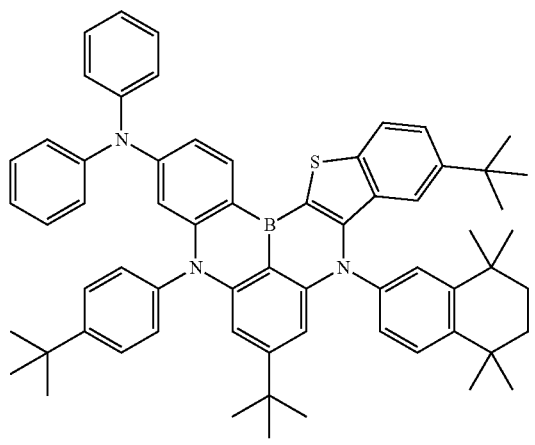
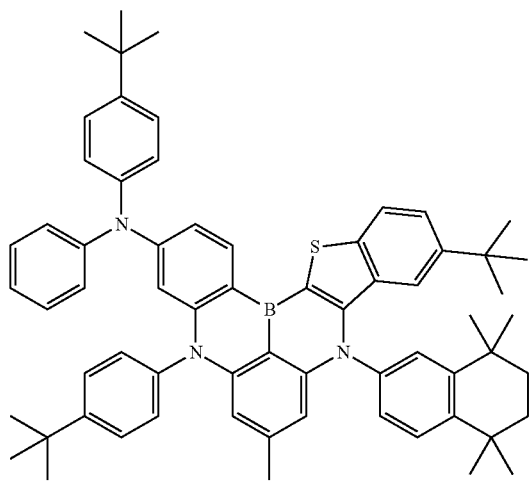
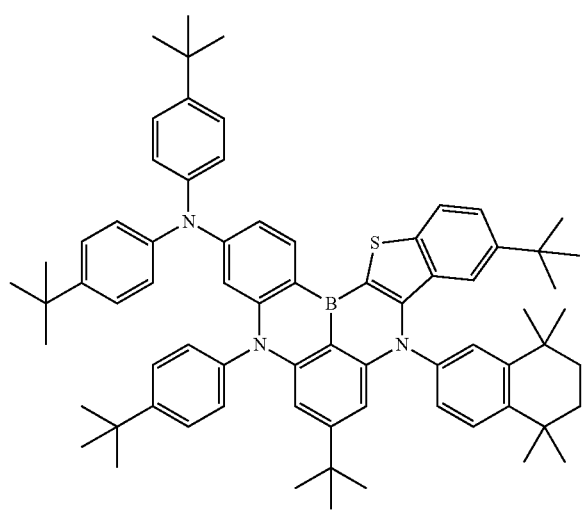
2156
-continued
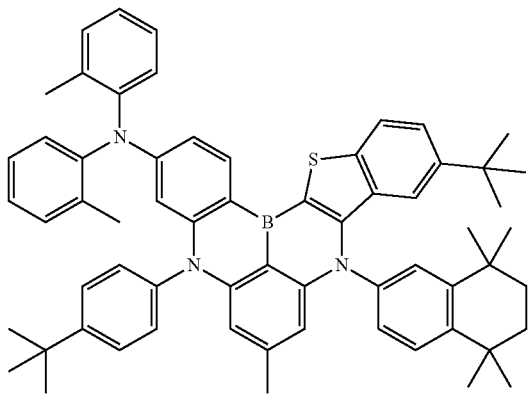
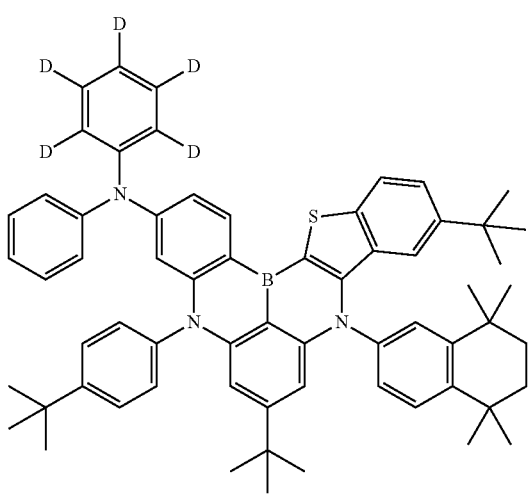
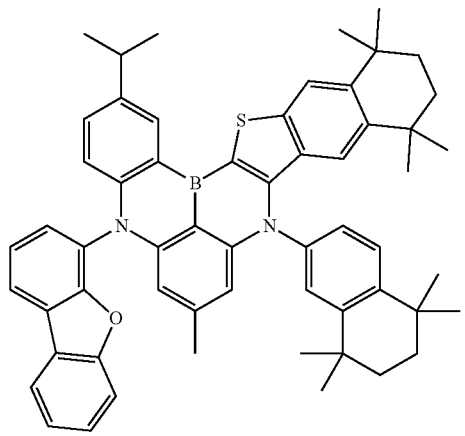

2157
-continued
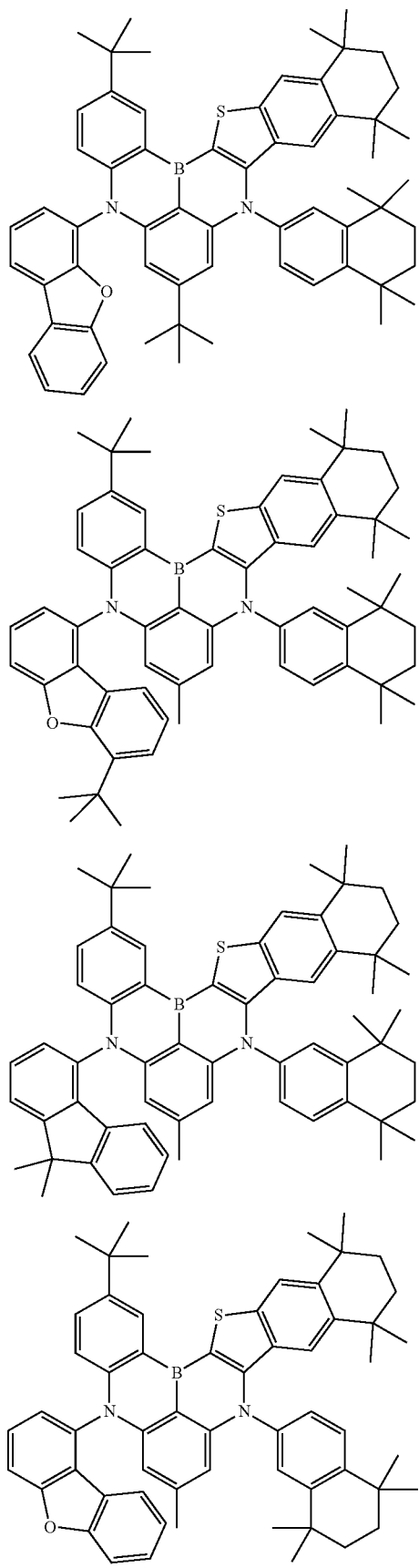
2158
-continued
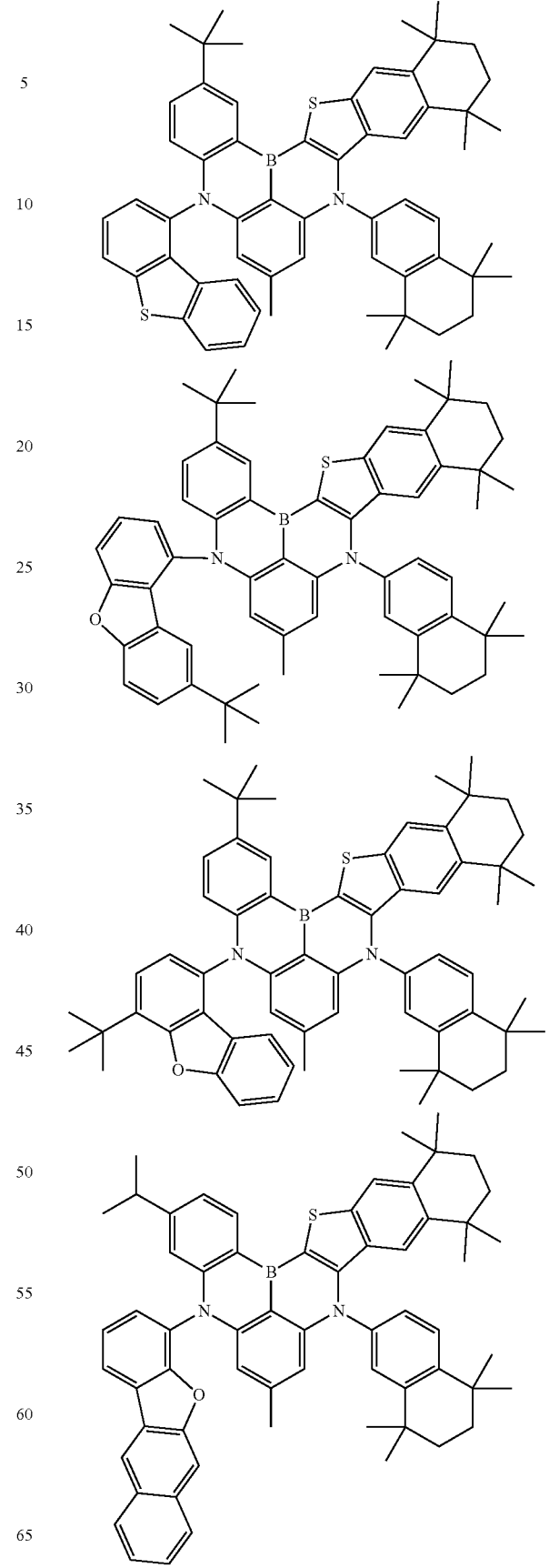

2159
-continued
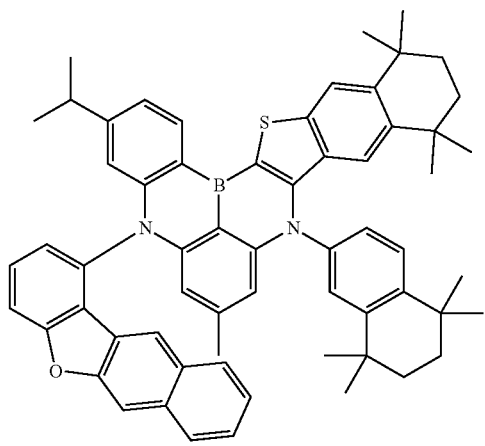
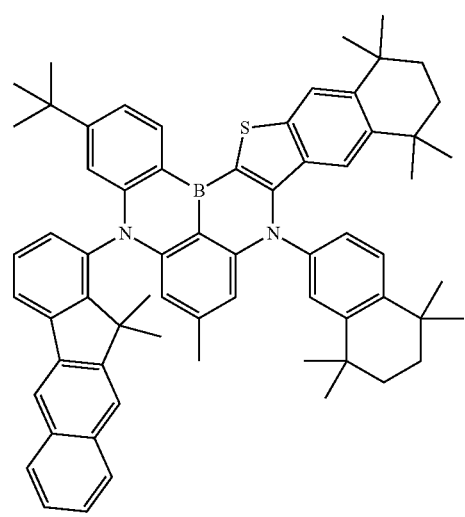
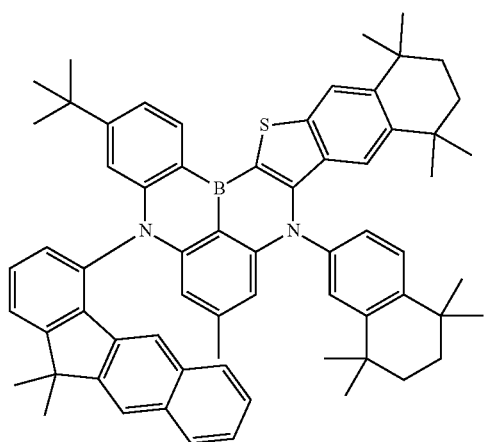
2160
-continued
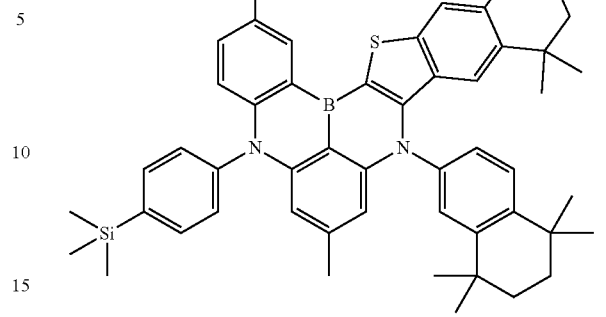
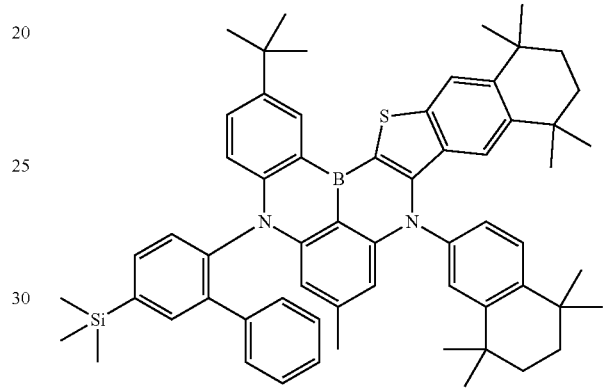
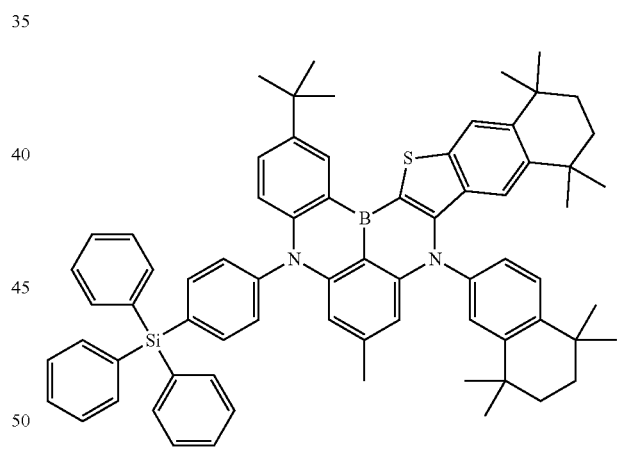
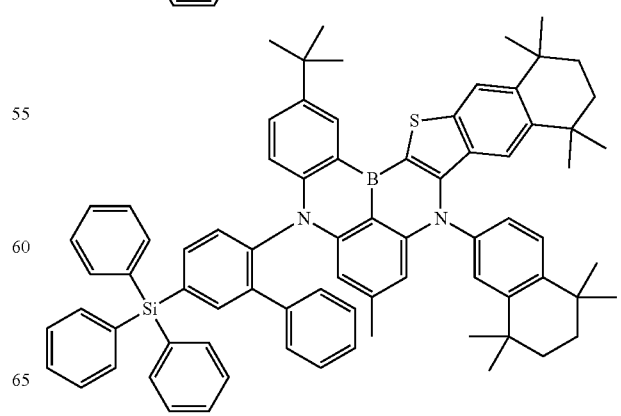

2161
-continued
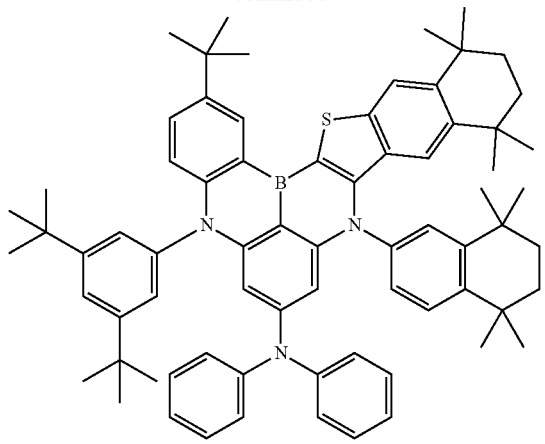
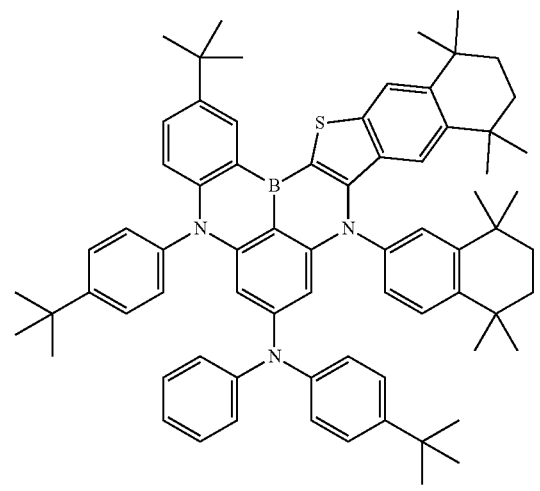
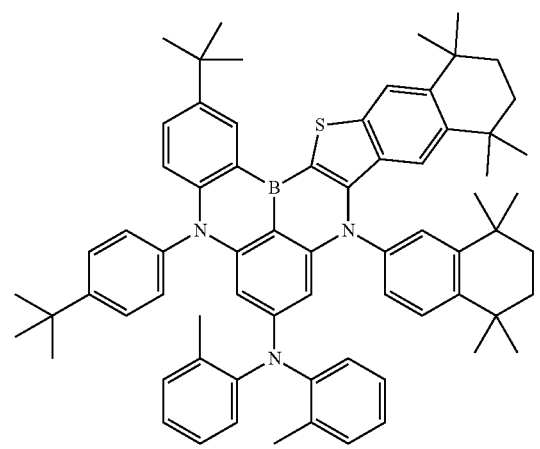
2162
-continued
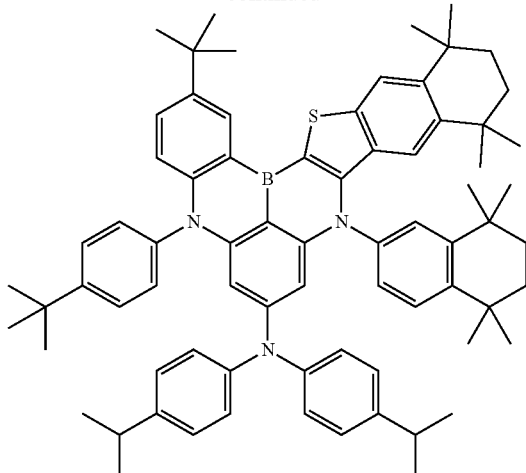
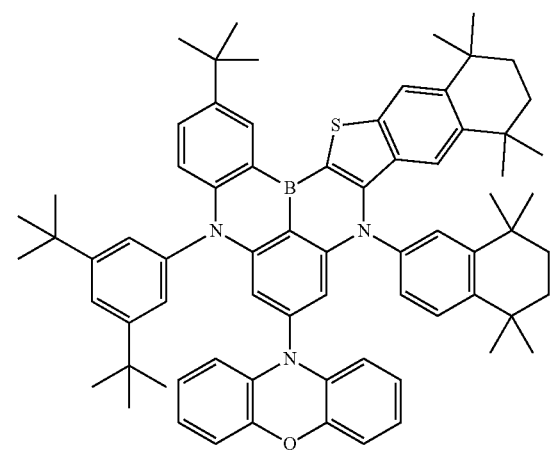
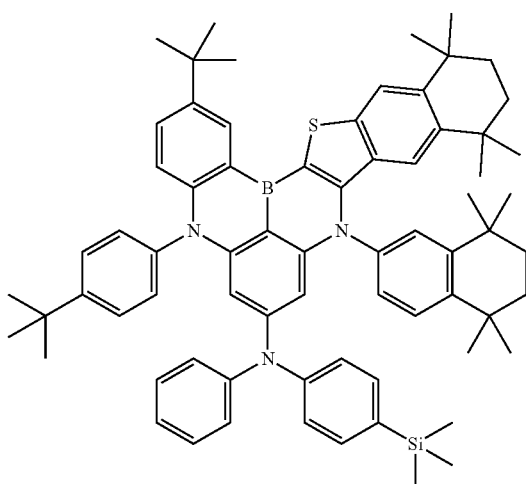

2163
-continued
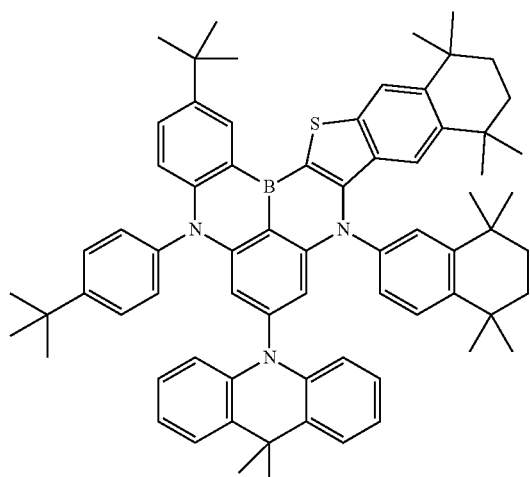
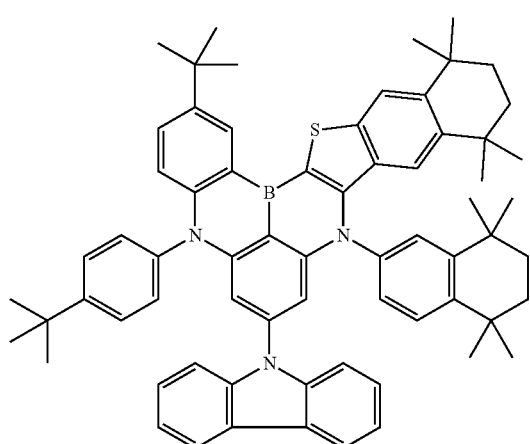
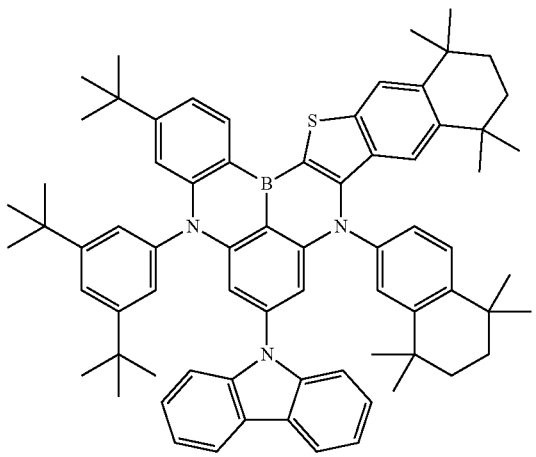
2164
-continued
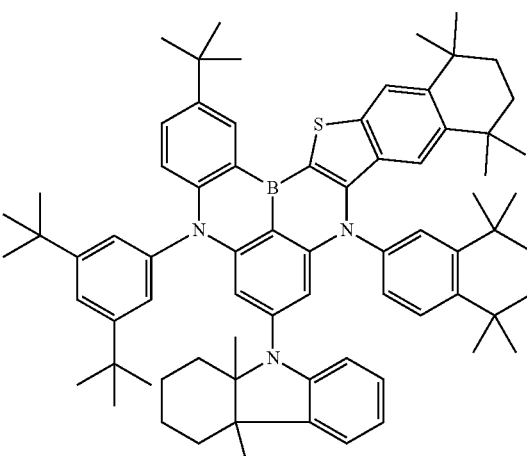
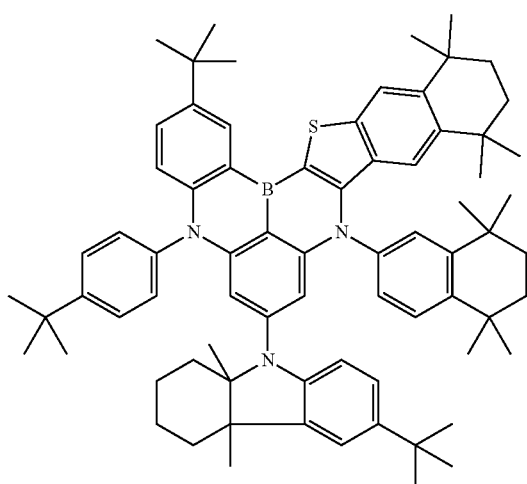
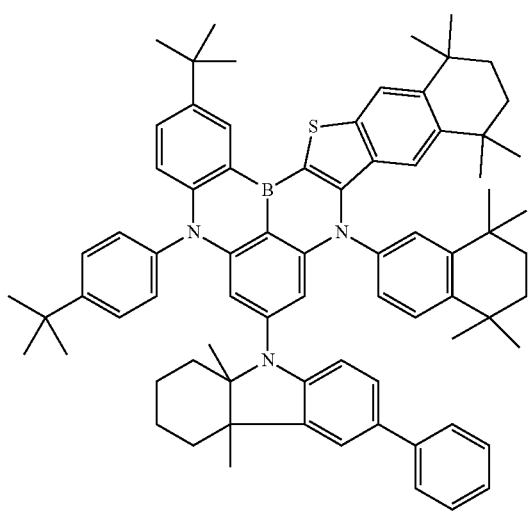

2165
-continued
2166
-continued
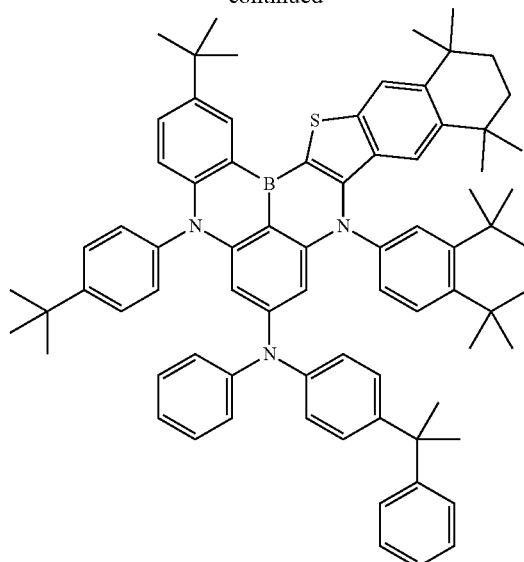
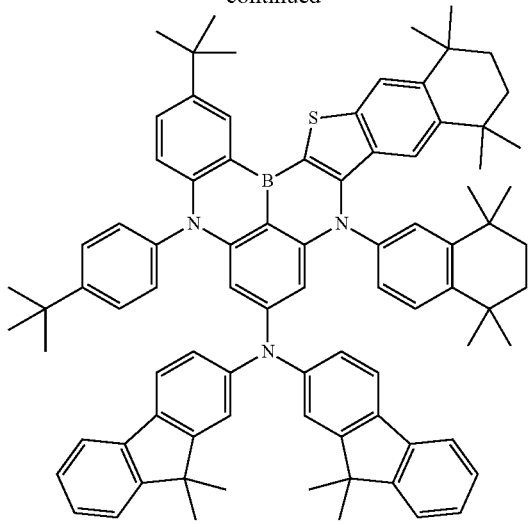
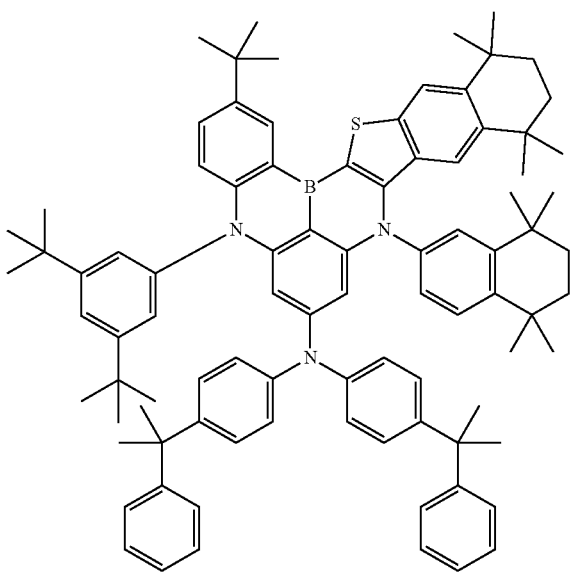
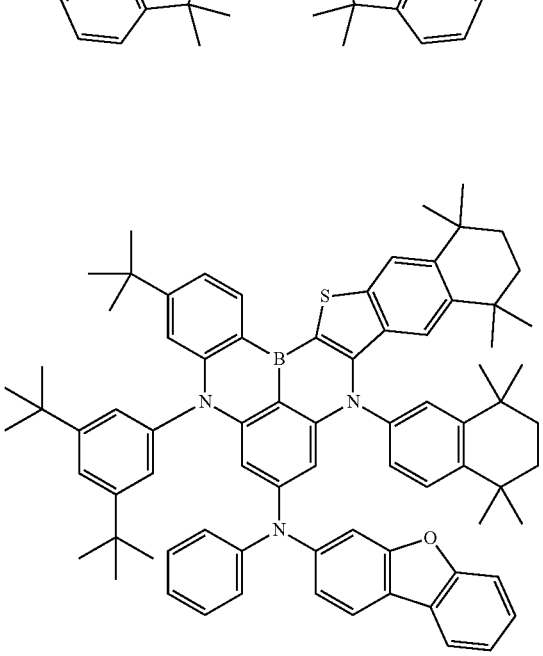
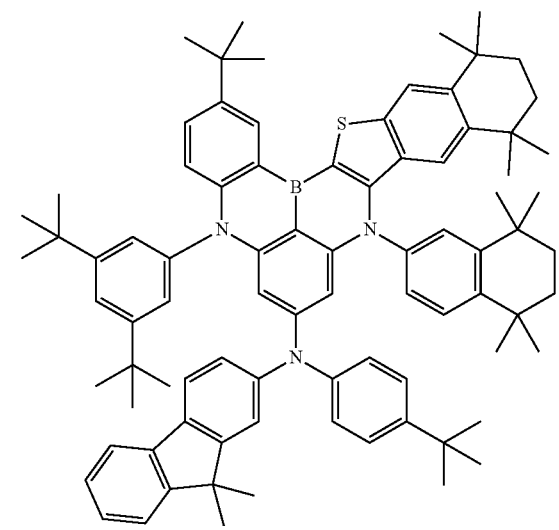
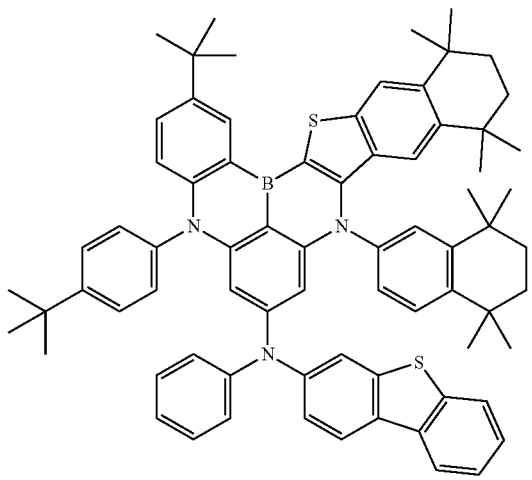

2167
-continued
2168
-continued
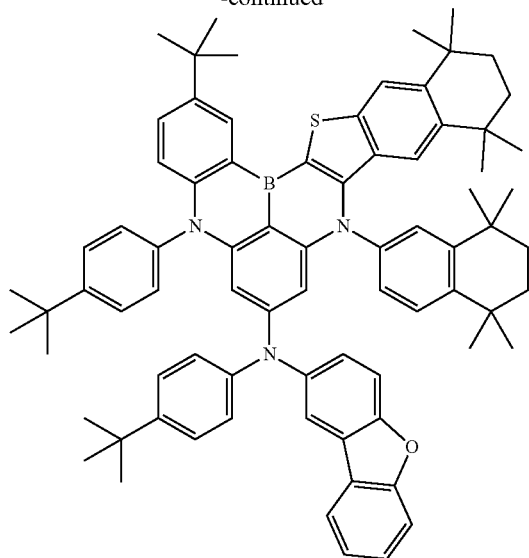
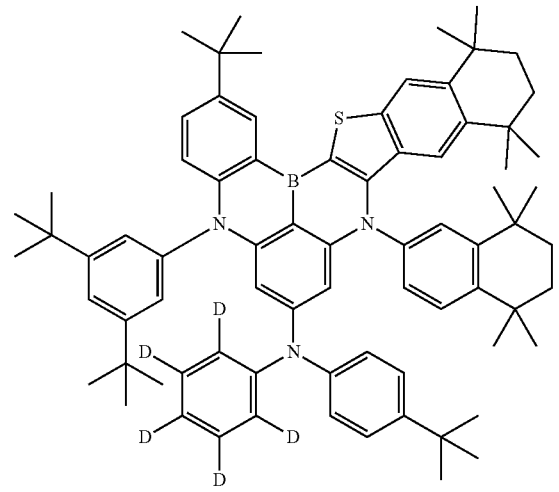
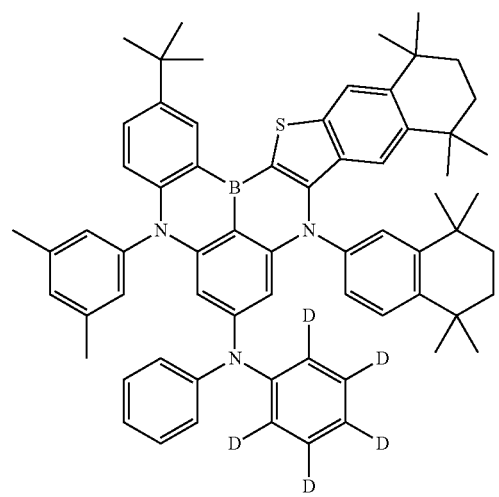
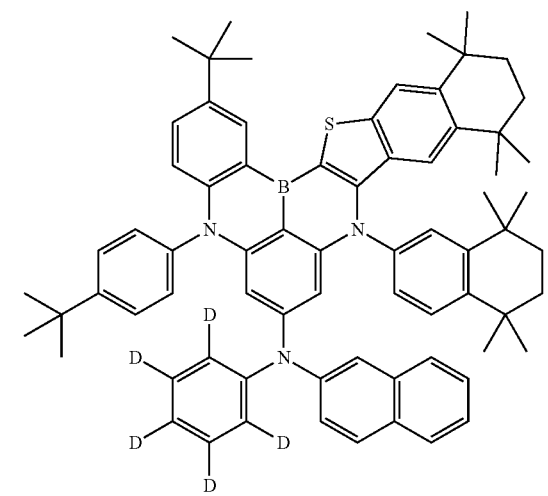
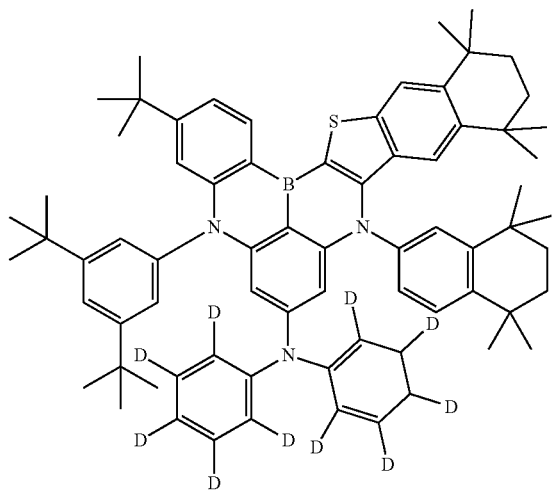
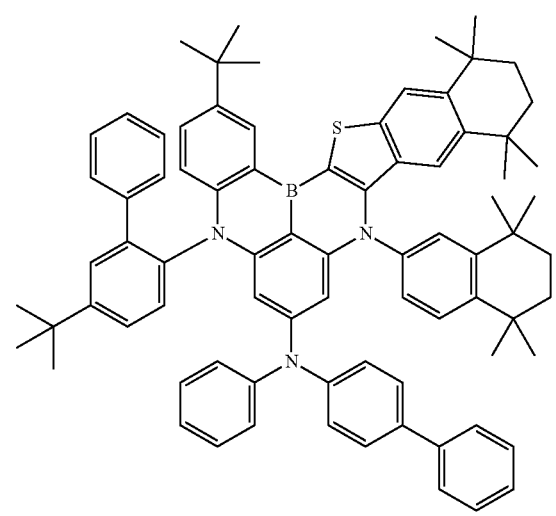

2169
-continued
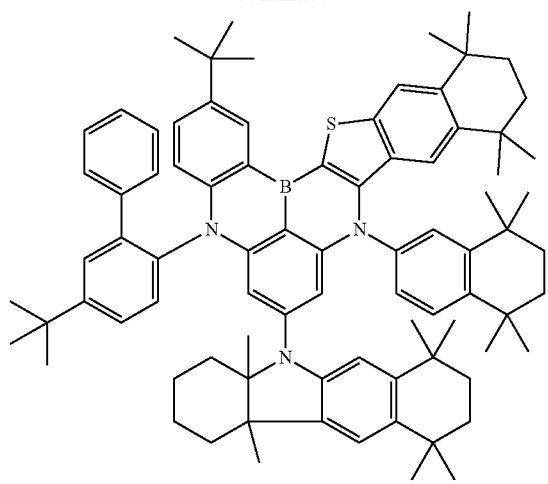
2170
-continued
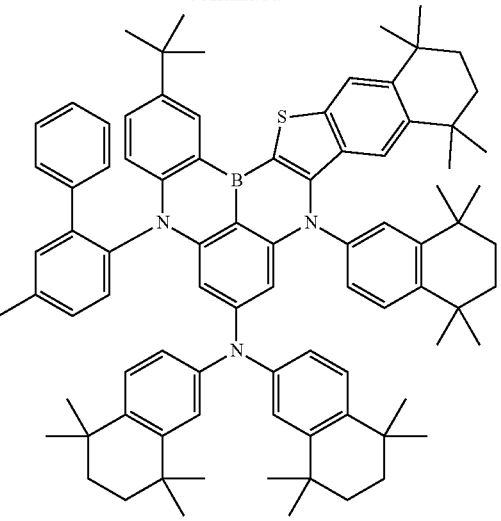
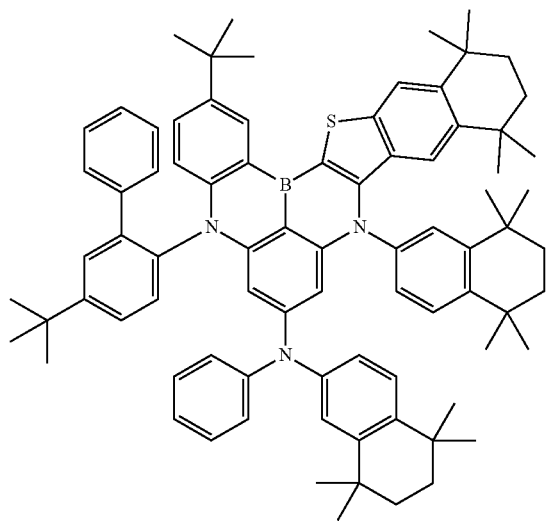
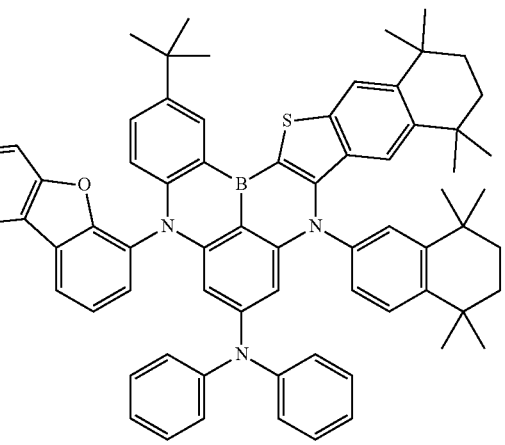
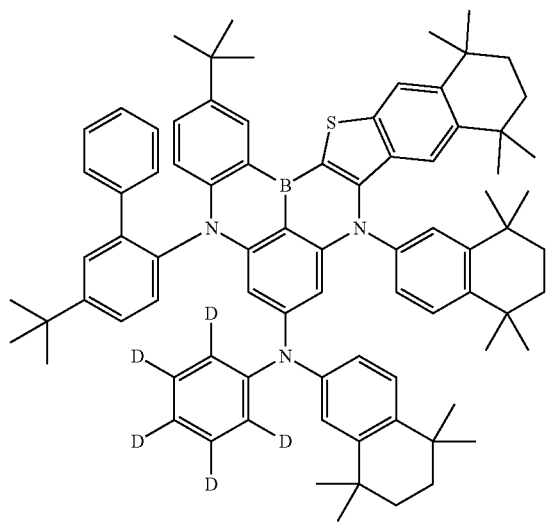
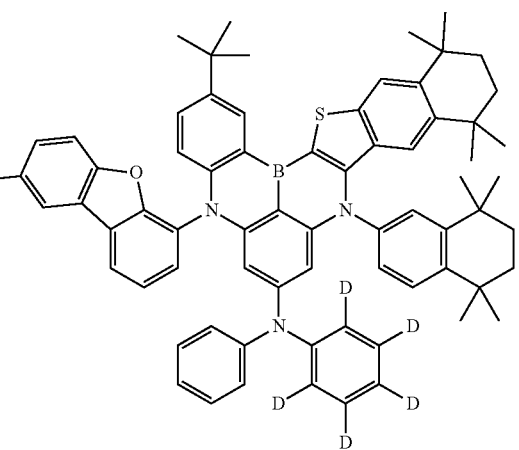

2171
-continued
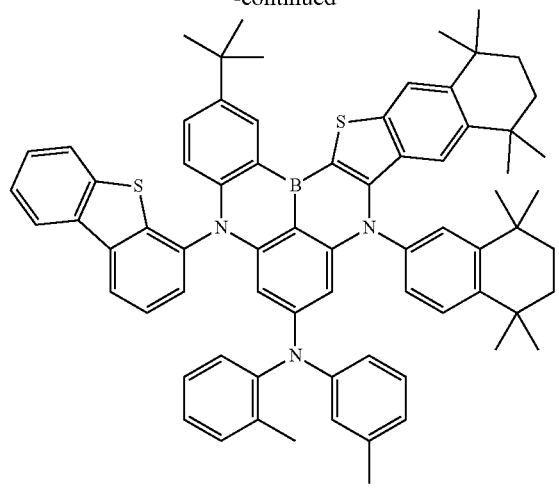
2172
-continued
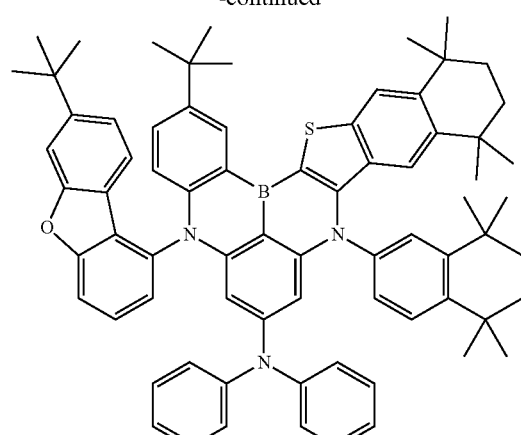
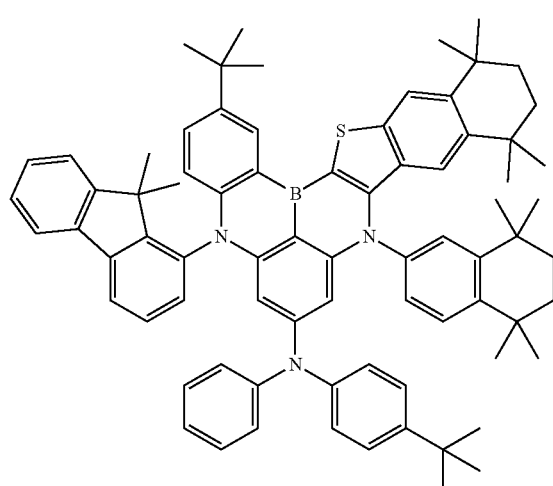
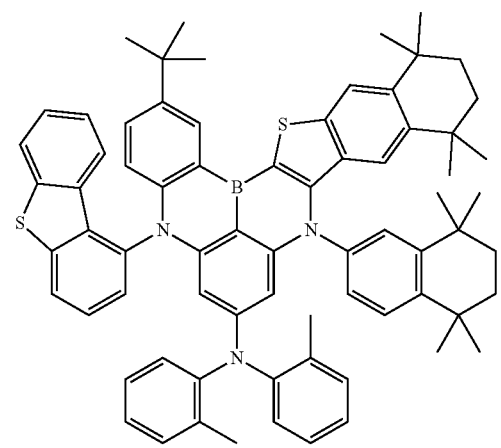
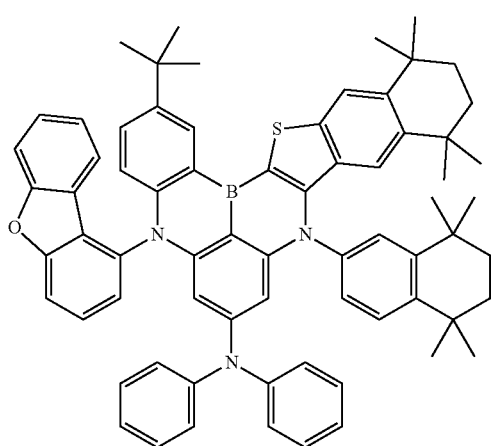
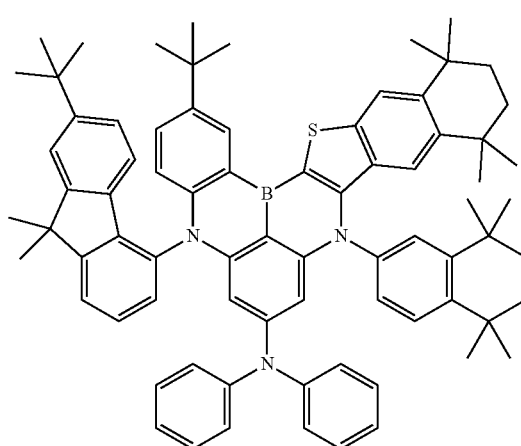

2173
-continued
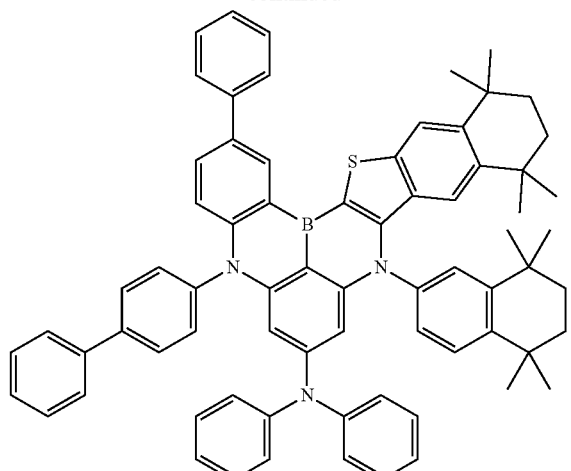
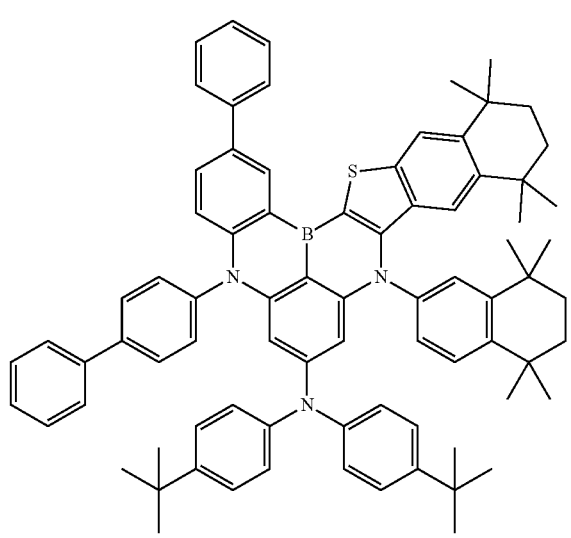
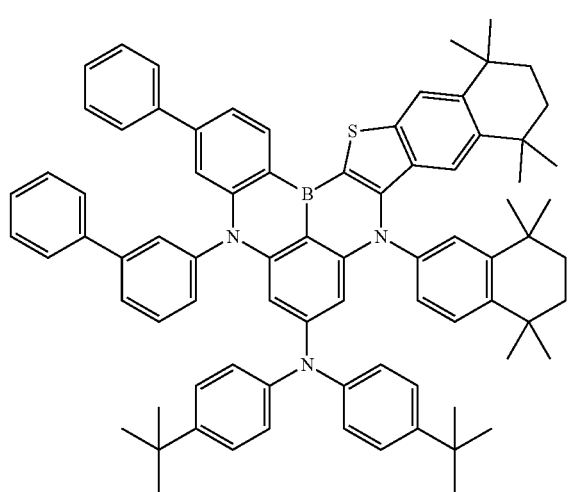
2174
-continued
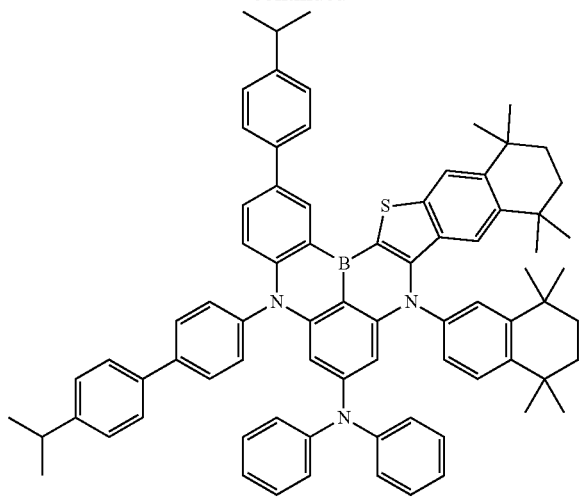
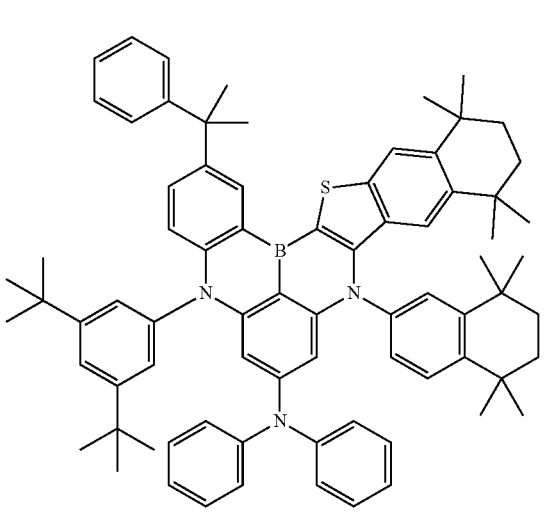
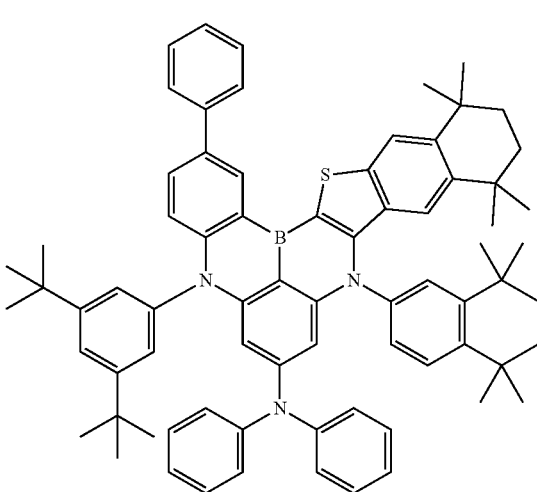

2175
-continued
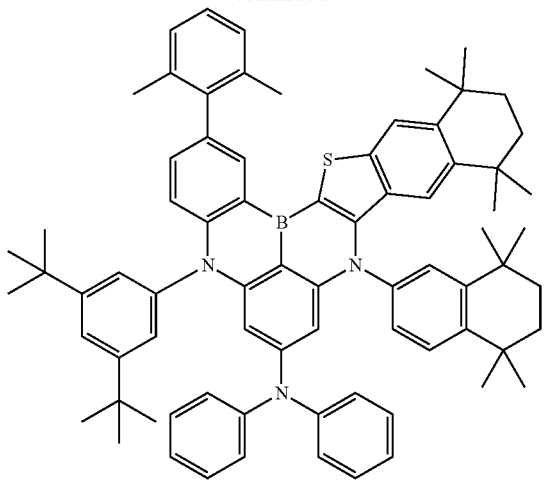
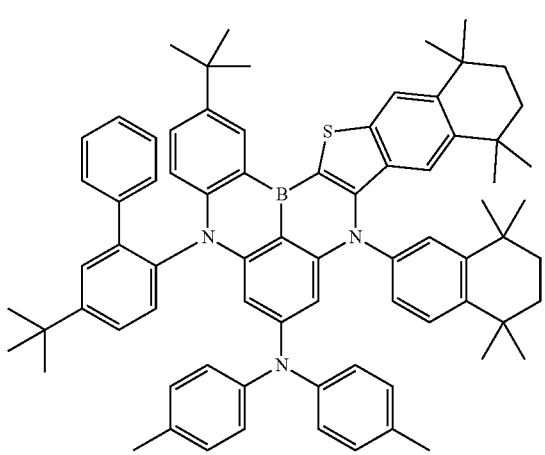
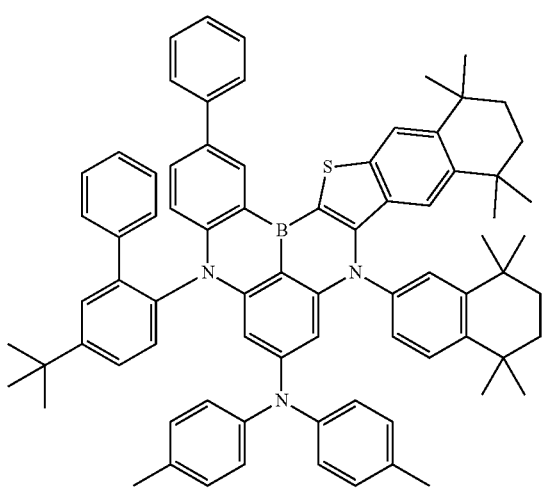
2176
-continued
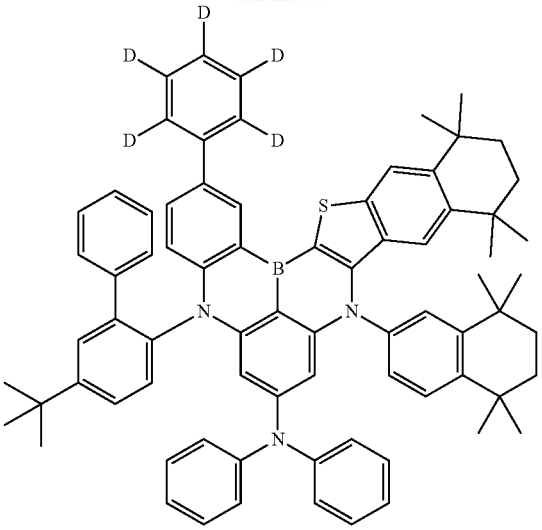
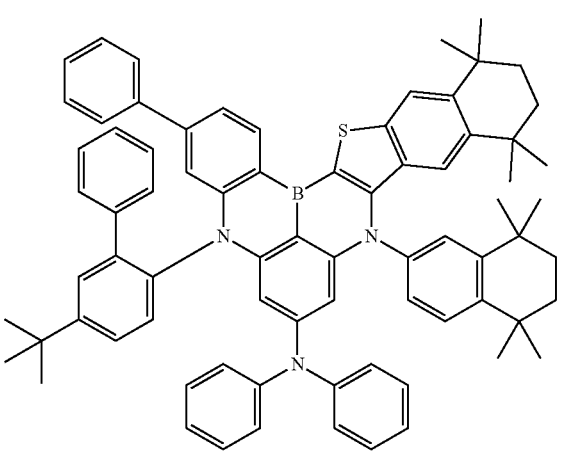
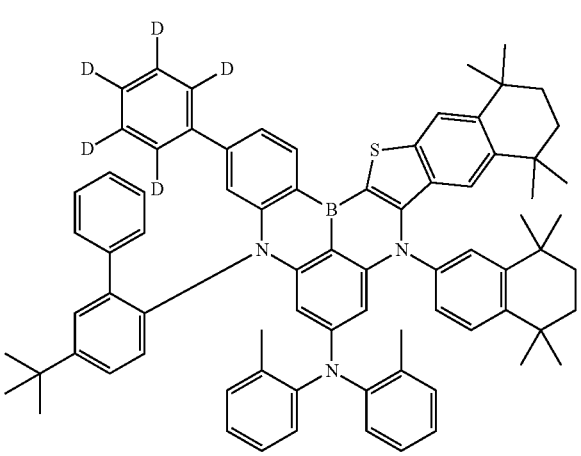

2177
-continued
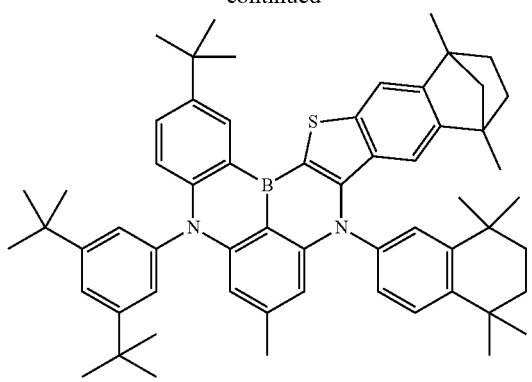
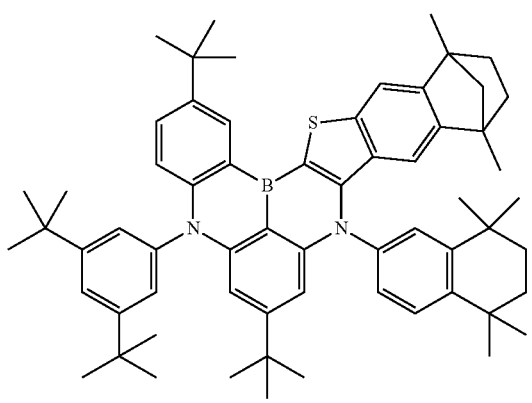
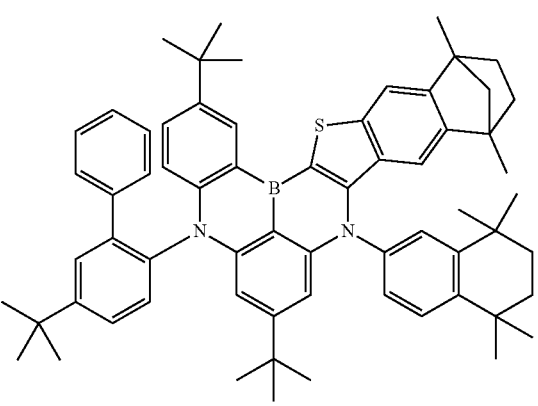
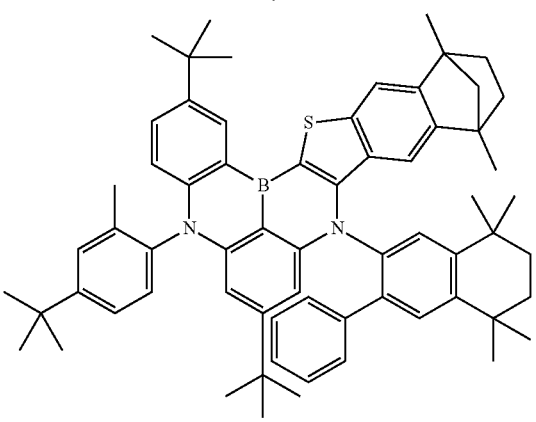
2178
-continued
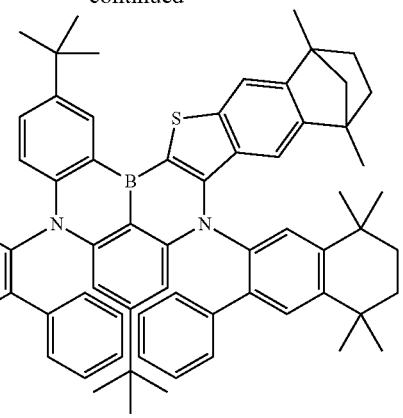
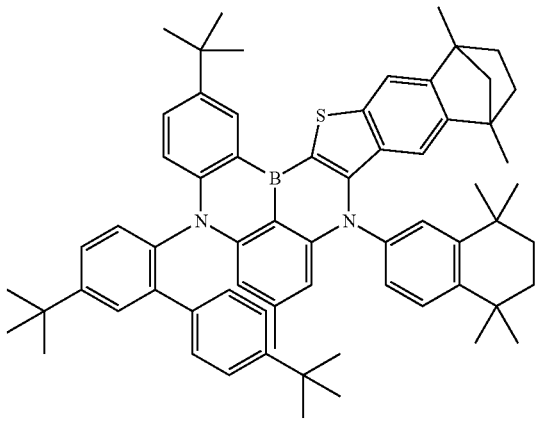
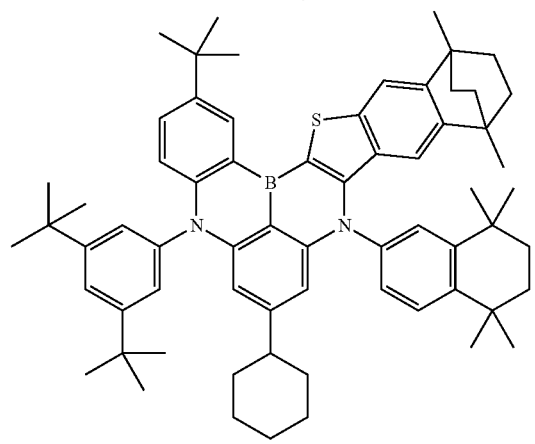
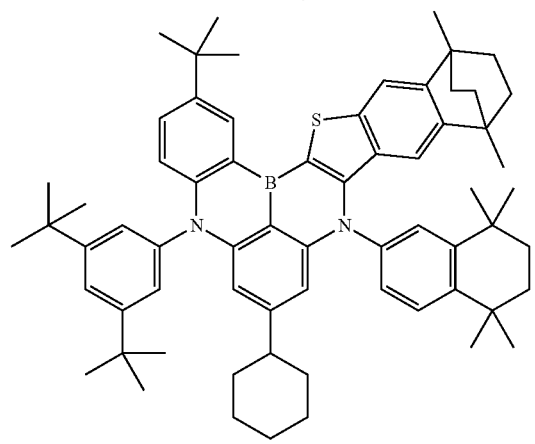

2179
-continued
2180
-continued
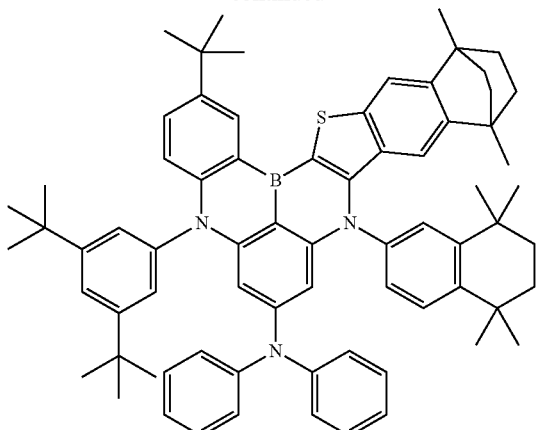
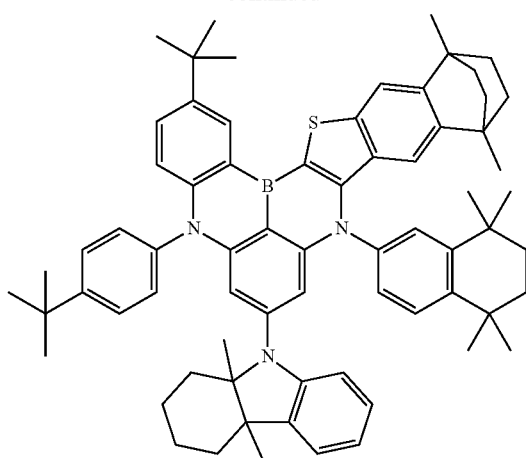
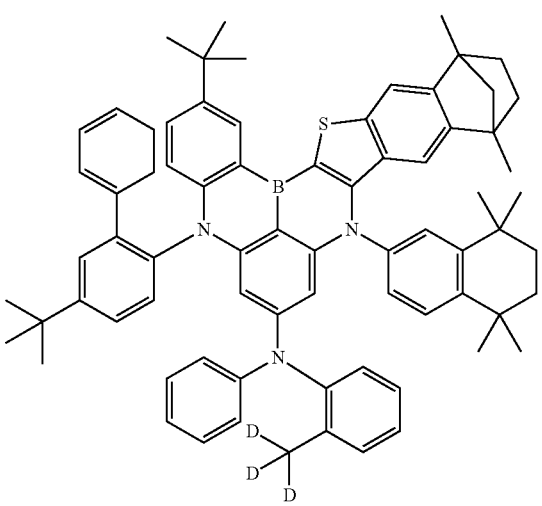
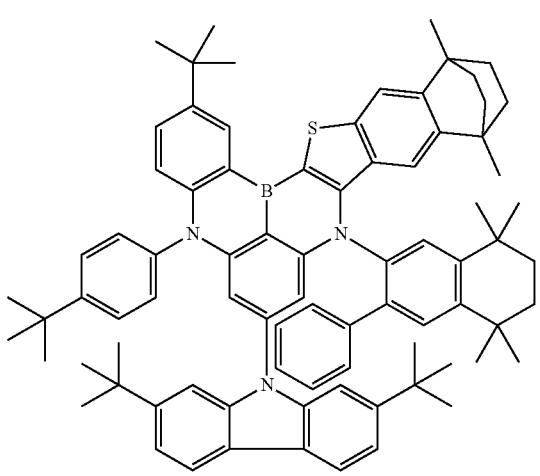
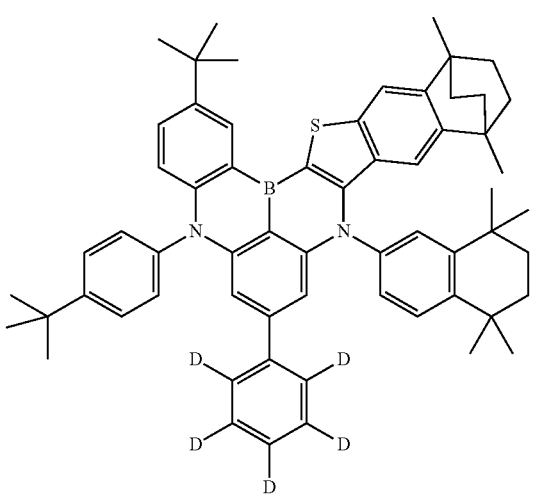

2181
-continued
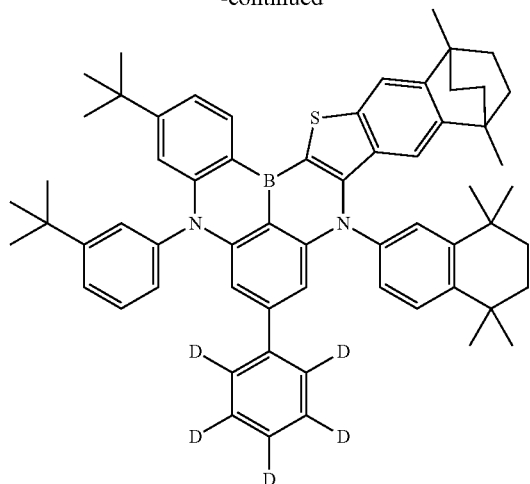
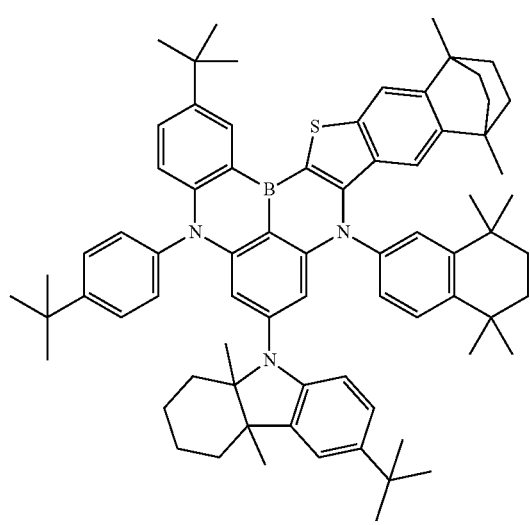
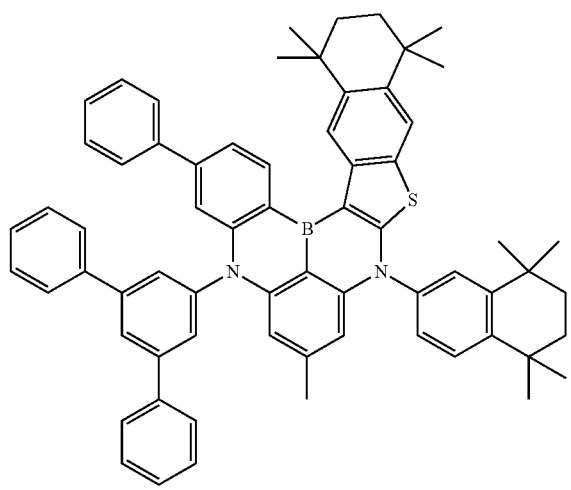
2182
-continued
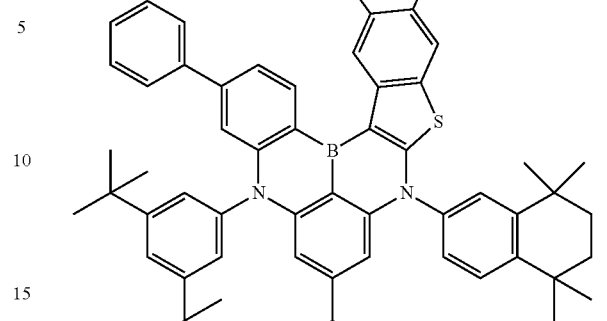
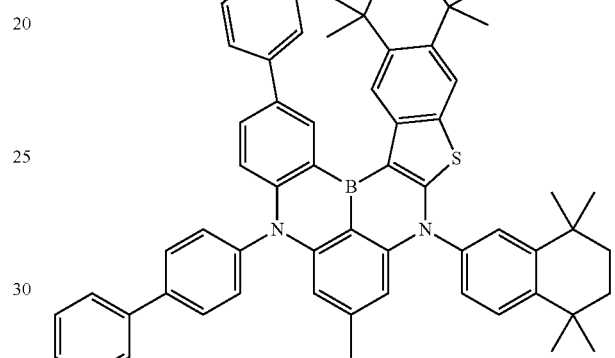
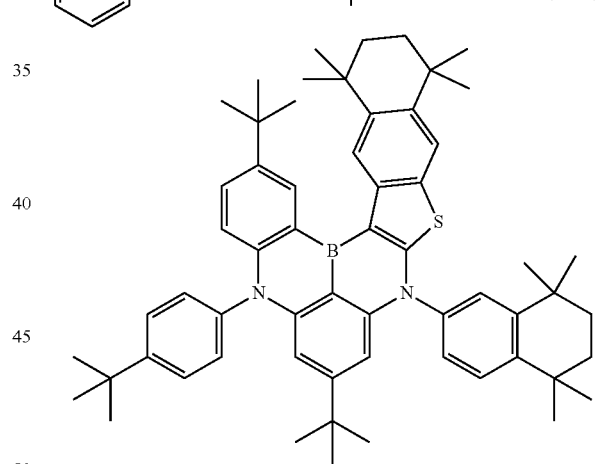
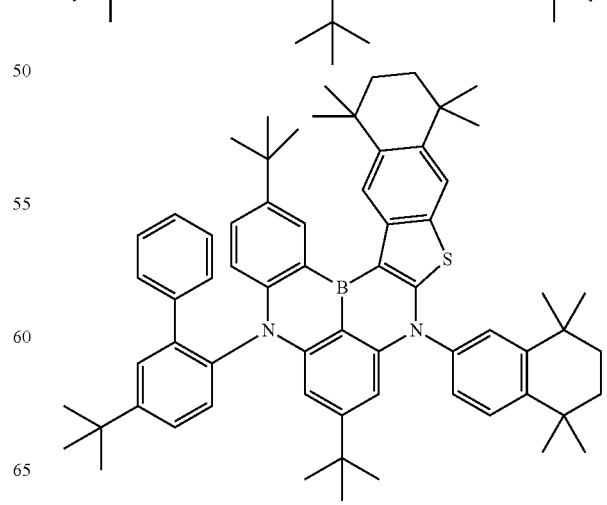

2183
-continued
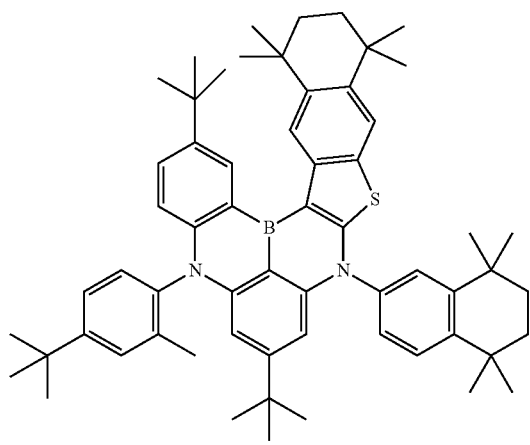
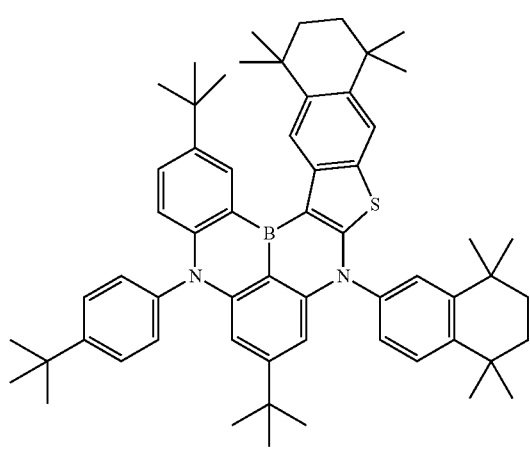
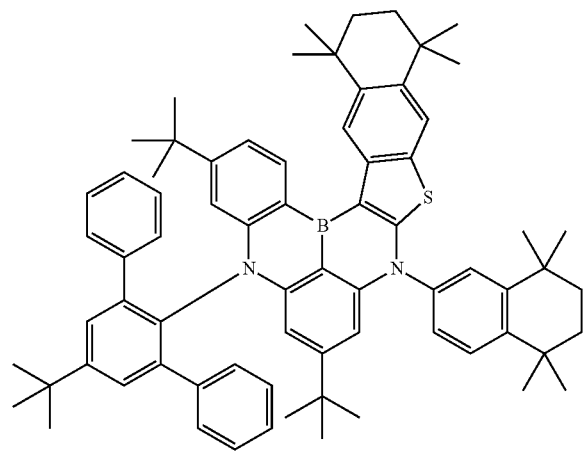
2184
-continued
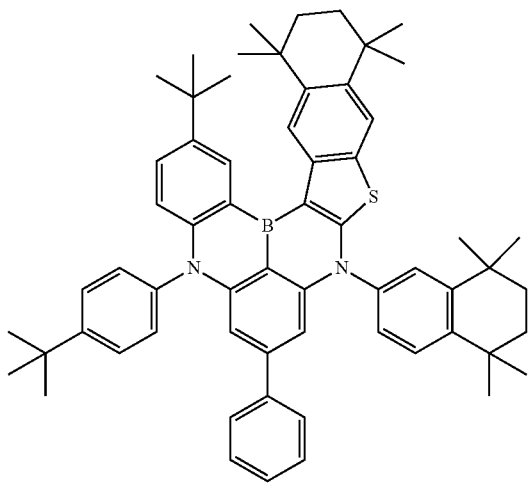
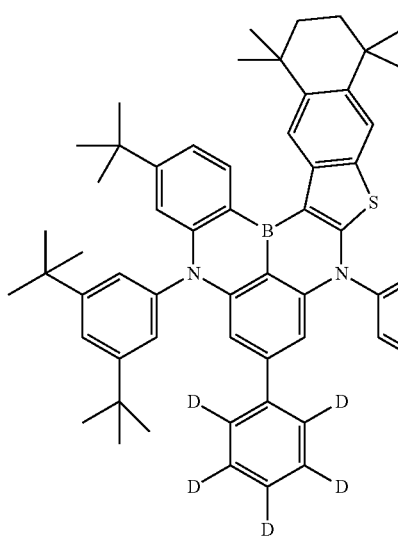
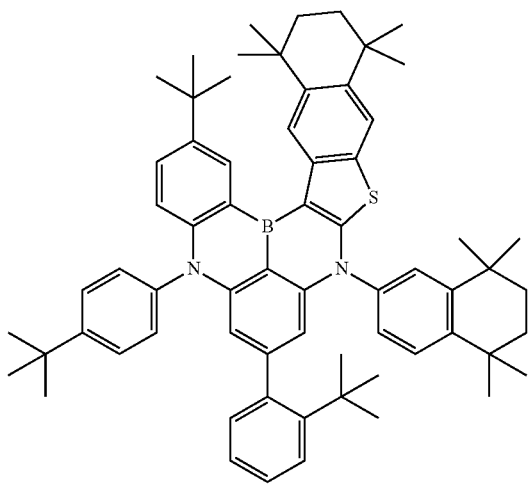

-continued
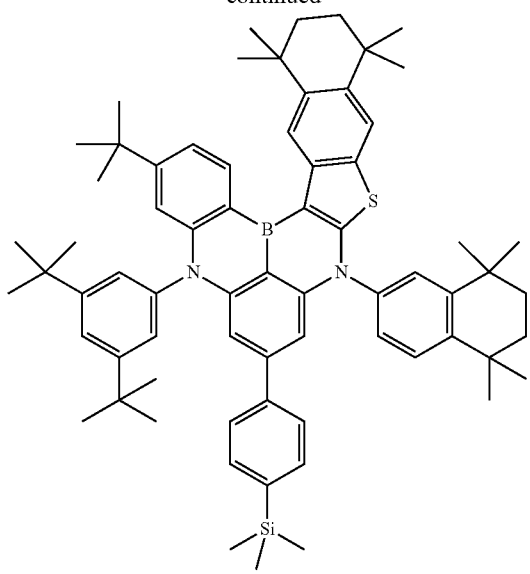
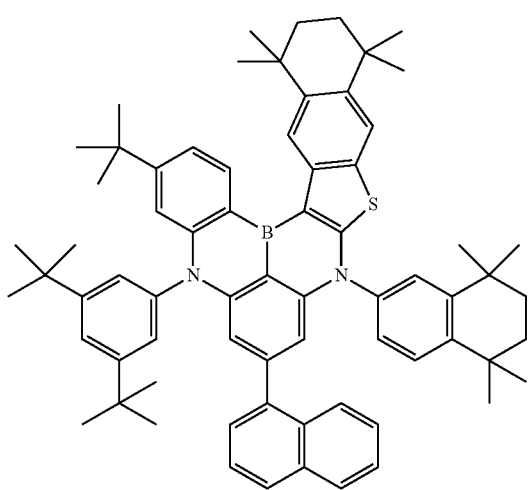
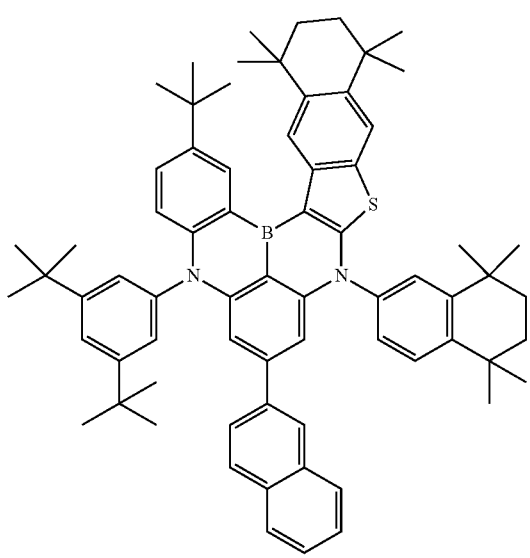
-continued
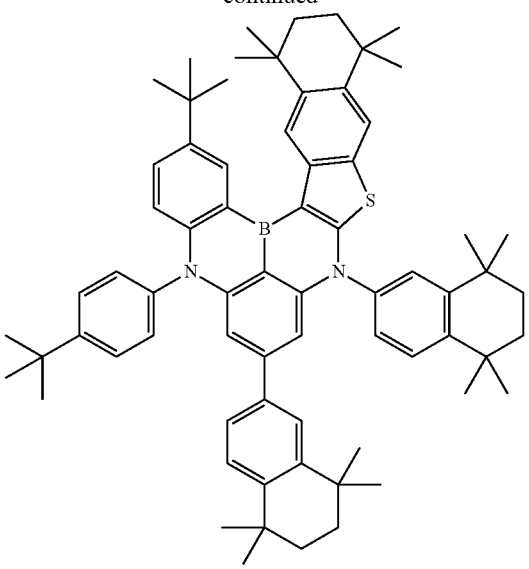
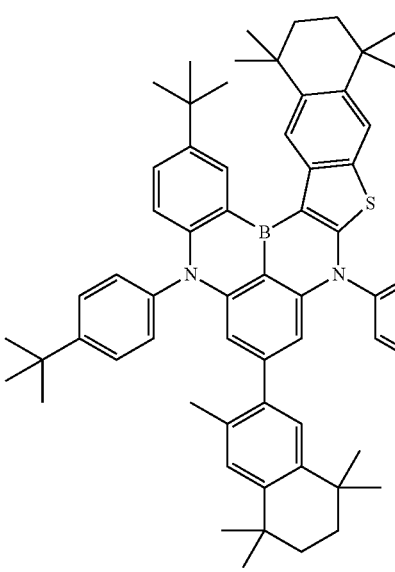
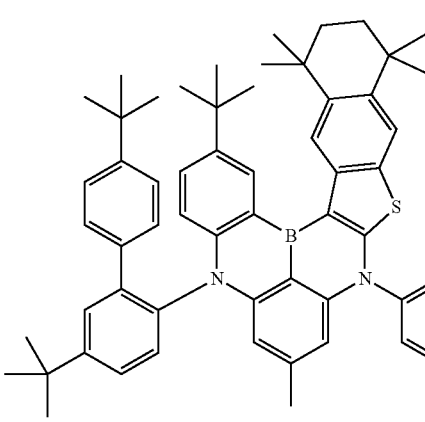

2187
-continued
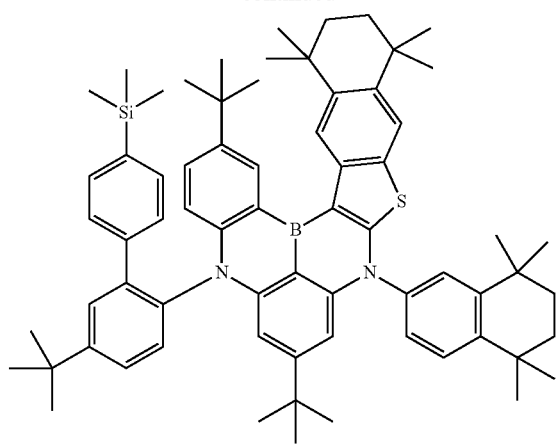
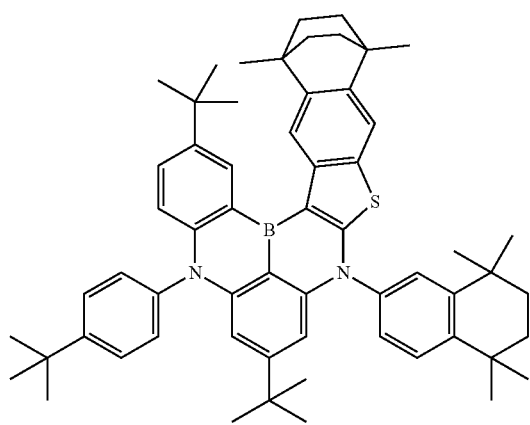
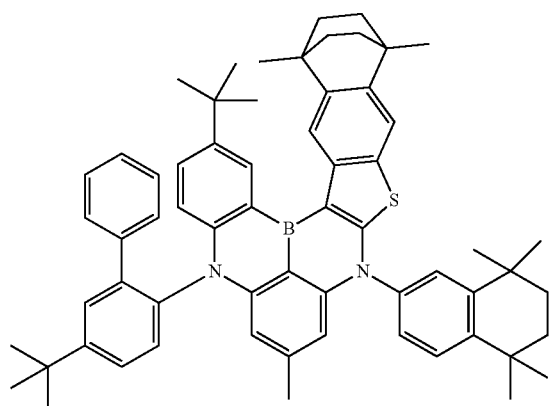
2188
-continued
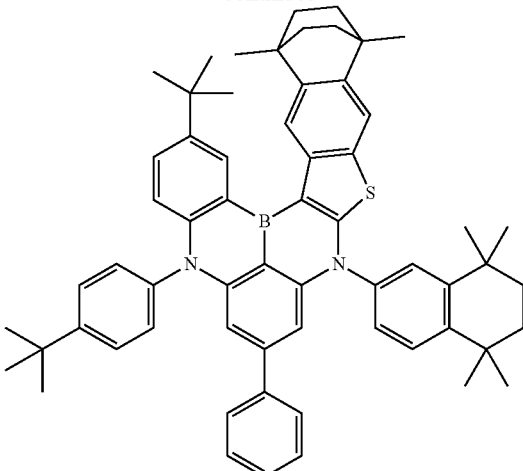
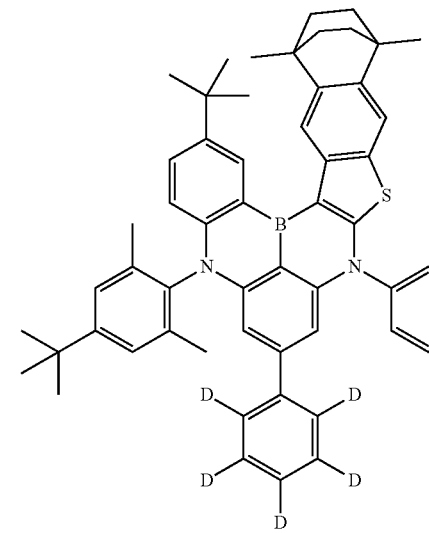
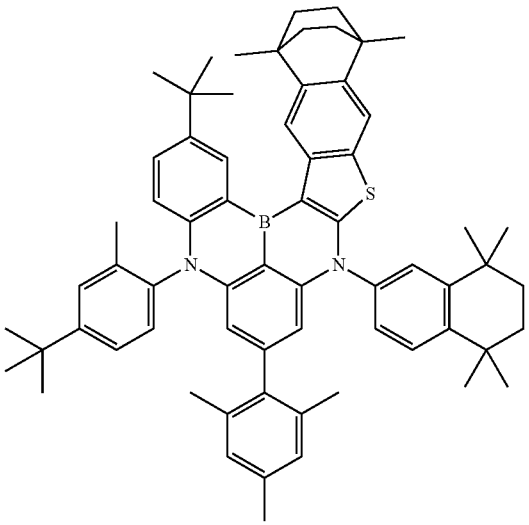

2189
-continued
2190
-continued
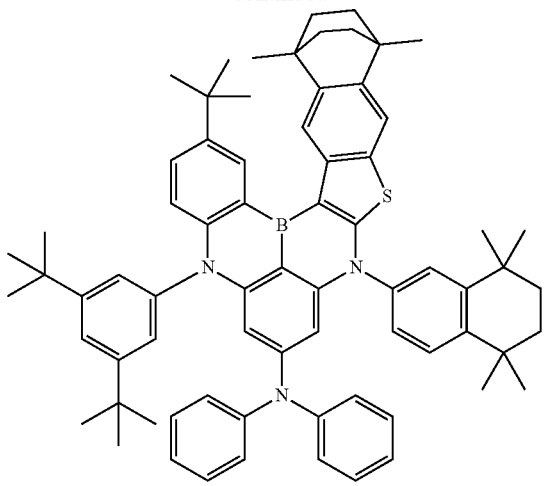
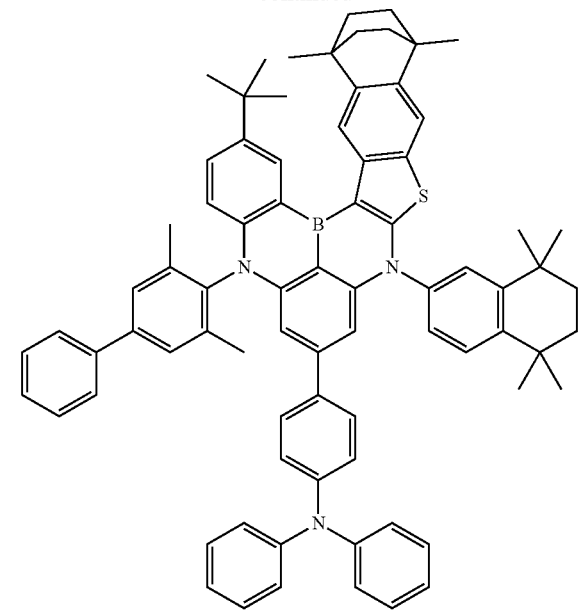
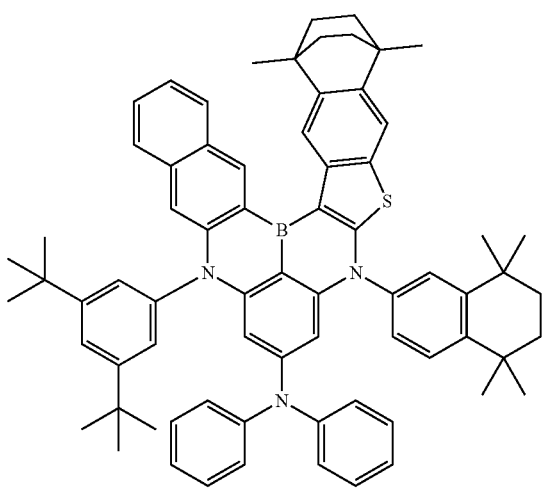
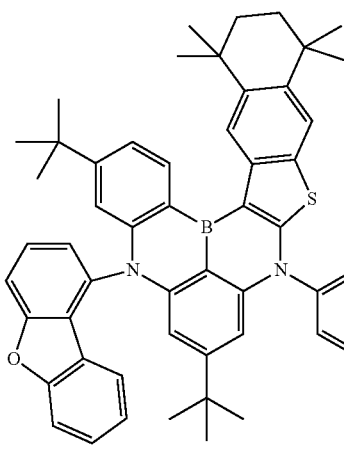
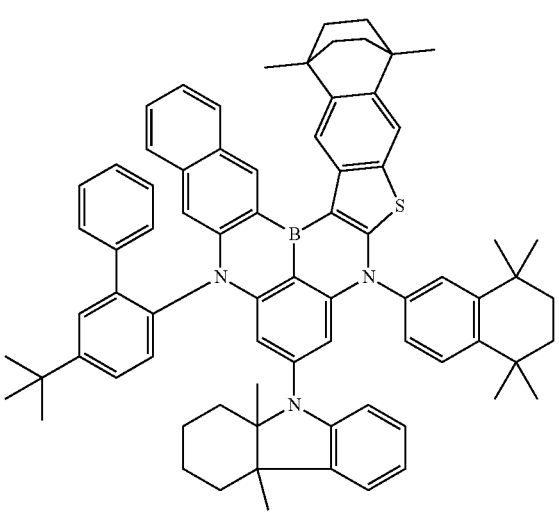
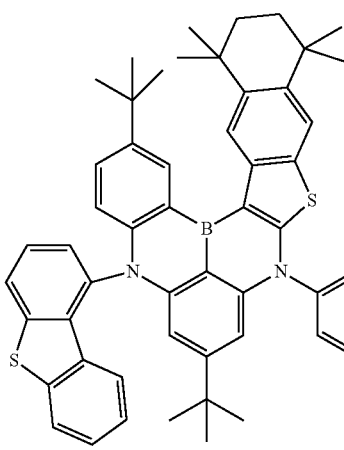

2191
-continued
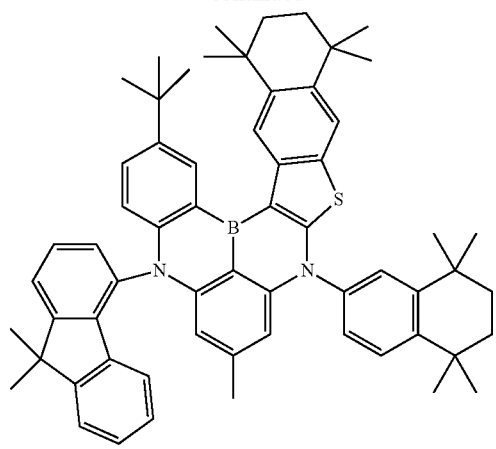
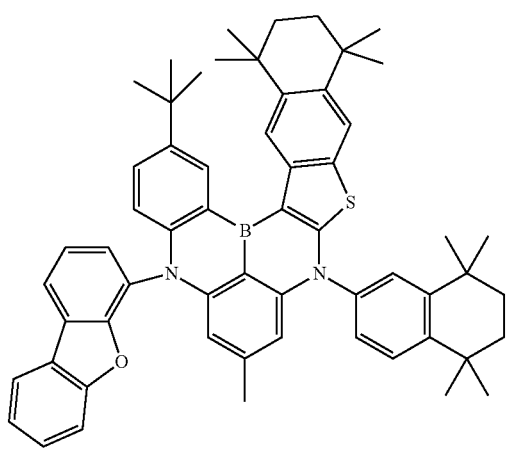
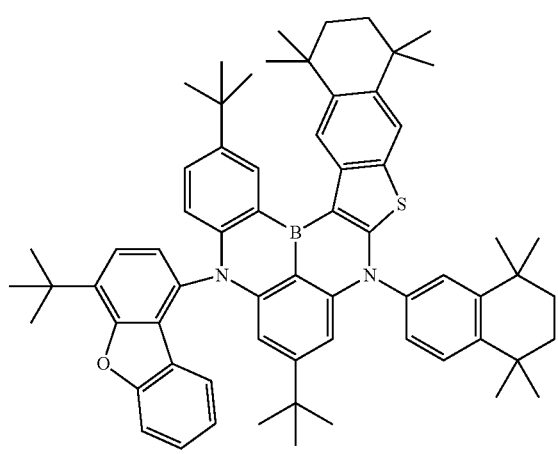
2192
-continued
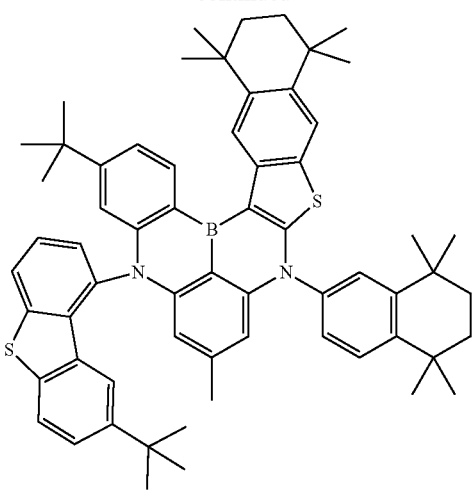
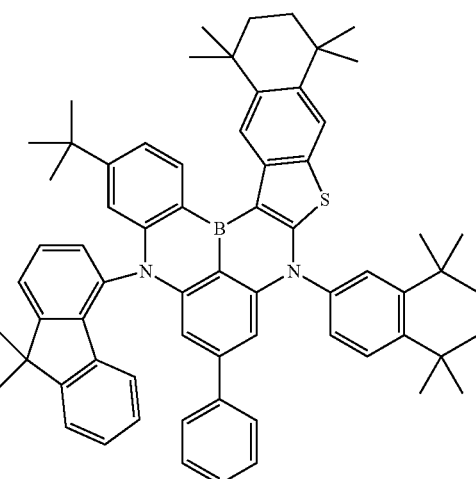
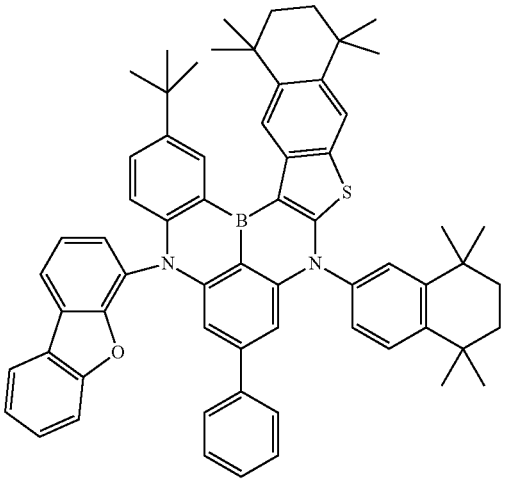

2193
-continued
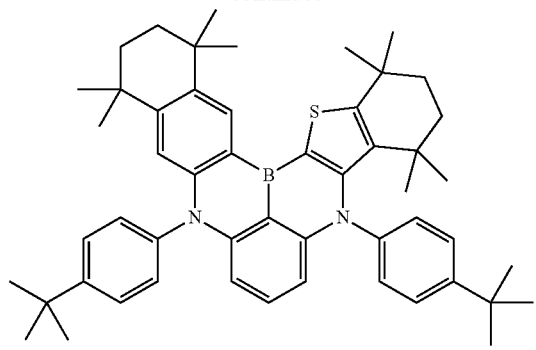
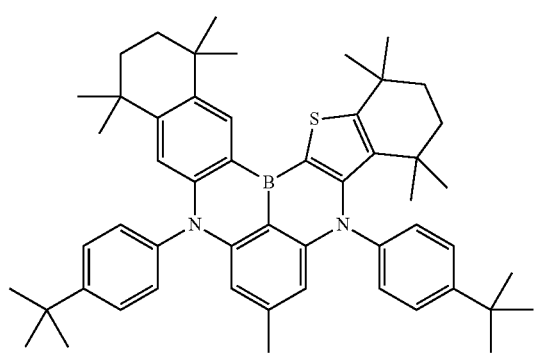
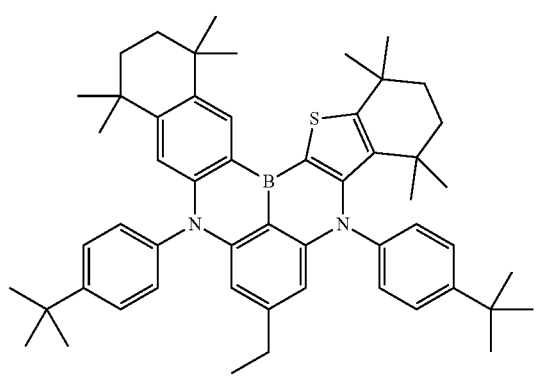
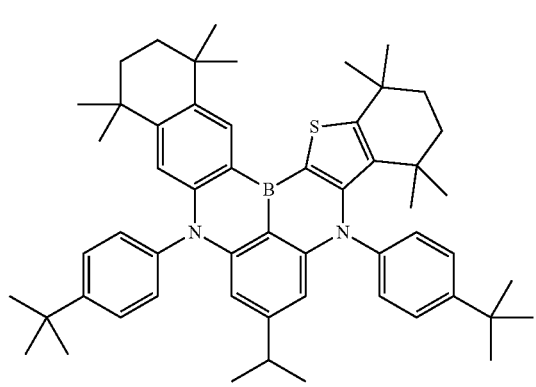
2194
-continued
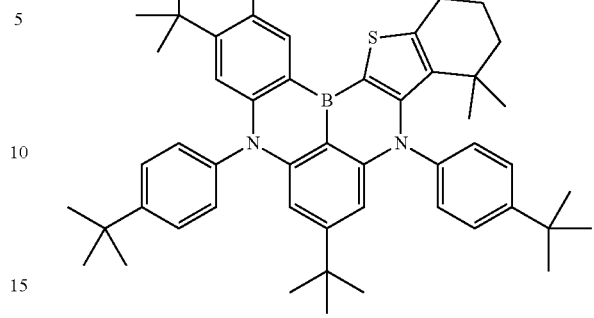
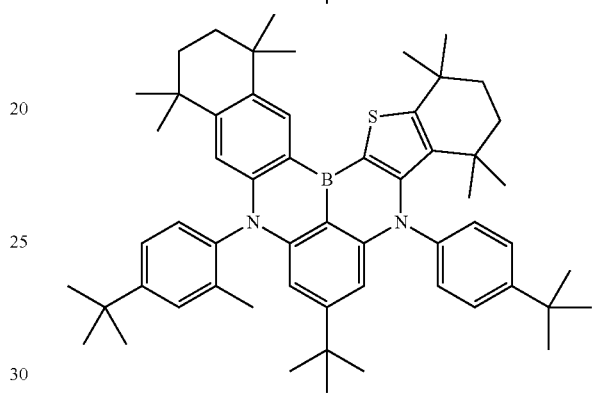
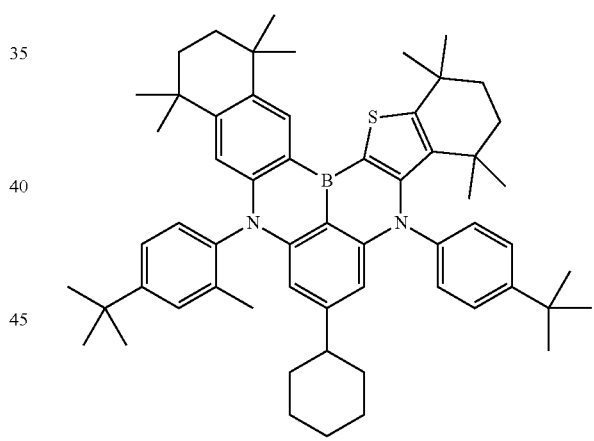
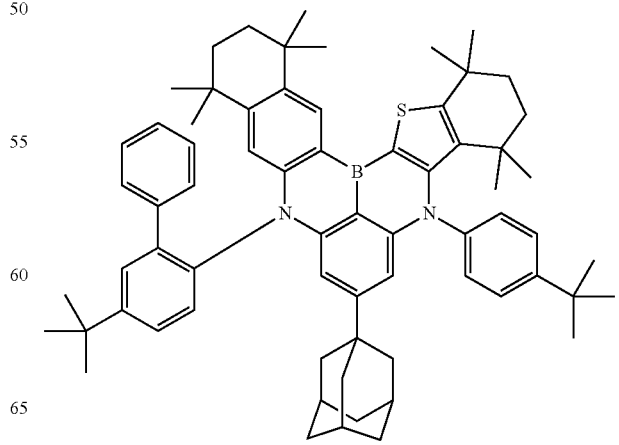

2195
-continued
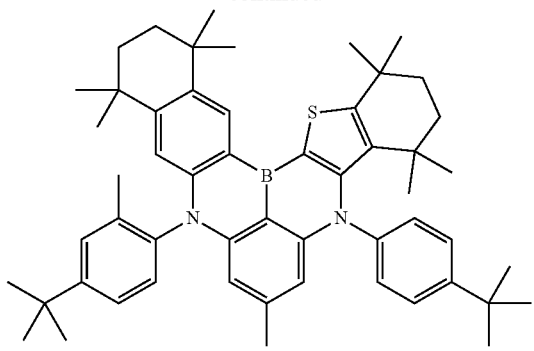
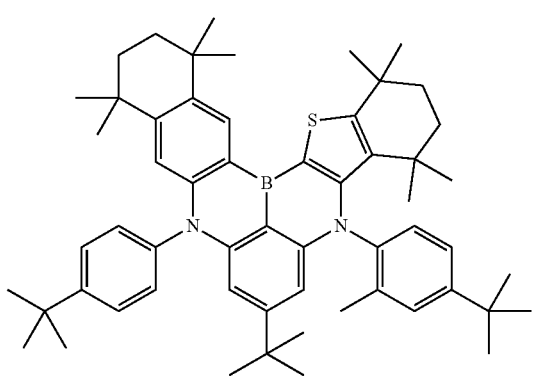
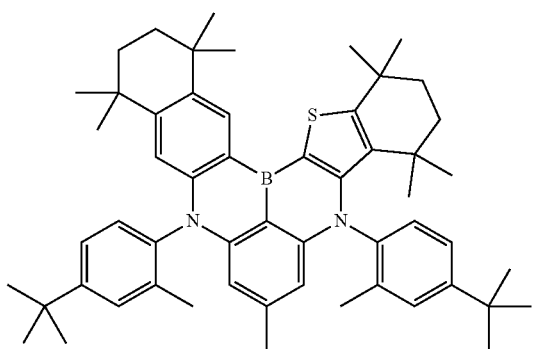
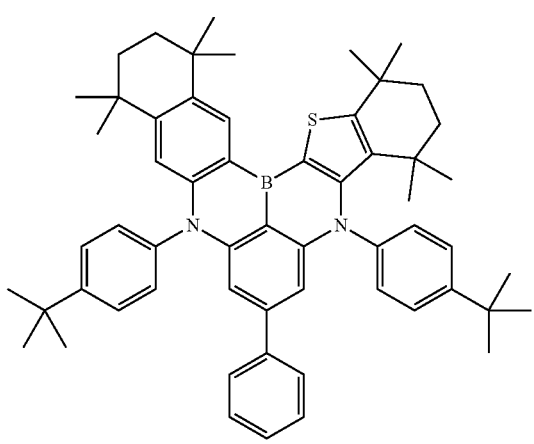
2196
-continued
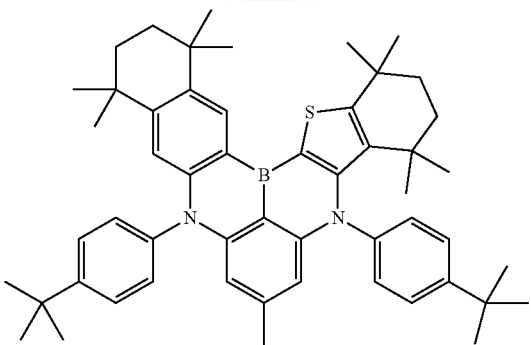
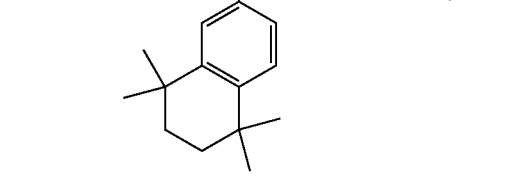
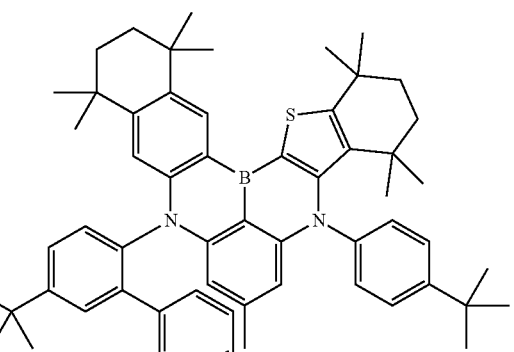
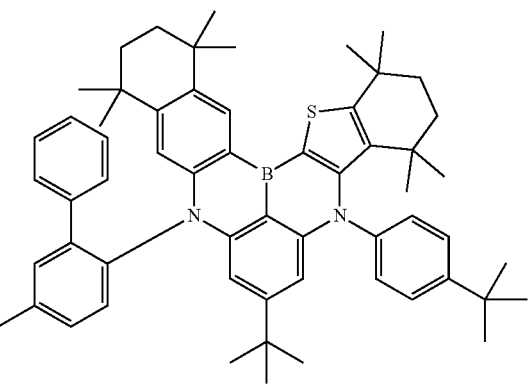
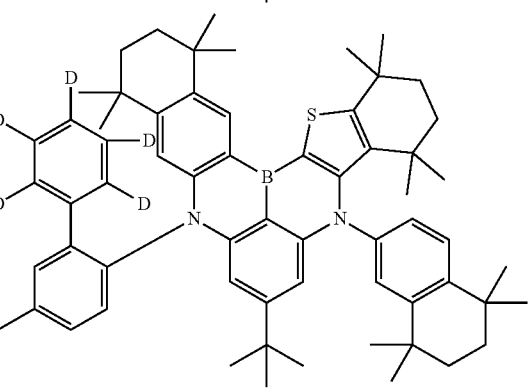

2197
-continued
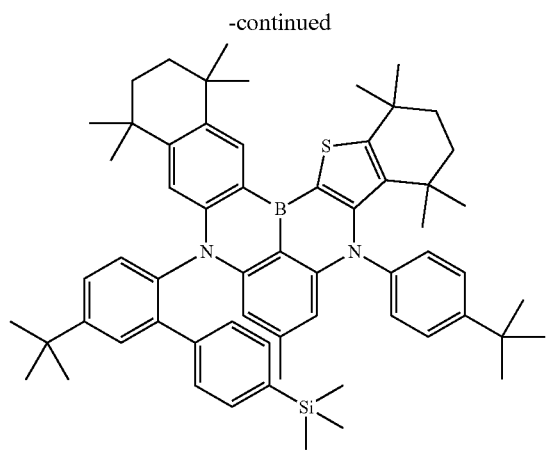
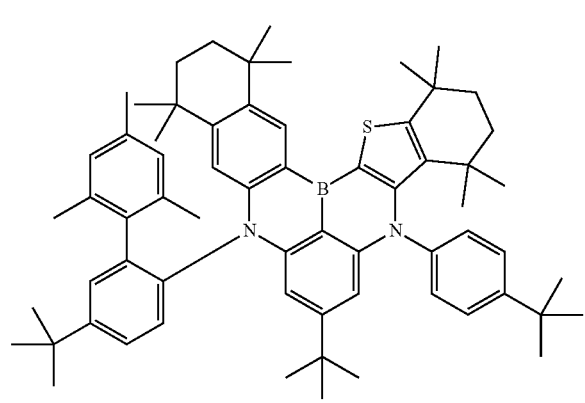
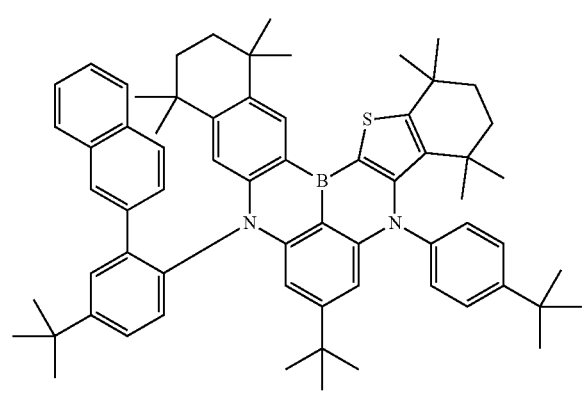
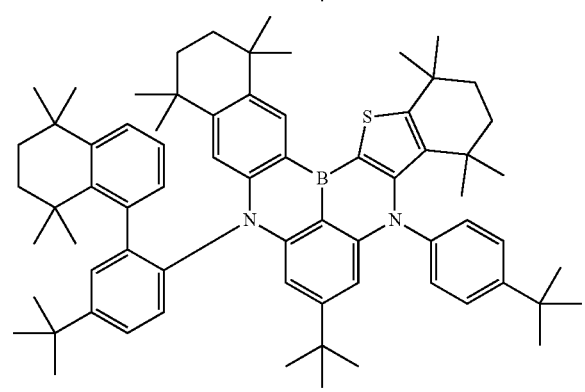
2198
-continued
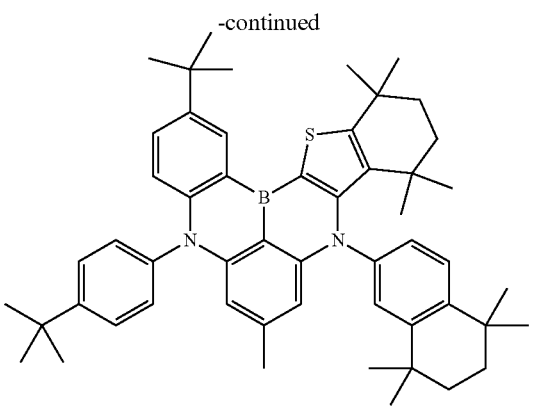
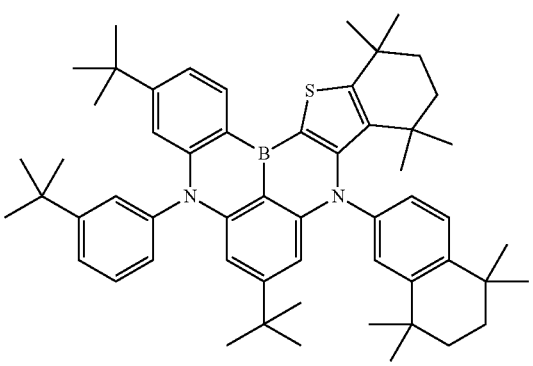
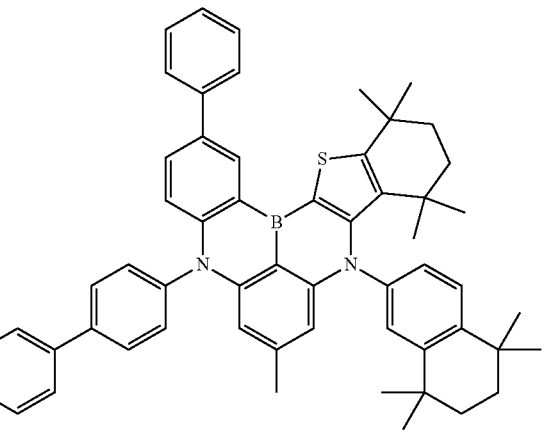
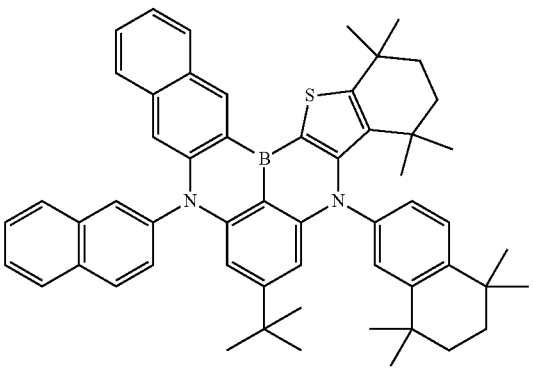

2199
-continued
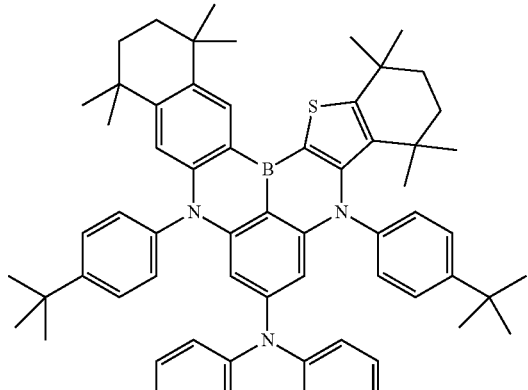
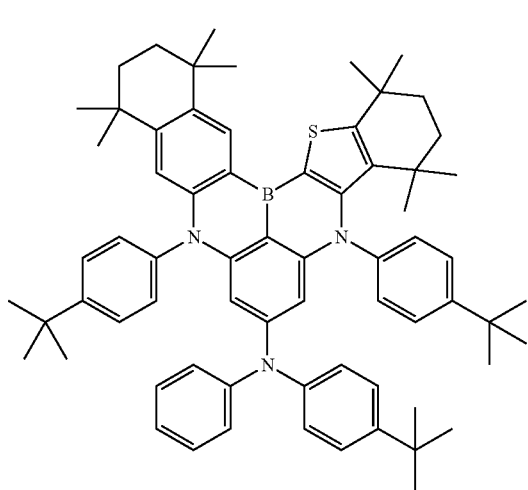
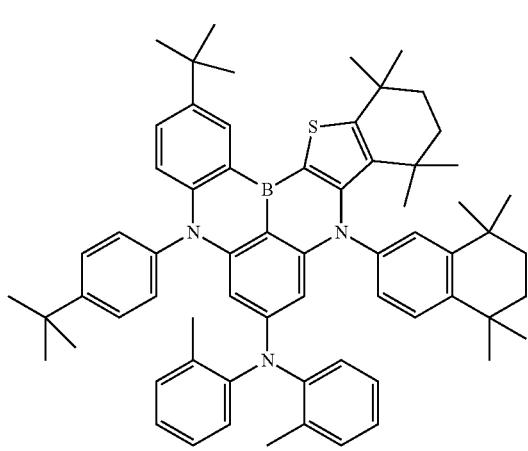
2200
-continued
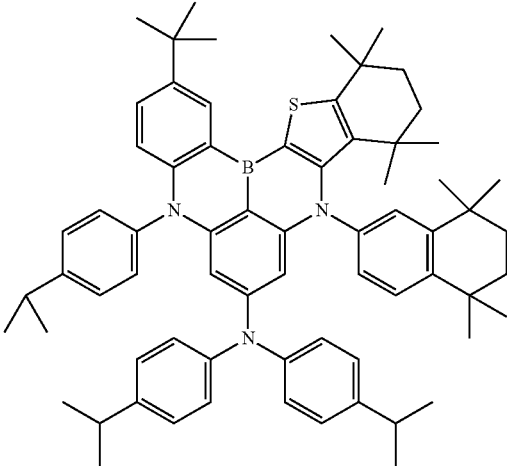
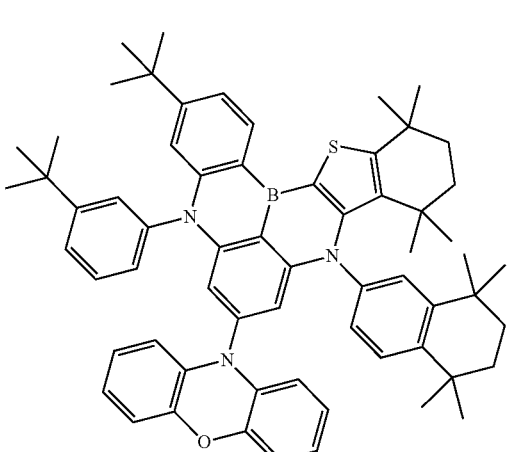
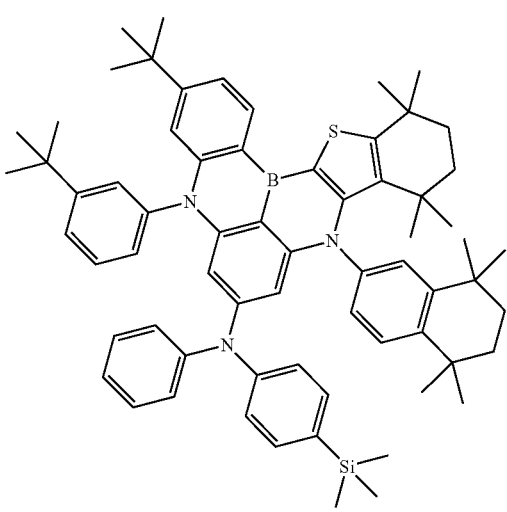

2201
-continued
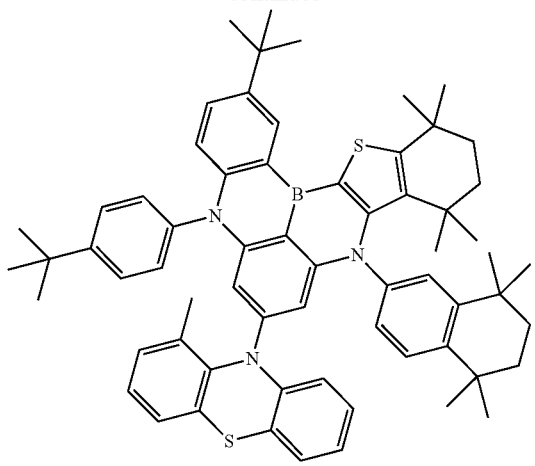
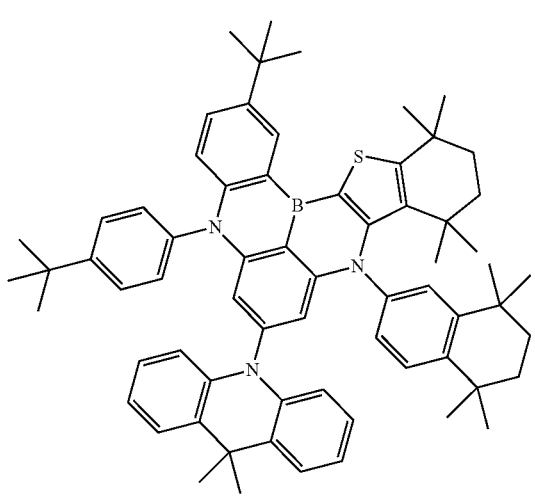
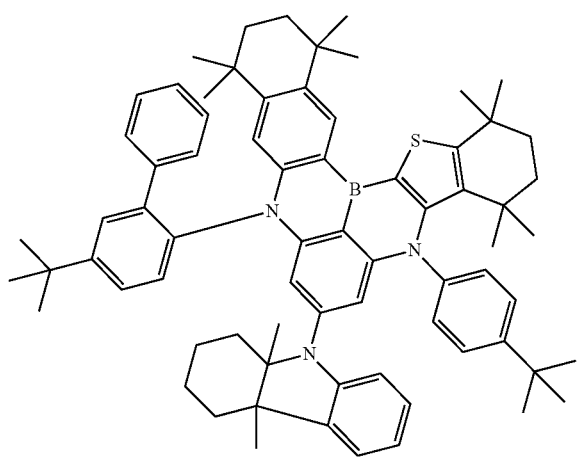
2202
-continued
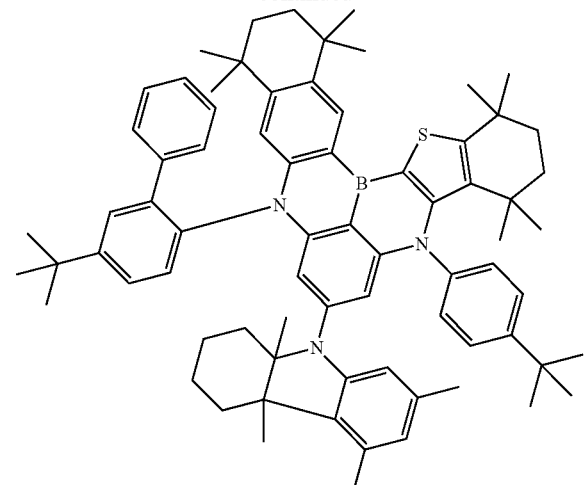
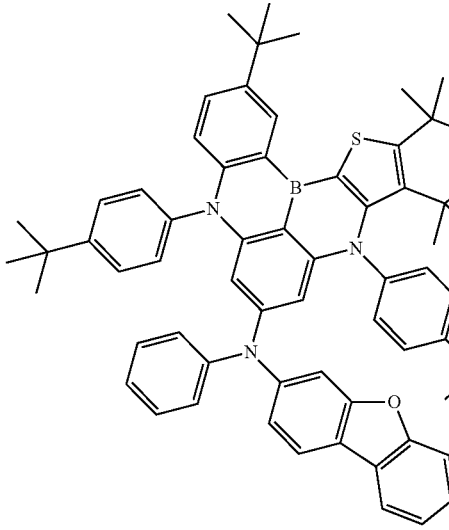
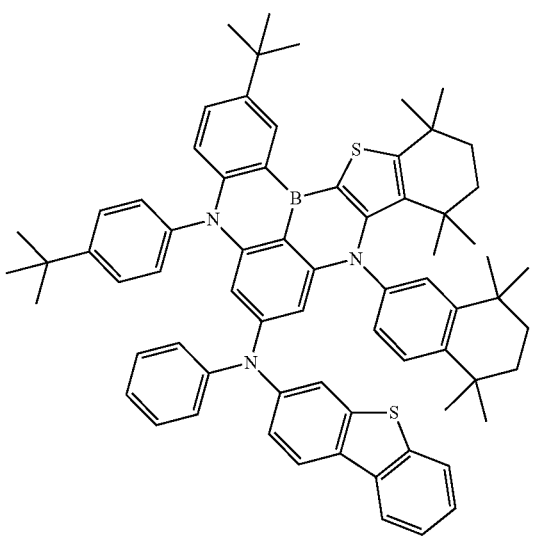

2203
-continued
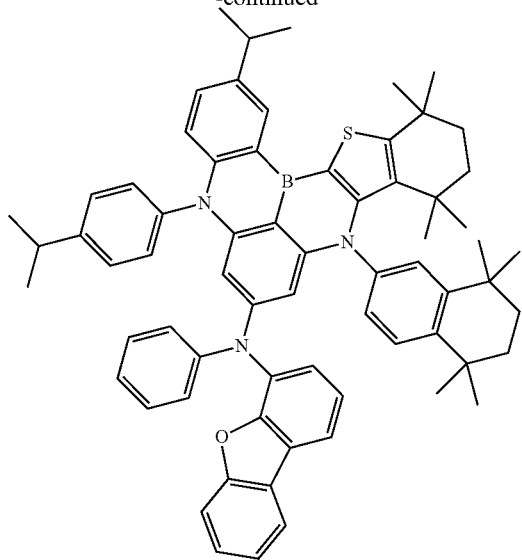
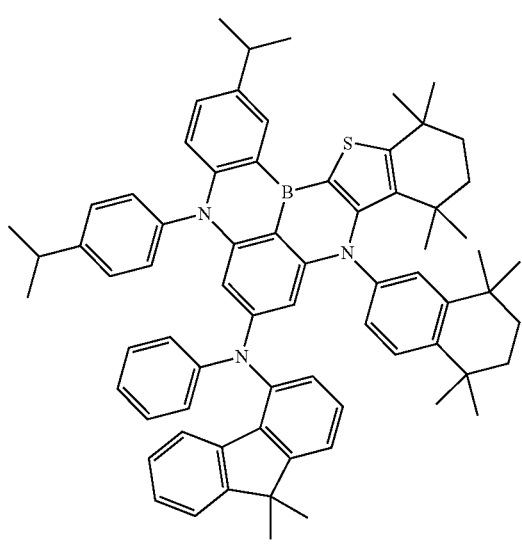
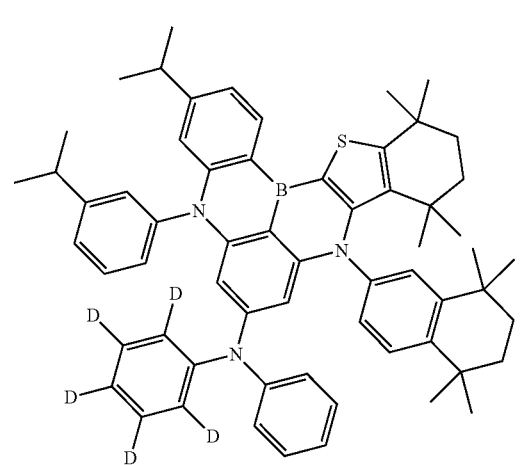
2204
-continued
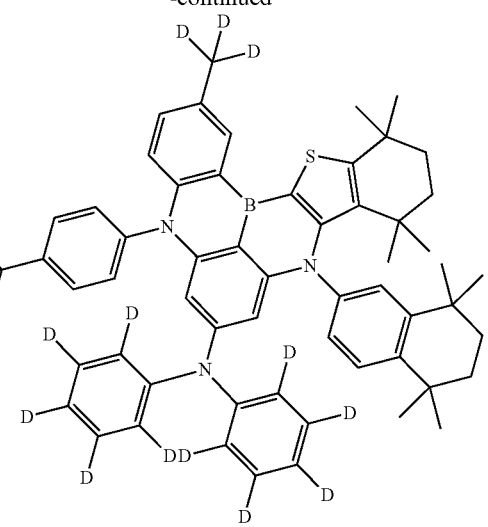
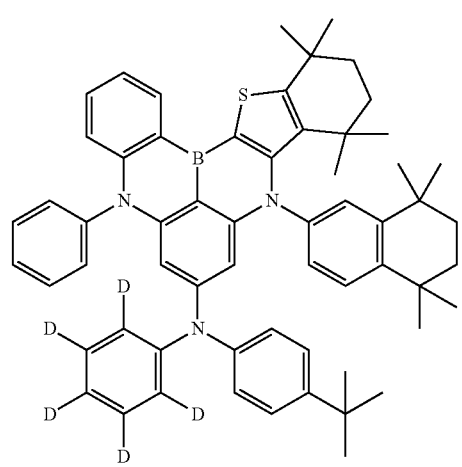
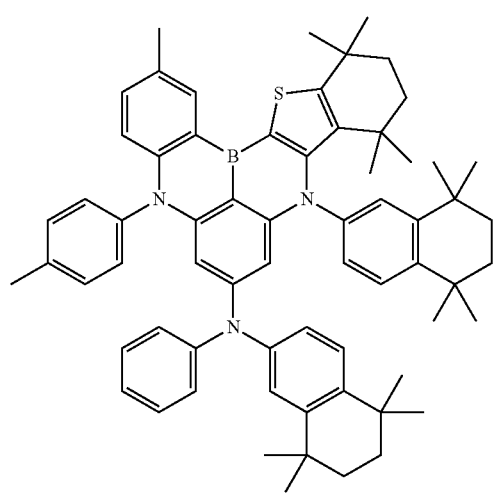

2205
-continued

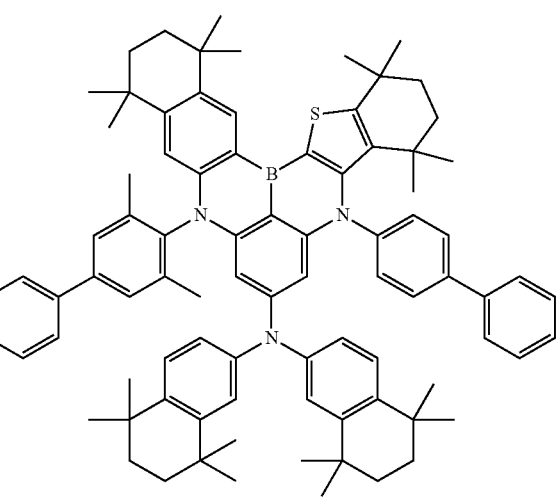
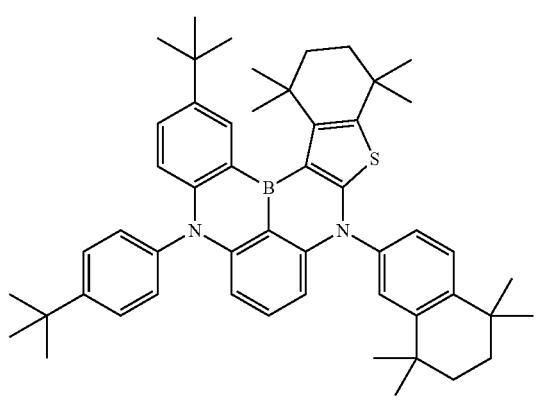
2206
-continued
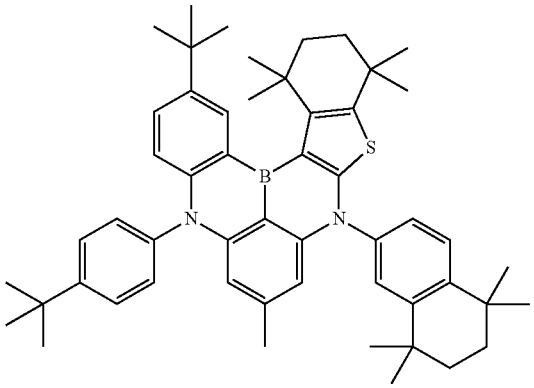
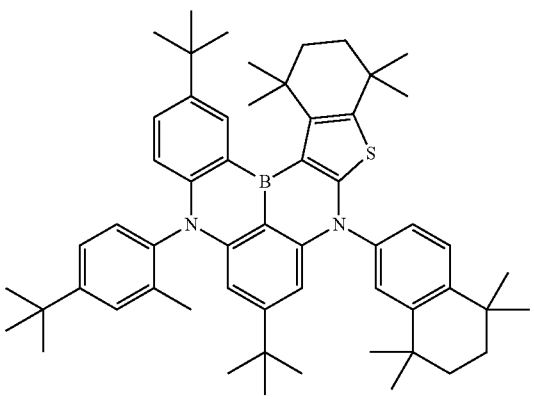
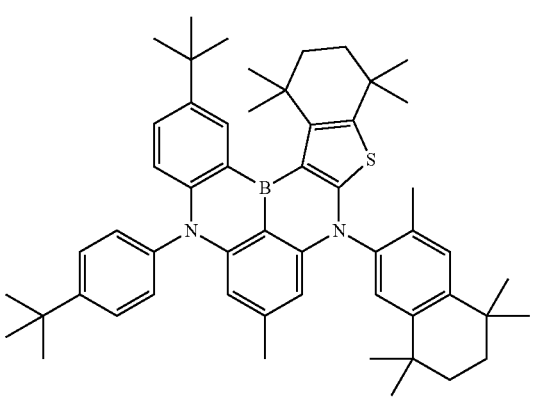

2207
-continued
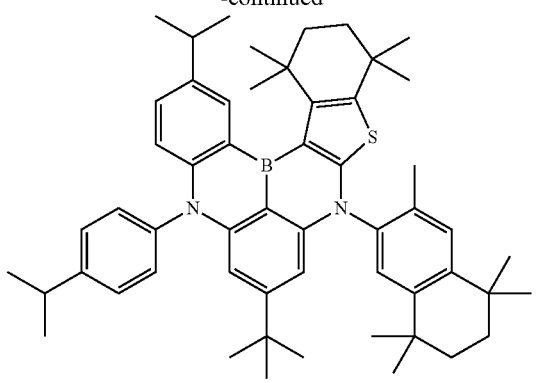
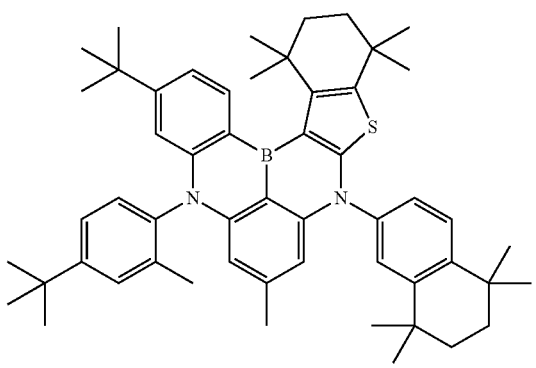
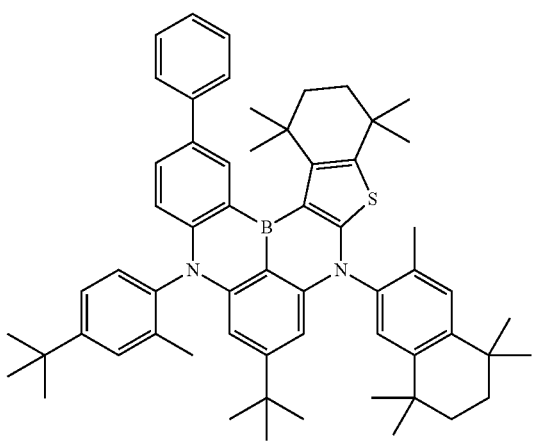
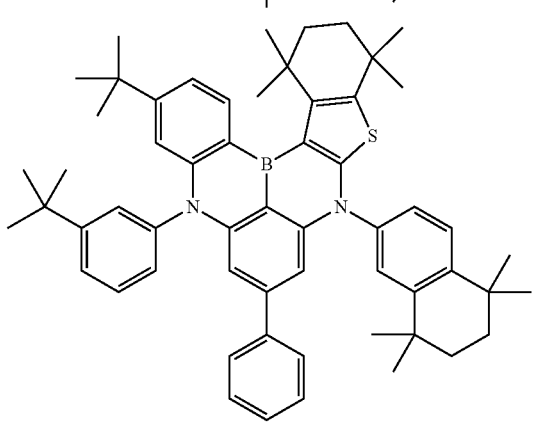
2208
-continued
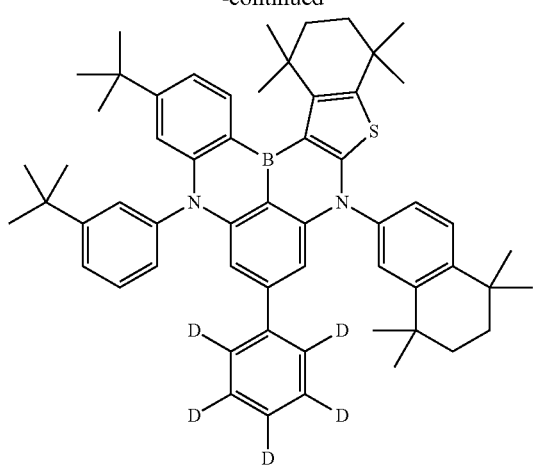
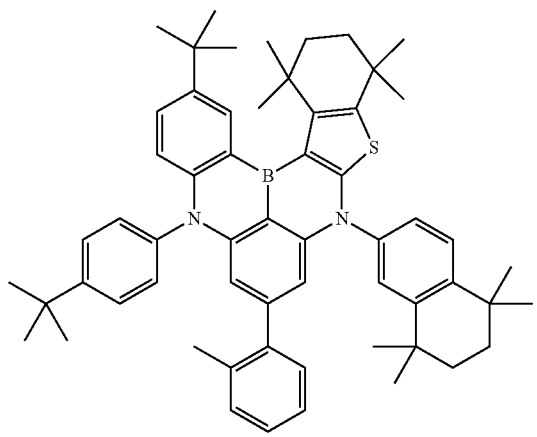
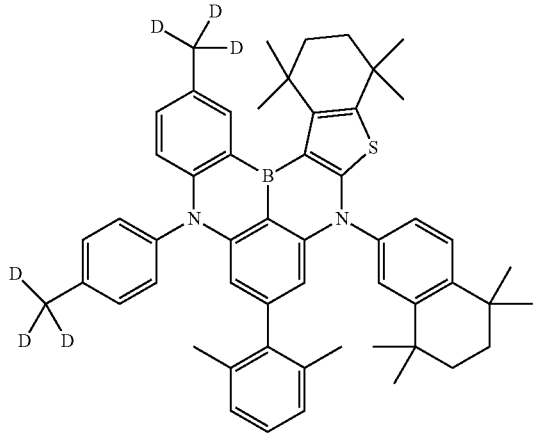

2209
-continued
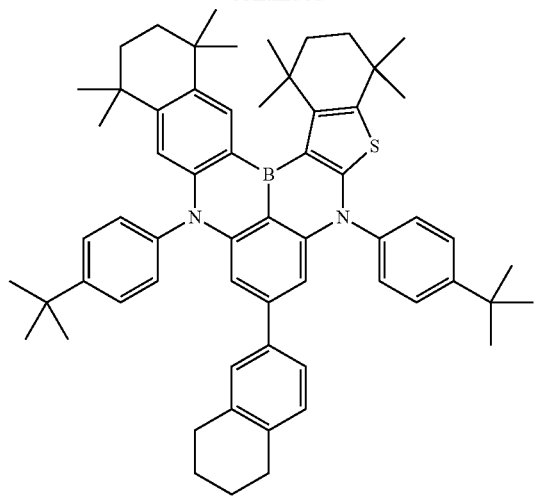
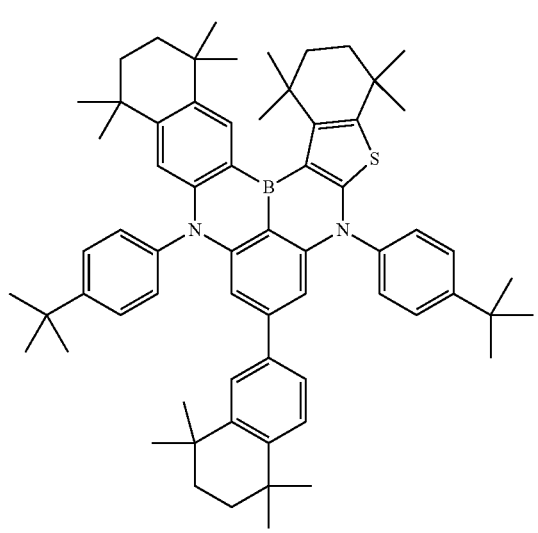
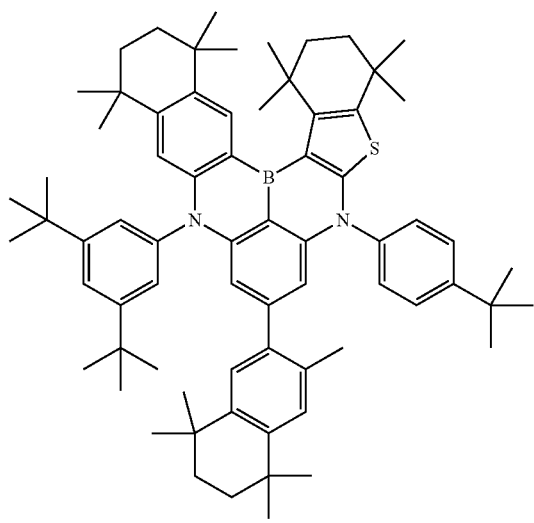
2210
-continued
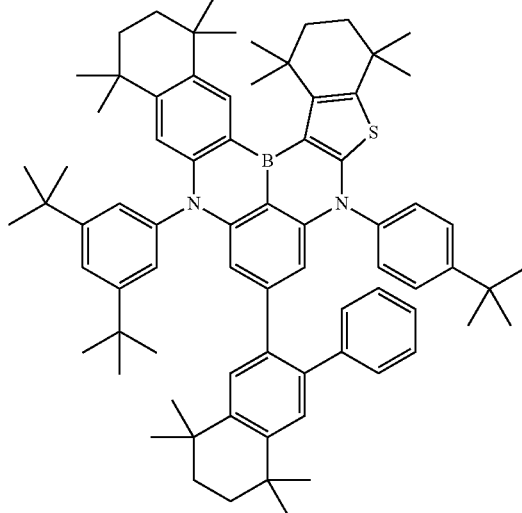
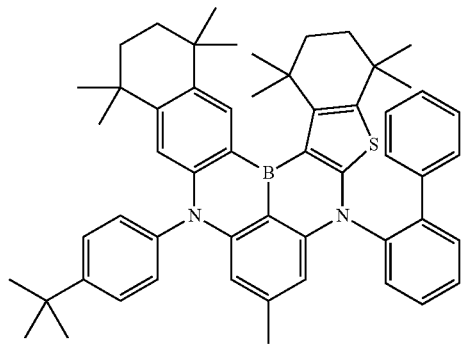
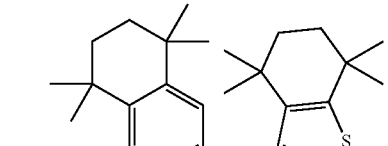
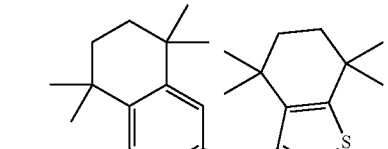
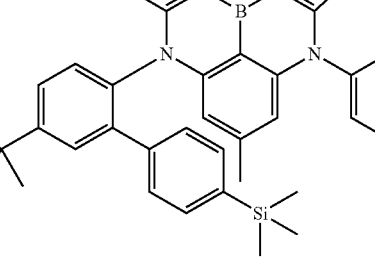

2211 -continued
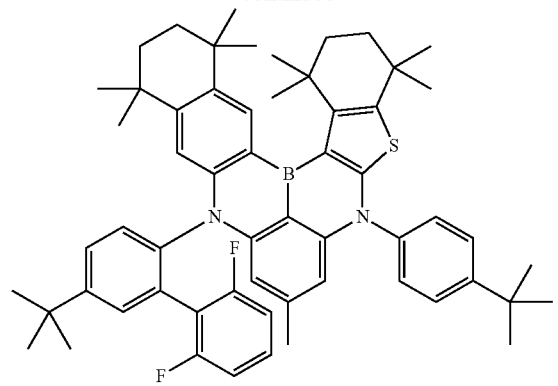
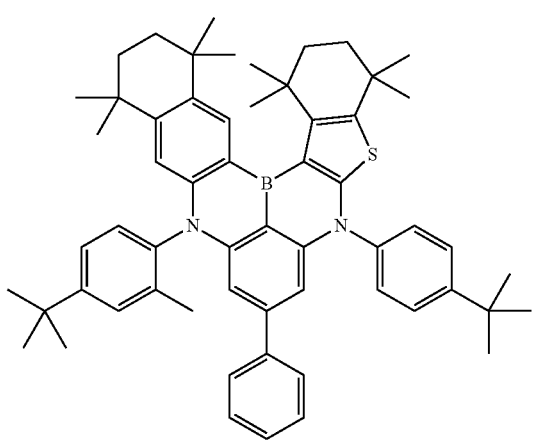
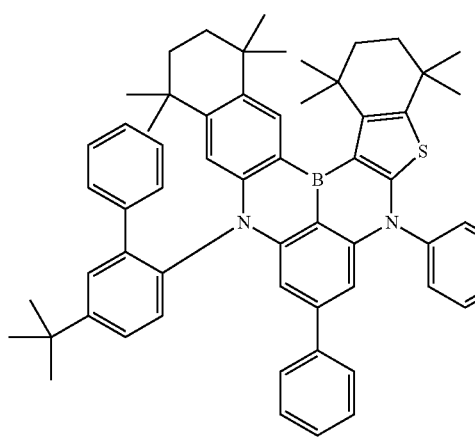
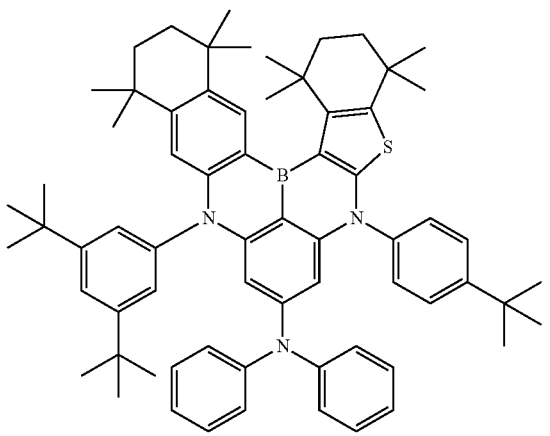
2212 -continued
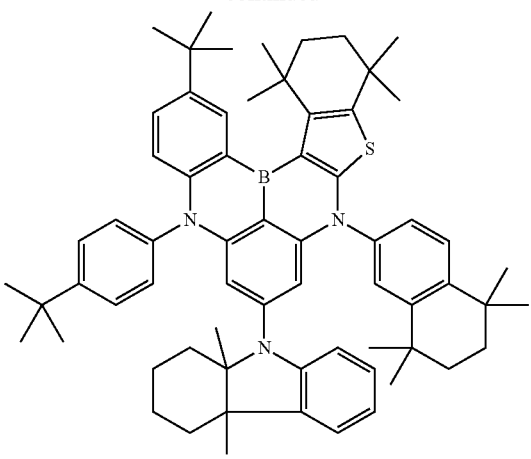
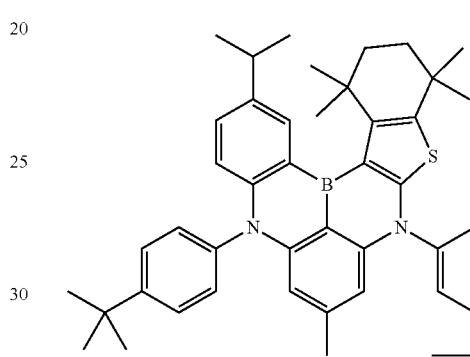
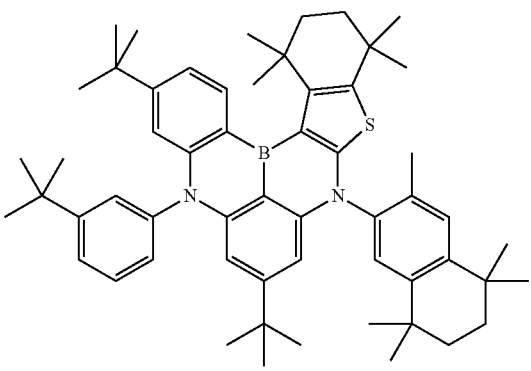
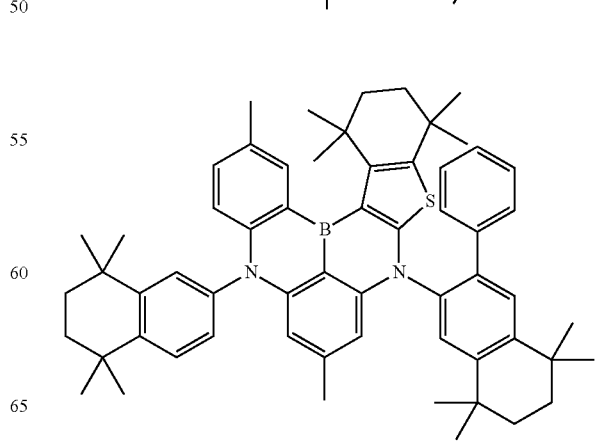

2213
-continued
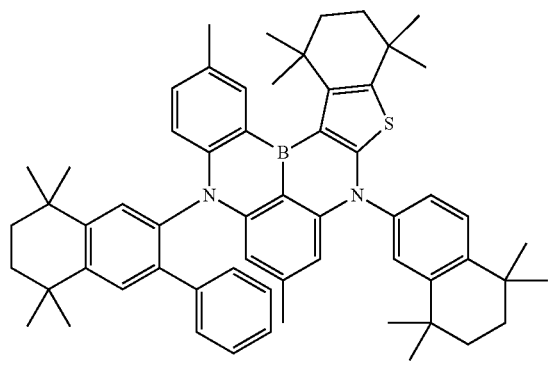
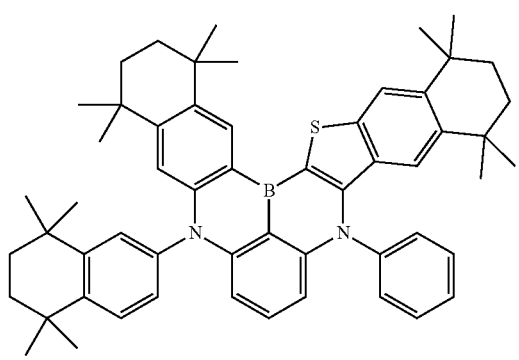
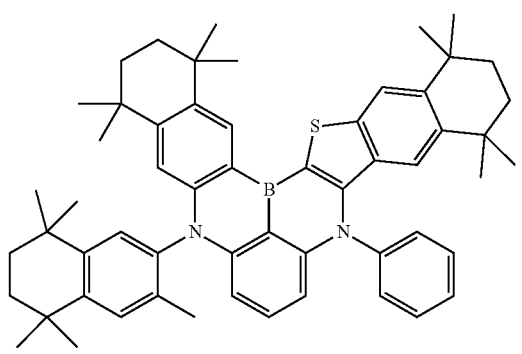
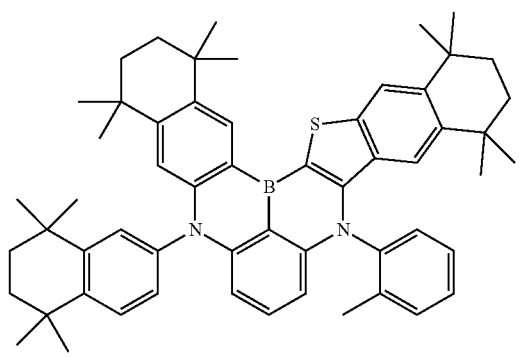
2214
-continued
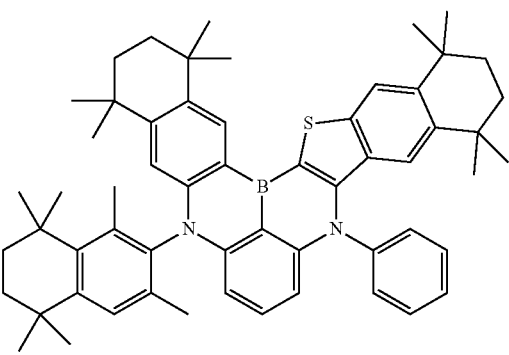
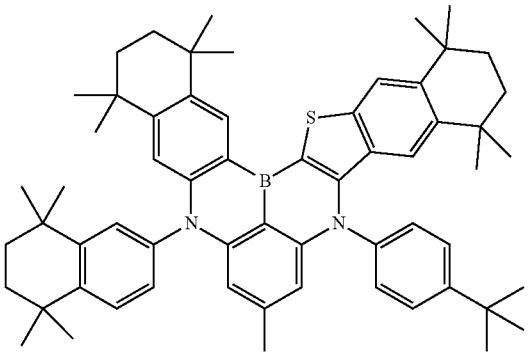
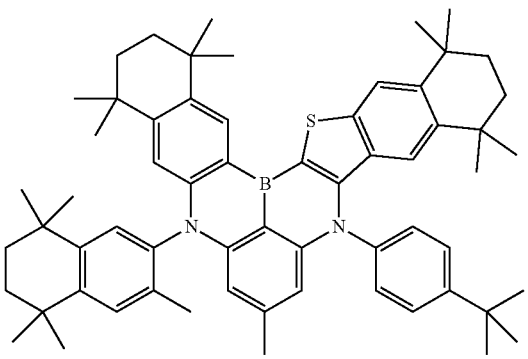
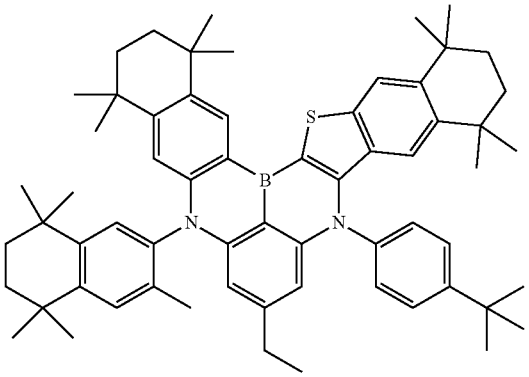

2215
-continued
2216
-continued
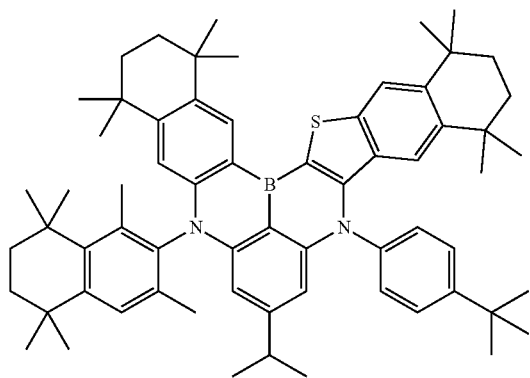
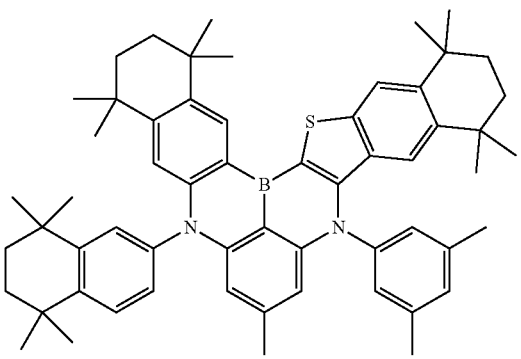

2217
-continued
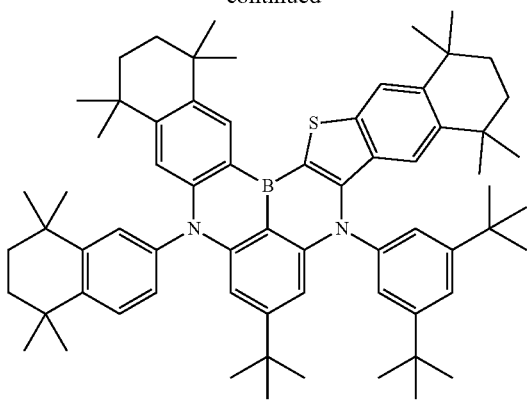
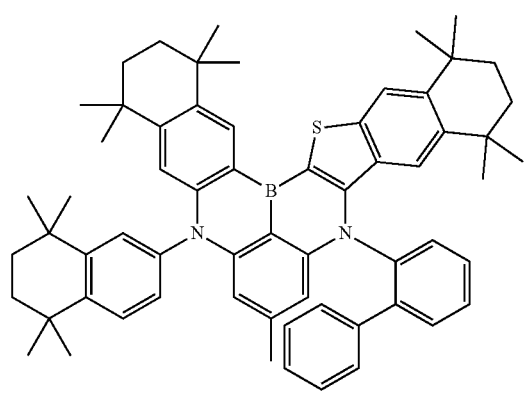
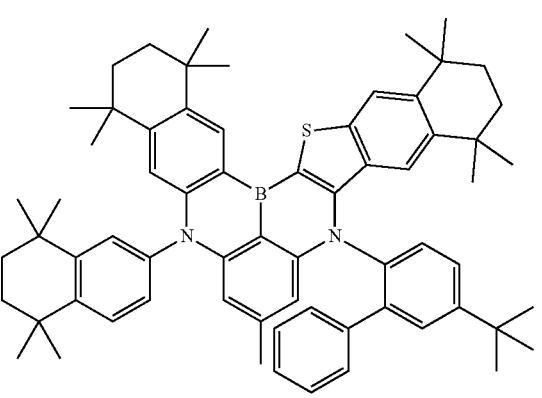
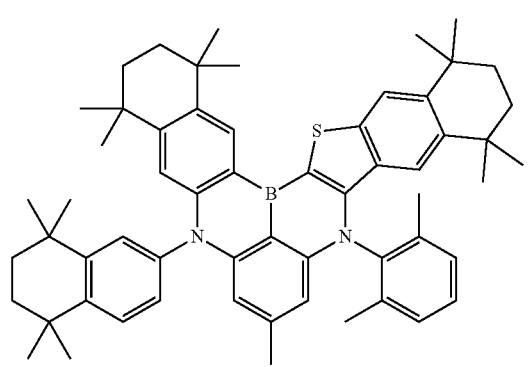
2218
-continued
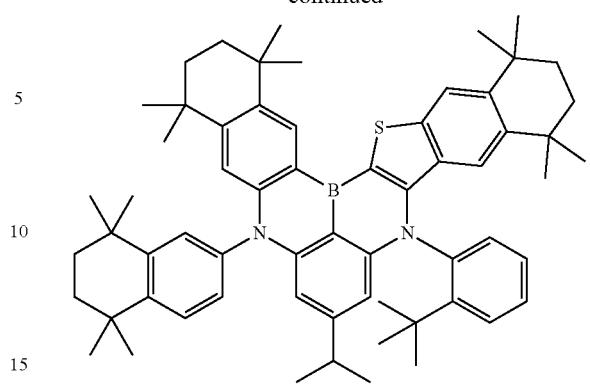
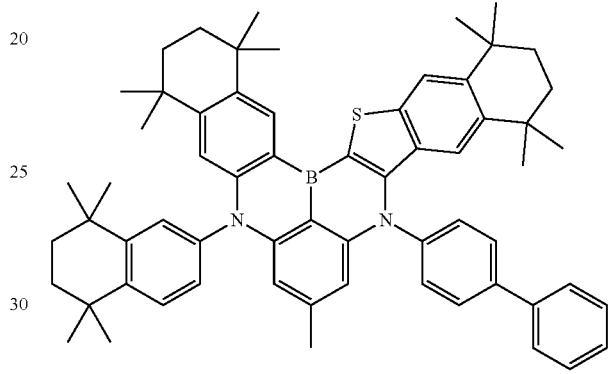
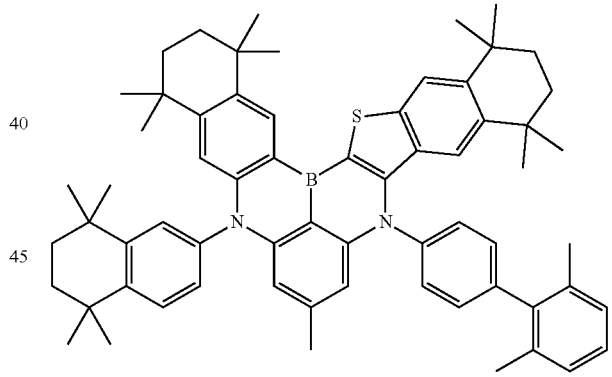
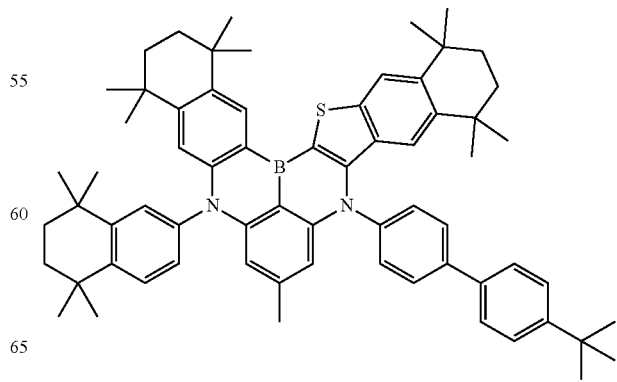

2219
-continued
2220
-continued
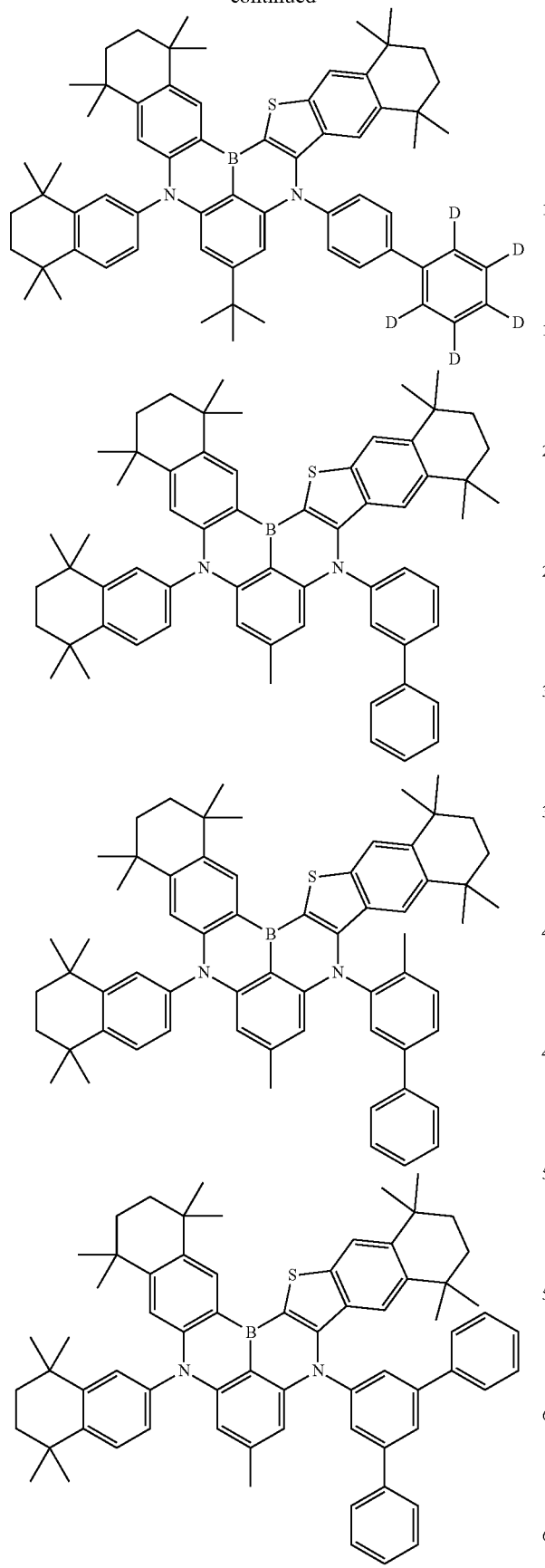
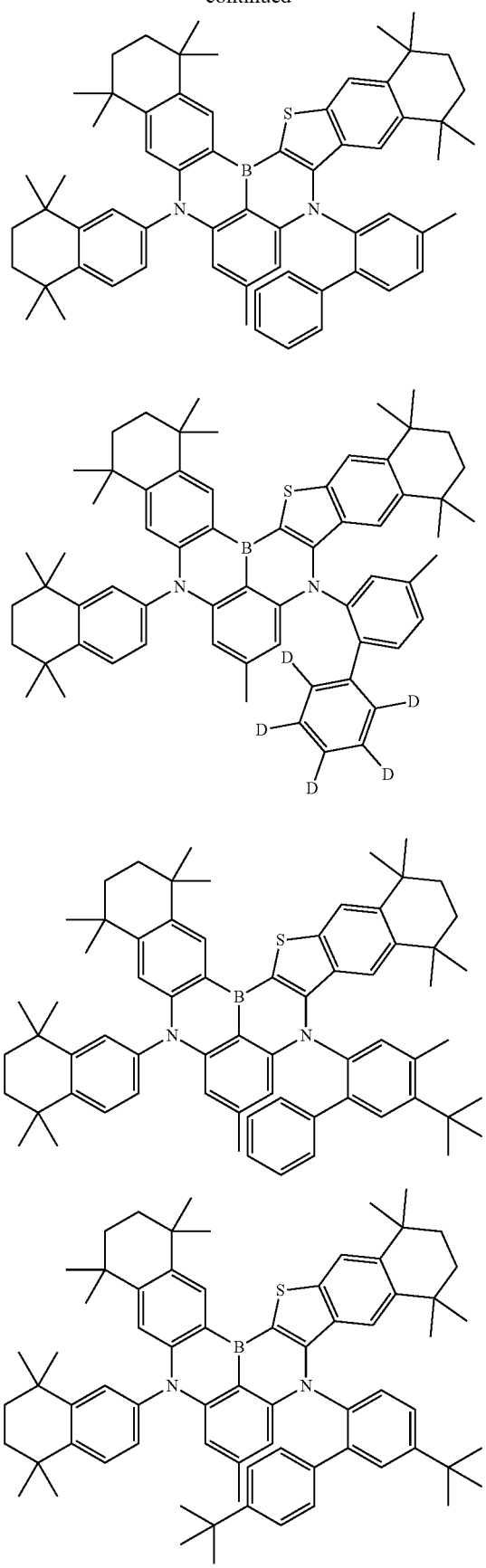

2221
-continued
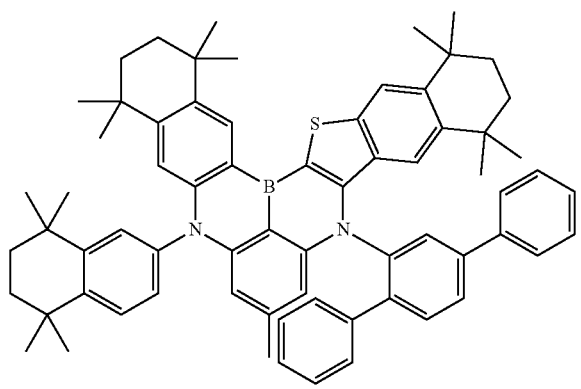
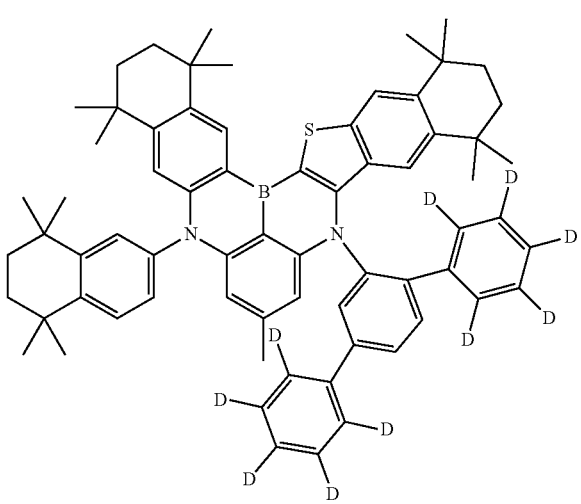
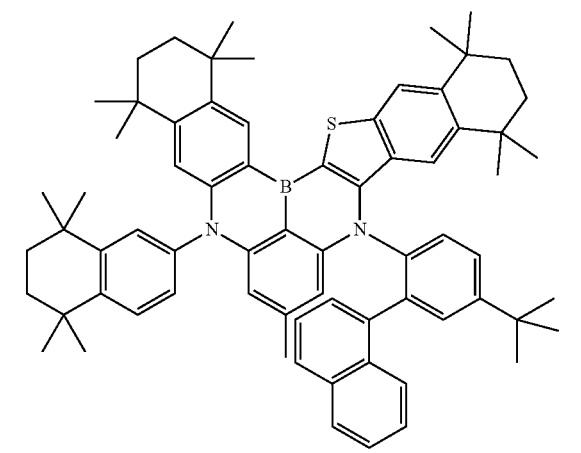
2222
-continued
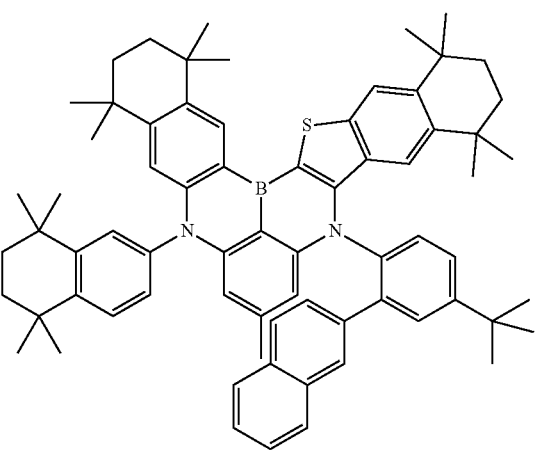
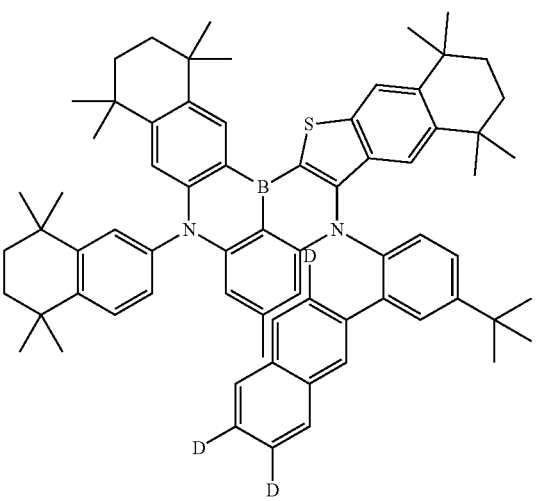
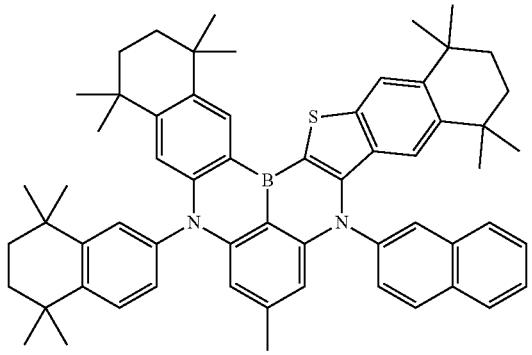

2223
-continued
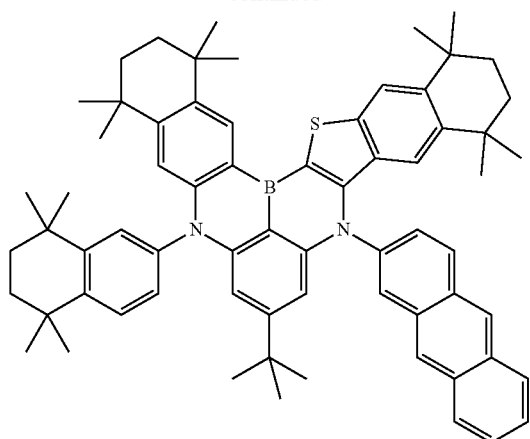
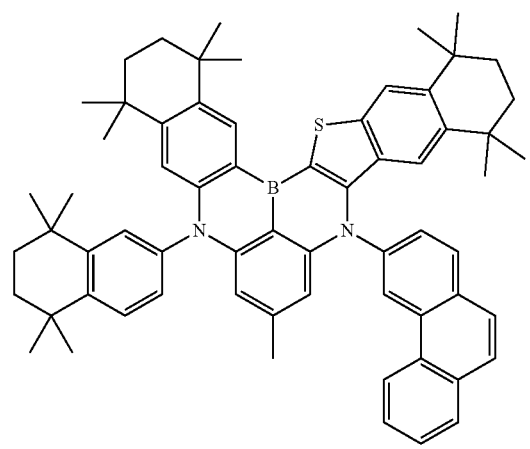
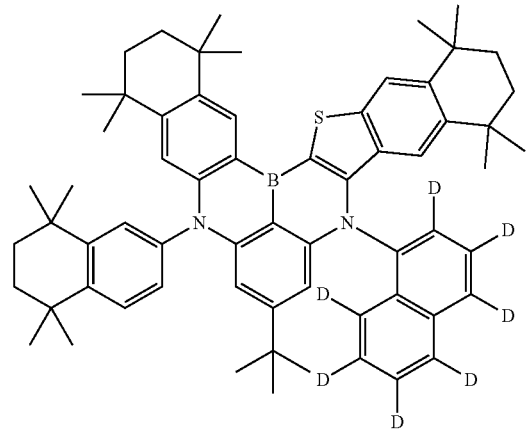
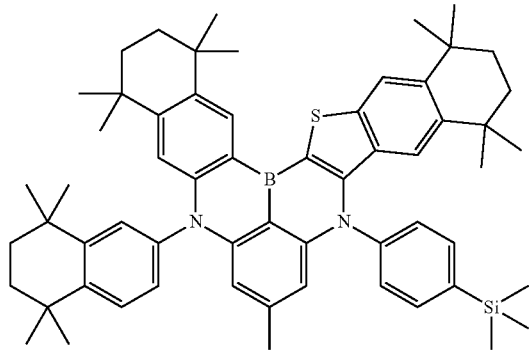
2224
-continued
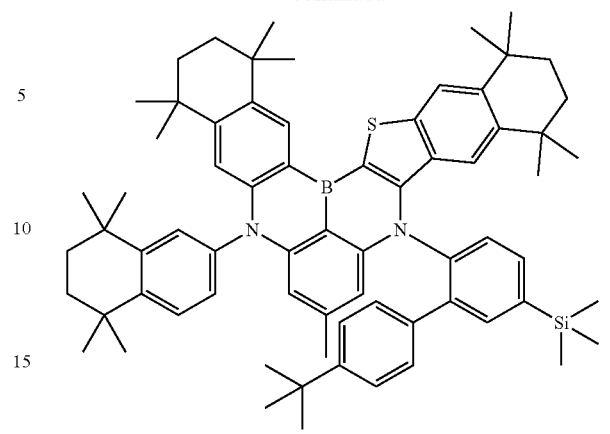
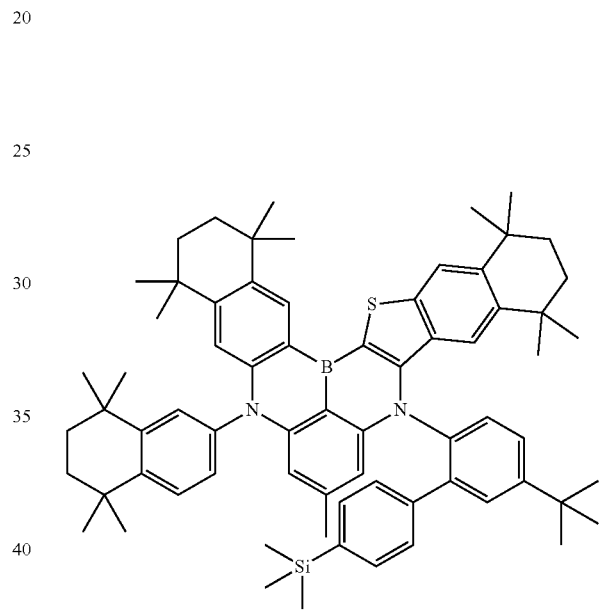
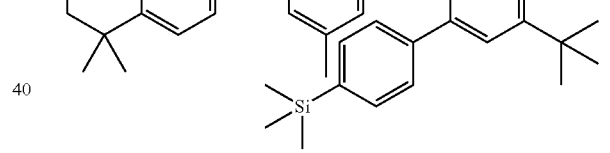
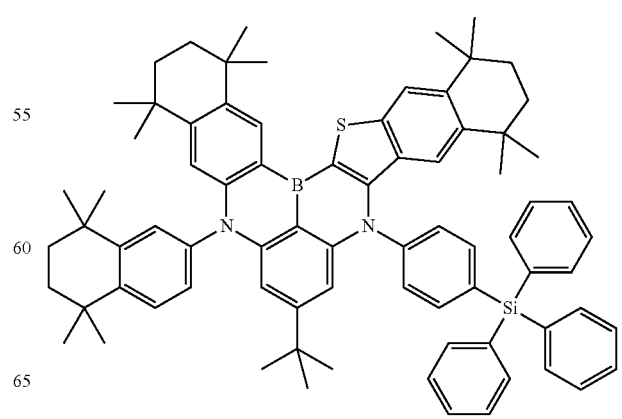

2225
-continued
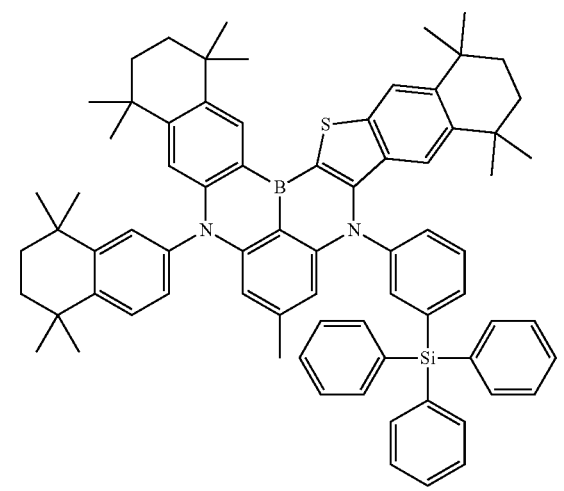
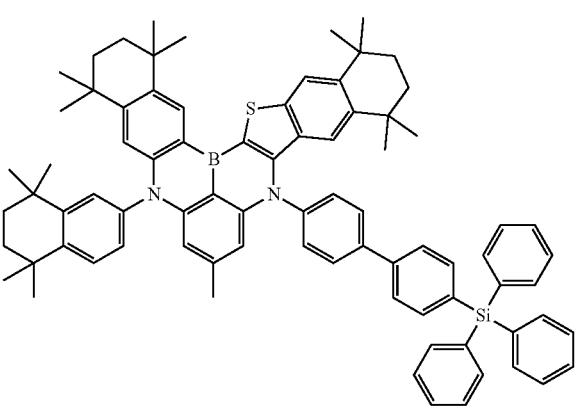
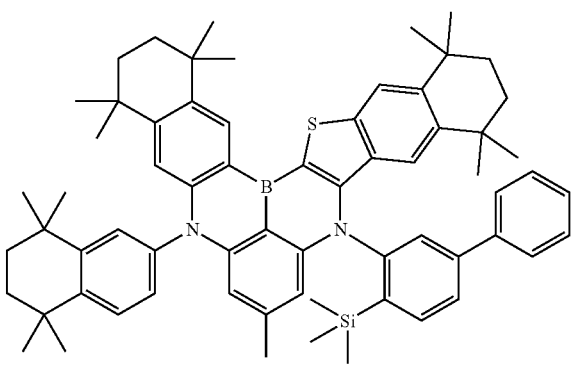
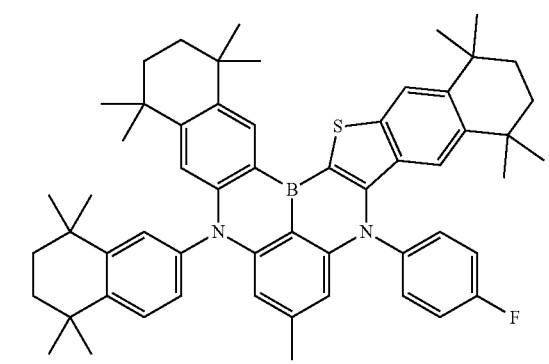
2226
-continued
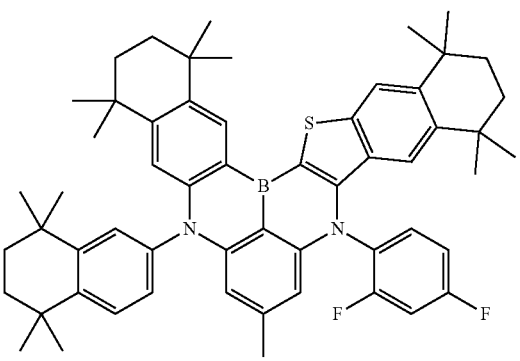
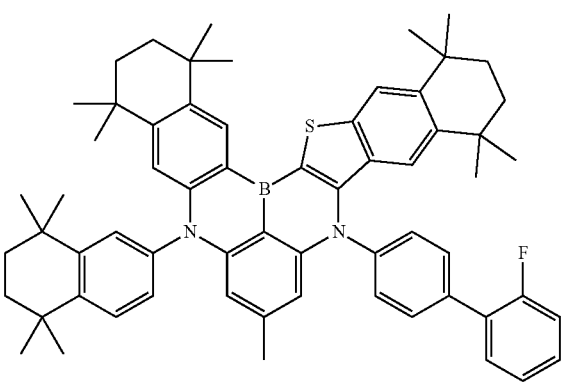
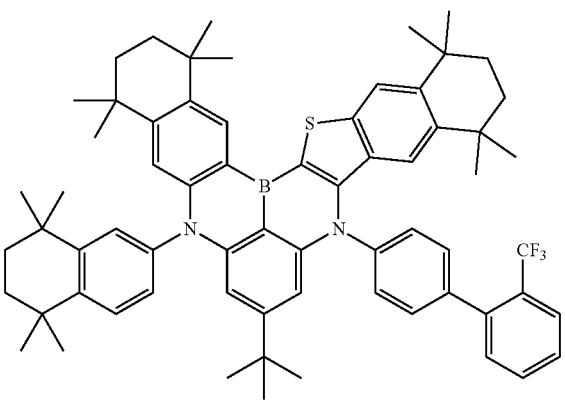
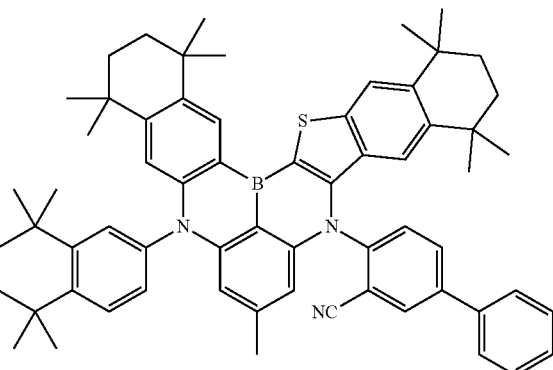

2227
-continued
2228
-continued
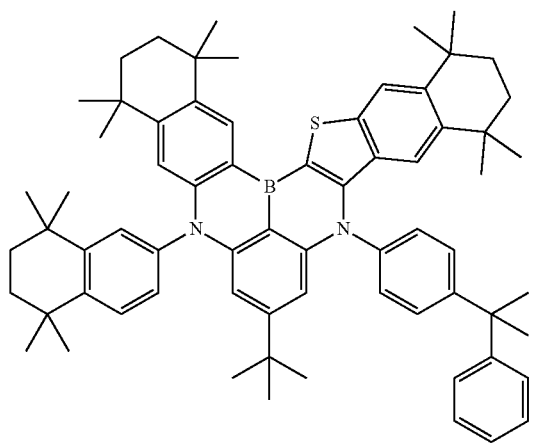
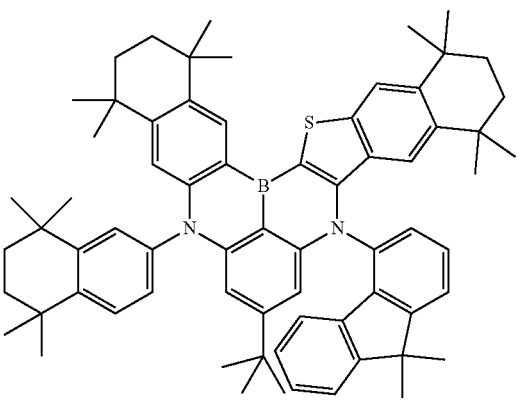
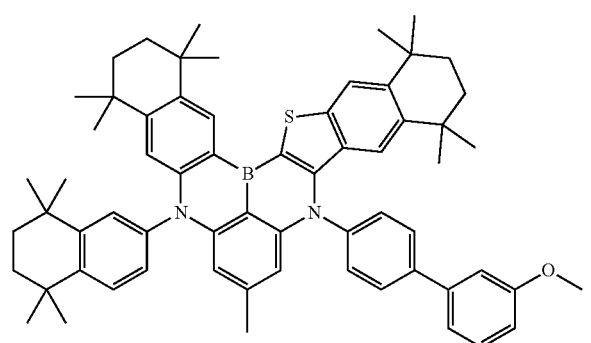
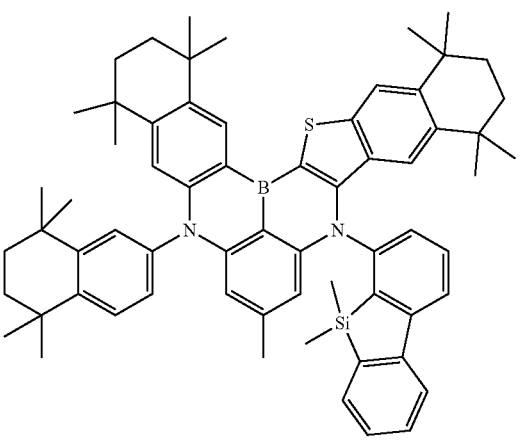
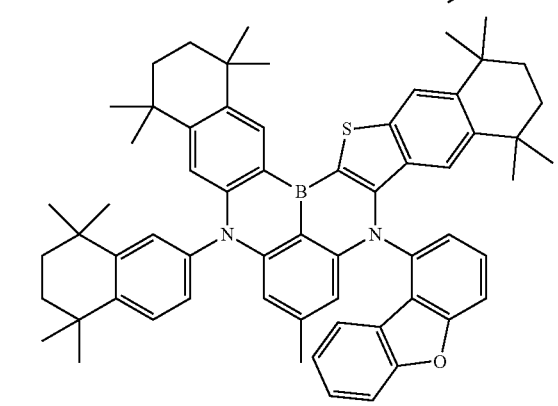
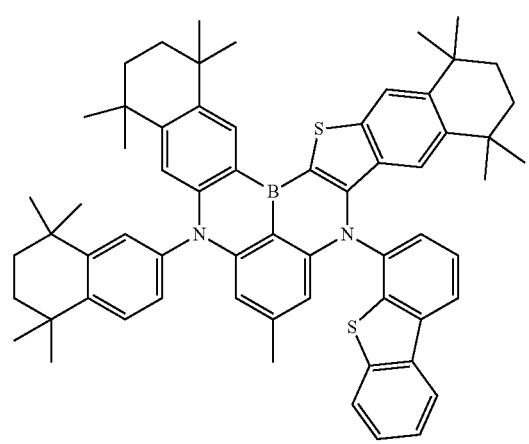
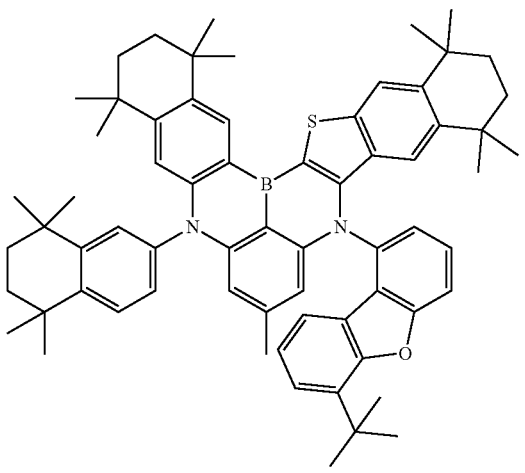

2229
-continued
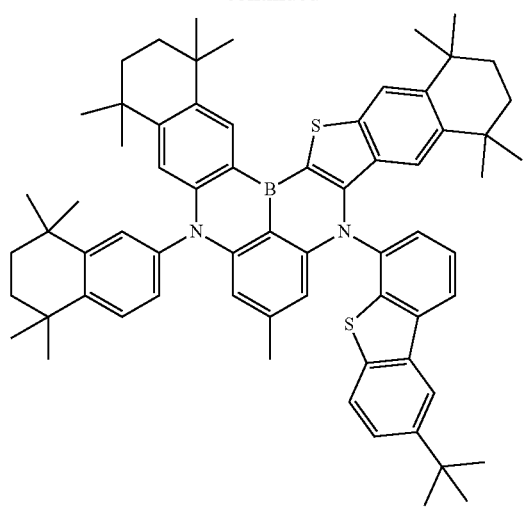
2230
-continued
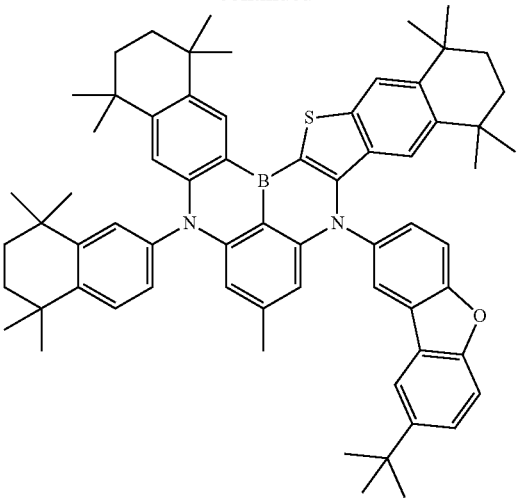
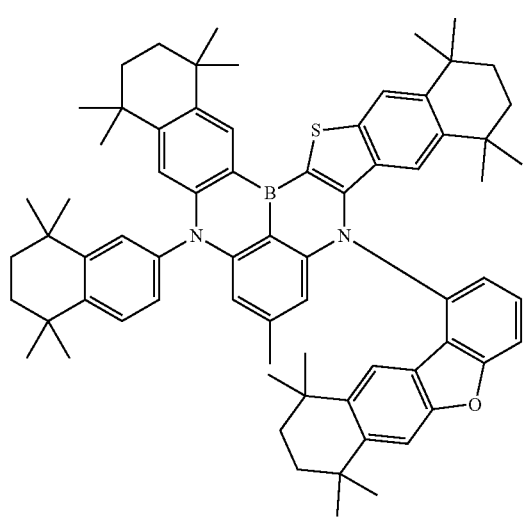
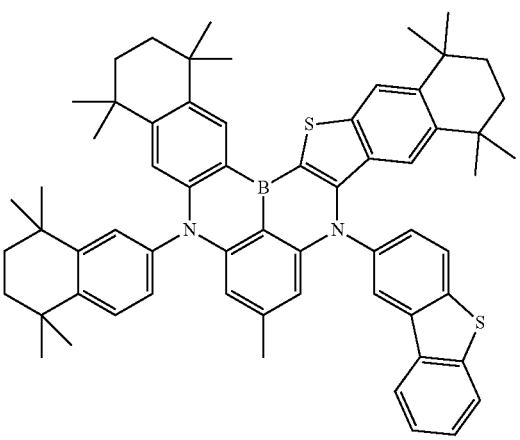
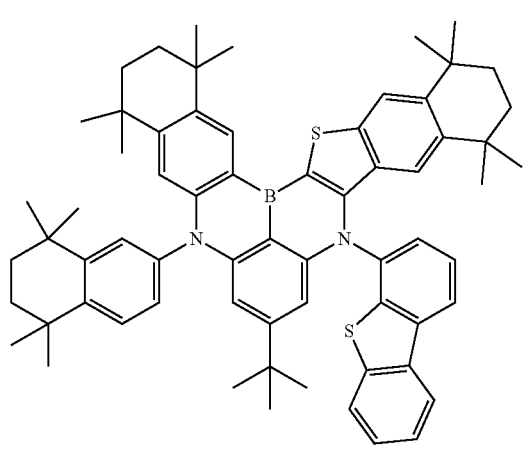
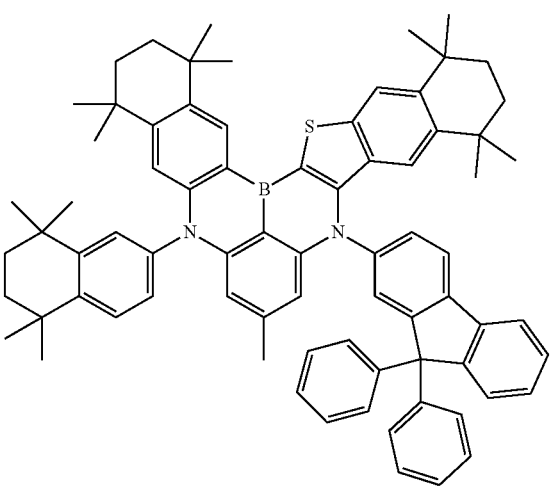

2231
-continued
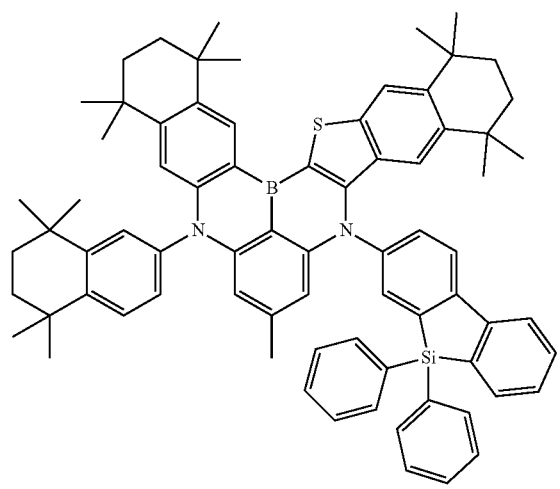
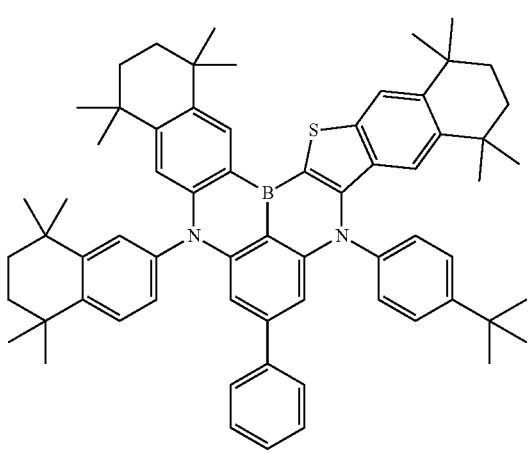
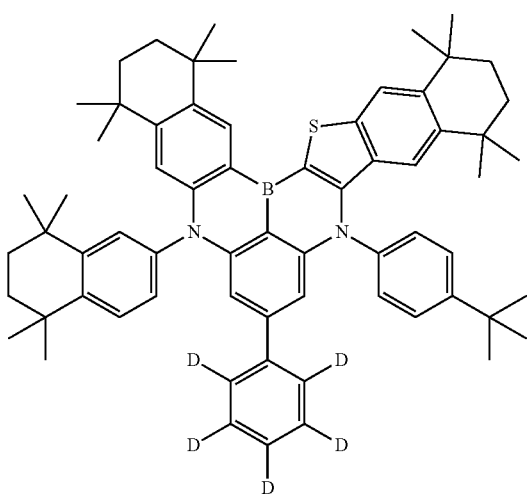
2232
-continued
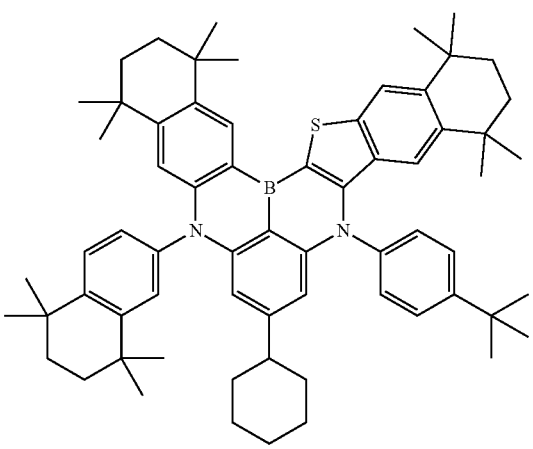
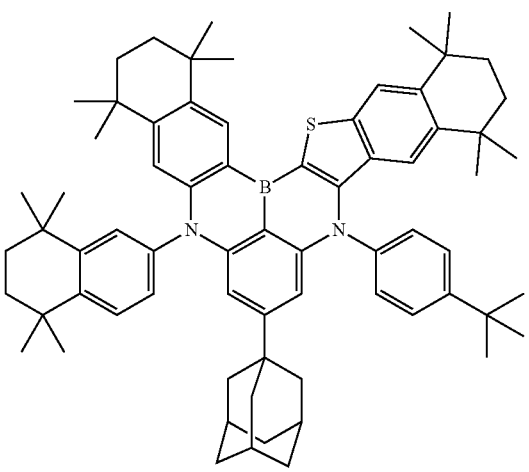
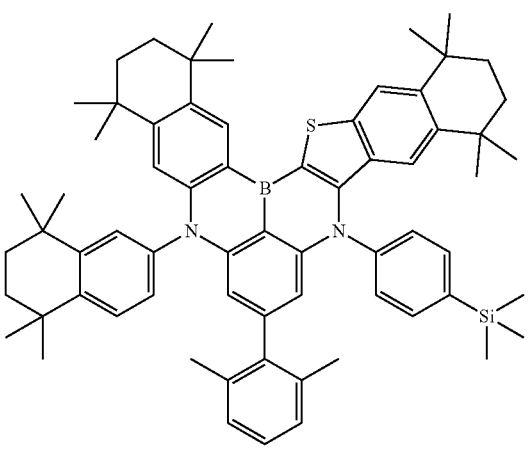

2233
-continued
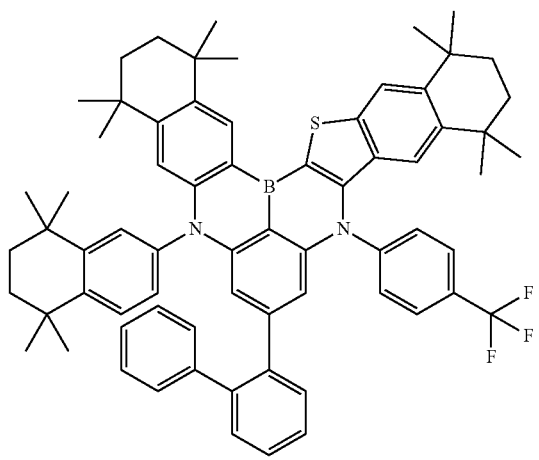
2234
-continued
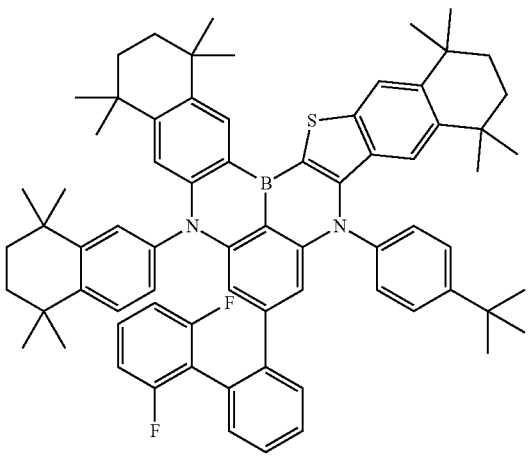
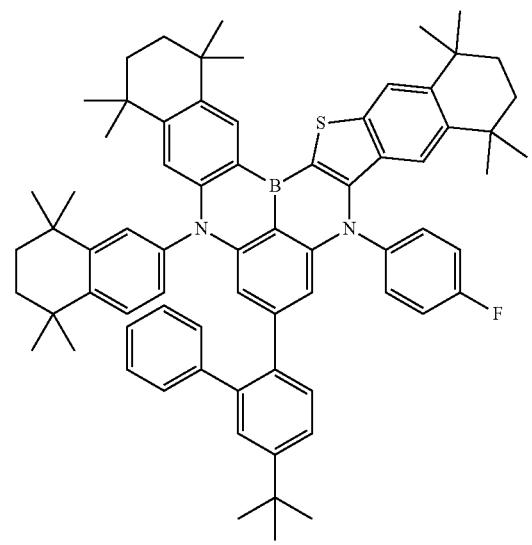
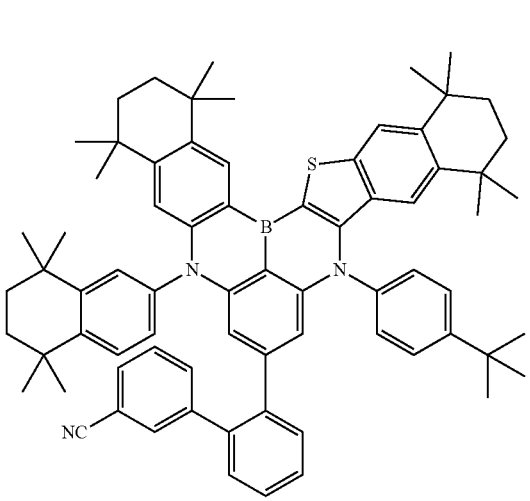
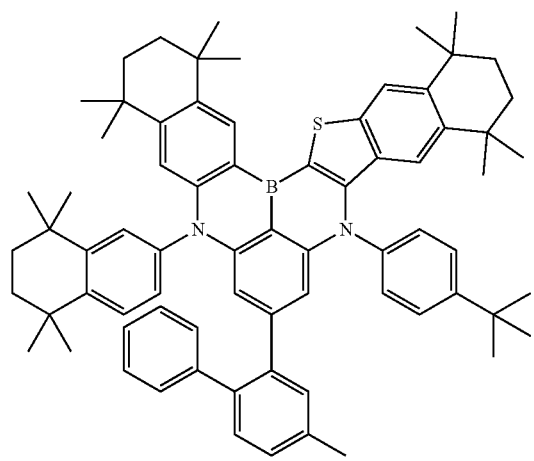
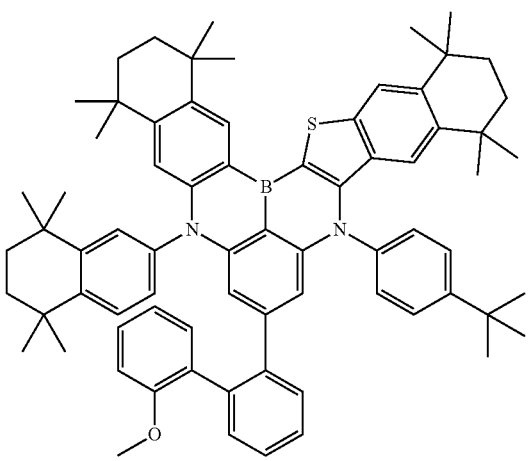

2235
-continued
2236
-continued
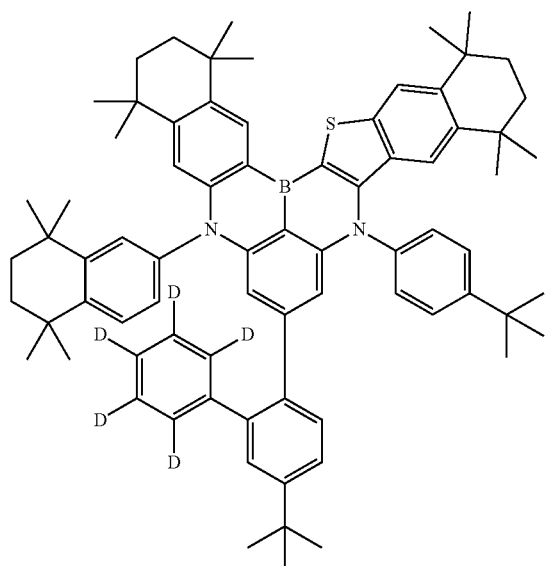
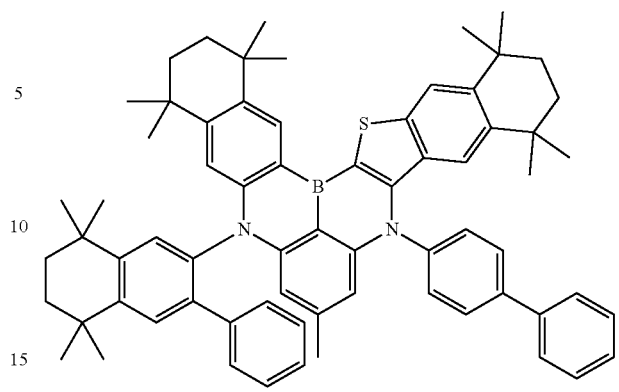
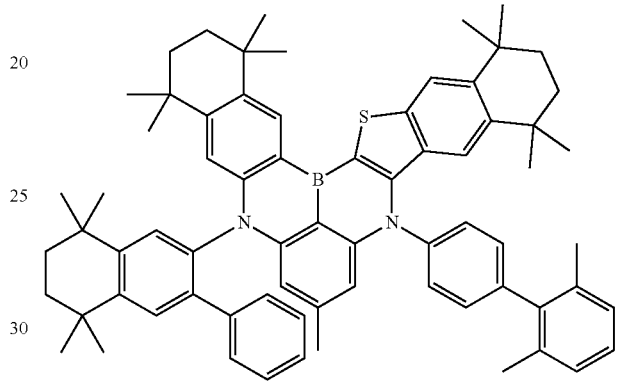
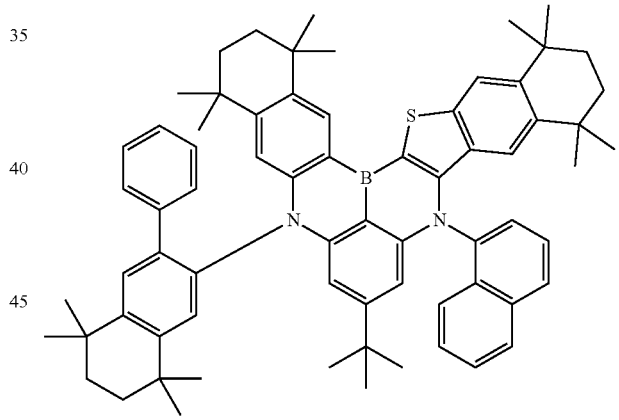
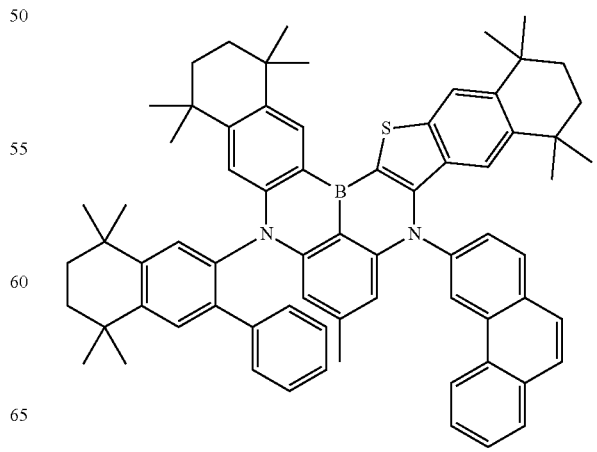

| 2237 | 2238 |
|---|---|
| 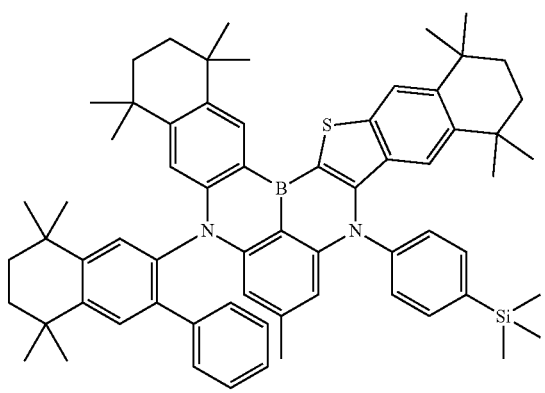 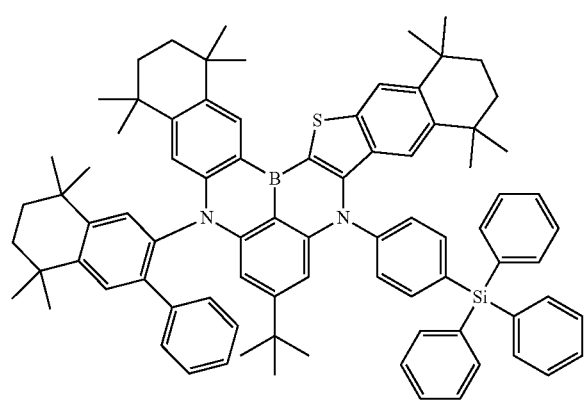 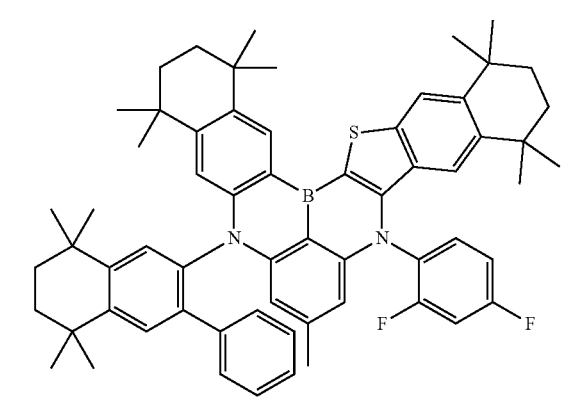 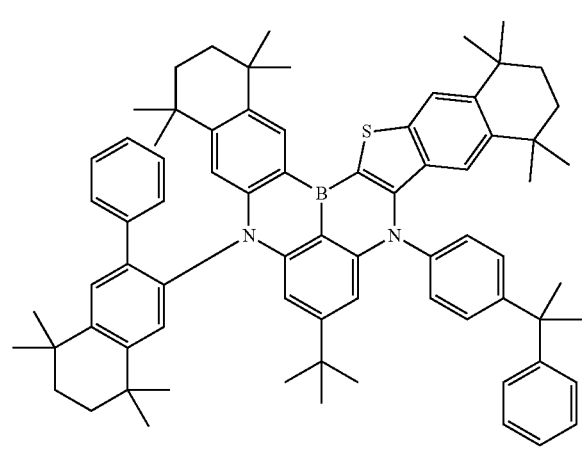 | 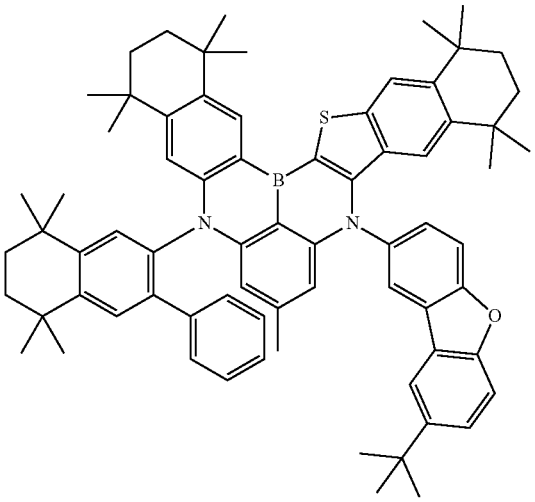 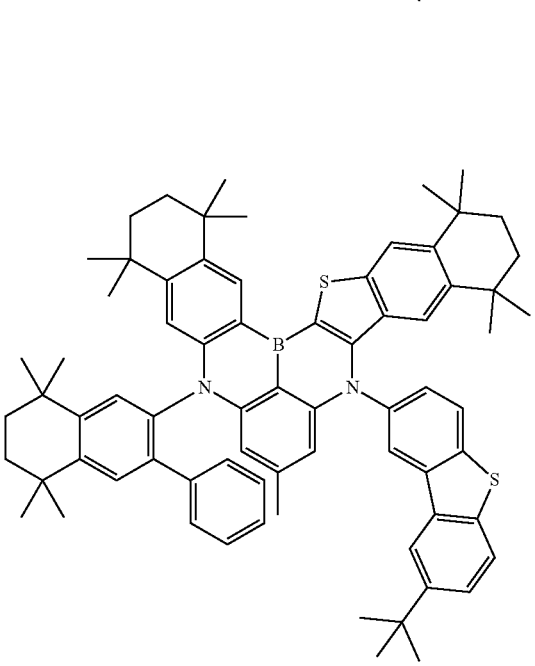 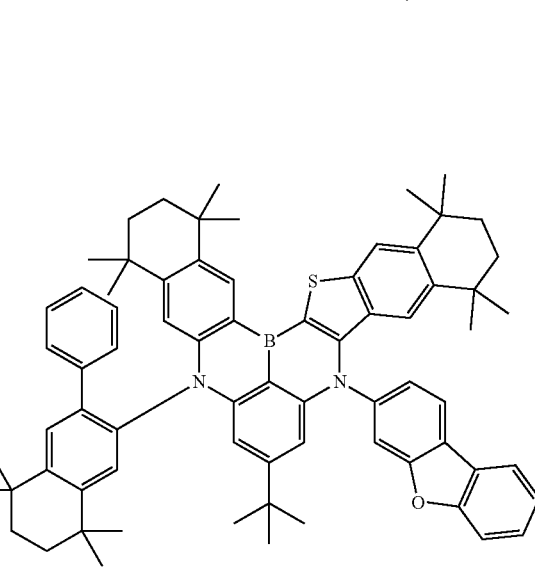 |

2239
-continued
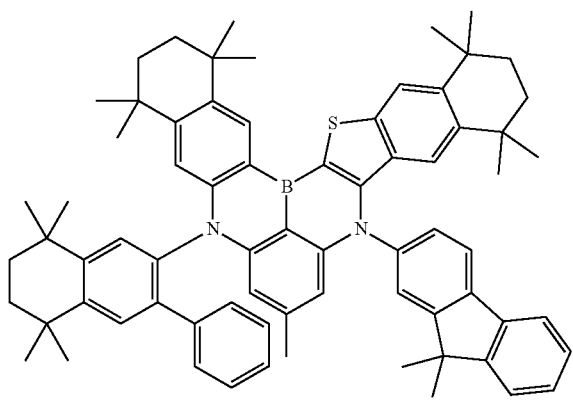
2240
-continued
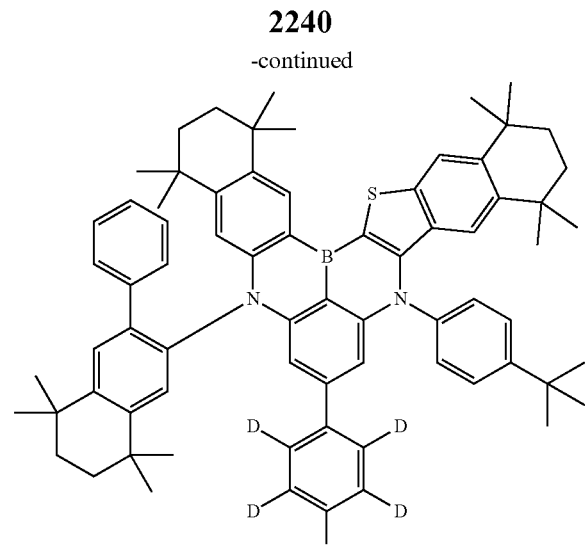
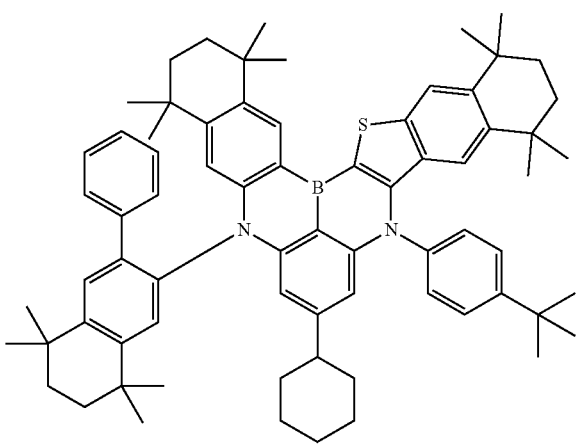
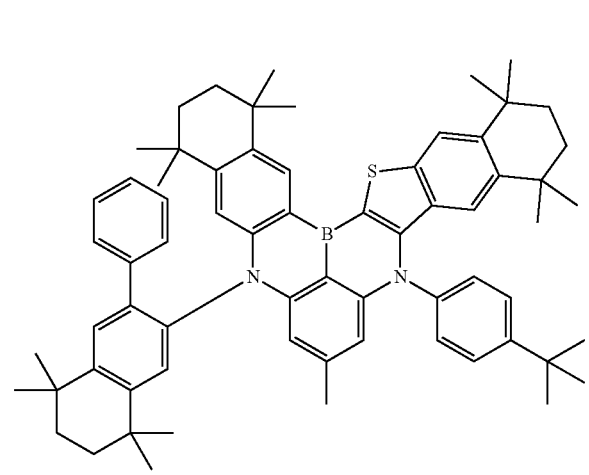
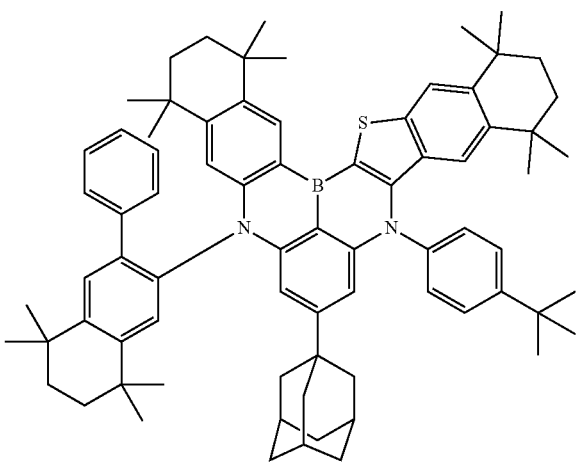
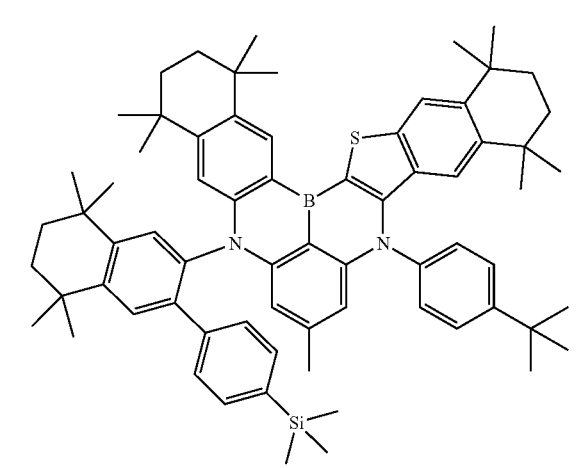

2241
-continued
2242
-continued
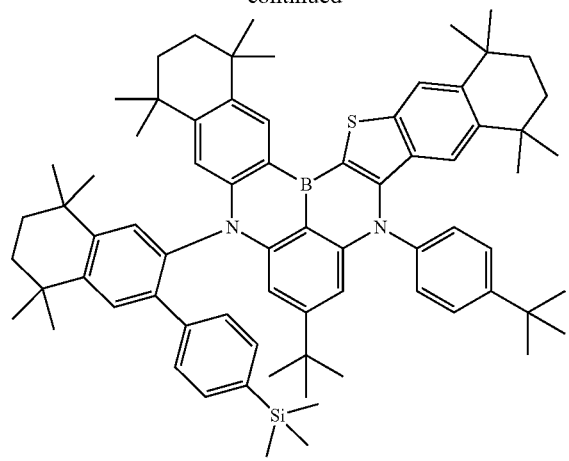
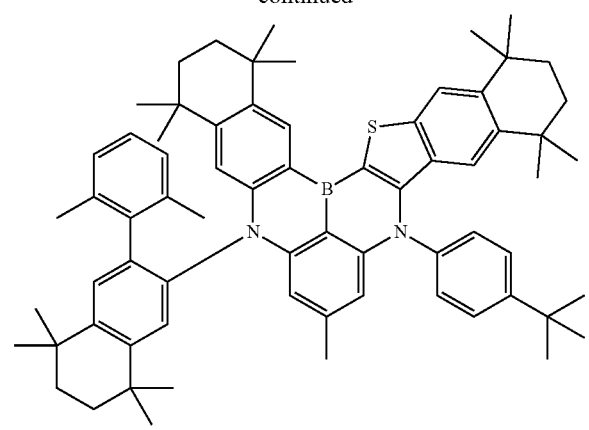
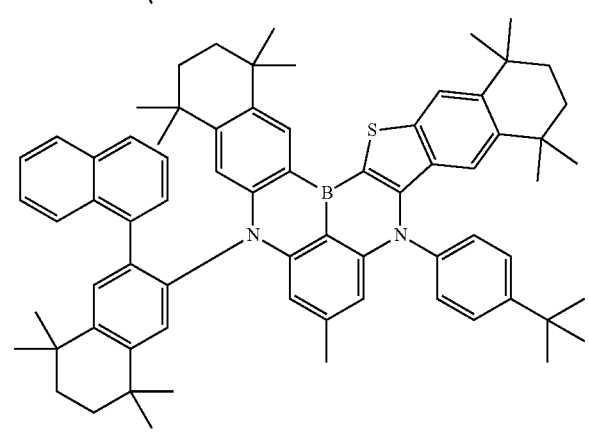
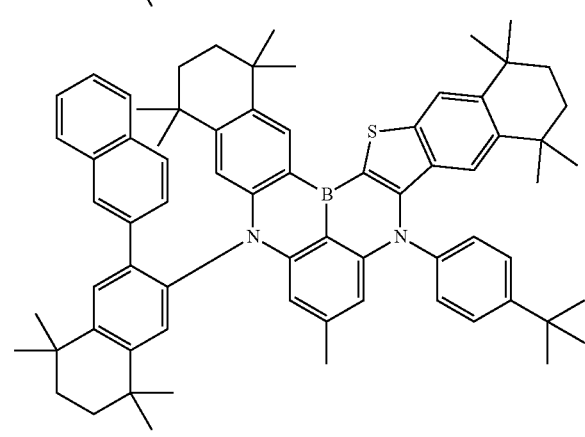

2243
-continued
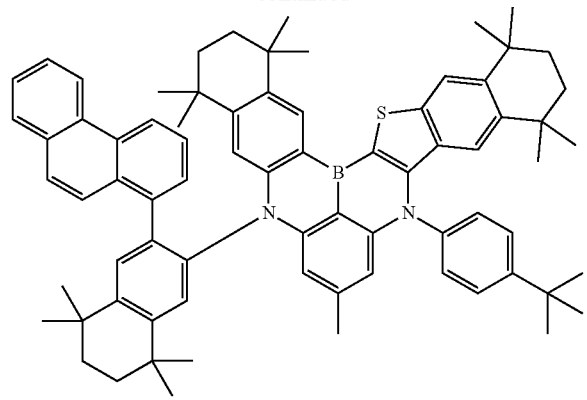
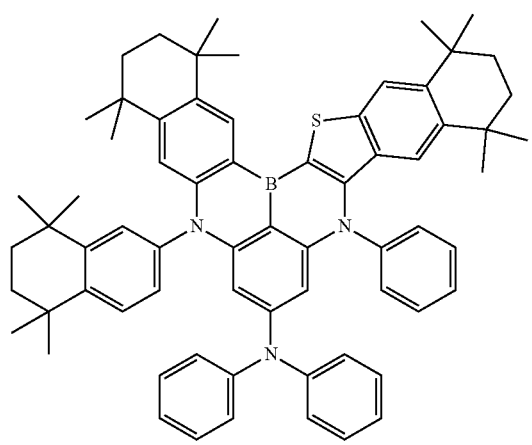
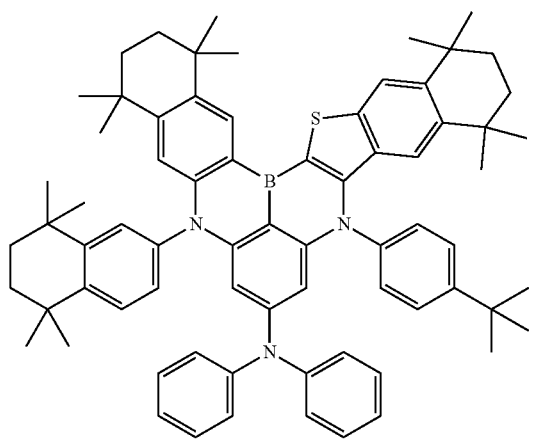
2244
-continued
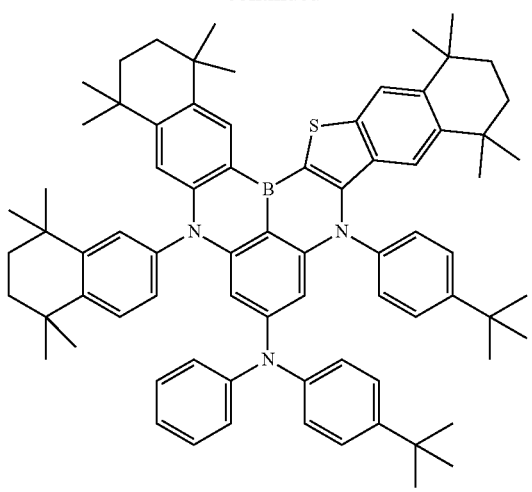
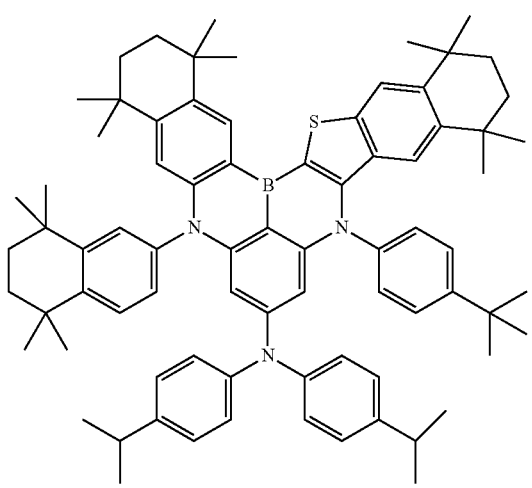
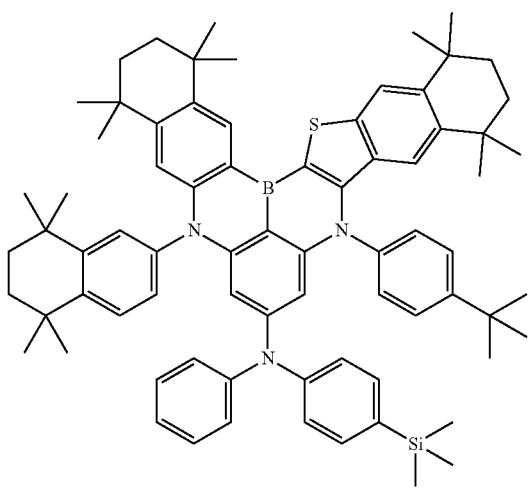

2245
-continued
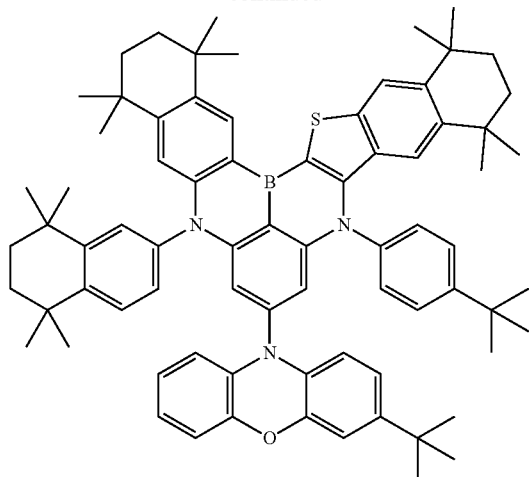
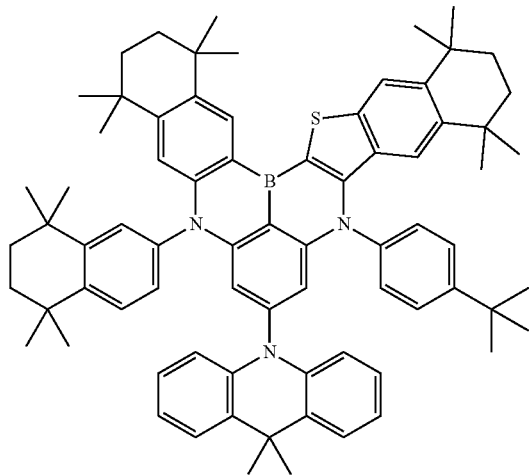
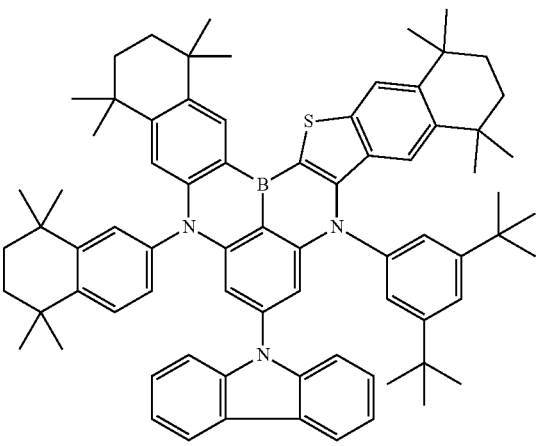
2246
-continued
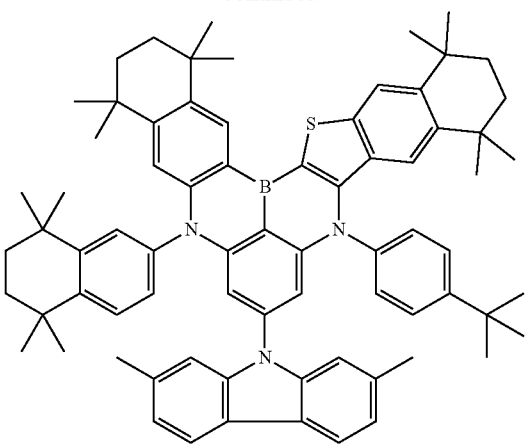
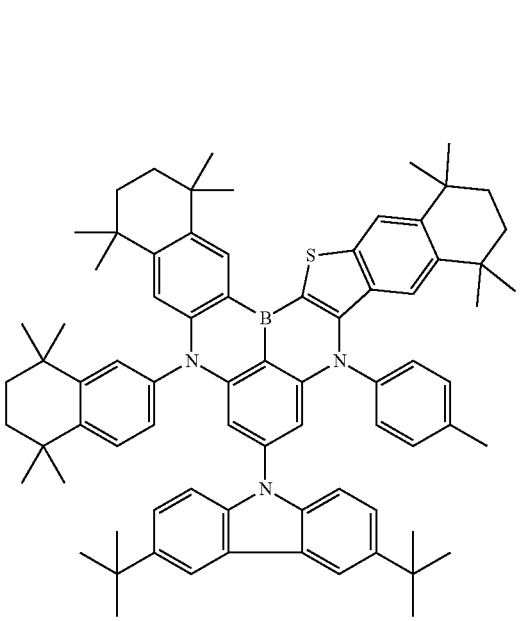
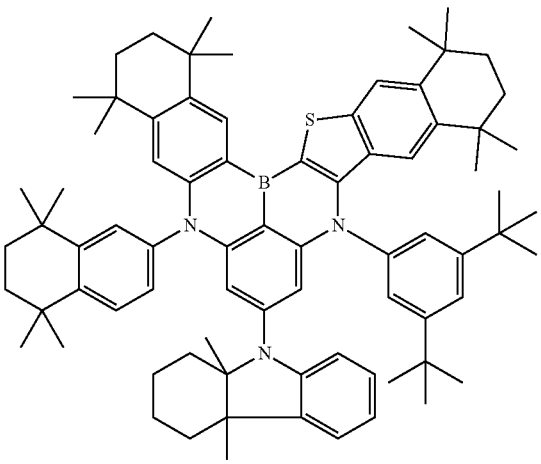

2247
-continued
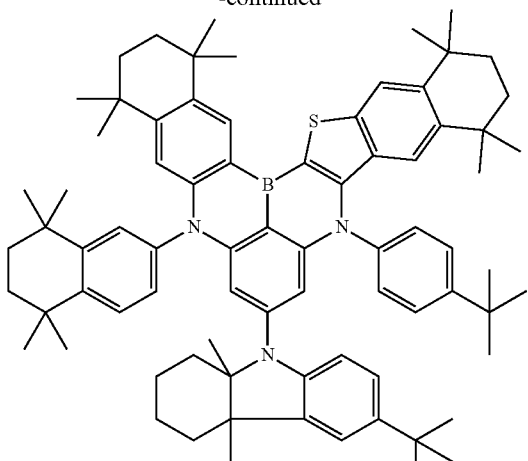
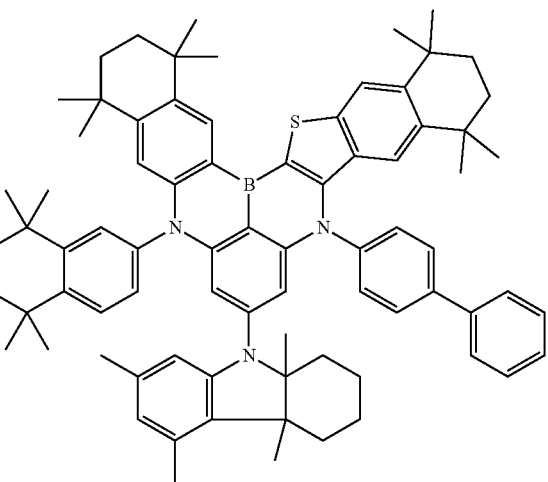
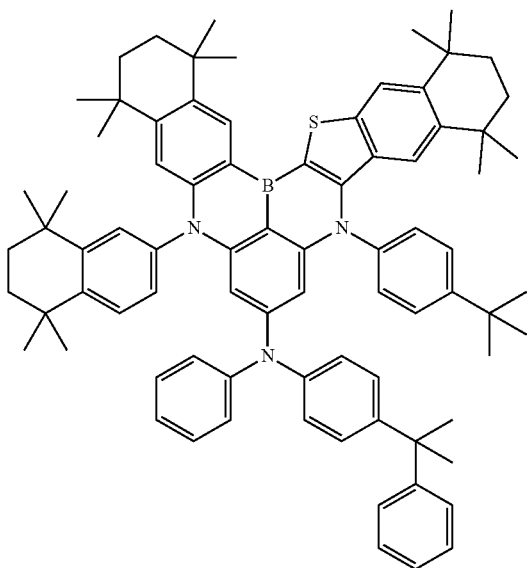
2248
-continued
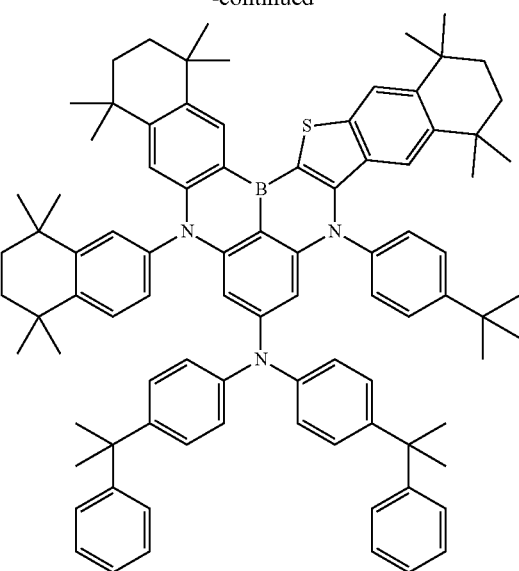
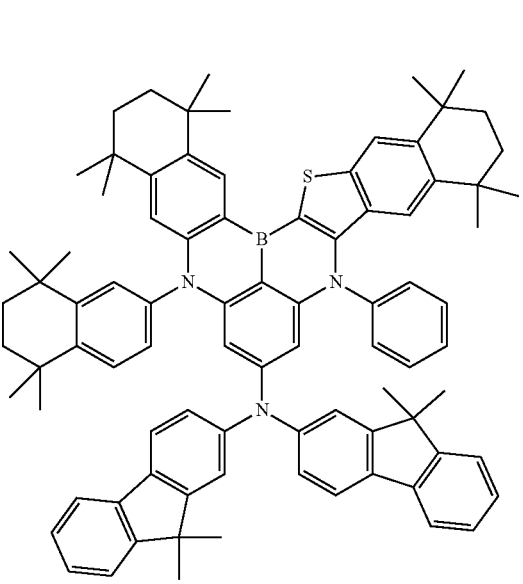
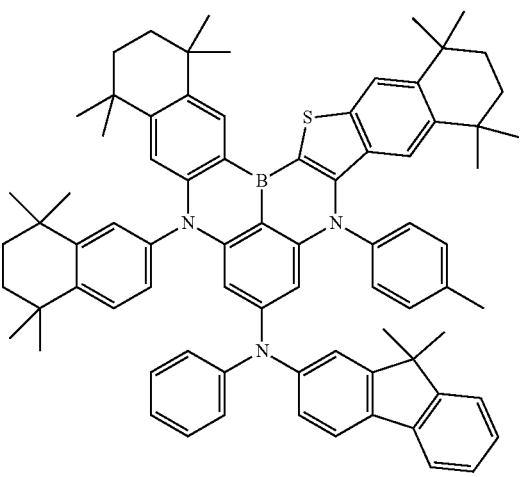

2249
-continued
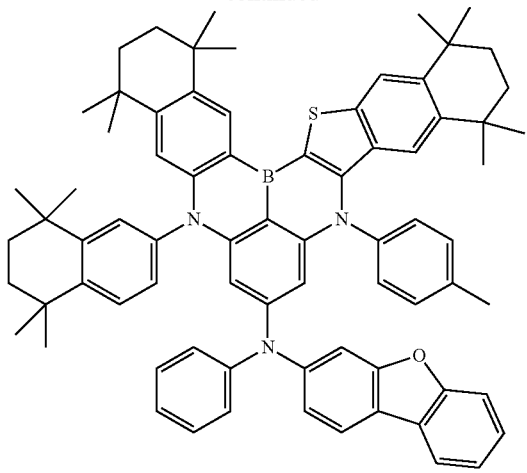
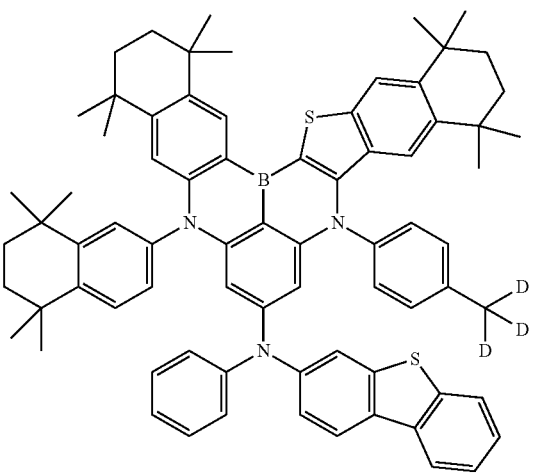
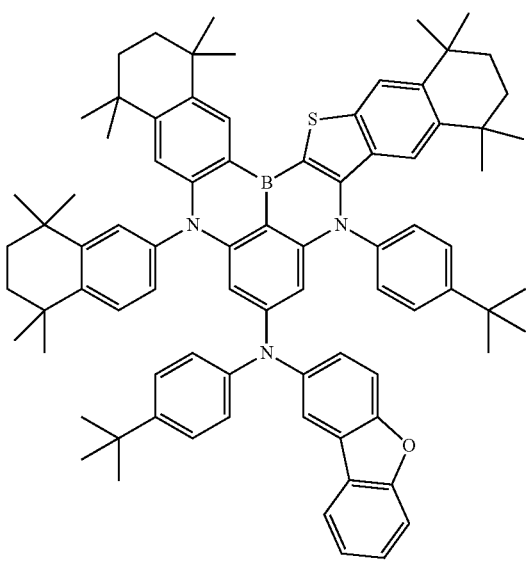
2250
-continued
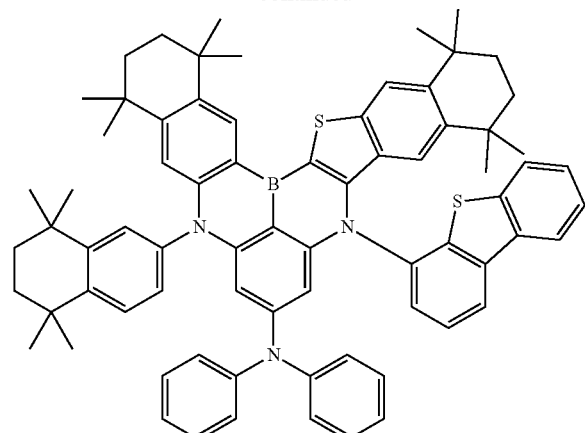
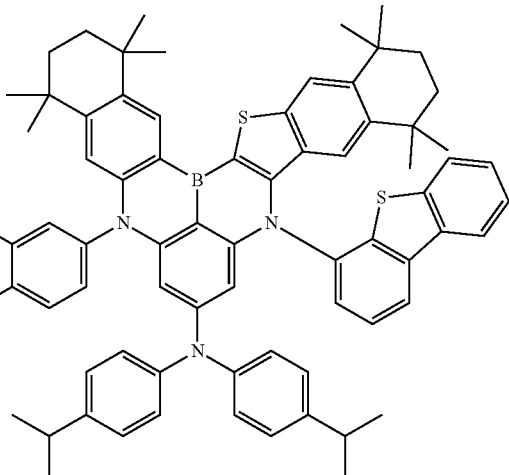
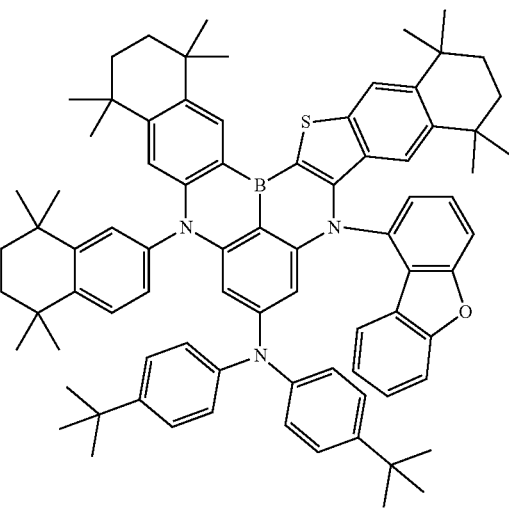

2251
-continued
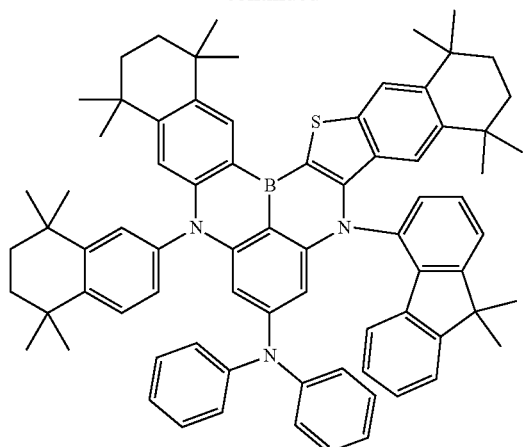
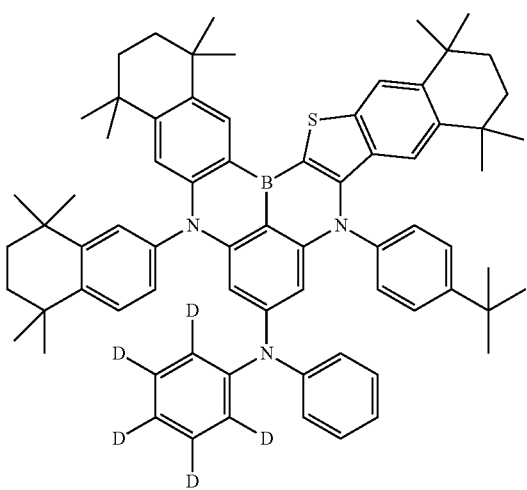
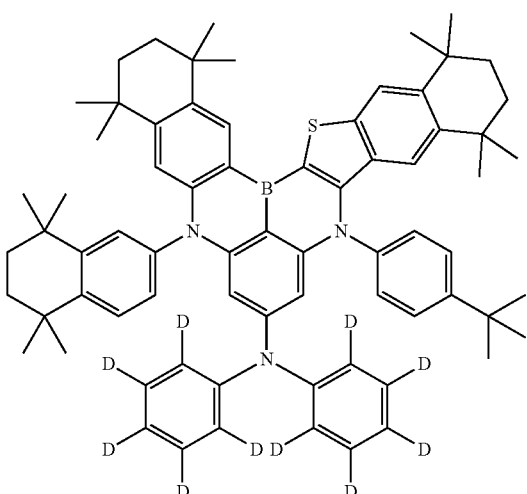
2252
-continued
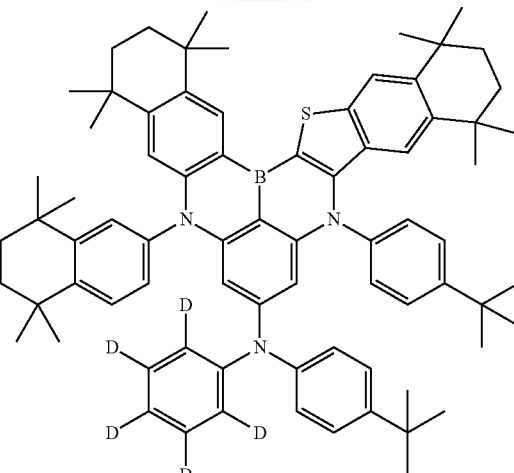
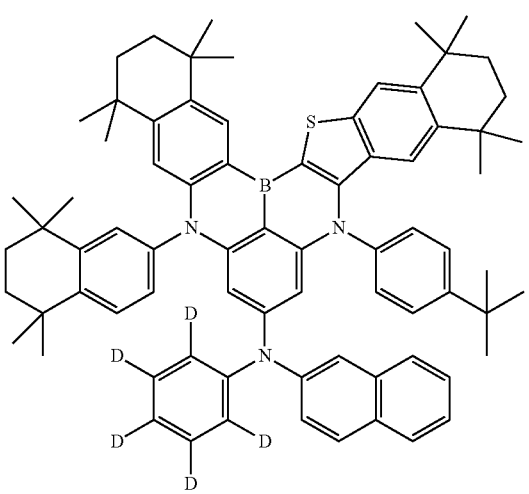
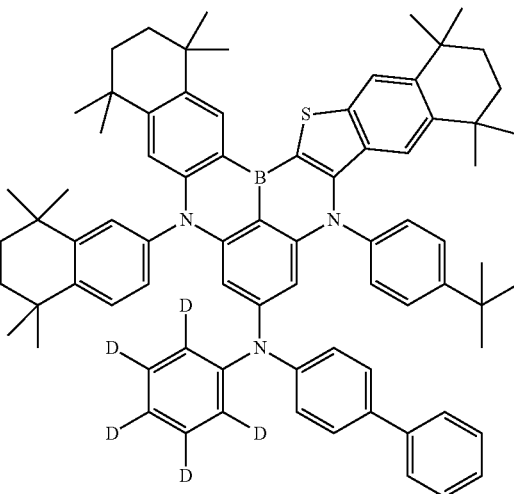

2253
-continued
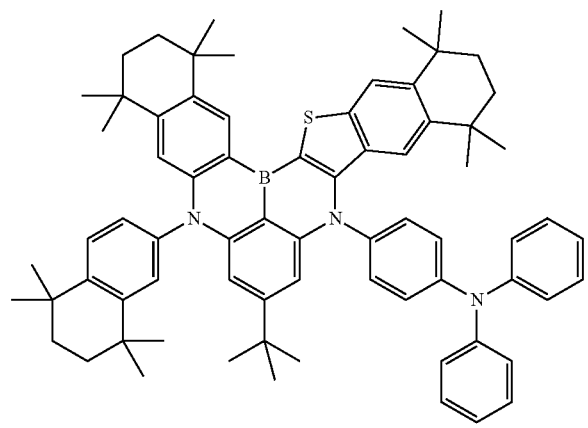
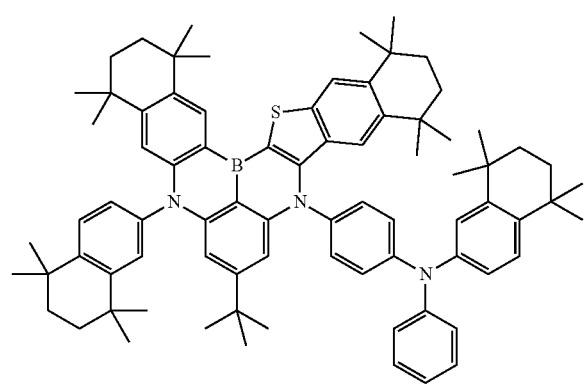
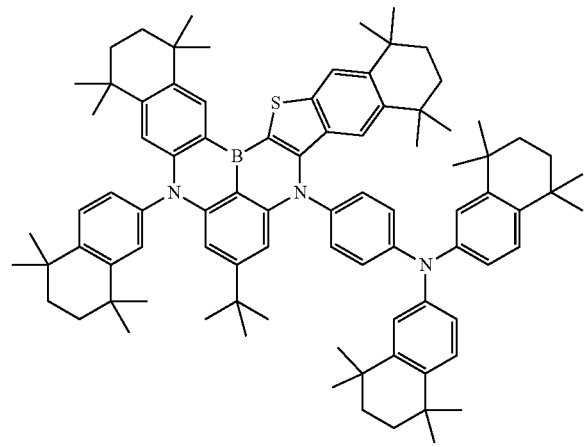
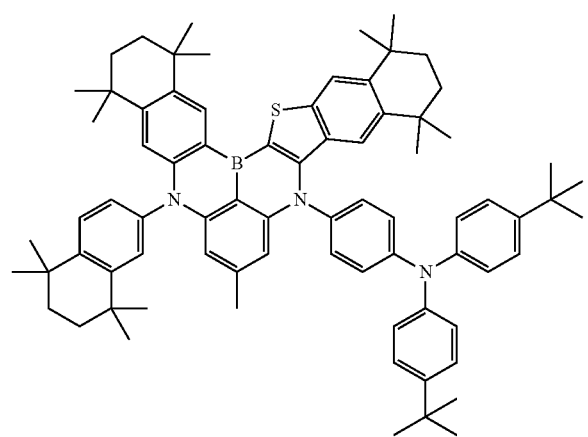
2254
-continued
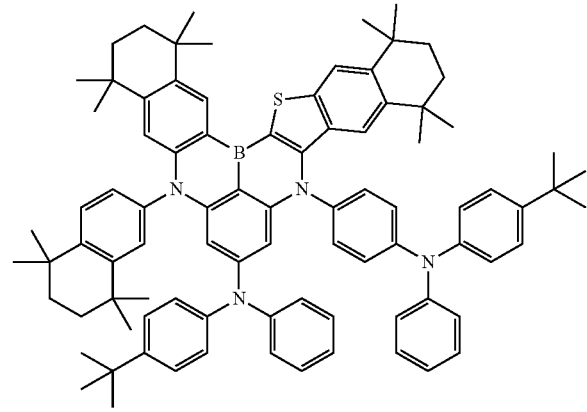
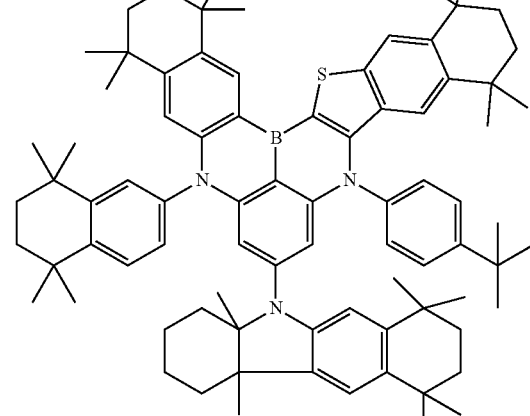
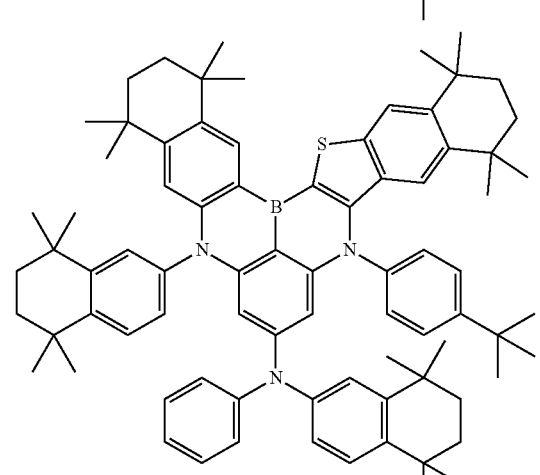
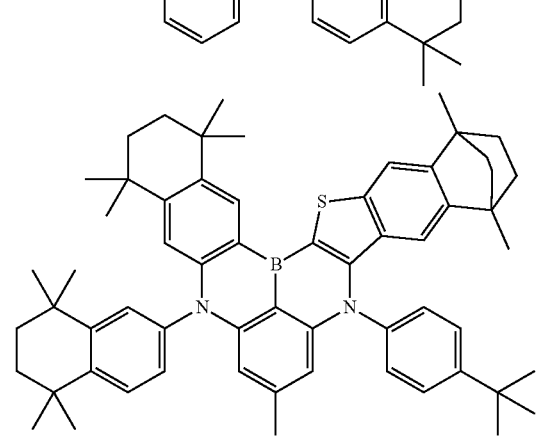

2255
-continued
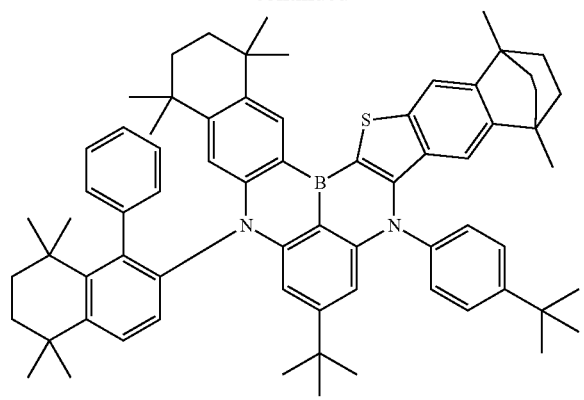
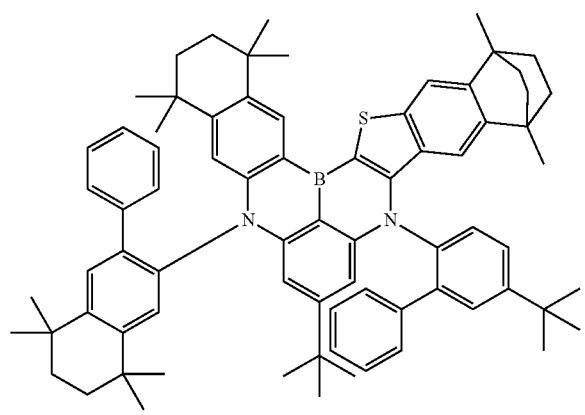
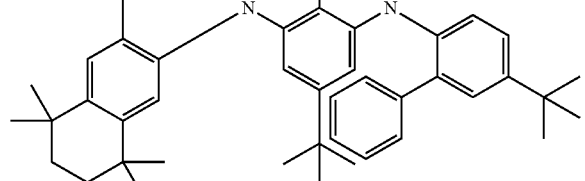
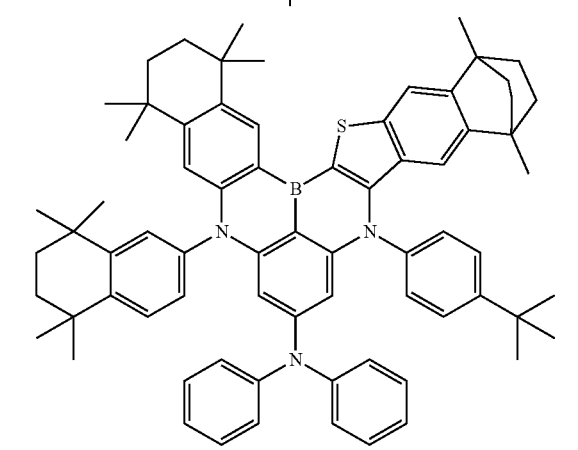
2256
-continued
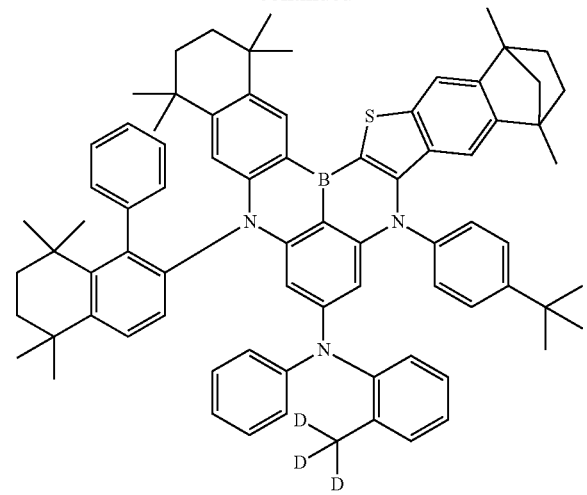

2257
-continued
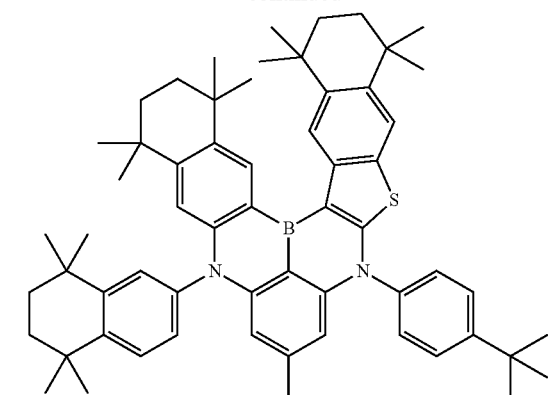
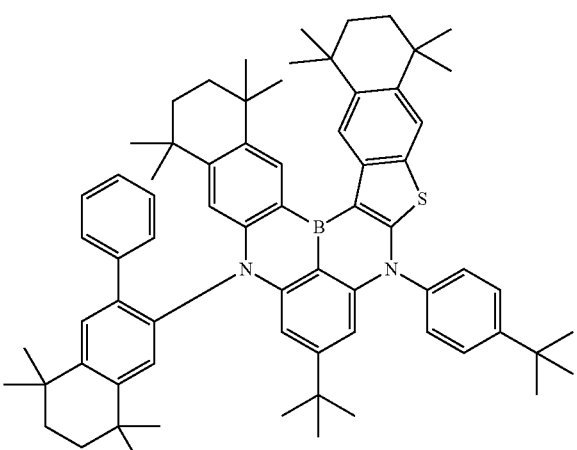
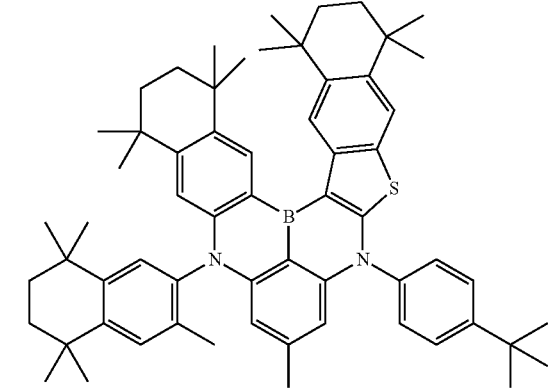
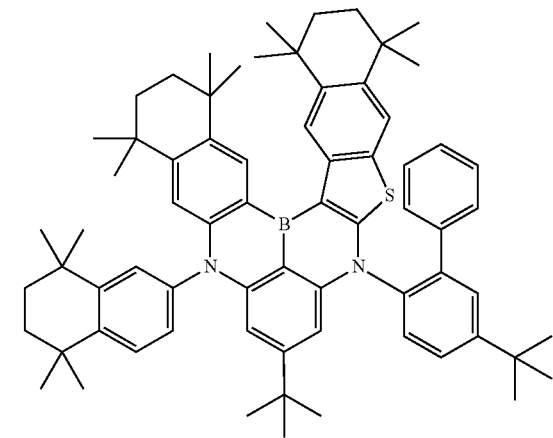
2258
-continued
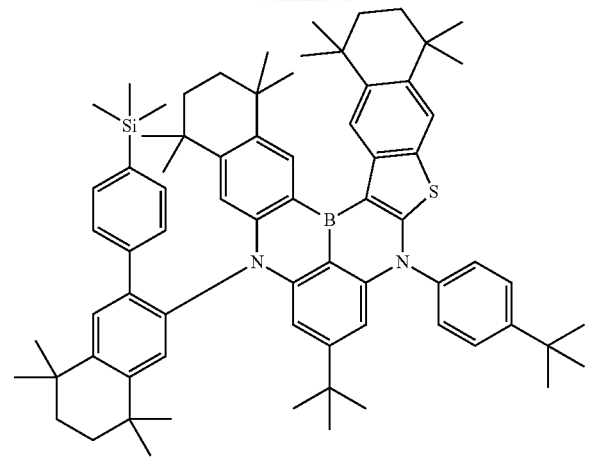
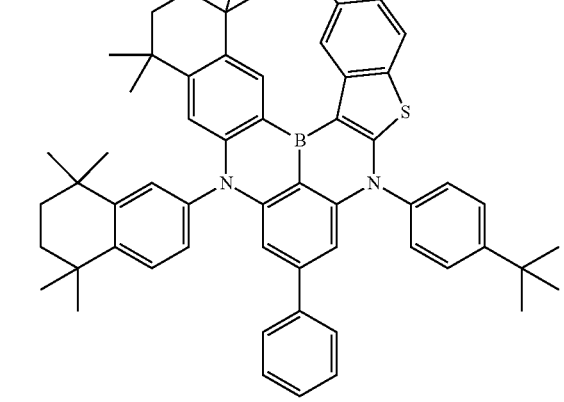
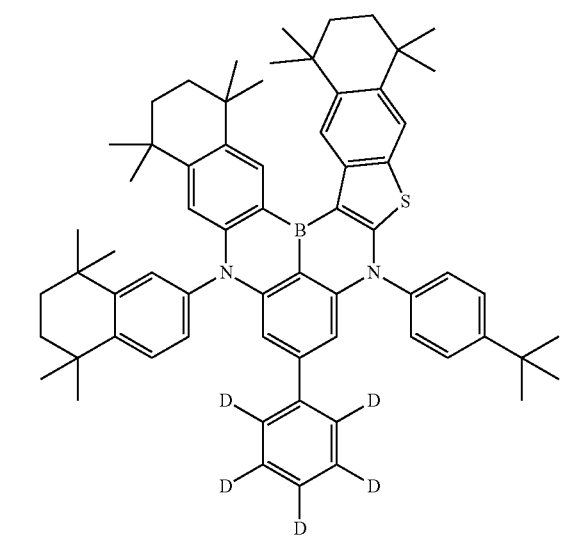

2259
-continued
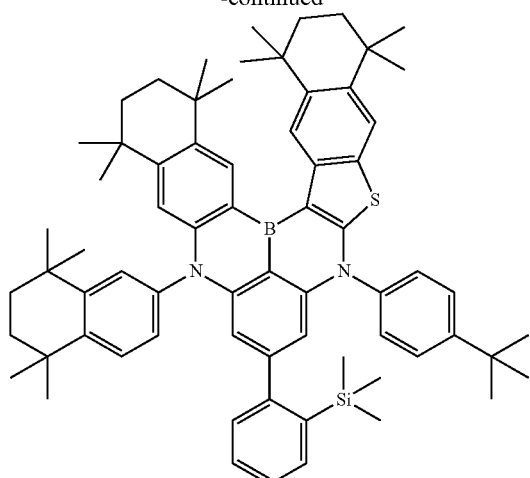
2260
-continued
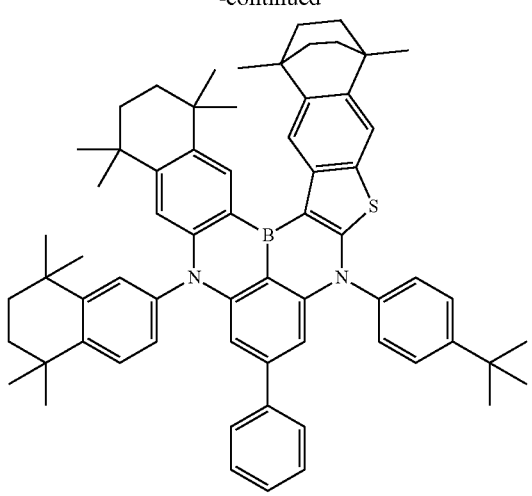
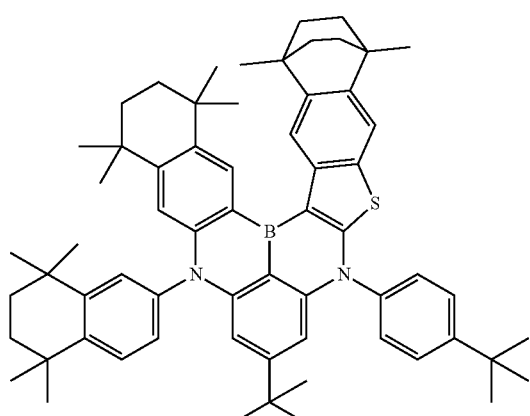
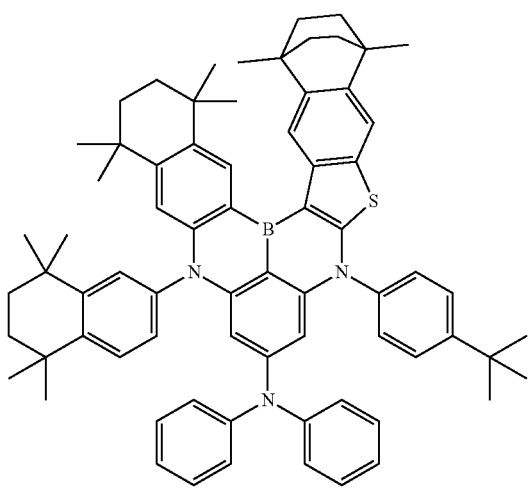
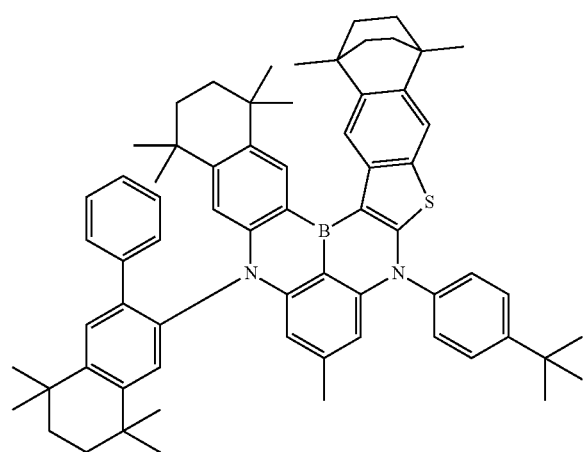
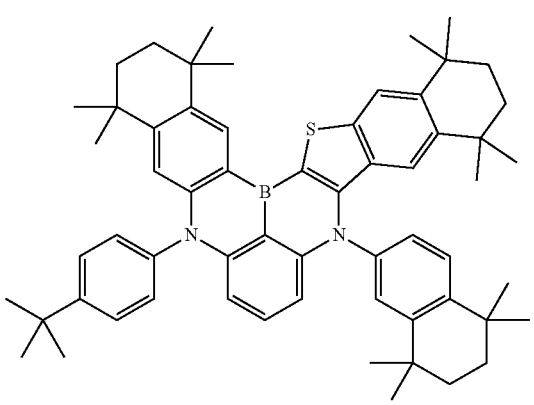

2261
-continued
2262
-continued
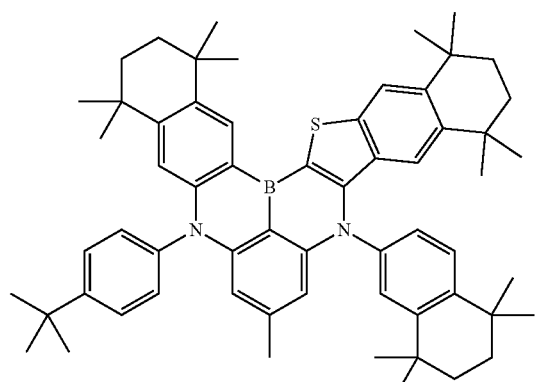
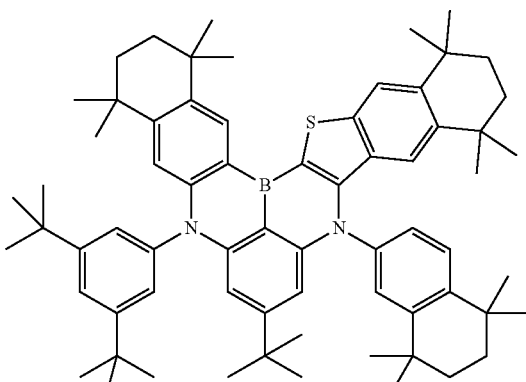
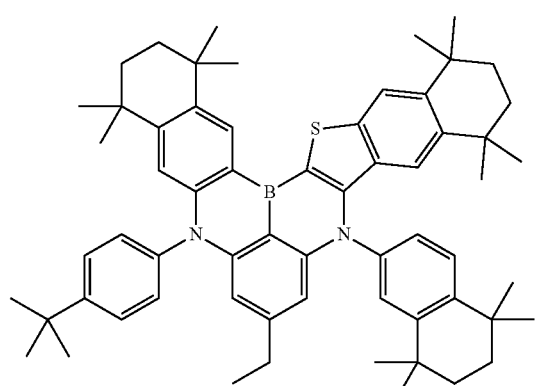
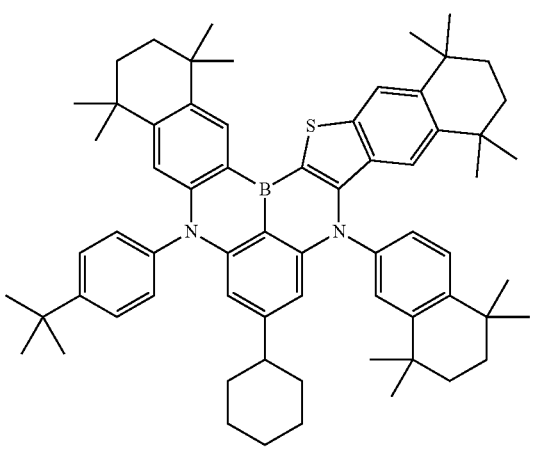
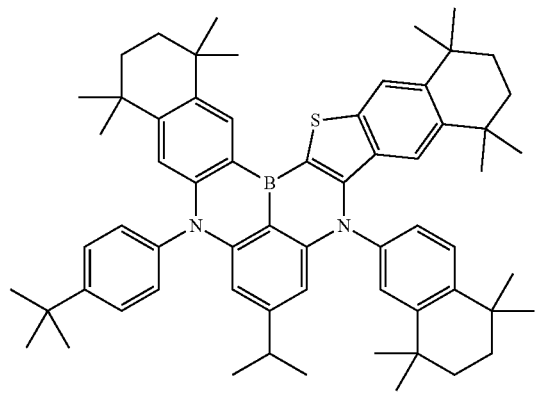
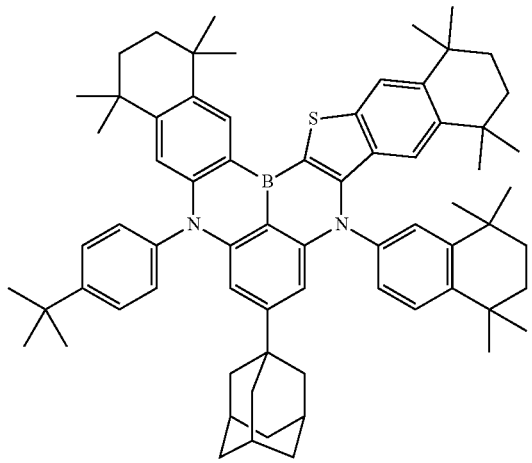
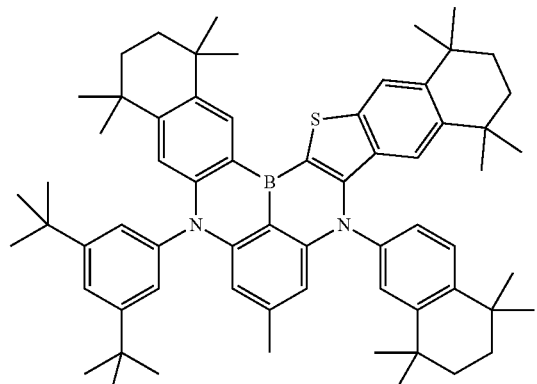
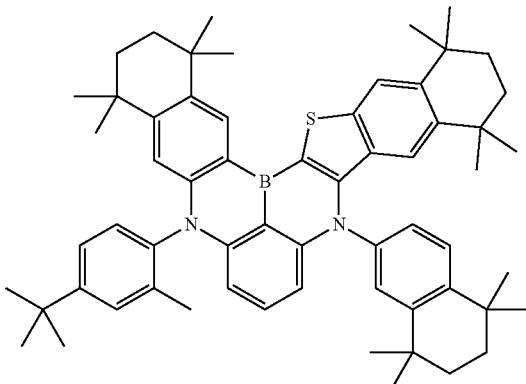

2263
-continued
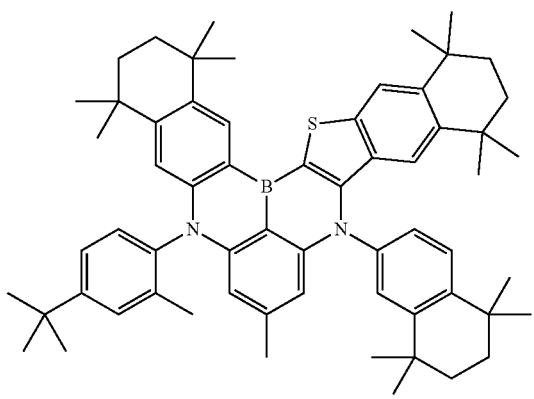
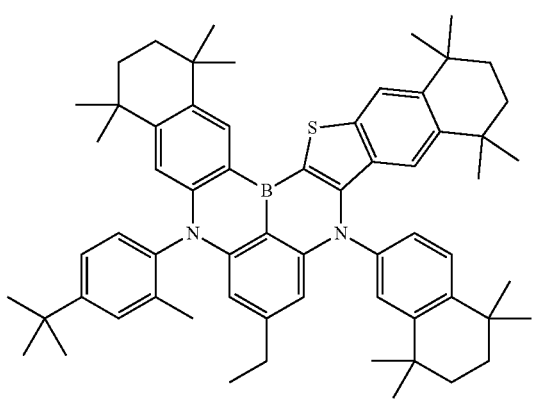
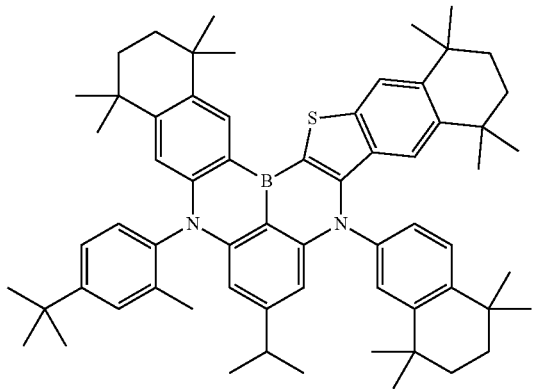
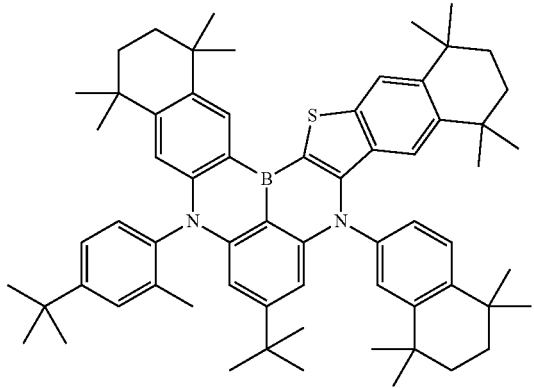
2264
-continued
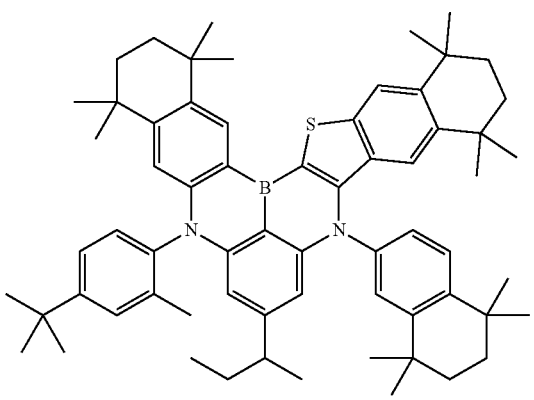
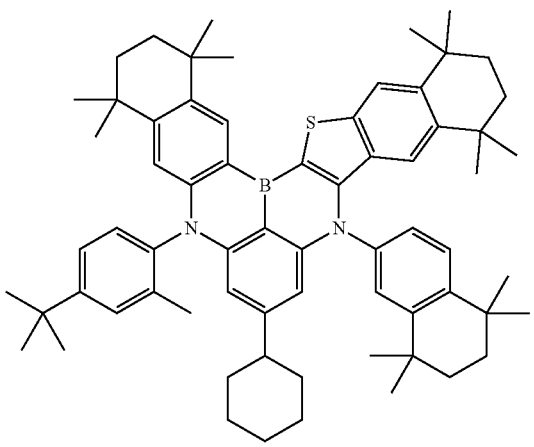
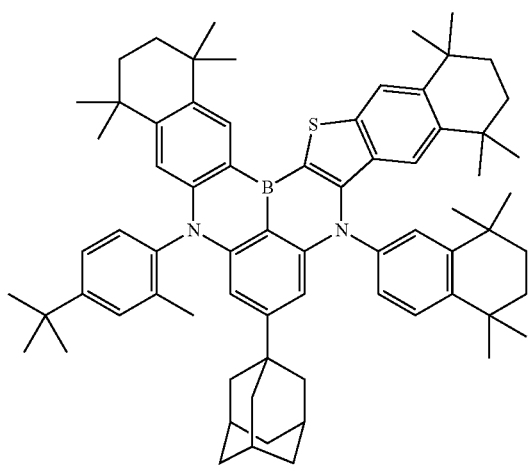
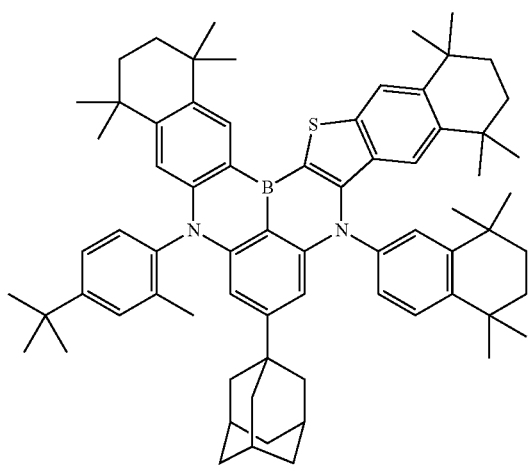

2265
-continued
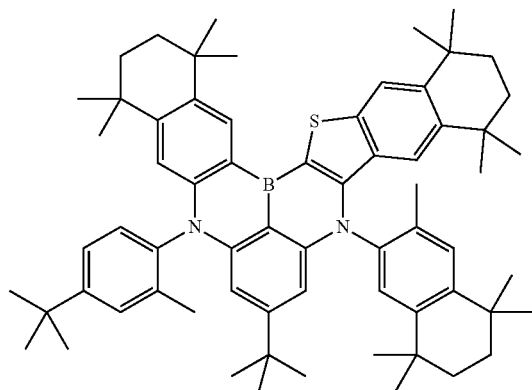
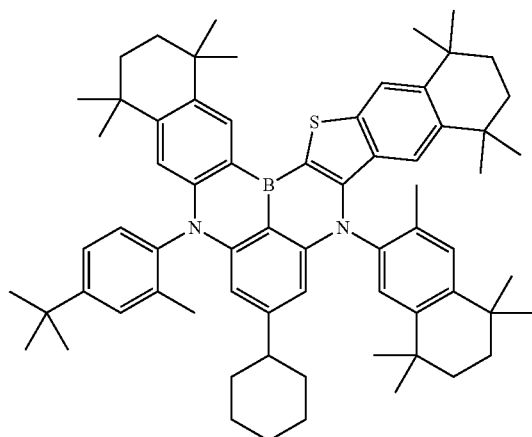
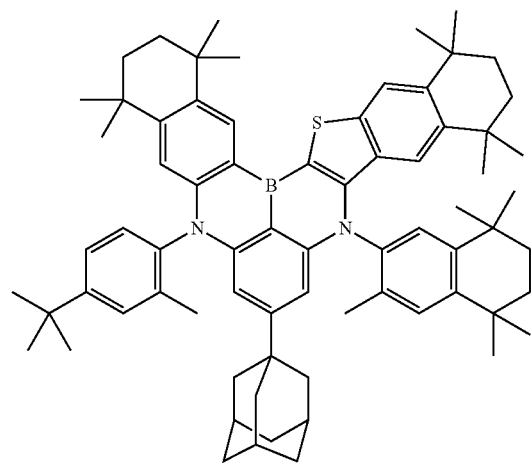
2266
-continued
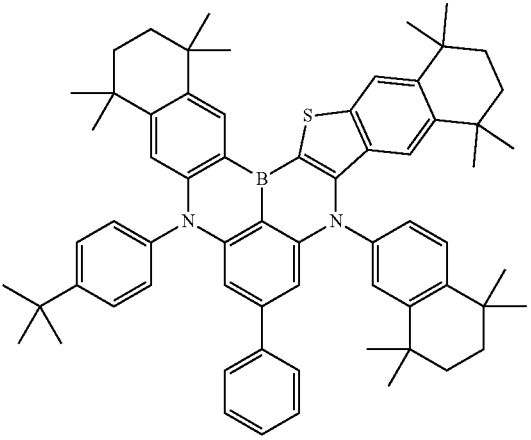
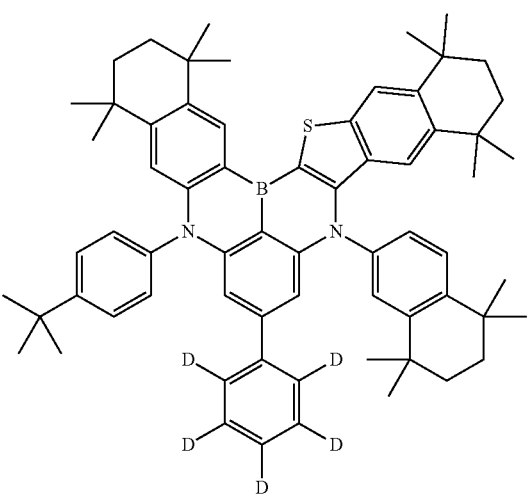
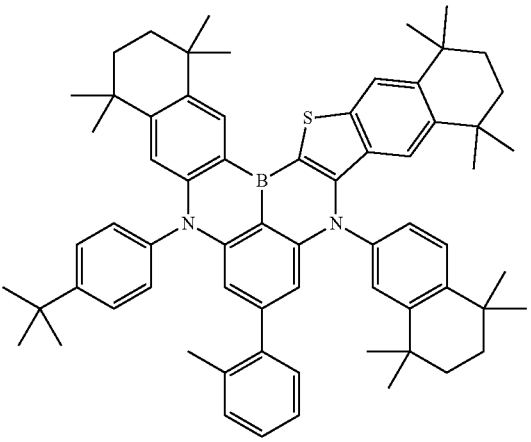

2267
-continued
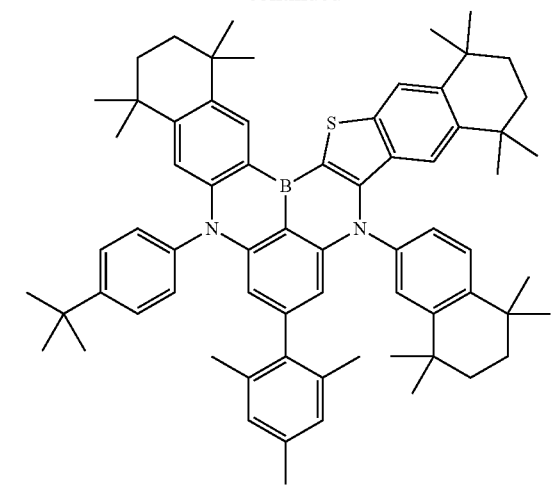
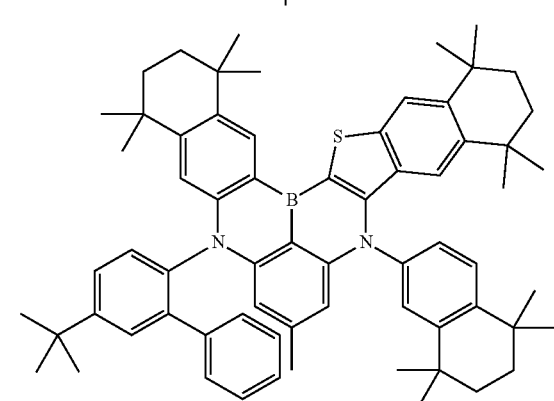
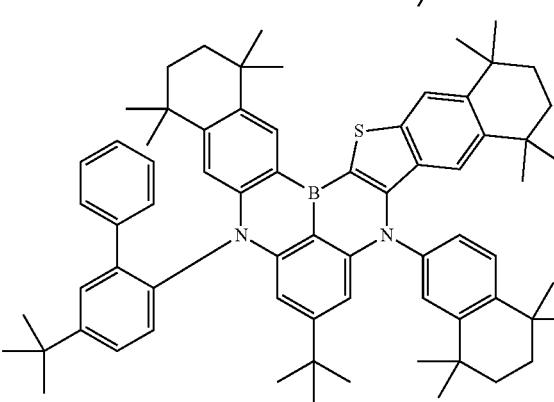
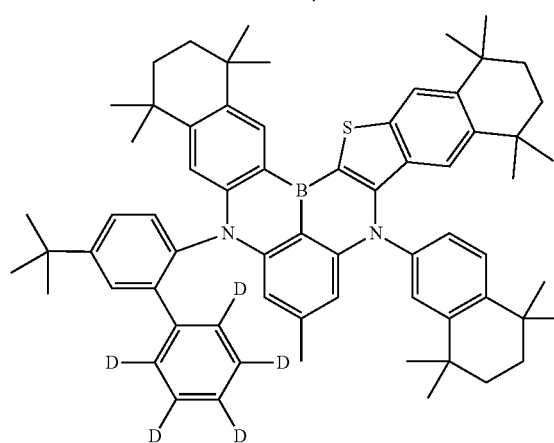
2268
-continued
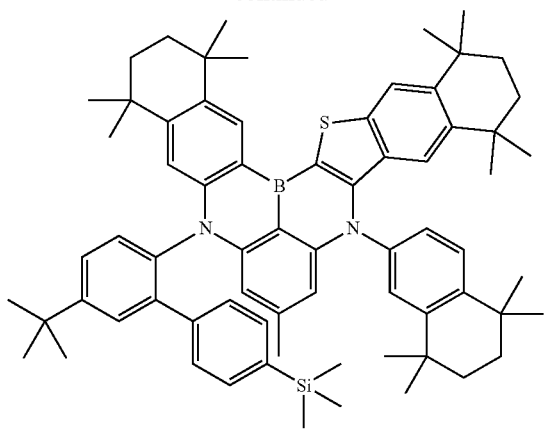
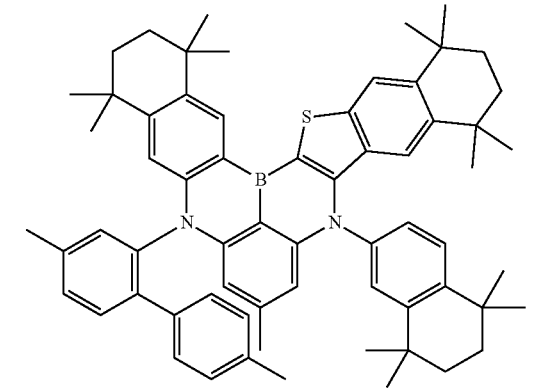
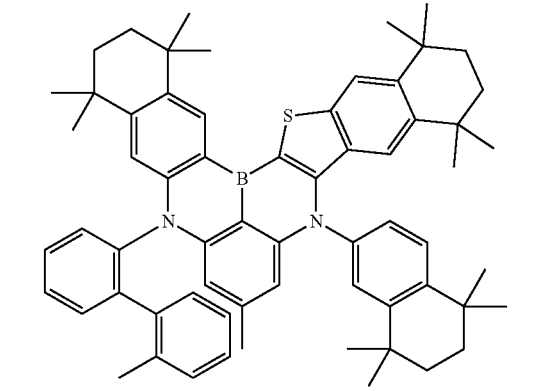
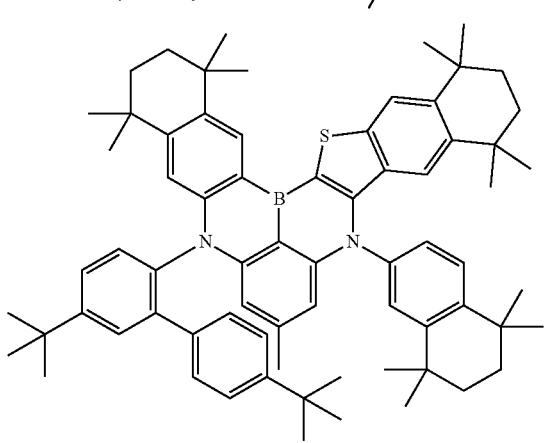

| 2269 | 2270 |
|---|---|
| -continued | -continued |
| 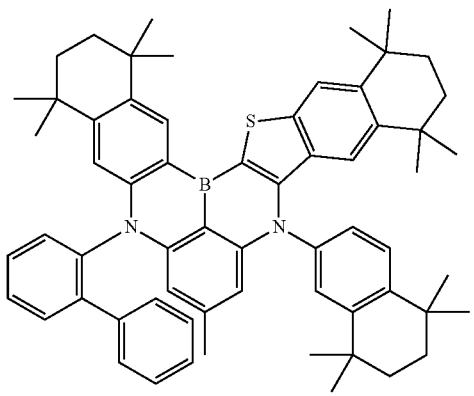 | 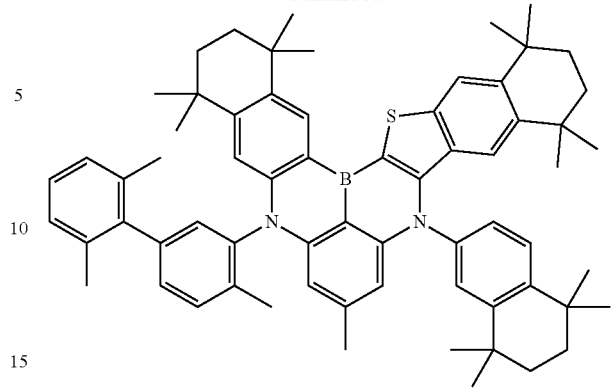 |
| 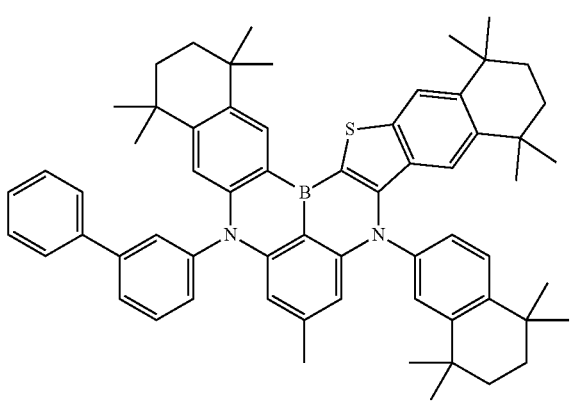 | 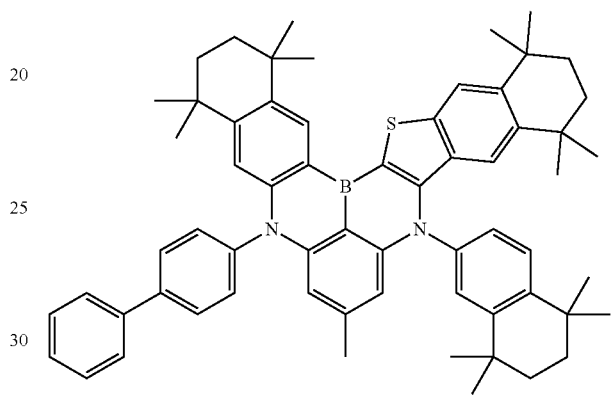 |
| 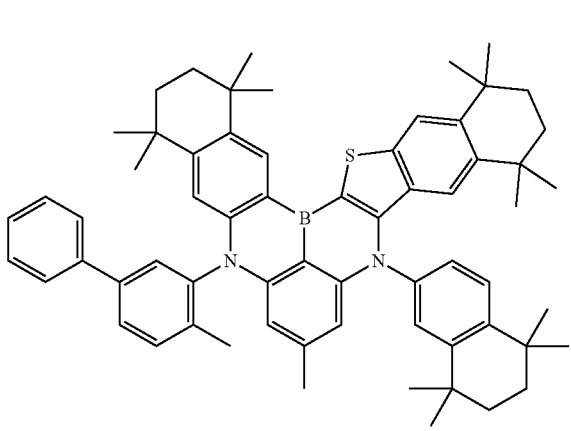 | 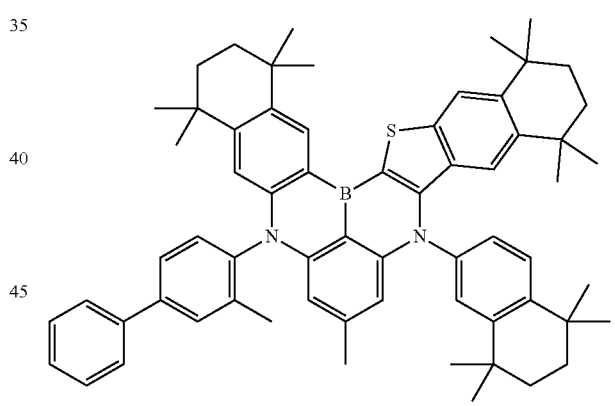 |
| 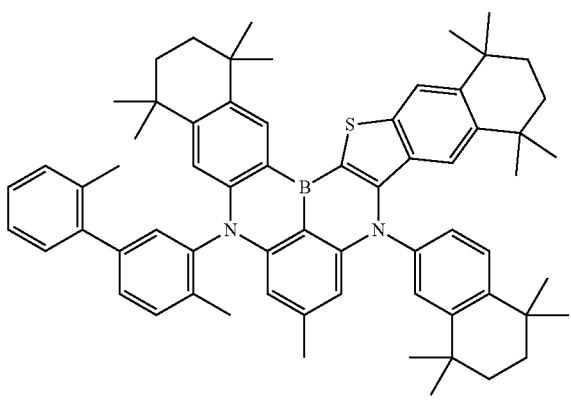 | 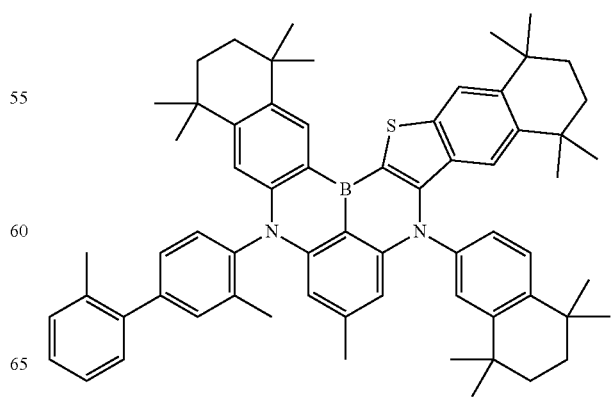 |

2271
-continued
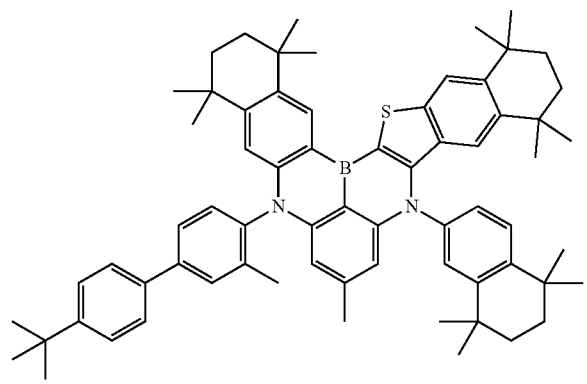
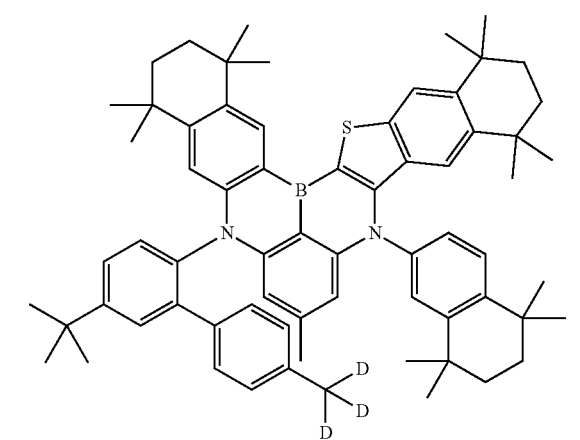
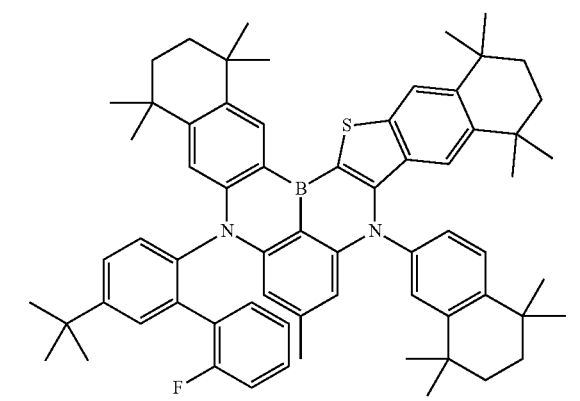
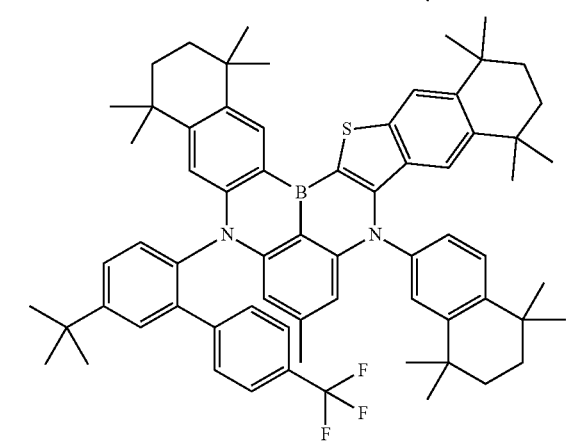
2272
-continued
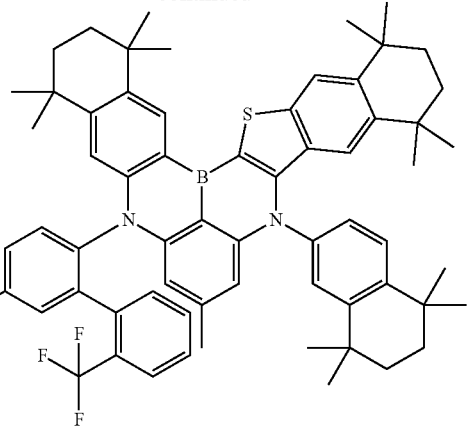
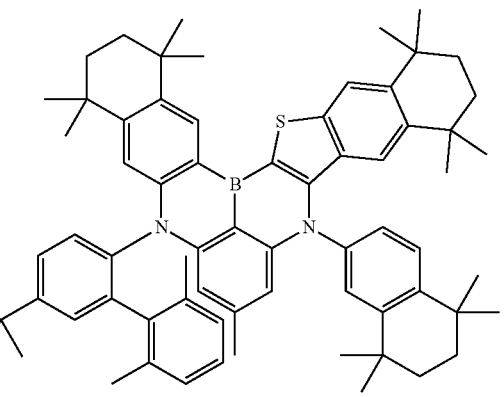
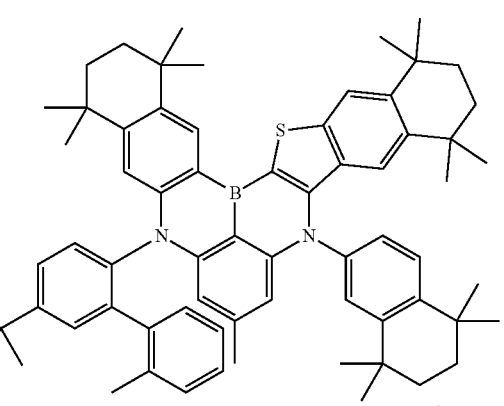
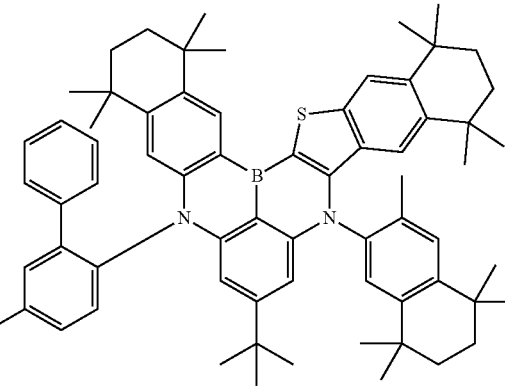

2273
-continued
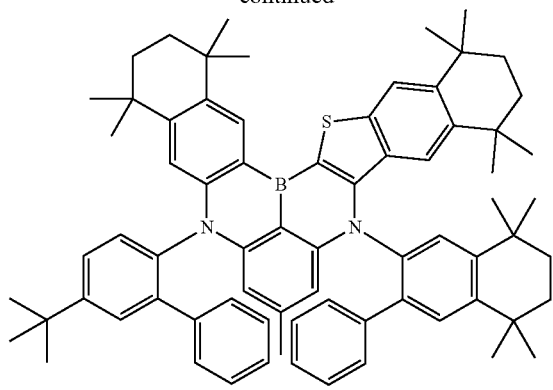
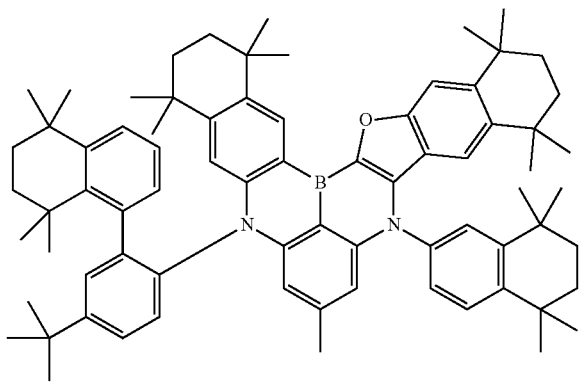
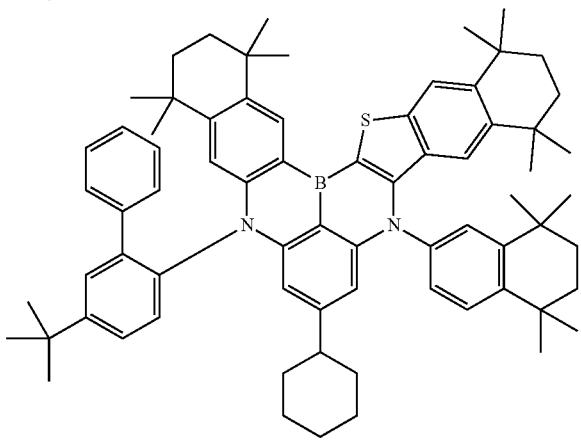
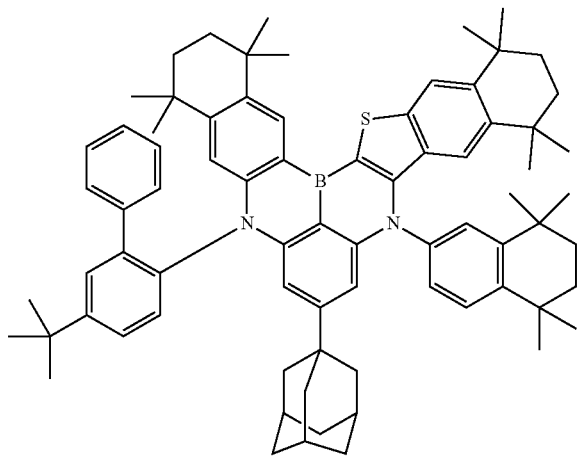
2274
-continued
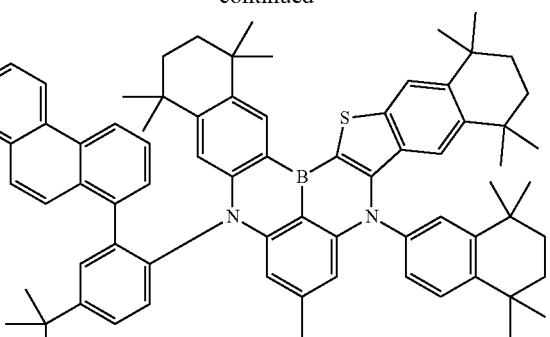
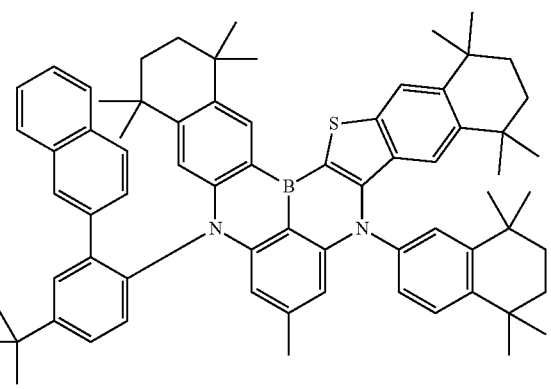
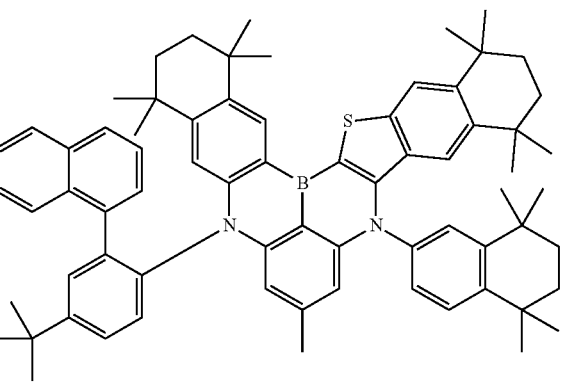
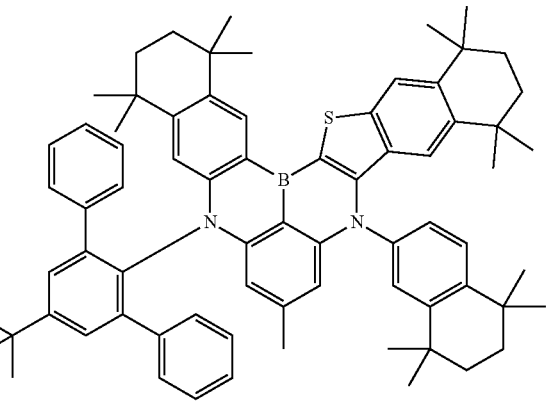

| 2275 -continued | 2276 -continued |
|---|---|
| 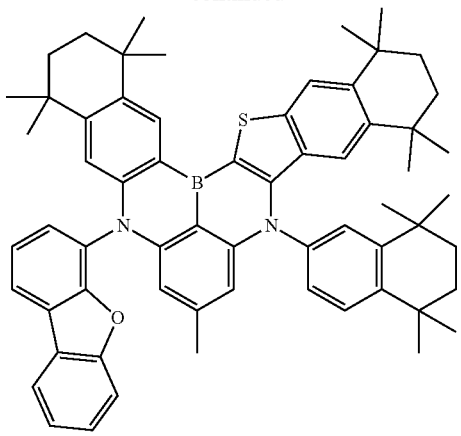 | 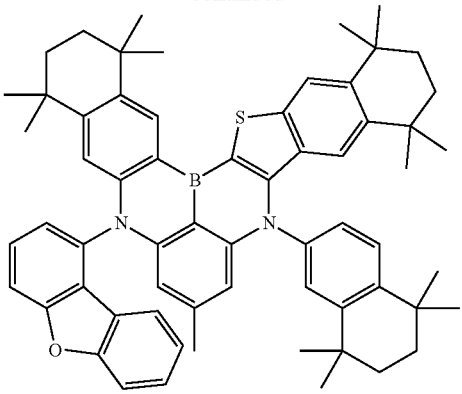 |
| 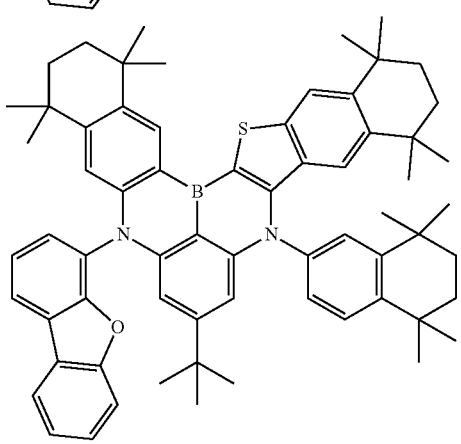 | 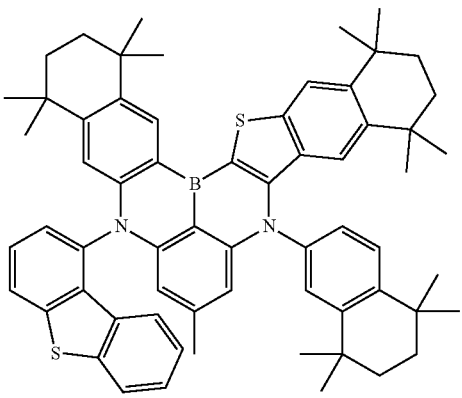 |
| 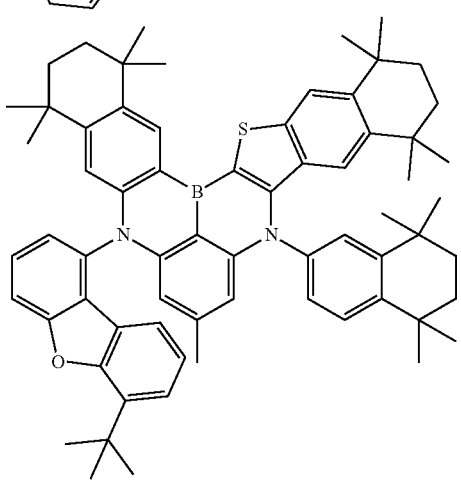 | 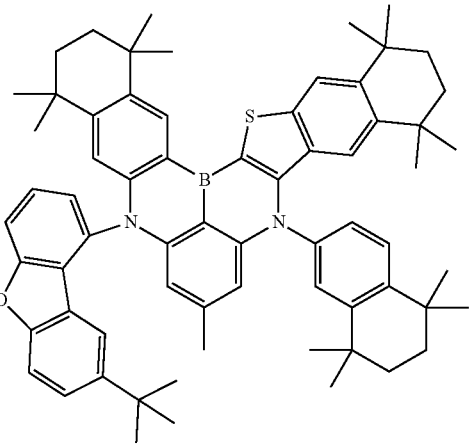 |
| 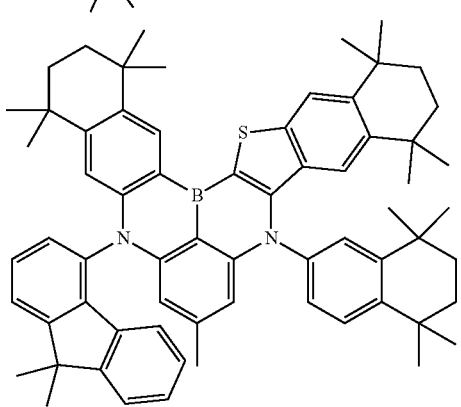 | 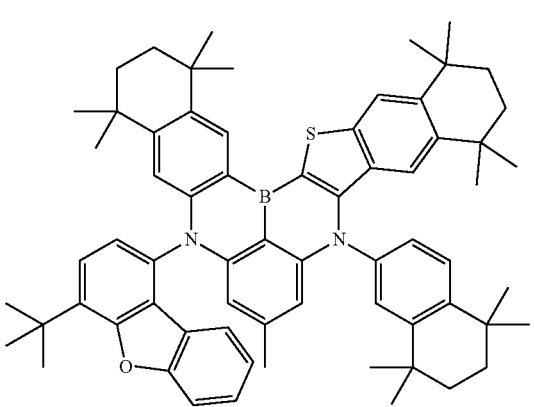 |

2277
-continued
2278
-continued
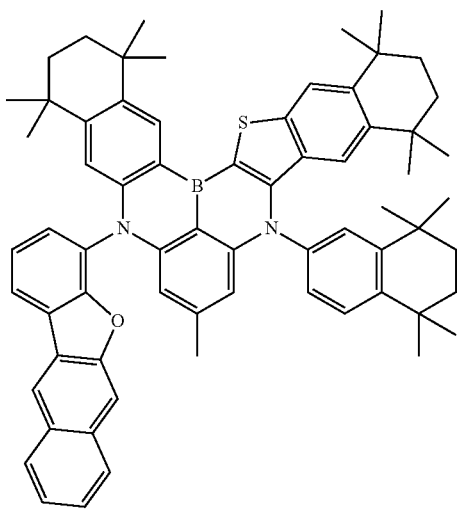
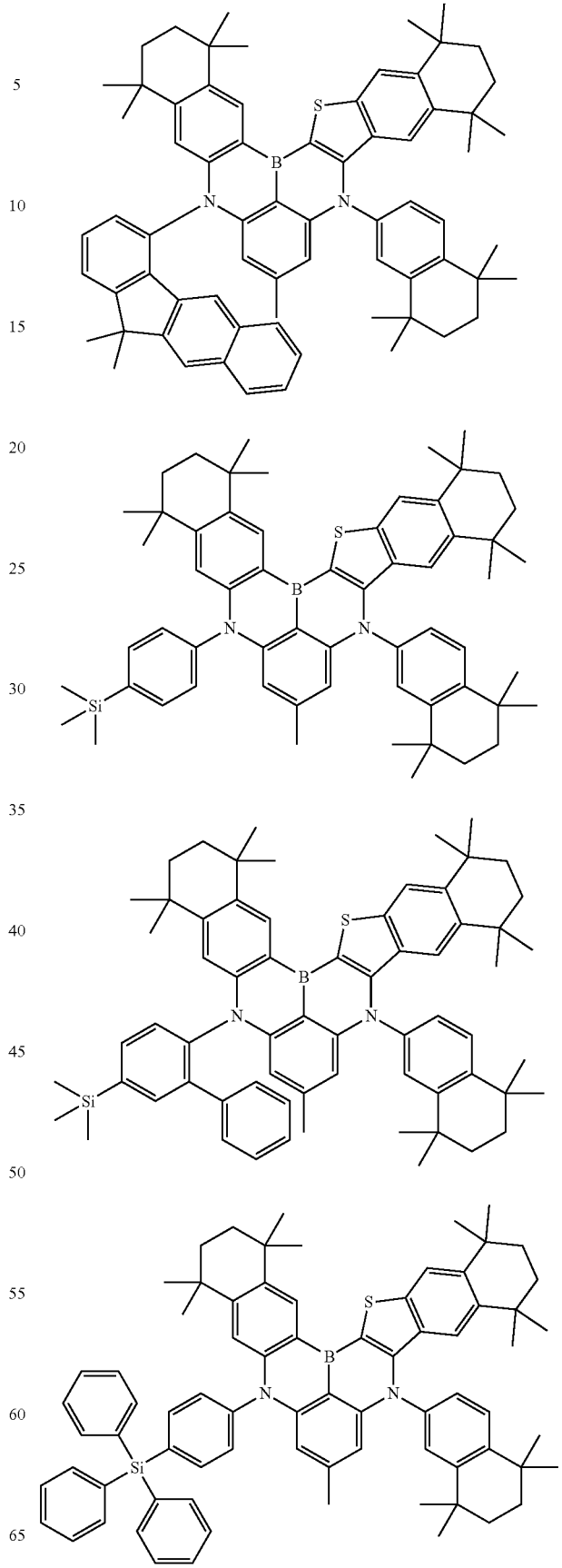

2279
-continued
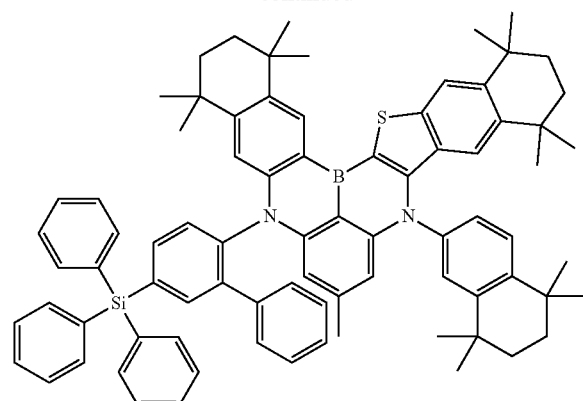
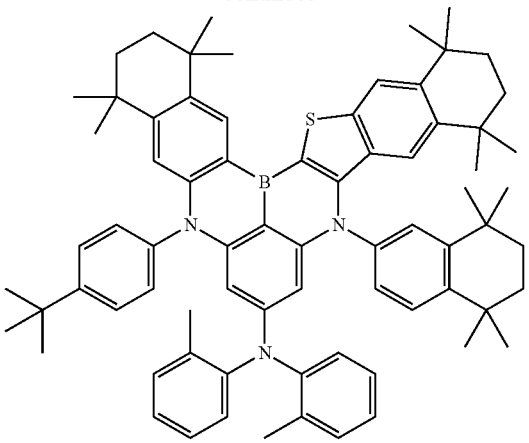
2280
-continued
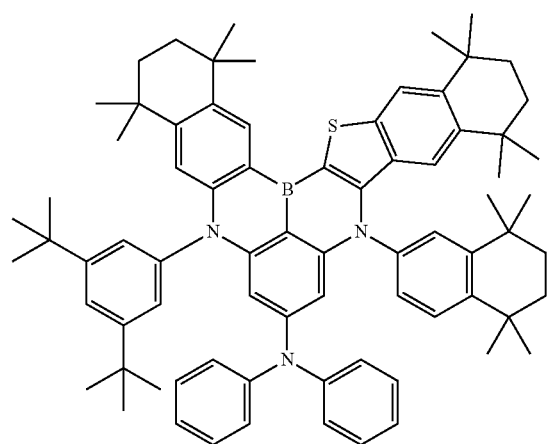
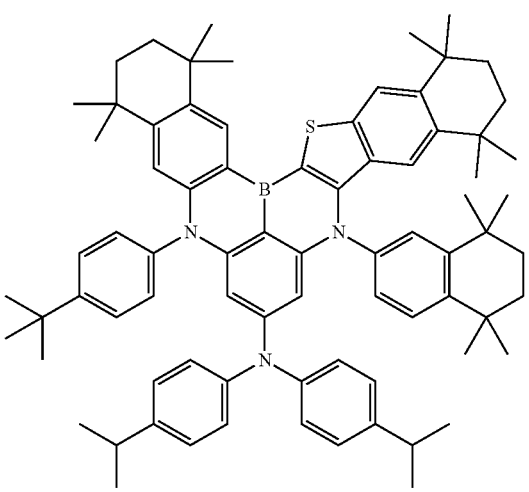
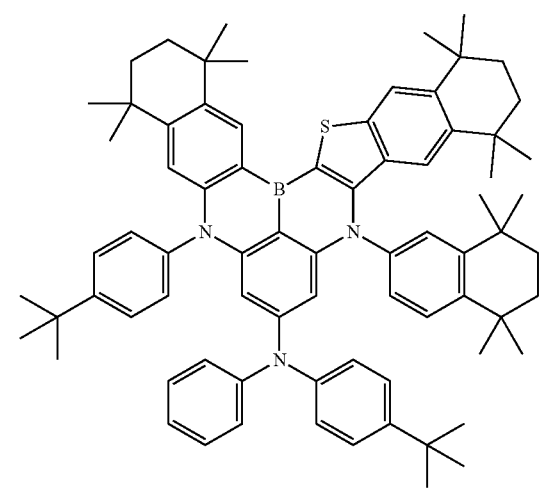
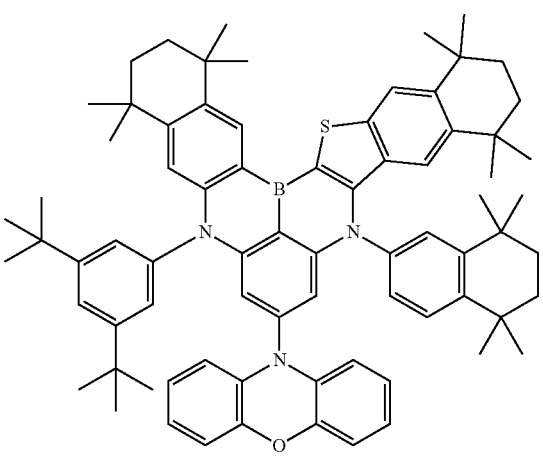

2281
-continued
2282
-continued
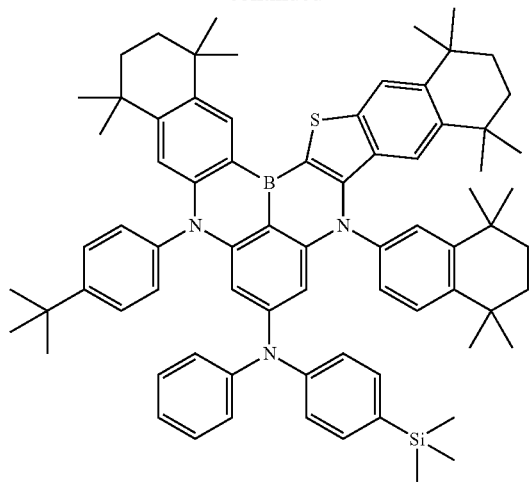
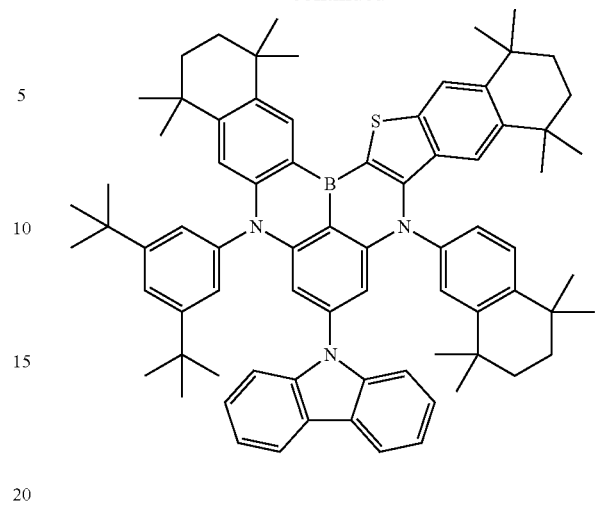
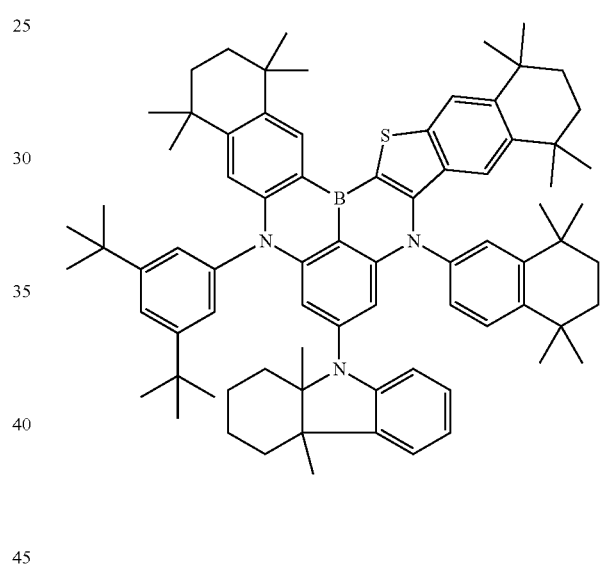
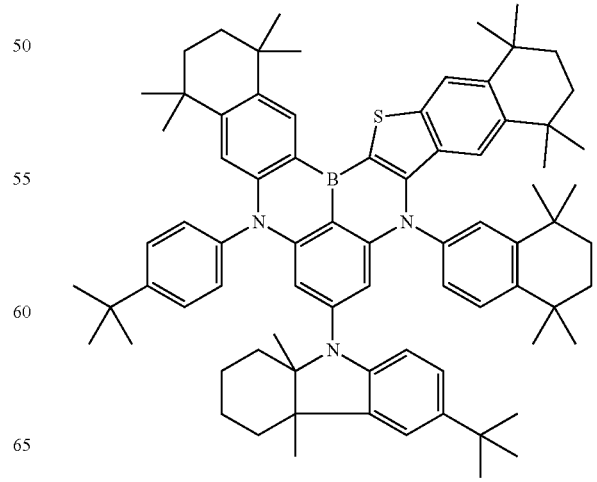

2283
-continued
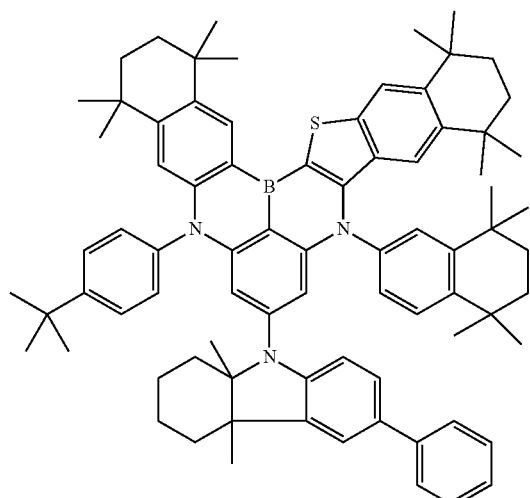
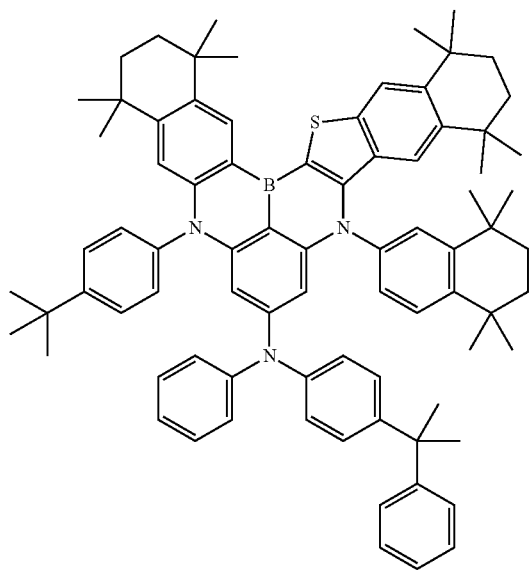
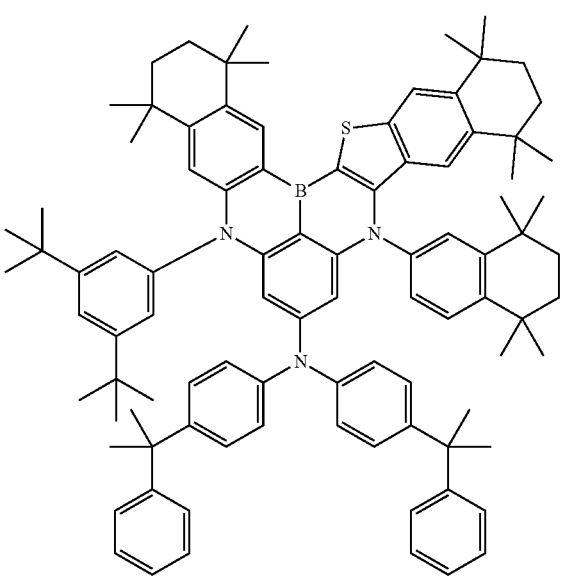
2284
-continued
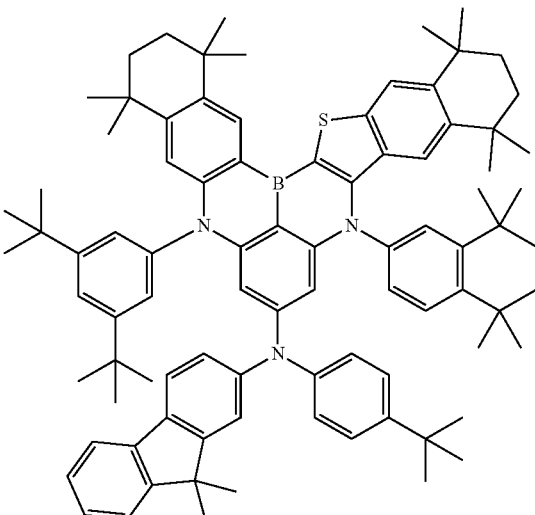
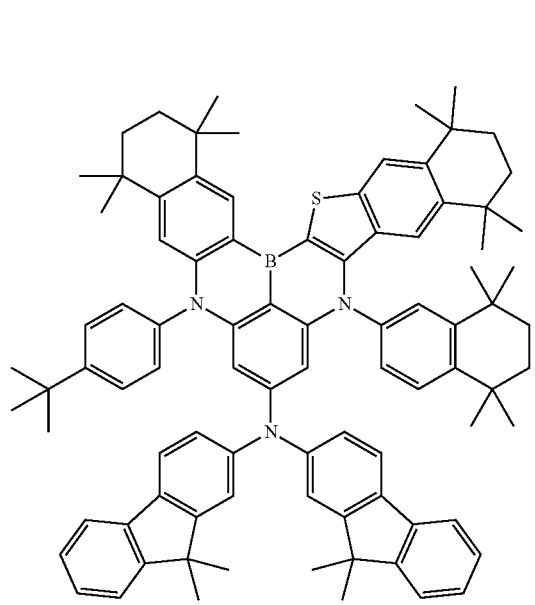
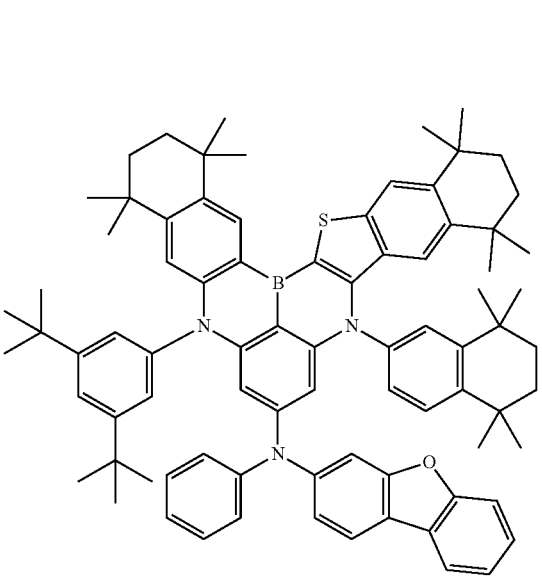

2285
-continued
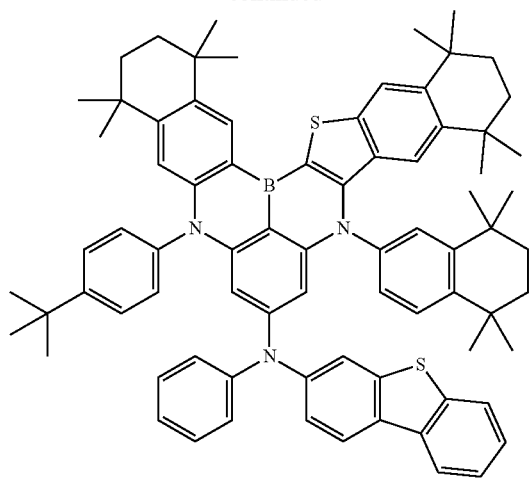
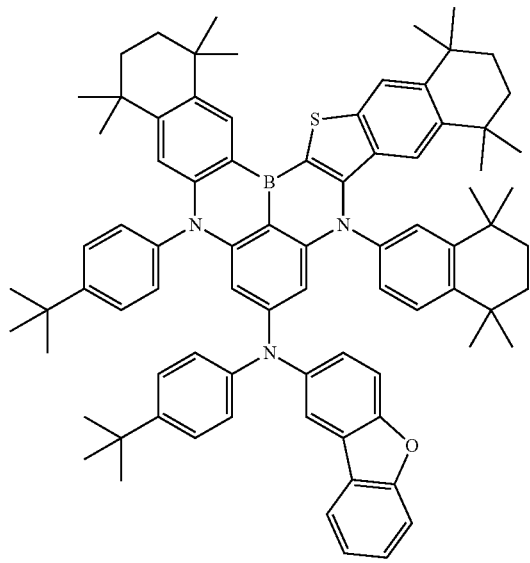
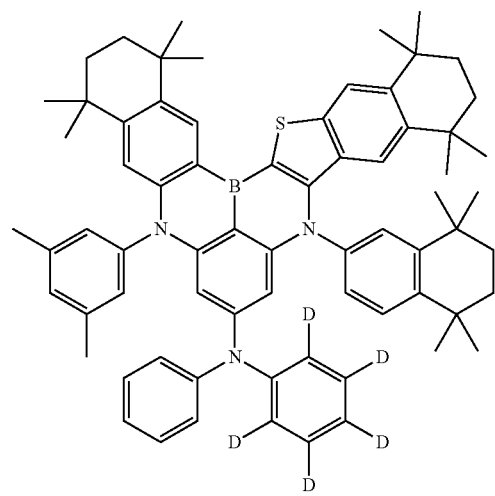
2286
-continued
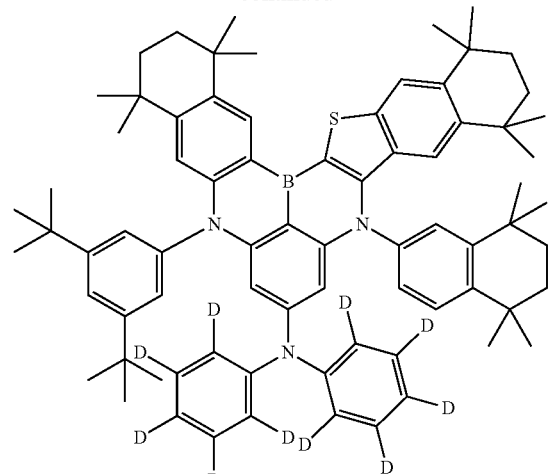
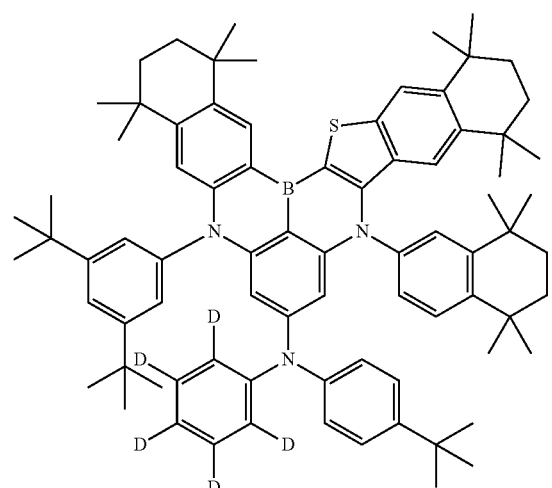
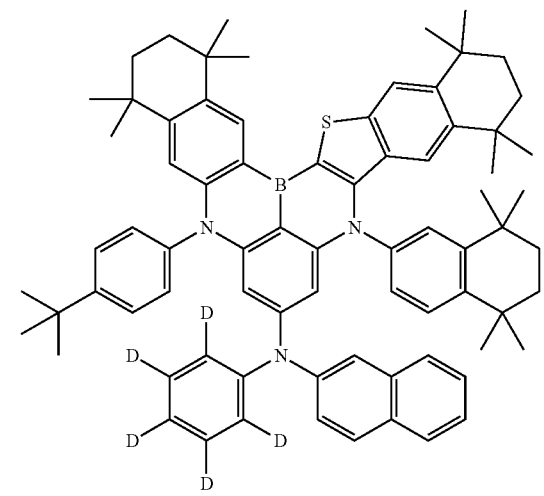

2287
-continued
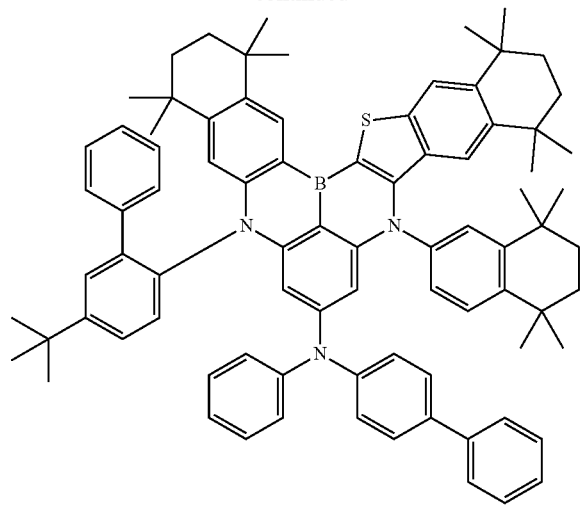
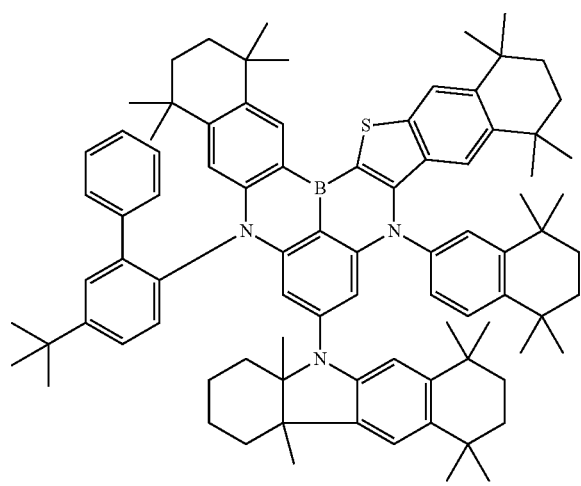
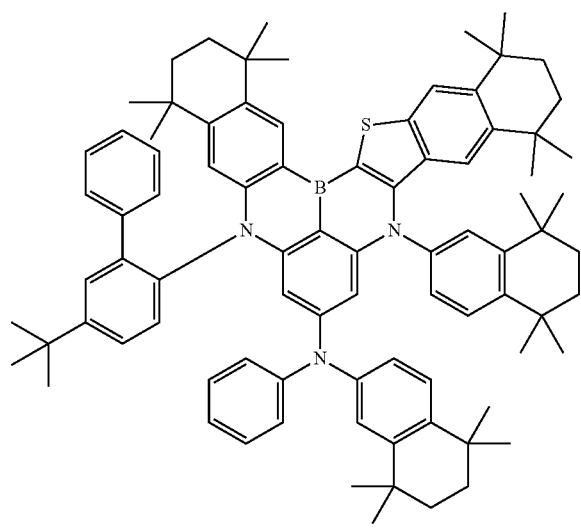
2288
-continued
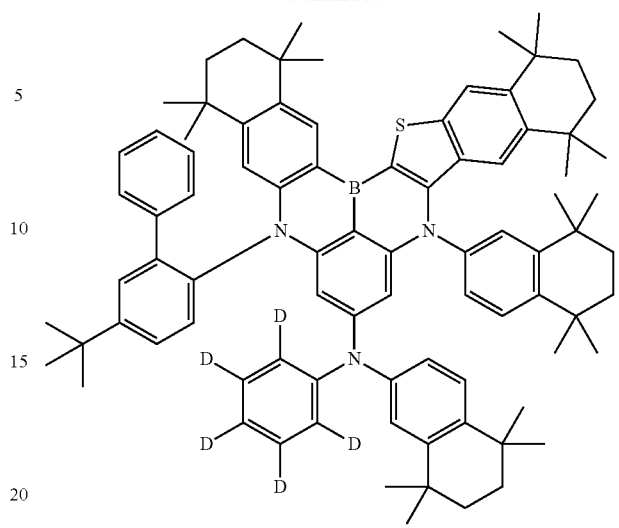
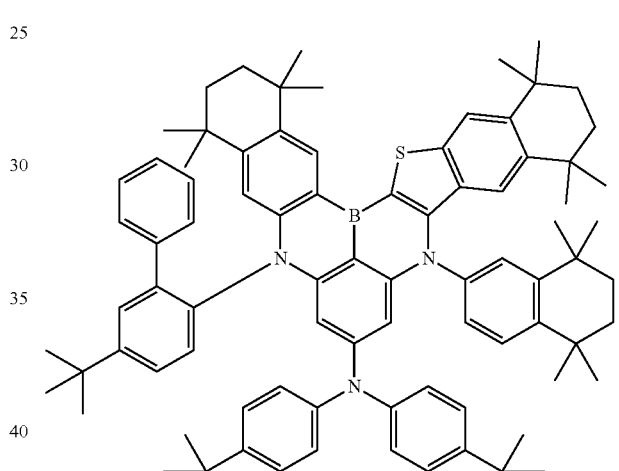
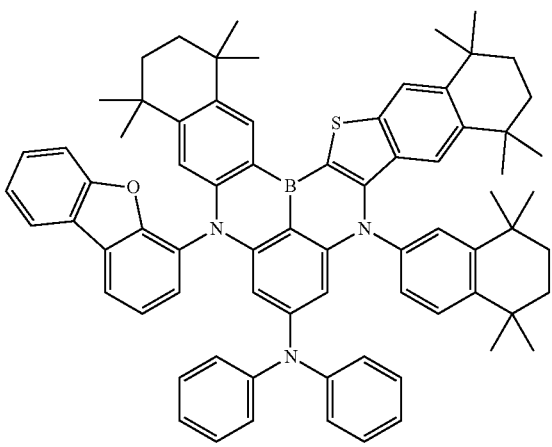

2289
-continued
2290
-continued
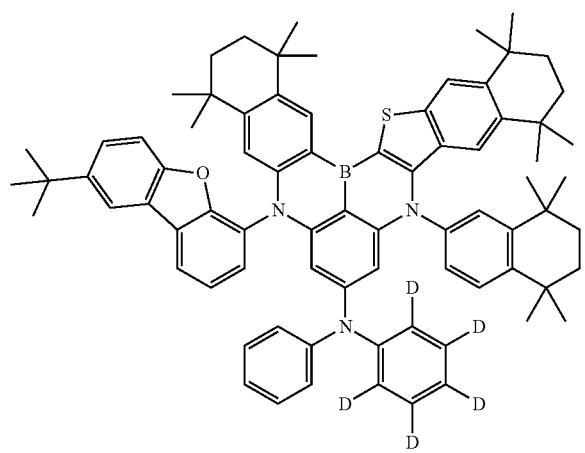
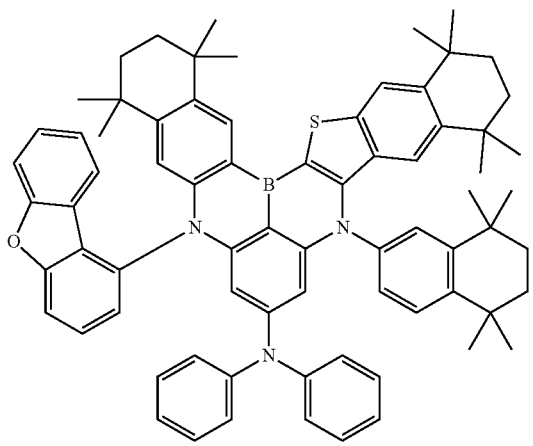
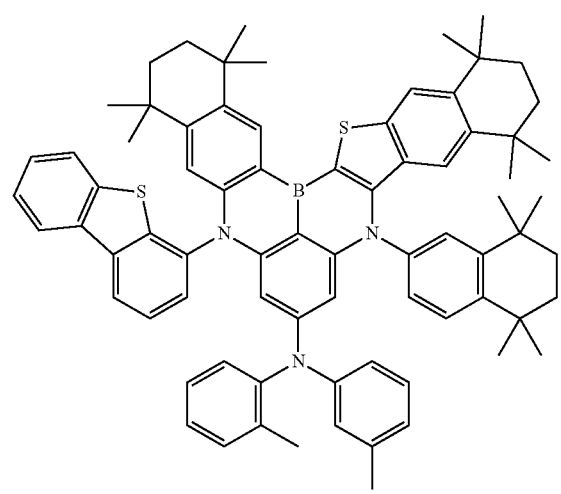
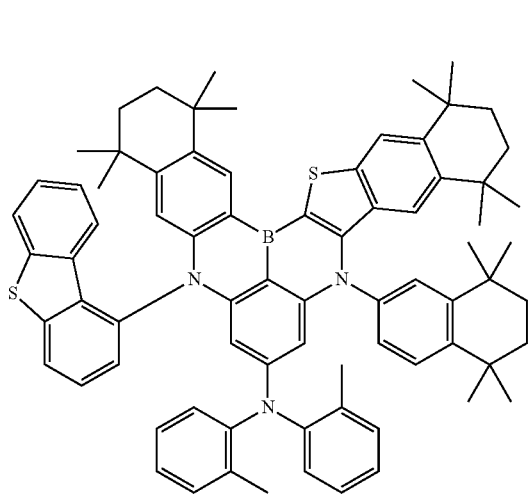
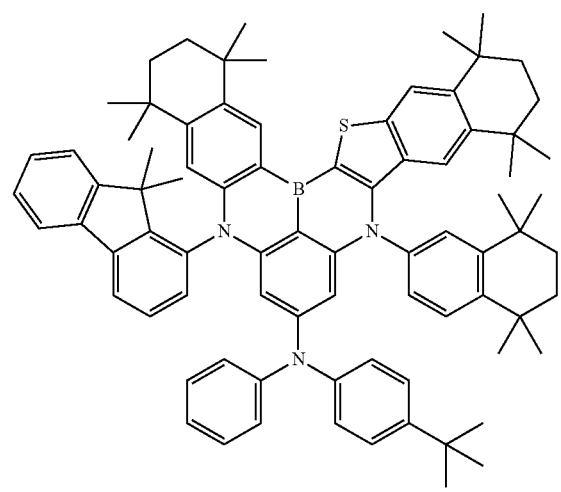

2291
-continued
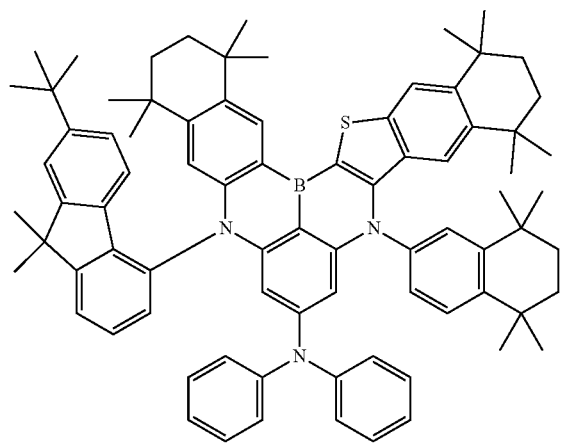
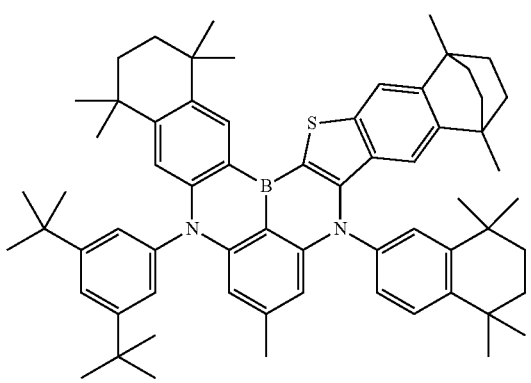
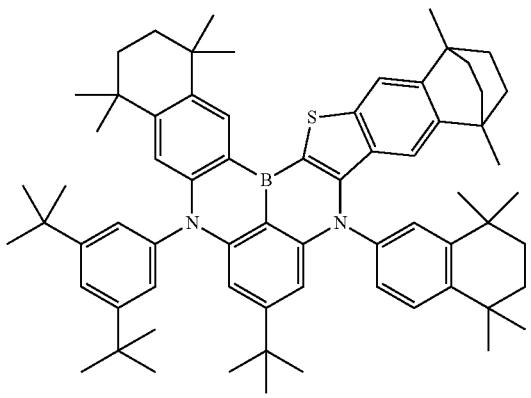
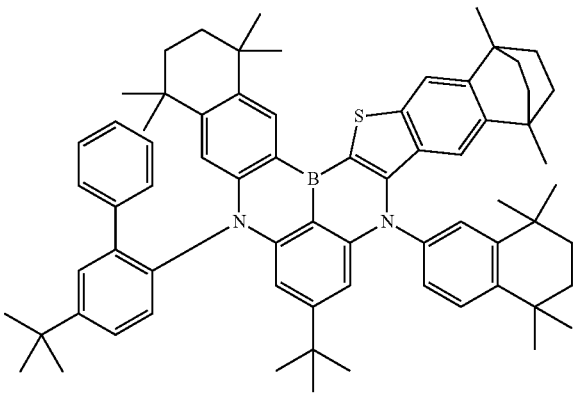
2292
-continued
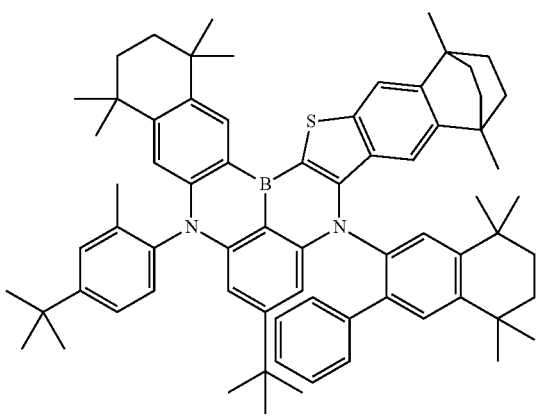
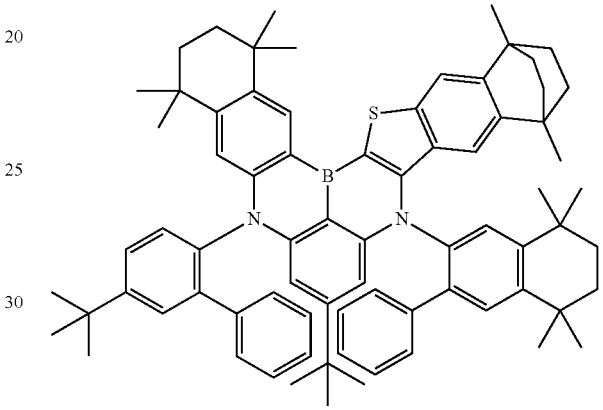
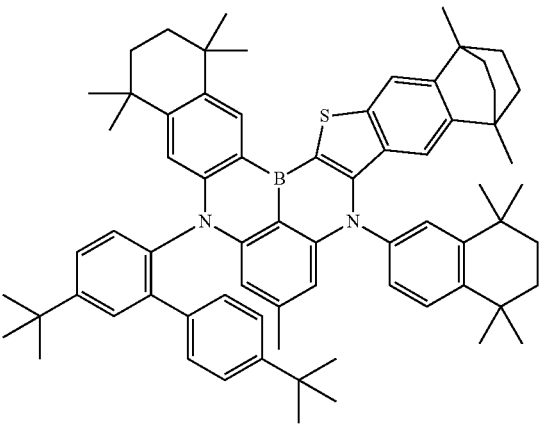
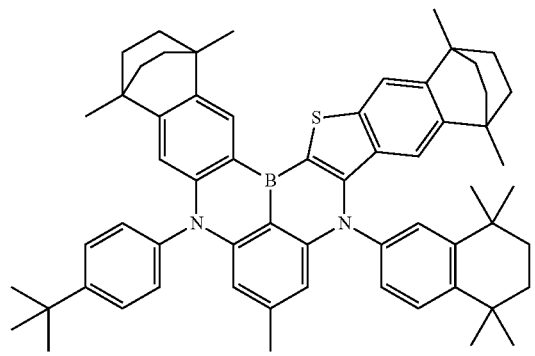

2293
-continued
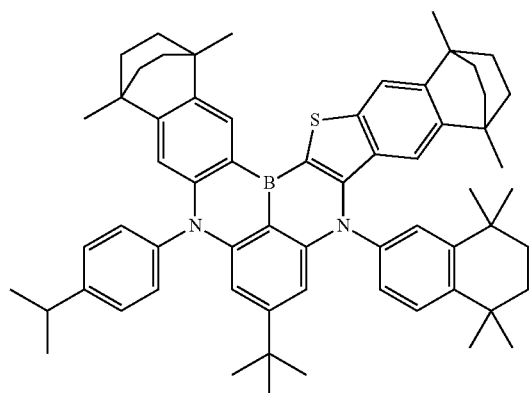
2294
-continued
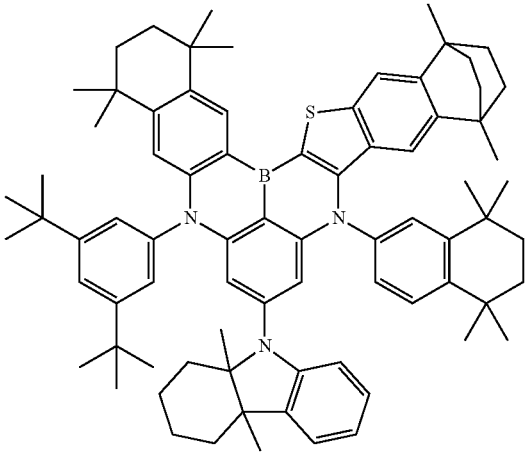
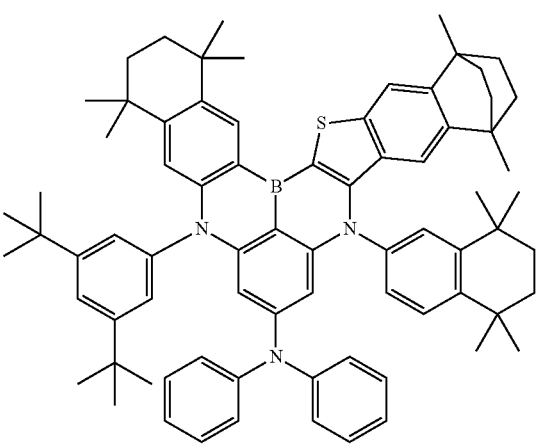
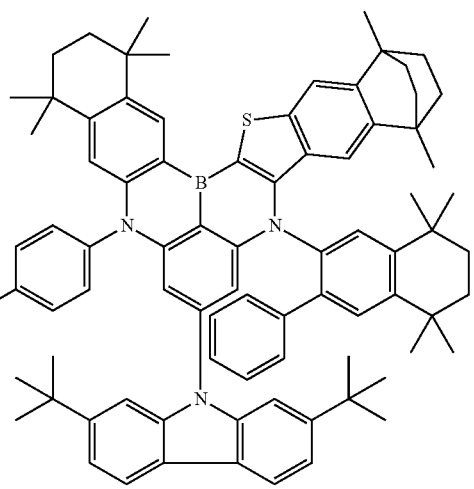
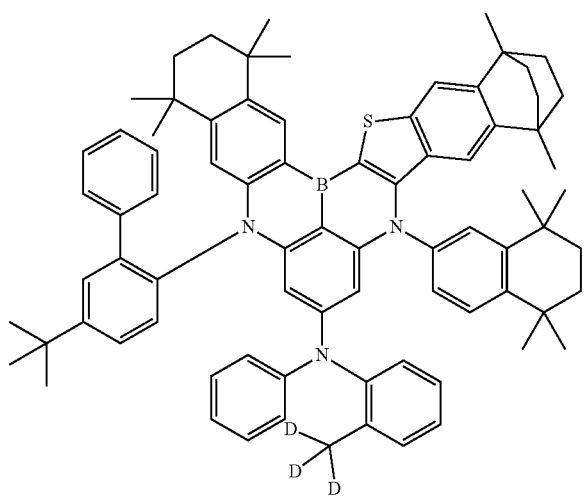
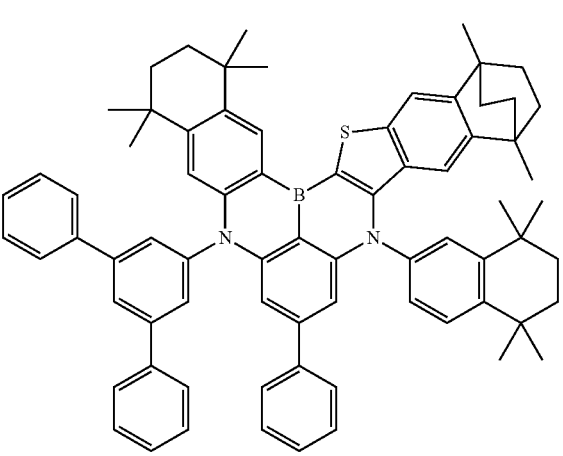

2295
-continued
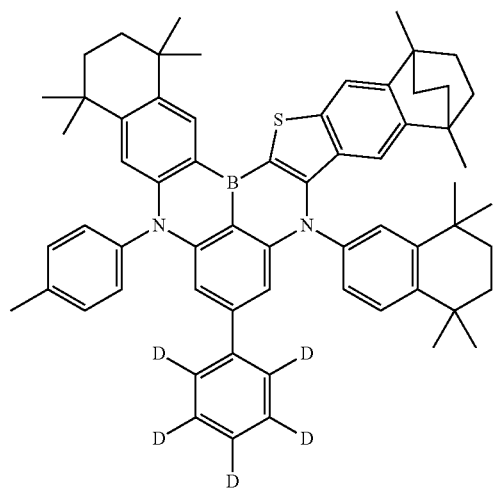
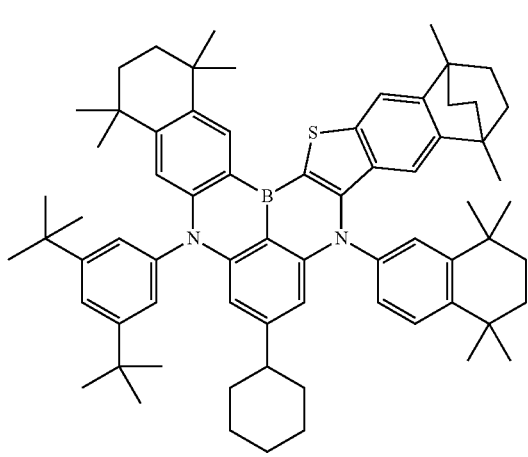
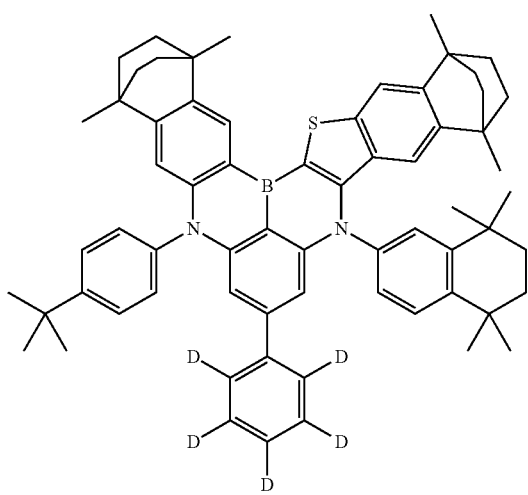
2296
-continued
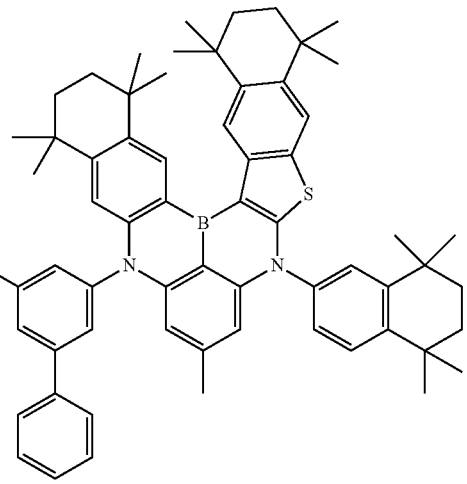
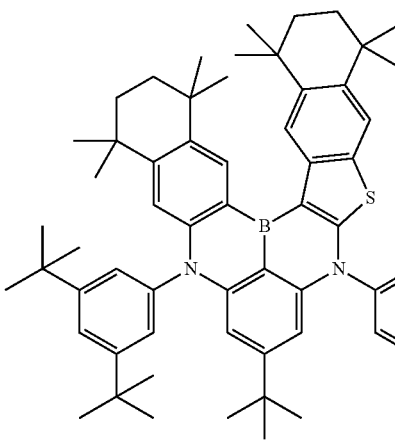
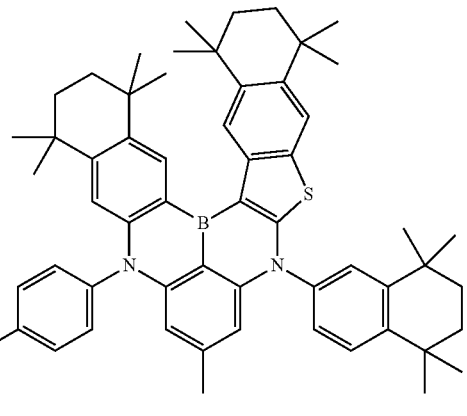

2297
-continued
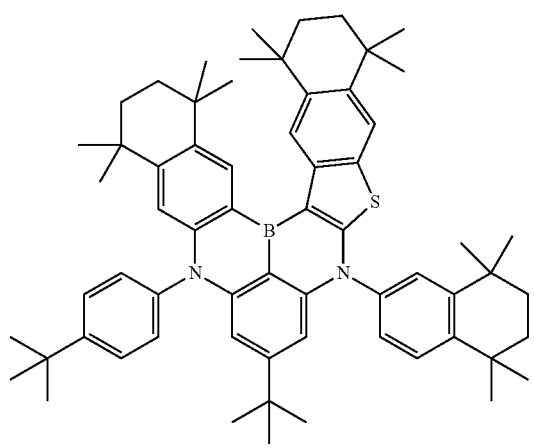
2298
-continued
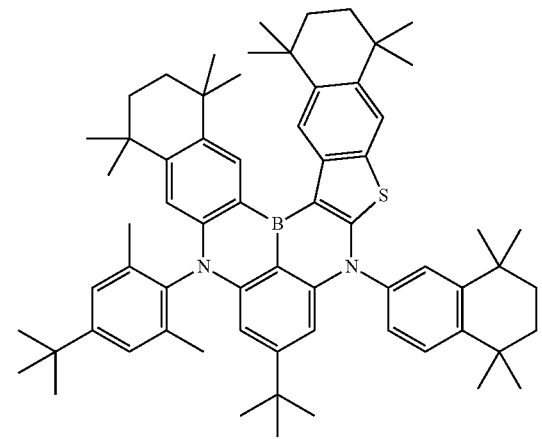
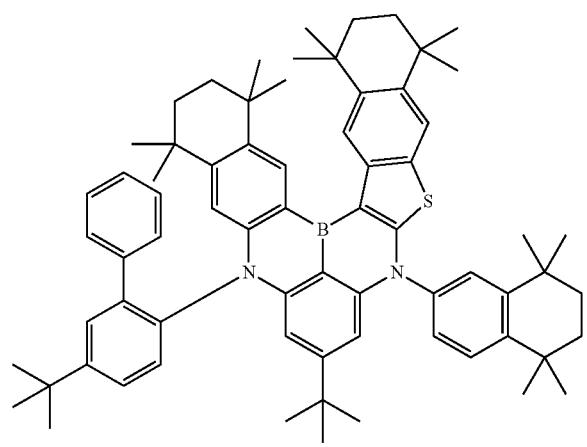
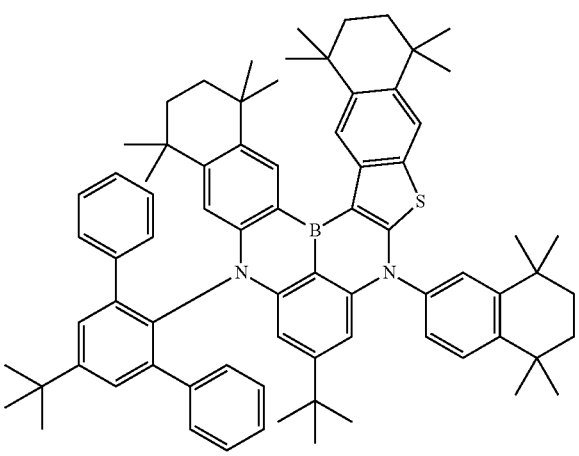
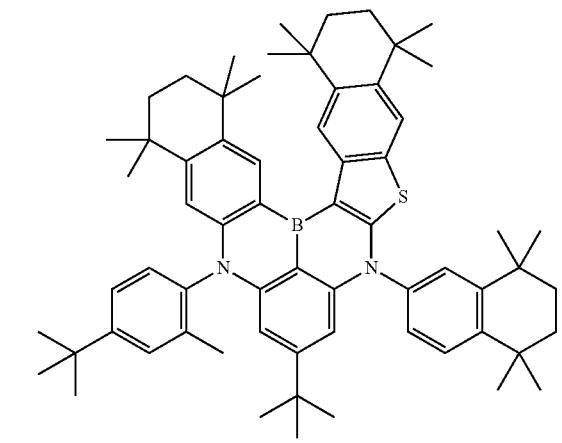

2299
-continued
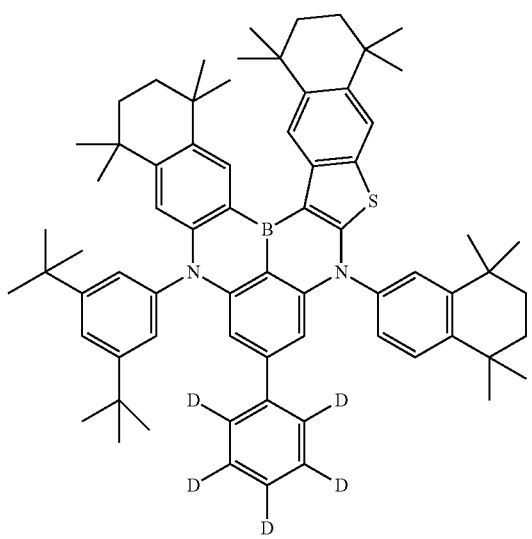
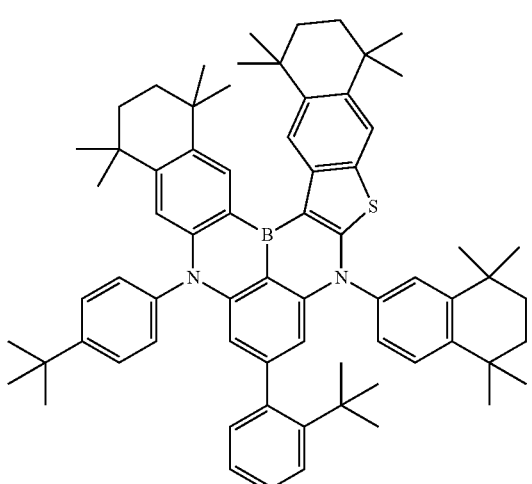
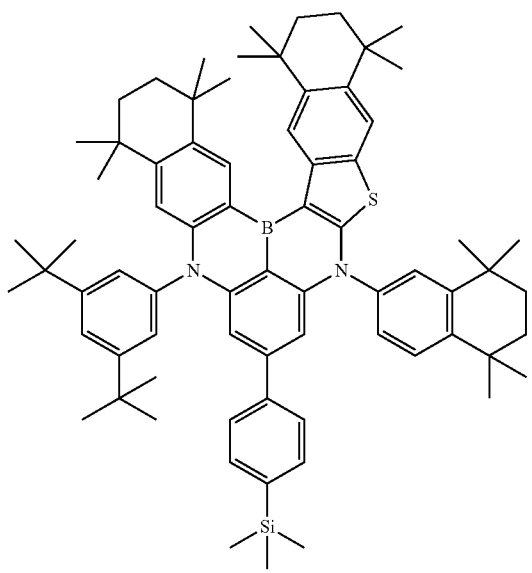
2300
-continued
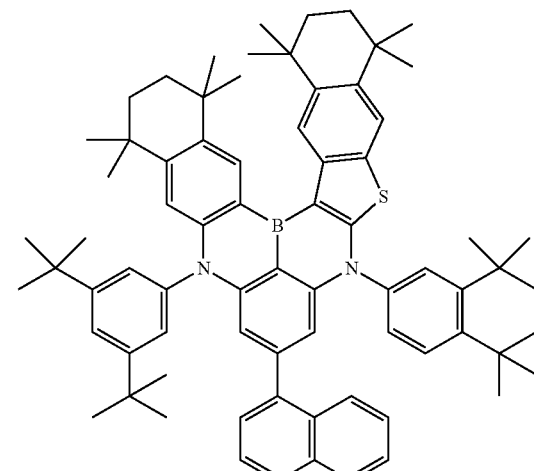
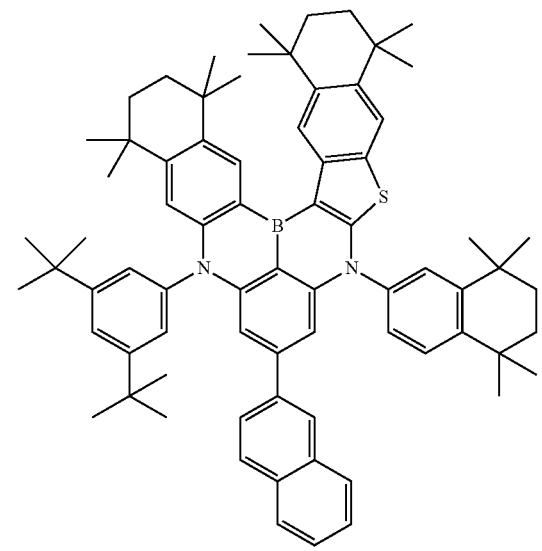
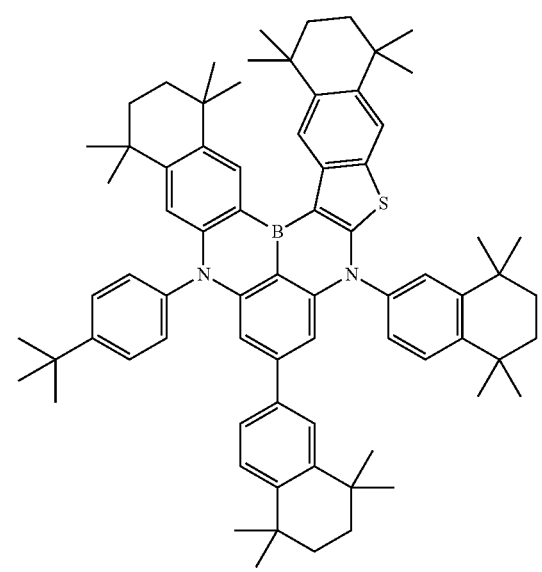

2301
-continued
2302
-continued
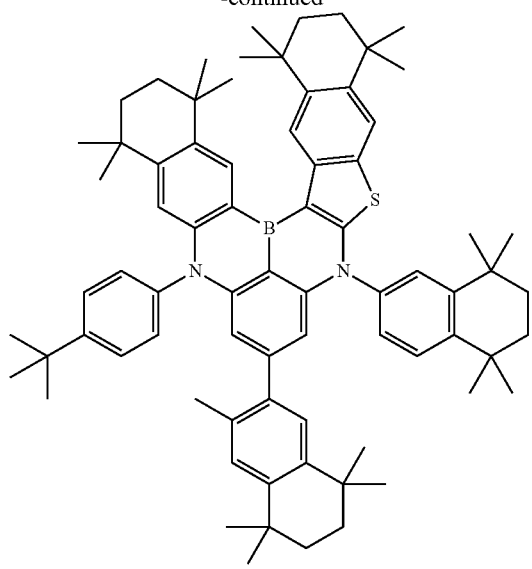
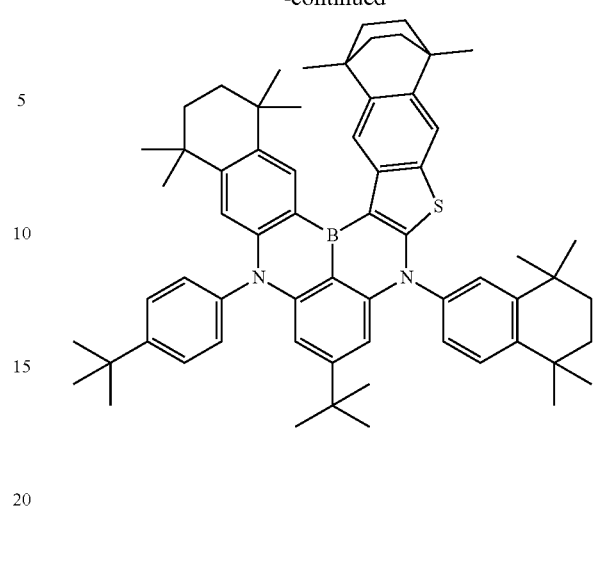
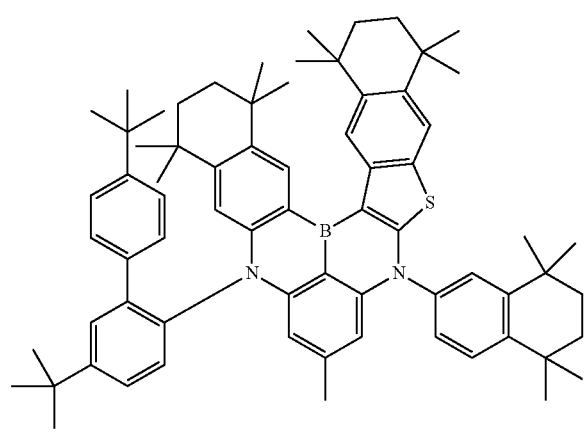
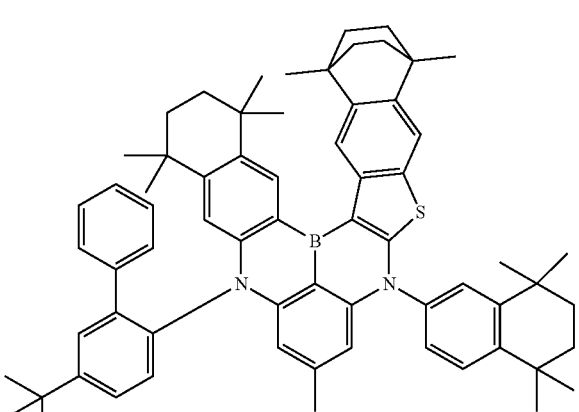
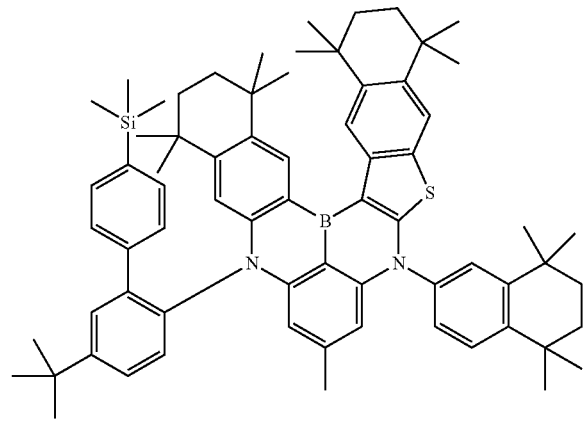
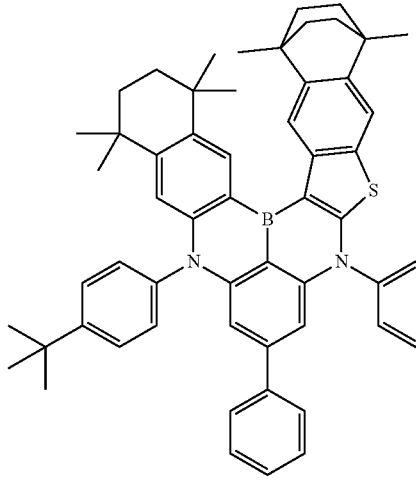

2303
-continued

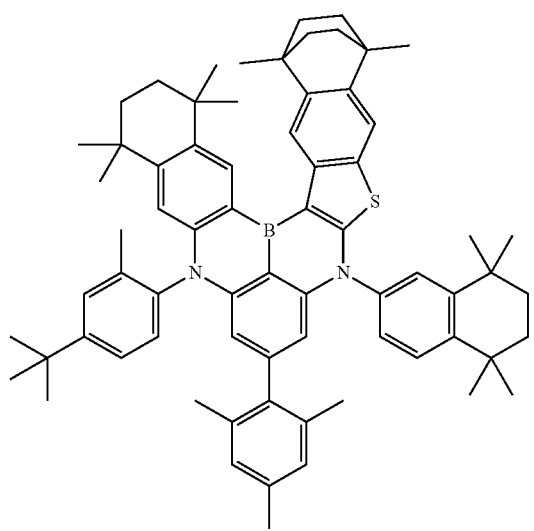
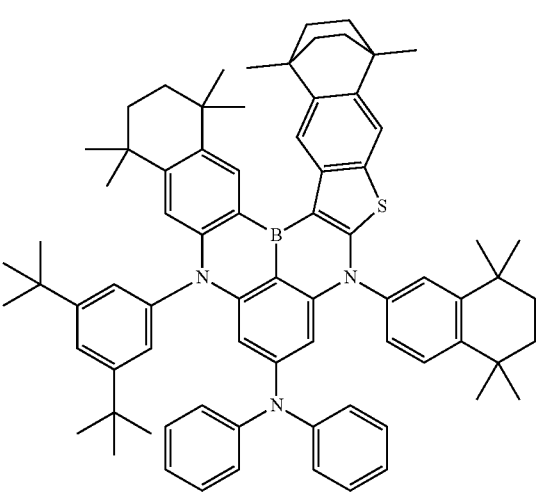
2304
-continued
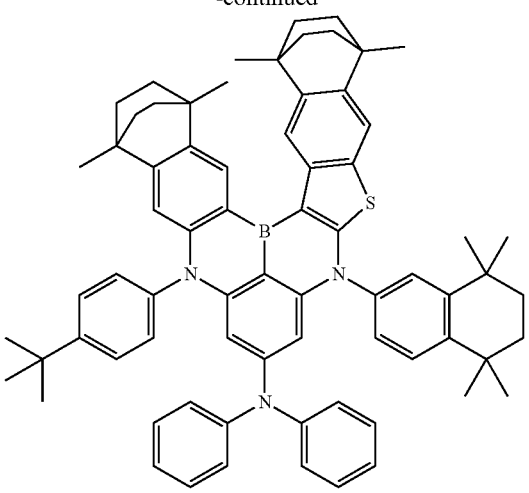
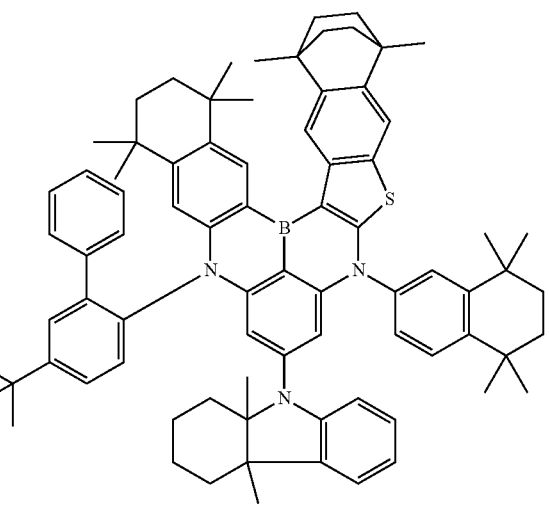
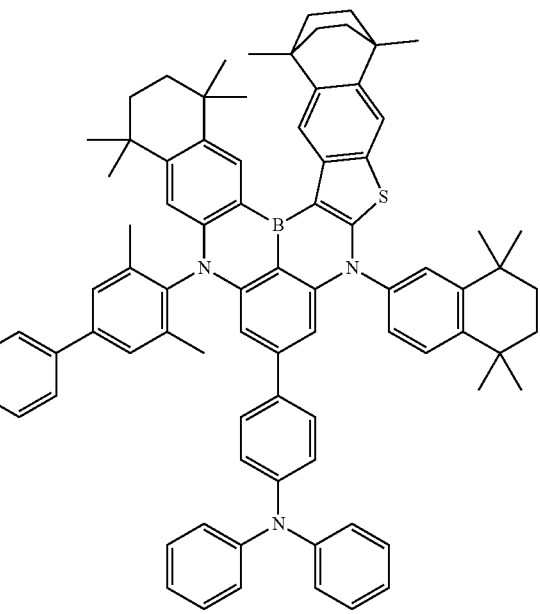

2305
-continued
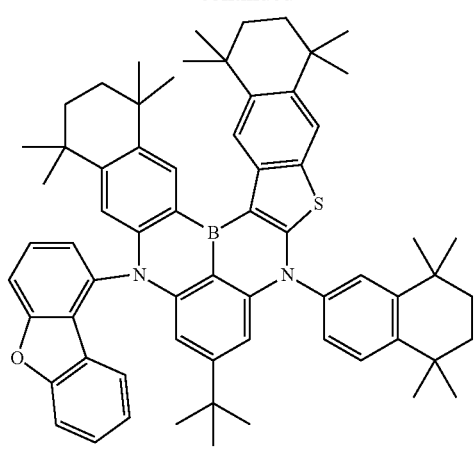
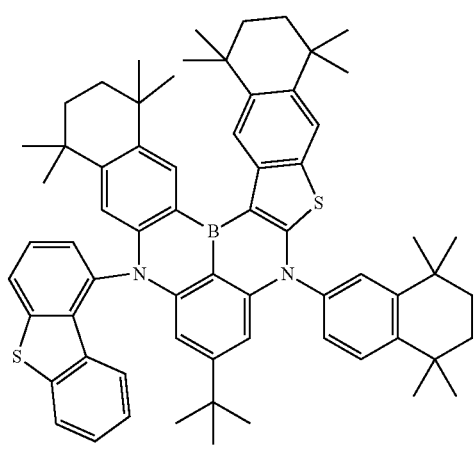
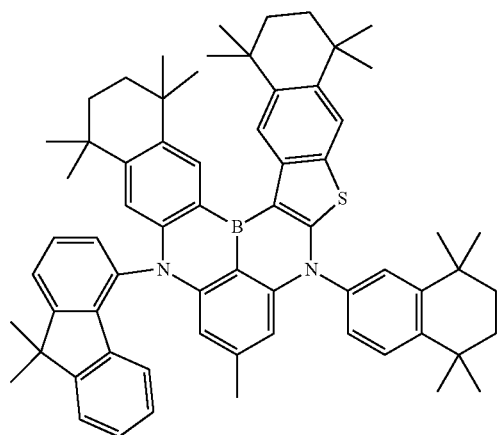
2306
-continued
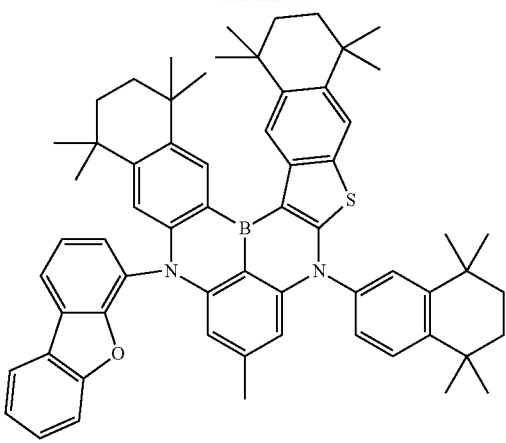
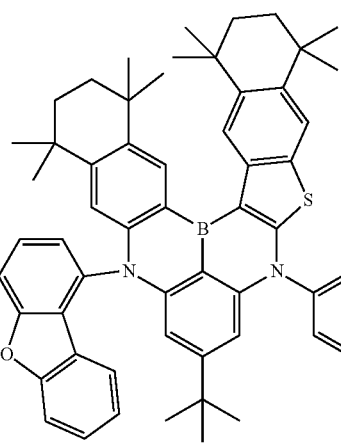
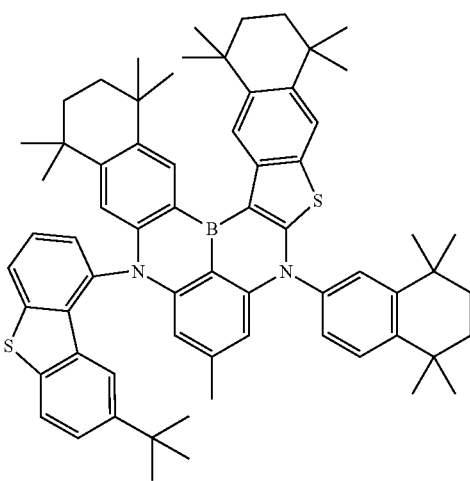

2307
-continued
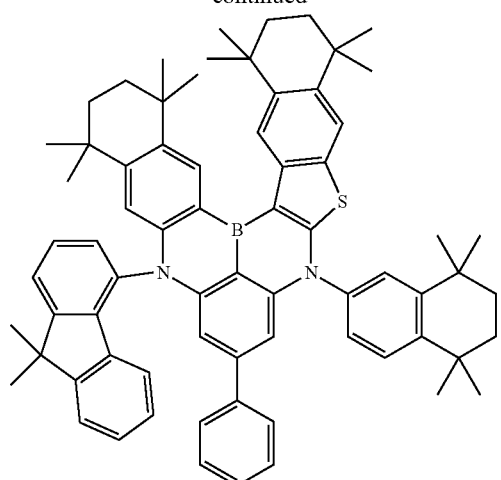
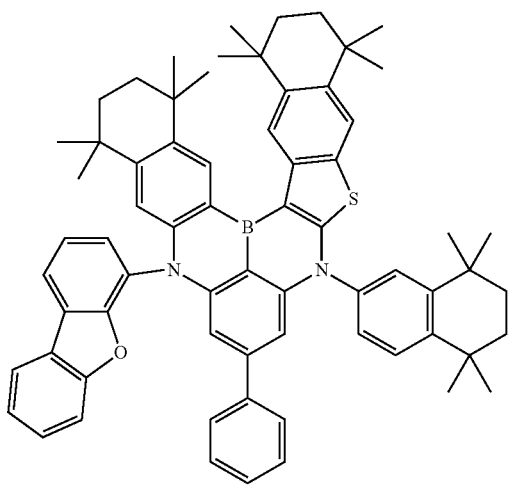
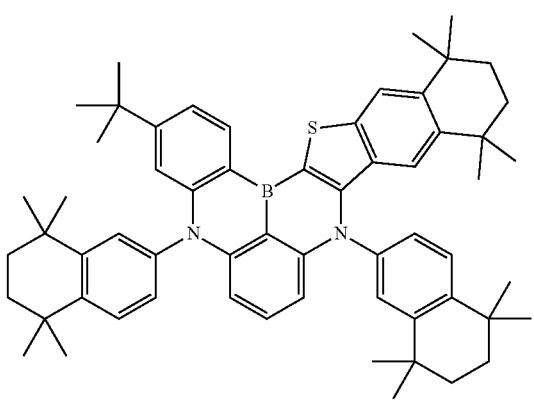
2308
-continued
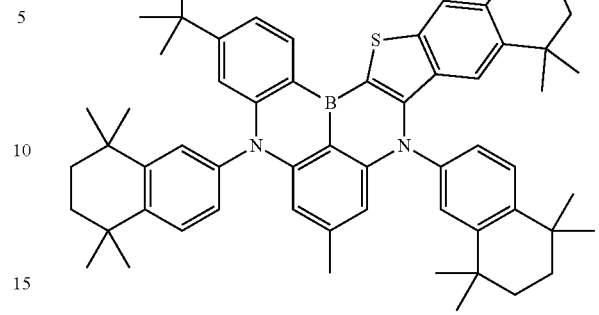
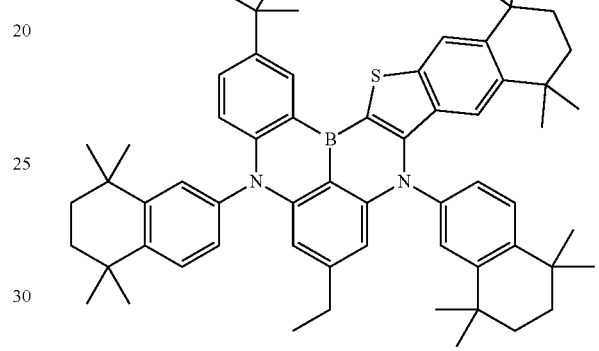
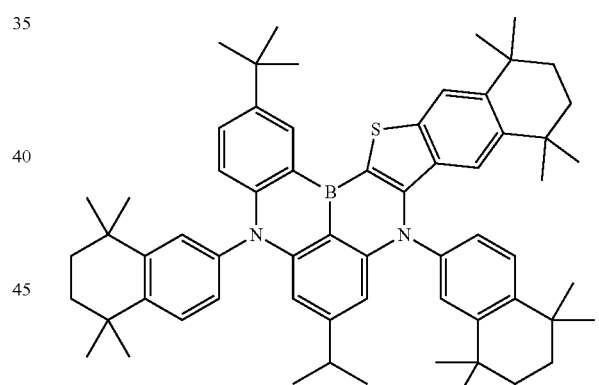
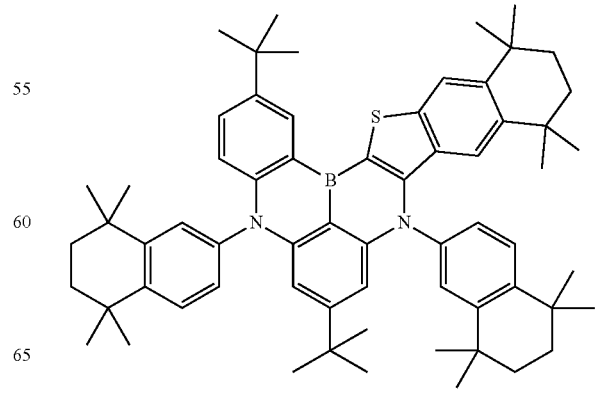

2309
-continued
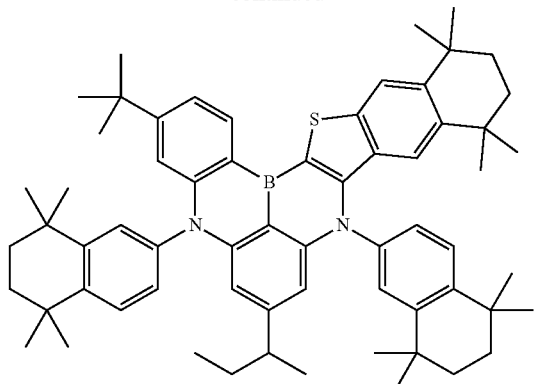
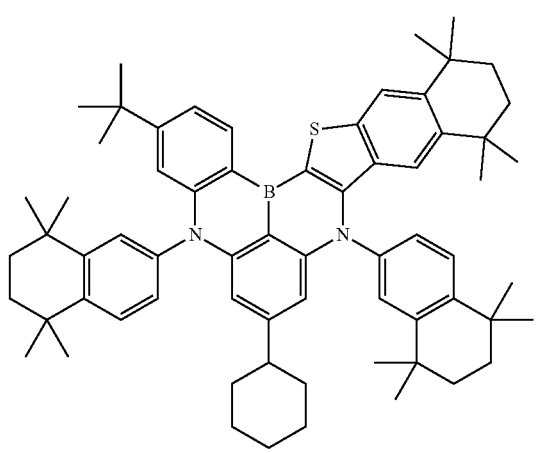
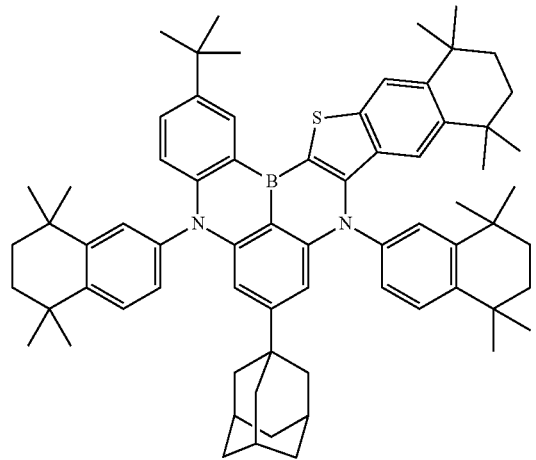
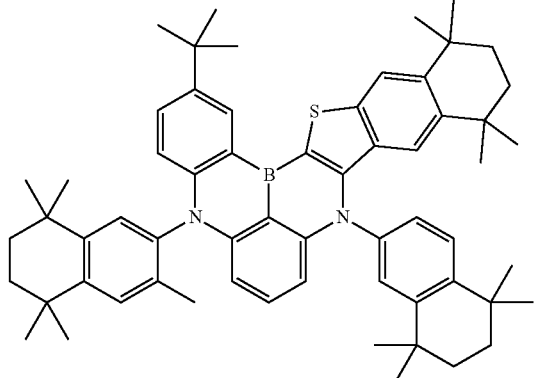
2310
-continued
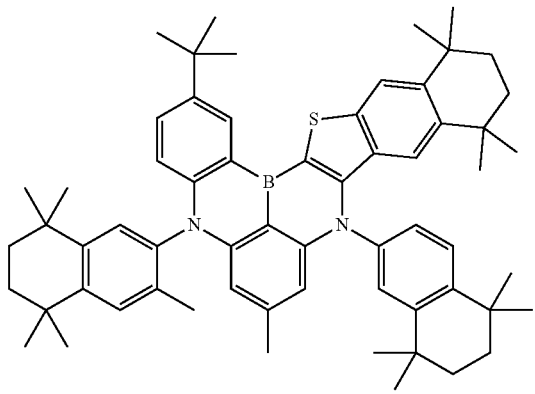
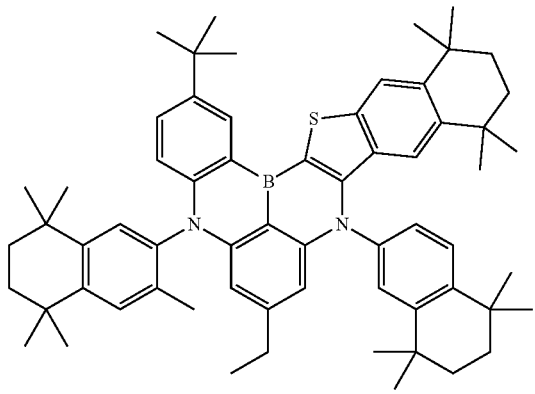
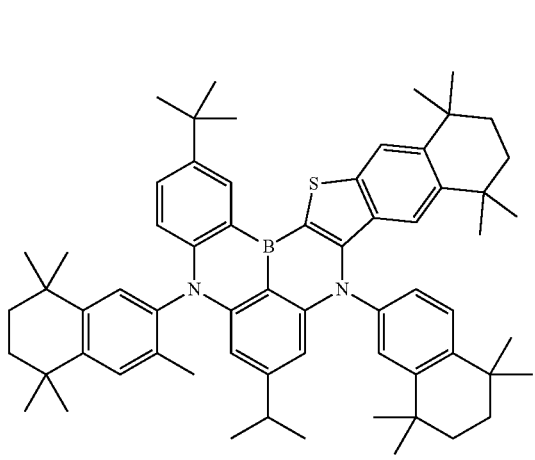
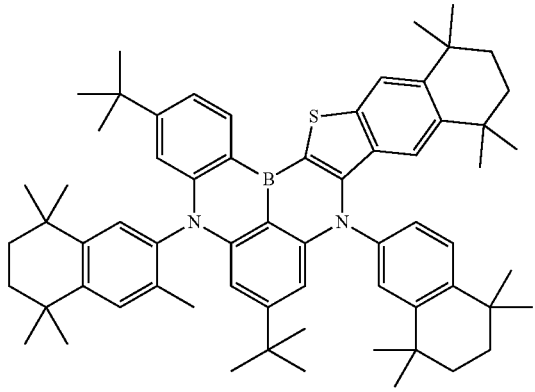

2311
-continued
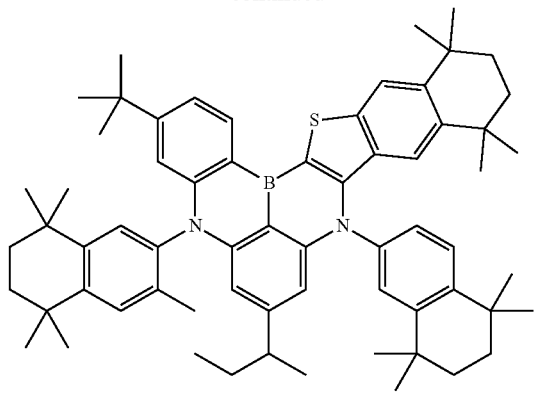
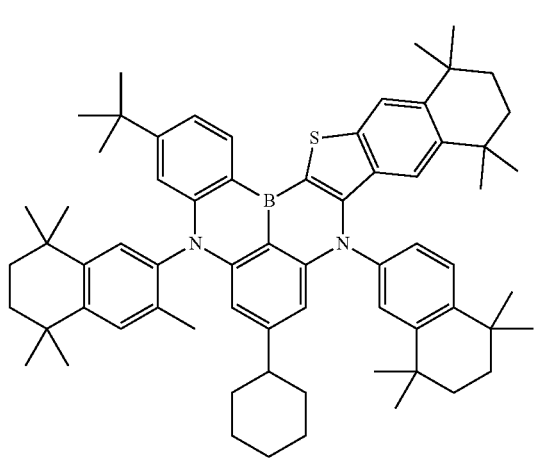
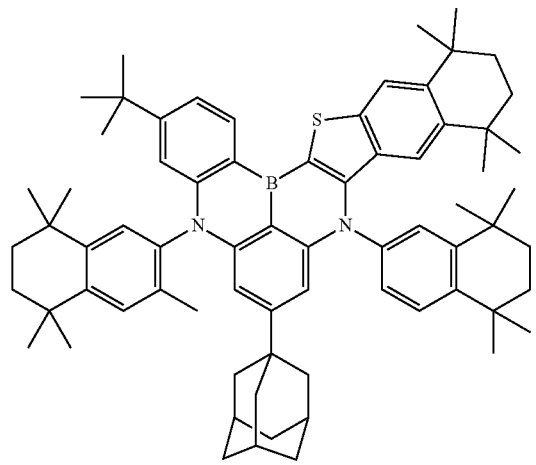
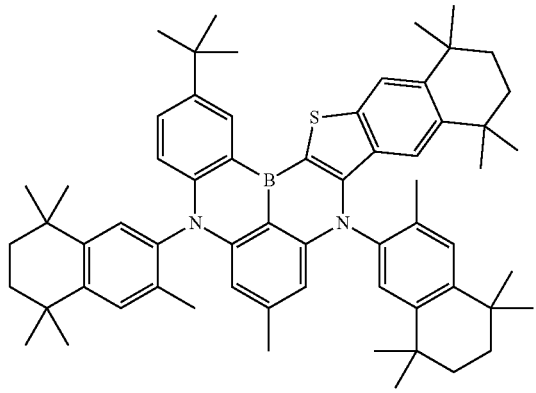
2312
-continued
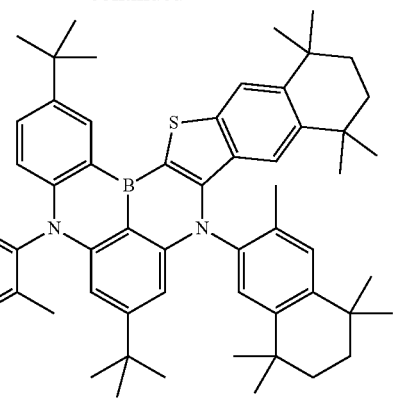
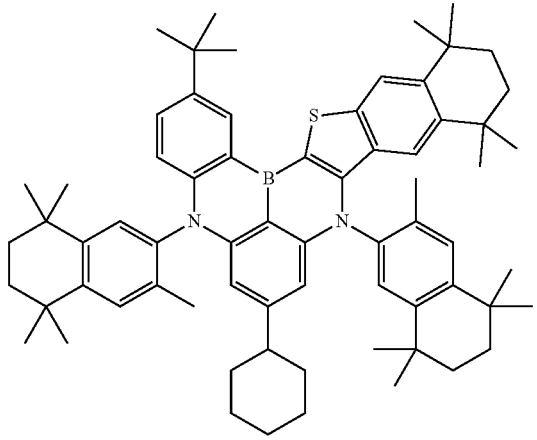
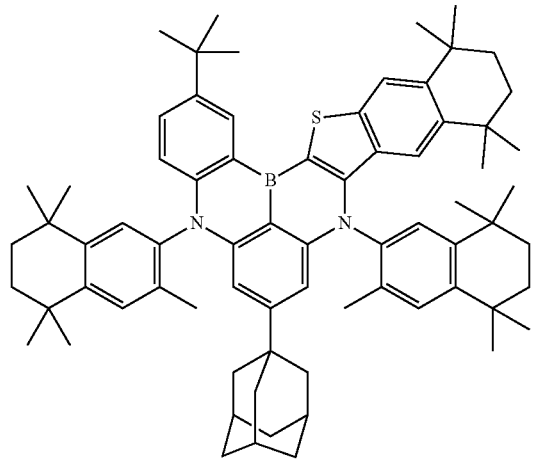
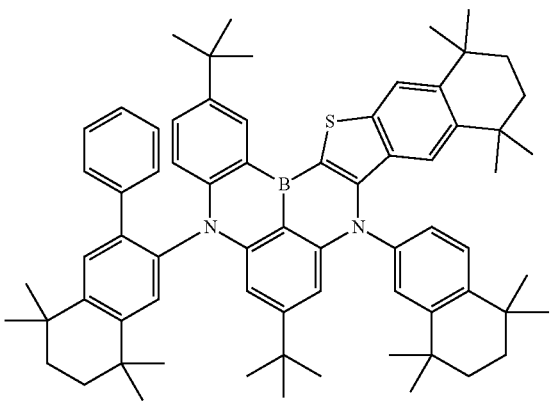

| 2313 | 2314 |
|---|---|
| -continued | -continued |
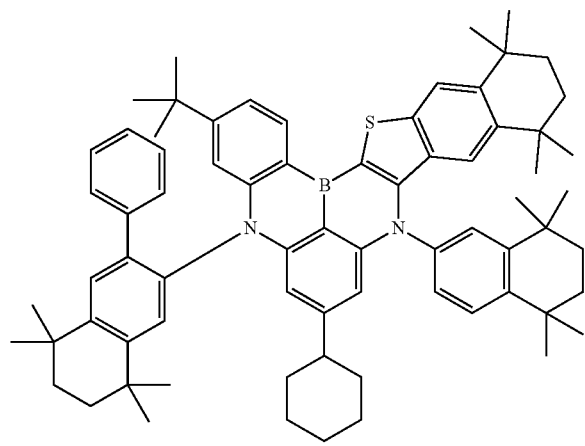
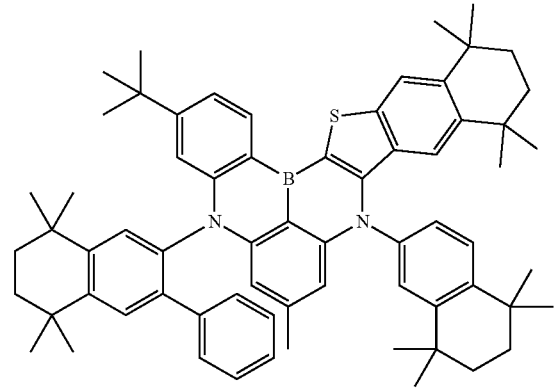
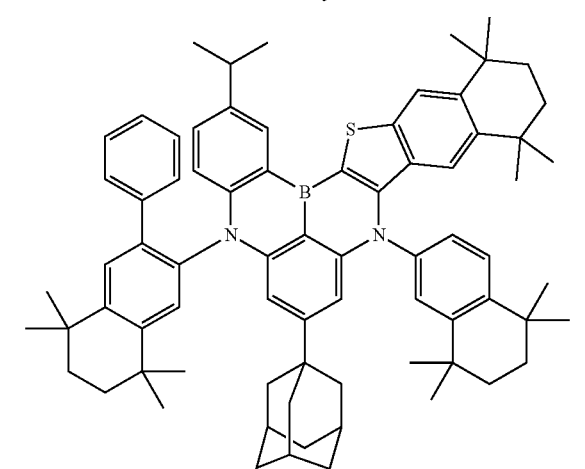
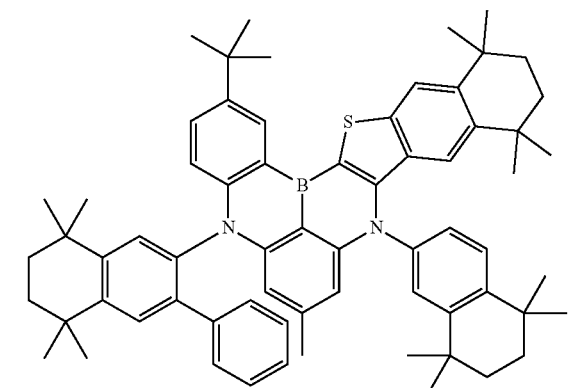
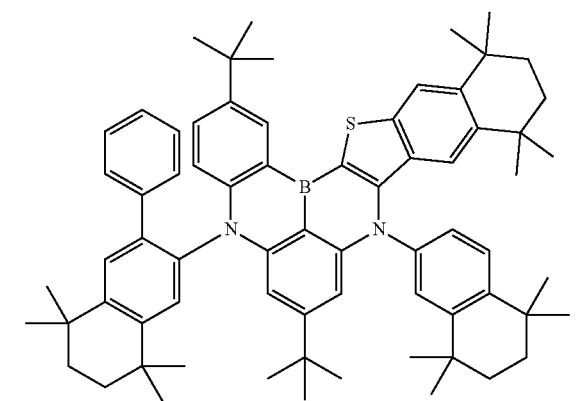

2315
-continued
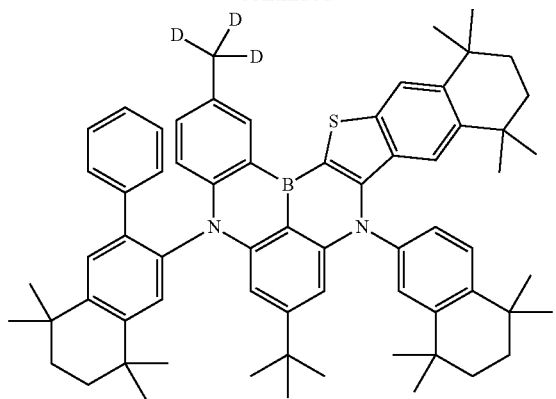
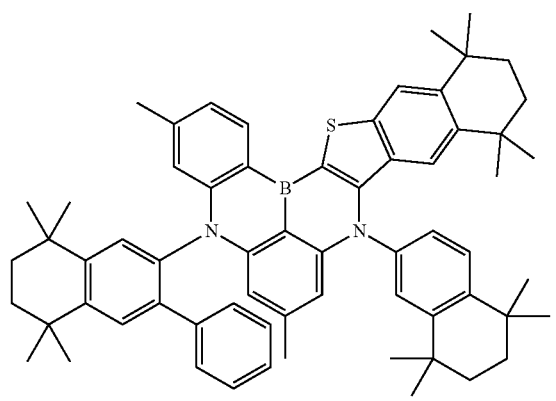
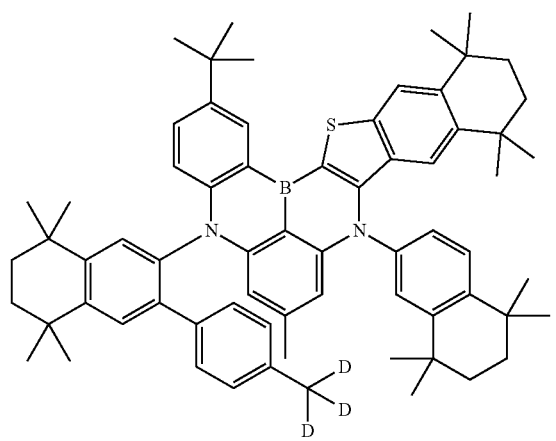
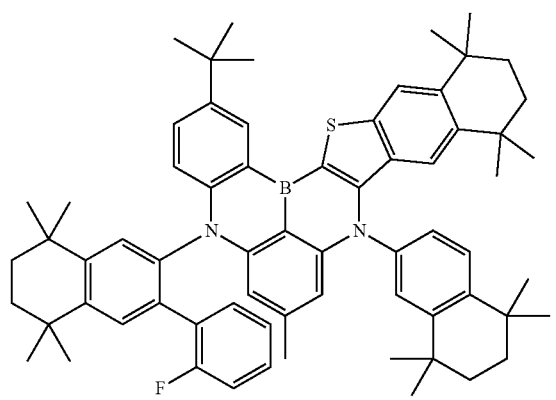
2316
-continued
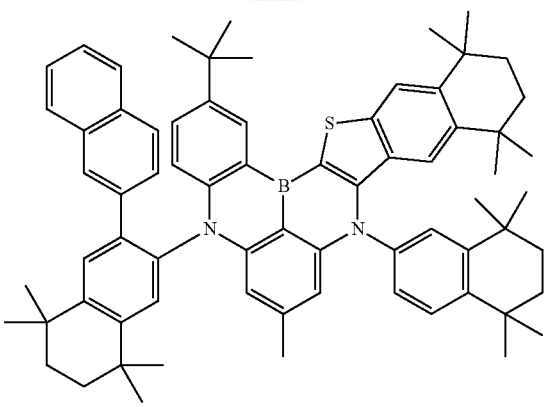
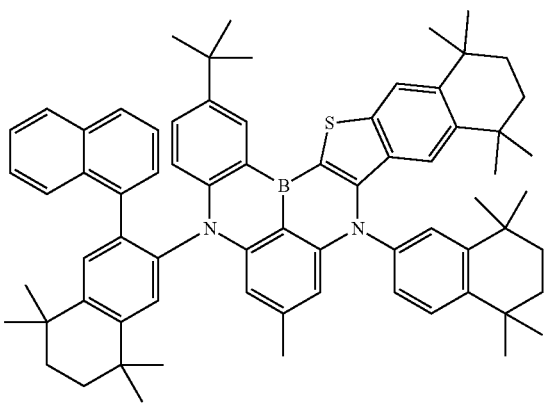
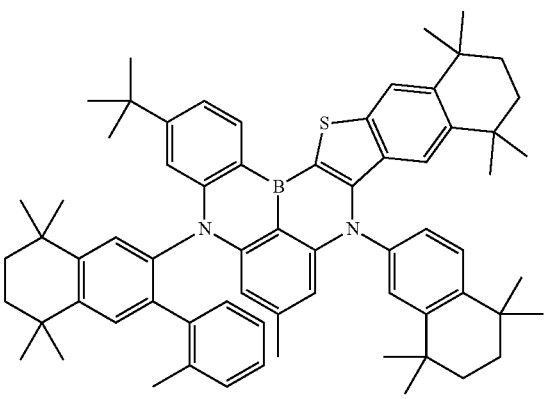

2317
-continued
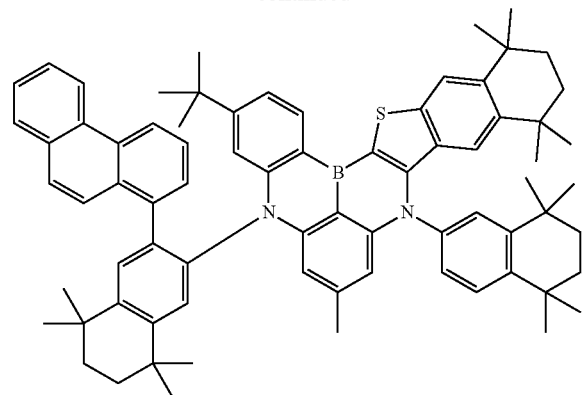
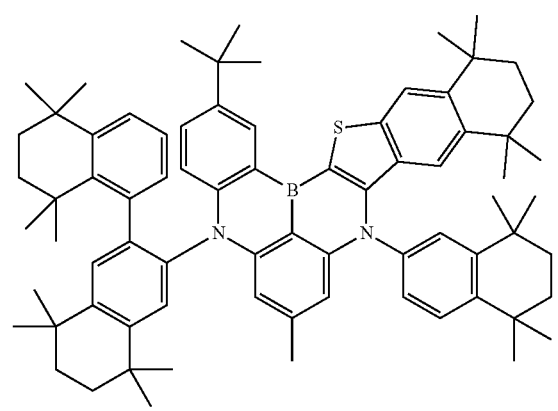
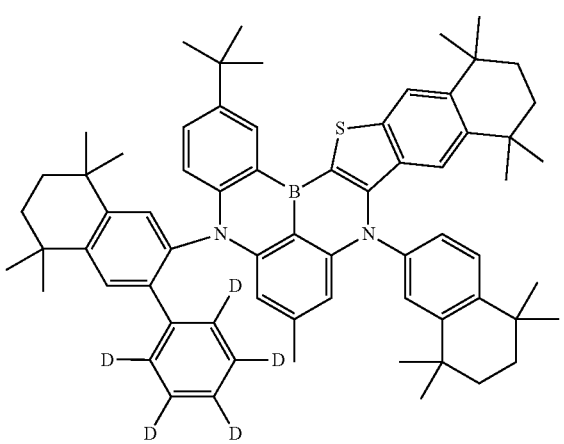
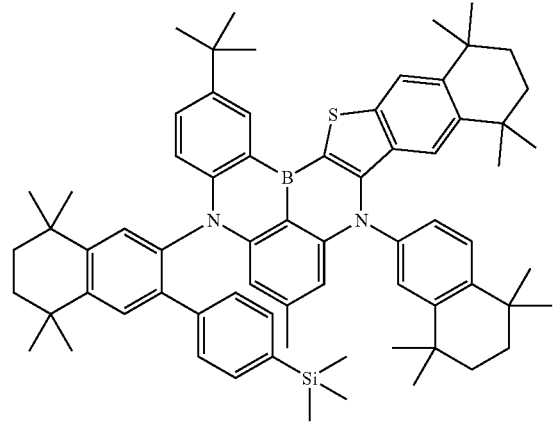
2318
-continued
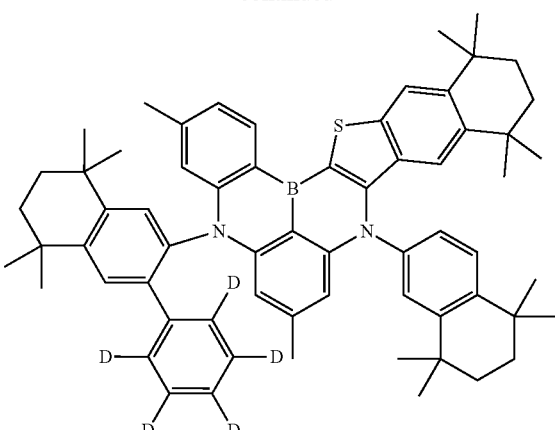
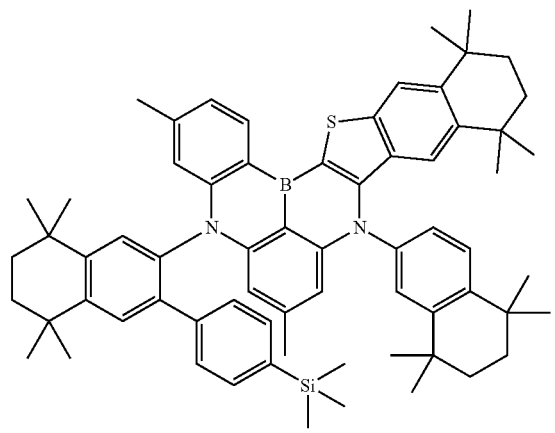
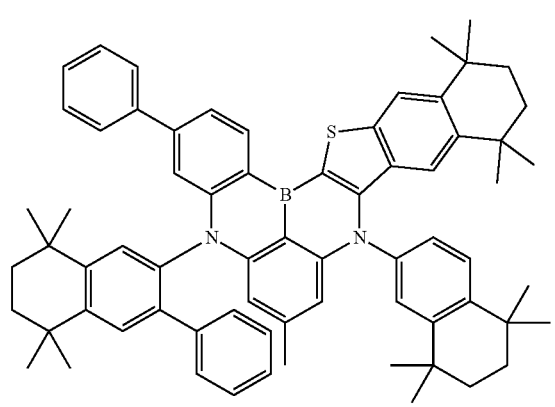
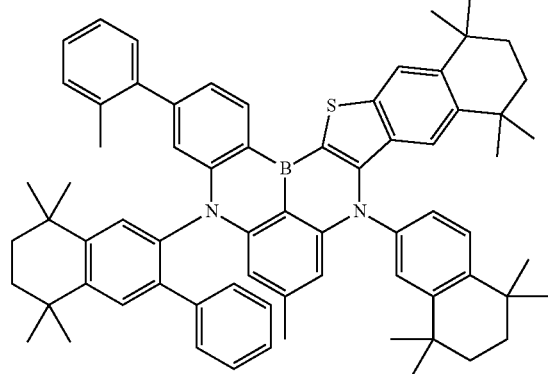

2319
-continued
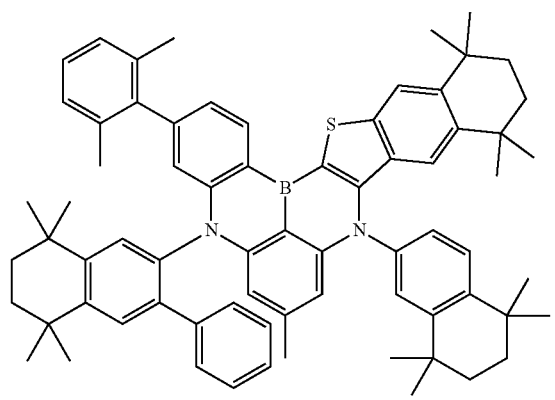
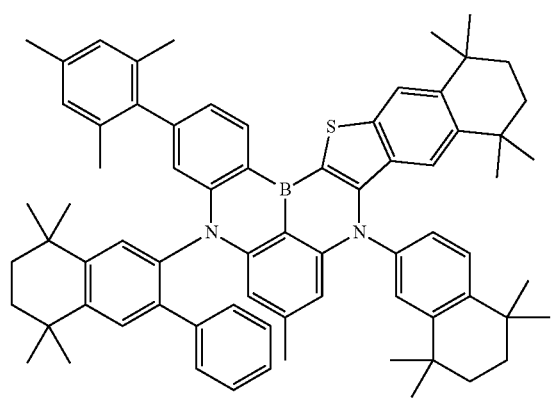
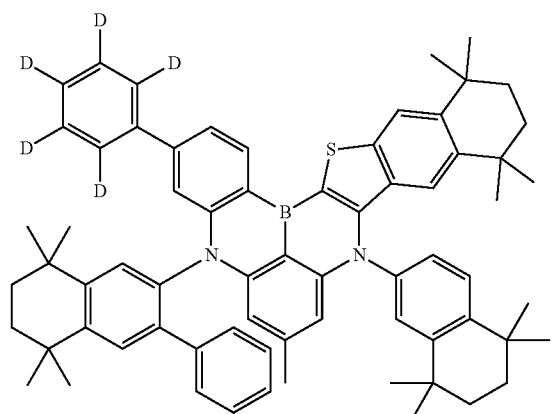
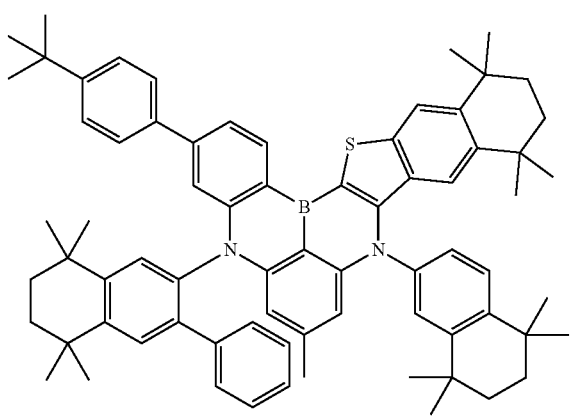
2320
-continued
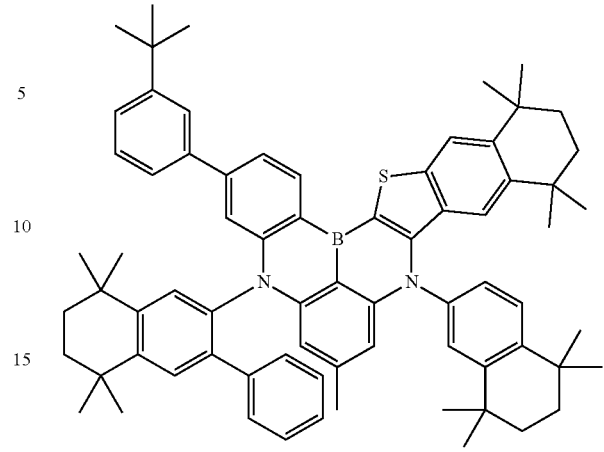
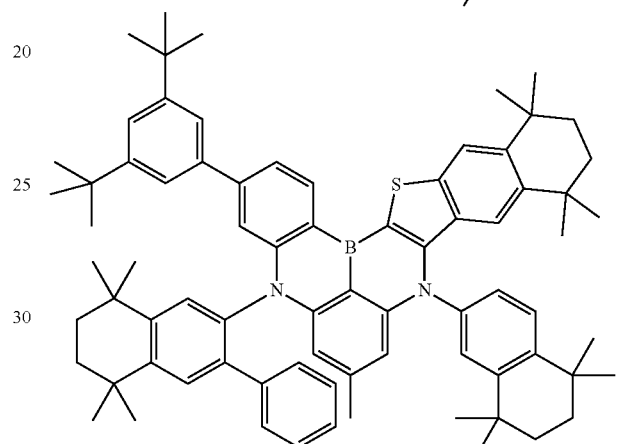
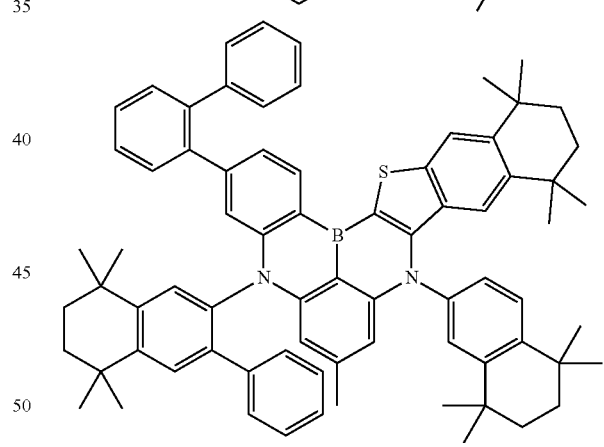
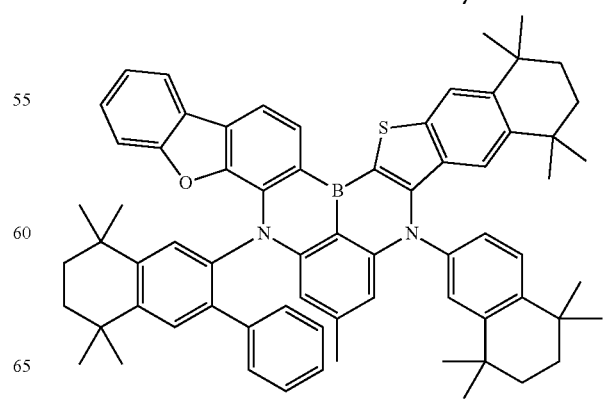

2321
-continued
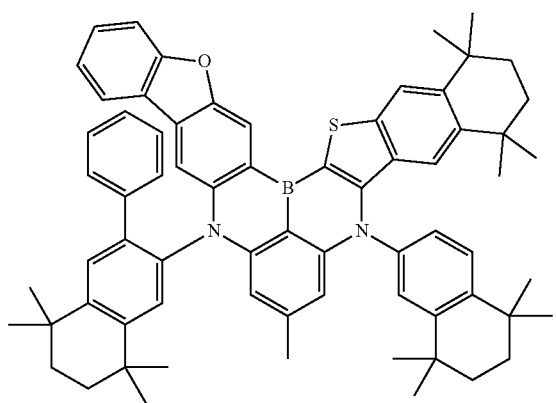
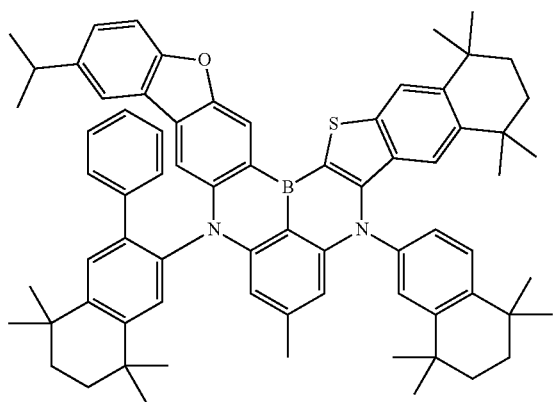
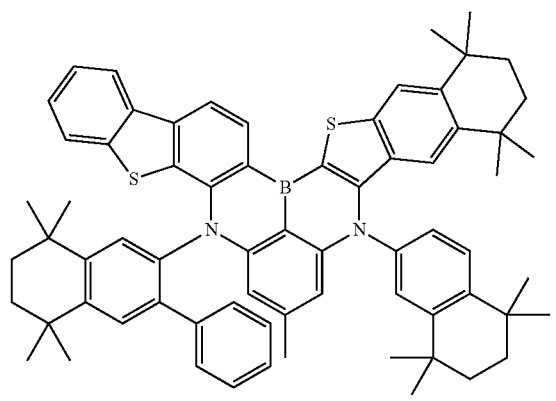
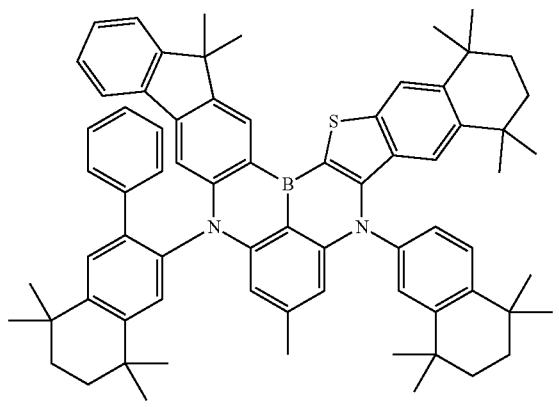
2322
-continued
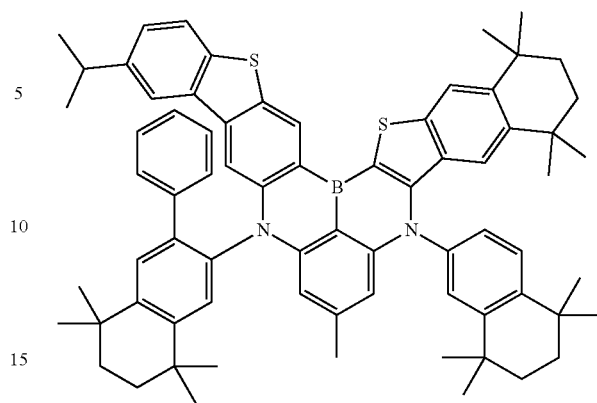
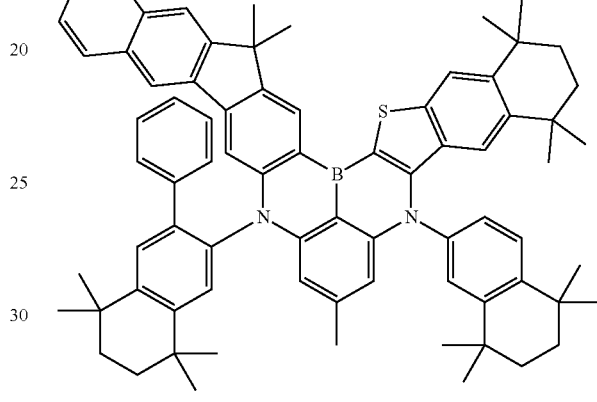

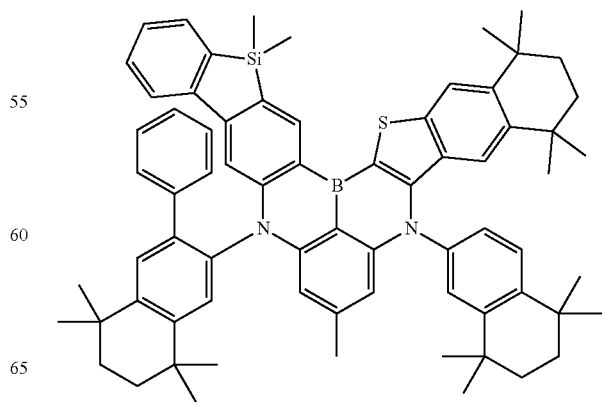

2323
-continued
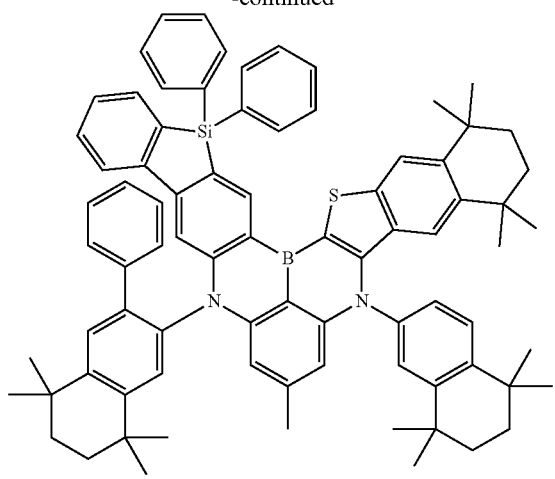
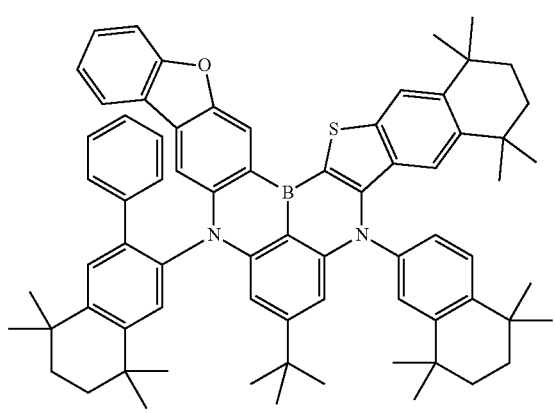
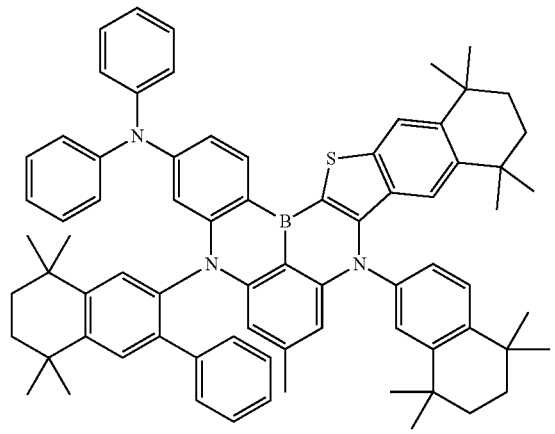
2324
-continued
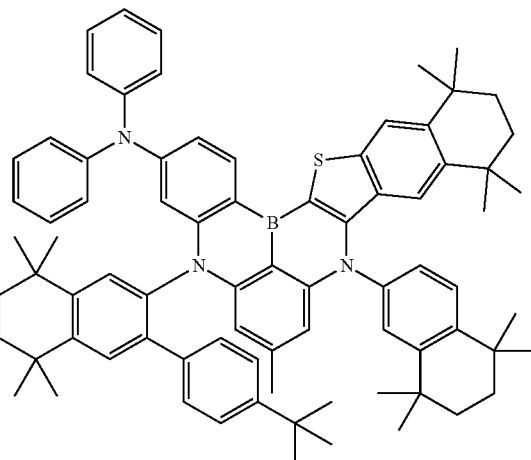
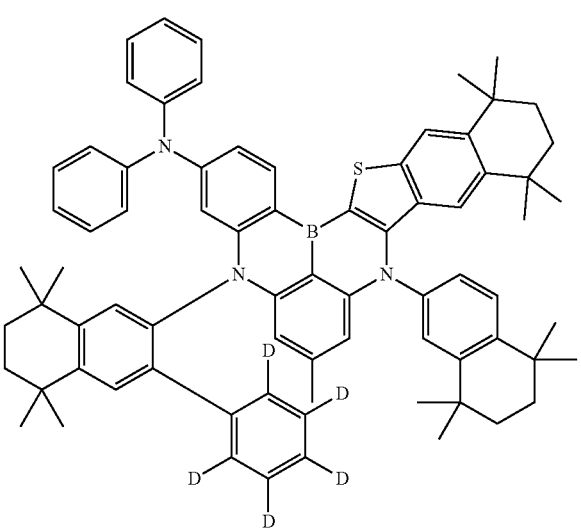
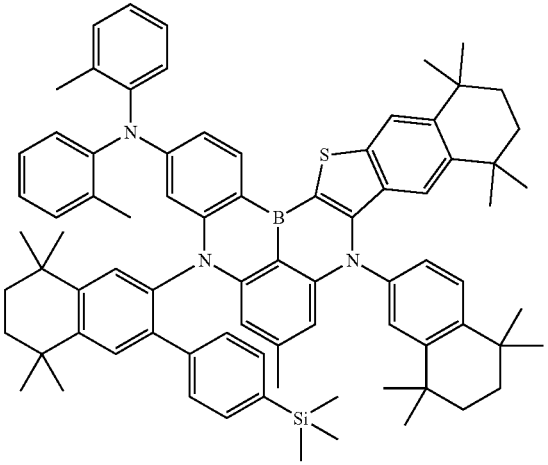

2325
-continued
2326
-continued
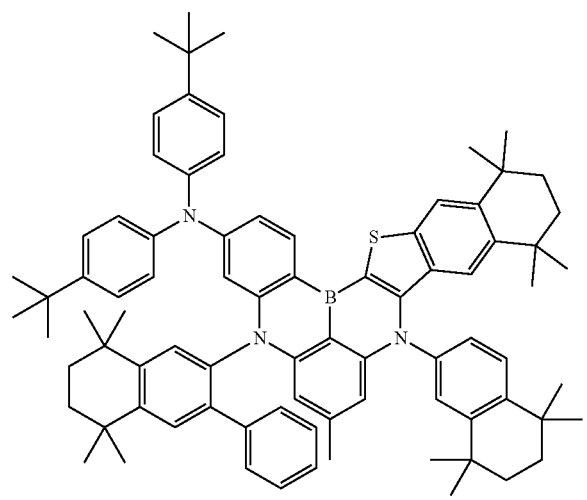
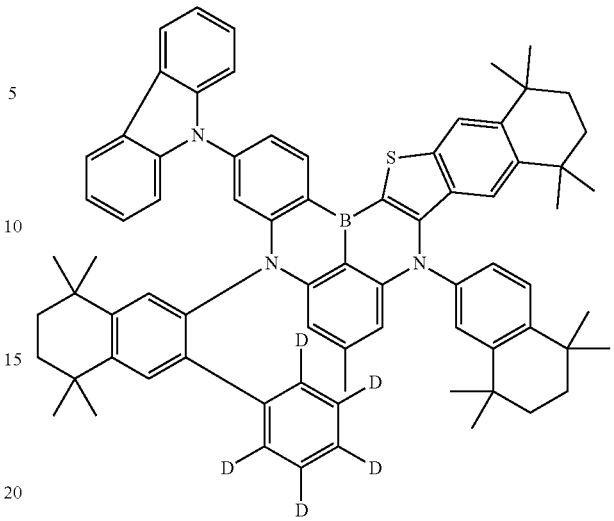
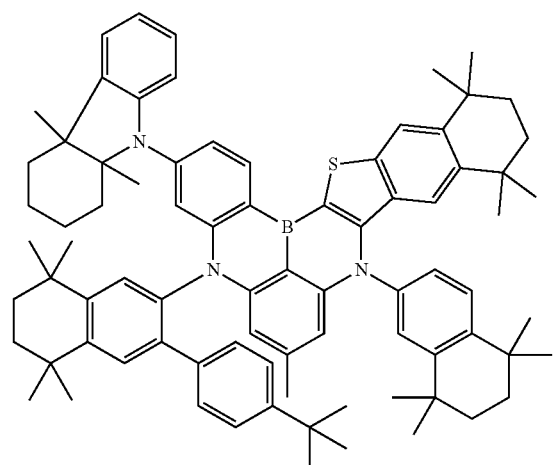
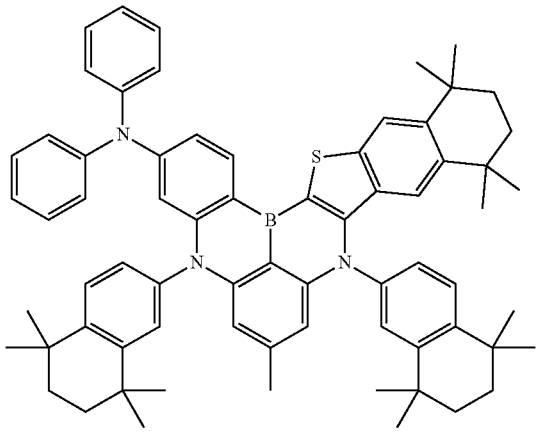
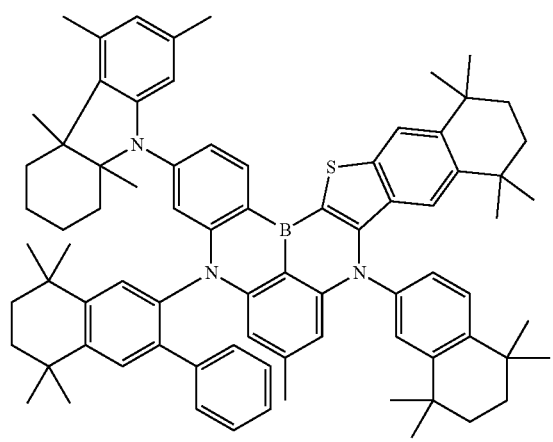
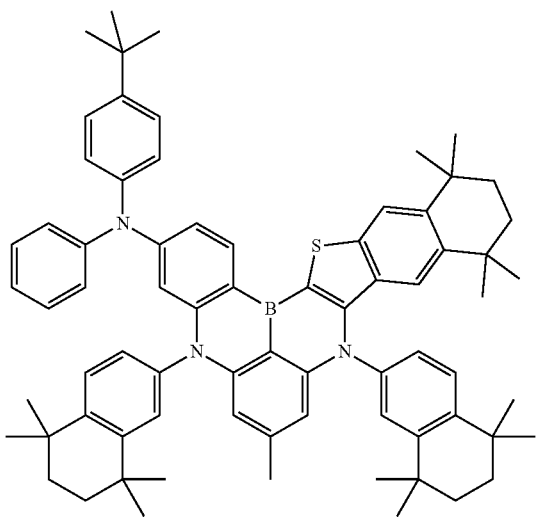

2327
-continued
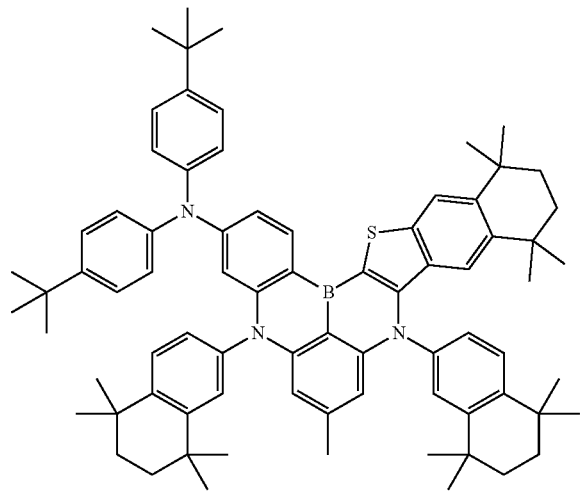
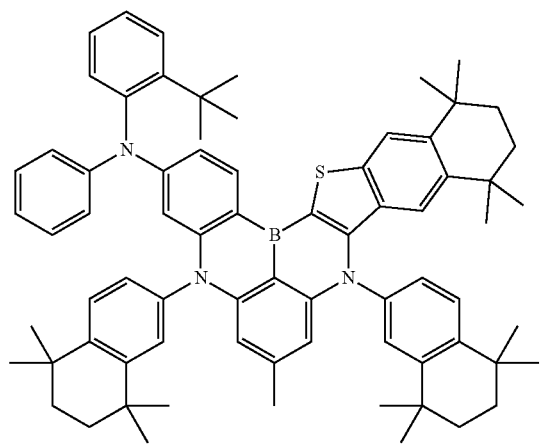
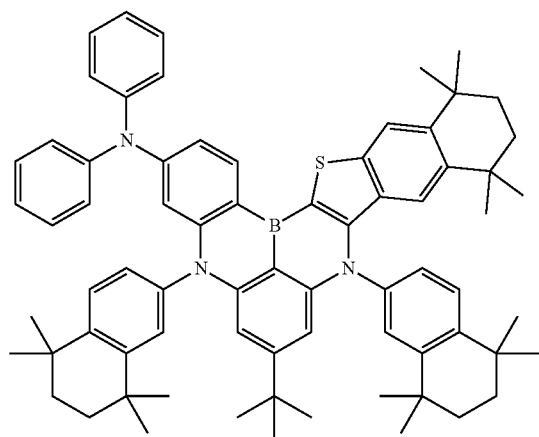
2328
-continued
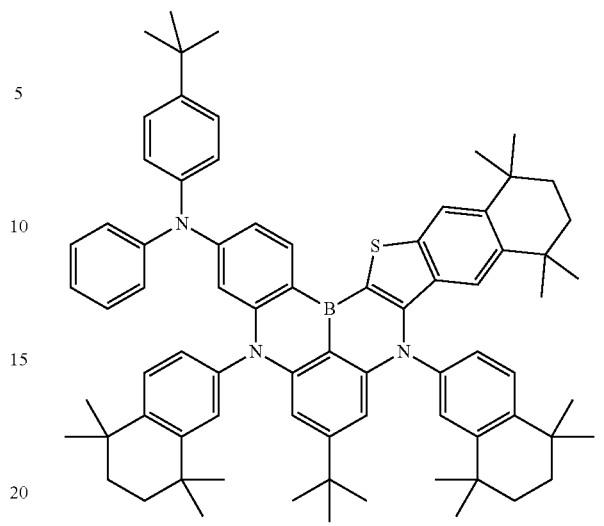
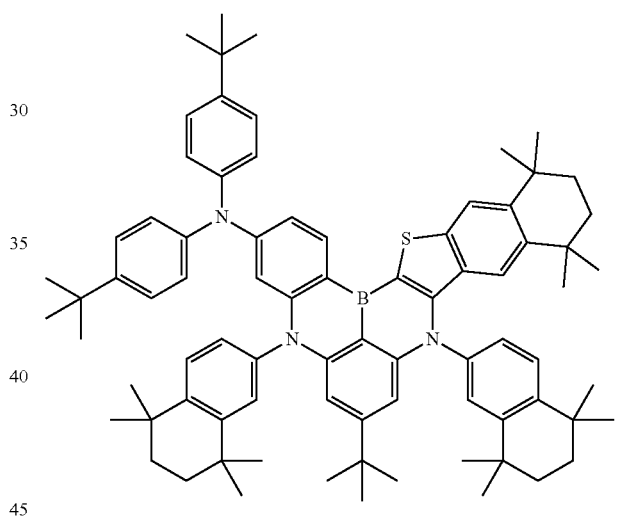
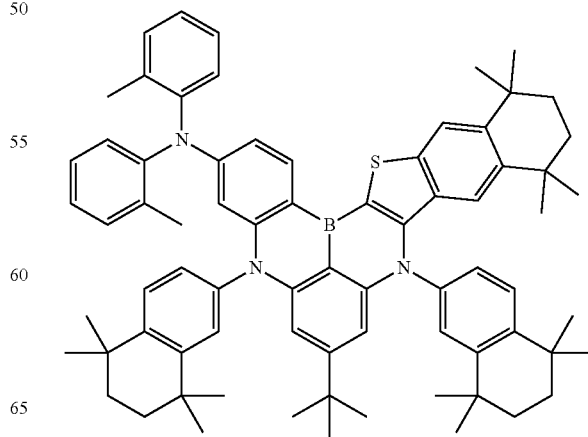

2329
-continued
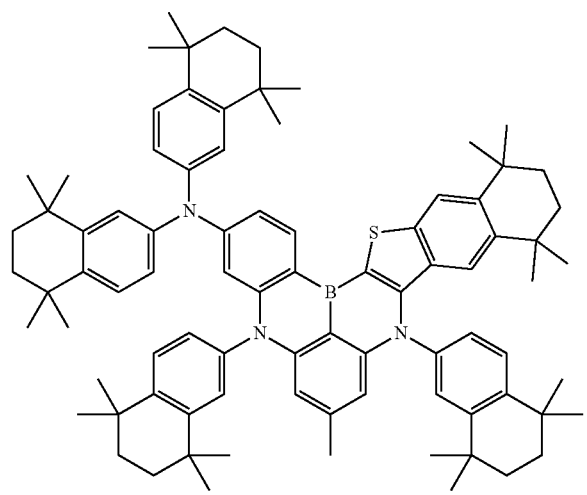
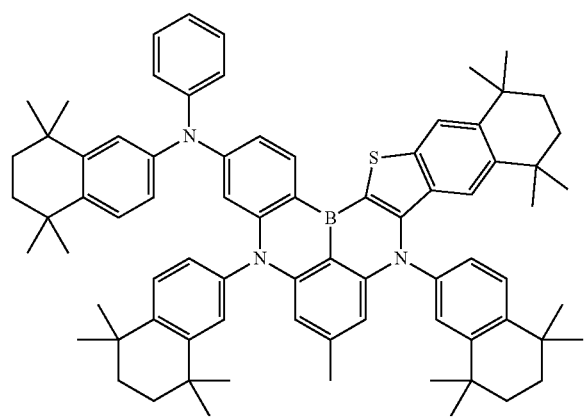
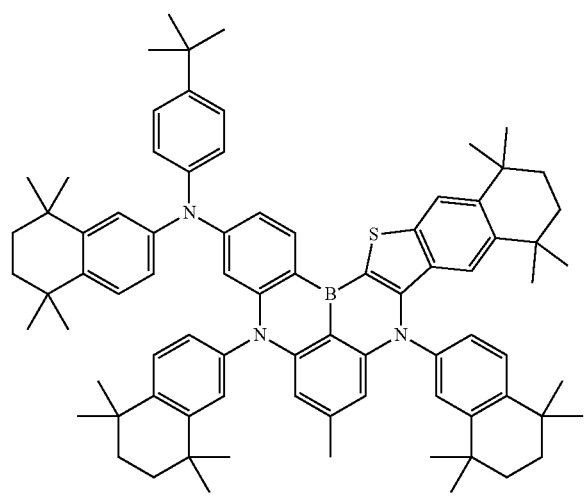
2330
-continued
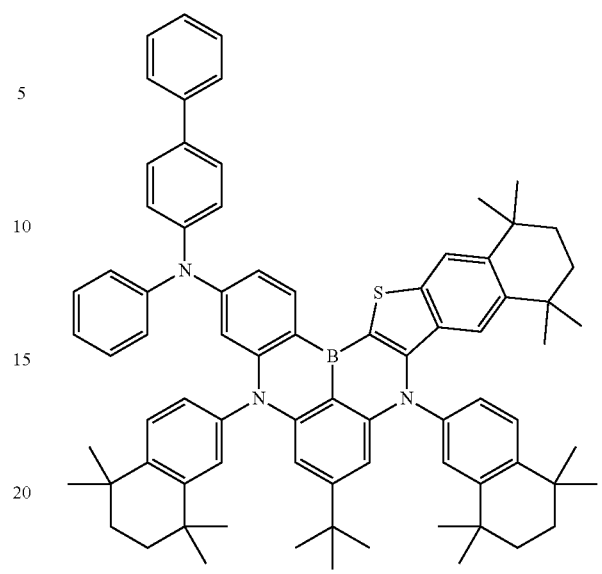
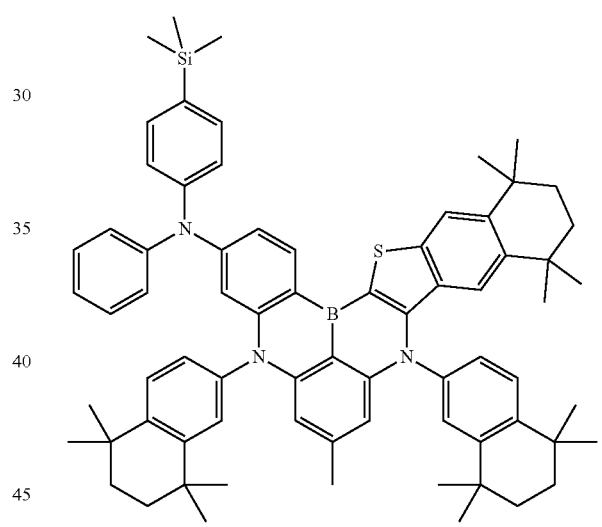
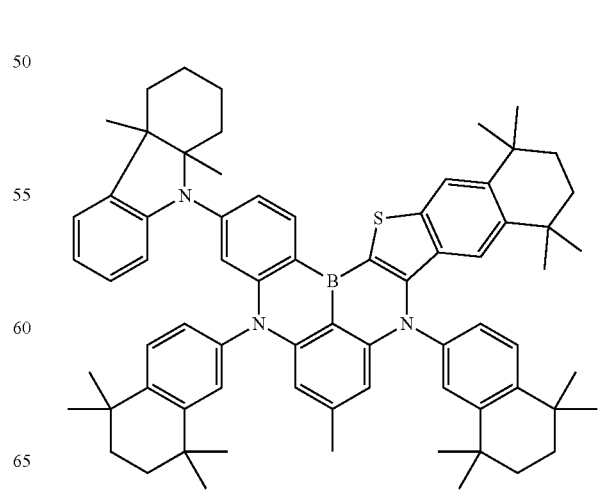

2331
-continued
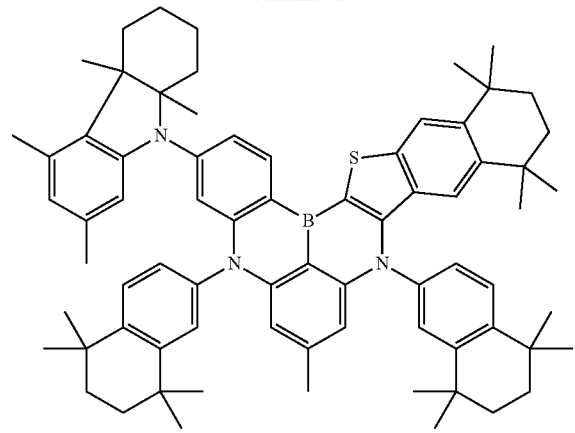
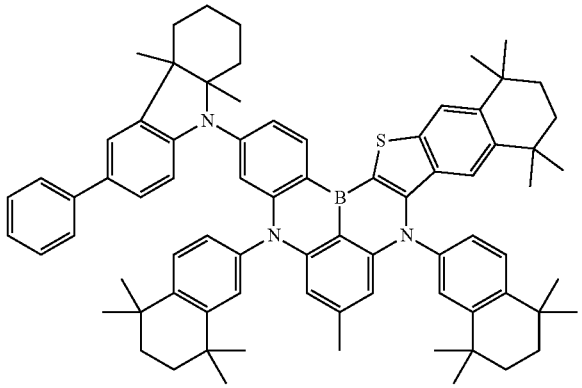
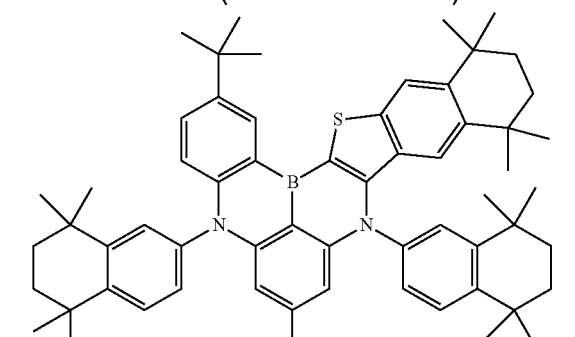
2332
-continued
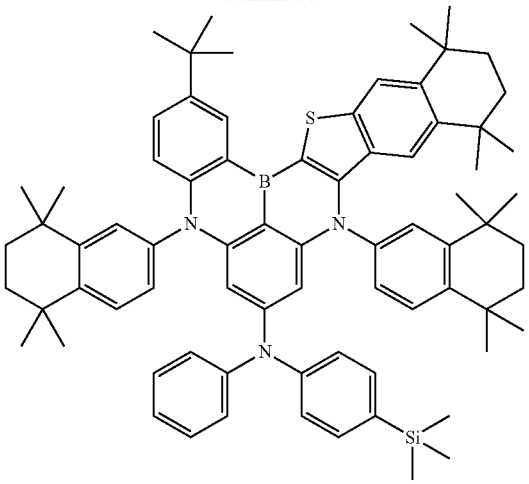
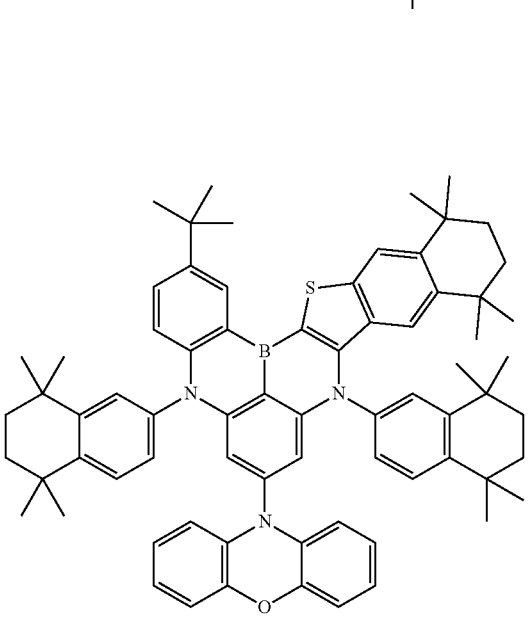
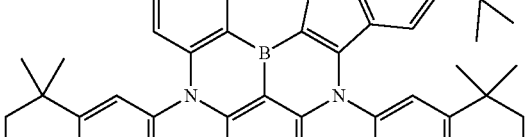
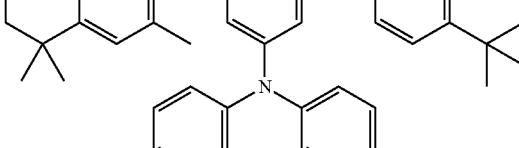

2333
-continued
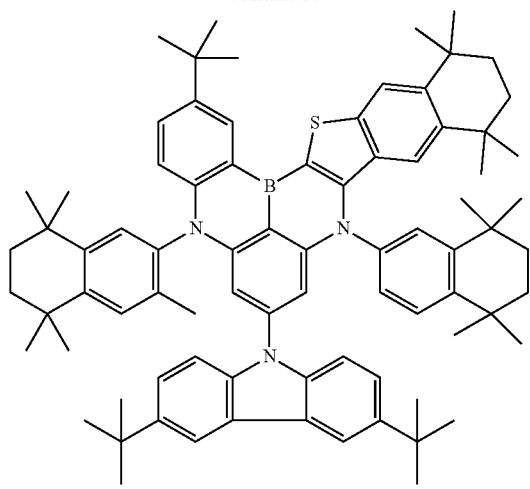
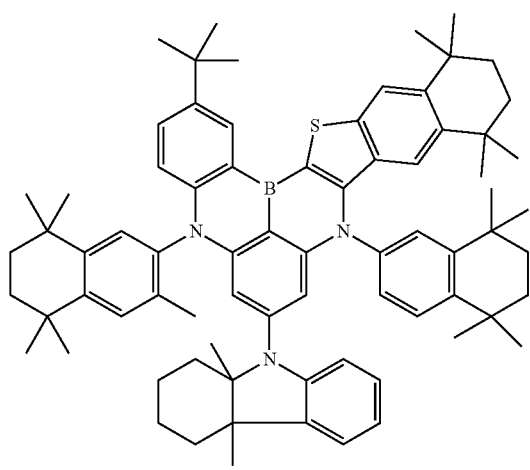
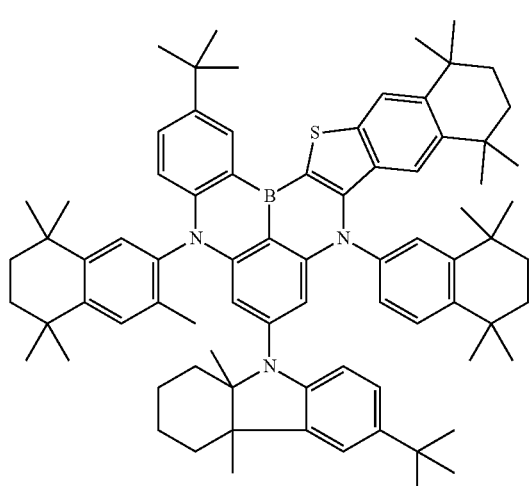
2334
-continued
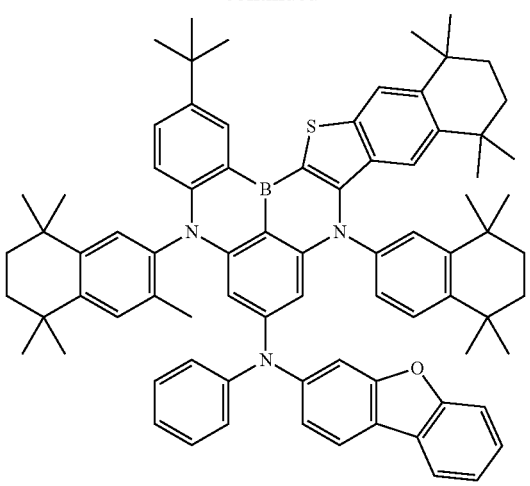
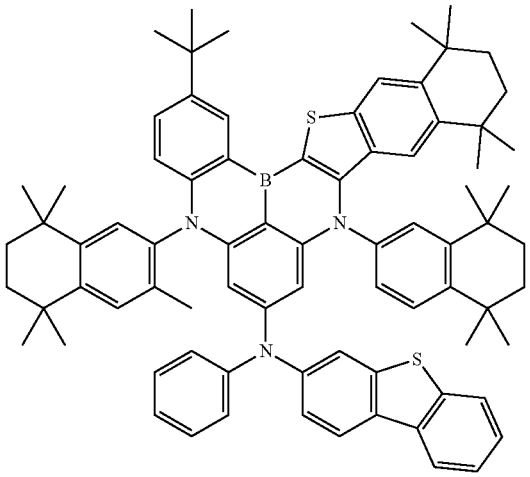
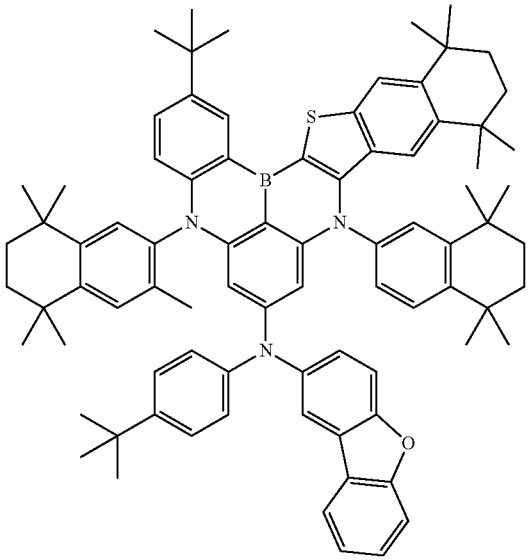

2335
-continued
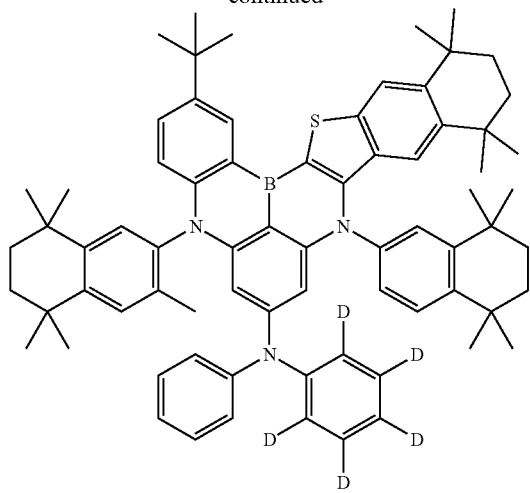
2336
-continued
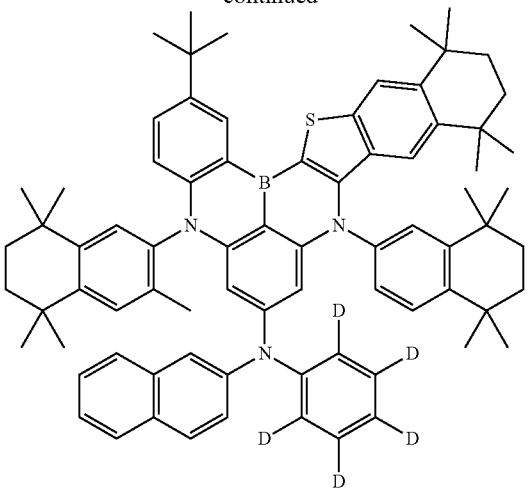
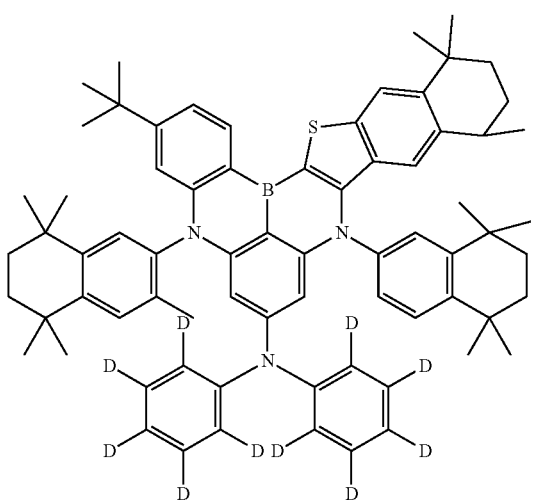
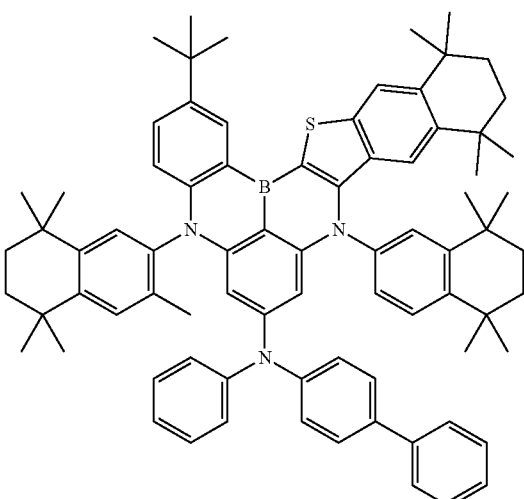
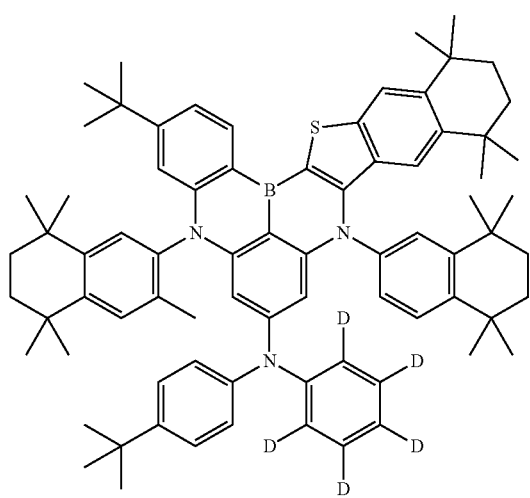
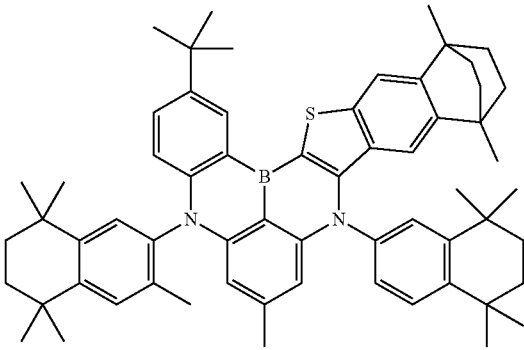

2337
-continued
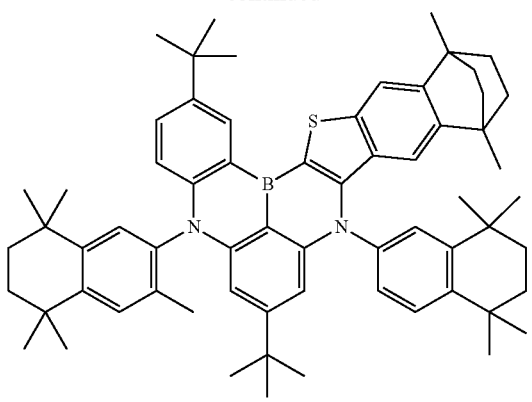
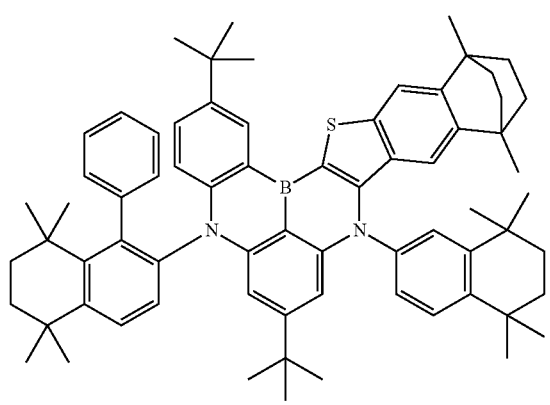
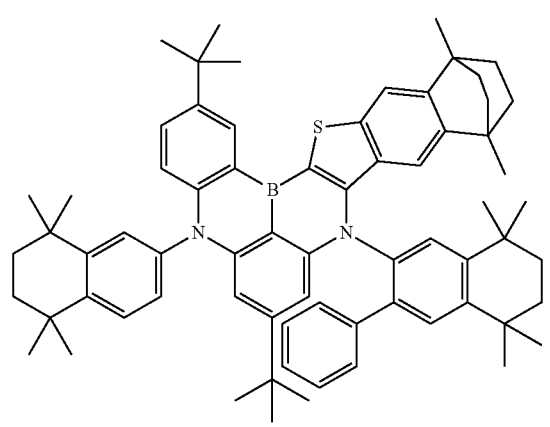
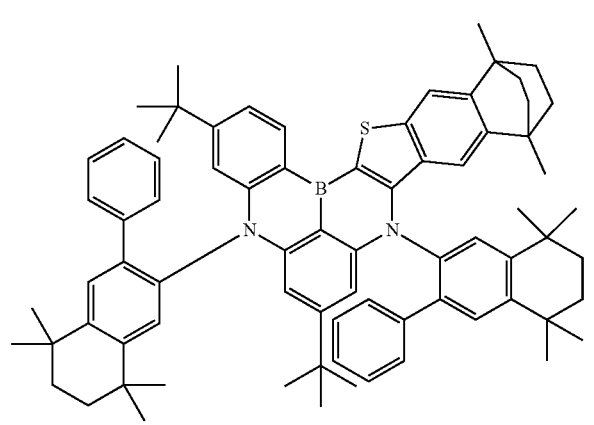
2338
-continued
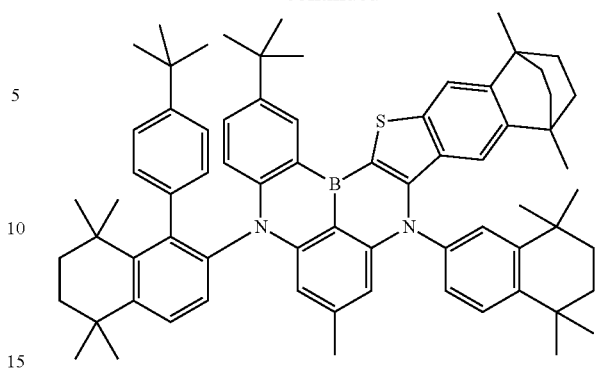
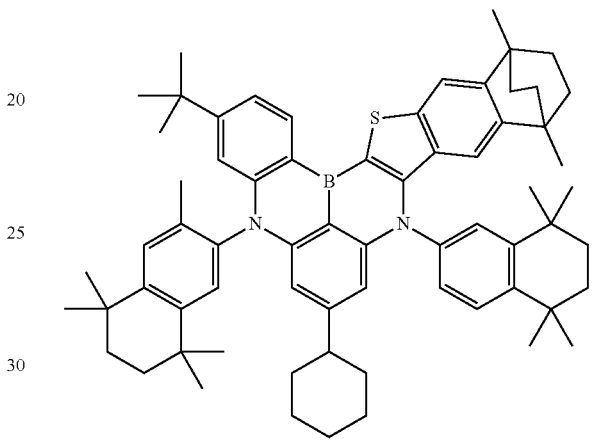
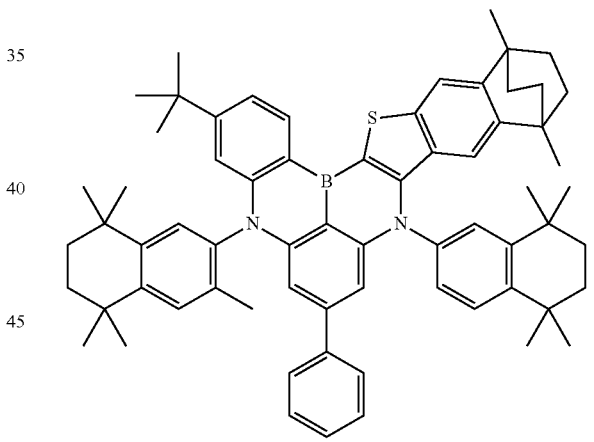
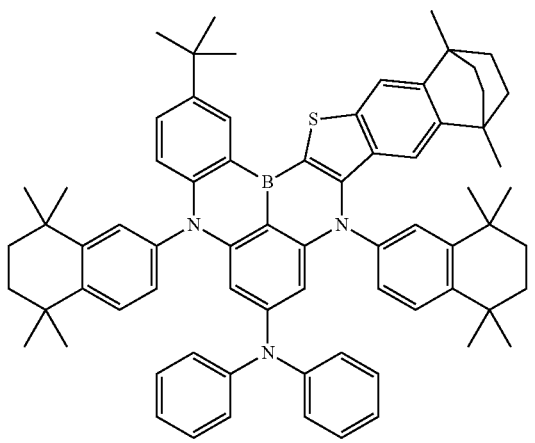

2339
-continued
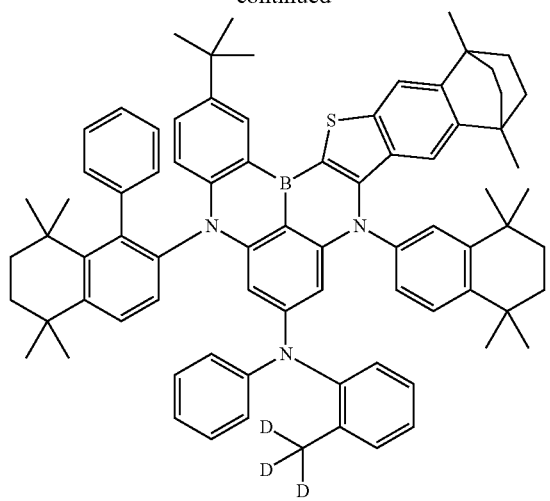
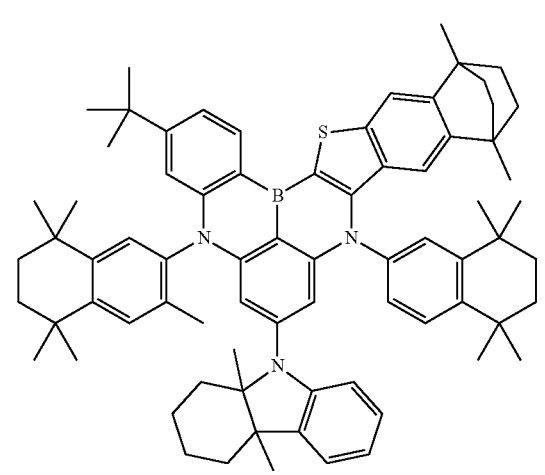
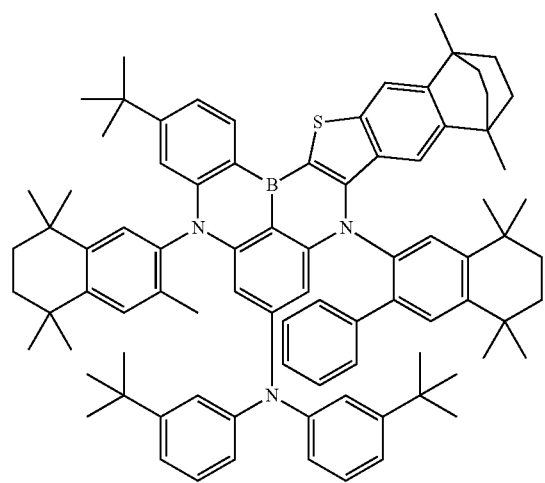
2340
-continued
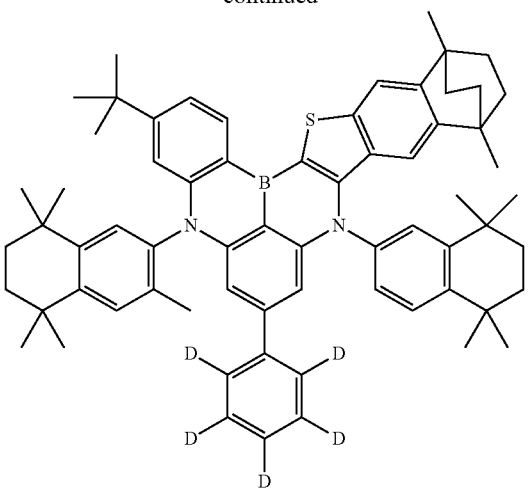
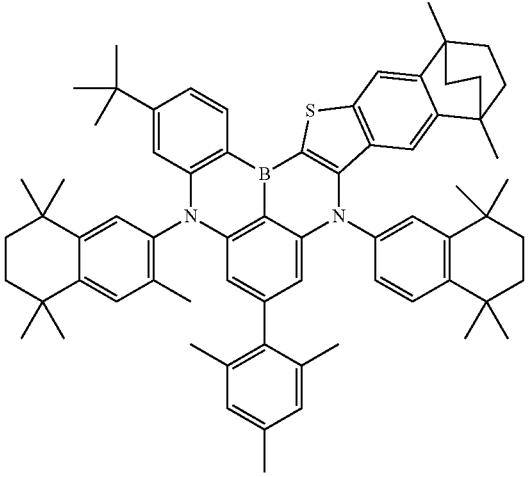
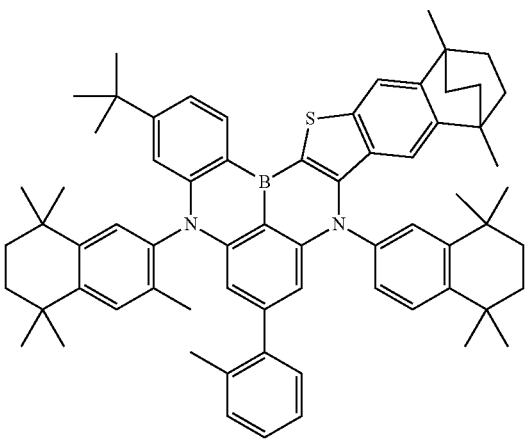

2341
-continued
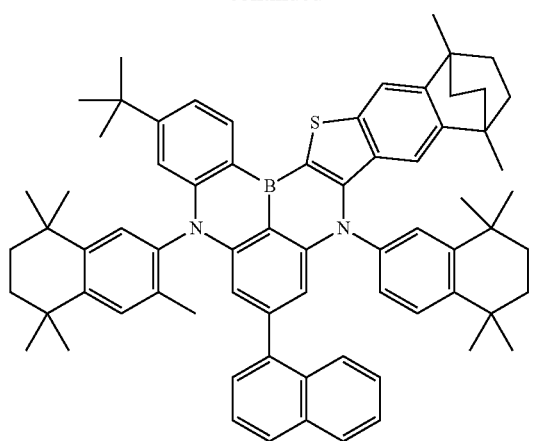
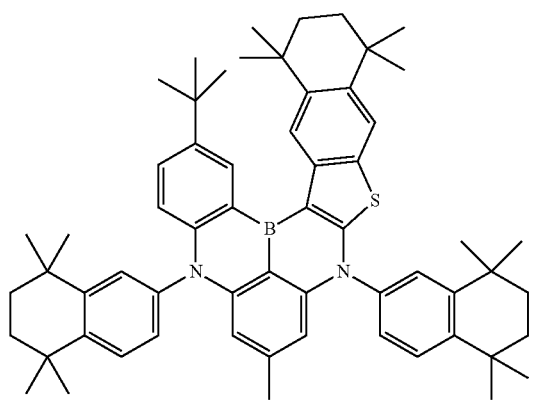
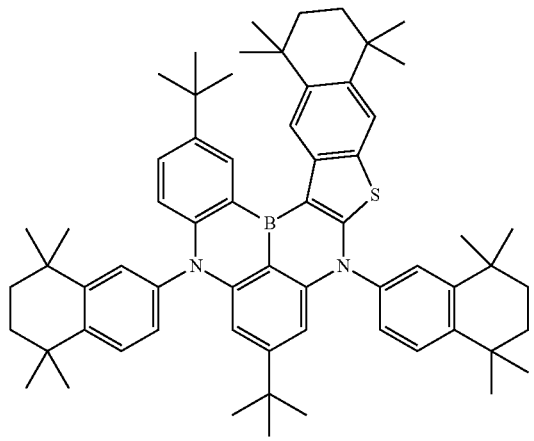
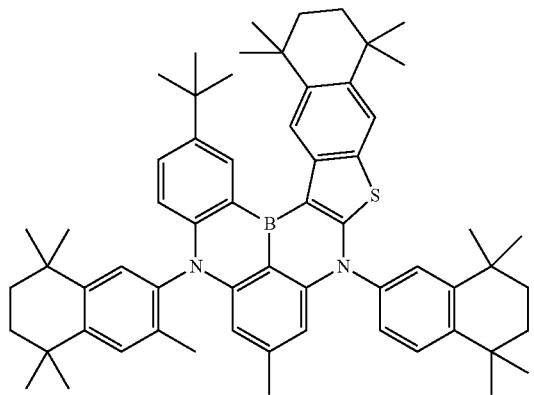
2342
-continued
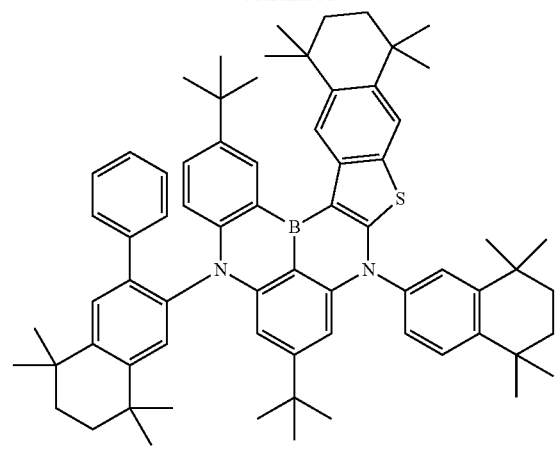
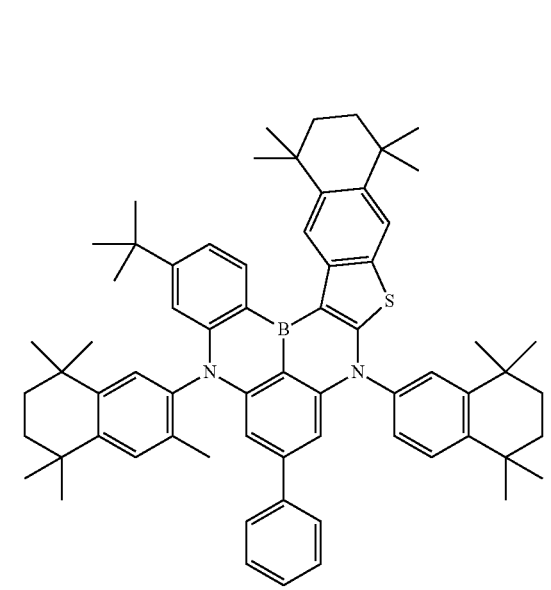
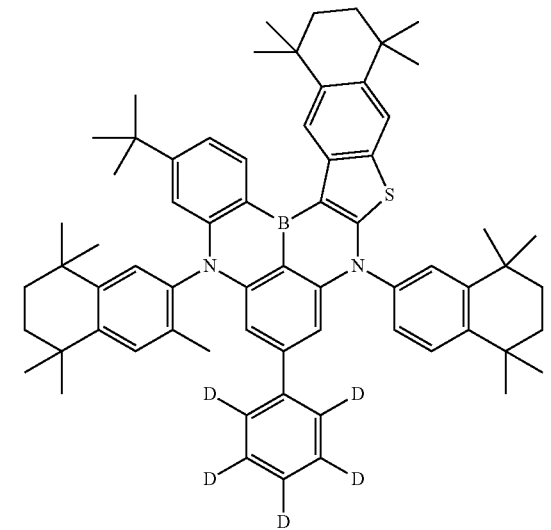

2343
-continued
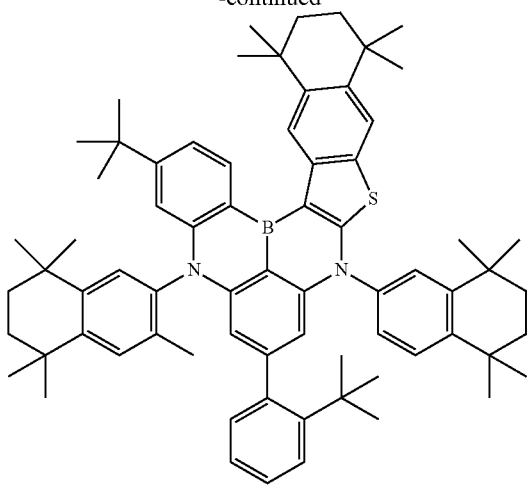
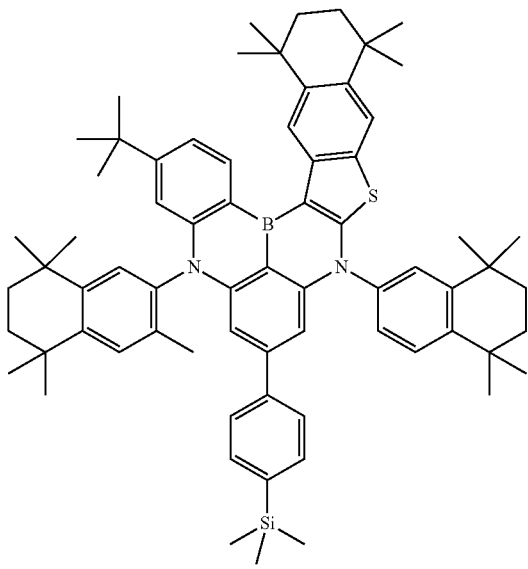
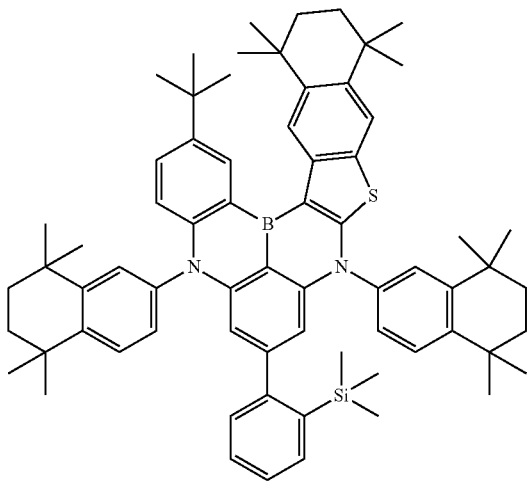
2344
-continued
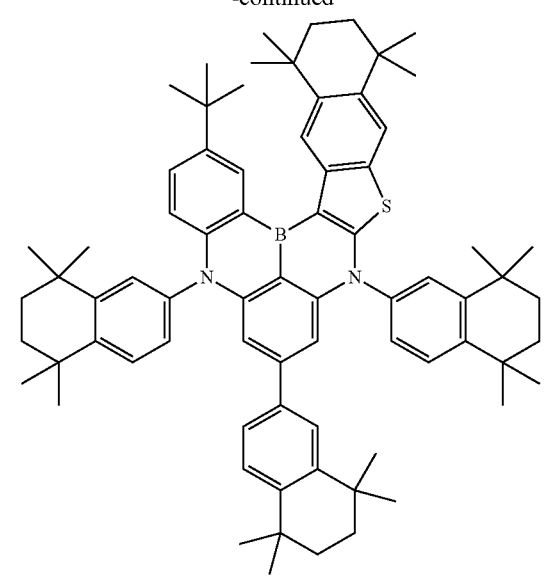
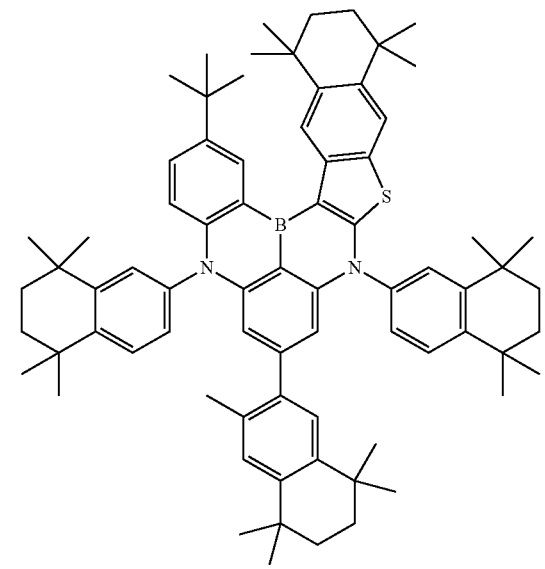
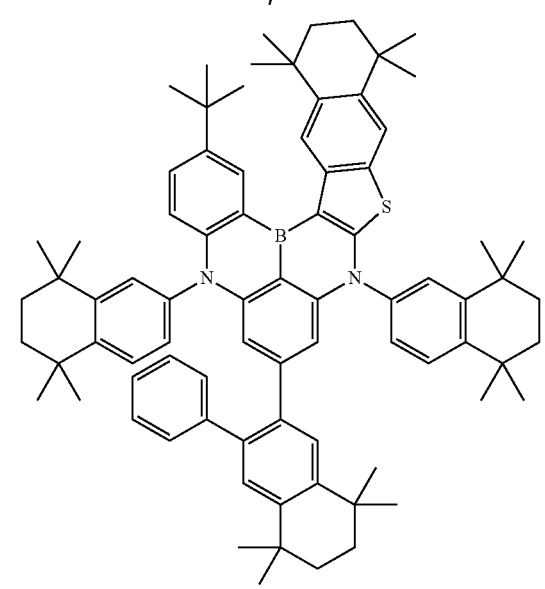

2345
-continued
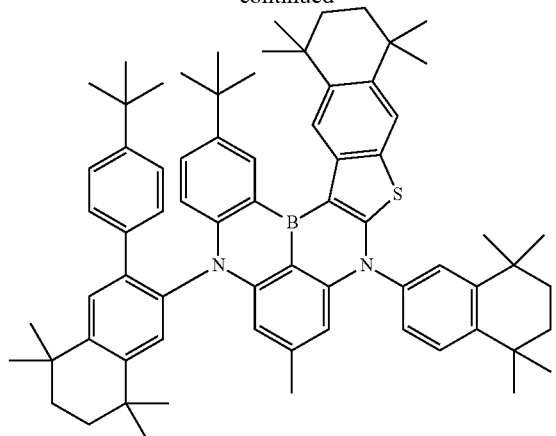
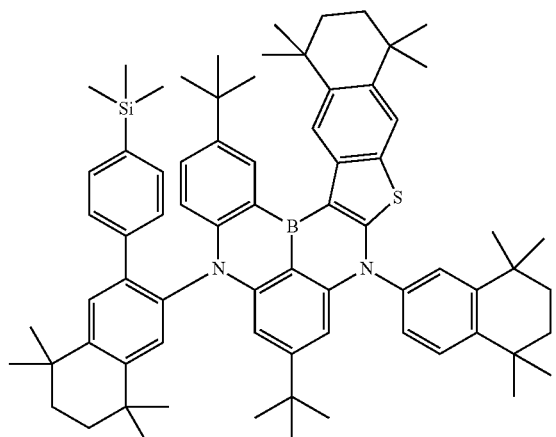
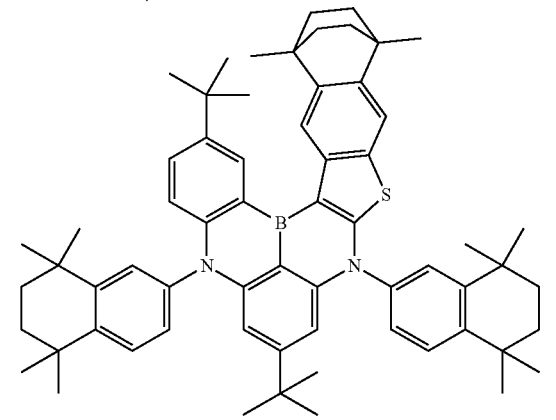
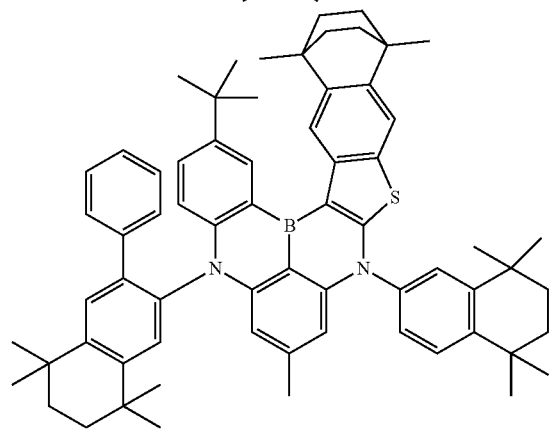
2346
-continued
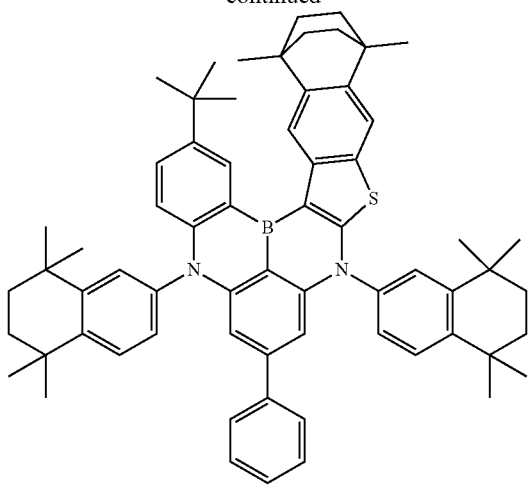
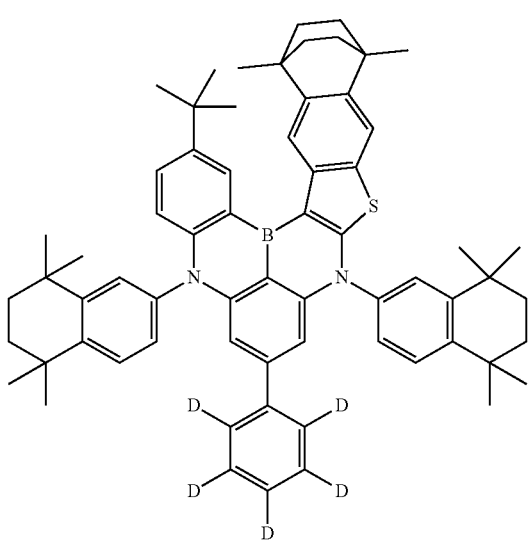
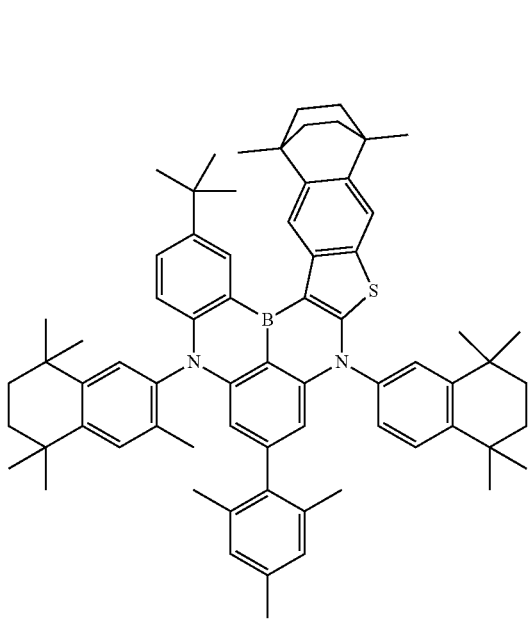

2347
-continued
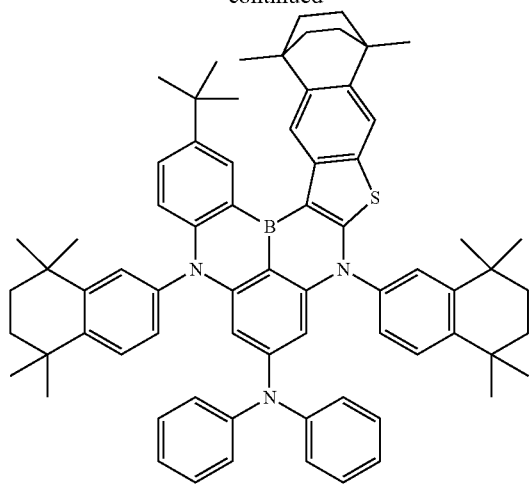
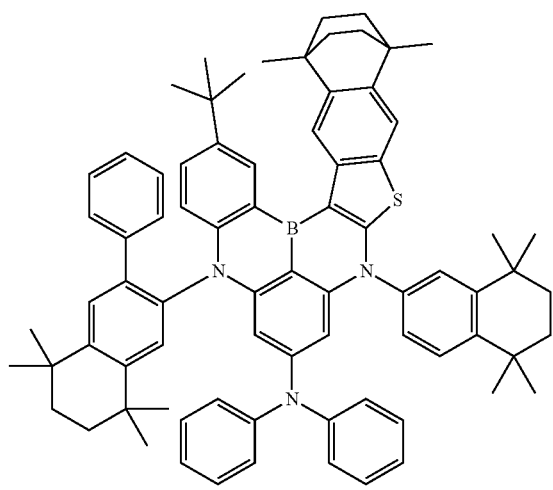
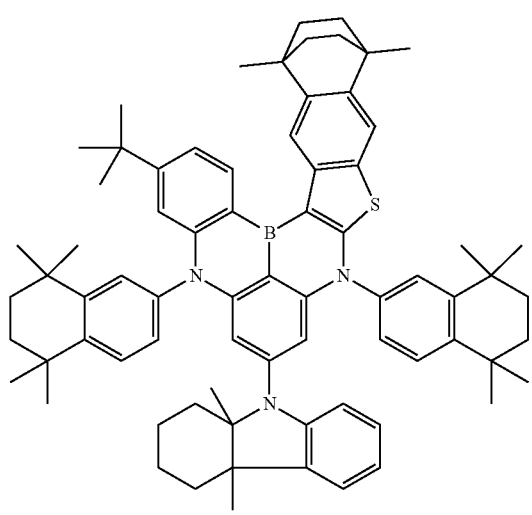
2348
-continued
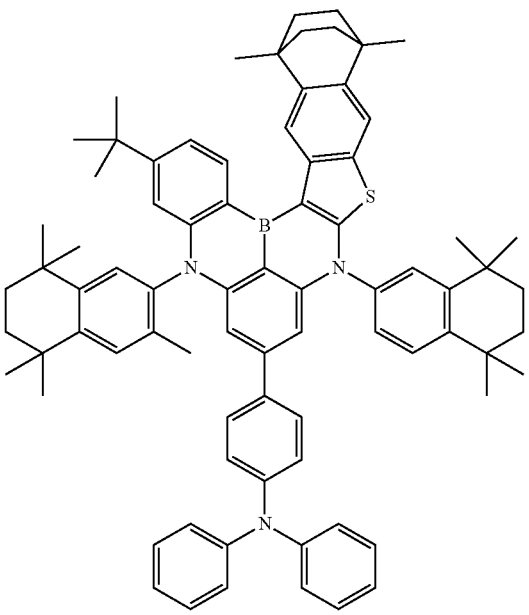
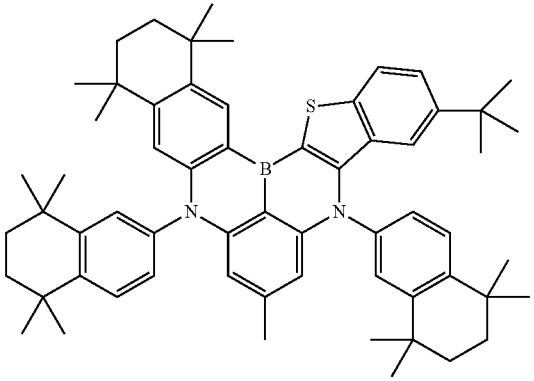
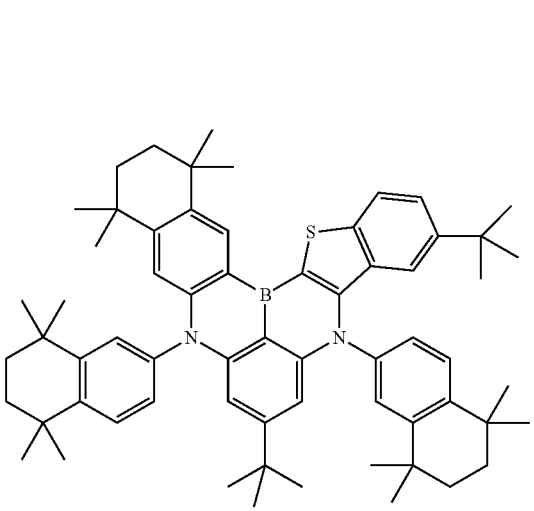

2349
-continued
2350
-continued
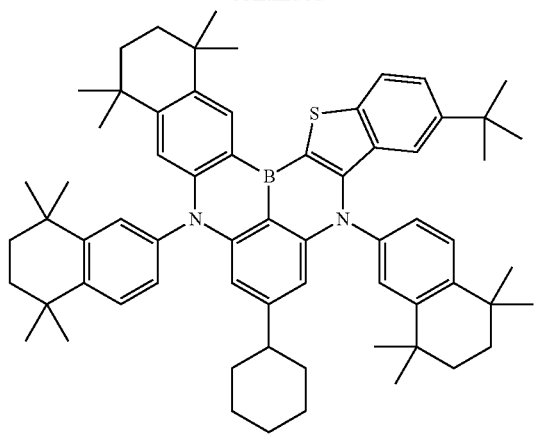
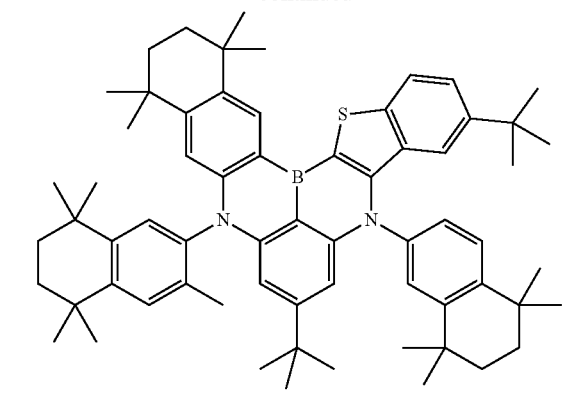
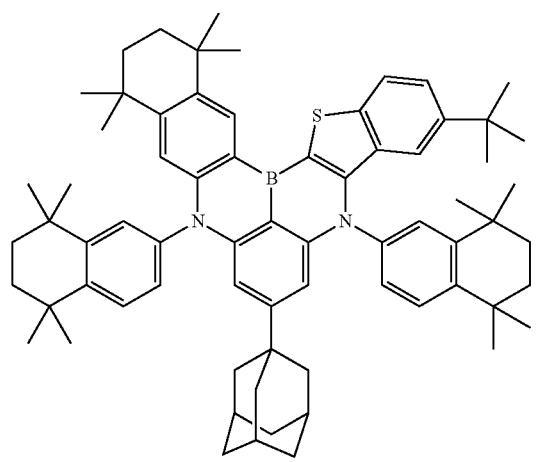
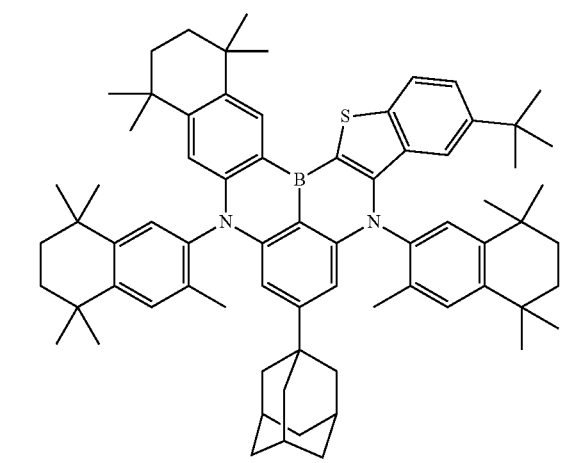
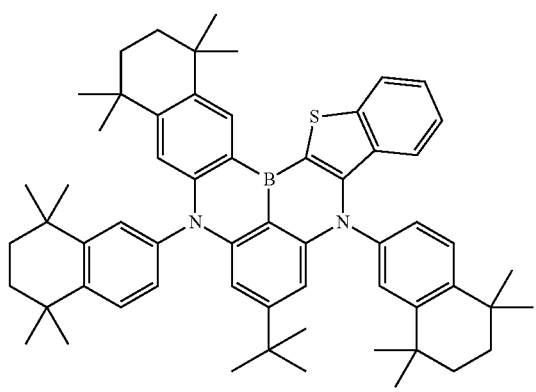
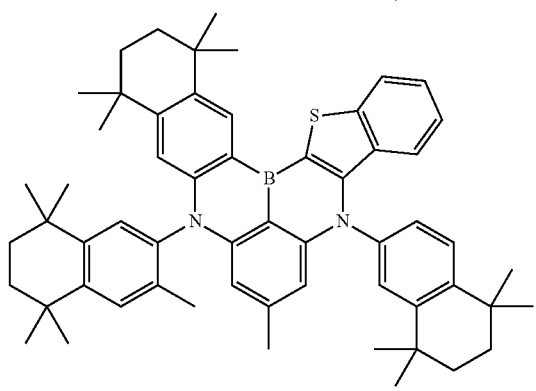
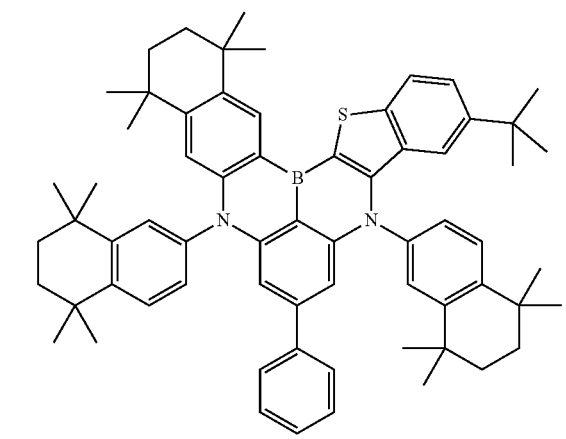

2351
-continued
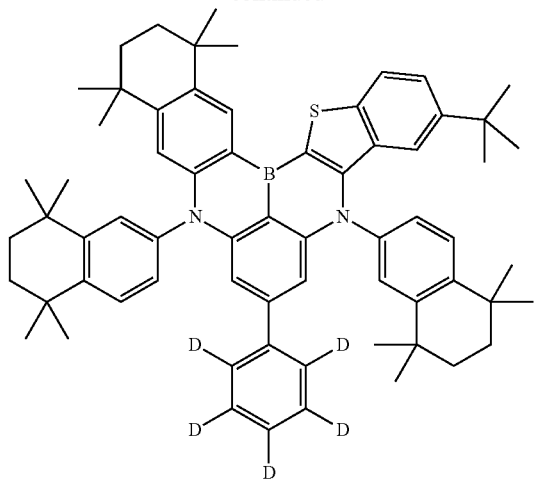
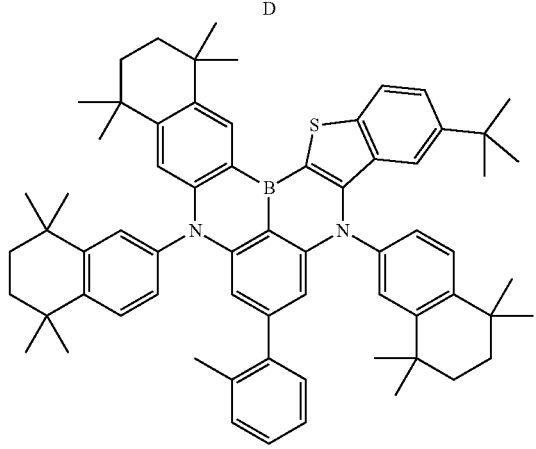
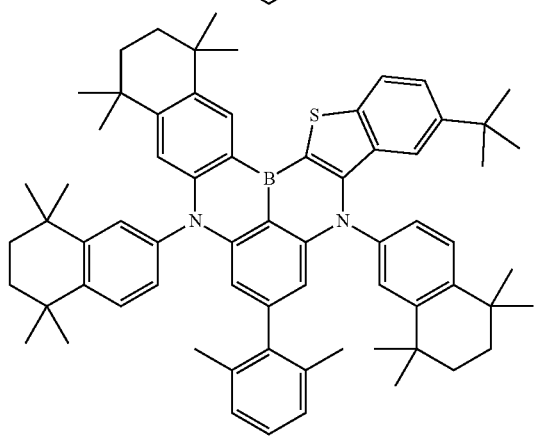
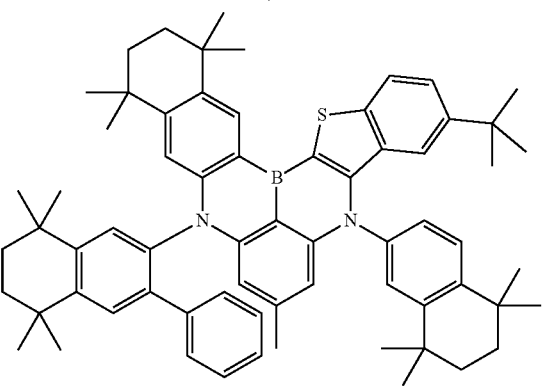
2352
-continued
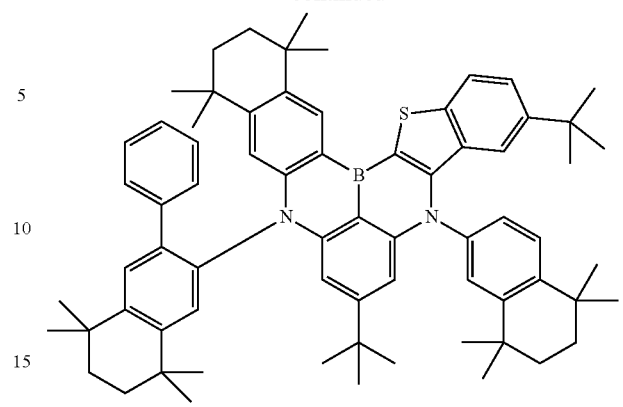
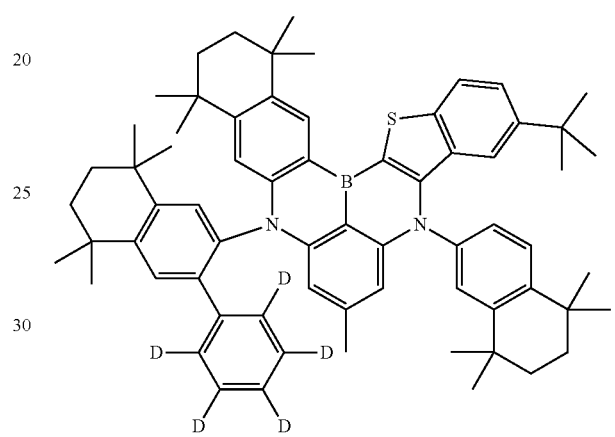
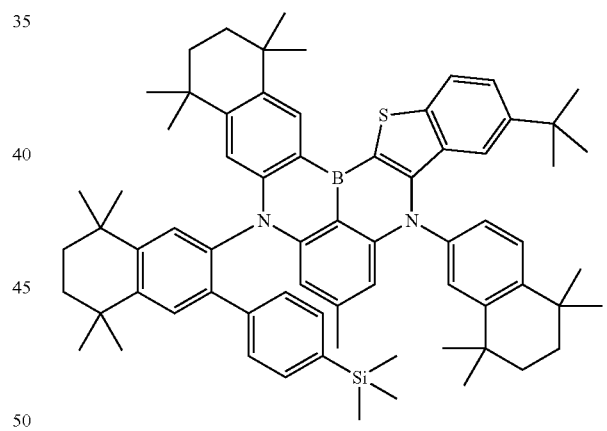
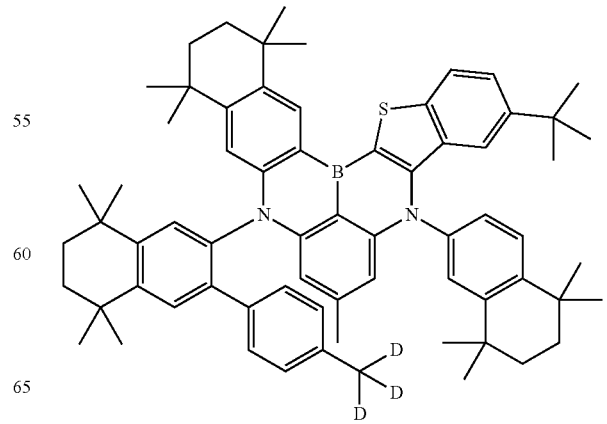

2353
-continued
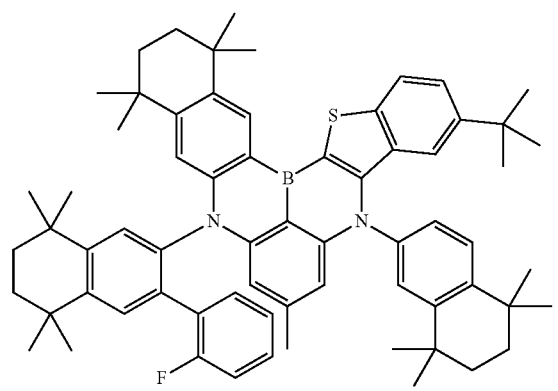
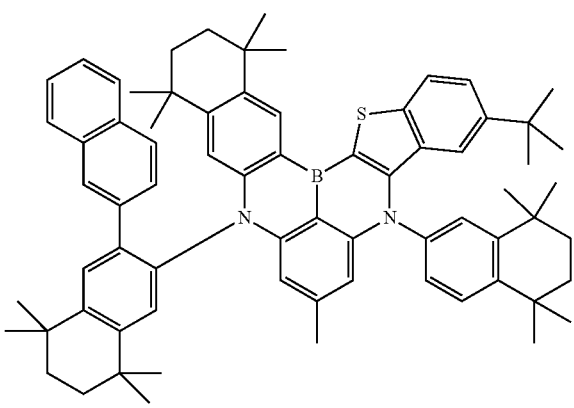
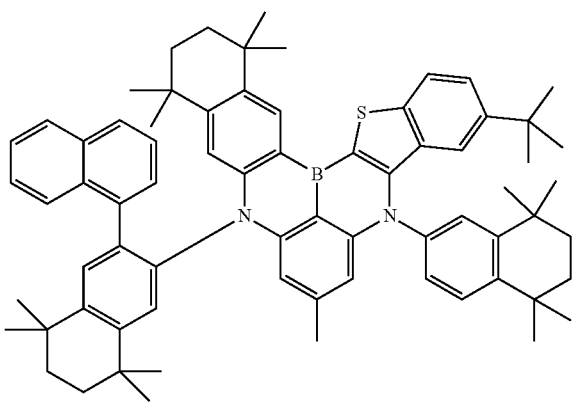
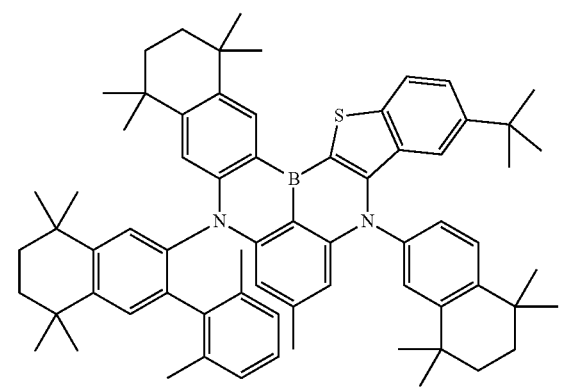
2354
-continued
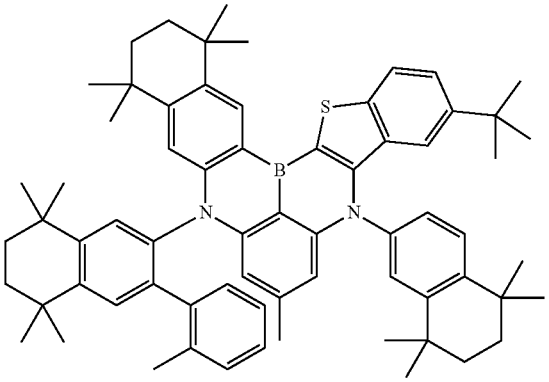
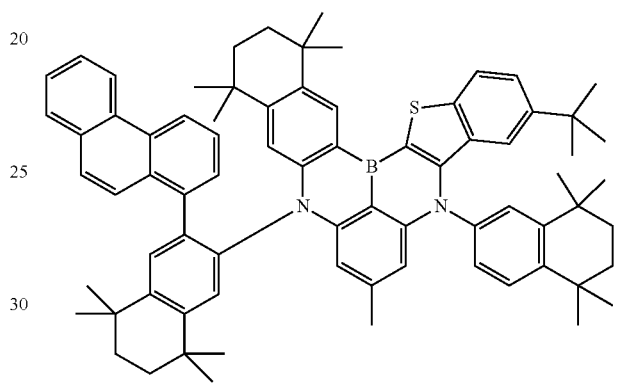
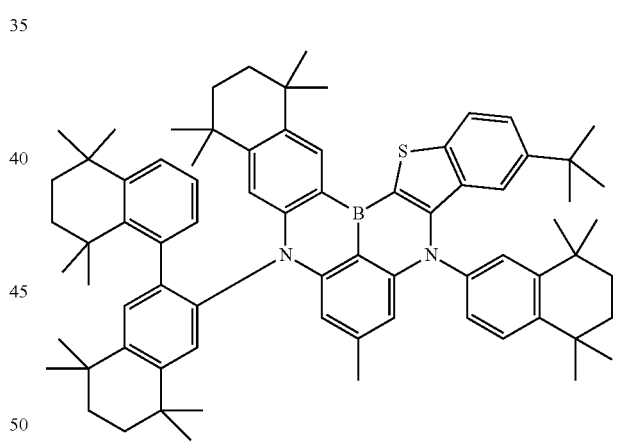
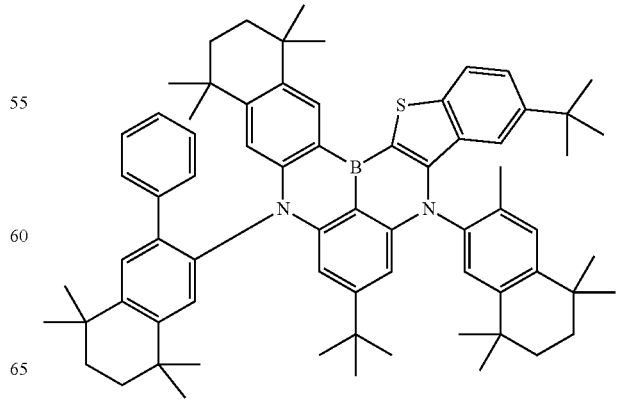

2355
-continued

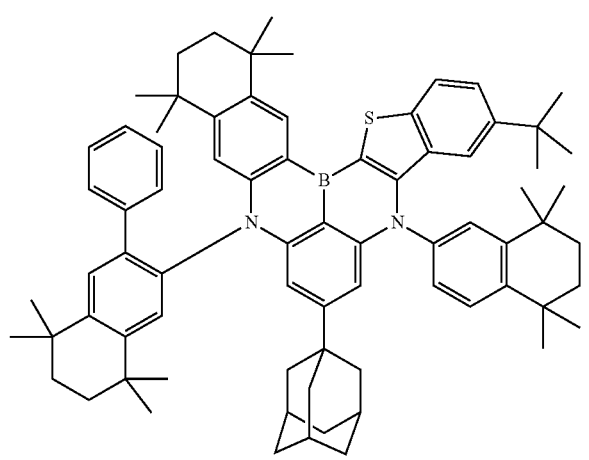
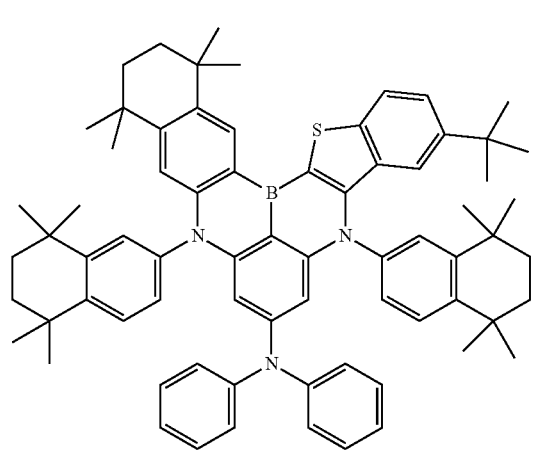
2356
-continued
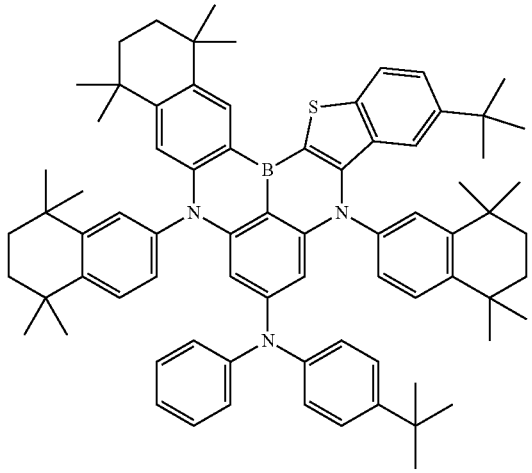
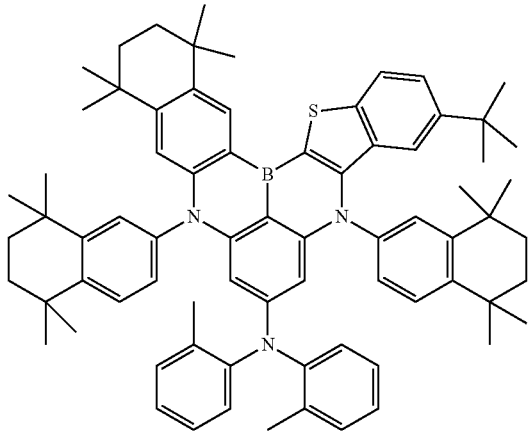
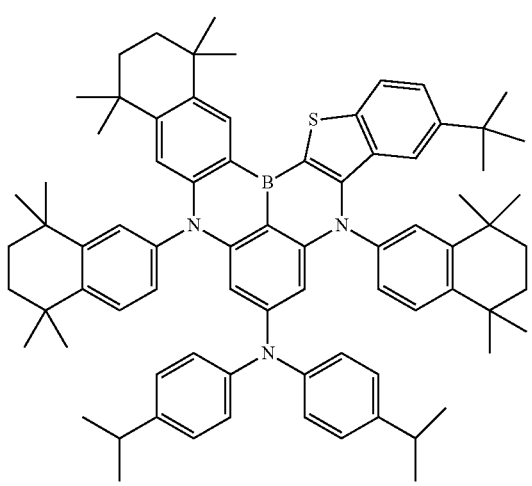

2357
-continued
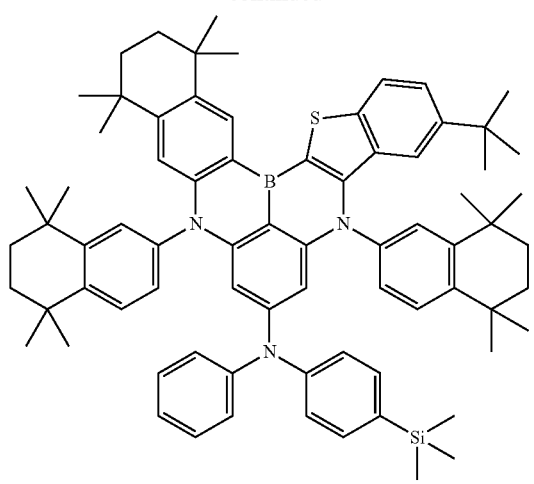
2358
-continued
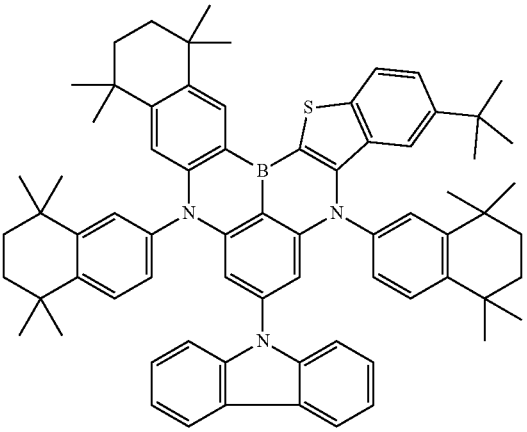
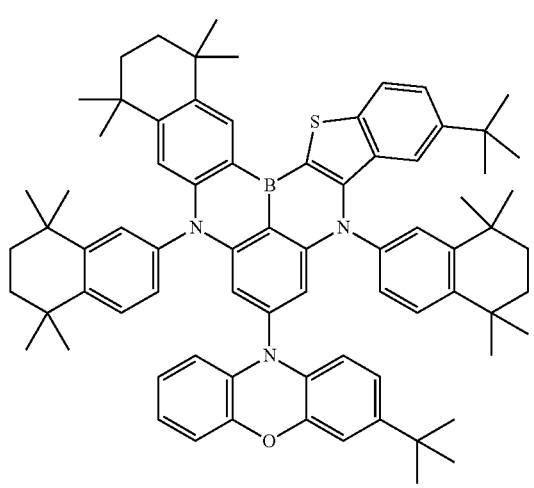
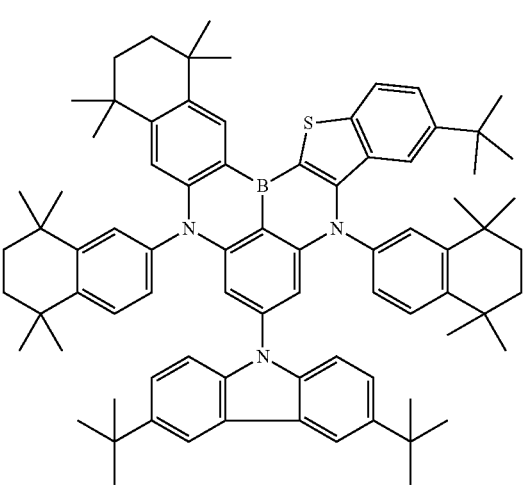
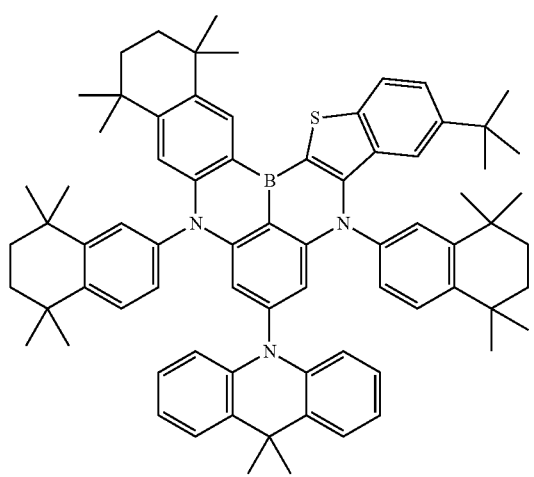
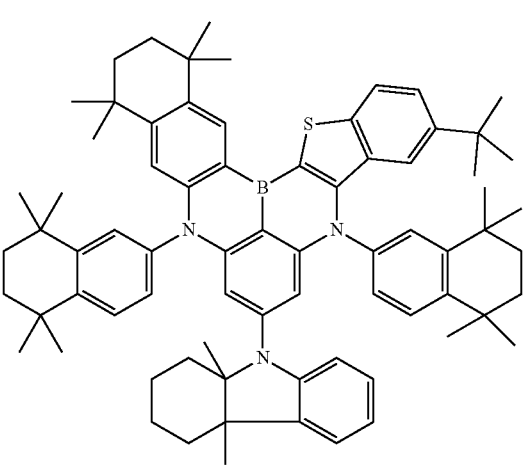

2359
-continued
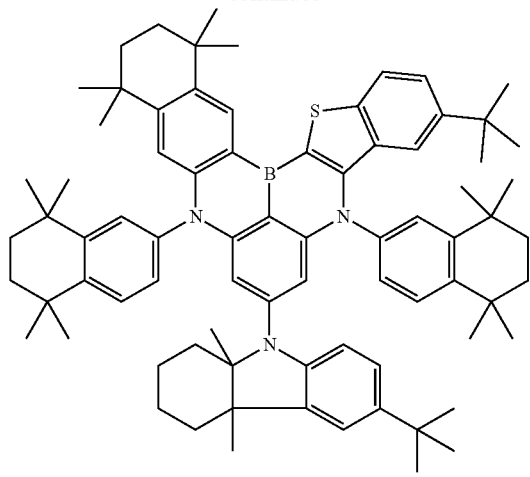
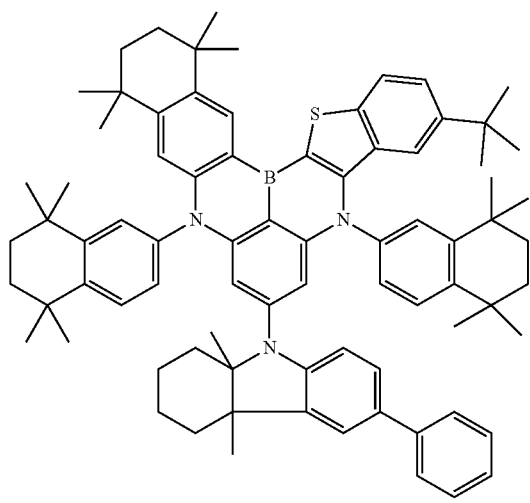
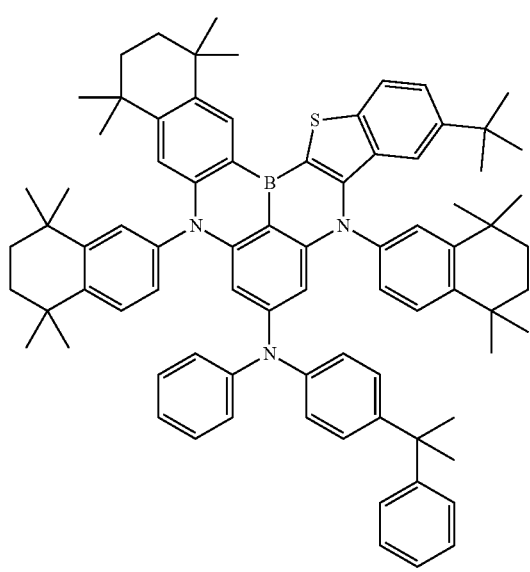
2360
-continued
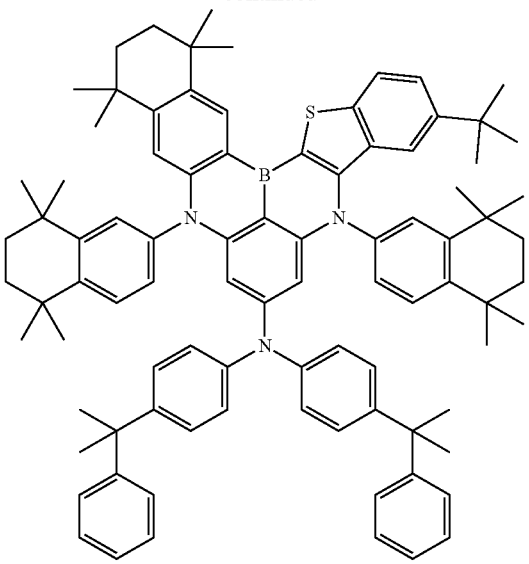
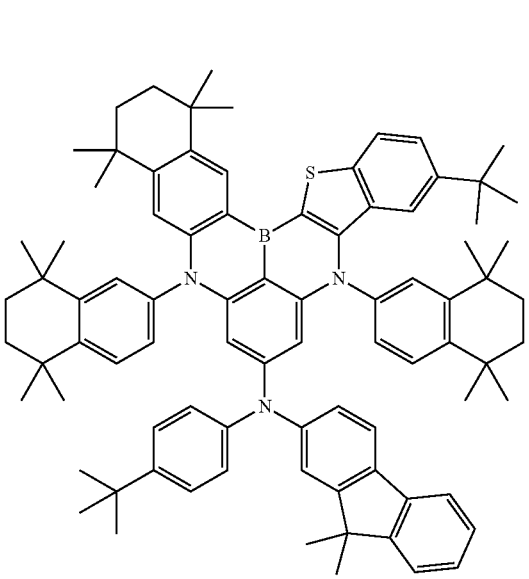
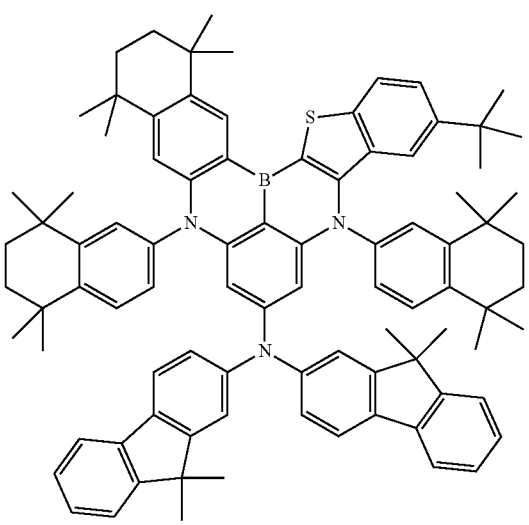

2361
-continued
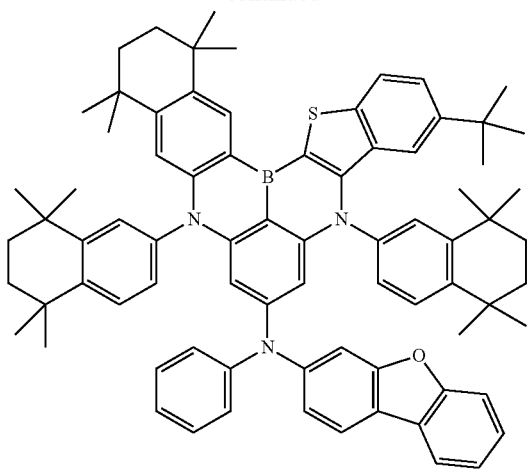
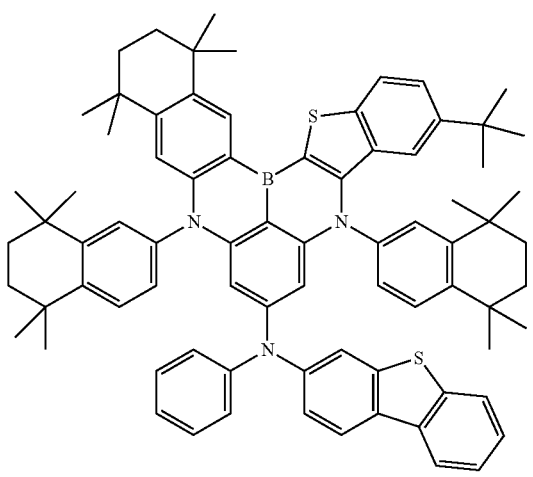
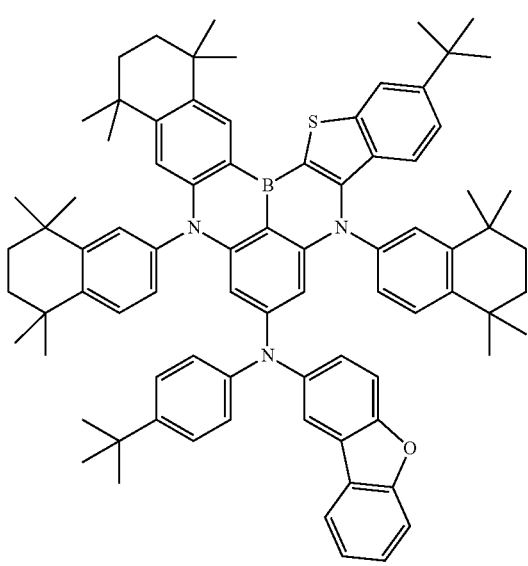
2362
-continued
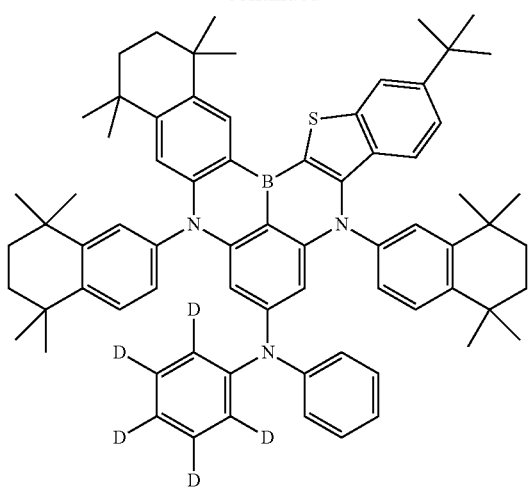
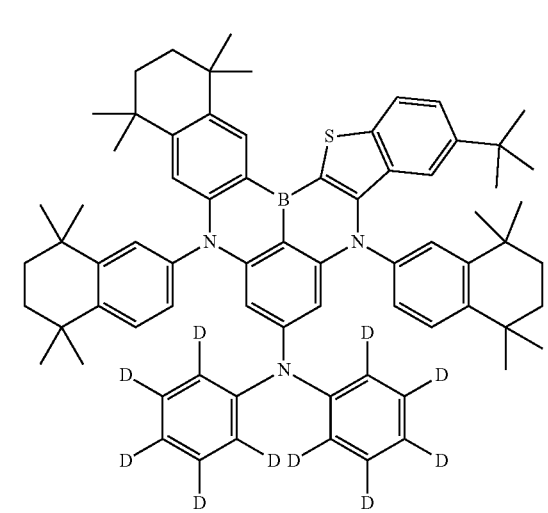
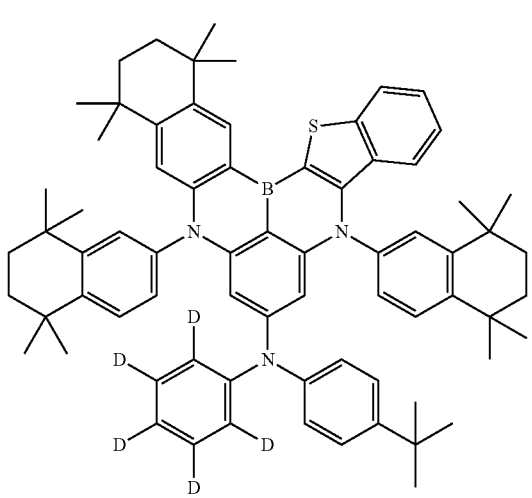

2363
-continued
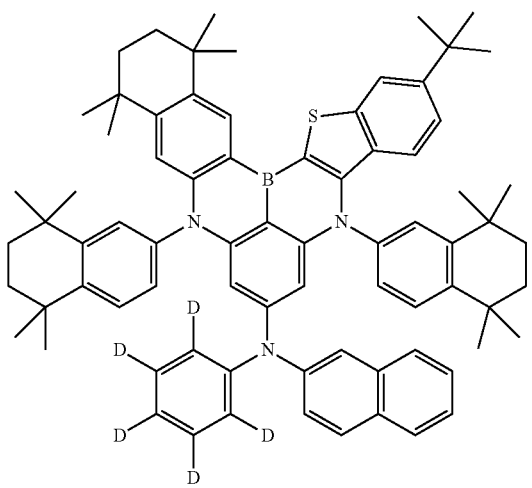
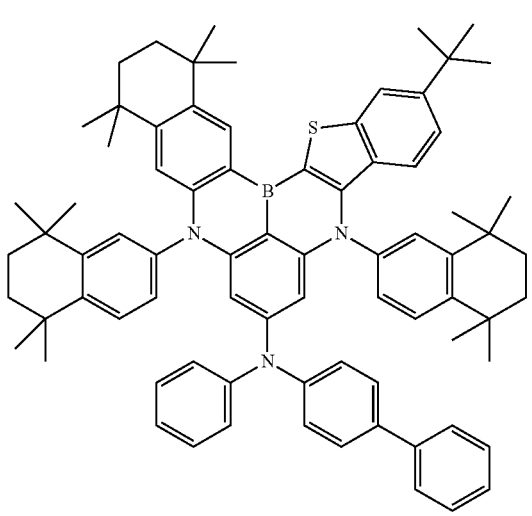
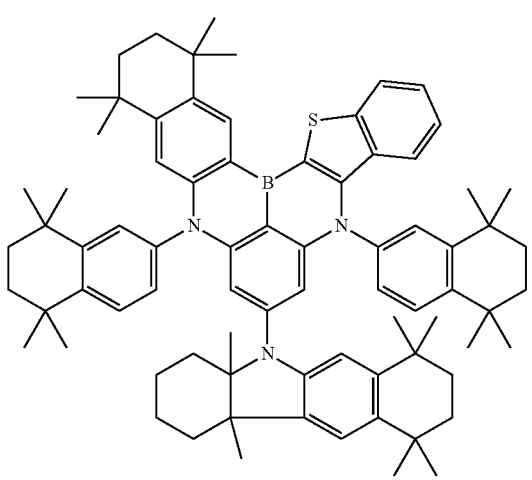
2364
-continued
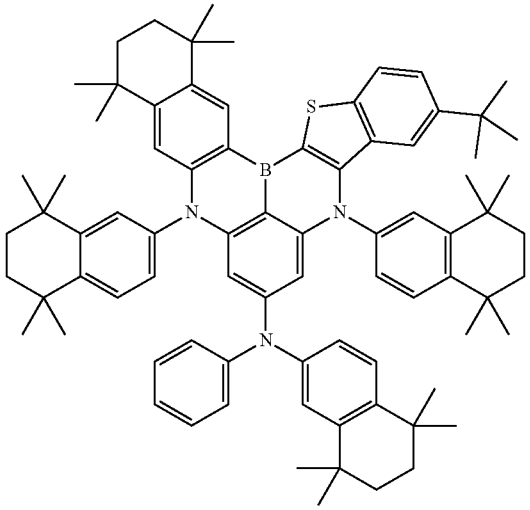
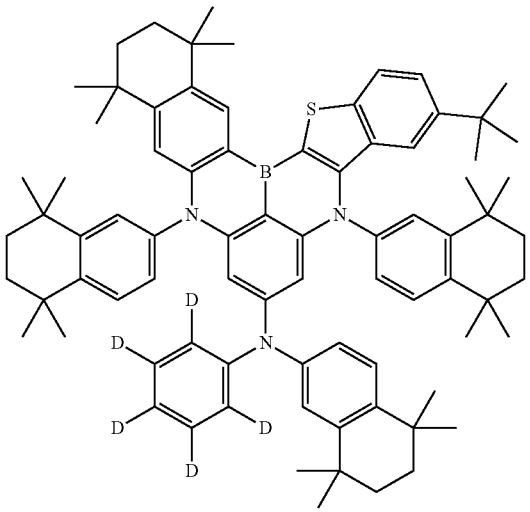
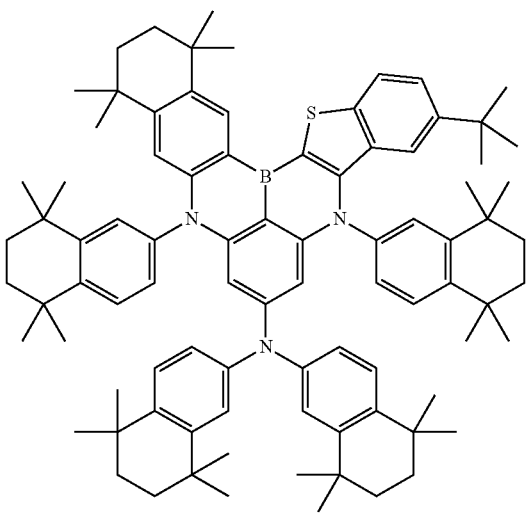

2365
-continued
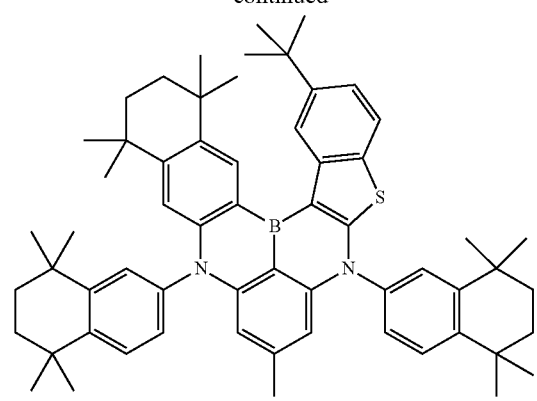
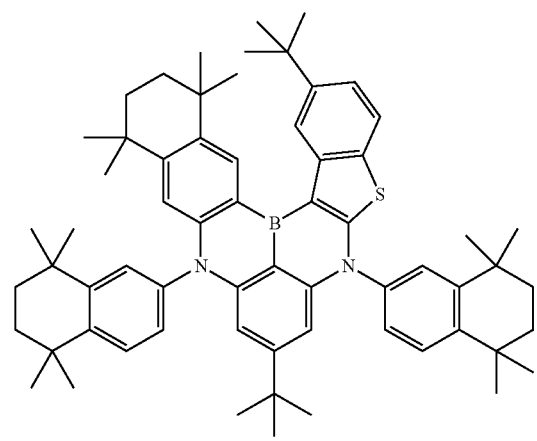
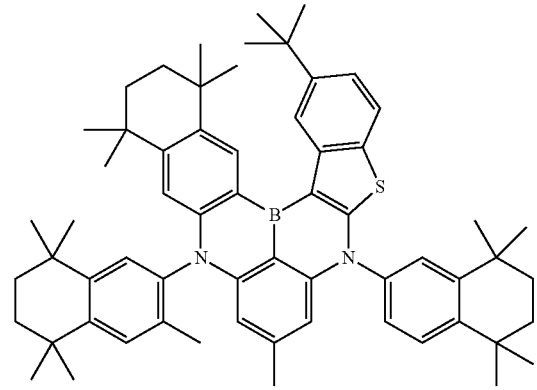
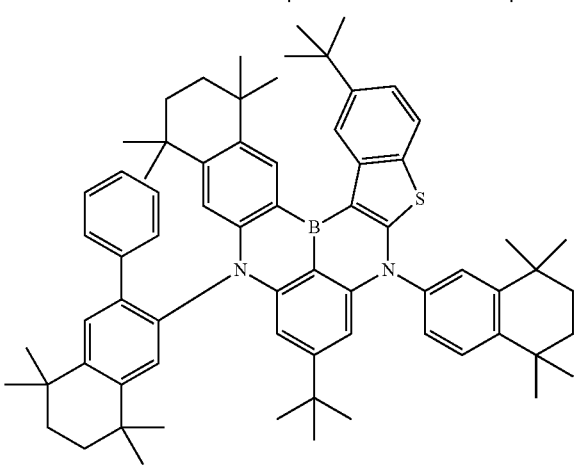
2366
-continued
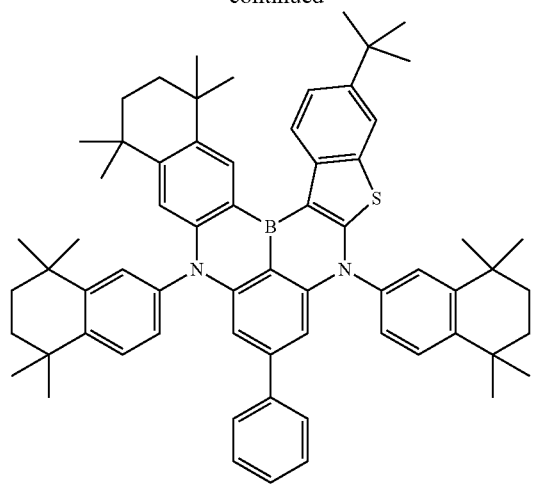
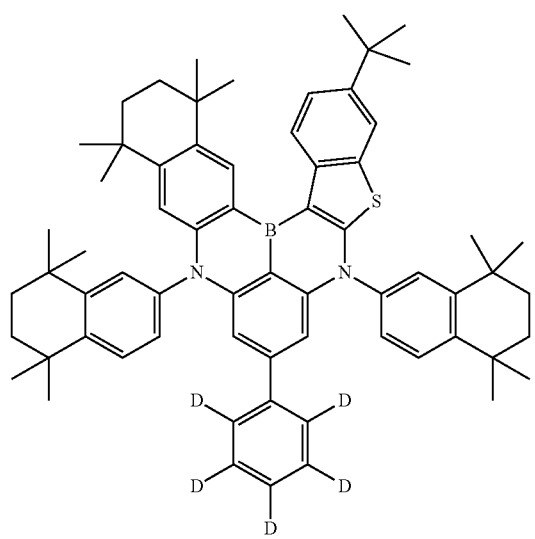
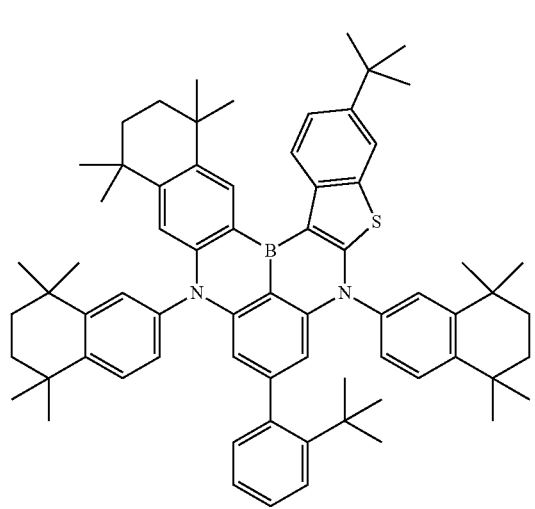

2367
-continued
2368
-continued
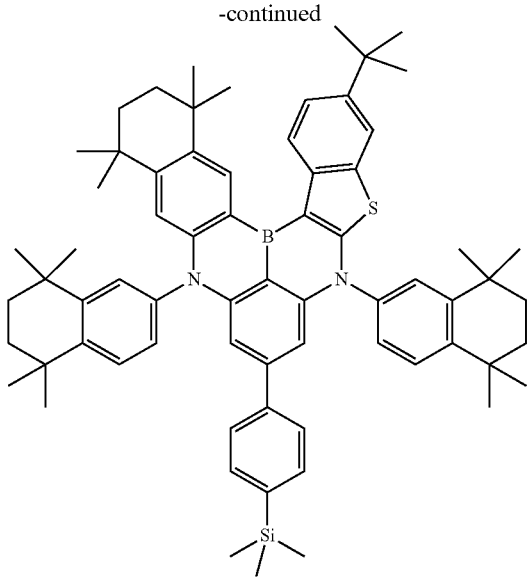
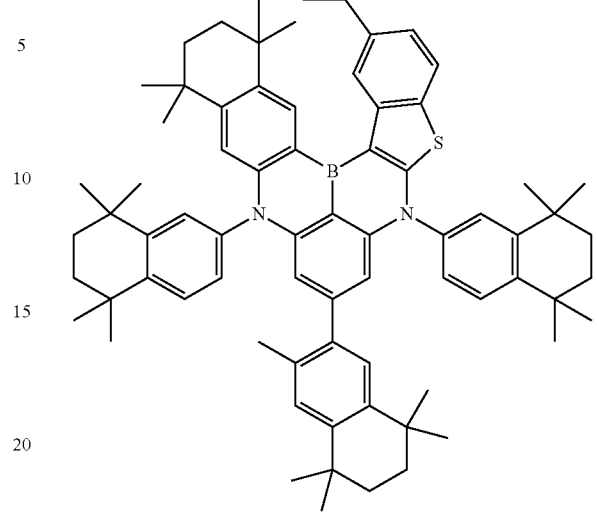
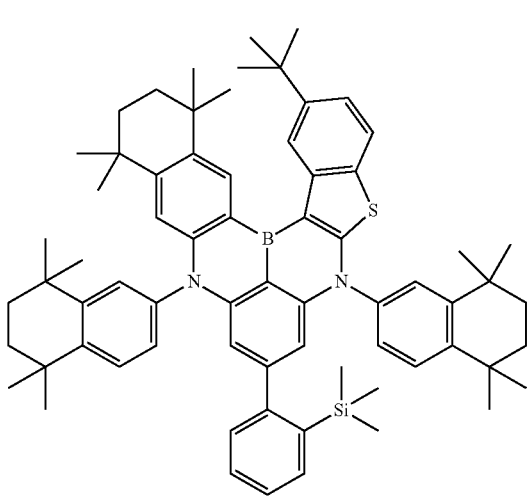
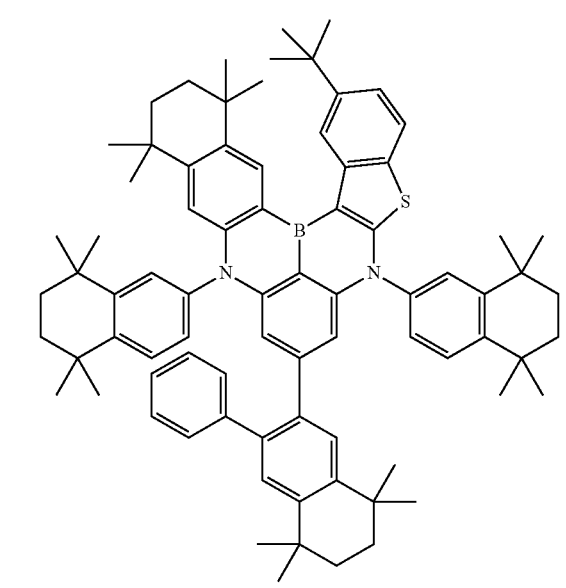
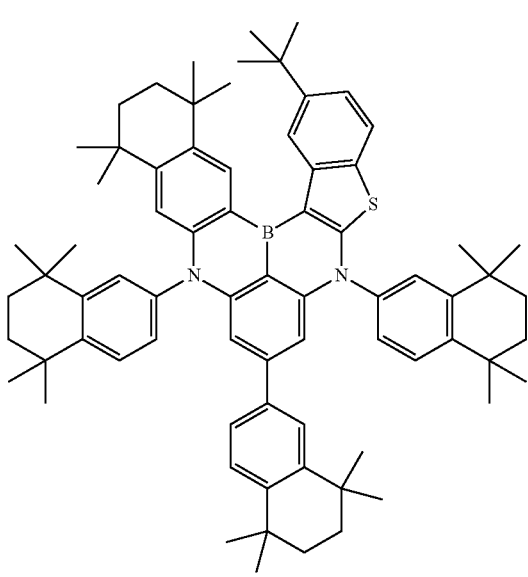
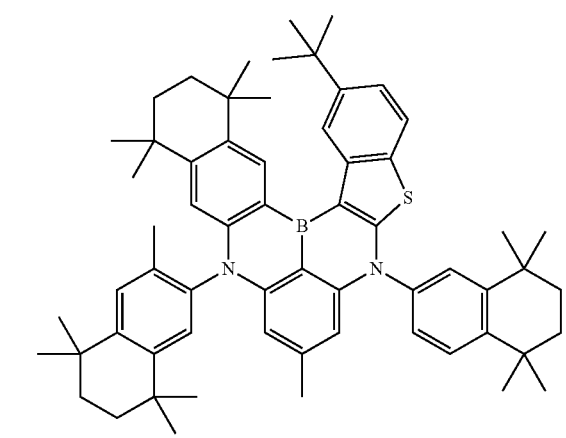

2369
-continued
2370
-continued
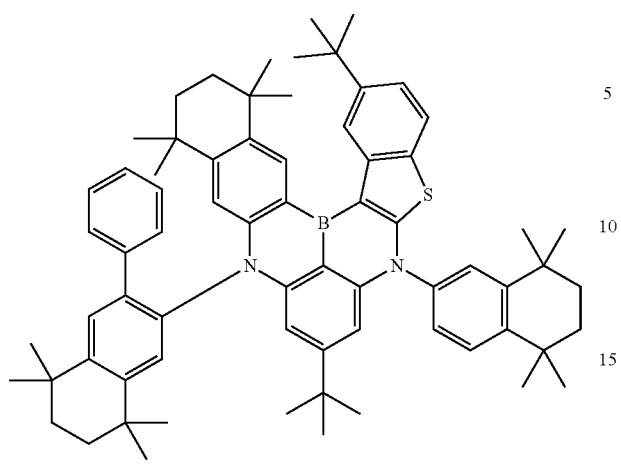
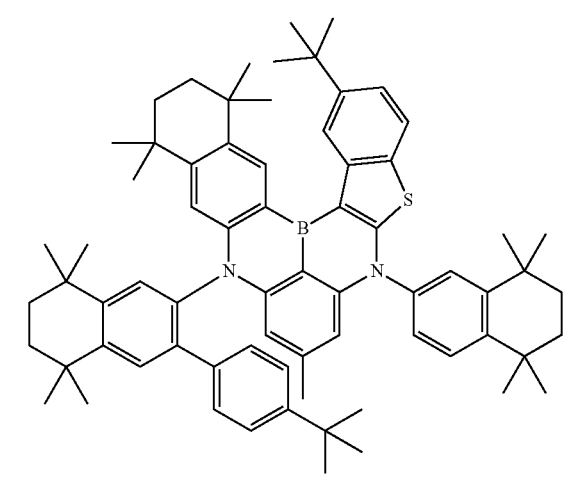
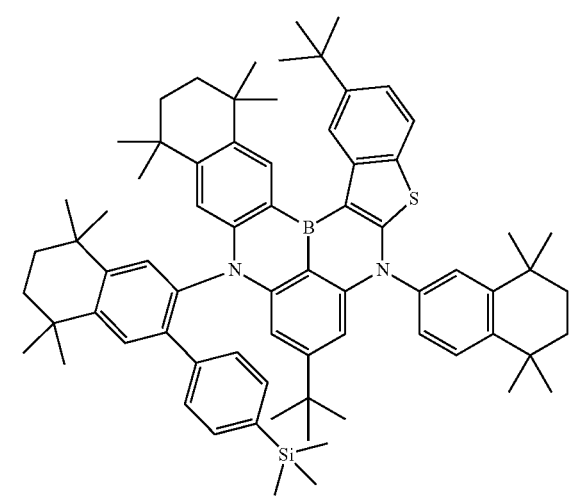

2371
-continued
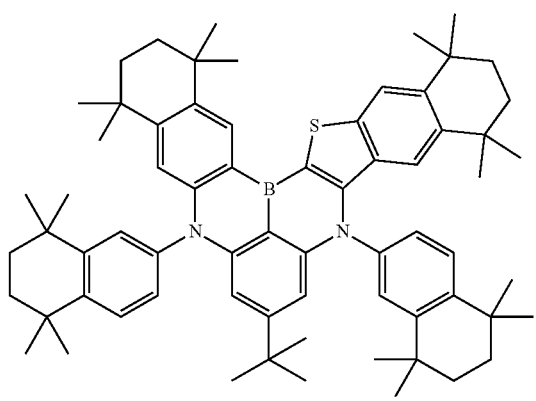
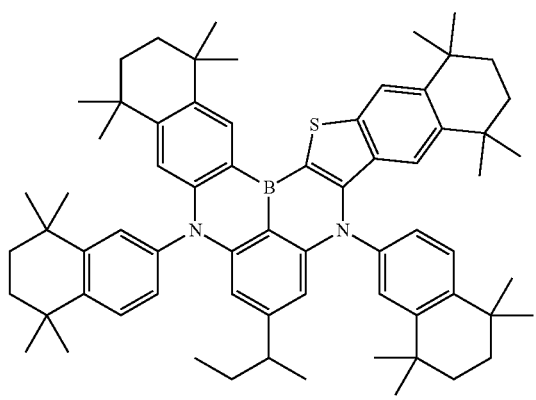
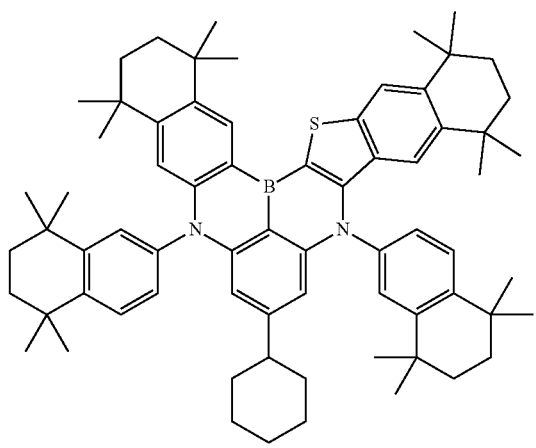
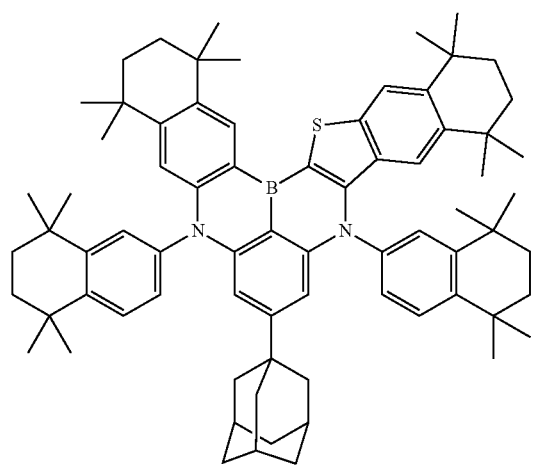
2372
-continued
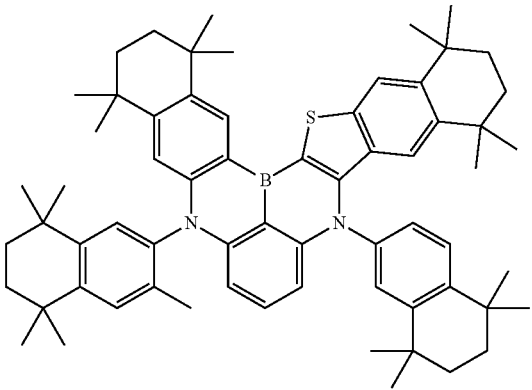
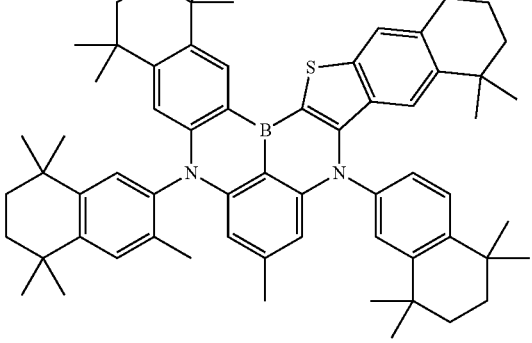
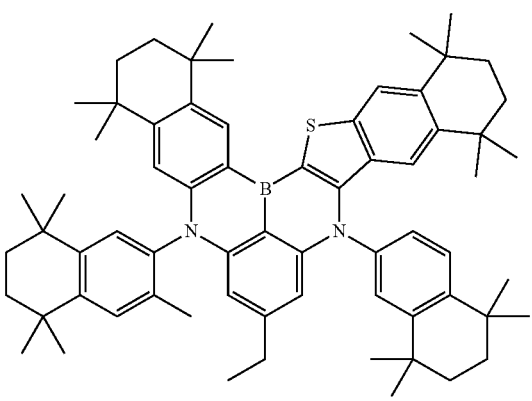
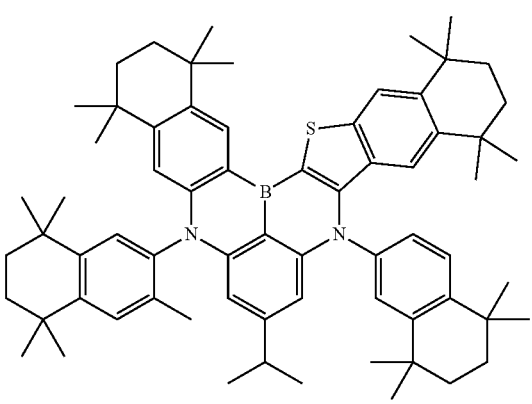

| 2373 | 2374 |
|---|---|
| 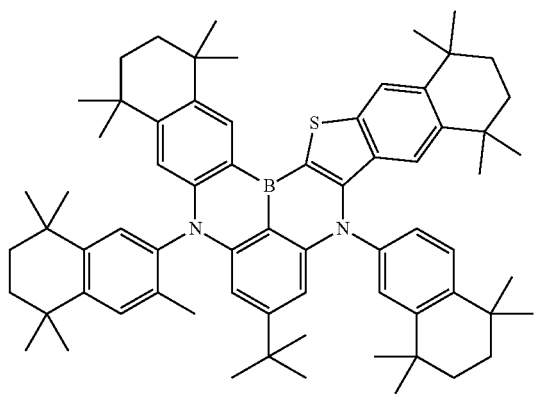 | 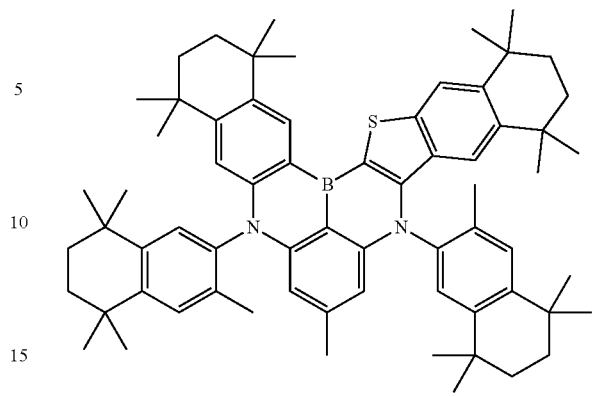 |
| 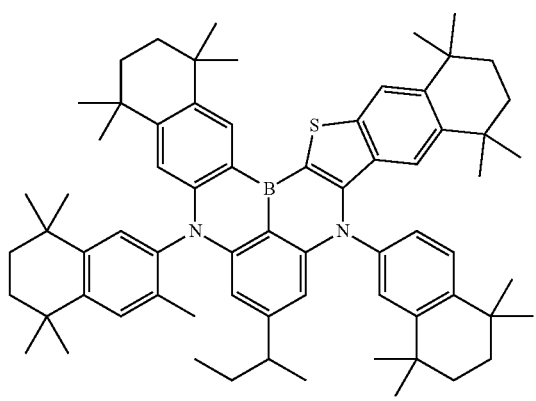 | 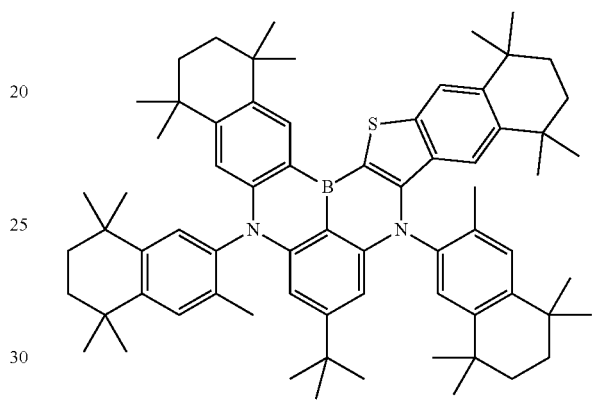 |
| 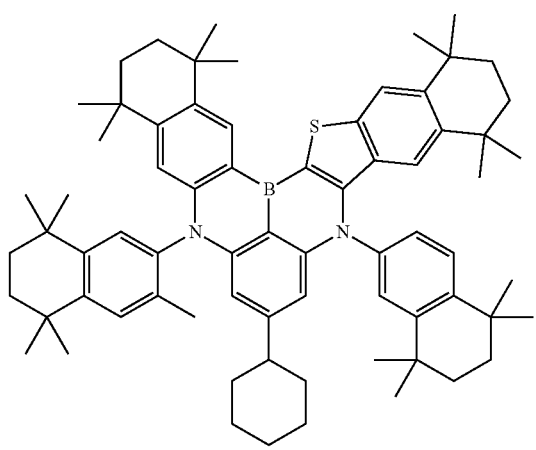 | 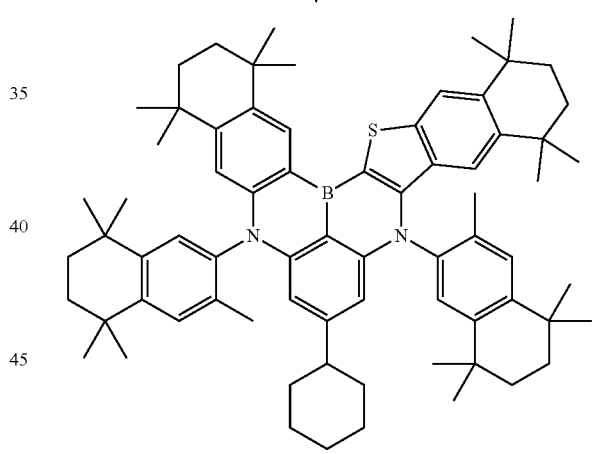 |
| 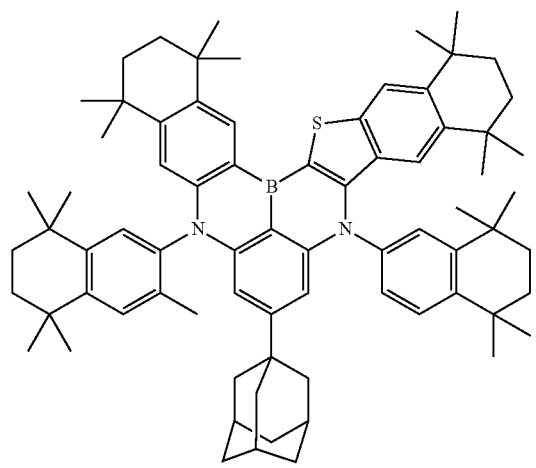 | 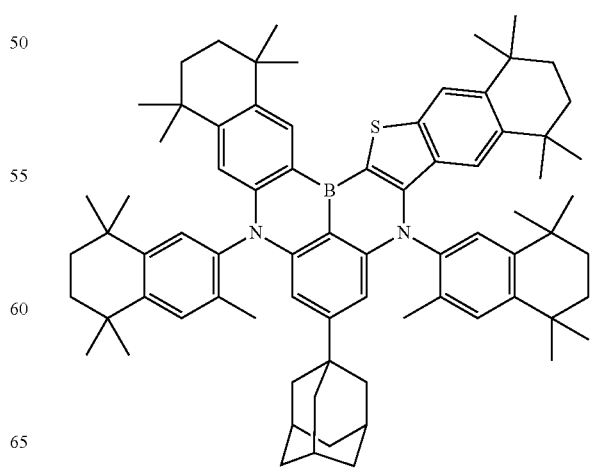 |

2375
-continued
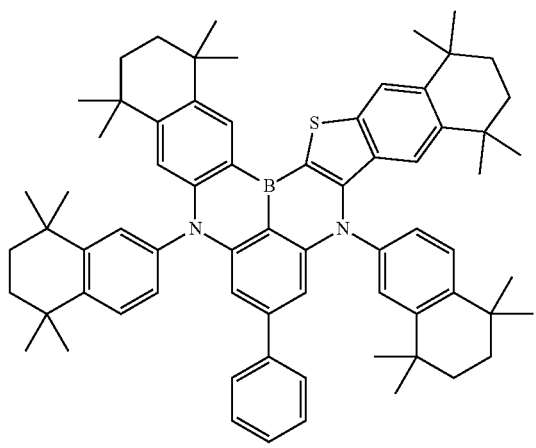
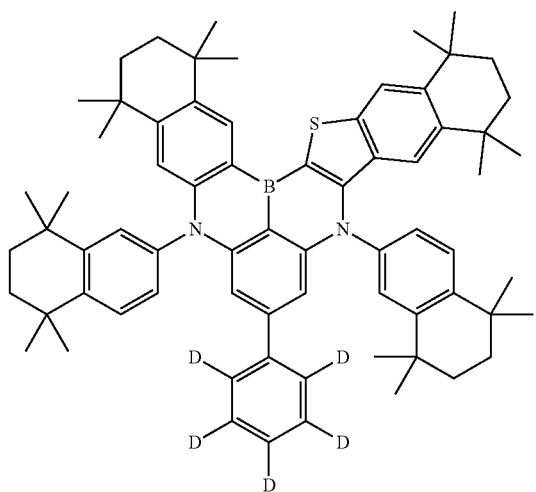
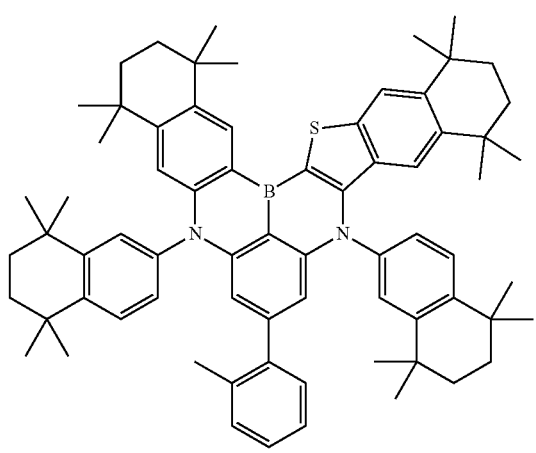
2376
-continued
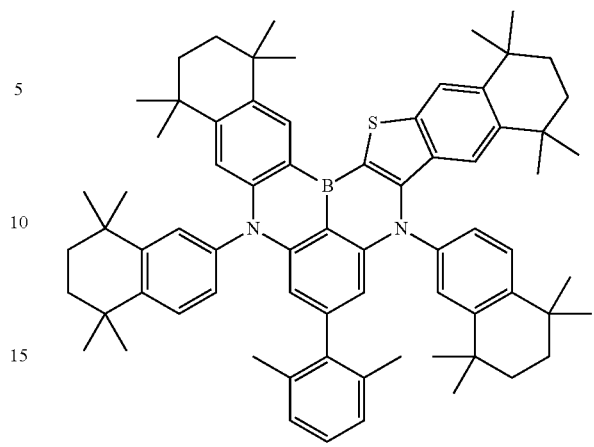
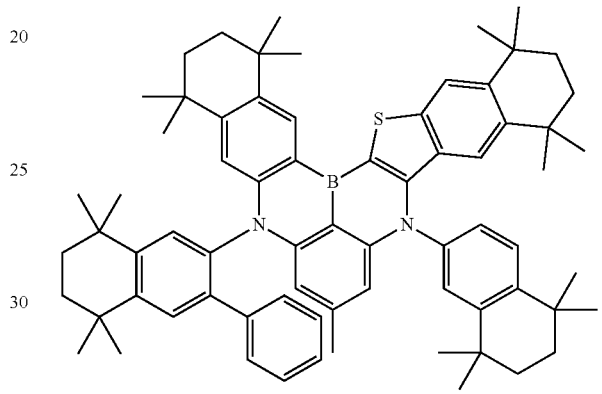
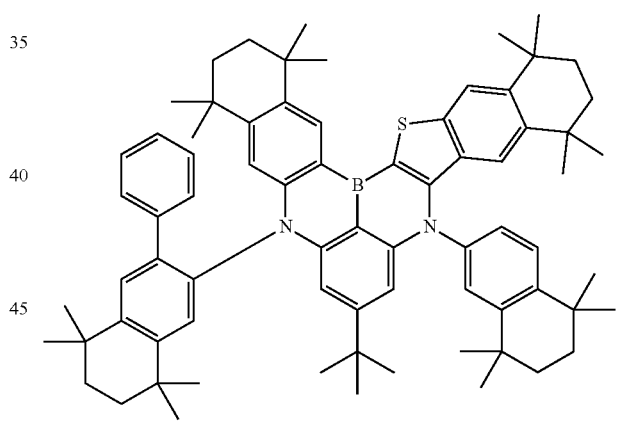
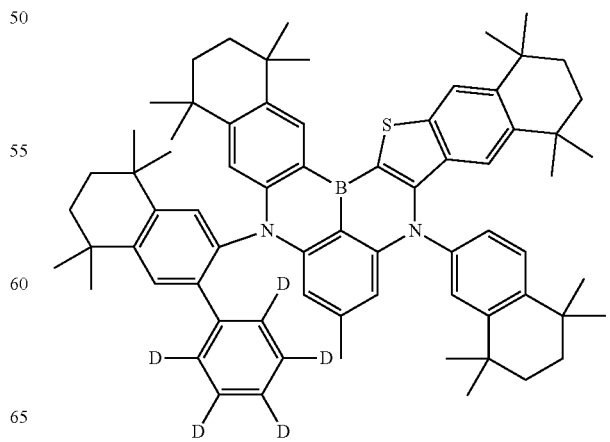

2377
-continued
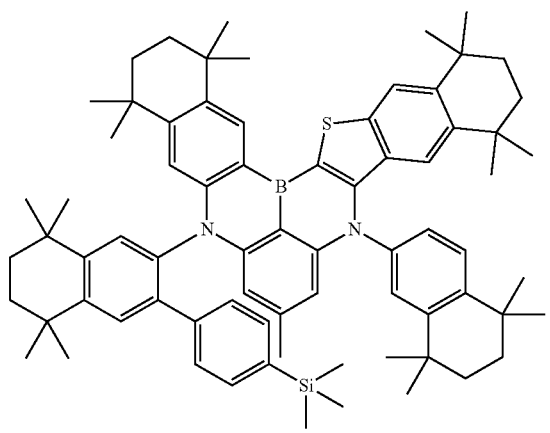
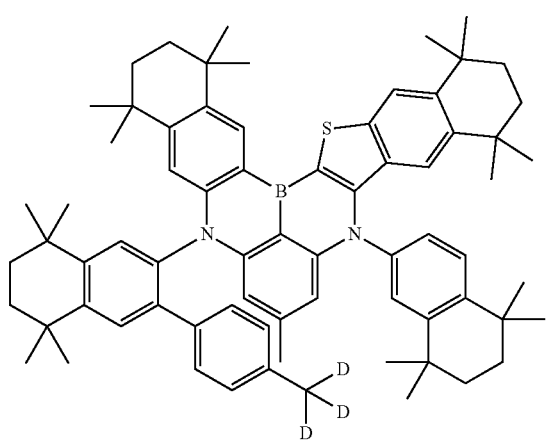
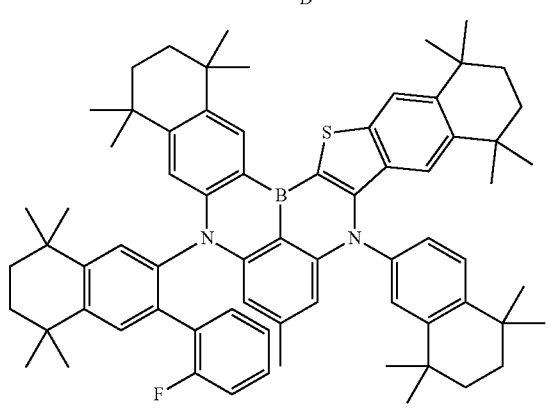
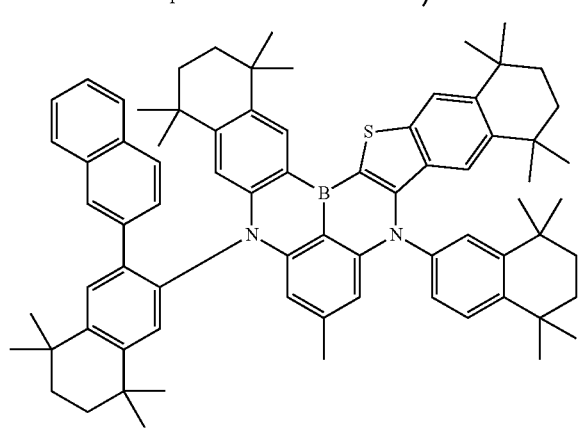
2378
-continued
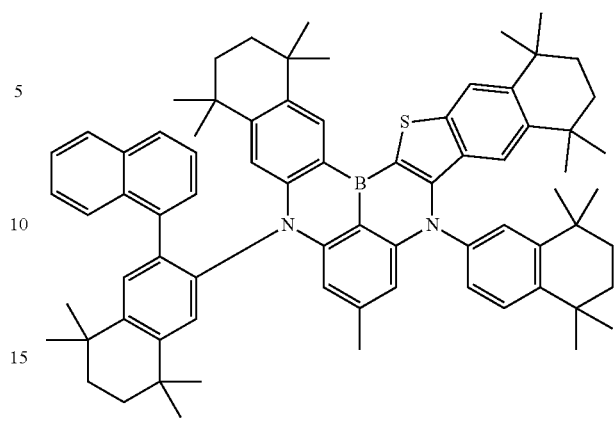
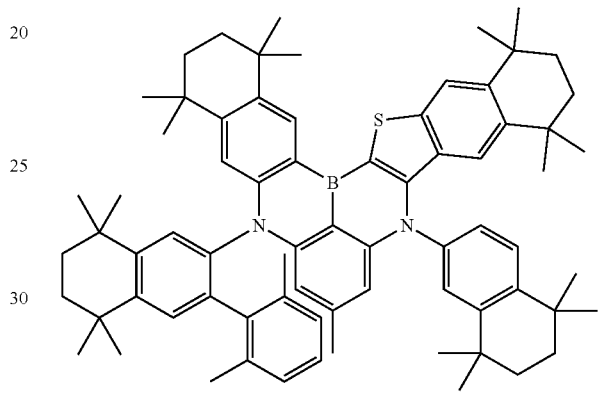
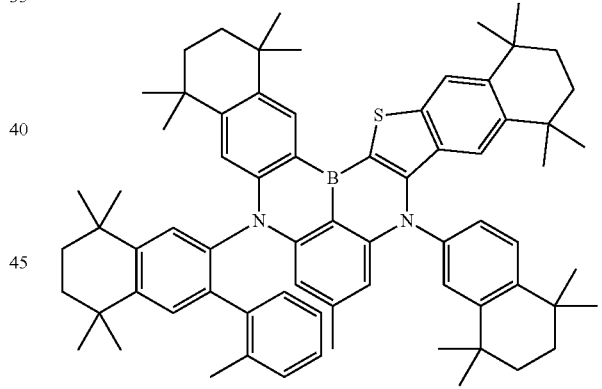
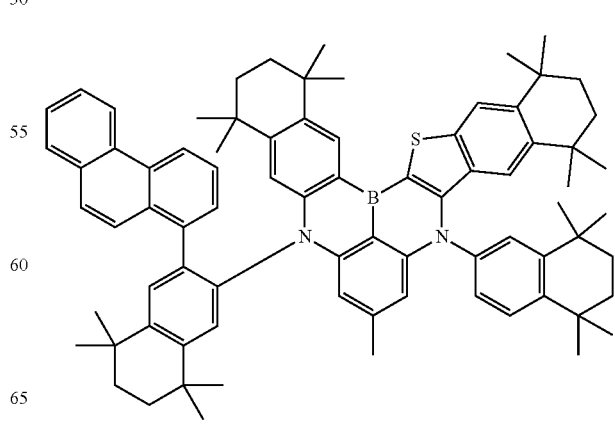

2379
-continued
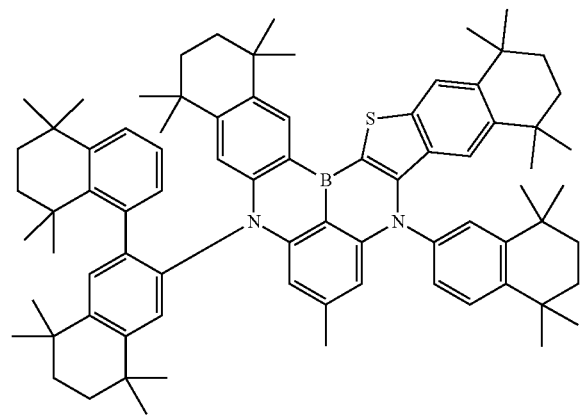
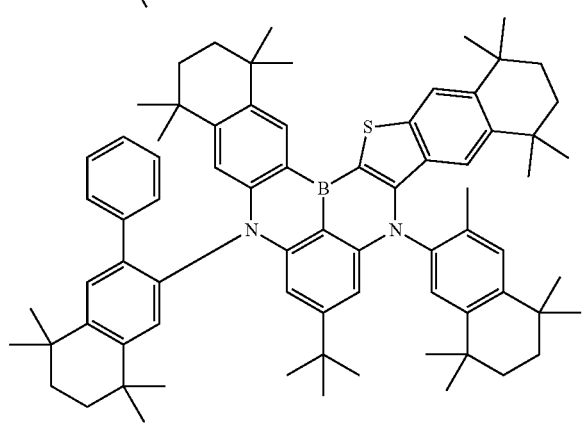
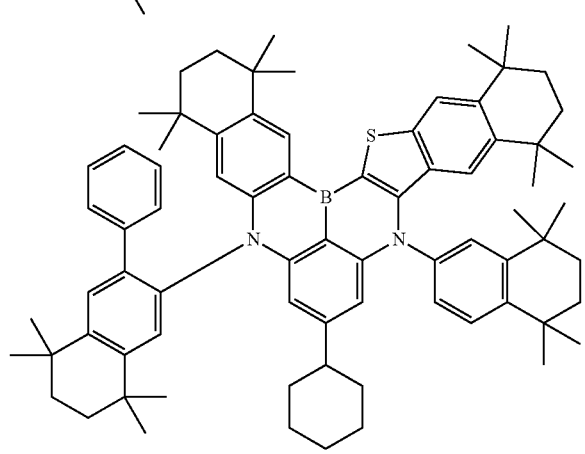
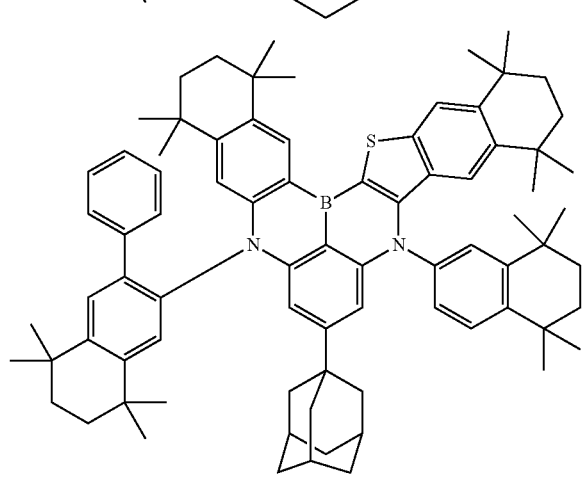
2380
-continued
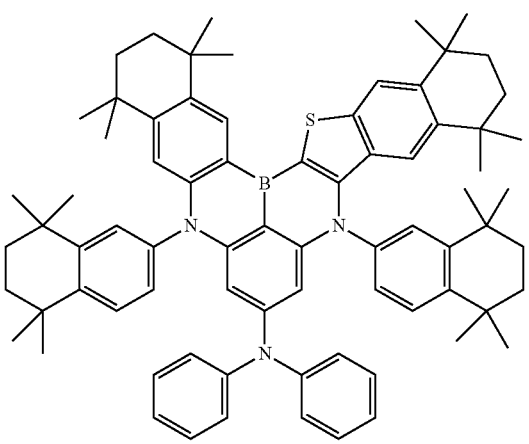
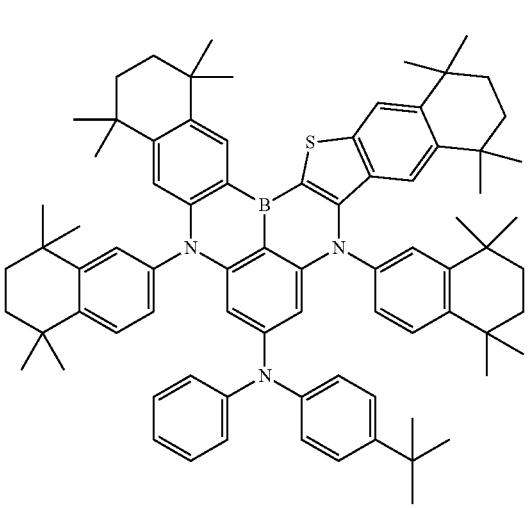
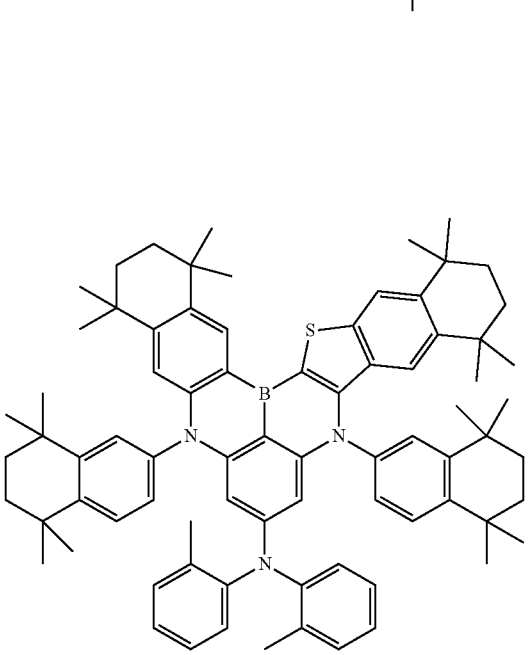

| 2381 | 2382 |
|---|---|
| -continued | -continued |
| 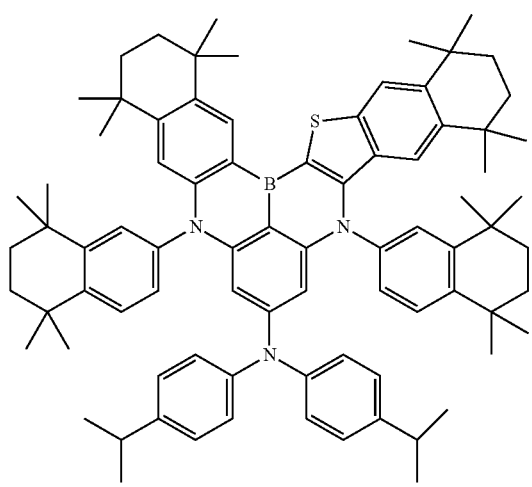 | 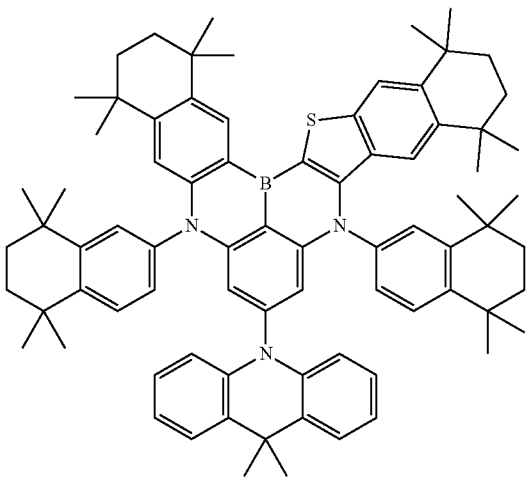 |
| 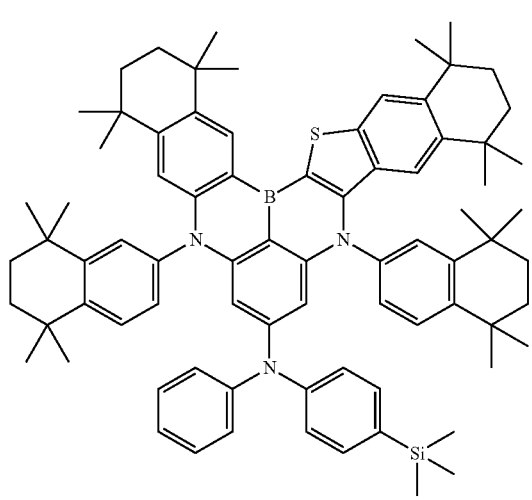 | 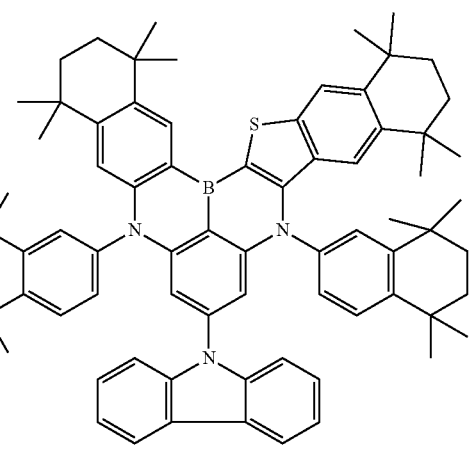 |
| 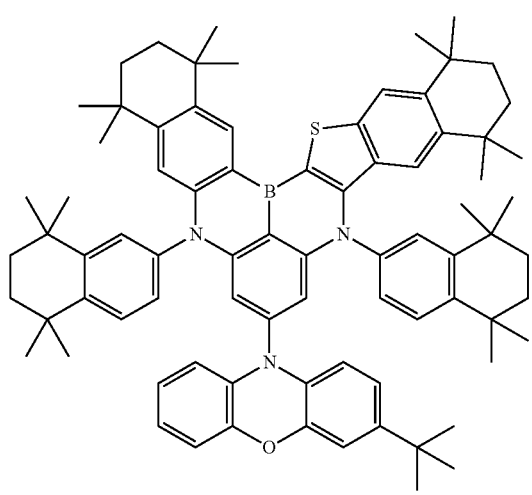 | 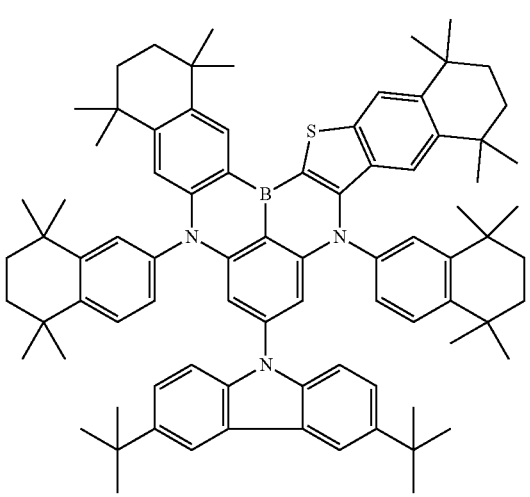 |

2383
-continued
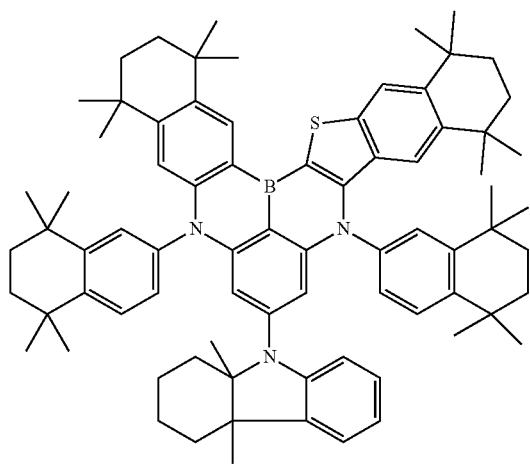
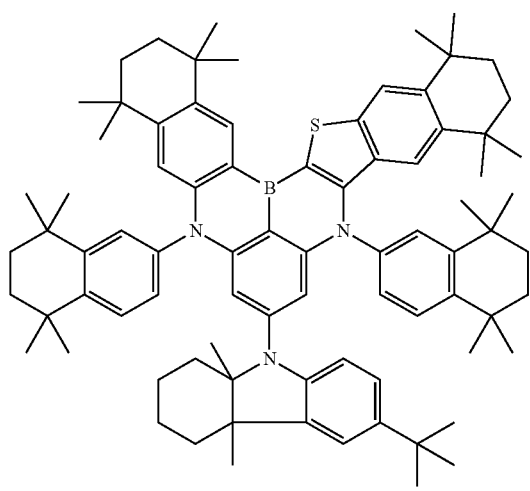
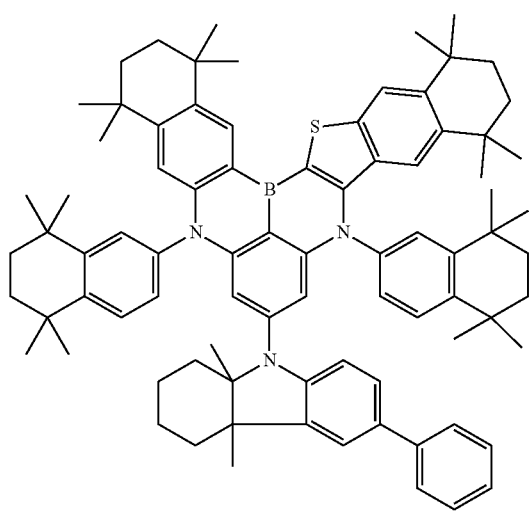
2384
-continued
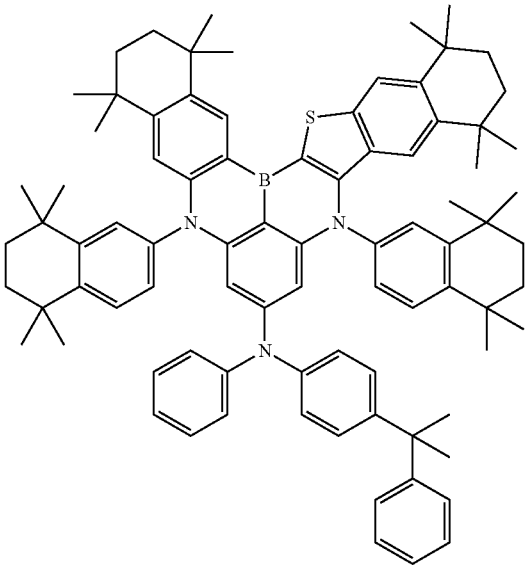
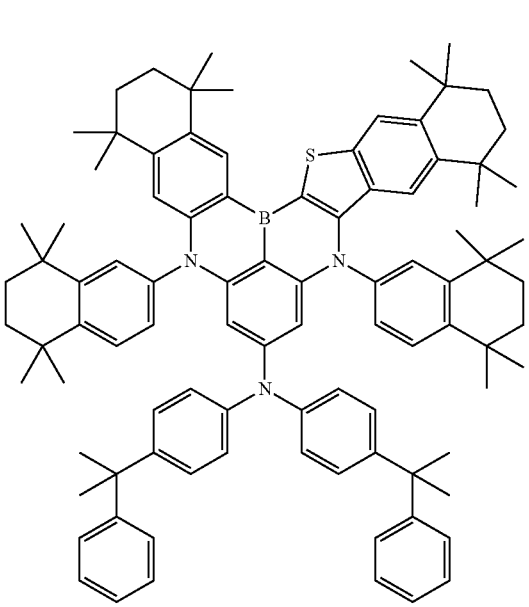
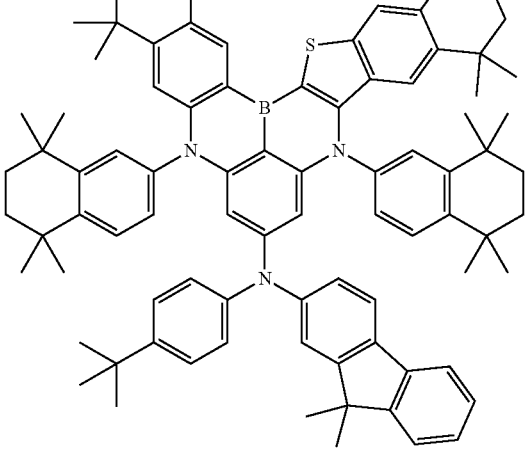

2385
-continued
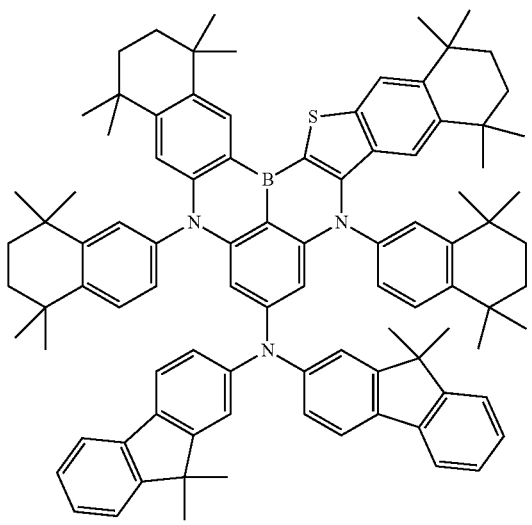
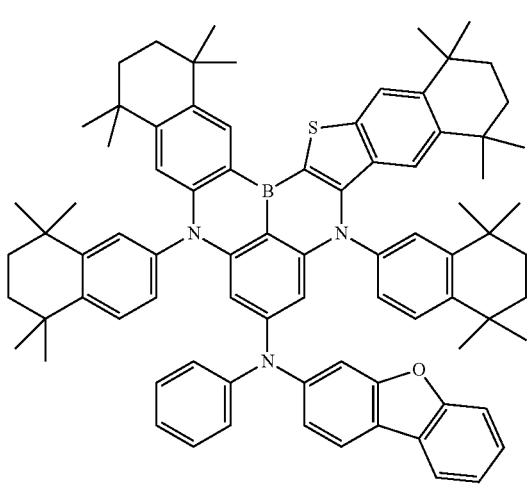
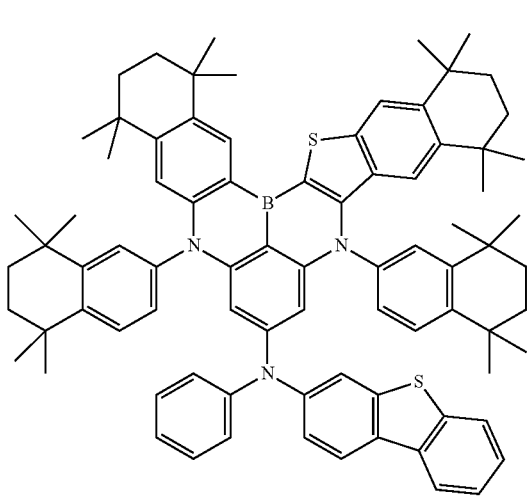
2386
-continued
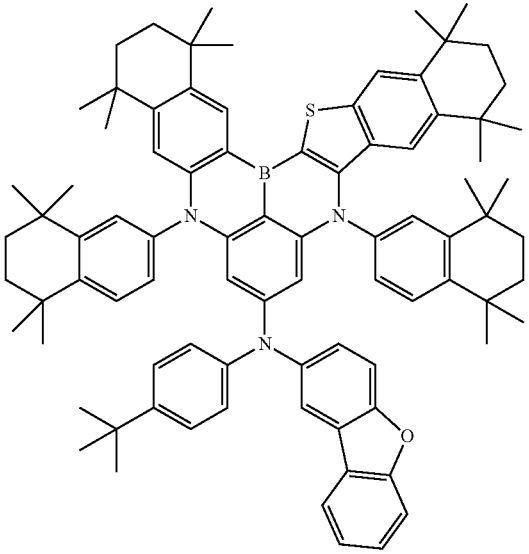
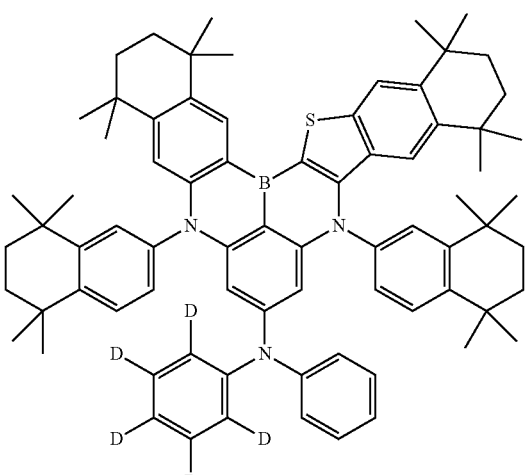
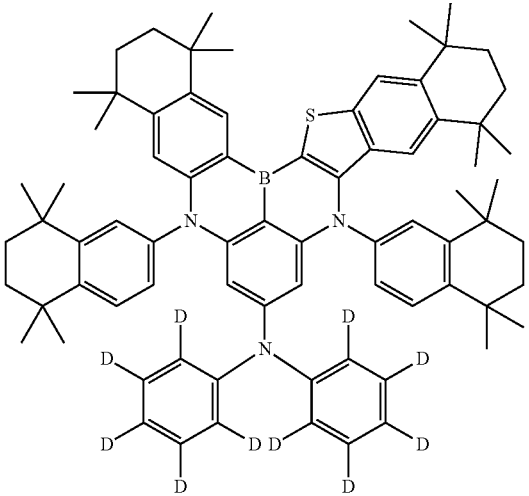

2387
-continued
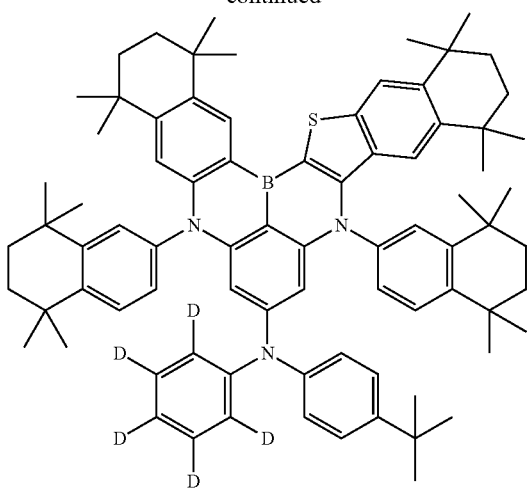
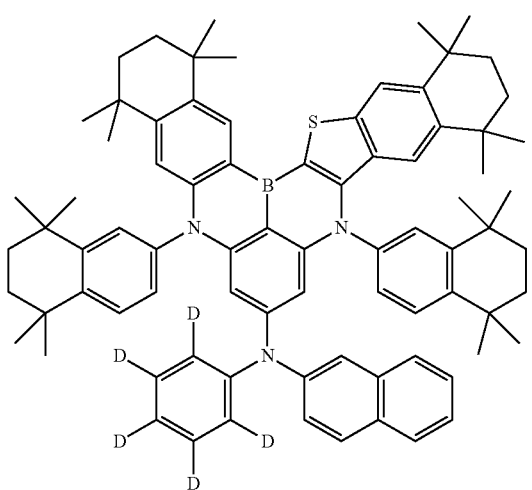
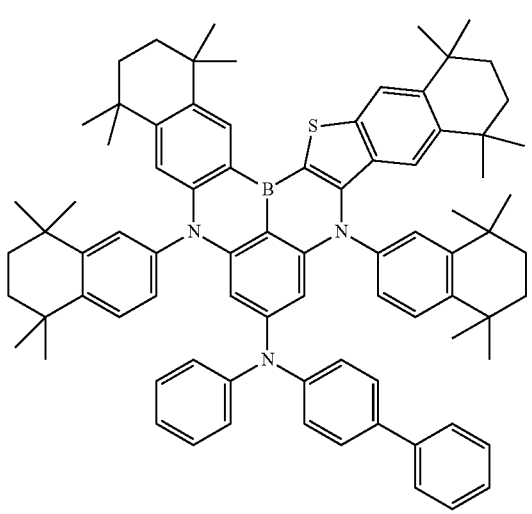
2388
-continued
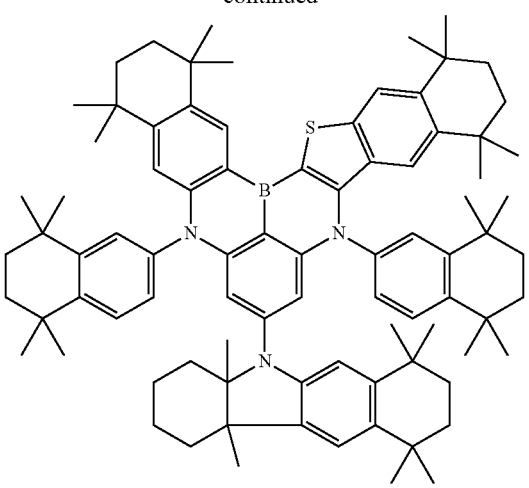
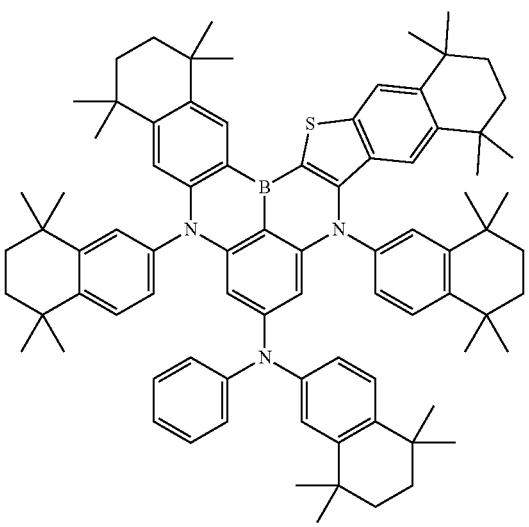
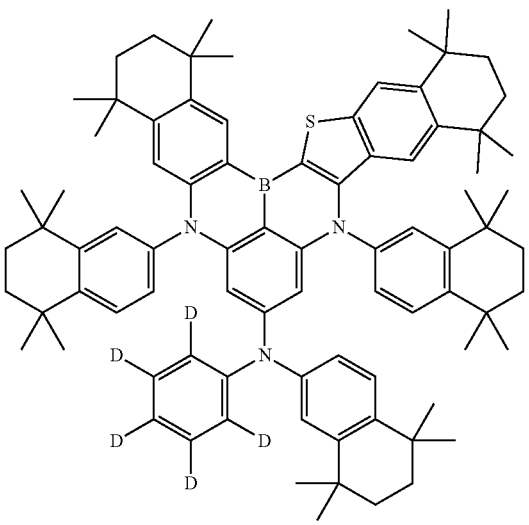

2389
-continued
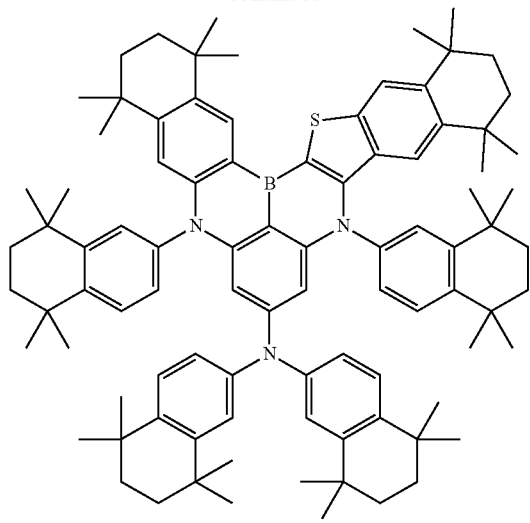
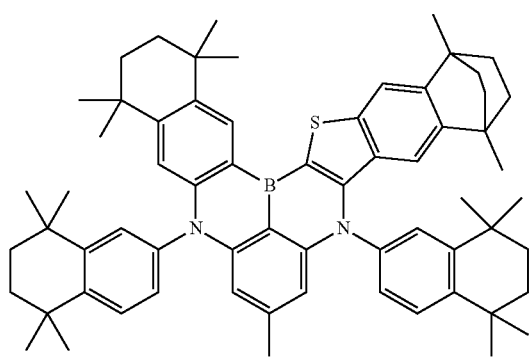
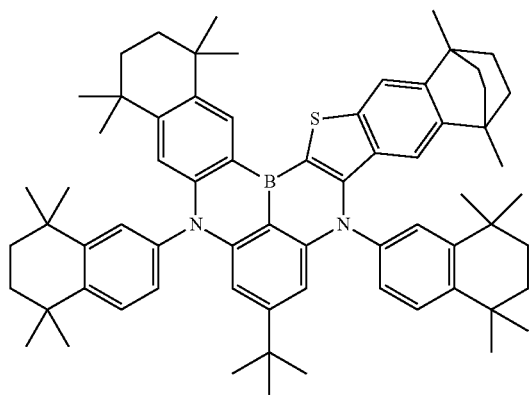
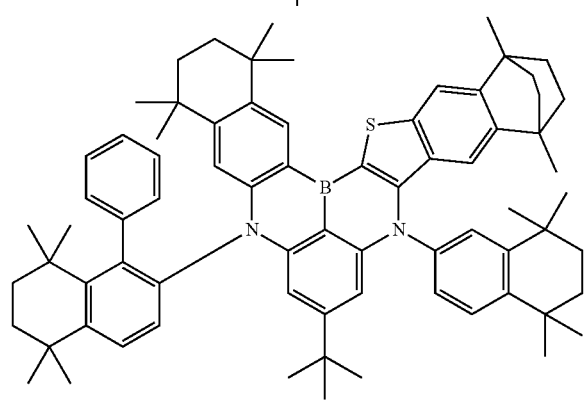
2390
-continued
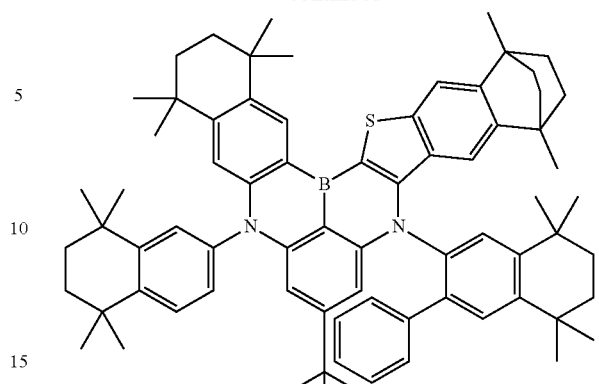
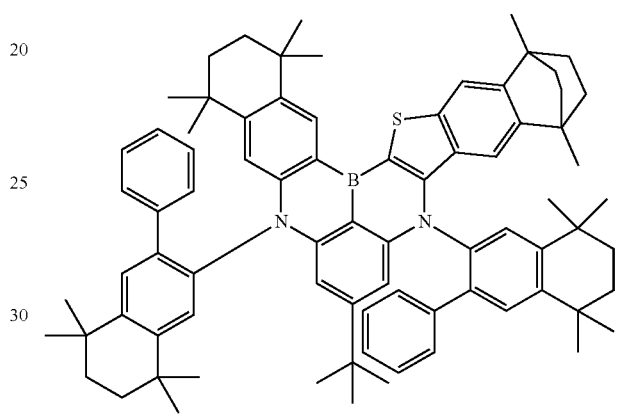
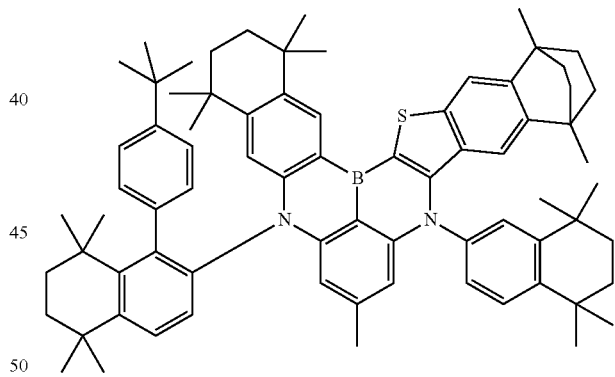
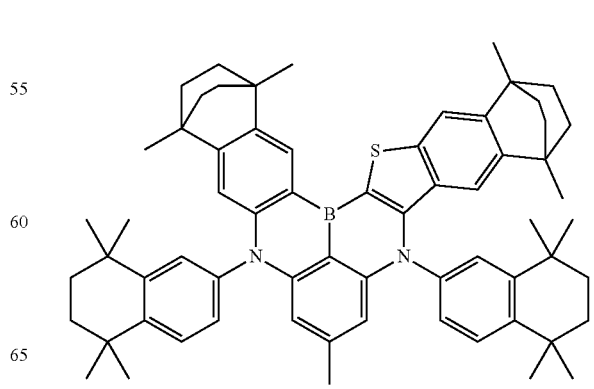

2391
-continued
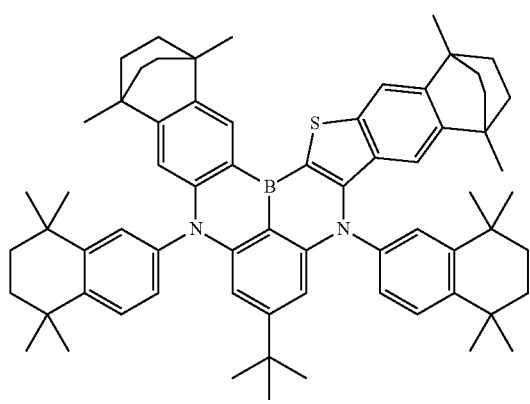
2392
-continued
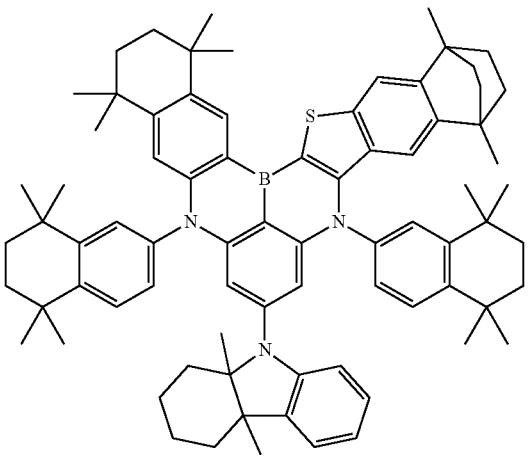
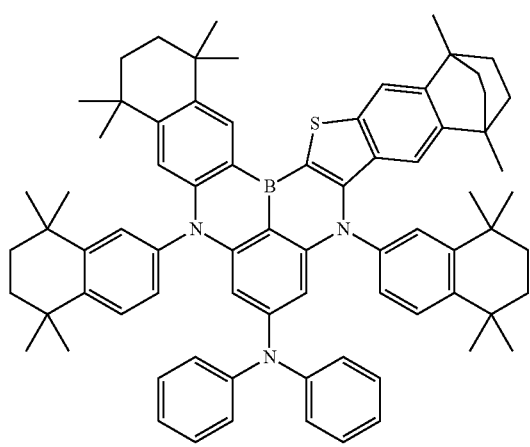
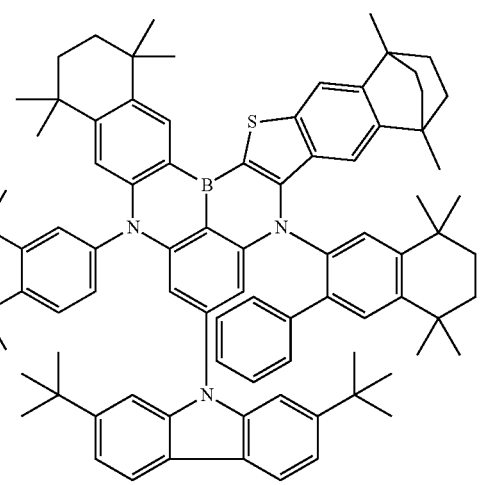
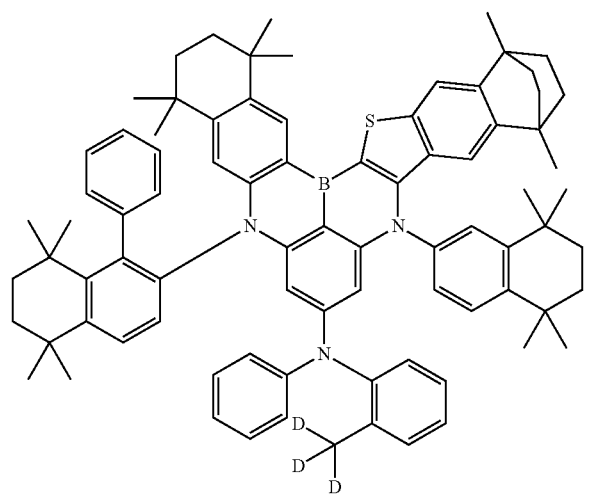
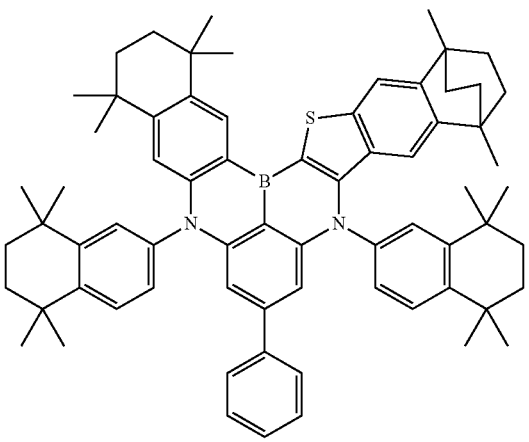

2393
-continued
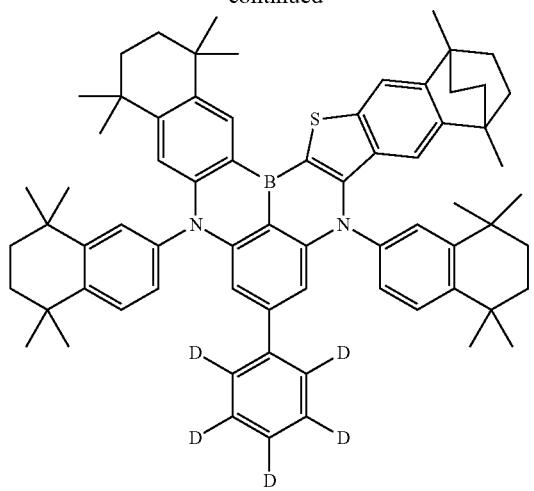
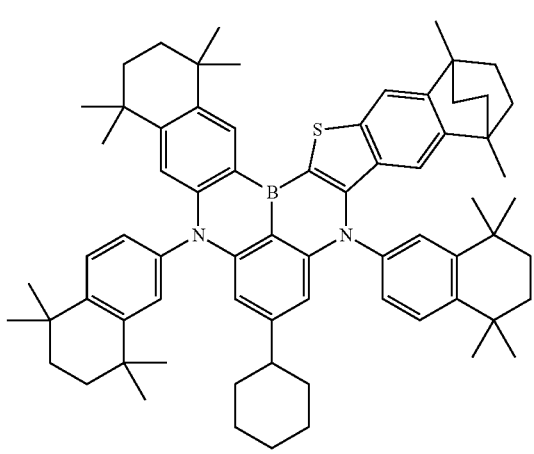
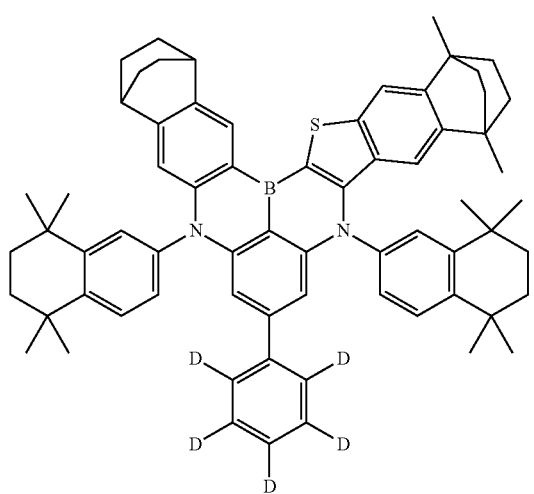
2394
-continued
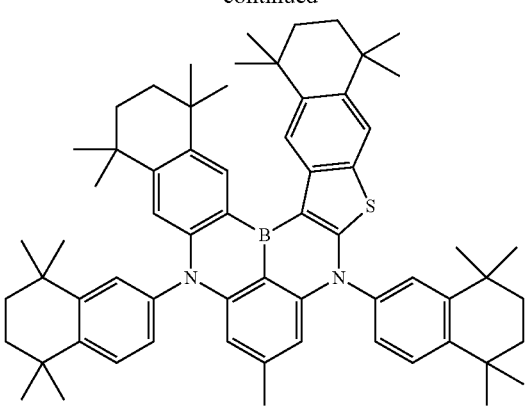
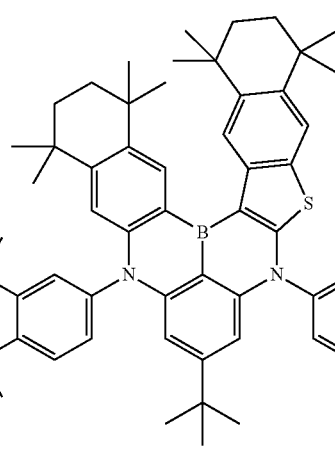
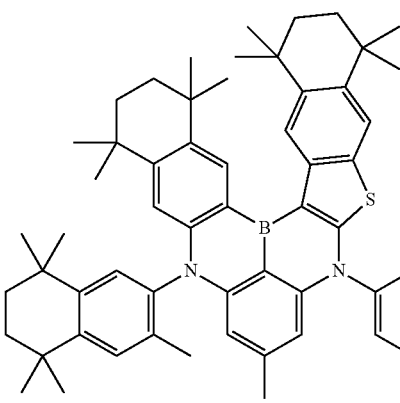
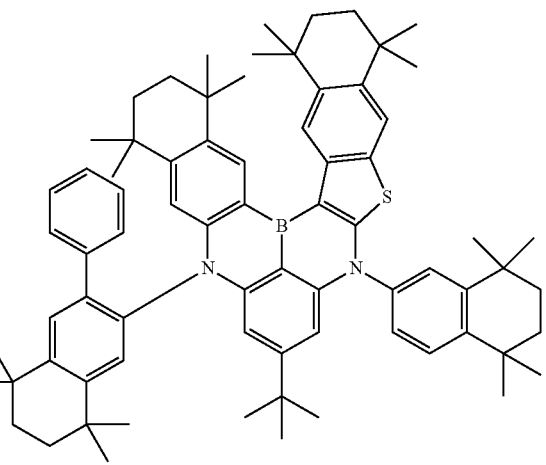

2395
-continued
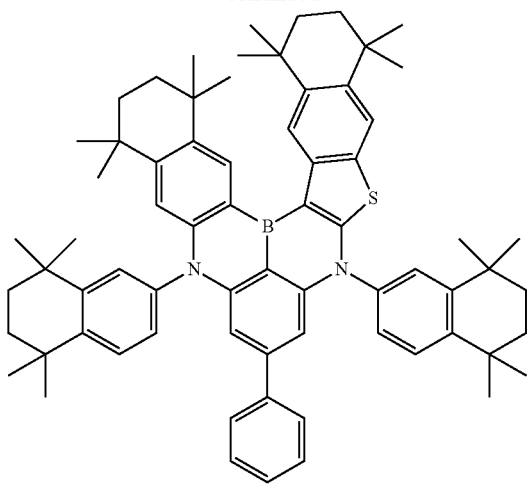
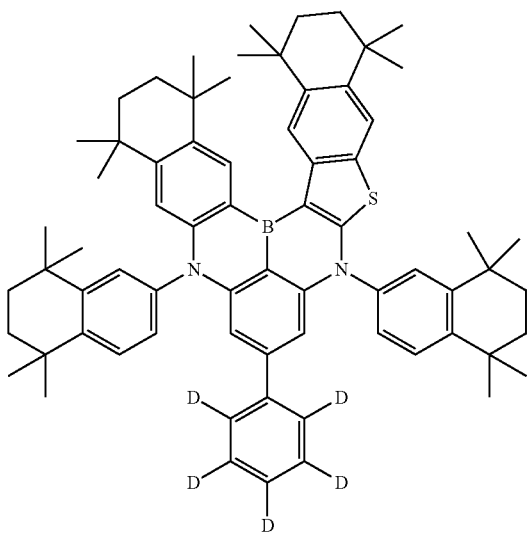
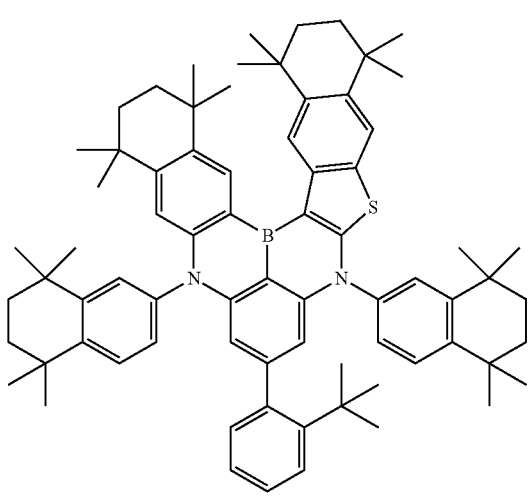
2396
-continued
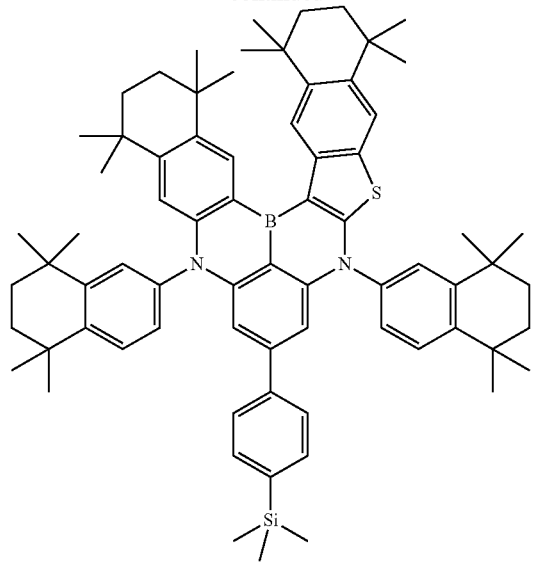
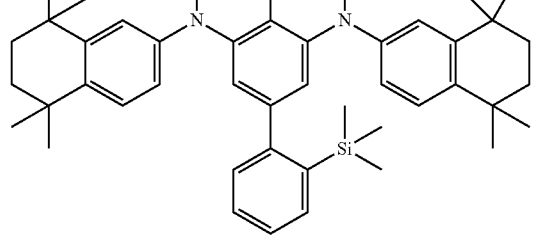
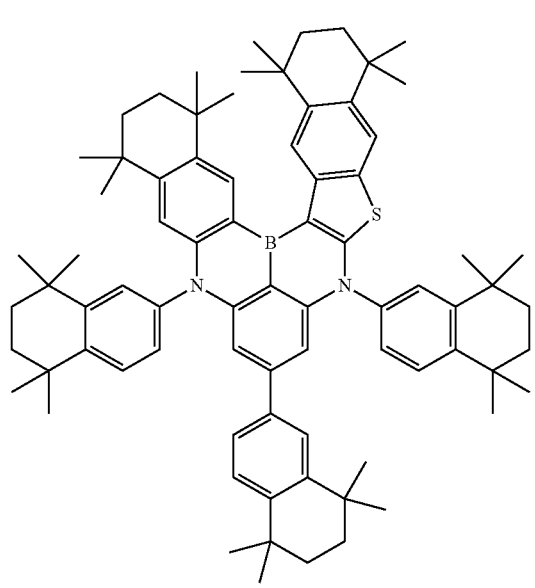

2397
-continued
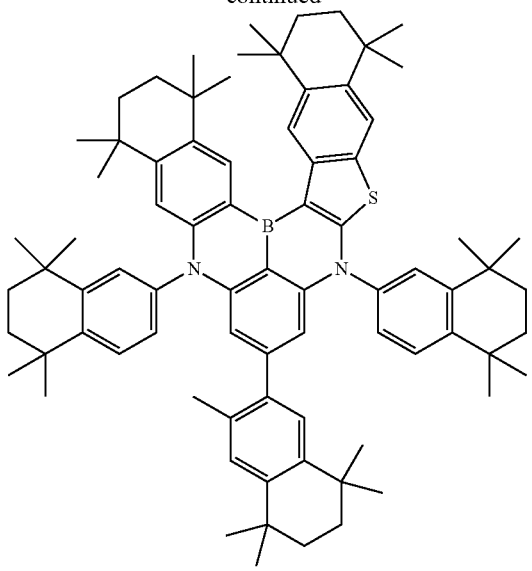
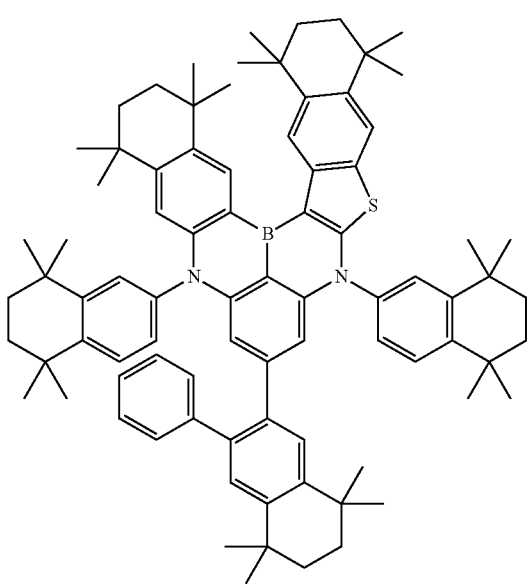
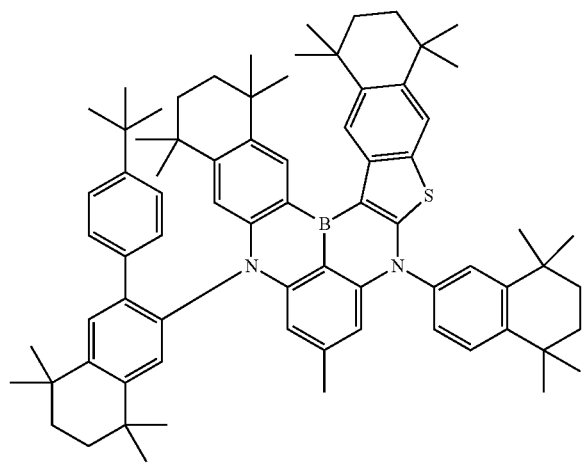
2398
-continued
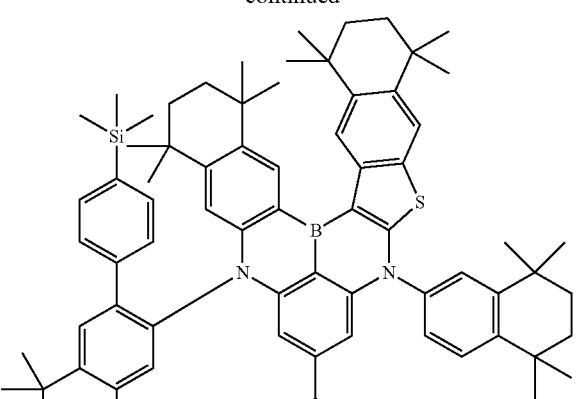
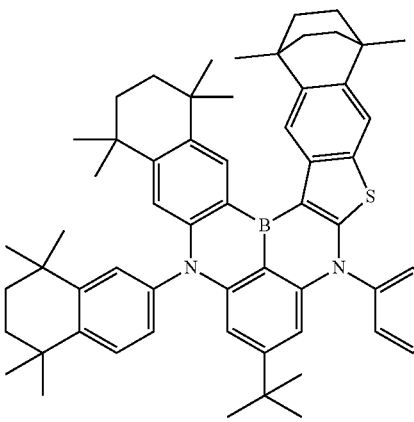
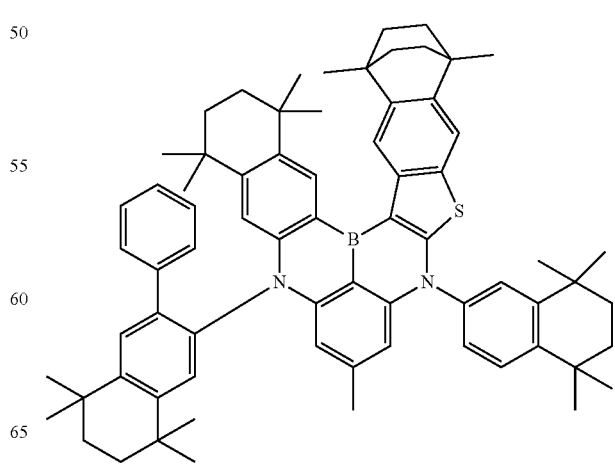

2399
-continued
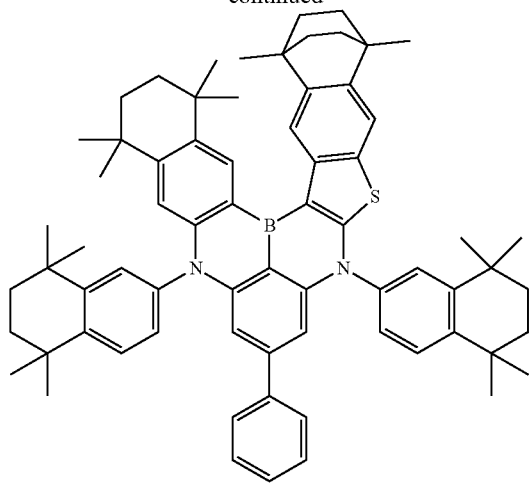
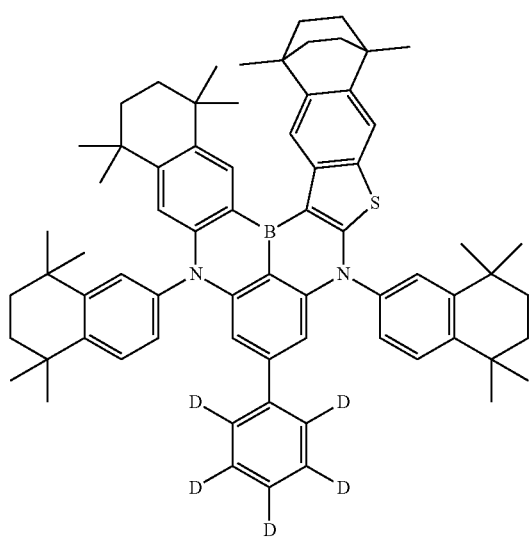
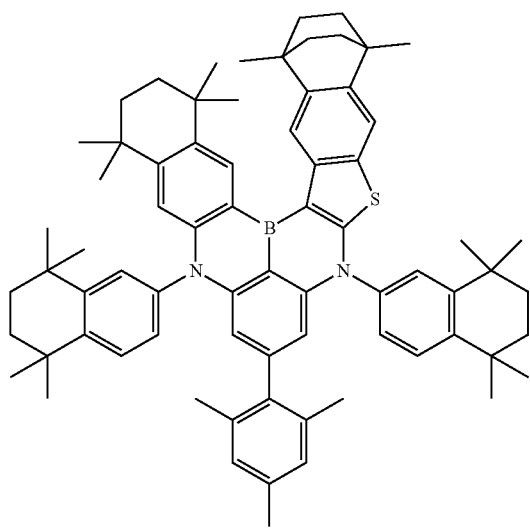
2400
-continued
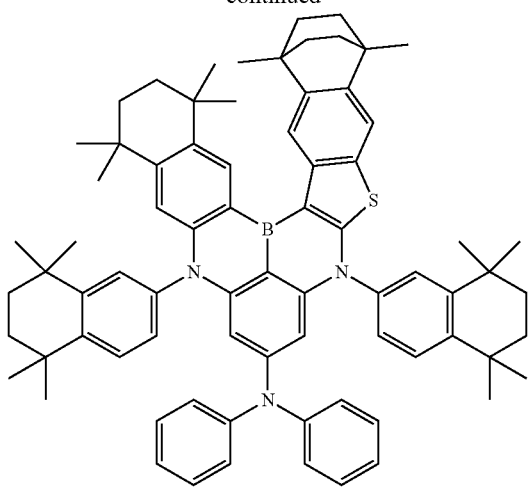
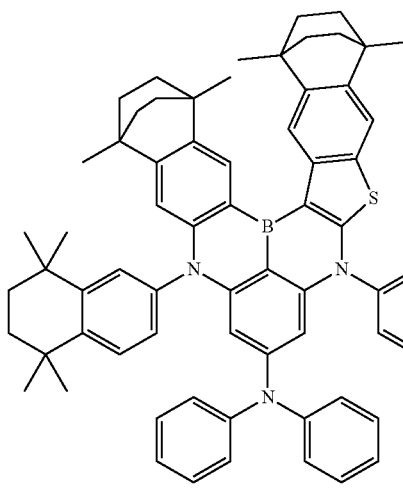
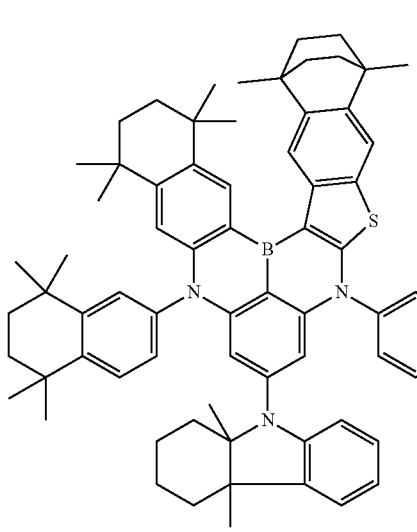

2401
-continued
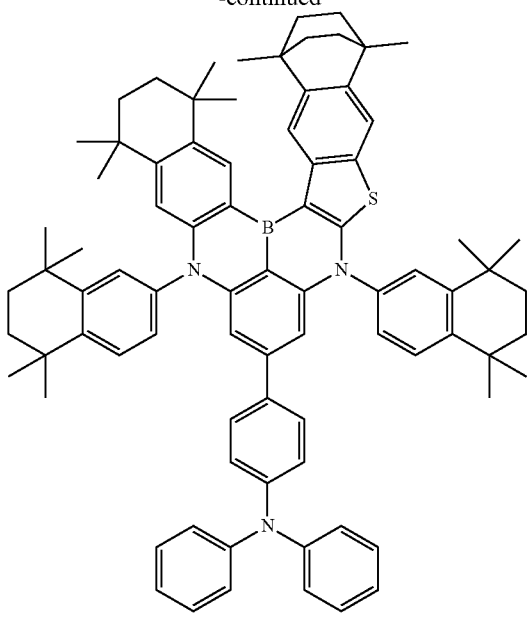
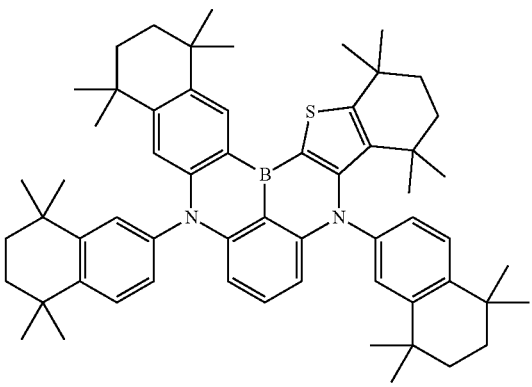
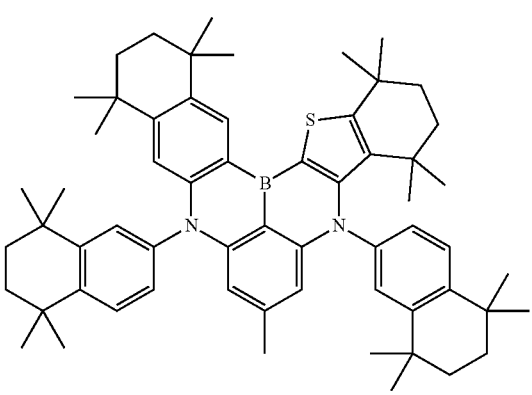
2402
-continued
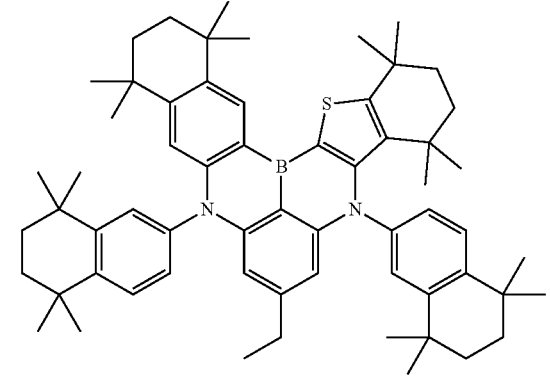
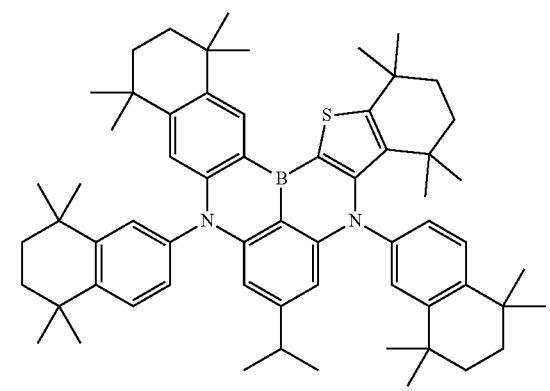
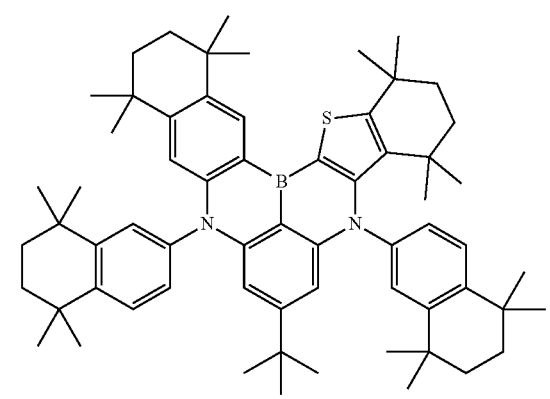
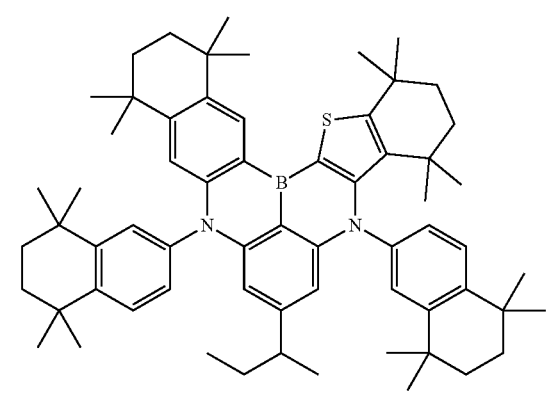

2403
-continued
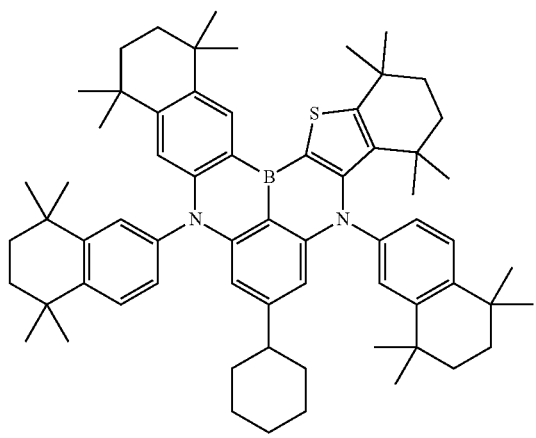
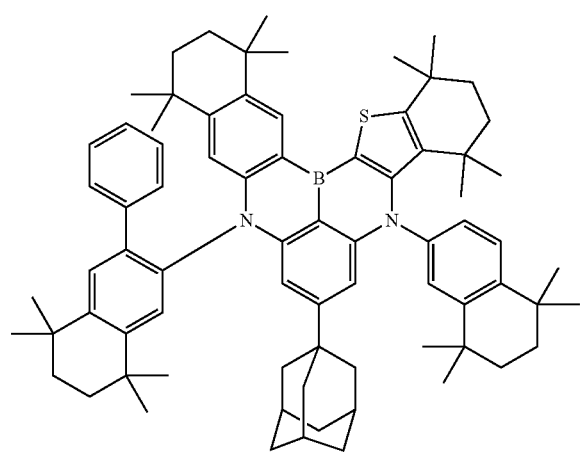
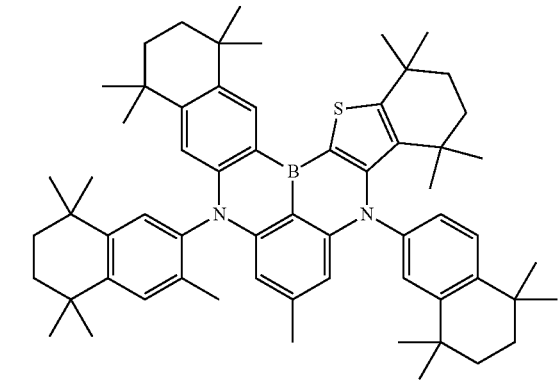
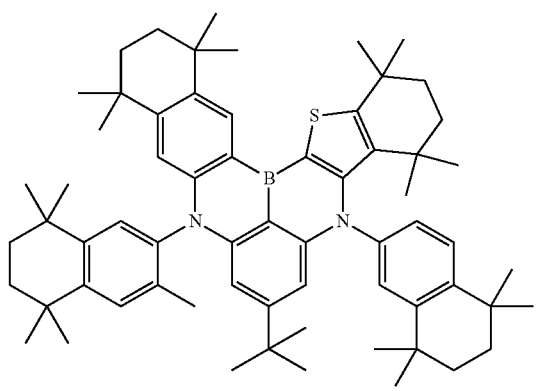
2404
-continued
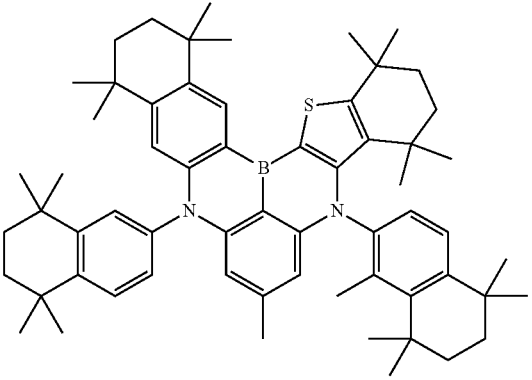
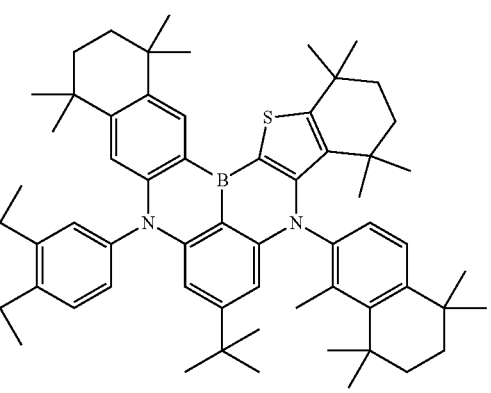
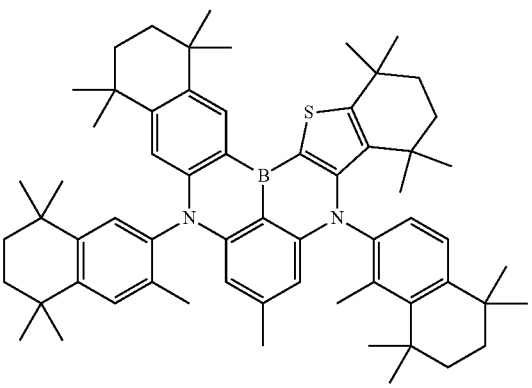
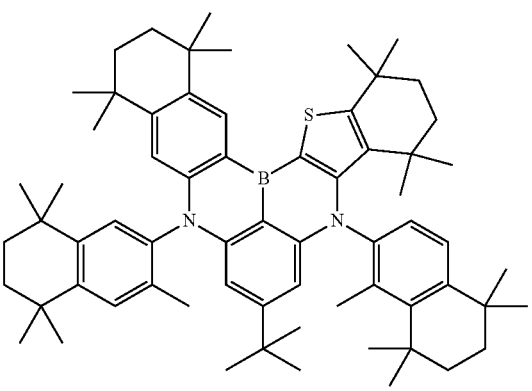

2405
-continued
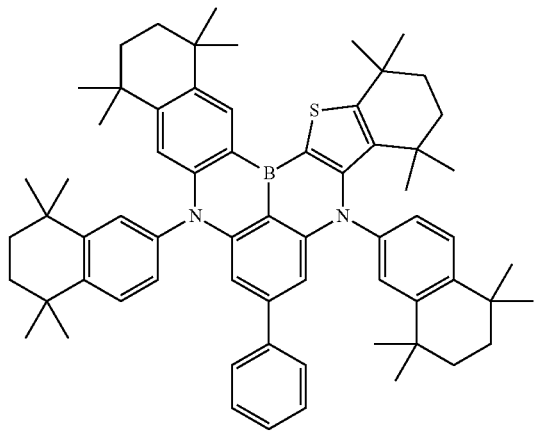
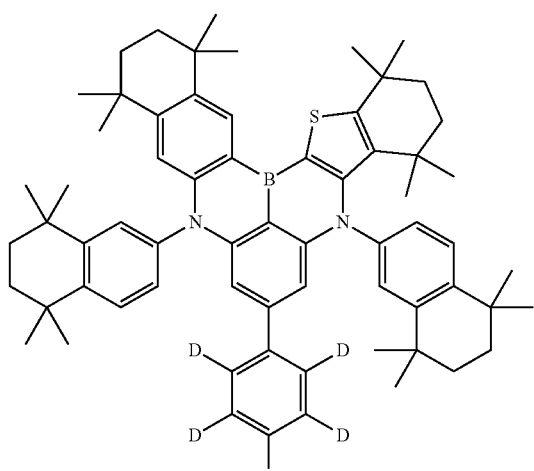
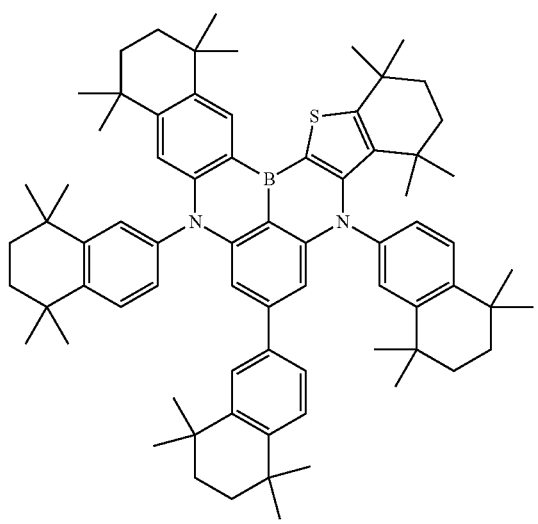
2406
-continued
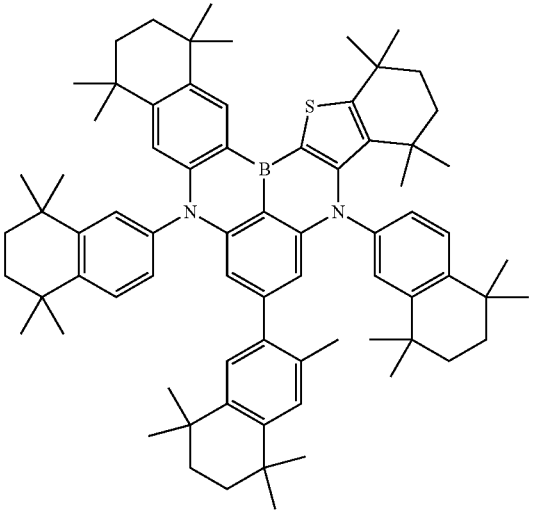
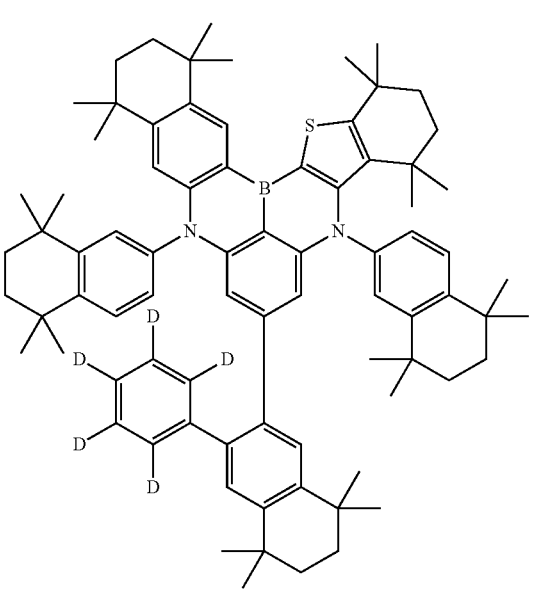
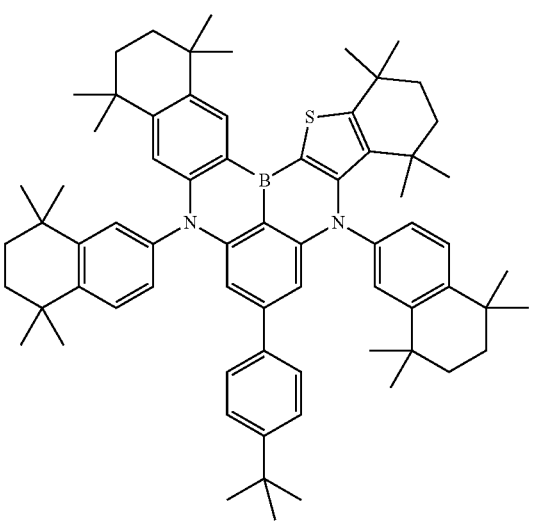

2407
-continued
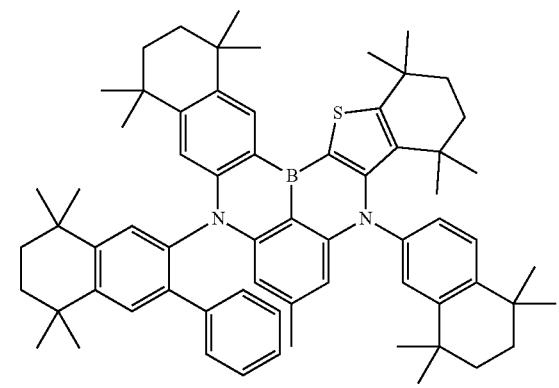
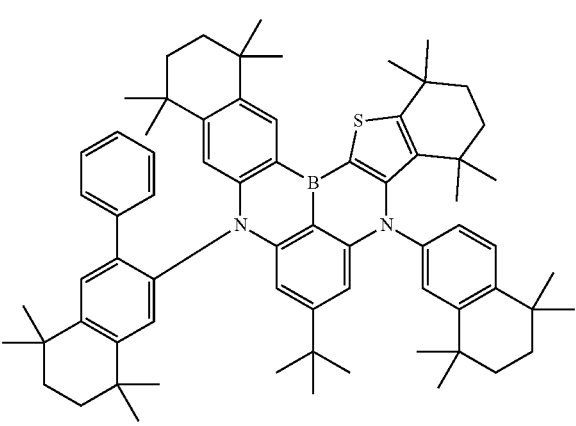
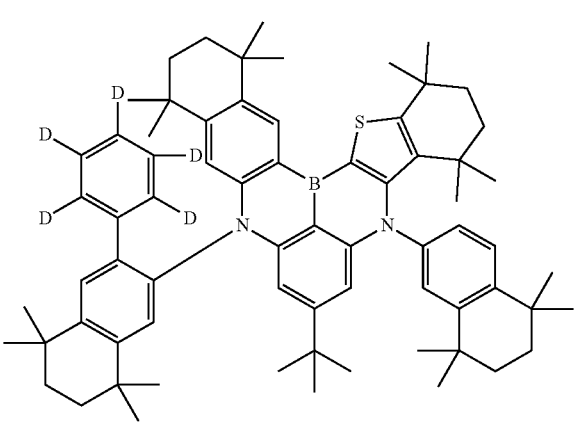
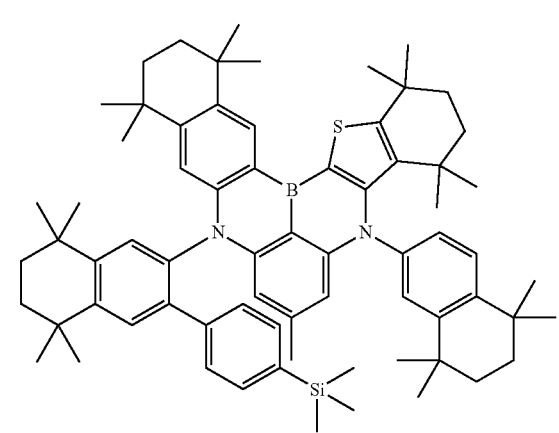
2408
-continued
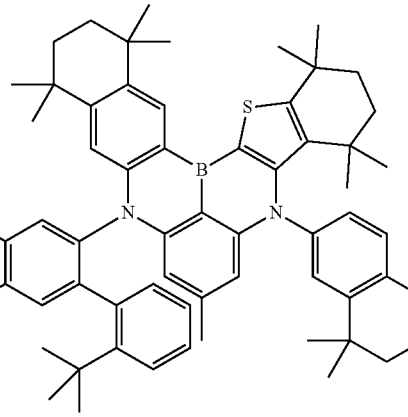
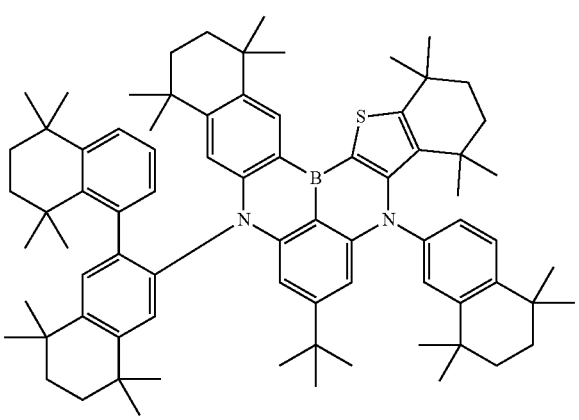
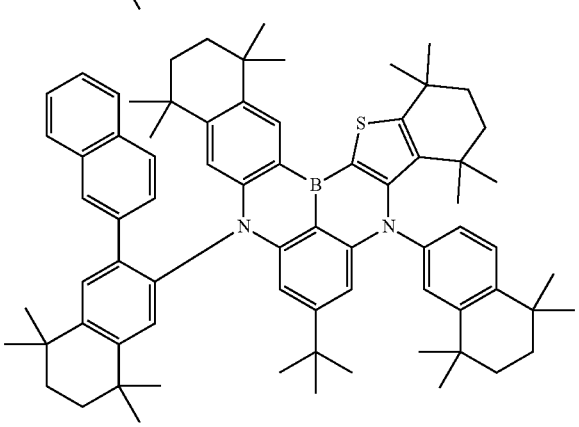

2409
-continued
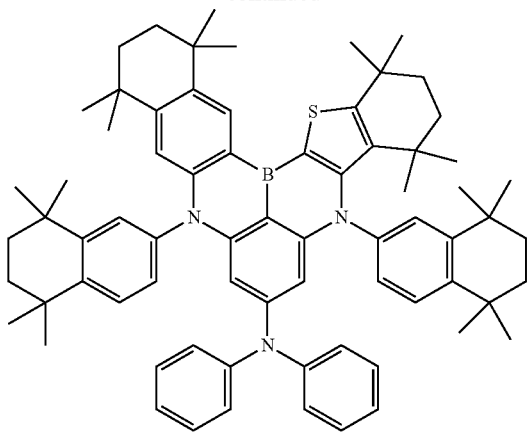
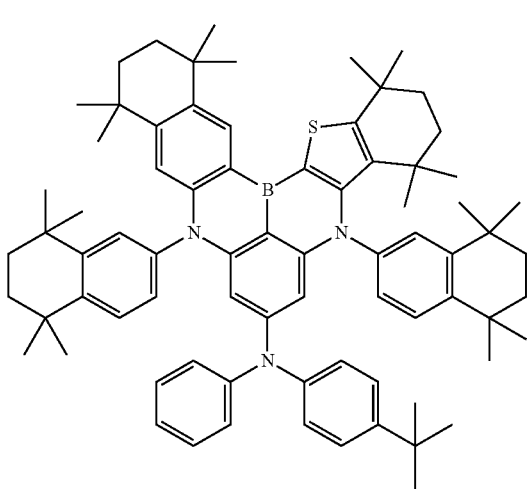
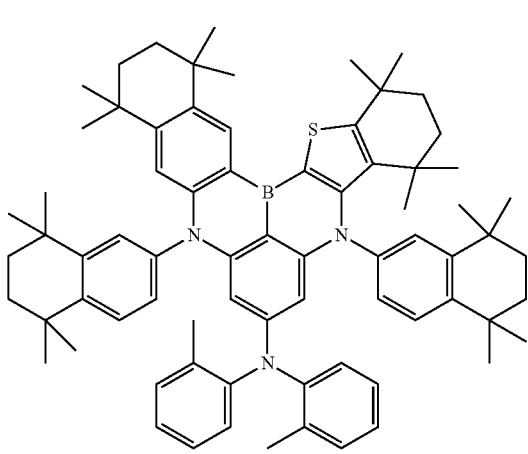
2410
-continued
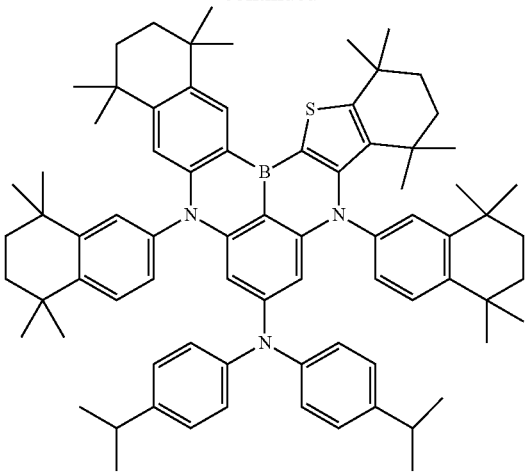
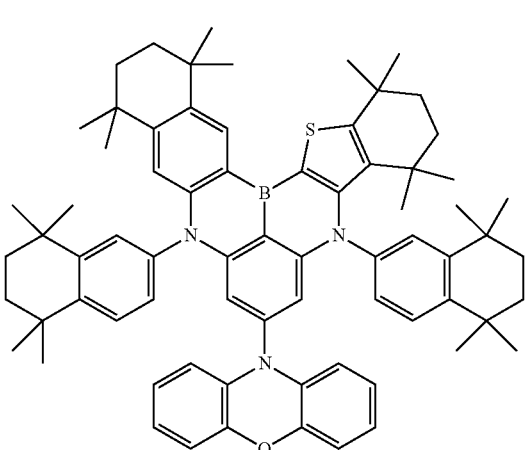
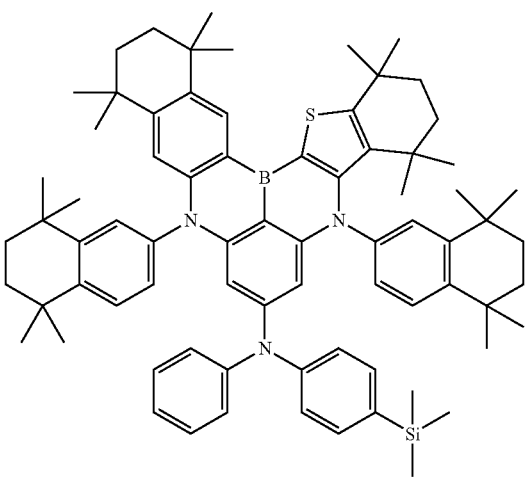

2411
-continued
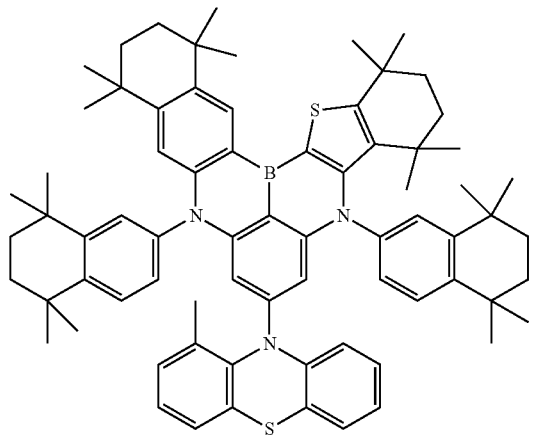
2412
-continued
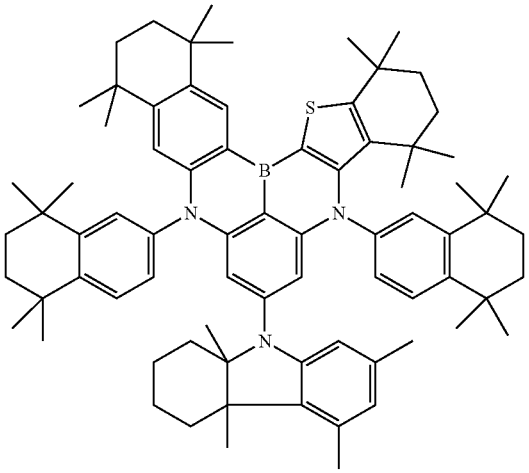
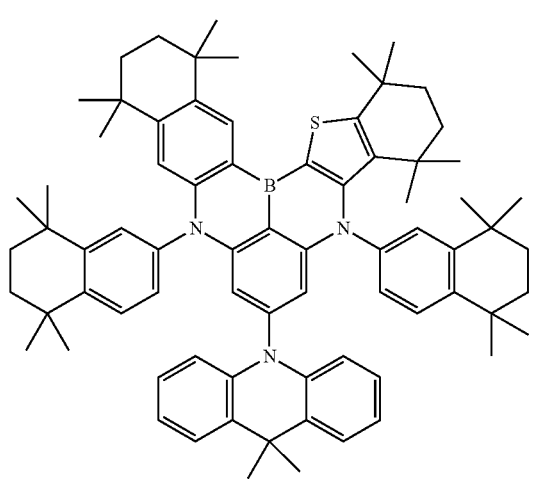
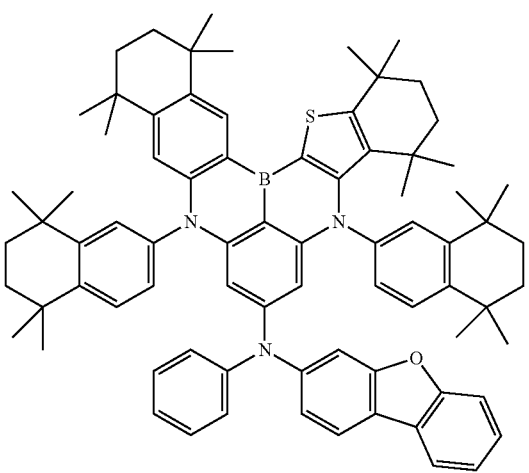
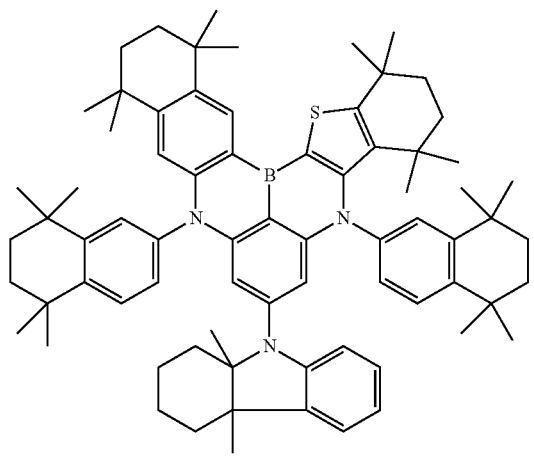
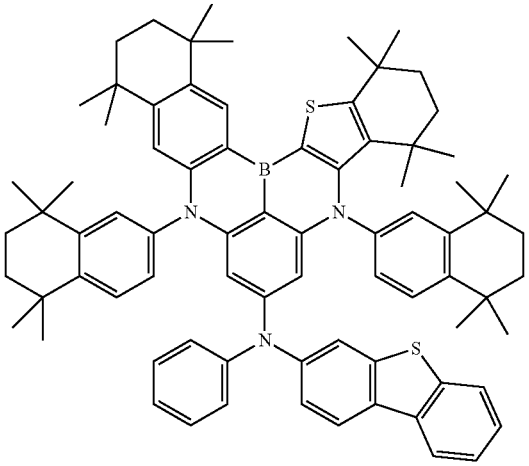

2413
-continued
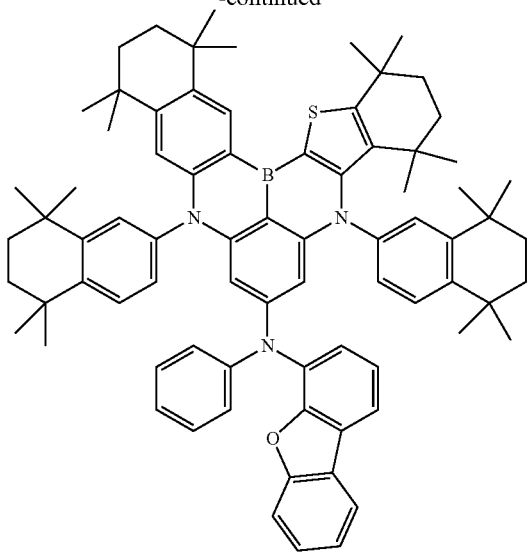
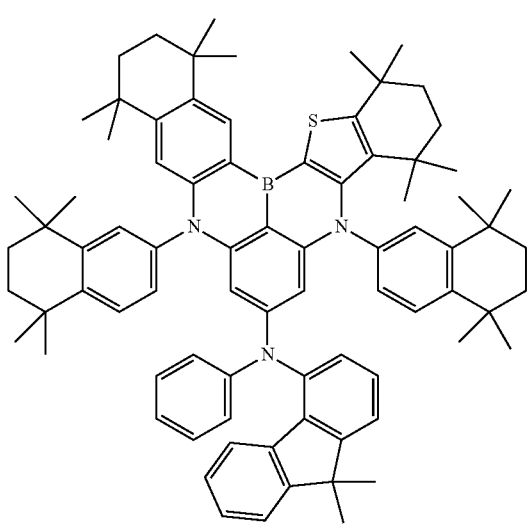
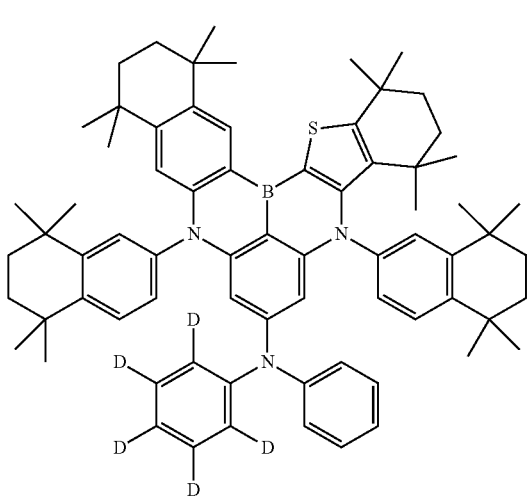
2414
-continued
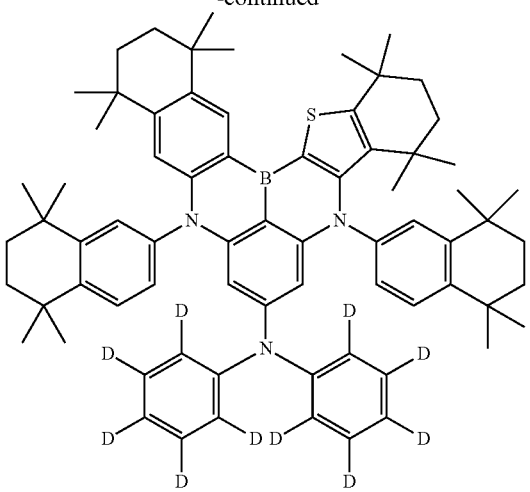
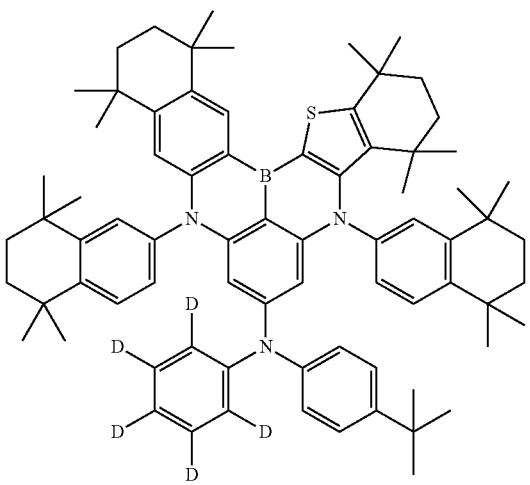
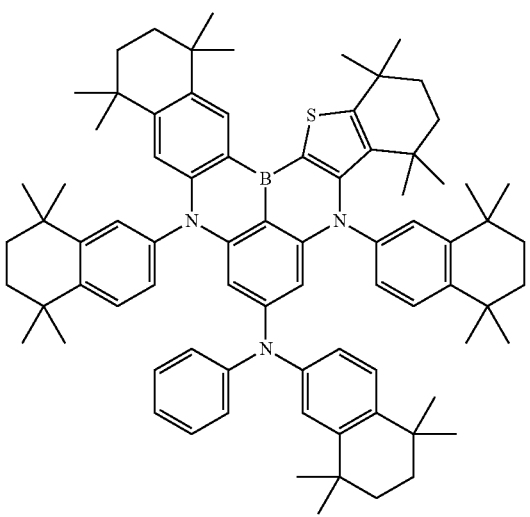

2415
-continued
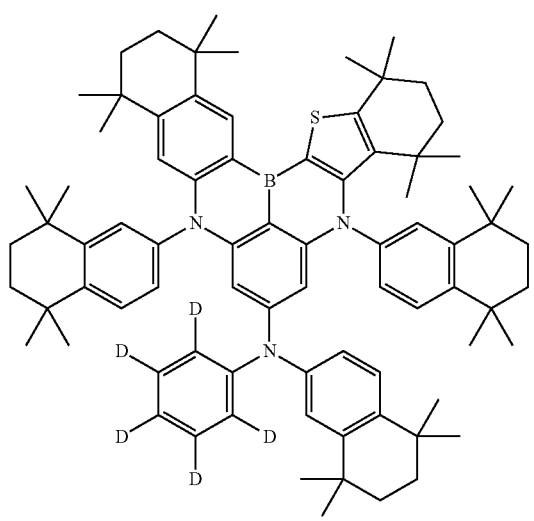
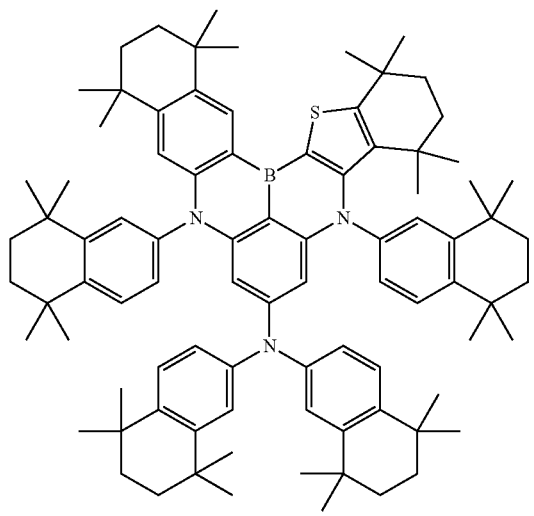
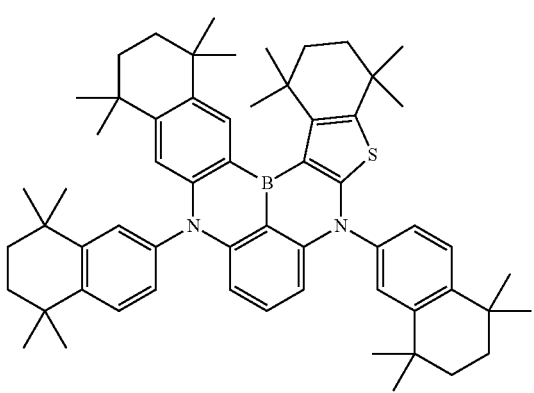
2416
-continued
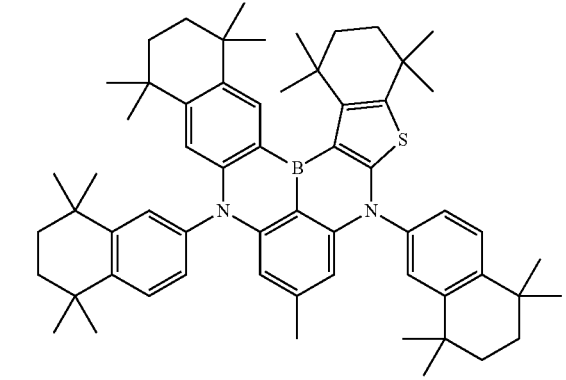
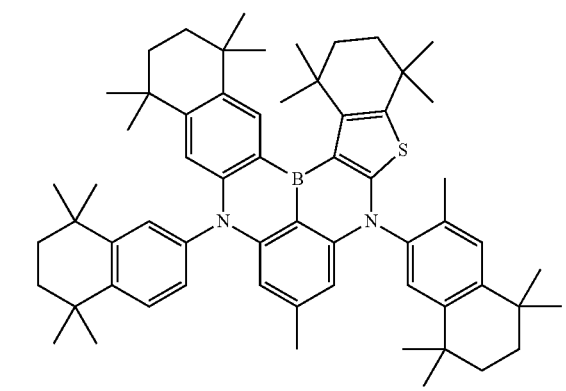

2417
-continued
2418
-continued
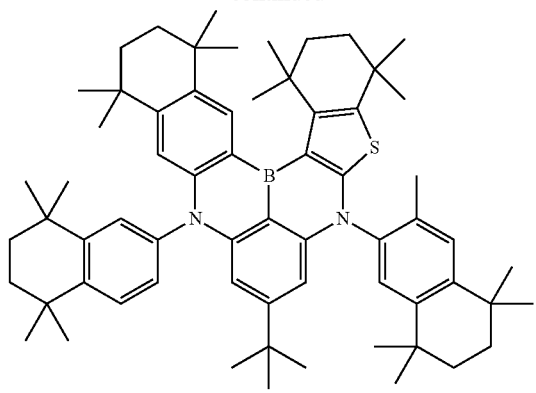
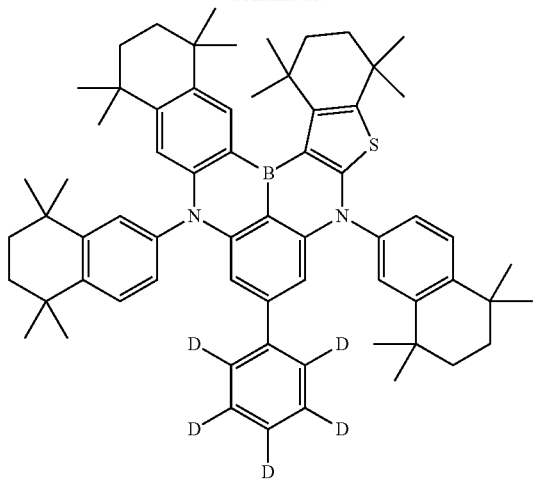
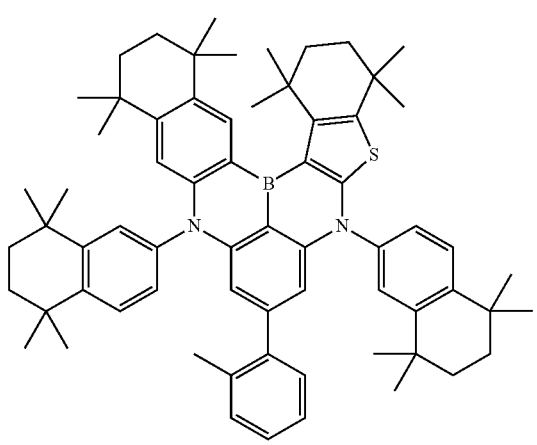
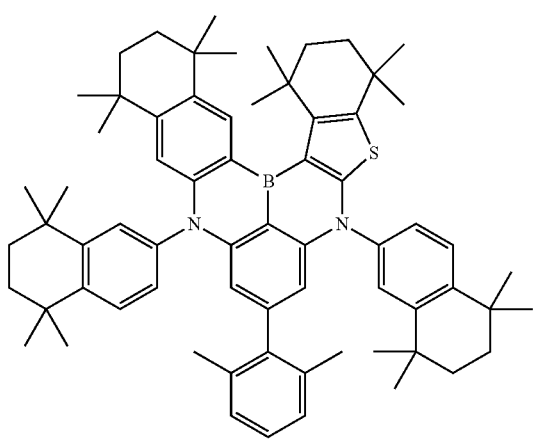

| 2419 -continued | 2420 -continued |
|---|---|
| 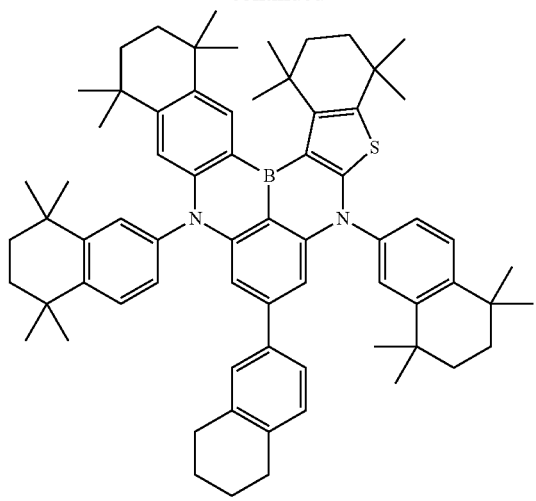 | 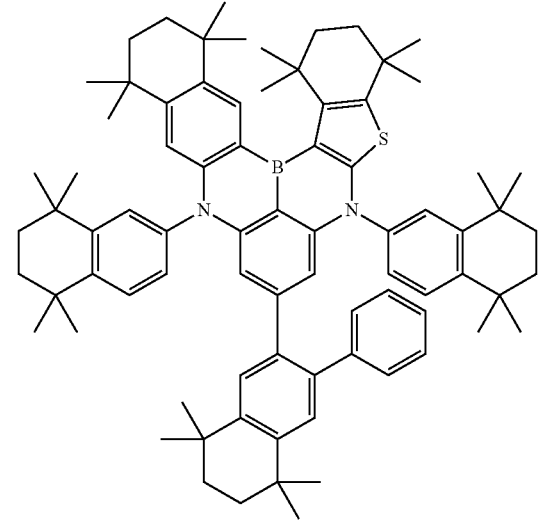 |
| 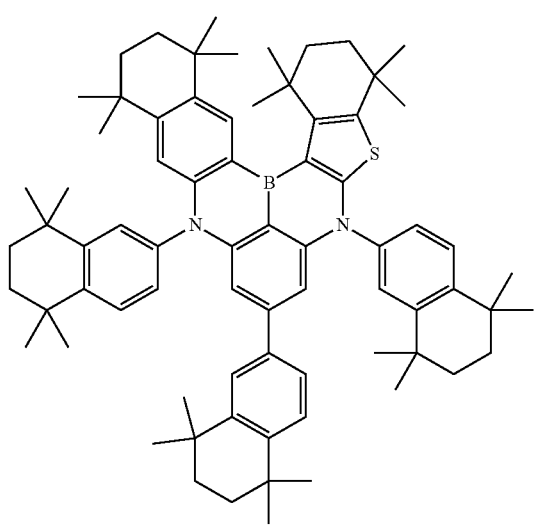 | 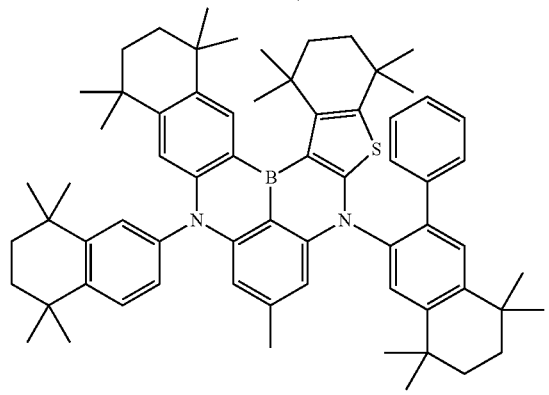 |
| | 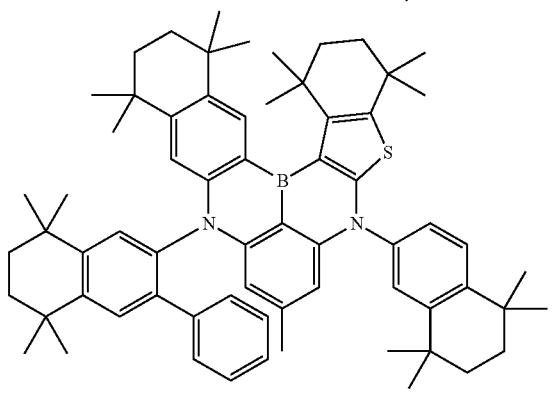 |
| 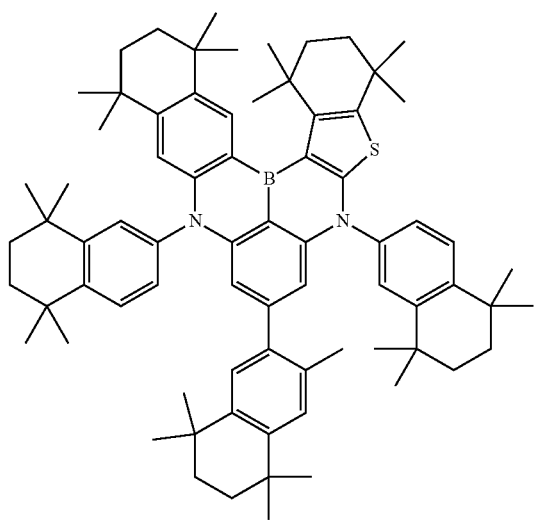 | 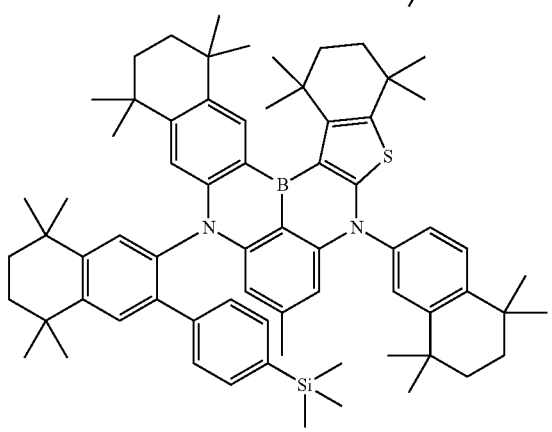 |

2421
-continued
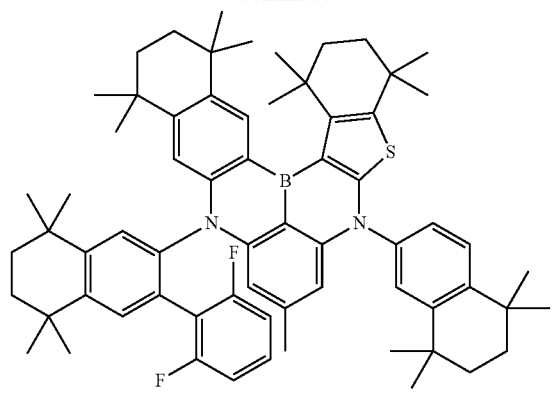
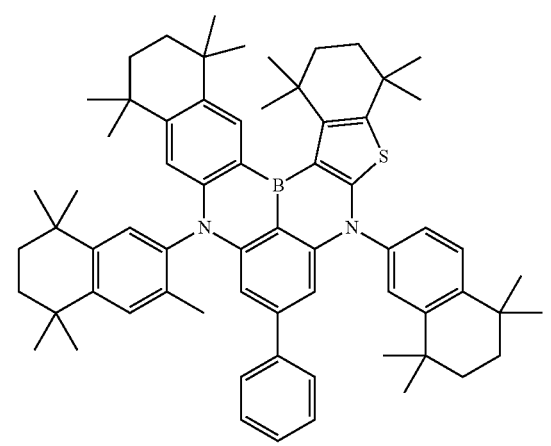
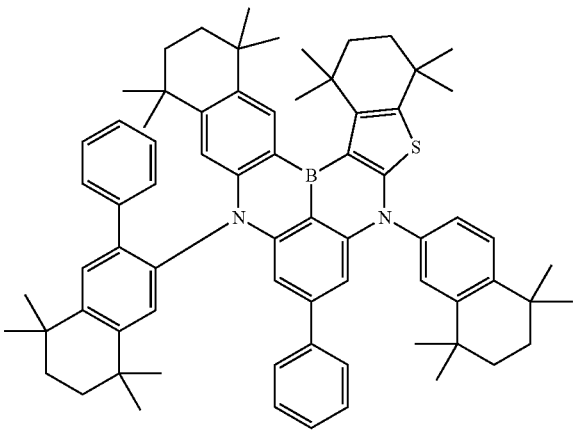
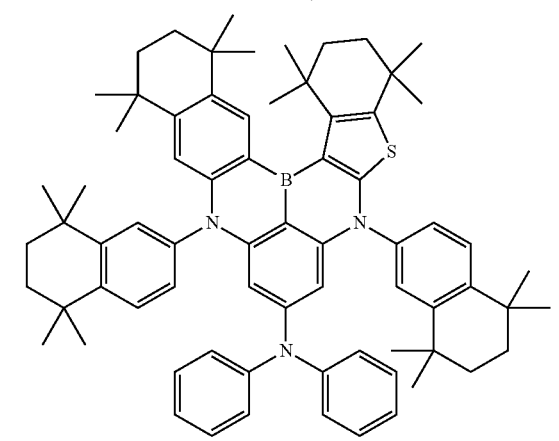
2422
-continued
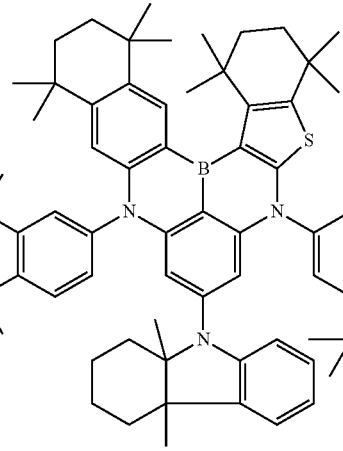
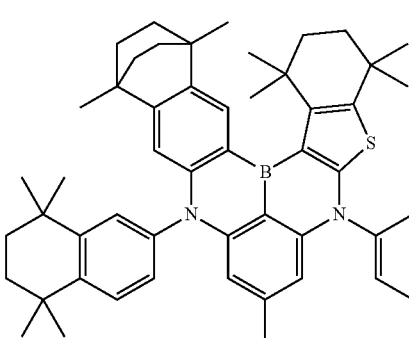
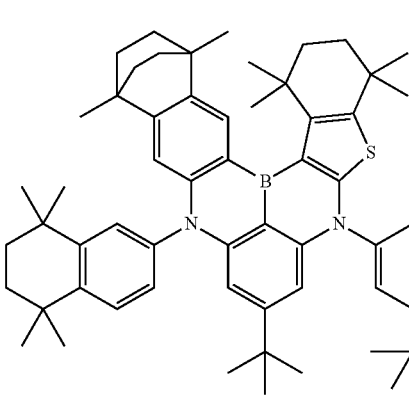
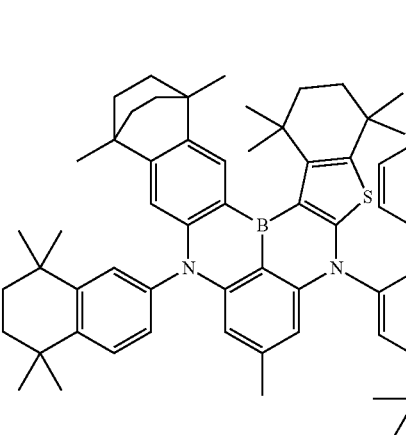

2423
-continued
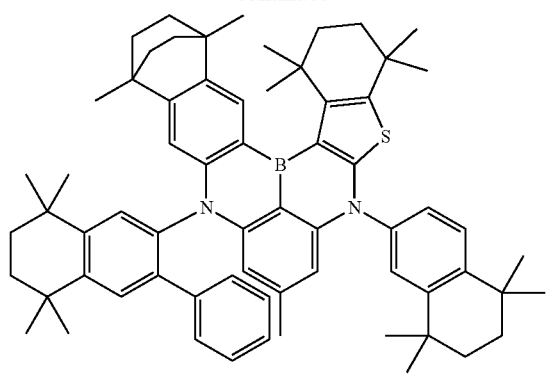
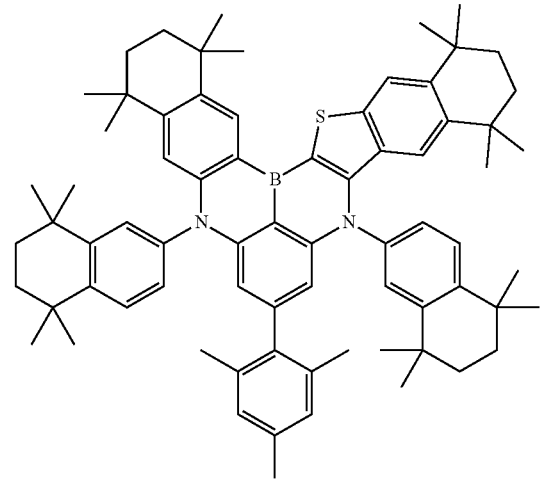
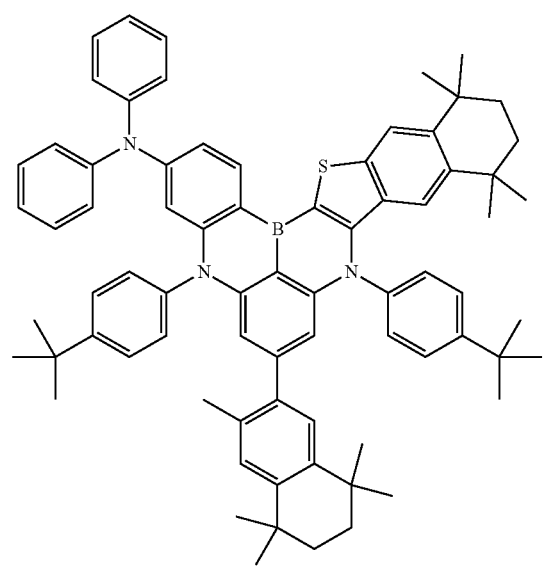
2424
-continued
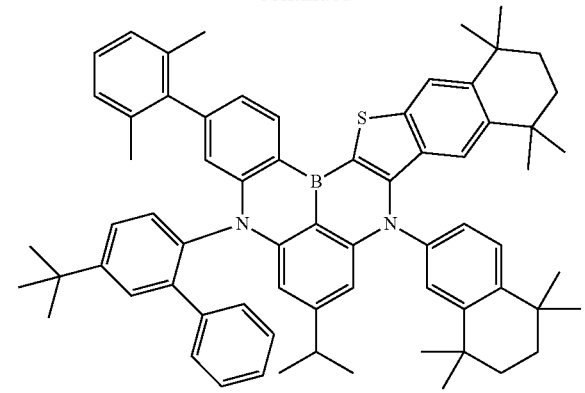
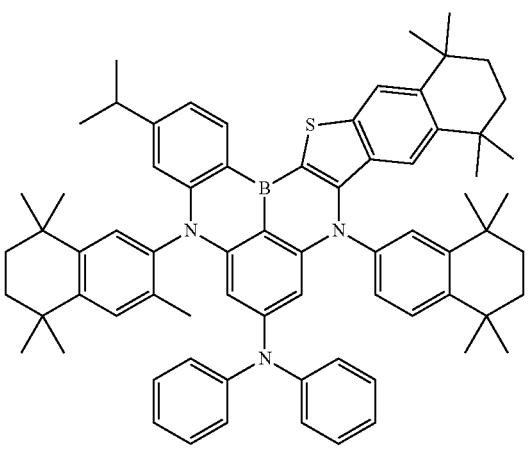
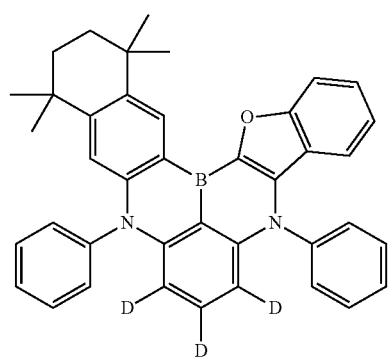
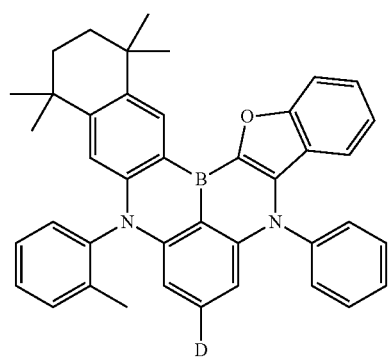

| 2425 -continued | 2426 -continued |
|---|---|
| 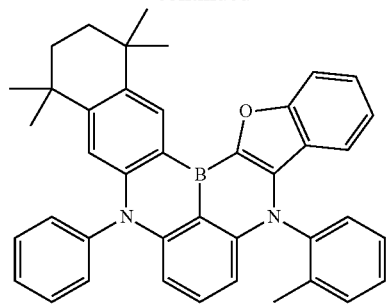 | 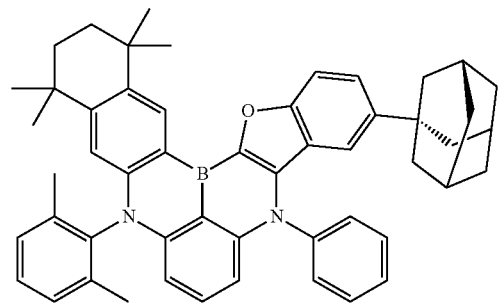 |
| 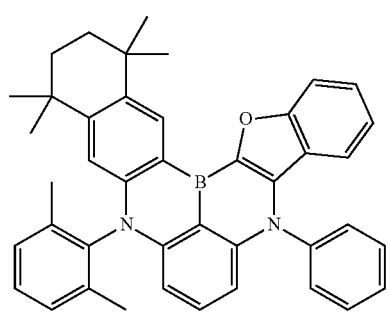 | 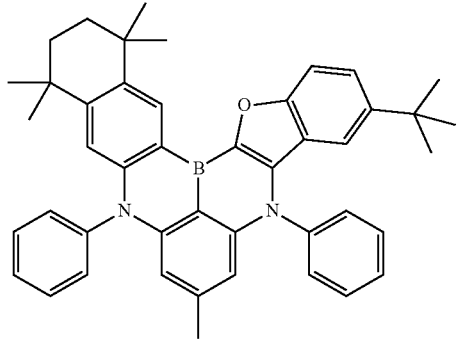 |
| 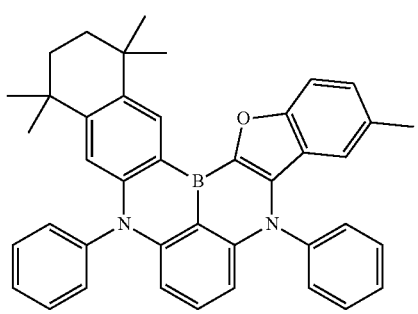 | 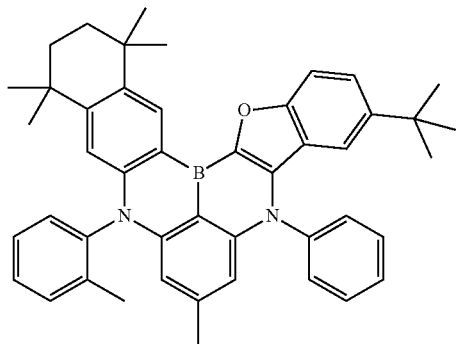 |
| 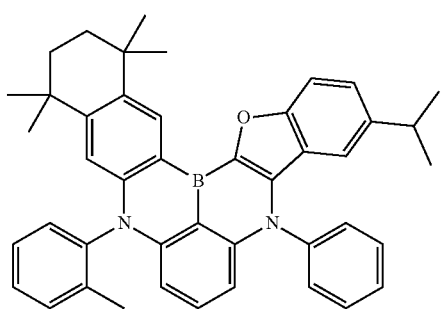 | 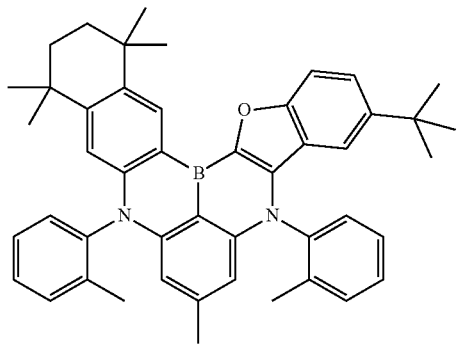 |
| 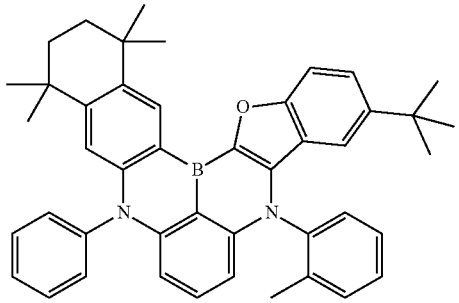 | 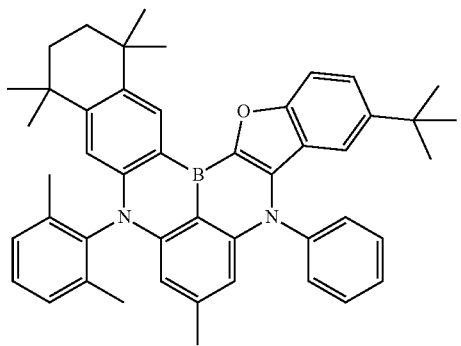 |

| 2427 -continued | 2428 -continued |
|---|---|
| 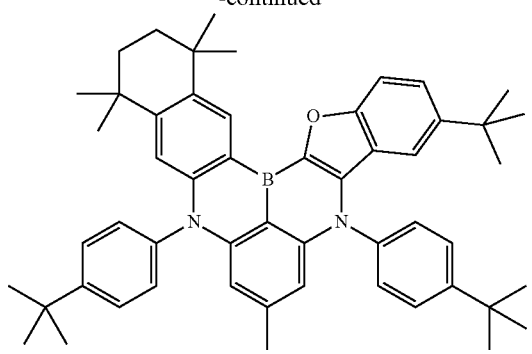 | 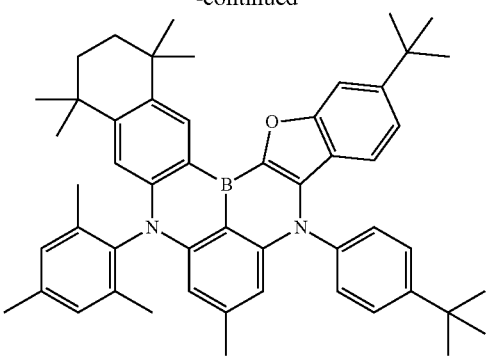 |
| 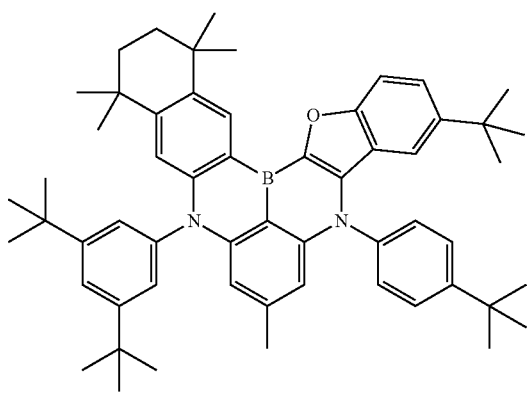 | 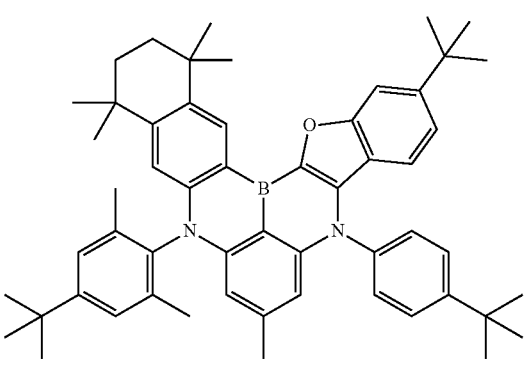 |
| 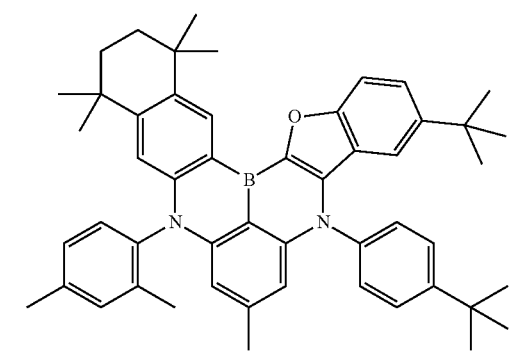 | 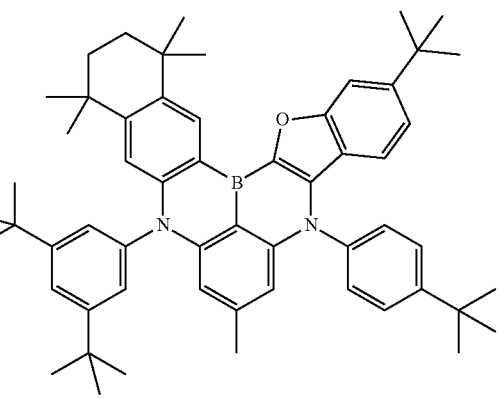 |
| 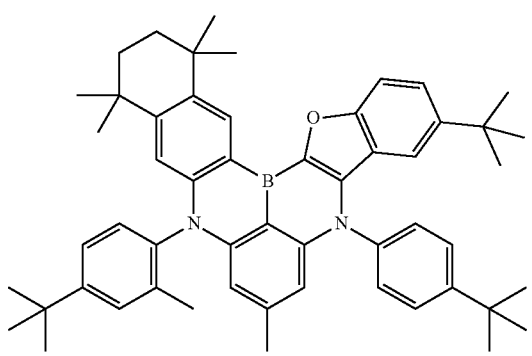 | 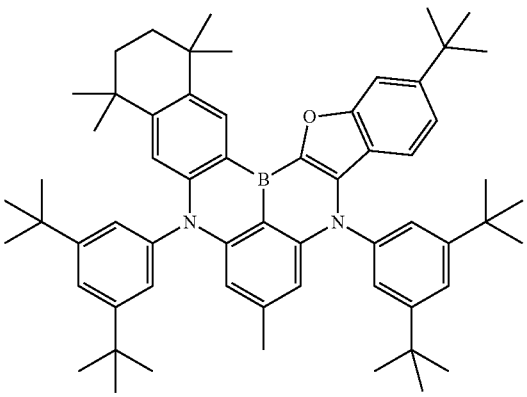 |

2429
-continued
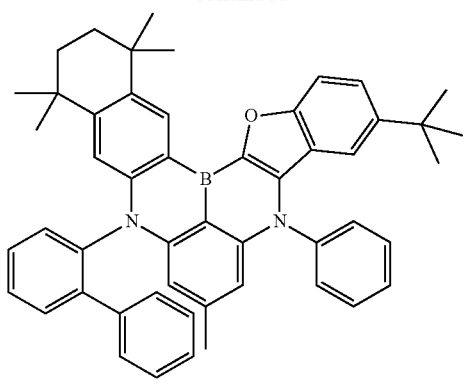
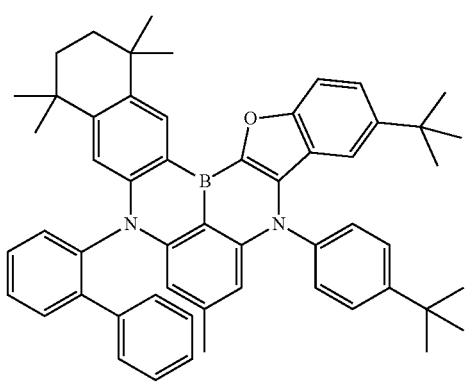
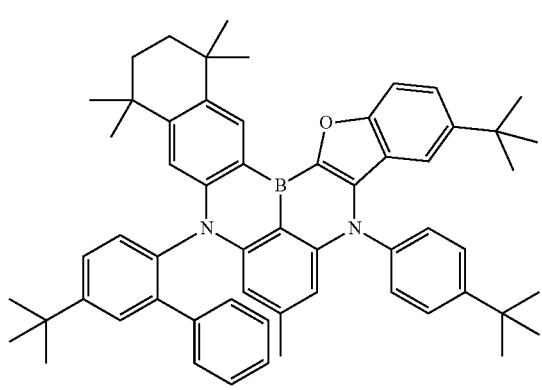
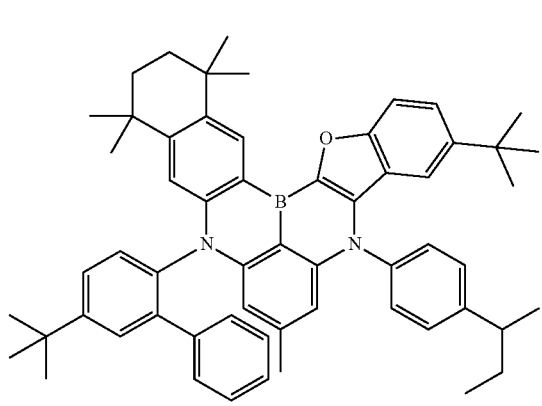
2430
-continued
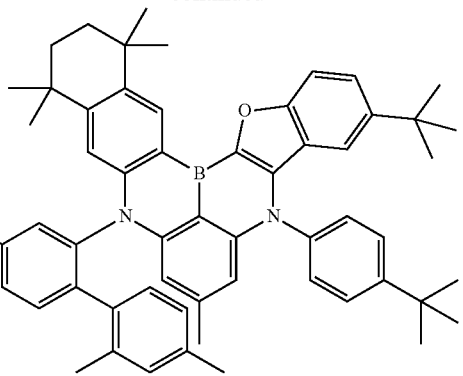
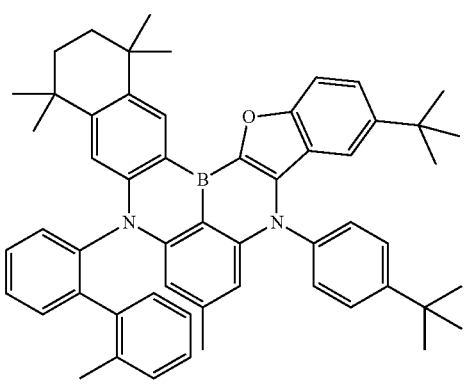
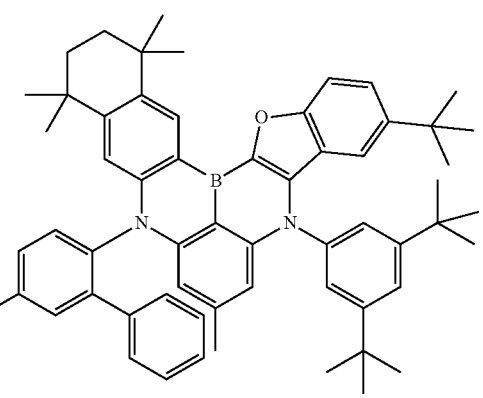
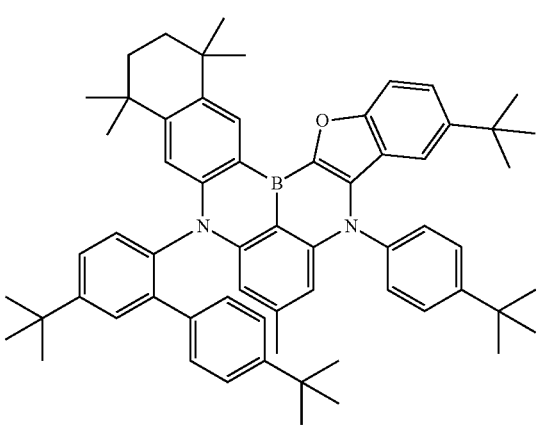

| 2431 -continued | 2432 -continued |
|---|---|
| 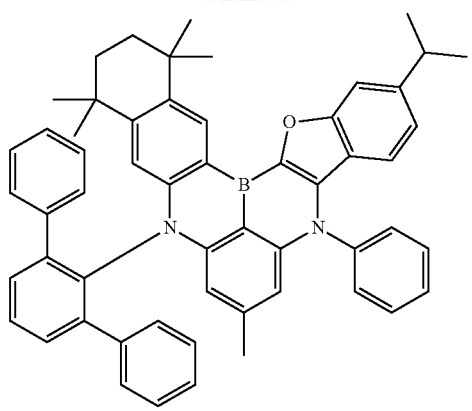 | 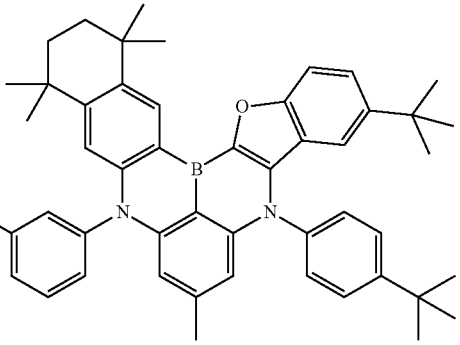 |
| 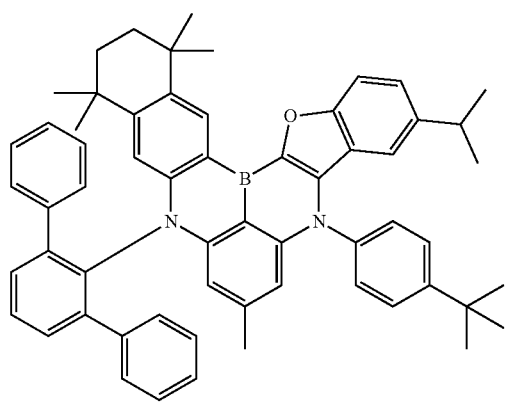 | 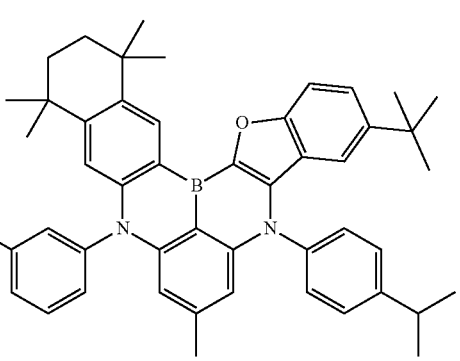 |
| 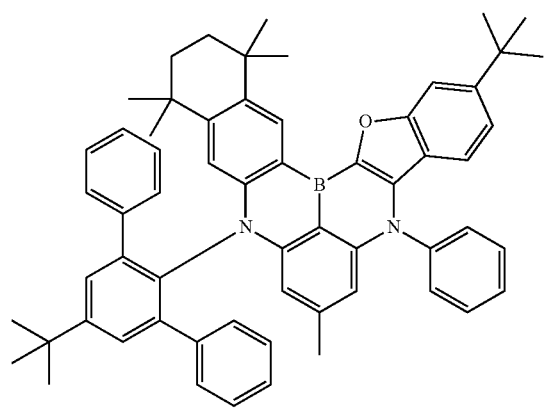 | 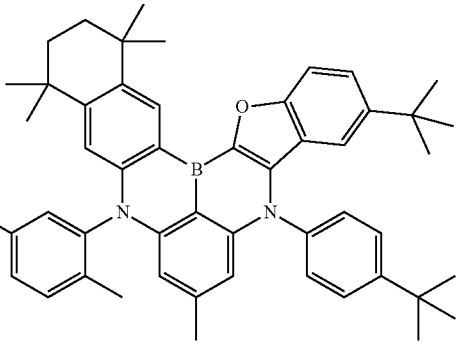 |
| 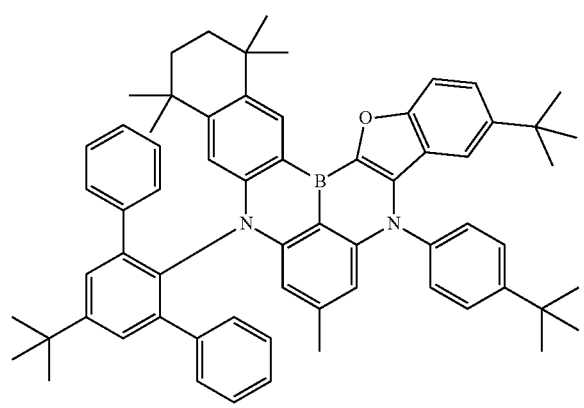 | 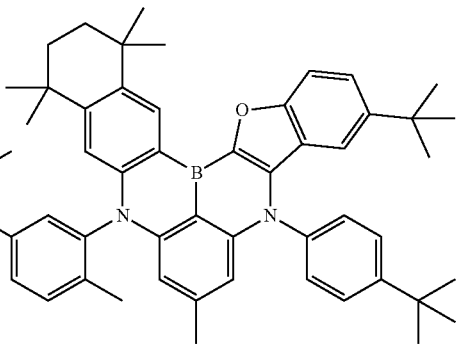 |

2433
-continued
2434
-continued
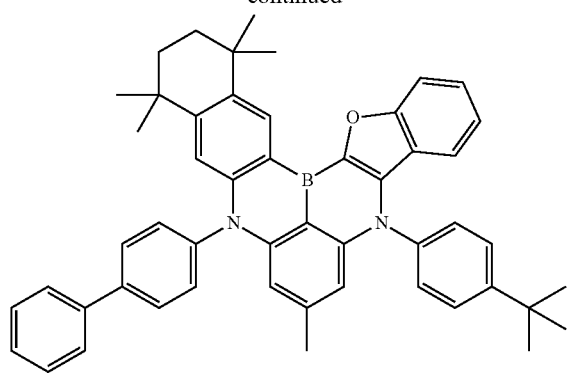
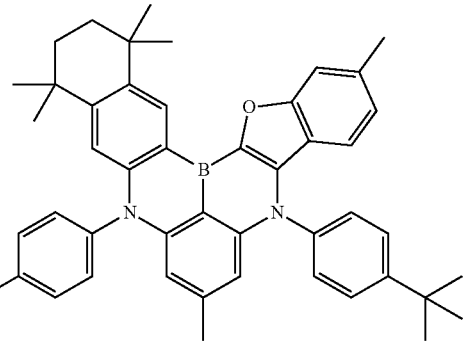
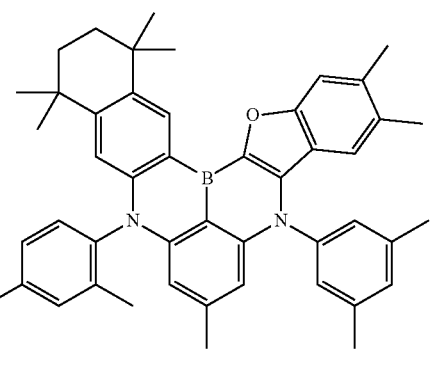
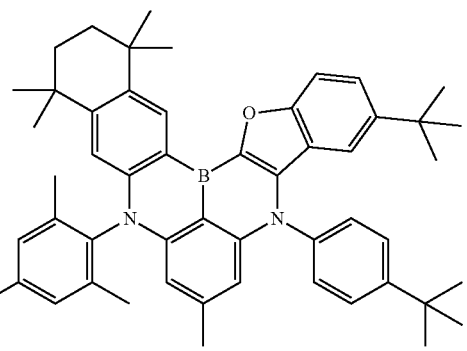
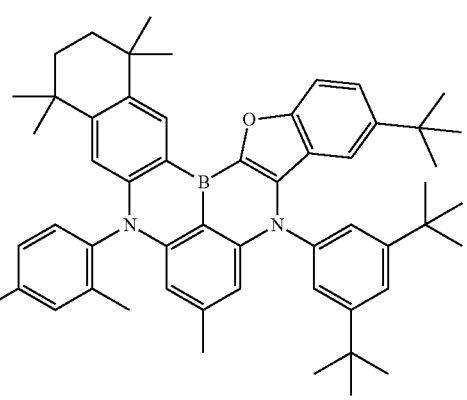

2435
-continued
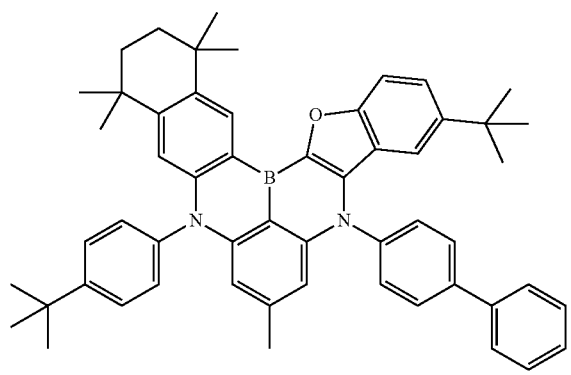
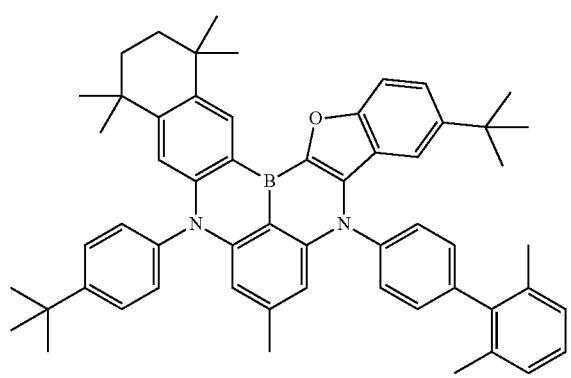
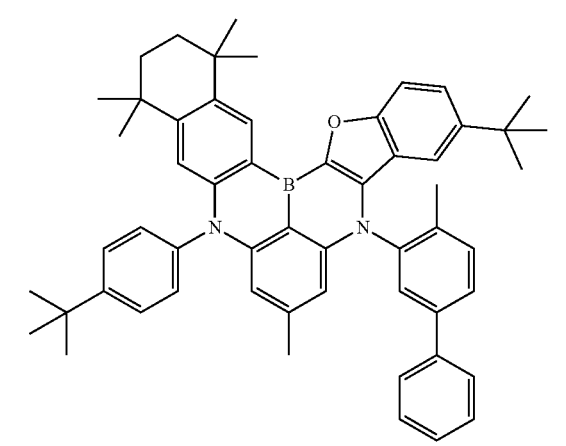
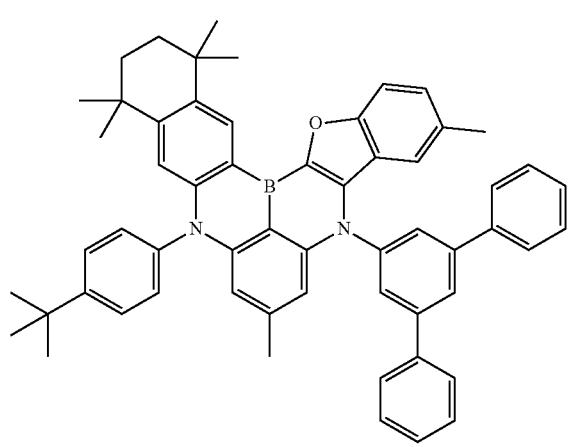
2436
-continued
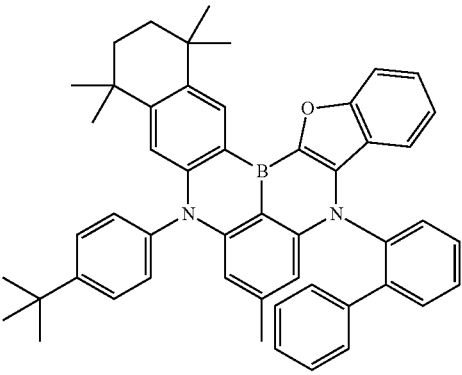
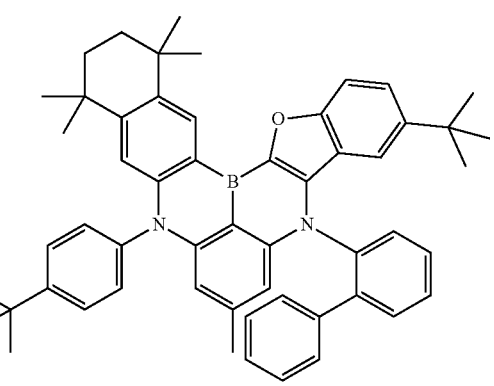
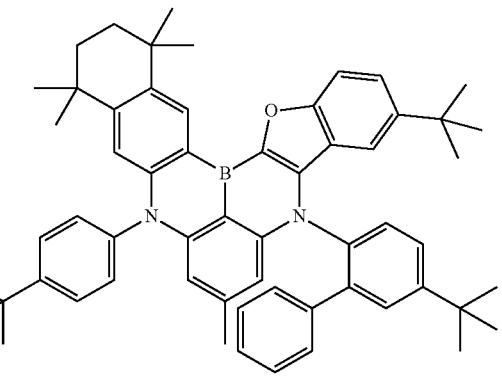
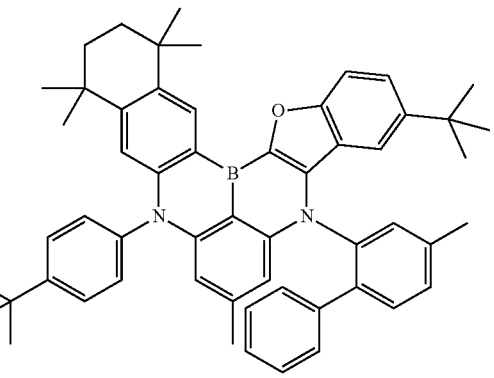

2437
-continued
2438
-continued
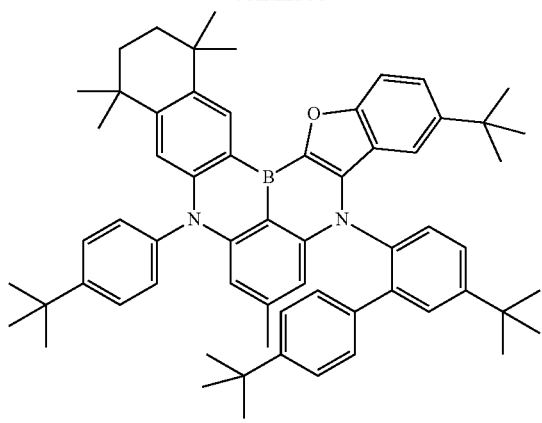
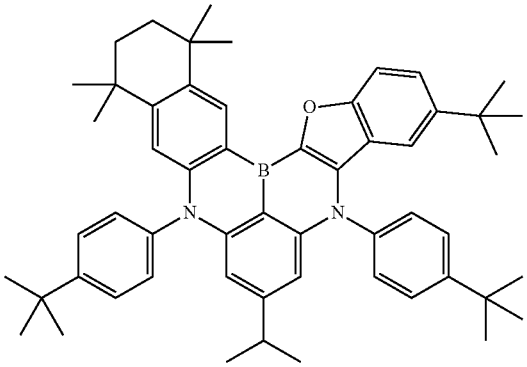
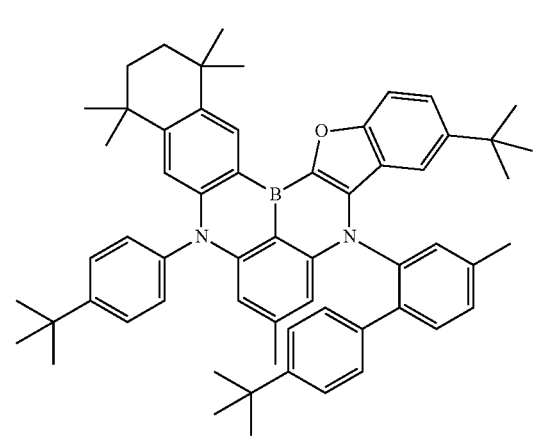
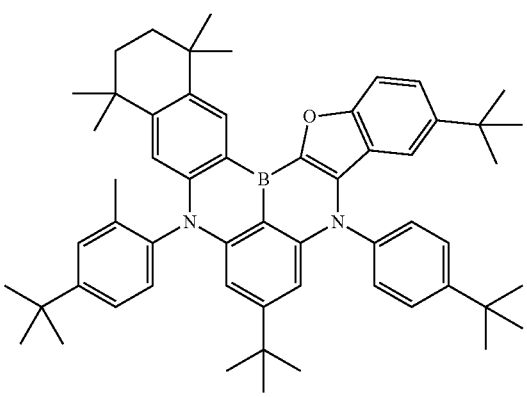
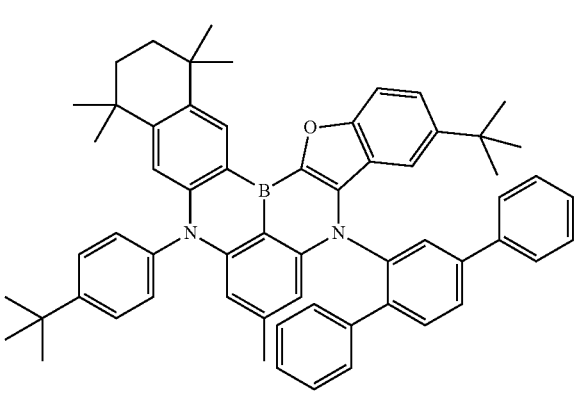
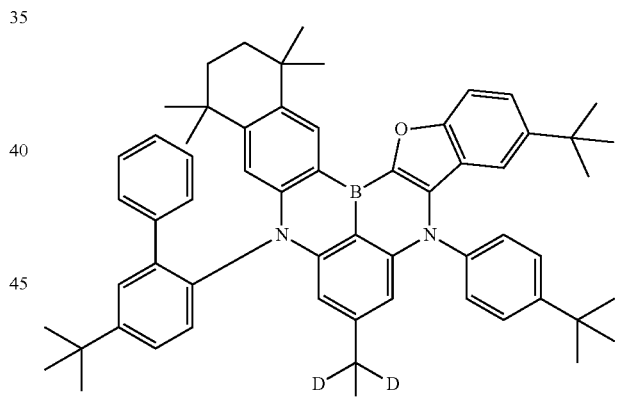
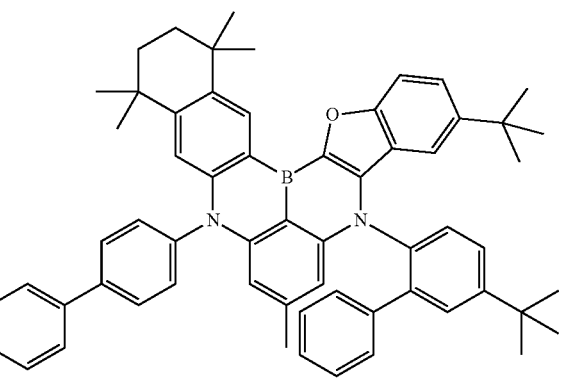
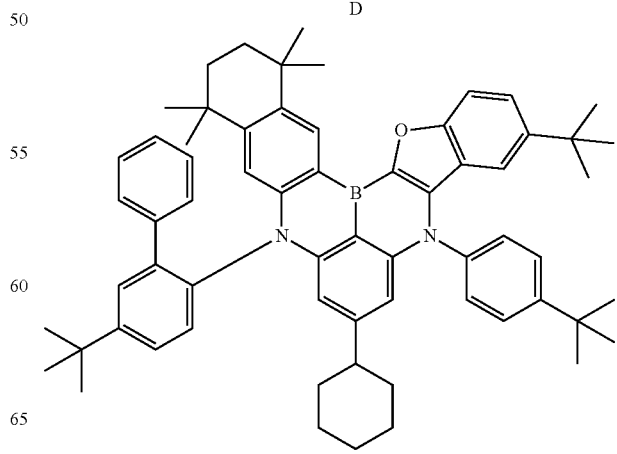

2439
-continued
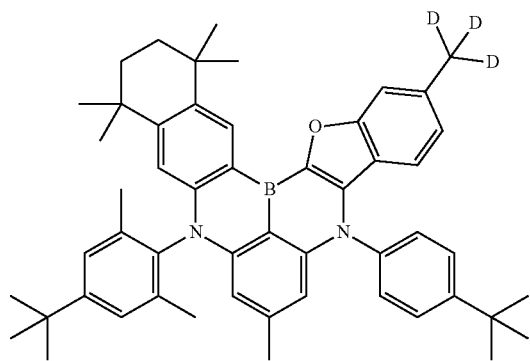
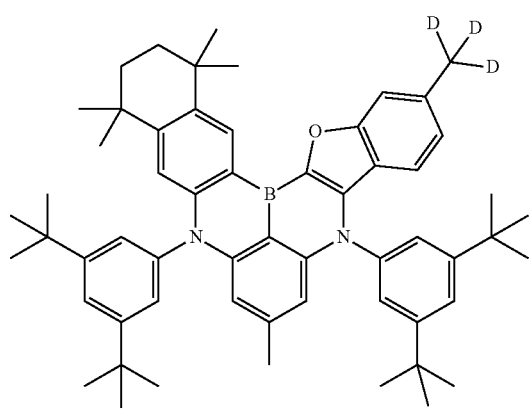
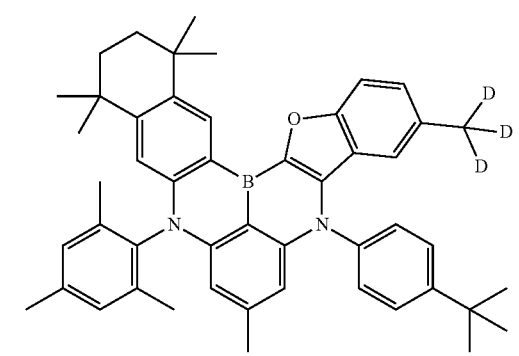
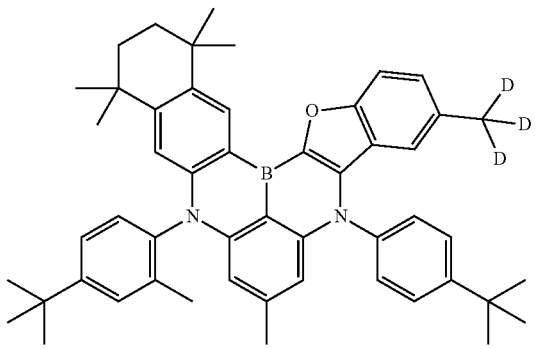
2440
-continued
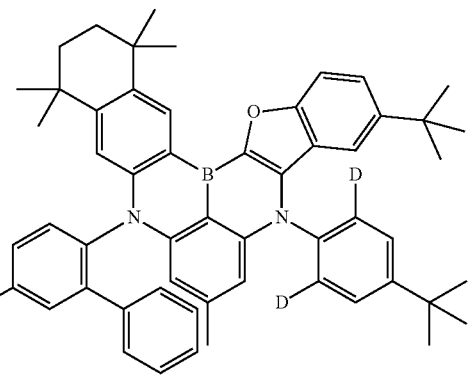
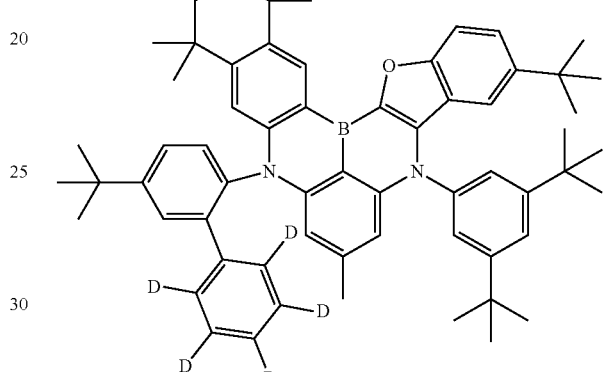
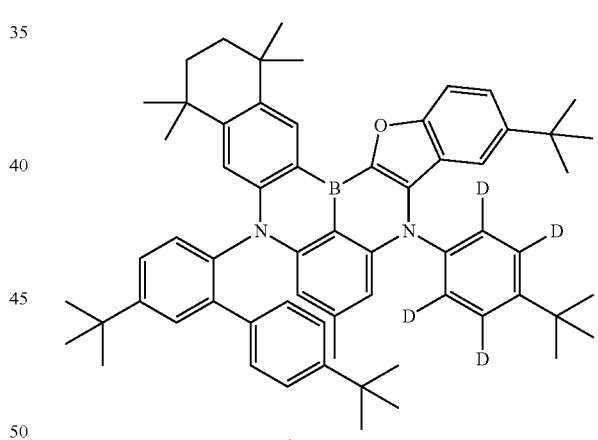
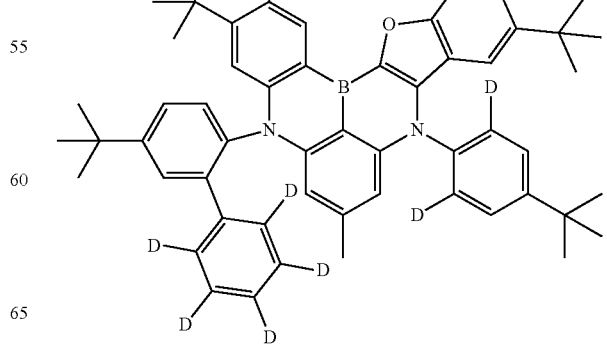

2441
-continued
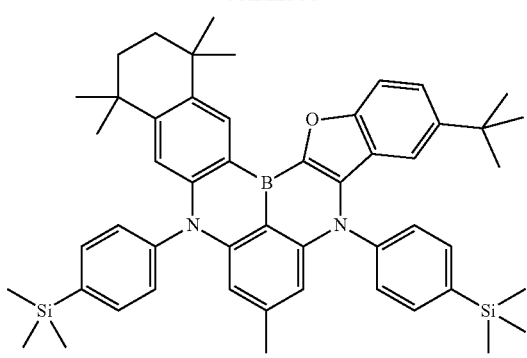
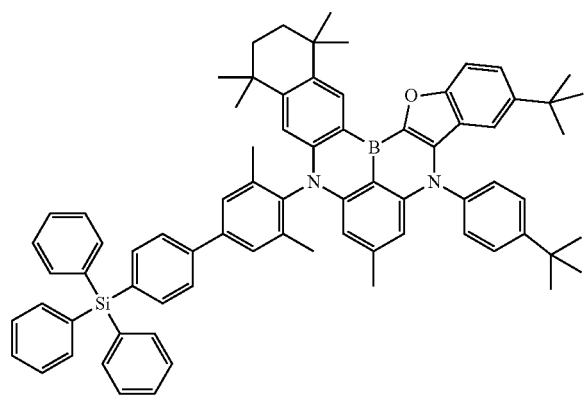
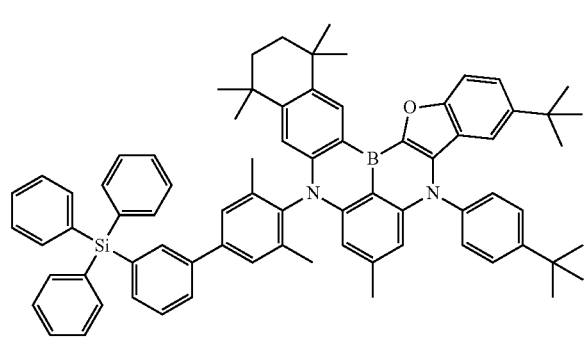
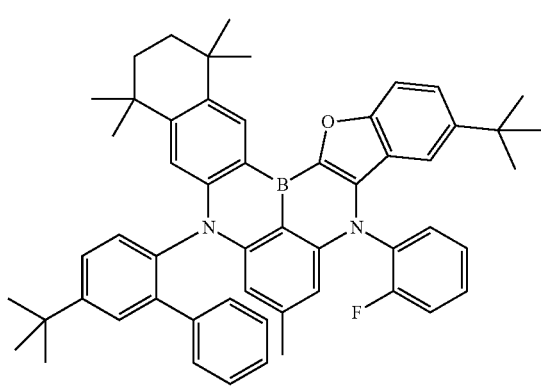
2442
-continued
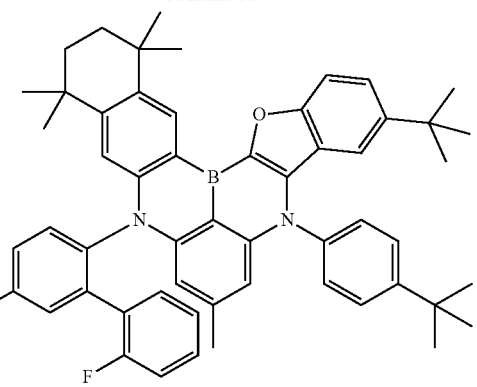
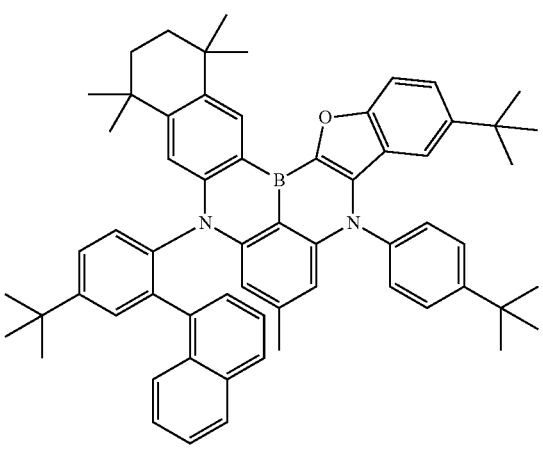
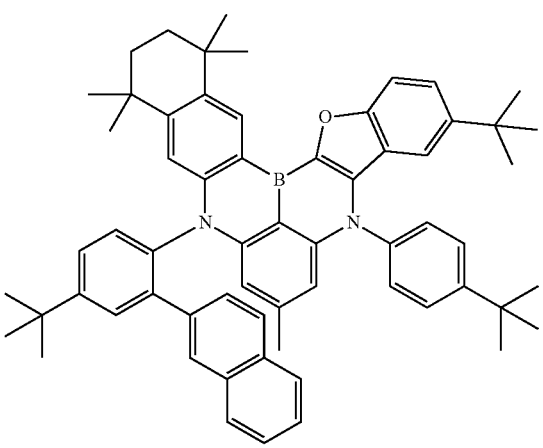
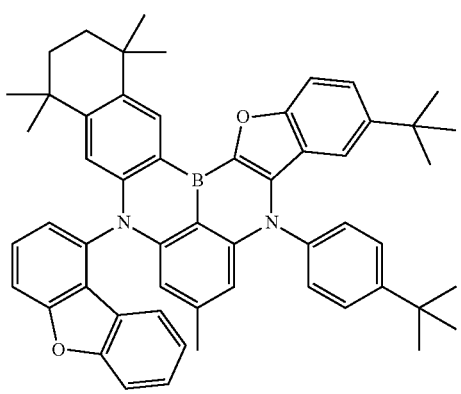

2443
-continued
2444
-continued
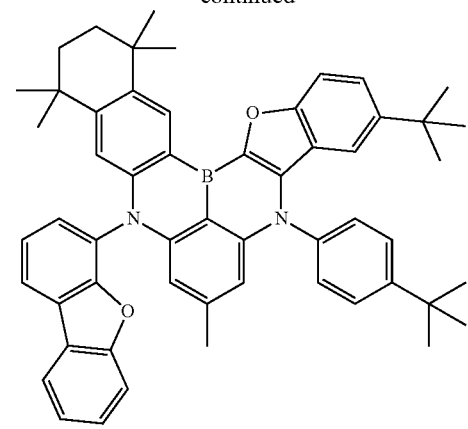
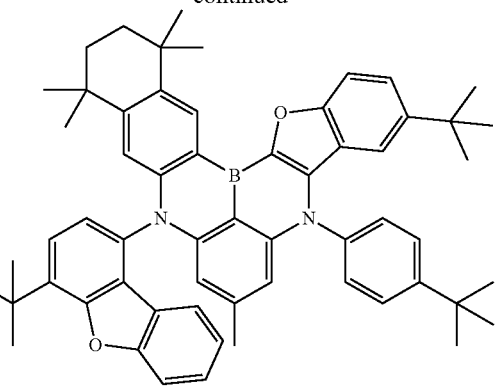
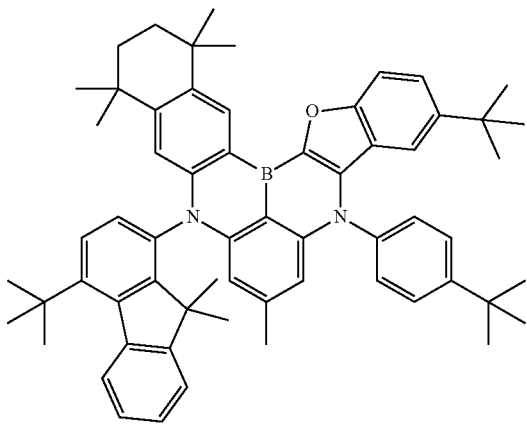
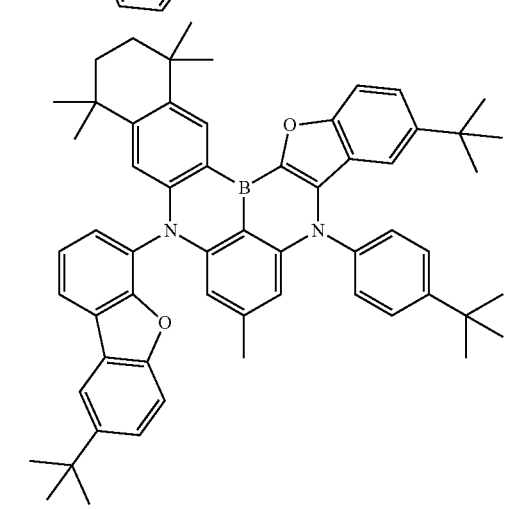

2445
-continued
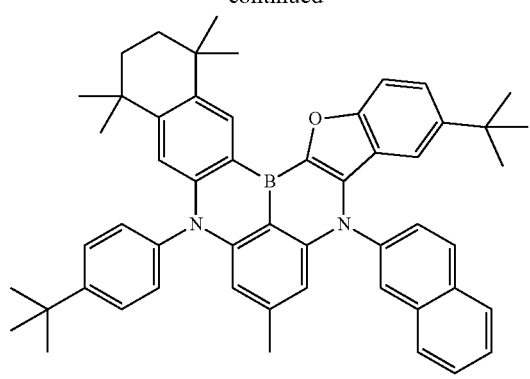
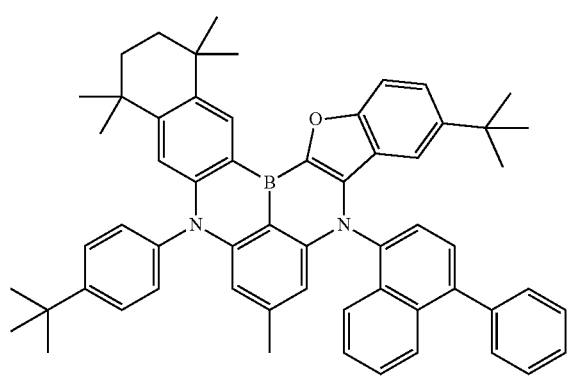
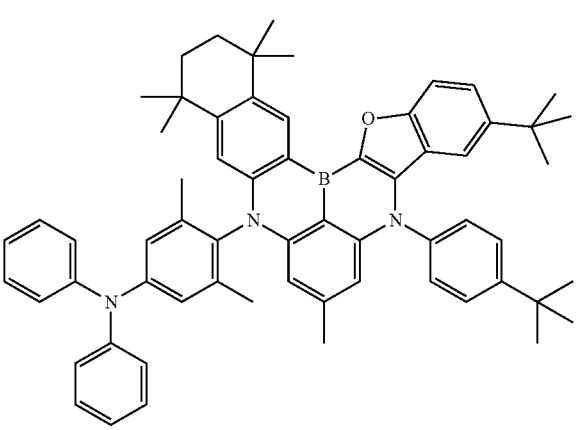
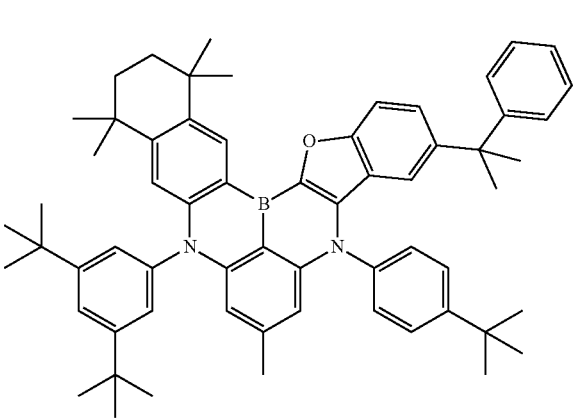
2446
-continued
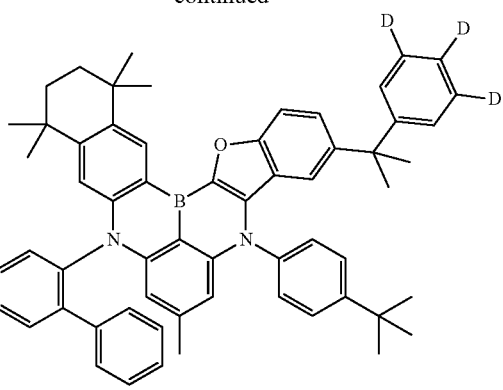
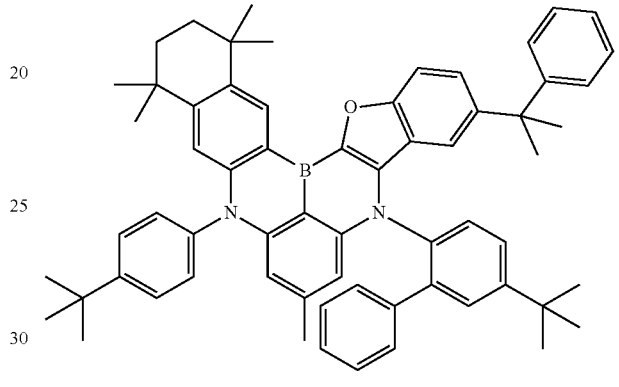
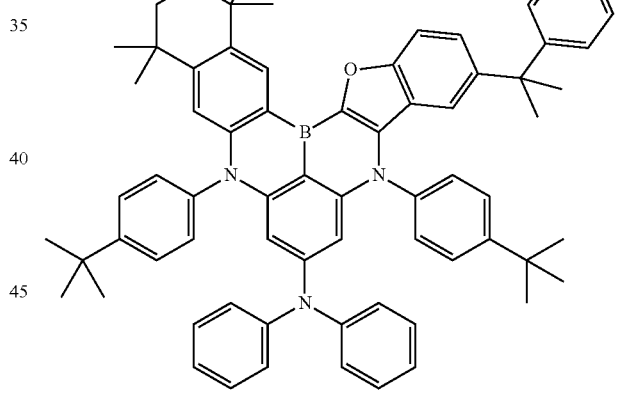
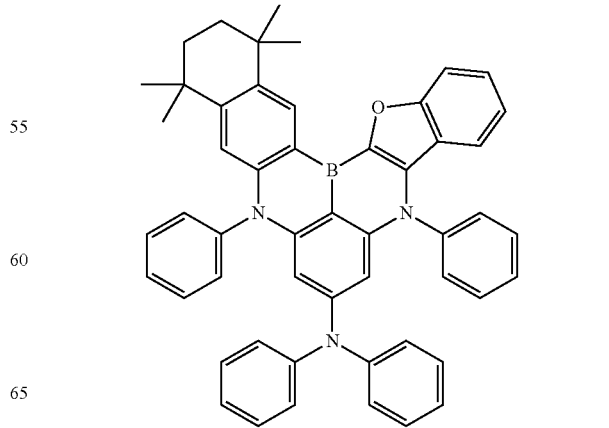

2447
-continued
2448
-continued
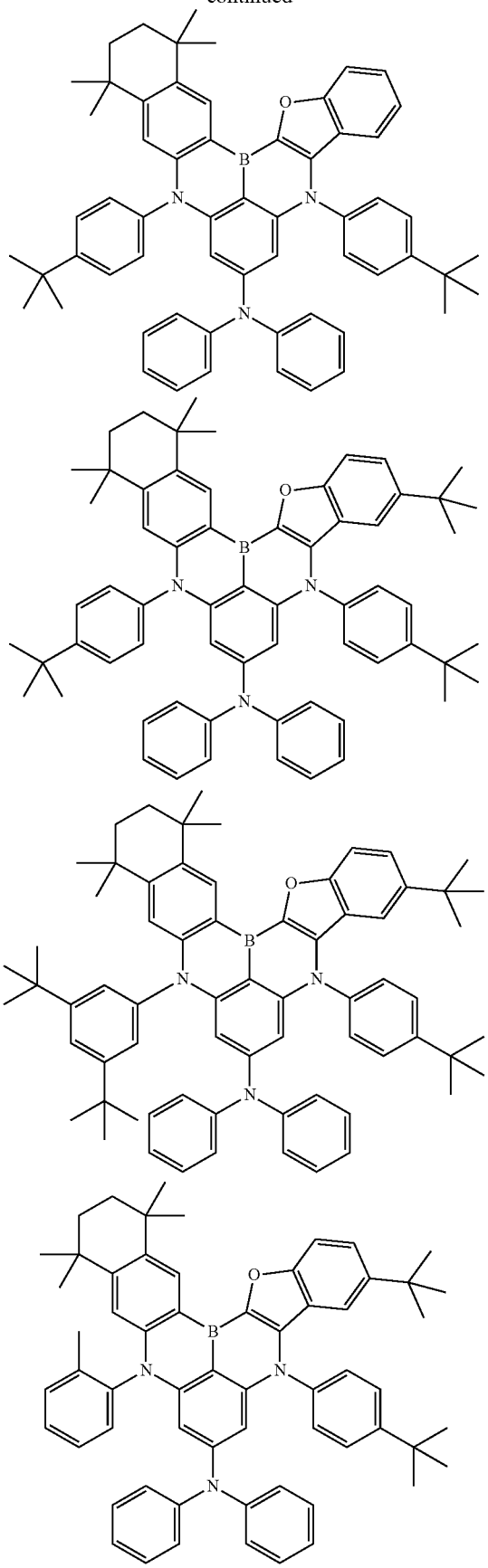
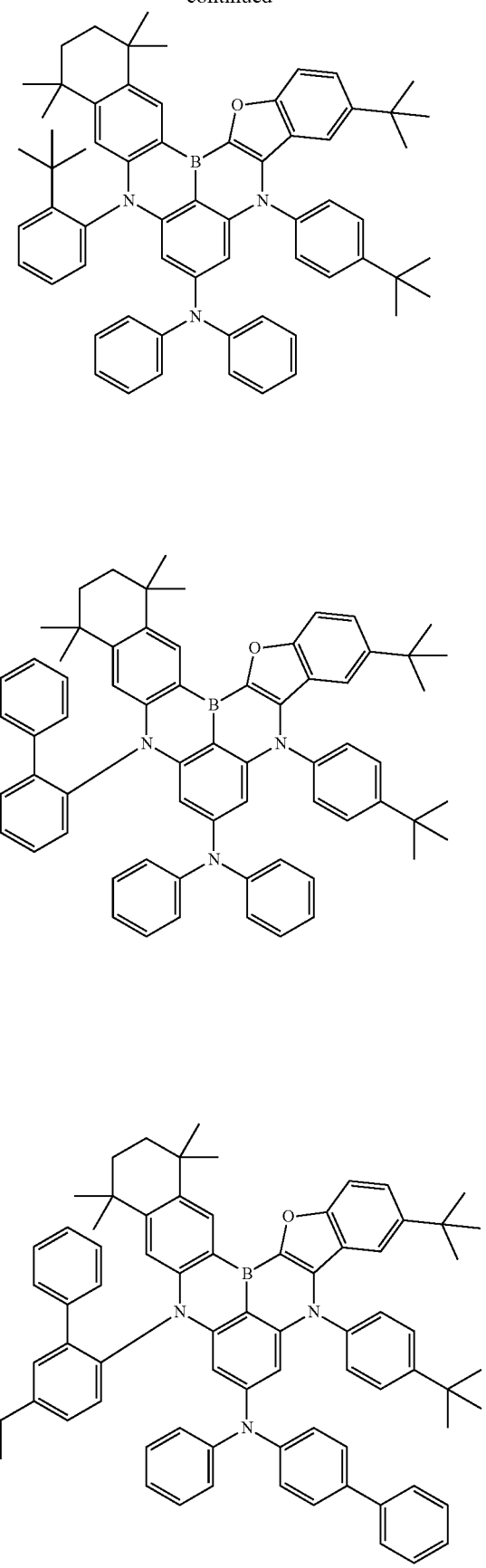

2449
-continued
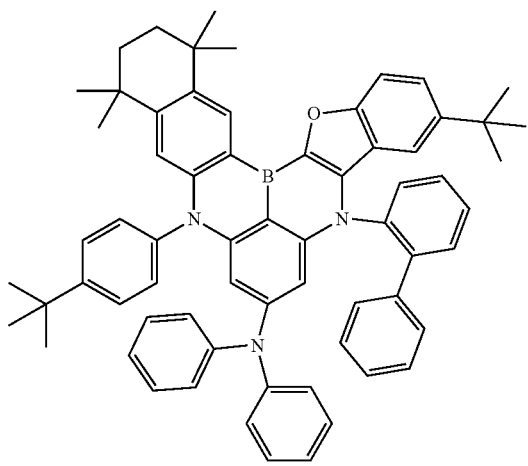
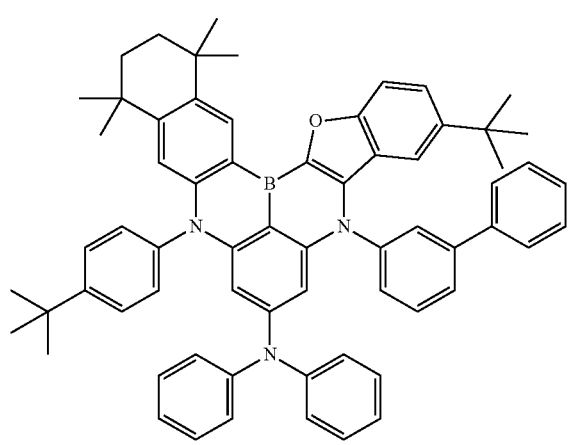
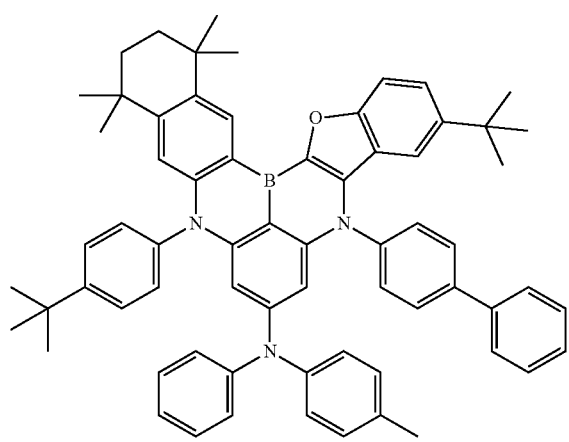
2450
-continued
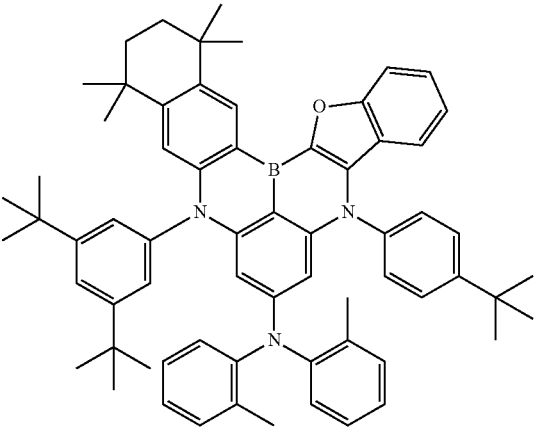
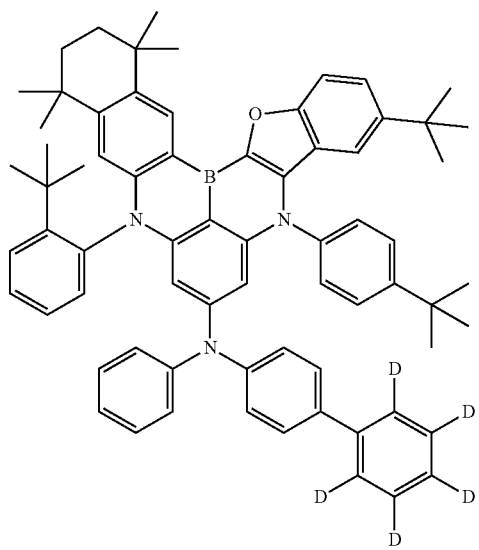
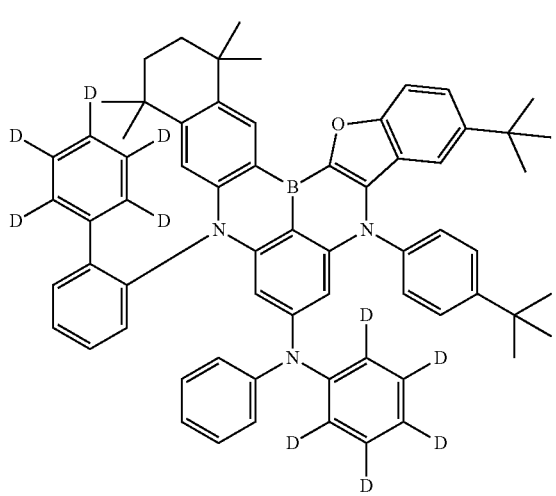

2451
-continued
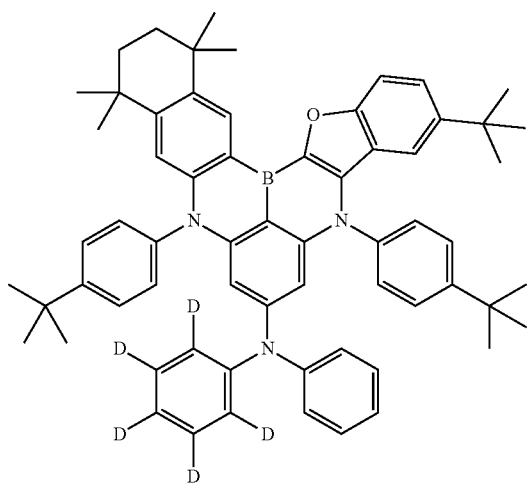
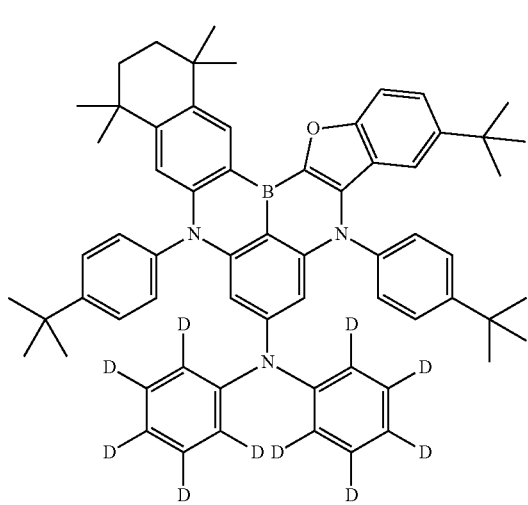
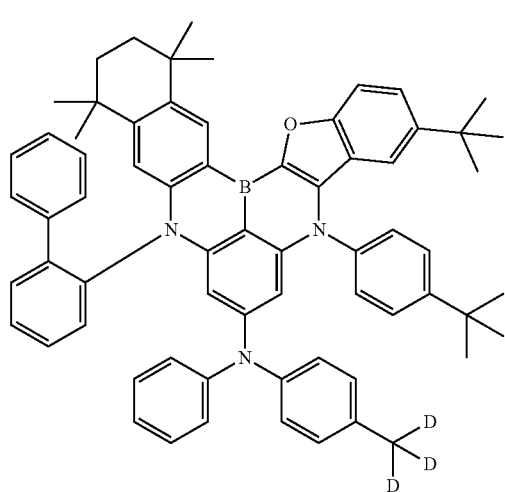
2452
-continued
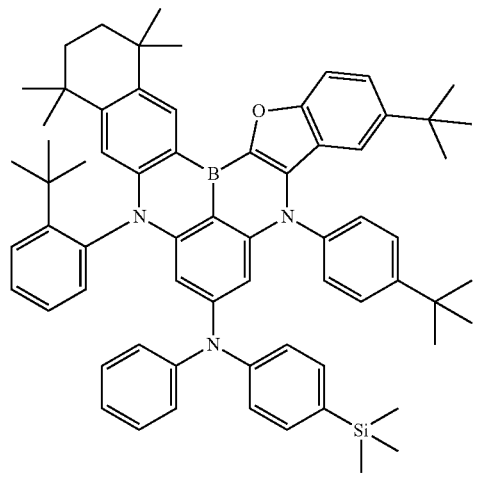
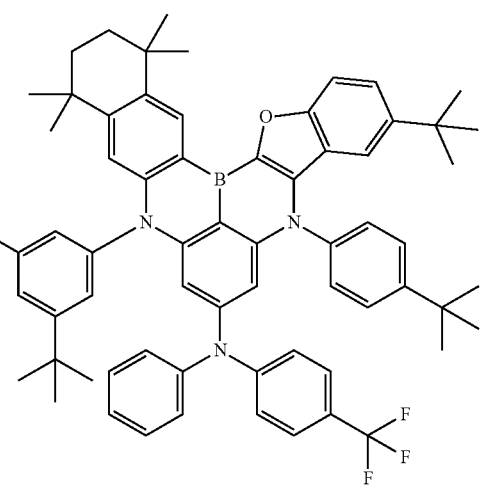
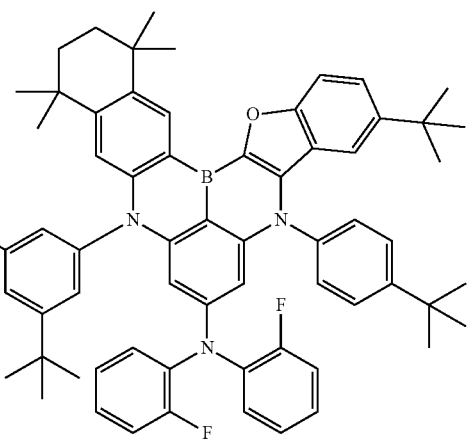

2453
-continued
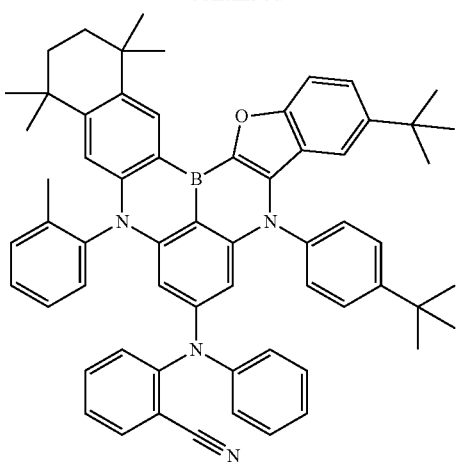
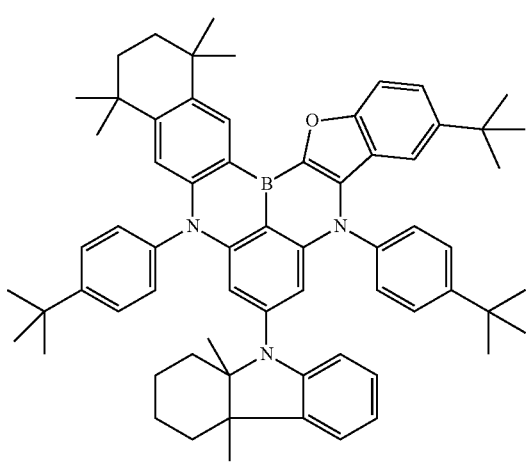
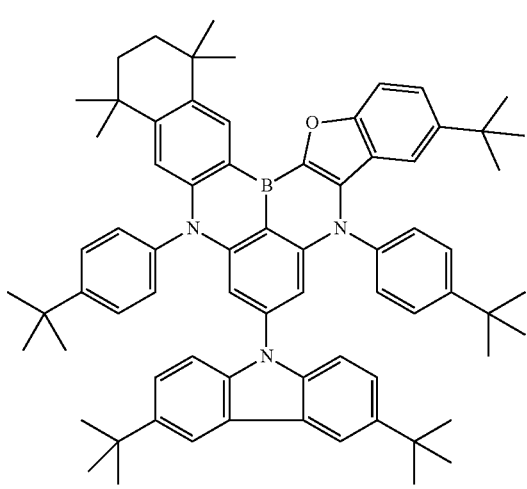
2454
-continued
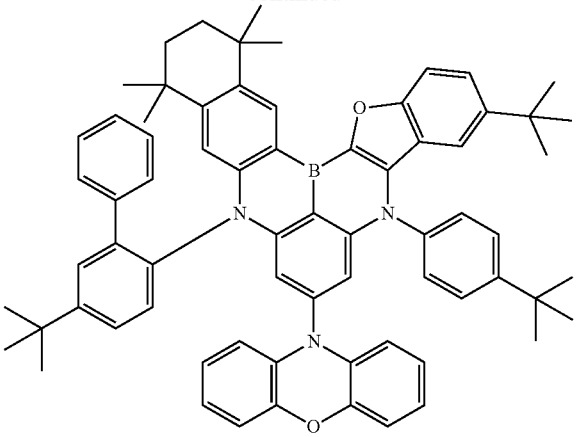
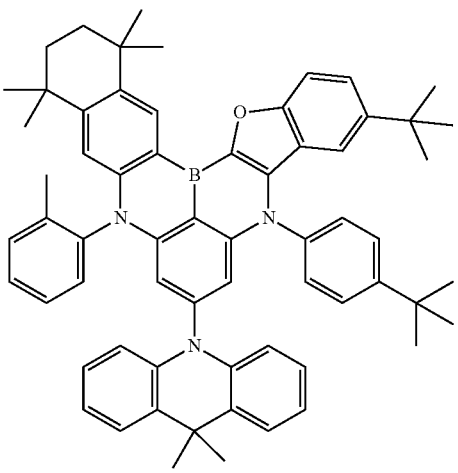
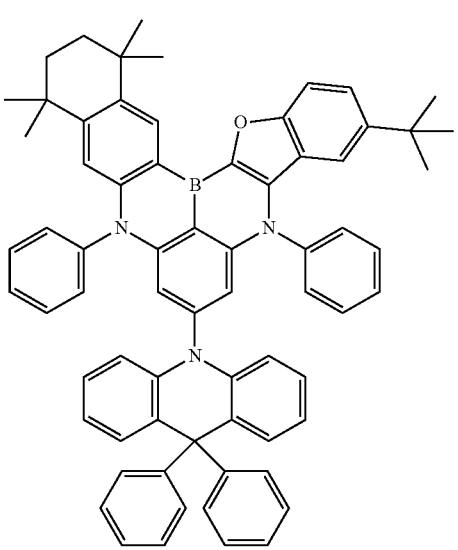

2455
-continued
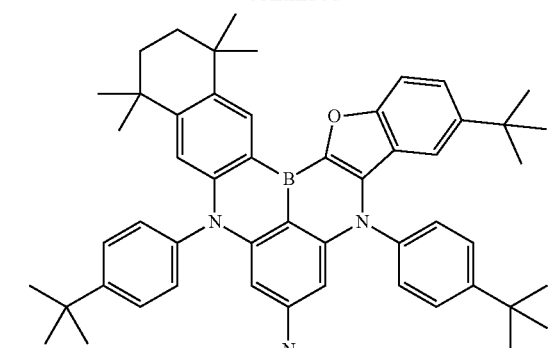
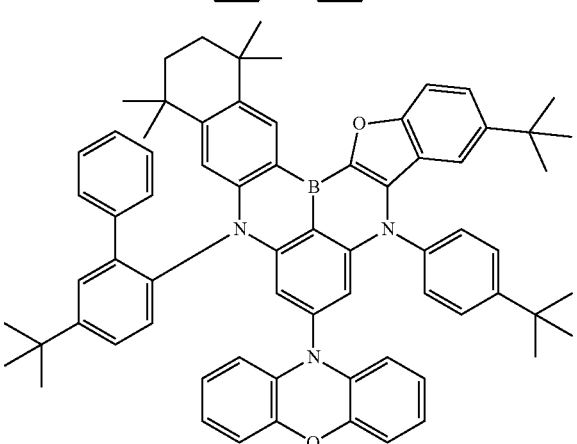
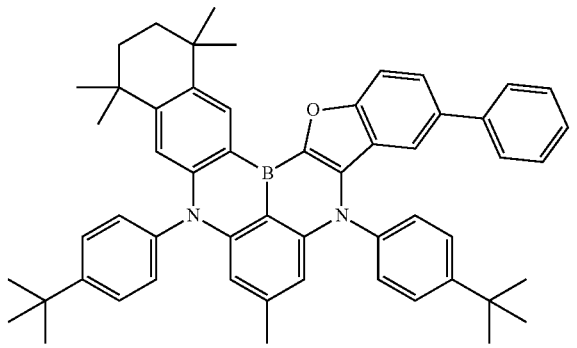
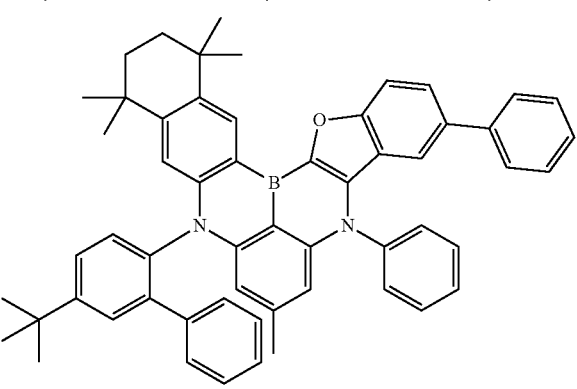
2456
-continued
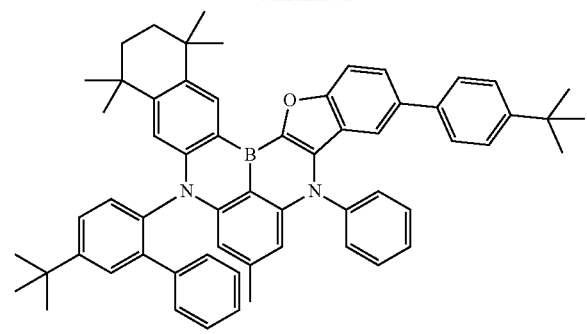
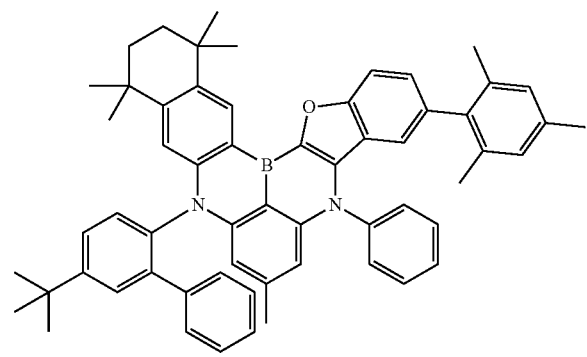
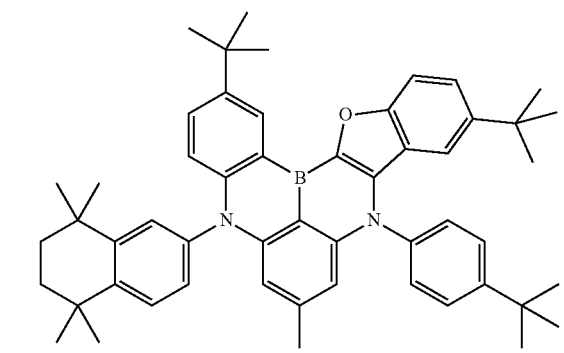
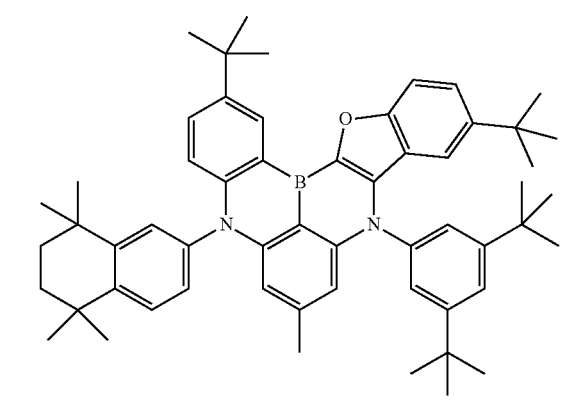

| 2457 -continued | 2458 -continued |
|---|---|
| 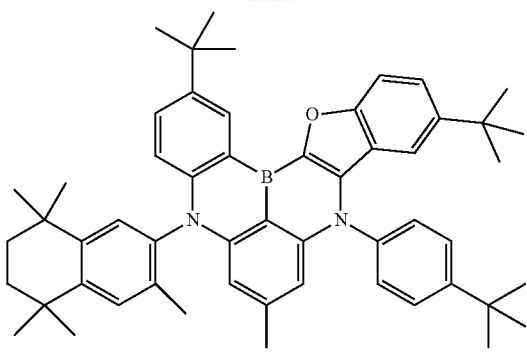 | 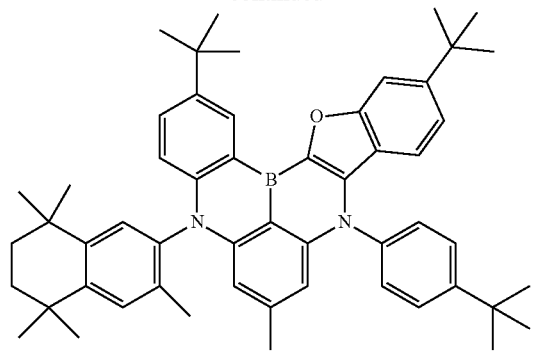 |
| 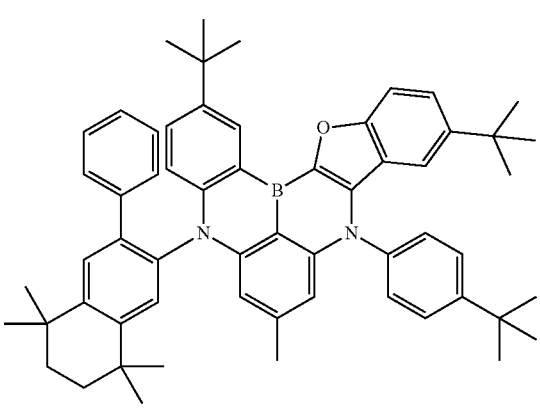 | 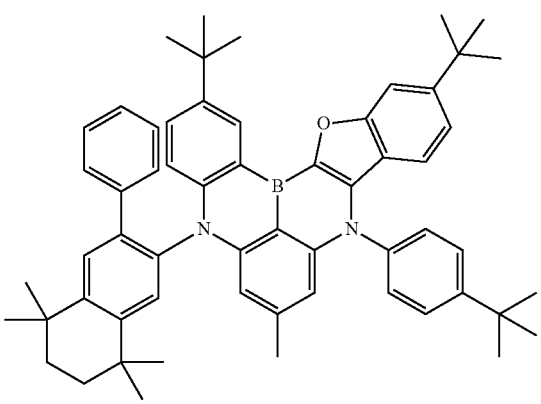 |
| 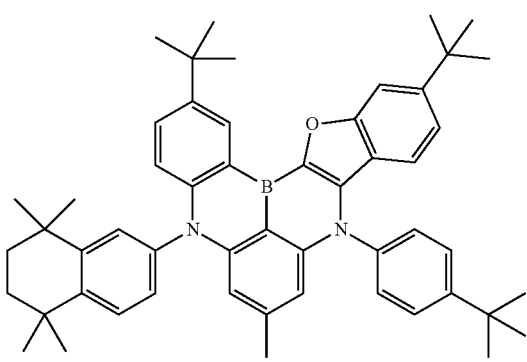 | 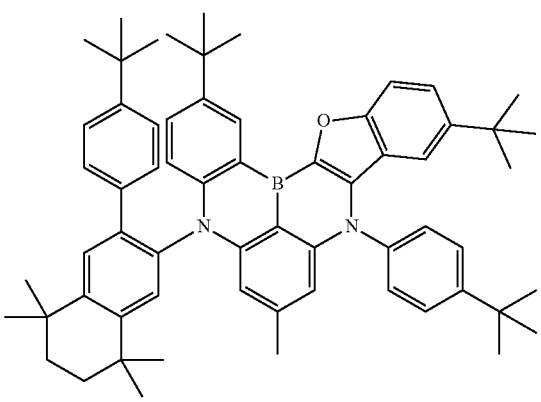 |
| 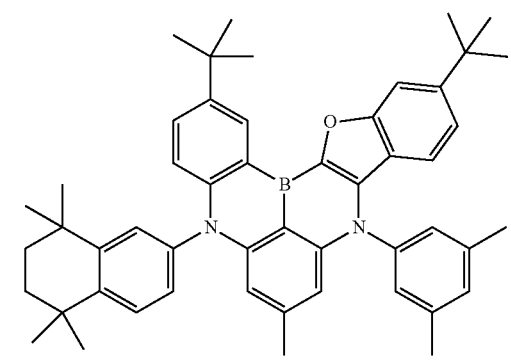 | 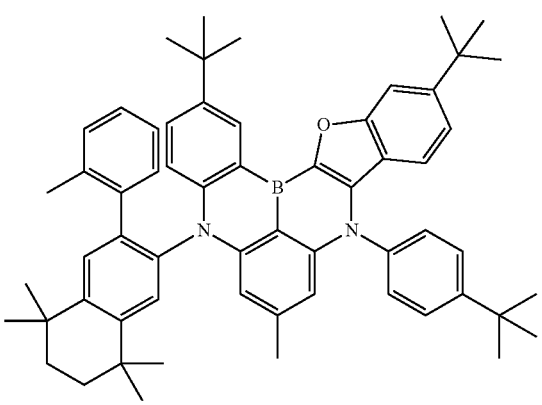 |

2459
-continued
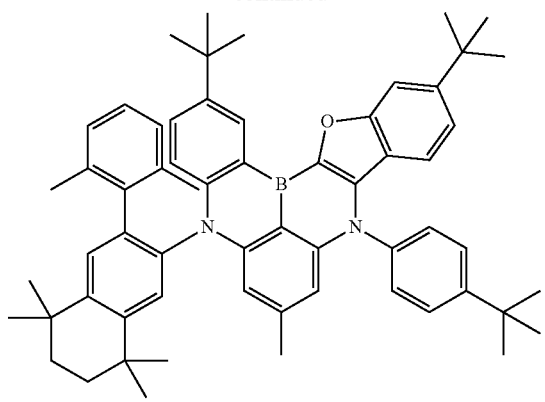
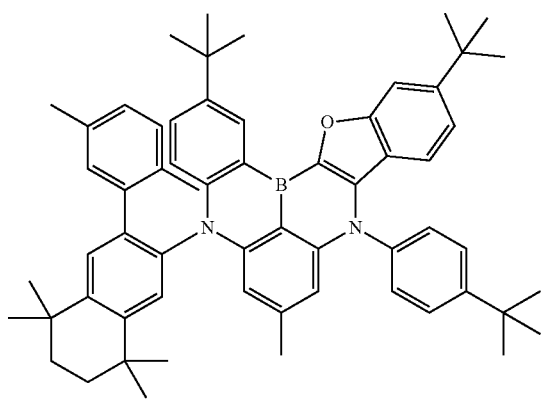
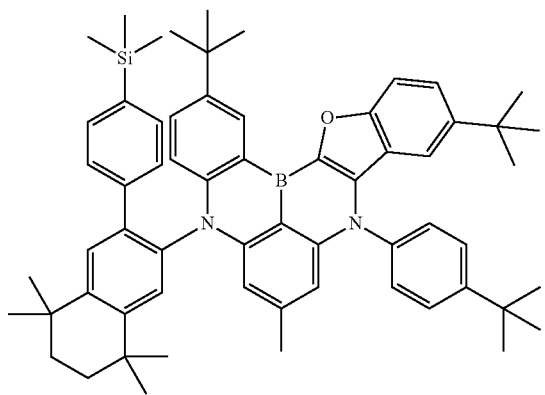
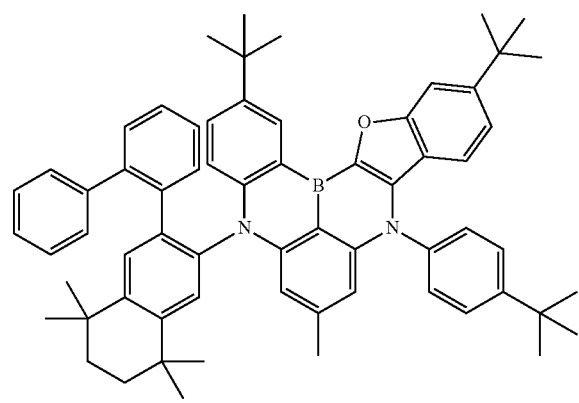
2460
-continued
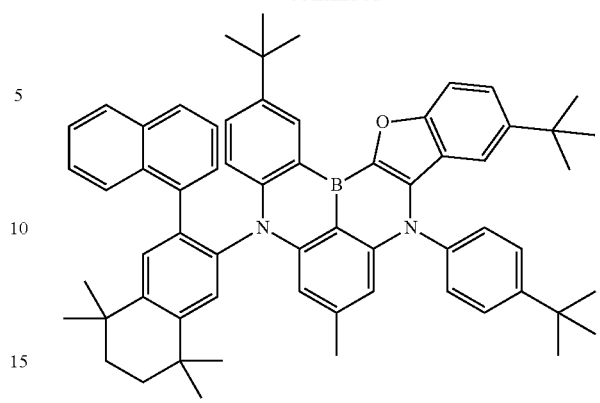
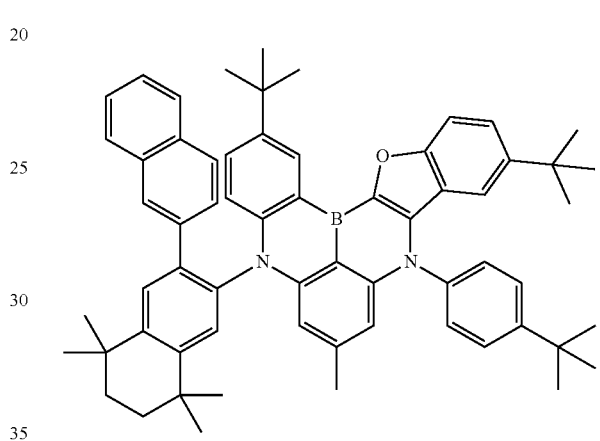
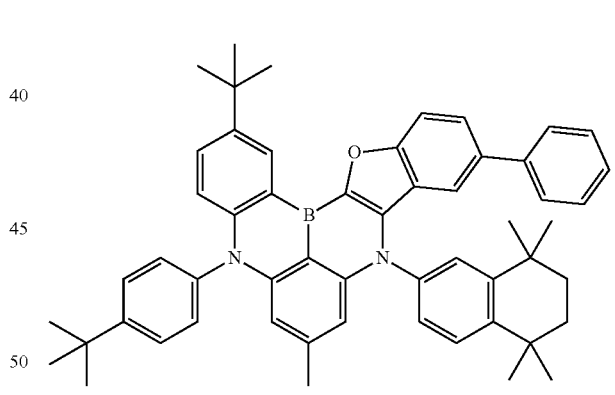
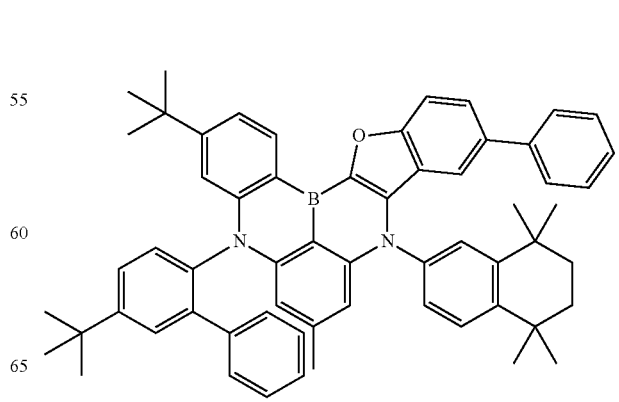

2461
-continued
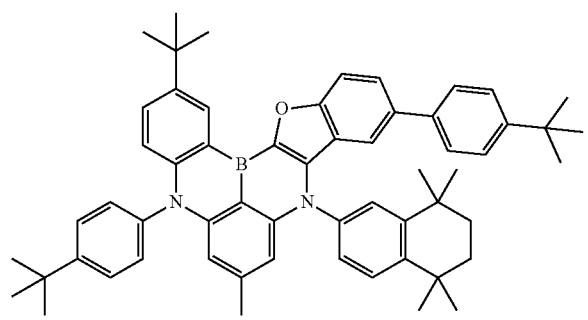
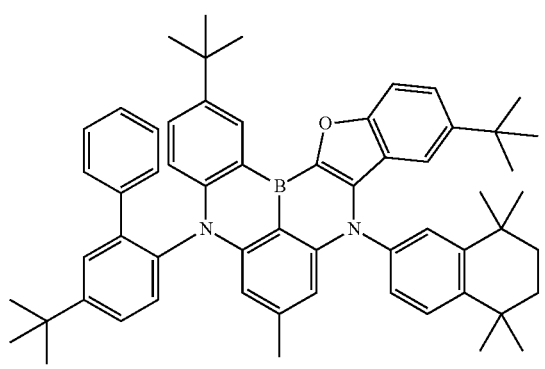
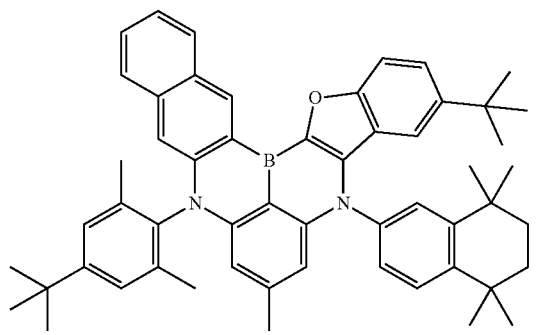
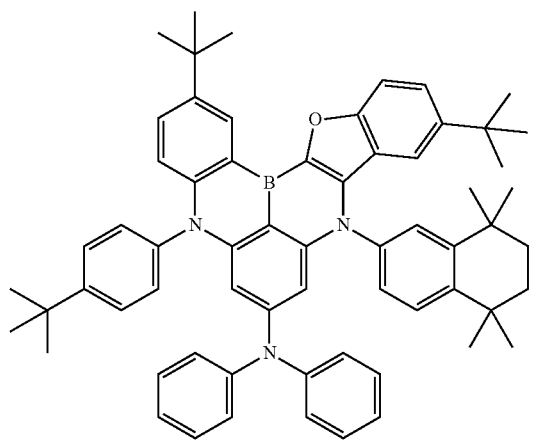
2462
-continued
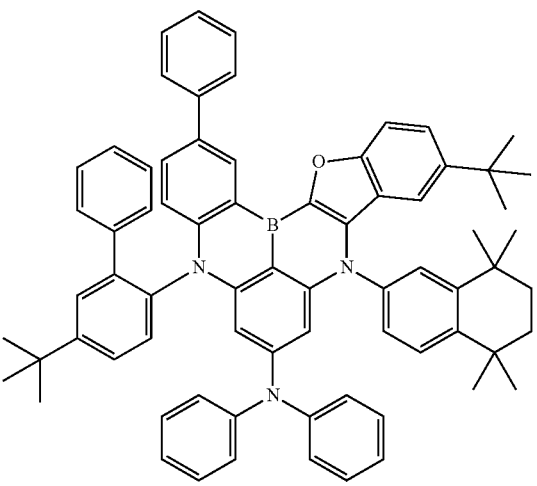
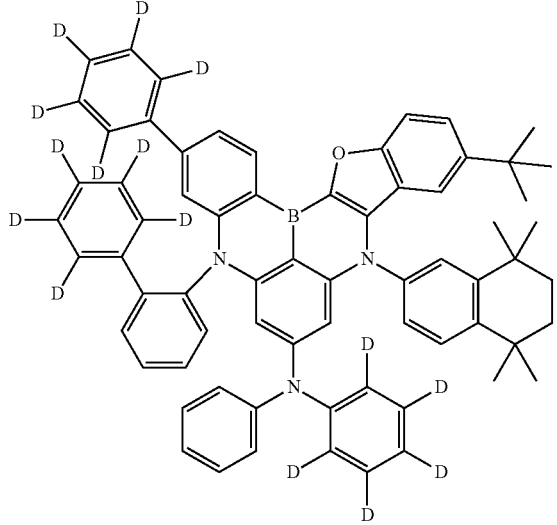
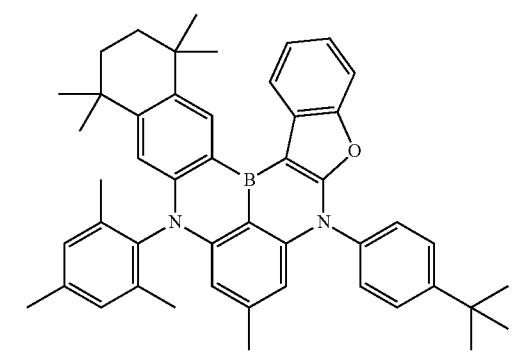
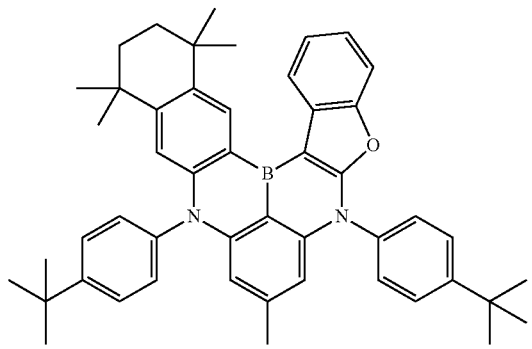

2463
-continued
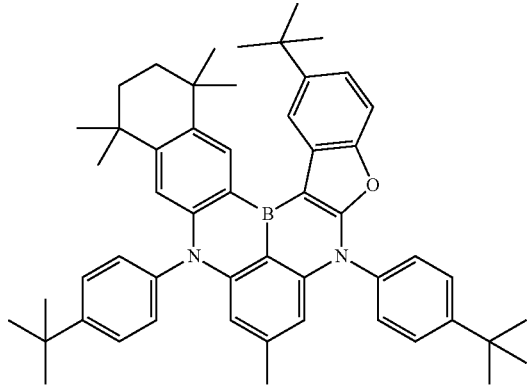
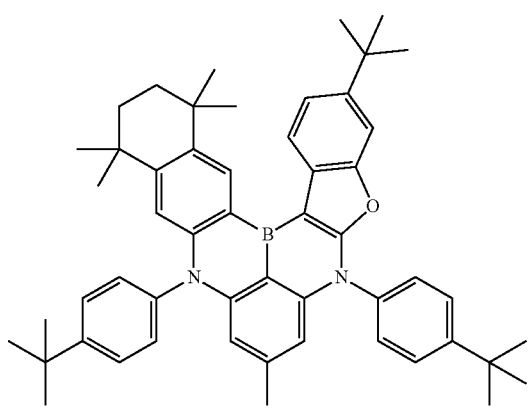
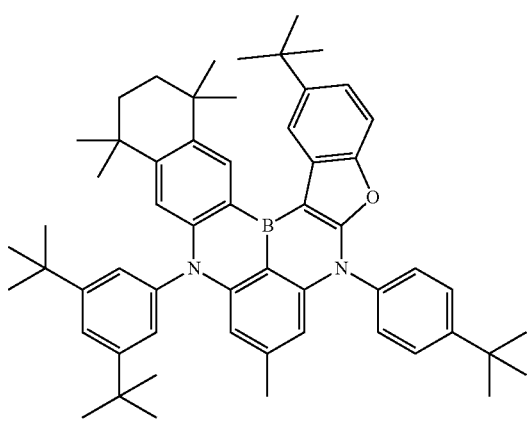
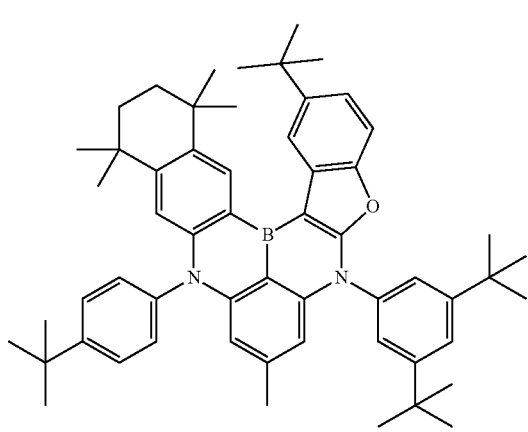
2464
-continued
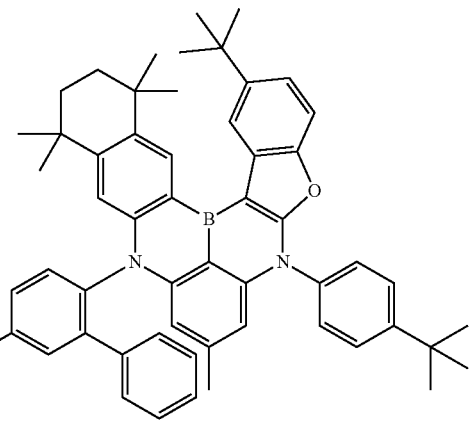
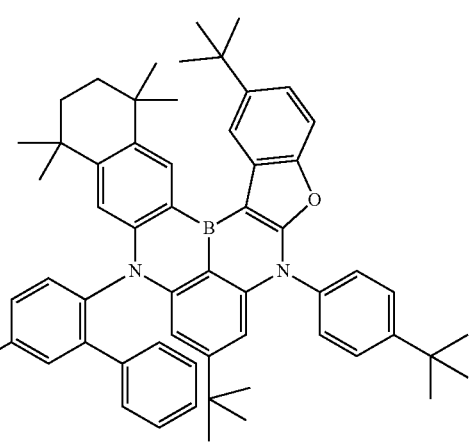
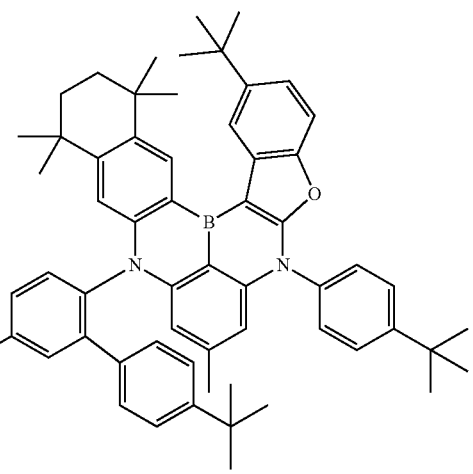

2465
-continued
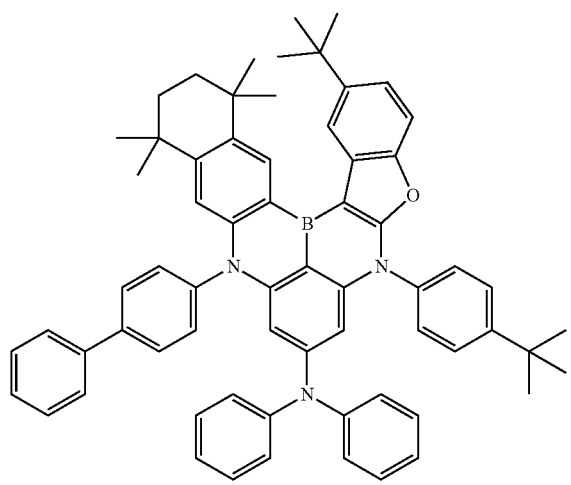
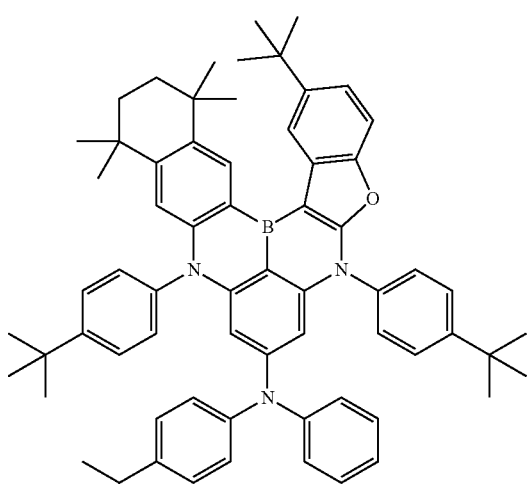
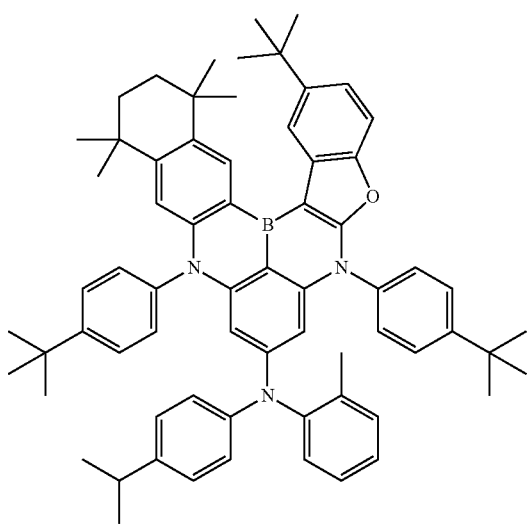
2466
-continued
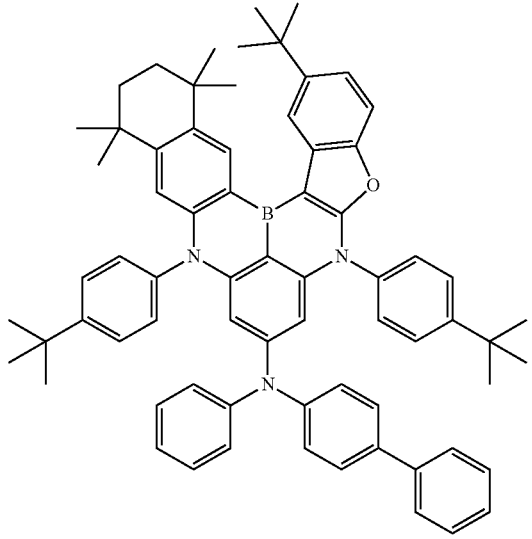
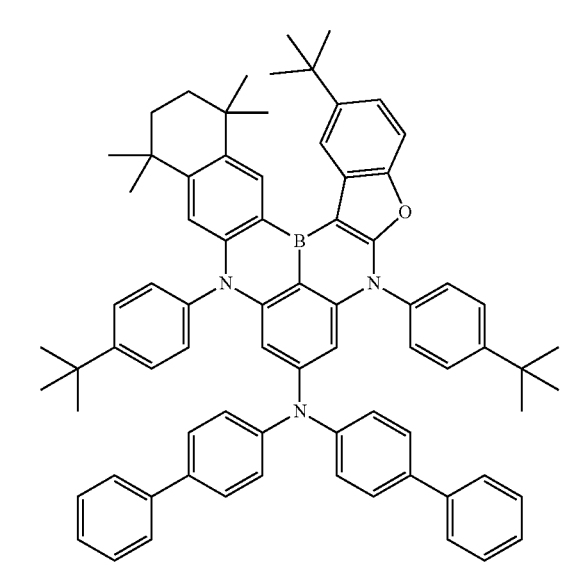
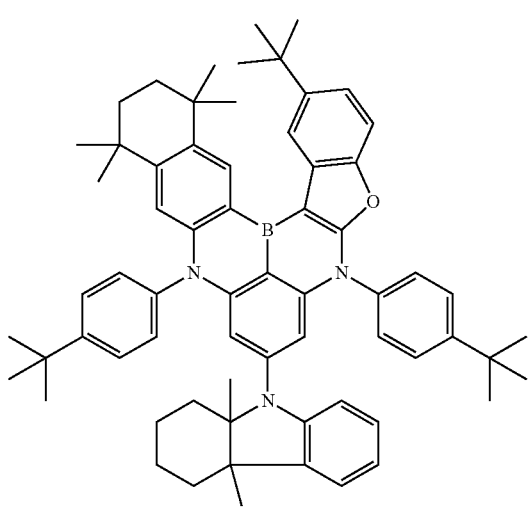

2467
-continued
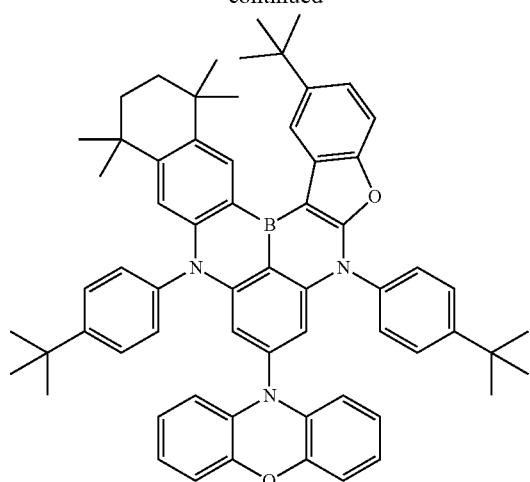
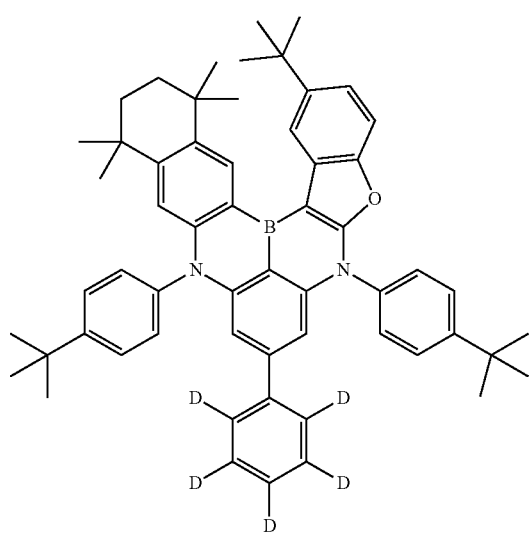
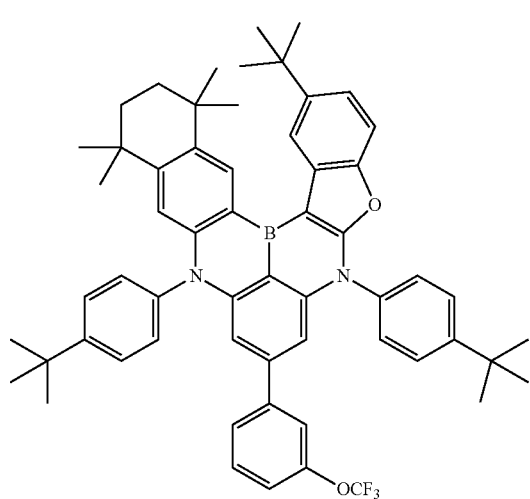
2468
-continued
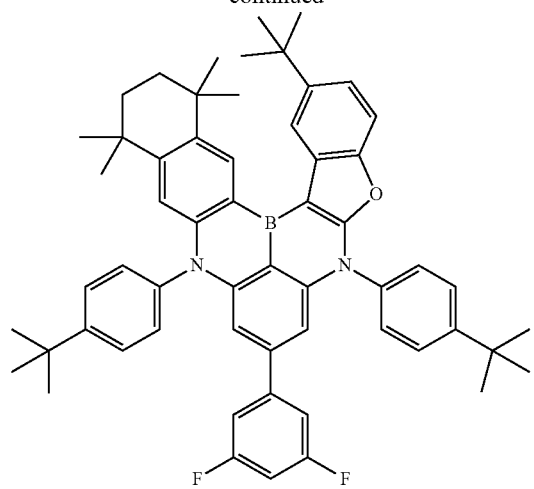
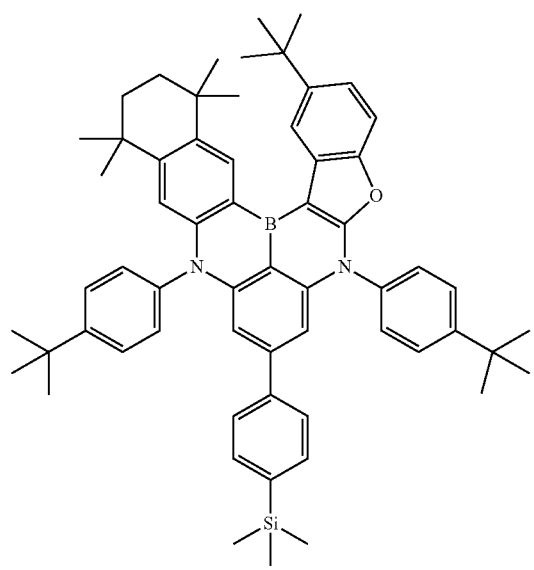
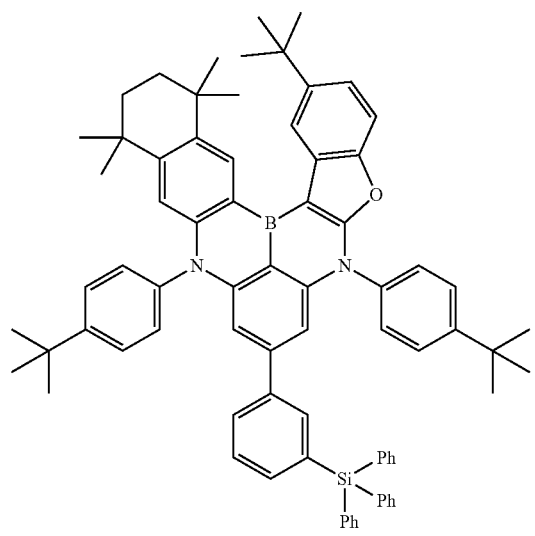

2469
-continued
2470
-continued
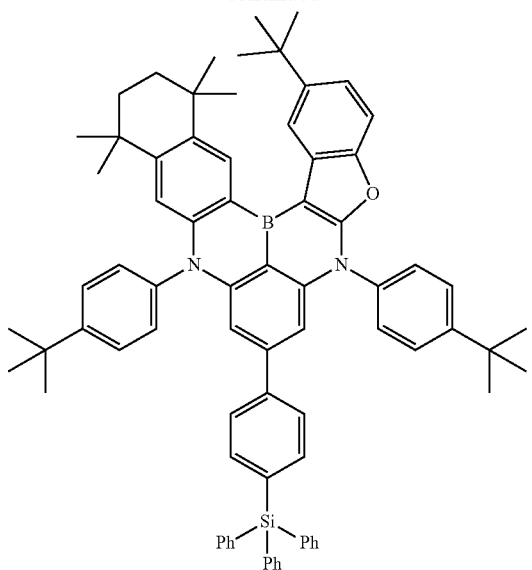
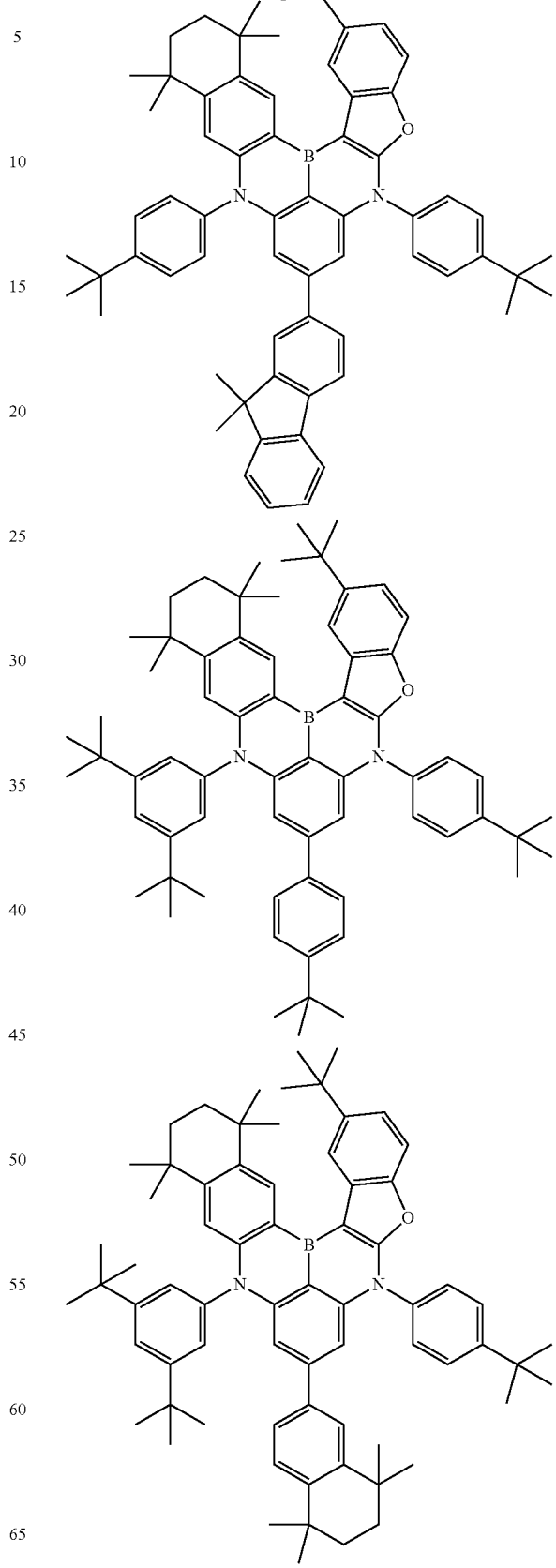
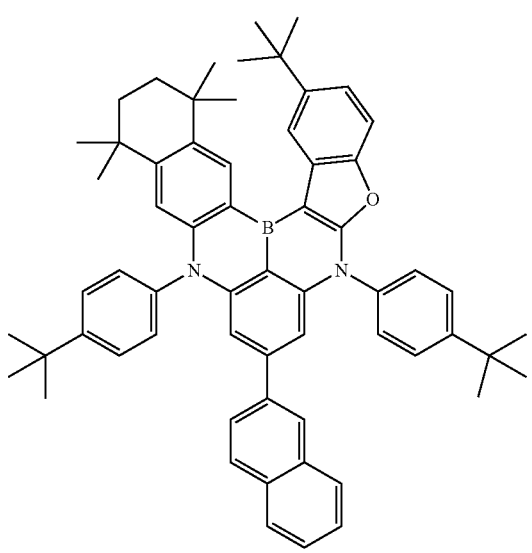
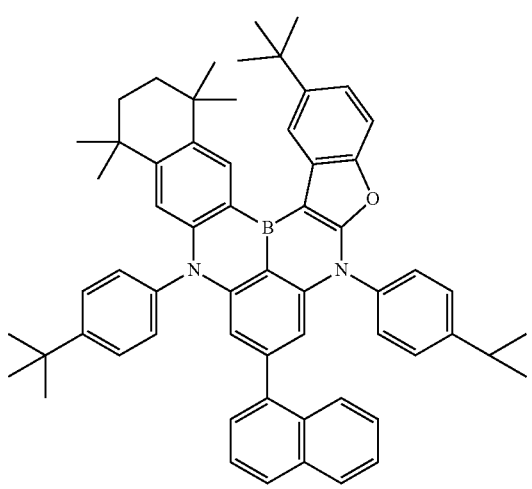

2471
-continued
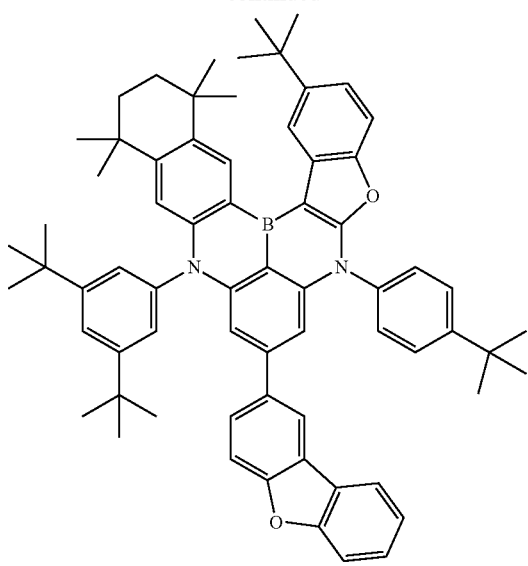
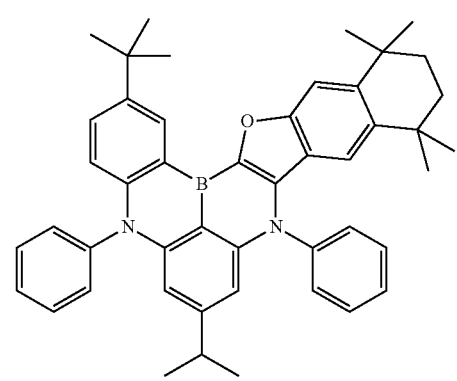
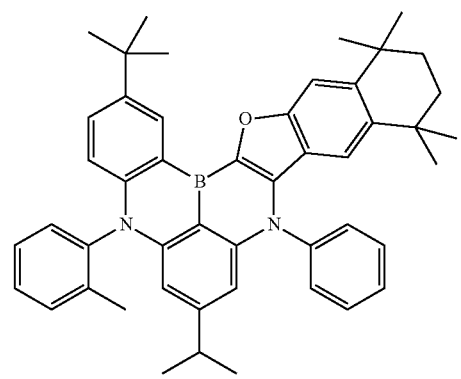
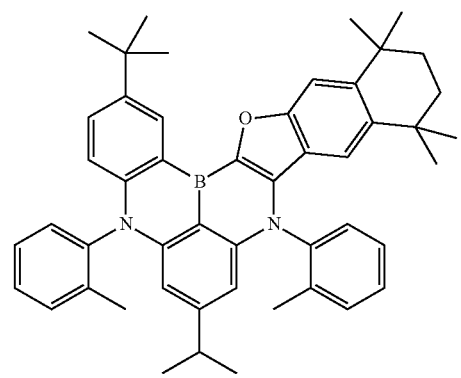
2472
-continued
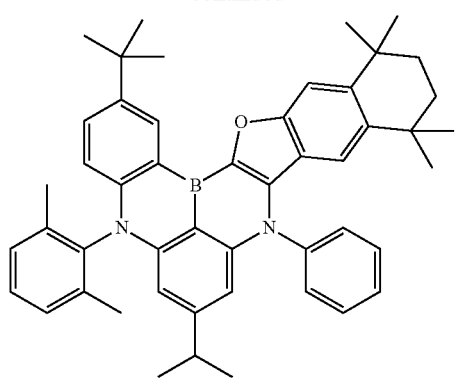
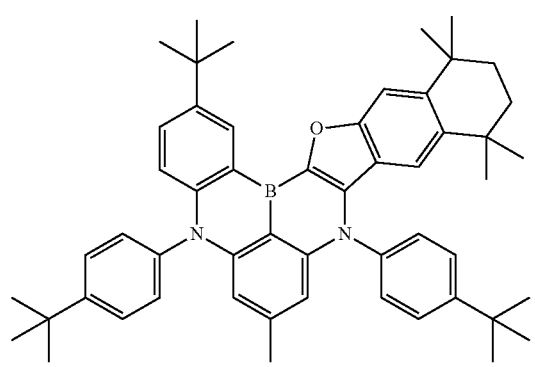
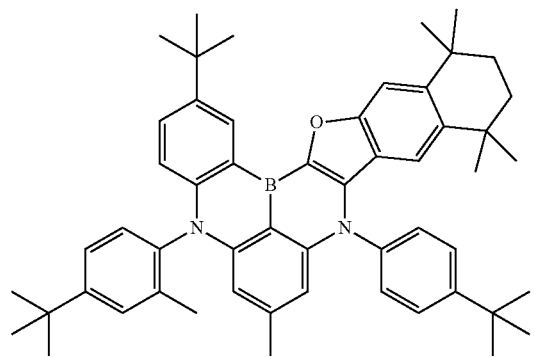
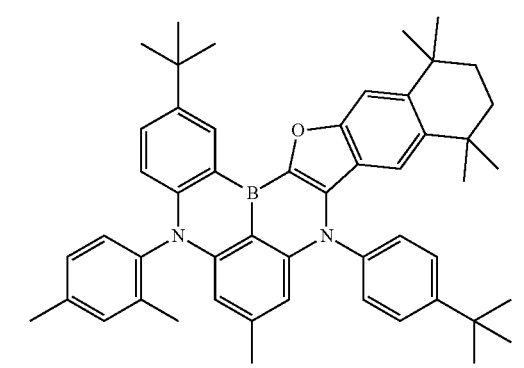

2473
-continued
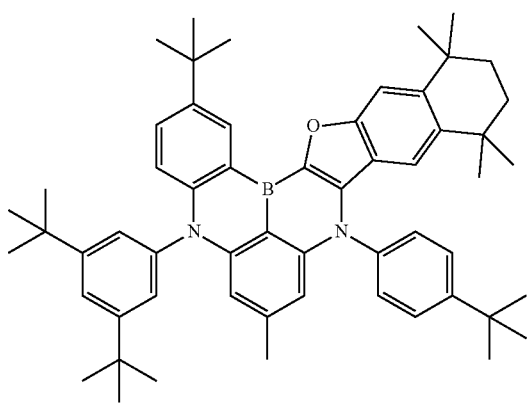
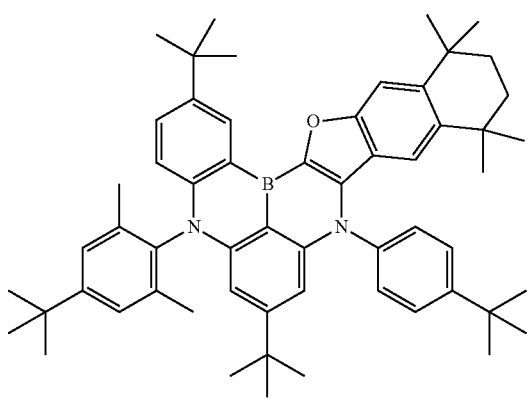
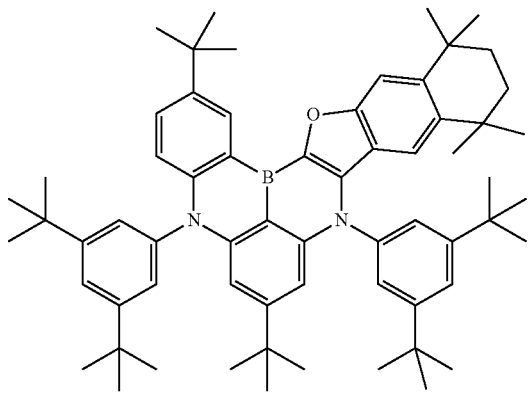
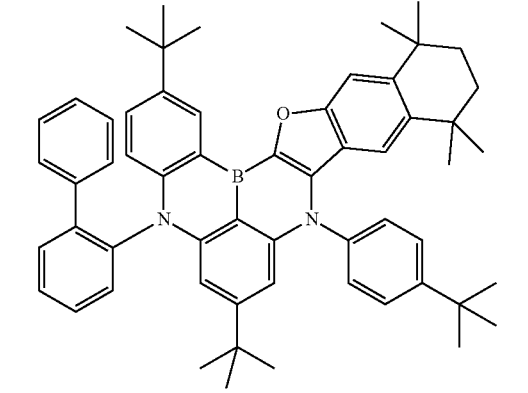
2474
-continued
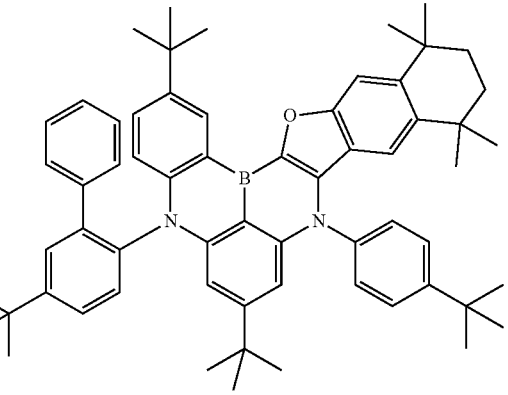
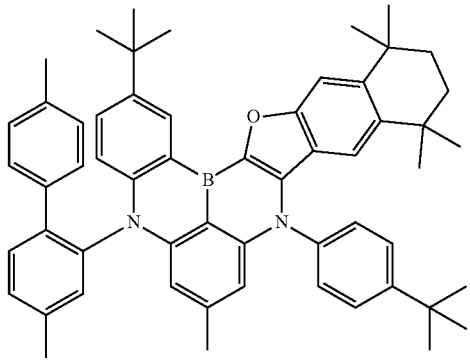
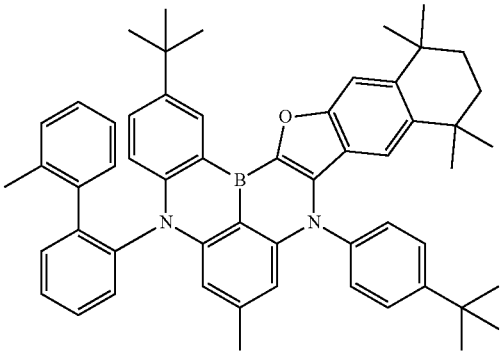

2475
-continued
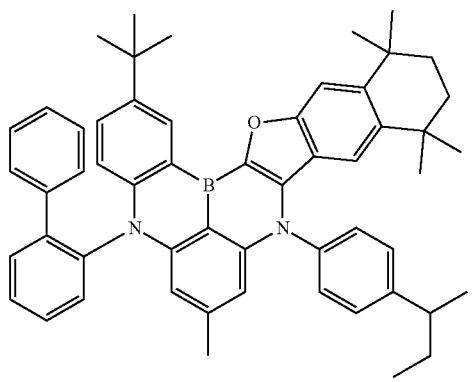
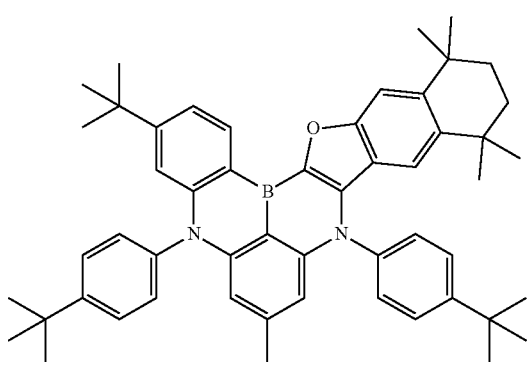
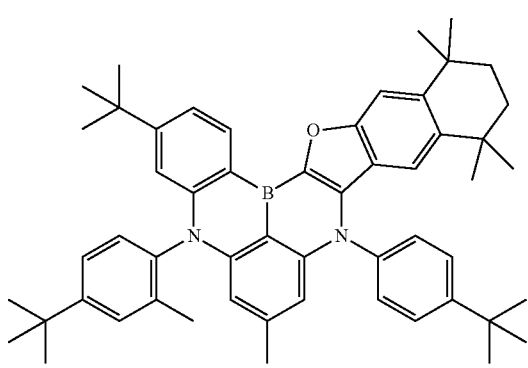
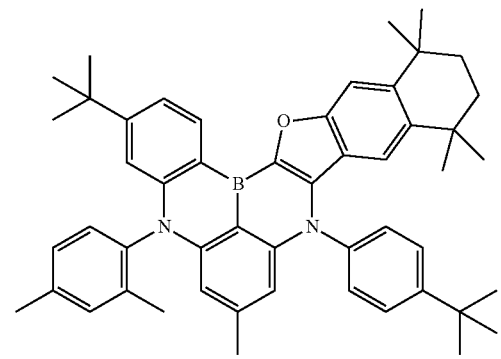
2476
-continued
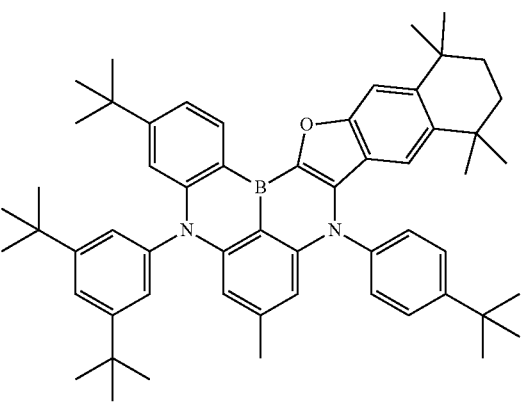
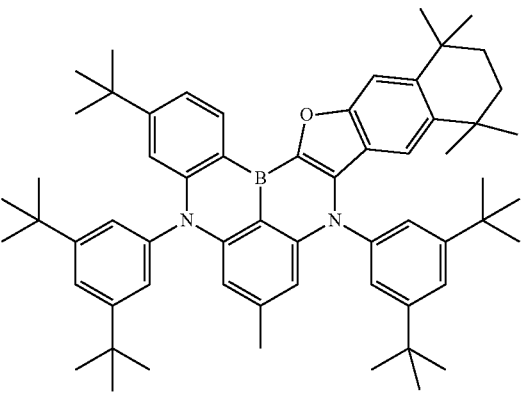
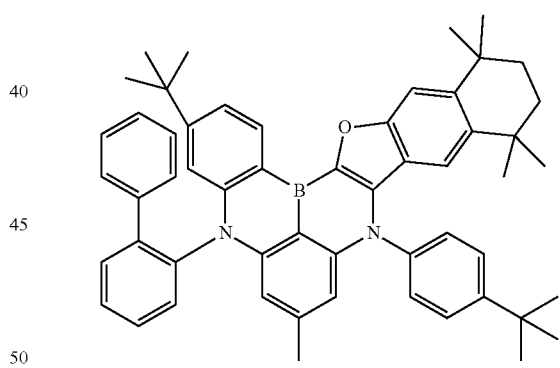
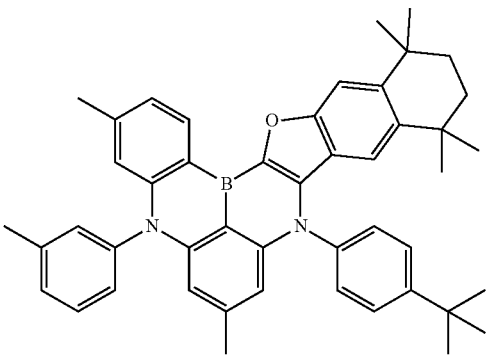

2477
-continued
2478
-continued
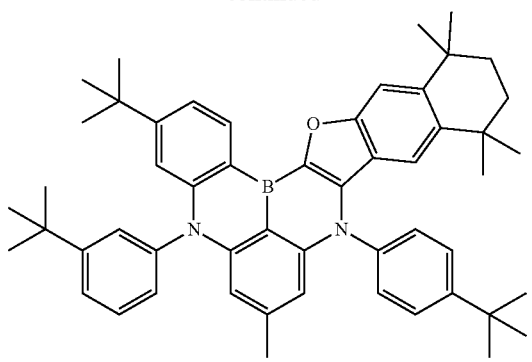
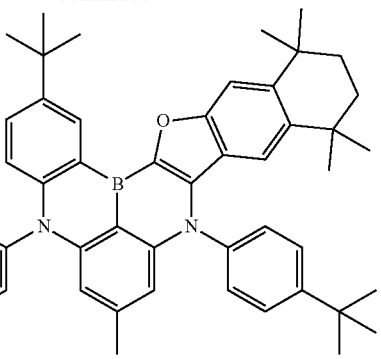
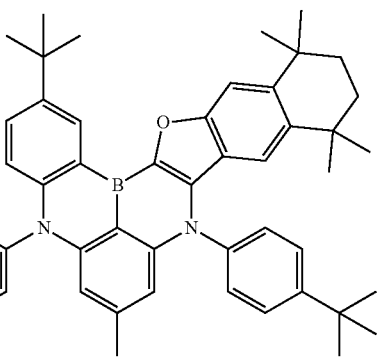
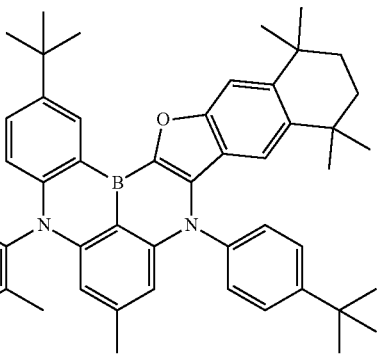
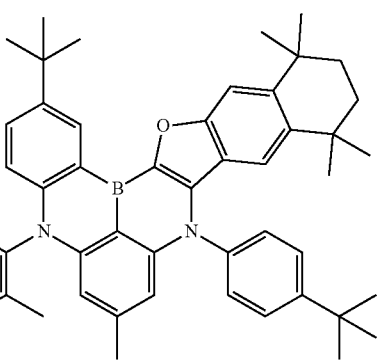

2479
-continued
2480
-continued
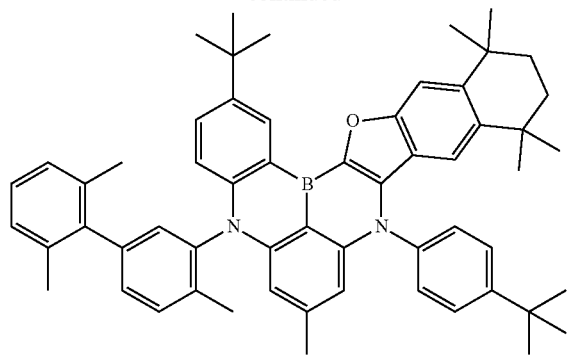
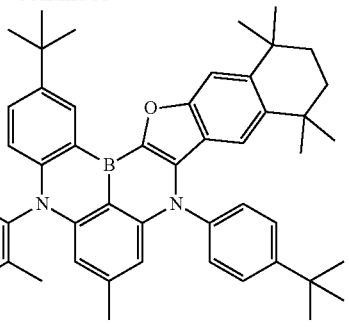
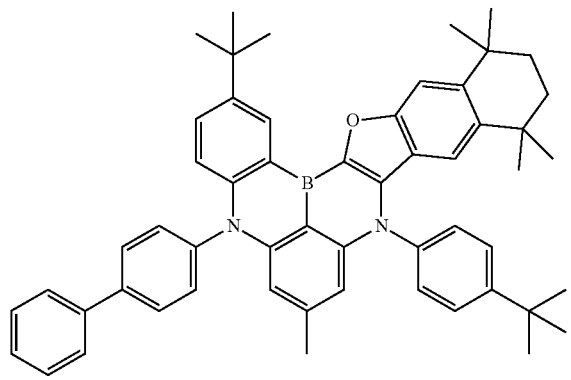
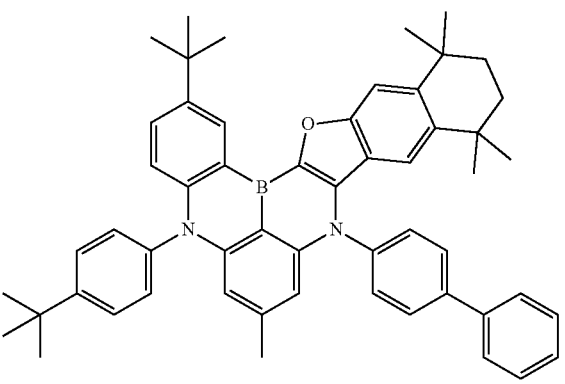
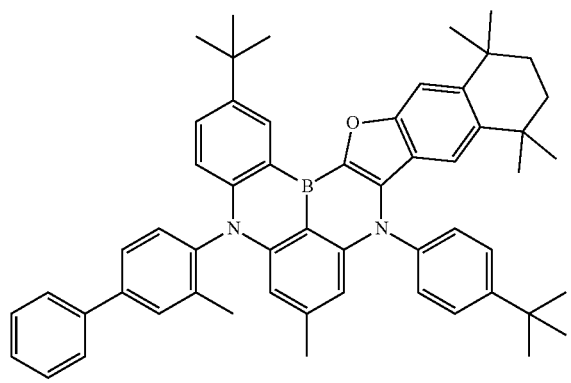
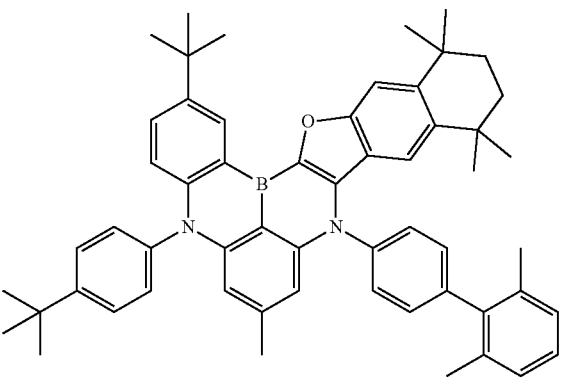
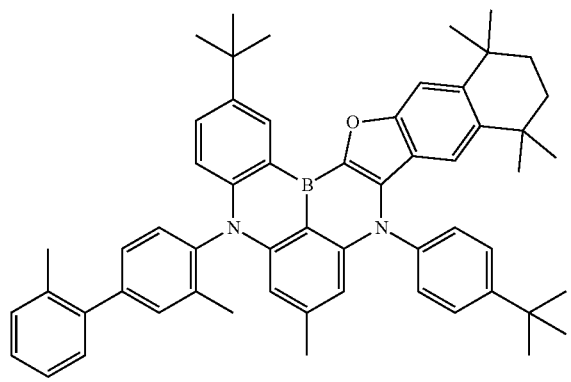
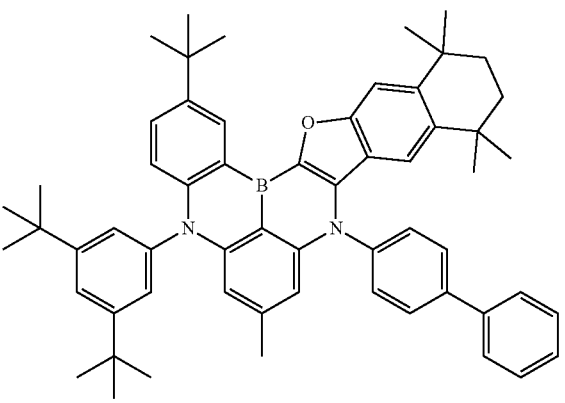

2481
-continued
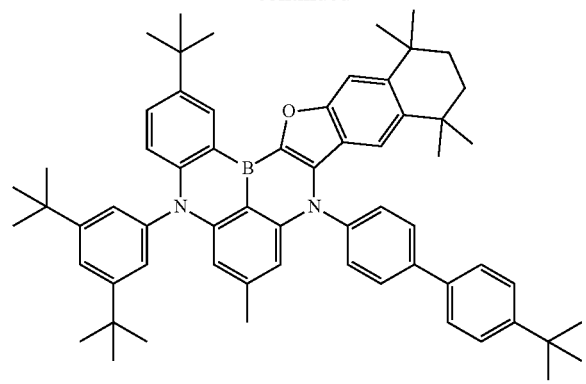
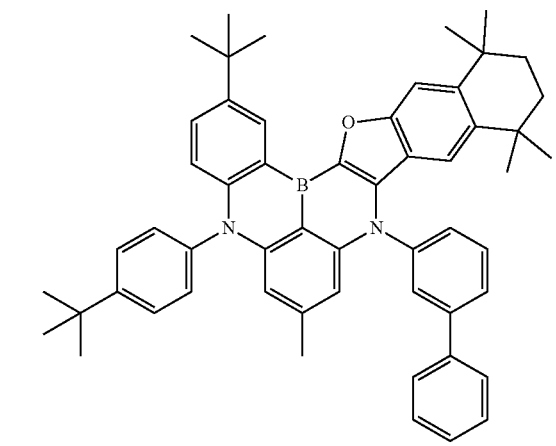
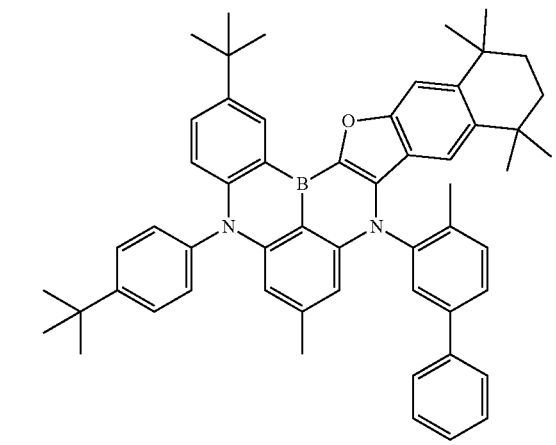
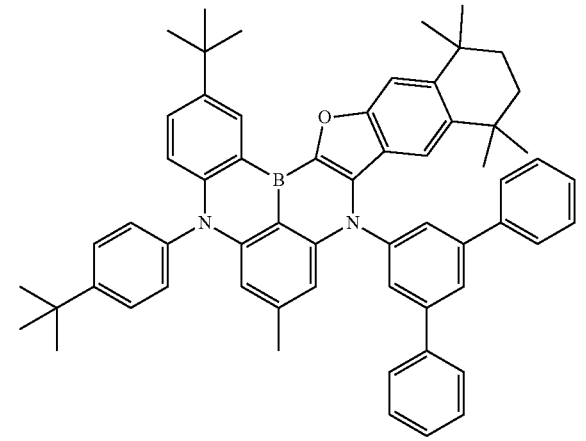
2482
-continued
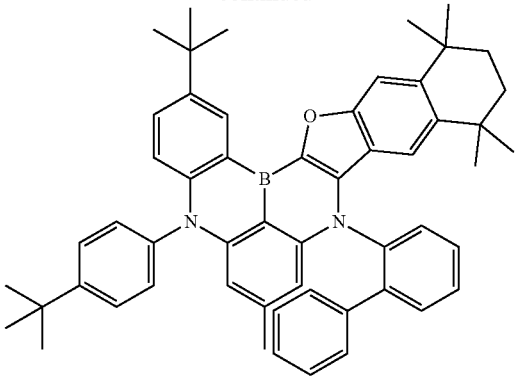
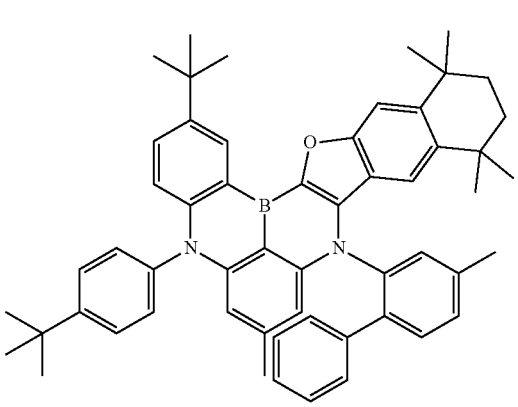
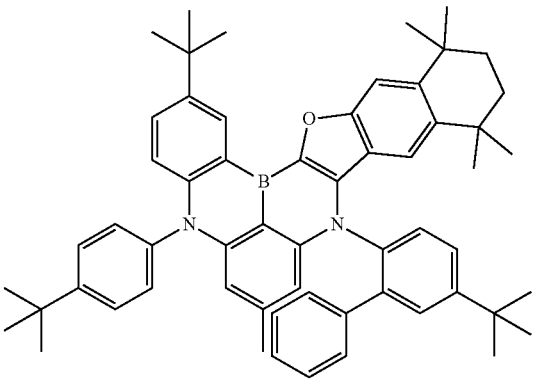
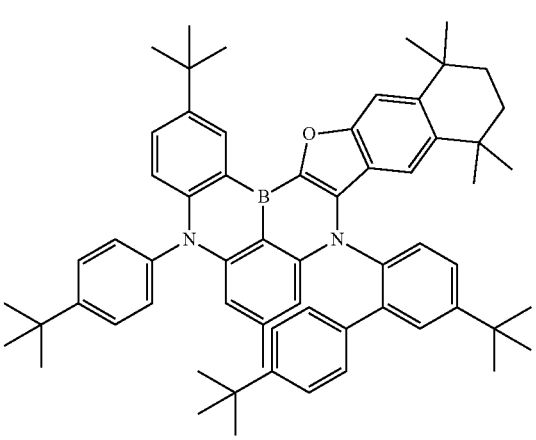

2483
-continued
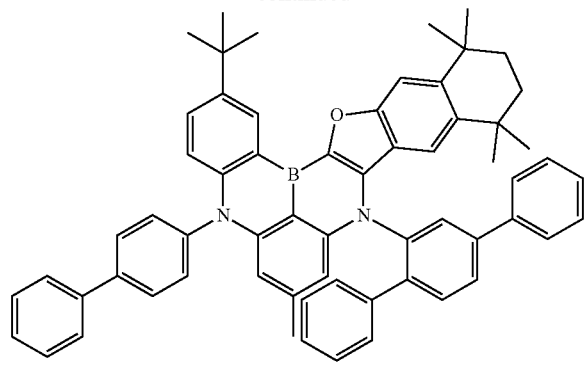
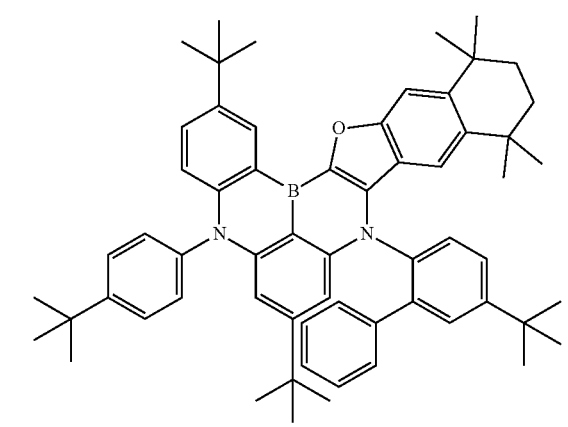
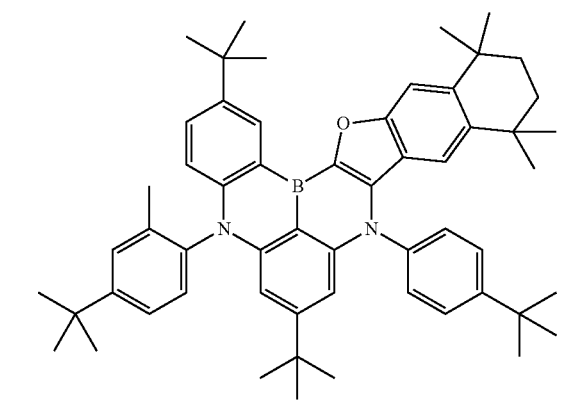
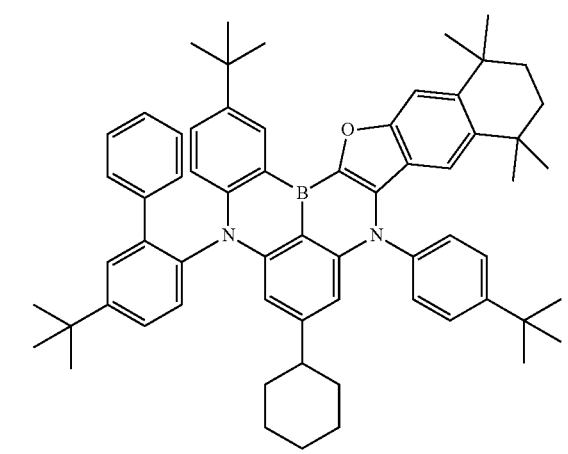
2484
-continued
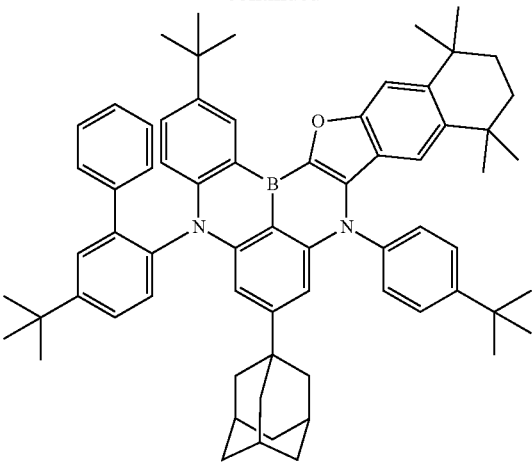
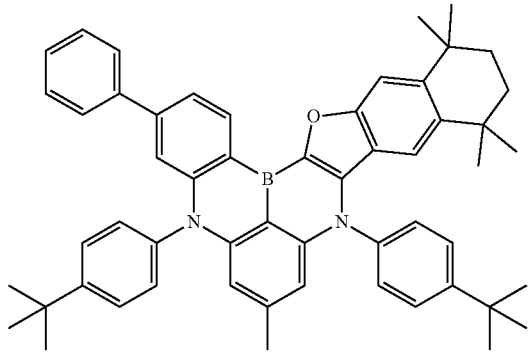
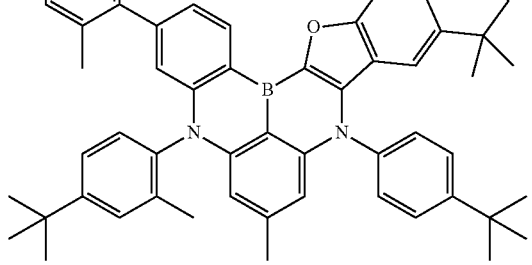
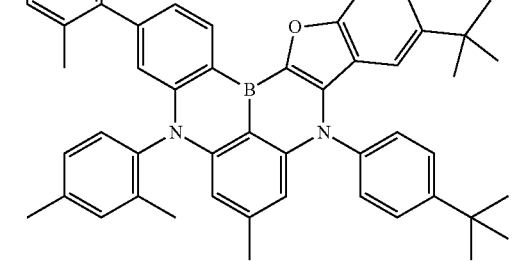

2485
-continued
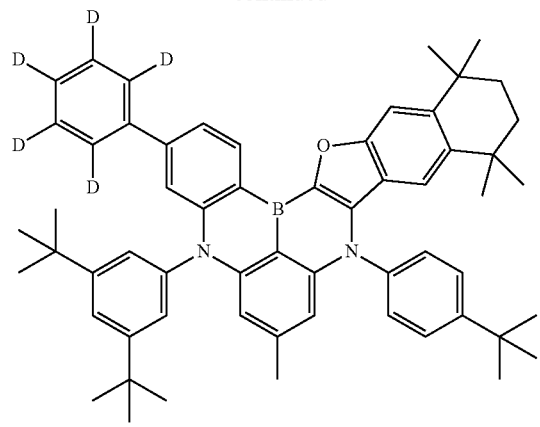
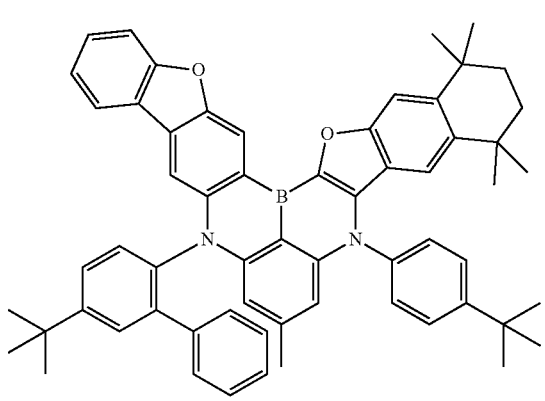
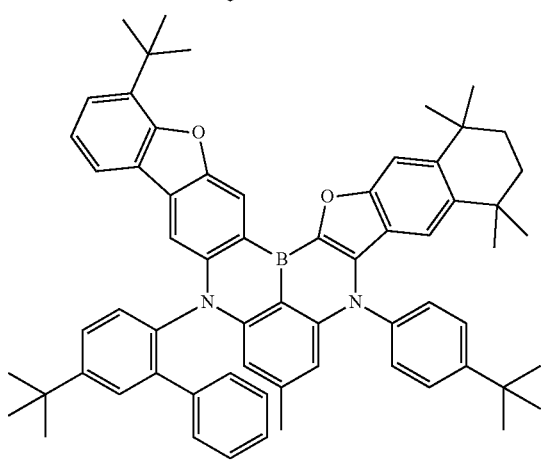
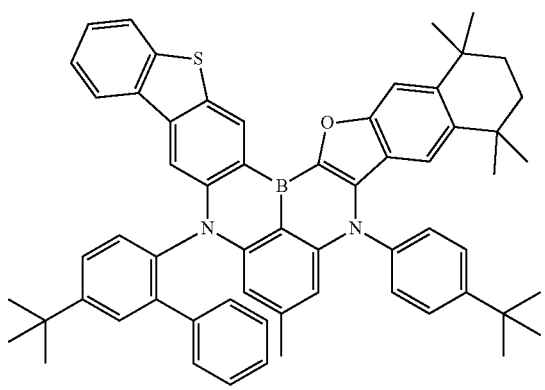
2486
-continued
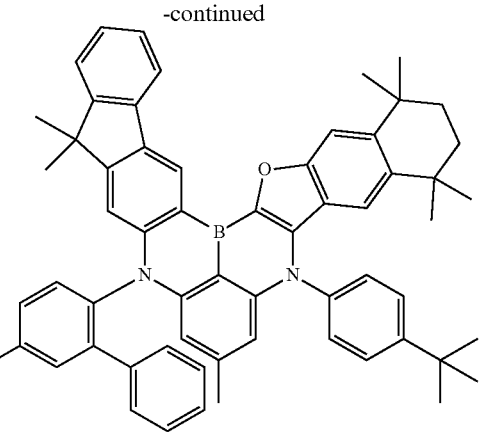
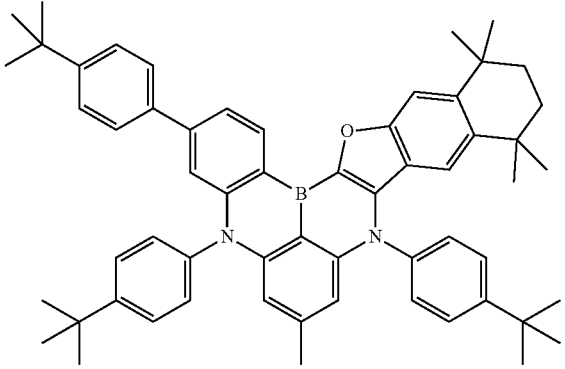
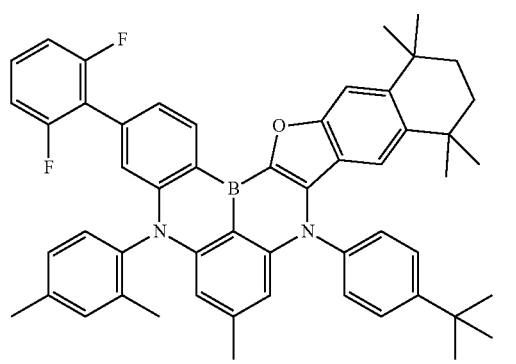
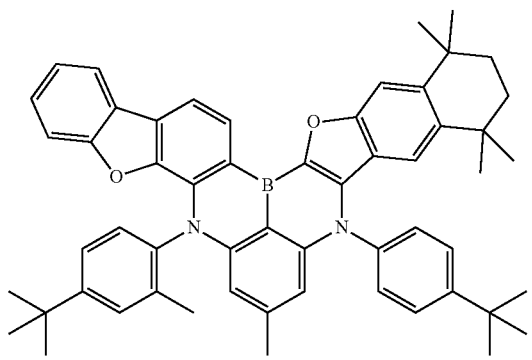

2487
-continued
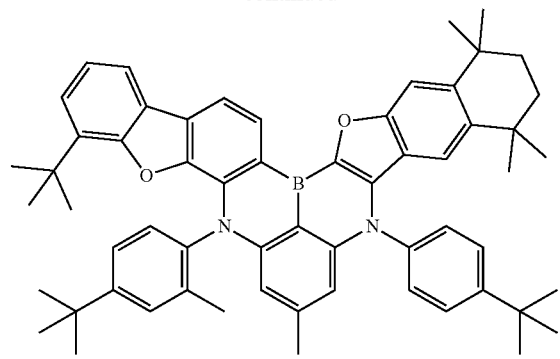
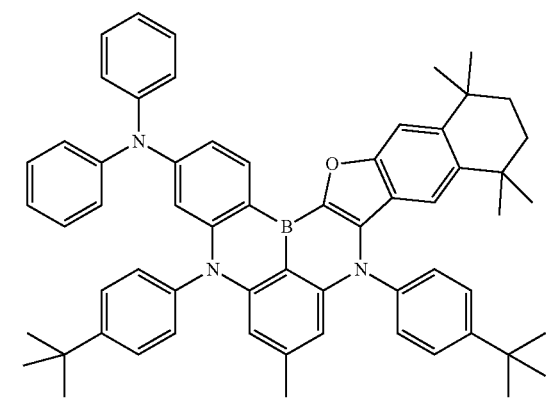
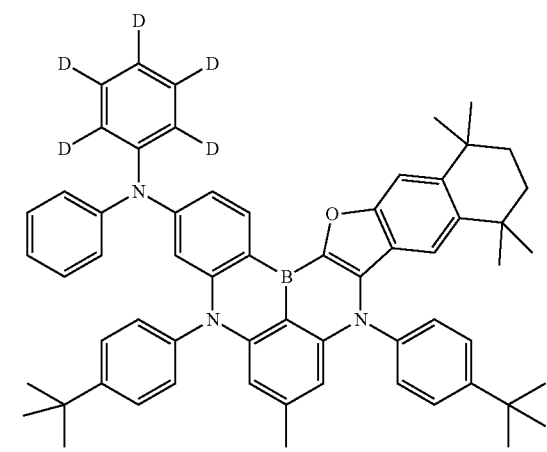
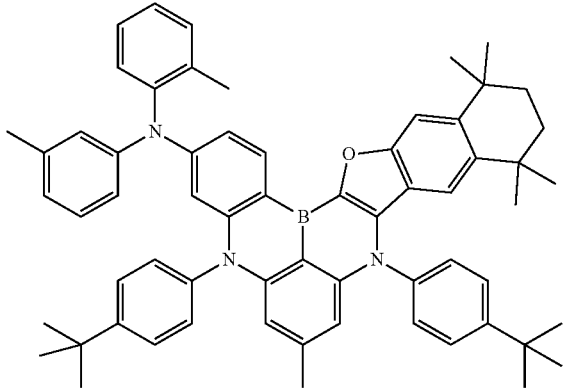
2488
-continued
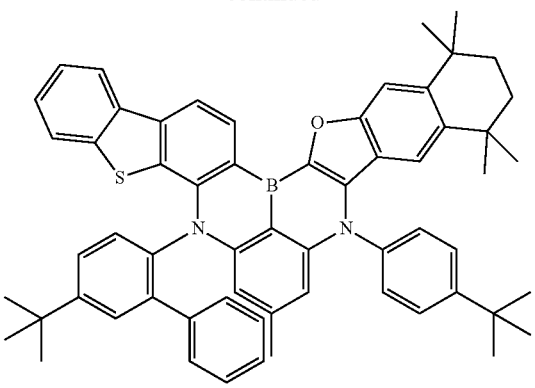
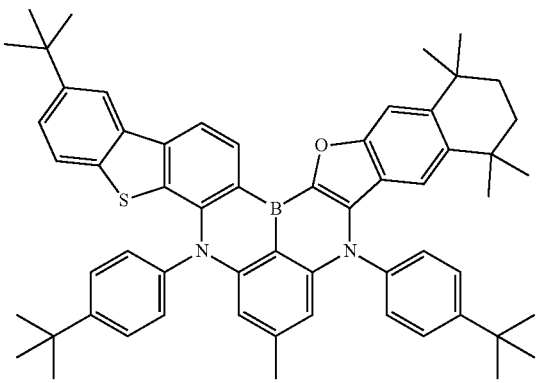
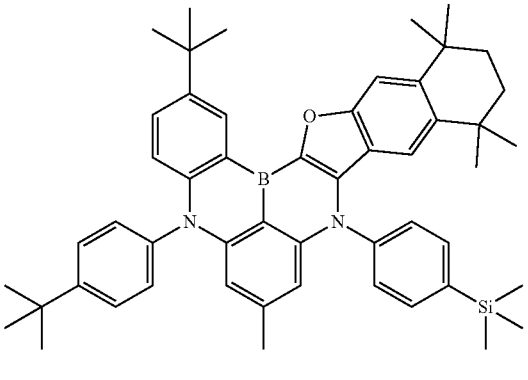
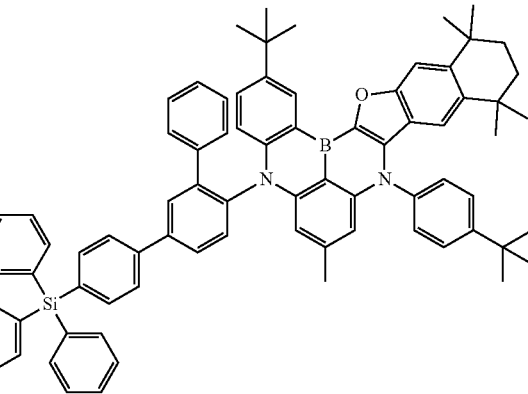

2489
-continued
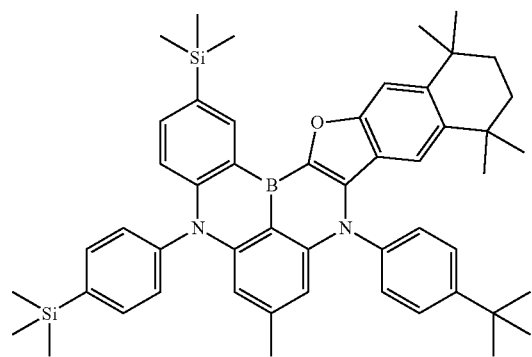
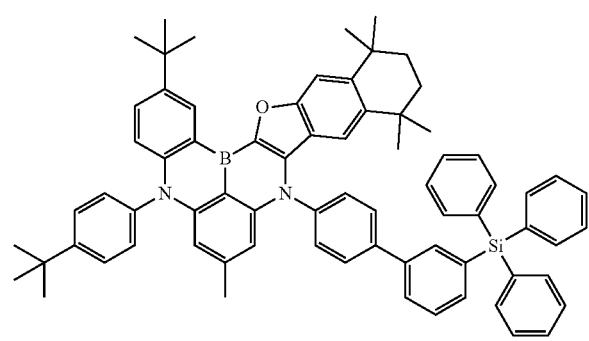
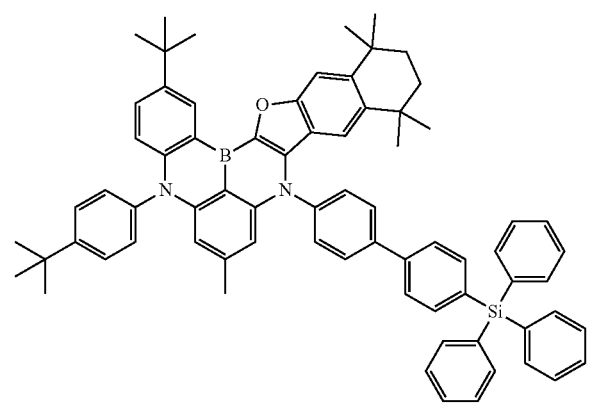
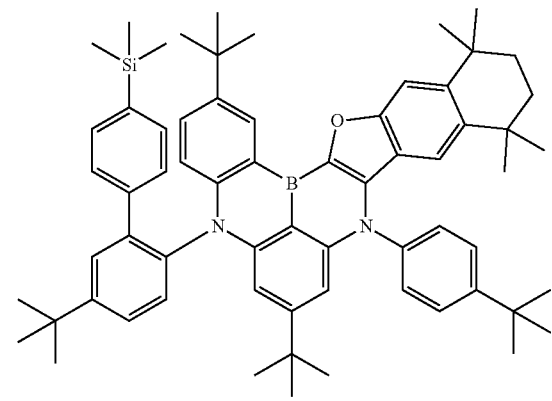
2490
-continued
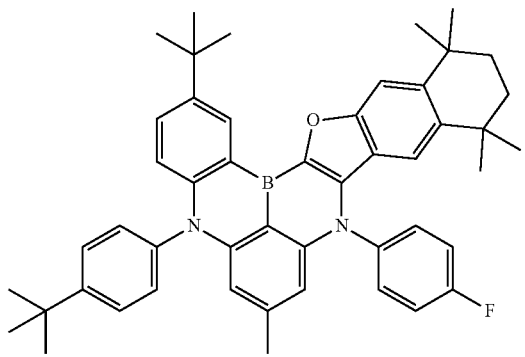
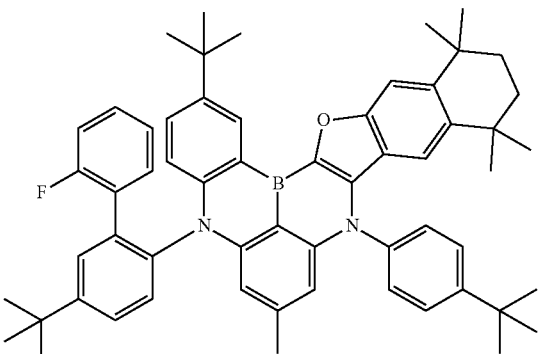
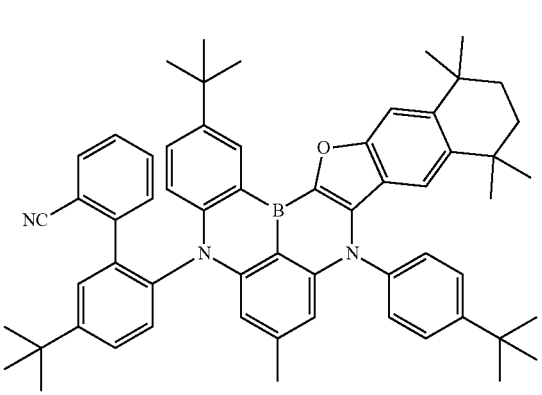
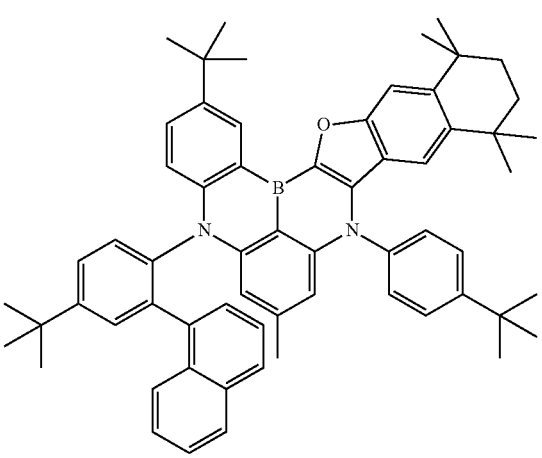

| 2491 -continued | 2492 -continued |
|---|---|
| 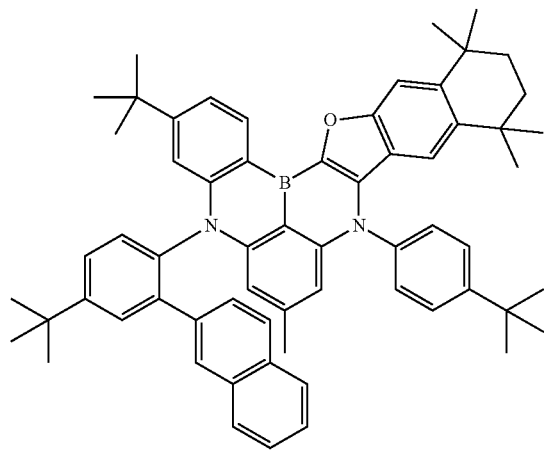 | 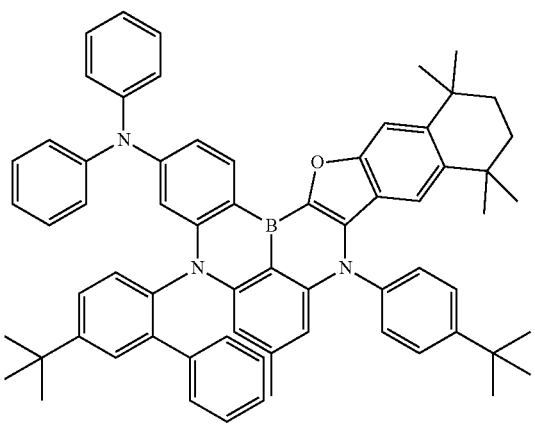 |
| 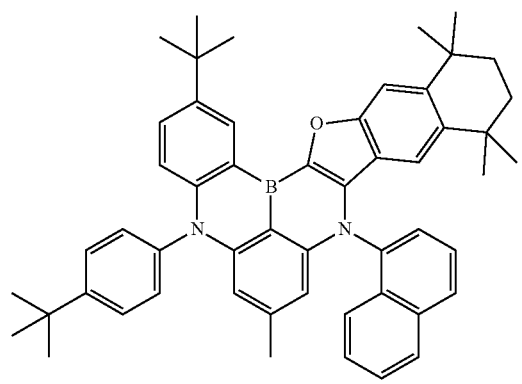 | 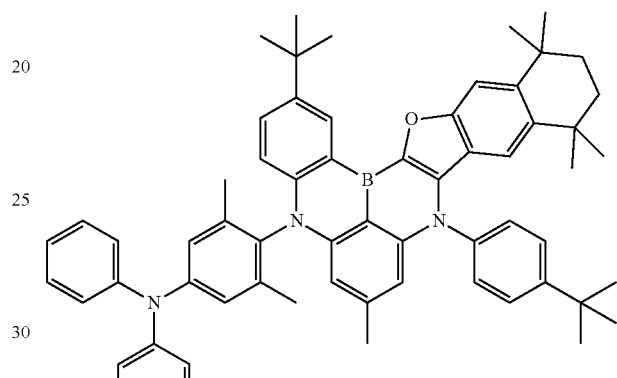 |
| 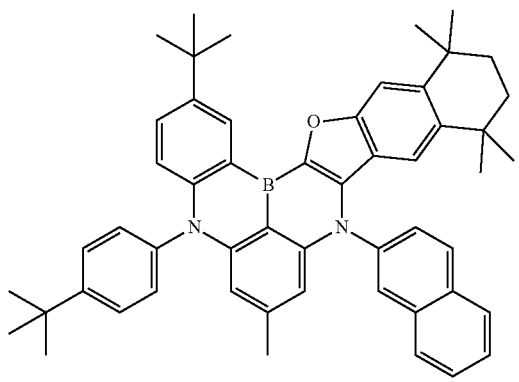 | 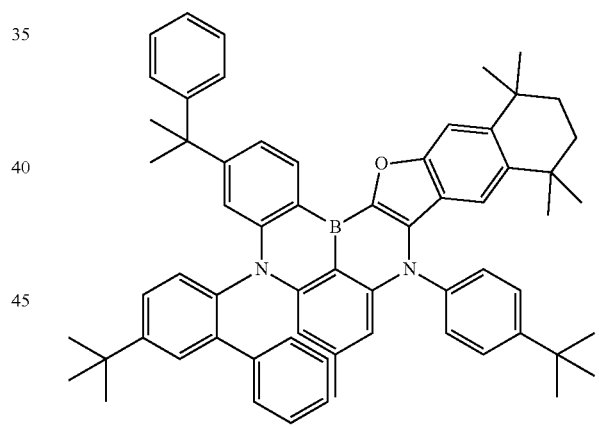 |
| 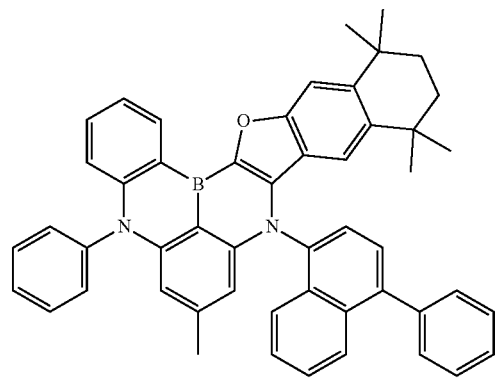 | 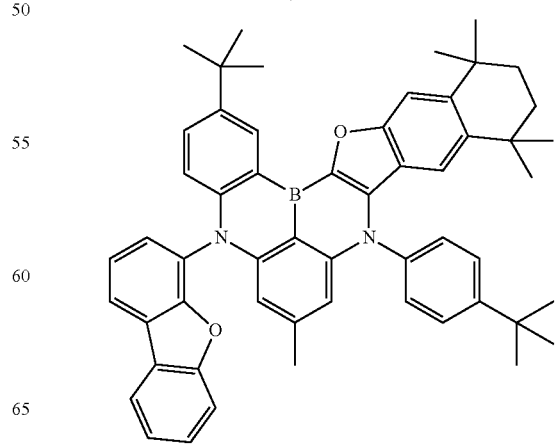 |

2493
-continued
2494
-continued
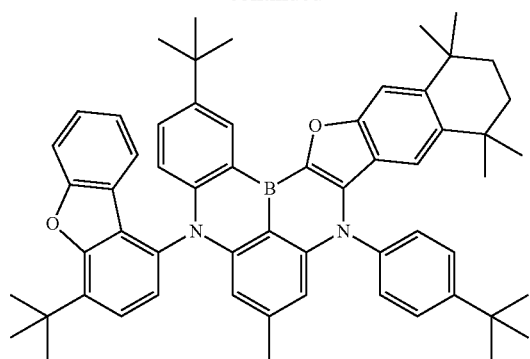
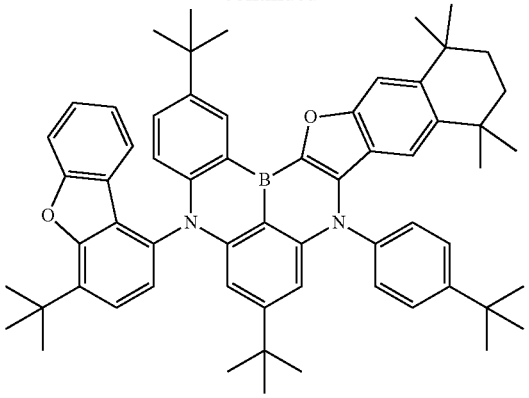
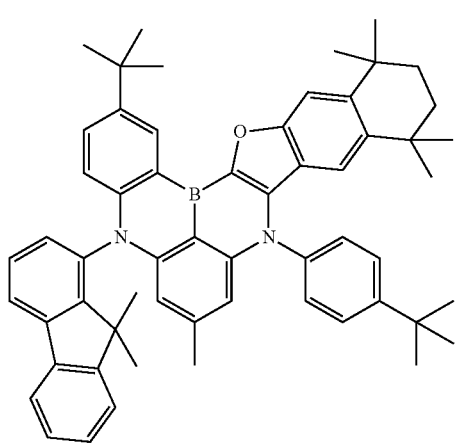
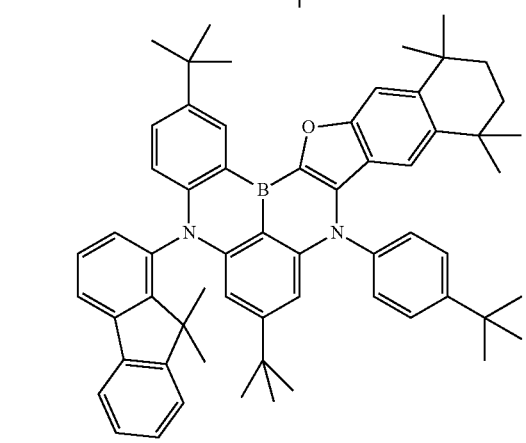
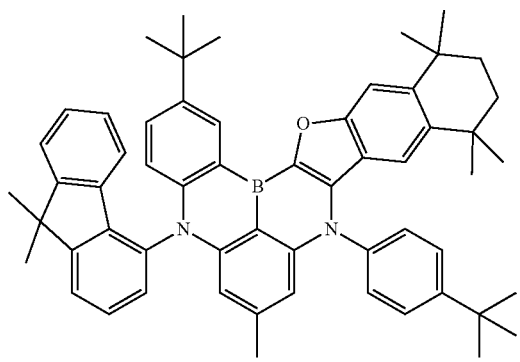
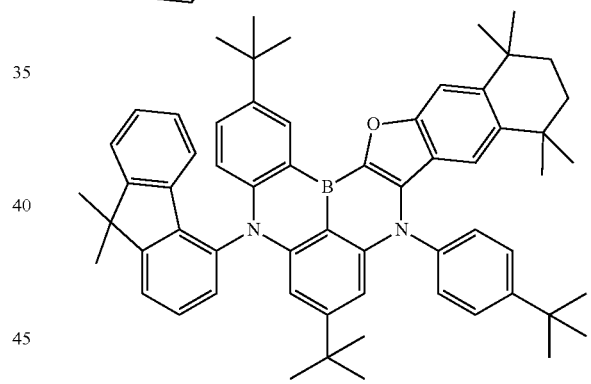
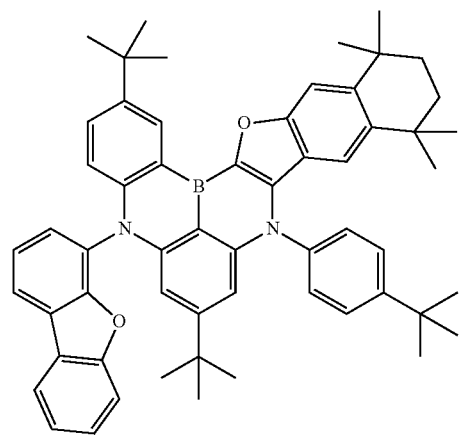
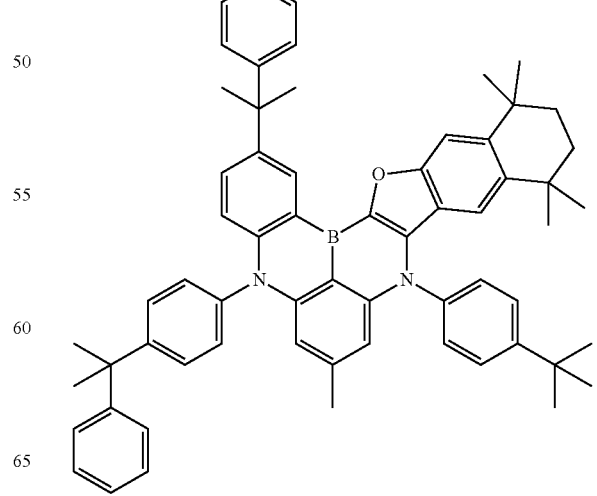

2495
-continued
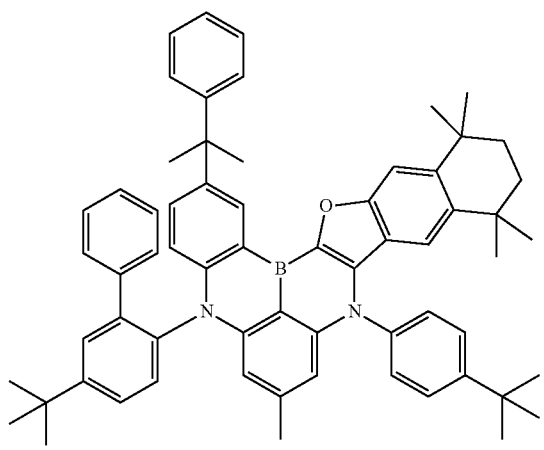
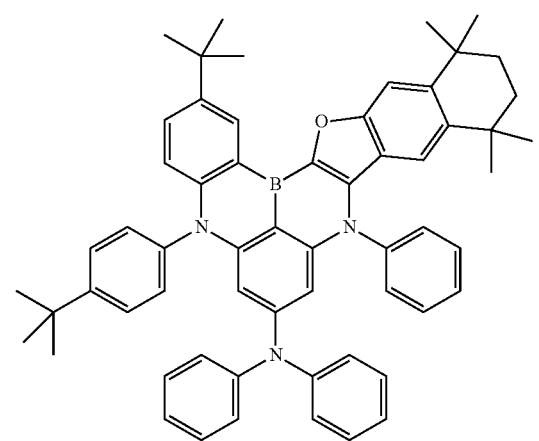
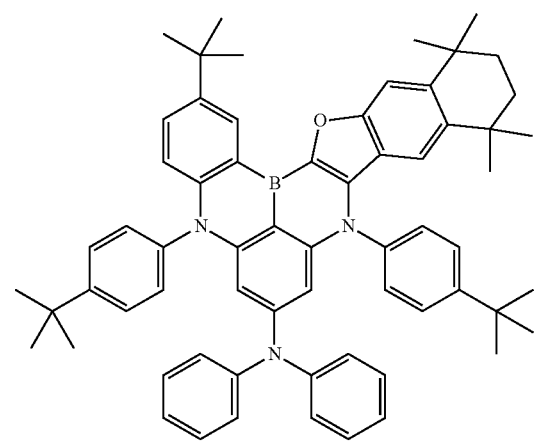
2496
-continued
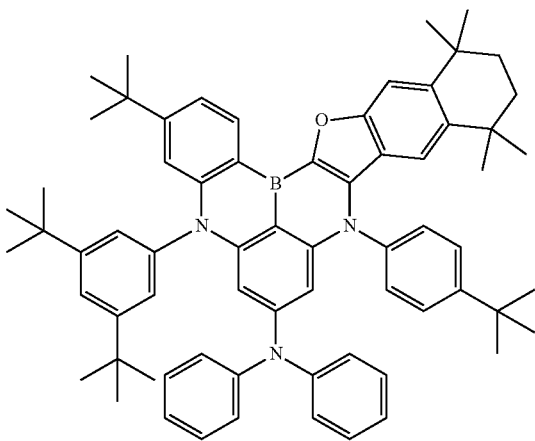
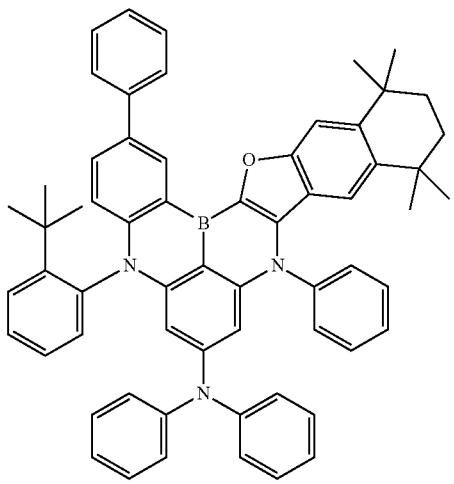
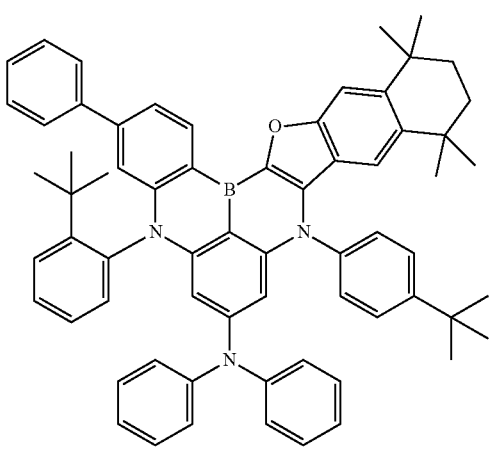

2497
-continued
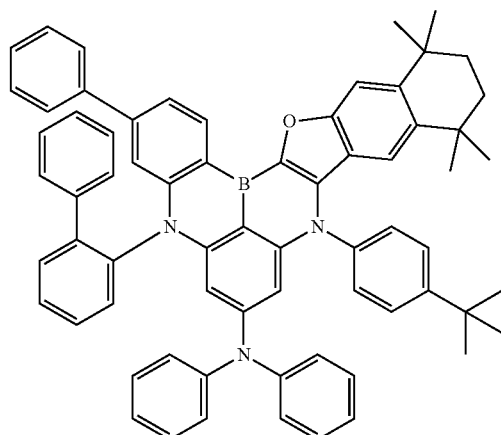
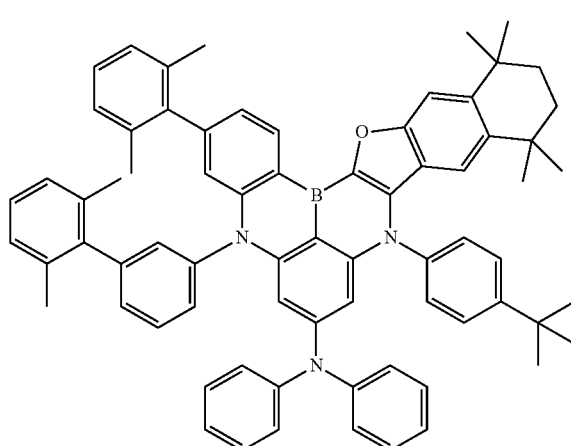
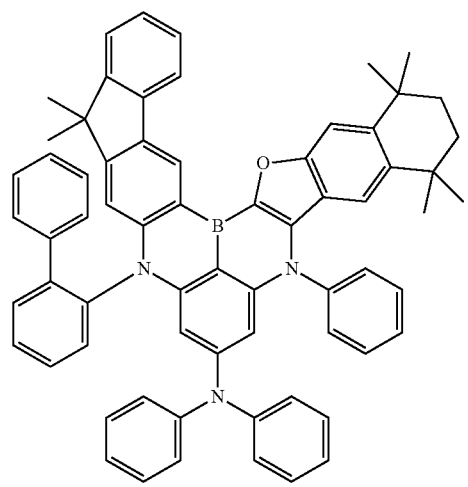
2498
-continued
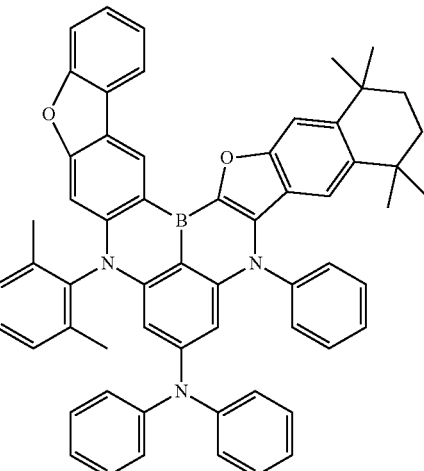
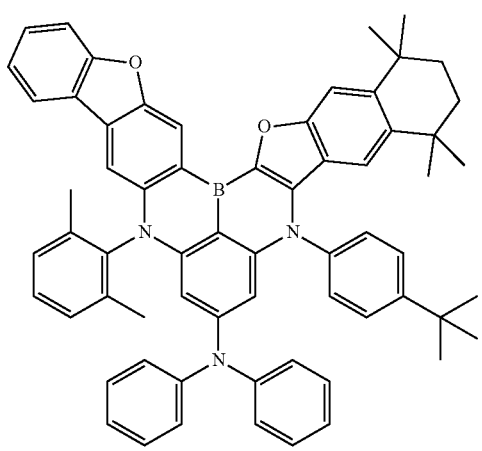
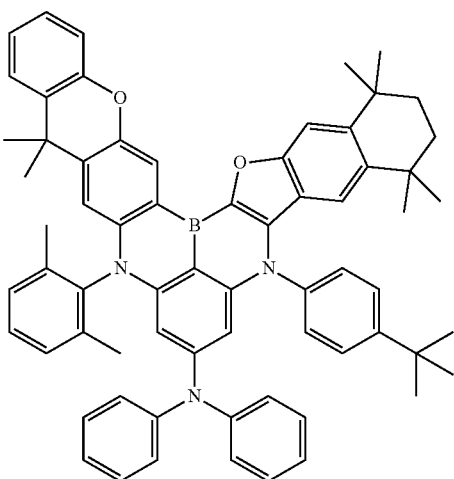

2499
-continued
2500
-continued
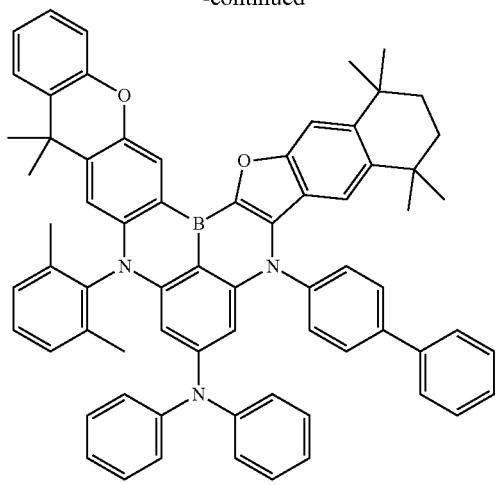
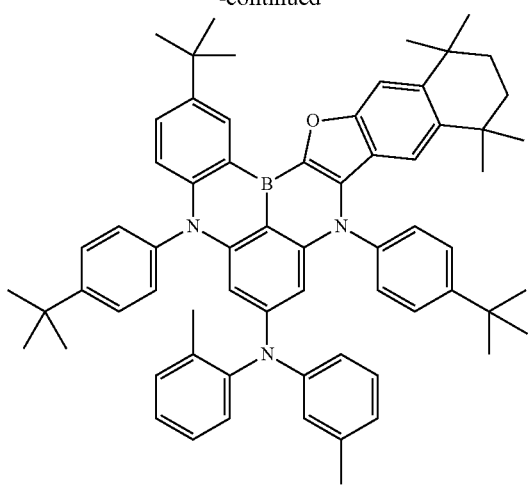
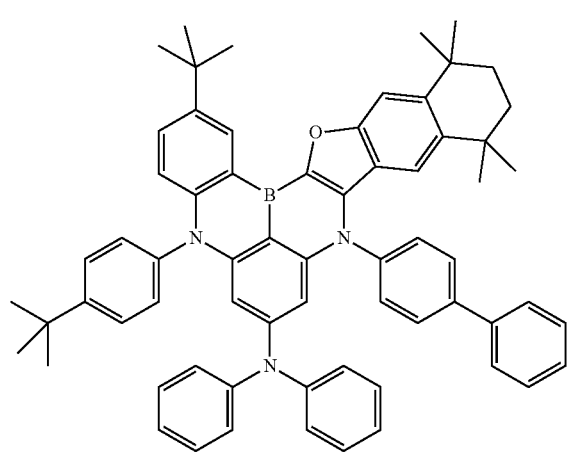
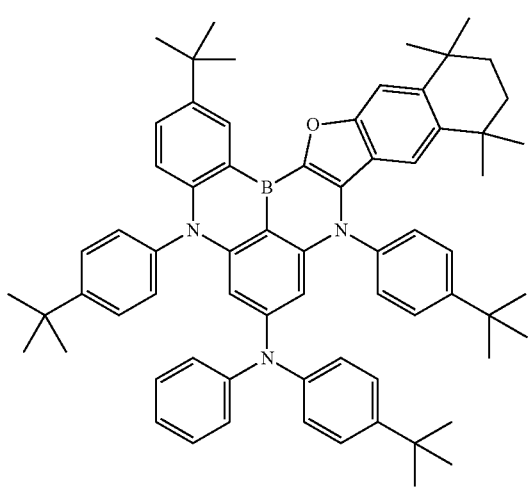
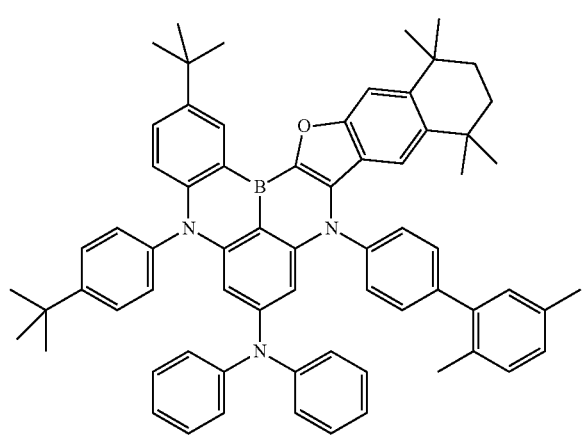
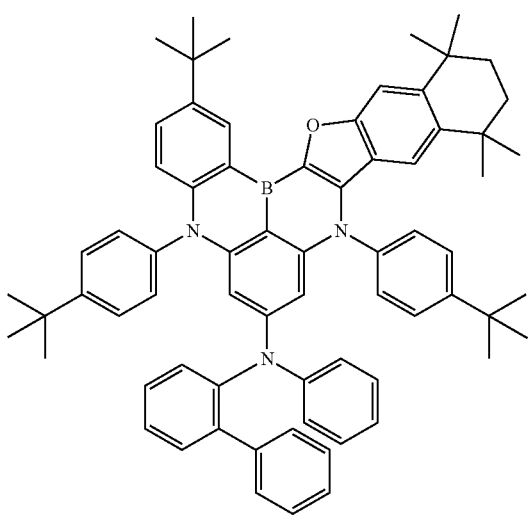

2501
-continued
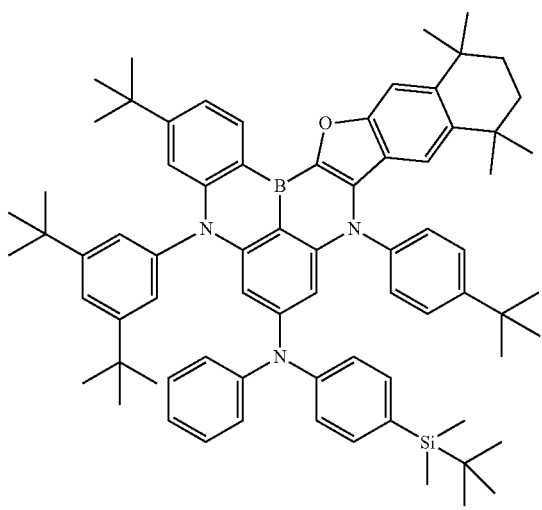
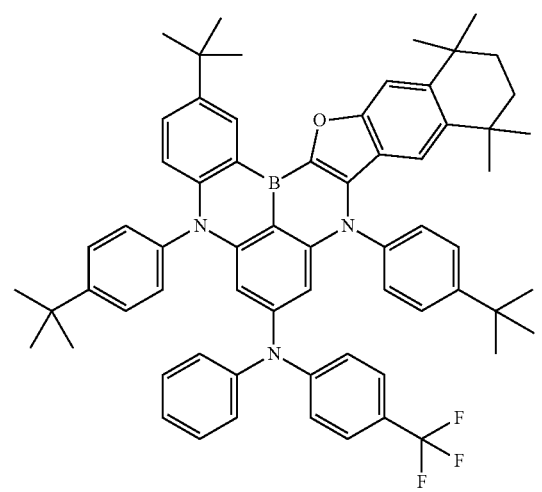
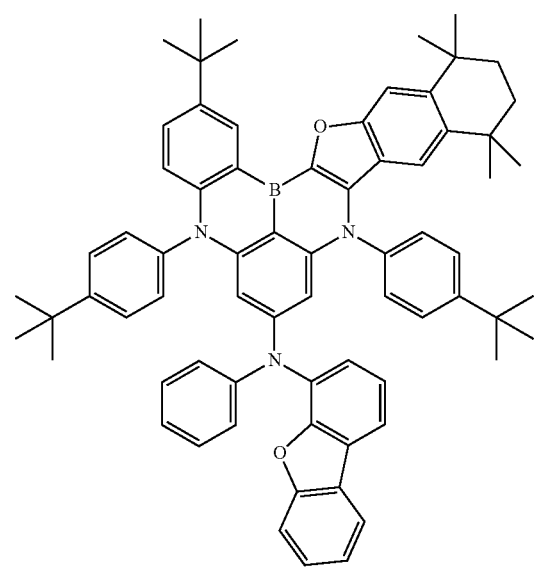
2502
-continued
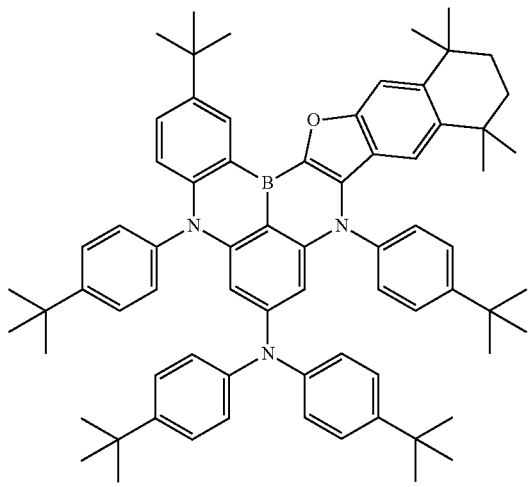
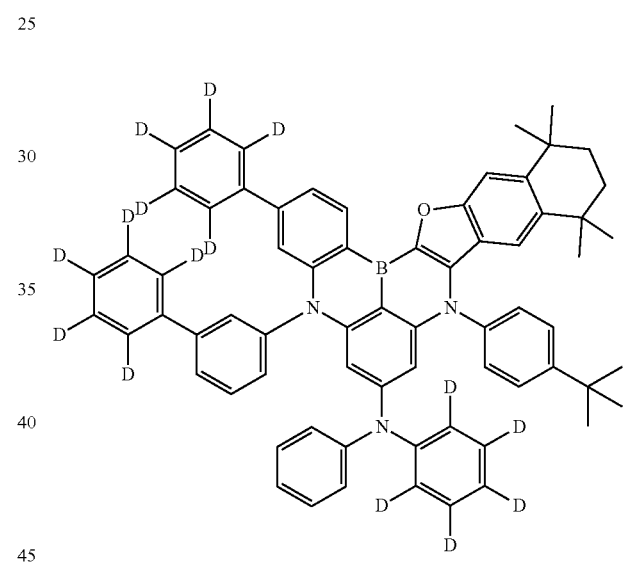
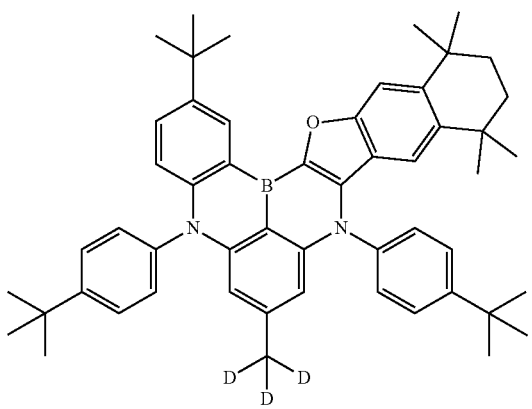

| 2503 | 2504 |
|---|---|
| -continued | -continued |
| 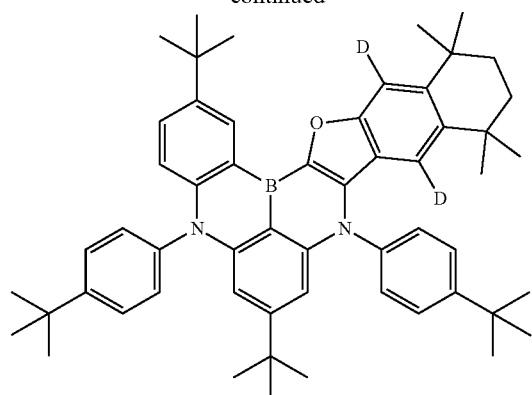 | 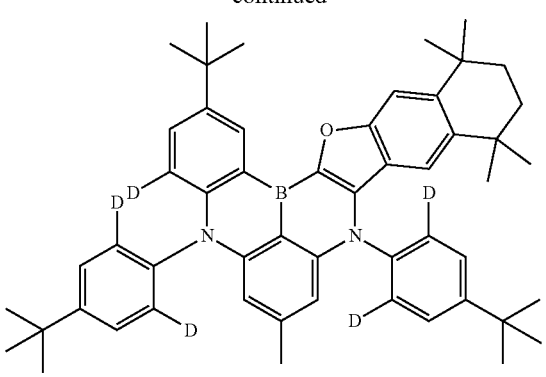 |
| 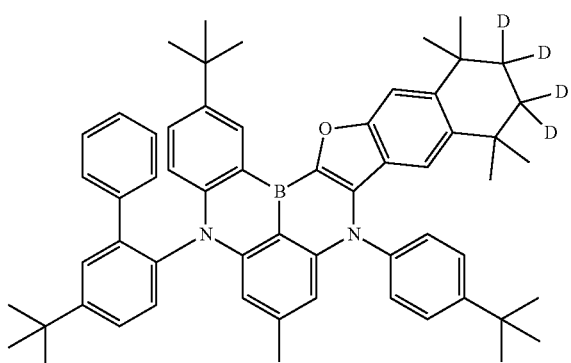 | 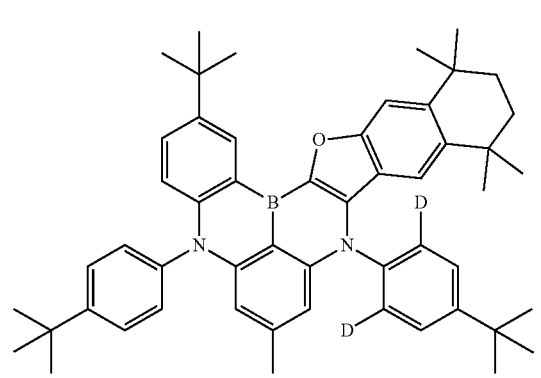 |
| 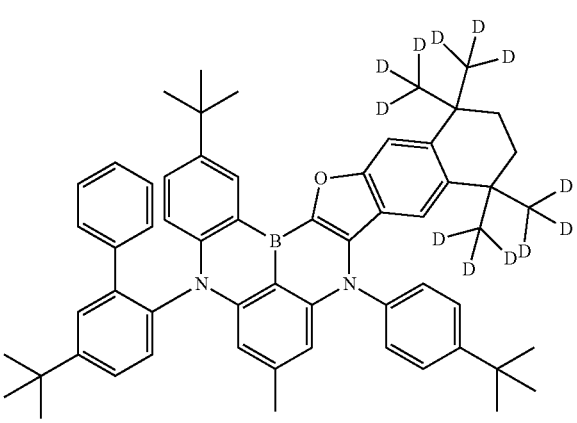 | 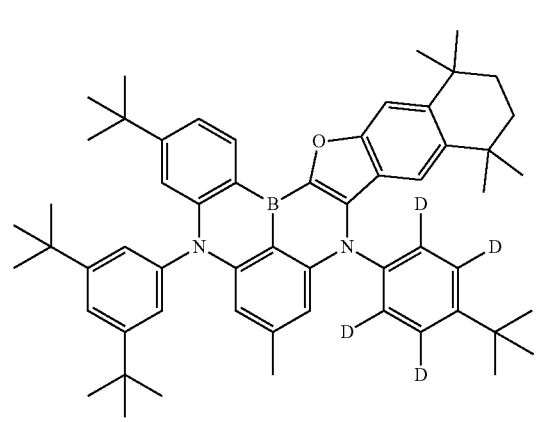 |
| 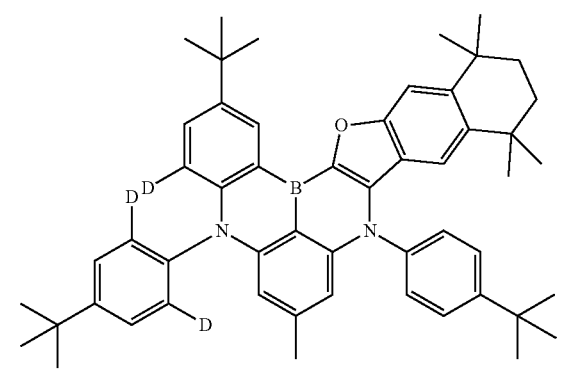 | 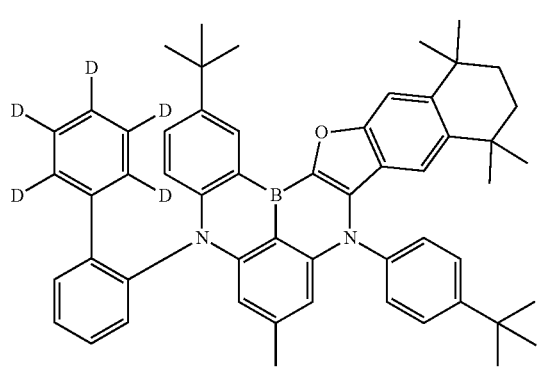 |

2505
-continued
2506
-continued
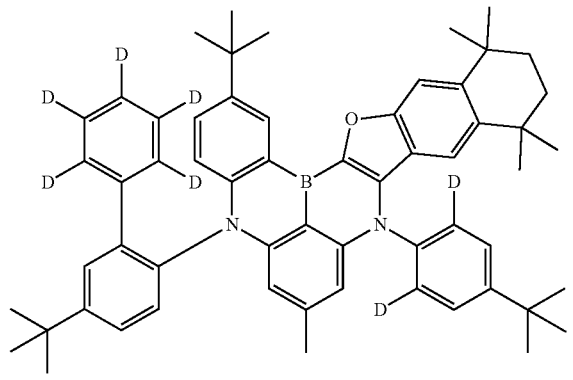
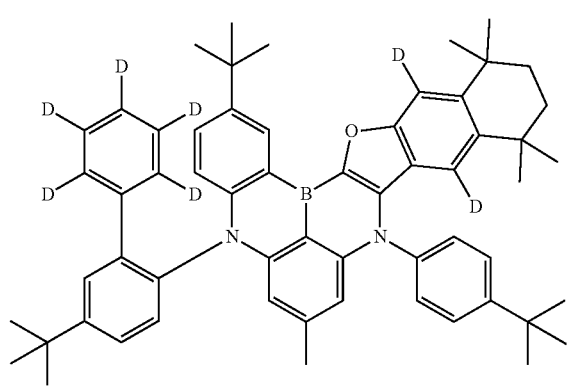
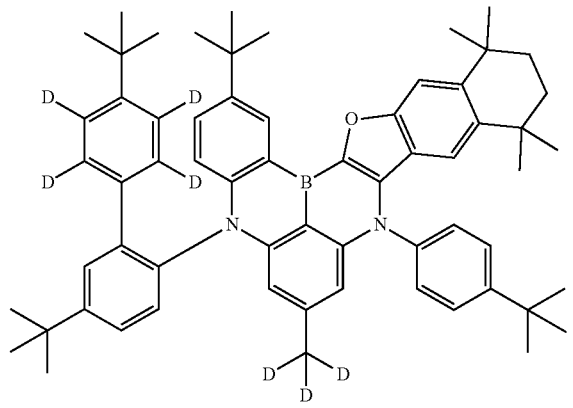
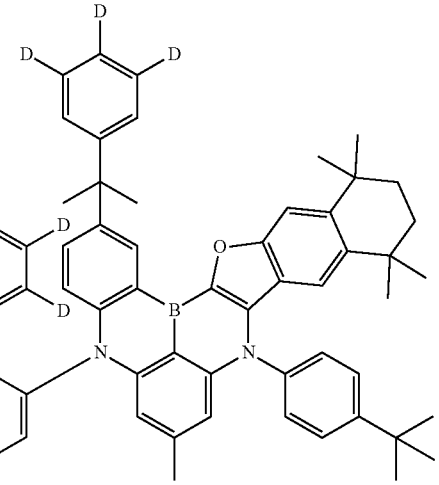
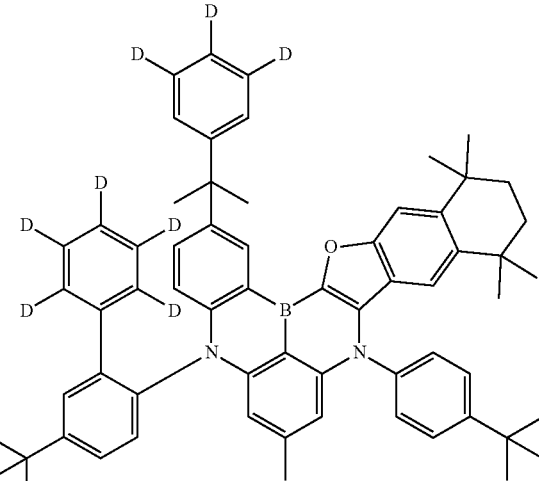
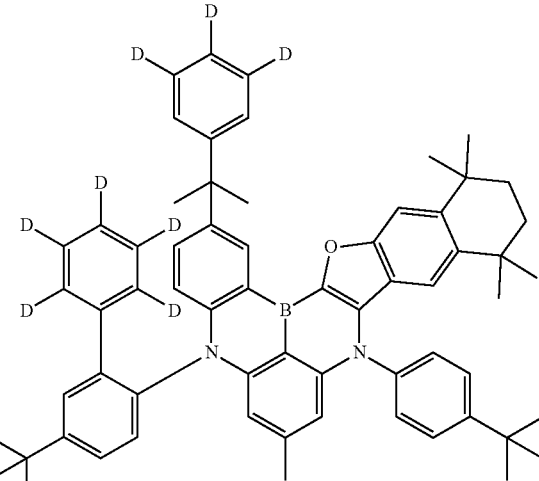

2507
-continued
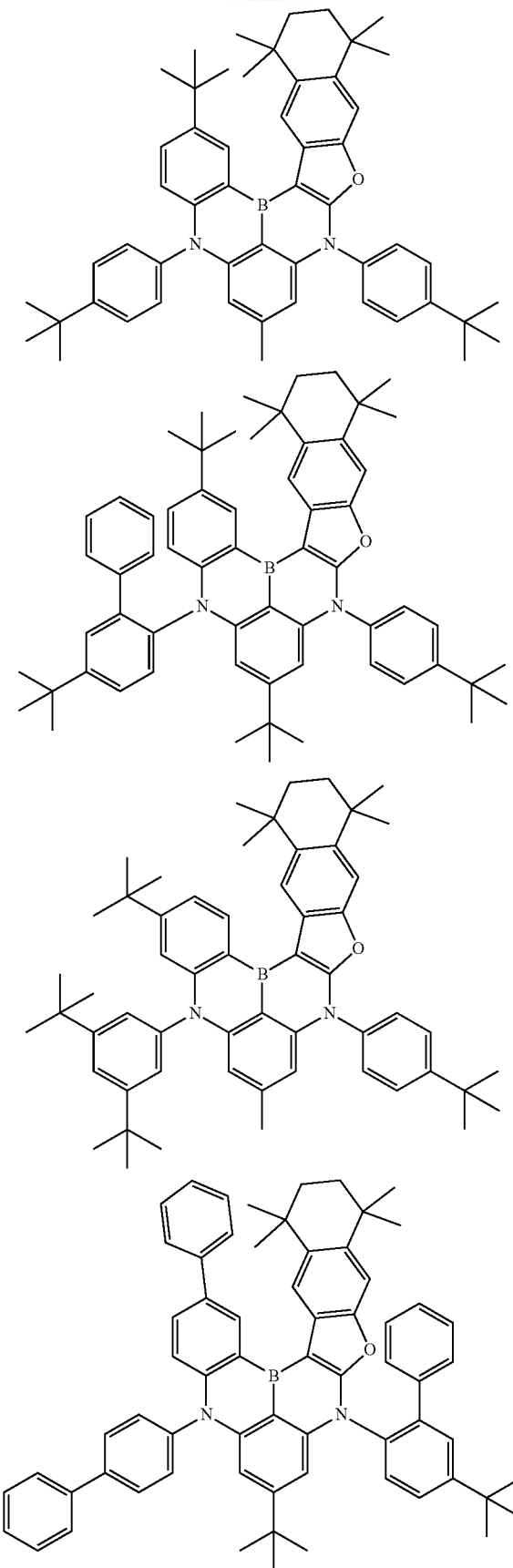
2508
-continued
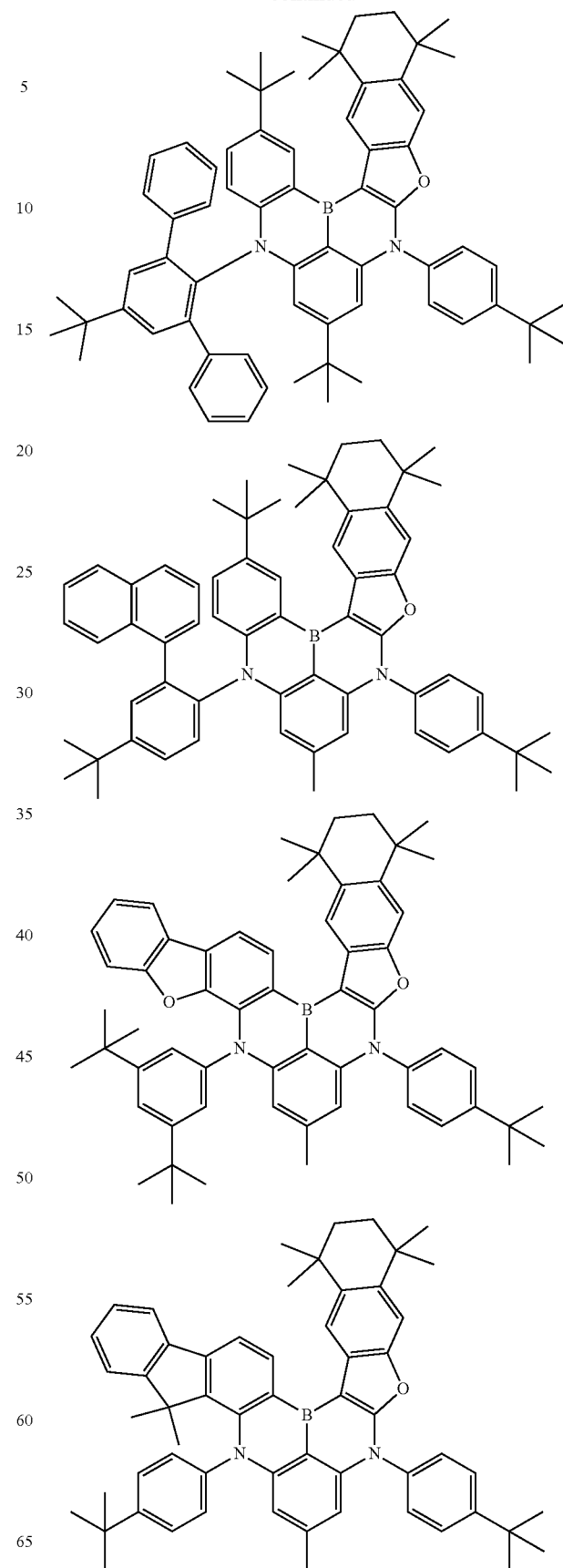

2509
-continued
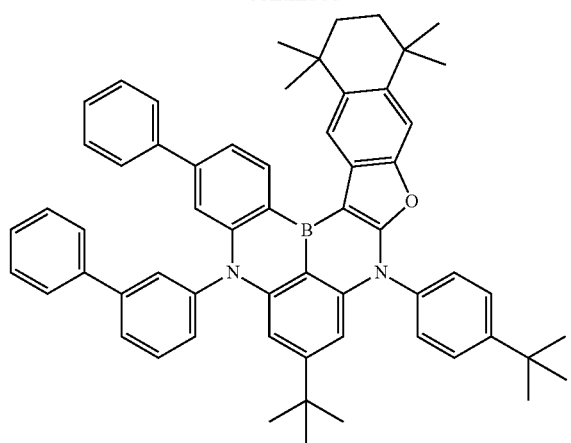
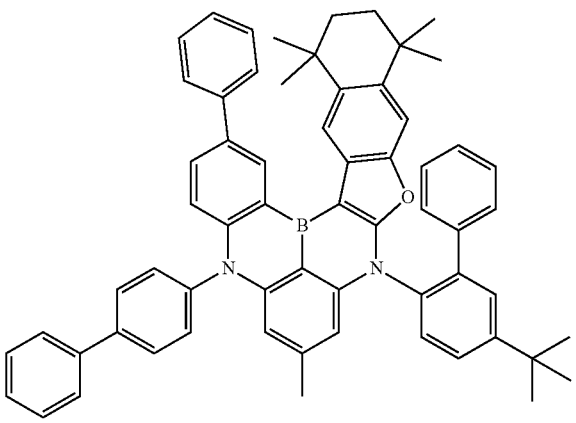
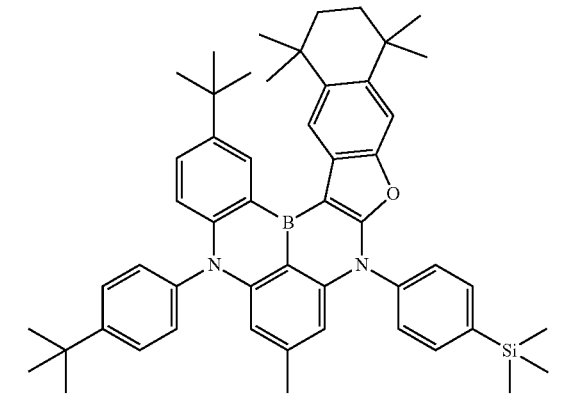
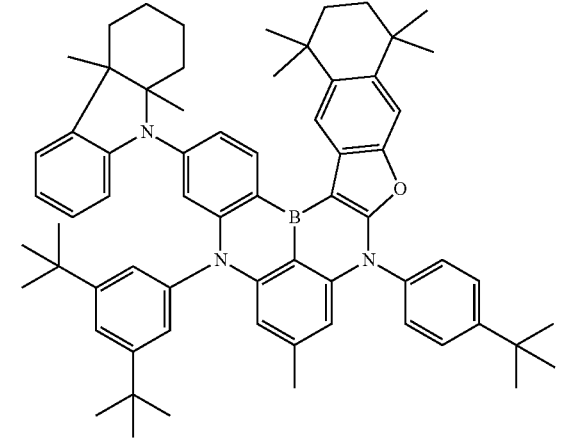
2510
-continued
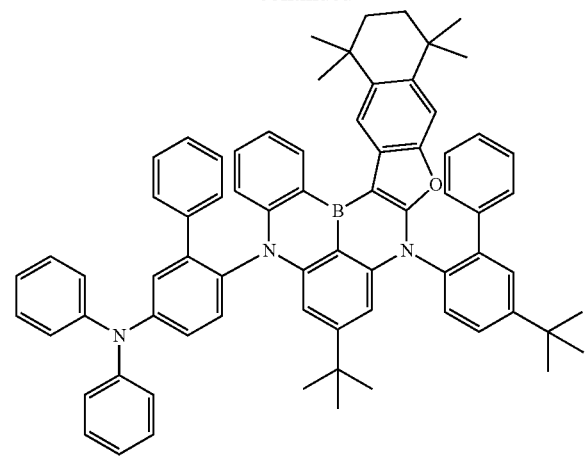
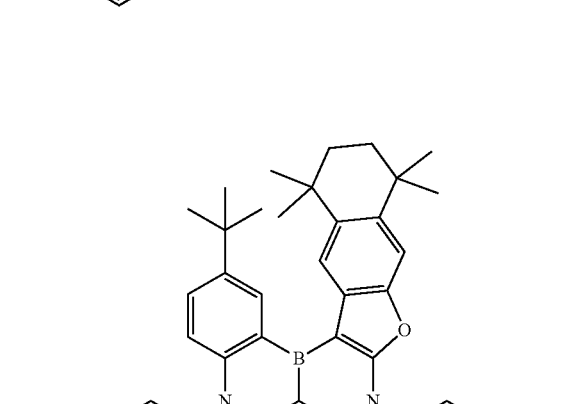
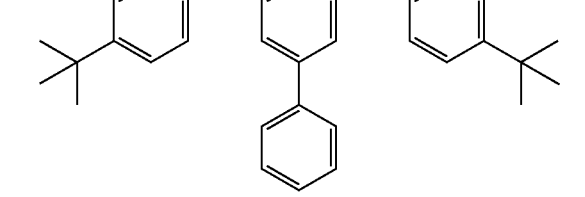

2511
-continued

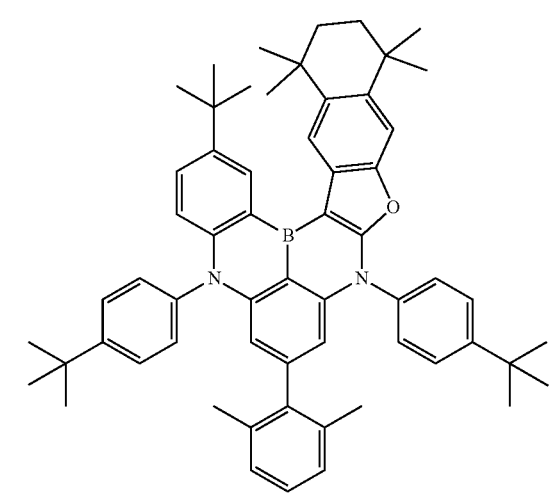
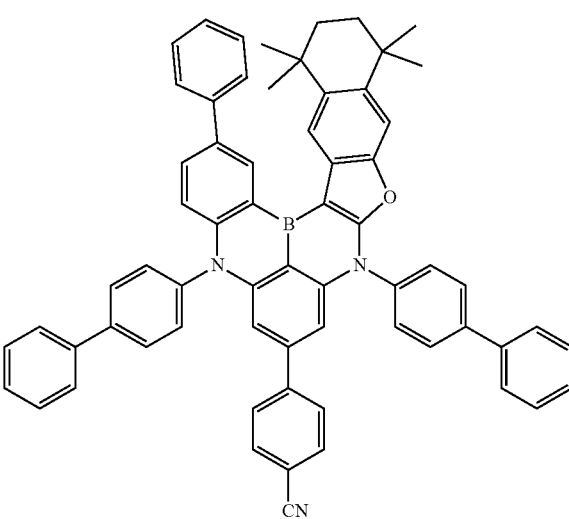
2512
-continued
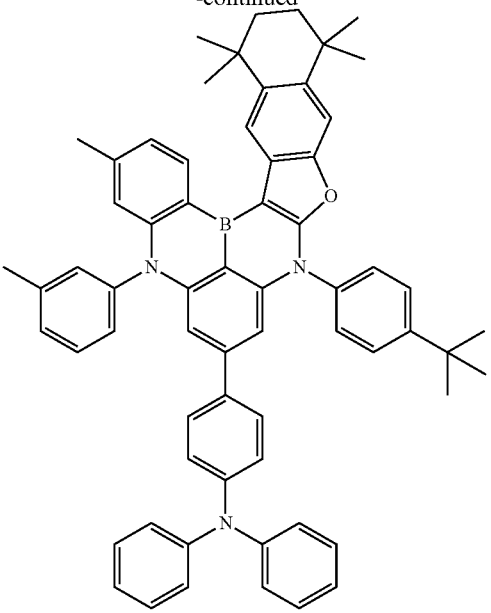
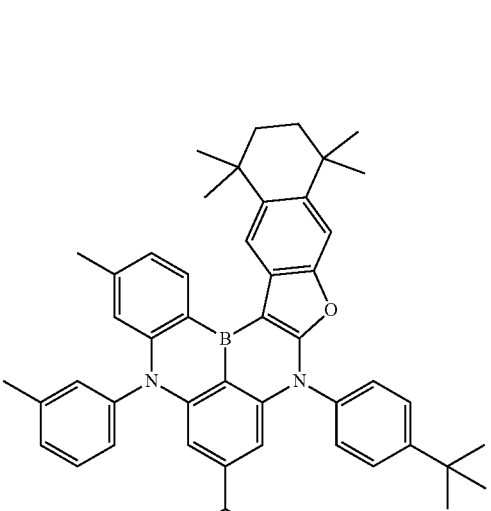
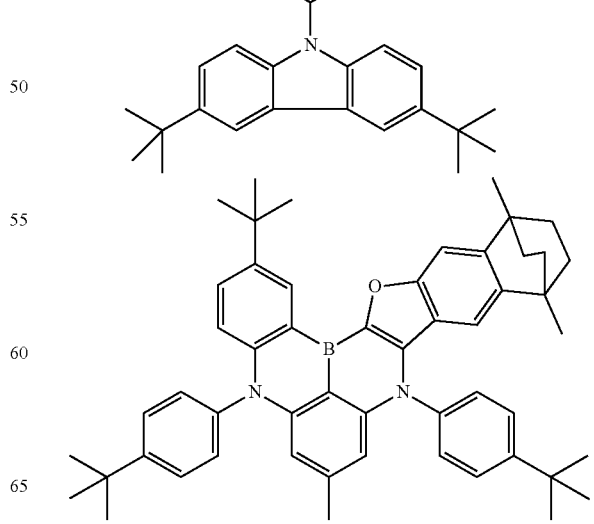

2513
-continued
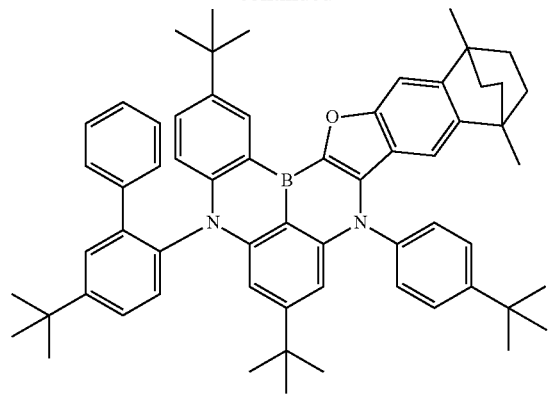
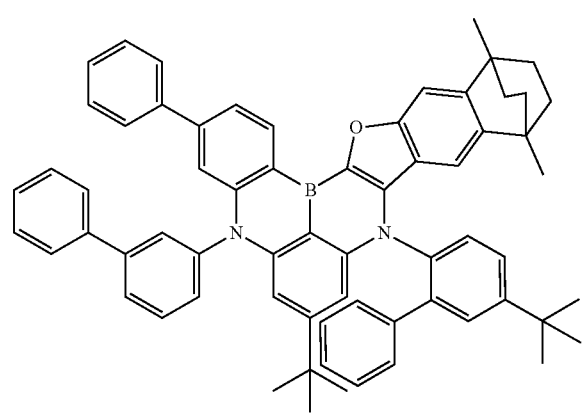
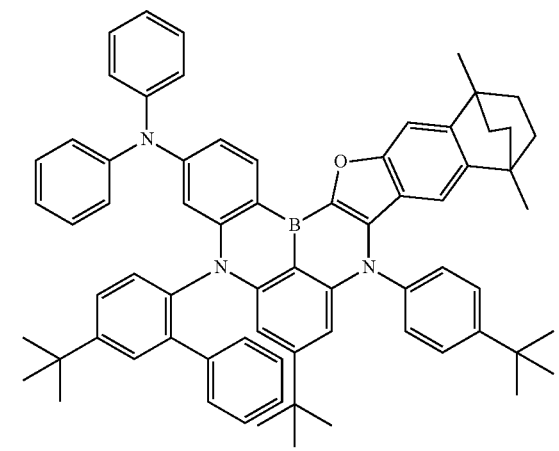
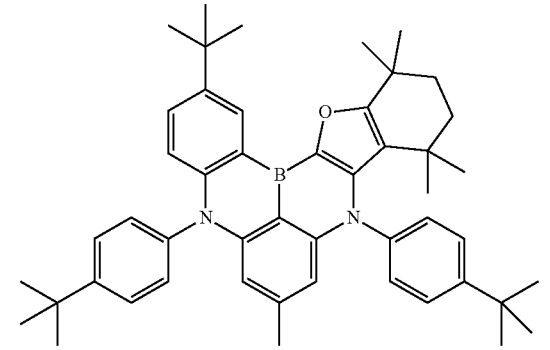
2514
-continued
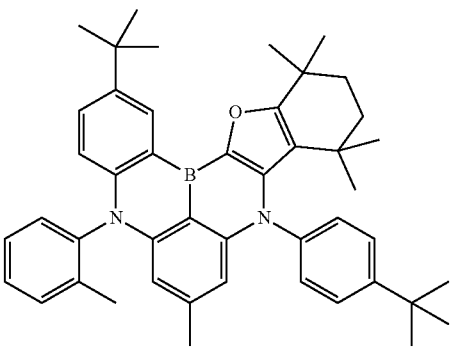
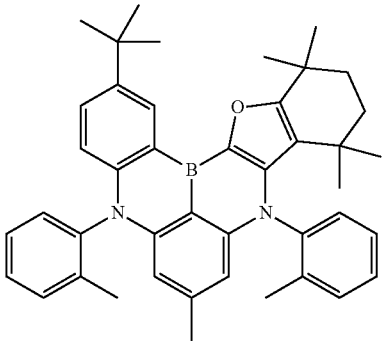
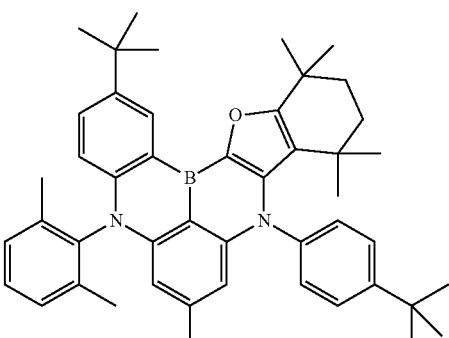
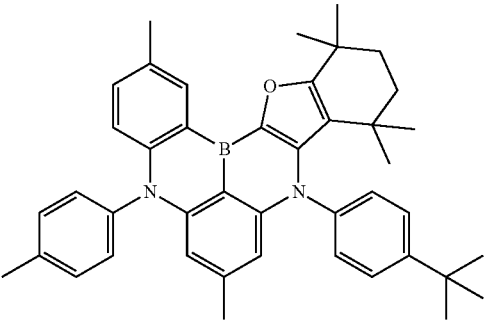
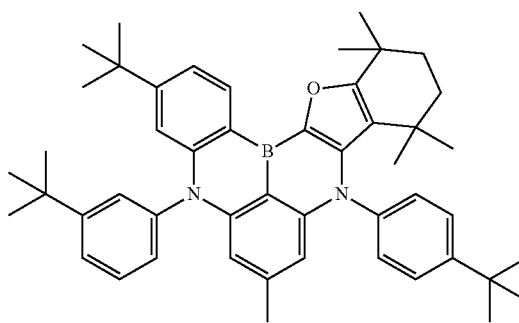

| 2515 -continued | 2516 -continued |
|---|---|
| 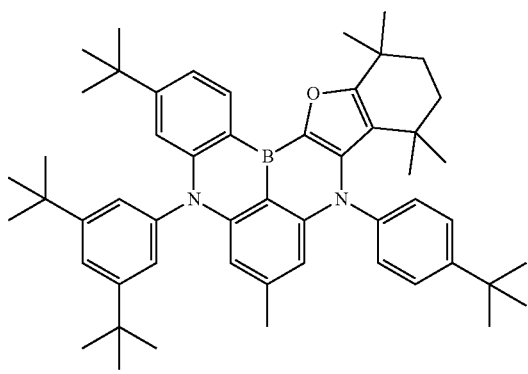 | 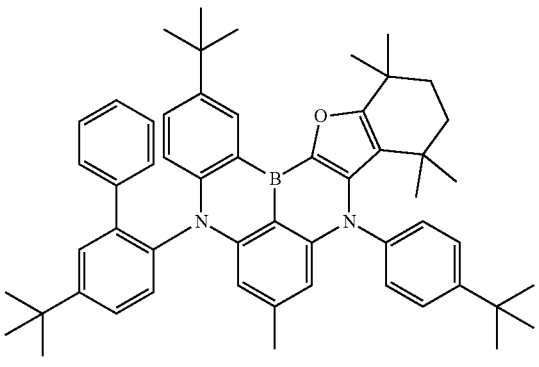 |
| 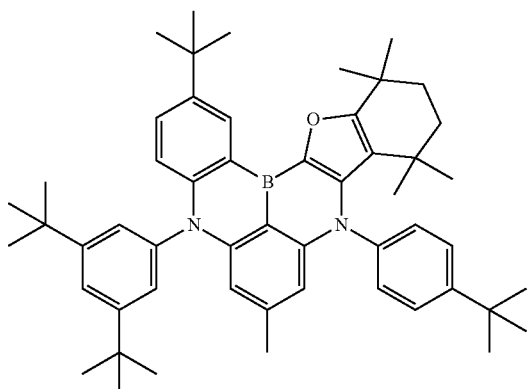 | 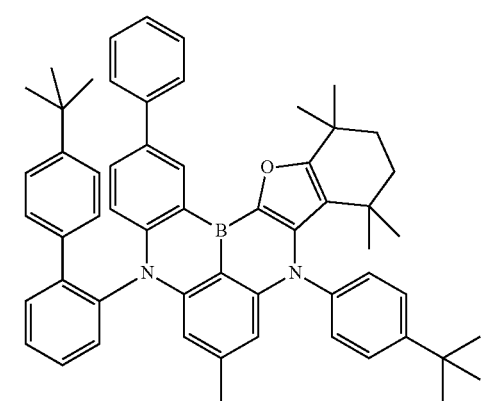 |
| 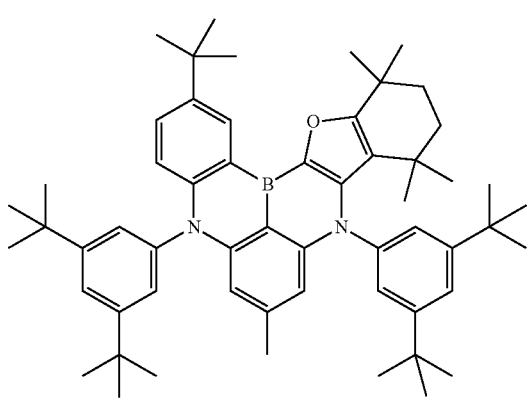 | 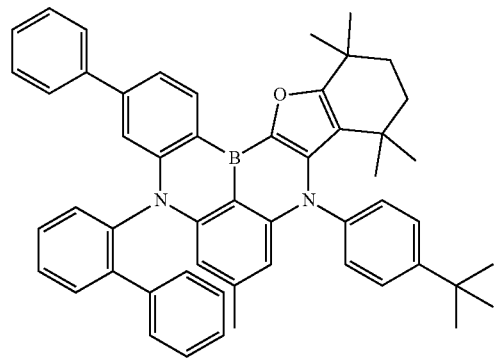 |
| 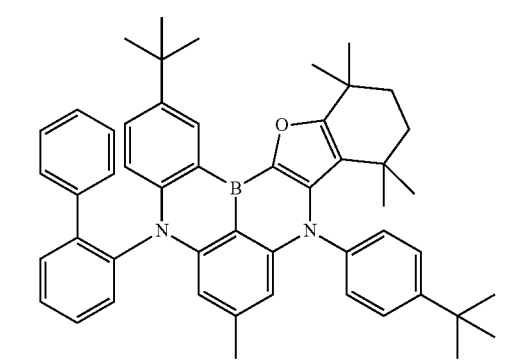 | 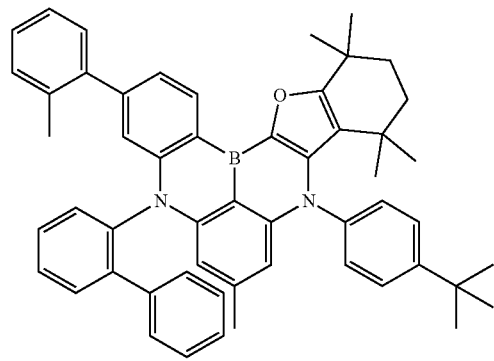 |

| 2517 -continued | 2518 -continued |
|---|---|
| 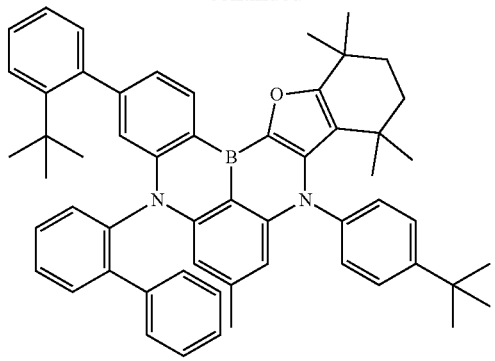 | 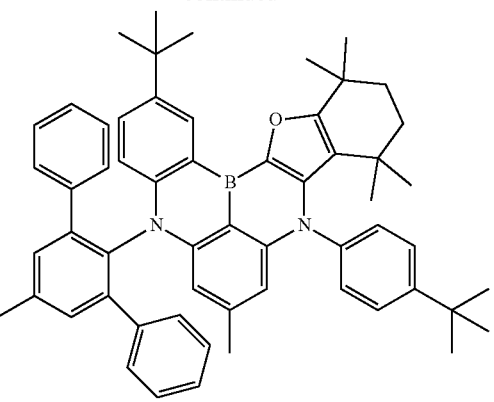 |
| 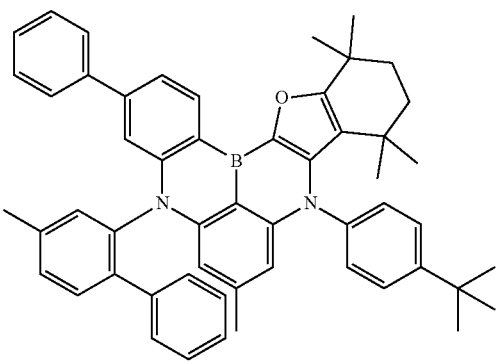 | 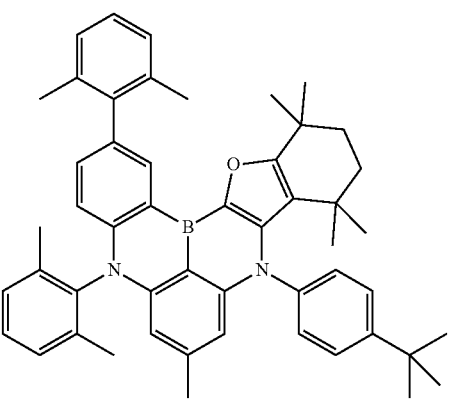 |
| 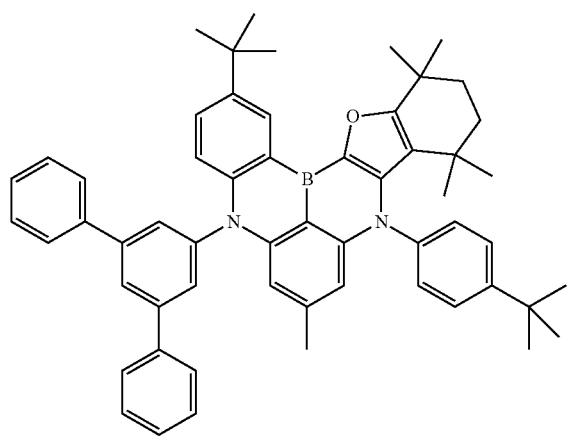 | 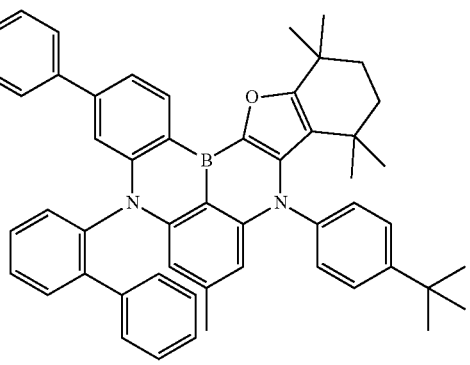 |
| 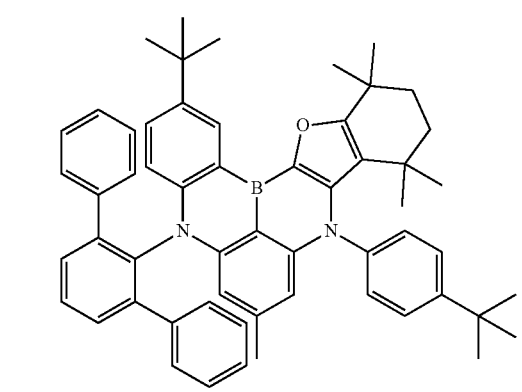 | 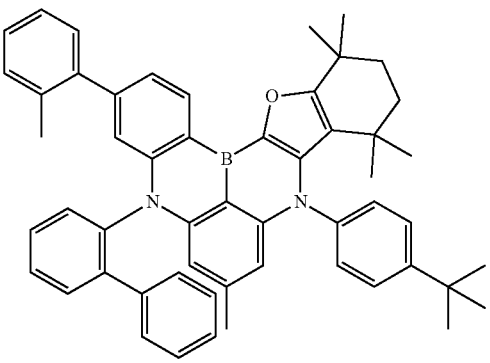 |

2519
-continued
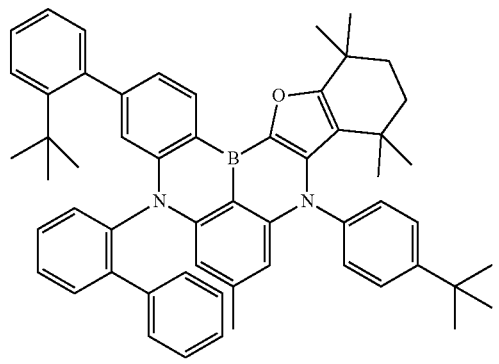
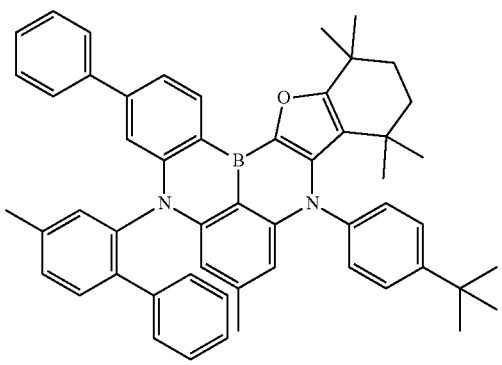
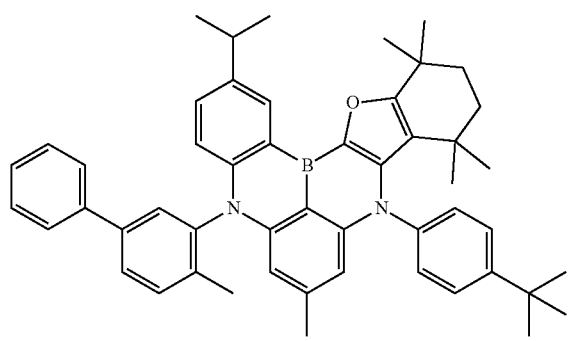
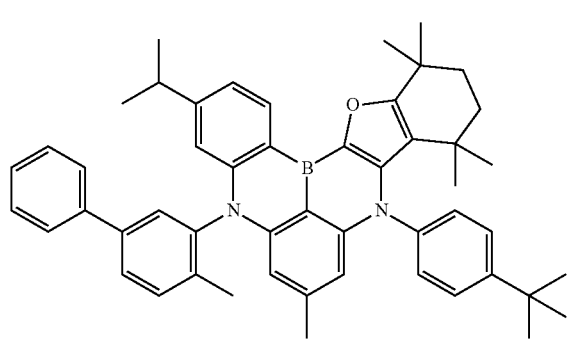
2520
-continued
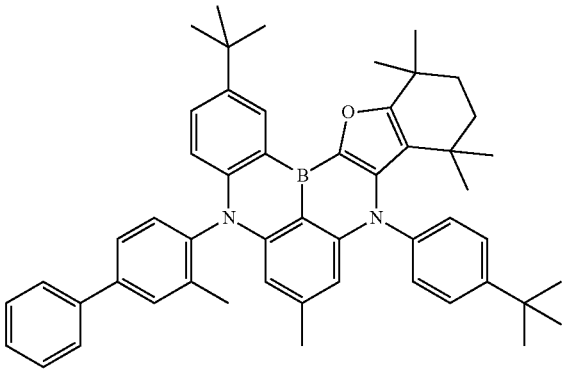
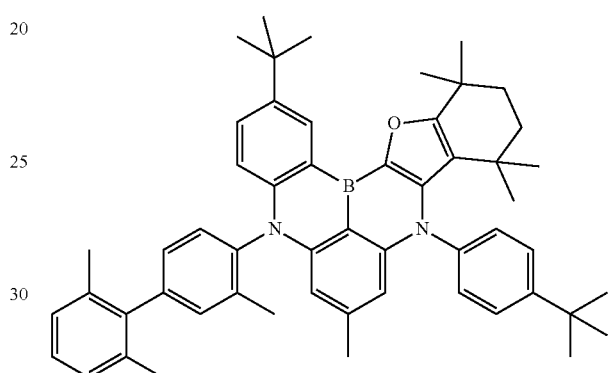
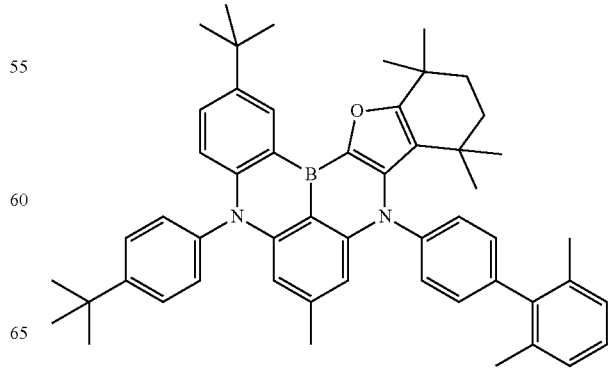

2521
-continued
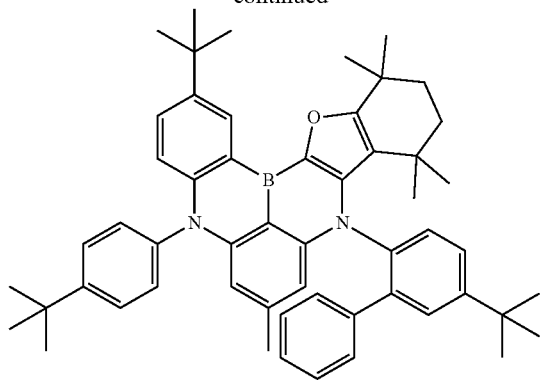
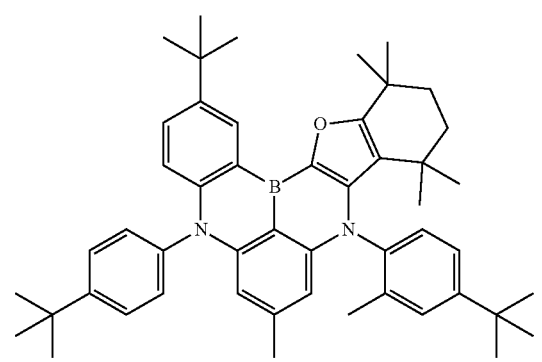
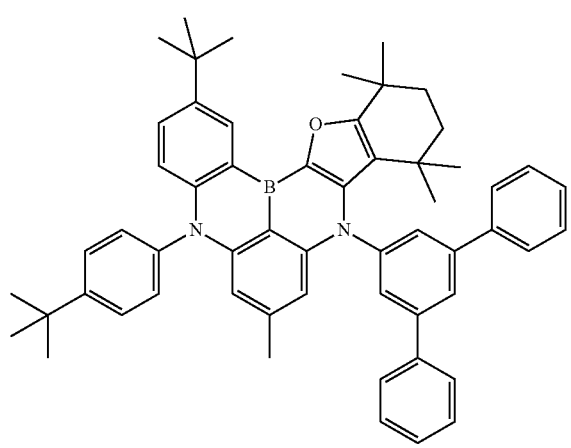
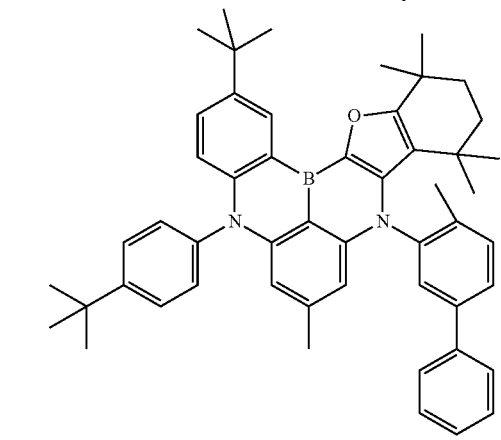
2522
-continued
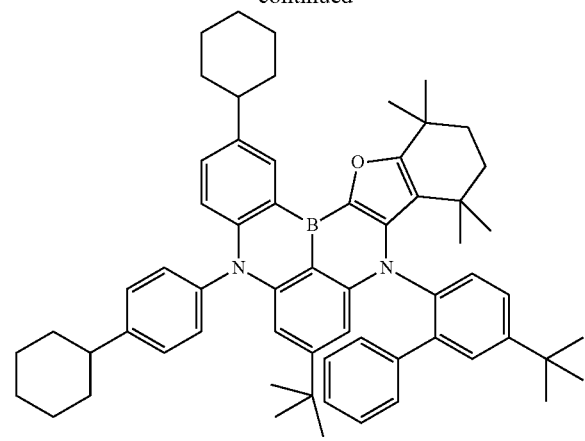
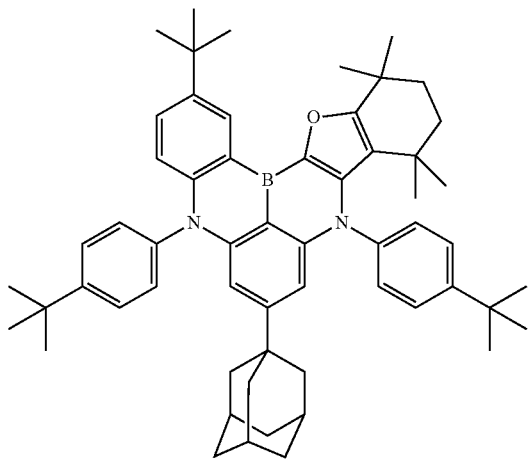
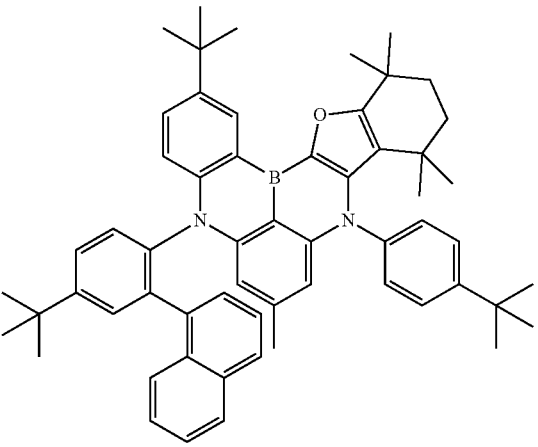

| 2523 -continued | 2524 -continued |
|---|---|
| 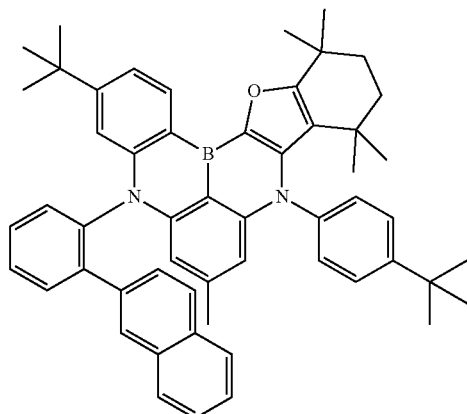 | 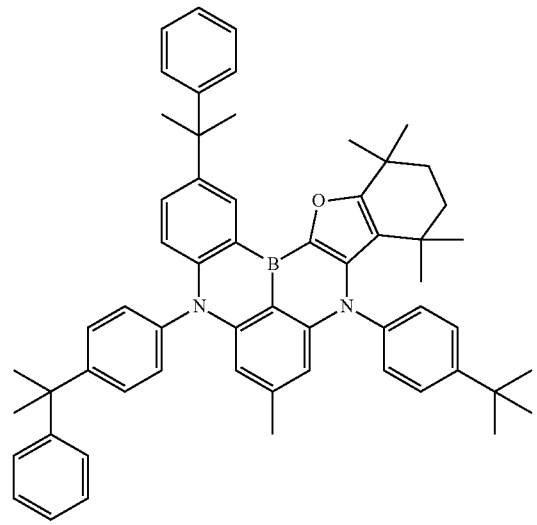 |
| 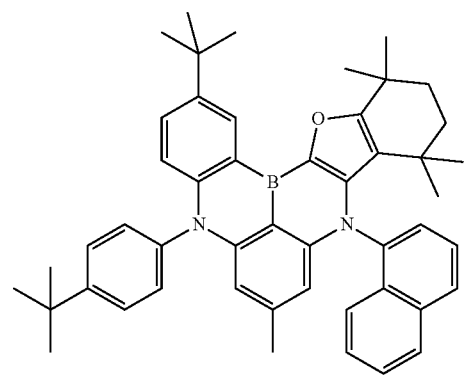 | |
| | 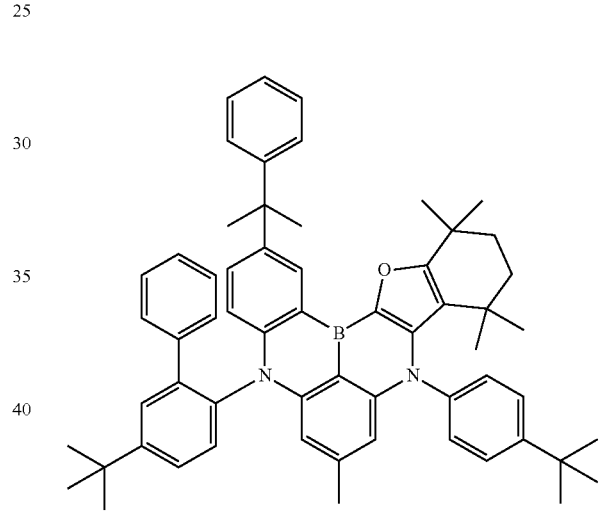 |
| 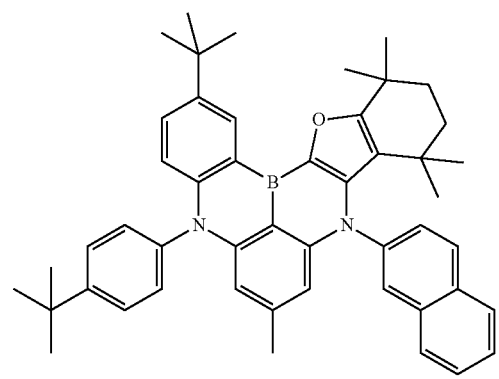 | |
| 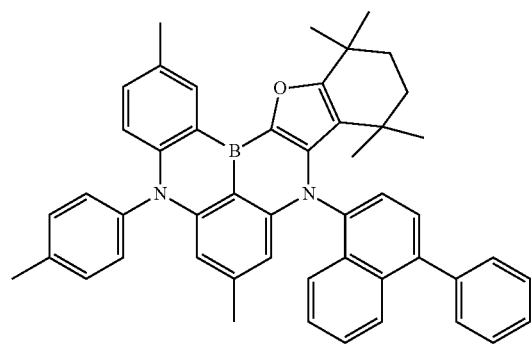 | 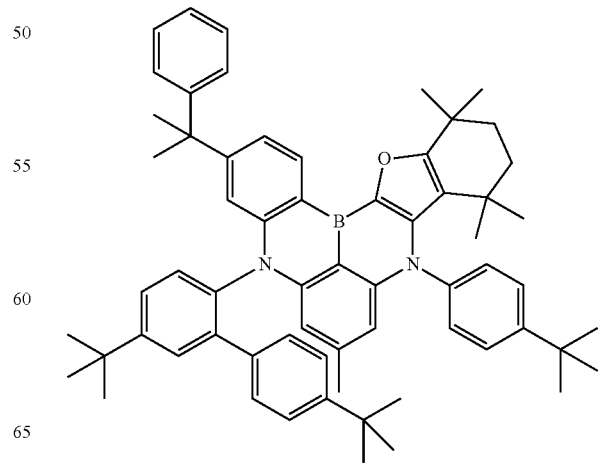 |

US 11,685,751 B2
2525
-continued
2526
-continued
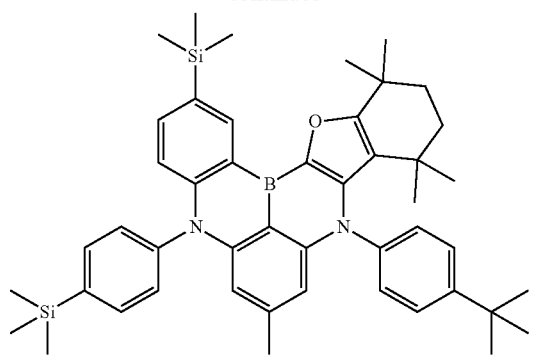
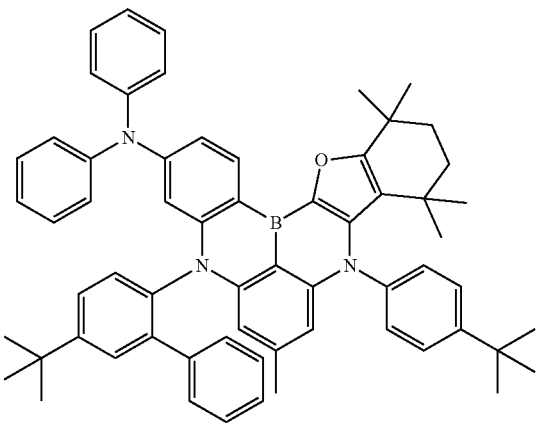
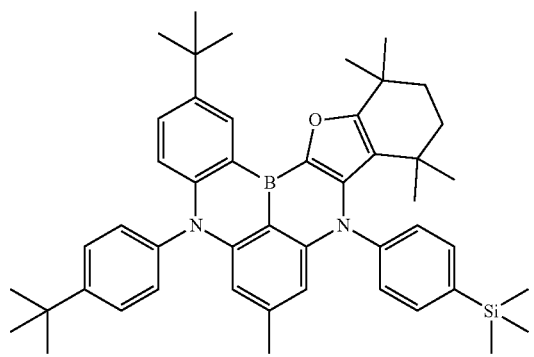
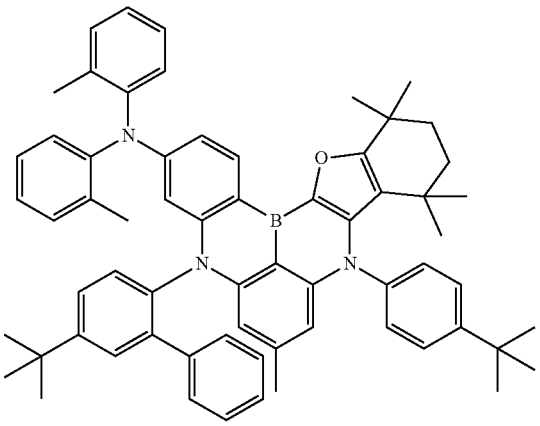
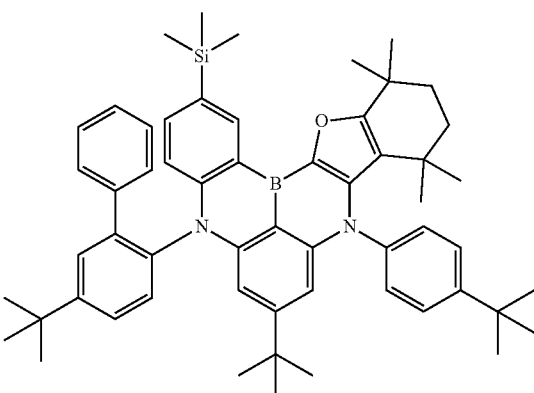
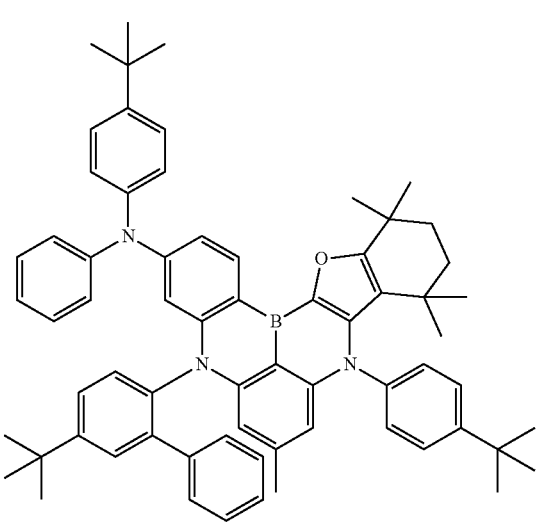
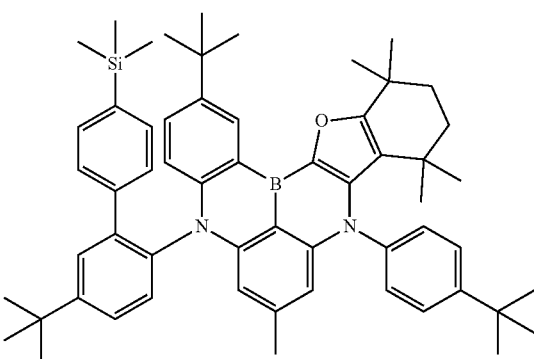

2527
-continued
2528
-continued
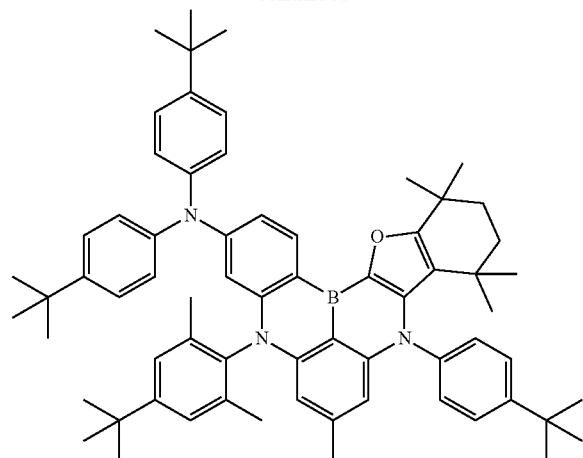
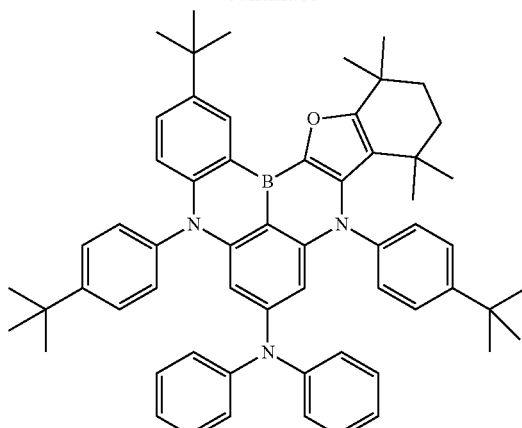
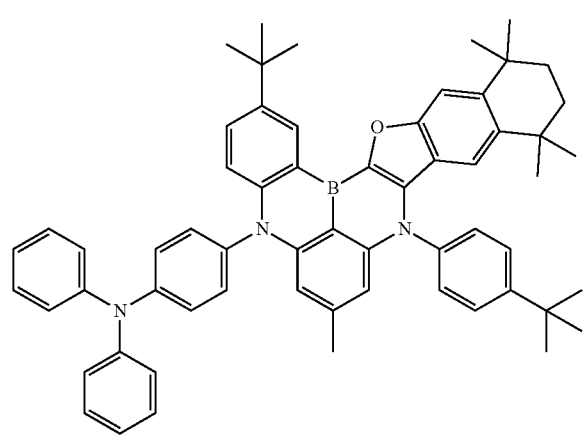
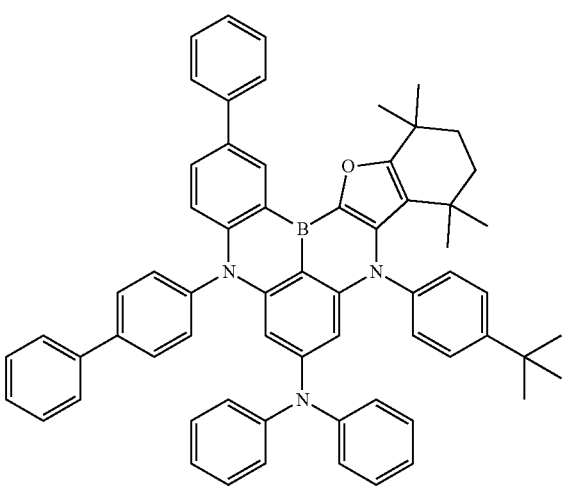
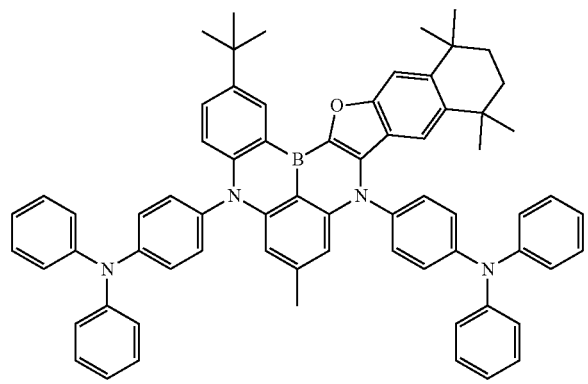
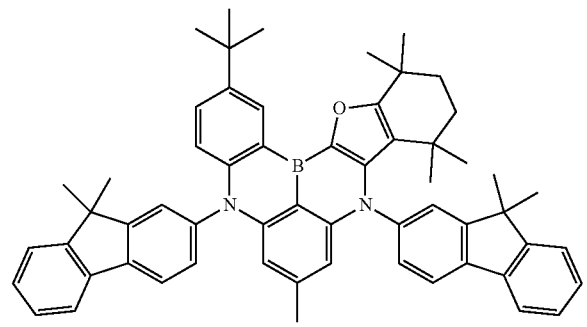
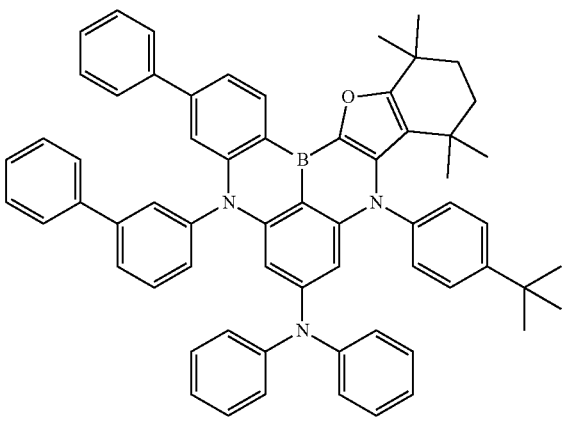

2529 -continued
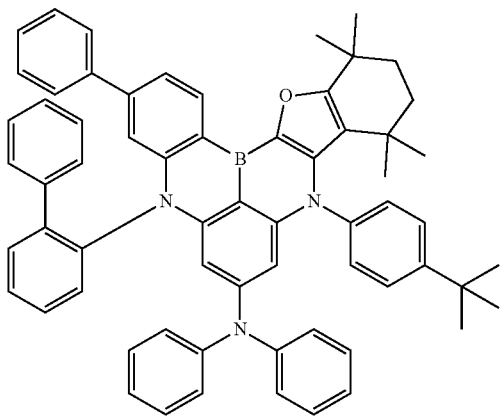
2530 -continued
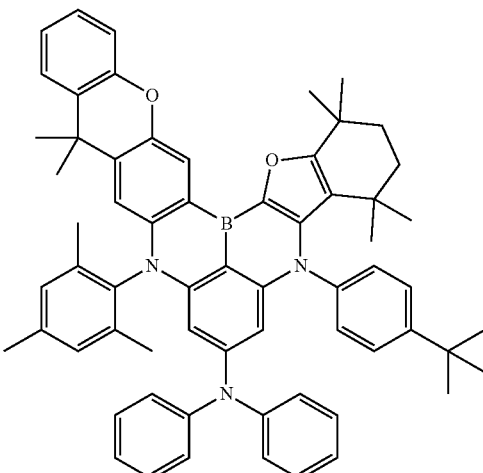
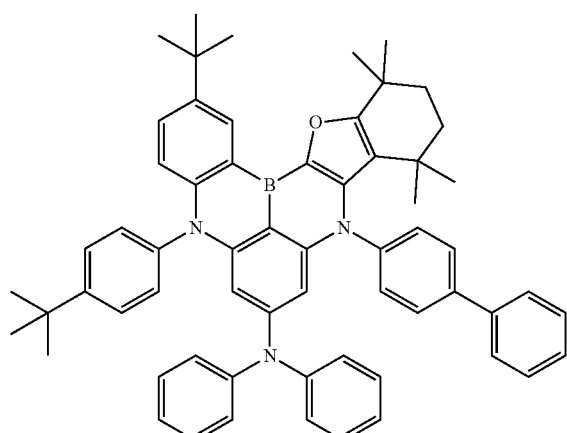
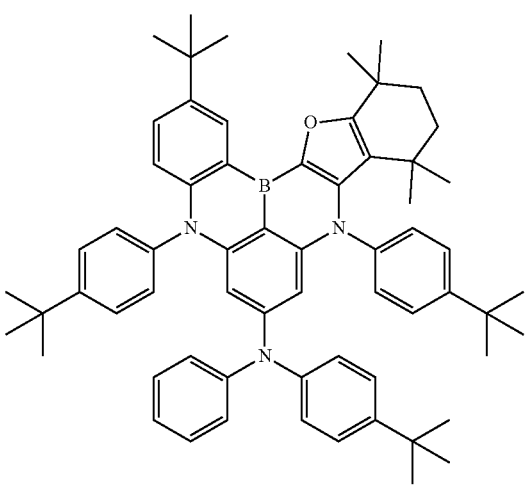
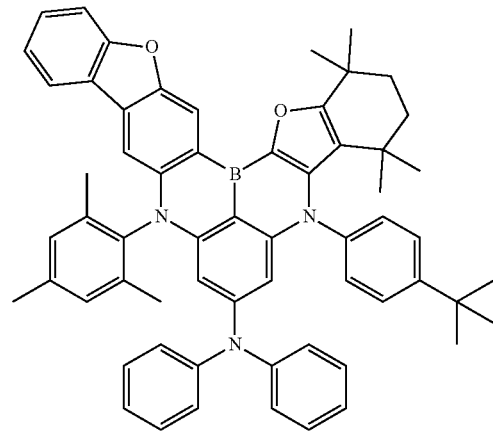
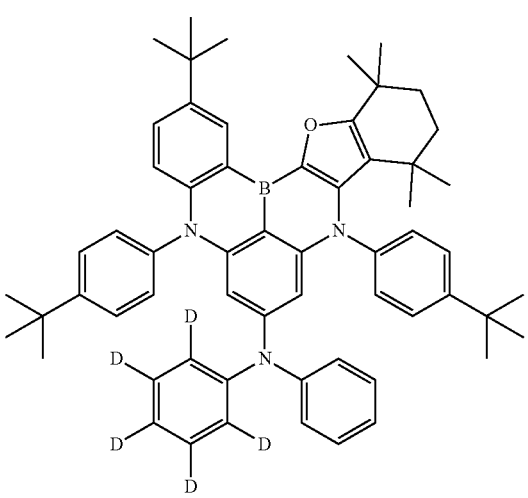

2531
-continued
2532
-continued
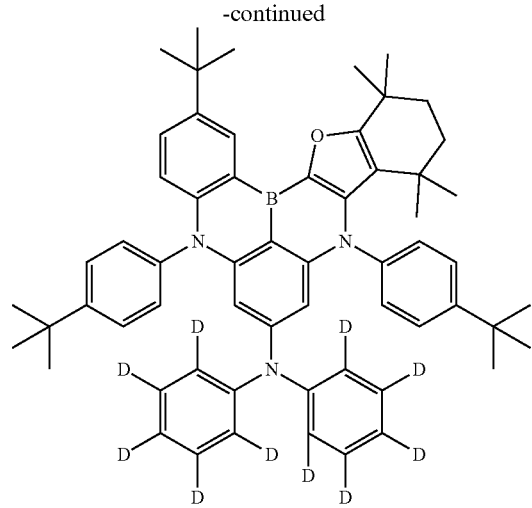
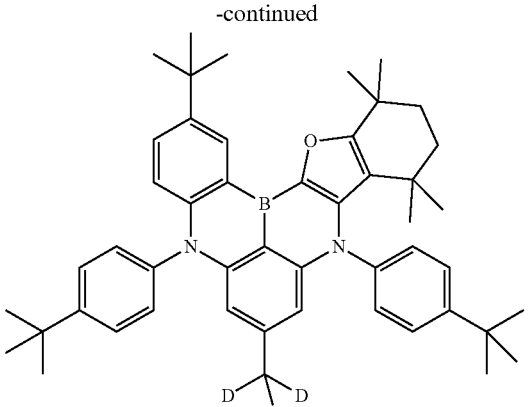
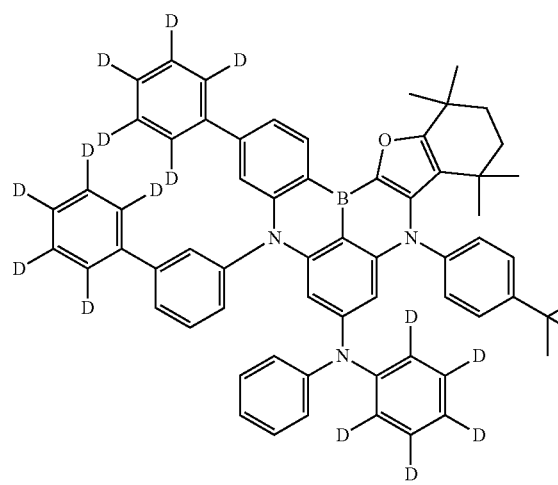
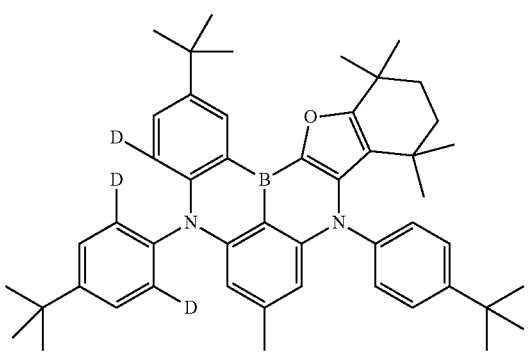
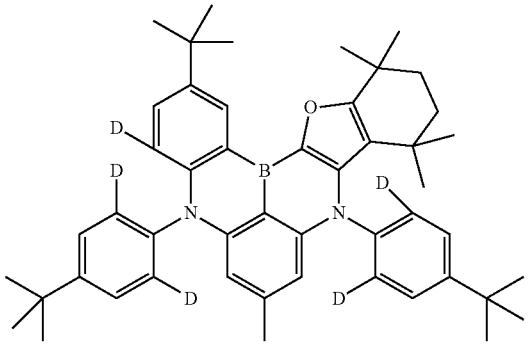
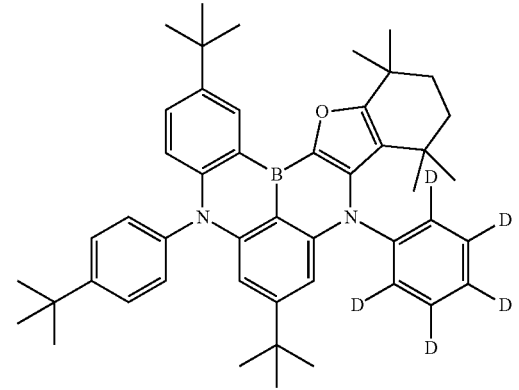

2533
-continued
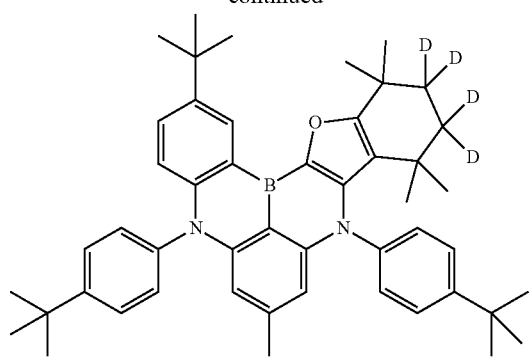
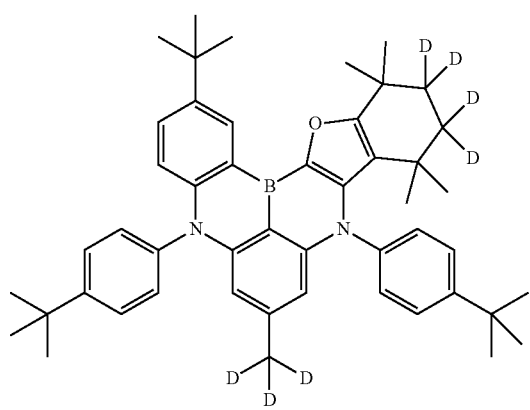
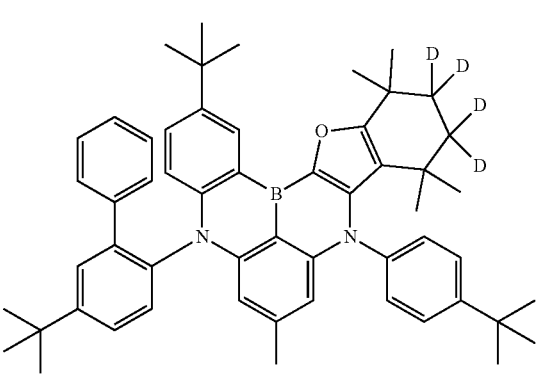
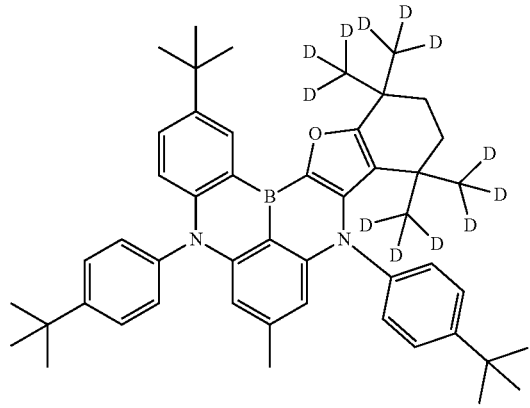
2534
-continued
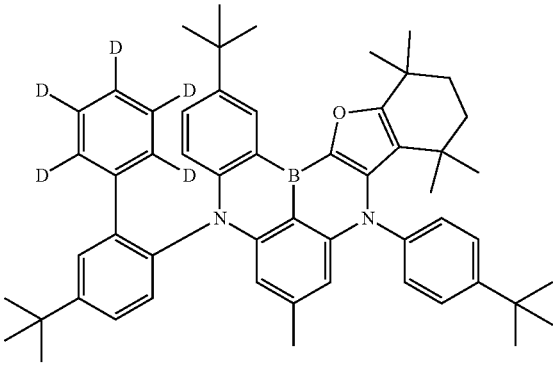
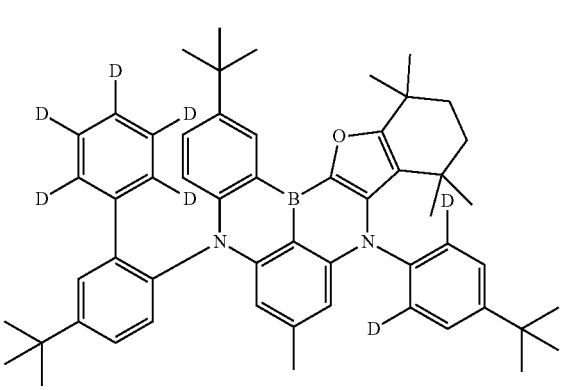
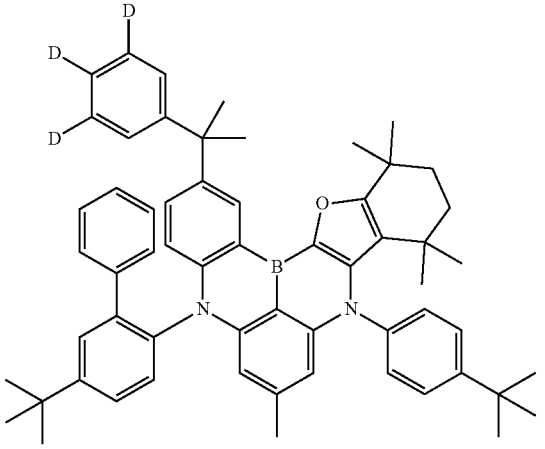
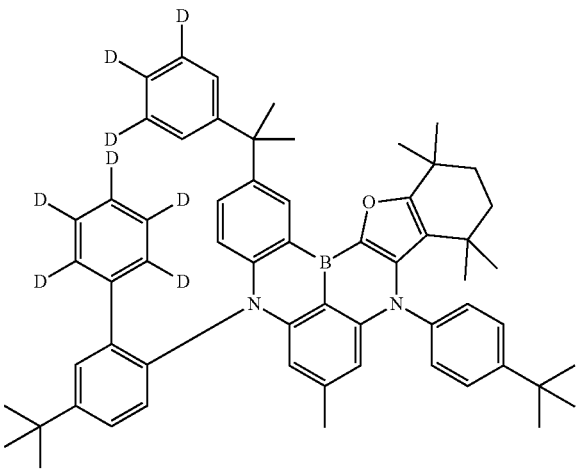

2535
-continued

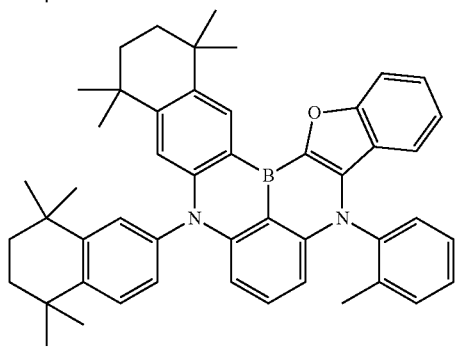
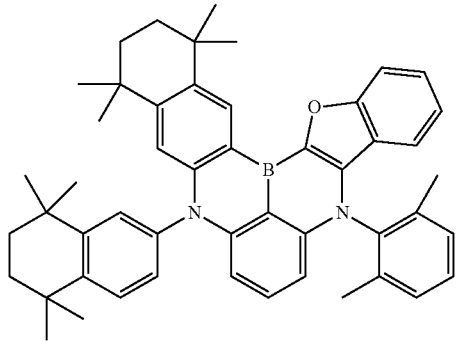
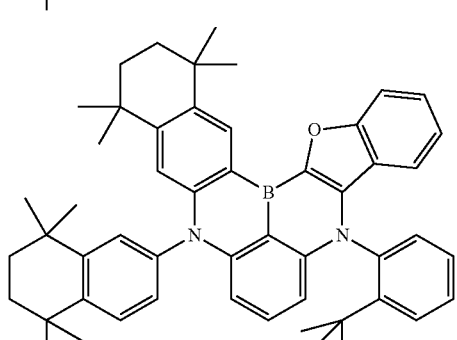
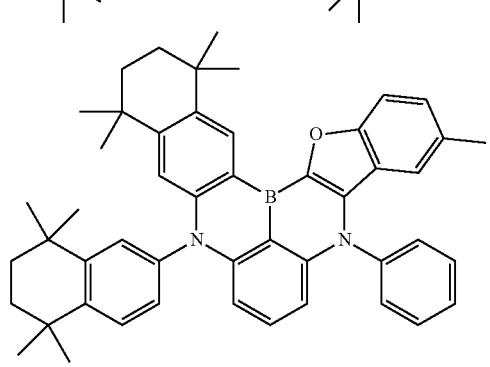
2536
-continued
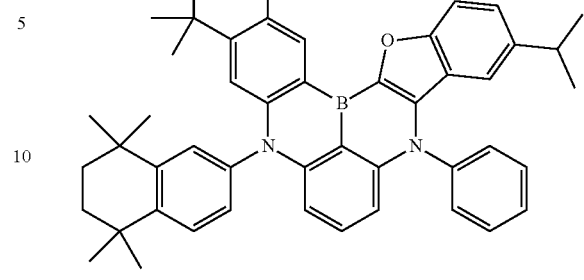
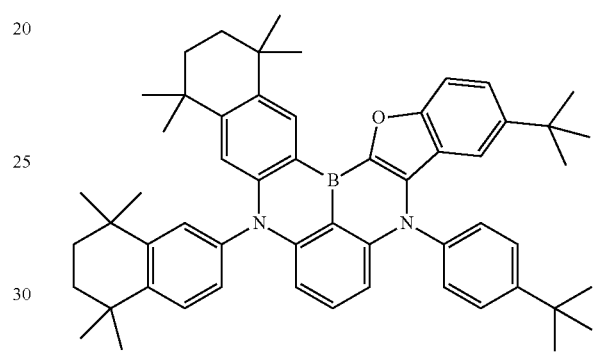
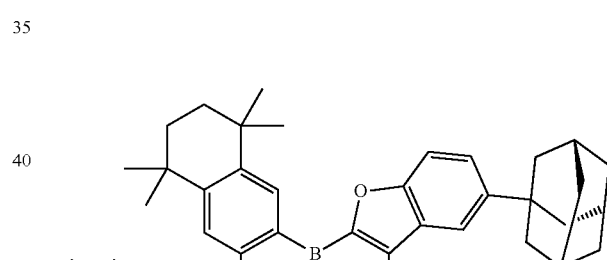
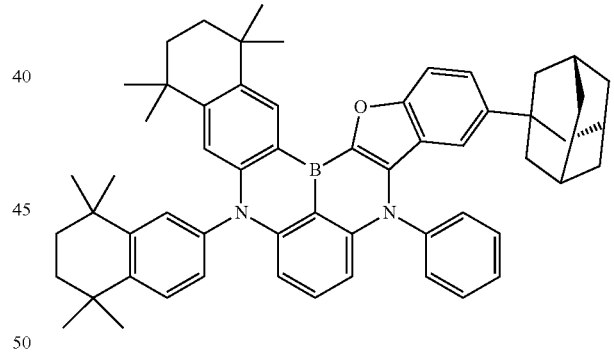
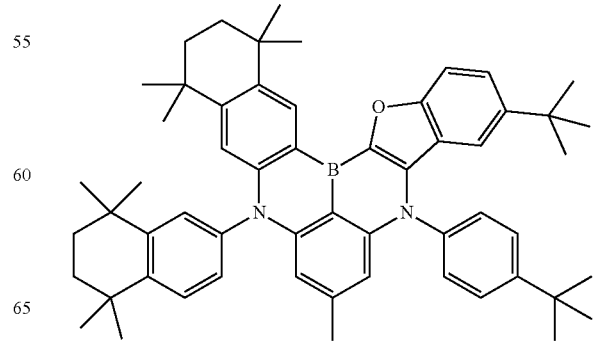

| 2537 -continued | 2538 -continued |
|---|---|
| 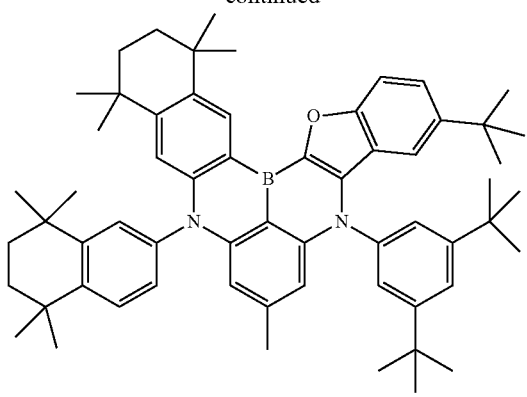 | 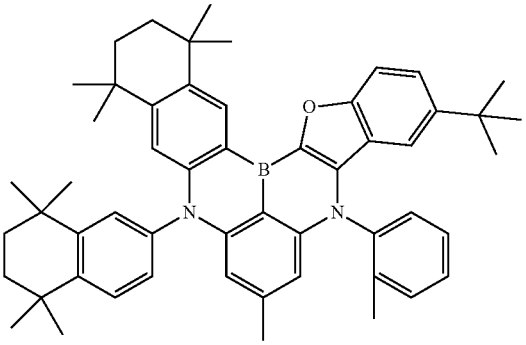 |
| 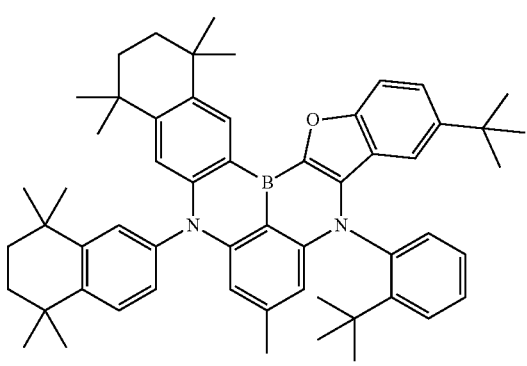 | 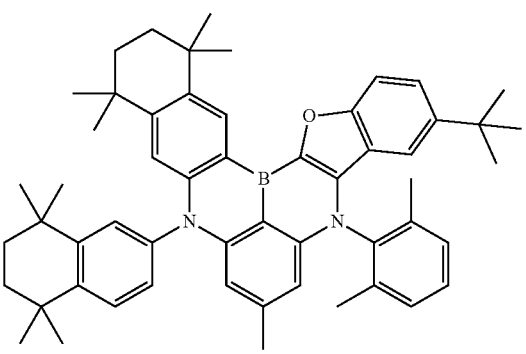 |
| 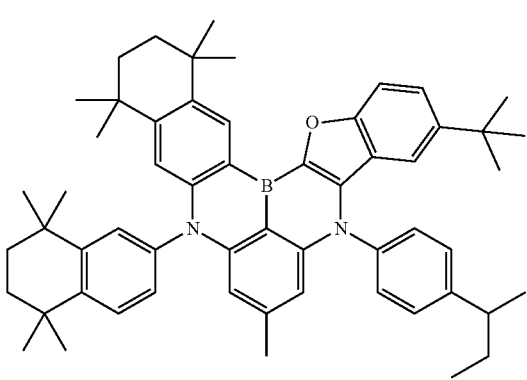 | 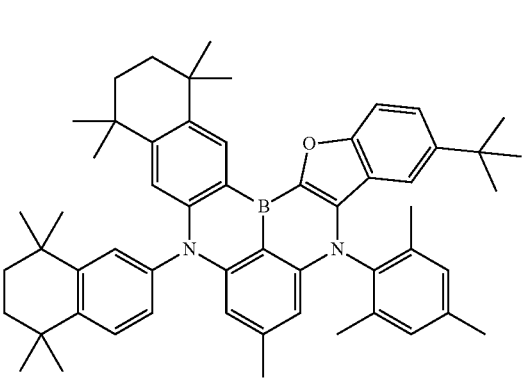 |
| 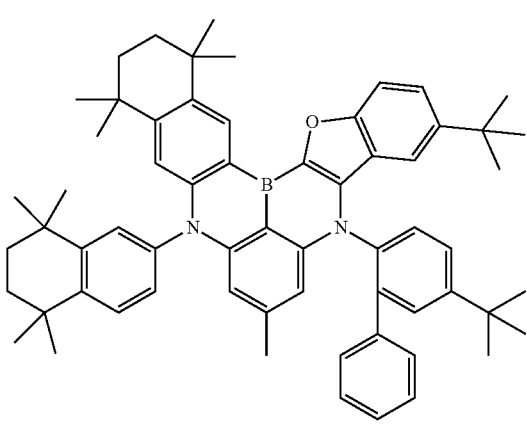 | 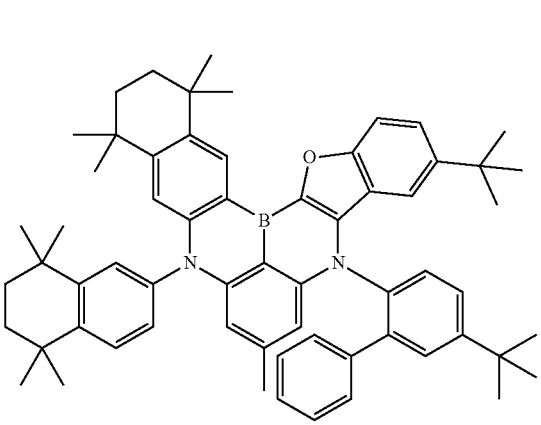 |

| 2539 -continued | 2540 -continued |
|---|---|
| 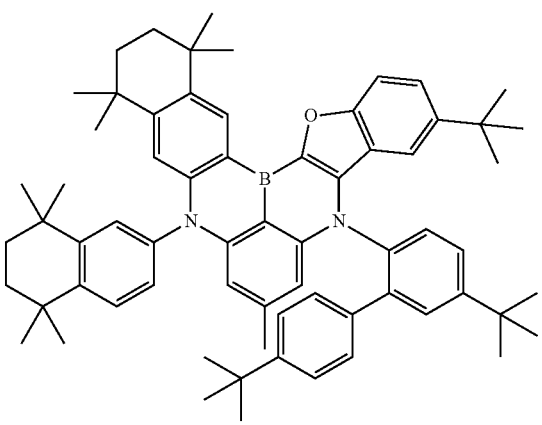 | 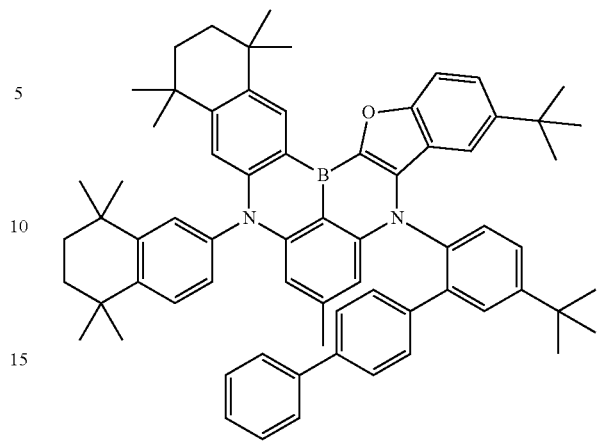 |
| 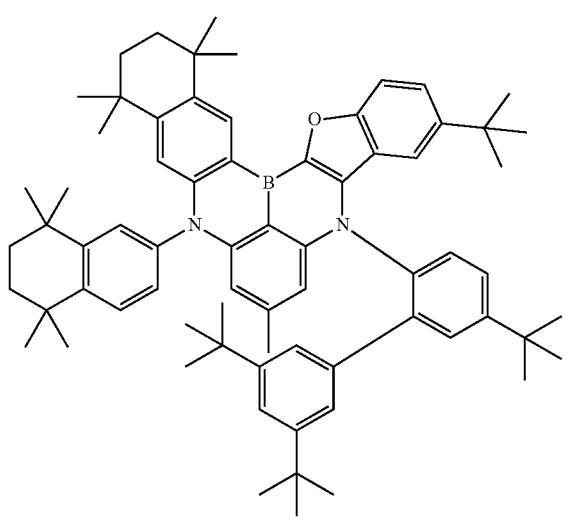 | 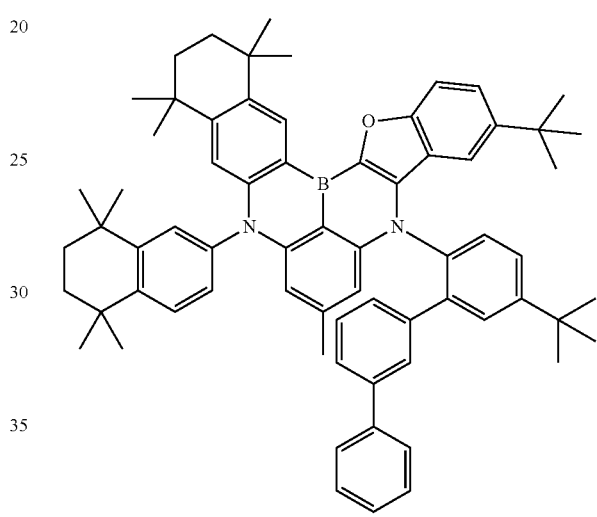 |
| | 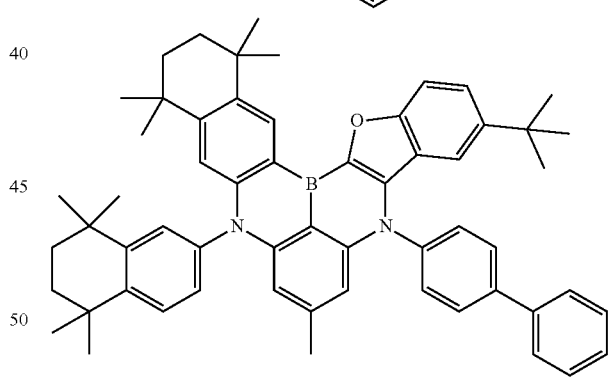 |
| 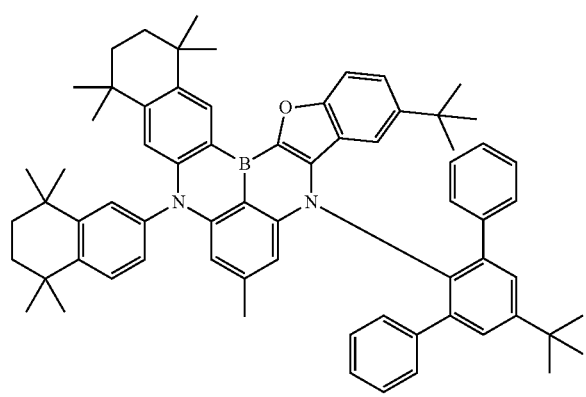 | 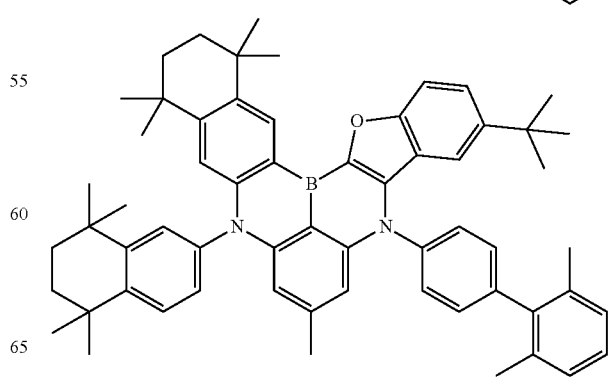 |

2541
-continued
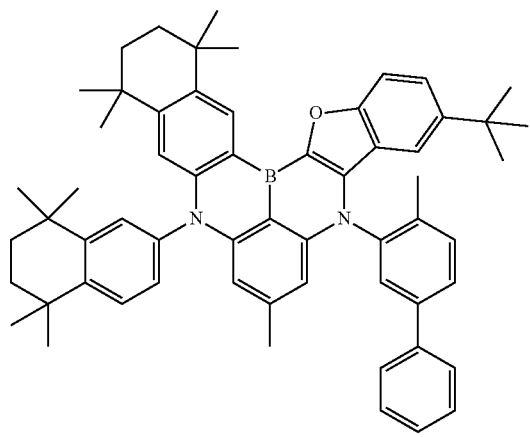
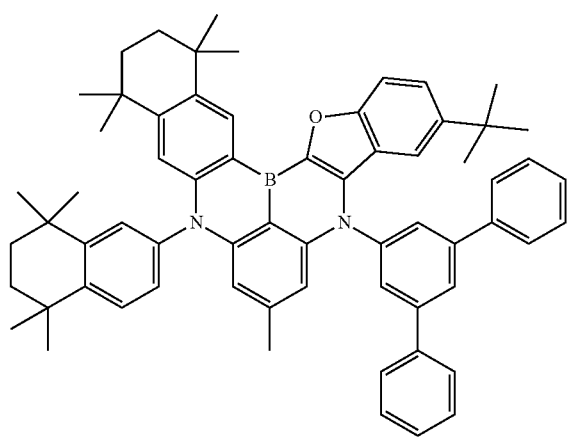
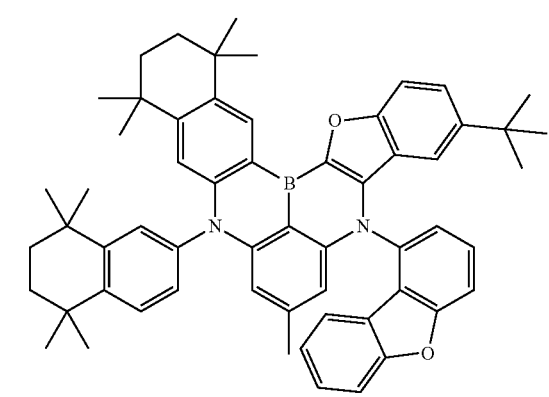
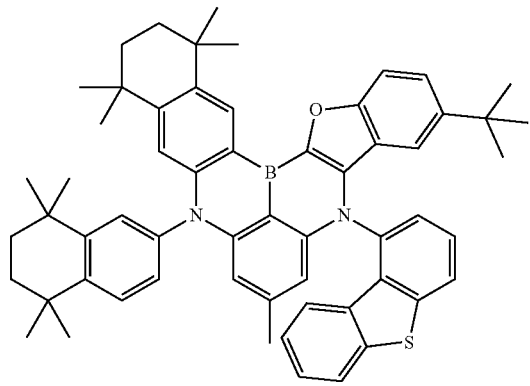
2542
-continued
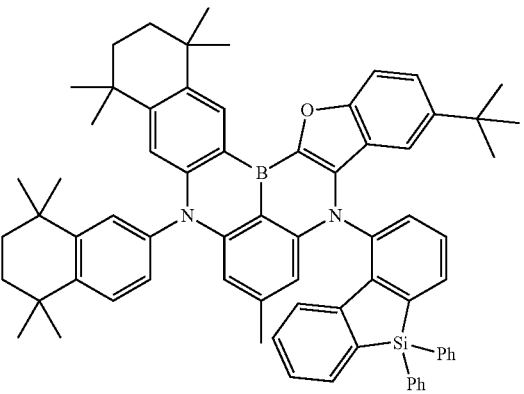
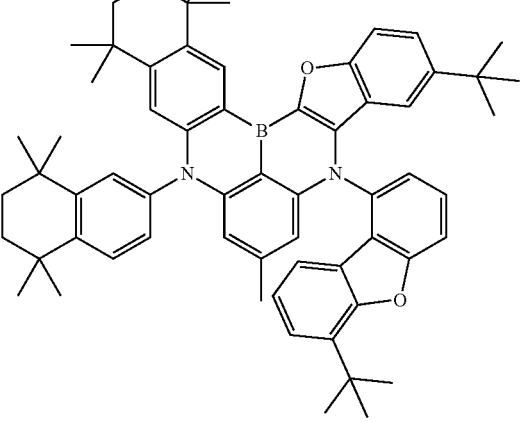
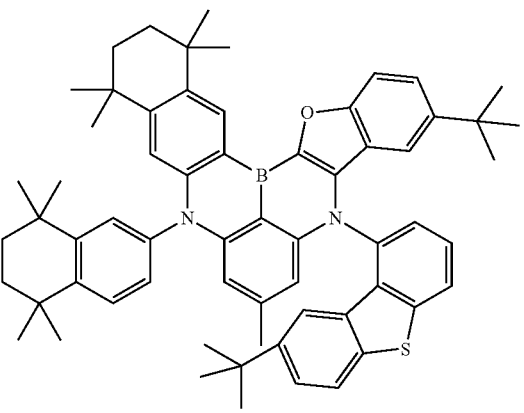
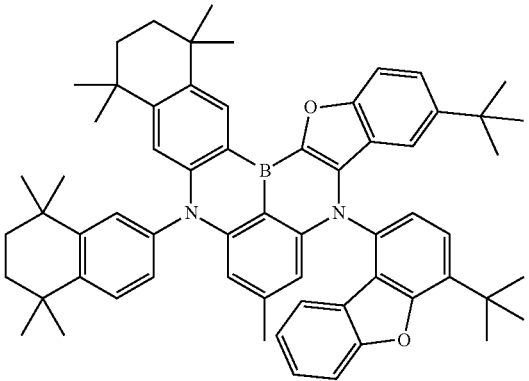

2543
-continued
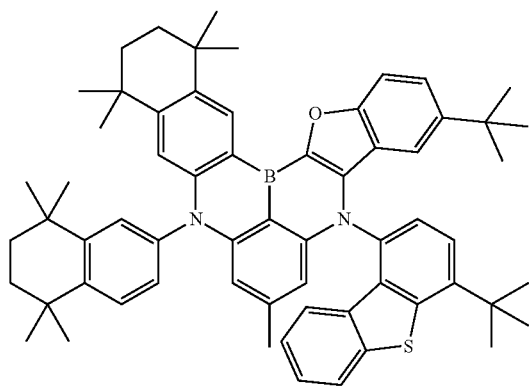
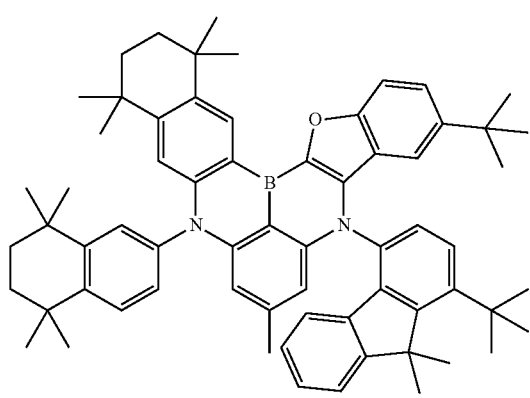
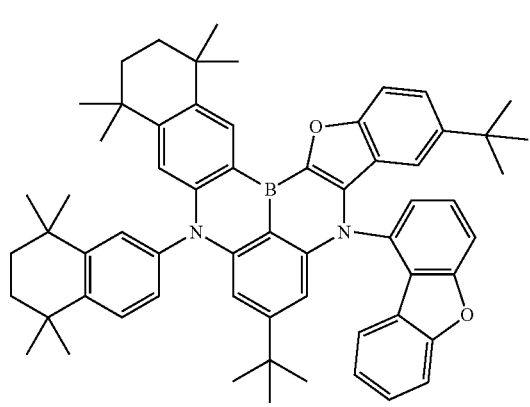
2544
-continued
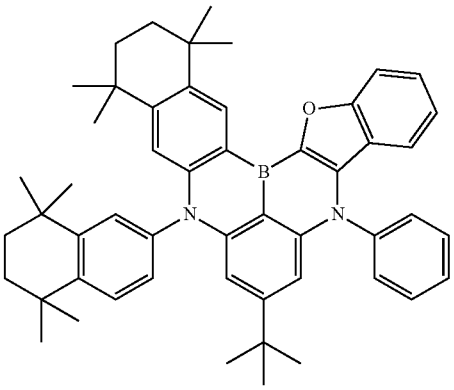
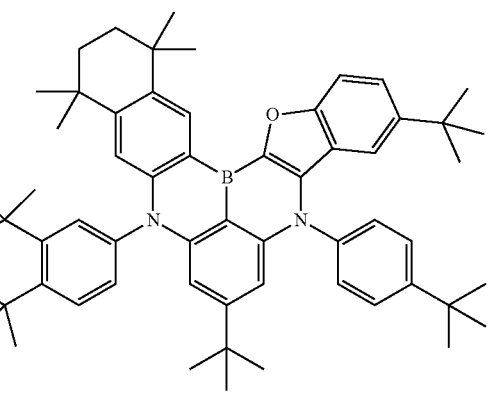
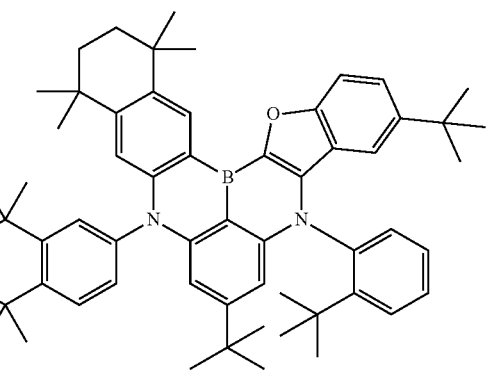
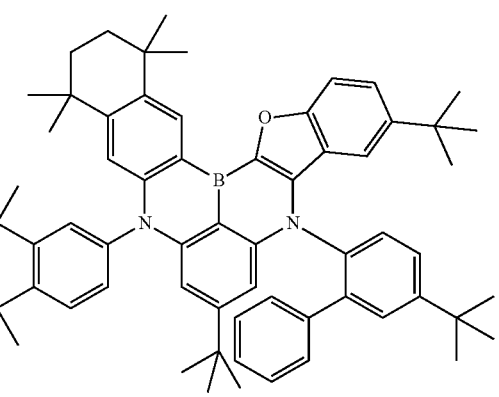

| 2545 -continued | 2546 -continued |
|---|---|
| 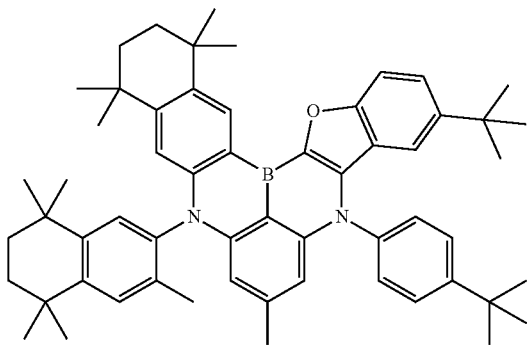 | 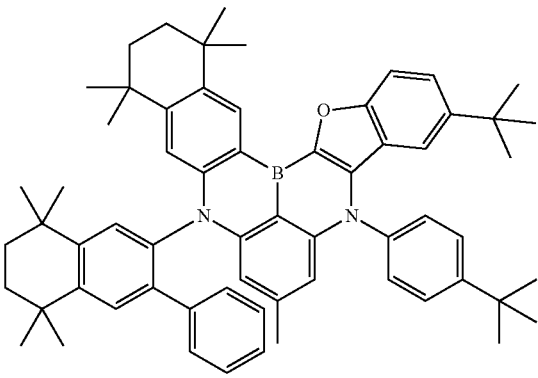 |
| 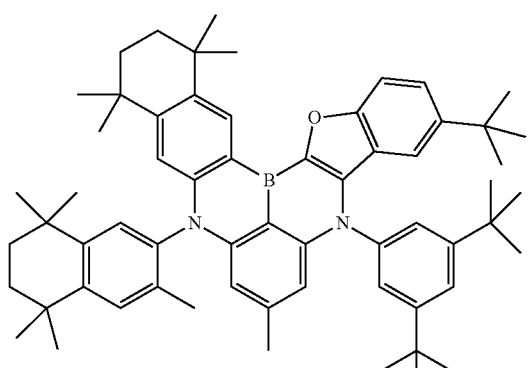 | 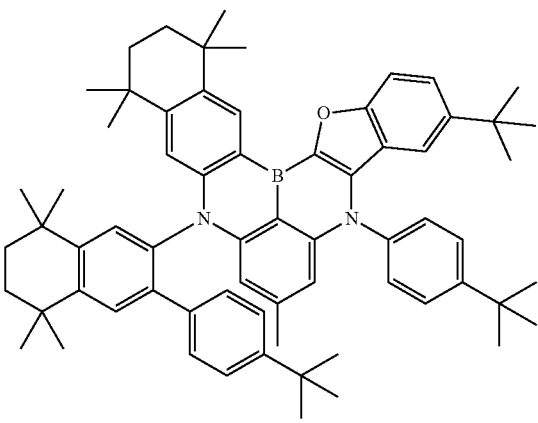 |
| 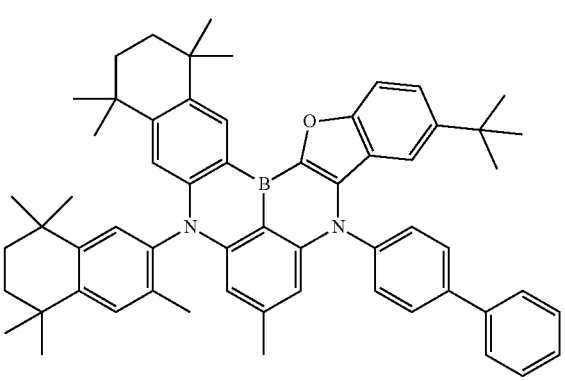 | 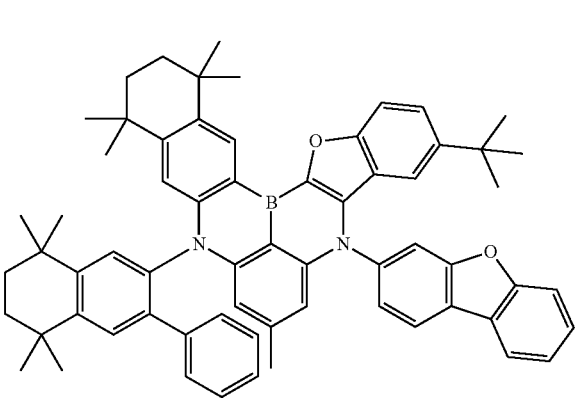 |
| 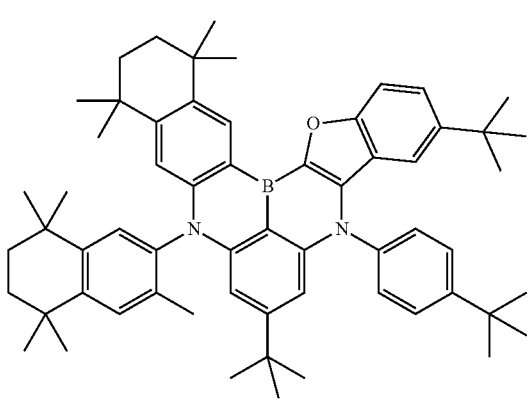 | 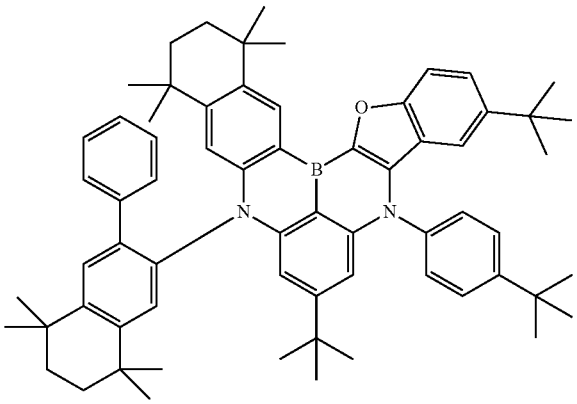 |

2547
-continued
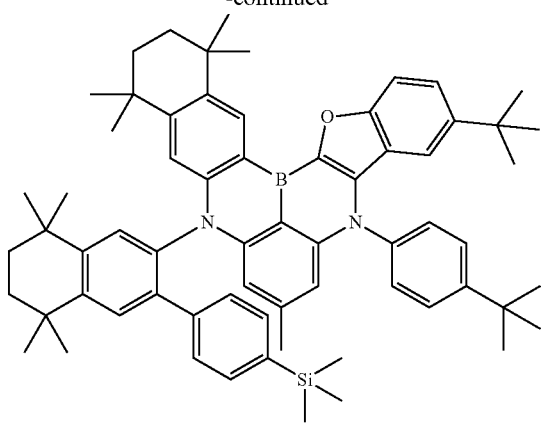
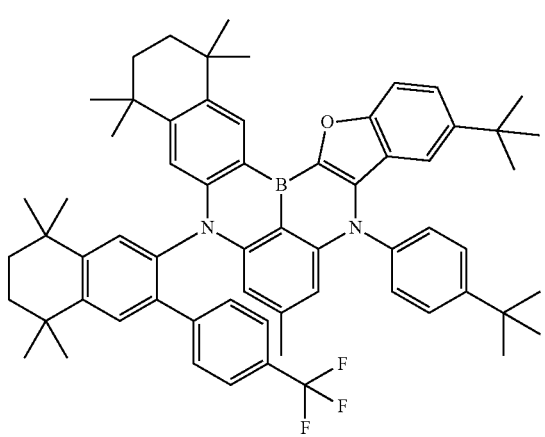
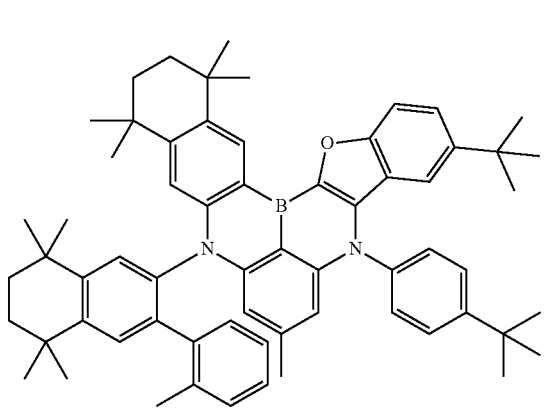
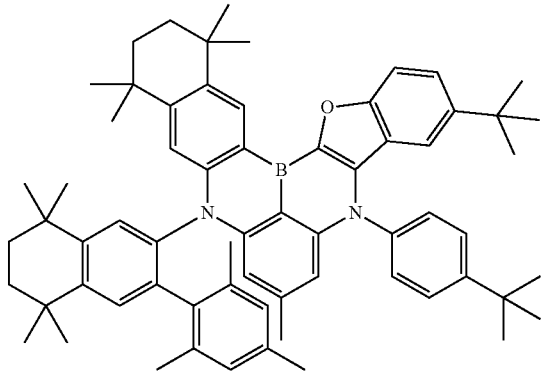
2548
-continued
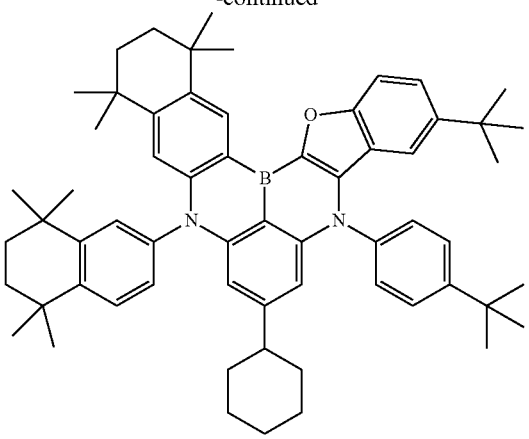
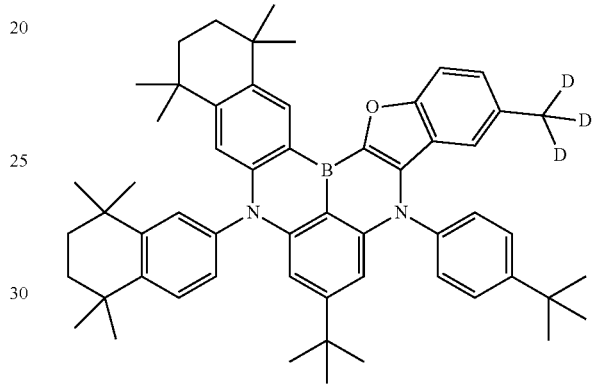
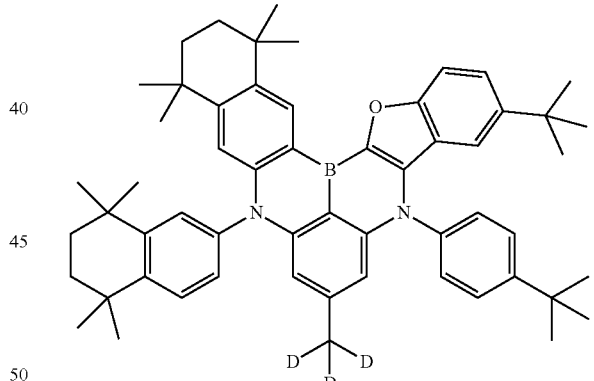

2549
-continued
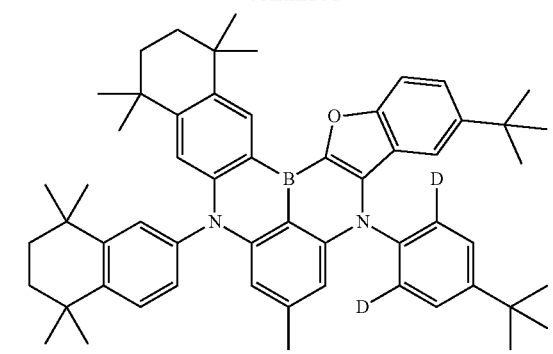
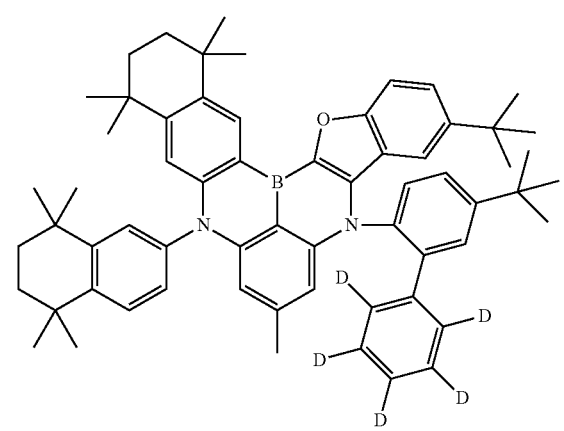
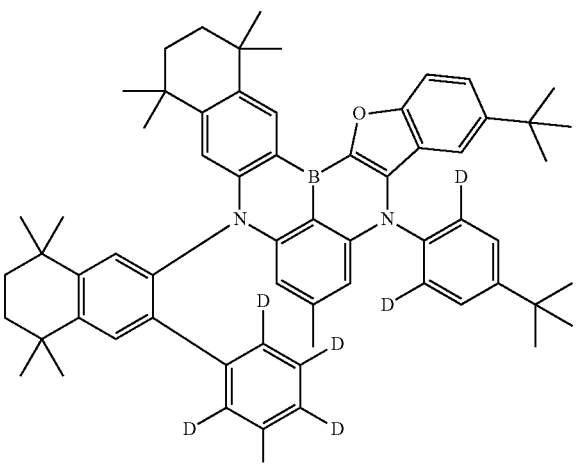
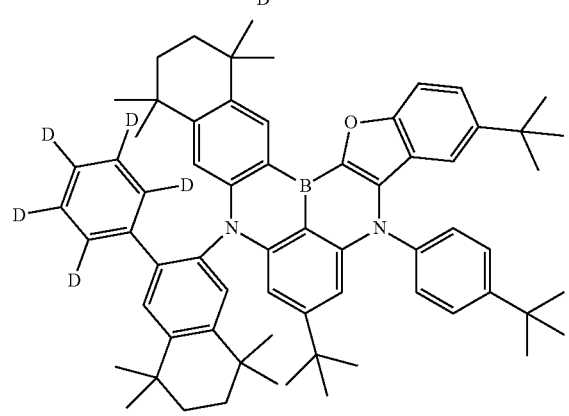
2550
-continued
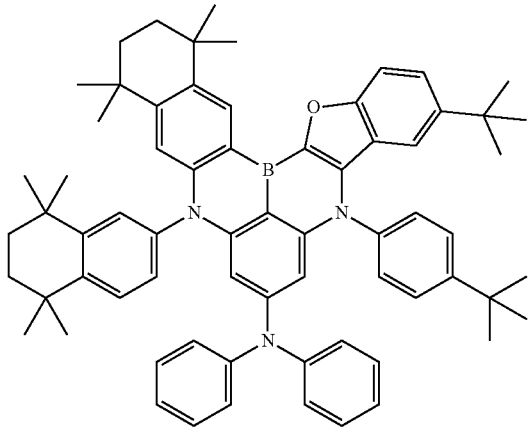
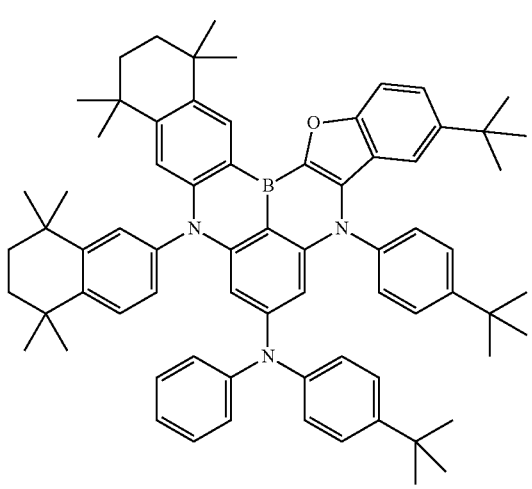
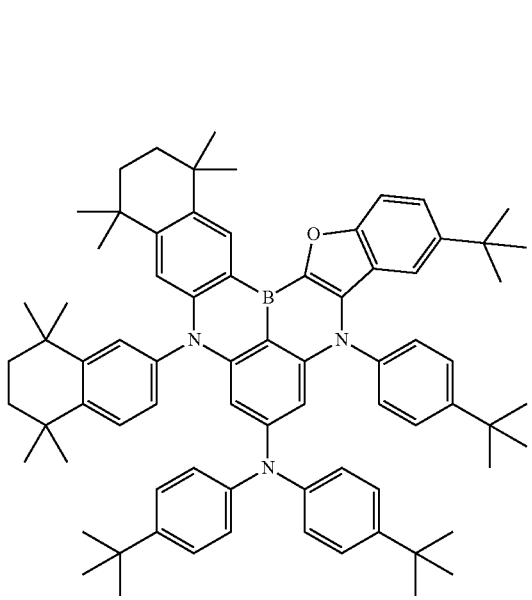

2551
-continued
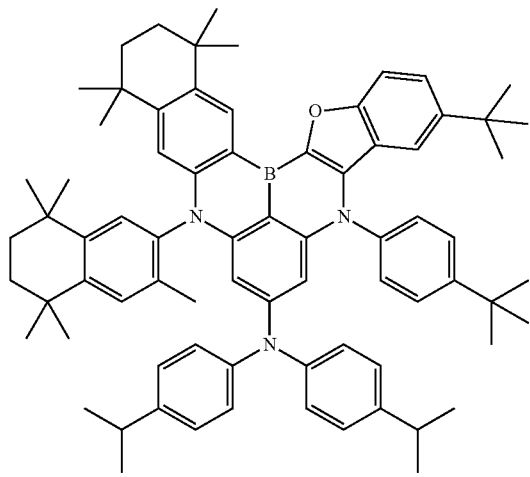
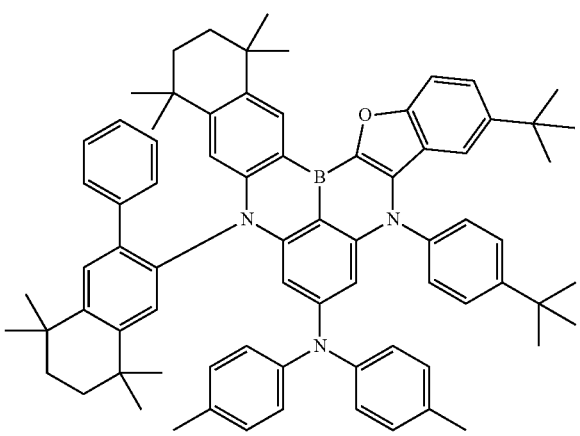
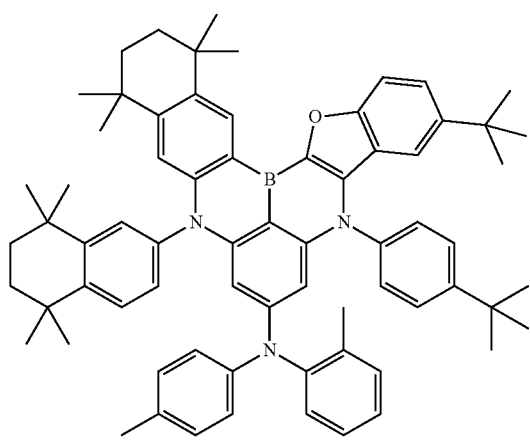
2552
-continued
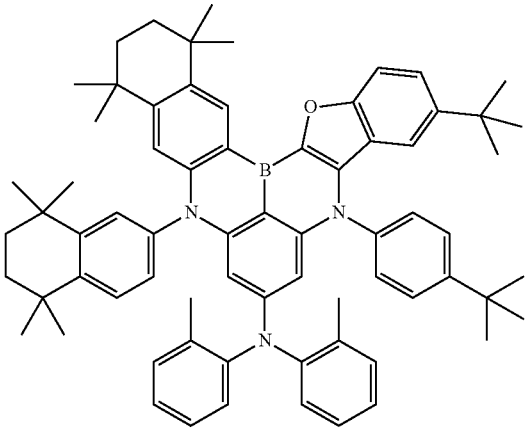
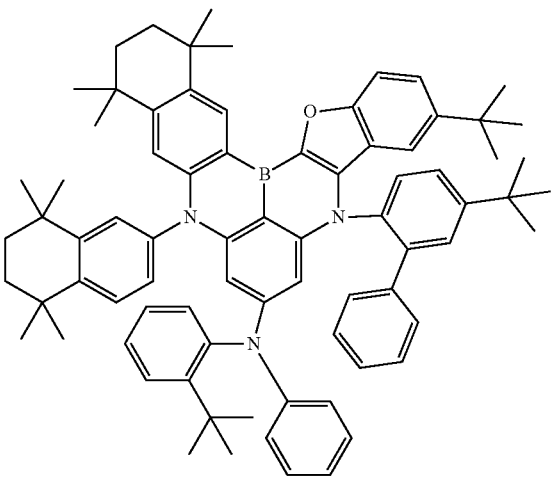
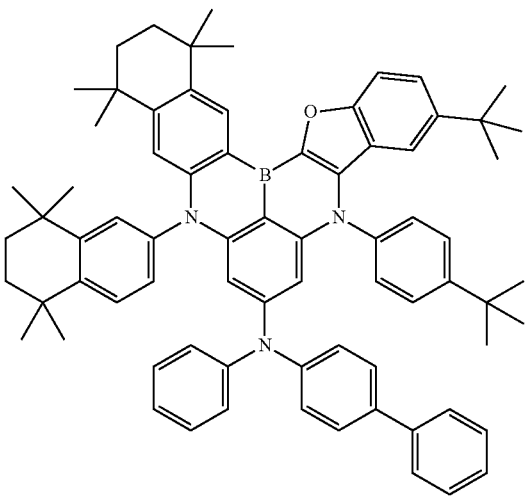

| 2553 -continued | 2554 -continued |
|---|---|
| 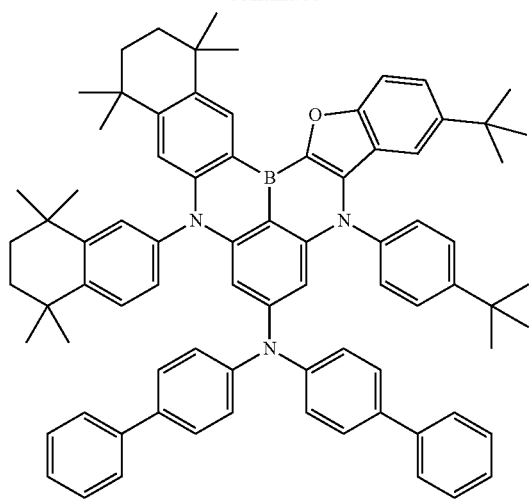 | 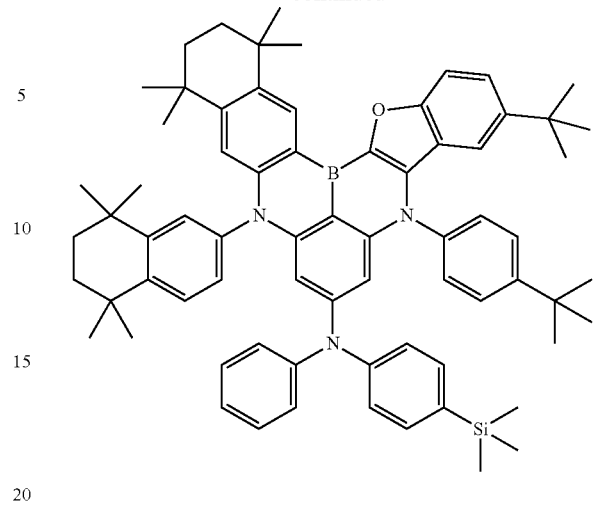 |
| 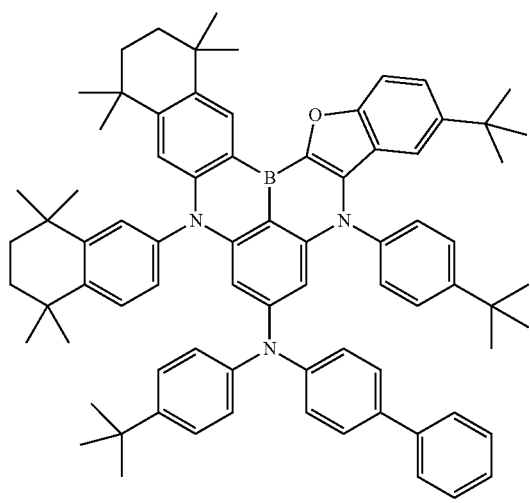 | 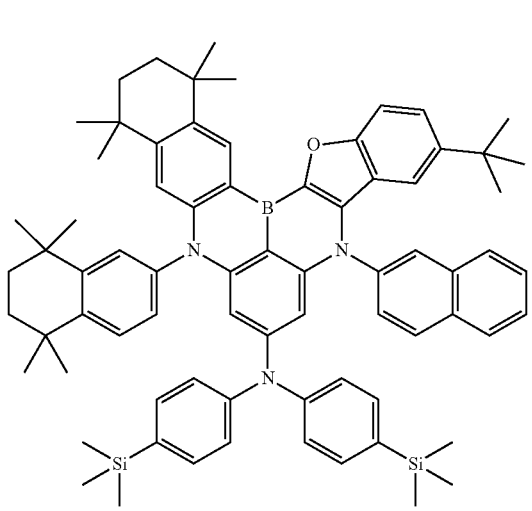 |
| 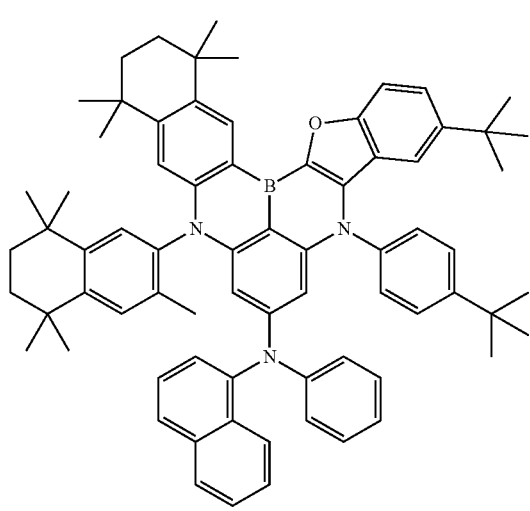 | 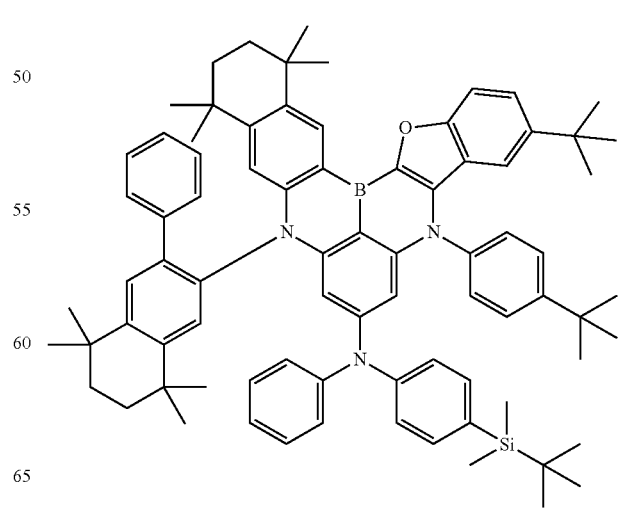 |

2555
-continued
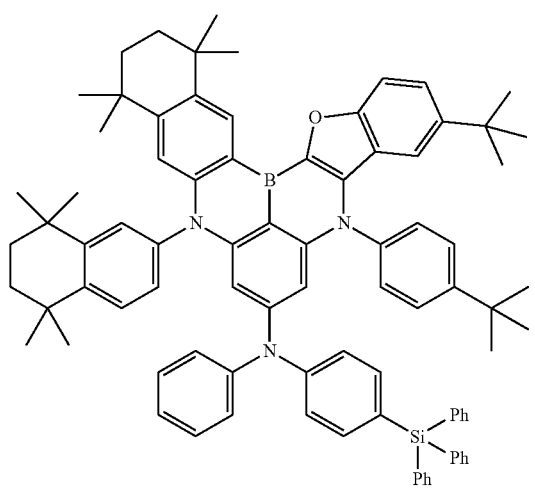
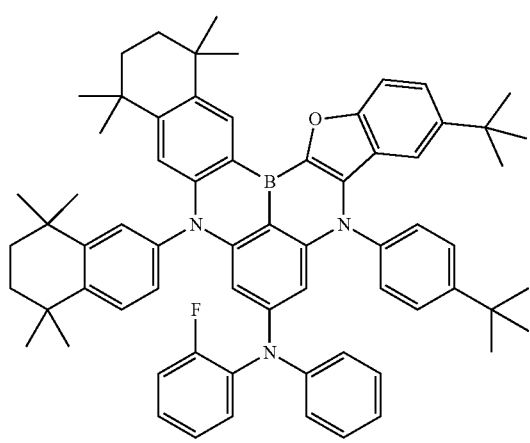
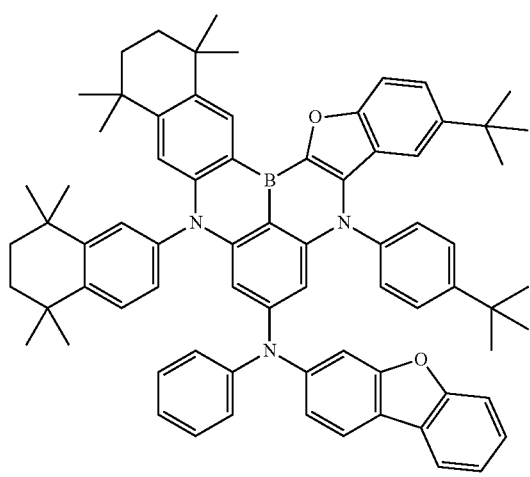
2556
-continued
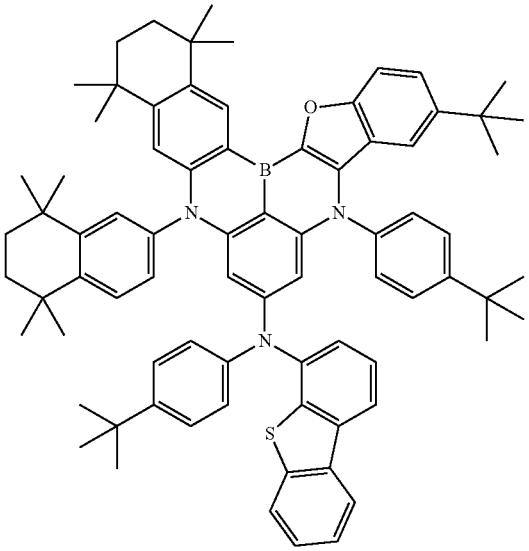
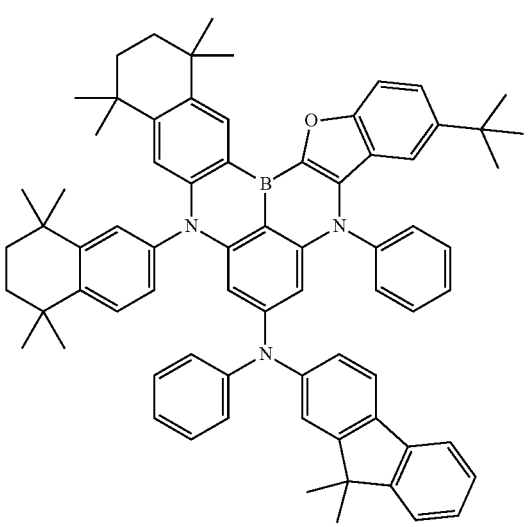
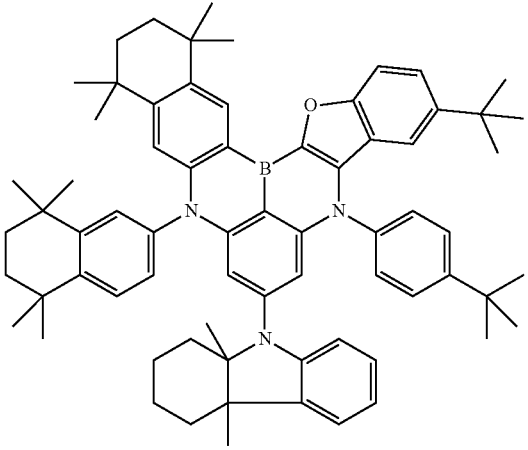

2557
-continued
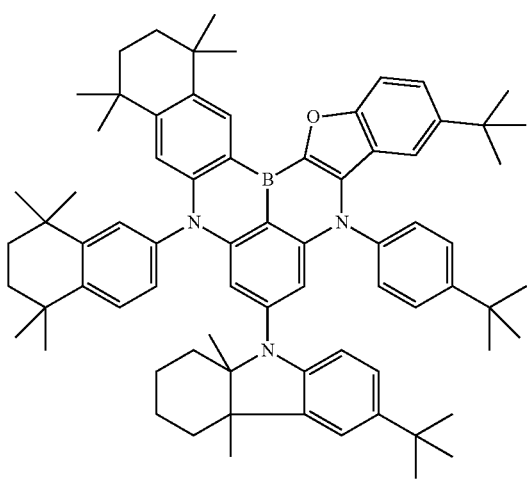
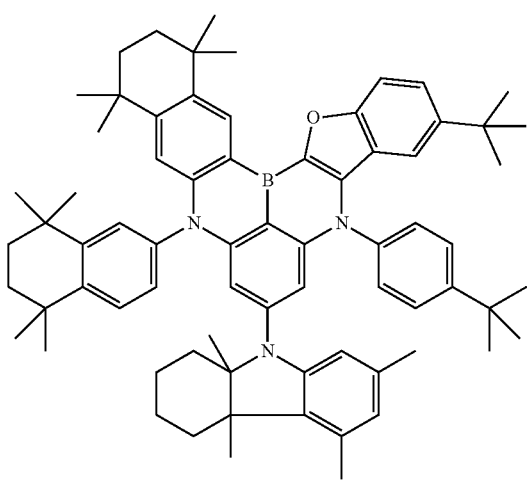
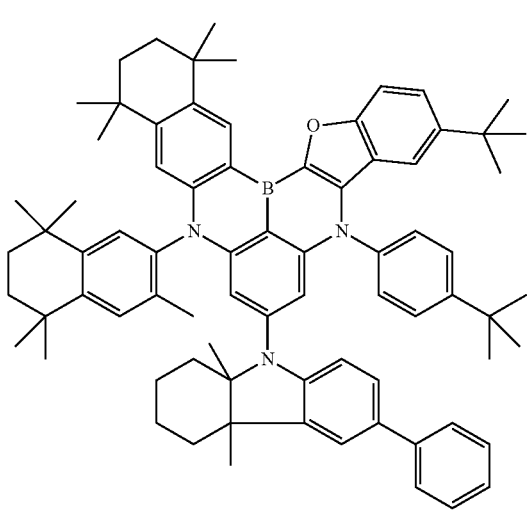
2558
-continued
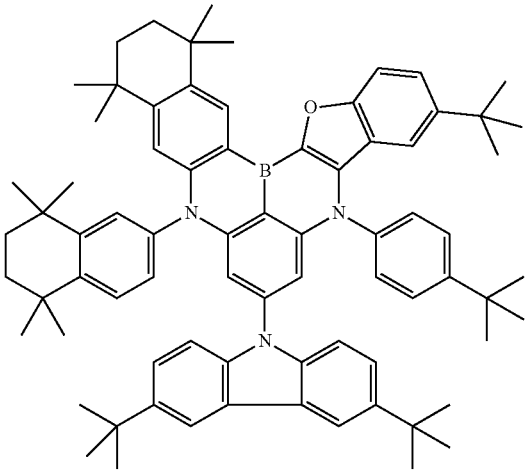
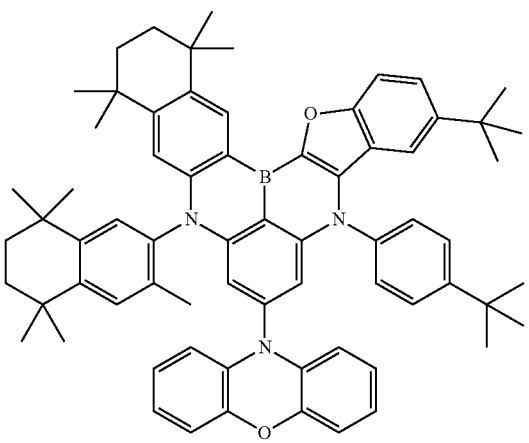
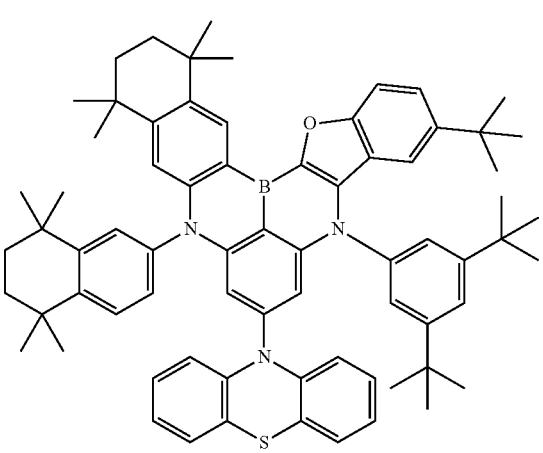

2559
-continued
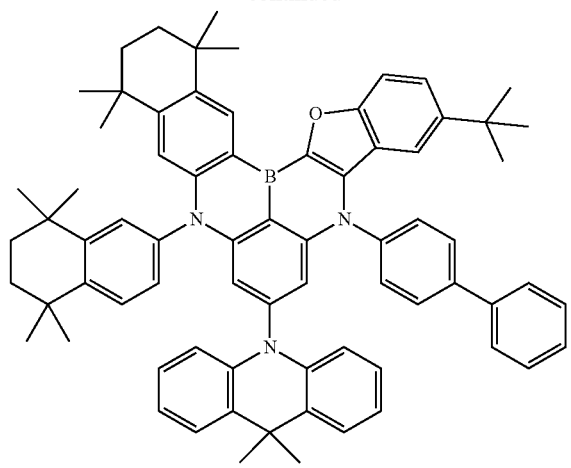
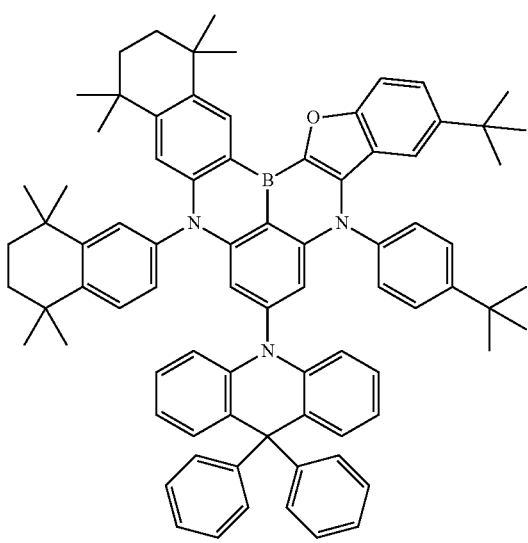
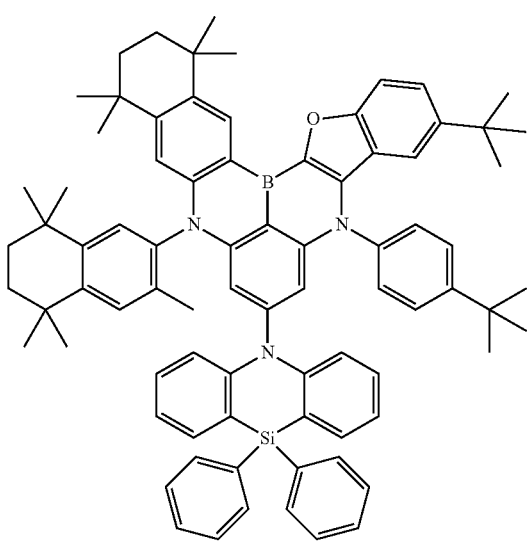
2560
-continued
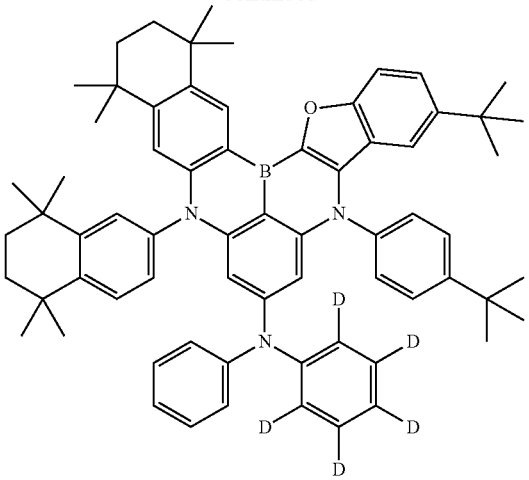
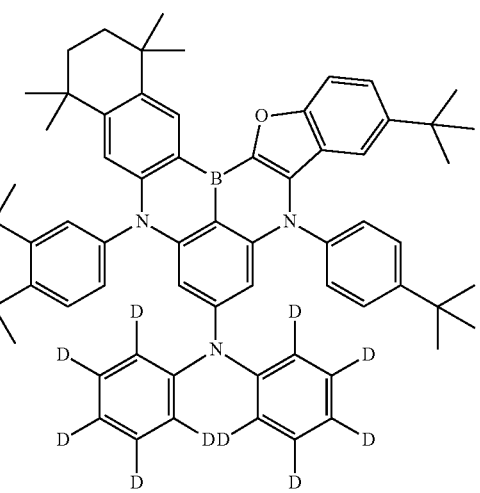
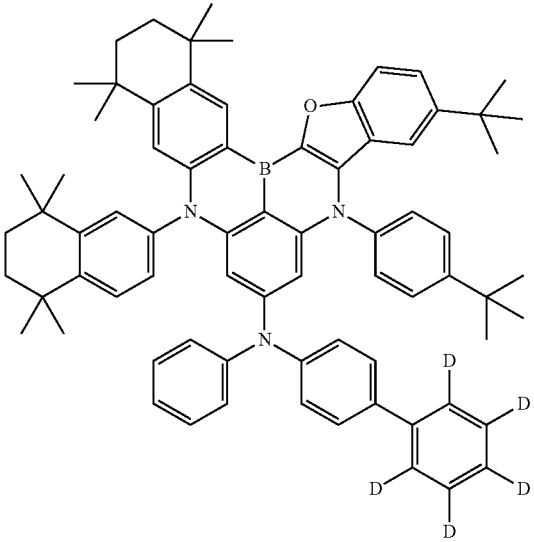

2561
-continued
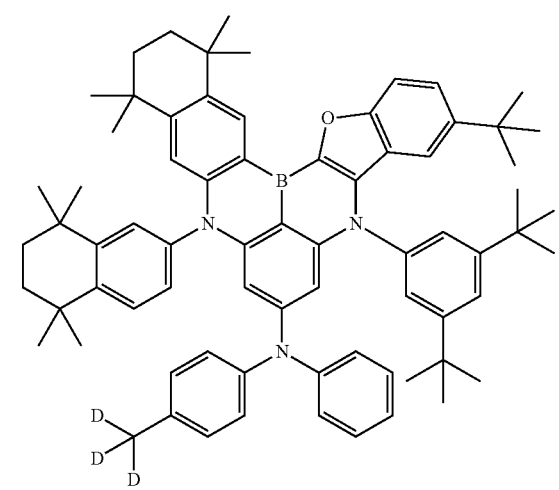
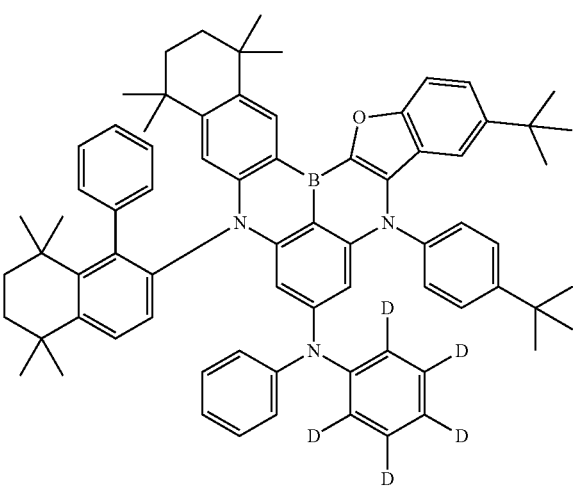
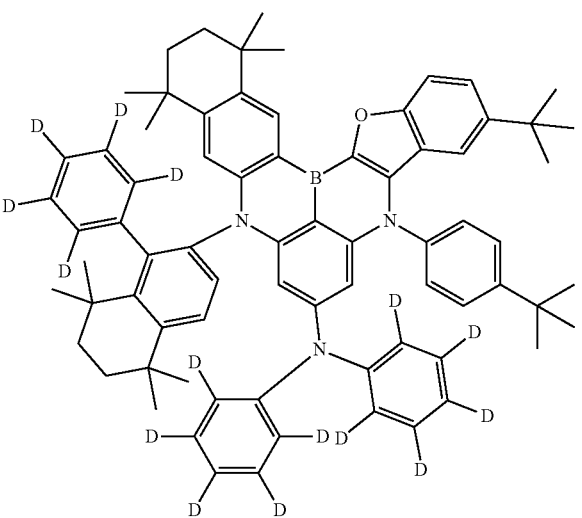
2562
-continued
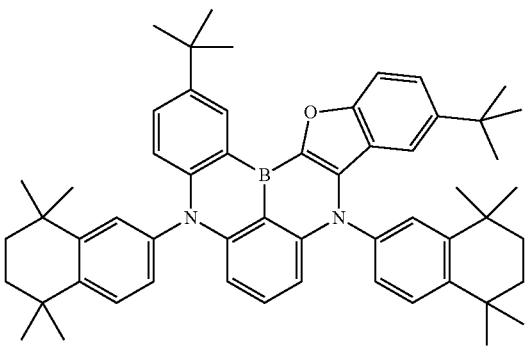
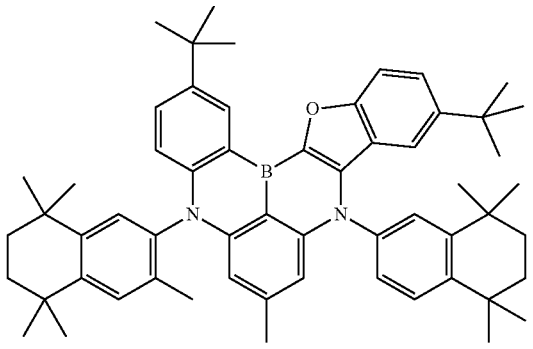
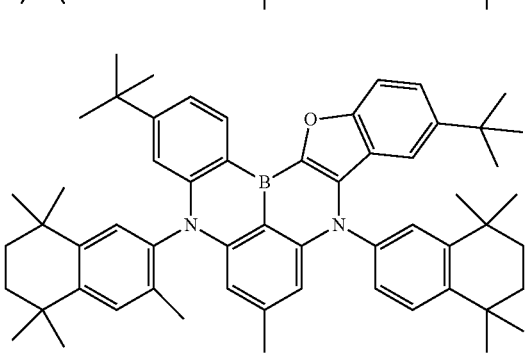
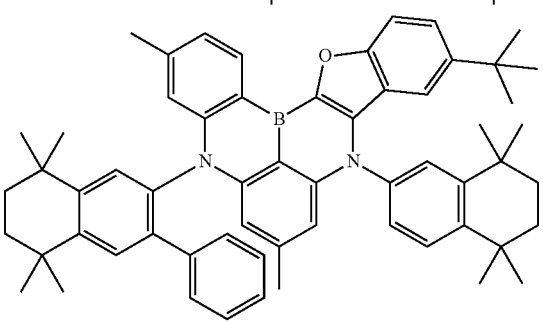
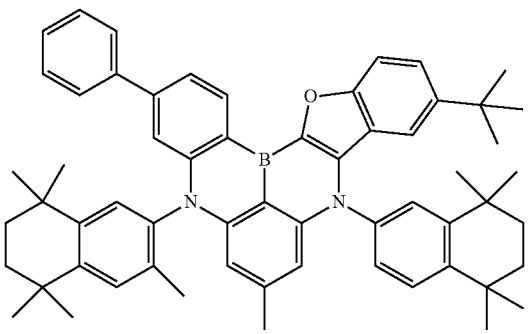

2563
-continued
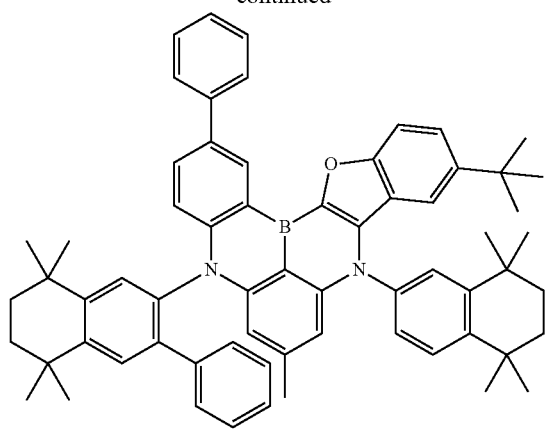
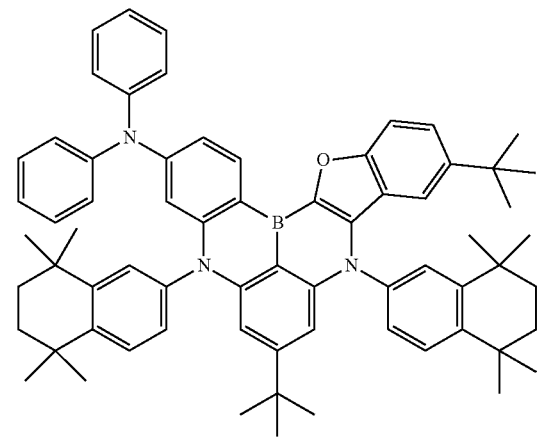
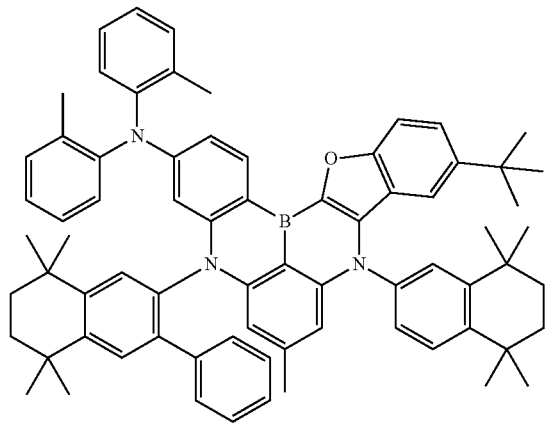
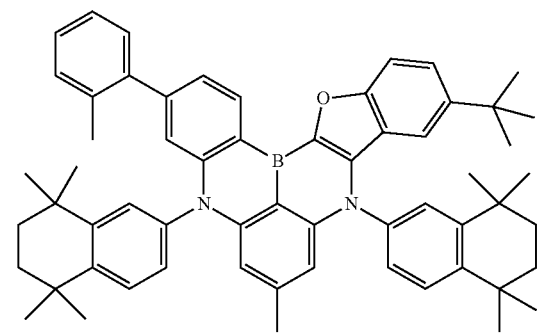
2564
-continued
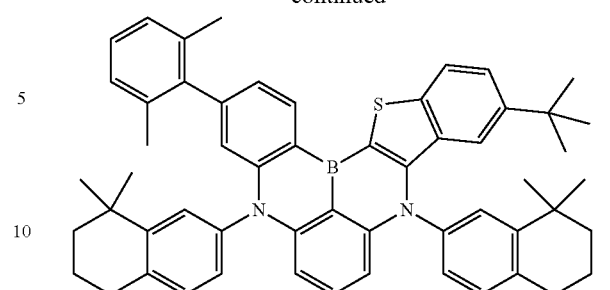
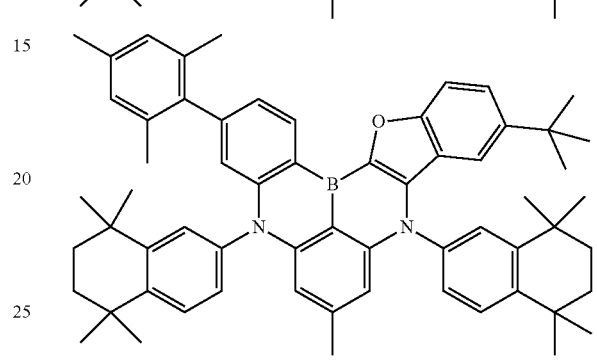
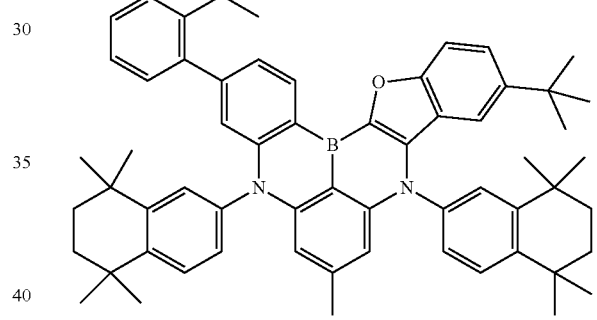
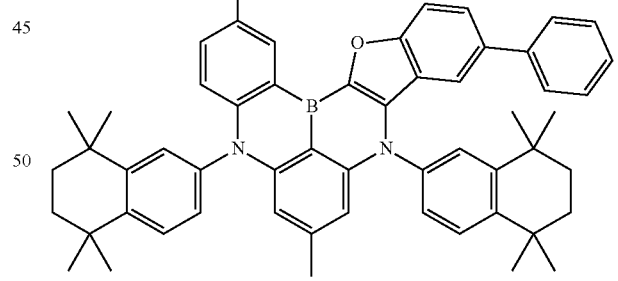
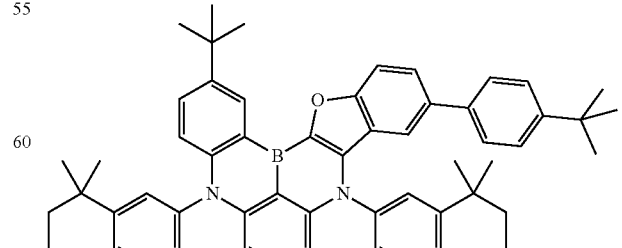

2565
-continued
2566
-continued
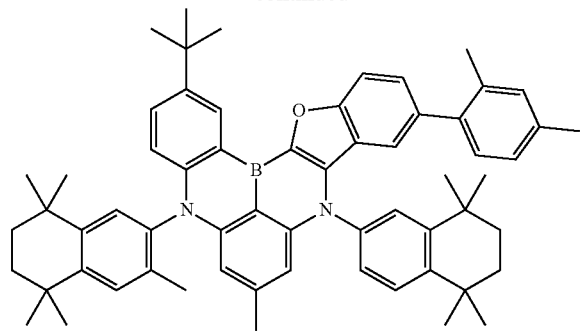
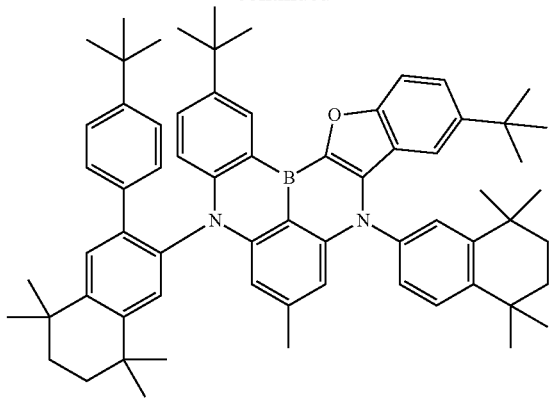
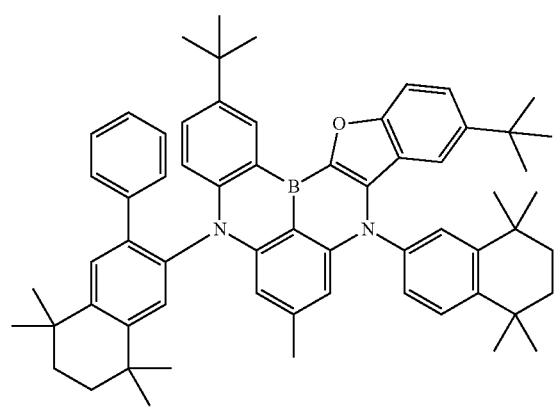
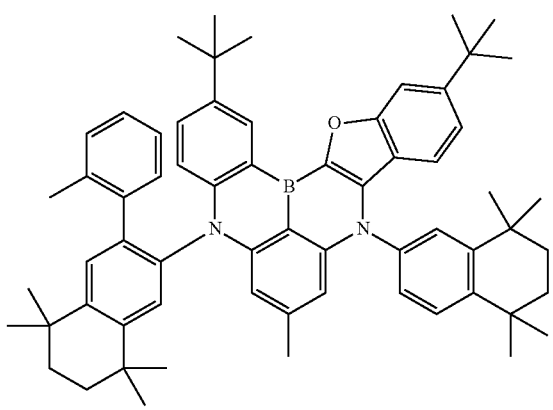
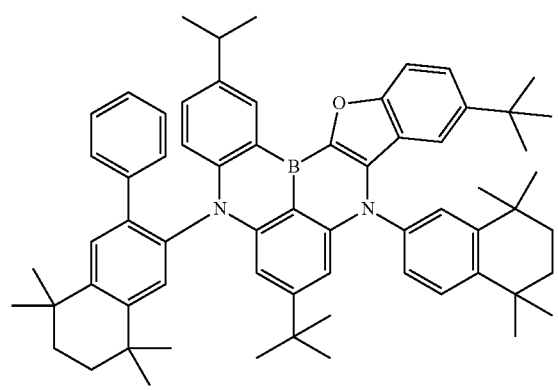
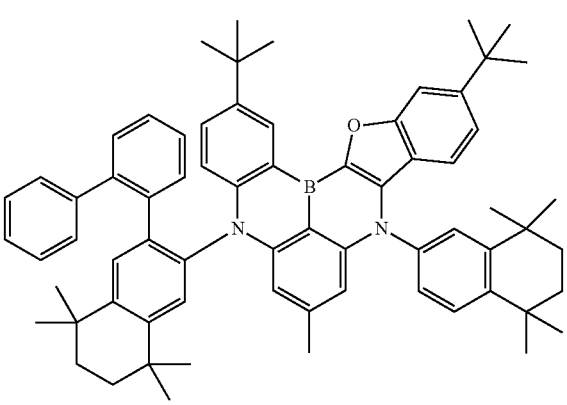
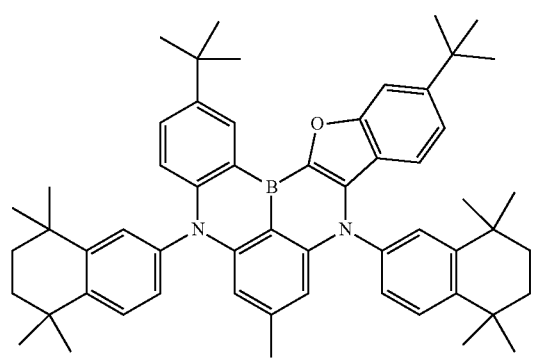
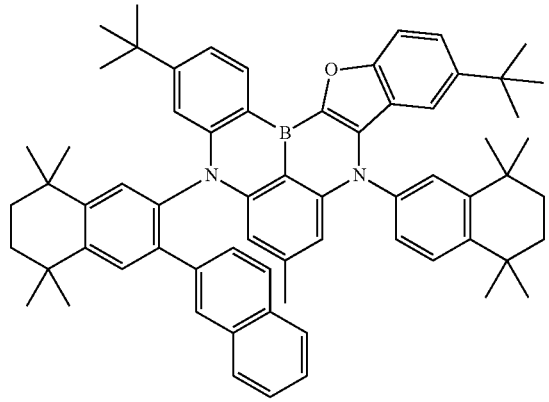

2567
-continued
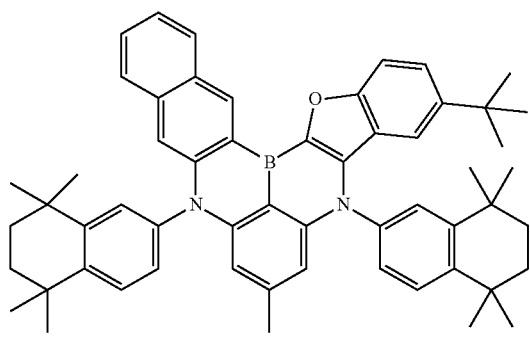
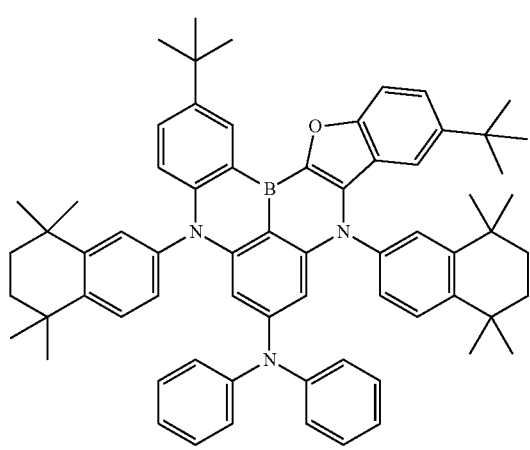
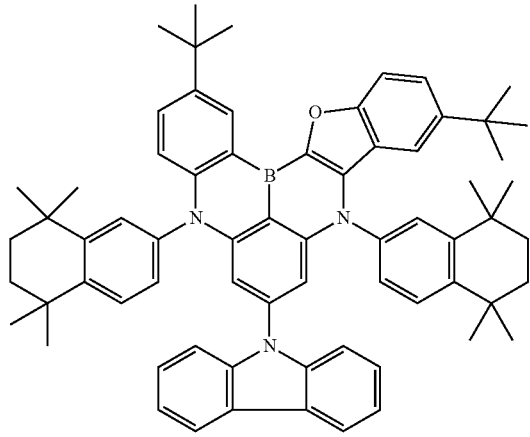
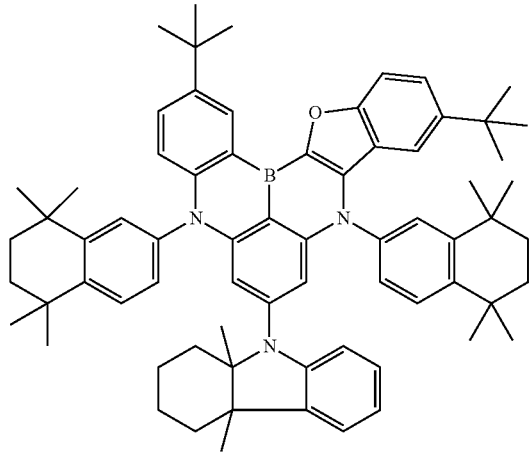
2568
-continued
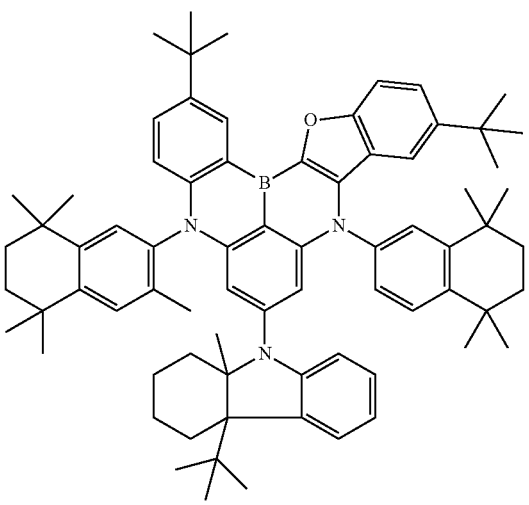
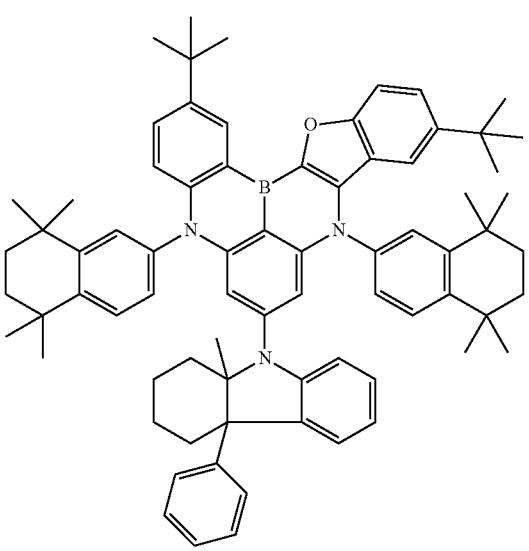
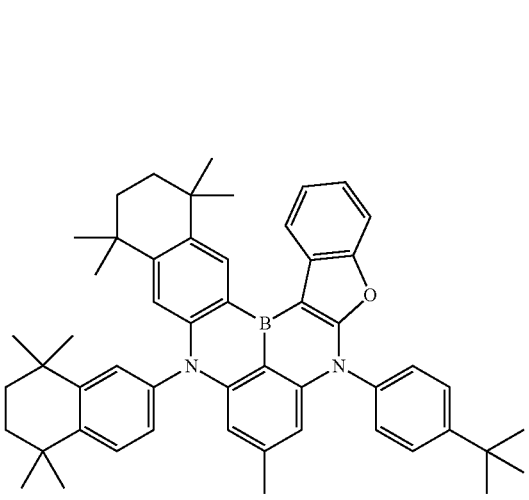

2569
-continued
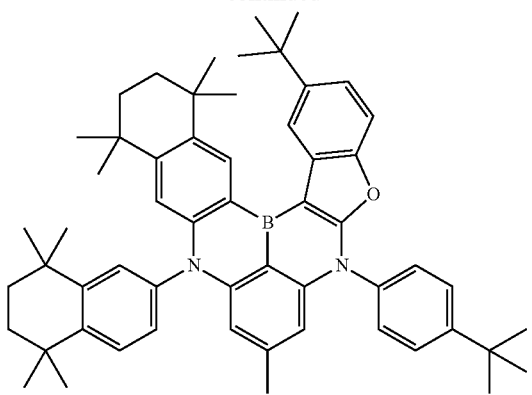
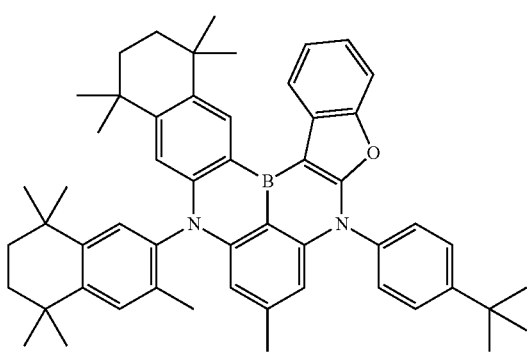
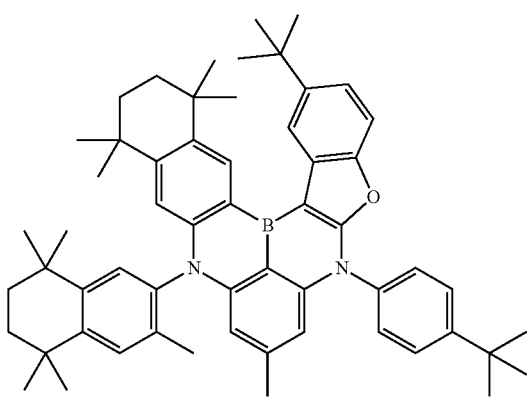
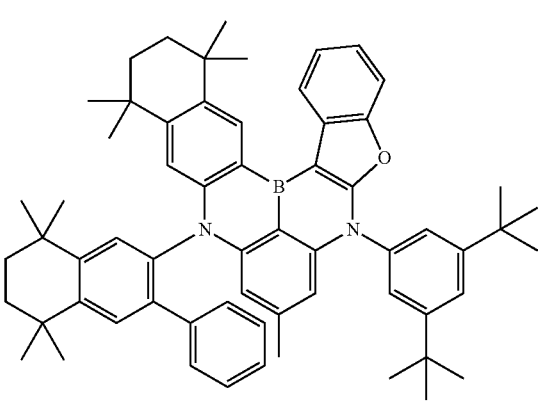
2570
-continued
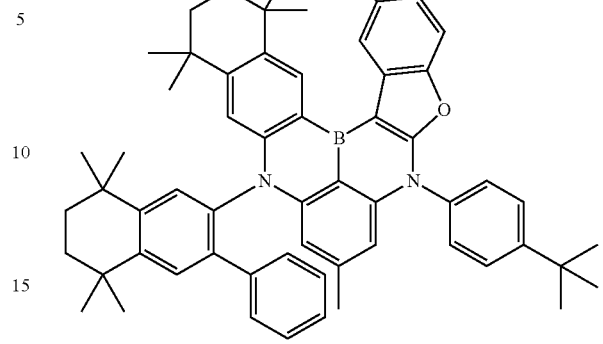
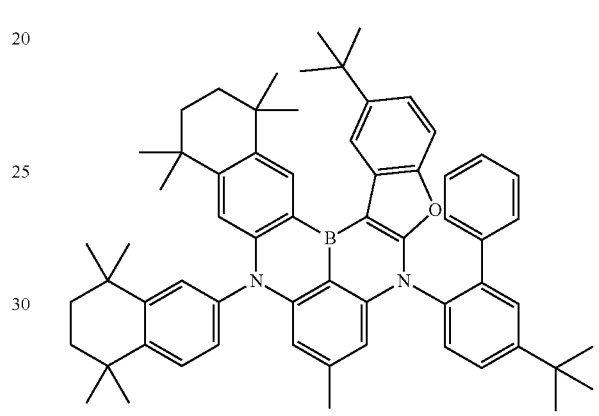
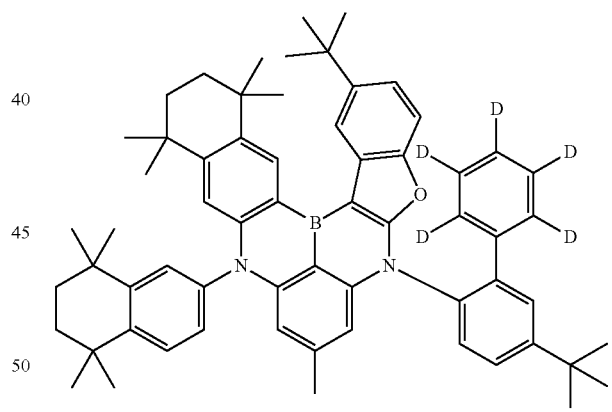
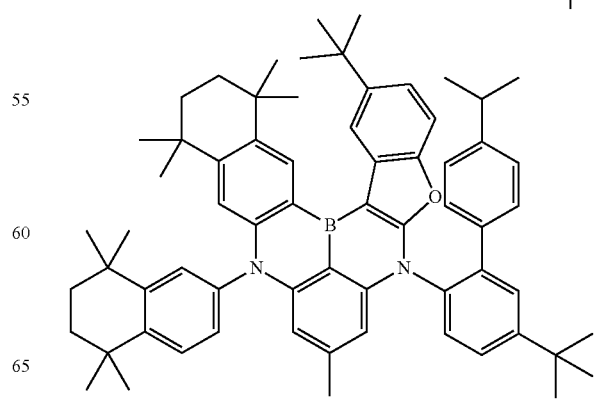

2571
-continued
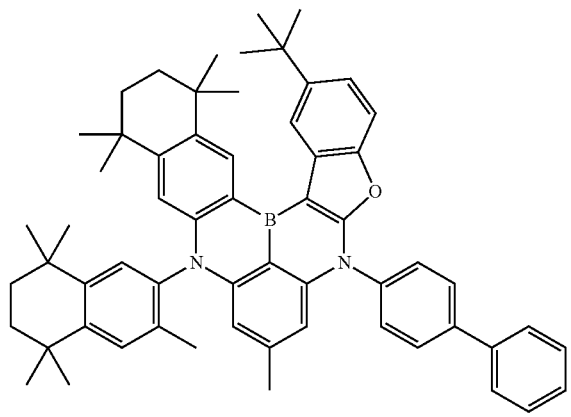
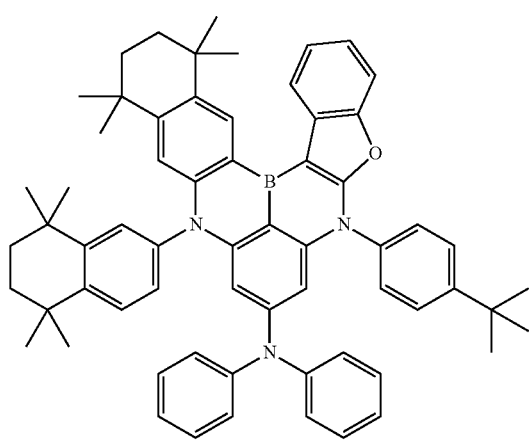
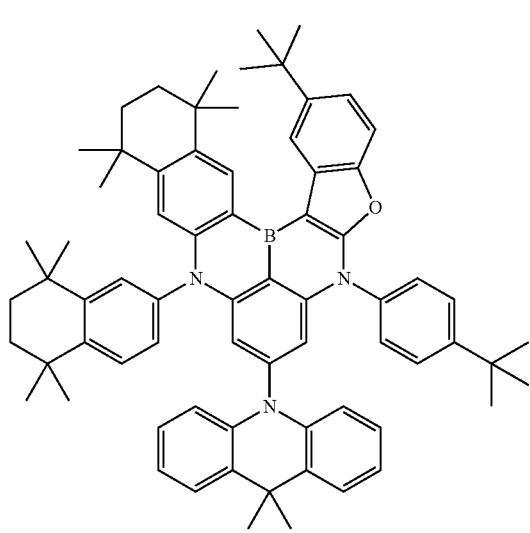
2572
-continued
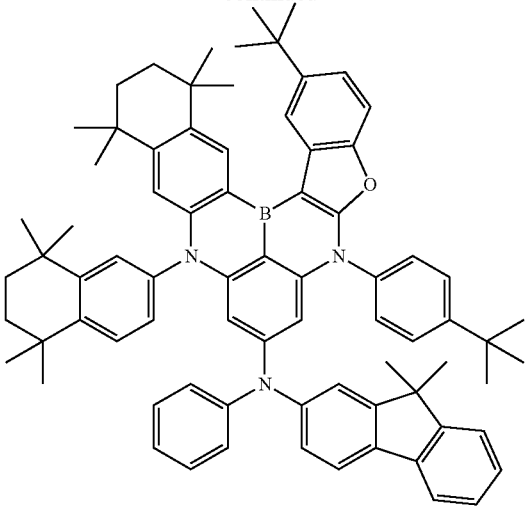
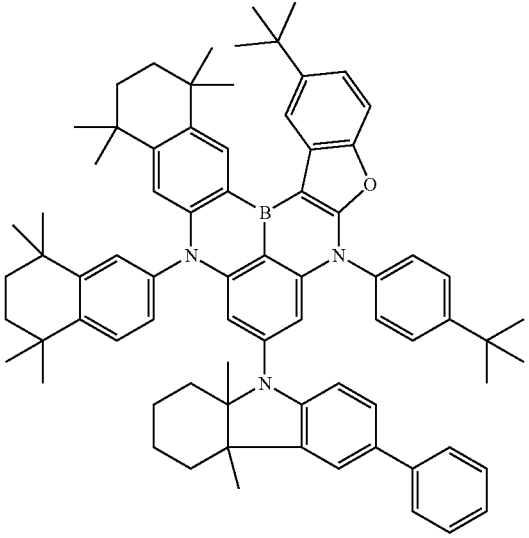
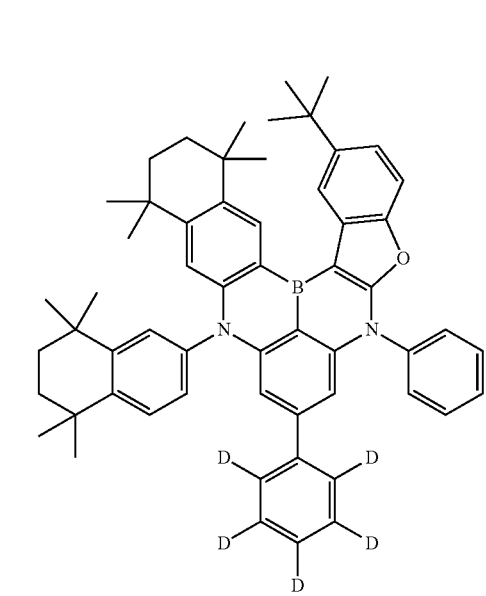

2573
-continued
2574
-continued
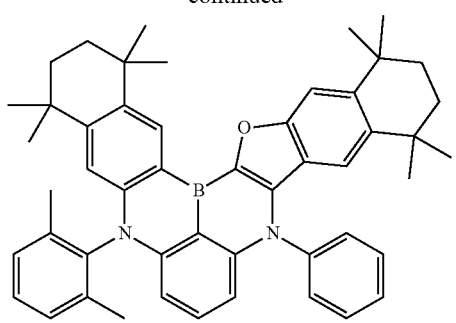
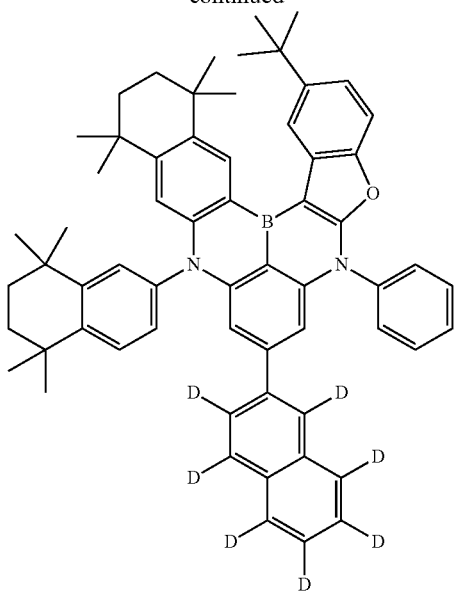
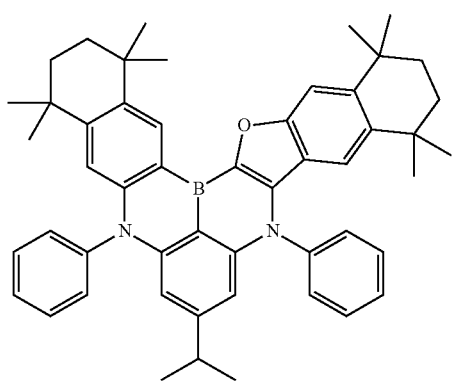
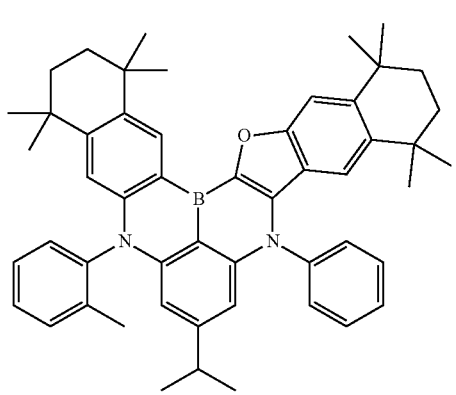
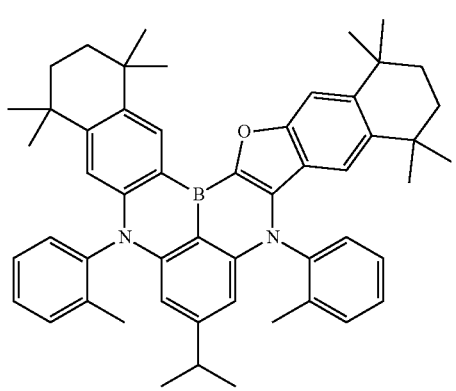

2575
-continued
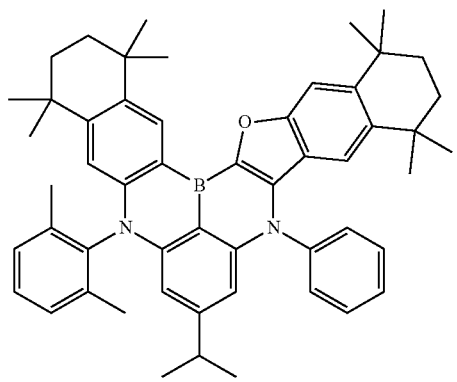
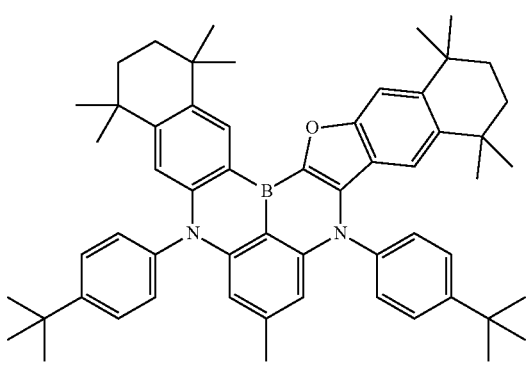
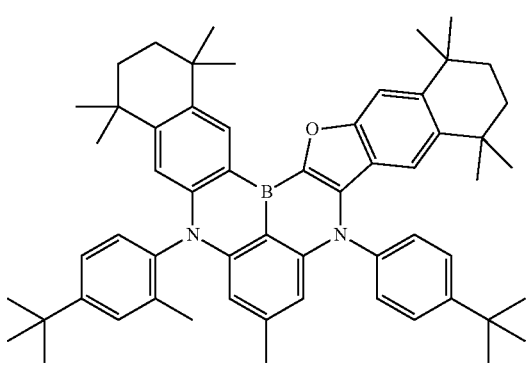
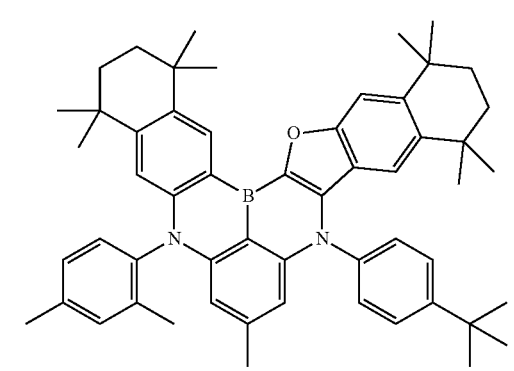
2576
-continued
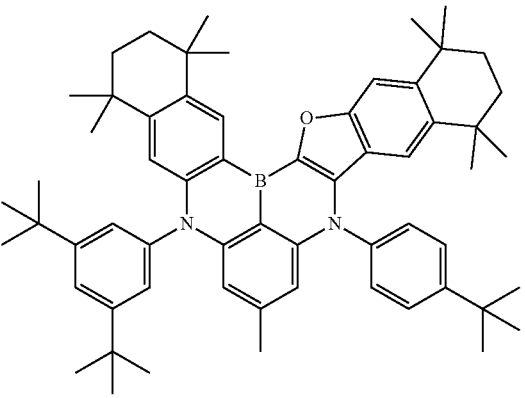
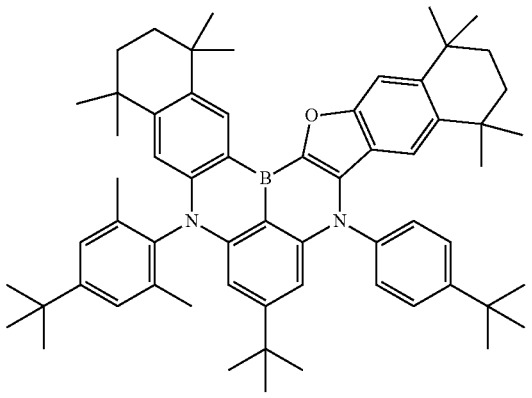
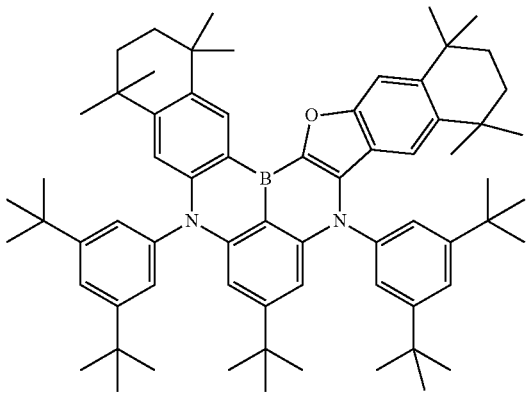
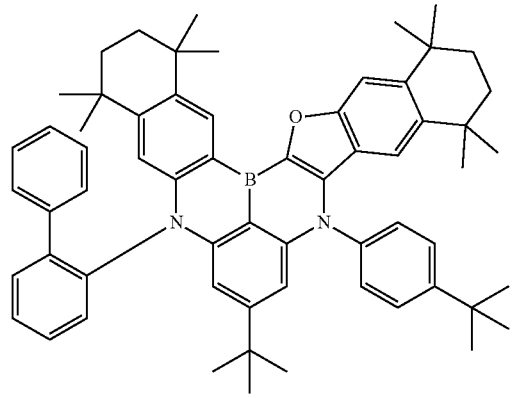

2577
-continued
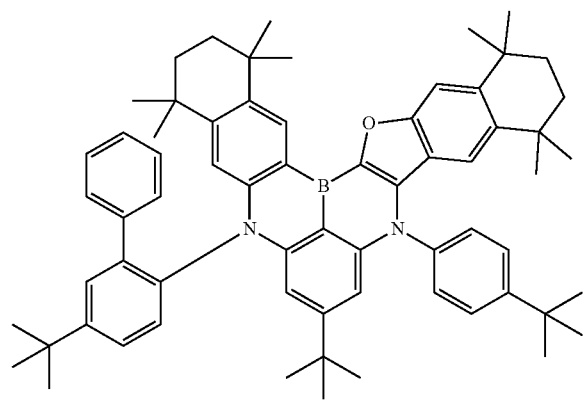
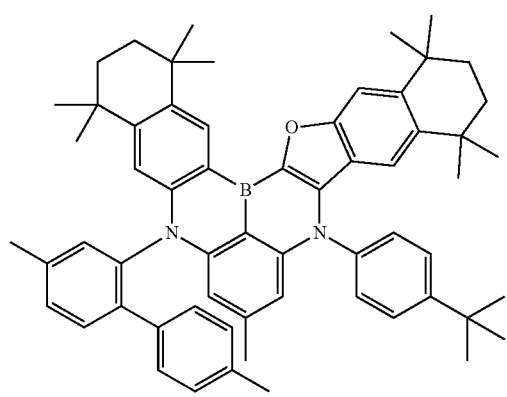
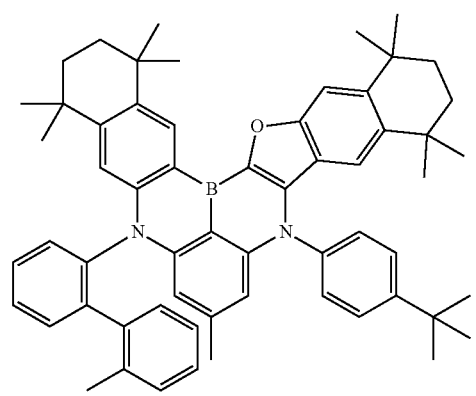
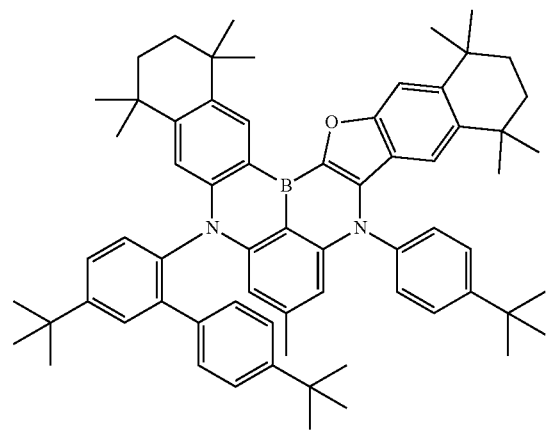
2578
-continued
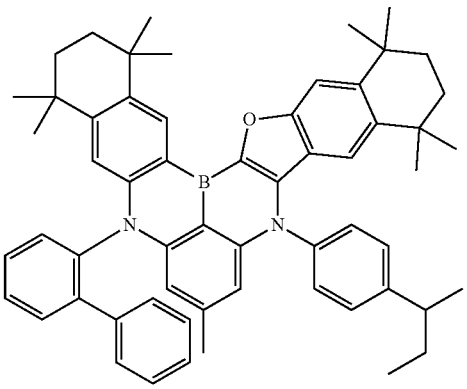
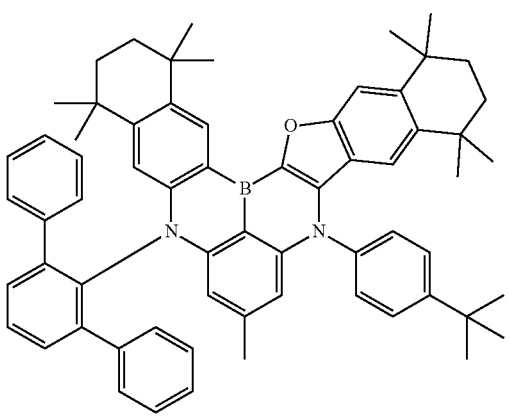
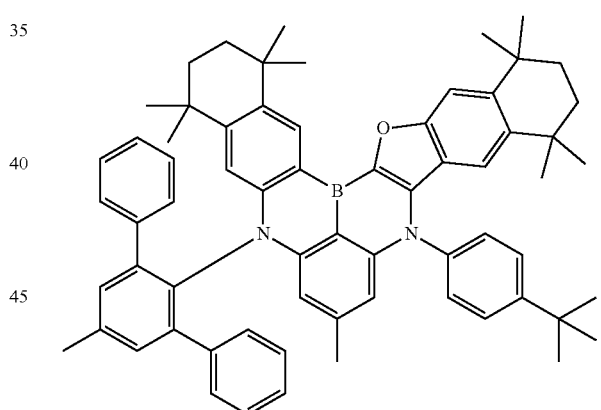
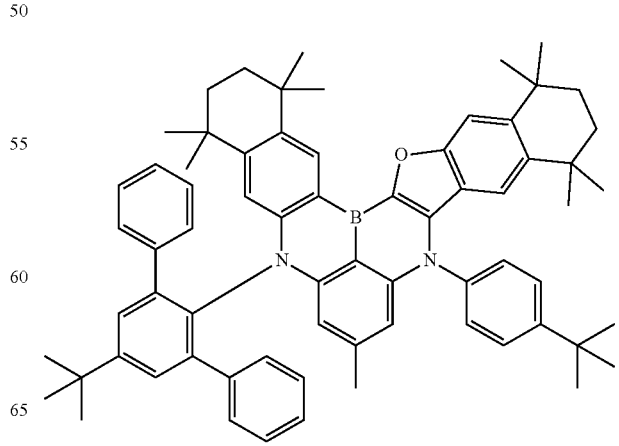

2579
-continued
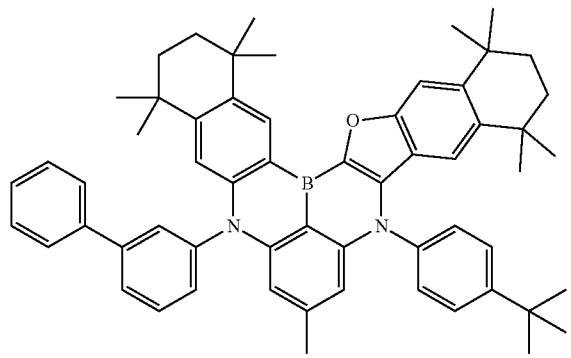
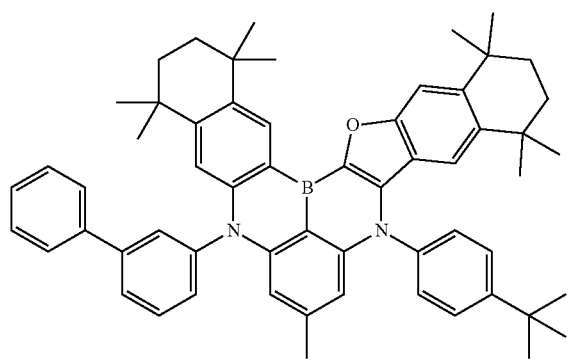
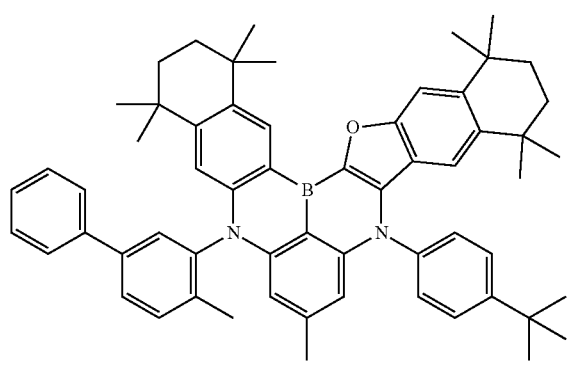
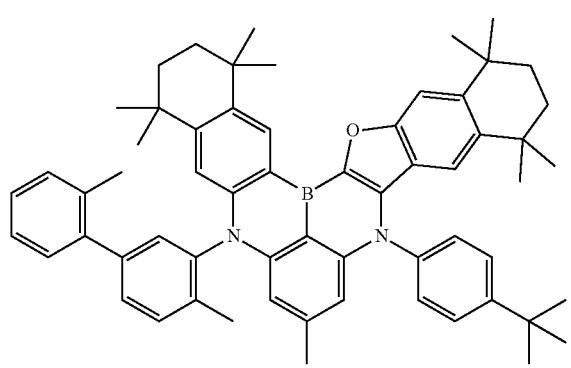
2580
-continued
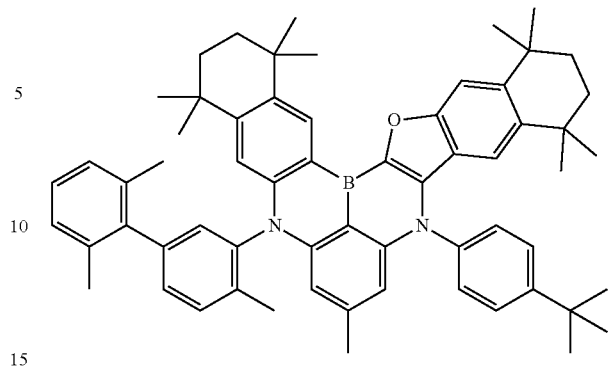
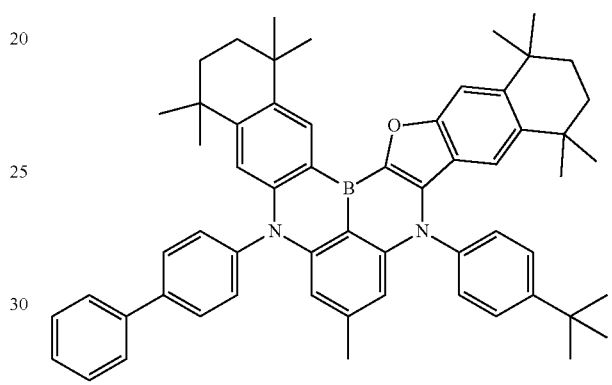
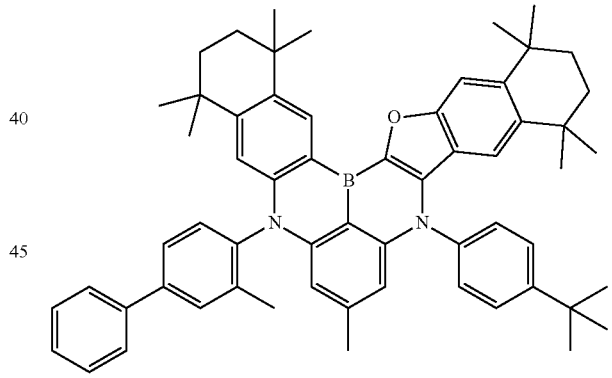
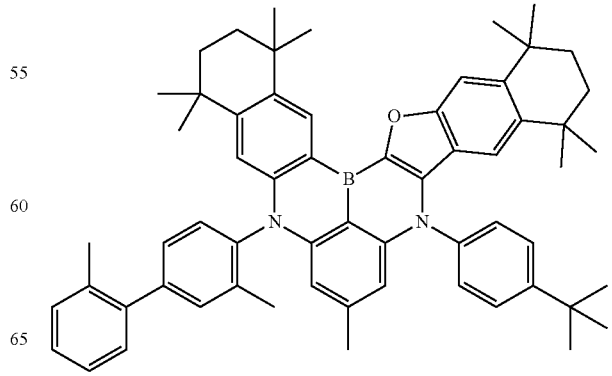

2581 -continued
2582 -continued
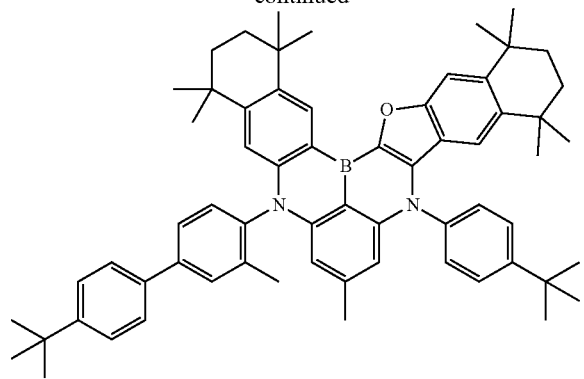
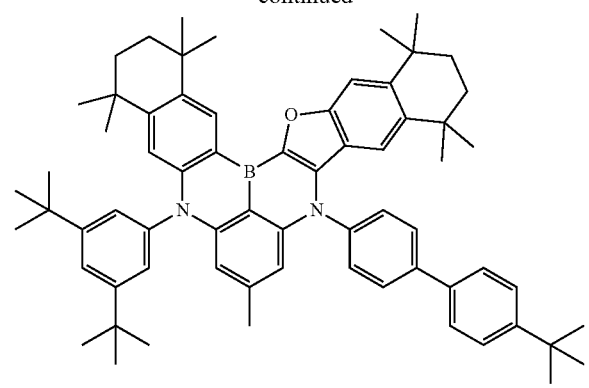

2583
-continued
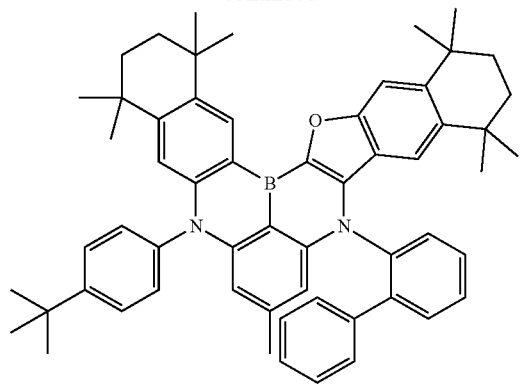
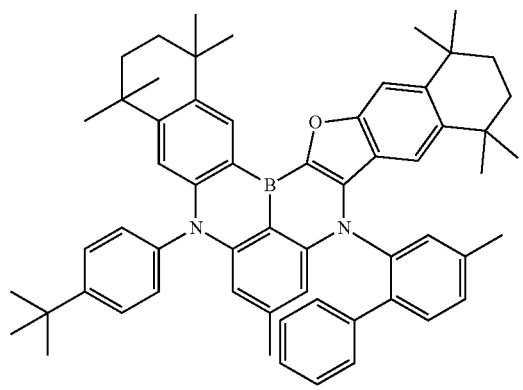
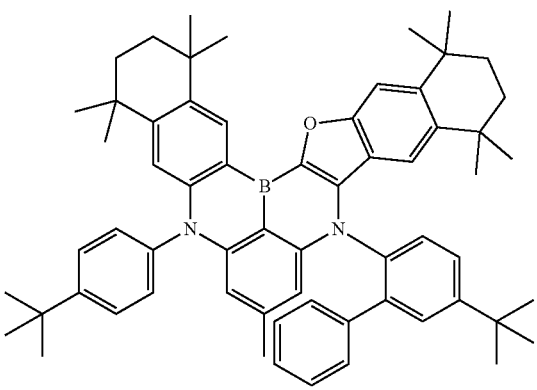
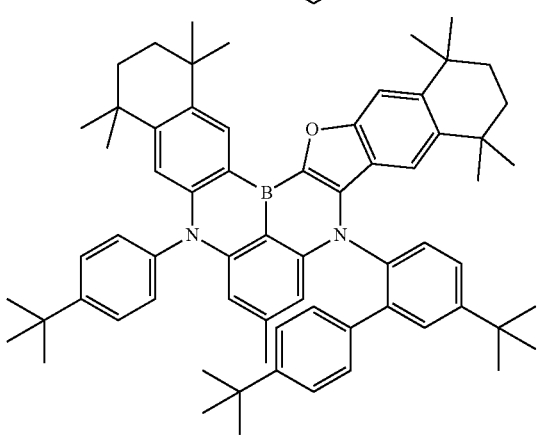
2584
-continued
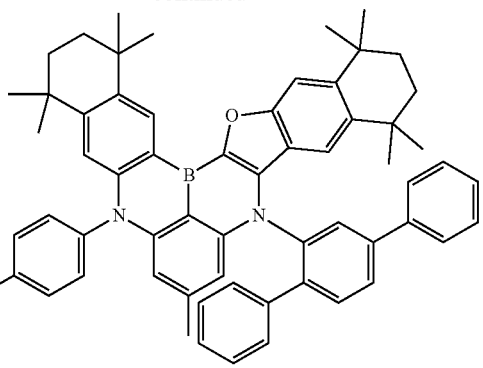
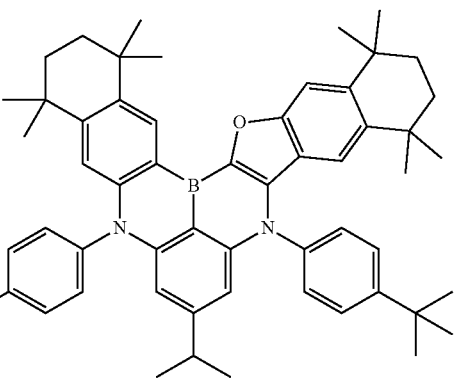
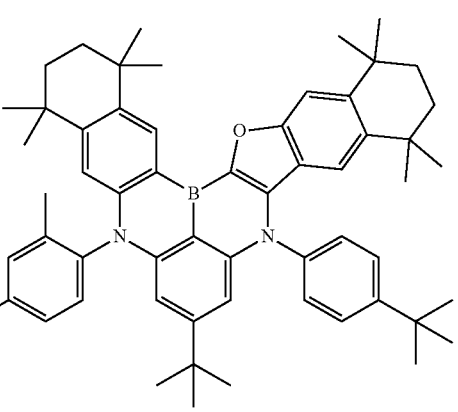
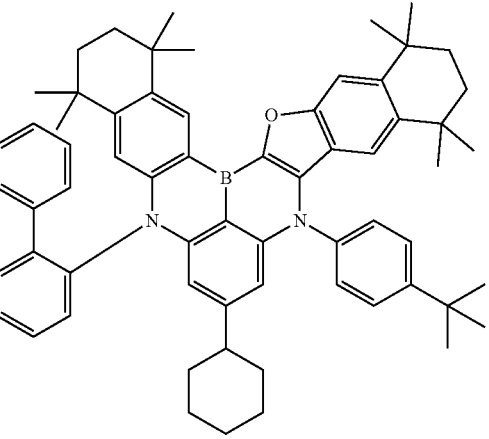

2585
-continued
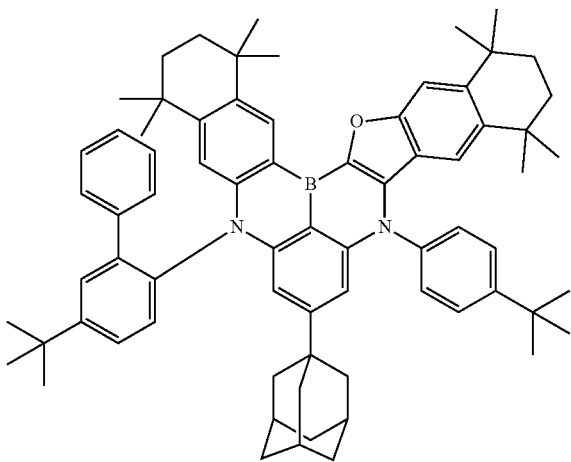
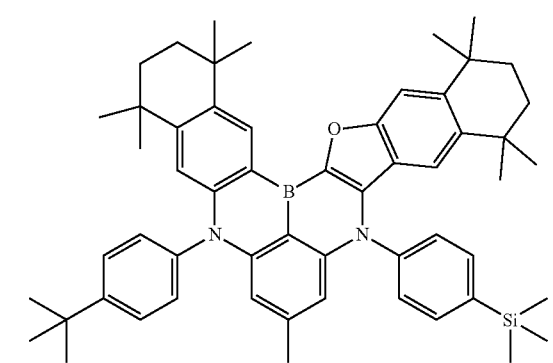
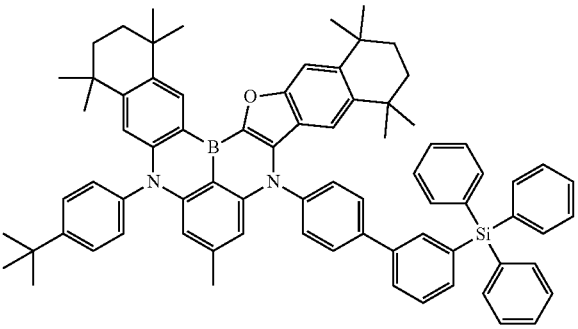
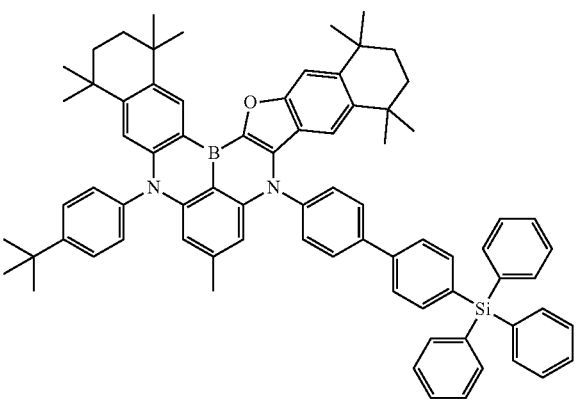
2586
-continued
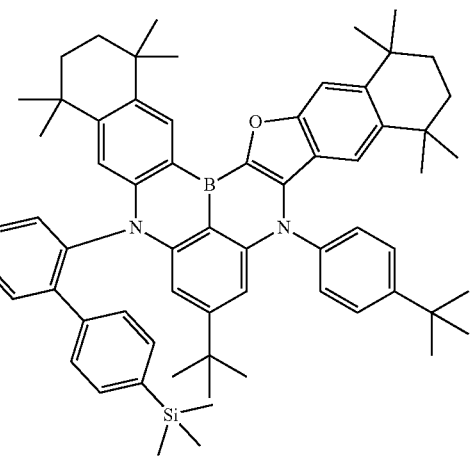
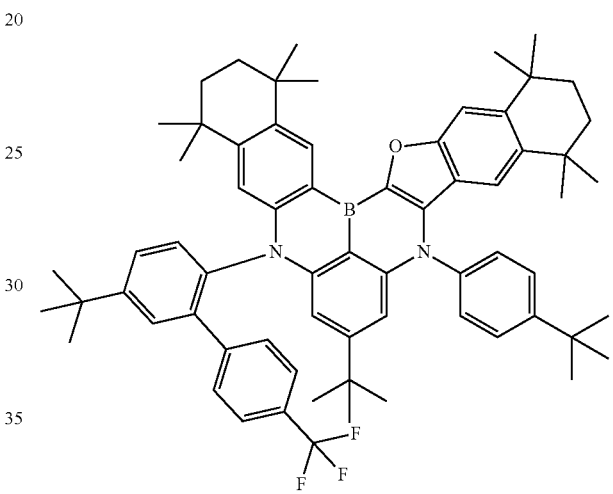
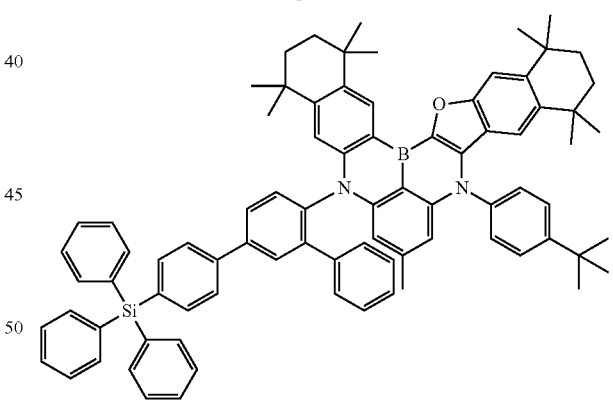
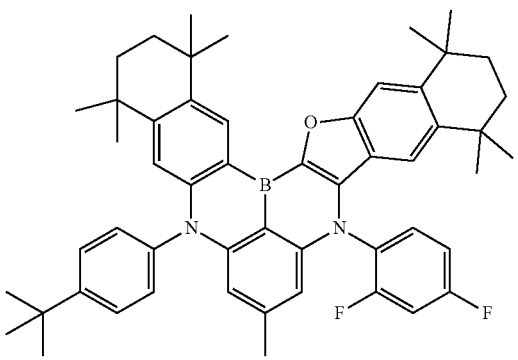

2587
-continued
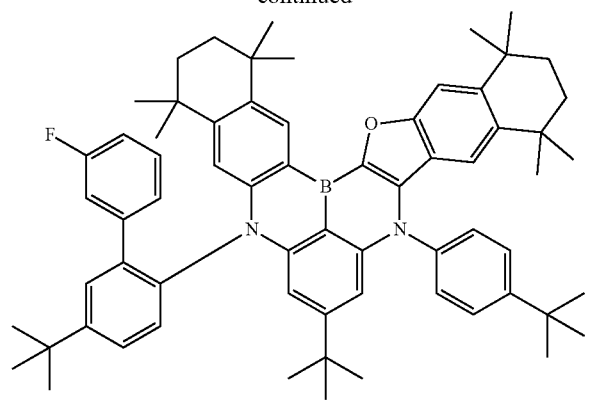
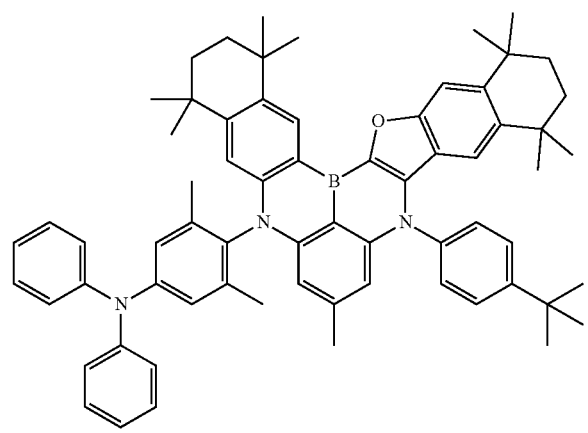
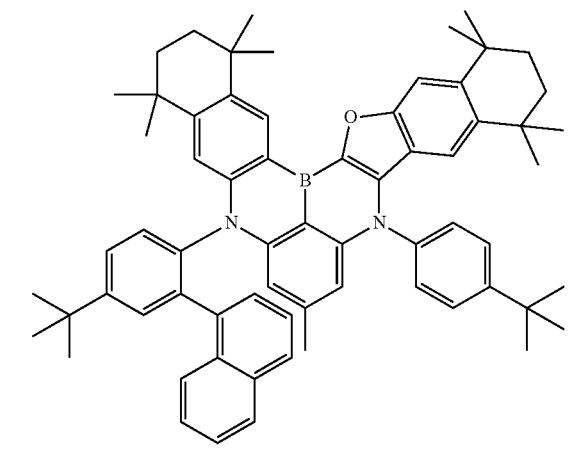
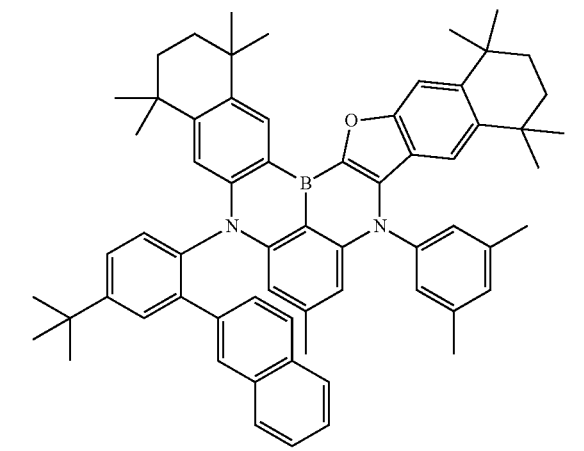
2588
-continued
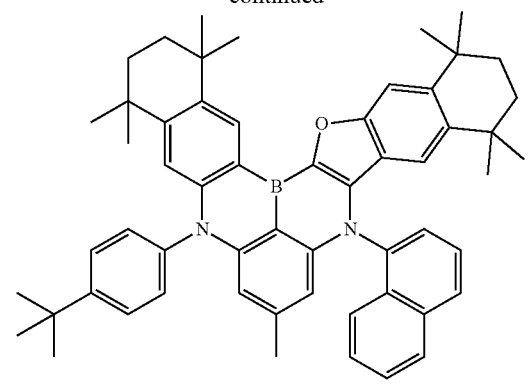
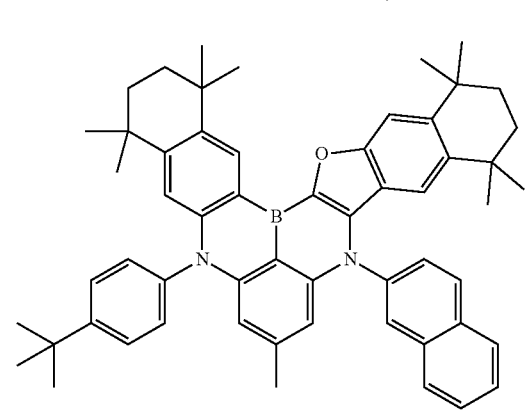
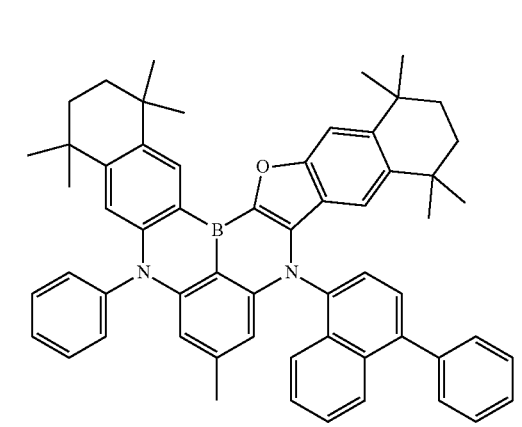
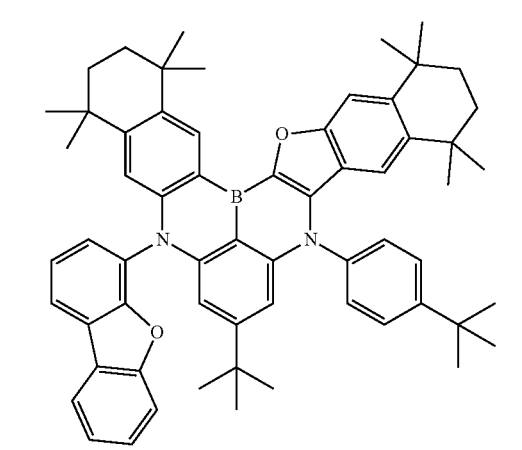

| 2589 -continued | 2590 -continued |
|---|---|
| 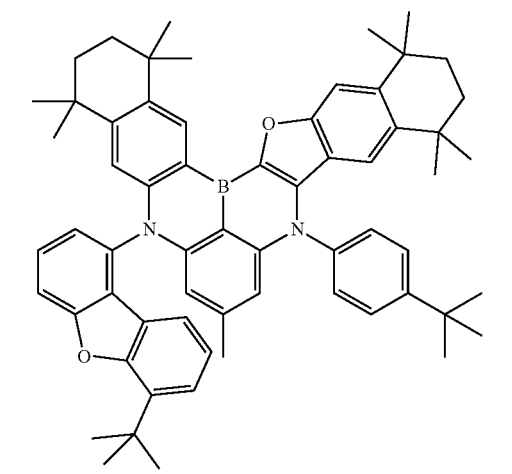 | 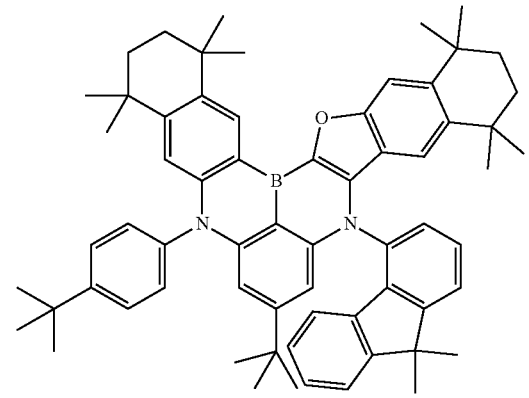 |
| 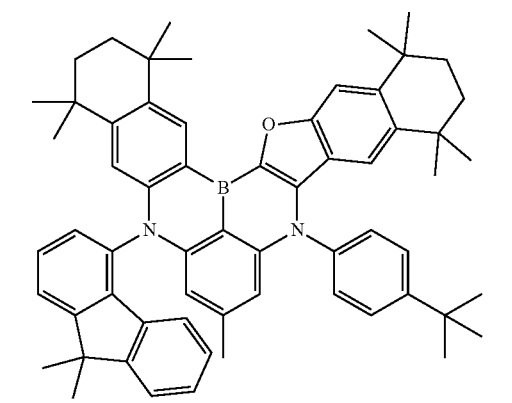 | 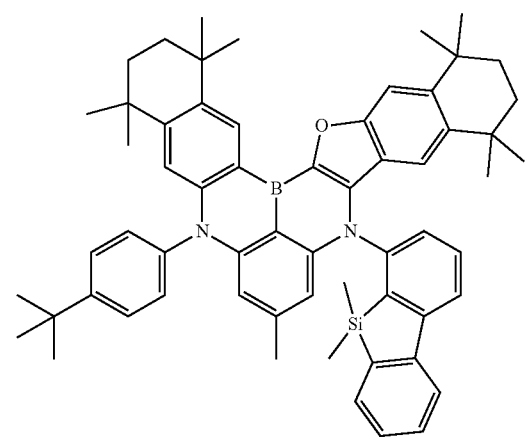 |
| 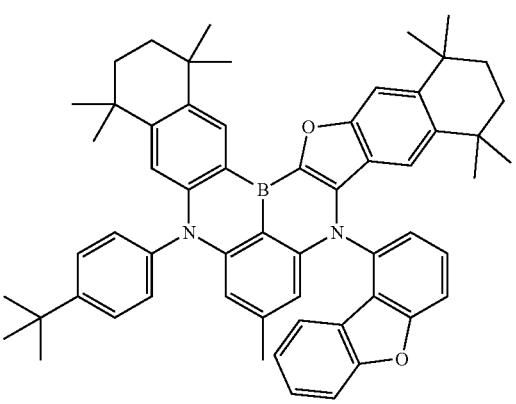 | 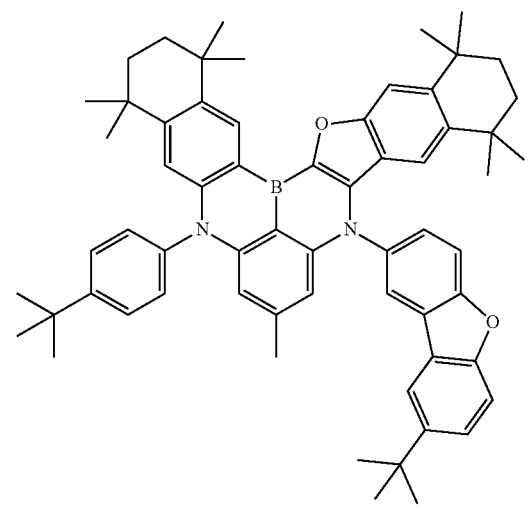 |
| 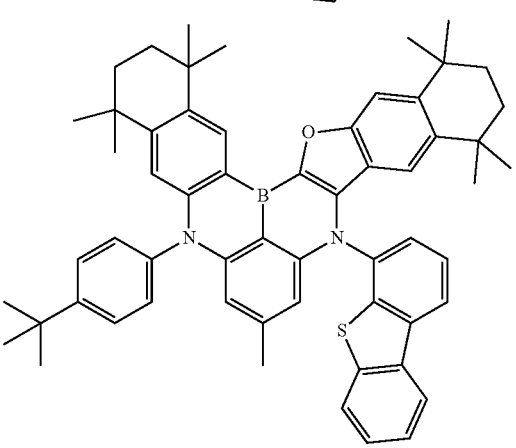 | |

2591
-continued
2592
-continued
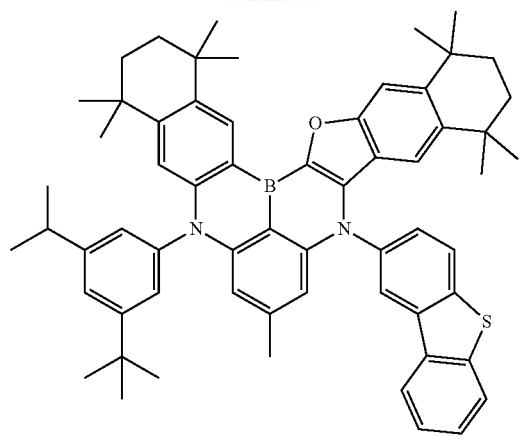
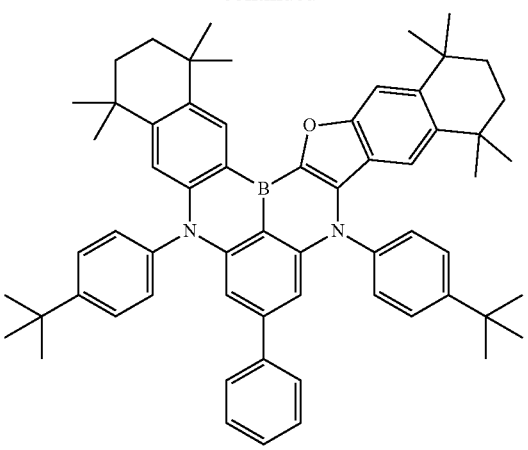
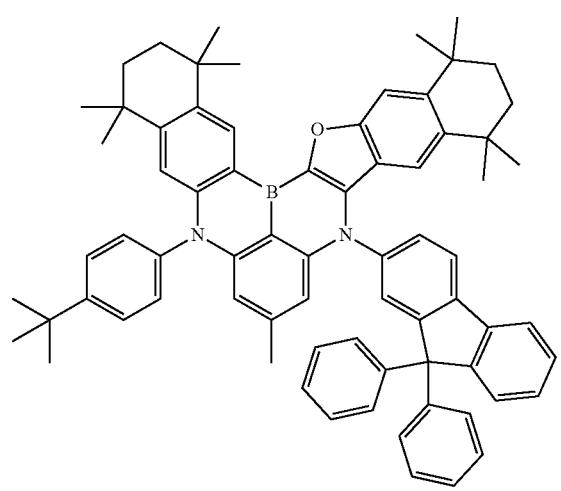
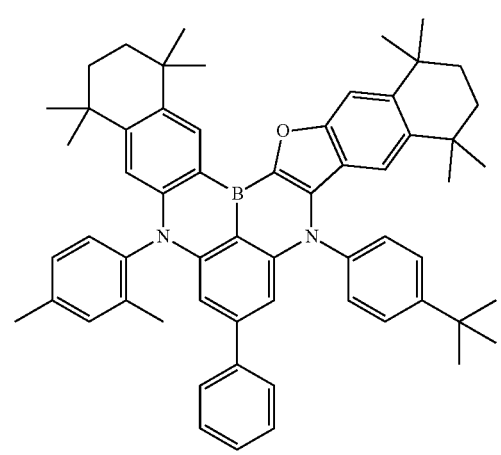
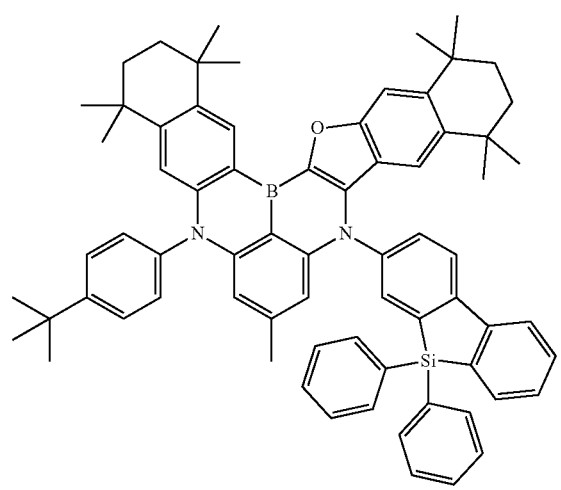

2593
-continued
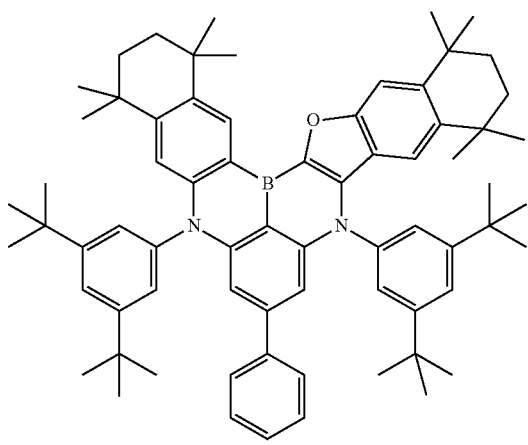
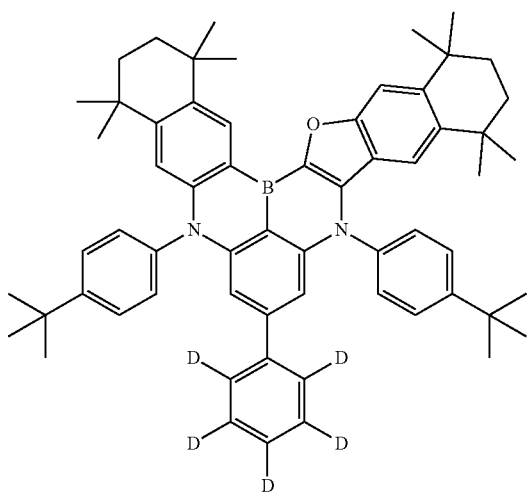
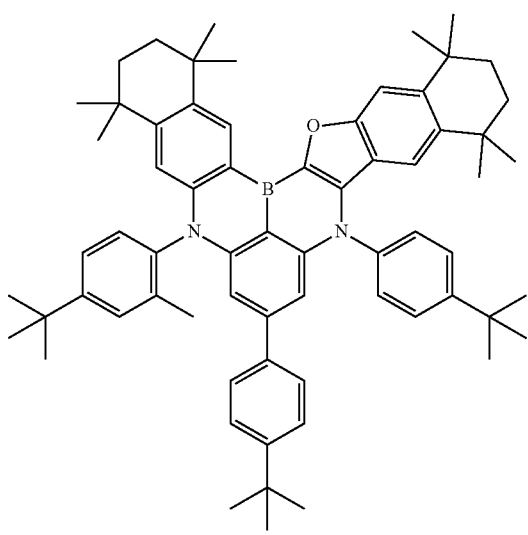
2594
-continued
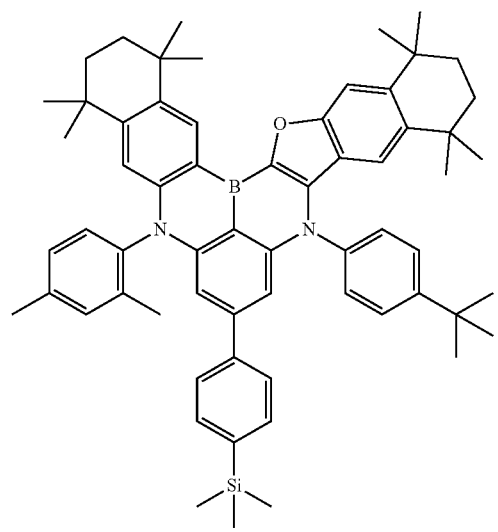
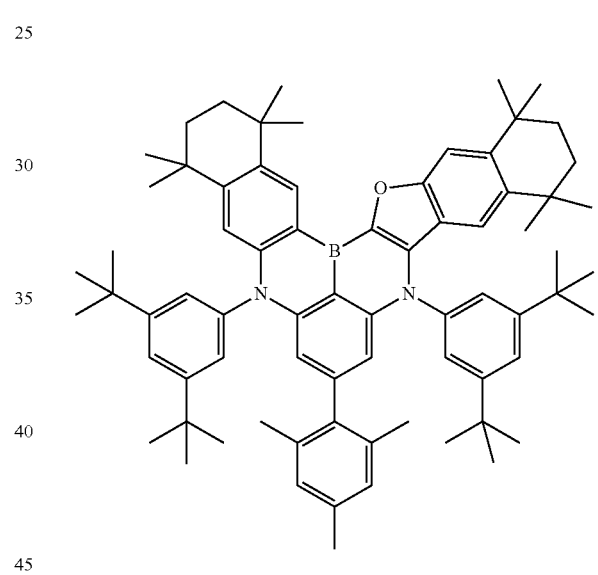
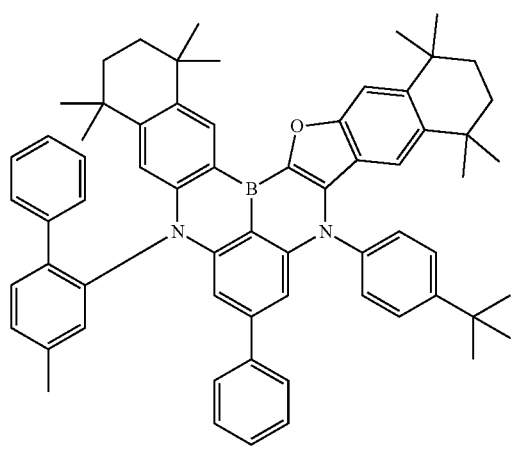

2595
-continued
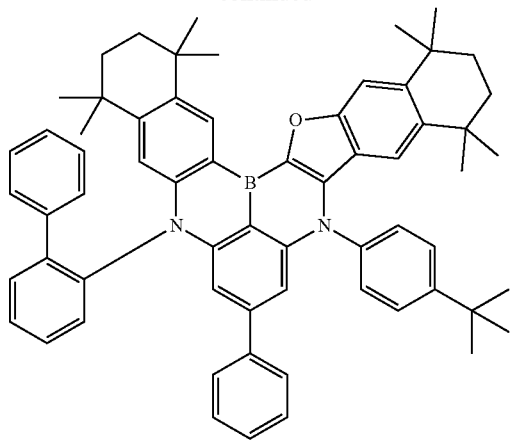
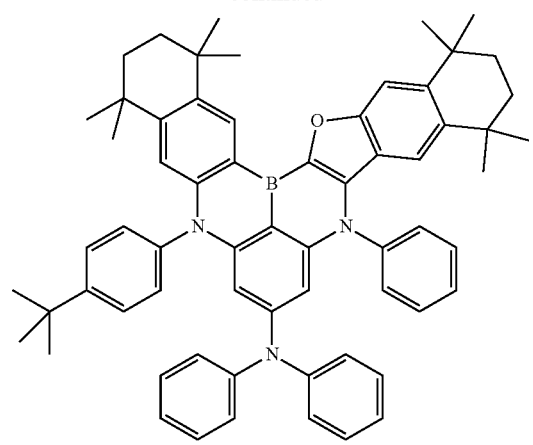
2596
-continued
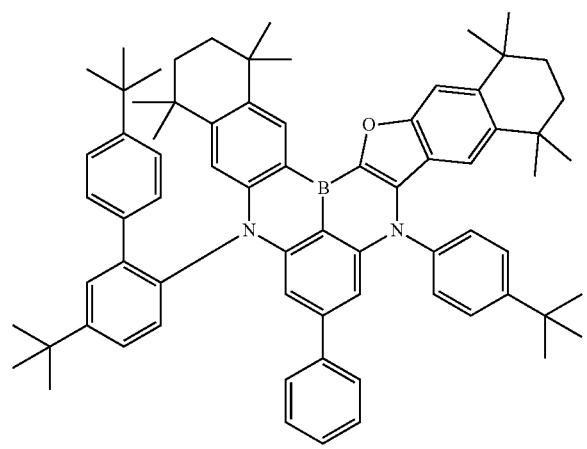
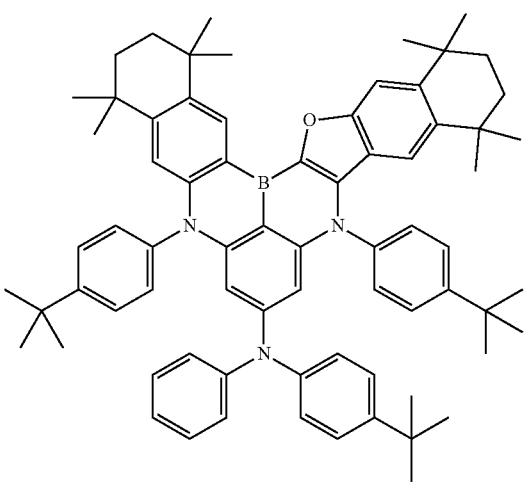
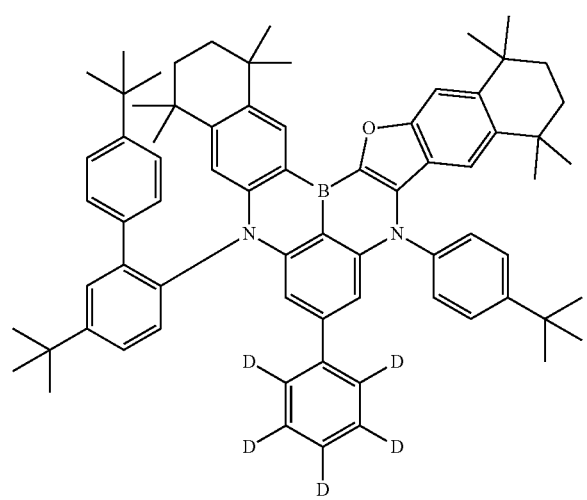
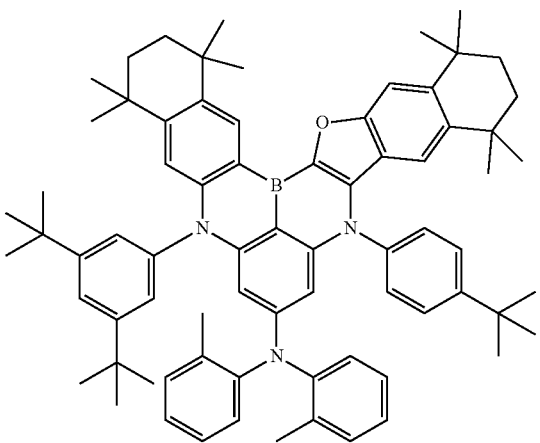

2597
-continued
2598
-continued
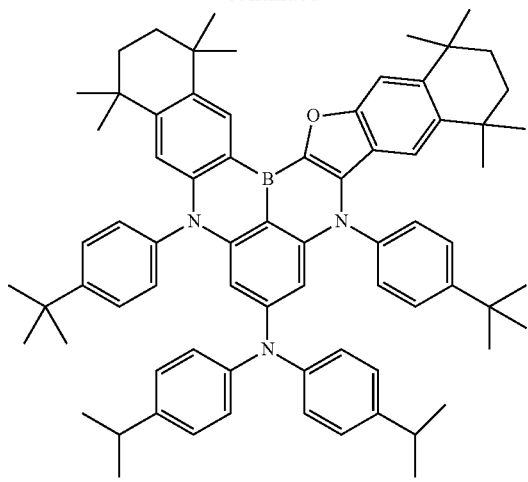
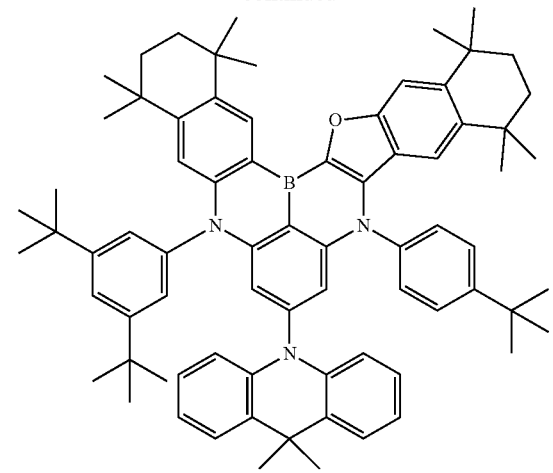
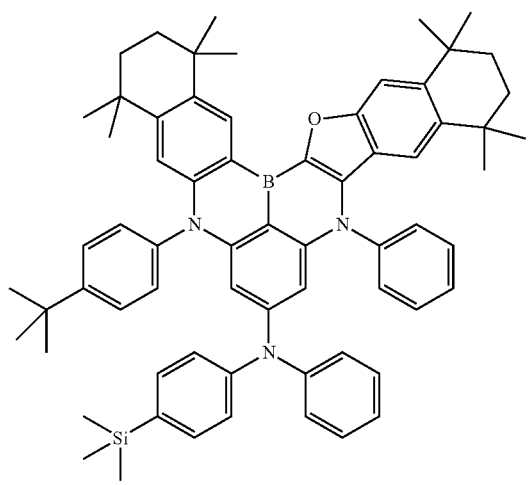
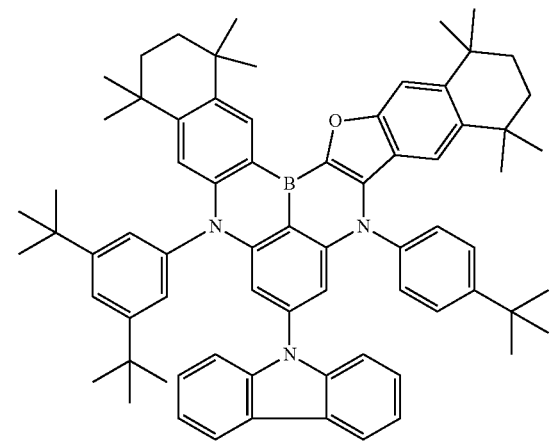
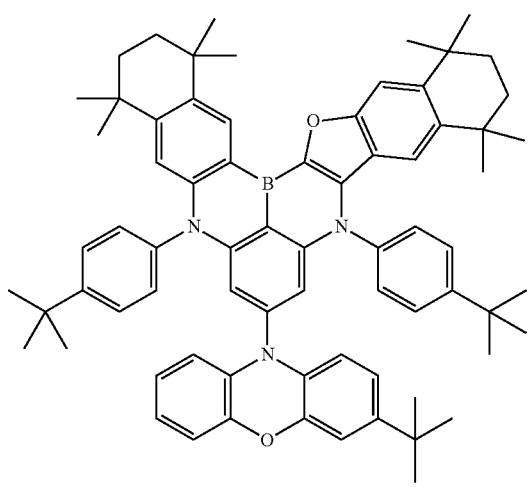
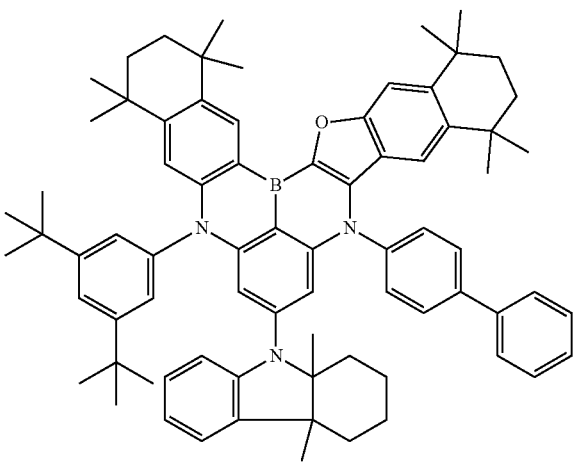

2599
-continued
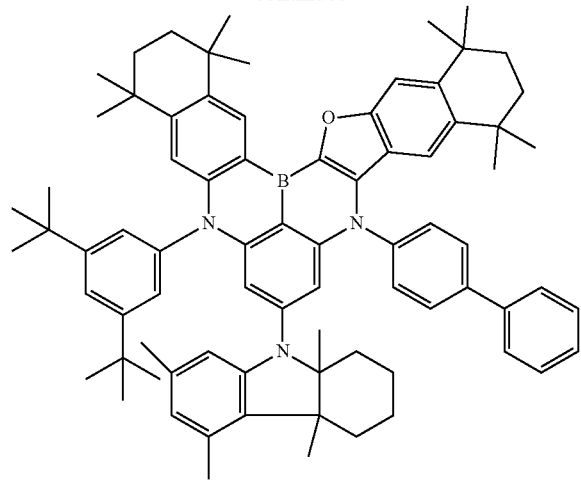
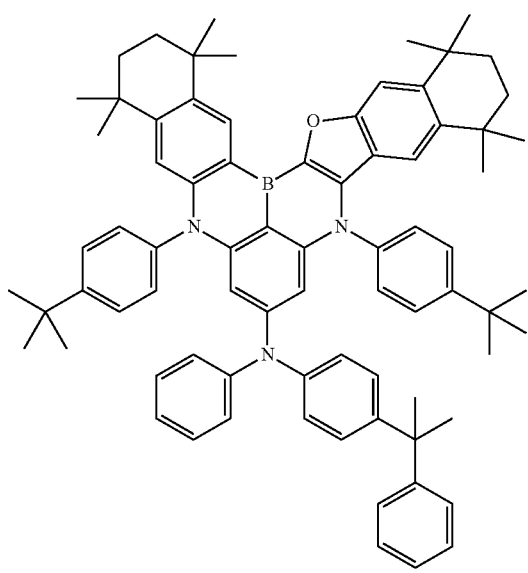
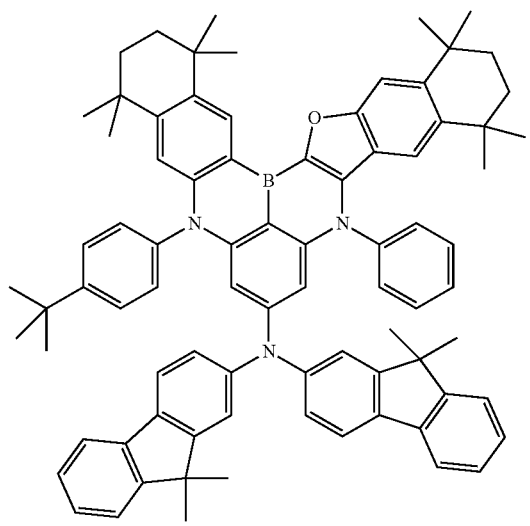
2600
-continued
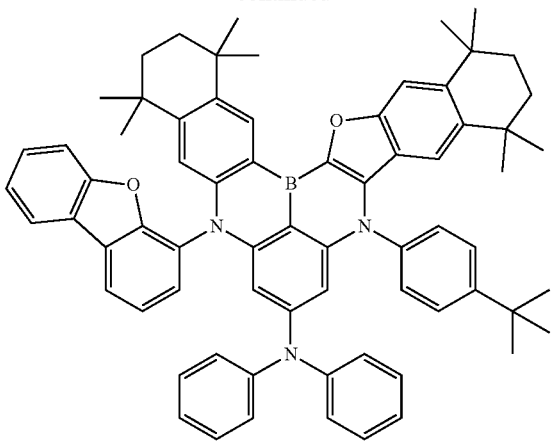
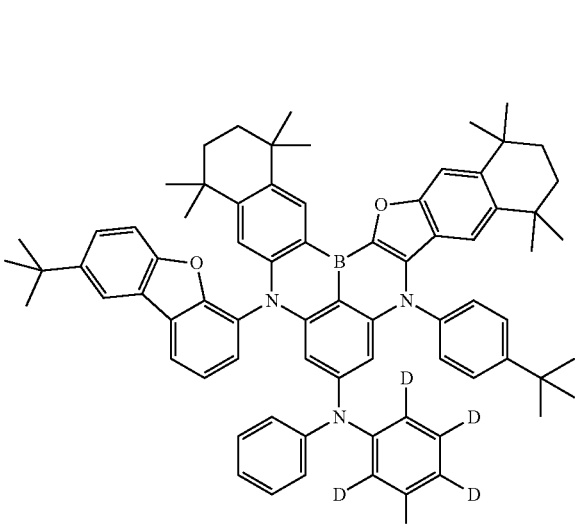
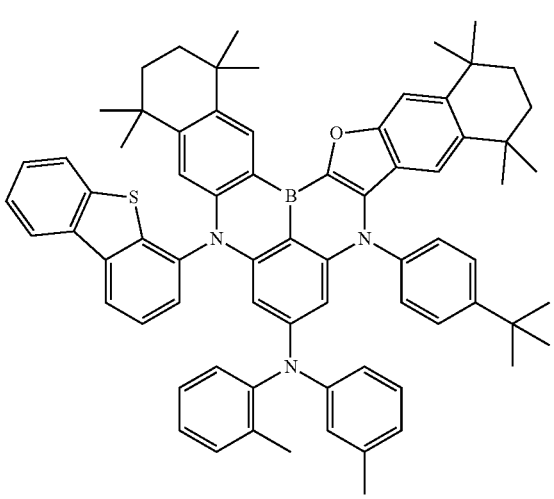

2601
-continued
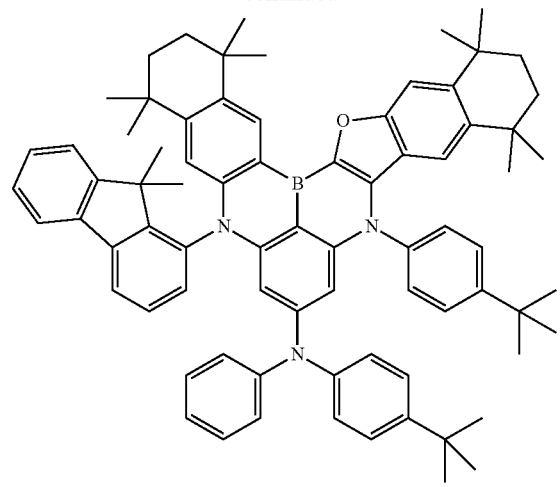
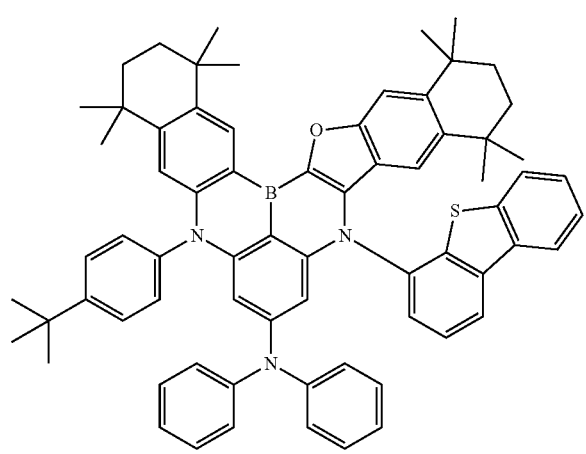
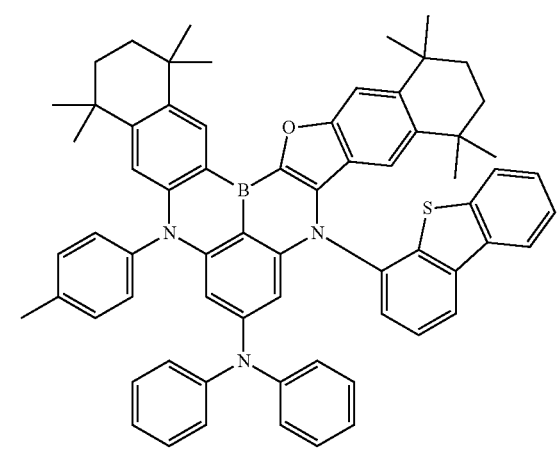
2602
-continued
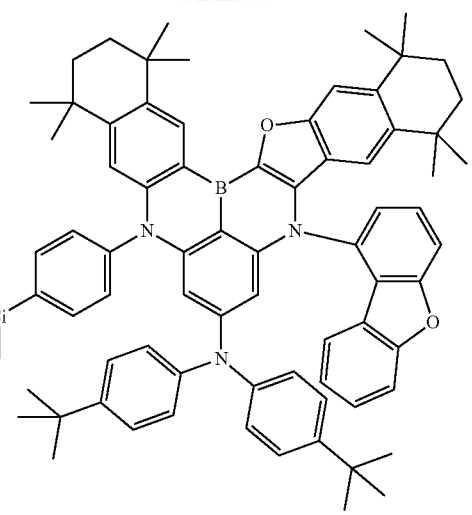
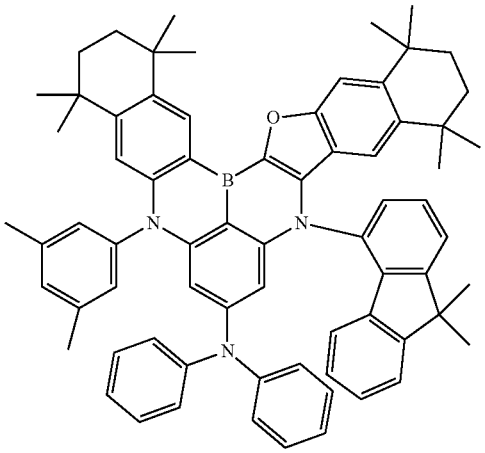
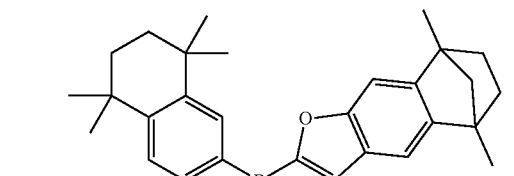
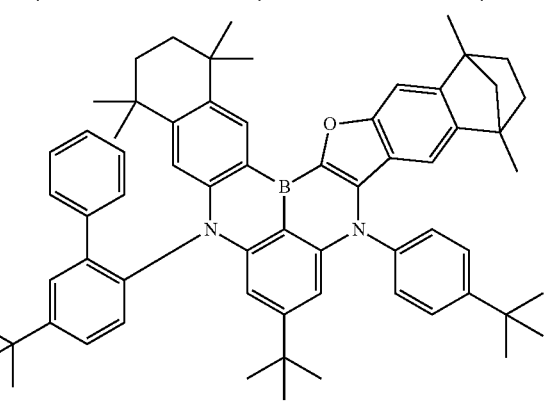

2603
-continued
2604
-continued
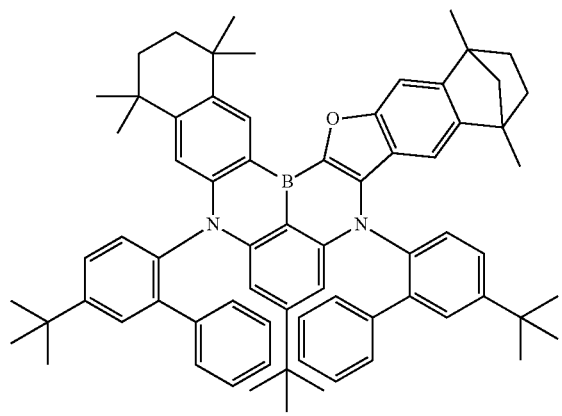
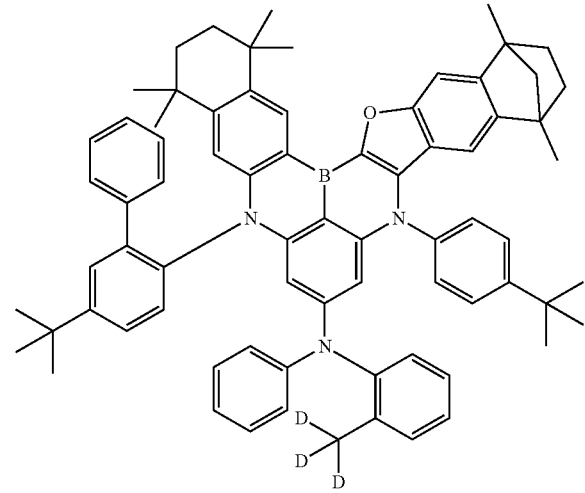
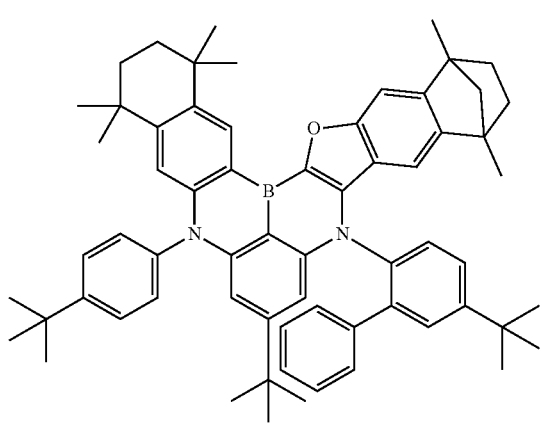
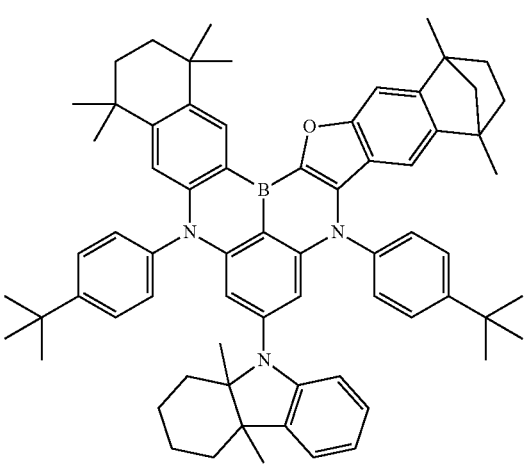
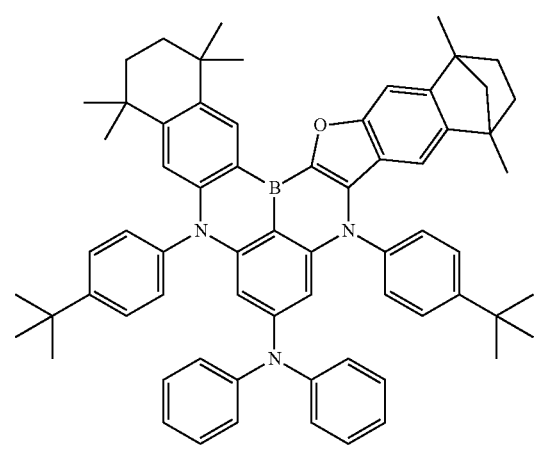
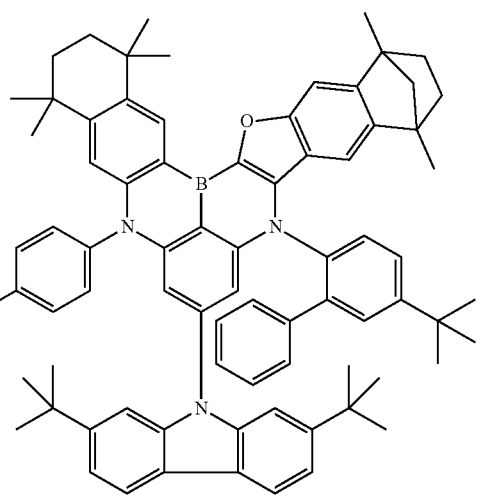

2605
-continued

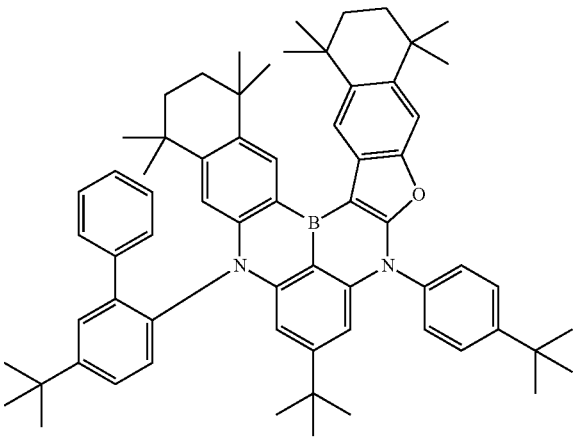
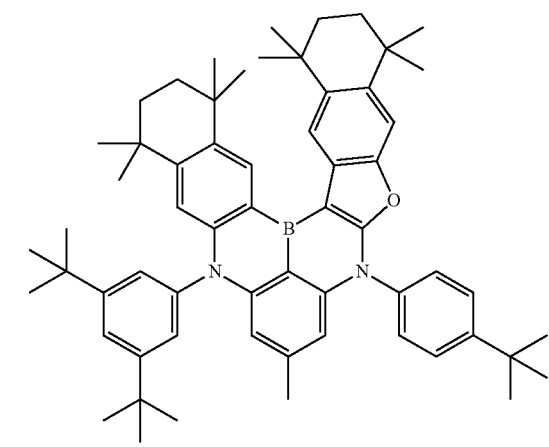
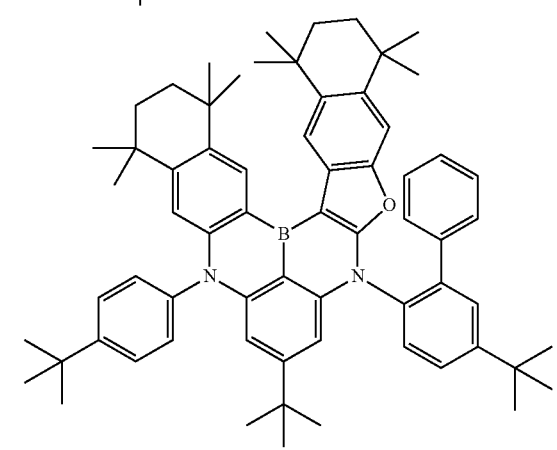
2606
-continued
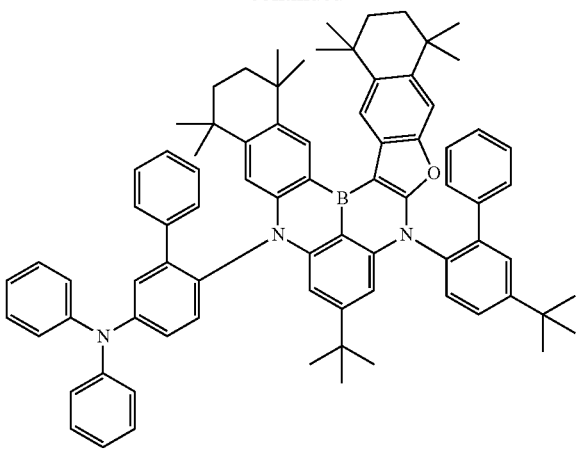
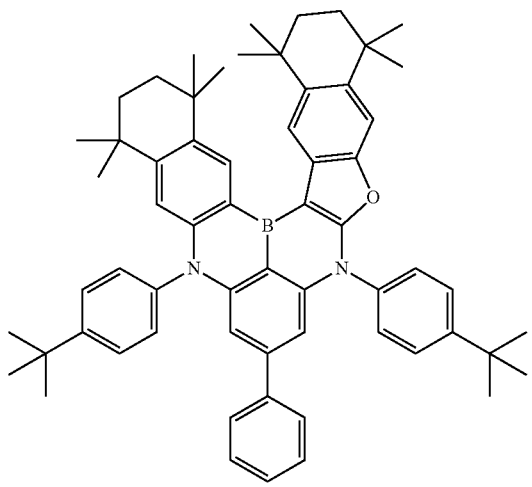
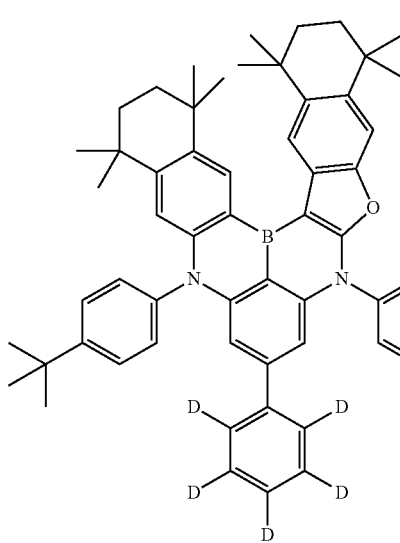

2607
-continued
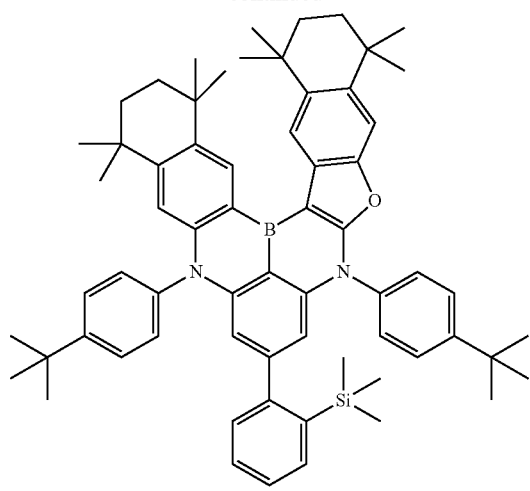
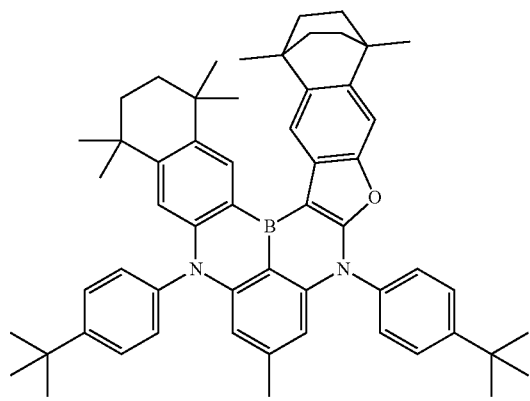
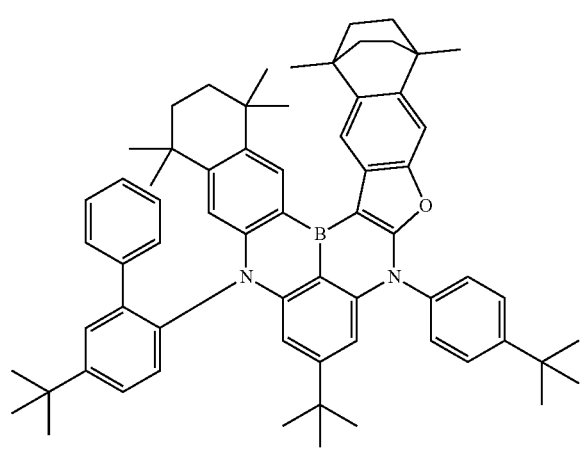
2608
-continued
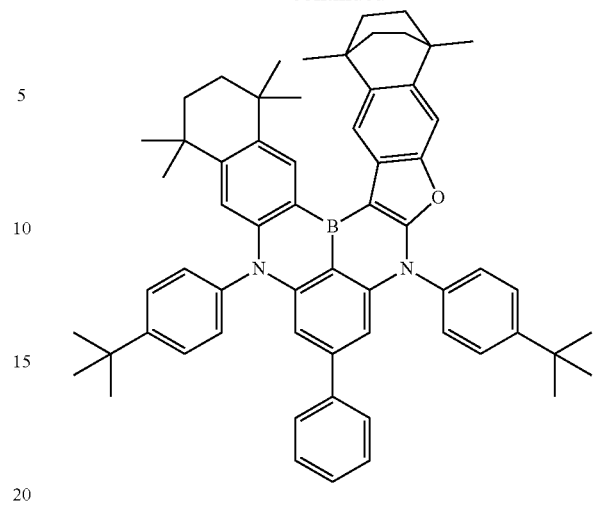
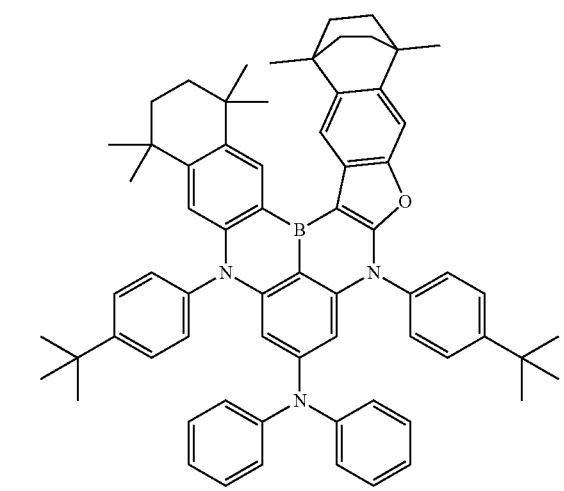
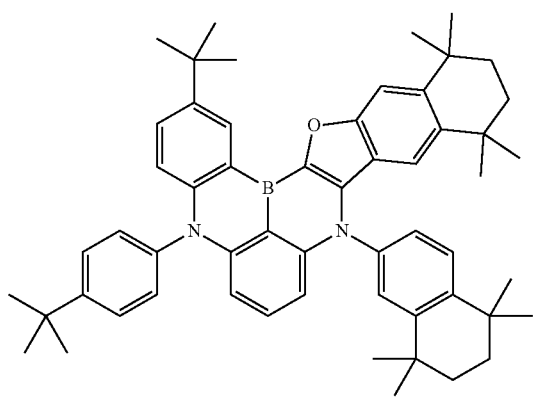

2609
-continued
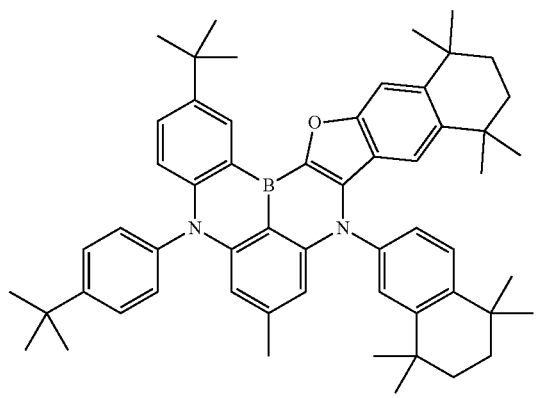
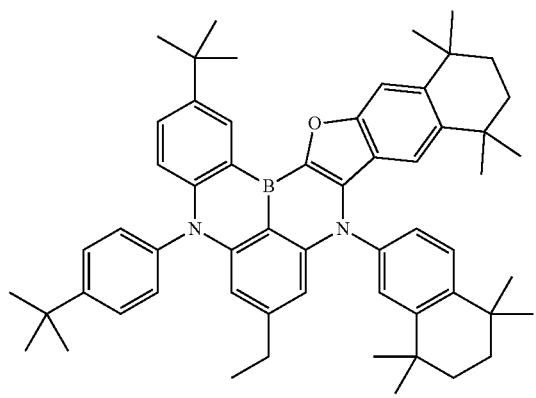
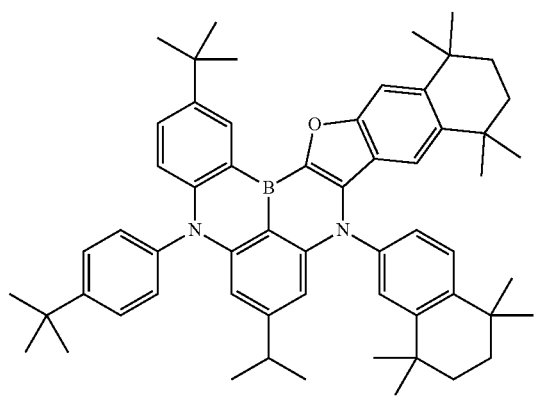
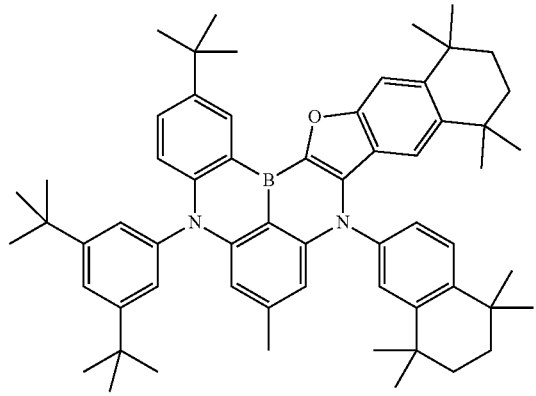
2610
-continued
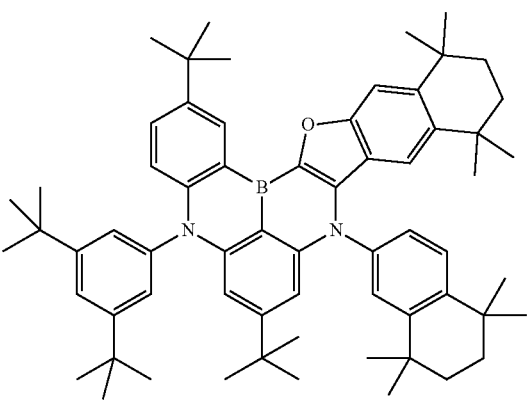
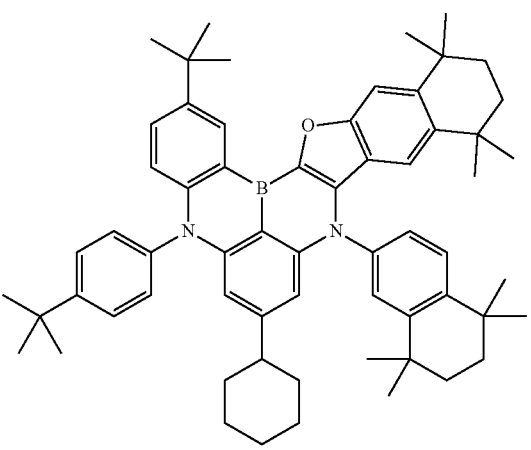
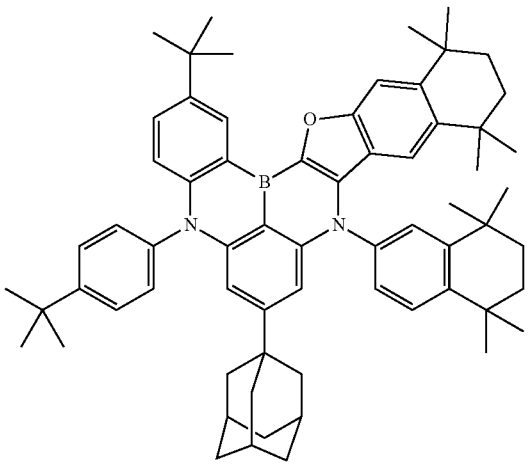
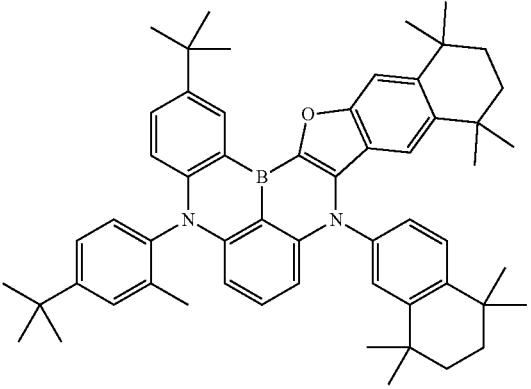

2611
-continued
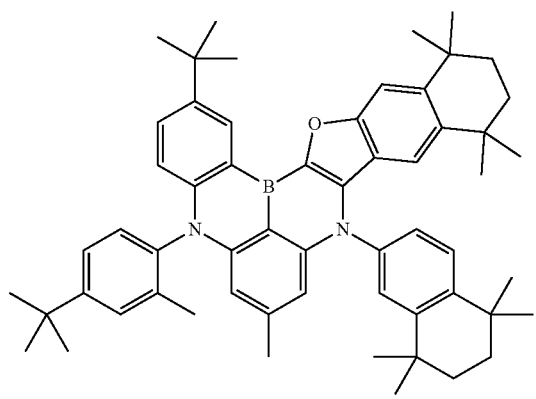
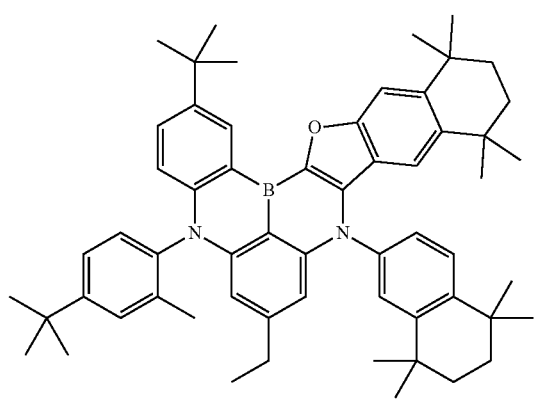
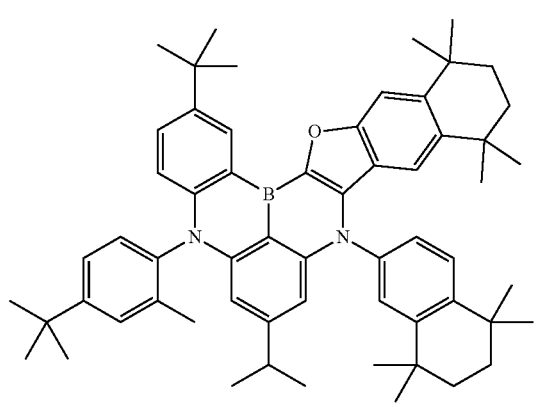
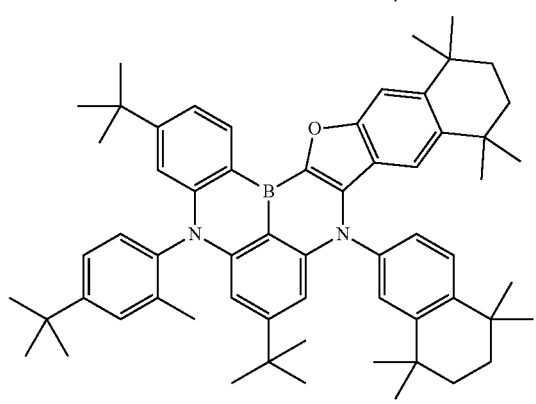
2612
-continued
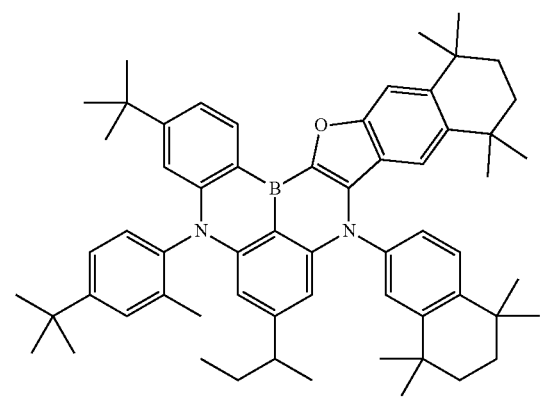
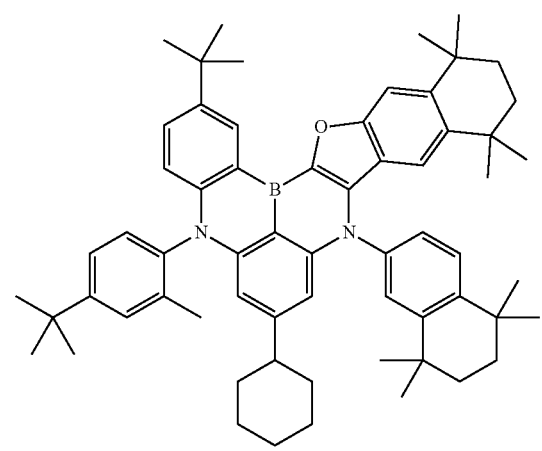
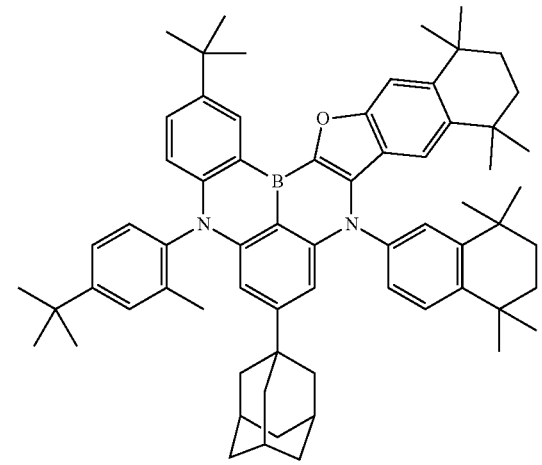
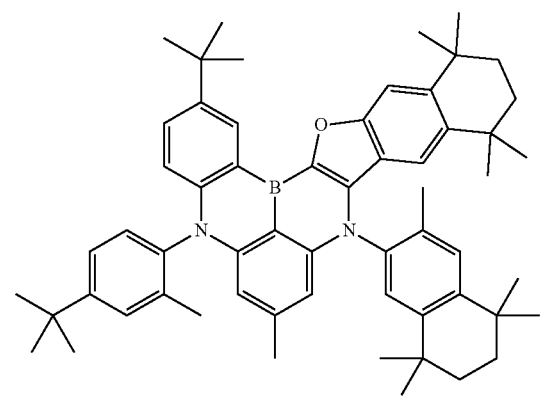

2613
-continued
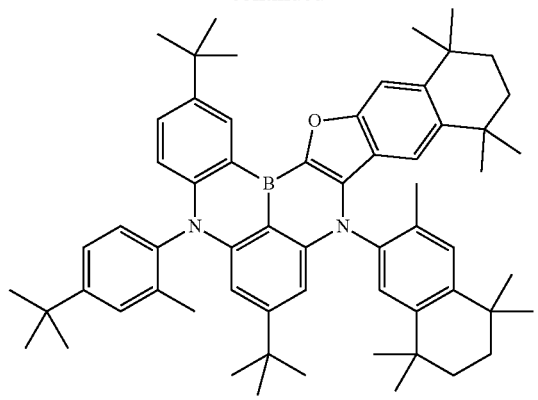
2614
-continued
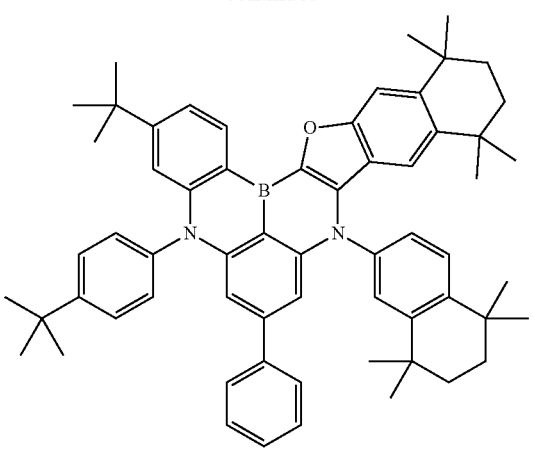
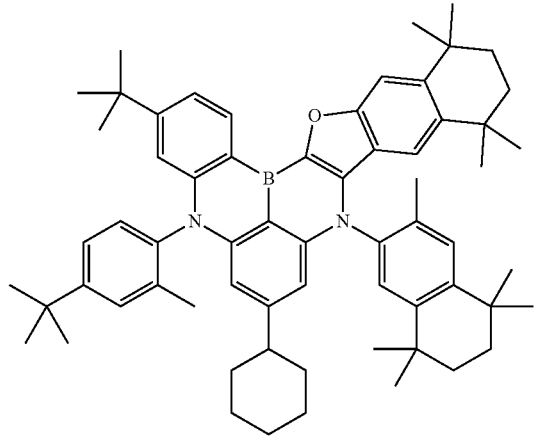
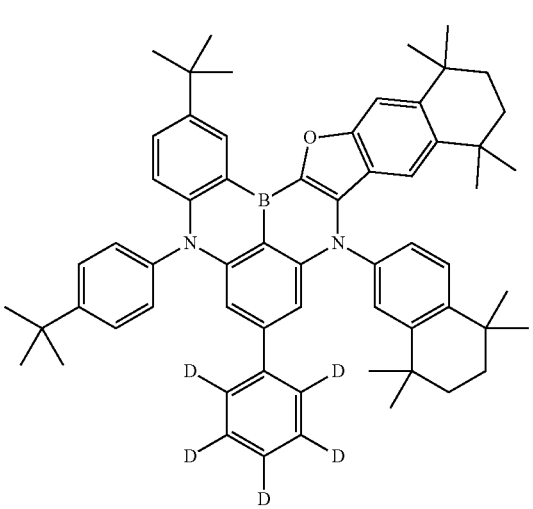
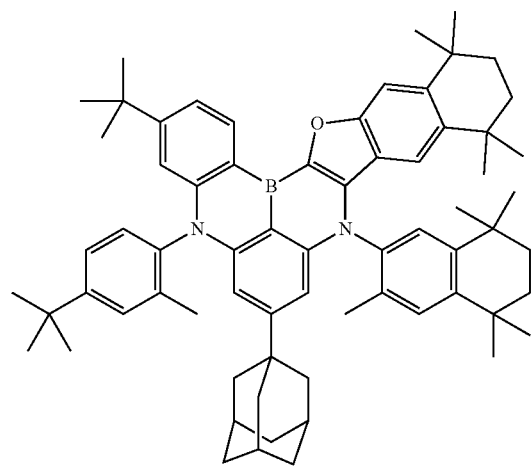
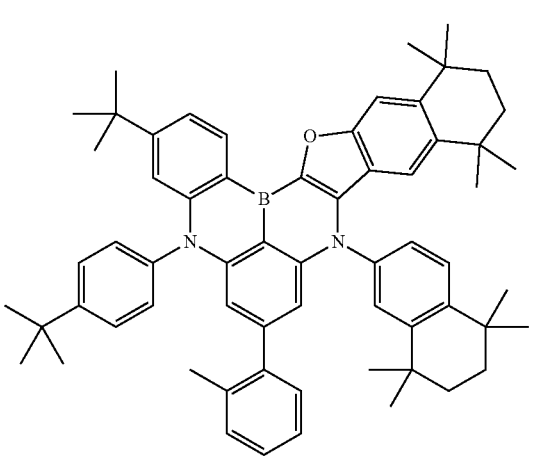

2615
-continued
2616
-continued
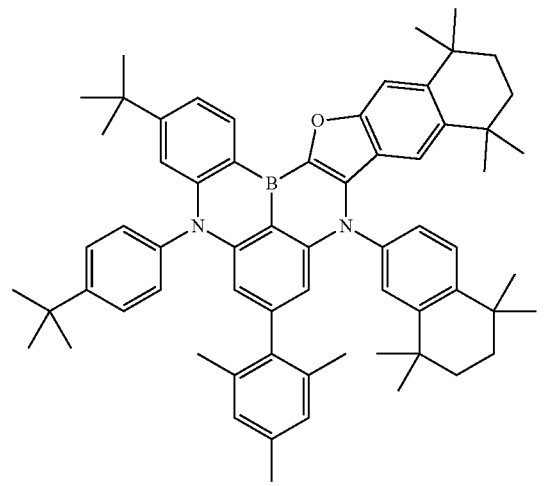
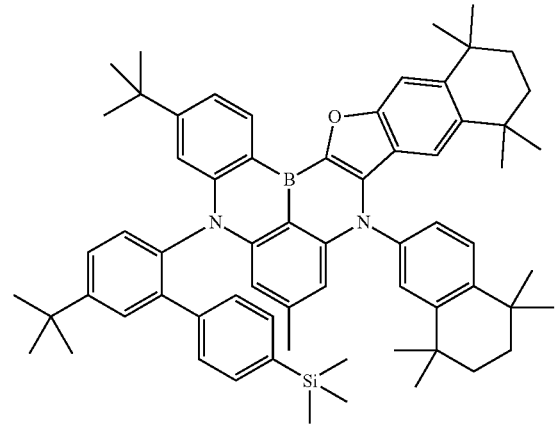
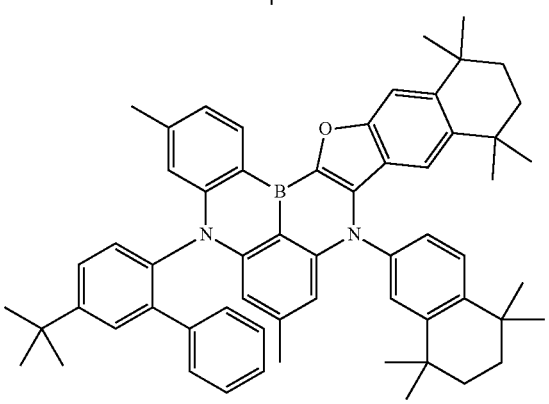
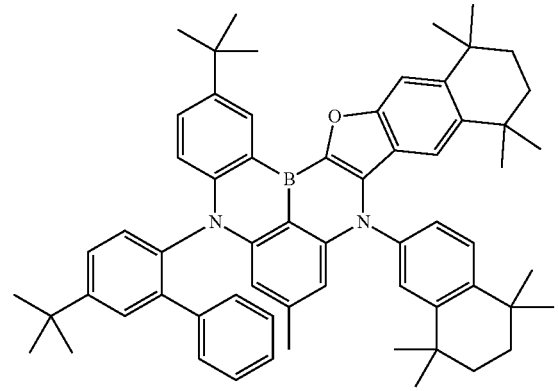
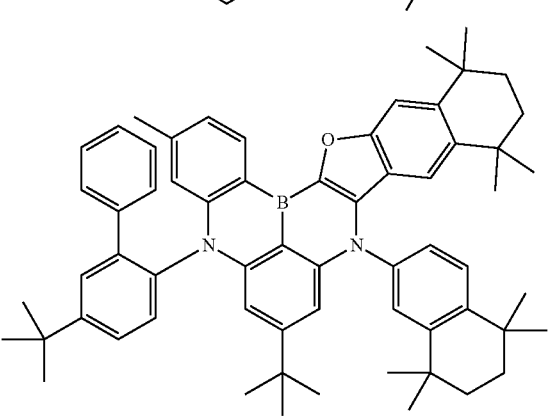
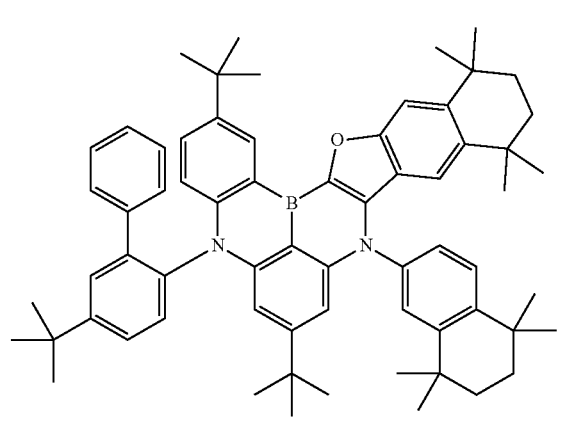
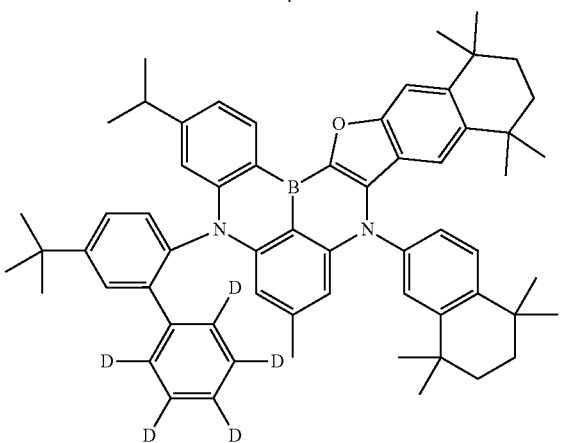
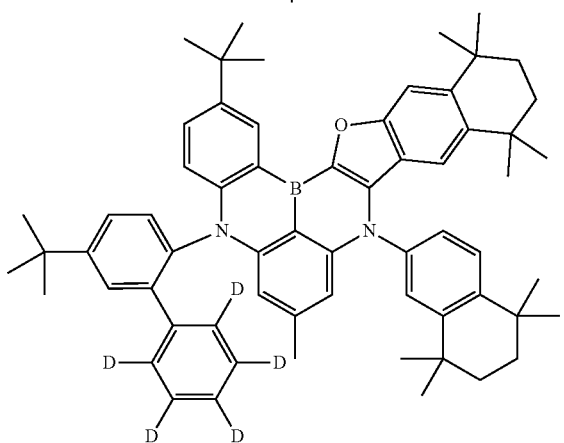

| 2617 -continued | 2618 -continued |
|---|---|
| 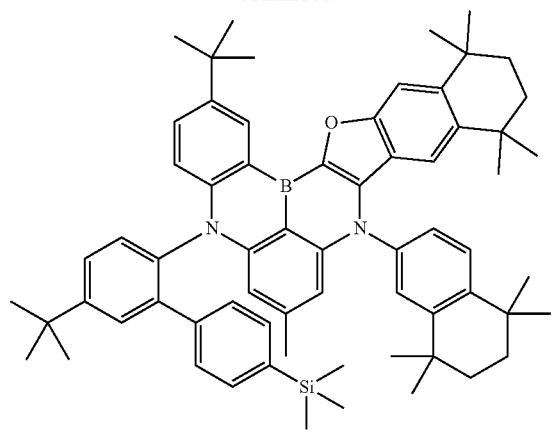 | 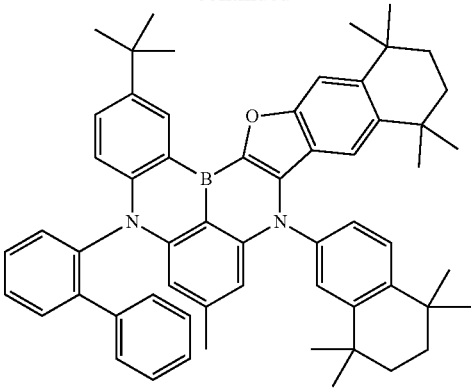 |
| 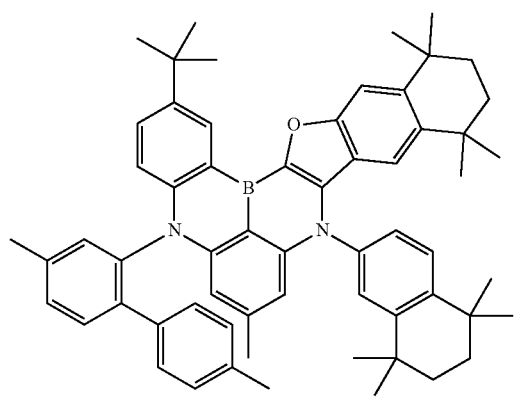 | 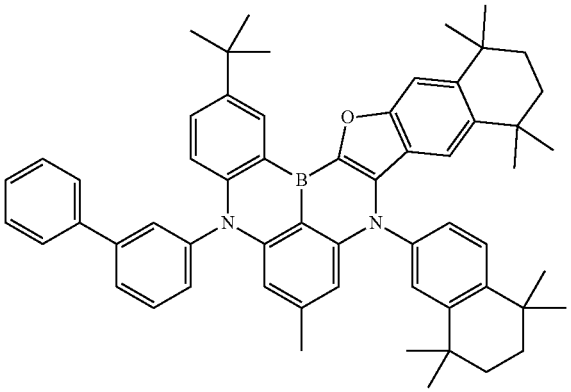 |
| 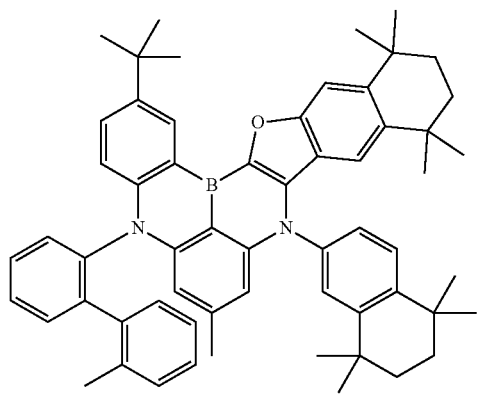 | 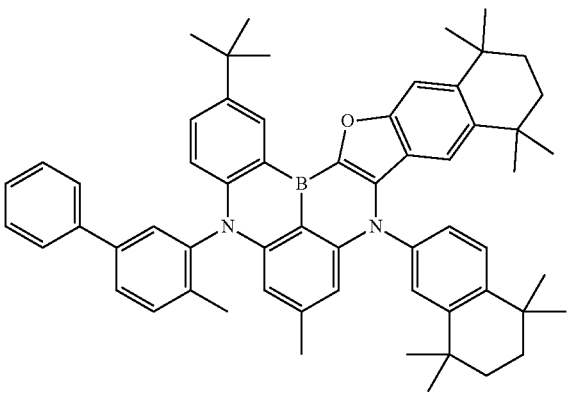 |
| 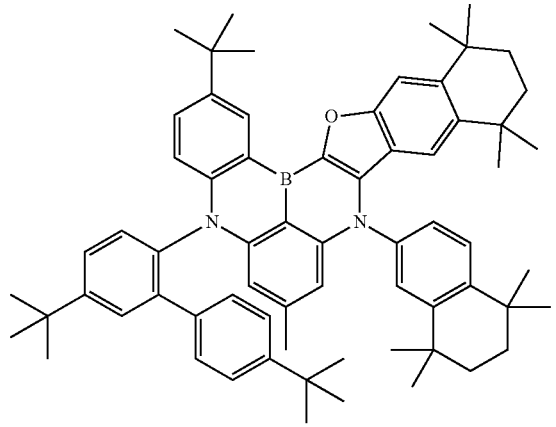 | 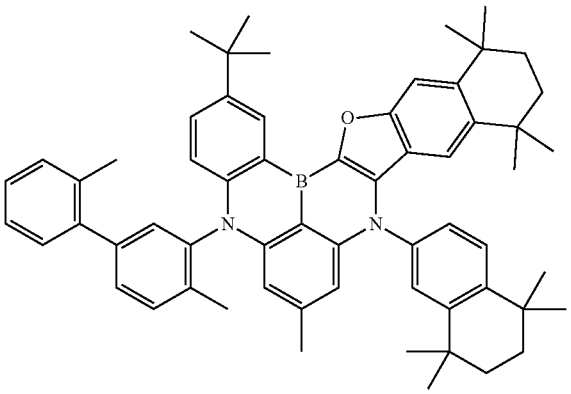 |

2619
-continued
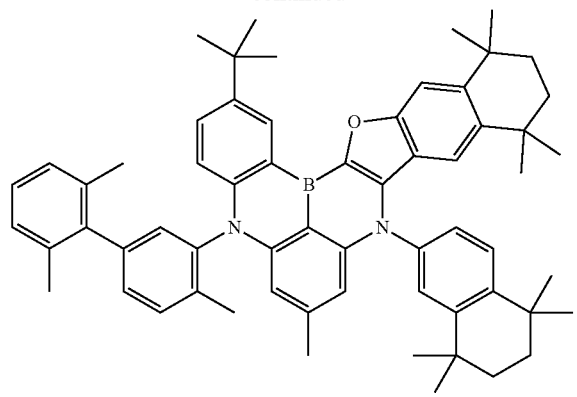
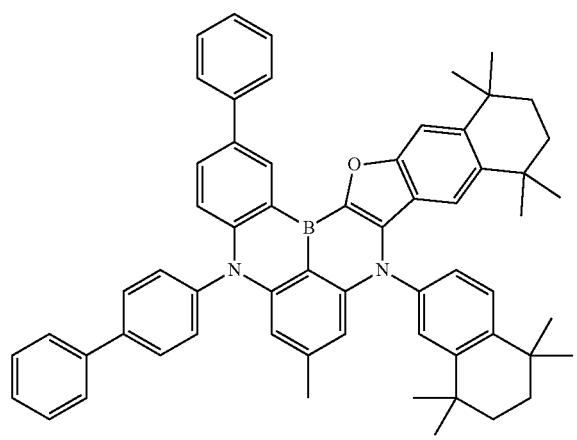
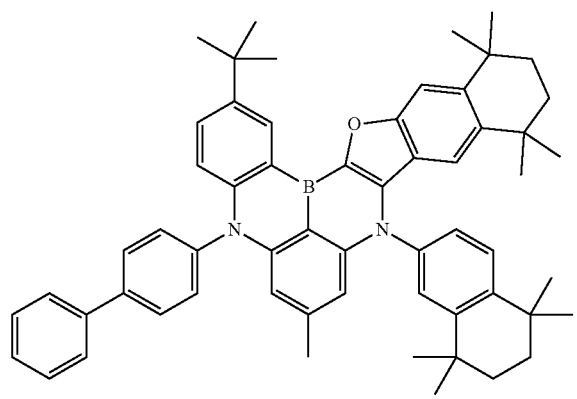
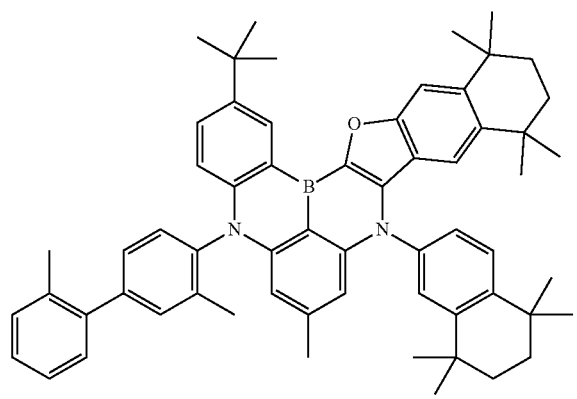
2620
-continued
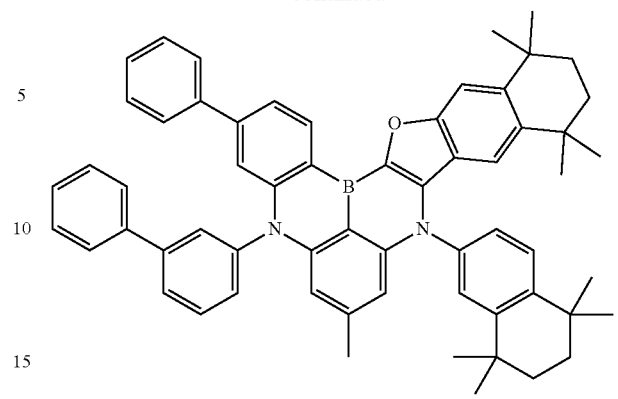
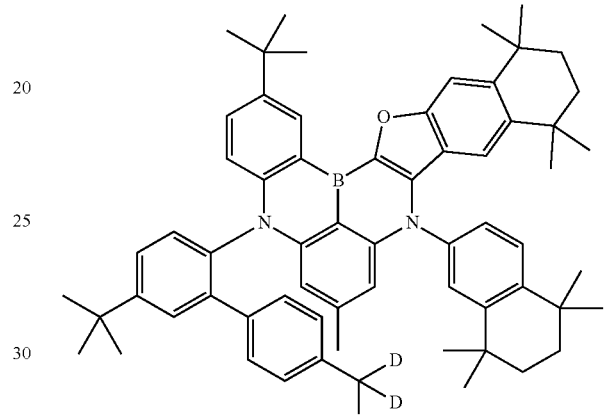
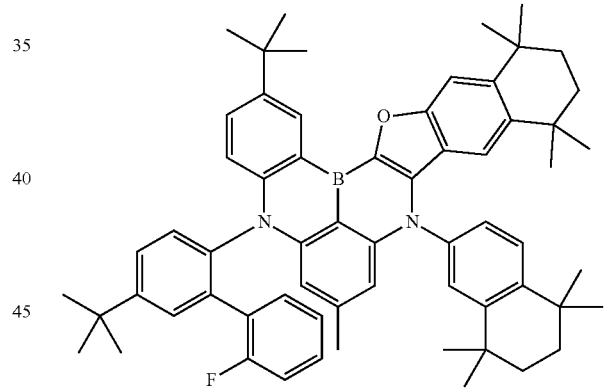
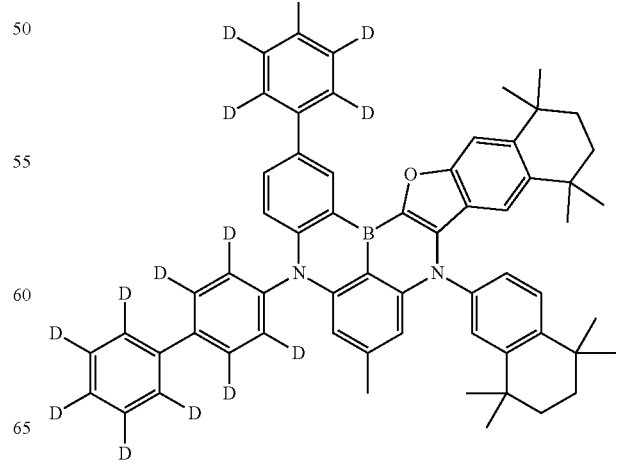

2621
-continued
2622
-continued
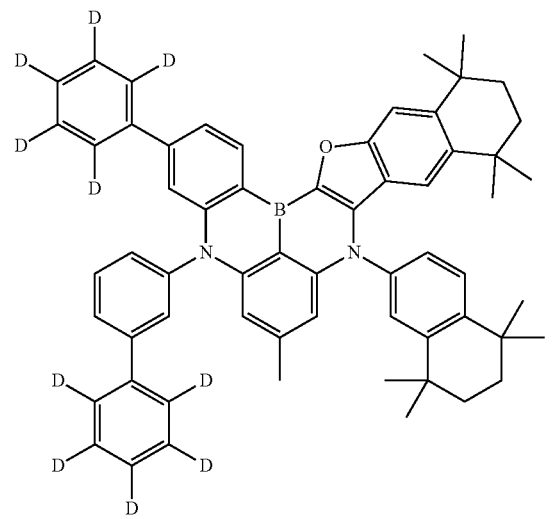
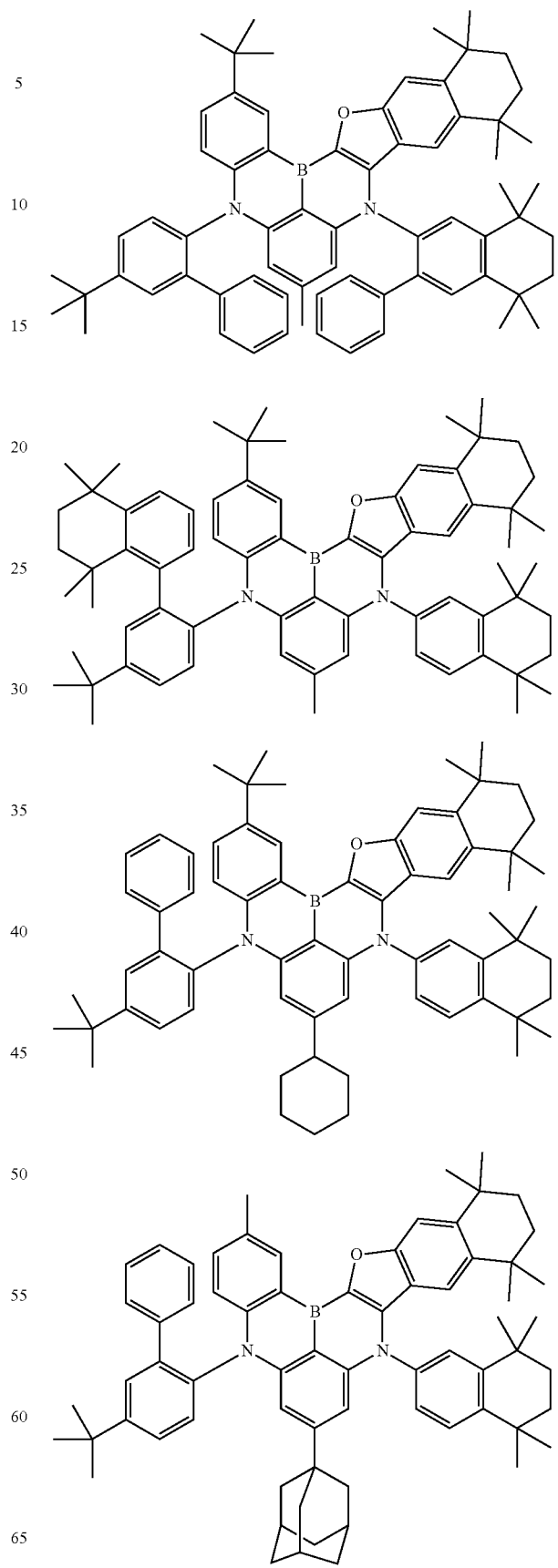

2623 -continued
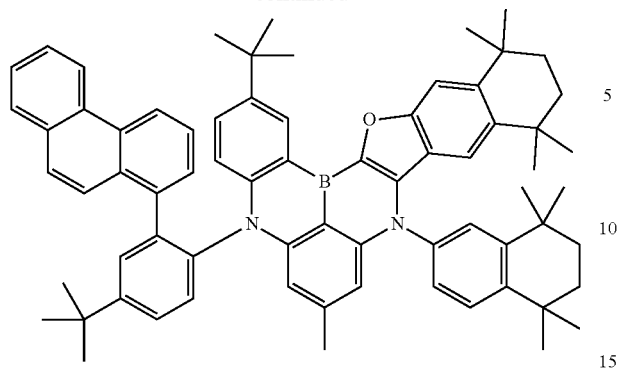

2624 -continued
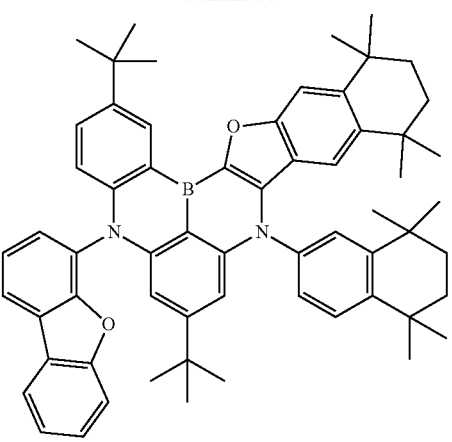
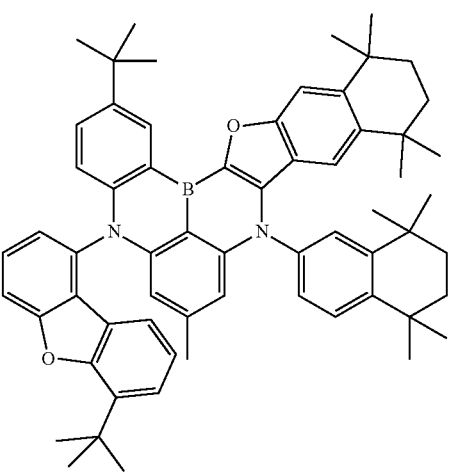
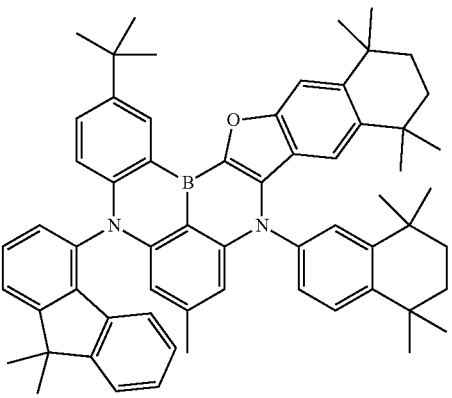
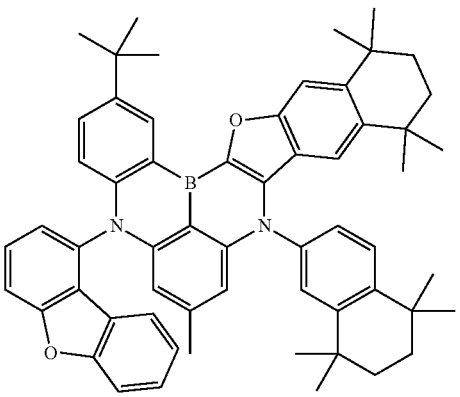

2625
-continued
2626
-continued
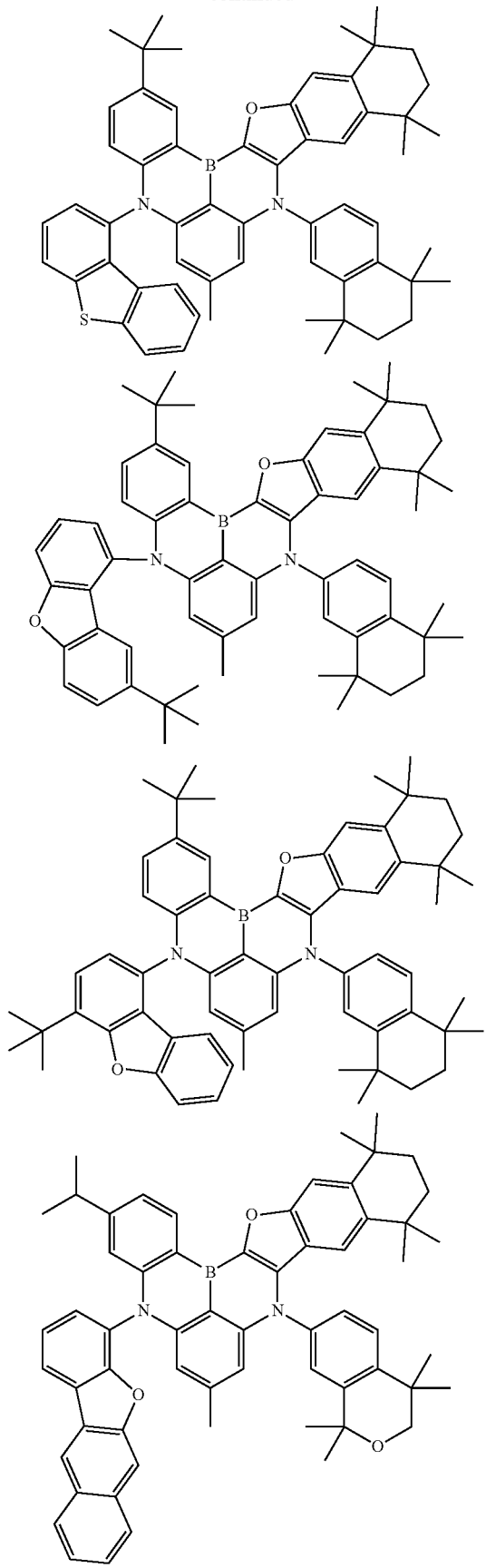
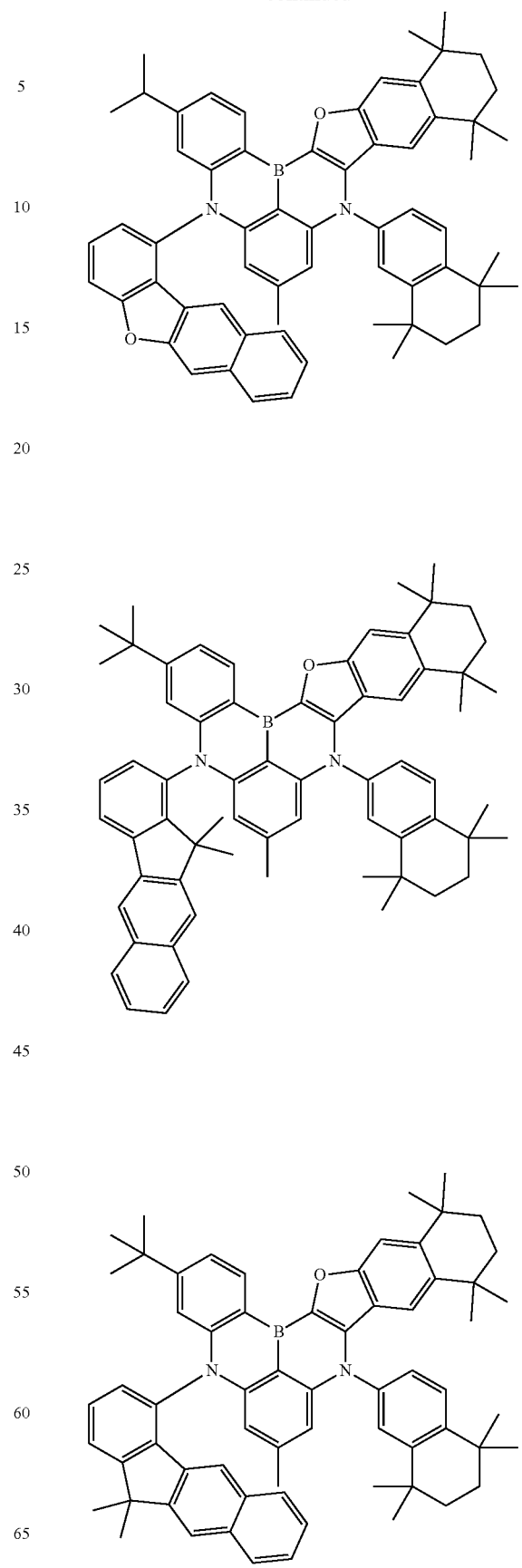

2627
-continued
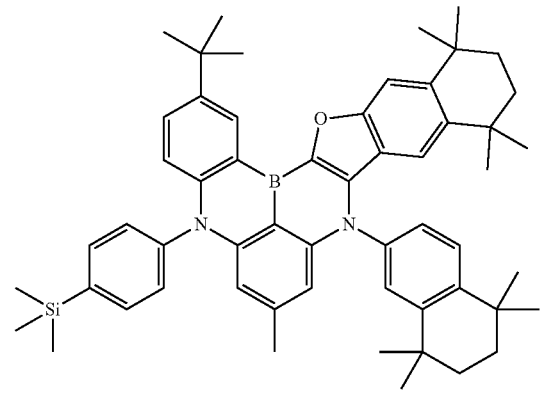
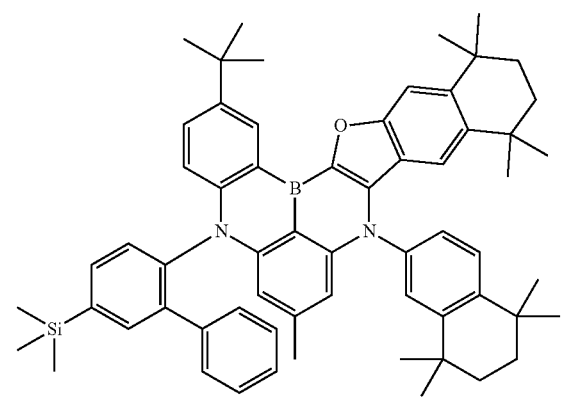
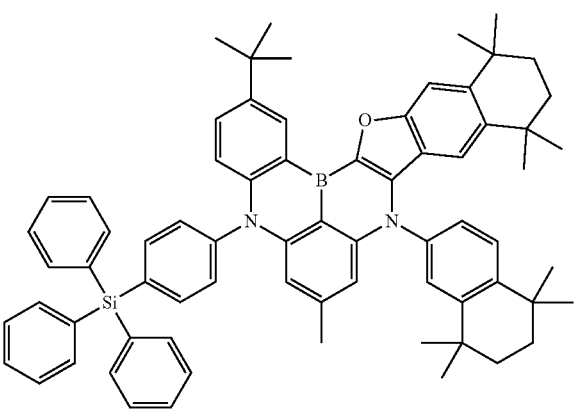
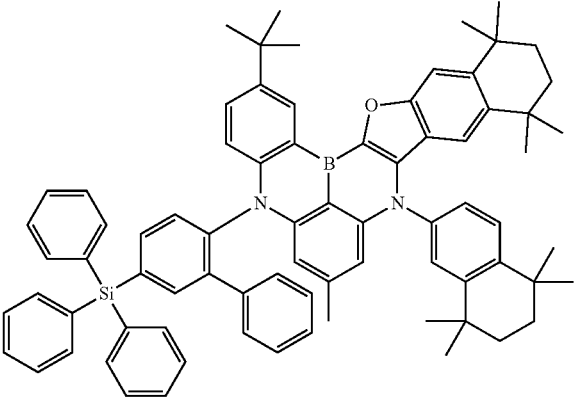
2628
-continued
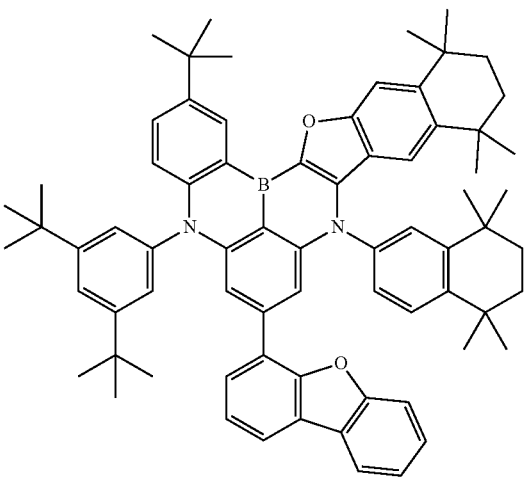
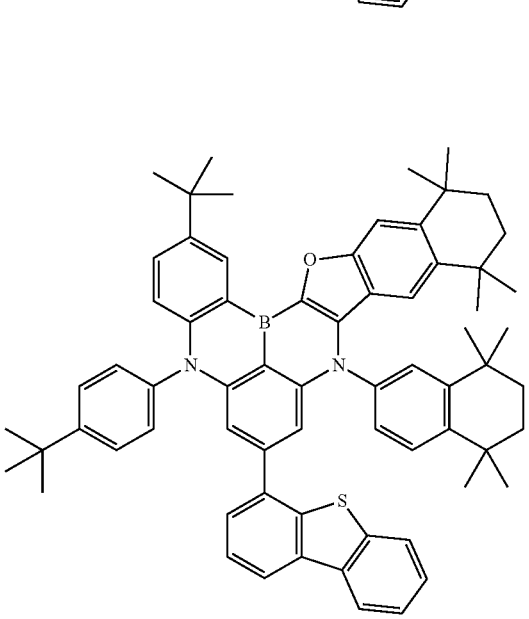
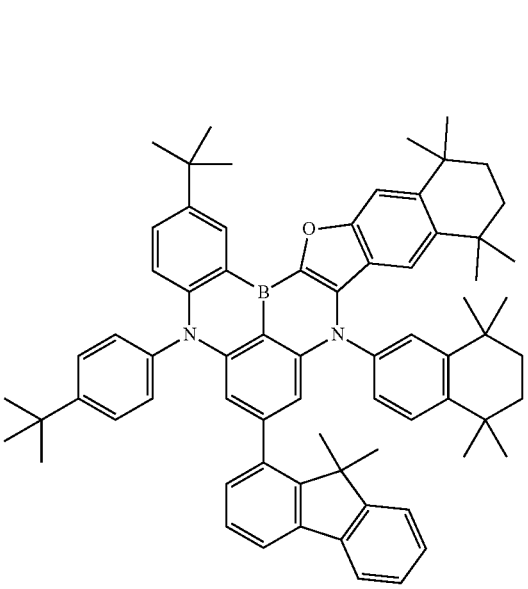

2629
-continued
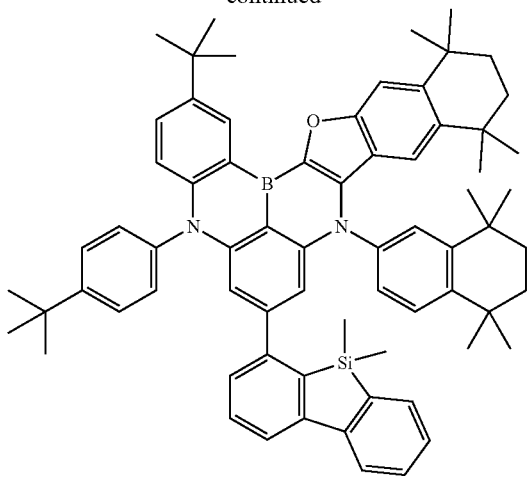
2630
-continued
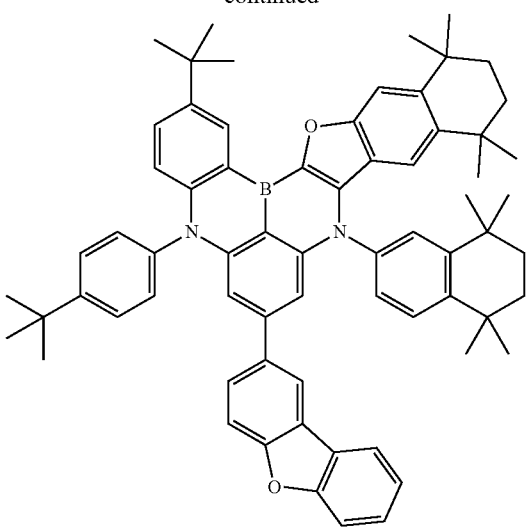
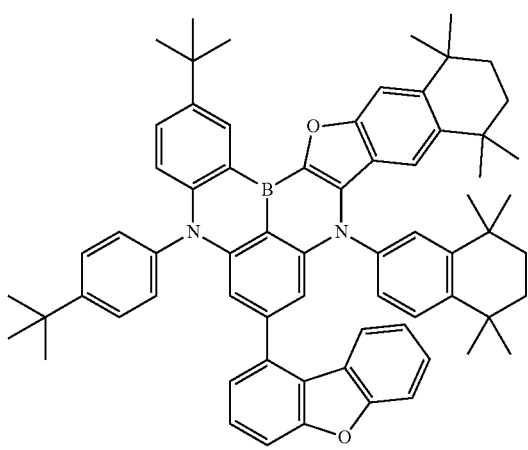
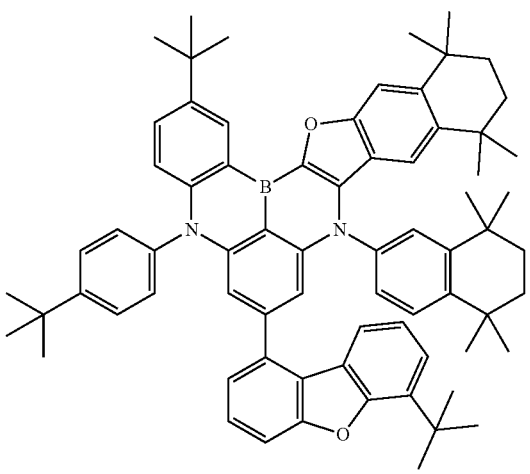
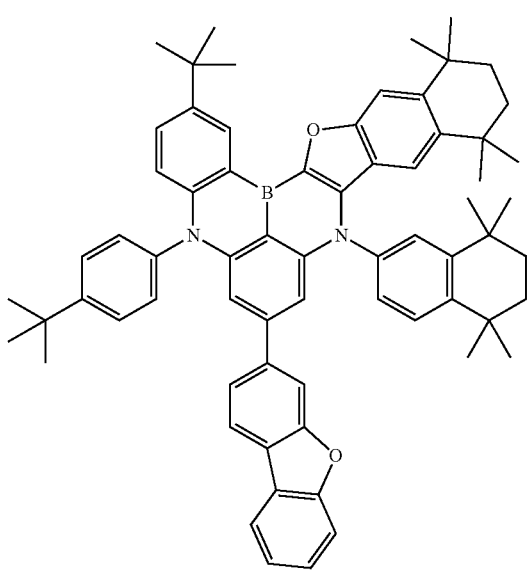
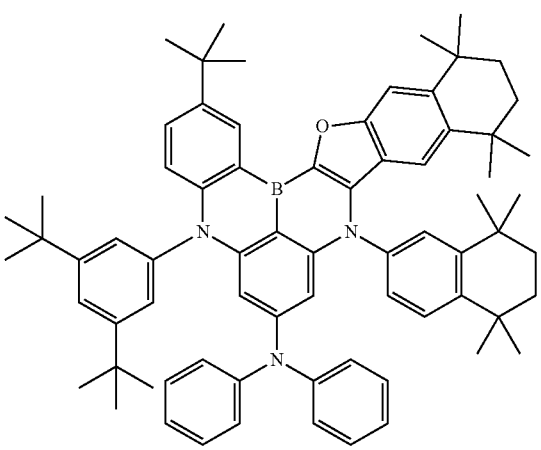

2631
-continued
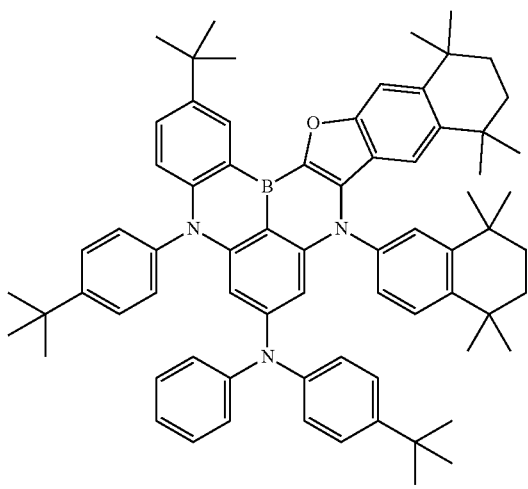
2632
-continued
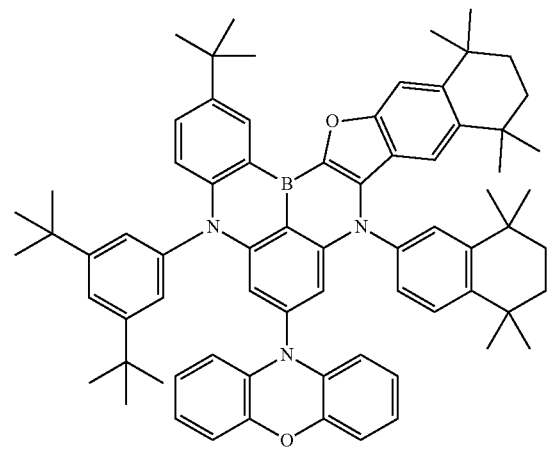
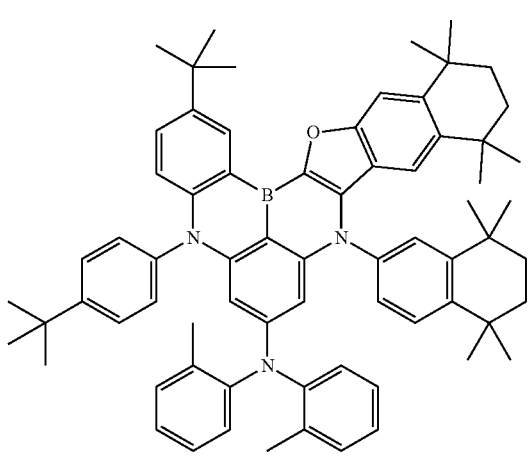
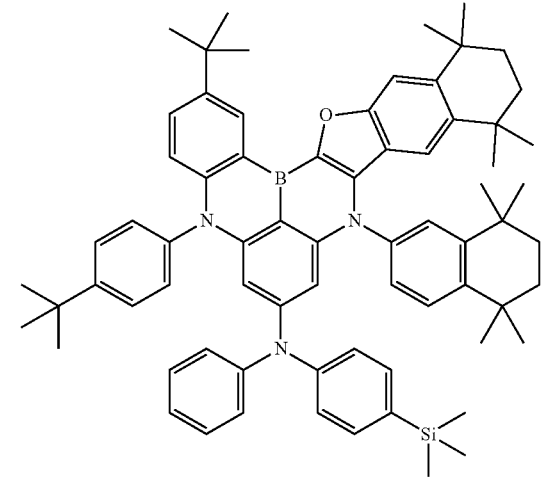
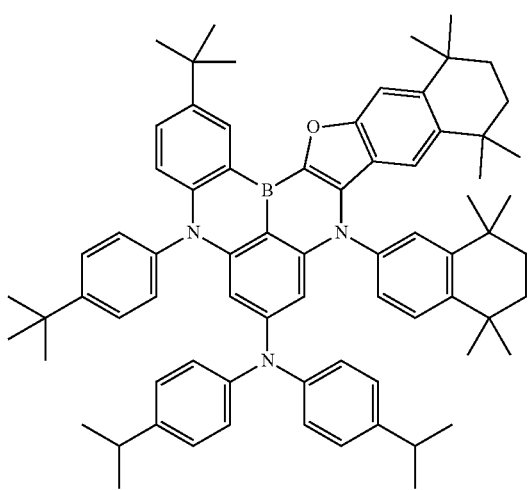
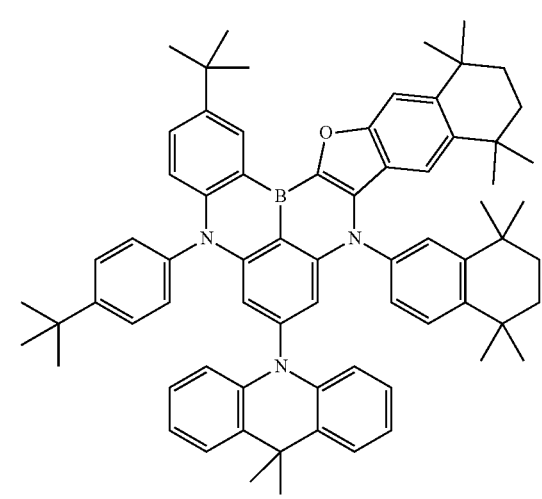

2633
-continued
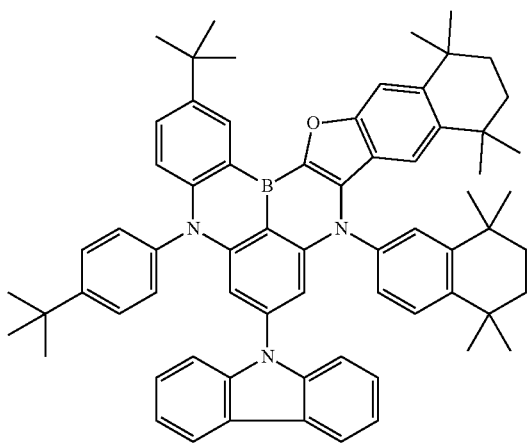
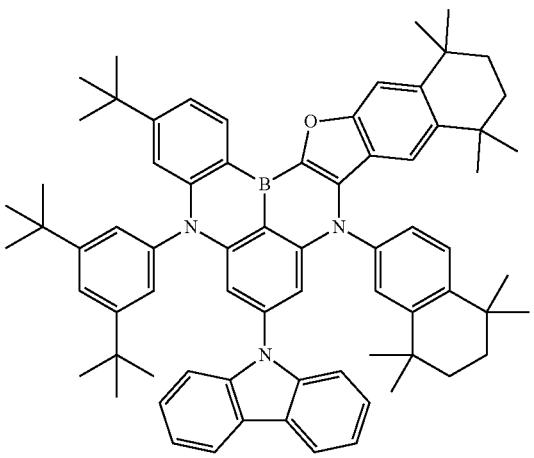
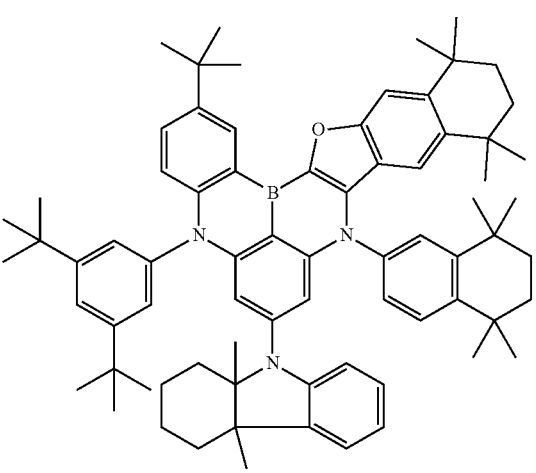
2634
-continued
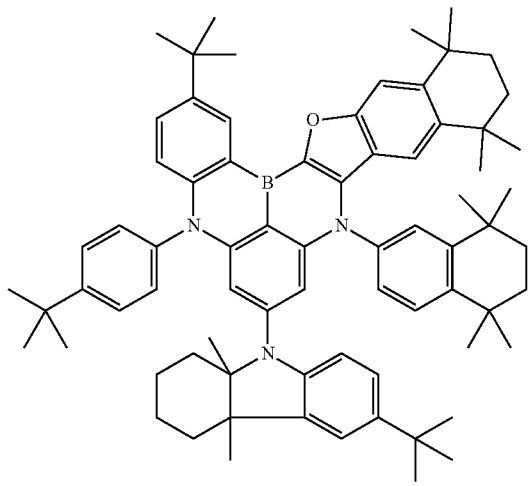
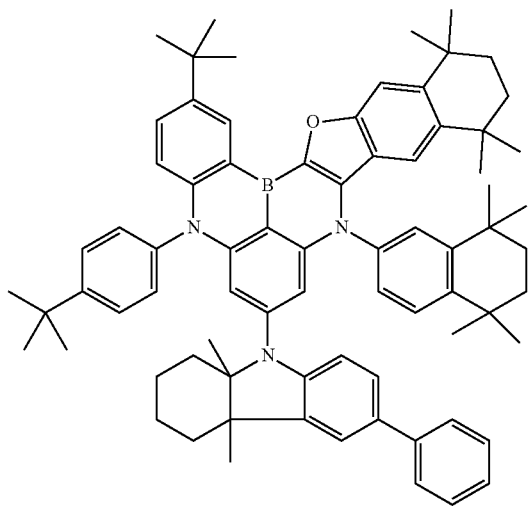
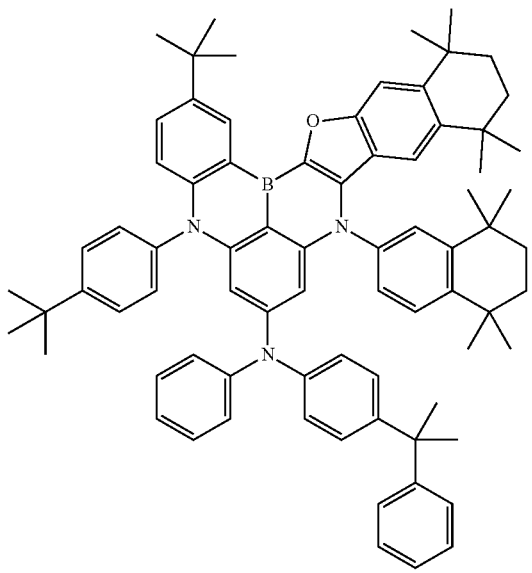

2635
-continued
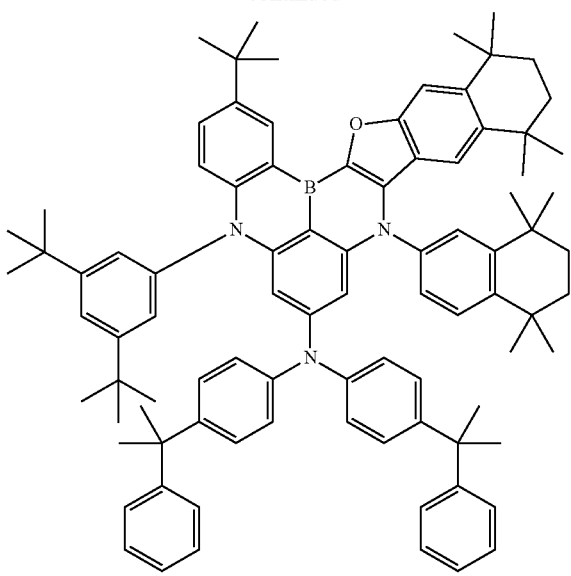
2636
-continued
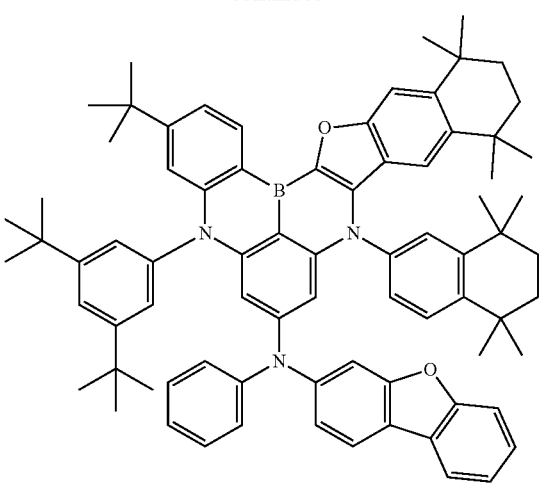
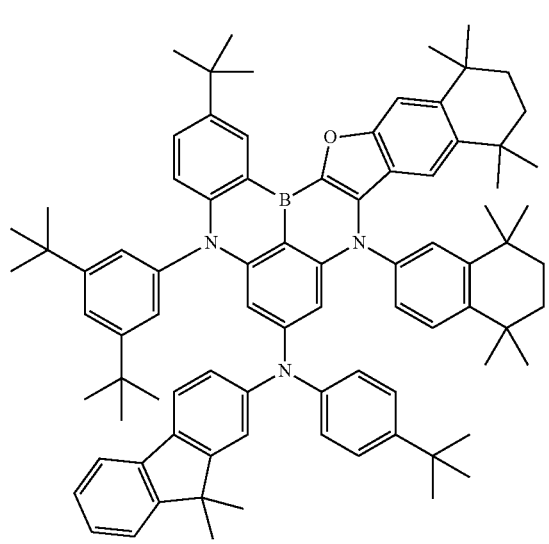
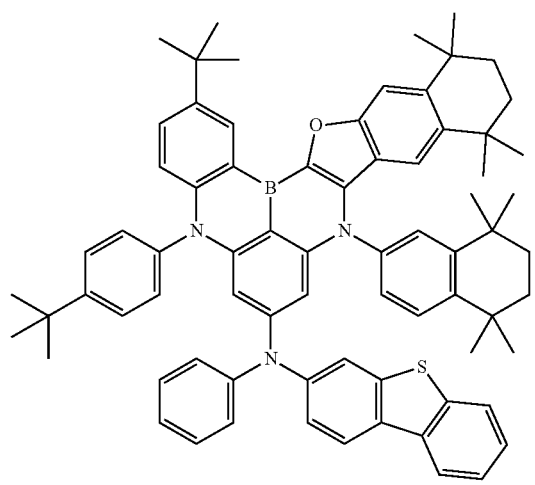
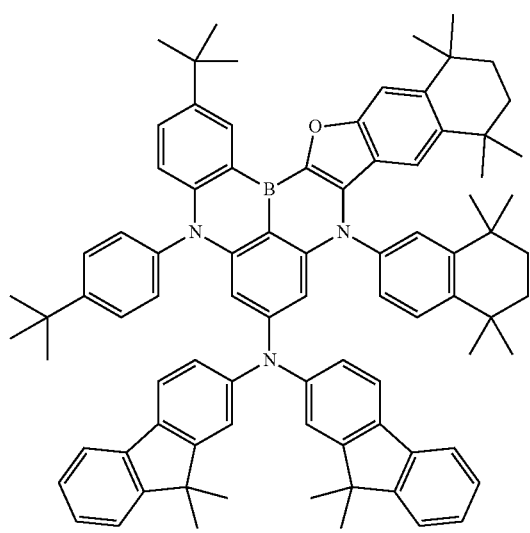
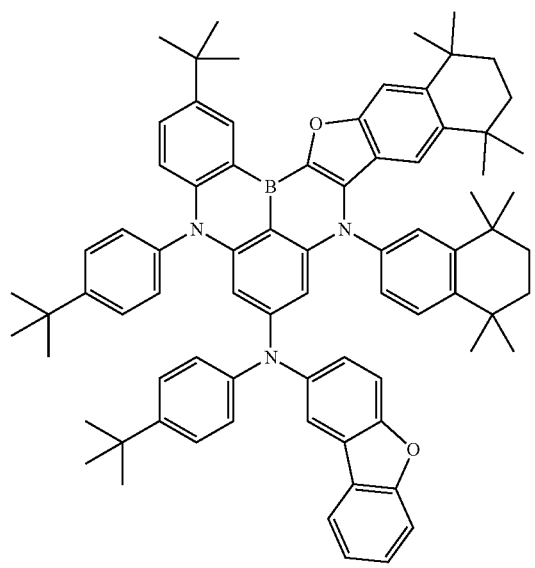

2637
-continued
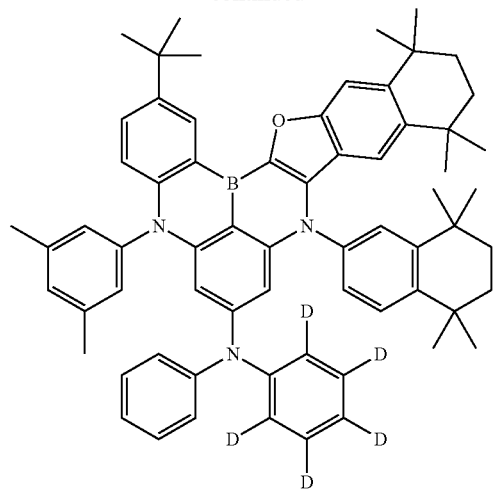
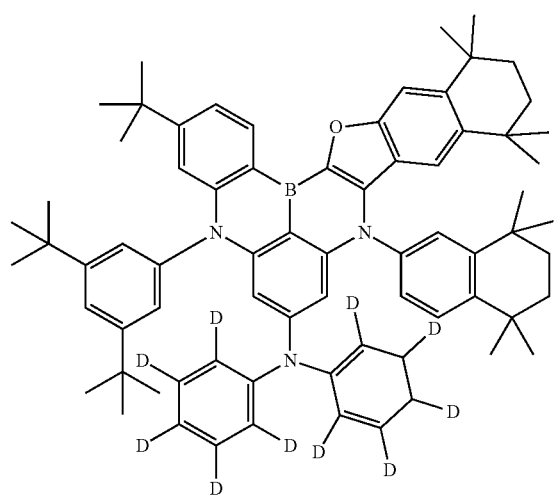
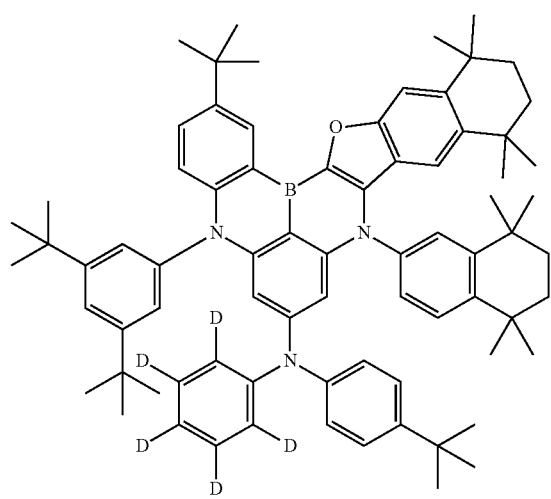
2638
-continued
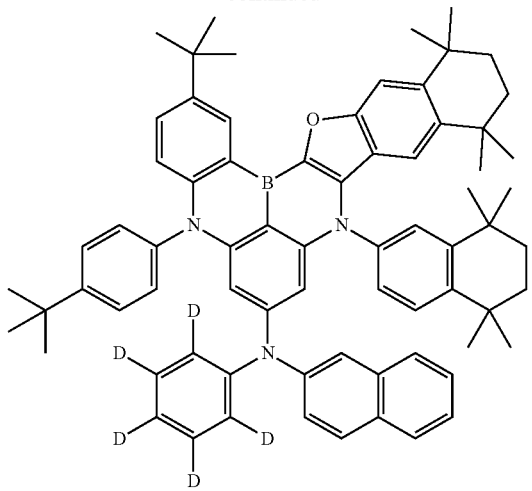
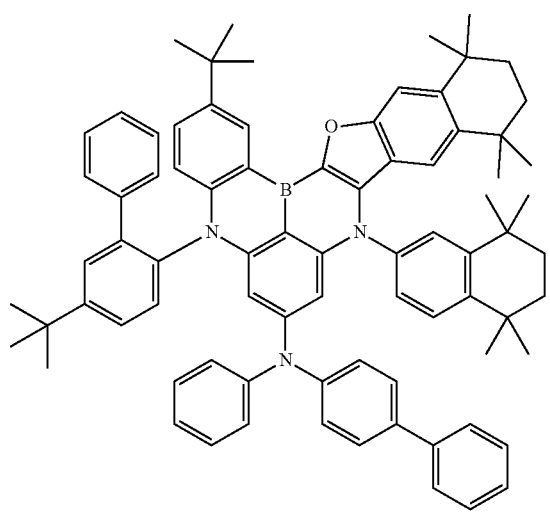
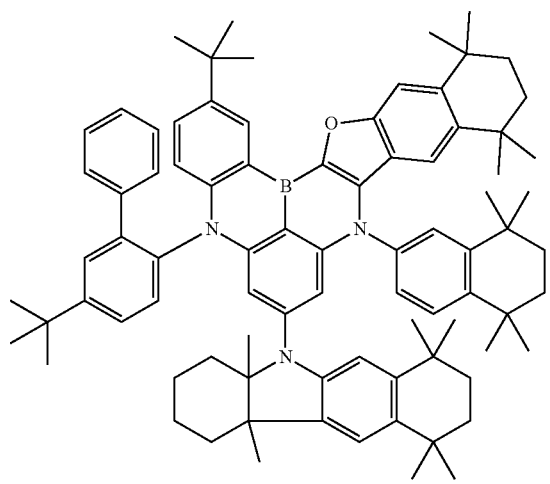

2639
-continued
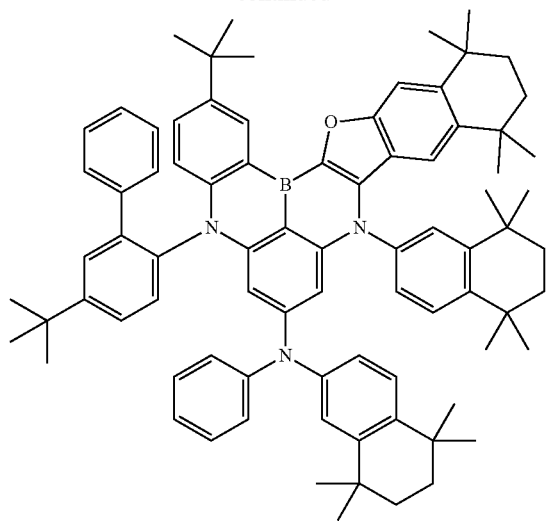
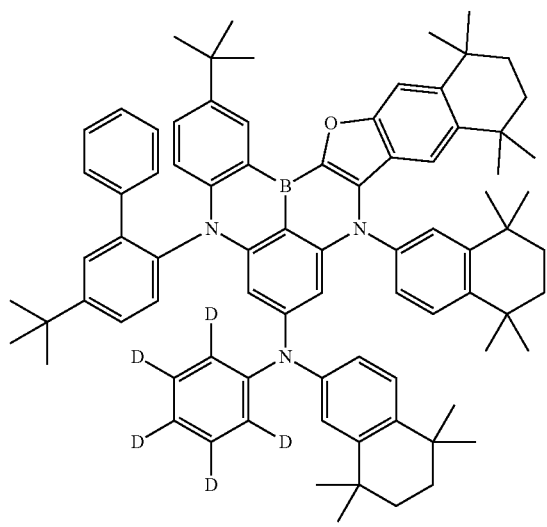
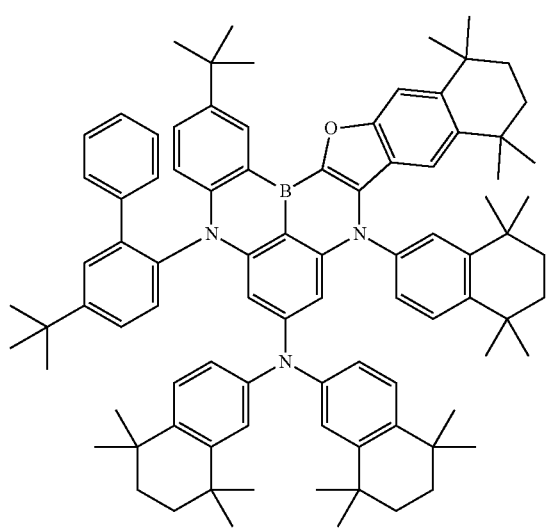
2640
-continued
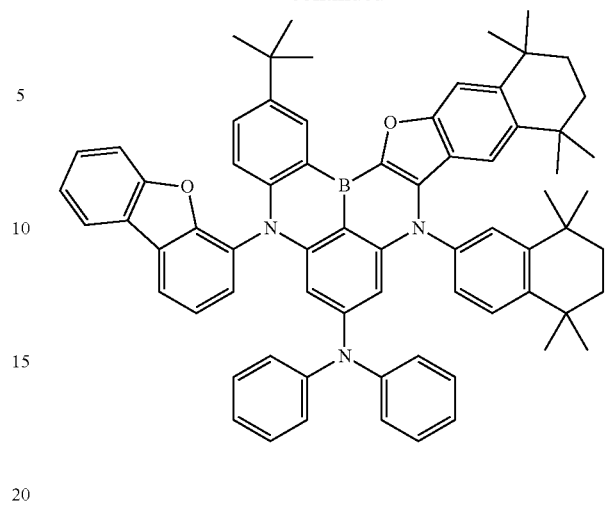
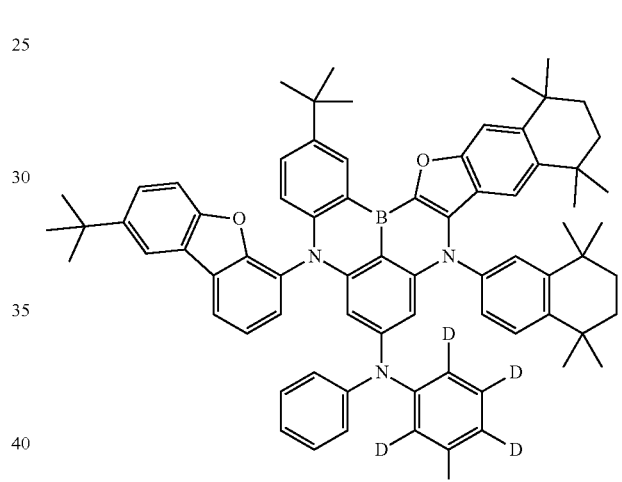
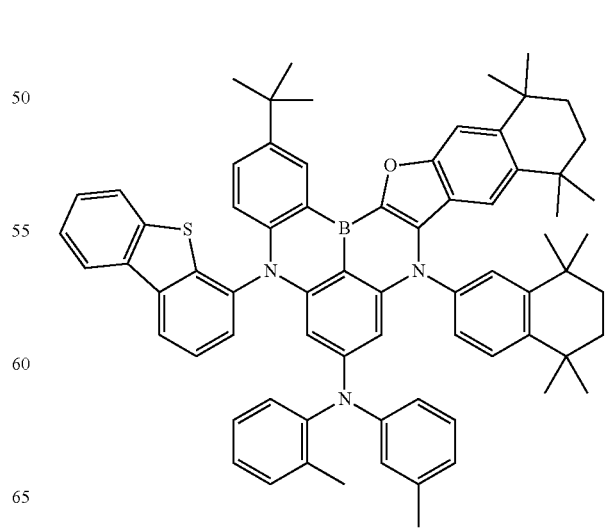

2641
-continued
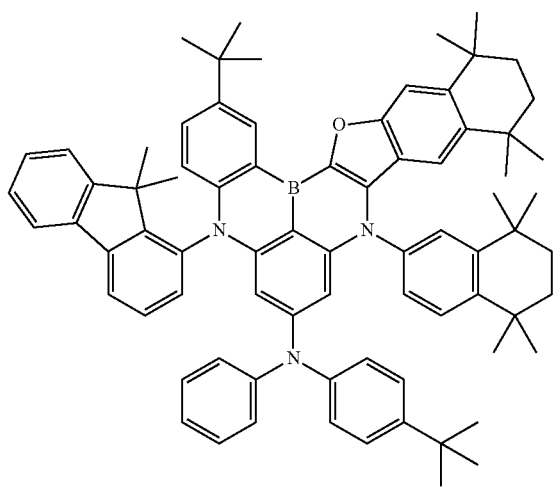
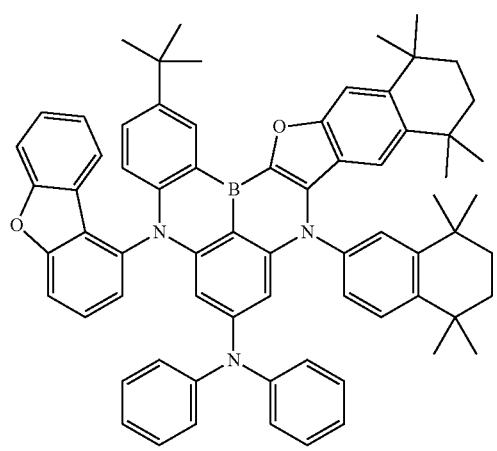
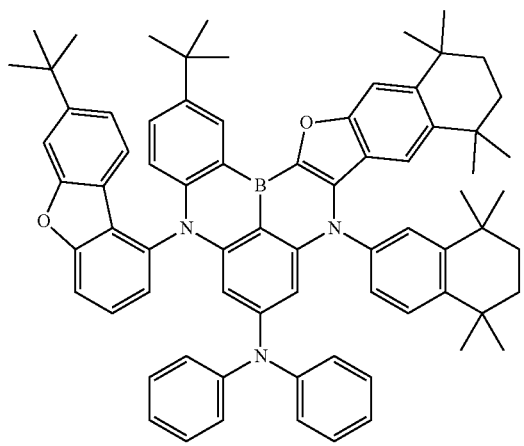
2642
-continued
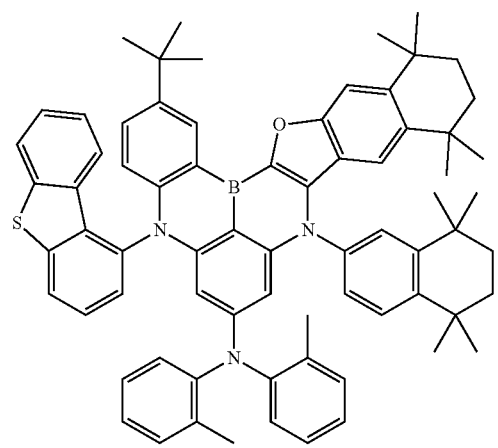
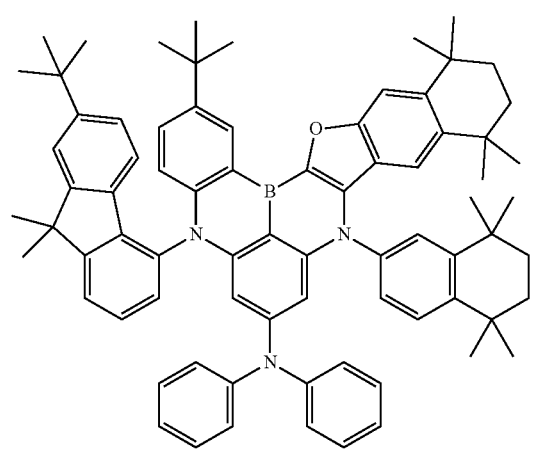
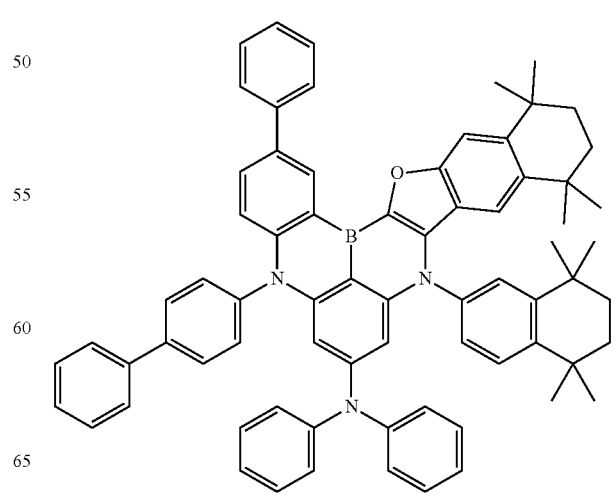

2643
-continued
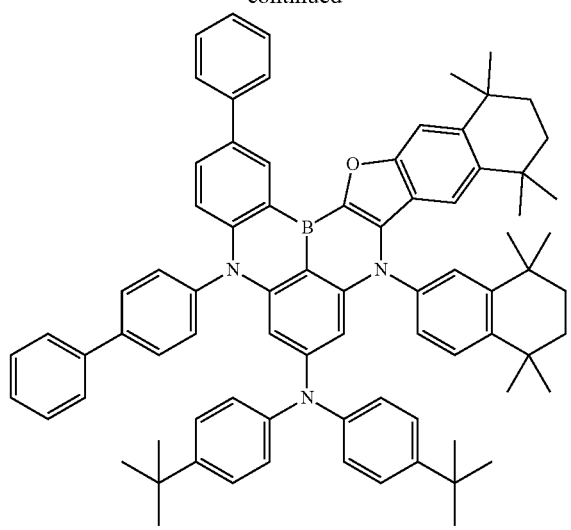
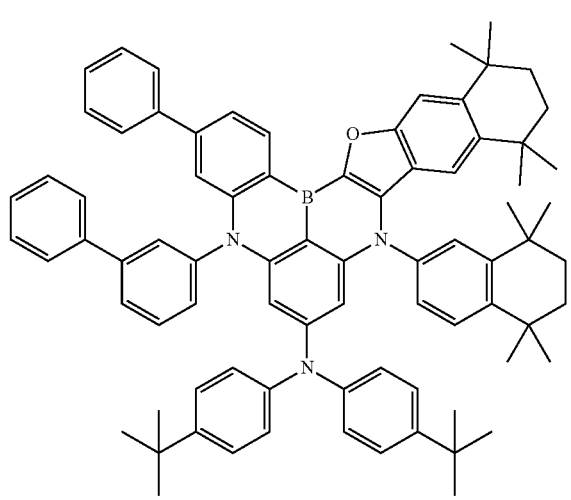
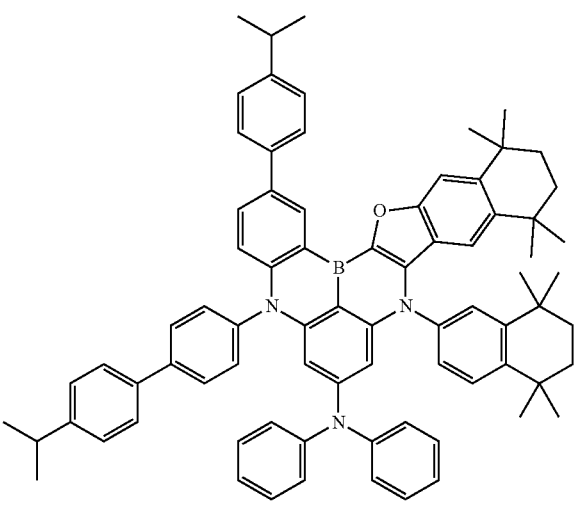
2644
-continued
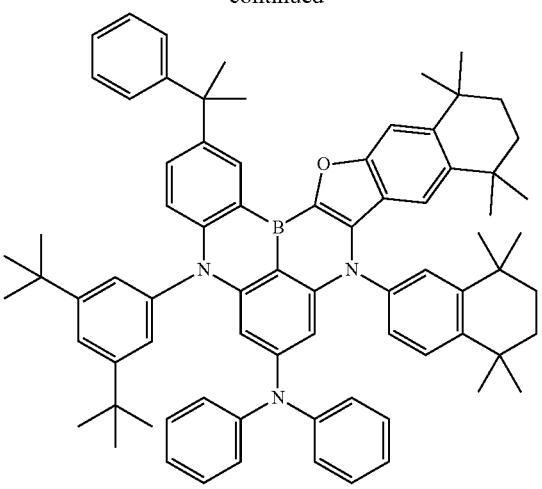
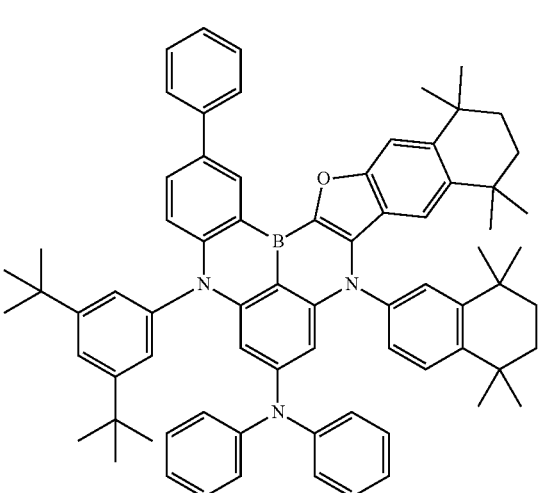
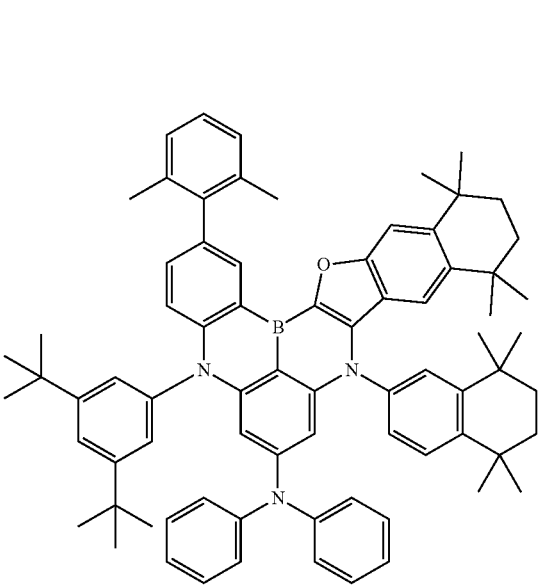

2645
-continued
2646
-continued
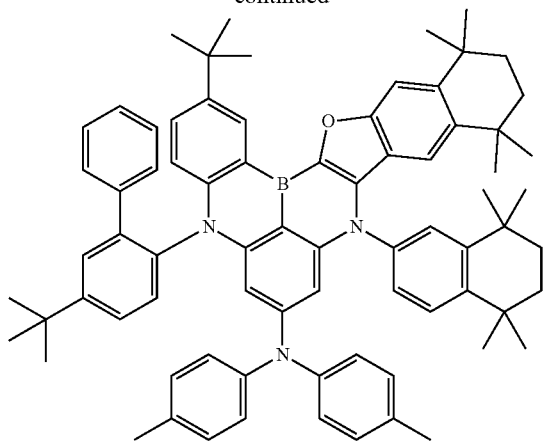
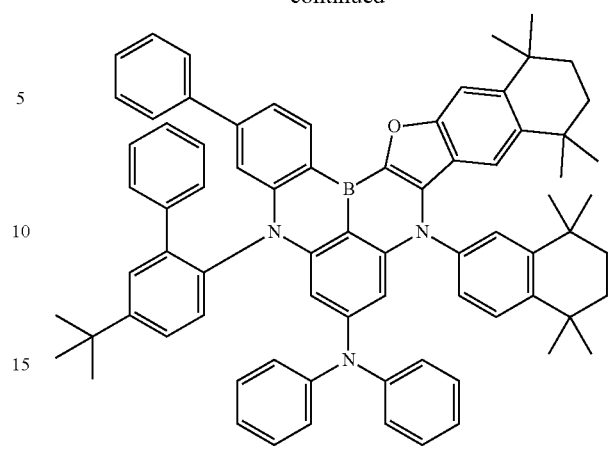
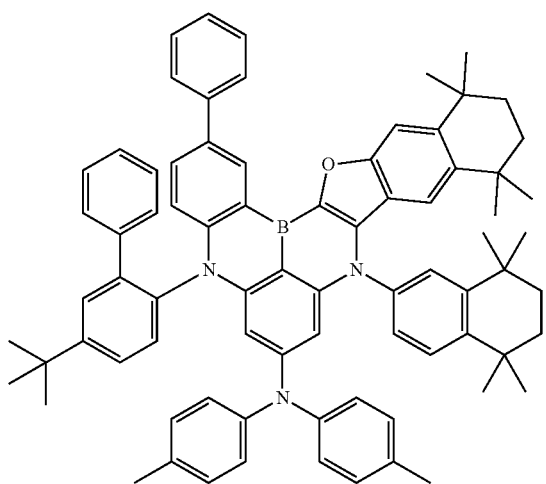
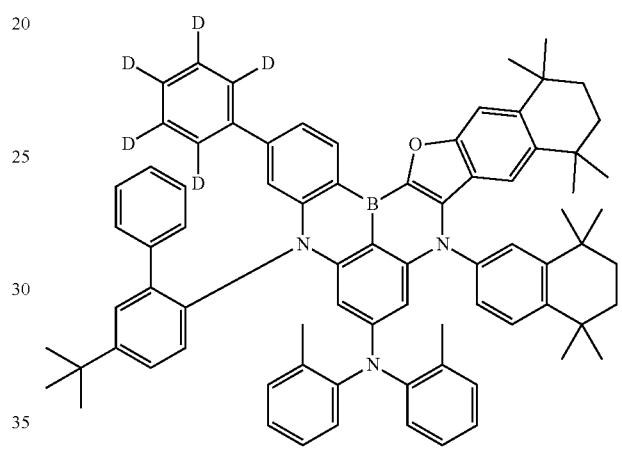
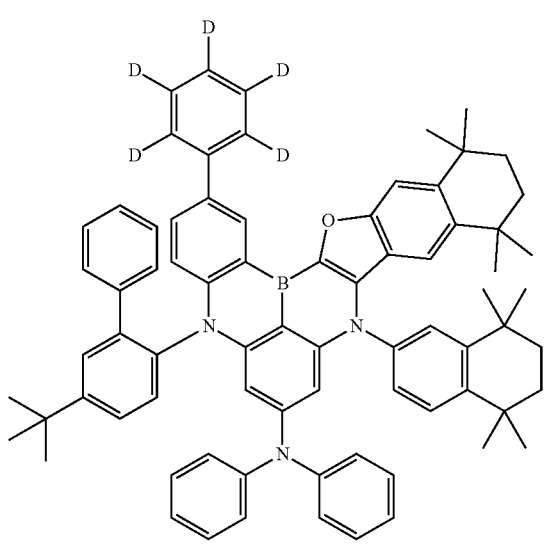
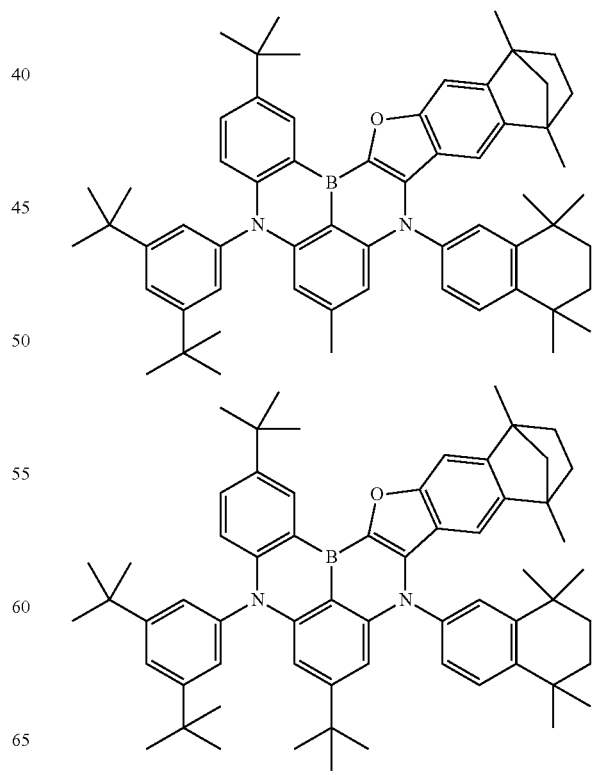

| 2647 | 2648 |
|---|---|
| -continued | -continued |
| 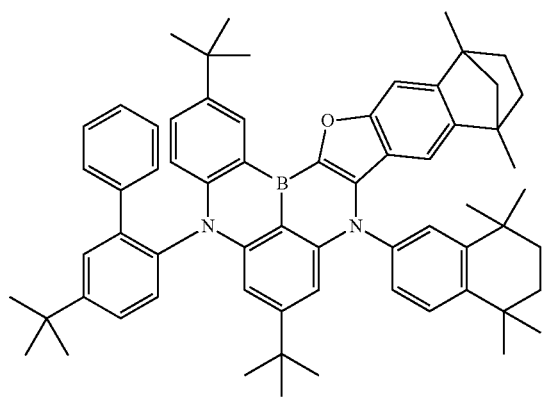 | 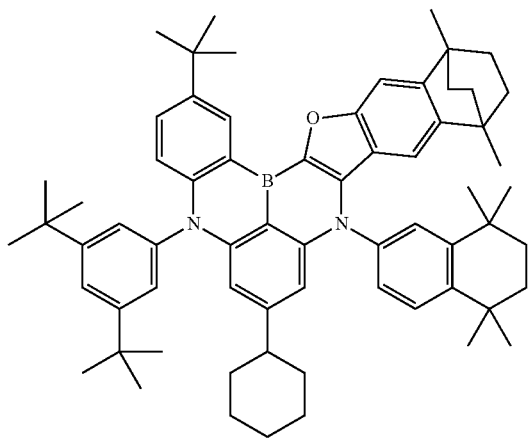 |
| 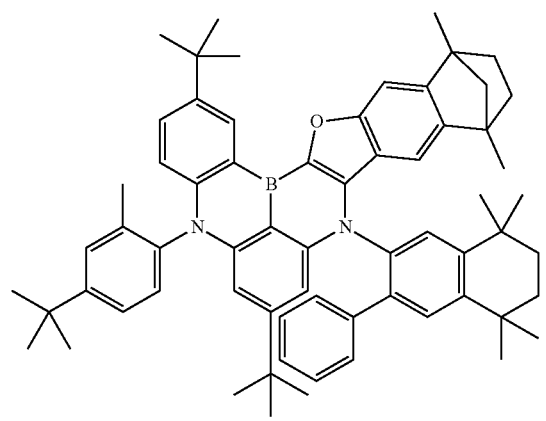 | 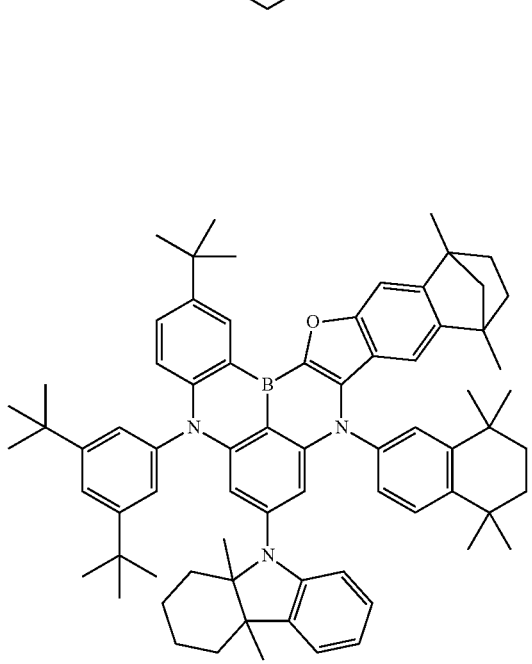 |
| 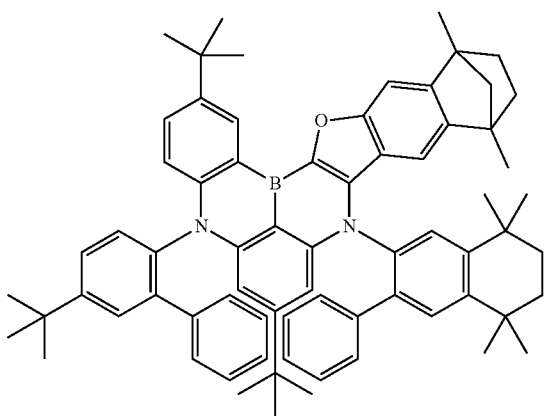 | |
| 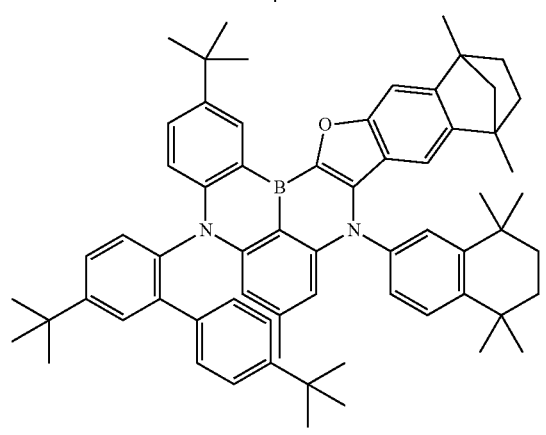 | 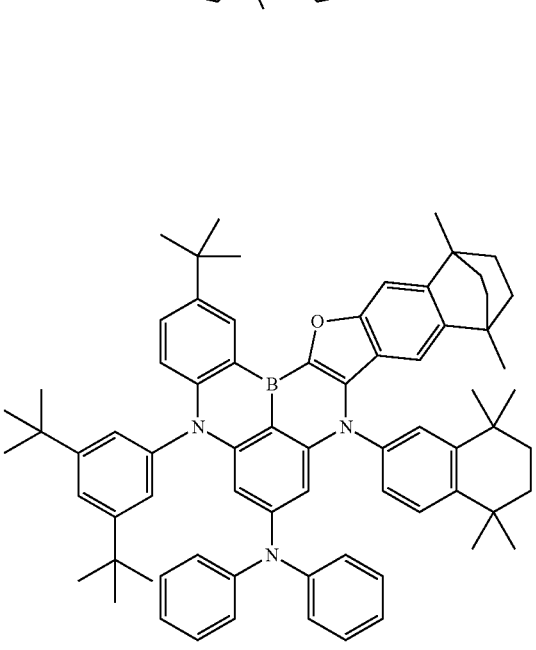 |

| 2649 -continued | 2650 -continued |
|---|---|
| 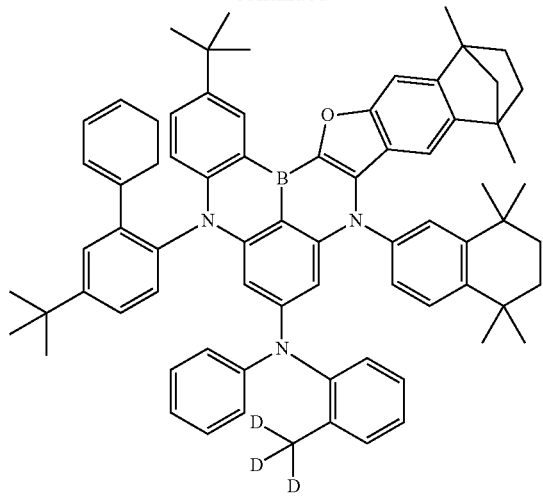 | 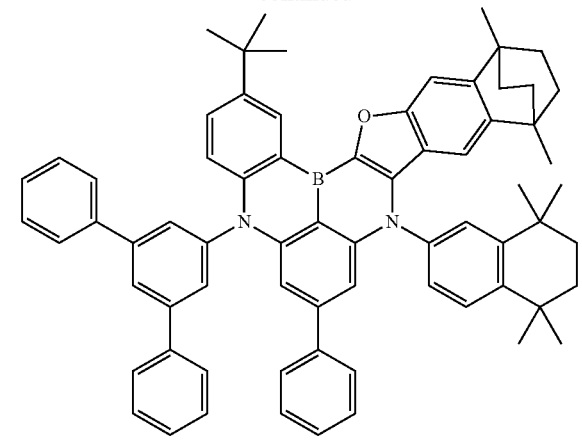 |
| 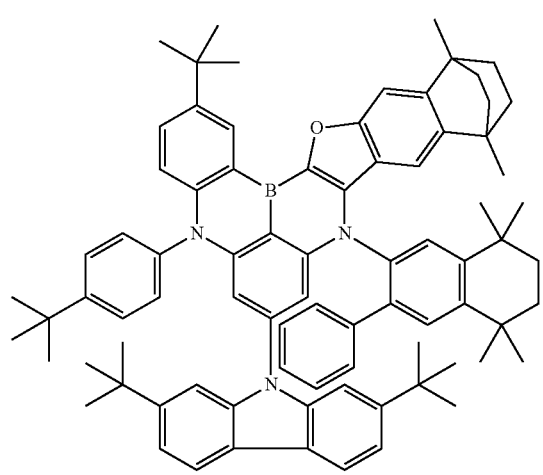 | 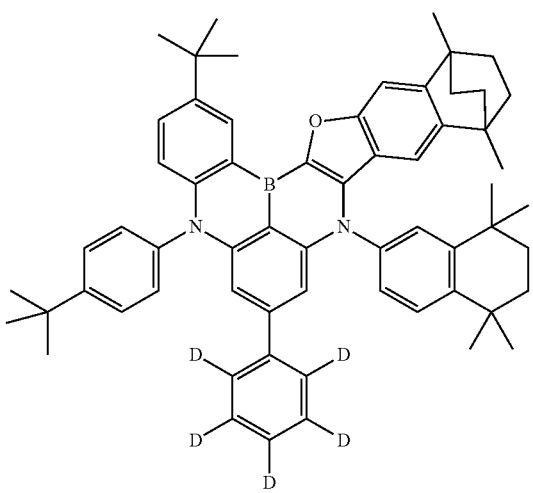 |
| 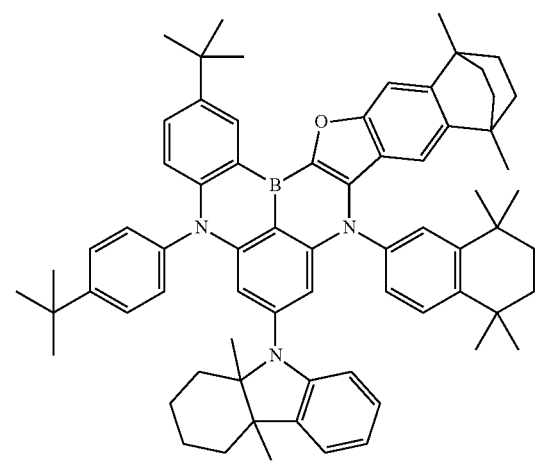 | 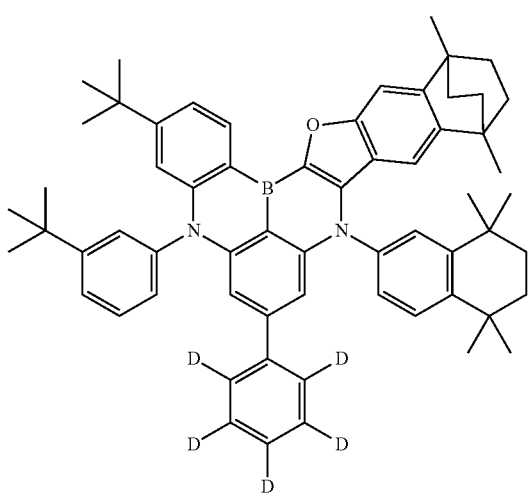 |

2651
-continued
2652
-continued
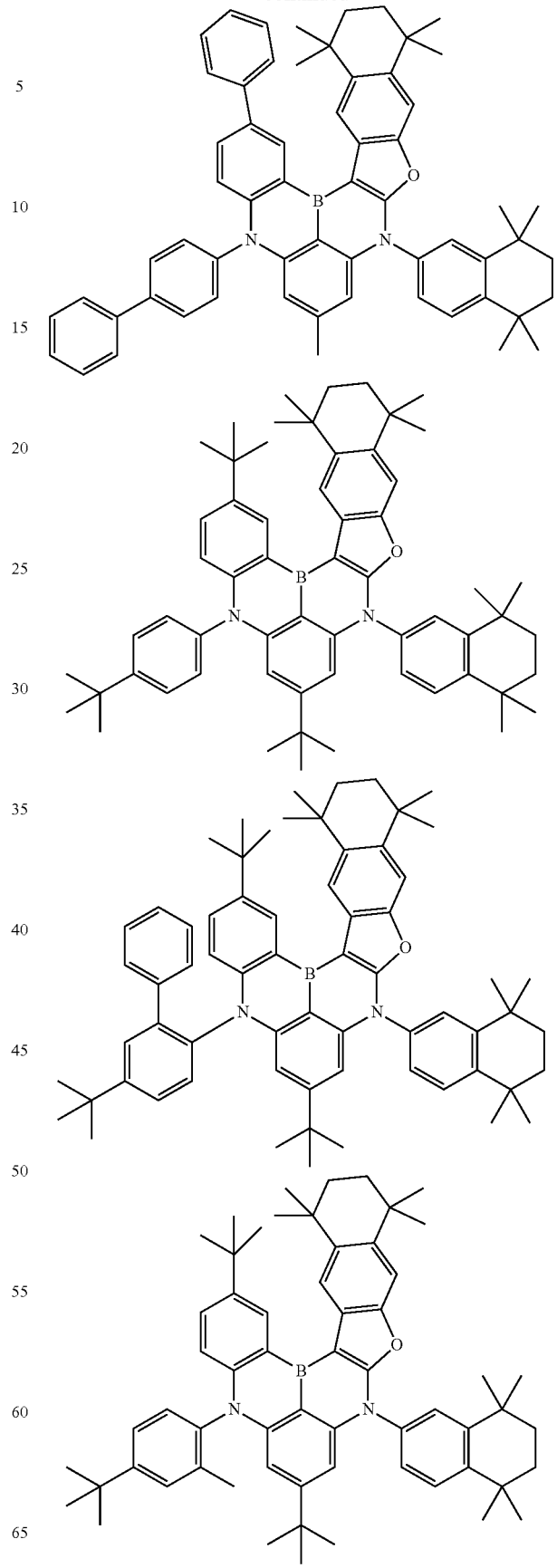
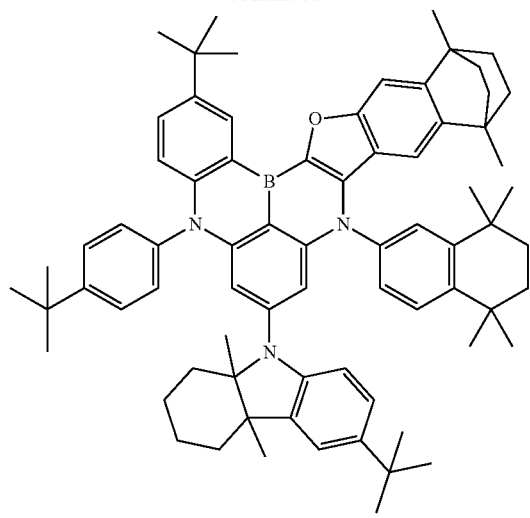

2653
-continued
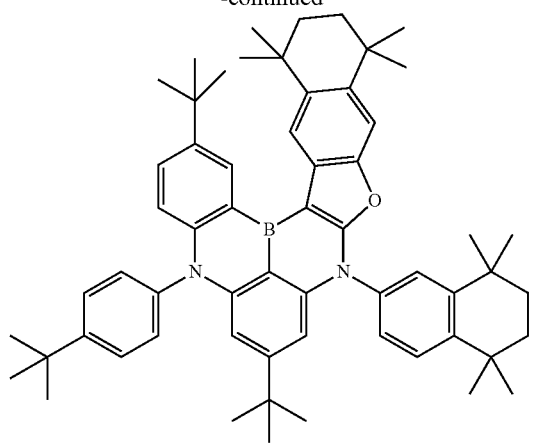
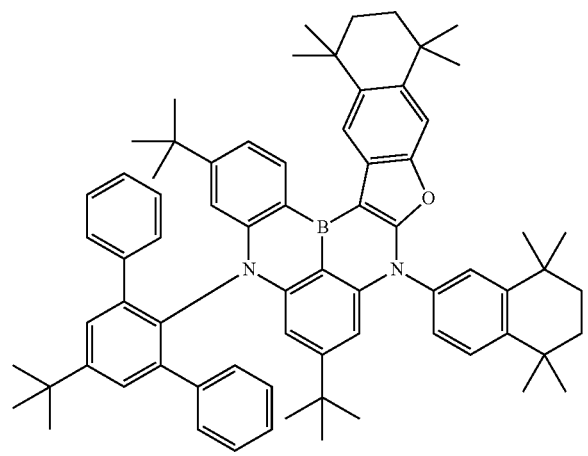
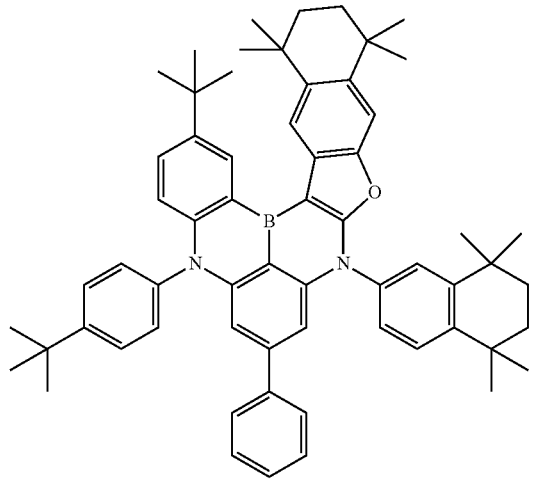
2654
-continued
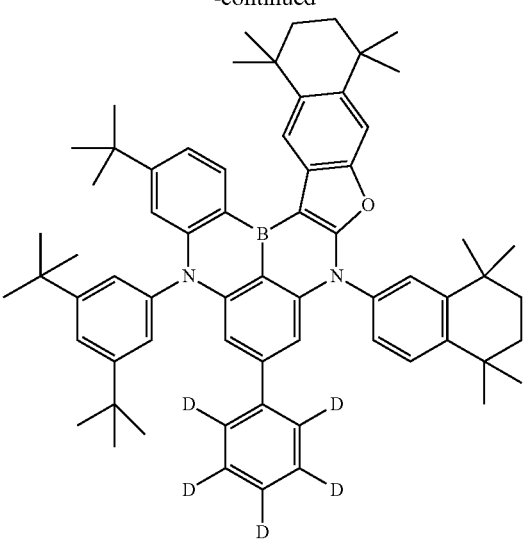
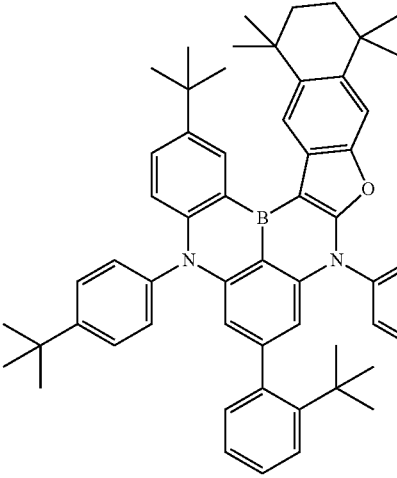
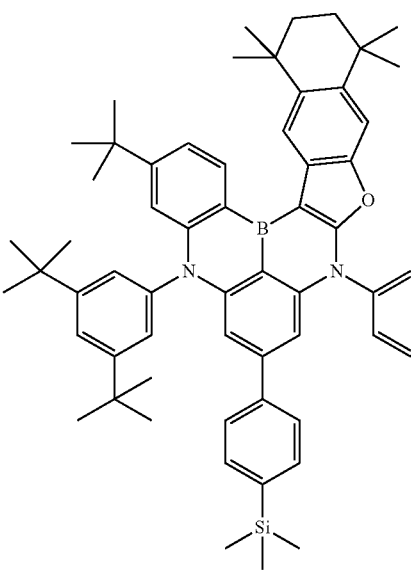

2655
-continued
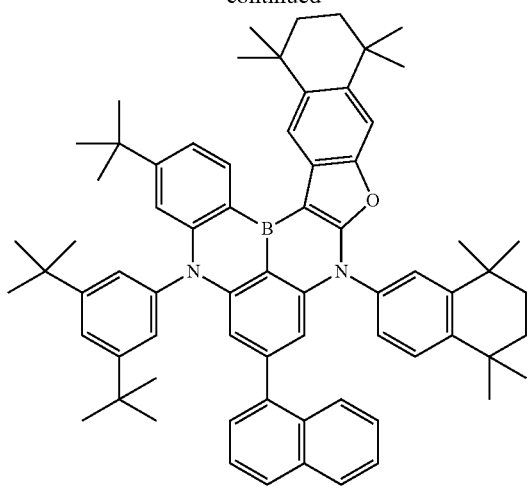
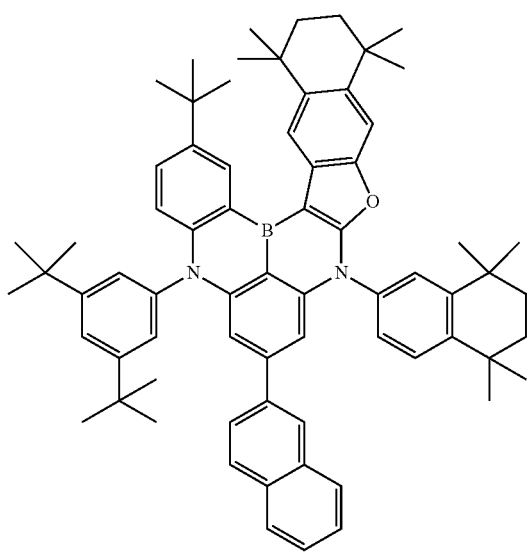
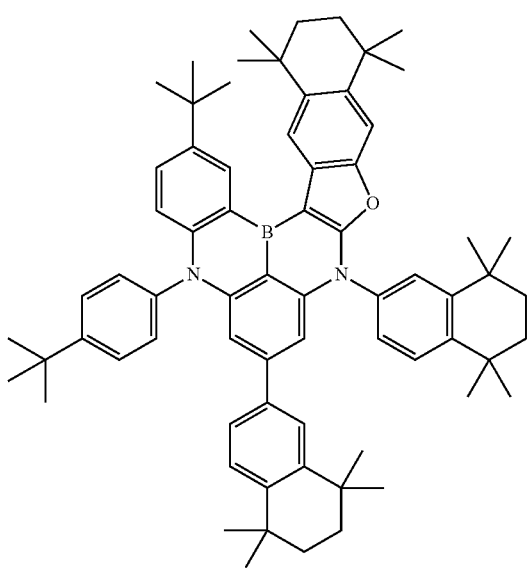
2656
-continued
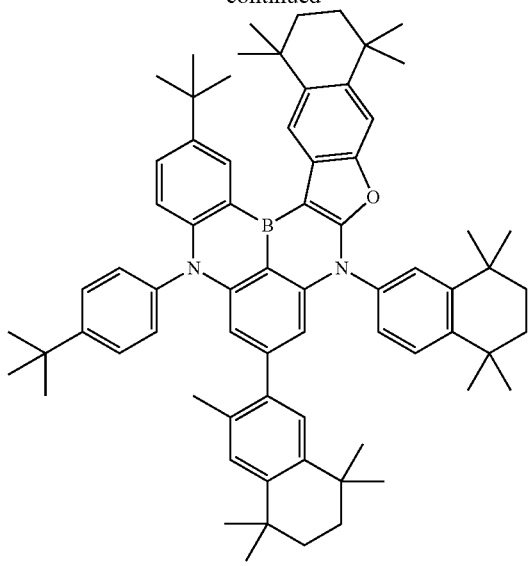
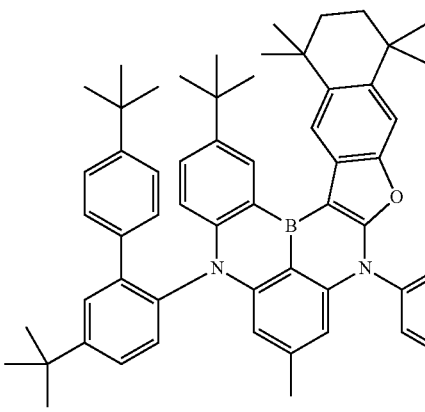
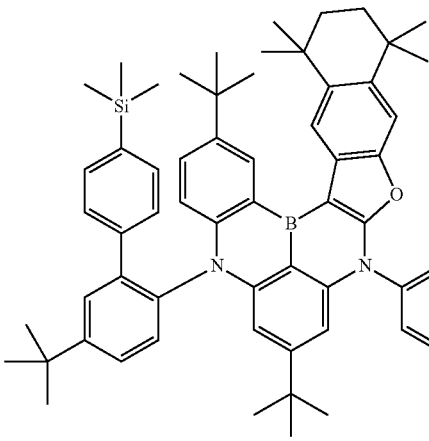

2657
-continued
2658
-continued
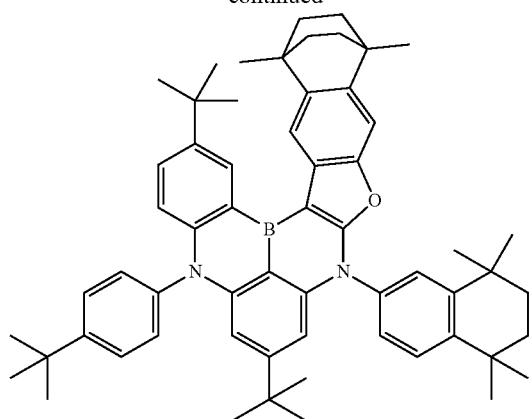
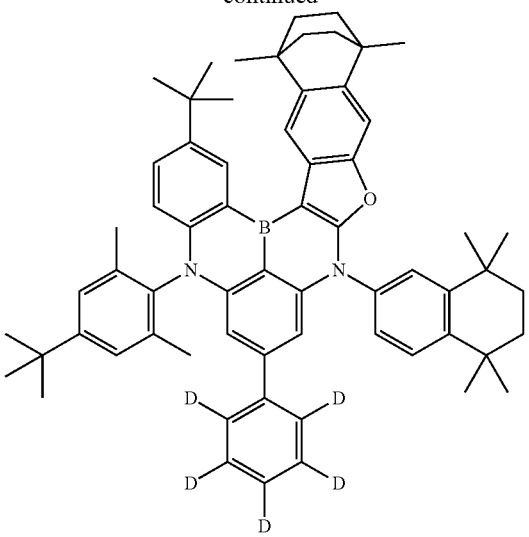
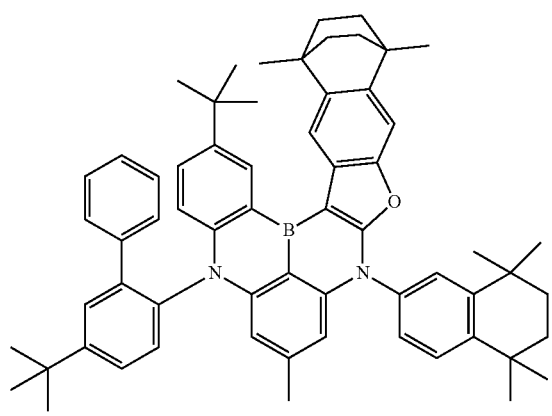
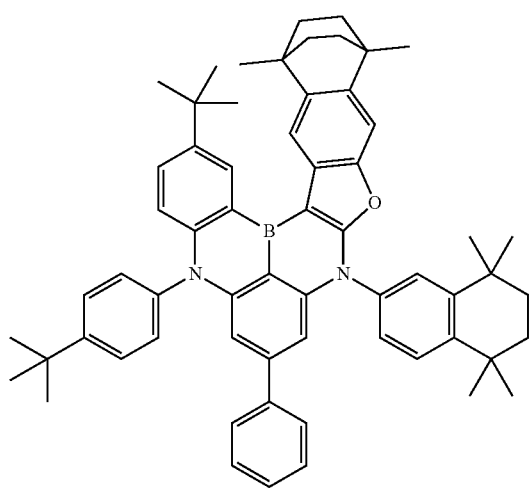
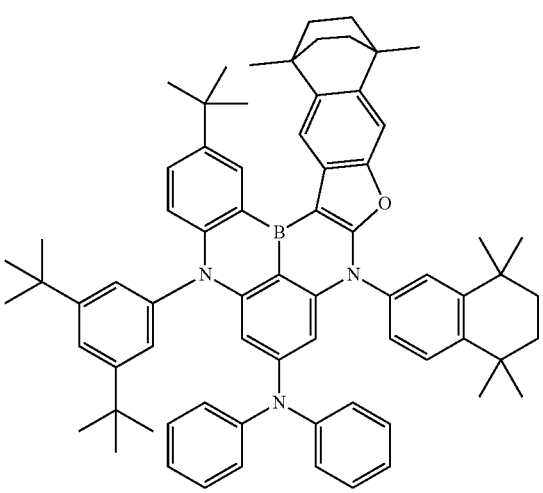

2659
-continued
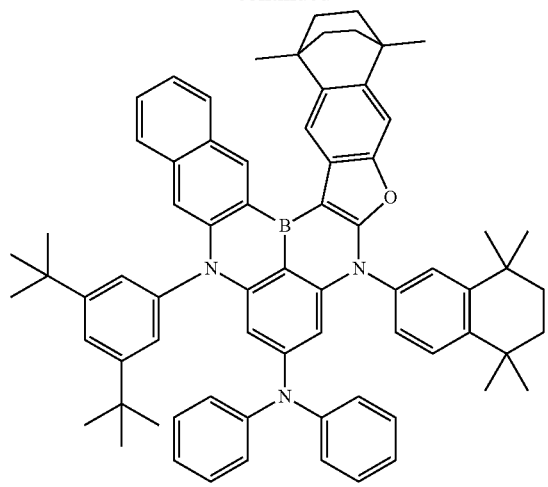
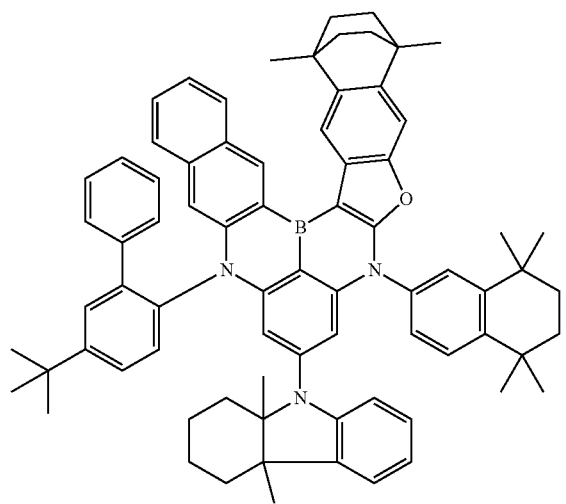
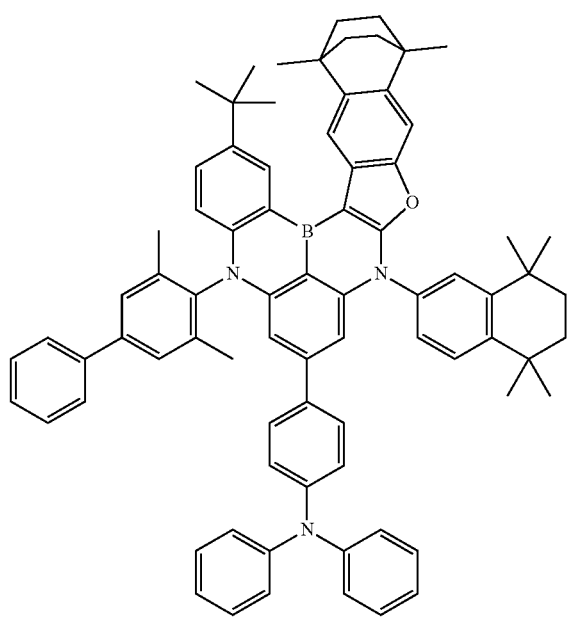
2660
-continued
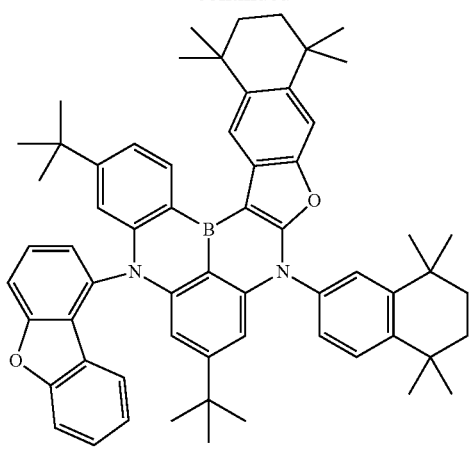
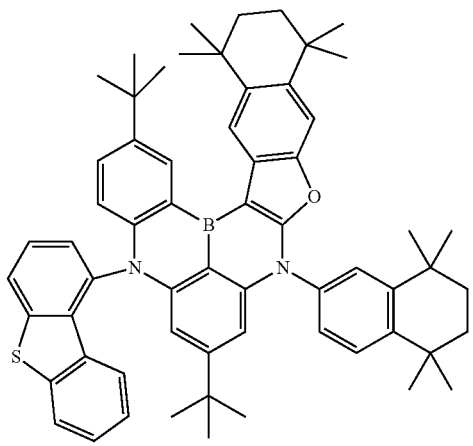
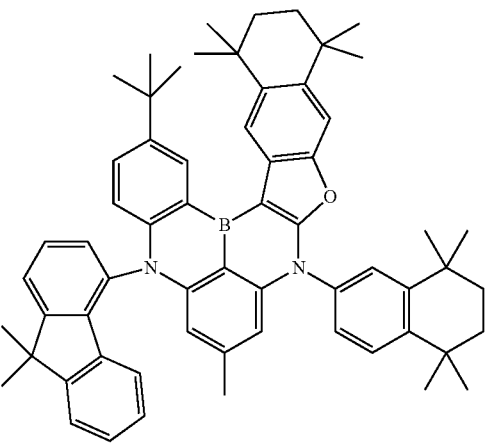

2661
-continued
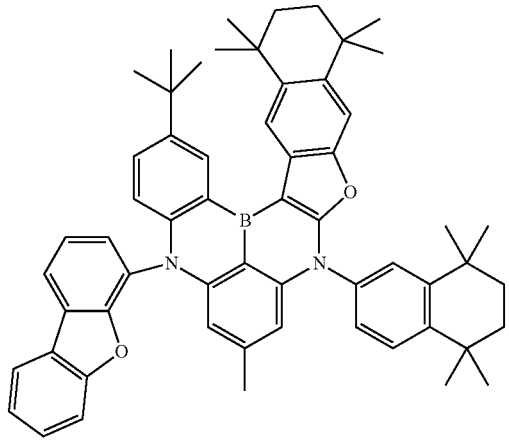
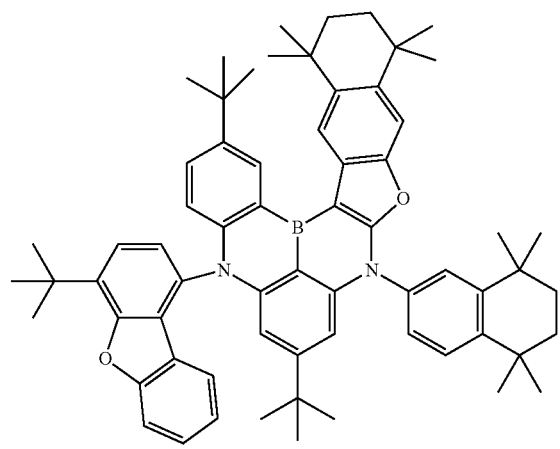
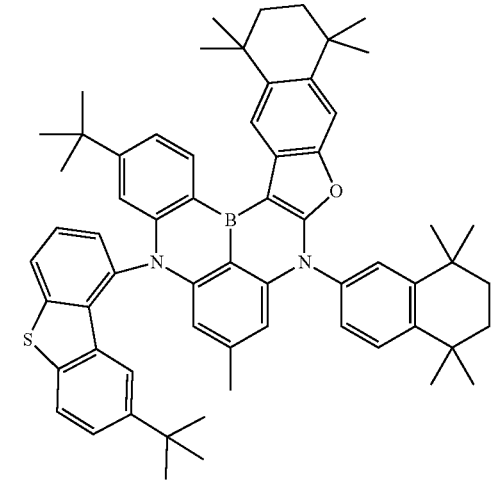
2662
-continued
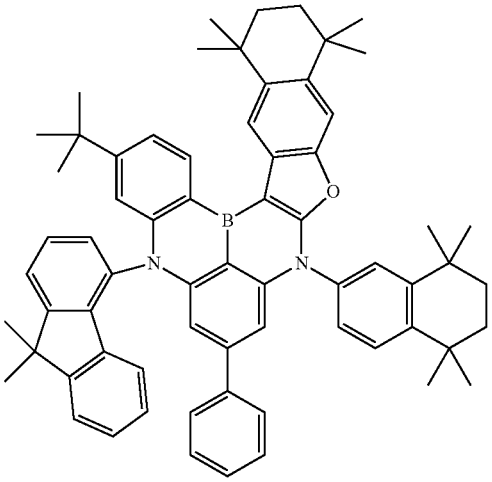
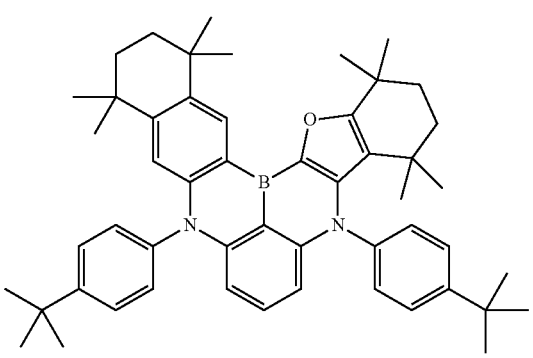
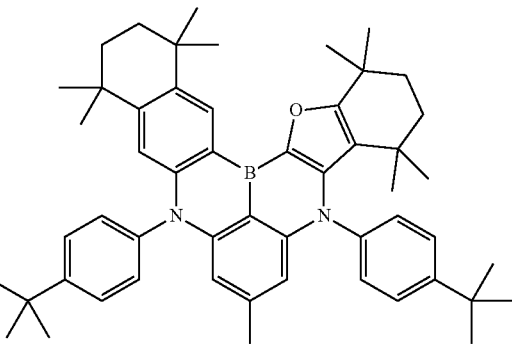

2663
-continued
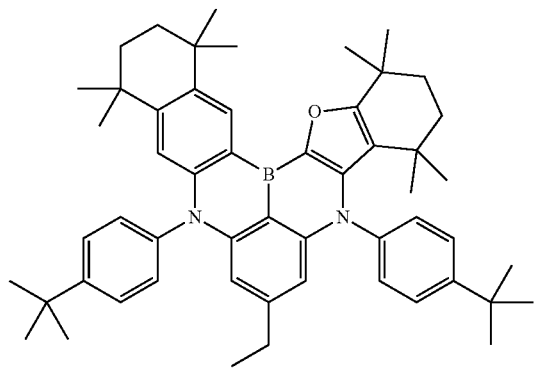
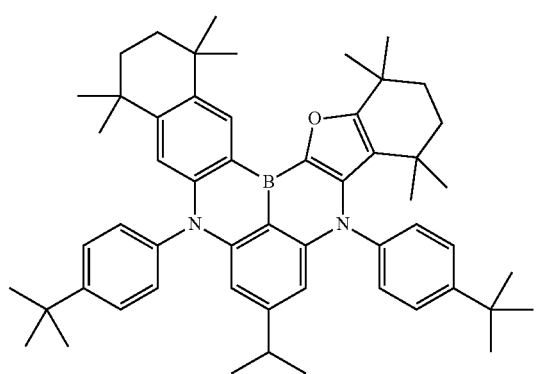
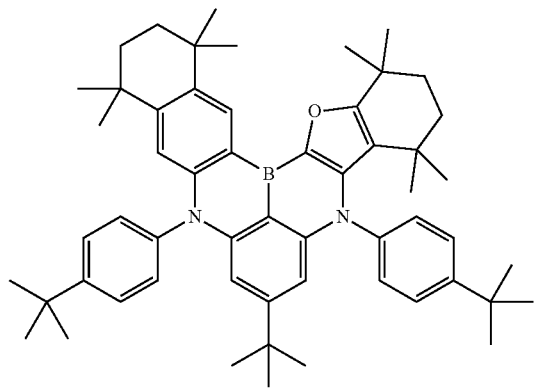
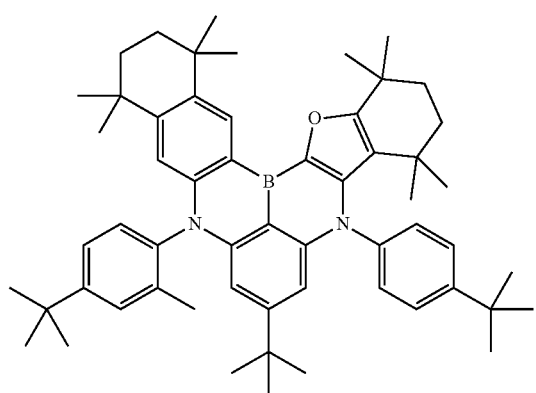
2664
-continued
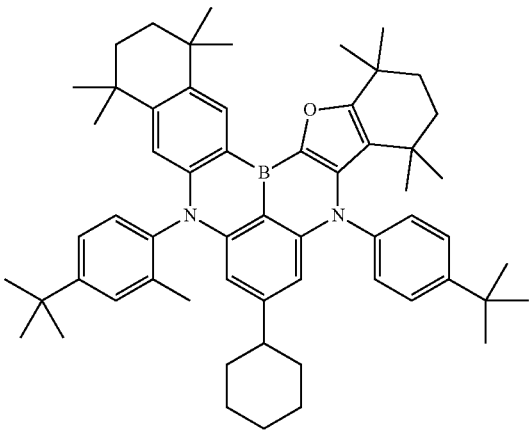
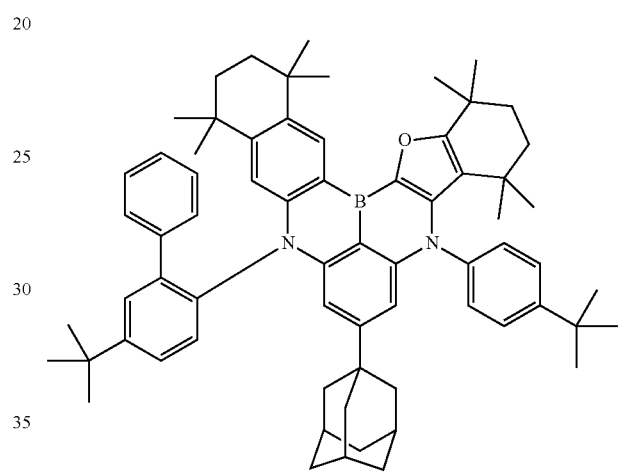
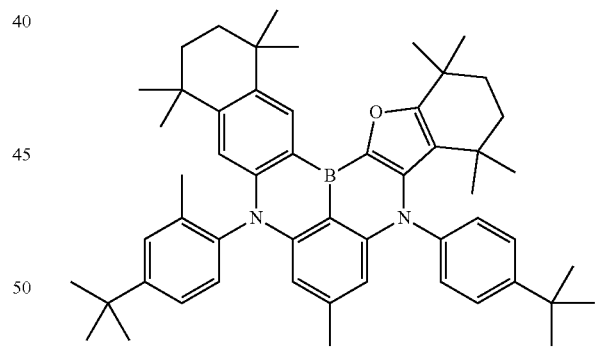
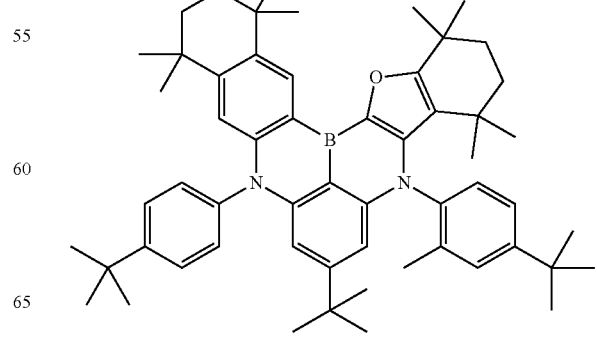

2665
-continued
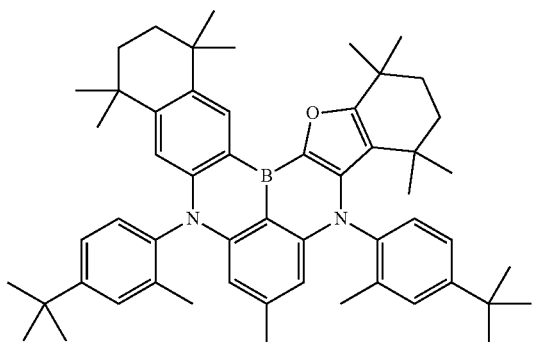
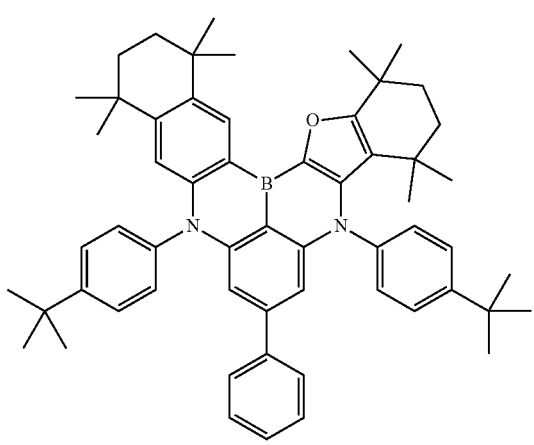
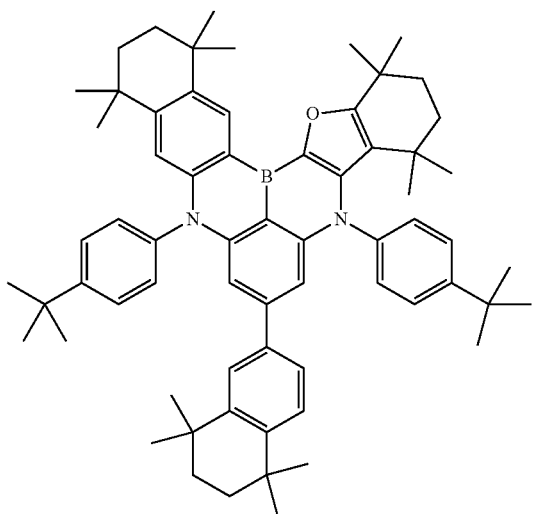
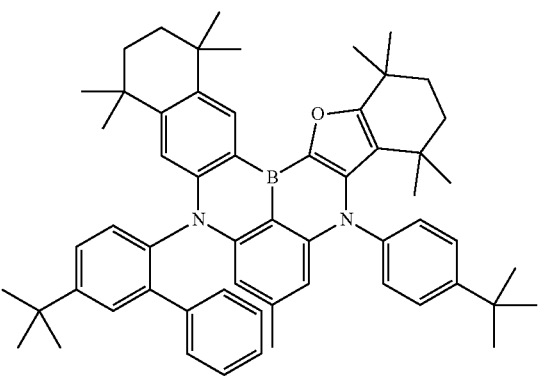
2666
-continued
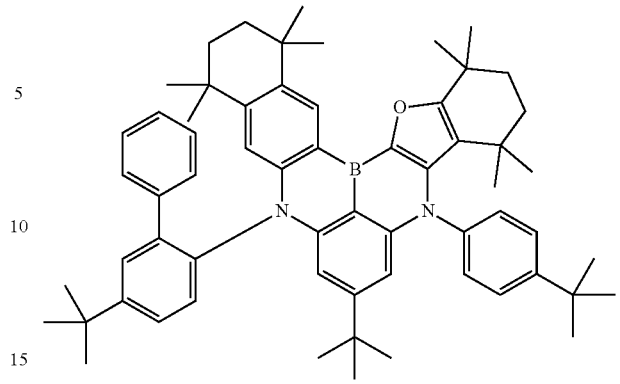
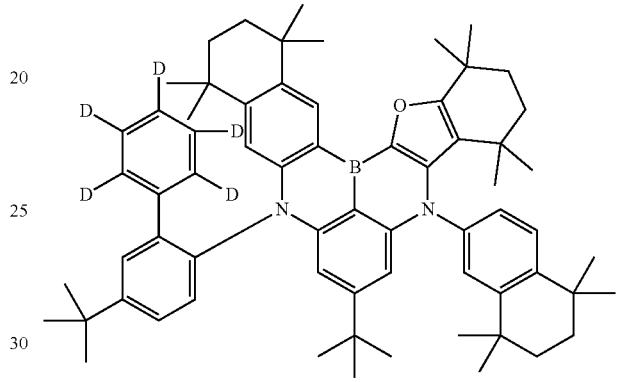
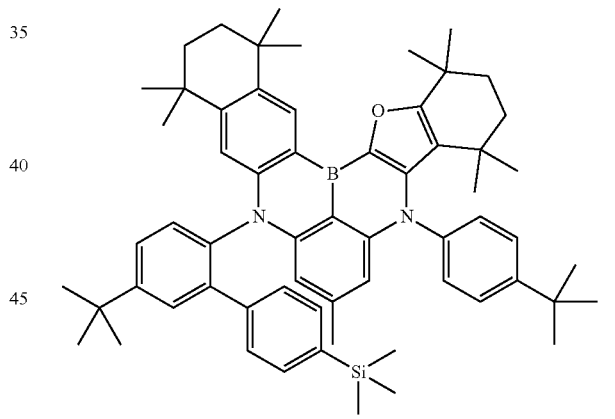
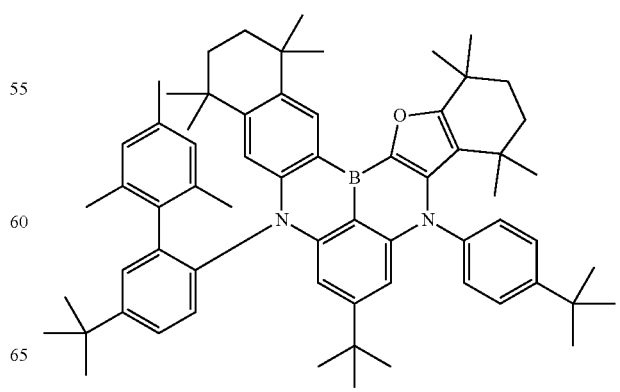

| 2667 -continued | 2668 -continued |
|---|---|
| 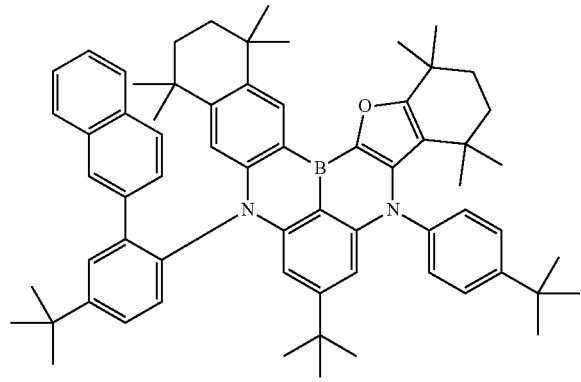 | 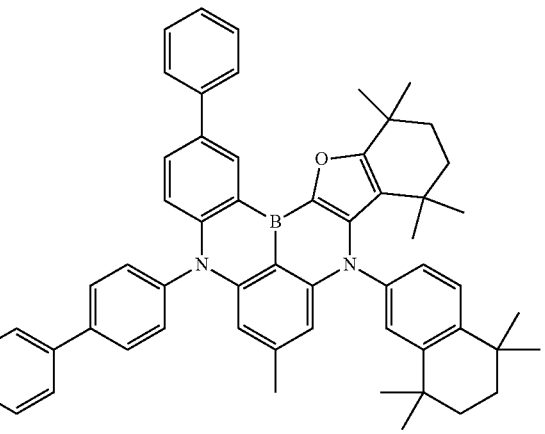 |
| 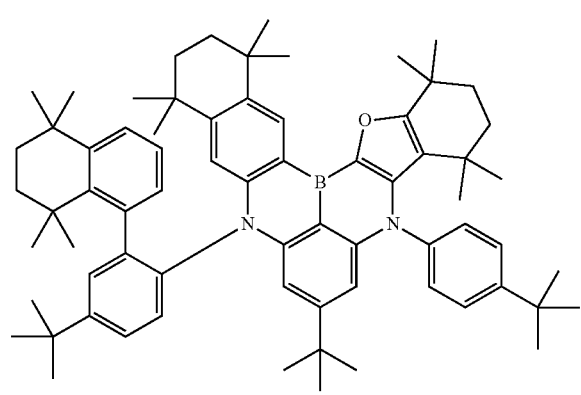 | 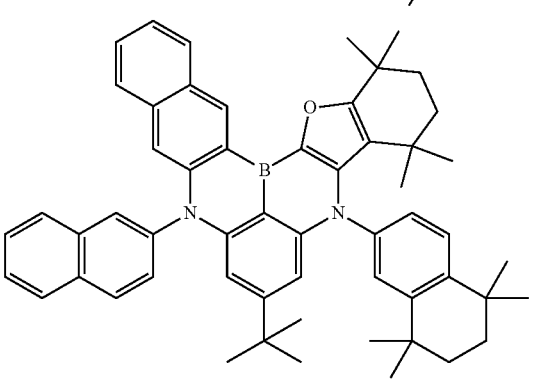 |
| 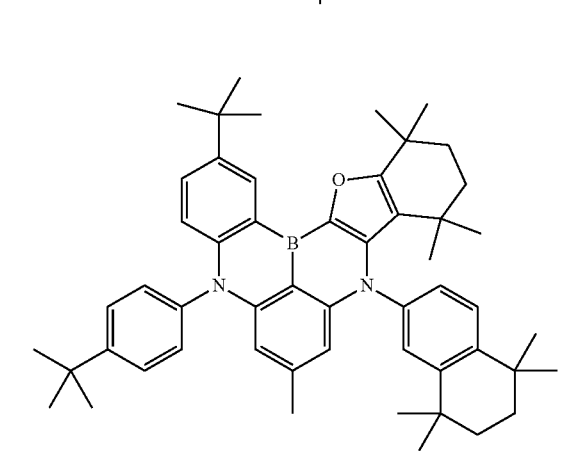 | 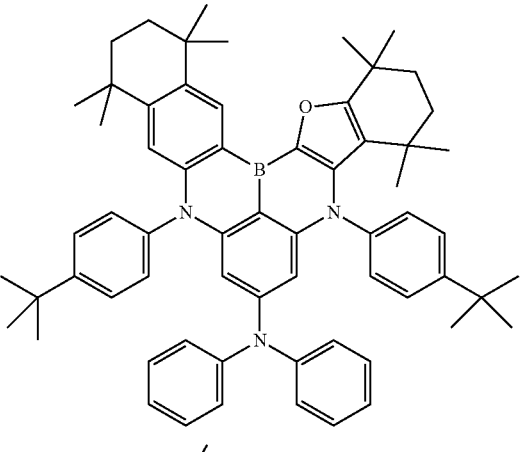 |
| 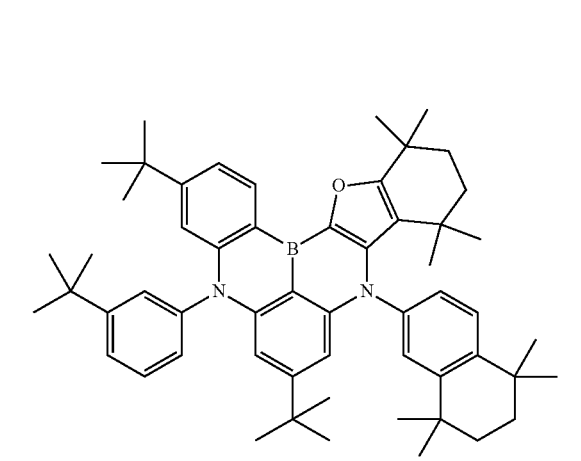 | 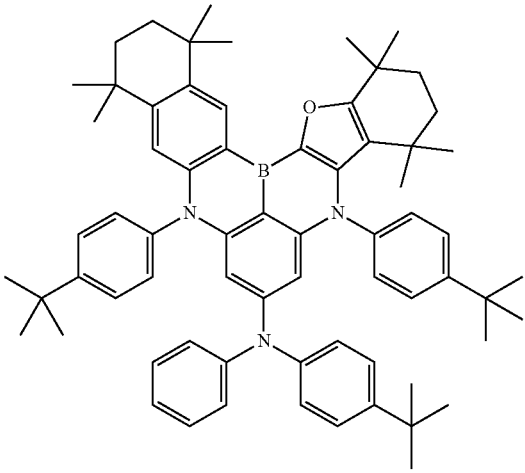 |

2669
-continued
2670
-continued
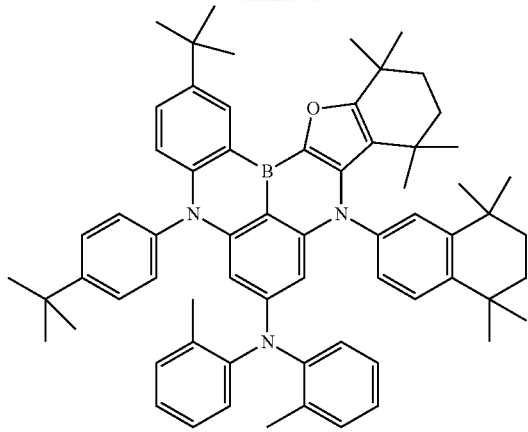
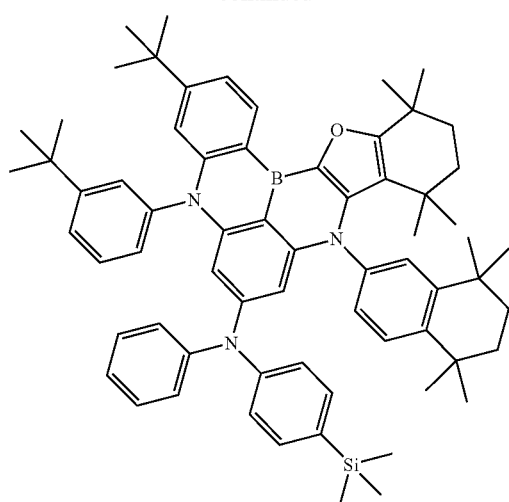
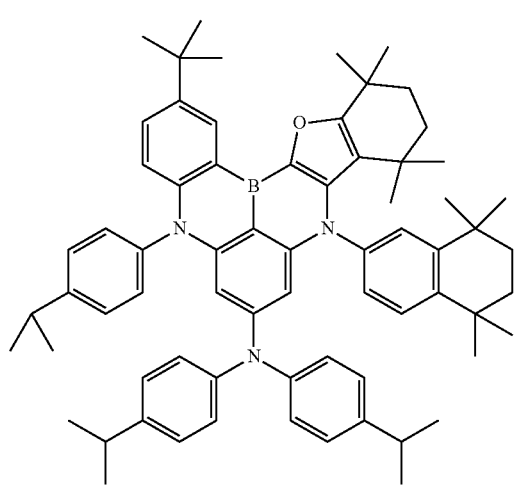
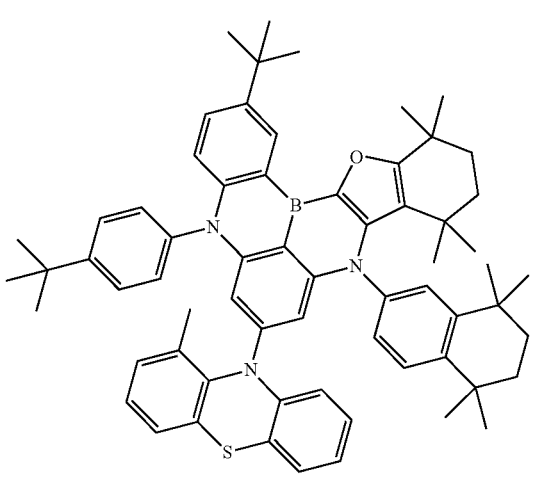
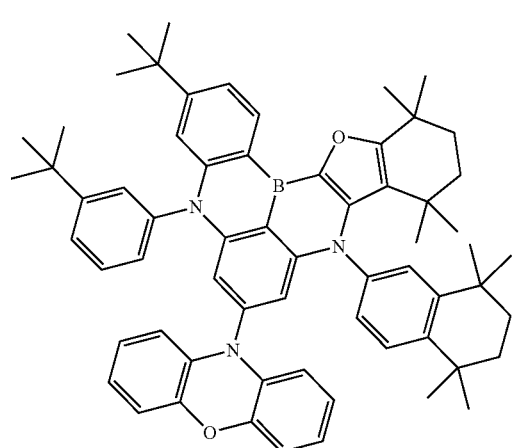
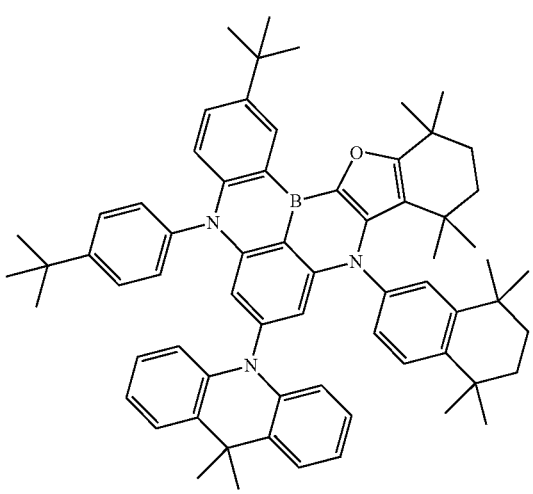

2671
-continued
2672
-continued
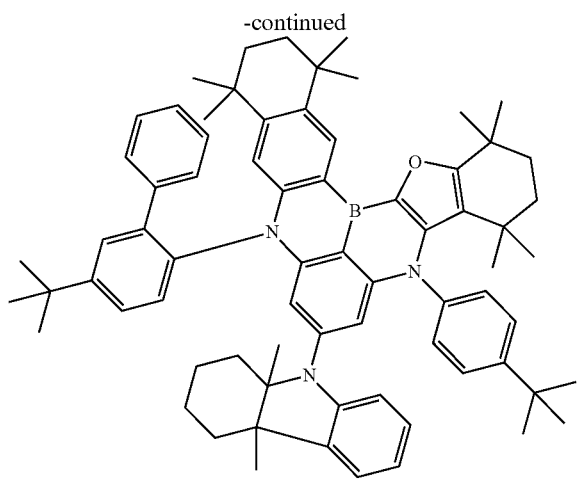
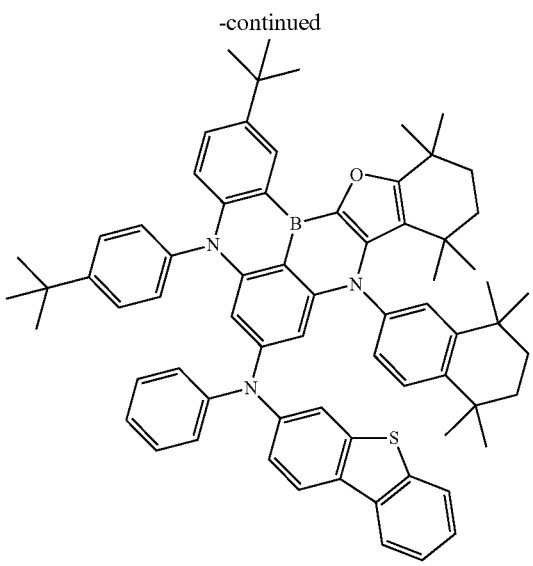
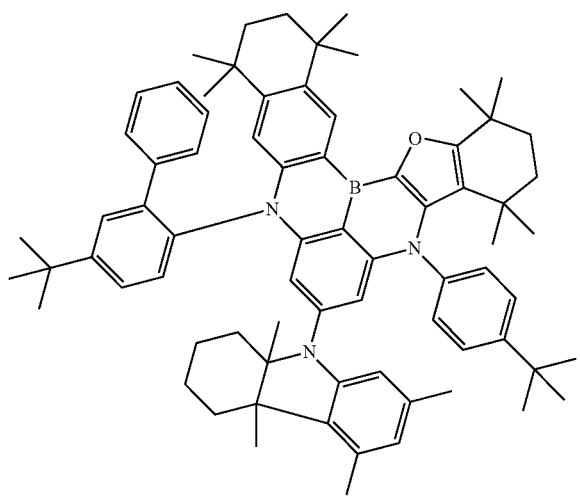
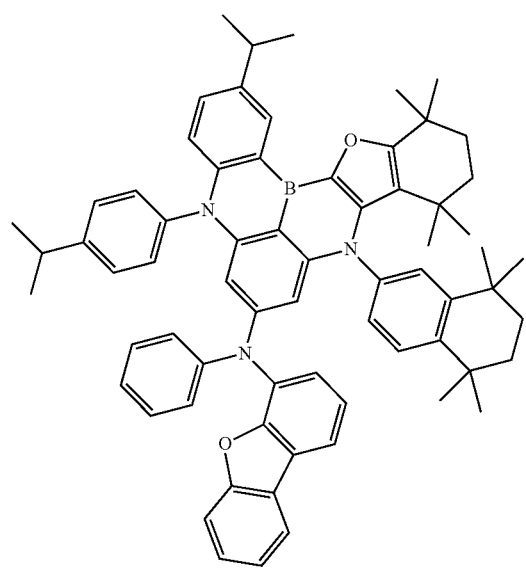
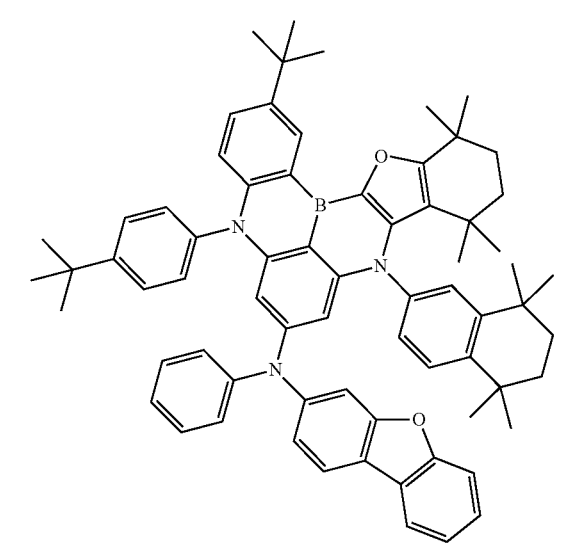
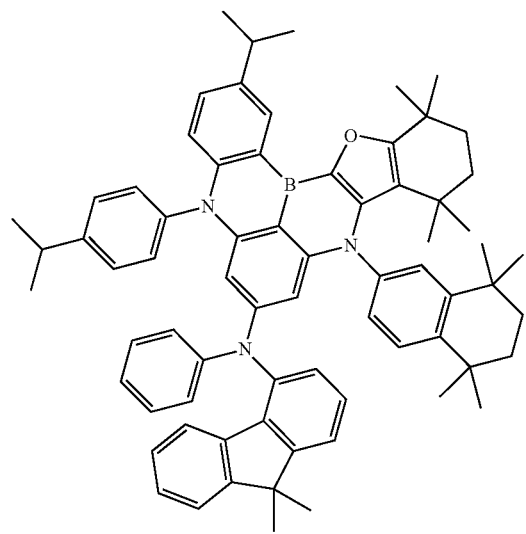

2673
-continued
2674
-continued
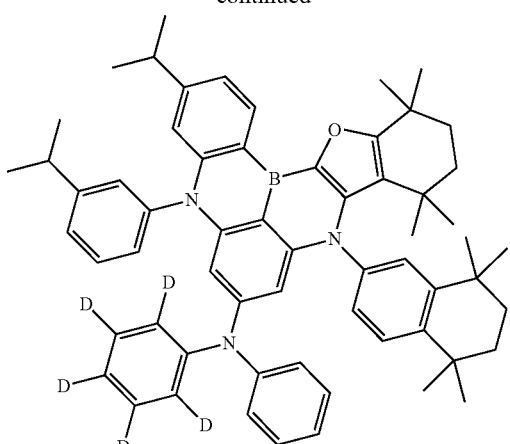
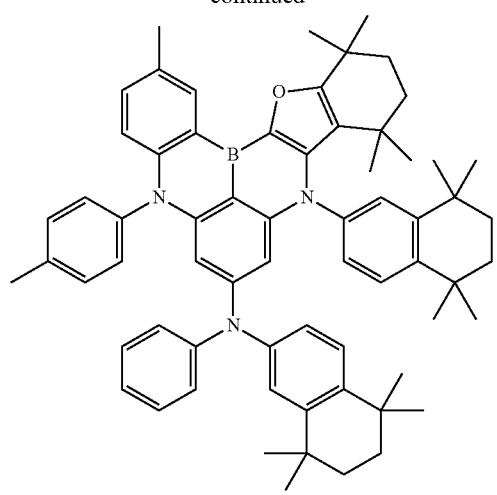
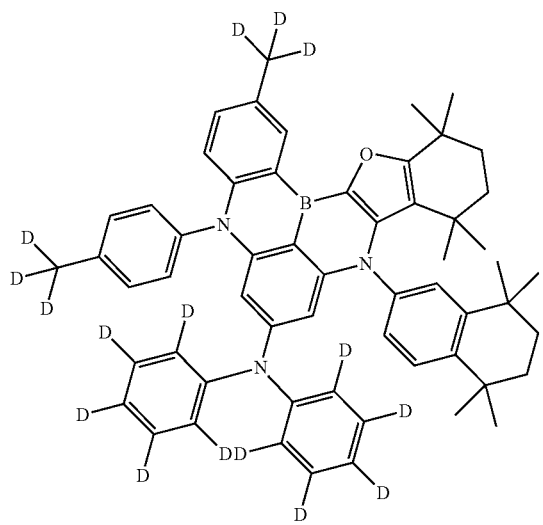
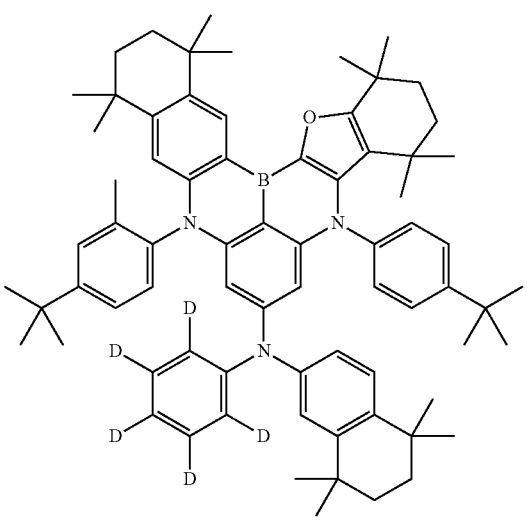
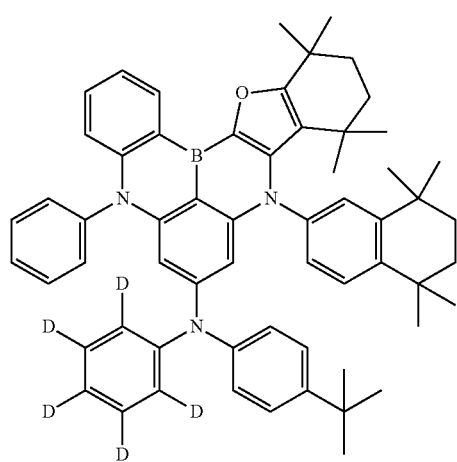
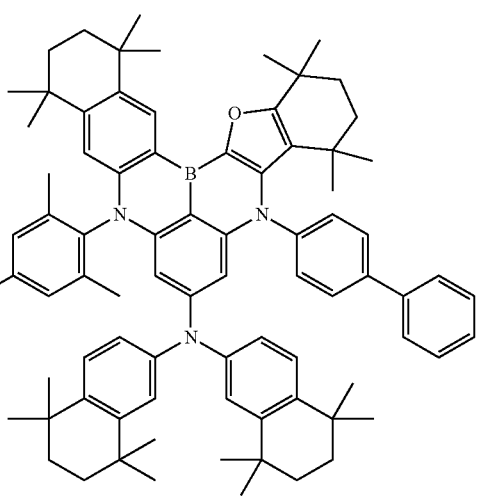

| 2675 -continued | 2676 -continued |
|---|---|
| 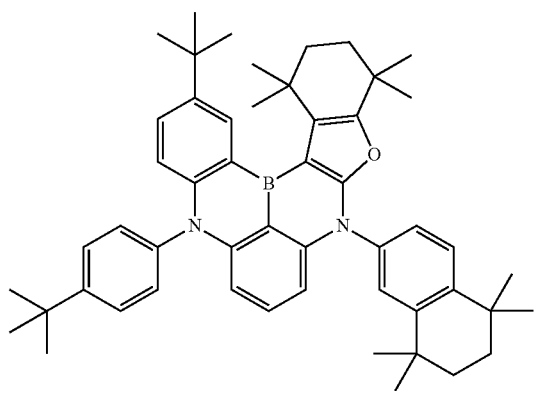 | 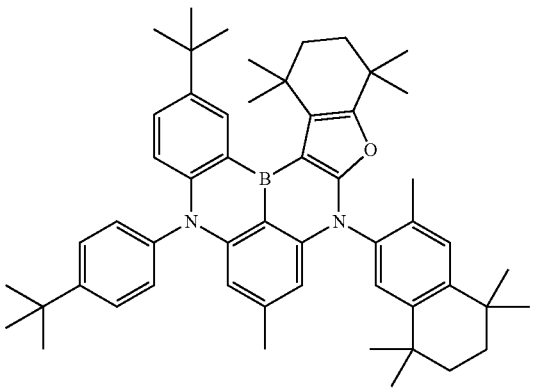 |
| 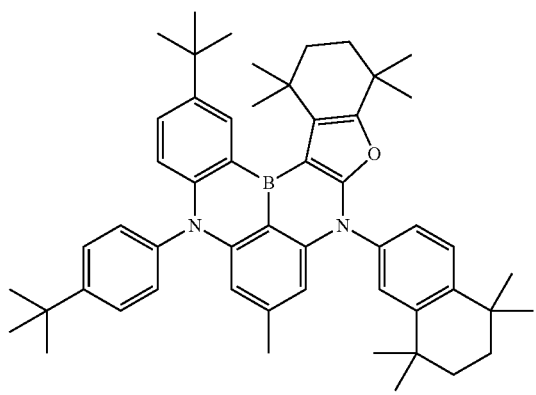 | 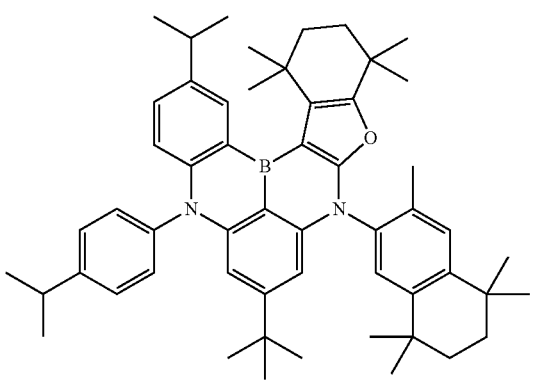 |
| 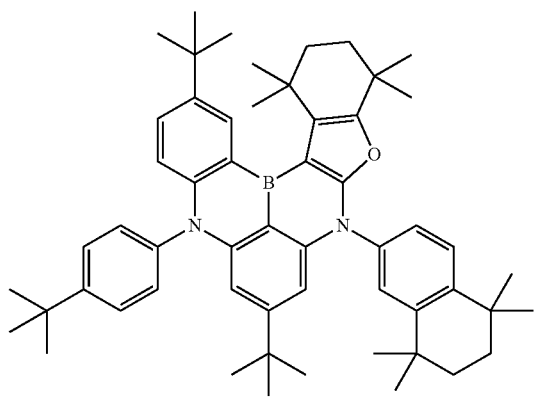 | 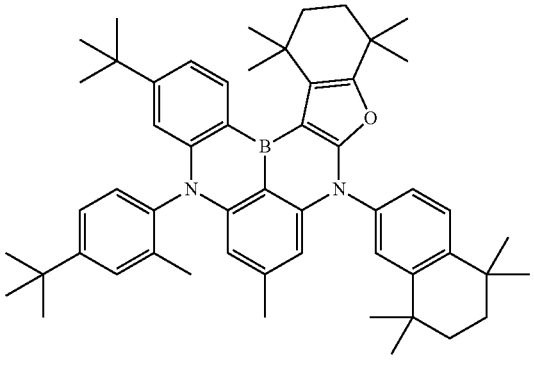 |
| 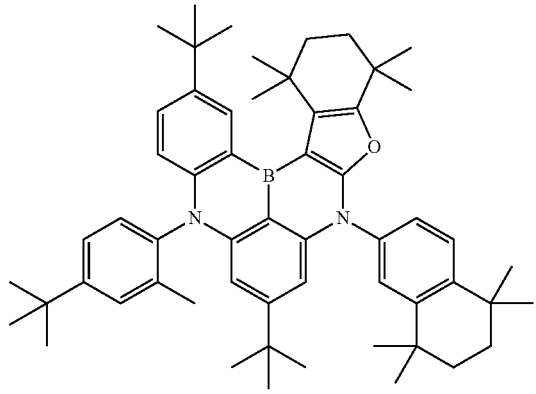 | 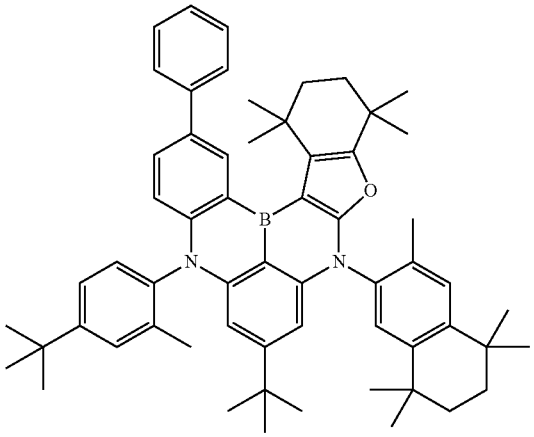 |

2677
-continued
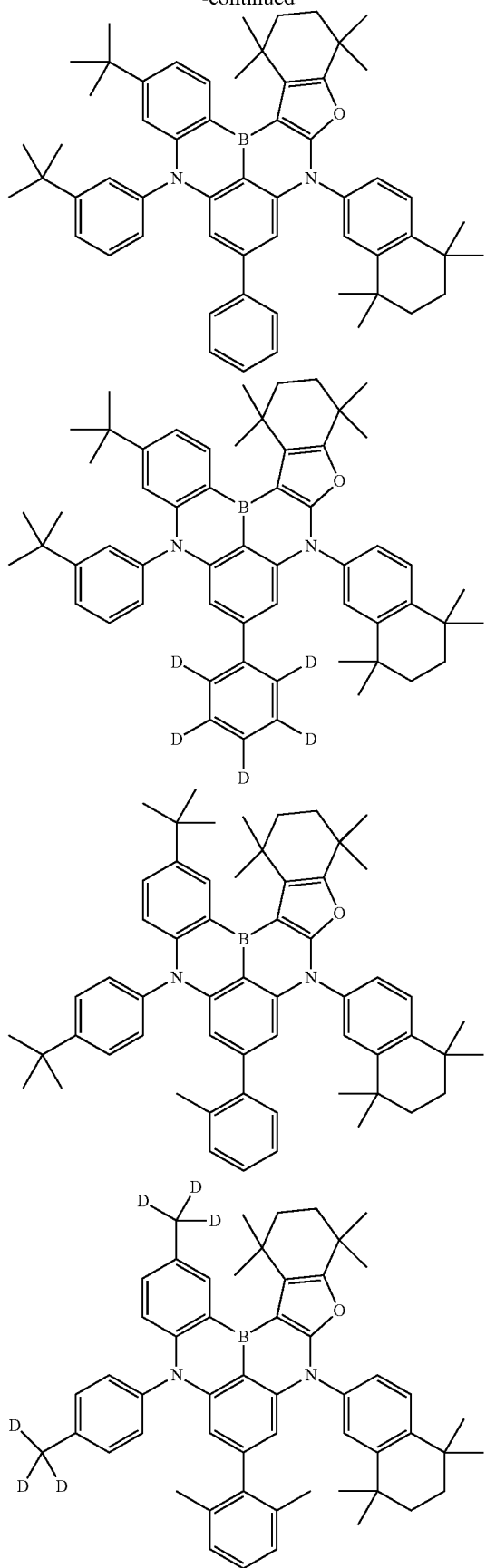
2678
-continued
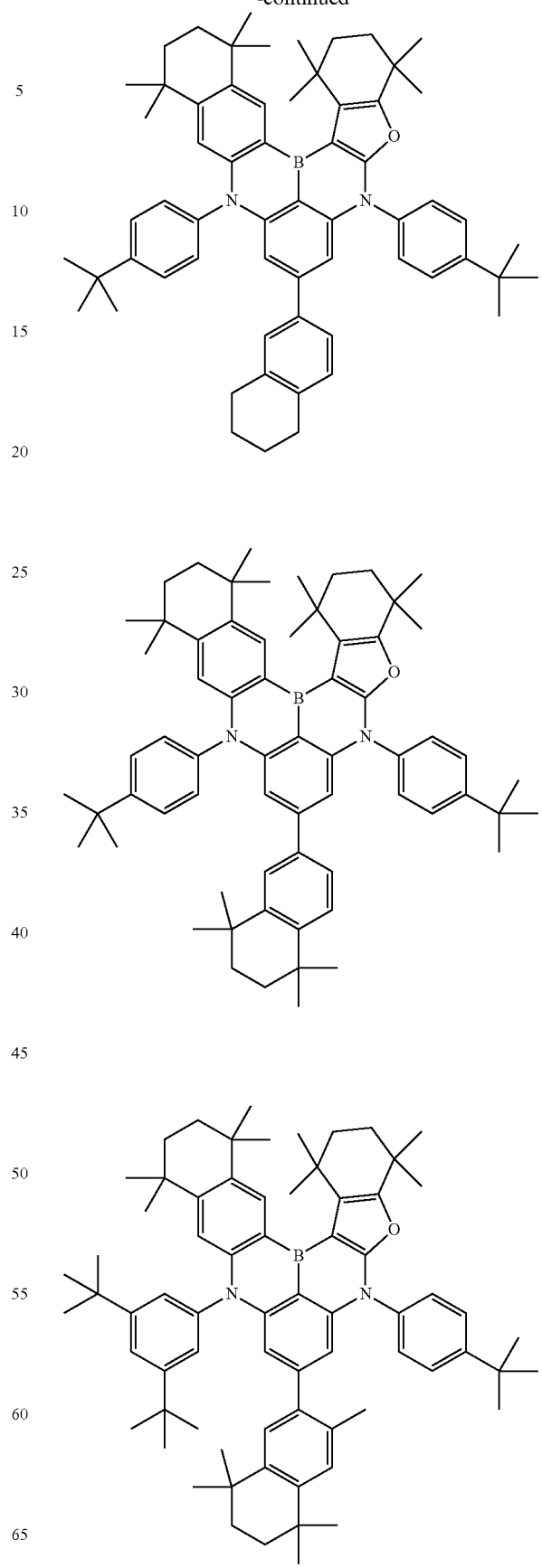

2679
-continued
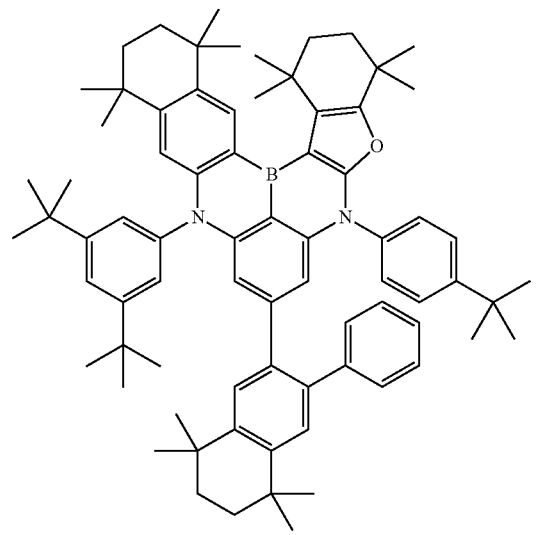
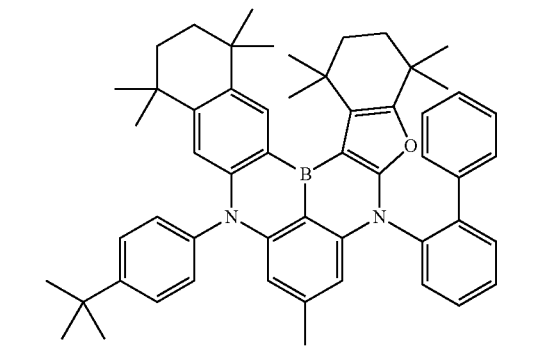
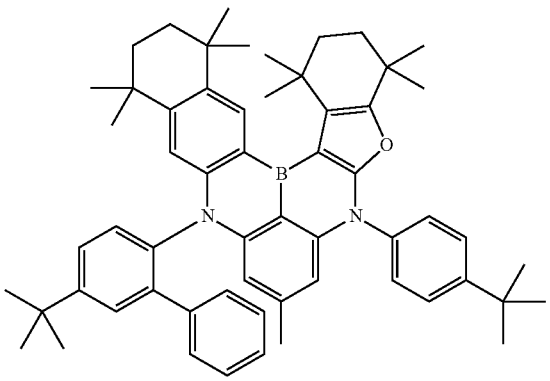
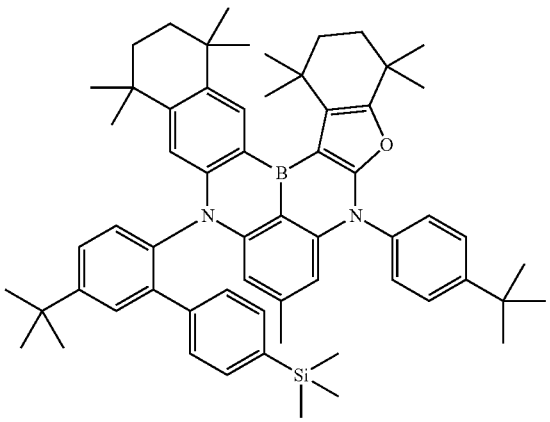
2680
-continued
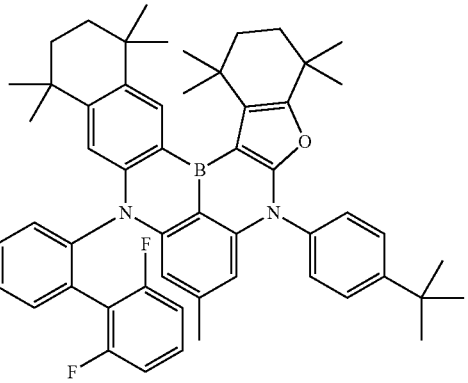
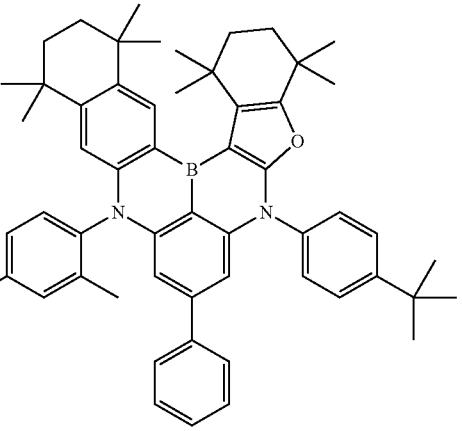
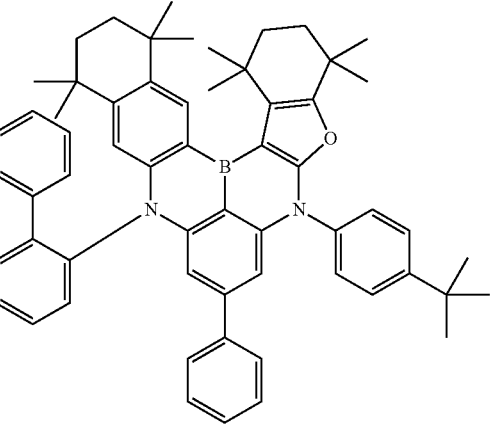
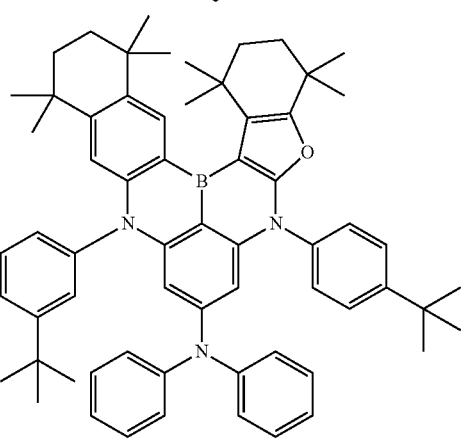

2681
-continued
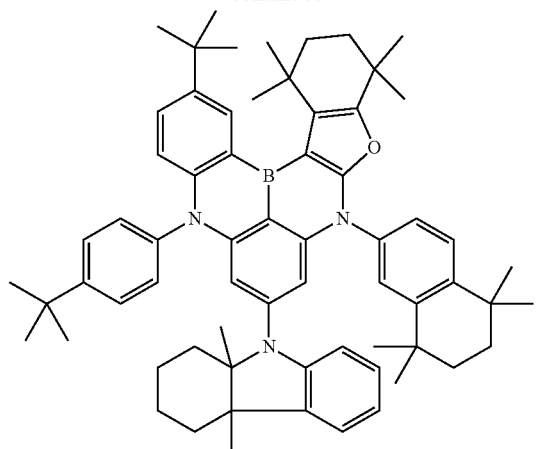
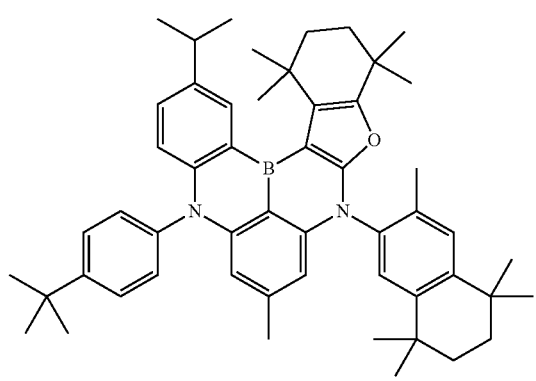
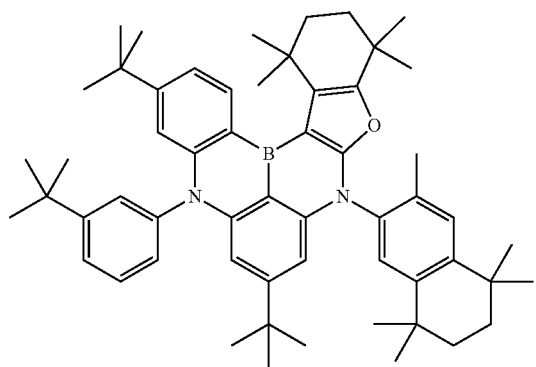
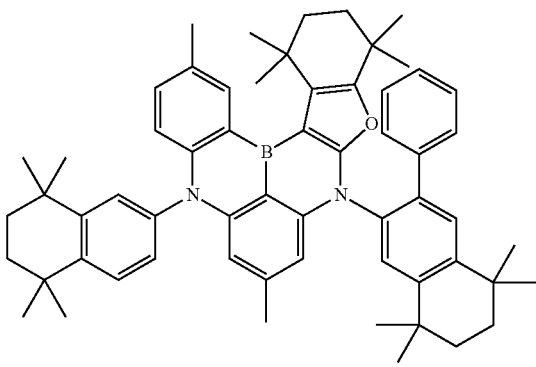
2682
-continued
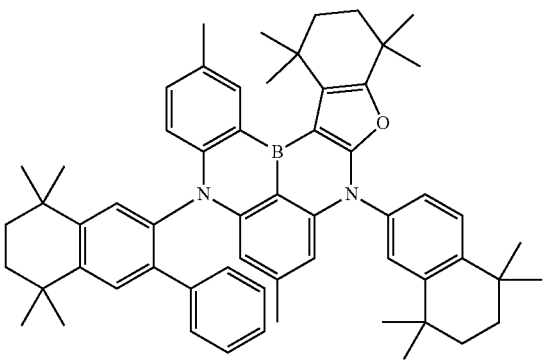
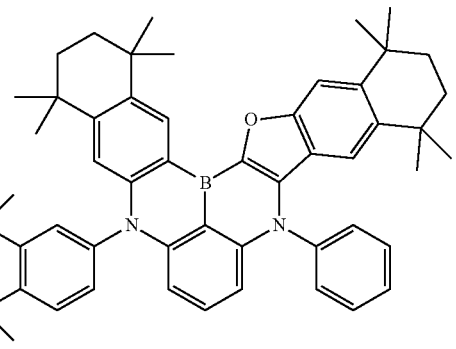
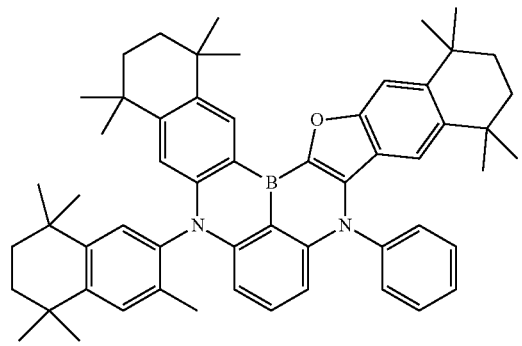
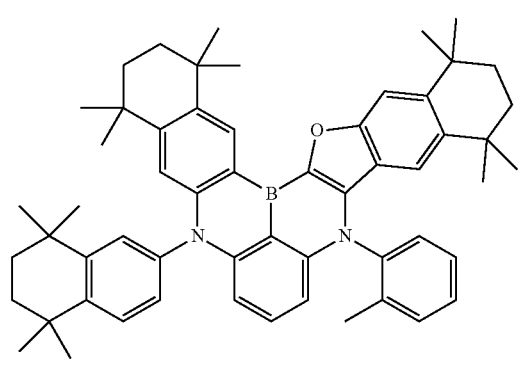

2683
-continued
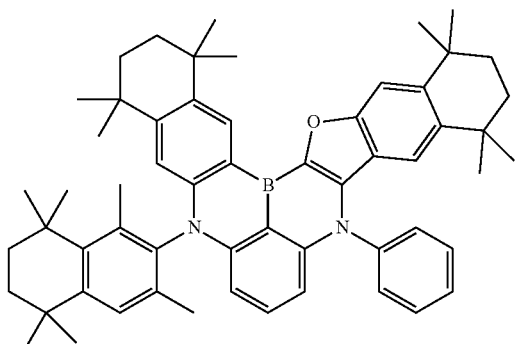
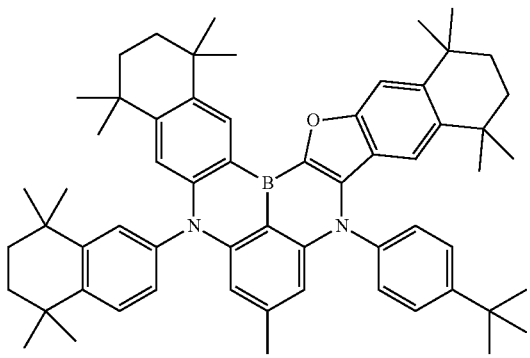
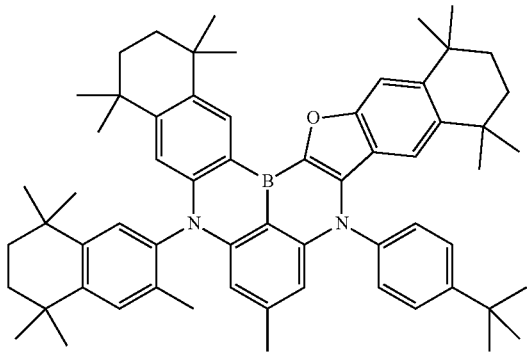
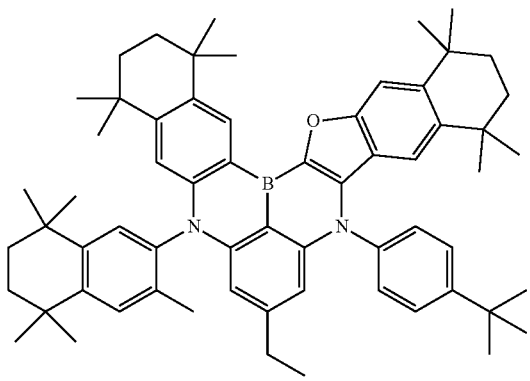
2684
-continued
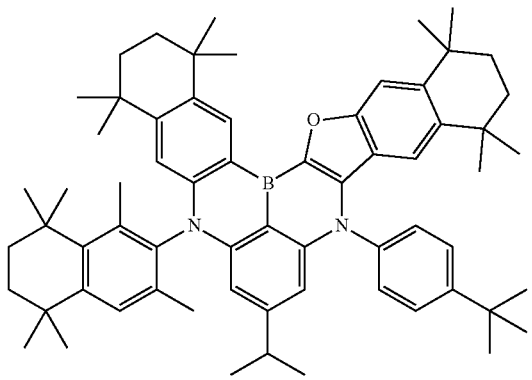
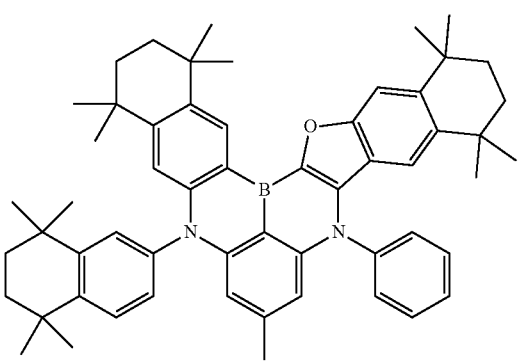
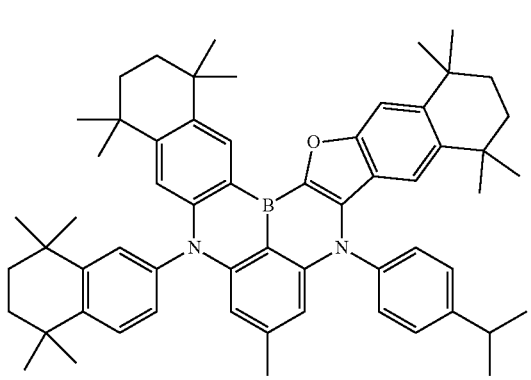
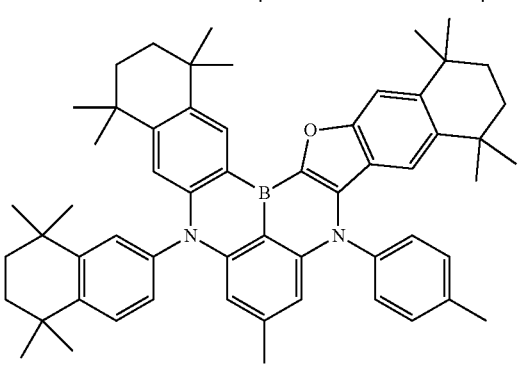

2685
-continued
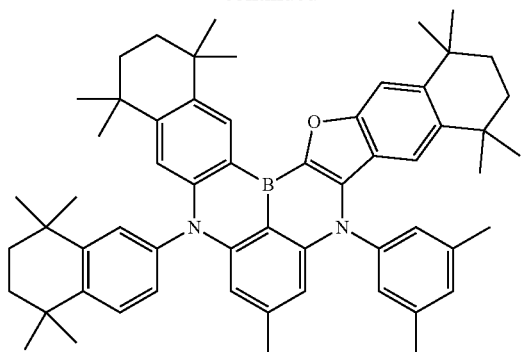
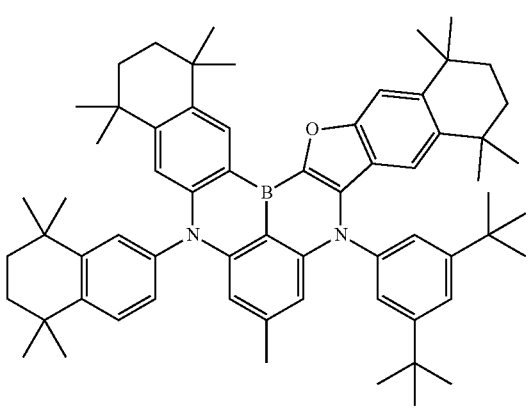
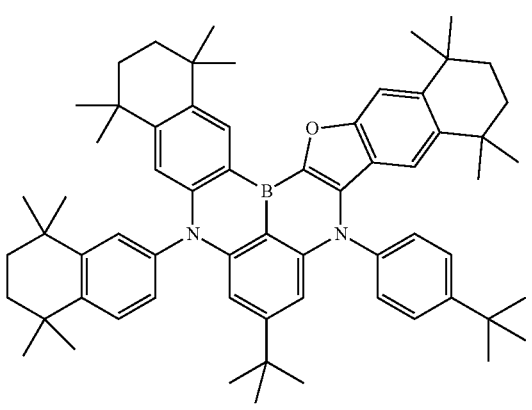
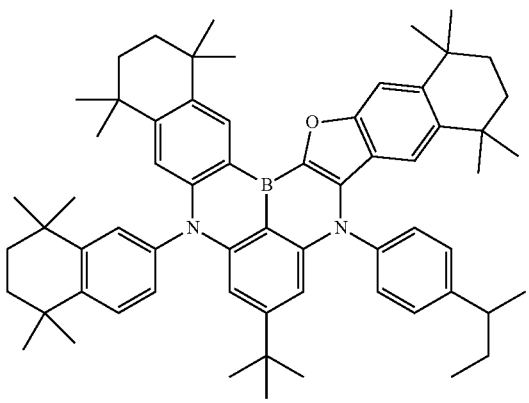
2686
-continued
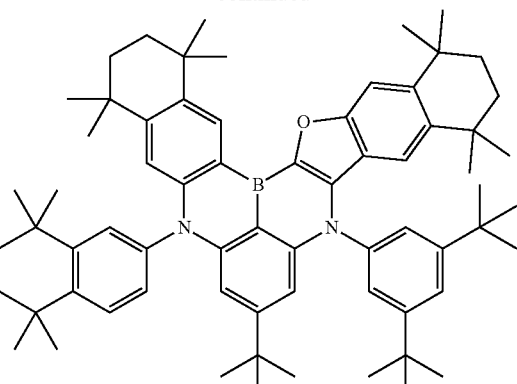
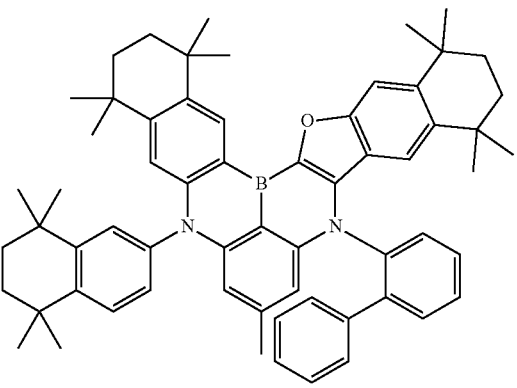
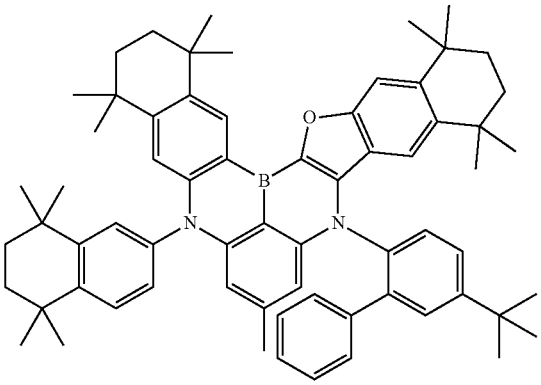
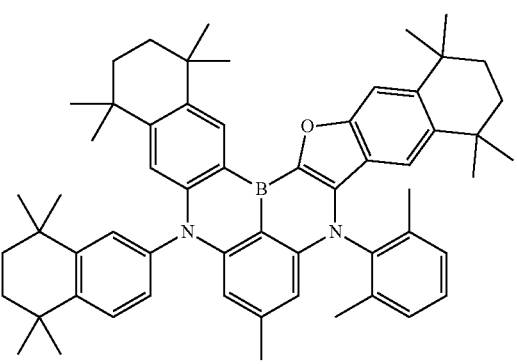

2687
-continued
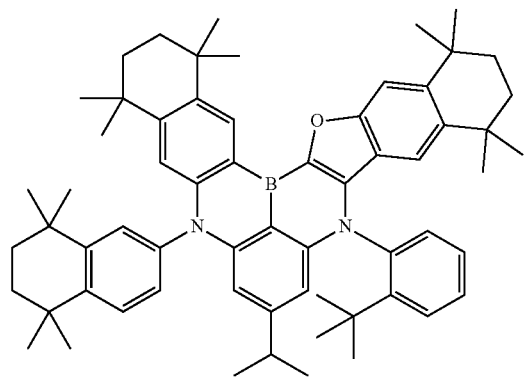
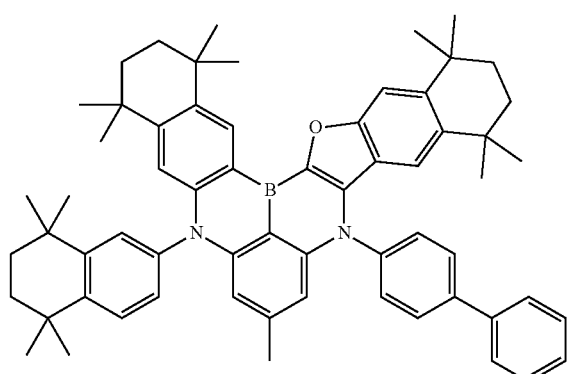
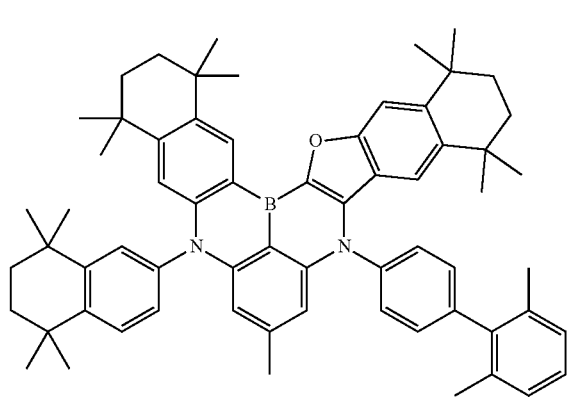
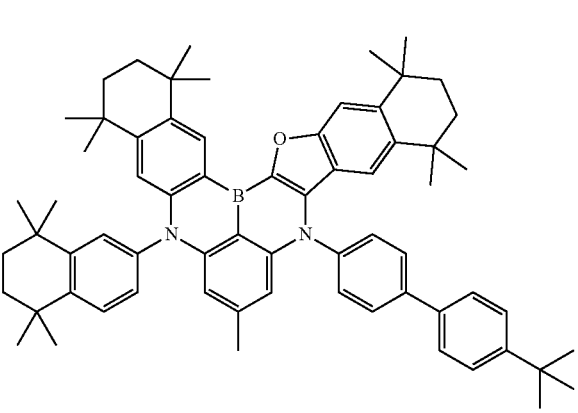
2688
-continued
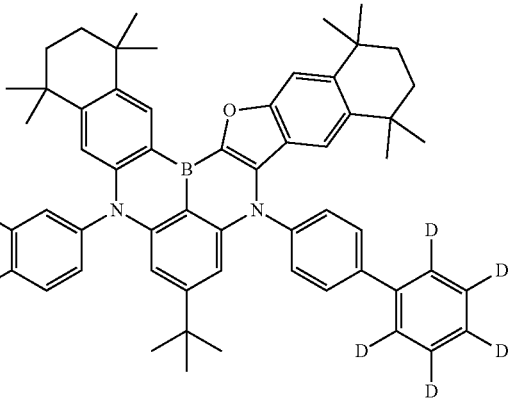
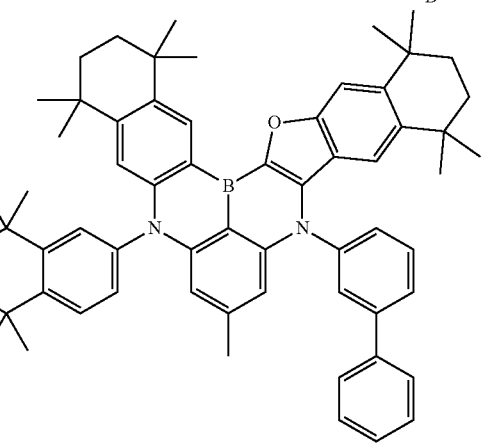
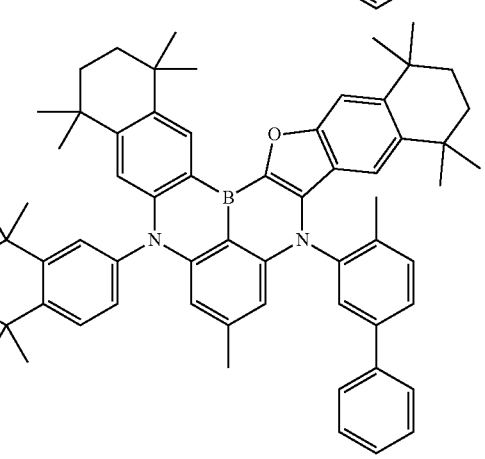
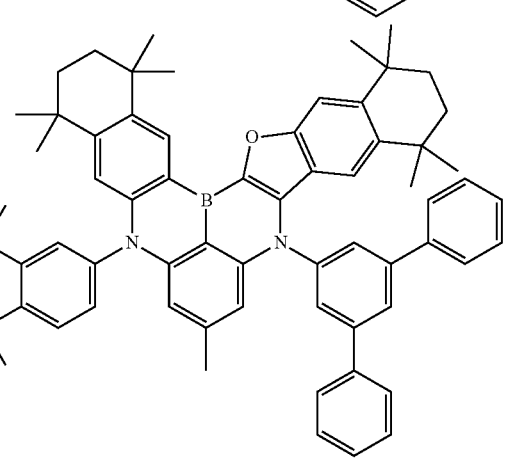

2689
-continued
2690
-continued
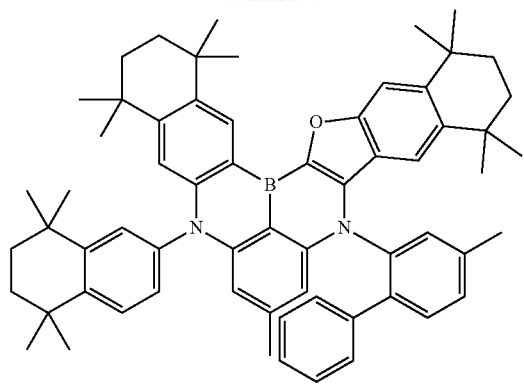
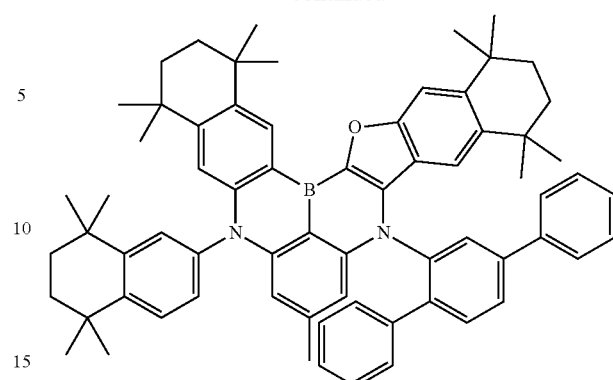
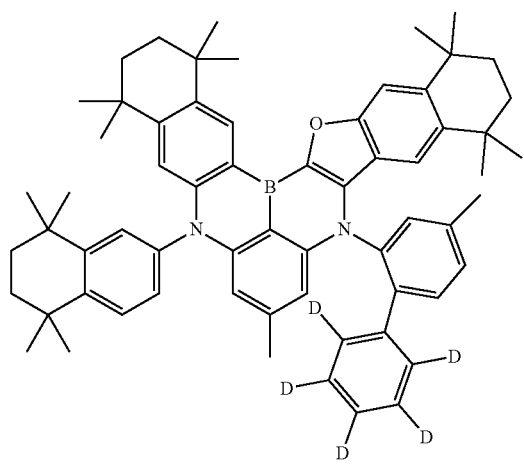
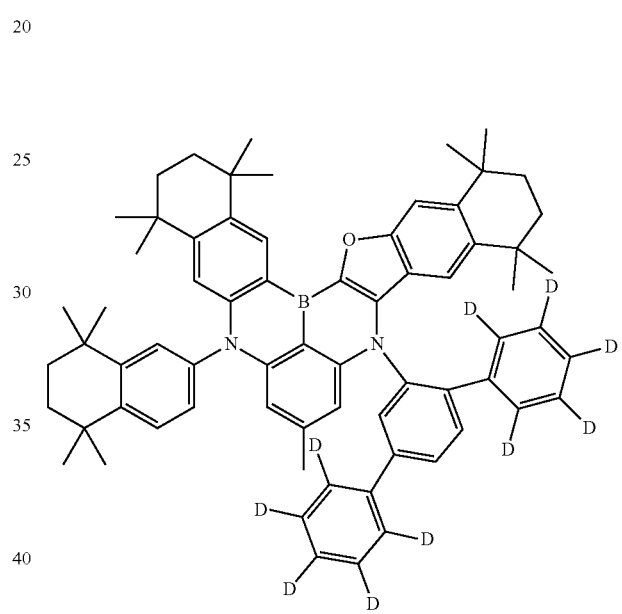
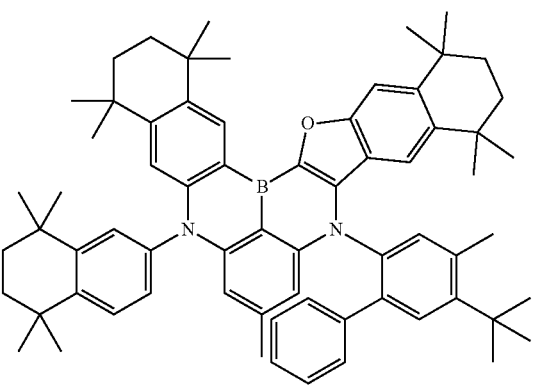
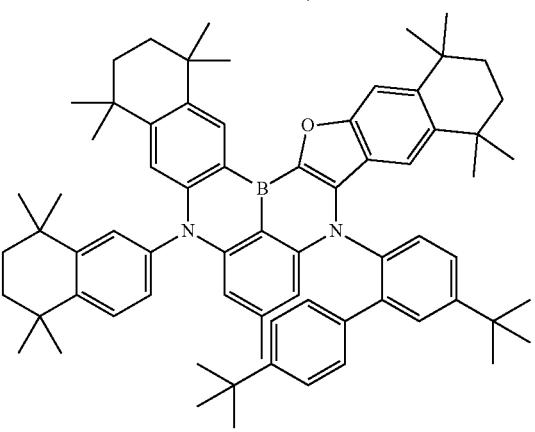
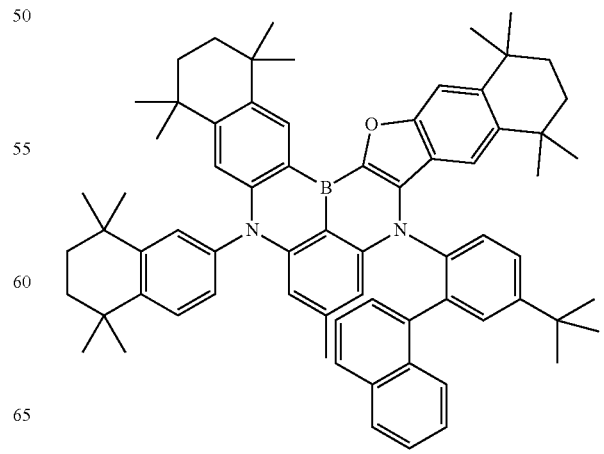

| 2691 | 2692 |
|---|---|
| -continued | -continued |
| 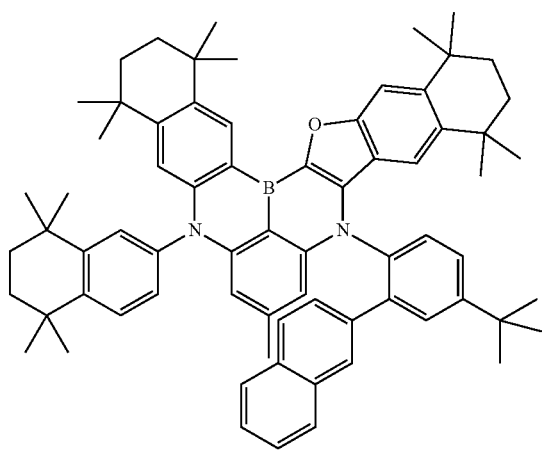 | 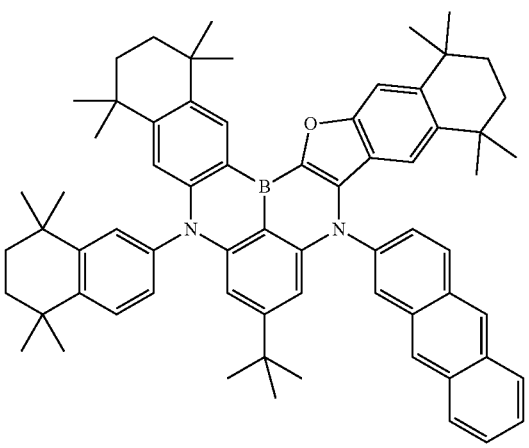 |
| 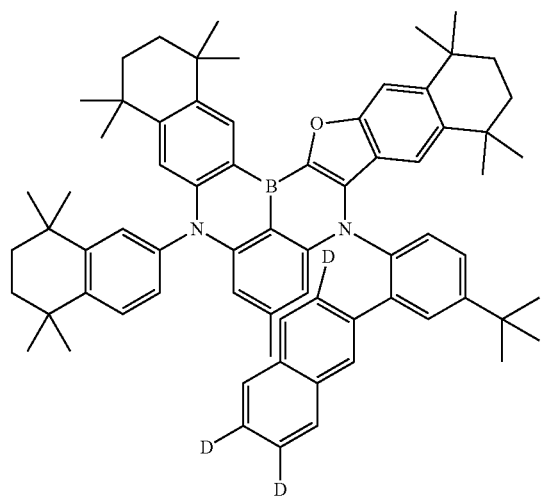 | 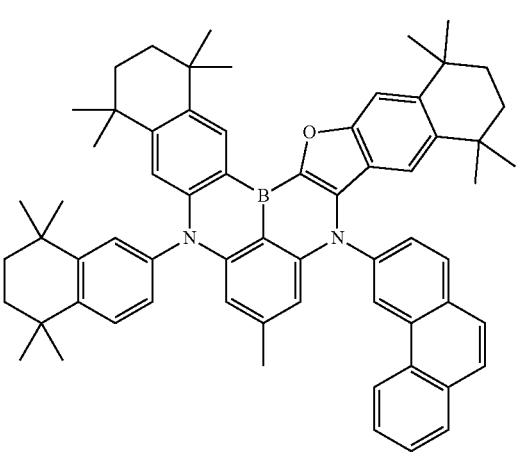 |
| 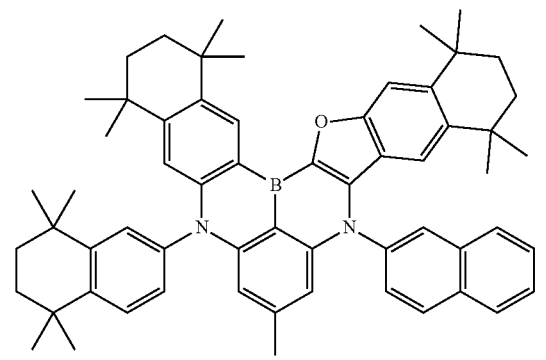 | 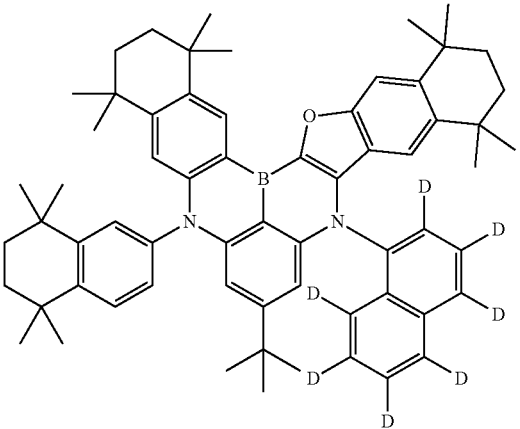 |
| 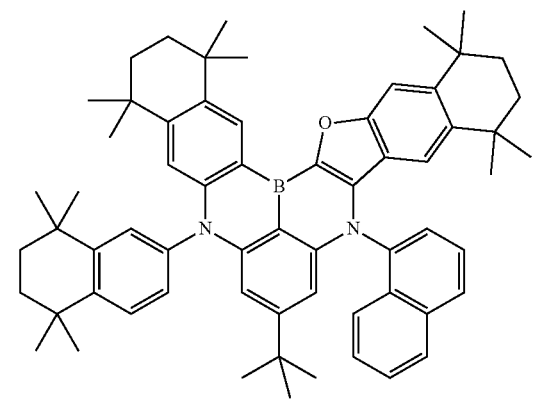 | 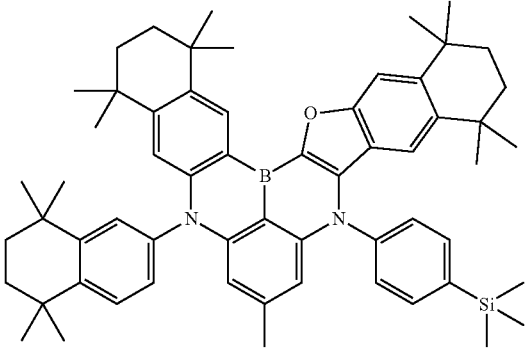 |

2693
-continued
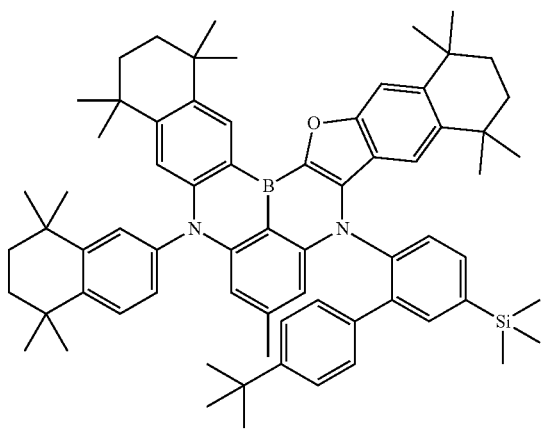
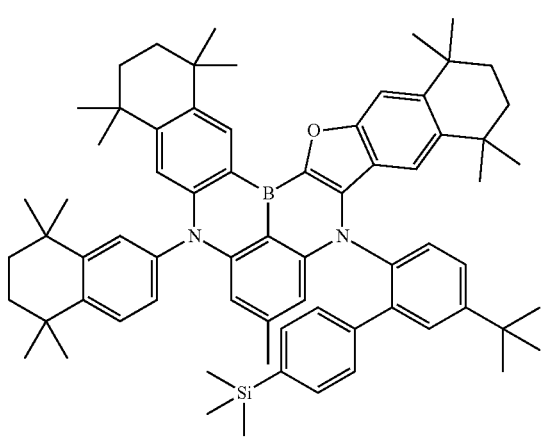
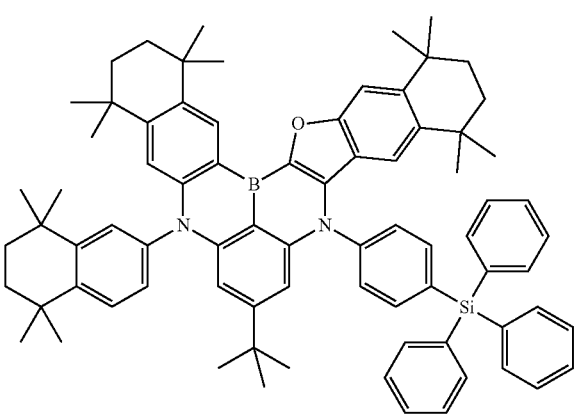
2694
-continued
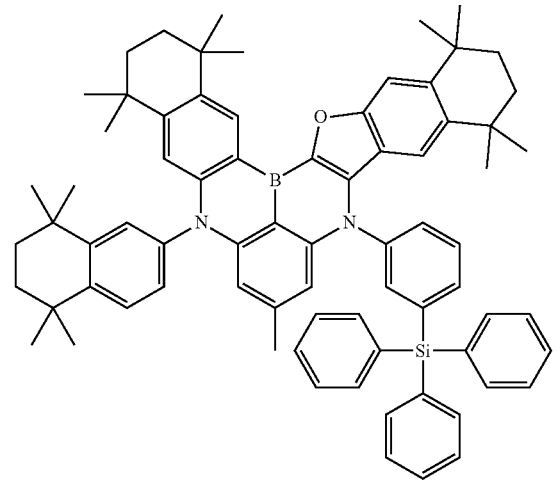
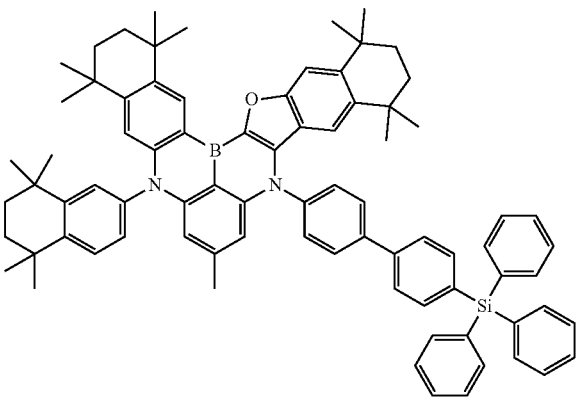
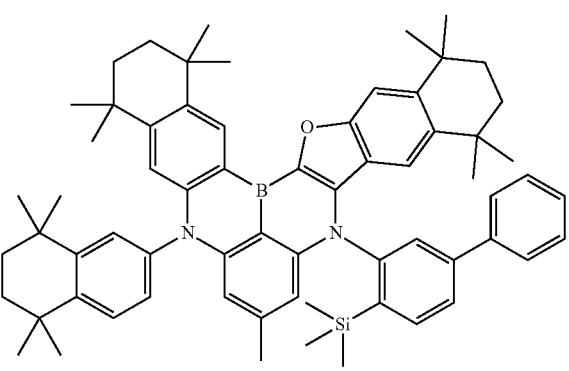
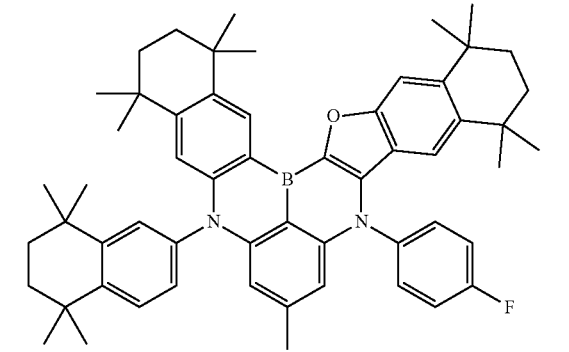

| 2695 -continued | 2696 -continued |
|---|---|
| 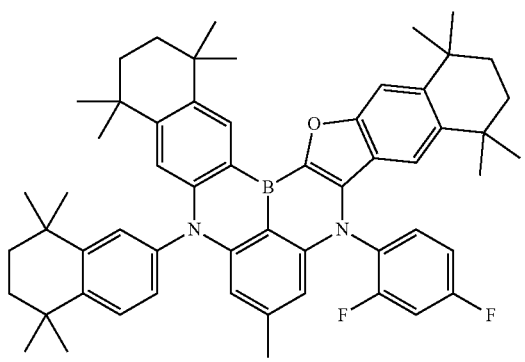 | 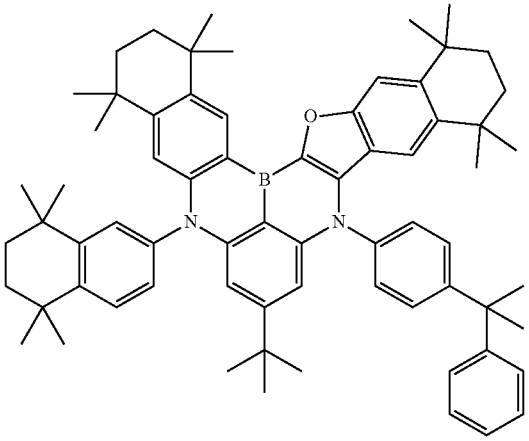 |
| 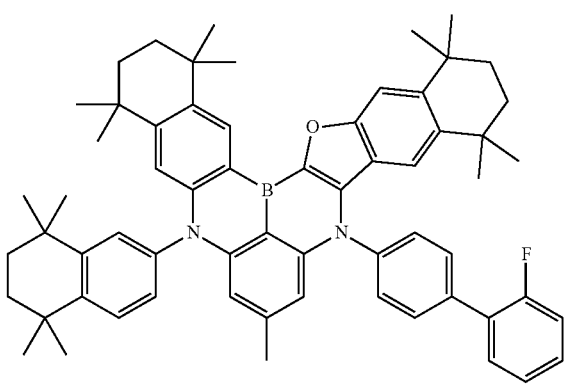 | 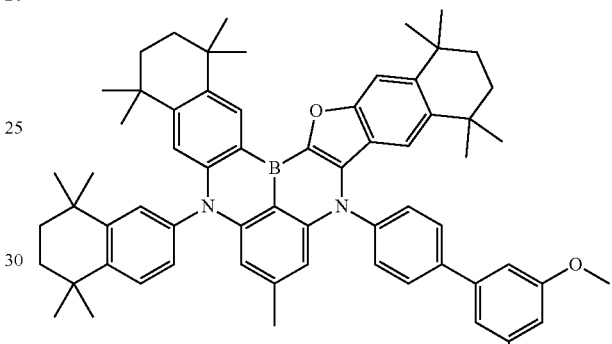 |
| 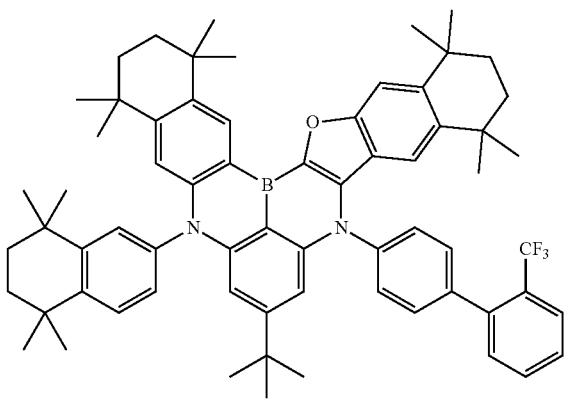 | 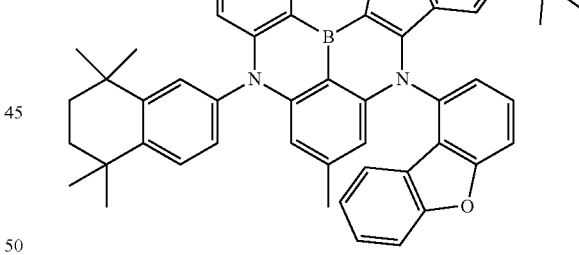 |
| 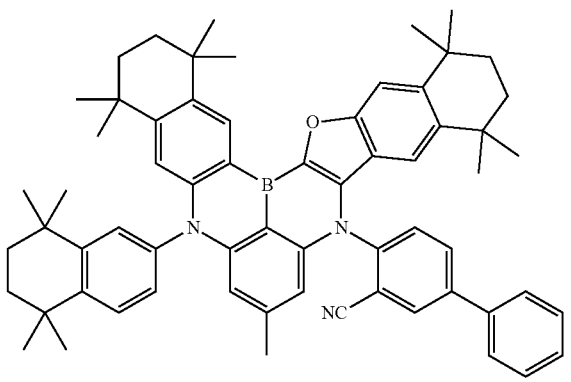 | 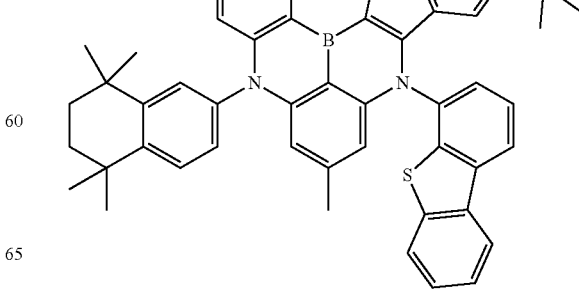 |

2697
-continued
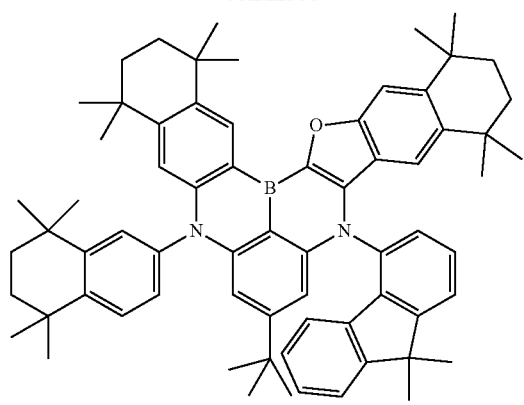
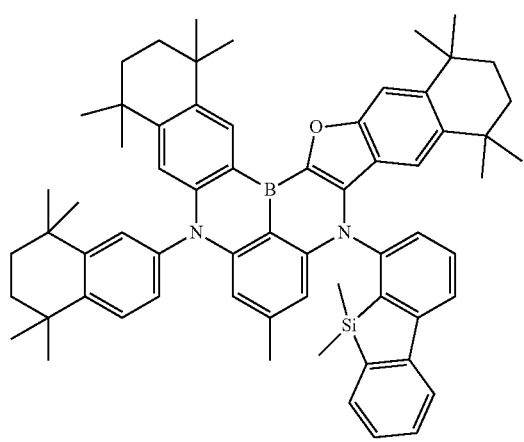
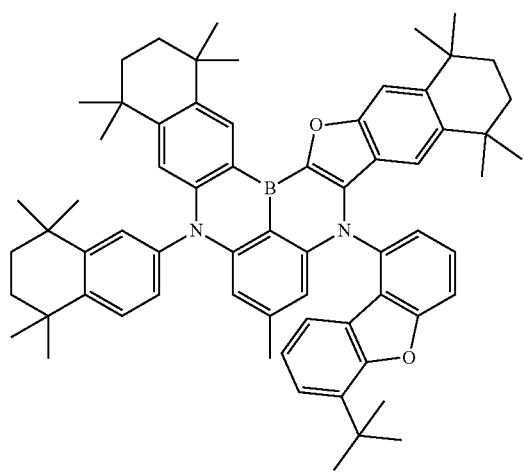
2698
-continued
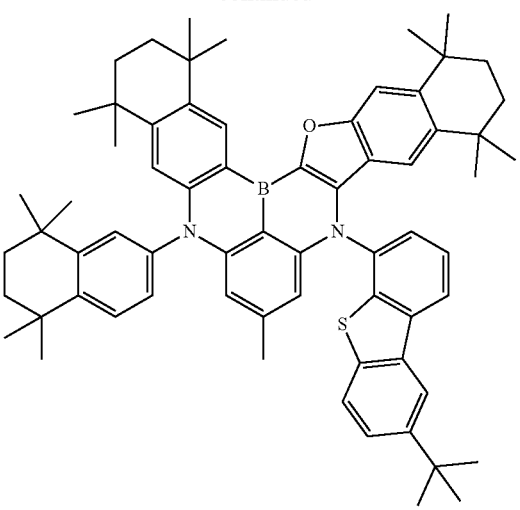
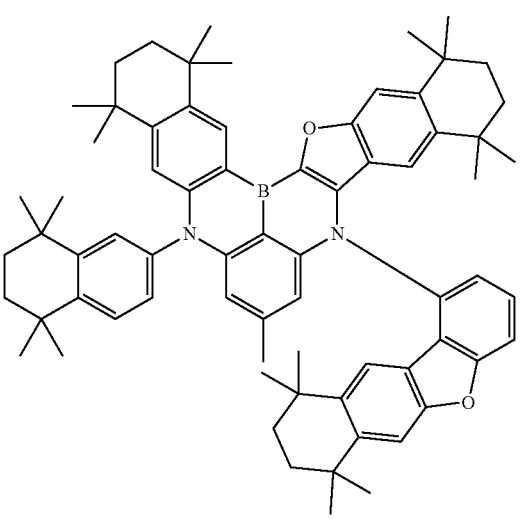
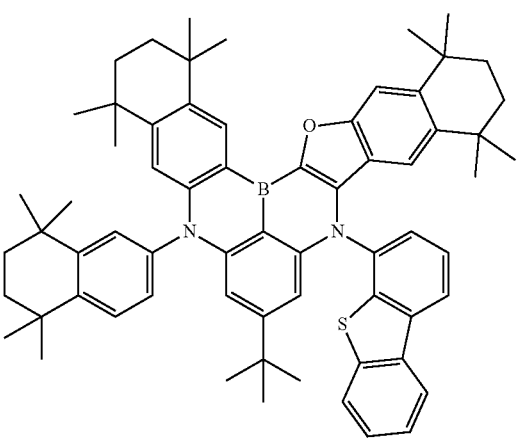

2699
-continued
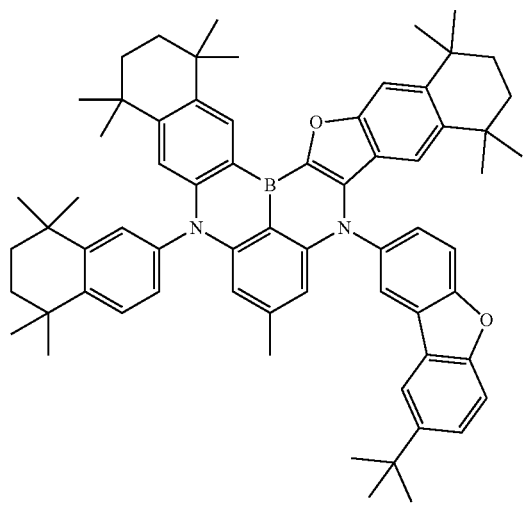
2700
-continued
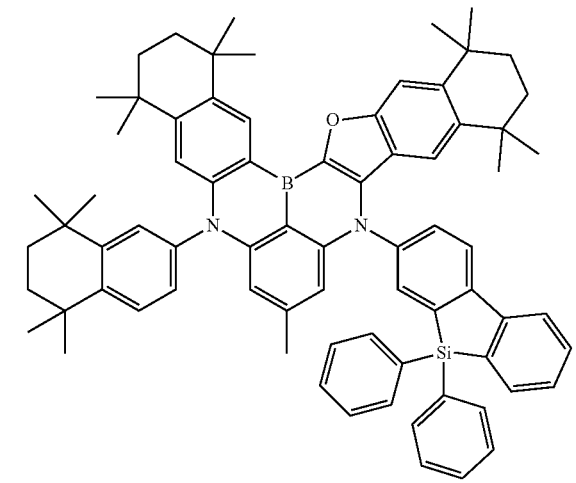
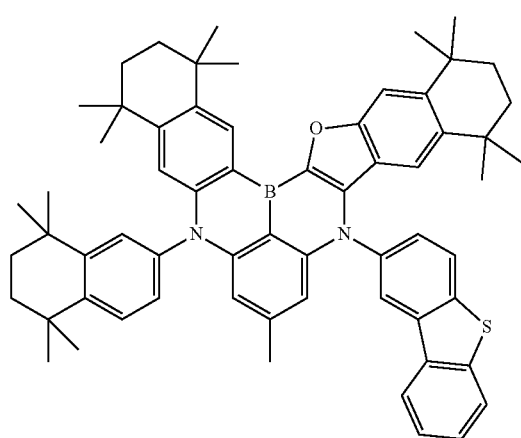
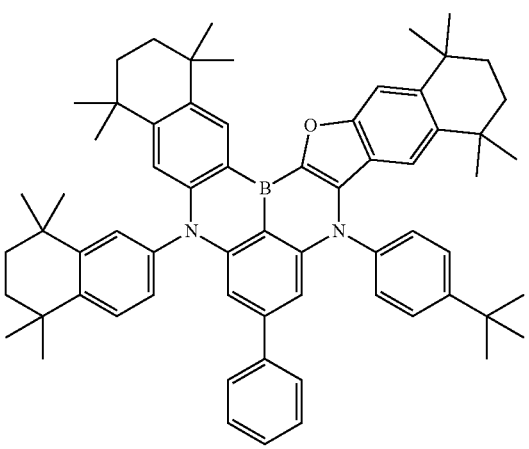
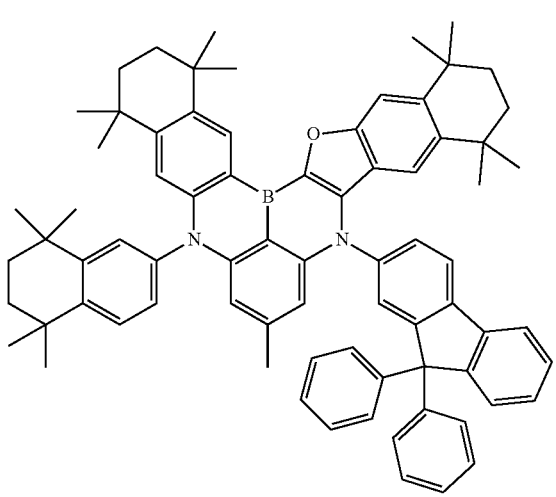
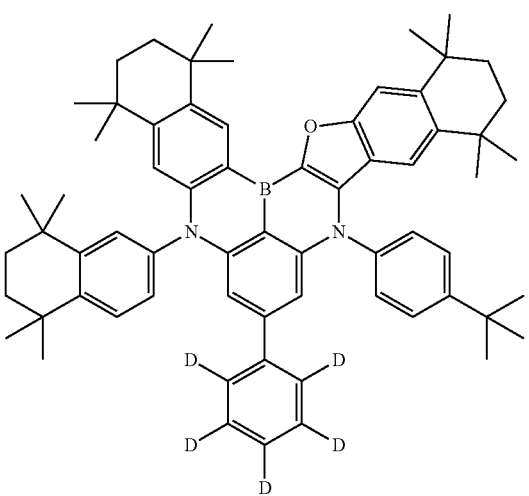

2701
-continued
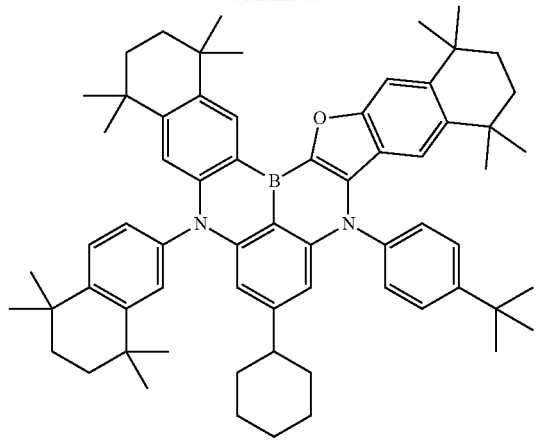
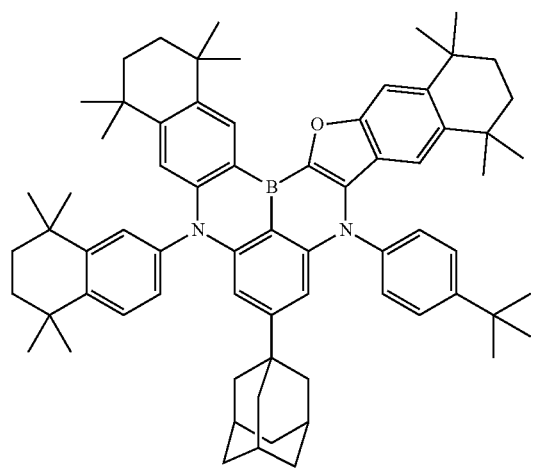
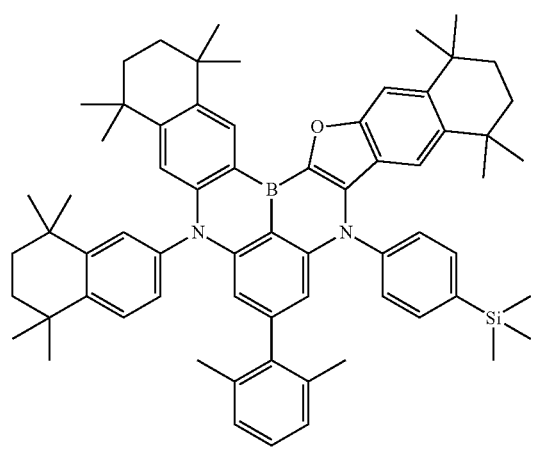
2702
-continued
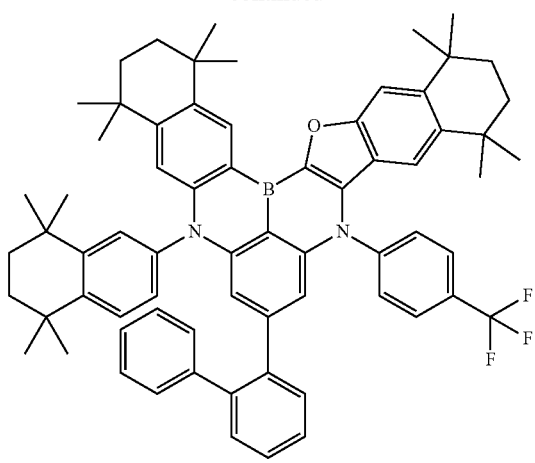
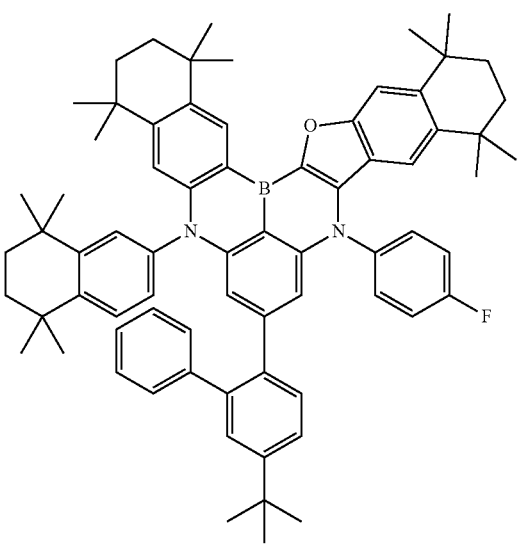
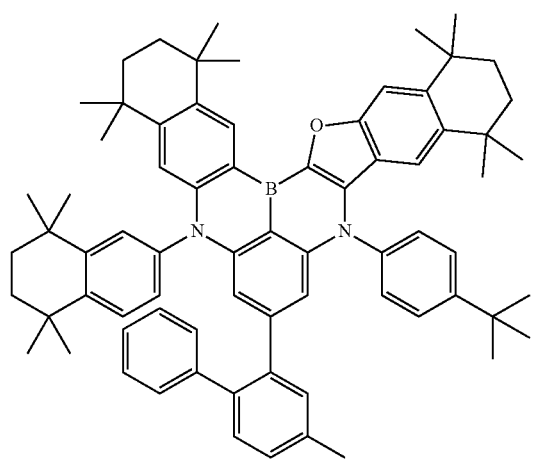

2703
-continued
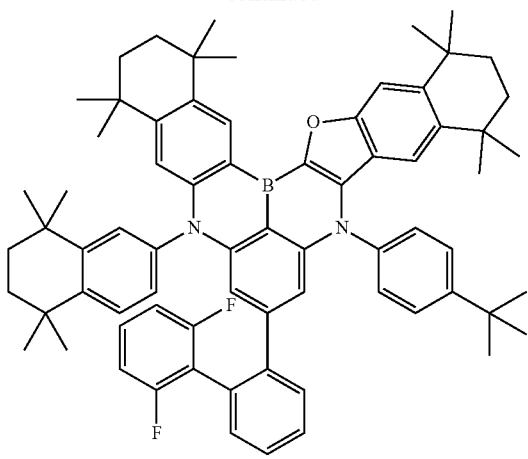
2704
-continued
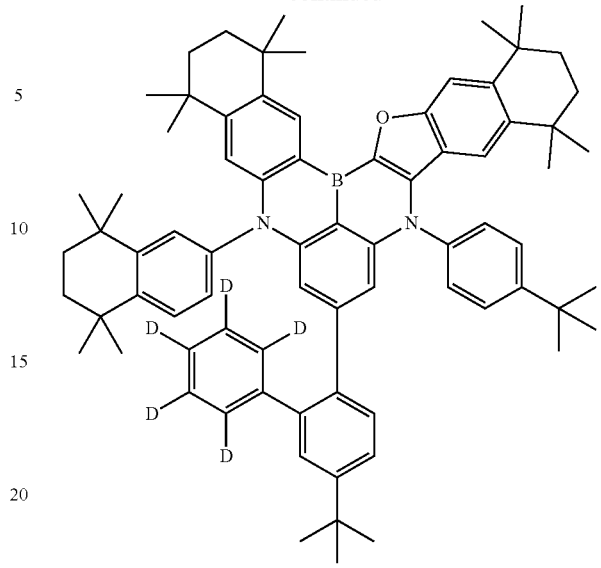
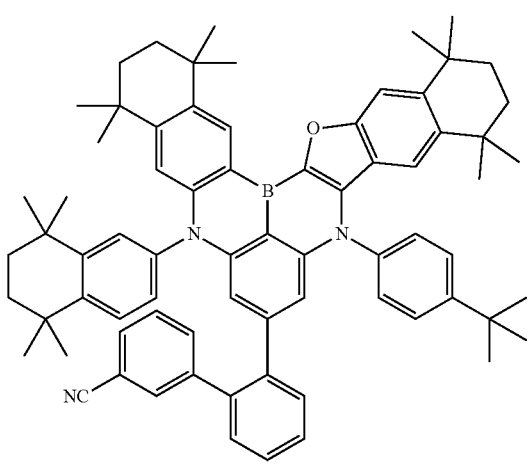
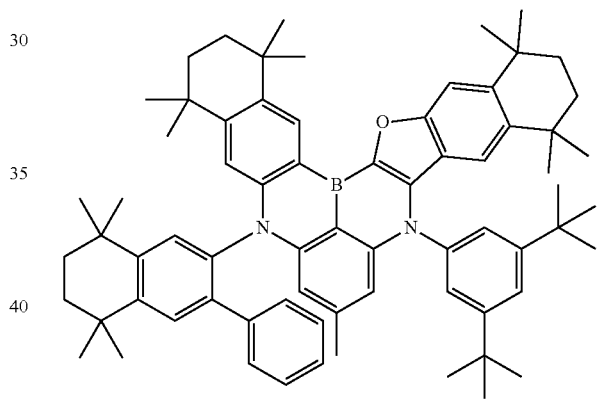
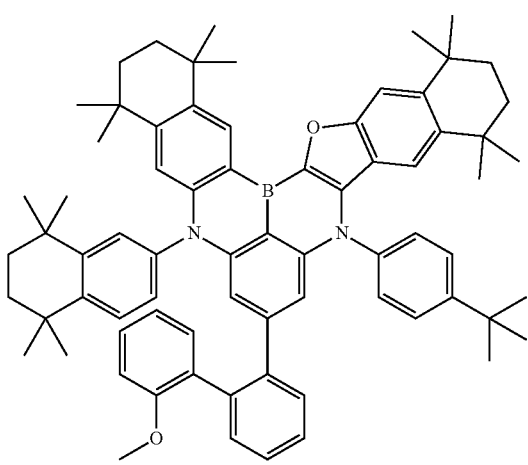
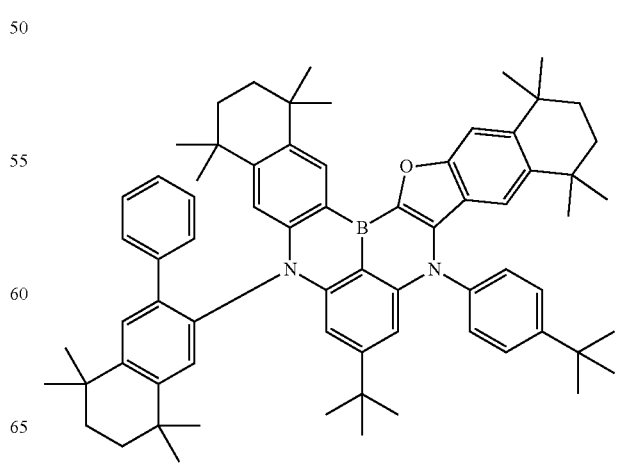

2705
-continued
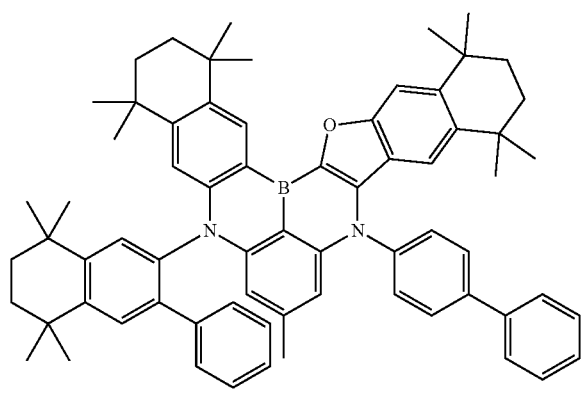
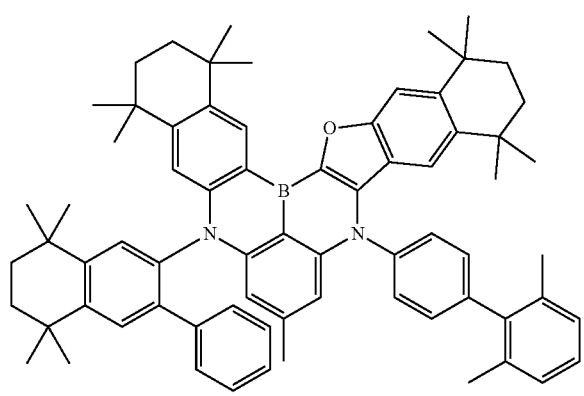
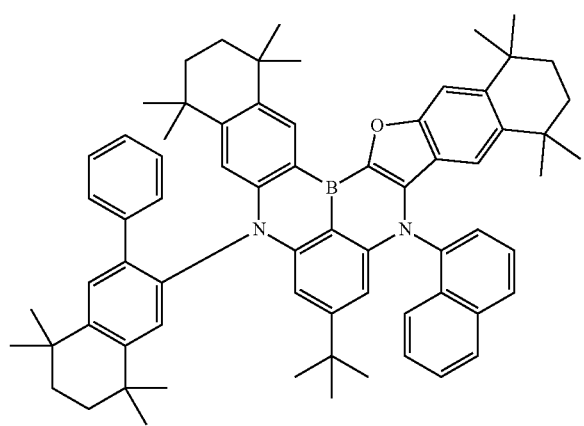
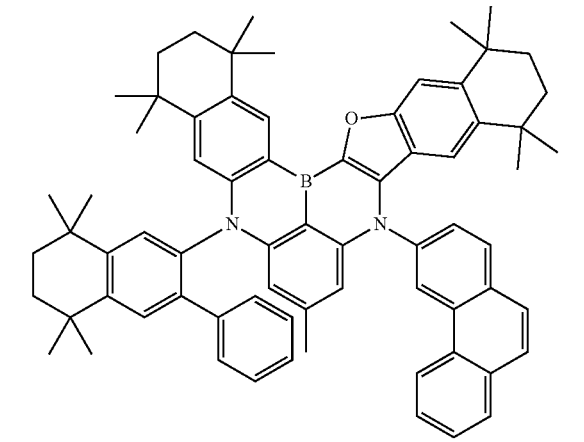
2706
-continued
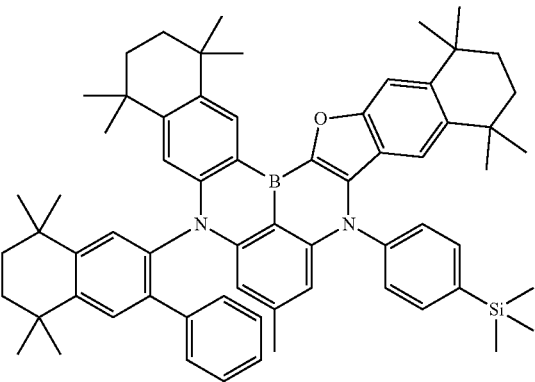
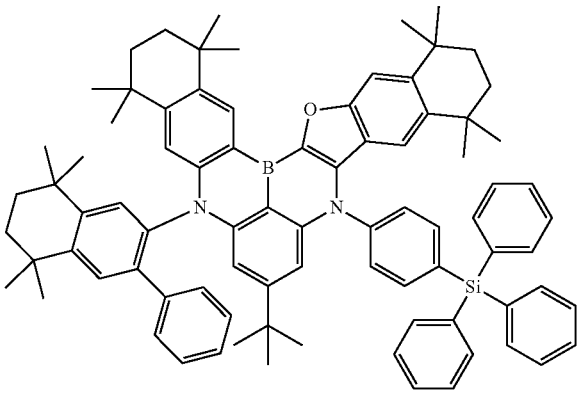
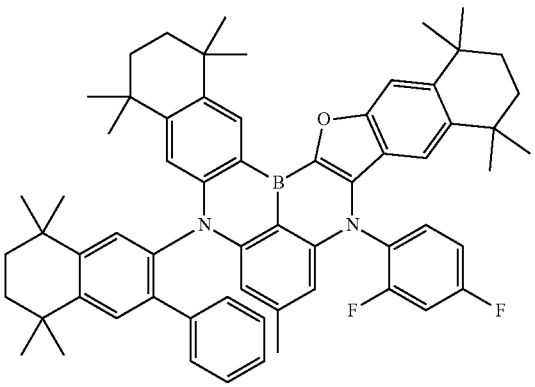
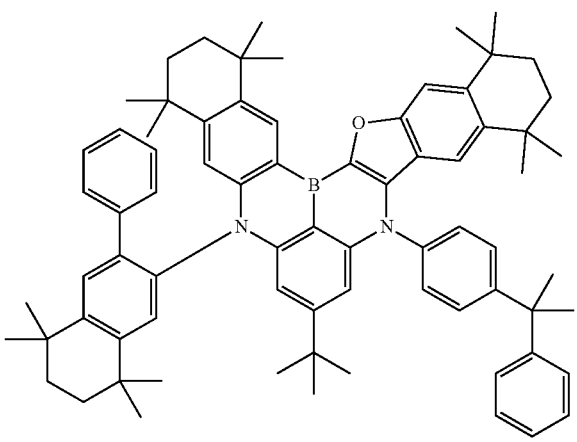

2707
-continued
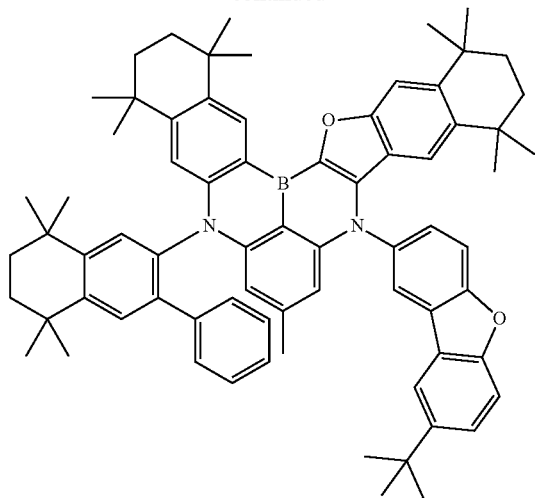
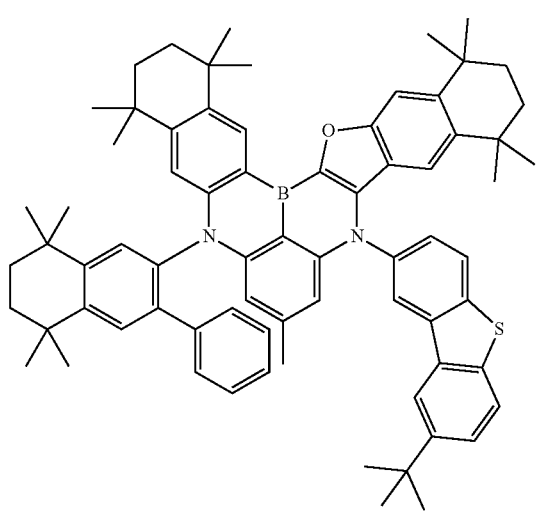
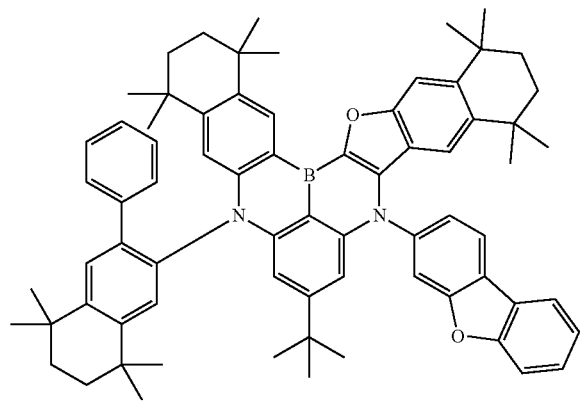
2708
-continued
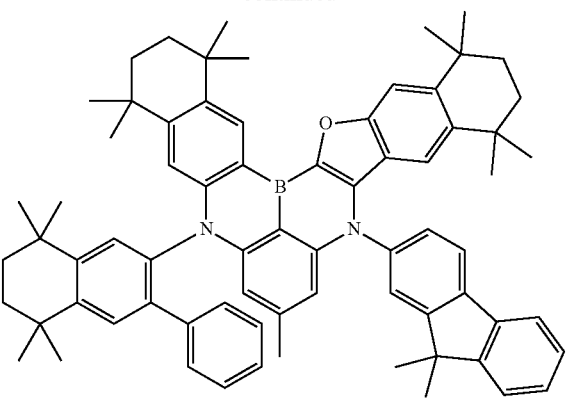
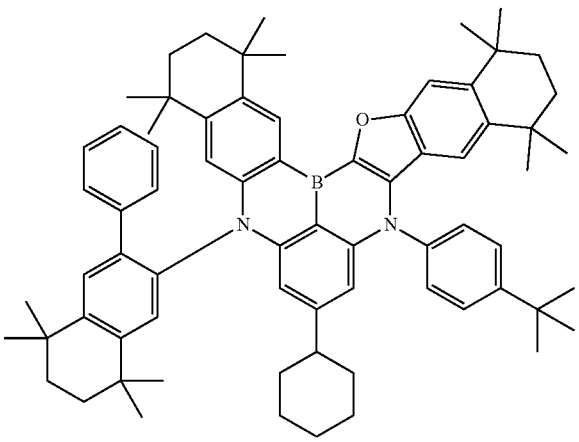
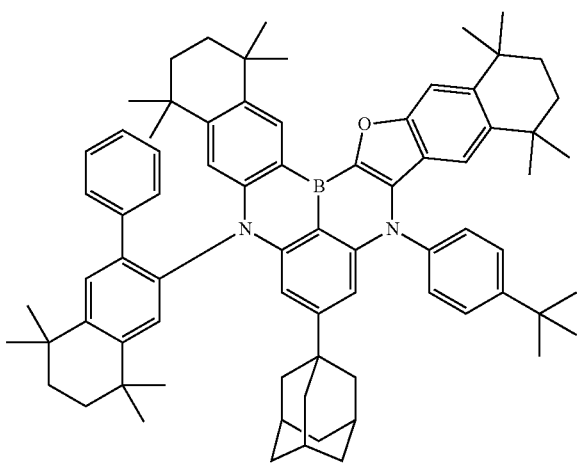

2709
-continued
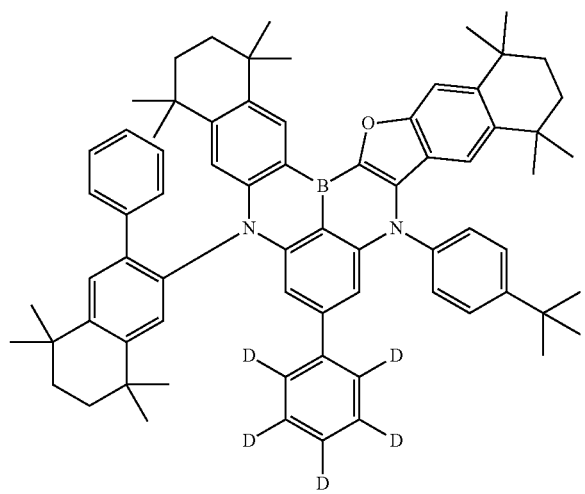
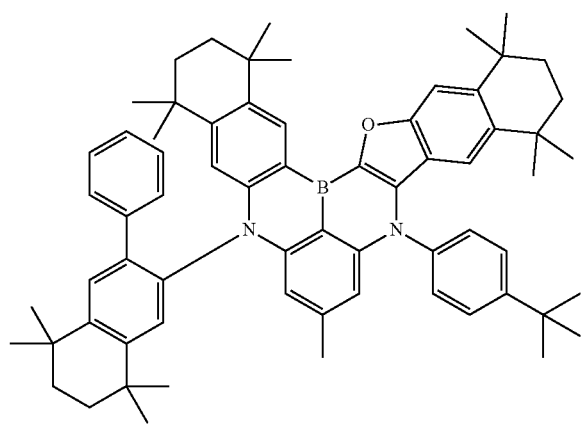
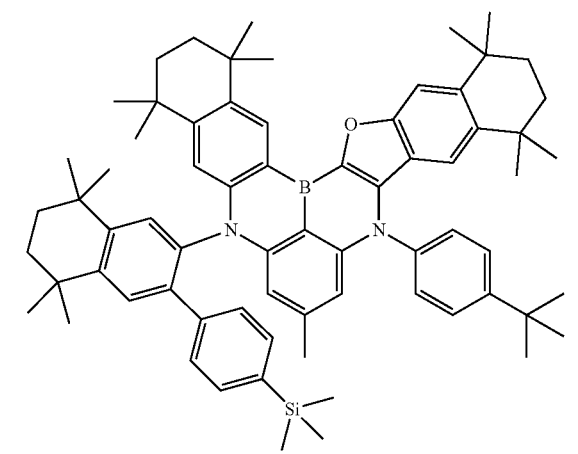
2710
-continued
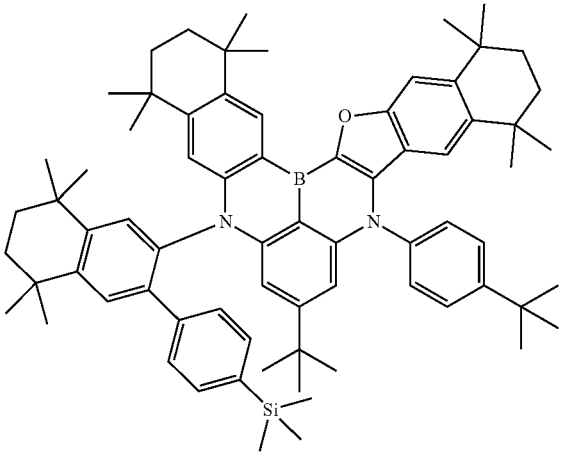
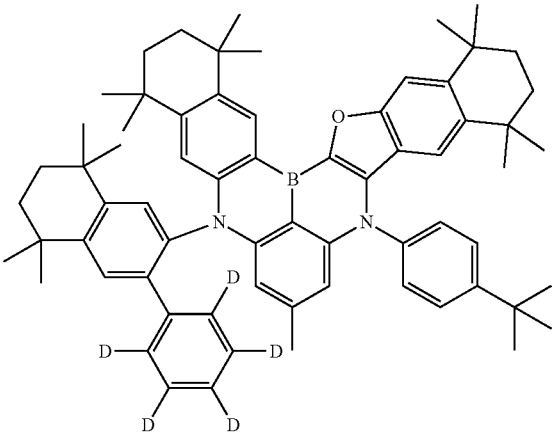
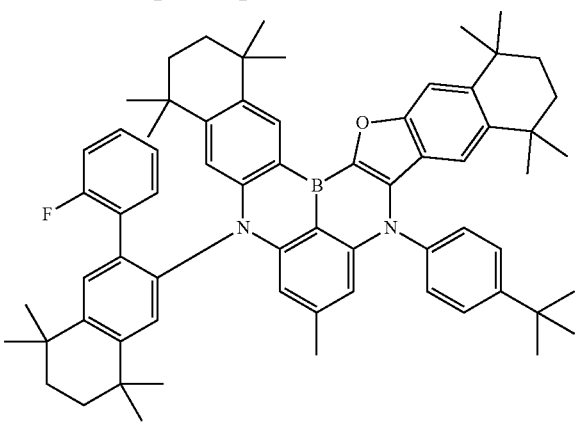
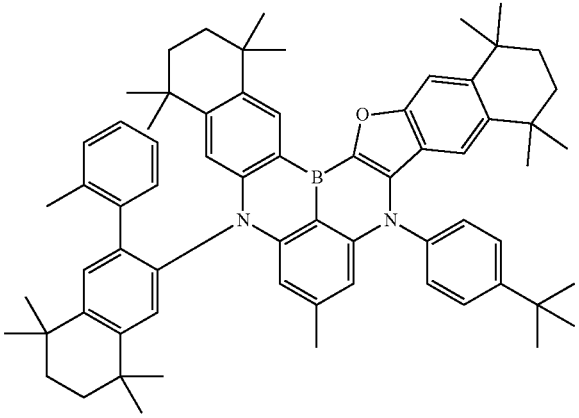

2711
-continued
2712
-continued
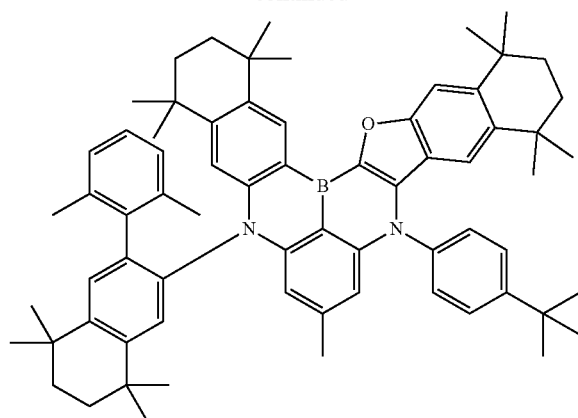
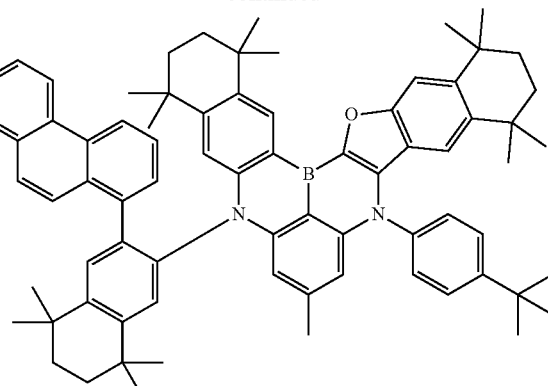
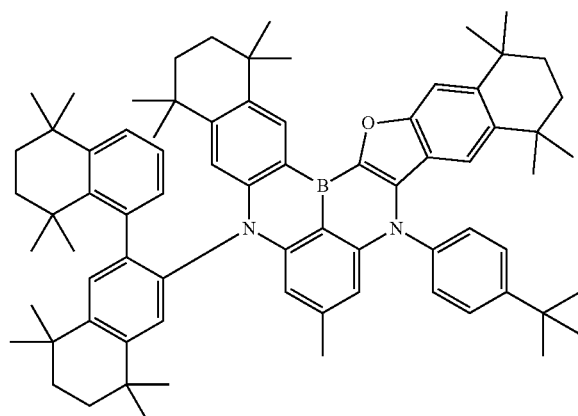
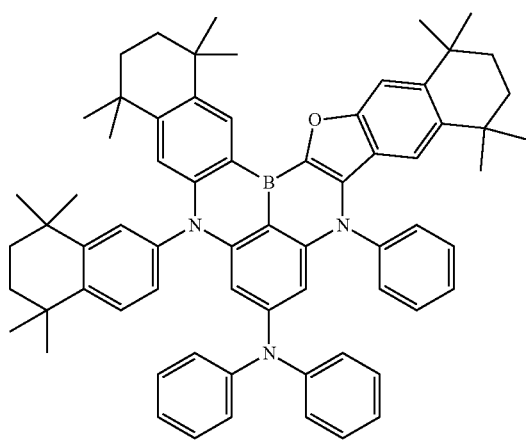
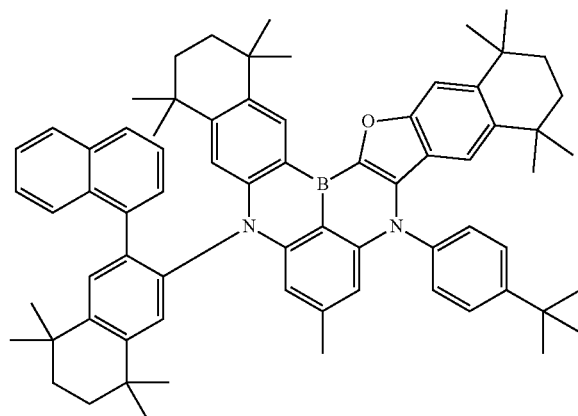
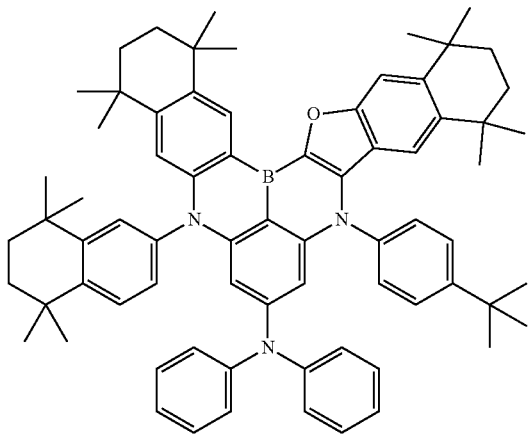

2713
-continued
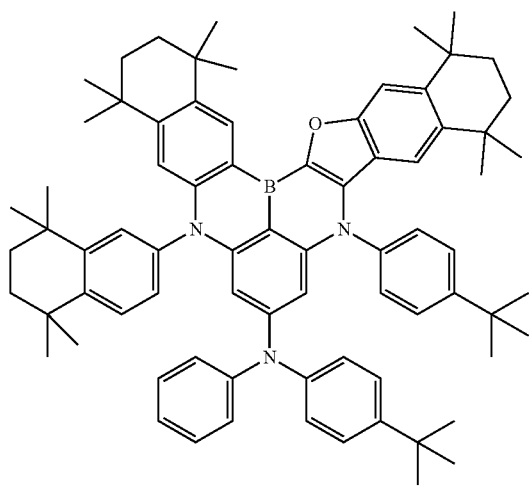
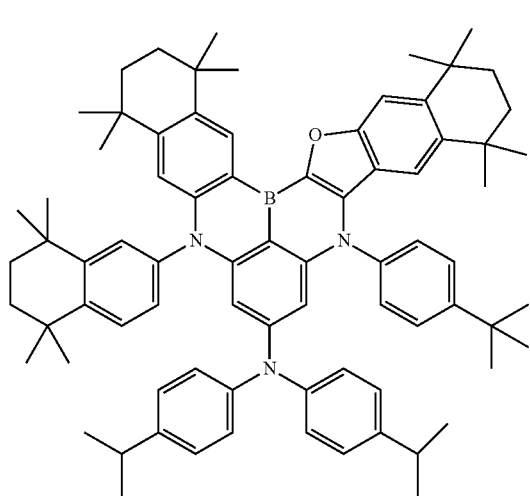
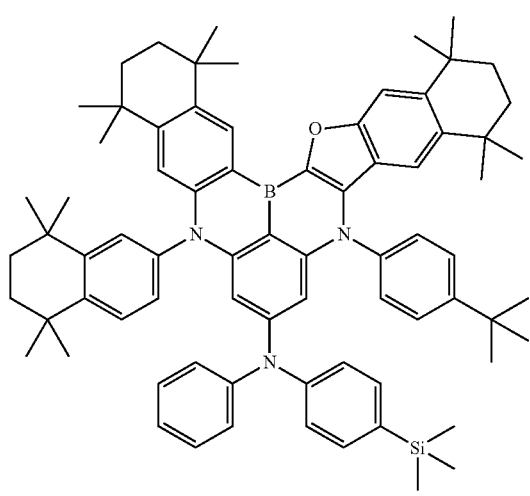
2714
-continued
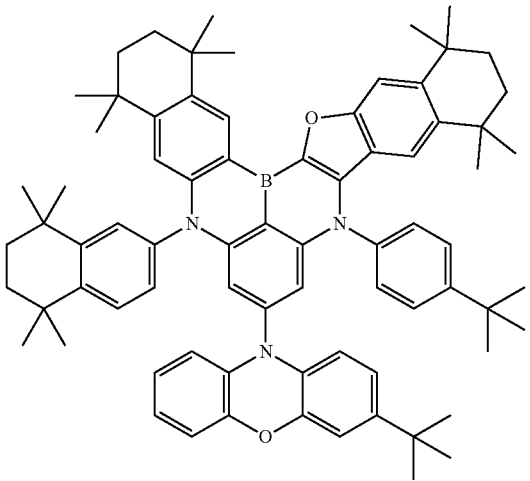
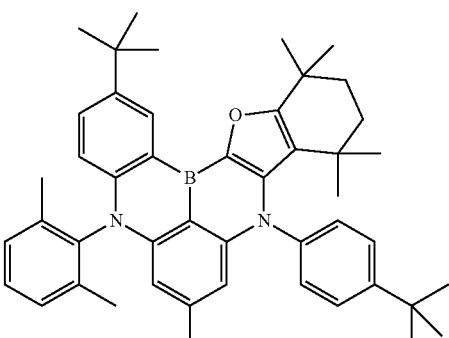
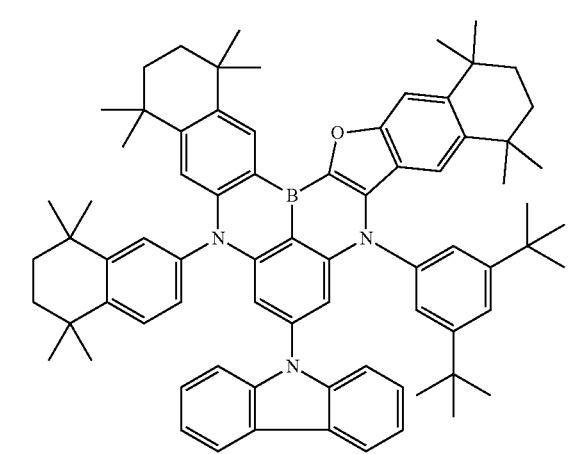

2715
-continued
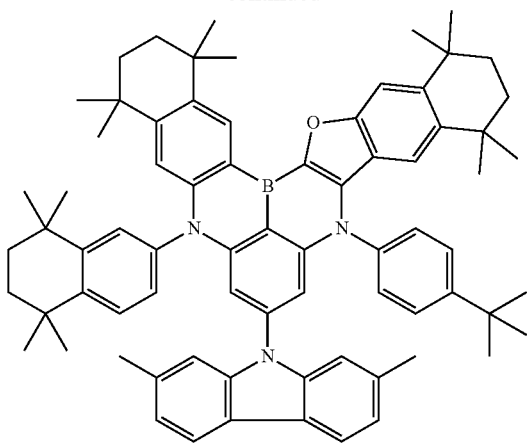
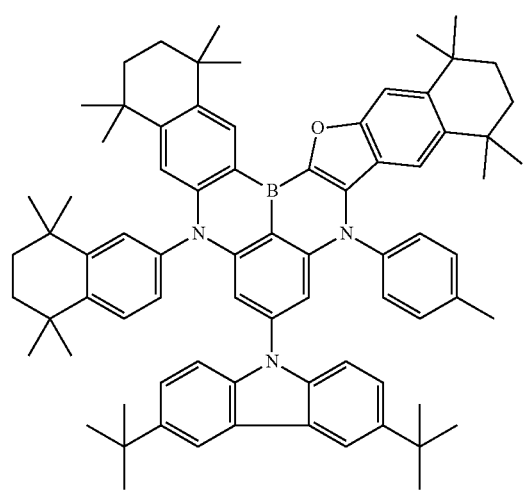
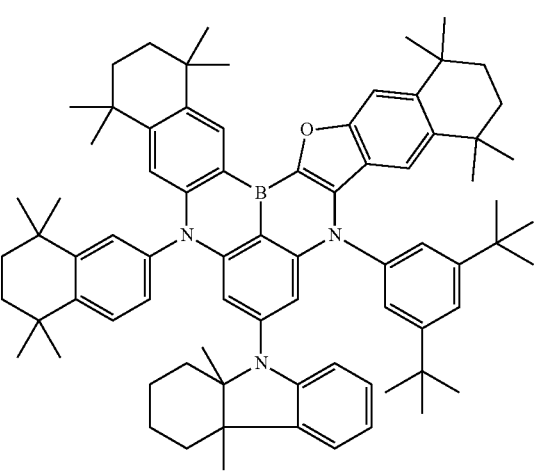
2716
-continued
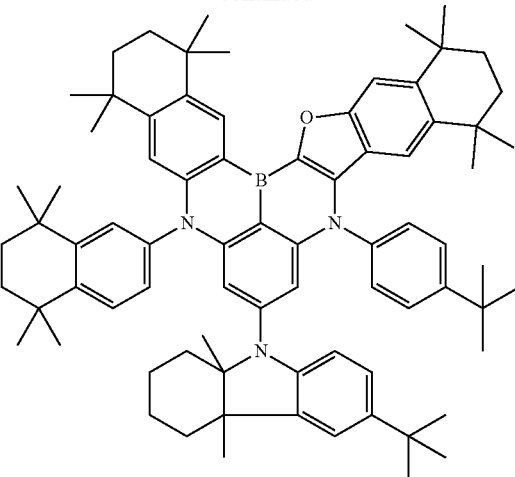
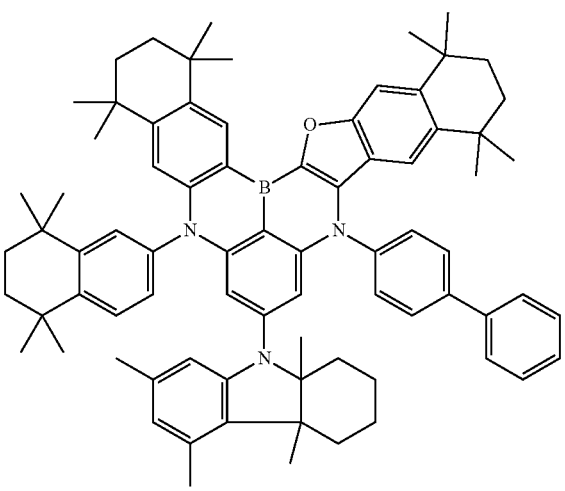
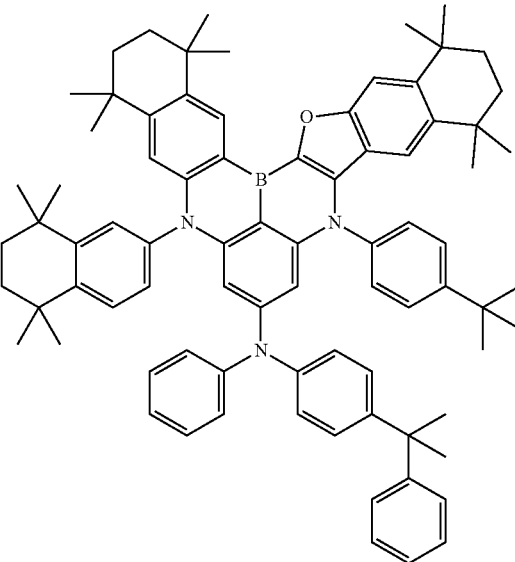

2717
-continued
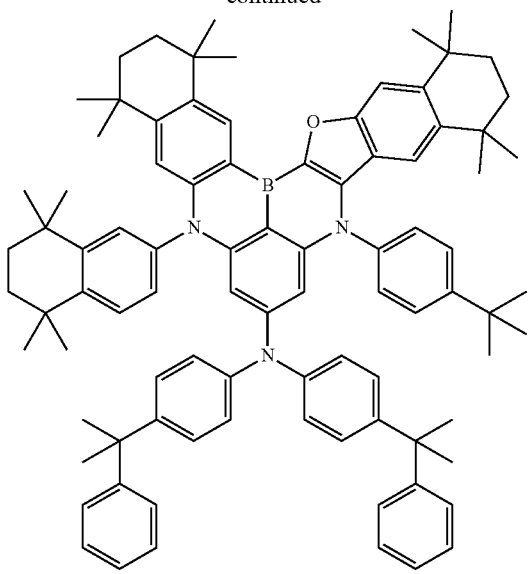
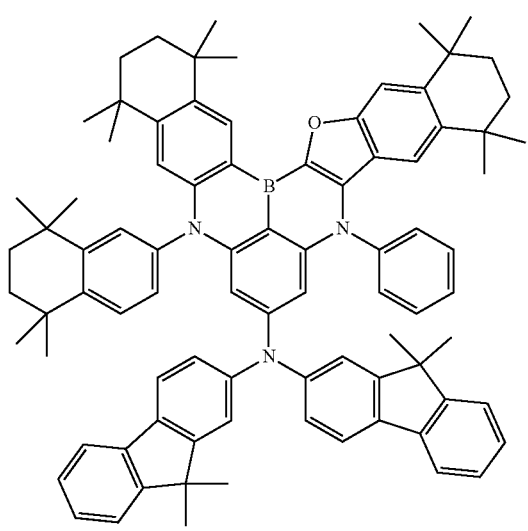
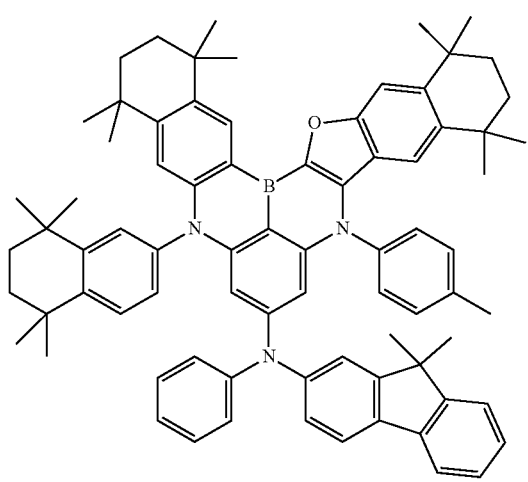
2718
-continued
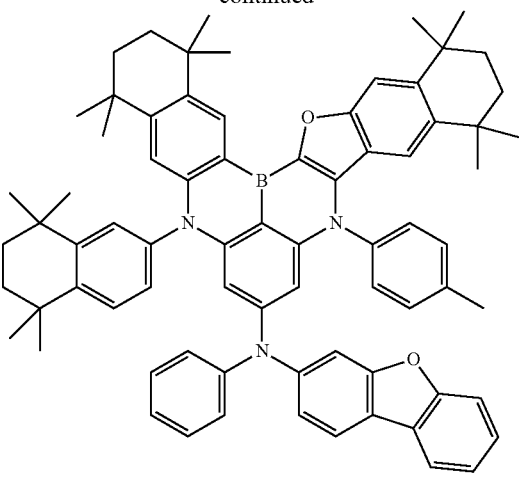
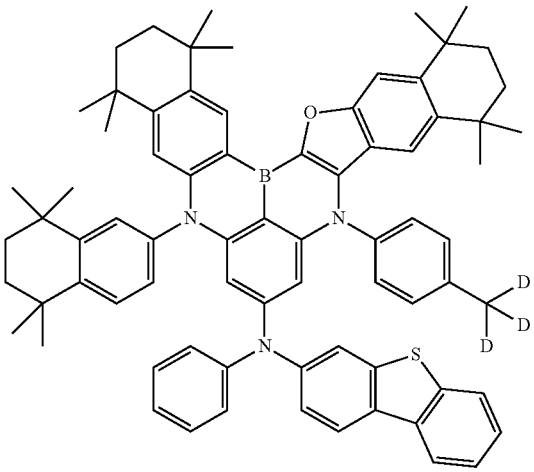
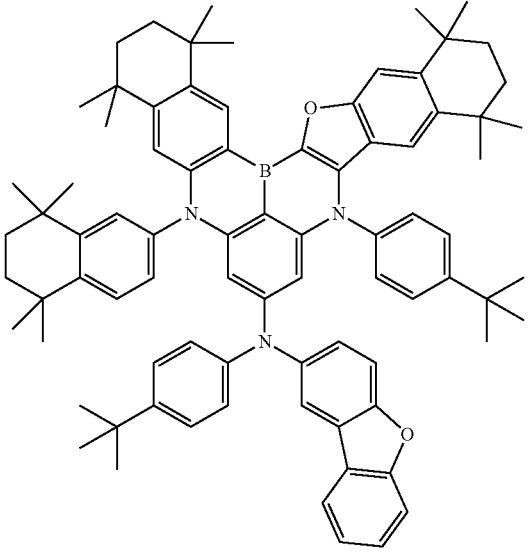

2719
-continued
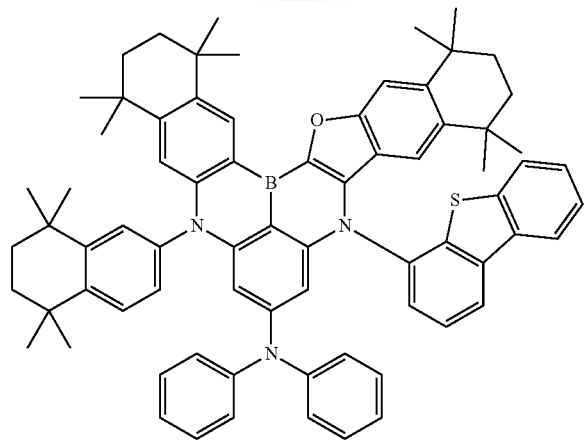
2720
-continued
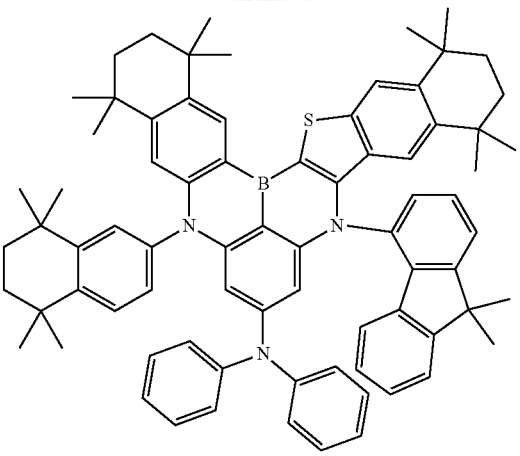
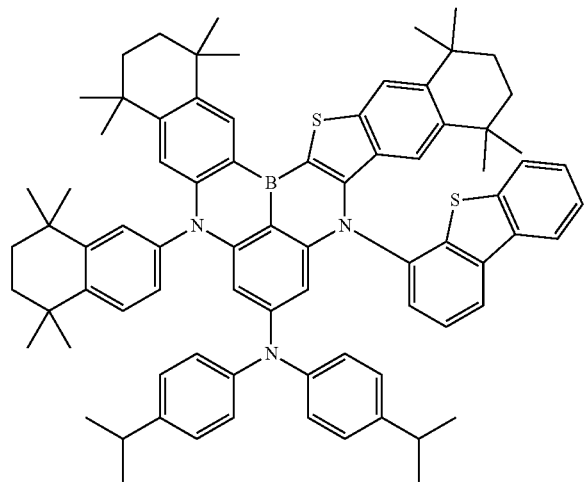
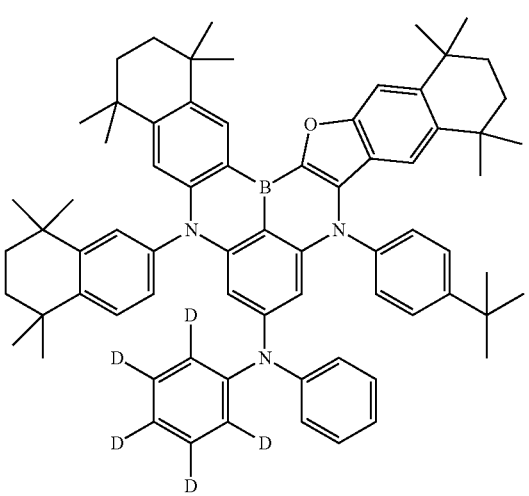
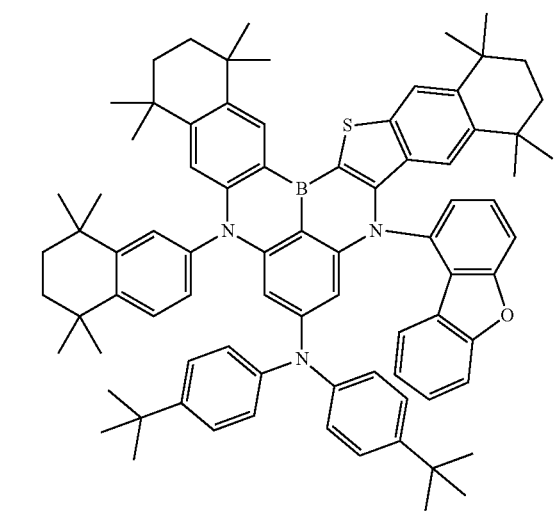
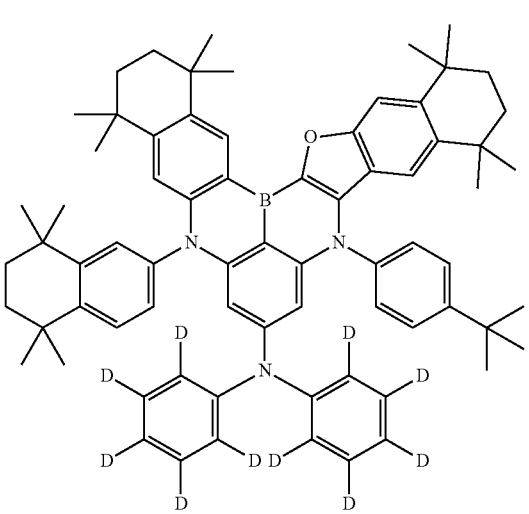

2721
-continued
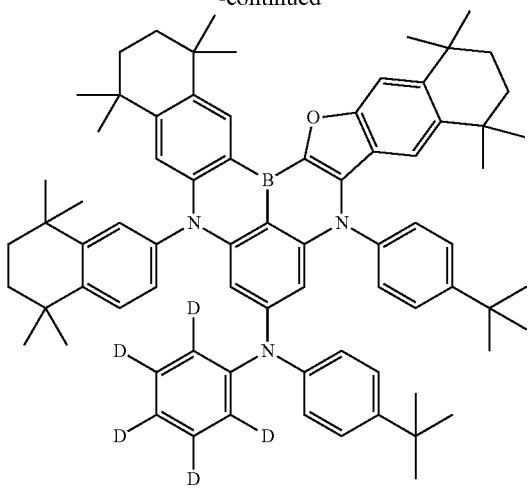
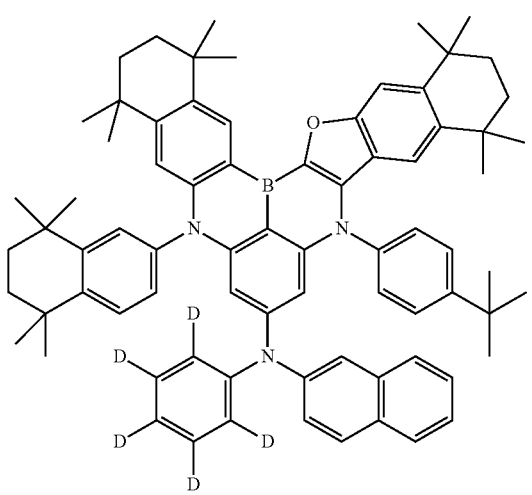
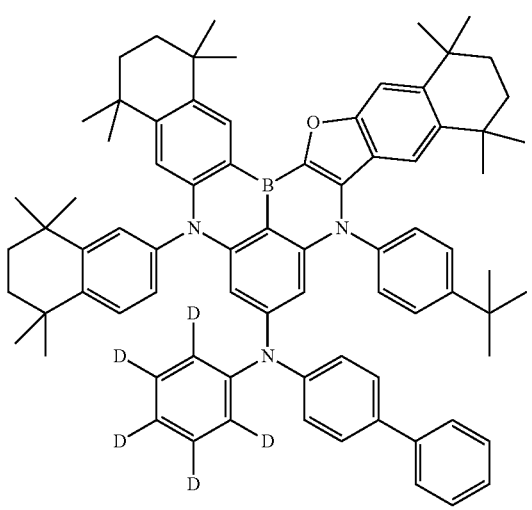
2722
-continued
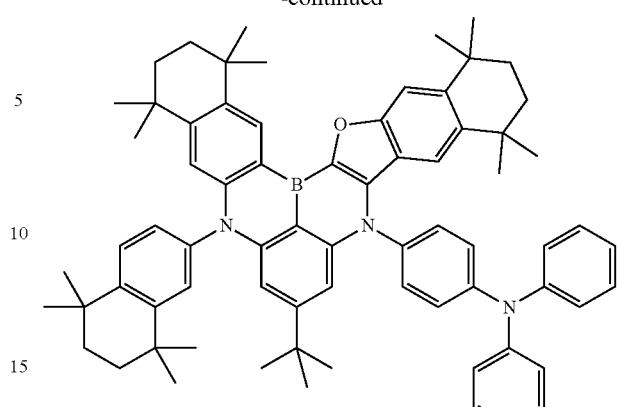
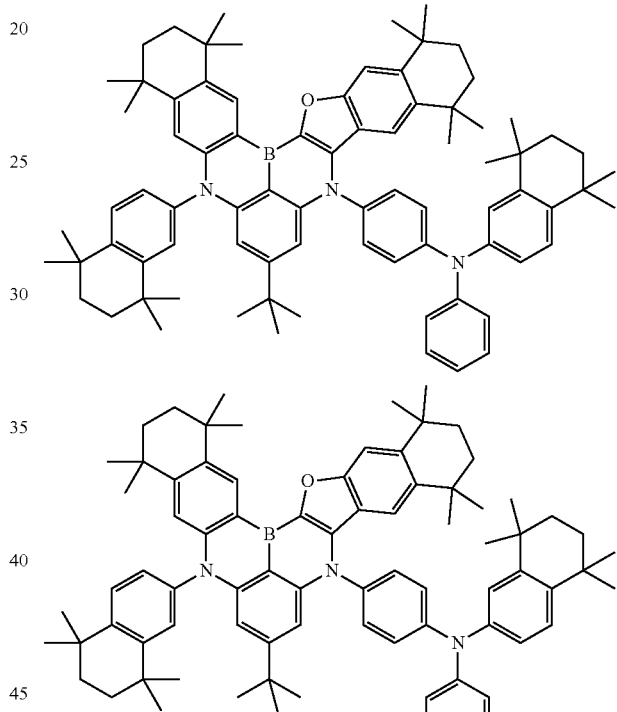
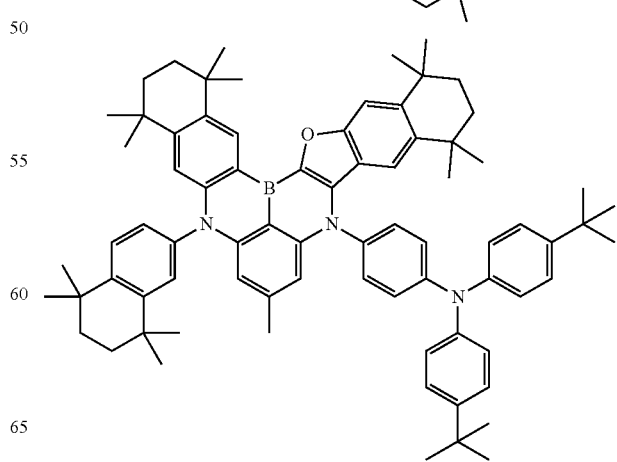

2723
-continued
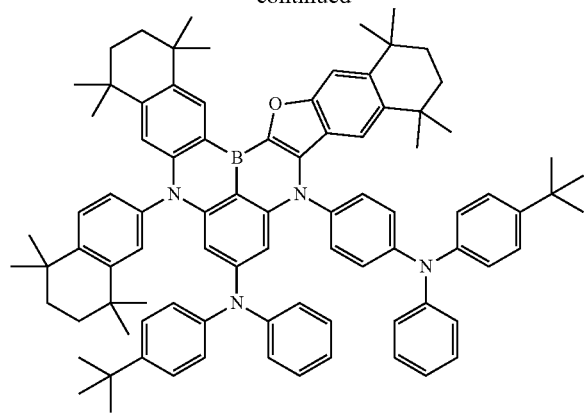
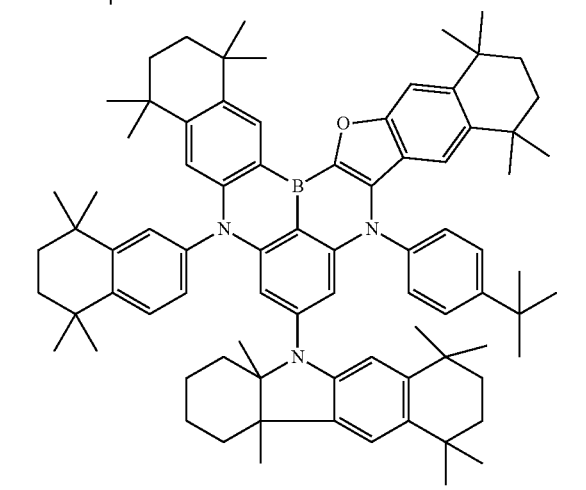
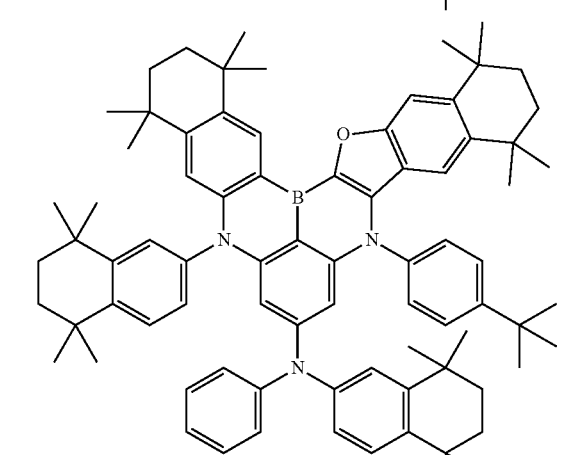
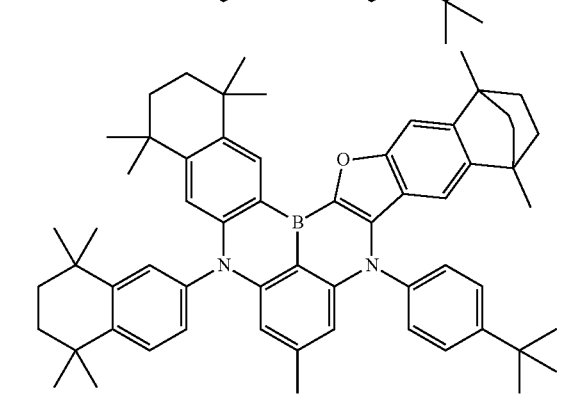
2724
-continued
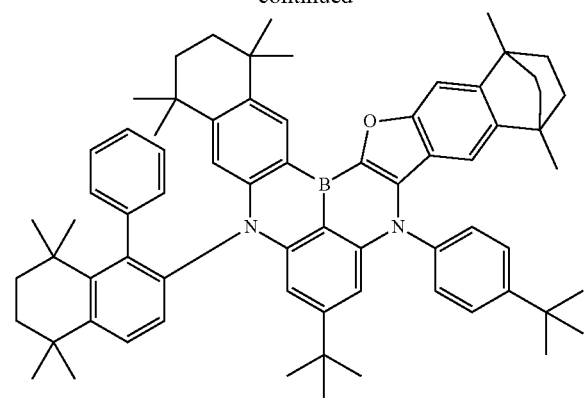
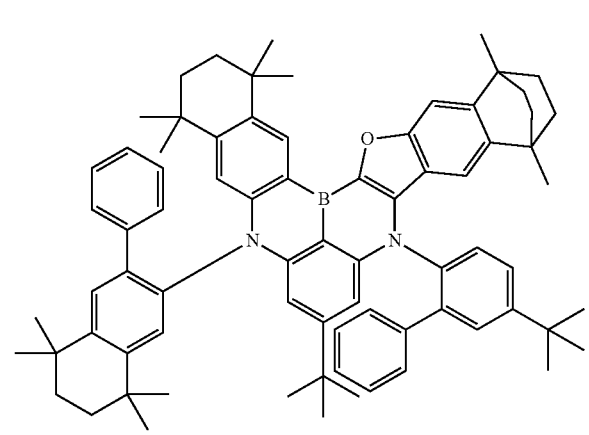
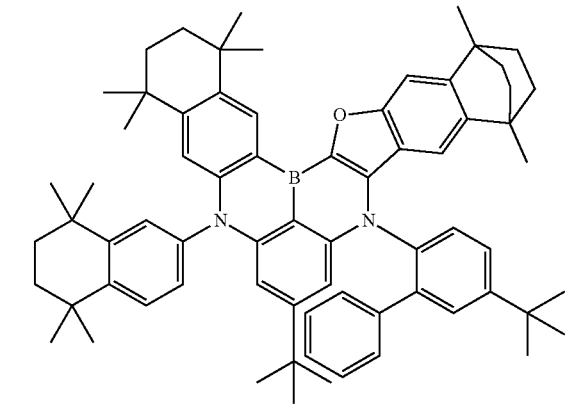
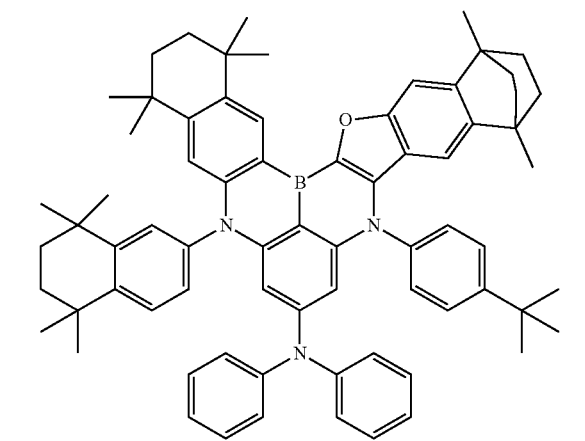

2725
-continued
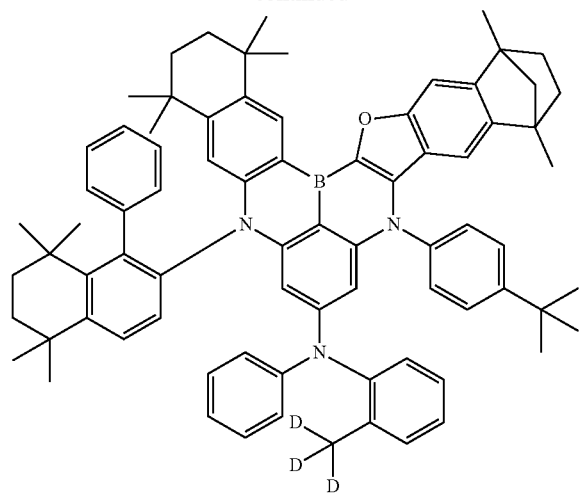
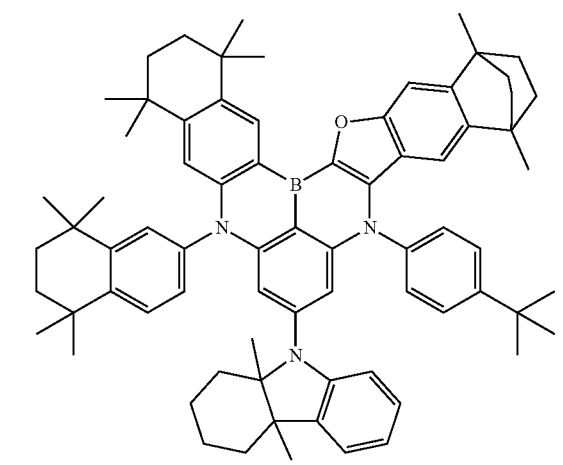
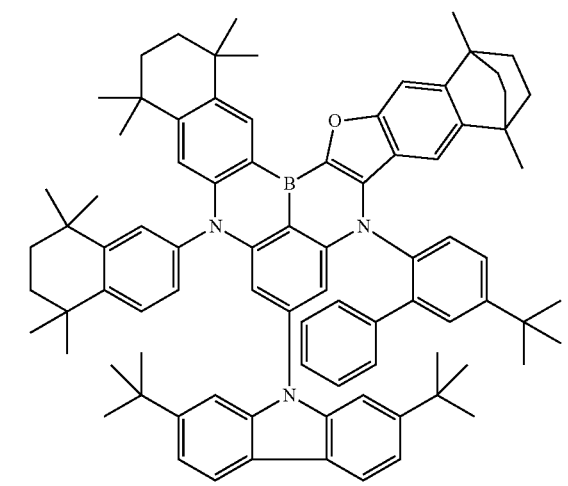
2726
-continued
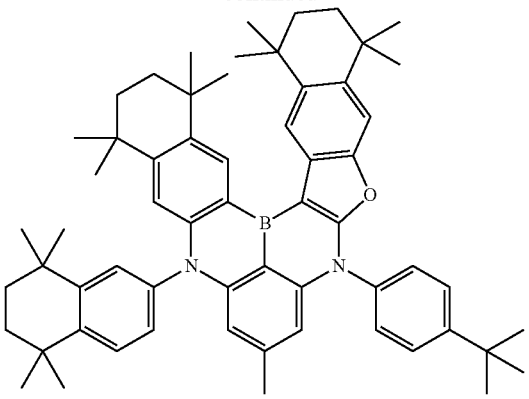
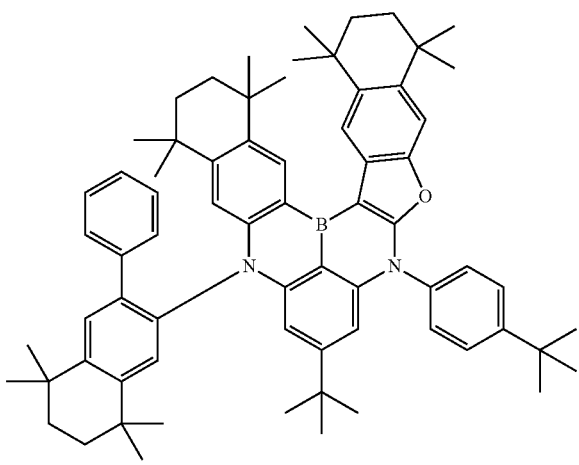
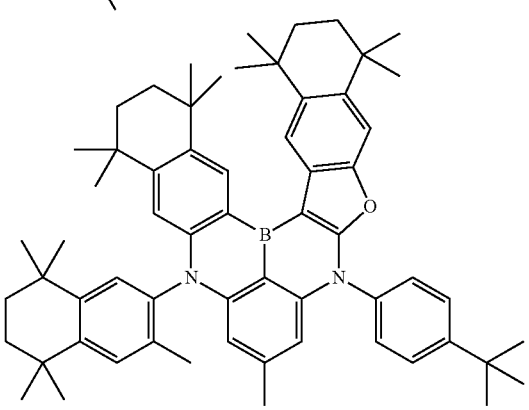
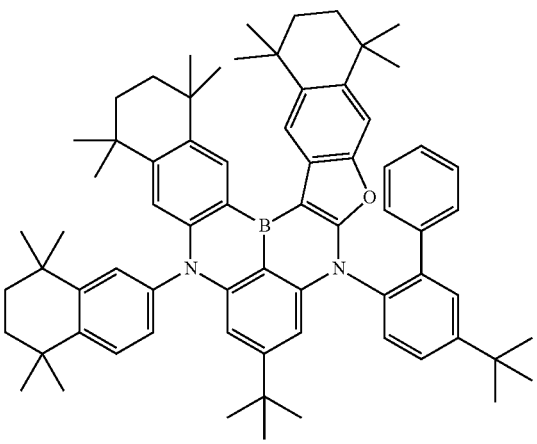

2727
-continued
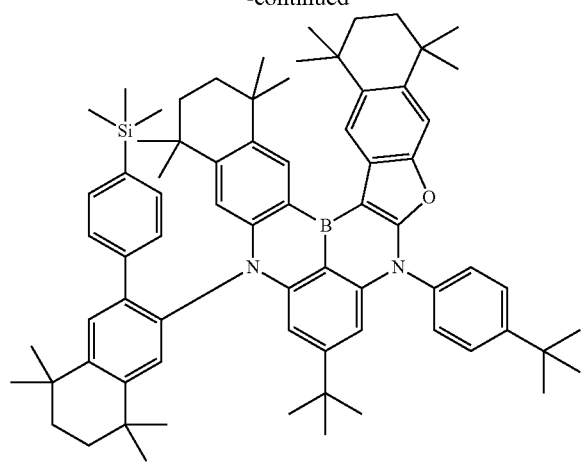
2728
-continued
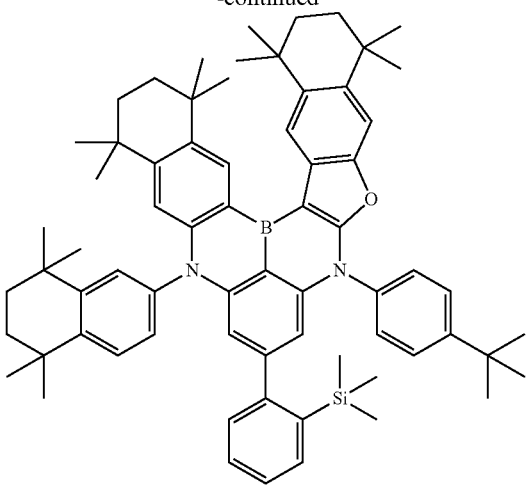
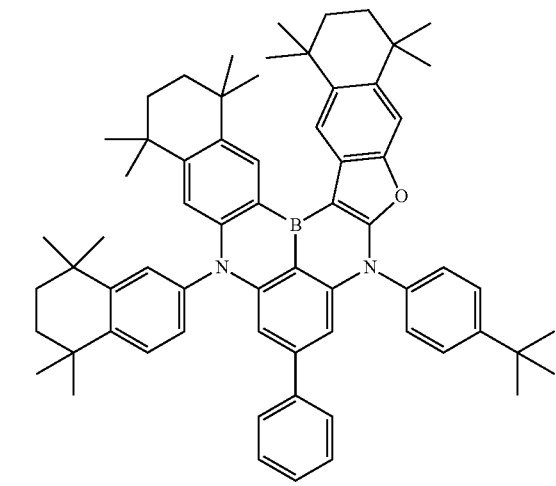
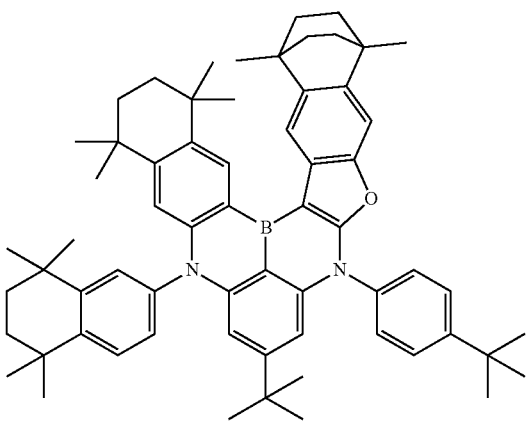
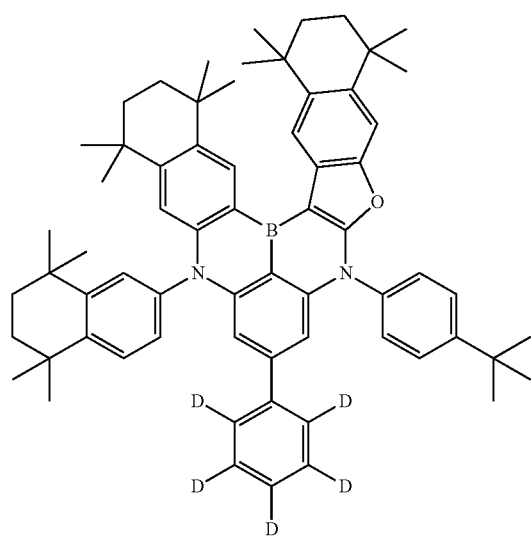
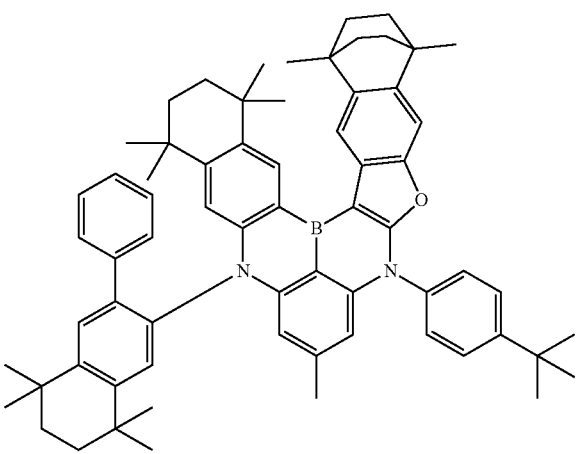

2729
-continued
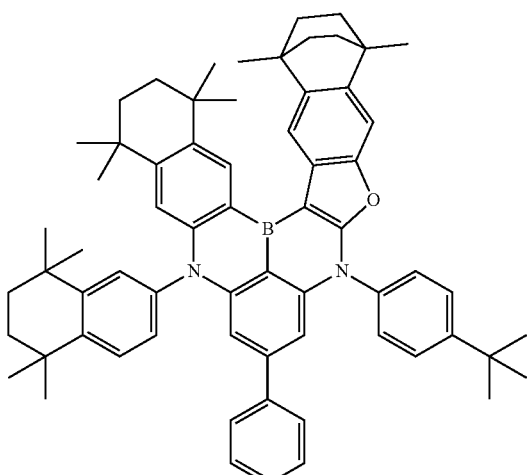
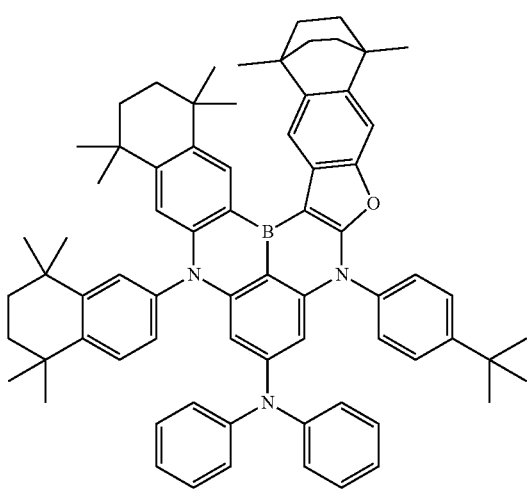
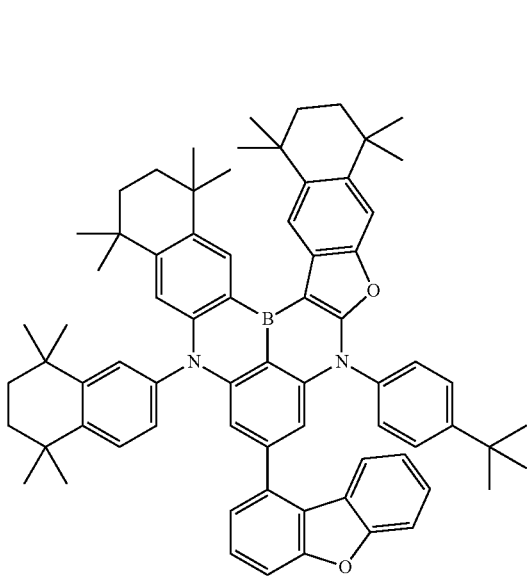
2730
-continued
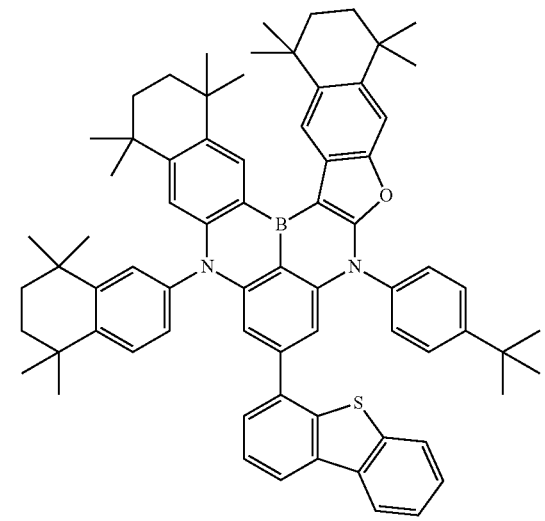
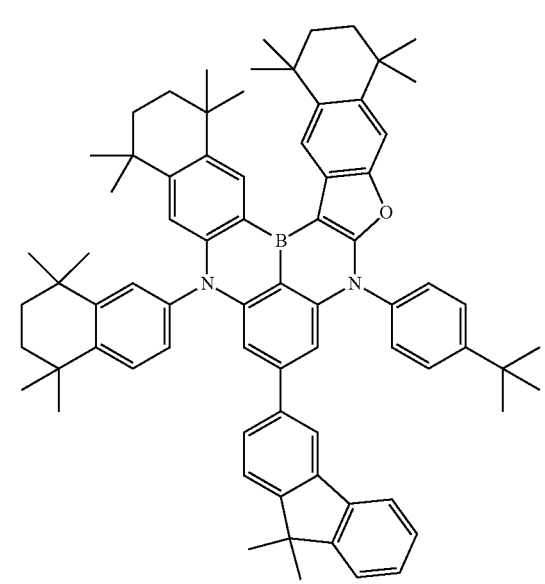

| 2731 -continued | 2732 -continued |
|---|---|
| 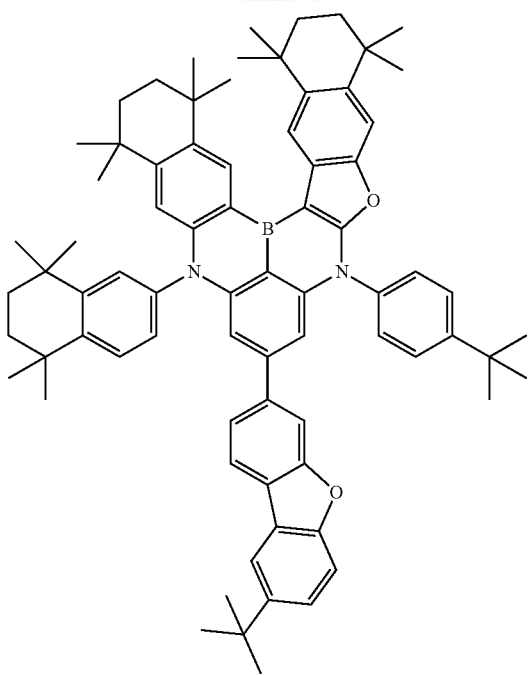 | 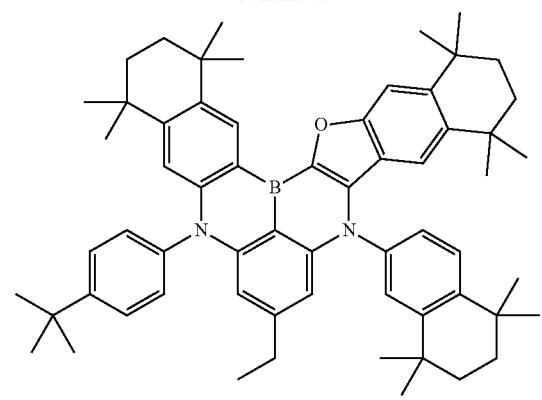 |
| | 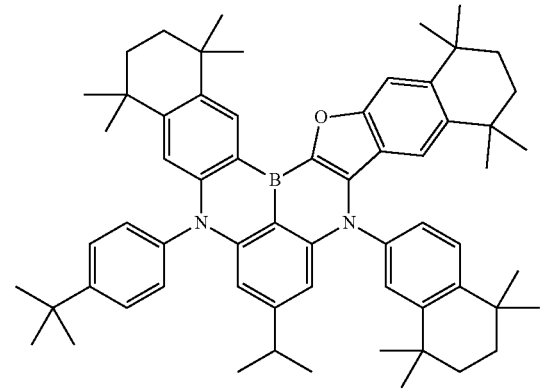 |
| 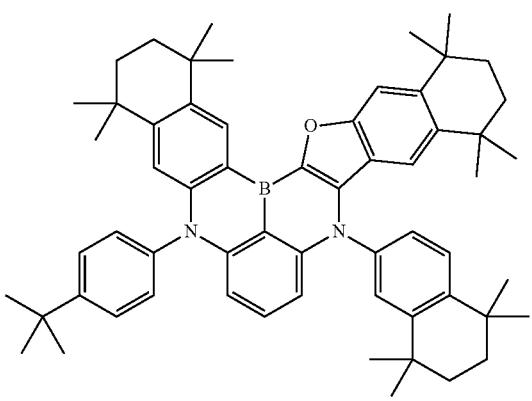 | 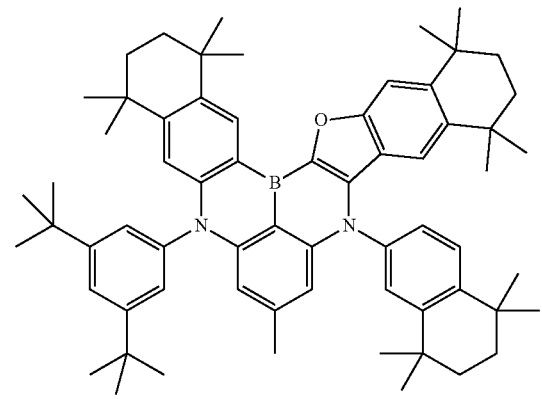 |
| 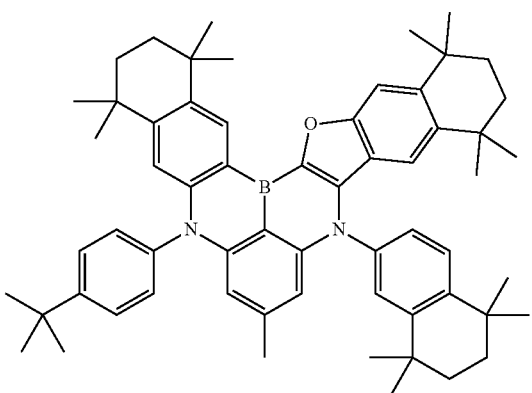 | 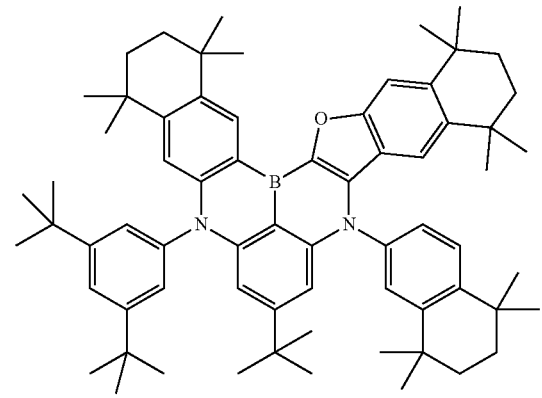 |

2733
-continued
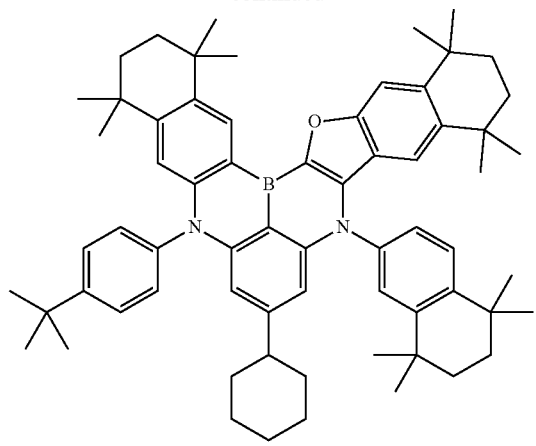
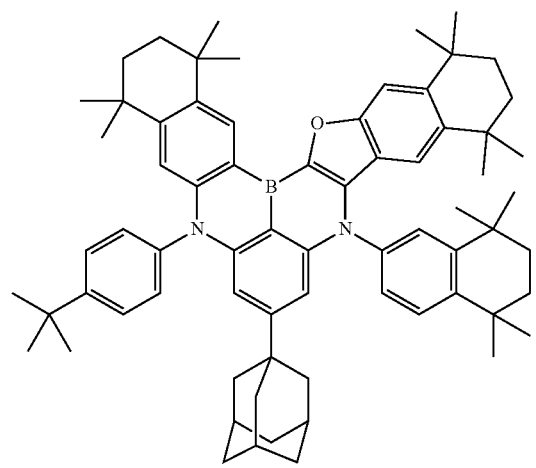
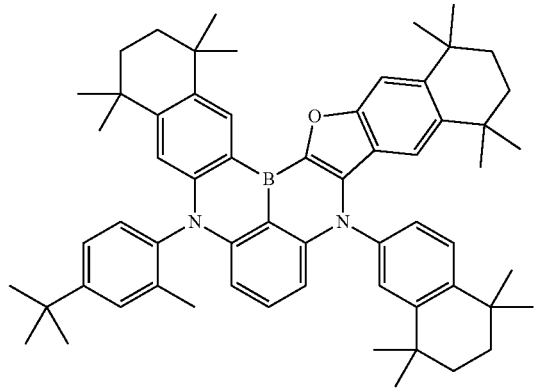
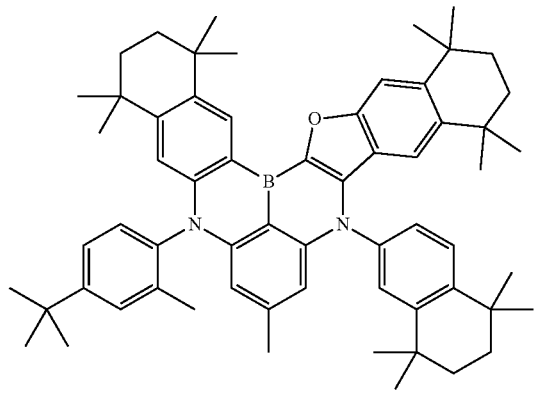
2734
-continued
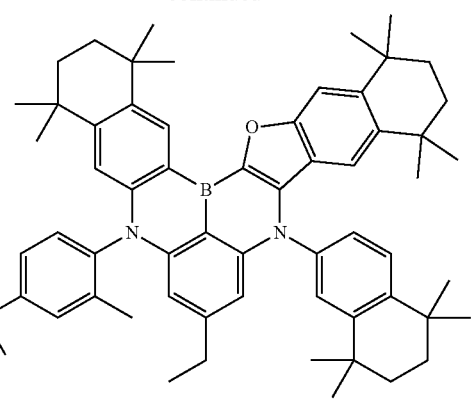
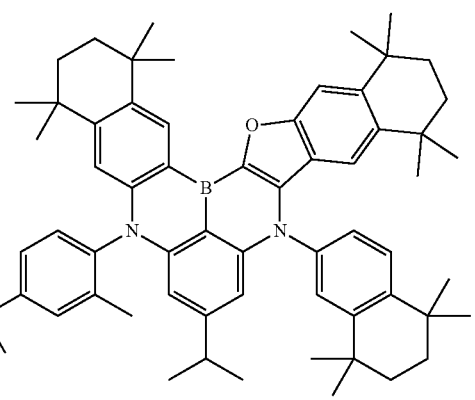
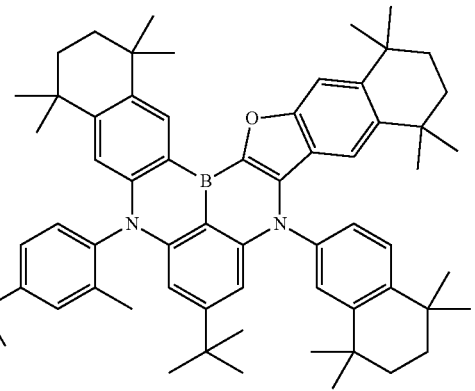
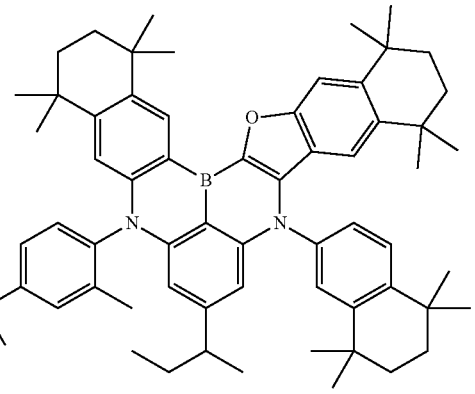

2735
-continued
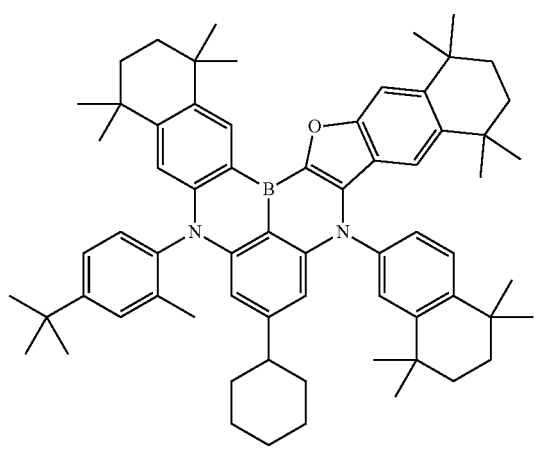
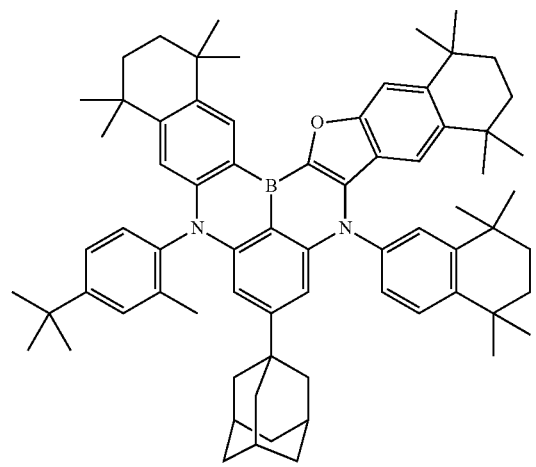
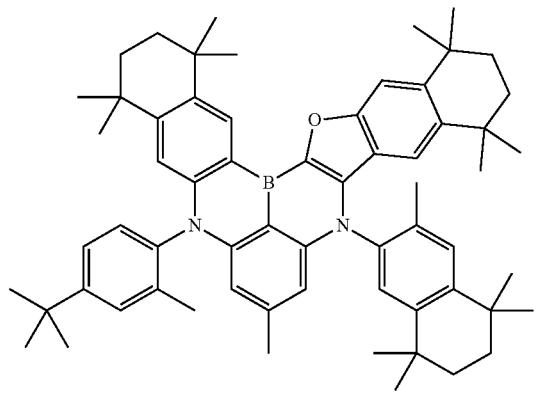
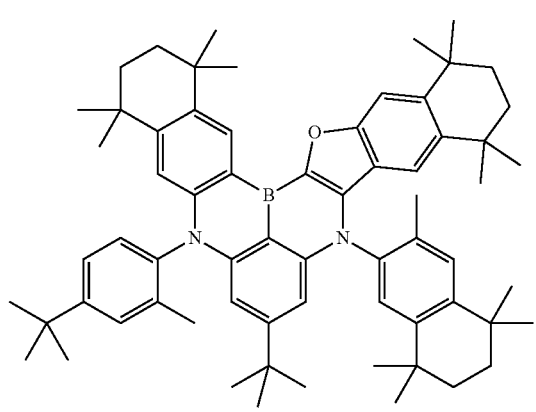
2736
-continued
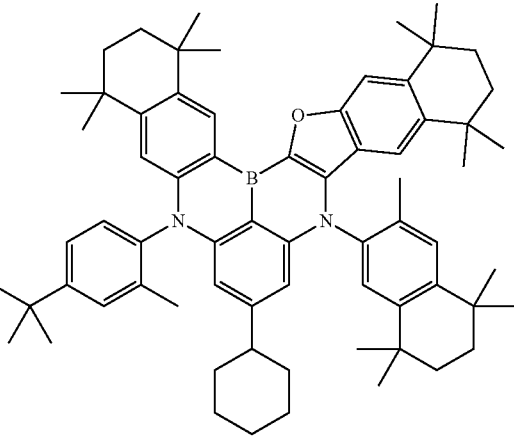
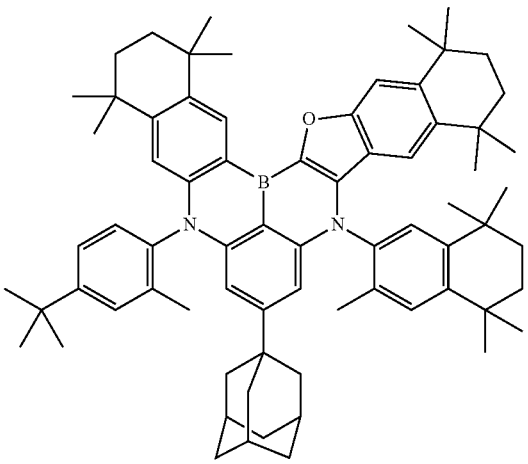
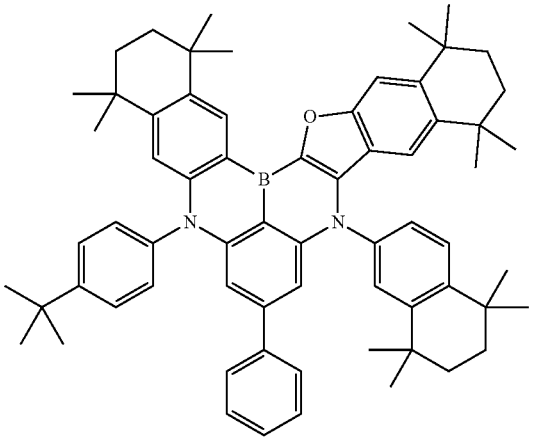

2737
-continued
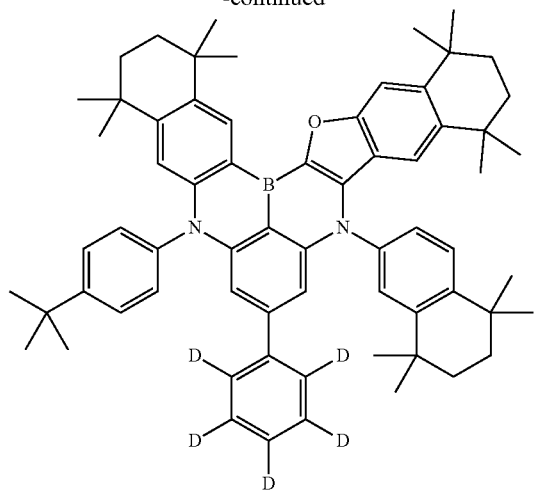
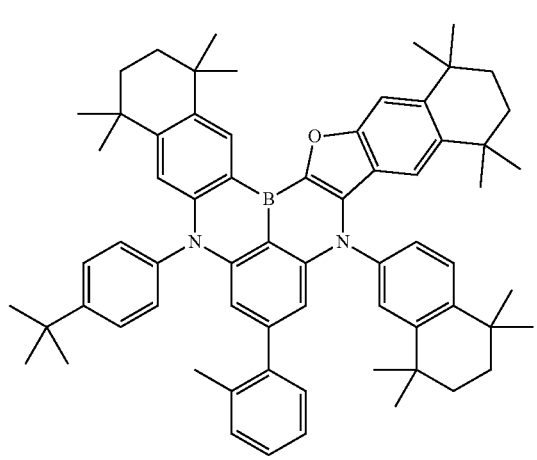
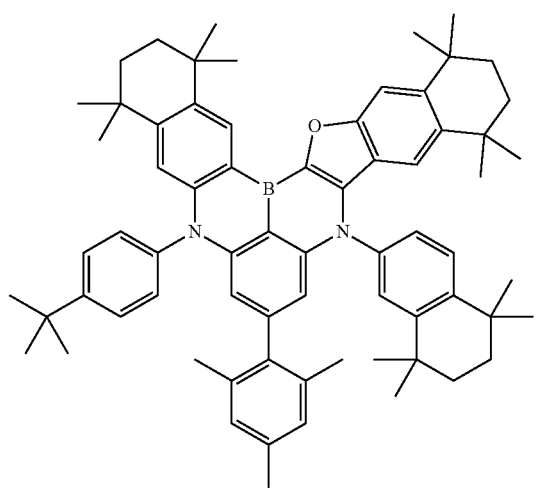
2738
-continued
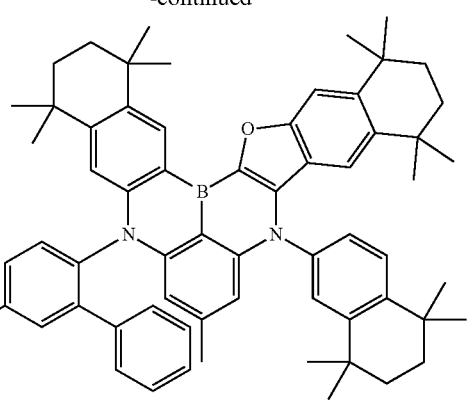
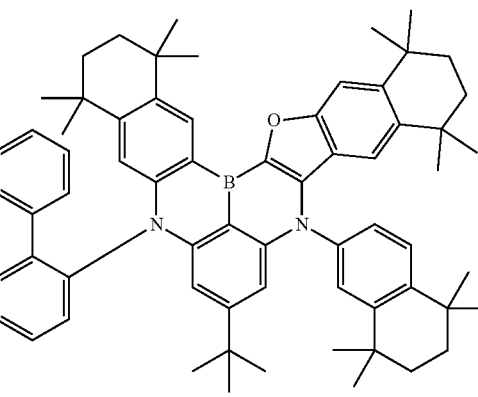
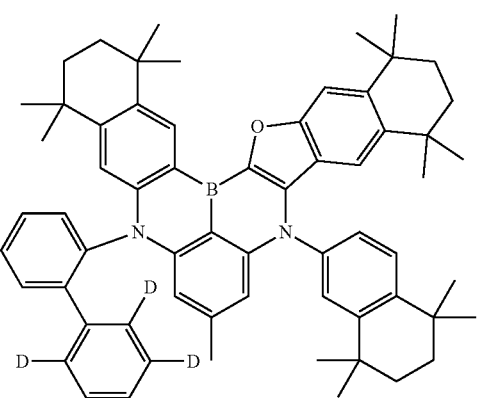
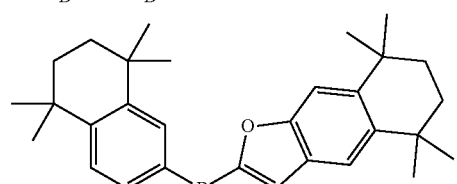
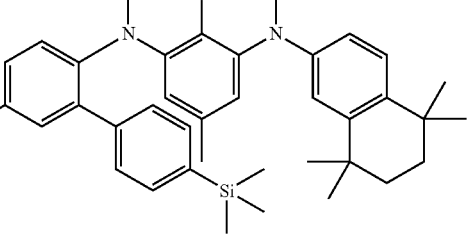

| 2739 -continued | 2740 -continued |
|---|---|
| 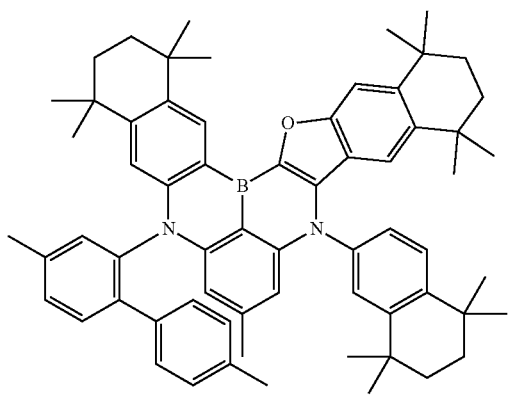 | 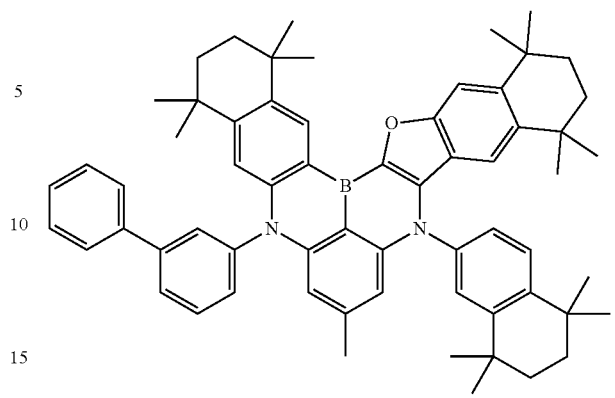 |
| 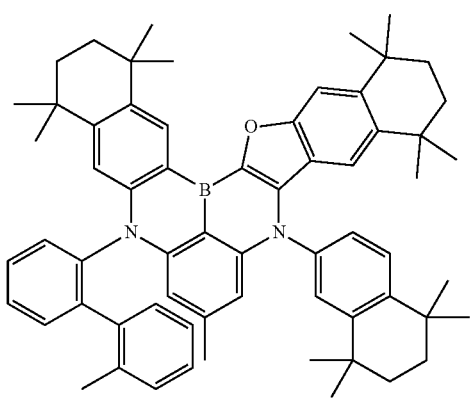 | 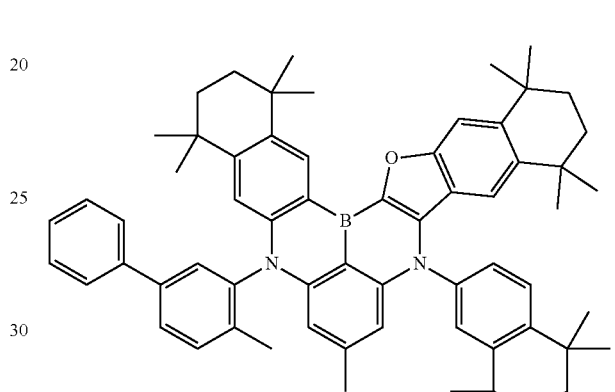 |
| 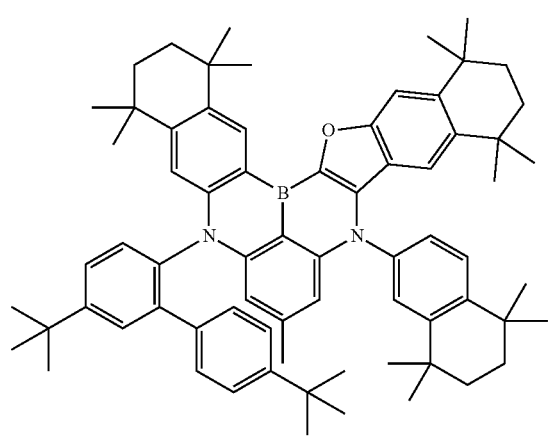 | 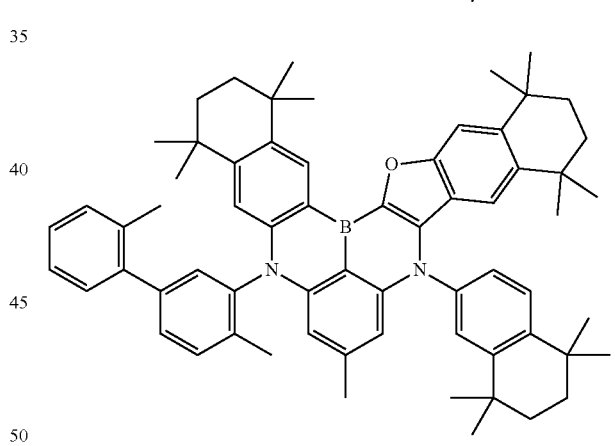 |
| 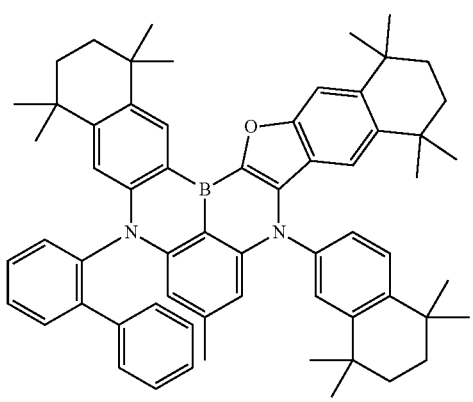 | 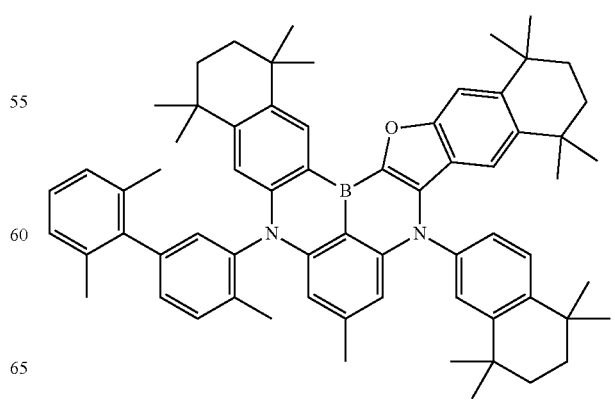 |

2741
-continued
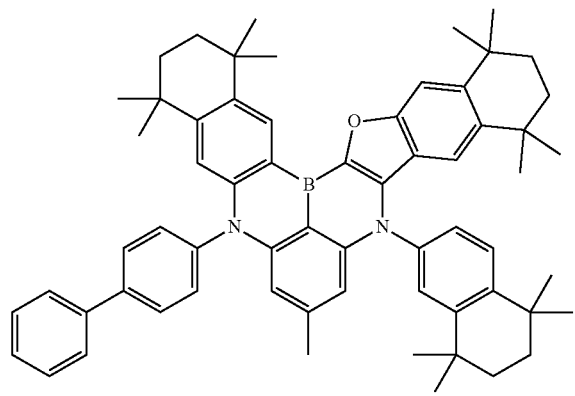
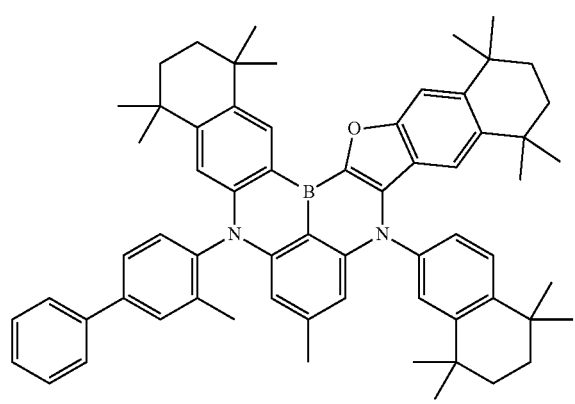
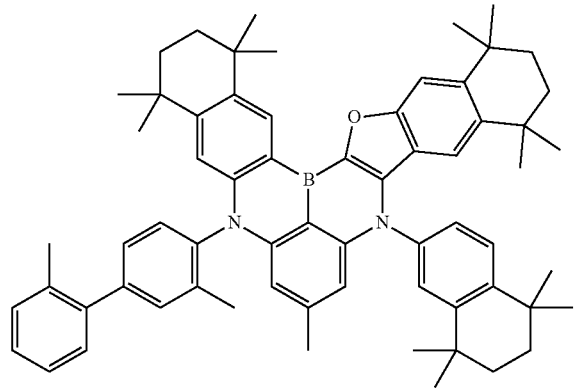
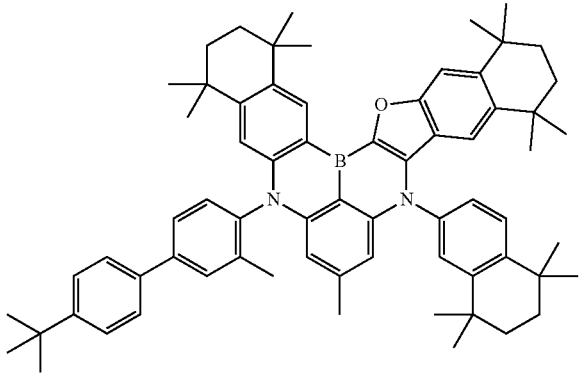
2742
-continued
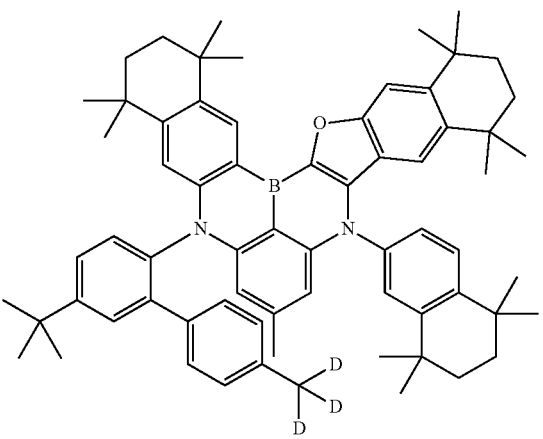
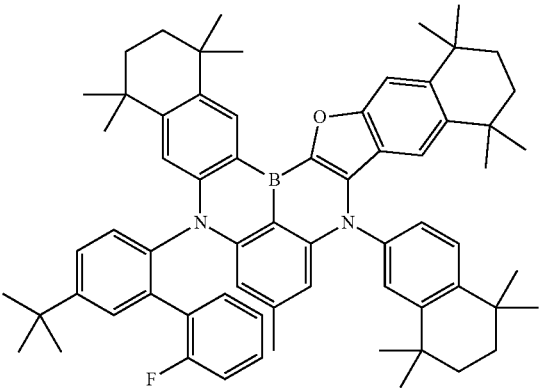
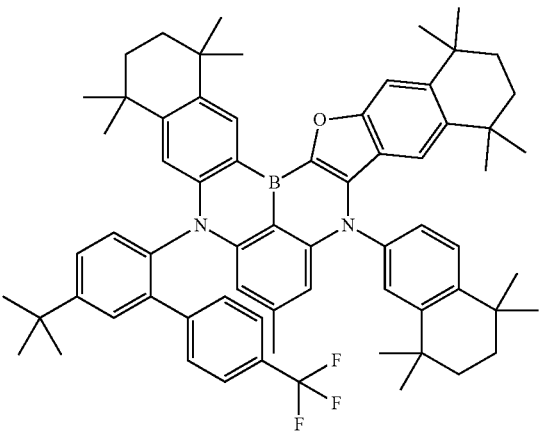
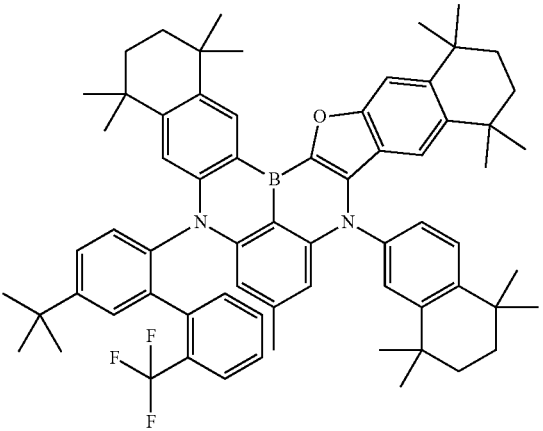

2743
-continued
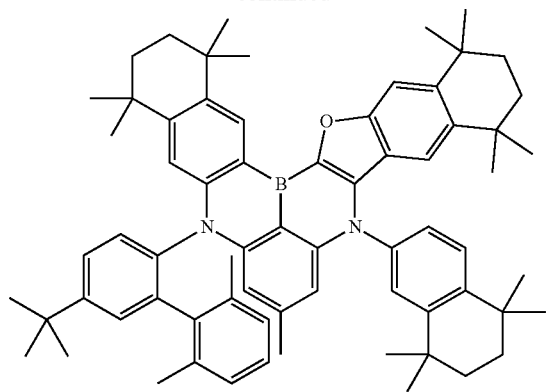
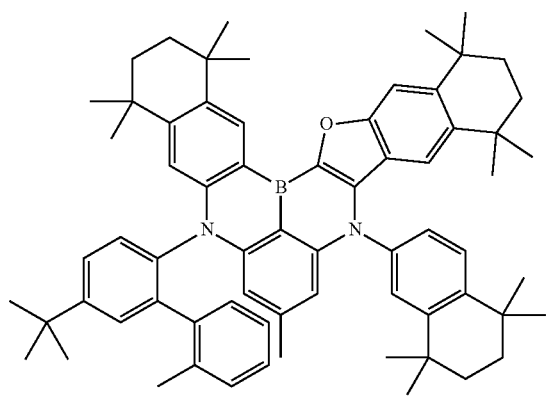
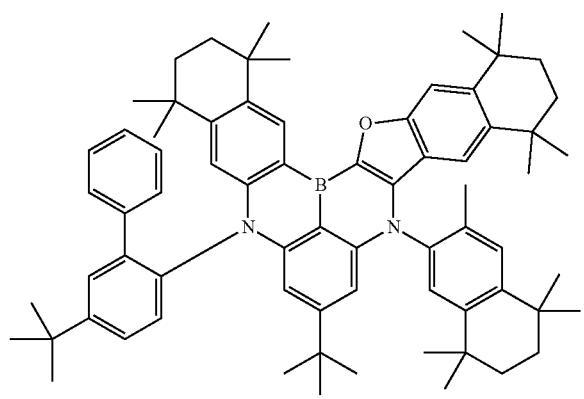
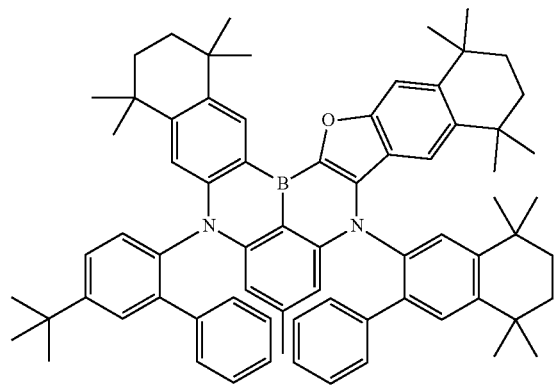
2744
-continued
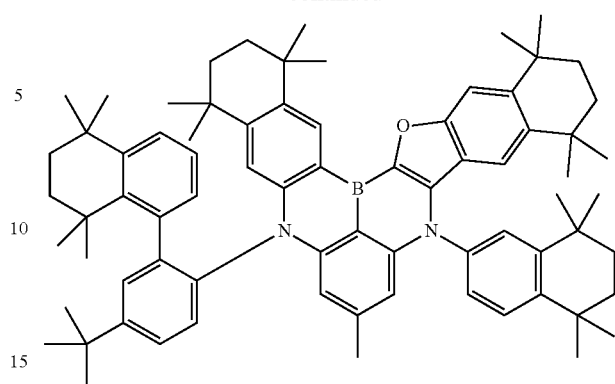
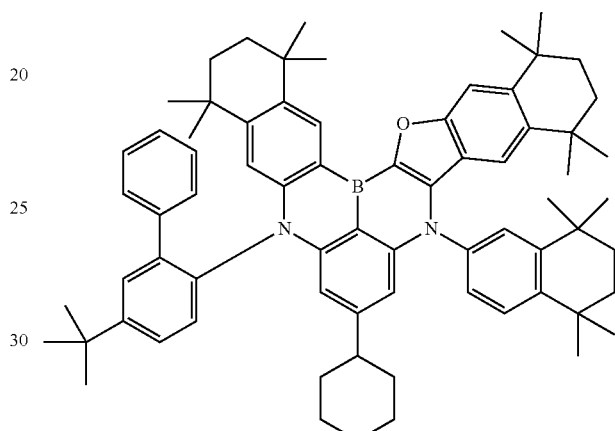
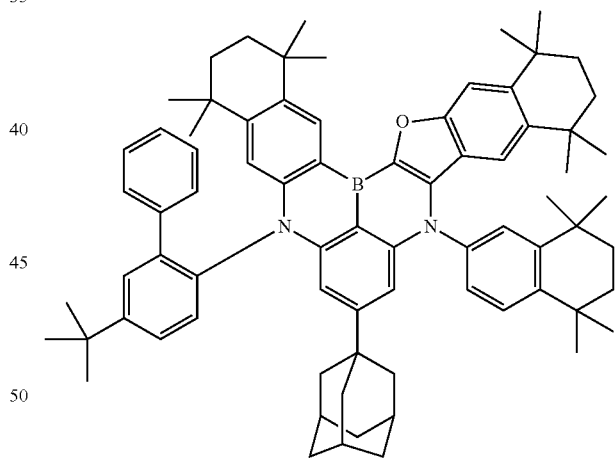
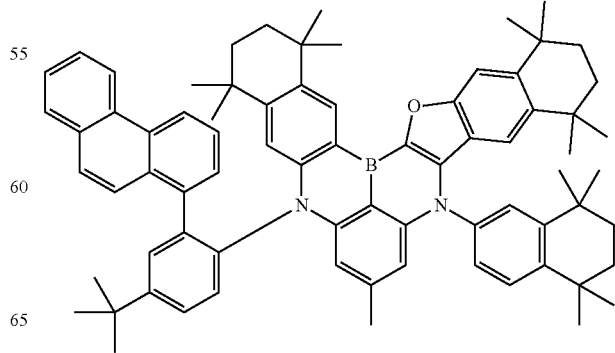

2745
-continued
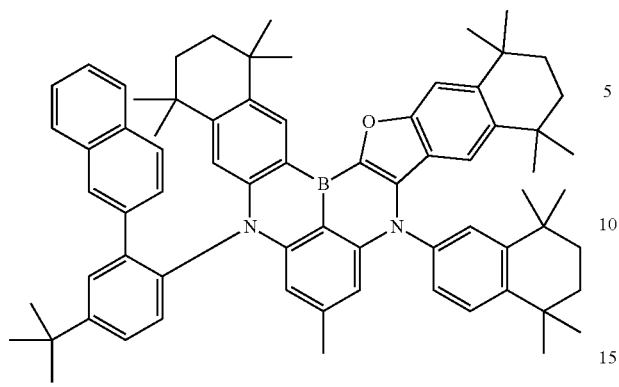
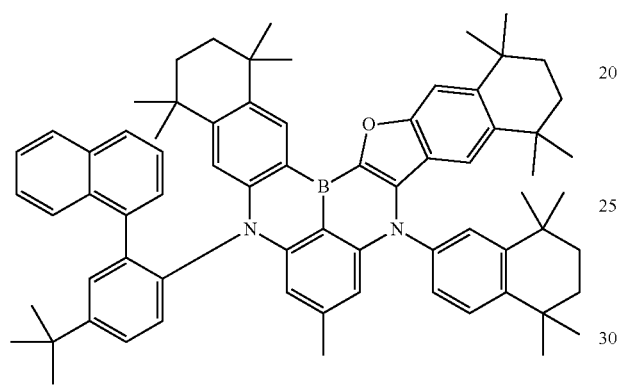
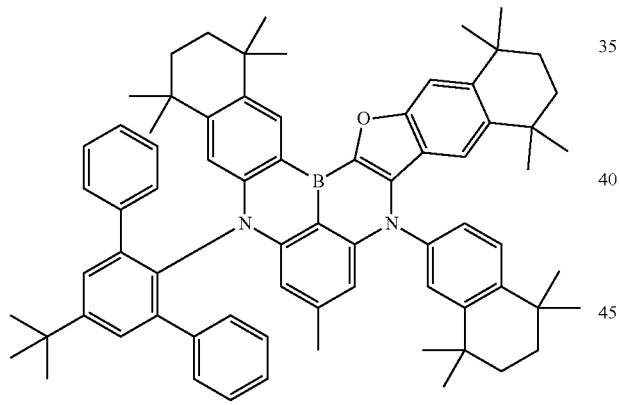
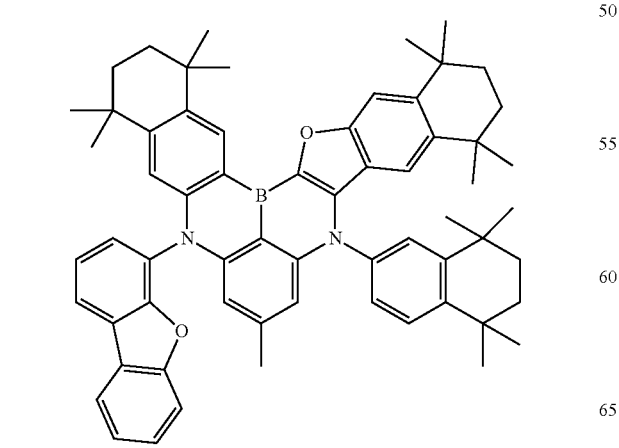
2746
-continued
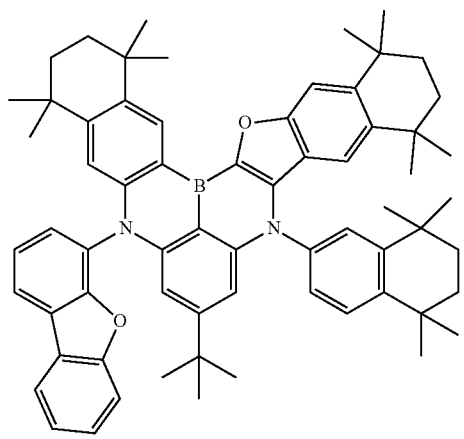
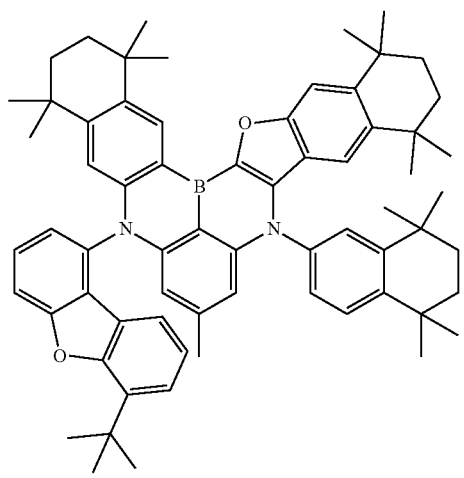
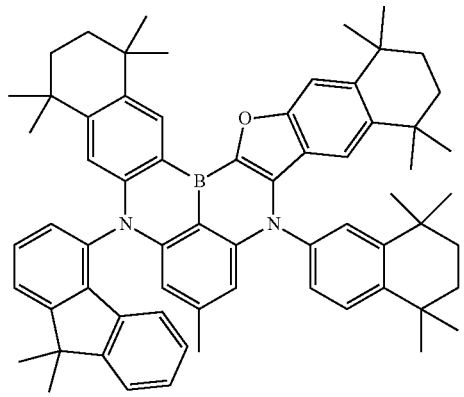
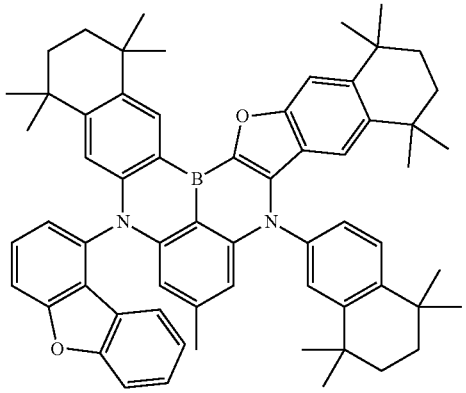

2747
-continued
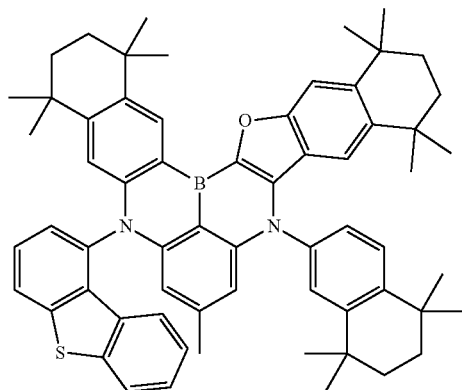
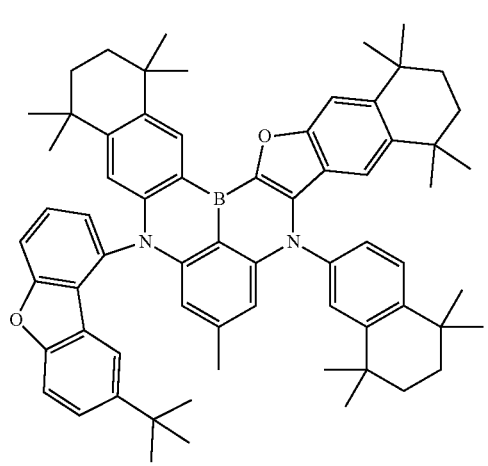
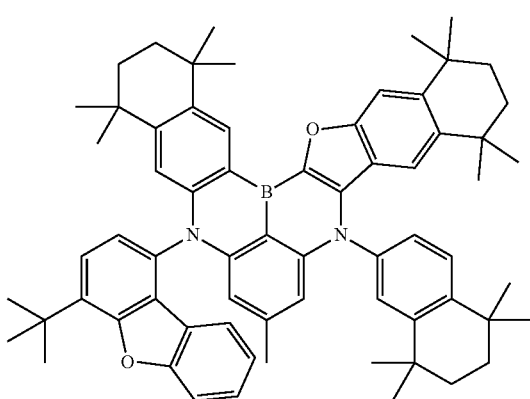
2748
-continued
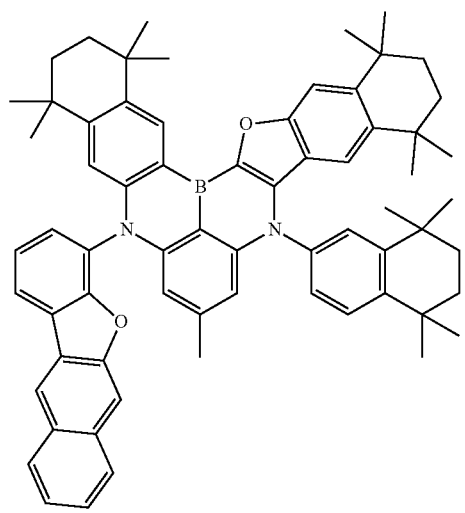
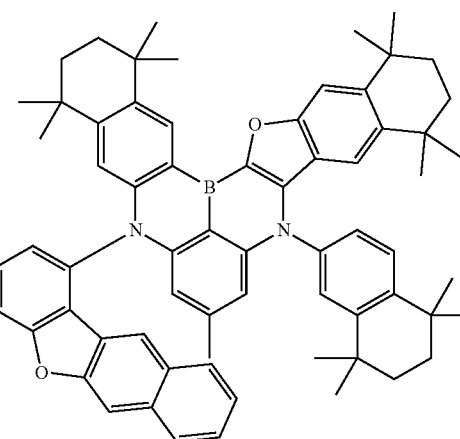
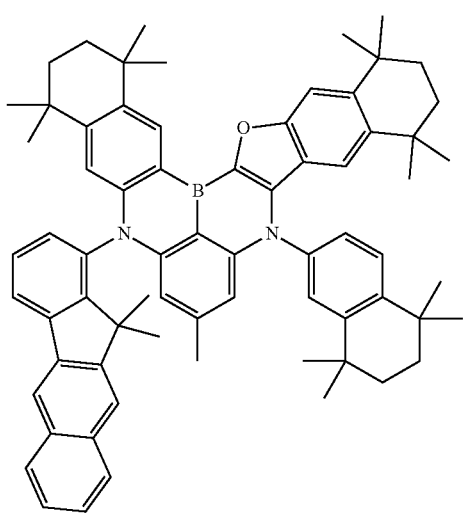

| 2749 | 2750 |
|---|---|
| -continued | -continued |
| 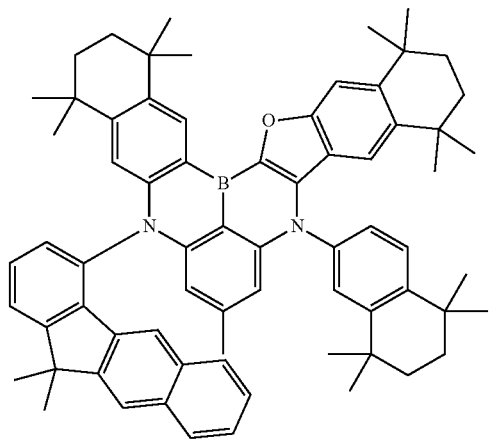 | 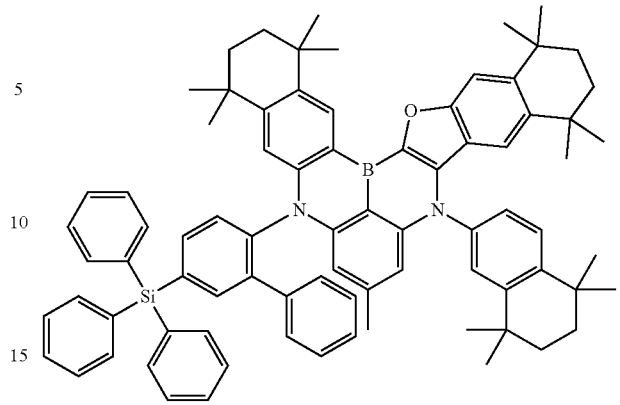 |
| 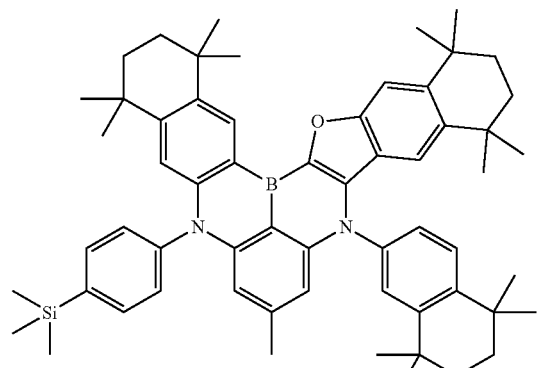 | 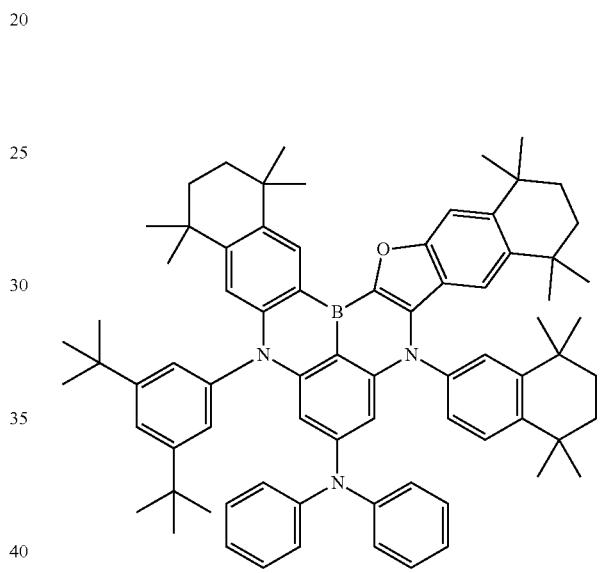 |
| 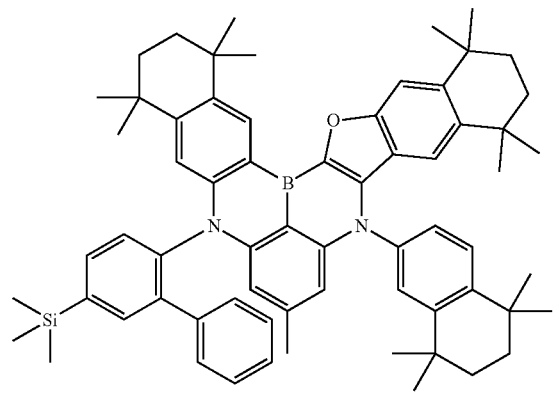 | |
| 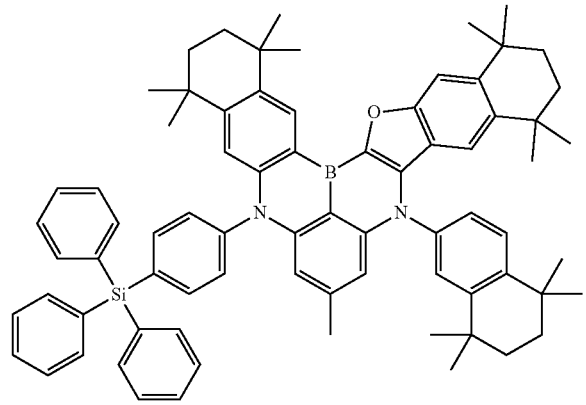 | 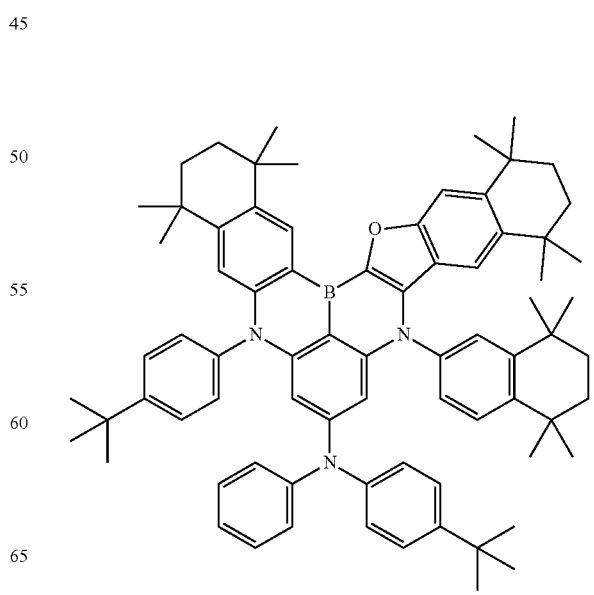 |

2751
-continued
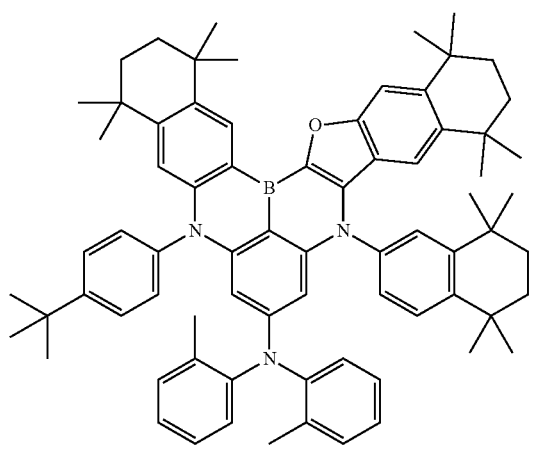
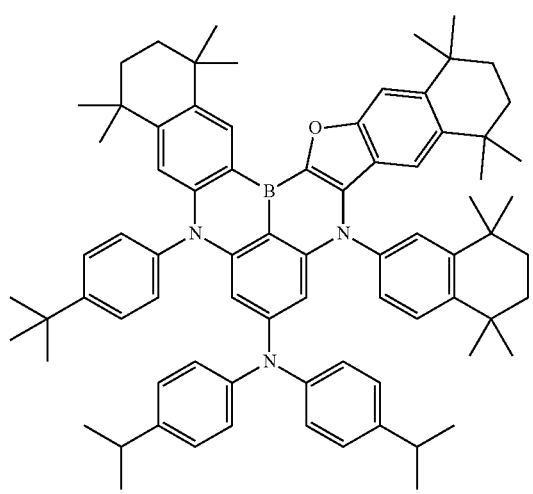
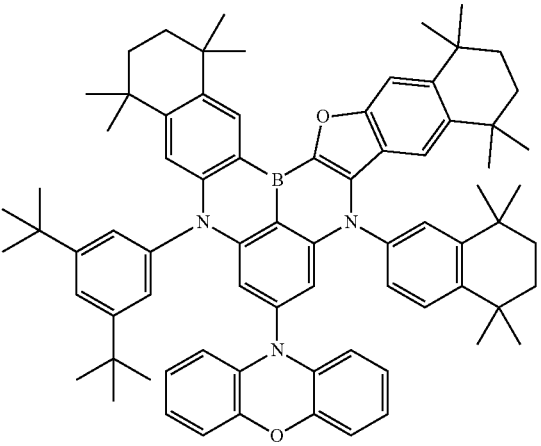
2752
-continued
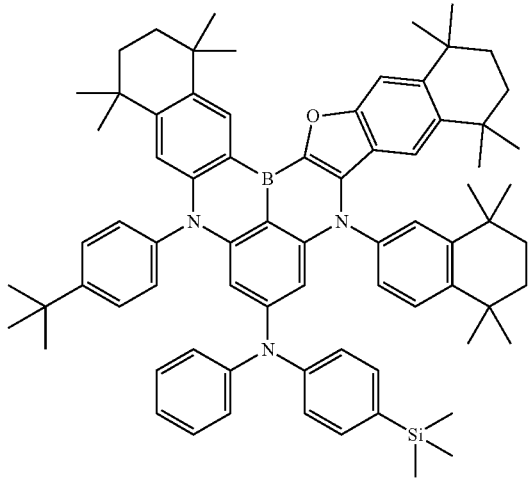
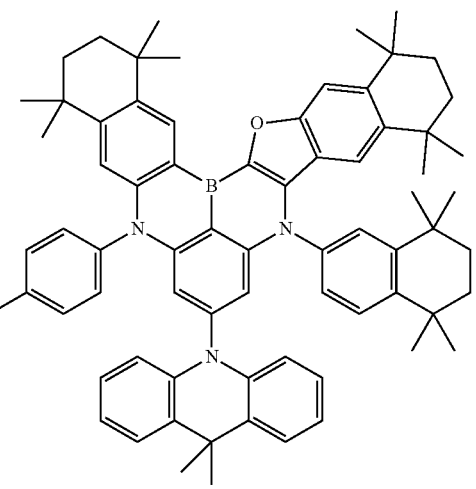
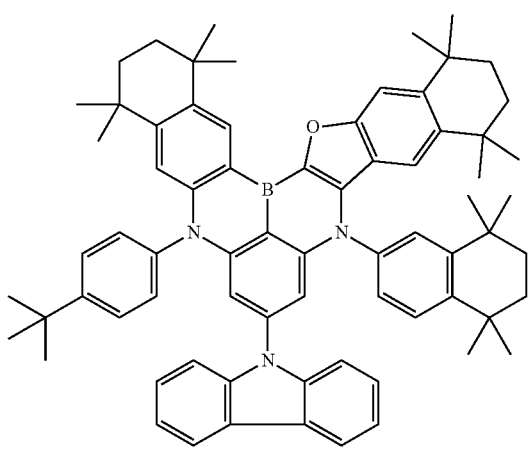

2753
-continued
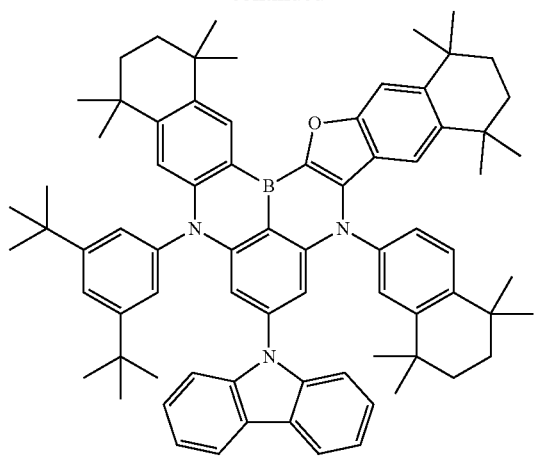
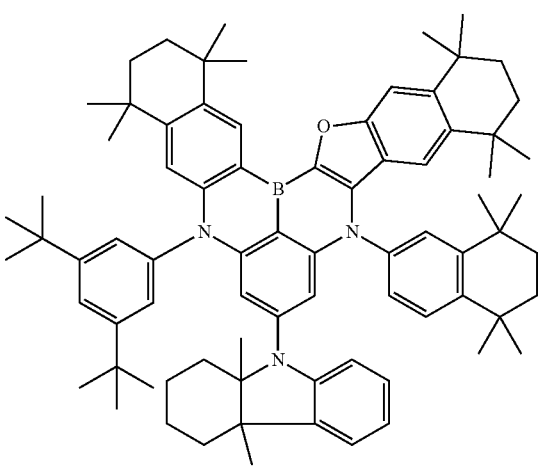
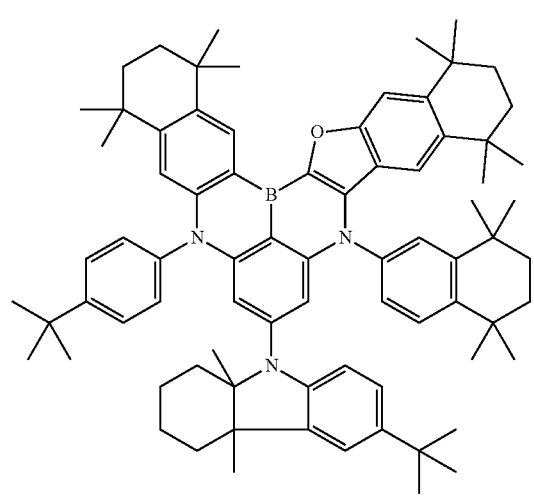
2754
-continued
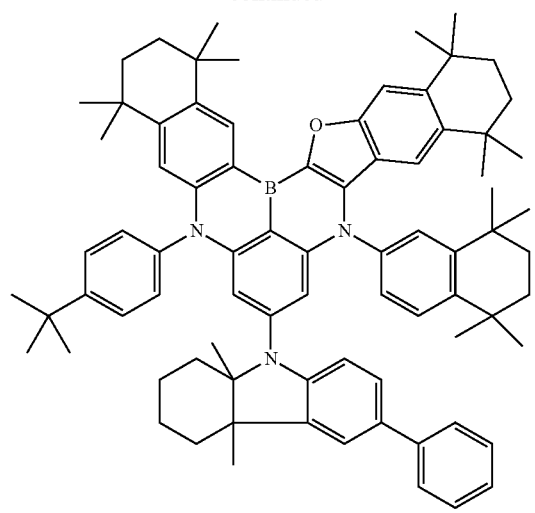
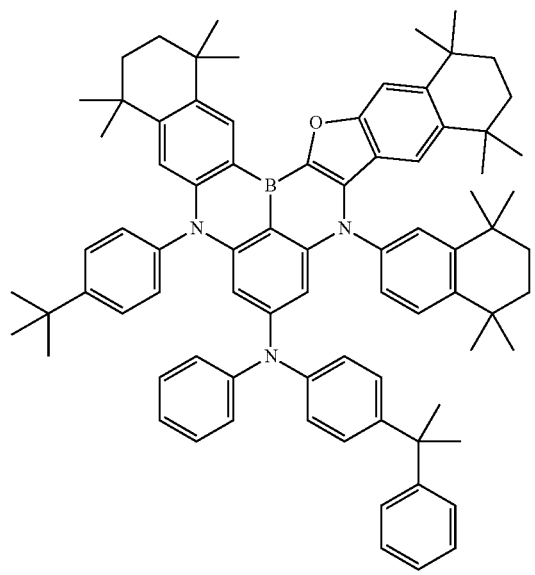
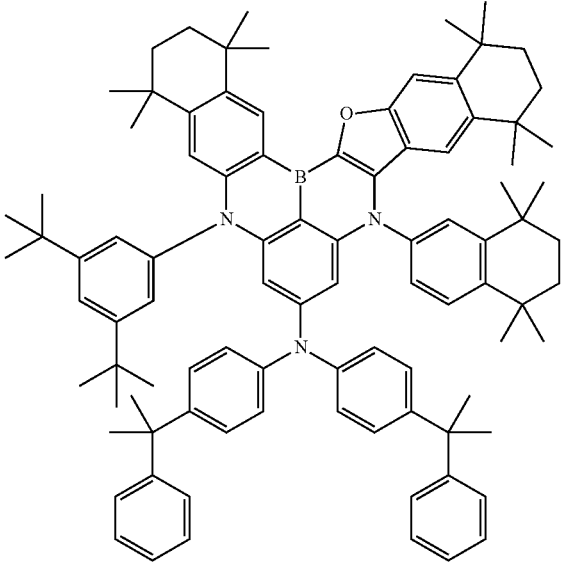

2755
-continued
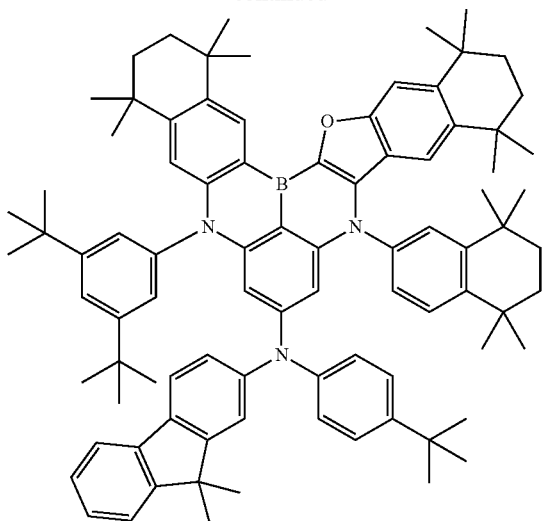
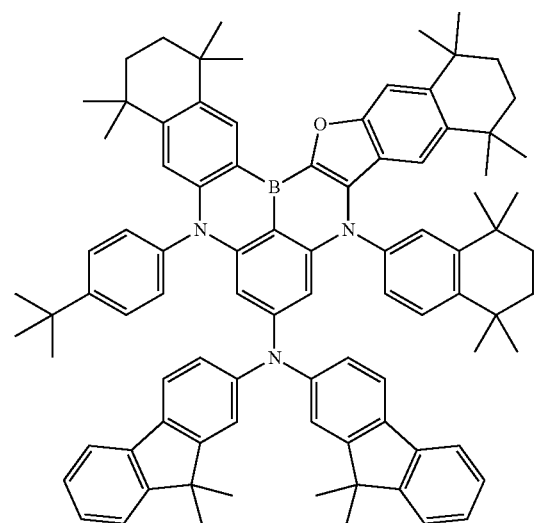
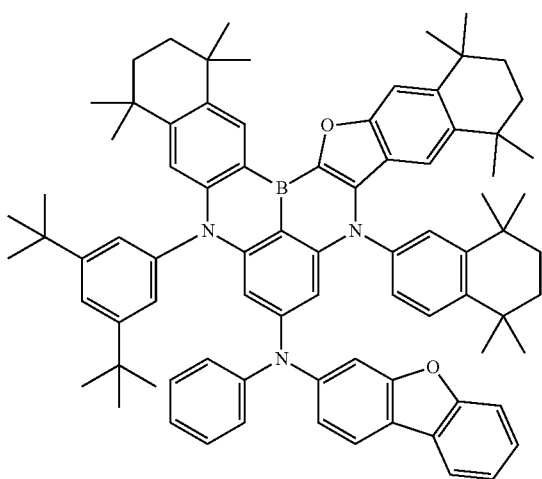
2756
-continued
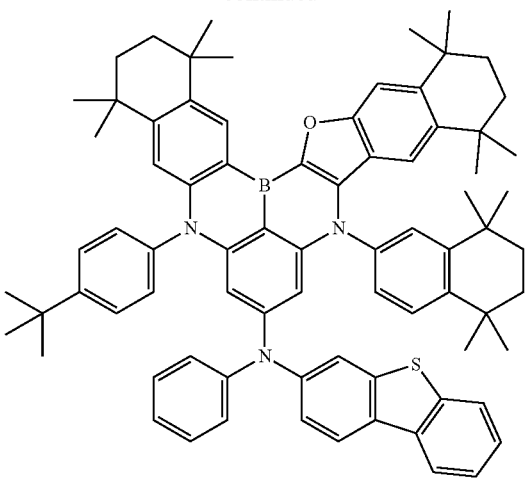
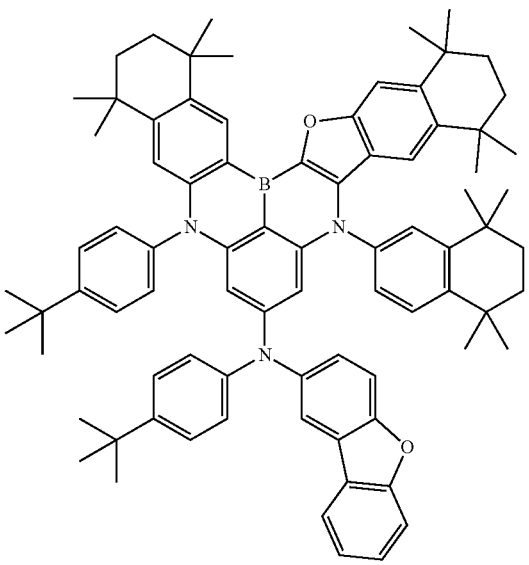
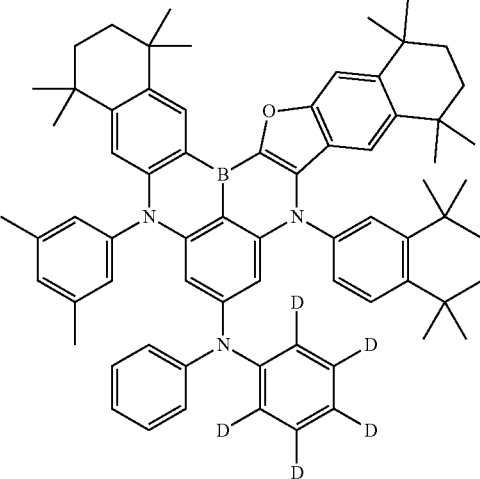

2757
-continued
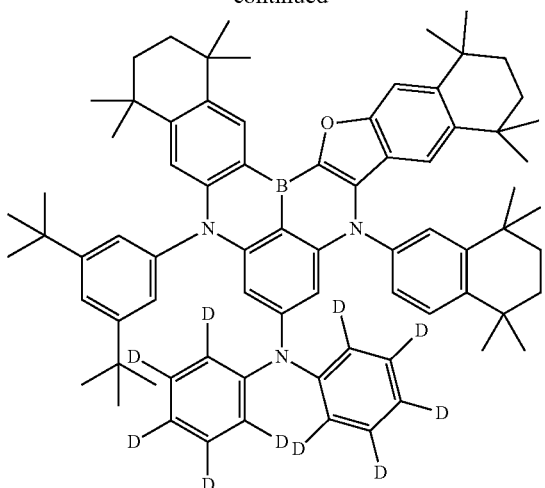
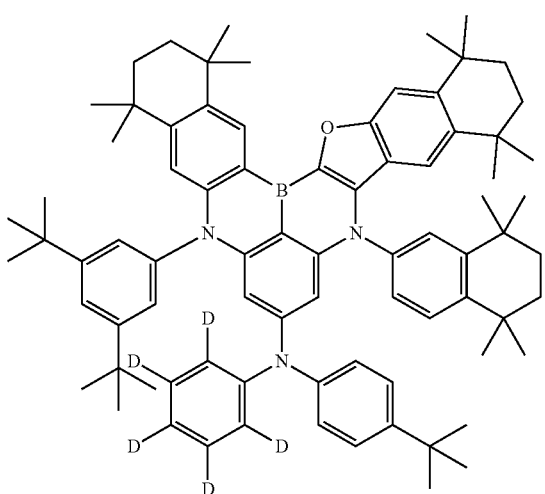
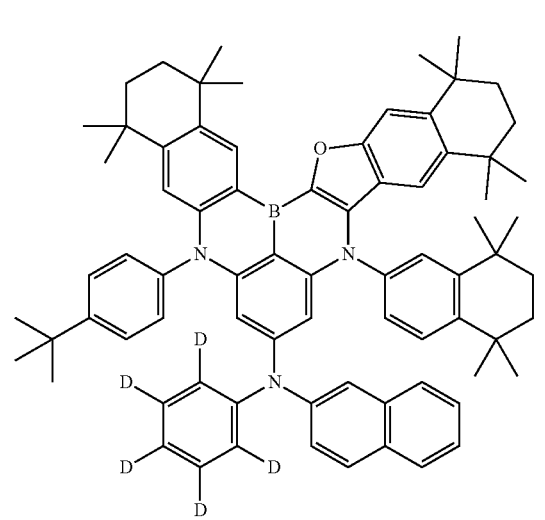
2758
-continued
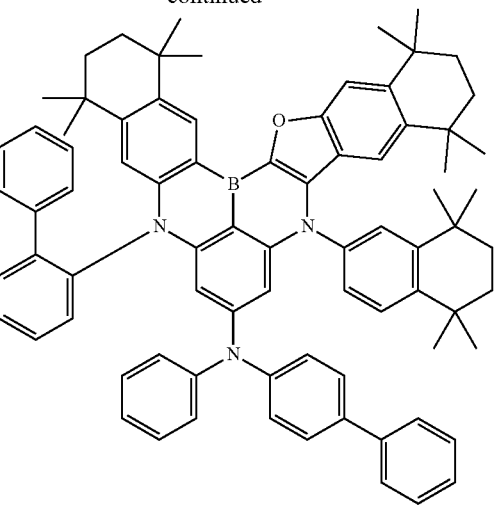
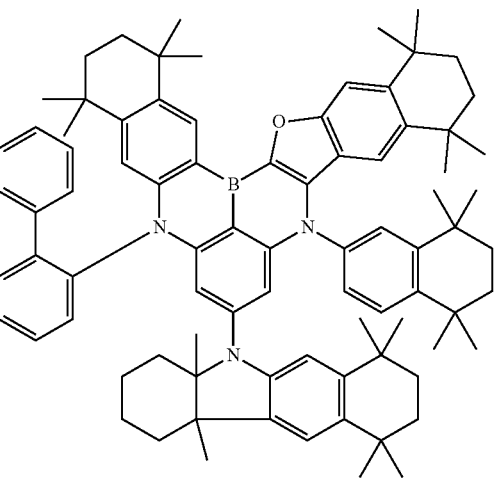
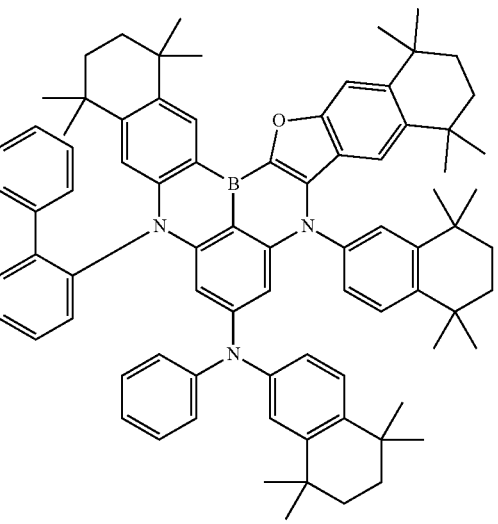

2759
-continued
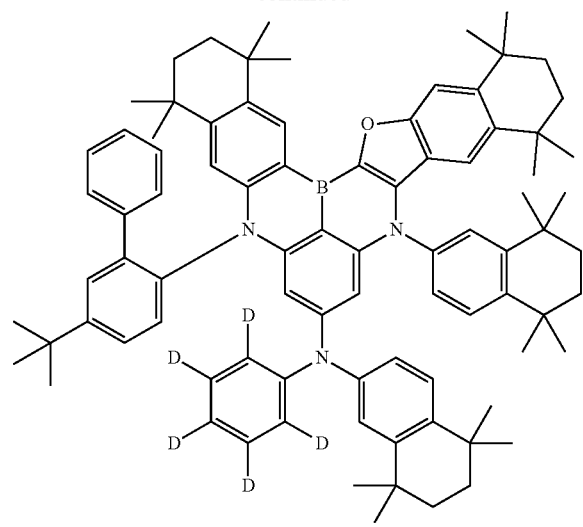
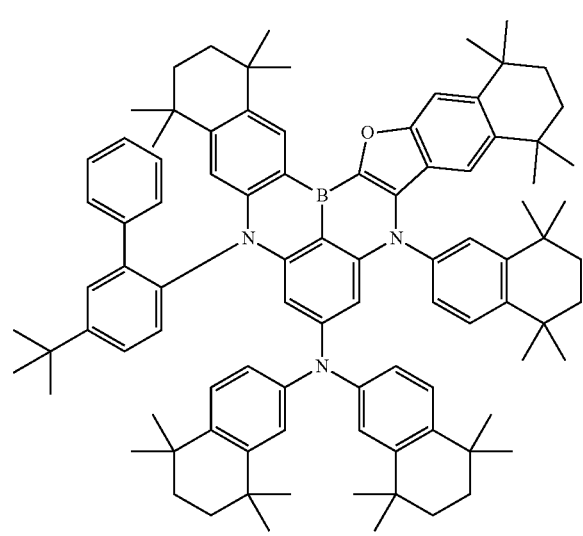
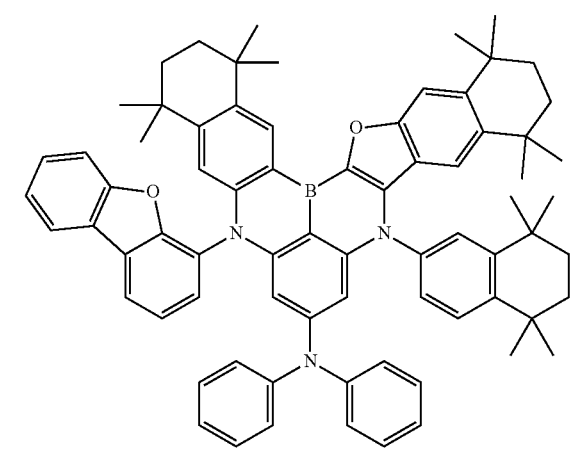
2760
-continued
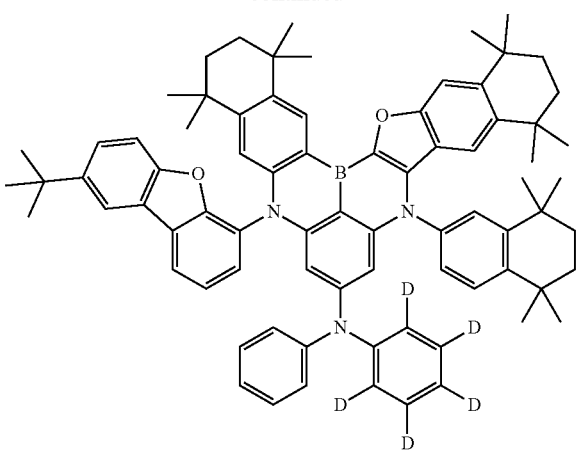
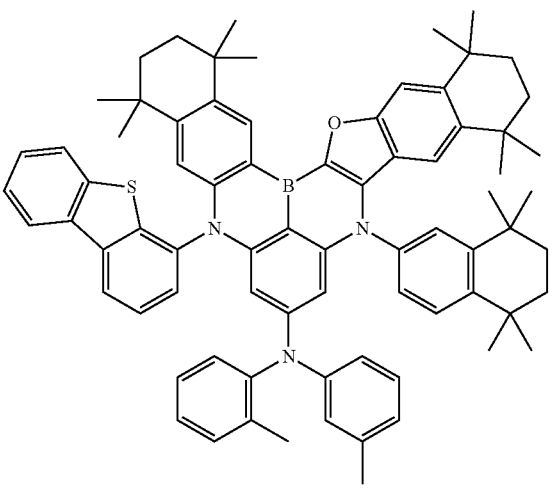
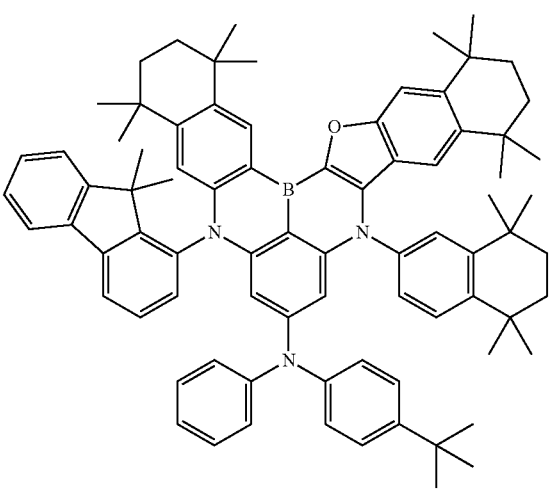

2761
-continued
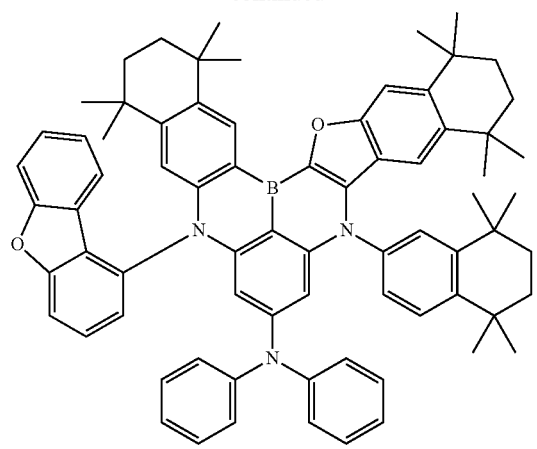
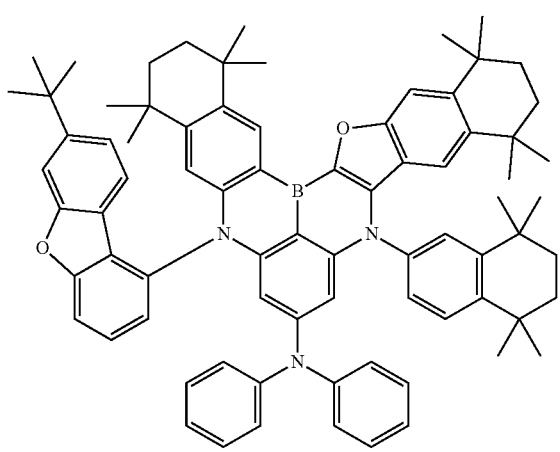
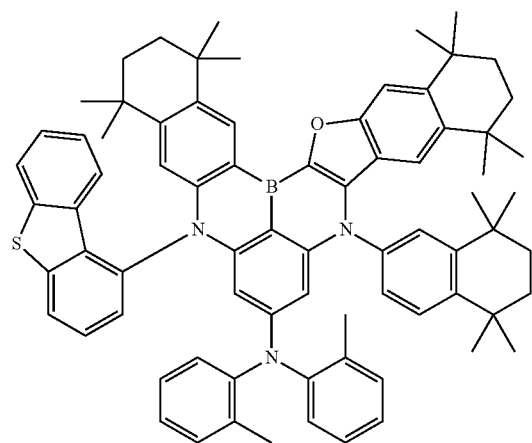
2762
-continued
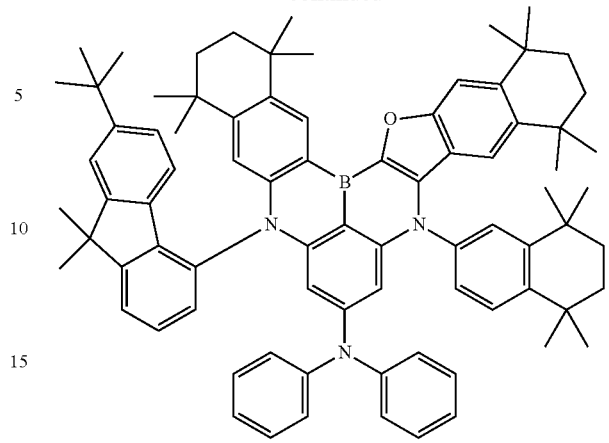
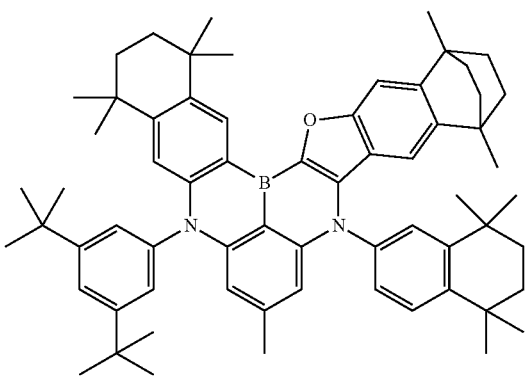
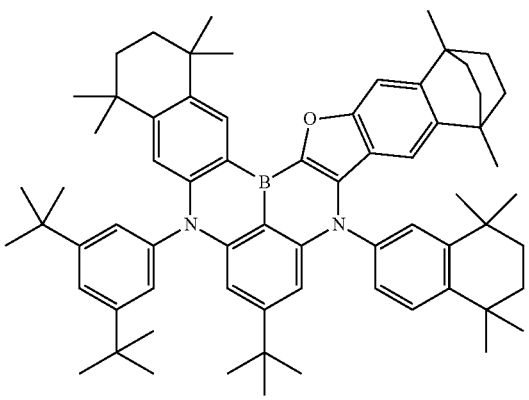
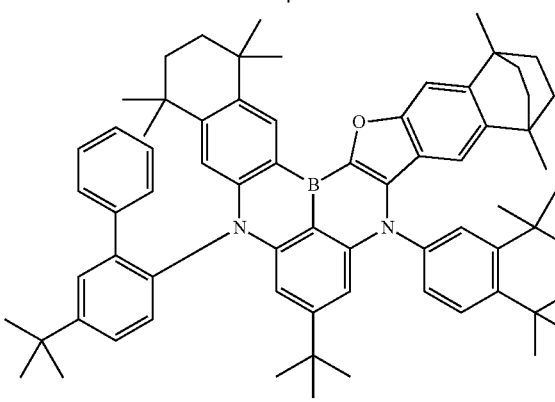

| 2763 -continued | 2764 -continued |
|---|---|
| 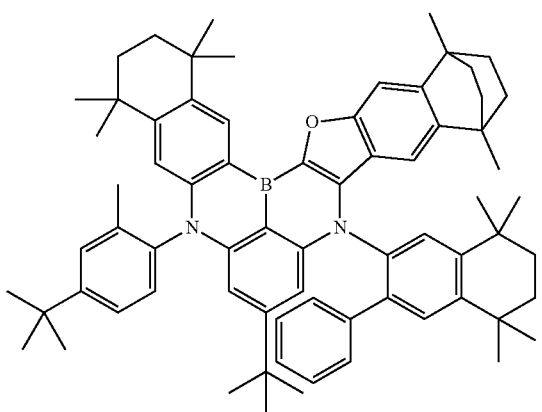 | 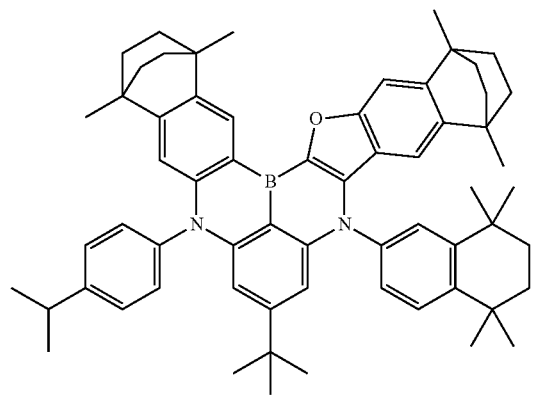 |
| 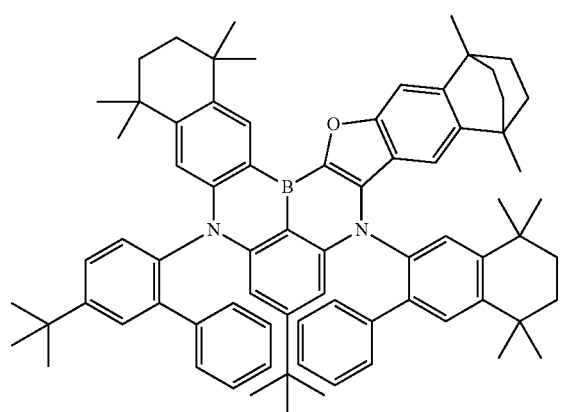 | 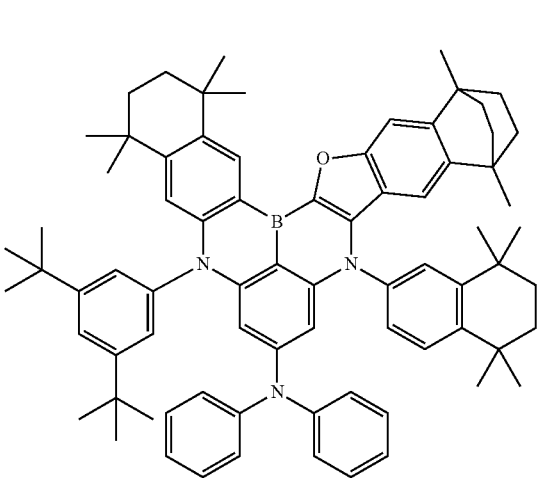 |
| 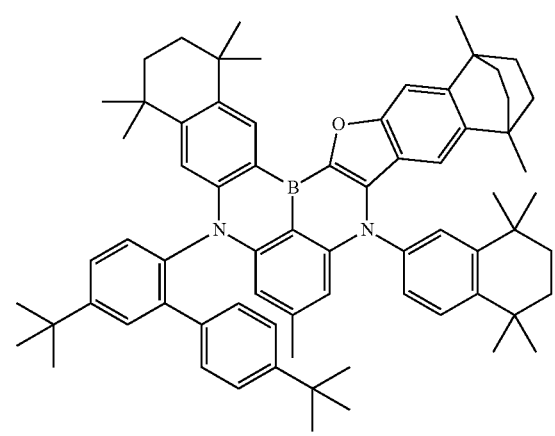 | |
| 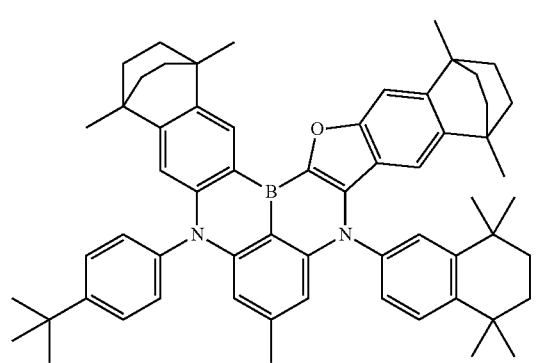 | 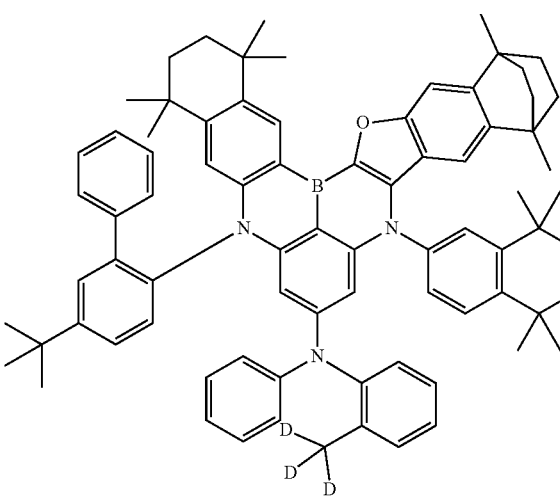 |

2765
-continued
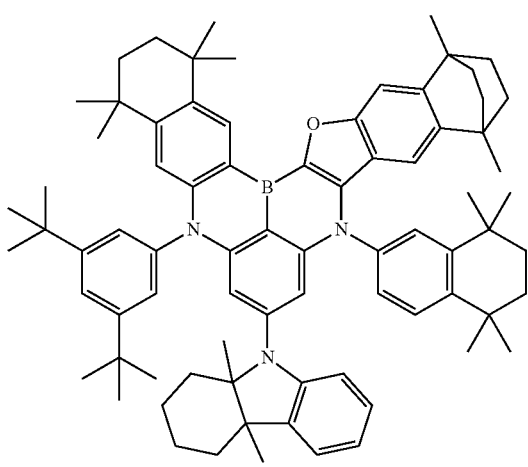
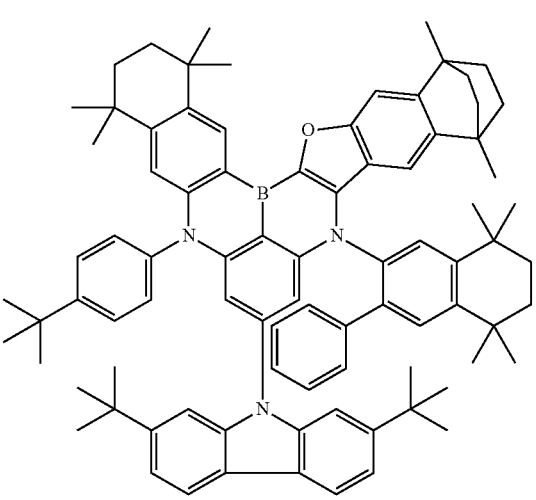
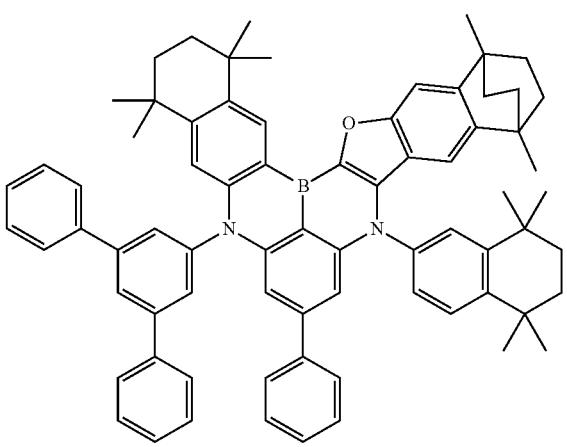
2766
-continued
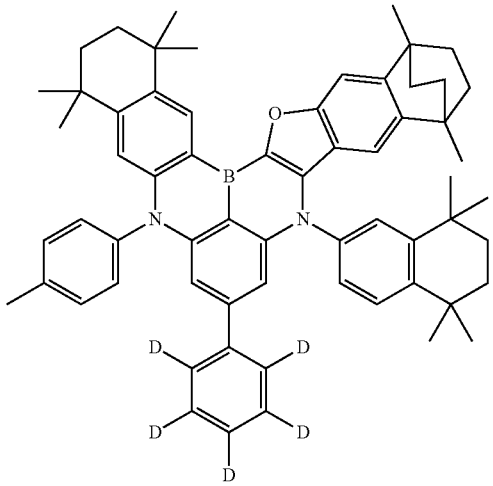
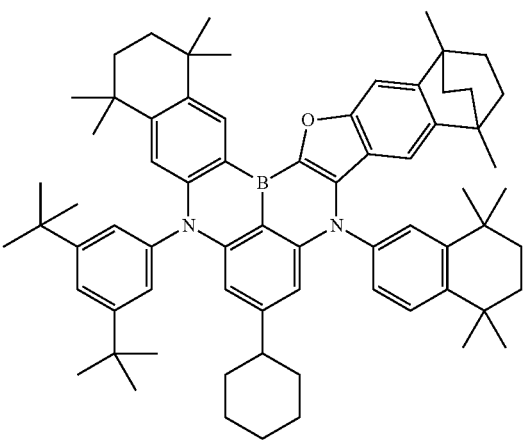
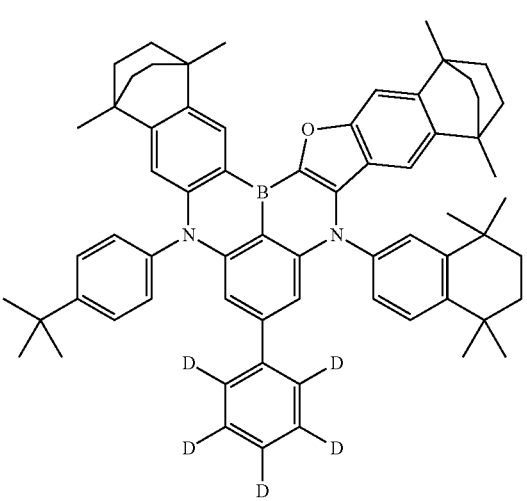

2767
-continued
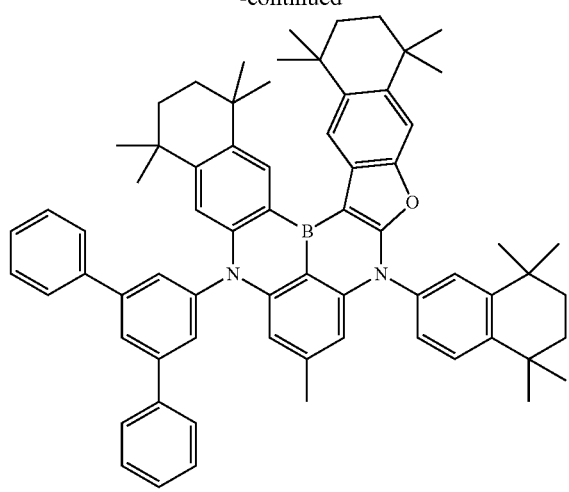
2768
-continued
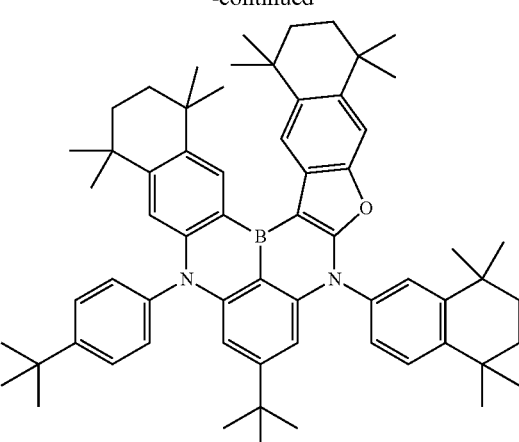
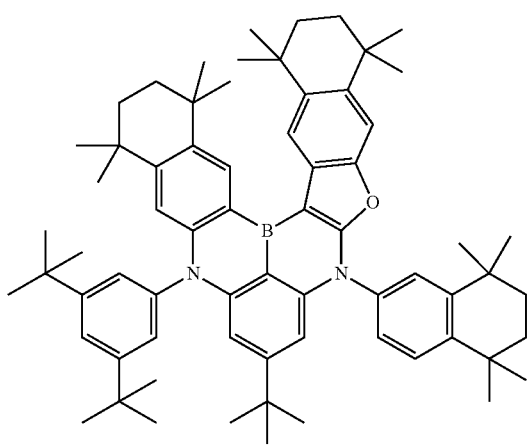
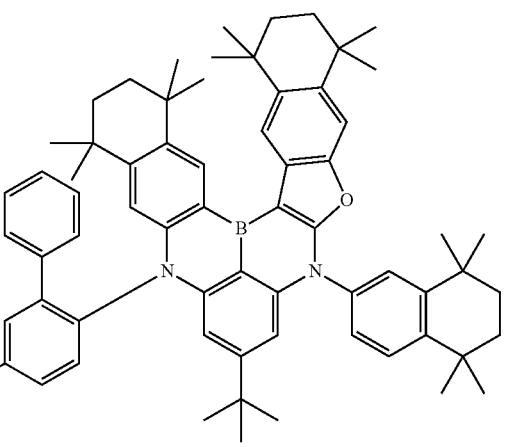
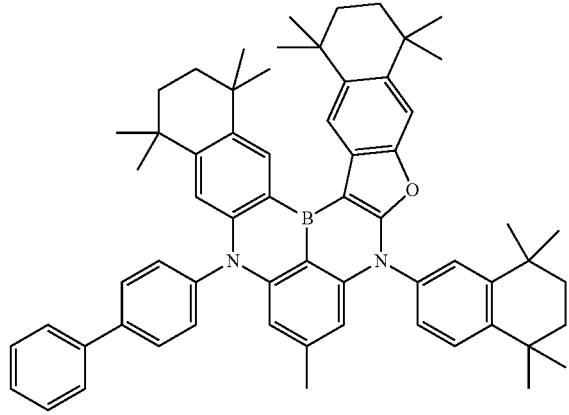
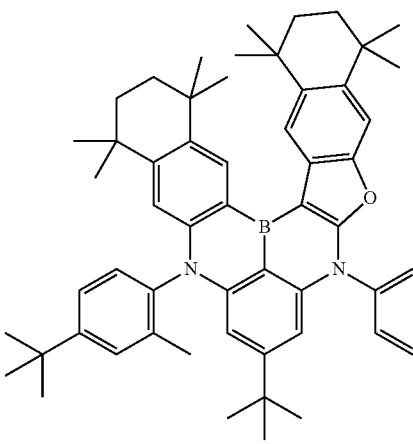

2769
-continued
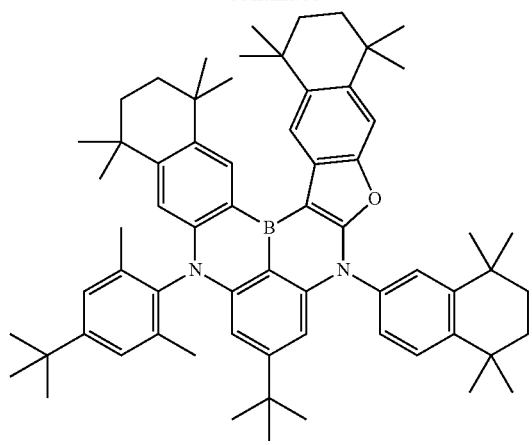
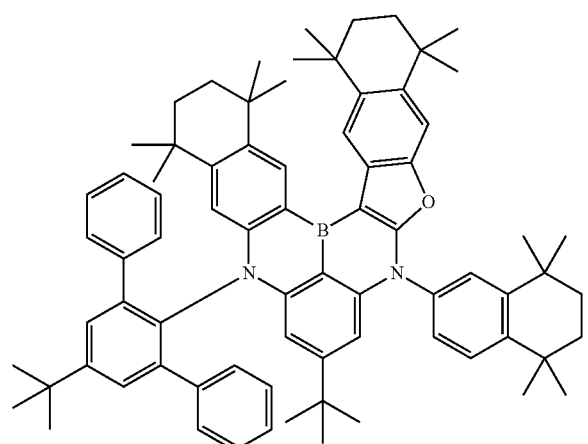
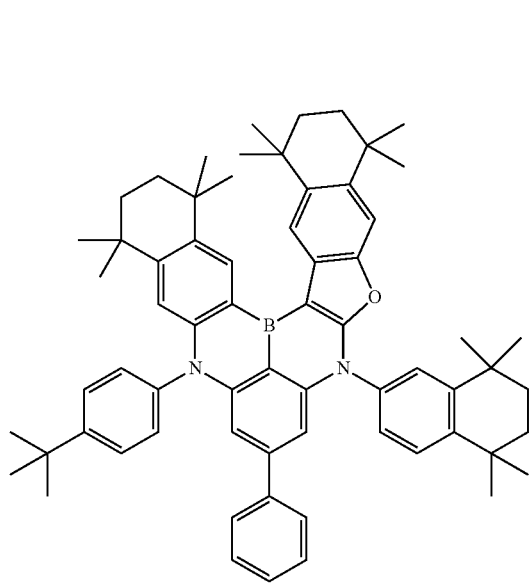
2770
-continued
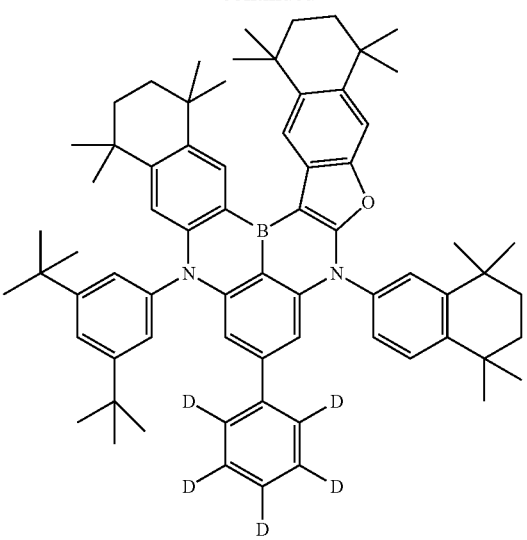
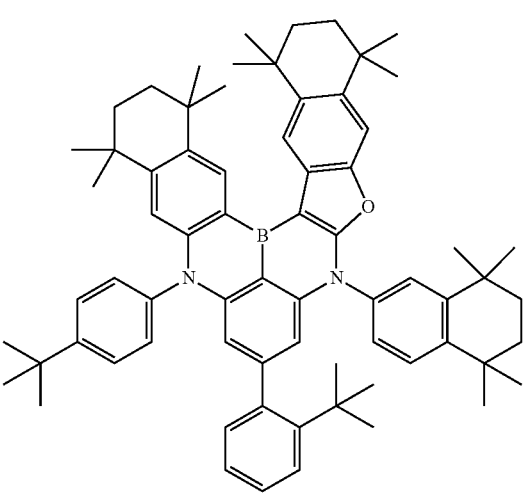
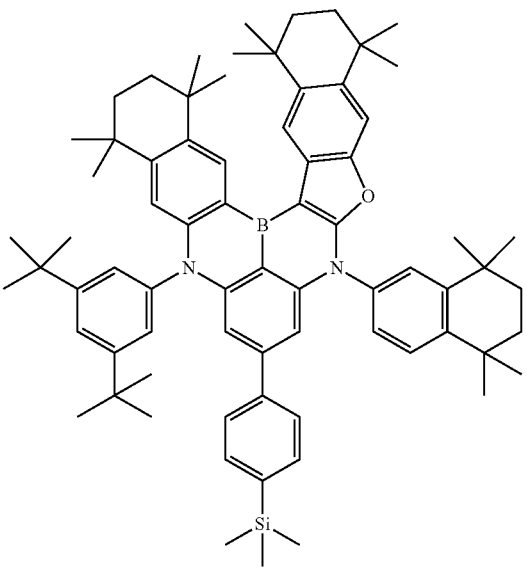

| 2771 | 2772 |
|---|---|
| -continued | -continued |
| 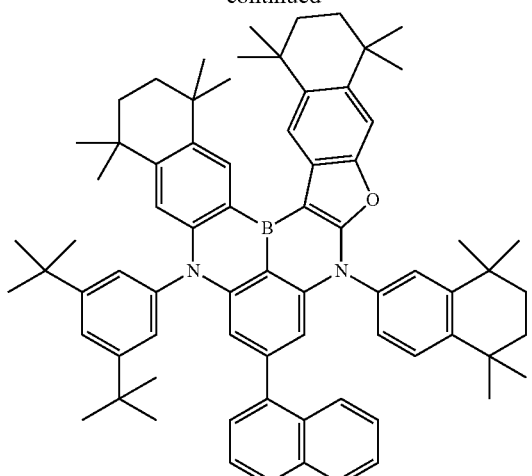 | 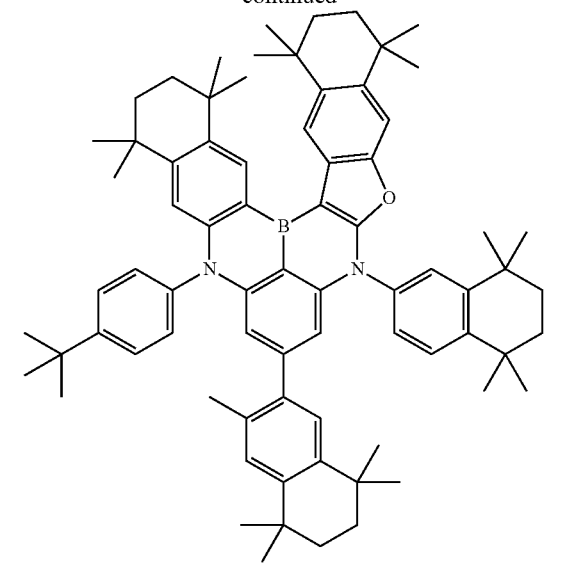 |
| 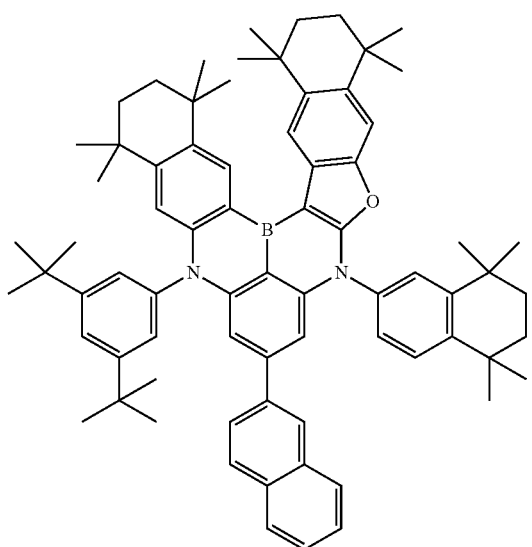 | 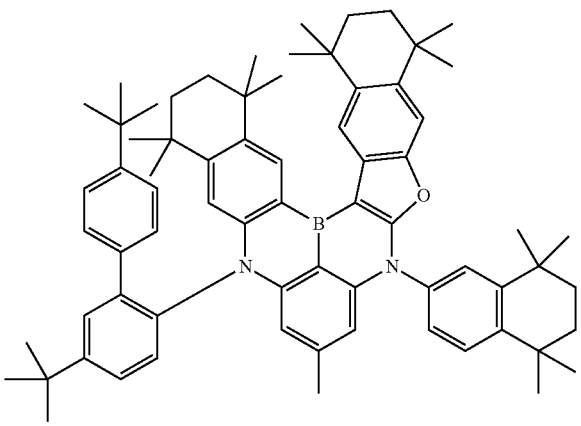 |
| 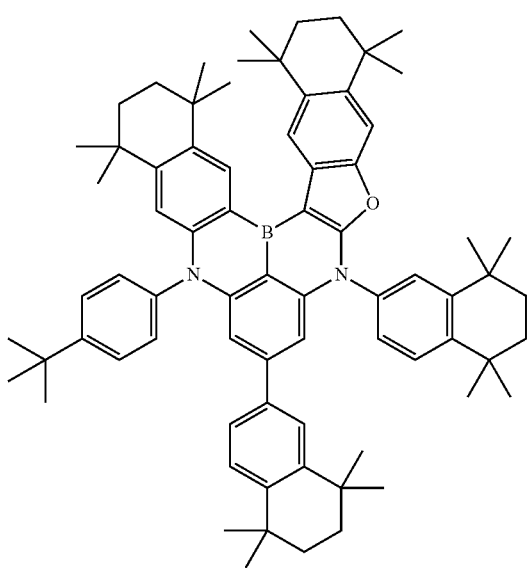 | 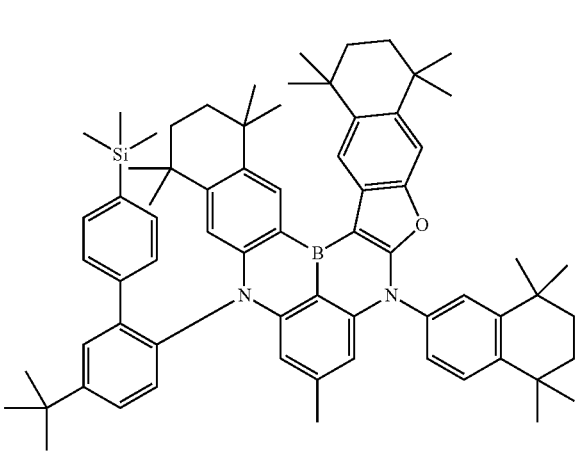 |

2773
-continued
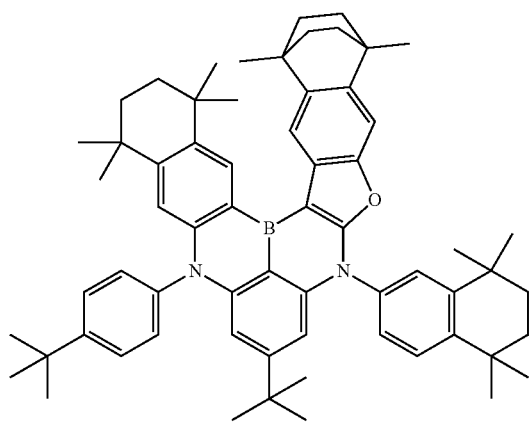
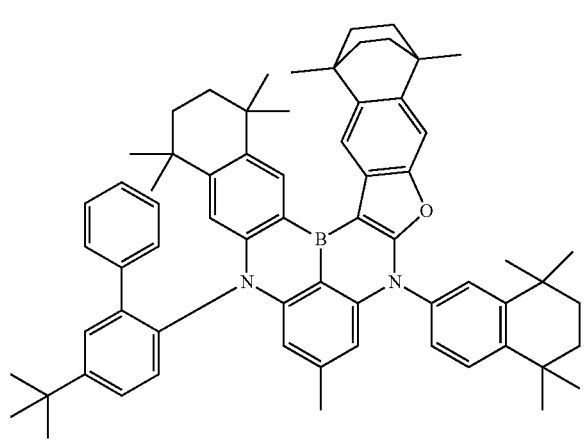
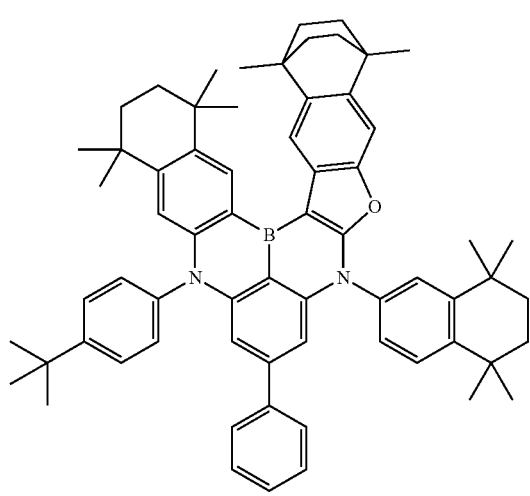
2774
-continued
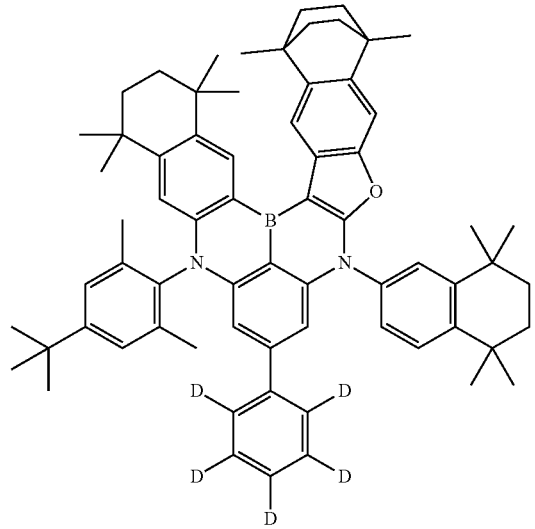
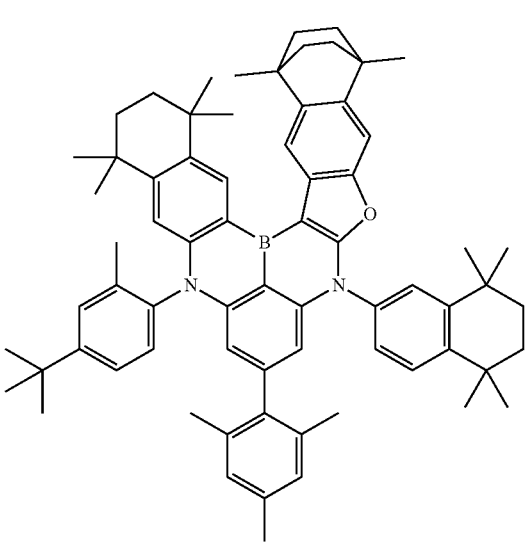
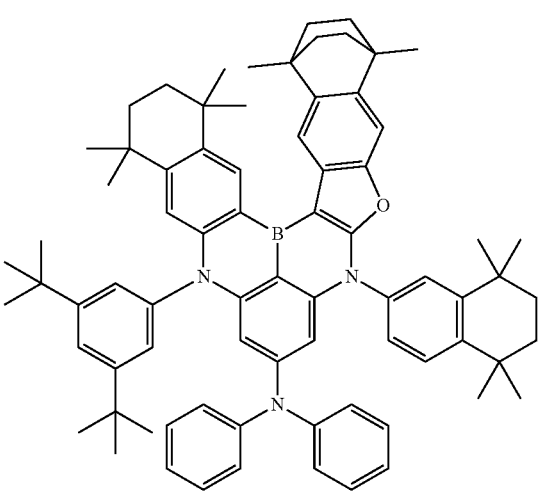

2775
-continued
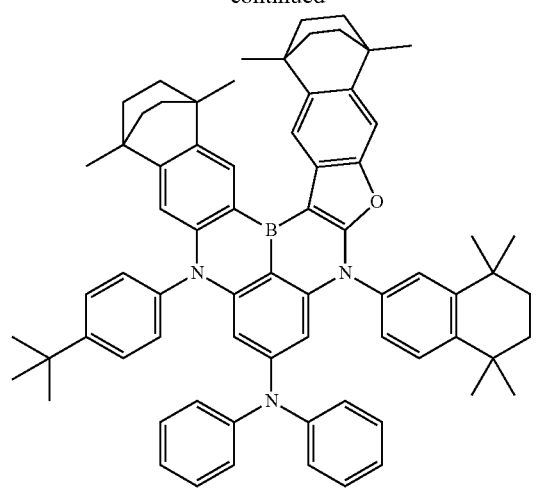
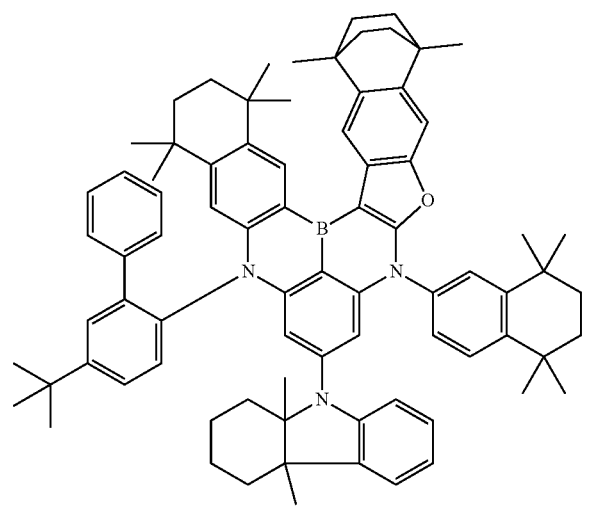
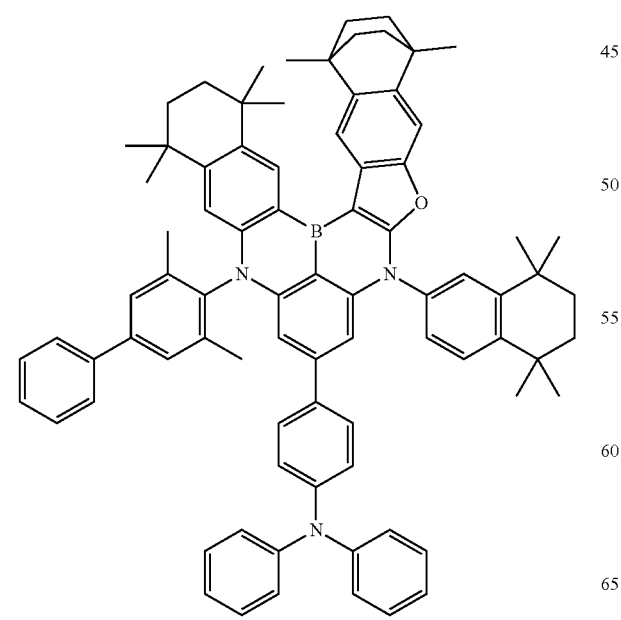
2776
-continued
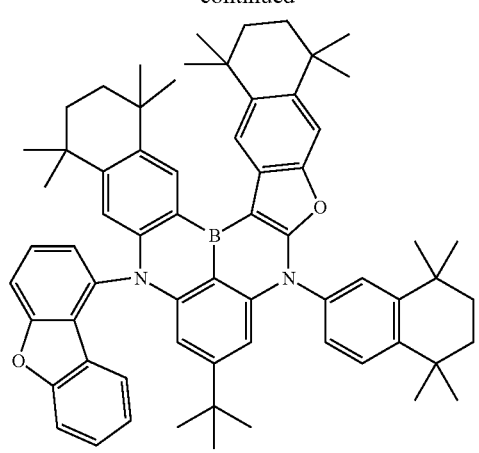
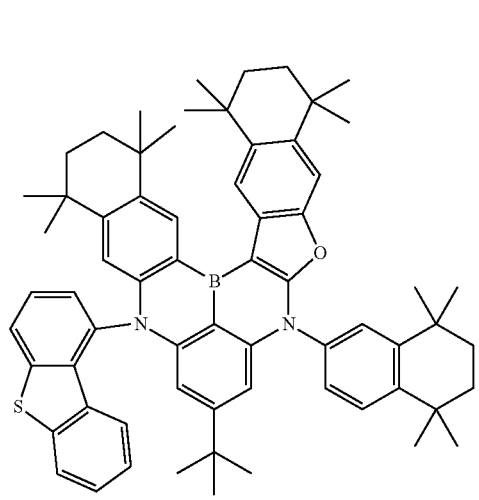
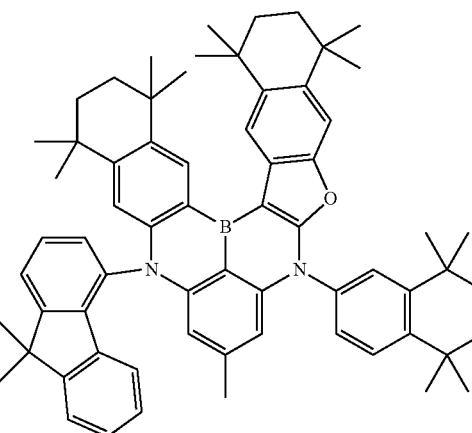

2777
-continued
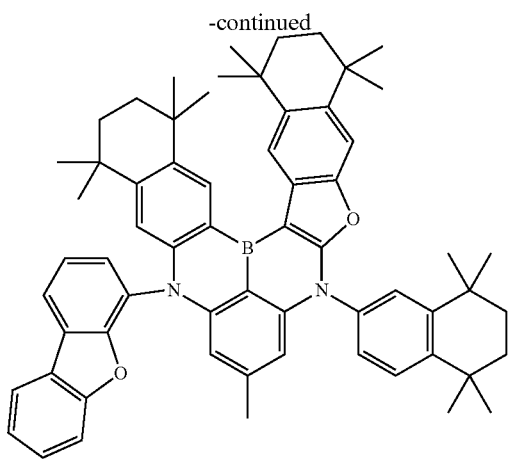
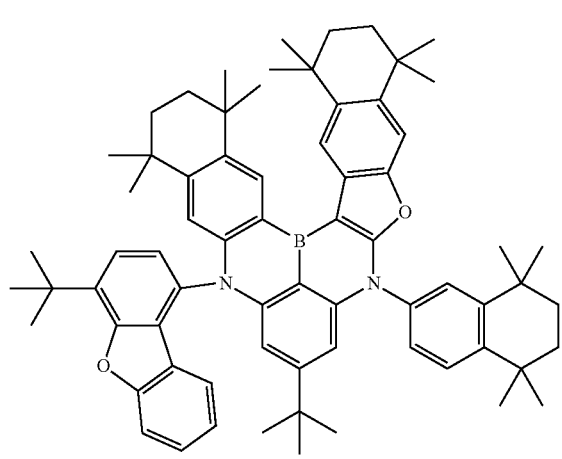
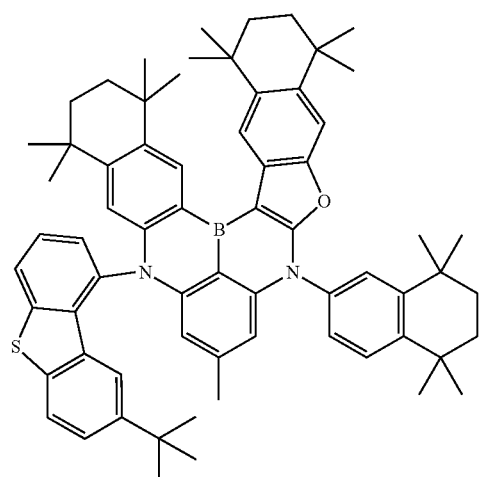
2778
-continued
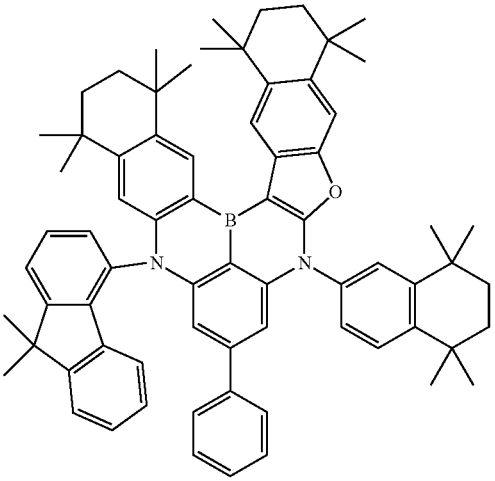
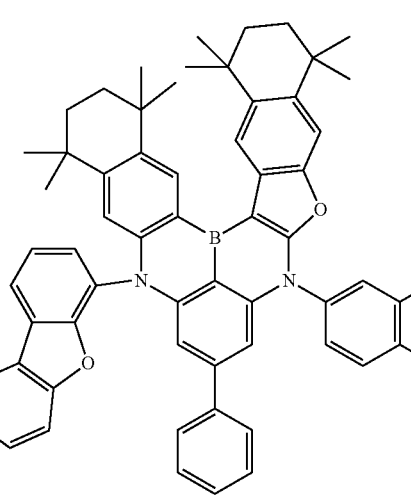
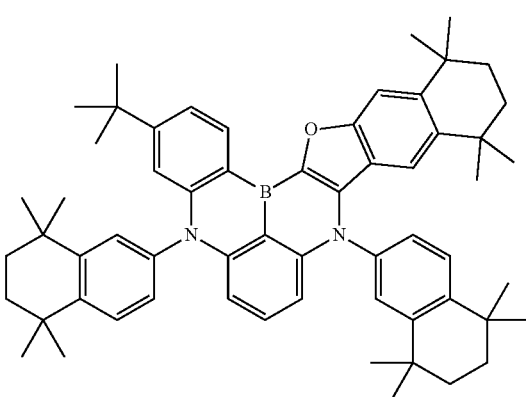

2779
-continued
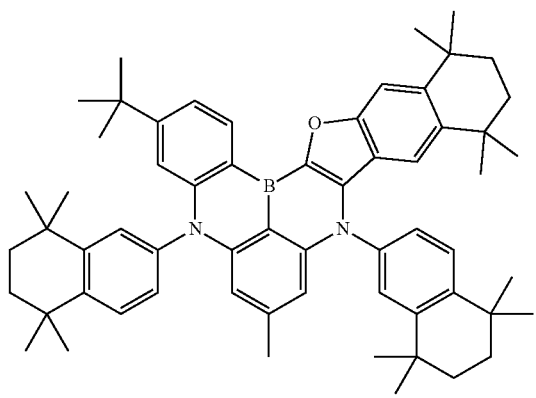
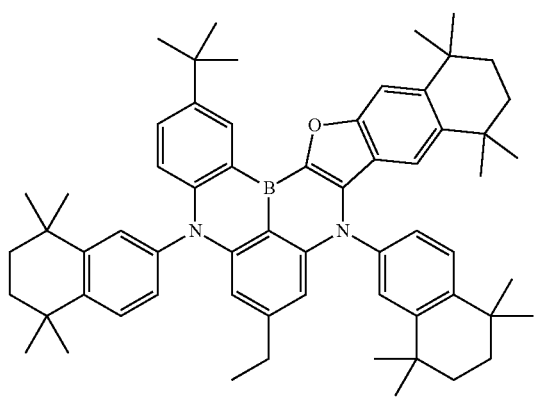
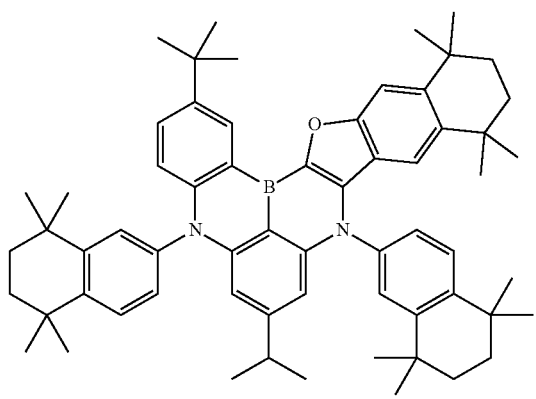
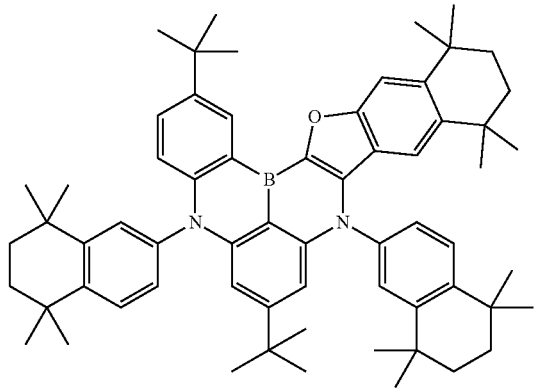
2780
-continued
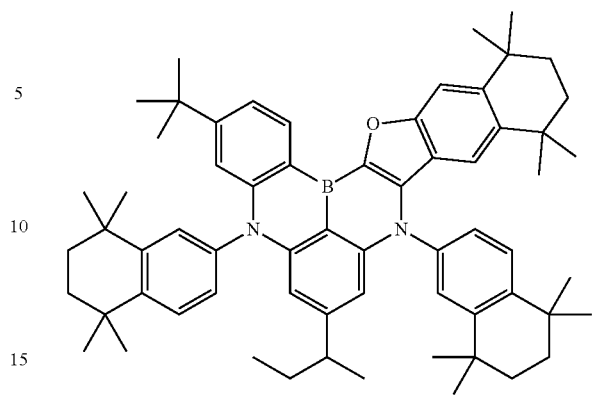
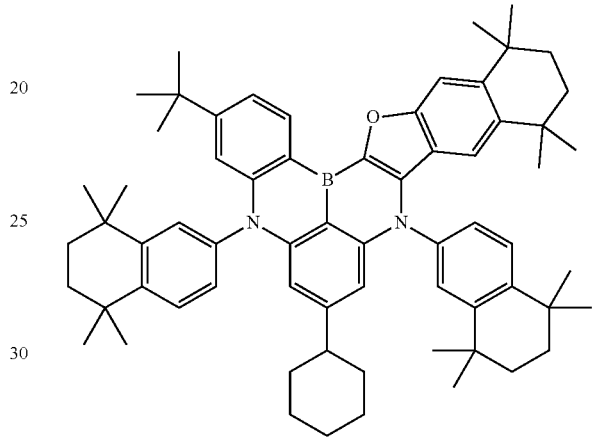
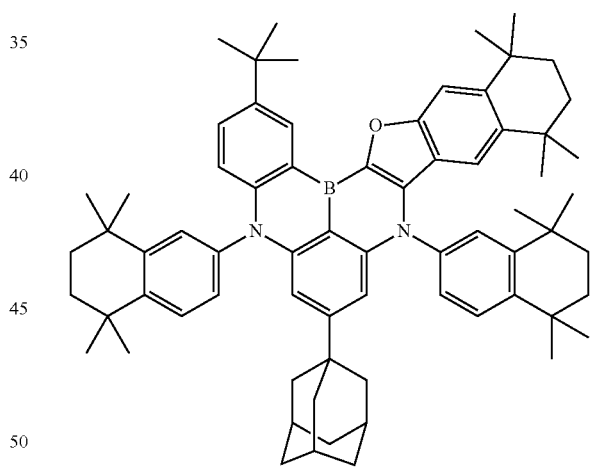
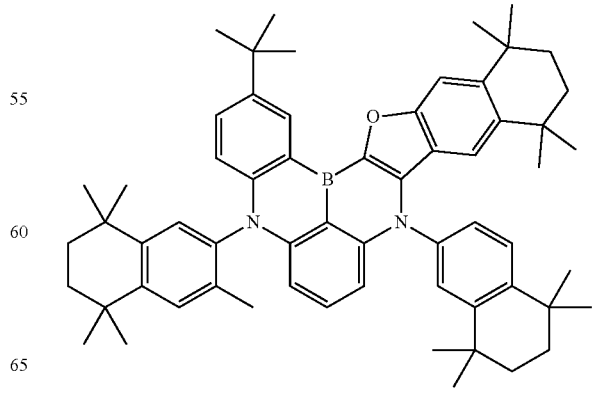

2781
-continued
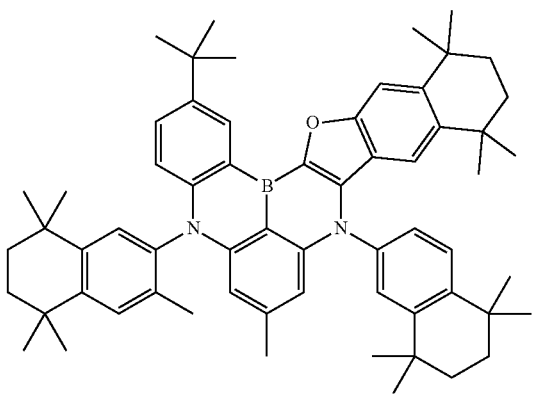
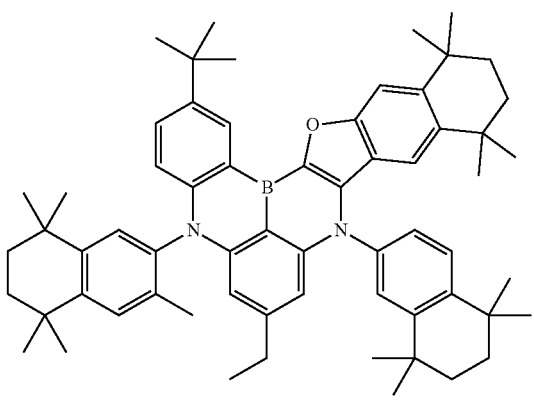
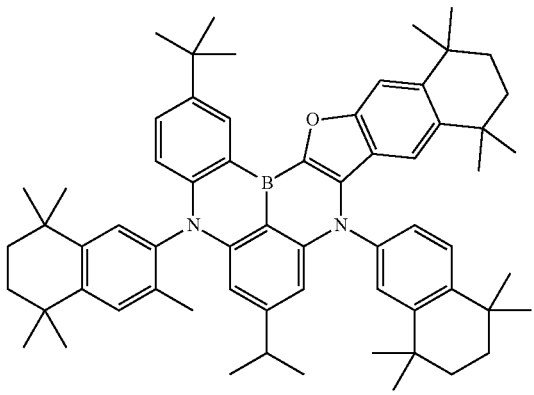
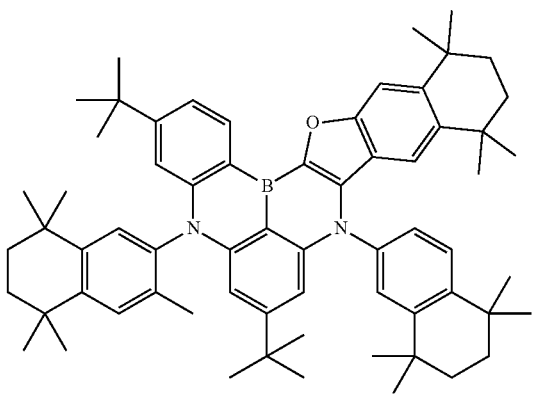
2782
-continued
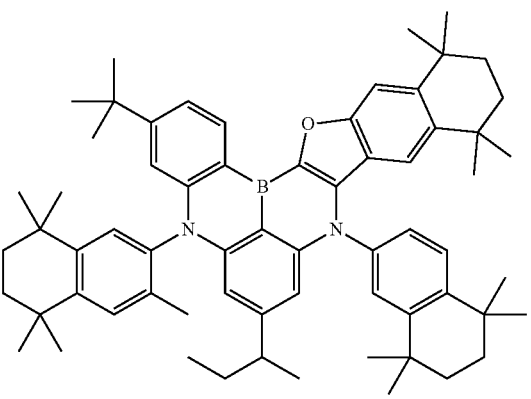
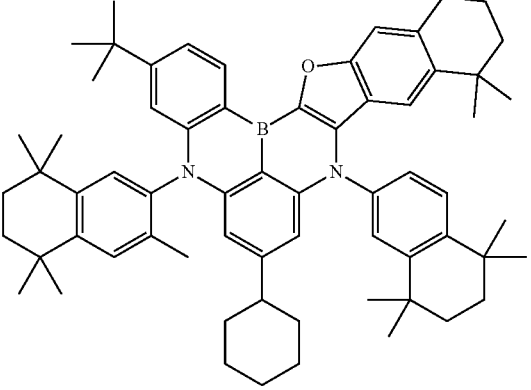
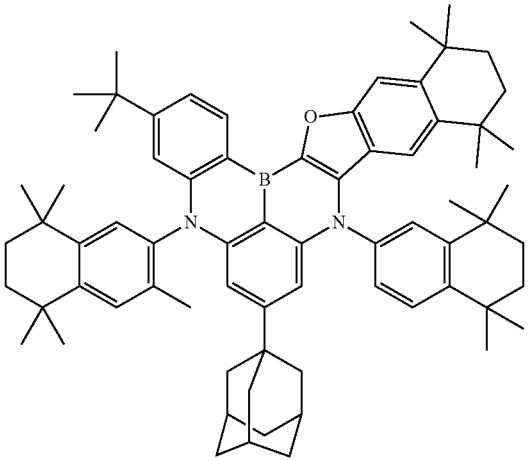
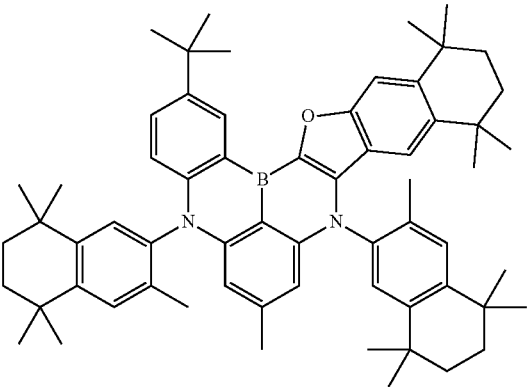

2783
-continued
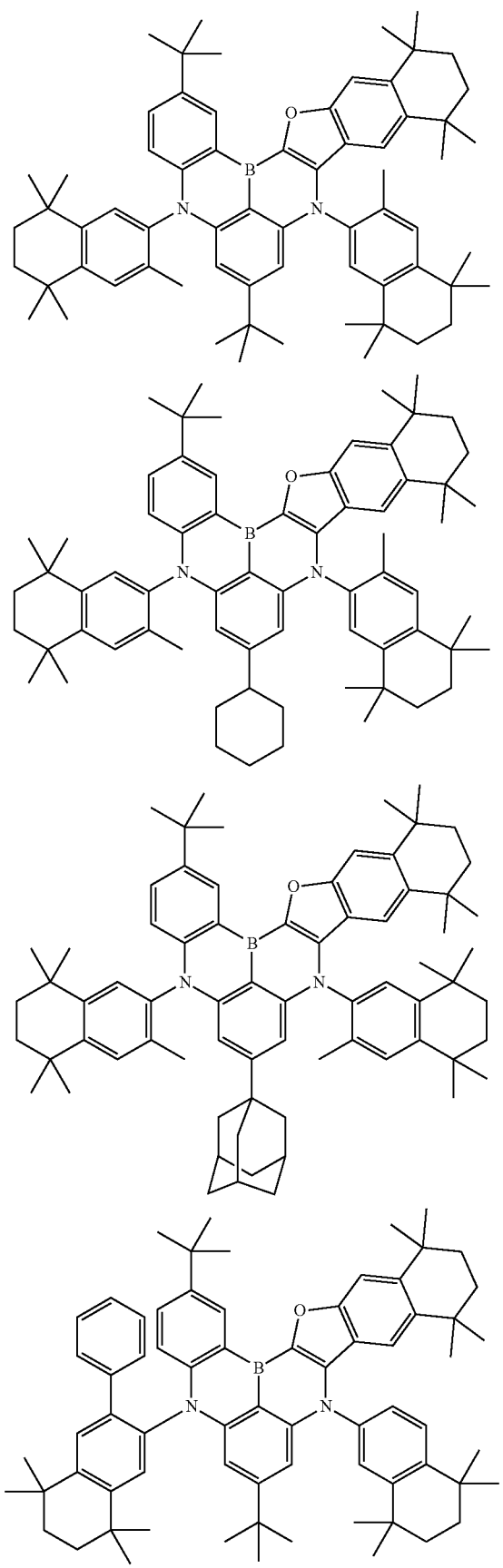
2784
-continued
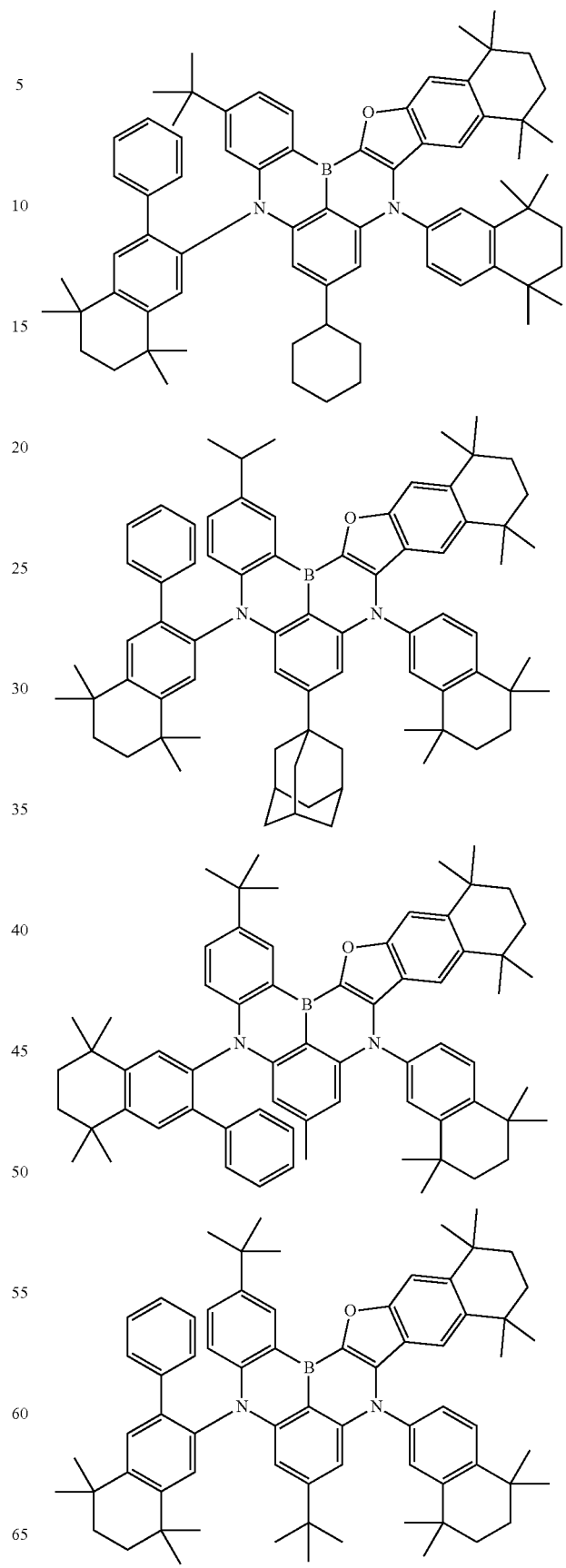

2785
-continued
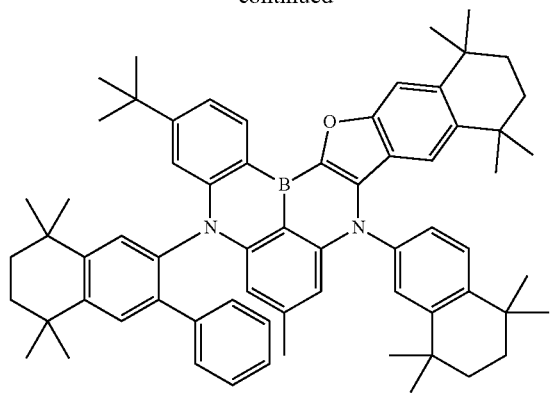
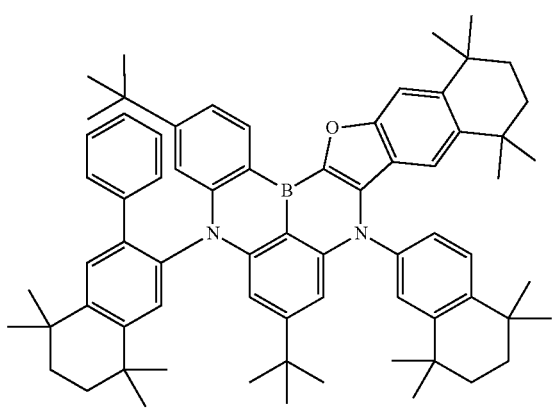
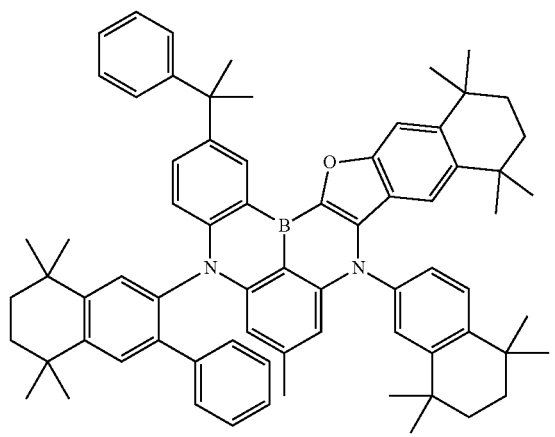
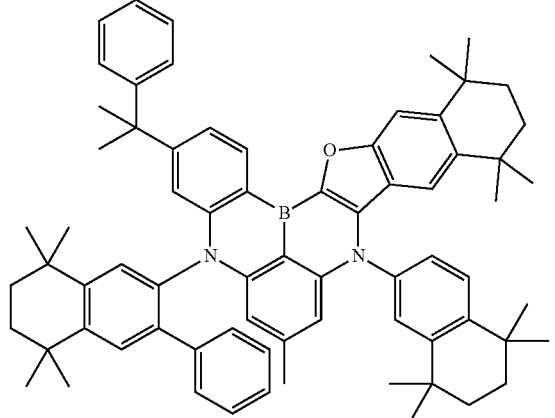
2786
-continued
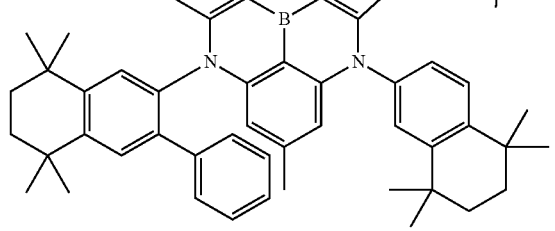

2787
-continued
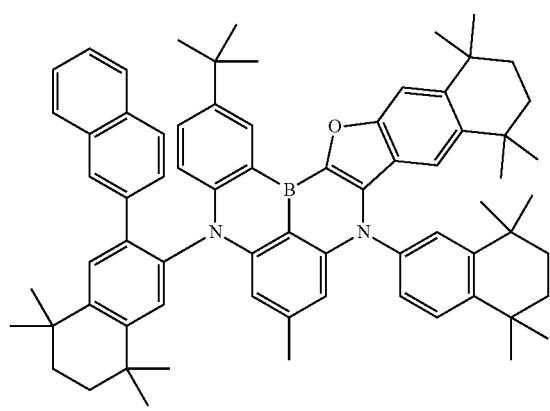
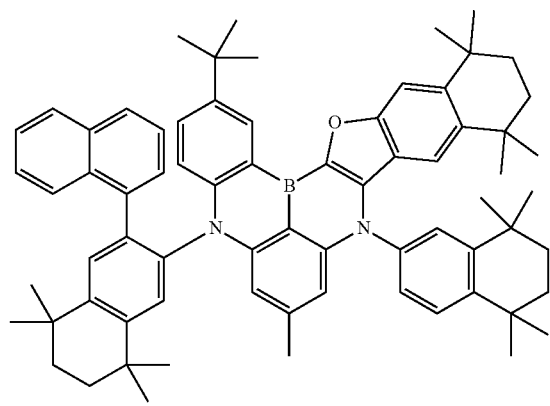
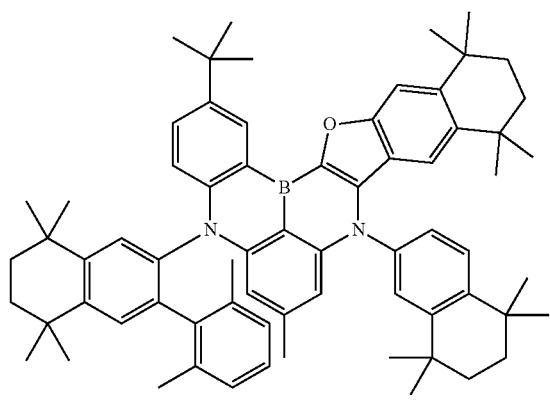
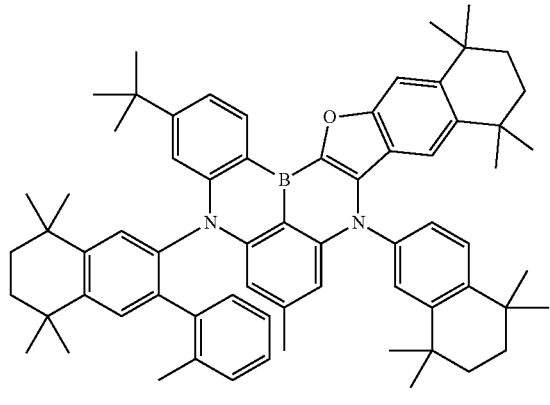
2788
-continued
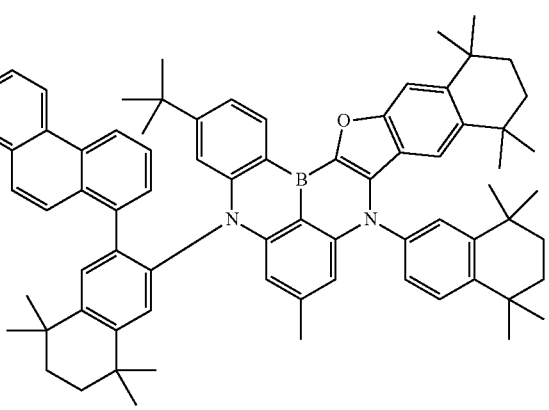
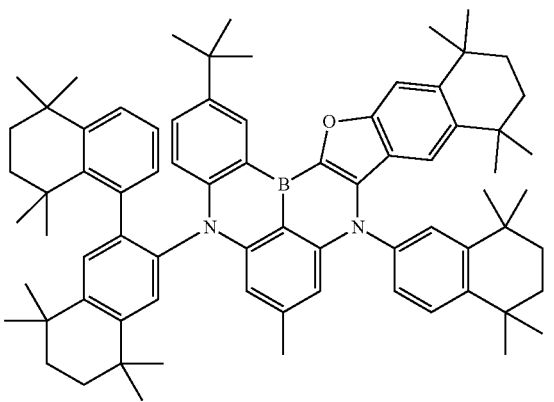
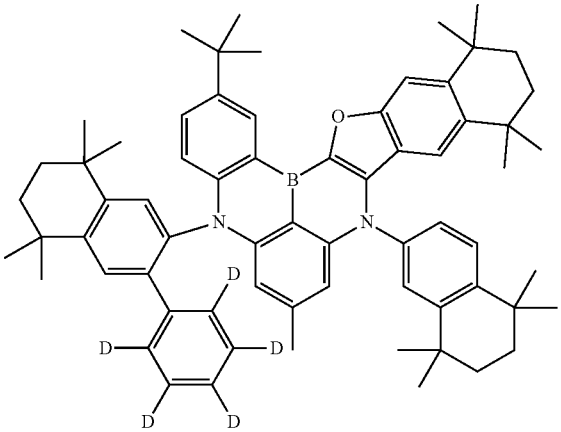
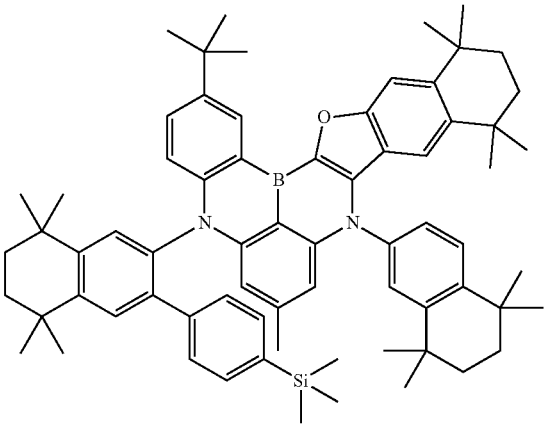

2789
-continued
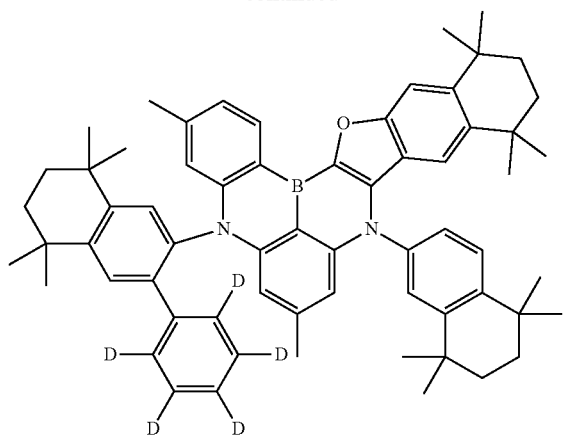
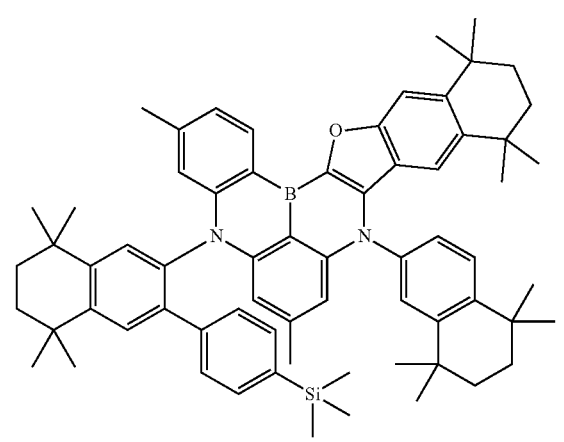
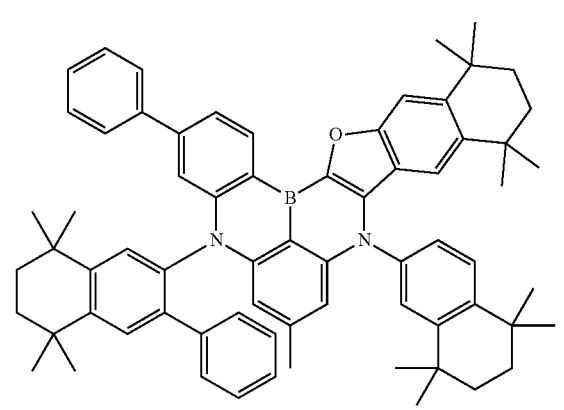
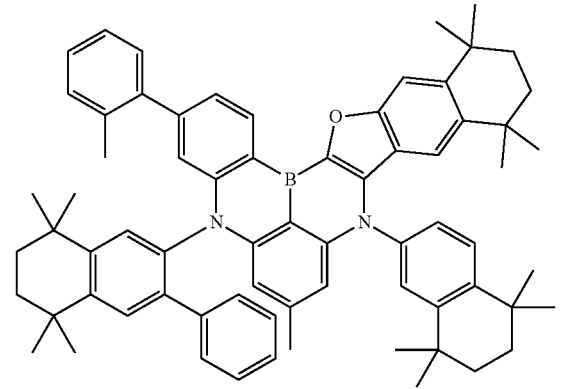
2790
-continued
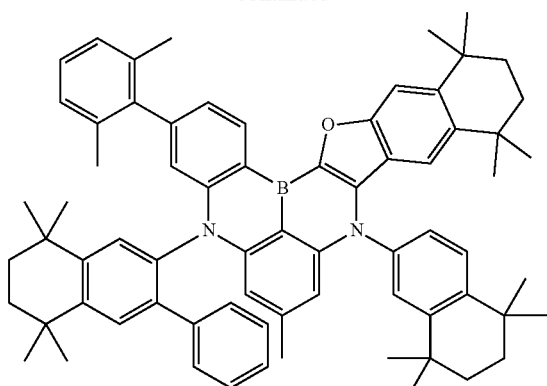
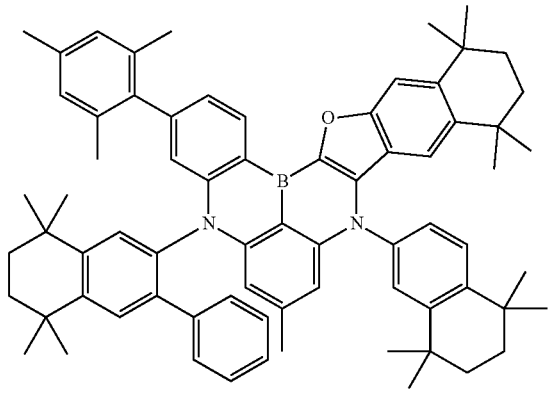
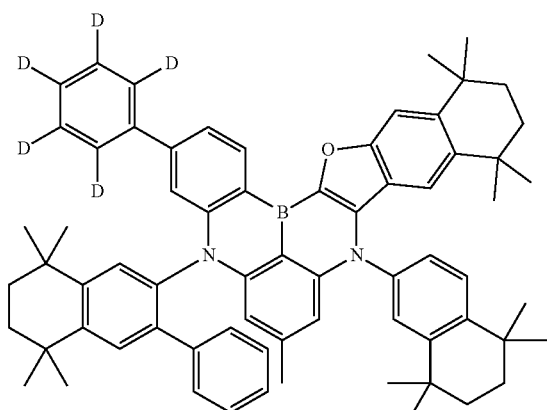
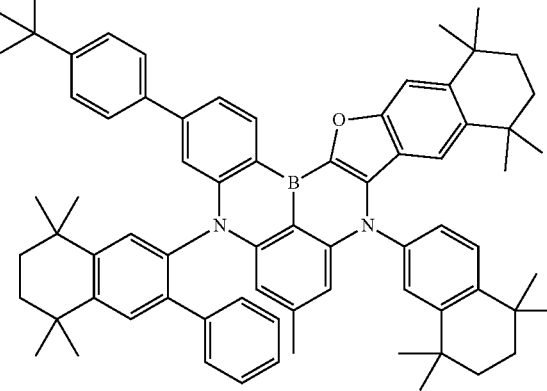

2791
-continued
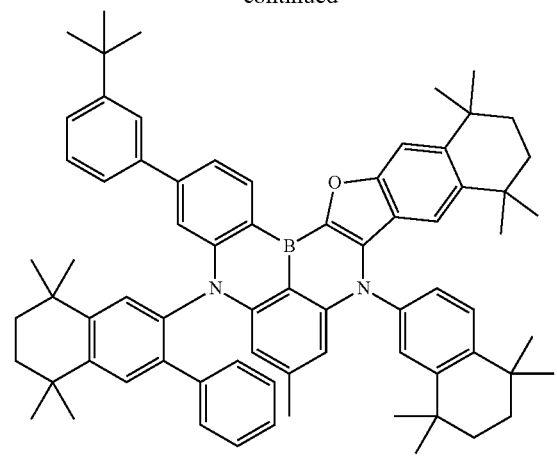
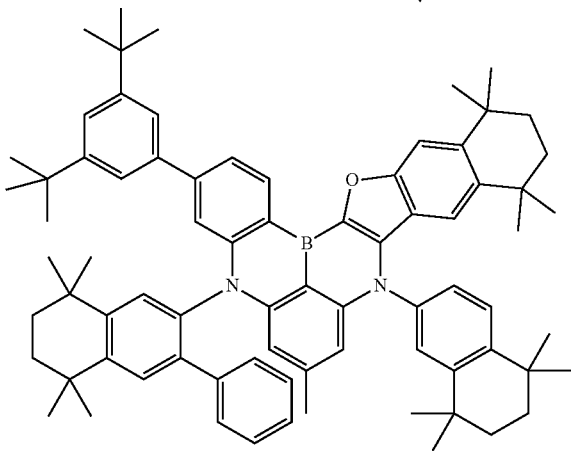
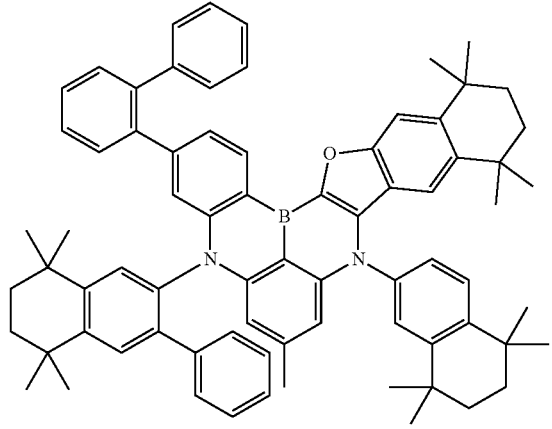
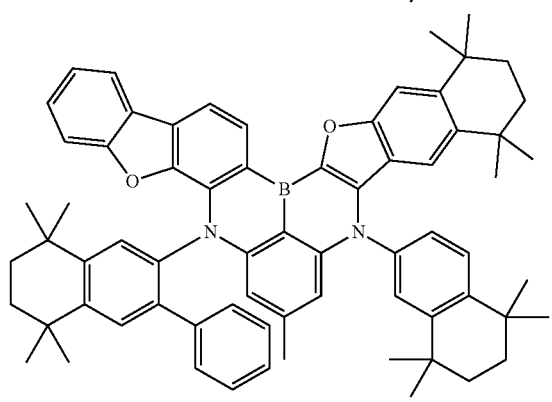
2792
-continued
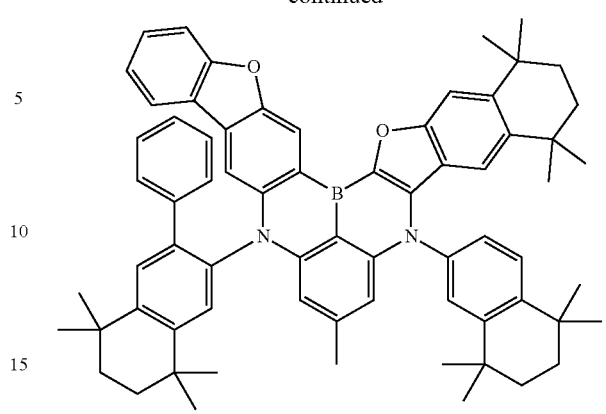
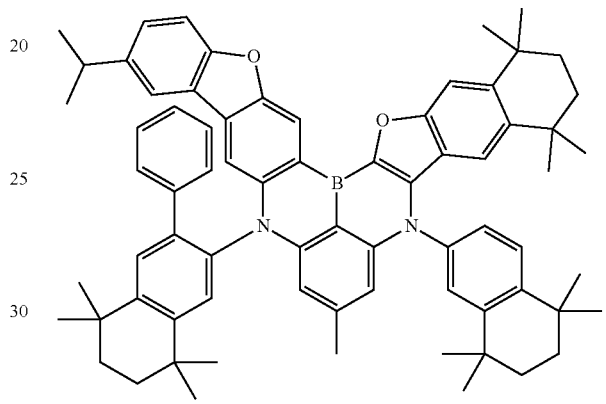
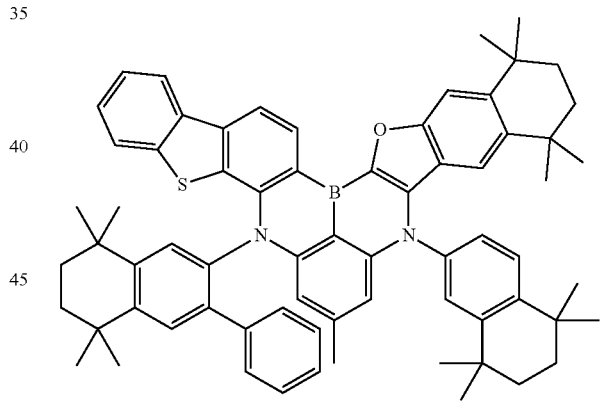
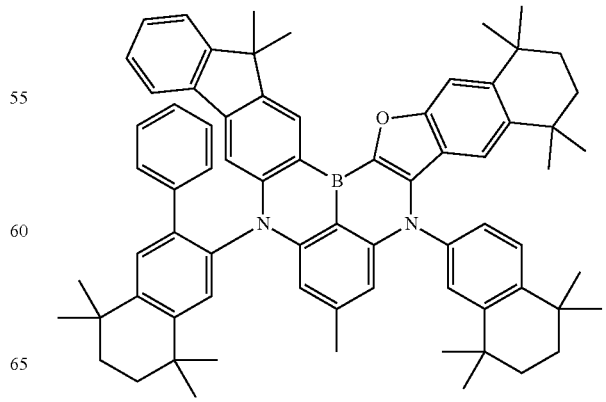

2793
-continued
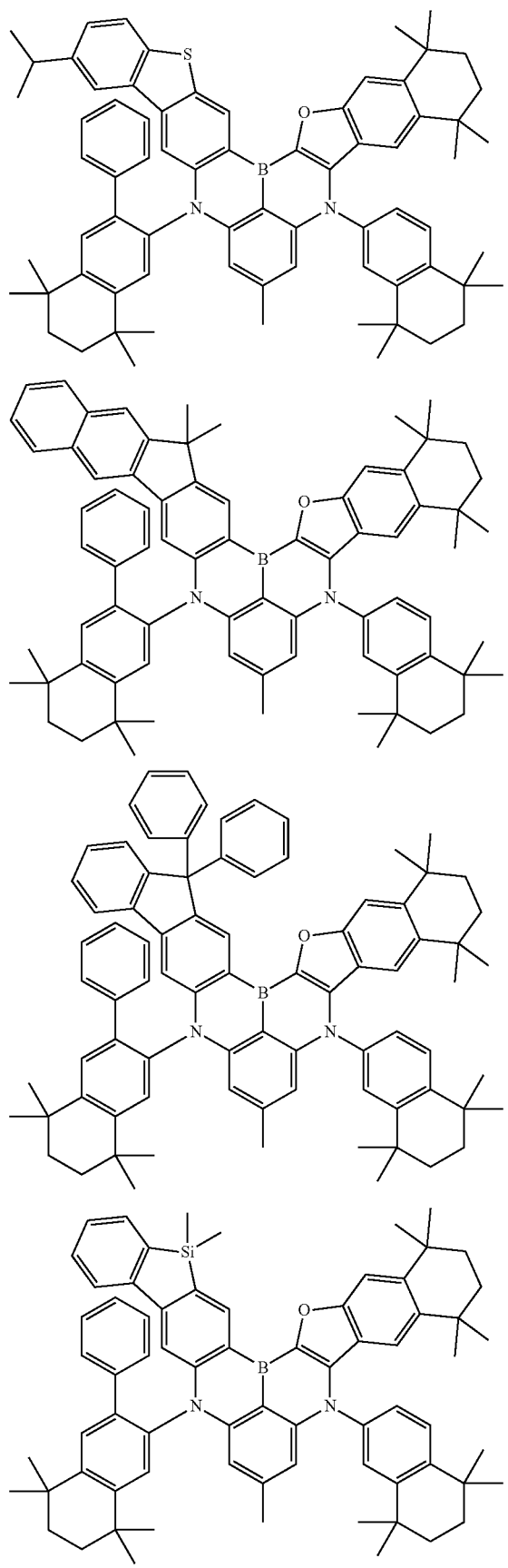
2794
-continued
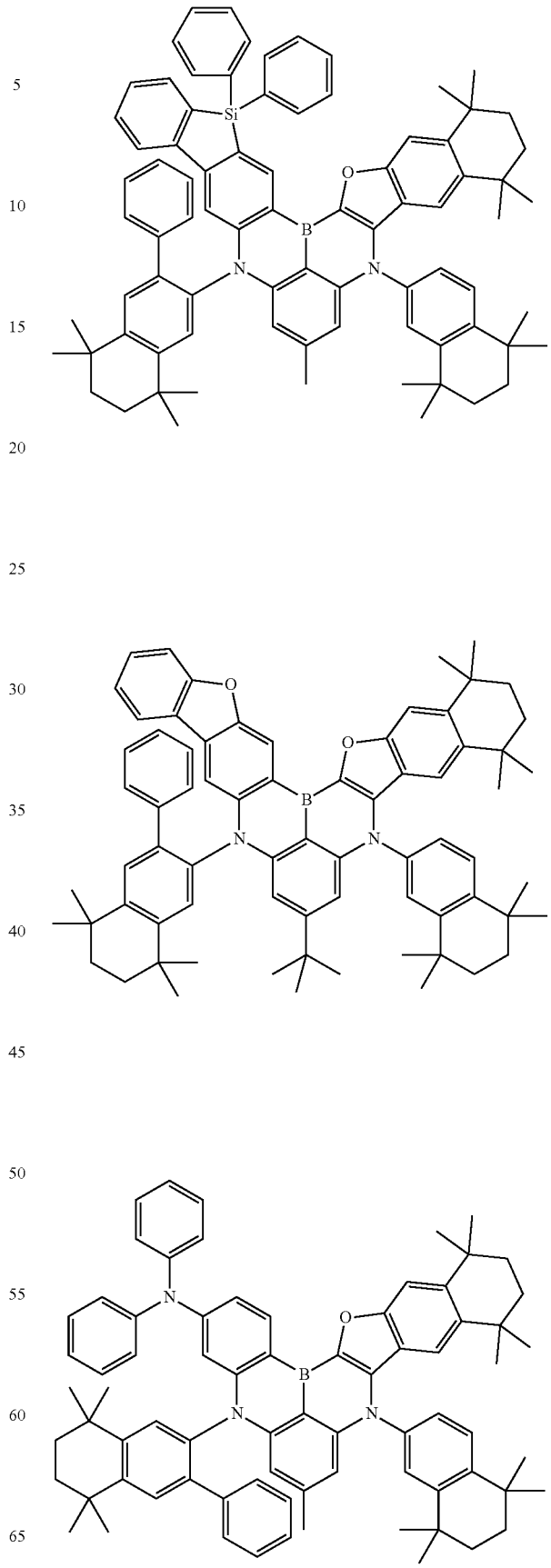

2795
-continued
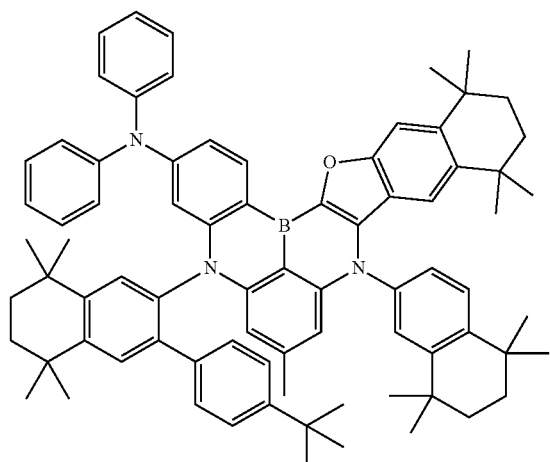
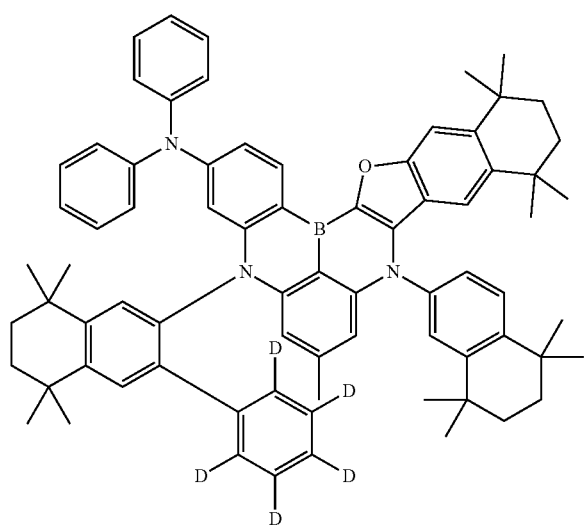
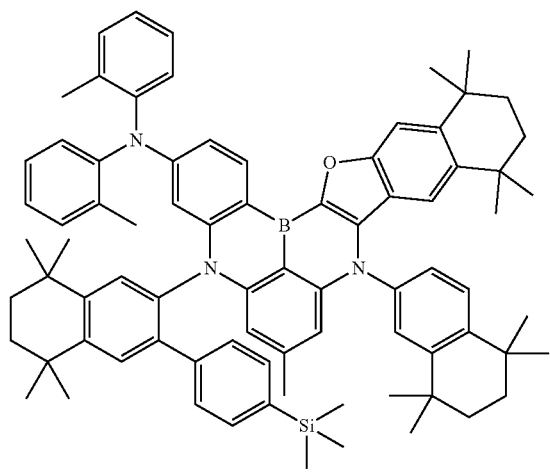
2796
-continued
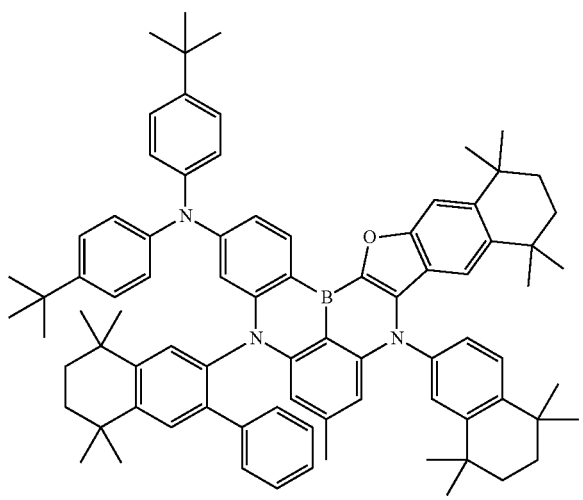
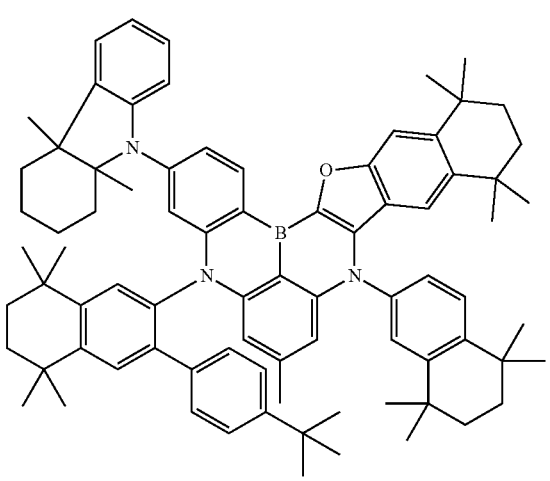
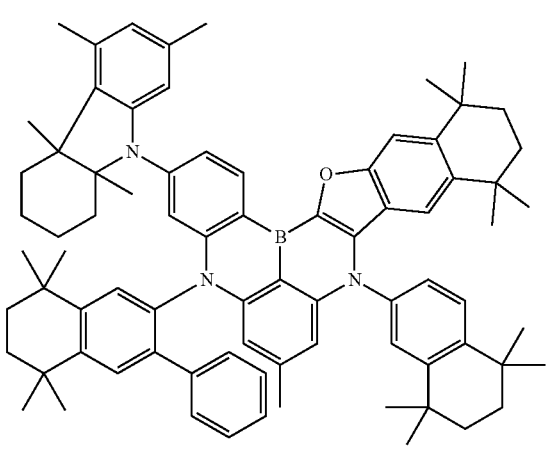

2797
-continued
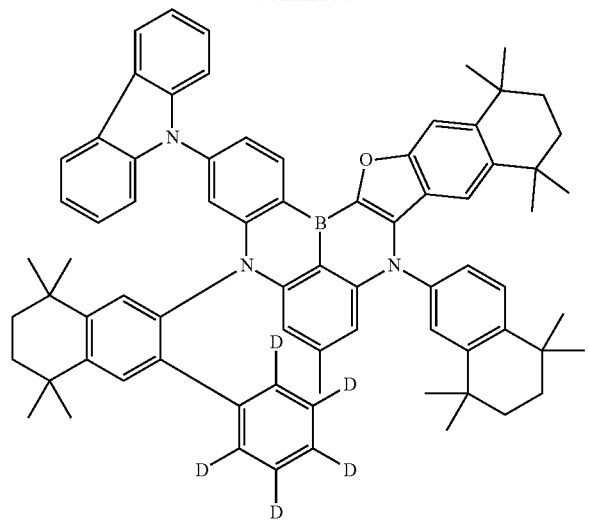
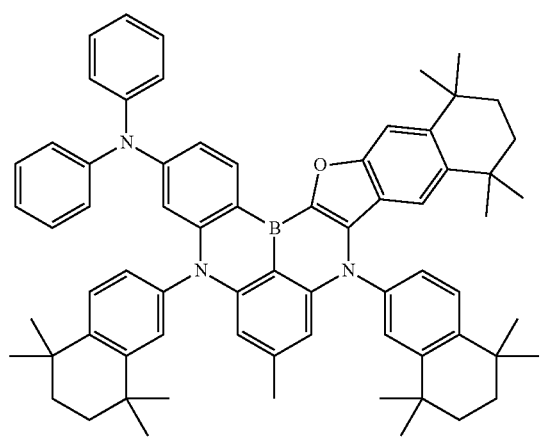
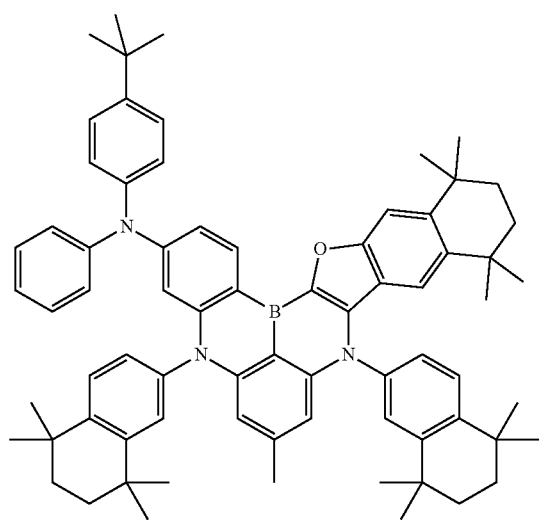
2798
-continued
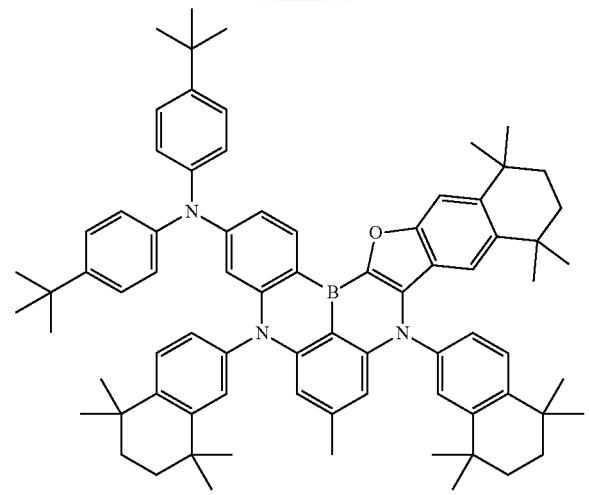
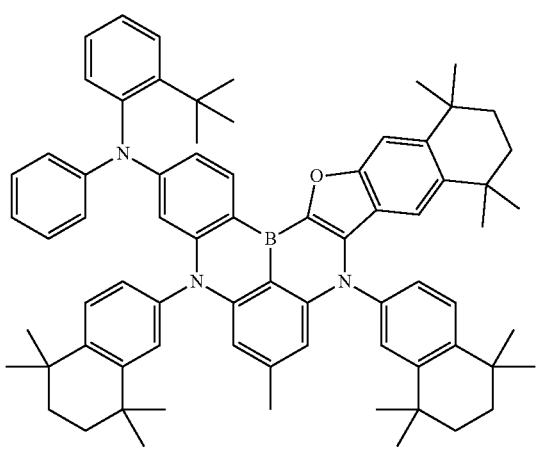
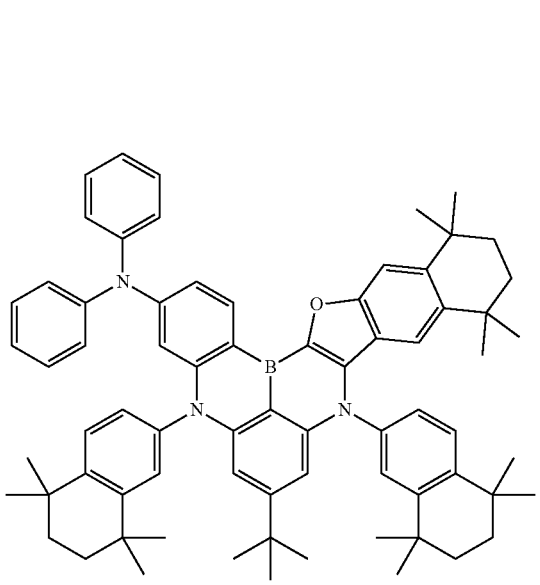

2799
-continued
2800
-continued
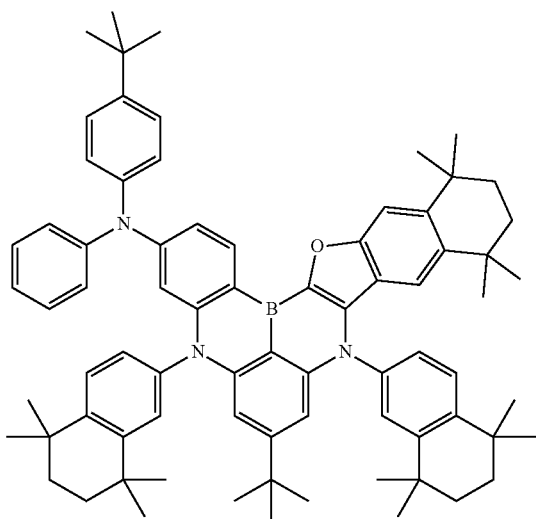
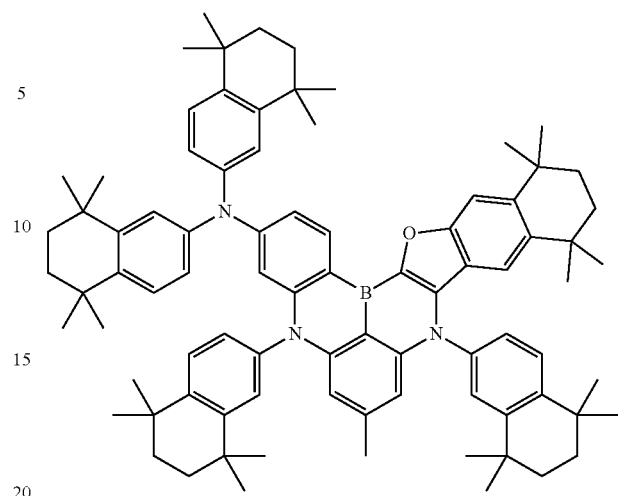
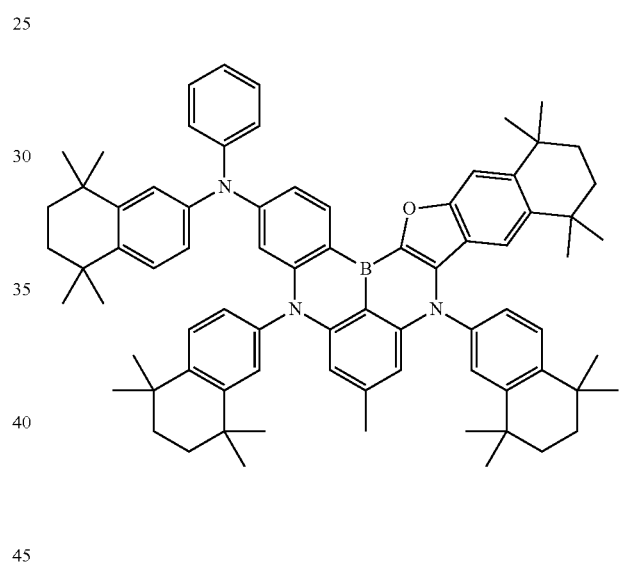
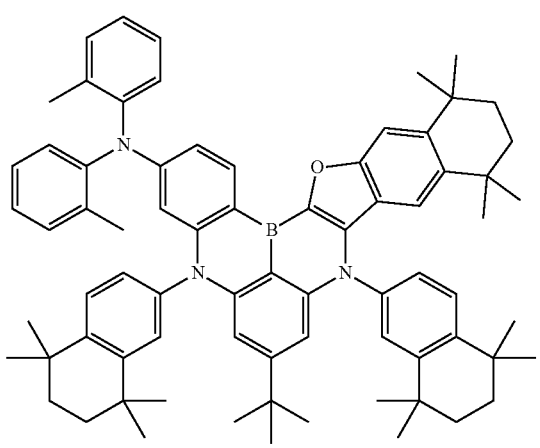
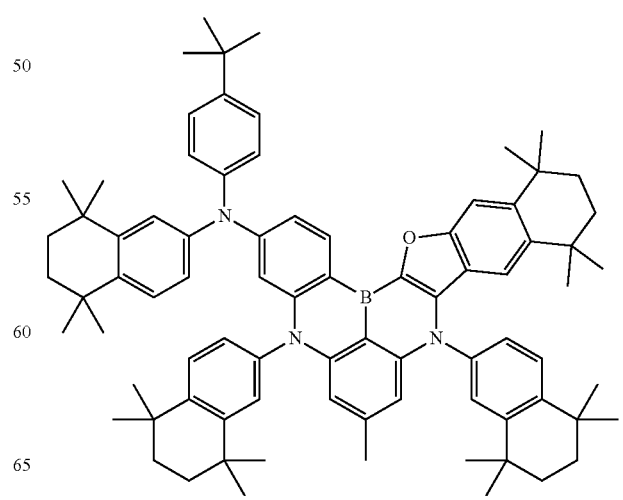

| 2801 | 2802 |
|---|---|
| -continued | -continued |
| 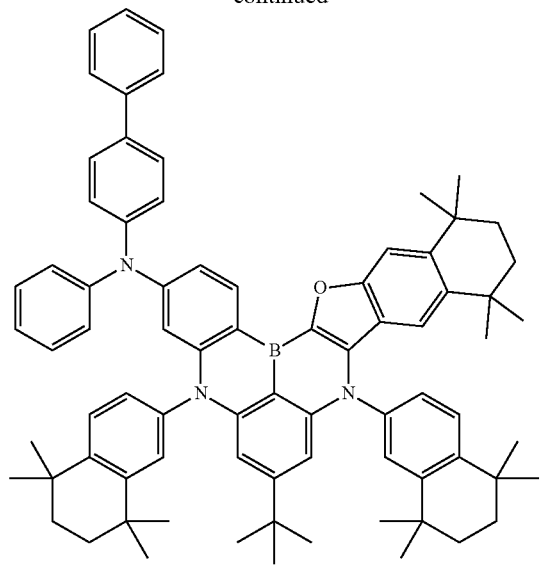 | 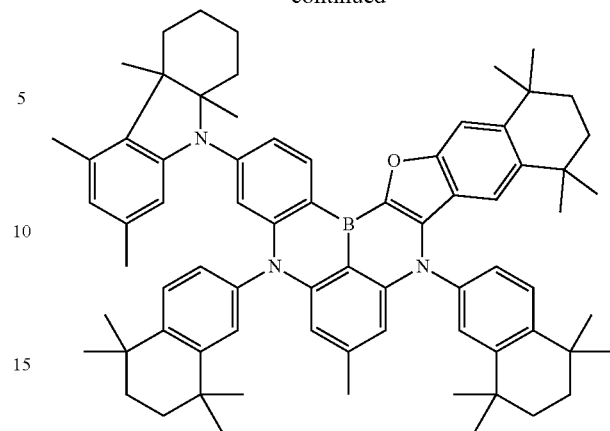 |
| 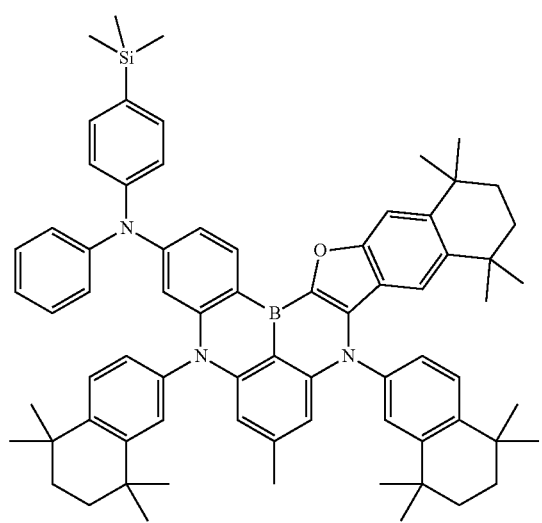 | 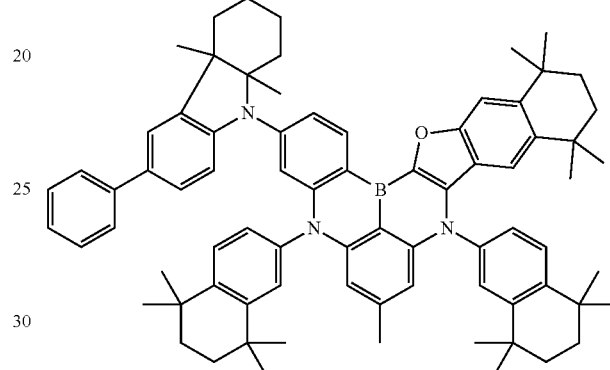 |
| 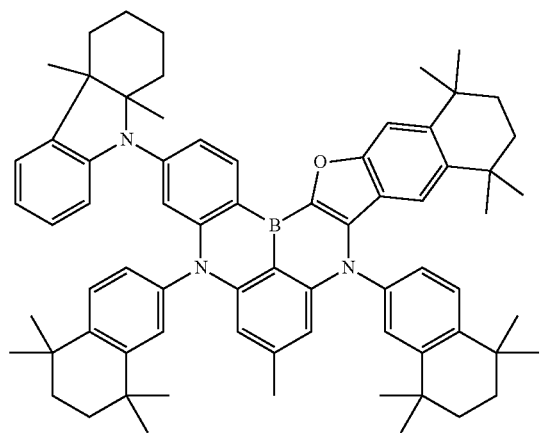 | 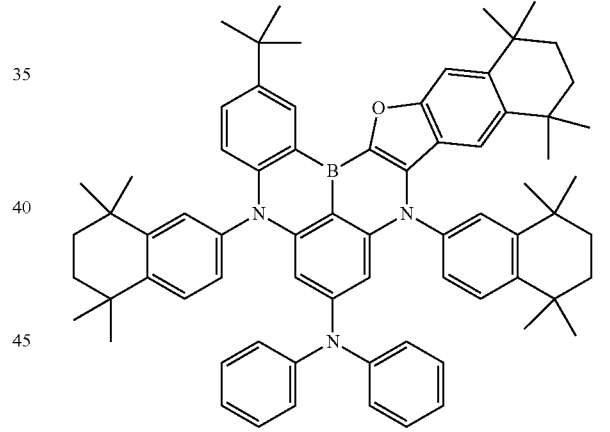 |
| | 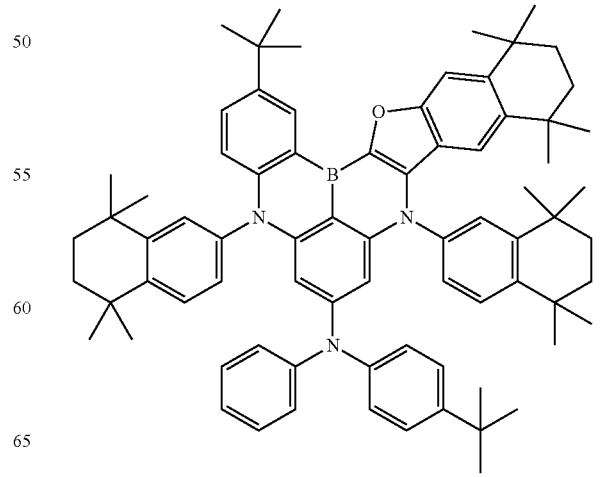 |

2803
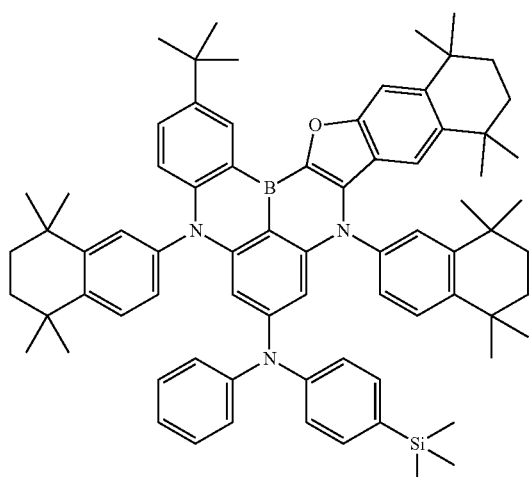
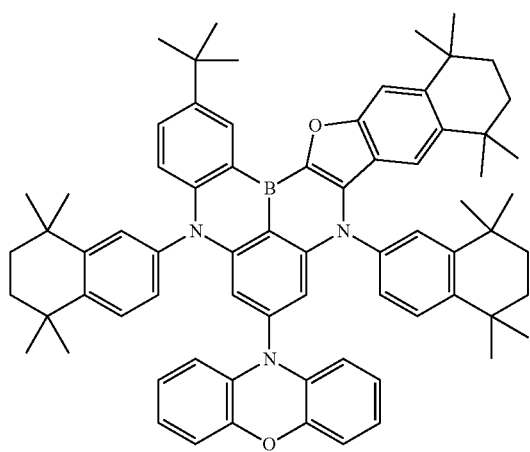
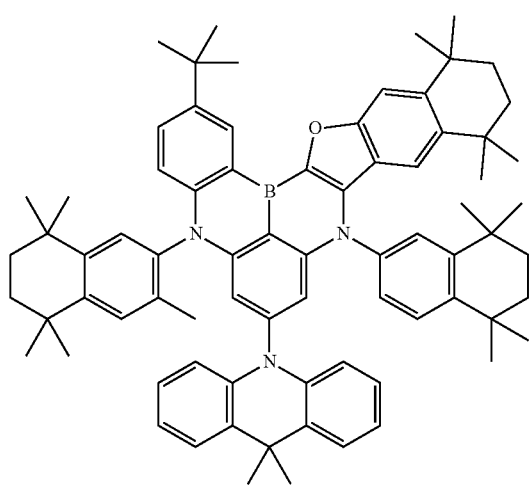
2804
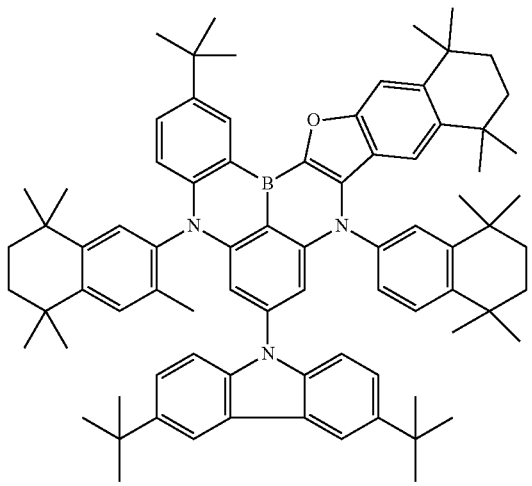
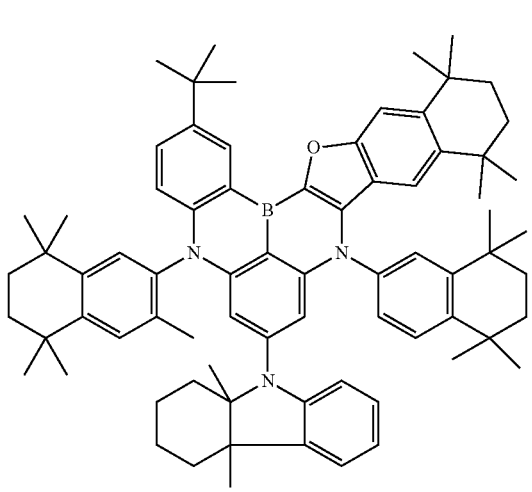
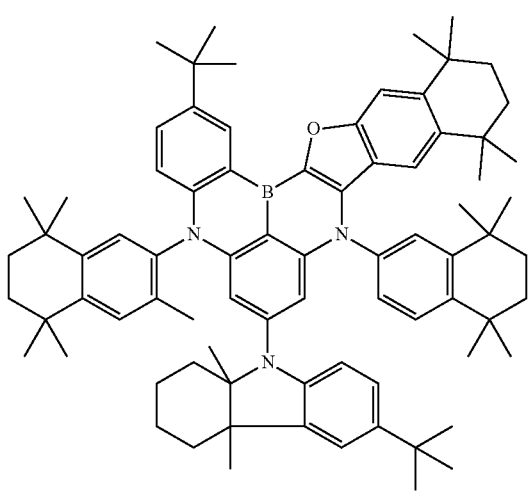

2805
-continued
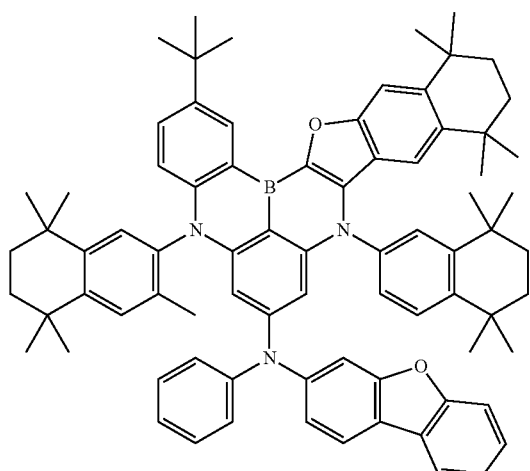
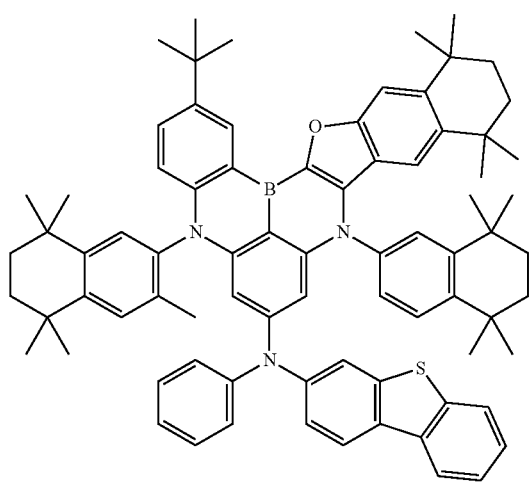
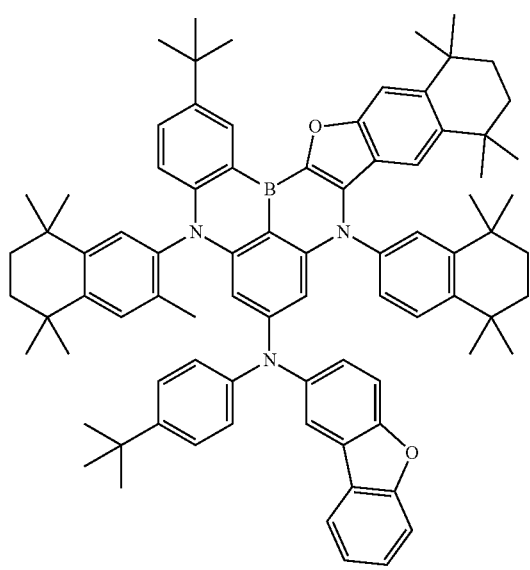
2806
-continued
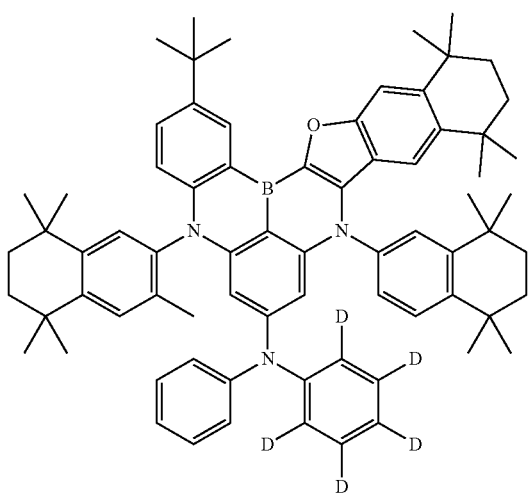
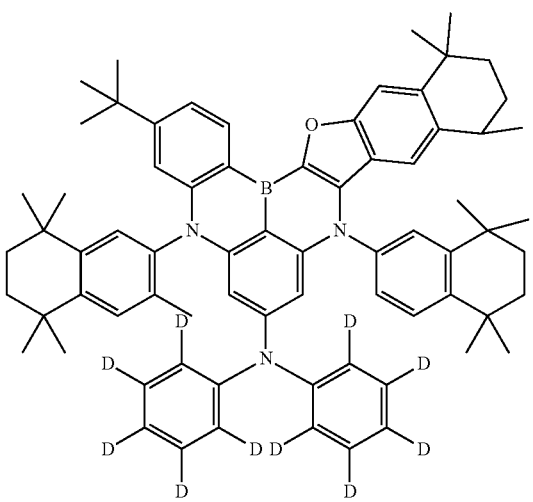
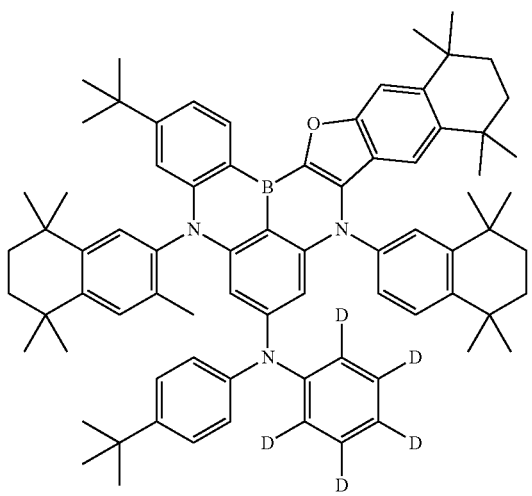

2807
-continued
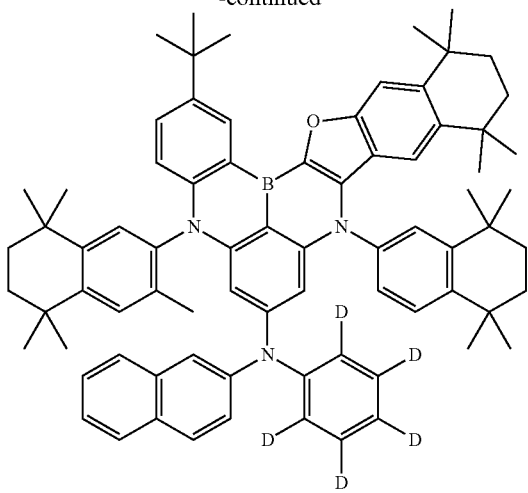
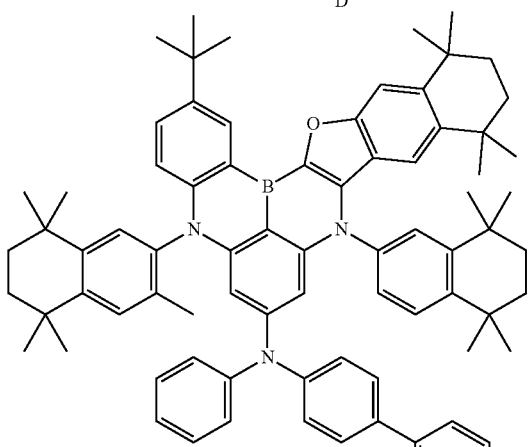
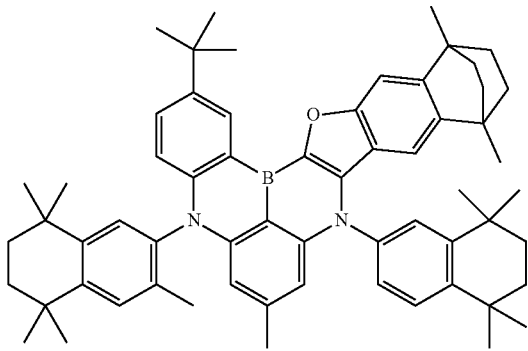
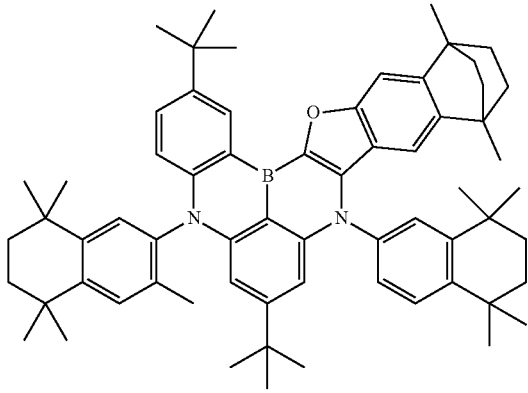
2808
-continued
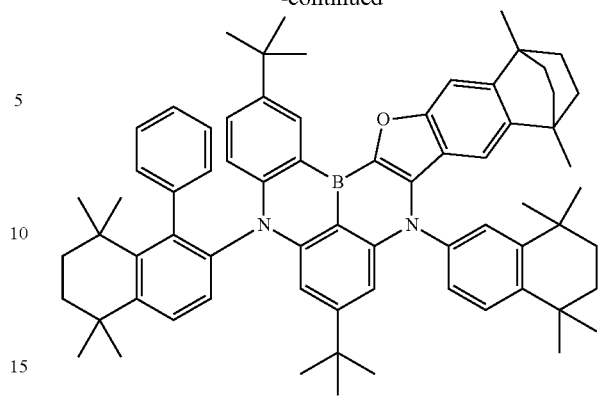
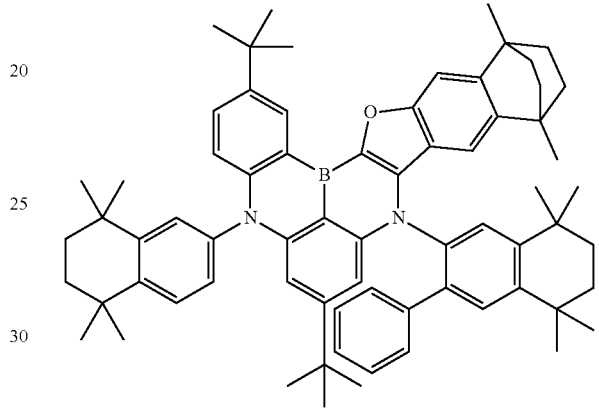
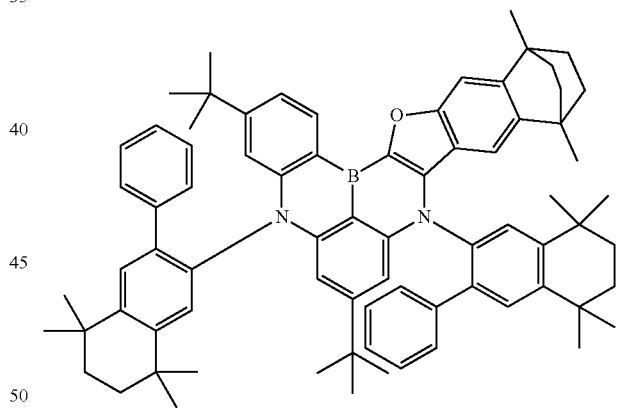
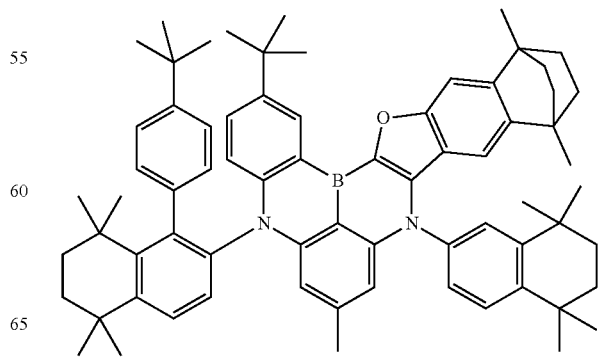

2809
-continued
2810
-continued
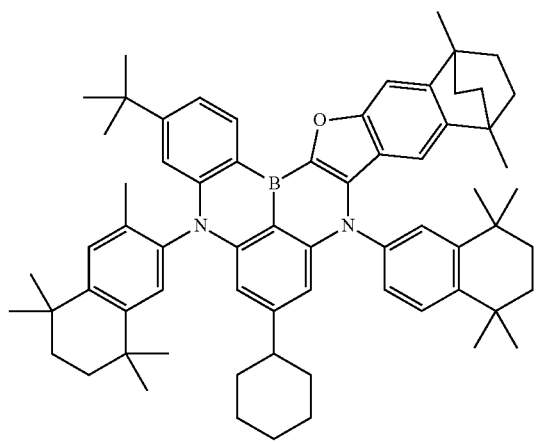
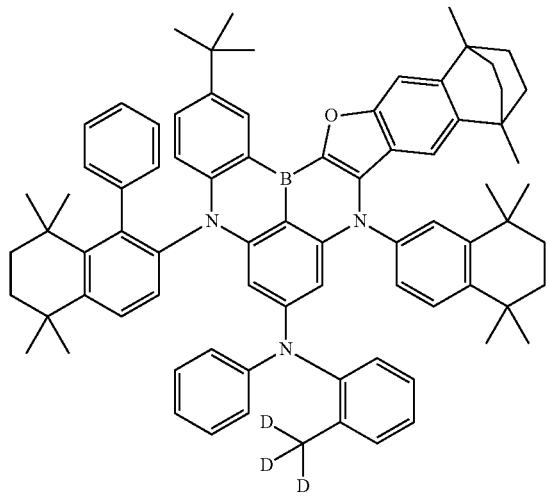
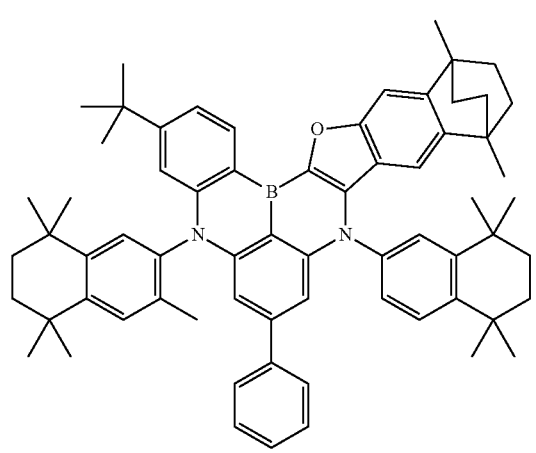
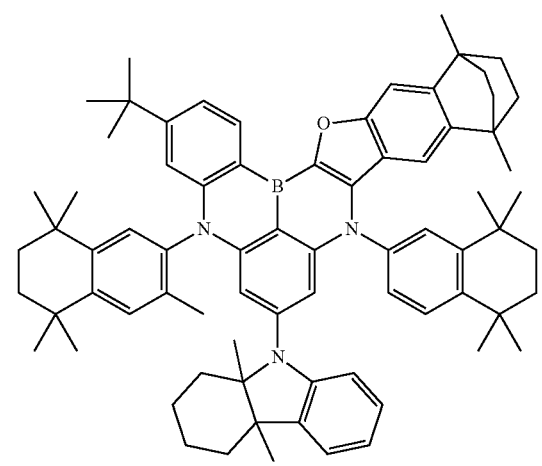
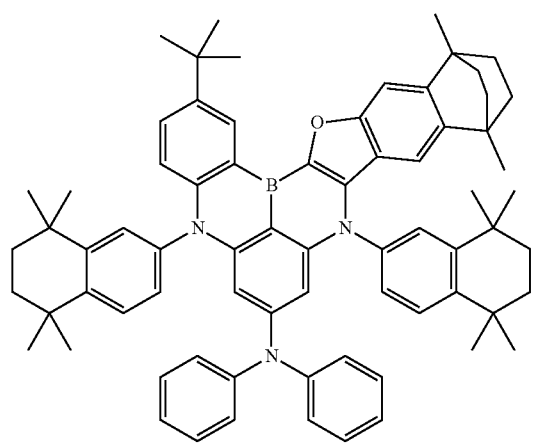
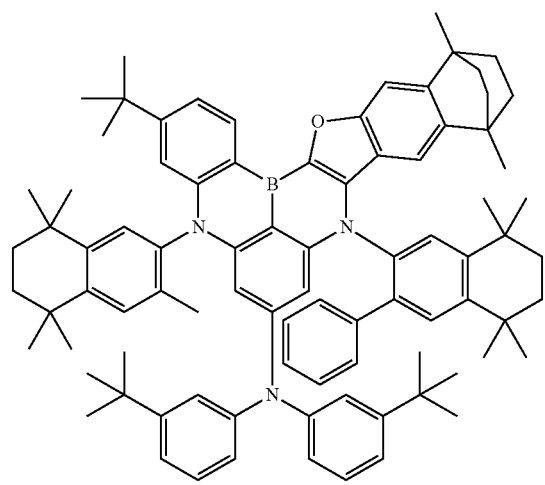

2811
-continued
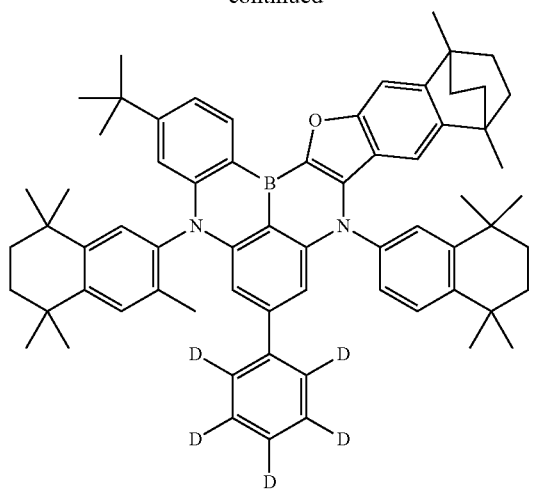
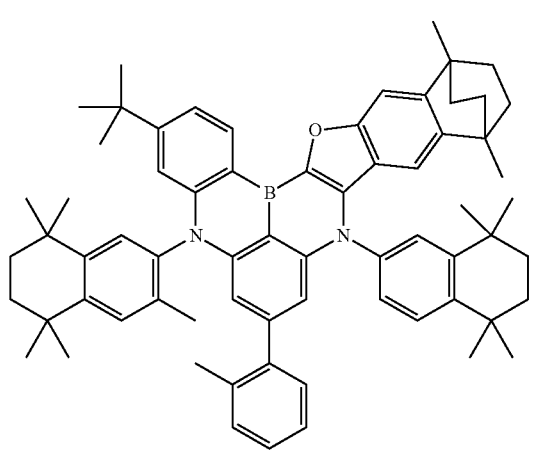
2812
-continued
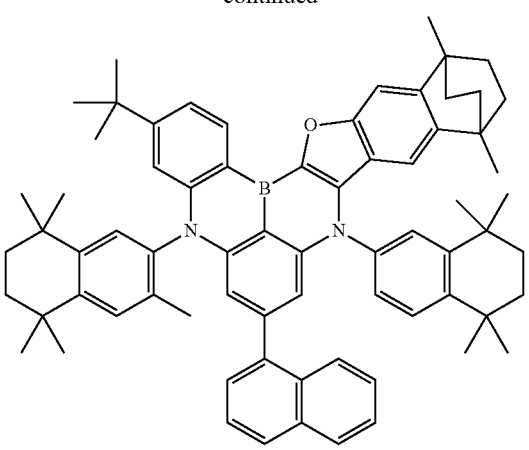
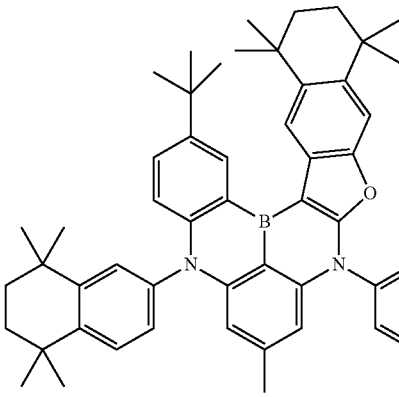
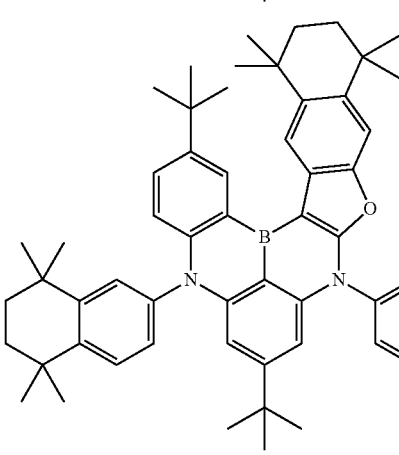
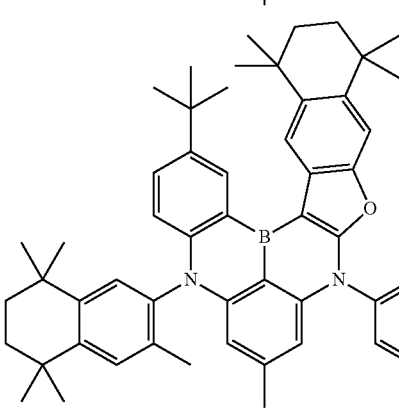

2813
-continued
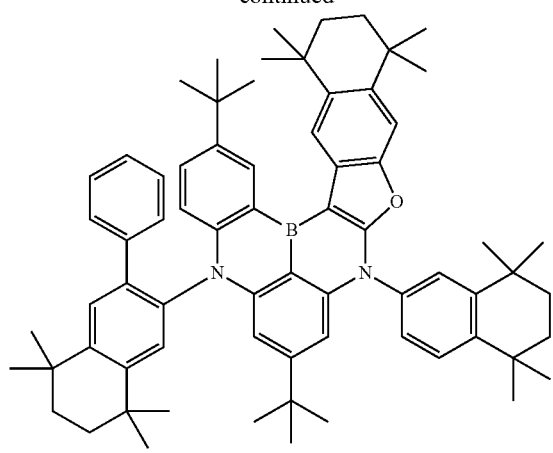
2814
-continued
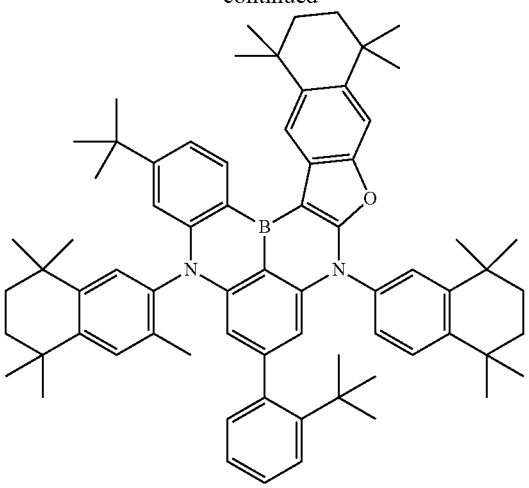
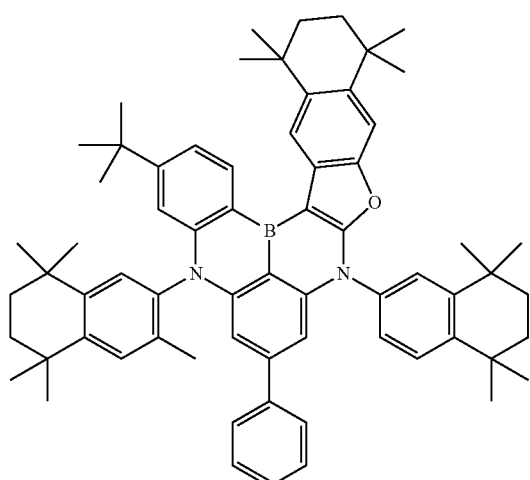
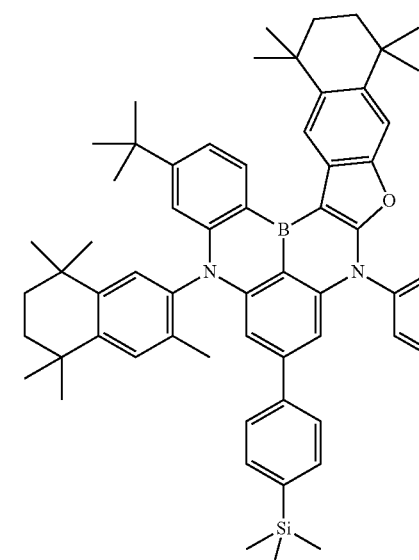
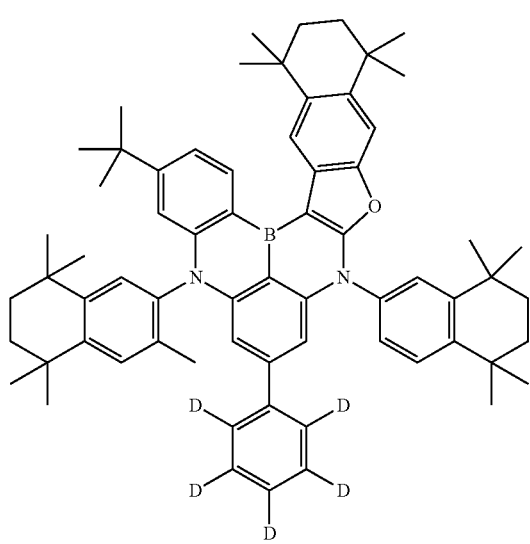
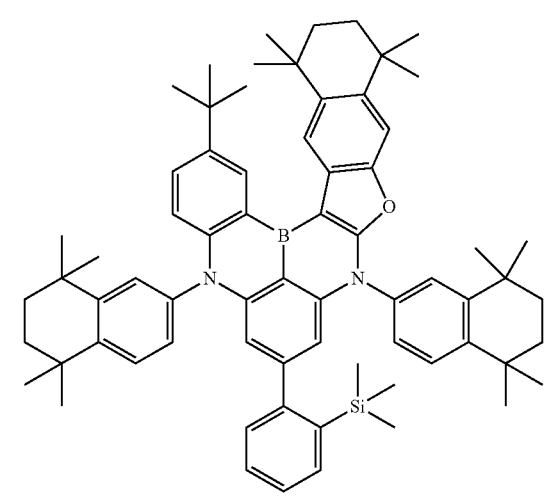

2815
-continued
2816
-continued
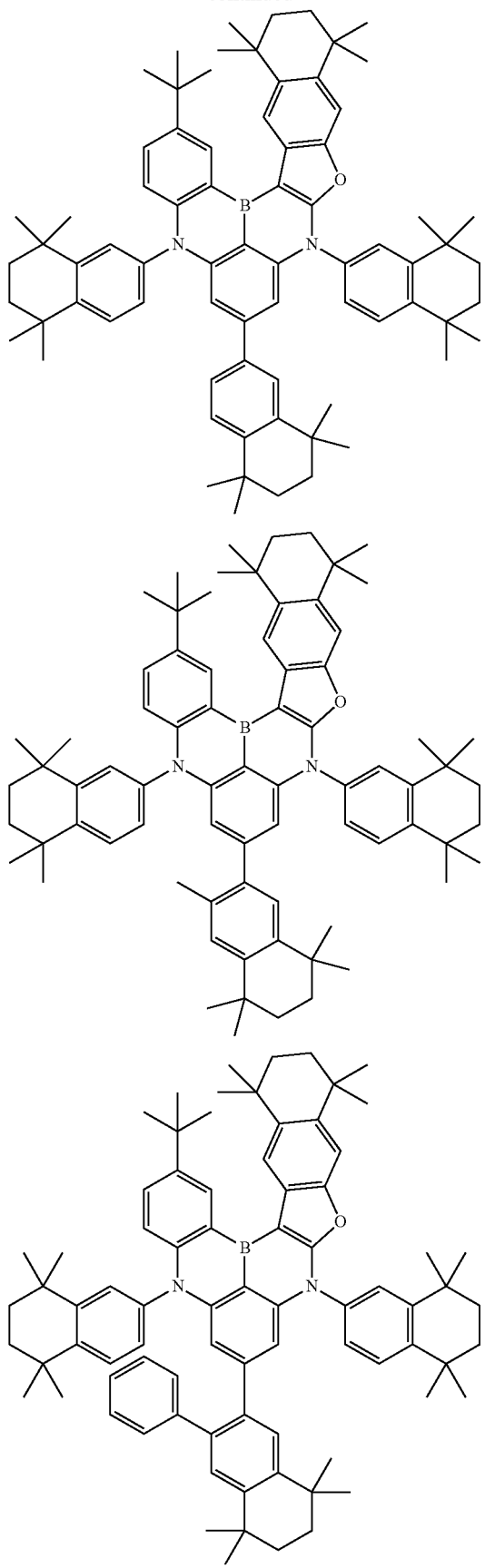
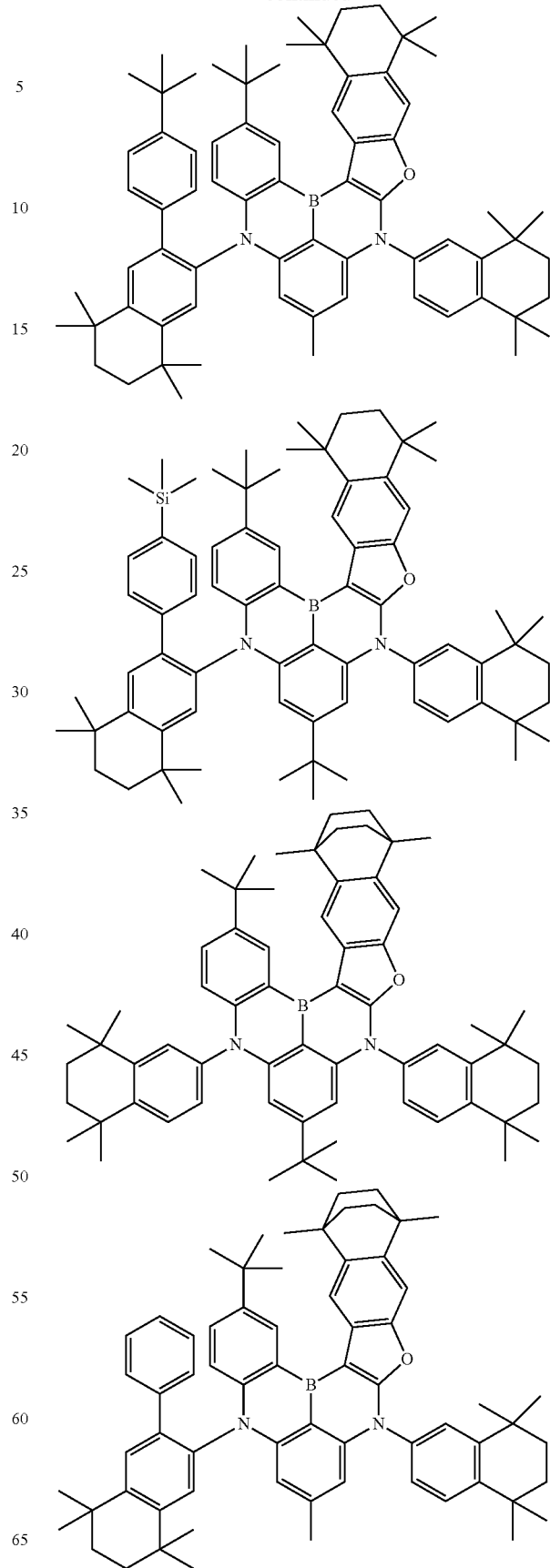

2817
-continued
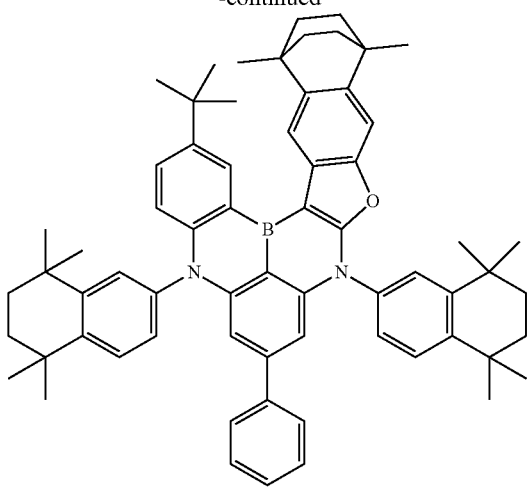
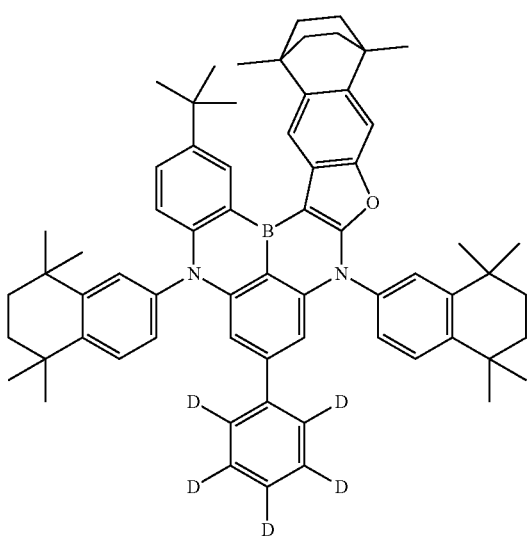
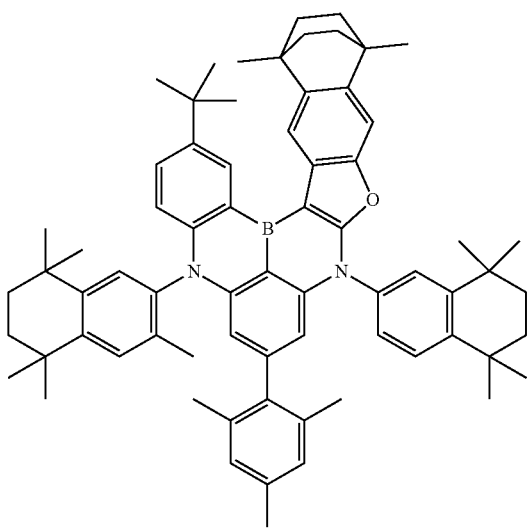
2818
-continued
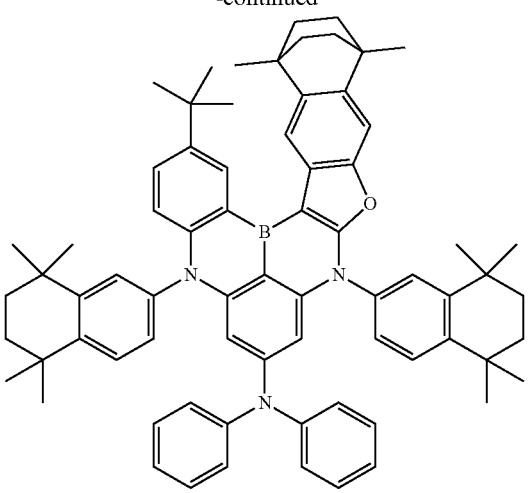
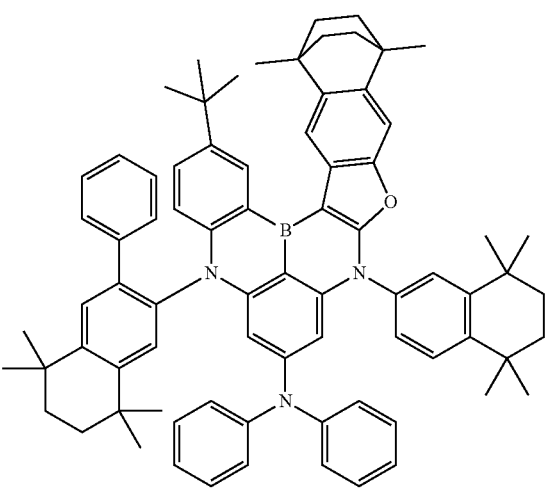
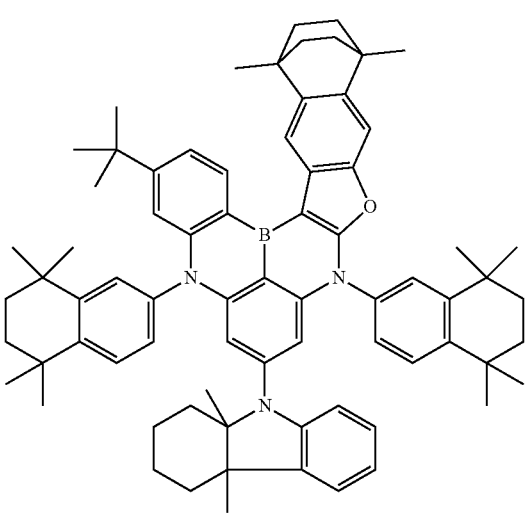

2819
-continued
2820
-continued
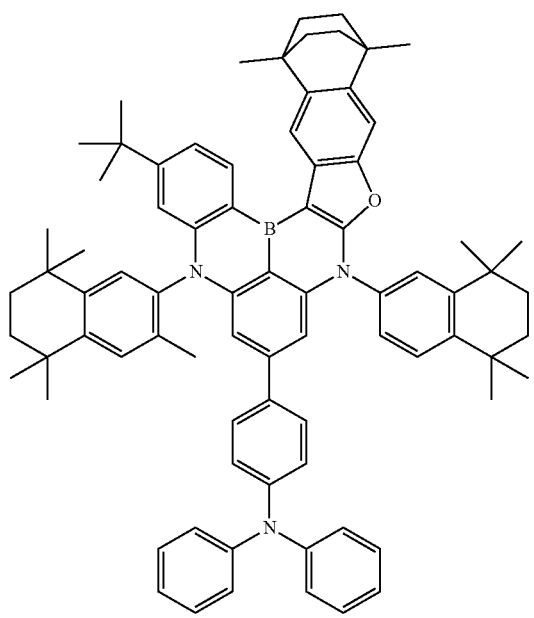
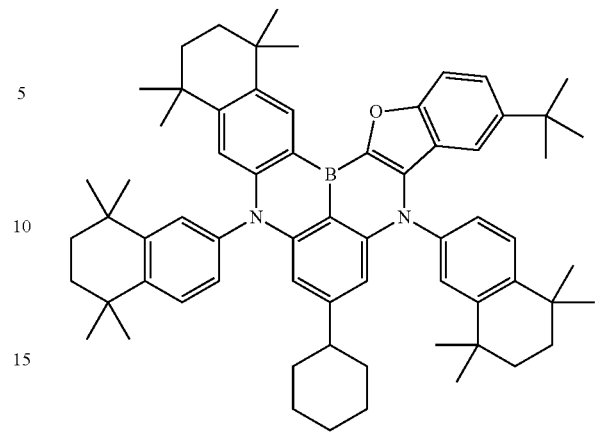
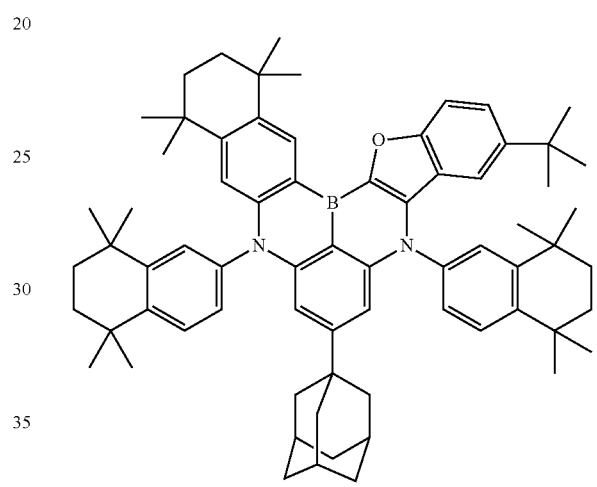
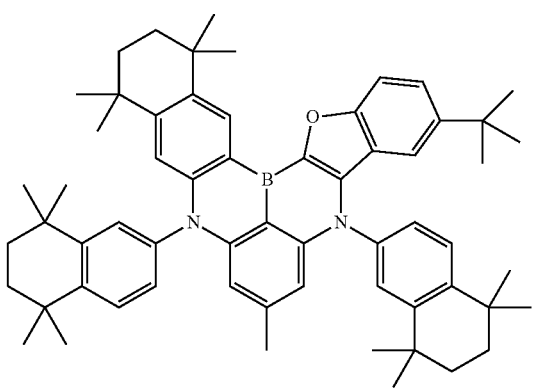
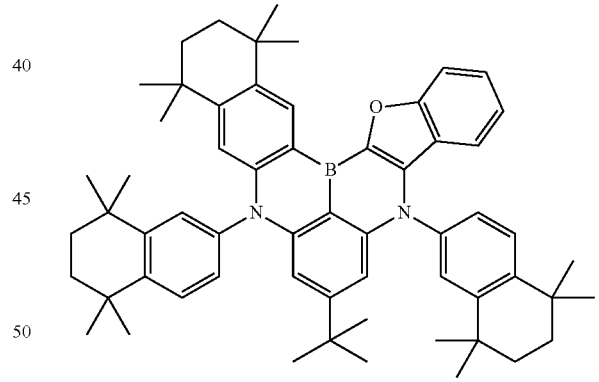
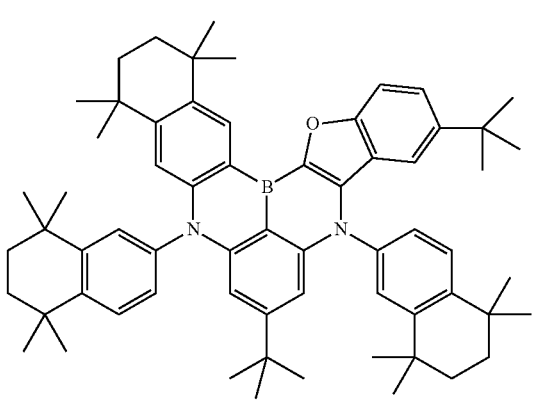
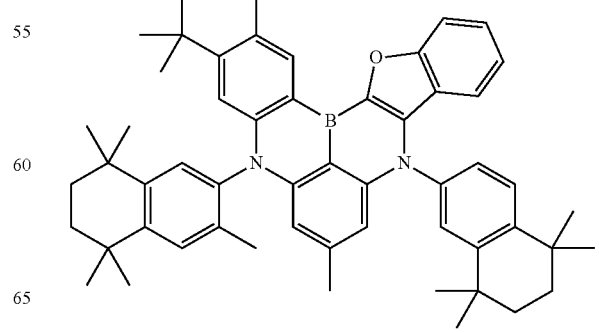

2821
-continued
2822
-continued
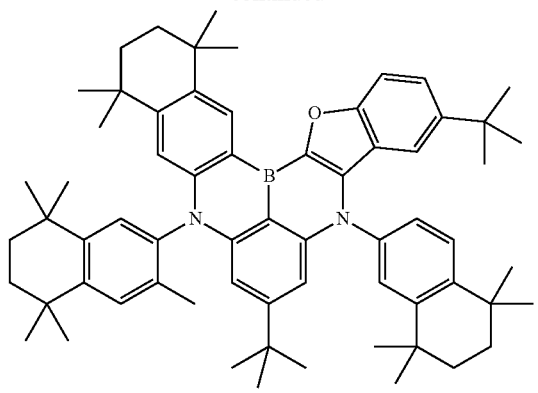
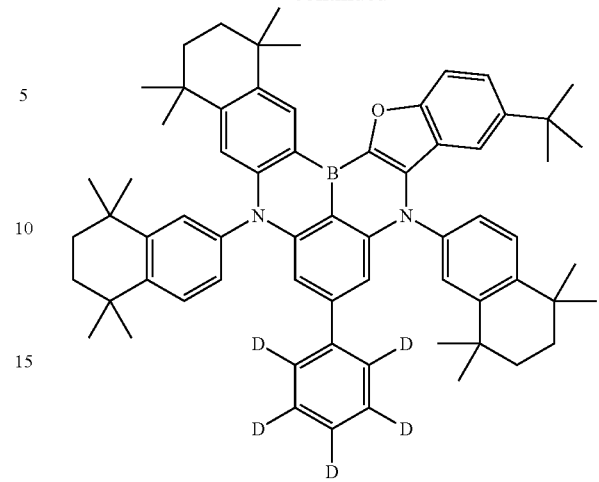
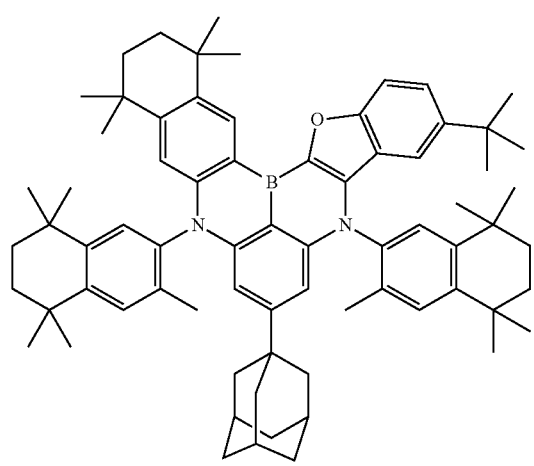
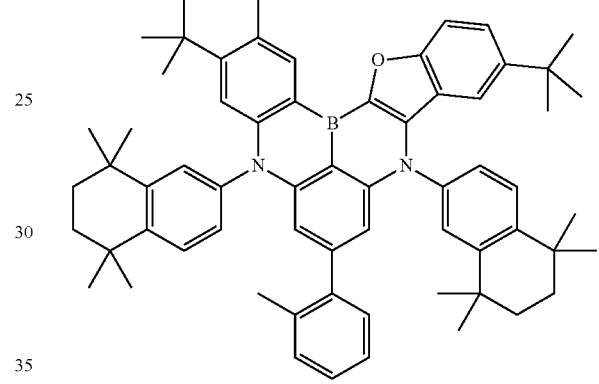
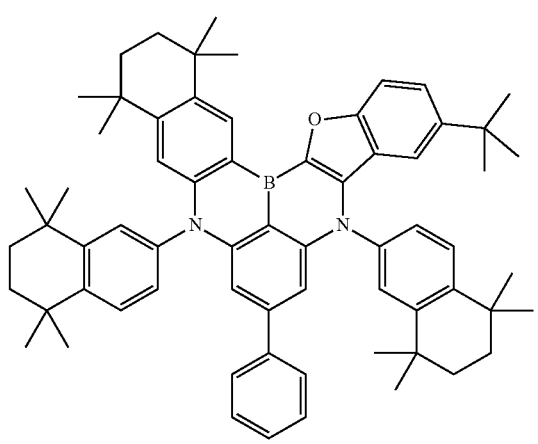
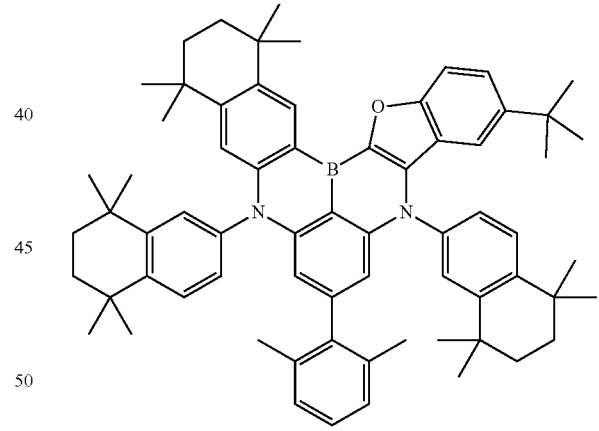
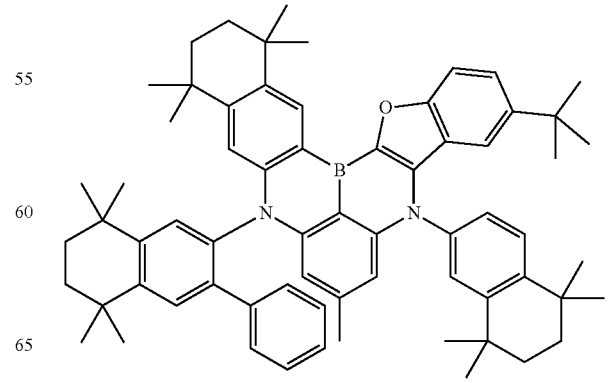

| 2823 -continued | 2824 -continued |
|---|---|
| 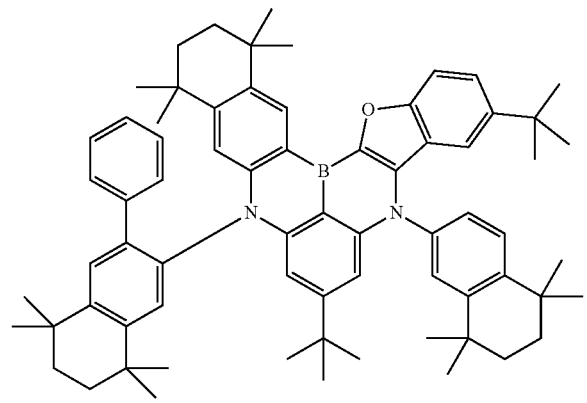 | 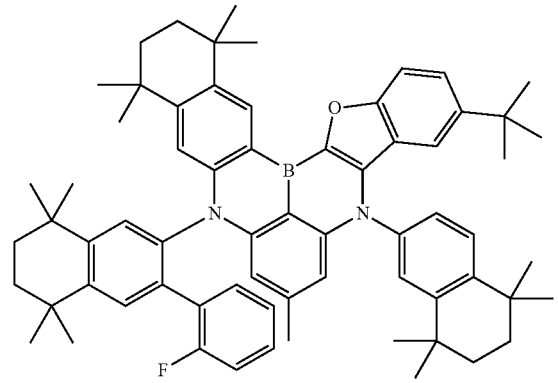 |
| 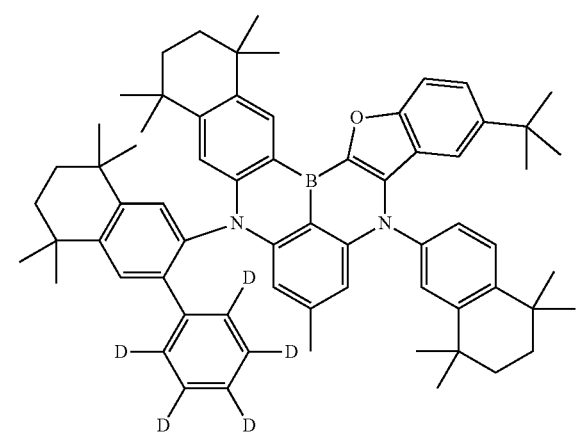 | 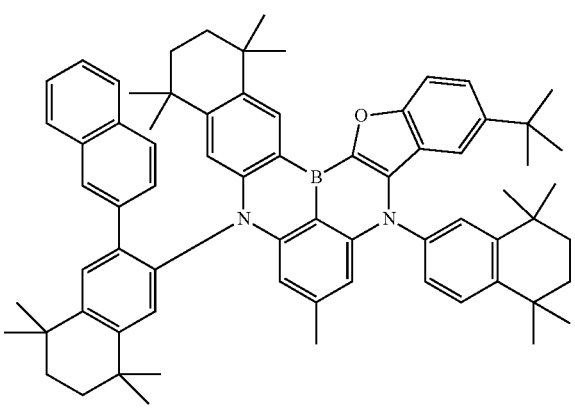 |
| 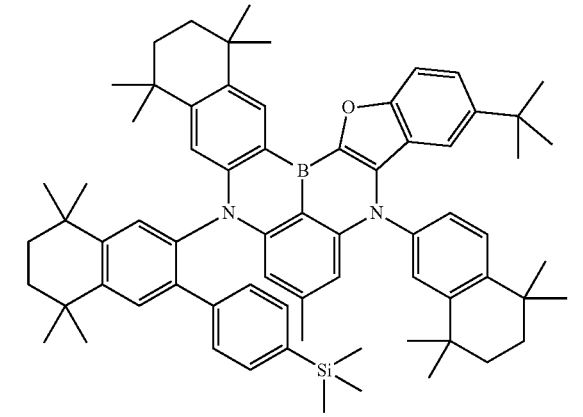 | 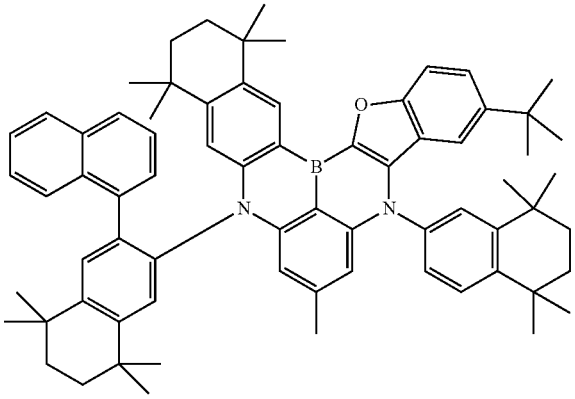 |
| 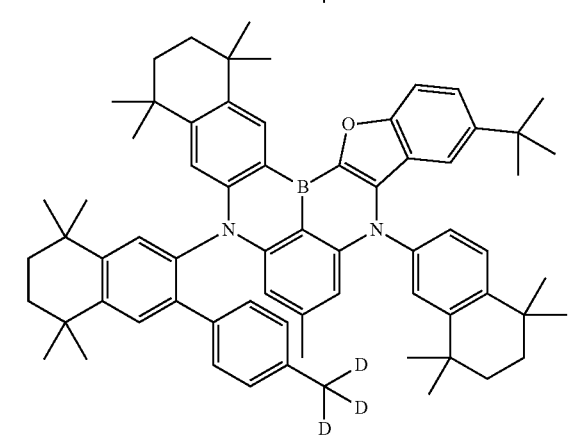 | 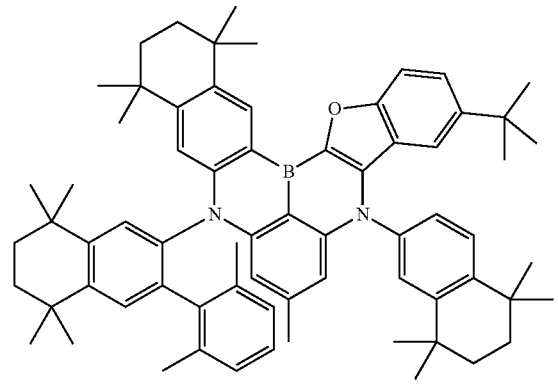 |

2825
-continued
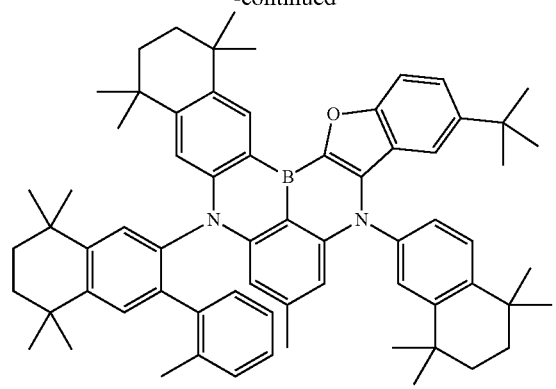
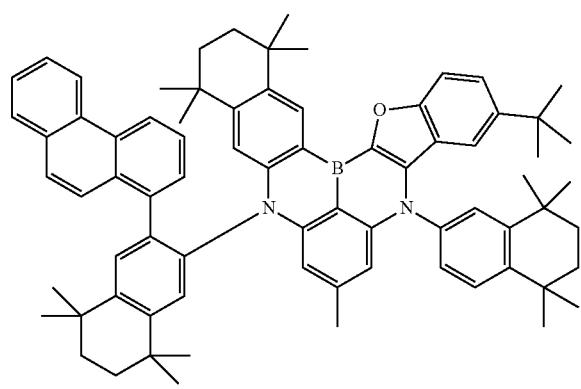
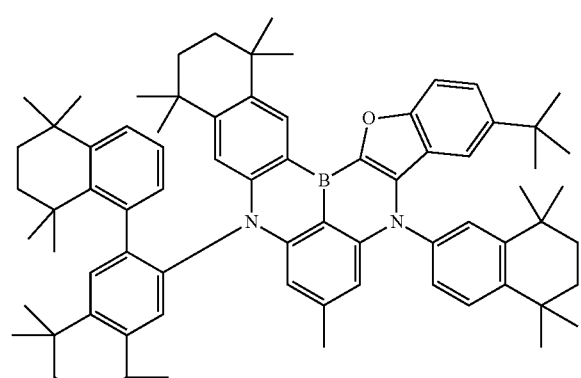
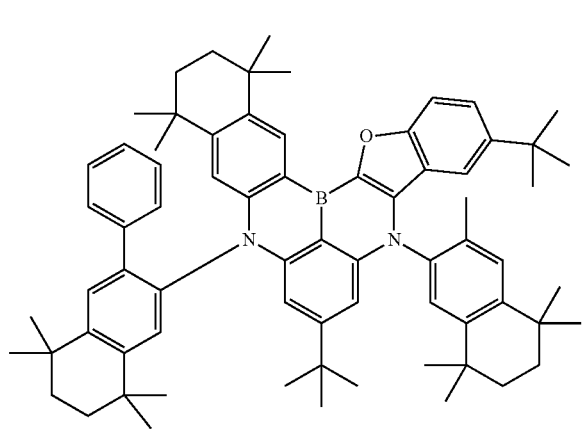
2826
-continued
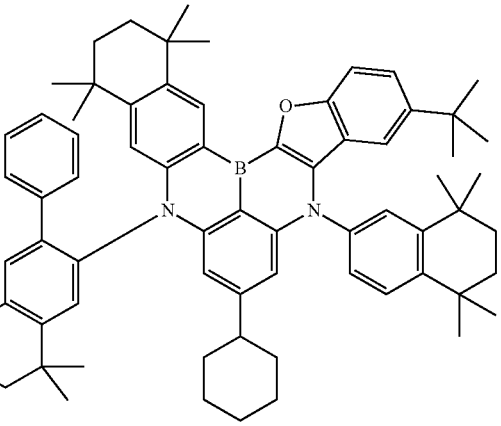
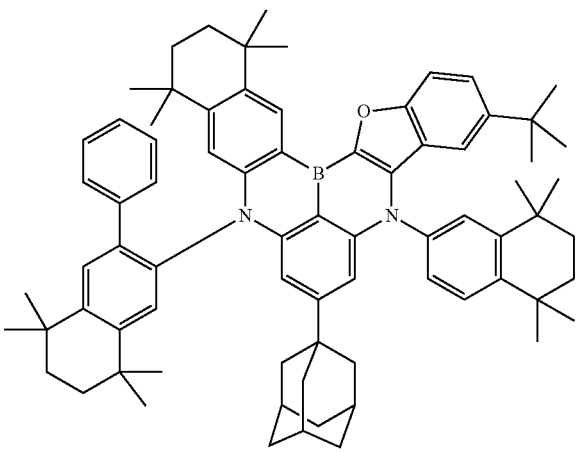
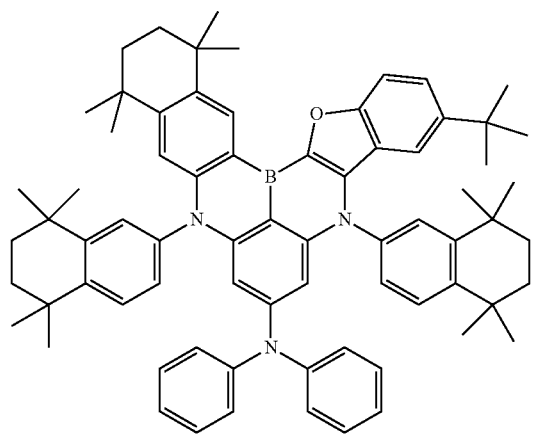

2827
-continued
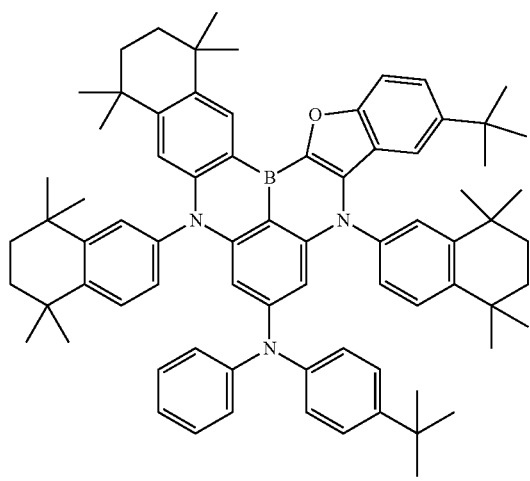
2828
-continued
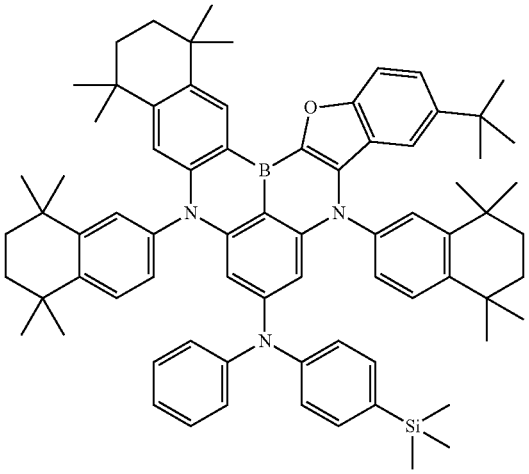
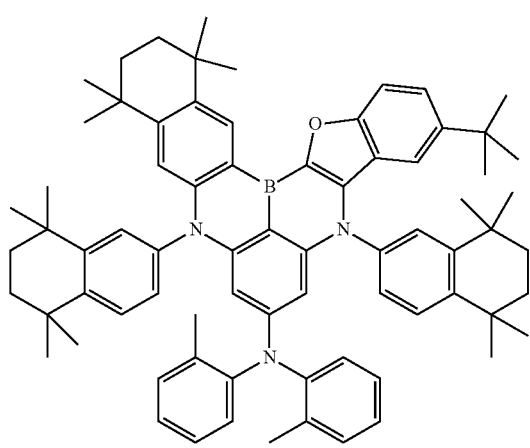
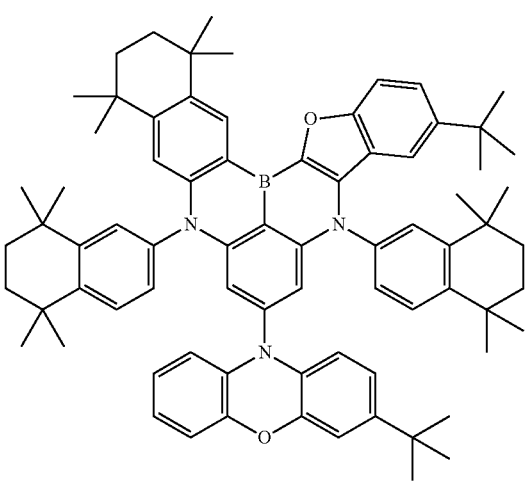
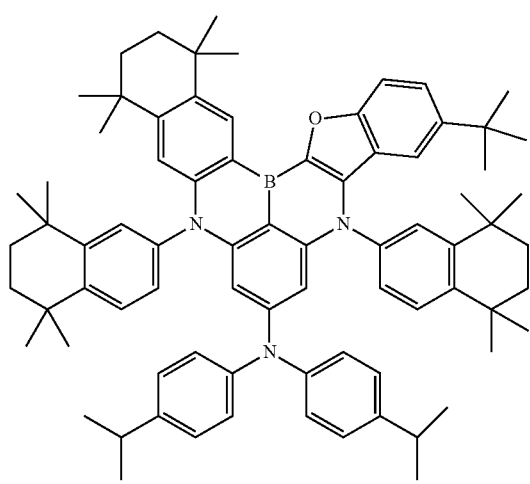
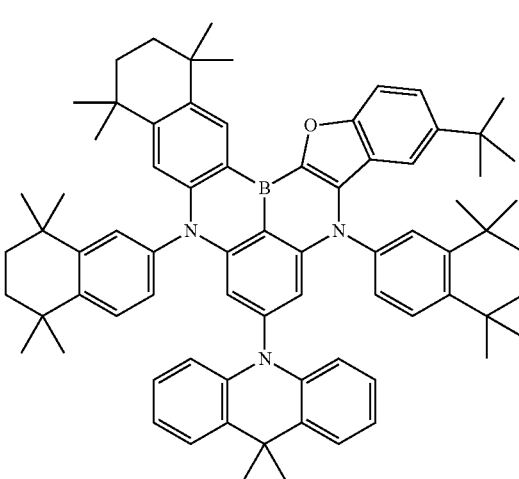

2829
-continued
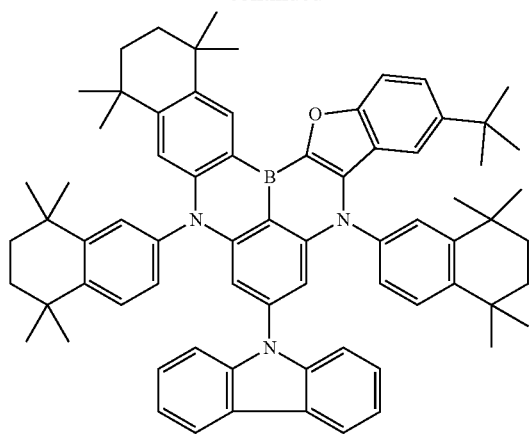
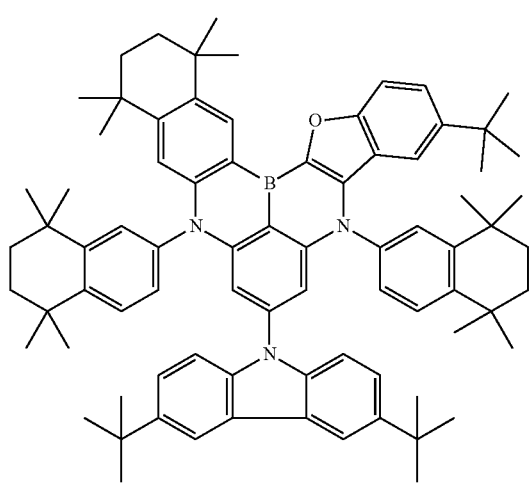
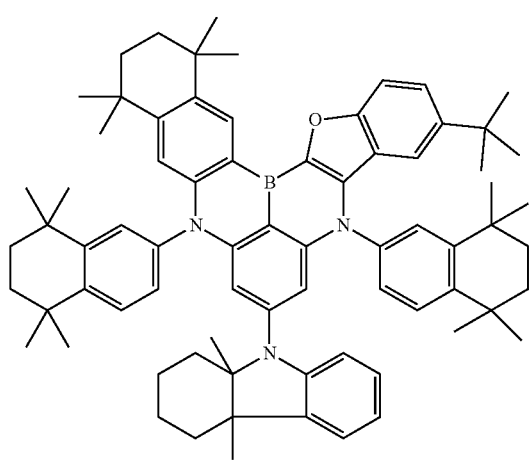
2830
-continued
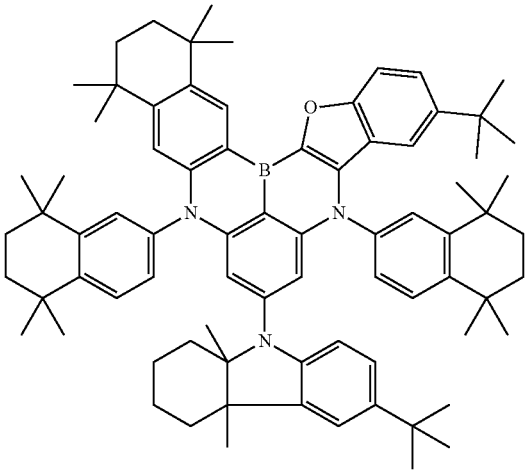
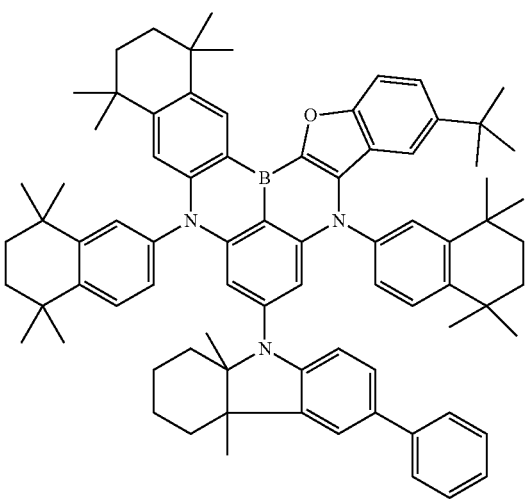
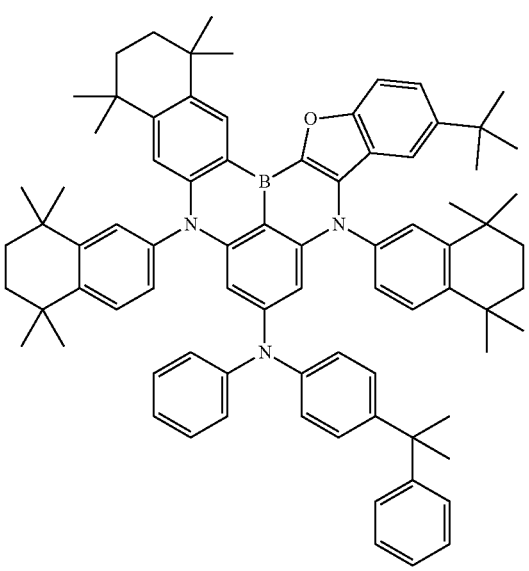

2831
-continued
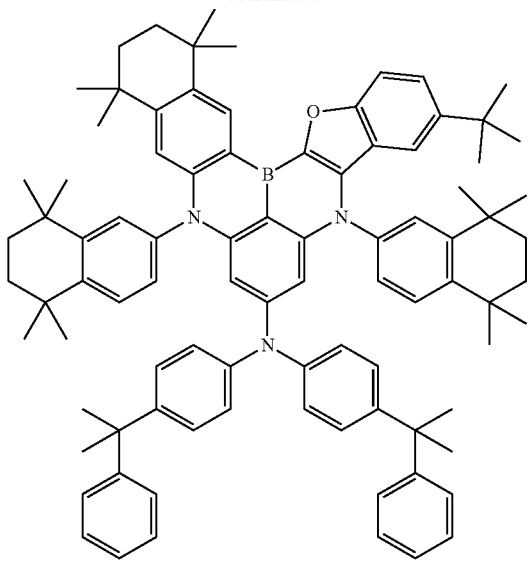
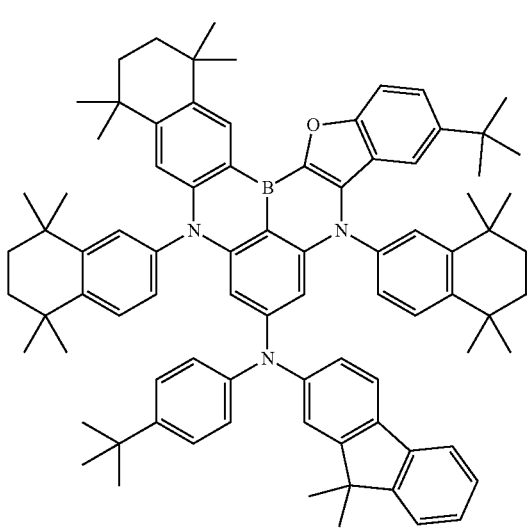
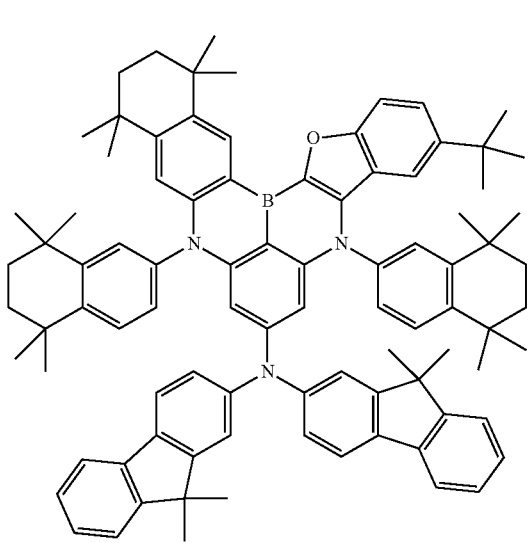
2832
-continued
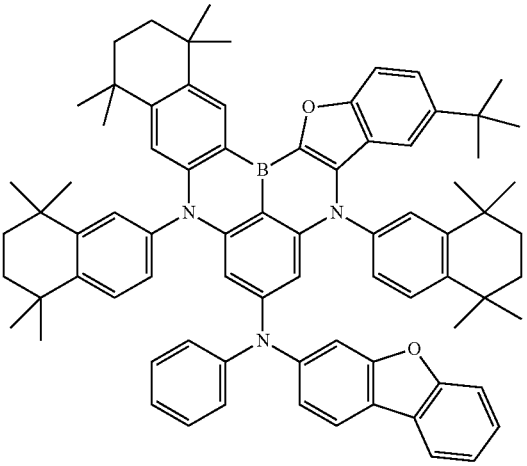
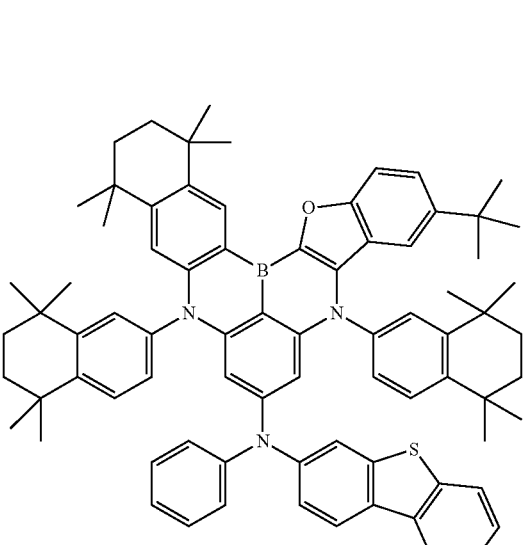
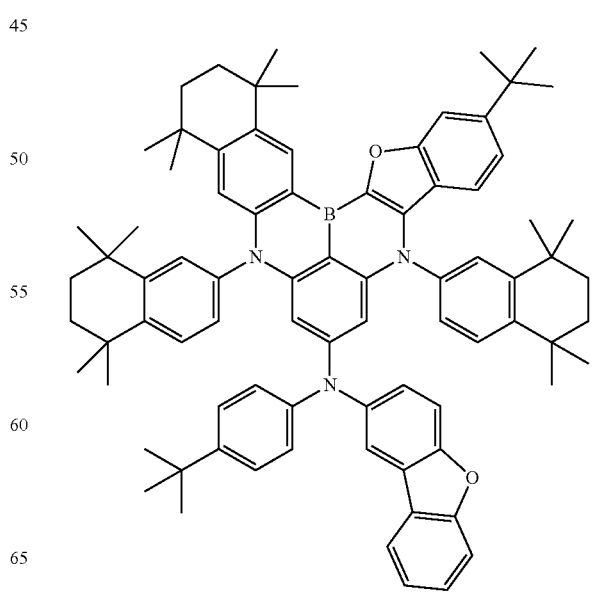

2833
-continued
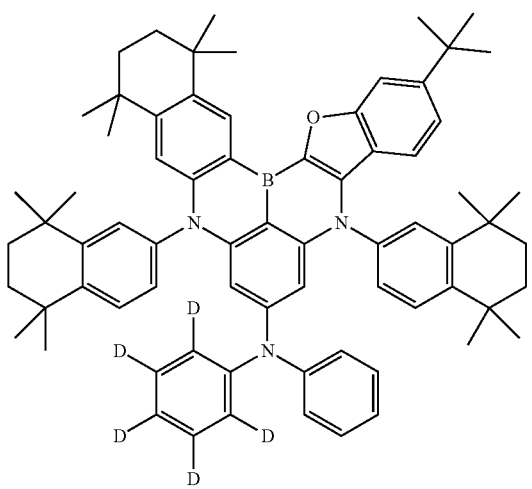
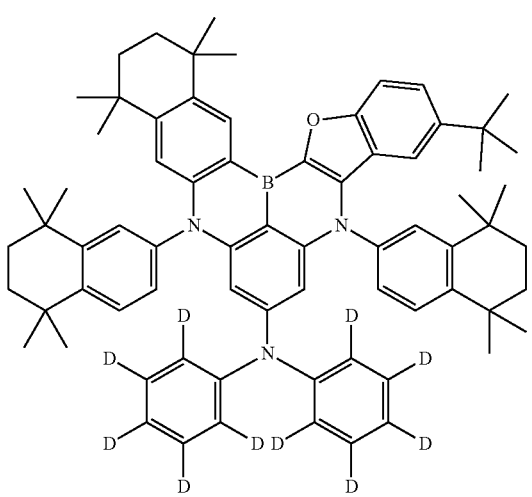
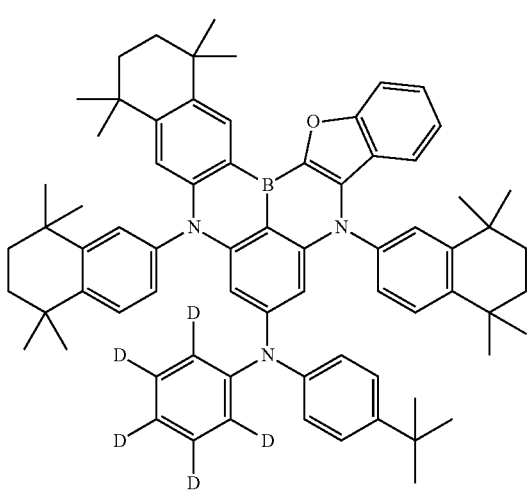
2834
-continued
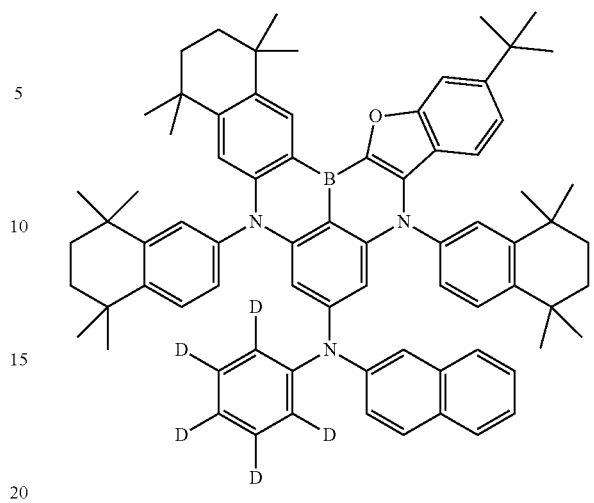
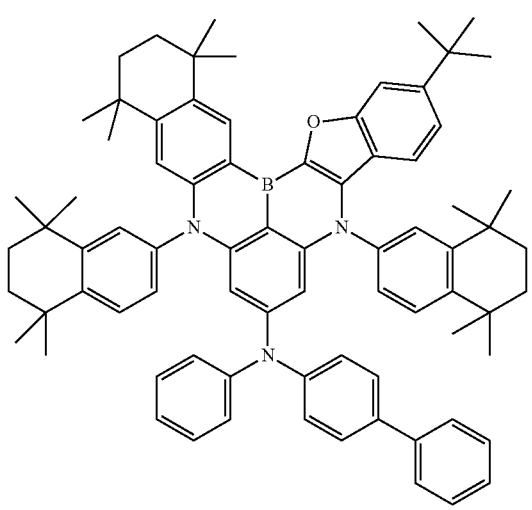
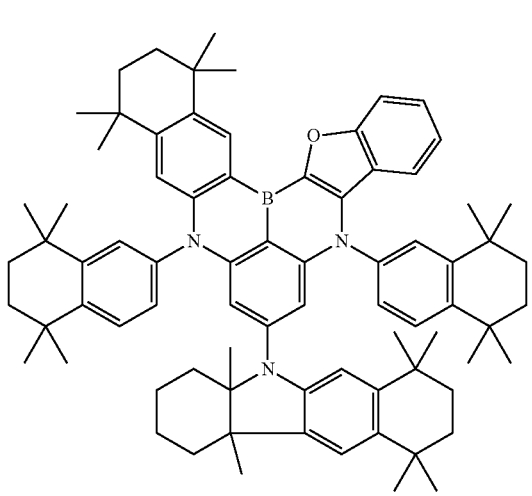

2835
-continued
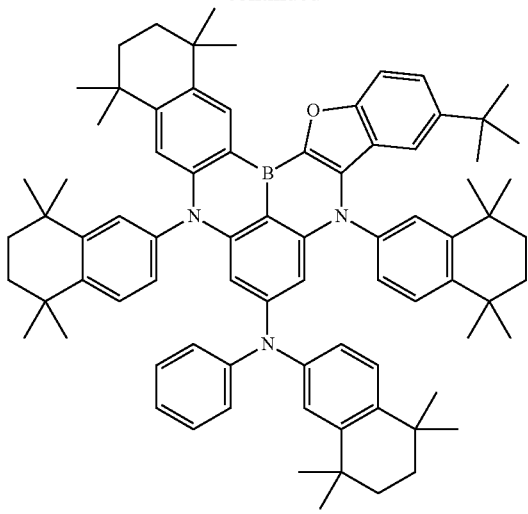
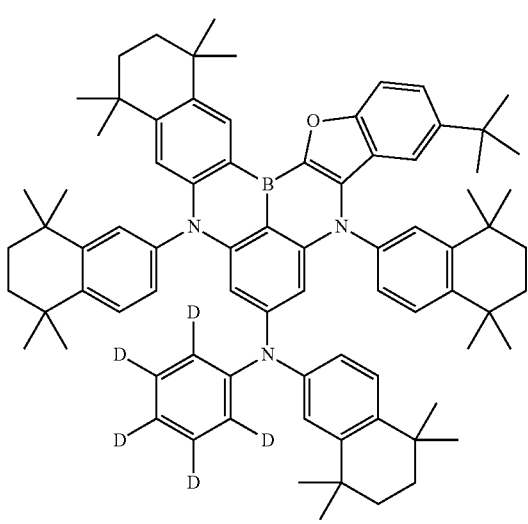
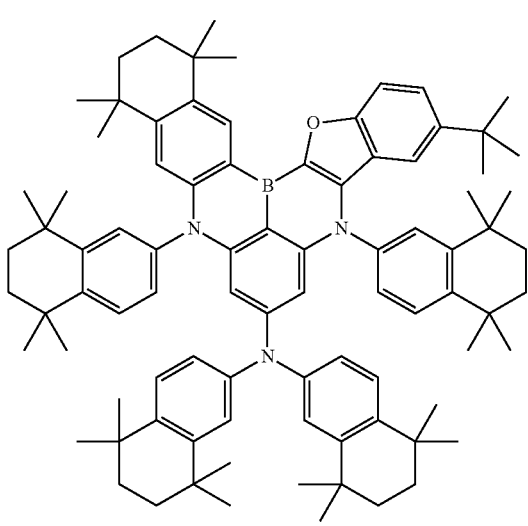
2836
-continued
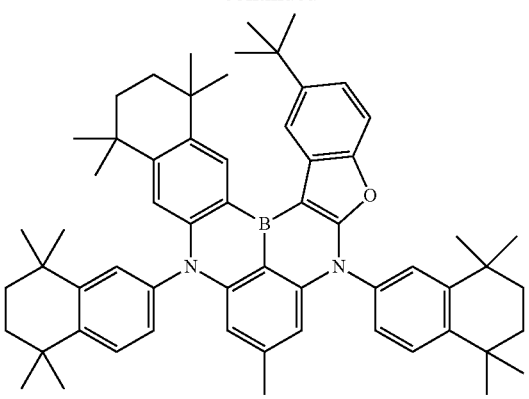
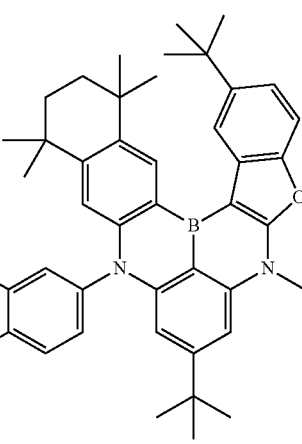
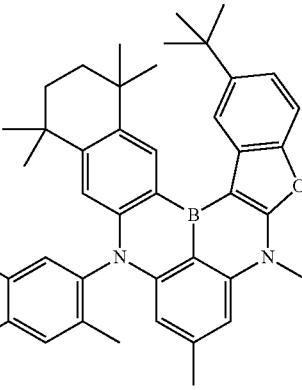
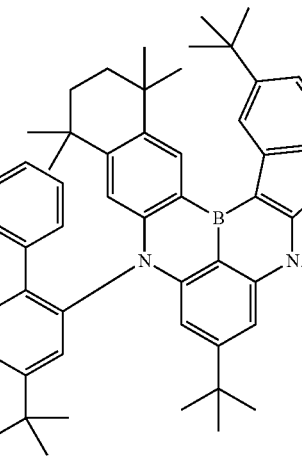

2837
-continued
2838
-continued
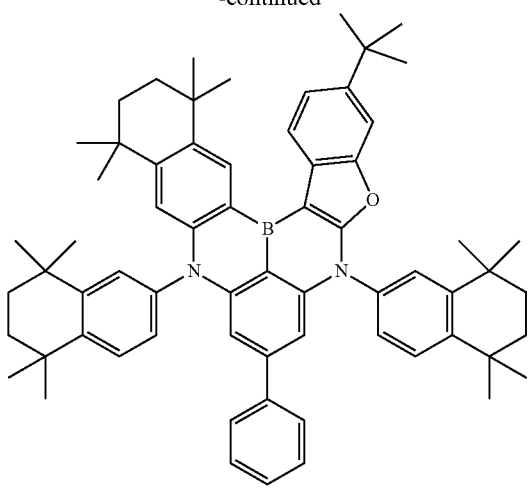
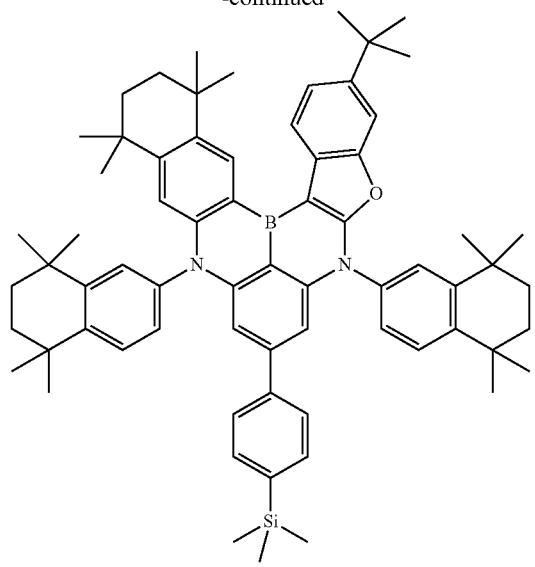
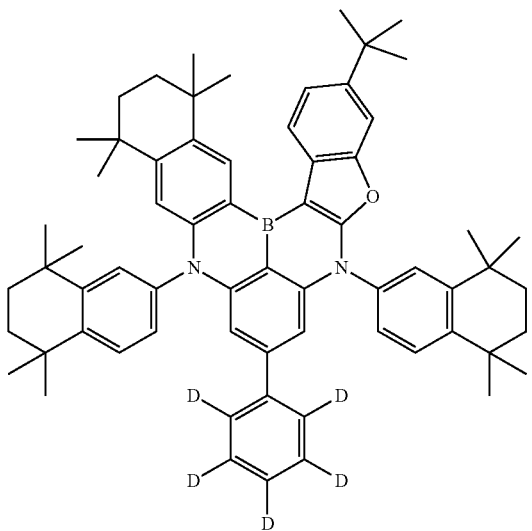
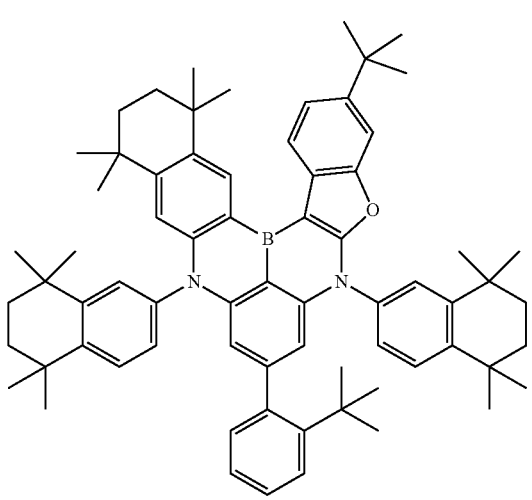
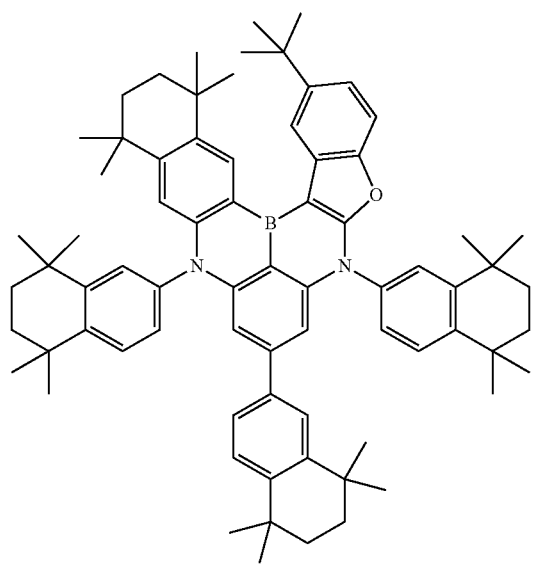

2839
-continued
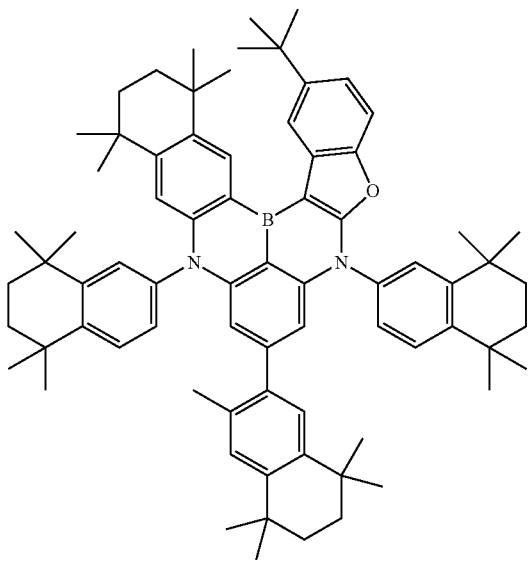
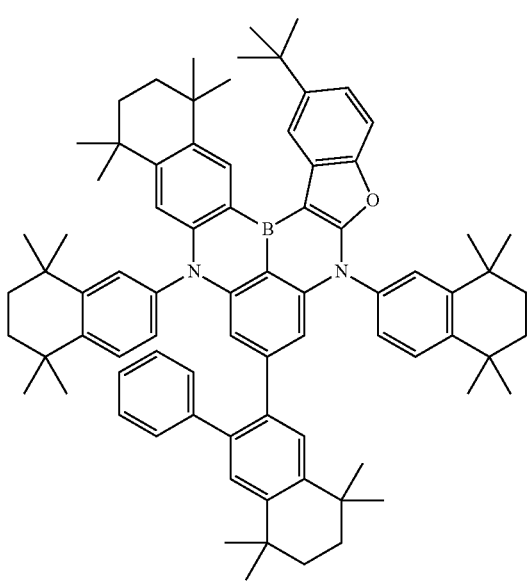
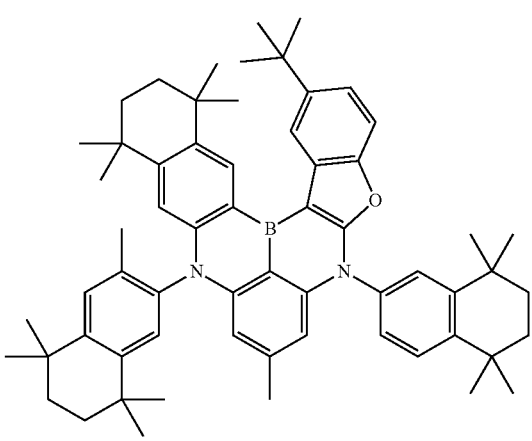
2840
-continued
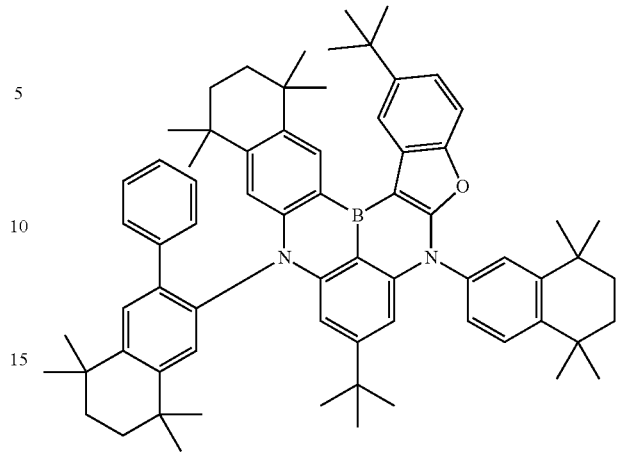
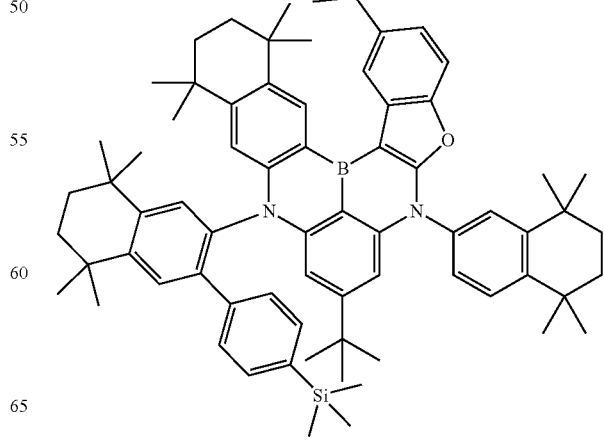

2841
-continued
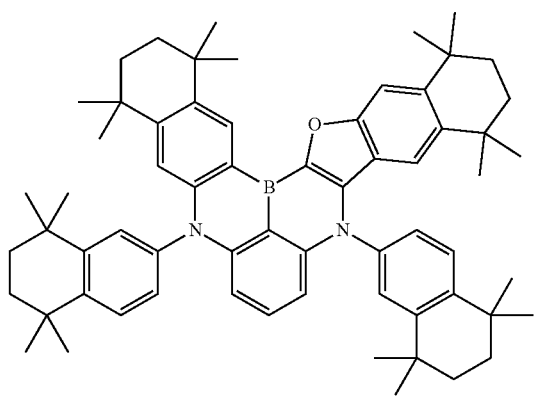
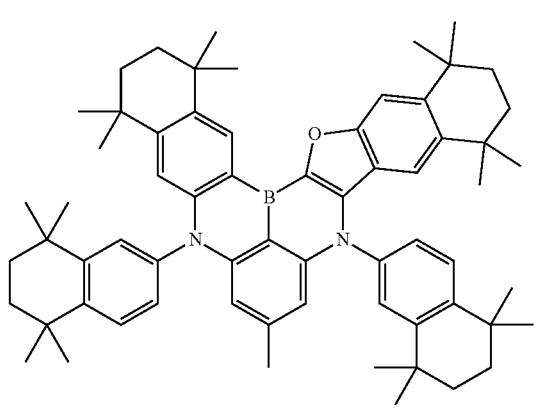
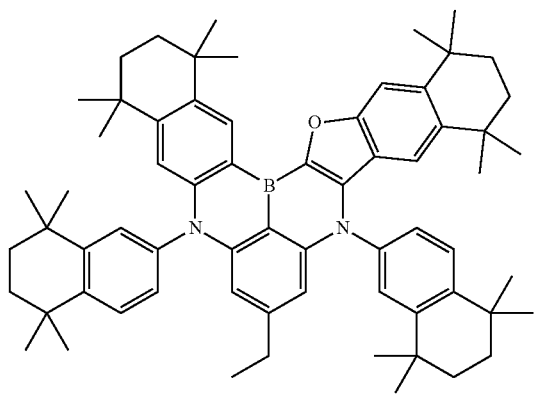
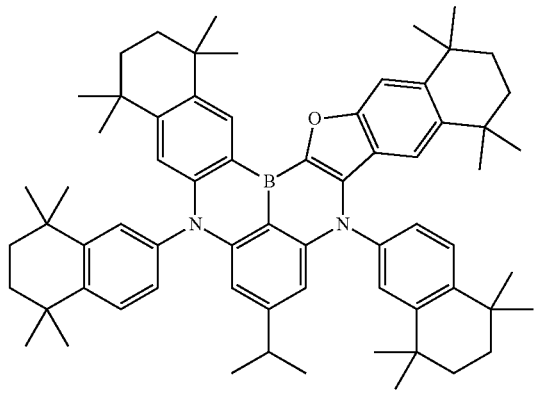
2842
-continued
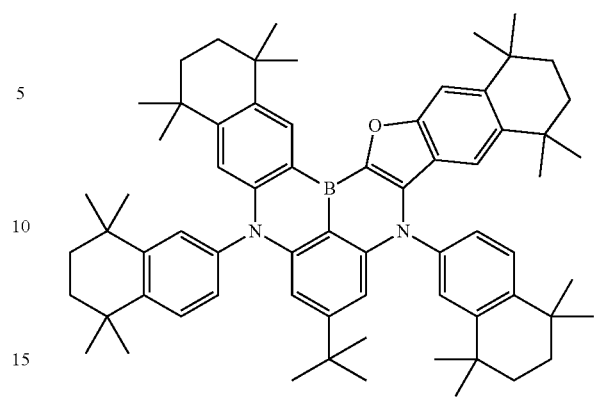
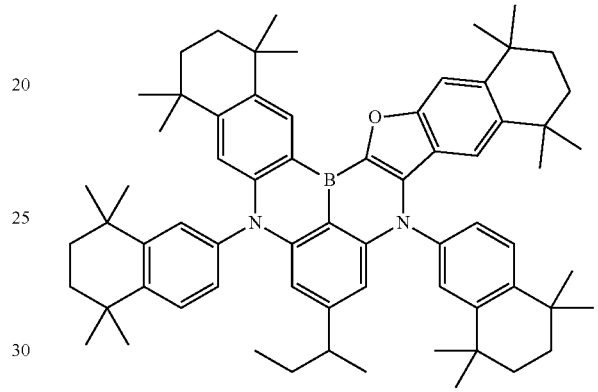
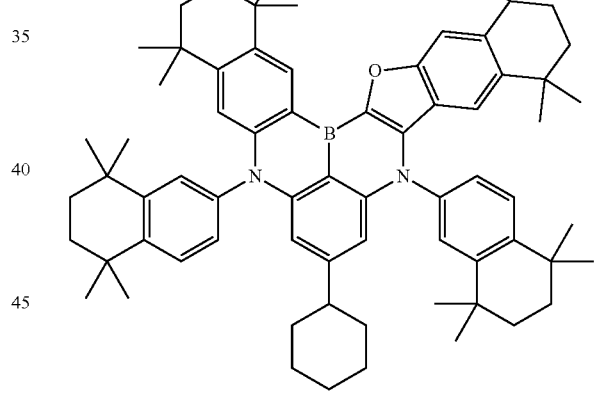
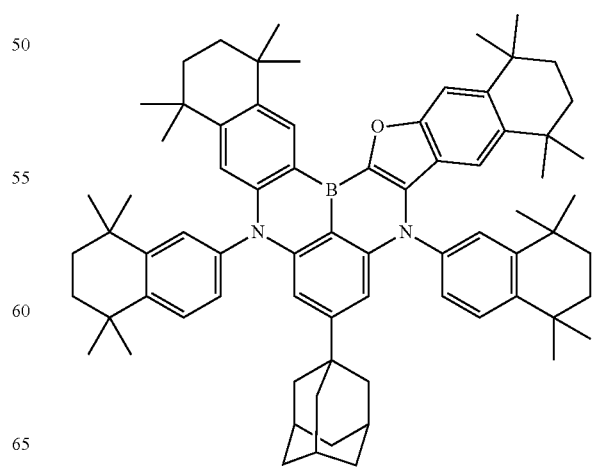

2843
-continued
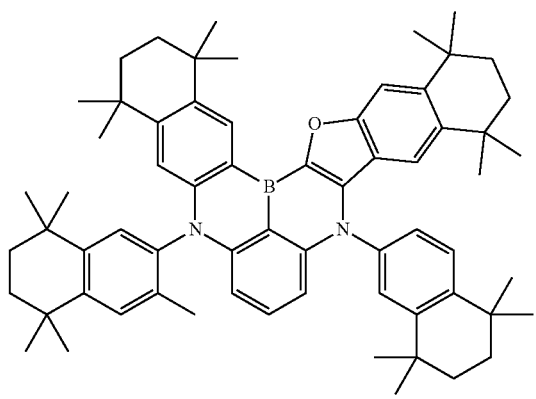
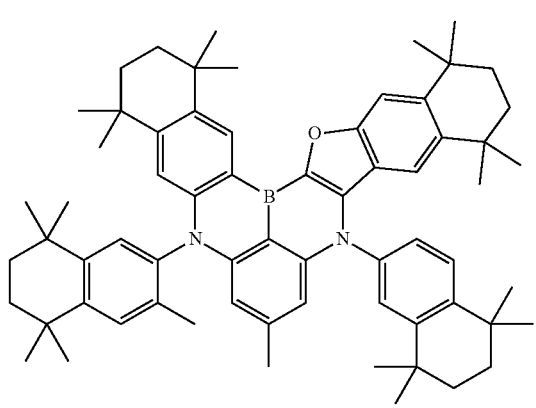
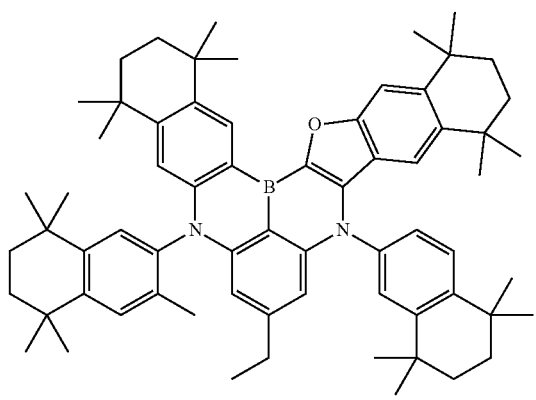
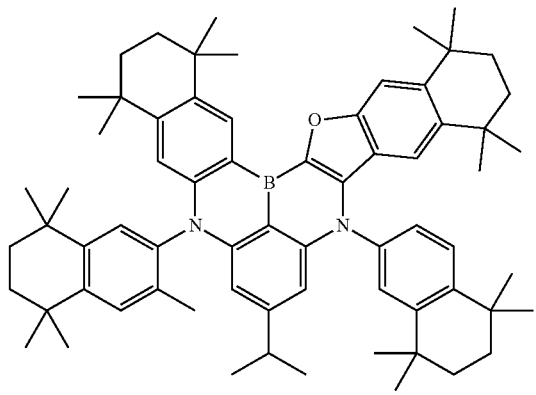
2844
-continued
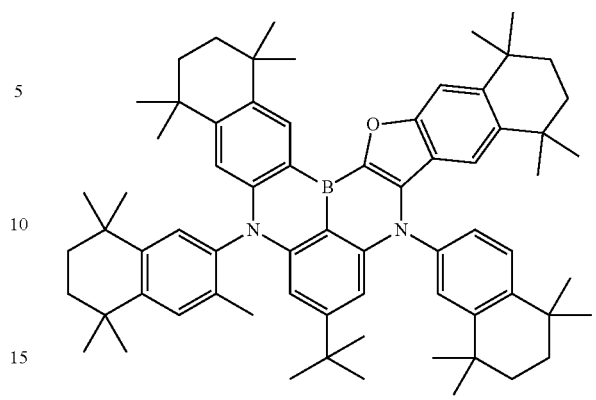
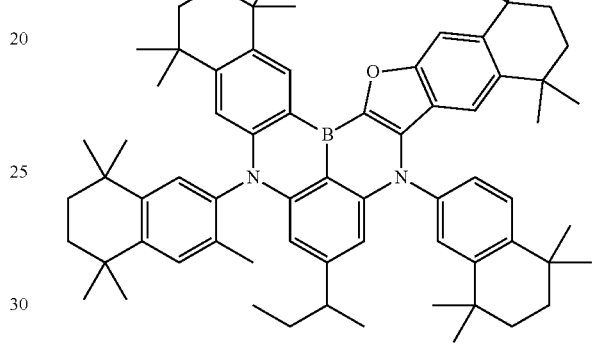
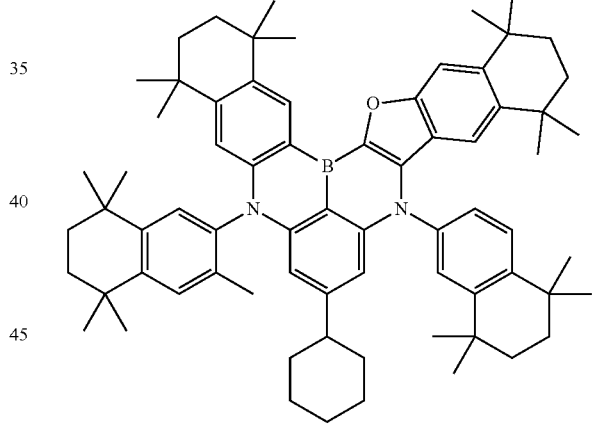
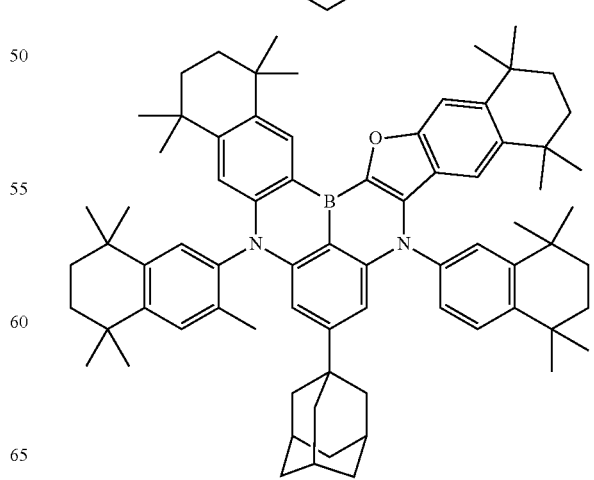

2845
-continued
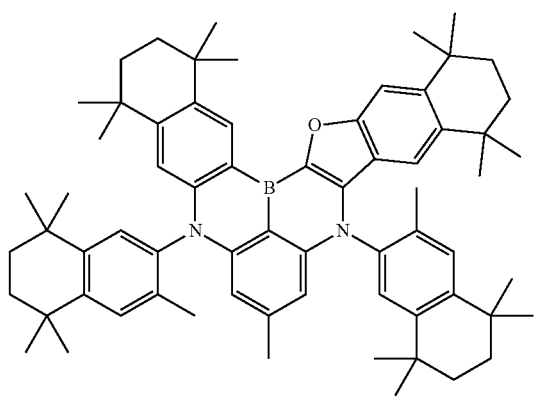
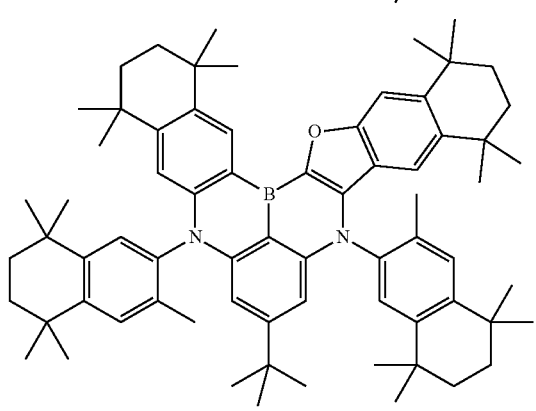
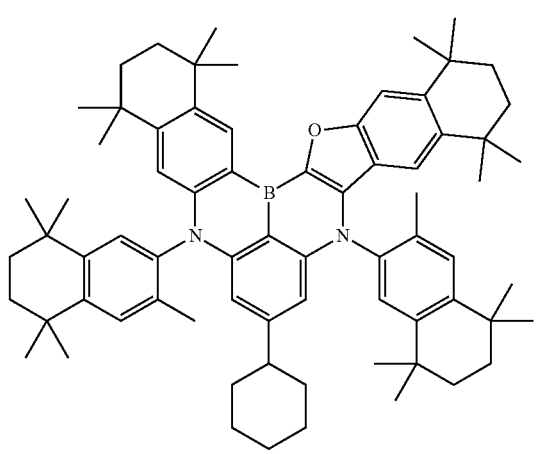
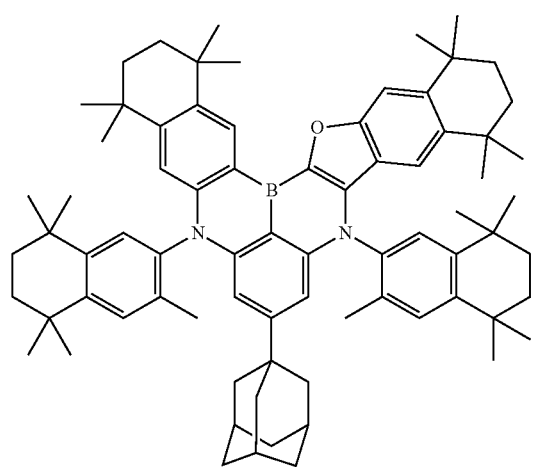
2846
-continued
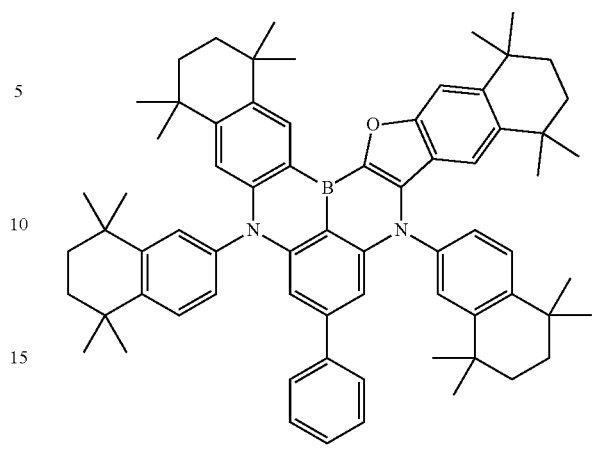
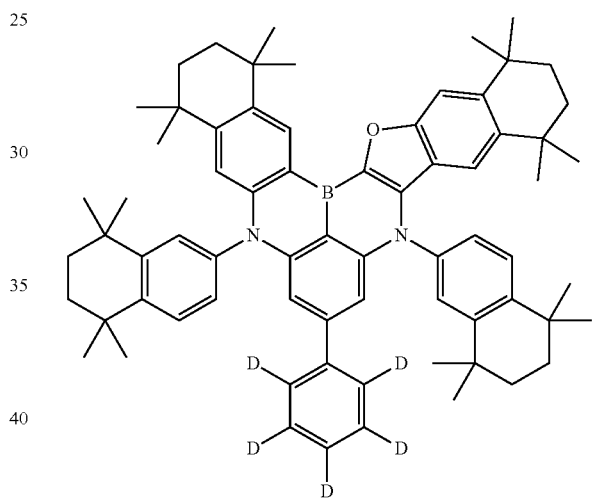
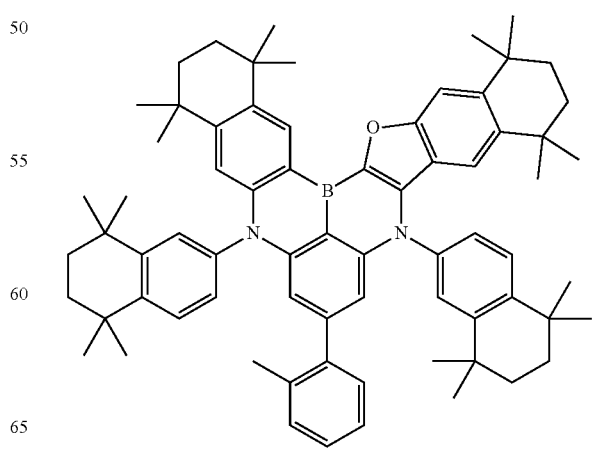

2847
-continued
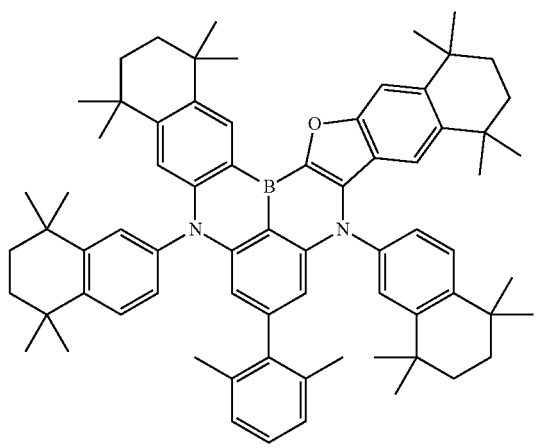
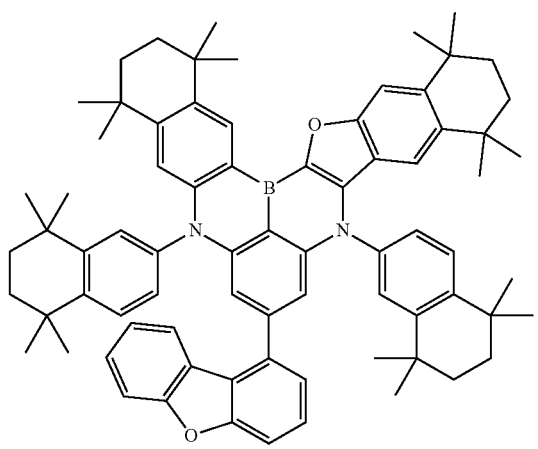
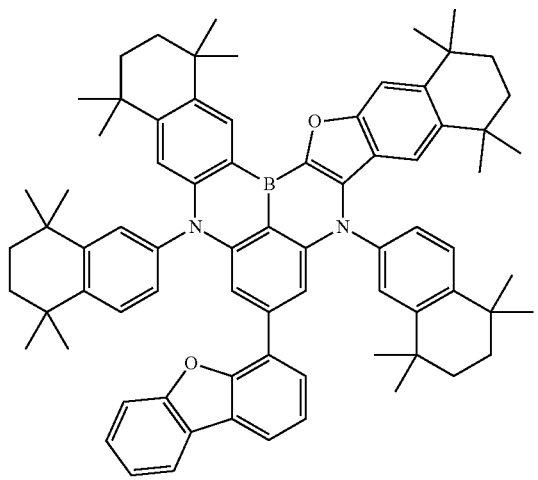
2848
-continued
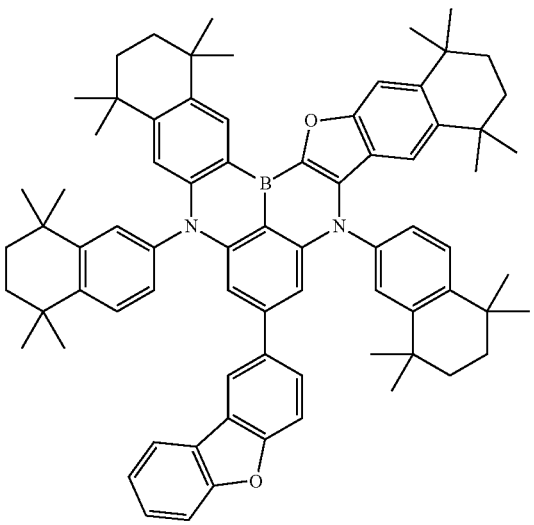
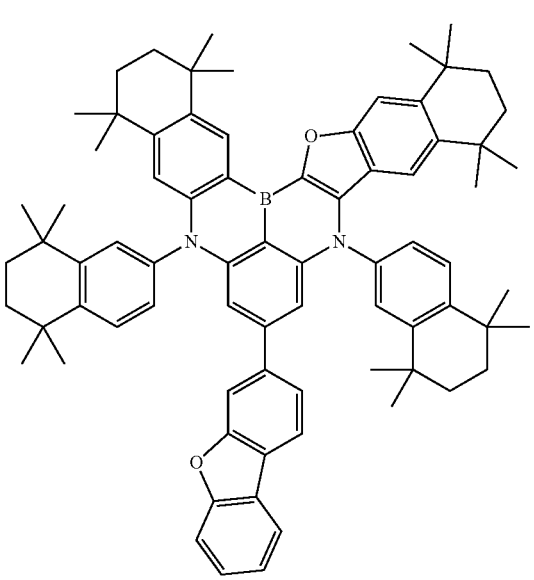
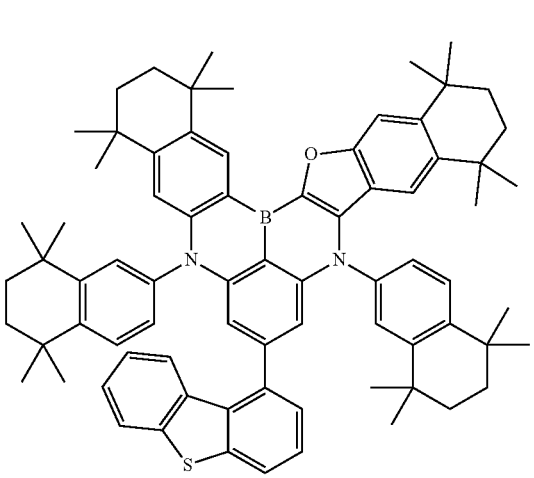

2849
-continued
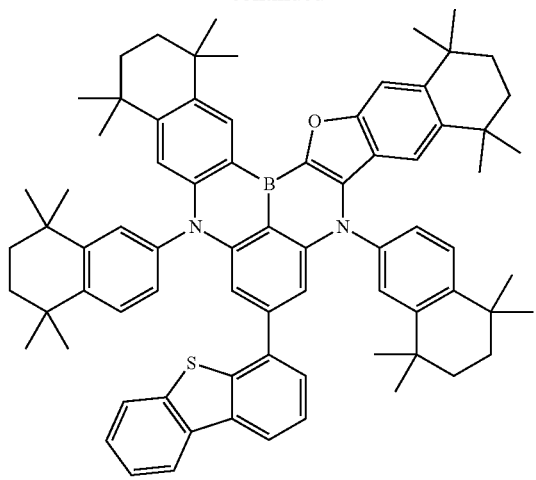
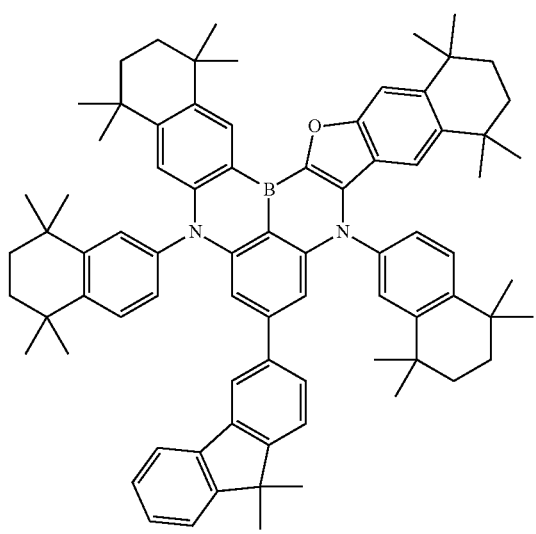
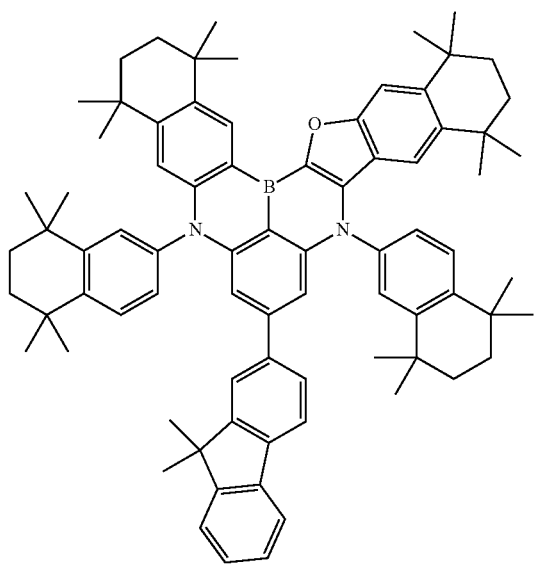
2850
-continued
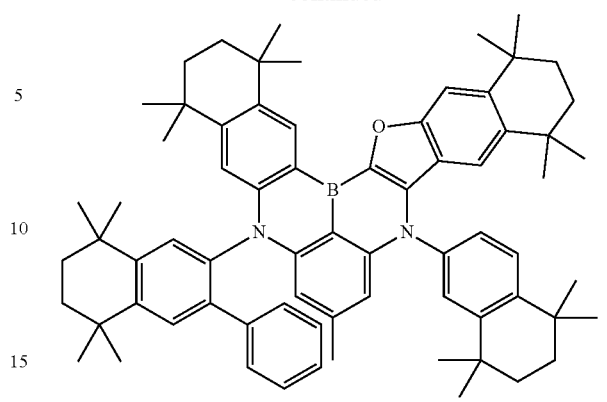
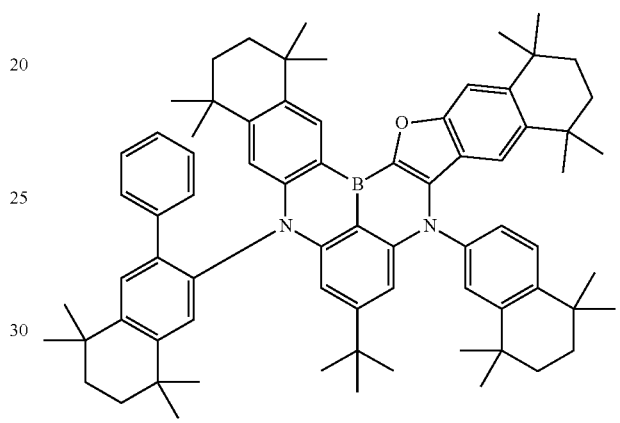
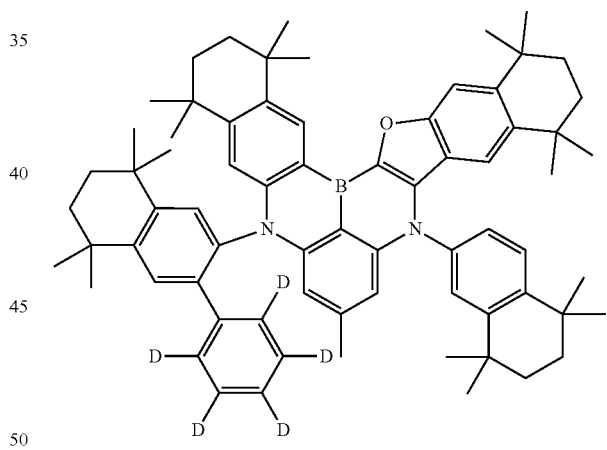
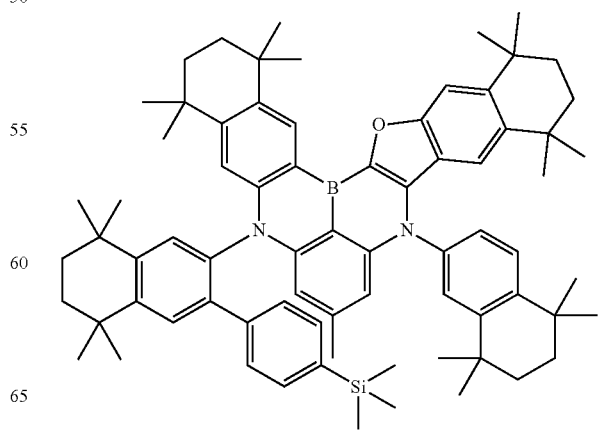

2851
-continued
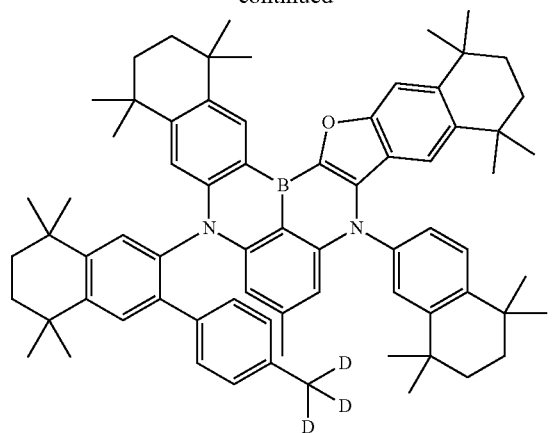
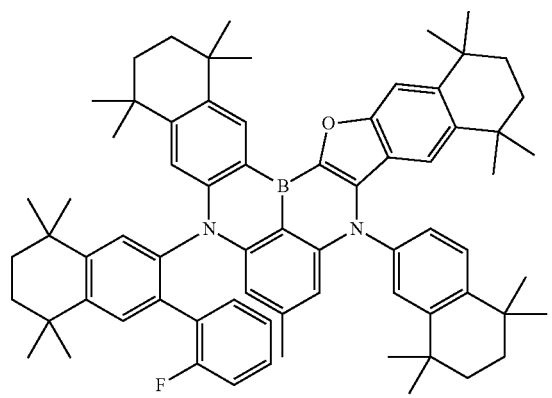
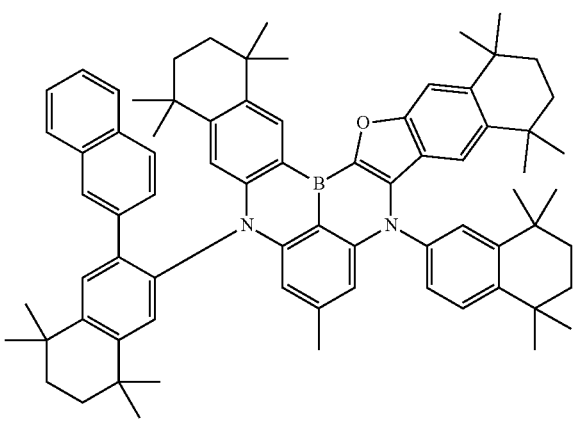
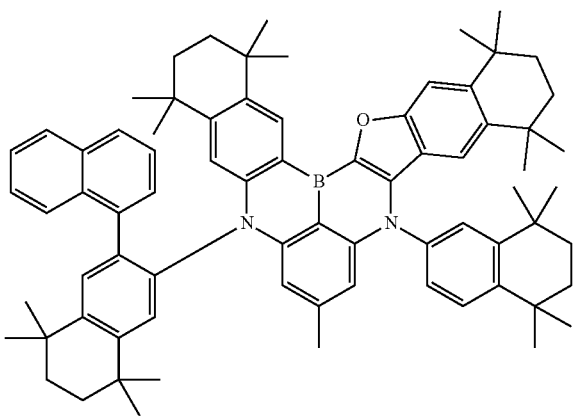
2852
-continued
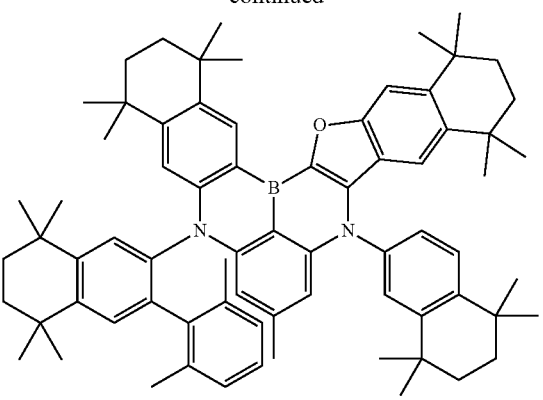
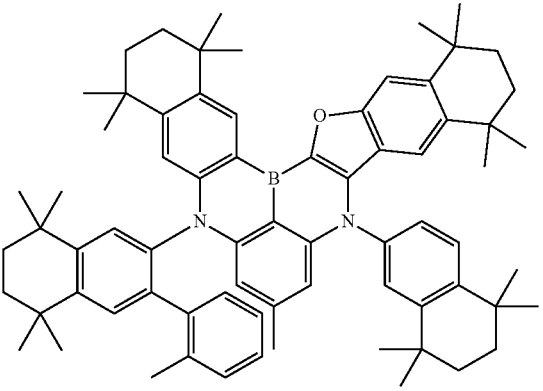
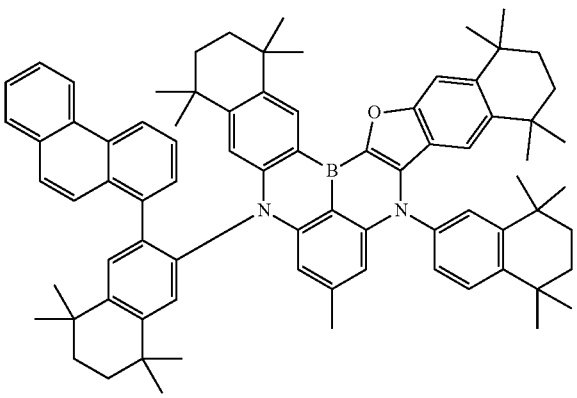
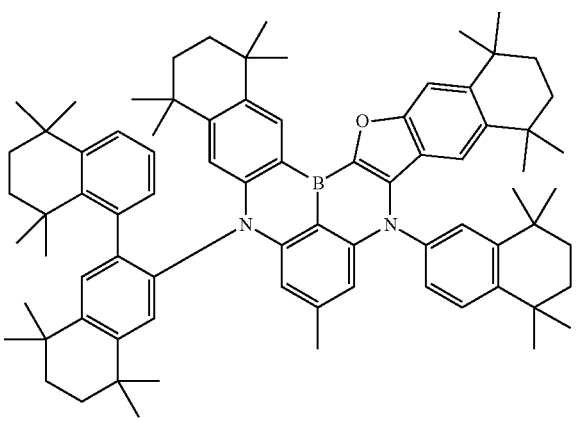

2853
-continued
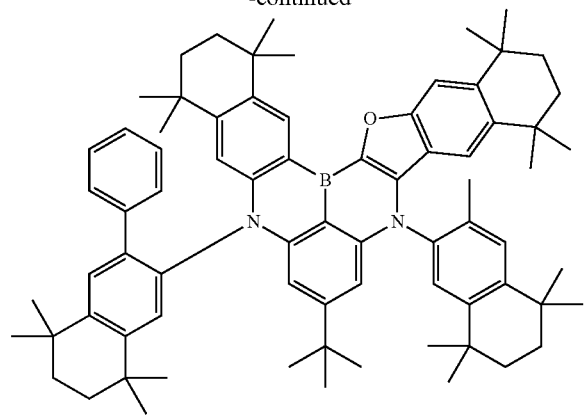
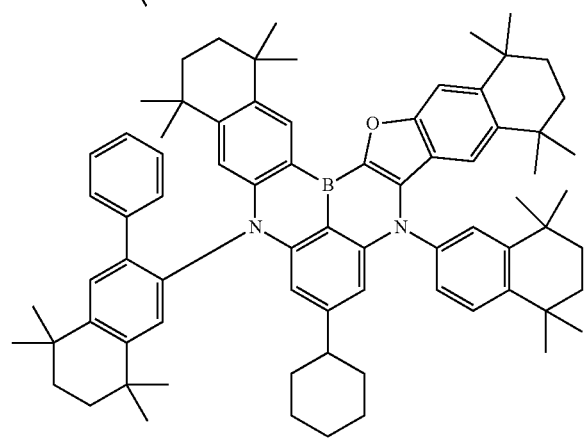
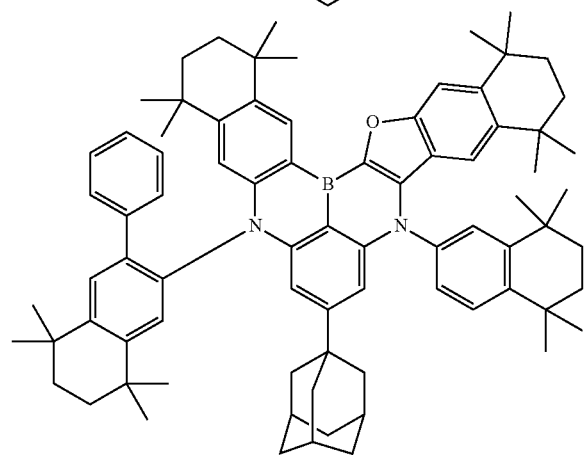
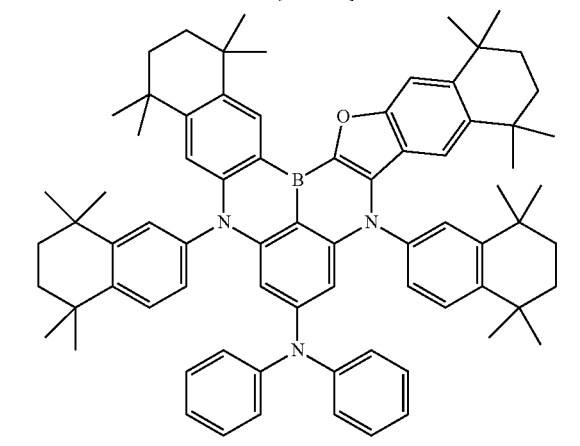
2854
-continued
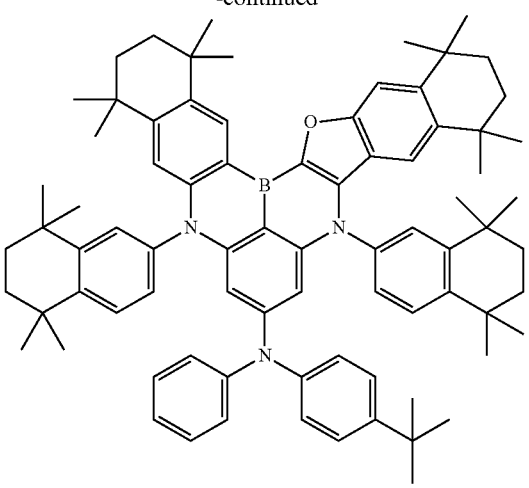
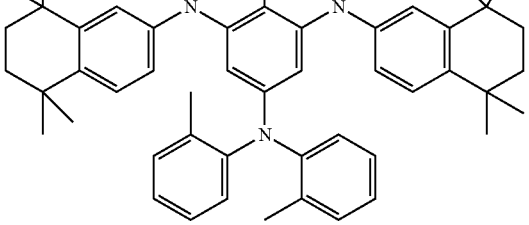
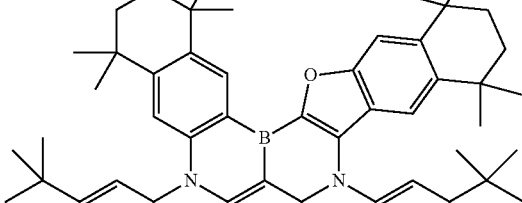
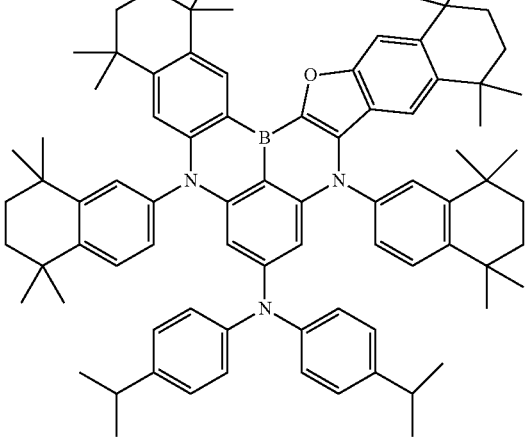

2855
-continued
2856
-continued
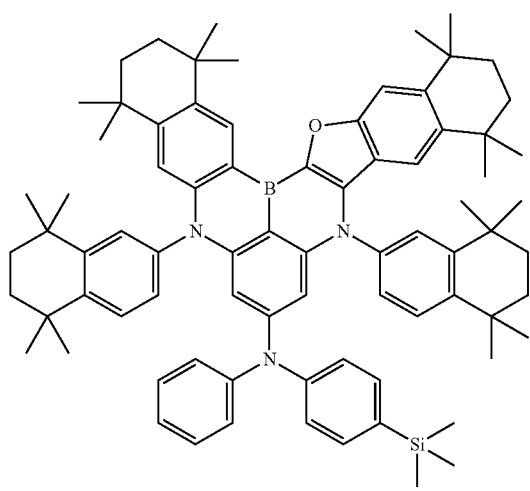
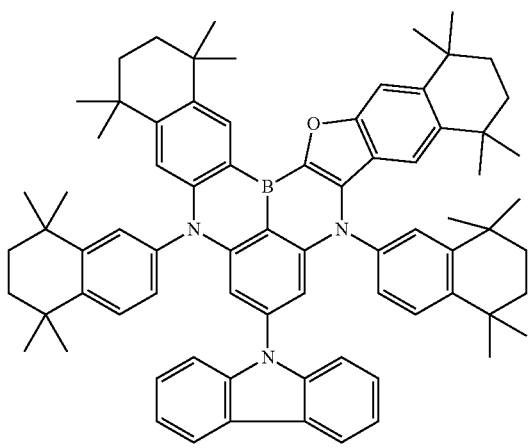
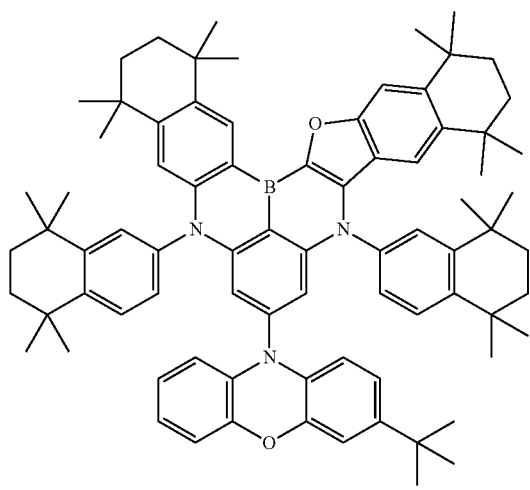
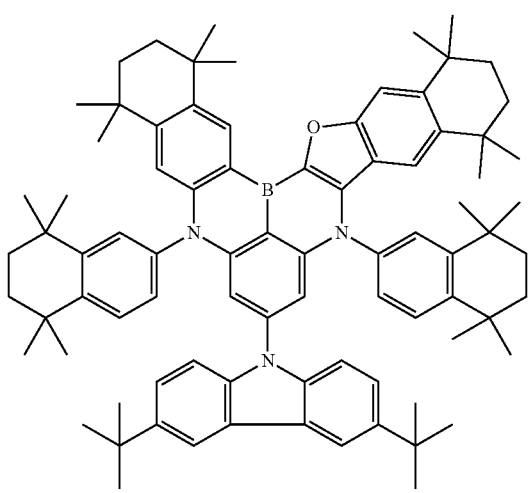
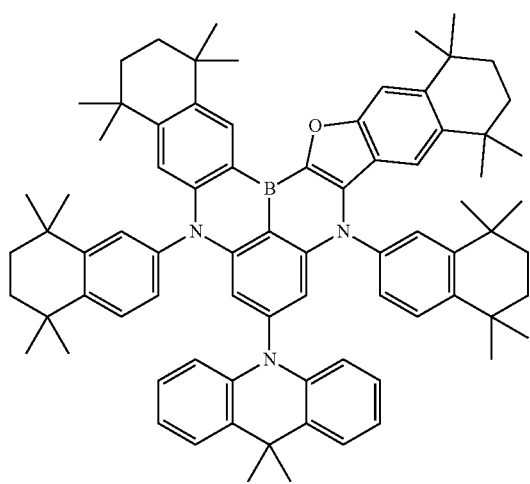
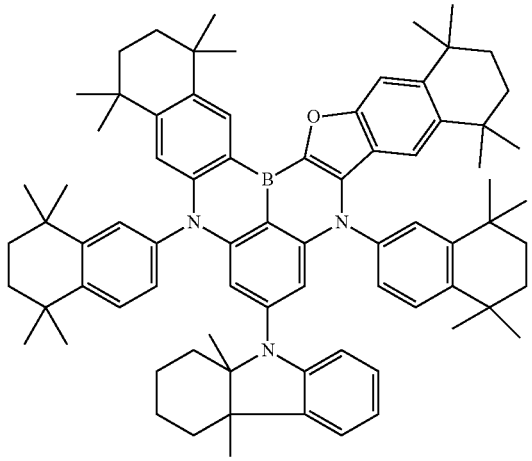

2857
-continued
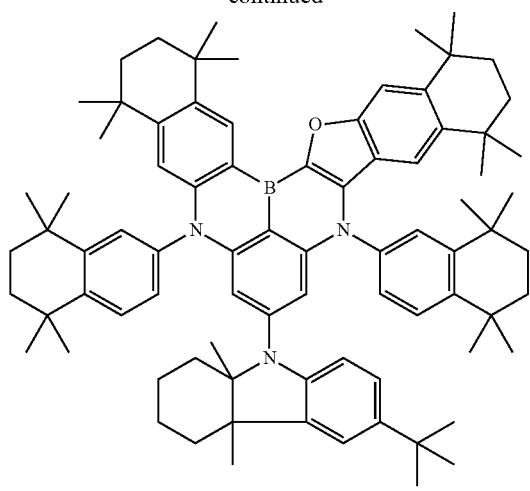
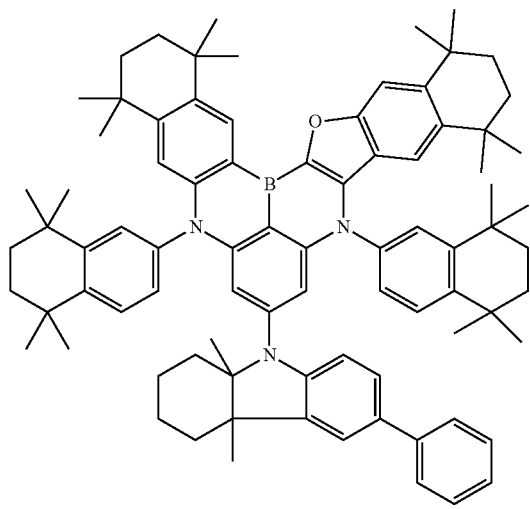
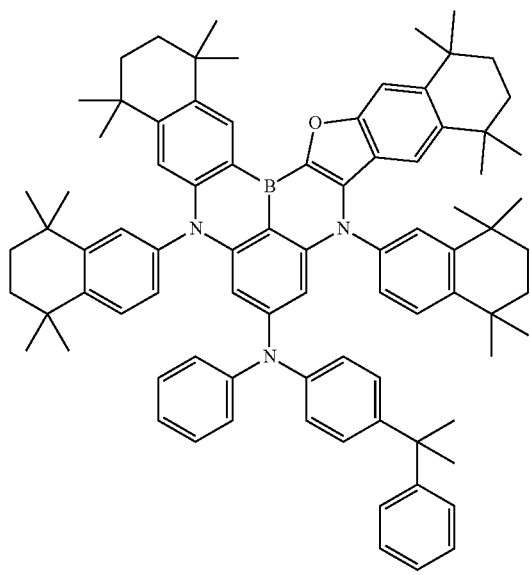
2858
-continued
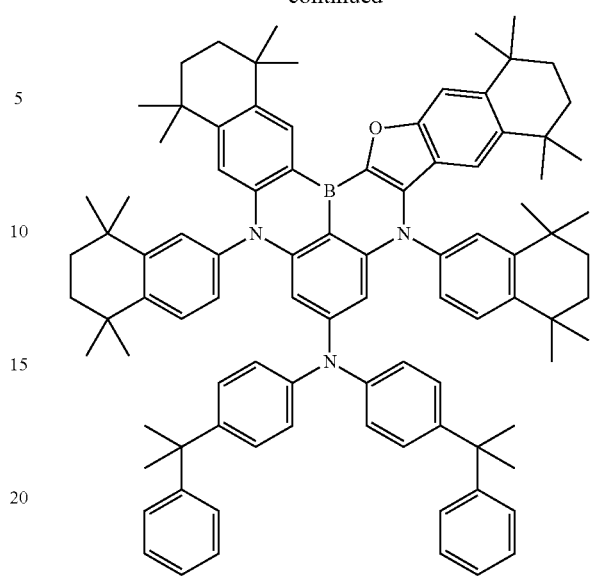
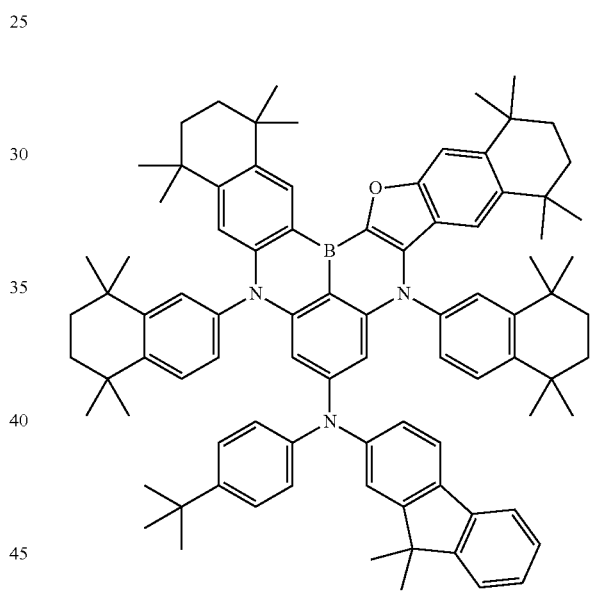
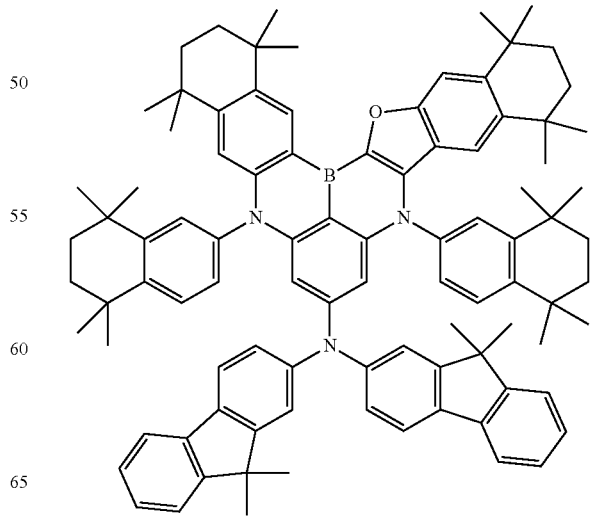

2859
-continued
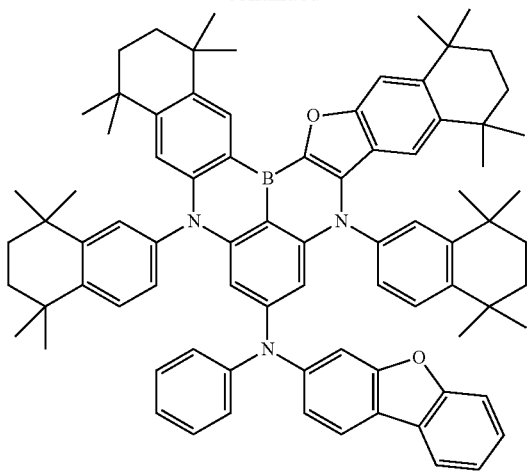
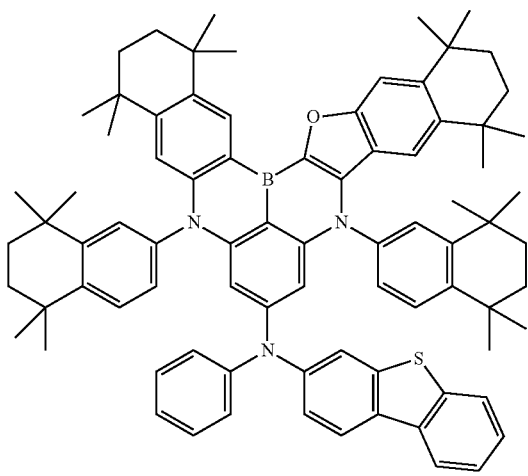
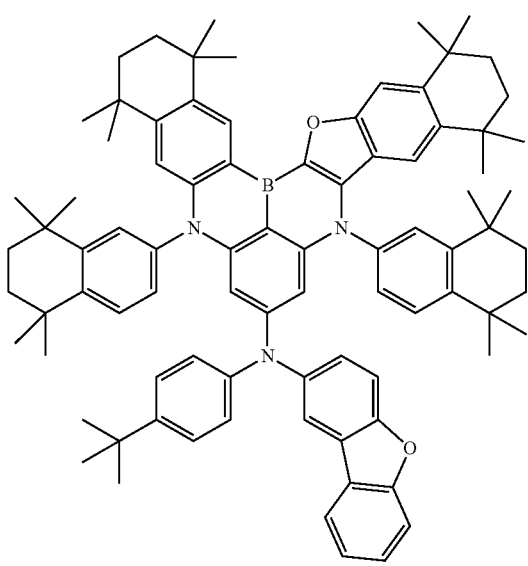
2860
-continued
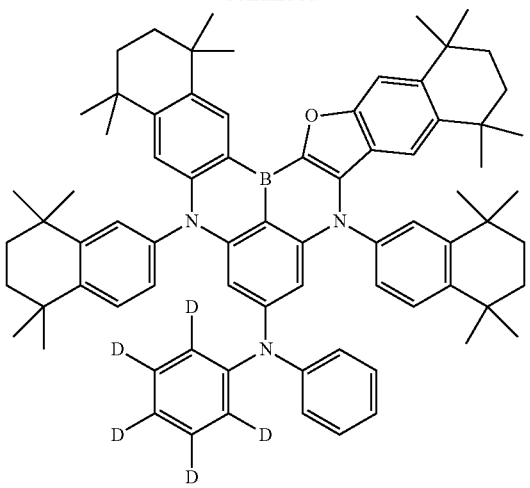
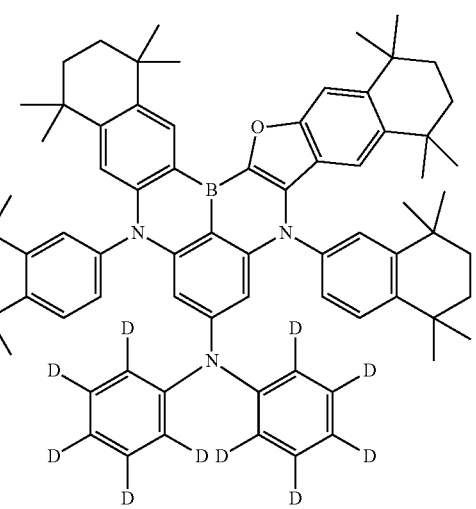
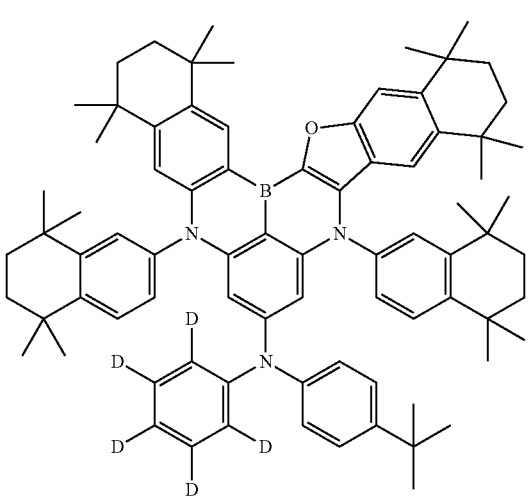

| 2861 -continued | 2862 -continued |
|---|---|
| 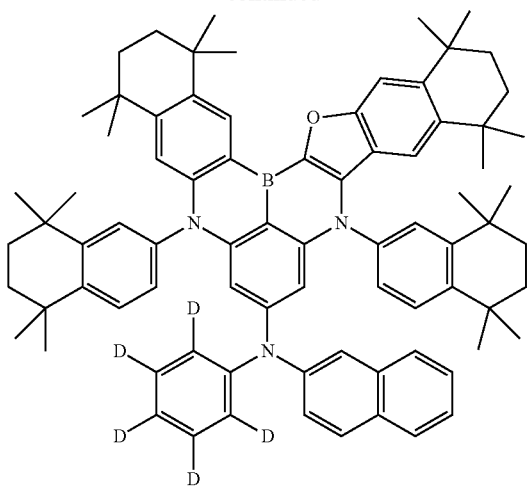 | 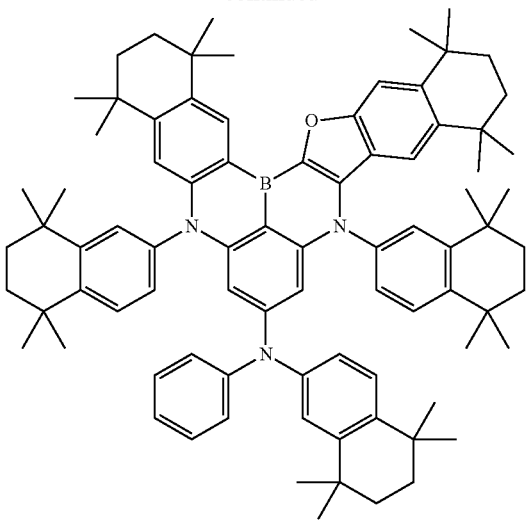 |
| 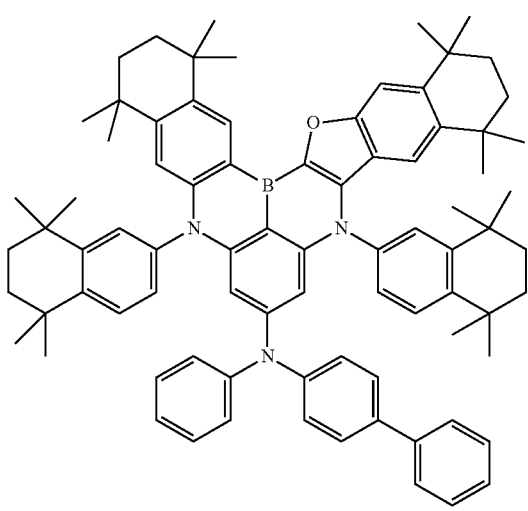 | |
| 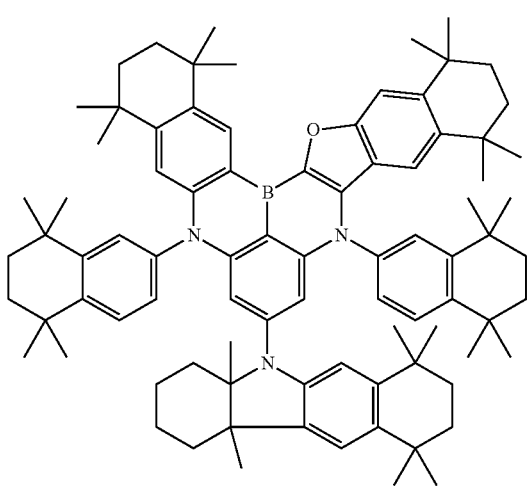 | 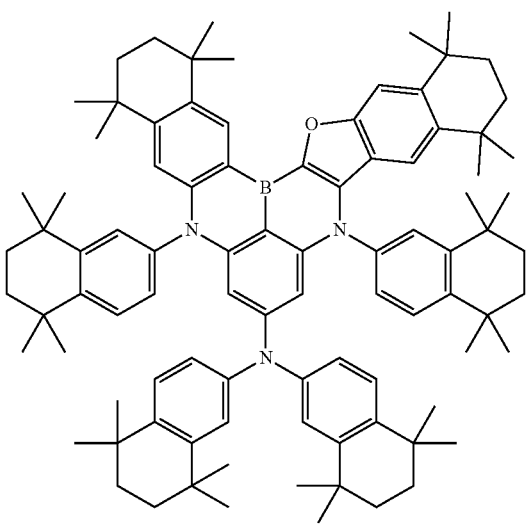 |

2863
-continued
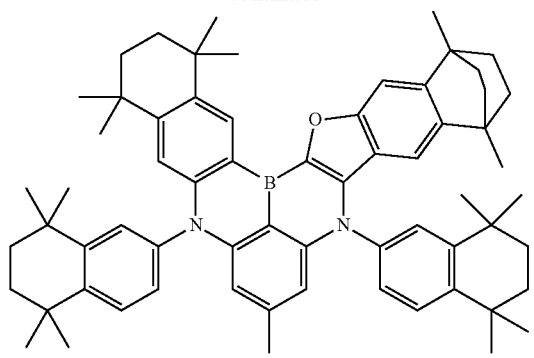
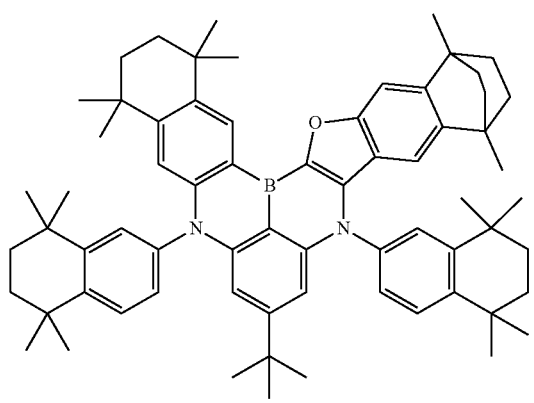
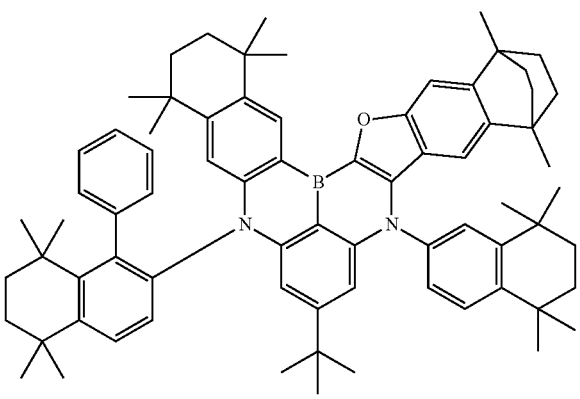
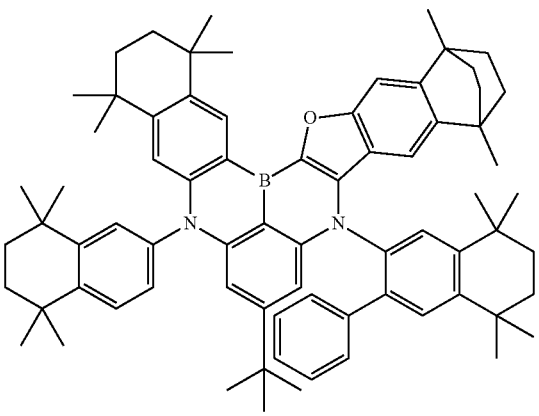
2864
-continued
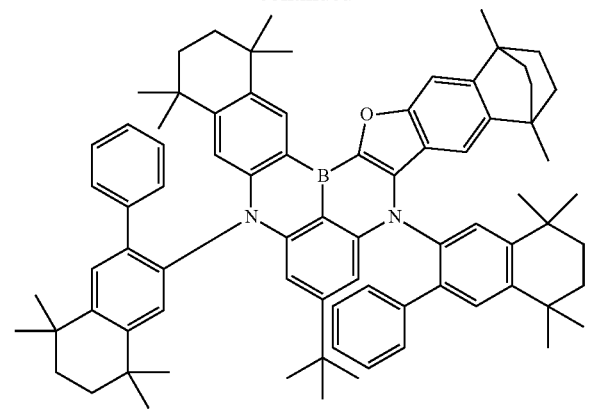
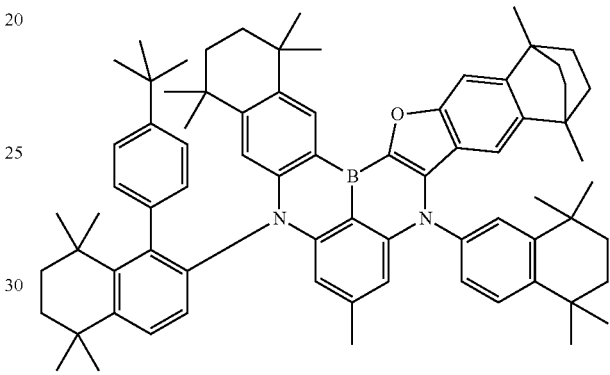
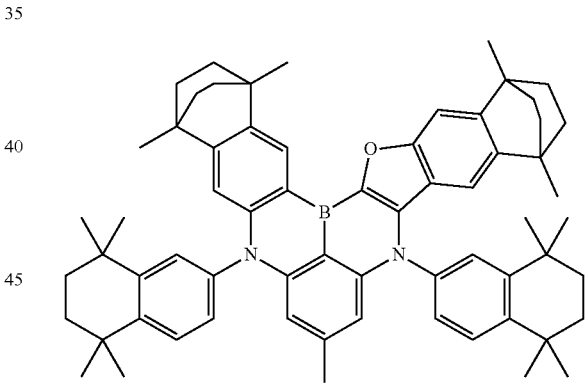
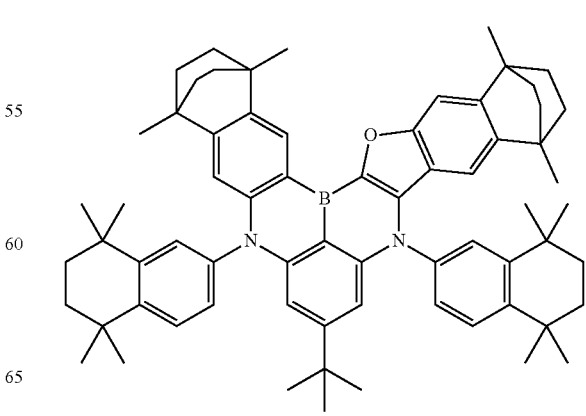

2865
-continued
2866
-continued
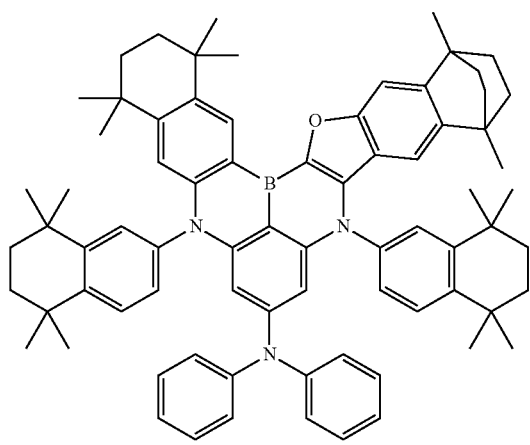
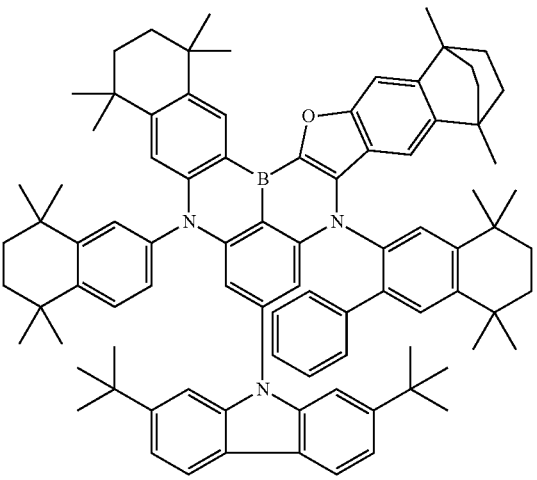
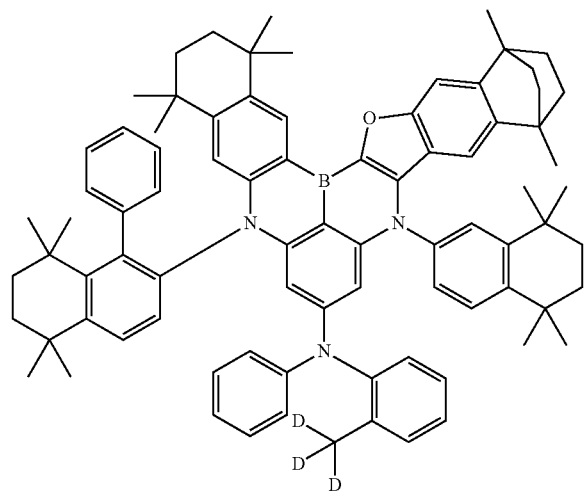
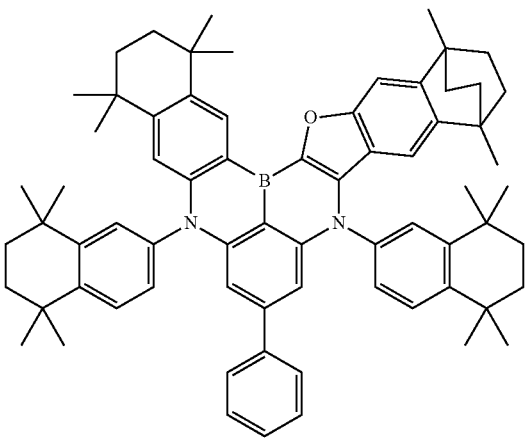
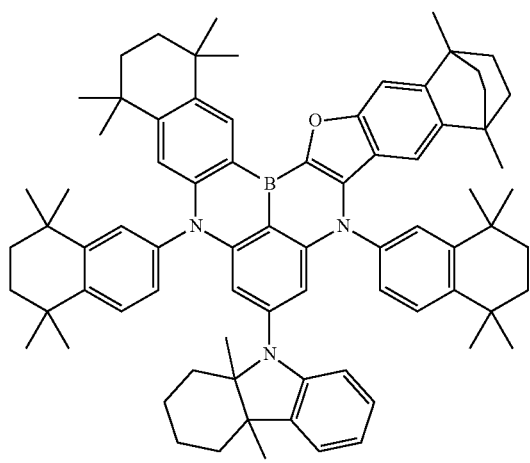
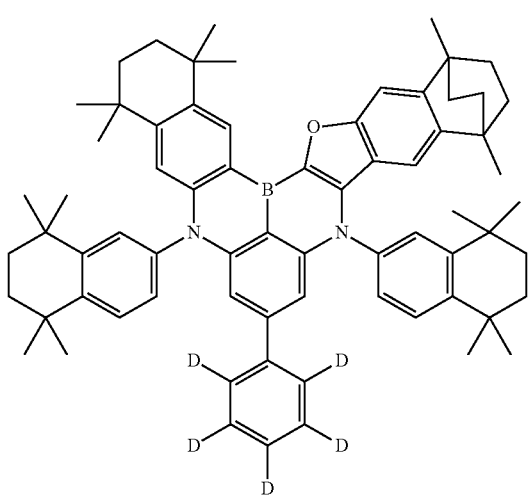

2867
-continued
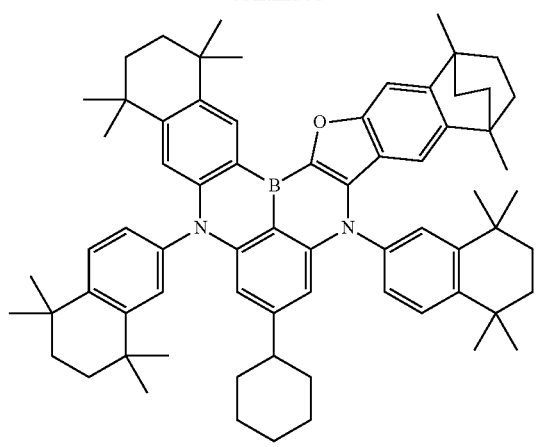
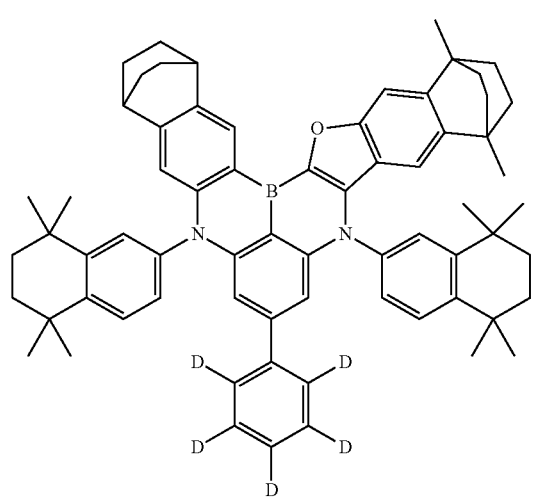
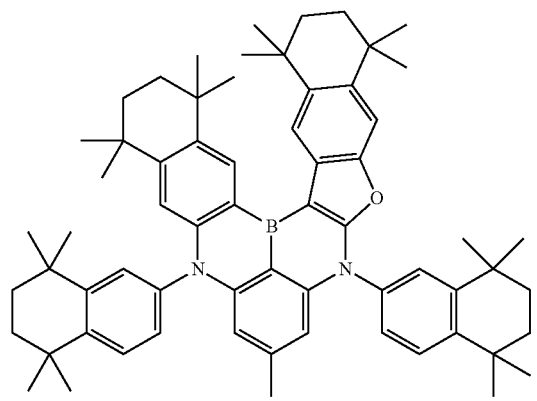
2868
-continued
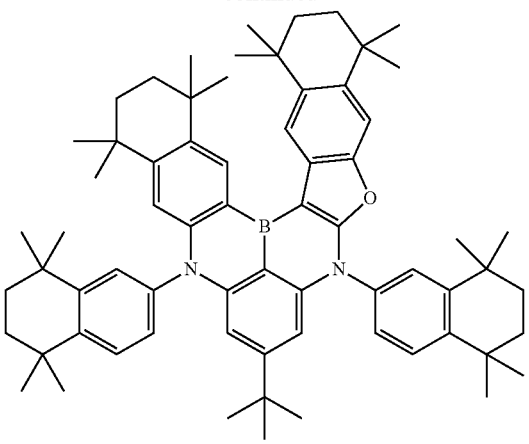
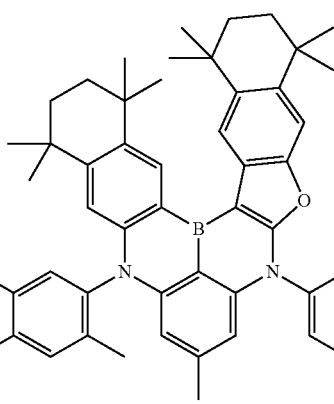
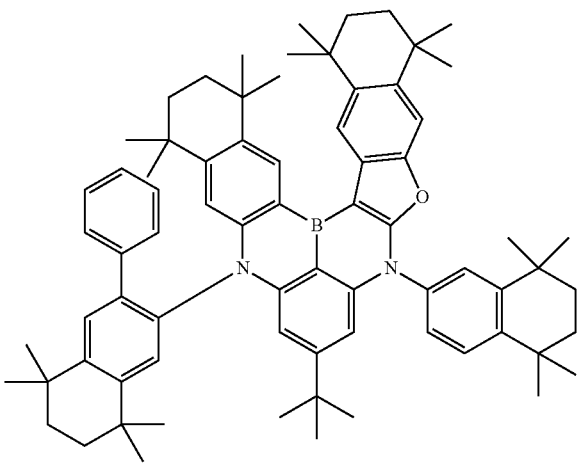

2869
-continued
2870
-continued
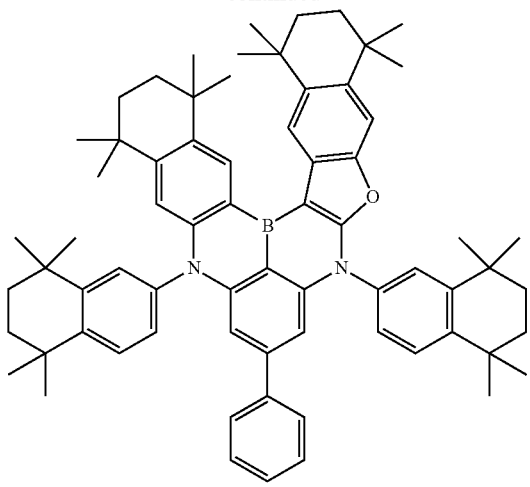
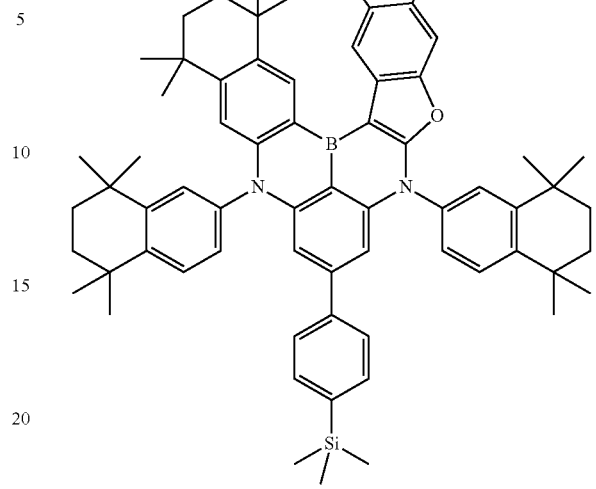
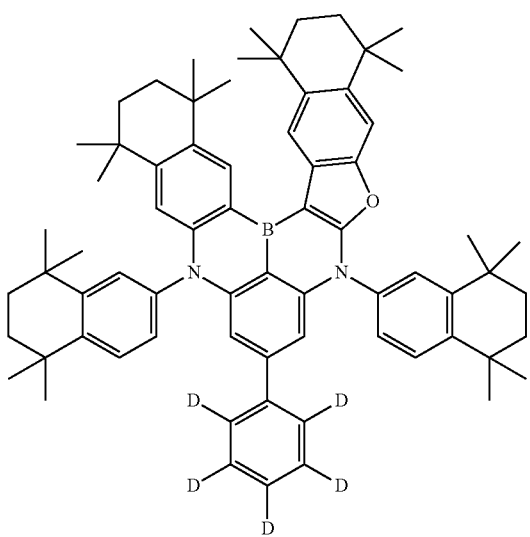
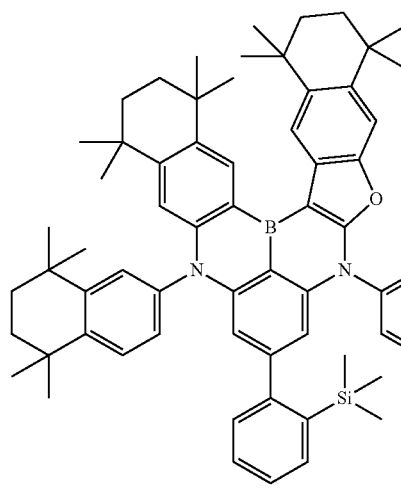
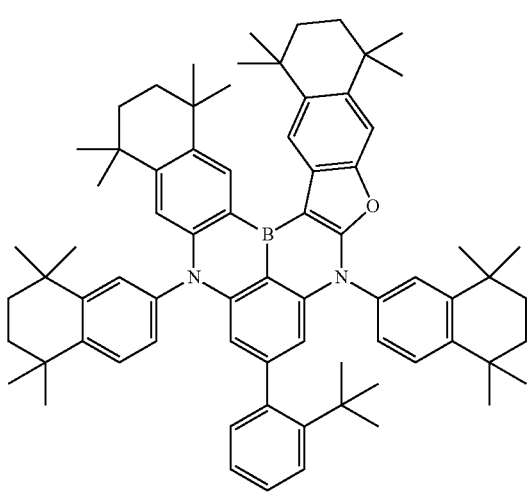
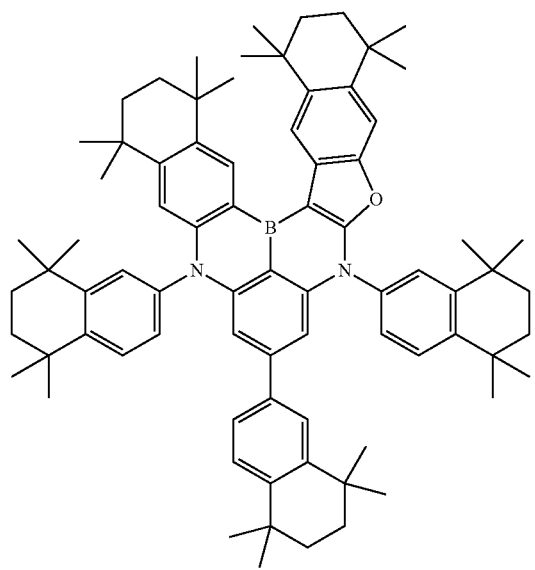

2871
-continued
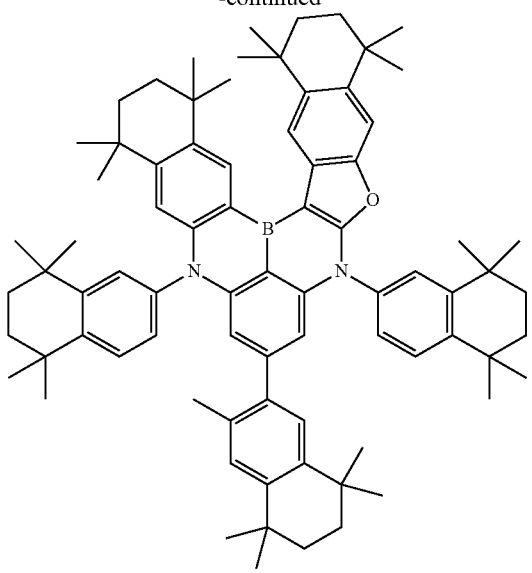
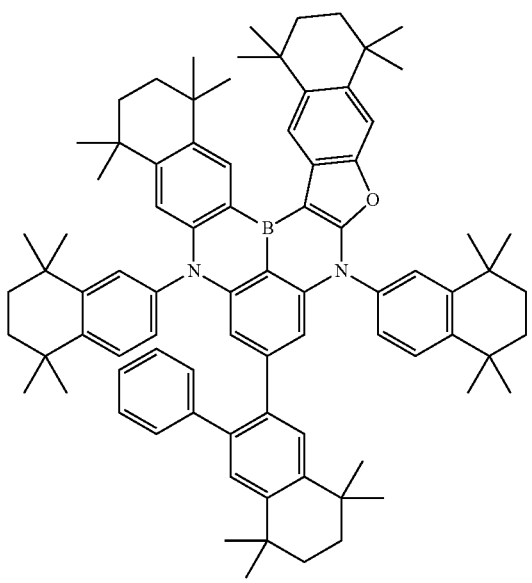
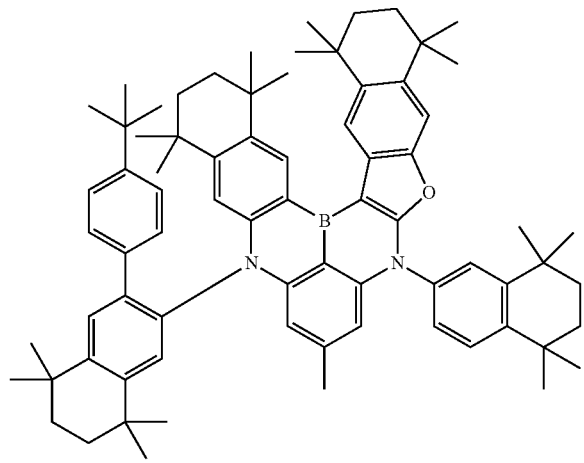
2872
-continued
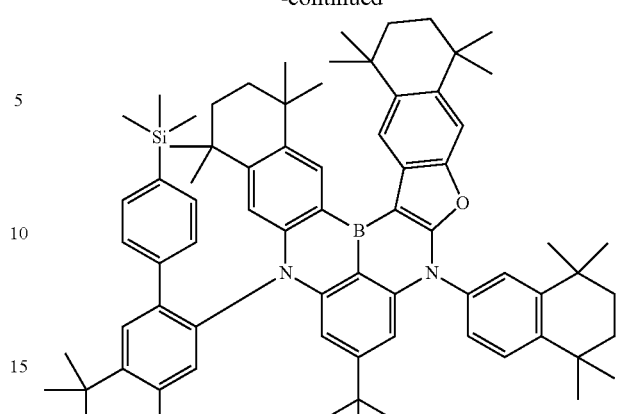
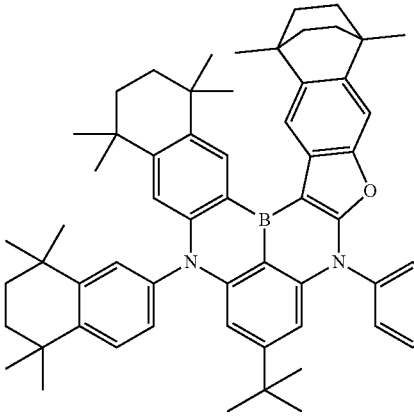
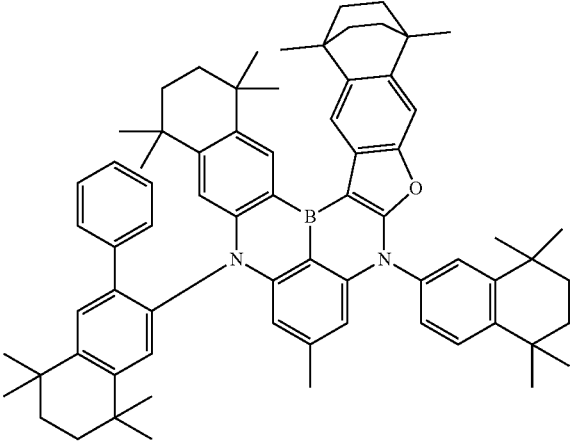

2873
-continued
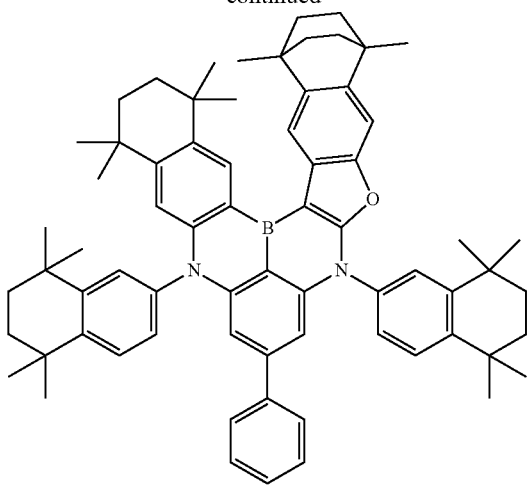
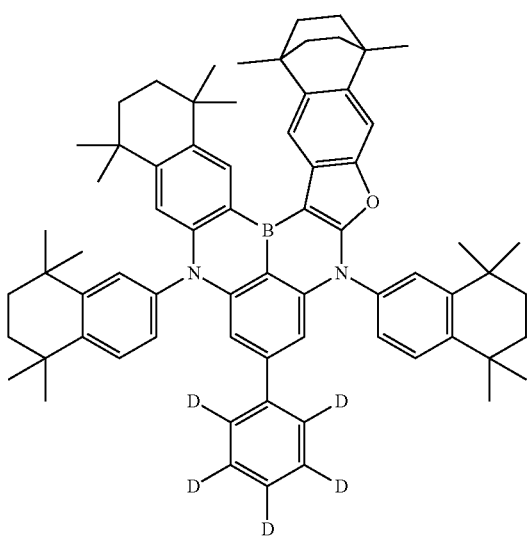
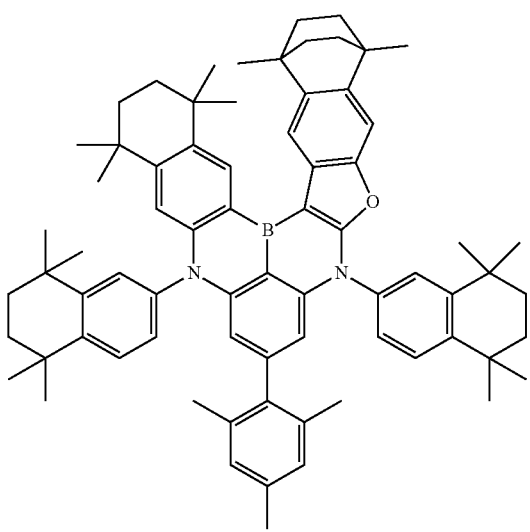
2874
-continued
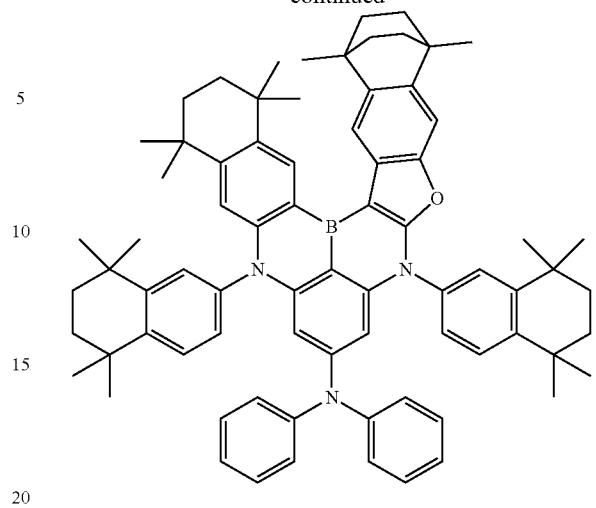
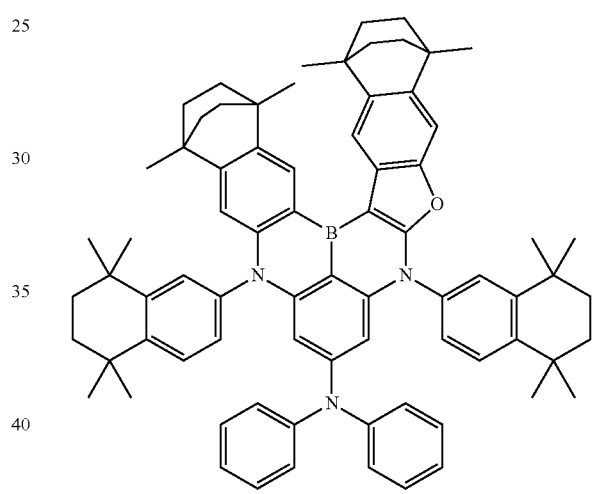
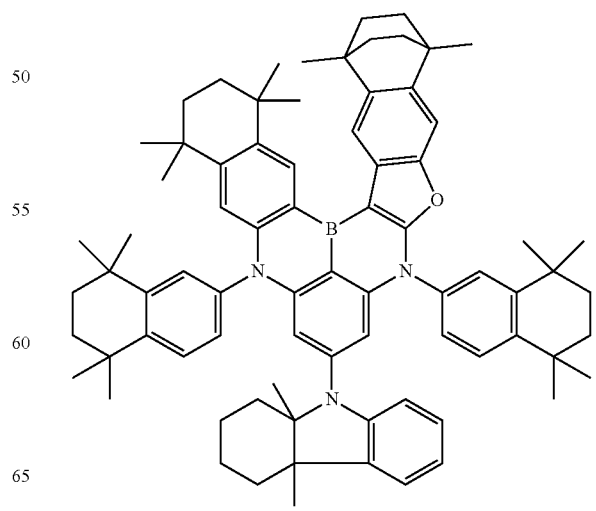

2875
-continued
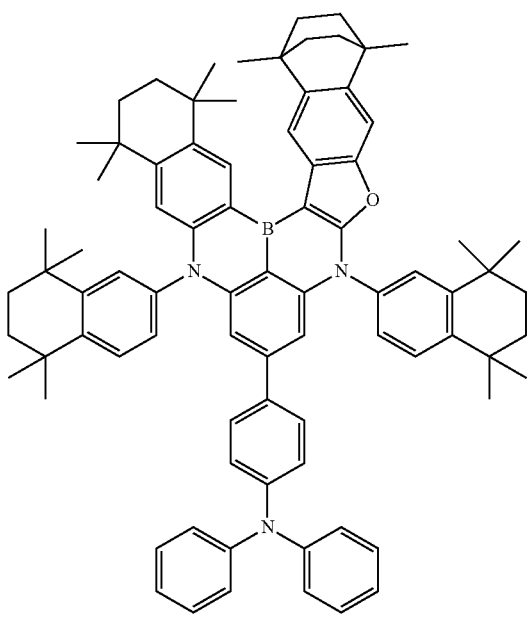
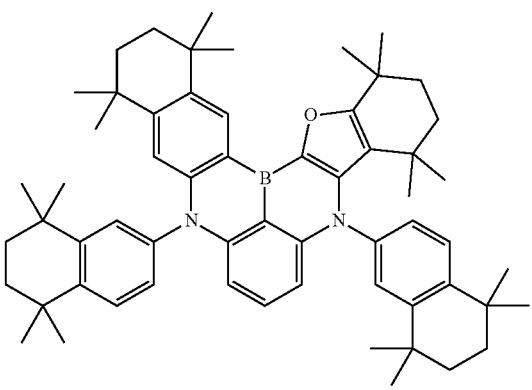
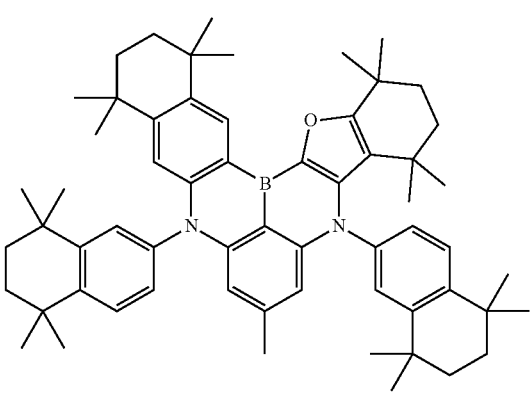
2876
-continued
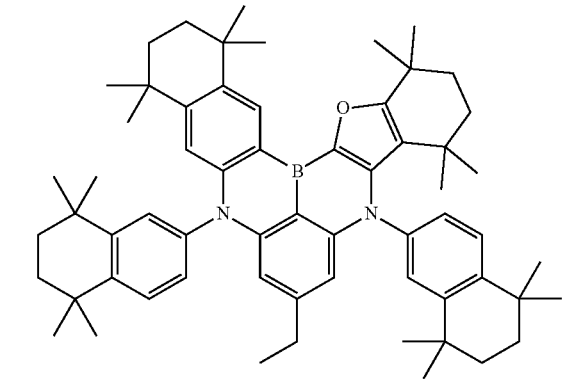
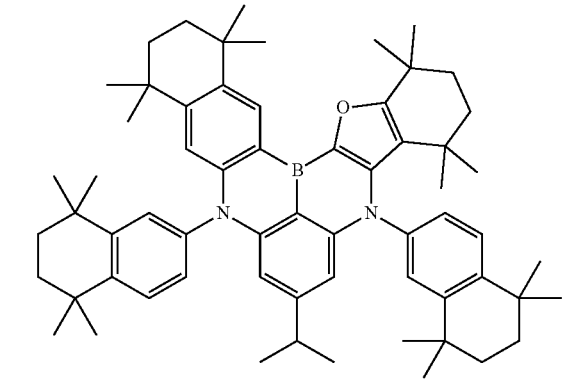
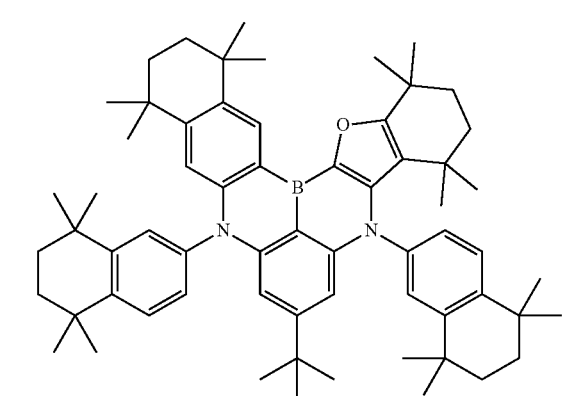
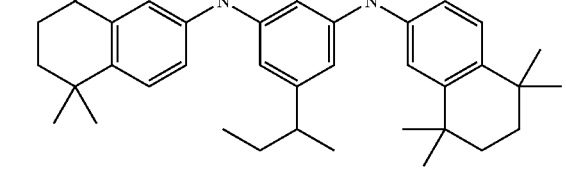

| 2877 -continued | 2878 -continued |
|---|---|
| 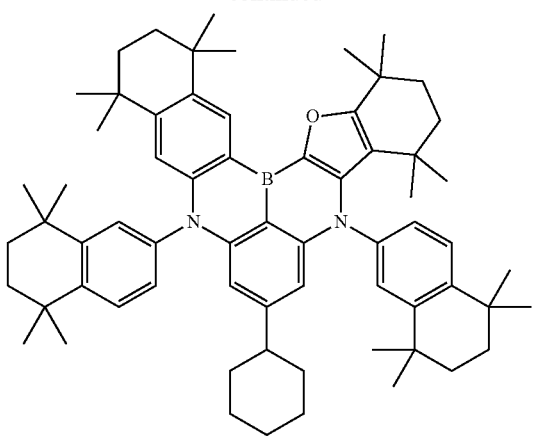 | 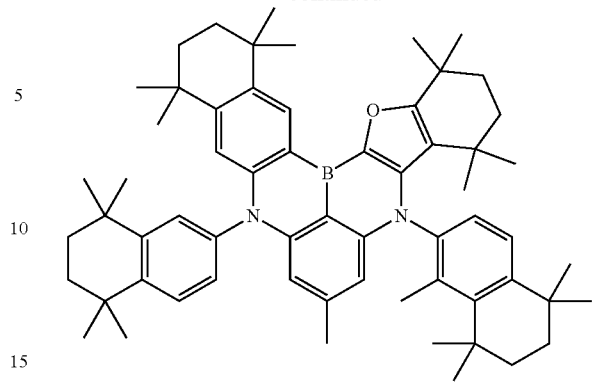 |
| 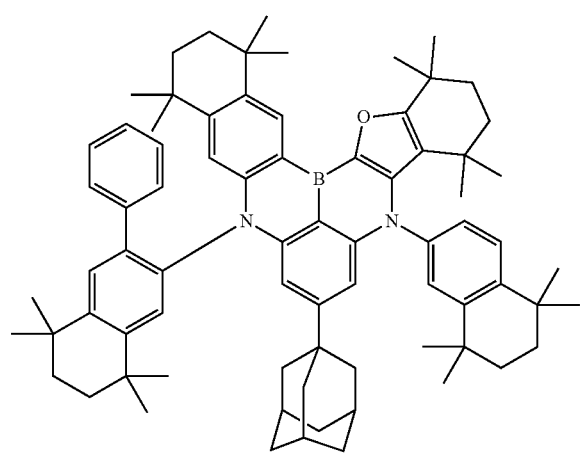 | 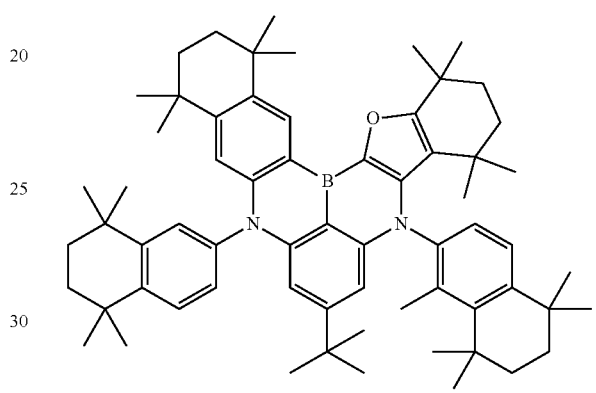 |
| 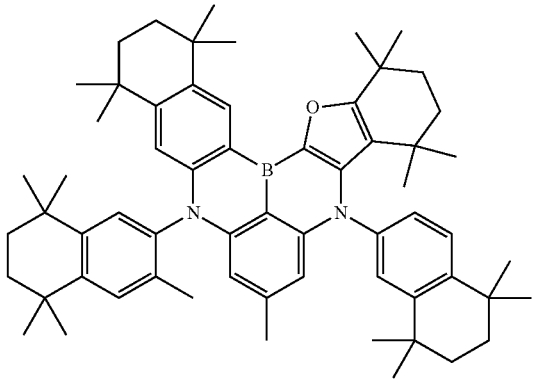 | 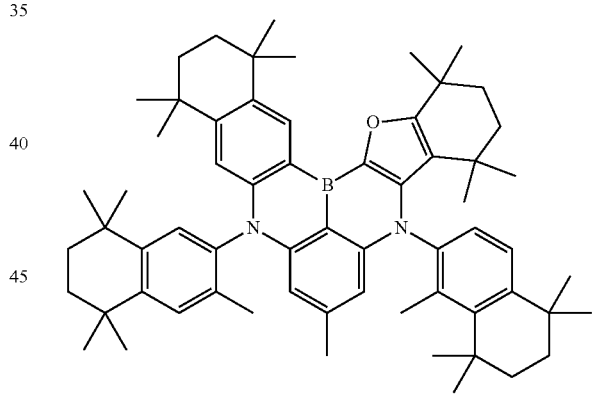 |
| 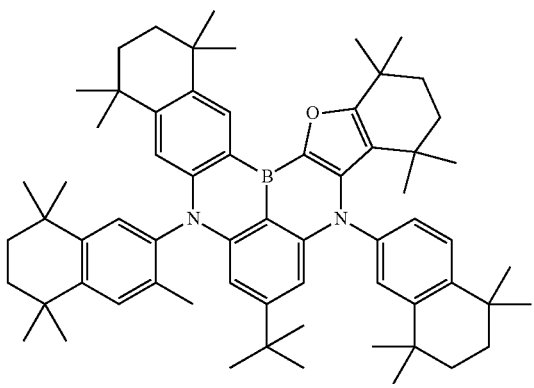 | 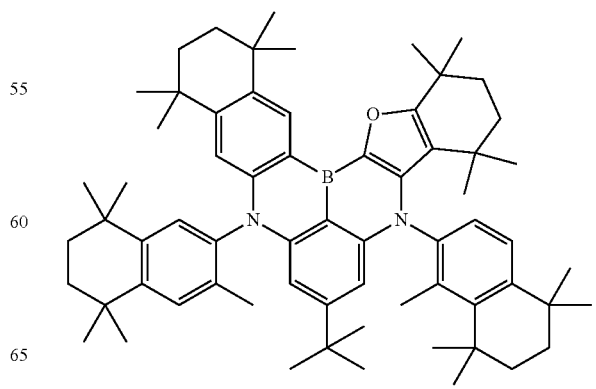 |

2879
-continued
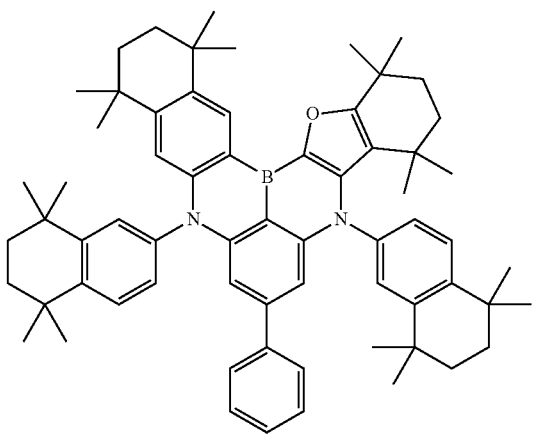
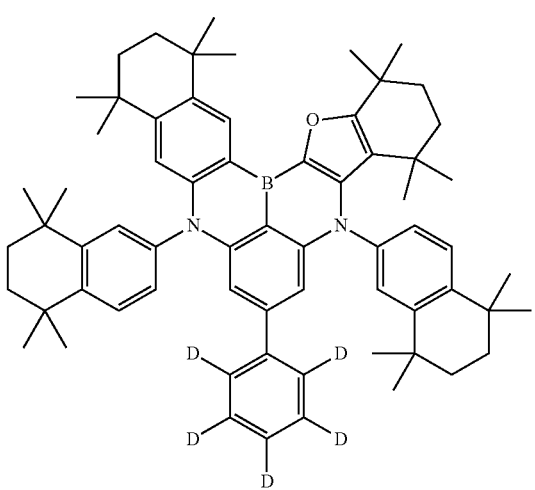
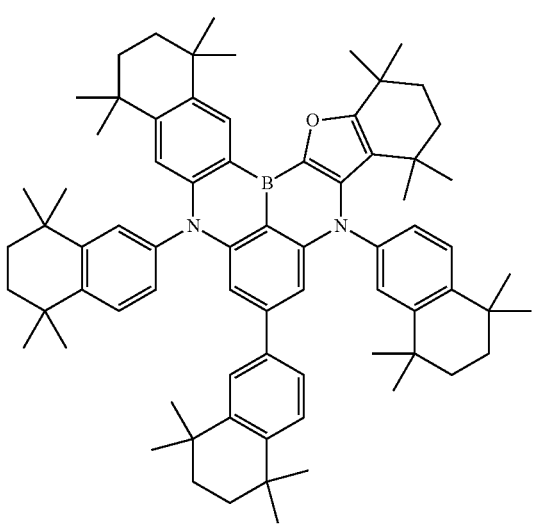
2880
-continued
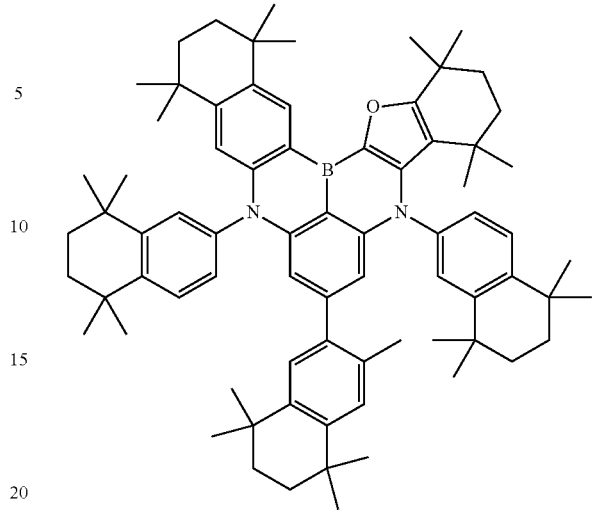
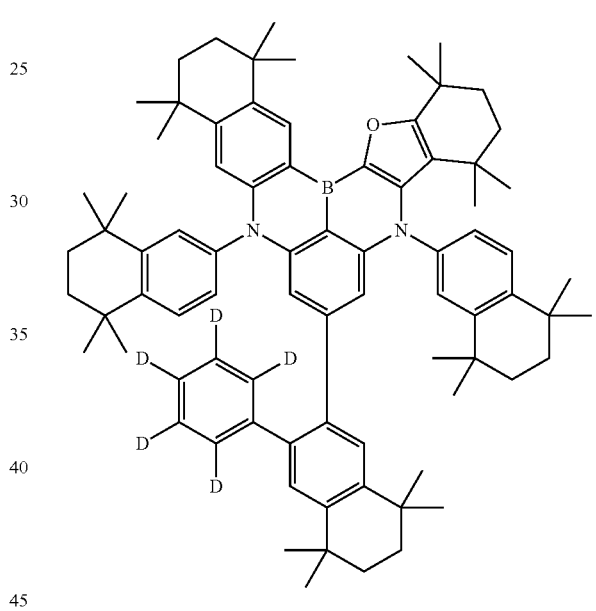
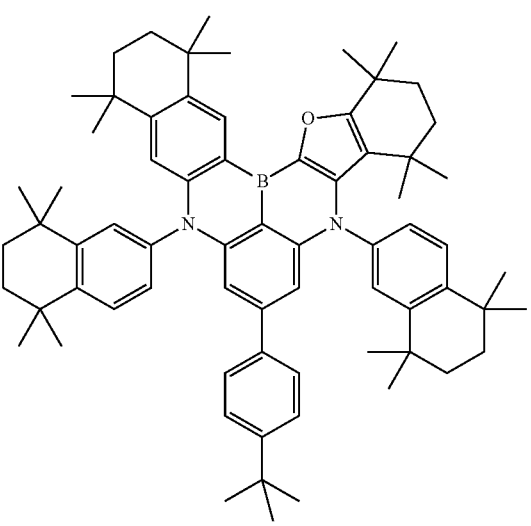

2881
-continued
2882
-continued
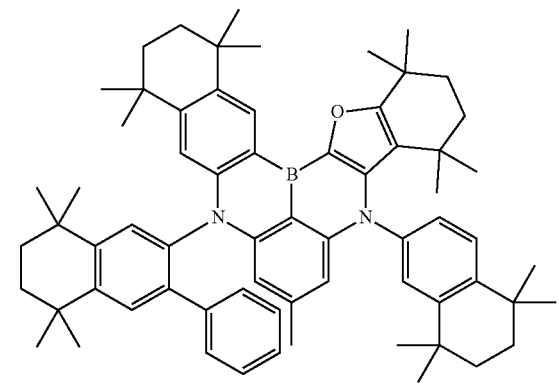
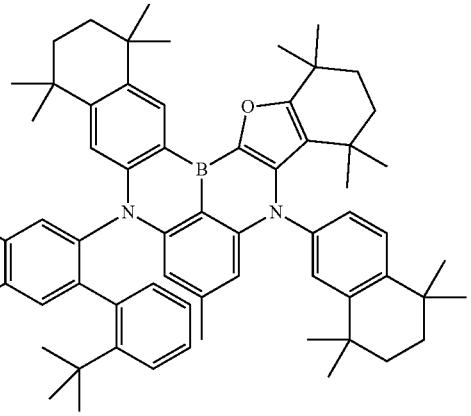
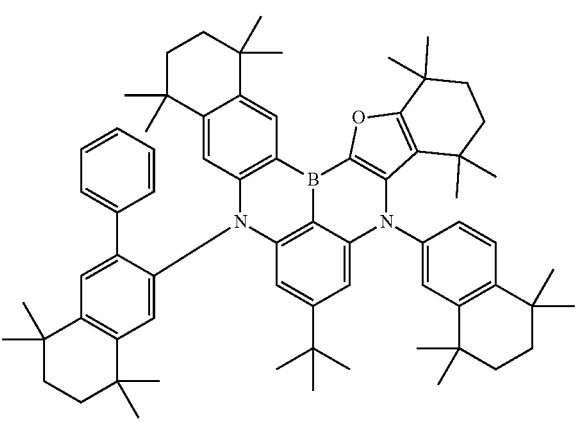
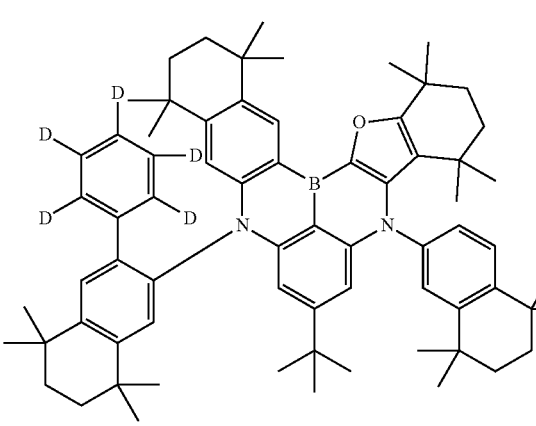
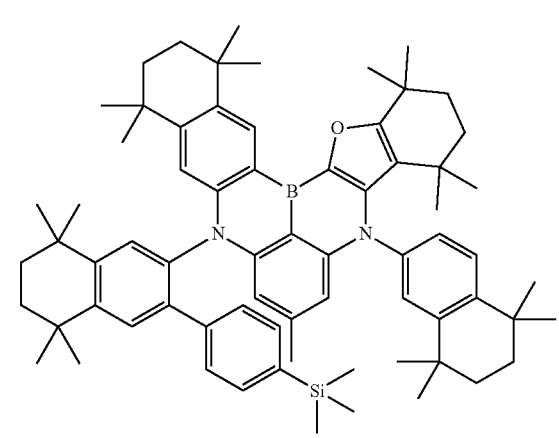

2883
-continued
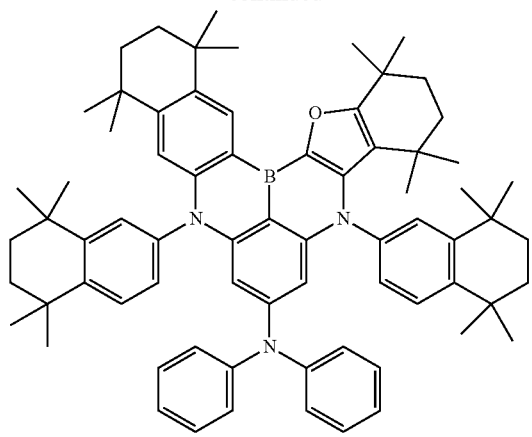
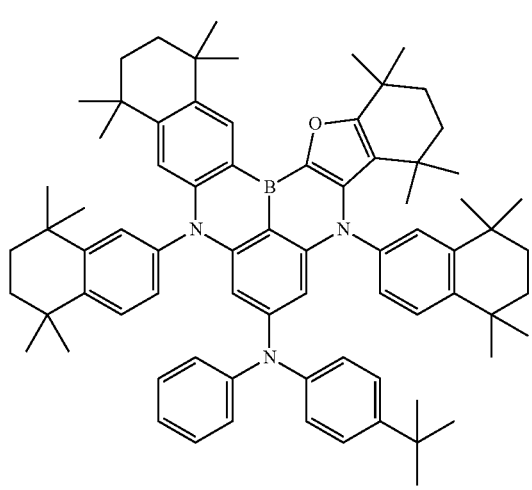
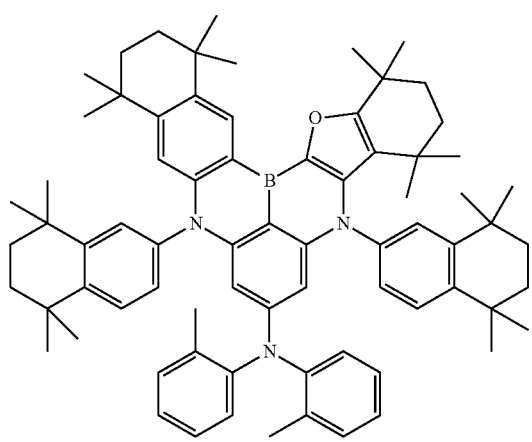
2884
-continued
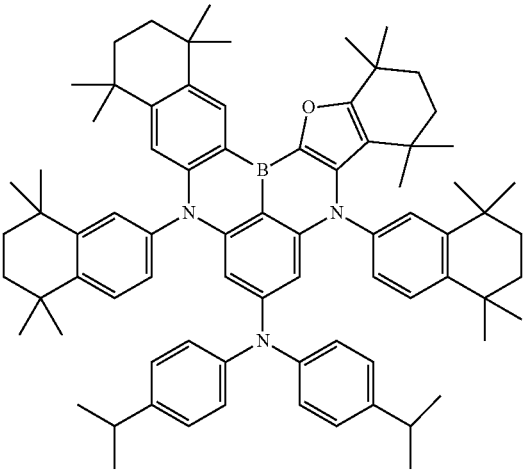
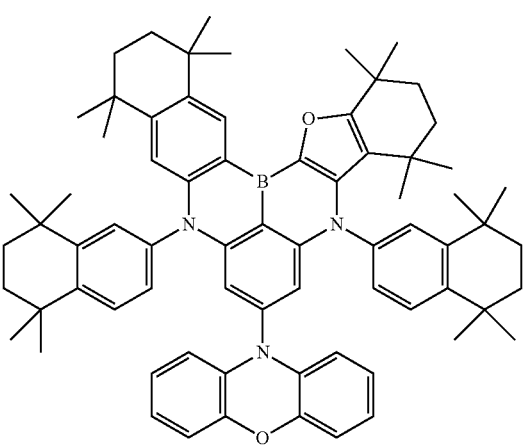
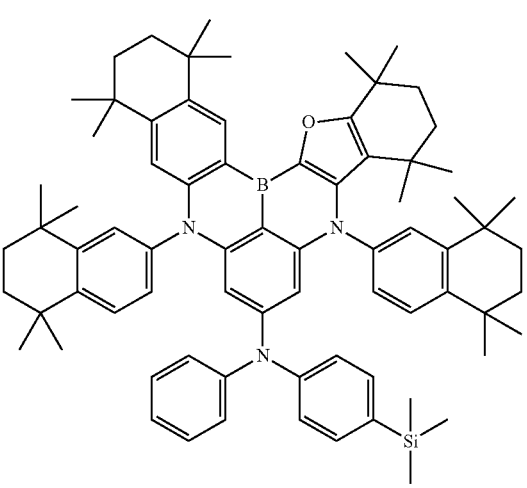

2885
-continued
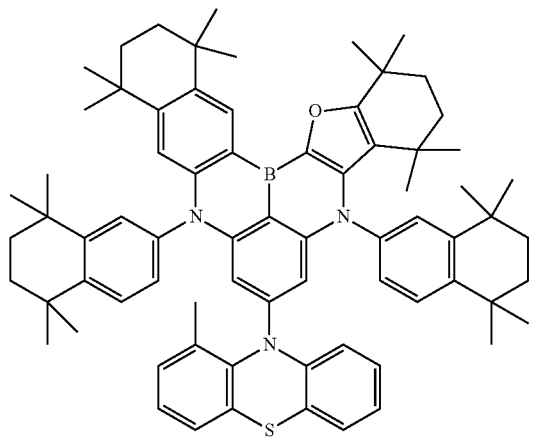
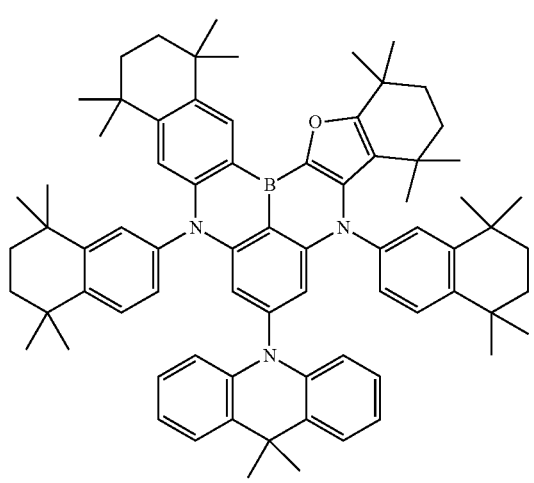
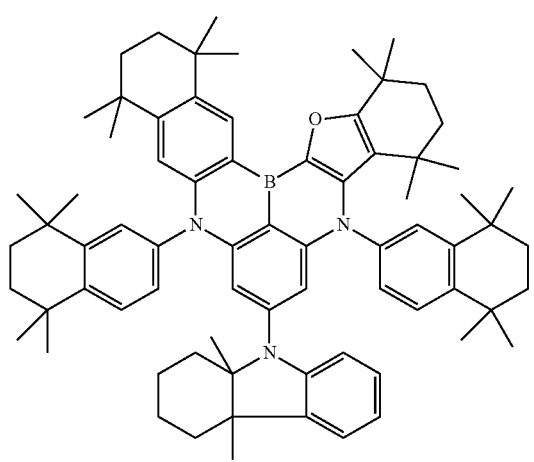
2886
-continued
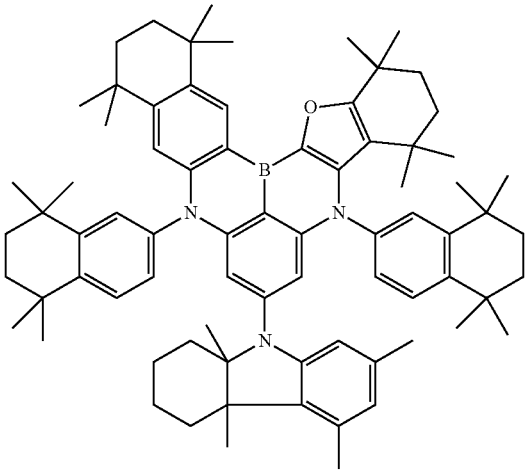
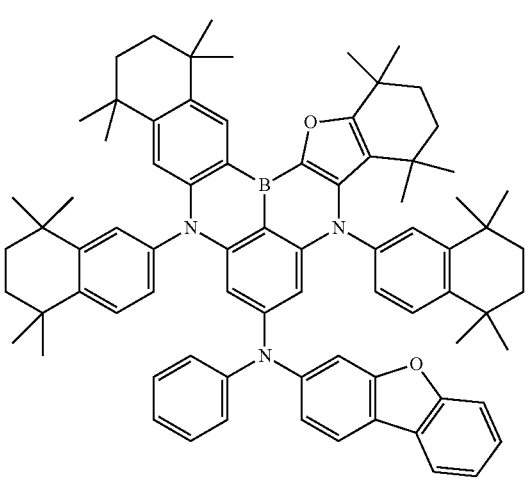
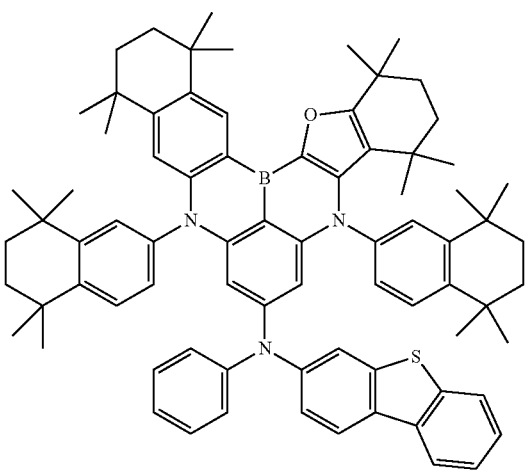

2887
-continued
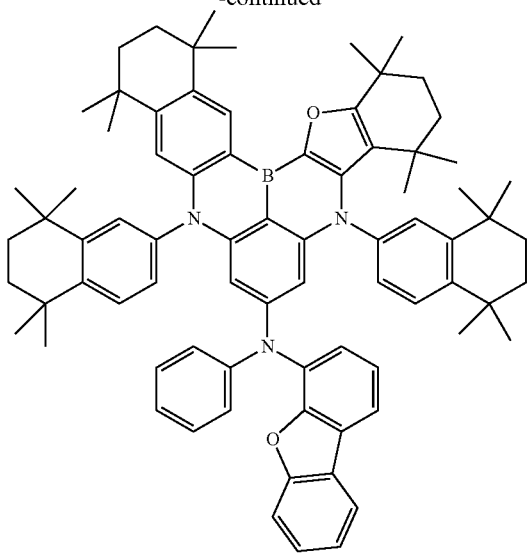
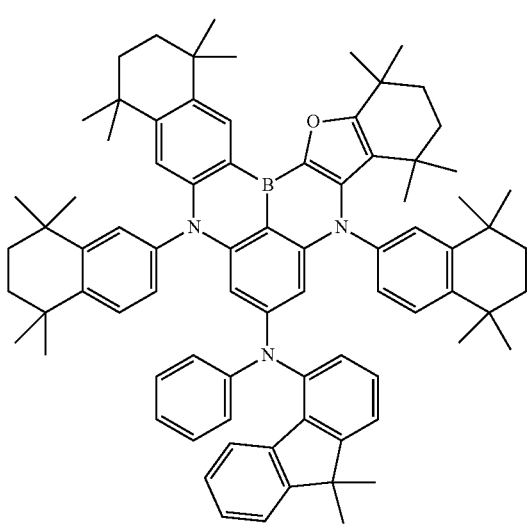
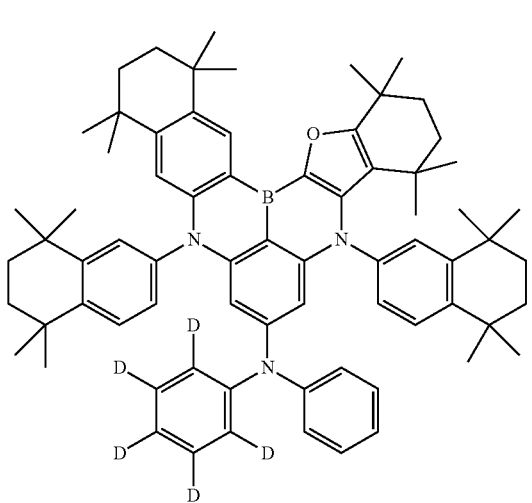
2888
-continued
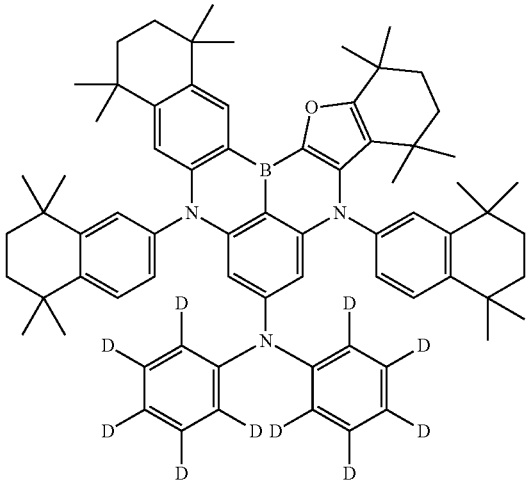
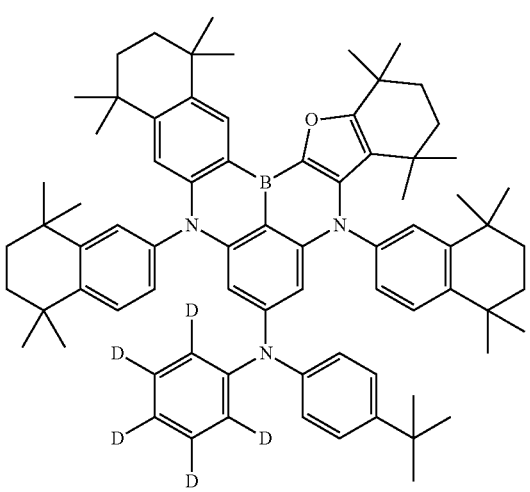
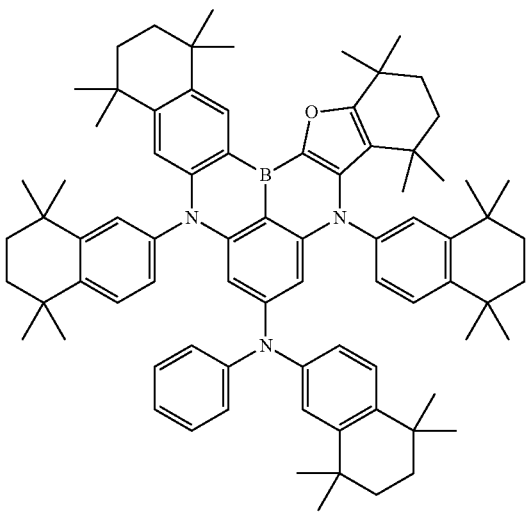

2889
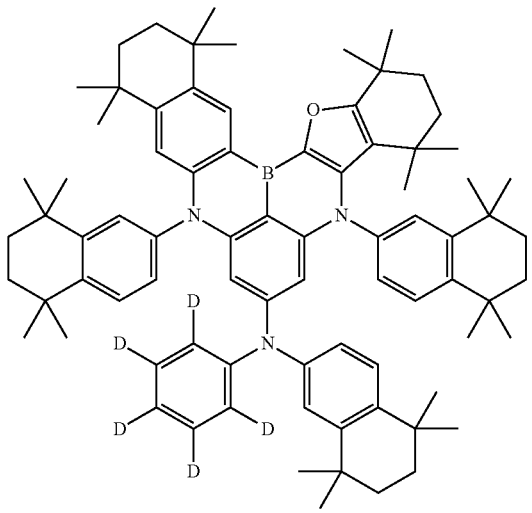
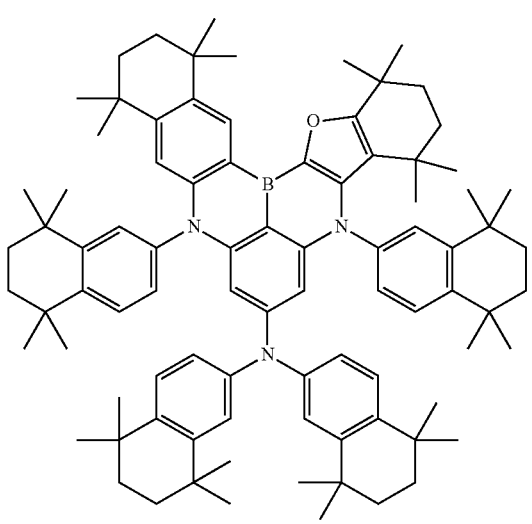
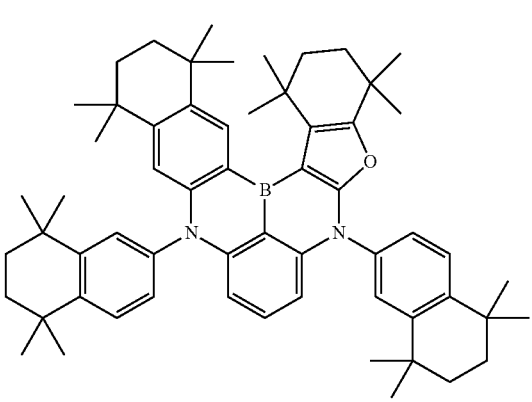
2890
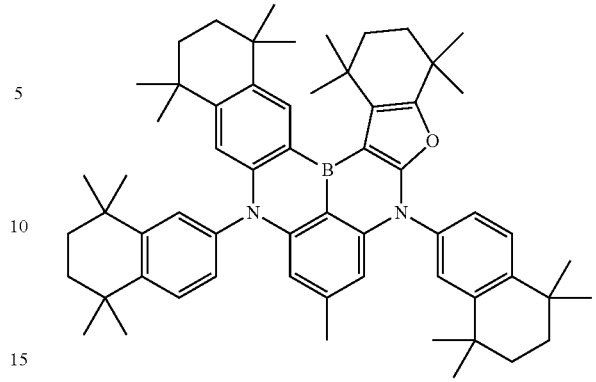
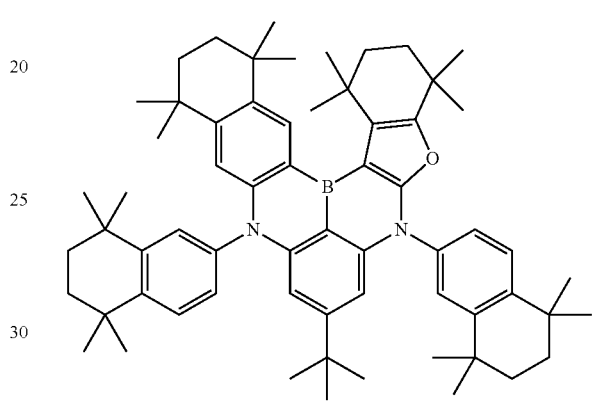
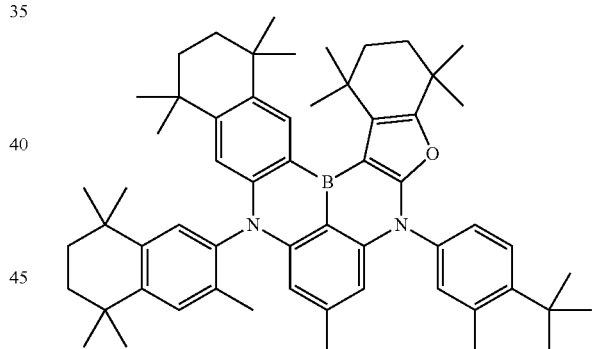
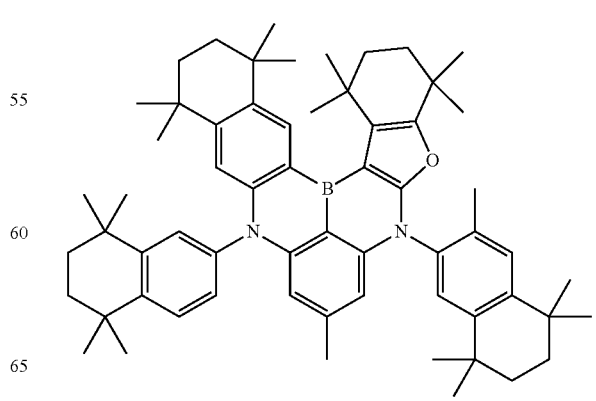

2891
-continued
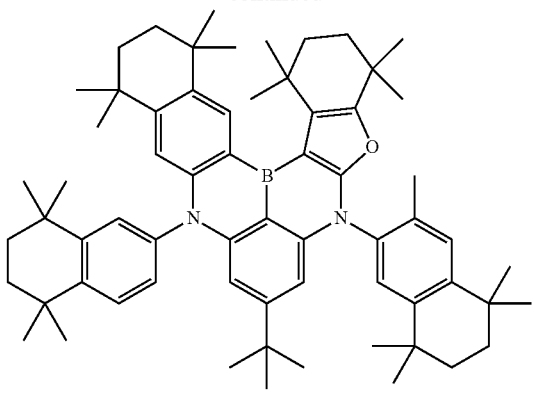
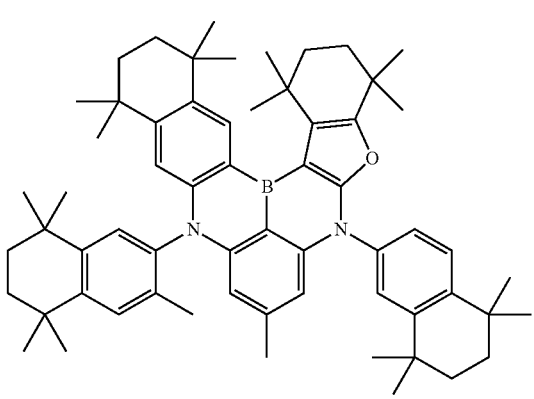
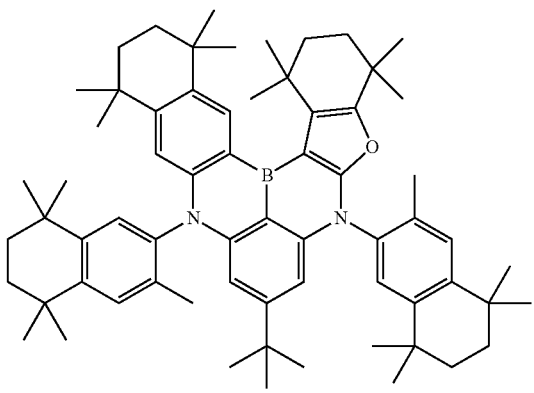
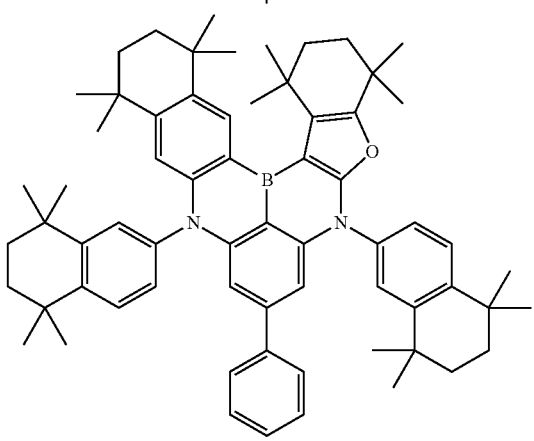
2892
-continued
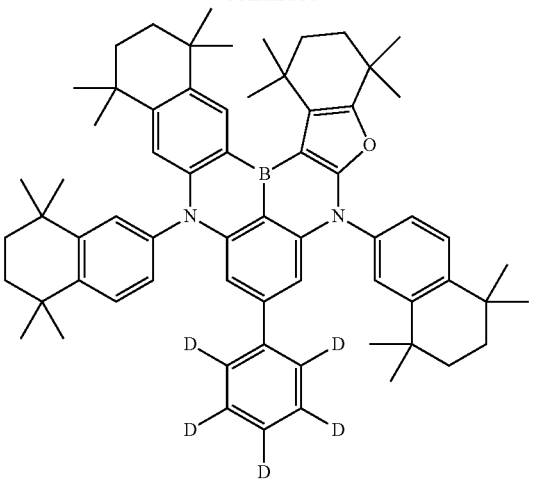
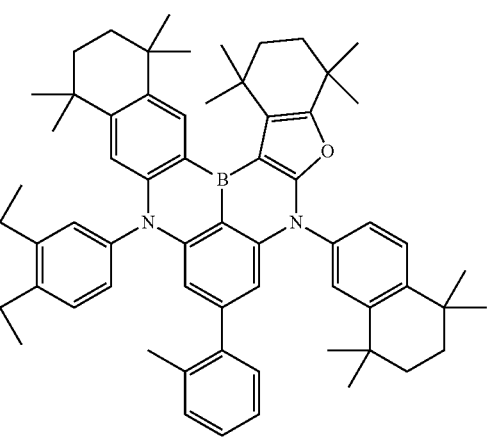
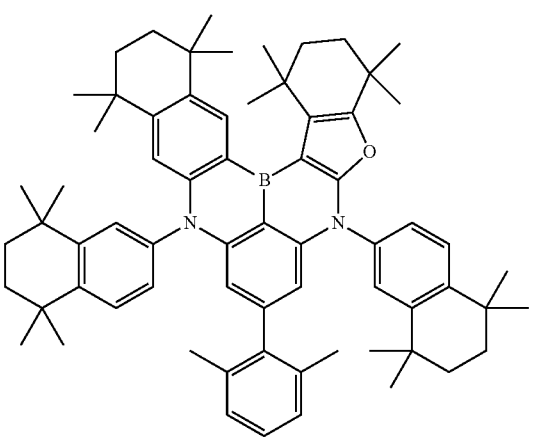

2893
-continued
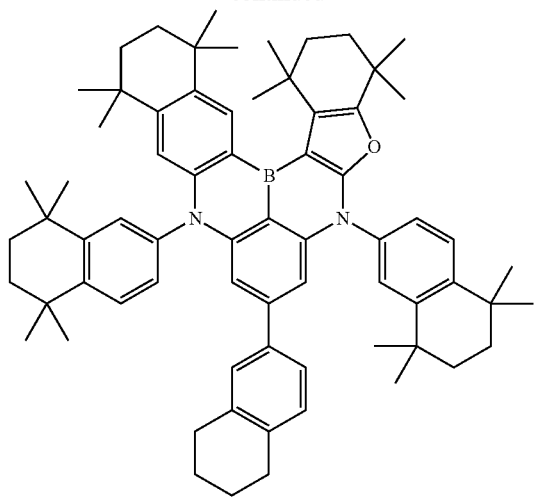
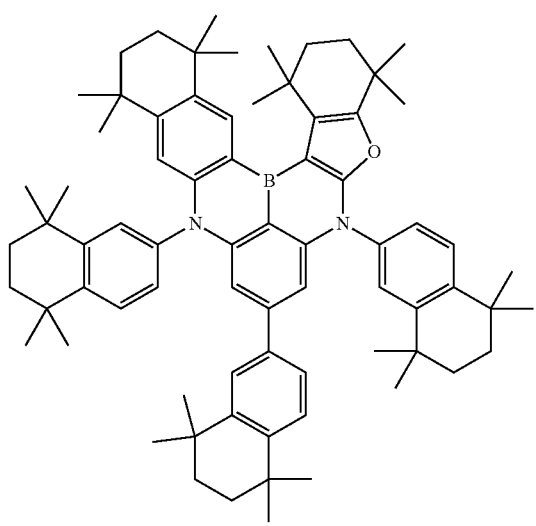
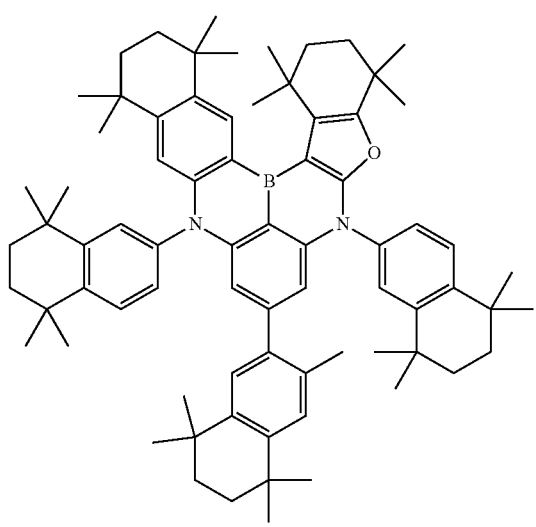
2894
-continued
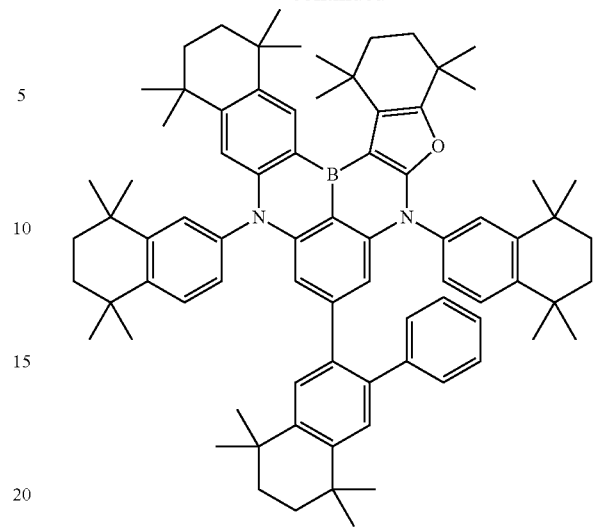
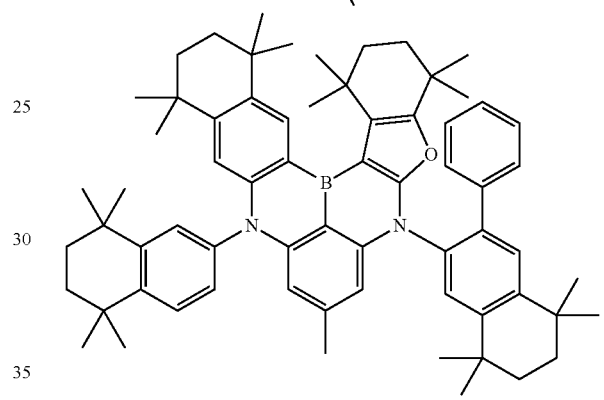
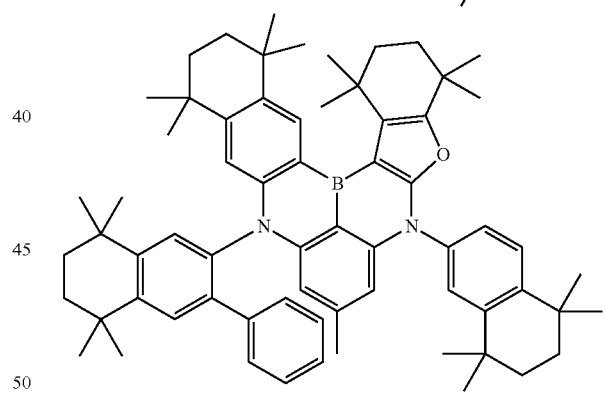
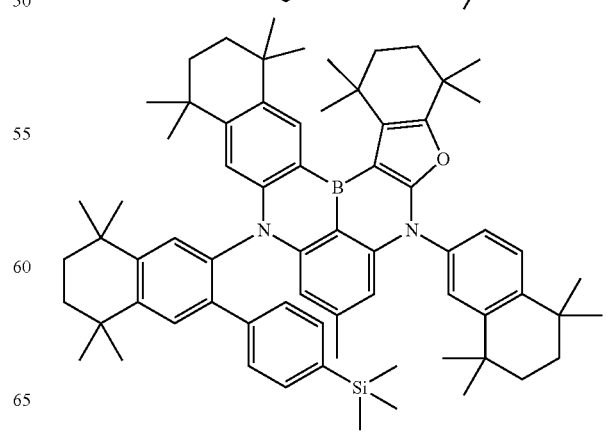

2895
-continued
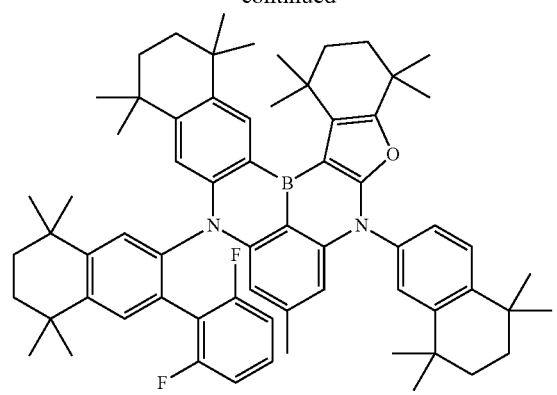
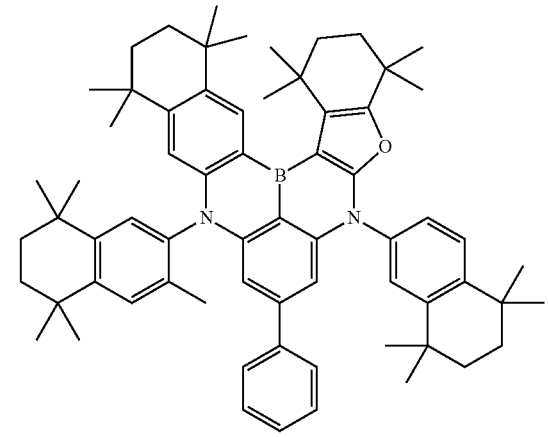
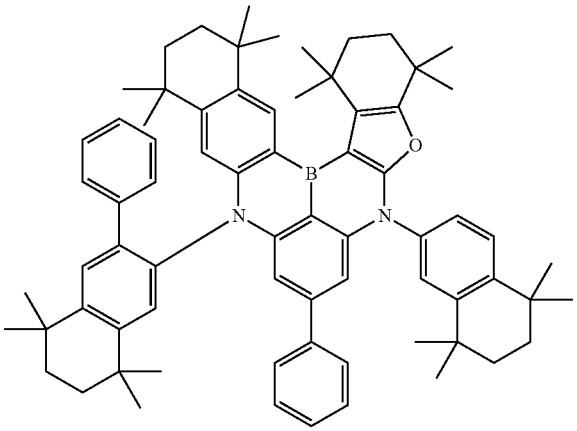
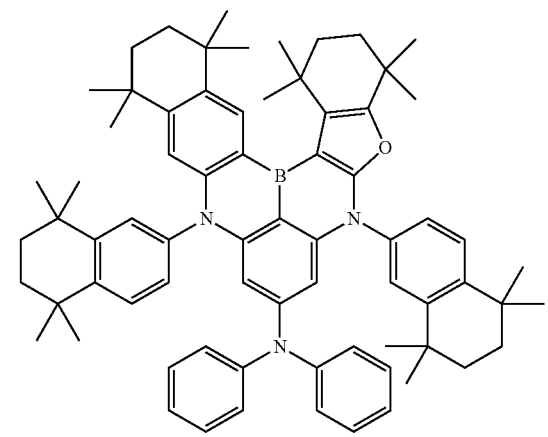
2896
-continued
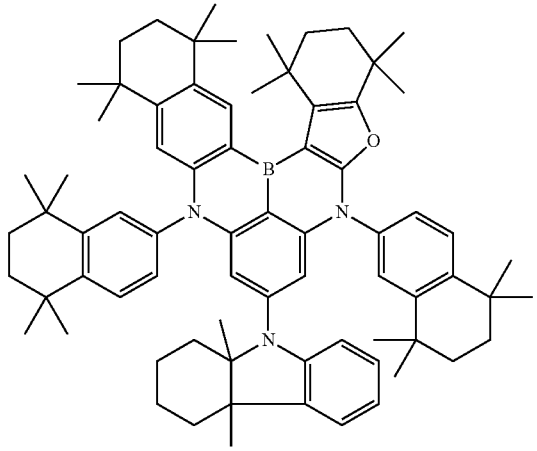
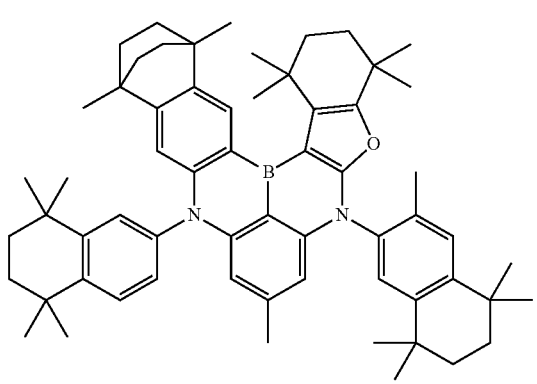
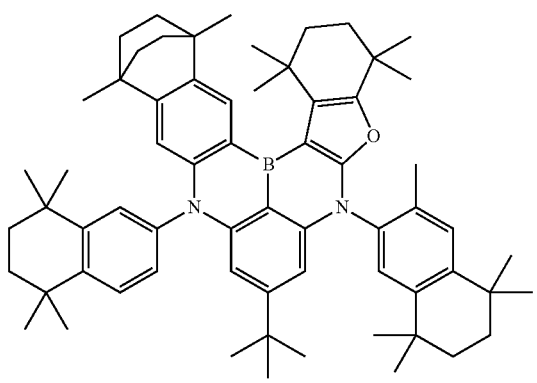
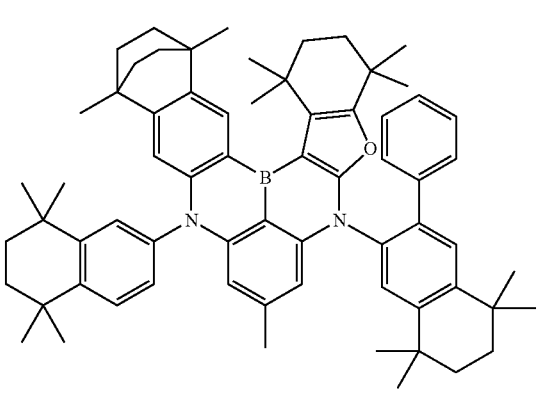

2897
-continued
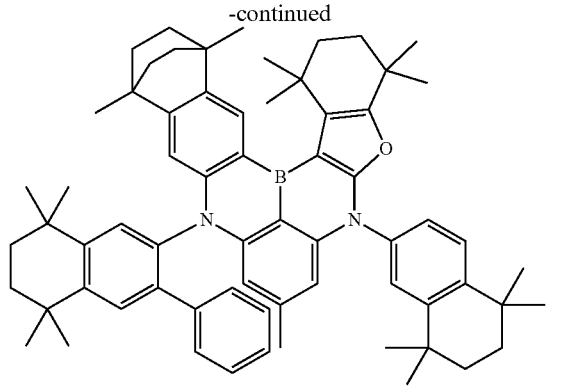
wherein,
Ph is a phenyl group, and D is deuterium.
* * * * *